United States Patent
Gross et al.

(10) Patent No.: US 12,024,750 B2
(45) Date of Patent: Jul. 2, 2024

(54) METHYLATION MARKERS AND TARGETED METHYLATION PROBE PANEL

(71) Applicant: GRAIL, LLC, Menlo Park, CA (US)

(72) Inventors: Samuel S. Gross, Menlo Park, CA (US); Hamed Amini, Menlo Park, CA (US); Arash Jamshidi, Menlo Park, CA (US); Seyedmehdi Shojaee, Menlo Park, CA (US); Srinka Ghosh, Menlo Park, CA (US); Rongsu Qi, Menlo Park, CA (US); M. Cyrus Maher, Menlo Park, CA (US); Alexander P. Fields, Menlo Park, CA (US); Oliver Claude Venn, Menlo Park, CA (US)

(73) Assignee: GRAIL, LLC, Menlo Park, CA (US)

( * ) Notice: Subject to any disclaimer, the term of this patent is extended or adjusted under 35 U.S.C. 154(b) by 0 days.

(21) Appl. No.: 17/061,048

(22) Filed: Oct. 1, 2020

(65) Prior Publication Data
US 2021/0025011 A1    Jan. 28, 2021

Related U.S. Application Data

(63) Continuation of application No. PCT/US2019/025358, filed on Apr. 2, 2019.

(60) Provisional application No. 62/651,643, filed on Apr. 2, 2018, provisional application No. 62/738,271, filed on Sep. 28, 2018.

(51) Int. Cl.
| | |
|---|---|
| C40B 40/06 | (2006.01) |
| C12Q 1/6806 | (2018.01) |
| C12Q 1/6886 | (2018.01) |
| C12Q 1/70 | (2006.01) |

(52) U.S. Cl.
CPC ........... *C12Q 1/6886* (2013.01); *C12Q 1/70* (2013.01); *C40B 40/06* (2013.01); *C12Q 2600/154* (2013.01)

(58) Field of Classification Search
None
See application file for complete search history.

(56) References Cited

U.S. PATENT DOCUMENTS

| | | |
|---|---|---|
| 6,773,897 B2 | 8/2004 | Herman et al. |
| 6,773,987 B1 | 8/2004 | Rahim et al. |
| 7,041,455 B2 | 5/2006 | Magness et al. |
| 7,371,526 B2 | 5/2008 | Zon et al. |
| 7,413,855 B2 | 8/2008 | Bergmann et al. |
| 7,655,399 B2 | 2/2010 | Cantor et al. |

(Continued)

FOREIGN PATENT DOCUMENTS

| | | |
|---|---|---|
| EP | 1342794 B1 | 12/2005 |
| EP | 1394173 B1 | 10/2007 |

(Continued)

OTHER PUBLICATIONS

Handbook of Chemistry and Physics, 49th Edition, 1968, Weast (ed.), The Chemical Rubber Co., Cleveland, Ohio, p. 245.*

(Continued)

*Primary Examiner* — Robert T. Crow
(74) *Attorney, Agent, or Firm* — Greenberg Traurig, LLP

(57) ABSTRACT

The present description provides a cancer assay panel for targeted detection of cancer-specific methylation patterns. Further provided herein includes methods of designing, making, and using the cancer assay panel for diagnosis of cancer.

21 Claims, 21 Drawing Sheets

(56) References Cited

U.S. PATENT DOCUMENTS

| | | |
|---|---|---|
| 7,700,282 B2 | 4/2010 | Tetzner et al. |
| 7,700,324 B1 | 4/2010 | Issa et al. |
| 7,749,702 B2 | 7/2010 | Lofton-Day et al. |
| 7,785,798 B2 | 8/2010 | Cantor et al. |
| 7,899,626 B2 | 3/2011 | Kruglyak et al. |
| 8,076,063 B2 | 12/2011 | Fan |
| 8,133,986 B2 | 3/2012 | Issa et al. |
| 8,137,937 B2 | 3/2012 | Markert-Hahn |
| 8,143,001 B2 | 3/2012 | Kurn et al. |
| 8,150,626 B2 | 4/2012 | Fan et al. |
| 8,318,433 B2 | 11/2012 | Brenner |
| 8,318,460 B2 | 11/2012 | Cantor et al. |
| 8,415,100 B2 | 4/2013 | Markert-Hahn et al. |
| 8,455,190 B2 | 6/2013 | Makrigiorgos |
| 8,481,292 B2 | 7/2013 | Casbon et al. |
| 8,486,634 B2 | 7/2013 | Lim et al. |
| 8,541,207 B2 | 9/2013 | Kester |
| 8,586,310 B2 | 11/2013 | Mitra et al. |
| 8,673,555 B2 | 3/2014 | Taylor et al. |
| 8,728,764 B2 | 5/2014 | Boutell |
| 8,741,567 B2 | 6/2014 | He et al. |
| 8,771,939 B2 | 7/2014 | Tetzner et al. |
| 8,822,155 B2 | 9/2014 | Sukumar et al. |
| 8,865,410 B2 | 10/2014 | Shendure et al. |
| 8,880,350 B2 | 11/2014 | Von Hoff et al. |
| 8,900,829 B2 | 12/2014 | Distler et al. |
| 8,927,209 B2 | 1/2015 | Hamamoto et al. |
| 9,040,239 B1 | 5/2015 | Zheng et al. |
| 9,115,386 B2 | 8/2015 | Rao et al. |
| 9,121,061 B2 | 9/2015 | Vaisvila et al. |
| 9,121,069 B2 | 9/2015 | Lo et al. |
| 9,128,086 B2 | 9/2015 | Bawden et al. |
| 9,183,349 B2 | 11/2015 | Kupershmidt et al. |
| 9,200,260 B2 | 12/2015 | Correa, Jr. et al. |
| 9,222,937 B2 | 12/2015 | Micallef |
| 9,260,745 B2 | 2/2016 | Rava et al. |
| 9,267,117 B2 | 2/2016 | Guan et al. |
| 9,290,803 B2 | 3/2016 | Laird et al. |
| 9,290,807 B2 | 3/2016 | Booth et al. |
| 9,292,660 B2 | 3/2016 | Von Hoff et al. |
| 9,315,853 B2 | 4/2016 | Domanico et al. |
| 9,371,566 B2 | 6/2016 | Lo et al. |
| 9,394,332 B2 | 7/2016 | Markert-Hahn et al. |
| 9,400,276 B2 | 7/2016 | Micallef |
| 9,447,452 B2 | 9/2016 | Rao et al. |
| 9,464,277 B2 | 10/2016 | Zheng et al. |
| 9,476,095 B2 | 10/2016 | Vogelstein et al. |
| 9,580,754 B2 | 2/2017 | Markowitz et al. |
| 9,598,731 B2 | 3/2017 | Talasaz |
| 9,670,530 B2 | 6/2017 | Kostem et al. |
| 9,702,002 B2 | 7/2017 | Boutell |
| 9,702,004 B2 | 7/2017 | Van Eijk et al. |
| 9,732,390 B2 | 8/2017 | Lo et al. |
| 9,745,614 B2 | 8/2017 | Schroeder |
| 9,745,627 B2 | 8/2017 | Van Eijk et al. |
| 9,752,188 B2 | 9/2017 | Schmitt et al. |
| 9,816,986 B2 | 11/2017 | Rao et al. |
| 9,834,822 B2 | 12/2017 | Talasaz |
| 9,840,743 B2 | 12/2017 | Talasaz |
| 9,850,523 B1 | 12/2017 | Chudova et al. |
| 9,862,995 B2 | 1/2018 | Patel |
| 9,868,756 B2 | 1/2018 | Markert-Hahn et al. |
| 9,896,725 B2 | 2/2018 | Lee et al. |
| 9,896,726 B2 | 2/2018 | Vaisvila et al. |
| 9,902,992 B2 | 2/2018 | Talasaz et al. |
| 9,920,363 B2 | 3/2018 | Gao et al. |
| 9,920,366 B2 | 3/2018 | Eltoukhy et al. |
| 9,938,575 B2 | 4/2018 | Tischfield et al. |
| 9,984,201 B2 | 5/2018 | Zhang et al. |
| 10,011,878 B2 | 7/2018 | Ahlquist et al. |
| 10,031,131 B2 | 7/2018 | Rao et al. |
| 10,093,986 B2 | 10/2018 | Zhang et al. |
| 10,144,953 B2 | 12/2018 | Domanico et al. |
| 10,297,342 B2 | 5/2019 | Lo et al. |
| 10,392,666 B2 | 8/2019 | Lo et al. |
| 10,435,754 B2 | 10/2019 | Lo et al. |
| 10,435,755 B2 | 10/2019 | Ahlquist et al. |
| 10,704,083 B2 | 7/2020 | Domanico et al. |
| 10,718,026 B2 | 7/2020 | Weinhausel et al. |
| 2002/0192698 A1 | 12/2002 | Pinkel et al. |
| 2003/0104464 A1 | 6/2003 | Berlin et al. |
| 2005/0196792 A1 | 9/2005 | Fodor et al. |
| 2005/0221314 A1 | 10/2005 | Berlin et al. |
| 2006/0286576 A1 | 12/2006 | Lofton-Day et al. |
| 2006/0292585 A1 | 12/2006 | Nautiyal et al. |
| 2007/0141582 A1 | 6/2007 | Li et al. |
| 2007/0161031 A1 | 7/2007 | Trinklein et al. |
| 2007/0264640 A1 | 11/2007 | Barrett |
| 2008/0081338 A1 | 4/2008 | Lo et al. |
| 2008/0102450 A1 | 5/2008 | Barrett |
| 2008/0200343 A1 | 8/2008 | Clemens et al. |
| 2008/0286787 A1 | 11/2008 | Campan et al. |
| 2008/0305481 A1* | 12/2008 | Whitman ............... C12Q 1/686 |
| | | 435/6.12 |
| 2009/0280479 A1 | 11/2009 | Hoon et al. |
| 2010/0068720 A1 | 3/2010 | Li et al. |
| 2010/0120022 A1 | 5/2010 | Ayalon-Soffer et al. |
| 2010/0304978 A1 | 12/2010 | Deng et al. |
| 2011/0027771 A1 | 2/2011 | Deng |
| 2011/0165565 A1 | 7/2011 | Wang et al. |
| 2011/0237444 A1 | 9/2011 | Clancy et al. |
| 2012/0053062 A1 | 3/2012 | Brooks |
| 2012/0149593 A1 | 6/2012 | Hicks et al. |
| 2012/0157324 A1 | 6/2012 | Lizardi et al. |
| 2012/0190023 A1 | 7/2012 | Wasserstrom |
| 2012/0208711 A1 | 8/2012 | Cortese |
| 2012/0221249 A1 | 8/2012 | Lizardi et al. |
| 2013/0017958 A1 | 1/2013 | Benz et al. |
| 2013/0059734 A1 | 3/2013 | Molloy et al. |
| 2013/0129668 A1 | 5/2013 | Firestein et al. |
| 2013/0130924 A1* | 5/2013 | Walrafen ............ C12Q 1/6883 |
| | | 506/9 |
| 2013/0186639 A1 | 7/2013 | Zhao et al. |
| 2013/0203605 A1 | 8/2013 | Shendure et al. |
| 2013/0261984 A1 | 10/2013 | Eberle et al. |
| 2013/0337447 A1* | 12/2013 | Porreca ................. C12Q 1/6886 |
| | | 435/6.11 |
| 2014/0024537 A1 | 1/2014 | Rigatti et al. |
| 2014/0080715 A1 | 3/2014 | Lo et al. |
| 2014/0256574 A1 | 9/2014 | Herold et al. |
| 2014/0274740 A1 | 9/2014 | Srinivasan et al. |
| 2014/0274748 A1* | 9/2014 | Ahlquist ............... C12Q 1/6886 |
| | | 506/7 |
| 2014/0274752 A1 | 9/2014 | Blume et al. |
| 2014/0274767 A1 | 9/2014 | Yegnasubramanian et al. |
| 2014/0342940 A1* | 11/2014 | Oliphant ............... C12Q 1/6858 |
| | | 506/9 |
| 2014/0357497 A1 | 12/2014 | Zhang et al. |
| 2014/0364323 A1 | 12/2014 | Fan et al. |
| 2015/0038352 A1 | 2/2015 | Cao et al. |
| 2015/0099670 A1 | 4/2015 | Li et al. |
| 2015/0104793 A1 | 4/2015 | Quake et al. |
| 2015/0159212 A1 | 6/2015 | Pantoja et al. |
| 2015/0197798 A1 | 7/2015 | Xu et al. |
| 2015/0197809 A1 | 7/2015 | Myers et al. |
| 2015/0209786 A1 | 7/2015 | Hage et al. |
| 2015/0259743 A1 | 9/2015 | Burgess et al. |
| 2015/0299781 A1 | 10/2015 | Ost |
| 2015/0322513 A1 | 11/2015 | Gromminger et al. |
| 2015/0368708 A1 | 12/2015 | Talasaz |
| 2016/0003848 A1 | 1/2016 | Holdenrieder |
| 2016/0017396 A1 | 1/2016 | Cann et al. |
| 2016/0017419 A1 | 1/2016 | Chiu et al. |
| 2016/0040229 A1 | 2/2016 | Talasaz et al. |
| 2016/0047001 A1* | 2/2016 | Larisch ................ C12Q 1/6886 |
| | | 514/245 |
| 2016/0138079 A1 | 5/2016 | Guan et al. |
| 2016/0144378 A1 | 5/2016 | Huang et al. |
| 2016/0168648 A1 | 6/2016 | Allawi et al. |
| 2016/0186267 A1 | 6/2016 | So et al. |
| 2016/0210403 A1 | 7/2016 | Zhang et al. |
| 2016/0232290 A1 | 8/2016 | Rava et al. |
| 2016/0239604 A1 | 8/2016 | Chudova et al. |
| 2016/0251704 A1 | 9/2016 | Talasaz et al. |

(56) References Cited

U.S. PATENT DOCUMENTS

| | | |
|---|---|---|
| 2016/0258014 A1 | 9/2016 | Booth et al. |
| 2016/0265027 A1 | 9/2016 | Sanches-Kuiper et al. |
| 2016/0265042 A1 | 9/2016 | Schroeder et al. |
| 2016/0275240 A1 | 9/2016 | Huelga |
| 2016/0281175 A1 | 9/2016 | Weinhausel et al. |
| 2016/0298183 A1 | 10/2016 | Wen et al. |
| 2016/0319345 A1 | 11/2016 | Gnerre et al. |
| 2016/0333417 A1 | 11/2016 | Talasaz |
| 2016/0333420 A1 | 11/2016 | Stern et al. |
| 2016/0340740 A1 | 11/2016 | Zhang |
| 2016/0340749 A1* | 11/2016 | Stelzer ............... C12N 15/907 |
| 2016/0348152 A1 | 12/2016 | Zheng et al. |
| 2016/0357903 A1 | 12/2016 | Shendure |
| 2016/0362748 A1 | 12/2016 | Mongan et al. |
| 2017/0024513 A1 | 1/2017 | Lo et al. |
| 2017/0029900 A1 | 2/2017 | Lo et al. |
| 2017/0101685 A1 | 4/2017 | Lo et al. |
| 2017/0121767 A1 | 5/2017 | Dor et al. |
| 2017/0137871 A1 | 5/2017 | Lai et al. |
| 2017/0175205 A1 | 6/2017 | Toung et al. |
| 2017/0176420 A1 | 6/2017 | Rao et al. |
| 2017/0191119 A1 | 7/2017 | Rao et al. |
| 2017/0198344 A1 | 7/2017 | Vaisvila et al. |
| 2017/0211143 A1 | 7/2017 | Shendure et al. |
| 2017/0218338 A1 | 8/2017 | Rao et al. |
| 2017/0219589 A1 | 8/2017 | Rao et al. |
| 2017/0233829 A1 | 8/2017 | Lo et al. |
| 2017/0235877 A1 | 8/2017 | Lo et al. |
| 2017/0240973 A1 | 8/2017 | Eltoukhy et al. |
| 2017/0249421 A1 | 8/2017 | Eberle et al. |
| 2017/0260590 A1 | 9/2017 | Eltoukhy et al. |
| 2017/0275689 A1 | 9/2017 | Maguire |
| 2017/0292147 A1 | 10/2017 | Kostem et al. |
| 2017/0321276 A1 | 11/2017 | Cantor et al. |
| 2017/0327869 A1 | 11/2017 | Schutz et al. |
| 2017/0356053 A1 | 12/2017 | Otto et al. |
| 2017/0362638 A1 | 12/2017 | Chudova et al. |
| 2018/0010176 A1 | 1/2018 | Patel |
| 2018/0010192 A1 | 1/2018 | Zhang et al. |
| 2018/0023125 A1 | 1/2018 | Talasaz et al. |
| 2018/0044632 A1 | 2/2018 | Rao et al. |
| 2018/0044633 A1 | 2/2018 | Rao et al. |
| 2018/0044731 A1 | 2/2018 | Valouev et al. |
| 2018/0045727 A1 | 2/2018 | Spetzler et al. |
| 2018/0066306 A1 | 3/2018 | Namsaraev et al. |
| 2018/0082012 A1 | 3/2018 | Jiang et al. |
| 2018/0094325 A1 | 4/2018 | Zhang et al. |
| 2018/0105884 A1 | 4/2018 | Lo et al. |
| 2018/0119113 A1 | 5/2018 | Rao et al. |
| 2018/0119225 A1 | 5/2018 | Rao et al. |
| 2018/0119230 A1 | 5/2018 | Velculescu et al. |
| 2018/0120304 A1 | 5/2018 | Rao et al. |
| 2018/0171397 A1 | 6/2018 | Vaisvila et al. |
| 2018/0179587 A1 | 6/2018 | Rao et al. |
| 2018/0180602 A1 | 6/2018 | Rao et al. |
| 2018/0216195 A1 | 8/2018 | Elnitski et al. |
| 2018/0237867 A1 | 8/2018 | Bajic et al. |
| 2018/0327859 A1 | 11/2018 | Van Engeland et al. |
| 2019/0032149 A1 | 1/2019 | Van Engeland et al. |
| 2019/0136327 A1 | 5/2019 | Zhang et al. |
| 2019/0256921 A1 | 8/2019 | Mueller |
| 2019/0287652 A1 | 9/2019 | Gross et al. |
| 2021/0017609 A1 | 1/2021 | Gross |
| 2021/0025011 A1 | 1/2021 | Gross |
| 2021/0238694 A1 | 8/2021 | Gross |
| 2022/0064737 A1 | 3/2022 | Gross |
| 2022/0098672 A1 | 3/2022 | Venn |

FOREIGN PATENT DOCUMENTS

| | | |
|---|---|---|
| EP | 1644519 B1 | 12/2008 |
| EP | 1567669 B1 | 3/2010 |
| EP | 2771483 A1 | 9/2014 |
| EP | 2391729 B1 | 9/2016 |
| EP | 2825675 B1 | 12/2017 |
| EP | 3265562 A2 | 1/2018 |
| EP | 3087204 B1 | 2/2018 |
| EP | 3288455 A1 | 3/2018 |
| EP | 3094747 B1 | 11/2018 |
| EP | 2893040 B1 | 1/2019 |
| EP | 3497220 A1 | 6/2019 |
| EP | 3207134 B1 | 7/2019 |
| EP | 3218523 B1 | 2/2020 |
| EP | 3289097 B1 | 3/2020 |
| WO | WO-0181620 A2 | 11/2001 |
| WO | WO-2003054219 A2 | 7/2003 |
| WO | WO-2005017207 A2 | 2/2005 |
| WO | WO-2005019477 A2 | 3/2005 |
| WO | WO-2005118852 A2 | 12/2005 |
| WO | WO-2006128192 A2 | 11/2006 |
| WO | WO-2007106802 A2 | 9/2007 |
| WO | WO-2008038000 A1 | 4/2008 |
| WO | WO-2008048508 A2 | 4/2008 |
| WO | WO-2008073303 A2 | 6/2008 |
| WO | WO-2008084219 A1 | 7/2008 |
| WO | WO-2010037001 A2 | 4/2010 |
| WO | WO-2010085343 A1 | 7/2010 |
| WO | WO-2011038507 A1 | 4/2011 |
| WO | WO-2011127136 A1 | 10/2011 |
| WO | WO-2012031329 A1 | 3/2012 |
| WO | WO-2012138973 A2 | 10/2012 |
| WO | WO-2012149171 A1 | 11/2012 |
| WO | WO-2012178074 A1 | 12/2012 |
| WO | WO-2013060762 A1 | 5/2013 |
| WO | WO-2013163207 A1 | 10/2013 |
| WO | WO-2013186639 A2 | 12/2013 |
| WO | WO-2014026768 A1 | 2/2014 |
| WO | WO-2014043763 A1 | 3/2014 |
| WO | WO-2014135469 A2 | 9/2014 |
| WO | WO-2014151117 A1 | 9/2014 |
| WO | WO-2014184684 A2 | 11/2014 |
| WO | WO-2014205981 A1 | 12/2014 |
| WO | WO-2015101515 A2 | 7/2015 |
| WO | WO-2015116837 A1 | 8/2015 |
| WO | WO-2015124955 A1 | 8/2015 |
| WO | WO-2015145133 A1 | 10/2015 |
| WO | WO-2015153284 A1 | 10/2015 |
| WO | WO-2015179672 A1 | 11/2015 |
| WO | WO-2016008451 A1 | 1/2016 |
| WO | WO-2016015058 A2 | 1/2016 |
| WO | WO-2016016639 A1 | 2/2016 |
| WO | WO-2016034908 A1 | 3/2016 |
| WO | WO-2016063034 A1 | 4/2016 |
| WO | WO-2016063059 A1 | 4/2016 |
| WO | WO-2016094813 A1 | 6/2016 |
| WO | WO-2016097251 A1 | 6/2016 |
| WO | WO-2016101258 A1 | 6/2016 |
| WO | WO-2016115530 A1 | 7/2016 |
| WO | WO-2016127844 A1 | 8/2016 |
| WO | WO-2016127944 A1 | 8/2016 |
| WO | WO-2016141324 A2 | 9/2016 |
| WO | WO-2016170319 A1 | 10/2016 |
| WO | WO-2016179049 A1 | 11/2016 |
| WO | WO-2016189288 A1 | 12/2016 |
| WO | WO-2016210224 A1 | 12/2016 |
| WO | WO-2017008912 A1 | 1/2017 |
| WO | WO-2017012544 A1 | 1/2017 |
| WO | WO-2017027835 A1 | 2/2017 |
| WO | WO-2017048932 A1 | 3/2017 |
| WO | WO-2017062970 A1 | 4/2017 |
| WO | WO-2017083562 A1 | 5/2017 |
| WO | WO-2017106481 A1 | 6/2017 |
| WO | 2017127741 A1 | 7/2017 |
| WO | WO-2017136603 A1 | 8/2017 |
| WO | WO-2017176630 A1 | 10/2017 |
| WO | WO-2017181079 A2 | 10/2017 |
| WO | WO-2017181111 A2 | 10/2017 |
| WO | WO-2017181134 A2 | 10/2017 |
| WO | WO-2017181146 A1 | 10/2017 |
| WO | WO-2017181202 A2 | 10/2017 |
| WO | WO-2017194668 A1 | 11/2017 |
| WO | WO-2017201102 A1 | 11/2017 |
| WO | WO-2017212428 A1 | 12/2017 |
| WO | WO-2018005983 A1 | 1/2018 |

(56) References Cited

FOREIGN PATENT DOCUMENTS

| | | |
|---|---|---|
| WO | WO-2018009696 A1 | 1/2018 |
| WO | WO-2018009702 A1 | 1/2018 |
| WO | WO-2018009703 A1 | 1/2018 |
| WO | WO-2018009705 A1 | 1/2018 |
| WO | WO-2018009709 A1 | 1/2018 |
| WO | WO-2018022890 A1 | 2/2018 |
| WO | WO-2018022906 A1 | 2/2018 |
| WO | WO-2018031760 A1 | 2/2018 |
| WO | WO-2018039463 A1 | 3/2018 |
| WO | WO-2018119216 A1 | 6/2018 |
| WO | WO-2018119452 A2 | 6/2018 |
| WO | WO-2018136881 A1 | 7/2018 |
| WO | WO-2018161031 A1 | 9/2018 |
| WO | WO-2018195211 A1 | 10/2018 |
| WO | WO-2018195217 A1 | 10/2018 |
| WO | WO-2018204764 A1 | 11/2018 |
| WO | 2019074700 A1 | 4/2019 |
| WO | WO-2019064063 A1 | 4/2019 |
| WO | WO-2019178277 A1 | 9/2019 |
| WO | WO-2019195268 A2 | 10/2019 |
| WO | WO-2019199696 A1 | 10/2019 |
| WO | WO-2020069350 A1 | 4/2020 |
| WO | WO-2020154682 A2 | 7/2020 |
| WO | 2020163403 A1 | 8/2020 |
| WO | 2020163410 A1 | 8/2020 |

OTHER PUBLICATIONS

Clinicaltrials.gov [retrieved on Jun. 1, 2021]. Retrieved from the Internet: <URL: www.clinicaltrials.gov/ct2/show/study/NCT02889978#armgroup>.*
A Guide to Reference Genome Selection, Oxford Genomics Centre, pp. 1-4, published Mar. 7, 2017 [retrieved on May 18, 2009]. Retrieved from the Internet: <URL: https://www.well.ox.ac.uk/ogc/guide-reference-genome-selection/. (Year: 2017).*
Liu et al, BMC Biotechnology, 8:91, pp. 1-10, published Dec. 4, 2008. (Year: 2008).*
Cheuk et al., Detection of Methylated Circulating DNA as Noninvasive Biomarkers for Breast Cancer Diagnosis. J. Breast Cancer 2017; 20(1): 12-17.
Laird. Early Detection: The power and the promise of DNA methylation markers. Nat Rev Cancer 3:253-266 (2003).
Warton et al., Methylation of cell-free circulating DNA in the diagnosis of cancer. Frontiers in Mol. Bio. 2015; vol. 2, Art. 13.
Avraham, A. et al. Tissue Specific DNA Methylation in Normal Human Breast Epithelium and in Breast Cancer. PLOS One, 9(3):e91805:1-8 (Mar. 20, 2014).
Burnham, et al. Single-stranded DNA library preparation uncovers the origin and diversity of ultrashort cell-free DNA in plasma. Sci Rep. Jun. 14, 2016;6:27859. doi: 10.1038/srep27859.
Chan, K.C. et al. Noninvasive detection of cancer-associated genome-wide hypomethylation and copy number aberrations by plasma DNA bisulfite sequencing. Proc. Natl. Acad. Sci. USA 110(47):18761-18768 (Nov. 19, 2013).
Chhibber et al. Single-molecule polymerase chain reaction reduces bias: Application to DNA methylation analysis by bisulfite sequencing. Anal. Biochem. vol. 377, Issue 1, Jun. 1, 2008, pp. 46-54.
Cohen, et al., Detection and localization of surgically resectable cancers with a multi-analyte blood test. Science Feb. 23, 2018:vol. 359, Issue 6378, pp. 926-930. DOI: 10.1126/science.aar3247.
Co-pending U.S. Appl. No. 17/061,013, inventors Gross; Samuel et al., filed Oct. 1, 2020.
Frimer et al. HPV16 methylation is a consistent biomarker of cervical intraepithelial neoplasia (CIN) 3 using a novel next-generation bisulfite-sequencing technology. Gynecologic Oncology. Jul. 2013, 130(1):e51-e52. Doi: https://doi.org/10.1016/j.ygyno.2013.04.182.
GenBank submission AC067721, Mar. 7, 2003 [online]. [Retrieved on Jun. 17, 2020].A Retrieved from the internet at< url: https://www.ncbi.nlm.nih.gov/nuccore/AC067721< /url:>.
GenBank submission AC093151.2, Jun. 25, 2002 [online]. [Retrieved on Jun. 17, 2020]. Retrieved from the internet at< url: https://www.ncbi.nlm.nih.gov/nuccore/AC093151</url:>.
Guo, S. et al. Identification of methylation haplotype blocks aids in deconvolution of heterogeneous tissue samples and tumor tissue-of-origin mapping from plasma DNA. Nat Genet 2017;49:635-42.
Hao et al. DNA methylation markers for diagnosis and prognosis of common cancers. PNAS USA 114(28):7414-7419 (w/Supplemental Information) (2017).
Huang et al., The Epigenome: Molecular Hide and Seek. Feb. 21, 2003, Chapter3, pp. 39-64. Doi: https://doi.org/10.1002/3527601511.ch3.
Husseiny, M. et al. Tissue-Specific Methylation of Human Insulin Gene and PCR Assay for Monitoring Beta Cell Death. PLoS One, 9(4):e9459:1-9 (Apr. 10, 2014).
Husseiny, M.I. et al. Development of a Quantitative Methylation-Specific Polymerase Chain Reaction Method for Monitoring Beta Cell Death in Type 1 Diabetes. PLoS One. Plos One 7(10): e47942 (Oct. 29, 2012).
Lebastchi, J. et al. Immune Therapy and B-Cell Death in Type 1 Diabetes. Diabetes, Brief Report 62(5):1676-1680 (May 2013).
Lehmann-Werman, R. et al. Identification of tissue-specific cell death using methylation patterns of circulating DNA. Proc Natl Acad Sci U S A 2016;113:E1826-34.
Liu et al. Targeted methylation sequencing of plasma cell-free DNA for cancer detection and classification. Annals of Oncology 29: 1445-1453, 2018.
Madi, T. et al. The determination of tissue-specific DNA methylation patterns in forensic biofluids using bisulfite modification and pyrosequencing. Electrophoresis,33(12):1736-1745 (Jul. 2012).
Miura et al., Highly sensitive targeted methylome sequencing by post-bisulfite adaptor tagging. DNA Research, vol. 22, Issue 1, Feb. 2015, pp. 13-18,https://doi.org/10.1093/dnares/dsu034.
PCT/US19/25358 International Search Report & Written Opinion dated Dec. 30, 2019.
Poon, Leo, L.M., et al., "Differential DNA Methylation between Fetus and Mother as a Strategy for Detecting Fetal DNA in Maternal Plasma," Clinical Chemistry, 2002, vol. 48, No. 1, pp. 35-41.
Raine, A. et al. Splinted Ligation Adapter Tagging (SPLAT), a novel library preparation method for whole genome bisulphite sequencing. Nucleic Acids Research, 110:1-15 (Nov. 28, 2016).
Shen et al., FACETS: allele-specific copy number and clonal heterogeneity analysis tool for high-throughput DNA sequencing. Nucleic Acids Research, 2016: 44(16) e131.
Shoemaker, et al., Allele-specific methylation is prevalent and is contributed by CpG-SNPs in the human genome. Genome Res. 2010.20:883-889.
Tanic, et al., Epigenome-wide association studies for cancer biomarker discovery in circulating cell-free DNA: technical advances and challenges. Current Opinion in Genetics & Development 2017, 42:48-55.
Varley, K.E. et al. Bisulfite Patch PCR enables multiplexed sequencing of promoter methylation across cancer samples. Genome Research 20:1279-1287 (2010).
Vrba et al., "A suite of DNA methylation markers that can detect most common human cancers", EPIGENETICS, 2018, pp. 1-13.
Yong, Ed. Written in Blood: DNA circulating in the bloodstream could guide cancer treatment—if researchers can work out how best to use it. Nature 2014: 511; 524-526.
AACRmeeting abstract in Apr. 2017, Liu et al., "Identify tissue-of-origin incancer cfDNA by whole genome sequencing" Abstract 5689/13.
Ashford, Molika. UCSD Methylation Haplotype Method Tracks cfDNA Origin; Singlera to Commercialize. Genome Web. Published Mar. 8, 2017. Accessed Dec. 7, 2020. Available at: https://www.genomeweb.com/molecular-diagnostics/ucsd-methylation-haplotype-method-tracks-cfdna-origin-singlera-commercialize#.X9P0pmiQGUk.
Diep et al. Library-free methylation sequencing with bisulfite padlock probes. Nature Methods 9(3):270-272 (2012).
EZ DNA Methylation-Lightning Kit, Instruction Manual. Zymo Research, ver. 1.0.5.

(56) References Cited

OTHER PUBLICATIONS

Kang et al., "CancerLocator: non-invasive cancer diagnosis and tissue-of-origin prediction using methylation profiles of cell-free DNA," Genome Biology vol. 18, Article No. 53 (2017).

Li et al. CancerDetector: ultrasensitive and non-invasive cancer detection at the resolution of individual reads using cell-free DNA methylation sequencing data. Nucleic Acids Research, vol. 46, Issue 15, Sep. 6, 2018, p. e89, https://doi.org/10.1093/nar/gky423.

Liu et al. Methylation-sensitive enrichment of minor DNA alleles using a double-strand DNA-specific nuclease. Nucleic Acids Research, 2017 vol. 45(6): e39.

Mouliere et al. Selecting short DNA fragments in plasma improves detection of circulating tumour DNA. May 2017. bioRxiv 134437; doi: https://doi.org/10.1101/134437.

Oncomine™ cfDNA Assays Part I: Library Preparation User Guide (2016).

Oncomine™ cfDNA Assays part II: Plan a Run, Template Preparation, and Sequencing User Guide (2016).

Ross, JP et al. Identification of differentially methylated regions usign streptavidin bisulfite ligand methylation enrichment (SuBLiME), a new method to enrich for methylated DNA prior to deep bisulfite genomic sequencing. Epigenetics, 8(1):113-127 (Jan. 2013) E-pub: Dec. 20, 2012.

Toyota et al. Identification of differentially methylated sequences in colorectal cancer by methylated CpG island amplification. Cancer Research. May 1999. 59(10).

Widschwendter, et al. Methylation patterns in serum DNA for early identification of disseminated breast cancer. Genome Medicine vol. 9, Article No. 115 (2017).

U.S. Appl. No. 17/061,013 Office Action dated Feb. 23, 2021.

Co-pending U.S. Appl. No. 17/214,038, inventors Gross; Samuel S. et al., filed Mar. 26, 2021.

Co-pending U.S. Appl. No. 17/214,105, inventors Gross; Samuel et al., filed Mar. 26, 2021.

Co-pending U.S. Appl. No. 17/214,190, inventors Gross; Samuel S. et al., filed Mar. 26, 2021.

Co-pending U.S. Appl. No. 17/214,682, inventors Xiang; Jing et al., filed Mar. 26, 2021.

PCT/US2019/053509 International Search Report dated Jan. 29, 2020.

Bejar, R., et al., Clinical Effect of Point Mutations in Myelodysplastic Syndromes, The New England Journal of Medicine, Jun. 2011, pp. 2496-2506.

Brandon, et al., "Mitochondrial mutations in cancer", Oncogene 25(34), 2006, 4647-4662.

Genome Reference Consortium with a reference No. GRCh37/hg19, and also available from Genome Browser provided by Santa Cruz Genomics Institute, Nucleic Acids REsearch, 2021, vol. 49, Nov. 22, 2020.

Harris, et al., "Single-Molecule DNA Sequencing of a Viral Genome", Science, vol. 320, 2008, 106-109.

Hashimoto, et al., "5'-end SAGE for the analysis of transcriptional start sites", Nature Biotechnology, 22, 2004, 1146-1149.

Illumina, Data Sheet; Epigenetics "Infinfium HumanMethylation450 BeadChip", 4 pgs., 2012.

International Classification of Diseases for Oncology (ICD-O-3) (codes.iarc.fr).

Kivioja, et al., "Counting absolute numbers of molecules using unique molecular identifiers", Nat Methods, 9(1), 2011, 72-4.

Li, et al., "Post-conversion targeted capture of modified cytosines in mammalian and plant genomes", NAR 43(12), e81, 16 pages, 2015.

Mardis, E. R., et al., Recurring Mutations Found by Sequencing an Acute Myeloid Leukemia Genome, The New England Journal of Medicine, 2009, pp. 1058-1066.

Masser, et al., "Bisulfite oligonucleotide-capture sequencing for targeted baseand strand-specific absolute 5-methylcytosine quantitation" AGE 38:49; 14 pages 2016.

Okamura, et al., Lists of HumanMethylation450 BeadChip probes with nucleotide-variant information obtained from the Phase 3 data of the 1000 Genomes Project, Genomics Data 7, 67-69, 2016.

Papaemmanuil, E., et al., Somatic SF3B1 Mutation in Myelodysplasia with Ring Sideroblasts, The New England Journal of Medicine, Sep. 26, 2011, pp. 1384-1395.

Reidmiller M, Braun H. RPROP—A Fast Adaptive Learning Algorithm. Proceedings of the International Symposium on Computer and Information Science VII, 1992).

Surveillance, Epidemiology, and End Results Program (SEER) (seer.cancer.gov).

The Circulating Cell-free Genome Atlas Study ("CCGA"; Clinical Trial.gov identifier NCT02889978).

The STRIVE Study: Development of a Blood Test for Early Detection of Multiple Cancer Types, CinicalTrials.gov Identifier: NCT03085888, 6 pages, 2017.

Walter, M., Clonal Architecture of Secondary Acute Myeloid Leukemia, The New England Journal of Medicine, , Mar. 14, 2012, pp. 1090-1098.

Zhai, et al., "Genome-wide DNA Methylation Profiling of Cell-Free Serum DNA in Esophageal Adenocarcinoma and Barrett Esophagus" Neoplasia, 14(1), 29-33, 2012.

Leygo, et al., "DNA Methylation as a Noninvasive Epigenetic Biomarker for the Detection of Cancer" Dis Markers.; 2017: 3726595.

\* cited by examiner

Generate data structure for a control group
300

```
Generate set of methylation state vectors
for a control group
100
```
↓
```
For each methylation state vector, subdivide
into strings of methylation sites
310
```
↓
```
Tally strings for each position and methylation
state combination
320
```
↓
```
Create data structure storing counts of all
possible strings from the control group
330
```
⇣
```
Validate data structure consistency
340
```

*FIG. 3A*

Validate data structure consistency
*340*

```
Generate set of methylation state vectors
for a validation group
100
          ↓
Calculate a p-value score for each
methylation state vector with control group
data structure
350
          ↓
Build cumulative density function (CDF) of all
p-values from the validation group
360
          ↓
Validate consistency of CDF
370
```

*FIG. 3B*

Calculate P-Value with Markov Chain Model
500

Test Methylation State Vector
505

$< M_{23}, M_{24}, M_{25}, U_{26} >$

↓ 410
↓ 420

| P | $< M_{23}, M_{24}, M_{25}, M_{26} >$ | $= P(M_{26} \mid M_{23}, M_{24}, M_{25}) * P(M_{25} \mid M_{23}, M_{24}) * P(M_{24} \mid M_{23}) * P(M_{23})$ |
| P | $< M_{23}, M_{24}, M_{25}, U_{26} >$ | $\approx P(M_{26} \mid M_{24}, M_{25}) * P(M_{25} \mid M_{23}, M_{24}) * P(M_{24} \mid M_{23}) * P(M_{23})$ |
| ⋯ | | |
| P | $< U_{23}, U_{24}, U_{25}, U_{26} >$ | $= P(U_{26} \mid U_{23}, U_{24}, U_{25}) * P(U_{25} \mid U_{23}, U_{24}) * P(U_{24} \mid U_{23}) * P(U_{23})$ |
| | | $\approx P(U_{26} \mid U_{24}, U_{25}) * P(U_{25} \mid U_{23}, U_{24}) * P(U_{24} \mid U_{23}) * P(U_{23})$ |

Probabilities of Possible Methylation State Vectors
515

↓ 430

| p-value | $< M_{23}, M_{24}, M_{25}, U_{26} >$ | $= \sum [\text{All probabilities} \leq P(<M_{23}, M_{24}, M_{25}, U_{26}>)]$ |

P-Value of Test Methylation State Vector
525

FIG. 5

Computing pairwise information gain
_680_

For each sample, define a feature vector for each cancer type at each region based on count of fragments above a log-likelihood ratio above various thresholds
_690_

↓

Calculate an informative score for each CpG site describing ability to distinguish between pairs of cancer type
_695_

*FIG. 6B*

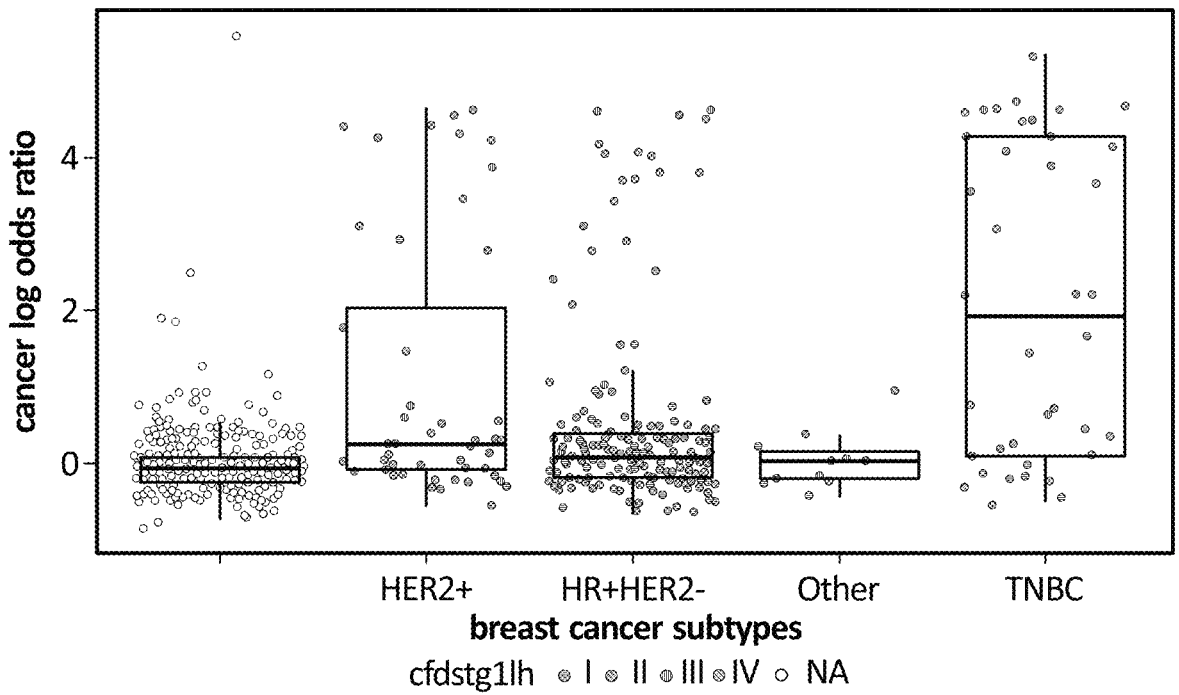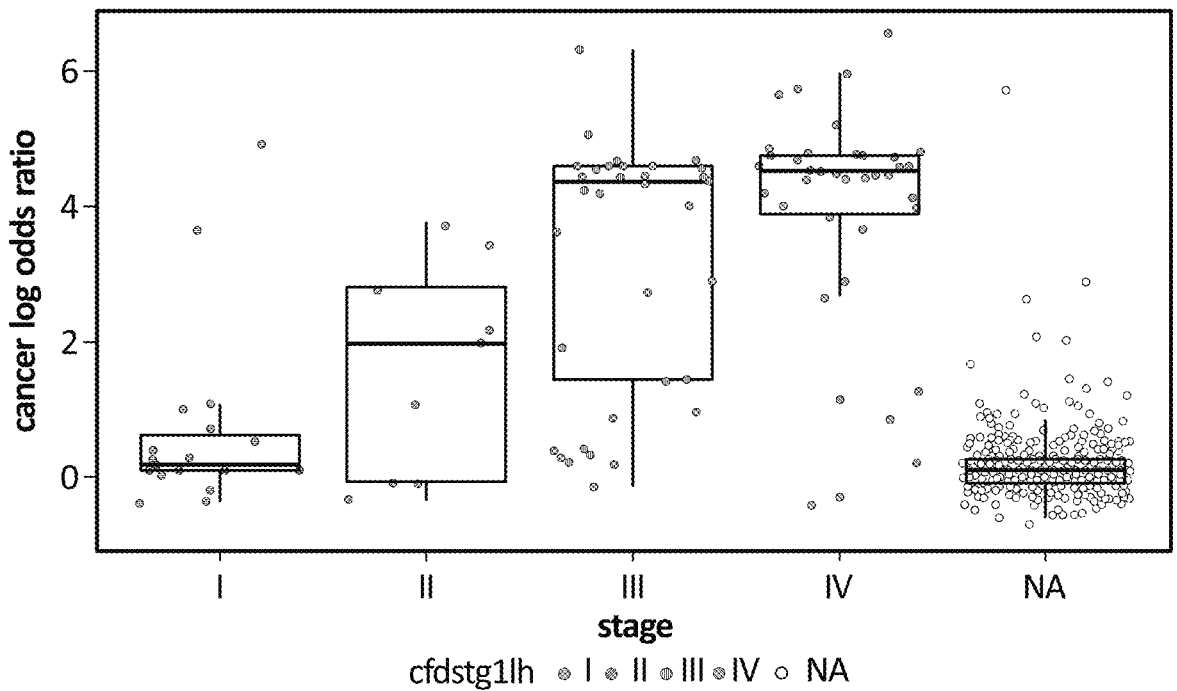
FIG. 11B

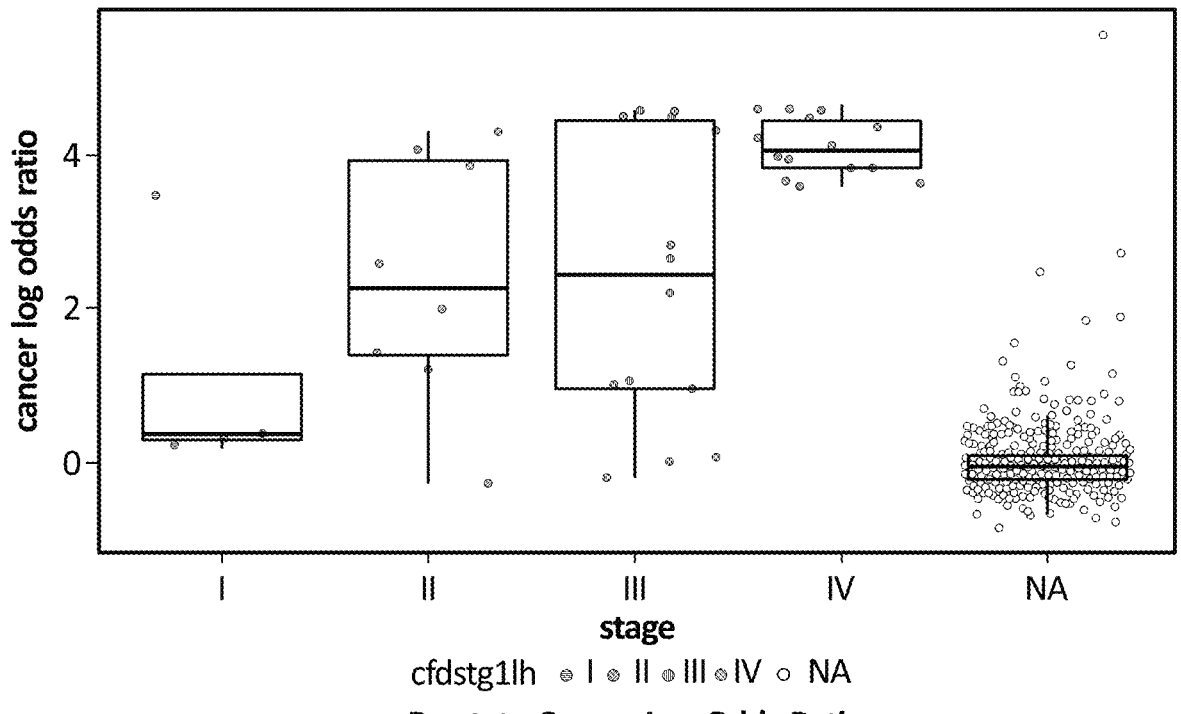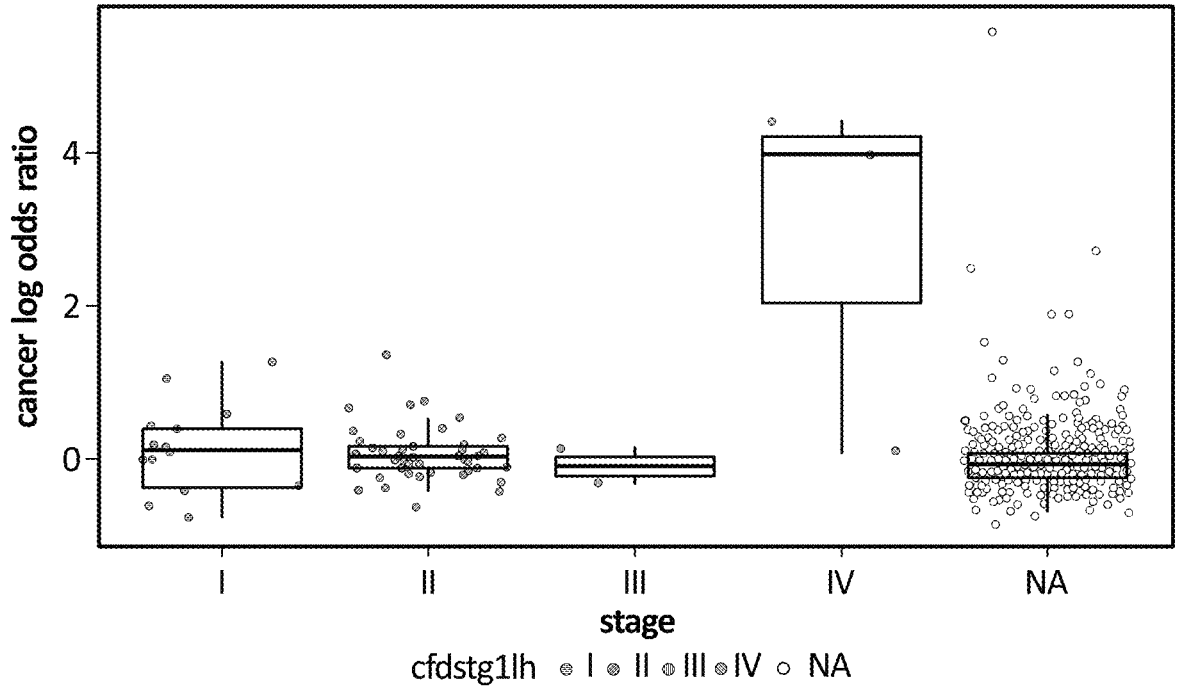
FIG. 11C

| metric | Sn_95Sp |
| --- | --- |
| Mscore.testV1 | 0.3606 |
| Mscore.testV1.cv | 0.3526 |
| Mscore.testV1.cv.panel | 0.3566 |

METHYLATION MARKERS AND TARGETED METHYLATION PROBE PANEL

CROSS REFERENCE TO RELATED APPLICATIONS

This is a continuation application, which claims priority to International Patent Application No. PCT/US2019/025358, filed Apr. 2, 2019, which claims the benefit of U.S. Provisional Patent Application No. 62/651,643, filed Apr. 2, 2018 and U.S. Provisional Patent Application No. 62/738,271, filed Sep. 28, 2018, both of which are hereby incorporated by reference in their entireties.

TABLES SUBMITTED ELECTRONICALLY

The instant application contains Tables which have been submitted electronically in ASCII format and are hereby incorporated by reference in its entirety. Said ASCII copy, created on Dec. 4, 2023, is named 202323-612302 US_T-ables_11-24.txt and is 7,885,160 bytes in size.

BACKGROUND

DNA methylation plays an important role in regulating gene expression. Aberrant DNA methylation has been implicated in many disease processes, including cancer. DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions may be useful as molecular markers for various diseases.

However, WGBS is not ideally suitable for a product assay. The reason is that the vast majority of the genome is either not differentially methylated in cancer, or the local CpG density is too low to provide a robust signal. Only a few percent of the genome is likely to be useful in classification.

Furthermore, there have been various challenges in identifying differentially methylated regions in various diseases. First off, determining differentially methylated regions in a disease group only holds weight in comparison with a group of control subjects, such that if the control group is small in number, the determination loses confidence with the small control group. Additionally, among a group of control subjects, methylation status can vary which can be difficult to account for when determining whether the regions are differentially methylated in a disease group. On another note, methylation of a cytosine at a CpG site is strongly correlated with methylation at a subsequent CpG site. To encapsulate this dependency is a challenge in itself.

Accordingly, a cost-effective method of accurately diagnosing a disease by detecting differentially methylated regions has not yet been available.

SUMMARY

Early detection of cancer in subjects is important as it allows for earlier treatment and therefore a greater chance for survival. Targeted detection of methylation patterns specific to cancer or tissue of origin, i.e., the organ, organ group, body region or cell type that the cancer arises or origins from, using cell-free DNA (cfDNA) fragments can make early detection of cancer possible by providing a cost-effective and non-invasive method for analyzing information relevant to cancer classification. By using a targeted genomic region panel rather than sequencing all nucleic acids in a test sample, also known as "whole genome sequencing," the method can increase sequencing depth of the target regions and lower costs compared to whole genome sequencing (WGS) or whole genome bisulfite sequencing (WGBS).

Towards that end, the present description provides cancer assay panels (e.g., bait sets) for detecting cancer and various tissue or origins by detecting methylation patterns of targeted genomic regions. The cancer assay panel can detect and differentiate methylation patterns specific to cancer in general or to different cancer types, such as, e.g., (1) blood cancer, (2) breast cancer, (3) colorectal cancer, (4) esophageal cancer, (5) head and neck cancer, (6) hepatobiliary cancer, (7) lung cancer, (8) ovarian cancer, and (9) pancreatic cancer.

Cancer assay panels can further provide information relevant to a cancer stage for each cancer type. The present description also provides a method of using cancer assay panels for diagnosis of cancer, wherein the diagnosis of cancer further includes a cancer type and/or cancer stage. Further provided herein are methods of identifying genomic sites having methylation patterns specific to cancer or various types of cancer as well as a list of genomic sites that can be used for the diagnosis of cancer and/or cancer tissue of origin. The methods described herein further include methods of designing probes to enrich for nucleic acids derived from the selected genomic regions efficiently without pulling down an excessive amount of undesired or non-targeted nucleic acid and methods of making the cancer assay panel with the probes. Also described are methods for enriching nucleic acids derived from the selected genomic regions by means other than hybridization capture.

Disclosed herein are assay panels for enriching cfDNA molecules for cancer diagnosis, the assay panel comprising at least 500 different pairs of polynucleotide probes, wherein each pair of the at least 500 pairs of probes (i) comprises two different probes configured to overlap with each other by an overlapping sequence of 30 or more nucleotides and (ii) is configured to hybridize to a modified fragment obtained from processing of the cfDNA molecules, wherein each of the cfDNA molecules corresponds to or is derived from one or more genomic regions and wherein each of the one or more genomic regions comprises at least five methylation sites and has an anomalous methylation pattern in cancerous training samples.

In some embodiments, the overlapping sequence comprises at least 40, 50, 75, or 100 nucleotides. In some embodiments, the assay panels comprise at least 50, 60, 70, 80, 90, 100, 120, 150, 200, 300 or 400 pairs of probes. In some embodiments, the assay panels comprise at least 1,000, 2,000, 2,500, 5,000, 6,000, 7,500, 10,000, 15,000, 20,000 or 25,000 pairs of probes.

Further disclosed herein are assay panels for enriching cfDNA molecules for cancer diagnosis, comprising at least 1,000 polynucleotide probes, wherein each of the at least 1,000 probes is configured to hybridize to a modified polynucleotide obtained from processing of the cfDNA molecules, wherein each of the cfDNA molecules corresponds to or is derived from, one or more genomic regions and wherein each of the one or more genomic regions comprises at least five methylation sites, and has an anomalous methylation pattern in cancerous training samples.

In some embodiments, the processing of the cfDNA molecules comprises converting unmethylated C (cytosine) to U (uracil) in the cfDNA molecules. In some embodiments, each of the polynucleotide probes in the panel is conjugated to an affinity moiety. In some embodiments, the affinity moiety is a biotin moiety. In some embodiments, the training samples are samples originating from a plurality of subjects determined to have cancer. The assay panel of any one of the above claims, wherein a genomic region has an anomalous methylation pattern in cancerous training samples when a methylation state vector representing the genomic region in the cancerous training samples is present less frequently in reference samples than a threshold value. In some embodiments, the threshold value is 0.1, 0.01, 0.001, or 0.0001. In some embodiments, each of the one or more genomic regions is either hypermethylated or hypomethylated in the cancerous training samples.

In some embodiments, at least 80, 85, 90, 92, 95, or 98% of the at least five methylation sites are either methylated or unmethylated in the cancerous training samples. In some embodiments, at least 3%, 5%, 10%, 15%, or 20%, 30%, or 40% of the probes on the panel comprise no G (Guanine). In some embodiments, at least 80, 85, 90, 92, 95, 98% of the probes on the panel have exclusively either CpG or CpA on CpG detection sites. In some embodiments, each of the probes on the panel comprises less than 20, 15, 10, 8, or 6 CpG detection sites. In some embodiments, each of the entire probes on the panel is designed to have sequence homology or sequence complementarity with fewer than 20, 15, 10, or 8 off-target genomic regions. In some embodiments, the fewer than 20 off-target genomic regions are identified using a k-mer seeding strategy. In some embodiments, the fewer than 20 off-target genomic regions are identified using k-mer seeding strategy combined to local alignment at seed locations.

In some embodiments, the assay panels comprise at least 1,000, 2,000, 2,500, 5,000, 10,000, 12,000, 15,000, 20,000, or 25,000 probes. In some embodiments, the at least 1,000 probes, or the at least 500 pairs of probes, together comprise at least 0.2 million, 0.4 million, 0.6 million, 0.8 million, 1 million, 2 million, or 4 million nucleotides. In some embodiments, each of the probes on the panel comprises at least 50, 75, 100, or 120 nucleotides. In some embodiments, each of the probes on the panel comprises less than 300, 250, 200, or 150 nucleotides. In some embodiments, each of the probes on the panel comprises 100-150 nucleotides. In some embodiments, at least 30% of the genomic regions are in exons or introns. In some embodiments, at least 15% of the genomic regions are in exons. In some embodiments, at least 20% of the genomic regions are in exons. In some embodiments, less than 10% of the genomic regions are in intergenic regions.

In some embodiments, the cancer panels further comprise a plurality of virus-specific probes, wherein each of the virus-specific probes is configured to hybridize to a viral genome fragment from cfDNA. In some embodiments, the viral genome fragment is from MCV, EBV, HBV, HCMV, HCV, HEWS, HPV16, or HPV18. In some embodiments, the cancer panels comprise at least 50, 100, 200, 500, 1000, 2000, or 3000 virus-specific probes.

In some embodiments, each of the one or more genomic regions is selected from one of Tables 1 or 11-15 (or combinations thereof). In some embodiments, each of the one or more genomic regions are selected from Table 13. In some embodiments, each of the one or more genomic regions are selected from Table 14. In some embodiments, each of the one or more genomic regions are selected from Table 15.

In some embodiments, the entire probes on the panel together are configured to hybridize to modified fragments obtained from the cfDNA molecules corresponding to or derived from at least 30%, 40%, 50%, 60%, 70%, 80%, 90% or 95% of the genomic regions in one or more of Tables 1 and 11-15.

In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one of the genomic regions of Table 13. In some embodiments, an entirety of entire probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 14.

In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 15.

In some embodiments, an entirety of probes on the panel together are configured to hybridize to modified fragments obtained from the cfDNA molecules corresponding to or derived from at least 500, 1,000, 5000, 10,000 or 15,000 genomic regions in in one or more of Tables 1 and 11-15. In some embodiments, an entirety of probes on the panel together are configured to hybridize to modified fragments obtained from the cfDNA molecules corresponding to or derived from at least 500, 1,000, 5000, 10,000 or 15,000 genomic regions in Table 13. In some embodiments, an entirety of probes on the panel together are configured to hybridize to modified fragments obtained from the cfDNA molecules corresponding to or derived from at least 500, 1,000, 5000, 10,000 or 15,000 genomic regions in Table 14. In some embodiments, an entirety of probes on the panel together are configured to hybridize to modified fragments obtained from the cfDNA molecules corresponding to or derived from at least 500, 1,000, 5000, 10,000 or 15,000 genomic regions in Table 15.

Further disclosed herein are assay panels for enriching cfDNA molecules for cancer diagnosis, comprising a plurality of polynucleotide probes, wherein each of the polynucleotide probes is configured to hybridize to a modified fragment obtained from processing of the cfDNA molecules, wherein each of the cfDNA molecules corresponds to or is derived from one or more genomic regions selected from any one of Tables 1-24.

In some embodiments, each of the cfDNA molecules corresponds to or is derived from one or more genomic regions selected from any one of Tables 2-10 or 16-24 (or a combination thereof). In some embodiments, each of the cfDNA molecules corresponds to or is derived from one or more genomic regions selected from any one of Tables 13, 14, or 15. In some embodiments, each of the cfDNA molecules corresponds to or is derived from one or more genomic regions selected from Table 13. In some embodiments, each of the cfDNA molecules corresponds to or is derived from one or more genomic regions selected from Table 14. In some embodiments, each of the cfDNA molecules corresponds to or is derived from one or more genomic regions selected from Table 15.

In some embodiments, an entirety of probes on the panel together are configured to hybridize to modified fragments obtained from the cfDNA molecules corresponding to or is derived from at least 30%, 40%, 50%, 60%, 70%, 80%, 90% or 95% of the genomic regions in any one of Tables 1-24. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in any one of Tables 2-10 or 16-24 (or combinations thereof). In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 13. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 14. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 15.

In some embodiments, an entirety of probes on the panel are configured to hybridize to modified fragments obtained from the cfDNA molecules corresponding to or derived from at least 50, 60, 70, 80, 90, 100, 120, 150, 200, 500, 1,000, 5000, 10,000 or 15,000 genomic regions in any one of Tables 1-24. In some embodiments, the entire probes on the panel are configured to hybridize to modified fragments obtained from the cfDNA molecules corresponding to or derived from at least 50, 60, 70, 80, 90, 100, 120, 150, or 200 genomic regions from any one of Tables 2-10 or 16-24.

In some embodiments, an entirety of probes on the panel are configured to hybridize to modified fragments obtained from the cfDNA molecules corresponding to or derived from at least 500, 1,000, 5000, 10,000 or 15,000 genomic regions in Table 13. In some embodiments, an entirety of probes on the panel are configured to hybridize to modified fragments obtained from the cfDNA molecules corresponding to or derived from at least 500, 1,000, 5000, 10,000 or 15,000 genomic regions in Table 14. In some embodiments, an entirety of probes on the panel are configured to hybridize to modified fragments obtained from the cfDNA molecules corresponding to or derived from at least 500, 1,000, 5000, 10,000 or 15,000 genomic regions in Table 15.

In some embodiments, the processing of the cfDNA molecules comprises converting unmethylated C (cytosine) to U (uracil) in the cfDNA molecules. In some embodiments, each of probes on the panel is conjugated to an affinity moiety, wherein the affinity moiety is not a nucleic acid affinity moiety. In some embodiments, the affinity moiety is a biotin moiety. In some embodiments, at least 3%, 5%, 10%, 15%, 20%, 30%, or 40% of the probes on the panel comprise no G (Guanine). In some embodiments, at least 80%, 85%, 90%, 92%, 95%, or 98% of the probes on the panel have exclusively either CpG or CpA on CpG detection sites.

Further disclosed herein are methods for providing sequence information informative of a presence or absence of cancer, comprising the steps of obtaining a test sample comprising a plurality of cfDNA test molecules; processing the cfDNA test molecules, thereby obtaining bisulfate-converted test fragments; contacting the bisulfate-converted test fragments with an assay panel, thereby enriching a subset of the bisulfate-converted test fragments by hybridization capture; and sequencing the subset of the bisulfate-converted test fragments, thereby obtaining a set of sequence reads. In some embodiments, the assay panel is selected from any of the panels described above.

In some embodiments, some methods further comprise the later step of: determining a cancer classification by evaluating the set of sequence reads, wherein the cancer classification is a presence or absence of cancer; a stage of cancer; a presence or absence of a type of cancer; or a presence or absence of at least 1, 2, 3, 4, or 5 different types of cancer.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from one of Tables 1, 12, 13, 14, and 15, wherein the cancer classification is a presence or absence of cancer or a stage of cancer. In some embodiments, the polynucleotide probes together are configured to hybridize to bisulfite-converted fragments obtained from the cfDNA molecules corresponding to or derived from at least 30%, 40%, 50%, 60%, 70%, 80%, 90% or 95% of the genomic regions in one of Tables 1, 12, 13, 14, and 15.

In some embodiments, wherein the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 2, wherein the cancer classification is a presence or absence of blood cancer or a stage of blood cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 2.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 3, wherein the cancer classification is a presence or absence of breast cancer or a stage of breast cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 3.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 4, wherein the cancer classification is a presence or absence of colorectal cancer or a stage of colorectal cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 4.

In some embodiments, the assay panel comprises a plurality of polynucleotide probes, wherein each of the polynucleotide probes is configured to hybridize to a bisulfite-converted fragment obtained from processing of cfDNA molecules, wherein each of the cfDNA molecules corresponds to or is derived from one or more genomic regions selected from Table 5, wherein the cancer classification is a presence or absence of esophageal cancer or a stage of esophageal cancer. In some embodiments, the polynucleotide probes together are configured to hybridize to bisulfite-converted fragments obtained from the cfDNA molecules corresponding to or derived from at least 30%, 40%, 50%, 60%, 70%, 80%, 90% or 95% of the genomic regions in Table 5.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 6, wherein the cancer classification is a presence or absence of head and neck cancer or a stage of head and neck cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 6.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 7, wherein the cancer classification is a presence or absence of hepatobiliary cancer or a stage of hepatobiliary cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 7.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 8, wherein the cancer classification is a presence or absence of lung cancer or a stage of lung cancer. In some embodiments, the polynucleotide probes together are configured to hybridize to bisulfite-converted fragments obtained from the cfDNA molecules corresponding to or derived from at least 30%, 40%, 50%, 60%, 70%, 80%, 90% or 95% of the genomic regions in Table 8.

In some embodiments, the assay panel comprises a plurality of polynucleotide probes, wherein each of the polynucleotide probes is configured to hybridize to a bisulfite-converted fragment obtained from processing of cfDNA molecules, wherein each of the cfDNA molecules corresponds to or is derived from one or more genomic regions selected from Table 9, wherein the cancer classification is a presence or absence of ovarian cancer or a stage of ovarian cancer. In some embodiments, the polynucleotide probes together are configured to hybridize to bisulfite-converted fragments obtained from the cfDNA molecules corresponding to or derived from at least 30%, 40%, 50%, 60%, 70%, 80%, 90% or 95% of the genomic regions in Table 9.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 10, wherein the cancer classification is a presence or absence of pancreatic cancer or a stage of pancreatic cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 10.

In some embodiments, wherein the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 16, wherein the cancer classification is a presence or absence of blood cancer or a stage of blood cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 16.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 17, wherein the cancer classification is a presence or absence of breast cancer or a stage of breast cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 17.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 18, wherein the cancer classification is a presence or absence of colorectal cancer or a stage of colorectal cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 18.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 19, wherein the cancer classification is a presence or absence of esophageal cancer or a stage of esophageal cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 19.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 20, wherein the cancer classification is a presence or absence of head and neck cancer or a stage of head and neck cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 20.

In some embodiments, the assay panel comprises a plurality of polynucleotide probes, wherein each of the polynucleotide probes is configured to hybridize to a bisulfite-converted fragment obtained from processing of cfDNA molecules, wherein each of the cfDNA molecules corresponds to or is derived from one or more genomic regions selected from Table 21, wherein the cancer classification is a presence or absence of hepatobiliary cancer or a stage of hepatobiliary cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 21.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 22, wherein the cancer classification is a presence or absence of lung cancer or a stage of lung cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 22.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 23, wherein the cancer classification is a presence or absence of ovarian cancer or a stage of ovarian cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 23.

In some embodiments, the assay panel comprises a plurality of polynucleotide probes, wherein each of the polynucleotide probes is configured to hybridize to a bisulfate-converted fragment obtained from processing of cfDNA molecules, wherein each of the cfDNA molecules corresponds to or is derived from one or more genomic regions selected from Table 24, wherein the cancer classification is a presence or absence of pancreatic cancer or a stage of pancreatic cancer. In some embodiments, the polynucleotide probes together are configured to hybridize to bisulfate-converted fragments obtained from the cfDNA molecules corresponding to or derived from at least 30%, 40%, 50%, 60%, 70%, 80%, 90% or 95% of the genomic regions in Table 24.

In some embodiments, the step of determining a cancer classification is performed by the method comprising generating a test feature vector based on the set of sequence reads; and applying the test feature vector to a model obtained by a training process with a cancer set of fragments from one or more training subjects with cancer and a non-cancer set of fragments from one or more training subjects without cancer, wherein both cancer set of fragments and the non-cancer set of fragments comprise a plurality of training fragments.

In some embodiments, the training process comprises obtaining sequence information of training fragments from a plurality of training subjects; for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each training subject, generating a training feature vector based on the hypomethylated training fragments and a training feature vector based on the hypermethylated training fragments, and training the model with the training feature vectors from the one or more training subjects without cancer and the training feature vectors from the one or more training subjects with cancer.

In some embodiments, the training process comprises obtaining sequence information of training fragments from a plurality of training subjects; for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each training subject, generating a training feature vector based on the hypomethylated training fragments and a training feature vector based on the hypermethylated training fragments, and training the model with the training feature vectors from the one or more training subjects without cancer and the training feature vectors from the one or more training subjects with cancer.

In some embodiments, the training process comprises obtaining sequence information of training fragments from a plurality of training subjects; for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; for each training fragment, generating an aggregate hypomethylation score based on the hypomethylation score of the CpG sites in the training fragment and an aggregate hypermethylation score based on the hypermethylation score of the CpG sites in the training fragment; for each training subject: ranking the plurality of training fragments based on aggregate hypomethylation score and ranking the plurality of training fragments based on aggregate hypermethylation score; and generating a feature vector based on the ranking of the training fragments; obtaining training feature vectors for one or more training subjects without cancer and training feature vectors for the one or more training subjects with cancer; and training the model with the feature vectors for the one or more training subjects without cancer and the feature vectors for the one or more training subjects with cancer. In some embodiments, the model comprises one of a kernel logistic regression classifier, a random forest classifier, a mixture model, a convolutional neural network, and an autoencoder model.

In some embodiments, the methods further comprises obtaining a cancer probability for the test sample based on the model; and comparing the cancer probability to a threshold probability to determine whether the test sample is from a subject with cancer or without cancer. In some embodiments, the methods further comprising administering an anti-cancer agent to the subject. In some embodiments, the methods comprise administering an anti-cancer agent to a subject who has been identified as a cancer subject by the methods disclosed herein. In some embodiments, the anti-cancer agent is a chemotherapeutic agent selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, and platinum-based agents.

Further disclosed herein are methods comprising obtaining a set of sequence reads of modified test fragments, wherein the modified test fragments are or have been obtained by processing a set of nucleic acid fragments from a test subject, wherein each of the nucleic acid fragments corresponds to or is derived from a plurality of genomic regions selected from one of Tables 1-24; and applying the set of sequence reads or a test feature vector obtained based on the set of sequence reads to a model obtained by a training process with a cancer set of fragments from one or more training subjects with cancer and a non-cancer set of fragments from one or more training subjects without cancer, wherein both cancer set of fragments and the non-cancer set of fragments comprise a plurality of training fragments.

In some embodiments, the methods further comprise the step of obtaining the test feature vector comprising: for each of the nucleic acid fragments, determining whether the nucleic acid fragment is hypomethylated or hypermethylated, wherein each of the hypomethylated and hypermethylated nucleic acid fragments comprises at least a threshold number of CpG sites with at least a threshold percentage of the CpG sites being unmethylated or methylated, respectively; for each of a plurality of CpG sites in a reference genome: quantifying a count of hypomethylated nucleic acid fragments which overlap the CpG site and a count of hypermethylated nucleic acid fragments which overlap the CpG site; and generating a hypomethylation score and a hypermethylation score based on the count of hypomethylated nucleic acid fragments and hypermethylated nucleic acid fragments; for each nucleic acid fragment, generating an aggregate hypomethylation score based on the hypomethylation score of the CpG sites in the nucleic acid fragment and an aggregate hypermethylation score based on the hypermethylation score of the CpG sites in the nucleic acid fragment; ranking the plurality of nucleic acid fragments based on aggregate hypomethylation score and ranking the plurality of nucleic fragments based on aggregate hypermethylation score; and generating the test feature vector based on the ranking of the nucleic acid fragments.

In some embodiments, the training process comprises: for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each training subject, generating a training feature vector based on the hypomethylated training fragments and a training feature vector based on the hypermethylated training fragments, and training the model with the training feature vectors from the one or more training subjects without cancer and the feature vectors from the one or more training subjects with cancer.

In some embodiments, the training process comprises: for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; for each training fragment, generating an aggregate hypomethylation score based on the hypomethylation score of the CpG sites in the training fragment and an aggregate hypermethylation score based on the hypermethylation score of the CpG sites in the training fragment; for each training subject: ranking the plurality of training fragments based on aggregate hypomethylation score and ranking the plurality of training fragments based on aggregate hypermethylation score; and generating a feature vector based on the ranking of the training fragments; obtaining training feature vectors for one or more training subjects without cancer and training feature vectors for the one or more training subjects with cancer; and training the model with the feature vectors for the one or more training subjects without cancer and the feature vectors for the one or more training subjects with cancer.

In some embodiments, for each CpG site in a reference genome, the methods comprise quantifying a count of hypomethylated training fragments which overlap that CpG site and a count of hypermethylated training fragments which overlap that CpG site further comprises: quantifying a cancer count of hypomethylated training fragments from the one or more training subjects with cancer that overlap that CpG site and a non-cancer count of hypomethylated training fragments from the one or more training subjects without cancer that overlap that CpG site; and quantifying a cancer count of hypermethylated training fragments from the one or more training subjects with cancer that overlap that CpG site and a non-cancer count of hypermethylated training fragments from the one or more training subjects without cancer that overlap that CpG site.

In some embodiments, for each CpG site in a reference genome, the methods comprise generating a hypomethylation score and a hypermethylation score based on the count of hypomethylated training fragments and hypermethylated training fragments further comprises: for generating the hypomethylation score, calculating a hypomethylation ratio of the cancer count of hypomethylated training fragments over a hypomethylation sum of the cancer count of hypomethylated training fragments and the non-cancer count of hypomethylated training fragments; and for generating the hypermethylation score, calculating a hypermethylation ratio of the cancer count of hypermethylated training fragments over a hypermethylation sum of the cancer count of hypermethylated training fragments and the non-cancer count of hypermethylated training fragments.

In some embodiments, the model comprises one of a kernel logistic regression classifier, a random forest classifier, a mixture model, a convolutional neural network, and an autoencoder model. In some embodiments, the set of sequence reads is obtained by using the assay panel of any one of the described panels above.

Further disclosed herein are methods for designing an assay panel for cancer diagnosis, comprising the steps of: identifying a plurality of genomic regions, wherein each of the plurality of genomic regions (i) comprises at least 30 nucleotides, and (ii) comprises at least five methylation sites, selecting a subset of the genomic regions, wherein the selection is made when cfDNA molecules corresponding to, or derived from each of the genomic regions in cancer training samples have an anomalous methylation pattern, wherein the anomalous methylation pattern comprises at least five methylation sites known to be, or identified as either hypomethylated or hypermethylated, and designing the assay panel comprising a plurality of probes, wherein each of the probes is configured to hybridize to a modified fragment obtained from processing cfDNA molecules corresponding to, or derived from one or more of the subset of the genomic regions. In some embodiments, the processing of the cfDNA molecules comprises converting unmethylated C (cytosine) to U (uracil) in the cfDNA molecules.

Further disclosed herein are bait sets for hybridization capture, the bait set comprising at least 50 different polynucleotide-containing probes, wherein each of the polynucleotide-containing probes has a nucleic acid sequence that is either (1) identical in sequence to a sequence within a genomic region selected from any genomic region listed in any one of Tables 1-24 or (2) varies with respect to a sequence within the genomic region only by one or more transitions, wherein each respective transition in the one or more transitions occurs at a nucleotide corresponding to a CpG site in the genomic region.

In some embodiments, each of the polynucleotide-containing probes has a nucleic acid sequence of at least 45 base pairs in length. In some embodiments, the polynucleotide-containing probes have a nucleic acid sequence of no more than 200 base pairs in length. In some embodiments, the at least 50 different polynucleotide-containing probes are organized into at least 25 pairs of polynucleotide-containing probes, wherein each pair of probes comprises a first probe and a second probe that differs from the first probe, wherein the first probe overlaps in sequence with the second probe by at least 30 nucleotides. In some embodiments, the first probe overlaps in sequence with the second probe by at least 40, 50, 75, or 100 nucleotides.

In some embodiments, the polynucleotide-containing probes are organized into at least 50, 60, 70, 80, 90, 100, 120, 150, or 200 pairs of polynucleotide containing probes. In some embodiments, the polynucleotide-containing probes are organized into at least 1,000, 2,000, 2,500, 5,000, 6,000, 7,500, 10,000, 15,000, 20,000, or 25,000 pairs of polynucleotide containing probes. In some embodiments, a uracil or thymine is positioned at the transition. In some embodiments, each of the polynucleotide-containing probes is conjugated to an affinity moiety, wherein the affinity moiety is not a nucleic acid affinity moiety. In some embodiments, the affinity moiety comprises biotin. In some embodiments, each of the polynucleotide-containing probes comprises less than 20, 15, 10, 8, or 6 CpG detection sites. In some embodiments, the bait set has no probes that are homologous to or complementary in sequence with more than 8, 10, 15, or 20 off-target genomic regions.

In some embodiments, the bait set has at least 50, 60, 70, 80, 90, 100, 120, 150, or 200 polynucleotide-containing probes. In some embodiments, the bait set has at least 1,000, 2,000, 2,500, 5,000, 10,000, 12,000, 15,000, 20,000, or 25,000 polynucleotide-containing probes. In some embodiments, at least 3%, 5%, 10%, 15%, 20%, 30%, or 40% of all of the polynucleotide-containing probes in the bait set lack G (Guanine). In some embodiments, the polynucleotide-containing probes together comprise at least 0.01 million, 0.02 million, 0.05 million, 0.2 million, 0.4 million, 0.6 million, 0.8 million, 1 million, 2 million, or 4 million nucleotides. In some embodiments, each probe of the plurality of polynucleotide probes comprises at least 50, 75, 100, or 120 nucleotides. In some embodiments, each probe of the plurality of polynucleotide probes has less than 300, 250, 200, or 150 nucleotides. In some embodiments, each probe of the plurality of polynucleotide probes has from 100 to 150 nucleotides.

In some embodiments, at least 80%, 85%, 90%, 92%, 95%, or 98% of the plurality of polynucleotide-containing probes have exclusively either CpG or CpA on CpG detection sites. In some embodiments, the polynucleotide-containing probes of the bait set correspond with a total number of genomic regions selected from the genomic regions of any one of Tables 1-24, wherein at least 30% of the genomic regions are in exons or introns. In some embodiments, the polynucleotide-containing probes of the bait set correspond with a total number of genomic regions, wherein at least 15% of the genomic regions are in exons. In some embodiments, the polynucleotide-containing probes of the bait set correspond with a total number of genomic regions, wherein at least 20% of the genomic regions are in exons. In some embodiments, the polynucleotide-containing probes of the bait set correspond with a total number of genomic regions, wherein less than 10% of the genomic regions are intergenic regions.

In some embodiments, the bait sets further comprise a plurality of virus-specific probes, wherein each of the virus-specific probes is configured to hybridize to a viral genome fragment. In some embodiments, the viral genome fragment is from MCV, EBV, HBV, HCMV, HCV, HHV5, HPV16, or HPV18. In some embodiments, the plurality of virus-specific probes comprises at least 50, 100, 200, 500, 1,000, 2,000, or 3,000 virus-specific probes. In some embodiments, each of the plurality of polynucleotide-containing probes either (1) is identical in sequence to a sequence within a genomic region selected from Table 2 or (2) varies with respect to a sequence within a genomic region selected from Table 2 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 3 or (2) varies with respect to a sequence within a genomic region selected from Table 3 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 4 or (2) varies with respect to a sequence within a genomic region selected from Table 4 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 5 or (2) varies with respect to a sequence within a genomic region selected from Table 5 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 6 or (2) varies with respect to a sequence within a genomic region selected from Table 6 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 7 or (2) varies with respect to a sequence within a genomic region selected from Table 7 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 8 or (2) varies with respect to a sequence within a genomic region selected from Table 8 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 9 or (2) varies with respect to a sequence within a genomic region selected from Table 9 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 10 or (2) varies with respect to a sequence within a genomic region selected from Table 10 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from any one of Tables 2-10 or (2) varies with respect to a sequence within a genomic region selected from any one of Tables 2-10 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 11 or (2) varies with respect to a sequence within a genomic region selected from Table 11 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 12 or (2) varies with respect to a sequence within a genomic region selected from Table 12 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 13 or (2) varies with respect to a sequence within a genomic region selected from Table 13 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 14 or (2) varies with respect to a sequence within a genomic region selected from Table 114 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 15 or (2) varies with respect to a sequence within a genomic region selected from Table 15 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 16 or (2) varies with respect to a sequence within a genomic region selected from Table 16 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 17 or (2) varies with respect to a sequence within a genomic region selected from Table 17 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 18 or (2) varies with respect to a sequence within a genomic region selected from Table 18 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 19 or (2) varies with respect to a sequence within a genomic region selected from Table 19 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 20 or (2) varies with respect to a sequence within a genomic region selected from Table 20 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 21 or (2) varies with respect to a sequence within a genomic region selected from Table 21 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 22 or (2) varies with respect to a sequence within a genomic region selected from Table 22 only by one or more transitions, wherein each respective transition of the one or more transitions occurs at a nucleotide corresponding to a CpG site in the genomic region.

In some embodiments, each of the plurality of polynucleotide-containing probes either (1) is identical in sequence to a sequence within a genomic region selected from Table 23 or (2) varies with respect to a sequence within a genomic region selected from Table 23 only by one or more transitions, wherein each respective transition of the one or more transitions occurs at a nucleotide corresponding to a CpG site in the genomic region. In some embodiments, each of the plurality of polynucleotide-containing probes either (1) is identical in sequence to a sequence within a genomic region selected from Table 24 or (2) varies with respect to a sequence within a genomic region selected from Table 24 only by one or more transitions, wherein each respective transition of the one or more transitions occurs at a nucleotide corresponding to a CpG site in the genomic region.

In some embodiments, an entirety of polynucleotide probes in the bait set are configured to hybridize to fragments obtained from cfDNA molecules corresponding to at least 30%, 40%, 50%, 60%, 70%, 80%, 90% or 95% of the genomic regions in a table selected from any one of Tables 1-24. In some embodiments, an entirety of polynucleotide-containing probes in the bait set are configured to hybridize to fragments obtained from cfDNA molecules corresponding to at least 30%, 40%, 50%, 60%, 70%, 80%, 90% or 95% of the genomic regions in any one of Tables 2-10 or 16-24. In some embodiments, an entirety of polynucleotide-containing probes in the bait set are configured to hybridize to fragments obtained from cfDNA molecules corresponding to at least 500, 1,000, 5000, 10,000 or 15,000 genomic regions in any one of Tables 1-24. In some embodiments, an entirety of polynucleotide-containing probes in the bait set are configured to hybridize to fragments obtained from cfDNA molecules corresponding to at least 50, 60, 70, 80, 90, 100, 120, 150, or 200 genomic regions in any one of Tables 2-10 or 16-24. In some embodiments, the nucleic acid sequence of each of the polynucleotide-containing probes varies with respect to a sequence within the genomic region only by one or more transitions, wherein each respective transition of the one or more transitions occurs at a nucleotide corresponding to a CpG site in the genomic region.

Further disclosed herein are mixtures comprising bisulfate-converted cell-free DNA and the bait set of any one of the bait sets described above.

Moreover, disclosed herein are methods for enriching a bisulfate-converted cell-free DNA sample, comprising contacting the bisulfate-converted cell-free DNA sample with the bait set to form a mixture; and enriching the sample for a first set of genomic regions by hybridization capture.

Further disclosed herein are methods for providing sequence information informative of a presence or absence of a cancer, a stage of cancer, or a type of cancer, comprising processing cell-free DNA from a biological sample with a deaminating agent to generate a cell-free DNA sample comprising deaminated nucleotides; and enriching the cell-free DNA sample for informative cell-free DNA molecules, wherein enriching the cell-free DNA sample informative cell-free DNA molecules comprises contacting the cell-free DNA with a plurality of probes that are configured to hybridize to cell-free DNA molecules that correspond to regions identified in any one of Tables 1-24; and sequencing the enriched cell-free DNA molecules, thereby obtaining a set of sequence reads informative of a presence or absence of a cancer, a stage of cancer, or a type of cancer.

In some embodiments, the plurality of probes comprise a plurality of primers, and enriching the cell-free DNA comprises amplifying (e.g., via PCR) the cell-free DNA fragments using the primers (optionally in the absence of hybridization capture). In some embodiments, the cell-free DNA sample is enriched by any suitable method described herein and the plurality of probes comprise the plurality of polynucleotide-containing probes.

In some embodiments, the methods further comprise the later step of: determining a cancer classification by evaluating the set of sequence reads, wherein the cancer classification is a presence or absence of cancer; a stage of cancer; a presence or absence of a type of cancer; or a presence or absence of at least 1, 2, 3, 4, or 5 different types of cancer.

In some embodiments, the plurality of probes are configured to hybridize to bisulfite-converted fragments obtained from processing of cfDNA molecules, wherein each of the cfDNA molecules corresponds to or is derived from one or more genomic regions selected from one of Tables 1, 11, 12, 13, 14, or 15, wherein the cancer classification is a presence or absence of cancer or a stage of cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in one of Tables 1, 11, 12, 13, 14, or 15.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 2, wherein the cancer classification is a presence or absence of blood cancer or a stage of blood cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 2.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 3, wherein the cancer classification is a presence or absence of breast cancer or a stage of breast cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 3.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 4, wherein the cancer classification is a presence or absence of colorectal cancer or a stage of colorectal cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 4.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 5, wherein the cancer classification is a presence or absence of esophageal cancer or a stage of esophageal cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 5.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 6, wherein the cancer classification is a presence or absence of head and neck cancer or a stage of head and neck cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 6.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 7, wherein the cancer classification is a presence or absence of hepatobiliary cancer or a stage of hepatobiliary cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 7.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 8, wherein the cancer classification is a presence or absence of lung cancer or a stage of lung cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 8.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 9, wherein the cancer classification is a presence or absence of ovarian cancer or a stage of ovarian cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 9.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 10, wherein the cancer classification is a presence or absence of pancreatic cancer or a stage of pancreatic cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 10.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 16, wherein the cancer classification is a presence or absence of blood cancer or a stage of blood cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 16.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 17, wherein the cancer classification is a presence or absence of breast cancer or a stage of breast cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 17.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 18, wherein the cancer classification is a presence or absence of colorectal cancer or a stage of colorectal cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 18.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 19, wherein the cancer classification is a presence or absence of esophageal cancer or a stage of esophageal cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 19.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 20, wherein the cancer classification is a presence or absence of head and neck cancer or a stage of head and neck cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 20.

In some embodiments, the plurality of probes are configured to hybridize to bisulfite-converted fragments obtained from processing of cfDNA molecules, wherein each of the cfDNA molecules corresponds to or is derived from one or more genomic regions selected from Table 21, wherein the cancer classification is a presence or absence of hepatobiliary cancer or a stage of hepatobiliary cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 21.

In some embodiments, the plurality of probes are configured to hybridize to bisulfate-converted fragments obtained from processing of cfDNA molecules, wherein each of the cfDNA molecules corresponds to or is derived from one or more genomic regions selected from Table 22, wherein the cancer classification is a presence or absence of lung cancer or a stage of lung cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 22.

In some embodiments, the plurality of probes are configured to hybridize to bisulfate-converted fragments obtained from processing of cfDNA molecules, wherein each of the cfDNA molecules corresponds to or is derived from one or more genomic regions selected from Table 23, wherein the cancer classification is a presence or absence of ovarian cancer or a stage of ovarian cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 23.

In some embodiments, the plurality of probes are configured to hybridize to bisulfate-converted fragments obtained from processing of cfDNA molecules, wherein each of the cfDNA molecules corresponds to or is derived from one or more genomic regions selected from Table 24, wherein the cancer classification is a presence or absence of pancreatic cancer or a stage of pancreatic cancer. In some embodiments, the plurality of probes are configured to hybridize to bisulfate-converted fragments obtained from the cfDNA molecules corresponding to or derived from at least 30%, 40%, 50%, 60%, 70%, 80%, 90% or 95% of the genomic regions in Table 24.

In some embodiments, determining a cancer classification comprises generating a test feature vector based on the set of sequence reads; and applying the test feature vector to a model obtained by a training process with a cancer set of fragments from one or more training subjects with cancer and a non-cancer set of fragments from one or more training subjects without cancer, wherein both cancer set of fragments and the non-cancer set of fragments comprise a plurality of training fragments.

In some embodiments, the training process comprises obtaining sequence information of training fragments from a plurality of training subjects; for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each training subject, generating a training feature vector based on the hypomethylated training fragments and hypermethylated training fragments, and training the model with the training feature vectors from the one or more training subjects without cancer and the training feature vectors from the one or more training subjects with cancer.

In some embodiments, the training process comprises obtaining sequence information of training fragments from a plurality of training subjects; for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; for each training fragment, generating an aggregate hypomethylation score based on the hypomethylation score of the CpG sites in the training fragment and an aggregate hypermethylation score based on the hypermethylation score of the CpG sites in the training fragment; for each training subject: ranking the plurality of training fragments based on aggregate hypomethylation score and ranking the plurality of training fragments based on aggregate hypermethylation score; and generating a feature vector based on the ranking of the training fragments; obtaining training feature vectors for one or more training subjects without cancer and training feature vectors for the one or more training subjects with cancer; and training the model with the feature vectors for the one or more training subjects without cancer and the feature vectors for the one or more training subjects with cancer.

In some embodiments, the model comprises one of a kernel logistic regression classifier, a random forest classifier, a mixture model, a convolutional neural network, and an autoencoder model. In some embodiments, the methods further comprise obtaining a cancer probability for the test sample based on the model; and comparing the cancer probability to a threshold probability to determine whether the test sample is from a subject with cancer or without cancer. In some embodiments, the methods further comprise administering an anti-cancer agent to the subject.

Further disclosed herein are methods for treating a cancer patient, comprising administering an anti-cancer agent to a subject who has been identified as a cancer subject by the methods disclosed herein. In some embodiments, the anti-cancer agent is a chemotherapeutic agent selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, and platinum-based agents.

Moreover disclosed herein are methods for providing sequence information informative of a presence or absence of a cancer, comprising contacting cell-free DNA from a biological sample with a deaminating agent to generate a cell-free DNA sample comprising deaminated nucleotides; enriching the cell-free DNA for a plurality of DNA fragments that together correspond to at least 100, 200, 500, or 1000 genomic regions selected from genomic regions identified in any one of Tables 1-24; and sequencing the enriched cell-free DNA molecules, thereby obtaining a set of sequence reads.

In some embodiments, enriching the cell-free DNA does not involve hybridization capture. In some embodiments, enriching the cell-free DNA comprises amplifying the plurality of DNA fragments. In some embodiments, amplifying the cell-free DNA molecules comprises contacting the cell-free DNA with a plurality of sets of primers and amplifying the cell-free DNA molecules via PCR, wherein each primer set comprises a forward primer and a reverse primer.

Further disclosed herein are assay panels for enriching cfDNA molecules for cancer diagnosis, comprising at least 50 different pairs of polynucleotide probes, wherein each pair of the at least 50 pairs of probes (i) comprises two different probes configured to overlap with each other by an overlapping sequence of 30 or more nucleotides and (ii) is configured to hybridize to a modified fragment obtained from processing of the cfDNA molecules, wherein each of the cfDNA molecules corresponds to or is derived from one or more genomic regions, wherein each of the one or more genomic regions comprises at least five methylation sites and has an anomalous methylation pattern in cancerous training samples.

In some embodiments, the overlapping sequence comprises at least 40, 50, 75, or 100 nucleotides. In some embodiments, the assay panels disclosed herein comprise at least 50, 60, 70, 80, 90, 100, 120, 150 or 200 pairs of probes.

Further disclosed herein are assay panels for enriching cfDNA molecules for cancer diagnosis, comprising at least 100 polynucleotide probes, wherein each of the at least 100 probes is configured to hybridize to a modified polynucleotide obtained from processing of the cfDNA molecules, wherein each of the cfDNA molecules corresponds to or is derived from, one or more genomic regions, wherein each of the one or more genomic regions comprises at least five methylation sites, and has an anomalous methylation pattern in cancerous training samples.

In some embodiments, the processing of the cfDNA molecules comprises converting unmethylated C (cytosine) to U (uracil) in the cfDNA molecules. In some embodiments, each of the probes on the panel is conjugated to a biotin moiety. In some embodiments, the training samples are samples originating from a plurality of subjects determined to have cancer. In some embodiments, a genomic region has an anomalous methylation pattern in cancerous training samples when a methylation state vector representing the genomic region in the cancerous training samples is present less frequently in reference samples than a threshold value. In some embodiments, the threshold value is 0.1, 0.01, 0.001, or 0.0001.

In some embodiments, each of the one or more genomic regions is either hypermethylated or hypomethylated in the cancerous training samples. In some embodiments, at least 80, 85, 90, 92, 95, or 98% of the at least five methylation sites are either methylated or unmethylated in the cancerous training samples. In some embodiments, at least 3%, 5%, 10%, 15%, 20%, 30%, or 40% of the probes on the panel comprise no G (Guanine). In some embodiments, at least 80, 85, 90, 92, 95, 98% of the probes on the panel have exclusively either CpG or CpA on CpG detection sites. In some embodiments, each of the probes on the panel comprises less than 20, 15, 10, 8, or 6 CpG detection sites.

In some embodiments, each of the probes on the panel is designed to have sequence homology or sequence complementarity with fewer than 20, 15, 10, or 8 off-target genomic regions. In some embodiments, the fewer than 20 off-target genomic regions are identified using a k-mer seeding strategy. In some embodiments, the fewer than 20 off-target genomic regions are identified using k-mer seeding strategy combined to local alignment at seed locations.

In some embodiments, the assay panels comprise at least 100, 200, 300, or 400 probes. In some embodiments, the at least 500 pairs of probes or the at least 100 probes together comprise at least 0.01 million, 0.02 million, or 0.05 million nucleotides. In some embodiments, each of the probes on the panel comprises at least 50, 75, 100, or 120 nucleotides. In some embodiments, each of the probes on the panel comprises less than 300, 250, 200, or 150 nucleotides. In some embodiments, each of the probes on the panel comprises 100-150 nucleotides.

In some embodiments, the assay panels further comprise a plurality of virus-specific probes, wherein each of the virus-specific probes is configured to hybridize to a viral genome fragment from cfDNA. In some embodiments, the viral genome fragment is from MCV, EBV, HBV, HCMV, HCV, HHV5, HPV16, or HPV18. In some embodiments, the assay panels comprise at least 50, 100, 200, 500, 1000, 2000, or 3000 virus-specific probes.

In some embodiments, each of the one or more genomic regions is selected from one or more of the genomic regions of Tables 2-10 or 16-24. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of Tables 2-10 or 16-24. In some embodiments, an entirety of probes on the panel together are configured to hybridize to modified fragments obtained from the cfDNA molecules corresponding to or derived from at least 50, 60, 70, 80, 90, 100, 120, 150 or 200 genomic regions from one or more of Tables 2-10 or 16-24.

BRIEF DESCRIPTION OF THE DRAWINGS

FIG. 3A is a flowchart describing a process of creating a data structure for a control group, according to an embodiment.

FIG. 3B is a flowchart describing an additional step of validating the data structure for the control group of FIG. 3A, according to an embodiment.

FIG. 5 is an illustration of an example p-value score calculation, according to an embodiment.

FIG. 6B is a flowchart describing a process of identifying fragments indicative of cancer determined by probabilistic models, according to an embodiment.

FIGS. 11A, 11B, and 11C include graphs showing the cancer log-odds ratio determined for various cancers across different stages and types of cancer.

Figure 1A:
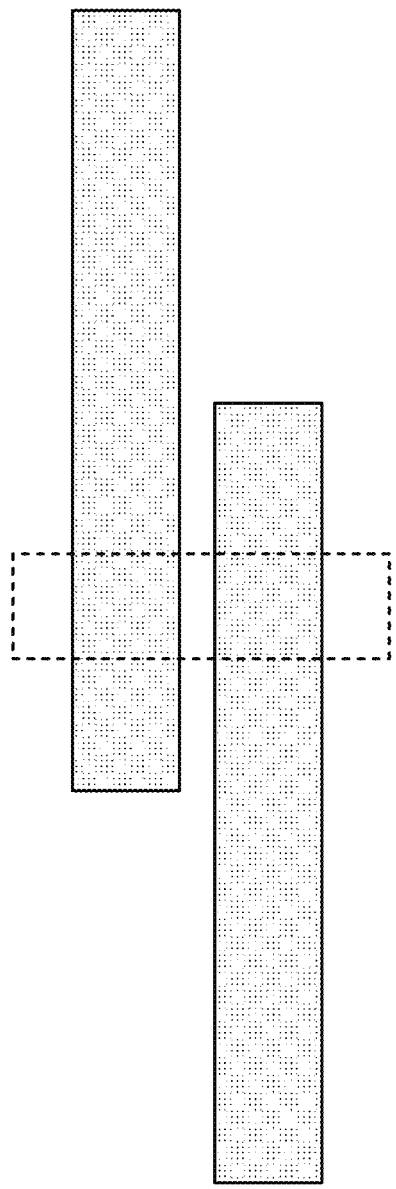
FIG. 1A illustrates 2× tiled probe design where each base in a target region (boxed in the dotted rectangle) is covered by exactly two probes, according to an embodiment.

The figures depict various embodiments of the present description for purposes of illustration only. One skilled in the art will readily recognize from the following discussion that alternative embodiments of the structures and methods illustrated herein may be employed without departing from the principles of the description described herein.

DETAILED DESCRIPTION

Definitions

Unless defined otherwise, all technical and scientific terms used herein have the meaning commonly understood by a person skilled in the art to which this description belongs. As used herein, the following terms have the meanings ascribed to them below.

The term "methylation" as used herein refers to a process by which a methyl group is added to a DNA molecule. Two of DNA's four bases, cytosine ("C") and adenine ("A") can be methylated. For example, a hydrogen atom on the pyrimidine ring of a cytosine base can be converted to a methyl group, forming 5-methylcytosine. Methylation tends to occur at dinucleotides of cytosine and guanine referred to herein as "CpG sites." In other instances, methylation may occur at a cytosine not part of a CpG site or at another nucleotide that is not cytosine; however, these are rarer occurrences. In this present disclosure, methylation is discussed in reference to CpG sites for the sake of clarity. However, the principles described herein are equally applicable for the detection of methylation in a non-CpG context, including non-cytosine methylation. For example, Adenine methylation has been observed in bacteria, plant and mammalian DNA, although it has received considerably less attention.

In such embodiments, the wet laboratory assay used to detect methylation may vary from those described herein as is well known in the art. Further, the methylation state vectors may contain elements that are generally vectors of sites where methylation has or has not occurred (even if those sites are not CpG sites specifically). With that substitution, the remainder of the processes described herein are the same, and consequently the inventive concepts described herein are applicable to those other forms of methylation.

The term "methylation site" as used herein refers to a site on a DNA molecule where a methyl group can be added. "CpG" sites are the most common methylation site, but methylation sites are not limited to CpG sites.

For example, DNA methylation may occur in cytosines in CHG and CHH, where H is adenine, cytosine or thymine. Cytosine methylation in the form of 5-hydroxymethylcytosine may also assessed (see, e.g., WO 2010/037001 and WO 2011/127136, which are incorporated herein by reference), and features thereof, using the methods and procedures disclosed herein.

The term "CpG site" as used herein refers to a region of a DNA molecule where a cytosine nucleotide is followed by a guanine nucleotide in the linear sequence of bases along its 5' to 3' direction. "CpG" is a shorthand for 5'-C-phosphate-G-3' that is cytosine and guanine separated by only one phosphate group; phosphate links any two nucleotides together in DNA. Cytosines in CpG dinucleotides can be methylated to form 5-methylcytosine.

The term "CpG detection site" as used herein refers to a region in a probe that is configured to hybridize to a CpG site of a target DNA molecule. The CpG site on the target DNA molecule can comprise cytosine and guanine separated by one phosphate group, where cytosine is methylated or unmethylated. The CpG site on the target DNA molecule can comprise uracil and guanine separated by one phosphate group, where the uracil is generated by the conversion of unmethylated cytosine.

The term "UpG" is a shorthand for 5'-U-phosphate-G-3' that is uracil and guanine separated by only one phosphate group. UpG can be generated by a bisulfite treatment of a DNA that converts unmethylated cytosines to uracils. Cytosines can be converted to uracils by other methods known in the art, such as chemical modification or synthesis.

The term "hypomethylated" or "hypermethylated" as used herein refers to a methylation status of a DNA molecule containing multiple CpG sites (e.g., more than 3, 4, 5, 6, 7, 8, 9, 10, etc.) where a high percentage of the CpG sites (e.g., more than 80%, 85%, 90%, or 95%, or any other percentage within the range of 50%-100%) are unmethylated or methylated, respectively.

The term "methylation state vector" or "methylation status vector" as used herein refers to a vector comprising multiple elements, where each element indicates methylation status of a methylation site in a DNA molecule comprising multiple methylation sites, in the order they appear from 5' to 3' in the DNA molecule. For example, $<M_x, M_{x+1}, M_{x+2}>$, $<M_x, M_{x+1}, U_{x+2}>$, ... $<U_x, U_{x+1}, U_{x+2}>$ can be methylation vectors for DNA molecules comprising three methylation sites, where M represents a methylated methylation site and U represents an unmethylated methylation site.

The term "abnormal methylation pattern" or "anomalous methylation pattern" as used herein refers to a methylation state vector or a methylation status of a DNA molecule having the methylation state vector that is expected to be found in a sample less frequently than a threshold value. In a particular embodiment provided herein, the expectedness of finding a specific methylation state vector in a healthy control group comprising healthy individuals is represented by a p-value. A low p-value score, thereby, generally corresponds to a methylation state vector which is relatively unexpected in comparison to other methylation state vectors within samples from healthy individuals in the healthy control group. A high p-value score generally corresponds to a methylation state vector which is relatively more expected in comparison to other methylation state vectors found in samples from healthy individuals in the healthy control group. A methylation state vector having a p-value lower than a threshold value (e.g., 0.1, 0.01, 0.001, 0.0001, etc.) can be defined as an abnormal methylation pattern. Various methods known in the art can be used to calculate a p-value or expectedness of a methylation pattern or a methylation state vector. Exemplary methods provided herein involve use of a Markov chain probability that assumes methylation statuses of CpG sites to be dependent on methylation statuses of neighboring CpG sites. Alternate methods provided herein calculate the expectedness of observing a specific methylation state vector in healthy individuals by utilizing a mixture model including multiple mixture components, each being an independent-sites model where methylation at each CpG site is assumed to be independent of methylation statuses at other CpG sites.

Methods provided herein use genomic regions having an anomalous methylation pattern. A genomic region can be determined to have an anomalous methylation pattern when cfDNA fragments corresponding to or originated from the genomic region have methylation state vectors that appear less frequently than a threshold value in reference samples. The reference samples can be samples from control subjects or healthy subjects. The frequency for a methylation state vector to appear in the reference samples can be represented as a p-value score. When cfDNA fragments corresponding to or originated from the genomic region do not have a single, uniform methylation state vector, the genomic region can have multiple p-value scores for multiple methylation state vectors. In this case, the multiple p-value scores can be summed or averaged before being compared to the threshold value. Various methods known in the art can be adopted to compare p-value scores corresponding to the genomic region and the threshold value, including but not limited to arithmetic mean, geometric mean, harmonic mean, median, mode, etc.

The term "cancerous sample" as used herein refers to a sample comprising genomic DNAs from an individual diagnosed with cancer. The genomic DNAs can be, but are not limited to, cfDNA fragments or chromosomal DNAs from a subject with cancer. The genomic DNAs can be sequenced and their methylation status can be assessed by methods known in the art, for example, bisulfite sequencing. When genomic sequences are obtained from public database (e.g., The Cancer Genome Atlas (TCGA)) or experimentally obtained by sequencing a genome of an individual diagnosed with cancer, cancerous sample can refer to genomic DNAs or cfDNA fragments having the genomic sequences. The term "cancerous samples" as a plural refers to samples comprising genomic DNAs from multiple individuals, each individual diagnosed with cancer. In various embodiments, cancerous samples from more than 100, 300, 500, 1,000, 10,000, 20,000, 40,000, 50,000, or more individuals diagnosed with cancer are used.

The term "non-cancerous sample" as used herein refers to a sample comprising genomic DNAs from an individual not diagnosed with cancer. The genomic DNAs can be, but are not limited to, cfDNA fragments or chromosomal DNAs from a subject without cancer. The genomic DNAs can be sequenced and their methylation status can be assessed by methods known in the art, for example, bisulfite sequencing. When genomic sequences are obtained from public database (e.g., The Cancer Genome Atlas (TCGA)) or experimentally obtained by sequencing a genome of an individual without cancer, non-cancerous sample can refer to genomic DNAs or cfDNA fragments having the genomic sequences. The term "non-cancerous samples" as a plural refers to samples comprising genomic DNAs from multiple individuals, each individual is not diagnosed with cancer. In various embodiments, cancerous samples from more than 100, 300, 500, 1,000, 10,000, 20,000, 40,000, 50,000, or more individuals without cancer are used.

The term "training sample" as used herein refers to a sample used to train a classifier described herein and/or to select one or more genomic regions for cancer diagnosis. The training samples can comprise genomic DNAs or a modification there of, from one or more healthy subjects and from one or more subjects having a disease condition for diagnosis (e.g., cancer, a specific type of cancer, a specific stage of cancer, etc.). The genomic DNAs can be, but are not limited to, cfDNA fragments or chromosomal DNAs. The genomic DNAs can be sequenced and their methylation status can be assessed by methods known in the art, for example, bisulfite sequencing. When genomic sequences are obtained from public database (e.g., The Cancer Genome Atlas (TCGA)) or experimentally obtained by sequencing a genome of an individual, a training sample can refer to genomic DNAs or cfDNA fragments having the genomic sequences.

The term "test sample" as used herein refers to a sample from a subject, whose health condition was, has been or will be tested using a classifier and/or an assay panel described herein. The test sample can comprise genomic DNAs or a modification there of. The genomic DNAs can be, but are not limited to, cfDNA fragments or chromosomal DNAs.

The term "target genomic region" as used herein refers to a region in a genome selected for designing a probe to be included in an assay panel. The probe can be designed to hybridize to (and optionally pull down) a nucleic acid fragment corresponding to, or derived from the target genomic region or a fragment thereof. A nucleic acid fragment corresponding to, or derived from the target genomic region refers to a nucleic acid fragment generated by degradation, cleavage, or other biological processing of the target genomic region or a nucleic acid fragment having a sequence homologous or complementary to the target genomic region.

The term "off-target genomic region" as used herein refers to a region in a genome which has not been selected for designing a probe to be included in an assay panel, but has sufficient homology to a target genomic region to be bound and pulled down by a probe designed to target the target genomic region. In one embodiment, the off-target genomic region is a genomic region that aligns to a probe along at least 45 bp with at least a 90% match rate.

The term "cell free nucleic acid," "cell free DNA," or "cfDNA" refers to nucleic acid fragments that circulate in an individual's body (e.g., bloodstream) and originate from one or more healthy cells and/or from one or more cancer cells. Additionally, cfDNA may come from other sources such as viruses, fetuses, etc.

The term "converted DNA molecules," "converted cfDNA molecules," or "modified fragment obtained from processing of the cfDNA molecules" refers to DNA molecules obtained by processing DNA or cfDNA molecules in the sample in a chemical reaction for the purpose of differentiating a methylated nucleotide and an unmethylated nucleotide in the DNA or cfDNA molecules. For example, in one embodiment, the sample can be treated with bisulfite ion (e.g., using sodium bisulfite), as is well-known in the art, to convert unmethylated cytosines ("C") to uracils ("U"). In another embodiment, the conversion of unmethylated cytosines to uracils is accomplished using an enzymatic conversion reaction, for example, using a cytidine deaminase (such as APOBEC). After treatment, converted DNA molecules or cfDNA molecules include additional uracils which are not present in the original cfDNA sample.

The term "circulating tumor DNA" or "ctDNA" refers to nucleic acid fragments that originate from tumor cells or other types of cells, which may be released into an individual's bloodstream as result of biological processes such as apoptosis or necrosis of dying cells or actively released by viable tumor cells.

The term "individual" refers to a human individual. The term "healthy individual" refers to an individual presumed not to have a cancer or disease.

The term "subject" refers to an individual whose DNA is being analyzed. A subject may be a test subject whose DNA is be evaluated using a targeted panel as described herein to evaluate whether or not the person has cancer or another disease. A subject may also be part of a control group known not to have cancer or another disease. A subject may also be part of a cancer or other disease group known to have cancer or another disease. Control and cancer/disease groups may be used to assist in designing or validating the targeted panel.

The term "sequence reads" as used herein refers to nucleotide sequences read from a sample. Sequence reads can be obtained through various methods provided herein or as known in the art.

The term "sequencing depth" as used herein refers to the count of the number of times a given target nucleic acid within a sample has been sequenced (e.g., the count of sequence reads at a given target region). Increasing sequencing depth can reduce required amounts of the target nucleic acids need for assessing a disease state (e.g., cancer or cancer tissue of origin).

The term "tissue of origin" or "TOO" as used herein refers to the organ, organ group, body region or cell type that cancer arises or originates from. The identification of a tissue of origin or cancer cell type typically allows for identification of the most appropriate next steps in the care continuum of cancer to further diagnose, stage and decide on treatment.

"An entirety of probes" of a panel or bait set or "an entirety of polynucleotide-containing probes" of a panel or bait set generally refers to all of the probes delivered with a specified panel or bait set. For instance, in some embodiments, a panel or bait set may include both (1) probes having features specified herein (e.g., probes for binding to cell-free DNA fragments corresponding to or derived from genomic regions set forth herein in one or more Tables) and (2) additional probes that do not contain such feature(s). The entirety of probes of a panel generally refers to all probes delivered with the panel or bait set, including such probes that do not contain the specified feature(s).

Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Cancer Assay Panel

In a first aspect, the present description provides a cancer assay panel (e.g., a bait set) comprising a plurality of probes or a plurality of probe pairs. The probes can be polynucleotide-containing probes that are specifically designed to target one or more nucleic acid molecules corresponding to, or derived from genomic regions differentially methylated between cancer and non-cancer samples, between different cancer tissue of origin types, between different cancer cell types, or between samples of different stages of cancer, as identified by methods provided herein. In some embodiments, probes target genomic regions (or nucleic acid molecules derived therefrom) having methylation patterns specific to a cancer type, e.g., (1) blood cancer, (2) breast cancer, (3) colorectal cancer, (4) esophageal cancer, (5) head and neck cancer, (6) hepatobiliary cancer, (7) lung cancer, (8) ovarian cancer, or (9) pancreatic cancer. In some embodiments, the panel includes probes targeting genomic regions specific to a single cancer type. In some embodiments, the panel includes probes specific to 2, 3, 4, 5, 6, 7, 8, or 9 or more cancer types. In some embodiments, the target genomic regions are selected to maximize classification accuracy, subject to a size limitation (which can be determined by a sequencing budget and a desired depth of sequencing).

Figure 2:
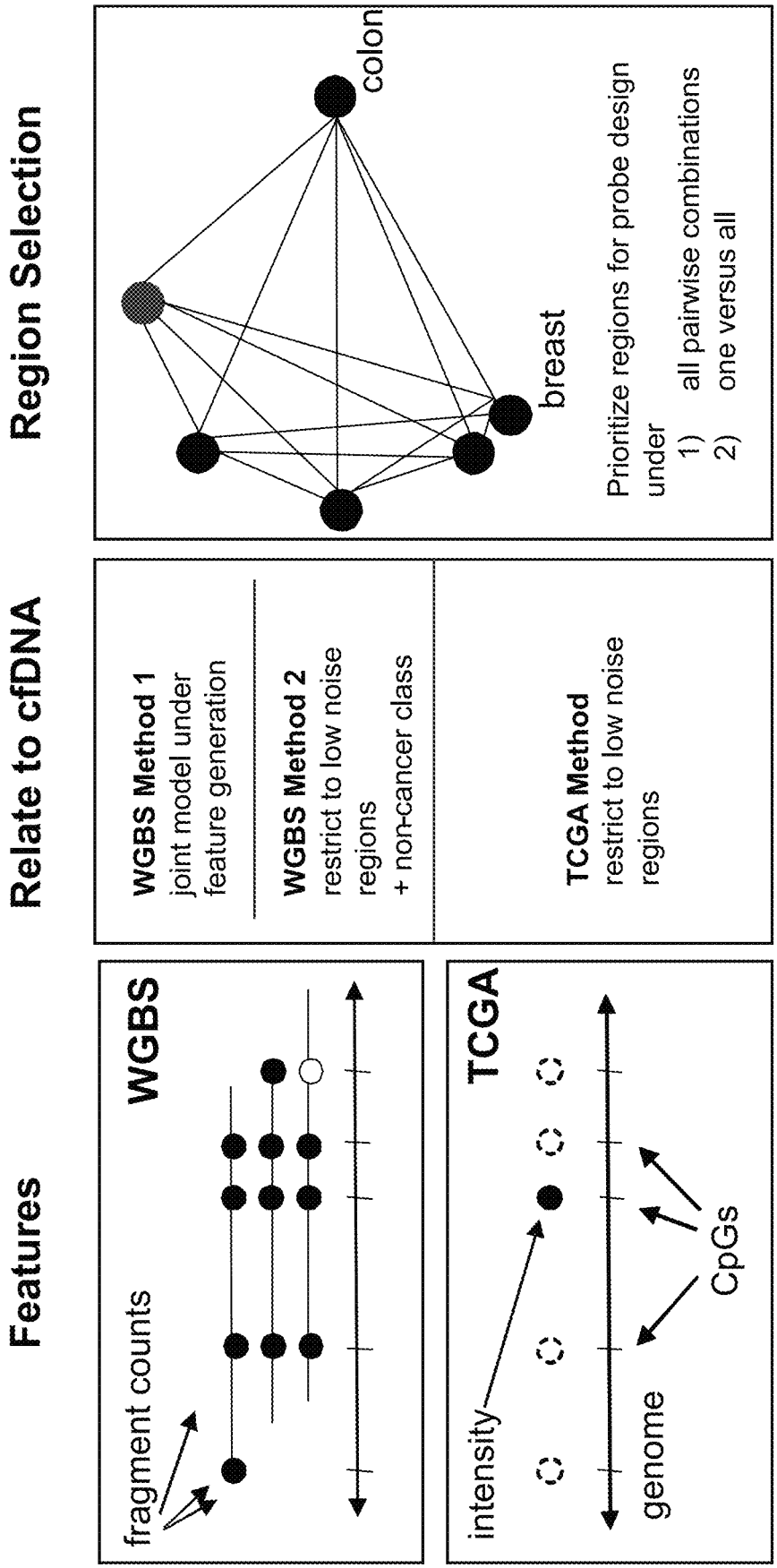
FIG. 2 is a schematic describing a process of generating a cancer assay panel, according to an embodiment.

Design features and potential utility of an exemplary cancer assay panel are shown in FIG. 2. For designing the cancer assay panel, an analytics system may collect samples corresponding to various outcomes under consideration, e.g., samples known to have cancer, samples considered to be healthy, samples from a known tissue of origin, etc. These samples may be processed with whole-genome bisulfite sequencing (WGBS) or obtained from public database (e.g., TCGA). The analytics system may be any generic computing system with a computer processor and a computer-readable storage medium with instructions for executing the computer processor to perform any or all operations described in this present disclosure. With the samples, the analytics system determines methylation statuses at one or more CpG sites for each nucleic acid fragment in the sample. The analytics system may then select target genomic regions based on methylation patterns of nucleic acid fragments. One approach considers pairwise distinguishability between pairs of outcomes for regions or more specifically one or more CpG sites. Another approach considers distinguishability for regions or more specifically one or more CpG sites when considering each outcome against the remaining outcomes. From the selected target genomic regions with high distinguishability power, the analytics system may design probes to target nucleic acid fragments inclusive of the selected genomic regions. The analytics system may generate variable sizes of the cancer assay panel, e.g., where a small sized cancer assay panel includes probes targeting the most informative genomic region, a medium sized cancer assay panel includes probes from the small sized cancer assay panel and additional probes targeting a second tier of informative genomic regions, and a large sized cancer assay panel includes probes from the small sized and the medium sized cancer assay panels and even more probes targeting a third tier of informative genomic regions. With such cancer assay panels, the analytics system may train classifiers with various classification techniques to predict a sample's likelihood of having a particular outcome, e.g., cancer, specific cancer type, other disorder, etc.

Specifically, in some embodiments, the cancer assay panel comprises at least 50 pairs of probes, wherein each pair of the at least 50 pairs comprises two probes configured to overlap each other by an overlapping sequence, wherein the overlapping sequence comprises a 30-nucleotide sequence, and wherein the 30-nucleotide sequence is configured to hybridize to a modified fragment obtained from processing of the cfDNA molecules corresponding to one or more genomic regions, wherein each of the genomic regions comprises at least five methylation sites, and wherein the at least five methylation sites have an anomalous methylation pattern in training samples. In other words, when cfDNA molecules in training samples corresponding to the genomic region are analyzed, they have methylation status vectors appearing less frequently than a threshold value in reference samples.

In other embodiments, the cancer assay panel comprises at least 500 pairs of probes, wherein each pair of the at least 500 pairs comprises two probes configured to overlap each other by an overlapping sequence, wherein the overlapping sequence comprises a 30-nucleotide sequence, and wherein the 30-nucleotide sequence is configured to hybridize to a modified fragment obtained from processing of the cfDNA molecules corresponding to one or more genomic regions, wherein each of the genomic regions comprises at least five methylation sites, and wherein the at least five methylation sites have an anomalous methylation pattern in training samples. Again, when cfDNA molecules in training samples corresponding to the genomic region are analyzed, they have methylation status vectors appearing less frequently than a threshold value in reference samples.

In a preferred embodiment, the at least five methylation sites are differentially methylated either between cancerous and non-cancerous samples or between one or more pairs of samples from different cancer types. In some embodiments, the converted cfDNA molecules comprise cfDNA molecules treated (e.g., via bisulfite treatment) to convert unmethylated C (cytosine) to U (uracil). In some cases, the uracil is further converted to thymine (e.g., upon PCR amplification).

Since the probes are configured to hybridize to a converted DNA or cfDNA molecule corresponding to, or derived from, one or more genomic regions, the probes can have a sequence different from the targeted genomic region. For example, a DNA molecule containing unmethylated CpG site will be converted to include UpG because unmethylated cytosines are converted to uracils by a conversion reaction (e.g., bisulfite treatment). As a result, a probe is configured to hybridize to a sequence including UpG instead of a naturally existing unmethylated CpG. Accordingly, a complementary site in the probe to the unmethylated site can comprise CpA instead of CpG, and some probes targeting a hypomethylated site where all methylation sites are unmethylated can have no guanine (G) bases. In some embodiments, at least 3%, 5%, 10%, 15%, 20%, 30%, or 40% of the probes lack G (Guanine). In some embodiments, at least 80, 85, 90, 92, 95, 98% of the probes on the panel have exclusively either CpG or CpA on CpG detection sites. Accordingly, in some embodiments, polynucleotide-containing probes have a nucleic acid sequence that is either (1) identical in sequence to a sequence within a target genomic region (e.g., target genomic regions set forth herein in Tables 1-24) or (2) varies with respect to a sequence within the genomic region only one or more transitions (e.g., changes in base composition at a site due to bisulfite conversion or other conversion techniques), wherein each respective transition in the one or more transitions occurs at a nucleotide corresponding to a CpG site in the genomic region.

In some embodiments, probes on the panel comprise less than 20, 15, 10, 8, or 6 CpG detection sites. In some embodiments, probes on the panel comprise more than 5, 6, 7, 8, 9, or 10 CpG detection sites.

In some embodiments, probes are conjugated to a tag (e.g., a non-nucleic acid affinity moiety), such as a biotin moiety.

The cancer assay panel can be used to detect the presence or absence of cancer generally and/or provide a cancer classification such as cancer type, or stage of cancer such as I, II, III, or IV, or where the cancer is believed to originate. The panel may include probes targeting nucleic acids derived from genomic regions differentially methylated between general cancerous (pan-cancer) samples and non-cancerous samples, or only in cancerous samples with a specific cancer type (e.g., lung cancer-specific targets). For example, in some embodiments, a cancer assay panel is designed to enrich nucleic acids derived from differentially methylated genomic regions in cancerous samples identified based on bisulfite sequencing data generated from the cfDNA from cancer and non-cancer individuals.

Each of the probes (or probe pairs) can be designed to target nucleic acids derived from one or more target genomic regions. The target genomic regions are selected based on several criteria designed to increase selective enrichment of informative cfDNA fragments while decreasing noise and non-specific bindings.

Figure 1B:
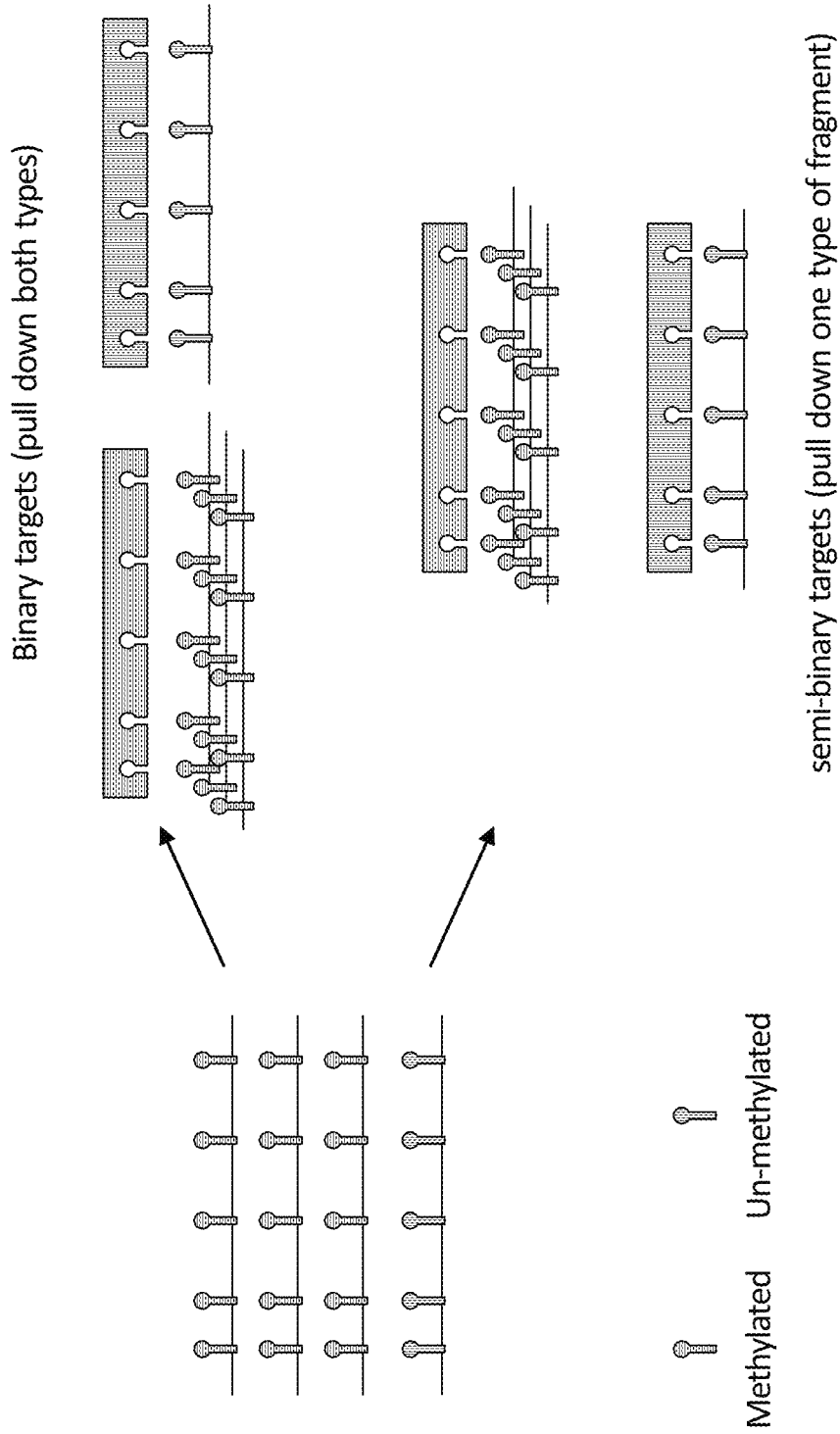
FIG. 1B illustrates probe design targeting hypomethylated and/or hypermethylated fragments in genomic regions, according to an embodiment.

In one example, a panel can include probes that can selectively hybridize to (i.e., bind to) and enrich cfDNA fragments that are differentially methylated in cancerous samples. In this case, sequencing of the enriched fragments can provide information relevant to diagnosis of cancer. Furthermore, the probes are designed to target genomic regions that are determined to have an anomalous methylation pattern in cancer samples, or in samples from certain tissue types or cell types. In one embodiment, probes are designed to target genomic regions determined to be hypermethylated or hypomethylated in certain cancers, or cancer tissue of origins, to provide additional selectivity and specificity of the detection. In some embodiments, a panel comprises probes targeting hypomethylated fragments. In some embodiments, a panel comprises probes targeting hypermethylated fragments. In some embodiments, a panel comprises both a first set of probes targeting hypermethylated fragments and a second set of probes targeting hypomethylated fragments (FIG. 1B). In some embodiments, the ratio between the first set of probes targeting hypermethylated fragments and the second set of probes targeting hypomethylated fragments (Hyper:Hypo ratio) ranges between 0.4 and 2, between 0.5 and 1.8, between 0.5 and 1.6, between 1.4 and 1.6, between 1.2 and 1.4, between 1 and 1.2, between 0.8 and 1, between 0.6 and 0.8 or between 0.4 and 0.6.

Methods of identifying genomic regions (i.e., genomic regions giving rise to anomalously methylated DNA molecules or differentially methylated DNA molecules between cancer and non-cancer samples, between different cancer tissue of origin types, between different cancer cell type, or between samples from different stages of cancer) are provided in detail in the Section titled "Methods of selecting target genomic regions" and methods of identifying anomalously methylated DNA molecules or fragments that are identified as indicative of cancer are provided in detail in the sub-section titled "Anomalously methylated fragments" and the sub-section titled "Filtration of anomalous methylated fragments," respectively.

In a second example, genomic regions can be selected when the genomic regions give rise to anomalously methylated DNA molecules in cancer samples or samples with a known cancer type. For example, as described herein, a Markov model trained on a set of reference samples (e.g., samples from healthy subject) can be used to identify genomic regions that give rise to anomalously methylated DNA molecules (i.e., DNA molecules having a methylation pattern below a p-value threshold).

Each of the probes can target a genomic region comprising at least 30 bp, 35 bp, 40 bp, 45 bp, 50 bp, 60 bp, 70 bp, 80 bp, 90 bp, 100 bp or more. In some embodiments, the genomic regions can be selected to have less than 30, 25, 20, 15, 12, 10, 8, or 6 methylation sites.

The genomic regions can be selected when at least 80, 85, 90, 92, 95, or 98% of the at least five methylation (e.g., CpG) sites within the region are either methylated or unmethylated in non-cancerous or cancerous samples, in cancer samples from a particular cancer type.

Genomic regions may be further filtered to select only those that are likely to be informative based on their methylation patterns, for example, CpG sites that are differentially methylated between cancerous and non-cancerous samples (e.g., abnormally methylated or unmethylated in cancer versus non-cancer), between cancerous samples of a tissue of origin and cancerous samples of a different tissue of origin, or CpG sites that are differentially methylated only in cancerous samples of a specific type. For the selection, calculation can be performed with respect to each CpG site or a plurality of CpG sites. For example, a first count is determined that is the number of cancer-containing samples (cancer count) that include a fragment overlapping that CpG, and a second count is determined that is the number of total samples containing fragments overlapping that CpG site (total). Genomic regions can be selected based on criteria positively correlated to the number of cancer-containing samples (cancer_count) that include a fragment indicative of cancer overlapping that CpG site, and inversely correlated with the number of total samples containing fragments indicative of cancer overlapping that CpG site (total). In one embodiment, the number of non-cancerous samples ($n_{non\text{-}cancer}$) and the number of cancerous samples ($n_{cancer}$) having a fragment overlapping a CpG site are counted. Then the probability that a sample is cancer is estimated, for example as $(n_{cancer}+1)/(n_{cancer}+n_{non\text{-}cancer}+2)$.

CpG sites by this metric can be ranked and greedily added to a panel until the panel size budget is exhausted. The process of selecting genomic regions indicative of cancer is further detailed in the sub-section titled "Genomic regions indicative of cancer and classifiers."

Depending on whether the assay is intended to be a pan-cancer assay or a single-cancer assay, or depending on what kind of flexibility is desired when picking which CpG sites are contributing to the panel. A panel for diagnosing a specific cancer type can be designed using a similar process. In this embodiment, for each cancer type, and for each CpG site, the information gain is computed to determine whether to include a probe targeting that CpG site. The information gain may be computed for samples with a given cancer type of a tissue of origin compared to all other samples. For example, two random variables, "AF" and "CT." "AF" is a binary variable that indicates whether there is an abnormal fragment overlapping a particular CpG site in a particular sample (yes or no). "CT" is a binary random variable indicating whether the cancer is of a particular type (e.g., lung cancer or cancer other than lung). One can compute the mutual information with respect to "CT" given "AF." That is, how many bits of information about the cancer type (lung vs. non-lung in the example) are gained if one knows whether there is an anomalous fragment overlapping a particular CpG site. This can be used to rank CpG's based on how lung-specific they are. This procedure is repeated for a plurality of cancer types. If a particular region is commonly differentially methylated only in lung cancer (and not other cancer types or non-cancer), CpG's in that region would tend to have high information gains for lung cancer. For each cancer type, CpG sites ranked by this information gain metric, and then greedily added to a panel until the size budget for that cancer type is exhausted.

Further filtration can be performed to select probes with high specificity for enrichment (i.e., high binding efficiency) of nucleic acids derived from targeted genomic regions. Probes can be filtered to reduce non-specific binding (or off-target binding) to nucleic acids derived from non-targeted genomic regions. For example, probes can be filtered to select only those probes having less than a set threshold of off-target binding events. In one embodiment, probes can be aligned to a reference genome (e.g., a human reference genome) to select probes that align to less than a set threshold of regions across the genome. For example, probes can be selected that align to less than 25, 24, 23, 22, 21, 20, 19, 18, 17, 16, 15, 14, 13, 12, 11, 10, 9 or 8 off-target regions across the reference genome. In other cases, filtration is performed to remove genomic regions when the sequence of the target genomic regions appears more than 5, 10, 15, 20, 21, 22, 23, 24, 25, 26, 27, 28, 29, 30, 31, 32, 33, 34 or 35 times in a genome. Further filtration can be performed to select target genomic regions when a sequence, or a set of sequences that are 90%, 91%, 92%, 93%, 94%, 95%, 96%, 97%, 98% or 99% homologous to the target genomic regions, appear less than 25, 24, 23, 22, 21, 20, 19, 18, 17, 16, 15, 14, 13, 12, 11, 10, 9 or 8 times in a reference genome, or to remove target genomic regions when the sequence, or a set of sequences that are 90%, 91%, 92%, 93%, 94%, 95%, 96%, 97%, 98% or 99% homologous to the target genomic regions appear more than 5, 10, 15, 20, 21, 22, 23, 24, 25, 26, 27, 28, 29, 30, 31, 32, 33, 34 or 35 times in a reference genome. This is for excluding probes that can pull down off-target fragments, which are not desired and can impact assay efficiency.

A fragment-probe overlap of at least 45 bp enabled a non-negligible amount of pulldown (though this number can be different depending on assay details) as provided in Example 1. Thus, in some embodiments, probes are at least 45 base pairs in length. In some embodiments, more than a 10% mismatch rate between the probe and fragment sequences in the region of overlap is sufficient to greatly disrupt binding, and thus pulldown efficiency. Therefore, sequences that can align to the probe along at least 45 bp with at least a 90% match rate are candidates for off-target pulldown. Thus, in one embodiment, the number of such regions are scored. The best probes have a score of 1, meaning they match in only one place (the intended target region). Probes with a low score (say, less than 5 or 10) are accepted, but any probes above the score are discarded. Other cutoff values can be used for specific samples.

Once the probes hybridize and capture DNA fragments corresponding to, or derived from, a target genomic region, the hybridized probe-DNA fragment intermediates are pulled down (or isolated), and the targeted DNA is amplified and sequenced. The sequence read provides information relevant for diagnosis of cancer. For this end, a panel is designed to include a plurality of probes that can capture fragments that can together provide information relevant to diagnosis of cancer. In some embodiments, a panel includes at least at least 50, 60, 70, 80, 90, 100, 120, 150, or 200 different pairs of probes. In other embodiments, a panel includes at least at least 500, 1,000, 2,000, 2,500, 5,000, 6,000, 7,500, 10,000, 15,000, 20,000, 25,000, or 50,000 different pairs of probes. In some embodiments, a panel includes at least 100, 120, 140, 160, 180, 200, 240, 300, or 400 different probes. In other embodiments, a panel includes at least 1,000, 2,000, 5,000, 10,000, 12,000, 15,000, 20,000, 30,000, 40,000, 50,000, or 100,000 different probes. The plurality of probes together can comprise at least 0.01 million, 0.02 million, 0.03 million, 0.04 million, 0.05 million, 0.1 million, 0.2 million, 0.4 million, 0.6 million, 0.8 million, 1 million, 2 million, 3 million, 4 million, 5 million, 6 million, 7 million, 8 million, 9 million, or 10 million nucleotides.

The selected target genomic regions can be located in various positions in a genome, including but not limited to exons, introns, intergenic regions, and other parts. In some embodiments, probes targeting non-human genomic regions, such as those targeting viral genomic regions, can be added.

Probes

Cancer assay panels (e.g., bait sets) provided herein can include a set of hybridization probes (also referred to herein as "probes") designed to, during enrichment, target and pull down (e.g., via hybridization capture) nucleic acid fragments of interest for the assay. In some embodiments, the probes are designed to hybridize and enrich a modified fragment obtained from processing of DNA or cfDNA molecules from samples from a subject with cancer or a subject with a specific cancer type. The processing step can convert unmethylated cytosines (C) to uracils (U). The probes can be designed to anneal (or hybridize) to a target (complementary) strand of the modified fragment (e.g., DNA or RNA). The target strand can be the "positive" strand (e.g., the strand transcribed into mRNA, and subsequently translated into a protein) or the complementary "negative" strand. In a particular embodiment, a cancer assay panel includes sets of two probes, one probe targeting the positive strand and the other probe targeting the negative strand of a target genomic region.

For each target genomic region, four possible probe sequences can be designed. DNA molecules corresponding to, or derived from, each target region is double-stranded, as such, a probe or probe set can target either the "positive" or forward strand or its reverse complement (the "negative" strand). Additionally, in some embodiments, the probes or probe sets are designed to enrich DNA molecules or fragments that have been processed to convert unmethylated cytosines (C) to uracils (U). Because the probes or probe sets are designed to enrich DNA molecules corresponding to, or derived from the targeted regions after conversion, the probe's sequence can be designed to enrich DNA molecules of fragments where unmethylated C's have been converted to U's (by utilizing A's in place of G's at sites that are unmethylated cytosines in DNA molecules or fragments corresponding to, or derived from, the targeted region). In one embodiment, probes are designed to bind to, or hybridize to, DNA molecules or fragments from genomic regions known to contain cancer-specific methylation patterns (e.g., hypermethylated or hypomethylated DNA molecules), thereby enriching for cancer-specific DNA molecules or fragments. Targeting genomic regions, or cancer-specific methylation patterns, can be advantageous allowing one to specifically enrich for DNA molecules or fragments identified as informative for cancer or cancer tissue of origin, and thus, lowering sequencing needs and sequencing costs. In other embodiments, two probe sequences can be designed per a target genomic region (one for each DNA strand). In still other cases, probes are designed to enrich for all DNA molecules or fragments corresponding to, or derived from, a targeted region (i.e., regardless of strand or methylation status). This might be because the cancer methylation status is not highly methylated or unmethylated, or because the probes are designed to target small mutations or other variations rather than methylation changes, with these other variations similarly indicative of the presence or absence of a cancer or the presence or absence of a cancer of one or more tissue of origins. In that case, all four possible probe sequences can be included per a target genomic region.

For instance, cancer assay panels, such as bait sets for hybridization capture can include polynucleotide-containing probes that each include a nucleic acid sequence that either (1) is identical in sequence to a sequence within a genomic region (e.g., a genomic region listed in any one of Tables 1-24) or (2) varies with respect to a sequence in the genomic region only by one or more transitions, wherein each respective transition in the one or more transitions occurs at a nucleotide corresponding to a CpG site in the genomic region. Probes that are identical in sequence to a sequence within a genomic region may be used to bind to "completely methylated" cell-free DNA molecules in which none of the cytosine bases are converted to uracil. Conversely, probes having a nucleic acid sequence that varies with respect to a sequence in the genomic region only by one or more transitions (e.g., at CpG sites) can be used to bind to partially or completely methylated probes in which one or more (e.g., all) of the cytosines are unmethylated and subsequently converted to uracil by a deaminating agent such as sodium bisulfite.

The probes can range in length from 10s, 100s, 200s, or 300s of base pairs. The probes can comprise at least 45, 50, 75, 100, or 120 nucleotides. The probes can comprise less than 300, 250, 200, or 150 nucleotides. In an embodiment, the probes comprise 45-200 or 100-150 nucleotides. In one particular embodiment, the probes comprise 120 nucleotides.

The probes are designed to analyze methylation status of target genomic regions (e.g., of the human or another organism) that are suspected to correlate with the presence or absence of cancer generally, presence or absence of certain types of cancers, cancer stage, or presence or absence of other types of diseases.

Furthermore, the probes can be designed to effectively hybridize to (or bind to) and pull down cfDNA fragments containing a target genomic region. In some embodiments, the probes are designed to cover overlapping portions of a target genomic region, so that each probe is "tiled" in coverage such that each probe overlaps in coverage at least partially with another probe in the library (FIG. 1A). In such embodiments, the panel contains multiple pairs of probes, where each pair comprises at least two probes overlapping each other by an overlapping sequence of at least 25, 30, 35, 40, 45, 50, 60, 70, 75 or 100 nucleotides. In some embodiments, the overlapping sequence can be designed to have sequence homology with or to be complementary to a target genomic region (or a converted version thereof), thus a nucleotide fragment corresponding to or derived from, or containing the target genomic region can be bound and pulled down by at least one of the probes.

In one embodiment, a 2× tiled design, as illustrated in FIG. 1A, is used, where each base in a target region (the dotted rectangle in FIG. 1A) is overlapped by two probes. For instance, each pair of probes may include a first probe and a second probe that both differs from the first probe and overlaps in sequence with the first probe (e.g., overlap by at least 30 nucleotides). This is done to ensure that even relatively short DNA fragments (e.g., 100 bp) corresponding to, or derived from a targeted region, are guaranteed to have a substantial overlap (or sequence complementarity) with at least one probe, allowing for efficient capture of the relatively short DNA fragment. For example, a 100-bp DNA fragment overlapping a 30 bp target region would have at least a 75 bp overlap with at least one of the two probes. Other levels of tiling are possible. For example, to increase target size and capture efficiency, more probes can be tilted over a given target region. To increase capture of any DNA fragment that overlaps the target region, the probes can be designed to extend past the ends of the target region on either side on both sides. For example, probes can be designed to extend past the ends of a 30-bp target region by at least 50 bp, 60 bp, 70 bp, 80 bp, 90, or 100 bp.

In one embodiment, the smallest target genomic region is 30 bp. When a new target region is added to the panel (based on the greedy selection as described above), the new target region of 30 bp can be centered on a specific CpG site of interest. Then, it is checked whether each edge of this new target is close enough to other targets such that they can be merged. This is based on a "merge distance" parameter which can be 200 bp by default but can be tuned. This allows close but distinct target regions to be enriched with overlapping probes. Depending on whether close enough targets exist to the left or right of the new target, the new target can be merged with nothing (increasing the number of panel targets by one), merged with just one target either to the left or the right (not changing the number of panel targets), or merged with existing targets both to the left and right (reducing the number of panel targets by one).

An assay panel provided herein comprises a plurality of polynucleotide probes configured to hybridize to a modified fragment obtained from processing of the cfDNA molecules, wherein each of the cfDNA molecules corresponds to or is derived from one or more genomic regions. Stated differently, the polynucleotide-containing probes of a bait set may, as a group, correspond with a number of genomic regions. In some embodiments, at least 15%, 20%, 30%, or 40% of the genomic regions are in exons or introns. In some embodiments, at least 5%, 10%, 15%, 20%, 30% or 40% of the genomic regions are in exons. In some embodiments, less than 5%, 10%, 15%, 20%, 25%, or 30% of the genomic regions are in intergenic regions.

In some embodiments, each of the one or more genomic regions is selected from one or more of Tables 1-24. In some embodiments, each of the one or more genomic regions is selected from one or more of Tables 2-10 or 16-24. In some embodiments, each of the one or more genomic regions is selected from Table 1. In some embodiments, each of the one or more genomic regions is selected from Table 2. In some embodiments, each of the one or more genomic regions is selected from Table 3. In some embodiments, each of the one or more genomic regions is selected from Table 4. In some embodiments, each of the one or more genomic regions is selected from Table 5. In some embodiments, each of the one or more genomic regions is selected from Table 6. In some embodiments, each of the one or more genomic regions is selected from Table 7. In some embodiments, each of the one or more genomic regions is selected from Table 8. In some embodiments, each of the one or more genomic regions is selected from Table 9. In some embodiments, each of the one or more genomic regions is selected from Table 10. In some embodiments, each of the one or more genomic regions is selected from Table 11. In some embodiments, each of the one or more genomic regions is selected from Table 12. In some embodiments, each of the one or more genomic regions is selected from Table 13. In some embodiments, each of the one or more genomic regions is selected from Table 14. In some embodiments, each of the one or more genomic regions is selected from Table 15. In some embodiments, each of the one or more genomic regions is selected from Table 16. In some embodiments, each of the one or more genomic regions is selected from Table 17. In some embodiments, each of the one or more genomic regions is selected from Table 18. In some embodiments, each of the one or more genomic regions is selected from Table 19. In some embodiments, each of the one or more genomic regions is selected from Table 20. In some embodiments, each of the one or more genomic regions is selected from Table 21. In some embodiments, each of the one or more genomic regions is selected from Table 22. In some embodiments, each of the one or more genomic regions is selected from Table 23. In some embodiments, each of the one or more genomic regions is selected from Table 24.

In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of Tables 1-24. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of Tables 2-10 or 16-24. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 1. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 2. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 3. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 4. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 5. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 6. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 7. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 8. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 9. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 10. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 11. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 12. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 13. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 14. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 15. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 16. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 17. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 18. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 19. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 20. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 21. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 22. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 23. In some embodiments, an entirety of probes on the panel together are configured to hybridize to modified fragments obtained from the cfDNA molecules corresponding to or derived from at least 30%, 40%, 50%, 60%, 70%, 80%, 90% or 95% of the genomic regions in one or more of the genomic regions in Table 24.

In some embodiments, an entirety of probes on the panel together are configured to hybridize to modified fragments obtained from the cfDNA molecules corresponding to or derived from at least 500, 1,000, 5000, 10,000 or 15,000 genomic regions in one or more of Tables 1 or 11-15. In some embodiments, an entirety of probes on the panel together are configured to hybridize to modified fragments obtained from the cfDNA molecules corresponding to or derived from at least 50, 60, 70, 80, 90, 100, 120, 150, or 200 genomic regions from one or more of Tables 2-10 or 16-24. In some embodiments, an entirety of probes on the panel together are configured to hybridize to modified fragments obtained from the cfDNA molecules corresponding to or derived from at least 500, 1,000, 5000, 10,000 or 15,000 genomic regions in Table 13. In some embodiments, an entirety of probes on the panel together are configured to hybridize to modified fragments obtained from the cfDNA molecules corresponding to or derived from at least 500, 1,000, 5000, 10,000 or 15,000 genomic regions in Table 14. In some embodiments, an entirety of probes on the panel together are configured to hybridize to modified fragments obtained from the cfDNA molecules corresponding to or derived from at least 500, 1,000, 5000, 10,000 or 15,000 genomic regions in Table 15.

In some embodiments, an assay panel further comprises virus-specific probes, wherein each of the virus-specific probes is configured to hybridize to a viral genome fragment. The probes can be configured to hybridize a viral genome fragment from a viral strain associated with cancer. In some embodiment, the viral genome fragment is from MCV, EBV, HBV, HCMV, HCV, HHV5, HPV16, or HPV18. In some embodiments, the panel comprises at least 50, 100, 200, 300, 400, 500, 600, 700, 800, 900, 1000, 1500, 2000, 2500, or 3000 virus-specific probes.

Methods of Selecting Target Genomic Regions

In another aspect, methods of selecting target genomic regions for diagnosing cancer and/or a tissue of origin are provided. The targeted genomic regions can be used to design and manufacture probes for a cancer assay panel. Methylation status of DNA or cfDNA molecules corresponding to, or derived from, the target genomic regions can be screened by targeted sequencing using the cancer assay panel. Alternative methods, for example by WGBS or other methods known in the art, can be also implemented to detect methylation status of DNA molecules or fragments corresponding to, or derived from, the target genomic regions.

Sample Processing

For selection of target genomic regions, a nucleic acid sample (DNA or RNA) extracted from one or more subjects are used. In the present disclosure, DNA and RNA may be used interchangeably unless otherwise indicated. That is, the embodiments described herein may be applicable to both DNA and RNA types of nucleic acid sequences. However, the examples described herein may focus on DNA for purposes of clarity and explanation. The sample may be any subset of the human genome, including the whole genome. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has a cancer or disease, ctDNA in an extracted sample may be present at a detectable level for diagnosis.

The cfDNA fragments are treated to convert unmethylated cytosines to uracils. In one embodiment, the method uses a bisulfite treatment of the DNA which converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

With the converted cfDNA fragments, a sequencing library is prepared. In a first step, a ssDNA adapter is added to the 3'-OH end of a bisulfite-converted ssDNA molecule using a ssDNA ligation reaction. In one embodiment, the ssDNA ligation reaction uses CircLigase II (Epicentre) to ligate the ssDNA adapter to the 3'-OH end of a bisulfite-converted ssDNA molecule, wherein the 5'-end of the adapter is phosphorylated and the bisulfite-converted ssDNA has been dephosphorylated (i.e., the 3' end has a hydroxyl group). In another embodiment, the ssDNA ligation reaction uses Thermostable 5' AppDNA/RNA ligase (available from New England BioLabs (Ipswich, MA)) to ligate the ssDNA adapter to the 3'-OH end of a bisulfite-converted ssDNA molecule. In this example, the first UMI adapter is adenylated at the 5'-end and blocked at the 3'-end. In another embodiment, the ssDNA ligation reaction uses a T4 RNA ligase (available from New England BioLabs) to ligate the ssDNA adapter to the 3'-OH end of a bisulfite-converted ssDNA molecule. In a second step, a second strand DNA is synthesized in an extension reaction. For example, an extension primer that hybridizes to a primer sequence included in the ssDNA adapter is used in a primer extension reaction to form a double-stranded bisulfite-converted DNA molecule. Optionally, in one embodiment, the extension reaction uses an enzyme that is able to read through uracil residues in the bisulfite-converted template strand. Optionally, in a third step, a dsDNA adapter is added to the double-stranded bisulfite-converted DNA molecule. Finally, the double-stranded bisulfite-converted DNA is amplified to add sequencing adapters. For example, PCR amplification using a forward primer that includes a P5 sequence and a reverse primer that includes a P7 sequence is used to add P5 and P7 sequences to the bisulfite-converted DNA. Optionally, during library preparation, unique molecular identifiers (UMI) may be added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment, which provides a way to identify sequence reads that came from the same original fragment in downstream analysis.

Sequence reads are generated from the DNA sequences. The method may include next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

Methylation state vectors are then generated from the sequence reads. To do so, a sequence read is aligned to a reference genome. The reference genome helps provide the context as to what position in a human genome the fragment cfDNA originates from. In a simplified example, the sequence read is aligned such that the three CpG sites correlate to CpG sites 23, 24, and 25 (arbitrary reference identifiers used for convenience of description). After alignment, there is information both on methylation status of all CpG sites on the cfDNA fragment and which position in the human genome the CpG sites map to. With the methylation status and location, a methylation state vector may be generated for the cfDNA fragment.

Generation of Data Structure

FIG. 3A is a flowchart describing a process 300 of generating a data structure for a healthy control group (e.g., reference samples), according to an embodiment. To create a healthy control group data structure, the analytics system obtains information related to methylation status of a plurality of CpG sites on sequence reads derived from a plurality of DNA molecules or fragments from a plurality of healthy subjects. The method provided herein for creating a healthy control group data structure can be performed similarly for subjects with cancer, subjects with cancer of a tissue of origin, subjects with a known cancer type, or subjects with another known disease state. A methylation state vector is generated for each DNA molecule or fragment, for example via the process 100.

With each fragment's methylation state vector, the analytics system subdivides 310 the methylation state vector into strings of CpG sites. In one embodiment, the analytics system subdivides 310 the methylation state vector such that the resulting strings are all less than a given length. For example, a methylation state vector of length 11 may be subdivided into strings of length less than or equal to 3 would result in 9 strings of length 3, 10 strings of length 2, and 11 strings of length 1. In another example, a methylation state vector of length 7 being subdivided into strings of length less than or equal to 4 would result in 4 strings of length 4, 5 strings of length 3, 6 strings of length 2, and 7 strings of length 1. If a methylation state vector is shorter than or the same length as the specified string length, then the methylation state vector may be converted into a single string containing all of the CpG sites of the vector.

The analytics system tallies 320 the strings by counting, for each possible CpG site and possibility of methylation states in the vector, the number of strings present in the control group having the specified CpG site as the first CpG site in the string and having that possibility of methylation states. For example, at a given CpG site and considering string lengths of 3, there are $2^3$ or 8 possible string configurations. At that given CpG site, for each of the 8 possible string configurations, the analytics system tallies 320 how many occurrences of each methylation state vector possibility come up in the control group. Continuing this example, this may involve tallying the following quantities: $<M_x, M_{x+1}, M_{x+2}>, <M_x, M_{x+1}, U_{x+2}>, \ldots, <U_x, U_{x+1}, U_{x+2}>$ for each starting CpG site x in the reference genome. The analytics system creates 330 the data structure storing the tallied counts for each starting CpG site and string possibility.

There are several benefits to setting an upper limit on string length. First, depending on the maximum length for a string, the size of the data structure created by the analytics system can dramatically increase in size. For instance, maximum string length of 4 means that every CpG site has at the very least $2^4$ numbers to tally for strings of length 4. Increasing the maximum string length to 5 means that every CpG site has an additional $2^4$ or 16 numbers to tally, doubling the numbers to tally (and computer memory required) compared to the prior string length. Reducing string size helps keep the data structure creation and performance (e.g., use for later accessing as described below), in terms of computational and storage, reasonable. Second, a statistical consideration to limiting the maximum string length is to avoid overfitting downstream models that use the string counts. If long strings of CpG sites do not, biologically, have a strong effect on the outcome (e.g., predictions of anomalousness that predictive of the presence of cancer), calculating probabilities based on large strings of CpG sites can be problematic as it requires a significant amount of data that may not be available, and thus would be too sparse for a model to perform appropriately. For example, calculating a probability of anomalousness/cancer conditioned on the prior 100 CpG sites would require counts of strings in the data structure of length 100, ideally some matching exactly the prior 100 methylation states. If only sparse counts of strings of length 100 are available, there will be insufficient data to determine whether a given string of length of 100 in a test sample is anomalous or not.

Validation of Data Structure

Once the data structure has been created, the analytics system may seek to validate 340 the data structure and/or any downstream models making use of the data structure. One type of validation checks consistency within the control group's data structure. For example, if there are any outlier subjects, samples, and/or fragments within a control group, then the analytics system may perform various calculations to determine whether to exclude any fragments from one of those categories. In a representative example, the healthy control group may contain a sample that is undiagnosed but cancerous such that the sample contains anomalously methylated fragments. This first type of validation ensures that potential cancerous samples are removed from the healthy control group so as to not affect the control group's purity.

A second type of validation checks the probabilistic model used to calculate p-values with the counts from the data structure itself (i.e., from the healthy control group). A process for p-value calculation is described below in conjunction with FIG. 5. Once the analytics system generates a p-value for the methylation state vectors in the validation group, the analytics system builds a cumulative density function (CDF) with the p-values. With the CDF, the analytics system may perform various calculations on the CDF to validate the control group's data structure. One test uses the fact that the CDF should ideally be at or below an identity function, such that $CDF(x) \leq x$. On the converse, being above the identity function reveals some deficiency within the probabilistic model used for the control group's data structure. For example, if 1/100 of fragments have a p-value score of 1/1000 meaning $CDF(1/1000)=1/100>1/1000$, then the second type of validation fails indicating an issue with the probabilistic model.

A third type of validation uses a healthy set of validation samples separate from those used to build the data structure, which tests if the data structure is properly built and the model works. An example process for carrying out this type of validation is described below in conjunction with FIG. 3B. The third type of validation can quantify how well the healthy control group generalizes the distribution of healthy samples. If the third type of validation fails, then the healthy control group does not generalize well to the healthy distribution.

A fourth type of validation tests with samples from a non-healthy validation group. The analytics system calculates p-values and builds the CDF for the non-healthy validation group. With a non-healthy validation group, the analytics system expects to see the $CDF(x)>x$ for at least some samples or, stated differently, the converse of what was expected in the second type of validation and the third type of validation with the healthy control group and the healthy validation group. If the fourth type of validation fails, then this is indicative that the model is not appropriately identifying the anomalousness that it was designed to identify.

FIG. 3B is a flowchart describing the additional step 340 of validating the data structure for the control group of FIG. 3A, according to an embodiment. In this embodiment of the step 340 of validating the data structure, the analytics system performs the fourth type of validation test as described above which utilizes a validation group with a supposedly similar composition of subjects, samples, and/or fragments as the control group. For example, if the analytics system selected healthy subjects without cancer for the control group, then the analytics system also uses healthy subjects without cancer in the validation group.

The analytics system takes the validation group and generates 100 a set of methylation state vectors as described in FIG. 3A. The analytics system performs a p-value calculation for each methylation state vector from the validation group. The p-value calculation process will be further described in conjunction with FIGS. 4 & 5. For each possibility of methylation state vector, the analytics system calculates a probability from the control group's data structure. Once the probabilities are calculated for the possibilities of methylation state vectors, the analytics system calculates 350 a p-value score for that methylation state vector based on the calculated probabilities. The p-value score represents an expectedness of finding that specific methylation state vector and other possible methylation state vectors having even lower probabilities in the control group. A low p-value score, thereby, generally corresponds to a methylation state vector which is relatively unexpected in comparison to other methylation state vectors within the control group, where a high p-value score generally corresponds to a methylation state vector which is relatively more expected in comparison to other methylation state vectors found in the control group. Once the analytics system generates a p-value score for the methylation state vectors in the validation group, the analytics system builds 360 a cumulative density function (CDF) with the p-value scores from the validation group. The analytics system validates 370 consistency of the CDF as described above in the fourth type of validation tests.

Anomalously Methylated Fragments

Figure 4:
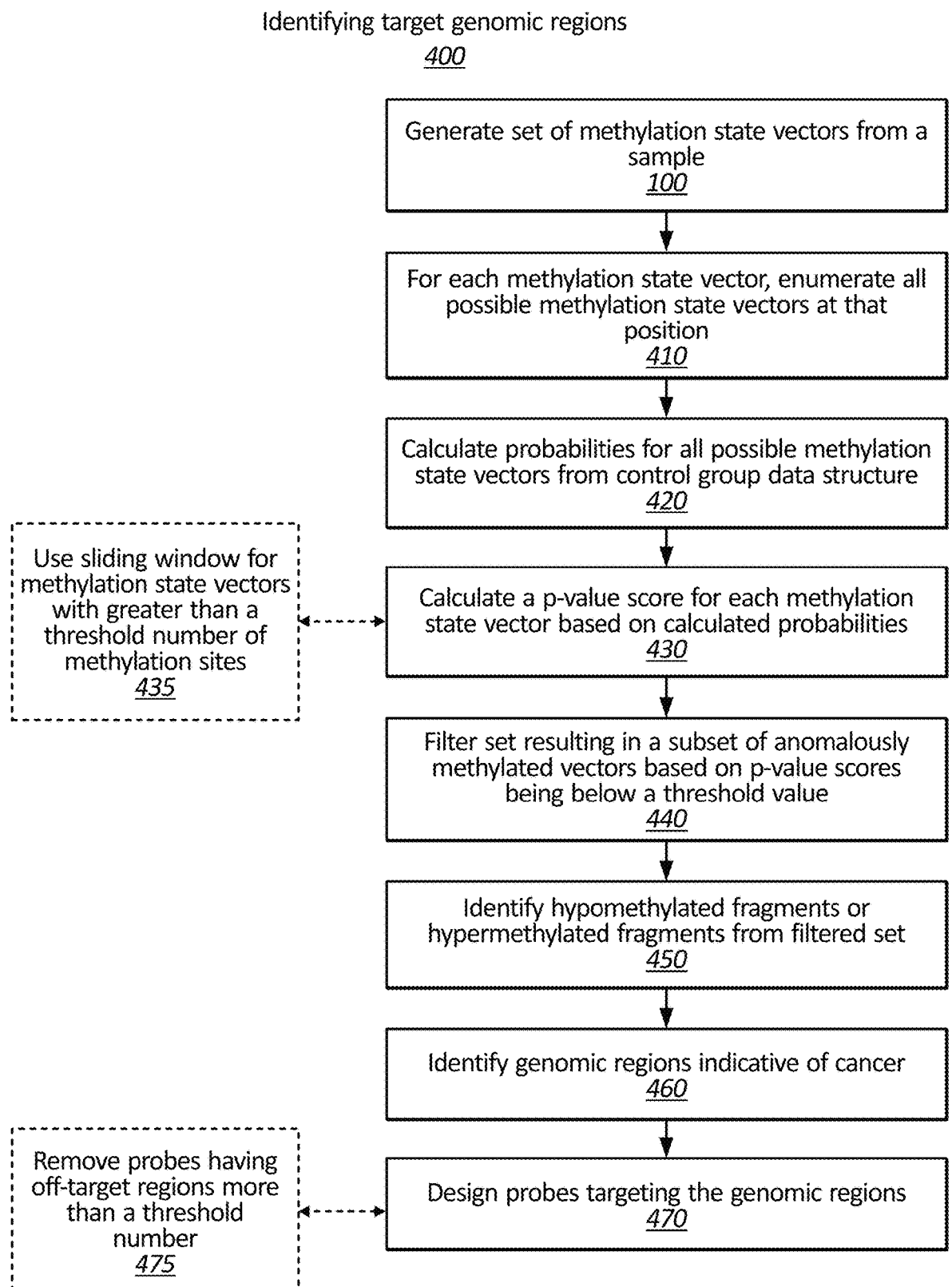
FIG. 4 is a flowchart describing a process for selecting genomic regions for designing probes for a cancer assay panel, according to an embodiment.

FIG. 4 is a flowchart describing a process 400 for identifying anomalously methylated fragments from a subject, according to an embodiment. An example of process 400 is visually illustrated in FIG. 5, and is further described below the description of FIG. 4. In process 400, the analytics system generates 100 methylation state vectors from cfDNA fragments of the subject. The analytics system handles each methylation state vector as follows.

In some embodiments, the analytics system filters fragments having indeterminate states at one or more CpG sites. In such embodiments, the analytics system implements a prediction model to identify fragments not likely to have an anomalous methylation pattern for filtering. For a sample fragment, the prediction model calculates a sample probability that the sample fragment's methylation state vector occurs in comparison to the healthy control group data structure. The prediction model randomly samples a subset of possible methylation state vectors encompassing the CpG sites in the sample fragment's methylation state vector. The prediction model calculates a probability corresponding to each of the sampled possible methylation state vectors. Probability calculations for the fragment's methylation state vector and the sampled possible methylation state vectors can be calculated according to a Markov chain model as will be described below in sub-section titled "P-value score calculation." The prediction model calculates a proportion of the sampled possible methylation state vectors corresponding to probabilities less than or equal to the sample probability. The prediction model generates an estimated p-value score for the fragment based on the calculated proportion. The prediction model may filter fragments corresponding to p-value scores above a threshold and retain fragments corresponding to p-value scores below the threshold.

In additional embodiments, the prediction model may calculate a confidence probability that is used by the prediction model to determine when to continue or when to terminate sampling. The confidence probability describes how likely the fragment's true p-value score (the calculation of the true p-value score further described below in sub-section titled P-value score calculation") is below a threshold based on the estimated p-value score and the probabilities of the sampled possible methylation state vectors. The prediction model may sample additional one or more possible methylation state vectors while iteratively calculating the estimated p-value score and the confidence probability. The prediction model may then terminate the sampling when the confidence probability is above a confidence threshold.

For a given methylation state vector, the analytics system enumerates 410 all possibilities of methylation state vectors having the same starting CpG site and same length (i.e., set of CpG sites) in the methylation state vector. As each observed methylation state may be methylated or unmethylated, there are only two possible states at each CpG site, and thus the count of distinct possibilities of methylation state vectors depends on a power of 2, such that a methylation state vector of length n would be associated with $2^n$ possibilities of methylation state vectors. With methylation state vectors inclusive of indeterminate states for one or more CpG sites, the analytics system may enumerate 410 possibilities of methylation state vectors considering only CpG sites that have observed states.

The analytics system calculates 420 the probability of observing each possibility of methylation state vector for the identified starting CpG site/methylation state vector length by accessing the healthy control group data structure. In one embodiment, calculating the probability of observing a given possibility uses a Markov chain probability to model the joint probability calculation which will be described in greater detail with respect to FIG. 5 below. In other embodiments, calculation methods other than Markov chain probabilities are used to determine the probability of observing each possibility of methylation state vector.

The analytics system calculates 430 a p-value score for the methylation state vector using the calculated probabilities for each possibility. In one embodiment, this includes identifying the calculated probability corresponding to the possibility that matches the methylation state vector in question. Specifically, this is the possibility having the same set of CpG sites, or similarly the same starting CpG site and length as the methylation state vector. The analytics system sums the calculated probabilities of any possibilities having probabilities less than or equal to the identified probability to generate the p-value score.

This p-value represents the probability of observing the methylation state vector of the fragment or other methylation state vectors even less probable in the healthy control group. A low p-value score, thereby, generally corresponds to a methylation state vector which is rare in a healthy subject, and which causes the fragment to be labeled anomalously methylated, relative to the healthy control group. A high p-value score generally relates to a methylation state vector expected to be present, in a relative sense, in a healthy subject. If the healthy control group is a non-cancerous group, for example, a low p-value indicates that the fragment is anomalously methylated relative to the non-cancer group, and therefore possibly indicative of the presence of cancer in the test subject.

As above, the analytics system calculates p-value scores for each of a plurality of methylation state vectors, each representing a cfDNA fragment in the test sample. To identify which of the fragments are anomalously methylated, the analytics system may filter 440 the set of methylation state vectors based on their p-value scores. In one embodiment, filtering is performed by comparing the p-values scores against a threshold and keeping only those fragments below the threshold. This threshold p-value score could be on the order of 0.1, 0.01, 0.001, 0.0001, or similar.

According to example results from the process 400, the analytics system can yield a median (range) of 2,800 (1,500-12,000) fragments with anomalous methylation patterns for participants without cancer in training, and a median (range) of 3,000 (1,200-220,000) fragments with anomalous methylation patterns for participants with cancer in training. These filtered sets of fragments with anomalous methylation patterns may be used for the downstream analyses as described below in the sub-section titled "Filtration of anomalously methylated fragments."

P-Value Score Calculation

FIG. 5 is an illustration 500 of an example p-value score calculation, according to an embodiment. To calculate a p-value score given a test methylation state vector 505, the analytics system takes that test methylation state vector 505 and enumerates 410 possibilities of methylation state vectors. In this illustrative example, the test methylation state vector 505 is <M23, M24, M25, U26>. As the length of the test methylation state vector 505 is 4, there are $2^4$ possibilities of methylation state vectors encompassing CpG sites 23-26. In a generic example, the number of possibilities of methylation state vectors is $2^n$, where n is the length of the test methylation state vector or alternatively the length of the sliding window (described further below).

The analytics system calculates 420 probabilities 515 for the enumerated possibilities of methylation state vectors. As methylation is conditionally dependent on methylation state of nearby CpG sites, one way to calculate the probability of observing a given methylation state vector possibility is to use Markov chain model. Generally a methylation state vector such as $<S_1, S_2, \ldots, S_n>$, where S denotes the methylation state whether methylated (denoted as M), unmethylated (denoted as U), or indeterminate (denoted as I), has a joint probability that can be expanded using the chain rule of probabilities as:

$$P(<S_1, S_2, \ldots, S_n>) = P(S_n|S_1, \ldots, S_{n-1}) * P(S_{n-1}|S_1, \ldots, S_{n-2}) * \ldots * P(S_2|S_1) * P(S_1) \quad (1)$$

Markov chain model can be used to make the calculation of the conditional probabilities of each possibility more efficient. In one embodiment, the analytics system selects a Markov chain order k which corresponds to how many prior CpG sites in the vector (or window) to consider in the conditional probability calculation, such that the conditional probability is modeled as $P(S_n|S_1, \ldots, S_1, \ldots, S_{n-1}) \sim P(S_n|S_{n-k-2}, \ldots, S_{n-1})$.

To calculate each Markov modeled probability for a possibility of methylation state vector, the analytics system accesses the control group's data structure, specifically the counts of various strings of CpG sites and states. To calculate $P(M_n|S_{n-k-2}, \ldots, S_{n-1})$, the analytics system takes a ratio of the stored count of the number of strings from the data structure matching $<S_{n-k-2}, \ldots, S_{n-1}, M_n>$ divided by the sum of the stored count of the number of strings from the data structure matching $<S_{n-k-2}, \ldots, S_{n-1}, M_n>$ and $<S_{n-k-2}, \ldots, S_{n-1}, U_n>$. Thus, $P(M_n|S_{n-k-2}, \ldots, S_{n-1})$, is calculated ratio having the form:

$$\frac{\# \text{ of } <S_{n-k-2}, \ldots, S_{n-1}, M_n>}{\# \text{ of } <S_{n-k-2}, \ldots, S_{n-1}, M_n> + \# \text{ of } <S_{n-k-2}, \ldots, S_{n-1}, U_n>} \quad (2)$$

The calculation may additionally implement a smoothing of the counts by applying a prior distribution. In one embodiment, the prior distribution is a uniform prior as in Laplace smoothing. As an example of this, a constant is added to the numerator and another constant (e.g., twice the constant in the numerator) is added to the denominator of the above equation. In other embodiments, an algorithmic technique such as Knesser-Ney smoothing is used.

In the illustration, the above denoted formulas are applied to the test methylation state vector 505 covering sites 23-26. Once the calculated probabilities 515 are completed, the analytics system calculates 430 a p-value score 525 that sums the probabilities that are less than or equal to the probability of possibility of methylation state vector matching the test methylation state vector 505.

In embodiments with indeterminate states, the analytics system may calculate a p-value score summing out CpG sites with indeterminate states in a fragment's methylation state vector. The analytics system identifies all possibilities that have consensus with the all methylation states of the methylation state vector excluding the indeterminate states. The analytics system may assign the probability to the methylation state vector as a sum of the probabilities of the identified possibilities. As an example, the analytics system calculates a probability of a methylation state vector of $<M_1, I_2, U_3>$ as a sum of the probabilities for the possibilities of methylation state vectors of $<M_1, M_2, U_3>$ and $<M_1, U_2, U_3>$ since methylation states for CpG sites 1 and 3 are observed and in consensus with the fragment's methylation states at CpG sites 1 and 3. This method of summing out CpG sites with indeterminate states uses calculations of probabilities of possibilities up to $2^i$, wherein i denotes the number of indeterminate states in the methylation state vector. In additional embodiments, a dynamic programming algorithm may be implemented to calculate the probability of a methylation state vector with one or more indeterminate states. Advantageously, the dynamic programming algorithm operates in linear computational time.

In one embodiment, the computational burden of calculating probabilities and/or p-value scores may be further reduced by caching at least some calculations. For example, the analytic system may cache in transitory or persistent memory calculations of probabilities for possibilities of methylation state vectors (or windows thereof). If other fragments have the same CpG sites, caching the possibility probabilities allows for efficient calculation of p-value scores without needing to re-calculate the underlying possibility probabilities. Equivalently, the analytics system may calculate p-value scores for each of the possibilities of methylation state vectors associated with a set of CpG sites from vector (or window thereof). The analytics system may cache the p-value scores for use in determining the p-value scores of other fragments including the same CpG sites. Generally, the p-value scores of possibilities of methylation state vectors having the same CpG sites may be used to determine the p-value score of a different one of the possibilities from the same set of CpG sites.

Sliding Window

In one embodiment, the analytics system uses 435 a sliding window to determine possibilities of methylation state vectors and calculate p-values. Rather than enumerating possibilities and calculating p-values for entire methylation state vectors, the analytics system enumerates possibilities and calculates p-values for only a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window identifies the sequential set of CpG sites from the vector within the window starting from the first CpG site in the vector. The analytic system calculates a p-value score for the window including the first CpG site. The analytics system then "slides" the window to the second CpG site in the vector, and calculates another p-value score for the second window. Thus, for a window size/and methylation vector length m, each methylation state vector will generate m−l+l p-value scores. After completing the p-value calculations for each portion of the vector, the lowest p-value score from all sliding windows is taken as the overall p-value score for the methylation state vector. In another embodiment, the analytics system aggregates the p-value scores for the methylation state vectors to generate an overall p-value score.

Using the sliding window helps to reduce the number of enumerated possibilities of methylation state vectors and their corresponding probability calculations that would otherwise need to be performed. Example probability calculations are shown in FIG. 5, but generally the number of possibilities of methylation state vectors increases exponentially by a factor of 2 with the size of the methylation state vector. To give a realistic example, it is possible for fragments to have upwards of 54 CpG sites. Instead of computing probabilities for $2^{54}$ (~$1.8 \times 10^{16}$) possibilities to generate a single p-value score, the analytics system can instead use a window of size 5 (for example) which results in 50 p-value calculations for each of the 50 windows of the methylation state vector for that fragment. Each of the 50 calculations enumerates $2^5$ (32) possibilities of methylation state vectors, which total results in $50 \times 2^5$ ($1.6 \times 10^3$) probability calculations. This results in a vast reduction of calculations to be performed, with no meaningful hit to the accurate identification of anomalous fragments. This additional step can also be applied when validating 240 the control group with the validation group's methylation state vectors.

Filtration of Anomalously Methylated Fragments

In some embodiments, additional filtration step is performed to identify genomic regions that can be targeted for diagnosis of cancer or a type or stage of cancer.

Hypomethylated and Hypermethylated Fragments

Figure 6A:
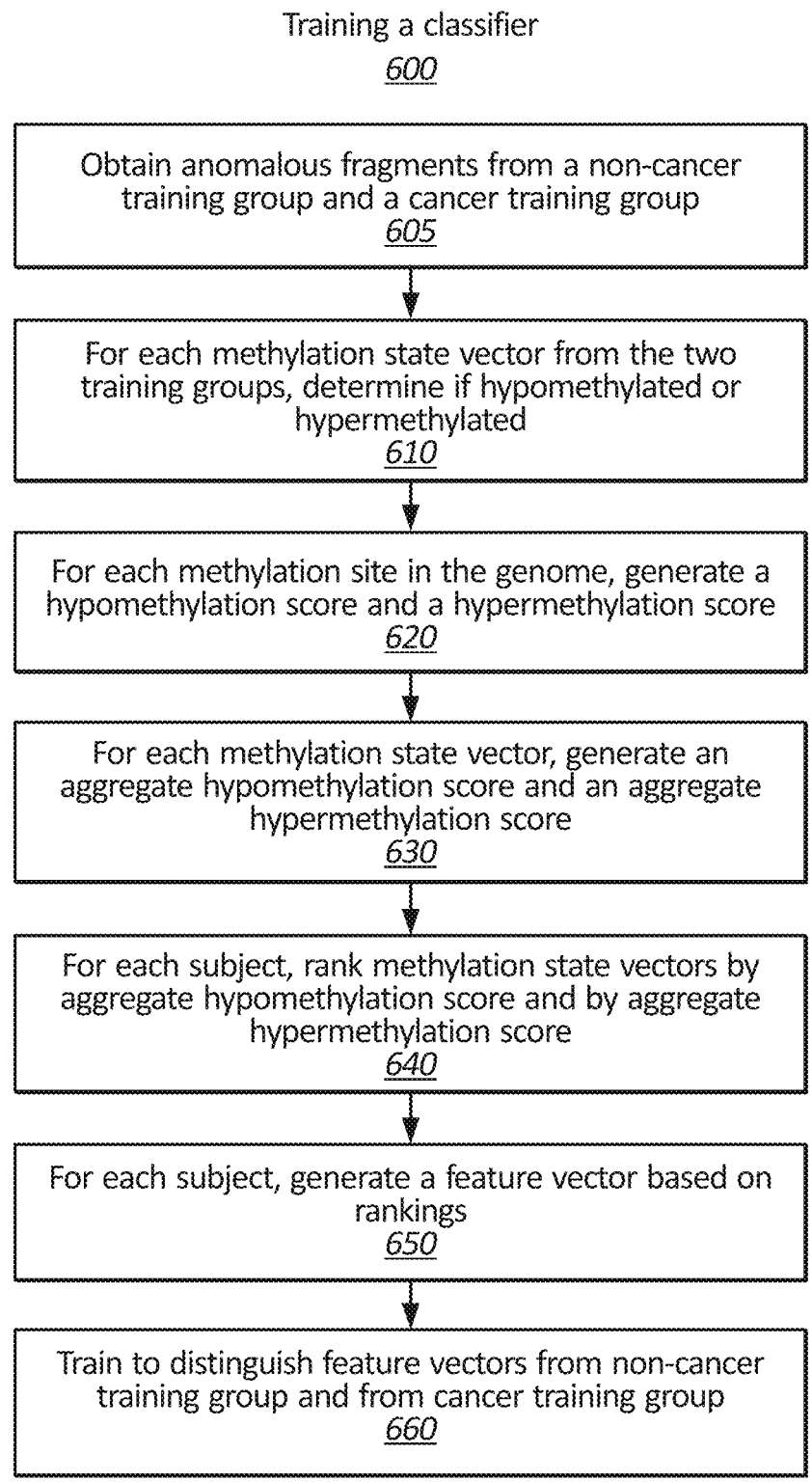
FIG. 6A is a flowchart describing a process of training a classifier based on hypomethylated and hypermethylated fragments indicative of cancer, according to an embodiment.

One additional analysis identifies 450 hypomethylated fragments or hypermethylated fragments from the filtered set. Fragments that are hypomethylated or hypermethylated may be defined as fragments of a certain length of CpG sites (e.g., more than 3, 4, 5, 6, 7, 8, 9, 10, etc.) with a high percentage of methylated CpG sites (e.g., more than 80%, 85%, 90%, or 95%, or any other percentage within the range of 50%-100%) or a high percentage of unmethylated CpG sites (e.g., more than 80%, 85%, 90%, or 95%, or any other percentage within the range of 50%-100%), respectively. FIGS. 6A-B, described below, illustrates an example process for identifying these hypomethylated or hypermethylated portions of a genome based on the set of anomalously methylated fragments.

Probabilistic Models

According to a second method, anomalous fragments are further filtered utilizing probabilistic models of methylation patterns fitted to either cancer type or non-cancer type. It calculates the log-odds ratio that the anomalous fragments from a subject are indicative of cancer generally, or of particular types of cancer. The log-odds ratio can be calculated by taking the log of a ratio of a probability of being cancerous over a probability of being non-cancerous (i.e., one minus the probability of being cancerous), both as determined by the applied 460 classification model.

In one embodiment of partitioning the genome, the analytics system partitions the genome into regions by multiple stages. In a first stage, the analytics system separates the genome into blocks of CpG sites. Each block is defined when there is a separation between two adjacent CpG sites that exceeds some threshold, e.g., greater than 200 bp, 300 bp, 400 bp, 500 bp, 600 bp, 700 bp, 800 bp, 900 bp, or 1,000 bp. From each block, the analytics system subdivides at a second stage each block into regions of a certain length, e.g., 500 bp, 600 bp, 700 bp, 800 bp, 900 bp, 1,000 bp, 1,100 bp, 1,200 bp, 1,300 bp, 1,400 bp, or 1,500 bp. The analytics system may further overlap adjacent regions by a percentage of the length, e.g., 10%, 20%, 30%, 40%, 50%, or 60%.

The analytics system analyzes sequence reads derived from DNA fragments for each region. The analytics system may process samples from tissue and/or high-signal cfDNA. High-signal cfDNA samples may be determined by a binary classification model, by cancer stage, or by another metric.

For each cancer type and non-cancer, the analytics system fits a separate probabilistic model for fragments. In one example, each probabilistic model is a mixture model comprising a combination of a plurality of mixture components with each mixture component being an independent-sites model where methylation at each CpG site is assumed to be independent of methylation statuses at other CpG sites.

In alternative embodiments, calculation is performed with respect to each CpG site. Specifically, a first count is determined that is the number of cancerous samples (cancer count) that include an anomalously methylated DNA fragment overlapping that CpG, and a second count is determined that is the total number of samples containing fragments overlapping that CpG (total) in the set. Genomic regions can be selected based on the numbers, for example, based on criteria positively correlated to the number of cancerous samples (cancer count) that include a DNA fragment overlapping that CpG, and inversely correlated to the total number of samples containing fragments overlapping that CpG (total) in the set.

The analytics system can further calculate log-likelihood ratios ("R") for a fragment indicating a likelihood of the fragment being indicative of cancer considering the various cancer types with the fitted probabilistic models for each cancer type and non-cancer type, or for a cancer tissue of origin. The two probabilities may be taken from probabilistic models fitted for each of the cancer types and the non-cancer type, the probabilistic models defined to calculate a likelihood of observing a methylation pattern on a fragment given each of the cancer types and the non-cancer type. For example, the probabilistic models may be fitted for each of the cancer types and the non-cancer type.

Figure 11A:
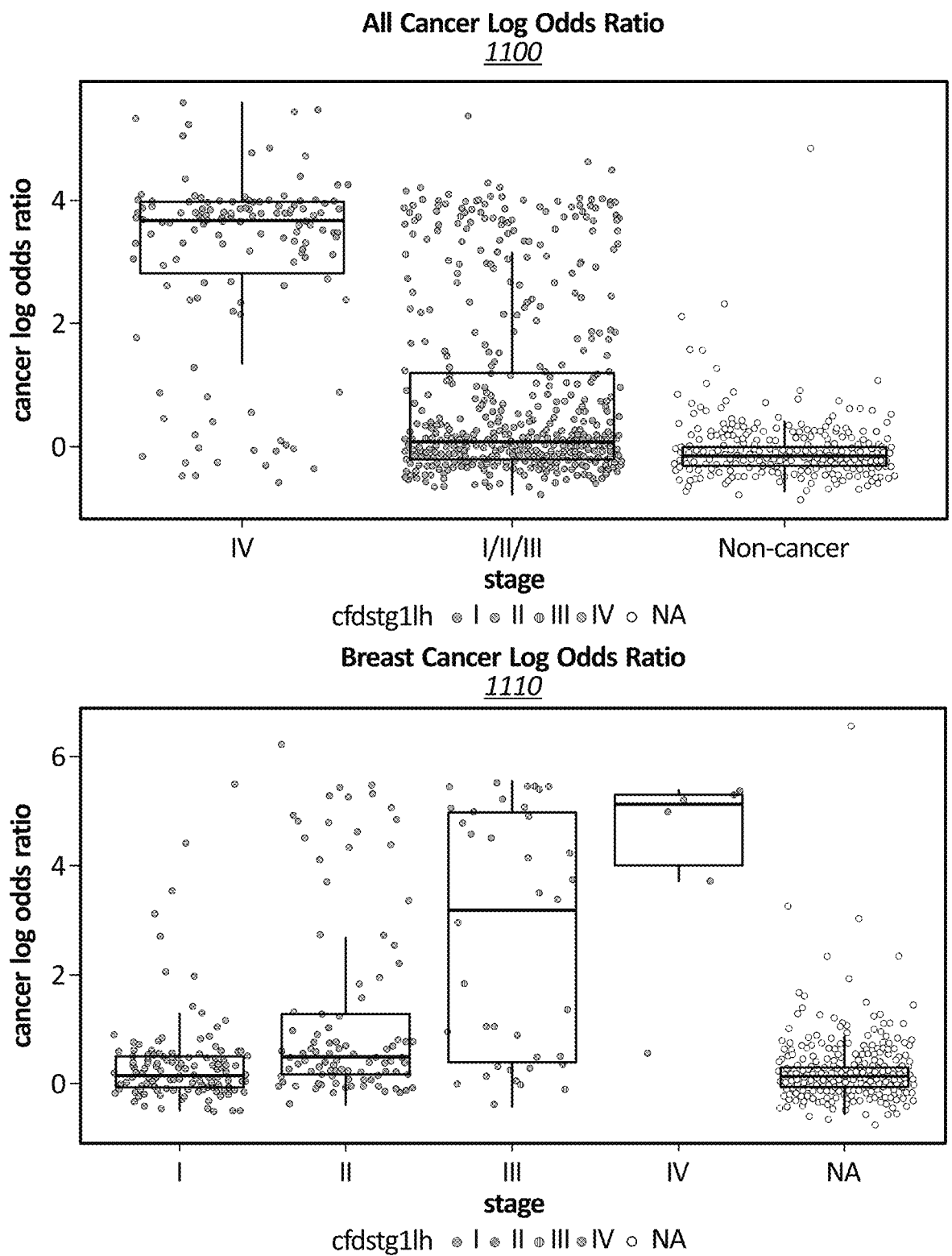

FIGS. 11A-11C show graphs of various cancers from various subjects across different stages, plotting the log-odds ratio of the anomalous fragments identified according to the process described with respect to FIG. 4 above. This underlying data was obtained via whole genome bisulfite sequencing of CCGA subjects (Clinical Trial.gov Identifier: NCT02889978 (https://www. clinicaltrials. gov/ct2/show/NCT02889978; see Example 3). Briefly, data was obtained for more than 1700 clinically evaluable subjects with over 1400 subjects filtered including nearly 600 subjects without cancer and just over 800 subjects with cancer. The first graph 1100 in FIG. 11A shows all cancer cases across three different levels—non-cancer; stage I/II/II; and stage IV. The cancer log-odds ratio for stage IV is significantly larger than those for stage I/II/II and non-cancer. The second graph 1110 in FIG. 11A shows breast cancer cases across all stages of cancer and non-cancer, with a similar progression in log-odds ratio increasing through the progressive stages of cancer. The third graph 1120 in FIG. 11B shows breast cancer sub-types. Noticeably sub-types HER2+ and TNBC are more spread out, whereas HR+/HER2− is concentrated closer to ~1. The fourth graph 1130 in FIG. 11C shows lung cancer cases across all stages of cancer and non-cancer with steady progression through progressive stages of the lung cancer. The fifth graph 1140 shows colorectal cancer cases across all stages of cancer and non-cancer, again showing steady progression through progressive stages of the colorectal cancer. The sixth graph 1150 in FIG. 11C shows prostate cancer cases across all stages of cancer and non-cancer. This example is different than most of the previously illustrated, only stage IV is significantly different compared to other stages I/II/II and non-cancer.

Genomic Regions Indicative of Cancer and Classifiers

The analytics system identifies 460 genomic regions indicative of cancer. To identify these informative regions, the analytics system calculates an information gain for each genomic region or more specifically each CpG site that describes an ability to distinguish between various outcomes.

A method for identifying genomic regions capable of distinguishing between cancer type and non-cancer type utilizes a trained classification model that can be applied on the set of anomalously methylated DNA molecules or fragments corresponding to, or derived from a cancerous or non-cancerous group. The trained classification model can be trained to identify any condition of interest that can be identified from the methylation state vectors.

In one embodiment, the trained classification model is a binary classifier trained based on methylation states for cfDNA fragments or genomic sequences obtained from a subject cohort with cancer or a cancer type, and a healthy subject cohort without cancer, and is then used to classify a test subject probability of having cancer, a cancer type, or not having cancer, based on methylation state vectors. In other embodiments, different classifiers may be trained using subject cohorts known to have particular cancer (e.g., breast, lung, prostrate, etc.); known to have cancer of particular tissue of origin where the cancer is believed to originate; or known to have different stages of particular cancer (e.g., breast, lung, prostrate, etc.). In these embodiments, different classifiers may be trained using sequence reads obtained from samples enriched for tumor cells from subject cohorts known to have particular cancer (e.g., breast, lung, prostrate, etc.). Each genomic region's ability to distinguish between cancer type and non-cancer type in the classification model is used to rank the genomic regions from most informative to least informative in classification performance. The analytics system may identify genomic regions from the ranking according to information gain in classification between non-cancer type and cancer type. Probes may be designed 470 to target the identified genome regions.

Computing Information Gain From Hypomethylated and Hypermethylated Fragments Indicative of Cancer With fragments indicative of cancer, the analytics system may train a classifier according to a process 600 illustrated in FIG. 6A, according to an embodiment. The process 600 accesses two training groups of samples—a non-cancer group and a cancer group—and obtains 605 a non-cancer set of methylation state vectors and a cancer set of methylation state vectors comprising anomalously methylated fragments, e.g., via step 440 from the process 400.

The process determines 610, for each methylation state vector, whether the methylation state vector is indicative of cancer. Here, fragments indicative of cancer may be defined as hypermethylated or hypomethylated fragments determined if at least some number of CpG sites have a particular state (methylated or unmethylated, respectively) and/or have a threshold percentage of sites that are the particular state (again, methylated or unmethylated, respectively). In one example, cfDNA fragments are identified as hypomethylated or hypermethylated, respectively, if the fragment overlaps at least 5 CpG sites, and at least 80% of its CpG sites are methylated or at least 80% are unmethylated. In an alternate embodiment, the process considers portions of the methylation state vector and determines whether the portion is hypomethylated or hypermethylated, and may distinguish that portion to be hypomethylated or hypermethylated. This alternative method resolves missing methylation state vectors which are large in size but contain at least one region of dense hypomethylation or hypermethylation. This process of defining hypomethylation and hypermethylation can be applied in step 450 of FIG. 4. In another embodiment, the fragments indicative of cancer may be defined according to likelihoods outputted from trained probabilistic models.

In one embodiment, the process generates 620 a hypomethylation score ($P_{hypo}$) and a hypermethylation score ($P_{hyper}$) per CpG site in the genome. To generate either score at hyper, a given CpG site, the classifier takes four counts at that CpG site—(1) count of (methylations state) vectors of the cancer set labeled hypomethylated that overlap the CpG site; (2) count of vectors of the cancer set labeled hypermethylated that overlap the CpG site; (3) count of vectors of the non-cancer set labeled hypomethylated that overlap the CpG site; and (4) count of vectors of the non-cancer set labeled hypermethylated that overlap the CpG site. Additionally, the process may normalize these counts for each group to account for variance in group size between the non-cancer group and the cancer group. In alternative embodiments wherein fragments indicative of cancer are more generally used, the scores may be more broadly defined as counts of fragments indicative of cancer at each genomic region and/or CpG site.

Specifically, in one embodiment, to generate 620 the hypomethylation score at a given CpG site, the process takes a ratio of (1) over (1) summed with (3). Similarly, the hypermethylation score is calculated by taking a ratio of (2) over (2) and (4). Additionally, these ratios may be calculated with an additional smoothing technique as discussed above. The hypomethylation score and the hypermethylation score relate to an estimate of cancer probability given the presence of hypomethylation or hypermethylation of fragments from the cancer set.

The process generates 630 an aggregate hypomethylation score and an aggregate hypermethylation score for each anomalous methylation state vector. The aggregate hyper and hypo methylation scores, are determined based on the hyper and hypo methylation scores of the CpG sites in the methylation state vector. In one embodiment, the aggregate hyper and hypo methylation scores are assigned as the largest hyper and hypo methylation scores of the sites in each state vector, respectively. However, in alternate embodiments, the aggregate scores could be based on means, medians, or other calculations that use the hyper/hypo methylation scores of the sites in each vector.

The process 600 ranks 640 all of that subject's methylation state vectors by their aggregate hypomethylation score and by their aggregate hypermethylation score, resulting in two rankings per subject. The process selects aggregate hypomethylation scores from the hypomethylation ranking and aggregate hypermethylation scores from the hypermethylation ranking. With the selected scores, the classifier generates 650 a single feature vector for each subject. In one embodiment, the scores selected from either ranking are selected with a fixed order that is the same for each generated feature vector for each subject in each of the training groups. As an example, in one embodiment the classifier selects the first, the second, the fourth, and the eighth aggregate hyper methylation score, and similarly for each aggregate hypo methylation score, from each ranking and writes those scores in the feature vector for that subject.

The process trains 660 a binary classifier to distinguish feature vectors between the cancer and non-cancer training groups. Generally, any one of a number of classification techniques may be used. In one embodiment the classifier is a non-linear classifier. In a specific embodiment, the classifier is a non-linear classifier utilizing a L2-regularized kernel logistic regression with a Gaussian radial basis function (RBF) kernel.

Specifically, in one embodiment, the number of non-cancer samples or different cancer type(s) ($n_{other}$) and the number of cancer samples or cancer type(s) ($n_{cancer}$) having an anomalously methylated fragment overlapping a CpG site are counted. Then the probability that a sample is cancer is estimated by a score ("S") that positively correlates to $n_{cancer}$ and inversely correlated to $n_{other}$. The score can be calculated using the equation: $(n_{cancer}+1)/(n_{cancer}+n_{other}+2)$ or $(n_{cancer})/(n_{cancer}+n_{other})$. The analytics system computes 670 an information gain for each cancer type and for each genomic region or CpG site to determine whether the genomic region or CpG site is indicative of cancer. The information gain is computed for training samples with a given cancer type compared to all other samples. For example, two random variables 'anomalous fragment' ('AF') and 'cancer type' ('CT') are used. In on embodiment, AF is a binary variable indicating whether there is an anomalous fragment overlapping a given CpG site in a given samples as determined for the anomaly score/feature vector above. CT is a random variable indicating whether the cancer is of a particular type. The analytics system computes the mutual information with respect to CT given AF. That is, how many bits of information about the cancer type are gained if it is known whether there is an anomalous fragment overlapping a particular CpG site.

For a given cancer type, the analytics system uses this information to rank CpG sites based on how cancer specific they are. This procedure is repeated for all cancer types under consideration. If a particular region is commonly anomalously methylated in training samples of a given cancer but not in training samples of other cancer types or in healthy training samples, then CpG sites overlapped by those anomalous fragments will tend to have high information gains for the given cancer type. The ranked CpG sites for each cancer type are greedily added (selected) to a selected set of CpG sites based on their rank for use in the cancer classifier.

Computing Pairwise Information Gain From Fragments Indicative of Cancer Identified From Probabilistic Models With fragments indicative of cancer identified according to the second method under the probabilistic models, the analytics may identify genomic regions according to the process 680 in FIG. 6B. The analytics system defines 690 a feature vector for each sample, for each region, for each cancer type by a count of DNA fragments that have a calculated log-likelihood ratio that the fragment is indicative of cancer above a plurality of thresholds, wherein each count is a value in the feature vector. In one embodiment, the analytics system counts the number of fragments present in a sample at a region for each cancer type with log-likelihood ratios above one or a plurality of possible threshold values. The analytics system defines a feature vector for each sample, by a count of DNA fragments for each genomic region for each cancer type that provides a calculated log-likelihood ratio for the fragment above a plurality of thresholds, wherein each count is a value in the feature vector. The analytics system uses the defined feature vectors to calculate an informative score for each genomic region describing that genomic region's ability to distinguish between each pair of cancer types. For each pair of cancer types, the analytics system ranks regions based on the informative scores. The analytics system may select regions based on the ranking according to informative scores.

The analytics system calculates 695 an informative score for each region describing that region's ability to distinguish between each pair of cancer types. For each pair of distinct cancer types, the analytics system may specify one type as a positive type and the other as a negative type. In one embodiment, a region's ability to distinguish between the positive type and the negative type is based on mutual information, calculated using the estimated fraction of cfDNA samples of the positive type and of the negative type for which the feature would be expected to be non-zero in the final assay, i.e., at least one fragment of that tier that would be sequenced in a targeted methylation assay. Those fractions are estimated using the observed rates at which the feature occurs in healthy cfDNA, and in high-signal cfDNA and/or tumor samples of each cancer type. For example, if a feature occurs frequently in healthy cfDNA, then it will also be estimated to occur frequently in cfDNA of any cancer type, and would likely result in a low informative score. The analytics system may choose a certain number of regions for each pair of cancer types from the ranking, e.g., 1024.

In additional embodiments, the analytics system further identifies predominantly hypermethylated or hypomethylated regions from the ranking of regions. The analytics system may load the set of fragments in the positive type(s) for a region that was identified as informative. The analytics system, from the loaded fragments, evaluates whether the loaded fragments are predominantly hypermethylated or hypomethylated. If the loaded fragments are predominately hypermethylated or hypomethylated, the analytics system may select probes corresponding to the predominant methylation pattern. If the loaded fragments are not predominantly hypermethylated or hypomethylated, the analytics system may use a mixture of probes for targeting both hypermethylation and hypomethylation. The analytics system may further identify a minimal set of CpG sites that overlap more than some percentage of the fragments.

In other embodiments, the analytics system, after ranking the regions based on informative scores, labels each region with the lowest informative ranking across all pairs of cancer types. For example, if a region was the 10th-most-informative region for distinguishing breast from lung, and the 5th-most-informative for distinguishing breast from colorectal, then it would be given an overall label of "5". The analytics system may design probes starting with the lowest-labeled regions while adding regions to the panel, e.g., until the panel's size budget has been exhausted.

Off-Target Genomic Regions

In some embodiments, probes targeting selected genomic regions are further filtered 475 based on the number of their off-target regions. This is for screening probes that pull down too many cfDNA fragments corresponding to, or derived from, off-target genomic regions. Exclusion of probes having many off-target regions can be valuable by decreasing off-target rates and increasing target coverage for a given amount of sequencing.

An off-target genomic region is a genomic region that has sufficient homology to a target genomic region, such that DNA molecules or fragments derived from off-target genomic regions are hybridized to and pulled down by a probe designed to hybridize to a target genomic region. An off-target genomic region can be a genomic region that aligns to a probe along at least 35 bp, 40 bp, 45 bp, 50 bp, 60 bp, 70 bp, or 80 bp with at least 80%, 85%, 90%, 95%, or 97% match rate. In one embodiment, an off-target genomic region is a genomic region that aligns to a probe along at least 45 bp with at least a 90% match rate. Various methods known in the art can be adopted to screen off-target genomic regions.

Exhaustively searching the genome to find all off-target genomic regions can be computationally challenging. In one embodiment, a k-mer seeding strategy (which can allow one or more mismatches) is combined to local alignment at the seed locations. In this case, exhaustive searching of good alignments can be guaranteed based on k-mer length, number of mismatches allowed, and number of k-mer seed hits at a particular location. This requires doing dynamic programing local alignment at a large number of locations, so this approach is highly optimized to use vector CPU instructions (e.g., AVX2, AVX512) and also can be parallelized across many cores within a machine and also across many machines connected by a network. A person of ordinary skill will recognize that modifications and variations of this approach can be implemented for the purpose of identifying off-target genomic regions.

In some embodiments, probes having sequence homology with off-target genomic regions, or DNA molecules corresponding to, or derived from off-target genomic regions comprising more than a threshold number are excluded (or filtered) from the panel. For example, probes having sequence homology with off-target genomic regions, or DNA molecules corresponding to, or derived from off-target genomic regions from more than 30, more than 25, more than 20, more than 18, more than 15, more than 12, more than 10, or more than 5 off-target regions are excluded.

In some embodiments, probes are divided into 2, 3, 4, 5, 6, or more separate groups depending on the numbers of off-target regions. For example, probes having sequence homology with no off-target regions or DNA molecules corresponding to, or derived from off-target regions are assigned to high-quality group, probes having sequence homology with 1-18 off-target regions or DNA molecules corresponding to, or derived from 1-18 off-target regions, are assigned to low-quality group, and probes having sequence homology with more than 19 off-target regions or DNA molecules corresponding to, or derived from 19 off-target regions, are assigned to poor-quality group. Other cut-off values can be used for the grouping.

In some embodiments, probes in the lowest quality group are excluded. In some embodiments, probes in groups other than the highest-quality group are excluded. In some embodiments, separate panels are made for the probes in each group. In some embodiments, all the probes are put on the same panel, but separate analysis is performed based on the assigned groups.

In some embodiments, a panel comprises a larger number of high-quality probes than the number of probes in lower groups. In some embodiments, a panel comprises a smaller number of poor-quality probes than the number of probes in other group. In some embodiments, more than 95%, 90%, 85%, 80%, 75%, or 70% of probes in a panel are high-quality probes. In some embodiments, less than 35%, 30%, 20%, 10%, 5%, 4%, 3%, 2% or 1% of the probes in a panel are low-quality probes. In some embodiments, less than 5%, 4%, 3%, 2% or 1% of the probes in a panel are poor-quality probes. In some embodiments, no poor-quality probes are included in a panel.

In some embodiments, probes having below 50%, below 40%, below 30%, below 20%, below 10% or below 5% are excluded. In some embodiments, probes having above 30%, above 40%, above 50%, above 60%, above 70%, above 80%, or above 90% are selectively included in a panel.

Methods of Using Cancer Assay Panel

In yet another aspect, methods of using a cancer assay panel are provided. The methods can comprise steps of treating DNA molecules or fragments to convert unmethylated cytosines to uracils (e.g., using bisulfite treatment), applying a cancer panel (as described herein) to the converted DNA molecules or fragments, enriching a subset of converted DNA molecules or fragments that hybridize (or bind) to the probes in the panel, and sequencing the enriched cfDNA fragments. The step of applying the cancer panel to the converted DNA molecules or fragments is performed in a condition where the converted DNA molecules or fragments can bind to probes on the cancer panel. Thus, converted DNA molecules or fragments bound to the probes can be selectively isolated. In some embodiments, the sequence reads can be compared to a reference genome (e.g., a human reference genome), allowing for identification of methylation states at a plurality of CpG sites within the DNA molecules or fragments and thus provide information relevant to diagnosis of cancer.

Sample Processing

Figure 7A:
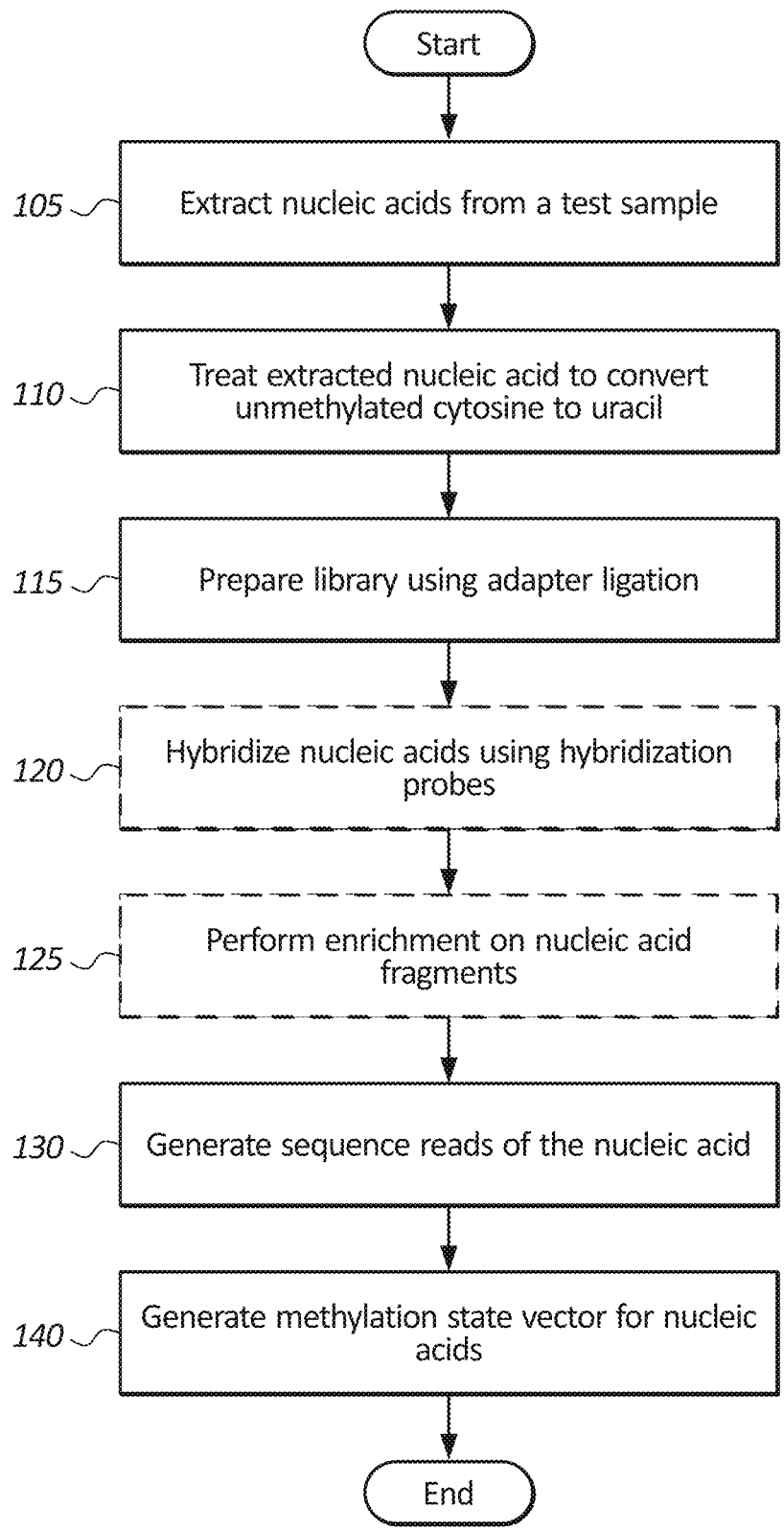
FIG. 7A is a flowchart describing a process of sequencing a fragment of cell-free (cf) DNA, according to an embodiment.

FIG. 7A is a flowchart of a method for preparing a nucleic acid sample for analyzing according to one embodiment. The method includes, but is not limited to, the following steps. For example, any step of the method may comprise a quantitation sub-step for quality control or other laboratory assay procedures known to one skilled in the art.

In step 105, a nucleic acid sample (DNA or RNA) is extracted from a subject. In the present disclosure, DNA and RNA may be used interchangeably unless otherwise indicated. That is, the embodiments described herein may be applicable to both DNA and RNA types of nucleic acid sequences. However, the examples described herein may focus on DNA for purposes of clarity and explanation. The sample may be any subset of the human genome, including the whole genome. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has a cancer or disease, ctDNA in an extracted sample may be present at a detectable level for diagnosis.

In step 110, the cfDNA fragments are treated to convert unmethylated cytosines to uracils. In one embodiment, the method uses a bisulfite treatment of the DNA which converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

In step 115, a sequencing library is prepared. In a first step, a ssDNA adapter is added to the 3'-OH end of a bisulfite-converted ssDNA molecule using a ssDNA ligation reaction. In one embodiment, the ssDNA ligation reaction uses CircLigase II (Epicentre) to ligate the ssDNA adapter to the 3'-OH end of a bisulfite-converted ssDNA molecule, wherein the 5'-end of the adapter is phosphorylated and the bisulfite-converted ssDNA has been dephosphorylated (i.e., the 3' end has a hydroxyl group). In another embodiment, the ssDNA ligation reaction uses Thermostable 5' AppDNA/RNA ligase (available from New England BioLabs (Ipswich, MA)) to ligate the ssDNA adapter to the 3'-OH end of a bisulfite-converted ssDNA molecule. In this example, the first UMI adapter is adenylated at the 5'-end and blocked at the 3'-end. In another embodiment, the ssDNA ligation reaction uses a T4 RNA ligase (available from New England BioLabs) to ligate the ssDNA adapter to the 3'-OH end of a bisulfate-converted ssDNA molecule. In a second step, a second strand DNA is synthesized in an extension reaction. For example, an extension primer that hybridizes to a primer sequence included in the ssDNA adapter is used in a primer extension reaction to form a double-stranded bisulfate-converted DNA molecule. Optionally, in one embodiment, the extension reaction uses an enzyme that is able to read through uracil residues in the bisulfite-converted template strand. Optionally, in a third step, a dsDNA adapter is added to the double-stranded bisulfate-converted DNA molecule. Finally, the double-stranded bisulfite-converted DNA is amplified to add sequencing adapters. For example, PCR amplification using a forward primer that includes a P5 sequence and a reverse primer that includes a P7 sequence is used to add P5 and P7 sequences to the bisulfate-converted DNA. Optionally, during library preparation, unique molecular identifiers (UMI) may be added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment, which provides a way to identify sequence reads that came from the same original fragment in downstream analysis.

In step 120, targeted DNA sequences may be enriched from the library (e.g., via hybridization). Any suitable method of enrichment may be used. For instance, in some embodiments, a targeted panel assay is performed on (e.g., comes into contact with) the samples. During enrichment, hybridization probes (also referred to herein as "probes") can be used to target and pull down nucleic acid fragments informative for the presence or absence of cancer (or disease), cancer status, or a cancer classification (e.g., cancer type or tissue of origin). For a given workflow, the probes may be designed to anneal (or hybridize) to a target (complementary) strand of DNA or RNA. The target strand may be the "positive" strand (e.g., the strand transcribed into mRNA, and subsequently translated into a protein) or the complementary "negative" strand. The probes may range in length from 10s, 100s, or 1000s of base pairs. Moreover, the probes may cover overlapping portions of a target region.

In some instances, primers may be used to specifically amplify targets/biomarkers of interest (e.g., by PCR), thereby enriching the sample for desired targets/biomarkers (optionally without hybridization capture). For example, forward and reverse primers can be prepared for each genomic region of interest and used to amplify fragments that correspond to or are derived from the desired genomic region. Thus, while the present disclosure pays particular attention to cancer assay panels and bait sets, the disclosure is broad enough to encompass other methods for enrichment of cell-free DNA. Accordingly, a skilled artisan, with the benefit of this disclosure, will recognize that methods analogous to those described herein in connection with hybridization capture can alternatively be accomplished by replacing hybridization capture with some other enrichment strategy, such as PCR amplification of cell-free DNA fragments that correspond with genomic regions of interest. In some embodiments, bisulfite padlock probe capture is used to enrich regions of interest, such as is described in Zhang et al. (US 2016/0340740). In some embodiments, additional or alternative methods are used for enrichment (e.g., non-targeted enrichment) such as reduced representation bisulfite sequencing, methylation restriction enzyme sequencing, methylation DNA immunoprecipitation sequencing, methyl-CpG-binding domain protein sequencing, methyl DNA capture sequencing, or microdroplet PCR.

After pull down and/or hybridization (see step 120), the hybridized nucleic acid fragments may optionally also be amplified using PCR (enrichment 125). For example, the target sequences can be enriched to obtain enriched sequences that can be subsequently sequenced. In general, any known method in the art can be used to isolate, and enrich for, probe-hybridized target nucleic acids. For example, as is well known in the art, a biotin moiety can be added to the 5'-end of the probes (i.e., biotinylated) to facilitate isolation of target nucleic acids hybridized to probes using a streptavidin-coated surface (e.g., streptavidin-coated beads). Nucleic acid fragments are applied to a panel comprising the probes in the condition that allows specific binding of the nucleic acid fragments to complementary probes. Thus, it enables selective isolation and enrichment of nucleic acid fragments that have high affinity to the probes.

In step 130, sequence reads are generated from the enriched DNA sequences, e.g., enriched sequences. Sequencing data may be acquired from the enriched DNA sequences by known means in the art. For example, the method may include next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

Analysis of Sequence Reads

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary alignment map) format may be generated and output for further analysis.

From the sequence reads, the location and methylation state for each of CpG site may be determined based on alignment to a reference genome. Further, a methylation state vector for each fragment may be generated specifying a location of the fragment in the reference genome (e.g., as specified by the position of the first CpG site in each fragment, or another similar metric), a number of CpG sites in the fragment, and the methylation state of each CpG site in the fragment whether methylated (e.g., denoted as M), unmethylated (e.g., denoted as U), or indeterminate (e.g., denoted as I). The methylation state vectors may be stored in temporary or persistent computer memory for later use and processing. Further, duplicate reads or duplicate methylation state vectors from a single subject may be removed. In an additional embodiment, it may be determined that a certain fragment has one or more CpG sites that have an indeterminate methylation status. Such fragments may be excluded from later processing or selectively included where downstream data model accounts for such indeterminate methylation statuses.

Figure 7B:
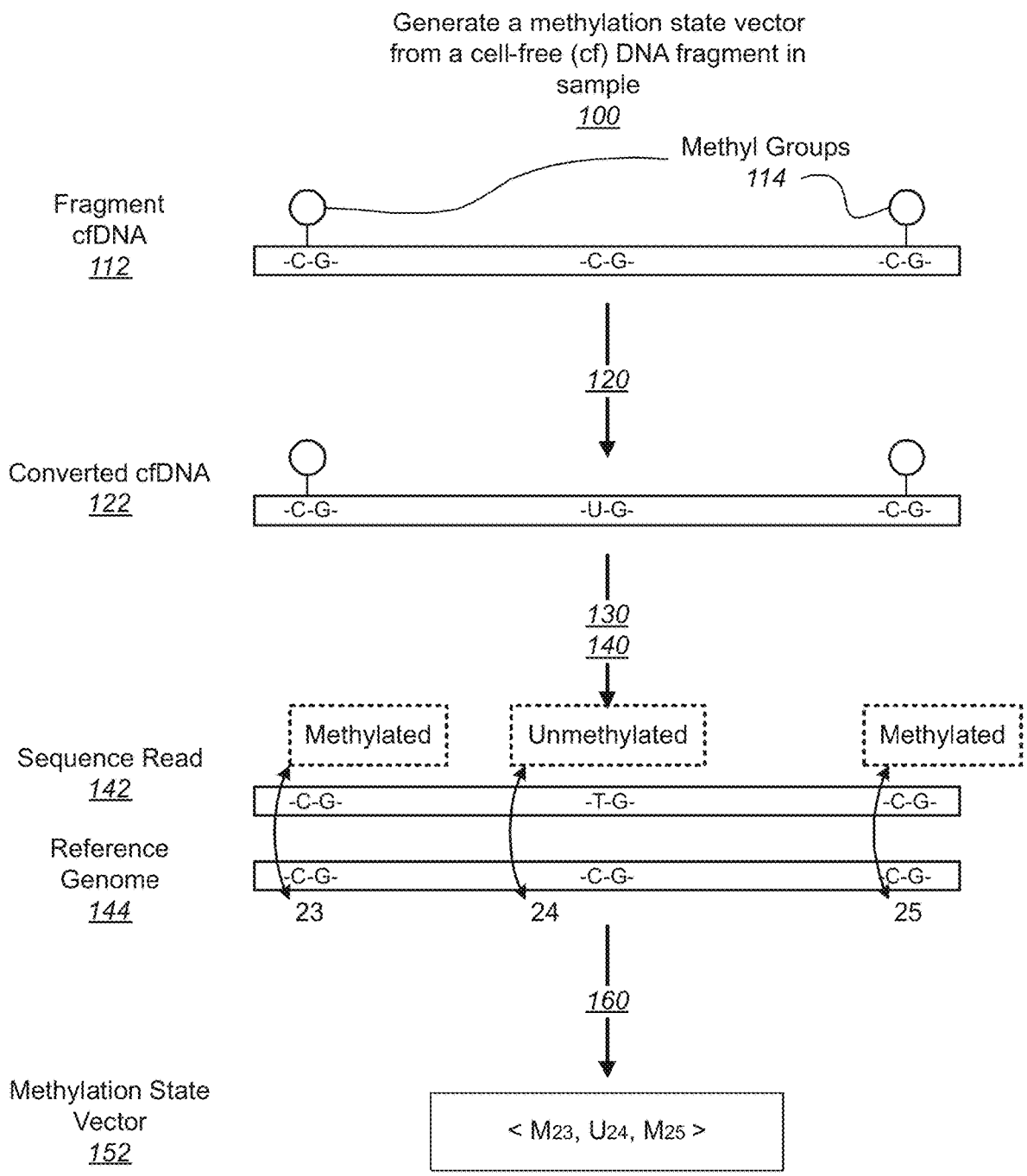
FIG. 7B is an illustration of the process of FIG. 7A of sequencing a fragment of cell-free (cf) DNA to obtain a methylation state vector, according to an embodiment.

FIG. 7B is an illustration of the process 100 of FIG. 7A of sequencing a cfDNA fragment to obtain a methylation state vector, according to an embodiment. As an example, the analytics system takes a cfDNA fragment 112. In this example, the cfDNA fragment 112 contains three CpG sites. As shown, the first and third CpG sites of the cfDNA fragment 112 are methylated 114. During the treatment step 120, the cfDNA fragment 112 is converted to generate a converted cfDNA fragment 122. During the treatment 120, the second CpG site which was unmethylated has its cytosine converted to uracil. However, the first and third CpG sites are not converted.

After conversion, a sequencing library 130 is prepared and sequenced 140 generating a sequence read 142. The analytics system aligns 150 the sequence read 142 to a reference genome 144. The reference genome 144 provides the context as to what position in a human genome the fragment cfDNA originates from. In this simplified example, the analytics system aligns 150 the sequence read such that the three CpG sites correlate to CpG sites 23, 24, and 25 (arbitrary reference identifiers used for convenience of description). The analytics system thus generates information both on methylation status of all CpG sites on the cfDNA fragment 112 and which to position in the human genome the CpG sites map. As shown, the CpG sites on sequence read 142 which were methylated are read as cytosines. In this example, the cytosines appear in the sequence read 142 only in the first and third CpG site which allows one to infer that the first and third CpG sites in the original cfDNA fragment were methylated. Whereas, the second CpG site is read as a thymine (U is converted to T during the sequencing process), and thus, one can infer that the second CpG site was unmethylated in the original cfDNA fragment. With these two pieces of information, the methylation status and location, the analytics system generates 160 a methylation state vector 152 for the fragment cfDNA 112. In this example, the resulting methylation state vector 152 is $<M_{23}, U_{24}, M_{25}>$, wherein M corresponds to a methylated CpG site, U corresponds to an unmethylated CpG site, and the subscript number corresponds to a position of each CpG site in the reference genome.

Figure 13A:
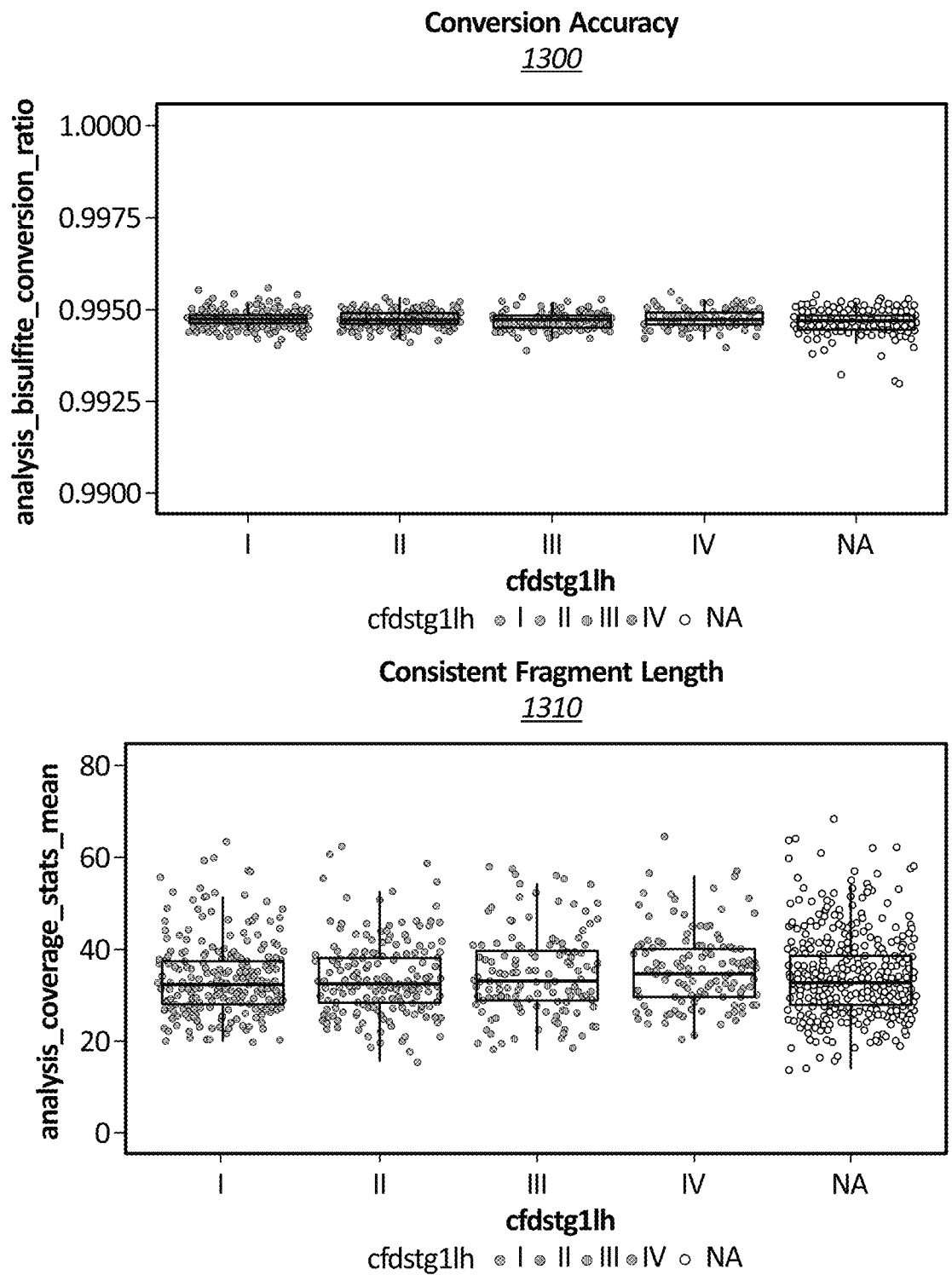
FIGS. 13A & 13B show three graphs of data validating consistency of sequencing from a control group.
Figure 13B:
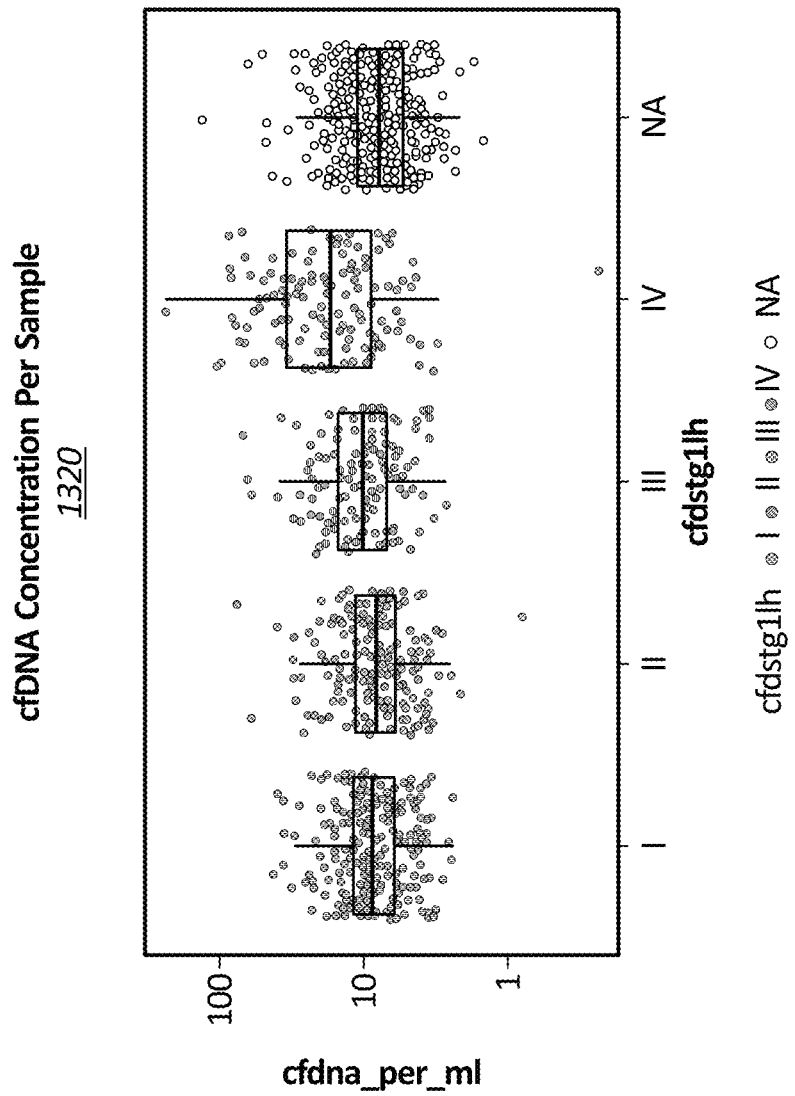

FIGS. 13A & 13B show three graphs of data validating consistency of sequencing from a control group. The first graph 1300 shows conversion accuracy of conversion of unmethylated cytosines to uracil (step 120) on cfDNA fragment obtained from a test sample across subjects in varying stages of cancer—stage 0, stage I, stage II, stage III, stage IV, and non-cancer. As shown, there was uniform consistency in converting unmethylated cytosines on cfDNA fragments into uracils. There was an overall conversion accuracy of 99.47% with a precision at ±0.024%. The second graph 1310 shows mean coverage over varying stages of cancer. The mean coverage over all groups being ~34× mean across the genome coverage of DNA fragments, using only those confidently mapped to the genome are counted. The third graph 1320 (FIG. 13B) shows concentration of cfDNA per sample across varying stages of cancer.

Diagnosis of Cancer

Sequence reads obtained by the methods provided herein can be further processed by automated algorithms. For example, the analytics system is used to receive sequencing data from a sequencer and perform various aspects of processing as described herein. The analytics system can be one of a personal computer (PC), a desktop computer, a laptop computer, a notebook, a tablet PC, a mobile device. A computing device can be communicatively coupled to the sequencer through a wireless, wired, or a combination of wireless and wired communication technologies. Generally, the computing device is configured with a processor and memory storing computer instructions that, when executed by the processor, cause the processor to perform steps as described in the remainder of this document. Generally, the amount of genetic data and data derived therefrom is sufficiently large, and the amount of computational power required so great, so as to be impossible to be performed on paper or by the human mind alone.

The clinical interpretation of methylation status of targeted genomic regions is a process that includes classifying the clinical effect of each or a combination of the methylation status and reporting the results in ways that are meaningful to a medical professional. The clinical interpretation can be based on comparison of the sequence reads with database specific to cancer or non-cancer subjects, and/or based on numbers and types of the cfDNA fragments having cancer-specific methylation patterns identified from a sample. In some embodiments, targeted genomic regions are ranked or classified based on their likeness to be differentially methylated in cancer samples, and the ranks or classifications are used in the interpretation process. The ranks and classifications can include (1) the type of clinical effect, (2) the strength of evidence of the effect, and (3) the size of the effect. Various methods for clinical analysis and interpretation of genome data can be adopted for analysis of the sequence reads. In some other embodiments, the clinical interpretation of the methylation states of such differentially methylated regions can be based on machine learning approaches that interpret a current sample based on a classification or regression method that was trained using the methylation states of such differentially methylated regions from samples from cancer and non-cancer patients with known cancer status, cancer type, cancer stage, tissue of origin, etc.

The clinically meaningful information can include the presence or absence of cancer generally, presence or absence of certain types of cancers, cancer stage, or presence or absence of other types of diseases. In some embodiments, the information relates to a presence or absence of one or more cancer types, selected from the group consisting of (1) blood cancer, (2) breast cancer, (3) colorectal cancer, (4) esophageal cancer, (5) head and neck cancer, (6) hepatobiliary cancer, (7) lung cancer, (8) ovarian cancer, and (9) pancreatic cancer.

Cancer Classifier

To train a cancer type classifier, the analytics system obtains a plurality of training samples each having a set of hypomethylated and hypermethylated fragments indicative of cancer, e.g., identified via step 450 in the process 400, and a label of the training sample's cancer type. The analytics system determines, for each training sample, a feature vector based on the set of hypomethylated and hypermethylated fragments indicative of cancer. The analytics system calculates an anomaly score for each CpG site in the targeted genomic regions. In one embodiment, the analytics system defines the anomaly score for the feature vector as a binary scoring based on whether there is a hypomethylated or hypermethylated fragment from the set that encompasses the CpG site. Once all anomaly scores are determined for a training sample, the analytics system determines the feature vector as a vector of elements including, for each element, one of the anomaly scores associated with one of the CpG sites. The analytics system may normalize the anomaly scores of the feature vector based on a coverage of the sample, i.e., a median or average sequencing depth over all CpG sites.

With the feature vectors of the training samples, the analytics system can train the cancer classifier. In one embodiment, the analytics system trains a binary cancer classifier to distinguish between the labels, cancer and non-cancer, based on the feature vectors of the training samples. In this embodiment, the classifier outputs a prediction score indicating the likelihood of the presence or absence of cancer. In another embodiment, the analytics system trains a multiclass cancer classifier to distinguish between many cancer types. In this multiclass cancer classifier embodiment, the cancer classifier is trained to determine a cancer prediction that comprises a prediction value for each of the cancer types being classified for. The prediction values may correspond to a likelihood that a given sample has each of the cancer types. For example, the cancer classifier returns a cancer prediction including a prediction value for breast cancer, lung cancer, and non-cancer. For example, the cancer classifier may return a cancer prediction for a test sample including a prediction score for breast cancer, lung cancer, and/or no cancer. In either embodiment, the analytics system trains the cancer classifier by inputting sets of training samples with their feature vectors into the cancer classifier and adjusting classification parameters so that a function of the classifier accurately relates the training feature vectors to their corresponding label. The analytics system may group the training samples into sets of one or more training samples for iterative batch training of the cancer classifier. After inputting all sets of training samples including their training feature vectors and adjusting the classification parameters, the cancer classifier is sufficiently trained to label test samples according to their feature vector within some margin of error. The analytics system may train the cancer classifier according to any one of a number of methods. As an example, the binary cancer classifier may be a L2-regularized logistic regression classifier that is trained using a log-loss function. As another example, the multi-cancer classifier may be a multinomial logistic regression. In practice either type of cancer classifier may be trained using other techniques. These techniques are numerous including potential use of kernel methods, machine learning algorithms such as multilayer neural networks, etc. In particular, methods as described in PCT/US2019/022122 and U.S. patent application Ser. No. 16/352,602 which are incorporated by reference in their entireties herein can be used for various embodiments.

In particular embodiments, a cancer classifier is trained by the process comprising the steps of: a. obtaining sequence information of training fragments from a plurality of training subjects; b. for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, c. for each training subject, generating a training feature vector based on the hypomethylated training fragments and hypermethylated training fragments, and d. training the model with the training feature vectors from the one or more training subjects without cancer and the training feature vectors from the one or more training subjects with cancer. The training method can further comprise the steps of: a. obtaining sequence information of training fragments from a plurality of training subjects; b. for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, c. for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; d. for each training fragment, generating an aggregate hypomethylation score based on the hypomethylation score of the CpG sites in the training fragment and an aggregate hypermethylation score based on the hypermethylation score of the CpG sites in the training fragment; e. for each training subject: ranking the plurality of training fragments based on aggregate hypomethylation score and ranking the plurality of training fragments based on aggregate hypermethylation score; and generating a feature vector based on the ranking of the training fragments; f obtaining training feature vectors for one or more training subjects without cancer and training feature vectors for the one or more training subjects with cancer; and g. training the model with the feature vectors for the one or more training subjects without cancer and the feature vectors for the one or more training subjects with cancer. In some embodiments, the model comprises one of a kernel logistic regression classifier, a random forest classifier, a mixture model, a convolutional neural network, and an autoencoder model.

In some embodiments, quantifying a count of hypomethylated training fragments which overlap that CpG site and a count of hypermethylated training fragments which overlap that CpG site further comprises: a. quantifying a cancer count of hypomethylated training fragments from the one or more training subjects with cancer that overlap that CpG site and a non-cancer count of hypomethylated training fragments from the one or more training subjects without cancer that overlap that CpG site; and b. quantifying a cancer count of hypermethylated training fragments from the one or more training subjects with cancer that overlap that CpG site and a non-cancer count of hypermethylated training fragments from the one or more training subjects without cancer that overlap that CpG site. In some embodiments, generating a hypomethylation score and a hypermethylation score based on the count of hypomethylated training fragments and hypermethylated training fragments further comprises: a. for generating the hypomethylation score, calculating a hypomethylation ratio of the cancer count of hypomethylated training fragments over a hypomethylation sum of the cancer count of hypomethylated training fragments and the non-cancer count of hypomethylated training fragments; and b. for generating the hypermethylation score, calculating a hypermethylation ratio of the cancer count of hypermethylated training fragments over a hypermethylation sum of the cancer count of hypermethylated training fragments and the non-cancer count of hypermethylated training fragments.

During deployment, the analytics system obtains sequence reads from a test sample collected from a subject. Various sequencing methods available in the art can be used to obtain sequence reads. In some embodiments, the sequence reads are obtained from whole genome sequencing or targeted sequencing. In some embodiments, the sequence reads include a set of sequence reads of modified test fragments, wherein the modified test fragments are obtained by processing a set of nucleic acid fragments, wherein each of the nucleic acid fragments corresponds to or is derived from a plurality of genomic regions selected from one or more of Tables 1-24. In some embodiments, the sequence reads are from the DNA samples enriched using the assay panel described herein.

The analytics system processes the sequence reads to obtain a test feature vector in a similar process as described for the training samples. In some embodiments, the test feature vector is obtained by the process comprising a. for each of the nucleic acid fragments, determining whether the nucleic acid fragment is hypomethylated or hypermethylated, wherein each of the hypomethylated and hypermethylated nucleic acid fragments comprises at least a threshold number of CpG sites with at least a threshold percentage of the CpG sites being unmethylated or methylated, respectively; b. for each of a plurality of CpG sites in a reference genome: quantifying a count of hypomethylated nucleic acid fragments which overlap the CpG site and a count of hypermethylated nucleic acid fragments which overlap the CpG site; and generating a hypomethylation score and a hypermethylation score based on the count of hypomethylated nucleic acid fragments and hypermethylated nucleic acid fragments; c. for each nucleic acid fragment, generating an aggregate hypomethylation score based on the hypomethylation score of the CpG sites in the nucleic acid fragment and an aggregate hypermethylation score based on the hypermethylation score of the CpG sites in the nucleic acid fragment; d. ranking the plurality of nucleic acid fragments based on aggregate hypomethylation score and ranking the plurality of nucleic fragments based on aggregate hypermethylation score; and e. generating the test feature vector based on the ranking of the nucleic acid fragments.

The analytics system then inputs the test feature vector into the trained cancer classifier to yield a cancer prediction, e.g., binary prediction (cancer or non-cancer) or multiclass cancer prediction (prediction score for each of a plurality of cancer types). In some embodiments, the analytics system outputs a cancer probability for the test sample. The cancer probability can be compared to a threshold probability to determine whether the test sample is from a subject with cancer or without cancer.

Exemplary Sequencer and Analytics System

Figure 8A:
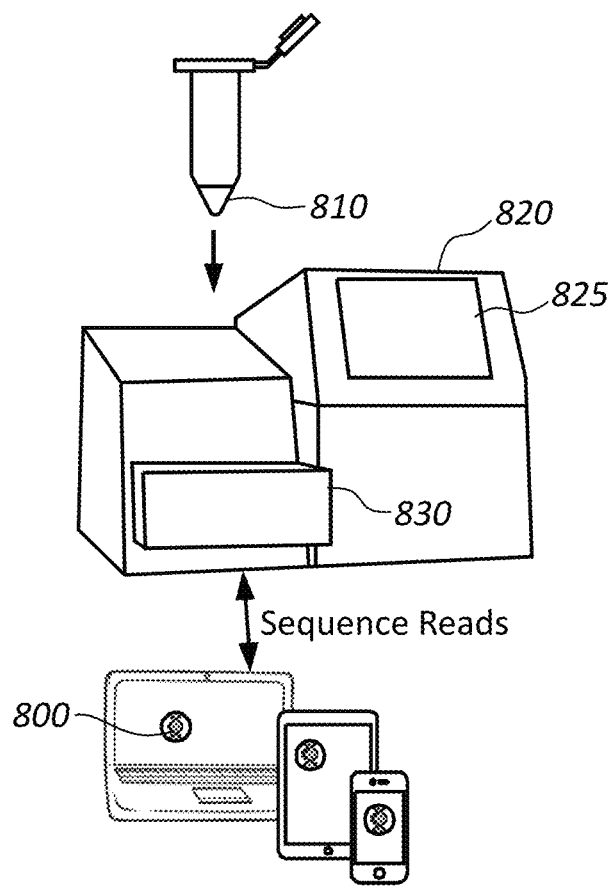
FIG. 8A is a flowchart of devices for sequencing nucleic acid samples according to one embodiment.

FIG. 8A is a flowchart of systems and devices for sequencing nucleic acid samples according to one embodiment. This illustrative flowchart includes devices such as a sequencer 820 and an analytics system 800. The sequencer 820 and the analytics system 800 may work in tandem to perform one or more steps in the processes described herein.

In various embodiments, the sequencer 820 receives an enriched nucleic acid sample 810. As shown in FIG. 8A, the sequencer 820 can include a graphical user interface 825 that enables user interactions with particular tasks (e.g., initiate sequencing or terminate sequencing) as well as one more loading stations 830 for loading a sequencing cartridge including the enriched fragment samples and/or for loading necessary buffers for performing the sequencing assays. Therefore, once a user of the sequencer 820 has provided the necessary reagents and sequencing cartridge to the loading station 830 of the sequencer 820, the user can initiate sequencing by interacting with the graphical user interface 825 of the sequencer 820. Once initiated, the sequencer 820 performs the sequencing and outputs the sequence reads of the enriched fragments from the nucleic acid sample 810.

In some embodiments, the sequencer 820 is communicatively coupled with the analytics system 800. The analytics system 800 includes some number of computing devices used for processing the sequence reads for various applications such as assessing methylation status at one or more CpG sites, variant calling or quality control. The sequencer 820 may provide the sequence reads in a BAM file format to the analytics system 800. The analytics system 800 can be communicatively coupled to the sequencer 820 through a wireless, wired, or a combination of wireless and wired communication technologies. Generally, the analytics system 800 is configured with a processor and non-transitory computer-readable storage medium storing computer instructions that, when executed by the processor, cause the processor to process the sequence reads or to perform one or more steps of any of the methods or processes disclosed herein.

In some embodiments, the sequence reads may be aligned to a reference genome using known methods in the art to determine alignment position information, e.g., part of step 140 of the process 100 in FIG. 3A. Alignment position may generally describe a beginning position and an end position of a region in the reference genome that corresponds to a beginning nucleotide based and an end nucleotide base of a given sequence read. Corresponding to methylation sequencing, the alignment position information may be generalized to indicate a first CpG site and a last CpG site included in the sequence read according to the alignment to the reference genome. The alignment position information may further indicate methylation statuses and locations of all CpG sites in a given sequence read. A region in the reference genome may be associated with a gene or a segment of a gene; as such, the analytics system 800 may label a sequence read with one or more genes that align to the sequence read. In one embodiment, fragment length (or size) is determined from the beginning and end positions.

In various embodiments, for example when a paired-end sequencing process is used, a sequence read is comprised of a read pair denoted as R_1 and R_2. For example, the first read R_1 may be sequenced from a first end of a double-stranded DNA (dsDNA) molecule whereas the second read R_2 may be sequenced from the second end of the double-stranded DNA (dsDNA). Therefore, nucleotide base pairs of the first read R_1 and second read R_2 may be aligned consistently (e.g., in opposite orientations) with nucleotide bases of the reference genome. Alignment position information derived from the read pair R_1 and R_2 may include a beginning position in the reference genome that corresponds to an end of a first read (e.g., R_1) and an end position in the reference genome that corresponds to an end of a second read (e.g., R_2). In other words, the beginning position and end position in the reference genome represent the likely location within the reference genome to which the nucleic acid fragment corresponds. An output file having SAM (sequence alignment map) format or BAM (binary) format may be generated and output for further analysis.

Figure 8B:
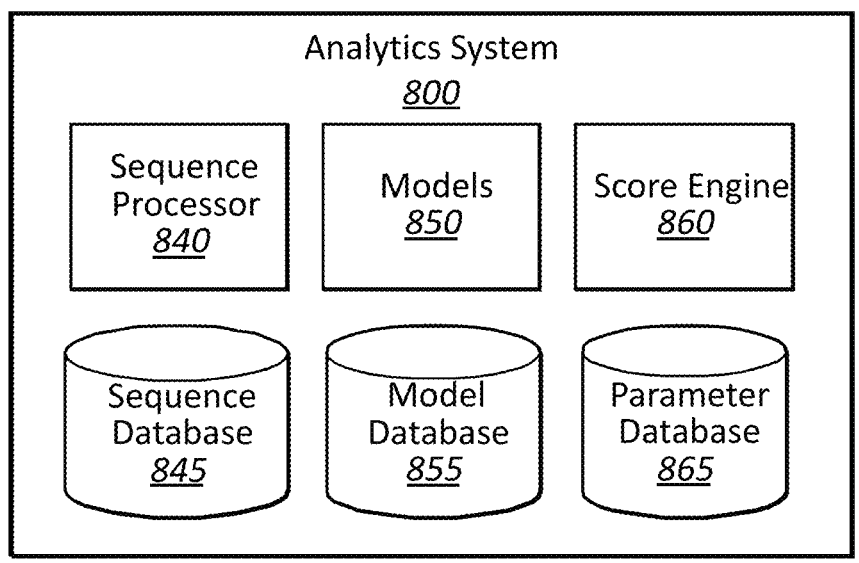
FIG. 8B provides an analytic system that analyzes methylation status of cfDNA according to one embodiment.

Referring now to FIG. 8B, FIG. 8B is a block diagram of an analytics system 800 for processing DNA samples according to one embodiment. The analytics system implements one or more computing devices for use in analyzing DNA samples. The analytics system 800 includes a sequence processor 840, sequence database 845, model database 855, models 850, parameter database 865, and score engine 860. In some embodiments, the analytics system 800 performs one or more steps in the processes 100 of FIG. 3A, 340 of FIG. 3B, 400 of FIG. 4, 500 of FIG. 5, 600 of FIG. 6A, or 680 of FIG. 6B and other process described herein.

The sequence processor 840 generates methylation state vectors for fragments from a sample. At each CpG site on a fragment, the sequence processor 840 generates a methylation state vector for each fragment specifying a location of the fragment in the reference genome, a number of CpG sites in the fragment, and the methylation state of each CpG site in the fragment whether methylated, unmethylated, or indeterminate via the process 100 of FIG. 3A. The sequence processor 840 may store methylation state vectors for fragments in the sequence database 845. Data in the sequence database 845 may be organized such that the methylation state vectors from a sample are associated to one another.

Further, multiple different models 850 may be stored in the model database 855 or retrieved for use with test samples. In one example, a model is a trained cancer classifier for determining a cancer prediction for a test sample using a feature vector derived from anomalous fragments. The training and use of the cancer classifier will be further discussed in conjunction with sub-section titled "Genomic regions indicative of cancer and classifiers." The analytics system 800 may train the one or more models 850 and store various trained parameters in the parameter database 865. The analytics system 800 stores the models 850 along with functions in the model database 855.

During inference, the score engine 860 uses the one or more models 850 to return outputs. The score engine 860 accesses the models 850 in the model database 855 along with trained parameters from the parameter database 865. According to each model, the score engine receives an appropriate input for the model and calculates an output based on the received input, the parameters, and a function of each model relating the input and the output. In some use cases, the score engine 860 further calculates metrics correlating to a confidence in the calculated outputs from the model. In other use cases, the score engine 860 calculates other intermediary values for use in the model Application In some embodiments, the methods, analytic systems and/or classifier of the present invention can be used to detect the presence of cancer, monitor cancer progression or recurrence, monitor therapeutic response or effectiveness, determine a presence or monitor minimum residual disease (MRD), or any combination thereof. For example, as described herein, a classifier can be used to generate a likelihood or probability score (e.g., from 0 to 100) that a sample feature vector is from a subject with cancer. In some embodiments, the probability score is compared to a threshold probability to determine whether or not the subject has cancer. In other embodiments, the likelihood or probability score can be assessed at different time points (e.g., before or after treatment) to monitor disease progression or to monitor treatment effectiveness (e.g., therapeutic efficacy). In still other embodiments, the likelihood or probability score can be used to make or influence a clinical decision (e.g., diagnosis of cancer, treatment selection, assessment of treatment effectiveness, etc.). For example, in one embodiment, if the likelihood or probability score exceeds a threshold, a physician can prescribe an appropriate treatment.

Early Detection of Cancer

In some embodiments, the methods and/or classifier of the present invention are used to detect the presence or absence of cancer in a subject suspected of having cancer. For example, a classifier (as described herein) can be used to determine a likelihood or probability score that a sample feature vector is from a subject that has cancer.

In one embodiment, a probability score of greater than or equal to 60 can indicated that the subject has cancer. In still other embodiments, a probability score greater than or equal to 65, greater than or equal to 70, greater than or equal to 75, greater than or equal to 80, greater than or equal to 85, greater than or equal to 90, or greater than or equal to 95, indicated that the subject has cancer. In other embodiments, a probability score can indicate the severity of disease. For example, a probability score of 80 may indicate a more severe form, or later stage, of cancer compared to a score below 80 (e.g., a score of 70). Similarly, an increase in the probability score over time (e.g., at a second, later time point) can indicate disease progression or a decrease in the probability score over time (e.g., at a second, later time point) can indicate successful treatment.

In another embodiment, a cancer log-odds ratio can be calculated for a test subject by taking the log of a ratio of a probability of being cancerous over a probability of being non-cancerous (i.e., one minus the probability of being cancerous), as described herein. In accordance with this embodiment, a cancer log-odds ratio greater than 1 can indicate that the subject has cancer. In still other embodiments, a cancer log-odds ratio greater than 1.2, greater than 1.3, greater than 1.4, greater than 1.5, greater than 1.7, greater than 2, greater than 2.5, greater than 3, greater than 3.5, or greater than 4, indicated that the subject has cancer.

In other embodiments, a cancer log-odds ratio can indicate the severity of disease. For example, a cancer log-odds ratio greater than 2 may indicate a more severe form, or later stage, of cancer compared to a score below 2 (e.g., a score of 1). Similarly, an increase in the cancer log-odds ratio over time (e.g., at a second, later time point) can indicate disease progression or a decrease in the cancer log-odds ratio over time (e.g., at a second, later time point) can indicate successful treatment.

According to aspects of the invention, the methods and systems of the present invention can be trained to detect or classify multiple cancer indications. For example, the methods, systems and classifiers of the present invention can be used to detect the presence of one or more, two or more, three or more, five or more, or ten or more different types of cancer.

In some embodiments, the cancer is one or more of (1) blood cancer, (2) breast cancer, (3) colorectal cancer, (4) esophageal cancer, (5) head and neck cancer, (6) hepatobiliary cancer, (7) lung cancer, (8) ovarian cancer, and (9) pancreatic cancer.

Cancer and Treatment Monitoring

In some embodiments, the likelihood or probability score can be assessed at different time points (e.g., or before or after treatment) to monitor disease progression or to monitor treatment effectiveness (e.g., therapeutic efficacy). For example, the present disclosure provides methods that involve obtaining a first sample (e.g., a first plasma cfDNA sample) from a cancer patient at a first time point, determining a first likelihood or probability score therefrom (as described herein), obtaining a second test sample (e.g., a second plasma cfDNA sample) from the cancer patient at a second time point, and determine a second likelihood or probability score therefrom (as described herein).

In certain embodiments, the first time point is before a cancer treatment (e.g., before a resection surgery or a therapeutic intervention), and the second time point is after a cancer treatment (e.g., after a resection surgery or therapeutic intervention), and the method utilized to monitor the effectiveness of the treatment. For example, if the second likelihood or probability score decreases compared to the first likelihood or probability score, then the treatment is considered to have been successful. However, if the second likelihood or probability score increases compared to the first likelihood or probability score, then the treatment is considered to have not been successful. In other embodiments, both the first and second time points are before a cancer treatment (e.g., before a resection surgery or a therapeutic intervention). In still other embodiments, both the first and the second time points are after a cancer treatment (e.g., before a resection surgery or a therapeutic intervention) and the method used to monitor the effectiveness of the treatment or loss of effectiveness of the treatment. In still other embodiments, cfDNA samples may be obtained from a cancer patient at a first and second time point and analyzed. e.g., to monitor cancer progression, to determine if a cancer is in remission (e.g., after treatment), to monitor or detect residual disease or recurrence of disease, or to monitor treatment (e.g., therapeutic) efficacy.

Those of skill in the art will readily appreciate that test samples can be obtained from a cancer patient over any desired set of time points and analyzed in accordance with the methods of the invention to monitor a cancer state in the patient. In some embodiments, the first and second time points are separated by an amount of time that ranges from about 15 minutes up to about 30 years, such as about 30 minutes, such as about 1, 2, 3, 4, 5, 6, 7, 8, 9, 10, 11, 12, 13, 14, 15, 16, 17, 18, 19, 20, 21, 22, 23, or about 24 hours, such as about 1, 2, 3, 4, 5, 10, 15, 20, 25 or about 30 days, or such as about 1, 2, 3, 4, 5, 6, 7, 8, 9, 10, 11, or 12 months, or such as about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5 or about 30 years. In other embodiments, test samples can be obtained from the patient at least once every 3 months, at least once every 6 months, at least once a year, at least once every 2 years, at least once every 3 years, at least once every 4 years, or at least once every 5 years.

Treatment

In still another embodiment, information obtained from any method described herein (e.g., the likelihood or probability score) can be used to make or influence a clinical decision (e.g., diagnosis of cancer, treatment selection, assessment of treatment effectiveness, etc.). For example, in one embodiment, if the likelihood or probability score exceeds a threshold, a physician can prescribe an appropriate treatment (e.g., a resection surgery, radiation therapy, chemotherapy, and/or immunotherapy). In some embodiments, information such as a likelihood or probability score can be provided as a readout to a physician or subject.

A classifier (as described herein) can be used to determine a likelihood or probability score that a sample feature vector is from a subject that has cancer. In one embodiment, an appropriate treatment (e.g., resection surgery or therapeutic) is prescribed when the likelihood or probability exceeds a threshold. For example, in one embodiment, if the likelihood or probability score is greater than or equal to 60, one or more appropriate treatments are prescribed. In another embodiments, if the likelihood or probability score is greater than or equal to 65, greater than or equal to 70, greater than or equal to 75, greater than or equal to 80, greater than or equal to 85, greater than or equal to 90, or greater than or equal to 95, one or more appropriate treatments are prescribed. In other embodiments, a cancer log-odds ratio can indicate the effectiveness of a cancer treatment. For example, an increase in the cancer log-odds ratio over time (e.g., at a second, after treatment) can indicate that the treatment was not effective. Similarly, a decrease in the cancer log-odds ratio over time (e.g., at a second, after treatment) can indicate successful treatment. In another embodiment, if the cancer log-odds ratio is greater than 1, greater than 1.5, greater than 2, greater than 2.5, greater than 3, greater than 3.5, or greater than 4, one or more appropriate treatments are prescribed.

In some embodiments, the treatment is one or more cancer therapeutic agents selected from the group consisting of a chemotherapy agent, a targeted cancer therapy agent, a differentiating therapy agent, a hormone therapy agent, and an immunotherapy agent. For example, the treatment can be one or more chemotherapy agents selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, platinum-based agents and any combination thereof. In some embodiments, the treatment is one or more targeted cancer therapy agents selected from the group consisting of signal transduction inhibitors (e.g. tyrosine kinase and growth factor receptor inhibitors), histone deacetylase (HDAC) inhibitors, retinoic receptor agonists, proteosome inhibitors, angiogenesis inhibitors, and monoclonal antibody conjugates. In some embodiments, the treatment is one or more differentiating therapy agents including retinoids, such as tretinoin, alitretinoin and bexarotene. In some embodiments, the treatment is one or more hormone therapy agents selected from the group consisting of anti-estrogens, aromatase inhibitors, progestins, estrogens, anti-androgens, and GnRH agonists or analogs. In one embodiment, the treatment is one or more immunotherapy agents selected from the group comprising monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID). It is within the capabilities of a skilled physician or oncologist to select an appropriate cancer therapeutic agent based on characteristics such as the type of tumor, cancer stage, previous exposure to cancer treatment or therapeutic agent, and other characteristics of the cancer.

EXAMPLES

The following examples are put forth so as to provide those of ordinary skill in the art with a complete disclosure and description of how to make and use the present description, and are not intended to limit the scope of what the inventors regard as their description nor are they intended to represent that the experiments below are all or the only experiments performed. Efforts have been made to ensure accuracy with respect to numbers used (e.g., amounts, temperature, etc.) but some experimental errors and deviations should be accounted for.

Example 1

Analysis of Probe Qualities

Figure 9:
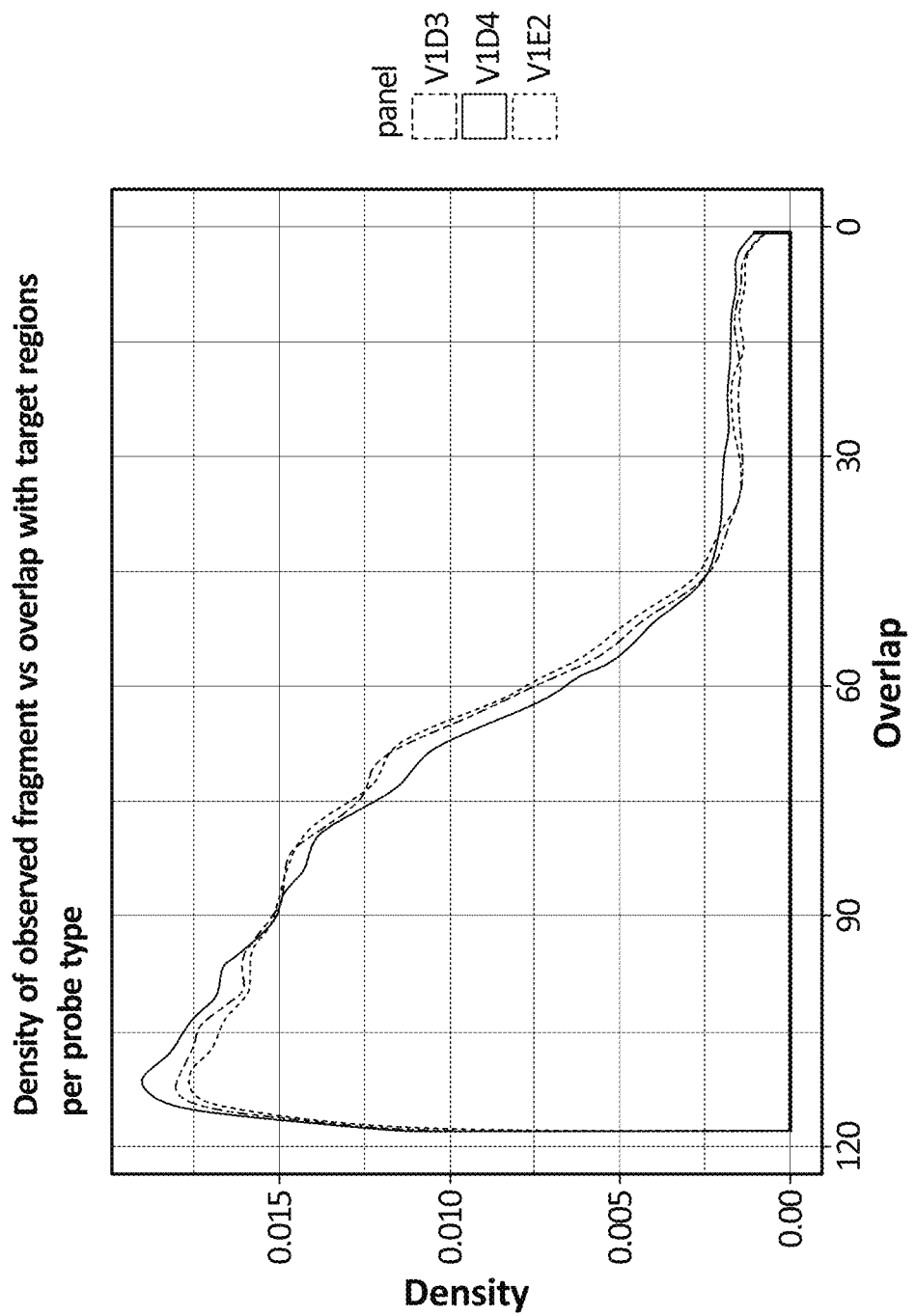
FIG. 9 is a graph of the amounts of DNA fragments hybridizing to probes depending on the sizes of overlaps between the DNA fragments and the probes.

To test how much overlap between a cfDNA fragment and a probe is required to achieve a non-negligible amount of pulldown, various lengths of overlaps were tested using panels designed to include three different types of probes (V1D3, V1D4, V1E2) having various overlaps with 175 bp target DNA fragments specific to each probe. Tested overlaps ranged between 0 bp and 120 bp. Samples comprising 175 bp target DNA fragments were applied to the panel and washed, and then DNA fragments bound to the probes were collected. The amounts of the collected DNA fragments were measured and the amounts were plotted as densities over the sizes of overlaps as provided in FIG. 9.

There was no significant binding and pull down of target DNA fragments when there were less than 45 bp of overlaps. These results suggest that a fragment-probe overlap of at least 45 bp is generally required to achieve a non-negligible amount of pulldown although this number can vary depending on the assay conditions.

Furthermore, it has been suggested that more than a 10% mismatch rate between the probe and fragment sequences in the region of overlap is sufficient to greatly disrupt binding, and thus pulldown efficiency. Therefore, sequences that can align to the probe along at least 45 bp with at least a 90% match rate are candidates for off-target pulldown.

Thus, we have performed an exhaustive searching of all genomic regions having 45 bp alignments with 90%+ match rate (i.e., off-target regions) for each probe. Specifically, we combined a k-mer seeding strategy (which can allow one or more mismatches) with local alignment at the seed locations. This guaranteed not missing any good alignments based on k-mer length, number of mismatches allowed, and number of k-mer seed hits at a particular location. This involves performing dynamic programing local alignment at a large number of locations, so the implementation was optimized to use vector CPU instructions (e.g., AVX2, AVX512) and parallelized across many cores within a machine and also across many machines connected by a network. This allows exhaustive search which is valuable in designing a high-performance panel (i.e., low off-target rate and high target coverage for a given amount of sequencing).

Following the exhaustive searching, each probe was scored based on the number of off-target regions. The best probes have a score of 1, meaning they match in only one place (high Q). Probes with a low score between 2-19 hits (low Q) were accepted but probes with a poor score more than 20 hits (poor Q) were discarded. Other cutoff values can be used for specific samples.

Figure 10:
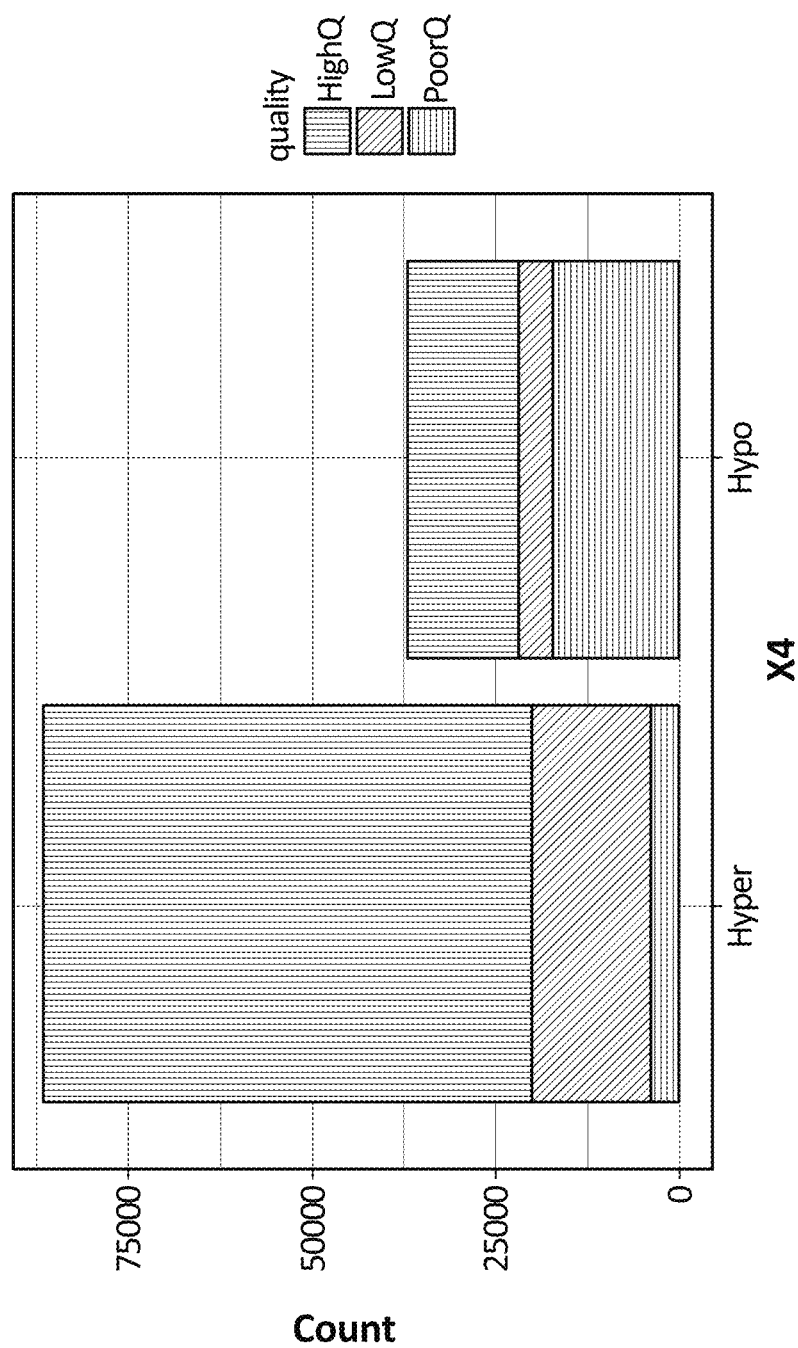
FIG. 10 compares the numbers of high quality (high Q), low quality (low Q), and poor quality (poor Q) probes among the probes targeting hypermethylated fragments (Hyper) or hypomethylated fragments (Hypo).

Numbers of high quality, low quality, and poor quality probes were then counted among probes targeting hypermethylated genomic regions or hypomethylated genomic regions. As provided in FIG. 10, probes targeting hypermethylated regions tend to have significantly less off-target regions.

Example 2

Annotation of Target Genomic Regions

Figure 12:
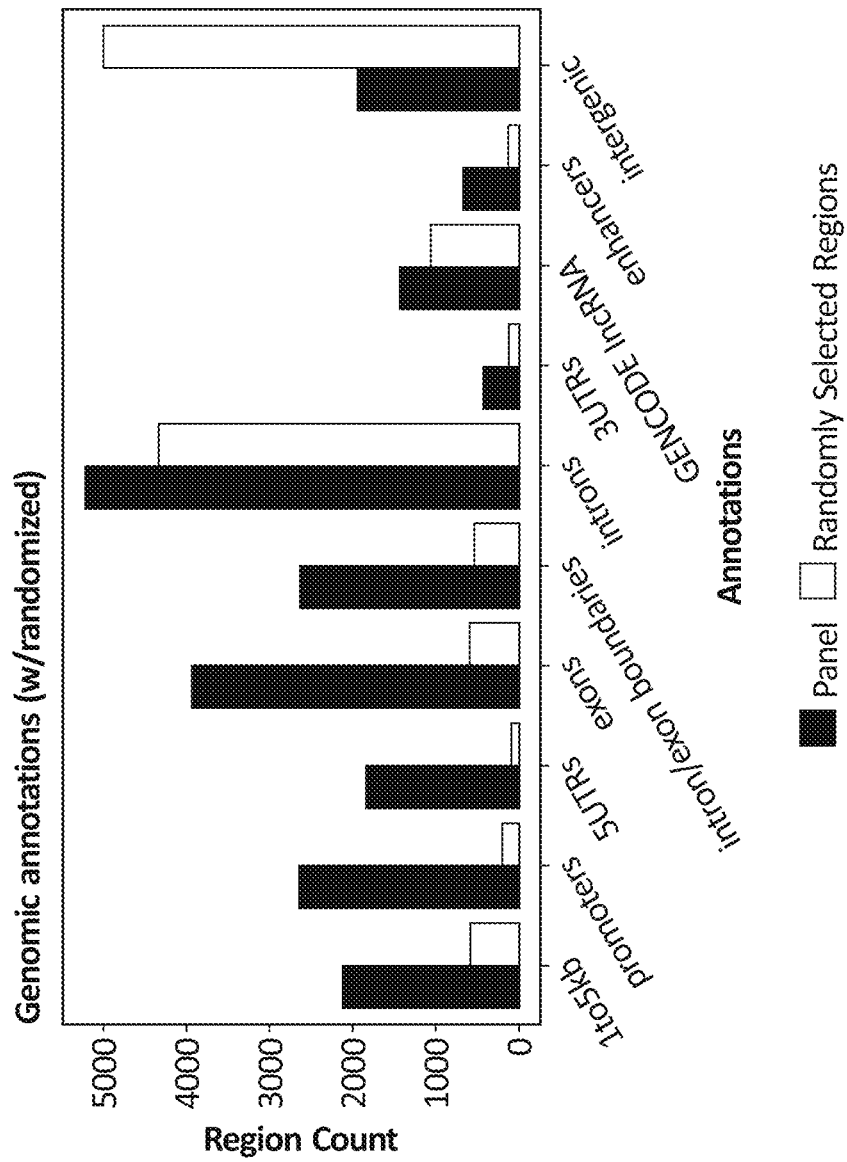
FIG. 12 summarizes frequencies of genomic annotations of targeted genomic regions (black) and randomly selected regions (gray).

Target genomic regions identified by the process outlined in FIG. 4 were analyzed to understand features of the target regions. Specifically, selected target genomic regions were aligned to a reference genome to determine alignment positions. The alignment position information was collected for each selected target genomic region, including the chromosome number, beginning nucleotide base, end nucleotide base, and the genomic annotations of the given genomic region. Target genomic regions were positioned in introns, exons, intergenic regions, 5'UTRs, 3'UTRs, or controlling regions such as promoters or enhancers. The number of target genomic regions that fall within each genomic annotation were counted and plotted in the graph provided in FIG. 12. FIG. 12 also compares numbers of the selected target genomic regions (black bars) or numbers of randomly selected genomic regions (gray bars) that fall within each genomic annotation.

The analysis shows that the selected target genomic regions are not random in their genomic distributions and they had higher enrichment for regulatory and functional elements such as promoters and 5UTRs and less representation of intergenic sequences in comparison with randomly selected targets of the same size. For example, target genomic regions were found to position in promoters, 5'UTR, exons, intron/exon boundaries, introns, 3'UTRs or enhancers, rather than intergenic regions.

Example 3

Cancer Assay Panels (CCGA)

Target genomic regions were selected using database generated by sequencing cfDNA fragments obtained from more than 1800 individuals. The cfDNA sequencing database is referred to as The Circulating Cell-free Genome Atlas Study ("CCGA") herein. The CCGA study was described with Clinical Trial.gov Identifier: NCT02889978 (https://www.clinicaltrials.gov/ct2/show/NCT02889978).

Specifically, cfDNA sequences in the database were filtered based on p-value using a non-cancer distribution, and only fragments with p<0.001 were retained. The selected cfDNAs were further filtered to retain only those that were at least 90% methylated or 90% unmethylated. Next, for each CpG site in the selected fragments, the numbers of cancer samples or non-cancer samples were counted that include fragments overlapping that CpG site. Specifically, P (cancer|overlapping fragment) for each CpG was calculated and genomic sites with high P values were selected as general cancer targets. By design, the selected fragments had very low noise (i.e., few non-cancer fragments overlapping).

To find cancer type specific targets, similar selection processes were performed. CpG sites were ranked based on their information gain, comparing one cancer type to all other samples (non-cancer plus other cancer types). We only attempted to find cancer type specific targets for the subset of the cancer types in CCGA that we felt should have enough signal to make this feasible. This intuition was supported by a good result using the same selection method to find features for a cancer type classifier.

Cancer assay panels comprising probes targeting the selected genomic regions were generated. Specifically, the panels were designed to detect the presence and/or stage of cancer generally (i.e., vs non-cancer) or a specific cancer type as listed below:

Table 1: Pan-cancer #1
Table 2: Blood cancer #1
Table 3: Breast cancer #1
Table 4: Colorectal cancer #1
Table 5: Esophageal cancer #1
Table 6: Head and neck cancer #1
Table 7: Hepatobiliary cancer #1
Table 8: Lung cancer #1
Table 9: Ovarian cancer #1
Table 10: Pancreatic cancer #1
Table 12: Pan-cancer #2
Table 13: Pan-cancer #3
Table 14: Pan-cancer #4
Table 15: Pan-cancer #5
Table 16: Blood cancer #2
Table 17: Breast cancer #2
Table 18: Colorectal cancer #2
Table 19: Esophageal cancer #2
Table 20: Head and neck cancer #2
Table 21: Hepatobiliary cancer #2
Table 22: Lung cancer #2
Table 23: Ovarian cancer #2
Table 24: Pancreatic cancer #2

The panels can include probes configured to hybridize to a modified fragment obtained from processing of the cfDNA molecules, where each of the cfDNA molecules corresponds to or is derived from one or more genomic regions included in the list provided as Tables 1-24. The genomic regions provided in Tables 1-10 and 12-13 were identified by the process outlined in FIG. 4 using the CCGA data set. Tables 14-24 represent subsets of Tables 1-13. Tables 1-10 list the genomic regions in the following column format, starting from the left-most column: chromosome on which the target genomic region is located, start and stop position of the target genomic region, whether the target genomic region is hypermethylated or hypomethylated, and an annotation (if known) of any gene located within 10,000 bp of the targeted region of the genome. Tables 12-24 have the following column formatting, starting from the left-most column: chromosome on which the target genomic region is located and start and stop position of the target genomic region on the chromosome. The chromosome numbers and the start and stop positions are provided relative to a known human reference genome, hg19. The sequence of the human reference genome, hg19, is available from Genome Reference Consortium with a reference number, GRCh37/hg19, and also available from Genome Browser provided by Santa Cruz Genomics Institute.

Generally, a probe can be designed to overlap any of the CpG sites included within the start/stop ranges of any of the targeted regions (e.g., anomalous fragments) included in Tables 1-24.

TABLE 1

| Chr | Start | Stop | Hypo/hyper | Annotation | Chr | Start | Stop | Hypo/hyper | Annotation |
|---|---|---|---|---|---|---|---|---|---|
| chr8 | 1085573 | 1085603 | Hypo | | chr8 | 1085573 | 1085603 | Hypo | |
| chr8 | 1444052 | 1444205 | Hypo | DLGAP2 | chr8 | 1325465 | 1325606 | Hypo | |
| chr8 | 8748422 | 8748713 | Hypo | MFHAS1 | chr8 | 8640024 | 8640100 | Hypo | MFHAS1 |
| chr8 | 9722850 | 9722896 | Hypo | | chr8 | 8748919 | 8748956 | Hypo | MFHAS1 |
| chr8 | 11705960 | 11706136 | Hypo | CTSB, FDFT1 | chr8 | 10980452 | 10980589 | Hypo | C8orf15 |
| chr8 | 11726469 | 11726975 | Hypo | | chr8 | 11706580 | 11706613 | Hypo | CTSB, FDFT1 |
| chr8 | 13319931 | 13319961 | Hypo | | chr8 | 11790579 | 11790653 | Hypo | TRNA_Pseudo |
| chr8 | 22101641 | 22101699 | Hypo | MIR320A, POLR3D | chr8 | 21876649 | 21876819 | Hypo | NPM2 |
| chr8 | 37755922 | 37755952 | Hypo | | chr8 | 23423923 | 23423974 | Hypo | FP15737, SLC25A37, AF116693 |
| chr8 | 38032345 | 38032827 | Hypo | LSM1, BAG4 | chr8 | 37961793 | 37961902 | Hypo | ASH2L |
| chr8 | 41700639 | 41700751 | Hypo | | chr8 | 38256378 | 38256412 | Hypo | LETM2 |
| chr8 | 41910270 | 41910339 | Hypo | KAT6A | chr8 | 41711325 | 41711447 | Hypo | |
| chr8 | 42350324 | 42350492 | Hypo | SLC20A2 | chr8 | 42147392 | 42147521 | Hypo | IKBKB |
| chr8 | 47093246 | 47093276 | Hypo | | chr8 | 42749816 | 42750012 | Hypo | MIR4469, HOOK3, RNF170 |
| chr8 | 49959230 | 49959260 | Hypo | C8orf22 | chr8 | 47334619 | 47334678 | Hypo | |
| chr8 | 55826087 | 55826117 | Hypo | | chr8 | 52230518 | 52230548 | Hypo | PXDNL |
| chr8 | 58105946 | 58106115 | Hypo | | chr8 | 56542925 | 56543064 | Hypo | |
| chr8 | 58130364 | 58130574 | Hypo | LOC100507651 | chr8 | 58117004 | 58117079 | Hypo | |
| chr8 | 61789974 | 61790004 | Hypo | | chr8 | 59747186 | 59747318 | Hypo | TOX |
| chr8 | 62763403 | 62763433 | Hypo | | chr8 | 62033879 | 62034059 | Hypo | |
| chr8 | 66560323 | 66560545 | Hypo | MTFR1 | chr8 | 66548717 | 66548800 | Hypo | MTFR1, ARMC1 |
| chr8 | 71017156 | 71017195 | Hypo | NCOA2 | chr8 | 67580735 | 67580829 | Hypo | C8orf44, C8orf44-SGK3, VCPIP1 |
| chr8 | 71447529 | 71447559 | Hypo | | chr8 | 71308096 | 71308126 | Hypo | |
| chr8 | 74759306 | 74759463 | Hypo | UBE2W | chr8 | 72470399 | 72470441 | Hypo | |
| chr8 | 74889486 | 74889592 | Hypo | TMEM70, TCEB1 | chr8 | 74759819 | 74759966 | Hypo | UBE2W |
| chr8 | 80894529 | 80894594 | Hypo | TPD52, MRPS28 | chr8 | 76316329 | 76316452 | Hypo | HNF4G |

TABLE 1-continued

| Chr | Start | Stop | Hypo/hyper | Annotation | Chr | Start | Stop | Hypo/hyper | Annotation |
|---|---|---|---|---|---|---|---|---|---|
| chr8 | 82902963 | 82902993 | Hypo | | chr8 | 82243813 | 82243843 | Hypo | |
| chr8 | 86131760 | 86131850 | Hypo | CA13, AB209185, C8orf59, E2F5 | chr8 | 84932902 | 84932942 | Hypo | |
| chr8 | 86436621 | 86436651 | Hypo | | chr8 | 86406716 | 86406849 | Hypo | |
| chr8 | 86544756 | 86544959 | Hypo | | chr8 | 86495193 | 86495287 | Hypo | |
| chr8 | 90913079 | 90913653 | Hypo | OSGIN2 | chr8 | 90702972 | 90703034 | Hypo | |
| chr8 | 92083523 | 92083751 | Hypo | OTUD6B, BC067244 | chr8 | 91411537 | 91411567 | Hypo | |
| chr8 | 95485999 | 95486029 | Hypo | RAD54B | chr8 | 94684190 | 94684560 | Hypo | LINC00535 |
| chr8 | 96219863 | 96219901 | Hypo | C8orf69 | chr8 | 96038540 | 96038580 | Hypo | NDUFAF6 |
| chr8 | 98744202 | 98744325 | Hypo | MTDH | chr8 | 97339846 | 97340195 | Hypo | PTDSS1 |
| chr8 | 101169625 | 101169659 | Hypo | SPAG1, POLR2K | chr8 | 99951897 | 99951939 | Hypo | OSR2 |
| chr8 | 103629590 | 103629882 | Hypo | | chr8 | 101736027 | 101736202 | Hypo | PABPC1 |
| chr8 | 106434115 | 106434145 | Hypo | ZFPM2 | chr8 | 106301844 | 106301978 | Hypo | |
| chr8 | 110406028 | 110406243 | Hypo | PKHD1L1 | chr8 | 110275006 | 110275040 | Hypo | NUDCD1 |
| chr8 | 111133092 | 111133257 | Hypo | | chr8 | 110592198 | 110592228 | Hypo | SYBU |
| chr8 | 118532128 | 118532292 | Hypo | MED30 | chr8 | 115516296 | 115516440 | Hypo | |
| chr8 | 120844095 | 120844285 | Hypo | TAF2, DSCC1 | chr8 | 119043568 | 119043732 | Hypo | EXT1 |
| chr8 | 122068889 | 122068919 | Hypo | | chr8 | 120845586 | 120845807 | Hypo | DSCC1, TAF2 |
| chr8 | 122346940 | 122347052 | Hypo | | chr8 | 122346689 | 122346719 | Hypo | |
| chr8 | 124055236 | 124055336 | Hypo | DERL1 | chr8 | 123695532 | 123695660 | Hypo | |
| chr8 | 125452366 | 125452541 | Hypo | | chr8 | 124427887 | 124428082 | Hypo | WDYHV1 |
| chr8 | 127354106 | 127354261 | Hypo | | chr8 | 126044442 | 126044563 | Hypo | SQLE, KIAA0196 |
| chr8 | 128872385 | 128872415 | Hypo | | chr8 | 128745542 | 128745633 | Hypo | MYC, HV975509, BC042052 |
| chr8 | 129356009 | 129356039 | Hypo | | chr8 | 128889324 | 128889422 | Hypo | |
| chr8 | 132054727 | 132054785 | Hypo | ADCY8 | chr8 | 130369244 | 130369364 | Hypo | CCDC26 |
| chr8 | 133686745 | 133687107 | Hypo | LRRC6 | chr8 | 133360080 | 133360194 | Hypo | KCNQ3 |
| chr8 | 140834237 | 140834321 | Hypo | TRAPPC9 | chr8 | 135301097 | 135301142 | Hypo | |
| chr8 | 141054845 | 141054875 | Hypo | TRAPPC9 | chr8 | 140963292 | 140963362 | Hypo | TRAPPC9 |
| chr8 | 141588056 | 141588132 | Hypo | AGO2 | chr8 | 141159919 | 141159949 | Hypo | |
| chr8 | 142361233 | 142361487 | Hypo | GPR20, LOC731779 | chr8 | 142292628 | 142292665 | Hypo | |
| chr8 | 142535343 | 142535496 | Hypo | | chr8 | 142444600 | 142444752 | Hypo | PTP4A3, MROH5 |
| chr8 | 142694847 | 142694953 | Hypo | | chr8 | 142568598 | 142568652 | Hypo | |
| chr8 | 143082777 | 143082810 | Hypo | | chr8 | 142984512 | 142984666 | Hypo | |
| chr8 | 143105244 | 143105377 | Hypo | | chr8 | 143089030 | 143089100 | Hypo | |
| chr8 | 143557980 | 143558080 | Hypo | BAI1 | chr8 | 143509457 | 143509594 | Hypo | |
| chr8 | 143621980 | 143622096 | Hypo | BAI1 | chr8 | 143587331 | 143587382 | Hypo | BAI1 |
| chr8 | 143819384 | 143819428 | Hypo | SLURP1, THEM6 | chr8 | 143702052 | 143702101 | Hypo | ARC |
| chr8 | 143993974 | 143994165 | Hypo | CYP11B2 | chr8 | 143876928 | 143876958 | Hypo | LY6D |
| chr8 | 144190378 | 144190432 | Hypo | | chr8 | 144069546 | 1440696 | Hypo | CDC42P3, LOC100133669 |
| chr8 | 144226174 | 144226204 | Hypo | | chr8 | 144203977 | 144204021 | Hypo | |
| chr8 | 144330193 | 144330380 | Hypo | ZFP41 | chr8 | 144238822 | 144238901 | Hypo | LY6H |
| chr8 | 144347397 | 144347740 | Hypo | GLI4 | chr8 | 144344293 | 144344442 | Hypo | GLI4 |
| chr8 | 144360394 | 144360453 | Hypo | GLI4 | chr8 | 144359977 | 144360076 | Hypo | GLI4 |
| chr8 | 144372323 | 144372503 | Hypo | ZNF696 | chr8 | 144361758 | 144361823 | Hypo | GLI4 |
| chr8 | 145753517 | 145753547 | Hypo | ARHGAP39, C8orf82, LRRC24, DQ579335, LRRC14 | chr8 | 144382679 | 144382775 | Hypo | TOP1MT, ZNF696 |
| chr8 | 145918683 | 145918835 | Hypo | ARHGAP39 | chr8 | 145758572 | 145758692 | Hypo | ARHGAP39, C8orf82, LRRC24 |
| chr8 | 146079215 | 146079379 | Hypo | COMMD5 | chr8 | 146013617 | 146013647 | Hypo | RPL8, DL491750, ZNF34 |
| chr8 | 146176756 | 146176795 | Hypo | ZNF16 | chr8 | 146175120 | 146175269 | Hypo | ZNF16 |
| chr18 | 597548 | 597578 | Hypo | CLUL1 | chr18 | 147543 | 147613 | Hypo | |
| chr18 | 2755770 | 2755878 | Hypo | SMCHD1 | chr18 | 697854 | 697901 | Hypo | ENOSF1 |
| chr18 | 8612252 | 8612282 | Hypo | RAB12 | chr18 | 5133207 | 5133343 | Hypo | |
| chr18 | 9912767 | 9912797 | Hypo | VAPA | chr18 | 9868137 | 9868174 | Hypo | |
| chr18 | 10589096 | 10589348 | Hypo | | chr18 | 10251324 | 10251432 | Hypo | AX747048 |
| chr18 | 11401654 | 11401817 | Hypo | | chr18 | 10733605 | 10733605 | Hypo | PIEZO2 |
| chr18 | 11979677 | 11979860 | Hypo | IMPA2 | chr18 | 11942728 | 11942838 | Hypo | |
| chr18 | 12375923 | 12376129 | Hypo | AFG3L2 | chr18 | 12375483 | 12375597 | Hypo | AFG3L2 |
| chr18 | 12948993 | 12949023 | Hypo | SEHIL | chr18 | 12890152 | 12890278 | Hypo | PTPN2 |
| chr18 | 19191525 | 19191585 | Hypo | SNRPD1 | chr18 | 13826393 | 13826536 | Hypo | MC5R |
| chr18 | 21035222 | 21035252 | Hypo | RIOK3 | chr18 | 20911541 | 20911571 | Hypo | TMEM241 |
| chr18 | 23686462 | 23686618 | Hypo | | chr18 | 21719938 | 21720064 | Hypo | CABYR, TTC39C |
| chr18 | 32957803 | 32957839 | Hypo | ZNF396 | chr18 | 29719775 | 29720012 | Hypo | RNF138 |
| chr18 | 43546048 | 43546134 | Hypo | EPG5 | chr18 | 33078363 | 33078406 | Hypo | INO80C |
| chr18 | 46142662 | 46142809 | Hypo | CTIF | chr18 | 44259903 | 44259990 | Hypo | ST8SIA5, AK095045 |
| chr18 | 51771058 | 51771128 | Hypo | | chr18 | 48636211 | 48636320 | Hypo | |
| chr18 | 55426948 | 55426978 | Hypo | | chr18 | 53989796 | 53989877 | Hypo | |
| chr18 | 56483918 | 56483958 | Hypo | | chr18 | 55850862 | 55850987 | Hypo | NEDD4L |
| chr18 | 60557729 | 60557759 | Hypo | PHLPP1 | chr18 | 56815734 | 56816107 | Hypo | SEC11C, AK311213 |
| chr18 | 75335093 | 75335123 | Hypo | | chr18 | 72845833 | 72845863 | Hypo | |
| chr18 | 75551271 | 75551301 | Hypo | | chr18 | 75339231 | 75339340 | Hypo | |
| chr18 | 76239541 | 76239616 | Hypo | | chr18 | 75999404 | 75999434 | Hypo | |
| chr18 | 76653631 | 76653661 | Hypo | | chr18 | 76501479 | 76501509 | Hypo | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr18 | 76689735 | 76689765 | Hypo | | chr18 | 76686249 | 76686279 | Hypo | |
| chr18 | 77143346 | 77143376 | Hypo | ATP9B | chr18 | 77050480 | 77050678 | Hypo | ATP9B |
| chr18 | 77181355 | 77181409 | Hypo | NFATC1 | chr18 | 77167824 | 77167854 | Hypo | NFATC1 |
| chr18 | 77205532 | 77205638 | Hypo | NFATC1 | chr18 | 77194936 | 77194978 | Hypo | NFATC1 |
| chr18 | 77300326 | 77300483 | Hypo | | chr18 | 77285897 | 77286028 | Hypo | NFATC1 |
| chr18 | 77329727 | 77330017 | Hypo | | chr18 | 77312866 | 77312927 | Hypo | |
| chr18 | 77512225 | 77512255 | Hypo | CTDP1 | chr18 | 77371430 | 77371547 | Hypo | |
| chr18 | 77543700 | 77543824 | Hypo | | chr18 | 77543249 | 77543481 | Hypo | |
| chr18 | 77576934 | 77577043 | Hypo | | chr18 | 77550206 | 77550348 | Hypo | |
| chr9 | 969788 | 969820 | Hypo | DMRT3, DMRT1 | chr18 | 77636591 | 77636621 | Hypo | KCNG2 |
| chr9 | 6182901 | 6182931 | Hypo | | chr9 | 5153325 | 5153380 | Hypo | |
| chr9 | 33000470 | 33000512 | Hypo | APTX | chr9 | 6756353 | 6756623 | Hypo | KDM4C |
| chr9 | 36318375 | 36318410 | Hypo | | chr9 | 36167272 | 36167544 | Hypo | CCIN, GLIPR2 |
| chr9 | 36832204 | 36832343 | Hypo | PAX5, MIR4475 | chr9 | 36433491 | 36433609 | Hypo | |
| chr9 | 37593684 | 37593795 | Hypo | TOMM5 | chr9 | 37467610 | 37467898 | Hypo | |
| chr9 | 38646763 | 38646839 | Hypo | | chr9 | 37697404 | 37697438 | Hypo | FRMPD1 |
| chr9 | 71734816 | 71735024 | Hypo | TJP2 | chr9 | 71200632 | 71200662 | Hypo | |
| chr9 | 73032801 | 73032831 | Hypo | KLF9 | chr9 | 72435189 | 72435317 | Hypo | |
| chr9 | 77823177 | 77823315 | Hypo | | chr9 | 74210499 | 74210654 | Hypo | |
| chr9 | 79638138 | 79638244 | Hypo | FOXB2 | chr9 | 79231003 | 79231033 | Hypo | PRUNE2 |
| chr9 | 85372494 | 85372596 | Hypo | | chr9 | 80303132 | 80303171 | Hypo | |
| chr9 | 90937357 | 90937387 | Hypo | | chr9 | 88694345 | 88694438 | Hypo | GOLM1 |
| chr9 | 94572641 | 94572743 | Hypo | ROR2 | chr9 | 91914276 | 91914306 | Hypo | |
| chr9 | 95560810 | 95560840 | Hypo | | chr9 | 95417551 | 95417651 | Hypo | |
| chr9 | 96230296 | 96230334 | Hypo | FAM120A | chr9 | 95761687 | 95761828 | Hypo | FGD3 |
| chr9 | 96857091 | 96857144 | Hypo | PTPDC1 | chr9 | 96573748 | 96573869 | Hypo | MIR4291 |
| chr9 | 98076746 | 98076776 | Hypo | FANCC | chr9 | 97020978 | 97021126 | Hypo | ZNF169 |
| chr9 | 100818295 | 100818437 | Hypo | NANS | chr9 | 100397821 | 100398016 | Hypo | NCBP1, TSTD2 |
| chr9 | 103174620 | 103174730 | Hypo | | chr9 | 100835828 | 100835870 | Hypo | NANS, TRIM14 |
| chr9 | 114247454 | 114247578 | Hypo | KIAA0368 | chr9 | 110126074 | 110126241 | Hypo | |
| chr9 | 115087567 | 115087597 | Hypo | | chr9 | 115067932 | 115068106 | Hypo | |
| chr9 | 115566363 | 115566583 | Hypo | SNX30 | chr9 | 115478932 | 115479502 | Hypo | INIP |
| chr9 | 117050981 | 117051030 | Hypo | | chr9 | 116633883 | 116633987 | Hypo | ZNF618 |
| chr9 | 124751485 | 124751554 | Hypo | TTLL11 | chr9 | 123295355 | 123295463 | Hypo | CDK5RAP2 |
| chr9 | 125704789 | 125704835 | Hypo | RABGAP1 | chr9 | 125676633 | 125676753 | Hypo | ZBTB26, ZBTB6 |
| chr9 | 126154304 | 126154575 | Hypo | DENND1A | chr9 | 126133778 | 126133856 | Hypo | DENND1A, CRB2 |
| chr9 | 128136065 | 128136095 | Hypo | GAPVD1 | chr9 | 127630125 | 127630205 | Hypo | ARPC5L, RPL35, WDR38 |
| chr9 | 129388710 | 129388796 | Hypo | LMX1B | chr9 | 128759852 | 128759954 | Hypo | |
| chr9 | 130325976 | 130325997 | Hypo | FAM129B | chr9 | 130248419 | 130248449 | Hypo | LRSAM1, AX747547 |
| chr9 | 130694413 | 130694684 | Hypo | DPM2, FAM102A, PIP5KL1 | chr9 | 130675509 | 130675615 | Hypo | PIP5KL1, ST6GALNAC4 |
| chr9 | 131177975 | 131178094 | Hypo | CERCAM | chr9 | 130694809 | 130694948 | Hypo | DPM2, FAM102A, PIP5KL1 |
| chr9 | 131580038 | 131580257 | Hypo | TBC1D13, ENDOG, C9orf114 | chr9 | 131417698 | 131417940 | Hypo | |
| chr9 | 131607770 | 131607800 | Hypo | CCBL1 | chr9 | 131607517 | 131607547 | Hypo | CCBL1 |
| chr9 | 131854564 | 131854732 | Hypo | CRAT, DOLPP1 | chr9 | 131854231 | 131854328 | Hypo | CRAT, DOLPP1 |
| chr9 | 132403149 | 132403216 | Hypo | ASB6, NTMT1 | chr9 | 132402840 | 132402883 | Hypo | ASB6, NTMT1 |
| chr9 | 132815175 | 132815205 | Hypo | GPR107, Mir_562, FNBP1 | chr9 | 132559377 | 132559456 | Hypo | TOR1B |
| chr9 | 133605601 | 133605631 | Hypo | ABL1 | chr9 | 132881814 | 132881844 | Hypo | |
| chr9 | 133927347 | 133927814 | Hypo | LAMC3 | chr9 | 133773766 | 133773923 | Hypo | FIBCD1, QRFP |
| chr9 | 134126670 | 134126741 | Hypo | FAM78A | chr9 | 133928236 | 133928266 | Hypo | LAMC3 |
| chr9 | 134207916 | 134248080 | Hypo | | chr9 | 134191085 | 134191218 | Hypo | PPAPDC3 |
| chr9 | 135135114 | 135135247 | Hypo | SETX | chr9 | 134717313 | 134717367 | Hypo | |
| chr9 | 135548238 | 135548313 | Hypo | GTF3C4, DDX31 | chr9 | 135231073 | 135231158 | Hypo | |
| chr9 | 135865090 | 135865161 | Hypo | GFI1B | chr9 | 135590218 | 135590334 | Hypo | |
| chr9 | 137002646 | 137002692 | Hypo | WDR5 | chr9 | 135898911 | 135899124 | Hypo | GTF3C5 |
| chr9 | 137656958 | 137657128 | Hypo | COL5A1 | chr9 | 137575915 | 137575945 | Hypo | COL5A1 |
| chr9 | 137718901 | 137719001 | Hypo | LOC101448202, COL5A1 | chr9 | 137667327 | 137667357 | Hypo | COL5A1 |
| chr9 | 138265123 | 138265251 | Hypo | | chr9 | 137722087 | 137722209 | Hypo | LOC101448202, COL5A1 |
| chr9 | 138563059 | 138563280 | Hypo | LCN9 | chr9 | 138474557 | 138474590 | Hypo | LOC100130954 |
| chr9 | 138634047 | 138634159 | Hypo | KCNT1 | chr9 | 138627636 | 138627893 | Hypo | KCNT1 |
| chr9 | 138661648 | 138661870 | Hypo | KCNT1 | chr9 | 138659800 | 138659905 | Hypo | KCNT1 |
| chr9 | 138880711 | 138880875 | Hypo | | chr9 | 138666455 | 138666558 | Hypo | KCNT1 |
| chr9 | 139012272 | 139012411 | Hypo | C9orf69 | chr9 | 139000566 | 139000642 | Hypo | C9orf69 |
| chr9 | 139047532 | 139047633 | Hypo | | chr9 | 139045653 | 139045683 | Hypo | |
| chr9 | 139421955 | 139421985 | Hypo | MIR4673 | chr9 | 139111268 | 139111298 | Hypo | QSOX2 |
| chr9 | 139704008 | 139704279 | Hypo | RABL6, KIAA1984-AS1, KIAA1984 | chr9 | 139698925 | 139699051 | Hypo | RABL6, KIAA1984-AS1, KIAA1984 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr9 | 140030498 | 140030528 | Hypo | GRIN1 | chr9 | 139859041 | 139859268 | Hypo | LCN12 |
| chr9 | 140127883 | 140128080 | Hypo | TUBB2C, FAM166A, SLC34A3, RNF224, C9orf169, AK128153, TUBB4B | chr9 | 140031944 | 140032082 | Hypo | GRIN1 |
| chr9 | 140205394 | 140205519 | Hypo | EXD3, NRARP | chr9 | 140137310 | 140137488 | Hypo | SLC34A3, FAM166A, LOC100129722, C9orf173, TUBB2C, TUBB4B |
| chr9 | 140332708 | 140333018 | Hypo | ENTPD8, NOXA1, NSMF | chr9 | 140245877 | 140245998 | Hypo | EXD3 |
| chr9 | 140392454 | 140392844 | Hypo | | chr9 | 140382557 | 140382596 | Hypo | PNPLA7 |
| chr9 | 140498318 | 140498394 | Hypo | ARRDC1 | chr9 | 140397029 | 140397097 | Hypo | |
| chr9 | 140769943 | 140769973 | Hypo | AK128414, CACNA1B | chr9 | 140507256 | 140507419 | Hypo | EHMT1, ARRDC1, C9orf37 |
| chr1 | 913532 | 913955 | Hypo | C1orf170, PLEKHN1 | chr1 | 715373 | 715447 | Hypo | LOC100288069 |
| chr1 | 1146734 | 1146818 | Hypo | SDF4, TNFRSF4, TNFRSF18 | chr1 | 1080583 | 1080824 | Hypo | LOC254099 |
| chr1 | 1223512 | 1223652 | Hypo | ACAP3, SCNN1D | chr1 | 1218737 | 1218820 | Hypo | UBE2J2, ACAP3, SCNN1D |
| chr1 | 1253356 | 1253386 | Hypo | CPSF3L, GLTPD1, PUSL1, ACAP3 | chr1 | 1235813 | 1236078 | Hypo | PUSL1, ACAP3, SCNN1D |
| chr1 | 1267462 | 1267699 | Hypo | DVL1, TAS1R3, GLTPD1, CPSF3L | chr1 | 1267014 | 1267151 | Hypo | DVL1, TAS1R3, GLTPD1, CPSF3L |
| chr1 | 1341668 | 1341743 | Hypo | MRPL20, LOC148413, CCNL2 | chr1 | 1267906 | 1268158 | Hypo | DVL1, TAS1R3, GLTPD1, CPSF3L |
| chr1 | 1563193 | 1563223 | Hypo | CDK11B, MIB2, MMP23B | chr1 | 1436043 | 1436211 | Hypo | ATAD3B |
| chr1 | 1874744 | 1874787 | Hypo | KIAA1751 | chr1 | 1857847 | 1857909 | Hypo | C1orf222, TMEM52, CALML6 |
| chr1 | 1974848 | 1974925 | Hypo | PRKCZ | chr1 | 1923457 | 1923521 | Hypo | KIAA1751 |
| chr1 | 2125216 | 2125483 | Hypo | C1orf86, BC018779 | chr1 | 2066490 | 2066679 | Hypo | PRKCZ |
| chr1 | 2267552 | 2267690 | Hypo | MORN1 | chr1 | 2263169 | 2263263 | Hypo | MORN1 |
| chr1 | 2307925 | 2307955 | Hypo | MORN1 | chr1 | 2304327 | 2304389 | Hypo | MORN1 |
| chr1 | 2309868 | 2309953 | Hypo | MORN1 | chr1 | 2308376 | 2308636 | Hypo | MORN1 |
| chr1 | 2428331 | 2428385 | Hypo | PLCH2 | chr1 | 2397001 | 2397031 | Hypo | |
| chr1 | 2830155 | 2830185 | Hypo | | chr1 | 2507063 | 2507183 | Hypo | |
| chr1 | 3102653 | 3102779 | Hypo | | chr1 | 2866038 | 2866068 | Hypo | |
| chr1 | 3183415 | 3183455 | Hypo | | chr1 | 3158823 | 3158962 | Hypo | |
| chr1 | 3601850 | 3601946 | Hypo | TP73 | chr1 | 3322090 | 3322170 | Hypo | |
| chr1 | 3664461 | 3664741 | Hypo | CCDC27, TP73-AS1 | chr1 | 3607081 | 3607173 | Hypo | TP73 |
| chr1 | 4111061 | 4111231 | Hypo | | chr1 | 3683686 | 3683818 | Hypo | CCDC27, SMIM1 |
| chr1 | 6166353 | 6166469 | Hypo | KCNAB2, CHD5 | chr1 | 4401433 | 4401463 | Hypo | |
| chr1 | 6280243 | 6280273 | Hypo | ICMT, RNF207 | chr1 | 6171763 | 6171810 | Hypo | CHD5 |
| chr1 | 6446131 | 6446308 | Hypo | ACOT7 | chr1 | 6360593 | 6360634 | Hypo | ACOT7 |
| chr1 | 6776304 | 6776388 | Hypo | | chr1 | 6672227 | 6672351 | Hypo | PHF13, KLHL21 |
| chr1 | 8550032 | 8550078 | Hypo | RERE | chr1 | 7973843 | 7973948 | Hypo | TNFRSF9 |
| chr1 | 10091888 | 10092060 | Hypo | UBE4B | chr1 | 9865110 | 9865140 | Hypo | CLSTN1 |
| chr1 | 10491694 | 10491724 | Hypo | APITD1-CORT, APITD1 | chr1 | 10095469 | 10095845 | Hypo | UBE4B |
| chr1 | 11936748 | 11936778 | Hypo | | chr1 | 11591719 | 11591826 | Hypo | PTCHD2 |
| chr1 | 12251443 | 12251737 | Hypo | TNFRSF1B, MIR4632 | chr1 | 12041374 | 12041525 | Hypo | MFN2, PLOD1 |
| chr1 | 14730425 | 14730472 | Hypo | NBL1 | chr1 | 14128478 | 14128588 | Hypo | |
| chr1 | 19980747 | 19980858 | Hypo | | chr1 | 17787472 | 17787502 | Hypo | |
| chr1 | 20248109 | 20248141 | Hypo | PLA2G2E, OTUD3 | chr1 | 20127338 | 20127471 | Hypo | TMCO4 |
| chr1 | 21026117 | 21026225 | Hypo | KIF17 | chr1 | 20492168 | 20492298 | Hypo | PLA2G2C |
| chr1 | 22927410 | 2292748 | Hypo | EPHA8 | chr1 | 21042894 | 21042924 | Hypo | SH2D5, KIF17 |
| chr1 | 24104000 | 24104062 | Hypo | PITHD1, LOC100506963 | chr1 | 23347997 | 23348043 | Hypo | KDM1A, LOC729059 |
| chr1 | 26467600 | 26467630 | Hypo | | chr1 | 24740603 | 24740829 | Hypo | NIPAL3 |
| chr1 | 26963625 | 26963789 | Hypo | | chr1 | 26917724 | 26917816 | Hypo | |
| chr1 | 27340252 | 27340412 | Hypo | FAM46B | chr1 | 27190175 | 27190278 | Hypo | SFN |
| chr1 | 28558539 | 28558571 | Hypo | ATPIF1, JA611241, DNAJC8 | chr1 | 27844518 | 27844548 | Hypo | |
| chr1 | 29060250 | 29060311 | Hypo | YTHDF2 | chr1 | 29047659 | 29048634 | Hypo | |
| chr1 | 30351554 | 30351742 | Hypo | | chr1 | 29065131 | 29065211 | Hypo | YTHDF2 |
| chr1 | 32533211 | 32533653 | Hypo | TMEM39B, KHDRBS1 | chr1 | 31863186 | 31863216 | Hypo | |
| chr1 | 32756498 | 32756581 | Hypo | HDAC1, LCK | chr1 | 32705488 | 32705550 | Hypo | FAM167B, MTMR9LP, EIF3I |
| chr1 | 35586911 | 35586962 | Hypo | ZMYM1 | chr1 | 32938720 | 32938750 | Hypo | ZBTB8A, ZBTB8B |
| chr1 | 36236269 | 36236299 | Hypo | CLSPN | chr1 | 35664625 | 35664746 | Hypo | SFPQ |
| chr1 | 36563479 | 36563522 | Hypo | COL8A2, ADPRHL2, TEKT2 | chr1 | 36334925 | 36335053 | Hypo | AGO1 |
| chr1 | 38398213 | 38398348 | Hypo | INPP5B | chr1 | 38060267 | 38060317 | Hypo | GNL2 |
| chr1 | 40072513 | 40072680 | Hypo | | chr1 | 39416980 | 39417182 | Hypo | RHBDL2 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr1 | 40625371 | 40625401 | Hypo | RLF | chr1 | 40349545 | 40349647 | Hypo | |
| chr1 | 41991640 | 41991702 | Hypo | HIVEP3 | chr1 | 41967342 | 41967418 | Hypo | HIVEP3 |
| chr1 | 43478202 | 43478255 | Hypo | | chr1 | 43188741 | 43188874 | Hypo | CLDN19 |
| chr1 | 44068774 | 44068804 | Hypo | PTPRF | chr1 | 43834741 | 43834922 | Hypo | ELOVL1, CDC20 |
| chr1 | 44494137 | 44494169 | Hypo | SLC6A9 | chr1 | 44109845 | 44109959 | Hypo | KDM4A |
| chr1 | 45240427 | 45240514 | Hypo | KIF2C, RPS8, SNORD55, SNORD46, SNORD38A, SNORD38B, BEST4 | chr1 | 44726912 | 44727268 | Hypo | ERI3 |
| chr1 | 45645870 | 45645998 | Hypo | ZSWIM5 | chr1 | 45308154 | 45308262 | Hypo | PTCH2, EIF2B3 |
| chr1 | 46347598 | 46347689 | Hypo | MAST2 | chr1 | 45768429 | 45768504 | Hypo | LOC400752 |
| chr1 | 51424099 | 51424224 | Hypo | CDKN2C | chr1 | 50881363 | 50881529 | Hypo | DMRTA2 |
| chr1 | 52832687 | 52832820 | Hypo | ORC1, CC2D1B | chr1 | 51763252 | 51763298 | Hypo | TTC39A |
| chr1 | 54586626 | 54586736 | Hypo | | chr1 | 53129154 | 53129244 | Hypo | FAM159A |
| chr1 | 61541602 | 61541718 | Hypo | NFIA | chr1 | 55231115 | 55231177 | Hypo | PARS2 |
| chr1 | 64734652 | 64734694 | Hypo | | chr1 | 62189908 | 62189974 | Hypo | TM2D1 |
| chr1 | 70672778 | 70672878 | Hypo | LRRC40, SRSF11 | chr1 | 70599012 | 70599169 | Hypo | LRRC7 |
| chr1 | 76354624 | 76354754 | Hypo | MSH4 | chr1 | 75600925 | 75601071 | Hypo | LHX8, AK055631 |
| chr1 | 84944491 | 84944568 | Hypo | RPF1 | chr1 | 78463647 | 78463677 | Hypo | DNAJB4 |
| chr1 | 86860608 | 86860969 | Hypo | ODF2L | chr1 | 86296345 | 86296375 | Hypo | COL24A1 |
| chr1 | 94343568 | 94343744 | Hypo | GCLM, DNTTIP2 | chr1 | 91177989 | 91178149 | Hypo | BARHL2 |
| chr1 | 100310827 | 100310979 | Hypo | AGL | chr1 | 100239507 | 100239544 | Hypo | |
| chr1 | 109585463 | 109585326 | Hypo | WDR47 | chr1 | 100437068 | 100437172 | Hypo | SLC35A3, BC112312 |
| chr1 | 109644226 | 109644336 | Hypo | C1orf194, SCARNA2, TMEM167B | chr1 | 109631549 | 109631682 | Hypo | TMEM167B |
| chr1 | 111440961 | 111440999 | Hypo | CD53 | chr1 | 110883542 | 110883965 | Hypo | BC069739, RBM15, LOC440600 |
| chr1 | 114448943 | 114448990 | Hypo | DCLRE1B, AP4B1 | chr1 | 112084954 | 112084984 | Hypo | RAP1A |
| chr1 | 116214104 | 116214318 | Hypo | VANGL1 | chr1 | 115055395 | 115055425 | Hypo | DENND2C |
| chr1 | 150603138 | 150603170 | Hypo | ENSA | chr1 | 117901133 | 117901264 | Hypo | MAN1A2 |
| chr1 | 151169248 | 151170206 | Hypo | PIP5K1A, VPS72 | chr1 | 151042405 | 151042496 | Hypo | GABPB2, MLLT11 |
| chr1 | 151300888 | 151300918 | Hypo | | chr1 | 151253426 | 151253427 | Hypo | BC021024, ZNF687 |
| chr1 | 153540096 | 153540154 | Hypo | S100A2 | chr1 | 153539476 | 153539637 | Hypo | S100A2 |
| chr1 | 153937124 | 153937330 | Hypo | CREB3L4, JTB, SLC39A1, CRTC2 | chr1 | 153896746 | 153896800 | Hypo | DENND4B, GATAD2B |
| chr1 | 154156468 | 154156717 | Hypo | TPM3, MIR190B | chr1 | 153948791 | 153948823 | Hypo | JTB, CREB3L4, RAB13 |
| chr1 | 154516810 | 154516845 | Hypo | UBE2Q1, TDRD10 | chr1 | 154491036 | 154491066 | Hypo | TDRD10 |
| chr1 | 155578375 | 155578921 | Hypo | MSTO1 | chr1 | 155161778 | 155162033 | Hypo | TRIM46, DM075093, MIR92B, THBS3, MUC1, AX746485 |
| chr1 | 155826248 | 155826336 | Hypo | SYT11 | chr1 | 155617837 | 155617962 | Hypo | BC041646 |
| chr1 | 156010448 | 156010548 | Hypo | UBQLN4 | chr1 | 155954282 | 155954396 | Hypo | ARHGEF2 |
| chr1 | 156432124 | 156432637 | Hypo | MEF2D | chr1 | 156030286 | 156030621 | Hypo | RAB25, LAMTOR2, UBQLN4 |
| chr1 | 157247347 | 157247388 | Hypo | | chr1 | 156838167 | 156838320 | Hypo | NTRK1 |
| chr1 | 157895413 | 157895443 | Hypo | AK057438 | chr1 | 157458909 | 157458961 | Hypo | |
| chr1 | 158245556 | 158245586 | Hypo | | chr1 | 158205040 | 158205070 | Hypo | |
| chr1 | 158591699 | 158591947 | Hypo | SPTA1 | chr1 | 158295829 | 158295935 | Hypo | CD1B |
| chr1 | 158672648 | 158672678 | Hypo | OR6K2 | chr1 | 158669704 | 158669882 | Hypo | OR6K2 |
| chr1 | 158748648 | 158748771 | Hypo | OR6N2 | chr1 | 158687415 | 158687550 | Hypo | OR6K3 |
| chr1 | 158778060 | 158778152 | Hypo | | chr1 | 158760197 | 158760235 | Hypo | |
| chr1 | 158907635 | 158907665 | Hypo | PYHIN1 | chr1 | 158815136 | 158815295 | Hypo | MNDA |
| chr1 | 159337419 | 159337615 | Hypo | BC038194 | chr1 | 159187279 | 159187429 | Hypo | |
| chr1 | 160693934 | 160694102 | Hypo | | chr1 | 160451043 | 160451202 | Hypo | SLAMF6 |
| chr1 | 160992336 | 160992587 | Hypo | F11R | chr1 | 160880758 | 160880788 | Hypo | |
| chr1 | 161086730 | 161086813 | Hypo | NIT1, DEDD, PFDN2 | chr1 | 161007587 | 161007746 | Hypo | USF1, ARHGAP30, TSTD1 |
| chr1 | 161359069 | 161359099 | Hypo | | chr1 | 161122645 | 161122778 | Hypo | UFC1, USP21 |
| chr1 | 161368283 | 161368507 | Hypo | TRNA_Val | chr1 | 161367631 | 161367701 | Hypo | TRNA Val |
| chr1 | 161466301 | 161466347 | Hypo | FCGR2A | chr1 | 161442441 | 161442471 | Hypo | TRNA_Gly, TRNA_Leu, TRNA_Asp, TRNA_Glu |
| chr1 | 165324305 | 165324357 | Hypo | LMX1A | chr1 | 164428741 | 164428831 | Hypo | |
| chr1 | 170063947 | 170064218 | Hypo | | chr1 | 167823339 | 167823461 | Hypo | ADCY10 |
| chr1 | 171625525 | 171625561 | Hypo | MYOC | chr1 | 170629999 | 170630029 | Hypo | PRRX1 |
| chr1 | 175346381 | 175346551 | Hypo | TNR | chr1 | 171665240 | 171665330 | Hypo | VAMP4 |
| chr1 | 179262226 | 179262256 | Hypo | SOAT1 | chr1 | 175388664 | 175388700 | Hypo | TNR |
| chr1 | 180925271 | 180925402 | Hypo | AK056657, KIAA1614 | chr1 | 180235730 | 180235760 | Hypo | LOC100527964, LHX4 |
| chr1 | 182862259 | 182862328 | Hypo | DHX9, SHCBP1L | chr1 | 182807578 | 182807742 | Hypo | DHX9, NPL |
| chr1 | 183462761 | 183463024 | Hypo | SMG7 | chr1 | 183129382 | 183129737 | Hypo | |
| chr1 | 184970783 | 184970847 | Hypo | | chr1 | 183627506 | 183627539 | Hypo | APOBEC4, RGL1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr1 | 195732322 | 195732539 | Hypo | | chr1 | 185336061 | 185336095 | Hypo | |
| chr1 | 197888831 | 197888945 | Hypo | LHX9 | chr1 | 197771547 | 197771893 | Hypo | |
| chr1 | 200478843 | 200478932 | Hypo | | chr1 | 198124799 | 198124932 | Hypo | NEK7 |
| chr1 | 201983113 | 201983200 | Hypo | ELF3, RNPEP | chr1 | 200591054 | 200591225 | Hypo | KIF14 |
| chr1 | 202311820 | 202311901 | Hypo | PPP1R12B, UBE2T | chr1 | 202081728 | 202081804 | Hypo | |
| chr1 | 203298307 | 203298710 | Hypo | | chr1 | 202856858 | 202856937 | Hypo | KLHL12, RABIF |
| chr1 | 204333609 | 204333668 | Hypo | LINC00628 | chr1 | 203429564 | 203429594 | Hypo | |
| chr1 | 206950282 | 206950328 | Hypo | IL10 | chr1 | 204478284 | 204478427 | Hypo | MDM4, TRNA_Lys |
| chr1 | 207227318 | 207227556 | Hypo | YOD1, PFKFB2 | chr1 | 207200870 | 207200962 | Hypo | PFKFB2, C1orf116 |
| chr1 | 207833206 | 207833370 | Hypo | CR1L | chr1 | 207794579 | 207794609 | Hypo | CR1 |
| chr1 | 211847706 | 211847787 | Hypo | NEK2 | chr1 | 209164972 | 209165091 | Hypo | |
| chr1 | 213189937 | 213190065 | Hypo | ANGEL2 | chr1 | 212963883 | 212964151 | Hypo | TATDN3, NSL1 |
| chr1 | 217309764 | 217309816 | Hypo | | chr1 | 217307624 | 217307654 | Hypo | |
| chr1 | 217805158 | 217805395 | Hypo | SPATA17, GPATCH2 | chr1 | 217311463 | 217311516 | Hypo | |
| chr1 | 220896508 | 220896568 | Hypo | | chr1 | 220636466 | 220636510 | Hypo | |
| chr1 | 223899470 | 223899500 | Hypo | CAPN2 | chr1 | 223894714 | 223894752 | Hypo | CAPN2 |
| chr1 | 224400490 | 224400524 | Hypo | | chr1 | 224267615 | 224267662 | Hypo | |
| chr1 | 224805564 | 224805620 | Hypo | CNIH3 | chr1 | 224804831 | 224804910 | Hypo | CNIH3 |
| chr1 | 225908076 | 225908184 | Hypo | AK124056 | chr1 | 225118306 | 225118474 | Hypo | DNAH14 |
| chr1 | 226384322 | 226384440 | Hypo | BC033346, ACBD3 | chr1 | 226265194 | 226265257 | Hypo | H3F3AP4, H3F3A, BC032899 |
| chr1 | 228528840 | 228529016 | Hypo | OBSCN | chr1 | 228201221 | 228201251 | Hypo | WNT3A |
| chr1 | 228693629 | 228693767 | Hypo | RNF187 | chr1 | 228558699 | 228559238 | Hypo | OBSCN |
| chr1 | 230404217 | 230404263 | Hypo | GALNT2 | chr] | 229476753 | 229476879 | Hypo | CCSAP |
| chr1 | 231475814 | 231476081 | Hypo | SPRTN, EXOC8 | chr1 | 231149928 | 231150098 | Hypo | MIR1182, FAM89A |
| chr1 | 234445373 | 234445403 | Hypo | MIR4671, SLC35F3 | chr1 | 233465473 | 233465503 | Hypo | KIAA1804 |
| chr1 | 234844955 | 234845079 | Hypo | | chr1 | 234798171 | 234798201 | Hypo | BC032040 |
| chr1 | 235665663 | 235665736 | Hypo | B3GALNT2 | chr1 | 235266920 | 235266950 | Hypo | TOMM20 |
| chr1 | 237970760 | 237970826 | Hypo | RYR2 | chr1 | 235669296 | 235669398 | Hypo | B3GALNT2 |
| chr1 | 241052096 | 241052126 | Hypo | RGS7 | chr1 | 240118848 | 240118973 | Hypo | |
| chr1 | 244115072 | 244115212 | Hypo | LOC339529 | chr1 | 243921295 | 243921330 | Hypo | |
| chr1 | 246330309 | 246330409 | Hypo | SMYD3 | chr1 | 245135753 | 245136064 | Hypo | EFCAB2 |
| chr1 | 247684856 | 247684929 | Hypo | GCSAML-AS1, OR2C3, AK130400, GCSAML | chr1 | 247284422 | 247284452 | Hypo | ZNF124, C1orf229 |
| chr1 | 248002278 | 248002437 | Hypo | OR11L1 | chr1 | 247910678 | 247910780 | Hypo | OR1C1 |
| chr1 | 248074729 | 248074927 | Hypo | OR2T8 | chr1 | 248028015 | 248028202 | Hypo | TRIM58 |
| chr1 | 248198552 | 248198721 | Hypo | OR2L2 | chr1 | 248099751 | 248099809 | Hypo | OR2L13 |
| chr1 | 248691575 | 248691616 | Hypo | OR2G6 | chr1 | 248328701 | 248328841 | Hypo | |
| chr1 | 249121600 | 249121704 | Hypo | MIR3124, SH3BP5L | chr1 | 248860898 | 248861046 | Hypo | |
| chr17 | 1136593 | 1136653 | Hypo | | chr17 | 617001 | 617064 | Hypo | VPS53 |
| chr17 | 1623703 | 1623735 | Hypo | WDR81, MIR22, AF070569, MIR22HG | chr17 | 1545976 | 1546442 | Hypo | RILP, PRPF8, SCARF1 |
| chr17 | 2219952 | 2220319 | Hypo | SRR, TSR1 | chr17 | 2207718 | 2208063 | Hypo | SMG6, SRR |
| chr17 | 2250051 | 2250081 | Hypo | SGSM2 | chr17 | 2220564 | 2221059 | Hypo | SRR, TSR1 |
| chr17 | 2538269 | 2538337 | Hypo | PAFAH1B1 | chr17 | 2496019 | 2496049 | Hypo | PAFAH1B1, DD413682 |
| chr17 | 2950959 | 2951091 | Hypo | RAPIGAP2 | chr17 | 2663898 | 2664032 | Hypo | |
| chr17 | 3658849 | 3659011 | Hypo | | chr17 | 3657502 | 3657553 | Hypo | |
| chr17 | 6470357 | 6470419 | Hypo | | chr17 | 4698990 | 4699252 | Hypo | GLTPD2, BC150535, VMO1, PSMB6 |
| chr17 | 7242844 | 7242899 | Hypo | ACAP1 | chr17 | 7043422 | 7043595 | Hypo | |
| chr17 | 8104145 | 8104260 | Hypo | AURKB | chr17 | 7488151 | 7488249 | Hypo | MPDU1, SOX15, SNORA67, SNORA48, SENP3-EIF4A1, FXR2, CD68, DD413682, SNORD10 |
| chr17 | 9790805 | 9790835 | Hypo | GLP2R | chr17 | 8774623 | 8774653 | Hypo | PIK3R5, PIK3R6 |
| chr17 | 12659029 | 12659063 | Hypo | MYOCD | chr17 | 10599510 | 10599546 | Hypo | ADPRM, SCO1 |
| chr17 | 16282251 | 16282300 | Hypo | UBB | chr17 | 16119860 | 16120047 | Hypo | PIGL, NCOR1 |
| chr17 | 19769739 | 19769812 | Hypo | TRNA_Gly | chr17 | 18162844 | 18163325 | Hypo | SMCR7, DQ596932, FLII |
| chr17 | 21003587 | 21003721 | Hypo | HP08942 | chr17 | 20817755 | 20817917 | Hypo | |
| chr17 | 25676959 | 25676989 | Hypo | | chr17 | 25620573 | 25620715 | Hypo | MIR4522, WSB1 |
| chr17 | 25907750 | 25907780 | Hypo | KSR1 | chr17 | 25680264 | 25680294 | Hypo | |
| chr17 | 26927249 | 26927410 | Hypo | SPAG5-AS1, SPAG5, SGK494 | chr17 | 26263183 | 26263322 | Hypo | |
| chr17 | 27036492 | 27037023 | Hypo | RAB34, NARR, RPL23A, PROCA1 | chr17 | 26961770 | 26961833 | Hypo | KIAA0100 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr17 | 27081845 | 27081963 | Hypo | FAM222B, TRAF4 | chr17 | 27056577 | 27056857 | Hypo | SNORD42B, RPL23A, NEK8, TLCD1, SNORD4B, SNORD42A, SNORD4A |
| chr17 | 27716114 | 27716220 | Hypo | MIR4523, TAOK1 | chr17 | 27170162 | 27170460 | Hypo | FAM222B |
| chr17 | 28112648 | 28112688 | Hypo | SSH2 | chr17 | 27716436 | 27716642 | Hypo | MIR4523, TAOK1 |
| chr17 | 29232244 | 29232350 | Hypo | TEFM | chr17 | 28112951 | 28113037 | Hypo | SSH2 |
| chr17 | 30243768 | 30243907 | Hypo | | chr17 | 29234283 | 29234313 | Hypo | TEFM |
| chr17 | 30710818 | 30710888 | Hypo | ZNF207 | chr17 | 30250325 | 30250364 | Hypo | |
| chr17 | 33721211 | 33721349 | Hypo | | chr17 | 32386720 | 32386875 | Hypo | |
| chr17 | 33917210 | 33917268 | Hypo | AP2B1 | chr17 | 33877286 | 33877439 | Hypo | SLFN14 |
| chr17 | 37011176 | 37011236 | Hypo | TRNA_Cys, SNORA21, RPL23 | chr17 | 37001415 | 37001921 | Hypo | C17orf98, RPL23, SNORA21 |
| chr17 | 37181771 | 37181865 | Hypo | LRRC37A11P | chr17 | 37131789 | 37132028 | Hypo | FBXO47 |
| chr17 | 37312431 | 37312477 | Hypo | ARL5C, TRNA_Cys, PLXDC1 | chr17 | 37192072 | 37192201 | Hypo | LRRC37A11P |
| chr17 | 37484062 | 37484128 | Hypo | FBXL20 | chr17 | 37369180 | 37369210 | Hypo | STAC2, RPL19 |
| chr17 | 38335459 | 38335533 | Hypo | CASC3, RAPGEFL1 | chr17 | 38179397 | 38179430 | Hypo | CSF3, MED24, SNORD124 |
| chr17 | 38574991 | 38575021 | Hypo | TOP2A | chr17 | 38380553 | 38380598 | Hypo | WIPF2 |
| chr17 | 39834201 | 39834287 | Hypo | | chr17 | 39682352 | 39682711 | Hypo | JUP, KRT19, AK090604, KRT15 |
| chr17 | 41175146 | 41175331 | Hypo | RND2, VAT1, IFI35 | chr17 | 40975413 | 40975677 | Hypo | PSME3, BECN1 |
| chr17 | 41651850 | 41651880 | Hypo | | chr17 | 41278621 | 41278700 | Hypo | NBR2, BRCA1 |
| chr17 | 42142661 | 421428000 | Hypo | G6PC3, AX746969, LSM12 | chr17 | 41745825 | 41745855 | Hypo | MEOX1 |
| chr17 | 42321590 | 42321647 | Hypo | SLC4A1 | chr17 | 42246452 | 42246521 | Hypo | ASB16, ASB16-AS1, C17orf65, C17orf53 |
| chr17 | 42587249 | 42587355 | Hypo | | chr17 | 42331412 | 42331659 | Hypo | SLC4A1 |
| chr17 | 42767947 | 42768198 | Hypo | CCDC43 | chr17 | 42590091 | 42590224 | Hypo | |
| chr17 | 42975726 | 42975756 | Hypo | EFTUD2, CCDC103, FAM187A, AK124465, GFAP | chr17 | 42787481 | 42787615 | Hypo | DBF4B |
| chr17 | 45022106 | 45022140 | Hypo | GOSR2 | chr17 | 43001891 | 43001946 | Hypo | KIF18B, GFAP |
| chr17 | 46567400 | 46567655 | Hypo | | chr17 | 45187608 | 45187638 | Hypo | CDC27 |
| chr17 | 47657544 | 47657583 | Hypo | NXPH3 | chr17 | 46827420 | 46827539 | Hypo | |
| chr17 | 48612223 | 48612308 | Hypo | EPN3, SPATA20, MYCBPAP | chr17 | 48473056 | 48473236 | Hypo | |
| chr17 | 48799820 | 48799866 | Hypo | LUC7L3 | chr17 | 48653128 | 48653158 | Hypo | CACNAIG |
| chr17 | 53814544 | 53814678 | Hypo | | chr17 | 49229267 | 49229703 | Hypo | NME1-NME2, NME1 |
| chr17 | 56092600 | 56092736 | Hypo | SRSF1 | chr17 | 55037326 | 55037626 | Hypo | COIL |
| chr17 | 57296865 | 57297129 | Hypo | GDPD1, SMG8 | chr17 | 56743206 | 56743249 | Hypo | TEX14 |
| chr17 | 57787402 | 57787546 | Hypo | PTRH2, VMP1 | chr17 | 57386255 | 57386735 | Hypo | |
| chr17 | 61677374 | 61677404 | Hypo | TACO1, BC024682, DQ577731, DCAF7 | chr17 | 57832475 | 57832607 | Hypo | VMP1 |
| chr17 | 62028596 | 62028790 | Hypo | SCN4A | chr17 | 61817576 | 61817955 | Hypo | STRADA, CCDC47 |
| chr17 | 65715296 | 65715493 | Hypo | NOL11 | chr17 | 64672366 | 64672544 | Hypo | |
| chr17 | 70586165 | 70586272 | Hypo | LINC00511, LINC00673 | chr17 | 67410305 | 67410397 | Hypo | MAP2K6 |
| chr17 | 73031637 | 73031935 | Hypo | KCTD2, ATP5H, Metazoa_SRP, TRNA_Arg, JB153618 | chr17 | 71229815 | 71229918 | Hypo | C17orf80, FAM104A |
| chr17 | 73115884 | 73115914 | Hypo | ARMC7 | chr17 | 73115588 | 73115658 | Hypo | ARMC7 |
| chr17 | 73147177 | 73147356 | Hypo | HN1 | chr17 | 73128301 | 73128338 | Hypo | HN1, NT5C, ARMC7 |
| chr17 | 73545998 | 73546299 | Hypo | LLGL2 | chr17 | 73147774 | 73147992 | Hypo | HN1 |
| chr17 | 73608306 | 73608336 | Hypo | MYO15B | chr17 | 73586015 | 73586418 | Hypo | MYO15B |
| chr17 | 73692986 | 73693122 | Hypo | SAP30BP | chr17 | 73636144 | 73636337 | Hypo | SMIM6, RECQL5, SMIM5 |
| chr17 | 73901630 | 73901893 | Hypo | FBF1, MRPL38, TRIM65 | chr17 | 73782870 | 73782947 | Hypo | UNK, MIR4738, H3F3B |
| chr17 | 74047797 | 74048063 | Hypo | SRP68 | chr17 | 74028346 | 74028413 | Hypo | SRP68, EVPL |
| chr17 | 74390363 | 74390393 | Hypo | UBE2O, SPHK1 | chr17 | 74299798 | 74299899 | Hypo | PRPSAP1, QRICH2 |
| chr17 | 75734101 | 75734131 | Hypo | | chr17 | 75523142 | 75523272 | Hypo | BC040189 |
| chr17 | 76021047 | 76021077 | Hypo | TNRC6C | chr17 | 75797111 | 75797179 | Hypo | |
| chr17 | 76137951 | 76138190 | Hypo | TMC8, C17orf99 | chr17 | 76135783 | 76136001 | Hypo | C17orf99, TMC8 |
| chr17 | 76207342 | 76207372 | Hypo | BIRC5, AFMID | chr17 | 76138498 | 76138622 | Hypo | C17orf99, TMC8 |
| chr17 | 76974447 | 76974499 | Hypo | LGALS3BP | chr17 | 76211302 | 76211506 | Hypo | BIRC5, AFMID, EPR-1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr17 | 76984053 | 76984188 | Hypo | CANT1, DQ595190, LGALS3BP | chr17 | 76983518 | 76983669 | Hypo | CANT1, LGALS3BP |
| chr17 | 77145129 | 77145242 | Hypo | RBFOX3 | chr17 | 77105055 | 77105198 | Hypo | RBFOX3 |
| chr17 | 77827114 | 77827201 | Hypo | | chr17 | 77825696 | 77825812 | Hypo | |
| chr17 | 78447127 | 78447157 | Hypo | NPTX1, AX746631 | chr17 | 78122158 | 78122190 | Hypo | EIF4A3 |
| chr17 | 78599596 | 78599628 | Hypo | RPTOR | chr17 | 78518031 | 78518198 | Hypo | RPTOR |
| chr17 | 78874441 | 78874559 | Hypo | | chr17 | 78667992 | 78668159 | Hypo | RPTOR |
| chr17 | 79094182 | 79094245 | Hypo | MIR657, MIR3065, MIR338, AATK | chr17 | 78975667 | 78975758 | Hypo | AF258550, CHMP6 |
| chr17 | 79626955 | 79626985 | Hypo | OXLD1, CCDC137, PDE6G | chr17 | 79626591 | 79626703 | Hypo | OXLD1, CCDC137, PDE6G |
| chr17 | 79850445 | 79850537 | Hypo | ANAPC11, NPB, ALYREF | chr17 | 79769433 | 79769693 | Hypo | GCGR |
| chr17 | 80254266 | 80254296 | Hypo | BC033560 | chr17 | 79939605 | 79939835 | Hypo | ASPSCR1 |
| chr17 | 80289858 | 80289892 | Hypo | SECTM1 | chr17 | 80289234 | 80289310 | Hypo | SECTM1 |
| chr17 | 80479311 | 80479559 | Hypo | FOXK2 | chr17 | 80294282 | 80294427 | Hypo | SECTM1 |
| chr17 | 80654983 | 80655013 | Hypo | RAB40B | chr17 | 80593754 | 80594107 | Hypo | WDR45B |
| chr17 | 80832305 | 80832411 | Hypo | | chr17 | 80797692 | 80798345 | Hypo | TBCD, ZNF750 |
| chr17 | 81008618 | 81008826 | Hypo | | chr17 | 80832712 | 80832796 | Hypo | |
| chr17 | 81048993 | 81049023 | Hypo | METRNL | chr17 | 81033487 | 81033517 | Hypo | METRNL |
| chr5 | 481012 | 481121 | Hypo | PP7080, AK023178, FLJ00157, BC013821, SLC9A3 | chr17 | 81049994 | 81050058 | Hypo | METRNL |
| chr5 | 538758 | 538806 | Hypo | MIR 4456 | chr5 | 491335 | 491536 | Hypo | |
| chr5 | 555158 | 555285 | Hypo | | chr5 | 554299 | 554538 | Hypo | |
| chr5 | 677889 | 678006 | Hypo | TPPP | chr5 | 555965 | 555995 | Hypo | |
| chr5 | 1117778 | 1118270 | Hypo | | chr5 | 1034600 | 1034653 | Hypo | NKD2 |
| chr5 | 1193381 | 1193521 | Hypo | SLC6A19 | chr5 | 1131217 | 1131378 | Hypo | |
| chr5 | 1221197 | 1221307 | Hypo | SLC6A18, SLC6A19 | chr5 | 1193880 | 1193944 | Hypo | SLC6A19 |
| chr5 | 1787378 | 1787418 | Hypo | | chr5 | 1747022 | 1747098 | Hypo | |
| chr5 | 2324383 | 2324413 | Hypo | | chr5 | 1950794 | 1950960 | Hypo | |
| chr5 | 2541487 | 2541611 | Hypo | | chr5 | 2367718 | 2367892 | Hypo | |
| chr5 | 3325042 | 3325272 | Hypo | | chr5 | 3031879 | 3032018 | Hypo | |
| chr5 | 4144367 | 4144516 | Hypo | | chr5 | 3674053 | 3674224 | Hypo | |
| chr5 | 6482458 | 6482620 | Hypo | UBE2QL1 | chr5 | 6228617 | 6228790 | Hypo | |
| chr5 | 16466784 | 16467120 | Hypo | ZNF622, FAM134B | chr5 | 10616516 | 10616550 | Hypo | ANKRD33B |
| chr5 | 23011928 | 23011958 | Hypo | | chr5 | 17203012 | 17203177 | Hypo | LOC285696 |
| chr5 | 31691477 | 31691652 | Hypo | PDZD2 | chr5 | 31572285 | 31572344 | Hypo | |
| chr5 | 32446143 | 32446274 | Hypo | ZFR | chr5 | 32314345 | 32314379 | Hypo | MTMR12 |
| chr5 | 33298005 | 33298076 | Hypo | | chr5 | 33234280 | 33234411 | Hypo | |
| chr5 | 33936486 | 33936516 | Hypo | RXFP3, SLC45A2 | chr5 | 33509607 | 33509776 | Hypo | |
| chr5 | 39343181 | 39343348 | Hypo | C9 | chr5 | 37376644 | 37376674 | Hypo | WDR70, NUP155 |
| chr5 | 42260181 | 42260453 | Hypo | | chr5 | 40775147 | 40775313 | Hypo | PRKAA1 |
| chr5 | 43215581 | 43215626 | Hypo | NIM1 | chr5 | 42931966 | 42931996 | Hypo | |
| chr5 | 43558065 | 43558099 | Hypo | PAIP1 | chr5 | 43402678 | 43403084 | Hypo | CCL28 |
| chr5 | 56077938 | 56078065 | Hypo | | chr5 | 52887899 | 52888047 | Hypo | NDUFS4 |
| chr5 | 65181732 | 65181778 | Hypo | | chr5 | 56467399 | 56467666 | Hypo | GPBP1 |
| chr5 | 72528434 | 72528464 | Hypo | | chr5 | 68391042 | 68391336 | Hypo | SLC30A5 |
| chr5 | 74991793 | 74991908 | Hypo | POC5 | chr5 | 74061571 | 74061786 | Hypo | NSA2, GFM2 |
| chr5 | 77655342 | 77655388 | Hypo | SCAMP1, BC039455 | chr5 | 76327468 | 76327697 | Hypo | AGGF1 |
| chr5 | 78910189 | 78910332 | Hypo | PAPD4 | chr5 | 78005726 | 78005913 | Hypo | |
| chr5 | 79598681 | 79598836 | Hypo | LOC644936 | chr5 | 79563425 | 79563643 | Hypo | |
| chr5 | 79947584 | 79947707 | Hypo | MSH3, MTRNR2L2, DHFR | chr5 | 79783240 | 79783421 | Hypo | FAM151B, ZFYVE16 |
| chr5 | 94889396 | 94889434 | Hypo | ARSK, TTC37 | chr5 | 86414242 | 86414297 | Hypo | BC034940, MIR4280 |
| chr5 | 115154758 | 115154825 | Hypo | ATG12, CDO1 | chr5 | 94982042 | 94982225 | Hypo | RFESD, SPATA9 |
| chr5 | 120399966 | 120400129 | Hypo | | chr5 | 115176039 | 115176228 | Hypo | AP3S1, ATG12 |
| chr5 | 130153448 | 130153623 | Hypo | | chr5 | 127088743 | 127088773 | Hypo | |
| chr5 | 133968996 | 133969192 | Hypo | SAR1B | chr5 | 133820008 | 133820040 | Hypo | |
| chr5 | 137404150 | 137404180 | Hypo | | chr5 | 134582864 | 134582894 | Hypo | LOC340073, LOC100996485 |
| chr5 | 147003444 | 147003536 | Hypo | JAKMIP2, JAKMIP2-AS1 | chr5 | 139779555 | 139779871 | Hypo | BC030152, ANKHD1, ANKHD1-EIF4EBP3 |
| chr5 | 154030048 | 154030160 | Hypo | | chr5 | 147326357 | 147326510 | Hypo | |
| chr5 | 154209926 | 154209987 | Hypo | FAXDC2 | chr5 | 154061801 | 154061894 | Hypo | |
| chr5 | 156485385 | 156485415 | Hypo | HAVCR1 | chr5 | 154318148 | 154318485 | Hypo | MRPL22, GEMIN5 |
| chr5 | 156655170 | 156655200 | Hypo | ITK | chr5 | 156558444 | 156558689 | Hypo | MED7 |
| chr5 | 157078419 | 157078449 | Hypo | SOX30 | chr5 | 156874257 | 156874308 | Hypo | ADAM19 |
| chr5 | 158524865 | 158524925 | Hypo | AK123543, EBF1 | chr5 | 157673799 | 157673964 | Hypo | |
| chr5 | 159437197 | 159437235 | Hypo | TTC1 | chr5 | 158612981 | 158613074 | Hypo | RNF145 |
| chr5 | 168233396 | 168233482 | Hypo | SLIT3 | chr5 | 166865449 | 166865616 | Hypo | TENM2 |
| chr5 | 169532927 | 169533012 | Hypo | FOXI1 | chr5 | 169366082 | 169366201 | Hypo | FAM196B, DOCK2 |
| chr5 | 172672477 | 172672663 | Hypo | | chr5 | 172485539 | 172485586 | Hypo | CREBRF, Y_RNA |
| chr5 | 174921456 | 174921629 | Hypo | SFXN1 | chr5 | 174159104 | 174159134 | Hypo | MSX2 |
| chr5 | 175971447 | 175971615 | Hypo | CDHR2 | chr5 | 175876388 | 175876504 | Hypo | FAF2 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr5 | 177020093 | 177020153 | Hypo | B4GALT7, TMED9 | chr5 | 175978889 | 175978976 | Hypo | CDHR2 |
| chr5 | 177408292 | 177408443 | Hypo | | chr5 | 177031167 | 177031197 | Hypo | B4GALT7, TMED9 |
| chr5 | 177556807 | 177557022 | Hypo | RMND5B, AK127224, N4BP3 | chr5 | 177512244 | 177512377 | Hypo | |
| chr5 | 177713376 | 177713468 | Hypo | | chr5 | 177579824 | 177580065 | Hypo | NHP2, RMND5B |
| chr5 | 178655753 | 178655871 | Hypo | ADAMTS2 | chr5 | 178576356 | 178576499 | Hypo | ADAMTS2 |
| chr5 | 178969722 | 178969752 | Hypo | RUFY1 | chr5 | 178955527 | 178955656 | Hypo | AX747985 |
| chr5 | 179060235 | 179060655 | Hypo | C5orf60 | chr5 | 178978946 | 178978976 | Hypo | RUFY1 |
| chr5 | 179214113 | 179214196 | Hypo | LTC4S, MAML1 | chr5 | 179098595 | 179098633 | Hypo | CBY3 |
| chr5 | 180030654 | 180030700 | Hypo | FLT4 | chr5 | 179553207 | 179553237 | Hypo | RASGEF1C |
| chr5 | 180326126 | 180326156 | Hypo | BTNL8 | chr5 | 180047440 | 180047606 | Hypo | FLT4 |
| chr5 | 180612346 | 180612376 | Hypo | TRNA_Leu, TRNA_Val, TRNA_Pro, TRNA_Thr, TRIM7 | chr5 | 180454232 | 180454334 | Hypo | |
| chr5 | 180636016 | 180636205 | Hypo | TRNA_Val, TRNA_Lys, TRNA_Ala, TRIM7 | chr5 | 180629320 | 180629350 | Hypo | TRIM7, TRNA_Ala, TRNA_Lys |
| chr14 | 23426755 | 23426785 | Hypo | MIR4707, HAUS4 | chr14 | 23400315 | 23400354 | Hypo | TRNA, TRNA_Arg, PRMT5 |
| chr14 | 24562744 | 24562774 | Hypo | PCK2 | chr14 | 23706727 | 23706765 | Hypo | |
| chr14 | 25155907 | 25155937 | Hypo | | chr14 | 25071566 | 25071612 | Hypo | GZMH |
| chr14 | 31925554 | 31925724 | Hypo | DTD2, BC041327 | chr14 | 31027323 | 31027367 | Hypo | G2E3 |
| chr14 | 35024446 | 35024546 | Hypo | SNX6 | chr14 | 35023111 | 35023322 | Hypo | SNX6 |
| chr14 | 39579800 | 39579830 | Hypo | GEMIN2 | chr14 | 35389907 | 35389943 | Hypo | |
| chr14 | 50233426 | 50233459 | Hypo | KLHDC2 | chr14 | 45602514 | 45602576 | Hypo | FKBP3, FANCM |
| chr14 | 50334254 | 50334355 | Hypo | Metazoa_SRP | chr14 | 50333754 | 50333994 | Hypo | Metazoa_SRP |
| chr14 | 52765920 | 52766075 | Hypo | | chr14 | 50777663 | 50777714 | Hypo | ATP5S, L2HGDH |
| chr14 | 55765372 | 55765606 | Hypo | FBXO34 | chr14 | 55370202 | 55370235 | Hypo | |
| chr14 | 57270936 | 57270987 | Hypo | OTX2, OTX2-AS1 | chr14 | 57045520 | 57045739 | Hypo | TMEM260 |
| chr14 | 58893052 | 58893183 | Hypo | KIAA0586, TIMM9 | chr14 | 58857094 | 58857355 | Hypo | TOMM20L |
| chr14 | 64222413 | 64222488 | Hypo | | chr14 | 64107335 | 64107600 | Hypo | |
| chr14 | 65233339 | 65233464 | Hypo | SPTB | chr14 | 65005696 | 65005833 | Hypo | HSPA2 |
| chr14 | 67585164 | 67585413 | Hypo | GPHN | chr14 | 66498931 | 66498975 | Hypo | |
| chr14 | 68334928 | 68335108 | Hypo | RAD51B | chr14 | 67886378 | 67886606 | Hypo | PLEK2 |
| chr14 | 69867022 | 69867196 | Hypo | SLC39A9, ERH | chr14 | 69866541 | 69866706 | Hypo | SLC39A9, ERH |
| chr14 | 73175026 | 73175148 | Hypo | DPF3 | chr14 | 73167750 | 73167899 | Hypo | DPF3 |
| chr14 | 73180208 | 73180314 | Hypo | DPF3 | chr14 | 73178807 | 73178865 | Hypo | DPF3 |
| chr14 | 73231266 | 73231414 | Hypo | DPF3 | chr14 | 73226952 | 73227005 | Hypo | DPF3 |
| chr14 | 73318471 | 73318629 | Hypo | DPF3 | chr14 | 73236095 | 73236178 | Hypo | DPF3 |
| chr14 | 73602250 | 73602389 | Hypo | PSEN1 | chr14 | 73333249 | 73333396 | Hypo | DPF3 |
| chr14 | 73855616 | 73855646 | Hypo | NUMB | chr14 | 73604570 | 73604718 | Hypo | PSEN1 |
| chr14 | 74529109 | 74529139 | Hypo | ALDH6A1, CCDC176 | chr14 | 73956853 | 73956913 | Hypo | HEATR4, C14orf169 |
| chr14 | 76128674 | 76128842 | Hypo | TTLL5, C14orf1 | chr14 | 75760311 | 75760347 | Hypo | LOC731223 |
| chr14 | 90983328 | 90983360 | Hypo | | chr14 | 88457599 | 88457685 | Hypo | U6, GALC |
| chr14 | 93155061 | 93155315 | Hypo | | chr14 | 92507578 | 92507639 | Hypo | AX721199, BC039675, TRIP11 |
| chr14 | 95233705 | 95233765 | Hypo | GSC | chr14 | 93706752 | 93706782 | Hypo | BTBD7 |
| chr14 | 95740035 | 95740116 | Hypo | CLMN | chr14 | 95240227 | 95240341 | Hypo | GSC |
| chr14 | 97045354 | 97045431 | Hypo | | chr14 | 96053974 | 96054020 | Hypo | BC038791 |
| chr14 | 100643350 | 100643481 | Hypo | | chr14 | 100148073 | 100148230 | Hypo | CYP46A1, MIR5698, HHIPL1 |
| chr14 | 101250109 | 101250272 | Hypo | | chr14 | 100843765 | 100843912 | Hypo | WDR25, WARS |
| chr14 | 102521602 | 102521758 | Hypo | | chr14 | 102418607 | 102418637 | Hypo | |
| chr14 | 102530007 | 102530234 | Hypo | | chr14 | 102529325 | 102529419 | Hypo | |
| chr14 | 102682077 | 102682123 | Hypo | MOK, AK130824, WDR20 | chr14 | 102530500 | 102530530 | Hypo | |
| chr14 | 103477643 | 103477794 | Hypo | | chr14 | 102772607 | 102772695 | Hypo | MOK |
| chr14 | 104202705 | 104202759 | Hypo | PPP1R13B, ZFYVE21 | chr14 | 104160060 | 104160134 | Hypo | XRCC3, AK097119, AX746968 |
| chr14 | 104386476 | 104387067 | Hypo | TDRD9, C14orf2 | chr14 | 104355204 | 104355273 | Hypo | |
| chr14 | 104571985 | 104572116 | Hypo | ASPG | chr14 | 104547785 | 104547909 | Hypo | ASPG |
| chr14 | 104627664 | 104627759 | Hypo | KIF26A | chr14 | 104620411 | 104620554 | Hypo | KIF26A |
| chr14 | 104646317 | 104646491 | Hypo | KIF26A | chr14 | 104645126 | 104645188 | Hypo | KIF26A |
| chr14 | 104682545 | 104682656 | Hypo | | chr14 | 104647257 | 104647287 | Hypo | KIF26A |
| chr14 | 104897228 | 104897294 | Hypo | | chr14 | 104862860 | 104863026 | Hypo | |
| chr14 | 105658349 | 105658425 | Hypo | | chr14 | 105157485 | 105157554 | Hypo | INF2 |
| chr6 | 373148 | 373290 | Hypo | | chr14 | 105714258 | 105714334 | Hypo | BTBD6, BRF1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr6 | 3053299 | 3053386 | Hypo | | chr6 | 2986688 | 2986718 | Hypo | NQO2, DKFZP686I15217 |
| chr6 | 3405645 | 3405713 | Hypo | SLC22A23 | chr6 | 3285222 | 3285513 | Hypo | SLC22A23, AX746991 |
| chr6 | 4951247 | 4951390 | Hypo | CDYL | chr6 | 4836002 | 4836458 | Hypo | CDYL |
| chr6 | 6367086 | 6367271 | Hypo | LY86-AS1 | chr6 | 5783325 | 5783496 | Hypo | |
| chr6 | 10734917 | 10735045 | Hypo | TMEM14C | chr6 | 10390384 | 10390447 | Hypo | TFAP2A |
| chr6 | 13797690 | 13797736 | Hypo | MCUR1 | chr6 | 12288517 | 12288681 | Hypo | EDN1 |
| chr6 | 14986483 | 14986522 | Hypo | | chr6 | 14687918 | 14688084 | Hypo | |
| chr6 | 17750276 | 17750306 | Hypo | KIF13A | chr6 | 16197030 | 16197112 | Hypo | |
| chr6 | 24647342 | 24647599 | Hypo | TDP2, KIAA0319 | chr6 | 19892448 | 19892627 | Hypo | |
| chr6 | 26189859 | 26189991 | Hypo | HIST1H3D, HIST1H3F, HIST1H2AD, HIST1H2BF, HIST1H4D, HIST1H2BE | chr6 | 24662439 | 24662469 | Hypo | ACOT13, TDP2 |
| chr6 | 26254617 | 26254647 | Hypo | HIST1H2BH, HIST1H3F, HIST1H4G | chr6 | 26214514 | 26214648 | Hypo | HIST1H2BG, HIST1H2AE, HIST1H3F, HIST1H4E |
| chr6 | 33955505 | 33955731 | Hypo | | chr6 | 27441812 | 27441842 | Hypo | TRNA_Ser, TRNA_Asp, ZNF184 |
| chr6 | 34219930 | 34219972 | Hypo | C6orf1, HMGA1 | chr6 | 34170970 | 34171061 | Hypo | |
| chr6 | 34535802 | 34535832 | Hypo | | chr6 | 34396431 | 34396542 | Hypo | RPS10 |
| chr6 | 35150041 | 35150080 | Hypo | | chr6 | 34724047 | 34724228 | Hypo | SNRPC |
| chr6 | 36165662 | 36165692 | Hypo | BRPF3, BC042825 | chr6 | 35470285 | 35470399 | Hypo | TULP1, TEAD3 |
| chr6 | 36392273 | 36392323 | Hypo | PXT1 | chr6 | 36313883 | 36313913 | Hypo | ETV7, C6orf222 |
| chr6 | 37024559 | 37024589 | Hypo | | chr6 | 36406316 | 36406370 | Hypo | KCTD20, PXT1 |
| chr6 | 37545401 | 37545495 | Hypo | | chr6 | 37392127 | 37392189 | Hypo | FTSJD2 |
| chr6 | 37776703 | 37776735 | Hypo | | chr6 | 37776410 | 37776440 | Hypo | |
| chr6 | 42062143 | 42062346 | Hypo | C6orf132 | chr6 | 41273881 | 41273942 | Hypo | |
| chr6 | 42111015 | 42111051 | Hypo | C6orf132 | chr6 | 42090977 | 42091027 | Hypo | C6orf132 |
| chr6 | 42773440 | 42773622 | Hypo | GLTSCR1L | chr6 | 42711893 | 42711923 | Hypo | TBCC |
| chr6 | 42990166 | 42990485 | Hypo | RRP36, KLHDC3, MEA1 | chr6 | 42846662 | 42846705 | Hypo | RPL7L1, DQ581019 |
| chr6 | 43424297 | 43424470 | Hypo | DLK2, ABCC10 | chr6 | 43119019 | 43119540 | Hypo | PTK7 |
| chr6 | 43425479 | 43425509 | Hypo | DLK2, ABCC10 | chr6 | 43425152 | 43425207 | Hypo | DLK2, ABCC10 |
| chr6 | 44240914 | 44241108 | Hypo | TCTE1, SPATS1, TMEM151B, NFKBIE | chr6 | 43478676 | 43478745 | Hypo | YIPF3, POLR1C, LRRC73, TJAP1 |
| chr6 | 47473194 | 47473287 | Hypo | CD2AP | chr6 | 44695763 | 44695795 | Hypo | BX647715 |
| chr6 | 49765146 | 49765202 | Hypo | | chr6 | 49590755 | 49590786 | Hypo | RHAG |
| chr6 | 52929051 | 52929233 | Hypo | ICK, FBXO9 | chr6 | 52928742 | 52928776 | Hypo | FBXO9, ICK |
| chr6 | 57694587 | 57694617 | Hypo | | chr6 | 53052723 | 53052859 | Hypo | |
| chr6 | 75995789 | 75995819 | Hypo | FILIP1, LOC100506804, TMEM30A | chr6 | 58147523 | 58147594 | Hypo | TRNA_Ile, TRNA_Ala |
| chr6 | 83546464 | 83546498 | Hypo | | chr6 | 82958615 | 82958917 | Hypo | IBTK |
| chr6 | 86302413 | 86302614 | Hypo | SNX14 | chr6 | 85050415 | 85050504 | Hypo | |
| chr6 | 99396456 | 99396609 | Hypo | | chr6 | 89672213 | 89672376 | Hypo | RNGTT |
| chr6 | 100135425 | 100135583 | Hypo | | chr6 | 100050765 | 100050815 | Hypo | PRDM13 |
| chr6 | 107075651 | 107075704 | Hypo | QRSL1, RTN4IP1 | chr6 | 105821423 | 105821453 | Hypo | PREP |
| chr6 | 108181556 | 108181721 | Hypo | SEC63 | chr6 | 107562769 | 107562859 | Hypo | PDSS2 |
| chr6 | 110437721 | 110437751 | Hypo | WASF1 | chr6 | 108280292 | 108280352 | Hypo | SEC63 |
| chr6 | 117000853 | 117001032 | Hypo | KPNA5, AX746765 | chr6 | 113852508 | 113852634 | Hypo | |
| chr6 | 119483052 | 119483082 | Hypo | | chr6 | 119254629 | 119254678 | Hypo | MCM9 |
| chr6 | 134176232 | 134176299 | Hypo | MGC34034, BC041459 | chr6 | 134067194 | 134067471 | Hypo | BC041459 |
| chr6 | 149868348 | 149868387 | Hypo | PPIL4 | chr6 | 134589500 | 134589767 | Hypo | SGK1 |
| chr6 | 151650396 | 151650453 | Hypo | AKAP12 | chr6 | 150183760 | 150183874 | Hypo | LOC100652739, LRP11 |
| chr6 | 157037549 | 157037677 | Hypo | | chr6 | 155569208 | 155569305 | Hypo | AB075492, AK022993, TFB1M, TIAM2 |
| chr6 | 157506082 | 157506112 | Hypo | | chr6 | 157502438 | 157502561 | Hypo | |
| chr6 | 159228187 | 159228217 | Hypo | AX747826, EZR | chr6 | 157637455 | 157637500 | Hypo | |
| chr6 | 161645992 | 161646255 | Hypo | | chr6 | 159419589 | 159419717 | Hypo | RSPH3 |
| chr6 | 164114396 | 164114524 | Hypo | AK093114 | chr6 | 161780056 | 161780139 | Hypo | PARK2 |
| chr6 | 164183602 | 164183632 | Hypo | AK093114 | chr6 | 164179636 | 164179668 | Hypo | AK093114 |
| chr6 | 164215532 | 164215633 | Hypo | | chr6 | 164196971 | 164197003 | Hypo | AK093114 |
| chr6 | 164246015 | 164246143 | Hypo | | chr6 | 164228294 | 164228363 | Hypo | |
| chr6 | 164314289 | 164314443 | Hypo | | chr6 | 164283254 | 164283377 | Hypo | |
| chr6 | 166944367 | 166944403 | Hypo | | chr6 | 164322666 | 164322775 | Hypo | |
| chr6 | 167835129 | 167835171 | Hypo | | chr6 | 167202601 | 167202801 | Hypo | |
| chr6 | 170240639 | 170240714 | Hypo | | chr6 | 168858122 | 168858296 | Hypo | SMOC2 |
| chr6 | 170475105 | 170475267 | Hypo | | chr6 | 170264728 | 170264761 | Hypo | |

TABLE 1-continued

| Chr | Start | Stop | Hypo/hyper | Annotation | Chr | Start | Stop | Hypo/hyper | Annotation |
|---|---|---|---|---|---|---|---|---|---|
| JH636052.4 | 2022736 | 2022766 | Hypo | | chr6 | 170894820 | 170894912 | Hypo | PDCD2 |
| chr16 | 199886 | 199943 | Hypo | HBZ | chr16 | 189744 | 189933 | Hypo | NPRL3 |
| chr16 | 280323 | 280395 | Hypo | ITFG3, LUC7L | chr16 | 232136 | 232166 | Hypo | LUC7L, HBQ1, HBA1, HBA2 |
| chr16 | 318498 | 318763 | Hypo | RGS11, ITFG3 | chr16 | 318104 | 318227 | Hypo | RGS11, ITFG3 |
| chr16 | 410377 | 410407 | Hypo | MRPL28, AXIN1 | chr16 | 337599 | 337659 | Hypo | AXIN1, PDIA2, ARHGDIG |
| chr16 | 611385 | 611520 | Hypo | NHLRC4, PIGQ, C16orf11, SOLH | chr16 | 571714 | 571959 | Hypo | LINC00235, SOLH, RAB11FIP3 |
| chr16 | 612869 | 613037 | Hypo | NHLRC4, PIGQ, C16orf11, SOLH | chr16 | 611969 | 612260 | Hypo | NHLRC4, PIGQ, C16orf11, SOLH |
| chr16 | 726626 | 726990 | Hypo | STUB1, JMJD8, WDR24, RHBDL1, RHOT2, WDR90 | chr16 | 700299 | 700329 | Hypo | WDR90, FAM195A |
| chr16 | 735205 | 735594 | Hypo | FBXL16, WDR24 JMJD8, STUB1, RHBDL1 | chr16 | 731488 | 731610 | Hypo | JMJD8, WDR24, STUB1, RHBDL1, RHOT2 |
| chr16 | 741376 | 741601 | Hypo | FBXL16, WDR24 JMJD8, STUB1 | chr16 | 740791 | 740914 | Hypo | FBXL16, WDR24 JMJD8, STUB1 |
| chr16 | 837361 | 837460 | Hypo | CHTF18, RPUSD1 | chr16 | 762523 | 762694 | Hypo | CCDC78, METRN, AL360260, FAM173A |
| chr16 | 882484 | 882588 | Hypo | | chr16 | 845955 | 845985 | Hypo | GNG13, PRR25, CHTF18, RPUSD1 |
| chr16 | 943481 | 943553 | Hypo | LMF1 | chr16 | 895093 | 895166 | Hypo | LMF1 |
| chr16 | 1052587 | 1052627 | Hypo | | chr16 | 1018120 | 1018150 | Hypo | LMF1 |
| chr16 | 1116661 | 1116691 | Hypo | SSTR5, SSTR5-AS1 | chr16 | 1102927 | 1102957 | Hypo | |
| chr16 | 1155162 | 1155212 | Hypo | C1QTNF8 | chr16 | 1129011 | 1129140 | Hypo | C1QTNF8, SSTR5, BC084558, SSTR5-AS1 |
| chr16 | 1217307 | 1217503 | Hypo | CACNA1H | chr16 | 1186809 | 1186850 | Hypo | |
| chr16 | 1228804 | 1228916 | Hypo | CACNA1H | chr16 | 1218034 | 1218090 | Hypo | CACNA1H |
| chr16 | 1248604 | 1248675 | Hypo | CACNA1H | chr16 | 1229970 | 1230142 | Hypo | CACNA1H |
| chr16 | 1271546 | 1271646 | Hypo | TPSG1, TPSB2, CACNA1H | chr16 | 1267925 | 1268120 | Hypo | TPSG1, TPSB2, CACNA1H |
| chr16 | 1323976 | 1324061 | Hypo | | chr16 | 1312526 | 1312611 | Hypo | TPSD1 |
| chr16 | 1407370 | 1407629 | Hypo | UNKL, GNPTG, STR3, BAIAP3 | chr16 | 1394502 | 1394596 | Hypo | TSR3, GNPTG, BALAP3 |
| chr16 | 1428508 | 1428873 | Hypo | UNKL | chr16 | 1408210 | 1408240 | Hypo | GNPTG, TSR3, BALAP3, UNKL |
| chr16 | 1469334 | 1469527 | Hypo | C16orf91, UNKL | chr16 | 1466425 | 1466455 | Hypo | C16orf91, UNKL |
| chr16 | 1523925 | 1523971 | Hypo | CLCN7 | chr16 | 1491567 | 1491613 | Hypo | CLCN7, CCDC154 |
| chr16 | 1730306 | 1730597 | Hypo | HN1L, CRAMP1L | chr16 | 1729868 | 1730022 | Hypo | HNIL, CRAMP1L |
| chr16 | 1993818 | 1993848 | Hypo | RPL3L, MSRB1 | chr16 | 1741853 | 1742079 | Hypo | HNIL, CRAMP1L |
| chr16 | 2141909 | 2141972 | Hypo | PKD1, MIR1225, TSC2 | chr16 | 2029072 | 2029137 | Hypo | GFER, NOXO1, TBL3 |
| chr16 | 2213313 | 2213343 | Hypo | TRAF7, SNORD60, RAB26 | chr16 | 2142546 | 2142628 | Hypo | PKD1, MIR1225, TSC2 |
| chr16 | 2234726 | 2235020 | Hypo | CASKIN1, TRAF7 | chr16 | 2232745 | 2233003 | Hypo | CASKIN1, TRAF7 |
| chr16 | 2466225 | 2466307 | Hypo | | chr16 | 2275129 | 2275182 | Hypo | E4F1 |
| chr16 | 2731530 | 2731560 | Hypo | KCTD5, ERVK13-1 | chr16 | 2531069 | 2531177 | Hypo | TBC1D24, NTN3 |
| chr16 | 2770122 | 2770602 | Hypo | PRSS27 | chr16 | 2764377 | 2764470 | Hypo | PRSS27, KCTD5 |
| chr16 | 2956451 | 2956670 | Hypo | FLYWCH1, FLYWCH2 | chr16 | 2818101 | 2818156 | Hypo | TCEB2, SRRM2 |
| chr16 | 3211708 | 3212019 | Hypo | TRNA_Lys, TRNA_Pseudo, TRNA_Pro, TRNA_Arg | chr16 | 3151127 | 3151186 | Hypo | ZNF205-AS1, ZSCAN10 |
| chr16 | 3492583 | 3492675 | Hypo | NAA60, ZNF597 | chr16 | 3269249 | 3269350 | Hypo | ZNF200, OR1F2P |
| chr16 | 3696694 | 3696724 | Hypo | DNASE1 | chr16 | 3598920 | 3598953 | Hypo | NLRC3 |
| chr16 | 4264529 | 4264694 | Hypo | SRL | chr16 | 3950127 | 3950279 | Hypo | |
| chr16 | 4310735 | 4310847 | Hypo | TFAP4, LOC100507501 | chr16 | 4303144 | 4303174 | Hypo | TFAP4, LOC100507501 |
| chr16 | 4846136 | 4846514 | Hypo | ROGDI, GLYR1, LOC440335, SEPT12 | chr16 | 4783226 | 4783375 | Hypo | C16orf71, ANKS3 |
| chr16 | 6035056 | 6035208 | Hypo | | chr16 | 5541116 | 5541158 | Hypo | BC108660 |
| chr16 | 8781032 | 8781177 | Hypo | ABAT | chr16 | 7525361 | 7525531 | Hypo | RBFOX1 |
| chr16 | 9009860 | 9009989 | Hypo | USP7 | chr16 | 8870353 | 8870383 | Hypo | ABAT |
| chr16 | 11427659 | 11427732 | Hypo | | chr16 | 11242000 | 11242138 | Hypo | CLEC16A |
| chr16 | 12011258 | 12011325 | Hypo | GSPT1 | chr16 | 11923005 | 11923035 | Hypo | RSL1D1, BCAR4 |
| chr16 | 12066767 | 12066806 | Hypo | SNX29, TNFRSF17 | chr16 | 12011940 | 12012073 | Hypo | GSPT1 |
| chr16 | 12971776 | 12971934 | Hypo | | chr16 | 12530169 | 12530199 | Hypo | |
| chr16 | 14724632 | 14724736 | Hypo | BFAR, PARN | chr16 | 14189948 | 14190069 | Hypo | MKL2 |
| chr16 | 15738905 | 15739042 | Hypo | NDE1, MIR484, KIAA0430 | chr16 | 14725842 | 14726005 | Hypo | BFAR, PARN |

TABLE 1-continued

| Chr | Start | Stop | Hypo/hyper | Annotation | Chr | Start | Stop | Hypo/hyper | Annotation |
|---|---|---|---|---|---|---|---|---|---|
| chr16 | 16868746 | 16868905 | Hypo | | chr16 | 15820825 | 15820865 | Hypo | AX747846, MYH11 |
| chr16 | 18802250 | 18802680 | Hypo | ARL6IP1, RPS15A | chr16 | 18163245 | 18163352 | Hypo | |
| chr16 | 19430908 | 19430949 | Hypo | TMC5 | chr16 | 18950928 | 18951018 | Hypo | |
| chr16 | 21541606 | 21541636 | Hypo | SLC7A5P2 | chr16 | 19531564 | 19531697 | Hypo | CCP110, GDE1 |
| chr16 | 22300599 | 22300637 | Hypo | TRNA, POLR3E, EEF2K, TRNA_Leu | chr16 | 21839328 | 21839470 | Hypo | LOC23117, LOC100132247, RRN3P1 |
| chr16 | 24172241 | 24172271 | Hypo | PRKCB | chr16 | 24127251 | 24127338 | Hypo | PRKCB |
| chr16 | 24415106 | 24415176 | Hypo | | chr16 | 24180710 | 24180760 | Hypo | PRKCB |
| chr16 | 25542301 | 25542452 | Hypo | | chr16 | 25266537 | 25266573 | Hypo | ZKSCAN2 |
| chr16 | 25921574 | 25921604 | Hypo | HS3ST4 | chr16 | 25551107 | 25551264 | Hypo | |
| chr16 | 26664739 | 26664775 | Hypo | | chr16 | 26302585 | 26302619 | Hypo | |
| chr16 | 27961122 | 27961254 | Hypo | | chr16 | 27459938 | 27460074 | Hypo | IL21R, IL21R-AS1 |
| chr16 | 28560309 | 28560381 | Hypo | CCDC101, NUPR1 | chr16 | 28093825 | 28093866 | Hypo | |
| chr16 | 29119008 | 29119058 | Hypo | AK075019, RRN3P2 | chr16 | 28823157 | 28823459 | Hypo | AK125489 |
| chr16 | 29244900 | 29244997 | Hypo | | chr16 | 29153284 | 29153356 | Hypo | |
| chr16 | 29936211 | 29936272 | Hypo | KCTD13, ASPHD1 | chr16 | 29830871 | 29831078 | Hypo | BC029255, PAGR1, PRRT2, AK097472, AB209061, MAZ, MVP |
| chr16 | 30065485 | 30065525 | Hypo | ALDOA | chr16 | 30017330 | 30017447 | Hypo | DOC2A, INO80E |
| chr16 | 30116285 | 30116315 | Hypo | MAPK3, GDPD3, AK097453, YPEL3 | chr16 | 30085867 | 30085995 | Hypo | ALDOA, PPP4C |
| chr16 | 30169925 | 30170103 | Hypo | | chr16 | 30124691 | 30124861 | Hypo | GDPD3, AK097453, MAPK3 |
| chr16 | 30402082 | 30402112 | Hypo | ZNF48, SEPT1 | chr16 | 30388542 | 30388574 | Hypo | SEPT1, ZNF48, MYLPF, TBC1D10B |
| chr16 | 30639693 | 30639735 | Hypo | | chr16 | 30609373 | 30609408 | Hypo | ZNF689 |
| chr16 | 30826334 | 30826509 | Hypo | | chr16 | 30804321 | 30804472 | Hypo | ZNF629 |
| chr16 | 31384593 | 31384623 | Hypo | ITGAX | chr16 | 30907070 | 30907100 | Hypo | CTF1, MIR762, BCL7C, BC073928 |
| chr16 | 31498008 | 31498165 | Hypo | TGFB1I1, BC054514, C16orf58, SLC5A2 | chr16 | 31446830 | 31447096 | Hypo | COX6A2, ITGAD, ZNF843 |
| chr16 | 46569239 | 46569474 | Hypo | | chr16 | 31500544 | 31500673 | Hypo | C16orf58, BC054514, SLC5A2 |
| chr16 | 48641663 | 48641693 | Hypo | N4BP1 | chr16 | 46721567 | 46721707 | Hypo | ORC6, VPS35 |
| chr16 | 49314810 | 49314840 | Hypo | CBLN1 | chr16 | 48642149 | 48642179 | Hypo | N4BP1 |
| chr16 | 50335767 | 50335797 | Hypo | ADCY7 | chr16 | 49638060 | 49638090 | Hypo | ZNF423 |
| chr16 | 53467271 | 53467395 | Hypo | U6, RBL2 | chr16 | 53447826 | 53448002 | Hypo | |
| chr16 | 57222663 | 57222709 | Hypo | RSPRY1 | chr16 | 53563622 | 53563654 | Hypo | |
| chr16 | 57935454 | 57935605 | Hypo | CNGB1 | chr16 | 57326422 | 57326613 | Hypo | TRNA_Leu, PLLP |
| chr16 | 58427501 | 58427542 | Hypo | GINS3 | chr16 | 58120795 | 58120961 | Hypo | |
| chr16 | 58969757 | 58969792 | Hypo | AK057513 | chr16 | 58550489 | 58550519 | Hypo | CNOT1, SETD6, NDRG4 |
| chr16 | 67241204 | 67241234 | Hypo | E2F4, LRRC29, MIR328, ELMO3 | chr16 | 66863917 | 66863959 | Hypo | NAE1 |
| chr16 | 67850955 | 67850985 | Hypo | TSNAXIP1 | chr16 | 67313865 | 67313895 | Hypo | KCTD19, PLEKHG4 |
| chr16 | 68770755 | 68770974 | Hypo | CDH1 | chr16 | 67871102 | 67871134 | Hypo | THAP11, NUTF2, CENPT, TSNA_XIP1 |
| chr16 | 69026784 | 69026814 | Hypo | TANGO6 | chr16 | 68876782 | 68876996 | Hypo | TANGO6, CDH1 |
| chr16 | 70489585 | 70489681 | Hypo | FUK | chr16 | 69564118 | 69564200 | Hypo | |
| chr16 | 70794492 | 70794633 | Hypo | BC033164, VAC14-AS1 | chr16 | 70595535 | 70595700 | Hypo | |
| chr16 | 71918889 | 71919024 | Hypo | IST1, ZNF821 | chr16 | 71507759 | 71507791 | Hypo | ZNF19, AK123826, ZNF23 |
| chr16 | 74886148 | 74886268 | Hypo | | chr16 | 72957763 | 72957795 | Hypo | |
| chr16 | 75019751 | 75019781 | Hypo | | chr16 | 74901594 | 74901659 | Hypo | WDR59 |
| chr16 | 77247440 | 77247470 | Hypo | SYCE1L | chr16 | 75549798 | 75549836 | Hypo | |
| chr16 | 84074836 | 84074871 | Hypo | SLC38A8 | chr16 | 81564199 | 81564229 | Hypo | CMIP |
| chr16 | 85075434 | 85075553 | Hypo | KIAA0513 | chr16 | 84153364 | 84153394 | Hypo | MBTPS1, HSDL1 |
| chr16 | 85485747 | 85485855 | Hypo | | chr16 | 85317850 | 85317882 | Hypo | LINC00311 |
| chr16 | 85517345 | 85517521 | Hypo | | chr16 | 85497445 | 85497475 | Hypo | |
| chr16 | 85678639 | 85678761 | Hypo | GSE1 | chr16 | 85651520 | 85651550 | Hypo | GSE1 |
| chr16 | 85834460 | 85834495 | Hypo | COX4I1, EMC8 | chr16 | 85684308 | 85684457 | Hypo | GSE1 |
| chr16 | 87092439 | 87092553 | Hypo | | chr16 | 86878150 | 86878180 | Hypo | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr16 | 87723735 | 87724098 | Hypo | FLJ00104, hCG_1980662 | chr16 | 87714272 | 87714381 | Hypo | |
| chr16 | 88498241 | 88498760 | Hypo | ZNF469 | chr16 | 88164401 | 88164468 | Hypo | |
| chr16 | 88506346 | 88506526 | Hypo | ZNF469 | chr16 | 88504058 | 88504315 | Hypo | ZNF469 |
| chr16 | 88550263 | 88550483 | Hypo | | chr16 | 88512427 | 88512529 | Hypo | ZFPM1, ZNF469 |
| chr16 | 88623960 | 88624167 | Hypo | C16orf85 | chr16 | 88603696 | 88603760 | Hypo | |
| chr16 | 88883238 | 88883377 | Hypo | CDT1, GALNS, APRT | chr16 | 88879949 | 88880124 | Hypo | GALNS, APRT, CDT1 |
| chr16 | 88943559 | 88944024 | Hypo | CBFA2T3 | chr16 | 88941058 | 88941141 | Hypo | CBFA2T3, PABPN1L |
| chr16 | 88955249 | 88955368 | Hypo | CBFA2T3 | chr16 | 88945815 | 88945995 | Hypo | CBFA2T3 |
| chr16 | 88957350 | 88957857 | Hypo | CBFA2T3 | chr16 | 88956230 | 88956399 | Hypo | CBFA2T3 |
| chr16 | 88963277 | 88963763 | Hypo | CBFA2T3 | chr16 | 88958397 | 88958431 | Hypo | CBFA2T3 |
| chr16 | 88968709 | 88968789 | Hypo | CBFA2T3 | chr16 | 88966303 | 88966588 | Hypo | CBFA2T3 |
| chr16 | 88993078 | 88993230 | Hypo | CBFA2T3 | chr16 | 88978024 | 88978072 | Hypo | CBFA2T3 |
| chr16 | 89000168 | 89000204 | Hypo | CBFA2T3 | chr16 | 88999617 | 88999647 | Hypo | CBFA2T3 |
| chr16 | 89047717 | 89047747 | Hypo | CBFA2T3 | chr16 | 89001094 | 89001124 | Hypo | CBFA2T3 |
| chr16 | 89086109 | 89086197 | Hypo | | chr16 | 89072503 | 89072774 | Hypo | |
| chr16 | 89109385 | 89109415 | Hypo | AK055272 | chr16 | 89107675 | 89107732 | Hypo | AK055272 |
| chr16 | 89120708 | 89120864 | Hypo | AK055272 | chr16 | 89120038 | 89120319 | Hypo | AK055272 |
| chr16 | 89220327 | 89220398 | Hypo | LINC00304, ACSF3 | chr16 | 89138016 | 89138060 | Hypo | |
| chr16 | 89254653 | 89254830 | Hypo | SLC22A31, CDH15 | chr16 | 89220655 | 89220922 | Hypo | LINC00304, ACSF3 |
| chr16 | 89575728 | 89575861 | Hypo | SPG7 | chr16 | 89558610 | 89558703 | Hypo | |
| chr16 | 89883972 | 89884185 | Hypo | FANCA | chr16 | 89676025 | 89676197 | Hypo | DPEP1 |
| chr16 | 89900124 | 89900180 | Hypo | SPIRE2 | chr16 | 89884966 | 89885142 | Hypo | SPIRE2, FANCA |
| chr16 | 90115428 | 90115458 | Hypo | PRDM7, LOC100130015, AK127378 | chr16 | 89900455 | 89900526 | Hypo | SPIRE2 |
| chr2 | 496228 | 496380 | Hypo | | chr2 | 142427 | 142468 | Hypo | |
| chr2 | 720836 | 720894 | Hypo | | chr2 | 602657 | 602687 | Hypo | |
| chr2 | 2646900 | 2646930 | Hypo | | chr2 | 875961 | 875991 | Hypo | |
| chr2 | 2844720 | 2844750 | Hypo | | chr2 | 2672620 | 2672732 | Hypo | |
| chr2 | 4019911 | 4020036 | Hypo | LOC100505964 | chr2 | 2893165 | 2893193 | Hypo | AK095310 |
| chr2 | 8835493 | 8835523 | Hypo | | chr2 | 7062891 | 7062959 | Hypo | RNF144A, RNF144A-AS1 |
| chr2 | 9960734 | 9960764 | Hypo | | chr2 | 9134404 | 9134493 | Hypo | MBOAT2 |
| chr2 | 10152798 | 10153325 | Hypo | | chr2 | 10115730 | 10115772 | Hypo | |
| chr2 | 10154930 | 10155298 | Hypo | | chr2 | 10154266 | 10154564 | Hypo | |
| chr2 | 10408398 | 10408459 | Hypo | | chr2 | 10156116 | 10156389 | Hypo | |
| chr2 | 12246114 | 12246217 | Hypo | | chr2 | 11142174 | 11142315 | Hypo | |
| chr2 | 15579989 | 15580019 | Hypo | | chr2 | 12297534 | 12297564 | Hypo | |
| chr2 | 20641988 | 20642081 | Hypo | RHOB | chr2 | 20442433 | 20442498 | Hypo | PUM2 |
| chr2 | 20710145 | 20710324 | Hypo | | chr2 | 20642541 | 20642648 | Hypo | RHOB |
| chr2 | 24318290 | 24318357 | Hypo | | chr2 | 22404181 | 22404227 | Hypo | |
| chr2 | 25374762 | 25374804 | Hypo | POMC, EFR3B | chr2 | 25029252 | 25029300 | Hypo | CENPO |
| chr2 | 26372967 | 26372997 | Hypo | | chr2 | 25439727 | 25439915 | Hypo | |
| chr2 | 27433532 | 27433601 | Hypo | ATRAID, CAD, SLC5A6 | chr2 | 27271699 | 27272218 | Hypo | AGBL5, TMEM214, TRNA, TRNA_Tyr, TRNA_Ala |
| chr2 | 27648172 | 27648294 | Hypo | NRBP1 | chr2 | 27578243 | 27578396 | Hypo | EIF2B4 |
| chr2 | 27887525 | 27887555 | Hypo | SUPT7L, SLC4A1AP | chr2 | 27764046 | 27764168 | Hypo | |
| chr2 | 30368444 | 30368586 | Hypo | YPEL5 | chr2 | 29091592 | 29091838 | Hypo | TRMT61B |
| chr2 | 32504169 | 32504378 | Hypo | YIPF4 | chr2 | 32275196 | 32275303 | Hypo | |
| chr2 | 38953573 | 38953603 | Hypo | GALM | chr2 | 38365525 | 38365748 | Hypo | CYP1B1-AS1 |
| chr2 | 43824133 | 43824353 | Hypo | THADA | chr2 | 43388448 | 43388486 | Hypo | |
| chr2 | 47597455 | 47598620 | Hypo | MIR559, EPCAM | chr2 | 47194037 | 47194136 | Hypo | TTC7A |
| chr2 | 48629615 | 48629685 | Hypo | | chr2 | 47599589 | 47599753 | Hypo | MIR559, EPCAM |
| chr2 | 48648878 | 48648940 | Hypo | | chr2 | 48636504 | 48636669 | Hypo | |
| chr2 | 55669261 | 55669454 | Hypo | | chr2 | 50573802 | 50573865 | Hypo | NRXN1 |
| chr2 | 59400384 | 59400424 | Hypo | | chr2 | 58552519 | 58552689 | Hypo | |
| chr2 | 60706759 | 60706804 | Hypo | BCL11A | chr2 | 60416280 | 60416494 | Hypo | |
| chr2 | 61242732 | 61242802 | Hypo | PEX13, PUS10 | chr2 | 61232163 | 61232232 | Hypo | PUS10, 5S_rRNA |
| chr2 | 61556203 | 61556239 | Hypo | | chr2 | 61395039 | 61395069 | Hypo | AHSA2, C2orf74 |
| chr2 | 65779892 | 65779983 | Hypo | FLJ16124 | chr2 | 61992076 | 61992289 | Hypo | |
| chr2 | 67626102 | 67626257 | Hypo | ETAA1 | chr2 | 67625453 | 67625770 | Hypo | ETAA1 |
| chr2 | 68672853 | 68672938 | Hypo | | chr2 | 68559261 | 68559365 | Hypo | |
| chr2 | 70418528 | 70418627 | Hypo | C2orf42 | chr2 | 70058262 | 70058292 | Hypo | GMCL1 |
| chr2 | 71355019 | 71355117 | Hypo | MPHOSPH10, MCEE | chr2 | 70430997 | 70431160 | Hypo | TIA1 |
| chr2 | 73147353 | 73147383 | Hypo | EMX1 | chr2 | 71355768 | 71355961 | Hypo | MPHOSPH10, MCEE |
| chr2 | 74010528 | 74010773 | Hypo | C2orf78, DUSP11 | chr2 | 73440206 | 73440293 | Hypo | SMYD5, NOTO |

TABLE 1-continued

| Chr | Start | Stop | Hypo/hyper | Annotation |
|---|---|---|---|---|
| chr2 | 74454074 | 74454261 | Hypo | SLC4A5 |
| chr2 | 74350410 | 74350497 | Hypo | |
| chr2 | 74679047 | 74679123 | Hypo | WBP1, MOGS, RTKN, INO80B, INO80B-WBP1 |
| chr2 | 74647864 | 74648007 | Hypo | WDR54, RTKN, DQ588163, C2orf81 |
| chr2 | 85838101 | 85838299 | Hypo | TMEM150A, USP39, C2orf68 |
| chr2 | 74874865 | 74874903 | Hypo | SEMA4F |
| chr2 | 86423330 | 86423592 | Hypo | IMMT, MRPL35, MIR4779 |
| chr2 | 86191145 | 86191309 | Hypo | |
| chr2 | 88469312 | 88469483 | Hypo | THNSL2 |
| chr2 | 86783725 | 86783755 | Hypo | RNF103-CHMP3, CHMP3 |
| chr2 | 89252535 | 89252679 | Hypo | |
| chr2 | 88990189 | 88990264 | Hypo | RPIA |
| chr2 | 97427515 | 97428093 | Hypo | CNNM4 |
| chr2 | 95941678 | 95941812 | Hypo | PROM2 |
| chr2 | 99798646 | 99799153 | Hypo | MRPL30, MITD1 |
| chr2 | 99796259 | 99796330 | Hypo | MRPL30, MITD1 |
| chr2 | 101834977 | 101835057 | Hypo | |
| chr2 | 101009832 | 101009927 | Hypo | CHST10 |
| chr2 | 105937344 | 105937498 | Hypo | TGFBRAP1 |
| chr2 | 105488437 | 105488496 | Hypo | AK095498 |
| chr2 | 106959368 | 106959558 | Hypo | |
| chr2 | 106730223 | 106730256 | Hypo | UXS1 |
| chr2 | 108364897 | 108364940 | Hypo | |
| chr2 | 106599916 | 106959988 | Hypo | |
| chr2 | 111544817 | 111544997 | Hypo | ACOXL |
| chr2 | 109335133 | 109335166 | Hypo | RANBP2 |
| chr2 | 114515528 | 114515618 | Hypo | SLC35F5 |
| chr2 | 113803960 | 113803990 | Hypo | IL36B |
| chr2 | 119600570 | 119600747 | Hypo | EN1 |
| chr2 | 114634867 | 114634988 | Hypo | |
| chr2 | 120980068 | 120980098 | Hypo | TMEM185B |
| chr2 | 120769511 | 120769746 | Hypo | EPB41L5 |
| chr2 | 122495267 | 122495413 | Hypo | MKI67IP |
| chr2 | 120980353 | 120980395 | Hypo | TMEM185B |
| chr2 | 127412291 | 127412386 | Hypo | GYPC |
| chr2 | 122809705 | 122809801 | Hypo | |
| chr2 | 127429010 | 127429044 | Hypo | GYPC |
| chr2 | 127423220 | 127423350 | Hypo | GYPC |
| chr2 | 128616617 | 128616838 | Hypo | AMMECR1L, POLR2D |
| chr2 | 127438633 | 127438663 | Hypo | GYPC |
| chr2 | 128847677 | 128847723 | Hypo | UGGT1 |
| chr2 | 128680057 | 128680087 | Hypo | |
| chr2 | 130937868 | 130937898 | Hypo | FLJ14346, SMPD4, MZT2B |
| chr2 | 129174888 | 129174918 | Hypo | |
| chr2 | 131477785 | 131477936 | Hypo | GPR148 |
| chr2 | 131084953 | 131085013 | Hypo | TRNA_Glu |
| chr2 | 136287358 | 136287390 | Hypo | R3HDM1, ZRANB3 |
| chr2 | 132208115 | 132208278 | Hypo | LOC401010 |
| chr2 | 144129765 | 144129795 | Hypo | ARHGAP15 |
| chr2 | 143569561 | 143569694 | Hypo | |
| chr2 | 148776809 | 148777035 | Hypo | MBD5, ORC4 |
| chr2 | 144299758 | 144299788 | Hypo | ARHGAP15 |
| chr2 | 161253293 | 161253455 | Hypo | RBMS1 |
| chr2 | 152248836 | 152248983 | Hypo | |
| chr2 | 166929478 | 166929613 | Hypo | BC051759, SCN1A |
| chr2 | 162166600 | 162166632 | Hypo | PSMD14 |
| chr2 | 170282981 | 170283080 | Hypo | |
| chr2 | 170255970 | 170256139 | Hypo | |
| chr2 | 170681880 | 170682422 | Hypo | UBR3, METTL5 |
| chr2 | 170551856 | 170551942 | Hypo | PHOSPHO2, PHOSPHO2-KLHL23, CCDC173 |
| chr2 | 172411136 | 172411166 | Hypo | CYBRD1 |
| chr2 | 171839017 | 171839047 | Hypo | TLK1 |
| chr2 | 173422685 | 173422734 | Hypo | PDK1 |
| chr2 | 172973111 | 172973141 | Hypo | DLX2 |
| chr2 | 175261402 | 175261432 | Hypo | SCRN3, CIR1 |
| chr2 | 175111870 | 175112092 | Hypo | OLA1 |
| chr2 | 176994031 | 176994136 | Hypo | HOXD8, HOXD-AS2, BC047605, AX747372, HOXD9, HOXD10 |
| chr2 | 175383935 | 175383965 | Hypo | |
| chr2 | 179316860 | 179317057 | Hypo | DFNB59 |
| chr2 | 179303534 | 179303727 | Hypo | AX747806, PRKRA, BX538254, MIR548N |
| chr2 | 197793125 | 197793267 | Hypo | PGAP1 |
| chr2 | 182202233 | 182202291 | Hypo | |
| chr2 | 198456480 | 198456719 | Hypo | RFTN2 |
| chr2 | 198238409 | 198238439 | Hypo | |
| chr2 | 202477462 | 202477621 | Hypo | TMEM237, ALS2CR11 |
| chr2 | 200818892 | 200819130 | Hypo | C2orf47, TYW5 |
| chr2 | 203880390 | 203880492 | Hypo | NBEAL1 |
| chr2 | 203484608 | 203484646 | Hypo | |
| chr2 | 207022702 | 207022802 | Hypo | NDUFS1, EEF1B2, SNORD51, SNORA41 |
| chr2 | 204194588 | 204194725 | Hypo | ABI2 |
| chr2 | 208588311 | 208588341 | Hypo | CCNYL1 |
| chr2 | 208574821 | 208574917 | Hypo | CCNYL1 |
| chr2 | 223166270 | 223166408 | Hypo | CCDC140, DD413687, PAX3 |
| chr2 | 209094739 | 209094845 | Hypo | IDH1 |
| chr2 | 228411020 | 228411050 | Hypo | AGFG1 |
| chr2 | 225464038 | 225464068 | Hypo | |
| chr2 | 228735680 | 228735736 | Hypo | DAW1 |
| chr2 | 228466625 | 228466777 | Hypo | C2orf83 |
| chr2 | 231576609 | 231576643 | Hypo | CAB39 |
| chr2 | 230795535 | 230795565 | Hypo | FBXO36, TRIP12 |
| chr2 | 232506220 | 232506294 | Hypo | |
| chr2 | 232330451 | 232330481 | Hypo | NCL, SNORD82, SNORD20, SNORA75 |
| chr2 | 232522844 | 232522874 | Hypo | |
| chr2 | 232506605 | 232506635 | Hypo | |
| chr2 | 232546736 | 232546842 | Hypo | |
| chr2 | 232544500 | 232544530 | Hypo | |
| chr2 | 233220227 | 233220382 | Hypo | |
| chr2 | 232827168 | 232827349 | Hypo | DIS3L2 |
| chr2 | 234776483 | 234776553 | Hypo | MSL3P1 |
| chr2 | 233750525 | 233750555 | Hypo | NGEF, C2orf82 |
| chr2 | 239051198 | 239051228 | Hypo | KLHL30, ESPNL |
| chr2 | 239031722 | 239031780 | Hypo | ESPNL |
| chr2 | 239482485 | 239482519 | Hypo | |
| chr2 | 239265496 | 239265787 | Hypo | TRAF3 IP1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr2 | 239957330 | 239957448 | Hypo | | chr2 | 239705305 | 239705337 | Hypo | U4 |
| chr2 | 240168811 | 240169051 | Hypo | | chr2 | 240167575 | 240167605 | Hypo | |
| chr2 | 240619459 | 240619604 | Hypo | | chr2 | 240582379 | 240582524 | Hypo | |
| chr2 | 240658667 | 240658697 | Hypo | | chr2 | 240658227 | 240658421 | Hypo | |
| chr2 | 241095604 | 241095772 | Hypo | | chr2 | 240812243 | 240812374 | Hypo | |
| chr2 | 241545001 | 241545031 | Hypo | GPR35, CAPN10 | chr2 | 241542198 | 241542297 | Hypo | GPR35, CAPN10 |
| chr2 | 242009391 | 242009421 | Hypo | SNED1 | chr2 | 241865194 | 241865346 | Hypo | |
| chr2 | 242314494 | 242314524 | Hypo | FARP2 | chr2 | 242021784 | 242021892 | Hypo | SNED1 |
| chr2 | 242554549 | 242554579 | Hypo | | chr2 | 242524008 | 242524147 | Hypo | 5S_rRNA, THAP4 |
| chr2 | 242640015 | 242640045 | Hypo | ING5 | chr2 | 242636726 | 242636812 | Hypo | ING5 |
| chr2 | 242756144 | 242756297 | Hypo | NEU4, PABL | chr2 | 242716723 | 242716760 | Hypo | GAL3ST2, D2HGDH |
| chr2 | 24283355 | 242833588 | Hypo | | chr2 | 242832984 | 242833159 | Hypo | |
| chr2 | 24283649 | 242836640 | Hypo | | chr2 | 242833797 | 242833863 | Hypo | |
| chr15 | 22822348 | 22822488 | Hypo | | chr2 | 242925496 | 242925641 | Hypo | AK097934 |
| chr15 | 23162337 | 23162372 | Hypo | | chr15 | 23035709 | 23035781 | Hypo | NIPA1, NIPA2 |
| chr15 | 23692316 | 23692453 | Hypo | LOC283685, GOLGA6L2 | chr15 | 23273146 | 23273330 | Hypo | HERC2P2, JB175342, DQ572979 |
| chr15 | 33879242 | 33879272 | Hypo | RYR3 | chr15 | 31455370 | 31455485 | Hypo | |
| chr15 | 34879708 | 34879866 | Hypo | | chr15 | 34630818 | 34630865 | Hypo | SLC12A6, NOP10, NUTM1 |
| chr15 | 40856224 | 40856254 | Hypo | RPUSD2, C15orf57 | chr15 | 35310631 | 35310868 | Hypo | |
| chr15 | 41165245 | 41165700 | Hypo | RHOV | chr15 | 40877650 | 40877714 | Hypo | TRNA_Ser, CCAS5 |
| chr15 | 41693679 | 41693794 | Hypo | NDUFAF1 | chr15 | 41541844 | 41541874 | Hypo | CHP1 |
| chr15 | 41835548 | 41835720 | Hypo | | chr15 | 41708225 | 41708305 | Hypo | RTF1 |
| chr15 | 44037568 | 44037699 | Hypo | PDIA3, CATSPER2P1 | chr15 | 42866975 | 42867049 | Hypo | STARD9, HAUS2 |
| chr15 | 51146606 | 51146636 | Hypo | AK091906 | chr15 | 50464583 | 50464622 | Hypo | SLC27A2 |
| chr15 | 54642236 | 54642352 | Hypo | UNC13C | chr15 | 52000818 | 52000937 | Hypo | SCG3 |
| chr15 | 55610440 | 55610698 | Hypo | PIGB, HP06981 | chr15 | 55452761 | 55452993 | Hypo | |
| chr15 | 55806758 | 55806900 | Hypo | DYX1C1 | chr15 | 55699089 | 55699164 | Hypo | DYX1C1, DYX1C1-CCPG1, FLJ27352 |
| chr15 | 59158488 | 59158537 | Hypo | unknown, FAM63B | chr15 | 56832508 | 56832546 | Hypo | BC037892 |
| chr15 | 59950198 | 59950363 | Hypo | BNIP2, GTF2A2 | chr15 | 59158781 | 59158848 | Hypo | unknown, FAM63B |
| chr15 | 64109724 | 64109788 | Hypo | HERC1 | chr15 | 60084984 | 60085014 | Hypo | |
| chr15 | 64649481 | 64649553 | Hypo | KIAA0101, CSNK1G1 | chr15 | 64618655 | 64618813 | Hypo | CSNK1G1 |
| chr15 | 65119265 | 65119295 | Hypo | PIF1 | chr15 | 65118954 | 65118984 | Hypo | PIF1 |
| chr15 | 65685591 | 65685621 | Hypo | IGDCC4 | chr15 | 65119499 | 65119632 | Hypo | PIF1 |
| chr15 | 65826189 | 65826359 | Hypo | PTPLAD1 | chr15 | 65823926 | 65824103 | Hypo | PTPLAD1 |
| chr15 | 66649915 | 66649945 | Hypo | | chr15 | 65862004 | 65862059 | Hypo | VWA9, PTPLAD1 |
| chr15 | 66963816 | 66963871 | Hypo | hCG_2003567 | chr15 | 66789220 | 66789321 | Hypo | SNORD18B, SNORD16, SNORD18A, ZWILCH, SNAPC5, MAP2K1, RPL4, SNORD18C |
| chr15 | 67545536 | 67545566 | Hypo | IQCH, AAGAB | chr15 | 67146145 | 67146431 | Hypo | BX538221 |
| chr15 | 72743741 | 72743771 | Hypo | | chr15 | 72412176 | 72412176 | Hypo | SENP8, MYO9A |
| chr15 | 74686021 | 74686051 | Hypo | | chr15 | 72979757 | 72979873 | Hypo | BBS4, HIGD2B |
| chr15 | 74906463 | 74906493 | Hypo | CLK3, AK095335 | chr15 | 74903896 | 74903926 | Hypo | CLK3, AK095335 |
| chr15 | 75412459 | 75412714 | Hypo | | chr15 | 75205413 | 75205481 | Hypo | COX5A, FAM219B |
| chr15 | 78501806 | 78501942 | Hypo | ACSBG1 | chr15 | 77448873 | 77449001 | Hypo | PEAK1 |
| chr15 | 78859435 | 78859603 | Hypo | CHRNA5 | chr15 | 78595791 | 78596218 | Hypo | WDR61 |
| chr15 | 80216803 | 80216884 | Hypo | C15orf37, ST20 | chr15 | 79151898 | 79152007 | Hypo | TRNA_Lys |
| chr15 | 83655843 | 83655934 | Hypo | C15orf40, FAM103A1, BC044934 | chr15 | 83314048 | 83314106 | Hypo | LOC283692 |
| chr15 | 84711204 | 84711367 | Hypo | | chr15 | 83866523 | 83866559 | Hypo | HDGFRP3 |
| chr15 | 85886518 | 85886604 | Hypo | | chr15 | 85142994 | 85143054 | Hypo | ZSCAN2 |
| chr15 | 90703262 | 90703345 | Hypo | | chr15 | 86002524 | 86002690 | Hypo | AKAP13 |
| chr15 | 93158592 | 93158739 | Hypo | FAM174B, DQ589911, DQ571124, DQ574028, DQ593762 | chr15 | 90755916 | 90756079 | Hypo | SEMA4B |
| chr15 | 94347602 | 94347632 | Hypo | BC037497 | chr15 | 93364552 | 93364624 | Hypo | |
| chr15 | 98634851 | 98634949 | Hypo | | chr15 | 97006372 | 97006533 | Hypo | |
| chr15 | 99295692 | 99295749 | Hypo | IGF1R | chr15 | 98776762 | 98776792 | Hypo | |
| chr15 | 99354999 | 99355041 | Hypo | | chr15 | 99346861 | 99346891 | Hypo | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr15 | 101818327 | 101818357 | Hypo | SNRPA1, VIMP | chr15 | 100274325 | 100274385 | Hypo | LYSMD4 |
| chr15 | 102193587 | 102193713 | Hypo | TARSL2, TM2D3 | chr15 | 102115873 | 102115905 | Hypo | |
| chr20 | 304259 | 304408 | Hypo | SOX12 | chr20 | 118577 | 118751 | Hypo | DEFB126 |
| chr20 | 401153 | 401183 | Hypo | RBCK1 | chr20 | 400007 | 400087 | Hypo | RBCK1 |
| chr20 | 523146 | 523193 | Hypo | CSNK2A1 | chr20 | 401591 | 401756 | Hypo | RBCK1 |
| chr20 | 799458 | 799706 | Hypo | | chr20 | 799104 | 799247 | Hypo | |
| chr20 | 2645540 | 2645795 | Hypo | SNORA51, IDH3B | chr20 | 1197670 | 1197711 | Hypo | RAD21L1, C20orf202 |
| chr20 | 3204870 | 3204952 | Hypo | SLC4A11, ITPA | chr20 | 3027758 | 3027931 | Hypo | MRPS26, GNRH2, PTPRA |
| chr20 | 3996688 | 3996726 | Hypo | RNF24 | chr20 | 3858389 | 3858632 | Hypo | BC012193, MAVS |
| chr20 | 4085057 | 4085087 | Hypo | | chr20 | 4040710 | 4040871 | Hypo | |
| chr20 | 5106720 | 5106750 | Hypo | CDS2, PCNA-AS1, PCNA | chr20 | 5025228 | 5025258 | Hypo | |
| chr20 | 14447971 | 14448144 | Hypo | | chr20 | 9488780 | 9488848 | Hypo | LAMP5 |
| chr20 | 18073183 | 18073276 | Hypo | | chr20 | 16554749 | 16555030 | Hypo | KIF16B |
| chr20 | 18489463 | 18489658 | Hypo | SEC23B | chr20 | 18448982 | 18449076 | Hypo | DZANK1, MIR3192, POLR3F |
| chr20 | 19928306 | 19928461 | Hypo | RIN2 | chr20 | 19128288 | 19128473 | Hypo | |
| chr20 | 21685385 | 21685526 | Hypo | PAX1 | chr20 | 21501381 | 21501420 | Hypo | NKX2-2 |
| chr20 | 23406698 | 23406830 | Hypo | | chr20 | 23138383 | 23138444 | Hypo | |
| chr20 | 24726701 | 24726825 | Hypo | | chr20 | 24505190 | 24505252 | Hypo | SYNDIG1 |
| chr20 | 25230509 | 25230799 | Hypo | PYGB | chr20 | 25086082 | 25086275 | Hypo | |
| chr20 | 25344027 | 25344118 | Hypo | ABHD12 | chr20 | 25334513 | 25334606 | Hypo | ABHD12 |
| chr20 | 29914002 | 29914139 | Hypo | | chr20 | 29832911 | 29833090 | Hypo | |
| chr20 | 30162296 | 30162459 | Hypo | HM13-AS1 | chr20 | 30101523 | 30101743 | Hypo | HM13 |
| chr20 | 30201236 | 30201360 | Hypo | MIR3193, ID1 | chr20 | 30174561 | 30174645 | Hypo | |
| chr20 | 30468319 | 30468349 | Hypo | TTLL9 | chr20 | 30297090 | 30297217 | Hypo | BCL2L1 |
| chr20 | 31151769 | 31151799 | Hypo | C20orf112 | chr20 | 31115683 | 31115799 | Hypo | C20orf112 |
| chr20 | 32450248 | 32450427 | Hypo | CHMP4B | chr20 | 31207211 | 31207283 | Hypo | |
| chr20 | 32716914 | 32716949 | Hypo | | chr20 | 32701064 | 32701320 | Hypo | EIF2S2 |
| chr20 | 33574914 | 33574992 | Hypo | MIR499A, MIR499B, MYH7B | chr20 | 32768669 | 32768728 | Hypo | |
| chr20 | 34148020 | 34148254 | Hypo | ERGIC3, FER1L4 | chr20 | 34041981 | 34042087 | Hypo | CEP250 |
| chr20 | 35892604 | 35892746 | Hypo | GHRH | chr20 | 35742487 | 35742607 | Hypo | MROH8 |
| chr20 | 40515378 | 40515504 | Hypo | | chr20 | 40500546 | 40500638 | Hypo | |
| chr20 | 42281425 | 42281455 | Hypo | IFT52 | chr20 | 42218429 | 42218664 | Hypo | IFT52, SGK2 |
| chr20 | 43952174 | 43952302 | Hypo | SDC4, TRNA_Pseudo, RBPJL | chr20 | 42852831 | 42852883 | Hypo | BC036500, OSER1-AS1 |
| chr20 | 44602074 | 44602364 | Hypo | ZNF335 | chr20 | 44601547 | 44601716 | Hypo | ZNF335 |
| chr20 | 47247239 | 47247450 | Hypo | PREX1, AX746653 | chr20 | 45337804 | 45337945 | Hypo | SLC2A10 |
| chr20 | 47296109 | 47296231 | Hypo | | chr20 | 47274032 | 47274062 | Hypo | PREX1 |
| chr20 | 47835328 | 47835358 | Hypo | DDX27 | chr20 | 47450370 | 47450490 | Hypo | |
| chr20 | 48695665 | 48696227 | Hypo | UBE2V1, TMEM189-UBE2V1 | chr20 | 47905426 | 47905603 | Hypo | SNORD12C, ZFAS1, SNORD12, SNORD12B |
| chr20 | 48774527 | 48774569 | Hypo | | chr20 | 48768118 | 48768148 | Hypo | |
| chr20 | 49261803 | 49262104 | Hypo | FAM65C | chr20 | 49204179 | 49204449 | Hypo | FAM65C, MIR645, PTPN1 |
| chr20 | 49350910 | 49351041 | Hypo | PARD6B | chr20 | 49323924 | 49324125 | Hypo | PARD6B |
| chr20 | 49358137 | 49358396 | Hypo | PARD6B | chr20 | 49351564 | 49351649 | Hypo | PARD6B |
| chr20 | 49381140 | 49381240 | Hypo | | chr20 | 49377755 | 49378043 | Hypo | PARD6B |
| chr20 | 50383224 | 50383423 | Hypo | ATP9A | chr20 | 50160756 | 50160850 | Hypo | |
| chr20 | 52401713 | 52401775 | Hypo | | chr20 | 50602134 | 50602264 | Hypo | |
| chr20 | 55008041 | 55008194 | Hypo | CASS4 | chr20 | 54522432 | 54522631 | Hypo | |
| chr20 | 55693527 | 55693662 | Hypo | | chr20 | 55499567 | 55499650 | Hypo | |
| chr20 | 59525138 | 59525300 | Hypo | | chr20 | 56766160 | 56766190 | Hypo | |
| chr20 | 59910175 | 59910346 | Hypo | CDH4 | chr20 | 59880433 | 59880477 | Hypo | CDH4 |
| chr20 | 60202594 | 60202624 | Hypo | CDH4 | chr20 | 59973028 | 59973072 | Hypo | CDH4 |
| chr20 | 60238381 | 60238472 | Hypo | CDH4 | chr20 | 60235333 | 60235526 | Hypo | CDH4 |
| chr20 | 60243944 | 60244107 | Hypo | CDH4 | chr20 | 60238877 | 60238980 | Hypo | CDH4 |
| chr20 | 60333880 | 60333969 | Hypo | | chr20 | 60329584 | 60329738 | Hypo | |
| chr20 | 60375036 | 60375070 | Hypo | | chr20 | 60359849 | 60359879 | Hypo | |
| chr20 | 60453925 | 60454091 | Hypo | | chr20 | 60439634 | 60439755 | Hypo | |
| chr20 | 60485374 | 60485425 | Hypo | | chr20 | 60477306 | 60477537 | Hypo | |
| chr20 | 60789965 | 60790124 | Hypo | HRH3 | chr20 | 60503030 | 60503060 | Hypo | |
| chr20 | 60926019 | 60926049 | Hypo | | chr20 | 60892164 | 60892222 | Hypo | LAMA5 |
| chr20 | 60983859 | 60984010 | Hypo | RBBP8NL, CABLES2 | chr20 | 60970953 | 60970983 | Hypo | CABLES2, RPS21 |
| chr20 | 61288068 | 61288156 | Hypo | LOC100127888, SLCO4A1 | chr20 | 60984341 | 60984465 | Hypo | RBBP8NL, CABLES2 |
| chr20 | 61294693 | 61294857 | Hypo | LOC100127888, SLCO4A1 | chr20 | 61288463 | 61288534 | Hypo | LOC100127888, SLCO4A1 |
| chr20 | 61505851 | 61506330 | Hypo | DIDO1 | chr20 | 61412313 | 61412438 | Hypo | LINC00659, AX747649 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr20 | 61714591 | 61714621 | Hypo | | chr20 | 61532546 | 61532605 | Hypo | DIDO1 |
| chr20 | 61765285 | 61765425 | Hypo | | chr20 | 61763598 | 61763628 | Hypo | |
| chr20 | 61974191 | 61974354 | Hypo | CHRNA4 | chr20 | 61823170 | 61823339 | Hypo | YTHDF1 |
| chr20 | 62031173 | 62031234 | Hypo | KCNQ2, AK056267 | chr20 | 61980860 | 61980975 | Hypo | CHRNA4 |
| chr20 | 62037559 | 62037598 | Hypo | KCNQ2 | chr20 | 62032058 | 62032095 | Hypo | KCNQ2, AK056267 |
| chr20 | 62090524 | 62090778 | Hypo | KCNQ2 | chr20 | 62046227 | 62046421 | Hypo | KCNQ2 |
| chr20 | 62126118 | 62126429 | Hypo | EEF1A2 | chr20 | 62115047 | 62115266 | Hypo | EEF1A2 |
| chr20 | 62165631 | 62165762 | Hypo | SRMS, PTK6 | chr20 | 62157151 | 62157307 | Hypo | PTK6, PPDPF |
| chr20 | 62170179 | 62170209 | Hypo | SRMS, PTK6 | chr20 | 62167554 | 62167584 | Hypo | SRMS, PTK6 |
| chr20 | 62260818 | 62260905 | Hypo | GMEB2 | chr20 | 62172945 | 62173055 | Hypo | SRMS, PTK6 |
| chr20 | 62321206 | 62321341 | Hypo | RTEL1-TNFRSF6B, TNFRSF6B, ARFRP1 | chr20 | 62261532 | 62261562 | Hypo | GMEB2, STMN3 |
| chr20 | 62340321 | 62340442 | Hypo | ZGPAT, ARFRP1 | chr20 | 62321638 | 62321679 | Hypo | TNFRSF6B, ARFRP1, RTEL1-TNFRSF6B |
| chr20 | 62488293 | 62488350 | Hypo | TPD52L2, ABHD16B | chr20 | 62383218 | 62383289 | Hypo | ZBTB46, SLC2A4RG |
| chr20 | 62786577 | 62786726 | Hypo | MYT1 | chr20 | 62497836 | 62497920 | Hypo | TPD52L2, ABHD16B |
| chr12 | 2046104 | 2046134 | Hypo | DCP1B, LINC00940 | chr12 | 1650475 | 1650577 | Hypo | |
| chr12 | 2566053 | 2566247 | Hypo | | chr12 | 2403658 | 2403714 | Hypo | CACNAIC-IT3 |
| chr12 | 2964465 | 2964577 | Hypo | FOXM1, LOC100507424 | chr12 | 2595199 | 2595339 | Hypo | |
| chr12 | 4231674 | 4231767 | Hypo | | chr12 | 4213973 | 4214157 | Hypo | |
| chr12 | 4362436 | 4362471 | Hypo | | chr12 | 4323835 | 4323912 | Hypo | |
| chr12 | 4405589 | 4405619 | Hypo | CCND2 | chr12 | 4392883 | 4392922 | Hypo | CCND2 |
| chr12 | 4554801 | 4554831 | Hypo | FGF6 | chr12 | 4431271 | 4431301 | Hypo | C12orf5 |
| chr12 | 6473721 | 6473762 | Hypo | SCNN1A | chr12 | 5840200 | 5840363 | Hypo | ANO2 |
| chr12 | 6678158 | 6678203 | Hypo | CHD4, AK096395, NOP2 | chr12 | 6483615 | 6483756 | Hypo | LTBR, SCNN1A |
| chr12 | 7559160 | 7559307 | Hypo | CD163L1 | chr12 | 7403914 | 7404060 | Hypo | |
| chr12 | 8122523 | 8122628 | Hypo | | chr12 | 8036526 | 8036634 | Hypo | NANOGP1 |
| chr12 | 8139203 | 8139233 | Hypo | | chr12 | 8127036 | 8127140 | Hypo | |
| chr12 | 8808599 | 8808769 | Hypo | MFAP5 | chr12 | 8163573 | 8163603 | Hypo | |
| chr12 | 9916313 | 9916343 | Hypo | CD69 | chr12 | 8975182 | 8975361 | Hypo | A2ML1 |
| chr12 | 10363278 | 10363607 | Hypo | GABARAPL1 | chr12 | 10085916 | 10085948 | Hypo | CLEC2A |
| chr12 | 12848390 | 12848556 | Hypo | GPR19 | chr12 | 12504616 | 12504850 | Hypo | LOH12CR2, LOH12CR1 |
| chr12 | 14719937 | 14719967 | Hypo | PLBD1 | chr12 | 13036048 | 13036078 | Hypo | RPL13AP20, GPRC5A |
| chr12 | 21833068 | 21833265 | Hypo | | chr12 | 14818824 | 14818867 | Hypo | GUCY2C |
| chr12 | 23229390 | 23229420 | Hypo | AK094733 | chr12 | 22698063 | 22698110 | Hypo | C2CD5 |
| chr12 | 27176441 | 27176539 | Hypo | MED21, TM7SF3 | chr12 | 26178334 | 26178376 | Hypo | RASSF8 |
| chr12 | 31366306 | 31366336 | Hypo | OVOS2 | chr12 | 31316012 | 31316362 | Hypo | OVOS2 |
| chr12 | 32340317 | 32340534 | Hypo | BICD1 | chr12 | 32086716 | 32086982 | Hypo | |
| chr12 | 34494888 | 34494918 | Hypo | | chr12 | 32831622 | 32831652 | Hypo | DNM1L |
| chr12 | 43944952 | 43944991 | Hypo | | chr12 | 34502733 | 34502803 | Hypo | |
| chr12 | 49515852 | 49515920 | Hypo | TUBA1A, TUBA1B | chr12 | 49074601 | 49074843 | Hypo | CCNT1 |
| chr12 | 50507349 | 50507522 | Hypo | COX14, GPD1 | chr12 | 49657705 | 49657916 | Hypo | D28390, TUBA1C |
| chr12 | 51400044 | 51400091 | Hypo | U7, SLC11A2 | chr12 | 50897763 | 50898273 | Hypo | DIP2B |
| chr12 | 51421556 | 51421586 | Hypo | | chr12 | 51420874 | 51421271 | Hypo | |
| chr12 | 51565269 | 51565548 | Hypo | | chr12 | 51441284 | 51441368 | Hypo | LETMD1 |
| chr12 | 53763427 | 53763885 | Hypo | | chr12 | 51930708 | 51930862 | Hypo | |
| chr12 | 53834392 | 53834475 | Hypo | PRR13, PCBP2, AMHR2 | chr12 | 53766833 | 53766964 | Hypo | SP1 |
| chr12 | 54613463 | 54613615 | Hypo | | chr12 | 53885346 | 53885651 | Hypo | TARBP2, MAP3K12 |
| chr12 | 54922624 | 54922803 | Hypo | NCKAP1L | chr12 | 54719808 | 54720232 | Hypo | COPZ1 |
| chr12 | 55561202 | 55561354 | Hypo | | chr12 | 55480923 | 55481067 | Hypo | |
| chr12 | 56400463 | 56400591 | Hypo | SUOX, RAB5B | chr12 | 56231108 | 56231148 | Hypo | DNAJC14, MMP19, AX747140 |
| chr12 | 57359920 | 57359950 | Hypo | RDH16 | chr12 | 57174355 | 57174452 | Hypo | HSD17B6 |
| chr12 | 57881127 | 57881383 | Hypo | MARS, ARHGAP9 | chr12 | 57559869 | 57559925 | Hypo | LRP1 |
| chr12 | 64028352 | 64028382 | Hypo | DPY19L2 | chr12 | 63326618 | 63326648 | Hypo | AK024134, PPM1H, Y_RNA |
| chr12 | 65557212 | 65557376 | Hypo | LEMD3 | chr12 | 65516360 | 65516455 | Hypo | WIF1 |
| chr12 | 68978322 | 68978576 | Hypo | | chr12 | 65562025 | 65562086 | Hypo | LEMD3 |
| chr12 | 69964176 | 69964264 | Hypo | FRS2 | chr12 | 69754451 | 69754729 | Hypo | YEATS4, E02193, LYZ |

TABLE 1-continued

| Chr | Start | Stop | Hypo/hyper | Annotation | Chr | Start | Stop | Hypo/hyper | Annotation |
|---|---|---|---|---|---|---|---|---|---|
| chr12 | 70698883 | 70699050 | Hypo | CNOT2 | chr12 | 70087493 | 70087568 | Hypo | BEST3 |
| chr12 | 89915009 | 89915043 | Hypo | GALNT4, POC1B POC1B-GALNT4 | chr12 | 85667353 | 85667465 | Hypo | ALX1 |
| chr12 | 95216830 | 95216960 | Hypo | | chr12 | 94852412 | 94852506 | Hypo | CCDC41-AS1, CCDC41 |
| chr12 | 95866563 | 95866609 | Hypo | METAP2 | chr12 | 95822981 | 95823011 | Hypo | |
| chr12 | 98948200 | 98948295 | Hypo | | chr12 | 96880822 | 96881029 | Hypo | C12orf55 |
| chr12 | 98986343 | 98986491 | Hypo | SLC25A3, SNORA53 | chr12 | 98961066 | 98961241 | Hypo | |
| chr12 | 102457208 | 102457238 | Hypo | CCDC53 | chr12 | 100595495 | 100595558 | Hypo | ACTR6, AX746635 |
| chr12 | 104671699 | 104671761 | Hypo | TXNRD1 | chr12 | 104671030 | 104671064 | Hypo | TXNRD1 |
| chr12 | 108080498 | 108080553 | Hypo | PWP1 | chr12 | 104696376 | 104696502 | Hypo | EID3, TXNRD1 |
| chr12 | 110717541 | 110717710 | Hypo | ATP2A2, JA611269 | chr12 | 110507084 | 110507207 | Hypo | C12orf76 |
| chr12 | 110854243 | 110854288 | Hypo | | chr12 | 110840344 | 110840404 | Hypo | ANAPC7 |
| chr12 | 111143726 | 111143756 | Hypo | | chr12 | 110887179 | 110887209 | Hypo | ARPC3, GPN3 |
| chr12 | 112547662 | 112547692 | Hypo | | chr12 | 111763122 | 111763152 | Hypo | |
| chr12 | 113795506 | 113795657 | Hypo | PLBD2 | chr12 | 112825760 | 112825896 | Hypo | |
| chr12 | 117526330 | 117526368 | Hypo | TESC | chr12 | 117474065 | 117474198 | Hypo | FBXW8, TESC, AK055849 |
| chr12 | 118920764 | 118920804 | Hypo | | chr12 | 118860397 | 118860654 | Hypo | SUDS3 |
| chr12 | 120148923 | 120148962 | Hypo | MIR1178, CIT | chr12 | 120148142 | 120148248 | Hypo | MIR1178, CIT |
| chr12 | 120971686 | 120971716 | Hypo | RNF10, COQ5 | chr12 | 120885215 | 120885245 | Hypo | TRIAP1, COX6A1, GATC |
| chr12 | 122278388 | 122278580 | Hypo | HPD, SETD1B | chr12 | 121622546 | 121622576 | Hypo | P2RX7 |
| chr12 | 122473581 | 122473611 | Hypo | BCL7A | chr12 | 122285067 | 122285108 | Hypo | HPD |
| chr12 | 123233646 | 123233846 | Hypo | DENR | chr12 | 123129129 | 123129550 | Hypo | HCAR1 |
| chr12 | 123942025 | 123942189 | Hypo | SNRNP35 | chr12 | 123410210 | 123410240 | Hypo | ABCB9 |
| chr12 | 124393560 | 124393604 | Hypo | | chr12 | 124117199 | 124117289 | Hypo | EIF2B1, GTF2H3 |
| chr12 | 125009276 | 125009306 | Hypo | | chr12 | 124397464 | 124397618 | Hypo | |
| chr12 | 130037653 | 130037778 | Hypo | | chr12 | 129447299 | 129447450 | Hypo | GLTID1 |
| chr12 | 130968621 | 130968654 | Hypo | RIMBP2 | chr12 | 130821371 | 130821621 | Hypo | PIWIL1 |
| chr12 | 131513345 | 131513403 | Hypo | AX748157, GPR133 | chr12 | 131403032 | 131403125 | Hypo | |
| chr12 | 132221689 | 132222076 | Hypo | SFSWAP | chr12 | 132169288 | 132169442 | Hypo | |
| chr12 | 132333434 | 132333597 | Hypo | MMP17 | chr12 | 132332910 | 132332940 | Hypo | MMP17 |
| chr12 | 132423516 | 132423854 | Hypo | PUS1 | chr12 | 132348651 | 132348684 | Hypo | |
| chr12 | 133002792 | 133003231 | Hypo | | chr12 | 132986495 | 132986581 | Hypo | |
| chr12 | 133199738 | 133199784 | Hypo | POLE, P2RX2 | chr12 | 133172907 | 133173021 | Hypo | LRCOL1 |
| chr11 | 394815 | 394968 | Hypo | PKP3 | chr12 | 133262698 | 133262926 | Hypo | POLE, PXMP2, PGAM5 |
| chr11 | 518400 | 518430 | Hypo | | chr11 | 505732 | 505869 | Hypo | RNH1 |
| chr11 | 763323 | 763686 | Hypo | BC048998, PDDC1, TALDO1 | chr11 | 526389 | 526419 | Hypo | HRAS |
| chr11 | 861612 | 861657 | Hypo | CHID1, AK126635, TSPAN4 | chr11 | 850555 | 850823 | Hypo | AK126635, TSPAN4, POLR2L |
| chr11 | 1006077 | 1006107 | Hypo | MUC6 | chr11 | 863062 | 863092 | Hypo | CHID1, AK126635, TSPAN4 |
| chr11 | 1030215 | 1030296 | Hypo | MUC6 | chr11 | 1029238 | 1029403 | Hypo | MUC6 |
| chr11 | 1081667 | 1081715 | Hypo | MUC2 | chr11 | 1080391 | 1080454 | Hypo | MUC2 |
| chr11 | 1215899 | 1215999 | Hypo | MUC5AC, MUC5B | chr11 | 1214665 | 1214917 | Hypo | MUC5AC, MUC5B |
| chr11 | 1244381 | 1244465 | Hypo | MUC5B | chr11 | 1229945 | 1229975 | Hypo | MUC5AC, MUC5B |
| chr11 | 1251183 | 1251351 | Hypo | MUC5B | chr11 | 1250889 | 1250924 | Hypo | MUC5B |
| chr11 | 1274085 | 1274189 | Hypo | MUC5B | chr11 | 1263602 | 1263644 | Hypo | MUC5B |
| chr11 | 1430714 | 1430794 | Hypo | BRSK2 | chr11 | 1374959 | 1375003 | Hypo | |
| chr11 | 1469228 | 1469379 | Hypo | BRSK2 | chr11 | 1464280 | 1464428 | Hypo | BRSK2 |
| chr11 | 1868081 | 1868237 | Hypo | LSP1, TNNI2 | chr11 | 1471920 | 1472058 | Hypo | BRSK2 |
| chr11 | 1957391 | 1957530 | Hypo | TNNT3 | chr11 | 1946130 | 1946160 | Hypo | TNNT3 |
| chr11 | 2209907 | 2210278 | Hypo | | chr11 | 1959077 | 1959187 | Hypo | MRPL23, TNNT3 |
| chr11 | 2278708 | 2278839 | Hypo | | chr11 | 2226048 | 2226078 | Hypo | |
| chr11 | 3767205 | 3767284 | Hypo | NUP98 | chr11 | 2437991 | 2438144 | Hypo | TRPM5 |
| chr11 | 5993897 | 5994029 | Hypo | OR56A5 | chr11 | 4038082 | 4038176 | Hypo | |
| chr11 | 9405392 | 9405752 | Hypo | IPO7 | chr11 | 6497192 | 6497222 | Hypo | ARFIP2, TIMM10B, TRIM3 |
| chr11 | 10811151 | 10811224 | Hypo | EIF4G2, CTR9 | chr11 | 10509678 | 10509807 | Hypo | AMPD3 |
| chr11 | 14543250 | 14543304 | Hypo | PSMA1 | chr11 | 10815867 | 10815998 | Hypo | EIF4G2, SNORD97 |
| chr11 | 20408219 | 20408341 | Hypo | PRMT3 | chr11 | 14866247 | 14866285 | Hypo | PDE3B |
| chr11 | 33858324 | 33858463 | Hypo | | chr11 | 33277455 | 33277485 | Hypo | HIPK3 |
| chr11 | 34535093 | 34535123 | Hypo | ELF5 | chr11 | 33993984 | 33994014 | Hypo | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr11 | 44337533 | 44337571 | Hypo | ALX4 | chr11 | 35684958 | 35685131 | Hypo | TRIM44 |
| chr11 | 46866293 | 46866510 | Hypo | LRP4-AS1 | chr11 | 46227561 | 46227654 | Hypo | |
| chr11 | 47358926 | 47359237 | Hypo | MYBPC3 | chr11 | 46959190 | 46959251 | Hypo | C11orf49 |
| chr11 | 57437157 | 57437234 | Hypo | ZDHHC5, CLP1 | chr11 | 57235406 | 57235436 | Hypo | RTN4RL2 |
| chr11 | 59329086 | 59329240 | Hypo | JB175310, TRNA_Phe, TRNA_Lys, U7, TRNA_Leu | chr11 | 57500982 | 57501068 | Hypo | TMX2-CTNND1, TMX2, C11orf31, BTBD18 |
| chr11 | 60927079 | 60927319 | Hypo | VPS37C | chr11 | 59841403 | 59841533 | Hypo | MS4A3 |
| chr11 | 61058283 | 61058341 | Hypo | DDB1, VWCE | chr11 | 61049694 | 61049736 | Hypo | VWCE |
| chr11 | 61664655 | 61664770 | Hypo | RAB3IL1, FADS3 | chr11 | 61154806 | 61154836 | Hypo | TMEM216 |
| chr11 | 61811996 | 61812151 | Hypo | | chr11 | 61666106 | 61666136 | Hypo | RAB3IL1, FADS3 |
| chr11 | 62370720 | 62370750 | Hypo | EML3, ROM1, MTA2 | chr11 | 61880361 | 61880398 | Hypo | |
| chr11 | 62497600 | 62497630 | Hypo | TTC9C, HNRNPUL2 | chr11 | 62440509 | 62440588 | Hypo | C11orf83, C11orf48, METTL12, SNORA57, UBXN1 |
| chr11 | 63202941 | 63203091 | Hypo | | chr11 | 62555752 | 62555782 | Hypo | TMEM223, NXF1, TMEM179B, TAF6L |
| chr11 | 63849394 | 63849426 | Hypo | MACROD1 | chr11 | 63609824 | 63610013 | Hypo | MARK2 |
| chr11 | 64105954 | 64106108 | Hypo | CCDC88B | chr11 | 63934498 | 63934619 | Hypo | |
| chr11 | 64140397 | 64140427 | Hypo | MIR 1237, RPS6KA4 | chr11 | 64120879 | 64120909 | Hypo | RPS6KA4, CCDC88B |
| chr11 | 64796439 | 64796571 | Hypo | ARL2-SNX15, ARL2 | chr11 | 64578577 | 64578743 | Hypo | MEN1, MAP4K2 |
| chr11 | 64903331 | 64903361 | Hypo | MRPL49, SYVN1 | chr11 | 64809584 | 64809906 | Hypo | NAALADL1, SAC3D1, ARL2-SNX15 |
| chr11 | 65091272 | 65091369 | Hypo | DPF2, CDC42EP2 | chr11 | 64950292 | 64950374 | Hypo | CAPN1, SPDYC |
| chr11 | 65478376 | 65478611 | Hypo | KAT5, RNASEH2C | chr11 | 65448943 | 65449022 | Hypo | |
| chr11 | 65511392 | 65511522 | Hypo | | chr11 | 65510941 | 65511172 | Hypo | |
| chr11 | 66114279 | 66114331 | Hypo | TRNA_Ser, B3GNT1, BRMS1 | chr11 | 65891131 | 65891227 | Hypo | PACS1 |
| chr11 | 66324254 | 66324447 | Hypo | CTSF, ACTN3 | chr11 | 66138094 | 66138260 | Hypo | AX747485, SLC29A2 |
| chr11 | 66513217 | 66513646 | Hypo | C11orf80 | chr11 | 66511223 | 66511431 | Hypo | C11orf80 |
| chr11 | 66625207 | 66625240 | Hypo | LRFN4, PC | chr11 | 66557543 | 66557710 | Hypo | C11orf80 |
| chr11 | 67072239 | 67072396 | Hypo | SSH3, ANKRD13D, AK057681 | chr11 | 66649028 | 66649058 | Hypo | |
| chr11 | 67248321 | 67248458 | Hypo | AIP | chr11 | 67210017 | 67210057 | Hypo | GPR152, CABP4, CORO1B, PTPRCAP, RPS6KB2 |
| chr11 | 67764187 | 67764254 | Hypo | UNC93B1 | chr11 | 67462643 | 67462833 | Hypo | |
| chr11 | 67999703 | 67999866 | Hypo | | chr11 | 67797202 | 67797420 | Hypo | NDUFS8, MIR4691, TCIRG1, ALDH3B1 |
| chr11 | 68804728 | 68804776 | Hypo | | chr11 | 68221758 | 68222056 | Hypo | PPP6R3, LRP5 |
| chr11 | 69280561 | 69280633 | Hypo | | chr11 | 69192566 | 69192784 | Hypo | |
| chr11 | 71792437 | 71792496 | Hypo | MIR3165, NUMA1, LRTOMT | chr11 | 71192746 | 71192889 | Hypo | NADSYN1 |
| chr11 | 72475677 | 72475711 | Hypo | STARD10 | chr11 | 71863650 | 71863785 | Hypo | |
| chr11 | 73072907 | 73072953 | Hypo | ARHGEF17 | chr11 | 72532348 | 72532378 | Hypo | ATG16L2 |
| chr11 | 74246487 | 74246521 | Hypo | | chr11 | 73310367 | 73310441 | Hypo | FAM168A |
| chr11 | 76371738 | 76372077 | Hypo | LRRC32 | chr11 | 75459486 | 75459775 | Hypo | LOC283214 |
| chr11 | 82998001 | 82998121 | Hypo | BC070093, CCDC90B | chr11 | 77533964 | 77534145 | Hypo | AAMDC, RSF1 |
| chr11 | 96517902 | 96517932 | Hypo | | chr11 | 89052235 | 89052282 | Hypo | NOX4 |
| chr11 | 102158378 | 102158427 | Hypo | | chr11 | 101723359 | 101723455 | Hypo | |
| chr11 | 108603233 | 108603263 | Hypo | DDX10 | chr11 | 102961347 | 102961649 | Hypo | DCUN1D5 |
| chr11 | 116984568 | 116984665 | Hypo | | chr11 | 116976126 | 116976156 | Hypo | |
| chr11 | 118991033 | 118991079 | Hypo | HINFP, C2CD2L | chr11 | 117055950 | 117056073 | Hypo | PAFAH1B2, SIDT2 |
| chr11 | 121152057 | 121152203 | Hypo | | chr11 | 120008105 | 120008504 | Hypo | TRIM29 |
| chr11 | 122961054 | 122961219 | Hypo | CLMP | chr11 | 122895443 | 122895485 | Hypo | LOC341056 |
| chr11 | 125220500 | 125220643 | Hypo | PKNOX2 | chr11 | 123963874 | 123963994 | Hypo | |
| chr11 | 125758604 | 125758660 | Hypo | PUS3, HYLS1 | chr11 | 125755612 | 125755710 | Hypo | HYLS1, PUS3 |
| chr11 | 129907552 | 129907714 | Hypo | | chr11 | 128657892 | 128657970 | Hypo | |
| chr11 | 130359769 | 130359915 | Hypo | | chr11 | 129931742 | 129931851 | Hypo | APLP2 |
| chr11 | 130854324 | 130854490 | Hypo | | chr11 | 130785487 | 130785622 | Hypo | SNX19 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr11 | 131766715 | 131766960 | Hypo | | chr11 | 131522763 | 131522947 | Hypo | |
| chr11 | 133231739 | 133231832 | Hypo | AK056505 | chr11 | 132484215 | 132484404 | Hypo | |
| chrX | 20160594 | 20160914 | Hypo | RPS6KA3, SCARNA9L, EIF1AX | chrX | 15807465 | 15807693 | Hypo | CA5B, ZRSR2, INE2 |
| NW_001838016.1_818233-828058 | 6174 | 6313 | Hypo | | chrX | 44730179 | 44730271 | Hypo | KDM6A |
| chr7 | 369494 | 369536 | Hypo | | chr7 | 68930 | 68960 | Hypo | |
| chr7 | 389663 | 389693 | Hypo | | chr7 | 369844 | 369980 | Hypo | |
| chr7 | 497782 | 497934 | Hypo | | chr7 | 431386 | 431492 | Hypo | LOC442497 |
| chr7 | 551599 | 551697 | Hypo | PDGFA, FLJ44511 | chr7 | 503811 | 503936 | Hypo | |
| chr7 | 579827 | 579857 | Hypo | PRKAR1B | chr7 | 578922 | 579020 | Hypo | PRKAR1B |
| chr7 | 1022224 | 1022254 | Hypo | CYP2W1, COX19 | chr7 | 842331 | 842414 | Hypo | |
| chr7 | 1054579 | 1054696 | Hypo | MIR339, C7orf50 | chr7 | 1030172 | 1030283 | Hypo | C7orf50, CYP2W1 |
| chr7 | 1308351 | 1308497 | Hypo | | chr7 | 1086199 | 1086319 | Hypo | GPR146 |
| chr7 | 1416020 | 1416131 | Hypo | | chr7 | 1325810 | 1325882 | Hypo | |
| chr7 | 1459041 | 1459191 | Hypo | | chr7 | 1423632 | 1423677 | Hypo | |
| chr7 | 1547311 | 1547394 | Hypo | INTS1 | chr7 | 1503417 | 1503596 | Hypo | INTS1, AK127339 |
| chr7 | 1607386 | 1607465 | Hypo | PSMG3-AS1, PSMG3 | chr7 | 1598639 | 1598697 | Hypo | PSMG3, TMEM184A |
| chr7 | 1611443 | 1611522 | Hypo | PSMG3-AS1, PSMG3 | chr7 | 1607971 | 1608001 | Hypo | PSMG3-AS1, PSMG3 |
| chr7 | 1627404 | 1627434 | Hypo | KIAA1908, PSMG3-AS1 | chr7 | 1615390 | 1615444 | Hypo | PSMG3-AS1, PSMG3 |
| chr7 | 1681189 | 1681239 | Hypo | | chr7 | 1641774 | 1641923 | Hypo | |
| chr7 | 1690745 | 1690851 | Hypo | | chr7 | 1688977 | 1689146 | Hypo | |
| chr7 | 1735223 | 1735354 | Hypo | LOC401296 | chr7 | 1733166 | 1733378 | Hypo | LOC401296 |
| chr7 | 1778875 | 1778914 | Hypo | JX046910, ELFN1 | chr7 | 1775831 | 1775861 | Hypo | JX046910, ELFN1 |
| chr7 | 1786514 | 1786899 | Hypo | ELFN1, JX046910 | chr7 | 1783551 | 1783623 | Hypo | ELFN1, JX046910 |
| chr7 | 1800882 | 1800912 | Hypo | | chr7 | 1787166 | 1787324 | Hypo | ELFN1, JX046910 |
| chr7 | 2208670 | 2208808 | Hypo | MAD1L1 | chr7 | 2163332 | 2163467 | Hypo | MAD1L1 |
| chr7 | 2233292 | 2233414 | Hypo | MAD1L1 | chr7 | 2232963 | 2233056 | Hypo | MAD1L1 |
| chr7 | 2361190 | 2361434 | Hypo | SNX8 | chr7 | 2300787 | 2300899 | Hypo | SNX8 |
| chr7 | 2566600 | 2566630 | Hypo | MIR4648, LFNG | chr7 | 2565919 | 2566041 | Hypo | MIR4648, LFNG |
| chr7 | 2720013 | 2720140 | Hypo | AMZ1 | chr7 | 2659340 | 2659370 | Hypo | |
| chr7 | 3283704 | 3283894 | Hypo | | chr7 | 3033658 | 3033688 | Hypo | CARD11 |
| chr7 | 4856984 | 4857048 | Hypo | RADIL | chr7 | 4215324 | 4215384 | Hypo | SDK1 |
| chr7 | 5648218 | 5648393 | Hypo | FSCN1 | chr7 | 5603717 | 5603947 | Hypo | |
| chr7 | 6099217 | 6099334 | Hypo | | chr7 | 6060590 | 6060634 | Hypo | EIF2AK1, AIMP2 |
| chr7 | 6307943 | 6308066 | Hypo | CYTH3 | chr7 | 6124585 | 6124714 | Hypo | |
| chr7 | 6443826 | 6443856 | Hypo | DAGLB, RAC1 | chr7 | 6443279 | 6443376 | Hypo | DAGLB, RAC1 |
| chr7 | 6524977 | 6525012 | Hypo | KDELR2 | chr7 | 6524573 | 6524744 | Hypo | KDELR2 |
| chr7 | 6560235 | 6560345 | Hypo | Mir_633, GRID2IP | chr7 | 6525477 | 6525606 | Hypo | KDELR2 |
| chr7 | 8343630 | 8343724 | Hypo | | chr7 | 7605441 | 7605822 | Hypo | MIOS |
| chr7 | 12776779 | 12776809 | Hypo | | chr7 | 8391475 | 8391573 | Hypo | AX746880 |
| chr7 | 22824965 | 22825009 | Hypo | | chr7 | 21403615 | 21403645 | Hypo | |
| chr7 | 23578703 | 23578857 | Hypo | TRA2A | chr7 | 23526549 | 23526698 | Hypo | RPS2P32 |
| chr7 | 25132558 | 25132726 | Hypo | | chr7 | 24580644 | 24580806 | Hypo | |
| chr7 | 25165921 | 25166061 | Hypo | CYCS, C7orf31 | chr7 | 25133492 | 25133650 | Hypo | |
| chr7 | 26283775 | 26283925 | Hypo | | chr7 | 26194906 | 26195024 | Hypo | NFE2L3 |
| chr7 | 28238339 | 28238444 | Hypo | JAZF1-AS1 | chr7 | 27245668 | 27245795 | Hypo | HOTTIP, HOXA13 |
| chr7 | 30030307 | 30030337 | Hypo | SCRN1 | chr7 | 28989065 | 28989159 | Hypo | TRIL, DQ601810 |
| chr7 | 35301086 | 35301216 | Hypo | TBX20 | chr7 | 35298755 | 35298819 | Hypo | TBX20 |
| chr7 | 37907440 | 37907470 | Hypo | NME8 | chr7 | 37352957 | 37353062 | Hypo | |
| chr7 | 44083283 | 44083416 | Hypo | DBNL, LINC00957, RASA4CP | chr7 | 43817999 | 43818119 | Hypo | BLVRA |
| chr7 | 44151795 | 44151933 | Hypo | MIR 4649, POLD2, AEBP1 | chr7 | 44151398 | 44151428 | Hypo | POLD2, AEBP1, MIR4649 |
| chr7 | 45026942 | 45027045 | Hypo | SNORA9, SNHG15, MYO1G | chr7 | 44835037 | 44835384 | Hypo | PPIA |
| chr7 | 45525402 | 45525432 | Hypo | | chr7 | 45038532 | 45038655 | Hypo | CCM2 |
| chr7 | 47704289 | 47704359 | Hypo | C7orf65 | chr7 | 47515359 | 47515405 | Hypo | TNS3 |
| chr7 | 50294451 | 50294481 | Hypo | | chr7 | 49654508 | 49654538 | Hypo | |
| chr7 | 50438618 | 50438648 | Hypo | IKZF1 | chr7 | 50365076 | 50365137 | Hypo | IKZF1 |
| chr7 | 50560588 | 50560637 | Hypo | DDC | chr7 | 50441145 | 50441285 | Hypo | IKZF1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr7 | 56031716 | 56031869 | Hypo | GBAS, MRPS17 | chr7 | 56018123 | 56018286 | Hypo | ZNF713, MRPS17 |
| chr7 | 64713317 | 64713449 | Hypo | | chr7 | 64330734 | 64330833 | Hypo | AK097702 |
| chr7 | 65879649 | 65879883 | Hypo | | chr7 | 65510006 | 65510096 | Hypo | |
| chr7 | 66204493 | 66204617 | Hypo | RABGEF1 | chr7 | 65880359 | 65880405 | Hypo | |
| chr7 | 66214923 | 66214961 | Hypo | RABGEF1 | chr7 | 66206923 | 66206953 | Hypo | RABGEF1 |
| chr7 | 68204793 | 68204948 | Hypo | | chr7 | 67579765 | 67579911 | Hypo | |
| chr7 | 69897780 | 69897827 | Hypo | AUTS2 | chr7 | 69352121 | 69352272 | Hypo | AUTS2 |
| chr7 | 71438424 | 71438454 | Hypo | CALN1 | chr7 | 70990312 | 70990342 | Hypo | |
| chr7 | 71871203 | 71871245 | Hypo | | chr7 | 71603924 | 71604082 | Hypo | |
| chr7 | 77309437 | 77309511 | Hypo | RSBN1L-AS1 | chr7 | 77308664 | 77308899 | Hypo | RSBN1L-AS1 |
| chr7 | 87706818 | 87706877 | Hypo | ADAM22 | chr7 | 77324362 | 77324593 | Hypo | RSBN1L-AS1, RSBN1L |
| chr7 | 92554253 | 92554452 | Hypo | | chr7 | 90269263 | 90269563 | Hypo | CDK14 |
| chr7 | 93220696 | 93220826 | Hypo | GNGT1 | chr7 | 92689705 | 92689818 | Hypo | |
| chr7 | 96627013 | 96627064 | Hypo | DLX6-AS1, DLX6 | chr7 | 94138158 | 94138315 | Hypo | CASD1 |
| chr7 | 97580497 | 97580648 | Hypo | MGC72080 | chr7 | 96651469 | 96651537 | Hypo | DLX5 |
| chr7 | 97839654 | 97839684 | Hypo | BHLHA15, TECPR1, LMTK2 | chr7 | 97600104 | 97600224 | Hypo | BC122864, MGC72080 |
| chr7 | 97869614 | 97869644 | Hypo | TECPR1 | chr7 | 97869290 | 97869391 | Hypo | TECPR1 |
| chr7 | 98969875 | 98969928 | Hypo | ARPC1B, ARPC1A | chr7 | 98197206 | 98197242 | Hypo | |
| chr7 | 99104258 | 99104388 | Hypo | ZKSCAN5, AJ297365, ZNF394 | chr7 | 98971509 | 98971549 | Hypo | ARPC1B, ARPC1A |
| chr7 | 99642049 | 99642100 | Hypo | ZSCAN21, ZKSCAN1 | chr7 | 99591579 | 99591762 | Hypo | AZGP1P1 |
| chr7 | 100088183 | 100088312 | Hypo | NYAP1 | chr7 | 99934913 | 99934943 | Hypo | PMS2P1, PILRB |
| chr7 | 100241592 | 100241697 | Hypo | ACTL6B, TFR2 | chr7 | 100179889 | 100179927 | Hypo | FBXO24, PCOLCE-AS1, LRCH4, ZASP, SAP25 |
| chr7 | 101241993 | 101242023 | Hypo | | chr7 | 100295321 | 100295424 | Hypo | POP7, GIGYF1 |
| chr7 | 101585887 | 101585917 | Hypo | CUX1 | chr7 | 101475790 | 101475858 | Hypo | CUX1 |
| chr7 | 101707502 | 101707532 | Hypo | CUX1 | chr7 | 101627741 | 101627787 | Hypo | CUX1 |
| chr7 | 106622834 | 106622961 | Hypo | | chr7 | 105279467 | 105279671 | Hypo | ATXN7L1 |
| chr7 | 121956724 | 121956754 | Hypo | FEZF1-AS1, CADPS2 | chr7 | 111203114 | 111203260 | Hypo | |
| chr7 | 125082621 | 125082698 | Hypo | | chr7 | 123175689 | 123175899 | Hypo | NDUFA5, IQUB |
| chr7 | 128486036 | 128486138 | Hypo | FLNC | chr7 | 128097059 | 128097089 | Hypo | HILPDA |
| chr7 | 128529023 | 128529053 | Hypo | KCP | chr7 | 128528749 | 128528779 | Hypo | KCP |
| chr7 | 129794593 | 129794721 | Hypo | TMEM209 | chr7 | 129229456 | 129229631 | Hypo | |
| chr7 | 136969053 | 136969083 | Hypo | SNORD81, PTN | chr7 | 129844226 | 129844493 | Hypo | TMEM209, SSMEM1 |
| chr7 | 139939160 | 139939318 | Hypo | | chr7 | 139878250 | 139878296 | Hypo | LOC100134229, JHDM1D |
| chr7 | 140097126 | 140097196 | Hypo | AK131347, RAB19 | chr7 | 140096812 | 140096882 | Hypo | RAB19, AK131347 |
| chr7 | 144712934 | 144713064 | Hypo | | chr7 | 142785612 | 142785728 | Hypo | |
| chr7 | 148640171 | 148640250 | Hypo | | chr7 | 148224541 | 148224686 | Hypo | |
| chr7 | 148846434 | 148846644 | Hypo | ZNF398 | chr7 | 148846138 | 148846180 | Hypo | ZNF398 |
| chr7 | 149109648 | 149109785 | Hypo | TRNA_Cys | chr7 | 148883821 | 148883973 | Hypo | ZNF282, ZNF398 |
| chr7 | 150081236 | 150081308 | Hypo | ZNF775 | chr7 | 150049604 | 150049718 | Hypo | |
| chr7 | 150870816 | 150870889 | Hypo | ASB10, GBX1 | chr7 | 150753942 | 150753981 | Hypo | SLC4A2, CDK5, ASIC3 |
| chr7 | 151591667 | 151591705 | Hypo | | chr7 | 151001356 | 151001435 | Hypo | |
| chr7 | 153633796 | 153633942 | Hypo | DPP6 | chr7 | 152913656 | 152913826 | Hypo | |
| chr7 | 154708275 | 154708338 | Hypo | | chr7 | 154561150 | 154561189 | Hypo | DPP6 |
| chr7 | 155302881 | 155302917 | Hypo | CNPY1 | chr7 | 154926351 | 154926397 | Hypo | |
| chr7 | 155580846 | 155580876 | Hypo | RBM33 | chr7 | 155363304 | 155363417 | Hypo | |
| chr7 | 155581765 | 155581980 | Hypo | RBM33 | chr7 | 155581330 | 155581553 | Hypo | RBM33 |
| chr7 | 155877196 | 155877283 | Hypo | | chr7 | 155582277 | 155582340 | Hypo | RBM33 |
| chr7 | 156744619 | 156744713 | Hypo | NOM1 | chr7 | 156707963 | 156708093 | Hypo | |
| chr7 | 156832223 | 156832402 | Hypo | | chr7 | 156779336 | 156779366 | Hypo | MNX1 |
| chr7 | 156880531 | 156880561 | Hypo | | chr7 | 156832848 | 156833162 | Hypo | |
| chr7 | 157085963 | 157086082 | Hypo | | chr7 | 157085373 | 157085487 | Hypo | |
| chr7 | 157263294 | 157263471 | Hypo | | chr7 | 157262815 | 157263018 | Hypo | |
| chr7 | 157584178 | 157584208 | Hypo | | chr7 | 157335172 | 157335202 | Hypo | PTPRN2 |
| chr7 | 157606706 | 157606736 | Hypo | | chr7 | 157588586 | 157588791 | Hypo | |
| chr7 | 158059762 | 158059794 | Hypo | | chr7 | 157690056 | 157690086 | Hypo | |
| chr19 | 403538 | 403809 | Hypo | C2CD4C | chr7 | 158065832 | 158065970 | Hypo | |
| chr19 | 468757 | 468787 | Hypo | ODF3L2, SHC2 | chr19 | 407189 | 407320 | Hypo | SHC2, C2CD4C |
| chr19 | 549361 | 549451 | Hypo | GZMM, CDC34 | chr19 | 485165 | 485394 | Hypo | |
| chr19 | 592589 | 592632 | Hypo | HCN2, BSG | chr19 | 555608 | 555768 | Hypo | GZMM |
| chr19 | 599214 | 599333 | Hypo | HCN2 | chr19 | 593290 | 593462 | Hypo | HCN2, BSG |
| chr19 | 752136 | 752462 | Hypo | MISP, PALM | chr19 | 690888 | 690940 | Hypo | PRSS57, FSTL3 |
| chr19 | 884018 | 884162 | Hypo | MED16, U6 | chr19 | 883624 | 883791 | Hypo | MED 16, U6 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr19 | 955757 | 956237 | Hypo | ARID3A | chr19 | 891516 | 891723 | Hypo | MED16, U6, R3HDM4 |
| chr19 | 1003669 | 1003734 | Hypo | TMEM259, GRIN3B, WDR18, FLJ00277 | chr19 | 1003305 | 1003384 | Hypo | FLJ00277, TMEM259, GRIN3B, WDR18 |
| chr19 | 1030176 | 1030225 | Hypo | ABCA7, CNN2 | chr19 | 1004915 | 1005441 | Hypo | FLJ00277, TMEM259, GRIN3B |
| chr19 | 1083314 | 1083437 | Hypo | POLR2E, HMHA1 | chr19 | 1047890 | 1047939 | Hypo | ABCA7 |
| chr19 | 1170185 | 1170230 | Hypo | | chr19 | 1156524 | 1156554 | Hypo | |
| chr19 | 1236474 | 1236678 | Hypo | STK11, ATP5D, C19orf26 | chr19 | 1171099 | 1171324 | Hypo | |
| chr19 | 1325788 | 1325889 | Hypo | | chr19 | 1274778 | 1274826 | Hypo | C19orf24, DL492057, CIRBP, CIRBP-AS1 |
| chr19 | 1496413 | 1496450 | Hypo | ADAMTSL5, REEP6, PCSK4 | chr19 | 1330064 | 1330214 | Hypo | |
| chr19 | 1525605 | 1525960 | Hypo | PLK5 | chr19 | 1496654 | 1496694 | Hypo | ADAMTSL5, REEP6, PCSK4 |
| chr19 | 1547233 | 1547263 | Hypo | MEX3D | chr19 | 1527227 | 1527394 | Hypo | PLK5 |
| chr19 | 1799466 | 1799516 | Hypo | ATP8B3 | chr19 | 1689436 | 1689595 | Hypo | |
| chr19 | 1807970 | 1808413 | Hypo | REXO1, MIR1909, ATP8B3 | chr19 | 1800032 | 1800300 | Hypo | ATP8B3 |
| chr19 | 2274677 | 2274713 | Hypo | C19orf35, SPPL2B, OAZ1 | chr19 | 2155031 | 2155061 | Hypo | DOT1L |
| chr19 | 2331413 | 2331443 | Hypo | SPPL2B, LSM7 | chr19 | 2330317 | 2330407 | Hypo | SPPL2B, LSM7 |
| chr19 | 2414257 | 2414337 | Hypo | TMPRSS9 | chr19 | 2413125 | 2413155 | Hypo | TMPRSS9 |
| chr19 | 2642877 | 2642947 | Hypo | BC022568, GNG7 | chr19 | 2513250 | 2513285 | Hypo | GNG7 |
| chr19 | 3041417 | 3041447 | Hypo | | chr19 | 2683911 | 2684080 | Hypo | |
| chr19 | 3219512 | 3219565 | Hypo | CELF5, NCLN | chr19 | 3093571 | 3093818 | Hypo | GNA11 |
| chr19 | 3562128 | 3562797 | Hypo | MFSD12 | chr19 | 3296613 | 3296670 | Hypo | CELF5 |
| chr19 | 3716179 | 3716241 | Hypo | TJP3 | chr19 | 3570230 | 3570371 | Hypo | HMG20B |
| chr19 | 3778130 | 3778394 | Hypo | JA611290, MATK, RAX2 | chr19 | 3718052 | 3718082 | Hypo | TJP3 |
| chr19 | 3821044 | 3821217 | Hypo | ZFR2 | chr19 | 3779277 | 3779435 | Hypo | JA611290, MATK, RAX2 |
| chr19 | 3966686 | 3966755 | Hypo | MIR637, DAPK3, EEF2 | chr19 | 3855407 | 3855595 | Hypo | ZFR2 |
| chr19 | 4160800 | 4160898 | Hypo | CREB3L3 | chr19 | 4095471 | 4095514 | Hypo | MAP2K2 |
| chr19 | 4311273 | 4311430 | Hypo | FSD1, TMIGD2 | chr19 | 4195767 | 4195853 | Hypo | ANKRD24 |
| chr19 | 4548134 | 4548364 | Hypo | SEMA6B, LRG1, PLIN5 | chr19 | 4509338 | 4509440 | Hypo | PLIN4, HDGFRP2 |
| chr19 | 4550246 | 4550330 | Hypo | SEMA6B | chr19 | 4549454 | 4549565 | Hypo | SEMA6B, LRG1 PLIN5 |
| chr19 | 4557098 | 4557235 | Hypo | SEMA6B | chr19 | 4555896 | 4556112 | Hypo | SEMA6B |
| chr19 | 4670765 | 4670949 | Hypo | DPP9, LOC100131094, C19orf10 | chr19 | 4572332 | 4572459 | Hypo | |
| chr19 | 4790142 | 4790264 | Hypo | FEM1A, AK126532 | chr19 | 4789697 | 4789805 | Hypo | FEM1A, AK126532 |
| chr19 | 5676212 | 5676242 | Hypo | HSD11B1L, C19orf70 | chr19 | 5608519 | 5608569 | Hypo | SAFB2 |
| chr19 | 5759744 | 5759774 | Hypo | CATSPERD | chr19 | 5759374 | 5759544 | Hypo | CATSPERD |
| chr19 | 5826179 | 5826209 | Hypo | FUT6, NRTN | chr19 | 5767703 | 5767733 | Hypo | CATSPERD |
| chr19 | 5910356 | 5910492 | Hypo | CAPS, RANBP3, VMAC, NDUFA11 | chr19 | 5905517 | 5905547 | Hypo | CAPS, VMAC, NDUFA11 |
| chr19 | 5914992 | 5915060 | Hypo | RANBP3, CAPS, VMAC | chr19 | 5914761 | 5914791 | Hypo | CAPS, VMAC, RANBP3 |
| chr19 | 6512913 | 6512943 | Hypo | | chr19 | 6303268 | 6303298 | Hypo | ACER1 |
| chr19 | 6889423 | 6889574 | Hypo | EMR1 | chr19 | 6658279 | 6658422 | Hypo | TNFSF14 |
| chr19 | 7635387 | 7635552 | Hypo | PNPLA6 | chr19 | 7554718 | 7554780 | Hypo | C19orf45, PEX11G |
| chr19 | 8391621 | 8391651 | Hypo | RPS28, NDUFA7, KANK3 | chr19 | 7870346 | 7870387 | Hypo | |
| chr19 | 9937291 | 9937386 | Hypo | UBL5, PIN1, FBXL12 | chr19 | 9239580 | 9239695 | Hypo | OR7G3 |
| chr19 | 10362045 | 10362182 | Hypo | MRPL4 | chr19 | 10231077 | 10231242 | Hypo | EIF3G, P2RY11 |
| chr19 | 10648372 | 10648546 | Hypo | ATG4D | chr19 | 10621768 | 10621829 | Hypo | S1PR5, KEAP1 |
| chr19 | 10827675 | 10827705 | Hypo | DNM2, MIR638, QTRT1 | chr19 | 10729811 | 10729899 | Hypo | SLC44A2 |
| chr19 | 11063941 | 11063971 | Hypo | SMARCA4 | chr19 | 10955456 | 10955585 | Hypo | C19orf38, TMED1 |
| chr19 | 12661175 | 12661221 | Hypo | ZNF564, ZNF709 | chr19 | 12147437 | 12147545 | Hypo | ZNF878, ZNF433, AX747405 |
| chr19 | 12860307 | 12860433 | Hypo | BEST2, ASNA1 | chr19 | 12846906 | 12847098 | Hypo | ASNA1, C19orf43 |
| chr19 | 13903520 | 13903603 | Hypo | ZSWIM4 | chr19 | 12863412 | 12863520 | Hypo | BEST2, ASNA1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr19 | 13988775 | 13988805 | Hypo | C19orf57, NANOS3, MIR181D, MIR181C | chr19 | 13965838 | 13965965 | Hypo | |
| chr19 | 14324876 | 14324906 | Hypo | | chr19 | 14085021 | 14085051 | Hypo | RFX1 |
| chr19 | 14411056 | 14411086 | Hypo | | chr19 | 14327101 | 14327158 | Hypo | |
| chr19 | 15292384 | 15292414 | Hypo | NOTCH3 | chr19 | 14869496 | 14869526 | Hypo | EMR2 |
| chr19 | 17335642 | 17335718 | Hypo | OCEL1, NR2F6, USE1 | chr19 | 17152333 | 17152363 | Hypo | HAUS8 |
| chr19 | 17359350 | 17359459 | Hypo | USHBP1, NR2F6 | chr19 | 17336042 | 17336111 | Hypo | OCEL1, NR2F6, USE1 |
| chr19 | 18041069 | 18041203 | Hypo | CCDC124 | chr19 | 17446897 | 17447045 | Hypo | AK310794, GTPBP3, ANO8 |
| chr19 | 18103711 | 18103741 | Hypo | ARRDC2, KCNN1 | chr19 | 18057603 | 18057655 | Hypo | KCNN1, CCDC124 |
| chr19 | 18300127 | 18300422 | Hypo | MPV17L2, RAB3A | chr19 | 18104472 | 18104606 | Hypo | ARRDC2, KCNN1 |
| chr19 | 18331031 | 18331136 | Hypo | PDE4C | chr19 | 18301007 | 18301037 | Hypo | MPV17L2, RAB3A |
| chr19 | 18488862 | 18488915 | Hypo | GDF15, MIR3189, PGPEP1 | chr19 | 18383211 | 18383351 | Hypo | JUND, MIR3188 |
| chr19 | 18633926 | 18633980 | Hypo | FKBP8, ELL | chr19 | 18523115 | 18523145 | Hypo | SSBP4 |
| chr19 | 18872825 | 18872900 | Hypo | CRTC1 | chr19 | 18681638 | 18681926 | Hypo | UBA52, DL491652, KXD1 |
| chr19 | 18994887 | 18995206 | Hypo | CERS1, GDF1 | chr19 | 18989821 | 18990281 | Hypo | CERS1, GDF1 |
| chr19 | 19489251 | 19489297 | Hypo | GATAD2A | chr19 | 19334831 | 19334915 | Hypo | NCAN |
| chr19 | 19775308 | 19775472 | Hypo | ZNF101, ATP13A1 | chr19 | 19645834 | 19645925 | Hypo | CILP2, YJEFN3, NDUFA13 |
| chr19 | 21512594 | 21512660 | Hypo | ZNF708 | chr19 | 21265890 | 21265920 | Hypo | ZNF714 |
| chr19 | 29505153 | 29505183 | Hypo | LOC100505835 | chr19 | 21665258 | 21665290 | Hypo | LINC00664 |
| chr19 | 30252296 | 30252369 | Hypo | | chr19 | 30130889 | 30130919 | Hypo | |
| chr19 | 30562775 | 30563017 | Hypo | | chr19 | 30555329 | 30555376 | Hypo | |
| chr19 | 30637494 | 30637531 | Hypo | | chr19 | 30582601 | 30582649 | Hypo | |
| chr19 | 31804724 | 31804754 | Hypo | TSHZ3 | chr19 | 30703436 | 30703469 | Hypo | |
| chr19 | 32380872 | 32380961 | Hypo | | chr19 | 32364365 | 32364403 | Hypo | |
| chr19 | 32835279 | 32835309 | Hypo | ZNF507 | chr19 | 32516399 | 32516516 | Hypo | AK097493 |
| chr19 | 33571250 | 33571280 | Hypo | GPATCH1 | chr19 | 32898335 | 32898490 | Hypo | DPY19L3, LOC400684 |
| chr19 | 35616341 | 35616397 | Hypo | LGI4, FXYD3 | chr19 | 34896324 | 34896360 | Hypo | PDCD2L, GPI |
| chr19 | 35783136 | 35783231 | Hypo | HAMP, MAG | chr19 | 35781374 | 35781459 | Hypo | MAG, HAMP |
| chr19 | 36200805 | 36200847 | Hypo | ZBTB32, KMT2B | chr19 | 35797916 | 35797965 | Hypo | MAG |
| chr19 | 36250029 | 36250134 | Hypo | C19orf55, HSPB6, LIN37, AL137752 | chr19 | 36222432 | 36222534 | Hypo | IGFLR1, KMT2B |
| chr19 | 36265053 | 36265186 | Hypo | ARHGAP33, C19orf55 | chr19 | 36264697 | 36264773 | Hypo | ARHGAP33, C19orf55 |
| chr19 | 36707435 | 36707467 | Hypo | ZNF146, ZNF565 | chr19 | 36413776 | 36413830 | Hypo | |
| chr19 | 38481044 | 38481217 | Hypo | SIPA1L3 | chr19 | 37702003 | 37702169 | Hypo | ZNF383, ZNF585B |
| chr19 | 38736072 | 38736127 | Hypo | PPP1R14A | chr19 | 38733924 | 38733954 | Hypo | PPP1R14A |
| chr19 | 38757128 | 38757308 | Hypo | SPINT2, PPPIR14A | chr19 | 38747729 | 38747767 | Hypo | SPINT2, PPP1R14A |
| chr19 | 38873935 | 38873965 | Hypo | PSMD8, GGN, SPRED3 | chr19 | 38789218 | 38789288 | Hypo | YIF1B, C19orf33, SPINT2 |
| chr19 | 38974232 | 38974262 | Hypo | RYR1 | chr19 | 38905548 | 38905702 | Hypo | FAM98C, RASGRP4 |
| chr19 | 39290904 | 39290944 | Hypo | LGALS4, LGALS7B | chr19 | 39135294 | 39135454 | Hypo | ACTN4, EIF3K |
| chr19 | 39934694 | 39934784 | Hypo | SUPT5H, RPS16 | chr19 | 39816936 | 39817085 | Hypo | BC110060, GMFG |
| chr19 | 40829866 | 40829939 | Hypo | C19orf47 | chr19 | 40210391 | 40210573 | Hypo | |
| chr19 | 40951175 | 40951357 | Hypo | BLVRB, SERTAD3 | chr19 | 40902425 | 40902812 | Hypo | PRX, HIPK4 |
| chr19 | 40991013 | 40991139 | Hypo | SPTBN4 | chr19 | 40951679 | 40951762 | Hypo | BLVRB, SERTAD3 |
| chr19 | 41694610 | 41694640 | Hypo | CYP2S1 | chr19 | 41473190 | 41473242 | Hypo | |
| chr19 | 42408300 | 42408330 | Hypo | ARHGEF1 | chr19 | 41881534 | 41881811 | Hypo | TMEM91, BCKDHA |
| chr19 | 45003211 | 45003323 | Hypo | CEACAM20, ZNF180 | chr19 | 44599783 | 44599883 | Hypo | ZNF284, LOC100379224, ZNF224 |
| chr19 | 45574465 | 45574495 | Hypo | CLASRP, ZNF296, GEMIN7 | chr19 | 45541556 | 45541679 | Hypo | CLASRP, RELB |
| chr19 | 45810102 | 45810267 | Hypo | CKM | chr19 | 45601380 | 45601410 | Hypo | GEMIN7, PPPIR37 |
| chr19 | 45997528 | 45997584 | Hypo | PPMIN, RTN2 | chr19 | 45835028 | 45835268 | Hypo | KLC3, CKM |
| chr19 | 46404522 | 46404601 | Hypo | MYPOP | chr19 | 46234803 | 46234887 | Hypo | LOC388553 |
| chr19 | 47329748 | 47329867 | Hypo | SNAR-E | chr19 | 47200361 | 47200536 | Hypo | PRKD2 |
| chr19 | 47515017 | 47515047 | Hypo | NPAS1, ARHGAP35 | chr19 | 47358646 | 47358751 | Hypo | AP2S1 |
| chr19 | 47976399 | 47976429 | Hypo | KPTN, SLC8A2 | chr19 | 47618255 | 47618434 | Hypo | ZC3H4 |
| chr19 | 48082100 | 48082130 | Hypo | | chr19 | 48003607 | 48003714 | Hypo | NAPA, NAPA-AS1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr19 | 48137171 | 48137307 | Hypo | GLTSCR1 | chr19 | 48108151 | 48108320 | Hypo | GLTSCR1 |
| chr19 | 48249451 | 48249602 | Hypo | GLTSCR2, SNORD23, EHD2 | chr19 | 48151265 | 48151337 | Hypo | GLTSCR1 |
| chr19 | 48771551 | 48771600 | Hypo | ZNF114 | chr19 | 48614843 | 48614873 | Hypo | LIG1, PLA2G4C |
| chr19 | 48800603 | 48800769 | Hypo | CCDC114, ZNF114 | chr19 | 48777059 | 48777121 | Hypo | ZNF114 |
| chr19 | 48902848 | 48902878 | Hypo | GRIN2D, KDELR1 | chr19 | 48857725 | 48857831 | Hypo | SYNGR4, TMEM143, Mir_324 |
| chr19 | 49119229 | 49119259 | Hypo | RPL18, SPHK2, SPACA4, FAM83E | chr19 | 49043242 | 49043272 | Hypo | |
| chr19 | 49285456 | 49285593 | Hypo | | chr19 | 49180462 | 49180558 | Hypo | NTN5 |
| chr19 | 49375050 | 49375216 | Hypo | PPP1R15A, TULP2, PLEKHA4 | chr19 | 49290711 | 49290844 | Hypo | BCAT2, Mir_324 |
| chr19 | 49498076 | 49498148 | Hypo | RUVBL2 | chr19 | 49402471 | 49402551 | Hypo | Mir_324, TULP2 NUCB1 |
| chr19 | 49628132 | 49628252 | Hypo | PPFIA3, C19orf73, Mir_324, LIN7B | chr19 | 49590284 | 49590399 | Hypo | SNRNP70 |
| chr19 | 49890887 | 49890929 | Hypo | CCDC155 | chr19 | 49784869 | 49784935 | Hypo | SLC6A16 |
| chr19 | 49998434 | 49998607 | Hypo | SNORD33, SNORD32A, FLT3LG, MIR150, SNORD35B, SNORD35A, SNORD34, RPL13A, RPS11 | chr19 | 49997263 | 49997324 | Hypo | RPS11, MIR150, SNORD35A, SNORD32A, RPL13A, FLT3LG, SNORD35B, SNORD34, SNORD33 |
| chr19 | 50049718 | 50049953 | Hypo | NOSIP | chr19 | 50028397 | 50028530 | Hypo | TRNA_Lys, FCGRT, RCN3 |
| chr19 | 50216042 | 50216072 | Hypo | CPT1C | chr19 | 50203173 | 50203203 | Hypo | CPT1C, ADM5 |
| chr19 | 50320233 | 50320277 | Hypo | MED25, FUZ, AP2A1 | chr19 | 50319874 | 50319916 | Hypo | AP2A1, MED25, FUZ |
| chr19 | 50874895 | 50874933 | Hypo | NR1H2, NAPSA | chr19 | 50353394 | 50353574 | Hypo | PTOV1, MIR4749, PTOV1-AS1 |
| chr19 | 51304554 | 51304602 | Hypo | C19orf48, ACPT, SNORD88C, SNORD88A, SNORD88B | chr19 | 50938547 | 50938691 | Hypo | MYBPC2, SPIB |
| chr19 | 52139210 | 52139326 | Hypo | SIGLEC14, SIGLEC5 | chr19 | 51715329 | 51715359 | Hypo | |
| chr19 | 53291021 | 53291081 | Hypo | ZNF28 | chr19 | 53028928 | 53029035 | Hypo | ZNF808 |
| chr19 | 53446951 | 53447130 | Hypo | ZNF816, ZNF816-ZNF321P, ZNF321P | chr19 | 53399814 | 53399848 | Hypo | ZNF320 |
| chr19 | 55849550 | 55849638 | Hypo | SUV420H2, TMEM150B | chr19 | 55728901 | 55729104 | Hypo | TMEM86B, PTPRH |
| chr19 | 56588656 | 56588780 | Hypo | ZNF787 | chr19 | 56340995 | 56341033 | Hypo | NLRP4, NLRP11 |
| chr19 | 58316915 | 58317096 | Hypo | ZNF552 | chr19 | 56858084 | 56858227 | Hypo | |
| chr19 | 58874735 | 58874987 | Hypo | ZNF837, BC023201, ZNF497, A1BG-AS1, A1BG | chr19 | 58325075 | 58325282 | Hypo | ZNF552, ZNF587, ZNF587B |
| chr19 | 59054642 | 59054774 | Hypo | TRIM28, CHMP2A | chr19 | 58964180 | 58964266 | Hypo | ZNF324B |
| chr22 | 18009969 | 18010121 | Hypo | CECR2 | GL000231.1 | 12576 | 12717 | Hypo | |
| chr22 | 18328209 | 18328268 | Hypo | MICAL3, BC064400 | chr22 | 18110495 | 18110593 | Hypo | BCL2L13, ATP6V1E1 |
| chr22 | 19117564 | 19117594 | Hypo | DGCR14, TSSK2 | chr22 | 18340822 | 18340868 | Hypo | MICAL3 |
| chr22 | 21042829 | 21043014 | Hypo | POM121L4P, DQ571461 | chr22 | 20864642 | 20864672 | Hypo | MED15 |
| chr22 | 21270750 | 21270834 | Hypo | CRKL | chr22 | 21153867 | 21154000 | Hypo | PI4KA |
| chr22 | 21304771 | 21305007 | Hypo | BC033281, BC127858, CRKL | chr22 | 21276140 | 21276261 | Hypo | CRKL |
| chr22 | 22023273 | 22023451 | Hypo | PPIL2 | chr22 | 21982792 | 21982972 | Hypo | CCDC116, YDJC, UBE2L3 |
| chr22 | 23791402 | 23791432 | Hypo | | chr22 | 22901105 | 22901455 | Hypo | PRAME, LOC648691 |
| chr22 | 29977614 | 29977863 | Hypo | NIPSNAP1 | chr22 | 28371649 | 28371679 | Hypo | TTC28 |
| chr22 | 30158330 | 30158639 | Hypo | UQCR10, ZMAT5 | chr22 | 30084358 | 30084388 | Hypo | NF2 |
| chr22 | 32061344 | 32061374 | Hypo | | chr22 | 30784196 | 30784278 | Hypo | SEC14L2, RNF215 |
| chr22 | 32868720 | 32868837 | Hypo | FBXO7, BPIFC | chr22 | 32748936 | 32748966 | Hypo | RFPL3, RFPL3S, JB153905 |
| chr22 | 35768531 | 35768719 | Hypo | HMOX1 | chr22 | 35079219 | 35079345 | Hypo | |
| chr22 | 36567866 | 36567896 | Hypo | | chr22 | 35848358 | 35848670 | Hypo | |
| chr22 | 36855568 | 36855598 | Hypo | TXN2 | chr22 | 36855297 | 36855335 | Hypo | TXN2 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr22 | 37302073 | 37302103 | Hypo | CSF2RB | chr22 | 36880362 | 36880462 | Hypo | FOXRED2, TXN2 |
| chr22 | 38199769 | 38199894 | Hypo | H1F0, GCAT | chr22 | 38002684 | 38002733 | Hypo | GGA1 |
| chr22 | 38592856 | 38593076 | Hypo | MAFF | chr22 | 38507316 | 38507346 | Hypo | PLA2G6 |
| chr22 | 39094890 | 39094964 | Hypo | GTPBP1, JOSD1 | chr22 | 38639229 | 38639259 | Hypo | TMEM184B |
| chr22 | 39932499 | 39932563 | Hypo | RPS19BP1 | chr22 | 39098022 | 39098064 | Hypo | GTPBP1, JOSD1 |
| chr22 | 40226345 | 40226389 | Hypo | ENTHD1 | chr22 | 40042627 | 40042743 | Hypo | CACNA1I |
| chr22 | 40895978 | 40896029 | Hypo | MKL1 | chr22 | 40767753 | 40767936 | Hypo | SGSM3, ADSL |
| chr22 | 41048732 | 41049109 | Hypo | | chr22 | 41048488 | 41048518 | Hypo | |
| chr22 | 41634497 | 41634542 | Hypo | RANGAP1, CHADL | chr22 | 41217105 | 41217199 | Hypo | ST13, MIR4766, SLC25A17 |
| chr22 | 41839432 | 41839498 | Hypo | TOB2 | chr22 | 41637064 | 41637129 | Hypo | RANGAP1, CHADL |
| chr22 | 42343416 | 42343676 | Hypo | LINC00634, CENPM | chr22 | 42068010 | 42068172 | Hypo | NHP2L1, XRCC6 |
| chr22 | 42916449 | 42916479 | Hypo | RRP7A, SERHL | chr22 | 42667358 | 42667432 | Hypo | LOC388906 |
| chr22 | 43083130 | 43083166 | Hypo | A4GALT | chr22 | 43012543 | 43012877 | Hypo | CYB5R3, DL490307, RNU12, POLDIP3 |
| chr22 | 44455707 | 44455740 | Hypo | PARVB | chr22 | 43434441 | 43434477 | Hypo | BC039353, TTLL1 |
| chr22 | 45088602 | 45088743 | Hypo | PRR5, PRR5-ARHGAP8 | chr22 | 45087614 | 45087649 | Hypo | PRR5 |
| chr22 | 45277292 | 45277322 | Hypo | PHF21B | chr22 | 45135939 | 45135979 | Hypo | PRR5-ARHGAP8, PRR5 |
| chr22 | 45604184 | 45604343 | Hypo | MIR1249, KIAA0930 | chr22 | 45593643 | 45593715 | Hypo | MIR1249, KIAA0930, NUP50 |
| chr22 | 46455833 | 46455905 | Hypo | LOC150381, C22orf26, LOC554174, MIRLET7BHG | chr22 | 46438085 | 46438217 | Hypo | LINC00899, C22orf26 |
| chr22 | 47193335 | 47193371 | Hypo | TBC1D22A | chr22 | 47005080 | 47005154 | Hypo | |
| chr22 | 47584867 | 47585024 | Hypo | | chr22 | 47525846 | 47525885 | Hypo | |
| chr22 | 49852617 | 49852647 | Hypo | BC033837 | chr22 | 48931881 | 48932027 | Hypo | LOC284933, FAM19A5 |
| chr22 | 50001699 | 50001882 | Hypo | BC033837 | chr22 | 49979646 | 49979757 | Hypo | BC033837 |
| chr22 | 50003204 | 50003234 | Hypo | BC033837 | chr22 | 50002787 | 50002819 | Hypo | BC033837 |
| chr22 | 50010461 | 50010585 | Hypo | C22orf34, BC033837 | chr22 | 50010113 | 50010258 | Hypo | C22orf34, BC033837 |
| chr22 | 50149431 | 50149470 | Hypo | | chr22 | 50031691 | 50031721 | Hypo | BC033837, C22orf34 |
| chr22 | 50467876 | 50468105 | Hypo | | chr22 | 50467005 | 50467035 | Hypo | |
| chr22 | 50899293 | 50899672 | Hypo | SBF1 | chr22 | 50768840 | 50768876 | Hypo | DENND6B |
| chr13 | 20451144 | 20451360 | Hypo | | chr22 | 50939073 | 50939111 | Hypo | LMF2, NCAPH2 |
| chr13 | 25668799 | 25668925 | Hypo | PABPC3 | chr13 | 21713233 | 21713513 | Hypo | SAP18 |
| chr13 | 27699893 | 27699981 | Hypo | USP12 | chr13 | 26340608 | 26340755 | Hypo | ATP8A2 |
| chr13 | 30141688 | 30141718 | Hypo | SLC7A1 | chr13 | 28706016 | 28706140 | Hypo | PAN3-AS1, PAN3 |
| chr13 | 31742953 | 31743177 | Hypo | HSPH1 | chr13 | 30707569 | 30707599 | Hypo | |
| chr13 | 41346048 | 41346088 | Hypo | MRPS31 | chr13 | 37643942 | 37644005 | Hypo | |
| chr13 | 41884500 | 41884688 | Hypo | NAA16 | chr13 | 41496324 | 41496478 | Hypo | ELF1, SUGT1P3 |
| chr13 | 46660839 | 46660869 | Hypo | CPB2, CPB2-AS1 | chr13 | 45905088 | 45905264 | Hypo | TPT1, SNORA31, DL489966, D28408 |
| chr13 | 48667877 | 48667907 | Hypo | | chr13 | 47526030 | 47526182 | Hypo | |
| chr13 | 50367946 | 50368123 | Hypo | KPNA3 | chr13 | 50266473 | 50266573 | Hypo | KPNA3, EBPL |
| chr13 | 52565068 | 52565194 | Hypo | | chr13 | 52270145 | 52270175 | Hypo | WDFY2 |
| chr13 | 77553779 | 77553809 | Hypo | | chr13 | 52580318 | 52580369 | Hypo | UTP14C, ALG11 |
| chr13 | 96031705 | 96031815 | Hypo | | chr13 | 91948489 | 91948519 | Hypo | |
| chr13 | 102197373 | 102197408 | Hypo | ITGBL1 | chr13 | 99851676 | 99851706 | Hypo | 7SK, UBAC2-AS1 UBAC2 |
| chr13 | 108869613 | 108869830 | Hypo | ABHD13, LIG4 | chr13 | 108816328 | 108816383 | Hypo | |
| chr13 | 111278255 | 111278426 | Hypo | CARKD | chr13 | 110434451 | 110434593 | Hypo | IRS2 |
| chr13 | 112272991 | 112273088 | Hypo | | chr13 | 111363787 | 111363972 | Hypo | ING1, DJ031140, CARS2 |
| chr13 | 112758274 | 112758426 | Hypo | AK055145 | chr13 | 112712499 | 112712582 | Hypo | SOX1 |
| chr13 | 113938542 | 113938603 | Hypo | | chr13 | 113598618 | 113598851 | Hypo | BC035340 |
| chr13 | 114055983 | 114056013 | Hypo | | chr13 | 113985679 | 113986053 | Hypo | GRTP1, LAMP1 |
| chr13 | 114074768 | 114074853 | Hypo | ADPRHL1 | chr13 | 114060064 | 114060333 | Hypo | |
| chr13 | 114221622 | 114221652 | Hypo | | chr13 | 114123168 | 114123291 | Hypo | DCUN1D2 |
| chr13 | 114479404 | 114479434 | Hypo | TMEM255B | chr13 | 114304565 | 114304927 | Hypo | ATP4B, TFDP1 |
| chr13 | 114568046 | 114568076 | Hypo | LOC100506394 | chr13 | 114498017 | 114498260 | Hypo | TMEM255B |
| chr13 | 114780561 | 114781061 | Hypo | RASA3 | chr13 | 114748342 | 114748638 | Hypo | RASA3 |
| chr13 | 114855635 | 114855669 | Hypo | | chr13 | 114807617 | 114807647 | Hypo | RASA3 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr13 | 114961823 | 114961933 | Hypo | | chr13 | 114862308 | 114862368 | Hypo | |
| chr21 | 31015201 | 31015231 | Hypo | GRIK1 | chr21 | 19274828 | 19274858 | Hypo | CHODL |
| chr21 | 33627549 | 33627649 | Hypo | | chr21 | 31056850 | 31056927 | Hypo | GRIK1 |
| chr21 | 33983236 | 33983488 | Hypo | C21orf59 | chr21 | 33721756 | 33721824 | Hypo | URB1 |
| chr21 | 34469746 | 34469844 | Hypo | | chr21 | 34397024 | 34397091 | Hypo | OLIG2 |
| chr21 | 37527928 | 37527958 | Hypo | CBR3, DOPEY2, CBR3-AS1 | chr21 | 35051159 | 35051231 | Hypo | ITSN1 |
| chr21 | 37775034 | 37775096 | Hypo | CHAF1B | chr21 | 37758570 | 37758652 | Hypo | CHAF1B |
| chr21 | 38638422 | 38638526 | Hypo | DSCR3 | chr21 | 38092179 | 38092221 | Hypo | SIM2 |
| chr21 | 43376373 | 43376403 | Hypo | | chr21 | 38935478 | 38935549 | Hypo | |
| chr21 | 43991463 | 43991493 | Hypo | SLC37A1 | chr21 | 43786683 | 43786713 | Hypo | TFF1, TMPRSS3 |
| chr21 | 44837088 | 44837213 | Hypo | SIK1 | chr21 | 44250815 | 44250855 | Hypo | |
| chr21 | 45131875 | 45131905 | Hypo | PDXK | chr21 | 44866603 | 44866711 | Hypo | LINC00319 |
| chr21 | 45271643 | 45271688 | Hypo | | chr21 | 45195149 | 45195319 | Hypo | CSTB |
| chr21 | 45277332 | 45277513 | Hypo | AGPAT3 | chr21 | 45273717 | 45273913 | Hypo | |
| chr21 | 45847832 | 45847973 | Hypo | TRPM2 | chr21 | 45791079 | 45791109 | Hypo | TRPM2 |
| chr21 | 46193414 | 46193542 | Hypo | UBE2G2 | chr21 | 46036642 | 46036767 | Hypo | KRTAP10-8 |
| chr21 | 46310428 | 46310491 | Hypo | ITGB2 | chr21 | 46257116 | 46257273 | Hypo | |
| chr21 | 46319156 | 46319459 | Hypo | ITGB2 | chr21 | 46318286 | 46318343 | Hypo | ITGB2 |
| chr21 | 46452374 | 46452539 | Hypo | | chr21 | 46359187 | 46359248 | Hypo | FAM207A, C21orf67, ITGB2-AS1 |
| chr21 | 46863658 | 46863708 | Hypo | | chr21 | 46677734 | 46677796 | Hypo | POFUT2, C21orf89 |
| chr21 | 46926459 | 46926565 | Hypo | COL18A1, SLC19A1 | chr21 | 46925780 | 46925925 | Hypo | COL18A1, SLC19A1 |
| chr21 | 47504861 | 47504895 | Hypo | | chr21 | 47404174 | 47404325 | Hypo | COL6A1 |
| chr4 | 628572 | 629061 | Hypo | PDE6B | chr21 | 47746270 | 47746393 | Hypo | PCNT, BC031638, C21orf58 |
| chr4 | 678471 | 678501 | Hypo | MFSD7, MYL5 | chr4 | 651196 | 651261 | Hypo | PDE6B, BC020343 |
| chr4 | 955367 | 955454 | Hypo | DGKQ, TMEM175 | chr4 | 829611 | 829641 | Hypo | CPLX1 |
| chr4 | 1016127 | 1016252 | Hypo | FGFRL1 | chr4 | 955867 | 955919 | Hypo | DGKQ, TMEM175 |
| chr4 | 1025928 | 1026074 | Hypo | FGFRL1 | chr4 | 1016586 | 1016747 | Hypo | FGFRL1 |
| chr4 | 1189021 | 1189051 | Hypo | LOC100130872, AX747178 | chr4 | 1041763 | 1041926 | Hypo | AK124578 |
| chr4 | 1339099 | 1339221 | Hypo | UVSSA, MAEA | chr4 | 1338715 | 1338812 | Hypo | UVSSA, MAEA |
| chr4 | 1556419 | 1556609 | Hypo | | chr4 | 1512368 | 1512398 | Hypo | |
| chr4 | 1616682 | 1617247 | Hypo | | chr4 | 1576484 | 1576528 | Hypo | AX748388 |
| chr4 | 1993771 | 1994180 | Hypo | NELFA, MIR943 | chr4 | 1687080 | 1687110 | Hypo | SLBP, FAM53A |
| chr4 | 2305672 | 2305827 | Hypo | ZFYVE28 | chr4 | 2066114 | 2066265 | Hypo | POLN, NAT8L |
| chr4 | 2532556 | 2532586 | Hypo | | chr4 | 2527907 | 2527937 | Hypo | |
| chr4 | 2926366 | 2926396 | Hypo | MFSD10 | chr4 | 2540073 | 2540297 | Hypo | |
| chr4 | 3447816 | 3448015 | Hypo | HGFAC | chr4 | 2978968 | 2979145 | Hypo | GRK4 |
| chr4 | 5519950 | 5520092 | Hypo | C4orf6 | chr4 | 4417568 | 4417603 | Hypo | STX18, NSG1 |
| chr4 | 6719599 | 6719637 | Hypo | BLOC1S4, MRFAP1L1 | chr4 | 6670184 | 6670214 | Hypo | LOC93622 |
| chr4 | 6955114 | 6955144 | Hypo | AX747238, TBC1D14 | chr4 | 6748346 | 6748557 | Hypo | |
| chr4 | 7647770 | 7647945 | Hypo | | chr4 | 6957481 | 6957620 | Hypo | |
| chr4 | 8607813 | 8607932 | Hypo | CPZ | chr4 | 8429086 | 8429178 | Hypo | ACOX3 |
| chr4 | 9423273 | 9423354 | Hypo | | chr4 | 8608556 | 8608600 | Hypo | CPZ |
| chr4 | 17430691 | 17430832 | Hypo | | chr4 | 10782701 | 10782741 | Hypo | |
| chr4 | 40910303 | 40910465 | Hypo | TRNA_Gln, APBB2 | chr4 | 39816807 | 39817064 | Hypo | PDS5A |
| chr4 | 41993676 | 41993815 | Hypo | SLC30A9, DCAF4L1 | chr4 | 41938449 | 41938479 | Hypo | TMEM33 |
| chr4 | 46067800 | 46067954 | Hypo | GABRG1 | chr4 | 44266683 | 44266780 | Hypo | KCTD8 |
| chr4 | 47914784 | 47914992 | Hypo | NFXL1, BC041434 | chr4 | 47197142 | 47197270 | Hypo | GABRB1 |
| chr4 | 75241080 | 75241435 | Hypo | EREG | chr4 | 73459699 | 73459762 | Hypo | |
| chr4 | 76912698 | 76912733 | Hypo | CXCL9, SDAD1 | chr4 | 76554873 | 76554935 | Hypo | CDKL2 |
| chr4 | 79861530 | 79861560 | Hypo | PAQR3 | chr4 | 79611132 | 79611294 | Hypo | LOC100505702 |
| chr4 | 83343366 | 83343396 | Hypo | HNRPDL, ENOPH1 | chr4 | 81188328 | 81188489 | Hypo | FGF5 |
| chr4 | 83955171 | 83955201 | Hypo | COPS4 | chr4 | 83809740 | 83809787 | Hypo | THAP9-AS1, AK128593, SEC31A |
| chr4 | 90043517 | 90043547 | Hypo | TIGD2 | chr4 | 83988361 | 83988511 | Hypo | COPS4 |
| chr4 | 95127590 | 95127717 | Hypo | SMARCAD1 | chr4 | 91079842 | 91079899 | Hypo | CCSER1 |
| chr4 | 95762672 | 95762896 | Hypo | BMPR1B | chr4 | 95128038 | 95128068 | Hypo | SMARCAD1 |
| chr4 | 103929647 | 103929796 | Hypo | SLC9B1 | chr4 | 102332467 | 102332611 | Hypo | BANK1 |
| chr4 | 110344202 | 110344294 | Hypo | SEC24B-AS1, AK058136 | chr4 | 103930065 | 103930095 | Hypo | SLC9B1 |
| chr4 | 113154896 | 113155129 | Hypo | AP1AR | chr4 | 110735672 | 110735702 | Hypo | GAR1 |
| chr4 | 123664228 | 123664363 | Hypo | BBS12 | chr4 | 113559163 | 113559422 | Hypo | MIR302B, LARP7, C4orf21 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr4 | 130018134 | 130018266 | Hypo | SCLT1, C4orf33 | chr4 | 128984386 | 128984464 | Hypo | LARP1B |
| chr4 | 144586035 | 144586088 | Hypo | FREM3 | chr4 | 134073862 | 134073919 | Hypo | PCDH10, BC040219 |
|  | 154216241 | 154216357 | Hypo |  | chr4 | 153702668 | 153702702 | Hypo | ARFIP1 |
| chr4 | 170865234 | 170865287 | Hypo | LOC100506085 | chr4 | 158101782 | 158102020 | Hypo | GLRB |
| chr4 | 172132870 | 172133019 | Hypo |  | chr4 | 171012375 | 171012409 | Hypo | AADAT |
| chr4 | 184491996 | 184492042 | Hypo |  | chr4 | 184375546 | 184375726 | Hypo | CDKN2AIP |
| chr3 | 3167720 | 3167750 | Hypo | TRNT1 | chr4 | 184922036 | 184922091 | Hypo | STOX2 |
| chr3 | 9924238 | 9924534 | Hypo | JAGN1, CIDEC | chr3 | 5165885 | 5165915 | Hypo | ARL8B |
| chr3 | 10027432 | 10027548 | Hypo | AX747493, AK125558, EMC3 | chr3 | 9941469 | 9941669 | Hypo | IL17RE, JAGN1 |
| chr3 | 12586149 | 12586179 | Hypo | C3orf83 | chr3 | 10183021 | 10183212 | Hypo | VHL |
| chr3 | 13679172 | 13679349 | Hypo |  | chr3 | 12870826 | 12870856 | Hypo | RPL32, CAND2 |
| chr3 | 17001303 | 17001333 | Hypo |  | chr3 | 15123848 | 15123902 | Hypo | ZFYVE20 |
| chr3 | 32708277 | 32708405 | Hypo |  | chr3 | 17735273 | 17735340 | Hypo | TRNA_Pseudo |
| chr3 | 38032331 | 38032361 | Hypo | VILL | chr3 | 37276385 | 37276490 | Hypo | GOLGA4 |
| chr3 | 40202174 | 40202255 | Hypo | MYRIP | chr3 | 38208158 | 38208259 | Hypo | OXSR1 |
| chr3 | 42329346 | 42329511 | Hypo |  | chr3 | 42222730 | 42222847 | Hypo | TRAK1 |
| chr3 | 43735604 | 43735634 | Hypo | ABHD5 | chr3 | 42640855 | 42640964 | Hypo | NKTR, SS18L2 |
| chr3 | 47555760 | 47555790 | Hypo | ELP6 | chr3 | 47521062 | 47521178 | Hypo |  |
| chr3 | 47831601 | 47831819 | Hypo |  | chr3 | 47830060 | 47830148 | Hypo |  |
| chr3 | 48236476 | 48236724 | Hypo | MIR4443, CDC25A | chr3 | 48227765 | 48227870 | Hypo | CDC25A |
| chr3 | 49142883 | 49142913 | Hypo | USP19, QARS | chr3 | 48978413 | 48978479 | Hypo | ARIH2 |
| chr3 | 50072827 | 50072925 | Hypo | RBM6 | chr3 | 49939931 | 49940398 | Hypo | MON1A, MST1R |
| chr3 | 50575616 | 50575658 | Hypo |  | chr3 | 50395506 | 50395536 | Hypo | CYB561D2, NPRL2, Mir_324, CACNA2D2, TMEM115 |
| chr3 | 52352194 | 52352326 | Hypo | DNAH1 | chr3 | 50968445 | 50968511 | Hypo | DOCK3 |
| chr3 | 52553469 | 52553499 | Hypo | STAB1, NT5DC2 | chr3 | 52552556 | 52552661 | Hypo | STAB1, NT5DC2 |
| chr3 | 53253306 | 53253599 | Hypo | TKT | chr3 | 53032733 | 53033524 | Hypo |  |
| chr3 | 53480528 | 53480683 | Hypo |  | chr3 | 53382392 | 53382565 | Hypo | DCP1A |
| chr3 | 57437452 | 57437482 | Hypo |  | chr3 | 55603443 | 55603632 | Hypo | ERC2 |
| chr3 | 69740944 | 69740990 | Hypo |  | chr3 | 63719169 | 63719303 | Hypo |  |
| chr3 | 73045340 | 73045583 | Hypo | PPP4R2 | chr3 | 69937703 | 69937848 | Hypo | MITF |
| chr3 | 93698033 | 93698063 | Hypo | ARL13B | chr3 | 88247941 | 88248049 | Hypo |  |
| chr3 | 98618182 | 98618376 | Hypo | DCBLD2 | chr3 | 98313191 | 98313253 | Hypo | CPOX |
| chr3 | 101230678 | 101231070 | Hypo | FAM172BP, SENP7 | chr3 | 100228688 | 100228768 | Hypo | TMEM45A |
| chr3 | 101397240 | 101397358 | Hypo | ZBTB11, RPL24, ZBTB11-AS1 | chr3 | 101354294 | 101354442 | Hypo |  |
| chr3 | 101645019 | 101645181 | Hypo |  | chr3 | 101406823 | 101407190 | Hypo | RPL24, ZBTB11-AS1 |
| chr3 | 106936157 | 106936336 | Hypo | LINC00882 | chr3 | 105015466 | 105015519 | Hypo |  |
| chr3 | 113847911 | 113847941 | Hypo | DRD3 | chr3 | 113557333 | 113557363 | Hypo | GRAMD1C |
| chr3 | 121657197 | 121657515 | Hypo | SLC15A2 | chr3 | 115502232 | 115502390 | Hypo |  |
| chr3 | 122162036 | 122162117 | Hypo | KPNA1 | chr3 | 121741545 | 121741575 | Hypo | ILDR1 |
| chr3 | 122234242 | 122234538 | Hypo | KPNA1 | chr3 | 122162890 | 122163054 | Hypo | KPNA1 |
| chr3 | 122702288 | 122702451 | Hypo | SEMA5B | chr3 | 122573688 | 122573826 | Hypo | DIRC2 |
| chr3 | 127534814 | 127534897 | Hypo | MGLL | chr3 | 125417341 | 125417424 | Hypo | TRNA_Glu |
| chr3 | 128384991 | 128385132 | Hypo |  | chr3 | 128056383 | 128056497 | Hypo | EEFSEC |
| chr3 | 129047978 | 129048008 | Hypo | H1FX-AS1 | chr3 | 128599405 | 128599477 | Hypo | ACAD9, LOC653712 |
| chr3 | 130519901 | 130520077 | Hypo |  | chr3 | 130502167 | 130502197 | Hypo |  |
| chr3 | 133970381 | 133970474 | Hypo | RYK | chr3 | 133217784 | 133217999 | Hypo |  |
| chr3 | 137490806 | 137490860 | Hypo | BC038725, SOX14 | chr3 | 136582883 | 136582951 | Hypo | NCK1, SLC35G2 |
| chr3 | 137894374 | 137894415 | Hypo | DBR1 | chr3 | 137892691 | 137892721 | Hypo | DBR1 |
| chr3 | 138635369 | 138635507 | Hypo |  | chr3 | 138058859 | 138058897 | Hypo | MRAS |
| chr3 | 141174349 | 141174606 | Hypo | ZBTB38 | chr3 | 138662266 | 138662296 | Hypo | C3orf72, AK304483, AK128202, FOXL2 |
| chr3 | 141657032 | 141657079 | Hypo | TFDP2, AX748420 | chr3 | 141481651 | 141482073 | Hypo |  |
| chr3 | 142718283 | 142718358 | Hypo | LOC100289361, U2SURP | chr3 | 141835935 | 141836077 | Hypo | TFDP2 |
| chr3 | 143280343 | 143280373 | Hypo |  | chr3 | 142896156 | 142896214 | Hypo |  |
| chr3 | 146187946 | 146187978 | Hypo | PLSCR2 | chr3 | 143614462 | 143614504 | Hypo |  |
| chr3 | 148803120 | 148803276 | Hypo | HLTF, HLTF-AS1 | chr3 | 148523213 | 148523297 | Hypo |  |
| chr3 | 152707390 | 152707460 | Hypo |  | chr3 | 150237792 | 150237822 | Hypo |  |
| chr3 | 155461030 | 155461195 | Hypo |  | chr3 | 155456372 | 155456514 | Hypo |  |

TABLE 1-continued

| Chr | Start | Stop | Hypo/hyper | Annotation | Chr | Start | Stop | Hypo/hyper | Annotation |
|---|---|---|---|---|---|---|---|---|---|
| chr3 | 169541070 | 169541102 | Hypo | LRRIQ4 | chr3 | 169539898 | 169540679 | Hypo | LRRIQ4, LRRC34 |
| chr3 | 171193088 | 171193311 | Hypo | | chr3 | 170602030 | 170602133 | Hypo | EIF5A2 |
| chr3 | 172342101 | 172342147 | Hypo | NCEH1 | chr3 | 171529811 | 171529958 | Hypo | |
| chr3 | 172383550 | 172383600 | Hypo | NCEH1 | chr3 | 172355895 | 172356038 | Hypo | NCEH1 |
| chr3 | 172469925 | 172470036 | Hypo | ECT2 | chr3 | 172425382 | 172425717 | Hypo | U6, NCEH1 |
| chr3 | 17687235 | 176872443 | Hypo | TBL1XR1 | chr3 | 173162817 | 173162847 | Hypo | NLGN1 |
| chr3 | 179367874 | 179367920 | Hypo | USP13 | chr3 | 178861259 | 178861447 | Hypo | PIK3CA, BC032034 |
| chr3 | 182815811 | 182816027 | Hypo | MCCC1 | chr3 | 181444108 | 181444236 | Hypo | |
| chr3 | 183183523 | 183183659 | Hypo | LINC00888 | chr3 | 182895956 | 182896144 | Hypo | MCF2L2 |
| chr3 | 183647996 | 183648026 | Hypo | ABCC5 | chr3 | 183208370 | 183208469 | Hypo | KLHL6 |
| chr3 | 183872490 | 183872524 | Hypo | DVL3 | chr3 | 183870824 | 183870858 | Hypo | DVL3 |
| chr3 | 184018038 | 184018136 | Hypo | PSMD2, ECE2 | chr3 | 183965599 | 183965907 | Hypo | ECE2, ALG3, MIR1224, VWA5B2 |
| chr3 | 184057254 | 184057557 | Hypo | FAM131A, CLCN2 | chr3 | 184031686 | 184031746 | Hypo | EIF4G1, PSMD2 |
| chr3 | 185271296 | 185271764 | Hypo | LIPH | chr3 | 185001696 | 185001919 | Hypo | MAP3K13 |
| chr3 | 185303241 | 185303277 | Hypo | SENP2 | chr3 | 185275856 | 185275886 | Hypo | LIPH |
| chr3 | 185629516 | 185629546 | Hypo | TRA2B | chr3 | 185363074 | 185363261 | Hypo | IGF2BP2 |
| chr3 | 185658513 | 185658543 | Hypo | TRA2B | chr3 | 185643324 | 185643405 | Hypo | TRA2B |
| chr3 | 186287130 | 186287270 | Hypo | DNAJB11, TBCCD1 | chr3 | 185668237 | 185668311 | Hypo | LOC344887 |
| chr3 | 193548637 | 193548835 | Hypo | | chr3 | 193312128 | 193312347 | Hypo | OPA1 |
| chr3 | 194981816 | 194981913 | Hypo | | chr3 | 194048751 | 194048919 | Hypo | |
| chr3 | 195538211 | 195538353 | Hypo | MUC4 | chr3 | 195536733 | 195536848 | Hypo | MUC4 |
| chr3 | 195648794 | 195649004 | Hypo | | chr3 | 195587032 | 195587118 | Hypo | TNK2 |
| chr3 | 196069743 | 196070340 | Hypo | TM4SF19, TM4SF19-TCTEX1D2 | chr3 | 195834581 | 195834611 | Hypo | |
| chr3 | 196387295 | 196387415 | Hypo | LRRC33 | chr3 | 196263303 | 196263471 | Hypo | |
| chr3 | 196388383 | 196388581 | Hypo | LRRC33 | chr3 | 196387628 | 196387665 | Hypo | LRRC33 |
| chr3 | 196731155 | 196731313 | Hypo | MFI2-AS1, MFI2 | chr3 | 196667872 | 196668080 | Hypo | PIGZ, NCBP2, SENP5, NCBP2-AS2 |
| chr3 | 197326860 | 197327042 | Hypo | LOC220729 | chr3 | 197313997 | 197314107 | Hypo | LOC220729 |
| chr3 | 197466364 | 197466540 | Hypo | FYTTD1, KIAA0226 | chr3 | 197330060 | 197330147 | Hypo | LOC220729 |
| chr3 | 197685826 | 197686085 | Hypo | LMLN, RPL35A, IQCG | chr3 | 197616707 | 197616861 | Hypo | IQCG, LRCH3 |
| chr10 | 978878 | 978933 | Hypo | BC127786, LARP4B | chr10 | 833307 | 833386 | Hypo | |
| chr10 | 1708327 | 1708478 | Hypo | | chr10 | 1585111 | 1585239 | Hypo | ADARB2-AS1 |
| chr10 | 3330499 | 3330618 | Hypo | | chr10 | 3285585 | 3285698 | Hypo | |
| chr10 | 4599917 | 4599965 | Hypo | | chr10 | 3895410 | 3895452 | Hypo | |
| chr10 | 5875140 | 5875396 | Hypo | | chr10 | 5530764 | 5530975 | Hypo | CALML5 |
| chr10 | 6162159 | 6162225 | Hypo | RBM17 | chr10 | 6042309 | 6042571 | Hypo | |
| chr10 | 6586721 | 6586847 | Hypo | | chr10 | 6577643 | 6577673 | Hypo | AX748236 |
| chr10 | 6984463 | 6984639 | Hypo | | chr10 | 6963079 | 6963111 | Hypo | |
| chr10 | 7212745 | 7213064 | Hypo | SFMBT2 | chr10 | 7205733 | 7205787 | Hypo | SFMBT2 |
| chr10 | 7236211 | 7236245 | Hypo | SFMBT2 | chr10 | 7216059 | 7216089 | Hypo | SFMBT2 |
| chr10 | 7371678 | 7371708 | Hypo | SFMBT2 | chr10 | 7323283 | 7323313 | Hypo | SFMBT2 |
| chr10 | 7436090 | 7436209 | Hypo | SFMBT2 | chr10 | 7414544 | 7414588 | Hypo | SFMBT2 |
| chr10 | 12554417 | 12554501 | Hypo | CAMK1D | chr10 | 11700918 | 11701075 | Hypo | |
| chr10 | 14966129 | 14966212 | Hypo | DCLRE1C | chr10 | 13140861 | 13141020 | Hypo | OPTN, AK311458 |
| chr10 | 15140484 | 15140526 | Hypo | C10orf111, ACBD7, RPP38, NMT2 | chr10 | 15002784 | 15003006 | Hypo | MEIG1 |
| chr10 | 17503402 | 17503520 | Hypo | | chr10 | 17429165 | 17429622 | Hypo | ST8SIA6-AS1, ST8SIA6 |
| chr10 | 22567093 | 22567322 | Hypo | | chr10 | 21728064 | 21728124 | Hypo | |
| chr10 | 26747051 | 26747159 | Hypo | APBB1IP | chr10 | 24988589 | 24988619 | Hypo | ARHGAP21 |
| chr10 | 26816766 | 26816938 | Hypo | | chr10 | 26803853 | 26803883 | Hypo | |
| chr10 | 27846637 | 27846816 | Hypo | | chr10 | 27794496 | 27794588 | Hypo | RAB18 |
| chr10 | 31892922 | 31893079 | Hypo | | chr10 | 30848200 | 30848230 | Hypo | |
| chr10 | 32672459 | 32672489 | Hypo | EPC1 | chr10 | 32499044 | 32499176 | Hypo | |
| chr10 | 38078948 | 38079105 | Hypo | ZNF33BP1, ZNF248 | chr10 | 33233313 | 33233361 | Hypo | ITGB1 |
| chr10 | 43858343 | 43858470 | Hypo | FXYD4 | chr10 | 43186151 | 43186181 | Hypo | AK123067 |
| chr10 | 44434176 | 44434206 | Hypo | LINC00841 | chr10 | 43905877 | 43906023 | Hypo | |
| chr10 | 50340119 | 50340149 | Hypo | FAM170B-AS1, FAM170B | chr10 | 49652977 | 49653080 | Hypo | ARHGAP22, MAPK8 |
| chr10 | 50748131 | 50748350 | Hypo | | chr10 | 50507557 | 50507619 | Hypo | C10orf71 |
| chr10 | 69578459 | 69578588 | Hypo | DNAJC12 | chr10 | 53107427 | 53107563 | Hypo | |
| chr10 | 70167678 | 70167708 | Hypo | DNA2, RUFY2 | chr10 | 69589153 | 69589407 | Hypo | DNAJC12 |
| chr10 | 70314814 | 70315148 | Hypo | TET1 | chr10 | 70232345 | 70232485 | Hypo | SLC25A16, |
| chr10 | 70586494 | 70586540 | Hypo | STOX1 | chr10 | 70565410 | 70565489 | Hypo | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr10 | 75388129 | 75388173 | Hypo | MYOZ1 | chr10 | 75386789 | 75386893 | Hypo | MYOZ1 |
| chr10 | 81023884 | 81023914 | Hypo | ZMIZ1 | chr10 | 75488953 | 75489125 | Hypo | GLUD1P3, BMS1P4, AGAP5 |
| chr10 | 81966737 | 81966828 | Hypo | LINC00857, ANXA11 | chr10 | 81860447 | 81860568 | Hypo | TMEM254 |
| chr10 | 88698834 | 88698914 | Hypo | MMRN2 | chr10 | 88304914 | 88304944 | Hypo | |
| chr10 | 98129822 | 98130033 | Hypo | TLL2 | chr10 | 96304020 | 96304329 | Hypo | HELLS, TBC1D12 |
| chr10 | 99051122 | 99051253 | Hypo | ARHGAP19 | chr10 | 98528023 | 98528107 | Hypo | |
| chr10 | 101492942 | 101493074 | Hypo | CUTC, COX15 | chr10 | 99161398 | 99161560 | Hypo | |
| chr10 | 103325743 | 103325773 | Hypo | DPCD, BTRC | chr10 | 101988223 | 101988404 | Hypo | SNORA12, CHUK, CWF19L1 |
| chr10 | 103814668 | 103814754 | Hypo | C10orf76 | chr10 | 103579635 | 103579713 | Hypo | LOC100289509, MGEA5, KCNIP2 |
| chr10 | 105126957 | 105127076 | Hypo | TAF5 | chr10 | 103930034 | 103930161 | Hypo | NOLC1 |
| chr10 | 105413621 | 105413784 | Hypo | SH3PXD2A | chr10 | 105155285 | 105155481 | Hypo | USMG5, TAF5, PDCD11, MIR1307 |
| chr10 | 112440378 | 112440408 | Hypo | RBM20 | chr10 | 108469972 | 108470093 | Hypo | SORCS1 |
| chr10 | 116331126 | 116331156 | Hypo | | chr10 | 115925505 | 115925552 | Hypo | MIR2110, C10orf118 |
| chr10 | 120707028 | 120707111 | Hypo | | chr10 | 119807026 | 119807056 | Hypo | CASC2, RAB11FIP2 |
| chr10 | 121307542 | 121307572 | Hypo | | chr10 | 120841558 | 120841590 | Hypo | |
| chr10 | 126198949 | 126199217 | Hypo | LHPP | chr10 | 123688711 | 123688741 | Hypo | ATE1 |
| chr10 | 129888804 | 129888885 | Hypo | MKI67, PTPRE | chr10 | 126697789 | 126698107 | Hypo | CTBP2 |
| chr10 | 130577764 | 130577794 | Hypo | | chr10 | 130203435 | 130203480 | Hypo | |
| chr10 | 131936451 | 131936626 | Hypo | GLRX3 | chr10 | 131647903 | 131647933 | Hypo | MIR4297, EBF3 |
| chr10 | 132001252 | 132001556 | Hypo | | chr10 | 132000973 | 132001015 | Hypo | |
| chr10 | 133979059 | 133979089 | Hypo | JAKMIP3 | chr10 | 133951602 | 133952025 | Hypo | JAKMIP3 |
| chr10 | 134022845 | 134022875 | Hypo | STK32C, DPYSL4 | chr10 | 134016203 | 134016388 | Hypo | STK32C, DPYSL4 |
| chr10 | 134095594 | 134095833 | Hypo | STK32C | chr10 | 134092153 | 134092202 | Hypo | STK32C |
| chr10 | 134301095 | 134301212 | Hypo | | chr10 | 134273064 | 134273156 | Hypo | |
| chr10 | 134607970 | 134608183 | Hypo | NKX6-2 | chr10 | 134481320 | 134481433 | Hypo | INPP5A |
| chr10 | 134679129 | 134679265 | Hypo | TTC40 | chr10 | 134665147 | 134665202 | Hypo | TTC40 |
| chr10 | 134693587 | 134693709 | Hypo | TTC40 | chr10 | 134690559 | 134690617 | Hypo | TTC40 |
| chr10 | 134733221 | 134733275 | Hypo | TTC40 | chr10 | 134699872 | 134699909 | Hypo | TTC40 |
| chr10 | 134738378 | 134738642 | Hypo | TTC40 | chr10 | 134733497 | 134733617 | Hypo | TTC40 |
| chr10 | 134794271 | 134794342 | Hypo | LOC399829 | chr10 | 134788083 | 134788251 | Hypo | LOC399829 |
| chr10 | 134916714 | 134916774 | Hypo | GPR123 | chr10 | 134796012 | 134796042 | Hypo | LOC399829 |
| chr10 | 134942840 | 134943214 | Hypo | GPR123 | chr10 | 134941145 | 134941178 | Hypo | GPR123 |
| chr10 | 134944742 | 134944772 | Hypo | GPR123 | chr10 | 134943445 | 134943542 | Hypo | GPR123 |
| chr10 | 135002063 | 135002156 | Hypo | KNDC1 | chr10 | 134959217 | 134959391 | Hypo | CS330190 |
| chr10 | 135017049 | 135017129 | Hypo | KNDC1 | chr10 | 135014963 | 135015132 | Hypo | KNDC1 |
| chr10 | 135020801 | 135020893 | Hypo | KNDC1 | chr10 | 135018825 | 135018960 | Hypo | KNDC1 |
| chr10 | 135076368 | 135076503 | Hypo | ADAM8 | chr10 | 135023470 | 135023500 | Hypo | KNDC1 |
| chr15 | 26107640 | 26107860 | Hyper | | chr15 | 23158397 | 23158948 | Hyper | |
| chr15 | 27018363 | 27018436 | Hyper | | chr15 | 26108096 | 26108701 | Hyper | |
| chr15 | 27216396 | 27216429 | Hyper | GABRG3 | chr15 | 27212887 | 27213172 | Hyper | GABRG3 |
| chr15 | 28341951 | 28342429 | Hyper | OCA2 | chr15 | 27604062 | 27604139 | Hyper | GABRG3 |
| chr15 | 28352240 | 28352850 | Hyper | OCA2, HERC2 | chr15 | 28344173 | 28344287 | Hyper | OCA2 |
| chr15 | 29130807 | 29131875 | Hyper | APBA2 | chr15 | 29077284 | 29077383 | Hyper | LOC646278 |
| chr15 | 33009747 | 33009946 | Hyper | AX747968, GREM1 | chr15 | 31775596 | 31776121 | Hyper | OTUD7A |
| chr15 | 33010691 | 33011348 | Hyper | GREM1, AX747968 | chr15 | 33010300 | 33010330 | Hyper | GREM1, AX747968 |
| chr15 | 33602801 | 33602886 | Hyper | RYR3 | chr15 | 33011601 | 33011633 | Hyper | AX747968, GREM1 |
| chr15 | 34729478 | 34729582 | Hyper | | chr15 | 33603194 | 33603624 | Hyper | RYR3 |
| chr15 | 35046607 | 35046637 | Hyper | AK092087, GJD2 | chr15 | 34786504 | 34787304 | Hyper | |
| chr15 | 35087666 | 35087698 | Hyper | ACTC1, AK092087 | chr15 | 35047034 | 35047133 | Hyper | AK092087, GJD2 |
| chr15 | 37402974 | 37403238 | Hyper | MEIS2 | chr15 | 37180309 | 37180743 | Hyper | LOC145845, MEIS2 |
| chr15 | 40575679 | 40575718 | Hyper | PLCB2, ANKRD63, PAK6 | chr15 | 40211819 | 40212190 | Hyper | GPR176 |
| chr15 | 41804878 | 41805772 | Hyper | RPAP1, LTK, ITPKA | chr15 | 41787804 | 41787852 | Hyper | LTK, ITPKA |
| chr15 | 41952572 | 41952711 | Hyper | MGA | chr15 | 41913750 | 41913807 | Hyper | MGA |
| chr15 | 45421385 | 45421435 | Hyper | DUOX1, DUOXA1 | chr15 | 45403636 | 45404130 | Hyper | DUOXA2, DUOXA1, DUOX2 |
| chr15 | 45427611 | 45427786 | Hyper | DUOX1, DUOXA1 | chr15 | 45427354 | 45427410 | Hyper | DUOX1, DUOXA1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr15 | 48483956 | 48483986 | Hyper | CTXN2, SLC12A1 | chr15 | 45479460 | 45479697 | Hyper | SHF |
| chr15 | 48938212 | 48938510 | Hyper | FBN1 | chr15 | 48936726 | 48937932 | Hyper | FBN1 |
| chr15 | 51634075 | 51634135 | Hyper | GLDN | chr15 | 51385913 | 51386181 | Hyper | TNFAIP8L3 |
| chr15 | 53077655 | 53077731 | Hyper | ONECUT1 | chr15 | 53075809 | 53077761 | Hyper | ONECUT1 |
| chr15 | 53079340 | 53080082 | Hyper | ONECUT1 | chr15 | 53078064 | 53078236 | Hyper | ONECUT1 |
| chr15 | 53080935 | 53081025 | Hyper | ONECUT1 | chr15 | 53080337 | 53080606 | Hyper | ONECUT1 |
| chr15 | 53096816 | 53096891 | Hyper |  | chr15 | 53081306 | 53081677 | Hyper | ONECUT1 |
| chr15 | 53097777 | 53097974 | Hyper |  | chr15 | 53097231 | 53097261 | Hyper |  |
| chr15 | 54270498 | 54270639 | Hyper |  | chr15 | 53098316 | 53098658 | Hyper |  |
| chr15 | 58357733 | 58357835 | Hyper | ALDH1A2 | chr15 | 58357318 | 58357451 | Hyper | ALDH1A2 |
| chr15 | 60287038 | 60287733 | Hyper | FOXB1 | chr15 | 58358072 | 58358200 | Hyper | ALDH1A2 |
| chr15 | 60289310 | 60289536 | Hyper | FOXB1 | chr15 | 60288786 | 60288844 | Hyper | FOXB1 |
| chr15 | 60296598 | 60297409 | Hyper | FOXB1 | chr15 | 60296122 | 60296209 | Hyper | FOXB1 |
| chr15 | 68112611 | 68112641 | Hyper | SKOR1 | chr15 | 60297637 | 60298108 | Hyper | FOXB1 |
| chr15 | 68114139 | 68114195 | Hyper | SKOR1 | chr15 | 68113868 | 68113898 | Hyper | SKOR1 |
| chr15 | 68117830 | 68118633 | Hyper | SKOR1 | chr15 | 68116369 | 68116621 | Hyper | SKOR1 |
| chr15 | 68119548 | 68120576 | Hyper | SKOR1 | chr15 | 68118886 | 68119218 | Hyper | SKOR1 |
| chr15 | 68121058 | 68122076 | Hyper | SKOR1 | chr15 | 68120827 | 68120857 | Hyper | SKOR1 |
| chr15 | 68125261 | 68125664 | Hyper | SKOR1 | chr15 | 68122643 | 68122673 | Hyper | SKOR1 |
| chr15 | 73660004 | 73660067 | Hyper | HCN4 | chr15 | 68127801 | 68128350 | Hyper | SKOR1 |
| chr15 | 74422006 | 74422146 | Hyper | ISLR2, LOC283731 | chr15 | 73661607 | 73661666 | Hyper | HCN4 |
| chr15 | 74658370 | 74658587 | Hyper | LOC729739, BC013681, CYP11A1 | chr15 | 74422869 | 74423002 | Hyper | LOC283731, ISLR2 |
| chr15 | 75251672 | 75251786 | Hyper | RPP25 | chr15 | 75251346 | 75251382 | Hyper | RPP25 |
| chr15 | 76627508 | 76627826 | Hyper | ISL2 | chr15 | 75471116 | 75471193 | Hyper |  |
| chr15 | 76629814 | 76630847 | Hyper | SCAPER, ISL2 | chr15 | 76629056 | 76629220 | Hyper | ISL2 |
| chr15 | 76635120 | 76635197 | Hyper | SCAPER, ISL2 | chr15 | 76632257 | 76632423 | Hyper | SCAPER, ISL2 |
| chr15 | 76638472 | 76638719 | Hyper | SCAPER, ISL2 | chr15 | 76635530 | 76635560 | Hyper | ISL2, SCAPER |
| chr15 | 78632727 | 78632823 | Hyper | CRABP1 | chr15 | 78111154 | 78111210 | Hyper |  |
| chr15 | 78912623 | 78912653 | Hyper | CHRNB4, AX748237, CHRNA3 | chr15 | 78912281 | 78912401 | Hyper | CHRNB4, AX748237, CHRNA3 |
| chr15 | 78913535 | 78913651 | Hyper | CHRNB4, AX748237, CHRNA3 | chr15 | 78912912 | 78912942 | Hyper | CHRNB4, AX748237, CHRNA3 |
| chr15 | 79382786 | 79383257 | Hyper |  | chr15 | 79381705 | 79382571 | Hyper |  |
| chr15 | 79575278 | 79575474 | Hyper | ANKRD34C | chr15 | 79502211 | 79502360 | Hyper | MIR184, LOC729911 |
| chr15 | 79724126 | 79724240 | Hyper | KIAA1024 | chr15 | 79576145 | 79576277 | Hyper | ANKRD34C |
| chr15 | 79725422 | 79725539 | Hyper | KIAA1024 | chr15 | 79724552 | 79725125 | Hyper | KIAA1024 |
| chr15 | 82340070 | 82340157 | Hyper | MEX3B | chr15 | 82336879 | 82336972 | Hyper | MEX3B |
| chr15 | 83316251 | 83317087 | Hyper | LOC283692 | chr15 | 83315336 | 83315393 | Hyper | LOC283692 |
| chr15 | 83776322 | 83776417 | Hyper | TM6SF1 | chr15 | 83349234 | 83349686 | Hyper | AP3B2 |
| chr15 | 83875745 | 83875901 | Hyper | HDGFRP3 | chr15 | 83776647 | 83776785 | Hyper | TM6SF1 |
| chr15 | 83953102 | 83953489 | Hyper | BNC1 | chr15 | 83952198 | 83952323 | Hyper | BNC1 |
| chr15 | 84115747 | 84115966 | Hyper | SH3GL3 | chr15 | 83953749 | 83953903 | Hyper | BNC1 |
| chr15 | 84748578 | 84749260 | Hyper | EFTUD1P1 | chr15 | 84322851 | 84323037 | Hyper | ADAMTSL3 |
| chr15 | 88799537 | 88800317 | Hyper | NTRK3-AS1, NTRK3 | chr15 | 88798688 | 88798791 | Hyper | NTRK3-AS1, NTRK3 |
| chr15 | 89149169 | 89149448 | Hyper | MIR1179, MIR7-2, MIR3529, AK054749 | chr15 | 88800541 | 88801103 | Hyper | NTRK3-AS1, NTRK3 |
| chr15 | 89346050 | 89346393 | Hyper | ACAN | chr15 | 89248753 | 89248783 | Hyper |  |
| chr15 | 89903484 | 89903814 | Hyper | LINC00925, MIR9-3 | chr15 | 89346670 | 89346934 | Hyper | ACAN |
| chr15 | 89911087 | 89911186 | Hyper | MIR9-3, LINC00925 | chr15 | 89910521 | 89910748 | Hyper | MIR9-3, LINC00925 |
| chr15 | 89914231 | 89914895 | Hyper | LINC00925, MIR9-3 | chr15 | 89913750 | 89913780 | Hyper | MIR9-3, LINC00925 |
| chr15 | 89921956 | 89922006 | Hyper | LINC00925 | chr15 | 89915240 | 89915369 | Hyper | LINC00925, MIR9-3 |
| chr15 | 89942755 | 89942945 | Hyper | AK054710, LINC00925 | chr15 | 89922211 | 89922546 | Hyper | LINC00925 |
| chr15 | 89950236 | 89951113 | Hyper | AK054710, LINC00925 | chr15 | 89949410 | 89949942 | Hyper | AK054710, LINC00925 |
| chr15 | 89952153 | 89953055 | Hyper |  | chr15 | 89951400 | 89951801 | Hyper | AK054710, LINC00925 |
| chr15 | 89956364 | 89956450 | Hyper |  | chr15 | 89954197 | 89954335 | Hyper |  |
| chr15 | 92936290 | 92936322 | Hyper | ST8SIA2 | chr15 | 90039563 | 90039711 | Hyper | LINC00928, RHCG |
| chr15 | 92937927 | 92938006 | Hyper | ST8SIA2 | chr15 | 92937153 | 92937192 | Hyper | ST8SIA2 |
| chr15 | 93632660 | 93633233 | Hyper |  | chr15 | 93631975 | 93632014 | Hyper |  |
| chr15 | 96897934 | 96898010 | Hyper |  | chr15 | 95388568 | 95388616 | Hyper | LOC440311 |
| chr15 | 96952696 | 96953209 | Hyper |  | chr15 | 96911559 | 96911710 | Hyper |  |

TABLE 1-continued

| Chr | Start | Stop | Hypo/hyper | Annotation | Chr | Start | Stop | Hypo/hyper | Annotation |
|---|---|---|---|---|---|---|---|---|---|
| chr15 | 96960376 | 96960409 | Hyper | | chr15 | 96959730 | 96959976 | Hyper | |
| chr15 | 98836178 | 98836393 | Hyper | | chr15 | 96960732 | 96960826 | Hyper | |
| chr15 | 101420521 | 101420610 | Hyper | ALDH1A3 | chr15 | 100913423 | 100913880 | Hyper | |
| chr15 | 101513607 | 101513754 | Hyper | LRRK1 | chr15 | 101420945 | 101420989 | Hyper | ALDH1A3 |
| chr21 | 22370688 | 22370718 | Hyper | NCAM2 | chr15 | 102286533 | 102286563 | Hyper | DQ588362, DQ597539, DQ582294, DQ588439, DQ588452, DQ571896, DQ586138, DQ593864, DQ582460, DQ593630, BC101079, DQ588428, DQ578285, DQ575740, DQ596486, DQ578289, DQ586526, DQ588425, DQ593624, DQ582666, DQ595661, DQ585237, DQ593627, DQ597461, DQ576888, DQ593353, DQ597703 |
| chr21 | 27944995 | 27945081 | Hyper | CYYR1 | chr21 | 26934707 | 26934786 | Hyper | MIR155HG |
| chr21 | 28218958 | 28219045 | Hyper | ADAMTS1 | chr21 | 28216585 | 28217690 | Hyper | ADAMTS1 |
| chr21 | 28339399 | 28339429 | Hyper | | chr21 | 28338836 | 28338887 | Hyper | |
| chr21 | 31311404 | 31311553 | Hyper | | chr21 | 28340041 | 28340318 | Hyper | |
| chr21 | 31312351 | 31312445 | Hyper | | chr21 | 31311944 | 31312057 | Hyper | |
| chr21 | 34392436 | 34392566 | Hyper | OLIG2 | chr21 | 34392171 | 34392225 | Hyper | OLIG2 |
| chr21 | 34396795 | 34397037 | Hyper | OLIG2 | chr21 | 34395468 | 34396269 | Hyper | OLIG2 |
| chr21 | 34398430 | 34398634 | Hyper | OLIG2 | chr21 | 34398095 | 34398128 | Hyper | OLIG2 |
| chr21 | 34401185 | 34401392 | Hyper | OLIG2 | chr21 | 34398933 | 34400258 | Hyper | OLIG2 |
| chr21 | 34443103 | 34443262 | Hyper | OLIG1 | chr21 | 34442547 | 34442665 | Hyper | OLIG1 |
| chr21 | 34443893 | 34443956 | Hyper | OLIG1 | chr21 | 34443509 | 34443592 | Hyper | OLIG1 |
| chr21 | 36041468 | 36041697 | Hyper | CLIC6 | chr21 | 34444163 | 34444598 | Hyper | OLIG1 |
| chr21 | 36042658 | 36042861 | Hyper | CLIC6 | chr21 | 36041985 | 36042238 | Hyper | CLIC6 |
| chr21 | 38064966 | 38065737 | Hyper | SIM2 | chr21 | 38064457 | 38064683 | Hyper | SIM2 |
| chr21 | 38067203 | 38067233 | Hyper | SIM2 | chr21 | 38065955 | 38066112 | Hyper | SIM2 |
| chr21 | 38068565 | 38068783 | Hyper | SIM2 | chr21 | 38068178 | 38068289 | Hyper | SIM2 |
| chr21 | 38069459 | 38069496 | Hyper | SIM2 | chr21 | 38069093 | 38069203 | Hyper | SIM2 |
| chr21 | 38073007 | 38073070 | Hyper | SIM2 | chr21 | 38069825 | 38070013 | Hyper | SIM2 |
| chr21 | 38076929 | 38077152 | Hyper | SIM2 | chr21 | 38073300 | 38073860 | Hyper | SIM2 |
| chr21 | 38079988 | 38080684 | Hyper | SIM2 | chr21 | 38078415 | 38078487 | Hyper | SIM2 |
| chr21 | 38082042 | 38082072 | Hyper | SIM2 | chr21 | 38081445 | 38081835 | Hyper | SIM2 |
| chr21 | 38082930 | 38083196 | Hyper | SIM2 | chr21 | 38082315 | 38082345 | Hyper | SIM2 |
| chr21 | 44494923 | 44495155 | Hyper | CBS | chr21 | 38119904 | 38120312 | Hyper | HLCS |
| chr21 | 46125933 | 46126721 | Hyper | KRTAP10-12 | chr21 | 45148615 | 45148758 | Hyper | PDXK |
| chr21 | 46127542 | 46127692 | Hyper | KRTAP10-12 | chr21 | 46127039 | 46127094 | Hyper | KRTAP10-12 |
| chr21 | 46129444 | 46129485 | Hyper | | chr21 | 46128902 | 46128938 | Hyper | |
| chr21 | 47062544 | 47062825 | Hyper | PCBP3 | chr21 | 47010243 | 47010451 | Hyper | |
| chr21 | 47064250 | 47064377 | Hyper | PCBP3 | chr21 | 47063538 | 47063962 | Hyper | PCBP3 |
| AC211950.2_11234-25326 | 129 | 257 | Hyper | | chr21 | 47518776 | 47518814 | Hyper | COL6A2 |
| AC211950.2_11234-25326 | 13743 | 13889 | Hyper | | AC211950.2_11234-25326 | 13335 | 13445 | Hyper | |
| chr2 | 287580 | 287641 | Hyper | FAM150B | JH636052.4 | 5118769 | 5118903 | Hyper | |
| chr2 | 468045 | 468078 | Hyper | | chr2 | 288404 | 288470 | Hyper | FAM150B |
| chr2 | 945913 | 946000 | Hyper | SNTG2 | chr2 | 468299 | 468672 | Hyper | |
| chr2 | 946526 | 946610 | Hyper | SNTG2 | chr2 | 946208 | 946263 | Hyper | SNTG2 |
| chr2 | 1746614 | 1747210 | Hyper | PXDN | chr2 | 946896 | 947159 | Hyper | SNTG2 |
| chr2 | 3751335 | 3751439 | Hyper | ALLC | chr2 | 1747670 | 1748727 | Hyper | PXDN |
| chr2 | 5831789 | 5831819 | Hyper | SOX11 | chr2 | 5831178 | 5831324 | Hyper | SOX11 |
| chr2 | 5832890 | 5834028 | Hyper | SOX11 | chr2 | 5832069 | 5832222 | Hyper | SOX11 |
| chr2 | 5836548 | 5836976 | Hyper | SOX11 | chr2 | 5836085 | 5836253 | Hyper | SOX11 |
| chr2 | 5866098 | 5866211 | Hyper | | chr2 | 5837278 | 5837414 | Hyper | SOX11 |
| chr2 | 10182827 | 10182904 | Hyper | KLF11 | chr2 | 7571510 | 7571655 | Hyper | LOC100506274 |
| chr2 | 11052517 | 11052559 | Hyper | KCNF1 | chr2 | 10688874 | 10688904 | Hyper | |
| chr2 | 17719688 | 17719812 | Hyper | VSNL1 | chr2 | 11809957 | 11810117 | Hyper | LPIN1, NTSR2 |
| chr2 | 19550214 | 19550244 | Hyper | OSR1, MIR4757 | chr2 | 18059035 | 18059085 | Hyper | KCNS3 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr2 | 19556318 | 19556672 | Hyper | OSR1, MIR4757 | chr2 | 19551322 | 19551366 | Hyper | OSR1, MIR4757 |
| chr2 | 19558832 | 19558893 | Hyper | OSR1 | chr2 | 19557068 | 19557098 | Hyper | OSR1, MIR4757 |
| chr2 | 19561517 | 19561685 | Hyper | OSR1 | chr2 | 19561131 | 19561316 | Hyper | OSR1 |
| chr2 | 20068798 | 20068885 | Hyper | LINC00954 | chr2 | 19563358 | 19563433 | Hyper | OSR1 |
| chr2 | 25390994 | 25391212 | Hyper | POMC, EFR3B | chr2 | 20865753 | 20865927 | Hyper | GDF7 |
| chr2 | 25438821 | 25439465 | Hyper | | chr2 | 25391684 | 25391725 | Hyper | EFR3B, POMC |
| chr2 | 26407492 | 26407895 | Hyper | HADHA, GAREML | chr2 | 26402030 | 26402060 | Hyper | GAREML |
| chr2 | 26915763 | 26916259 | Hyper | KCNK3 | chr2 | 26521972 | 26522221 | Hyper | GPR113, HADHB |
| chr2 | 27072492 | 27072534 | Hyper | DPYSL5 | chr2 | 27070324 | 27070414 | Hyper | DPYSL5 |
| chr2 | 29033336 | 29033924 | Hyper | SPDYA, PPP1CB | chr2 | 27072822 | 27072989 | Hyper | DPYSL5 |
| chr2 | 29338750 | 29338969 | Hyper | CLIP4 | chr2 | 29338084 | 29338446 | Hyper | CLIP4 |
| chr2 | 30144041 | 30144084 | Hyper | | chr2 | 30143304 | 30143492 | Hyper | |
| chr2 | 30453714 | 30453941 | Hyper | LBH | chr2 | 30144378 | 30144411 | Hyper | |
| chr2 | 39187218 | 39187722 | Hyper | LOC375196, ARHGEF33 | chr2 | 38302253 | 38302876 | Hyper | CYP1B1 |
| chr2 | 39893972 | 39894059 | Hyper | TMEM178A | chr2 | 39893090 | 39893501 | Hyper | TMEM178A |
| chr2 | 42720262 | 42720546 | Hyper | MTA3, KCNG3 | chr2 | 40678673 | 40679620 | Hyper | SLC8A1 |
| chr2 | 45029682 | 45029712 | Hyper | | chr2 | 45028988 | 45029371 | Hyper | |
| chr2 | 45159956 | 45160267 | Hyper | SIX3 | chr2 | 45155125 | 45157711 | Hyper | |
| chr2 | 45161663 | 45162112 | Hyper | SIX3 | chr2 | 45160596 | 45160634 | Hyper | SIX3 |
| chr2 | 45162751 | 45162913 | Hyper | SIX3 | chr2 | 45162394 | 45162481 | Hyper | SIX3 |
| chr2 | 45165564 | 45165594 | Hyper | SIX3 | chr2 | 45164663 | 45164693 | Hyper | SIX3 |
| chr2 | 45169770 | 45170029 | Hyper | SIX3 | chr2 | 45168803 | 45168833 | Hyper | SIX3 |
| chr2 | 45176601 | 45176768 | Hyper | SIX3 | chr2 | 45171385 | 45171862 | Hyper | SIX3 |
| chr2 | 45179939 | 45180203 | Hyper | SIX3 | chr2 | 45179620 | 45179650 | Hyper | SIX3 |
| chr2 | 45181887 | 45182001 | Hyper | SIX3 | chr2 | 45181520 | 45181672 | Hyper | SIX3 |
| chr2 | 45231805 | 45232131 | Hyper | SIX2 | chr2 | 45231320 | 45231396 | Hyper | SIX2 |
| chr2 | 45235594 | 45235926 | Hyper | SIX2 | chr2 | 45233385 | 45233586 | Hyper | SIX2 |
| chr2 | 45240724 | 45240784 | Hyper | SIX2 | chr2 | 45237673 | 45237715 | Hyper | SIX2 |
| chr2 | 45395854 | 45395920 | Hyper | UNQ6975 | chr2 | 45241136 | 45241184 | Hyper | SIX2 |
| chr2 | 45396688 | 45396995 | Hyper | UNQ6975 | chr2 | 45396315 | 45396451 | Hyper | UNQ6975 |
| chr2 | 47797043 | 47797329 | Hyper | KCNK12 | chr2 | 47748494 | 47748494 | Hyper | KCNK12 |
| chr2 | 47798180 | 47798663 | Hyper | KCNK12 | chr2 | 47797564 | 47797818 | Hyper | KCNK12 |
| chr2 | 48982582 | 48982866 | Hyper | LHCGR | chr2 | 47798954 | 47799109 | Hyper | KCNK12 |
| chr2 | 50574121 | 50574313 | Hyper | NRXN1 | chr2 | 50573595 | 50573803 | Hyper | NRXN1 |
| chr2 | 56149836 | 56149866 | Hyper | EFEMP1 | chr2 | 50574743 | 50574859 | Hyper | NRXN1 |
| chr2 | 58656061 | 58656125 | Hyper | | chr2 | 56150729 | 56150759 | Hyper | EFEMP1 |
| chr2 | 60797137 | 60797281 | Hyper | | chr2 | 60796587 | 60796646 | Hyper | |
| chr2 | 63275563 | 63275855 | Hyper | OTX1, LOC100132215 | chr2 | 62798343 | 62798386 | Hyper | |
| chr2 | 63280952 | 63281651 | Hyper | OTX1, LOC100132215 | chr2 | 63278962 | 63278992 | Hyper | OTX1, LOC100132215 |
| chr2 | 63284777 | 63284811 | Hyper | OTX1, LOC100132215 | chr2 | 63282716 | 63282786 | Hyper | OTX1, LOC100132215 |
| chr2 | 66653238 | 66653496 | Hyper | MEIS1, MEIS1-AS3 | chr2 | 63285081 | 63287368 | Hyper | OTX1 |
| chr2 | 66808525 | 66809361 | Hyper | MEIS 1 | chr2 | 66653764 | 66653914 | Hyper | MEIS1, MEIS1-AS3 |
| chr2 | 68546738 | 68546892 | Hyper | CNRIP1 | chr2 | 68546324 | 68546532 | Hyper | CNRIP1 |
| chr2 | 71504103 | 71504148 | Hyper | ZNF638 | chr2 | 71503790 | 71503823 | Hyper | ZNF638 |
| chr2 | 72374375 | 72374432 | Hyper | CYP26B1 | chr2 | 71680833 | 71680863 | Hyper | DYSF |
| chr2 | 73145640 | 73145694 | Hyper | EMX1 | chr2 | 72374694 | 72374765 | Hyper | CYP26B1 |
| chr2 | 73148193 | 73148193 | Hyper | EMX1 | chr2 | 73145924 | 73146040 | Hyper | EMX1 |
| chr2 | 73151187 | 73151831 | Hyper | EMX1 | chr2 | 73150924 | 73150954 | Hyper | EMX1 |
| chr2 | 73429523 | 73429614 | Hyper | NOTO | chr2 | 73152683 | 73152754 | Hyper | EMX1 |
| chr2 | 73430322 | 73430743 | Hyper | NOTO | chr2 | 73429952 | 73430069 | Hyper | NOTO |
| chr2 | 73519579 | 73519841 | Hyper | U6, EGR4, AK125051 | chr2 | 73518448 | 73518919 | Hyper | EGR4, U6, AK125051 |
| chr2 | 74740852 | 74741387 | Hyper | TLX2, DQX1, PCGF1, LBX2-AS1 | chr2 | 74726744 | 74726774 | Hyper | LBX2-AS1, PCGF1, LBX2, TTC31 |
| | 74742176 | 74743732 | Hyper | DQX1, TLX2, PCGF1, LBX2-AS1 | chr2 | 74741835 | 74741955 | Hyper | PCGF1, LBX2-AS1, DQX1, TLX2 |
| chr2 | 75427040 | 75427114 | Hyper | | chr2 | 74782114 | 74782271 | Hyper | MIAP, LOXL3, DOK1 |
| chr2 | 80529378 | 80529443 | Hyper | CTNNA2, LRRTM1 | chr2 | 75427980 | 75428177 | Hyper | |
| chr2 | 80530505 | 80530558 | Hyper | CTNNA2, LRRTM1 | chr2 | 80529662 | 80530022 | Hyper | CTNNA2, LRRTM1 |
| chr2 | 80549585 | 80549745 | Hyper | CTNNA2 | chr2 | 80531725 | 80531755 | Hyper | LRRTM1, CTNNA2 |
| chr2 | 85361317 | 85361609 | Hyper | TCF7L1 | chr2 | 85107454 | 85107538 | Hyper | TRABD2A |
| chr2 | 87017796 | 87018195 | Hyper | CD8A, RMND5A | chr2 | 87016579 | 87016636 | Hyper | CD8A, RMND5A |

TABLE 1-continued

| Chr | Start | Stop | Hypo/hyper | Annotation | Chr | Start | Stop | Hypo/hyper | Annotation |
|---|---|---|---|---|---|---|---|---|---|
| chr2 | 88752080 | 88752137 | Hyper | FOXI3 | chr2 | 88751281 | 88751780 | Hyper | FOXI3 |
| chr2 | 89064610 | 89065278 | Hyper | ANKRD36BP2 | chr2 | 88752603 | 88752785 | Hyper | FOXI3 |
| chr2 | 95690747 | 95690793 | Hyper | MAL | chr2 | 95663969 | 95664014 | Hyper | |
| chr2 | 95691994 | 95692480 | Hyper | MAL | chr2 | 95691530 | 95691601 | Hyper | MAL |
| chr2 | 97193097 | 97193626 | Hyper | ARIDSA | chr2 | 96990898 | 96991316 | Hyper | ITPRIPL1 |
| chr2 | 98963329 | 98963599 | Hyper | CNGA3 | chr2 | 98962898 | 98962940 | Hyper | CNGA3 |
| chr2 | 98964596 | 98964645 | Hyper | CNGA3 | chr2 | 98963838 | 98964200 | Hyper | CNGA3 |
| chr2 | 100937947 | 100938056 | Hyper | LONRF2 | chr2 | 99439138 | 99439478 | Hyper | KIAA1211L |
| chr2 | 100939016 | 100939048 | Hyper | LONRF2 | chr2 | 100938314 | 100938626 | Hyper | LONRF2 |
| chr2 | 10545990 | 105460599 | Hyper | LOC100506421 | chr2 | 105459081 | 105459518 | Hyper | LOC100506421 |
| chr2 | 105461187 | 105461243 | Hyper | LOC100506421 | chr2 | 105460921 | 105460951 | Hyper | LOC100506421 |
| chr2 | 105462165 | 105462222 | Hyper | POU3F3, LOC100506421 | chr2 | 105461564 | 105461896 | Hyper | LOC100506421 |
| chr2 | 105469645 | 105470091 | Hyper | POU3F3, LOC100506421 | chr2 | 105468791 | 105468908 | Hyper | POU3F3, LOC100506421 |
| chr2 | 105472231 | 105472845 | Hyper | AK095498, POU3F3, LOC100506421 | chr2 | 105470350 | 105470840 | Hyper | POU3F3, LOC100506421 |
| chr2 | 105478762 | 105479089 | Hyper | AK095498, POU3F3 | chr2 | 105473248 | 105473553 | Hyper | AK095498, POU3F3, LOC100506421 |
| chr2 | 105483655 | 105483719 | Hyper | AK095498 | chr2 | 105480530 | 105480595 | Hyper | POU3F3, AK095498 |
| chr2 | 105760981 | 105761037 | Hyper | | chr2 | 105484450 | 105484522 | Hyper | AK095498 |
| chr2 | 106682012 | 106682098 | Hyper | C2orf40 | chr2 | 106681733 | 106681767 | Hyper | C2orf40 |
| chr2 | 107502670 | 107502754 | Hyper | ST6GAL2 | chr2 | 107103865 | 107103928 | Hyper | |
| chr2 | 10750388 | 107504018 | Hyper | ST6GAL2 | chr2 | 107503277 | 107503328 | Hyper | ST6GAL2 |
| chr2 | 109746289 | 109746477 | Hyper | SH3RF3, SH3RF3-AS1 | chr2 | 109745989 | 109746079 | Hyper | SH3RF3, SH3RF3-AS1 |
| chr2 | 111876698 | 111876870 | Hyper | BCL2L11, AK125994 | chr2 | 111875434 | 111875611 | Hyper | BCL2L11, AK125994 |
| chr2 | 114034892 | 114035180 | Hyper | PAX8 | chr2 | 112657033 | 112657092 | Hyper | MERTK |
| chr2 | 114261300 | 114261458 | Hyper | CBWD2, FOXD4L1 | chr2 | 114256978 | 114257137 | Hyper | FOXD4L1, CBWD2 |
| chr2 | 115919103 | 115919594 | Hyper | DPP10, LOC389023 | chr2 | 115918661 | 115918884 | Hyper | DPP10, LOC389023 |
| chr2 | 118981151 | 118982497 | Hyper | | chr2 | 115919934 | 115920534 | Hyper | LOC389023, DPP10 |
| chr2 | 119532161 | 119532255 | Hyper | | chr2 | 119067732 | 119068049 | Hyper | |
| chr2 | 119591351 | 119591465 | Hyper | EN1 | chr2 | 119566239 | 119566272 | Hyper | |
| chr2 | 119592997 | 119593198 | Hyper | EN1 | chr2 | 119592738 | 119592777 | Hyper | EN1 |
| chr2 | 119599926 | 119599967 | Hyper | EN1 | chr2 | 119593535 | 119593567 | Hyper | EN1 |
| chr2 | 119600949 | 119601061 | Hyper | EN1 | chr2 | 119600332 | 119600555 | Hyper | EN1 |
| chr2 | 119604032 | 119604158 | Hyper | EN1 | chr2 | 119602601 | 119603086 | Hyper | EN1 |
| chr2 | 119606135 | 119606558 | Hyper | EN1 | chr2 | 119604809 | 119604851 | Hyper | EN1 |
| chr2 | 119607176 | 119607411 | Hyper | EN1 | chr2 | 119606783 | 119606839 | Hyper | EN1 |
| chr2 | 119610844 | 119610969 | Hyper | EN1 | chr2 | 119607783 | 119607842 | Hyper | EN1 |
| chr2 | 119612324 | 119612354 | Hyper | EN1 | chr2 | 119611745 | 119611799 | Hyper | EN1 |
| chr2 | 119614780 | 119614852 | Hyper | EN1 | chr2 | 119614130 | 119614171 | Hyper | EN1 |
| chr2 | 119616155 | 119616582 | Hyper | | chr2 | 119615055 | 119615627 | Hyper | EN1 |
| chr2 | 119914720 | 119914752 | Hyper | C1QL2 | chr2 | 119616809 | 119616870 | Hyper | |
| chr2 | 119916299 | 119916526 | Hyper | C1QL2 | chr2 | 119916049 | 119916082 | Hyper | C1QL2 |
| chr2 | 120281923 | 120281953 | Hyper | SCTR | chr2 | 120281646 | 120281693 | Hyper | SCTR |
| chr2 | 121345081 | 121345111 | Hyper | | chr2 | 121200390 | 121200433 | Hyper | |
| chr2 | 124782692 | 124783097 | Hyper | CNTNAP5 | chr2 | 124782333 | 124782458 | Hyper | CNTNAP5 |
| chr2 | 127783043 | 127783257 | Hyper | | chr2 | 127413918 | 127414036 | Hyper | GYPC |
| chr2 | 128421866 | 128421947 | Hyper | | chr2 | 127976467 | 127976672 | Hyper | CYP27C1 |
| chr2 | 130971283 | 130971321 | Hyper | | chr2 | 130763584 | 130763623 | Hyper | |
| chr2 | 131721461 | 131721949 | Hyper | ARHGEF4 | chr2 | 131720852 | 131721253 | Hyper | ARHGEF4 |
| chr2 | 132088770 | 132088828 | Hyper | | chr2 | 131792260 | 131793131 | Hyper | ARHGEF4 |
| chr2 | 132182790 | 132183089 | Hyper | | chr2 | 132152361 | 132152495 | Hyper | LOC389043, TRNA_Pseudo |
| chr2 | 132795240 | 132795419 | Hyper | | chr2 | 132767457 | 132767707 | Hyper | |
| chr2 | 133014598 | 133014638 | Hyper | JA668105, MIR663B, ANKRD30BL | chr2 | 132795670 | 132795728 | Hyper | |
| chr2 | 133062326 | 133062389 | Hyper | AK094599 | chr2 | 133015275 | 133015323 | Hyper | JA668105, MIR663B, ANKRD30BL |
| chr2 | 133426637 | 133426674 | Hyper | NCKAP5, LYPD1 | chr2 | 133426249 | 133426279 | Hyper | NCKAP5, LYPD1 |
| chr2 | 137523825 | 137523855 | Hyper | THSD7B | chr2 | 137522445 | 137522475 | Hyper | THSD7B |
| chr2 | 139537443 | 139537865 | Hyper | NXPH2 | chr2 | 139536937 | 139537145 | Hyper | NXPH2 |
| chr2 | 144694367 | 144695047 | Hyper | GTDC1 | chr2 | 142888348 | 142888418 | Hyper | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr2 | 145274285 | 145274315 | Hyper | ZEB2_AS1_1, ZEB2-AS1, ZEB2_AS1_3, ZEB2_AS1_4, AK124806, ZEB2 | chr2 | 145273404 | 145273751 | Hyper | ZEB2_AS1_1, ZEB2-AS1, ZEB2_AS1_3, ZEB2_AS1_4, AK124806, ZEB2 |
| chr2 | 149633232 | 149633399 | Hyper | JB137817, KIF5C | chr2 | 145274814 | 145275091 | Hyper | ZEB2_AS1_1, ZEB2-AS1, ZEB_AS1_3, ZEB2_AS1_4, AK124806, ZEB2 |
| chr2 | 149645496 | 149645894 | Hyper | JB137817, KIF5C | chr2 | 149633744 | 149633965 | Hyper | JB137817, KIF5C |
| chr2 | 154334272 | 154334665 | Hyper | RPRM | chr2 | 154333535 | 154333567 | Hyper | RPRM |
| chr2 | 154728042 | 154728092 | Hyper | GALNT13 | chr2 | 154335139 | 154335271 | Hyper | RPRM |
| chr2 | 154729559 | 154729589 | Hyper | GALNT13 | chr2 | 154729210 | 154729240 | Hyper | GALNT13 |
| chr2 | 157177003 | 157178310 | Hyper | NR4A2 | chr2 | 157176592 | 157177170 | Hyper | NR4A2 |
| chr2 | 162273495 | 162274338 | Hyper | TBR1 | chr2 | 162273136 | 162273245 | Hyper | TBR1 |
| chr2 | 162275146 | 162275802 | Hyper | TBR1 | chr2 | 162274717 | 162274866 | Hyper | TBR1 |
| chr2 | 162283365 | 162284055 | Hyper | TBR1 | chr2 | 162280003 | 162280956 | Hyper | TBR1 |
| chr2 | 168150069 | 168150245 | Hyper | | chr2 | 164593096 | 164593137 | Hyper | FIGN |
| chr2 | 171570082 | 171570428 | Hyper | SP5, AK023515, LOC440925 | chr2 | 168150751 | 168150945 | Hyper | |
| chr2 | 171670349 | 171670467 | Hyper | GAD1 | chr2 | 171570684 | 171570733 | Hyper | LOC440925, SP5, AK023515 |
| chr2 | 171674739 | 171675066 | Hyper | GAD1 | chr2 | 171671487 | 171671881 | Hyper | GAD1 |
| chr2 | 171676684 | 171676785 | Hyper | GAD1 | chr2 | 171675361 | 171675592 | Hyper | GAD1 |
| chr2 | 172945896 | 172946211 | Hyper | DLX1, METAP1D | chr2 | 172945124 | 172945167 | Hyper | DLX1, METAP1D |
| chr2 | 172948709 | 172948751 | Hyper | DLX1, METAP1D | chr2 | 172947717 | 172948314 | Hyper | METAP1D, DLX1 |
| chr2 | 172951596 | 172951689 | Hyper | DLX1, METAP1D | chr2 | 172949186 | 172949711 | Hyper | DLX1, METAP1D |
| chr2 | 172955441 | 172955545 | Hyper | DLX1, METAP1D, DLX2 | chr2 | 172952521 | 172953046 | Hyper | DLX1, METAP1D |
| chr2 | 172961398 | 172961598 | Hyper | DLX2, DLX1 | chr2 | 172957907 | 172958066 | Hyper | DLX2, DLX1 |
| chr2 | 172966264 | 172966442 | Hyper | DLX2 | chr2 | 172964821 | 172965802 | Hyper | DLX2 |
| chr2 | 173099784 | 173099814 | Hyper | | chr2 | 172972735 | 172973218 | Hyper | DLX2 |
| chr2 | 175190871 | 175192468 | Hyper | SP9, LOC285084 | chr2 | 173100262 | 173100430 | Hyper | |
| chr2 | 175195831 | 175195861 | Hyper | SP9, LOC285084 | chr2 | 175193268 | 175193823 | Hyper | SP9, LOC285084 |
| chr2 | 175197089 | 175197119 | Hyper | SP9, LOC285084 | chr2 | 175196432 | 175196575 | Hyper | SP9, LOC285084 |
| chr2 | 175199527 | 175199935 | Hyper | SP9, LOC285084 | chr2 | 175198752 | 175198900 | Hyper | SP9, LOC285084 |
| chr2 | 175204174 | 175204204 | Hyper | CIR1, SP9, LOC285084 | chr2 | 175200140 | 175202652 | Hyper | SP9, LOC285084 |
| chr2 | 175206833 | 175207028 | Hyper | CIR1, SP9 | chr2 | 175204786 | 175205799 | Hyper | CIR1, SP9, LOC285084 |
| chr2 | 175207536 | 175207653 | Hyper | SP9, CIR1 | chr2 | 175207228 | 175207258 | Hyper | CIR1, SP9 |
| chr2 | 176940167 | 176940315 | Hyper | EVX2 | chr2 | 175208311 | 175209135 | Hyper | CIR1, SP9 |
| chr2 | 176943861 | 176943902 | Hyper | EVX2 | chr2 | 176943269 | 176943568 | Hyper | EVX2 |
| chr2 | 176946578 | 176947389 | Hyper | EVX2 | chr2 | 176944426 | 176945784 | Hyper | EVX2 |
| chr2 | 176948599 | 176948629 | Hyper | HOXD13, EVX2 | chr2 | 176947748 | 176947903 | Hyper | HOXD13, EVX2 |
| chr2 | 176949695 | 176949869 | Hyper | HOXD13, EVX2 | chr2 | 176949045 | 176949075 | Hyper | HOXD13, EVX2 |
| chr2 | 176956610 | 176956640 | Hyper | HOXD13, HOXD12, EVX2 | chr2 | 176950142 | 176950258 | Hyper | HOXD13, EVX2 |
| chr2 | 176957497 | 176957919 | Hyper | HOXD13, HOXD12, EVX2 | chr2 | 176956921 | 176957199 | Hyper | HOXD12, EVX2, HOXD13 |
| chr2 | 176959289 | 176959511 | Hyper | HOXD12, HOXD11, HOXD13 | chr2 | 176958138 | 176958489 | Hyper | HOXD13, EVX2, HOXD12 |
| chr2 | 176964085 | 176964115 | Hyper | HOXD12, HOXD11, HOXD13 | chr2 | 176963448 | 176963522 | Hyper | HOXD11, HOXD13, HOXD12 |
| chr2 | 176969463 | 176969908 | Hyper | HOXD11, HOXD12, HOXD13 | chr2 | 176964369 | 176965492 | Hyper | HOXD13, HOXD12, HOXD11 |
| chr2 | 176980750 | 176981506 | Hyper | HOXD 10, HOXD9, HOXD11 | chr2 | 176976029 | 176976116 | Hyper | HOXD10, HOXD11 |
| chr2 | 176986715 | 176986848 | Hyper | HOXD9, AX747372, HOXD8, HOXD10 | chr2 | 176982584 | 176982627 | Hyper | HOXD9, AX747372, HOXD10, HOXD11 |
| chr2 | 176993547 | 176993791 | Hyper | HOXD8, HOXD-AS2, BC047605, AX747372, HOXD9, HOXD10 | chr2 | 176987057 | 176988304 | Hyper | HOXD9, AX747372, HOXD8, HOXD10 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr2 | 176995072 | 176995668 | Hyper | HOXD-AS2, BC047605, HOXD8, AX747372, HOXD9 | chr2 | 176994124 | 176994600 | Hyper | BC047605, AX747372, HOXD9, HOXD10, HOXD8, HOXD-AS2 |
| chr2 | 177004566 | 177004658 | Hyper | BC047605, HOXD-AS2, HOXD8 | chr2 | 177001102 | 177001897 | Hyper | BC047605, HOXD-AS2, HOXD8, AX747372 |
| chr2 | 177043427 | 177043515 | Hyper | HOXD1, HOXD-AS1, HOXD3 | chr2 | 177042984 | 177043226 | Hyper | HOXD-AS1, HOXD3 |
| chr2 | 177054113 | 177054351 | Hyper | HOXD1, HOXD-AS1 | chr2 | 177053276 | 177053816 | Hyper | HOXD1, HOXD-AS1 |
| chr2 | 182321839 | 182322170 | Hyper | ITGA4 | chr2 | 182321397 | 182321637 | Hyper | ITGA4 |
| chr2 | 182542903 | 182542933 | Hyper | NEUROD1 | chr2 | 182322379 | 182323042 | Hyper | ITGA4 |
| chr2 | 182543764 | 182543925 | Hyper | NEUROD1 | chr2 | 182543321 | 182543418 | Hyper | NEUROD1 |
| chr2 | 182545539 | 182545694 | Hyper | NEUROD1 | chr2 | 182545211 | 182545275 | Hyper | NEUROD1 |
| chr2 | 182546435 | 182546465 | Hyper | NEUROD1 | chr2 | 182545986 | 182546085 | Hyper | NEUROD1 |
| chr2 | 182547937 | 182548161 | Hyper | NEUROD1 | chr2 | 182547385 | 182547613 | Hyper | NEUROD1 |
| chr2 | 182549337 | 182549454 | Hyper | NEUROD1 | chr2 | 182549088 | 182549134 | Hyper | NEUROD1 |
| chr2 | 182819048 | 182819216 | Hyper |  | chr2 | 182550094 | 182550124 | Hyper | NEUROD1 |
| chr2 | 183731868 | 183731898 | Hyper | FRZB | chr2 | 183731294 | 183731524 | Hyper | FRZB |
| chr2 | 185463193 | 185463817 | Hyper | ZNF804A | chr2 | 185462869 | 185462980 | Hyper | ZNF804A |
| chr2 | 188419047 | 188419204 | Hyper | TFPI | chr2 | 186603488 | 186603518 | Hyper | FSIP2, BC039382 |
| chr2 | 193059025 | 193060067 | Hyper | TMEFF2 | chr2 | 189157658 | 189157688 | Hyper | MIR561, GULP1 |
| chr2 | 193060683 | 193060825 | Hyper | TMEFF2 | chr2 | 193060385 | 193060441 | Hyper | TMEFF2 |
| chr2 | 200327287 | 200327565 | Hyper | SATB2-AS1, AK056625, AK125157 | chr2 | 193061388 | 193061480 | Hyper | TMEFF2 |
| chr2 | 200333775 | 200333834 | Hyper | AK125157, AK056625, SATB2-AS1 | chr2 | 200328747 | 200329668 | Hyper | SATB2-AS1, AK056625, AK125157 |
| chr2 | 201450556 | 201450707 | Hyper | SGOL2, AOX1 | chr2 | 200334976 | 200335952 | Hyper | AK056625, SATB2-AS1 |
| chr2 | 207139072 | 207139102 | Hyper | ZDBF2, BC028329 | chr2 | 206551056 | 206551311 | Hyper | NRP2 |
| chr2 | 207307528 | 207307562 | Hyper | ADAM23 | chr2 | 207139475 | 207139605 | Hyper | ZDBF2, BC028329 |
| chr2 | 207506691 | 207507181 | Hyper | LOC200726, DYTN | chr2 | 207308802 | 207308857 | Hyper | ADAM23 |
| chr2 | 209271322 | 209271551 | Hyper | PTH2R | chr2 | 208635643 | 208635774 | Hyper | FZD5 |
| chr2 | 213401235 | 213401339 | Hyper |  | chr2 | 210636466 | 210636892 | Hyper | UNC80 |
| chr2 | 213403110 | 213403337 | Hyper |  | chr2 | 213401613 | 213401947 | Hyper |  |
| chr2 | 217559966 | 217559999 | Hyper | IGFBP5 | chr2 | 217559296 | 217559326 | Hyper | IGFBP5 |
| chr2 | 219736151 | 219736691 | Hyper | WNT10A, WNT6 | chr2 | 218806147 | 218806302 | Hyper | TNS1 |
| chr2 | 219847462 | 219847555 | Hyper | CRYBA2, FEV, LINC00608 | chr2 | 219828049 | 219828117 | Hyper | CDK5R2 |
| chr2 | 219857723 | 219857756 | Hyper | CRYBA2, FEV, MIR375, LOC100129175, CCDC108 | chr2 | 219848809 | 219849001 | Hyper | CRYBA2, FEV, LINC00608 |
| chr2 | 220174235 | 220174296 | Hyper |  | chr2 | 220173989 | 220174029 | Hyper |  |
| chr2 | 220223098 | 220223128 | Hyper |  | chr2 | 220196354 | 220196567 | Hyper | RESP18 |
| chr2 | 220283338 | 220283519 | Hyper | DES | chr2 | 220223648 | 220223703 | Hyper |  |
| chr2 | 220313621 | 220313692 | Hyper | SPEG | chr2 | 220299588 | 220300059 | Hyper | DES, SPEG |
| chr2 | 220361447 | 220361531 | Hyper | GMPPA | chr2 | 220349029 | 220349706 | Hyper |  |
| chr2 | 220416848 | 220417649 | Hyper | CHPF, OBSL1, MIR3132, TMEM198 | chr2 | 220416379 | 220416513 | Hyper | OBSL1, MIR3132, TMEM198, CHPF |
| chr2 | 223155722 | 223156188 | Hyper | PAX3, CCDC140, DD413687 | chr2 | 222435773 | 222435863 | Hyper | AX747413, EPHA4 |
| chr2 | 223159959 | 223160065 | Hyper | DD413687, PAX3, CCDC140 | chr2 | 223158730 | 223159453 | Hyper | CCDC140, DD413687, PAX3 |
| chr2 | 223161247 | 223162026 | Hyper | CCDC140, DD413687, PAX3 | chr2 | 223160342 | 223160379 | Hyper | CCDC140, DD413687, PAX3 |
| chr2 | 223163768 | 223163954 | Hyper | CCDC140, DD413687, PAX3 | chr2 | 223162779 | 223163535 | Hyper | CCDC140, DD413687, PAX3 |
| chr2 | 223165434 | 223165832 | Hyper | CCDC140, DD413687, PAX3 | chr2 | 223164534 | 223164883 | Hyper | DD413687, PAX3, CCDC140 |
| chr2 | 223167380 | 223167573 | Hyper | PAX3, CCDC140, DD413687 | chr2 | 223166449 | 223166721 | Hyper | CCDC140, DD413687, PAX3 |
| chr2 | 223169640 | 223169733 | Hyper | CCDC140, DD413687, PAX3 | chr2 | 223168437 | 223168852 | Hyper | DD413687, PAX3, CCDC140 |
| chr2 | 223171109 | 223171180 | Hyper | PAX3, CCDC140, DD413687 | chr2 | 223170375 | 223170434 | Hyper | CCDC140, DD413687, PAX3 |
| chr2 | 223175663 | 223176126 | Hyper | LOC440934, CCDC140 | chr2 | 223172924 | 223173173 | Hyper | CCDC140, DD413687, PAX3 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr2 | 223177315 | 223177610 | Hyper | LOC440934, CCDC140 | chr2 | 223176456 | 223176983 | Hyper | LOC440934, CCDC140 |
| chr2 | 229046107 | 229046503 | Hyper | SPHKAP | chr2 | 228736215 | 228736272 | Hyper | DAW1 |
| chr2 | 232791704 | 232792012 | Hyper | NPPC | chr2 | 231693216 | 231693268 | Hyper | CAB39 |
| chr2 | 233352025 | 233352853 | Hyper | ECEL1 | chr2 | 233350208 | 233351394 | Hyper | ECEL1 |
| chr2 | 235404545 | 235404575 | Hyper | ARL4C | chr2 | 233498710 | 233499239 | Hyper | EFHD1 |
| chr2 | 237073354 | 237073414 | Hyper | GBX2 | chr2 | 237072413 | 237073030 | Hyper | GBX2 |
| chr2 | 237077846 | 237078348 | Hyper | GBX2 | chr2 | 237077562 | 237077608 | Hyper | GBX2 |
| chr2 | 237081341 | 237081826 | Hyper | GBX2 | chr2 | 237080264 | 237080294 | Hyper | GBX2 |
| chr2 | 237086349 | 237086468 | Hyper | GBX2 | chr2 | 237082117 | 237082720 | Hyper | GBX2 |
| chr2 | 237416216 | 237416429 | Hyper | IQCA1 | chr2 | 237145557 | 237145601 | Hyper | ASB18 |
| chr2 | 238864644 | 238864913 | Hyper |  | chr2 | 238395291 | 238395356 | Hyper | MLPH |
| chr2 | 239755164 | 239755194 | Hyper | TWIST2 | chr2 | 239140025 | 239140249 | Hyper | HES6, LOC151174, LOC643387 |
| chr2 | 239756373 | 239756648 | Hyper | TWIST2 | chr2 | 239755736 | 239755778 | Hyper | TWIST2 |
| chr2 | 239758078 | 239758144 | Hyper | TWIST2 | chr2 | 239757636 | 239757824 | Hyper | TWIST2 |
| chr2 | 241393200 | 241393469 | Hyper | MIR149, PP14571, GPC1 | chr2 | 239758345 | 239758394 | Hyper | TWIST2 |
| chr2 | 241759597 | 241759694 | Hyper | KIF1A | chr2 | 241758377 | 241758715 | Hyper | KIF1A |
| AC241851.2_88-34049 | 14729 | 14973 | Hyper |  | chr2 | 241771165 | 241771257 | Hyper |  |
| chrY | 2655316 | 2655346 | Hyper | SRY, RPS4Y1, XGPY2 | AC241851.2_88-34049 | 15261 | 15350 | Hyper |  |
| chr6 | 392307 | 393650 | Hyper | IRF4 | chr6 | 391173 | 392000 | Hyper | IRF4 |
| chr6 | 1379584 | 1379614 | Hyper |  | chr6 | 1378222 | 1379242 | Hyper |  |
| chr6 | 1383677 | 1384644 | Hyper | FOXF2 | chr6 | 1379909 | 1379952 | Hyper |  |
| chr6 | 1386071 | 1386112 | Hyper | FOXF2 | chr6 | 1385118 | 1385170 | Hyper | FOXF2 |
| chr6 | 1390241 | 1390613 | Hyper | FOXF2 | chr6 | 1389124 | 1389262 | Hyper | FOXF2 |
| chr6 | 1391318 | 1391379 | Hyper | FOXF2 | chr6 | 1390934 | 1391035 | Hyper | FOXF2 |
| chr6 | 1605387 | 1605454 | Hyper | FOXC1 | chr6 | 1524199 | 1524283 | Hyper |  |
| chr6 | 1625257 | 1625818 | Hyper | GMDS | chr6 | 1614833 | 1615184 | Hyper | FOXC1, GMDS |
| chr6 | 3229423 | 3229510 | Hyper | AK096219, TUBB2A, TUBB2B | chr6 | 3229029 | 3229059 | Hyper | AK096219, TUBB2A, TUBB2B |
| chr6 | 5997802 | 5997832 | Hyper | NRN1 | chr6 | 5996952 | 5996989 | Hyper | NRN1 |
| chr6 | 6006374 | 6006419 | Hyper | NRN1 | chr6 | 6003287 | 6005417 | Hyper | NRN1 |
| chr6 | 6007593 | 6008277 | Hyper | NRN1 | chr6 | 6006674 | 6006883 | Hyper | NRN1 |
| chr6 | 7728108 | 7728142 | Hyper | BMP6 | chr6 | 7727699 | 7727837 | Hyper | BMP6 |
| chr6 | 10381507 | 10382299 | Hyper |  | chr6 | 7728849 | 7728941 | Hyper | BMP6 |
| chr6 | 10383739 | 10383774 | Hyper |  | chr6 | 10382722 | 10383049 | Hyper |  |
| chr6 | 10386210 | 10386273 | Hyper |  | chr6 | 10384950 | 10385939 | Hyper |  |
| chr6 | 10410518 | 10410578 | Hyper | LOC100130275, TFAP2A | chr6 | 10390023 | 10391187 | Hyper | TFAP2A |
| chr6 | 10415113 | 10415215 | Hyper | LOC100130275, TFAP2A | chr6 | 10411356 | 10411510 | Hyper | LOC100130275, TFAP2A |
| chr6 | 10416118 | 10416351 | Hyper | LOC100130275, TFAP2A | chr6 | 10415559 | 10415713 | Hyper | LOC100130275, TFAP2A |
| chr6 | 10419086 | 10419506 | Hyper | LINC00518, LOC100130275, TFAP2A | chr6 | 10417158 | 10417557 | Hyper | LOC100130275, TFAP2A |
| chr6 | 10421053 | 10422635 | Hyper | LINC00518, LOC100130275, TFAP2A | chr6 | 10419744 | 10419941 | Hyper | LINC00518, LOC100130275, TFAP2A |
| chr6 | 10425496 | 10426884 | Hyper | LINC00518, LOC100130275, TFAP2A | chr6 | 10423613 | 10423704 | Hyper | LINC00518, LOC100130275, TFAP2A |
| chr6 | 10883008 | 10883038 | Hyper | GCM2, SYCP2L | chr6 | 10881835 | 10882057 | Hyper | SYCP2L, GCM2 |
| chr6 | 10887078 | 10887686 | Hyper | SYCP2L, GCM2 | chr6 | 10883444 | 10883474 | Hyper | SYCP2L, GCM2 |
| chr6 | 12749899 | 12749976 | Hyper | PHACTR1 | chr6 | 11044062 | 11044363 | Hyper | ELOVL2-AS1, ELOVL2 |
| chr6 | 17281417 | 17281534 | Hyper | RBM24 | chr6 | 12750210 | 12750255 | Hyper | PHACTR1 |
| chr6 | 19692066 | 19692246 | Hyper |  | chr6 | 19691638 | 19691841 | Hyper |  |
| chr6 | 21664719 | 21664749 | Hyper | LINC00340 | chr6 | 19837064 | 19837140 | Hyper | ID4 |
| chr6 | 24494679 | 24494766 | Hyper | GPLD1, ALDH5A1 | chr6 | 21665004 | 21665043 | Hyper | LINC00340 |
| chr6 | 26184095 | 26184391 | Hyper | HIST1H4D, HIST1H2BE | chr6 | 26034268 | 26034311 | Hyper | HIST1H2BB, HIST1H2AB, HIST1H3B, HIST1H4B |
| chr6 | 26240527 | 26241118 | Hyper | HIST1H4F, HIST1H4G, HIST1H3F, HIST1H1D | chr6 | 26188696 | 26189393 | Hyper | HIST1H4D, HIST1H3D, HIST1H3F, HIST1H2AD, HIST1H2BE |
| chr6 | 26251054 | 26251182 | Hyper | HIST1H4G, HIST1H2BH, HIST1H3F | chr6 | 26250468 | 26250822 | Hyper | HIST1H2BH, HIST1H3F, HIST1H4G, HIST1H4F |

TABLE 1-continued

| Chr | Start | Stop | Hypo/hyper | Annotation | Chr | Start | Stop | Hypo/hyper | Annotation |
|---|---|---|---|---|---|---|---|---|---|
| chr6 | 26271406 | 26271762 | Hyper | HIST1H3G, BC079832, HIST1H2BI, HIST1H4H | chr6 | 26251883 | 26252151 | Hyper | HIST1H3F, HIST1H4G, HIST1H2BH |
| chr6 | 26272512 | 26272617 | Hyper | HIST1H3G, HIST1H2BI, HIST1H4H, BC079832 | chr6 | 26271971 | 26272001 | Hyper | BC079832, HIST1H2BI, HIST1H4H, HIST1H3G |
| chr6 | 26327806 | 26327982 | Hyper | TRNA_Ser, TRNA_Arg, TRNA_Met, TRNA_Trp | chr6 | 26273400 | 26273480 | Hyper | HIST1H3G, HIST1H4H, HIST1H2BI, BC079832 |
| chr6 | 26501857 | 26502209 | Hyper | BTN1A1 | chr6 | 26328294 | 26328457 | Hyper | TRNA_Trp, TRNA_Ser, TRNA_Arg, TRNA_Met |
| chr6 | 26577158 | 26577475 | Hyper | TRNA_Tyr, TRNA_Ala, BC033330 | chr6 | 26550994 | 26551034 | Hyper | HMGN4, TRNA_Ala, TRNA_Ile, TRNA_Pro, TRNA_Lys |
| chr6 | 27064682 | 27065198 | Hyper | TRNA_Ser, TRNA_Pro | chr6 | 27059783 | 27059848 | Hyper | TRNA_Ser, TRNA_Pro |
| chr6 | 27182869 | 27182899 | Hyper | TRNA_Arg, TRNA_Ser, TRNA_Val | chr6 | 27173528 | 27174181 | Hyper | TRNA_Val, TRNA_Ser, TRNA_Arg |
| chr6 | 27205300 | 27205441 | Hyper | TRNA_Ile, TRNA_Val, TRNA_Leu | chr6 | 27203269 | 27203363 | Hyper | TRNA_Val, TRNA_Ile, TRNA_Leu |
| chr6 | 27228180 | 27228395 | Hyper | PRSS16 | chr6 | 27205671 | 27206040 | Hyper | PRSS16, TRNA_Ile, TRNA_Val, TRNA_Leu |
| chr6 | 27256097 | 27256173 | Hyper | TRNA_Val, TRNA_Pseudo, TRNA_Gln, TRNA_Ser | chr6 | 27247636 | 27247724 | Hyper | TRNA Ile, TRNA_Val, TRNA_Pseudo |
| chr6 | 27264332 | 27264364 | Hyper | TRNA_Ser, TRNA_Thr, TRNA_Gln, TRNA_Pseudo, TRNA_Val | chr6 | 27256383 | 27256420 | Hyper | TRNA_Val, TRNA_Pseudo, TRNA_Gln, TRNA_Ser |
| chr6 | 27463029 | 27463687 | Hyper | TRNA_Ser, TRNA_Asp | chr6 | 27279845 | 27280012 | Hyper | POM121L2, TRNA_Thr |
| chr6 | 27533822 | 27534341 | Hyper | TRNA_Lys, TRNA_Arg | chr6 | 27512761 | 27513487 | Hyper | TRNA_Ser, TRNA_Gln |
| chr6 | 27573171 | 27573392 | Hyper | TRNA_Leu | chr6 | 27559809 | 27560075 | Hyper | TRNA Met, TRNA_Lys, TRNA_Asp |
| chr6 | 27599159 | 27599341 | Hyper | TRNA_Ile | chr6 | 27598738 | 27598860 | Hyper | TRNA Ile |
| chr6 | 27648912 | 27648965 | Hyper | TRNA_Val, TRNA_Thr, TRNA_Ile, TRNA_Ser | chr6 | 27635265 | 27635434 | Hyper | TRNA_Ile, TRNA_Arg, TRNA_Ser, TRNA_Phe |
| chr6 | 27835047 | 27835417 | Hyper | HIST1H2AL, HIST1H3I, HIST1H4L, HIST1H1B | chr6 | 27834676 | 27834835 | Hyper | HIST1H3I, HIST1H4L, HIST1H1B, HIST1H2AL |
| chr6 | 27840543 | 27840617 | Hyper | HIST1H2AL, HIST1H4L, HIST1H3I, HIST1H1B | chr6 | 27839726 | 27840082 | Hyper | HIST1H2AL, HIST1H4L, HIST1H3I, HIST1H1B |
| chr6 | 27858515 | 27858548 | Hyper | HIST1H3J, HIST1H2AM, HIST1H2BO | chr6 | 27841104 | 27841136 | Hyper | HIST1H2AL, HIST1H4L, HIST1H3I, HIST1H1B |
| chr6 | 28367109 | 28367774 | Hyper | ZSCAN12 | chr6 | 28175189 | 28176212 | Hyper | TRNA_Ser, TOB2P1 |
| chr6 | 28414977 | 28415034 | Hyper |  | chr6 | 28410976 | 28411353 | Hyper | ZSCAN23 |
| chr6 | 28457870 | 28458158 | Hyper | TRNA_Thr | chr6 | 28457608 | 28457638 | Hyper | TRNA_Thr |
| chr6 | 36252984 | 36253171 | Hyper | PNPLA1 | chr6 | 35992428 | 35992458 | Hyper | MAPK14, SLC26A8 |
| chr6 | 37664140 | 37664187 | Hyper |  | chr6 | 36808323 | 36808441 | Hyper | AK096023, CPNES |
| chr6 | 39281824 | 39281875 | Hyper | KCNK17, KCNK16 | chr6 | 39281088 | 39281133 | Hyper | KCNK16, KCNK17 |
| chr6 | 41337072 | 41337128 | Hyper |  | chr6 | 40554653 | 40554699 | Hyper | LRFN2 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr6 | 41340902 | 41341024 | Hyper | | chr6 | 41339263 | 41339838 | Hyper | |
| chr6 | 41342243 | 41342275 | Hyper | | chr6 | 41341501 | 41341549 | Hyper | |
| chr6 | 41605937 | 41606542 | Hyper | MDFI | chr6 | 41342807 | 41342837 | Hyper | |
| chr6 | 43612825 | 43613067 | Hyper | RSPH9, MAD2L1BP | chr6 | 42879554 | 42879718 | Hyper | PTCRA |
| chr6 | 46703350 | 46703436 | Hyper | PLA2G7 | chr6 | 45388716 | 45388775 | Hyper | RUNX2 |
| chr6 | 50681699 | 50681942 | Hyper | TFAP2D | chr6 | 50674372 | 50674750 | Hyper | TFAP2D |
| chr6 | 50682659 | 50683227 | Hyper | TFAP2D | chr6 | 50682319 | 50682386 | Hyper | TFAP2D |
| chr6 | 50689913 | 50690039 | Hyper | TFAP2D | chr6 | 50684939 | 50684969 | Hyper | TFAP2D |
| chr6 | 50787216 | 50788352 | Hyper | TFAP2B | chr6 | 50692083 | 50692481 | Hyper | TFAP2D |
| chr6 | 50791222 | 50791632 | Hyper | TFAP2B | chr6 | 50789374 | 50789404 | Hyper | TFAP2B |
| chr6 | 50793728 | 50793882 | Hyper | TFAP2B | chr6 | 50793335 | 50793404 | Hyper | TFAP2B |
| chr6 | 50803834 | 50803867 | Hyper | TFAP2B | chr6 | 50794531 | 50794693 | Hyper | TFAP2B |
| chr6 | 50808681 | 50808854 | Hyper | TFAP2B | chr6 | 50804131 | 50804368 | Hyper | TFAP2B |
| chr6 | 50811062 | 50811488 | Hyper | TFAP2B | chr6 | 50810551 | 50810839 | Hyper | TFAP2B |
| chr6 | 50814569 | 50814599 | Hyper | TFAP2B | chr6 | 50813258 | 50813939 | Hyper | TFAP2B |
| chr6 | 50817905 | 50817935 | Hyper | TFAP2B | chr6 | 50817023 | 50817229 | Hyper | TFAP2B |
| chr6 | 50818920 | 50819000 | Hyper | TFAP2B | chr6 | 50818449 | 50818706 | Hyper | TFAP2B |
| chr6 | 56112262 | 56112386 | Hyper | COL21A1 | chr6 | 55443691 | 55443946 | Hyper | HMGCLL1 |
| chr6 | 56818656 | 56818937 | Hyper | BEND6 | chr6 | 56716332 | 56716410 | Hyper | |
| chr6 | 58147447 | 58147480 | Hyper | TRNA_Ile, TRNA_Ala | chr6 | 56819217 | 56819256 | Hyper | BEND6 |
| chr6 | 62995356 | 62996133 | Hyper | KHDRBS2 | chr6 | 58147790 | 58147976 | Hyper | TRNA_Ile, TRNA_Ala |
| chr6 | 70992057 | 70992162 | Hyper | COL9A1 | chr6 | 62996443 | 62996489 | Hyper | KHDRBS2 |
| chr6 | 70992830 | 70993015 | Hyper | COL9A1 | chr6 | 70992415 | 70992500 | Hyper | COL9A1 |
| chr6 | 72129789 | 72129829 | Hyper | LINC00472 | chr6 | 71666901 | 71666986 | Hyper | B3GAT2 |
| chr6 | 72596950 | 72596980 | Hyper | RIMS1 | chr6 | 72130107 | 72130464 | Hyper | LINC00472 |
| chr6 | 73330834 | 73331176 | Hyper | KCNQ5 | chr6 | 73329784 | 73330126 | Hyper | KCNQ5 |
| chr6 | 73332157 | 73332435 | Hyper | KCNQ5 | chr6 | 73331527 | 73331569 | Hyper | KCNQ5 |
| chr6 | 78173696 | 78173984 | Hyper | HTR1B | chr6 | 78172287 | 78172572 | Hyper | HTR1B |
| chr6 | 79620399 | 79620611 | Hyper | IRAK1BP1 | chr6 | 78176790 | 78176820 | Hyper | HTR1B |
| chr6 | 84417436 | 84417778 | Hyper | SNAP91 | chr6 | 80656930 | 80657180 | Hyper | ELOVL4 |
| chr6 | 84418652 | 84418686 | Hyper | SNAP91 | chr6 | 84418172 | 84418281 | Hyper | SNAP91 |
| chr6 | 84563080 | 84563242 | Hyper | RIPPLY2, CYB5R4 | chr6 | 84419157 | 84419415 | Hyper | SNAP91 |
| chr6 | 85472407 | 85473267 | Hyper | TBX18 | chr6 | 84563489 | 84563542 | Hyper | CYB5R4, RIPPLY2 |
| chr6 | 85473928 | 85474378 | Hyper | TBX18 | chr6 | 85473508 | 85473703 | Hyper | TBX18 |
| chr6 | 85476233 | 85476285 | Hyper | TBX18 | chr6 | 85474594 | 85474736 | Hyper | TBX18 |
| chr6 | 85478514 | 85478724 | Hyper | TBX18 | chr6 | 85476998 | 85477028 | Hyper | TBX18 |
| chr6 | 85483345 | 85483375 | Hyper | TBX18 | chr6 | 85482530 | 85482822 | Hyper | TBX18 |
| chr6 | 87862092 | 87862172 | Hyper | ZNF292 | chr6 | 85483635 | 85484920 | Hyper | TBX18 |
| chr6 | 91320285 | 91320318 | Hyper | | chr6 | 88876963 | 88877437 | Hyper | |
| chr6 | 94127455 | 94127544 | Hyper | EPHA7 | chr6 | 94126973 | 94127064 | Hyper | EPHA7 |
| chr6 | 94129509 | 94129575 | Hyper | EPHA7 | chr6 | 94128365 | 94128399 | Hyper | EPHA7 |
| chr6 | 99271926 | 99272810 | Hyper | POU3F2 | chr6 | 96464000 | 96464204 | Hyper | FUT9 |
| chr6 | 99277180 | 99277330 | Hyper | POU3F2 | chr6 | 99273369 | 99273410 | Hyper | POU3F2 |
| chr6 | 99280557 | 99280744 | Hyper | POU3F2 | chr6 | 99279556 | 99279612 | Hyper | POU3F2 |
| chr6 | 99283512 | 99283582 | Hyper | POU3F2 | chr6 | 99281014 | 99281385 | Hyper | POU3F2 |
| chr6 | 99290657 | 99290693 | Hyper | POU3F2 | chr6 | 99290360 | 99290398 | Hyper | POU3F2 |
| chr6 | 99292252 | 99292417 | Hyper | POU3F2 | chr6 | 99291264 | 99291438 | Hyper | POU3F2 |
| chr6 | 100038682 | 100038964 | Hyper | | chr6 | 99295726 | 99296467 | Hyper | POU3F2 |
| chr6 | 100050754 | 100051971 | Hyper | PRDM13 | chr6 | 100039259 | 100039289 | Hyper | |
| chr6 | 100054866 | 100054917 | Hyper | PRDM13 | chr6 | 100053221 | 100053511 | Hyper | PRDM13 |
| chr6 | 100061311 | 100061419 | Hyper | PRDM13 | chr6 | 100061022 | 100061076 | Hyper | PRDM13 |
| chr6 | 100062178 | 100062586 | Hyper | PRDM13 | chr6 | 100061757 | 100061835 | Hyper | PRDM13 |
| chr6 | 100441364 | 100441966 | Hyper | LOC728012, MCHR2 | chr6 | 100062944 | 100063068 | Hyper | PRDM13 |
| chr6 | 100904214 | 100904275 | Hyper | SIM1 | chr6 | 100903384 | 100903631 | Hyper | SIM1 |
| chr6 | 100912070 | 100912119 | Hyper | SIM1 | chr6 | 100905969 | 100906016 | Hyper | SIM1 |
| chr6 | 100912919 | 100913149 | Hyper | SIM1 | chr6 | 100912421 | 100912480 | Hyper | SIM1 |
| chr6 | 101840708 | 101840820 | Hyper | GRIK2 | chr6 | 100915142 | 100915205 | Hyper | SIM1 |
| chr6 | 101850147 | 101850275 | Hyper | GRIK2 | chr6 | 101847185 | 101847215 | Hyper | GRIK2 |
| chr6 | 105388913 | 105389710 | Hyper | LINC00577 | chr6 | 101850570 | 101850600 | Hyper | GRIK2 |
| chr6 | 105401620 | 105401874 | Hyper | LIN28B | chr6 | 105400913 | 105400943 | Hyper | LIN28B |
| chr6 | 105405656 | 105405772 | Hyper | LIN28B | chr6 | 105404574 | 105404674 | Hyper | LIN28B |
| chr6 | 105584264 | 105585554 | Hyper | BVES-AS1, BVES | chr6 | 105406098 | 105406128 | Hyper | LIN28B |
| chr6 | 106441869 | 106442979 | Hyper | | chr6 | 106429049 | 106429624 | Hyper | |
| chr6 | 107955952 | 107955982 | Hyper | SOBP | chr6 | 106960908 | 106961023 | Hyper | AIM1 |
| chr6 | 108436072 | 108436526 | Hyper | AF520419 | chr6 | 108435075 | 108435263 | Hyper | AF520419 |
| chr6 | 108440091 | 108440961 | Hyper | AF520419 | chr6 | 108438245 | 108438577 | Hyper | AF520419 |
| chr6 | 108484909 | 108485406 | Hyper | NR2E1, AF520419 | chr6 | 108479290 | 108479665 | Hyper | NR2E1, AF520419 |
| chr6 | 108486158 | 108486394 | Hyper | NR2E1, AF520419 | chr6 | 108485665 | 108485905 | Hyper | NR2E1, AF520419 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr6 | 108489385 | 108490633 | Hyper | NR2E1 | chr6 | 108487724 | 108488416 | Hyper | AF520419, NR2E1 |
| chr6 | 108492303 | 108492451 | Hyper | NR2E1 | chr6 | 108490978 | 108491423 | Hyper | NR2E1 |
| chr6 | 108496208 | 108496649 | Hyper | NR2E1 | chr6 | 108495681 | 108495951 | Hyper | NR2E1 |
| chr6 | 110679123 | 110679414 | Hyper | METTL24 | chr6 | 108497494 | 108497881 | Hyper | NR2E1 |
| chr6 | 116783448 | 116783493 | Hyper | FAM26F | chr6 | 110797678 | 110797708 | Hyper | SLC22A16 |
| chr6 | 117585967 | 117586004 | Hyper | VGLL2 | chr6 | 117086249 | 117086738 | Hyper | FAM162B |
| chr6 | 117587480 | 117587577 | Hyper | VGLL2 | chr6 | 117587123 | 117587169 | Hyper | VGLL2 |
| chr6 | 117591411 | 117591743 | Hyper | VGLL2 | chr6 | 117591161 | 117591191 | Hyper | VGLL2 |
| chr6 | 118228747 | 118228828 | Hyper | SLC35F1 | chr6 | 118228102 | 118228151 | Hyper | SLC35F1 |
| chr6 | 118229711 | 118229818 | Hyper | SLC35F1 | chr6 | 118229154 | 118229383 | Hyper | SLC35F1 |
| chr6 | 12175867 | 121758702 | Hyper | GJA1 | chr6 | 118241281 | 118241387 | Hyper | SLC35F1 |
| chr6 | 123317797 | 123317833 | Hyper | CLVS2 | chr6 | 123317029 | 123317589 | Hyper | CLVS2 |
| chr6 | 125284131 | 125284175 | Hyper | RNF217, STL, Metazoa_SRP | chr6 | 124124432 | 124124466 | Hyper | NKAIN2 |
| chr6 | 127439370 | 127439453 | Hyper | RSPO3 | chr6 | 126068092 | 126068178 | Hyper | HEY2, BC036196 |
| chr6 | 127440406 | 127441123 | Hyper | RSPO3 | chr6 | 127440033 | 127440127 | Hyper | RSPO3 |
| chr6 | 127442021 | 127442104 | Hyper | RSPO3 | chr6 | 127441554 | 127441762 | Hyper | RSPO3 |
| chr6 | 129204459 | 129204524 | Hyper | LAMA2 | chr6 | 127840501 | 127840681 | Hyper | |
| chr6 | 130686883 | 130687057 | Hyper | TMEM200A | chr6 | 130686534 | 130686564 | Hyper | TMEM200A |
| chr6 | 132722078 | 132722196 | Hyper | MOXD1 | chr6 | 131602584 | 131602694 | Hyper | AKAP7 |
| chr6 | 133562374 | 133563058 | Hyper | EYA4 | chr6 | 133561740 | 133562070 | Hyper | EYA4 |
| chr6 | 134176549 | 134176579 | Hyper | MGC34034, BC041459 | chr6 | 133563380 | 133563918 | Hyper | EYA4 |
| chr6 | 134213944 | 134214364 | Hyper | AX747860, TCF21 | chr6 | 134210528 | 134211367 | Hyper | AX747860, TCF21 |
| chr6 | 137241928 | 137242205 | Hyper | SLC35D3, PEX7 | chr6 | 134638950 | 134639003 | Hyper | SGK1 |
| chr6 | 137311158 | 137311380 | Hyper | IL20RA, NHEG1 | chr6 | 137244114 | 137244616 | Hyper | SLC35D3, PEX7 |
| chr6 | 137813787 | 137813895 | Hyper | OLIG3 | chr6 | 137809141 | 137811088 | Hyper | OLIG3 |
| chr6 | 137815008 | 137815662 | Hyper | OLIG3 | chr6 | 137814604 | 137814763 | Hyper | OLIG3 |
| chr6 | 137818505 | 137819368 | Hyper | OLIG3 | chr6 | 137816472 | 137817351 | Hyper | OLIG3 |
| chr6 | 150285351 | 150286639 | Hyper | ULBP1 | chr6 | 146755567 | 146755649 | Hyper | |
| chr6 | 151561016 | 151561182 | Hyper | AKAP12 | chr6 | 150359114 | 150359407 | Hyper | |
| chr6 | 151562066 | 151562563 | Hyper | AKAP12 | chr6 | 151561501 | 151561857 | Hyper | AKAP12 |
| chr6 | 152957909 | 152958076 | Hyper | SYNE1 | chr6 | 152623054 | 152623349 | Hyper | SYNE1 |
| chr6 | 153451890 | 153451968 | Hyper | RGS17 | chr6 | 153451299 | 153451426 | Hyper | RGS17 |
| chr6 | 155316235 | 155316265 | Hyper | | chr6 | 154360650 | 154360746 | Hyper | OPRM1 |
| chr6 | 159590048 | 159590986 | Hyper | FNDC1 | chr6 | 157556764 | 157557912 | Hyper | |
| chr6 | 161188513 | 161188543 | Hyper | | chr6 | 159654923 | 159655003 | Hyper | FNDC1 |
| chr6 | 166074119 | 166074412 | Hyper | | chr6 | 161352101 | 161352135 | Hyper | |
| chr6 | 166077378 | 166077660 | Hyper | | chr6 | 166076788 | 166077021 | Hyper | |
| chr6 | 166401254 | 166401307 | Hyper | LINC00602, LINC00473, AK090688 | chr6 | 166267582 | 166268082 | Hyper | AK090688 |
| chr6 | 166421911 | 166422185 | Hyper | | chr6 | 166402240 | 166402546 | Hyper | LINC00602, LINC00473, AK090688 |
| chr6 | 166580344 | 166581494 | Hyper | T | chr6 | 166579723 | 166580144 | Hyper | T |
| chr6 | 166582505 | 166582797 | Hyper | T | chr6 | 166581705 | 166582239 | Hyper | T |
| chr6 | 169653638 | 169653668 | Hyper | THBS2 | chr6 | 168842847 | 168842944 | Hyper | SMOC2 |
| chr4 | 330392 | 330445 | Hyper | ZNF141 | chr4 | 107711 | 107759 | Hyper | |
| chr4 | 570966 | 571013 | Hyper | | chr4 | 568429 | 569914 | Hyper | |
| chr4 | 682798 | 682919 | Hyper | MFSD7, | chr4 | 571508 | 571689 | Hyper | |
| chr4 | 996639 | 996708 | Hyper | MYL5FGFRL1, SLC26A1, IDUA | chr4 | 995855 | 996357 | Hyper | FGFRL1, SLC26A1, IDUA |
| chr4 | 1396727 | 1396835 | Hyper | CRIPAK | chr4 | 1165379 | 1165470 | Hyper | SPON2 |
| chr4 | 1398303 | 1398378 | Hyper | CRIPAK | chr4 | 1397396 | 1397495 | Hyper | CRIPAK |
| chr4 | 1400728 | 1400785 | Hyper | | chr4 | 1399723 | 1399768 | Hyper | CRIPAK |
| chr4 | 2042106 | 2042556 | Hyper | C4orf48 | chr4 | 1401711 | 1401743 | Hyper | |
| chr4 | 3768833 | 3769342 | Hyper | ADRA2C | chr4 | 2765862 | 2765910 | Hyper | TNIP2 |
| chr4 | 3873694 | 3873769 | Hyper | | chr4 | 3769542 | 3769574 | Hyper | ADRA2C |
| chr4 | 4229689 | 4229781 | Hyper | TMEM128, OTOP1 | chr4 | 4228185 | 4228241 | Hyper | TMEM128, OTOP1 |
| chr4 | 4855102 | 4855171 | Hyper | MSX1 | chr4 | 4387533 | 4387627 | Hyper | NSG1 |
| chr4 | 4862769 | 4863110 | Hyper | MSX1 | chr4 | 4855371 | 4855433 | Hyper | MSX1 |
| chr4 | 4868566 | 4868691 | Hyper | MSX1 | chr4 | 4867698 | 4867886 | Hyper | MSX1 |
| chr4 | 4872088 | 4872167 | Hyper | MSX1 | chr4 | 4868898 | 4869087 | Hyper | MSX1 |
| chr4 | 5053136 | 5053518 | Hyper | STK32B | chr4 | 4872777 | 4872850 | Hyper | MSX1 |
| chr4 | 5709906 | 5710269 | Hyper | EVC, EVC2 | chr4 | 5053747 | 5054093 | Hyper | STK32B |
| chr4 | 5889948 | 5890045 | Hyper | FLJ46481, CRMP1 | chr4 | 5712979 | 5713281 | Hyper | EVC, EVC2 |
| chr4 | 5892750 | 5892780 | Hyper | FLJ46481, CRMP1 | chr4 | 5891966 | 5892124 | Hyper | FLJ46481, CRMP1 |
| chr4 | 5894721 | 5894787 | Hyper | FLJ46481, CRMP1 | chr4 | 5893981 | 5894347 | Hyper | FLJ46481, CRMP1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr4 | 6202103 | 6202276 | Hyper | LOC285484, JAKMIP1 | chr4 | 6200897 | 6201235 | Hyper | LOC285484, JAKMIP1 |
| chr4 | 6565004 | 6565042 | Hyper | | chr4 | 6247351 | 6247381 | Hyper | LOC285484 |
| chr4 | 8858827 | 8859738 | Hyper | HMX1 | chr4 | 8582549 | 8582579 | Hyper | CPZ, GPR78 |
| chr4 | 8861649 | 8862014 | Hyper | HMX1 | chr4 | 8859974 | 8860553 | Hyper | HMX1 |
| chr4 | 8863441 | 8863774 | Hyper | HMX1 | chr4 | 8862797 | 8862911 | Hyper | HMX1 |
| chr4 | 8864831 | 8865058 | Hyper | HMX1 | chr4 | 8864499 | 8864598 | Hyper | HMX1 |
| chr4 | 8869601 | 8869813 | Hyper | HMX1 | chr4 | 8868822 | 8869364 | Hyper | HMX1 |
| chr4 | 8873809 | 8873984 | Hyper | HMX1 | chr4 | 8873054 | 8873337 | Hyper | HMX1 |
| chr4 | 8875877 | 8875907 | Hyper | HMX1 | chr4 | 8874485 | 8874787 | Hyper | HMX1 |
| chr4 | 8893794 | 8893931 | Hyper | | chr4 | 8893501 | 8893531 | Hyper | |
| chr4 | 8895554 | 8895584 | Hyper | | chr4 | 8894641 | 8895350 | Hyper | |
| chr4 | 9782992 | 9783167 | Hyper | DRD5 | chr4 | 8895915 | 8896052 | Hyper | |
| chr4 | 10458395 | 10459121 | Hyper | ZNF518B | chr4 | 9783382 | 9783412 | Hyper | DRD5 |
| chr4 | 11429506 | 11429633 | Hyper | | chr4 | 10462833 | 10463519 | Hyper | ZNF518B |
| chr4 | 13524665 | 13524775 | Hyper | LOC285547 | chr4 | 13524400 | 13524430 | Hyper | LOC285547 |
| chr4 | 13540983 | 13541068 | Hyper | NKX3-2, LOC285548, LOC285547 | chr4 | 13537569 | 13537688 | Hyper | NKX3-2, LOC285547 |
| chr4 | 13543859 | 13544113 | Hyper | NKX3-2, LOC285548 | chr4 | 13541408 | 13541447 | Hyper | LOC285547, NKX3-2, LOC285548 |
| chr4 | 13546026 | 13546078 | Hyper | LOC285548, NKX3-2 | chr4 | 13545563 | 13545731 | Hyper | LOC285548, NKX3-2 |
| chr4 | 16084741 | 16085381 | Hyper | | chr4 | 13548502 | 13548895 | Hyper | LOC285548, NKX3-2 |
| chr4 | 17783003 | 17783033 | Hyper | FAM184B | chr4 | 16085618 | 16085682 | Hyper | |
| chr4 | 20254693 | 20254723 | Hyper | SLIT2 | chr4 | 17783390 | 17783600 | Hyper | FAM184B |
| chr4 | 20256152 | 20256340 | Hyper | SLIT2 | chr4 | 20255414 | 20255861 | Hyper | SLIT2 |
| chr4 | 24801809 | 24801985 | Hyper | CCDC149, SOD3 | chr4 | 21950248 | 21950341 | Hyper | |
| chr4 | 27086432 | 27086462 | Hyper | | chr4 | 25657437 | 25657477 | Hyper | SLC34A2 |
| chr4 | 30723811 | 30723862 | Hyper | PCDH7 | chr4 | 30722243 | 30722273 | Hyper | PCDH7 |
| chr4 | 37245726 | 37245851 | Hyper | KIAA1239, MIR4801 | chr4 | 30724249 | 30724372 | Hyper | PCDH7 |
| chr4 | 37247096 | 37247216 | Hyper | KIAA1239, MIR4801 | chr4 | 37246134 | 37246883 | Hyper | KIAA1239, MIR4801 |
| chr4 | 41747009 | 41747133 | Hyper | PHOX2B | chr4 | 41258716 | 41259176 | Hyper | UCHL1-AS1, UCHL1 |
| chr4 | 41747958 | 41748296 | Hyper | PHOX2B | chr4 | 41747493 | 41747582 | Hyper | PHOX2B |
| chr4 | 41749033 | 41749063 | Hyper | PHOX2B | chr4 | 41748660 | 41748803 | Hyper | PHOX2B |
| chr4 | 41750426 | 41750504 | Hyper | PHOX2B | chr4 | 41749270 | 41749761 | Hyper | PHOX2B |
| chr4 | 41752451 | 41752693 | Hyper | PHOX2B | chr4 | 41751870 | 41752006 | Hyper | PHOX2B |
| chr4 | 41753610 | 41754071 | Hyper | PHOX2B | chr4 | 41752968 | 41753398 | Hyper | PHOX2B |
| chr4 | 41880331 | 41880412 | Hyper | BC025350 | chr4 | 41875430 | 41875902 | Hyper | BC025350 |
| chr4 | 41882553 | 41882627 | Hyper | BC025350 | chr4 | 41881385 | 41881425 | Hyper | BC025350 |
| chr4 | 41883510 | 41883610 | Hyper | BC025350 | chr4 | 41883091 | 41883302 | Hyper | BC025350 |
| chr4 | 42154280 | 42154359 | Hyper | BEND4 | chr4 | 42154787 | 42154997 | Hyper | BEND4 |
| chr4 | 42399137 | 42399191 | Hyper | SHISA3 | chr4 | 42154787 | 42154025 | Hyper | BEND4 |
| chr4 | 44450263 | 44450375 | Hyper | KCTD8 | chr4 | 44449480 | 44449651 | Hyper | KCTD8 |
| chr4 | 46995161 | 46995789 | Hyper | GABRA4 | chr4 | 46391353 | 46391383 | Hyper | GABRA2 |
| chr4 | 48485067 | 48485510 | Hyper | SLC10A4, ZAR1 | chr4 | 47034908 | 47034938 | Hyper | GABRB1 |
| chr4 | 48486356 | 48486389 | Hyper | ZAR1, SLC10A4 | chr4 | 48485742 | 48486000 | Hyper | ZAR1, SLC10A4 |
| chr4 | 53728691 | 53728955 | Hyper | RASL11B | chr4 | 48492322 | 48492433 | Hyper | ZAR1, SLC10A4FRYL |
| chr4 | 54967342 | 54967484 | Hyper | GSX2 | chr4 | 54966854 | 54967032 | Hyper | GSX2 |
| chr4 | 54970369 | 54970482 | Hyper | GSX2 | chr4 | 54969833 | 54970095 | Hyper | GSX2 |
| chr4 | 55093048 | 55093255 | Hyper | PDGFRA | chr4 | 54975936 | 54976131 | Hyper | GSX2 |
| chr4 | 55097404 | 55097634 | Hyper | PDGFRA | chr4 | 55096239 | 55096344 | Hyper | PDGFRA |
| chr4 | 55098674 | 55098744 | Hyper | PDGFRA | chr4 | 55097973 | 55098290 | Hyper | PDGFRA |
| chr4 | 55524220 | 55524274 | Hyper | KIT | chr4 | 55099016 | 55099062 | Hyper | PDGFRA |
| chr4 | 55992129 | 55992169 | Hyper | KDR | chr4 | 55991107 | 55991228 | Hyper | KDR |
| chr4 | 57371897 | 57371963 | Hyper | ARL9, SRP72 | chr4 | 56659692 | 56660021 | Hyper | U6 |
| chr4 | 57396946 | 57397264 | Hyper | THEGL, ARL9 | chr4 | 57372336 | 57372504 | Hyper | ARL9, SRP72 |
| chr4 | 62067511 | 62067624 | Hyper | LPHN3 | chr4 | 57521470 | 57522709 | Hyper | HOPX |
| chr4 | 66535407 | 66535443 | Hyper | EPHA5, LOC100144602 | chr4 | 62068072 | 62068150 | Hyper | LPHN3 |
| chr4 | 74809877 | 74809933 | Hyper | | chr4 | 74702479 | 74702516 | Hyper | CXCL6 |
| chr4 | 81106351 | 81106786 | Hyper | PRDM8 | chr4 | 76555668 | 76555713 | Hyper | CDKL2 |
| chr4 | 81187046 | 81187076 | Hyper | FGF5 | chr4 | 81124277 | 81124662 | Hyper | PRDM8 |
| chr4 | 81188491 | 81188556 | Hyper | FGF5 | chr4 | 81187559 | 81187589 | Hyper | FGF5 |
| chr4 | 81952170 | 81952234 | Hyper | BMP3 | chr4 | 81189419 | 81189911 | Hyper | FGF5 |
| chr4 | 82136495 | 82136548 | Hyper | PRKG2 | chr4 | 82135873 | 82136056 | Hyper | PRKG2 |
| chr4 | 85402377 | 85402511 | Hyper | | chr4 | 82136807 | 82136837 | Hyper | PRKG2 |
| chr4 | 85403913 | 85404693 | Hyper | NKX6-1 | chr4 | 85402776 | 85403423 | Hyper | |
| chr4 | 85414373 | 85414405 | Hyper | NKX6-1 | chr4 | 85414045 | 85414142 | Hyper | NKX6-1 |
| chr4 | 85417336 | 85417564 | Hyper | NKX6-1 | chr4 | 85414725 | 85414846 | Hyper | NKX6-1 |
| chr4 | 85418393 | 85418963 | Hyper | NKX6-1 | chr4 | 85417953 | 85418079 | Hyper | NKX6-1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr4 | 85422188 | 85422432 | Hyper | NKX6-1 | chr4 | 85420591 | 85420621 | Hyper | NKX6-1 |
| chr4 | 85424401 | 85424483 | Hyper | NKX6-1 | chr4 | 85422953 | 85423316 | Hyper | NKX6-1 |
| chr4 | 89378744 | 89378888 | Hyper | HERC5 | chr4 | 89378464 | 89378497 | Hyper | HERC5 |
| chr4 | 90758843 | 90758883 | Hyper | LOC644248, SNCA | chr4 | 90757517 | 90757669 | Hyper | LOC644248, SNCA |
| chr4 | 94751009 | 94751039 | Hyper | ATOH1 | chr4 | 93226820 | 93227129 | Hyper | GRID2 |
| chr4 | 94753415 | 94753445 | Hyper | ATOH1 | chr4 | 94751419 | 94751502 | Hyper | ATOH1 |
| chr4 | 96470752 | 96470782 | Hyper | UNC5C | chr4 | 94755963 | 94756109 | Hyper | ATOH1 |
| chr4 | 101111901 | 101111970 | Hyper | DDIT4L | chr4 | 101111298 | 101111504 | Hyper | DDIT4L |
| chr4 | 102711994 | 102712065 | Hyper | BANK1 | chr4 | 102711731 | 102711787 | Hyper | BANK1 |
| chr4 | 107956676 | 107957033 | Hyper | DKK2 | chr4 | 107955311 | 107955826 | Hyper | DKK2 |
| chr4 | 109093101 | 109093168 | Hyper | LEF1-AS1 | chr4 | 107957373 | 107957466 | Hyper | DKK2 |
| chr4 | 110223090 | 110223811 | Hyper | COL25A1 | chr4 | 109093405 | 109093506 | Hyper | LEF1-AS1 |
| chr4 | 111536288 | 111536693 | Hyper | PITX2 | chr4 | 111532632 | 111532961 | Hyper | PITX2 |
| chr4 | 111537407 | 111537497 | Hyper | PITX2 | chr4 | 111536960 | 111537042 | Hyper | PITX2 |
| chr4 | 111542187 | 111542757 | Hyper | PITX2 | chr4 | 111540199 | 111540360 | Hyper | PITX2 |
| chr4 | 111543661 | 111543735 | Hyper | PITX2 | chr4 | 111543232 | 111543450 | Hyper | PITX2 |
| chr4 | 111549800 | 111549830 | Hyper | PITX2 | chr4 | 111544381 | 111544583 | Hyper | PITX2 |
| chr4 | 111552118 | 111552148 | Hyper | PITX2 | chr4 | 111550618 | 111550834 | Hyper | PITX2 |
| chr4 | 111553916 | 111553951 | Hyper | PITX2 | chr4 | 111553099 | 111553450 | Hyper | PITX2 |
| chr4 | 111557965 | 111558049 | Hyper |  | chr4 | 111554950 | 111555343 | Hyper |  |
| chr4 | 111560249 | 111560636 | Hyper |  | chr4 | 111558803 | 111559233 | Hyper |  |
| chr4 | 113430640 | 113430672 | Hyper | NEUROG2 | chr4 | 111562576 | 111562648 | Hyper |  |
| chr4 | 113436216 | 113436287 | Hyper | NEUROG2 | chr4 | 113431834 | 113432573 | Hyper | NEUROG2 |
| chr4 | 113442098 | 113442525 | Hyper | NEUROG2 | chr4 | 113441592 | 113441733 | Hyper | NEUROG2 |
| chr4 | 117847399 | 117847458 | Hyper |  | chr4 | 113444020 | 113444448 | Hyper | NEUROG2 |
| chr4 | 121992265 | 121992312 | Hyper | 7SK, NDNF | chr4 | 121844063 | 121844206 | Hyper | PRDM5 |
| chr4 | 122301422 | 122301846 | Hyper | QRFPR | chr4 | 121993997 | 121994251 | Hyper |  |
| chr4 | 122685807 | 122685951 | Hyper | PP12613, TMEM155 | chr4 | 122302116 | 122302246 | Hyper | QRFPR |
| chr4 | 122871294 | 122871334 | Hyper |  | chr4 | 122686209 | 122686470 | Hyper | PP12613, TMEM155 |
| chr4 | 126237355 | 126237387 | Hyper | FAT4 | chr4 | 122871573 | 122872000 | Hyper |  |
| chr4 | 128544048 | 128544161 | Hyper | INTU | chr4 | 126238024 | 126238173 | Hyper | FAT4 |
| chr4 | 134067974 | 134068004 | Hyper | PCDH10, BC040219 | chr4 | 128544646 | 128544789 | Hyper | INTU |
| chr4 | 134069793 | 134069896 | Hyper | PCDH10, BC040219 | chr4 | 134068662 | 134068739 | Hyper | PCDH10, BC040219 |
| chr4 | 134073184 | 134073322 | Hyper | PCDH10, BC040219 | chr4 | 134071850 | 134072967 | Hyper | PCDH10, BC040219 |
| chr4 | 134074030 | 134074156 | Hyper | PCDH10, BC040219 | chr4 | 134073568 | 134073641 | Hyper | PCDH10, BC040219 |
| chr4 | 140656643 | 140656691 | Hyper | MAML3 | chr4 | 140200529 | 140201462 | Hyper | NDUFC1, MGARP |
| chr4 | 141347942 | 141348151 | Hyper | CLGN | chr4 | 140656968 | 140657089 | Hyper | MAML3 |
| chr4 | 141488870 | 141489128 | Hyper | UCP1 | chr4 | 141418921 | 141419418 | Hyper | LOC152586 |
| chr4 | 142053520 | 142053652 | Hyper | RNF150 | chr4 | 142053130 | 142053160 | Hyper | RNF150 |
| chr4 | 144621336 | 144622058 | Hyper | FREM3 | chr4 | 143766796 | 143766930 | Hyper |  |
| chr4 | 145568459 | 145568741 | Hyper | HHIP, HHIP-AS1 | chr4 | 145568052 | 145568147 | Hyper | HHIP, HHIP-AS1 |
| chr4 | 147559321 | 147560617 | Hyper | POU4F2 | chr4 | 147558272 | 147558504 | Hyper | POU4F2 |
| chr4 | 147568636 | 147569060 | Hyper | POU4F2 | chr4 | 147560933 | 147562055 | Hyper | POU4F2 |
| chr4 | 147576177 | 147576639 | Hyper |  | chr4 | 147569620 | 147569650 | Hyper | POU4F2 |
| chr4 | 154712172 | 154712539 | Hyper | SFRP2 | chr4 | 154709524 | 154710914 | Hyper | SFRP2 |
| chr4 | 154713949 | 154714010 | Hyper | SFRP2 | chr4 | 154713500 | 154713530 | Hyper | SFRP2 |
| chr4 | 155411501 | 155412279 | Hyper | DCHS2 | chr4 | 155254166 | 155254196 | Hyper | DCHS2 |
| chr4 | 156129153 | 156129183 | Hyper | NPY2R | chr4 | 155663209 | 155663647 | Hyper | LRAT, DQ266889 |
| chr4 | 156129746 | 156129797 | Hyper | NPY2R | chr4 | 156129451 | 156129495 | Hyper | NPY2R |
| chr4 | 156297513 | 156297543 | Hyper | MAP9 | chr4 | 156130047 | 156130297 | Hyper | NPY2R |
| chr4 | 156680257 | 156680383 | Hyper | GUCY1B3 | chr4 | 156589273 | 156589323 | Hyper | GUCY1A3 |
| chr4 | 158142847 | 158142999 | Hyper | GRIA2 | chr4 | 158141576 | 158141606 | Hyper | GRIA2 |
| chr4 | 16425329 | 164253447 | Hyper | NPY1R, NPYY1 | chr4 | 158143443 | 158143564 | Hyper | GRIA2 |
| chr4 | 165305030 | 165305163 | Hyper |  | chr4 | 165304515 | 165304578 | Hyper |  |
| chr4 | 166796011 | 166796212 | Hyper | TLL1 | chr4 | 166414834 | 166414864 | Hyper |  |
| chr4 | 172734168 | 172734203 | Hyper | GALNTL6 | chr4 | 168155124 | 168155269 | Hyper |  |
| chr4 | 174429658 | 174429688 | Hyper |  | chr4 | 172734550 | 172734790 | Hyper | GALNTL6 |
| chr4 | 174438567 | 174438744 | Hyper | HAND2 | chr4 | 174430310 | 174431072 | Hyper |  |
| chr4 | 174440635 | 174440713 | Hyper | HAND2 | chr4 | 174439822 | 174440257 | Hyper | HAND2 |
| chr4 | 174443563 | 174443934 | Hyper | HAND2, NBLA00301 | chr4 | 174443212 | 174443242 | Hyper | HAND2, NBLA00301 |
| chr4 | 174446952 | 174447005 | Hyper | HAND2, NBLA00301 | chr4 | 174446486 | 174446525 | Hyper | HAND2, NBLA00301 |
| chr4 | 174451855 | 174452098 | Hyper | NBLA00301, HAND2 | chr4 | 174449950 | 174451482 | Hyper | NBLA00301, HAND2 |
| chr4 | 174460186 | 174460221 | Hyper | NBLA00301, HAND2 | chr4 | 174459185 | 174459840 | Hyper | NBLA00301, HAND2 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr4 | 175133085 | 175133201 | Hyper | AK125257 | chr4 | 175132735 | 175132765 | Hyper | AK125257 |
|  | 175135921 | 175136011 | Hyper | AK125257 | chr4 | 175134897 | 175135672 | Hyper | AK125257 |
| chr4 | 175138964 | 175139254 | Hyper | AK125257 | chr4 | 175138411 | 175138546 | Hyper | AK125257 |
| chr4 | 175750456 | 175750738 | Hyper | AK093264, BC034301, GLRA3 | chr4 | 175139559 | 175139685 | Hyper | AK125257 |
| chr4 | 176987324 | 176987373 | Hyper | WDR17 | chr4 | 176923499 | 176923536 | Hyper |  |
| chr4 | 180979270 | 180979300 | Hyper |  | chr4 | 177713228 | 177713310 | Hyper | VEGFC |
| chr4 | 183063666 | 183063950 | Hyper | TENM3, MGC45800 | chr4 | 180980297 | 180980356 | Hyper |  |
| chr4 | 184019249 | 184019316 | Hyper | WWC2, WWC2-AS2 | chr4 | 183064617 | 183064655 | Hyper | TENM3, MGC45800 |
| chr4 | 184826238 | 184826400 | Hyper | STOX2 | chr4 | 184718260 | 184718352 | Hyper |  |
| chr4 | 185937333 | 185937889 | Hyper | HELT | chr4 | 184827161 | 184827271 | Hyper | STOX2 |
| chr4 | 185940338 | 185940460 | Hyper | HELT | chr4 | 185938497 | 185938564 | Hyper | HELT |
| chr22 | 17081932 | 17082001 | Hyper | TPTEP1, CCT8L2 | chr4 | 185941585 | 185942760 | Hyper | HELT |
| chr22 | 17083396 | 17083426 | Hyper | TPTEP1, CCT8L2 | chr22 | 17082943 | 17083003 | Hyper | TPTEP1, CCT8L2 |
| chr22 | 17602511 | 17602624 | Hyper | BC021738, CECR6, IL17RA | chr22 | 17601086 | 17601368 | Hyper | BC021738, CECR6, IL17RA |
| chr22 | 19017532 | 19017567 | Hyper | DGCR10, DGCR9 DGCR2 | chr22 | 17850454 | 17850621 | Hyper | CECR2 |
| chr22 | 19511849 | 19511891 | Hyper | CLDN5, CDC45 | chr22 | 19510799 | 19511567 | Hyper | CLDN5, CDC45 |
| chr22 | 19742834 | 19742969 | Hyper | TBX1 | chr22 | 19706329 | 19706514 | Hyper | SEPT5-GP1BB |
| chr22 | 20792535 | 20792641 | Hyper | KLHL22, SCARF2 | chr22 | 19748644 | 19748956 | Hyper | TBX1 |
| chr22 | 22862825 | 22863159 | Hyper | ZNF280A | chr22 | 22090595 | 22090742 | Hyper | YPEL1 |
| chr22 | 25678748 | 25679337 | Hyper | BC040576 | chr22 | 24180687 | 24180766 | Hyper | DERL3, AK096976 |
| chr22 | 25817458 | 25817612 | Hyper |  | chr22 | 25817107 | 25817180 | Hyper |  |
| chr22 | 28838509 | 28838551 | Hyper |  | chr22 | 28198569 | 28198605 | Hyper | MN1 |
| chr22 | 30938521 | 30938584 | Hyper | SEC14L6 | chr22 | 29877223 | 29877299 | Hyper | KIAA0845, NEFH |
| chr22 | 31218794 | 31218829 | Hyper | OSBP2 | chr22 | 31218510 | 31218540 | Hyper | OSBP2 |
| chr22 | 38220653 | 38220972 | Hyper | GCAT, ANKRD54, GALR3 | chr22 | 33453877 | 33454366 | Hyper |  |
| chr22 | 39954413 | 39954516 | Hyper |  | chr22 | 38477069 | 38477794 | Hyper | BALAP2L2, SLC16A8, PICK1 |
| chr22 | 42311521 | 42311587 | Hyper | TNFRSF13C, SHISA8 | chr22 | 42310087 | 42310220 | Hyper | SHISA8 |
| chr22 | 42679729 | 42679841 | Hyper | LOC388906 | chr22 | 42353611 | 42353892 | Hyper | LINC00634 |
| chr22 | 43808280 | 43808428 | Hyper | MPPED1 | chr22 | 43740084 | 43740128 | Hyper |  |
| chr22 | 44287650 | 44287696 | Hyper | PNPLA5 | chr22 | 44258366 | 44258506 | Hyper | SULT4A1 |
| chr22 | 45404345 | 45404433 | Hyper | PHF21B | chr22 | 45403086 | 45403133 | Hyper | PHF21B |
| chr22 | 45406271 | 45406328 | Hyper | PHF21B | chr22 | 45404994 | 45405061 | Hyper | PHF21B |
| chr22 | 46263088 | 46263809 | Hyper |  | chr22 | 46262452 | 46262869 | Hyper |  |
| chr22 | 46368029 | 46368059 | Hyper | WNT7B | chr22 | 46276749 | 46276820 | Hyper |  |
| chr22 | 48885031 | 48885061 | Hyper | FAM19A5 | chr22 | 46658791 | 46658846 | Hyper | TTC38, PKDREJ |
| chr22 | 48886659 | 48886849 | Hyper | FAM19A5 | chr22 | 48885296 | 48885901 | Hyper | FAM19A5 |
| chr22 | 48972144 | 48972181 | Hyper | FAM19A5 | chr22 | 48971130 | 48971748 | Hyper | FAM19A5 |
| chr22 | 50496841 | 50496940 | Hyper | MLC1 | chr22 | 48972411 | 48972657 | Hyper | FAM19A5 |
| chr22 | 50623700 | 50623815 | Hyper | TRABD, PANX2 | chr22 | 50497147 | 50497287 | Hyper | MLC1 |
| chr11 | 406876 | 406939 | Hyper | SIGIRR, PKP3 | chr22 | 51042278 | 51042810 | Hyper | MAPK8IP2 |
| chr11 | 627074 | 627104 | Hyper | SCT, CDHR5 | chr11 | 407427 | 407463 | Hyper | SIGIRR, PKP3 |
| chr11 | 637298 | 637441 | Hyper | DRD4, DEAF1 | chr11 | 636895 | 636925 | Hyper | DRD4, DEAF1, SCT |
| chr11 | 829543 | 829708 | Hyper | CD151, EFCAB4A, PNPLA2, JB050151 | chr11 | 726417 | 726466 | Hyper | EPS8L2 |
| chr11 | 1358291 | 1358332 | Hyper |  | chr11 | 830174 | 830265 | Hyper | JB050151, CD151, POLR2L, EFCAB4A, PNPLA2 |
| chr11 | 1770192 | 1770248 | Hyper | CTSD, IFITM10 | chr11 | 1411875 | 1411905 | Hyper | BRSK2 |
| chr11 | 2291984 | 2292526 | Hyper | ASCL2 | chr11 | 2291440 | 2291728 | Hyper | ASCL2 |
| chr11 | 7274215 | 7274245 | Hyper | SYT9 | chr11 | 7273286 | 7273375 | Hyper | SYT9 |
| chr11 | 8289517 | 8289745 | Hyper | LMO1 | chr11 | 8189987 | 8190766 | Hyper | RIC3 |
| chr11 | 9025970 | 9026348 | Hyper | NRIP3 | chr11 | 8290195 | 8290335 | Hyper | LMO1 |
| chr11 | 12029957 | 12030147 | Hyper | DKK3 | chr11 | 9112446 | 9112741 | Hyper | KRT8P41, MIR5691, SCUBE2 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr11 | 16632493 | 16632670 | Hyper | | chr11 | 15136085 | 15136308 | Hyper | INSC |
| chr11 | 17740493 | 17740570 | Hyper | MYOD1 | chr11 | 17497492 | 17497685 | Hyper | ABCC8 |
| chr11 | 17743742 | 17743775 | Hyper | MYOD1 | chr11 | 17741806 | 17742445 | Hyper | MYOD1 |
| chr11 | 18813032 | 18813086 | Hyper | PTPN5 | chr11 | 18812614 | 18812653 | Hyper | PTPN5 |
| chr11 | 18813792 | 18813947 | Hyper | PTPN5 | chr11 | 18813478 | 18813508 | Hyper | PTPN5 |
| chr11 | 19367102 | 19367330 | Hyper | NAV2 | chr11 | 19263848 | 19263878 | Hyper | E2F8 |
| chr11 | 20153718 | 20153764 | Hyper | | chr11 | 19735730 | 19735760 | Hyper | NAV2, LOC100126784 |
| chr11 | 20180279 | 20180793 | Hyper | DBX1 | chr11 | 20178066 | 20178305 | Hyper | DBX1 |
| chr11 | 20181701 | 20181993 | Hyper | DBX1 | chr11 | 20181213 | 20181254 | Hyper | DBX1 |
| chr11 | 20183251 | 20183421 | Hyper | DBX1 | chr11 | 20182864 | 20182959 | Hyper | DBX1 |
| chr11 | 20184569 | 20185410 | Hyper | DBX1 | chr11 | 20183674 | 20183773 | Hyper | DBX1 |
| chr11 | 20229863 | 20230091 | Hyper | TRNA | chr11 | 20229058 | 20229550 | Hyper | TRNA |
| chr11 | 20618445 | 20619131 | Hyper | SLC6A5 | chr11 | 20230398 | 20230644 | Hyper | TRNA |
| chr11 | 20621341 | 20621644 | Hyper | SLC6A5 | chr11 | 20619717 | 20619974 | Hyper | SLC6A5 |
| chr11 | 20690653 | 20690935 | Hyper | NELL1 | chr11 | 20622705 | 20623350 | Hyper | SLC6A5 |
| chr11 | 20691685 | 20691914 | Hyper | NELL1 | chr11 | 20691219 | 20691452 | Hyper | NELL1 |
| chr11 | 22215123 | 22215287 | Hyper | ANO5 | chr11 | 20692453 | 20692529 | Hyper | NELL1 |
| chr11 | 22364821 | 22364975 | Hyper | SLC17A6 | chr11 | 22362934 | 22363189 | Hyper | SLC17A6 |
| chr11 | 27742185 | 27742215 | Hyper | | chr11 | 22365407 | 22365477 | Hyper | SLC17A6 |
| chr11 | 27743436 | 27743608 | Hyper | | chr11 | 27743115 | 27743173 | Hyper | |
| chr11 | 27744711 | 27744744 | Hyper | | chr11 | 27744147 | 27744238 | Hyper | |
| chr11 | 30038689 | 30038739 | Hyper | KCNA4 | chr11 | 30037593 | 30037743 | Hyper | KCNA4 |
| chr11 | 30606763 | 30606864 | Hyper | MPPED2 | chr11 | 30605919 | 30606123 | Hyper | MPPED2 |
| chr11 | 31818458 | 31818652 | Hyper | PAX6 | chr11 | 30607367 | 30607409 | Hyper | MPPED2 |
| chr11 | 31820045 | 31821025 | Hyper | PAX6 | chr11 | 31819302 | 31819833 | Hyper | PAX6 |
| chr11 | 31822325 | 31822393 | Hyper | PAX6 | chr11 | 31821297 | 31821778 | Hyper | PAX6 |
| chr11 | 31824564 | 31824680 | Hyper | PAX6 | chr11 | 31824300 | 31824355 | Hyper | PAX6 |
| chr11 | 31825696 | 31827204 | Hyper | PAX6 | chr11 | 31825017 | 31825280 | Hyper | PAX6 |
| chr11 | 31833097 | 31833155 | Hyper | DKFZp686K1684, RCN1, PAX6 | chr11 | 31827438 | 31828123 | Hyper | DKFZp686K1684, RCN1, PAX6 |
| chr11 | 31836046 | 31836470 | Hyper | DKFZp686K1684, RCN1, PAX6 | chr11 | 31835707 | 31835797 | Hyper | DKFZp686K1684, RCN1, PAX6 |
| chr11 | 31838678 | 31839051 | Hyper | DKFZp686K1684, RCN1 | chr11 | 31837019 | 31838392 | Hyper | DKFZp686K1684, RCN1, PAX6 |
| chr11 | 31840587 | 31840922 | Hyper | RCN1, DKFZp686K1684 | chr11 | 31839307 | 31840080 | Hyper | RCN1, DKFZp686K1684 |
| chr11 | 31846022 | 31846230 | Hyper | RCN1, DKFZp686K1684 | chr11 | 31841376 | 31842276 | Hyper | RCN1, DKFZp686K1684 |
| chr11 | 31847250 | 31847925 | Hyper | RCN1, DKFZp686K1684 | chr11 | 31846434 | 31846985 | Hyper | RCN1, DKFZp686K1684 |
| chr11 | 32009104 | 32009160 | Hyper | RCN1 | chr11 | 31848472 | 31849300 | Hyper | RCN1, DKFZp686K1684 |
| chr11 | 32448583 | 32448979 | Hyper | WT1-AS, WT1 | chr11 | 32354844 | 32355197 | Hyper | |
| chr11 | 32455841 | 32456025 | Hyper | WT1-AS, WT1 | chr11 | 32455602 | 32455634 | Hyper | WT1-AS, WT1 |
| chr11 | 32457851 | 32458175 | Hyper | WT1, WT1-AS | chr11 | 32456279 | 32457069 | Hyper | WT1-AS, WT1 |
| chr11 | 32459684 | 32460071 | Hyper | WT1, WT1-AS | chr11 | 32458389 | 32458823 | Hyper | WT1, WT1-AS |
| chr11 | 32460796 | 32460864 | Hyper | WT1, WT1-AS | chr11 | 32460468 | 32460515 | Hyper | WT1, WT1-AS |
| chr11 | 35641683 | 35641718 | Hyper | FJX1 | chr11 | 33890297 | 33890334 | Hyper | LMO2 |
| chr11 | 43600453 | 43600557 | Hyper | BC031305, MIR129-2, JA715139 | chr11 | 43596513 | 43596608 | Hyper | MIR129-2, JA715139, BC031305 |
| chr11 | 43602468 | 43603228 | Hyper | MIR129-2, JA715139 | chr11 | 43601094 | 43601467 | Hyper | MIR129-2, JA715139, BC031305 |
| chr11 | 44325688 | 44325747 | Hyper | ALX4 | chr11 | 43603628 | 43604177 | Hyper | JA715139, MIR129-2 |
| chr11 | 44326439 | 44326481 | Hyper | ALX4 | chr11 | 44326137 | 44326184 | Hyper | ALX4 |
| chr11 | 44333371 | 44333480 | Hyper | ALX4 | chr11 | 44330656 | 44331711 | Hyper | ALX4 |
| chr11 | 44338335 | 44338367 | Hyper | ALX4 | chr11 | 44337690 | 44338077 | Hyper | ALX4 |
| chr11 | 44341966 | 44342034 | Hyper | | chr11 | 44340823 | 44340858 | Hyper | ALX4 |
| chr11 | 47209044 | 47209189 | Hyper | PACSIN3 | chr11 | 46316860 | 46317680 | Hyper | CREB3L1 |
| chr11 | 59323596 | 59323729 | Hyper | TRNA_Val, TRNA_Lys, TRNA_Phe, U7, JB175310, TRNA_Leu, TRNA_Arg | chr11 | 58672746 | 58673064 | Hyper | AK294973 |
| chr11 | 60718668 | 60719163 | Hyper | SLC15A3 | chr11 | 59333405 | 59333541 | Hyper | TRNA_Phe, OSBP, JB175310, TRNA_Lys, U7 |
| chr11 | 61063108 | 61063138 | Hyper | DDB1, VWCE | chr11 | 61062868 | 61062903 | Hyper | DDB1, VWCE |
| chr11 | 61595086 | 61595262 | Hyper | FADS2 | chr11 | 61277113 | 61277220 | Hyper | SYT7, LRRC10B, MIR4488 |
| chr11 | 61723067 | 61723159 | Hyper | BEST1, FTH1 | chr11 | 61596420 | 61596640 | Hyper | FADS2 |
| chr11 | 64480429 | 64480593 | Hyper | | chr11 | 63767984 | 63768131 | Hyper | MACROD1, OTUB1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr11 | 64739468 | 64739508 | Hyper | | chr11 | 64480824 | 64481042 | Hyper | |
| chr11 | 65600810 | 65601640 | Hyper | SNX32 | chr11 | 65185548 | 65185728 | Hyper | NEAT1, FRMD8 |
| chr11 | 66188115 | 66188145 | Hyper | NPAS4 | chr11 | 65816447 | 65816564 | Hyper | SF3B2, GAL3ST3 |
| chr11 | 69516968 | 69517174 | Hyper | FGF19 | chr11 | 66188473 | 66188974 | Hyper | NPAS4 |
| chr11 | 69588930 | 69589184 | Hyper | FGF4 | chr11 | 69518030 | 69518083 | Hyper | FGF19 |
| chr11 | 69590149 | 69590222 | Hyper | FGF4 | chr11 | 69589824 | 69589854 | Hyper | FGF4 |
| chr11 | 71951639 | 71951738 | Hyper | PHOX2A, INPPL1 | chr11 | 71318332 | 71318967 | Hyper | |
| chr11 | 71954612 | 71954642 | Hyper | PHOX2A, INPPL1 | chr11 | 71952340 | 71952541 | Hyper | PHOX2A, INPPL1 |
| chr11 | 71956007 | 71956340 | Hyper | PHOX2A, INPPL1 | chr11 | 71955344 | 71955377 | Hyper | PHOX2A, INPPL1 |
| chr11 | 74394491 | 74394600 | Hyper | | chr11 | 72432837 | 72432916 | Hyper | |
| chr11 | 75379252 | 75379895 | Hyper | MAP6 | chr11 | 74953265 | 74953422 | Hyper | TPBGL |
| chr11 | 82444376 | 82445101 | Hyper | FAM181B | chr11 | 78672917 | 78672964 | Hyper | ODZ4, TENM4 |
| chr11 | 88241705 | 88242448 | Hyper | GRM5-AS1, GRM5 | chr11 | 86085786 | 86085968 | Hyper | CCDC81 |
| chr11 | 91957500 | 91957674 | Hyper | | chr11 | 88799082 | 88799209 | Hyper | GRM5 |
| chr11 | 91958734 | 91958908 | Hyper | | chr11 | 91958083 | 91958230 | Hyper | |
| chr11 | 91959899 | 91960045 | Hyper | | chr11 | 91959394 | 91959430 | Hyper | |
| chr11 | 93063870 | 93063948 | Hyper | CCDC67 | chr11 | 93063583 | 93063645 | Hyper | CCDC67 |
| chr11 | 94473600 | 94473733 | Hyper | | chr11 | 94134086 | 94134853 | Hyper | GPR83 |
| chr11 | 100997649 | 100997981 | Hyper | LOC101054525, PGR | chr11 | 98891795 | 98891882 | Hyper | CNTN5 |
| chr11 | 100998667 | 100998747 | Hyper | LOC101054525, PGR | chr11 | 100998276 | 100998318 | Hyper | LOC101054525, PGR |
| chr11 | 101454190 | 101454490 | Hyper | | chr11 | 101453180 | 101453518 | Hyper | |
| chr11 | 105480755 | 105480806 | Hyper | GRIA4 | chr11 | 104034521 | 104034788 | Hyper | |
| chr11 | 105481541 | 105481571 | Hyper | GRIA4 | chr11 | 105481216 | 105481458 | Hyper | GRIA4 |
| chr11 | 106888717 | 106888747 | Hyper | GUCY1A2 | chr11 | 106888308 | 106888429 | Hyper | GUCY1A2 |
| chr11 | 109293720 | 109293847 | Hyper | C11orf87 | chr11 | 109292906 | 109293052 | Hyper | C11orf87 |
| chr11 | 111383183 | 111383682 | Hyper | BTG4, MIR34B, MIR34C, C11orf88, BC021736 | chr11 | 110583574 | 110583730 | Hyper | |
| chr11 | 115375120 | 115375177 | Hyper | CADM1 | chr11 | 111411093 | 111412061 | Hyper | LAYN, C11orf88 |
| chr11 | 115630515 | 115630910 | Hyper | LINC00900 | chr11 | 115530134 | 115530422 | Hyper | |
| chr11 | 119292779 | 119292809 | Hyper | THY1, LOC100499227 | chr11 | 115631307 | 115631364 | Hyper | LINC00900 |
| chr11 | 119612861 | 119613044 | Hyper | | chr11 | 119612227 | 119612399 | Hyper | |
| chr11 | 120435800 | 120435830 | Hyper | GRIK4 | chr11 | 120435405 | 120435477 | Hyper | GRIK4 |
| chr11 | 122848079 | 122848591 | Hyper | BSX | chr11 | 122847265 | 122847696 | Hyper | BSX |
| chr11 | 122849642 | 122850163 | Hyper | BSX | chr11 | 122849301 | 122849331 | Hyper | BSX |
| chr11 | 122851177 | 122851209 | Hyper | BSX | chr11 | 122850424 | 122850536 | Hyper | BSX |
| chr11 | 123066433 | 123066463 | Hyper | CLMP | chr11 | 122852438 | 122852475 | Hyper | BSX |
| chr11 | 123301160 | 123302026 | Hyper | | chr11 | 123229382 | 123229422 | Hyper | |
| chr11 | 124736196 | 124736252 | Hyper | ROBO3 | chr11 | 124735437 | 124735482 | Hyper | ROBO3 |
| chr11 | 125035763 | 125036208 | Hyper | PKNOX2 | chr11 | 124738777 | 124739088 | Hyper | ROBO3 |
| chr11 | 125773675 | 125774034 | Hyper | DDX25, HYLS1, PUS3 | chr11 | 125036598 | 125036645 | Hyper | PKNOX2 |
| chr11 | 126870453 | 126870543 | Hyper | KIRREL3-AS3 | chr11 | 126870182 | 126870212 | Hyper | KIRREL3-AS3 |
| chr11 | 128562892 | 128563351 | Hyper | FLI1, FLI1-AS1, AX747861 | chr11 | 126873390 | 126873515 | Hyper | KIRREL3-AS3 |
| chr11 | 128564740 | 128565379 | Hyper | FLI1, FLI1-AS1, AX747861 | chr11 | 128563940 | 128564329 | Hyper | FLI1, FLI1-AS1, AX747861 |
| chr11 | 129243849 | 129244603 | Hyper | BARX2 | chr11 | 129242876 | 129243587 | Hyper | BARX2 |
| chr11 | 130319527 | 130319613 | Hyper | ADAMTS15 | chr11 | 129244893 | 129244923 | Hyper | BARX2 |
| chr11 | 132813619 | 132813949 | Hyper | | chr11 | 131780469 | 131781033 | Hyper | NTM |
| chr11 | 132934123 | 132934176 | Hyper | | chr11 | 132864134 | 132864175 | Hyper | |
| chr11 | 133402206 | 133402260 | Hyper | | chr11 | 132952768 | 132953320 | Hyper | |
| chr11 | 133906783 | 133906918 | Hyper | LOC100128239 | chr11 | 133825226 | 133825543 | Hyper | IGSF9B |
| chr11 | 134145703 | 134146393 | Hyper | GLB1L3 | chr11 | 133939002 | 133939177 | Hyper | JAM3 |
| chr11 | 134281365 | 134281509 | Hyper | LOC283177 | chr11 | 134146682 | 134146894 | Hyper | GLB1L3 |
| chr5 | 320840 | 320982 | Hyper | AHRR, PDCD6 | chr5 | 53849 | 53900 | Hyper | |
| chr5 | 528641 | 528685 | Hyper | MIR4456 | chr5 | 524337 | 524404 | Hyper | |
| chr5 | 1295031 | 1295075 | Hyper | TERT | chr5 | 1294630 | 1294767 | Hyper | TERT |
| chr5 | 1445171 | 1445282 | Hyper | SLC6A3 | chr5 | 1295322 | 1295662 | Hyper | TERT |
| chr5 | 1446319 | 1446599 | Hyper | SLC6A3 | chr5 | 1445738 | 1445928 | Hyper | SLC6A3 |
| chr5 | 1875453 | 1875497 | Hyper | IRX4 | chr5 | 1874892 | 1875099 | Hyper | IRX4 |
| chr5 | 1877160 | 1877239 | Hyper | IRX4 | chr5 | 1875870 | 1876860 | Hyper | IRX4 |
| chr5 | 1878739 | 1879045 | Hyper | IRX4 | chr5 | 1878014 | 1878528 | Hyper | IRX4 |
| chr5 | 1882294 | 1882605 | Hyper | IRX4 | chr5 | 1879605 | 1879719 | Hyper | IRX4 |
| chr5 | 1883515 | 1883820 | Hyper | IRX4 | chr5 | 1882844 | 1883089 | Hyper | IRX4 |
| chr5 | 1884557 | 1884698 | Hyper | IRX4 | chr5 | 1884178 | 1884237 | Hyper | IRX4 |
| chr5 | 1885985 | 1886192 | Hyper | IRX4 | chr5 | 1885158 | 1885458 | Hyper | IRX4 |
| chr5 | 1886812 | 1887737 | Hyper | IRX4 | chr5 | 1886542 | 1886581 | Hyper | IRX4 |
| chr5 | 1952624 | 1952654 | Hyper | | chr5 | 1931174 | 1931754 | Hyper | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr5 | 2738848 | 2739422 | Hyper | IRX2 | chr5 | 2038705 | 2038850 | Hyper | |
| chr5 | 2740243 | 2741061 | Hyper | IRX2 | chr5 | 2739967 | 2739997 | Hyper | IRX2 |
| chr5 | 2748374 | 2748459 | Hyper | C5orf38, IRX2 | chr5 | 2743617 | 2743713 | Hyper | C5orf38, IRX2 |
| chr5 | 2749699 | 2749729 | Hyper | C5orf38, IRX2 | chr5 | 2749213 | 2749425 | Hyper | IRX2, C5orf38 |
| chr5 | 2751694 | 2751894 | Hyper | C5orf38, IRX2 | chr5 | 2750435 | 2751368 | Hyper | C5orf38, IRX2 |
| chr5 | 2755323 | 2755489 | Hyper | IRX2, C5orf38 | chr5 | 2752991 | 2753040 | Hyper | C5orf38, IRX2 |
| chr5 | 2756599 | 2757427 | Hyper | C5orf38, IRX2 | chr5 | 2755732 | 2756388 | Hyper | C5orf38, IRX2 |
| chr5 | 3591354 | 3591388 | Hyper | IRX1 | chr5 | 3590405 | 3590760 | Hyper | IRX1 |
| chr5 | 3592728 | 3592881 | Hyper | IRX1 | chr5 | 3591857 | 3592037 | Hyper | IRX1 |
| chr5 | 3595090 | 3595178 | Hyper | IRX1 | chr5 | 3594250 | 3594717 | Hyper | IRX1 |
| chr5 | 3596540 | 3596880 | Hyper | IRX1 | chr5 | 3595448 | 3595802 | Hyper | IRX1 |
| chr5 | 3599833 | 3599863 | Hyper | IRX1 | chr5 | 3597411 | 3597461 | Hyper | IRX1 |
| chr5 | 3600868 | 3600898 | Hyper | IRX1 | chr5 | 3600150 | 3600180 | Hyper | IRX1 |
| chr5 | 3606633 | 3606668 | Hyper | IRX1 | chr5 | 3602804 | 3603320 | Hyper | IRX1 |
| chr5 | 5140170 | 5140225 | Hyper | ADAMTS16, AK094462 | chr5 | 5139673 | 5139900 | Hyper | ADAMTS16, AK094462 |
| chr5 | 6448930 | 6449582 | Hyper | UBE2QL1 | chr5 | 5140630 | 5140901 | Hyper | ADAMTS16, AK094462 |
| chr5 | 6687277 | 6687431 | Hyper | | chr5 | 6583461 | 6583579 | Hyper | LOC255167 |
| chr5 | 7851015 | 7851121 | Hyper | FASTKD3, C5orf49 | chr5 | 7395263 | 7395538 | Hyper | ADCY2 |
| chr5 | 10333688 | 10334132 | Hyper | | chr5 | 9546612 | 9546648 | Hyper | SNORD123, LOC100505806 |
| chr5 | 11384906 | 11385363 | Hyper | CTNND2 | chr5 | 10565021 | 10565607 | Hyper | ANKRD33B |
| chr5 | 11904896 | 11904943 | Hyper | | chr5 | 11903760 | 11904696 | Hyper | |
| chr5 | 16179049 | 16179141 | Hyper | MARCH11, BC043001 | chr5 | 15500748 | 15500807 | Hyper | FBXL7 |
| chr5 | 16180128 | 16180260 | Hyper | BC043001, MARCH11 | chr5 | 16179516 | 16179713 | Hyper | BC043001, MARCH11 |
| chr5 | 22853443 | 22853508 | Hyper | | chr5 | 17218943 | 172190100 | Hyper | BASP1, LOC285696 |
| chr5 | 31194375 | 31194641 | Hyper | CDH6 | chr5 | 31193937 | 31193989 | Hyper | CDH6 |
| chr5 | 32710331 | 32710470 | Hyper | NPR3 | chr5 | 31639778 | 31639845 | Hyper | PDZD2 |
| chr5 | 32711316 | 32711896 | Hyper | NPR3 | chr5 | 32710802 | 32710896 | Hyper | NPR3 |
| chr5 | 32712077 | 32712491 | Hyper | NPR3 | chr5 | 32711826 | 32711870 | Hyper | NPR3 |
| chr5 | 33892083 | 33892115 | Hyper | U6, ADAMTS12 | chr5 | 32712764 | 32712908 | Hyper | NPR3 |
| chr5 | 33936216 | 33936276 | Hyper | RXFP3, SLC45A2 | chr5 | 33892413 | 33892443 | Hyper | U6, ADAMTS12 |
| chr5 | 37834684 | 37834714 | Hyper | GDNF-AS1, GDNF | chr5 | 33936599 | 33936663 | Hyper | SLC45A2, RXFP3 |
| chr5 | 37838600 | 37838885 | Hyper | GDNF-AS1, GDNF | chr5 | 37836649 | 37837992 | Hyper | GDNF, GDNF-AS1 |
| chr5 | 37840381 | 37840853 | Hyper | GDNF, GDNF-AS1 | chr5 | 37839780 | 37840125 | Hyper | GDNF-AS1, GDNF |
| chr5 | 38257842 | 38257959 | Hyper | EGFLAM | chr5 | 38257485 | 38257606 | Hyper | EGFLAM |
| chr5 | 40681150 | 40681367 | Hyper | PTGER4 | chr5 | 38845834 | 38845872 | Hyper | OSMR |
| chr5 | 42424822 | 42425060 | Hyper | GHR | chr5 | 40681676 | 40682004 | Hyper | PTGER4 |
| chr5 | 42991825 | 42992934 | Hyper | AK056817 | chr5 | 42951105 | 42952441 | Hyper | |
| chr5 | 42995115 | 42995153 | Hyper | AK056817 | chr5 | 42993150 | 42994193 | Hyper | AK056817 |
| chr5 | 43017953 | 43018183 | Hyper | LOC648987 | chr5 | 43008515 | 43008562 | Hyper | LOC648987 |
| chr5 | 43019238 | 43019347 | Hyper | LOC648987 | chr5 | 43018410 | 43018767 | Hyper | LOC648987 |
| chr5 | 43040886 | 43040964 | Hyper | ANXA2R, LOC153684, DQ601842 | chr5 | 43019809 | 43019887 | Hyper | LOC648987 |
| chr5 | 44389766 | 44389852 | Hyper | FGF10 | chr5 | 43397002 | 43397246 | Hyper | CCL28 |
| chr5 | 45695906 | 45695947 | Hyper | HCN1 | chr5 | 45695186 | 45695533 | Hyper | HCN1 |
| chr5 | 49736592 | 49736685 | Hyper | | chr5 | 45696336 | 45696439 | Hyper | HCN1 |
| chr5 | 50263568 | 50263641 | Hyper | | chr5 | 50262893 | 50263014 | Hyper | |
| chr5 | 50265325 | 50265429 | Hyper | | chr5 | 50264307 | 50264603 | Hyper | |
| chr5 | 50674152 | 50674188 | Hyper | ISL1, LOC642366 | chr5 | 50265720 | 50265880 | Hyper | |
| chr5 | 50675013 | 50675075 | Hyper | ISL1, LOC642366 | chr5 | 50674560 | 50674590 | Hyper | ISL1, LOC642366 |
| chr5 | 50695280 | 50695463 | Hyper | ISL1 | chr5 | 50678346 | 50678490 | Hyper | ISL1, LOC642366 |
| chr5 | 54180063 | 54180093 | Hyper | | chr5 | 54179587 | 54179633 | Hyper | |
| chr5 | 54518651 | 54519321 | Hyper | CCNO, MCIDAS | chr5 | 54516522 | 54517017 | Hyper | CCNO, MCIDAS |
| chr5 | 57878271 | 57878375 | Hyper | RAB3C | chr5 | 54527304 | 54527343 | Hyper | CCNO, MCIDAS |
| chr5 | 59189055 | 59189206 | Hyper | | chr5 | 59188291 | 59188327 | Hyper | |
| chr5 | 63254903 | 63255265 | Hyper | HTR1A | chr5 | 59189863 | 59189948 | Hyper | |
| chr5 | 63257727 | 63257861 | Hyper | HTR1A | chr5 | 63256863 | 63256895 | Hyper | HTR1A |
| chr5 | 63986488 | 63986584 | Hyper | FAM159B | chr5 | 63802007 | 63802514 | Hyper | RGS7BP |
| chr5 | 71015180 | 71015728 | Hyper | CARTPT | chr5 | 71014720 | 71014895 | Hyper | CARTPT |
| chr5 | 72526413 | 72526643 | Hyper | | chr5 | 71403566 | 71403653 | Hyper | MAP1B |
| chr5 | 72594802 | 72595059 | Hyper | | chr5 | 72529289 | 72530609 | Hyper | |
| chr5 | 72599079 | 72599833 | Hyper | | chr5 | 72595542 | 72595788 | Hyper | |
| chr5 | 72715204 | 72715768 | Hyper | | chr5 | 72677672 | 72678319 | Hyper | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr5 | 72732801 | 72732884 | Hyper | FOXD1 | chr5 | 72716102 | 72716180 | Hyper | |
| chr5 | 72746680 | 72746710 | Hyper | FOXD1 | chr5 | 72740147 | 72740184 | Hyper | FOXD1 |
| chr5 | 75380163 | 75380193 | Hyper | SV2C | chr5 | 75377883 | 75378033 | Hyper | SV2C |
| chr5 | 76011285 | 76011337 | Hyper | F2R, NCRUPAR | chr5 | 75380624 | 75380974 | Hyper | SV2C |
| chr5 | 76250435 | 76250504 | Hyper | CRHBP | chr5 | 76249270 | 76250150 | Hyper | CRHBP |
| chr5 | 76924930 | 76924960 | Hyper | OTP | chr5 | 76923679 | 76924409 | Hyper | OTP |
| chr5 | 76928157 | 76928397 | Hyper | OTP | chr5 | 76925561 | 76925690 | Hyper | OTP |
| chr5 | 76932302 | 76932332 | Hyper | OTP | chr5 | 76928688 | 76928906 | Hyper | OTP |
| chr5 | 76934173 | 76934870 | Hyper | OTP | chr5 | 76932542 | 76933281 | Hyper | OTP |
| chr5 | 76939420 | 76939774 | Hyper | OTP | chr5 | 76936016 | 76936721 | Hyper | OTP |
| chr5 | 77140527 | 77140711 | Hyper | | chr5 | 76941201 | 76941326 | Hyper | OTP |
| chr5 | 77148498 | 77148712 | Hyper | | chr5 | 77147563 | 77148195 | Hyper | |
| chr5 | 77806057 | 77806128 | Hyper | LHFPL2 | chr5 | 77268367 | 77269309 | Hyper | |
| chr5 | 78408192 | 78408461 | Hyper | BHMT | chr5 | 78407651 | 78407840 | Hyper | BHMT |
| chr5 | 79866062 | 79866414 | Hyper | | chr5 | 79864898 | 79865078 | Hyper | ANKRD34B |
| chr5 | 80689543 | 80689735 | Hyper | ACOT12 | chr5 | 80255816 | 80256074 | Hyper | RASGRF2 |
| chr5 | 82767429 | 82767793 | Hyper | VCAN | chr5 | 80690118 | 80690148 | Hyper | ACOT12 |
| chr5 | 83679681 | 83679921 | Hyper | | chr5 | 83679195 | 83679225 | Hyper | |
| chr5 | 83680615 | 83680708 | Hyper | | chr5 | 83680165 | 83680340 | Hyper | |
| chr5 | 87956199 | 87956964 | Hyper | LINC00461, MIR9-2 | chr5 | 87955460 | 87955797 | Hyper | MIR9-2, LINC00461 |
| chr5 | 87963390 | 87963511 | Hyper | MIR9-2, LINC00461 | chr5 | 87962966 | 87963002 | Hyper | MIR9-2, LINC00461 |
| chr5 | 87968486 | 87968858 | Hyper | MIR 9-2, LINC00461 | chr5 | 87967773 | 87968077 | Hyper | MIR9-2, LINC00461 |
| chr5 | 87974104 | 87974307 | Hyper | | chr5 | 87970193 | 87970872 | Hyper | MIR9-2, LINC00461 |
| chr5 | 87979756 | 87979912 | Hyper | | chr5 | 87974868 | 87975023 | Hyper | |
| chr5 | 87980954 | 87981325 | Hyper | | chr5 | 87980142 | 87980250 | Hyper | |
| chr5 | 87985922 | 87985954 | Hyper | | chr5 | 87984532 | 87984657 | Hyper | |
| chr5 | 87988516 | 87988584 | Hyper | | chr5 | 87986210 | 87986281 | Hyper | |
| chr5 | 88185470 | 88185868 | Hyper | AL050132 | chr5 | 87990408 | 87990452 | Hyper | |
| chr5 | 92939916 | 92940136 | Hyper | | chr5 | 89854856 | 89854902 | Hyper | GPR98 |
| chr5 | 94956935 | 94957000 | Hyper | GPR150 | chr5 | 94955681 | 94955919 | Hyper | GPR150 |
| chr5 | 95768920 | 95769093 | Hyper | PCSK1 | chr5 | 95767894 | 95768384 | Hyper | PCSK1 |
| chr5 | 100238882 | 100239151 | Hyper | ST8SIA4 | chr5 | 100236682 | 100236757 | Hyper | ST8SIA4 |
| chr5 | 112629427 | 112629674 | Hyper | MCC | chr5 | 101631487 | 101631533 | Hyper | SLCO4C1 |
| chr5 | 113391801 | 113392018 | Hyper | | chr5 | 113391532 | 113391565 | Hyper | |
| chr5 | 113699008 | 113699119 | Hyper | KCNN2 | chr5 | 113698567 | 113698783 | Hyper | KCNN2 |
| chr5 | 115151267 | 115152638 | Hyper | CDO1 | chr5 | 114514960 | 114515671 | Hyper | TRIM36 |
| chr5 | 115297928 | 115298042 | Hyper | AX747550, AQPEP | chr5 | 115297192 | 115297556 | Hyper | AQPEP, AX747550 |
| chr5 | 115298985 | 115299041 | Hyper | AQPEP, AX747550 | chr5 | 115298686 | 115298741 | Hyper | AQPEP, AX747550 |
| chr5 | 119801299 | 119801445 | Hyper | PRR16 | chr5 | 119799931 | 119799986 | Hyper | PRR16 |
| chr5 | 122422616 | 122422651 | Hyper | PRDM6 | chr5 | 122422240 | 122422292 | Hyper | PRDM6 |
| chr5 | 122425128 | 122425168 | Hyper | PRDM6 | chr5 | 122423328 | 122423376 | Hyper | PRDM6 |
| chr5 | 126626514 | 126626738 | Hyper | MEGF10 | chr5 | 122431118 | 122431378 | Hyper | PRDM6 |
| chr5 | 127873281 | 127873710 | Hyper | FBN2 | chr5 | 127872942 | 127872990 | Hyper | FBN2 |
| chr5 | 128300680 | 128300794 | Hyper | SLC27A6 | chr5 | 127874782 | 127874829 | Hyper | FBN2 |
| chr5 | 128796867 | 128796985 | Hyper | ADAMTS19 | chr5 | 128796081 | 128796244 | Hyper | ADAMTS19 |
| chr5 | 131992096 | 131992157 | Hyper | IL13, BC042122 | chr5 | 128797344 | 128797386 | Hyper | ADAMTS19 |
| chr5 | 134364195 | 134364513 | Hyper | LOC100996485, PITX1 | chr5 | 132947734 | 132947836 | Hyper | |
| chr5 | 134367108 | 134367203 | Hyper | PITX1, LOC100996485 | chr5 | 134366718 | 134366788 | Hyper | LOC100996485, PITX1 |
| chr5 | 134376222 | 134376375 | Hyper | LOC100996485, PITX1 | chr5 | 134374447 | 134375210 | Hyper | LOC100996485, PITX1 |
| chr5 | 134385952 | 134386383 | Hyper | LOC100996485 | chr5 | 134376697 | 134376824 | Hyper | LOC100996485, PITX1 |
| chr5 | 134825889 | 134826006 | Hyper | | chr5 | 134825463 | 134825518 | Hyper | |
| chr5 | 134870780 | 134871196 | Hyper | NEUROG1 | chr5 | 134870446 | 134870515 | Hyper | NEUROG1 |
| chr5 | 134879478 | 134880501 | Hyper | NEUROG1 | chr5 | 134871601 | 134872049 | Hyper | NEUROG1 |
| chr5 | 135266114 | 135266672 | Hyper | FBXL21 | chr5 | 135265737 | 135265767 | Hyper | FBXL21 |
| chr5 | 136834050 | 136834406 | Hyper | SPOCK1 | chr5 | 135528201 | 135528233 | Hyper | LOC389332, SMAD5 |
| chr5 | 137225092 | 137225129 | Hyper | MYOT, PKD2L2 | chr5 | 136834720 | 136834826 | Hyper | SPOCK1 |
| chr5 | 139525728 | 139525758 | Hyper | | chr5 | 139227773 | 139227909 | Hyper | NRG2, PSD2 |
| chr5 | 140187094 | 140187146 | Hyper | PCDHA4, PCDHA3, PCDHA2 | chr5 | 140174798 | 140174901 | Hyper | PCDHA1, PCDHA3, PCDHA2 |
| chr5 | 140306321 | 140306733 | Hyper | PCDHAC1, PCDHA13 | chr5 | 140305978 | 140306050 | Hyper | PCDHAC1, PCDHA13 |
| chr5 | 140514891 | 140514921 | Hyper | PCDHB4, PCDHB5 | chr5 | 140346595 | 140346671 | Hyper | PCDHAC2 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr5 | 140613926 | 140614014 | Hyper | PCDHB 19P, PCDHB14, PCDHB18 | chr5 | 140604459 | 140604501 | Hyper | PCDHB18, PCDHB14, PCDHB13 |
| chr5 | 140777328 | 140777487 | Hyper | PCDHGB5, PCDHGA9, PCDHGA8, PCDHGB4, PCDHGA7 | chr5 | 140614314 | 140614383 | Hyper | PCDHB19P, PCDHB18, PCDHB14 |
| chr5 | 140800479 | 140801246 | Hyper | PCDHGA10, PCDHGB6, PCDHGA11, PCDHGB8P, PCDHGA12, PCDHGB7 | chr5 | 140797076 | 140797342 | Hyper | PCDHGA10, PCDHGB6, PCDHGA9, PCDHGB7, PCDHGA11, PCDHGB8P |
| chr5 | 141263035 | 141263065 | Hyper | BC127870, PCDH1 | chr5 | 140855598 | 140856622 | Hyper | PCDHGC4, PCDHGC3 |
| chr5 | 145713645 | 145713896 | Hyper | POU4F3 | chr5 | 141931340 | 141931539 | Hyper | |
| chr5 | 145718802 | 145719925 | Hyper | POU4F3 | chr5 | 145717175 | 145717437 | Hyper | POU4F3 |
| chr5 | 145722116 | 145723027 | Hyper | POU4F3 | chr5 | 145720812 | 145720917 | Hyper | POU4F3 |
| chr5 | 145725212 | 145725844 | Hyper | POU4F3 | chr5 | 145724502 | 145724698 | Hyper | POU4F3 |
| chr5 | 146889220 | 146889575 | Hyper | DPYSL3 | chr5 | 146257499 | 146257582 | Hyper | PPP2R2B |
| chr5 | 150051101 | 150051667 | Hyper | MYOZ3 | chr5 | 149682074 | 149682166 | Hyper | ARS1 |
| chr5 | 151066442 | 151066474 | Hyper | BC039364, SPARC | chr5 | 150400123 | 150400203 | Hyper | TNIP1, GPX3 |
| chr5 | 153852664 | 153852792 | Hyper | HAND1 | chr5 | 151304371 | 151304401 | Hyper | |
| chr5 | 153854330 | 153854360 | Hyper | HAND1 | chr5 | 153853420 | 153853478 | Hyper | HAND1 |
| chr5 | 153855591 | 153855839 | Hyper | HAND1 | chr5 | 153855175 | 153855264 | Hyper | HAND1 |
| chr5 | 153856936 | 153855996 | Hyper | HAND1 | chr5 | 153856090 | 153856396 | Hyper | HAND1 |
| chr5 | 153858319 | 153858599 | Hyper | HAND1 | chr5 | 153857379 | 153857429 | Hyper | HAND1 |
| chr5 | 153862037 | 153862577 | Hyper | HAND1 | chr5 | 153859676 | 153859708 | Hyper | HAND1 |
| chr5 | 155107794 | 155107848 | Hyper | | chr5 | 153863421 | 153863451 | Hyper | HAND1 |
| chr5 | 155108733 | 155108763 | Hyper | | chr5 | 155108097 | 155108526 | Hyper | |
| chr5 | 157098362 | 157098571 | Hyper | C5orf52 | chr5 | 157001739 | 157001843 | Hyper | ADAM19 |
| chr5 | 158524692 | 158524748 | Hyper | AK123543, EBF1 | chr5 | 158478483 | 158478764 | Hyper | EBF1 |
| chr5 | 159399095 | 159399233 | Hyper | TRNA_Leu, ADRA1B | chr5 | 158527576 | 158528069 | Hyper | AK123543, EBF1 |
| chr5 | 161274310 | 161274405 | Hyper | GABRA1 | chr5 | 160975724 | 160975754 | Hyper | GABRB2 |
| chr5 | 168727924 | 168727988 | Hyper | | chr5 | 167956177 | 167956366 | Hyper | FBLL1, RARS |
| chr5 | 17010828 | 170108372 | Hyper | KCNIP1 | chr5 | 169064327 | 169064805 | Hyper | DOCK2 |
| chr5 | 170735518 | 170735788 | Hyper | TLX3, AX746723, RANBP17 | chr5 | 170735154 | 170735206 | Hyper | TLX3, AX746723, RANBP17 |
| chr5 | 170737741 | 170739481 | Hyper | TLX3, AX746723 | chr5 | 170736116 | 170737479 | Hyper | TLX3, AX746723, RANBP17 |
| chr5 | 170740461 | 170741240 | Hyper | TLX3, AX746723 | chr5 | 170739823 | 170740027 | Hyper | TLX3, AX746723 |
| chr5 | 170744375 | 170744562 | Hyper | TLX3, AX746723 | chr5 | 170741465 | 170744128 | Hyper | TLX3, AX746723 |
| chr5 | 17265587 | 172656215 | Hyper | NKX2-5 | chr5 | 170745389 | 170745480 | Hyper | TLX3, AX746723 |
| chr5 | 172659496 | 172659655 | Hyper | NKX2-5 | chr5 | 172659225 | 172659290 | Hyper | NKX2-5 |
| chr5 | 172660719 | 172661684 | Hyper | NKX2-5 | chr5 | 172659855 | 172660218 | Hyper | NKX2-5 |
| chr5 | 172665590 | 172665812 | Hyper | NKX2-5 | chr5 | 172664226 | 172664487 | Hyper | NKX2-5 |
| chr5 | 172671345 | 172671483 | Hyper | NKX2-5 | chr5 | 172670983 | 172671018 | Hyper | NKX2-5 |
| chr5 | 172754580 | 172754621 | Hyper | STC2 | chr5 | 172671783 | 172671968 | Hyper | NKX2-5 |
| chr5 | 172755470 | 172755663 | Hyper | STC2 | chr5 | 172754832 | 172754931 | Hyper | STC2 |
| chr5 | 17411538 | 174115861 | Hyper | | chr5 | 172757048 | 172757111 | Hyper | STC2 |
| chr5 | 174150415 | 174150445 | Hyper | MSX2 | chr5 | 174147523 | 174147596 | Hyper | MSX2 |
| chr5 | 174162874 | 174162904 | Hyper | MSX2 | chr5 | 174158808 | 174159588 | Hyper | MSX2 |
| chr5 | 174871174 | 174871497 | Hyper | DRD1 | chr5 | 174870738 | 174870786 | Hyper | DRD1 |
| chr5 | 175085476 | 175085719 | Hyper | HRH2 | chr5 | 175085147 | 175085209 | Hyper | HRH2 |
| chr5 | 175224016 | 175224271 | Hyper | CPLX2 | chr5 | 175223671 | 175223709 | Hyper | CPLX2 |
| chr5 | 175300351 | 175300381 | Hyper | Hfb1, CPLX2 | chr5 | 175299294 | 175299396 | Hyper | CPLX2 |
| chr5 | 175792957 | 175793031 | Hyper | ARL10, KIAA1191 | chr5 | 175621390 | 175621501 | Hyper | |
| chr5 | 176046363 | 176046554 | Hyper | SNCB, MIR4281 | chr5 | 176023916 | 176024318 | Hyper | GPRIN1, CDHR2 |
| chr5 | 176236721 | 176236898 | Hyper | UNC5A | chr5 | 176107274 | 176107586 | Hyper | |
| chr5 | 17741163 | 177412141 | Hyper | PROP1 | chr5 | 176264805 | 176264915 | Hyper | UNC5A |
| chr5 | 178004325 | 178004374 | Hyper | | chr5 | 178003708 | 178003848 | Hyper | |
| chr5 | 178017482 | 178017867 | Hyper | | chr5 | 178016575 | 178017217 | Hyper | |
| chr5 | 178421474 | 178421504 | Hyper | GRM6 | chr5 | 178368074 | 178368383 | Hyper | ZNF454, ZFP2 |
| chr5 | 178487107 | 178487300 | Hyper | ZNF354C | chr5 | 178421766 | 178421930 | Hyper | GRM6 |
| chr5 | 178772205 | 178772272 | Hyper | ADAMTS2 | chr5 | 178771588 | 178771955 | Hyper | ADAMTS2 |
| chr5 | 178957637 | 178957913 | Hyper | AX747985 | chr5 | 178772603 | 178772745 | Hyper | ADAMTS2 |
| chr5 | 179780104 | 179780144 | Hyper | GFPT2 | chr5 | 179243984 | 179244277 | Hyper | SQSTM1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr5 | 179867486 | 179867548 | Hyper | | chr5 | 179780706 | 179780985 | Hyper | GFPT2 |
| chr5 | 180017721 | 180017933 | Hyper | SCGB3A1 | chr5 | 180017118 | 180017198 | Hyper | SCGB3A1 |
| chr5 | 180075846 | 180076317 | Hyper | FLT4 | chr5 | 180018311 | 180018498 | Hyper | SCGB3A1 |
| chr5 | 180076804 | 180076846 | Hyper | FLT4 | chr5 | 180076567 | 180076602 | Hyper | FLT4 |
| chr5 | 180527719 | 180527766 | Hyper | TRNA_Val, TRNA_Leu | chr5 | 180100915 | 180101332 | Hyper | DQ589679 |
| chr7 | 329805 | 329838 | Hyper | LOC100288524 | chr5 | 180600858 | 180601218 | Hyper | TRNA_Leu, TRNA_Val, TRNA_Pseudo |
| chr7 | 752120 | 752221 | Hyper | | chr7 | 751842 | 751874 | Hyper | |
| chr7 | 1268318 | 1268366 | Hyper | UNCX | chr7 | 1263761 | 1263960 | Hyper | UNCX |
| chr7 | 1270406 | 1270440 | Hyper | UNCX | chr7 | 1269305 | 1269808 | Hyper | UNCX |
| chr7 | 1274641 | 1274677 | Hyper | UNCX | chr7 | 1273167 | 1273330 | Hyper | UNCX |
| chr7 | 1275579 | 1275680 | Hyper | UNCX | chr7 | 1275008 | 1275038 | Hyper | UNCX |
| chr7 | 1279099 | 1279129 | Hyper | UNCX | chr7 | 1277817 | 1277865 | Hyper | UNCX |
| chr7 | 1281131 | 1281232 | Hyper | UNCX | chr7 | 1279965 | 1279995 | Hyper | UNCX |
| chr7 | 1282042 | 1282150 | Hyper | UNCX | chr7 | 1281493 | 1281555 | Hyper | UNCX |
| chr7 | 1286244 | 1286338 | Hyper | UNCX | chr7 | 1282506 | 1282644 | Hyper | UNCX |
| chr7 | 1288582 | 1288753 | Hyper | | chr7 | 1286810 | 1286858 | Hyper | |
| chr7 | 2728085 | 2728165 | Hyper | AMZ1 | chr7 | 1709138 | 1709235 | Hyper | |
| chr7 | 4923072 | 4923331 | Hyper | MMD2 | chr7 | 3341489 | 3341597 | Hyper | SDK1 |
| chr7 | 4998698 | 4998736 | Hyper | MMD2 | chr7 | 4998201 | 4998388 | Hyper | MMD2 |
| chr7 | 8473070 | 8473674 | Hyper | NXPH1 | chr7 | 6703555 | 6703959 | Hyper | AK123300 |
| chr7 | 8474814 | 8475057 | Hyper | NXPH1 | chr7 | 8473956 | 8474562 | Hyper | NXPH1 |
| chr7 | 8481642 | 8481833 | Hyper | NXPH1 | chr7 | 8480640 | 8481159 | Hyper | NXPH1 |
| chr7 | 8483147 | 8483950 | Hyper | NXPH1 | chr7 | 8482056 | 8482921 | Hyper | NXPH1 |
| chr7 | 12443317 | 12443403 | Hyper | VWDE | chr7 | 12151440 | 12151678 | Hyper | |
| chr7 | 15725983 | 15726081 | Hyper | BX538274, MEOX2 | chr7 | 12443841 | 12443871 | Hyper | VWDE |
| chr7 | 15727290 | 15727320 | Hyper | BX538274, MEOX2 | chr7 | 15726686 | 15727077 | Hyper | BX538274, MEOX2 |
| chr7 | 19146502 | 19146558 | Hyper | TWIST1 | chr7 | 19145808 | 19146249 | Hyper | TWIST1 |
| chr7 | 19152191 | 19152291 | Hyper | TWIST1 | chr7 | 19147122 | 19147798 | Hyper | TWIST1 |
| chr7 | 19157144 | 19157935 | Hyper | TWIST1 | chr7 | 19156070 | 19156828 | Hyper | TWIST1 |
| chr7 | 20816252 | 20816447 | Hyper | SP8 | chr7 | 19184058 | 19184255 | Hyper | FERD3L, BC043576 |
| chr7 | 20818130 | 20818362 | Hyper | SP8 | chr7 | 20817380 | 20817410 | Hyper | SP8 |
| chr7 | 20823904 | 20824784 | Hyper | SP8 | chr7 | 20823292 | 20823432 | Hyper | SP8 |
| chr7 | 20833167 | 20833322 | Hyper | SP8 | chr7 | 20830670 | 20830700 | Hyper | SP8 |
| chr7 | 21583263 | 21583326 | Hyper | DNAH11 | chr7 | 21582593 | 21582868 | Hyper | DNAH11 |
| chr7 | 22589356 | 22589870 | Hyper | | chr7 | 22539833 | 22539909 | Hyper | STEAP1B |
| chr7 | 24796478 | 24796536 | Hyper | DFNA5 | chr7 | 23287253 | 23287624 | Hyper | GPNMB |
| chr7 | 25896521 | 25896864 | Hyper | | chr7 | 25892510 | 25892588 | Hyper | |
| chr7 | 27135327 | 27135786 | Hyper | HOXA1, HOTAIRM1, HOXA2, AK291164 | chr7 | 27127863 | 27127898 | Hyper | HOXA1, HOTAIRM1 |
| chr7 | 27187535 | 27187570 | Hyper | HOXA6, HOXA5, HOXA7, DQ655986, HOXA-AS3 | chr7 | 27136013 | 27136790 | Hyper | HOTAIRM1, HOXA1, HOXA2, AK291164, HOXA3 |
| chr7 | 27192061 | 27192098 | Hyper | HOXA5, HOXA7, HOXA9, HOXA10-HOXA9, DQ655986, HOXA-AS3, HOXA6 | chr7 | 27190591 | 27191154 | Hyper | HOXA-AS3, HOXA6, HOXA5, HOXA7, DQ655986 |
| chr7 | 27204487 | 27205395 | Hyper | HOXA-AS4, MIR196B, HOXA10, HOXA10-HOXA9, HOXA9, HOXA7 | chr7 | 27195462 | 27196580 | Hyper | HOXA9, HOXA10-HOXA9, HOXA7, DQ655986, HOXA-AS3, HOXA6 |
| chr7 | 27212499 | 27212899 | Hyper | HOXA-AS4, HOXA10-HOXA9, HOXA9, HOXA11, HOXA10, MIR196B | chr7 | 27205678 | 27206058 | Hyper | HOXA7, HOXA-AS4, MIR196B, HOXA10, HOXA10-HOXA9, HOXA9 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr7 | 27223114 | 27223151 | Hyper | HOXA11-AS, LOC402470, HOXA11, HOXA10 | chr7 | 27213172 | 27214310 | Hyper | HOXA9, HOXA11, HOXA10, MIR196B, HOXA-AS4, HOXA10-HOXA9 |
| chr7 | 27224069 | 27224609 | Hyper | HOXA10, HOXA11-AS, LOC402470, HOXA11 | chr7 | 27223601 | 27223696 | Hyper | LOC402470, HOXA11, HOXA10, HOXA11-AS |
| chr7 | 27227874 | 27227953 | Hyper | HOXA13, LOC402470, HOXA11-AS, HOXA11, HOXA10 | chr7 | 27225035 | 27225092 | Hyper | LOC402470, HOXA11-AS, HOXA11, HOXA10 |
| chr7 | 27238887 | 27238917 | Hyper | HOTTIP, HOXA13, LOC402470, HOXA11-AS | chr7 | 27232289 | 27232962 | Hyper | HOXA13, HOTTIP, LOC402470, HOXA11-AS, HOXA11 |
| chr7 | 27240230 | 27240381 | Hyper | HOTTIP, HOXA13 | chr7 | 27239177 | 27239234 | Hyper | HOTTIP, HOXA13 |
| chr7 | 27252380 | 27252410 | Hyper | HOTTIP | chr7 | 27244515 | 27245310 | Hyper | HOTTIP, HOXA13 |
| chr7 | 27265538 | 27265584 | Hyper | | chr7 | 27264875 | 27265325 | Hyper | |
| chr7 | 27282089 | 27283013 | Hyper | EVX1 | chr7 | 27279115 | 27279453 | Hyper | EVX1 |
| chr7 | 27285522 | 27285967 | Hyper | EVX1 | chr7 | 27283351 | 27283627 | Hyper | EVX1 |
| chr7 | 27291143 | 27291851 | Hyper | EVX1 | chr7 | 27288946 | 27289449 | Hyper | EVX1 |
| chr7 | 28996457 | 28996487 | Hyper | DQ601810, TRIL | chr7 | 28449331 | 28449682 | Hyper | CREB5, BC087859 |
| chr7 | 28997193 | 28997367 | Hyper | TRIL, DQ601810 | chr7 | 28996840 | 28996879 | Hyper | DQ601810, TRIL |
| chr7 | 28998053 | 28998110 | Hyper | DQ601810, TRIL | chr7 | 28997584 | 28997625 | Hyper | DQ601810, TRIL |
| chr7 | 30722290 | 30722375 | Hyper | CRHR2 | chr7 | 30721280 | 30721835 | Hyper | CRHR2 |
| chr7 | 31375965 | 31376135 | Hyper | NEUROD6 | chr7 | 31093003 | 31093133 | Hyper | ADCYAP1R1 |
| chr7 | 32337807 | 32337837 | Hyper | | chr7 | 32110698 | 32110772 | Hyper | |
| chr7 | 32338900 | 32338930 | Hyper | | chr7 | 32338088 | 32338410 | Hyper | |
| chr7 | 33943459 | 33943759 | Hyper | BMPER | chr7 | 32467461 | 32468062 | Hyper | |
| chr7 | 35226193 | 35226464 | Hyper | | chr7 | 35225809 | 35225876 | Hyper | |
| chr7 | 35293654 | 35294141 | Hyper | TBX20 | chr7 | 35292970 | 35293293 | Hyper | TBX20 |
| chr7 | 35295104 | 35295134 | Hyper | TBX20 | chr7 | 35294502 | 35294536 | Hyper | TBX20 |
| chr7 | 35296935 | 35298032 | Hyper | TBX20 | chr7 | 35295908 | 35295944 | Hyper | TBX20 |
| chr7 | 35301317 | 3530194 | Hyper | TBX20 | chr7 | 35300951 | 35301088 | Hyper | TBX20 |
| chr7 | 37487164 | 37487826 | Hyper | | chr7 | 35494353 | 35494440 | Hyper | |
| chr7 | 37488920 | 37488992 | Hyper | | chr7 | 37488257 | 37488857 | Hyper | |
| chr7 | 37956271 | 37956439 | Hyper | EPDR1, SFRP4 | chr7 | 37955878 | 37955979 | Hyper | EPDR1, SFRP4 |
| chr7 | 38670357 | 38671001 | Hyper | | chr7 | 37960301 | 37960335 | Hyper | EPDR1, SFRP4 |
| chr7 | 42267647 | 42267677 | Hyper | GLI3 | chr7 | 39015542 | 39015981 | Hyper | POU6F2, AK023033 |
| chr7 | 43152109 | 43152700 | Hyper | HECW1, AX748020 | chr7 | 42276346 | 42276634 | Hyper | GLI3 |
| chr7 | 45613785 | 45613898 | Hyper | ADCY1 | chr7 | 43152957 | 43152987 | Hyper | HECW1, AX748020 |
| chr7 | 45614738 | 45614809 | Hyper | ADCY1 | chr7 | 45614341 | 45614474 | Hyper | ADCY1 |
| chr7 | 45960743 | 45960794 | Hyper | IGFBP3 | chr7 | 45615440 | 45615495 | Hyper | ADCY1 |
| chr7 | 45961508 | 45961576 | Hyper | IGFBP3 | chr7 | 45961146 | 45961176 | Hyper | IGFBP3 |
| chr7 | 49812820 | 49813994 | Hyper | VWC2 | chr7 | 45961833 | 45961888 | Hyper | IGFBP3 |
| chr7 | 49815101 | 49815765 | Hyper | VWC2 | chr7 | 49814531 | 49814738 | Hyper | VWC2 |
| chr7 | 50343698 | 50343994 | Hyper | IKZF1 | chr7 | 50343263 | 50343401 | Hyper | IKZF1 |
| chr7 | 52156231 | 52156261 | Hyper | | chr7 | 50344226 | 50344491 | Hyper | IKZF1 |
| chr7 | 54612418 | 54612730 | Hyper | VSTM2A | chr7 | 54609852 | 54610153 | Hyper | VSTM2A |
| chr7 | 64349331 | 64349470 | Hyper | ZNF273, AK097702 | chr7 | 64349026 | 64349056 | Hyper | ZNF273, AK097702 |
| chr7 | 64712422 | 64712510 | Hyper | | chr7 | 64700283 | 64700329 | Hyper | |
| chr7 | 65037609 | 65037664 | Hyper | | chr7 | 64974382 | 64974422 | Hyper | |
| chr7 | 65878743 | 65878793 | Hyper | | chr7 | 65508995 | 65509043 | Hyper | |
| chr7 | 70596942 | 70597079 | Hyper | WBSCR17 | chr7 | 70596436 | 70596688 | Hyper | WBSCR17 |
| chr7 | 70597835 | 70598387 | Hyper | WBSCR17 | chr7 | 70597406 | 70597451 | Hyper | WBSCR17 |
| chr7 | 71800676 | 71801359 | Hyper | | chr7 | 71217108 | 71217332 | Hyper | |
| chr7 | 71802410 | 71802637 | Hyper | | chr7 | 71801632 | 71801899 | Hyper | |
| chr7 | 79083093 | 79083177 | Hyper | MAGI2-AS3 | chr7 | 79082167 | 79082218 | Hyper | MAGI2-AS3 |
| chr7 | 82072350 | 82072503 | Hyper | | chr7 | 79083392 | 79083834 | Hyper | MAGI2-AS3 |
| chr7 | 86273208 | 86273541 | Hyper | GRM3 | chr7 | 84815744 | 84815788 | Hyper | SEMA3D |
| chr7 | 87229658 | 87230433 | Hyper | ABCB1 | chr7 | 86274117 | 86274457 | Hyper | GRM3 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr7 | 88387982 | 88388183 | Hyper | ZNF804B | chr7 | 87257012 | 87257047 | Hyper | RUNDC3B, ABCB1 |
| chr7 | 89747996 | 89748340 | Hyper | DPY19L2P4 | chr7 | 88388879 | 88389219 | Hyper | ZNF804B |
| chr7 | 93203708 | 93203756 | Hyper | | chr7 | 89950183 | 89950810 | Hyper | C7orf63 |
| chr7 | 93551323 | 93551425 | Hyper | GNG11 | chr7 | 93519351 | 93520137 | Hyper | TFPI2 |
| chr7 | 96619560 | 96619603 | Hyper | DLX6-AS1 | chr7 | 94284302 | 94284873 | Hyper | PEG10, SGCE |
| chr7 | 96622107 | 96622349 | Hyper | DLX6-AS1 | chr7 | 96621715 | 96621811 | Hyper | DLX6-AS1 |
| chr7 | 96625998 | 96626051 | Hyper | DLX6, DLX6-AS1 | chr7 | 96625537 | 96625720 | Hyper | DLX6, DLX6-AS1 |
| chr7 | 96635846 | 96636645 | Hyper | DLX6, DLX6-AS1 | chr7 | 96635345 | 96635473 | Hyper | DLX6, DLX6-AS1 |
| chr7 | 96646662 | 96647131 | Hyper | DLX6-AS1, DLX5, DLX6 | chr7 | 96639318 | 96639348 | Hyper | DLX6-AS1, DLX6 |
| chr7 | 96650080 | 96650116 | Hyper | DLX6-AS1, DLX5, DLX6 | chr7 | 96647809 | 96648219 | Hyper | DLX6, DLX6-AS1, DLX5 |
| chr7 | 96651472 | 96651502 | Hyper | DLX5 | chr7 | 96650884 | 96651151 | Hyper | DLX5 |
| chr7 | 96653507 | 96653993 | Hyper | DLX5 | chr7 | 96652144 | 96652174 | Hyper | DLX5 |
| chr7 | 97362292 | 97362607 | Hyper | TAC1 | chr7 | 97361098 | 97361781 | Hyper | TAC1 |
| chr7 | 98247126 | 98247656 | Hyper | NPTX2 | chr7 | 98245885 | 9824686 | Hyper | NPTX2 |
| chr7 | 99595194 | 99595337 | Hyper | | chr7 | 99177742 | 99177870 | Hyper | ZNF655 |
| chr7 | 100318505 | 100318575 | Hyper | EPO | chr7 | 100091210 | 100091252 | Hyper | NYAP1 |
| chr7 | 100823436 | 100823497 | Hyper | NAT16 | chr7 | 100547037 | 100547073 | Hyper | MUC3A, MUC3B |
| chr7 | 103085876 | 103086117 | Hyper | | chr7 | 101005968 | 101005998 | Hyper | COL26A1 |
| chr7 | 103630739 | 103630824 | Hyper | | chr7 | 103629059 | 103630125 | Hyper | |
| chr7 | 103969694 | 103969794 | Hyper | JB175200, LHFPL3 | chr7 | 103969217 | 103969341 | Hyper | LHFPL3, JB175200 |
| chr7 | 108095329 | 108095362 | Hyper | NRCAM | chr7 | 107301494 | 107301640 | Hyper | SLC26A4, SLC26A4-AS1 |
| chr7 | 112726558 | 112726614 | Hyper | GPR85 | chr7 | 108097397 | 108097450 | Hyper | NRCAM |
| chr7 | 113724956 | 113725081 | Hyper | FOXP2 | chr7 | 113722810 | 113723439 | Hyper | FOXP2 |
| chr7 | 113727722 | 113727781 | Hyper | FOXP2 | chr7 | 113727442 | 113727486 | Hyper | FOXP2 |
| chr7 | 116962893 | 116963476 | Hyper | WNT2 | chr7 | 115117552 | 115117647 | Hyper | |
| chr7 | 120969672 | 120969800 | Hyper | WNT16 | chr7 | 117119448 | 117120271 | Hyper | CFTR |
| chr7 | 121940935 | 121941052 | Hyper | FEZF1, FEZF1-AS1 | chr7 | 121939677 | 121940448 | Hyper | FEZF1, FEZF1-AS1 |
| chr7 | 121944001 | 121944166 | Hyper | FEZF1-AS1, FEZF1 | chr7 | 121941881 | 121942170 | Hyper | FEZF1-AS1, FEZF1 |
| chr7 | 121950137 | 121951069 | Hyper | CADPS2, FEZF1-AS1, FEZF1 | chr7 | 121946478 | 121947406 | Hyper | FEZF1-AS1, FEZF1 |
| chr7 | 121956486 | 121956567 | Hyper | FEZF1-AS1, CADPS2 | chr7 | 121951877 | 121952169 | Hyper | FEZF1, CADPS2, FEZF1-AS1 |
| chr7 | 123173150 | 123173244 | Hyper | NDUFA5, IQUB | chr7 | 121956830 | 121957331 | Hyper | CADPS2, FEZF1-AS1 |
| chr7 | 124404415 | 124404522 | Hyper | GPR37 | chr7 | 123672048 | 123672086 | Hyper | EU233817, TMEM229A, L13779, BC041947 |
| chr7 | 126891504 | 126891593 | Hyper | | chr7 | 126891220 | 126891250 | Hyper | |
| chr7 | 127806634 | 127806664 | Hyper | | chr7 | 127744122 | 127744631 | Hyper | |
| chr7 | 127841505 | 127841704 | Hyper | MIR129-1 | chr7 | 127808047 | 127808792 | Hyper | |
| chr7 | 128337467 | 128337921 | Hyper | | chr7 | 127991826 | 127992135 | Hyper | PRRT4, RBM28 |
| chr7 | 128828195 | 128828272 | Hyper | SMO | chr7 | 128470897 | 128471032 | Hyper | FLNC, CCDC136 |
| chr7 | 129422160 | 129423418 | Hyper | MIR183, MIR96 | chr7 | 129418271 | 129418428 | Hyper | MIR183, MIR96, MIR182 |
| chr7 | 129424655 | 129425887 | Hyper | MIR183 | chr7 | 129423834 | 129424034 | Hyper | MIR183, MIR96 |
| chr7 | 131242738 | 131242824 | Hyper | PODXL | chr7 | 129426195 | 129426236 | Hyper | |
| chr7 | 134143164 | 134143475 | Hyper | AKR1B1 | chr7 | 131514824 | 131514854 | Hyper | |
| chr7 | 136553311 | 136554366 | Hyper | CHRM2 | chr7 | 134143822 | 134144132 | Hyper | AKR1B1 |
| chr7 | 136555235 | 136555412 | Hyper | CHRM2 | chr7 | 136554638 | 136554966 | Hyper | CHRM2 |
| chr7 | 137028481 | 137028524 | Hyper | | chr7 | 136555681 | 136556091 | Hyper | CHRM2 |
| chr7 | 139167617 | 139167744 | Hyper | KLRG2 | chr7 | 137531265 | 137532337 | Hyper | DGKI |
| chr7 | 139208772 | 139208810 | Hyper | CLEC2L | chr7 | 139168042 | 139168379 | Hyper | KLRG2 |
| chr7 | 140773024 | 140773228 | Hyper | TMEM178B | chr7 | 140339934 | 140339962 | Hyper | DENND2A |
| chr7 | 145812992 | 145813082 | Hyper | CNTNAP2 | chr7 | 143579739 | 143580069 | Hyper | FAM115A |
| chr7 | 149112058 | 149112403 | Hyper | TRNA_Cys | chr7 | 145813891 | 145813947 | Hyper | CNTNAP2 |
| chr7 | 149744505 | 149744560 | Hyper | AL162052 | chr7 | 149119948 | 149120073 | Hyper | TRNA_Cys, ZNF777 |
| chr7 | 149918119 | 149918149 | Hyper | | chr7 | 149917286 | 149917336 | Hyper | |
| chr7 | 150748192 | 150748406 | Hyper | ABCB8, CDK5, SLC4A2, ASIC3 | chr7 | 150716169 | 150716305 | Hyper | ABCB8, ATG9B |
| chr7 | 151107486 | 151107651 | Hyper | WDR86-AS1, WDR86 | chr7 | 151106451 | 151107004 | Hyper | WDR86-AS1, WDR86 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr7 | 152623016 | 152623057 | Hyper | | chr7 | 152622621 | 152622697 | Hyper | |
| chr7 | 153584389 | 153584457 | Hyper | DPP6 | chr7 | 153583595 | 153584069 | Hyper | DPP6 |
| chr7 | 153585418 | 153585606 | Hyper | DPP6 | chr7 | 153584848 | 153585206 | Hyper | DPP6 |
| chr7 | 154862046 | 154862266 | Hyper | HTR5A, LOC100128264 | chr7 | 153749720 | 153750115 | Hyper | DPP6, AK127966 |
| chr7 | 155165875 | 155166784 | Hyper | BC150495 | chr7 | 155164454 | 155165562 | Hyper | BC150495 |
| chr7 | 155174656 | 155174788 | Hyper | BC150495 | chr7 | 155167034 | 155167909 | Hyper | BC150495 |
| chr7 | 155242729 | 155243102 | Hyper | EN2 | chr7 | 155241318 | 155242049 | Hyper | EN2 |
| chr7 | 155243825 | 155243895 | Hyper | EN2 | chr7 | 155243346 | 155243561 | Hyper | EN2 |
| chr7 | 155246886 | 155247584 | Hyper | EN2 | chr7 | 155244180 | 155244361 | Hyper | EN2 |
| chr7 | 155249512 | 155249565 | Hyper | EN2 | chr7 | 155248913 | 155248943 | Hyper | EN2 |
| chr7 | 155250283 | 155250355 | Hyper | EN2 | chr7 | 155249925 | 155250011 | Hyper | EN2 |
| chr7 | 155252247 | 155252490 | Hyper | EN2 | chr7 | 155250787 | 155250996 | Hyper | EN2 |
| chr7 | 155254848 | 155255324 | Hyper | EN2 | chr7 | 155252862 | 155253041 | Hyper | EN2 |
| chr7 | 155257040 | 155257189 | Hyper | EN2 | chr7 | 155256237 | 155256312 | Hyper | EN2 |
| chr7 | 155258949 | 155260137 | Hyper | EN2 | chr7 | 155258193 | 155258487 | Hyper | EN2 |
| chr7 | 155301838 | 155301931 | Hyper | CNPY1 | chr7 | 155260992 | 155261210 | Hyper | EN2 |
| chr7 | 155325796 | 155325872 | Hyper | CNPY1 | chr7 | 155302328 | 155303335 | Hyper | CNPY1 |
| chr7 | 155580165 | 155580211 | Hyper | RBM33 | chr7 | 155326169 | 155326527 | Hyper | CNPY1 |
| chr7 | 156409144 | 156409347 | Hyper | | chr7 | 155600629 | 155600723 | Hyper | SHH |
| chr7 | 156701846 | 156701908 | Hyper | | chr7 | 156409665 | 156409028 | Hyper | |
| chr7 | 156794443 | 156794485 | Hyper | LOC645249, MNX1 | chr7 | 156794153 | 156794235 | Hyper | MNX1, LOC645249 |
| chr7 | 156796534 | 156799467 | Hyper | MNX1, LOC645249 | chr7 | 156794998 | 156795914 | Hyper | MNX1, LOC645249 |
| chr7 | 156801403 | 156801601 | Hyper | LOC645249, MNX1 | chr7 | 156800999 | 156801029 | Hyper | LOC645249, MNX1 |
| chr7 | 156809983 | 156811436 | Hyper | LOC645249, MNX1 | chr7 | 156808858 | 156809199 | Hyper | LOC645249, MNX1 |
| chr7 | 156871168 | 156871297 | Hyper | | chr7 | 156812852 | 156815092 | Hyper | LOC645249, MNX1 |
| chr7 | 157476879 | 157477272 | Hyper | | chr7 | 157361605 | 157361635 | Hyper | PTPRN2, MIR153-2 |
| chr7 | 157481364 | 157481756 | Hyper | | chr7 | 157477473 | 157477914 | Hyper | |
| chr7 | 157482492 | 157482667 | Hyper | | chr7 | 157481969 | 157482168 | Hyper | |
| chr7 | 157484877 | 157485277 | Hyper | | chr7 | 157483325 | 157483538 | Hyper | |
| chr7 | 157485976 | 157486503 | Hyper | | chr7 | 157485527 | 157485705 | Hyper | |
| chr7 | 158937158 | 158937567 | Hyper | VIPR2 | chr7 | 158936492 | 158936880 | Hyper | VIPR2 |
| chr13 | 20875763 | 20875919 | Hyper | | chr7 | 158938210 | 158938399 | Hyper | VIPR2 |
| chr13 | 22243273 | 22243409 | Hyper | FGF9 | chr13 | 21649636 | 21649775 | Hyper | |
| chr13 | 23733447 | 23734020 | Hyper | | chr13 | 23489851 | 23489914 | Hyper | |
| chr13 | 24477643 | 24477906 | Hyper | ANKRD20A19P, C1QTNF9B | chr13 | 23734327 | 23734678 | Hyper | |
| chr13 | 25319856 | 25320093 | Hyper | | chr13 | 25115713 | 25115771 | Hyper | |
| chr13 | 25321699 | 25321942 | Hyper | | chr13 | 25320345 | 25321350 | Hyper | |
| chr13 | 25744716 | 25745910 | Hyper | BC022569, AMER2 | chr13 | 25621045 | 25621394 | Hyper | |
| chr13 | 25946620 | 25946796 | Hyper | ATP8A2 | chr13 | 25946283 | 25946315 | Hyper | ATP8A2 |
| chr13 | 26625343 | 26625727 | Hyper | SHISA2 | chr13 | 26042678 | 26043499 | Hyper | ATP8A2 |
| chr13 | 27334772 | 27334894 | Hyper | GPR12 | chr13 | 27334211 | 27334563 | Hyper | GPR12 |
| chr13 | 28366482 | 28366577 | Hyper | GSX1 | chr13 | 28365705 | 28366081 | Hyper | GSX1 |
| chr13 | 28367794 | 28368168 | Hyper | GSX1 | chr13 | 28367024 | 28367059 | Hyper | GSX1 |
| chr13 | 28368952 | 28369990 | Hyper | GSX1 | chr13 | 28368451 | 28368593 | Hyper | GSX1 |
| chr13 | 28394766 | 28394866 | Hyper | | chr13 | 28370947 | 28371061 | Hyper | GSX1 |
| chr13 | 28395998 | 28396073 | Hyper | | chr13 | 28395501 | 28395553 | Hyper | |
| chr13 | 28492244 | 28492553 | Hyper | PDX1 | chr13 | 28491793 | 28491946 | Hyper | PDX1 |
| chr13 | 28528534 | 28528748 | Hyper | CDX2, ATP5EP2 | chr13 | 28503042 | 28503074 | Hyper | PDX1 |
| chr13 | 28543212 | 28543242 | Hyper | PRHOXNB, CDX2 | chr13 | 28540745 | 28540927 | Hyper | CDX2 |
| chr13 | 28549497 | 28550552 | Hyper | CDX2, PRHOXNB | chr13 | 28544397 | 28544903 | Hyper | PRHOXNB, CDX2 |
| chr13 | 28551950 | 28552167 | Hyper | PRHOXNB, CDX2 | chr13 | 28551417 | 28551461 | Hyper | PRHOXNB, CDX2 |
| chr13 | 28552794 | 28552824 | Hyper | PRHOXNB, CDX2 | chr13 | 28552555 | 28552585 | Hyper | PRHOXNB, CDX2 |
| chr13 | 28674018 | 28674257 | Hyper | FLT3 | chr13 | 28553030 | 28553138 | Hyper | PRHOXNB, CDX2 |
| chr13 | 29067773 | 29068416 | Hyper | BC048278, FLT1 | chr13 | 28674578 | 28674656 | Hyper | FLT3 |
| chr13 | 29106308 | 29107134 | Hyper | | chr13 | 29068926 | 29069065 | Hyper | BC048278, FLT1 |
| chr13 | 33591300 | 33591419 | Hyper | KL | chr13 | 33590822 | 33590949 | Hyper | KL |
| chr13 | 36044829 | 36044930 | Hyper | NBEA, MIR548F5 | chr13 | 33924666 | 33924790 | Hyper | |
| chr13 | 36704939 | 36704994 | Hyper | | chr13 | 36045267 | 36045297 | Hyper | NBEA, MIR548F5 |
| chr13 | 36729093 | 36729125 | Hyper | | chr13 | 36705451 | 36705489 | Hyper | |
| chr13 | 36920669 | 36920699 | Hyper | SPG20OS, SPG20 | chr13 | 36920363 | 36920413 | Hyper | SPG20OS, SPG20 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr13 | 37005657 | 37006762 | Hyper | CCNA1 | chr13 | 37004771 | 37005129 | Hyper | CCNA1 |
| chr13 | 38443618 | 38443827 | Hyper | Mir_720, TRPC4 | chr13 | 37248979 | 37249030 | Hyper | SERTM1 |
| chr13 | 44947746 | 44948197 | Hyper | SERP2 | chr13 | 43566297 | 43566647 | Hyper | EPSTI1 |
| chr13 | 49794216 | 49795168 | Hyper | MLNR | chr13 | 46425548 | 46425584 | Hyper | SIAH3 |
| chr13 | 53419734 | 53419775 | Hyper | PCDH8 | chr13 | 53312991 | 53313029 | Hyper | LECT1 |
| chr13 | 53420492 | 53420720 | Hyper | PCDH8 | chr13 | 53420020 | 53420080 | Hyper | PCDH8 |
| chr13 | 53422315 | 53422362 | Hyper | PCDH8 | chr13 | 53421253 | 53421787 | Hyper | PCDH8 |
| chr13 | 58203602 | 58203644 | Hyper | PCDH17 | chr13 | 53423838 | 53423978 | Hyper | PCDH8 |
| chr13 | 58206042 | 58206983 | Hyper | PCDH17 | chr13 | 58203851 | 58204103 | Hyper | PCDH17 |
| chr13 | 58208495 | 58208926 | Hyper | PCDH17 | chr13 | 58207462 | 58208020 | Hyper | PCDH17 |
| chr13 | 67805191 | 67805247 | Hyper | PCDH9 | chr13 | 67803735 | 67803861 | Hyper | PCDH9 |
| chr13 | 72439142 | 72439250 | Hyper | DACH1 | chr13 | 70681626 | 70682071 | Hyper | ATXN8OS, KLHL1 |
| chr13 | 78493166 | 78493196 | Hyper | RNF219-AS1, EDNRB | chr13 | 78492810 | 78492840 | Hyper | RNF219-AS1, EDNRB |
| chr13 | 79169818 | 79170884 | Hyper | POU4F1, RNF219-AS1 | chr13 | 78493455 | 78493809 | Hyper | RNF219-AS1, EDNRB |
| chr13 | 79175770 | 79176783 | Hyper | POU4F1, RNF219-AS1 | chr13 | 79171118 | 79171196 | Hyper | POU4F1, RNF219-AS1 |
| chr13 | 79183406 | 79183485 | Hyper | RNF219, POU4F1 RNF219-AS1 | chr13 | 79176993 | 79177998 | Hyper | POU4F1, RNF219-AS1 |
| chr13 | 84455581 | 84455715 | Hyper | SLITRK1 | chr13 | 84455236 | 84455292 | Hyper | SLITRK1 |
| chr13 | 88323579 | 88323782 | Hyper | SLITRK5 | chr13 | 84457491 | 84457521 | Hyper | SLITRK1 |
| chr13 | 88325300 | 88325460 | Hyper | SLITRK5 | chr13 | 88324516 | 88324564 | Hyper | SLITRK5 |
| chr13 | 88326538 | 88327014 | Hyper | SLITRK5 | chr13 | 88325819 | 88326061 | Hyper | SLITRK5 |
| chr13 | 93879670 | 93879700 | Hyper | GPC6 | chr13 | 92051374 | 92051529 | Hyper | GPC5 |
| chr13 | 95357311 | 95357341 | Hyper | SOX21, AK055459 | chr13 | 93880089 | 93880718 | Hyper | GPC6 |
| chr13 | 95358041 | 95358165 | Hyper | SOX21, AK055459 | chr13 | 95357574 | 95357775 | Hyper | SOX21, AK055459 |
| chr13 | 95360322 | 95360371 | Hyper | AK055459, SOX21 | chr13 | 95359747 | 95359803 | Hyper | SOX21, AK055459 |
| chr13 | 95363894 | 95364196 | Hyper | AK055459, SOX21 | chr13 | 95363210 | 95363429 | Hyper | AK055459, SOX21 |
| chr13 | 95620021 | 95620078 | Hyper | | chr13 | 95364570 | 95364769 | Hyper | AK055459, SOX21 |
| chr13 | 96204895 | 96205363 | Hyper | CLDN10 | chr13 | 95620647 | 95620683 | Hyper | |
| chr13 | 96296981 | 96297137 | Hyper | | chr13 | 96296225 | 96296473 | Hyper | |
| chr13 | 100547868 | 100547911 | Hyper | | chr13 | 96743788 | 96744019 | Hyper | HS6ST3 |
| chr13 | 100621941 | 100622015 | Hyper | ZIC5 | chr13 | 100608257 | 100609055 | Hyper | ZIC5 |
| chr13 | 100624587 | 100624729 | Hyper | ZIC2, ZIC5 | chr13 | 100624316 | 100624348 | Hyper | ZIC2, ZIC5 |
| chr13 | 100627295 | 100627348 | Hyper | ZIC2, ZIC5 | chr13 | 100626929 | 100627009 | Hyper | ZIC2, ZIC5 |
| chr13 | 100635406 | 100635451 | Hyper | ZIC2 | chr13 | 100630630 | 100630997 | Hyper | ZIC2, ZIC5 |
| chr13 | 100637390 | 100637485 | Hyper | ZIC2 | chr13 | 100636167 | 100636238 | Hyper | ZIC2 |
| chr13 | 100643296 | 100643435 | Hyper | ZIC2 | chr13 | 100641282 | 100642201 | Hyper | ZIC2 |
| chr13 | 100649325 | 100649931 | Hyper | | chr13 | 100644055 | 100644212 | Hyper | ZIC2 |
| chr13 | 102568856 | 102568929 | Hyper | FGF14 | chr13 | 102568454 | 102568484 | Hyper | FGF14 |
| chr13 | 103046965 | 103046995 | Hyper | FGF14-AS2 | chr13 | 102569203 | 102569542 | Hyper | FGF14 |
| chr13 | 108518355 | 108518392 | Hyper | | chr13 | 103052892 | 103052940 | Hyper | FGF14-AS2 |
| chr13 | 108519254 | 108519367 | Hyper | | chr13 | 108518813 | 108518933 | Hyper | |
| chr13 | 108520979 | 108521076 | Hyper | | chr13 | 108520520 | 108520580 | Hyper | |
| chr13 | 109148783 | 109149032 | Hyper | | chr13 | 109147685 | 109148351 | Hyper | |
| chr13 | 110959220 | 110959255 | Hyper | COL4A2, COL4A1 | chr13 | 110958816 | 110958981 | Hyper | COL4A2, COL4A1 |
| chr13 | 110960250 | 110960282 | Hyper | COL4A2, COL4A1 | chr13 | 110959705 | 110959970 | Hyper | COL4A2, COL4A1 |
| chr13 | 112707694 | 112707869 | Hyper | | chr13 | 110960541 | 110960603 | Hyper | COL4A2, COL4A1 |
| chr13 | 112709388 | 112709617 | Hyper | | chr13 | 112708088 | 112708513 | Hyper | |
| chr13 | 112710344 | 112710508 | Hyper | | chr13 | 112709883 | 112709928 | Hyper | |
| chr13 | 112712017 | 112713029 | Hyper | SOX1 | chr13 | 112710759 | 112711776 | Hyper | |
| chr13 | 112715985 | 112716313 | Hyper | SOX1 | chr13 | 112715370 | 112715642 | Hyper | SOX1 |
| chr13 | 112717026 | 112717536 | Hyper | SOX1 | chr13 | 112716677 | 112716721 | Hyper | SOX1 |
| chr13 | 112720033 | 112720505 | Hyper | SOX1 | chr13 | 112717835 | 112717949 | Hyper | SOX1 |
| chr13 | 112721012 | 112721042 | Hyper | SOX1 | chr13 | 112720723 | 112720767 | Hyper | SOX1 |
| chr13 | 112724505 | 112724535 | Hyper | SOX1 | chr13 | 112721261 | 112722312 | Hyper | SOX1 |
| chr13 | 112727984 | 112728270 | Hyper | SOX1 | chr13 | 112726337 | 112726560 | Hyper | SOX1 |
| chr13 | 112758463 | 112758613 | Hyper | AK055145 | chr13 | 112758107 | 112758257 | Hyper | AK055145 |
| chr13 | 112759612 | 112759642 | Hyper | AK055145 | chr13 | 112758849 | 112759248 | Hyper | AK055145 |
| chr13 | 112760795 | 112761214 | Hyper | AK055145 | chr13 | 112759959 | 112760327 | Hyper | AK055145 |
| chr18 | 500046 | 500738 | Hyper | COLEC12 | chr18 | 499367 | 499482 | Hyper | COLEC12 |
| chr18 | 905000 | 905030 | Hyper | ADCYAP1 | chr18 | 904462 | 904648 | Hyper | ADCYAP1 |
| chr18 | 906871 | 906907 | Hyper | ADCYAP1 | chr18 | 905434 | 905642 | Hyper | ADCYAP1 |
| chr18 | 907912 | 907977 | Hyper | ADCYAP1 | chr18 | 907472 | 907594 | Hyper | ADCYAP1 |
| chr18 | 909120 | 909150 | Hyper | ADCYAP1 | chr18 | 908454 | 908589 | Hyper | ADCYAP1 |
| chr18 | 3499067 | 3499371 | Hyper | DLGAP1 | chr18 | 909487 | 909587 | Hyper | ADCYAP1 |
| chr18 | 4455074 | 4455181 | Hyper | | chr18 | 4453964 | 4454163 | Hyper | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr18 | 5197202 | 5197347 | Hyper | C18orf42 | chr18 | 5196516 | 5196959 | Hyper | C18orf42 |
| chr18 | 5543640 | 5543853 | Hyper | EPB41L3 | chr18 | 5543231 | 5543331 | Hyper | EPB41L3 |
| chr18 | 5629774 | 5629984 | Hyper | | chr18 | 5628167 | 5628515 | Hyper | |
| chr18 | 5890619 | 5891317 | Hyper | TMEM200C | chr18 | 5630312 | 5630362 | Hyper | |
| chr18 | 6729952 | 6729993 | Hyper | | chr18 | 5895023 | 5895205 | Hyper | TMEM200C |
| chr18 | 7567783 | 7567966 | Hyper | PTPRM | chr18 | 7116924 | 7116981 | Hyper | LAMA1 |
| chr18 | 8608748 | 8608968 | Hyper | RAB12 | chr18 | 7568246 | 7568291 | Hyper | PTPRM |
| chr18 | 11148969 | 11149045 | Hyper | | chr18 | 9771586 | 9771753 | Hyper | RAB31 |
| chr18 | 11751637 | 11751676 | Hyper | GNAL | chr18 | 11149561 | 11149888 | Hyper | |
| chr18 | 11752700 | 11752730 | Hyper | GNAL | chr18 | 11751966 | 11752379 | Hyper | GNAL |
| chr18 | 12307247 | 12307751 | Hyper | TUBB6 | chr18 | 12254453 | 12254578 | Hyper | CIDEA |
| chr18 | 13868713 | 13868945 | Hyper | | chr18 | 12911384 | 12911476 | Hyper | |
| chr18 | 18822392 | 18822553 | Hyper | GREB1L | chr18 | 15198110 | 15198248 | Hyper | |
| chr18 | 22929081 | 22930105 | Hyper | ZNF521 | chr18 | 18822843 | 18823274 | Hyper | GREB1L |
| chr18 | 22930790 | 22931178 | Hyper | ZNF521 | chr18 | 22930372 | 22930435 | Hyper | ZNF521 |
| chr18 | 24130809 | 24131187 | Hyper | | chr18 | 24127748 | 24128030 | Hyper | |
| chr18 | 25756685 | 25756729 | Hyper | | chr18 | 25756010 | 25756040 | Hyper | |
| chr18 | 25758084 | 25758141 | Hyper | | chr18 | 25757787 | 25757824 | Hyper | |
| chr18 | 28621328 | 28621393 | Hyper | DSC3 | chr18 | 28620899 | 28621097 | Hyper | DSC3 |
| chr18 | 28622419 | 28622488 | Hyper | DSC3 | chr18 | 28621729 | 28621932 | Hyper | DSC3 |
| chr18 | 31020495 | 31020527 | Hyper | CCDC178 | chr18 | 30349740 | 30349781 | Hyper | KLHL14 |
| chr18 | 31739035 | 31739469 | Hyper | | chr18 | 31158093 | 31158158 | Hyper | ASXL3 |
| chr18 | 31802938 | 31802968 | Hyper | | chr18 | 31802132 | 31802167 | Hyper | |
| chr18 | 32073885 | 32074086 | Hyper | DTNA | chr18 | 31803438 | 31803472 | Hyper | |
| chr18 | 35065072 | 35065438 | Hyper | | chr18 | 34833596 | 34833859 | Hyper | CELF4 |
| chr18 | 35147487 | 35147569 | Hyper | | chr18 | 35144845 | 35145465 | Hyper | |
| chr18 | 44336901 | 44336946 | Hyper | ST8SIA5 | chr18 | 44336034 | 44336697 | Hyper | ST8SIA5 |
| chr18 | 44773060 | 44773197 | Hyper | | chr18 | 44337174 | 44338074 | Hyper | ST8SIA5 |
| chr18 | 44774406 | 44774890 | Hyper | | chr18 | 44773592 | 44774153 | Hyper | |
| chr18 | 44776972 | 44777088 | Hyper | | chr18 | 44775380 | 44775554 | Hyper | |
| chr18 | 44777596 | 44777750 | Hyper | | chr18 | 44777301 | 44777331 | Hyper | |
| chr18 | 44781003 | 44781041 | Hyper | | chr18 | 44778049 | 44778326 | Hyper | |
| chr18 | 44788251 | 44788281 | Hyper | | chr18 | 44787781 | 44787846 | Hyper | |
| chr18 | 44789872 | 44789937 | Hyper | | chr18 | 44789474 | 44789514 | Hyper | |
| chr18 | 49867303 | 49867399 | Hyper | DCC | chr18 | 45058069 | 45058240 | Hyper | BC040860 |
| chr18 | 52989009 | 52989220 | Hyper | TCF4 | chr18 | 49868634 | 49868664 | Hyper | DCC |
| chr18 | 53257137 | 53257204 | Hyper | TCF4 | chr18 | 52989741 | 52989882 | Hyper | TCF4 |
| chr18 | 54789070 | 54789256 | Hyper | | chr18 | 53446970 | 53447816 | Hyper | AK127787 |
| chr18 | 55020655 | 55020727 | Hyper | ST8SIA3 | chr18 | 55019812 | 55019871 | Hyper | ST8SIA3 |
| chr18 | 55103381 | 55103411 | Hyper | ONECUT2 | chr18 | 55021078 | 55021242 | Hyper | ST8SIA3 |
| chr18 | 55105728 | 55105830 | Hyper | ONECUT2 | chr18 | 55104808 | 55105140 | Hyper | ONECUT2 |
| chr18 | 56887076 | 56887112 | Hyper | GRP | chr18 | 55114480 | 55114644 | Hyper | ONECUT2 |
| chr18 | 56931541 | 56931583 | Hyper | RAX | chr18 | 56888554 | 56888623 | Hyper | GRP |
| chr18 | 56932352 | 56932637 | Hyper | RAX | chr18 | 56931967 | 56932107 | Hyper | RAX |
| chr18 | 56936004 | 56936074 | Hyper | RAX | chr18 | 56935010 | 56935319 | Hyper | RAX |
| chr18 | 56939423 | 56940722 | Hyper | RAX | chr18 | 56939113 | 56939174 | Hyper | RAX |
| chr18 | 57363706 | 57363743 | Hyper | CCBE1 | chr18 | 56940955 | 56941788 | Hyper | RAX |
| chr18 | 59000988 | 59001022 | Hyper | CDH20 | chr18 | 57364275 | 57364392 | Hyper | CCBE1 |
| chr18 | 60263547 | 60263895 | Hyper | DKFZp451A185 | chr18 | 59001301 | 59001679 | Hyper | CDH20 |
| chr18 | 67067558 | 67067655 | Hyper | DOK6 | chr18 | 60985498 | 60985597 | Hyper | BCL2, KDSR |
| chr18 | 67068777 | 67068811 | Hyper | DOK6 | chr18 | 67068152 | 67068203 | Hyper | DOK6 |
| chr18 | 70209148 | 70209205 | Hyper | CBLN2 | chr18 | 67069216 | 67069246 | Hyper | DOK6 |
| chr18 | 70210467 | 70210497 | Hyper | CBLN2 | chr18 | 70209422 | 70209452 | Hyper | CBLN2 |
| chr18 | 70534282 | 70534969 | Hyper | NETO1 | chr18 | 70211626 | 70211666 | Hyper | CBLN2 |
| chr18 | 70536010 | 70536604 | Hyper | NETO1 | chr18 | 70535373 | 70535582 | Hyper | NETO1 |
| chr18 | 70537188 | 70537218 | Hyper | NETO1 | chr18 | 70536833 | 70536871 | Hyper | NETO1 |
| chr18 | 73628019 | 73628068 | Hyper | | chr18 | 73167585 | 73167832 | Hyper | |
| chr18 | 74962550 | 74962652 | Hyper | GALR1 | chr18 | 74961326 | 74961940 | Hyper | GALR1 |
| chr18 | 75612225 | 75612286 | Hyper | | chr18 | 74962970 | 74963599 | Hyper | GALR1 |
| chr18 | 77558082 | 77558358 | Hyper | | chr18 | 77548078 | 77548609 | Hyper | |
| chrX | 6145459 | 6145688 | Hyper | NLGN4X | AEKP01168736.1_1-4752 | 1754 | 2287 | Hyper | |
| chrX | 8699504 | 8699566 | Hyper | KAL1 | chrX | 8698863 | 8698897 | Hyper | KAL1 |
| chr20 | 590434 | 590502 | Hyper | TCF15 | chr20 | 291148 | 291373 | Hyper | |
| chr20 | 592405 | 592449 | Hyper | TCF15 | chr20 | 590751 | 590868 | Hyper | TCF15 |
| chr20 | 982749 | 982989 | Hyper | RSPO4 | chr20 | 644182 | 644787 | Hyper | SCRT2 |
| chr20 | 2539331 | 2539771 | Hyper | TMC2 | chr20 | 1783761 | 1784344 | Hyper | |
| chr20 | 2780753 | 2781281 | Hyper | CPXM1 | chr20 | 2668770 | 2668922 | Hyper | EBF4 |
| chr20 | 2785659 | 2786060 | Hyper | TMEM239, C20orf141, CPXM1 | chr20 | 2781731 | 2781761 | Hyper | CPXM1 |
| chr20 | 3073488 | 3073899 | Hyper | AVP | chr20 | 3052583 | 3052836 | Hyper | OXT |
| chr20 | 3229576 | 3229612 | Hyper | SLC4A11, C20orf194 | chr20 | 3220893 | 3220943 | Hyper | C20orf194, SLC4A11 |
| chr20 | 3663020 | 3663174 | Hyper | SIGLEC1, ADAM33 | chr20 | 3641733 | 3641937 | Hyper | GFRA4, ADAM33, AX748440 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr20 | 4229786 | 4230532 | Hyper | ADRA1D | chr20 | 4229402 | 4229432 | Hyper | ADRA1D |
| chr20 | 5296172 | 5296900 | Hyper | AX746654, PROKR2 | chr20 | 4803070 | 4803324 | Hyper | RASSF2 |
| chr20 | 8112378 | 8112408 | Hyper | PLCB1 | chr20 | 5297206 | 5297603 | Hyper | AX746654, PROKR2 |
| chr20 | 8113557 | 8113605 | Hyper | PLCB1 | chr20 | 8112974 | 8113022 | Hyper | PLCB1 |
| chr20 | 9488376 | 9488795 | Hyper | LAMP5 | chr20 | 9487385 | 9487997 | Hyper | LAMP5 |
| chr20 | 9489424 | 9489708 | Hyper | LAMP5 | chr20 | 9489070 | 9489214 | Hyper | LAMP5 |
| chr20 | 9496330 | 9496833 | Hyper | LAMP5 | chr20 | 9495271 | 9495509 | Hyper | LAMP5 |
| chr20 | 10198289 | 10198600 | Hyper | SNAP25 | chr20 | 9497035 | 9497109 | Hyper | LAMP5 |
| chr20 | 13200599 | 13200634 | Hyper | ISM1, AY927515 | chr20 | 10198915 | 10198945 | Hyper | SNAP25 |
| chr20 | 17207874 | 17207930 | Hyper | PCSK2 | chr20 | 17206513 | 17206747 | Hyper | PCSK2 |
| chr20 | 19739592 | 19739696 | Hyper |  | chr20 | 17208585 | 17208620 | Hyper | PCSK2 |
| chr20 | 20345686 | 20346106 | Hyper | C20orf26, INSM1 | chr20 | 20344498 | 20344559 | Hyper | INSM1, C20orf26 |
| chr20 | 21080714 | 21082253 | Hyper |  | chr20 | 20347460 | 20348154 | Hyper | INSM1, C20orf26 |
| chr20 | 21083421 | 21084361 | Hyper |  | chr20 | 21082532 | 21082917 | Hyper |  |
| chr20 | 21086176 | 21086451 | Hyper |  | chr20 | 21085831 | 21085864 | Hyper |  |
| chr20 | 21372174 | 21372725 | Hyper | NKX2-4, XRN2 | chr20 | 21086866 | 21087188 | Hyper |  |
| chr20 | 21486375 | 21486881 | Hyper | NKX2-2 | chr20 | 21376250 | 21378551 | Hyper | NKX2-4, XRN2 |
| chr20 | 21488158 | 21488351 | Hyper | NKX2-2 | chr20 | 21487153 | 21487761 | Hyper | NKX2-2 |
| chr20 | 21490175 | 21491529 | Hyper | NKX2-2 | chr20 | 21489224 | 21489703 | Hyper | NKX2-2 |
| chr20 | 21493308 | 21494265 | Hyper | NKX2-2 | chr20 | 21492378 | 21492983 | Hyper | NKX2-2 |
| chr20 | 21495942 | 21495986 | Hyper | NKX2-2 | chr20 | 21494531 | 21494703 | Hyper | NKX2-2 |
| chr20 | 21496637 | 21497136 | Hyper | NKX2-2 | chr20 | 21496260 | 21496294 | Hyper | NKX2-2 |
| chr20 | 21499961 | 21500134 | Hyper | NKX2-2 | chr20 | 21497413 | 21498638 | Hyper | NKX2-2 |
| chr20 | 21502037 | 21502330 | Hyper | NKX2-2 | chr20 | 21501424 | 21501724 | Hyper | NKX2-2 |
| chr20 | 21503690 | 21503773 | Hyper | NKX2-2 | chr20 | 21502590 | 21503117 | Hyper | NKX2-2 |
| chr20 | 21683311 | 21683651 | Hyper | PAX1 | chr20 | 21682399 | 21682456 | Hyper | PAX1 |
| chr20 | 21687009 | 21687731 | Hyper | PAX1 | chr20 | 21686235 | 21686677 | Hyper | PAX1 |
| chr20 | 21694499 | 21694529 | Hyper | PAX1 | chr20 | 21689956 | 21690185 | Hyper | PAX1 |
| chr20 | 21748445 | 21748491 | Hyper |  | chr20 | 21695088 | 21695148 | Hyper | PAX1 |
| chr20 | 22557979 | 22558114 | Hyper | FOXA2, LINC00261 | chr20 | 22557396 | 22557675 | Hyper | FOXA2, LINC00261 |
| chr20 | 22559645 | 22559690 | Hyper | FOXA2, LINC00261 | chr20 | 22558637 | 22558669 | Hyper | FOXA2, LINC00261 |
| chr20 | 22563563 | 22563602 | Hyper | FOXA2, LINC00261 | chr20 | 22562721 | 22562840 | Hyper | FOXA2, LINC00261 |
| chr20 | 23029387 | 23030325 | Hyper | THBD, AX747264 | chr20 | 23029110 | 23029151 | Hyper | THBD, AX747264 |
| chr20 | 24450782 | 24451019 | Hyper | SYNDIG1 | chr20 | 24450231 | 24450513 | Hyper | SYNDIG1 |
| chr20 | 25058385 | 25058616 | Hyper | VSX1 | chr20 | 24451450 | 24451592 | Hyper | SYNDIG1 |
| chr20 | 25063780 | 25064458 | Hyper | VSX1 | chr20 | 25061746 | 25062880 | Hyper | VSX1 |
| chr20 | 25129384 | 25129464 | Hyper | LOC284798 | chr20 | 25065179 | 25065395 | Hyper | VSX1 |
| chr20 | 30582750 | 30582978 | Hyper | XKR7 | chr20 | 26188812 | 26189011 | Hyper | MIR663A, |
| chr20 | 30639632 | 30639847 | Hyper | HCK | chr20 | 30639141 | 30639276 | Hyper | HCK |
| chr20 | 34188617 | 34189391 | Hyper | FER1L4 | chr20 | 30778051 | 30778249 | Hyper | PLAGL2, TSPY26P |
| chr20 | 36781324 | 36781354 | Hyper | HV531014, HV531011, HV531005, TGM2, HV531029, HV530979, HV531015 | chr20 | 34189635 | 34189910 | Hyper | FER1L4 |
| chr20 | 37351793 | 37352626 | Hyper | SLC32A1 | chr20 | 37302720 | 37303343 | Hyper |  |
| chr20 | 37353455 | 37353779 | Hyper | SLC32A1 | chr20 | 37353193 | 37353236 | Hyper | SLC32A1 |
| chr20 | 37355847 | 37357353 | Hyper | SLC32A1 | chr20 | 37354145 | 37355202 | Hyper | SLC32A1 |
| chr20 | 37435461 | 37435860 | Hyper | PPP1R16B | chr20 | 37357825 | 37358190 | Hyper | SLC32A1 |
| chr20 | 39319126 | 39319653 | Hyper | MAFB | chr20 | 39316893 | 39317392 | Hyper | MAFB |
| chr20 | 41817865 | 41818085 | Hyper |  | chr20 | 39995146 | 39995813 | Hyper | EMILIN3, LPIN3 |
| chr20 | 42136330 | 42136411 | Hyper | L3MBTL1 | chr20 | 41818567 | 41818914 | Hyper |  |
| chr20 | 42544091 | 42544984 | Hyper | TOX2 | chr20 | 42543754 | 42543853 | Hyper | TOX2 |
| chr20 | 43438071 | 43438466 | Hyper | RIMS4 | chr20 | 42876525 | 42876575 | Hyper | GDAP1L1 |
| chr20 | 43439291 | 43439510 | Hyper | RIMS4 | chr20 | 43438982 | 43439022 | Hyper | RIMS4 |
| chr20 | 44519077 | 44519107 | Hyper | ZSWIM1, CTSA, PLTP, NEURL2, SPATA25 | chr20 | 44452919 | 44452957 | Hyper | TNNC2, UBE2C, SNX21 |
| chr20 | 44660750 | 44660877 | Hyper | SLC12A5 | chr20 | 44639181 | 44639496 | Hyper | MMP9 |
| chr20 | 44803174 | 44803675 | Hyper | CDH22 | chr20 | 44686190 | 44686762 | Hyper | SLC12A5, NCOA5 |
| chr20 | 44879801 | 44880076 | Hyper |  | chr20 | 44875240 | 44875411 | Hyper |  |
| chr20 | 44941518 | 44941661 | Hyper |  | chr20 | 44937550 | 44937643 | Hyper |  |

TABLE 1-continued

| Chr | Start | Stop | Hypo/hyper | Annotation | Chr | Start | Stop | Hypo/hyper | Annotation |
|---|---|---|---|---|---|---|---|---|---|
| chr20 | 45279854 | 45280302 | Hyper | SLC13A3 | chr20 | 45142000 | 45142202 | Hyper | ZNF334 |
| chr20 | 47443729 | 47444282 | Hyper | | chr20 | 45524523 | 45524553 | Hyper | EYA2 |
| chr20 | 47935495 | 47935567 | Hyper | | chr20 | 47934824 | 47935268 | Hyper | |
| chr20 | 48184381 | 48184435 | Hyper | PTGIS | chr20 | 47935928 | 47936027 | Hyper | |
| chr20 | 49639777 | 49639920 | Hyper | KCNG1 | chr20 | 49575909 | 49575939 | Hyper | MOCS3, DPM1 |
| chr20 | 50720892 | 50721625 | Hyper | ZFP64 | chr20 | 50720437 | 50720599 | Hyper | ZFP64 |
| chr20 | 50722695 | 50722821 | Hyper | ZFP64 | chr20 | 50721915 | 50722193 | Hyper | ZFP64 |
| chr20 | 52789445 | 52789475 | Hyper | CYP24A1 | chr20 | 51589766 | 51589908 | Hyper | TSHZ2 |
| chr20 | 53092192 | 53092376 | Hyper | DOK5 | chr20 | 52789853 | 52789998 | Hyper | CYP24A1 |
| chr20 | 54578507 | 54578725 | Hyper | CBLN4 | chr20 | 53093085 | 53093115 | Hyper | DOK5 |
| chr20 | 54580574 | 54580604 | Hyper | CBLN4 | chr20 | 54579892 | 54580323 | Hyper | CBLN4 |
| chr20 | 55200922 | 55201092 | Hyper | TFAP2C | chr20 | 55200035 | 55200706 | Hyper | TFAP2C |
| chr20 | 55201764 | 55202626 | Hyper | TFAP2C | chr20 | 55201486 | 55201549 | Hyper | TFAP2C |
| chr20 | 55204322 | 55204604 | Hyper | TFAP2C | chr20 | 55202826 | 55203107 | Hyper | TFAP2C |
| chr20 | 55206056 | 55206393 | Hyper | TFAP2C | chr20 | 55204966 | 55205000 | Hyper | TFAP2C |
| chr20 | 55499496 | 55499709 | Hyper | | chr20 | 55206739 | 55206774 | Hyper | TFAP2C |
| chr20 | 55500410 | 55500949 | Hyper | | chr20 | 55500016 | 55500085 | Hyper | |
| chr20 | 56803398 | 56803441 | Hyper | PPP4R1L | chr20 | 55842096 | 55842189 | Hyper | BC037891, |
| chr20 | 57089452 | 57089496 | Hyper | APCDD1L-AS1, APCDD1L | chr20 | 56803842 | 56803920 | Hyper | PPP4R1L |
| chr20 | 57224842 | 57225307 | Hyper | STX16 | chr20 | 57089804 | 57090173 | Hyper | APCDD1L-AS1, |
| chr20 | 58179809 | 58179854 | Hyper | PHACTR3 | chr20 | 58152637 | 58152714 | Hyper | PHACTR3 |
| chr20 | 59826962 | 59827034 | Hyper | CDH4 | chr20 | 58180099 | 58180414 | Hyper | PHACTR3 |
| chr20 | 61340581 | 61340689 | Hyper | NTSR1 | chr20 | 59827795 | 59828446 | Hyper | CDH4 |
| chr20 | 61585771 | 61586004 | Hyper | SLC17A9, GID8 | chr20 | 61560418 | 61560922 | Hyper | GID8 |
| chr20 | 61637468 | 61638631 | Hyper | LOC63930, BHLHE23 | chr20 | 61636858 | 61636890 | Hyper | BHLHE23, LOC63930 |
| chr20 | 61734420 | 61734481 | Hyper | HAR1A, HAR1B | chr20 | 61703709 | 61703875 | Hyper | |
| chr20 | 61808181 | 61808270 | Hyper | MIR 124-3 | chr20 | 61747894 | 61747934 | Hyper | |
| chr20 | 61862380 | 61862452 | Hyper | BIRC7, MIR3196, NKAIN4 | chr20 | 61808485 | 61810089 | Hyper | MIR 124-3 |
| chr20 | 61886068 | 61886258 | Hyper | FLJ16779, NKAIN4 | chr20 | 61885712 | 61885744 | Hyper | FLJ16779, NKAIN4 |
| chr20 | 62058700 | 62058786 | Hyper | KCNQ2 | chr20 | 61886725 | 61886755 | Hyper | FLJ16779, |
| chr20 | 62461349 | 62461475 | Hyper | BC002534, ZBTB46 | chr20 | 62119339 | 62120171 | Hyper | EEF1A2 |
| chr8 | 687745 | 687843 | Hyper | ERICH1-AS1 | chr8 | 686870 | 687316 | Hyper | ERICH1-AS1 |
| chr8 | 688985 | 689043 | Hyper | ERICH1-AS1 | chr8 | 688360 | 688390 | Hyper | ERICH1-AS1 |
| chr8 | 4849466 | 4849500 | Hyper | | chr8 | 4849141 | 4849177 | Hyper | |
| chr8 | 4852088 | 4852118 | Hyper | | chr8 | 4850247 | 4850516 | Hyper | |
| chr8 | 9760735 | 9760790 | Hyper | MIR124-1, AK091593, LINC00599 | chr8 | 9756051 | 9756476 | Hyper | LINC00599, AK091593, MIR124-1 |
| chr8 | 9763143 | 9763275 | Hyper | MIR124-1, AK091593, LINC00599 | chr8 | 9762586 | 9762864 | Hyper | MIR124-1, AK091593, LINC00599 |
| chr8 | 9764434 | 9764551 | Hyper | MIR 124-1, AK091593, LINC00599 | chr8 | 9763895 | 9764214 | Hyper | MIR124-1, AK091593, LINC00599 |
| chr8 | 11204479 | 11204509 | Hyper | TDH, BC038546 | chr8 | 10588383 | 10588456 | Hyper | BC043573, SOX |
| chr8 | 11536827 | 11536857 | Hyper | GATA4 | chr8 | 11204804 | 11204905 | Hyper | TDH, BC038546 |
| chr8 | 11554885 | 11554915 | Hyper | GATA4 | chr8 | 11537225 | 11537259 | Hyper | GATA4 |
| chr8 | 11559759 | 11560375 | Hyper | GATA4 | chr8 | 11555152 | 11555521 | Hyper | GATA4 |
| chr8 | 11561442 | 11562169 | Hyper | GATA4 | chr8 | 11560711 | 11560793 | Hyper | GATA4 |
| chr8 | 11562701 | 11562917 | Hyper | GATA4 | chr8 | 11562422 | 11562485 | Hyper | GATA4 |
| chr8 | 12990664 | 12990784 | Hyper | DLC1 | chr8 | 12990386 | 12990431 | Hyper | DLC1 |
| chr8 | 15397735 | 15397845 | Hyper | TUSC3 | chr8 | 15094505 | 15094582 | Hyper | |
| chr8 | 19797433 | 19797463 | Hyper | LPL | chr8 | 16885205 | 16885241 | Hyper | MICU3 |
| chr8 | 20160762 | 20160894 | Hyper | | chr8 | 19797939 | 19798019 | Hyper | LPL |
| chr8 | 22562345 | 22562483 | Hyper | PEBP4 | chr8 | 22089409 | 22089560 | Hyper | PHYHIP |
| chr8 | 23260683 | 23260870 | Hyper | ENTPD4 | chr8 | 22960648 | 22960723 | Hyper | TNFRSF10C, LOC254896 |
| chr8 | 23563791 | 23564388 | Hyper | NKX2-6 | chr8 | 23559385 | 23560525 | Hyper | NKX2-6 |
| chr8 | 23566803 | 23567492 | Hyper | NKX2-6 | chr8 | 23564652 | 23565024 | Hyper | NKX2-6 |
| chr8 | 23572377 | 23572554 | Hyper | NKX2-6 | chr8 | 23571681 | 23571973 | Hyper | NKX2-6 |
| chr8 | 24770314 | 24770581 | Hyper | AK308605, NEFM | chr8 | 23584078 | 23584596 | Hyper | |
| chr8 | 24771431 | 24771562 | Hyper | NEFM, AK308605 | chr8 | 24771168 | 24771213 | Hyper | NEFM, AK308605 |
| chr8 | 24813750 | 24813912 | Hyper | NEFL | chr8 | 24813188 | 24813287 | Hyper | NEFL |
| chr8 | 24857776 | 24857808 | Hyper | | chr8 | 24814265 | 24814407 | Hyper | NEFL |
| chr8 | 24858856 | 24859161 | Hyper | | chr8 | 24858336 | 24858440 | Hyper | |
| chr8 | 25900408 | 25901317 | Hyper | EBF2 | chr8 | 24859496 | 24859526 | Hyper | |
| chr8 | 25902146 | 25902176 | Hyper | EBF2 | chr8 | 25901540 | 25901765 | Hyper | EBF2 |
| chr8 | 25903662 | 25903854 | Hyper | EBF2 | chr8 | 25902619 | 25902649 | Hyper | EBF2 |
| chr8 | 25905096 | 25905126 | Hyper | EBF2 | chr8 | 25904157 | 25904191 | Hyper | EBF2 |
| chr8 | 25909197 | 25909597 | Hyper | EBF2 | chr8 | 25905762 | 25905811 | Hyper | EBF2 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr8 | 26723985 | 26724080 | Hyper | AK311558, ADRA1A | chr8 | 26372863 | 26372893 | Hyper | DPYSL2, PNMA2 |
| chr8 | 30769249 | 30769411 | Hyper | | chr8 | 30243388 | 30243423 | Hyper | RBPMS, LOC100128750 |
| chr8 | 31497024 | 31497152 | Hyper | NRG1 | chr8 | 31496481 | 31496757 | Hyper | NRG1 |
| chr8 | 31498117 | 31498150 | Hyper | NRG1 | chr8 | 31497499 | 31497630 | Hyper | NRG1 |
| chr8 | 33372069 | 33372125 | Hyper | TTI2 | chr8 | 32406813 | 32406914 | Hyper | NRG1 |
| chr8 | 35092985 | 35093054 | Hyper | UNC5D | chr8 | 33457142 | 33457379 | Hyper | DUSP26 |
| chr8 | 37655454 | 37655517 | Hyper | GPR124 | chr8 | 35093951 | 35093981 | Hyper | UNC5D |
| chr8 | 37822796 | 37823423 | Hyper | ADRB3 | chr8 | 37655810 | 37656081 | Hyper | GPR124 |
| chr8 | 38008234 | 38008557 | Hyper | STAR | chr8 | 37823678 | 37823726 | Hyper | ADRB3 |
| chr8 | 41165865 | 41166723 | Hyper | SFRP1 | chr8 | 38323911 | 38323941 | Hyper | FGFR1 |
| chr8 | 41424760 | 41424842 | Hyper | | chr8 | 41166974 | 41167035 | Hyper | SFRP1 |
| chr8 | 41753593 | 41753761 | Hyper | | chr8 | 41733505 | 41733640 | Hyper | |
| chr8 | 41755178 | 41755208 | Hyper | | chr8 | 41754152 | 41754885 | Hyper | |
| chr8 | 49468682 | 49469127 | Hyper | | chr8 | 49293385 | 49293560 | Hyper | |
| chr8 | 50822686 | 50822734 | Hyper | SNTG1 | chr8 | 50822179 | 50822308 | Hyper | SNTG1 |
| chr8 | 53477408 | 53477780 | Hyper | FAM150A | chr8 | 50823452 | 50823562 | Hyper | SNTG1 |
| chr8 | 53478480 | 53478702 | Hyper | FAM150A | chr8 | 53478209 | 53478275 | Hyper | FAM150A |
| chr8 | 54163316 | 54164089 | Hyper | OPRK1 | chr8 | 53853811 | 53854216 | Hyper | NPBWR1 |
| chr8 | 54789632 | 54790077 | Hyper | RGS20 | chr8 | 54789278 | 54789310 | Hyper | RGS20 |
| chr8 | 54791809 | 54792237 | Hyper | RGS20 | chr8 | 54790291 | 54790855 | Hyper | RGS20 |
| chr8 | 54794217 | 54794327 | Hyper | RGS20 | chr8 | 54792634 | 54792760 | Hyper | RGS20 |
| chr8 | 55366188 | 55367600 | Hyper | SOX17 | chr8 | 54794713 | 54795196 | Hyper | RGS20 |
| chr8 | 55371178 | 55372538 | Hyper | SOX17 | chr8 | 55370113 | 5537085 | Hyper | SOX17 |
| chr8 | 55382766 | 55383237 | Hyper | SOX17 | chr8 | 55379280 | 55379962 | Hyper | SOX17 |
| chr8 | 56014157 | 56014317 | Hyper | XKR4 | chr8 | 56013641 | 56013927 | Hyper | XKR4 |
| chr8 | 56015038 | 56015357 | Hyper | XKR4 | chr8 | 56014623 | 56014783 | Hyper | XKR4 |
| chr8 | 57025692 | 57025943 | Hyper | SNORA3, MOS | chr8 | 56015560 | 56015619 | Hyper | XKR4 |
| chr8 | 57026503 | 57026547 | Hyper | SNORA3, MOS | chr8 | 57026168 | 57026213 | Hyper | SNORA3, MOS |
| chr8 | 57358147 | 57359636 | Hyper | AX747062, PENK | chr8 | 57069553 | 57070157 | Hyper | PLAG1 |
| chr8 | 58907698 | 58907835 | Hyper | FAM110B | chr8 | 57360570 | 57360791 | Hyper | AX747062, PENK |
| chr8 | 62200502 | 62200776 | Hyper | CLVS1 | chr8 | 60032680 | 60032738 | Hyper | TOX |
| chr8 | 65281616 | 65281760 | Hyper | LOC100130155, BX537900, MIR124-2 | chr8 | 63161658 | 63161800 | Hyper | NKAIN3 |
| chr8 | 65283799 | 65284094 | Hyper | LOC100130155, BX537900, MIR124-2 | chr8 | 65281984 | 65283341 | Hyper | LOC100130155, BX537900, MIR124-2 |
| chr8 | 65286682 | 65286753 | Hyper | MIR 124-2, LOC100130155 BX537900 | chr8 | 65286056 | 65286366 | Hyper | BX537900, MIR124-2, LOC100130155 |
| chr8 | 65289123 | 65289241 | Hyper | MIR124-2, LOC100130155 BX537900 | chr8 | 65286963 | 65287251 | Hyper | LOC100130155, BX537900, MIR124-2 |
| chr8 | 65290655 | 65290798 | Hyper | MIR124-2, BX537900, LOC100130155 | chr8 | 65289614 | 65290295 | Hyper | BX537900, MIR124-2, LOC100130155 |
| chr8 | 65292185 | 65292727 | Hyper | MIR124-2, BX537900, LOC100130155 | | | | | |
| chr8 | 65488661 | 65488697 | Hyper | BHLHE22, LOC401463 | chr8 | 65291034 | 65291284 | Hyper | LOC100130155, MIR124-2, BX537900 |
| chr8 | 65492949 | 65492979 | Hyper | BHLHE22, LOC401463 | chr8 | 65488271 | 65488322 | Hyper | BHLHE22, LOC401463 |
| chr8 | 65493658 | 65493751 | Hyper | BHLHE22, LOC401463 | chr8 | 65489099 | 65489129 | Hyper | BHLHE22, LOC401463 |
| chr8 | 65498566 | 65498841 | Hyper | LOC401463, CYP7B1, BHLHE22 | chr8 | 65493195 | 65493433 | Hyper | BHLHE22, LOC401463 |
| chr8 | 65710938 | 65711046 | Hyper | CYP7B1 | chr8 | 65493961 | 65494193 | Hyper | BHLHE22, LOC401463 |
| chr8 | 67873327 | 67875682 | Hyper | TCF24 | chr8 | 65499757 | 65500015 | Hyper | CYP7B1, BHLHE22, LOC401463 |
| chr8 | 68864578 | 68864765 | Hyper | PREX2, BC036055 | chr8 | 67344594 | 67344771 | Hyper | ADHFE1, RRS1, LOC100505676 |
| chr8 | 69243269 | 69243994 | Hyper | C8orf34, LOC286189 | chr8 | 67940624 | 67940875 | Hyper | |
| chr8 | 70744860 | 70744925 | Hyper | SLCOSA1 | chr8 | 69242905 | 69242976 | Hyper | C8orf34, LOC286189 |
| chr8 | 70981944 | 70983226 | Hyper | PRDM14 | chr8 | 69244370 | 69244500 | Hyper | LOC286189, C8orf34 |
| chr8 | 72273998 | 72274033 | Hyper | EYA1 | | | | | |

TABLE 1-continued

| Chr | Start | Stop | Hypo/hyper | Annotation | Chr | Start | Stop | Hypo/hyper | Annotation |
|---|---|---|---|---|---|---|---|---|---|
| chr8 | 72468569 | 72469567 | Hyper | | chr8 | 70946760 | 70947658 | Hyper | |
| chr8 | 72754394 | 72754609 | Hyper | LOC100132891, MSC | chr8 | 70983504 | 70984978 | Hyper | PRDM14 |
| chr8 | 72755666 | 72756896 | Hyper | LOC100132891, MSC | chr8 | 72460007 | 72460269 | Hyper | |
| chr8 | 73163777 | 73164180 | Hyper | LOC392232 | chr8 | 72471053 | 72471083 | Hyper | |
| chr8 | 73450515 | 73450559 | Hyper | KCNB2 | chr8 | 72754821 | 72755066 | Hyper | LOC100132891, MSC |
| chr8 | 77585219 | 77585698 | Hyper | ZFHX4, ZFHX4-AS1 | chr8 | 72987600 | 72988036 | Hyper | TRPA1 |
| chr8 | 77586563 | 77586617 | Hyper | ZFHX4, ZFHX4-AS1 | chr8 | 77586175 | 77586278 | Hyper | ZFHX4, ZFHX4-AS1 |
| chr8 | 77593110 | 77593376 | Hyper | ZFHX4-AS1, ZFHX4 | chr8 | 77590239 | 77590466 | Hyper | ZFHX4, ZFHX4-AS1 |
| chr8 | 77594648 | 77594993 | Hyper | ZFHX4, ZFHX4-AS1 | chr8 | 77593889 | 77594124 | Hyper | ZFHX4, ZFHX4-AS1 |
| chr8 | 79428297 | 79428401 | Hyper | PKIA | chr8 | 77595339 | 77595494 | Hyper | ZFHX4, ZFHX4-AS1 |
| chr8 | 80524253 | 80524318 | Hyper | STMN2 | chr8 | 80523983 | 80524029 | Hyper | STMN2 |
| chr8 | 80525604 | 80525733 | Hyper | STMN2 | chr8 | 80524946 | 80525020 | Hyper | STMN2 |
| chr8 | 80803694 | 80803872 | Hyper | | chr8 | 80695902 | 80695932 | Hyper | AK055332 |
| chr8 | 85095482 | 85095668 | Hyper | RALYL | chr8 | 81478185 | 81478350 | Hyper | |
| chr8 | 85097015 | 85097220 | Hyper | RALYL | chr8 | 85096583 | 85096805 | Hyper | RALYL |
| chr8 | 89340270 | 89340345 | Hyper | MMP16 | chr8 | 89339669 | 89339745 | Hyper | MMP16 |
| chr8 | 91803676 | 91803718 | Hyper | NECAB1 | chr8 | 91094221 | 91094251 | Hyper | Metazoa_SRP, CALB1 |
| chr8 | 91997046 | 91997947 | Hyper | LOC100127983, TMEM55A | chr8 | 91803991 | 91804253 | Hyper | NECAB1 |
| chr8 | 97157085 | 97158066 | Hyper | GDF6 | chr8 | 93114380 | 93114528 | Hyper | |
| chr8 | 97166425 | 97166455 | Hyper | GDF6 | chr8 | 97165644 | 97165676 | Hyper | GDF6 |
| chr8 | 97169838 | 97169876 | Hyper | GDF6 | chr8 | 97167178 | 97167223 | Hyper | GDF6 |
| chr8 | 97170867 | 97170897 | Hyper | GDF6 | chr8 | 97170158 | 97170334 | Hyper | GDF6 |
| chr8 | 97172433 | 97172871 | Hyper | GDF6 | chr8 | 97171129 | 97172200 | Hyper | GDF6 |
| chr8 | 97173822 | 97173935 | Hyper | GDF6 | chr8 | 97173174 | 97173458 | Hyper | GDF6 |
| chr8 | 97507115 | 97507284 | Hyper | SDC2 | chr8 | 97506034 | 97506524 | Hyper | SDC2 |
| chr8 | 99439382 | 99439473 | Hyper | KCNS2 | chr8 | 98289825 | 98290260 | Hyper | TSPYL5 |
| chr8 | 99951404 | 99951434 | Hyper | OSR2 | chr8 | 99440073 | 99440354 | Hyper | KCNS2 |
| chr8 | 99954490 | 99954727 | Hyper | OSR2 | chr8 | 99951836 | 99952815 | Hyper | OSR2 |
| chr8 | 99960329 | 99960971 | Hyper | OSR2 | chr8 | 99955180 | 99955327 | Hyper | OSR2 |
| chr8 | 99961792 | 99961822 | Hyper | OSR2 | chr8 | 99961187 | 99961272 | Hyper | OSR2 |
| chr8 | 101118241 | 101118577 | Hyper | | chr8 | 99985866 | 99987014 | Hyper | |
| chr8 | 104153202 | 104153246 | Hyper | BAALC, C8orf56, AK001351 | chr8 | 101821973 | 101822047 | Hyper | |
| chr8 | 104512123 | 104512175 | Hyper | RIMS2 | chr8 | 104153449 | 104153641 | Hyper | BAALC, C8orf56, AK001351 |
| chr8 | 104513462 | 104513492 | Hyper | RIMS2 | chr8 | 104512419 | 104512756 | Hyper | RIMS2 |
| chr8 | 105235369 | 105235664 | Hyper | | chr8 | 104513694 | 104513926 | Hyper | RIMS2 |
| chr8 | 105478725 | 105479176 | Hyper | | chr8 | 105235870 | 105236054 | Hyper | |
| chr8 | 106331160 | 106331237 | Hyper | ZFPM2 | chr8 | 105479404 | 105479464 | Hyper | |
| chr8 | 108509667 | 108509769 | Hyper | | chr8 | 107284038 | 107284075 | Hyper | OXR1 |
| chr8 | 109094485 | 109094595 | Hyper | RSPO2 | chr8 | 109093679 | 109094180 | Hyper | RSPO2 |
| chr8 | 109095657 | 109095932 | Hyper | RSPO2 | chr8 | 109094840 | 109095413 | Hyper | RSPO2 |
| chr8 | 114444580 | 114445192 | Hyper | CSMD3 | chr8 | 110986443 | 110986682 | Hyper | KCNV1 |
| chr8 | 114446405 | 114446435 | Hyper | CSMD3 | chr8 | 114445763 | 114446068 | Hyper | CSMD3 |
| chr8 | 114449039 | 114449257 | Hyper | CSMD3 | chr8 | 114446931 | 114447368 | Hyper | CSMD3 |
| chr8 | 116660527 | 116660760 | Hyper | TRPS1 | chr8 | 114449550 | 114449602 | Hyper | CSMD3 |
| chr8 | 117950783 | 117950914 | Hyper | AARD, AL832163 | chr8 | 117950438 | 117950468 | Hyper | AARD, AL832163 |
| chr8 | 122651872 | 122651905 | Hyper | HAS2-AS1, HAS2 | chr8 | 121136879 | 121137668 | Hyper | COL14A1 |
| chr8 | 132052147 | 132053164 | Hyper | ADCY8 | chr8 | 124173246 | 124173418 | Hyper | TRNA_Met, WDR67 |
| chr8 | 139508757 | 139509295 | Hyper | | chr8 | 132053715 | 132054749 | Hyper | ADCY8 |
| chr8 | 140714570 | 140714877 | Hyper | KCNK9 | chr8 | 139509741 | 139509928 | Hyper | |
| chr8 | 140715469 | 140715599 | Hyper | KCNK9 | chr8 | 140715090 | 140715120 | Hyper | KCNK9 |
| chr8 | 142528609 | 142528702 | Hyper | | chr8 | 140715965 | 140716382 | Hyper | KCNK9 |
| chr8 | 143532122 | 143532771 | Hyper | | chr8 | 142528930 | 142529004 | Hyper | |
| chr8 | 143592657 | 143592687 | Hyper | BAI1 | chr8 | 143533611 | 143533906 | Hyper | |
| chr8 | 143859322 | 143859361 | Hyper | LY6D, LYNX1 | chr8 | 143858522 | 143858699 | Hyper | LY6D, LYNX1 |
| chr8 | 144241543 | 144241582 | Hyper | LY6H | chr8 | 144241250 | 144241287 | Hyper | LY6H |
| chr8 | 144328321 | 144328565 | Hyper | ZFP41 | chr8 | 144241871 | 144242100 | Hyper | LY6H |
| chr8 | 144511225 | 144511424 | Hyper | ZC3H3, MAFA | chr8 | 144509325 | 144510529 | Hyper | MAFA, ZC3H3 |
| chr8 | 145698347 | 145698379 | Hyper | FOXH1, KIFC2, CYHR1 | chr8 | 144512080 | 144512134 | Hyper | ZC3H3, MAFA |
| chr19 | 591365 | 591416 | Hyper | HCN2, BSG | chr8 | 145925461 | 145925491 | Hyper | DQ588968 |
| chr19 | 1467423 | 1468188 | Hyper | C19orf25, APC2 | chr19 | 1450319 | 1450390 | Hyper | APC2, RPS15 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr19 | 1754172 | 1754254 | Hyper | ONECUT3 | chr19 | 1524368 | 1524447 | Hyper | PLK5 |
| chr19 | 1757416 | 1757615 | Hyper | ONECUT3 | chr19 | 1754739 | 1754804 | Hyper | ONECUT3 |
| chr19 | 1776376 | 1776429 | Hyper | ATP8B3, ONECUT3 | chr19 | 1762474 | 1762575 | Hyper | ONECUT3 |
| chr19 | 2252066 | 2252658 | Hyper | JSRP1, MIR4321, AMH, SF3A2 | chr19 | 2251152 | 2251715 | Hyper | JSRP1, MIR4321, AMH, SF3A2 |
| chr19 | 2253696 | 2253775 | Hyper | JSRP1, MIR4321, AMH, SF3A2 | chr19 | 2252984 | 2253428 | Hyper | JSRP1, MIR4321, AMH, SF3A2 |
| chr19 | 2302793 | 2302951 | Hyper |  | chr19 | 2290253 | 2290956 | Hyper | AX747191, LINGO3, C19orf35, SPPL2B |
| chr19 | 5338914 | 5339143 | Hyper |  | chr19 | 3785649 | 3786075 | Hyper | JA611290, MATK |
| chr19 | 7795012 | 7795244 | Hyper | CD209, CLEC4G | chr19 | 6590325 | 6590478 | Hyper | CD70 |
| chr19 | 7853361 | 7853460 | Hyper | CLEC4GP1 | chr19 | 7853028 | 7853157 | Hyper | CLEC4GP1 |
| chr19 | 9473699 | 9474056 | Hyper | ZNF177, ZNF559-ZNF177 | chr19 | 8115235 | 8115276 | Hyper | CCL25 |
| chr19 | 9608895 | 9609036 | Hyper | ZNF560 | chr19 | 9517609 | 9517771 | Hyper | ZNF266 |
| chr19 | 9903913 | 9904003 | Hyper |  | chr19 | 9609319 | 9609436 | Hyper | ZNF560 |
| chr19 | 10405972 | 10406349 | Hyper | ICAM5, ICAM4, ICAMI, ZGLP1, FDX1L | chr19 | 10398209 | 10398285 | Hyper | ICAM5, ICAM4, ICAM1 |
| chr19 | 10531964 | 10531994 | Hyper | PDE4A | chr19 | 10406806 | 10407135 | Hyper | FDX1L, ICAM5, ICAM4, ICAM1, ZGLP1 |
| chr19 | 11591031 | 11591185 | Hyper | ZNF653, ELAVL3 | chr19 | 10624751 | 10625465 | Hyper | S1PR5 |
| chr19 | 11593022 | 11593159 | Hyper | ZNF653, ELAVL3 | chr19 | 11592710 | 11592750 | Hyper | ZNF653, ELAVL3 |
| chr19 | 11959912 | 11960077 | Hyper | ZNF439 | chr19 | 11689460 | 11689564 | Hyper | ACP5, BC039523 |
| chr19 | 12203289 | 12203744 | Hyper | ZNF788 | chr19 | 12175814 | 12176005 | Hyper | ZNF844 |
| chr19 | 12267613 | 12267667 | Hyper | ZNF136, ZNF625 | chr19 | 12267019 | 12267251 | Hyper | ZNF136, ZNF625 |
| chr19 | 12750987 | 12751056 | Hyper | MAN2B1 | chr19 | 12305875 | 12306263 | Hyper | AK023304, AX721123, ZNF136 |
| chr19 | 13210225 | 13210316 | Hyper | TRMT1, LYL1, NFIX | chr19 | 12952000 | 12952139 | Hyper | MAST1, RTBDN |
| chr19 | 13618288 | 13618381 | Hyper | CACNA1A | chr19 | 13616696 | 13617256 | Hyper | CACNA1A |
| chr19 | 15090172 | 15090499 | Hyper | SLC1A6 | chr19 | 14584240 | 14584775 | Hyper | GIPC1, PTGER1, PKN1 |
| chr19 | 15288433 | 15288856 | Hyper | NOTCH3 | chr19 | 15121685 | 15121894 | Hyper | CCDC105 |
| chr19 | 15344107 | 15344325 | Hyper | BRD4, EPHX3 | chr19 | 15342781 | 15343099 | Hyper | BRD4, EPHX3 |
| chr19 | 17008523 | 17008799 | Hyper | CPAMD8, F2RL3 | chr19 | 17007086 | 17007662 | Hyper | CPAMD8, F2RL3 |
| chr19 | 18343439 | 18343569 | Hyper | PDE4C | chr19 | 17983537 | 17983834 | Hyper | SLC5A5 |
| chr19 | 18714552 | 18714675 | Hyper | TMEM59L, CRLF1 | chr19 | 18343921 | 18343963 | Hyper | PDE4C |
| chr19 | 18901915 | 18902006 | Hyper | COMP, CRTC1 | chr19 | 18899432 | 18899652 | Hyper | CRTC1, COMP |
| chr19 | 20011955 | 20012102 | Hyper | ZNF93, ZNF253 | chr19 | 18980760 | 18980897 | Hyper | CERS1, GDF1, UPF1 |
| chr19 | 20189322 | 20189438 | Hyper | ZNF90 | chr19 | 20188693 | 20188872 | Hyper | ZNF90 |
| chr19 | 22034198 | 22034813 | Hyper | ZNF43 | chr19 | 21646407 | 21646437 | Hyper | CR627135 |
| chr19 | 22715140 | 22715443 | Hyper |  | chr19 | 22610635 | 22610747 | Hyper | ZNF98 |
| chr19 | 23257703 | 23258694 | Hyper |  | chr19 | 23254189 | 23254219 | Hyper |  |
| chr19 | 23598274 | 23598326 | Hyper | AK022793, BC043213 | chr19 | 23299748 | 23300003 | Hyper | ZNF730 |
| chr19 | 30015934 | 30016712 | Hyper | VSTM2B, LOC284395 | chr19 | 29284452 | 29284719 | Hyper |  |
| chr19 | 30019145 | 30019838 | Hyper | VSTM2B, LOC284395 | chr19 | 30016914 | 30018608 | Hyper | VSTM2B, LOC284395 |
| chr19 | 30021125 | 30021193 | Hyper | VSTM2B, LOC284395 | chr19 | 30020093 | 30020473 | Hyper | LOC284395, VSTM2B |
| chr19 | 30713909 | 30714047 | Hyper |  | chr19 | 30713480 | 30713706 | Hyper |  |
| chr19 | 30715402 | 30715766 | Hyper |  | chr19 | 30714403 | 30714433 | Hyper |  |
| chr19 | 30716812 | 30718149 | Hyper |  | chr19 | 30716313 | 30716576 | Hyper |  |
| chr19 | 30719449 | 30720067 | Hyper |  | chr19 | 30718847 | 30718913 | Hyper |  |
| chr19 | 31839765 | 31839873 | Hyper | TSHZ3 | chr19 | 30865713 | 30866436 | Hyper | ZNF536 |
| chr19 | 31842596 | 31842646 | Hyper | TSHZ3 | chr19 | 31842359 | 31842389 | Hyper | TSHZ3 |
| chr19 | 33167116 | 33167431 | Hyper | RGS9BP, ANKRD27 | chr19 | 32715673 | 32715741 | Hyper |  |
| chr19 | 34112524 | 34112973 | Hyper | CHST8 | chr19 | 34112288 | 34112320 | Hyper | CHST8 |
| chr19 | 34114006 | 34114113 | Hyper | CHST8 | chr19 | 34113349 | 34113587 | Hyper | CHST8 |
| chr19 | 34973656 | 34973697 | Hyper | WTIP | chr19 | 34973225 | 34973255 | Hyper | WTIP |
| chr19 | 36048595 | 36048749 | Hyper | ATP4A | chr19 | 35396013 | 35396370 | Hyper | LINC00904, BC031235 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr19 | 36450272 | 36450302 | Hyper | | chr19 | 36334979 | 36335147 | Hyper | NPHS1 |
| chr19 | 36736027 | 36736057 | Hyper | ZNF146 | chr19 | 36523333 | 36523480 | Hyper | BC071809, THAP8, CLIP3 |
| chr19 | 36822324 | 36822892 | Hyper | ZFP14, LINC00665 | chr19 | 36736319 | 36736491 | Hyper | ZNF146 |
| chr19 | 36912354 | 36912398 | Hyper | LOC644189, ZFP82 | chr19 | 36909050 | 36909935 | Hyper | ZFP82, LOC644189 |
| chr19 | 37264222 | 37264421 | Hyper | BC024306, AX747375, ZNF850 | chr19 | 37095665 | 37096575 | Hyper | ZNF382, ZNF529 |
| chr19 | 37407127 | 37407443 | Hyper | ZNF568, ZNF829 | chr19 | 37288013 | 37288765 | Hyper | ZNF790-AS1 |
| chr19 | 37464410 | 37464696 | Hyper | ZNF568 | chr19 | 37464048 | 37464164 | Hyper | ZNF568 |
| chr19 | 37997433 | 37997541 | Hyper | ZNF793 | chr19 | 37959858 | 37959963 | Hyper | ZNF570, ZNF569 |
| chr19 | 38042365 | 38042693 | Hyper | ZNF540, ZNF571-AS1, ZNF571 | chr19 | 37997838 | 37998138 | Hyper | ZNF793 |
| chr19 | 38308080 | 38308466 | Hyper | LOC100631378, LOC644554 | chr19 | 38182884 | 38183299 | Hyper | ZNF607 |
| chr19 | 39687663 | 39687844 | Hyper | SYCN, NCCRP1 | chr19 | 38747358 | 38747582 | Hyper | SPINT2, PPP1R14A |
| chr19 | 39993477 | 39993664 | Hyper | DLL3 | chr19 | 39754874 | 39755358 | Hyper | IFNL2 |
| chr19 | 40006576 | 40006639 | Hyper | SELV, DLL3 | chr19 | 39997688 | 39997813 | Hyper | SELV, DLL3 |
| chr19 | 41018510 | 41018590 | Hyper | SPTBN4 | chr19 | 40724000 | 40724263 | Hyper | CNTD2, TTC9B, MAP3K10 |
| chr19 | 41025539 | 41025683 | Hyper | SPTBN4 | chr19 | 41018962 | 41019031 | Hyper | SPTBN4 |
| chr19 | 41073587 | 41073677 | Hyper | SPTBN4, SHKBP1 | chr19 | 41059909 | 41060306 | Hyper | |
| chr19 | 41354666 | 41354722 | Hyper | CYP2A6 | chr19 | 41119177 | 41119633 | Hyper | LTBP4 |
| chr19 | 42827891 | 42828266 | Hyper | MEGF8, TMEM145 | chr19 | 41641831 | 41641886 | Hyper | DQ590318, CYP2F1 |
| chr19 | 44405908 | 44406087 | Hyper | LOC100505715 | chr19 | 44203830 | 44203877 | Hyper | |
| chr19 | 44952282 | 44952881 | Hyper | ZNF229 | chr19 | 44905499 | 44905529 | Hyper | ZNF285 |
| chr19 | 45655393 | 45656363 | Hyper | TRAPPC6A, NKPD1, PPP1R37 | chr19 | 45300144 | 45300197 | Hyper | CBLC |
| chr19 | 45657212 | 45657284 | Hyper | TRAPPC6A, NKPD1, PPP1R37 | chr19 | 45656682 | 45656913 | Hyper | TRAPPC6A, NKPD1, PPP1R37 |
| chr19 | 46002048 | 46002320 | Hyper | VASP, RTN2, PPM1N | chr19 | 45888946 | 45889397 | Hyper | PPP1R13L |
| chr19 | 46930129 | 46930200 | Hyper | | chr19 | 46916725 | 46917037 | Hyper | CCDC8 |
| chr19 | 46992718 | 46992866 | Hyper | PNMAL2, BC132841, PPP5D1 | chr19 | 46974568 | 46974700 | Hyper | PNMAL1, PPP5D1 |
| chr19 | 46996589 | 46996666 | Hyper | PNMAL2, PPP5D1, BC132841 | chr19 | 46993164 | 4699338 | Hyper | PNMAL2, BC132841, PPP5D1 |
| chr19 | 47152617 | 47153011 | Hyper | DACT3 | chr19 | 46996871 | 46996918 | Hyper | PPP5D1, BC132841, PNMAL2 |
| chr19 | 47933311 | 47933732 | Hyper | SLC8A2 | chr19 | 47910482 | 47910517 | Hyper | MEIS3 |
| chr19 | 48918100 | 48918598 | Hyper | GRIN2D, Mir_324 | chr19 | 48076642 | 48076672 | Hyper | |
| chr19 | 49399218 | 49399310 | Hyper | NUCB1, Mir_324, TULP2 | chr19 | 49127373 | 49127470 | Hyper | SPHK2, DBP, RPL18 |
| chr19 | 49935736 | 49936174 | Hyper | LOC100507003, PTH2, SLC17A7 | chr19 | 49646149 | 49646213 | Hyper | PPFIA3, HRC |
| chr19 | 50553997 | 50554302 | Hyper | FLJ26850, ZNF473 | chr19 | 49936864 | 49936894 | Hyper | SLC17A7, LOC100507003 |
| chr19 | 50833828 | 50833863 | Hyper | NAPSB, NR1H2, KCNC3 | chr19 | 50816431 | 50816474 | Hyper | KCNC3, MYH14 |
| chr19 | 51162197 | 51162401 | Hyper | SHANK1, C19orf81 | chr19 | 51161225 | 51161255 | Hyper | SHANK1, C19orf81 |
| chr19 | 51171828 | 51171861 | Hyper | C19orf81, SHANK1 | chr19 | 51171219 | 51171278 | Hyper | SHANK1, C19orf81 |
| chr19 | 51228308 | 51228507 | Hyper | CLEC11A, SHANK1 | chr19 | 51227719 | 51227785 | Hyper | CLEC11A, SHANK1 |
| chr19 | 51830845 | 51831128 | Hyper | IGLON5, VSIG10L | chr19 | 51520423 | 51520453 | Hyper | KLK11, KLK10, KLK9 |
| chr19 | 52222523 | 52223131 | Hyper | HAS1 | chr19 | 51831360 | 51831390 | Hyper | VSIG10L, IGLON5 |
| chr19 | 52872924 | 52873421 | Hyper | ZNF610, ZNF880 | chr19 | 52839751 | 52839938 | Hyper | ZNF610, AK09759 |
| chr19 | 53073293 | 53073354 | Hyper | ZNF701 | chr19 | 52956805 | 52956848 | Hyper | ZNF578 |
| chr19 | 53194281 | 53194396 | Hyper | | chr19 | 53073563 | 53073987 | Hyper | ZNF701 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr19 | 53661718 | 53661902 | Hyper | ZNF665, ZNF347 | chr19 | 53561668 | 53561733 | Hyper | ZNF160, ERVV-2 |
| chr19 | 53696414 | 53696580 | Hyper | ZNF665 | chr19 | 53662174 | 53662244 | Hyper | ZNF665, ZNF347 |
| chr19 | 53758053 | 53758178 | Hyper | VNIR2, ZNF677 | chr19 | 53700596 | 53700729 | Hyper | ZNF665 |
| chr19 | 53970501 | 53970725 | Hyper | ZNF813, ZNF761 | chr19 | 53811858 | 53811988 | Hyper | |
| chr19 | 54024521 | 54024573 | Hyper | ZNF331 | chr19 | 53970968 | 53971157 | Hyper | ZNF813, ZNF761 |
| chr19 | 54411125 | 54411168 | Hyper | CACNG7 | chr19 | 54024818 | 54024884 | Hyper | ZNF331 |
| chr19 | 54412873 | 54412985 | Hyper | CACNG7 | chr19 | 54411556 | 54411586 | Hyper | CACNG7 |
| chr19 | 54481771 | 54481968 | Hyper | MIR935, CACNG8 | chr19 | 54445344 | 54445513 | Hyper | CACNG7 |
| chr19 | 54485524 | 54485823 | Hyper | MIR935, CACNG6, CACNG8 | chr19 | 54483391 | 54483517 | Hyper | MIR935, CACNG8 |
| chr19 | 56728678 | 56728976 | Hyper | ZSCAN5A | chr19 | 55629883 | 55630028 | Hyper | |
| chr19 | 56904863 | 56905203 | Hyper | ZNF582-AS1, ZNF582 | chr19 | 56879501 | 56880008 | Hyper | ZNF542 |
| chr19 | 56988557 | 56988716 | Hyper | ZNF667-AS1, ZNF667 | chr19 | 56915320 | 56915428 | Hyper | ZNF583, ZNF582-AS1 |
| chr19 | 57050463 | 57050493 | Hyper | BX647249, ZFP28 | chr19 | 56989575 | 56989615 | Hyper | ZNF667, ZNF667-AS1 |
| chr19 | 57154885 | 57155017 | Hyper | SMIM17 | chr19 | 57149579 | 57149619 | Hyper | SMIM17 |
| chr19 | 57276656 | 57276700 | Hyper | BC036412, ZIM2, FJ997633 | chr19 | 57182994 | 57183356 | Hyper | ZNF835 |
| chr19 | 57683148 | 57683295 | Hyper | DUXA | chr19 | 57617522 | 57618121 | Hyper | |
| chr19 | 58011124 | 58011281 | Hyper | ZNF773, ZNF419 | chr19 | 57863009 | 57863148 | Hyper | ZNF304 |
| chr19 | 58095006 | 58095835 | Hyper | ZIK1, ZNF416 | chr19 | 58038805 | 58038969 | Hyper | ZNF549 |
| chr19 | 58238326 | 58239088 | Hyper | ZNF671 | chr19 | 58219839 | 58220732 | Hyper | ZNF154 |
| chr19 | 58400417 | 58400518 | Hyper | ZNF814 | chr19 | 58400079 | 58400175 | Hyper | ZNF814 |
| chr19 | 58514518 | 58514552 | Hyper | ZNF606, LOC100128398 | chr19 | 58459164 | 58459201 | Hyper | ZNF256 |
| chr19 | 58545160 | 58545416 | Hyper | ZSCAN1 | chr19 | 58520739 | 58520941 | Hyper | LOC100128398, ZNF606 |
| chr19 | 58570528 | 58570666 | Hyper | ZNF135, ZSCAN1 | chr19 | 58545638 | 58545668 | Hyper | ZSCAN1 |
| chr19 | 58661894 | 58662094 | Hyper | | chr19 | 58609498 | 58609854 | Hyper | ZSCAN18 |
| chr19 | 58907689 | 58908195 | Hyper | MIR4754, LOC646862, RPS5 | chr19 | 58666171 | 58666313 | Hyper | |
| chr9 | 113433 | 113556 | Hyper | FOXD4, CBWD1 | chr19 | 58951271 | 58951916 | Hyper | ZNF132, DQ581862 |
| chr9 | 117884 | 118090 | Hyper | FOXD4, CBWD1 | chr9 | 113850 | 113885 | Hyper | FOXD4, CBWD1 |
| chr9 | 842558 | 842673 | Hyper | DMRT1 | chr9 | 841691 | 842230 | Hyper | DMRT1 |
| chr9 | 969799 | 969846 | Hyper | DMRT3, DMRT1 | chr9 | 969556 | 969586 | Hyper | DMRT3, DMRT1 |
| chr9 | 970495 | 970525 | Hyper | DMRT3, DMRT1 | chr9 | 970096 | 970225 | Hyper | DMRT3, DMRT1 |
| chr9 | 972307 | 972759 | Hyper | DMRT3, DMRT1 | chr9 | 970897 | 971572 | Hyper | DMRT3, DMRT1 |
| chr9 | 974514 | 974547 | Hyper | DMRT3, DMRT1 | chr9 | 973143 | 973289 | Hyper | DMRT1, DMRT3 |
| chr9 | 975783 | 976321 | Hyper | DMRT3, DMRT1 | chr9 | 975117 | 975167 | Hyper | DMRT3, DMRT1 |
| chr9 | 981797 | 981830 | Hyper | DMRT3 | chr9 | 976618 | 976961 | Hyper | DMRT3, DMRT1 |
| chr9 | 1051848 | 1052166 | Hyper | DMRT2 | chr9 | 1042402 | 1042986 | Hyper | DMRT2 |
| chr9 | 6412571 | 6412809 | Hyper | UHRF2 | chr9 | 3181752 | 3181869 | Hyper | |
| chr9 | 6645017 | 6645333 | Hyper | GLDC | chr9 | 6644297 | 6644554 | Hyper | GLDC |
| chr9 | 13278818 | 13278864 | Hyper | | chr9 | 6645625 | 6645700 | Hyper | GLDC |
| chr9 | 14348314 | 14348452 | Hyper | | chr9 | 14347633 | 14347673 | Hyper | |
| chr9 | 17907004 | 17907061 | Hyper | | chr9 | 17906404 | 17906694 | Hyper | |
| chr9 | 19789107 | 19789301 | Hyper | SLC24A2 | chr9 | 17907416 | 17907472 | Hyper | |
| chr9 | 21402617 | 21403021 | Hyper | IFNA8 | chr9 | 21031734 | 21031836 | Hyper | PTPLAD2 |
| chr9 | 21968419 | 21968475 | Hyper | CDKN2A, C9orf53 | chr9 | 21965057 | 21965715 | Hyper | C9orf53, CDKN2A |
| chr9 | 21973940 | 21974237 | Hyper | CDKN2A, C9orf53 | chr9 | 21970959 | 21971029 | Hyper | C9orf53, CDKN2A |
| chr9 | 23822568 | 23822606 | Hyper | | chr9 | 21974563 | 21974708 | Hyper | CDKN2A, C9orf53 |
| chr9 | 23831100 | 23831399 | Hyper | | chr9 | 23824561 | 23824591 | Hyper | |
| chr9 | 29213508 | 29213651 | Hyper | | chr9 | 29212170 | 29212294 | Hyper | |
| chr9 | 29214360 | 29214430 | Hyper | | chr9 | 29214030 | 29214144 | Hyper | |
| chr9 | 32782630 | 32783121 | Hyper | TMEM215 | chr9 | 29214681 | 29215086 | Hyper | |
| chr9 | 33524609 | 33524687 | Hyper | ANKRD18B | chr9 | 32783346 | 32783657 | Hyper | TMEM215 |
| chr9 | 33677360 | 33677415 | Hyper | PTENP1 | chr9 | 33676771 | 33676801 | Hyper | PTENP1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr9 | 34809749 | 34809981 | Hyper | | chr9 | 34589062 | 34589156 | Hyper | LOC415056, CNTFR |
| chr9 | 36739755 | 36739980 | Hyper | | chr9 | 35675539 | 35676049 | Hyper | TPM2, CA9, HV781757 |
| chr9 | 37025564 | 37025601 | Hyper | PAX5 | chr9 | 37002454 | 37003077 | Hyper | PAX5 |
| chr9 | 37026831 | 37027412 | Hyper | PAX5 | chr9 | 37026146 | 37026622 | Hyper | PAX5 |
| chr9 | 37029534 | 37030655 | Hyper | PAX5 | chr9 | 37028944 | 37029119 | Hyper | PAX5 |
| chr9 | 37034616 | 37034731 | Hyper | PAX5 | chr9 | 37034197 | 37034247 | Hyper | PAX5 |
| chr9 | 37036425 | 37036647 | Hyper | PAX5 | chr9 | 37035591 | 37035734 | Hyper | PAX5 |
| chr9 | 66455999 | 66456047 | Hyper | CR627148, AK308561 | chr9 | 37037671 | 37038354 | Hyper | |
| chr9 | 74061838 | 74062070 | Hyper | TRPM3 | chr9 | 71788952 | 71789757 | Hyper | TJP2, AK096834 |
| chr9 | 77112993 | 77113694 | Hyper | RORB | chr9 | 74764547 | 74764648 | Hyper | GDA |
| chr9 | 77115210 | 77115447 | Hyper | RORB | chr9 | 77114745 | 77114851 | Hyper | RORB |
| chr9 | 79626876 | 79627370 | Hyper | FOXB2 | chr9 | 77115657 | 77115687 | Hyper | RORB |
| chr9 | 79629095 | 79629471 | Hyper | FOXB2 | chr9 | 79628289 | 79628329 | Hyper | FOXB2 |
| chr9 | 79631192 | 79631335 | Hyper | FOXB2 | chr9 | 79629879 | 79630420 | Hyper | FOXB2 |
| chr9 | 79631865 | 79632182 | Hyper | FOXB2 | chr9 | 79631555 | 79631591 | Hyper | FOXB2 |
| chr9 | 79633397 | 79633904 | Hyper | FOXB2 | chr9 | 79632860 | 79632890 | Hyper | FOXB2 |
| chr9 | 79636258 | 79637274 | Hyper | FOXB2 | chr9 | 79634170 | 79636043 | Hyper | FOXB2 |
| chr9 | 86152387 | 86152417 | Hyper | | chr9 | 79637555 | 79638150 | Hyper | FOXB2 |
| chr9 | 86886706 | 86886736 | Hyper | SLC28A3 | chr9 | 86755532 | 86755597 | Hyper | |
| chr9 | 87283677 | 87283709 | Hyper | NTRK2 | chr9 | 87283008 | 87283038 | Hyper | NTRK2 |
| chr9 | 87285279 | 87285472 | Hyper | NTRK2 | chr9 | 87284706 | 87284798 | Hyper | NTRK2 |
| chr9 | 89517699 | 89517835 | Hyper | | chr9 | 88137524 | 88137923 | Hyper | |
| chr9 | 89561063 | 89561109 | Hyper | LOC100506834, GAS1 | chr9 | 89560760 | 89560827 | Hyper | LOC100506834, GAS1 |
| chr9 | 91606004 | 91606058 | Hyper | S1PR3, C9orf47 | chr9 | 91150222 | 91150335 | Hyper | NXNL2 |
| chr9 | 91792776 | 91792907 | Hyper | SHC3 | chr9 | 91792357 | 91792387 | Hyper | SHC3 |
| chr9 | 94183870 | 94183954 | Hyper | | chr9 | 91793455 | 91793526 | Hyper | SHC3 |
| chr9 | 95569759 | 95569822 | Hyper | ANKRD19P | chr9 | 94712163 | 94712236 | Hyper | ROR2 |
| chr9 | 95571617 | 95571760 | Hyper | ANKRD19P | chr9 | 95570247 | 95570434 | Hyper | ANKRD19P |
| chr9 | 96588804 | 96588885 | Hyper | MIR4291 | chr9 | 95947130 | 95947296 | Hyper | WNK2 |
| chr9 | 96710647 | 96710991 | Hyper | BARX1 | chr9 | 96710377 | 96710407 | Hyper | BARX1 |
| chr9 | 96711975 | 96712005 | Hyper | BARX1 | chr9 | 96711258 | 96711617 | Hyper | BARX1 |
| chr9 | 96715095 | 96715660 | Hyper | BARX1 | chr9 | 96713378 | 96713893 | Hyper | BARX1 |
| chr9 | 96717979 | 96718149 | Hyper | JB148981, BARX1 | chr9 | 96716837 | 96717466 | Hyper | JB148981, BARX1 |
| chr9 | 96722576 | 96722693 | Hyper | JB148981, BARX1 | chr9 | 96720803 | 96721802 | Hyper | BARX1, JB148981 |
| chr9 | 98111365 | 98112395 | Hyper | | chr9 | 96723093 | 96723202 | Hyper | JB148981, BARX1 |
| chr9 | 98789651 | 98790000 | Hyper | LINC00092, C9orf102 | chr9 | 98784772 | 98784802 | Hyper | LINC00092, C9orf102, ERCC6L2 |
| chr9 | 99639621 | 99639942 | Hyper | LOC100132781, ZNF782 | chr9 | 99449135 | 99449380 | Hyper | |
| chr9 | 99983411 | 99983824 | Hyper | | chr9 | 99983140 | 99983170 | Hyper | |
| chr9 | 100503625 | 100503937 | Hyper | | chr9 | 99984026 | 99984242 | Hyper | |
| chr9 | 100610681 | 100611640 | Hyper | FOXE1 | chr9 | 100609991 | 100610218 | Hyper | FOXE1 |
| chr9 | 100614541 | 100616902 | Hyper | FOXE1 | chr9 | 100613828 | 100614325 | Hyper | FOXE1 |
| chr9 | 100617682 | 100618055 | Hyper | FOXE1 | chr9 | 100617293 | 100617365 | Hyper | FOXE1 |
| chr9 | 100620330 | 100620783 | Hyper | FOXE1 | chr9 | 100619722 | 100620069 | Hyper | FOXE1 |
| chr9 | 101469603 | 101469796 | Hyper | GABBR2 | chr9 | 101469269 | 101469307 | Hyper | GABBR2 |
| chr9 | 101470968 | 101471071 | Hyper | GABBR2 | chr9 | 101470116 | 101470250 | Hyper | GABBR2 |
| chr9 | 101471860 | 101472009 | Hyper | GABBR2 | chr9 | 101471570 | 101471621 | Hyper | GABBR2 |
| chr9 | 104248579 | 104248623 | Hyper | TMEM246 | chr9 | 101705996 | 101706695 | Hyper | COL15A1 |
| chr9 | 110228200 | 110228602 | Hyper | | chr9 | 104500625 | 104500774 | Hyper | |
| chr9 | 113341522 | 113341760 | Hyper | | chr9 | 112403170 | 112403200 | Hyper | Mir_548, PALM2 |
| chr9 | 115652966 | 115653425 | Hyper | SLC46A2 | chr9 | 113342299 | 113342340 | Hyper | |
| chr9 | 120175795 | 120175832 | Hyper | | chr9 | 118917024 | 118917079 | Hyper | PAPPA |
| chr9 | 120176867 | 120176897 | Hyper | | chr9 | 120176104 | 120176151 | Hyper | |
| chr9 | 122131481 | 122131642 | Hyper | DBC1 | chr9 | 120507409 | 120507439 | Hyper | |
| chr9 | 126770257 | 126770298 | Hyper | LHX2, AK131516 | chr9 | 122132112 | 122132227 | Hyper | DBC1 |
| chr9 | 126774517 | 126775144 | Hyper | AK131516, LHX2 | chr9 | 126771532 | 126771705 | Hyper | LHX2, AK131516 |
| chr9 | 126776044 | 126776119 | Hyper | LHX2, AK131516 | chr9 | 126775530 | 126775560 | Hyper | LHX2, AK131516 |
| chr9 | 126778320 | 126778496 | Hyper | LHX2, AK131516 | chr9 | 126777529 | 126777982 | Hyper | LHX2, AK131516 |
| chr9 | 126780811 | 126780898 | Hyper | LHX2, AK131516 | chr9 | 126779485 | 126780315 | Hyper | LHX2, AK131516 |
| chr9 | 127212851 | 127213006 | Hyper | GPR144 | chr9 | 126783295 | 126783499 | Hyper | LHX2 |
| chr9 | 127266387 | 127266534 | Hyper | NR5A1 | chr9 | 127265688 | 127266025 | Hyper | NR5A1 |
| chr9 | 129276718 | 129276820 | Hyper | | chr9 | 128652200 | 128652232 | Hyper | PBX3 |
| chr9 | 129377214 | 129377316 | Hyper | LMX1B | chr9 | 129372929 | 129373223 | Hyper | LMX1B |

TABLE 1-continued

| Chr | Start | Stop | Hypo/hyper | Annotation | Chr | Start | Stop | Hypo/hyper | Annotation |
|---|---|---|---|---|---|---|---|---|---|
| chr9 | 129381111 | 129381180 | Hyper | LMX1B | chr9 | 129377604 | 129377911 | Hyper | LMX1B |
| chr9 | 129387800 | 129388200 | Hyper | LMX1B | chr9 | 129387434 | 129387464 | Hyper | LMX1B |
| chr9 | 129400986 | 129401195 | Hyper | LMX1B | chr9 | 129388996 | 129389192 | Hyper | LMX1B |
| chr9 | 129445783 | 129445813 | Hyper | LMX1B | chr9 | 129445255 | 129445566 | Hyper | LMX1B |
| chr9 | 130461642 | 130461742 | Hyper | C9orf117, BC032117, MIR3911, STXBP1 | chr9 | 129485841 | 129485923 | Hyper | |
| chr9 | 133308893 | 133308941 | Hyper | AK074396 | chr9 | 132382383 | 132382746 | Hyper | NTMT1, C9orf50 |
| chr9 | 133535734 | 133535839 | Hyper | PRDM12 | chr9 | 133534683 | 133534713 | Hyper | PRDM12 |
| chr9 | 133537182 | 133537549 | Hyper | PRDM12 | chr9 | 133536097 | 133536344 | Hyper | PRDM12 |
| chr9 | 133539606 | 133539709 | Hyper | PRDM12 | chr9 | 133538169 | 133538728 | Hyper | PRDM12 |
| chr9 | 133541689 | 133542337 | Hyper | PRDM12 | chr9 | 133541059 | 133541192 | Hyper | PRDM12 |
| chr9 | 135455996 | 135456065 | Hyper | C9orf171, BARHL1 | chr9 | 135455407 | 135455585 | Hyper | BARHL1, C9orf171 |
| chr9 | 135456897 | 135456932 | Hyper | BARHL1, C9orf171 | chr9 | 135456496 | 135456526 | Hyper | BARHL1, C9orf171 |
| chr9 | 135460001 | 135460176 | Hyper | DDX31, BARHL1 | chr9 | 135458477 | 135458597 | Hyper | BARHL1, C9orf171 |
| chr9 | 135461511 | 135461773 | Hyper | BARHL1, DDX31 | chr9 | 135460869 | 135460899 | Hyper | DDX31, BARHL1 |
| chr9 | 135464798 | 135464918 | Hyper | DDX31, BARHL1 | chr9 | 135462048 | 135462967 | Hyper | DDX31, BARHL1 |
| chr9 | 135466344 | 135466660 | Hyper | DDX31, BARHL1 | chr9 | 135465948 | 135466132 | Hyper | DDX31, BARHL1 |
| chr9 | 137299119 | 137299254 | Hyper | RXRA | chr9 | 136474490 | 136474607 | Hyper | |
| chr9 | 137979893 | 137980011 | Hyper | OLFM1 | chr9 | 137533974 | 137534238 | Hyper | COL5A1 |
| chr9 | 137980880 | 137980910 | Hyper | OLFM1 | chr9 | 137980258 | 137980288 | Hyper | OLFM1 |
| chr9 | 139024723 | 139024782 | Hyper | | chr9 | 138606307 | 138606576 | Hyper | KCNT1 |
| chr9 | 139085924 | 139085978 | Hyper | LHX3, RBSG2 | chr9 | 139085228 | 139085360 | Hyper | LHX3, RBSG2 |
| chr9 | 139090793 | 139091369 | Hyper | QSOX2, LHX3, RBSG2 | chr9 | 139090500 | 139090578 | Hyper | LHX3, RBSG2, QSOX2 |
| chr9 | 139094705 | 139094873 | Hyper | QSOX2, LHX3, RBSG2 | chr9 | 139093681 | 139093890 | Hyper | QSOX2, LHX3, RBSG2 |
| chr9 | 139096650 | 139097006 | Hyper | QSOX2, LHX3 | chr9 | 139095340 | 139095485 | Hyper | QSOX2, LHX3, RBSG2 |
| chr9 | 140024893 | 140024987 | Hyper | GRIN1 | chr9 | 139739236 | 139739300 | Hyper | MAMDC4, C9orf172, RABL6, PHPT1 |
| chr9 | 140033426 | 140033642 | Hyper | GRIN1 | chr9 | 140032891 | 140032951 | Hyper | GRIN1 |
| chr9 | 140050969 | 140051354 | Hyper | GRIN1 | chr9 | 140033909 | 140034079 | Hyper | GRIN1 |
| chr9 | 140772586 | 140773301 | Hyper | CACNA1B, AK128414 | chr9 | 140772149 | 140772347 | Hyper | CACNA1B, AK128414 |
| chr3 | 239622 | 240223 | Hyper | CHL1 | chr3 | 238536 | 239094 | Hyper | CHL1 |
| chr3 | 3840498 | 3840534 | Hyper | LRRN1, BC141932, SUMF1 | chr3 | 2140277 | 2140398 | Hyper | CNTN4 |
| chr3 | 6903425 | 6903463 | Hyper | GRM7 | chr3 | 6902288 | 6902353 | Hyper | GRM7 |
| chr3 | 9593979 | 9594101 | Hyper | LHFPL4 | chr3 | 8810136 | 8810220 | Hyper | Mir 548, OXTR |
| chr3 | 9904233 | 9904554 | Hyper | CIDEC | chr3 | 9595292 | 9595584 | Hyper | LHFPL4 |
| chr3 | 9957451 | 9957677 | Hyper | IL17RC, IL17RE | chr3 | 9957064 | 9957142 | Hyper | IL17RC, IL17RE |
| chr3 | 11035070 | 11035330 | Hyper | SLC6A1 | chr3 | 10857987 | 10858019 | Hyper | SLC6A11 |
| chr3 | 13323494 | 13323973 | Hyper | | chr3 | 12917606 | 12917655 | Hyper | DQ581328 |
| chr3 | 13324847 | 13324912 | Hyper | | chr3 | 13324358 | 13324433 | Hyper | |
| chr3 | 13921407 | 13921463 | Hyper | WNT7A | chr3 | 13590416 | 13590863 | Hyper | FBLN2 |
| chr3 | 14852325 | 14852472 | Hyper | FGD5 | chr3 | 14851850 | 14851897 | Hyper | FGD5 |
| chr3 | 16554347 | 16554558 | Hyper | | chr3 | 16554052 | 16554111 | Hyper | |
| chr3 | 27754478 | 27754508 | Hyper | EOMES | chr3 | 26664045 | 26664119 | Hyper | LRRC3B |
| chr3 | 27762857 | 27762887 | Hyper | EOMES | chr3 | 27762336 | 27762650 | Hyper | EOMES |
| chr3 | 27765181 | 27765347 | Hyper | EOMES | chr3 | 27764457 | 27764503 | Hyper | EOMES |
| chr3 | 28616869 | 28617675 | Hyper | LINC00693, AX746710 | chr3 | 27771497 | 27772004 | Hyper | EOMES |
| chr3 | 32860068 | 32860273 | Hyper | TRIM71 | chr3 | 32858353 | 32859693 | Hyper | TRIM71 |
| chr3 | 35680842 | 35680872 | Hyper | ARPP21 | chr3 | 33259904 | 33260776 | Hyper | SUSD5 |
| chr3 | 36806151 | 36806193 | Hyper | | chr3 | 36805815 | 36805863 | Hyper | |
| chr3 | 38080685 | 38080781 | Hyper | DLEC1, PLCD1 | chr3 | 38035767 | 38035989 | Hyper | VILL |
| chr3 | 38690624 | 38690668 | Hyper | SCN5A | chr3 | 38081148 | 38081271 | Hyper | DLEC1, PLCD1 |
| chr3 | 42814569 | 42814603 | Hyper | HIGD1A, CCDC13 | chr3 | 39851772 | 39851814 | Hyper | MYRIP |
| chr3 | 44036260 | 44036330 | Hyper | | chr3 | 42947411 | 42947552 | Hyper | ZNF662 |
| chr3 | 44036820 | 44037140 | Hyper | | chr3 | 44036570 | 44036600 | Hyper | |
| chr3 | 44037874 | 44038646 | Hyper | | chr3 | 44037625 | 44037662 | Hyper | |
| chr3 | 44040511 | 44040553 | Hyper | | chr3 | 44039348 | 44040006 | Hyper | |
| chr3 | 44063434 | 44063872 | Hyper | | chr3 | 44040943 | 44041039 | Hyper | |
| chr3 | 44596716 | 44596809 | Hyper | ZKSCAN7 | chr3 | 44596479 | 44596509 | Hyper | ZKSCAN7 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr3 | 44726875 | 44727193 | Hyper | | chr3 | 44626451 | 44626537 | Hyper | ZKSCAN7, ZNF660 |
| chr3 | 48698810 | 48699767 | Hyper | | chr3 | 48693304 | 48694170 | Hyper | |
| chr3 | 50402170 | 50402410 | Hyper | CACNA2D2, Mir_324, TMEM115 | chr3 | 50243383 | 50243480 | Hyper | GNAT1, SLC38A3 |
| chr3 | 54157878 | 54157919 | Hyper | CACNA2D3 | chr3 | 54157381 | 54157450 | Hyper | CACNA2D3 |
| chr3 | 62304560 | 62304669 | Hyper | C3orf14, PTPRG-AS1 | chr3 | 55523106 | 55523290 | Hyper | WNT5A |
| chr3 | 62354283 | 62354328 | Hyper | FEZF2 | chr3 | 62353371 | 62354049 | Hyper | FEZF2 |
| chr3 | 62355424 | 62355478 | Hyper | FEZF2 | chr3 | 62354625 | 62354914 | Hyper | FEZF2 |
| chr3 | 62357624 | 62357667 | Hyper | FEZF2 | chr3 | 62355774 | 62357347 | Hyper | FEZF2 |
| chr3 | 62358530 | 62358595 | Hyper | FEZF2 | chr3 | 62358161 | 62358194 | Hyper | FEZF2 |
| chr3 | 62359376 | 62359893 | Hyper | FEZF2 | chr3 | 62358858 | 62359011 | Hyper | FEZF2 |
| chr3 | 62362902 | 62363200 | Hyper | FEZF2 | chr3 | 62360302 | 62360560 | Hyper | FEZF2 |
| chr3 | 62363906 | 62364329 | Hyper | FEZF2 | chr3 | 62363626 | 62363693 | Hyper | FEZF2 |
| chr3 | 62861118 | 62861148 | Hyper | | chr3 | 62364702 | 62365154 | Hyper | FEZF2 |
| chr3 | 68056904 | 68057145 | Hyper | FAM19A1, AX747367 | chr3 | 63264139 | 63264169 | Hyper | SYNPR |
| chr3 | 68981552 | 68981624 | Hyper | | chr3 | 68980931 | 68981113 | Hyper | |
| chr3 | 69591363 | 69591512 | Hyper | | chr3 | 69590939 | 69590969 | Hyper | |
| chr3 | 71803126 | 71803372 | Hyper | GPR27, EIF4E3 | chr3 | 69592011 | 69592063 | Hyper | |
| chr3 | 75956011 | 75956375 | Hyper | | chr3 | 71803643 | 71803821 | Hyper | GPR27, EIF4E3 |
| chr3 | 79816778 | 79817015 | Hyper | | chr3 | 79815522 | 79815557 | Hyper | |
| chr3 | 85008553 | 85008708 | Hyper | CADM2 | chr3 | 79817288 | 79817318 | Hyper | |
| chr3 | 96534035 | 96534096 | Hyper | EPHA6 | chr3 | 96533383 | 96533458 | Hyper | EPHA6 |
| chr3 | 117715549 | 117716473 | Hyper | | chr3 | 99594925 | 99595105 | Hyper | FILIP1L |
| chr3 | 120627317 | 120627453 | Hyper | STXBP5L | chr3 | 120004040 | 120004106 | Hyper | |
| chr3 | 123167073 | 123167353 | Hyper | | chr3 | 121902975 | 121903619 | Hyper | CASR |
| chr3 | 125898597 | 125899207 | Hyper | ALDH1L1-AS2, ALDH1L1 | chr3 | 123167769 | 123167827 | Hyper | |
| chr3 | 125932252 | 125932500 | Hyper | ALDH1L1-AS2 | chr3 | 125899525 | 125899962 | Hyper | ALDHIL1-AS2, ALDHIL1 |
| chr3 | 127634186 | 127634216 | Hyper | KBTBD12 | chr3 | 126854699 | 126854796 | Hyper | |
| chr3 | 128202447 | 128202477 | Hyper | GATA2 | chr3 | 127794546 | 127794860 | Hyper | RUVBL1, SEC61A1 |
| chr3 | 128273993 | 128274098 | Hyper | | chr3 | 128208903 | 128209232 | Hyper | GATA2 |
| chr3 | 128417201 | 128417231 | Hyper | | chr3 | 128274327 | 128274400 | Hyper | |
| chr3 | 128720882 | 128721229 | Hyper | KIAA1257, EFCC1 | chr3 | 128720061 | 128720611 | Hyper | EFCC1, KIAA1257 |
| chr3 | 129693108 | 129694299 | Hyper | TRH | chr3 | 128764489 | 128764632 | Hyper | EFCC1 |
| chr3 | 130064451 | 130064484 | Hyper | COL6A5 | chr3 | 129694504 | 129694534 | Hyper | TRH |
| chr3 | 130236049 | 130236273 | Hyper | | chr3 | 130064818 | 130064848 | Hyper | COL6A5 |
| chr3 | 132757065 | 132757104 | Hyper | TMEM108 | chr3 | 131754031 | 131754061 | Hyper | |
| chr3 | 134515186 | 134515369 | Hyper | EPHB1 | chr3 | 134369803 | 134369855 | Hyper | KY |
| chr3 | 136537642 | 136537730 | Hyper | SLC35G2 | chr3 | 134515676 | 134516222 | Hyper | EPHB1 |
| chr3 | 137479233 | 137479302 | Hyper | SOX14 | chr3 | 136538585 | 136538715 | Hyper | SLC35G2 |
| chr3 | 137479980 | 137480764 | Hyper | SOX14 | chr3 | 137479601 | 137479687 | Hyper | SOX14 |
| chr3 | 137481858 | 137482183 | Hyper | SOX14 | chr3 | 137481170 | 137481315 | Hyper | SOX14 |
| chr3 | 137483848 | 137484002 | Hyper | BC038725, SOX14 | chr3 | 137483498 | 137483589 | Hyper | SOX14, BC038725 |
| chr3 | 137486029 | 137486310 | Hyper | BC038725, SOX14 | chr3 | 137484405 | 137484531 | Hyper | BC038725, SOX14 |
| chr3 | 137487964 | 137488021 | Hyper | BC038725, SOX14 | chr3 | 137486516 | 137486550 | Hyper | BC038725, SOX14 |
| chr3 | 138153963 | 138153993 | Hyper | ESYT3 | chr3 | 137488950 | 137491040 | Hyper | BC038725, SOX14 |
| chr3 | 138655934 | 138656138 | Hyper | AK128202, FOXL2, C3orf72 | chr3 | 138154340 | 138154377 | Hyper | ESYT3 |
| chr3 | 138657650 | 138659099 | Hyper | C3orf72, AK304483, AK128202, FOXL2 | chr3 | 138656834 | 138656889 | Hyper | FOXL2, C3orf72, AK304483, AK128202 |
| chr3 | 138662382 | 138662448 | Hyper | AK128202, FOXL2, C3orf72, AK304483 | chr3 | 138662134 | 138662164 | Hyper | AK128202, FOXL2, C3orf72, AK304483 |
| chr3 | 138663613 | 138664165 | Hyper | AK128202, C3orf72, AK304483, FOXL2 | chr3 | 138662799 | 138662842 | Hyper | FOXL2, C3orf72, AK304483, AK128202 |
| chr3 | 138664928 | 138665323 | Hyper | C3orf72, AK304483, FOXL2, AK128202 | chr3 | 138664408 | 138664489 | Hyper | C3orf72, AK304483, FOXL2, AK128202 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr3 | 138665953 | 138666294 | Hyper | AK304483, FOXL2, AK128202, C3orf72 | chr3 | 138665562 | 138665619 | Hyper | C3orf72, AK304483, FOXL2, AK128202 |
| chr3 | 138679462 | 138679526 | Hyper | AK304483, C3orf72 | chr3 | 138668742 | 138669387 | Hyper | AK304483, C3orf72, FOXL2, AK128202 |
| chr3 | 139653491 | 139653693 | Hyper | CLSTN2 | chr3 | 139258267 | 139258316 | Hyper | RBP1 |
| chr3 | 14076990 | 140769999 | Hyper | SPSB4 | chr3 | 140769513 | 140769705 | Hyper | SPSB4 |
| chr3 | 140771305 | 140771335 | Hyper | SPSB4 | chr3 | 140770297 | 140770829 | Hyper | SPSB4 |
| chr3 | 141516389 | 141516719 | Hyper | GRK7 | chr3 | 140771816 | 140771854 | Hyper | SPSB4 |
| chr3 | 142838621 | 142839036 | Hyper | CHST2 | chr3 | 142838066 | 142838370 | Hyper | CHST2 |
| chr3 | 147074457 | 147074487 | Hyper | | chr3 | 142839612 | 142840236 | Hyper | CHST2 |
| chr3 | 147077289 | 147077418 | Hyper | | chr3 | 147074974 | 147075006 | Hyper | |
| chr3 | 147087562 | 147087799 | Hyper | | chr3 | 147078959 | 147079188 | Hyper | |
| chr3 | 147088939 | 147089099 | Hyper | | chr3 | 147088440 | 147088523 | Hyper | |
| chr3 | 147108841 | 147109932 | Hyper | ZIC4 | chr3 | 147098431 | 147098470 | Hyper | ZIC4 |
| chr3 | 147110927 | 147111089 | Hyper | ZIC4 | chr3 | 147110145 | 147110683 | Hyper | ZIC4 |
| chr3 | 147127037 | 147127067 | Hyper | ZIC1, ZIC4 | chr3 | 147111545 | 147111579 | Hyper | ZIC4 |
| chr3 | 147128287 | 147128326 | Hyper | ZIC1, ZIC4 | chr3 | 147127681 | 147127902 | Hyper | ZIC1, ZIC4 |
| chr3 | 147138768 | 147138856 | Hyper | ZIC1 | chr3 | 147136931 | 147137164 | Hyper | ZIC1 |
| chr3 | 147139374 | 147139528 | Hyper | ZIC1 | chr3 | 147139126 | 147139156 | Hyper | ZIC1 |
| chr3 | 148415427 | 148415644 | Hyper | AGTR1 | chr3 | 147142225 | 147142265 | Hyper | ZIC1 |
| chr3 | 150802981 | 150803080 | Hyper | MED12L, CLRN1-AS1 | chr3 | 149374947 | 149375023 | Hyper | WWTR1-AS1, AK309441 |
| chr3 | 152553343 | 152553384 | Hyper | P2RY1 | chr3 | 150804967 | 150805030 | Hyper | MED12L, CLRN1-AS1 |
| chr3 | 154146133 | 154146412 | Hyper | GPR149 | chr3 | 153839930 | 153840057 | Hyper | ARHGEF26, ARHGEF26-AS1 |
| chr3 | 154797622 | 154797703 | Hyper | MME | chr3 | 154146654 | 154146908 | Hyper | GPR149 |
| chr3 | 156534302 | 156534332 | Hyper | AK094480, LEKR1, PA2G4P4, LINC00886 | chr3 | 156008976 | 156009425 | Hyper | KCNAB1 |
| chr3 | 157155982 | 157156045 | Hyper | Mir_584, PTX3, VEPH1 | chr3 | 157155252 | 157155332 | Hyper | VEPH1, Mir_584, PTX3 |
| chr3 | 157812912 | 157813070 | Hyper | SHOX2 | chr3 | 157812196 | 157812645 | Hyper | SHOX2 |
| chr3 | 157821085 | 157821662 | Hyper | SHOX2, RSRC1 | chr3 | 157813608 | 157813644 | Hyper | SHOX2 |
| chr3 | 157824729 | 157824871 | Hyper | RSRC1, SHOX2 | chr3 | 157823073 | 157823143 | Hyper | RSRC1, SHOX2 |
| chr3 | 159756687 | 159756856 | Hyper | | chr3 | 157825176 | 157825408 | Hyper | SHOX2, RSRC1 |
| chr3 | 160168003 | 160168033 | Hyper | | chr3 | 159944486 | 159944546 | Hyper | IFT80, C3orf80 |
| chr3 | 164912907 | 164913576 | Hyper | SLITRK3 | chr3 | 164912376 | 164912545 | Hyper | SLITRK3 |
| chr3 | 169376183 | 169376215 | Hyper | | chr3 | 164914980 | 164915129 | Hyper | SLITRK3 |
| chr3 | 169378825 | 169379024 | Hyper | | chr3 | 169376680 | 169376780 | Hyper | |
| chr3 | 170137667 | 170137772 | Hyper | CLDN11 | chr3 | 170136627 | 170136751 | Hyper | CLDN11 |
| chr3 | 170303087 | 170303129 | Hyper | BC039437, SLC7A14 | chr3 | 170302617 | 170302677 | Hyper | SLC7A14, BC039437 |
| chr3 | 170303684 | 170303844 | Hyper | BC039437, SLC7A14 | chr3 | 170303331 | 170303423 | Hyper | BC039437, SLC7A14 |
| chr3 | 172166879 | 172167044 | Hyper | GHSR, GU289929 | chr3 | 172165443 | 172166627 | Hyper | GHSR, GU289929 |
| chr3 | 172167660 | 172167917 | Hyper | GHSR, GU289929 | chr3 | 172167297 | 172167327 | Hyper | GU289929, GHSR |
| chr3 | 173302992 | 173303225 | Hyper | NLGN1 | chr3 | 173302542 | 173302684 | Hyper | NLGN1 |
| chr3 | 179754178 | 179755372 | Hyper | | chr3 | 179168661 | 179169220 | Hyper | GNB4 |
| chr3 | 181413742 | 181414330 | Hyper | SOX2-OT, JA611300 | chr3 | 181413084 | 181413355 | Hyper | JA611300, SOX2-OT |
| chr3 | 181420316 | 181420374 | Hyper | SOX2, JA611300, SOX2-OT | chr3 | 181420065 | 181420116 | Hyper | SOX2, JA611300, SOX2-OT |
| chr3 | 181422541 | 181422985 | Hyper | JA611300, SOX2-OT, SOX2 | chr3 | 181421411 | 181422282 | Hyper | SOX2, JA611300, SOX2-OT |
| chr3 | 181430695 | 181430771 | Hyper | SOX2 | chr3 | 181428388 | 181428772 | Hyper | SOX2 |
| chr3 | 181438194 | 181438353 | Hyper | SOX2 | chr3 | 181437129 | 181437349 | Hyper | SOX2 |
| chr3 | 181442145 | 181442410 | Hyper | SOX2 | chr3 | 181440892 | 181441927 | Hyper | SOX2 |
| chr3 | 181443760 | 181443861 | Hyper | | chr3 | 181443014 | 181443557 | Hyper | |
| chr3 | 181445369 | 181445464 | Hyper | | chr3 | 181444434 | 181445013 | Hyper | |
| chr3 | 183145412 | 183145618 | Hyper | | chr3 | 181445735 | 181445861 | Hyper | |
| chr3 | 186078766 | 186078898 | Hyper | | chr3 | 184301734 | 184301772 | Hyper | EPHB3 |
| chr3 | 186080188 | 186080218 | Hyper | | chr3 | 186079204 | 186079331 | Hyper | |
| chr3 | 187387850 | 187388239 | Hyper | SST | chr3 | 186857152 | 186857298 | Hyper | |
| chr3 | 192126146 | 192126499 | Hyper | FGF12 | chr3 | 192125828 | 192125858 | Hyper | FGF12 |
| chr3 | 192232097 | 192232175 | Hyper | FGF12 | chr3 | 192127354 | 192128074 | Hyper | FGF12 |
| chr3 | 192232834 | 192233150 | Hyper | FGF12 | chr3 | 192232452 | 192232570 | Hyper | FGF12 |
| chr3 | 194208286 | 194208562 | Hyper | AX746839, LINC00884 | chr3 | 193776089 | 193776119 | Hyper | BC038368 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr16 | 215416 | 216224 | Hyper | HBM, HBA2 | chr3 | 194408375 | 194409021 | Hyper | FAM43A |
| chr16 | 230265 | 230535 | Hyper | HBQ1, LUC7L, HBA1, HBA2 | chr16 | 216676 | 217036 | Hyper | HBA1, HBM, HBA2 |
| chr16 | 1203970 | 1204034 | Hyper | CACNA1H | chr16 | 1030302 | 1030655 | Hyper | SOX8, LMF1 |
| chr16 | 2040914 | 2042160 | Hyper | NOXO1, ZNF598, SYNGR3, GFER | chr16 | 1382901 | 1382940 | Hyper | BAIAP3 |
| chr16 | 2892542 | 2892729 | Hyper | PRSS22, PRSS30P | chr16 | 2287295 | 2287370 | Hyper | E4F1, ECI1, DNASE1L2 |
| chr16 | 3068171 | 3068201 | Hyper | CLDN6, CLDN9, TNFRSF12A, HCFC1R1, THOC6, CCDC64B | chr16 | 3017052 | 3017628 | Hyper | PKMYT1, KREMEN2, PAQR4 |
| chr16 | 3221101 | 3222239 | Hyper | TRNA_Pro, TRNA_Lys, TRNA_Pseudo | chr16 | 3220566 | 3220879 | Hyper | TRNA_Pro, TRNA_Lys, TRNA_Pseudo |
| chr16 | 3232739 | 3234452 | Hyper | TRNA_Pro, TRNA_Lys, TRNA_Arg | chr16 | 3225471 | 3225607 | Hyper | TRNA_Lys, TRNA_Pro, TRNA_Pseudo |
| chr16 | 3238993 | 3239848 | Hyper | TRNA_Pro, TRNA_Lys, TRNA_Arg, TRNA_Pseudo | chr16 | 3237857 | 3238546 | Hyper | TRNA_Arg, TRNA_Pseudo, TRNA_Pro, TRNA_Lys |
| chr16 | 3241936 | 3241966 | Hyper | TRNA_Pro, TRNA_Arg, TRNA_Pseudo, TRNA_Lys | chr16 | 3241549 | 3241663 | Hyper | TRNA_Pro, TRNA_Arg, TRNA_Pseudo, TRNA_Lys |
| chr16 | 5037900 | 5038004 | Hyper | SEC14L5 | chr16 | 3355279 | 3355718 | Hyper | ZNF75A, TIGD7, ZNF263 |
| chr16 | 7354634 | 7354664 | Hyper | RBFOX1 | chr16 | 6069925 | 6070019 | Hyper | RBFOX1 |
| chr16 | 10275308 | 10275392 | Hyper | GRIN2A | chr16 | 10274399 | 10274429 | Hyper | GRIN2A |
| chr16 | 10277036 | 10277437 | Hyper | GRIN2A | chr16 | 10276597 | 10276763 | Hyper | GRIN2A |
| chr16 | 12994459 | 12994737 | Hyper | SHISA9 | chr16 | 10479815 | 10479980 | Hyper | ATF7IP2 |
| chr16 | 12995505 | 12995593 | Hyper | SHISA9 | chr16 | 12995062 | 12995237 | Hyper | SHISA9 |
| chr16 | 12996617 | 12996720 | Hyper | SHISA9 | chr16 | 12995803 | 12996328 | Hyper | SHISA9 |
| chr16 | 19567202 | 19567449 | Hyper | CCP110, C16orf62 | chr16 | 12997386 | 12997703 | Hyper | SHISA9 |
| chr16 | 22824701 | 22825094 | Hyper | HS3ST2 | chr16 | 19895125 | 19895155 | Hyper | GPRC5B |
| chr16 | 23706317 | 23706520 | Hyper | ERN2, PLK1 | chr16 | 22825327 | 22826081 | Hyper | HS3ST2 |
| chr16 | 24267115 | 24267208 | Hyper | CACNG3 | chr16 | 23847309 | 23847956 | Hyper | PRKCB |
| chr16 | 25702955 | 25702992 | Hyper | HS3ST4 | chr16 | 24267485 | 24267578 | Hyper | CACNG3 |
| chr16 | 28074176 | 28074215 | Hyper |  | chr16 | 25703642 | 25704628 | Hyper | HS3ST4 |
| chr16 | 29888136 | 29888227 | Hyper | SEZ6L2, CDIPT-AS1 | chr16 | 28074654 | 28074684 | Hyper |  |
| chr16 | 31227914 | 31228277 | Hyper | PYDC1, TRIM72 | chr16 | 29888624 | 29888658 | Hyper | CDIPT-AS1, SEZ6L2 |
| chr16 | 48844792 | 48845125 | Hyper |  | chr16 | 31580560 | 31581036 | Hyper | YBX3P1 |
| chr16 | 49311523 | 49312299 | Hyper | CBLN1 | chr16 | 49309170 | 49309262 | Hyper | CBLN1 |
| chr16 | 49314022 | 49314118 | Hyper | CBLN1 | chr16 | 49313363 | 49313710 | Hyper | CBLN1 |
| chr16 | 49314784 | 49314837 | Hyper | CBLN1 | chr16 | 49314419 | 49314561 | Hyper | CBLN1 |
| chr16 | 49315919 | 49316580 | Hyper | CBLN1 | chr16 | 49315276 | 49315306 | Hyper | CBLN1 |
| chr16 | 51184807 | 51185360 | Hyper | SALL1 | chr16 | 51183900 | 51184406 | Hyper | SALL1 |
| chr16 | 51186592 | 51186939 | Hyper | SALL1 | chr16 | 51185844 | 51186079 | Hyper | SALL1 |
| chr16 | 54318898 | 54318988 | Hyper | IRX3 | chr16 | 51189922 | 51190215 | Hyper | SALL1 |
| chr16 | 54321638 | 54321834 | Hyper | IRX3 | chr16 | 54319420 | 54319468 | Hyper | IRX3 |
| chr16 | 54628691 | 54628867 | Hyper |  | chr16 | 54324999 | 54325131 | Hyper | IRX3 |
| chr16 | 54971060 | 54971090 | Hyper | IRX5, CRNDE | chr16 | 54966830 | 54967283 | Hyper | IRX5, CRNDE |
| chr16 | 55090666 | 55090861 | Hyper |  | chr16 | 54971400 | 54971430 | Hyper | IRX5, CRNDE |
| chr16 | 55358316 | 55358528 | Hyper | IRX6 | chr16 | 55357926 | 55358086 | Hyper | IRX6 |
| chr16 | 55363009 | 55363223 | Hyper | IRX6 | chr16 | 55358798 | 55359071 | Hyper | IRX6 |
| chr16 | 55365103 | 55365234 | Hyper | IRX6 | chr16 | 55364716 | 55364843 | Hyper | IRX6 |
| chr16 | 55690293 | 55690809 | Hyper | SLC6A2 | chr16 | 55512843 | 55512884 | Hyper | MMP2 |
| chr16 | 56228479 | 56228581 | Hyper | LOC283856, DKFZP434H168, GNA01 | chr16 | 56224557 | 56224879 | Hyper | GNAO1, DKFZP434H168, LOC283856 |
| chr16 | 56659175 | 56659673 | Hyper | MTIE, MT1M, MT1JP, MTIL, MT1A | chr16 | 56651094 | 56651275 | Hyper | MT1L, MT1M, MT1E, MT1A, MT2A |
| chr16 | 56709837 | 56710030 | Hyper | MTE, MT1X, MT1IP, MT1H, MT1G | chr16 | 56672158 | 56672543 | Hyper | MT1A, MT1DP, MT1JP, MT1M |
| chr16 | 58019225 | 58019430 | Hyper | ZNF319, TEPP | chr16 | 58018634 | 58018845 | Hyper | ZNF319, TEPP |
| chr16 | 62068952 | 62068982 | Hyper |  | chr16 | 62068463 | 62068517 | Hyper |  |
| chr16 | 65154933 | 65155091 | Hyper |  | chr16 | 62070743 | 62070773 | Hyper |  |
| chr16 | 66461786 | 66461840 | Hyper | BEAN1 | chr16 | 65156385 | 65156489 | Hyper |  |

TABLE 1-continued

| Chr | Start | Stop | Hypo/hyper | Annotation | Chr | Start | Stop | Hypo/hyper | Annotation |
|---|---|---|---|---|---|---|---|---|---|
| chr16 | 67197698 | 67197769 | Hyper | TRADD, HSF4, NOL3, FBXL8 | chr16 | 66612882 | 66613238 | Hyper | CMTM2, CMTM1 |
| chr16 | 67198917 | 67198957 | Hyper | TRADD, NOL3, HSF4, FBXL8 | chr16 | 67198009 | 67198039 | Hyper | TRADD, HSF4, NOL3, FBXL8 |
| chr16 | 68676408 | 68676984 | Hyper | CDH3 | chr16 | 68544259 | 68544378 | Hyper | |
| chr16 | 73100460 | 73100524 | Hyper | | chr16 | 71460027 | 71460351 | Hyper | TRNA_Met |
| chr16 | 77822589 | 77822874 | Hyper | VAT1L | chr16 | 77468261 | 77468775 | Hyper | ADAMTS18 |
| chr16 | 79623602 | 79623645 | Hyper | MAF | chr16 | 78079969 | 78080054 | Hyper | |
| chr16 | 85932828 | 85932858 | Hyper | IRF8 | chr16 | 82660360 | 82660496 | Hyper | CDH13 |
| chr16 | 86320755 | 86320800 | Hyper | LOC146513 | chr16 | 86320354 | 86320391 | Hyper | LOC146513 |
| chr16 | 86530947 | 86531046 | Hyper | FENDRR | chr16 | 86321020 | 86321068 | Hyper | LOC146513 |
| chr16 | 86541591 | 86541968 | Hyper | FENDRR, FOXF1 | chr16 | 86531310 | 86531573 | Hyper | FENDRR |
| chr16 | 86544191 | 86544972 | Hyper | FOXF1, FENDRR | chr16 | 86542373 | 86542457 | Hyper | FOXF1, FENDRR |
| chr16 | 86600483 | 86600686 | Hyper | FOXC2, FLJ30679 | chr16 | 86599477 | 86599844 | Hyper | FOXC2, FLJ30679 |
| chr16 | 86601286 | 86601539 | Hyper | FOXC2 | chr16 | 86600958 | 86601015 | Hyper | FOXC2 |
| chr16 | 87635103 | 87635133 | Hyper | JPH3 | chr16 | 86601945 | 86602514 | Hyper | FOXC2, FOXL1 |
| chr16 | 87636807 | 87636907 | Hyper | JPH3 | chr16 | 87636518 | 87636580 | Hyper | JPH3 |
| chr16 | 89267808 | 89267847 | Hyper | SLC22A31, CDH15 | chr16 | 89267334 | 89267364 | Hyper | SLC22A31, CDH15 |
| chr14 | 22005029 | 22005073 | Hyper | | chr14 | 21093454 | 21093631 | Hyper | TRNA_Pro, TRNA_Leu, TRNA_Thr |
| chr14 | 24803594 | 24804409 | Hyper | RIPK3, ADCY4 | chr14 | 24045513 | 24045603 | Hyper | JPH4, AP1G2 |
| chr14 | 26674699 | 26674729 | Hyper | | chr14 | 26674384 | 26674414 | Hyper | |
| chr14 | 29225531 | 29225561 | Hyper | | chr14 | 27067161 | 27067386 | Hyper | NOVA1 |
| chr14 | 29228654 | 29228778 | Hyper | FOXG1 | chr14 | 29226071 | 29226198 | Hyper | |
| chr14 | 29231071 | 29231217 | Hyper | FOXG1 | chr14 | 29229107 | 29229386 | Hyper | FOXG1 |
| chr14 | 29235003 | 29235356 | Hyper | FOXG1, C14orf23 | chr14 | 29231425 | 29231590 | Hyper | FOXG1 |
| chr14 | 29242763 | 29242908 | Hyper | BC034423, C14orf23, FOXG1 | chr14 | 29237063 | 29237107 | Hyper | C14orf23, FOXG1 |
| chr14 | 29243856 | 29243888 | Hyper | BC034423, C14orf23, FOXG1 | chr14 | 29243516 | 29243560 | Hyper | FOXG1, BC034423, C14orf23 |
| chr14 | 29247689 | 29247740 | Hyper | BC034423, C14orf23, FOXG1 | chr14 | 29244224 | 29244308 | Hyper | BC034423, C14orf23, FOXG1 |
| chr14 | 31344346 | 31344549 | Hyper | LOC100506071, COCH | chr14 | 29254575 | 29254713 | Hyper | BC034423, C14orf23 |
| chr14 | 33403270 | 33403316 | Hyper | NPAS3 | chr14 | 33402462 | 33402762 | Hyper | NPAS3 |
| chr14 | 36004063 | 36004493 | Hyper | RALGAPA1, INSM2 | chr14 | 33403866 | 33404418 | Hyper | NPAS3 |
| chr14 | 36972803 | 36972912 | Hyper | SFTA3 | chr14 | 36004711 | 36004983 | Hyper | RALGAPA1, INSM2 |
| chr14 | 36974294 | 36974745 | Hyper | SFTA3 | chr14 | 36973254 | 36973538 | Hyper | SFTA3 |
| chr14 | 36977645 | 36978009 | Hyper | NKX2-1, SFTA3 | chr14 | 36975299 | 36975399 | Hyper | SFTA3 |
| chr14 | 36979619 | 36979649 | Hyper | NKX2-1, BX161496, SFTA3 | chr14 | 36978548 | 36978578 | Hyper | SFTA3, NKX2-1, BX161496 |
| chr14 | 36983708 | 36984146 | Hyper | NKX2-1, BX161496, SFTA3 | chr14 | 36982927 | 36982969 | Hyper | BX161496, SFTA3, NKX2-1 |
| chr14 | 36986301 | 36986841 | Hyper | BX161496, NKX2-1, SFTA3 | chr14 | 36985841 | 36985871 | Hyper | NKX2-1, SFTA3, BX161496 |
| chr14 | 36987939 | 36988143 | Hyper | BX161496, NKX2-1, SFTA3 | chr14 | 36987168 | 36987685 | Hyper | BX161496, NKX2-1, SFTA3 |
| chr14 | 36991532 | 36991613 | Hyper | BX161496, NKX2-1, SFTA3 | chr14 | 36990858 | 36991177 | Hyper | BX161496, NKX2-1, SFTA3 |
| chr14 | 36993473 | 36993956 | Hyper | NKX2-1, BX161496 | chr14 | 36991936 | 36992417 | Hyper | BX161496, NKX2-1, SFTA3 |
| chr14 | 37050752 | 37050794 | Hyper | NKX2-8 | chr14 | 36994248 | 36994999 | Hyper | BX161496, NKX2-1 |
| chr14 | 37117611 | 37117697 | Hyper | PAX9 | chr14 | 37116105 | 37116381 | Hyper | |
| chr14 | 37124364 | 37124572 | Hyper | PAX9 | chr14 | 37123438 | 37124077 | Hyper | PAX9 |
| chr14 | 37126241 | 37126297 | Hyper | PAX9 | chr14 | 37124992 | 37125488 | Hyper | PAX9 |
| chr14 | 37127281 | 37127311 | Hyper | PAX9 | chr14 | 37126566 | 37126897 | Hyper | PAX9 |
| chr14 | 37128553 | 37128723 | Hyper | PAX9 | chr14 | 37127655 | 37128021 | Hyper | PAX9 |
| chr14 | 37132375 | 37132695 | Hyper | PAX9 | chr14 | 37130077 | 37130260 | Hyper | PAX9 |
| chr14 | 37135784 | 37136345 | Hyper | PAX9 | chr14 | 37133001 | 37133052 | Hyper | PAX9 |
| chr14 | 38060677 | 38060916 | Hyper | FOXA1 | chr14 | 37136588 | 37136618 | Hyper | PAX9 |
| chr14 | 38724780 | 38725258 | Hyper | CLEC14A | chr14 | 38724294 | 38724560 | Hyper | CLEC14A |

TABLE 1-continued

| Chr | Start | Stop | Hypo/hyper | Annotation | Chr | Start | Stop | Hypo/hyper | Annotation |
|---|---|---|---|---|---|---|---|---|---|
| chr14 | 42075588 | 42076212 | Hyper | LRFN5 | chr14 | 42074544 | 42074987 | Hyper | LRFN5 |
| chr14 | 42077230 | 42077268 | Hyper | LRFN5 | chr14 | 42076823 | 42076853 | Hyper | LRFN5 |
| chr14 | 42079289 | 42079328 | Hyper | LRFN5 | chr14 | 42077770 | 42077800 | Hyper | LRFN5 |
| chr14 | 48144298 | 48144401 | Hyper | | chr14 | 42143755 | 42144097 | Hyper | |
| chr14 | 51338730 | 51338972 | Hyper | ABHD12B | chr14 | 48144699 | 48145257 | Hyper | |
| chr14 | 52534648 | 52534791 | Hyper | NID2 | chr14 | 51560304 | 51561428 | Hyper | TRIM9 |
| chr14 | 52734509 | 52734557 | Hyper | PTGDR | chr14 | 52535012 | 52536404 | Hyper | NID2 |
| chr14 | 52781525 | 52781916 | Hyper | PTGER2 | chr14 | 52734777 | 52735255 | Hyper | PTGDR |
| chr14 | 57260946 | 57261821 | Hyper | OTX2 | chr14 | 54422651 | 54422694 | Hyper | BMP4, MIR5580 |
| chr14 | 57264079 | 57265240 | Hyper | OTX2 | chr14 | 57262072 | 57262179 | Hyper | OTX2 |
| chr14 | 57272009 | 57272067 | Hyper | OTX2-AS1, OTX2 | chr14 | 57270995 | 57271266 | Hyper | OTX2, OTX2-AS1 |
| chr14 | 57275596 | 57276104 | Hyper | OTX2-AS1, OTX2 | chr14 | 57274486 | 57275305 | Hyper | OTX2-AS1, OTX2 |
| chr14 | 57277920 | 57279657 | Hyper | OTX2-AS1, OTX2 | chr14 | 57276440 | 57276666 | Hyper | OTX2-AS1, OTX2 |
| chr14 | 58332297 | 58332403 | Hyper | | chr14 | 57283314 | 57284659 | Hyper | OTX2-AS1 |
| chr14 | 60386207 | 60386252 | Hyper | LRRC9 | chr14 | 60097193 | 60097566 | Hyper | RTN1 |
| chr14 | 60794635 | 60794667 | Hyper | JB175233 | chr14 | 60386638 | 60386701 | Hyper | LRRC9 |
| chr14 | 60973151 | 60973324 | Hyper | SIX6 | chr14 | 60952166 | 60952959 | Hyper | C14orf39 |
| chr14 | 60974368 | 60974403 | Hyper | SIX6 | chr14 | 60973697 | 60974077 | Hyper | SIX6 |
| chr14 | 60976813 | 60976860 | Hyper | SIX6 | chr14 | 60975384 | 60976514 | Hyper | SIX6 |
| chr14 | 60981202 | 60981268 | Hyper | SIX6 | chr14 | 60977337 | 60978147 | Hyper | SIX6 |
| chr14 | 60982110 | 60982622 | Hyper | SIX6 | chr14 | 60981676 | 60981793 | Hyper | SIX6 |
| chr14 | 61104291 | 61104864 | Hyper | SIX1 | chr14 | 60982841 | 60982911 | Hyper | SIX6 |
| chr14 | 61109429 | 61109470 | Hyper | SIX1 | chr14 | 61108620 | 61108996 | Hyper | SIX1 |
| chr14 | 61114137 | 61114456 | Hyper | SIX1 | chr14 | 61109839 | 61110243 | Hyper | SIX1 |
| chr14 | 61118965 | 61119136 | Hyper | SIX1 | chr14 | 61115311 | 61115517 | Hyper | SIX1 |
| chr14 | 62279578 | 62280006 | Hyper | | chr14 | 61119536 | 61119639 | Hyper | SIX1 |
| chr14 | 63512100 | 63512291 | Hyper | KCNH5 | chr14 | 62583809 | 62583909 | Hyper | LINC00643 |
| chr14 | 63513124 | 63513154 | Hyper | KCNH5 | chr14 | 63512779 | 63512816 | Hyper | KCNH5 |
| chr14 | 70014723 | 70014934 | Hyper | | chr14 | 65008994 | 65009193 | Hyper | PPP1R36, HSPA2 |
| chr14 | 70038990 | 70039025 | Hyper | CCDC177 | chr14 | 70038540 | 70038635 | Hyper | CCDC177 |
| chr14 | 70654343 | 70654713 | Hyper | | chr14 | 70346314 | 70346441 | Hyper | SMOC1 |
| chr14 | 72398743 | 72399019 | Hyper | RGS6 | chr14 | 70655530 | 70656090 | Hyper | |
| chr14 | 72399929 | 72400029 | Hyper | RGS6 | chr14 | 72399361 | 72399453 | Hyper | RGS6 |
| chr14 | 74706458 | 74707873 | Hyper | VSX2 | chr14 | 74706015 | 74706222 | Hyper | VSX2 |
| chr14 | 74893074 | 74893113 | Hyper | SYNDIG1L | chr14 | 74708862 | 74708955 | Hyper | VSX2 |
| chr14 | 76604682 | 76604716 | Hyper | | chr14 | 75078170 | 75078507 | Hyper | LTBP2 |
| chr14 | 76843461 | 76843504 | Hyper | ESRRB | chr14 | 76605072 | 76605376 | Hyper | |
| chr14 | 77607025 | 77607058 | Hyper | ZDHHC22 | chr14 | 76843742 | 76843953 | Hyper | ESRRB |
| chr14 | 79745138 | 79745175 | Hyper | NRXN3 | chr14 | 77737212 | 77737356 | Hyper | MIR1260A, NGB, POMT2 |
| chr14 | 85996851 | 85996906 | Hyper | FLRT2, BX248253 | chr14 | 85996479 | 85996608 | Hyper | FLRT2, BX248253 |
| chr14 | 85998288 | 85998392 | Hyper | FLRT2, BX248253 | chr14 | 85997821 | 85998006 | Hyper | FLRT2, BX248253 |
| chr14 | 85999569 | 85999613 | Hyper | FLRT2, BX248253 | chr14 | 85998614 | 85998683 | Hyper | FLRT2, BX248253 |
| chr14 | 86000918 | 86001114 | Hyper | FLRT2, BX248253 | chr14 | 86000400 | 86000511 | Hyper | FLRT2, BX248253 |
| chr14 | 90527714 | 90527758 | Hyper | KCNK13 | chr14 | 89817889 | 89818034 | Hyper | |
| chr14 | 92790863 | 92790169 | Hyper | SLC24A4 | chr14 | 92789512 | 92789542 | Hyper | SLC24A4 |
| chr14 | 93389679 | 93389776 | Hyper | CHGA | chr14 | 92790637 | 92790703 | Hyper | SLC24A4 |
| chr14 | 94405734 | 94405785 | Hyper | ASB2 | chr14 | 94254389 | 94254513 | Hyper | PRIMA1 |
| chr14 | 95235989 | 95236111 | Hyper | GSC | chr14 | 95234773 | 95235369 | Hyper | GSC |
| chr14 | 95240127 | 95240157 | Hyper | GSC | chr14 | 95239380 | 95239633 | Hyper | GSC |
| chr14 | 96342648 | 96342692 | Hyper | LINC00617 | chr14 | 95240392 | 95240422 | Hyper | GSC |
| chr14 | 96343643 | 96343701 | Hyper | LINC00617 | chr14 | 96342897 | 96343024 | Hyper | LINC00617 |
| chr14 | 97499277 | 97499315 | Hyper | | chr14 | 97058856 | 97059083 | Hyper | BC035096 |
| chr14 | 97685044 | 97685288 | Hyper | | chr14 | 97499706 | 97499944 | Hyper | |
| chr14 | 99584575 | 99584664 | Hyper | | chr14 | 97685707 | 97685959 | Hyper | |
| chr14 | 100437794 | 100437977 | Hyper | EVL | chr14 | 99736151 | 99736183 | Hyper | BCL11B |
| chr14 | 101193242 | 101193286 | Hyper | DLK1 | chr14 | 100438705 | 100438811 | Hyper | EVL |
| chr14 | 101923114 | 101923250 | Hyper | | chr14 | 101543868 | 101543967 | Hyper | BC148240, MEG9 |
| chr14 | 10192395 | 101924047 | Hyper | | chr14 | 101923600 | 101923738 | Hyper | |
| chr14 | 101925701 | 101925901 | Hyper | | chr14 | 101925049 | 101925439 | Hyper | |
| chr14 | 102031231 | 102031271 | Hyper | DIO3, MIR1247, DIO3AS, DIO3OS | chr14 | 102026360 | 102026484 | Hyper | MIR1247, DIO3, DIO3AS, DIO3OS |
| chr14 | 102247912 | 102248214 | Hyper | PPP2R5C | chr14 | 102031512 | 102031580 | Hyper | DIO3, MIR1247, DIO3AS, DIO3OS |

TABLE 1-continued

| Chr | Start | Stop | Hypo/hyper | Annotation | Chr | Start | Stop | Hypo/hyper | Annotation |
|---|---|---|---|---|---|---|---|---|---|
| chr14 | 103395035 | 103395101 | Hyper | CDC42BPB, AMN | chr14 | 103021391 | 103022003 | Hyper | |
| chr14 | 10367407 | 103674143 | Hyper | | chr14 | 103655226 | 103655601 | Hyper | LINC00605 |
| chr14 | 103739967 | 103740150 | Hyper | | chr14 | 103687082 | 103687219 | Hyper | |
| chr14 | 103745690 | 103745750 | Hyper | | chr14 | 103740358 | 103740430 | Hyper | |
| chr14 | 104602033 | 104602063 | Hyper | KIF26A | chr14 | 104601737 | 104601832 | Hyper | KIF26A |
| chr10 | 1651331 | 1651374 | Hyper | | chr14 | 104605032 | 104605114 | Hyper | KIF26A |
| chr10 | 7449954 | 7451279 | Hyper | SFMBT2 | chr10 | 1779473 | 1779640 | Hyper | |
| chr10 | 7453313 | 7453930 | Hyper | SFMBT2 | chr10 | 7452742 | 7452777 | Hyper | SFMBT2 |
| chr10 | 7708842 | 7708912 | Hyper | ITIH5 | chr10 | 7708274 | 7708304 | Hyper | ITIH5 |
| chr10 | 8076338 | 8076487 | Hyper | | chr10 | 8075930 | 8075971 | Hyper | |
| chr10 | 8077874 | 8078218 | Hyper | | chr10 | 8076804 | 8077374 | Hyper | |
| chr10 | 8085978 | 8086010 | Hyper | GATA3-AS1, BC036297 | chr10 | 8085039 | 8085721 | Hyper | GATA3-AS1, BC036297 |
| chr10 | 8093738 | 8093985 | Hyper | GATA3, GATA3-AS1, BC036297 | chr10 | 8091895 | 8091982 | Hyper | GATA3, GATA3-AS1, BC036297 |
| chr10 | 8096160 | 8096190 | Hyper | GATA3, BC036297, GATA3-AS1 | chr10 | 8095603 | 8095655 | Hyper | GATA3-AS1, GATA3, BC036297 |
| chr10 | 8097474 | 8097537 | Hyper | GATA3, BC036297, GATA3-AS1 | chr10 | 8096975 | 8097197 | Hyper | BC036297, GATA3-AS1, GATA3 |
| chr10 | 11207179 | 11207276 | Hyper | CELF2 | chr10 | 11059928 | 11060062 | Hyper | CELF2 |
| chr10 | 13933005 | 13933035 | Hyper | FRMD4A | chr10 | 13043386 | 13043425 | Hyper | AK311458 |
| chr10 | 15761292 | 15761671 | Hyper | ITGA8 | chr10 | 13934183 | 13934211 | Hyper | FRMD4A |
| chr10 | 16562086 | 16562297 | Hyper | C1QL3 | chr10 | 15762124 | 15762154 | Hyper | ITGA8 |
| chr10 | 17271223 | 17271625 | Hyper | VIM, BC078172 | chr10 | 16562545 | 16563909 | Hyper | C1QL3 |
| chr10 | 18429245 | 18429287 | Hyper | CACNB2 | chr10 | 17496214 | 17496734 | Hyper | |
| chr10 | 22541638 | 22542265 | Hyper | LOC100130992 | chr10 | 21805217 | 21805277 | Hyper | AK303207, SKIDA1, AK055656 |
| chr10 | 22633985 | 22634504 | Hyper | SPAG6 | chr10 | 22624022 | 22625978 | Hyper | COMMD3-BMI1, SPAG6, BMI1 |
| chr10 | 23216865 | 23216945 | Hyper | ARMC3 | chr10 | 22764649 | 22765901 | Hyper | |
| chr10 | 23461222 | 23461754 | Hyper | SNORA40 | chr10 | 23460355 | 23460471 | Hyper | SNORA40 |
| chr10 | 23463150 | 23464077 | Hyper | SNORA40 | chr10 | 23462059 | 23462910 | Hyper | SNORA40 |
| chr10 | 23481321 | 23481515 | Hyper | PTF1A | chr10 | 23479876 | 23481086 | Hyper | PTF1A |
| chr10 | 23483828 | 23484618 | Hyper | PTF1A | chr10 | 23481936 | 23482445 | Hyper | PTF1A |
| chr10 | 23487742 | 23487978 | Hyper | PTF1A | chr10 | 23486264 | 23486328 | Hyper | PTF1A |
| chr10 | 23489409 | 23489439 | Hyper | PTF1A | chr10 | 23488393 | 23489158 | Hyper | PTF1A |
| chr10 | 23983194 | 23983247 | Hyper | KIAA1217 | chr10 | 23982438 | 23982820 | Hyper | KIAA1217 |
| chr10 | 23984087 | 23984226 | Hyper | KIAA1217 | chr10 | 23983482 | 23983552 | Hyper | KIAA1217 |
| chr10 | 25464619 | 25464915 | Hyper | GPR158, GPR158-AS1 | chr10 | 23984923 | 23984991 | Hyper | KIAA1217 |
| chr10 | 26055811 | 26055841 | Hyper | | chr10 | 25465421 | 25465517 | Hyper | GPR158, GPR158-AS1 |
| chr10 | 26224031 | 26224061 | Hyper | MYO3A | chr10 | 26223001 | 26223424 | Hyper | MYO3A |
| chr10 | 26501539 | 26501589 | Hyper | GAD2, MYO3A | chr10 | 26500619 | 26500915 | Hyper | GAD2, MYO3A |
| chr10 | 26504159 | 26504159 | Hyper | MYO3A, GAD2 | chr10 | 26503693 | 26503731 | Hyper | GAD2, MYO3A |
| chr10 | 26505440 | 26505705 | Hyper | GAD2, MYO3A | chr10 | 26504491 | 26505227 | Hyper | GAD2, MYO3A |
| chr10 | 26506373 | 26507400 | Hyper | GAD2, MYO3A | chr10 | 26506057 | 26506163 | Hyper | MYO3A, GAD2 |
| chr10 | 26727098 | 26727368 | Hyper | APBB1IP | chr10 | 26681099 | 26681129 | Hyper | |
| chr10 | 27547946 | 27548484 | Hyper | AK125237, LRRC37A6P | chr10 | 26727604 | 26727832 | Hyper | APBB1IP |
| chr10 | 28032966 | 28033020 | Hyper | MKX | chr10 | 28030892 | 28030925 | Hyper | MKX |
| chr10 | 28033770 | 28034088 | Hyper | MKX | chr10 | 28033410 | 28033481 | Hyper | MKX |
| chr10 | 28034575 | 28035300 | Hyper | MKX | chr10 | 28034295 | 28034341 | Hyper | MKX |
| chr10 | 28287777 | 28288070 | Hyper | | chr10 | 28035615 | 28035782 | Hyper | MKX |
| chr10 | 29011047 | 29011162 | Hyper | | chr10 | 28958086 | 28958129 | Hyper | BAMBI |
| chr10 | 35929498 | 35929528 | Hyper | FZD8 | chr10 | 35929150 | 35929216 | Hyper | FZD8 |
| chr10 | 43250406 | 43250886 | Hyper | | chr10 | 43250009 | 43250039 | Hyper | |
| chr10 | 43429004 | 43429100 | Hyper | | chr10 | 43428424 | 43428592 | Hyper | |
| chr10 | 43572685 | 43572734 | Hyper | RET | chr10 | 43429376 | 43429411 | Hyper | |
| chr10 | 43697887 | 43697996 | Hyper | RASGEF1A | chr10 | 43600561 | 43600609 | Hyper | RET |
| chr10 | 44880869 | 44880915 | Hyper | CXCL12 | chr10 | 44879944 | 44880228 | Hyper | CXCL12 |
| chr10 | 49732060 | 49732103 | Hyper | | chr10 | 49731642 | 49731749 | Hyper | |
| chr10 | 50323222 | 50323258 | Hyper | FAM170B-AS1, VSTM4 | chr10 | 49732398 | 49732498 | Hyper | |
| chr10 | 50604608 | 50604645 | Hyper | DRGX | chr10 | 50603967 | 50604159 | Hyper | DRGX |
| chr10 | 50606027 | 50606433 | Hyper | DRGX | chr10 | 50605057 | 50605654 | Hyper | DRGX |
| chr10 | 50817858 | 50817935 | Hyper | SLC18A3, CHAT | chr10 | 50817015 | 50817132 | Hyper | CHAT, SLC18A3 |
| chr10 | 50818823 | 50819102 | Hyper | CHAT, SLC18A3 | chr10 | 50818382 | 50818432 | Hyper | CHAT, SLC18A3 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr10 | 50887655 | 50887816 | Hyper | C10orf53 | chr10 | 50821472 | 50821701 | Hyper | SLC18A3, CHAT |
| chr10 | 54068526 | 54068610 | Hyper | PRKG1-AS1, DKK1 | chr10 | 50976880 | 50977048 | Hyper | OGDHL |
| chr10 | 54073265 | 54073295 | Hyper | PRKG1-AS1, DKK1 | chr10 | 54072982 | 54073020 | Hyper | DKK1, PRKG1-AS1 |
| chr10 | 57387429 | 57387796 | Hyper | | chr10 | 54074744 | 54074789 | Hyper | DKK1, PRKG1-AS1 |
| chr10 | 57390290 | 57390637 | Hyper | | chr10 | 57388325 | 57388510 | Hyper | |
| chr10 | 60273130 | 60273294 | Hyper | BICC1 | chr10 | 57391166 | 57391215 | Hyper | |
| chr10 | 60936524 | 60936732 | Hyper | PHYHIPL | chr10 | 60935887 | 60935996 | Hyper | PHYHIPL |
| chr10 | 63212324 | 63212701 | Hyper | BC041470, TMEM26 | chr10 | 60937073 | 60937103 | Hyper | PHYHIPL |
| chr10 | 64578470 | 64578540 | Hyper | EGR2 | chr10 | 64575526 | 64575638 | Hyper | EGR2, ADO |
| chr10 | 71328773 | 71328821 | Hyper | NEUROG3 | chr10 | 71327725 | 71327764 | Hyper | NEUROG3 |
| chr10 | 71329544 | 71329618 | Hyper | NEUROG3 | chr10 | 71329079 | 71329118 | Hyper | NEUROG3 |
| chr10 | 71332821 | 71333018 | Hyper | NEUROG3 | chr10 | 71332052 | 71332572 | Hyper | NEUROG3 |
| chr10 | 72043638 | 72043894 | Hyper | NPFFR1 | chr10 | 72015150 | 72015339 | Hyper | NPFFR 1 |
| chr10 | 72200354 | 72201285 | Hyper | NODAL | chr10 | 72200102 | 72200138 | Hyper | NODAL |
| chr10 | 77191224 | 77191368 | Hyper | | chr10 | 73847886 | 73848114 | Hyper | ASCC1, SPOCK2 |
| chr10 | 81664867 | 81664899 | Hyper | LOC100288974 | chr10 | 79396921 | 79397089 | Hyper | KCNMA1 |
| chr10 | 88149363 | 88149601 | Hyper | | chr10 | 83635515 | 83635545 | Hyper | NRG3 |
| chr10 | 90967671 | 90968040 | Hyper | LIPA, CH25H | chr10 | 90966708 | 90966865 | Hyper | LIPA, CH25H |
| chr10 | 91295531 | 91295725 | Hyper | | chr10 | 91295029 | 91295067 | Hyper | |
| chr10 | 94450675 | 94450726 | Hyper | HHEX | chr10 | 92617242 | 92617308 | Hyper | HTR7 |
| chr10 | 94826023 | 94826056 | Hyper | CYP26A1, CYP26C1, EXOC6 | chr10 | 94451448 | 94451653 | Hyper | HHEX |
| chr10 | 94828735 | 94828828 | Hyper | CYP26C1, EXOC6, CYP26A1 | chr10 | 94828163 | 94828498 | Hyper | CYP26A1, CYP26C1, EXOC6 |
| chr10 | 99080262 | 99080447 | Hyper | FRAT1 | chr10 | 94834413 | 94835047 | Hyper | CYP26A1, CYP26C1 |
| chr10 | 99531219 | 99531275 | Hyper | SFRP5 | chr10 | 99080862 | 99080984 | Hyper | FRAT1 |
| chr10 | 99790261 | 99790318 | Hyper | | chr10 | 99789175 | 99789282 | Hyper | |
| chr10 | 99790947 | 99791161 | Hyper | | chr10 | 99790590 | 99790664 | Hyper | |
| chr10 | 100992882 | 100992916 | Hyper | HPSE2 | chr10 | 100991907 | 100992409 | Hyper | HPSE2 |
| chr10 | 100996046 | 100996224 | Hyper | HPSE2 | chr10 | 100993537 | 100994016 | Hyper | HPSE2 |
| chr10 | 101089908 | 101090203 | Hyper | CNNM1 | chr10 | 101088995 | 101089415 | Hyper | CNNM1 |
| chr10 | 101290117 | 101291191 | Hyper | NKX2-3, chromosome 10 open reading frame 139, DQ372722 | chr10 | 101280204 | 101280485 | Hyper | DQ372722, chromosome 10 open reading frame 139 |
| chr10 | 101293156 | 101293343 | Hyper | NKX2-3, chromosome 10 open reading frame 139, DQ372722 | chr10 | 101292297 | 101292919 | Hyper | DQ372722, NKX2-3, chromosome 10 open reading frame 139 |
| chr10 | 101296768 | 101296800 | Hyper | NKX2-3, chromosome 10 open reading frame 139, DQ372722 | chr10 | 101294756 | 101295586 | Hyper | NKX2-3, chromosome 10 open reading frame 139, DQ372722 |
| chr10 | 102419316 | 102419681 | Hyper | | chr10 | 102322230 | 102322260 | Hyper | HIF1AN |
| chr10 | 102473856 | 102473932 | Hyper | | chr10 | 102430699 | 102430761 | Hyper | |
| chr10 | 102495508 | 102495741 | Hyper | PAX2 | chr10 | 102483993 | 102484554 | Hyper | |
| chr10 | 102497525 | 102497708 | Hyper | PAX2 | chr10 | 102497273 | 102497325 | Hyper | PAX2 |
| chr10 | 102501359 | 102501389 | Hyper | PAX2 | chr10 | 102498280 | 102498433 | Hyper | PAX2 |
| chr10 | 102508996 | 102509285 | Hyper | PAX2 | chr10 | 102507509 | 102507605 | Hyper | PAX2 |
| chr10 | 102589425 | 102589493 | Hyper | | chr10 | 102586505 | 102586822 | Hyper | |
| chr10 | 102590152 | 102590415 | Hyper | | chr10 | 102589786 | 102589915 | Hyper | |
| chr10 | 102891823 | 102892025 | Hyper | TLX1, TLX1NB | chr10 | 102890941 | 102891582 | Hyper | TLX1NB, TLX1 |
| chr10 | 102899173 | 102899601 | Hyper | TLX1, TLX1NB | chr10 | 102893624 | 102895289 | Hyper | TLX1, TLX1NB |
| chr10 | 102906523 | 102906620 | Hyper | TLX1 | chr10 | 102899807 | 102900575 | Hyper | TLX1, TLX1NB |
| chr10 | 102976150 | 102976180 | Hyper | | chr10 | 102975619 | 102975834 | Hyper | |
| chr10 | 102983153 | 102983749 | Hyper | LBX1, FLJ41350 | chr10 | 102977051 | 102977412 | Hyper | LBX1 |
| chr10 | 102985772 | 102985963 | Hyper | LBX1, FLJ41350 | chr10 | 102984407 | 102984516 | Hyper | LBX1, FLJ41350 |
| chr10 | 102989629 | 102989659 | Hyper | FLJ41350, LBX1 | chr10 | 102986534 | 102987558 | Hyper | LBX1, FLJ41350 |
| chr10 | 102997329 | 102997406 | Hyper | FLJ41350, LBX1 | chr10 | 102996116 | 102996638 | Hyper | LBX1, FLJ41350 |
| chr10 | 103043975 | 103044366 | Hyper | | chr10 | 102998576 | 102999028 | Hyper | FLJ41350, LBX1 |
| chr10 | 104170096 | 104170527 | Hyper | PSD, FBXL15, NFKB2 | chr10 | 103536227 | 103536416 | Hyper | NPM3, MGEA5, FGF8 |
| chr10 | 105037223 | 105037830 | Hyper | INA | chr10 | 105036542 | 105036625 | Hyper | INA |
| chr10 | 106399581 | 106400387 | Hyper | SORCS3 | chr10 | 106398644 | 106398886 | Hyper | SORCS3 |
| chr10 | 106402712 | 106402825 | Hyper | SORCS3 | chr10 | 106400970 | 106402325 | Hyper | SORCS3 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr10 | 108924463 | 108924684 | Hyper | | chr10 | 108924045 | 108924095 | Hyper | |
| chr10 | 110671972 | 110672245 | Hyper | | chr10 | 110226258 | 110226304 | Hyper | |
| chr10 | 112403151 | 112403297 | Hyper | RBM20, Y_RNA | chr10 | 111216789 | 111216927 | Hyper | |
| chr10 | 118030642 | 118030875 | Hyper | GFRA1 | chr10 | 115804840 | 115805014 | Hyper | ADRB1 |
| chr10 | 118031942 | 118032547 | Hyper | GFRA1 | chr10 | 118031302 | 118031436 | Hyper | GFRA1 |
| chr10 | 118034138 | 118034168 | Hyper | GFRA1 | chr10 | 118032917 | 118033542 | Hyper | GFRA1 |
| chr10 | 118891517 | 118891774 | Hyper | KIAA1598, VAX1 | chr10 | 118890980 | 118891104 | Hyper | VAX1, KIAA1598 |
| chr10 | 118893582 | 118894283 | Hyper | VAX1, KIAA1598 | chr10 | 118892013 | 118893266 | Hyper | VAX1, KIAA1598 |
| chr10 | 118897913 | 118897968 | Hyper | VAX1 | chr10 | 118896629 | 118896805 | Hyper | VAX1 |
| chr10 | 118900166 | 118900498 | Hyper | VAX1 | chr10 | 118899511 | 118899957 | Hyper | VAX1 |
| chr10 | 118922787 | 118922886 | Hyper | MIR3663, BC039338 | chr10 | 118922143 | 118922208 | Hyper | MIR3663, BC039338 |
| chr10 | 118924604 | 118924896 | Hyper | MIR3663, BC039338 | chr10 | 118923138 | 118923259 | Hyper | MIR3663, BC039338 |
| chr10 | 118928548 | 118928727 | Hyper | MIR3663, BC039338 | chr10 | 118927086 | 118927296 | Hyper | MIR3663, BC039338 |
| chr10 | 119001534 | 119001564 | Hyper | SLC18A2 | chr10 | 119000662 | 119001304 | Hyper | SLC18A2 |
| chr10 | 119294352 | 119294461 | Hyper | EMX2OS, EMX2 | chr10 | 119292277 | 119292320 | Hyper | EMX2, EMX2OS |
| chr10 | 119296706 | 119296788 | Hyper | EMX2OS, EMX2 | chr10 | 119294847 | 119295245 | Hyper | EMX2, EMX2OS |
| chr10 | 119301365 | 119301669 | Hyper | EMX2, EMX2OS | chr10 | 119297384 | 119297529 | Hyper | EMX2, EMX2OS |
| chr10 | 119302962 | 119303174 | Hyper | EMX2, EMX2OS | chr10 | 119302141 | 119302266 | Hyper | EMX2, EMX2OS |
| chr10 | 119304896 | 119305109 | Hyper | EMX2, EMX2OS | chr10 | 119304363 | 119304393 | Hyper | EMX2, EMX2OS |
| chr10 | 119311867 | 119311897 | Hyper | EMX2, EMX2OS | chr10 | 119307022 | 119307052 | Hyper | EMX2, EMX2OS |
| chr10 | 120354243 | 120354273 | Hyper | PRLHR | chr10 | 119312751 | 119313193 | Hyper | EMX2, EMX2OS |
| chr10 | 122708495 | 122708691 | Hyper | | chr10 | 120355548 | 120355614 | Hyper | PRLHR |
| chr10 | 123922645 | 123923464 | Hyper | TACC2 | chr10 | 122708992 | 122709022 | Hyper | |
| chr10 | 124893635 | 124893765 | Hyper | HMX3 | chr10 | 124893178 | 124893350 | Hyper | HMX3 |
| chr10 | 124894889 | 124894922 | Hyper | HMX3 | chr10 | 124893965 | 124894479 | Hyper | HMX3 |
| chr10 | 124896861 | 124896913 | Hyper | HMX3 | chr10 | 124895742 | 124896456 | Hyper | HMX3 |
| chr10 | 124899035 | 124899116 | Hyper | HMX2, HMX3 | chr10 | 124897220 | 124897973 | Hyper | HMX3, HMX2 |
| chr10 | 124901892 | 124903238 | Hyper | HMX2, HMX3 | chr10 | 124899754 | 124899786 | Hyper | HMX3, HMX2 |
| chr10 | 124905481 | 124905511 | Hyper | HMX2, BUB3, HMX3 | chr10 | 124904921 | 124905119 | Hyper | HMX2, BUB3, HMX3 |
| chr10 | 124906436 | 124906544 | Hyper | HMX2, BUB3, HMX3 | chr10 | 124905911 | 124906174 | Hyper | HMX3, HMX2, BUB3 |
| chr10 | 124908091 | 124908121 | Hyper | BUB3, HMX2 | chr10 | 124907312 | 124907534 | Hyper | HMX2, BUB3 |
| chr10 | 124909625 | 124909701 | Hyper | BUB3, HMX2 | chr10 | 124909086 | 124909377 | Hyper | BUB3, HMX2 |
| chr10 | 124910625 | 124911048 | Hyper | BUB3, HMX2 | chr10 | 124910382 | 124910412 | Hyper | BUB3, HMX2 |
| chr10 | 12565086 | 125651348 | Hyper | CPXM2 | chr10 | 125425515 | 125425547 | Hyper | GPR26 |
| chr10 | 126135927 | 126136065 | Hyper | NKX1-2 | chr10 | 125851328 | 125851372 | Hyper | CHST15 |
| chr10 | 126137181 | 126137405 | Hyper | NKX1-2 | chr10 | 126136506 | 126136651 | Hyper | NKX1-2 |
| chr10 | 128077262 | 128077292 | Hyper | ADAM12 | chr10 | 128076561 | 128076630 | Hyper | ADAM12 |
| chr10 | 128994727 | 128994783 | Hyper | FAM196A | chr10 | 128993904 | 128994357 | Hyper | FAM196A |
| chr10 | 129536080 | 129536310 | Hyper | BC132944, FOXI2 | chr10 | 129534597 | 129535733 | Hyper | FOXI2, BC132944 |
| chr10 | 130338896 | 130338976 | Hyper | | chr10 | 130085295 | 130085362 | Hyper | AK124226 |
| chr10 | 131757946 | 131758056 | Hyper | EBF3 | chr10 | 131757091 | 131757430 | Hyper | EBF3 |
| chr10 | 131761687 | 131761725 | Hyper | EBF3 | chr10 | 131761378 | 131761441 | Hyper | EBF3 |
| chr10 | 131762592 | 131762631 | Hyper | EBF3 | chr10 | 131762087 | 131762124 | Hyper | EBF3 |
| chr10 | 131763348 | 131763717 | Hyper | EBF3 | chr10 | 131762904 | 131762940 | Hyper | EBF3 |
| chr10 | 131768724 | 131769029 | Hyper | EBF3 | chr10 | 131767608 | 131767649 | Hyper | EBF3 |
| chr10 | 131770657 | 131770687 | Hyper | EBF3 | chr10 | 131769533 | 131770237 | Hyper | EBF3 |
| chr10 | 133109192 | 133109297 | Hyper | | chr10 | 131770988 | 131771245 | Hyper | EBF3 |
| chr10 | 133110353 | 133110704 | Hyper | | chr10 | 133109634 | 133109781 | Hyper | |
| chr10 | 133795316 | 133795369 | Hyper | BNIP3 | chr10 | 133794883 | 133795020 | Hyper | BNIP3 |
| chr10 | 133849818 | 133850008 | Hyper | | chr10 | 133795682 | 133796221 | Hyper | BNIP3 |
| chr10 | 134001114 | 134001260 | Hyper | AL137551, JAKMIP3, DPYSL4 | chr10 | 133850658 | 133850693 | Hyper | |
| chr10 | 134598336 | 134598530 | Hyper | INPP5A, NKX6-2 | chr10 | 134598087 | 134598117 | Hyper | NKX6-2, INPP5A |
| chr10 | 134599452 | 134599482 | Hyper | INPP5A, NKX6-2 | chr10 | 134599062 | 134599225 | Hyper | NKX6-2, INPP5A |
| chr10 | 134600301 | 134600801 | Hyper | NKX6-2, INPP5A | chr10 | 134599995 | 134600055 | Hyper | NKX6-2, INPP5A |
| chr10 | 134602183 | 134602269 | Hyper | INPP5A, NKX6-2 | chr10 | 134601556 | 134601798 | Hyper | NKX6-2, INPP5A |

TABLE 1-continued

| Chr | Start | Stop | Hypo/hyper | Annotation | Chr | Start | Stop | Hypo/hyper | Annotation |
|---|---|---|---|---|---|---|---|---|---|
| chr10 | 134756083 | 134756138 | Hyper | TTC40 | chr10 | 134755757 | 134755808 | Hyper | TTC40 |
| chr10 | 135043088 | 135043538 | Hyper | UTF1, VENTX | chr10 | 134902008 | 134902307 | Hyper | GPR123 |
| chr10 | 135044511 | 135044573 | Hyper | VENTX, UTF1 | chr10 | 135043968 | 135044002 | Hyper | VENTX, UTF1 |
| chr10 | 135050551 | 135050679 | Hyper | VENTX, UTF1 | chr10 | 135048782 | 135048939 | Hyper | VENTX, UTF1 |
| chr12 | 1639135 | 1639222 | Hyper | | chr12 | 570090 | 570171 | Hyper | B4GALNT3 |
| chr12 | 2163164 | 2163276 | Hyper | CACNA1C | chr12 | 2162554 | 2162817 | Hyper | CACNA1C |
| chr12 | 3600315 | 3600345 | Hyper | PRMT8, AK125333, DQ579489, DQ583138, DQ596092 | chr12 | 2862068 | 2862225 | Hyper | LOC283440 |
| chr12 | 3603100 | 3603156 | Hyper | PRMT8, AK125333 | chr12 | 3602270 | 3602879 | Hyper | DQ579489, PRMT8, AK125333 |
| chr12 | 5018073 | 5018243 | Hyper | KCNA1 | chr12 | 4274054 | 4274188 | Hyper | |
| chr12 | 5019050 | 5020416 | Hyper | KCNA1 | chr12 | 5018570 | 5018692 | Hyper | KCNA1 |
| chr12 | 5542325 | 5542439 | Hyper | NTF3 | chr12 | 5153073 | 5153520 | Hyper | KCNA5 |
| chr12 | 6664508 | 6665325 | Hyper | NOP2, IFFO1 | chr12 | 5542759 | 5542911 | Hyper | NTF3 |
| chr12 | 11653449 | 11653479 | Hyper | | chr12 | 8171360 | 8171745 | Hyper | |
| chr12 | 14133619 | 14133881 | Hyper | | chr12 | 14133152 | 14133263 | Hyper | |
| chr12 | 15374258 | 15374291 | Hyper | RERG | chr12 | 14135111 | 14135339 | Hyper | |
| chr12 | 20522457 | 20522487 | Hyper | PDE3A | chr12 | 20521704 | 20521841 | Hyper | PDE3A |
| chr12 | 21680435 | 21680465 | Hyper | C12orf39, GYS2, GOLT1B | chr12 | 20522769 | 20522891 | Hyper | PDE3A |
| chr12 | 22095095 | 22095136 | Hyper | ABCC9 | chr12 | 22093825 | 22094810 | Hyper | ABCC9 |
| chr12 | 25056227 | 25056634 | Hyper | BCAT1 | chr12 | 22486799 | 22487455 | Hyper | ST8SIA1 |
| chr12 | 25101919 | 25102086 | Hyper | | chr12 | 25101592 | 25101660 | Hyper | |
| chr12 | 28128547 | 28129084 | Hyper | PTHLH | chr12 | 28127767 | 28128214 | Hyper | PTHLH |
| chr12 | 29936602 | 29936864 | Hyper | TMTC1 | chr12 | 29936016 | 29936048 | Hyper | TMTC1 |
| chr12 | 30322774 | 30323517 | Hyper | | chr12 | 29937331 | 29937374 | Hyper | TMTC1 |
| chr12 | 31079268 | 31079499 | Hyper | TSPAN11 | chr12 | 30975572 | 30975895 | Hyper | |
| chr12 | 33592613 | 33592889 | Hyper | SYT10 | chr12 | 33591774 | 33591804 | Hyper | SYT10 |
| chr12 | 39539353 | 39539436 | Hyper | | chr12 | 39299475 | 39299560 | Hyper | CPNE8 |
| chr12 | 41086784 | 41087106 | Hyper | CNTN1 | chr12 | 40618404 | 40618470 | Hyper | LRRK2 |
| chr12 | 41583374 | 41583419 | Hyper | PDZRN4 | chr12 | 41582735 | 41582988 | Hyper | PDZRN4 |
| chr12 | 43945356 | 43945526 | Hyper | | chr12 | 43944893 | 43945124 | Hyper | |
| chr12 | 45444118 | 45445258 | Hyper | DBX2 | chr12 | 43945844 | 43946298 | Hyper | |
| chr12 | 48397195 | 48398070 | Hyper | COL2A1 | chr12 | 47225381 | 47225579 | Hyper | SLC38A4 |
| chr12 | 49297802 | 49297915 | Hyper | CCDC65 | chr12 | 48398641 | 48398671 | Hyper | COL2A1 |
| chr12 | 49374914 | 49375119 | Hyper | WNT1, WNT10B | chr12 | 49366374 | 49366423 | Hyper | WNT10B, WNT1 |
| chr12 | 49390873 | 49391877 | Hyper | PRKAG1, DDN | chr12 | 49375499 | 49375529 | Hyper | WNT1, WNT10B |
| chr12 | 49729728 | 49730090 | Hyper | C1QL4, TROAP | chr12 | 49727049 | 49727127 | Hyper | C1QL4, TROAP |
| chr12 | 50355275 | 50355469 | Hyper | AQP2, AQP5, AQP6 | chr12 | 50297497 | 50298055 | Hyper | BC034605, FAIM2, LOC283332 |
| chr12 | 52262983 | 52263106 | Hyper | | chr12 | 50426748 | 50426799 | Hyper | RACGAP1 |
| chr12 | 52400831 | 52401339 | Hyper | GRASP, ACVR1B | chr12 | 52301280 | 52301367 | Hyper | ACVRL1 |
| chr12 | 52652153 | 52652613 | Hyper | KRT121P, KRT86, KRT7 | chr12 | 52627184 | 52627286 | Hyper | KRT7, LINC00592 |
| chr12 | 53359345 | 53359563 | Hyper | | chr12 | 53108089 | 53108218 | Hyper | |
| chr12 | 54132252 | 54132329 | Hyper | | chr12 | 54089093 | 54089351 | Hyper | |
| chr12 | 54321250 | 54321628 | Hyper | HOXC-AS5 | chr12 | 54145843 | 54145895 | Hyper | |
| chr12 | 54324799 | 54324937 | Hyper | HOXC-AS5, HOXC13 | chr12 | 54322201 | 54322252 | Hyper | HOXC-AS5 |
| chr12 | 54331062 | 54331135 | Hyper | HOXC13, HOXC-AS5 | chr12 | 54329358 | 54329947 | Hyper | HOXC13, HOXC-AS5 |
| chr12 | 54338666 | 54339681 | Hyper | HOXC-AS5, HOXC12, HOXC13 | chr12 | 54332868 | 54333337 | Hyper | HOXC13, HOXC-AS5 |
| chr12 | 54345611 | 54346032 | Hyper | HOXC12, HOXC13 | chr12 | 54343812 | 5434386 | Hyper | HOXC12, HOXC13 |
| chr12 | 54354514 | 54354621 | Hyper | HOTAIR_5, HOXC12, HOTAIR, HOTAIR_4 | chr12 | 54348844 | 54349336 | Hyper | HOTAIR, HOXC12, HOXC13 |
| chr12 | 54359960 | 54360084 | Hyper | HOXC12, HOTAIR_4, HOTAIR_5, HOXC11, HOTAIR | chr12 | 54354905 | 54355474 | Hyper | HOTAIR_4, HOTAIR_5, HOXC12, HOTAIR |
| chr12 | 54377912 | 54378115 | Hyper | HOXC10, MIR196A2, HOXC11 | chr12 | 54360608 | 54360649 | Hyper | HOTAIR 4, HOTAIR_5, HOXC11, HOTAIR |

TABLE 1-continued

| Chr | Start | Stop | Hypo/hyper | Annotation | Chr | Start | Stop | Hypo/hyper | Annotation |
|---|---|---|---|---|---|---|---|---|---|
| chr12 | 54379888 | 54380459 | Hyper | MIR196A2, HOXC10, HOXC11 | chr12 | 54379174 | 54379623 | Hyper | HOXC11, MIR196A2, HOXC10 |
| chr12 | 54388215 | 54388245 | Hyper | MIR196A2, HOXC10, HOXC9 | chr12 | 54387842 | 54387950 | Hyper | HOXC10, HOXC9, MIR196A2 |
| chr12 | 54393479 | 54393684 | Hyper | HOXC9, HOXC8, MIR196A2, HOXC10 | chr12 | 54391369 | 54391403 | Hyper | HOXC9, MIR196A2, HOXC10 |
| chr12 | 54394410 | 54394442 | Hyper | HOXC8, HOXC9, MIR196A2 | chr12 | 54393950 | 54394162 | Hyper | HOXC9, MIR196A2, HOXC10, HOXC8 |
| chr12 | 54402690 | 54402796 | Hyper | HOXC6, HOXC4, HOXC5, HOXC9, HOXC8 | chr12 | 54398793 | 54398959 | Hyper | HOXC8, HOXC9 |
| chr12 | 54408411 | 54408726 | Hyper | HOXC4, HOXC5, HOXC8, HOXC6 | chr12 | 54403067 | 54403360 | Hyper | HOXC9, HOXC6, HOXC4, HOXC5, HOXC8 |
| chr12 | 54424746 | 54424788 | Hyper | HOXC5, MIR615, HOXC6, HOXC4 | chr12 | 54423565 | 54423697 | Hyper | HOXC4, HOXC5, MIR615, HOXC6 |
| chr12 | 54447351 | 54447581 | Hyper | HOXC4, FLJ12825 | chr12 | 54425003 | 54425119 | Hyper | HOXC5, MIR615, HOXC6, HOXC4 |
| chr12 | 54520745 | 54520868 | Hyper | LOC400043 | chr12 | 54447883 | 54447977 | Hyper | FLJ12825, HOXC4 |
| chr12 | 57618574 | 57618920 | Hyper | SHMT2, NDUFA4L2, NXPH4 | chr12 | 54812238 | 54812359 | Hyper | ITGA5 |
| chr12 | 58021320 | 58021639 | Hyper | SLC26A10, BC073932, B4GALNT1 | chr12 | 57944081 | 57944117 | Hyper | KIF5A, DCTN2 |
| chr12 | 62584838 | 62585930 | Hyper | FAM19A2 | chr12 | 58025646 | 58025873 | Hyper | JA611266, B4GALNT1, SLC26A10 |
| chr12 | 63543848 | 63544727 | Hyper | AVPR1A | chr12 | 63025714 | 63026160 | Hyper | |
| chr12 | 64061821 | 64062159 | Hyper | DPY19L2 | chr12 | 63545313 | 63545343 | Hyper | AVPR1A |
| chr12 | 64784092 | 64784187 | Hyper | | chr12 | 64062921 | 64063096 | Hyper | DPY19L2 |
| chr12 | 65218102 | 65219156 | Hyper | TBC1D30 | chr12 | 64784534 | 64784564 | Hyper | |
| chr12 | 65220205 | 65220350 | Hyper | TBC1D30 | chr12 | 65219376 | 65219784 | Hyper | TBC1D30 |
| chr12 | 66122800 | 66123519 | Hyper | | chr12 | 65514863 | 65515596 | Hyper | WIF1 |
| chr12 | 66582827 | 66583137 | Hyper | IRAK3 | chr12 | 66135984 | 66136014 | Hyper | |
| chr12 | 72665186 | 72665788 | Hyper | BC093903, TRHDE, TRHDE-AS1 | chr12 | 69327259 | 69327463 | Hyper | CPM |
| chr12 | 72666713 | 72667425 | Hyper | TRHDE, BC093903, TRHDE-AS1 | chr12 | 72666115 | 72666211 | Hyper | TRHDE, BC093903, TRHDE-AS1 |
| chr12 | 75601264 | 75601910 | Hyper | KCNC2 | chr12 | 72667652 | 72667682 | Hyper | TRHDE-AS1, TRHDE, BC093903 |
| chr12 | 75728336 | 75728447 | Hyper | GLIPR1L1, CAPS2 | chr12 | 75602976 | 75603231 | Hyper | KCNC2 |
| chr12 | 81102185 | 81102530 | Hyper | MYF5, MYF6 | chr12 | 79258924 | 79258954 | Hyper | SYT1 |
| chr12 | 85306519 | 85306578 | Hyper | SLC6A15 | chr12 | 81471517 | 81472111 | Hyper | ACSS3 |
| chr12 | 85673460 | 85674807 | Hyper | ALX1 | chr12 | 85667272 | 85667731 | Hyper | ALX1 |
| chr12 | 93966998 | 93967239 | Hyper | SOCS2, SOCS2-AS1 | chr12 | 93966429 | 93966603 | Hyper | SOCS2-AS1, SOCS2 |
| chr12 | 94543899 | 94543961 | Hyper | PLXNC1 | chr12 | 94543409 | 94543445 | Hyper | PLXNC1 |
| chr12 | 95941891 | 95942978 | Hyper | USP44 | chr12 | 95267865 | 95267976 | Hyper | |
| chr12 | 99288825 | 99289309 | Hyper | ANKS1B | chr12 | 99288312 | 99288487 | Hyper | ANKS1B |
| chr12 | 101111373 | 101111479 | Hyper | ANO4 | chr12 | 101111029 | 101111061 | Hyper | ANO4 |
| chr12 | 103350324 | 103350354 | Hyper | ASCL1 | chr12 | 103218495 | 103218595 | Hyper | LINC00485 |
| chr12 | 103352107 | 103352681 | Hyper | ASCL1 | chr12 | 103351564 | 103351732 | Hyper | ASCL1 |
| chr12 | 103359556 | 103359586 | Hyper | ASCL1 | chr12 | 103358865 | 103358899 | Hyper | ASCL1 |
| chr12 | 104609435 | 104610100 | Hyper | TXNRD 1 | chr12 | 103889746 | 103889812 | Hyper | C12orf42 |
| chr12 | 106974353 | 106974383 | Hyper | RFX4, LOC100287944 | chr12 | 104852315 | 104852508 | Hyper | CHST11 |
| chr12 | 106977321 | 106977497 | Hyper | RFX4, LOC100287944 | chr12 | 106976725 | 106976795 | Hyper | RFX4, LOC100287944 |
| chr12 | 106979799 | 106979995 | Hyper | RFX4, LOC100287944 | chr12 | 106979161 | 106979534 | Hyper | RFX4, LOC100287944 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr12 | 106980854 | 106981406 | Hyper | RFX4, LOC100287944 | chr12 | 106980223 | 106980333 | Hyper | RFX4, LOC100287944 |
| chr12 | 107714866 | 107715153 | Hyper | BTBD11 | chr12 | 107713205 | 107713235 | Hyper | BTBD11 |
| chr12 | 108237466 | 108237586 | Hyper | | chr12 | 108168971 | 108169573 | Hyper | ASCL4 |
| chr12 | 108238582 | 108238616 | Hyper | | chr12 | 108238102 | 108238363 | Hyper | |
| chr12 | 111127324 | 111127455 | Hyper | HVCN1 | chr12 | 108297411 | 108297466 | Hyper | LOC728739 |
| chr12 | 111471971 | 111472752 | Hyper | CUX2 | chr12 | 111471397 | 111471559 | Hyper | CUX2 |
| chr12 | 113541661 | 113542099 | Hyper | RASAL1, DTX1 | chr12 | 113012954 | 113013157 | Hyper | RPH3A |
| chr12 | 113901074 | 113901591 | Hyper | LHX5 | chr12 | 113592238 | 113592359 | Hyper | DDX54, CCDC42B |
| chr12 | 113903468 | 113903498 | Hyper | LHX5 | chr12 | 113902026 | 113902353 | Hyper | LHX5 |
| chr12 | 113908990 | 113909455 | Hyper | LHX5 | chr12 | 113904779 | 113905016 | Hyper | LHX5 |
| chr12 | 113913267 | 113914050 | Hyper | LHX5 | chr12 | 113909667 | 113909708 | Hyper | LHX5 |
| chr12 | 113916972 | 113917012 | Hyper | LHX5 | chr12 | 113916222 | 113916316 | Hyper | LHX5 |
| chr12 | 113917775 | 113917890 | Hyper | LHX5 | chr12 | 113917232 | 113917310 | Hyper | LHX5 |
| chr12 | 114833985 | 114834102 | Hyper | TBX5 | chr12 | 114076029 | 114076093 | Hyper | |
| chr12 | 114839104 | 114839147 | Hyper | TBX5-AS1, TBX5 | chr12 | 114838325 | 114838726 | Hyper | TBX5-AS1, TBX5 |
| chr12 | 114841425 | 114841493 | Hyper | TBX5-AS1, TBX5 | chr12 | 114841046 | 114841084 | Hyper | TBX5-AS1, TBX5 |
| chr12 | 114843545 | 114843660 | Hyper | TBX5-AS1, TBX5 | chr12 | 114843112 | 114843278 | Hyper | TBX5, TBX5-AS1 |
| chr12 | 114846715 | 114846768 | Hyper | TBX5-AS1, TBX5 | chr12 | 114844201 | 114844300 | Hyper | TBX5-AS1, TBX5 |
| chr12 | 114852040 | 114852082 | Hyper | TBX5-AS1 | chr12 | 114846979 | 114847691 | Hyper | TBX5-AS1, TBX5 |
| chr12 | 114878550 | 114878584 | Hyper | | chr12 | 114877171 | 114877262 | Hyper | |
| chr12 | 114881634 | 114881764 | Hyper | | chr12 | 114878813 | 114879012 | Hyper | |
| chr12 | 114883473 | 114883535 | Hyper | | chr12 | 114882555 | 114882646 | Hyper | |
| chr12 | 114918594 | 114918717 | Hyper | | chr12 | 114885222 | 114885284 | Hyper | |
| chr12 | 116946086 | 116946548 | Hyper | | chr12 | 115136159 | 115136363 | Hyper | |
| chr12 | 117798690 | 117798965 | Hyper | NOS1 | chr12 | 117798065 | 117798095 | Hyper | NOS1 |
| chr12 | 119212216 | 119212381 | Hyper | | chr12 | 117799413 | 117799529 | Hyper | NOS1 |
| chr12 | 119419436 | 119419466 | Hyper | SRRM4 | chr12 | 119418594 | 119418847 | Hyper | SRRM4 |
| chr12 | 120032862 | 120033169 | Hyper | TMEM233, AF086288 | chr12 | 119419720 | 119419899 | Hyper | SRRM4 |
| chr12 | 125670117 | 125670289 | Hyper | | chr12 | 125533949 | 125534407 | Hyper | |
| chr12 | 127210965 | 127211378 | Hyper | LINC00944 | chr12 | 126168554 | 126168620 | Hyper | |
| chr12 | 128751384 | 128751443 | Hyper | TMEM132C | chr12 | 127765158 | 127765432 | Hyper | |
| chr12 | 128752499 | 128752944 | Hyper | TMEM132C | chr12 | 128751821 | 128752240 | Hyper | TMEM132C |
| chr12 | 128850534 | 128850644 | Hyper | | chr12 | 128753210 | 128753240 | Hyper | TMEM132C |
| chr12 | 130387776 | 130387811 | Hyper | | chr12 | 129338003 | 129338816 | Hyper | GLTID1 |
| chr12 | 130589202 | 130589266 | Hyper | | chr12 | 130388410 | 130389152 | Hyper | |
| chr12 | 130646686 | 130647047 | Hyper | FZD10, FZD10-AS1 | chr12 | 130645233 | 130645627 | Hyper | FZD10, FZD10-AS1 |
| chr12 | 131400816 | 131400919 | Hyper | | chr12 | 130647408 | 130648472 | Hyper | FZD10, FZD10-AS1 |
| chr12 | 133484896 | 133485355 | Hyper | AK055957 | chr12 | 133481398 | 133481655 | Hyper | AK055957 |
| chr1 | 1475556 | 1476318 | Hyper | TMEM240, AX747755, ATAD3A, SSU72 | chr12 | 133485557 | 133485847 | Hyper | AK055957 |
| chr1 | 2375191 | 2375543 | Hyper | | chr1 | 2165895 | 2165999 | Hyper | SKI |
| chr1 | 2984719 | 2984749 | Hyper | PRDM16, FLJ42875 | chr1 | 2706197 | 2706469 | Hyper | TTC34 |
| chr1 | 4714024 | 4714345 | Hyper | AJAP1 | chr1 | 3567093 | 3568226 | Hyper | TP73, WRAP73 |
| chr1 | 4716598 | 4716701 | Hyper | AJAP1 | chr1 | 4714741 | 4716102 | Hyper | AJAP1 |
| chr1 | 6480514 | 6480831 | Hyper | ESPN, MIR4252, HES2 | chr1 | 6304201 | 6304242 | Hyper | HES3, GPR153, C1orf211, ICMT |
| chr1 | 8277374 | 8277718 | Hyper | | chr1 | 6501001 | 6501179 | Hyper | ESPN |
| chr1 | 10948552 | 10948582 | Hyper | | chr1 | 9712883 | 9713014 | Hyper | C1orf200, PIK3CD |
| chr1 | 11752476 | 11752511 | Hyper | DRAXIN | chr1 | 11540129 | 11540238 | Hyper | PTCHD2 |
| chr1 | 12123421 | 12123640 | Hyper | TNFRSF8 | chr1 | 11959093 | 11959196 | Hyper | |
| chr1 | 13839955 | 13839985 | Hyper | LRRC38 | chr1 | 12227911 | 12227941 | Hyper | TNFRSF1B |
| chr1 | 13910682 | 13910712 | Hyper | PDPN | chr1 | 13910436 | 13910468 | Hyper | PDPN |
| chr1 | 16861522 | 16861552 | Hyper | BC036435, TRNA_Asn, AX747988 | chr1 | 14925501 | 14926050 | Hyper | KAZN |
| chr1 | 18437457 | 18437526 | Hyper | IGSF21 | chr1 | 18434449 | 18434520 | Hyper | IGSF21 |
| chr1 | 18956574 | 18956655 | Hyper | PAX7 | chr1 | 18956211 | 18956304 | Hyper | PAX7 |
| chr1 | 18957507 | 18957587 | Hyper | PAX7 | chr1 | 18956856 | 18957246 | Hyper | PAX7 |
| chr1 | 18959440 | 18959550 | Hyper | PAX7 | chr1 | 18958033 | 18958264 | Hyper | PAX7 |
| chr1 | 18962727 | 18963135 | Hyper | PAX7 | chr1 | 18960897 | 18960990 | Hyper | PAX7 |
| chr1 | 18971852 | 18971929 | Hyper | PAX7 | chr1 | 18969625 | 18969819 | Hyper | PAX7 |
| chr1 | 19043563 | 19043678 | Hyper | PAX7 | chr1 | 18972130 | 18972160 | Hyper | PAX7 |
| chr1 | 20618329 | 20618369 | Hyper | VWA5B1 | chr1 | 19992349 | 19992432 | Hyper | HTR6, NBL1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr1 | 20879562 | 20879640 | Hyper | FAM43B | chr1 | 20879035 | 20879289 | Hyper | FAM43B |
| chr1 | 20880182 | 20880475 | Hyper | FAM43B | chr1 | 20879845 | 20879957 | Hyper | FAM43B |
| chr1 | 21835943 | 21836007 | Hyper | ALPL | chr1 | 21044125 | 21044161 | Hyper | KIF17, SH2D5 |
| chr1 | 23748982 | 23749070 | Hyper | ASAP3, TCEA3 | chr1 | 22140753 | 22141178 | Hyper | LDLRAD2, HSPG2 |
| chr1 | 26552086 | 26552130 | Hyper | CEP85, BC030768 | chr1 | 25257042 | 25257072 | Hyper | RUNX3 |
| chr1 | 26737946 | 26738182 | Hyper | LIN28A | chr1 | 26737583 | 26737613 | Hyper | LIN28A |
| chr1 | 29804947 | 29805094 | Hyper | | chr1 | 29586072 | 29586491 | Hyper | PTPRU |
| chr1 | 32237584 | 32238507 | Hyper | | chr1 | 30815412 | 30815578 | Hyper | |
| chr1 | 34628948 | 34628978 | Hyper | C1orf94 | chr1 | 32410276 | 32410306 | Hyper | PTP4A2 |
| chr1 | 34630548 | 34630635 | Hyper | C1orf94 | chr1 | 34629469 | 34629728 | Hyper | C1orf94 |
| chr1 | 34631580 | 34631662 | Hyper | C1orf94 | chr1 | 34630859 | 34630978 | Hyper | C1orf94 |
| chr1 | 34642380 | 34642573 | Hyper | C1orf94 | chr1 | 34631933 | 34631963 | Hyper | C1orf94 |
| chr1 | 35351078 | 35351659 | Hyper | DLGAP3 | chr1 | 35258637 | 35258714 | Hyper | GJA4, GJB3 |
| chr1 | 37498792 | 37499181 | Hyper | GRIK3 | chr1 | 36042679 | 36043489 | Hyper | PSMB2, TFAP2E |
| chr1 | 37500468 | 37500806 | Hyper | GRIK3 | chr1 | 37499460 | 37500153 | Hyper | GRIK3 |
| chr1 | 38100689 | 38100735 | Hyper | RSPO1 | chr1 | 37501072 | 37501102 | Hyper | GRIK3 |
| chr1 | 38230042 | 38230297 | Hyper | EPHA10 | chr1 | 38219712 | 38219795 | Hyper | EPHA10 |
| chr1 | 38412668 | 38412758 | Hyper | SF3A3, INPP5B | chr1 | 38230779 | 38230809 | Hyper | EPHA10 |
| chr1 | 38510563 | 38510624 | Hyper | POU3F1 | chr1 | 38510217 | 38510247 | Hyper | POU3F1 |
| chr1 | 38511337 | 38511824 | Hyper | POU3F1 | chr1 | 38510854 | 38511069 | Hyper | POU3F1 |
| chr1 | 40237141 | 40237203 | Hyper | BMP8B, OXCT2 | chr1 | 39269869 | 39270121 | Hyper | |
| chr1 | 41847583 | 41847702 | Hyper | | chr1 | 41283958 | 41284463 | Hyper | KCNQ4 |
| chr1 | 44872812 | 44873706 | Hyper | RNF220 | chr1 | 41848810 | 41848840 | Hyper | |
| chr1 | 44884080 | 44884197 | Hyper | RNF220 | chr1 | 44883121 | 44883846 | Hyper | RNF220 |
| chr1 | 46913837 | 46914283 | Hyper | LOC729041 | chr1 | 46632876 | 46632923 | Hyper | TSPAN1 |
| chr1 | 46951207 | 46951739 | Hyper | | chr1 | 46914656 | 46914686 | Hyper | LOC729041 |
| chr1 | 46956823 | 46957171 | Hyper | | chr1 | 46956454 | 46956603 | Hyper | |
| chr1 | 47695122 | 47695422 | Hyper | STIL, JA375062, TAL1 | chr1 | 47009929 | 47010070 | Hyper | KNCN, MKNK1-AS1 |
| chr1 | 47696821 | 47697110 | Hyper | TAL1, STIL, JA375062 | chr1 | 47696295 | 47696597 | Hyper | STIL, JA375062, TAL1 |
| chr1 | 47697732 | 47698210 | Hyper | STIL, JA375062, TAL1 | chr1 | 47697356 | 47697476 | Hyper | STIL, JA375062, TAL1 |
| chr1 | 47882769 | 47882803 | Hyper | FOXE3 | chr1 | 47882063 | 47882311 | Hyper | FOXE3 |
| chr1 | 47910523 | 47910875 | Hyper | FOXD2 | chr1 | 47909718 | 47910160 | Hyper | FOXD2, FOXD2-AS1 |
| chr1 | 50513629 | 50513745 | Hyper | ELAVL4 | chr1 | 48059078 | 48059243 | Hyper | |
| chr1 | 50880911 | 50881302 | Hyper | DMRTA2 | chr1 | 50799278 | 50799400 | Hyper | |
| chr1 | 50882808 | 50883611 | Hyper | DMRTA2 | chr1 | 50881521 | 50882529 | Hyper | DMRTA2 |
| chr1 | 50885336 | 50885366 | Hyper | DMRTA2 | chr1 | 50883882 | 50884916 | Hyper | DMRTA2 |
| chr1 | 50888781 | 50888811 | Hyper | DMRTA2 | chr1 | 50886188 | 50887284 | Hyper | DMRTA2 |
| chr1 | 50889820 | 50890379 | Hyper | DMRTA2 | chr1 | 50889104 | 50889496 | Hyper | DMRTA2 |
| chr1 | 50892153 | 50892351 | Hyper | DMRTA2 | chr1 | 50890683 | 50891595 | Hyper | DMRTA2 |
| chr1 | 53068181 | 53068232 | Hyper | GPX7 | chr1 | 50892804 | 50893871 | Hyper | DMRTA2 |
| chr1 | 53308568 | 53309248 | Hyper | ZYG11A | chr1 | 53068490 | 53068546 | Hyper | GPX7 |
| chr1 | 54203516 | 54204399 | Hyper | GLIS1 | chr1 | 53528374 | 53528439 | Hyper | PODN |
| chr1 | 57888367 | 57888397 | Hyper | DAB1 | chr1 | 55462673 | 55462703 | Hyper | BSND, TMEM61 |
| chr1 | 57889478 | 57889654 | Hyper | DAB1 | chr1 | 57888987 | 57889087 | Hyper | DAB1 |
| chr1 | 58715153 | 58715194 | Hyper | | chr1 | 57890431 | 57890548 | Hyper | DAB1 |
| chr1 | 61519360 | 61519394 | Hyper | | chr1 | 58715475 | 58715993 | Hyper | |
| chr1 | 63785333 | 63786329 | Hyper | FOXD3 | chr1 | 63539509 | 63539851 | Hyper | |
| chr1 | 63787302 | 63787568 | Hyper | FOXD3 | chr1 | 63787031 | 63787063 | Hyper | FOXD3 |
| chr1 | 63790045 | 63790278 | Hyper | U7, FOXD3 | chr1 | 63788788 | 63789837 | Hyper | FOXD3, U7 |
| chr1 | 63795263 | 63796277 | Hyper | U7, FOXD3 | chr1 | 63792561 | 63793072 | Hyper | U7, FOXD3 |
| chr1 | 65731337 | 65731367 | Hyper | DNAJC6, AK123450 | chr1 | 63796498 | 63796575 | Hyper | U7, FOXD3 |
| chr1 | 65990955 | 65991034 | Hyper | LEPR | chr1 | 65731649 | 65731679 | Hyper | DNAJC6, AK123450 |
| chr1 | 66258180 | 66258493 | Hyper | PDE4B | chr1 | 65991506 | 65991620 | Hyper | LEPR |
| chr1 | 66259137 | 66259174 | Hyper | PDE4B | chr1 | 66258696 | 66258759 | Hyper | PDE4B |
| chr1 | 66999636 | 66999673 | Hyper | SGIP1 | chr1 | 66998790 | 66999332 | Hyper | SGIP1 |
| chr1 | 67773159 | 67773297 | Hyper | IL12RB2 | chr1 | 67218064 | 67218343 | Hyper | TCTEX1D1, SGIP1 |
| chr1 | 70034459 | 70034574 | Hyper | LRRC7 | chr1 | 67773519 | 67773780 | Hyper | IL12RB2 |
| chr1 | 72749641 | 72749715 | Hyper | | chr1 | 70035088 | 70035537 | Hyper | LRRC7 |
| chr1 | 75596687 | 75597584 | Hyper | LHX8, AK055631 | chr1 | 75595798 | 75596384 | Hyper | LHX8, AK055631 |
| chr1 | 75598384 | 75598414 | Hyper | AK055631, LHX8 | chr1 | 75597923 | 75598179 | Hyper | LHX8, AK055631 |
| chr1 | 75600225 | 75600848 | Hyper | AK055631, LHX8 | chr1 | 75599427 | 75599621 | Hyper | LHX8, AK055631 |
| chr1 | 75601983 | 75603052 | Hyper | LHX8, AK055631 | chr1 | 75601058 | 75601428 | Hyper | LHX8, AK055631 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr1 | 76082129 | 76082209 | Hyper | SLC44A5 | chr1 | 76080484 | 76080768 | Hyper | SLC44A5 |
| chr1 | 77333058 | 77333088 | Hyper | ST6GALNAC5 | chr1 | 76540524 | 76540666 | Hyper | ST6GALNAC3 |
| chr1 | 77334099 | 77334658 | Hyper | ST6GALNAC5 | chr1 | 77333384 | 77333544 | Hyper | ST6GALNAC5 |
| chr1 | 77747939 | 77748024 | Hyper | AK5 | chr1 | 77747366 | 77747453 | Hyper | AK5 |
| chr1 | 78957292 | 78957522 | Hyper | PTGFR | chr1 | 78511466 | 78512354 | Hyper | GIPC2 |
| chr1 | 86621660 | 86621726 | Hyper | COL24A1 | chr1 | 85358622 | 85358822 | Hyper | LPAR3 |
| chr1 | 87617774 | 87617807 | Hyper | | chr1 | 86622526 | 86622716 | Hyper | COL24A1 |
| chr1 | 91177941 | 91178207 | Hyper | BARHL2 | chr1 | 91172012 | 91172677 | Hyper | BARHL2 |
| chr1 | 91181932 | 91182132 | Hyper | BARHL2 | chr1 | 91180075 | 91180306 | Hyper | BARHL2 |
| chr1 | 91183105 | 91183379 | Hyper | BARHL2 | chr1 | 91182338 | 91182665 | Hyper | BARHL2 |
| chr1 | 91184423 | 91184672 | Hyper | BARHL2 | chr1 | 91183951 | 91183986 | Hyper | BARHL2 |
| chr1 | 91188983 | 91189383 | Hyper | BARHL2 | chr1 | 91185190 | 91185707 | Hyper | BARHL2 |
| chr1 | 91190869 | 91191310 | Hyper | BARHL2 | chr1 | 91189688 | 91190380 | Hyper | BARHL2 |
| chr1 | 91194414 | 91194569 | Hyper | | chr1 | 91192274 | 91192761 | Hyper | BARHL2 |
| chr1 | 91195879 | 91196502 | Hyper | | chr1 | 91195117 | 91195390 | Hyper | |
| chr1 | 91316627 | 91316682 | Hyper | | chr1 | 91316261 | 91316313 | Hyper | |
| chr1 | 92948841 | 92948976 | Hyper | GFI1 | chr1 | 92948324 | 92948597 | Hyper | GFI1 |
| chr1 | 98510791 | 98511335 | Hyper | MIR2682, MIR137, MIR137HG | chr1 | 92952145 | 92952481 | Hyper | GFI1 |
| chr1 | 98514225 | 98514255 | Hyper | MIR137HG, MIR137, MIR2682 | chr1 | 98511628 | 98511922 | Hyper | MIR137, MIR2682, MIR137HG |
| chr1 | 98519221 | 98519518 | Hyper | MIR2682, MIR137HG, MIR137 | chr1 | 98515256 | 98515319 | Hyper | MIR137, MIR2682, MIR137HG |
| chr1 | 99470785 | 99470847 | Hyper | LOC100129620, LPPR5 | chr1 | 99469682 | 99469788 | Hyper | LOC100129620, LPPR5 |
| chr1 | 101005071 | 101005144 | Hyper | GPR88 | chr1 | 101004456 | 101004737 | Hyper | GPR88 |
| chr1 | 101702552 | 101702592 | Hyper | S1PR1 | chr1 | 101005360 | 101005675 | Hyper | GPR88 |
| chr1 | 107682735 | 107682765 | Hyper | NTNG1 | chr1 | 101703612 | 101703642 | Hyper | S1PR1 |
| chr1 | 108507320 | 108507497 | Hyper | VAV3-AS1 | chr1 | 107683439 | 107683517 | Hyper | NTNG1 |
| chr1 | 108508166 | 108508640 | Hyper | VAV3-AS1 | chr1 | 108507717 | 108507810 | Hyper | VAV3-AS1 |
| chr1 | 110612846 | 110613152 | Hyper | DQ574855, ALX3 | chr1 | 110610586 | 110611925 | Hyper | DQ574855, ALX3 |
| chr1 | 110672880 | 110673233 | Hyper | | chr1 | 110626684 | 110627578 | Hyper | |
| chr1 | 110693827 | 110694117 | Hyper | SLC6A17 | chr1 | 110692973 | 110693425 | Hyper | SLC6A17 |
| chr1 | 111097906 | 111097936 | Hyper | | chr1 | 110754309 | 110754830 | Hyper | KCNC4 |
| chr1 | 111216763 | 111217372 | Hyper | KCNA3 | chr1 | 111098196 | 111098316 | Hyper | |
| chr1 | 111506007 | 111506212 | Hyper | LRIF1 | chr1 | 111217595 | 111217982 | Hyper | KCNA3 |
| chr1 | 114695439 | 114695469 | Hyper | | chr1 | 111813546 | 111813587 | Hyper | CHIAP2 |
| chr1 | 114696210 | 114696712 | Hyper | | chr1 | 114695703 | 114695943 | Hyper | |
| chr1 | 115880184 | 115880245 | Hyper | | chr1 | 115632469 | 115632555 | Hyper | TSPAN2 |
| chr1 | 116371139 | 116371201 | Hyper | NHLH2 | chr1 | 115881152 | 115881218 | Hyper | |
| chr1 | 116382387 | 116382478 | Hyper | NHLH2 | chr1 | 116380651 | 116381287 | Hyper | NHLH2 |
| chr1 | 119522839 | 119522940 | Hyper | TBX15 | chr1 | 119522074 | 119522530 | Hyper | TBX15 |
| chr1 | 119528653 | 119529118 | Hyper | TBX15 | chr1 | 119527072 | 119527205 | Hyper | TBX15 |
| chr1 | 119530100 | 119530725 | Hyper | TBX15 | chr1 | 119529804 | 119529839 | Hyper | TBX15 |
| chr1 | 119536142 | 119536377 | Hyper | TBX15 | chr1 | 119531029 | 119531157 | Hyper | TBX15 |
| chr1 | 119542997 | 119543230 | Hyper | | chr1 | 119542322 | 119542352 | Hyper | |
| chr1 | 119549058 | 119549929 | Hyper | | chr1 | 119543532 | 119544182 | Hyper | |
| chr1 | 119550533 | 119550633 | Hyper | | chr1 | 119550155 | 119550278 | Hyper | |
| chr1 | 151694260 | 151694351 | Hyper | RIJAD1, CELF3 | chr1 | 119550904 | 119551269 | Hyper | |
| chr1 | 152488150 | 152488197 | Hyper | CRCT1, LCE5A | chr1 | 152085398 | 152085504 | Hyper | TCHH |
| chr1 | 154475153 | 154475531 | Hyper | TDRD10, SHE | chr1 | 153651965 | 153652379 | Hyper | NPR1, TRNA_Met, ILF2 |
| chr1 | 156215607 | 156215805 | Hyper | SMG5, PAQR6, BGLAP | chr1 | 156215329 | 156215359 | Hyper | SMG5, PAQR6, BGLAP |
| chr1 | 156390135 | 156390698 | Hyper | C1orf61, MIR9-1 | chr1 | 156357993 | 156358508 | Hyper | RHBG |
| chr1 | 156594974 | 156595021 | Hyper | HAPLN2 | chr1 | 156405518 | 156406431 | Hyper | C1orf61 |
| chr1 | 156626589 | 156626658 | | BCAN | chr1 | 156611889 | 156612119 | Hyper | BCAN, BC005081 |
| chr1 | 156646593 | 156646647 | | NES | chr1 | 156626891 | 156627034 | Hyper | BCAN |
| chr1 | 156815445 | 156815496 | | INSRR, NTRK1 | chr1 | 156814933 | 156815146 | Hyper | NTRK1, INSRR |
| chr1 | 156863662 | 156863724 | | PEAR1 | chr1 | 156863107 | 156863331 | Hyper | PEAR1 |
| chr1 | 161228784 | 161228891 | | PCP4L1 | chr1 | 159158348 | 159158511 | Hyper | CADM3, LOC100131825 |
| chr1 | 161591472 | 161591546 | | FCGR3B, TRNA_Asn, TRNA_Glu, TRNA_Leu | chr1 | 161275564 | 161276026 | Hyper | SDHC, MPZ |
| chr1 | 164290615 | 164290689 | | | chr1 | 162792306 | 162792533 | Hyper | HSD17B7, C1orf110 |
| chr1 | 165205079 | 165205146 | | LMX1A | chr1 | 165086988 | 165087027 | Hyper | |
| chr1 | 165323151 | 165323181 | | LMX1A | chr1 | 165321747 | 165321852 | Hyper | LMX1A |
| chr1 | 165324488 | 165324668 | Hyper | LMX1A | chr1 | 165324196 | 165324249 | Hyper | LMX1A |

TABLE 1-continued

| Chr | Start | Stop | Hypo/hyper | Annotation | Chr | Start | Stop | Hypo/hyper | Annotation |
|---|---|---|---|---|---|---|---|---|---|
| chr1 | 165325896 | 165325950 | Hyper | LMX1A | chr1 | 165325108 | 165325521 | Hyper | LMX1A |
| chr1 | 165414191 | 165414272 | Hyper | RXRG | chr1 | 165326204 | 165326469 | Hyper | LMX1A |
| chr1 | 166134728 | 166134796 | Hyper | | chr1 | 166134247 | 166134306 | Hyper | |
| chr1 | 167599179 | 167599330 | Hyper | RCSD1 | chr1 | 166916866 | 166917100 | Hyper | ILDR2 |
| chr1 | 169396376 | 169396923 | Hyper | CCDC181 | chr1 | 167599662 | 167599735 | Hyper | RCSD1 |
| chr1 | 170631084 | 170631163 | Hyper | PRRX1 | chr1 | 170630458 | 170630810 | Hyper | PRRX1 |
| chr1 | 170637666 | 170637796 | Hyper | PRRX1 | chr1 | 170631477 | 170631559 | Hyper | PRRX1 |
| chr1 | 171810200 | 171810765 | Hyper | DNM3 | chr1 | 170640517 | 170640691 | Hyper | PRRX1 |
| chr1 | 177133721 | 177133814 | Hyper | FAM5B | chr1 | 173638647 | 173639085 | Hyper | ANKRD45 |
| chr1 | 179544967 | 179545098 | Hyper | | chr1 | 177140105 | 177140714 | Hyper | FAM5B |
| chr1 | 180198061 | 180198209 | Hyper | LHX4 | chr1 | 179712164 | 179713399 | Hyper | FAM163A |
| chr1 | 180203413 | 180204140 | Hyper | LHX4 | chr1 | 180202424 | 180203016 | Hyper | LHX4 |
| chr1 | 181287679 | 181287757 | Hyper | | chr1 | 180204483 | 180204924 | Hyper | LHX4 |
| chr1 | 181451407 | 181452120 | Hyper | CACNA1E, Mir_544 | chr1 | 181288014 | 181288188 | Hyper | |
| chr1 | 181454873 | 181454912 | Hyper | CACNA1E, Mir_544 | chr1 | 181452871 | 181452967 | Hyper | Mir_544, CACNA1E |
| chr1 | 183386150 | 183386288 | Hyper | | chr1 | 181455183 | 181455263 | Hyper | Mir 544, CACNA1E |
| chr1 | 183386838 | 183386964 | Hyper | | chr1 | 183386500 | 183386626 | Hyper | |
| chr1 | 184005701 | 184005814 | Hyper | COLGALT2 | chr1 | 183387266 | 183387319 | Hyper | |
| chr1 | 190445181 | 190445276 | Hyper | CR936711, FAM5C | chr1 | 190444855 | 190444885 | Hyper | CR936711, FAM5C |
| chr1 | 196577773 | 196577858 | Hyper | | chr1 | 190447373 | 190447519 | Hyper | FAM5C, CR936711 |
| chr1 | 197879400 | 197880156 | Hyper | LHX9, C1orf53 | chr1 | 196578101 | 196578150 | Hyper | |
| chr1 | 197882453 | 197882611 | Hyper | LHX9, C1orf53 | chr1 | 197882140 | 197882201 | Hyper | LHX9, C1orf53 |
| chr1 | 197888052 | 197888319 | Hyper | LHX9 | chr1 | 197887052 | 197887741 | Hyper | LHX9 |
| chr1 | 200009357 | 200009450 | Hyper | NR5A2 | chr1 | 197888643 | 197889286 | Hyper | LHX9 |
| chr1 | 200011323 | 200012068 | Hyper | NR5A2 | chr1 | 200009750 | 200010114 | Hyper | NR5A2 |
| chr1 | 205312596 | 205312950 | Hyper | KLHDC8A | chr1 | 204653561 | 204653807 | Hyper | |
| chr1 | 205537663 | 205537772 | Hyper | MFSD4 | chr1 | 205424654 | 205424957 | Hyper | AK095633, MIR135B |
| chr1 | 208084289 | 208084488 | Hyper | CD34 | chr1 | 207669496 | 207670060 | Hyper | CR1 |
| chr1 | 210111526 | 210112140 | Hyper | SYT14 | chr1 | 210111146 | 210111176 | Hyper | SYT14 |
| chr1 | 214156419 | 214156902 | Hyper | PROX1 | chr1 | 213124653 | 213124805 | Hyper | VASH2 |
| chr1 | 214160107 | 214160184 | Hyper | PROX1 | chr1 | 214158838 | 214158966 | Hyper | PROX1 |
| chr1 | 215255094 | 215255799 | Hyper | KCNK2 | chr1 | 214360777 | 214360878 | Hyper | |
| chr1 | 217307486 | 217308274 | Hyper | | chr1 | 216897216 | 216897307 | Hyper | |
| chr1 | 217311265 | 217311839 | Hyper | | chr1 | 217309007 | 217309105 | Hyper | |
| chr1 | 218520074 | 218520399 | Hyper | TGFB2, LOC728463, RRP15 | chr1 | 217313042 | 217313747 | Hyper | |
| chr1 | 220700814 | 220700897 | Hyper | MARK1 | chr1 | 220101145 | 220101345 | Hyper | SLC30A10, RNU5F-1 |
| chr1 | 221053610 | 221053862 | Hyper | HLX | chr1 | 221052038 | 221052492 | Hyper | HLX |
| chr1 | 223302825 | 223302890 | Hyper | | chr1 | 221067506 | 221067688 | Hyper | HLX |
| chr1 | 224528814 | 224528844 | Hyper | | chr1 | 223936633 | 223937057 | Hyper | CAPN2 |
| chr1 | 224804097 | 224804187 | Hyper | CNIH3 | chr1 | 224803717 | 224803751 | Hyper | CNIH3 |
| chr1 | 224805131 | 224805808 | Hyper | CNIH3 | chr1 | 224804409 | 224804791 | Hyper | CNIH3 |
| chr1 | 227729780 | 227730075 | Hyper | | chr1 | 226925156 | 226925188 | Hyper | ITPKB |
| chr1 | 228248302 | 228248332 | Hyper | WNT3A | chr1 | 228195377 | 228196349 | Hyper | WNT3A |
| chr1 | 228566622 | 228566672 | Hyper | | chr1 | 228463311 | 228463706 | Hyper | OBSCN |
| chr1 | 228633990 | 228634261 | Hyper | | chr1 | 228604102 | 228604163 | Hyper | TRIM17, TRIM11, HIST3H3 |
| chr1 | 228651432 | 228651626 | Hyper | Histone3, MIR4666A, HIST3H2BB, HIST3H2A | chr1 | 228645160 | 228645734 | Hyper | HIST3H2BB, MIR4666A, Histone3, HIST3H2A |
| chr1 | 229542838 | 229543139 | Hyper | | chr1 | 228651879 | 228652629 | Hyper | MIR4666A, HIST3H2BB, HIST3H2A, Histone3 |
| chr1 | 229569810 | 229569852 | Hyper | NUP133, ACTA1 | chr1 | 229566753 | 229568204 | Hyper | ACTA1, NUP133 |
| chr1 | 234040241 | 234040319 | Hyper | SLC35F3 | chr1 | 231297103 | 231297221 | Hyper | TRIM67 |
| chr1 | 234041400 | 234041624 | Hyper | SLC35F3 | chr1 | 234040817 | 234041064 | Hyper | SLC35F3 |
| chr1 | 235813781 | 235814202 | Hyper | | chr1 | 234350042 | 234350100 | Hyper | SLC35F3, AK054726 |
| chr1 | 236228582 | 236228789 | Hyper | AX747246, NID1 | chr1 | 236227637 | 236228096 | Hyper | AX747246, NID1 |
| chr1 | 23684945 | 236850142 | Hyper | ACTN2 | chr1 | 236559176 | 236559271 | Hyper | EDARADD |
| chr1 | 237205687 | 237206735 | Hyper | RYR2 | chr1 | 237205434 | 237205478 | Hyper | RYR2 |
| chr1 | 240161098 | 240161493 | Hyper | RPS7P5 | chr1 | 239550594 | 239551193 | Hyper | CHRM3 |
| chr1 | 240255361 | 240255500 | Hyper | FMN2 | chr1 | 240254944 | 240255011 | Hyper | FMN2 |
| chr1 | 240256663 | 240256721 | Hyper | FMN2 | chr1 | 240255819 | 240256197 | Hyper | FMN2 |
| chr1 | 241587034 | 241587113 | Hyper | | chr1 | 240775425 | 240775455 | Hyper | |
| chr1 | 242686734 | 242687219 | Hyper | PLD5 | chr1 | 241587679 | 241587724 | Hyper | |
| chr1 | 242688184 | 242688259 | Hyper | PLD5 | chr1 | 242687614 | 242687688 | Hyper | PLD5 |
| chr1 | 243646610 | 243646673 | Hyper | AKT3 | chr1 | 242688477 | 242688695 | Hyper | PLD5 |
| chr1 | 244893214 | 244893315 | Hyper | | chr1 | 244080672 | 244080702 | Hyper | LOC339529 |
| chr17 | 1173996 | 1174413 | Hyper | TUSC5, BHLHA9 | chr1 | 248020479 | 248021349 | Hyper | TRIM58 |
| chr17 | 3438914 | 3438959 | Hyper | TRPV3 | chr17 | 1959468 | 1959520 | Hyper | HIC1, SMG6, AX747853, MIR212, MIR132 |
| chr17 | 5000428 | 5000790 | Hyper | ZNF232, ZFP3 | chr17 | 4544607 | 4544710 | Hyper | ALOX15 |
| chr17 | 6616911 | 6616943 | Hyper | SLC13A5 | chr17 | 6616637 | 6616686 | Hyper | SLC13A5 |
| chr17 | 6946107 | 6946141 | Hyper | SLC16A11, SLC16A13 | chr17 | 6679190 | 6679296 | Hyper | XAF1, FBXO39 |
| chr17 | 8230564 | 8230694 | Hyper | ARHGEF15 | chr17 | 7906254 | 7906375 | Hyper | GUCY2D |
| chr17 | 8906266 | 8906518 | Hyper | | chr17 | 8868620 | 8869385 | Hyper | PIK3R5 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr17 | 8926060 | 8926102 | Hyper | NTN1 | chr17 | 8906993 | 8907575 | Hyper | |
| chr17 | 10102415 | 10102665 | Hyper | | chr17 | 10101084 | 10101984 | Hyper | |
| chr17 | 11144926 | 11144989 | Hyper | SHISA6 | chr17 | 11144167 | 11144320 | Hyper | SHISA6 |
| chr17 | 13504557 | 13504681 | Hyper | HS3ST3A1 | chr17 | 13503972 | 13504195 | Hyper | HS3ST3A1 |
| chr17 | 13505493 | 13505572 | Hyper | HS3ST3A1 | chr17 | 13504975 | 13505007 | Hyper | HS3ST3A1 |
| chr17 | 15245050 | 15245139 | Hyper | TEKT3 | chr17 | 14201041 | 14201181 | Hyper | HS3ST3B1, MGC12916 |
| chr17 | 18538154 | 18538275 | Hyper | CCDC144B, TBC1D28 | chr17 | 16570699 | 16570794 | Hyper | |
| chr17 | 27038806 | 27038848 | Hyper | PROCA1, RAB34, NARR, RPL23A, SNORD42B | chr17 | 26554634 | 26554705 | Hyper | PYY2 |
| chr17 | 27940359 | 27940911 | Hyper | CORO6, ANKRD13B | chr17 | 27332453 | 27332660 | Hyper | SEZ6 |
| chr17 | 29249717 | 29249930 | Hyper | ADAP2 | chr17 | 28562701 | 28562765 | Hyper | SLC6A4 |
| chr17 | 29719187 | 29719242 | Hyper | RAB11FIP4 | chr17 | 29718215 | 29718269 | Hyper | RAB11FIP4 |
| chr17 | 31619951 | 31620026 | Hyper | ASIC2 | chr17 | 31618425 | 31619319 | Hyper | ASIC2 |
| chr17 | 32908132 | 32908374 | Hyper | TMEM132E, C17orf102 | chr17 | 32907652 | 32907753 | Hyper | TMEM132E, C17orf102 |
| chr17 | 33672916 | 33672986 | Hyper | SLFN11 | chr17 | 32908647 | 32908931 | Hyper | TMEM132E, C17orf102 |
| chr17 | 35165986 | 35166016 | Hyper | | chr17 | 35165645 | 35165691 | Hyper | |
| chr17 | 35290388 | 35290655 | Hyper | LHX1, BC084573 | chr17 | 35285542 | 35285666 | Hyper | BC084573, LHX1 |
| chr17 | 35291829 | 35292626 | Hyper | LHX1, BC084573 | chr17 | 35291320 | 35291354 | Hyper | LHX1, BC084573 |
| chr17 | 35295047 | 35295160 | Hyper | LHX1, BC084573 | chr17 | 35294006 | 35294154 | Hyper | LHX1, BC084573 |
| chr17 | 35296728 | 35296888 | Hyper | AATF, LHX1, BC084573 | chr17 | 35296143 | 35296292 | Hyper | AATF, LHX1, BC084573 |
| chr17 | 35299251 | 35300854 | Hyper | AATF, LHX1, BC084573 | chr17 | 35297619 | 35298153 | Hyper | AATF, LHX1, BC084573 |
| chr17 | 36103117 | 36103326 | Hyper | HNF1B | chr17 | 35303340 | 35303535 | Hyper | AATF, LHX1, BC084573 |
| chr17 | 36104120 | 36104779 | Hyper | | chr17 | 36103571 | 36103601 | Hyper | HNF1B |
| chr17 | 37321359 | 37321972 | Hyper | CACNB1, ARL5C | chr17 | 36105223 | 36105596 | Hyper | |
| chr17 | 37381011 | 37381742 | Hyper | STAC2 | chr17 | 37366337 | 37366552 | Hyper | STAC2, RPL19 |
| chr17 | 37761997 | 37762334 | Hyper | NEUROD2 | chr17 | 37760460 | 37760561 | Hyper | NEUROD2 |
| chr17 | 40400867 | 40401031 | Hyper | STAT5B | chr17 | 38347560 | 38347624 | Hyper | RAPGEFL1 |
| chr17 | 40464517 | 40464607 | Hyper | AK024535, STAT3, AK092965, STAT5A | chr17 | 40464278 | 40464317 | Hyper | AK024535, STAT3, AK092965, STAT5A |
| chr17 | 42082522 | 42082557 | Hyper | NAGS, TMEM101 | chr17 | 42030329 | 42030756 | Hyper | PYY |
| chr17 | 42635305 | 42635760 | Hyper | FZD2 | chr17 | 42393842 | 42394024 | Hyper | SLC25A39, RUNDC3A, AK055254 |
| chr17 | 42907826 | 42907951 | Hyper | | chr17 | 42733802 | 42733884 | Hyper | C17orf104 |
| chr17 | 43044658 | 43044688 | Hyper | C1QL1 | chr17 | 43037399 | 43037429 | Hyper | C1QL1 |
| chr17 | 43047436 | 43047751 | Hyper | C1QL1 | chr17 | 43045049 | 43045116 | Hyper | C1QL1 |
| chr17 | 43339609 | 43339899 | Hyper | MAP3K14, MAP3K14-AS1, SPATA32 | chr17 | 43339109 | 43339333 | Hyper | MAP3K14-AS1, MAP3K14, SPATA32 |
| chr17 | 45811146 | 45811341 | Hyper | TBX21 | chr17 | 43974256 | 43974358 | Hyper | MAPT-IT1, MAPT |
| chr17 | 46621353 | 46621458 | Hyper | HOXB2, HOXB-AS1, HOXB3 | chr17 | 46620494 | 46621094 | Hyper | HOXB-AS1, HOXB3, HOXB2 |
| chr17 | 46655435 | 46656365 | Hyper | MIR10A, HOXB4, HOXB3 | chr17 | 46621856 | 46621909 | Hyper | HOXB-AS1, HOXB2, HOXB3 |
| chr17 | 46663743 | 46663789 | Hyper | HOXB-AS3, HOXB5, HOXB6, MIR10A, HOXB4 | chr17 | 46659429 | 46659859 | Hyper | HOXB-AS3, HOXB5, MIR10A, HOXB4, HOXB3 |
| chr17 | 46675170 | 46675600 | Hyper | HOXB-AS3, HOXB6, HOXB5, HOXB7 | chr17 | 46674873 | 46674970 | Hyper | HOXB7, HOXB-AS3, HOXB6, HOXB5 |
| chr17 | 46691505 | 46691592 | Hyper | HOXB9, HOXB8, HOXB7 | chr17 | 46690467 | 46690664 | Hyper | HOXB9, HOXB8, HOXB7 |
| chr17 | 46710946 | 46711031 | Hyper | MIR196A1, HOXB9 | chr17 | 46691813 | 46692110 | Hyper | HOXB9, HOXB8, HOXB7 |
| chr17 | 46713959 | 46714072 | Hyper | MIR196A1 | chr17 | 46711281 | 46711375 | Hyper | MIR196A1, HOXB9 |
| chr17 | 46799801 | 46799896 | Hyper | HOXB13, PRAC, HOXB-AS5, MIR3185 | chr17 | 46795641 | 46797582 | Hyper | HOXB13, PRAC, HOXB-AS5, MIR3185 |
| chr17 | 46800961 | 46801416 | Hyper | MIR3185, HOXB13, HOXB-AS5, PRAC | chr17 | 46800601 | 46800668 | Hyper | MIR3185, HOXB13, HOXB-AS5, PRAC |
| chr17 | 46804107 | 46804428 | Hyper | HOXB13, MIR3185, HOXB-AS5, PRAC | chr17 | 46802459 | 46803286 | Hyper | MIR3185, HOXB-AS5, PRAC, HOXB13 |
| chr17 | 46811354 | 46811541 | Hyper | HOXB13, MIR3185, HOXB-AS5 | chr17 | 46810416 | 46810958 | Hyper | HOXB13, MIR3185, HOXB-AS5 |
| chr17 | 46824224 | 46825054 | Hyper | | chr17 | 46816282 | 46816877 | Hyper | |
| chr17 | 46826930 | 46827127 | Hyper | | chr17 | 46825284 | 46825514 | Hyper | |
| chr17 | 46829498 | 46829579 | Hyper | | chr17 | 46827330 | 46827756 | Hyper | |
| chr17 | 46831779 | 46832639 | Hyper | TTLL6 | chr17 | 46829979 | 46830110 | Hyper | TTLL6 |
| chr17 | 47073988 | 47074228 | Hyper | IGF2BP1 | chr17 | 47072805 | 47073465 | Hyper | IGF2BP1 |

TABLE 1-continued

| Chr | Start | Stop | Hypo/hyper | Annotation | Chr | Start | Stop | Hypo/hyper | Annotation |
|---|---|---|---|---|---|---|---|---|---|
| chr17 | 47075225 | 47075364 | Hyper | IGF2BP1 | chr17 | 47074778 | 47074895 | Hyper | IGF2BP1 |
| chr17 | 47865514 | 47865555 | Hyper | KAT7, FAM117A | chr17 | 47075715 | 47076055 | Hyper | IGF2BP1 |
| chr17 | 47987930 | 47988114 | Hyper | | chr17 | 47987525 | 47987619 | Hyper | |
| chr17 | 48041672 | 48041721 | Hyper | DLX4 | chr17 | 48041152 | 48041320 | Hyper | DLX4 |
| chr17 | 48042435 | 48042956 | Hyper | DLX4 | chr17 | 48042039 | 48042069 | Hyper | DLX4 |
| chr17 | 48049307 | 48050526 | Hyper | DLX4 | chr17 | 48048952 | 48049059 | Hyper | DLX4 |
| chr17 | 48636581 | 48637136 | Hyper | CACNA1G, CACNA1G-AS1, SPATA20 | chr17 | 48071791 | 48071894 | Hyper | DLX3 |
| chr17 | 50235631 | 50235952 | Hyper | CA10 | chr17 | 50235216 | 50235274 | Hyper | CA10 |
| chr17 | 53342876 | 53342919 | Hyper | HLF | chr17 | 53341252 | 53341536 | Hyper | HLF |
| chr17 | 54675082 | 54675272 | Hyper | NOG | chr17 | 53922649 | 53922790 | Hyper | |
| chr17 | 56234405 | 56234743 | Hyper | MSX2P1, OR4D1 | chr17 | 54755969 | 54756014 | Hyper | |
| chr17 | 56833127 | 56833221 | Hyper | PPM1E | chr17 | 56326949 | 56326994 | Hyper | LPO |
| chr17 | 58218765 | 58218993 | Hyper | CA4 | chr17 | 58216613 | 58217551 | Hyper | CA4 |
| chr17 | 58498777 | 58499314 | Hyper | C17orf64 | chr17 | 58227374 | 58227426 | Hyper | CA4 |
| chr17 | 59474833 | 59475100 | Hyper | TBX2, BCAS3 | chr17 | 59474157 | 59474620 | Hyper | TBX2, BCAS3 |
| chr17 | 59476410 | 59476635 | Hyper | TBX2, BCAS3 | chr17 | 59475678 | 59476127 | Hyper | BCAS3, TBX2 |
| chr17 | 59528876 | 59530352 | Hyper | TBX4 | chr17 | 59478147 | 59478602 | Hyper | TBX2, BCAS3 |
| chr17 | 59533828 | 59534491 | Hyper | TBX4 | chr17 | 59531667 | 59532139 | Hyper | TBX4 |
| chr17 | 59535137 | 59535219 | Hyper | TBX4 | chr17 | 59534751 | 59534781 | Hyper | TBX4 |
| chr17 | 61778085 | 61778300 | Hyper | LIMD2, MAP3K3, STRADA, LOC729683 | chr17 | 59539329 | 59539426 | Hyper | TBX4 |
| chr17 | 66596471 | 66596525 | Hyper | FAM20A | chr17 | 61926172 | 61926603 | Hyper | TCAM1P |
| chr17 | 70026568 | 70026652 | Hyper | D43770 | chr17 | 68164733 | 68164763 | Hyper | KCNJ2, KCNJ2-AS1 |
| chr17 | 70215683 | 70216585 | Hyper | | chr17 | 70112916 | 70114517 | Hyper | SOX9, AL833139, AK094963 |
| chr17 | 71948439 | 71948863 | Hyper | | chr17 | 71641544 | 71641683 | Hyper | |
| chr17 | 72321933 | 72321975 | Hyper | KIF19 | chr17 | 72270228 | 72270415 | Hyper | DNAI2 |
| chr17 | 72353213 | 72353397 | Hyper | BTBD17, KIF19 | chr17 | 72322263 | 72322604 | Hyper | KIF19 |
| chr17 | 72849010 | 72849079 | Hyper | FDXR, GRIN2C | chr17 | 72667337 | 72667565 | Hyper | RAB37 |
| chr17 | 72920796 | 72921032 | Hyper | OTOP2, USH1G | chr17 | 72857194 | 72857244 | Hyper | FDXR, GRIN2C |
| chr17 | 73584821 | 73584883 | Hyper | MYO15B | chr17 | 73073684 | 73073745 | Hyper | |
| chr17 | 74070281 | 74070582 | Hyper | GALR2, ZACN, EXOC7, SRP68 | chr17 | 73709838 | 73709955 | Hyper | ITGB4, SAP30BP |
| chr17 | 74071689 | 74071729 | Hyper | ZACN, EXOC7, GALR2, SRP68 | chr17 | 74071445 | 74071481 | Hyper | SRP68, ZACN, EXOC7, GALR2 |
| chr17 | 74073269 | 74073433 | Hyper | ZACN, EXOC7, GALR2, SRP68 | chr17 | 74072941 | 74073036 | Hyper | ZACN, EXOC7, GALR2, SRP68 |
| chr17 | 74581182 | 74581221 | Hyper | ST6GALNAC2 | chr17 | 74534246 | 74534310 | Hyper | PRCD, CYGB |
| chr17 | 75368913 | 75368968 | Hyper | 9-Sep | chr17 | 74865698 | 74866243 | Hyper | MGAT5B, BC038218 |
| chr17 | 75370281 | 75370316 | Hyper | 9-Sep | chr17 | 75369440 | 75369860 | Hyper | 9-Sep |
| chr17 | 75525049 | 75525194 | Hyper | BC040189 | chr17 | 75524636 | 75524747 | Hyper | BC040189 |
| chr17 | 77179113 | 77179278 | Hyper | RBFOX3 | chr17 | 76227849 | 76228357 | Hyper | TMEM235, EPR-1, BIRC5 |
| chr17 | 77776827 | 77777056 | Hyper | CBX8 | chr17 | 77179630 | 77179735 | Hyper | RBFOX3 |
| chr17 | 77778943 | 77779179 | Hyper | CBX8 | chr17 | 77777585 | 77777748 | Hyper | CBX8 |
| chr17 | 77789296 | 77789500 | Hyper | | chr17 | 77788841 | 77788969 | Hyper | |
| chr17 | 78452296 | 78452340 | Hyper | NPTX1 | chr17 | 78451931 | 78452051 | Hyper | NPTX1 |
| chr17 | 79615176 | 79615356 | Hyper | PDE6G, TSPAN10 | chr17 | 78452681 | 78452833 | Hyper | NPTX1 |
| | | | | | chr17 | 80329709 | 80330085 | Hyper | UTS2R, AF075112, TEX19 |

TABLE 2

Blood Cancer

| chr | start | end | hypo/hyper | gene annotation | chr | start | end | hypo/hyper | gene annotation |
|---|---|---|---|---|---|---|---|---|---|
| chr8 | 8681258 | 8681353 | Hypo | MFHAS1 | chr8 | 144421487 | 144421517 | Hypo | TOP1MT |
| chr8 | 145218226 | 145218301 | Hypo | MROH1 | chr16 | 11490632 | 11490662 | Hypo | |
| chr20 | 30280423 | 30280509 | Hypo | BCL2L1 | chr20 | 44003765 | 44003811 | Hypo | TP53TG5, SYS1, SYS1-DBNDD2 |
| chr13 | 31185432 | 31185548 | Hypo | USPL1 | chr17 | 72862371 | 72862460 | Hypo | FDXR, GRIN2C |
| chr17 | 75207514 | 75207630 | Hypo | SEC14L1 | chr17 | 75207839 | 75207987 | Hypo | SEC14L1 |
| chr17 | 79896013 | 79896043 | Hypo | MYADML2, PYCR1, MAFG-AS1 | chr21 | 43256565 | 43256603 | Hypo | PRDM15 |
| chr2 | 219276888 | 219276918 | Hypo | VIL1, MIR26B, CTDSP1 | chr11 | 65364470 | 65364557 | Hypo | MAP3K11, KCNK7, EHBP1L1 |
| chr3 | 12926053 | 12926102 | Hypo | | chr5 | 1059523 | 1059556 | Hypo | MIR4635, SLC12A7 |

TABLE 2-continued

Blood Cancer

| chr | start | end | hypo/hyper gene annotation | chr | start | end | hypo/hyper gene annotation |
| --- | --- | --- | --- | --- | --- | --- | --- |
| chr1 | 161013554 | 161013677 | Hypo USF1, TSTD1, ARHGAP30 | chr1 | 203681332 | 203681362 | Hypo ATP2B4 |
| chr7 | 102091406 | 102091534 | Hypo ALKBH4, ORAI2 | chr22 | 24179940 | 24179982 | Hypo AK096976, DERL3 |
| chr15 | 30115185 | 30115228 | Hyper TJP1 | chr15 | 62456922 | 62456952 | Hyper C2CD4B |
| chr15 | 71055636 | 71055815 | Hyper | chr15 | 81071827 | 81071867 | Hyper KIAA1199 |
| chr15 | 96874362 | 96874514 | Hyper NR2F2, MIR1469, NR2F2-AS1 | chr15 | 98504114 | 98504144 | Hyper ARRDC4 |
| chr15 | 99193206 | 99193465 | Hyper IGF1R | chr22 | 31198492 | 31198637 | Hyper OSBP2 |
| chr18 | 19750308 | 19750346 | Hyper GATA6, LOC100128893 | chr18 | 21269349 | 21269390 | Hyper LAMA3 |
| chr18 | 21269659 | 21269740 | Hyper LAMA3 | chr18 | 47720492 | 47720522 | Hyper |
| chr18 | 78004993 | 78005051 | Hyper PARD6G | chr17 | 42061336 | 42061381 | Hyper |
| chr17 | 72427853 | 72427999 | Hyper GPRC5C | chr17 | 72428344 | 72428381 | Hyper GPRC5C |
| chr17 | 80693317 | 80693554 | Hyper FN3K, FN3KRP | chr6 | 1312000 | 1312096 | Hyper FOXQ1 |
| chr6 | 1312356 | 1312708 | Hyper FOXQ1 | chr6 | 1314088 | 1314118 | Hyper FOXQ1 |
| chr6 | 26987967 | 26988166 | Hyper TRNA_Ile, LOC100270746, LINC00240 | chr6 | 42928321 | 42928454 | Hyper GNMT, BC040637, PEX6 |
| chr6 | 54711448 | 54711626 | Hyper FAM83B | chr6 | 82463270 | 82463310 | Hyper FAM46A |
| chr20 | 1206855 | 1207034 | Hyper RAD21L1 | chr20 | 6748925 | 6749096 | Hyper BMP2 |
| chr20 | 18039823 | 18039897 | Hyper OVOL2 | chr20 | 22564235 | 22564265 | Hyper FOXA2, LINC00261 |
| chr20 | 50384767 | 50384896 | Hyper ATP9A | chr9 | 14312994 | 14313096 | Hyper NFIB |
| chr9 | 14313319 | 14313785 | Hyper NFIB | chr9 | 21559294 | 21559381 | Hyper |
| chr9 | 21559673 | 21559702 | Hyper | chr9 | 38620530 | 38620725 | Hyper FAM201A, ANKRD18A |
| chr9 | 85677905 | 85677992 | Hyper RASEF | chr9 | 99146020 | 99146153 | Hyper ZNF367, SLC35D2 |
| chr9 | 110251388 | 110251418 | Hyper KLF4 | chr9 | 110252363 | 110252515 | Hyper KLF4 |
| chr9 | 134421797 | 134421835 | Hyper | chr11 | 12132524 | 12132559 | Hyper MICAL2 |
| chr11 | 12399040 | 12399222 | Hyper PARVA | chr11 | 12399791 | 12399791 | Hyper PARVA |
| chr11 | 12695481 | 12695611 | Hyper TEAD1, DD413619 | chr11 | 12696611 | 12696746 | Hyper TEAD1, DD413619 |
| chr11 | 16628819 | 16628933 | Hyper | chr11 | 33037467 | 33037556 | Hyper DEPDC7 |
| chr11 | 66725600 | 66725637 | Hyper | chr11 | 66790621 | 66790655 | Hyper SYT12 |
| chr11 | 72929747 | 72929883 | Hyper P2RY2 | chr11 | 120039833 | 120039865 | Hyper |
| chr11 | 129245673 | 129245810 | Hyper BARX2 | chr11 | 129246070 | 129246129 | Hyper BARX2 |
| chr11 | 130318960 | 130318997 | Hyper ADAMTS15 | chr11 | 134201502 | 134201543 | Hyper GLB1L2 |
| chr11 | 134201841 | 134202084 | Hyper GLB1L2 | chr19 | 462181 | 462269 | Hyper ODF3L2, SHC2 |
| chr19 | 33792159 | 33792524 | Hyper CEBPA-AS1, CEBPA | chr19 | 34972464 | 34972494 | Hyper WTIP |
| chr19 | 41698787 | 41698920 | Hyper CYP2S1 | chr12 | 16500576 | 16500621 | Hyper MGST1 |
| chr12 | 19282333 | 19282363 | Hyper PLEKHA5 | chr12 | 56882240 | 56882380 | Hyper BC059370, GLS2 |
| chr12 | 59314159 | 59314189 | Hyper LRIG3 | chr12 | 88973544 | 88973582 | Hyper U1 |
| chr12 | 88974159 | 88974253 | Hyper U1 | chr12 | 107486550 | 107486672 | Hyper CRY1 |
| chr12 | 107487194 | 107487855 | Hyper CRY1 | chr12 | 107712273 | 107712303 | Hyper BTBD11 |
| chr21 | 33785288 | 33785325 | Hyper EVA1C | chr21 | 38070705 | 38070765 | Hyper SIM2 |
| chr21 | 38071791 | 38071905 | Hyper SIM2 | chr21 | 43186698 | 43186889 | Hyper RIPK4 |
| chr8 | 25041746 | 25041864 | Hyper DOCK5 | chr8 | 25042534 | 25042567 | Hyper DOCK5 |
| chr8 | 95651538 | 95651655 | Hyper ESRP1, LOC100288748 | chr8 | 102505797 | 102505934 | Hyper GRHL2 |
| chr8 | 120220428 | 120220592 | Hyper MAL2 | chr8 | 127569621 | 127569676 | Hyper FAM84B |
| chr8 | 144512473 | 144512503 | Hyper ZC3H3, MAFA | chr4 | 24914638 | 24914668 | Hyper CCDC149 |
| chr4 | 74735076 | 74735137 | Hyper CXCL1 | chr4 | 94749725 | 94749755 | Hyper ATOH1 |
| chr4 | 152246132 | 152246314 | Hyper | chr4 | 170947287 | 170947325 | Hyper BC031941 |
| chr4 | 184019692 | 184019736 | Hyper WWC2, WWC2-AS2 | chr4 | 184020106 | 184020179 | Hyper WWC2, WWC2-AS2 |
| chr4 | 187647073 | 187647457 | Hyper FAT1 | chr3 | 37901923 | 37901953 | Hyper CTDSPL, BC040563 |
| chr3 | 45187296 | 45187582 | Hyper CDCP1 | chr3 | 126373520 | 126373704 | Hyper TXNRD3, NUP210P1 |
| chr3 | 133748140 | 133748245 | Hyper SLCO2A1 | chr3 | 133748481 | 133748576 | Hyper SLCO2A1 |
| chr3 | 138067717 | 138067747 | Hyper MRAS | chr3 | 145878665 | 145878695 | Hyper |
| chr3 | 153838818 | 153838870 | Hyper ARHGEF26, ARHGEF26-AS1 | chr3 | 153839518 | 153839775 | Hyper ARHGEF26-AS1, ARHGEF26 |
| chr3 | 171527930 | 171527971 | Hyper | chr16 | 54964948 | 54965114 | Hyper CRNDE, IRX5 |
| chr16 | 57318379 | 57318412 | Hyper PLLP | chr16 | 68771134 | 68771298 | Hyper CDH1 |
| chr16 | 80966399 | 80966431 | Hyper | chr16 | 84402244 | 84402319 | Hyper ATP2C2 |
| chr16 | 84853288 | 84853376 | Hyper CRISPLD2 | chr16 | 87525622 | 87525701 | Hyper BC131758 |
| chr5 | 34656932 | 34657034 | Hyper RAI14 | chr5 | 52084073 | 52084134 | Hyper PELO, ITGA1 |
| chr5 | 72416246 | 72416751 | Hyper TMEM171 | chr5 | 72733093 | 72733185 | Hyper FOXD1 |
| chr5 | 107005983 | 107006186 | Hyper EFNA5 | chr5 | 121413537 | 121413590 | Hyper LOX |
| chr13 | 100633089 | 100633184 | Hyper ZIC2, ZIC5 | chr13 | 100634314 | 100634617 | Hyper ZIC2 |
| chr2 | 46214 | 46450 | Hyper FAM110C | chr2 | 14772761 | 14772823 | Hyper FAM84A, AX747684 |
| chr2 | 14774281 | 14774567 | Hyper AX747684, FAM84A | chr2 | 19557685 | 19557727 | Hyper OSR1, MIR4757 |
| chr2 | 46526302 | 46526448 | Hyper EPAS1 | chr2 | 75427369 | 75427399 | Hyper |
| chr2 | 101436632 | 101436708 | Hyper NPAS2 | chr2 | 103236165 | 103236292 | Hyper SLC9A2 |
| chr2 | 110370941 | 110371219 | Hyper SOWAHC | chr2 | 151342903 | 151343277 | Hyper RND3 |
| chr2 | 171571264 | 171571315 | Hyper AK023515, LOC440925, SP5 | chr2 | 171571889 | 171572068 | Hyper AK023515, SP5, LOC440925 |
| chr2 | 171673873 | 171673939 | Hyper GAD1 | chr2 | 189157427 | 189157617 | Hyper MIR561, GULP1 |
| chr2 | 201172444 | 201172480 | Hyper SPATS2L | chr2 | 235860746 | 235860808 | Hyper SH3BP4 |

TABLE 2-continued

Blood Cancer

| chr | start | end | hypo/hyper | gene annotation | chr | start | end | hypo/hyper | gene annotation |
|---|---|---|---|---|---|---|---|---|---|
| chr2 | 235861389 | 235861533 | Hyper | SH3BP4 | chr2 | 236402771 | 236403013 | Hyper | AGAP1 |
| chr2 | 236403270 | 236403736 | Hyper | AGAP1 | chr2 | 236578362 | 236578677 | Hyper | AGAP1 |
| chr2 | 238395906 | 238395961 | Hyper | MLPH | chr7 | 556928 | 556983 | Hyper | FLJ44511, PDGFA |
| chr7 | 12610339 | 12610476 | Hyper | SCIN, BC075797 | chr7 | 27275513 | 27275543 | Hyper | EVX1 |
| chr7 | 28995657 | 28995978 | Hyper | DQ601810, TRIL | chr7 | 28996457 | 28996495 | Hyper | DQ601810, TRIL |
| chr7 | 31232909 | 31232939 | Hyper |  | chr7 | 32997124 | 32997454 | Hyper | FKBP9 |
| chr7 | 50860226 | 50861121 | Hyper |  | chr7 | 51383754 | 51383790 | Hyper | COBL |
| chr7 | 51384327 | 51384440 | Hyper | COBL | chr7 | 51384915 | 51384951 | Hyper | COBL |
| chr7 | 55086473 | 55086601 | Hyper | EGFR | chr7 | 55086983 | 55087533 | Hyper | EGFR |
| chr7 | 80548257 | 80548403 | Hyper | SEMA3C | chr7 | 82073495 | 82073533 | Hyper |  |
| chr7 | 117513675 | 117513849 | Hyper | CTTNBP2 | chr7 | 121945822 | 121945920 | Hyper | FEZF1-AS1, FEZF1 |
| chr7 | 122526833 | 122526873 | Hyper |  | chr7 | 155602751 | 155602805 | Hyper | SHH |
| chr14 | 34420250 | 34420288 | Hyper | EGLN3 | chr14 | 38064401 | 38064549 | Hyper | FOXA1 |
| chr14 | 61747300 | 61748033 | Hyper | TMEM30B | chr14 | 99737398 | 99737462 | Hyper | BCL11B |
| chr1 | 8085685 | 8085715 | Hyper | ERRFI1 | chr1 | 15251120 | 15251211 | Hyper | KAZN |
| chr1 | 15480593 | 15480892 | Hyper | TMEM51-AS1, TMEM51 | chr1 | 20693317 | 20693420 | Hyper | LOC339505 |
| chr1 | 64240026 | 64240118 | Hyper | ROR1 | chr1 | 64240617 | 64240673 | Hyper | ROR1 |
| chr1 | 95006795 | 95006902 | Hyper | F3 | chr1 | 183774244 | 183774363 | Hyper | RGL1 |
| chr1 | 201368582 | 201368727 | Hyper | TNNI1, LAD1 | chr1 | 202183371 | 202183401 | Hyper | LGR6 |
| chr1 | 214724531 | 214724561 | Hyper | PTPN14 | chr1 | 228871865 | 228872003 | Hyper | RHOU |
| chr1 | 232765195 | 232765301 | Hyper |  | chr1 | 233750082 | 233750302 | Hyper | MIR4427, KCNK1 |
| chr10 | 21462533 | 21462607 | Hyper | NEBL-AS1 | chr10 | 21462970 | 21463023 | Hyper | NEBL-AS1 |
| chr10 | 30025970 | 30026090 | Hyper |  | chr10 | 33624166 | 33624230 | Hyper |  |
| chr10 | 33624492 | 33624560 | Hyper |  | chr10 | 72973130 | 72973180 | Hyper | UNC5B-AS1, UNC5B |
| chr10 | 95360716 | 95360750 | Hyper | RBP4 | chr10 | 116164248 | 116164341 | Hyper | AFAP1L2 |
| chr10 | 123357206 | 123357242 | Hyper | FGFR2 | chr10 | 123357766 | 123357893 | Hyper | FGFR2 |

TABLE 3

Breast Cancer

| chr | start | end | hypo/hyper | gene annotation | chr | start | end | hypo/hyper | gene annotation |
|---|---|---|---|---|---|---|---|---|---|
| chr12 | 47629349 | 47629379 | Hypo | PCED1B | chr12 | 93476304 | 93476342 | Hypo | LOC643339 |
| chr12 | 110353414 | 110353451 | Hypo | TCHP | chr12 | 112792829 | 112792944 | Hypo |  |
| chr12 | 122192723 | 122192843 | Hypo | TMEM120B | chr2 | 7236859 | 7236974 | Hypo |  |
| chr2 | 9289969 | 9290114 | Hypo |  | chr2 | 38594819 | 38594874 | Hypo | ATL2 |
| chr2 | 38727561 | 38727707 | Hypo |  | chr2 | 44497708 | 44497875 | Hypo | SLC3A1 |
| chr2 | 61135032 | 61135137 | Hypo | REL | chr2 | 61656393 | 61656423 | Hypo |  |
| chr2 | 96070057 | 96070165 | Hypo | FAHD2A | chr17 | 2278801 | 2278925 | Hypo | SGSM2, MNT |
| chr17 | 4693354 | 4693388 | Hypo | GLTPD2, BC150535, VMO1, TM4SF5, PSMB6 | chr17 | 5167638 | 5167681 | Hypo |  |
| chr17 | 5168597 | 5168732 | Hypo |  | chr17 | 17117365 | 17117395 | Hypo | FLCN, PLD6 |
| chr17 | 17719242 | 17719355 | Hypo | SREBF1, MIR33B, SREBP-1 | chr17 | 26961770 | 26961833 | Hypo | KIAA0100 |
| chr17 | 30568137 | 30568174 | Hypo |  | chr17 | 42580695 | 42580793 | Hypo |  |
| chr17 | 73351981 | 73352086 | Hypo | GRB2 | chr17 | 78272278 | 78272313 | Hypo | RNF213 |
| chr17 | 79945037 | 79945074 | Hypo | ASPSCR1 | chr17 | 80394063 | 80394185 | Hypo | HEXDC, C17orf62 |
| chr17 | 80751650 | 80751714 | Hypo | TBCD | chr6 | 5359500 | 5359539 | Hypo | FARS2 |
| chr6 | 17666654 | 17666707 | Hypo | NUP153 | chr6 | 41773520 | 41773903 | Hypo | USP49 |
| chr6 | 41774459 | 41774576 | Hypo | USP49 | chr6 | 43748463 | 43748616 | Hypo | HV983065, VEGFA |
| chr6 | 47590439 | 47590604 | Hypo | CD2AP | chr6 | 157266063 | 157266109 | Hypo | ARID1B |
| chr1 | 1047531 | 1047647 | Hypo | C1orf159 | chr1 | 1805049 | 1805089 | Hypo | GNB1 |
| chr1 | 2336397 | 2336427 | Hypo | PEX10, RER1 | chr1 | 2521024 | 2521063 | Hypo | MMEL1, FAM213B |
| chr1 | 9402465 | 9402616 | Hypo | SPSB1 | chr1 | 21573283 | 21573362 | Hypo | ECE1 |
| chr1 | 21573668 | 21574203 | Hypo | ECE1 | chr1 | 22222711 | 22222793 | Hypo | HSPG2 |
| chr1 | 26183522 | 26183579 | Hypo | PAQR7, AUNIP | chr1 | 41915253 | 41915283 | Hypo |  |
| chr1 | 46744657 | 46744733 | Hypo | LRRC41, RAD54L | chr1 | 53192045 | 53192075 | Hypo | ZYG11B |
| chr1 | 89394066 | 89394163 | Hypo | CCBL2 | chr1 | 94911234 | 94911328 | Hypo | ABCD3 |
| chr1 | 150941425 | 150941847 | Hypo | CERS2, SETDB1 | chr1 | 155283218 | 155283248 | Hypo | RUSC1-AS1, RUSC1, FDPS |
| chr1 | 167823339 | 167823461 | Hypo | ADCY10 | chr1 | 169838016 | 169838187 | Hypo | Metazoa_SRP, SCYL3 |
| chr1 | 178063112 | 178063150 | Hypo | RASAL2, RASAL2-AS1 | chr1 | 180919682 | 180919718 | Hypo | AK056657, KIAA1614 |
| chr1 | 185073818 | 185073966 | Hypo | RNF2 | chr1 | 202531939 | 202532087 | Hypo | PPP1R12B |
| chr1 | 204531203 | 204531757 | Hypo | MDM4 | chr1 | 246198078 | 246198203 | Hypo | SMYD3 |
| chr1 | 246654652 | 246654851 | Hypo | SMYD3 | chr10 | 1080377 | 1080513 | Hypo | IDI1, IDI2-AS1, IDI2 |
| chr10 | 5765021 | 5765059 | Hypo | FAM208B | chr10 | 6003402 | 6003855 | Hypo | IL15RA |
| chr10 | 22047336 | 22047635 | Hypo | DNAJC1 | chr10 | 65262111 | 65262304 | Hypo |  |

TABLE 3-continued

| Breast Cancer | | | | | | | | |
|---|---|---|---|---|---|---|---|---|
| chr | start | end | hypo/hyper | gene annotation | chr | start | end | hypo/hyper | gene annotation |
| chr10 | 70275831 | 70275979 | Hypo | SLC25A16 | chr10 | 105420861 | 105420891 | Hypo | SH3PXD2A |
| chr10 | 120937014 | 120937139 | Hypo | PRDX3 | chr10 | 123667184 | 123667222 | Hypo | ATE1 |
| chr4 | 488816 | 488875 | Hypo | PIGG, ZNF721 | chr4 | 3217107 | 3217154 | Hypo | |
| chr4 | 7038560 | 7038688 | Hypo | CCDC96, TADA2B, LOC100129931, TBC1D14 | chr4 | 106335495 | 106335617 | Hypo | PPA2 |
| chr15 | 40782219 | 40782249 | Hypo | | chr15 | 41732398 | 41732471 | Hypo | RTF1 |
| chr15 | 60705106 | 60705204 | Hypo | NARG2 | chr13 | 28239909 | 28240164 | Hypo | |
| chr13 | 114082984 | 114083014 | Hypo | ADPRHL1 | chr7 | 564237 | 564271 | Hypo | FLJ44511 |
| chr7 | 907656 | 907709 | Hypo | SUN1, GET4 | chr7 | 5397777 | 5397938 | Hypo | TNRC18 |
| chr7 | 6188610 | 6189061 | Hypo | USP42 | chr7 | 26283775 | 26283954 | Hypo | |
| chr7 | 28110701 | 28110828 | Hypo | JAZF1 | chr7 | 45046874 | 45046982 | Hypo | CCM2 |
| chr7 | 55410019 | 55410126 | Hypo | | chr7 | 127371129 | 127371249 | Hypo | SND1 |
| chr7 | 129800243 | 129800434 | Hypo | TMEM209 | chr7 | 131041515 | 131041596 | Hypo | MKLN1 |
| chr7 | 134918503 | 134918637 | Hypo | STRA8 | chr7 | 148851143 | 148851234 | Hypo | ZNF398 |
| chr7 | 151298870 | 151299029 | Hypo | PRKAG2 | chr7 | 158741193 | 158741267 | Hypo | WDR60 |
| chr9 | 2115824 | 2115981 | Hypo | SMARCA2 | chr9 | 34224348 | 34224474 | Hypo | UBAP1, KIF24 |
| chr9 | 34372805 | 34372983 | Hypo | C9orf24, KIAA1161 | chr9 | 127853274 | 127853304 | Hypo | |
| chr9 | 132373058 | 132373091 | Hypo | C9orf50 | chr9 | 139269039 | 139269121 | Hypo | SNAPC4, CARD9 |
| chr9 | 139888945 | 139888980 | Hypo | CLIC3, C9orf142, LCNL1 | chr3 | 12977067 | 12977144 | Hypo | IQSEC1 |
| chr3 | 57529094 | 57529218 | Hypo | DNAH12 | chr3 | 105684885 | 105684987 | Hypo | |
| chr3 | 126157586 | 126157663 | Hypo | UNQ2790, ZXDC, CCDC37 | chr3 | 138318827 | 138318918 | Hypo | FAIM, CEP70 |
| chr3 | 141363466 | 141363496 | Hypo | | chr3 | 142159804 | 142159841 | Hypo | ATR, XRN1 |
| chr3 | 142537638 | 142537779 | Hypo | PCOLCE2 | chr3 | 183728793 | 183728952 | Hypo | ABCC5-AS1, ABCC5 |
| chr8 | 28266438 | 28266484 | Hypo | | chr8 | 30475450 | 30475480 | Hypo | GTF2E2 |
| chr8 | 42293603 | 42293722 | Hypo | SLC20A2 | chr8 | 54698973 | 54699103 | Hypo | ATP6V1H |
| chr8 | 61777575 | 61777699 | Hypo | | chr8 | 81128658 | 81128782 | Hypo | |
| chr8 | 99234962 | 99235037 | Hypo | NIPAL2 | chr8 | 100117651 | 100117765 | Hypo | VPS13B |
| chr8 | 128964114 | 128964309 | Hypo | MIR1205, TMEM75, PVT1 | chr8 | 140755383 | 140755550 | Hypo | TRAPPC9 |
| chr8 | 141614252 | 141614287 | Hypo | AGO2 | chr8 | 142367368 | 142367790 | Hypo | GPR20 |
| chr8 | 144668566 | 144668667 | Hypo | NAPRT1, BC034020, EEF1D | chr8 | 144668909 | 144668972 | Hypo | BC034020, EEF1D, NAPRT1 |
| chr22 | 21977314 | 21977347 | Hypo | YDJC, CCDC116, UBE2L3 | chr22 | 23801459 | 23801610 | Hypo | LOC388882 |
| chr22 | 24560375 | 24560526 | Hypo | CABIN1 | chr22 | 30090739 | 30090769 | Hypo | NF2 |
| chr22 | 39830355 | 39830457 | Hypo | LOC100506472, TAB1 | chr22 | 41657233 | 41657350 | Hypo | RANGAP1 |
| chr22 | 43540672 | 43540702 | Hypo | TSPO, MCAT | chr22 | 47395475 | 47395505 | Hypo | |
| chr22 | 50251536 | 50251582 | Hypo | ZBED4 | chr11 | 232863 | 233062 | Hypo | PSMD13, SIRT3 |
| chr11 | 18100096 | 18100259 | Hypo | SAAL1 | chr11 | 47260168 | 47260258 | Hypo | ACP2, NR1H3, DDB2 |
| chr11 | 47478438 | 47478500 | Hypo | CELF1, RAPSN | chr11 | 62484517 | 62484547 | Hypo | HNRNPUL2, GNG3 |
| chr11 | 63641072 | 63641256 | Hypo | MARK2 | chr18 | 29413805 | 29413839 | Hypo | TRAPPC8 |
| chr18 | 74755670 | 74755590 | Hypo | MBP | chr18 | 77698881 | 77698919 | Hypo | |
| chr20 | 3154172 | 3154204 | Hypo | LZTS3 | chr20 | 6022797 | 6023045 | Hypo | LRRN4, CRLS1 |
| chr20 | 6023268 | 6023351 | Hypo | CRLS1, LRRN4 | chr20 | 31035471 | 31035518 | Hypo | C20orf112, ASXL1 |
| chr20 | 31282734 | 31282903 | Hypo | COMMD7 | chr20 | 32301797 | 32301953 | Hypo | PXMP4 |
| chr20 | 50693423 | 50693468 | Hypo | ZFP64 | chr20 | 60545561 | 60545792 | Hypo | TAF4 |
| chr20 | 60620122 | 60620557 | Hypo | TAF4 | chr20 | 60772853 | 60773878 | Hypo | MTG2 |
| chr20 | 62314848 | 62314955 | Hypo | RTEL1-TNFRSF6B, RTEL1 | chrX | 3631506 | 3631633 | Hypo | PRKX |
| chr5 | 230673 | 230709 | Hypo | SDHA | chr5 | 96114587 | 96114632 | Hypo | ERAP1, CAST |
| chr5 | 176764100 | 176764169 | Hypo | LMAN2 | chr16 | 1704656 | 1704800 | Hypo | CRAMP1L |
| chr16 | 3802981 | 3803074 | Hypo | CREBBP | chr16 | 4887144 | 4887244 | Hypo | UBN1, GLYR1 |
| chr16 | 27749857 | 27750033 | Hypo | | chr16 | 28850998 | 28851028 | Hypo | TUFM, MIR4721, SH2B1, ATXN2L |
| chr16 | 54128645 | 54128713 | Hypo | FTO | chr16 | 69969260 | 69969290 | Hypo | MIR140, WWP2 |
| chr16 | 71677557 | 71677661 | Hypo | KIAA0931,PHLPP2, MARVELD3 | chr16 | 81929362 | 81929392 | Hypo | PLCG2 |
| chr16 | 84823626 | 84823656 | Hypo | | chr16 | 85699689 | 85699921 | Hypo | GSE1 |
| chr16 | 88106322 | 88106398 | Hypo | BANP | chr14 | 50681598 | 50681859 | Hypo | |
| chr14 | 55823079 | 55823218 | Hypo | ATG14, FBXO34 | chr14 | 59770326 | 59770452 | Hypo | DAAM1 |
| chr14 | 93571193 | 93571326 | Hypo | | chr14 | 102564464 | 102564605 | Hypo | |
| chr21 | 33043985 | 33044051 | Hypo | SCAF4, SOD1 | chr21 | 37775034 | 37775141 | Hypo | CHAF1B |
| chr21 | 44886709 | 44886765 | Hypo | LINC00313 | chr21 | 45521343 | 45521438 | Hypo | TRAPPC10, PWP2 |
| chr21 | 45621533 | 45621573 | Hypo | | chr21 | 46935739 | 46935936 | Hypo | SLC19A1, COL18A1 |
| chr19 | 4910361 | 4910410 | Hypo | UHRF1, C19orf31, ARRDC5 | chr19 | 12303495 | 12303551 | Hypo | AX721123, AK023304, ZNF136 |
| chr19 | 14181305 | 14181846 | Hypo | LOC113230 | chr19 | 14663925 | 14664183 | Hypo | TECR |
| chr19 | 14664479 | 14664561 | Hypo | TECR | chr19 | 33468018 | 33468055 | Hypo | RHPN2, C19orf40, CEP89 |
| chr19 | 38441488 | 38441518 | Hypo | SIPA1L3 | chr19 | 38782559 | 38782589 | Hypo | SPINT2 |
| chr19 | 39650791 | 39650967 | Hypo | PAK4 | chr19 | 40829079 | 40829211 | Hypo | C19orf47 |
| chr19 | 40829793 | 40830032 | Hypo | C19orf47 | chr19 | 45570401 | 45570450 | Hypo | CLASRP, ZNF296 |

TABLE 3-continued

Breast Cancer

| chr | start | end | hypo/hyper | gene annotation | chr | start | end | hypo/hyper | gene annotation |
|---|---|---|---|---|---|---|---|---|---|
| chr19 | 45574773 | 45574888 | Hypo | GEMIN7, ZNF296, CLASRP | chr1 | 6507963 | 6508126 | Hyper | ESPN |
| chr1 | 23885070 | 23885100 | Hyper | ID3 | chr1 | 155043331 | 155043657 | Hyper | EFNA3, EFNA4, ADAM15 |
| chr2 | 127863601 | 127863725 | Hyper | BIN1 | chr17 | 42092190 | 42092220 | Hyper | NAGS, TMEM101 |
| chr17 | 70026543 | 70026667 | Hyper | D43770 | chr9 | 129401097 | 129401195 | Hyper | LMX1B |
| chr5 | 43007936 | 43007966 | Hyper | LOC648987 | chr5 | 43020245 | 43020294 | Hyper | LOC648987 |

TABLE 4

Colorectal Cancer

| chr | start | end | hypo/hyper | gene annotation | chr | start | end | hypo/hyper | gene annotation |
|---|---|---|---|---|---|---|---|---|---|
| chr7 | 1016343 | 1016373 | Hypo | CYP2W1, COX19 | chr7 | 12751410 | 12751496 | Hypo | |
| chr7 | 22824965 | 22824995 | Hypo | | chr7 | 23253573 | 23253671 | Hypo | AK057873 |
| chr7 | 76033151 | 76033289 | Hypo | ZP3 | chr7 | 99751578 | 99751630 | Hypo | C7orf43, MIR4658, GAL3ST4, LAMTOR4 |
| chr7 | 106797774 | 106797804 | Hypo | PRKAR2B | chr7 | 107483694 | 107483918 | Hypo | |
| chr7 | 140027008 | 140027079 | Hypo | SLC37A3 | chr7 | 140219405 | 140219435 | Hypo | DENND2A |
| chr7 | 150069098 | 150069346 | Hypo | ZNF775, RNU6-34P, REPIN1 | | | | | |
| chr7 | 150070021 | 150070058 | Hypo | ZNF775, REPIN1, RNU6-34P | chr11 | 2040107 | 2040148 | Hypo | |
| chr11 | 3169665 | 3169835 | Hypo | | chr11 | 61148730 | 61148768 | Hypo | |
| chr11 | 75858210 | 75858240 | Hypo | UVRAG | chr11 | 75859012 | 75859053 | Hypo | UVRAG |
| chr11 | 93911651 | 93911800 | Hypo | PANX1 | chr11 | 94275794 | 94275951 | Hypo | PIWIL4, FUT4 |
| chr11 | 118724458 | 118724605 | Hypo | | chr9 | 93698029 | 93698133 | Hypo | |
| chr9 | 111894386 | 111894520 | Hypo | FRRS1L, AL390170 | chr9 | 129517783 | 129517821 | Hypo | |
| chr9 | 134126711 | 134126741 | Hypo | FAM78A | chr16 | 28491774 | 28491924 | Hypo | CLN3 |
| chr16 | 71715779 | 71715809 | Hypo | TRNA_Gln, PHLPP2 | chr14 | 50355854 | 50355924 | Hypo | ARF6 |
| chr14 | 55668368 | 55668526 | Hypo | DLGAP5 | chr14 | 62106193 | 62106242 | Hypo | FLJ22447 |
| chr10 | 3641378 | 3641413 | Hypo | BC037918 | chr10 | 14393819 | 14393893 | Hypo | FRMD4A |
| chr10 | 98558129 | 98558200 | Hypo | | chr10 | 99481747 | 99481905 | Hypo | MARVELD1 |
| chr10 | 101363207 | 101363418 | Hypo | SLC25A28 | chr5 | 32333032 | 32333111 | Hypo | |
| chr5 | 79554097 | 79554169 | Hypo | SERINC5 | chr5 | 82168369 | 82168480 | Hypo | |
| chr5 | 111987744 | 111987818 | Hypo | | chr5 | 124128410 | 124128497 | Hypo | |
| chr5 | 175831257 | 175831326 | Hypo | CLTB | chr5 | 177644565 | 177644601 | Hypo | AGXT2L2, HNRNPAB |
| chr3 | 31494108 | 31494138 | Hypo | | chr3 | 36984378 | 36984425 | Hypo | TRANK1 |
| chr3 | 101094160 | 101094190 | Hypo | SENP7 | chr3 | 128786496 | 128786526 | Hypo | GP9 |
| chr3 | 142791151 | 142791255 | Hypo | | chr3 | 195184022 | 195184140 | Hypo | |
| chr1 | 1095420 | 1095459 | Hypo | MIR200B, MIR200A, JA715134, MIR429, JA715143 | chr1 | 3659550 | 3659716 | Hypo | TP73, CCDC27, TP73-AS1 |
| chr1 | 17757538 | 17757570 | Hypo | RCC2 | chr1 | 24161782 | 24161882 | Hypo | FUCA1 |
| chr1 | 44310283 | 44310324 | Hypo | ST3GAL3 | chr1 | 47788247 | 47788348 | Hypo | |
| chr1 | 151362640 | 151362779 | Hypo | PSMB4 | chr1 | 182862133 | 182862163 | Hypo | SHCBP1L, DHX9 |
| chr1 | 220132075 | 220132115 | Hypo | EPRS | chr1 | 241052360 | 241052419 | Hypo | RGS7 |
| chr8 | 81414643 | 81414831 | Hypo | ZBTB10 | chr19 | 3578138 | 3578223 | Hypo | GIPC3, HMG20B |
| chr19 | 3994540 | 3994595 | Hypo | | chr19 | 4835778 | 4835926 | Hypo | PLIN3 |
| chr19 | 10823678 | 10823721 | Hypo | QTRT1, DNM2, MIR638 | chr19 | 10851287 | 10851362 | Hypo | |
| chr19 | 14334020 | 14334060 | Hypo | | chr19 | 39306433 | 39306545 | Hypo | ECH1, HNRNPL, LGALS4 |
| chr19 | 39310469 | 39310584 | Hypo | HNRNPL, ECH1, LGALS4 | chr19 | 42460961 | 42461113 | Hypo | ATP1A3, RABAC1 |
| chr19 | 50898558 | 50898727 | Hypo | POLD1 | chr12 | 65561778 | 65561940 | Hypo | LEMD3 |
| chr12 | 68433260 | 68433321 | Hypo | | chr12 | 105017109 | 105017228 | Hypo | |
| chr12 | 122940449 | 122940479 | Hypo | | chr15 | 90667461 | 90667586 | Hypo | |
| chr6 | 6753803 | 6753839 | Hypo | | chr6 | 10542836 | 10542977 | Hypo | GCNT2 |
| chr6 | 36178031 | 36178301 | Hypo | BRPF3 | chr6 | 43119078 | 43119580 | Hypo | PTK7 |
| chr6 | 52763812 | 52763982 | Hypo | GSTA3 | chr6 | 88518712 | 88518742 | Hypo | AY927641 |
| chr20 | 5610356 | 5610386 | Hypo | | chr20 | 33547485 | 33547585 | Hypo | MYH7B, GSS |
| chr20 | 42852751 | 42852915 | Hypo | BC036500, OSER1-AS1 | chr20 | 49969348 | 49969515 | Hypo | |
| chr20 | 55959212 | 55959250 | Hypo | RBM38 | chr20 | 62391938 | 62391968 | Hypo | ZBTB46 |
| chr2 | 32580386 | 32580476 | Hypo | BIRC6 | chr2 | 38762382 | 38762412 | Hypo | |
| chr2 | 43388330 | 43388529 | Hypo | | chr2 | 55612770 | 55612800 | Hypo | |
| chr2 | 98581819 | 98581849 | Hypo | TMEM131 | chr2 | 112817735 | 112817765 | Hypo | TMEM87B |

TABLE 4-continued

| Colorectal Cancer | | | | | | | | | |
|---|---|---|---|---|---|---|---|---|---|
| chr | start | end | hypo/hyper | gene annotation | chr | start | end | hypo/hyper | gene annotation |
| chr2 | 114461746 | 114461879 | Hypo | | chr2 | 172367021 | 172367125 | Hypo | |
| chr2 | 201693680 | 201693718 | Hypo | BZW1 | chr2 | 241541932 | 241542357 | Hypo | GPR35, CAPN10 |
| chr17 | 7471610 | 7471709 | Hypo | SNORA67, DD413682, SENP3, TNFSF13, SENP3-EIF4A1, SNORA48, SNORD10 | chr17 | 27686651 | 27686783 | Hypo | |
| chr17 | 48589801 | 48589831 | Hypo | MYCBPAP | chr17 | 53479184 | 53479316 | Hypo | MMD |
| chr17 | 56471121 | 56471167 | Hypo | RNF43 | chr17 | 76404615 | 76404659 | Hypo | PGS1 |
| chr17 | 77070307 | 77070457 | Hypo | ENGASE | chr17 | 80535382 | 80535487 | Hypo | FOXK2 |
| chr13 | 43620862 | 43621006 | Hypo | DNAJC15 | chr13 | 73619660 | 73619784 | Hypo | KLF5 |
| chr13 | 76440730 | 76440760 | Hypo | C13orf45, AK123459 | chr13 | 114189737 | 114189809 | Hypo | TMCO3 |
| chr4 | 718052 | 718112 | Hypo | PCGF3 | chr4 | 718321 | 718456 | Hypo | PCGF3 |
| chr4 | 79689651 | 79689732 | Hypo | BMP2K | chr4 | 128967250 | 128967329 | Hypo | |
| chr21 | 45508617 | 45508647 | Hypo | TRAPPC10 | chr22 | 46599623 | 46599725 | Hypo | PPARA |
| chr18 | 77459762 | 77459877 | Hypo | CTDP1 | chr20 | 4803921 | 4804008 | Hyper | RASSF2 |
| chr20 | 36531799 | 36531910 | Hyper | VSTM2L | chr20 | 37434552 | 37434744 | Hyper | PPP1R16B |
| chr20 | 39317087 | 39317196 | Hyper | MAFB | chr11 | 94473682 | 94473984 | Hyper | |
| chr11 | 94502489 | 94502489 | Hyper | AMOTL1 | chr6 | 73331515 | 73331620 | Hyper | KCNQ5 |
| chr6 | 73332391 | 73332674 | Hyper | KCNQ5 | chr6 | 73332986 | 73333122 | Hyper | KCNQ5 |
| chr6 | 127440331 | 127440524 | Hyper | RSPO3 | chr6 | 151815055 | 151815089 | Hyper | CCDC170 |
| chr6 | 152957953 | 152957995 | Hyper | SYNE1 | chr6 | 163834314 | 163834637 | Hyper | QKI, CAHM |
| chr6 | 163836568 | 163836900 | Hyper | QKI, CAHM | chr17 | 27044770 | 27044800 | Hyper | RPL23A, SNORD42A, TLCD1, PROCA1, SNORD42B, SNORD4A, SNORD4B, NARR, RAB34 |
| chr17 | 32908286 | 32908371 | Hyper | TMEM132E, C17orf102 | chr17 | 46124991 | 46125061 | Hyper | NFE2L1 |
| chr17 | 47574090 | 47574149 | Hyper | NGFR | chr10 | 7450524 | 7450567 | Hyper | SFMBT2 |
| chr10 | 7452349 | 7452550 | Hyper | SFMBT2 | chr10 | 7453491 | 7453521 | Hyper | SFMBT2 |
| chr10 | 49731642 | 49731749 | Hyper | | chr10 | 64578318 | 64578355 | Hyper | EGR2 |
| chr10 | 101089409 | 101089439 | Hyper | CNNM1 | chr10 | 125851517 | 125851645 | Hyper | CHST15 |
| chr10 | 125852299 | 125852524 | Hyper | CHST15 | chr10 | 125852753 | 125853191 | Hyper | CHST15 |
| chr10 | 133795400 | 133795430 | Hyper | BNIP3 | chr8 | 53853997 | 53854027 | Hyper | NPBWR1 |
| chr8 | 80803673 | 80803831 | Hyper | | chr8 | 97506144 | 97506174 | Hyper | SDC2 |
| chr8 | 97507149 | 97507246 | Hyper | SDC2 | chr8 | 143533744 | 143533774 | Hyper | |
| chr15 | 45670462 | 45670879 | Hyper | GATM-AS1, BC039389, GATM | chr15 | 48937058 | 48937095 | Hyper | FBN1 |
| chr15 | 48937427 | 48937987 | Hyper | FBN1 | chr15 | 79383947 | 79383977 | Hyper | |
| chr15 | 83776496 | 83776596 | Hyper | TM6SF1 | chr1 | 3663532 | 3663562 | Hyper | CCDC27, TP73-AS1 |
| chr1 | 12123243 | 12123276 | Hyper | TNFRSF8 | chr1 | 38511661 | 38511757 | Hyper | POU3F1 |
| chr1 | 226814346 | 226814408 | Hyper | ITPKB | chr16 | 10276757 | 10276841 | Hyper | GRIN2A |
| chr7 | 2728068 | 2728108 | Hyper | AMZ1 | chr7 | 28449276 | 28449640 | Hyper | CREB5, BC087859 |
| chr7 | 44364838 | 44364903 | Hyper | CAMK2B | chr7 | 69064590 | 69064858 | Hyper | AUTS2 |
| chr7 | 90226289 | 90226363 | Hyper | CDK14 | chr7 | 108095686 | 108095716 | Hyper | NRCAM |
| chr7 | 134143807 | 134143908 | Hyper | AKR1B1 | chr7 | 149411541 | 149412304 | Hyper | KRBA1, TRNA_Cys |
| chr4 | 156297416 | 156297556 | Hyper | MAP9 | chr4 | 156297979 | 156298073 | Hyper | MAP9 |
| chr19 | 50316244 | 50316330 | Hyper | MED25, FUZ, AP2A1 | chr19 | 57862639 | 57862783 | Hyper | ZNF304 |
| chr19 | 57863024 | 57863148 | Hyper | ZNF304 | chr22 | 39853521 | 39853592 | Hyper | MGAT3 |
| chr5 | 38845675 | 38845705 | Hyper | OSMR | chr5 | 38846224 | 38846431 | Hyper | OSMR |
| chr5 | 82769014 | 82769061 | Hyper | VCAN | chr5 | 146257499 | 146257602 | Hyper | PPP2R2B |
| chr13 | 26625301 | 26625502 | Hyper | SHISA2 | chr13 | 28366065 | 28366122 | Hyper | GSX1 |
| chr13 | 36920349 | 36920379 | Hyper | SPG20, SPG20OS | chr13 | 36920628 | 36920769 | Hyper | SPG20OS, SPG20 |
| chr13 | 88324554 | 88324611 | Hyper | SLITRK5 | chr13 | 93880456 | 93880486 | Hyper | GPC6 |
| chr13 | 95364498 | 95364528 | Hyper | AK055459, SOX21 | chr13 | 95364770 | 95364800 | Hyper | AK055459, SOX21 |
| chr13 | 95620021 | 95620057 | Hyper | | chr13 | 110959796 | 110959860 | Hyper | COL4A2, COL4A1 |
| chr9 | 37026963 | 37026993 | Hyper | PAX5 | chr9 | 140024842 | 140025023 | Hyper | GRIN1 |
| chr21 | 27012373 | 27012431 | Hyper | JAM2 | chr2 | 12858452 | 12858499 | Hyper | TRIB2 |
| chr2 | 29338111 | 29338969 | Hyper | CLIP4 | chr2 | 31360306 | 31360831 | Hyper | GALNT14 |
| chr2 | 31456892 | 31457039 | Hyper | CAPN14, EHD3, 5S_rRNA | chr2 | 100937836 | 100938164 | Hyper | LONRF2 |
| chr2 | 100938480 | 100939155 | Hyper | LONRF2 | chr2 | 144694752 | 144695135 | Hyper | GTDC1 |
| chr12 | 104850505 | 104850592 | Hyper | CHST11 | chr12 | 104851077 | 104851186 | Hyper | CHST11 |
| chr3 | 142839539 | 142839607 | Hyper | CHST2 | chr3 | 179168976 | 179169016 | Hyper | GNB4 |

TABLE 5

Esophageal Cancer

| chr | start | end | hypo/hyper | gene annotation | chr | start | end | hypo/hyper | gene annotation |
|---|---|---|---|---|---|---|---|---|---|
| chr18 | 6908056 | 6908243 | Hypo | ARHGAP28 | chr22 | 35938746 | 35939000 | Hypo | RASD2 |
| chr3 | 13171814 | 13171844 | Hypo | | chr3 | 15780510 | 15780638 | Hypo | BC041363, ANKRD28 |
| chr3 | 196344683 | 196344796 | Hypo | | chr12 | 125589840 | 125589872 | Hypo | AACS |
| chr13 | 50421504 | 50421696 | Hypo | | chr17 | 18817198 | 18817284 | Hypo | PRPSAP2 |
| chr17 | 59481657 | 59481694 | Hypo | C17orf82, TBX2 | chr17 | 73827213 | 73827243 | Hypo | UNK, UNC13D |
| chr15 | 43551059 | 43551196 | Hypo | | chr6 | 26260956 | 26260986 | Hypo | HIST1H2BH |
| chr6 | 97412429 | 97412529 | Hypo | KLHL32 | chr6 | 163602842 | 163602872 | Hypo | AK296276, AK311212 |
| chr6 | 168719983 | 168720019 | Hypo | DACT2 | chr6 | 169002054 | 169002084 | Hypo | SMOC2 |
| chr7 | 409826 | 409892 | Hypo | LOC442497 | chr7 | 38588471 | 38588501 | Hypo | |
| chr7 | 99035152 | 99035191 | Hypo | CPSF4, ATP5J2-PTCD1, PTCD1 | chr5 | 42260050 | 42260080 | Hypo | |
| chr5 | 179217377 | 179217447 | Hypo | LTC4S, MGAT4B, MIR1229 | chr19 | 570156 | 570194 | Hypo | BSG |
| chr19 | 13491305 | 13491340 | Hypo | CACNA1A | chr19 | 36410956 | 36411042 | Hypo | |
| chr19 | 42911568 | 42911598 | Hypo | LIPE-AS1, LIPE | chr14 | 23234956 | 23235032 | Hypo | OXA1L, SLC7A7 |
| chr1 | 3733551 | 3733581 | Hypo | CEP104 | chr1 | 9722138 | 9722215 | Hypo | C1orf200, PIK3CD |
| chr1 | 14097878 | 14098015 | Hypo | PRDM2 | chr1 | 46077719 | 46077805 | Hypo | CCDC17, NASP |
| chr1 | 54837089 | 54837119 | Hypo | SSBP3 | chr9 | 21974207 | 21974237 | Hypo | CDKN2A, C9orf53 |
| chr9 | 112403364 | 112403394 | Hypo | Mir_548, PALM2 | chr9 | 138991798 | 138991828 | Hypo | NACC2 |
| chr16 | 3284117 | 3284147 | Hypo | MEFV, ZNF200 | chr16 | 28877839 | 28877883 | Hypo | SH2B1 |
| chr4 | 3036118 | 3036148 | Hypo | GRK4 | chr4 | 155665445 | 155665475 | Hypo | LRAT, DQ266889 |
| chr11 | 20618292 | 20618322 | Hypo | SLC6A5 | chr11 | 20618526 | 20618556 | Hypo | SLC6A5 |
| chr21 | 45118492 | 45118644 | Hypo | RRP1B | chr2 | 113227024 | 113227225 | Hypo | |
| chr2 | 217448294 | 217448441 | Hypo | | chrY | 13316007 | 13316132 | Hypo | |
| chr8 | 110704001 | 110704144 | Hypo | | chr5 | 129240068 | 129240101 | Hyper | CHSY3 |
| chr19 | 9420142 | 9420240 | Hyper | ZNF699 | chr19 | 10527165 | 10527243 | Hyper | PDE4A |
| chr19 | 12163448 | 12163672 | Hyper | ZNF878 | chr19 | 12163893 | 12163923 | Hyper | ZNF878 |
| chr19 | 12175445 | 12175504 | Hyper | ZNF844 | chr19 | 12476492 | 12476556 | Hyper | ZNF442 |
| chr19 | 12595109 | 12595307 | Hyper | ZNF709 | chr19 | 12595845 | 12595896 | Hyper | ZNF709 |
| chr19 | 12606381 | 12606511 | Hyper | ZNF709 | chr19 | 21688814 | 21688912 | Hyper | ZNF429, LINC00664 |
| chr19 | 23432562 | 23432723 | Hyper | AK023040, ZNF724P | chr19 | 23433143 | 23433296 | Hyper | AK023040, ZNF724P |
| chr19 | 23456615 | 23456881 | Hyper | AK023040 | chr19 | 24216975 | 24217023 | Hyper | ZNF254, AK092150, AK092080 |
| chr19 | 33685544 | 33685581 | Hyper | LRP3 | chr19 | 35264085 | 35264119 | Hyper | ZNF599 |
| chr19 | 37263532 | 37263584 | Hyper | BC024306, ZNF850, AX747375 | chr19 | 37341761 | 37341962 | Hyper | ZNF345, ZNF790 |
| chr19 | 37569289 | 37569554 | Hyper | ZNF420 | chr19 | 37808445 | 37808485 | Hyper | HKR1 |
| chr19 | 38085254 | 38086066 | Hyper | ZNF540, ZNF571 | chr19 | 38146062 | 38146247 | Hyper | ZFP30 |
| chr19 | 38146457 | 38146568 | Hyper | ZFP30 | chr19 | 52097689 | 52097732 | Hyper | FLJ30403, AX748312, ZNF175 |
| chr19 | 53031185 | 53031215 | Hyper | ZNF808 | chr19 | 53193858 | 53193893 | Hyper | |
| chr19 | 53836936 | 53836975 | Hyper | ZNF845 | chr19 | 53837377 | 53837432 | Hyper | ZNF845 |
| chr19 | 58740086 | 58740118 | Hyper | ZNF544 | chr12 | 8549178 | 8549208 | Hyper | LINC00937 |
| chr12 | 8850658 | 8850744 | Hyper | RIMKLB | chr12 | 95267524 | 95267554 | Hyper | |
| chr12 | 133463736 | 133463876 | Hyper | CHFR | chr12 | 133464108 | 133464166 | Hyper | CHFR |
| chr12 | 133758048 | 133758107 | Hyper | ZNF268 | chr14 | 51561765 | 51562012 | Hyper | TRIM9 |
| chr13 | 46961494 | 46961533 | Hyper | KIAA0226L | chr13 | 46961952 | 46961982 | Hyper | KIAA0226L |
| chr13 | 49794117 | 49794179 | Hyper | MLNR | chr13 | 78492684 | 78492748 | Hyper | RNF219-AS1, EDNRB |
| chr13 | 92050760 | 92050814 | Hyper | GPC5 | chr16 | 23313464 | 23313522 | Hyper | SCNN1B |
| chr16 | 23313749 | 23313836 | Hyper | SCNN1B | chr16 | 28891040 | 28891072 | Hyper | ATP2A1, LOC100289092, SH2B1 |
| chr16 | 80837962 | 80838143 | Hyper | CDYL2 | chr16 | 89007880 | 89007995 | Hyper | CBFA2T3 |
| chr18 | 5237878 | 5238247 | Hyper | LINC00667, LINC00526, LOC339290 | chr18 | 11689190 | 11689220 | Hyper | GNAL |
| chr18 | 33877683 | 33877754 | Hyper | FHOD3 | chr15 | 34517058 | 34517334 | Hyper | SLC12A6, EMC4 |
| chr15 | 53082443 | 53082491 | Hyper | ONECUT1 | chr15 | 65669859 | 65669899 | Hyper | IGDCC4 |
| chr15 | 83378212 | 83378370 | Hyper | LOC338963, AP3B2 | chr15 | 91643360 | 91643586 | Hyper | SV2B |
| chr15 | 98964786 | 98965138 | Hyper | | chr8 | 81398018 | 81398155 | Hyper | ZBTB10, DJ031142 |
| chr8 | 81398428 | 81399496 | Hyper | DJ031142, ZBTB10 | chr8 | 107282163 | 107282195 | Hyper | OXR1 |
| chr6 | 53212491 | 53213970 | Hyper | | chr6 | 71665638 | 71665723 | Hyper | B3GAT2 |
| chr21 | 33244921 | 33245040 | Hyper | HUNK | chr21 | 33245683 | 33245718 | Hyper | HUNK |
| chr21 | 33246009 | 33246190 | Hyper | HUNK | chr1 | 3663874 | 3663921 | Hyper | CCDC27, TP73-AS1 |

TABLE 5-continued

Esophageal Cancer

| chr | start | end | hypo/hyper | gene annotation | chr | start | end | hypo/hyper | gene annotation |
|---|---|---|---|---|---|---|---|---|---|
| chr1 | 9712074 | 9712104 | Hyper | C1orf200, PIK3CD | chr1 | 11538705 | 11538821 | Hyper | PTCHD2 |
| chr1 | 11539175 | 11539205 | Hyper | PTCHD2 | chr1 | 11539410 | 11539440 | Hyper | PTCHD2 |
| chr1 | 21058635 | 21058776 | Hyper | SH2D5 | chr1 | 29450491 | 29450543 | Hyper | TMEM200B, EPB41 |
| chr1 | 38512385 | 38512415 | Hyper | POU3F1 | chr1 | 40915590 | 40915620 | Hyper | ZFP69B |
| chr1 | 53019468 | 53019568 | Hyper | ZCCHC11 | chr1 | 53068386 | 53068425 | Hyper | GPX7 |
| chr1 | 91869988 | 91870018 | Hyper | HFM1 | chr1 | 170633607 | 170633637 | Hyper | PRRX1 |
| chr1 | 202679215 | 202679327 | Hyper | SYT2 | chr1 | 209381132 | 209381165 | Hyper | |
| chr1 | 230561779 | 230561824 | Hyper | PGBD5 | chr1 | 244014221 | 244014376 | Hyper | |
| chr17 | 8534493 | 8534582 | Hyper | | chr17 | 14204212 | 14204242 | Hyper | HS3ST3B1, MGC12916 |
| chr17 | 14204527 | 14204620 | Hyper | MGC12916, HS3ST3B1 | chr17 | 33288229 | 33288351 | Hyper | ZNF830, CCT6B |
| chr17 | 33288890 | 33288988 | Hyper | ZNF830, CCT6B | chr17 | 40333044 | 40333226 | Hyper | GHDC, KCNH4, HCRT |
| chr17 | 42907564 | 42907630 | Hyper | | chr17 | 45331014 | 45331313 | Hyper | ITGB3 |
| chr17 | 48071020 | 48071050 | Hyper | DLX3 | chr17 | 51901004 | 51901034 | Hyper | KIF2B |
| chr17 | 56327271 | 56327301 | Hyper | LPO | chr17 | 56833707 | 56833953 | Hyper | PPM1E |
| chr10 | 12390825 | 12390995 | Hyper | CAMK1D | chr10 | 12391870 | 12392327 | Hyper | CAMK1D |
| chr10 | 116853875 | 116853908 | Hyper | ATRNL1 | chr10 | 118609305 | 118609390 | Hyper | ENO4, KIAA1598 |
| chr10 | 134755904 | 134755934 | Hyper | TTC40 | chr2 | 31456682 | 31456712 | Hyper | EHD3, 5S_rRNA, CAPN14 |
| chr2 | 56410817 | 56410996 | Hyper | CCDC85A, AK311113, AK295617 | chr2 | 56411691 | 56411733 | Hyper | CCDC85A, AK311113, AK295617 |
| chr2 | 224903260 | 224903440 | Hyper | SERPINE2 | chr2 | 224903690 | 224903755 | Hyper | SERPINE2 |
| chr2 | 224904108 | 224904237 | Hyper | SERPINE2 | chr2 | 228029470 | 228029500 | Hyper | COL4A3 |
| chr22 | 19702265 | 19702410 | Hyper | SEPT5-GP1BB | chr22 | 21368587 | 21368617 | Hyper | P2RX6, TUBA3FP, THAP7-AS1 |
| chr22 | 24820330 | 24820396 | Hyper | ADORA2A, ADORA2A-AS1, EU036692, SPECC1L | chr22 | 44208418 | 44208448 | Hyper | |
| GL000225.1 | 37720 | 37842 | Hyper | | chr4 | 331322 | 331352 | Hyper | ZNF141 |
| chr4 | 57687720 | 57687782 | Hyper | SPINK2 | chr4 | 58030191 | 58030524 | Hyper | LOC255130 |
| chr4 | 75858573 | 75858629 | Hyper | PARM1 | chr4 | 87515337 | 87515367 | Hyper | PTPN13 |
| chr7 | 41982690 | 41982874 | Hyper | | chr7 | 54609976 | 54610006 | Hyper | VSTM2A |
| chr7 | 87104816 | 87105101 | Hyper | ABCB4 | chr7 | 87257931 | 87258054 | Hyper | RUNDC3B, ABCB1 |
| chr7 | 87563370 | 87563614 | Hyper | ADAM22 | chr7 | 87563829 | 87563890 | Hyper | ADAM22 |
| chr7 | 106685282 | 106685345 | Hyper | PRKAR2B | chr7 | 113726509 | 113726539 | Hyper | FOXP2 |
| chr7 | 126894076 | 126894197 | Hyper | | chr7 | 149570368 | 149570406 | Hyper | ZNF862, DQ590227, ATP6V0E2, ATP6V0E2-AS1 |
| chr3 | 8725296 | 8725348 | Hyper | | chr3 | 12729424 | 12729454 | Hyper | |
| chr3 | 37493519 | 37493621 | Hyper | ITGA9 | chr3 | 38691348 | 38691466 | Hyper | SCN5A |
| chr3 | 46924934 | 46924964 | Hyper | PTH1R | chr3 | 49591832 | 49592076 | Hyper | BSN, BSN-AS2 |
| chr3 | 49907093 | 49907130 | Hyper | CAMKV | chr3 | 55519219 | 55519253 | Hyper | WNT5A |
| chr3 | 98620891 | 98620980 | Hyper | DCBLD2 | chr3 | 120169104 | 120169149 | Hyper | FSTL1 |
| chr3 | 180320256 | 180320294 | Hyper | TTC14 | chr9 | 36037068 | 36037098 | Hyper | RECK |
| chr9 | 123004898 | 123004928 | Hyper | MIR147A | chr9 | 132804405 | 132804455 | Hyper | FNBP1 |
| chr9 | 132804796 | 132804974 | Hyper | FNBP1 | chr9 | 132805318 | 132805445 | Hyper | FNBP1 |
| chr9 | 132805737 | 132805893 | Hyper | FNBP1 | chr9 | 137702189 | 137702222 | Hyper | LOC101448202, COL5A1 |
| chr11 | 46413042 | 46413304 | Hyper | AMBRA1, CHRM4, MDK | chr11 | 64410723 | 64410759 | Hyper | NRXN2 |
| chr11 | 64490435 | 64490561 | Hyper | RASGRP2 | chr11 | 64490792 | 64491159 | Hyper | RASGRP2 |
| chr11 | 107461623 | 107461653 | Hyper | ELMOD1, LOC643923 | chr11 | 110166519 | 110166935 | Hyper | |
| chr11 | 114113022 | 114113052 | Hyper | ZBTB16 | chr11 | 120894800 | 120895026 | Hyper | TBCEL |
| chr20 | 1876110 | 1876176 | Hyper | SIRPA | chr20 | 4230570 | 4230600 | Hyper | ADRA1D |
| chr20 | 20348526 | 20348605 | Hyper | INSM1, C20orf26 | chr20 | 20349574 | 20349604 | Hyper | INSM1, C20orf26 |
| chr20 | 39317750 | 39318166 | Hyper | MAFB | chr20 | 39318383 | 39318415 | Hyper | MAFB |
| chr20 | 62680657 | 62680739 | Hyper | TCEA2, SOX18, LINC00176 | chr20 | 62715014 | 62715069 | Hyper | OPRL1, C20orf201, RGS19 |

TABLE 6

Head and Neck Cancer

| chr | start | end | hypo/hyper | gene annotation | chr | start | end | hypo/hyper | gene annotation |
|---|---|---|---|---|---|---|---|---|---|
| chr21 | 43485279 | 43485348 | Hypo | UMODL1, AX748362 | chr21 | 44283581 | 44283774 | Hypo | WDR4 |
| chr21 | 45290014 | 45290044 | Hypo | AGPAT3 | chr4 | 512978 | 513008 | Hypo | PIGG |
| chr4 | 513704 | 513734 | Hypo | PIGG | chr4 | 6839352 | 6839402 | Hypo | KIAA0232 |
| chr4 | 38566328 | 38566418 | Hypo |  | chr4 | 48848428 | 48848554 | Hypo | OCIAD1 |
| chr4 | 128968647 | 128968800 | Hypo |  | chr4 | 128969310 | 128969382 | Hypo |  |
| chr4 | 146853951 | 146853981 | Hypo | ZNF827 | chr4 | 154374504 | 154374630 | Hypo |  |
| chr4 | 159149784 | 159149824 | Hypo | TMEM144 | chr4 | 178285756 | 178285879 | Hypo |  |
| chr2 | 25600736 | 25600804 | Hypo | DTNB | chr2 | 25928094 | 25928166 | Hypo | Y_RNA |
| chr2 | 38983213 | 38983333 | Hypo | GEMIN6, SRSF7 | chr2 | 44226958 | 44226988 | Hypo | LRPPRC |
| chr2 | 44227193 | 44227223 | Hypo | LRPPRC | chr2 | 65251310 | 65251340 | Hypo | SLC1A4 |
| chr2 | 68287707 | 68287799 | Hypo | C1D | chr2 | 97126702 | 97126832 | Hypo |  |
| chr2 | 174148058 | 174148157 | Hypo | MLK7-AS1 | chrX | 3746612 | 3746642 | Hypo | TRNA_Ile, LOC389906 |
| chrX | 100228394 | 100228431 | Hypo | ARL13A | chr18 | 74501144 | 74501183 | Hypo | LOC100131655 |
| chrY | 21204734 | 21205113 | Hypo |  | chrY | 22530026 | 22530073 | Hypo |  |
| chr14 | 21100748 | 21100778 | Hypo | TRNA_Leu, TRNA_Pro, OR6S1, TRNA_Thr | chr14 | 23701644 | 23701737 | Hypo |  |
| chr14 | 34269897 | 34270004 | Hypo |  | chr14 | 102973169 | 102973268 | Hypo | ANKRD9, TECPR2 |
| chr7 | 44097690 | 44097876 | Hypo | PGAM2, DBNL | chr7 | 44912004 | 44912034 | Hypo | PURB |
| chr3 | 101331792 | 101331861 | Hypo |  | chr3 | 121215241 | 121215271 | Hypo | POLQ |
| chr3 | 124410075 | 124410157 | Hypo |  | chr3 | 129008841 | 129009004 | Hypo | C3orf37 |
| chr3 | 136016868 | 136016942 | Hypo | PCCB | chr3 | 141832939 | 141833015 | Hypo | TFDP2 |
| chr3 | 195639755 | 195639785 | Hypo | AK127609, TNK2 | chr3 | 196046702 | 196046830 | Hypo | AK124973, TCTEX1D2, TM4SF19, TM4SF19-TCTEX1D2 |
| chr3 | 196433946 | 196434104 | Hypo | U6, PIGX, CEP19 | chr3 | 196440510 | 196440676 | Hypo | PIGX, U6, CEP19 |
| chr3 | 196728418 | 196728448 | Hypo | MFI2, MFI2-AS1 | chr8 | 11700190 | 11700284 | Hypo | CTSB, FDFT1 |
| chr8 | 22458657 | 22458687 | Hypo | KIAA1967, C8orf58, PDLIM2 | chr8 | 28737884 | 28738023 | Hypo | HMBOX1, INTS9 |
| chr8 | 37906396 | 37906513 | Hypo | EIF4EBP1 | chr8 | 38020213 | 38020272 | Hypo | LSM1 |
| chr8 | 125411827 | 125411857 | Hypo |  | chr8 | 144557003 | 144557088 | Hypo | ZC3H3 |
| chr13 | 50639705 | 50639799 | Hypo | DLEU2 | chr13 | 96177285 | 96177315 | Hypo | CLDN10-AS1, CLDN10 |
| chr13 | 114807744 | 114807815 | Hypo | RASA3 | chr1 | 898654 | 898690 | Hypo | PLEKHN1, KLHL17, NOC2L |
| chr1 | 1473125 | 1473207 | Hypo | SSU72, TMEM240, AX747755, ATAD3A | chr1 | 1483186 | 1483363 | Hypo | SSU72, TMEM240 |
| chr1 | 1856436 | 1856466 | Hypo | C1orf222, TMEM52, CALML6 | chr1 | 1910415 | 1910445 | Hypo | KIAA1751 |
| chr1 | 6410456 | 6410486 | Hypo | ACOT7 | chr1 | 10123736 | 10123928 | Hypo | UBE4B |
| chr1 | 10166521 | 10166551 | Hypo | UBE4B | chr1 | 11886250 | 11886280 | Hypo | CLCN6 |
| chr1 | 13984525 | 13984742 | Hypo |  | chr1 | 14149749 | 14149867 | Hypo | AK124197 |
| chr1 | 21050471 | 21050511 | Hypo | SH2D5, KIF17 | chr1 | 21713716 | 21713792 | Hypo |  |
| chr1 | 23449766 | 23449859 | Hypo | LUZP1 | chr1 | 27724093 | 27724093 | Hypo | WASF2, GPR3 |
| chr1 | 33163605 | 33163786 | Hypo | SYNC | chr1 | 40708443 | 40708578 | Hypo | RLF, TMCO2 |
| chr1 | 43400336 | 43400386 | Hypo | SLC2A1 | chr1 | 47078736 | 47078782 | Hypo | MOB3C, MKNK1 |
| chr1 | 97185262 | 97185609 | Hypo | PTBP2 | chr1 | 113166315 | 113166394 | Hypo | CAPZA1, ST7L |
| chr1 | 114428007 | 114428160 | Hypo | BCL2L15, AP4B1-AS1, AP4B1 | chr1 | 155653788 | 155653868 | Hypo | DAP3, YY1AP1 |
| chr1 | 181014878 | 181014997 | Hypo | MR1 | chr1 | 204524704 | 204524744 | Hypo | MDM4 |
| chr1 | 246488175 | 246488336 | Hypo | SMYD3 | chr6 | 8014600 | 8014772 | Hypo | BLOC1S5, EEF1E1-MUTED |
| chr15 | 50450454 | 50450574 | Hypo |  | chr15 | 66113240 | 66113270 | Hypo |  |
| chr10 | 524754 | 524784 | Hypo | DIP2C | chr10 | 13715208 | 13715401 | Hypo | FRMD4A |
| chr10 | 94062288 | 94062318 | Hypo | 5-Mar | chr10 | 126101966 | 126102095 | Hypo | OAT |
| chr22 | 20940868 | 20940898 | Hypo | MED15 | chr22 | 22201344 | 22201568 | Hypo | MAPK1 |
| chr22 | 36902291 | 36902381 | Hypo | EIF3D, FOXRED2 | chr22 | 38087310 | 38087367 | Hypo | TRIOBP, NOL12 |
| chr22 | 38182815 | 38182981 | Hypo |  | chr22 | 38874215 | 38874362 | Hypo | DDX17, KDELR3 |
| chr22 | 39112502 | 39112584 | Hypo | GTPBP1 | chr22 | 41648414 | 41648444 | Hypo | RANGAP1 |
| chr22 | 41690119 | 41690149 | Hypo | ZC3H7B, RANGAP1 | chr22 | 42096002 | 42096190 | Hypo | FLJ23584, C22orf46, MEI1 |
| chr22 | 47023044 | 47023191 | Hypo | GRAMD4 | chr22 | 47054686 | 47054716 | Hypo | GRAMD4 |
| chr5 | 909204 | 909304 | Hypo | TRIP13 | chr5 | 1136590 | 1136845 | Hypo |  |
| chr5 | 71106820 | 71107027 | Hypo |  | chr5 | 78039632 | 78039673 | Hypo |  |
| chr5 | 112340666 | 112340704 | Hypo | DCP2 | chr5 | 138196197 | 138196408 | Hypo | LRRTM2, CTNNA1 |
| chr5 | 171352123 | 171352153 | Hypo | FBXW11 | chr20 | 7980362 | 7980392 | Hypo | TMX4 |
| chr20 | 35640448 | 35640561 | Hypo | RBL1 | chr20 | 60816241 | 60816271 | Hypo | OSBPL2, AK126744 |
| chr17 | 556252 | 556282 | Hypo | VPS53 | chr17 | 631704 | 631734 | Hypo | FAM57A |
| chr17 | 1536116 | 1536146 | Hypo | SCARF1 | chr17 | 15926819 | 15926849 | Hypo | NCOR1, TTC19 |
| chr17 | 16326144 | 16326216 | Hypo | TRPV2 | chr17 | 16428708 | 16428738 | Hypo |  |

TABLE 6-continued

Head and Neck Cancer

| chr | start | end | hypo/hyper | gene annotation | chr | start | end | hypo/hyper | gene annotation |
|---|---|---|---|---|---|---|---|---|---|
| chr17 | 17062574 | 17062763 | Hypo | MPRIP | chr17 | 17123963 | 17123993 | Hypo | FLCN, PLD6 |
| chr17 | 19886035 | 19886221 | Hypo | AKAP10 | chr17 | 30258469 | 30258499 | Hypo | SUZ12 |
| chr17 | 42110423 | 42110561 | Hypo | LSM12 | chr17 | 73808631 | 73808671 | Hypo | UNK |
| chr17 | 74087118 | 74087185 | Hypo | EXOC7, ZACN | chr17 | 74663258 | 74663288 | Hypo | MXRA7 |
| chr17 | 80491572 | 80491602 | Hypo | FOXK2 | chr17 | 80859239 | 80859269 | Hypo | TBCD |
| chr11 | 392576 | 392720 | Hypo | PKP3 | chr11 | 1027540 | 1027574 | Hypo | MUC6 |
| chr11 | 3027425 | 3027562 | Hypo | CARS | chr11 | 33264773 | 33264935 | Hypo | |
| chr11 | 47363557 | 47363625 | Hypo | MYBPC3 | chr11 | 66454424 | 66454454 | Hypo | SPTBN2, RBM4B |
| chr11 | 76293588 | 76293618 | Hypo | | chr16 | 93831 | 93932 | Hypo | POLR3K, SNRNP25 |
| chr16 | 672730 | 672806 | Hypo | AK128777, WFIKKN1, RAB40C | chr16 | 1397454 | 1397484 | Hypo | GNPTG, BAIAP3, TSR3 |
| chr16 | 1750769 | 1750907 | Hypo | MAPK8IP3, HN1L | chr16 | 2042875 | 2042905 | Hypo | ZNF598, SYNGR3, GFER |
| chr16 | 2128577 | 2129581 | Hypo | TSC2, PKD1 | chr16 | 2485858 | 2485917 | Hypo | CCNF |
| chr16 | 2974601 | 2974650 | Hypo | FLYWCH1 | chr16 | 12210772 | 12210896 | Hypo | SNX29 |
| chr16 | 12211279 | 12211416 | Hypo | SNX29 | chr16 | 21665540 | 21665570 | Hypo | IGSF6 |
| chr16 | 21666641 | 21666771 | Hypo | IGSF6 | chr16 | 22326397 | 22326427 | Hypo | POLR3E |
| chr16 | 27207774 | 27207852 | Hypo | KDM8 | chr16 | 48450544 | 48450574 | Hypo | |
| chr16 | 88007072 | 88007108 | Hypo | BANP | chr16 | 88757466 | 88757496 | Hypo | RNF166, SNAI3 |
| chr16 | 89240843 | 89240873 | Hypo | CDH15, LOC400558 | chr16 | 89584136 | 89584417 | Hypo | SPG7 |
| chr9 | 34136792 | 34136903 | Hypo | DQ574810, DQ585850, DQ594696, DQ597117, DQ587955 | chr9 | 37119301 | 37119331 | Hypo | ZCCHC7 |
| chr9 | 97845915 | 97845947 | Hypo | MIR23B, MIR3074 | chr9 | 106998039 | 106998134 | Hypo | |
| chr9 | 119603412 | 119603535 | Hypo | | chr9 | 127605297 | 127605327 | Hypo | |
| chr9 | 131542193 | 131542267 | Hypo | TBC1D13, ZER1 | chr9 | 138826382 | 138826412 | Hypo | UBAC1 |
| chr9 | 139477862 | 139478020 | Hypo | | chr9 | 140709046 | 140709174 | Hypo | EHMT1 |
| chr9 | 140727471 | 140727511 | Hypo | MIR602, EHMT1 | chr9 | 140727845 | 140727930 | Hypo | MIR602, EHMT1 |
| chr19 | 607070 | 607110 | Hypo | HCN2 | chr19 | 8554173 | 8554218 | Hypo | PRAM1, DKFZp547H118, HNRNPM |
| chr19 | 16766902 | 16766932 | Hypo | TMEM38A, SMIM7 | chr19 | 17436061 | 17436203 | Hypo | GTPBP3, ANO8, DDA1 |
| chr19 | 18496000 | 18496030 | Hypo | GDF15, MIR3189, LRRC25 | chr19 | 50243339 | 50243379 | Hypo | TSKS |
| chr12 | 49035233 | 49035414 | Hypo | | chr12 | 122108464 | 122108601 | Hypo | MORN3 |
| chr12 | 132643233 | 132643279 | Hypo | NOC4L | chr11 | 69484356 | 69484454 | Hyper | ORAOV1 |
| chr11 | 94884130 | 94884160 | Hyper | AK055250 | chr12 | 54399616 | 54399646 | Hyper | HOXC8, HOXC9 |
| chr14 | 21100801 | 21100831 | Hyper | TRNA_Leu, TRNA_Pro, OR6S1, TRNA_Thr | chr14 | 94889856 | 94889886 | Hyper | |
| chr21 | 39047776 | 39047838 | Hyper | KCNJ6 | chr21 | 45717477 | 45717548 | Hyper | PFKL, AIRE |
| chr17 | 7348885 | 7348997 | Hyper | CHRNB1, FGF11, TMEM102 | chr17 | 49027838 | 49027876 | Hyper | |
| chr22 | 30881582 | 30881612 | Hyper | SEC14L4, SDC4P | chr22 | 50943093 | 50943262 | Hyper | NCAPH2, LMF2 |
| chr2 | 129494389 | 129494421 | Hyper | | chrY | 14532822 | 14532852 | Hyper | GYG2P1 |
| chrY | 14533556 | 14533613 | Hyper | GYG2P1 | chr1 | 2375148 | 2375355 | Hyper | |
| chr1 | 32180397 | 32180427 | Hyper | | chr1 | 161368993 | 161369405 | Hyper | TRNA_Val |
| chr1 | 161369859 | 161369945 | Hyper | TRNA_Val | chr1 | 177150773 | 177150803 | Hyper | FAM5B |
| chr8 | 67025063 | 67025640 | Hyper | TRNA_Tyr, TRNA_Ala | chr8 | 67025920 | 67026578 | Hyper | TRNA_Tyr, TRNA_Ala |
| chr8 | 67026812 | 67026990 | Hyper | TRNA_Ala, TRNA_Tyr | chr8 | 101920382 | 101920468 | Hyper | |
| chr4 | 185089696 | 185089797 | Hyper | ENPP6 | chr5 | 57878710 | 57878752 | Hyper | RAB3C |
| chr5 | 87976028 | 87976308 | Hyper | | chr5 | 87976525 | 87976559 | Hyper | |
| chr5 | 174220971 | 174221001 | Hyper | | chr5 | 180594851 | 180595002 | Hyper | TRNA_Val, TRNA_Leu, TRNA_Pseudo |
| chr19 | 1308047 | 1308081 | Hyper | EFNA2 | chr19 | 1775076 | 1775239 | Hyper | ATP8B3, ONECUT3 |
| chr19 | 34533139 | 34533169 | Hyper | | chr19 | 51041149 | 51041189 | Hyper | LRRC4B |
| chr19 | 58144494 | 58144701 | Hyper | ZNF211 | chr3 | 154797383 | 154797416 | Hyper | MME |
| chr18 | 13824025 | 13824102 | Hyper | MC5R | chr18 | 32557832 | 32557864 | Hyper | MAPRE2 |

TABLE 7

Hepatobiliary Cancer

| chr | start | end | hypo/hyper | gene annotation | chr | start | end | hypo/hyper | gene annotation |
|---|---|---|---|---|---|---|---|---|---|
| chr20 | 4061323 | 4061452 | Hypo | | chr11 | 3511446 | 3511501 | Hypo | |
| chr11 | 13711492 | 13711529 | Hypo | FAR1 | chr11 | 68409558 | 68409588 | Hypo | |
| chr11 | 130343061 | 130343100 | Hypo | ADAMTS15 | chr11 | 133792055 | 133792214 | Hypo | IGSF9B |
| chr21 | 42596911 | 42597043 | Hypo | | chr21 | 42617963 | 42617995 | Hypo | BACE2 |
| chr21 | 42649172 | 42649202 | Hypo | BACE2 | chr3 | 54583435 | 54583465 | Hypo | |
| chr3 | 70661011 | 70661079 | Hypo | | chr3 | 112185933 | 112185975 | Hypo | BTLA |
| chr3 | 129372419 | 129372546 | Hypo | TMCC1 | chr3 | 158319235 | 158319359 | Hypo | MLF1 |
| chr19 | 3834572 | 3834641 | Hypo | ZFR2 | chr19 | 9331918 | 9331955 | Hypo | OR7D4 |
| chr19 | 12205385 | 12205434 | Hypo | ZNF788 | chr19 | 13782965 | 13783028 | Hypo | |
| chr19 | 21237609 | 21237655 | Hypo | ZNF430 | chr19 | 21239053 | 21239129 | Hypo | ZNF430 |
| chr19 | 21245066 | 21245152 | Hypo | ZNF430 | chr19 | 21289719 | 21289749 | Hypo | ZNF714 |
| chr19 | 21290153 | 21290216 | Hypo | ZNF714 | chr19 | 21303863 | 21303993 | Hypo | AX746719, ZNF714 |
| chr19 | 21305707 | 21305737 | Hypo | AX746719, ZNF714 | chr19 | 21370382 | 21370479 | Hypo | ZNF431 |
| chr19 | 53204758 | 53204837 | Hypo | ZNF611 | chr19 | 53398908 | 53399031 | Hypo | ZNF320 |
| chr19 | 53436895 | 53437067 | Hypo | ZNF816-ZNF321P, ZNF321P | chr19 | 53688015 | 53688059 | Hypo | ZNF665 |
| chr19 | 53860082 | 53860151 | Hypo | ZNF525, ZNF765, ZNF845 | chr19 | 53873182 | 53873212 | Hypo | ZNF765, ZNF525 |
| chr19 | 54271479 | 54271509 | Hypo | MIR519A2, MIR516A2, MIR1283-2 | chr1 | 5919973 | 5920071 | Hypo | MIR4689, NPHP4 |
| chr1 | 5920650 | 5920710 | Hypo | NPHP4, MIR4689 | chr1 | 5924296 | 5924431 | Hypo | NPHP4, MIR4689 |
| chr1 | 5924851 | 5924984 | Hypo | NPHP4, MIR4689 | chr1 | 5926596 | 5926645 | Hypo | NPHP4, MIR4689 |
| chr1 | 5933086 | 5933144 | Hypo | NPHP4 | chr1 | 5934925 | 5935061 | Hypo | NPHP4 |
| chr1 | 5940517 | 5940547 | Hypo | NPHP4 | chr1 | 5940945 | 5941132 | Hypo | NPHP4 |
| chr1 | 5944299 | 5944449 | Hypo | NPHP4 | chr1 | 5944962 | 5945001 | Hypo | NPHP4 |
| chr1 | 5945348 | 5945435 | Hypo | NPHP4 | chr1 | 5947258 | 5947288 | Hypo | NPHP4 |
| chr1 | 5949491 | 5949575 | Hypo | NPHP4 | chr1 | 5950965 | 5951039 | Hypo | NPHP4 |
| chr1 | 5957473 | 5957503 | Hypo | NPHP4 | chr1 | 5967237 | 5967267 | Hypo | NPHP4 |
| chr1 | 5969001 | 5969283 | Hypo | NPHP4 | chr1 | 5972104 | 5972134 | Hypo | NPHP4 |
| chr1 | 5972878 | 5972922 | Hypo | NPHP4 | chr1 | 6021621 | 6021651 | Hypo | |
| chr1 | 6025872 | 6025950 | Hypo | | chr1 | 6036766 | 6036796 | Hypo | |
| chr1 | 6056157 | 6056201 | Hypo | KCNAB2 | chr1 | 6056506 | 6056651 | Hypo | KCNAB2 |
| chr1 | 6059910 | 6059974 | Hypo | KCNAB2 | chr1 | 9601954 | 9601984 | Hypo | SLC25A33 |
| chr1 | 14032304 | 14032347 | Hypo | PRDM2 | chr1 | 14746206 | 14746245 | Hypo | |
| chr1 | 15128565 | 15128595 | Hypo | KAZN | chr1 | 108722798 | 108722828 | Hypo | SLC25A24 |
| chr1 | 158318949 | 158318979 | Hypo | CD1E | chr1 | 163393034 | 163393064 | Hypo | |
| chr1 | 164518220 | 164518270 | Hypo | | chr1 | 164730649 | 164730796 | Hypo | LOC100505795 |
| chr1 | 186570930 | 186571030 | Hypo | | chr1 | 226997660 | 226997719 | Hypo | |
| chr1 | 228461158 | 228461197 | Hypo | OBSCN | chr1 | 245849914 | 245849944 | Hypo | KIF26B |
| chr1 | 247608784 | 247608814 | Hypo | OR2B11, NLRP3 | chr8 | 142282078 | 142282202 | Hypo | |
| chr8 | 143611232 | 143611262 | Hypo | BAI1 | chr18 | 12277243 | 12277273 | Hypo | CIDEA |
| chr18 | 77309533 | 77309563 | Hypo | | chr14 | 91780382 | 91780512 | Hypo | |
| chr14 | 91801036 | 91801164 | Hypo | CCDC88C | chr6 | 22172209 | 22172305 | Hypo | LINC00340 |
| chr6 | 22172536 | 22172566 | Hypo | LINC00340 | chr6 | 33632930 | 33633000 | Hypo | ITPR3 |
| chr6 | 33636388 | 33636418 | Hypo | ITPR3 | chr6 | 73980676 | 73980722 | Hypo | BC031876, KHDC1, C6orf147, AL832252 |
| chr6 | 73982025 | 73982058 | Hypo | AL832252, BC031876, KHDC1, C6orf147 | chr6 | 97930083 | 97930113 | Hypo | AK091365 |
| chr6 | 121797231 | 121797265 | Hypo | | chr6 | 168972472 | 168972502 | Hypo | SMOC2 |
| chr4 | 26256826 | 26256867 | Hypo | | chr4 | 56594679 | 56594720 | Hypo | |
| chr4 | 57017387 | 57017459 | Hypo | | chr4 | 80273120 | 80273150 | Hypo | |
| chr4 | 159063301 | 159063331 | Hypo | FAM198B | chr4 | 164819191 | 164819221 | Hypo | |
| chr4 | 173953411 | 173953594 | Hypo | | chr4 | 174083164 | 174083431 | Hypo | GALNT7, BC040577 |
| chr4 | 174124429 | 174124477 | Hypo | GALNT7 | chr4 | 174136704 | 174136734 | Hypo | GALNT7 |
| chr4 | 174224186 | 174224216 | Hypo | GALNT7 | chr10 | 1577394 | 1577424 | Hypo | ADARB2-AS1 |
| chr10 | 6513976 | 6514006 | Hypo | PRKCQ | chr10 | 7213505 | 7213535 | Hypo | SFMBT2 |
| chr10 | 7255730 | 7255821 | Hypo | SFMBT2 | chr10 | 7334737 | 7334767 | Hypo | SFMBT2 |
| chr10 | 7363436 | 7363466 | Hypo | SFMBT2 | chr10 | 7424626 | 7424687 | Hypo | SFMBT2 |
| chr10 | 16175687 | 16175801 | Hypo | | chr10 | 17509450 | 17509503 | Hypo | |
| chr10 | 21101525 | 21101555 | Hypo | NEBL | chr10 | 71084706 | 71085116 | Hypo | HK1 |
| chr10 | 85792257 | 85792287 | Hypo | | chr10 | 121267480 | 121267626 | Hypo | RGS10 |
| chr10 | 125527754 | 125527784 | Hypo | CPXM2 | chr10 | 126782965 | 126783048 | Hypo | |
| chr10 | 126828994 | 126829024 | Hypo | | chr10 | 127693923 | 127693959 | Hypo | ADAM12, FANK1 |
| chr10 | 134039087 | 134039117 | Hypo | STK32C | chr10 | 134119401 | 134119447 | Hypo | STK32C |
| chr10 | 134896060 | 134896092 | Hypo | GPR123 | chr13 | 23653781 | 23653813 | Hypo | |
| chr13 | 24099683 | 24099713 | Hypo | | chr13 | 29112395 | 29112444 | Hypo | |
| chr13 | 36909206 | 36909236 | Hypo | SPG20 | chr13 | 40000498 | 40000528 | Hypo | LHFP |
| chr13 | 66697959 | 66698124 | Hypo | | chr13 | 91755723 | 91755837 | Hypo | |
| chr13 | 107827301 | 107827331 | Hypo | FAM155A | chr2 | 1652837 | 1653230 | Hypo | PXDN |

TABLE 7-continued

Hepatobiliary Cancer

| chr | start | end | hypo/hyper | gene annotation | chr | start | end | hypo/hyper | gene annotation |
|---|---|---|---|---|---|---|---|---|---|
| chr2 | 1670168 | 1670216 | Hypo | PXDN | chr2 | 9090685 | 9090760 | Hypo | MBOAT2 |
| chr2 | 9192356 | 9192402 | Hypo |  | chr2 | 13557899 | 13558057 | Hypo |  |
| chr2 | 30514753 | 30514783 | Hypo |  | chr2 | 41789816 | 41789853 | Hypo |  |
| chr2 | 183251240 | 183251303 | Hypo | PDE1A | chr2 | 221853201 | 221853352 | Hypo |  |
| chr2 | 222285828 | 222285858 | Hypo | EPHA4 | chr2 | 222310068 | 222310105 | Hypo | EPHA4 |
| chr22 | 40075157 | 40075302 | Hypo | CACNA1I | chr22 | 45252427 | 45252463 | Hypo | ARHGAP8 |
| chr22 | 45313416 | 45313446 | Hypo | PHF21B | chr9 | 14884008 | 14884061 | Hypo |  |
| chr9 | 20199955 | 20199985 | Hypo |  | chr9 | 71500847 | 71500886 | Hypo |  |
| chr9 | 71584152 | 71584254 | Hypo | AK057188 | chr9 | 79197119 | 79197149 | Hypo |  |
| chr9 | 90907408 | 90907438 | Hypo |  | chr9 | 94686919 | 94686957 | Hypo | ROR2 |
| chr9 | 135073463 | 135073506 | Hypo | NTNG2 | chr17 | 2811362 | 2811392 | Hypo | RAP1GAP2 |
| chr17 | 2873476 | 2873551 | Hypo | RAP1GAP2 | chr17 | 20039589 | 20039676 | Hypo | SPECC1 |
| chr17 | 20081131 | 20081161 | Hypo | SPECC1 | chr17 | 20205055 | 20205181 | Hypo | SPECC1 |
| chr17 | 20238152 | 20238198 | Hypo | CCDC144CP | chr17 | 20468021 | 20468090 | Hypo | DQ584223 |
| chr17 | 72236510 | 72236548 | Hypo | TTYH2 | chr17 | 76877177 | 76877212 | Hypo | LOC100653515, TIMP2 |
| chr17 | 76884417 | 76884447 | Hypo | LOC100653515, TIMP2 | chr5 | 1259524 | 1259558 | Hypo | TERT |
| chr5 | 1271339 | 1271396 | Hypo | TERT | chr5 | 1779526 | 1779556 | Hypo |  |
| chr5 | 3152146 | 3152176 | Hypo |  | chr5 | 16793851 | 16794008 | Hypo | MYO10 |
| chr5 | 16845452 | 16845619 | Hypo | MYO10 | chr5 | 16968118 | 16968148 | Hypo |  |
| chr5 | 17095895 | 17095927 | Hypo |  | chr5 | 17311046 | 17311076 | Hypo |  |
| chr5 | 17512114 | 17512144 | Hypo |  | chr5 | 18034335 | 18034365 | Hypo |  |
| chr5 | 31879243 | 31879282 | Hypo | PDZD2 | chr5 | 116143325 | 116143325 | Hypo |  |
| chr5 | 176295786 | 176295892 | Hypo | UNC5A | chr5 | 178151333 | 178151363 | Hypo | ZNF354A |
| chr15 | 29452432 | 29452462 | Hypo | FAM189A1 | chr15 | 99254040 | 99254208 | Hypo | IGF1R |
| chr15 | 99453230 | 99453440 | Hypo | IGF1R, AF020763 | chr15 | 99456299 | 99456329 | Hypo | IGF1R |
| chr15 | 99497059 | 99497132 | Hypo |  | chr12 | 8127565 | 8127595 | Hypo |  |
| chr12 | 10772771 | 10772896 | Hypo | MAGOHB, STYK1 | chr16 | 76008985 | 76009154 | Hypo |  |
| chr16 | 84519974 | 84520010 | Hypo | TLDC1 | chr16 | 88711337 | 88711507 | Hypo | BC033739, MVD, BC028224, IL17C, CYBA |
| chr16 | 88942119 | 88942160 | Hypo | CBFA2T3, PABPN1L | chrY | 3446305 | 3446441 | Hypo | TGIF2LY |
| chrY | 3968100 | 3968132 | Hypo |  | chr7 | 427454 | 427484 | Hypo | LOC442497 |
| chr7 | 1195270 | 1195364 | Hypo | AK090593, AK123998, ZFAND2A | chr7 | 4657806 | 4657857 | Hypo |  |
| chr7 | 20089670 | 20089700 | Hypo |  | chr7 | 20183238 | 20183283 | Hypo | MACC1-AS1, MACC1 |
| chr7 | 64330411 | 64330470 | Hypo | AK097702 | chr7 | 87825006 | 87825137 | Hypo | SRI |
| chr7 | 97490474 | 97490508 | Hypo | ASNS | chr7 | 158198597 | 158198648 | Hypo |  |
| chr7 | 158298861 | 158299036 | Hypo |  | chr3 | 101497841 | 101497996 | Hyper | NXPE3 |
| chr3 | 155463041 | 155463071 | Hyper |  | chr3 | 197236945 | 197237111 | Hyper | BDH1 |
| chr1 | 152009415 | 152009510 | Hyper | S100A11, AC2 | chr1 | 155164415 | 155164455 | Hyper | MIR92B, THBS3, DM075093, MUC1, AX746485, TRIM46 |
| chr1 | 213123889 | 213123919 | Hyper | VASH2 | chr7 | 6543150 | 6543216 | Hyper | GRID2IP |
| chr15 | 40763811 | 40763862 | Hyper | CHST14, BAHD1 | chr15 | 72612540 | 72612906 | Hyper | CELF6 |
| chr12 | 105478323 | 105478359 | Hyper | ALDH1L2 | chr13 | 20175911 | 20175941 | Hyper |  |
| chr13 | 114897194 | 114897240 | Hyper |  | chr4 | 184644053 | 184644249 | Hyper |  |
| chr6 | 24360074 | 24360170 | Hyper | KAAG1, DCDC2 | chr6 | 26284811 | 26284898 | Hyper | HIST1H4H, TRNA_Met |
| chr10 | 99474393 | 99474467 | Hyper | MARVELD1 | chr16 | 47177525 | 47177606 | Hyper |  |
| chr17 | 29298080 | 29298581 | Hyper | DPRXP4, RNF135 | chr17 | 42402884 | 42402917 | Hyper | SLC25A39, RUNDC3A |
| chr17 | 62777335 | 62777450 | Hyper | PLEKHMIP, LOC146880 | chr2 | 98703675 | 98703736 | Hyper | VWA3B |
| chr | 140197122 | 140197263 | Hyper | EXD3, NRARP | chr11 | 73694609 | 73694659 | Hyper | UCP2 |
| chr19 | 49256396 | 49256438 | Hyper | FGF21, FUT1, IZUMO1 |  |  |  |  |  |

TABLE 8

Lung Cancer

| chr | start | end | hypo/hyper | gene annotation | chr | start | end | hypo/hyper | gene annotation |
|---|---|---|---|---|---|---|---|---|---|
| chr6 | 18035867 | 18036015 | Hypo |  | chr6 | 34714803 | 34714896 | Hypo | SNRPC |
| chr6 | 154970558 | 154970676 | Hypo |  | chr6 | 170047467 | 170047499 | Hypo | WDR27 |

TABLE 8-continued

Lung Cancer

| chr | start | end | hypo/hyper | gene annotation | chr | start | end | hypo/hyper | gene annotation |
|---|---|---|---|---|---|---|---|---|---|
| chr9 | 80833933 | 80834011 | Hypo | | chr9 | 99450020 | 99450142 | Hypo | |
| chr9 | 126349038 | 126349104 | Hypo | DENND1A | chr14 | 55765285 | 55765714 | Hypo | FBXO34 |
| chr14 | 73231384 | 73231414 | Hypo | DPF3 | chr14 | 73318471 | 73318629 | Hypo | DPF3 |
| chr14 | 73855616 | 73855646 | Hypo | NUMB | chr14 | 91691163 | 91691306 | Hypo | GPR68 |
| chr14 | 91691696 | 91691822 | Hypo | GPR68 | chr14 | 91766154 | 91766450 | Hypo | |
| chr14 | 94603542 | 94603670 | Hypo | IFI27L2 | chr14 | 102682119 | 102682149 | Hypo | AK130824, WDR20, MOK |
| chr12 | 54894048 | 54894173 | Hypo | NCKAP1L | chr12 | 64783185 | 64783308 | Hypo | |
| chr12 | 104684181 | 104684258 | Hypo | TXNRD1 | chr12 | 109488519 | 109488686 | Hypo | USP30-AS1, USP30 |
| chr12 | 110983706 | 110983736 | Hypo | PPTC7 | chr12 | 112574734 | 112574995 | Hypo | TRAFD1 |
| chr12 | 114337763 | 114337793 | Hypo | RBM19 | chr12 | 117474065 | 117474125 | Hypo | AK055849, FBXW8, TESC |
| chr2 | 27543012 | 27543074 | Hypo | GTF3C2, MPV17 | chr2 | 54322431 | 54322576 | Hypo | |
| chr2 | 55289011 | 55289296 | Hypo | | chr2 | 70367670 | 70367710 | Hypo | C2orf42 |
| chr2 | 70427556 | 70427646 | Hypo | TIA1, C2orf42 | chr2 | 73416356 | 73416535 | Hypo | |
| chr2 | 96974486 | 96974516 | Hypo | | chr2 | 106060615 | 106060792 | Hypo | |
| chr2 | 120825608 | 120825769 | Hypo | EPB41L5 | chr2 | 170373281 | 170373413 | Hypo | KLHL41 |
| chr2 | 208662170 | 208662376 | Hypo | | chr2 | 208662672 | 208662710 | Hypo | |
| chr2 | 228638272 | 228638302 | Hypo | | chr2 | 230795535 | 230795565 | Hypo | FBXO36, TRIP12 |
| chr2 | 236877262 | 236877399 | Hypo | AGAP1 | chr2 | 242523907 | 242523985 | Hypo | 5S_rRNA, THAP4 |
| chr11 | 548731 | 548800 | Hypo | C11orf35, AX748330, LRRC56 | chr11 | 5641077 | 5641140 | Hypo | TRIM34, TRIM6, TRIM6-TRIM34 |
| chr11 | 47485995 | 47486141 | Hypo | CELF1 | chr11 | 67781196 | 67781564 | Hypo | ALDH3B1, UNC93B1 |
| chr18 | 55850845 | 55850987 | Hypo | NEDD4L | chr18 | 77550280 | 77550367 | Hypo | |
| chr8 | 80998526 | 80998601 | Hypo | TPD52 | chr8 | 86405788 | 86405818 | Hypo | |
| chr8 | 101726865 | 101726945 | Hypo | PABPC1 | chr8 | 109500408 | 109500507 | Hypo | EMC2 |
| chr8 | 124014063 | 124014111 | Hypo | | chr8 | 128931133 | 128931261 | Hypo | PVT1 |
| chr8 | 142210914 | 142211043 | Hypo | SLC45A4, DENND3 | chr8 | 142292552 | 142292774 | Hypo | |
| chr22 | 18328127 | 18328268 | Hypo | MICAL3, BC064400 | chr22 | 22058203 | 22058238 | Hypo | PPIL2, YPEL1 |
| chr22 | 29076592 | 29076622 | Hypo | CHEK2 | chr22 | 29445752 | 29445923 | Hypo | C22orf31 |
| chr22 | 41217129 | 41217405 | Hypo | ST13, MIR4766, SLC25A17 | chr17 | 27181180 | 27181371 | Hypo | MIR451B, MIR144, MIR4732, ERAL1, MIR451A |
| chr17 | 66420718 | 66420837 | Hypo | MIR635, WIPI1, ARSG | chr17 | 73904093 | 73904127 | Hypo | FBF1, MRPL38 |
| chr17 | 75733978 | 75734244 | Hypo | | chr17 | 76135926 | 76136001 | Hypo | C17orf99, TMC8 |
| chr17 | 80571380 | 80571776 | Hypo | WDR45B, FOXK2 | chr1 | 1253330 | 1253360 | Hypo | CPSF3L, GLTPD1, PUSL1, ACAP3 |
| chr1 | 1547129 | 1547348 | Hypo | MIB2, AK094692 | chr1 | 8549986 | 8550071 | Hypo | RERE |
| chr1 | 9867157 | 9867316 | Hypo | CLSTN1 | chr1 | 12251873 | 12251958 | Hypo | MIR4632, TNFRSF1B |
| chr1 | 26467523 | 26467630 | Hypo | | chr1 | 43842664 | 43842779 | Hypo | MED8, ELOVL1 |
| chr1 | 61541646 | 61541678 | Hypo | NFIA | chr1 | 156010377 | 156010548 | Hypo | UBQLN4 |
| chr1 | 160986299 | 160986385 | Hypo | F11R | chr1 | 161367577 | 161367607 | Hypo | TRNA_Val |
| chr1 | 161471657 | 161471779 | Hypo | FCGR2A | chr1 | 162427088 | 162427153 | Hypo | |
| chr1 | 224493975 | 224494083 | Hypo | NVL | chr1 | 234845467 | 234845497 | Hypo | |
| chr1 | 245032517 | 245032603 | Hypo | HNRNPU | chr4 | 3446991 | 3447021 | Hypo | HGFAC |
| chr4 | 76554873 | 76554935 | Hypo | CDKL2 | chr4 | 83323506 | 83323708 | Hypo | |
| chr16 | 142649 | 142783 | Hypo | NPRL3, MPG | chr16 | 667141 | 667297 | Hypo | RAB40C |
| chr16 | 667547 | 667622 | Hypo | RAB40C | chr16 | 667876 | 668074 | Hypo | RAB40C |
| chr16 | 677972 | 678084 | Hypo | WFIKKN1, C16orf13, TRNA_Gly, TRNA, AK301549, RAB40C, AK128777 | chr16 | 1407787 | 1407846 | Hypo | UNKL, GNPTG, TSR3, BAIAP3 |
| chr16 | 2281249 | 2281314 | Hypo | DNASE1L2, ECI1, E4F1 | chr16 | 2508414 | 2508453 | Hypo | C16orf59, CCNF |
| chr16 | 30907010 | 30907148 | Hypo | BC073928, CTF1, MIR762, BCL7C | chr16 | 46803280 | 46803355 | Hypo | |
| chr16 | 85517345 | 85517388 | Hypo | | chr10 | 1120778 | 1120937 | Hypo | WDR37 |
| chr10 | 3678597 | 3678625 | Hypo | BC037918 | chr10 | 131937355 | 131937428 | Hypo | GLRX3 |
| chr15 | 65862004 | 65862121 | Hypo | VWA9, PTPLAD1 | chr15 | 93350668 | 93350698 | Hypo | |
| chr20 | 25223141 | 25223277 | Hypo | PYGB | chr20 | 36183184 | 36183340 | Hypo | |
| chr20 | 56998280 | 56998337 | Hypo | VAPB | chr13 | 79993101 | 79993142 | Hypo | RBM26-AS1 |
| chr5 | 2225439 | 2225469 | Hypo | | chr5 | 32042283 | 32042419 | Hypo | |
| chr5 | 39281800 | 39281943 | Hypo | C9 | chr5 | 43215538 | 43215738 | Hypo | NIM1 |
| chr5 | 158612981 | 158613074 | Hypo | RNF145 | chr7 | 2238118 | 2238235 | Hypo | MAD1L1 |

TABLE 8-continued

Lung Cancer

| chr | start | end | hypo/hyper | gene annotation | chr | start | end | hypo/hyper | gene annotation |
|---|---|---|---|---|---|---|---|---|---|
| chr7 | 2473452 | 2473605 | Hypo | BC034268, CHST12 | chr7 | 5262433 | 5262562 | Hypo | WIPI2 |
| chr7 | 6484445 | 6484545 | Hypo | DAGLB | chr7 | 30857157 | 30857292 | Hypo | FAM188B, INMT-FAM188B |
| chr7 | 33725803 | 33725938 | Hypo | | chr7 | 55506288 | 55506348 | Hypo | LANCL2 |
| chr7 | 77129743 | 77129907 | Hypo | | chr7 | 98966786 | 98966916 | Hypo | ARPC1B, ARPC1A |
| chr7 | 102801710 | 102801804 | Hypo | | chr7 | 129483356 | 129483449 | Hypo | UBE2H, AL832212 |
| chr7 | 151423571 | 151423639 | Hypo | PRKAG2 | chr19 | 7157547 | 7157628 | Hypo | INSR |
| chr19 | 8576914 | 8577000 | Hypo | MYO1F, ZNF414, PRAM1 | chr19 | 10246506 | 10246566 | Hypo | DNMT1 |
| chr19 | 30186141 | 30186278 | Hypo | C19orf12 | chr19 | 33571236 | 33571280 | Hypo | GPATCH1 |
| chr19 | 42856453 | 42856483 | Hypo | MEGF8 | chr3 | 12673006 | 12673036 | Hypo | |
| chr3 | 15123848 | 15123992 | Hypo | ZFYVE20 | chr3 | 66053446 | 66053613 | Hypo | |
| chr3 | 101411545 | 101411666 | Hypo | RPL24 | chr3 | 184057335 | 184057557 | Hypo | FAM131A, CLCN2 |
| chr6 | 10416118 | 10416148 | Hyper | LOC100130275, TFAP2A | chr6 | 26332178 | 26332218 | Hyper | TRNA_Trp, TRNA_Met, TRNA_Arg, TRNA_Ser |
| chr6 | 28303562 | 28303607 | Hyper | ZSCAN31 | chr6 | 28303815 | 28304263 | Hyper | ZSCAN31 |
| chr6 | 50691065 | 50691095 | Hyper | TFAP2D | chr6 | 126068092 | 126068158 | Hyper | BC036196, HEY2 |
| chr6 | 152623015 | 152623493 | Hyper | SYNE1 | chr14 | 37124037 | 37124067 | Hyper | PAX9 |
| chr18 | 31902793 | 31902945 | Hyper | | chr12 | 28127930 | 28127997 | Hyper | PTHLH |
| chr12 | 28128619 | 28129054 | Hyper | PTHLH | chr12 | 72332641 | 72332696 | Hyper | TPH2 |
| chr10 | 71327725 | 71327755 | Hyper | NEUROG3 | chr10 | 102986585 | 102986758 | Hyper | LBX1, FLJ41350 |
| chr10 | 118890980 | 118891010 | Hyper | VAX1, KIAA1598 | chr10 | 124910363 | 124910439 | Hyper | HMX2, BUB3 |
| chr3 | 50402317 | 50402944 | Hyper | TMEM115, CACNA2D2, Mir_324 | chr3 | 181442376 | 181442410 | Hyper | |
| chr22 | 19706633 | 19706677 | Hyper | SEPT5-GP1BB | chr22 | 28838200 | 28838292 | Hyper | |
| chr9 | 21965101 | 21965372 | Hyper | C9orf53, CDKN2A | chr9 | 21965685 | 21965757 | Hyper | C9orf53, CDKN2A |
| chr9 | 96721120 | 96721275 | Hyper | BARX1, JB148981 | chr9 | 96722445 | 96722786 | Hyper | JB148981, BARX1 |
| chr2 | 43451909 | 43452327 | Hyper | LOC100129726, THADA, ZFP36L2 | chr2 | 111875191 | 111875611 | Hyper | BCL2L11, AK125994 |
| chr2 | 118981667 | 118981738 | Hyper | | chr2 | 162272989 | 162273057 | Hyper | TBR1 |
| chr2 | 175192103 | 175192136 | Hyper | SP9, LOC285084 | chr2 | 175193268 | 175193324 | Hyper | SP9, LOC285084 |
| chr2 | 175200140 | 175200170 | Hyper | SP9, LOC285084 | chr2 | 177001531 | 177001561 | Hyper | HOXD-AS2, HOXD8, AX747372, BC047605 |
| chr2 | 223158969 | 223158999 | Hyper | CCDC140, DD413687, PAX3 | chr2 | 223165434 | 223165513 | Hyper | CCDC140, DD413687, PAX3 |
| chr2 | 223169834 | 223169864 | Hyper | CCDC140, DD413687, PAX3 | chr2 | 223172337 | 223172367 | Hyper | PAX3, CCDC140, DD413687 |
| chr2 | 223176151 | 223176181 | Hyper | CCDC140, LOC440934 | chr1 | 29586243 | 29586563 | Hyper | PTPRU |
| chr1 | 50891346 | 50891376 | Hyper | DMRTA2 | chr1 | 78511637 | 78511718 | Hyper | GIPC2 |
| chr1 | 91180276 | 91180306 | Hyper | BARHL2 | chr1 | 180204062 | 180204092 | Hyper | LHX4 |
| chr1 | 200012189 | 200012227 | Hyper | NR5A2 | chr1 | 223936894 | 223937014 | Hyper | CAPN2 |
| chr1 | 228645140 | 228645536 | Hyper | MIR4666A, Histone3, HIST3H2A, HIST3H2BB | chr7 | 27136760 | 27136790 | Hyper | HOXA2, AK291164, HOXA3, HOTAIRM1, HOXA1 |
| chr1 | 27195462 | 27195492 | Hyper | HOXA-AS3, HOXA6, HOXA9, HOXA10-HOXA9, HOXA7, DQ655986 | chr7 | 113722939 | 113722969 | Hyper | FOXP2 |
| chr7 | 129423846 | 129423880 | Hyper | MIR183, MIR96 | chr7 | 156801416 | 156801446 | Hyper | LOC645249, MNX1 |
| chr15 | 37402974 | 37403127 | Hyper | MEIS2 | chr15 | 68125458 | 68125496 | Hyper | SKOR1 |
| chr15 | 76629494 | 76629531 | Hyper | ISL2 | chr5 | 6687380 | 6687431 | Hyper | |
| chr5 | 10333725 | 10333762 | Hyper | | chr5 | 50264820 | 50264850 | Hyper | |
| chr5 | 72732801 | 72732831 | Hyper | FOXD1 | chr4 | 41750223 | 41750273 | Hyper | PHOX2B |
| chr4 | 42398842 | 42398872 | Hyper | SHISA3 | chr4 | 166414878 | 166414921 | Hyper | |
| chr16 | 79623804 | 79623854 | Hyper | MAF | chr8 | 108509543 | 108509650 | Hyper | |
| chr17 | 37757153 | 37757217 | Hyper | NEUROD2 | chr17 | 46655148 | 46655178 | Hyper | MIR10A, HOXB4, HOXB3 |
| chr17 | 46675419 | 46675449 | Hyper | HOXB7, HOXB-AS3, HOXB6, HOXB5 | chr17 | 46691966 | 46692022 | Hyper | HOXB9, HOXB8, HOXB7 |
| chr17 | 46801218 | 46801277 | Hyper | MIR3185, HOXB13, HOXB-AS5, PRAC | chr17 | 59539491 | 59539601 | Hyper | TBX4 |

TABLE 8-continued

| | | | | Lung Cancer | | | | |
|---|---|---|---|---|---|---|---|---|
| chr | start | end | hypo/hyper | gene annotation | chr | start | end | hypo/hyper | gene annotation |
| chr19 | 10407090 | 10407120 | Hyper | ICAM5, ICAM4, ICAM1, ZGLP1, FDX1L | chr19 | 11492252 | 11492528 | Hyper | RGL3, EPOR, SWSAP1 |
| chr20 | 44452731 | 44453063 | Hyper | SNX21, TNNC2, UBE2C | | | | | |

TABLE 9

| | | | | Ovarian Cancer | | | | |
|---|---|---|---|---|---|---|---|---|
| chr | start | end | hypo/hyper | gene annotation | chr | start | end | hypo/hyper | gene annotation |
| chr14 | 51829264 | 51829396 | Hypo | LINC00640 | chr21 | 43240082 | 43240112 | Hypo | PRDM15 |
| chr4 | 1008740 | 1008902 | Hypo | FGFRL1 | chr4 | 1214894 | 1215162 | Hypo | HV535487, HV535469, CTBP1 |
| chr4 | 1215415 | 1215451 | Hypo | HV535469, CTBP1, HV535487 | chr4 | 1282515 | 1282545 | Hypo | MAEA, C4orf42 |
| chr4 | 1336755 | 1336902 | Hypo | UVSSA, MAEA | chr4 | 6628453 | 6628500 | Hypo | MAN2B2 |
| chr4 | 42348266 | 42348331 | Hypo | | chr4 | 57777437 | 57777595 | Hypo | REST |
| chr4 | 57813490 | 57813763 | Hypo | REST | chr4 | 74142341 | 74142434 | Hypo | |
| chr5 | 126231644 | 126231674 | Hypo | 3-Mar | chr5 | 131134159 | 131134203 | Hypo | LOC728637, ACSL6, FNIP1 |
| chr5 | 137912037 | 137912148 | Hypo | | chr5 | 139454108 | 139454202 | Hypo | |
| chr5 | 150029147 | 150029245 | Hypo | SYNPO | chr5 | 172354043 | 172354118 | Hypo | ERGIC1 |
| chr5 | 175790961 | 175790991 | Hypo | ARL10, KIAA1191 | chr5 | 179270584 | 179270748 | Hypo | AK095057, C5orf45, SQSTM1 |
| chr22 | 18627328 | 18627537 | Hypo | USP18 | chr22 | 46931260 | 46931332 | Hypo | |
| chr6 | 7892314 | 7892412 | Hypo | TXNDC5, BLOC1S5-TXNDC5 | chr6 | 15513780 | 15513981 | Hypo | DTNBP1, JARID2 |
| chr6 | 43639548 | 43639710 | Hypo | MRPS18A, RSPH9 | chr6 | 71090933 | 71090963 | Hypo | |
| chr6 | 74097722 | 74097763 | Hypo | DDX43 | chr6 | 106731509 | 106731597 | Hypo | ATG5 |
| chr6 | 110848558 | 110848682 | Hypo | | chr15 | 40671495 | 40671620 | Hypo | KNSTRN, DISP2 |
| chr15 | 45444061 | 45444141 | Hypo | DUOX1 | chr15 | 65436137 | 65436213 | Hypo | CLPX, PDCD7 |
| chr15 | 83622512 | 83622565 | Hypo | BC044934, HOMER2 | chr15 | 100339980 | 100340010 | Hypo | DQ590616, DQ571121, DQ575742, DQ595494, DNM1P46, DQ575741, DJ031154 |
| chr20 | 1094560 | 1094682 | Hypo | PSMF1 | chr20 | 5433047 | 5433085 | Hypo | LINC00658 |
| chr20 | 30186068 | 30186165 | Hypo | ID1, MIR3193 | chr20 | 32893006 | 32893125 | Hypo | AHCY |
| chr20 | 33540284 | 33540550 | Hypo | GSS, MYH7B | chr20 | 47815615 | 47815711 | Hypo | |
| chr20 | 55071563 | 55071717 | Hypo | GCNT7, RTFDC1 | chr20 | 62631351 | 62631593 | Hypo | PRPF6 |
| chr3 | 20070714 | 20070903 | Hypo | | chr3 | 23964882 | 23965019 | Hypo | RPL15, NKIRAS1 |
| chr3 | 42852329 | 42852359 | Hypo | CCBP2, HIGD1A | chr3 | 47352704 | 47352734 | Hypo | KLHL18 |
| chr3 | 48698251 | 48698431 | Hypo | | chr3 | 49196747 | 49196831 | Hypo | LAMB2P1, CCDC71 |
| chr3 | 58153446 | 58153608 | Hypo | BC041347 | chr3 | 126261929 | 126262000 | Hypo | CHST13, C3orf22 |
| chr3 | 145735852 | 145735882 | Hypo | | chr3 | 176710106 | 176710241 | Hypo | |
| chr3 | 183217676 | 183217706 | Hypo | KLHL6 | chr3 | 193419702 | 193419732 | Hypo | |
| chr3 | 195095450 | 195095543 | Hypo | ACAP2 | chr3 | 195409773 | 195409813 | Hypo | SDHAP2 |
| chr16 | 1019640 | 1019685 | Hypo | LMF1 | chr16 | 4431126 | 4431189 | Hypo | VASN, CORO7-PAM16, CORO7 |
| chr16 | 21674664 | 21674777 | Hypo | | chr16 | 28224516 | 28224546 | Hypo | XPO6 |
| chr18 | 13132080 | 13132246 | Hypo | CEP192 | chr7 | 6059024 | 6059182 | Hypo | EIF2AK1, AIMP2 |
| chr7 | 7015498 | 7015673 | Hypo | | chr7 | 33167928 | 33168030 | Hypo | BBS9 |
| chr7 | 44740467 | 44740672 | Hypo | OGDH | chr7 | 127615921 | 127615951 | Hypo | SND1 |
| chr7 | 138042221 | 138042288 | Hypo | | chr7 | 140180094 | 140180444 | Hypo | MKRN1 |
| chr9 | 36036323 | 36036353 | Hypo | RECK | chr9 | 36196920 | 36197005 | Hypo | CLTA |
| chr9 | 86578079 | 86578366 | Hypo | C9orf64, HNRNPK, MIR7-1 | chr9 | 92053911 | 92053949 | Hypo | SEMA4D |
| chr9 | 99259362 | 99259405 | Hypo | CDC14B, HABP4 | chr9 | 124749865 | 124749953 | Hypo | TTLL11 |
| chr9 | 128635180 | 128635210 | Hypo | PBX3 | chr9 | 140015209 | 140015241 | Hypo | DPP7 |
| chr9 | 140704046 | 140704131 | Hypo | EHMT1 | chr13 | 114766270 | 114766300 | Hypo | RASA3 |
| chr2 | 8735932 | 8736064 | Hypo | | chr2 | 11356651 | 11356762 | Hypo | ROCK2 |
| chr2 | 27356168 | 27356198 | Hypo | C2orf53, PREB, AK074615, ABHD1 | chr2 | 38551124 | 38551390 | Hypo | ATL2 |

TABLE 9-continued

Ovarian Cancer

| chr | start | end | hypo/hyper | gene annotation | chr | start | end | hypo/hyper | gene annotation |
|---|---|---|---|---|---|---|---|---|---|
| chr2 | 44809187 | 44809217 | Hypo | | chr2 | 47200591 | 47200621 | Hypo | TTC7A |
| chr2 | 47249725 | 47249848 | Hypo | TTC7A | chr2 | 86791221 | 86791251 | Hypo | RNF103-CHMP3, CHMP3 |
| chr2 | 101186368 | 101186458 | Hypo | PDCL3 | chr2 | 110015080 | 110015110 | Hypo | |
| chr2 | 114470022 | 114470201 | Hypo | SLC35F5, MIR4782 | chr2 | 178973003 | 178973042 | Hypo | RBM45 |
| chr2 | 201156690 | 201156804 | Hypo | | chr2 | 203498452 | 203498489 | Hypo | FAM117B |
| chr2 | 209225237 | 209225275 | Hypo | PTH2R | chr2 | 217396039 | 217396069 | Hypo | |
| chr2 | 220080510 | 220081033 | Hypo | ATG9A, ABCB6, ZFAND2B | chr2 | 233073078 | 233073223 | Hypo | |
| chr2 | 240319920 | 240320012 | Hypo | | chr1 | 2331363 | 2331437 | Hypo | PEX10, RER1, MORN1 |
| chr1 | 2514330 | 2514376 | Hypo | FAM213B, MMEL1 | chr1 | 3182883 | 3182917 | Hypo | |
| chr1 | 3700384 | 3700414 | Hypo | LRRC47, SMIM1 | chr1 | 6713914 | 6714041 | Hypo | DNAJC11 |
| chr1 | 6714348 | 6714378 | Hypo | DNAJC11 | chr1 | 9795995 | 9796196 | Hypo | PIK3CD, CLSTN1 |
| chr1 | 12460299 | 12460356 | Hypo | VPS13D | chr1 | 25919307 | 25919337 | Hypo | |
| chr1 | 28726724 | 28726812 | Hypo | PHACTR4 | chr1 | 28727177 | 28727324 | Hypo | PHACTR4 |
| chr1 | 28727894 | 28728020 | Hypo | PHACTR4 | chr1 | 47035373 | 47035403 | Hypo | MKNK1 |
| chr1 | 54877027 | 54877451 | Hypo | SSBP3 | chr1 | 67669791 | 67669853 | Hypo | IL23R, U6 |
| chr1 | 109595405 | 109595534 | Hypo | | chr1 | 150994889 | 150995152 | Hypo | U6, PRUNE |
| chr1 | 156017591 | 156017683 | Hypo | LAMTOR2, UBQLN4 | chr1 | 185076172 | 185076270 | Hypo | RNF2 |
| chr1 | 212484610 | 212484816 | Hypo | PPP2R5A | chr1 | 234620866 | 234620979 | Hypo | TARBP1 |
| chr1 | 234839889 | 234840058 | Hypo | | chr1 | 245494495 | 245494578 | Hypo | KIF26B |
| chr17 | 7368947 | 7369139 | Hypo | ZBTB4, CHRNB1 | chr17 | 40897739 | 40897788 | Hypo | RAMP2-AS1, BC047651, EZH1 |
| chr17 | 72491378 | 72491531 | Hypo | | chr17 | 73215289 | 73215423 | Hypo | NUP85 |
| chr17 | 76187407 | 76187544 | Hypo | AFMID, TK1 | chr17 | 77084518 | 77084727 | Hypo | RBFOX3, ENGASE |
| chr17 | 77394706 | 77394850 | Hypo | RBFOX3 | chr17 | 80749152 | 80749276 | Hypo | TBCD |
| chr12 | 8180999 | 8181065 | Hypo | FOXJ2 | chr12 | 27114515 | 27114639 | Hypo | TM7SF3, FGFR1OP2 |
| chr12 | 49989786 | 49989816 | Hypo | FAM186B | chr12 | 51625514 | 51625587 | Hypo | DAZAP2 |
| chr12 | 56558381 | 56558519 | Hypo | SMARCC2, MYL6, MYL6B | chr12 | 56653281 | 56653369 | Hypo | COQ10A, ANKRD52 |
| chr12 | 57983314 | 57983348 | Hypo | PIP4K2C, BC033961, KIF5A | chr12 | 62603907 | 62603937 | Hypo | |
| chr12 | 62858444 | 62858575 | Hypo | MON2 | chr12 | 68964473 | 68964503 | Hypo | |
| chr12 | 98949938 | 98949972 | Hypo | | chr12 | 133280578 | 133280682 | Hypo | PXMP2, PGAM5 |
| chr19 | 418225 | 418255 | Hypo | SHC2, C2CD4C | chr19 | 1048348 | 1048465 | Hypo | ABCA7 |
| chr19 | 8579592 | 8579705 | Hypo | MYO1F, ZNF414 | chr19 | 15519444 | 15519474 | Hypo | AKAP8L |
| chr19 | 18126412 | 18126442 | Hypo | ARRDC2 | chr19 | 18856379 | 18856409 | Hypo | CRTC1 |
| chr19 | 19636877 | 19636907 | Hypo | YJEFN3, NDUFA13 | chr19 | 36194934 | 36194996 | Hypo | ZBTB32 |
| chr19 | 36531924 | 36531954 | Hypo | BC071809, THAP8, CLIP3 | chr19 | 39273027 | 39273062 | Hypo | LGALS7B, LGALS7 |
| chr19 | 41846193 | 41846325 | Hypo | TGFB1 | chr19 | 45678395 | 45678555 | Hypo | TRAPPC6A, BLOC1S3 |
| chr19 | 50589044 | 50589079 | Hypo | SNAR-A3 | chr19 | 56201643 | 56201938 | Hypo | EPN1 |
| chr19 | 58807869 | 58807931 | Hypo | LOC113386, ZNF8 | chr11 | 4095819 | 4095864 | Hypo | STIM1 |
| chr11 | 31760124 | 31760235 | Hypo | ELP4 | chr11 | 63431856 | 63431918 | Hypo | ATL3 |
| chr11 | 63432139 | 63432218 | Hypo | ATL3 | chr11 | 66658224 | 66658290 | Hypo | |
| chr11 | 72414010 | 72414010 | Hypo | BC150585, ARAP1 | chr11 | 73481055 | 73481085 | Hypo | RAB6A |
| chr11 | 73561763 | 73561798 | Hypo | MRPL48 | chr11 | 73685698 | 73685845 | Hypo | UCP2, DNAJB13 |
| chr11 | 76594692 | 76594722 | Hypo | ACER3 | chr11 | 85709169 | 85709254 | Hypo | PICALM |
| chr11 | 117017686 | 117017773 | Hypo | PAFAH1B2, AB231710, AB231711 | chr11 | 120367948 | 120368008 | Hypo | |
| chr11 | 120998701 | 120998825 | Hypo | TECTA | chr11 | 130781550 | 130781781 | Hypo | SNX19 |
| chr8 | 10652917 | 10653017 | Hypo | | chr8 | 31044103 | 31044133 | Hypo | |
| chr8 | 48044710 | 48044753 | Hypo | | chr8 | 59058941 | 59059343 | Hypo | FAM110B |
| chr8 | 96285420 | 96285553 | Hypo | LOC100616530, C8orf37, TRNA_Ser | chr8 | 98786343 | 98786387 | Hypo | LAPTM4B |
| chr8 | 98786918 | 98786972 | Hypo | LAPTM4B | chr8 | 126007690 | 126008051 | Hypo | SQLE |
| chr8 | 128893019 | 128893049 | Hypo | PVT1 | chr8 | 141596886 | 141597022 | Hypo | AGO2 |
| chr8 | 142265206 | 142265339 | Hypo | | chr8 | 143558472 | 143558604 | Hypo | BAI1 |
| chr8 | 144303562 | 144303592 | Hypo | GPIHBP1 | chr8 | 144617065 | 144617347 | Hypo | ZC3H3 |
| chr8 | 145223902 | 145224061 | Hypo | MROH1 | chr10 | 3197004 | 3197113 | Hypo | BC039685, PITRM1-AS1, PITRM1 |
| chr10 | 6167619 | 6167742 | Hypo | RBM17 | chr10 | 6372343 | 6372373 | Hypo | LOC399715 |
| chr10 | 28964745 | 28964800 | Hypo | BAMBI | chr10 | 63669223 | 63669344 | Hypo | ARID5B |
| chr10 | 75384100 | 75384130 | Hypo | MYOZ1 | chr10 | 103425950 | 103426174 | Hypo | FBXW4 |

TABLE 9-continued

Ovarian Cancer

| chr | start | end | hypo/hyper | gene annotation | chr | start | end | hypo/hyper | gene annotation |
|---|---|---|---|---|---|---|---|---|---|
| chr10 | 120800789 | 120800835 | Hypo | EIF3A, NANOS1 | chr10 | 127406313 | 127406386 | Hypo | FLJ37035, LOC283038, C10orf137 |
| chr10 | 134491021 | 134491114 | Hypo | INPP5A | chr10 | 134593329 | 134593416 | Hypo | NKX6-2, INPP5A |
| chr10 | 135018032 | 135018070 | Hypo | KNDC1 | chr10 | 135153956 | 135154001 | Hypo | PRAP1, CALY |
| AC160854.2_10710-13495 | 1027 | 1057 | Hypo | | chr15 | 45493209 | 45493371 | Hyper | TRNA, TRNA_His |
| chr14 | 105512063 | 105512395 | Hyper | GPR132 | chr17 | 16284630 | 16285065 | Hyper | UBB |
| chr8 | 144203653 | 144203708 | Hyper | | chr1 | 90309292 | 90309490 | Hyper | LRRC8D |
| chr1 | 219346992 | 219347035 | Hyper | LYPLAL1, LOC643723 | chr1 | 219347394 | 219347472 | Hyper | LYPLAL1, LOC643723 |

TABLE 10

Pancreatic Cancer

| chr | start | end | hypo/hyper | gene annotation | chr | start | end | hypo/hyper | gene annotation |
|---|---|---|---|---|---|---|---|---|---|
| chr16 | 15708247 | 15708309 | Hypo | KIAA0430 | chr16 | 86571984 | 86572014 | Hypo | MTHFSD |
| chr7 | 1970842 | 1970872 | Hypo | MAD1L1 | chr7 | 2109874 | 2109904 | Hypo | MAD1L1 |
| chr7 | 2595825 | 2595943 | Hypo | IQCE, BRAT1 | chr7 | 45614929 | 45615020 | Hypo | ADCY1 |
| chr9 | 135456476 | 135456544 | Hypo | C9orf171, BARHL1 | chr9 | 140033001 | 140033092 | Hypo | GRIN1 |
| chr2 | 3259989 | 3260103 | Hypo | TSSC1 | chr2 | 7164467 | 7164788 | Hypo | |
| chr2 | 10369155 | 10369242 | Hypo | | chr2 | 11903450 | 11903480 | Hypo | LPIN1 |
| chr2 | 47193930 | 47193960 | Hypo | TTC7A | chr2 | 69975443 | 69975523 | Hypo | ANXA4 |
| chr2 | 118380865 | 118380904 | Hypo | | chr2 | 171822428 | 171822480 | Hypo | GORASP2 |
| chr2 | 176987367 | 176987397 | Hypo | HOXD10, HOXD9, AX747372, HOXD8 | chr2 | 224661521 | 224661701 | Hypo | AP1S3 |
| chr17 | 77919429 | 77919477 | Hypo | TBC1D16 | chr17 | 77924259 | 77924351 | Hypo | TBC1D16 |
| chr17 | 78194821 | 78194861 | Hypo | SLC26A11, SGSH | chr12 | 4274271 | 4274409 | Hypo | |
| chr12 | 4379357 | 4379491 | Hypo | CCND2 | chr12 | 12456859 | 12456889 | Hypo | |
| chr12 | 13055966 | 13055996 | Hypo | GPRC5A | chr12 | 27494550 | 27494580 | Hypo | ARNTL2 |
| chr12 | 50673944 | 50674096 | Hypo | | chr12 | 94544022 | 94544052 | Hypo | PLXNC1 |
| chr12 | 101025380 | 101025410 | Hypo | GAS2L3 | chr12 | 104506691 | 104506783 | Hypo | NFYB, HCFC2 |
| chr12 | 123211316 | 123211390 | Hypo | HCAR1, HCAR3 | chr13 | 46649031 | 46649141 | Hypo | CPB2, CPB2-AS1 |
| chr13 | 97761876 | 97761925 | Hypo | | chr11 | 775261 | 775291 | Hypo | NS3BP, PDDC1, BC048998 |
| chr11 | 33318780 | 33318945 | Hypo | HIPK3 | chr11 | 47372828 | 47373002 | Hypo | SPI1, SLC39A13, MYBPC3 |
| chr11 | 67918044 | 67918145 | Hypo | SUV420H1 | chr11 | 71647544 | 71647574 | Hypo | RNF121, LOC100133315 |
| chr11 | 111976911 | 111976941 | Hypo | | chr5 | 2753048 | 2753078 | Hypo | C5orf38, IRX2 |
| chr5 | 87986547 | 87986581 | Hypo | | chr5 | 126245097 | 126245133 | Hypo | 3-Mar |
| chr5 | 138273817 | 138273854 | Hypo | SIL1, CTNNA1 | chr8 | 38262470 | 38262502 | Hypo | FGFR1, LETM2 |
| chr8 | 41166305 | 41166374 | Hypo | SFRP1 | chr8 | 42082721 | 42082874 | Hypo | |
| chr8 | 103575128 | 103575296 | Hypo | ODF1 | chr8 | 143368318 | 143368469 | Hypo | TSNARE1 |
| chrY | 3838889 | 3838919 | Hypo | | chr18 | 3214441 | 3214825 | Hypo | MYOM1 |
| chr18 | 3215042 | 3215256 | Hypo | MYOM1 | chr20 | 52311463 | 52311728 | Hypo | |
| chr20 | 62321823 | 62321881 | Hypo | RTEL1-TNFRSF6B, TNFRSF6B, ARFRP1 | chr4 | 1093536 | 1093675 | Hypo | RNF212 |
| chr4 | 1331675 | 1331705 | Hypo | UVSSA, MAEA | chr4 | 7758476 | 7758561 | Hypo | AFAP1, AFAP1-AS1 |
| chr4 | 13524957 | 13525008 | Hypo | LOC285547 | chr4 | 57803498 | 57803558 | Hypo | REST |
| chr4 | 113431900 | 113431930 | Hypo | NEUROG2 | chr4 | 151974287 | 151974510 | Hypo | |
| chr4 | 183064874 | 183064966 | Hypo | TENM3, MGC45800 | chr4 | 184921876 | 184921885 | Hypo | STOX2 |
| chr21 | 43393528 | 43393713 | Hypo | | chr21 | 46847654 | 46847684 | Hypo | COL18A1-AS1 |
| chr10 | 5855154 | 5855184 | Hypo | GDI2 | chr10 | 6206142 | 6206217 | Hypo | |
| chr10 | 8055681 | 8055764 | Hypo | TAF3 | chr10 | 37051865 | 37051895 | Hypo | |
| chr10 | 73157867 | 73158027 | Hypo | CDH23 | chr10 | 131348513 | 131348793 | Hypo | MGMT |
| chr10 | 134499773 | 134499803 | Hypo | INPP5A | chr1 | 1281214 | 1281244 | Hypo | MXRA8, DVL1 |
| chr1 | 6186511 | 6186546 | Hypo | CHD5 | chr1 | 6284828 | 6284858 | Hypo | ICMT, RNF207 |
| chr1 | 16474413 | 16474576 | Hypo | EPHA2 | chr1 | 16475031 | 16475207 | Hypo | EPHA2 |
| chr1 | 27332448 | 27332673 | Hypo | FAM46B | chr1 | 53705647 | 53705701 | Hypo | LRP8, LOC100507564, MAGOH |
| chr1 | 62793237 | 62793267 | Hypo | | chr1 | 91182805 | 91182835 | Hypo | BARHL2 |
| chr1 | 98515142 | 98515191 | Hypo | MIR137, MIR2682, MIR137HG | chr1 | 169355697 | 169355727 | Hypo | CCDC181, BLZF1 |

TABLE 10-continued

Pancreatic Cancer

| chr | start | end | hypo/hyper | gene annotation | chr | start | end | hypo/hyper | gene annotation |
|---|---|---|---|---|---|---|---|---|---|
| chr1 | 169930112 | 169930305 | Hypo | KIFAP3 | chr1 | 179046338 | 179046385 | Hypo | TOR3A, FAM20B |
| chr1 | 217307369 | 217307437 | Hypo | | chr1 | 240256663 | 240256780 | Hypo | FMN2 |
| chr19 | 869337 | 869394 | Hypo | MED16, CFD | chr19 | 959128 | 959187 | Hypo | ARID3A |
| chr19 | 4054435 | 4054471 | Hypo | ZBTB7A | chr19 | 41919917 | 41919971 | Hypo | BCKDHA |
| chr19 | 50304736 | 50304766 | Hypo | AP2A1, FUZ | chr22 | 20229079 | 20229239 | Hypo | MIR1286, RTN4R |
| chr22 | 21299605 | 21299635 | Hypo | BC033281, CRKL | chr22 | 23991201 | 23991272 | Hypo | GUSBP11 |
| chr22 | 41634393 | 41634423 | Hypo | RANGAP1, CHADL | chr6 | 52344375 | 52344405 | Hypo | EFHC1 |
| chr6 | 109057882 | 109057928 | Hypo | | chr6 | 109058799 | 109058861 | Hypo | |
| chr6 | 159211558 | 159211701 | Hypo | AX747826, EZR | chr15 | 46021437 | 46021467 | Hypo | |
| chr15 | 74818772 | 74818806 | Hypo | | chr15 | 99347007 | 99347040 | Hypo | |
| chr3 | 38030618 | 38030782 | Hypo | VILL | chr3 | 115512319 | 115512448 | Hypo | LSAMP |
| chr3 | 152107022 | 152107052 | Hypo | | chr3 | 152877666 | 152877696 | Hypo | RAP2B |
| chr3 | 155456596 | 155456630 | Hypo | | chr3 | 195601239 | 195601312 | Hypo | TNK2 |
| chr3 | 195602330 | 195602576 | Hypo | TNK2 | chr3 | 197247047 | 197247110 | Hypo | BDH1 |
| chr3 | 197278926 | 197278988 | Hypo | BDH1 | chr14 | 32597620 | 32597657 | Hypo | ARHGAP5 |
| chr14 | 69014044 | 69014110 | Hypo | | chr14 | 92507762 | 92507792 | Hypo | BC039675, TRIP11, AX721199 |
| chr14 | 92979917 | 92979991 | Hyper | RIN3 | chr14 | 105714415 | 105715529 | Hyper | BTBD6, BRF1 |
| chr22 | 22005794 | 22006759 | Hyper | SDF2L1, MIR301B, MIR130B | chr18 | 57364658 | 57364691 | Hyper | CCBE1 |
| chr18 | 75362931 | 75362985 | Hyper | | chr16 | 12996948 | 12997011 | Hyper | SHISA9 |
| chr16 | 89007520 | 89007558 | Hyper | CBFA2T3 | chr16 | 89008562 | 89008592 | Hyper | CBFA2T3 |
| chr17 | 1494550 | 1494613 | Hyper | SLC43A2 | chr17 | 17398404 | 17398440 | Hyper | RASD1, MED9 |
| chr2 | 5833899 | 5833932 | Hyper | SOX11 | chr2 | 7571717 | 7571747 | Hyper | LOC100506274 |
| chr2 | 18059781 | 18059841 | Hyper | KCNS3 | chr2 | 99439477 | 99439507 | Hyper | KIAA1211L |
| chr2 | 131594989 | 131595019 | Hyper | AK127124, AX746725 | chr2 | 145282119 | 145282149 | Hyper | ZEB2-AS1, ZEB2_AS11, ZEB2_AS1_4, ZEB2_AS1_3 |
| chr2 | 176971628 | 176971712 | Hyper | HOXD11, HOXD10, HOXD12115154825 | chr2 | 239072648 | 239072692 | Hyper | FAM132B, ILKAP |
| chr3 | 5137960 | 5138019 | Hyper | | chr3 | 13679284 | 13679319 | Hyper | |
| chr3 | 128274100 | 128274148 | Hyper | | chr3 | 140770069 | 140770099 | Hyper | SPSB4 |
| chr3 | 184319424 | 184319612 | Hyper | | chr3 | 184319828 | 184319891 | Hyper | |
| chr3 | 194407998 | 194408028 | Hyper | FAM43A | chr5 | 1930990 | 1931024 | Hyper | |
| chr5 | 3595786 | 3595876 | Hyper | IRX1 | chr5 | 17217928 | 17217958 | Hyper | BASP1, LOC285696 |
| chr5 | 17218195 | 17218225 | Hyper | BASP1, LOC285696 | chr5 | 76940340 | 76940374 | Hyper | OTP |
| chr5 | 170289444 | 170289498 | Hyper | RANBP17 | chr5 | 170735422 | 170735452 | Hyper | TLX3, AX746723, RANBP17 |
| chr15 | 29396330 | 29396360 | Hyper | APBA2 | chr15 | 43810405 | 43810435 | Hyper | MAP1A |
| chr15 | 59158809 | 59158901 | Hyper | unknown, FAM63B | chr15 | 68128594 | 68128688 | Hyper | SKOR1 |
| chr15 | 89943410 | 89943440 | Hyper | AK054710, LINC00925 | chr19 | 1764293 | 1764339 | Hyper | ONECUT3 |
| chr19 | 1776504 | 1776534 | Hyper | ONECUT3, ATP8B3 | chr19 | 5292812 | 5292844 | Hyper | PTPRS |
| chr19 | 12996169 | 12996280 | Hyper | GCDH, KLF1, DNASE2 | chr19 | 34973932 | 34973965 | Hyper | WTIP |
| chr19 | 41018716 | 41018746 | Hyper | SPTBN4 | chr19 | 42028502 | 42028549 | Hyper | |
| chr19 | 51228049 | 51228079 | Hyper | CLEC11A, SHANK1 | chr19 | 52552104 | 52552151 | Hyper | ZNF432 |
| chr19 | 58545480 | 58545577 | Hyper | ZSCAN1 | chr4 | 5892135 | 5892194 | Hyper | CRMP1, FLJ46481 |
| chr4 | 8893060 | 8893093 | Hyper | | chr4 | 42154662 | 42154697 | Hyper | BEND4 |
| chr9 | 77113795 | 77113825 | Hyper | RORB | chr13 | 32605034 | 32605966 | Hyper | FRY, BC035084 |
| chr13 | 36049995 | 36050025 | Hyper | NBEA, MIR548F5 | chr13 | 79168067 | 79168102 | Hyper | POU4F1, RNF219-AS1 |
| chr13 | 113244509 | 113244595 | Hyper | TUBGCP3 | chr12 | 3862254 | 3862298 | Hyper | EFCAB4B |
| chr12 | 4382006 | 4382162 | Hyper | CCND2 | chr12 | 5541100 | 5541177 | Hyper | NTF3 |
| chr12 | 79257222 | 79257351 | Hyper | SYT1 | chr12 | 103889160 | 103889211 | Hyper | C12orf42 |
| chr12 | 127940086 | 127940247 | Hyper | | chr12 | 129427424 | 129427557 | Hyper | GLT1D1 |
| chr12 | 130388732 | 130388762 | Hyper | GDF6 | chr8 | 56015908 | 56015938 | Hyper | XKR4 |
| chr8 | 97167811 | 97167855 | Hyper | GDF6 | chr11 | 27744450 | 27744480 | Hyper | |
| chr11 | 57414633 | 57414663 | Hyper | YPEL4, MIR130A, AK096335 | chr11 | 102962922 | 102963062 | Hyper | DCUN1D5 |
| chr11 | 116147253 | 116147283 | Hyper | | chr11 | 131564970 | 131565073 | Hyper | |
| chr20 | 18073312 | 18073461 | Hyper | | chr20 | 52311483 | 52311602 | Hyper | |
| chr20 | 59804170 | 59804235 | Hyper | | chr6 | 711142 | 711293 | Hyper | AX747750 |
| chr6 | 26199137 | 26199167 | Hyper | HIST1H2BF, HIST1H4E, HIST1H2AD, HIST1H3F, HIST1H3D, HIST1H4D | chr6 | 26199686 | 26199716 | Hyper | HIST1H3D, HIST1H2BF, HIST1H4E, HIST1H2AD, HIST1H3F |

TABLE 10-continued

Pancreatic Cancer

| chr | start | end | hypo/hyper | gene annotation | chr | start | end | hypo/hyper | gene annotation |
|---|---|---|---|---|---|---|---|---|---|
| chr6 | 27799464 | 27799581 | Hyper | HIST1H2AK, HIST1H2BN, HIST1H4K, BC016143, FKSG63, HIST1H4J | chr6 | 72596272 | 72596315 | Hyper | RIMS1 |
| chr6 | 84141298 | 84141412 | Hyper | ME1 | chr1 | 2472174 | 2472301 | Hyper | LOC115110 |
| chr1 | 17445857 | 17445943 | Hyper | PADI2 | chr1 | 98519023 | 98519056 | Hyper | MIR2682, MIR137HG, MIR137 |
| chr1 | 115631867 | 115631915 | Hyper | TSPAN2 | chr1 | 115880363 | 115880395 | Hyper | |
| chr1 | 156815692 | 156815745 | Hyper | INSRR, NTRK1 | chr1 | 182584048 | 182584613 | Hyper | LOC284648 |
| chr1 | 202081571 | 202081641 | Hyper | | chr7 | 20826884 | 20826976 | Hyper | SP8 |
| chr7 | 25897216 | 25897246 | Hyper | | chr7 | 41739785 | 41739879 | Hyper | INHBA-AS1, INHBA |
| chr7 | 100609750 | 100609780 | Hyper | AK096803, AK057259, MUC3A, MUC12, MUC3B | chr7 | 100808466 | 100808502 | Hyper | NAT16, VGF, MIR4653, AP1S1 |
| chr7 | 129418057 | 129418092 | Hyper | MIR183, MIR96, MIR182 | chr7 | 157481130 | 157481160 | Hyper | |
| chr10 | 11059860 | 11059923 | Hyper | CELF2 | chr10 | 52177545 | 52177575 | Hyper | SGMS1 |
| chr10 | 85954425 | 85954457 | Hyper | CDHR1, C10orf99 | chr10 | 128994870 | 128994903 | Hyper | FAM196A |
| chr10 | 130338727 | 130338761 | Hyper | | chr10 | 133849598 | 133849628 | Hyper | |

TABLE 11

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 147543 | 147613 | Hypo | cancer_general | ENOSF1 | chr18 | 597548 | 597578 | Hypo | cancer_general | CLUL1 |
| chr18 | 697854 | 697901 | Hypo | cancer_general | MYOM1 | chr18 | 2755770 | 2755878 | Hypo | cancer_general | SMCHD1 |
| chr18 | 3214441 | 3214825 | Hypo | pancreas | | chr18 | 3215042 | 3215256 | Hypo | pancreas | MYOM1 |
| chr18 | 5133207 | 5133343 | Hypo | cancer_general | | chr18 | 6908056 | 6908243 | Hypo | esophageal | ARHGAP28 |
| chr18 | 8612252 | 8612282 | Hypo | cancer_general | RAB12 | chr18 | 9868137 | 9868174 | Hypo | cancer_general | AX747048 |
| chr18 | 9912767 | 9912797 | Hypo | cancer_general | VAPA | chr18 | 10251324 | 10251432 | Hypo | cancer_general | PIEZO2 |
| chr18 | 10589096 | 10589348 | Hypo | cancer_general | | chr18 | 10733492 | 10733605 | Hypo | cancer_general | |
| chr18 | 11401654 | 11401817 | Hypo | cancer_general | | chr18 | 11942728 | 11942838 | Hypo | cancer_general | |
| chr18 | 11979677 | 11979860 | Hypo | cancer_general | IMPA2 | chr18 | 12277243 | 12277273 | Hypo | hepatobiliary | CIDEA |
| chr18 | 12375483 | 12375597 | Hypo | cancer_general | AFG3L2 | chr18 | 12375923 | 12376129 | Hypo | cancer_general | AFG3L2 |
| chr18 | 12890152 | 12890278 | Hypo | cancer_general | PTPN2 | chr18 | 12948993 | 12949023 | Hypo | cancer_general | SEH1L |
| chr18 | 13132080 | 13132246 | Hypo | ovarian | CEP192 | chr18 | 13826393 | 13826536 | Hypo | cancer_general | MC5R |
| chr18 | 19191525 | 19191585 | Hypo | cancer_general | SNRPD1 | chr18 | 20911541 | 20911571 | Hypo | cancer_general | TMEM241 |
| chr18 | 21035222 | 21035252 | Hypo | cancer_general | RIOK3 | chr18 | 21719938 | 21720064 | Hypo | cancer_general | CABYR, TTC39C |
| chr18 | 23686462 | 23686618 | Hypo | cancer_general | RNF138 | chr18 | 29413805 | 29413839 | Hypo | breast | TRAPPC8 |
| chr18 | 29719775 | 29720012 | Hypo | cancer_general | INO80C | chr18 | 32957803 | 32957839 | Hypo | cancer_general | ZNF396 |
| chr18 | 33078363 | 33078662 | Hypo | cancer_general | STSSIA5, AK095045 | chr18 | 43546048 | 43546134 | Hypo | cancer_general | EPG5 |
| chr18 | 44259903 | 44259990 | Hypo | cancer_general | | chr18 | 46142662 | 46142809 | Hypo | cancer_general | CTIF |
| chr18 | 48604773 | 48604802 | Hypo | literature | SMAD4 | chr18 | 48636211 | 48636320 | Hypo | cancer_general | |
| chr18 | 51771058 | 51771128 | Hypo | cancer_general | | chr18 | 53989796 | 53989877 | Hypo | cancer_general | |
| chr18 | 55426948 | 55426978 | Hypo | cancer_general | | chr18 | 55850845 | 55850987 | Hypo | lung, cancer_general | NEDD4L |
| chr18 | 56483918 | 56483958 | Hypo | cancer_general | | chr18 | 56815734 | 56816107 | Hypo | cancer_general | SEC11C, AK311213 |
| chr18 | 60557729 | 60557759 | Hypo | cancer_general | PHLPP1 | chr18 | 61143911 | 61143975 | Hypo | literature | SERPINB5 |
| chr18 | 72845833 | 72845863 | Hypo | cancer_general | | chr18 | 74501144 | 74501183 | Hypo | head_neck | LOC100131655 |
| chr18 | 74755508 | 74755590 | Hypo | breast | MBP | chr18 | 75335093 | 75335123 | Hypo | cancer_general | |
| chr18 | 75339231 | 75339340 | Hypo | cancer_general | | chr18 | 75551271 | 75551301 | Hypo | cancer_general | |
| chr18 | 75999404 | 75999434 | Hypo | cancer_general | | chr18 | 76239541 | 76239616 | Hypo | cancer_general | |
| chr18 | 76501479 | 76501509 | Hypo | cancer_general | | chr18 | 76653631 | 76653661 | Hypo | cancer_general | |
| chr18 | 76686249 | 76686279 | Hypo | cancer_general | | chr18 | 76689735 | 76689765 | Hypo | cancer_general | |
| chr18 | 77050480 | 77050678 | Hypo | cancer_general | ATP9B | chr18 | 77143346 | 77143376 | Hypo | cancer_general | ATP9B |
| chr18 | 77167824 | 77167854 | Hypo | cancer_general | NFATC1 | chr18 | 77181355 | 77181409 | Hypo | cancer_general | NFATC1 |
| chr18 | 77194936 | 77194978 | Hypo | cancer_general | NFATC1 | chr18 | 77205532 | 77205638 | Hypo | cancer_general | NFATC1 |
| chr18 | 77285897 | 77286028 | Hypo | cancer_general | NFATC1 | chr18 | 77300326 | 77300483 | Hypo | cancer_general | |
| chr18 | 77309533 | 77309563 | Hypo | hepatobiliary | | chr18 | 77312866 | 77312927 | Hypo | cancer_general | |
| chr18 | 77329727 | 77330017 | Hypo | colorectal | CTDP1 | chr18 | 77371430 | 77371547 | Hypo | cancer_general | |
| chr18 | 77459762 | 77459877 | Hypo | cancer_general | | chr18 | 77512225 | 77512255 | Hypo | cancer_general | CTDP1 |
| chr18 | 77543249 | 77543481 | Hypo | cancer_general | | chr18 | 77543700 | 77543824 | Hypo | cancer_general | |
| chr18 | 77550206 | 77550367 | Hypo | lung, cancer_general | | chr18 | 77576934 | 77577043 | Hypo | cancer_general | |
| chr18 | 77636591 | 77636621 | Hypo | cancer_general | KCNG2 | chr18 | 77698881 | 77698919 | Hypo | breast | |
| HCV | 111 | 140 | Hypo | virus | | HCV | 374 | 403 | Hypo | virus | |
| HCV | 637 | 666 | Hypo | virus | | HCV | 900 | 929 | Hypo | virus | |
| HCV | 1163 | 1192 | Hypo | virus | | HCV | 1426 | 1455 | Hypo | virus | |
| HCV | 1689 | 1718 | Hypo | virus | | HCV | 1952 | 1981 | Hypo | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HCV | 2215 | 2244 | Hypo | virus | | HCV | 2478 | 2507 | Hypo | virus | |
| HCV | 2741 | 2770 | Hypo | virus | | HCV | 3004 | 3033 | Hypo | virus | |
| HCV | 3267 | 3296 | Hypo | virus | | HCV | 3530 | 3559 | Hypo | virus | |
| HCV | 3793 | 3822 | Hypo | virus | | HCV | 4056 | 4085 | Hypo | virus | |
| HCV | 4319 | 4348 | Hypo | virus | | HCV | 4582 | 4611 | Hypo | virus | |
| HCV | 4845 | 4874 | Hypo | virus | | HCV | 5108 | 5137 | Hypo | virus | |
| HCV | 5371 | 5400 | Hypo | virus | | HCV | 5634 | 5663 | Hypo | virus | |
| HCV | 5897 | 5926 | Hypo | virus | | HCV | 6160 | 6189 | Hypo | virus | |
| HCV | 6423 | 6452 | Hypo | virus | | HCV | 6686 | 6715 | Hypo | virus | |
| HCV | 6949 | 6978 | Hypo | virus | | HCV | 7212 | 7241 | Hypo | virus | |
| HCV | 7475 | 7504 | Hypo | virus | | HCV | 7738 | 7767 | Hypo | virus | |
| HCV | 8001 | 8030 | Hypo | virus | | HCV | 8264 | 8293 | Hypo | virus | |
| HCV | 8527 | 8556 | Hypo | virus | | HCV | 8790 | 8819 | Hypo | virus | |
| HCV | 9053 | 9082 | Hypo | virus | | chr8 | 1085573 | 1085603 | Hypo | cancer_general | DLGAP2 |
| chr8 | 1325465 | 1325606 | Hypo | cancer_general | | chr8 | 1444052 | 1444205 | Hypo | cancer_general | MFHAS1 |
| chr8 | 8640024 | 8640100 | Hypo | cancer_general | MFHAS1 | chr8 | 8681258 | 8681353 | Hypo | blood | MFHAS1 |
| chr8 | 8748422 | 8748713 | Hypo | cancer_general | MFHAS1 | chr8 | 8748919 | 8748956 | Hypo | cancer_general | |
| chr8 | 9722850 | 9722896 | Hypo | cancer_general | | chr8 | 10653917 | 10653017 | Hypo | ovarian | CTSB, FDFT1 |
| chr8 | 10980452 | 10980589 | Hypo | cancer_general | C8orfl5 | chr8 | 11700190 | 11700284 | Hypo | head_neck | CTSB, FDFT1 |
| chr8 | 11705960 | 11706136 | Hypo | cancer_general | FDFT1, CTSB | chr8 | 11706580 | 11706613 | Hypo | cancer_general | TRNA_Pseudo |
| chr8 | 11726469 | 11726975 | Hypo | cancer_general | | chr8 | 11790579 | 11790653 | Hypo | cancer_general | |
| chr8 | 13319931 | 13319961 | Hypo | cancer_general | | chr8 | 20375563 | 20375592 | Hypo | literature | MIR320A, POLR3D |
| chr8 | 21876649 | 21876819 | Hypo | cancer_general | | chr8 | 22101641 | 22101699 | Hypo | cancer_general | SLC25A37, AF116693, FP15737 |
| chr8 | 22458657 | 22458687 | Hypo | head_neck | KIAA1967, C8orf58, PDLIM2 | chr8 | 23423923 | 23423974 | Hypo | cancer_general | HMBOX1, INTS9 |
| chr8 | 28266438 | 28266484 | Hypo | breast | | chr8 | 28377884 | 28738023 | Hypo | cancer_general | |
| chr8 | 30475450 | 30475480 | Hypo | breast | GTF2E2 | chr8 | 31044103 | 31044133 | Hypo | ovarian | EIF4EBP1 |
| chr8 | 37755922 | 37755952 | Hypo | cancer_general | ASH2L | chr8 | 37906396 | 37906513 | Hypo | head_neck | LSM1 |
| chr8 | 37961793 | 37961902 | Hypo | cancer_general | BAG4, LSM1 | chr8 | 38020213 | 38020272 | Hypo | head_neck | LETM2 |
| chr8 | 38032345 | 38032827 | Hypo | cancer_general | | chr8 | 38256378 | 38256412 | Hypo | cancer_general | |
| chr8 | 38262472 | 38262502 | Hypo | pancreas | FGFR1, LETM2 | chr8 | 38274835 | 38274864 | Hypo | literature | FGFR1, LETM2 |
| chr8 | 39172082 | 39172134 | Hypo | literature | ADAM5 | chr8 | 41166305 | 41166374 | Hypo | pancreas | SFRP1 |
| chr8 | 41700639 | 41700751 | Hypo | cancer_general | | chr8 | 41711325 | 41711447 | Hypo | cancer_general | |
| chr8 | 41910270 | 41910339 | Hypo | cancer_general | KAT6A | chr8 | 42082721 | 42082874 | Hypo | pancreas | |
| chr8 | 42147392 | 42147521 | Hypo | cancer_general | IKBKB | chr8 | 42293604 | 42293722 | Hypo | breast | SLC20A2 |
| chr8 | 42350324 | 42350492 | Hypo | cancer_general | SLC20A2 | chr8 | 42749816 | 42750012 | Hypo | cancer_general | MIR4469, HOOK3, RNF170 |
| chr8 | 47093246 | 47093276 | Hypo | cancer_general | | chr8 | 47334619 | 47334678 | Hypo | cancer_general | |
| chr8 | 48044710 | 48044753 | Hypo | ovarian | | chr8 | 49572029 | 49572058 | Hypo | literature | |
| chr8 | 49836145 | 49836174 | Hypo | literature | SNAI2 | chr8 | 49959230 | 49959260 | Hypo | cancer_general | C8orf22 |
| chr8 | 52230518 | 52230548 | Hypo | cancer_general | PXDNL | chr8 | 53322495 | 53322524 | Hypo | literature | ST18 |
| chr8 | 54698973 | 54699103 | Hypo | breast | ATP6V1H | chr8 | 55826087 | 55826117 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 56542925 | 56543064 | Hypo | cancer_general | | chr8 | 57360211 | 57360240 | Hypo | literature | AX747062, PENK |
| chr8 | 58105946 | 58106115 | Hypo | cancer_general | | chr8 | 58117004 | 58117079 | Hypo | cancer_general | |
| chr8 | 58130364 | 58130574 | Hypo | cancer_general | LOC100507651 | chr8 | 59058941 | 59059343 | Hypo | ovarian | FAM110B |
| chr8 | 59747186 | 59747318 | Hypo | cancer_general | TOX | chr8 | 61775575 | 61777699 | Hypo | breast | |
| chr8 | 61789974 | 61790004 | Hypo | cancer_general | | chr8 | 62033879 | 62034059 | Hypo | cancer_general | MTFR1, ARMC1 |
| chr8 | 62763403 | 62763433 | Hypo | cancer_general | | chr8 | 66548717 | 66548800 | Hypo | cancer_general | |
| chr8 | 66560323 | 66560545 | Hypo | cancer_general | MTFR1 | chr8 | 67580735 | 67580829 | Hypo | cancer_general | C8orf44-SGK3, VCPIP1, C8orf44 |
| chr8 | 71017156 | 71017195 | Hypo | cancer_general | NCOA2 | chr8 | 71308096 | 71308126 | Hypo | cancer_general | |
| chr8 | 71447529 | 71447559 | Hypo | cancer_general | | chr8 | 72470399 | 72470441 | Hypo | cancer_general | |
| chr8 | 74759306 | 74759463 | Hypo | cancer_general | UBE2W, TCEB1, TMEM70 | chr8 | 74759819 | 74759966 | Hypo | cancer_general | UBE2W |
| chr8 | 74889486 | 74889592 | Hypo | cancer_general | | chr8 | 76316329 | 76316452 | Hypo | cancer_general | HNF4G |
| chr8 | 80894529 | 80894594 | Hypo | cancer_general | TPD52, MRPS28 | chr8 | 80998526 | 80998601 | Hypo | lung | TPD52 |
| chr8 | 81128658 | 81128782 | Hypo | breast | | chr8 | 81414643 | 81414831 | Hypo | colorectal | ZBTB10 |
| chr8 | 82243813 | 82243843 | Hypo | cancer_general | | chr8 | 82902963 | 82902993 | Hypo | cancer_general | |
| chr8 | 84932902 | 84932942 | Hypo | cancer_general | | chr8 | 86131760 | 86131850 | Hypo | cancer_general | E2F5, CA13, AB209185, C8orf59 |
| chr8 | 86405788 | 86405818 | Hypo | lung | | chr8 | 86406716 | 86406849 | Hypo | cancer_general | |
| chr8 | 86436621 | 86436651 | Hypo | cancer_general | | chr8 | 86495193 | 86495287 | Hypo | cancer_general | |
| chr8 | 86544756 | 86544959 | Hypo | cancer_general | | chr8 | 90702972 | 90703034 | Hypo | cancer_general | |
| chr8 | 90913079 | 90913653 | Hypo | cancer_general | OSGIN2, OTUD6B, BC067244 | chr8 | 91411537 | 91411567 | Hypo | cancer_general | |
| chr8 | 92083523 | 92083751 | Hypo | cancer_general | RAD54B, C8orf69 | chr8 | 94684190 | 94684560 | Hypo | cancer_general | LINC00535 |
| chr8 | 95485999 | 95486029 | Hypo | cancer_general | | chr8 | 96038540 | 96038580 | Hypo | cancer_general | NDUFAF6, C8orf37, TRNA_Ser, LOC100616530 |
| chr8 | 96219863 | 96219901 | Hypo | cancer_general | | chr8 | 96285420 | 96285553 | Hypo | ovarian | |
| chr8 | 97339846 | 97340195 | Hypo | cancer_general | PTDSS1 | chr8 | 98744202 | 98744325 | Hypo | cancer_general | MTDH |
| chr8 | 98786343 | 98786387 | Hypo | ovarian | LAPTM4B | chr8 | 98786918 | 98786972 | Hypo | ovarian | LAPTM4B |
| chr8 | 99234962 | 99235037 | Hypo | breast | NIPAL2 | chr8 | 99951897 | 99951939 | Hypo | cancer_general | OSR2 |
| chr8 | 100117651 | 100117765 | Hypo | breast | VPS13B | chr8 | 101169625 | 101169659 | Hypo | cancer_general | SPAG1, POLR2K |
| chr8 | 101726865 | 101726945 | Hypo | lung | PABPC1 | chr8 | 101736027 | 101736202 | Hypo | cancer_general | PABPC1 |
| chr8 | 103575128 | 103575296 | Hypo | pancreas | ODF1 | chr8 | 103629590 | 103629882 | Hypo | cancer_general | |
| chr8 | 106301844 | 106301978 | Hypo | cancer_general | | chr8 | 106434115 | 106434145 | Hypo | cancer_general | |
| chr8 | 109500408 | 109500507 | Hypo | lung | EMC2 | chr8 | 110275006 | 110275040 | Hypo | cancer_general | ZFPM2 |
| chr8 | 110406028 | 110406243 | Hypo | cancer_general | PKHD1L1 | chr8 | 110592198 | 110592228 | Hypo | cancer_general | NUDCD1 |
| chr8 | 110704001 | 110704144 | Hypo | esophageal | | chr8 | 111133092 | 111133257 | Hypo | cancer_general | SYBU |
| chr8 | 115516296 | 115516440 | Hypo | cancer_general | | chr8 | 118532128 | 118532292 | Hypo | cancer_general | |
| chr8 | 119043568 | 119043732 | Hypo | cancer_general | EXT1 | chr8 | 120219912 | 120219941 | Hypo | literature | MED30 |
| chr8 | 120844095 | 120844285 | Hypo | cancer_general | DSCC1, TAF2 | chr8 | 120845586 | 120845807 | Hypo | cancer_general | MAL2 DSCC1, TAF2 |
| chr8 | 121825455 | 121825484 | Hypo | literature | | chr8 | 122068889 | 122068919 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 122346689 | 122346719 | Hypo | cancer_general | | chr8 | 122346940 | 122347052 | Hypo | cancer_general | |
| chr8 | 123695532 | 123695660 | Hypo | cancer_general | | chr8 | 124014063 | 124014111 | Hypo | lung | ATAD2 |
| chr8 | 124055236 | 124055336 | Hypo | cancer_general | | chr8 | 124332846 | 124332875 | Hypo | literature | |
| chr8 | 124427887 | 124428082 | Hypo | cancer_general | DERL1 | chr8 | 125411827 | 125411857 | Hypo | head_neck | |
| chr8 | 125452366 | 125452541 | Hypo | cancer_general | WDYHV1 | chr8 | 126007690 | 126008051 | Hypo | ovarian | SQLE |
| chr8 | 126044442 | 126044563 | Hypo | cancer_general | KIAA0196, SQLE | chr8 | 127354106 | 127354261 | Hypo | cancer_general | |
| chr8 | 128403354 | 128403383 | Hypo | literature | DQ515899, DQ515898, LOC727677 | chr8 | 128745542 | 128745633 | Hypo | cancer_general | MYC, HV975509, BC042052 |
| chr8 | 128808002 | 128808077 | Hypo | literature | MIR1204, PVT1, MYC | chr8 | 128872385 | 128872415 | Hypo | cancer_general | |
| chr8 | 128889324 | 128889422 | Hypo | cancer_general | PVT1 | chr8 | 128893019 | 128893049 | Hypo | ovarian | PVT1 |
| chr8 | 128931133 | 128931261 | Hypo | lung | | chr8 | 128964114 | 128964309 | Hypo | breast | MIR1205, TMEM75, PVT1 |
| chr8 | 129356009 | 129356039 | Hypo | cancer_general | | chr8 | 130369244 | 130369364 | Hypo | cancer_general | CCDC26 |
| chr8 | 132054727 | 132054785 | Hypo | cancer_general | ADCY8 | chr8 | 133360080 | 133360194 | Hypo | cancer_general | KCNQ3 |
| chr8 | 133686745 | 133687107 | Hypo | cancer_general | LRRC6 | chr8 | 135301097 | 135301142 | Hypo | cancer_general | |
| chr8 | 140755383 | 140755550 | Hypo | breast | TRAPPC9 | chr8 | 140834237 | 140834321 | Hypo | cancer_general | TRAPPC9 |
| chr8 | 140963292 | 140963362 | Hypo | cancer_general | TRAPPC9 | chr8 | 141054845 | 141054875 | Hypo | cancer_general | TRAPPC9 |
| chr8 | 141159919 | 141159949 | Hypo | cancer_general | | chr8 | 141588056 | 141588132 | Hypo | cancer_general | AGO2 |
| chr8 | 141596886 | 141597022 | Hypo | ovarian | AGO2 | chr8 | 141614252 | 141614287 | Hypo | breast | AGO2 |
| chr8 | 142210914 | 142211043 | Hypo | lung | DENND3, SLC45A4 | chr8 | 142265206 | 142265339 | Hypo | ovarian | |
| chr8 | 142282078 | 142282202 | Hypo | hepatobiliary | | chr8 | 142292552 | 142292774 | Hypo | cancer_general, lung | |
| chr8 | 142361233 | 142361487 | Hypo | cancer_general | GPR20, LOC731779 | chr8 | 142367368 | 142367790 | Hypo | breast | GPR20 |
| chr8 | 142444600 | 142444752 | Hypo | cancer_general | MROH5, PTP4A3 | chr8 | 142535343 | 142535496 | Hypo | cancer_general | |
| chr8 | 142568598 | 142568652 | Hypo | cancer_general | | chr8 | 142632436 | 142632465 | Hypo | literature | |
| chr8 | 142694847 | 142694953 | Hypo | cancer_general | | chr8 | 142984512 | 142984666 | Hypo | cancer_general | |
| chr8 | 143082777 | 143082810 | Hypo | cancer_general | | chr8 | 143089030 | 143089100 | Hypo | cancer_general | |
| chr8 | 143105244 | 143105377 | Hypo | cancer_general | | chr8 | 143368318 | 143368469 | Hypo | pancreas | |
| chr8 | 143509457 | 143509594 | Hypo | cancer_general | | chr8 | 143557980 | 143558080 | Hypo | cancer_general | TSNARE1 |
| chr8 | 143558472 | 143558604 | Hypo | ovarian | BAI1 | chr8 | 143587331 | 143587382 | Hypo | cancer_general | BAI1 |
| chr8 | 143611232 | 143611262 | Hypo | hepatobiliary | BAI1 | chr8 | 143621980 | 143622096 | Hypo | cancer_general | BAI1 |
| chr8 | 143702052 | 143702101 | Hypo | cancer_general | ARC | chr8 | 143819384 | 143819428 | Hypo | cancer_general | SLURP1, THEM6 |
| chr8 | 143876928 | 143876958 | Hypo | cancer_general | LY6D | chr8 | 143993974 | 143994165 | Hypo | cancer_general | CYP11B2 |
| chr8 | 144069546 | 144069651 | Hypo | cancer_general | CDC42P3, LOC100133669 | chr8 | 144190378 | 144190432 | Hypo | cancer_general | |
| chr8 | 144203977 | 144204021 | Hypo | cancer_general | LY6H | chr8 | 144226174 | 144226204 | Hypo | cancer_general | GPIHBP1 |
| chr8 | 144238822 | 144238901 | Hypo | cancer_general | ZFP41 | chr8 | 144303562 | 144303592 | Hypo | ovarian | GLI4 |
| chr8 | 144330193 | 144330380 | Hypo | cancer_general | GLI4 | chr8 | 144344293 | 144344442 | Hypo | cancer_general | GLI4 |
| chr8 | 144347397 | 144347740 | Hypo | cancer_general | GLI4 | chr8 | 144359977 | 144360076 | Hypo | cancer_general | GLI4 |
| chr8 | 144360394 | 144360453 | Hypo | cancer_general | ZNF696 | chr8 | 144361758 | 144361823 | Hypo | cancer_general | |
| chr8 | 144372323 | 144372503 | Hypo | cancer_general | | chr8 | 144382679 | 144382775 | Hypo | cancer_general | TOP1MT, ZNF696 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 144421487 | 144421517 | Hypo | blood | TOP1MT | chr8 | 144557003 | 144557088 | Hypo | head_neck | ZC3H3 |
| chr8 | 144617065 | 144617347 | Hypo | ovarian | ZC3H3 | chr8 | 144668566 | 144668667 | Hypo | breast | BC034020, EEF1D, NAPRT1 |
| chr8 | 144668909 | 144668972 | Hypo | breast | BC034020, EEF1D, NAPRT1 | chr8 | 145218226 | 145218301 | Hypo | blood | MROH1 |
| chr8 | 145223902 | 145224061 | Hypo | ovarian | MROH1 | chr8 | 145753517 | 145753547 | Hypo | cancer_general | DQ579335, LRRC14, ARHGAP39, C8orf82, LRRC24 |
| chr8 | 145758572 | 145758692 | Hypo | cancer_general | ARHGAP39, C8orf82, LRRC24 | chr8 | 145918683 | 145918835 | Hypo | cancer_general | ARHGAP39 |
| chr8 | 146013617 | 146013647 | Hypo | cancer_general | RPL8, DL491750, ZNF34 | chr8 | 146079215 | 146079379 | Hypo | cancer_general | COMMD5 |
| chr8 | 146175120 | 146175269 | Hypo | cancer_general | ZNF16 | chr8 | 146176756 | 146176795 | Hypo | cancer_general | ZNF16 |
| chr21 | 19274828 | 19274858 | Hypo | cancer_general | CHODL | chr21 | 31015201 | 31015231 | Hypo | cancer_general | GRIK1 |
| chr21 | 31056850 | 31056927 | Hypo | hepatobiliary | GRIK1 | chr21 | 32253745 | 32253774 | Hypo | literature | KRTAP11-1 |
| chr21 | 33043985 | 33044051 | Hypo | breast | SOD1, SCAF4 | chr21 | 33627549 | 33627649 | Hypo | cancer_general | |
| chr21 | 33721756 | 33721824 | Hypo | cancer_general | URB1 | chr21 | 33983236 | 33983488 | Hypo | cancer_general | C21orf59 |
| chr21 | 34397024 | 34397091 | Hypo | cancer_general | OLIG2 | chr21 | 34469746 | 34469844 | Hypo | cancer_general | DOPEY2, CBR3-AS1, CBR3 |
| chr21 | 35051159 | 35051231 | Hypo | cancer_general | ITSN1 | chr21 | 37527928 | 37527958 | Hypo | cancer_general | CHAF1B |
| chr21 | 37758570 | 37758652 | Hypo | cancer_general | CHAF1B | chr21 | 37775034 | 37775141 | Hypo | cancer_general, breast | |
| chr21 | 38092179 | 38092221 | Hypo | cancer_general | SIM2 | chr21 | 38638422 | 38638526 | Hypo | cancer_general | DSCR3 |
| chr21 | 38935478 | 38935549 | Hypo | cancer_general | | chr21 | 40034756 | 40034785 | Hypo | literature | ERG |
| chr21 | 42596911 | 42597043 | Hypo | hepatobiliary | | chr21 | 42617963 | 42617995 | Hypo | hepatobiliary | BACE2 |
| chr21 | 42649172 | 42649202 | Hypo | hepatobiliary | | chr21 | 43240082 | 43240112 | Hypo | ovarian | PRDM15 |
| chr21 | 43256565 | 43256603 | Hypo | blood | BACE2 | chr21 | 43376373 | 43376403 | Hypo | cancer_general | AX748362, UMODL1 |
| chr21 | 43393528 | 43393713 | Hypo | pancreas | PRDM15 | chr21 | 43485279 | 43485348 | Hypo | head_neck | SLC37A1 |
| chr21 | 43786683 | 43786713 | Hypo | cancer_general | TMPRSS3, TFF1 | chr21 | 43991463 | 43991493 | Hypo | cancer_general | |
| chr21 | 44250815 | 44250855 | Hypo | cancer_general | | chr21 | 44283581 | 44283774 | Hypo | head_neck | WDR4 |
| chr21 | 44514762 | 44514791 | Hypo | literature | U2AF1 | chr21 | 44524441 | 44524470 | Hypo | literature | U2AF1 |
| chr21 | 44837088 | 44837213 | Hypo | cancer_general | SIK1 | chr21 | 44866603 | 44866711 | Hypo | cancer_general | LINC00319 |
| chr21 | 44886709 | 44886870 | Hypo | breast | LINC00313 | chr21 | 45118492 | 45118644 | Hypo | esophageal | RRP1B |
| chr21 | 45131875 | 45131905 | Hypo | cancer_general | PDXK | chr21 | 45195149 | 45195319 | Hypo | cancer_general | CSTB |
| chr21 | 45271643 | 45271688 | Hypo | cancer_general | | chr21 | 45273717 | 45273913 | Hypo | cancer_general | |
| chr21 | 45277332 | 45277513 | Hypo | cancer_general | AGPAT3 | chr21 | 45290014 | 45290044 | Hypo | head_neck | AGPAT3 |
| chr21 | 45508617 | 45508647 | Hypo | colorectal | TRAPPC10 | chr21 | 45521343 | 45521438 | Hypo | breast | PWP2, TRAPPC10 |
| chr21 | 45621533 | 45621573 | Hypo | breast | | chr21 | 45791079 | 45791109 | Hypo | cancer_general | TRPM2 |
| chr21 | 45847832 | 45847973 | Hypo | cancer_general | TRPM2 | chr21 | 46036642 | 46036767 | Hypo | cancer_general | KRTAP10-8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr21 | 46193414 | 46193542 | Hypo | cancer_general | UBE2G2 | chr21 | 46257116 | 46257273 | Hypo | cancer_general | ITGB2 |
| chr21 | 46310428 | 46310491 | Hypo | cancer_general | ITGB2 | chr21 | 46318286 | 46318343 | Hypo | cancer_general | FAM207A, C21orf67, ITGB2-AS1 |
| chr21 | 46319156 | 46319459 | Hypo | cancer_general | ITGB2 | chr21 | 46359187 | 46359248 | Hypo | cancer_general | POFUT2, C21orf89 |
| chr21 | 46452374 | 46452539 | Hypo | cancer_general |  | chr21 | 46677734 | 46677796 | Hypo | cancer_general |  |
| chr21 | 46847654 | 46847684 | Hypo | pancreas | COL18A1-AS1 | chr21 | 46863658 | 46863708 | Hypo | cancer_general |  |
| chr21 | 46925780 | 46925925 | Hypo | breast | COL18A1, SLC19A1 | chr21 | 46926459 | 46926565 | Hypo | cancer_general | SLC19A1, COL18A1 |
| chr21 | 46935739 | 46935936 | Hypo | breast | SLC19A1, COL18A1 | chr21 | 47404174 | 47404325 | Hypo | cancer_general | COL6A1 |
| chr21 | 47504861 | 47504895 | Hypo | cancer_general |  | chr21 | 47746270 | 47746393 | Hypo | cancer_general | PCNT, BC031638, C21orf58 |
| chr11 | 232863 | 233062 | Hypo | cancer_general | PSMD13, SIRT3 | chr11 | 392576 | 392720 | Hypo | head_neck | PKP3 |
| chr11 | 394815 | 394968 | Hypo | cancer_general | PKP3 | chr11 | 505732 | 505869 | Hypo | cancer_general | RNH1 |
| chr11 | 518400 | 518430 | Hypo | literature |  | chr11 | 526389 | 526419 | Hypo | cancer_general | HRAS |
| chr11 | 533451 | 533567 | Hypo | literature | LRRC56, HRAS | chr11 | 533859 | 533888 | Hypo | literature | LRRC56, HRAS |
| chr11 | 534273 | 534302 | Hypo | literature | LRRC56, HRAS | chr11 | 548731 | 548800 | Hypo | lung | C11orf35, AX748330, LRRC56 |
| chr11 | 763323 | 763686 | Hypo | cancer_general | BC048998, PDDC1, TALDO1 | chr11 | 775261 | 775291 | Hypo | pancreas | NS3BP, PDDC1, BC048998 |
| chr11 | 850555 | 850823 | Hypo | cancer_general | TSPAN4, POLR2L, AK126635 | chr11 | 861612 | 861657 | Hypo | cancer_general | CHID1, AK126635, TSPAN4 |
| chr11 | 863062 | 863092 | Hypo | cancer_general | CHID1, AK126635, TSPAN4 | chr11 | 1006077 | 1006107 | Hypo | cancer_general | MUC6 |
| chr11 | 1027540 | 1027574 | Hypo | head_neck | MUC6 | chr11 | 1029238 | 1029403 | Hypo | cancer_general | MUC6 |
| chr11 | 1030215 | 1030296 | Hypo | cancer_general | MUC6 | chr11 | 1080391 | 1080454 | Hypo | cancer_general | MUC2 |
| chr11 | 1081667 | 1081715 | Hypo | cancer_general | MUC2 | chr11 | 1214665 | 1214917 | Hypo | cancer_general | MUC5AC, MUC5B |
| chr11 | 1215899 | 1215999 | Hypo | cancer_general | MUC5AC, MUC5B | chr11 | 1229945 | 1229975 | Hypo | cancer_general | MUC5AC, MUC5B |
| chr11 | 1244381 | 1244465 | Hypo | cancer_general | MUC5B | chr11 | 1250889 | 1250924 | Hypo | cancer_general | MUC5B |
| chr11 | 1251183 | 1251351 | Hypo | cancer_general | MUC5B | chr11 | 1263602 | 1263644 | Hypo | cancer_general | MUC5B |
| chr11 | 1274085 | 1274189 | Hypo | cancer_general | MUC5B | chr11 | 1374959 | 1375003 | Hypo | cancer_general | MUC5B |
| chr11 | 1430714 | 1430794 | Hypo | cancer_general | BRSK2 | chr11 | 1464280 | 1464428 | Hypo | cancer_general | BRSK2 |
| chr11 | 1469228 | 1469379 | Hypo | cancer_general | BRSK2 | chr11 | 1471920 | 1472058 | Hypo | cancer_general | BRSK2 |
| chr11 | 1868081 | 1868237 | Hypo | cancer_general | TNNT2, LSP1 | chr11 | 1946130 | 1946160 | Hypo | cancer_general | TNNT3 |
| chr11 | 1957391 | 1957530 | Hypo | cancer_general | TNNT3 | chr11 | 1959077 | 1959187 | Hypo | cancer_general | MRPL23, TNNT3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 2040107 | 2040148 | Hypo | colorectal | | chr11 | 2209907 | 2210278 | Hypo | cancer_general | |
| chr11 | 2226048 | 2226078 | Hypo | cancer_general | | chr11 | 2278708 | 2278839 | Hypo | cancer_general | |
| chr11 | 2437991 | 2438144 | Hypo | cancer_general | | chr11 | 3027425 | 3027562 | Hypo | head_neck | CARS |
| chr11 | 3169665 | 3169835 | Hypo | colorectal | | chr11 | 3182104 | 3182133 | Hypo | tcga | NUP98 |
| chr11 | 3511446 | 3511501 | Hypo | hepatobiliary | | chr11 | 3767205 | 3767284 | Hypo | cancer_general | STIM1 |
| chr11 | 4038082 | 4038176 | Hypo | cancer_general | | chr11 | 4095819 | 4095864 | Hypo | ovarian | TRIM34, TRIM6, TRIM6-TRIM34 |
| chr11 | 4209382 | 4209411 | Hypo | tcga | RRM1, LOC100506082 | chr11 | 5641077 | 5641140 | Hypo | lung | |
| chr11 | 5993897 | 5994029 | Hypo | cancer_general | OR56A5 | chr11 | 6497192 | 6497222 | Hypo | cancer_general | ARFIP2, TIMM10B, TRIM3 |
| chr11 | 9405392 | 9405752 | Hypo | cancer_general | IPO7 | chr11 | 10509678 | 10509807 | Hypo | cancer_general | AMPD3 |
| chr11 | 10811151 | 10811224 | Hypo | cancer_general | EIF4G2, CTR9 | chr11 | 10815867 | 10815998 | Hypo | cancer_general | EIF4G2, SNORD97 |
| chr11 | 13711492 | 13711529 | Hypo | hepatobiliary | FAR1 | chr11 | 14316375 | 14316404 | Hypo | literature | RRAS2 |
| chr11 | 14543250 | 14543304 | Hypo | cancer_general | PSMA1 | chr11 | 14866247 | 14866285 | Hypo | cancer_general | PDE3B |
| chr11 | 17741679 | 17741708 | Hypo | literature | MYOD1 | chr11 | 18100096 | 18100259 | Hypo | breast | SAAL1 |
| chr11 | 20408219 | 20408341 | Hypo | cancer_general | PRMT3 | chr11 | 20618292 | 20618322 | Hypo | esophageal | SLC6A5 |
| chr11 | 20618526 | 20618556 | Hypo | esophageal | SLC6A5 | chr11 | 31760124 | 31760235 | Hypo | ovarian | ELP4 |
| chr11 | 33264773 | 33264935 | Hypo | head_neck | | chr11 | 33277455 | 33277485 | Hypo | cancer_general | HIPK3 |
| chr11 | 33318780 | 33318945 | Hypo | pancreas | | chr11 | 33858324 | 33858463 | Hypo | cancer_general | |
| chr11 | 33993984 | 33994014 | Hypo | cancer_general | | chr11 | 34535093 | 34535123 | Hypo | cancer_general | ELF5 |
| chr11 | 35684958 | 35685131 | Hypo | cancer_general | TRIM44 | chr11 | 44337533 | 44337571 | Hypo | cancer_general | ALX4 |
| chr11 | 46227561 | 46227654 | Hypo | cancer_general | | chr11 | 46866293 | 46866510 | Hypo | cancer_general | LRP4-AS1 |
| chr11 | 46959190 | 46959251 | Hypo | cancer_general | C11orf49 | chr11 | 47260168 | 47260258 | Hypo | breast | NR1H3, DDB2, ACP2 |
| chr11 | 47358926 | 47359237 | Hypo | cancer_general | MYBPC3 SP1, SLC39A13, MYBPC3 | chr11 | 47363557 | 47363625 | Hypo | head_neck | MYBPC3 CELF1, RAPSN |
| chr11 | 47372828 | 47373002 | Hypo | pancreas | | chr11 | 47478438 | 47478500 | Hypo | breast | |
| chr11 | 47485995 | 47486141 | Hypo | lung | CELF1 CLP1, ZDHHC5 | chr11 | 57235406 | 57235436 | Hypo | cancer_general | RTN4RL2 TMX2, C11orf31, BTBD18, TMX2-CTNND1 |
| chr11 | 57437157 | 57437234 | Hypo | cancer_general | | chr11 | 57500982 | 57501068 | Hypo | cancer_general | |
| chr11 | 59329086 | 59329240 | Hypo | cancer_general | TRNA_Lys, U7, TRNA_Leu, JB175310, TRNA_Phe | chr11 | 59841403 | 59841533 | Hypo | cancer_general | MS4A3 |
| chr11 | 60927079 | 60927319 | Hypo | cancer_general | VPS37C DDB1, VWCE | chr11 | 61049694 | 61049736 | Hypo | cancer_general | VWCE |
| chr11 | 61058283 | 61058341 | Hypo | cancer_general | | chr11 | 61148730 | 61148768 | Hypo | colorectal | |
| chr11 | 61154806 | 61154836 | Hypo | cancer_general | TMEM216 RAB3IL1, FADS3 | chr11 | 61536985 | 61537014 | Hypo | literature | MYRF |
| chr11 | 61664655 | 61664770 | Hypo | cancer_general | | chr11 | 61666106 | 61666136 | Hypo | cancer_general | RAB3IL1, FADS3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 61811996 | 61812151 | Hypo | cancer_general | EML3, ROM1, MTA2 | chr11 | 61880361 | 61880398 | Hypo | cancer_general | UBXN1, C11orf83, |
| chr11 | 62370720 | 62370750 | Hypo | cancer_general | | chr11 | 62440509 | 62440588 | Hypo | cancer_general | C11orf48, METTL12, SNORA57 |
| chr11 | 62484517 | 62484547 | Hypo | breast | HNRNPUL2, GNG3 | | 62497600 | 62497630 | Hypo | cancer_general | TTC9C, HNRNPUL2 |
| chr11 | 62555752 | 62555782 | Hypo | cancer_general | NXF1, TMEM179B, TAF6L, TMEM223 | chr11 | 63202941 | 63203091 | Hypo | cancer_general | |
| chr11 | 63431856 | 63431918 | Hypo | ovarian | ATL3 | chr11 | 63432139 | 63432218 | Hypo | ovarian | ATL3 |
| chr11 | 63609824 | 63610013 | Hypo | cancer_general | MARK2 | chr11 | 63641072 | 63641256 | Hypo | breast | MARK2 |
| chr11 | 63849394 | 63849426 | Hypo | cancer_general | MACROD1 | chr11 | 63934498 | 63934619 | Hypo | cancer_general | RPS6KA4, |
| chr11 | 64105954 | 64106108 | Hypo | cancer_general | CCDC88B | chr11 | 64120879 | 64120909 | Hypo | cancer_general | CCDC88B |
| chr11 | 64140397 | 64140427 | Hypo | cancer_general | MIR1237, RPS6KA4 | chr11 | 64578577 | 64578743 | Hypo | cancer_general | MEN1, MAP4K2 |
| chr11 | 64796439 | 64796571 | Hypo | cancer_general | ARL2-SNX15, ARL2 | chr11 | 64809584 | 64809906 | Hypo | cancer_general | NAALADL1, SAC3D1, ARL2-SNX15 |
| chr11 | 64903331 | 64903361 | Hypo | cancer_general | SYVN1, MRPL49 | chr11 | 64950292 | 64950374 | Hypo | cancer_general | CAPN1, SPDYC |
| chr11 | 65091272 | 65091369 | Hypo | cancer_general | DPF2, CDC42EP2 | chr11 | 65364470 | 65364557 | Hypo | blood | MAP3K11, KCNK7, EHBP1L1 |
| chr11 | 65448943 | 65449022 | Hypo | cancer_general | | chr11 | 65478376 | 65478611 | Hypo | cancer_general | KAT5, RNASEH2C |
| chr11 | 65510941 | 65511172 | Hypo | cancer_general | EIF1AD, AX747517, CST6, CATSPER1, BANF1 | chr11 | 65511392 | 65511522 | Hypo | cancer_general | PACS1 |
| chr11 | 65778952 | 65778981 | Hypo | literature | | chr11 | 65891131 | 65891227 | Hypo | cancer_general | |
| chr11 | 66114279 | 66114331 | Hypo | cancer_general | TRNA_Ser, B3GNT1, BRMS1 | chr11 | 66138094 | 66138260 | Hypo | cancer_general | SLC29A2, AX747485 |
| chr11 | 66324254 | 66324447 | Hypo | cancer_general | CTSF, ACTN3 | chr11 | 66454424 | 66454454 | Hypo | head_neck | SPTBN2, RBM4B |
| chr11 | 66511223 | 66511431 | Hypo | cancer_general | C11orf80 | chr11 | 66513217 | 66513646 | Hypo | cancer_general | C11orf80 |
| chr11 | 66557543 | 66557710 | Hypo | cancer_general | C11orf80 | chr11 | 66625207 | 66625240 | Hypo | cancer_general | LRFN4, PC |
| chr11 | 66649028 | 66649058 | Hypo | cancer_general | | chr11 | 66658224 | 66658290 | Hypo | ovarian | |
| chr11 | 67072239 | 67072396 | Hypo | cancer_general | SSH3, ANKRD13D, AK057681 | chr11 | 67210017 | 67210057 | Hypo | cancer_general | |
| chr11 | 67248321 | 67248458 | Hypo | cancer_general | AIP | chr11 | 67462643 | 67462833 | Hypo | cancer_general | GPR152, CABP4, CORO1B, PTPRCAP, RPS6KB2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 67764187 | 67764254 | Hypo | cancer_general | UNC93B1 | chr11 | 67781196 | 67781564 | Hypo | lung | ALDH3B1, UNC93B1 |
| chr11 | 67797202 | 67797420 | Hypo | cancer_general | ALDH3B1, NDUFS8, MIR4691, TCIRG1 | chr11 | 67918044 | 67918145 | Hypo | pancreas | SUV420H1 |
| chr11 | 67999703 | 67999866 | Hypo | cancer_general | | chr11 | 68221758 | 68222056 | Hypo | cancer_general | PPP6R3, LRP5 |
| chr11 | 68409558 | 68409588 | Hypo | hepatobiliary | | chr11 | 68804728 | 68804776 | Hypo | cancer_general | |
| chr11 | 69192566 | 69192784 | Hypo | cancer_general | | chr11 | 69280561 | 69280633 | Hypo | cancer_general | |
| chr11 | 69466004 | 69466042 | Hypo | literature | BC133018, CCND1, AK294004, ORAOV1 | chr11 | 71192746 | 71192889 | Hypo | cancer_general | NADSYN1 |
| chr11 | 71647544 | 71647574 | Hypo | pancreas | RNF121, LOC100133315 | chr11 | 71792437 | 71792496 | Hypo | cancer_general | MIR3165, NUMA1, LRTOMT |
| chr11 | 71863650 | 71863785 | Hypo | cancer_general | | chr11 | 72413980 | 72414010 | Hypo | ovarian | BC150585, ARAP1 |
| chr11 | 72475677 | 72475711 | Hypo | cancer_general | STARD10 | chr11 | 72532348 | 72532378 | Hypo | cancer_general | ATG16L2 |
| chr11 | 73072907 | 73072953 | Hypo | cancer_general | ARHGEF17 | chr11 | 73310367 | 73310441 | Hypo | cancer_general | FAM168A |
| chr11 | 73481055 | 73481085 | Hypo | ovarian | RAB6A UCP2, DNAJB13 | chr11 | 73561763 | 73561798 | Hypo | ovarian | MRPL48 |
| chr11 | 73685698 | 73685845 | Hypo | ovarian | | chr11 | 74246487 | 74246521 | Hypo | cancer_general | |
| chr11 | 75459486 | 75459775 | Hypo | cancer_general | LOC283214 | chr11 | 75858210 | 75858240 | Hypo | colorectal | UVRAG |
| chr11 | 75859012 | 75859053 | Hypo | colorectal | UVRAG | chr11 | 76293588 | 76293618 | Hypo | head_neck | |
| chr11 | 76371738 | 76372077 | Hypo | cancer_general | LRRC32 | chr11 | 76594692 | 76594722 | Hypo | ovarian | ACER3 |
| chr11 | 77533964 | 77534145 | Hypo | cancer_general | AAMDC, RSF1 | chr11 | 82998001 | 82998121 | Hypo | cancer_general | BC070093, CCDC90B |
| chr11 | 85709169 | 85709254 | Hypo | ovarian | PICALM | chr11 | 89052235 | 89052282 | Hypo | cancer_general | NOX4 |
| chr11 | 93911651 | 93911800 | Hypo | colorectal | PANX1 | chr11 | 94275794 | 94275951 | Hypo | colorectal | PIWIL4, FUT4 |
| chr11 | 96517902 | 96517932 | Hypo | cancer_general | | chr11 | 101723359 | 101723455 | Hypo | cancer_general | |
| chr11 | 102158378 | 102158427 | Hypo | literature | C11orf65 | chr11 | 102961347 | 102961649 | Hypo | cancer_general | DCUN1D5 |
| chr11 | 108236072 | 108236101 | Hypo | literature | HSPB2, HSPB2-C11orf52, CRYAB | chr11 | 108603233 | 108603263 | Hypo | cancer_general | DDX10 |
| chr11 | 111783548 | 111783577 | Hypo | literature | | chr11 | 111976911 | 111976941 | Hypo | pancreas | |
| chr11 | 116976126 | 116976156 | Hypo | cancer_general | PAFAH1B2, AB231710, AB231711 | chr11 | 116984568 | 116984665 | Hypo | cancer_general | PAFAH1B2, SIDT2 |
| chr11 | 117017686 | 117017773 | Hypo | ovarian | | chr11 | 117055950 | 117056073 | Hypo | cancer_general | |
| chr11 | 118724458 | 118724605 | Hypo | colorectal | | chr11 | 118991033 | 118991079 | Hypo | cancer_general | HINFP, C2CD2L |
| chr11 | 119148865 | 119148945 | Hypo | literature | CBL | chr11 | 119149236 | 119149265 | Hypo | literature | CBL |
| chr11 | 120008105 | 120008504 | Hypo | cancer_general | TRIM29 | chr11 | 120367948 | 120368008 | Hypo | ovarian | |
| chr11 | 120998701 | 120998825 | Hypo | ovarian | TECTA | chr11 | 121152057 | 121152203 | Hypo | cancer_general | |
| chr11 | 122895443 | 122895485 | Hypo | cancer_general | LOC341056 | chr11 | 122961054 | 122961219 | Hypo | cancer_general | CLMP |
| chr11 | 123963874 | 123963994 | Hypo | cancer_general | | chr11 | 125220500 | 125220643 | Hypo | cancer_general | PKNOX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 125755612 | 125755710 | Hypo | cancer_general | HYLS1, PUS3 | chr11 | 125758604 | 125758660 | Hypo | cancer_general | PUS3, HYLS1 |
| chr11 | 128657892 | 128657970 | Hypo | cancer_general | | chr11 | 129907552 | 129907714 | Hypo | cancer_general | |
| chr11 | 129931742 | 129931851 | Hypo | cancer_general | APLP2 | chr11 | 130343061 | 130343100 | Hypo | hepatobiliary | ADAMTS15 |
| chr11 | 130359769 | 130359915 | Hypo | cancer_general | | chr11 | 130781550 | 130781781 | Hypo | ovarian | |
| chr11 | 130785487 | 130785622 | Hypo | cancer_general | SNX19 | chr11 | 130854324 | 130854490 | Hypo | cancer_general | SNX19 |
| chr11 | 131522763 | 131522947 | Hypo | cancer_general | | chr11 | 131766715 | 131766960 | Hypo | cancer_general | |
| chr11 | 132484215 | 132484404 | Hypo | cancer_general | | chr11 | 133231739 | 133231832 | Hypo | cancer_general | AK056505 |
| chr11 | 133792055 | 133792214 | Hypo | hepatobiliary | IGSF9B | chr5 | 230673 | 230709 | Hypo | breast | SDHA |
| chr5 | 303272 | 303301 | Hypo | literature | AHRR, PDCD6 | chr5 | 373363 | 373392 | Hypo | literature | AHRR |
| chr5 | 415870 | 415899 | Hypo | literature | AHRR | chr5 | 481012 | 481121 | Hypo | cancer_general | SLC9A3, PP7080, AK023178, FLJ00157, BC013821 |
| chr5 | 491335 | 491536 | Hypo | cancer_general | | | | | | | MIR4456 |
| chr5 | 554299 | 554538 | Hypo | cancer_general | | chr5 | 538758 | 538806 | Hypo | cancer_general | |
| chr5 | 555158 | 555285 | Hypo | cancer_general | | chr5 | 554871 | 554900 | Hypo | literature | |
| chr5 | 677889 | 678006 | Hypo | cancer_general | TPPP | chr5 | 555965 | 555995 | Hypo | cancer_general | |
| chr5 | 912806 | 912835 | Hypo | literature | TRIP13 | chr5 | 909204 | 909304 | Hypo | head_neck | TRIP13 |
| chr5 | 1059523 | 1059556 | Hypo | blood | MIR4635, SLC12A7 | chr5 | 1034600 | 1034653 | Hypo | cancer_general | NKD2 |
| | | | | | | chr5 | 1117778 | 1118270 | Hypo | cancer_general | |
| chr5 | 1131217 | 1131378 | Hypo | cancer_general | SLC6A19 | chr5 | 1136590 | 1136845 | Hypo | head_neck | |
| chr5 | 1193381 | 1193521 | Hypo | cancer_general | SLC6A19, SLC6A18 | chr5 | 1193880 | 1193944 | Hypo | cancer_general | SLC6A19 |
| chr5 | 1221197 | 1221307 | Hypo | cancer_general | | chr5 | 1259524 | 1259558 | Hypo | hepatobiliary | TERT |
| chr5 | 1271339 | 1271396 | Hypo | hepatobiliary | TERT | chr5 | 1295214 | 1295265 | Hypo | literature | TERT |
| chr5 | 1747022 | 1747098 | Hypo | cancer_general | | chr5 | 1779526 | 1779556 | Hypo | hepatobiliary | |
| chr5 | 1787378 | 1787418 | Hypo | cancer_general | | chr5 | 1950794 | 1950960 | Hypo | cancer_general | |
| chr5 | 2225439 | 2225469 | Hypo | lung | | chr5 | 2324383 | 2324413 | Hypo | cancer_general | |
| chr5 | 2367718 | 2367892 | Hypo | cancer_general | | chr5 | 2541487 | 2541611 | Hypo | cancer_general | |
| chr5 | 2753048 | 2753078 | Hypo | pancreas | C5orf38, IRX2 | chr5 | 3031879 | 3032018 | Hypo | cancer_general | |
| chr5 | 3152146 | 3152176 | Hypo | hepatobiliary | | chr5 | 3325042 | 3325272 | Hypo | cancer_general | UBE2QL1 |
| chr5 | 3674053 | 3674224 | Hypo | cancer_general | | chr5 | 4144367 | 4144516 | Hypo | cancer_general | ANKRD33B |
| chr5 | 6228617 | 6228790 | Hypo | cancer_general | CCT5, FAM173B | chr5 | 6482458 | 6482620 | Hypo | cancer_general | |
| chr5 | 10249098 | 10249127 | Hypo | literature | | chr5 | 10616516 | 10616550 | Hypo | cancer_general | |
| chr5 | 16466784 | 16467120 | Hypo | cancer_general | FAM134B, ZNF622 | chr5 | 16793851 | 16794008 | Hypo | hepatobiliary | MYO10 |
| chr5 | 16845452 | 16845619 | Hypo | hepatobiliary | MYO10 | chr5 | 16968118 | 16968148 | Hypo | hepatobiliary | |
| chr5 | 17095895 | 17095927 | Hypo | hepatobiliary | | chr5 | 17203012 | 17203177 | Hypo | cancer_general | LOC285696 |
| chr5 | 17311046 | 17311076 | Hypo | hepatobiliary | | chr5 | 17512114 | 17512144 | Hypo | hepatobiliary | |
| chr5 | 18034335 | 18034365 | Hypo | cancer_general | | chr5 | 23011928 | 23011958 | Hypo | cancer_general | |
| chr5 | 31572285 | 31572344 | Hypo | hepatobiliary | PDZD2 | chr5 | 31691477 | 31691652 | Hypo | cancer_general | PDZD2 |
| chr5 | 31879243 | 31879282 | Hypo | hepatobiliary | MTMR12 | chr5 | 32042283 | 32042419 | Hypo | lung | |
| chr5 | 32314345 | 32314379 | Hypo | cancer_general | ZFR | chr5 | 32333032 | 32333111 | Hypo | colorectal | |
| chr5 | 32446143 | 32446274 | Hypo | cancer_general | | chr5 | 33234280 | 33234411 | Hypo | cancer_general | |
| chr5 | 33298005 | 33298076 | Hypo | cancer_general | | chr5 | 33509607 | 33509776 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 33936486 | 33936516 | Hypo | cancer_general | SLC45A2, RXFP3 | chr5 | 35874560 | 35874589 | Hypo | literature | IL7R |
| chr5 | 35939832 | 35939861 | Hypo | literature | CAPSL | chr5 | 37376644 | 37376674 | Hypo | cancer_general | WDR70, NUP155 |
| chr5 | 39281800 | 39281943 | Hypo | lung | C9 | chr5 | 39343181 | 39343348 | Hypo | cancer_general esophageal, cancer_general | C9 |
| chr5 | 40775147 | 40775313 | Hypo | cancer_general | PRKAA1 | chr5 | 42260050 | 42260453 | Hypo | | |
| chr5 | 42931966 | 42931996 | Hypo | cancer_general | | chr5 | 43215538 | 43215738 | Hypo | lung, cancer_general | NIM1 |
| chr5 | 43402678 | 43403084 | Hypo | cancer_general | CCL28 | chr5 | 43558065 | 43558099 | Hypo | cancer_general | PAIP1 |
| chr5 | 52887899 | 52888047 | Hypo | cancer_general | NDUFS4 | chr5 | 56077938 | 56078065 | Hypo | cancer_general | |
| chr5 | 56467399 | 56467666 | Hypo | cancer_general | GPBP1 | chr5 | 65181732 | 65181778 | Hypo | cancer_general | |
| chr5 | 67569803 | 67569832 | Hypo | literature | PIK3R1 | chr5 | 67588937 | 67589162 | Hypo | literature | PIK3R1 |
| chr5 | 67589598 | 67589627 | Hypo | literature | PIK3R1 | chr5 | 67590431 | 67590460 | Hypo | literature | PIK3R1 |
| chr5 | 67591068 | 67591157 | Hypo | literature | PIK3R1 | chr5 | 68391042 | 68391336 | Hypo | cancer_general | SLC30A5 |
| chr5 | 71106820 | 71107027 | Hypo | head_neck | | chr5 | 72528434 | 72528464 | Hypo | cancer_general | |
| chr5 | 74061571 | 74061786 | Hypo | cancer_general | NSA2, GFM2 | chr5 | 74991793 | 74991908 | Hypo | cancer_general | POC5 |
| chr5 | 76327468 | 76327697 | Hypo | cancer_general | AGGF1 | chr5 | 77655342 | 77655388 | Hypo | cancer_general | SCAMP1, BC039455 |
| chr5 | 78005726 | 78005913 | Hypo | cancer_general | | chr5 | 78039632 | 78039673 | Hypo | head_neck | |
| chr5 | 78910189 | 78910332 | Hypo | cancer_general | | chr5 | 79954097 | 79954169 | Hypo | colorectal | SERINC5 |
| chr5 | 79563425 | 79563643 | Hypo | cancer_general | PAPD4 | chr5 | 79598681 | 79598836 | Hypo | cancer_general | LOC644936 |
| chr5 | 79783240 | 79783421 | Hypo | cancer_general | ZFYVE16, FAM151B | chr5 | 79947584 | 79947707 | Hypo | cancer_general | DHFR, MSH3, MTRNR2L2 |
| chr5 | 82168369 | 82168480 | Hypo | colorectal | | chr5 | 86414242 | 86414297 | Hypo | cancer_general | BC034940, MIR4280 |
| chr5 | 87986547 | 87986581 | Hypo | pancreas | | chr5 | 94889396 | 94889434 | Hypo | cancer_general | ARSK, TTC37 |
| chr5 | 94982042 | 94982225 | Hypo | cancer_general | RFESD, SPATA9 | chr5 | 96114587 | 96114632 | Hypo | breast | ERAP1, CAST |
| chr5 | 111987744 | 111987818 | Hypo | colorectal | | chr5 | 112042844 | 112042873 | Hypo | literature | APC |
| chr5 | 112170808 | 112170837 | Hypo | literature | APC | chr5 | 112175198 | 112175227 | Hypo | literature | APC |
| chr5 | 112175640 | 112175669 | Hypo | literature | APC | chr5 | 112340666 | 112340704 | Hypo | head_neck | DCP2 |
| chr5 | 115154758 | 115154825 | Hypo | cancer_general | ATG12, CDO1 | chr5 | 115176039 | 115176228 | Hypo | cancer_general | ATG12, AP3S1 |
| chr5 | 116143271 | 116143325 | Hypo | hepatobiliary | | chr5 | 120399966 | 120400129 | Hypo | cancer_general | |
| chr5 | 124128410 | 124128497 | Hypo | colorectal | | chr5 | 126231644 | 126231674 | Hypo | ovarian | |
| chr5 | 126245097 | 126245133 | Hypo | pancreas | 3-Mar | chr5 | 127088743 | 127088773 | Hypo | cancer_general | 3-Mar |
| chr5 | 130153448 | 130153623 | Hypo | cancer_general | | chr5 | 131134159 | 131134203 | Hypo | ovarian | |
| chr5 | 133820008 | 133820040 | Hypo | cancer_general | LOC340073, LOC100996485 | chr5 | 133968996 | 133969192 | Hypo | cancer_general | LOC728637, ACSL6, FNIP1 |
| chr5 | 134582864 | 134582894 | Hypo | cancer_general | | chr5 | 137404150 | 137404180 | Hypo | cancer_general | SAR1B |
| chr5 | 137912037 | 137912148 | Hypo | ovarian | | chr5 | 138196197 | 138196408 | Hypo | head_neck | |
| chr5 | 138273817 | 138273854 | Hypo | pancreas | SIL1, CTNNA1 | chr5 | 139454108 | 139454202 | Hypo | ovarian | LRRTM2, CTNNA1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 139779555 | 139779871 | Hypo | cancer_general | ANKHD1, ANKHD1-EIF4EBP3, BC030152 | chr5 | 147003444 | 147003536 | Hypo | cancer_general | JAKMIP2, JAKMIP2-AS1 |
| chr5 | 147326357 | 147326510 | Hypo | cancer_general | SYNPO | chr5 | 149503827 | 149503856 | Hypo | literature | PDGFRB |
| chr5 | 150029147 | 150029245 | Hypo | ovarian | | chr5 | 154030048 | 154030160 | Hypo | cancer_general | |
| chr5 | 154061801 | 154061894 | Hypo | cancer_general | MRPL22, GEMIN5 | chr5 | 154209926 | 154209987 | Hypo | cancer_general | FAXDC2 |
| chr5 | 154318148 | 154318329 | Hypo | cancer_general | | chr5 | 156485385 | 156485415 | Hypo | cancer_general | HAVCR1 |
| chr5 | 156558444 | 156558689 | Hypo | cancer_general | MED7 | chr5 | 156655170 | 156655200 | Hypo | cancer_general | ITK |
| chr5 | 156874257 | 156874308 | Hypo | cancer_general | ADAM19 | chr5 | 157078419 | 157078449 | Hypo | cancer_general | SOX30 |
| chr5 | 157673799 | 157673964 | Hypo | cancer_general | | chr5 | 158524865 | 158524925 | Hypo | cancer_general | AK123543, EBF1 |
| chr5 | 158612981 | 158613074 | Hypo | lung, cancer_general | RNF145 | chr5 | 159437197 | 159437235 | Hypo | cancer_general | TTC1 |
| chr5 | 166865449 | 166865616 | Hypo | cancer_general | TENM2 | chr5 | 168233396 | 168233482 | Hypo | cancer_general | SLIT3 |
| chr5 | 169366082 | 169366201 | Hypo | cancer_general | FAM196B, DOCK2 | chr5 | 169532927 | 169533012 | Hypo | cancer_general | FOXI1 |
| chr5 | 171352123 | 171352153 | Hypo | head_neck | FBXW11 | chr5 | 172354043 | 172354118 | Hypo | ovarian | ERGIC1 |
| chr5 | 172485539 | 172485586 | Hypo | cancer_general | CREBRF, Y_RNA | chr5 | 172672477 | 172672663 | Hypo | cancer_general | |
| chr5 | 174159104 | 174159134 | Hypo | cancer_general | MSX2 | chr5 | 174921456 | 174921629 | Hypo | cancer_general | SFXN1 |
| chr5 | 175790961 | 175790991 | Hypo | ovarian | ARL10, KIAA1191 | chr5 | 175831257 | 175831326 | Hypo | colorectal | CLTB |
| chr5 | 175876388 | 175876504 | Hypo | cancer_general | FAF2 | chr5 | 175971447 | 175971615 | Hypo | cancer_general | CDHR2 |
| chr5 | 175978889 | 175978976 | Hypo | cancer_general | CDHR2 | chr5 | 176295786 | 176295892 | Hypo | hepatobiliary | UNC5A |
| chr5 | 176520166 | 176520195 | Hypo | literature | FGFR4 | chr5 | 176522400 | 176522566 | Hypo | literature | FGFR4 |
| chr5 | 176764100 | 176764169 | Hypo | breast | LMAN2 | chr5 | 177020093 | 177020153 | Hypo | cancer_general | B4GALT7, TMED9 |
| chr5 | 177031167 | 177031197 | Hypo | cancer_general | B4GALT7, TMED9 | chr5 | 177408292 | 177408443 | Hypo | cancer_general | |
| chr5 | 177512244 | 177512377 | Hypo | cancer_general | | chr5 | 177556807 | 177557022 | Hypo | cancer_general | AK127224, N4BP3, RMND5B |
| chr5 | 177579824 | 177580065 | Hypo | cancer_general | NHP2, RMND5B | chr5 | 177644565 | 177644601 | Hypo | colorectal | AGXT2L2, HNRNPAB |
| chr5 | 177713376 | 177713468 | Hypo | cancer_general | | chr5 | 178151333 | 178151363 | Hypo | hepatobiliary | ZNF354A |
| chr5 | 178576356 | 178576499 | Hypo | cancer_general | ADAMTS2 | chr5 | 178655753 | 178655871 | Hypo | cancer_general | ADAMTS2 |
| chr5 | 178781548 | 178781577 | Hypo | literature | ADAMTS2 | chr5 | 178955527 | 178955656 | Hypo | cancer_general | AX747985 |
| chr5 | 178969722 | 178969752 | Hypo | cancer_general | RUFY1 | chr5 | 178978946 | 178978976 | Hypo | cancer_general | RUFY1 |
| chr5 | 179060235 | 179060655 | Hypo | cancer_general | C5orf60 | chr5 | 179098595 | 179098633 | Hypo | cancer_general | CBY3 |
| chr5 | 179214113 | 179214196 | Hypo | cancer_general | LTC4S, MAML1 | chr5 | 179217377 | 179217447 | Hypo | esophageal | LTC4S, MGAT4B, MIR1229 |
| chr5 | 179270584 | 179270748 | Hypo | ovarian | AK095057, C5orf45, SQSTM1 | chr5 | 179553207 | 179553237 | Hypo | cancer_general | RASGEF1C |
| chr5 | 180030654 | 180030700 | Hypo | cancer_general | FLT4 | chr5 | 180047440 | 180047606 | Hypo | cancer_general | FLT4 |
| chr5 | 180326126 | 180326156 | Hypo | cancer_general | BTNL8 | chr5 | 180454232 | 180454334 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 180612346 | 180612376 | Hypo | cancer_general | TRNA_Leu, TRNA_Val, TRNA_Pro, TRNA_Thr, TRIM7 | chr5 | 180629320 | 180629350 | Hypo | cancer_general | TRIM7, TRNA_Ala, TRNA_Lys |
| chr5 | 180636016 | 180636205 | Hypo | cancer_general | TRNA_Ala, TRIM7, TRNA_Val, TRNA_Lys | JH636052.4 | 2022736 | 2022766 | Hypo | cancer_general | |
| HPV16 | 111 | 140 | Hypo | virus | | HPV16 | 367 | 396 | Hypo | virus | |
| HPV16 | 623 | 652 | Hypo | virus | | HPV16 | 879 | 908 | Hypo | virus | |
| HPV16 | 1135 | 1164 | Hypo | virus | | HPV16 | 1391 | 1420 | Hypo | virus | |
| HPV16 | 1647 | 1676 | Hypo | virus | | HPV16 | 1903 | 1932 | Hypo | virus | |
| HPV16 | 2159 | 2188 | Hypo | virus | | HPV16 | 2415 | 2444 | Hypo | virus | |
| HPV16 | 2671 | 2700 | Hypo | virus | | HPV16 | 2927 | 2956 | Hypo | virus | |
| HPV16 | 3183 | 3212 | Hypo | virus | | HPV16 | 3439 | 3468 | Hypo | virus | |
| HPV16 | 3695 | 3724 | Hypo | virus | | HPV16 | 3951 | 3980 | Hypo | virus | |
| HPV16 | 4207 | 4236 | Hypo | virus | | HPV16 | 4463 | 4492 | Hypo | virus | |
| HPV16 | 4719 | 4748 | Hypo | virus | | HPV16 | 4975 | 5004 | Hypo | virus | |
| HPV16 | 5231 | 5260 | Hypo | virus | | HPV16 | 5487 | 5516 | Hypo | virus | |
| HPV16 | 5743 | 5772 | Hypo | virus | | HPV16 | 5999 | 6028 | Hypo | virus | |
| HPV16 | 6255 | 6284 | Hypo | virus | | HPV16 | 6511 | 6540 | Hypo | virus | |
| HPV16 | 6767 | 6796 | Hypo | virus | | HPV16 | 7023 | 7052 | Hypo | virus | |
| HPV16 | 7279 | 7308 | Hypo | virus | | HPV16 | 7535 | 7564 | Hypo | virus | |
| chr13 | 20451144 | 20451360 | Hypo | cancer_general | | chr13 | 21713233 | 21713513 | Hypo | cancer_general | SAP18 |
| chr13 | 23653781 | 23653813 | Hypo | hepatobiliary | | chr13 | 24099683 | 24099713 | Hypo | hepatobiliary | ATP8A2 |
| chr13 | 25668799 | 25668829 | Hypo | cancer_general | PABPC3 | chr13 | 26340608 | 26340755 | Hypo | cancer_general | |
| chr13 | 27699893 | 27699981 | Hypo | cancer_general | USP12 | chr13 | 28239909 | 28240164 | Hypo | breast | |
| chr13 | 28589765 | 28589794 | Hypo | literature | FLT3 | chr13 | 28592605 | 28592658 | Hypo | literature | FLT3 |
| chr13 | 28601345 | 28601374 | Hypo | literature | FLT3 | chr13 | 28602326 | 28602355 | Hypo | literature | FLT3 |
| chr13 | 28608233 | 28608355 | Hypo | cancer_general | PAN3-AS1, PAN3 | chr13 | 28610123 | 28610152 | Hypo | hepatobiliary | |
| chr13 | 28706016 | 28706140 | Hypo | cancer_general | | chr13 | 29112395 | 29112444 | Hypo | hepatobiliary | |
| chr13 | 30141688 | 30141718 | Hypo | cancer_general | SLC7A1 | chr13 | 30707569 | 30707599 | Hypo | cancer_general | |
| chr13 | 31185432 | 31185548 | Hypo | blood | USPL1 | chr13 | 31742953 | 31743177 | Hypo | cancer_general | HSPH1 |
| chr13 | 36269480 | 36269509 | Hypo | literature | | chr13 | 36541300 | 36541329 | Hypo | literature | |
| chr13 | 36553399 | 36553428 | Hypo | literature | | chr13 | 36588100 | 36588129 | Hypo | literature | |
| chr13 | 36909206 | 36909236 | Hypo | hepatobiliary | SPG20 | chr13 | 37643942 | 37644005 | Hypo | cancer_general | LHFP |
| chr13 | 38402239 | 38402268 | Hypo | literature | TRPC4 | chr13 | 40000498 | 40000528 | Hypo | hepatobiliary | ELF1, SUGT1P3 |
| chr13 | 41346048 | 41346088 | Hypo | cancer_general | MRPS31 | chr13 | 41496324 | 41496478 | Hypo | cancer_general | DNAJC15 CPB2, CPB2-AS1 |
| chr13 | 41884500 | 41884688 | Hypo | cancer_general | NAA16 | chr13 | 43620862 | 43621006 | Hypo | colorectal | |
| chr13 | 45905088 | 45905264 | Hypo | cancer_general | TPT1, SNORA31, DL489966, D28408 | chr13 | 46649031 | 46649141 | Hypo | pancreas | |
| chr13 | 46660839 | 46660869 | Hypo | cancer_general | CPB2, CPB2-AS1 | chr13 | 47407767 | 47407796 | Hypo | literature | HTR2A |
| chr13 | 47472315 | 47472344 | Hypo | literature | HTR2A | chr13 | 47526030 | 47526182 | Hypo | cancer_general | |
| chr13 | 48478576 | 48478605 | Hypo | literature | | chr13 | 48667877 | 48667907 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 50266473 | 50266573 | Hypo | cancer_general | KPNA3, EBPL | chr13 | 50367946 | 50368123 | Hypo | cancer_general | KPNA3 |
| chr13 | 50421504 | 50421696 | Hypo | esophageal | | chr13 | 50639705 | 50639799 | Hypo | head_neck | DLEU2 |
| chr13 | 52270175 | 52270175 | Hypo | cancer_general | WDFY2 | chr13 | 52265068 | 52565194 | Hypo | cancer_general | |
| chr13 | 52580318 | 52580369 | Hypo | cancer_general | UTP14C, ALG11 | chr13 | 55146522 | 55146551 | Hypo | literature | |
| chr13 | 55373897 | 55373926 | Hypo | literature | | chr13 | 55628658 | 55628687 | Hypo | literature | |
| chr13 | 56762456 | 56762485 | Hypo | literature | | chr13 | 57714539 | 57714568 | Hypo | literature | PRR20D |
| chr13 | 58892774 | 58892803 | Hypo | literature | | chr13 | 59531686 | 59531715 | Hypo | literature | |
| chr13 | 62132346 | 62132375 | Hypo | literature | | chr13 | 64650200 | 64650229 | Hypo | literature | |
| chr13 | 65532258 | 65532287 | Hypo | literature | | chr13 | 66697959 | 66698124 | Hypo | hepatobiliary | |
| chr13 | 67196371 | 67196400 | Hypo | literature | U7 | chr13 | 67197158 | 67197187 | Hypo | literature | U7 |
| chr13 | 68488923 | 68488952 | Hypo | literature | | chr13 | 68682015 | 68682044 | Hypo | literature | |
| chr13 | 68745282 | 68745311 | Hypo | literature | | chr13 | 69796842 | 69796871 | Hypo | literature | |
| chr13 | 71498386 | 71498415 | Hypo | literature | | chr13 | 73184723 | 73184752 | Hypo | literature | |
| chr13 | 73336049 | 73336078 | Hypo | literature | DIS3, BORA | chr13 | 73619660 | 73619784 | Hypo | colorectal | KLF5 |
| chr13 | 76440730 | 76440760 | Hypo | colorectal | C13orf45, AK123459 | chr13 | 76869421 | 76869450 | Hypo | literature | |
| chr13 | 77553779 | 77553809 | Hypo | cancer_general | | chr13 | 79693095 | 79693124 | Hypo | literature | |
| chr13 | 79993101 | 79993142 | Hypo | lung | RBM26-AS1 | chr13 | 87731371 | 87731400 | Hypo | literature | |
| chr13 | 88629123 | 88629152 | Hypo | literature | | chr13 | 88788883 | 88788912 | Hypo | literature | |
| chr13 | 88997906 | 88997935 | Hypo | literature | | chr13 | 89815436 | 89815465 | Hypo | literature | |
| chr13 | 90015503 | 90015532 | Hypo | literature | | chr13 | 90015897 | 90015926 | Hypo | literature | |
| chr13 | 91755723 | 91755837 | Hypo | hepatobiliary | | chr13 | 91948489 | 91948519 | Hypo | cancer_general | |
| chr13 | 93859304 | 93859333 | Hypo | literature | | chr13 | 94107209 | 94107238 | Hypo | literature | GPC6 |
| chr13 | 95086143 | 95086172 | Hypo | head_neck | | chr13 | 96031705 | 96031815 | Hypo | cancer_general | |
| chr13 | 96177285 | 96177315 | Hypo | | DCT CLDN10-AS1, CLDN10 | chr13 | 97761876 | 97761925 | Hypo | pancreas | |
| chr13 | 99851676 | 99851706 | Hypo | cancer_general | UBAC2-AS1, UBAC2, 7SK | chr13 | 102197373 | 102197408 | Hypo | cancer_general | ITGBL1 |
| chr13 | 103821419 | 103821448 | Hypo | literature | FAM155A ABHD13, LIG4 | chr13 | 105484285 | 105484314 | Hypo | literature | |
| chr13 | 107827301 | 107827331 | Hypo | hepatobiliary | | chr13 | 108816328 | 108816383 | Hypo | cancer_general | |
| chr13 | 108869613 | 108869830 | Hypo | cancer_general | | chr13 | 110434451 | 110434593 | Hypo | cancer_general | IRS2 |
| chr13 | 111278255 | 111278426 | Hypo | cancer_general | CARKD | chr13 | 111363787 | 111363972 | Hypo | cancer_general | |
| chr13 | 112272991 | 112273088 | Hypo | cancer_general | | chr13 | 112712499 | 112712582 | Hypo | cancer_general | ING1, DJ031140, CARS2 |
| chr13 | 112758274 | 112758426 | Hypo | cancer_general | AK055145 | chr13 | 113598618 | 113598851 | Hypo | cancer_general | SOX1 BC035340 |
| chr13 | 113938542 | 113938603 | Hypo | cancer_general | | chr13 | 113985679 | 113986053 | Hypo | cancer_general | GRTP1, LAMP1 |
| chr13 | 114055983 | 114056137 | Hypo | literature, cancer_general | | chr13 | 114060064 | 114060333 | Hypo | cancer_general | |
| chr13 | 114074768 | 114074853 | Hypo | cancer_general | ADPRHL1 DCUN1D2 | chr13 | 114082984 | 114083014 | Hypo | breast | ADPRHL1 |
| chr13 | 114123168 | 114123291 | Hypo | cancer_general | | chr13 | 114189737 | 114189809 | Hypo | colorectal | TMCO3 |

TABLE 11-continued

| chr | Start | Stop | Hypo/hyper | classification | annotation |
|---|---|---|---|---|---|
| chr13 | 114221622 | 114221652 | Hypo | cancer_general | |
| chr13 | 114479404 | 114479434 | Hypo | cancer_general | TMEM255B |
| chr13 | 114568046 | 114568076 | Hypo | cancer_general | LOC100506394 |
| chr13 | 114766270 | 114766300 | Hypo | ovarian | RASA3 |
| chr13 | 114807617 | 114807815 | Hypo | head_neck, cancer_general | RASA3 |
| chr13 | 114862308 | 114862368 | Hypo | cancer_general | |
| EBV-B95-8 | 967 | 996 | Hypo | virus | |
| EBV-B95-8 | 4234 | 4263 | Hypo | virus | |
| EBV-B95-8 | 6553 | 6582 | Hypo | virus | |
| EBV-B95-8 | 13471 | 13500 | Hypo | virus | |
| EBV-B95-8 | 48222 | 48251 | Hypo | virus | |
| EBV-B95-8 | 53561 | 53590 | Hypo | virus | |
| EBV-B95-8 | 54778 | 54807 | Hypo | virus | |
| EBV-B95-8 | 55893 | 55922 | Hypo | virus | |
| EBV-B95-8 | 58227 | 58256 | Hypo | virus | |
| EBV-B95-8 | 59581 | 59610 | Hypo | virus | |
| EBV-B95-8 | 60877 | 60906 | Hypo | virus | |
| EBV-B95-8 | 62302 | 62331 | Hypo | virus | |
| EBV-B95-8 | 63178 | 63207 | Hypo | virus | |
| EBV-B95-8 | 63935 | 63964 | Hypo | virus | |
| EBV-B95-8 | 66726 | 66755 | Hypo | virus | |
| EBV-B95-8 | 67857 | 67886 | Hypo | virus | |
| EBV-B95-8 | 69798 | 69827 | Hypo | virus | |
| EBV-B95-8 | 70839 | 70868 | Hypo | virus | |
| EBV-B95-8 | 72204 | 72233 | Hypo | virus | |
| EBV-B95-8 | 72983 | 73012 | Hypo | virus | |
| EBV-B95-8 | 74304 | 74333 | Hypo | virus | |
| EBV-B95-8 | 74978 | 75007 | Hypo | virus | |
| EBV-B95-8 | 77784 | 77813 | Hypo | virus | |
| EBV-B95-8 | 80289 | 80318 | Hypo | virus | |
| EBV-B95-8 | 81198 | 81227 | Hypo | virus | |
| EBV-B95-8 | 81888 | 81917 | Hypo | virus | |
| EBV-B95-8 | 82703 | 82732 | Hypo | virus | |
| EBV-B95-8 | 85345 | 85374 | Hypo | virus | |
| EBV-B95-8 | 87104 | 87133 | Hypo | virus | |
| EBV-B95-8 | 90915 | 90944 | Hypo | virus | |
| EBV-B95-8 | 94071 | 94100 | Hypo | virus | |
| EBV-B95-8 | 95084 | 95113 | Hypo | virus | |
| EBV-B95-8 | 98245 | 98274 | Hypo | virus | |
| EBV-B95-8 | 100235 | 100264 | Hypo | virus | |
| EBV-B95-8 | 102716 | 102745 | Hypo | virus | |
| EBV-B95-8 | 105019 | 105048 | Hypo | virus | |
| EBV-B95-8 | 107231 | 107260 | Hypo | virus | |
| EBV-B95-8 | 108370 | 108399 | Hypo | virus | |
| EBV-B95-8 | 110250 | 110279 | Hypo | virus | |
| EBV-B95-8 | 111690 | 111719 | Hypo | virus | |
| EBV-B95-8 | 114429 | 114458 | Hypo | virus | |
| EBV-B95-8 | 115006 | 115035 | Hypo | virus | |
| chr13 | 114304565 | 114304927 | Hypo | cancer_general | ATP4B, TFDP1 |
| chr13 | 114498017 | 114498260 | Hypo | cancer_general | TMEM255B |
| chr13 | 114748342 | 114748638 | Hypo | cancer_general | RASA3 |
| chr13 | 114780561 | 114781061 | Hypo | cancer_general | RASA3 |
| chr13 | 114855635 | 114855669 | Hypo | cancer_general | |
| chr13 | 114961823 | 114961933 | Hypo | | |
| EBV-B95-8 | 3766 | 3795 | Hypo | virus | |
| EBV-B95-8 | 5326 | 5355 | Hypo | virus | |
| EBV-B95-8 | 8800 | 8829 | Hypo | virus | |
| EBV-B95-8 | 46577 | 46606 | Hypo | virus | |
| EBV-B95-8 | 52842 | 52871 | Hypo | virus | |
| EBV-B95-8 | 54377 | 54406 | Hypo | virus | |
| EBV-B95-8 | 55067 | 55096 | Hypo | virus | |
| EBV-B95-8 | 56735 | 56764 | Hypo | virus | |
| EBV-B95-8 | 58926 | 58955 | Hypo | virus | |
| EBV-B95-8 | 60099 | 60128 | Hypo | virus | |
| EBV-B95-8 | 61319 | 61348 | Hypo | virus | |
| EBV-B95-8 | 62840 | 62869 | Hypo | virus | |
| EBV-B95-8 | 63601 | 63630 | Hypo | virus | |
| EBV-B95-8 | 64590 | 64619 | Hypo | virus | |
| EBV-B95-8 | 67486 | 67515 | Hypo | virus | |
| EBV-B95-8 | 69228 | 69257 | Hypo | virus | |
| EBV-B95-8 | 70439 | 70468 | Hypo | virus | |
| EBV-B95-8 | 71938 | 71967 | Hypo | virus | |
| EBV-B95-8 | 72535 | 72564 | Hypo | virus | |
| EBV-B95-8 | 73950 | 73979 | Hypo | virus | |
| EBV-B95-8 | 74689 | 74718 | Hypo | virus | |
| EBV-B95-8 | 75256 | 75285 | Hypo | virus | |
| EBV-B95-8 | 79618 | 79647 | Hypo | virus | |
| EBV-B95-8 | 80704 | 80733 | Hypo | virus | |
| EBV-B95-8 | 81629 | 81658 | Hypo | virus | |
| EBV-B95-8 | 82225 | 82254 | Hypo | virus | |
| EBV-B95-8 | 83438 | 83467 | Hypo | virus | |
| EBV-B95-8 | 86299 | 86328 | Hypo | virus | |
| EBV-B95-8 | 89959 | 89988 | Hypo | virus | |
| EBV-B95-8 | 92531 | 92560 | Hypo | virus | |
| EBV-B95-8 | 94731 | 94760 | Hypo | virus | |
| EBV-B95-8 | 97482 | 97511 | Hypo | virus | |
| EBV-B95-8 | 99224 | 99253 | Hypo | virus | |
| EBV-B95-8 | 101009 | 101038 | Hypo | virus | |
| EBV-B95-8 | 104004 | 104033 | Hypo | virus | |
| EBV-B95-8 | 105284 | 105313 | Hypo | virus | |
| EBV-B95-8 | 108023 | 108052 | Hypo | virus | |
| EBV-B95-8 | 109086 | 109115 | Hypo | virus | |
| EBV-B95-8 | 110626 | 110655 | Hypo | virus | |
| EBV-B95-8 | 112112 | 112141 | Hypo | virus | |
| EBV-B95-8 | 114749 | 114778 | Hypo | virus | |
| EBV-B95-8 | 115597 | 115626 | Hypo | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| EBV-B95-8 | 116382 | 116411 | Hypo | virus | | EBV-B95-8 | 116649 | 116678 | Hypo | virus | |
| EBV-B95-8 | 118647 | 118676 | Hypo | virus | | EBV-B95-8 | 119542 | 119571 | Hypo | virus | |
| EBV-B95-8 | 120350 | 120379 | Hypo | virus | | EBV-B95-8 | 121382 | 121411 | Hypo | virus | |
| EBV-B95-8 | 123037 | 123066 | Hypo | virus | | EBV-B95-8 | 123570 | 123599 | Hypo | virus | |
| EBV-B95-8 | 124913 | 124942 | Hypo | virus | | EBV-B95-8 | 125376 | 125405 | Hypo | virus | |
| EBV-B95-8 | 125805 | 125834 | Hypo | virus | | EBV-B95-8 | 126337 | 126366 | Hypo | virus | |
| EBV-B95-8 | 127493 | 127522 | Hypo | virus | | EBV-B95-8 | 127905 | 127934 | Hypo | virus | |
| EBV-B95-8 | 128805 | 128834 | Hypo | virus | | EBV-B95-8 | 130244 | 130273 | Hypo | virus | |
| EBV-B95-8 | 130690 | 130719 | Hypo | virus | | EBV-B95-8 | 131603 | 131632 | Hypo | virus | |
| EBV-B95-8 | 134325 | 134354 | Hypo | virus | | EBV-B95-8 | 135032 | 135061 | Hypo | virus | |
| EBV-B95-8 | 135599 | 135628 | Hypo | virus | | EBV-B95-8 | 136148 | 136177 | Hypo | virus | |
| EBV-B95-8 | 136680 | 136709 | Hypo | virus | | EBV-B95-8 | 137805 | 137834 | Hypo | virus | |
| EBV-B95-8 | 138375 | 138404 | Hypo | virus | | EBV-B95-8 | 139745 | 139774 | Hypo | virus | |
| EBV-B95-8 | 140610 | 140639 | Hypo | virus | | EBV-B95-8 | 141137 | 141166 | Hypo | virus | |
| EBV-B95-8 | 142290 | 142319 | Hypo | virus | | EBV-B95-8 | 142763 | 142792 | Hypo | virus | |
| EBV-B95-8 | 143078 | 143107 | Hypo | virus | | EBV-B95-8 | 144318 | 144347 | Hypo | virus | |
| EBV-B95-8 | 145216 | 145245 | Hypo | virus | | EBV-B95-8 | 145638 | 145667 | Hypo | virus | |
| EBV-B95-8 | 147044 | 147073 | Hypo | virus | | EBV-B95-8 | 148404 | 148433 | Hypo | virus | |
| EBV-B95-8 | 150099 | 150128 | Hypo | virus | | EBV-B95-8 | 150443 | 150472 | Hypo | virus | |
| EBV-B95-8 | 152230 | 152259 | Hypo | virus | | EBV-B95-8 | 153127 | 153156 | Hypo | virus | |
| EBV-B95-8 | 153468 | 153497 | Hypo | virus | | EBV-B95-8 | 153800 | 153829 | Hypo | virus | |
| EBV-B95-8 | 154204 | 154233 | Hypo | virus | | EBV-B95-8 | 156501 | 156530 | Hypo | virus | |
| EBV-B95-8 | 156773 | 156802 | Hypo | virus | | EBV-B95-8 | 157345 | 157374 | Hypo | virus | |
| EBV-B95-8 | 159211 | 159240 | Hypo | virus | | EBV-B95-8 | 159561 | 159590 | Hypo | virus | |
| EBV-B95-8 | 161193 | 161222 | Hypo | virus | | EBV-B95-8 | 161698 | 161727 | Hypo | virus | |
| EBV-B95-8 | 162343 | 162372 | Hypo | virus | | EBV-B95-8 | 163798 | 163827 | Hypo | virus | |
| EBV-B95-8 | 164471 | 164500 | Hypo | virus | | EBV-B95-8 | 165234 | 165263 | Hypo | virus | |
| EBV-B95-8 | 166280 | 166309 | Hypo | virus | | EBV-B95-8 | 167347 | 167376 | Hypo | virus | |
| EBV-B95-8 | 167600 | 167629 | Hypo | virus | | EBV-B95-8 | 167942 | 167971 | Hypo | virus | |
| EBV-B95-8 | 168551 | 168580 | Hypo | virus | | EBV-B95-8 | 171304 | 171333 | Hypo | virus | |
| HBV | 111 | 140 | Hypo | virus | | HBV | 381 | 410 | Hypo | virus | |
| HBV | 651 | 680 | Hypo | virus | | HBV | 921 | 950 | Hypo | virus | |
| HBV | 1191 | 1220 | Hypo | virus | | HBV | 1461 | 1490 | Hypo | virus | |
| HBV | 1731 | 1760 | Hypo | virus | | HBV | 2001 | 2030 | Hypo | virus | |
| HBV | 2271 | 2300 | Hypo | virus | | HBV | 2541 | 2570 | Hypo | virus | |
| HBV | 2811 | 2840 | Hypo | virus | | chrX | 3631506 | 3631633 | Hypo | breast | PRKX INE2, CA5B, ZRSR2 |
| chrX | 3746612 | 3746642 | Hypo | head_neck | TRNA_Ile, LOC389906 | chrX | 15807465 | 15807693 | Hypo | cancer_general | RPS6KA3, SCARNA9L, EIF1AX |
| chrX | 20148710 | 20148739 | Hypo | literature | SCARNA9L, EIF1AX | chrX | 20160594 | 20160914 | Hypo | cancer_general | RBM10 |
| chrX | 44730179 | 44730271 | Hypo | cancer_general | KDM6A | chrX | 47039370 | 47039399 | Hypo | literature | SYN1, ARAF |
| chrX | 47426106 | 47426144 | Hypo | literature | SYN1, ARAF | chrX | 47426780 | 47426821 | Hypo | literature | |
| chrX | 66931448 | 66931477 | Hypo | literature | AR | chrX | 66937356 | 66937385 | Hypo | literature | AR |
| chrX | 66943529 | 66943567 | Hypo | literature | AR | chrX | 70339239 | 70339268 | Hypo | literature | MED12, IL2RG |
| chr15 | 100228394 | 100228431 | Hypo | head_neck | ARL13A | chr15 | 22822348 | 22822488 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 23035709 | 23035781 | Hypo | cancer_general | NIPA1, NIPA2 | chr15 | 23162337 | 23162372 | Hypo | cancer_general | |
| chr15 | 23273146 | 23273330 | Hypo | cancer_general | HERC2P2, JB175342, DQ572979 | chr15 | 23692316 | 23692453 | Hypo | cancer_general | LOC283685, GOLGA6L2 |
| chr15 | 29452432 | 29452462 | Hypo | hepatobiliary | FAM189A1 | chr15 | 31455370 | 31455485 | Hypo | cancer_general | |
| chr15 | 33879242 | 33879272 | Hypo | cancer_general | RYR3 | chr15 | 34630515 | 34630544 | Hypo | tcga | NOP10, NUTM1, SLC12A6 |
| chr15 | 34630818 | 34630865 | Hypo | cancer_general | NOP10, NUTM1, SLC12A6 | chr15 | 34879708 | 34879866 | Hypo | cancer_general | |
| chr15 | 35310631 | 35310868 | Hypo | literature | KNSTRN | chr15 | 40671495 | 40671620 | Hypo | ovarian | KNSTRN, DISP2 |
| chr15 | 40675092 | 40675121 | Hypo | literature | RPUSD2, C15orf57 | chr15 | 40782219 | 40782249 | Hypo | breast | |
| chr15 | 40856224 | 40856254 | Hypo | cancer_general | | chr15 | 40877650 | 40877714 | Hypo | cancer_general | TRNA_Ser, CASC5 |
| chr15 | 41165245 | 41165700 | Hypo | cancer_general | RHOV | chr15 | 41541844 | 41541874 | Hypo | cancer_general | CHP1 |
| chr15 | 41693679 | 41693794 | Hypo | cancer_general | NDUFAF1 | chr15 | 41708225 | 41708305 | Hypo | cancer_general | RTF1 |
| chr15 | 41732398 | 41732471 | Hypo | breast | RTF1 | chr15 | 41835548 | 41835720 | Hypo | cancer_general | |
| chr15 | 42749733 | 42749899 | Hypo | literature | ZNF106 | chr15 | 42866975 | 42867049 | Hypo | cancer_general | |
| chr15 | 43551059 | 43551196 | Hypo | esophageal | | chr15 | 44037568 | 44037699 | Hypo | cancer_general | STARD9, HAUS2 PDIA3, CATSPER2P1 |
| chr15 | 45444061 | 45444141 | Hypo | ovarian | DUOX1 | chr15 | 46021437 | 46021467 | Hypo | pancreas | |
| chr15 | 50450454 | 50450574 | Hypo | head_neck | | chr15 | 50464583 | 50464622 | Hypo | cancer_general | SLC27A2 |
| chr15 | 51146606 | 51146636 | Hypo | cancer_general | AK091906 | chr15 | 52000818 | 52000937 | Hypo | cancer_general | SCG3 |
| chr15 | 54642236 | 54642352 | Hypo | cancer_general | UNC13C | chr15 | 55452761 | 55452993 | Hypo | cancer_general | |
| chr15 | 55610440 | 55610698 | Hypo | literature, cancer_general | PIGB, HP06981 | chr15 | 55699089 | 55699164 | Hypo | cancer_general | FLJ27352, DYX1C1, DYX1C1-CCPG1 |
| chr15 | 55806758 | 55806900 | Hypo | cancer_general | DYX1C1, unknown, FAM63B | chr15 | 56832508 | 56832546 | Hypo | cancer_general | BC037892 |
| chr15 | 59158488 | 59158537 | Hypo | cancer_general | | chr15 | 59158781 | 59158848 | Hypo | cancer_general | FAM63B, unknown |
| chr15 | 59950198 | 59950363 | Hypo | cancer_general | BNIP2, GTF2A2 | chr15 | 60084984 | 60085014 | Hypo | cancer_general | |
| chr15 | 60705106 | 60705204 | Hypo | breast | NARG2 | chr15 | 64109724 | 64109788 | Hypo | cancer_general | HERC1 |
| chr15 | 64618655 | 64618813 | Hypo | cancer_general | CSNK1G1 | chr15 | 64649481 | 64649553 | Hypo | cancer_general | KIAA0101, CSNK1G1 |
| chr15 | 65118954 | 65118984 | Hypo | cancer_general | PIF1 | chr15 | 65119265 | 65119295 | Hypo | cancer_general | PIF1 |
| chr15 | 65119499 | 65119632 | Hypo | cancer_general | PIF1 | chr15 | 65436137 | 65436213 | Hypo | ovarian | CLPX, PDCD7 |
| chr15 | 65685591 | 65685708 | Hypo | cancer_general | IGDCC4 | chr15 | 65823926 | 65824103 | Hypo | cancer_general | PTPLAD1 |
| chr15 | 65826189 | 65826359 | Hypo | cancer_general | PTPLAD1 | chr15 | 65862004 | 65862121 | Hypo | lung, cancer_general | VWA9, PTPLAD1 |
| chr15 | 66113240 | 66113270 | Hypo | head_neck | | chr15 | 66649915 | 66649945 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 66722409 | 66722498 | Hypo | literature | MAP2K1 | chr15 | 66729148 | 66729177 | Hypo | literature | MAP2K1 |
| chr15 | 66774117 | 66774203 | Hypo | literature | SNAPC5, MAP2K1 | chr15 | 66789220 | 66789321 | Hypo | cancer_general | SNAPC5, MAP2K1, RPL4, SNORD18C, SNORD18B, SNORD16, SNORD18A, ZWILCH |
| chr15 | 66963816 | 66963871 | Hypo | cancer_general | hCG_2003567 | chr15 | 67146145 | 67146431 | Hypo | cancer_general | BX538221 |
| chr15 | 67545536 | 67545566 | Hypo | cancer_general | IQCH, AAGAB | chr15 | 72411929 | 72412176 | Hypo | cancer_general | SENP8, MYO9A |
| chr15 | 72743741 | 72743796 | Hypo | cancer_general |  | chr15 | 72779757 | 72779873 | Hypo | cancer_general | HIGD2B, BBS4 |
| chr15 | 74686021 | 74686051 | Hypo | cancer_general |  | chr15 | 74818772 | 74818806 | Hypo | pancreas |  |
| chr15 | 74903896 | 74903926 | Hypo | cancer_general | AK095335, CLK3 | chr15 | 74906463 | 74906493 | Hypo | cancer_general | CLK3, AK095335 |
| chr15 | 75205413 | 75205481 | Hypo | cancer_general | COX5A, FAM219B | chr15 | 75412459 | 75412714 | Hypo | cancer_general |  |
| chr15 | 77448873 | 77449001 | Hypo | cancer_general | PEAK1 | chr15 | 78501806 | 78501942 | Hypo | cancer_general | ACSBG1 |
| chr15 | 78595791 | 78596218 | Hypo | cancer_general | WDR61 | chr15 | 78859435 | 78859603 | Hypo | cancer_general | CHRNA5 |
| chr15 | 79151898 | 79152007 | Hypo | cancer_general | TRNA_Lys | chr15 | 80216803 | 80216884 | Hypo | cancer_general | C15orf37, ST20 |
| chr15 | 83314048 | 83314106 | Hypo | cancer_general | LOC283692 | chr15 | 83622512 | 83622565 | Hypo | ovarian | BC044934, HOMER2 |
| chr15 | 83655843 | 83655934 | Hypo | cancer_general | C15orf40, FAM103A1, BC044934 | chr15 | 83866523 | 83866559 | Hypo | cancer_general | HDGFRP3 |
| chr15 | 84711204 | 84711367 | Hypo | cancer_general |  | chr15 | 85142994 | 85143054 | Hypo | cancer_general | ZSCAN2 |
| chr15 | 85886518 | 85886604 | Hypo | cancer_general |  | chr15 | 86002524 | 86002690 | Hypo | cancer_general | AKAP13 |
| chr15 | 90631823 | 90631948 | Hypo | literature | IDH2 | chr15 | 90667461 | 90667586 | Hypo | colorectal |  |
| chr15 | 90703262 | 90703345 | Hypo | cancer_general |  | chr15 | 90755916 | 90756079 | Hypo | cancer_general | SEMA4B |
| chr15 | 93158592 | 93158739 | Hypo | cancer_general | FAM174B, DQ589911, DQ571124, DQ574028, DQ593762 | chr15 | 93350668 | 93350698 | Hypo | lung |  |
| chr15 | 93364552 | 93364624 | Hypo | cancer_general |  | chr15 | 94347602 | 94347632 | Hypo | cancer_general | BC037497 |
| chr15 | 97006372 | 97006533 | Hypo | cancer_general |  | chr15 | 98634851 | 98634949 | Hypo | cancer_general |  |
| chr15 | 98776762 | 98776792 | Hypo | cancer_general |  | chr15 | 99254040 | 99254208 | Hypo | hepatobiliary | IGF1R |
| chr15 | 99295692 | 99295749 | Hypo | cancer_general | IGF1R | chr15 | 99346861 | 99347040 | Hypo | cancer_general, pancreas |  |
| chr15 | 99354999 | 99355041 | Hypo | cancer_general |  | chr15 | 99453230 | 99453440 | Hypo | hepatobiliary | IGF1R, AF020763 |
| chr15 | 99456299 | 99456329 | Hypo | hepatobiliary | IGF1R | chr15 | 99497059 | 99497132 | Hypo | hepatobiliary |  |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 100274325 | 100274385 | Hypo | cancer_general | LYSMD4 | chr15 | 100339980 | 100340010 | Hypo | ovarian | DJ031154, DQ590616, DQ571121, DQ575742, DQ595494, DNM1P46, DQ575741 |
| chr15 | 101818327 | 101818357 | Hypo | cancer_general | VIMP, SNRPA1 | chr15 | 102115873 | 102115905 | Hypo | cancer_general | |
| chr15 | 102193587 | 102193713 | Hypo | cancer_general | TARSL2, TM2D3 | NW_001838016.1_818233-828058 | 6174 | 6313 | Hypo | cancer_general | |
| chr12 | 1650475 | 1650577 | Hypo | cancer_general | | chr12 | 2046104 | 2046134 | Hypo | cancer_general | DCP1B, LINC00940 |
| chr12 | 2403658 | 2403714 | Hypo | cancer_general | CACNA1C-IT3 | chr12 | 2566053 | 2566247 | Hypo | cancer_general | |
| chr12 | 2595199 | 2595339 | Hypo | cancer_general | | chr12 | 2964465 | 2964577 | Hypo | cancer_general | FOXM1, LOC100507424 |
| chr12 | 4213973 | 4214157 | Hypo | cancer_general | | chr12 | 4231674 | 4231767 | Hypo | cancer_general | CCND2 |
| chr12 | 4274271 | 4274409 | Hypo | pancreas | | chr12 | 4323835 | 4323912 | Hypo | cancer_general | CCND2 |
| chr12 | 4362436 | 4362471 | Hypo | cancer_general | | chr12 | 4379357 | 4379491 | Hypo | pancreas | |
| chr12 | 4392883 | 4392922 | Hypo | cancer_general | CCND2 | chr12 | 4405589 | 4405619 | Hypo | cancer_general | FGF6 |
| chr12 | 4431271 | 4431301 | Hypo | cancer_general | C12orf5 | chr12 | 4554801 | 4554831 | Hypo | cancer_general | SCNN1A |
| chr12 | 5840200 | 5840363 | Hypo | cancer_general | ANO2 | chr12 | 6473721 | 6473762 | Hypo | cancer_general | CHD4, AK096395, NOP2 |
| chr12 | 6483615 | 6483756 | Hypo | cancer_general | LITBR, SCNN1A | chr12 | 6678158 | 6678203 | Hypo | cancer_general | |
| chr12 | 7403914 | 7404060 | Hypo | cancer_general | NANOGP1 | chr12 | 7559160 | 7559307 | Hypo | cancer_general | CD163L1 |
| chr12 | 8036526 | 8036634 | Hypo | cancer_general | | chr12 | 8122523 | 8122628 | Hypo | cancer_general | |
| chr12 | 8127140 | 8127140 | Hypo | cancer_general | | chr12 | 8127565 | 8127595 | Hypo | hepatobiliary | |
| chr12 | 8139203 | 8139233 | Hypo | cancer_general | | chr12 | 8163573 | 8163603 | Hypo | cancer_general | |
| chr12 | 8180999 | 8181065 | Hypo | ovarian | FOXJ2 | chr12 | 8808599 | 8808709 | Hypo | cancer_general | MFAP5 |
| chr12 | 8975182 | 8975361 | Hypo | cancer_general | A2ML1 | chr12 | 9916313 | 9916343 | Hypo | cancer_general | CD69 |
| chr12 | 10085916 | 10085948 | Hypo | cancer_general | CLEC2A | chr12 | 10363278 | 10363607 | Hypo | cancer_general | GABARAPL1 |
| chr12 | 10772771 | 10772896 | Hypo | hepatobiliary | STYK1, MAGOHB | chr12 | 12456859 | 12456889 | Hypo | pancreas | |
| chr12 | 12504616 | 12504850 | Hypo | cancer_general | LOH12CR2, LOH12CR1 | chr12 | 12848390 | 12848556 | Hypo | cancer_general | GPR19 |
| chr12 | 13036048 | 13036078 | Hypo | cancer_general | GPRC5A, RPL13AP20 | chr12 | 13055966 | 13055996 | Hypo | pancreas | GPRC5A |
| chr12 | 14719937 | 14719967 | Hypo | cancer_general | PLBD1 | chr12 | 14818824 | 14818867 | Hypo | cancer_general | GUCY2C |
| chr12 | 21833068 | 21833265 | Hypo | cancer_general | | chr12 | 22698063 | 22698110 | Hypo | cancer_general | C2CD5 |
| chr12 | 23229390 | 23229420 | Hypo | cancer_general | AK094733 | chr12 | 25362824 | 25362853 | Hypo | literature | LYRM5, KRAS |
| chr12 | 25368463 | 25368492 | Hypo | literature | KRAS | chr12 | 25378543 | 25378662 | Hypo | literature | KRAS |
| chr12 | 25380231 | 25380299 | Hypo | literature | KRAS | chr12 | 25398203 | 25398319 | Hypo | literature | DD157417, KRAS |
| chr12 | 26178334 | 26178376 | Hypo | cancer_general | RASSF8 | chr12 | 27114515 | 27114639 | Hypo | ovarian | TM7SF3, FGFR1OP2 |
| chr12 | 27176441 | 27176539 | Hypo | cancer_general | MED21, TM7SF3 | chr12 | 27494550 | 27494580 | Hypo | pancreas | ARNTL2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 31316012 | 31316362 | Hypo | cancer_general | OVOS2 | chr12 | 31366306 | 31366336 | Hypo | cancer_general | OVOS2 |
| chr12 | 32086716 | 32086982 | Hypo | cancer_general | | chr12 | 32340317 | 32340534 | Hypo | cancer_general | BICD1 |
| chr12 | 32831622 | 32831652 | Hypo | cancer_general | DNM1L | chr12 | 34494888 | 34494918 | Hypo | cancer_general | |
| chr12 | 34502733 | 34502803 | Hypo | cancer_general | | chr12 | 43944952 | 43944991 | Hypo | cancer_general | |
| chr12 | 47629349 | 47629379 | Hypo | breast | PCED1B | chr12 | 49035233 | 49035414 | Hypo | head_neck | |
| chr12 | 49074601 | 49074843 | Hypo | cancer_general | CCNT1 | chr12 | 49915852 | 49915920 | Hypo | cancer_general | TUBA1A, TUBA1B |
| chr12 | 49657705 | 49657901 | Hypo | cancer_general | D28390, TUBA1C | chr12 | 49989786 | 49989816 | Hypo | ovarian | FAM186B |
| chr12 | 50507349 | 50507522 | Hypo | cancer_general | COX14, GPD1 | chr12 | 50673944 | 50674096 | Hypo | pancreas | |
| chr12 | 50897763 | 50898273 | Hypo | cancer_general | DIP2B | chr12 | 51400044 | 51400091 | Hypo | cancer_general | U7, SLC11A2 |
| chr12 | 51420874 | 51421271 | Hypo | cancer_general | LETMD1 | chr12 | 51421556 | 51421586 | Hypo | cancer_general | |
| chr12 | 51441284 | 51441368 | Hypo | cancer_general | DAZAP2 | chr12 | 51565269 | 51565548 | Hypo | cancer_general | |
| chr12 | 51625514 | 51625587 | Hypo | ovarian | | chr12 | 51930708 | 51930862 | Hypo | cancer_general | |
| chr12 | 53763427 | 53763885 | Hypo | cancer_general | PRR13, PCBP2, AMHR2 | chr12 | 53766833 | 53766964 | Hypo | cancer_general | SP1 |
| chr12 | 53834392 | 53834475 | Hypo | cancer_general | | chr12 | 53885346 | 53885651 | Hypo | cancer_general | TARBP2, MAP3K12 |
| chr12 | 54613463 | 54613615 | Hypo | cancer_general | | chr12 | 54719808 | 54720232 | Hypo | cancer_general | COPZ1 |
| chr12 | 54894048 | 54894173 | Hypo | lung | NCKAP1L | chr12 | 54922624 | 54922803 | Hypo | cancer_general | NCKAP1L |
| chr12 | 55480923 | 55481067 | Hypo | cancer_general | AX747140, DNAJC14, MMP19 | chr12 | 55561202 | 55561354 | Hypo | cancer_general | SUOX, RAB5B |
| chr12 | 56231108 | 56231148 | Hypo | cancer_general | | chr12 | 56400463 | 56400591 | Hypo | cancer_general | |
| chr12 | 56478840 | 56478869 | Hypo | literature | ERBB3 | chr12 | 56481645 | 56481937 | Hypo | literature | ERBB3 |
| chr12 | 56486572 | 56486601 | Hypo | literature | ERBB3, PA2G4 | chr12 | 56490965 | 56490994 | Hypo | literature | ERBB3, PA2G4 |
| chr12 | 56491630 | 56491659 | Hypo | literature | | chr12 | 56492618 | 56492647 | Hypo | literature | PA2G4, ERBB3 |
| chr12 | 56558381 | 56558519 | Hypo | ovarian | SMARCC2, MYL6, MYL6B | chr12 | 56653281 | 56653369 | Hypo | ovarian | COQ10A, ANKRD52 |
| chr12 | 57174355 | 57174452 | Hypo | cancer_general | HSD17B6 | chr12 | 57359920 | 57359950 | Hypo | cancer_general | RDH16 |
| chr12 | 57559869 | 57559925 | Hypo | cancer_general | LRP1 | chr12 | 57881127 | 57881383 | Hypo | cancer_general | MARS, ARHGAP9 |
| chr12 | 57983314 | 57983348 | Hypo | ovarian | PIP4K2C, BC033961, KIF5A | chr12 | 58145415 | 58145450 | Hypo | literature | CDK4, TSPAN31, DM110804, MARCH9 |
| chr12 | 62603907 | 62603937 | Hypo | ovarian | Y_RNA, AK024134, PPM1H | chr12 | 62858444 | 62858575 | Hypo | ovarian | MON2 |
| chr12 | 63326618 | 63326648 | Hypo | cancer_general | | chr12 | 64028352 | 64028382 | Hypo | cancer_general | DPY19L2 |
| chr12 | 64783185 | 64783308 | Hypo | lung | LEMD3 | chr12 | 65516360 | 65516455 | Hypo | cancer_general, colorectal | WIF1 |
| chr12 | 65557212 | 65557376 | Hypo | cancer_general | | chr12 | 65561778 | 65562086 | Hypo | cancer_general | LEMD3 |
| chr12 | 68433260 | 68433321 | Hypo | colorectal | | chr12 | 68964473 | 68964503 | Hypo | ovarian | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 68978322 | 68978576 | Hypo | cancer_general | | chr12 | 69754451 | 69754729 | Hypo | cancer_general | YEATS4, E02193, LYZ |
| chr12 | 69964176 | 69964264 | Hypo | cancer_general | FRS2 | chr12 | 70087493 | 70087568 | Hypo | cancer_general | BEST3 |
| chr12 | 70698883 | 70699050 | Hypo | cancer_general | CNOT2 | chr12 | 85667353 | 85667465 | Hypo | cancer_general | ALX1 |
| chr12 | 89915009 | 89915043 | Hypo | cancer_general | POC1B-GALNT4, GALNT4, POC1B | chr12 | 93476304 | 93476342 | Hypo | breast | LOC643339 |
| chr12 | 94544022 | 94544052 | Hypo | pancreas | PLXNC1 | chr12 | 94852412 | 94852506 | Hypo | cancer_general | CCDC41-AS1, CCDC41 |
| chr12 | 95216830 | 95216960 | Hypo | cancer_general | | chr12 | 95822981 | 95823011 | Hypo | cancer_general | C12orf55 |
| chr12 | 95866563 | 95866609 | Hypo | cancer_general | METAP2 | chr12 | 96880822 | 96881029 | Hypo | cancer_general | |
| chr12 | 98948200 | 98948295 | Hypo | cancer_general | | chr12 | 98949938 | 98949972 | Hypo | ovarian | SLC25A3, SNORA53 |
| chr12 | 98961066 | 98961241 | Hypo | cancer_general | | chr12 | 98986343 | 98986491 | Hypo | cancer_general | GAS2L3 |
| chr12 | 100595495 | 100595558 | Hypo | cancer_general | AX746635, ACTR6 | chr12 | 101025380 | 101025410 | Hypo | pancreas | NFYB, HCFC2 |
| chr12 | 102457208 | 102457238 | Hypo | cancer_general | CCDC53 | chr12 | 104506691 | 104506783 | Hypo | pancreas | |
| chr12 | 104671030 | 104671064 | Hypo | cancer_general | TXNRD1 | chr12 | 104671699 | 104671761 | Hypo | cancer_general | TXNRD1 EID3, TXNRD1 |
| chr12 | 104684181 | 104684258 | Hypo | lung | TXNRD1 | chr12 | 104696376 | 104696502 | Hypo | cancer_general | |
| chr12 | 105017109 | 105017228 | Hypo | colorectal | USP30-AS1, USP30 | chr12 | 108080498 | 108080553 | Hypo | cancer_general | PWP1 |
| chr12 | 109488519 | 109488686 | Hypo | lung | C12orf76 | chr12 | 110353414 | 110353451 | Hypo | breast | TCHP |
| chr12 | 110507084 | 110507207 | Hypo | cancer_general | | chr12 | 110717541 | 110717710 | Hypo | cancer_general | ATP2A2, JA611269 |
| chr12 | 110840344 | 110840404 | Hypo | cancer_general | ANAPC7 GPN3, ARPC3 | chr12 | 110854243 | 110854288 | Hypo | cancer_general | PPTC7 |
| chr12 | 110887179 | 110887209 | Hypo | cancer_general | | chr12 | 110983706 | 110983736 | Hypo | lung | |
| chr12 | 111143726 | 111143756 | Hypo | cancer_general | | chr12 | 111763122 | 111763152 | Hypo | cancer_general | TRAFD1 |
| chr12 | 112547662 | 112547692 | Hypo | cancer_general | | chr12 | 112574734 | 112574995 | Hypo | lung | |
| chr12 | 112792829 | 112792944 | Hypo | breast | | chr12 | 112825760 | 112825896 | Hypo | cancer_general | |
| chr12 | 112888151 | 112888315 | Hypo | literature | PTPN11 | chr12 | 112910821 | 112910850 | Hypo | literature | PTPN11 |
| chr12 | 112915509 | 112915538 | Hypo | literature | PTPN11 | chr12 | 112926255 | 112926284 | Hypo | literature | PTPN11 |
| chr12 | 112926876 | 112926914 | Hypo | literature | PTPN11 | chr12 | 113795506 | 113795657 | Hypo | cancer_general | PLBD2 |
| chr12 | 114337763 | 114337793 | Hypo | lung | RBM19 | chr12 | 117474065 | 117474198 | Hypo | cancer_general | TESC, AK055849, FBXW8 |
| chr12 | 117526330 | 117526368 | Hypo | cancer_general | TESC | chr12 | 118860397 | 118860654 | Hypo | cancer_general | SUDS3 |
| chr12 | 118920764 | 118920804 | Hypo | cancer_general | | chr12 | 120148142 | 120148248 | Hypo | cancer_general | MIR1178, CIT |
| chr12 | 120148923 | 120148962 | Hypo | cancer_general | MIR1178, CIT | chr12 | 120535158 | 120535187 | Hypo | literature | RAB35, CCDC64 |
| chr12 | 120536625 | 120536654 | Hypo | literature | CCDC64, RAB35 | chr12 | 120885215 | 120885245 | Hypo | cancer_general | GATC, TRIAP1, COX6A1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 120971686 | 120971716 | Hypo | cancer_general | RNF10, COQ5 | chr12 | 121622546 | 121622576 | Hypo | cancer_general | P2RX7 |
| chr12 | 122108464 | 122108601 | Hypo | head_neck | MORN3 | chr12 | 122192723 | 122192843 | Hypo | breast | TMEM120B |
| chr12 | 122278388 | 122278580 | Hypo | cancer_general | HPD, SETD1B | chr12 | 122285067 | 122285108 | Hypo | cancer_general | HPD |
| chr12 | 122473581 | 122473611 | Hypo | cancer_general | BCL7A | chr12 | 122940449 | 122940479 | Hypo | colorectal | HCAR1, HCAR3 |
| chr12 | 123129129 | 123129550 | Hypo | cancer_general | HCAR1 | chr12 | 123211316 | 123211390 | Hypo | pancreas | |
| chr12 | 123233646 | 123233846 | Hypo | cancer_general | DENR | chr12 | 123410210 | 123410240 | Hypo | cancer_general | ABCB9 |
| chr12 | 123942025 | 123942189 | Hypo | cancer_general | SNRNP35 | chr12 | 124117199 | 124117289 | Hypo | cancer_general | EIF2B1, GTF2H3 |
| chr12 | 124393560 | 124393604 | Hypo | cancer_general | | chr12 | 124397464 | 124397618 | Hypo | cancer_general | AACS |
| chr12 | 125009276 | 125009306 | Hypo | cancer_general | | chr12 | 125589840 | 125589872 | Hypo | esophageal | |
| chr12 | 129447299 | 129447450 | Hypo | cancer_general | GLT1D1 | chr12 | 130037653 | 130037778 | Hypo | cancer_general | RIMBP2 |
| chr12 | 130821371 | 130821621 | Hypo | cancer_general | PIWIL1 | chr12 | 130968621 | 130968654 | Hypo | cancer_general | AX748157, GPR133 |
| chr12 | 131403032 | 131403125 | Hypo | cancer_general | | chr12 | 131513345 | 131513403 | Hypo | cancer_general | |
| chr12 | 132102173 | 132102202 | Hypo | literature | SFSWAP | chr12 | 132169288 | 132169442 | Hypo | cancer_general | MMP17 |
| chr12 | 132221689 | 132222076 | Hypo | cancer_general | MMP17 | chr12 | 132332910 | 132332940 | Hypo | cancer_general | |
| chr12 | 132333434 | 132333597 | Hypo | cancer_general | PUS1 | chr12 | 132348651 | 132348684 | Hypo | cancer_general | NOC4L |
| chr12 | 132423516 | 132423854 | Hypo | cancer_general | | chr12 | 132643233 | 132643279 | Hypo | head_neck | |
| chr12 | 132986495 | 132986581 | Hypo | cancer_general | LRCOL1 | chr12 | 133002792 | 133003231 | Hypo | cancer_general | P2RX2, POLE |
| chr12 | 133172907 | 133173021 | Hypo | cancer_general | | chr12 | 133199738 | 133199784 | Hypo | cancer_general | PGAM5, PXMP2 |
| chr12 | 133262698 | 133262926 | Hypo | cancer_general | PXMP2, PGAM5, POLE | chr12 | 133280578 | 133280682 | Hypo | ovarian | |
| chr6 | 373148 | 373290 | Hypo | cancer_general | | chr6 | 2986688 | 2986718 | Hypo | cancer_general | NQO2, DKFZP686I15217 |
| chr6 | 3053299 | 3053386 | Hypo | cancer_general | | chr6 | 3247675 | 3247704 | Hypo | literature | AK096219 |
| chr6 | 3285222 | 3285513 | Hypo | cancer_general | SLC22A23, AX746991 | chr6 | 3405645 | 3405713 | Hypo | cancer_general | SLC22A23 |
| chr6 | 4836002 | 4836458 | Hypo | cancer_general | CDYL | chr6 | 4951247 | 4951390 | Hypo | cancer_general | CDYL |
| chr6 | 5359500 | 5359539 | Hypo | breast | FARS2 | chr6 | 5783325 | 5783496 | Hypo | cancer_general | |
| chr6 | 6367086 | 6367271 | Hypo | cancer_general | LY86-AS1 | chr6 | 6753803 | 6753839 | Hypo | colorectal | |
| chr6 | 7731054 | 7731083 | Hypo | literature | BMP6 | chr6 | 7892314 | 7892412 | Hypo | ovarian | |
| chr6 | 8014600 | 8014772 | Hypo | head_neck | BLOC1S5, EEF1E1-MUTED | chr6 | 10390384 | 10390447 | Hypo | cancer_general | TXNDC5, BLOC1S5-TXNDC5 TFAP2A |
| chr6 | 10542836 | 10542977 | Hypo | colorectal | GCNT2 | chr6 | 10734917 | 10735045 | Hypo | cancer_general | TMEM14C |
| chr6 | 12288517 | 12288681 | Hypo | cancer_general | EDN1 | chr6 | 13797690 | 13797736 | Hypo | cancer_general | MCUR1 |
| chr6 | 14687918 | 14688084 | Hypo | cancer_general | | chr6 | 14986483 | 14986522 | Hypo | cancer_general | |
| chr6 | 15513780 | 15513981 | Hypo | ovarian | DTNBP1, JARID2 | chr6 | 16197030 | 16197112 | Hypo | cancer_general | |
| chr6 | 16729595 | 16729624 | Hypo | literature | ATXN1 | chr6 | 17666654 | 17666707 | Hypo | breast | NUP153 |
| chr6 | 17750276 | 17750306 | Hypo | cancer_general | KIF13A | chr6 | 18035867 | 18036015 | Hypo | lung | |
| chr6 | 19892448 | 19892627 | Hypo | cancer_general | | chr6 | 22172209 | 22172305 | Hypo | hepatobiliary | LINC00340 |

TABLE 11-continued

| chr | Start | Stop | Hypo/hyper | classification | annotation |
|---|---|---|---|---|---|
| chr6 | 22172536 | 22172566 | Hypo | hepatobiliary | LINC00340 |
| chr6 | 24662439 | 24662469 | Hypo | cancer_general | ACOT13, TDP2 |
| chr6 | 26214514 | 26214648 | Hypo | cancer_general | HIST1H2BG, HIST1H2AE, HIST1H3F, HIST1H4E |
| chr6 | 26260956 | 26260986 | Hypo | esophageal | HIST1H2BH |
| chr6 | 30095233 | 30095262 | Hypo | literature | TRIM40, DQ580846 |
| chr6 | 32374147 | 32374176 | Hypo | literature | BTNL2 |
| chr6 | 32376051 | 32376080 | Hypo | literature | BTNL2 |
| chr6 | 33632930 | 33633000 | Hypo | hepatobiliary | ITPR3 |
| chr6 | 33955505 | 33955731 | Hypo | cancer_general | |
| chr6 | 34170970 | 34171061 | Hypo | cancer_general | |
| chr6 | 34396431 | 34396542 | Hypo | cancer_general | RPS10 |
| chr6 | 34714803 | 34714896 | Hypo | lung | SNRPC |
| chr6 | 35150041 | 35150080 | Hypo | cancer_general | |
| chr6 | 36165662 | 36165692 | Hypo | cancer_general | BRPF3, BC042825 |
| chr6 | 36313883 | 36313913 | Hypo | cancer_general | ETV7, C6orf222 |
| chr6 | 36406316 | 36406370 | Hypo | cancer_general | KCTD20, PXT1 |
| chr6 | 37392127 | 37392189 | Hypo | cancer_general | FTSID2 |
| chr6 | 37776410 | 37776440 | Hypo | cancer_general | |
| chr6 | 39508464 | 39508493 | Hypo | literature | KIF6 |
| chr6 | 41773520 | 41773903 | Hypo | breast | USP49 |
| chr6 | 42062143 | 42062346 | Hypo | cancer_general | C6orf132 |
| chr6 | 42111015 | 42111051 | Hypo | cancer_general | C6orf132 |
| chr6 | 42773440 | 42773622 | Hypo | cancer_general | GLTSCR1L |
| chr6 | 42990166 | 42990485 | Hypo | cancer_general | RRP36, KLHDC3, MEA1 |
| chr6 | 43424297 | 43424470 | Hypo | cancer_general | DLK2, ABCC10 |
| chr6 | 24647342 | 24647599 | Hypo | cancer_general | TDP2, KIAA0319 |
| chr6 | 26189859 | 26189991 | Hypo | cancer_general | HIST1H3D, HIST1H3F, HIST1H2AD, HIST1H2BF, HIST1H4D, HIST1H2BE |
| chr6 | 26254617 | 26254647 | Hypo | cancer_general | HIST1H2BH, HIST1H3F, HIST1H4G |
| chr6 | 27441812 | 27441842 | Hypo | cancer_general | TRNA_Ser, TRNA_Asp, ZNF184 |
| chr6 | 30130804 | 30130895 | Hypo | literature | TRIM15, TRIM10 |
| chr6 | 32374739 | 32374768 | Hypo | literature | BTNL2 |
| chr6 | 33161275 | 33161342 | Hypo | literature | RXRB, JA611279, SLC39A7, COL11A2 |
| chr6 | 33636388 | 33636418 | Hypo | hepatobiliary | ITPR3 |
| chr6 | 34113872 | 34113957 | Hypo | tcga | |
| chr6 | 34219930 | 34219972 | Hypo | cancer_general | C6orf1, HMGA1 |
| chr6 | 34535802 | 34535832 | Hypo | cancer_general | |
| chr6 | 34724047 | 34724228 | Hypo | cancer_general | SNRPC, TULP1, TEAD3 |
| chr6 | 35470285 | 35470399 | Hypo | cancer_general | BRPF3 |
| chr6 | 36178031 | 36178301 | Hypo | colorectal | |
| chr6 | 36392273 | 36392323 | Hypo | cancer_general | PXT1 |
| chr6 | 37024559 | 37024589 | Hypo | cancer_general | |
| chr6 | 37545401 | 37545495 | Hypo | cancer_general | |
| chr6 | 37776703 | 37776735 | Hypo | cancer_general | |
| chr6 | 41273881 | 41273942 | Hypo | cancer_general | |
| chr6 | 41774459 | 41774576 | Hypo | breast | |
| chr6 | 42090977 | 42091027 | Hypo | cancer_general | USP49 |
| chr6 | 42711893 | 42711923 | Hypo | cancer_general | C6orf132 |
| chr6 | 42846662 | 42846705 | Hypo | cancer_general | TBCC, RPL7L1, DQ581019 |
| chr6 | 43119019 | 43119580 | Hypo | colorectal, cancer_general | PTK7 |
| chr6 | 43425152 | 43425207 | Hypo | cancer_general | ABCC10, DLK2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 43425479 | 43425509 | Hypo | cancer_general | DLK2, ABCC10 | chr6 | 43478676 | 43478745 | Hypo | cancer_general | YIPF3, POLR1C, LRRC73, TJAP1 |
| chr6 | 43639548 | 43639710 | Hypo | ovarian | MRPS18A, RSPH9 | chr6 | 43748463 | 43748616 | Hypo | breast | HV983065, VEGFA |
| chr6 | 44240914 | 44241108 | Hypo | cancer_general | TCTE1, SPATS1, TMEM151B, NFKBIE | chr6 | 44695763 | 44695795 | Hypo | cancer_general | BX647715 |
| chr6 | 47473194 | 47473287 | Hypo | cancer_general | CD2AP | chr6 | 47590439 | 47590604 | Hypo | breast | CD2AP |
| chr6 | 49590555 | 49590786 | Hypo | cancer_general | RHAG | chr6 | 49765146 | 49765202 | Hypo | cancer_general | GSTA3 |
| chr6 | 52344375 | 52344405 | Hypo | pancreas | EFHC1 | chr6 | 52763812 | 52763982 | Hypo | colorectal | ICK, FBXO9 |
| chr6 | 52928742 | 52928776 | Hypo | cancer_general | FBXO9, ICK | chr6 | 52929051 | 52929233 | Hypo | cancer_general | |
| chr6 | 53052723 | 53052859 | Hypo | cancer_general | TRNA_Ile, TRNA_Ala | chr6 | 57694587 | 57694617 | Hypo | cancer_general | |
| chr6 | 58147523 | 58147594 | Hypo | cancer_general | | chr6 | 71090933 | 71090963 | Hypo | ovarian | |
| chr6 | 73980676 | 73980722 | Hypo | hepatobiliary | C6orf147, AL832252, BC031876, KHDC1 | chr6 | 73982025 | 73982058 | Hypo | hepatobiliary | C6orf147, AL832252, BC031876, KHDC1 |
| chr6 | 74097722 | 74097763 | Hypo | ovarian | DDX43 | chr6 | 75995789 | 75995819 | Hypo | cancer_general | FILIP1, LOC100506804, TMEM30A |
| chr6 | 82958615 | 82958917 | Hypo | cancer_general | IBTK | chr6 | 83546464 | 83546498 | Hypo | cancer_general | SNX14 |
| chr6 | 85050415 | 85050504 | Hypo | cancer_general | | chr6 | 86302413 | 86302614 | Hypo | cancer_general | RNGTT |
| chr6 | 88518712 | 88518742 | Hypo | colorectal | AY927641 | chr6 | 89672213 | 89672376 | Hypo | cancer_general | AK091365 |
| chr6 | 97412529 | 97412529 | Hypo | esophageal | KLHL32 | chr6 | 97930083 | 97930113 | Hypo | hepatobiliary | PNISR, BC033061, COQ3 |
| chr6 | 99396456 | 99396609 | Hypo | cancer_general | | chr6 | 99842336 | 99842382 | Hypo | tcga | |
| chr6 | 100050765 | 100050815 | Hypo | cancer_general | PRDM13 | chr6 | 100135425 | 100135583 | Hypo | cancer_general | ATG5 |
| chr6 | 105821423 | 105821453 | Hypo | cancer_general | PREP | chr6 | 106731509 | 106731597 | Hypo | ovarian | PDSS2 |
| chr6 | 107075651 | 107075704 | Hypo | cancer_general | QRSL1, RTN4IP1 | chr6 | 107562769 | 107562859 | Hypo | cancer_general | |
| chr6 | 108181556 | 108181721 | Hypo | cancer_general | SEC63 | chr6 | 108280292 | 108280352 | Hypo | cancer_general | SEC63 |
| chr6 | 109057882 | 109057928 | Hypo | pancreas | | chr6 | 109058799 | 109058861 | Hypo | pancreas | |
| chr6 | 110437721 | 110437751 | Hypo | cancer_general | WASF1 | chr6 | 110848558 | 110848682 | Hypo | ovarian | |
| chr6 | 113852508 | 113852634 | Hypo | cancer_general | | chr6 | 117000853 | 117001032 | Hypo | cancer_general | |
| chr6 | 119254629 | 119254678 | Hypo | cancer_general | MCM9 | chr6 | 119483052 | 119483082 | Hypo | cancer_general | KPNA5, AX746765 |
| chr6 | 121797231 | 121797265 | Hypo | hepatobiliary | | chr6 | 134067194 | 134067471 | Hypo | cancer_general | BC041459 |
| chr6 | 134176232 | 134176299 | Hypo | cancer_general | MGC34034, BC041459 | chr6 | 134589500 | 134589767 | Hypo | cancer_general | SGK1 |
| chr6 | 137366354 | 137366383 | Hypo | literature | IL20RA | chr6 | 149868348 | 149868387 | Hypo | cancer_general | PPIL4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 150183760 | 150183874 | Hypo | cancer_general | LOC100652739, LRP11 | chr6 | 151650396 | 151650453 | Hypo | cancer_general | AKAP12 |
| chr6 | 152419908 | 152419940 | Hypo | literature | ESR1 | chr6 | 154970558 | 154970676 | Hypo | lung | |
| chr6 | 155569208 | 155569305 | Hypo | cancer_general | AB075492, AK022993, TFB1M, TIAM2 | chr6 | 157037549 | 157037677 | Hypo | cancer_general | |
| chr6 | 157266063 | 157266109 | Hypo | breast | ARID1B | chr6 | 157502438 | 157502561 | Hypo | cancer_general | |
| chr6 | 157506082 | 157506112 | Hypo | cancer_general | | chr6 | 157637455 | 157637500 | Hypo | cancer_general | |
| chr6 | 159211558 | 159211701 | Hypo | pancreas | AX747826, EZR | chr6 | 159228187 | 159228217 | Hypo | cancer_general | AX747826, EZR |
| chr6 | 159419589 | 159419717 | Hypo | cancer_general | RSPH3 | chr6 | 161645992 | 161646255 | Hypo | cancer_general | AK311212, AK296276 |
| chr6 | 161780056 | 161780139 | Hypo | esophageal | PARK2 | chr6 | 163602842 | 163602872 | Hypo | esophageal | |
| chr6 | 164114396 | 164114524 | Hypo | cancer_general | AK093114 | chr6 | 164179636 | 164179668 | Hypo | cancer_general | AK093114 |
| chr6 | 164183602 | 164183632 | Hypo | cancer_general | AK093114 | chr6 | 164196971 | 164197003 | Hypo | cancer_general | AK093114 |
| chr6 | 164215532 | 164215633 | Hypo | cancer_general | | chr6 | 164228294 | 164228363 | Hypo | cancer_general | |
| chr6 | 164246015 | 164246143 | Hypo | cancer_general | | chr6 | 164283254 | 164283377 | Hypo | cancer_general | |
| chr6 | 164314289 | 164314443 | Hypo | cancer_general | | chr6 | 164322666 | 164322775 | Hypo | cancer_general | |
| chr6 | 166944367 | 166944403 | Hypo | cancer_general | | chr6 | 167202601 | 167202801 | Hypo | cancer_general | |
| chr6 | 167835129 | 167835171 | Hypo | cancer_general | | chr6 | 168719983 | 168720019 | Hypo | esophageal | DACT2 |
| chr6 | 168858122 | 168858296 | Hypo | esophageal | SMOC2 | chr6 | 168972472 | 168972502 | Hypo | hepatobiliary | SMOC2 |
| chr6 | 169002054 | 169002084 | Hypo | cancer_general | SMOC2 | chr6 | 170047467 | 170047499 | Hypo | lung | WDR27 |
| chr6 | 170240639 | 170240714 | Hypo | cancer_general | | chr6 | 170264728 | 170264761 | Hypo | cancer_general | |
| chr6 | 170475105 | 170475267 | Hypo | cancer_general | | chr6 | 170494286 | 170494315 | Hypo | literature | |
| chr6 | 170894820 | 170894912 | Hypo | cancer_general | PDCD2 | chr6 | 969788 | 969820 | Hypo | cancer_general | DMRT3, DMRT1 |
| chr9 | 2115824 | 2115981 | Hypo | breast | SMARCA2 | chr9 | 5070006 | 5070050 | Hypo | literature | JAK2 |
| chr9 | 5073756 | 5073788 | Hypo | literature | JAK2 | chr9 | 5078346 | 5078375 | Hypo | literature | JAK2 |
| chr9 | 5089711 | 5089740 | Hypo | literature | TRNA_Gln, JAK2 | chr9 | 5153325 | 5153380 | Hypo | cancer_general | |
| chr9 | 6182901 | 6182931 | Hypo | cancer_general | | chr9 | 6756353 | 6756623 | Hypo | cancer_general | KDM4C |
| chr9 | 14884008 | 14884061 | Hypo | hepatobiliary | | chr9 | 20199955 | 20199985 | Hypo | hepatobiliary | |
| chr9 | 21970966 | 21971220 | Hypo | literature | CDKN2A, C9orf53 | chr9 | 21974207 | 21974237 | Hypo | esophageal | |
| chr9 | 21974663 | 21974794 | Hypo | literature | CDKN2A, C9orf53 | chr9 | 22006131 | 22006160 | Hypo | literature | CDKN2A, C9orf53 |
| chr9 | 22008819 | 22008899 | Hypo | literature | CDKN2B, CDKN2B-AS1 | chr9 | 33000470 | 33000512 | Hypo | cancer_general | CDKN2B, CDKN2B-AS1 APTX |
| chr9 | 34136792 | 34136903 | Hypo | head_neck | DQ585850, DQ594696, DQ597117, DQ587955, DQ574810 | chr9 | 34224348 | 34224474 | Hypo | breast | UBAP1, KIF24 |
| chr9 | 34372805 | 34372983 | Hypo | breast | C9orf24, KIAA1161 | chr9 | 36036323 | 36036353 | Hypo | ovarian | RECK |

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 36167272 | 36167544 | Hypo | cancer_general | CCIN, GLIPR2 | chr9 | 36196920 | 36197005 | Hypo | ovarian | CLTA |
| chr9 | 36318375 | 36318410 | Hypo | cancer_general | PAX5, MIR4475 | chr9 | 36433491 | 36433629 | Hypo | cancer_general | ZCCHC7 |
| chr9 | 36832204 | 36832343 | Hypo | cancer_general | | chr9 | 37119301 | 37119331 | Hypo | head_neck | |
| chr9 | 37467610 | 37467898 | Hypo | cancer_general | FRMPD1 | chr9 | 37593684 | 37593795 | Hypo | cancer_general | TOMM5 |
| chr9 | 37697404 | 37697438 | Hypo | cancer_general | | chr9 | 38646763 | 38646839 | Hypo | cancer_general | |
| chr9 | 71200632 | 71200662 | Hypo | cancer_general | | chr9 | 71500847 | 71500886 | Hypo | hepatobiliary | |
| chr9 | 71584152 | 71584254 | Hypo | hepatobiliary | AK057188 BC039385, C9orf135, LOC494558 | chr9 | 71734816 | 71735024 | Hypo | cancer_general | TJP2 |
| chr9 | 72435189 | 72435317 | Hypo | cancer_general | | chr9 | 73032801 | 73032831 | Hypo | cancer_general | KLF9 |
| chr9 | 74210499 | 74210654 | Hypo | cancer_general | | chr9 | 77823177 | 77823315 | Hypo | cancer_general | PRUNE2 |
| chr9 | 79197119 | 79197149 | Hypo | hepatobiliary | FOXB2 | chr9 | 79231003 | 79231033 | Hypo | cancer_general | |
| chr9 | 79638138 | 79638244 | Hypo | cancer_general | GNAQ | chr9 | 80303132 | 80303171 | Hypo | cancer_general | |
| chr9 | 80409473 | 80409502 | Hypo | literature | | chr9 | 80833933 | 80834011 | Hypo | lung | C9orf64, HNRNPK, MIR7-1 |
| chr9 | 85372494 | 85372596 | Hypo | cancer_general | | chr9 | 86578079 | 86578366 | Hypo | ovarian | |
| chr9 | 88694345 | 88694438 | Hypo | cancer_general | GOLM1 | chr9 | 90907408 | 90907438 | Hypo | hepatobiliary | |
| chr9 | 90937357 | 90937387 | Hypo | ovarian | | chr9 | 91914276 | 91914306 | Hypo | cancer_general | |
| chr9 | 92053911 | 92053949 | Hypo | cancer_general | SEMA4D | chr9 | 93698029 | 93698133 | Hypo | colorectal | ROR2 |
| chr9 | 94572641 | 94572743 | Hypo | cancer_general | ROR2 | chr9 | 94686919 | 94686957 | Hypo | hepatobiliary | |
| chr9 | 95417551 | 95417651 | Hypo | cancer_general | | chr9 | 95560810 | 95560840 | Hypo | cancer_general | FAM120A |
| chr9 | 95761687 | 95761828 | Hypo | cancer_general | FGD3 | chr9 | 96230296 | 96230334 | Hypo | cancer_general | PTPDC1 |
| chr9 | 96573748 | 96573869 | Hypo | cancer_general | MIR4291 | chr9 | 96855991 | 96857144 | Hypo | cancer_general | MIR23B, MIR3074 |
| chr9 | 97020978 | 97021126 | Hypo | cancer_general | ZNF169 | chr9 | 97845915 | 97845947 | Hypo | head_neck | |
| chr9 | 98076746 | 98076776 | Hypo | cancer_general | FANCC | chr9 | 99259362 | 99259405 | Hypo | ovarian | CDC14B, HABP4 |
| chr9 | 99450020 | 99450142 | Hypo | lung | | chr9 | 100397821 | 100398016 | Hypo | cancer_general | NCBP1, TSTD2 |
| chr9 | 100818295 | 100818437 | Hypo | cancer_general | NANS | chr9 | 100835828 | 100835870 | Hypo | cancer_general | TRIM14, NANS |
| chr9 | 103174620 | 103174730 | Hypo | cancer_general | | chr9 | 106998039 | 106998134 | Hypo | head_neck | |
| chr9 | 110126074 | 110126247 | Hypo | cancer_general | | chr9 | 111894386 | 111894520 | Hypo | colorectal | FRRS1L, AL390170 |
| chr9 | 112403364 | 112403394 | Hypo | esophageal | Mir_548, PALM2 | chr9 | 114247454 | 114247578 | Hypo | cancer_general | KIAA0368 |
| chr9 | 115067932 | 115068106 | Hypo | cancer_general | | chr9 | 115087567 | 115087597 | Hypo | cancer_general | |
| chr9 | 115478932 | 115479250 | Hypo | cancer_general | INIP | chr9 | 115566363 | 115566583 | Hypo | cancer_general | SNX30 |
| chr9 | 116633883 | 116633987 | Hypo | cancer_general | ZNF618 | chr9 | 117050981 | 117051030 | Hypo | cancer_general | |
| chr9 | 119603412 | 119603535 | Hypo | head_neck | TTLL11 | chr9 | 123295355 | 123295463 | Hypo | cancer_general | CDK5RAP2 |
| chr9 | 124749865 | 124749953 | Hypo | ovarian | ZBTB26, ZBTB6 | chr9 | 124751485 | 124751515 | Hypo | cancer_general | TTLL11 |
| chr9 | 125676633 | 125676753 | Hypo | cancer_general | DENND1A, CRB2 | chr9 | 125704789 | 125704835 | Hypo | cancer_general | RABGAP1 |
| chr9 | 126133778 | 126133856 | Hypo | cancer_general | | chr9 | 126154304 | 126154575 | Hypo | cancer_general | DENND1A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 126349038 | 126349104 | Hypo | lung | DENND1A | chr9 | 127605297 | 127605327 | Hypo | head_neck | |
| chr9 | 127630125 | 127630205 | Hypo | cancer_general | ARPC5L, RPL35, WDR38 | chr9 | 127853274 | 127853304 | Hypo | breast | |
| chr9 | 127920543 | 127920572 | Hypo | literature | PP6C | chr9 | 128136065 | 128136095 | Hypo | cancer_general | GAPVD1 |
| chr9 | 128635180 | 128635210 | Hypo | ovarian | PBX3 | chr9 | 128759852 | 128759954 | Hypo | cancer_general | |
| chr9 | 129388719 | 129388796 | Hypo | cancer_general | LMX1B | chr9 | 129517783 | 129517821 | Hypo | colorectal | |
| chr9 | 130248419 | 130248449 | Hypo | cancer_general | AX747547, LRSAM1 | chr9 | 130325967 | 130325997 | Hypo | cancer_general | FAM129B |
| chr9 | 130675509 | 130675615 | Hypo | cancer_general | PIP5KL1, ST6GALNAC4 | chr9 | 130694413 | 130694468 | Hypo | cancer_general | DPM2, FAM102A, PIP5KL1 |
| chr9 | 130694809 | 130694948 | Hypo | cancer_general | DPM2, FAM102A, PIP5KL1 | chr9 | 131177975 | 131178094 | Hypo | cancer_general | CERCAM |
| chr9 | 131417698 | 131417940 | Hypo | cancer_general | | chr9 | 131542193 | 131542267 | Hypo | head_neck | TBC1D13, ZER1 |
| chr9 | 131580038 | 131580257 | Hypo | cancer_general | ENDOG, C9orf114, TBC1D13 | chr9 | 131607517 | 131607547 | Hypo | cancer_general | CCBL1 |
| chr9 | 131607770 | 131607800 | Hypo | cancer_general | CCBL1 | chr9 | 131854231 | 131854328 | Hypo | cancer_general | CRAT, DOLPP1 |
| chr9 | 131854564 | 131854732 | Hypo | literature | CRAT, DOLPP1 | chr9 | 132373058 | 132373091 | Hypo | breast | C9orf50 |
| chr9 | 132383347 | 132383376 | Hypo | cancer_general | C9orf50, NTMT1 | chr9 | 132402840 | 132402883 | Hypo | cancer_general | ASB6, NTMT1 |
| chr9 | 132403149 | 132403216 | Hypo | cancer_general | ASB6, NTMT1 | chr9 | 132559377 | 132559456 | Hypo | cancer_general | TOR1B |
| chr9 | 132815175 | 132815205 | Hypo | cancer_general | Mir_562, FNBP1, GPR107 | chr9 | 132881814 | 132881844 | Hypo | cancer_general | |
| chr9 | 133605601 | 133605631 | Hypo | cancer_general | ABL1 | chr9 | 133738343 | 133738372 | Hypo | literature | AX748265, ABL1 |
| chr9 | 133747505 | 133747534 | Hypo | literature | AX748265, ABL1 | chr9 | 133773766 | 133773923 | Hypo | cancer_general | FIBCD1, QRFP |
| chr9 | 133927347 | 133927481 | Hypo | cancer_general | LAMC3 | chr9 | 133928236 | 133928266 | Hypo | cancer_general | LAMC3 |
| chr9 | 134126670 | 134126741 | Hypo | colorectal, cancer_general | FAM78A | chr9 | 134191085 | 134191218 | Hypo | cancer_general | PPAPDC3 |
| chr9 | 134207916 | 134208048 | Hypo | cancer_general | | chr9 | 134717313 | 134717367 | Hypo | cancer_general | SETX |
| chr9 | 135073463 | 135073506 | Hypo | hepatobiliary | NTNG2 | chr9 | 135135114 | 135135247 | Hypo | cancer_general | BARHL1, C9orf171 |
| chr9 | 135231073 | 135231158 | Hypo | cancer_general | | chr9 | 135456476 | 135456544 | Hypo | pancreas | |
| chr9 | 135548238 | 135548313 | Hypo | cancer_general | GTF3C4, DDX31 | chr9 | 135590218 | 135590334 | Hypo | cancer_general | |
| chr9 | 135796801 | 135796830 | Hypo | literature | TSC1 | chr9 | 135865090 | 135865161 | Hypo | cancer_general | GFI1B |
| chr9 | 135898911 | 135899124 | Hypo | cancer_general | GTF3C5 | chr9 | 137002646 | 137002692 | Hypo | cancer_general | WDR5 |
| chr9 | 137299670 | 137299699 | Hypo | tcga | RXRA | chr9 | 137575915 | 137575945 | Hypo | cancer_general | COL5A1 |
| chr9 | 137656958 | 137657128 | Hypo | cancer_general | COL5A1 | chr9 | 137667327 | 137667357 | Hypo | cancer_general | COL5A1 |
| chr9 | 137718901 | 137719001 | Hypo | cancer_general | LOC101448202, COL5A1 | chr9 | 137722087 | 137722209 | Hypo | cancer_general | LOC101448202, COL5A1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 138265123 | 138265251 | Hypo | cancer_general | LCN9 | chr9 | 138474557 | 138474590 | Hypo | cancer_general | LOC100130954 |
| chr9 | 138563059 | 138563280 | Hypo | cancer_general | KCNT1 | chr9 | 138627636 | 138627893 | Hypo | cancer_general | KCNT1 |
| chr9 | 138634047 | 138634159 | Hypo | cancer_general | KCNT1 | chr9 | 138659800 | 138659905 | Hypo | cancer_general | KCNT1 |
| chr9 | 138660943 | 138661012 | Hypo | literature | KCNT1 | chr9 | 138661648 | 138661870 | Hypo | cancer_general | KCNT1 |
| chr9 | 138666455 | 138666558 | Hypo | cancer_general | | chr9 | 138826382 | 138826412 | Hypo | head_neck | UBAC1 |
| chr9 | 138880711 | 138880875 | Hypo | cancer_general | | chr9 | 138991798 | 138991828 | Hypo | esophageal | NACC2 |
| chr9 | 139000566 | 139000642 | Hypo | cancer_general | C9orf69 | chr9 | 139012272 | 139012411 | Hypo | cancer_general | C9orf69 |
| chr9 | 139045653 | 139045683 | Hypo | cancer_general | | chr9 | 139047532 | 139047633 | Hypo | cancer_general | |
| chr9 | 139111268 | 139111298 | Hypo | cancer_general | QSOX2 | chr9 | 139269039 | 139269121 | Hypo | breast | SNAPC4, CARD9 |
| chr9 | 139399407 | 139399436 | Hypo | literature | NOTCH1 | chr9 | 139421955 | 139421985 | Hypo | cancer_general | MIR4673 |
| chr9 | 139477862 | 139478020 | Hypo | head_neck | | chr9 | 139698925 | 139699051 | Hypo | cancer_general | RABL6, KIAA1984-AS1, KIAA1984 |
| chr9 | 139704008 | 139704279 | Hypo | cancer_general | RABL6, KIAA1984-AS1, KIAA1984 | chr9 | 139859041 | 139859268 | Hypo | cancer_general | LCN12 |
| chr9 | 139888945 | 139888980 | Hypo | breast | CLIC3, C9orf142, LCNL1 | | | | | | |
| chr9 | 140030498 | 140030528 | Hypo | cancer_general | GRIN1 | chr9 | 140015209 | 140015241 | Hypo | ovarian | DPP7 |
| chr9 | 140033001 | 140033092 | Hypo | pancreas | GRIN1 | chr9 | 140031944 | 140032082 | Hypo | cancer_general | GRIN1 |
| | | | | | | chr9 | 140127883 | 140128080 | Hypo | cancer_general | FAM166A, SLC34A3, RNF224, C9orf169, AK128153, TUBB4B, TUBB2C |
| chr9 | 140137310 | 140137488 | Hypo | cancer_general | FAM166A, LOC100129722, C9orf173, TUBB2C, TUBB4B, SLC34A3 | chr9 | 140205394 | 140205519 | Hypo | cancer_general | EXD3, NRARP |
| chr9 | 140245877 | 140245998 | Hypo | cancer_general | EXD3 | chr9 | 140332708 | 140333018 | Hypo | cancer_general | NSMF, ENTPD8, NOXA1 |
| chr9 | 140382557 | 140382596 | Hypo | cancer_general | PNPLA7 | chr9 | 140392454 | 140392484 | Hypo | cancer_general | ARRDC1 |
| chr9 | 140397029 | 140397097 | Hypo | cancer_general | | chr9 | 140498318 | 140498394 | Hypo | cancer_general | EHMT1 |
| chr9 | 140507256 | 140507419 | Hypo | cancer_general | ARRDC1, C9orf37, EHMT1 | chr9 | 140704046 | 140704131 | Hypo | ovarian | |
| chr9 | 140709046 | 140709174 | Hypo | head_neck | EHMT1 | chr9 | 140727471 | 140727511 | Hypo | head_neck | MIR602, EHMT1 |
| chr9 | 140727845 | 140727930 | Hypo | head_neck | MIR602, EHMT1 | chr9 | 140769943 | 140769973 | Hypo | cancer_general | CACNA1B, AK128414 |
| chr16 | 93831 | 93932 | Hypo | head_neck | POLR3K, SNRNP25 | chr16 | 142649 | 142783 | Hypo | lung | NPRL3, MPG |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 189744 | 189933 | Hypo | cancer_general | NPRL3 | chr16 | 199886 | 199943 | Hypo | cancer_general | HBZ |
| chr16 | 232136 | 232166 | Hypo | cancer_general | HBQ1, HBA1, HBA2, LUC7L | chr16 | 280323 | 280395 | Hypo | cancer_general | ITFG3, LUC7L |
| chr16 | 318104 | 318227 | Hypo | cancer_general | RGS11, ITFG3 | chr16 | 318498 | 318763 | Hypo | cancer_general | RGS11, ITFG3 |
| chr16 | 337599 | 337659 | Hypo | cancer_general | AXIN1, PDIA2, ARHGDIG | chr16 | 410377 | 410407 | Hypo | cancer_general | AXIN1, MRPL28 |
| chr16 | 571714 | 571959 | Hypo | cancer_general | LINC00235, SOLH, RAB11FIP3 | chr16 | 611385 | 611520 | Hypo | cancer_general | NHLRC4, PIGQ, C16orf11, SOLH |
| chr16 | 611969 | 612260 | Hypo | cancer_general | NHLRC4, PIGQ, C16orf11, SOLH | chr16 | 612869 | 613037 | Hypo | cancer_general | NHLRC4, PIGQ, C16orf11, SOLH |
| chr16 | 667141 | 667297 | Hypo | lung | RAB40C | chr16 | 667547 | 667622 | Hypo | lung | RAB40C, WFIKKN1, |
| chr16 | 667876 | 668074 | Hypo | lung | RAB40C | chr16 | 672730 | 672806 | Hypo | head_neck | RAB40C, AK128777 |
| chr16 | 677972 | 678084 | Hypo | lung | AK301549, RAB40C, AK128777, WFIKKN1, C16orf13, TRNA_Gly, TRNA | chr16 | 700299 | 700329 | | | WDR90, FAM195A |
| chr16 | 726626 | 726990 | Hypo | cancer_general | STUB1, JMJD8, WDR24, RHBDL1, RHOT2, WDR90 | chr16 | 731488 | 731610 | Hypo | cancer_general | STUB1, RHBDL1, RHOT2, JMJD8, WDR24 |
| chr16 | 735205 | 735594 | Hypo | cancer_general | FBXL16, WDR24, JMJD8, STUB1, RHBDL1 | chr16 | 740791 | 740914 | Hypo | cancer_general | STUB1, FBXL16, WDR24, JMJD8 |
| chr16 | 741376 | 741601 | Hypo | cancer_general | STUB1, FBXL16, WDR24, JMJD8 | chr16 | 762523 | 762694 | Hypo | cancer_general | METRN, AL360260, FAM173A, CCDC78 |
| chr16 | 837361 | 837460 | Hypo | cancer_general | CHTF18, RPUSD1 | chr16 | 845955 | 845985 | Hypo | cancer_general | GNG13, PRR25, CHTF18, RPUSD1 |
| chr16 | 882484 | 882588 | Hypo | cancer_general | LMF1 | chr16 | 895093 | 895166 | Hypo | cancer_general | LMF1 |
| chr16 | 943481 | 943553 | Hypo | cancer_general | | chr16 | 1018120 | 1018150 | Hypo | cancer_general | LMF1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 1019640 | 1019685 | Hypo | ovarian | LMF1 | chr16 | 1052587 | 1052627 | Hypo | cancer_general | SSTR5, SSTR5-AS1 |
| chr16 | 1102927 | 1102957 | Hypo | cancer_general | | chr16 | 1116661 | 1116691 | Hypo | cancer_general | SSTR5, SSTR5-AS1 |
| chr16 | 1129011 | 1129140 | Hypo | cancer_general | C1QTNF8, SSTR5, BC084558, SSTR5-AS1 | chr16 | 1155162 | 1155212 | Hypo | cancer_general | C1QTNF8 |
| chr16 | 1186809 | 1186850 | Hypo | cancer_general | CACNA1H | chr16 | 1217307 | 1217503 | Hypo | cancer_general | CACNA1H |
| chr16 | 1218034 | 1218090 | Hypo | cancer_general | CACNA1H | chr16 | 1228804 | 1228916 | Hypo | cancer_general | CACNA1H |
| chr16 | 1229970 | 1230142 | Hypo | cancer_general | TPSG1, TPSB2, CACNA1H | chr16 | 1248604 | 1248675 | Hypo | cancer_general | CACNA1H |
| chr16 | 1267925 | 1268120 | Hypo | cancer_general | | chr16 | 1271546 | 1271646 | Hypo | cancer_general | TPSB2, CACNA1H, TPSG1 |
| chr16 | 1312526 | 1312611 | Hypo | cancer_general | TPSD1 | chr16 | 1323976 | 1324061 | Hypo | cancer_general | BAIAP3, TSR3, GNPTG |
| chr16 | 1394502 | 1394596 | Hypo | cancer_general | TSR3, GNPTG, BAIAP3 | chr16 | 1397454 | 1397484 | Hypo | head_neck | |
| chr16 | 1407370 | 1407846 | Hypo | lung, cancer_general | UNKL, GNPTG, TSR3, BAIAP3 | chr16 | 1408210 | 1408240 | Hypo | cancer_general | UNKL, GNPTG, TSR3, BAIAP3 |
| chr16 | 1428508 | 1428873 | Hypo | cancer_general | UNKL | chr16 | 1466425 | 1466455 | Hypo | cancer_general | UNKL, C16orf91 |
| chr16 | 1469334 | 1469527 | Hypo | cancer_general | C16orf91, UNKL | chr16 | 1491567 | 1491613 | Hypo | cancer_general | CLCN7, CCDC154 |
| chr16 | 1523925 | 1523971 | Hypo | cancer_general | CLCN7 | chr16 | 1704656 | 1704800 | Hypo | breast | CRAMP1L, HN1L |
| chr16 | 1729868 | 1730022 | Hypo | cancer_general | CRAMP1L, HN1L | chr16 | 1730306 | 1730597 | Hypo | cancer_general | CRAMP1L |
| chr16 | 1741853 | 1742079 | Hypo | cancer_general | HN1L, CRAMP1L | chr16 | 1750769 | 1750907 | Hypo | head_neck | MAPK8IP3, HN1L |
| chr16 | 1993818 | 1993848 | Hypo | cancer_general | RPL3L, MSRB1 | chr16 | 2029072 | 2029137 | Hypo | cancer_general | GFER, NOXO1, TBL3 |
| chr16 | 2042875 | 2042905 | Hypo | head_neck | ZNF598, SYNGR3, GFER | chr16 | 2106703 | 2106732 | Hypo | literature | TSC2, NTHL1 |
| chr16 | 2111966 | 2111995 | Hypo | literature | TSC2 | chr16 | 2120515 | 2120544 | Hypo | literature | TSC2 |
| chr16 | 2122243 | 2122272 | Hypo | literature | | chr16 | 2124205 | 2124348 | Hypo | literature | PKD1, TSC2 |
| chr16 | 2126080 | 2126109 | Hypo | literature | TSC2 | chr16 | 2128577 | 2129581 | Hypo | head_neck | TSC2 |
| chr16 | 2130361 | 2130390 | Hypo | literature | TSC2, PKD1, MIR1225 | chr16 | 2135301 | 2135330 | Hypo | literature | PKD1, MIR1225, TSC2 |
| chr16 | 2136228 | 2136257 | Hypo | literature | PKD1, MIR1225, TSC2 | chr16 | 2136727 | 2136855 | Hypo | literature | PKD1, TSC2 |
| chr16 | 2141909 | 2141972 | Hypo | cancer_general | PKD1, MIR1225, TSC2 | chr16 | 2142546 | 2142628 | Hypo | cancer_general | PKD1, MIR1225, TSC2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 2213313 | 2213343 | Hypo | cancer_general | TRAF7, SNORD60, RAB26 | chr16 | 2232745 | 2233003 | Hypo | cancer_general | CASKIN1, TRAF7 |
| chr16 | 2234726 | 2235020 | Hypo | cancer_general | CASKIN1, TRAF7 | chr16 | 2275129 | 2275182 | Hypo | cancer_general | E4F1 |
| chr16 | 2281249 | 2281314 | Hypo | lung | E4F1, DNASE1L2, ECI1 | chr16 | 2466225 | 2466307 | Hypo | cancer_general | |
| chr16 | 2485858 | 2485917 | Hypo | head_neck | CCNF | chr16 | 2508414 | 2508453 | Hypo | lung | C16orf59, CCNF |
| chr16 | 2531069 | 2531177 | Hypo | cancer_general | TBC1D24, NTN3 | chr16 | 2731530 | 2731560 | Hypo | cancer_general | KCTD5, ERVK13-1 |
| chr16 | 2764377 | 2764470 | Hypo | cancer_general | PRSS27, KCTD5 | chr16 | 2770122 | 2770602 | Hypo | cancer_general | PRSS27 |
| chr16 | 2818101 | 2818156 | Hypo | cancer_general | TCEB2, SRRM2 | chr16 | 2956451 | 2956670 | Hypo | cancer_general | FLYWCH1, FLYWCH2 |
| chr16 | 2974601 | 2974650 | Hypo | head_neck | FLYWCH1 | chr16 | 3151127 | 3151186 | Hypo | cancer_general | ZNF205-AS1, ZSCAN10 |
| chr16 | 3211708 | 3212019 | Hypo | cancer_general | TRNA_Lys, TRNA_Pseudo, TRNA_Pro, TRNA_Arg | chr16 | 3269249 | 3269350 | Hypo | cancer_general | ZNF200, OR1F2P |
| chr16 | 3284117 | 3284147 | Hypo | esophageal | MEFV, ZNF200 | chr16 | 3492583 | 3492675 | Hypo | cancer_general | NAA60, ZNF597 |
| chr16 | 3598920 | 3598953 | Hypo | cancer_general | NLRC3 | chr16 | 3696694 | 3696724 | Hypo | cancer_general | DNASE1 |
| chr16 | 3802981 | 3803074 | Hypo | breast | CREBBP | chr16 | 3950127 | 3950279 | Hypo | cancer_general | |
| chr16 | 4264529 | 4264694 | Hypo | cancer_general | SRL | chr16 | 4303144 | 4303174 | Hypo | cancer_general | TFAP4, LOC100507501 |
| chr16 | 4310735 | 4310847 | Hypo | cancer_general | TFAP4, LOC100507501 | chr16 | 4431126 | 4431189 | Hypo | ovarian | VASN, CORO7-PAM16, CORO7 |
| chr16 | 4783226 | 4783375 | Hypo | cancer_general | C16orf71, ANKS3 | chr16 | 4846136 | 4846514 | Hypo | cancer_general | GLYR1, LOC440335, SEPT12, ROGDI |
| chr16 | 4887144 | 4887244 | Hypo | breast | UBN1, GLYR1 | chr16 | 5541116 | 5541158 | Hypo | cancer_general | BC108660 |
| chr16 | 6035056 | 6035208 | Hypo | cancer_general | | chr16 | 7382499 | 7382534 | Hypo | literature | RBFOX1 |
| chr16 | 7525361 | 7525531 | Hypo | cancer_general | RBFOX1 | chr16 | 8781032 | 8781177 | Hypo | cancer_general | ABAT |
| chr16 | 8870353 | 8870383 | Hypo | cancer_general | ABAT | chr16 | 9009860 | 9009989 | Hypo | cancer_general | USP7 |
| chr16 | 11242000 | 11242138 | Hypo | cancer_general | CLEC16A | chr16 | 11427659 | 11427732 | Hypo | cancer_general | |
| chr16 | 11490632 | 11490662 | Hypo | blood | | chr16 | 11923005 | 11923035 | Hypo | cancer_general | RSL1D1, BCAR4 |
| chr16 | 12011258 | 12011325 | Hypo | cancer_general | GSPT1 | chr16 | 12011940 | 12012073 | Hypo | cancer_general | GSPT1 |
| chr16 | 12066767 | 12066806 | Hypo | cancer_general | SNX29, TNFRSF17 | chr16 | 12210772 | 12210896 | Hypo | head_neck | SNX29 |
| chr16 | 12211279 | 12211416 | Hypo | head_neck | SNX29 | chr16 | 12530169 | 12530199 | Hypo | cancer_general | |
| chr16 | 12971776 | 12971934 | Hypo | cancer_general | | chr16 | 14021974 | 14022003 | Hypo | literature | ERCC4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 14041504 | 14041533 | Hypo | literature | ERCC4 | chr16 | 14041795 | 14041824 | Hypo | literature | ERCC4 |
| chr16 | 14042062 | 14042091 | Hypo | literature | ERCC4 | chr16 | 14189948 | 14190069 | Hypo | cancer_general | MKL2 |
| chr16 | 14724632 | 14724736 | Hypo | cancer_general | BFAR, PARN | chr16 | 14725842 | 14726005 | Hypo | cancer_general | BFAR, PARN |
| chr16 | 15708247 | 15708309 | Hypo | pancreas | KIAA0430 | chr16 | 15738905 | 15739042 | Hypo | cancer_general | KIAA0430, NDE1, MIR484 |
| chr16 | 15820825 | 15820865 | Hypo | cancer_general | AX747846, MYH11 | chr16 | 16868746 | 16868905 | Hypo | cancer_general | |
| chr16 | 18163245 | 18163352 | Hypo | cancer_general | | chr16 | 18802250 | 18802680 | Hypo | cancer_general | ARL6IP1, RPS15A |
| chr16 | 18950928 | 18951018 | Hypo | cancer_general | GDE1, CCP110 | chr16 | 19430908 | 19430949 | Hypo | cancer_general | TMC5 |
| chr16 | 19531564 | 19531697 | Hypo | cancer_general | | chr16 | 21541606 | 21541636 | Hypo | cancer_general | SLC7A5P2 |
| chr16 | 21665540 | 21665570 | Hypo | head_neck | IGSF6 | chr16 | 21666641 | 21666771 | Hypo | head_neck | IGSF6 |
| chr16 | 21674664 | 21674777 | Hypo | ovarian | | chr16 | 21839328 | 21839470 | Hypo | cancer_general | RRN3P1, LOC23117, LOC100132247 |
| chr16 | 22300599 | 22300637 | Hypo | cancer_general | TRNA_Leu, TRNA, POLR3E, EEF2K | chr16 | 22326397 | 22326427 | Hypo | head_neck | POLR3E |
| chr16 | 24127251 | 24127338 | Hypo | cancer_general | PRKCB | chr16 | 24172241 | 24172271 | Hypo | cancer_general | PRKCB |
| chr16 | 24180710 | 24180760 | Hypo | cancer_general | PRKCB | chr16 | 24415106 | 24415176 | Hypo | cancer_general | |
| chr16 | 25266537 | 25266573 | Hypo | cancer_general | ZKSCAN2 | chr16 | 25542301 | 25542452 | Hypo | cancer_general | |
| chr16 | 25551107 | 25551264 | Hypo | cancer_general | | chr16 | 25921574 | 25921604 | Hypo | cancer_general | HS3ST4 |
| chr16 | 26302585 | 26302619 | Hypo | cancer_general | KDM8 | chr16 | 26664739 | 26664775 | Hypo | cancer_general | |
| chr16 | 27207774 | 27207852 | Hypo | head_neck | | chr16 | 27459938 | 27460074 | Hypo | cancer_general | IL21R-AS1, IL21R |
| chr16 | 27749857 | 27750033 | Hypo | breast | | chr16 | 27961122 | 27961254 | Hypo | cancer_general | XPO6 |
| chr16 | 28093825 | 28093866 | Hypo | cancer_general | | chr16 | 28224516 | 28224546 | Hypo | ovarian | CCDC101, NUPR1 |
| chr16 | 28491774 | 28491924 | Hypo | colorectal | CLN3 | chr16 | 28560309 | 28560381 | Hypo | breast | |
| chr16 | 28823157 | 28823459 | Hypo | cancer_general | AK125489 | chr16 | 28850998 | 28851028 | Hypo | breast | ATXN2L, TUFM, MIR4721, SH2B1 |
| chr16 | 28877839 | 28877883 | Hypo | esophageal | SH2B1 | chr16 | 29119008 | 29119058 | Hypo | cancer_general | AK075019, RRN3P2 |
| chr16 | 29153284 | 29153356 | Hypo | cancer_general | | chr16 | 29244900 | 29244997 | Hypo | cancer_general | |
| chr16 | 29830871 | 29831078 | Hypo | cancer_general | BC029255, PAGR1, PRRT2, AK097472, AB209061, MAZ, MVP | chr16 | 29936211 | 29936272 | Hypo | cancer_general | KCTD13, ASPHD1 |
| chr16 | 30017330 | 30017447 | Hypo | cancer_general | DOC2A, INO80E | chr16 | 30065485 | 30065525 | Hypo | cancer_general | ALDOA |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 30085867 | 30085995 | Hypo | cancer_general | PPP4C, ALDOA | chr16 | 30116285 | 30116315 | Hypo | cancer_general | MAPK3, GDPD3, AK097453, YPEL3 |
| chr16 | 30124691 | 30124861 | Hypo | cancer_general | MAPK3, GDPD3, AK097453 | chr16 | 30169925 | 30170103 | Hypo | cancer_general | ZNF48, SEPT1 |
| chr16 | 30388542 | 30388574 | Hypo | cancer_general | SEPT1, ZNF48, MYLPF, TBC1D10B | chr16 | 30402082 | 30402112 | Hypo | cancer_general | |
| chr16 | 30609373 | 30609408 | Hypo | cancer_general | ZNF689 | chr16 | 30639693 | 30639735 | Hypo | cancer_general | |
| chr16 | 30804321 | 30804472 | Hypo | cancer_general | ZNF629 | chr16 | 30826334 | 30826509 | Hypo | cancer_general | |
| chr16 | 30907010 | 30907148 | Hypo | lung | BC073928, CTF1, MIR762, BCL7C | chr16 | 31384593 | 31384623 | Hypo | cancer_general | ITGAX |
| chr16 | 31446830 | 31447096 | Hypo | cancer_general | ZNF843, COX6A2, ITGAD | chr16 | 31498008 | 31498165 | Hypo | cancer_general | C16orf58, SLC5A2, TGFB1I1, BC054514 |
| chr16 | 31500544 | 31500673 | Hypo | cancer_general | SLC5A2, C16orf58, BC054514 | chr16 | 46569239 | 46569474 | Hypo | cancer_general | |
| chr16 | 46721567 | 46721707 | Hypo | head_neck | ORC6, VPS35 | chr16 | 46803280 | 46803355 | Hypo | lung | |
| chr16 | 48450544 | 48450574 | Hypo | cancer_general | N4BP1 | chr16 | 48641663 | 48641693 | Hypo | cancer_general | N4BP1 |
| chr16 | 48642149 | 48642179 | Hypo | cancer_general | ZNF423 | chr16 | 49314810 | 49314840 | Hypo | cancer_general | CBLN1 |
| chr16 | 49638060 | 49638090 | Hypo | cancer_general | | chr16 | 50335767 | 50335797 | Hypo | cancer_general | ADCY7 |
| chr16 | 53447826 | 53448002 | Hypo | cancer_general | | chr16 | 53467271 | 53467395 | Hypo | cancer_general | RBL2, U6 FTO |
| chr16 | 53563622 | 53563654 | Hypo | tcga | MT1A, MT1JP, MT1M, MT1DP | chr16 | 54128645 | 54128713 | Hypo | breast | |
| chr16 | 56672656 | 56672685 | Hypo | cancer_general | | chr16 | 57222663 | 57222709 | Hypo | cancer_general | RSPRY1 |
| chr16 | 57326422 | 57326613 | Hypo | cancer_general | PLLP, TRNA_Leu | chr16 | 57935454 | 57935605 | Hypo | cancer_general | CNGB1 |
| chr16 | 58120795 | 58120961 | Hypo | cancer_general | SETD6, CNOT1, NDRG4 | chr16 | 58427501 | 58427542 | Hypo | cancer_general | GINS3 NDRG4, CNOT1, SETD6 |
| chr16 | 58545487 | 58545516 | Hypo | literature | | chr16 | 58550489 | 58550519 | Hypo | cancer_general | |
| chr16 | 58969757 | 58969792 | Hypo | cancer_general | AK057513 | chr16 | 66863917 | 66863959 | Hypo | cancer_general | NAE1 |
| chr16 | 67241204 | 67241234 | Hypo | cancer_general | LRRC29, MIR328, ELMO3, E2F4 | chr16 | 67313865 | 67313895 | Hypo | cancer_general | KCTD19, PLEKHG4 |
| chr16 | 67850955 | 67850985 | Hypo | cancer_general | TSNAXIP1 | chr16 | 67871102 | 67871134 | Hypo | cancer_general | NUTF2, CENPT, TSNAXIP1, THAP11 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 68770755 | 68770974 | Hypo | cancer_general | CDH1 | chr16 | 68844158 | 68844187 | Hypo | literature | CDH1 |
| chr16 | 68846033 | 68846062 | Hypo | literature | CDH1 | chr16 | 68856078 | 68856107 | Hypo | literature | CDH1 |
| chr16 | 68876782 | 68876996 | Hypo | cancer_general | TANGO6, CDH1 | chr16 | 69026784 | 69028814 | Hypo | cancer_general | TANGO6 |
| chr16 | 69564118 | 69564200 | Hypo | cancer_general | | chr16 | 69969260 | 69969290 | Hypo | breast | MIR140, WWP2 |
| chr16 | 70489585 | 70489681 | Hypo | cancer_general | FUK | chr16 | 70595535 | 70595700 | Hypo | cancer_general | ZNF19, AK123826, ZNF23 |
| chr16 | 70794492 | 70794633 | Hypo | cancer_general | BC033164, VAC14-AS1 | chr16 | 71507759 | 71507791 | Hypo | cancer_general | |
| chr16 | 71677557 | 71677661 | Hypo | breast | KIAA0931, PHLPP2, MARVELD3 | chr16 | 71715779 | 71715809 | Hypo | colorectal | PHLPP2, TRNA_Gln |
| chr16 | 71918889 | 71919024 | Hypo | cancer_general | IST1, ZNF821 | chr16 | 72957763 | 72957795 | Hypo | cancer_general | WDR59 |
| chr16 | 74886148 | 74886268 | Hypo | cancer_general | | chr16 | 74901594 | 74901659 | Hypo | cancer_general | |
| chr16 | 75019751 | 75019781 | Hypo | cancer_general | | chr16 | 75549798 | 75549836 | Hypo | cancer_general | |
| chr16 | 76008985 | 76009154 | Hypo | hepatobiliary | | chr16 | 77247440 | 77247470 | Hypo | cancer_general | SYCE1L |
| chr16 | 81564199 | 81564229 | Hypo | cancer_general | CMIP | chr16 | 81929362 | 81929392 | Hypo | breast | PLCG2 |
| chr16 | 81946246 | 81946275 | Hypo | literature | PLCG2 | chr16 | 81962167 | 81962196 | Hypo | literature | PLCG2 |
| chr16 | 84074836 | 84074871 | Hypo | cancer_general | SLC38A8 | chr16 | 84153364 | 84153394 | Hypo | cancer_general | MBTPS1, HSDL1 |
| chr16 | 84519974 | 84520010 | Hypo | hepatobiliary | TLDC1 | chr16 | 84823626 | 84823656 | Hypo | breast | |
| chr16 | 85075434 | 85075553 | Hypo | cancer_general | KIAA0513 | chr16 | 85317850 | 85317882 | Hypo | cancer_general | LINC00311 |
| chr16 | 85485747 | 85485855 | Hypo | cancer_general | | chr16 | 85497445 | 85497475 | Hypo | cancer_general | |
| chr16 | 85517345 | 85517521 | Hypo | lung, cancer_general | | chr16 | 86511520 | 86511550 | Hypo | cancer_general | GSE1 |
| chr16 | 85678639 | 85678761 | Hypo | cancer_general | GSE1 | chr16 | 85684308 | 85684457 | Hypo | cancer_general | GSE1 |
| chr16 | 85699689 | 85699921 | Hypo | breast | GSE1 | chr16 | 85834460 | 85834495 | Hypo | cancer_general | COX4I1, EMC8 |
| chr16 | 86571984 | 86572014 | Hypo | pancreas | MTHFSD | chr16 | 86878150 | 86878180 | Hypo | cancer_general | |
| chr16 | 87092439 | 87092553 | Hypo | cancer_general | | chr16 | 87714272 | 87714381 | Hypo | cancer_general | |
| chr16 | 87723735 | 87724098 | Hypo | cancer_general | FLJ00104, hCG_1980662 | chr16 | 88007072 | 88007108 | Hypo | head_neck | BANP |
| chr16 | 88106322 | 88106398 | Hypo | breast | BANP | chr16 | 88164401 | 88164468 | Hypo | cancer_general | ZNF469 |
| chr16 | 88498241 | 88498760 | Hypo | cancer_general | ZNF469 | chr16 | 88504058 | 88504315 | Hypo | cancer_general | ZFPM1, ZNF469 |
| chr16 | 88506346 | 88506526 | Hypo | cancer_general | ZNF469 | chr16 | 88512427 | 88512529 | Hypo | cancer_general | |
| chr16 | 88550263 | 88550483 | Hypo | cancer_general | | chr16 | 88603696 | 88603760 | Hypo | cancer_general | |
| chr16 | 88623960 | 88624167 | Hypo | cancer_general | C16orf85 | chr16 | 88711337 | 88711507 | Hypo | hepatobiliary | BC033739, MVD, BC028224, IL17C, CYBA |
| chr16 | 88757466 | 88757496 | Hypo | head_neck | RNF166, SNAI3 | chr16 | 88879949 | 88880124 | | | GALNS, APRT, CDT1 |
| chr16 | 88883238 | 88883377 | Hypo | cancer_general | GALNS, APRT, CDT1 | chr16 | 89941058 | 89941141 | Hypo | cancer_general | CBFA2T3, PABPN1L |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 88942119 | 88942160 | Hypo | hepatobiliary | PABPN1L, CBFA2T3 | chr16 | 88943559 | 88944024 | Hypo | cancer_general | CBFA2T3 |
| chr16 | 88945815 | 88945995 | Hypo | cancer_general | CBFA2T3 | chr16 | 88955249 | 88955368 | Hypo | cancer_general | CBFA2T3 |
| chr16 | 88956230 | 88956399 | Hypo | cancer_general | CBFA2T3 | chr16 | 88957350 | 88957857 | Hypo | cancer_general | CBFA2T3 |
| chr16 | 88958397 | 88958431 | Hypo | cancer_general | CBFA2T3 | chr16 | 88963277 | 88963763 | Hypo | cancer_general | CBFA2T3 |
| chr16 | 88966303 | 88966588 | Hypo | cancer_general | CBFA2T3 | chr16 | 88968709 | 88968789 | Hypo | cancer_general | CBFA2T3 |
| chr16 | 88978024 | 88978072 | Hypo | cancer_general | CBFA2T3 | chr16 | 88993078 | 88993230 | Hypo | cancer_general | CBFA2T3 |
| chr16 | 88999617 | 88999647 | Hypo | cancer_general | CBFA2T3 | chr16 | 89000168 | 89000204 | Hypo | cancer_general | CBFA2T3 |
| chr16 | 89001094 | 89001124 | Hypo | cancer_general | CBFA2T3 | chr16 | 89047717 | 89047747 | Hypo | cancer_general | CBFA2T3 |
| chr16 | 89072503 | 89072774 | Hypo | cancer_general | | chr16 | 89086109 | 89086197 | Hypo | cancer_general | |
| chr16 | 89107675 | 89107732 | Hypo | cancer_general | AK055272 | chr16 | 89109385 | 89109415 | Hypo | cancer_general | AK055272 |
| chr16 | 89120038 | 89120319 | Hypo | cancer_general | AK055272 | chr16 | 89120708 | 89120864 | Hypo | cancer_general | AK055272 |
| chr16 | 89138016 | 89138060 | Hypo | cancer_general | | chr16 | 89220327 | 89220398 | Hypo | cancer_general | LINC00304, ACSF3 |
| chr16 | 89220655 | 89220922 | Hypo | cancer_general | LINC00304, ACSF3 | chr16 | 89240843 | 89240873 | Hypo | head_neck | CDH15, LOC400558 |
| chr16 | 89254653 | 89254830 | Hypo | cancer_general | SLC22A31, CDH15 | chr16 | 89558610 | 89558703 | Hypo | cancer_general | |
| chr16 | 89575728 | 89575861 | Hypo | cancer_general | SPG7 | chr16 | 89584136 | 89584417 | Hypo | head_neck | SPG7 |
| chr16 | 89676025 | 89676197 | Hypo | cancer_general | DPEP1 | chr16 | 89883972 | 89884185 | Hypo | cancer_general | FANCA |
| chr16 | 89884966 | 89885142 | Hypo | cancer_general | SPIRE2, FANCA | chr16 | 89900124 | 89900180 | Hypo | cancer_general | SPIRE2 |
| chr16 | 89900455 | 89900526 | Hypo | cancer_general | SPIRE2 | chr16 | 90115428 | 90115458 | Hypo | cancer_general | LOC100130015, AK127378, PRDM7 |
| chr2 | 142427 | 142468 | Hypo | cancer_general | | chr2 | 496228 | 496380 | Hypo | cancer_general | |
| chr2 | 602657 | 602687 | Hypo | cancer_general | | chr2 | 720836 | 720894 | Hypo | cancer_general | |
| chr2 | 875961 | 875991 | Hypo | cancer_general | | chr2 | 1652837 | 1653230 | Hypo | hepatobiliary | |
| chr2 | 1670168 | 1670216 | Hypo | hepatobiliary | | chr2 | 2321773 | 2321802 | Hypo | literature | |
| chr2 | 2336413 | 2336442 | Hypo | literature | | chr2 | 2646900 | 2646930 | Hypo | cancer_general | |
| chr2 | 2672620 | 2672732 | Hypo | cancer_general | PXDN | chr2 | 2844720 | 2844750 | Hypo | cancer_general | PXDN |
| chr2 | 2893165 | 2893195 | Hypo | cancer_general | LOC730811 | chr2 | 3259989 | 3260103 | Hypo | pancreas | LOC730811 |
| chr2 | 4019911 | 4020036 | Hypo | cancer_general | AK095310 | chr2 | 4050752 | 4050781 | Hypo | literature | |
| chr2 | 7062891 | 7062959 | Hypo | ovarian | LOC100505964 RNF144A, RNF144A-AS1 | chr2 | 7164467 | 7164788 | Hypo | pancreas | TSSC1 |
| chr2 | 7236859 | 7236974 | Hypo | breast | | chr2 | 8735932 | 8736064 | Hypo | ovarian | |
| chr2 | 8835493 | 8835523 | Hypo | cancer_general | | chr2 | 9090685 | 9090760 | Hypo | hepatobiliary | |
| chr2 | 9134404 | 9134493 | Hypo | breast | | chr2 | 9192356 | 9192402 | Hypo | hepatobiliary | |
| chr2 | 9289969 | 9290114 | Hypo | cancer_general | MBOAT2 | chr2 | 9960734 | 9960764 | Hypo | cancer_general | MBOAT2 |
| chr2 | 10115730 | 10115772 | Hypo | cancer_general | | chr2 | 10152798 | 10153325 | Hypo | cancer_general | |
| chr2 | 10154266 | 10154564 | Hypo | cancer_general | | chr2 | 10154930 | 10155298 | Hypo | cancer_general | |
| chr2 | 10156116 | 10156389 | Hypo | cancer_general | | chr2 | 10369155 | 10369242 | Hypo | pancreas | |
| chr2 | 10408398 | 10408459 | Hypo | cancer_general | | chr2 | 11142174 | 11142315 | Hypo | cancer_general | |
| chr2 | 11356651 | 11356762 | Hypo | ovarian | ROCK2 | chr2 | 11672746 | 11672775 | Hypo | literature | GREB1, MIR4429 |
| chr2 | 11903450 | 11903480 | Hypo | pancreas | LPIN1 | chr2 | 12246114 | 12246217 | Hypo | cancer_general | |
| chr2 | 12297534 | 12297564 | Hypo | cancer_general | | chr2 | 13557899 | 13558057 | Hypo | hepatobiliary | |
| chr2 | 15579989 | 15580019 | Hypo | cancer_general | | chr2 | 20442433 | 20442498 | Hypo | cancer_general | PUM2 |
| chr2 | 20641988 | 20642081 | Hypo | cancer_general | RHOB | chr2 | 20642541 | 20642648 | Hypo | cancer_general | RHOB |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 20710145 | 20710324 | Hypo | cancer_general | | chr2 | 22404181 | 22404227 | Hypo | cancer_general | CENPO |
| chr2 | 24318290 | 24318357 | Hypo | cancer_general | | chr2 | 25029252 | 25029300 | Hypo | cancer_general | |
| chr2 | 25374762 | 25374804 | Hypo | cancer_general | POMC, EFR3B | chr2 | 25439727 | 25439915 | Hypo | cancer_general | |
| chr2 | 25600736 | 25600804 | Hypo | head_neck | DTNB | chr2 | 25928094 | 25928166 | Hypo | head_neck | Y_RNA TMEM214, TRNA, TRNA_Tyr, TRNA_Ala, AGBL5 |
| chr2 | 26372967 | 26372997 | Hypo | cancer_general | | chr2 | 27271699 | 27272218 | Hypo | cancer_general | ATRAID, CAD, SLC5A6 |
| chr2 | 27356168 | 27356198 | Hypo | ovarian | C2orf53, PREB, AK074615, ABHD1 | chr2 | 27433532 | 27433601 | Hypo | cancer_general | |
| chr2 | 27543012 | 27543074 | Hypo | lung | GTF3C2, MPV17 | chr2 | 27578243 | 27578396 | Hypo | cancer_general | EIF2B4 |
| chr2 | 27648172 | 27648294 | Hypo | cancer_general | NRBP1 | chr2 | 27764046 | 27764168 | Hypo | cancer_general | |
| chr2 | 27887525 | 27887555 | Hypo | cancer_general | SLC4A1AP, SUPT7L | chr2 | 29091592 | 29091838 | Hypo | cancer_general | TRMT61B |
| chr2 | 29420483 | 29420512 | Hypo | literature | ALK | chr2 | 29432640 | 29432696 | Hypo | literature | ALK |
| chr2 | 29436844 | 29436888 | Hypo | literature | ALK | chr2 | 29443573 | 29443710 | Hypo | literature | ALK |
| chr2 | 29445198 | 29445482 | Hypo | literature | ALK | chr2 | 29446361 | 29446396 | Hypo | literature | ALK |
| chr2 | 30368444 | 30368586 | Hypo | cancer_general | YPEL5 | chr2 | 30514753 | 30514783 | Hypo | hepatobiliary | YIPF4 |
| chr2 | 32275196 | 32275303 | Hypo | cancer_general | | chr2 | 32504169 | 32504378 | Hypo | cancer_general | CYP1B1-AS1 |
| chr2 | 32580386 | 32580476 | Hypo | colorectal | BIRC6 | chr2 | 38365525 | 38365748 | Hypo | cancer_general | |
| chr2 | 38551124 | 38551390 | Hypo | ovarian | ATL2 | chr2 | 38594819 | 38594874 | Hypo | breast | ATL2 |
| chr2 | 38727561 | 38727707 | Hypo | breast | | chr2 | 38762382 | 38762412 | Hypo | colorectal | |
| chr2 | 38955573 | 38955603 | Hypo | cancer_general | GALM | chr2 | 38983213 | 38983333 | Hypo | head_neck | GEMIN6, SRSF7 |
| chr2 | 41789816 | 41789853 | Hypo | hepatobiliary | | chr2 | 43388330 | 43388529 | Hypo | colorectal, cancer_general | |
| chr2 | 43824133 | 43824353 | Hypo | cancer_general | THADA | chr2 | 44226958 | 44226988 | Hypo | head_neck | LRPPRC |
| chr2 | 44227193 | 44227223 | Hypo | head_neck | LRPPRC | chr2 | 44497708 | 44497875 | Hypo | breast | SLC3A1 |
| chr2 | 44809187 | 44809217 | Hypo | ovarian | | chr2 | 47193930 | 47194136 | Hypo | pancreas, cancer_general | TTC7A |
| chr2 | 47200591 | 47200621 | Hypo | ovarian | TTC7A | chr2 | 47249725 | 47249848 | Hypo | ovarian | TTC7A |
| chr2 | 47597455 | 47598620 | Hypo | cancer_general | MIR559, EPCAM | chr2 | 47599589 | 47599753 | Hypo | cancer_general | MIR559, EPCAM |
| chr2 | 48629615 | 48629685 | Hypo | cancer_general | | chr2 | 48636504 | 48636669 | Hypo | cancer_general | |
| chr2 | 48648878 | 48648940 | Hypo | cancer_general | | chr2 | 50573802 | 50573865 | Hypo | cancer_general | NRXN1 |
| chr2 | 54322431 | 54322576 | Hypo | lung | | chr2 | 55289011 | 55289296 | Hypo | lung | |
| chr2 | 55612770 | 55612800 | Hypo | colorectal | | chr2 | 55669261 | 55669454 | Hypo | cancer_general | |
| chr2 | 58552519 | 58552689 | Hypo | cancer_general | | chr2 | 59400384 | 59400424 | Hypo | cancer_general | |
| chr2 | 60416280 | 60416494 | Hypo | cancer_general | | chr2 | 60706759 | 60706804 | Hypo | cancer_general | BCL11A PUS10 |
| chr2 | 61135032 | 61135137 | Hypo | breast | REL | chr2 | 61232163 | 61232232 | Hypo | cancer_general | 5S_rRNA |
| chr2 | 61242732 | 61242802 | Hypo | cancer_general | PEX13, PUS10 | chr2 | 61395039 | 61395069 | Hypo | cancer_general | C2orf74, AHSA2 |
| chr2 | 61556203 | 61556239 | Hypo | cancer_general | | chr2 | 61656393 | 61656423 | Hypo | breast | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 61992076 | 61992289 | Hypo | cancer_general | FLJ16124 | chr2 | 65251310 | 65251340 | Hypo | head_neck | SLC1A4 |
| chr2 | 65779892 | 65779983 | Hypo | cancer_general | | chr2 | 67625453 | 67625770 | Hypo | cancer_general | ETAA1 |
| chr2 | 67626102 | 67626257 | Hypo | cancer_general | ETAA1 | chr2 | 68287707 | 68287799 | Hypo | head_neck | C1D |
| chr2 | 68559265 | 68559365 | Hypo | cancer_general | | chr2 | 68672853 | 68672938 | Hypo | cancer_general | |
| chr2 | 69027024 | 69027053 | Hypo | literature | ARHGAP25 | chr2 | 69975443 | 69975523 | Hypo | pancreas | ANXA4 |
| chr2 | 70058262 | 70058292 | Hypo | cancer_general | GMCL1 | chr2 | 70367670 | 70367710 | Hypo | lung | C2orf42 |
| chr2 | 70418528 | 70418627 | Hypo | cancer_general | C2orf42 | chr2 | 70427556 | 70427646 | Hypo | lung | TIA1, C2orf42 |
| chr2 | 70430997 | 70431160 | Hypo | cancer_general | TIA1 | chr2 | 71355019 | 71355117 | Hypo | cancer_general | MPHOSPH10, MCEE |
| chr2 | 71355768 | 71355961 | Hypo | cancer_general | MPHOSPH10, MCEE | chr2 | 73147353 | 73147383 | Hypo | cancer_general | EMX1 |
| chr2 | 73416356 | 73416535 | Hypo | lung | | chr2 | 73440206 | 73440293 | Hypo | cancer_general | SMYD5, NOTO |
| chr2 | 74010528 | 74010773 | Hypo | cancer_general | C2orf78, DUSP11 | chr2 | 74153198 | 74153227 | Hypo | literature | DGUOK, ACTG2 |
| chr2 | 74350410 | 74350497 | Hypo | cancer_general | WDR54, RTKN, DQ588163, C2orf81 | chr2 | 74454074 | 74454261 | Hypo | cancer_general | SLC4A5 |
| chr2 | 74647864 | 74648007 | Hypo | cancer_general | | chr2 | 74679047 | 74679123 | Hypo | cancer_general | INO80B, INO80B-WBP1, WBP1, MOGS, RTKN |
| chr2 | 74874865 | 74874903 | Hypo | cancer_general | SEMA4F | chr2 | 79347459 | 79347546 | Hypo | literature | REG1A |
| chr2 | 85838101 | 85838299 | Hypo | cancer_general | C2orf68, TMEM150A, USP39 | chr2 | 86191145 | 86191309 | Hypo | cancer_general | |
| chr2 | 86423330 | 86423592 | Hypo | cancer_general | MRPL35, MIR4779, IMMT | chr2 | 86783725 | 86783755 | Hypo | cancer_general | RNF103-CHMP3, CHMP3 |
| chr2 | 86791221 | 86791251 | Hypo | ovarian | RNF103-CHMP3, CHMP3 | chr2 | 88469312 | 88469483 | Hypo | cancer_general | THNSL2 |
| chr2 | 88990189 | 88990264 | Hypo | cancer_general | RPIA | chr2 | 89252535 | 89252679 | Hypo | cancer_general | |
| chr2 | 95941678 | 95941812 | Hypo | cancer_general | PROM2 | chr2 | 96070057 | 96070165 | Hypo | breast | |
| chr2 | 96974486 | 96974516 | Hypo | lung | | chr2 | 97126702 | 97126832 | Hypo | head_neck | FAHD2A |
| chr2 | 97427215 | 97428093 | Hypo | cancer_general | CNNM4 | chr2 | 98581819 | 98581849 | Hypo | colorectal | |
| chr2 | 99796259 | 99796330 | Hypo | cancer_general | MRPL30, MITD1 | chr2 | 99799646 | 99799153 | Hypo | cancer_general | TMEM131 MRPL30, MITD1 |
| chr2 | 100618451 | 100618480 | Hypo | literature | AFF3 | chr2 | 101009832 | 101009927 | Hypo | cancer_general | CHST10 |
| chr2 | 101186368 | 101186458 | Hypo | ovarian | PDCL3 | chr2 | 101834977 | 101835057 | Hypo | cancer_general | |
| chr2 | 105488437 | 105488496 | Hypo | cancer_general | AK095498 | chr2 | 105937344 | 105937498 | Hypo | cancer_general | TGFBRAP1 |
| chr2 | 106060615 | 106060792 | Hypo | lung | | chr2 | 106730223 | 106730256 | Hypo | cancer_general | UXS1 |
| chr2 | 106959368 | 106959568 | Hypo | cancer_general | | chr2 | 106959916 | 106959988 | Hypo | cancer_general | |
| chr2 | 108364897 | 108364940 | Hypo | cancer_general | | chr2 | 109335133 | 109335166 | Hypo | cancer_general | RANBP2 |
| chr2 | 110015080 | 110015110 | Hypo | ovarian | | chr2 | 111544817 | 111544997 | Hypo | cancer_general | ACOXL |
| chr2 | 112817735 | 112817765 | Hypo | colorectal | TMEM87B | chr2 | 113227024 | 113227225 | Hypo | esophageal | |
| chr2 | 113803960 | 113803990 | Hypo | cancer_general | IL36B | chr2 | 114461746 | 114461879 | Hypo | colorectal | |
| chr2 | 114470022 | 114470201 | Hypo | ovarian | SLC35F5, MIR4782 | chr2 | 114515528 | 114515618 | Hypo | cancer_general | SLC35F5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 114634867 | 114634988 | Hypo | cancer_general | | chr2 | 118380865 | 118380904 | Hypo | pancreas | EPB41L5 |
| chr2 | 119600570 | 119600747 | Hypo | cancer_general | | chr2 | 120769511 | 120769746 | Hypo | cancer_general | TMEM185B |
| chr2 | 120825608 | 120825769 | Hypo | lung | EN1 | chr2 | 120980068 | 120980098 | Hypo | cancer_general | MKI67IP |
| chr2 | 120980353 | 120980395 | Hypo | cancer_general | EPB41L5 | chr2 | 122495267 | 122495413 | Hypo | cancer_general | GYPC |
| chr2 | 122809705 | 122809801 | Hypo | cancer_general | TMEM185B | chr2 | 127412291 | 127412386 | Hypo | cancer_general | GYPC |
| chr2 | 127423220 | 127423350 | Hypo | cancer_general | | chr2 | 127429010 | 127429044 | Hypo | cancer_general | AMMECR1L, POLR2D |
| chr2 | 127438633 | 127438663 | Hypo | cancer_general | GYPC | chr2 | 128616617 | 128616838 | Hypo | cancer_general | |
| chr2 | 128680057 | 128680087 | Hypo | cancer_general | GYPC | chr2 | 128847677 | 128847723 | Hypo | cancer_general | UGGT1 |
| chr2 | 129174888 | 129174918 | Hypo | cancer_general | | chr2 | 130937868 | 130937898 | Hypo | cancer_general | MZT2B, FLJ14346, SMPD4 |
| chr2 | 131084953 | 131085013 | Hypo | cancer_general | TRNA_Glu | chr2 | 131477785 | 131477936 | Hypo | cancer_general | GPR148 |
| chr2 | 132208115 | 132208278 | Hypo | cancer_general | LOC401010 | chr2 | 136287358 | 136287390 | Hypo | cancer_general | R3HDM1, ZRANB3 |
| chr2 | 143569561 | 143569694 | Hypo | cancer_general | | chr2 | 144129765 | 144129795 | Hypo | cancer_general | ARHGAP15 |
| chr2 | 144299758 | 144299788 | Hypo | cancer_general | ARHGAP15 | chr2 | 148776809 | 148777035 | Hypo | cancer_general | MBD5, ORC4 |
| chr2 | 152248836 | 152248983 | Hypo | cancer_general | | chr2 | 161253293 | 161253455 | Hypo | cancer_general | RBMS1 |
| chr2 | 162166600 | 162166632 | Hypo | cancer_general | PSMD14 | chr2 | 166929478 | 166929613 | Hypo | cancer_general | BC051759, SCN1A |
| chr2 | 170255970 | 170256139 | Hypo | cancer_general | | chr2 | 170282981 | 170283080 | Hypo | cancer_general | PHOSPHO2, PHOSPHO2-KLHL23, CCDC173 |
| chr2 | 170373281 | 170373413 | Hypo | lung | KLHL41 | chr2 | 170551730 | 170551942 | Hypo | cancer_general, literature | GORASP2 |
| chr2 | 170681880 | 170682422 | Hypo | cancer_general | UBR3, METTL5 | chr2 | 171822428 | 171822480 | Hypo | pancreas | |
| chr2 | 171839017 | 171839047 | Hypo | cancer_general | TLK1 | chr2 | 172367021 | 172367125 | Hypo | colorectal | DLX2 |
| chr2 | 172411136 | 172411166 | Hypo | cancer_general | CYBRD1 | chr2 | 172973111 | 172973141 | Hypo | cancer_general | MLK7-AS1 |
| chr2 | 173422685 | 173422734 | Hypo | cancer_general | PDK1 | chr2 | 174148058 | 174148157 | Hypo | head_neck | |
| chr2 | 175111870 | 175112092 | Hypo | cancer_general | OLA1 | chr2 | 175261402 | 175261432 | Hypo | cancer_general | SCRN3, CIR1 |
| chr2 | 175383935 | 175383965 | Hypo | cancer_general | | chr2 | 176987367 | 176987397 | Hypo | pancreas | HOXD9, AX747372, HOXD8, HOXD10 |
| chr2 | 176994031 | 176994136 | Hypo | cancer_general | HOXD9, HOXD10, HOXD8, HOXD-AS2, BC047605, AX747372 | chr2 | 177872600 | 177872629 | Hypo | literature | |
| chr2 | 178098791 | 178098967 | Hypo | literature | NFE2L2 | chr2 | 178973003 | 178973042 | Hypo | ovarian | RBM45 |
| chr2 | 179303534 | 179303727 | Hypo | cancer_general | AX747806, PRKRA, BX538254, MIR548N | chr2 | 179316860 | 179317057 | Hypo | cancer_general | DFNB59 |

TABLE 11-continued

| chr | Start | Stop | Hypo/hyper | classification | annotation |
|---|---|---|---|---|---|
| chr2 | 182202233 | 182202291 | Hypo | cancer_general | |
| chr2 | 190708790 | 190708819 | Hypo | literature | PMS1 |
| chr2 | 198238409 | 198238439 | Hypo | cancer_general | |
| chr2 | 198456480 | 198456719 | Hypo | cancer_general | RFTN2 |
| chr2 | 201156690 | 201156804 | Hypo | ovarian | |
| chr2 | 202477462 | 202477621 | Hypo | cancer_general | TMEM237, ALS2CR11 |
| chr2 | 203498452 | 203498489 | Hypo | ovarian | FAM117B |
| chr2 | 204194588 | 204194725 | Hypo | cancer_general | ABI2 |
| chr2 | 208574821 | 208574917 | Hypo | cancer_general | CCNYL1 |
| chr2 | 208662170 | 208662376 | Hypo | lung | |
| chr2 | 209094739 | 209094845 | Hypo | cancer_general | IDH1 |
| chr2 | 209225237 | 209225275 | Hypo | ovarian | PTH2R |
| chr2 | 212288927 | 212288956 | Hypo | literature | ERBB4 |
| chr2 | 212530120 | 212530149 | Hypo | literature | ERBB4 |
| chr2 | 212566811 | 212566840 | Hypo | literature | ERBB4 |
| chr2 | 212587132 | 212587161 | Hypo | literature | ERBB4 |
| chr2 | 217396039 | 217396069 | Hypo | ovarian | |
| chr2 | 219276888 | 219276918 | Hypo | blood | VIL1, MIR26B, CTDSP1 |
| chr2 | 221853201 | 221853352 | Hypo | hepatobiliary | |
| chr2 | 222310068 | 222310105 | Hypo | hepatobiliary | EPHA4 |
| chr2 | 224661521 | 224661701 | Hypo | pancreas | AP1S3 |
| chr2 | 228411020 | 228411050 | Hypo | cancer_general | AGFG1 |
| chr2 | 228638272 | 228638302 | Hypo | lung | |
| chr2 | 230795535 | 230795565 | Hypo | cancer_general | |
| chr2 | 232330451 | 232330481 | Hypo | cancer_general | TRIP12, FBXO36 |
| chr2 | 232506605 | 232506635 | Hypo | cancer_general | SNORD82, SNORD20, SNORA75, NCL |
| chr2 | 232544500 | 232544530 | Hypo | cancer_general | |
| chr2 | 232827168 | 232827349 | Hypo | cancer_general | DIS3L2 |
| chr2 | 233220227 | 233220382 | Hypo | cancer_general | |
| chr2 | 234776483 | 234776553 | Hypo | cancer_general | MSL3P1 |
| chr2 | 236877262 | 236877399 | Hypo | lung | AGAP1 |
| chr2 | 239051198 | 239051228 | Hypo | cancer_general | KLHL30, ESPNL |
| chr2 | 183251240 | 183251303 | Hypo | hepatobiliary | PDE1A |
| chr2 | 197793125 | 197793267 | Hypo | cancer_general | PGAP1 |
| chr2 | 198267345 | 198267374 | Hypo | literature | SnR39B, SF3B1 |
| chr2 | 200818892 | 200819130 | Hypo | cancer_general | C2orf47, TYW5 |
| chr2 | 201693680 | 201693718 | Hypo | colorectal | |
| chr2 | 203484608 | 203484646 | Hypo | cancer_general | BZW1 |
| chr2 | 203880390 | 203880492 | Hypo | cancer_general | NBEAL1 |
| chr2 | 207022702 | 207022802 | Hypo | cancer_general | EEF1B2, SNORD51, SNORA41, NDUFS1 |
| chr2 | 208588311 | 208588341 | Hypo | cancer_general | CCNYL1 |
| chr2 | 208662672 | 208662710 | Hypo | lung | |
| chr2 | 209113097 | 209113126 | Hypo | literature | IDH1-AS1, IDH1 |
| chr2 | 212248428 | 212248457 | Hypo | literature | ERBB4 |
| chr2 | 212295683 | 212295820 | Hypo | literature | ERBB4 |
| chr2 | 212537902 | 212537994 | Hypo | literature | ERBB4 |
| chr2 | 212578292 | 212578321 | Hypo | literature | ERBB4 |
| chr2 | 215276310 | 215276339 | Hypo | literature | VWC2L |
| chr2 | 217448294 | 1217448441 | Hypo | esophageal | |
| chr2 | 220080510 | 220081033 | Hypo | ovarian | ABCB6, ZFAND2B, ATG9A |
| chr2 | 222285828 | 222285858 | Hypo | hepatobiliary | EPHA4 |
| chr2 | 223166270 | 223166408 | Hypo | cancer_general | CCDC140, DD413687, PAX3 |
| chr2 | 225464038 | 225464068 | Hypo | cancer_general | |
| chr2 | 228466625 | 228466777 | Hypo | cancer_general | C2orf83 |
| chr2 | 228735680 | 228735736 | Hypo | cancer_general | DAW1 |
| chr2 | 231576609 | 231576643 | Hypo | cancer_general | CAB39 |
| chr2 | 232506220 | 232506294 | Hypo | cancer_general | |
| chr2 | 233522844 | 233522874 | Hypo | cancer_general | |
| chr2 | 233546736 | 233546842 | Hypo | cancer_general | |
| chr2 | 233073078 | 233073223 | Hypo | ovarian | |
| chr2 | 233750525 | 233750555 | Hypo | cancer_general | |
| chr2 | 236444269 | 236444298 | Hypo | literature | NGEF, C2orf82 |
| chr2 | 239031722 | 239031780 | Hypo | cancer_general | AGAP1, ESPNL |
| chr2 | 239265496 | 239265787 | Hypo | cancer_general | TRAF3IP1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 239482485 | 239482519 | Hypo | cancer_general | | chr2 | 239705305 | 239705337 | Hypo | cancer_general | U4 |
| chr2 | 239957330 | 239957448 | Hypo | cancer_general | | chr2 | 240167575 | 240167605 | Hypo | cancer_general | |
| chr2 | 240168811 | 240169051 | Hypo | cancer_general | | chr2 | 240319920 | 240320012 | Hypo | ovarian | |
| chr2 | 240582379 | 240582524 | Hypo | cancer_general | | chr2 | 240619459 | 240619604 | Hypo | cancer_general | |
| chr2 | 240658227 | 240658421 | Hypo | cancer_general | | chr2 | 240658667 | 240658697 | Hypo | cancer_general | |
| chr2 | 240812243 | 240812374 | Hypo | cancer_general | | chr2 | 241095604 | 241095772 | Hypo | cancer_general | |
| chr2 | 241541932 | 241542357 | Hypo | cancer_general, colorectal | GPR35, CAPN10 | chr2 | 241545001 | 241545031 | Hypo | cancer_general | GPR35, CAPN10 |
| chr2 | 241865194 | 241865346 | Hypo | cancer_general | SNED1 | chr2 | 242009391 | 242009421 | Hypo | cancer_general | SNED1 |
| chr2 | 242021784 | 242021892 | Hypo | cancer_general | 5S_rRNA, THAP4 | chr2 | 242314494 | 242314524 | Hypo | cancer_general | FARP2 |
| chr2 | 242523907 | 242524147 | Hypo | lung, cancer_general | | chr2 | 242554549 | 242554579 | Hypo | cancer_general | |
| chr2 | 242636726 | 242636812 | Hypo | cancer_general | ING5 | chr2 | 242640015 | 242640045 | Hypo | cancer_general | ING5 |
| chr2 | 242716723 | 242716760 | Hypo | cancer_general | GAL3ST2, D2HGDH | chr2 | 242756144 | 242756297 | Hypo | cancer_general | NEU4, PABL |
| chr2 | 242832984 | 242833159 | Hypo | cancer_general | | chr2 | 242833558 | 242833588 | Hypo | cancer_general | |
| chr2 | 242833797 | 242833863 | Hypo | cancer_general | | chr2 | 242836495 | 242836640 | Hypo | cancer_general | |
| chr2 | 242925496 | 242925641 | Hypo | pancreas | AK097934 | chrY | 3446305 | 3446441 | Hypo | hepatobiliary | TGIF2LY |
| chrY | 3838889 | 3838919 | Hypo | esophageal | | chrY | 3968100 | 3968132 | Hypo | hepatobiliary | |
| chrY | 13316007 | 13316132 | Hypo | head_neck | | chrY | 21204734 | 21205113 | Hypo | head_neck | |
| chrY | 22530026 | 22530073 | Hypo | | | HHV5-CINCY-TOWNE | 1181 | 1210 | Hypo | virus | |
| HHV5-CINCY-TOWNE | 1988 | 2017 | Hypo | virus | | HHV5-CINCY-TOWNE | 2389 | 2418 | Hypo | virus | |
| HHV5-CINCY-TOWNE | 3290 | 3319 | Hypo | virus | | HHV5-CINCY-TOWNE | 3665 | 3694 | Hypo | virus | |
| HHV5-CINCY-TOWNE | 4704 | 4733 | Hypo | virus | | HHV5-CINCY-TOWNE | 5400 | 5429 | Hypo | virus | |
| HHV5-CINCY-TOWNE | 7790 | 7819 | Hypo | virus | | HHV5-CINCY-TOWNE | 9656 | 9685 | Hypo | virus | |
| HHV5-CINCY-TOWNE | 10781 | 10810 | Hypo | virus | | HHV5-CINCY-TOWNE | 11109 | 11138 | Hypo | virus | |
| HHV5-CINCY-TOWNE | 12663 | 12692 | Hypo | virus | | HHV5-CINCY-TOWNE | 13688 | 13717 | Hypo | virus | |
| HHV5-CINCY-TOWNE | 14223 | 14252 | Hypo | virus | | HHV5-CINCY-TOWNE | 14911 | 14940 | Hypo | virus | |
| HHV5-CINCY-TOWNE | 15206 | 15235 | Hypo | virus | | HHV5-CINCY-TOWNE | 15938 | 15967 | Hypo | virus | |
| HHV5-CINCY-TOWNE | 16440 | 16469 | Hypo | virus | | HHV5-CINCY-TOWNE | 16884 | 16913 | Hypo | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 17347 | 17376 | Hypo | virus | | HHV5-CINCY-TOWNE | 17696 | 17725 | Hypo | virus | |
| HHV5-CINCY-TOWNE | 17958 | 17987 | Hypo | virus | | HHV5-CINCY-TOWNE | 18372 | 18401 | Hypo | virus | |
| HHV5-CINCY-TOWNE | 19417 | 19446 | Hypo | virus | | HHV5-CINCY-TOWNE | 19910 | 19939 | Hypo | virus | |
| HHV5-CINCY-TOWNE | 20248 | 20277 | Hypo | virus | | HHV5-CINCY-TOWNE | 20671 | 20700 | Hypo | virus | |
| HHV5-CINCY-TOWNE | 21899 | 21928 | Hypo | virus | | HHV5-CINCY-TOWNE | 22798 | 22827 | Hypo | virus | |
| HHV5-CINCY-TOWNE | 23095 | 23124 | Hypo | virus | | HHV5-CINCY-TOWNE | 26713 | 26742 | Hypo | virus | |
| HHV5-CINCY-TOWNE | 27211 | 27240 | Hypo | virus | | HHV5-CINCY-TOWNE | 29784 | 29813 | Hypo | virus | |
| HHV5-CINCY-TOWNE | 31141 | 31170 | Hypo | virus | | HHV5-CINCY-TOWNE | 32660 | 32689 | Hypo | virus | |
| HHV5-CINCY-TOWNE | 35651 | 35680 | Hypo | virus | | HHV5-CINCY-TOWNE | 36393 | 36422 | Hypo | virus | |
| HHV5-CINCY-TOWNE | 37224 | 37253 | Hypo | virus | | HHV5-CINCY-TOWNE | 37895 | 37924 | Hypo | virus | |
| HHV5-CINCY-TOWNE | 39244 | 39273 | Hypo | virus | | HHV5-CINCY-TOWNE | 43188 | 43217 | Hypo | virus | |
| HHV5-CINCY-TOWNE | 44447 | 44476 | Hypo | virus | | HHV5-CINCY-TOWNE | 44799 | 44828 | Hypo | virus | |
| HHV5-CINCY-TOWNE | 45394 | 45423 | Hypo | virus | | HHV5-CINCY-TOWNE | 46445 | 46474 | Hypo | virus | |
| HHV5-CINCY-TOWNE | 46944 | 46973 | Hypo | virus | | HHV5-CINCY-TOWNE | 47916 | 47945 | Hypo | virus | |
| HHV5-CINCY-TOWNE | 48504 | 48533 | Hypo | virus | | HHV5-CINCY-TOWNE | 49094 | 49123 | Hypo | virus | |
| HHV5-CINCY-TOWNE | 49903 | 49932 | Hypo | virus | | HHV5-CINCY-TOWNE | 50230 | 50259 | Hypo | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 51421 | 51450 | Hypo | virus | | HHV5-CINCY-TOWNE | 53772 | 53801 | Hypo | virus | |
| HHV5-CINCY-TOWNE | 55651 | 55680 | Hypo | virus | | HHV5-CINCY-TOWNE | 56380 | 56409 | Hypo | virus | |
| HHV5-CINCY-TOWNE | 57291 | 57320 | Hypo | virus | | HHV5-CINCY-TOWNE | 58491 | 58520 | Hypo | virus | |
| HHV5-CINCY-TOWNE | 59023 | 59052 | Hypo | virus | | HHV5-CINCY-TOWNE | 59792 | 59821 | Hypo | virus | |
| HHV5-CINCY-TOWNE | 60124 | 60153 | Hypo | virus | | HHV5-CINCY-TOWNE | 60392 | 60421 | Hypo | virus | |
| HHV5-CINCY-TOWNE | 60900 | 60929 | Hypo | virus | | HHV5-CINCY-TOWNE | 63894 | 63923 | Hypo | virus | |
| HHV5-CINCY-TOWNE | 65843 | 65872 | Hypo | virus | | HHV5-CINCY-TOWNE | 68089 | 68118 | Hypo | virus | |
| HHV5-CINCY-TOWNE | 72454 | 72483 | Hypo | virus | | HHV5-CINCY-TOWNE | 81185 | 81214 | Hypo | virus | |
| HHV5-CINCY-TOWNE | 84144 | 84173 | Hypo | virus | | HHV5-CINCY-TOWNE | 85524 | 85553 | Hypo | virus | |
| HHV5-CINCY-TOWNE | 85943 | 85972 | Hypo | virus | | HHV5-CINCY-TOWNE | 86889 | 86918 | Hypo | virus | |
| HHV5-CINCY-TOWNE | 87195 | 87224 | Hypo | virus | | HHV5-CINCY-TOWNE | 87455 | 87484 | Hypo | virus | |
| HHV5-CINCY-TOWNE | 87769 | 87798 | Hypo | virus | | HHV5-CINCY-TOWNE | 88564 | 88593 | Hypo | virus | |
| HHV5-CINCY-TOWNE | 93096 | 93125 | Hypo | virus | | HHV5-CINCY-TOWNE | 93776 | 93805 | Hypo | virus | |
| HHV5-CINCY-TOWNE | 97621 | 97650 | Hypo | virus | | HHV5-CINCY-TOWNE | 98737 | 98766 | Hypo | virus | |
| HHV5-CINCY-TOWNE | 99460 | 99489 | Hypo | virus | | HHV5-CINCY-TOWNE | 107540 | 107569 | Hypo | virus | |
| HHV5-CINCY-TOWNE | 108823 | 108852 | Hypo | virus | | HHV5-CINCY-TOWNE | 109725 | 109754 | Hypo | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 112036 | 112065 | Hypo | virus | | HHV5-CINCY-TOWNE | 112319 | 112348 | Hypo | virus | |
| HHV5-CINCY-TOWNE | 112595 | 112624 | Hypo | virus | | HHV5-CINCY-TOWNE | 112892 | 112921 | Hypo | virus | |
| HHV5-CINCY-TOWNE | 113194 | 113223 | Hypo | virus | | HHV5-CINCY-TOWNE | 113535 | 113564 | Hypo | virus | |
| HHV5-CINCY-TOWNE | 113927 | 113956 | Hypo | virus | | HHV5-CINCY-TOWNE | 114267 | 114296 | Hypo | virus | |
| HHV5-CINCY-TOWNE | 114593 | 114622 | Hypo | virus | | HHV5-CINCY-TOWNE | 114867 | 114896 | Hypo | virus | |
| HHV5-CINCY-TOWNE | 115177 | 115206 | Hypo | virus | | HHV5-CINCY-TOWNE | 115432 | 115461 | Hypo | virus | |
| HHV5-CINCY-TOWNE | 115685 | 115714 | Hypo | virus | | HHV5-CINCY-TOWNE | 115986 | 116015 | Hypo | virus | |
| HHV5-CINCY-TOWNE | 116382 | 116411 | Hypo | virus | | HHV5-CINCY-TOWNE | 116700 | 116729 | Hypo | virus | |
| HHV5-CINCY-TOWNE | 118193 | 118222 | Hypo | virus | | HHV5-CINCY-TOWNE | 118995 | 119024 | Hypo | virus | |
| HHV5-CINCY-TOWNE | 120028 | 120057 | Hypo | virus | | HHV5-CINCY-TOWNE | 121485 | 121514 | Hypo | virus | |
| HHV5-CINCY-TOWNE | 122199 | 122228 | Hypo | virus | | HHV5-CINCY-TOWNE | 122606 | 122635 | Hypo | virus | |
| HHV5-CINCY-TOWNE | 124559 | 124588 | Hypo | virus | | HHV5-CINCY-TOWNE | 125276 | 125305 | Hypo | virus | |
| HHV5-CINCY-TOWNE | 132497 | 132526 | Hypo | virus | | HHV5-CINCY-TOWNE | 135460 | 135489 | Hypo | virus | |
| HHV5-CINCY-TOWNE | 135730 | 135759 | Hypo | virus | | HHV5-CINCY-TOWNE | 137379 | 137408 | Hypo | virus | |
| HHV5-CINCY-TOWNE | 139067 | 139096 | Hypo | virus | | HHV5-CINCY-TOWNE | 139472 | 139501 | Hypo | virus | |
| HHV5-CINCY-TOWNE | 140147 | 140176 | Hypo | virus | | HHV5-CINCY-TOWNE | 140722 | 140751 | Hypo | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 142023 | 142052 | Hypo | virus | | HHV5-CINCY-TOWNE | 143692 | 143721 | Hypo | virus | |
| HHV5-CINCY-TOWNE | 144080 | 144109 | Hypo | virus | | HHV5-CINCY-TOWNE | 147310 | 147339 | Hypo | virus | |
| HHV5-CINCY-TOWNE | 149465 | 149494 | Hypo | virus | | HHV5-CINCY-TOWNE | 150359 | 150388 | Hypo | virus | |
| HHV5-CINCY-TOWNE | 151593 | 151622 | Hypo | virus | | HHV5-CINCY-TOWNE | 152153 | 152182 | Hypo | virus | |
| HHV5-CINCY-TOWNE | 154148 | 154177 | Hypo | virus | | HHV5-CINCY-TOWNE | 154610 | 154639 | Hypo | virus | |
| HHV5-CINCY-TOWNE | 157018 | 157047 | Hypo | virus | | HHV5-CINCY-TOWNE | 157367 | 157396 | Hypo | virus | |
| HHV5-CINCY-TOWNE | 169038 | 169067 | Hypo | virus | | HHV5-CINCY-TOWNE | 171503 | 171532 | Hypo | virus | |
| HHV5-CINCY-TOWNE | 175146 | 175175 | Hypo | virus | | HHV5-CINCY-TOWNE | 177553 | 177582 | Hypo | virus | |
| HHV5-CINCY-TOWNE | 182254 | 182283 | Hypo | virus | | HHV5-CINCY-TOWNE | 183115 | 183144 | Hypo | virus | |
| HHV5-CINCY-TOWNE | 184120 | 184149 | Hypo | virus | | HHV5-CINCY-TOWNE | 185558 | 185587 | Hypo | virus | |
| HHV5-CINCY-TOWNE | 186027 | 186056 | Hypo | virus | | HHV5-CINCY-TOWNE | 186435 | 186464 | Hypo | virus | |
| HHV5-CINCY-TOWNE | 186707 | 186736 | Hypo | virus | | HHV5-CINCY-TOWNE | 187115 | 187144 | Hypo | virus | |
| HHV5-CINCY-TOWNE | 187514 | 187543 | Hypo | virus | | HHV5-CINCY-TOWNE | 187859 | 187888 | Hypo | virus | |
| HHV5-CINCY-TOWNE | 188473 | 188502 | Hypo | virus | | HHV5-CINCY-TOWNE | 188768 | 188797 | Hypo | virus | |
| HHV5-CINCY-TOWNE | 189050 | 189079 | Hypo | virus | | HHV5-CINCY-TOWNE | 189302 | 189331 | Hypo | virus | |
| HHV5-CINCY-TOWNE | 189936 | 189965 | Hypo | virus | | HHV5-CINCY-TOWNE | 190655 | 190684 | Hypo | virus | |

TABLE 11-continued

| chr | Start | Stop | Hypo/hyper | classification | annotation |
|---|---|---|---|---|---|
| HHV5-CINCY-TOWNE | 190954 | 190983 | Hypo | virus | |
| HHV5-CINCY-TOWNE | 191882 | 191911 | Hypo | virus | |
| HHV5-CINCY-TOWNE | 192541 | 192570 | Hypo | virus | |
| HHV5-CINCY-TOWNE | 193325 | 193354 | Hypo | virus | |
| HHV5-CINCY-TOWNE | 194165 | 194194 | Hypo | virus | |
| HHV5-CINCY-TOWNE | 194848 | 194877 | Hypo | virus | |
| HHV5-CINCY-TOWNE | 195651 | 195680 | Hypo | virus | |
| HHV5-CINCY-TOWNE | 196343 | 196372 | Hypo | virus | |
| HHV5-CINCY-TOWNE | 197218 | 197247 | Hypo | virus | |
| HHV5-CINCY-TOWNE | 198792 | 198821 | Hypo | virus | |
| HHV5-CINCY-TOWNE | 200113 | 200142 | Hypo | virus | |
| HHV5-CINCY-TOWNE | 201373 | 201402 | Hypo | virus | |
| HHV5-CINCY-TOWNE | 202264 | 202293 | Hypo | virus | |
| HHV5-CINCY-TOWNE | 203319 | 203348 | Hypo | virus | |
| HHV5-CINCY-TOWNE | 204008 | 204037 | Hypo | virus | |
| HHV5-CINCY-TOWNE | 206735 | 206764 | Hypo | virus | |
| HHV5-CINCY-TOWNE | 191453 | 191482 | Hypo | virus | |
| HHV5-CINCY-TOWNE | 192183 | 192212 | Hypo | virus | |
| HHV5-CINCY-TOWNE | 193045 | 193074 | Hypo | virus | |
| HHV5-CINCY-TOWNE | 193597 | 193626 | Hypo | virus | |
| HHV5-CINCY-TOWNE | 194461 | 194490 | Hypo | virus | |
| HHV5-CINCY-TOWNE | 195324 | 195353 | Hypo | virus | |
| HHV5-CINCY-TOWNE | 196018 | 196047 | Hypo | virus | |
| HHV5-CINCY-TOWNE | 196941 | 196970 | Hypo | virus | |
| HHV5-CINCY-TOWNE | 198315 | 198344 | Hypo | virus | |
| HHV5-CINCY-TOWNE | 199162 | 199191 | Hypo | virus | |
| HHV5-CINCY-TOWNE | 200571 | 200600 | Hypo | virus | |
| HHV5-CINCY-TOWNE | 201905 | 201934 | Hypo | virus | |
| HHV5-CINCY-TOWNE | 202537 | 202566 | Hypo | virus | |
| HHV5-CINCY-TOWNE | 203720 | 203749 | Hypo | virus | |
| HHV5-CINCY-TOWNE | 206213 | 206242 | Hypo | virus | |
| HHV5-CINCY-TOWNE | 211676 | 211705 | Hypo | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 212340 | 212369 | Hypo | virus | | HHV5-CINCY-TOWNE | 212609 | 212638 | Hypo | virus | |
| HHV5-CINCY-TOWNE | 213813 | 213842 | Hypo | virus | | HHV5-CINCY-TOWNE | 214695 | 214724 | Hypo | virus | |
| HHV5-CINCY-TOWNE | 214950 | 214979 | Hypo | virus | | HHV5-CINCY-TOWNE | 215930 | 215959 | Hypo | virus | |
| HHV5-CINCY-TOWNE | 216228 | 216257 | Hypo | virus | | HHV5-CINCY-TOWNE | 222672 | 222701 | Hypo | virus | |
| HHV5-CINCY-TOWNE | 223515 | 223544 | Hypo | virus | | HHV5-CINCY-TOWNE | 225150 | 225179 | Hypo | virus | |
| HHV5-CINCY-TOWNE | 226058 | 226087 | Hypo | virus | | HHV5-CINCY-TOWNE | 226887 | 226916 | Hypo | virus | |
| chr20 | 118577 | 118751 | Hypo | cancer_general | DEFB126 | chr20 | 304259 | 304408 | Hypo | cancer_general | SOX12 |
| chr20 | 400007 | 400087 | Hypo | cancer_general | RBCK1 | chr20 | 401153 | 401183 | Hypo | cancer_general | RBCK1 |
| chr20 | 401591 | 401756 | Hypo | cancer_general | RBCK1 | chr20 | 523146 | 523193 | Hypo | cancer_general | CSNK2A1 |
| chr20 | 799104 | 799247 | Hypo | cancer_general | PSMF1 | chr20 | 799458 | 799706 | Hypo | cancer_general | RAD21L1, C20orf202 |
| chr20 | 1094560 | 1094682 | Hypo | ovarian | | chr20 | 1197670 | 1197711 | Hypo | cancer_general | IDH3B, SNORA51 |
| chr20 | 1975357 | 1975386 | Hypo | literature | PDYN, AK090681 | chr20 | 2645540 | 2645795 | Hypo | cancer_general | LZTS3 |
| chr20 | 3027758 | 3027931 | Hypo | cancer_general | MRPS26, GNRH2, PTPRA | chr20 | 3154172 | 3154204 | Hypo | breast | |
| chr20 | 3204870 | 3204952 | Hypo | cancer_general | SLC4A11, ITPA | chr20 | 3762407 | 3762436 | Hypo | tcga | CENPB, CDC25B, SPEF1 |
| chr20 | 3858389 | 3858632 | Hypo | cancer_general | BC012193, MAVS | chr20 | 3996688 | 3996726 | Hypo | cancer_general | RNF24 |
| chr20 | 4040710 | 4040871 | Hypo | cancer_general | | chr20 | 4061323 | 4061452 | Hypo | hepatobiliary | RASSF2 |
| chr20 | 4085057 | 4085087 | Hypo | cancer_general | | chr20 | 4804703 | 4804732 | Hypo | tcga | CDS2, PCNA-AS1, PCNA |
| chr20 | 5025228 | 5025258 | Hypo | cancer_general | | chr20 | 5106720 | 5106750 | Hypo | cancer_general | |
| chr20 | 5433047 | 5433085 | Hypo | ovarian | LINC00658 | chr20 | 5610356 | 5610386 | Hypo | colorectal | CRLS1, LRRN4 |
| chr20 | 6022797 | 6023045 | Hypo | breast | LRRN4, CRLS1 | chr20 | 6023268 | 6023351 | Hypo | breast | |
| chr20 | 7980362 | 7980392 | Hypo | head_neck | TMX4 | chr20 | 9488780 | 9488848 | Hypo | cancer_general | LAMP5 |
| chr20 | 14447971 | 14448144 | Hypo | cancer_general | | chr20 | 16554749 | 16555030 | Hypo | cancer_general | KIF16B |
| chr20 | 18073183 | 18073276 | Hypo | cancer_general | | chr20 | 18449082 | 18449076 | Hypo | cancer_general | POLR3F, DZANK1, MIR3192 |
| chr20 | 18489463 | 18489658 | Hypo | cancer_general | SEC23B | chr20 | 19128288 | 19128473 | Hypo | cancer_general | |
| chr20 | 19928306 | 19928461 | Hypo | cancer_general | RIN2 | chr20 | 21501381 | 21501417 | Hypo | cancer_general | NKX2-2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 21685385 | 21685526 | Hypo | cancer_general | PAX1 | chr20 | 22401392 | 22401421 | Hypo | literature | LOC284788 |
| chr20 | 23138383 | 23138444 | Hypo | cancer_general | | chr20 | 23406698 | 23406830 | Hypo | cancer_general | |
| chr20 | 24505190 | 24505252 | Hypo | cancer_general | SYNDIG1 | chr20 | 24726701 | 24726825 | Hypo | cancer_general | PYGB |
| chr20 | 25086082 | 25086275 | Hypo | cancer_general | | chr20 | 25223141 | 25223277 | Hypo | lung | ABHD12 |
| chr20 | 25230509 | 25230799 | Hypo | cancer_general | PYGB | chr20 | 25334513 | 25334650 | Hypo | cancer_general | |
| chr20 | 25344027 | 25344118 | Hypo | cancer_general | ABHD12 | chr20 | 29832911 | 29833090 | Hypo | cancer_general | DEFB118, DEFB119 |
| chr20 | 29914002 | 29914139 | Hypo | cancer_general | | chr20 | 29956013 | 29956042 | Hypo | literature | HM13 |
| chr20 | 29956570 | 29956599 | Hypo | literature | DEFB119, DEFB118 | chr20 | 30101523 | 30101743 | Hypo | cancer_general | |
| chr20 | 30162296 | 30162459 | Hypo | ovarian | HM13-AS1 | chr20 | 30174561 | 30174645 | Hypo | cancer_general | |
| chr20 | 30186068 | 30186165 | Hypo | ovarian | MIR3193, ID1 | chr20 | 30201236 | 30201360 | Hypo | cancer_general | MIR3193, ID1 |
| chr20 | 30280423 | 30280509 | Hypo | blood | BCL2L1 | chr20 | 30297090 | 30297217 | Hypo | cancer_general | BCL2L1 |
| chr20 | 30468319 | 30468349 | Hypo | cancer_general | TTLL9 | chr20 | 31035471 | 31035518 | Hypo | breast | C20orf112, ASXL1 |
| chr20 | 31115683 | 31115799 | Hypo | cancer_general | C20orf112 | chr20 | 31151769 | 31151799 | Hypo | cancer_general | C20orf112 |
| chr20 | 31207211 | 31207283 | Hypo | cancer_general | | chr20 | 31282734 | 31282903 | Hypo | breast | COMMD7 |
| chr20 | 32301797 | 32301953 | Hypo | breast | PXMP4 | chr20 | 32450248 | 32450427 | Hypo | cancer_general | CHMP4B |
| chr20 | 32701064 | 32701320 | Hypo | cancer_general | EIF2S2 | chr20 | 32716914 | 32716949 | Hypo | cancer_general | |
| chr20 | 32768669 | 32768728 | Hypo | ovarian | | chr20 | 33893006 | 33893125 | Hypo | ovarian | AHCY, GSS, MYH7B |
| chr20 | 33540284 | 33540550 | Hypo | cancer_general | MYH7B, GSS | chr20 | 33547485 | 33547585 | Hypo | colorectal | CEP250 |
| chr20 | 33574914 | 33574992 | Hypo | cancer_general | MIR499A, MIR499B, MYH7B | chr20 | 34041981 | 34042087 | Hypo | cancer_general | |
| chr20 | 34148020 | 34148254 | Hypo | cancer_general | FER1L4, ERGIC3 | chr20 | 35640448 | 35640561 | Hypo | head_neck | RBL1 |
| chr20 | 35742487 | 35742607 | Hypo | cancer_general | MROH8 | chr20 | 35892604 | 35892746 | Hypo | cancer_general | GHRH |
| chr20 | 36183184 | 36183340 | Hypo | lung | | chr20 | 40500546 | 40500638 | Hypo | cancer_general | |
| chr20 | 40515378 | 40515504 | Hypo | cancer_general | | chr20 | 40743859 | 40743888 | Hypo | literature | PTPRT |
| chr20 | 42218429 | 42218664 | Hypo | cancer_general | IFT52, SGK2 | chr20 | 42281425 | 42281455 | Hypo | cancer_general | IFT52 |
| chr20 | 42852751 | 42852915 | Hypo | colorectal, cancer_general | BC036500, OSER1-AS1 | chr20 | 43952174 | 43952302 | Hypo | cancer_general | SDC4, TRNA_Pseudo, RBPJL |
| chr20 | 44003765 | 44003811 | Hypo | blood | SYS1, SYS1-DBNDD2, TP53TG5 | chr20 | 44601547 | 44601716 | Hypo | cancer_general | ZNF335 |
| chr20 | 44602074 | 44602364 | Hypo | cancer_general | ZNF335 | chr20 | 45280344 | 45280428 | Hypo | tcga | SLC13A3 |
| chr20 | 45337804 | 45337945 | Hypo | cancer_general | SLC2A10 | chr20 | 47247239 | 47247450 | Hypo | cancer_general | PREX1, AX746653 |
| chr20 | 47274032 | 47274062 | Hypo | cancer_general | PREX1 | chr20 | 47296109 | 47296231 | Hypo | ovarian | |
| chr20 | 47450370 | 47450490 | Hypo | cancer_general | | chr20 | 47815615 | 47815711 | Hypo | ovarian | |
| chr20 | 47835328 | 47835358 | Hypo | cancer_general | DDX27 | chr20 | 47905426 | 47905603 | Hypo | cancer_general | ZFAS1, SNORD12, SNORD12B, SNORD12C |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 48695665 | 48696227 | Hypo | cancer_general | UBE2V1, TMEM189-UBE2V1 | chr20 | 48768118 | 48768148 | Hypo | cancer_general | |
| chr20 | 48774527 | 48774569 | Hypo | cancer_general | | chr20 | 49204179 | 49204449 | Hypo | cancer_general | FAM65C, MIR645, PTPN1 |
| chr20 | 49261803 | 49262104 | Hypo | cancer_general | FAM65C | chr20 | 49323924 | 49324125 | Hypo | cancer_general | |
| chr20 | 49350910 | 49351041 | Hypo | cancer_general | PARD6B | chr20 | 49351564 | 49351649 | Hypo | cancer_general | PARD6B |
| chr20 | 49358137 | 49358396 | Hypo | cancer_general | PARD6B | chr20 | 49377755 | 49378043 | Hypo | cancer_general | PARD6B |
| chr20 | 49381140 | 49381240 | Hypo | cancer_general | | chr20 | 49969348 | 49969515 | Hypo | colorectal | |
| chr20 | 50160756 | 50160905 | Hypo | cancer_general | | chr20 | 50833224 | 50833423 | Hypo | cancer_general | ATP9A |
| chr20 | 50602134 | 50602264 | Hypo | cancer_general | | chr20 | 50693423 | 50693468 | Hypo | breast | ZFP64 |
| chr20 | 52311463 | 52311728 | Hypo | pancreas | | chr20 | 52401713 | 52401775 | Hypo | cancer_general | |
| chr20 | 54522432 | 54522631 | Hypo | cancer_general | | chr20 | 55008041 | 55008194 | Hypo | cancer_general | CASS4 |
| chr20 | 55071563 | 55071717 | Hypo | ovarian | GCNT7, RTFDC1 | chr20 | 55499567 | 55499650 | Hypo | cancer_general | |
| chr20 | 55693527 | 55693662 | Hypo | cancer_general | | chr20 | 55959212 | 55959250 | Hypo | colorectal | RBM38 |
| chr20 | 56766160 | 56766190 | Hypo | cancer_general | | chr20 | 56998280 | 56998337 | Hypo | lung | VAPB |
| chr20 | 57484406 | 57484445 | Hypo | literature | GNAS | chr20 | 59525138 | 59525300 | Hypo | cancer_general | |
| chr20 | 59826192 | 59826221 | Hypo | literature | | chr20 | 59880433 | 59880477 | Hypo | cancer_general | |
| chr20 | 59910175 | 59910346 | Hypo | cancer_general | CDH4 | chr20 | 59973028 | 59973072 | Hypo | cancer_general | CDH4 |
| chr20 | 60202594 | 60202624 | Hypo | cancer_general | CDH4 | chr20 | 60235333 | 60235526 | Hypo | cancer_general | CDH4 |
| chr20 | 60238381 | 60238472 | Hypo | cancer_general | CDH4 | chr20 | 60238877 | 60238980 | Hypo | cancer_general | CDH4 |
| chr20 | 60243944 | 60244107 | Hypo | cancer_general | CDH4 | chr20 | 60329584 | 60329738 | Hypo | cancer_general | |
| chr20 | 60333880 | 60333969 | Hypo | cancer_general | | chr20 | 60359849 | 60359879 | Hypo | cancer_general | |
| chr20 | 60375036 | 60375070 | Hypo | cancer_general | | chr20 | 60439634 | 60439755 | Hypo | cancer_general | |
| chr20 | 60453925 | 60454091 | Hypo | cancer_general | | chr20 | 60477306 | 60477537 | Hypo | cancer_general | |
| chr20 | 60485374 | 60485425 | Hypo | cancer_general | | chr20 | 60503030 | 60503060 | Hypo | cancer_general | |
| chr20 | 60545374 | 60545792 | Hypo | breast | TAF4 | chr20 | 60620122 | 60620557 | Hypo | cancer_general | TAF4 |
| chr20 | 60772853 | 60773878 | Hypo | breast | MTG2 | chr20 | 60789965 | 60790124 | Hypo | cancer_general | HRH3 |
| chr20 | 60816241 | 60816271 | Hypo | head_neck | OSBPL2, AK126744 | chr20 | 60892164 | 60892222 | Hypo | cancer_general | LAMA5 |
| chr20 | 60926019 | 60926049 | Hypo | cancer_general | | chr20 | 60970953 | 60970983 | Hypo | cancer_general | CABLES2, RPS21 |
| chr20 | 60983859 | 60984010 | Hypo | cancer_general | RBBP8NL, CABLES2 | chr20 | 60984341 | 60984465 | Hypo | cancer_general | RBBP8NL, CABLES2 |
| chr20 | 61288068 | 61288156 | Hypo | cancer_general | SLCO4A1, LOC100127888 | chr20 | 61288463 | 61288534 | Hypo | cancer_general | LOC100127888, SLCO4A1 |
| chr20 | 61294693 | 61294857 | Hypo | cancer_general | LOC100127888 | chr20 | 61412313 | 61412438 | Hypo | cancer_general | LINC00659, AX747649 |
| chr20 | 61505851 | 61506330 | Hypo | cancer_general | DIDO1 | chr20 | 61532546 | 61532605 | Hypo | cancer_general | DIDO1 |
| chr20 | 61714591 | 61714621 | Hypo | cancer_general | | chr20 | 61763598 | 61763628 | Hypo | cancer_general | |
| chr20 | 61765285 | 61765425 | Hypo | cancer_general | | chr20 | 61823170 | 61823339 | Hypo | cancer_general | YTHDF1 |
| chr20 | 61974191 | 61974354 | Hypo | cancer_general | CHRNA4 | chr20 | 61980860 | 61980975 | Hypo | cancer_general | CHRNA4 |
| chr20 | 62031173 | 62031234 | Hypo | cancer_general | AK056267, KCNQ2 | chr20 | 62032058 | 62032095 | Hypo | cancer_general | AK056267 |
| chr20 | 62037559 | 62037598 | Hypo | cancer_general | KCNQ2 | chr20 | 62046227 | 62046421 | Hypo | cancer_general | KCNQ2 |
| chr20 | 62090524 | 62090778 | Hypo | cancer_general | KCNQ2 | chr20 | 62097666 | 62097695 | Hypo | literature | KCNQ2 |
| chr20 | 62115047 | 62115266 | Hypo | cancer_general | EEF1A2 | chr20 | 62126118 | 62126429 | Hypo | cancer_general | EEF1A2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 62157151 | 62157307 | Hypo | cancer_general | PTK6, PPDPF | chr20 | 62165631 | 62165762 | Hypo | cancer_general | SRMS, PTK6 |
| chr20 | 62167554 | 62167584 | Hypo | cancer_general | SRMS, PTK6 | chr20 | 62170179 | 62170209 | Hypo | cancer_general | SRMS, PTK6 |
| chr20 | 62172945 | 62173055 | Hypo | cancer_general | SRMS, PTK6 | chr20 | 62260818 | 62260905 | Hypo | cancer_general | GMEB2 |
| chr20 | 62261532 | 62261562 | Hypo | cancer_general | STMN3, GMEB2 | chr20 | 62314848 | 62314955 | Hypo | breast | RTEL1-TNFRSF6B, RTEL1 |
| chr20 | 62321206 | 62321341 | Hypo | cancer_general | TNFRSF6B, ARFRP1, RTEL1-TNFRSF6B | chr20 | 62321638 | 62321881 | Hypo | pancreas, cancer_general | RTEL1-TNFRSF6B, TNFRSF6B, ARFRP1 |
| chr20 | 62340321 | 62340442 | Hypo | cancer_general | ZGPAT, ARFRP1 | chr20 | 62383218 | 62383289 | Hypo | cancer_general | ZBTB46, SLC2A4RG |
| chr20 | 62391938 | 62391968 | Hypo | colorectal | ZBTB46 | chr20 | 62488293 | 62488350 | Hypo | cancer_general | ABHD16B, TPD52L2 |
| chr20 | 62497836 | 62497920 | Hypo | cancer_general | TPD52L2, ABHD16B | chr20 | 62631351 | 62631593 | Hypo | ovarian | PRPF6 |
| chr20 | 62786577 | 62786726 | Hypo | cancer_general | MYT1 | chr20 | 62795643 | 62795672 | Hypo | literature | MYT1 |
| chr22 | 18009969 | 18010121 | Hypo | cancer_general | CECR2 | chr22 | 18110495 | 18110593 | Hypo | cancer_general | BCL2L13, ATP6V1E1 |
| chr22 | 18328127 | 18328268 | Hypo | cancer_general, lung | MICAL3, BC064400 | chr22 | 18340822 | 18340868 | Hypo | cancer_general | MICAL3 |
| chr22 | 18627328 | 18627537 | Hypo | ovarian | USP18 | chr22 | 19117564 | 19117594 | Hypo | cancer_general | DGCR14, TSSK2 |
| chr22 | 19136907 | 19136936 | Hypo | literature | GSC2 | chr22 | 19137859 | 19137888 | Hypo | literature | GSC2 |
| chr22 | 19138109 | 19138138 | Hypo | literature | GSC2 | chr22 | 20229079 | 20229239 | Hypo | pancreas | MIR1286, RTN4R |
| chr22 | 20864642 | 20864672 | Hypo | cancer_general | MED15 | chr22 | 20940868 | 20940898 | Hypo | head_neck | MED15 |
| chr22 | 21042829 | 21043014 | Hypo | cancer_general | DQ571461, POM121L4P | chr22 | 21153867 | 21154000 | Hypo | cancer_general | PI4KA |
| chr22 | 21270750 | 21270834 | Hypo | cancer_general | CRKL | chr22 | 21276140 | 21276261 | Hypo | cancer_general | CRKL, BC033281, BC127858, CRKL |
| chr22 | 21299605 | 21299635 | Hypo | pancreas | BC033281, CRKL | chr22 | 21304771 | 21305007 | Hypo | cancer_general | |
| chr22 | 21977314 | 21977347 | Hypo | breast | YDJC, CCDC116, UBE2L3 | chr22 | 21982792 | 21982972 | Hypo | cancer_general | CCDC116, YDJC, UBE2L3 |
| chr22 | 22023273 | 22023451 | Hypo | cancer_general | PPIL2 | chr22 | 22058203 | 22058238 | Hypo | lung | YPEL1, PPIL2 |
| chr22 | 22201344 | 22201568 | Hypo | head_neck | MAPK1 | chr22 | 22901105 | 22901455 | Hypo | cancer_general | LOC648691, PRAME |
| chr22 | 23791402 | 23791432 | Hypo | cancer_general | GUSBP11 | chr22 | 23801459 | 23801610 | Hypo | breast | LOC388882 |
| chr22 | 23991201 | 23991272 | Hypo | pancreas | AK096976, DERL3 | chr22 | 24145484 | 24145513 | Hypo | literature | SMARCB1 |
| chr22 | 24179940 | 24179982 | Hypo | blood | | chr22 | 24560375 | 24560526 | Hypo | breast | CABIN1 |
| chr22 | 28371649 | 28371679 | Hypo | cancer_general | TTC28 | chr22 | 29076592 | 29076622 | Hypo | lung | CHEK2 |
| chr22 | 29091824 | 29091853 | Hypo | literature | CHEK2 | chr22 | 29445752 | 29445923 | Hypo | lung | C22orf31 |
| chr22 | 29977614 | 29977863 | Hypo | cancer_general | NIPSNAP1 | chr22 | 30084358 | 30084388 | Hypo | cancer_general | NF2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 30090739 | 30090769 | Hypo | breast | NF2 | chr22 | 30158330 | 30158639 | Hypo | cancer_general | UQCR10, ZMAT5 |
| chr22 | 30784196 | 30784278 | Hypo | cancer_general | SEC14L2, RNF215 | chr22 | 32061344 | 32061374 | Hypo | cancer_general | |
| chr22 | 32748936 | 32748966 | Hypo | cancer_general | RFPL3, RFPL3S, JB153905 | chr22 | 32868720 | 32868837 | Hypo | cancer_general | FBXO7, BPIFC |
| chr22 | 35079219 | 35079345 | Hypo | cancer_general | | chr22 | 35768531 | 35768719 | Hypo | cancer_general | HMOX1 |
| chr22 | 35848358 | 35848670 | Hypo | cancer_general | | chr22 | 35938746 | 35939000 | Hypo | esophageal | RASD2 |
| chr22 | 36567866 | 36567896 | Hypo | cancer_general | | chr22 | 36855297 | 36855335 | Hypo | cancer_general | TXN2 |
| chr22 | 36855568 | 36855598 | Hypo | cancer_general | TXN2 | chr22 | 36880362 | 36880462 | Hypo | cancer_general | FOXRED2, TXN2 |
| chr22 | 36902291 | 36902381 | Hypo | head_neck | EIF3D, FOXRED2 | chr22 | 37302073 | 37302103 | Hypo | cancer_general | CSF2RB |
| chr22 | 38002684 | 38002733 | Hypo | head_neck | GGA1 | chr22 | 38087310 | 38087367 | Hypo | head_neck | TRIOBP, NOL12 |
| chr22 | 38182815 | 38182981 | Hypo | head_neck | | chr22 | 38199769 | 38199894 | Hypo | cancer_general | H1F0, GCAT |
| chr22 | 38507316 | 38507346 | Hypo | cancer_general | PLA2G6 | chr22 | 38593856 | 38593076 | Hypo | cancer_general | MAFF DDX17, KDELR3 |
| chr22 | 38639229 | 38639259 | Hypo | hepatobiliary | TMEM184B | chr22 | 38874215 | 38874362 | Hypo | head_neck | |
| chr22 | 39094890 | 39094964 | Hypo | cancer_general | GTPBP1, JOSD1 | chr22 | 39098022 | 39098064 | Hypo | cancer_general | GTPBP1, JOSD1 |
| chr22 | 39112502 | 39112584 | Hypo | head_neck | GTPBP1 | chr22 | 39830355 | 39830457 | Hypo | breast | LOC100506472, TAB1 |
| chr22 | 39932499 | 39932563 | Hypo | cancer_general | RPS19BP1 | chr22 | 40042627 | 40042743 | Hypo | cancer_general | CACNA1I |
| chr22 | 40075157 | 40075302 | Hypo | hepatobiliary | CACNA1I | chr22 | 40226345 | 40226389 | Hypo | cancer_general | ENTHD1 |
| chr22 | 40767753 | 40767936 | Hypo | cancer_general | ADSL, SGSM3 | chr22 | 40895978 | 40896029 | Hypo | cancer_general | MKL1 |
| chr22 | 41048488 | 41048518 | Hypo | cancer_general | | chr22 | 41048732 | 41049109 | Hypo | cancer_general | RANGAP1, CHADL |
| chr22 | 41217105 | 41217405 | Hypo | lung, cancer_general | ST13, MIR4766, SLC25A17 | chr22 | 41634393 | 41634542 | Hypo | pancreas, cancer_general | |
| chr22 | 41637064 | 41637129 | Hypo | cancer_general | CHADL, RANGAP1 | chr22 | 41648414 | 41648444 | Hypo | head_neck | RANGAP1 |
| chr22 | 41657233 | 41657350 | Hypo | breast | RANGAP1 | chr22 | 41690119 | 41690149 | Hypo | head_neck | ZC3H7B, RANGAP1 |
| chr22 | 41839432 | 41839498 | Hypo | cancer_general | TOB2 | chr22 | 42068010 | 42068172 | Hypo | cancer_general | NHP2L1, XRCC6 |
| chr22 | 42096002 | 42096190 | Hypo | head_neck | C22orf46, MEI1, FLJ23584 | chr22 | 42343416 | 42343676 | Hypo | cancer_general | LINC00634, CENPM |
| chr22 | 42667358 | 42667432 | Hypo | cancer_general | LOC388906 | chr22 | 42916449 | 42916479 | Hypo | cancer_general | RRP7A, SERHL |
| chr22 | 43012543 | 43012877 | Hypo | cancer_general | CYB5R3, DL490307, RNU12, POLDIP3 | chr22 | 43083130 | 43083166 | Hypo | cancer_general | A4GALT |
| chr22 | 43434441 | 43434477 | Hypo | cancer_general | TTLL1, BC039353 | chr22 | 43540672 | 43540702 | Hypo | breast | TSPO, MCAT |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 44455707 | 44455740 | Hypo | cancer_general | PARVB | chr22 | 45087614 | 45087649 | Hypo | cancer_general | PRR5 |
| chr22 | 45088602 | 45088743 | Hypo | cancer_general | PRR5, PRR5-ARHGAP8 | chr22 | 45135939 | 45135979 | Hypo | cancer_general | PRR5, PRR5-ARHGAP8 |
| chr22 | 45252427 | 45252463 | Hypo | hepatobiliary | ARHGAP8 | chr22 | 45277292 | 45277322 | Hypo | cancer_general | PHF21B |
| chr22 | 45313416 | 45313446 | Hypo | hepatobiliary | PHF21B | chr22 | 45593643 | 45593715 | Hypo | cancer_general | KIAA0930, NUP50, MIR1249 |
| chr22 | 45604184 | 45604343 | Hypo | cancer_general | MIR1249, KIAA0930 | chr22 | 46438085 | 46438217 | Hypo | cancer_general | C22orf26, LINC00899 |
| chr22 | 46455833 | 46455905 | Hypo | cancer_general | MIRLET7BHG, LOC150381, C22orf26, LOC554174 | chr22 | 46599623 | 46599725 | Hypo | colorectal | PPARA |
| chr22 | 46931260 | 46931332 | Hypo | ovarian | GRAMD4 | chr22 | 47005080 | 47005154 | Hypo | cancer_general | GRAMD4 |
| chr22 | 47023044 | 47023191 | Hypo | head_neck | TBC1D22A | chr22 | 47054686 | 47054716 | Hypo | head_neck | |
| chr22 | 47193335 | 47193371 | Hypo | cancer_general | | chr22 | 47394475 | 47395505 | Hypo | breast | |
| chr22 | 47525846 | 47525885 | Hypo | cancer_general | AK093107, BC039485, LINC00898 | chr22 | 47584867 | 47585024 | Hypo | cancer_general | LOC284933, FAM19A5 |
| chr22 | 48027626 | 48027655 | Hypo | literature | | chr22 | 48931881 | 48932027 | Hypo | cancer_general | |
| chr22 | 49852617 | 49852647 | Hypo | cancer_general | BC033837 | chr22 | 49979646 | 49979757 | Hypo | cancer_general | BC033837 |
| chr22 | 50001699 | 50001882 | Hypo | cancer_general | BC033837 | chr22 | 50002787 | 50002819 | Hypo | cancer_general | BC033837 |
| chr22 | 50003204 | 50003234 | Hypo | cancer_general | BC033837 | chr22 | 50010113 | 50010258 | Hypo | cancer_general | C22orf34, BC033837 |
| chr22 | 50010461 | 50010585 | Hypo | cancer_general | C22orf34, BC033837 | chr22 | 50031691 | 50031721 | Hypo | cancer_general | C22orf34, BC033837 |
| chr22 | 50149431 | 50149470 | Hypo | cancer_general | DENND6B LMF2, NCAPH2 | chr22 | 50251536 | 50251582 | Hypo | breast | ZBED4 |
| chr22 | 50467005 | 50467035 | Hypo | cancer_general | | chr22 | 50467876 | 50468105 | Hypo | cancer_general | |
| chr22 | 50768840 | 50768876 | Hypo | cancer_general | | chr22 | 50899293 | 50899672 | Hypo | cancer_general | SBF1 SYCE3, KLHDC7B |
| chr22 | 50939073 | 50939111 | Hypo | cancer_general | | chr22 | 50986016 | 50986045 | Hypo | literature | |
| chr10 | 524754 | 524784 | Hypo | head_neck | DIP2C | chr10 | 833307 | 833386 | Hypo | cancer_general | IDI1, IDI2-AS1, IDI2 |
| chr10 | 978878 | 978933 | Hypo | cancer_general | BC127786, LARP4B | chr10 | 1080377 | 1080513 | Hypo | breast | ADARB2-AS1 |
| chr10 | 1120778 | 1120937 | Hypo | lung | WDR37 | chr10 | 1577394 | 1577424 | Hypo | hepatobiliary | |
| chr10 | 1585111 | 1585239 | Hypo | cancer_general | ADARB2-AS1 | chr10 | 1708327 | 1708478 | Hypo | cancer_general | |
| chr10 | 3197004 | 3197113 | Hypo | ovarian | BC039685, PTTRM1-AS1, PTTRM1 | chr10 | 3285585 | 3285698 | Hypo | cancer_general | |
| chr10 | 3330499 | 3330618 | Hypo | cancer_general | | chr10 | 3641378 | 3641413 | Hypo | colorectal | BC037918 |
| chr10 | 3678597 | 3678637 | Hypo | lung | BC037918 | chr10 | 3895410 | 3895452 | Hypo | cancer_general | |
| chr10 | 4599917 | 4599965 | Hypo | cancer_general | | chr10 | 5530764 | 5530975 | Hypo | cancer_general | CALML5 |
| chr10 | 5765021 | 5765059 | Hypo | breast | FAM208B | chr10 | 5855154 | 5855184 | Hypo | pancreas | GDI2 |
| chr10 | 5875140 | 5875396 | Hypo | cancer_general | | chr10 | 6003402 | 6003855 | Hypo | breast | IL15RA |
| chr10 | 6042309 | 6042571 | Hypo | cancer_general | | chr10 | 6162159 | 6162225 | Hypo | cancer_general | RBM17 |
| chr10 | 6167619 | 6167742 | Hypo | ovarian | RBM17 | chr10 | 6206142 | 6206217 | Hypo | pancreas | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 6372243 | 6372373 | Hypo | ovarian | LOC399715 | chr10 | 6513976 | 6514006 | Hypo | hepatobiliary | PRKCQ |
| chr10 | 6377643 | 6377673 | Hypo | cancer_general | AX748236 | chr10 | 6586721 | 6586847 | Hypo | cancer_general | |
| chr10 | 6963079 | 6963111 | Hypo | cancer_general | | chr10 | 6984463 | 6984639 | Hypo | cancer_general | |
| chr10 | 7205733 | 7205787 | Hypo | cancer_general | SFMBT2 | chr10 | 7212745 | 7213064 | Hypo | cancer_general | SFMBT2 |
| chr10 | 7213505 | 7213535 | Hypo | hepatobiliary | SFMBT2 | chr10 | 7216059 | 7216089 | Hypo | cancer_general | SFMBT2 |
| chr10 | 7236211 | 7236245 | Hypo | cancer_general | SFMBT2 | chr10 | 7255730 | 7255821 | Hypo | hepatobiliary | SFMBT2 |
| chr10 | 7323283 | 7323313 | Hypo | cancer_general | SFMBT2 | chr10 | 7334737 | 7334767 | Hypo | hepatobiliary | SFMBT2 |
| chr10 | 7363436 | 7363466 | Hypo | hepatobiliary | SFMBT2 | chr10 | 7371678 | 7371708 | Hypo | cancer_general | SFMBT2 |
| chr10 | 7414544 | 7414588 | Hypo | cancer_general | SFMBT2 | chr10 | 7424626 | 7424687 | Hypo | hepatobiliary | TAF3 |
| chr10 | 7436090 | 7436209 | Hypo | cancer_general | | chr10 | 8055681 | 8055764 | Hypo | pancreas | CAMK1D |
| chr10 | 11700918 | 11701075 | Hypo | cancer_general | | chr10 | 12554417 | 12554501 | Hypo | cancer_general | FRMD4A |
| chr10 | 13140861 | 13141020 | Hypo | cancer_general | OPTN, AK311458 | chr10 | 13715208 | 13715401 | Hypo | head_neck | DCLRE1C RPP38, NMT2, C10orf111, ACBD7 |
| chr10 | 14393819 | 14393893 | Hypo | colorectal | FRMD4A | chr10 | 14966129 | 14966212 | Hypo | cancer_general | C1QL3 |
| chr10 | 15002784 | 15003006 | Hypo | cancer_general | MEIG1 | chr10 | 15140484 | 15140526 | Hypo | cancer_general | VIM, BC078172 |
| chr10 | 16175687 | 16175801 | Hypo | hepatobiliary | | chr10 | 16564087 | 16564116 | Hypo | literature | VIM, |
| chr10 | 16564537 | 16564566 | Hypo | literature | C1QL3 | chr10 | 17269259 | 17269288 | Hypo | literature | BC078172 |
| chr10 | 17275584 | 17275613 | Hypo | literature | VIM, BC078172 | chr10 | 17277741 | 17277770 | Hypo | literature | |
| chr10 | 17429165 | 17429622 | Hypo | cancer_general | ST8SIA6-AS1, ST8SIA6 | chr10 | 17503402 | 17503520 | Hypo | cancer_general | |
| chr10 | 17509450 | 17509503 | Hypo | hepatobiliary | | chr10 | 21101525 | 21101555 | Hypo | hepatobiliary | NEBL |
| chr10 | 21728064 | 21728124 | Hypo | cancer_general | APBB1IP | chr10 | 22047336 | 22047635 | Hypo | breast | DNAJC1 |
| chr10 | 22567093 | 22567322 | Hypo | cancer_general | | chr10 | 24988589 | 24988679 | Hypo | cancer_general | ARHGAP21 |
| chr10 | 26747051 | 26747159 | Hypo | cancer_general | | chr10 | 26803853 | 26803883 | Hypo | literature | |
| chr10 | 26816766 | 26816938 | Hypo | cancer_general | RAB18 | chr10 | 26931897 | 26931926 | Hypo | cancer_general | LINC00202-2 |
| chr10 | 27794496 | 27794588 | Hypo | cancer_general | BAMBI | chr10 | 27846637 | 27846816 | Hypo | cancer_general | |
| chr10 | 28964745 | 28964800 | Hypo | ovarian | | chr10 | 30848200 | 30848230 | Hypo | cancer_general | |
| chr10 | 31892922 | 31893079 | Hypo | cancer_general | EPC1 | chr10 | 32499044 | 32499176 | Hypo | cancer_general | ITGB1 |
| chr10 | 32672459 | 32672489 | Hypo | cancer_general | | chr10 | 33233313 | 33233361 | Hypo | cancer_general | ZNF33BP1, ZNF248 |
| chr10 | 37051865 | 37051895 | Hypo | pancreas | | chr10 | 38078948 | 38079105 | Hypo | cancer_general | |
| chr10 | 43186151 | 43186181 | Hypo | cancer_general | AK123067 | chr10 | 43609055 | 43609117 | Hypo | literature | RET |
| chr10 | 43609922 | 43609963 | Hypo | literature | RET | chr10 | 43613890 | 43613919 | Hypo | literature | RET |
| chr10 | 43614982 | 43615011 | Hypo | literature | RET | chr10 | 43615554 | 43615607 | Hypo | literature | RET |
| chr10 | 43617401 | 43617430 | Hypo | literature | RET | chr10 | 43858343 | 43858470 | Hypo | cancer_general | FXYD4 |
| chr10 | 43905877 | 43906023 | Hypo | cancer_general | ARHGAP22, MAPK8 | chr10 | 44434176 | 44434206 | Hypo | cancer_general | LINC00841 FAM170B, FAM170B-AS1 |
| chr10 | 49652977 | 49653080 | Hypo | cancer_general | | chr10 | 50340119 | 50340149 | Hypo | cancer_general | |
| chr10 | 50507557 | 50507619 | Hypo | cancer_general | C10orf71 | chr10 | 50748131 | 50748350 | Hypo | cancer_general | ARID5B |
| chr10 | 53107427 | 53107563 | Hypo | cancer_general | | chr10 | 63669223 | 63669344 | Hypo | ovarian | DNAJC12 |
| chr10 | 65262111 | 65262304 | Hypo | breast | | chr10 | 69578459 | 69578888 | Hypo | cancer_general | DNA2, |
| chr10 | 69589153 | 69589407 | Hypo | cancer_general | DNAJC12 | chr10 | 70167678 | 70167708 | Hypo | cancer_general | RUFY2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 70232345 | 70232485 | Hypo | cancer_general | SLC25A16, DNA2 | chr10 | 70275831 | 70275979 | Hypo | breast | SLC25A16 |
| chr10 | 70314814 | 70315148 | Hypo | cancer_general | TET1 | chr10 | 70565410 | 70565489 | Hypo | cancer_general | HK1 |
| chr10 | 70586494 | 70586540 | Hypo | cancer_general | STOX1 | chr10 | 71084981 | 71085116 | Hypo | hepatobiliary | MYOZ1 |
| chr10 | 73157867 | 73158027 | Hypo | pancreas | CDH23 | chr10 | 75384100 | 75384130 | Hypo | ovarian | MYOZ1 |
| chr10 | 75386789 | 75386893 | Hypo | cancer_general | MYOZ1 | chr10 | 75388129 | 75388173 | Hypo | cancer_general | ZMIZ1 |
| chr10 | 75488953 | 75489125 | Hypo | cancer_general | GLUD1P3, BMS1P4, AGAP5 | chr10 | 81023884 | 81023914 | Hypo | cancer_general | |
| chr10 | 81860447 | 81860568 | Hypo | cancer_general | TMEM254 | chr10 | 81966737 | 81966828 | Hypo | cancer_general | LINC00857, ANXA11 |
| chr10 | 85792257 | 85792287 | Hypo | hepatobiliary | | chr10 | 88304914 | 88304944 | Hypo | cancer_general | MMRN2 |
| chr10 | 88684005 | 88684034 | Hypo | literature | BMPR1A | chr10 | 88698834 | 88698914 | Hypo | cancer_general | PTEN |
| chr10 | 89624255 | 89624311 | Hypo | literature | PTEN, KLLN | chr10 | 89653788 | 89653859 | Hypo | literature | |
| chr10 | 89685272 | 89685322 | Hypo | literature | PTEN | chr10 | 89690790 | 89690819 | Hypo | literature | PTEN |
| chr10 | 89692776 | 89693015 | Hypo | literature | PTEN | chr10 | 89711861 | 89711992 | Hypo | literature | AK130076, PTEN |
| chr10 | 89717610 | 89717744 | Hypo | literature | AK130076, PTEN | chr10 | 89720790 | 89720885 | Hypo | literature | |
| chr10 | 89725030 | 89725071 | Hypo | literature | | chr10 | 94062288 | 94062318 | Hypo | head_neck | 5-Mar |
| chr10 | 96304020 | 96304329 | Hypo | cancer_general | HELLS, TBC1D12 | chr10 | 98129822 | 98130033 | Hypo | cancer_general | TLL2 |
| chr10 | 98528023 | 98528107 | Hypo | cancer_general | ARHGAP19 | chr10 | 98558129 | 98558200 | Hypo | colorectal | |
| chr10 | 99051122 | 99051253 | Hypo | cancer_general | MARVELD1 | chr10 | 99161398 | 99161560 | Hypo | cancer_general | SLC25A28 |
| chr10 | 99481747 | 99481905 | Hypo | colorectal | CUTC, COX15 | chr10 | 101363207 | 101363418 | Hypo | colorectal | CWF19L1, SNORA12, CHUK |
| chr10 | 101492942 | 101493074 | Hypo | cancer_general | | chr10 | 101988223 | 101988404 | Hypo | cancer_general | |
| chr10 | 103325743 | 103325773 | Hypo | cancer_general | DPCD, BTRC | chr10 | 103425950 | 103426174 | Hypo | ovarian | FBXW4 |
| chr10 | 103579635 | 103579713 | Hypo | cancer_general | KCNIP2, LOC100289509, MGEA5 | chr10 | 103814668 | 103814754 | Hypo | cancer_general | C10orf76 |
| chr10 | 103930034 | 103930161 | Hypo | cancer_general | NOLC1 | chr10 | 105126957 | 105127076 | Hypo | cancer_general | TAF5 |
| chr10 | 105155285 | 105155481 | Hypo | cancer_general | PDCD11, MIR1307, USMG5, TAF5 | chr10 | 105413627 | 105413784 | Hypo | cancer_general | SH3PXD2A |
| chr10 | 105420861 | 105420891 | Hypo | breast | SH3PXD2A | chr10 | 105527028 | 105527057 | Hypo | literature | |
| chr10 | 108469972 | 108470093 | Hypo | cancer_general | SORCS1 | chr10 | 112440378 | 112440408 | Hypo | cancer_general | |
| chr10 | 115925505 | 115925552 | Hypo | cancer_general | MIR2110, C10orf118 | chr10 | 116331126 | 116331156 | Hypo | cancer_general | RBM20 |
| chr10 | 119807026 | 119807056 | Hypo | cancer_general | CASC2, RAB11FIP2 | chr10 | 120707028 | 120707111 | Hypo | cancer_general | |
| chr10 | 120800789 | 120800835 | Hypo | ovarian | EIF3A, NANOS1 | chr10 | 120841558 | 120841590 | Hypo | cancer_general | |
| chr10 | 120937014 | 120937139 | Hypo | breast | PRDX3 | chr10 | 121267480 | 121267626 | Hypo | hepatobiliary | RGS10 |
| chr10 | 121307542 | 121307572 | Hypo | cancer_general | | chr10 | 123256044 | 123256232 | Hypo | literature | FGFR2 |
| chr10 | 123258020 | 123258091 | Hypo | literature | FGFR2 | chr10 | 123274758 | 123274787 | Hypo | literature | FGFR2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 123279548 | 123279697 | Hypo | literature | FGFR2 | chr10 | 123667184 | 123667222 | Hypo | breast | ATE1 |
| chr10 | 123688711 | 123688741 | Hypo | cancer_general | ATE1 | chr10 | 125527754 | 125527784 | Hypo | hepatobiliary | CPXM2 |
| chr10 | 126101966 | 126102095 | Hypo | head_neck | OAT | chr10 | 126198949 | 126199077 | Hypo | cancer_general | LHPP |
| chr10 | 126697789 | 126698107 | Hypo | cancer_general | CTBP2 | chr10 | 126782965 | 126783048 | Hypo | hepatobiliary | |
| chr10 | 126828994 | 126829024 | Hypo | hepatobiliary | | chr10 | 127406313 | 127406386 | Hypo | ovarian | C10orf137, FLJ37035, LOC283038 |
| chr10 | 127693923 | 127693959 | Hypo | hepatobiliary | ADAM12, FANK1 | chr10 | 129379338 | 129379367 | Hypo | literature | |
| chr10 | 129888804 | 129888885 | Hypo | cancer_general | MKI67, PTPRE | chr10 | 130203435 | 130203480 | Hypo | cancer_general | |
| chr10 | 130577764 | 130577794 | Hypo | cancer_general | | chr10 | 131348513 | 131348793 | Hypo | pancreas | MGMT |
| chr10 | 131647903 | 131647933 | Hypo | cancer_general | MIR4297, EBF3 | chr10 | 131936451 | 131936626 | Hypo | cancer_general | GLRX3 |
| chr10 | 131937355 | 131937428 | Hypo | lung | GLRX3 | chr10 | 132000973 | 132001015 | Hypo | cancer_general | JAKMIP3 |
| chr10 | 132001252 | 132001556 | Hypo | cancer_general | | chr10 | 133951602 | 133952025 | Hypo | cancer_general | STK32C, DPYSL4 |
| chr10 | 133979059 | 133979089 | Hypo | cancer_general | JAKMIP3 | chr10 | 134016203 | 134016388 | Hypo | cancer_general | STK32C |
| chr10 | 134022845 | 134022875 | Hypo | cancer_general | STK32C, DPYSL4 | chr10 | 134039087 | 134039117 | Hypo | hepatobiliary | |
| chr10 | 134092153 | 134092202 | Hypo | cancer_general | STK32C | chr10 | 134095594 | 134095833 | Hypo | cancer_general | STK32C |
| chr10 | 134119401 | 134119447 | Hypo | hepatobiliary | STK32C | chr10 | 134273064 | 134273156 | Hypo | cancer_general | |
| chr10 | 134301095 | 134301212 | Hypo | cancer_general | | chr10 | 134481320 | 134481433 | Hypo | cancer_general | |
| chr10 | 134491021 | 134491114 | Hypo | ovarian | INPP5A | chr10 | 134499773 | 134499803 | Hypo | pancreas | INPP5A |
| chr10 | 134593329 | 134593416 | Hypo | ovarian | INPP5A, NKX6-2, INPP5A | chr10 | 134607970 | 134608183 | Hypo | cancer_general | NKX6-2 |
| chr10 | 134665147 | 134665202 | Hypo | cancer_general | TTC40 | chr10 | 134679129 | 134679265 | Hypo | cancer_general | TTC40 |
| chr10 | 134690559 | 134690617 | Hypo | cancer_general | TTC40 | chr10 | 134693587 | 134693709 | Hypo | cancer_general | TTC40 |
| chr10 | 134699872 | 134699909 | Hypo | cancer_general | TTC40 | chr10 | 134733221 | 134733275 | Hypo | cancer_general | TTC40 |
| chr10 | 134733497 | 134733617 | Hypo | cancer_general | TTC40 | chr10 | 134738378 | 134738642 | Hypo | cancer_general | TTC40 |
| chr10 | 134788083 | 134788251 | Hypo | cancer_general | LOC399829 | chr10 | 134794271 | 134794342 | Hypo | cancer_general | LOC399829 |
| chr10 | 134796012 | 134796042 | Hypo | cancer_general | LOC399829 | chr10 | 134896060 | 134896092 | Hypo | hepatobiliary | GPR123 |
| chr10 | 134916714 | 134916774 | Hypo | cancer_general | GPR123 | chr10 | 134941145 | 134941178 | Hypo | cancer_general | GPR123 |
| chr10 | 134942840 | 134943114 | Hypo | cancer_general | GPR123 | chr10 | 134943445 | 134943542 | Hypo | cancer_general | GPR123 |
| chr10 | 134944742 | 134944772 | Hypo | cancer_general | KNDC1 | chr10 | 134959217 | 134959391 | Hypo | cancer_general | CS330190 |
| chr10 | 135002063 | 135002156 | Hypo | cancer_general | KNDC1 | chr10 | 135014963 | 135015132 | Hypo | cancer_general | KNDC1 |
| chr10 | 135017049 | 135017129 | Hypo | cancer_general | KNDC1 | chr10 | 135018032 | 135018070 | Hypo | ovarian | KNDC1 |
| chr10 | 135018825 | 135018960 | Hypo | cancer_general | KNDC1 | chr10 | 135020801 | 135020893 | Hypo | cancer_general | KNDC1 |
| chr10 | 135023470 | 135023500 | Hypo | cancer_general | PRAP1, ZNF511, TUBGCP2 | chr10 | 135076368 | 135076503 | Hypo | cancer_general | ADAM8 |
| chr10 | 135122991 | 135123020 | Hypo | literature | | chr10 | 135153956 | 135154001 | Hypo | ovarian | PRAP1, CALY |
| chr14 | 21100748 | 21100778 | Hypo | head_neck | TRNA_Pro, OR6S1, TRNA_Thr, TRNA_Leu | chr14 | 23234956 | 23235032 | Hypo | esophageal | OXA1L, SLC7A7 |
| chr14 | 23400315 | 23400354 | Hypo | cancer_general | TRNA, TRNA_Arg, PRMT5 | chr14 | 23426755 | 23426785 | Hypo | cancer_general | MIR4707, HAUS4 |
| chr14 | 23701644 | 23701737 | Hypo | head_neck | | chr14 | 23706727 | 23706765 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 24562744 | 24562774 | Hypo | cancer_general | PCK2 | chr14 | 25071566 | 25071612 | Hypo | cancer_general | GZMH |
| chr14 | 25155907 | 25155985 | Hypo | cancer_general | BC041327, | chr14 | 31027323 | 31027367 | Hypo | cancer_general | G2E3 |
| chr14 | 31925554 | 31925724 | Hypo | cancer_general | DTD2 | chr14 | 32597620 | 32597657 | Hypo | pancreas | ARHGAP5 |
| chr14 | 34269897 | 34270004 | Hypo | head_neck | | chr14 | 35023111 | 35023322 | Hypo | cancer_general | SNX6 |
| chr14 | 35024446 | 35024546 | Hypo | cancer_general | SNX6 | chr14 | 35389907 | 35389943 | Hypo | cancer_general | FANCM, |
| chr14 | 39579800 | 39579830 | Hypo | cancer_general | GEMIN2 | chr14 | 45602514 | 45602576 | Hypo | cancer_general | FKBP3 |
| chr14 | 50233426 | 50233459 | Hypo | cancer_general | KLHDC2 | chr14 | 50333754 | 50333994 | Hypo | cancer_general | Metazoa_SRP |
| chr14 | 50334254 | 50334355 | Hypo | cancer_general | Metazoa_SRP | chr14 | 50355854 | 50355924 | Hypo | colorectal | ARF6 |
| chr14 | 50681598 | 50681859 | Hypo | breast | | chr14 | 50777663 | 50777714 | Hypo | cancer_general | ATP5S, L2HGDH |
| chr14 | 51829264 | 51829396 | Hypo | ovarian | LINC00640 | chr14 | 51955509 | 51955538 | Hypo | literature | FRMD6, FRMD6-AS2 |
| chr14 | 52765920 | 52766075 | Hypo | cancer_general | | chr14 | 55370202 | 55370235 | Hypo | cancer_general | FBXO34 |
| chr14 | 55668368 | 55668526 | Hypo | colorectal | DLGAP5 | chr14 | 55765285 | 55765714 | Hypo | lung, cancer_general | |
| chr14 | 55823079 | 55823218 | Hypo | breast | ATG14, FBXO34 | chr14 | 57045520 | 57045739 | Hypo | cancer_general | TMEM260 |
| chr14 | 57270936 | 57270987 | Hypo | cancer_general | OTX2, OTX2-AS1 | chr14 | 58857094 | 58857355 | Hypo | cancer_general | TOMM20L |
| chr14 | 58893052 | 58893183 | Hypo | cancer_general | KIAA0586, TIMM9 | chr14 | 59770326 | 59770452 | Hypo | breast | DAAM1 |
| chr14 | 62106193 | 62106242 | Hypo | colorectal | FLJ22447 | chr14 | 64107335 | 64107600 | Hypo | cancer_general | |
| chr14 | 64222413 | 64222488 | Hypo | cancer_general | | chr14 | 65005696 | 65005833 | Hypo | cancer_general | |
| chr14 | 65233339 | 65233464 | Hypo | cancer_general | SPTB | chr14 | 66498931 | 66498975 | Hypo | cancer_general | HSPA2 |
| chr14 | 67585164 | 67585413 | Hypo | cancer_general | GPHN | chr14 | 67886378 | 67886606 | Hypo | cancer_general | PLEK2 |
| chr14 | 68334928 | 68335108 | Hypo | cancer_general | RAD51B | chr14 | 69014044 | 69014110 | Hypo | pancreas | |
| chr14 | 69866541 | 69866706 | Hypo | cancer_general | SLC39A9, ERH | chr14 | 69867022 | 69867196 | Hypo | cancer_general | SLC39A9, ERH |
| chr14 | 73167750 | 73167899 | Hypo | cancer_general | DPF3 | chr14 | 73175026 | 73175148 | Hypo | cancer_general | DPF3 |
| chr14 | 73178807 | 73178865 | Hypo | cancer_general | DPF3 | chr14 | 73180208 | 73180314 | Hypo | cancer_general | DPF3 |
| chr14 | 73226952 | 73227005 | Hypo | cancer_general | DPF3 | chr14 | 73231266 | 73231414 | Hypo | lung, cancer_general | DPF3 |
| chr14 | 73236095 | 73236178 | Hypo | cancer_general | | chr14 | 73318471 | 73318629 | Hypo | lung, cancer_general | DPF3 |
| chr14 | 73333249 | 73333396 | Hypo | cancer_general | DPF3 | chr14 | 73602250 | 73602389 | Hypo | cancer_general | PSEN1 |
| chr14 | 73604570 | 73604718 | Hypo | cancer_general | PSEN1 | chr14 | 73855616 | 73855646 | Hypo | cancer_general | NUMB |
| chr14 | 73956853 | 73956913 | Hypo | cancer_general | C14orf169, HEATR4 | chr14 | 74529109 | 74529139 | Hypo | cancer_general | ALDH6A1, CCDC176 |
| chr14 | 75760311 | 75760347 | Hypo | cancer_general | LOC731223 | chr14 | 76128674 | 76128842 | Hypo | cancer_general | C14orf1, TTLL5 |
| chr14 | 77737785 | 77737814 | Hypo | tcga | POMT2, MIR1260A, NGB | chr14 | 88457599 | 88457685 | Hypo | cancer_general | U6, GALC |
| chr14 | 90983328 | 90983360 | Hypo | cancer_general | GPR68 | chr14 | 91691163 | 91691306 | Hypo | lung | GPR68 |
| chr14 | 91691696 | 91691822 | Hypo | lung | | chr14 | 91766154 | 91766450 | Hypo | lung | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 91780382 | 91780512 | Hypo | hepatobiliary | AX721199, BC039675, TRIP11 | chr14 | 91801036 | 91801164 | Hypo | hepatobiliary | CCDC88C |
| chr14 | 92507578 | 92507792 | Hypo | pancreas, cancer_general | | chr14 | 93155061 | 93155315 | Hypo | cancer_general | |
| chr14 | 93571193 | 93571326 | Hypo | breast | IFI27L2 | chr14 | 93706752 | 93706782 | Hypo | cancer_general | BTBD7 |
| chr14 | 94603542 | 94603670 | Hypo | lung | GSC | chr14 | 95233705 | 95233765 | Hypo | cancer_general | GSC |
| chr14 | 95240227 | 95240341 | Hypo | cancer_general | DICER1 | chr14 | 95557626 | 95557655 | Hypo | literature | DICER1 |
| chr14 | 95560448 | 95560477 | Hypo | literature | BC038791 | chr14 | 95740035 | 95740116 | Hypo | cancer_general | CLMN |
| chr14 | 96053974 | 96054020 | Hypo | cancer_general | HHIPL1, CYP46A1, MIR5698 | chr14 | 97045354 | 97045431 | Hypo | cancer_general | |
| chr14 | 100148073 | 100148230 | Hypo | cancer_general | | chr14 | 100643350 | 100643481 | Hypo | cancer_general | |
| chr14 | 100843765 | 100843912 | Hypo | cancer_general | WDR25, WARS | chr14 | 101250109 | 101250272 | Hypo | cancer_general | |
| chr14 | 101506231 | 101506260 | Hypo | literature | MIR539, JA715142, MIR376C, MIR543, MIR376A2, MIR1185-1, MIR381, MIR487B, MIR654, MIR1185-2, Mir_544, Mir_654, MIR1193, MIR300, MIR889, Mir_154, MIR495, MIR376B, MIR376A1, MIR655 | chr14 | 102418607 | 102418637 | Hypo | cancer_general | |
| chr14 | 102521602 | 102521758 | Hypo | cancer_general | | chr14 | 102529325 | 102529419 | Hypo | cancer_general | |
| chr14 | 102530007 | 102530234 | Hypo | cancer_general | | chr14 | 102530500 | 102530530 | Hypo | cancer_general | |
| chr14 | 102564464 | 102564605 | Hypo | breast | | chr14 | 102682077 | 102682149 | Hypo | lung, cancer_general | MOK, AK130824, WDR20 |
| chr14 | 102772607 | 102772695 | Hypo | cancer_general | MOK | chr14 | 102973169 | 102973268 | Hypo | head_neck | ANKRD9, TECPR2 |
| chr14 | 103477643 | 103477794 | Hypo | cancer_general | | chr14 | 104160060 | 104160134 | Hypo | cancer_general | AK097119, AX746968, XRCC3 |
| chr14 | 104202705 | 104202759 | Hypo | cancer_general | PPP1R13B, ZFYVE21 | chr14 | 104355204 | 104355273 | Hypo | cancer_general | |
| chr14 | 104386476 | 104387067 | Hypo | cancer_general | C14orf2, TDRD9 | chr14 | 104547785 | 104547909 | Hypo | cancer_general | ASPG |
| chr14 | 104571985 | 104572116 | Hypo | cancer_general | ASPG | chr14 | 104620411 | 104620554 | Hypo | cancer_general | KIF26A |
| chr14 | 104627664 | 104627759 | Hypo | cancer_general | KIF26A | chr14 | 104645126 | 104645188 | Hypo | cancer_general | KIF26A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 104646317 | 104646491 | Hypo | cancer_general | KIF26A | chr14 | 104647257 | 104647287 | Hypo | cancer_general | KIF26A |
| chr14 | 104682545 | 104682656 | Hypo | cancer_general |  | chr14 | 104862860 | 104863026 | Hypo | cancer_general |  |
| chr14 | 104897228 | 104897294 | Hypo | cancer_general |  | chr14 | 105157485 | 105157554 | Hypo | cancer_general | INF2 |
| chr14 | 105239389 | 105239439 | Hypo | literature | AKT1 | chr14 | 105239793 | 105239825 | Hypo | literature | AKT1 |
| chr14 | 105241309 | 105241428 | Hypo | literature | AKT1 | chr14 | 105243032 | 105243064 | Hypo | literature | AKT1 |
| chr14 | 105246427 | 105246582 | Hypo | literature | AKT1 | chr14 | 105658349 | 105658425 | Hypo | cancer_general |  |
| chr14 | 105714258 | 105714334 | Hypo | cancer_general | BTBD6, BRF1 | GL000231.1 | 12576 | 12717 | Hypo | cancer_general |  |
| HCMV-AD169 | 17724 | 17753 | Hypo | virus |  | HCMV-AD169 | 18691 | 18720 | Hypo | virus |  |
| HCMV-AD169 | 23851 | 23880 | Hypo | virus |  | HCMV-AD169 | 27296 | 27325 | Hypo | virus |  |
| HCMV-AD169 | 42909 | 42938 | Hypo | virus |  | HCMV-AD169 | 57909 | 57938 | Hypo | virus |  |
| HCMV-AD169 | 68427 | 68456 | Hypo | virus |  | HCMV-AD169 | 76862 | 76891 | Hypo | virus |  |
| HCMV-AD169 | 78956 | 78985 | Hypo | virus |  | HCMV-AD169 | 81188 | 81217 | Hypo | virus |  |
| HCMV-AD169 | 84448 | 84477 | Hypo | virus |  | HCMV-AD169 | 88920 | 88949 | Hypo | virus |  |
| HCMV-AD169 | 99889 | 99918 | Hypo | virus |  | HCMV-AD169 | 101238 | 101267 | Hypo | virus |  |
| HCMV-AD169 | 108021 | 108050 | Hypo | virus |  | HCMV-AD169 | 114824 | 114853 | Hypo | virus |  |
| HCMV-AD169 | 128011 | 128040 | Hypo | virus |  | HCMV-AD169 | 129567 | 129596 | Hypo | virus |  |
| HCMV-AD169 | 149187 | 149216 | Hypo | virus |  | HCMV-AD169 | 162299 | 162328 | Hypo | virus |  |
| HCMV-AD169 | 169250 | 169279 | Hypo | virus |  | HCMV-AD169 | 171221 | 171250 | Hypo | virus |  |
| HCMV-AD169 | 172561 | 172590 | Hypo | virus |  | HCMV-AD169 | 177053 | 177082 | Hypo | virus |  |
| HCMV-AD169 | 193060 | 193089 | Hypo | virus |  | HCMV-AD169 | 193858 | 193887 | Hypo | virus |  |
| HCMV-AD169 | 194176 | 194205 | Hypo | virus |  | HCMV-AD169 | 195222 | 195251 | Hypo | virus |  |
| HCMV-AD169 | 196060 | 196089 | Hypo | virus |  | HCMV-AD169 | 196817 | 196846 | Hypo | virus |  |
| HCMV-AD169 | 199152 | 199181 | Hypo | virus |  | HCMV-AD169 | 199906 | 199935 | Hypo | virus |  |
| HCMV-AD169 | 201145 | 201174 | Hypo | virus |  | HCMV-AD169 | 204433 | 204462 | Hypo | virus |  |
| HCMV-AD169 | 207682 | 207711 | Hypo | virus |  | HCMV-AD169 | 209510 | 209539 | Hypo | virus |  |
| HCMV-AD169 | 210069 | 210098 | Hypo | virus |  | HCMV-AD169 | 212133 | 212162 | Hypo | virus |  |
| HCMV-AD169 | 212591 | 212620 | Hypo | virus |  | HCMV-AD169 | 214453 | 214482 | Hypo | virus |  |
| HCMV-AD169 | 220316 | 220345 | Hypo | virus |  | MCV-R17b | 111 | 140 | Hypo | virus |  |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| MCV-R17b | 368 | 397 | Hypo | virus | | MCV-R17b | 625 | 654 | Hypo | virus | |
| MCV-R17b | 882 | 911 | Hypo | virus | | MCV-R17b | 1139 | 1168 | Hypo | virus | |
| MCV-R17b | 1396 | 1425 | Hypo | virus | | MCV-R17b | 1653 | 1682 | Hypo | virus | |
| MCV-R17b | 1910 | 1939 | Hypo | virus | | MCV-R17b | 2167 | 2196 | Hypo | virus | |
| MCV-R17b | 2424 | 2453 | Hypo | virus | | MCV-R17b | 2681 | 2710 | Hypo | virus | |
| MCV-R17b | 2938 | 2967 | Hypo | virus | | MCV-R17b | 3195 | 3224 | Hypo | virus | |
| MCV-R17b | 3452 | 3481 | Hypo | virus | | MCV-R17b | 3709 | 3738 | Hypo | virus | |
| MCV-R17b | 3966 | 3995 | Hypo | virus | | MCV-R17b | 4223 | 4252 | Hypo | virus | |
| MCV-R17b | 4480 | 4509 | Hypo | virus | | MCV-R17b | 4737 | 4766 | Hypo | virus | |
| MCV-R17b | 4994 | 5023 | Hypo | virus | | chr7 | 68930 | 68960 | Hypo | cancer_general | |
| chr7 | 369494 | 369536 | Hypo | cancer_general | | chr7 | 369844 | 369980 | Hypo | cancer_general | |
| chr7 | 389663 | 389693 | Hypo | cancer_general | | chr7 | 409826 | 409892 | Hypo | esophageal | |
| chr7 | 427454 | 427484 | Hypo | hepatobiliary | | chr7 | 431386 | 431492 | Hypo | cancer_general | LOC442497 |
| chr7 | 497782 | 497934 | Hypo | cancer_general | LOC442497 | chr7 | 503811 | 503936 | Hypo | cancer_general | LOC442497 |
| chr7 | 551599 | 551697 | Hypo | cancer_general | FLJ44511, PDGFA | chr7 | 564237 | 564271 | Hypo | breast | FLJ44511 |
| chr7 | 578922 | 579020 | Hypo | cancer_general | PRKAR1B | chr7 | 579827 | 579857 | Hypo | cancer_general | PRKAR1B SUN1, GET4 |
| chr7 | 842331 | 842414 | Hypo | cancer_general | | chr7 | 907656 | 907709 | Hypo | breast | |
| chr7 | 915058 | 915087 | Hypo | literature | GET4, SUN1 | chr7 | 1016343 | 1016373 | Hypo | colorectal | CYP2W1, COX19 |
| chr7 | 1022224 | 1022254 | Hypo | cancer_general | CYP2W1, COX19 | chr7 | 1030172 | 1030283 | Hypo | cancer_general | C7orf50, CYP2W1 |
| chr7 | 1054579 | 1054696 | Hypo | cancer_general | MIR339, C7orf50 | chr7 | 1086199 | 1086319 | Hypo | cancer_general | GPR146 |
| chr7 | 1195270 | 1195364 | Hypo | hepatobiliary | AK090593, AK123998, ZFAND2A | chr7 | 1308351 | 1308497 | Hypo | cancer_general | |
| chr7 | 1325810 | 1325882 | Hypo | cancer_general | | chr7 | 1416020 | 1416131 | Hypo | cancer_general | |
| chr7 | 1423632 | 1423677 | Hypo | cancer_general | | chr7 | 1459041 | 1459191 | Hypo | cancer_general | |
| chr7 | 1503417 | 1503596 | Hypo | cancer_general | AK127339, INTS1 | chr7 | 1547311 | 1547394 | Hypo | cancer_general | INTS1 |
| chr7 | 1598639 | 1598697 | Hypo | cancer_general | TMEM184A, PSMG3 | chr7 | 1607386 | 1607465 | Hypo | cancer_general | PSMG3-AS1, PSMG3 |
| chr7 | 1607971 | 1608001 | Hypo | cancer_general | PSMG3-AS1, PSMG3 | chr7 | 1611443 | 1611522 | Hypo | cancer_general | PSMG3-AS1, PSMG3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 1615390 | 1615444 | Hypo | cancer_general | PSMG3, PSMG3-AS1 | chr7 | 1627404 | 1627434 | Hypo | cancer_general | KIAA1908, PSMG3-AS1 |
| chr7 | 1641774 | 1641923 | Hypo | cancer_general | | chr7 | 1681189 | 1681239 | Hypo | cancer_general | |
| chr7 | 1688977 | 1689146 | Hypo | cancer_general | | chr7 | 1690745 | 1690851 | Hypo | cancer_general | |
| chr7 | 1733166 | 1733378 | Hypo | cancer_general | LOC401296 | chr7 | 1735223 | 1735554 | Hypo | cancer_general | LOC401296 |
| chr7 | 1775831 | 1775861 | Hypo | cancer_general | ELFN1, JX046910 | chr7 | 1778875 | 1778914 | Hypo | cancer_general | ELFN1, JX046910 |
| chr7 | 1783551 | 1783623 | Hypo | cancer_general | JX046910, ELFN1 | chr7 | 1786514 | 1786899 | Hypo | cancer_general | ELFN1, JX046910 |
| chr7 | 1787166 | 1787324 | Hypo | cancer_general | ELFN1, JX046910 | chr7 | 1800882 | 1800912 | Hypo | cancer_general | |
| chr7 | 1970842 | 1970872 | Hypo | pancreas | MAD1L1 | chr7 | 2109874 | 2109904 | Hypo | pancreas | MAD1L1 |
| chr7 | 2163332 | 2163467 | Hypo | cancer_general | MAD1L1 | chr7 | 2208670 | 2208808 | Hypo | cancer_general | MAD1L1 |
| chr7 | 2232963 | 2233056 | Hypo | cancer_general | MAD1L1 | chr7 | 2233292 | 2233414 | Hypo | cancer_general | MAD1L1 |
| chr7 | 2238118 | 2238235 | Hypo | lung | MAD1L1 | chr7 | 2300787 | 2300899 | Hypo | cancer_general | SNX8 |
| chr7 | 2361190 | 2361434 | Hypo | cancer_general | SNX8 | chr7 | 2473452 | 2473605 | Hypo | lung | BC034268, CHST12 |
| chr7 | 2565919 | 2566041 | Hypo | cancer_general | MIR4648, LFNG | chr7 | 2566600 | 2566630 | Hypo | cancer_general | MIR4648, LFNG |
| chr7 | 2595825 | 2595943 | Hypo | pancreas | IQCE, BRAT1 | chr7 | 2659340 | 2659370 | Hypo | cancer_general | |
| chr7 | 2720013 | 2720140 | Hypo | cancer_general | AMZ1 | chr7 | 2979480 | 2979512 | Hypo | literature | CARD11 |
| chr7 | 2985518 | 2985547 | Hypo | literature | CARD11 | chr7 | 3033658 | 3033688 | Hypo | cancer_general | CARD11 |
| chr7 | 3283704 | 3283894 | Hypo | cancer_general | | chr7 | 4215324 | 4215384 | Hypo | cancer_general | SDK1 |
| chr7 | 4657806 | 4657857 | Hypo | hepatobiliary | | chr7 | 4856984 | 4857048 | Hypo | cancer_general | RADIL |
| chr7 | 5262433 | 5262562 | Hypo | lung | WIPI2 | chr7 | 5397777 | 5397938 | Hypo | breast | TNRC18 |
| chr7 | 5603717 | 5603947 | Hypo | cancer_general | | chr7 | 5648107 | 5648393 | Hypo | literature, cancer_general | FSCN1 |
| chr7 | 6045612 | 6045641 | Hypo | literature | AIMP2, PMS2 | chr7 | 6059024 | 6059182 | Hypo | ovarian | EIF2AK1, AIMP2 |
| chr7 | 6060590 | 6060634 | Hypo | cancer_general | EIF2AK1, AIMP2 | chr7 | 6099217 | 6099334 | Hypo | cancer_general | |
| chr7 | 6124585 | 6124714 | Hypo | cancer_general | | chr7 | 6188610 | 6189061 | Hypo | breast | USP42 |
| chr7 | 6307943 | 6308066 | Hypo | cancer_general | CYTH3 | chr7 | 6414386 | 6414415 | Hypo | literature | RAC1 |
| chr7 | 6426878 | 6426907 | Hypo | literature | RAC1 | chr7 | 6443279 | 6443376 | Hypo | cancer_general | RAC1, DAGLB |
| chr7 | 6443826 | 6443856 | Hypo | cancer_general | DAGLB, RAC1 | chr7 | 6484445 | 6484545 | Hypo | lung | DAGLB |
| chr7 | 6524573 | 6524744 | Hypo | cancer_general | KDELR2 | chr7 | 6524977 | 6525012 | Hypo | cancer_general | KDELR2 |
| chr7 | 6525477 | 6525606 | Hypo | cancer_general | KDELR2 | chr7 | 6560235 | 6560345 | Hypo | cancer_general | Mir 633, GRID2IP |
| chr7 | 7015498 | 7015673 | Hypo | ovarian | | chr7 | 7605441 | 7605822 | Hypo | cancer_general | MIOS |
| chr7 | 8343630 | 8343724 | Hypo | cancer_general | | chr7 | 8391475 | 8391573 | Hypo | cancer_general | AX746880 |
| chr7 | 12751410 | 12751496 | Hypo | colorectal | | chr7 | 12776779 | 12776811 | Hypo | cancer_general | |
| chr7 | 20089670 | 20089700 | Hypo | hepatobiliary | | chr7 | 20183238 | 20183283 | Hypo | hepatobiliary | MACC1-AS1, MACC1 |
| chr7 | 21403615 | 21403645 | Hypo | cancer_general | | chr7 | 22824965 | 22825009 | Hypo | colorectal, cancer_general | |

TABLE 11-continued

| chr | Start | Stop | Hypo/hyper | classification | annotation |
|---|---|---|---|---|---|
| chr7 | 23253573 | 23253671 | Hypo | colorectal | AK057873 |
| chr7 | 23526549 | 23526698 | Hypo | cancer_general | RPS2P32 |
| chr7 | 23578703 | 23578857 | Hypo | cancer_general | TRA2A |
| chr7 | 24580644 | 24580806 | Hypo | cancer_general | |
| chr7 | 25132558 | 25132726 | Hypo | cancer_general | |
| chr7 | 25133492 | 25133650 | Hypo | cancer_general | |
| chr7 | 25165921 | 25166061 | Hypo | cancer_general | C7orf31, CYCS |
| chr7 | 26194906 | 26195024 | Hypo | cancer_general | NFE2L3 |
| chr7 | 26283775 | 26283954 | Hypo | cancer_general, breast | |
| chr7 | 27184015 | 27184190 | Hypo | literature | HOXA7, HOXA5, HOXA6, HOXA-AS3, DQ65986 JAZF1 |
| chr7 | 27245668 | 27245795 | Hypo | cancer_general | HOTTIP, HOXA13 |
| chr7 | 28110701 | 28110828 | Hypo | breast | |
| chr7 | 28238339 | 28238444 | Hypo | cancer_general | JAZF1-AS1 |
| chr7 | 28989065 | 28989159 | Hypo | cancer_general | TRIL, DQ601810 |
| chr7 | 30029923 | 30029952 | Hypo | tcga | SCRN1 |
| chr7 | 30030307 | 30030337 | Hypo | cancer_general | SCRN1 |
| chr7 | 30857157 | 30857292 | Hypo | lung | FAM188B, INMT-FAM188B |
| chr7 | 33167928 | 33168030 | Hypo | ovarian | BBS9 |
| chr7 | 33725803 | 33725938 | Hypo | lung | TBX20 |
| chr7 | 35298755 | 35298819 | Hypo | cancer_general | TBX20 |
| chr7 | 35301086 | 35301216 | Hypo | cancer_general | NME8 |
| chr7 | 37352957 | 37353062 | Hypo | cancer_general | |
| chr7 | 37907440 | 37907470 | Hypo | cancer_general | |
| chr7 | 38588471 | 38588501 | Hypo | esophageal | |
| chr7 | 42377468 | 42377497 | Hypo | literature | |
| chr7 | 43817999 | 43818119 | Hypo | cancer_general | BLVRA |
| chr7 | 44083283 | 44083416 | Hypo | cancer_general | RASA4CP, DBNL, LINC00957 |
| chr7 | 44097690 | 44097876 | Hypo | head_neck | PGAM2, DBNL |
| chr7 | 44151398 | 44151428 | Hypo | cancer_general | POLD2, AEBP1, MIR4649 |
| chr7 | 44151795 | 44151933 | Hypo | cancer_general | POLD2, AEBP1, MIR4649 |
| chr7 | 44740467 | 44740672 | Hypo | ovarian | OGDH |
| chr7 | 44835037 | 44835384 | Hypo | cancer_general | PPIA |
| chr7 | 44912004 | 44912034 | Hypo | head_neck | PURB |
| chr7 | 45026942 | 45027045 | Hypo | cancer_general | SNORA9, SNHG15, MYO1G |
| chr7 | 45038532 | 45038655 | Hypo | cancer_general | CCM2 |
| chr7 | 45046874 | 45046982 | Hypo | breast | CCM2 |
| chr7 | 45525402 | 45525432 | Hypo | cancer_general | |
| chr7 | 45614929 | 45615020 | Hypo | pancreas | ADCY1 |
| chr7 | 47515359 | 47515405 | Hypo | cancer_general | TNS3 |
| chr7 | 47704289 | 47704359 | Hypo | cancer_general | C7orf65 |
| chr7 | 49654508 | 49654538 | Hypo | cancer_general | |
| chr7 | 49819674 | 49819703 | Hypo | literature | VWC2 |
| chr7 | 50294451 | 50294481 | Hypo | cancer_general | |
| chr7 | 50365076 | 50365137 | Hypo | cancer_general | IKZF1 |
| chr7 | 50438618 | 50438648 | Hypo | cancer_general | |
| chr7 | 50441145 | 50441285 | Hypo | cancer_general | IKZF1 |
| chr7 | 50560588 | 50560637 | Hypo | literature | IKZF1 |
| chr7 | 55209976 | 55210005 | Hypo | literature | EGFR |
| chr7 | 55211065 | 55211094 | Hypo | literature | DDC |
| chr7 | 55221729 | 55221836 | Hypo | literature | EGFR |
| chr7 | 55223589 | 55223636 | Hypo | literature | EGFR |
| chr7 | 55227993 | 55228022 | Hypo | literature | EGFR-AS1, EGFR |
| chr7 | 55233028 | 55233123 | Hypo | literature | EGFR |
| chr7 | 55241663 | 55241737 | Hypo | literature | EGFR, EGFR-AS1 |
| chr7 | 55242419 | 55242493 | Hypo | literature | EGFR-AS1, EGFR |
| chr7 | 55248975 | 55249085 | Hypo | literature | |
| chr7 | 55259404 | 55259547 | Hypo | literature | EGFR, EGFR-AS1 |
| chr7 | 55260469 | 55260498 | Hypo | literature | EGFR, EGFR-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 55268867 | 55268896 | Hypo | literature | GU228584, EGFR | chr7 | 55410019 | 55410126 | Hypo | breast | |
| chr7 | 55506288 | 55506348 | Hypo | lung | LANCL2 | chr7 | 56018123 | 56018286 | Hypo | cancer_general | MRPS17, ZNF713 |
| chr7 | 56031716 | 56031869 | Hypo | cancer_general | GBAS, MRPS17 | chr7 | 63667431 | 63667460 | Hypo | literature | ZNF735 |
| chr7 | 64330411 | 64330470 | Hypo | hepatobiliary | AK097702 | chr7 | 64330734 | 64330833 | Hypo | cancer_general | AK097702 |
| chr7 | 64713317 | 64713449 | Hypo | cancer_general | | chr7 | 65510006 | 65510096 | Hypo | cancer_general | |
| chr7 | 65879649 | 65879883 | Hypo | cancer_general | | chr7 | 65880359 | 65880405 | Hypo | cancer_general | |
| chr7 | 66204493 | 66204617 | Hypo | cancer_general | RABGEF1 | chr7 | 66206923 | 66206953 | Hypo | cancer_general | RABGEF1 |
| chr7 | 66214923 | 66214961 | Hypo | cancer_general | RABGEF1 | chr7 | 67579765 | 67579911 | Hypo | cancer_general | |
| chr7 | 68204793 | 68204948 | Hypo | cancer_general | | chr7 | 69352121 | 69352272 | Hypo | cancer_general | |
| chr7 | 69897780 | 69897827 | Hypo | cancer_general | AUTS2 | chr7 | 70990312 | 70990342 | Hypo | cancer_general | AUTS2 |
| chr7 | 71438424 | 71438454 | Hypo | cancer_general | CALN1 | chr7 | 71603924 | 71604082 | Hypo | cancer_general | |
| chr7 | 71871203 | 71871245 | Hypo | cancer_general | | chr7 | 76033151 | 76033289 | Hypo | colorectal | ZP3 |
| chr7 | 77129743 | 77129907 | Hypo | lung | | chr7 | 77308664 | 77308899 | Hypo | cancer_general | RSBN1L-AS1 |
| chr7 | 77309437 | 77309511 | Hypo | cancer_general | RSBN1L-AS1 | chr7 | 77324362 | 77324593 | Hypo | cancer_general | RSBN1L, RSBN1L-AS1 |
| chr7 | 87105401 | 87105430 | Hypo | tcga | ABCB4 | chr7 | 87706818 | 87706877 | Hypo | cancer_general | ADAM22 |
| chr7 | 87825006 | 87825137 | Hypo | hepatobiliary | SRI | chr7 | 88388631 | 88388660 | Hypo | tcga | ZNF804B |
| chr7 | 90269263 | 90269563 | Hypo | literature, cancer_general | CDK14 | chr7 | 90797539 | 90797568 | Hypo | literature | CDK14 |
| chr7 | 92554253 | 92554452 | Hypo | cancer_general | GNGT1 | chr7 | 92689705 | 92689818 | Hypo | cancer_general | CASD1 |
| chr7 | 93220696 | 93220826 | Hypo | cancer_general | DLX6, DLX6-AS1 | chr7 | 94138158 | 94138315 | Hypo | cancer_general | DLX5 |
| chr7 | 96627013 | 96627064 | Hypo | cancer_general | ASNS | chr7 | 96651469 | 96651537 | Hypo | cancer_general | |
| chr7 | 97490474 | 97490508 | Hypo | hepatobiliary | BC122864, MGC72080 | chr7 | 97580497 | 97580648 | Hypo | cancer_general | MGC72080 BHLHA15, TECPR1, LMTK2 |
| chr7 | 97600104 | 97600224 | Hypo | cancer_general | | chr7 | 97839654 | 97839684 | Hypo | cancer_general | |
| chr7 | 97869290 | 97869391 | Hypo | cancer_general | TECPR1 | chr7 | 97869614 | 97869644 | Hypo | cancer_general | TECPR1 |
| chr7 | 98197206 | 98197242 | Hypo | cancer_general | | chr7 | 98966786 | 98966916 | Hypo | lung | ARPC1B, ARPC1A |
| chr7 | 98969875 | 98969928 | Hypo | cancer_general | ARPC1B, ARPC1A | chr7 | 98971509 | 98971549 | Hypo | cancer_general | ARPC1B, ARPC1A |
| chr7 | 99035152 | 99035191 | Hypo | esophageal | CPSF4, ATP5J2-PTCD1, PTCD1 | chr7 | 99104258 | 99104388 | Hypo | cancer_general | ZKSCAN5, AJ297365, ZNF394 |
| chr7 | 995591579 | 99591762 | Hypo | cancer_general | AZGP1P1 | chr7 | 99642049 | 99642100 | Hypo | cancer_general | ZSCAN21, ZKSCAN1 |
| chr7 | 99751578 | 99751630 | Hypo | colorectal | C7orf43, MIR4658, GAL3ST4, LAMTOR4 | chr7 | 99934913 | 99934943 | Hypo | cancer_general | PMS2P1, PILRB |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 100088183 | 100088312 | Hypo | cancer_general | NYAP1 | chr7 | 100179889 | 100179927 | Hypo | cancer_general | FBXO24, PCOLCE-AS1, LRCH4, ZASP, SAP25 |
| chr7 | 100241592 | 100241697 | Hypo | cancer_general | ACTL6B, TFR2 | chr7 | 100295321 | 100295424 | Hypo | cancer_general | GIGYF1, POP7 |
| chr7 | 100320690 | 100320719 | Hypo | literature | EPO | chr7 | 101241993 | 101242023 | Hypo | cancer_general | |
| chr7 | 101475790 | 101475858 | Hypo | cancer_general | CUX1 | chr7 | 101585887 | 101585917 | Hypo | cancer_general | CUX1 |
| chr7 | 101627741 | 101627787 | Hypo | cancer_general | CUX1 | chr7 | 101707502 | 101707532 | Hypo | cancer_general | CUX1 |
| chr7 | 102091406 | 102091534 | Hypo | blood | ALKBH4, ORAI2 | chr7 | 102801710 | 102801804 | Hypo | lung | |
| chr7 | 105279467 | 105279671 | Hypo | cancer_general | ATXN7L1 | chr7 | 106622834 | 106622961 | Hypo | cancer_general | |
| chr7 | 106797774 | 106797804 | Hypo | colorectal | PRKAR2B | chr7 | 107483694 | 107483918 | Hypo | colorectal | |
| chr7 | 111202993 | 111203260 | Hypo | literature, cancer_general | | chr7 | 116412008 | 116412058 | Hypo | literature | |
| chr7 | 116415100 | 116415129 | Hypo | literature | | chr7 | 116417443 | 116417496 | Hypo | literature | |
| chr7 | 116422067 | 116422132 | Hypo | literature | | chr7 | 116423399 | 116423488 | Hypo | literature | |
| chr7 | 121956724 | 121956754 | Hypo | cancer_general | CADPS2, FEZF1-AS1 | chr7 | 123175689 | 123175899 | Hypo | cancer_general | NDUFA5, IQUB |
| chr7 | 125082621 | 125082698 | Hypo | cancer_general | SND1 | chr7 | 127371129 | 127371249 | Hypo | breast | SND1 |
| chr7 | 127615921 | 127615951 | Hypo | ovarian | FLNC | chr7 | 128097059 | 128097089 | Hypo | cancer_general | HILPDA |
| chr7 | 128486036 | 128486138 | Hypo | cancer_general | KCP | chr7 | 128528749 | 128528779 | Hypo | cancer_general | KCP |
| chr7 | 128529023 | 128529053 | Hypo | cancer_general | UBE2H, AL832212 | chr7 | 129229456 | 129229631 | Hypo | cancer_general | |
| chr7 | 129483356 | 129483449 | Hypo | lung | TMEM209 | chr7 | 129794593 | 129794721 | Hypo | cancer_general | TMEM209 |
| chr7 | 129800243 | 129800434 | Hypo | breast | | chr7 | 129844226 | 129844493 | Hypo | cancer_general | SSMEM1, TMEM209 |
| chr7 | 1310441515 | 1310441596 | Hypo | breast | MKLN1 | chr7 | 134918503 | 134918637 | Hypo | breast | STRA8 |
| chr7 | 136969053 | 136969083 | Hypo | cancer_general | SNORD81, PTN | chr7 | 138042221 | 138042288 | Hypo | ovarian | |
| chr7 | 139878250 | 139878296 | Hypo | cancer_general | LOC100134229, JHDM1D | chr7 | 139939160 | 139939318 | Hypo | cancer_general | |
| chr7 | 140027008 | 140027079 | Hypo | colorectal | SLC37A3 | chr7 | 140096812 | 140096882 | Hypo | cancer_general | AK131347, RAB19 |
| chr7 | 140097126 | 140097196 | Hypo | cancer_general | AK131347, RAB19 | chr7 | 140180094 | 140180444 | Hypo | ovarian | MKRN1 |
| chr7 | 140218123 | 140218352 | Hypo | tcga | DENND2A | chr7 | 140219405 | 140219435 | Hypo | colorectal | DENND2A |
| chr7 | 140453121 | 140453167 | Hypo | literature | BRAF | chr7 | 140477779 | 140477868 | Hypo | literature | BRAF |
| chr7 | 140481381 | 140481431 | Hypo | literature | BRAF | chr7 | 142785612 | 142785728 | Hypo | cancer_general | |
| chr7 | 144712934 | 144713064 | Hypo | cancer_general | | chr7 | 148224541 | 148224686 | Hypo | cancer_general | |
| chr7 | 148508712 | 148508741 | Hypo | literature | EZH2 | chr7 | 148640171 | 148640250 | Hypo | cancer_general | |
| chr7 | 148846138 | 148846180 | Hypo | cancer_general | ZNF398 | chr7 | 148846434 | 148846644 | Hypo | cancer_general | ZNF398 |
| chr7 | 148851143 | 148851234 | Hypo | breast | ZNF398 | chr7 | 148883821 | 148883973 | Hypo | cancer_general | ZNF282, ZNF398 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 149109648 | 149109785 | Hypo | cancer_general | TRNA_Cys | chr7 | 150049604 | 150049718 | Hypo | cancer_general | ZNF775, |
| chr7 | 150069098 | 150069346 | Hypo | colorectal | ZNF775, RNU6-34P, REPIN1 | chr7 | 150069679 | 150069820 | Hypo | colorectal | REPIN1, RNU6-34P |
| chr7 | 150070021 | 150070058 | Hypo | colorectal | ZNF775, REPIN1, RNU6-34P | chr7 | 150081236 | 150081308 | Hypo | cancer_general | ZNF775 |
| chr7 | 150753942 | 150753981 | Hypo | cancer_general | SLC4A2, CDK5, ASIC3 | chr7 | 150870816 | 150870889 | Hypo | cancer_general | ASB10, GBX1 |
| chr7 | 151001356 | 151001435 | Hypo | cancer_general | | chr7 | 151188034 | 151188063 | Hypo | literature | RHEB |
| chr7 | 151298870 | 151299029 | Hypo | breast | PRKAG2 | chr7 | 151423571 | 151423639 | Hypo | lung | PRKAG2 |
| chr7 | 151591667 | 151591705 | Hypo | cancer_general | | chr7 | 152913656 | 152913826 | Hypo | cancer_general | |
| chr7 | 153663796 | 153663942 | Hypo | cancer_general | DPP6 | chr7 | 154561150 | 154561189 | Hypo | cancer_general | DPP6 |
| chr7 | 154708275 | 154708338 | Hypo | cancer_general | | chr7 | 154926351 | 154926397 | Hypo | cancer_general | |
| chr7 | 155302881 | 155302917 | Hypo | cancer_general | CNPY1 | chr7 | 155363304 | 155363417 | Hypo | cancer_general | |
| chr7 | 155580846 | 155580876 | Hypo | cancer_general | RBM33 | chr7 | 155581330 | 155581553 | Hypo | cancer_general | RBM33 |
| chr7 | 155581765 | 155581980 | Hypo | cancer_general | RBM33 | chr7 | 155582277 | 155582340 | Hypo | cancer_general | RBM33 |
| chr7 | 155877196 | 155877283 | Hypo | cancer_general | | chr7 | 156259192 | 156259221 | Hypo | literature | |
| chr7 | 156707963 | 156708093 | Hypo | cancer_general | MNX1 | chr7 | 156744619 | 156744713 | Hypo | cancer_general | NOM1 |
| chr7 | 156779336 | 156779366 | Hypo | cancer_general | | chr7 | 156832223 | 156832402 | Hypo | cancer_general | |
| chr7 | 156832848 | 156833162 | Hypo | cancer_general | | chr7 | 156880531 | 156880561 | Hypo | cancer_general | |
| chr7 | 157085373 | 157085487 | Hypo | cancer_general | | chr7 | 157085963 | 157086082 | Hypo | cancer_general | |
| chr7 | 157262815 | 157263018 | Hypo | cancer_general | PTPRN2 | chr7 | 157263294 | 157263471 | Hypo | cancer_general | |
| chr7 | 157335172 | 157335202 | Hypo | cancer_general | | chr7 | 157584178 | 157584208 | Hypo | cancer_general | |
| chr7 | 157588586 | 157588791 | Hypo | cancer_general | | chr7 | 157606706 | 157606736 | Hypo | cancer_general | |
| chr7 | 157690056 | 157690086 | Hypo | cancer_general | | chr7 | 158059762 | 158059794 | Hypo | cancer_general | |
| chr7 | 158065832 | 158065970 | Hypo | cancer_general | | chr7 | 158198597 | 158198648 | Hypo | hepatobiliary | |
| chr7 | 158298861 | 158299036 | Hypo | hepatobiliary | LINC00689 | chr7 | 158741193 | 158741267 | Hypo | breast | WDR60 |
| chr7 | 158799762 | 158799791 | Hypo | literature | ARL8B | chr3 | 3167720 | 3167750 | Hypo | cancer_general | TRNT1 |
| chr3 | 5165885 | 5165915 | Hypo | cancer_general | | chr3 | 9924238 | 9924534 | Hypo | cancer_general | JAGN1, CIDEC |
| chr3 | 9941469 | 9941669 | Hypo | cancer_general | IL17RE, JAGN1 | chr3 | 10027432 | 10027548 | Hypo | cancer_general | AX747493, AK125558, EMC3 |
| chr3 | 10182839 | 10183212 | Hypo | cancer_general, literature | VHL | chr3 | 10183753 | 10183782 | Hypo | literature | VHL |
| chr3 | 10184304 | 10184333 | Hypo | literature | VHL | chr3 | 10191477 | 10191620 | Hypo | literature | VHL |
| chr3 | 12586149 | 12586179 | Hypo | cancer_general | C3orf83 | chr3 | 12632309 | 12632401 | Hypo | literature | RAF1, MKRN2 |
| chr3 | 12645678 | 12645713 | Hypo | literature | RAF1 | chr3 | 12673006 | 12673036 | Hypo | lung | |
| chr3 | 12870826 | 12870856 | Hypo | cancer_general | RPL32, CAND2 | chr3 | 12926053 | 12926102 | Hypo | blood | |
| chr3 | 12977067 | 12977144 | Hypo | breast | IQSEC1 | chr3 | 13171814 | 13171844 | Hypo | esophageal | |
| chr3 | 13679172 | 13679349 | Hypo | cancer_general | | chr3 | 15123848 | 15123992 | Hypo | lung, cancer_general | ZFYVE20 |
| chr3 | 15780510 | 15780638 | Hypo | esophageal | BC041363, ANKRD28 | chr3 | 17001303 | 17001333 | Hypo | cancer_general | |
| chr3 | 17735273 | 17735340 | Hypo | cancer_general | TRNA_Pseudo | chr3 | 20070714 | 20070903 | Hypo | ovarian | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 23964882 | 23965019 | Hypo | ovarian | RPL15, NKIRAS1 | chr3 | 31494108 | 31494138 | Hypo | colorectal | |
| chr3 | 32708277 | 32708405 | Hypo | cancer_general | GOLGA4 | chr3 | 36984378 | 36984425 | Hypo | colorectal | TRANK1 |
| chr3 | 37276385 | 37276490 | Hypo | cancer_general | VILL | chr3 | 38030618 | 38030782 | Hypo | pancreas | VILL |
| chr3 | 38032331 | 38032361 | Hypo | cancer_general | | chr3 | 38182244 | 38182306 | Hypo | literature | MYD88, ACAA1 |
| chr3 | 38182626 | 38182655 | Hypo | literature | MYD88, ACAA1 | chr3 | 38208158 | 38208226 | Hypo | cancer_general | OXSR1 |
| chr3 | 40202174 | 40202255 | Hypo | cancer_general | MYRIP | chr3 | 41266086 | 41266151 | Hypo | literature | AK095242, AK311005, CTNNB1 |
| chr3 | 42222730 | 42222847 | Hypo | cancer_general | TRAK1 | chr3 | 42329346 | 42329511 | Hypo | cancer_general | CCBP2, HIGD1A |
| chr3 | 42640855 | 42640964 | Hypo | cancer_general | NKTR, SS18L2 | chr3 | 42852329 | 42852359 | Hypo | ovarian | |
| chr3 | 43735604 | 43735634 | Hypo | cancer_general | ABHD5 | chr3 | 47144864 | 47144893 | Hypo | literature | |
| chr3 | 47352704 | 47352734 | Hypo | ovarian | KLHL18 | chr3 | 47521062 | 47521178 | Hypo | cancer_general | |
| chr3 | 47555760 | 47555790 | Hypo | cancer_general | ELP6 | chr3 | 47830060 | 47830148 | Hypo | cancer_general | |
| chr3 | 47831601 | 47831819 | Hypo | cancer_general | | chr3 | 48227765 | 48227870 | Hypo | cancer_general | CDC25A |
| chr3 | 48236476 | 48236724 | Hypo | cancer_general | MIR4443, CDC25A | chr3 | 48698251 | 48698431 | Hypo | ovarian | |
| chr3 | 48978413 | 48978479 | Hypo | cancer_general | ARIH2 | chr3 | 49124883 | 49142913 | Hypo | cancer_general | QARS, USP19 |
| chr3 | 49196747 | 49196831 | Hypo | ovarian | CCDC71, LAMB2P1 | chr3 | 49405953 | 49405982 | Hypo | literature | RHOA |
| chr3 | 49412883 | 49412987 | Hypo | literature | RHOA | chr3 | 49939931 | 49940398 | Hypo | cancer_general | MON1A, MST1R |
| chr3 | 50072827 | 50072925 | Hypo | cancer_general | RBM6 | chr3 | 50395506 | 50395536 | Hypo | cancer_general | Mir_324, CACNA2D2, TMEM115, CYB561D2, NPRL2 |
| chr3 | 50575616 | 50575658 | Hypo | cancer_general | | chr3 | 50968445 | 50968511 | Hypo | cancer_general | DOCK3 |
| chr3 | 52352194 | 52352326 | Hypo | cancer_general | DNAH1 | chr3 | 52442062 | 52442091 | Hypo | literature | PHF7, BAP1, DNAH1 |
| chr3 | 52552556 | 52552661 | Hypo | cancer_general | STAB1, NT5DC2 | chr3 | 52553469 | 52553499 | Hypo | cancer_general | STAB1, NT5DC2 |
| chr3 | 53032733 | 53033524 | Hypo | cancer_general | DCP1A | chr3 | 53253306 | 53253599 | Hypo | cancer_general | TKT |
| chr3 | 53382392 | 53382565 | Hypo | cancer_general | | chr3 | 53480528 | 53480683 | Hypo | cancer_general | |
| chr3 | 54583435 | 54583465 | Hypo | hepatobiliary | | chr3 | 55603443 | 55603632 | Hypo | cancer_general | |
| chr3 | 57437452 | 57437482 | Hypo | cancer_general | BC041347 | chr3 | 57529094 | 57529218 | Hypo | breast | ERC2 |
| chr3 | 58153446 | 58153608 | Hypo | ovarian | | chr3 | 63719169 | 63719303 | Hypo | cancer_general | DNAH12 |
| chr3 | 66053446 | 66053613 | Hypo | lung | MITF | chr3 | 69740944 | 69740990 | Hypo | cancer_general | |
| chr3 | 69937703 | 69937848 | Hypo | cancer_general | PPP4R2 | chr3 | 70661011 | 70661079 | Hypo | hepatobiliary | |
| chr3 | 73045340 | 73045583 | Hypo | cancer_general | ARL13B | chr3 | 88247941 | 88248049 | Hypo | cancer_general | |
| chr3 | 93698033 | 93698063 | Hypo | cancer_general | DCBLD2 | chr3 | 98113191 | 98113253 | Hypo | cancer_general | CPOX |
| chr3 | 98618182 | 98618376 | Hypo | cancer_general | SENP7 | chr3 | 100228688 | 100228768 | Hypo | cancer_general | TMEM45A SENP7, |
| chr3 | 101094160 | 101094190 | Hypo | colorectal | | chr3 | 101230678 | 101231070 | Hypo | cancer_general | FAM172BP |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 101331792 | 101331861 | Hypo | head_neck | ZBTB11, RPL24, ZBTB11-AS1 | chr3 | 101354294 | 101354442 | Hypo | cancer_general | RPL24, ZBTB11-AS1 |
| chr3 | 101397240 | 101397358 | Hypo | cancer_general | | chr3 | 101406823 | 101407190 | Hypo | cancer_general | |
| chr3 | 101411545 | 101411666 | Hypo | lung | RPL24 | chr3 | 101645019 | 101645181 | Hypo | cancer_general | |
| chr3 | 105015466 | 105015519 | Hypo | cancer_general | | chr3 | 105684885 | 105684987 | Hypo | breast | BTLA |
| chr3 | 106936157 | 106936336 | Hypo | cancer_general | LINC00882 | chr3 | 112185933 | 112185975 | Hypo | hepatobiliary | DRD3 |
| chr3 | 113557333 | 113557363 | Hypo | cancer_general | GRAMD1C | chr3 | 113847911 | 113847941 | Hypo | cancer_general | LSAMP |
| chr3 | 115502232 | 115502390 | Hypo | cancer_general | | chr3 | 115512319 | 115512448 | Hypo | pancreas | POLQ |
| chr3 | 120004468 | 120004497 | Hypo | tcga | | chr3 | 121215241 | 121215271 | Hypo | head_neck | ILDR1 |
| chr3 | 121657197 | 121657515 | Hypo | cancer_general | SLC15A2 | chr3 | 121741545 | 121741598 | Hypo | cancer_general | KPNA1 |
| chr3 | 122162036 | 122162117 | Hypo | cancer_general | KPNA1 | chr3 | 122162890 | 122163054 | Hypo | cancer_general | DIRC2 |
| chr3 | 122234242 | 122234538 | Hypo | cancer_general | KPNA1 | chr3 | 122573688 | 122573826 | Hypo | cancer_general | |
| chr3 | 122702288 | 122702451 | Hypo | cancer_general | SEMA5B | chr3 | 124410075 | 124410157 | Hypo | head_neck | UNQ2790, ZXDC, CCDC37 |
| chr3 | 125417341 | 125417424 | Hypo | cancer_general | TRNA_Glu | chr3 | 126157586 | 126157663 | Hypo | breast | |
| chr3 | 126261929 | 126262000 | Hypo | ovarian | C3orf22, CHST13 | chr3 | 127534814 | 127534897 | Hypo | cancer_general | MGLL |
| chr3 | 128056383 | 128056497 | Hypo | cancer_general | EEFSEC | chr3 | 128384991 | 128385132 | Hypo | cancer_general | |
| chr3 | 128599405 | 128599477 | Hypo | cancer_general | LOC653712, ACAD9 | chr3 | 128786496 | 128786526 | Hypo | colorectal | GP9 |
| chr3 | 129008841 | 129009004 | Hypo | head_neck | C3orf37 | chr3 | 129047978 | 129048008 | Hypo | cancer_general | H1FX-AS1 |
| chr3 | 129372419 | 129372546 | Hypo | hepatobiliary | TMCC1 | chr3 | 130502167 | 130502197 | Hypo | cancer_general | |
| chr3 | 130519901 | 130520077 | Hypo | cancer_general | | chr3 | 133217784 | 133217999 | Hypo | head_neck | PCCB SOX14, BC038725 |
| chr3 | 133970381 | 133970474 | Hypo | cancer_general | RYK | chr3 | 136016868 | 136016942 | Hypo | cancer_general | |
| chr3 | 136582883 | 136582951 | Hypo | cancer_general | NCK1, SLC35G2 | chr3 | 137490806 | 137490860 | Hypo | cancer_general | DBR1 FAIM, CEP70 |
| chr3 | 137892691 | 137892721 | Hypo | cancer_general | DBR1 | chr3 | 137894374 | 137894415 | Hypo | cancer_general | |
| chr3 | 138058859 | 138058897 | Hypo | cancer_general | MRAS | chr3 | 138318827 | 138318918 | Hypo | breast | |
| chr3 | 138374229 | 138374258 | Hypo | literature | PIK3CB FOXL2, C3orf72, AK304483, AK128202 | chr3 | 138635369 | 138635507 | Hypo | cancer_general | ZBTB38 |
| chr3 | 138662266 | 138662296 | Hypo | cancer_general | | chr3 | 141174349 | 141174606 | Hypo | cancer_general | |
| chr3 | 141363466 | 141363496 | Hypo | breast | TFDP2, AX748420 | chr3 | 141481651 | 141482073 | Hypo | cancer_general | TFDP2 |
| chr3 | 141657032 | 141657079 | Hypo | cancer_general | | chr3 | 141832939 | 141833015 | Hypo | head_neck | |
| chr3 | 141835935 | 141836077 | Hypo | cancer_general | TFDP2 | chr3 | 142159804 | 142159841 | Hypo | breast | |
| chr3 | 142537638 | 142537779 | Hypo | breast | PCOLCE2 | chr3 | 142718283 | 142718358 | Hypo | cancer_general | XRN1, ATR |
| chr3 | 142791151 | 142791255 | Hypo | colorectal | | chr3 | 142896156 | 142896214 | Hypo | cancer_general | LOC100289361, U2SURP |
| chr3 | 143280343 | 143280373 | Hypo | cancer_general | | chr3 | 143614462 | 143614504 | Hypo | cancer_general | |
| chr3 | 145735852 | 145735882 | Hypo | ovarian | | chr3 | 146187946 | 146187978 | Hypo | cancer_general | PLSCR2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 148523213 | 148523297 | Hypo | cancer_general | | chr3 | 148803120 | 148803276 | Hypo | cancer_general | HLTF-AS1, HLTF |
| chr3 | 150237792 | 150237822 | Hypo | cancer_general | | chr3 | 152107022 | 152107052 | Hypo | pancreas | RAP2B |
| chr3 | 152707390 | 152707460 | Hypo | cancer_general | | chr3 | 152877666 | 152877696 | Hypo | pancreas | |
| chr3 | 155456372 | 155456630 | Hypo | pancreas, cancer_general | | chr3 | 155461030 | 155461195 | Hypo | cancer_general | |
| chr3 | 156007772 | 156007801 | Hypo | literature | KCNAB1 | chr3 | 158319235 | 158319359 | Hypo | hepatobiliary | MLF1 |
| chr3 | 169539898 | 169540679 | Hypo | cancer_general | LRRIQ4, LRRC34 | chr3 | 169541070 | 169541102 | Hypo | cancer_general | LRRIQ4 |
| chr3 | 170602030 | 170602133 | Hypo | cancer_general | EIF5A2 | chr3 | 171193088 | 171193311 | Hypo | cancer_general | |
| chr3 | 171529811 | 171529958 | Hypo | cancer_general | | chr3 | 172342101 | 172342147 | Hypo | cancer_general | NCEH1 |
| chr3 | 172355895 | 172356038 | Hypo | cancer_general | NCEH1 | chr3 | 172383550 | 172383600 | Hypo | cancer_general | NCEH1 |
| chr3 | 172425382 | 172425717 | Hypo | cancer_general | U6, NCEH1 | chr3 | 172469925 | 172470036 | Hypo | cancer_general | ECT2 |
| chr3 | 173162817 | 173162847 | Hypo | cancer_general | NLGN1 | chr3 | 176710106 | 176710241 | Hypo | ovarian | |
| chr3 | 176872357 | 176872443 | Hypo | cancer_general | TBLXR1 | chr3 | 178861259 | 178861447 | Hypo | cancer_general | PIK3CA, BC032034 |
| chr3 | 178916711 | 178916959 | Hypo | literature | PIK3CA | chr3 | 178921537 | 178921568 | Hypo | literature | PIK3CA |
| chr3 | 178927966 | 178928094 | Hypo | literature | PIK3CA | chr3 | 178936059 | 178936111 | Hypo | literature | PIK3CA |
| chr3 | 178952004 | 178952105 | Hypo | literature | KCNMB3, PIK3CA | chr3 | 179367874 | 179367920 | Hypo | cancer_general | USP13 |
| chr3 | 181444108 | 181444236 | Hypo | cancer_general | | chr3 | 182815811 | 182816027 | Hypo | cancer_general | MCCC1 |
| chr3 | 182895956 | 182896144 | Hypo | cancer_general | MCF2L2 | chr3 | 182911545 | 182911574 | Hypo | literature | MCF2L2 |
| chr3 | 183109854 | 183109883 | Hypo | literature | | chr3 | 183183523 | 183183659 | Hypo | cancer_general | LINC00888 |
| chr3 | 183208370 | 183208469 | Hypo | cancer_general | KLHL6 | chr3 | 183217676 | 183217706 | Hypo | ovarian | KLHL6 |
| chr3 | 183647996 | 183648026 | Hypo | cancer_general | ABCC5 | chr3 | 183728793 | 183728952 | Hypo | breast | ABCC5-AS1, ABCC5 |
| chr3 | 183870824 | 183870858 | Hypo | cancer_general | DVL3 | chr3 | 183872490 | 183872524 | Hypo | cancer_general | DVL3 |
| chr3 | 183965599 | 183965907 | Hypo | cancer_general | ECE2, ALG3, MIR1224, VWA5B2 | chr3 | 184018038 | 184018136 | Hypo | cancer_general | PSMD2, ECE2 |
| chr3 | 184031686 | 184031746 | Hypo | cancer_general | PSMD2, EIF4G1 | chr3 | 184057254 | 184057557 | Hypo | lung, cancer_general | FAM131A, CLCN2 |
| chr3 | 185001696 | 185001919 | Hypo | cancer_general | MAP3K13 | chr3 | 185271296 | 185271764 | Hypo | cancer_general | LIPH |
| chr3 | 185275856 | 185275886 | Hypo | cancer_general | LIPH | chr3 | 185303247 | 185303277 | Hypo | cancer_general | SENP2 |
| chr3 | 185363074 | 185363261 | Hypo | cancer_general | IGF2BP2 | chr3 | 185629516 | 185629546 | Hypo | cancer_general | TRA2B |
| chr3 | 185643324 | 185643405 | Hypo | cancer_general | TRA2B | chr3 | 185658513 | 185658543 | Hypo | cancer_general | TRA2B |
| chr3 | 185668237 | 185668311 | Hypo | cancer_general | LOC344887 | chr3 | 186287130 | 186287270 | Hypo | cancer_general | DNAJB11, TBCCD1 |
| chr3 | 186914705 | 186914734 | Hypo | literature | RTP1 | chr3 | 193312128 | 193312347 | Hypo | cancer_general | OPA1 |
| chr3 | 193419702 | 193419732 | Hypo | ovarian | | chr3 | 193548637 | 193548835 | Hypo | cancer_general | |
| chr3 | 194048751 | 194048919 | Hypo | cancer_general | | chr3 | 194120812 | 194120841 | Hypo | literature | ATP13A3, GP5 |
| chr3 | 194981913 | 194981913 | Hypo | cancer_general | | chr3 | 195095450 | 195095543 | Hypo | ovarian | ACAP2 |
| chr3 | 195184022 | 195184140 | Hypo | colorectal | | chr3 | 195409773 | 195409813 | Hypo | ovarian | SDHAP2 |
| chr3 | 195536733 | 195536848 | Hypo | cancer_general | MUC4 | chr3 | 195538217 | 195538353 | Hypo | cancer_general | MUC4 |
| chr3 | 195587032 | 195587118 | Hypo | cancer_general | TNK2 | chr3 | 195601239 | 195601312 | Hypo | pancreas | TNK2 |

TABLE 11-continued

| chr | Start | Stop | Hypo/hyper | classification | annotation |
|---|---|---|---|---|---|
| chr3 | 195602330 | 195602576 | Hypo | pancreas | TNK2 |
| chr3 | 195648794 | 195649004 | Hypo | cancer_general | |
| chr3 | 196046702 | 196046830 | Hypo | head_neck | TM4SF19, TM4SF19-TCTEX1D2, AK124973, TCTEX1D2 |
| chr3 | 196069743 | 196070340 | Hypo | cancer_general | TM4SF19, TM4SF19-TCTEX1D2 |
| chr3 | 196344683 | 196344796 | Hypo | esophageal | LRRC33 |
| chr3 | 196387628 | 196387665 | Hypo | cancer_general | |
| chr3 | 196433946 | 196434104 | Hypo | head_neck | PIGX, CEP19, U6 |
| chr3 | 196667872 | 196668080 | Hypo | cancer_general | NCBP2-AS2, PIGZ, NCBP2, SENP5 |
| chr3 | 196731155 | 196731313 | Hypo | cancer_general | MFI2-AS1, MFI2 |
| chr3 | 197247047 | 197247110 | Hypo | pancreas | BDH1 |
| chr3 | 197313997 | 197314107 | Hypo | cancer_general | LOC220729 |
| chr3 | 197330060 | 197330147 | Hypo | cancer_general | LOC220729 |
| chr3 | 197616707 | 197616861 | Hypo | cancer_general | IQCG, LRCH3 |
| chr3 | 197686495 | 197686524 | Hypo | literature | LMLN, RPL35A, IQCG |
| chr1 | 898654 | 898690 | Hypo | head_neck | PLEKHN1, KLHL17, NOC2L |
| chr1 | 1047531 | 1047647 | Hypo | breast | C1orf159, MIR429, JA715143, MIR200B, MIR200A, JA715134 |
| chr1 | 1095420 | 1095459 | Hypo | colorectal | |
| chr1 | 1218737 | 1218820 | Hypo | cancer_general | UBE2J2, ACAP3, SCNN1D |
| chr1 | 1235813 | 1236078 | Hypo | cancer_general | PUSL1, ACAP3, SCNN1D |
| chr3 | 195639755 | 195639785 | Hypo | head_neck | AK127609, TNK2 |
| chr3 | 195834581 | 195834611 | Hypo | cancer_general | TM4SF19 |
| chr3 | 196065342 | 196065583 | Hypo | literature | TM4SF19-TCTEX1D2 |
| chr3 | 196263303 | 196263471 | Hypo | cancer_general | |
| chr3 | 196387295 | 196387415 | Hypo | cancer_general | LRRC33 |
| chr3 | 196388383 | 196388581 | Hypo | cancer_general | LRRC33 |
| chr3 | 196440510 | 196440676 | Hypo | head_neck | PIGX, U6, CEP19 |
| chr3 | 196728418 | 196728448 | Hypo | head_neck | MFI2, MFI2-AS1 |
| chr3 | 197209019 | 197209048 | Hypo | literature | |
| chr3 | 197278926 | 197278988 | Hypo | pancreas | BDH1 |
| chr3 | 197326860 | 197327042 | Hypo | cancer_general | LOC220729 |
| chr3 | 197466364 | 197466540 | Hypo | cancer_general | FYTTD1, KIAA0226 |
| chr3 | 197685788 | 197686085 | Hypo | literature, cancer_general | LMLN, RPL35A, IQCG |
| chr1 | 715373 | 715447 | Hypo | cancer_general | LOC100288069 |
| chr1 | 913532 | 913955 | Hypo | cancer_general | PLEKHN1, C1orf170 |
| chr1 | 1080583 | 1080824 | Hypo | cancer_general | LOC254099, SDF4, TNFRSF4, TNFRSF18 |
| chr1 | 1146734 | 1146818 | Hypo | cancer_general | |
| chr1 | 1223512 | 1223652 | Hypo | cancer_general | ACAP3, SCNN1D |
| chr1 | 1253330 | 1253386 | Hypo | lung, cancer_general | CPSF3L, GLTPD1, PUSL1, ACAP3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 1267014 | 1267151 | Hypo | cancer_general | DVL1, TAS1R3, GLTPD1, CPSF3L | chr1 | 1267462 | 1267699 | Hypo | cancer_general | CPSF3L, DVL1, TAS1R3, GLTPD1 |
| chr1 | 1267906 | 1268158 | Hypo | cancer_general | CPSF3L, DVL1, TAS1R3, GLTPD1 | chr1 | 1281214 | 1281244 | Hypo | pancreas | MXRA8, DVL1 |
| chr1 | 1341668 | 1341743 | Hypo | cancer_general | MRPL20, LOC148413, CCNL2 | chr1 | 1436043 | 1436211 | Hypo | cancer_general | ATAD3B |
| chr1 | 1473125 | 1473207 | Hypo | head_neck | AX747755, ATAD3A, SSU72, TMEM240 | chr1 | 1483186 | 1483363 | Hypo | head_neck | TMEM240, SSU72 |
| chr1 | 1547129 | 1547348 | Hypo | lung | MIB2, AK094692 | chr1 | 1563193 | 1563223 | Hypo | cancer_general | CDK11B, MIB2, MMP23B |
| chr1 | 1805049 | 1805089 | Hypo | breast | GNB1 | chr1 | 1856436 | 1856466 | Hypo | head_neck | C1orf222, TMEM52, CALML6 |
| chr1 | 1857847 | 1857909 | Hypo | cancer_general | C1orf222, TMEM52, CALML6 | chr1 | 1874744 | 1874787 | Hypo | cancer_general | KIAA1751 |
| chr1 | 1910415 | 1910445 | Hypo | head_neck | KIAA1751 | chr1 | 1923457 | 1923521 | Hypo | cancer_general | KIAA1751 |
| chr1 | 1974848 | 1974925 | Hypo | cancer_general | PRKCZ | chr1 | 2066490 | 2066679 | Hypo | cancer_general | PRKCZ |
| chr1 | 2125216 | 2125483 | Hypo | cancer_general | C1orf86, BC018779 | chr1 | 2263169 | 2263263 | Hypo | cancer_general | MORN1 |
| chr1 | 2267552 | 2267690 | Hypo | cancer_general | MORN1 | chr1 | 2304327 | 2304389 | Hypo | cancer_general | MORN1 |
| chr1 | 2307925 | 2307955 | Hypo | cancer_general | MORN1 | chr1 | 2308376 | 2308636 | Hypo | cancer_general | MORN1 |
| chr1 | 2309868 | 2309953 | Hypo | cancer_general | MORN1 | chr1 | 2331363 | 2331437 | Hypo | ovarian | PEX10, RER1, MORN1 |
| chr1 | 2336397 | 2336427 | Hypo | breast | PEX10, RER1 | chr1 | 2397001 | 2397031 | Hypo | cancer_general | |
| chr1 | 2428331 | 2428385 | Hypo | cancer_general | PLCH2 | chr1 | 2507063 | 2507183 | Hypo | cancer_general | MMEL1 |
| chr1 | 2514330 | 2514376 | Hypo | ovarian | FAM213B, MMEL1 | chr1 | 2521024 | 2521063 | Hypo | breast | FAM213B |
| chr1 | 2830155 | 2830185 | Hypo | cancer_general | | chr1 | 2866038 | 2866068 | Hypo | cancer_general | |
| chr1 | 3102653 | 3102779 | Hypo | cancer_general | | chr1 | 3158823 | 3158962 | Hypo | cancer_general | |
| chr1 | 3182883 | 3182917 | Hypo | ovarian | | chr1 | 3183415 | 3183455 | Hypo | cancer_general | |
| chr1 | 3322090 | 3322170 | Hypo | cancer_general | | chr1 | 3601850 | 3601946 | Hypo | cancer_general | |
| chr1 | 3607081 | 3607236 | Hypo | literature, cancer_general | TP73 | chr1 | 3659550 | 3659716 | Hypo | colorectal | TP73 |
| chr1 | 3664461 | 3664741 | Hypo | cancer_general | CCDC27, TP73-AS1, LRRC47, SMIM1 | chr1 | 3683686 | 3683818 | Hypo | cancer_general | TP73-AS1, TP73, CCDC27 SMIM1, CCDC27 |
| chr1 | 3700384 | 3700414 | Hypo | ovarian | | chr1 | 3733551 | 3733581 | Hypo | esophageal | CEP104 |
| chr1 | 4111061 | 4111231 | Hypo | cancer_general | | chr1 | 4401433 | 4401463 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 5919973 | 5920071 | Hypo | hepatobiliary | MIR4689, NPHP4 | chr1 | 5920650 | 5920710 | Hypo | hepatobiliary | MIR4689, NPHP4 |
| chr1 | 5924296 | 5924431 | Hypo | hepatobiliary | NPHP4, MIR4689 | chr1 | 5924851 | 5924984 | Hypo | hepatobiliary | NPHP4, MIR4689 |
| chr1 | 5926596 | 5926645 | Hypo | hepatobiliary | NPHP4, MIR4689 | chr1 | 5933086 | 5933144 | Hypo | hepatobiliary | NPHP4 |
| chr1 | 5934925 | 5935061 | Hypo | hepatobiliary | NPHP4 | chr1 | 5940517 | 5940547 | Hypo | hepatobiliary | NPHP4 |
| chr1 | 5940945 | 5941132 | Hypo | hepatobiliary | NPHP4 | chr1 | 5944299 | 5944449 | Hypo | hepatobiliary | NPHP4 |
| chr1 | 5944962 | 5945001 | Hypo | hepatobiliary | NPHP4 | chr1 | 5945348 | 5945435 | Hypo | hepatobiliary | NPHP4 |
| chr1 | 5947258 | 5947288 | Hypo | hepatobiliary | NPHP4 | chr1 | 5949491 | 5949575 | Hypo | hepatobiliary | NPHP4 |
| chr1 | 5950965 | 5951039 | Hypo | hepatobiliary | NPHP4 | chr1 | 5957473 | 5957503 | Hypo | hepatobiliary | NPHP4 |
| chr1 | 5967237 | 5967267 | Hypo | hepatobiliary | NPHP4 | chr1 | 5969001 | 5969283 | Hypo | hepatobiliary | NPHP4 |
| chr1 | 5972104 | 5972134 | Hypo | hepatobiliary | NPHP4 | chr1 | 5972878 | 5972922 | Hypo | hepatobiliary | NPHP4 |
| chr1 | 6021621 | 6021651 | Hypo | hepatobiliary |  | chr1 | 6025872 | 6025950 | Hypo | hepatobiliary |  |
| chr1 | 6036766 | 6036796 | Hypo | hepatobiliary |  | chr1 | 6056157 | 6056201 | Hypo | hepatobiliary | KCNAB2 |
| chr1 | 6056506 | 6056651 | Hypo | hepatobiliary | KCNAB2 CHD5, KCNAB2 | chr1 | 6059910 | 6059974 | Hypo | hepatobiliary | KCNAB2 |
| chr1 | 6166353 | 6166469 | Hypo | cancer_general |  | chr1 | 6171763 | 6171810 | Hypo | cancer_general | CHD5 |
| chr1 | 6186511 | 6186546 | Hypo | pancreas | CHD5 | chr1 | 6280243 | 6280273 | Hypo | cancer_general | ICMT, RNF207 |
| chr1 | 6284828 | 6284858 | Hypo | pancreas | ICMT, RNF207 | chr1 | 6360593 | 6360634 | Hypo | cancer_general | ACOT7 |
| chr1 | 6410456 | 6410486 | Hypo | head_neck | ACOT7 | chr1 | 6446131 | 6446308 | Hypo | cancer_general | ACOT7 |
| chr1 | 6672227 | 6672351 | Hypo | cancer_general | PHF13, KLHL21 | chr1 | 6713914 | 6714041 | Hypo | ovarian | DNAJC11 |
| chr1 | 6714348 | 6714378 | Hypo | ovarian | DNAJC11 | chr1 | 6776304 | 6776388 | Hypo | cancer_general | RERE |
| chr1 | 7973843 | 7973948 | Hypo | cancer_general | TNFRSF9 | chr1 | 8549986 | 8550078 | Hypo | lung, cancer_general |  |
| chr1 | 9402465 | 9402616 | Hypo | breast | SPSB1 | chr1 | 9601954 | 9601984 | Hypo | hepatobiliary | SLC25A33 |
| chr1 | 9722138 | 9722215 | Hypo | esophageal | C1orf200, PIK3CD | chr1 | 9795995 | 9796196 | Hypo | ovarian | CLSTN1, PIK3CD |
| chr1 | 9865110 | 9865140 | Hypo | cancer_general | CLSTN1 | chr1 | 9867157 | 9867316 | Hypo | lung | CLSTN1 |
| chr1 | 10091888 | 10092060 | Hypo | cancer_general | UBE4B | chr1 | 10095469 | 10095845 | Hypo | cancer_general | UBE4B |
| chr1 | 10123736 | 10123928 | Hypo | head_neck | UBE4B | chr1 | 10166521 | 10166551 | Hypo | head_neck | UBE4B |
| chr1 | 10491694 | 10491724 | Hypo | cancer_general | APITD1-CORT, APITD1 | chr1 | 11169346 | 11169375 | Hypo | literature | MTOR, EXOSC10 |
| chr1 | 11174404 | 11174433 | Hypo | literature | MTOR | chr1 | 11181358 | 11181432 | Hypo | literature | MTOR |
| chr1 | 11182142 | 11182171 | Hypo | literature | MTOR | chr1 | 11188149 | 11188178 | Hypo | literature | MTOR |
| chr1 | 11210182 | 11210211 | Hypo | literature | MTOR-AS1, MTOR | chr1 | 11217215 | 11217337 | Hypo | literature | MTOR-AS1, MTOR |
| chr1 | 11591719 | 11591826 | Hypo | cancer_general | PTCHD2 | chr1 | 11886250 | 11886280 | Hypo | head_neck | CLCN6 |
| chr1 | 11936748 | 11936778 | Hypo | cancer_general |  | chr1 | 12041374 | 12041525 | Hypo | cancer_general | MFN2, PLOD1 |
| chr1 | 12251443 | 12251958 | Hypo | lung, cancer_general | MIR4632, TNFRSF1B | chr1 | 12460299 | 12460356 | Hypo | ovarian | VPS13D |
| chr1 | 13984525 | 13984742 | Hypo | head_neck |  | chr1 | 14032304 | 14032347 | Hypo | hepatobiliary |  |
| chr1 | 14097878 | 14098015 | Hypo | esophageal | PRDM2 | chr1 | 14128478 | 14128588 | Hypo | cancer_general | PRDM2 |
| chr1 | 14149749 | 14149867 | Hypo | head_neck | AK124197 | chr1 | 14730425 | 14730472 | Hypo | cancer_general |  |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 14746206 | 14746245 | Hypo | hepatobiliary | | chr1 | 15128565 | 15128595 | Hypo | hepatobiliary | KAZN |
| chr1 | 16474413 | 16474576 | Hypo | pancreas | EPHA2 | chr1 | 16475031 | 16475207 | Hypo | pancreas | EPHA2 |
| chr1 | 17757538 | 17757570 | Hypo | colorectal | RCC2 | chr1 | 17787472 | 17787502 | Hypo | cancer_general | TMCO4 |
| chr1 | 19980747 | 19980858 | Hypo | cancer_general | NBL1 | chr1 | 20127338 | 20127471 | Hypo | cancer_general | |
| chr1 | 20248109 | 20248141 | Hypo | cancer_general | PLA2G2E, OTUD3 | chr1 | 20492168 | 20492298 | Hypo | cancer_general | PLA2G2C |
| chr1 | 21026117 | 21026225 | Hypo | cancer_general | KIF17 | chr1 | 21042894 | 21042924 | Hypo | cancer_general | KIF17, SH2D5 |
| chr1 | 21050471 | 21050511 | Hypo | head_neck | SH2D5, KIF17 | chr1 | 21573283 | 21573362 | Hypo | breast | ECE1 |
| chr1 | 21573668 | 21574203 | Hypo | breast | ECE1 | chr1 | 21713716 | 21713792 | Hypo | head_neck | |
| chr1 | 22141326 | 22141355 | Hypo | tcga | LDLRAD2, HSPG2 | chr1 | 22222711 | 22222793 | Hypo | breast | HSPG2 |
| chr1 | 22927410 | 22927482 | Hypo | cancer_general | EPHA8 | chr1 | 23347997 | 23348043 | Hypo | cancer_general | KDMIA, LOC729059 |
| chr1 | 23449766 | 23449859 | Hypo | head_neck | LUZP1 | chr1 | 24104000 | 24104062 | Hypo | cancer_general | LOC100506963, PITHD1 |
| chr1 | 24161782 | 24161882 | Hypo | colorectal | FUCA1 | chr1 | 24740603 | 24740829 | Hypo | cancer_general | NIPAL3 |
| chr1 | 25257490 | 25257529 | Hypo | literature | RUNX3 | chr1 | 25257916 | 25258250 | Hypo | literature | RUNX3 |
| chr1 | 25919307 | 25919337 | Hypo | ovarian | | chr1 | 26183522 | 26183579 | Hypo | breast | PAQR7, AUNIP |
| chr1 | 26467523 | 26467630 | Hypo | cancer_general, lung | | chr1 | 26917724 | 26917816 | Hypo | cancer_general | |
| chr1 | 26963625 | 26963789 | Hypo | pancreas | FAM46B | chr1 | 27190175 | 27190278 | Hypo | cancer_general | SFN |
| chr1 | 27332448 | 27332673 | Hypo | head_neck | WASF2, GPR3 | chr1 | 27340252 | 27340412 | Hypo | cancer_general | FAM46B |
| chr1 | 27724058 | 27724093 | Hypo | cancer_general | ATPIF1, JA611241, DNAJC8 | chr1 | 27844518 | 27844548 | Hypo | cancer_general | |
| chr1 | 28558539 | 28558571 | Hypo | cancer_general | PHACTR4 | chr1 | 28726724 | 28726812 | Hypo | ovarian | PHACTR4 |
| chr1 | 28727177 | 28727324 | Hypo | ovarian | YTHDF2 | chr1 | 28727894 | 28728020 | Hypo | ovarian | PHACTR4 |
| chr1 | 29047659 | 29048643 | Hypo | cancer_general | | chr1 | 29060250 | 29060311 | Hypo | cancer_general | YTHDF2 |
| chr1 | 29065131 | 29065211 | Hypo | cancer_general | | chr1 | 30351554 | 30351742 | Hypo | cancer_general | TMEM39B, KHDRBS1 |
| chr1 | 31863186 | 31863216 | Hypo | cancer_general | FAM167B, MTM9RLP, EIF3I | chr1 | 32533211 | 32533653 | Hypo | cancer_general | HDAC1, LCK |
| chr1 | 32705488 | 32705550 | Hypo | cancer_general | ZBTB8A, ZBTB8B | chr1 | 32756498 | 32756581 | Hypo | cancer_general | |
| chr1 | 32938720 | 32938750 | Hypo | cancer_general | ZMYM1 | chr1 | 33163605 | 33163786 | Hypo | head_neck | SYNC |
| chr1 | 35586911 | 35586962 | Hypo | cancer_general | CLSPN | chr1 | 35664625 | 35664746 | Hypo | cancer_general | SFPQ |
| chr1 | 36236269 | 36236299 | Hypo | cancer_general | COL8A2, ADPRHL2, TEKT2 | chr1 | 36334925 | 36335053 | Hypo | cancer_general | AGO1 |
| chr1 | 36563479 | 36563522 | Hypo | cancer_general | | chr1 | 38060267 | 38060317 | Hypo | cancer_general | GNL2 |
| chr1 | 38398213 | 38398348 | Hypo | cancer_general | INPP5B | chr1 | 39416980 | 39417182 | Hypo | cancer_general | RHBDL2 |
| chr1 | 40072513 | 40072680 | Hypo | cancer_general | | chr1 | 40349545 | 40349647 | Hypo | cancer_general | |
| chr1 | 40625371 | 40625401 | Hypo | cancer_general | RLF | chr1 | 40708443 | 40708578 | Hypo | head_neck | TMCO2, RLF |
| chr1 | 41915253 | 41915283 | Hypo | breast | | chr1 | 41967342 | 41967418 | Hypo | cancer_general | HIVEP3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 41991640 | 41991702 | Hypo | cancer_general | HIVEP3 | chr1 | 43188741 | 43188874 | Hypo | cancer_general | CLDN19 |
| chr1 | 43400336 | 43400386 | Hypo | head_neck | SLC2A1 | chr1 | 43478202 | 43478255 | Hypo | cancer_general | ELOVL1, CDC20 |
| chr1 | 43814994 | 43815023 | Hypo | literature | CDC20, MPL | chr1 | 43834741 | 43834922 | Hypo | cancer_general | PTPRF |
| chr1 | 43842664 | 43842779 | Hypo | lung | MED8, ELOVL1 | chr1 | 44068774 | 44068804 | Hypo | cancer_general | |
| chr1 | 44109845 | 44109959 | Hypo | cancer_general | KDM4A | chr1 | 44310283 | 44310324 | Hypo | colorectal | ST3GAL3 |
| chr1 | 44494137 | 44494169 | Hypo | cancer_general | SLC6A9 | chr1 | 44726912 | 44727268 | Hypo | cancer_general | ERI3 |
| chr1 | 45240427 | 45240514 | Hypo | cancer_general | SNORD38B, BEST4, KIF2C, RPS8, SNORD55, SNORD46, SNORD38A | chr1 | 45308154 | 45308262 | Hypo | cancer_general | PTCH2, EIF2B3 |
| chr1 | 45645870 | 45645998 | Hypo | cancer_general | ZSWIM5 | chr1 | 45768429 | 45768504 | Hypo | cancer_general | LOC400752 |
| chr1 | 46077719 | 46077805 | Hypo | esophageal | CCDC17, NASP | chr1 | 46347598 | 46347689 | Hypo | cancer_general | MAST2 |
| chr1 | 46744657 | 46744733 | Hypo | breast | RAD54L, LRRC41 | chr1 | 47035373 | 47035403 | Hypo | ovarian | |
| chr1 | 47078736 | 47078782 | Hypo | head_neck | MOB3C, MKNK1 | chr1 | 47788247 | 47788348 | Hypo | colorectal | MKNK1 |
| chr1 | 50881363 | 50881529 | Hypo | cancer_general | DMRTA2 | chr1 | 51424099 | 51424224 | Hypo | cancer_general | CDKN2C ORC1, CC2D1B |
| chr1 | 51763252 | 51763298 | Hypo | cancer_general | TTC39A | chr1 | 52832687 | 52832820 | Hypo | cancer_general | |
| chr1 | 53129154 | 53129244 | Hypo | cancer_general | FAM159A | chr1 | 53192045 | 53192075 | Hypo | breast | ZYG11B |
| chr1 | 53705647 | 53705701 | Hypo | pancreas | LOC100507564, MAGOH, LRP8 | chr1 | 54586626 | 54586736 | Hypo | cancer_general | |
| chr1 | 54337089 | 54337119 | Hypo | esophageal | SSBP3 | chr1 | 54877027 | 54877451 | Hypo | ovarian | SSBP3 |
| chr1 | 55231115 | 55231177 | Hypo | cancer_general | PARS2 | chr1 | 61541602 | 61541718 | Hypo | cancer_general, lung | NFIA |
| chr1 | 62189908 | 62189987 | Hypo | cancer_general | TM2D1 | chr1 | 62793237 | 62793267 | Hypo | pancreas | |
| chr1 | 64734652 | 64734694 | Hypo | cancer_general | | chr1 | 65303636 | 65303692 | Hypo | literature | |
| chr1 | 65304227 | 65304256 | Hypo | literature | JAK1, RAVER2 | chr1 | 65305384 | 65305413 | Hypo | literature | JAK1, RAVER2 |
| chr1 | 65306926 | 65306955 | Hypo | literature | JAK1, RAVER2 | chr1 | 65309787 | 65309816 | Hypo | literature | JAK1, RAVER2 |
| chr1 | 65310487 | 65310531 | Hypo | literature | JAK1 | chr1 | 65311188 | 65311217 | Hypo | literature | JAK1 |
| chr1 | 65312331 | 65312432 | Hypo | literature | JAK1 | chr1 | 67669791 | 67669853 | Hypo | ovarian | JAK1 |
| chr1 | 70599012 | 70599169 | Hypo | cancer_general | LRRC7 | chr1 | 70672778 | 70672878 | Hypo | cancer_general | IL23R, U6 SRSF11, LRRC40 |
| chr1 | 75600925 | 75601071 | Hypo | cancer_general | LHX8, AK055631 | chr1 | 76354624 | 76354754 | Hypo | cancer_general | MSH4 |
| chr1 | 78463647 | 78463677 | Hypo | cancer_general | DNAJB4 | chr1 | 84944491 | 84944568 | Hypo | cancer_general | RPF1 |
| chr1 | 85725639 | 85725668 | Hypo | tcga | BCL10, C1orf52 | chr1 | 86296345 | 86296375 | Hypo | cancer_general | COL24A1 |
| chr1 | 86860608 | 86860949 | Hypo | cancer_general | ODF2L | chr1 | 89394066 | 89394163 | Hypo | breast | CBL2 |
| chr1 | 91177989 | 91178149 | Hypo | cancer_general | BARHL2 | chr1 | 91182805 | 91182835 | Hypo | pancreas | BARHL2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 94147816 | 94147845 | Hypo | tcga | | chr1 | 94343568 | 94343744 | Hypo | cancer_general | GCLM, DNTTIP2 |
| chr1 | 94911234 | 94911328 | Hypo | breast | ABCD3 | chr1 | 97185262 | 97185609 | Hypo | head_neck | PTBP2 |
| chr1 | 98515142 | 98515191 | Hypo | pancreas | MIR2682, MIR137HG, MIR137 | chr1 | 100239507 | 100239544 | Hypo | cancer_general | |
| chr1 | 100310827 | 100310979 | Hypo | cancer_general | AGL | chr1 | 100437068 | 100437172 | Hypo | cancer_general | SLC35A3, BC112312 |
| chr1 | 108722798 | 108722828 | Hypo | hepatobiliary | SLC25A24 | chr1 | 109585463 | 109585632 | Hypo | cancer_general | WDR47 |
| chr1 | 109595405 | 109595534 | Hypo | ovarian | | chr1 | 109631549 | 109631682 | Hypo | cancer_general | TMEM167B |
| chr1 | 109644226 | 109644336 | Hypo | cancer_general | C1orf194, SCARNA2, TMEM167B | chr1 | 110883542 | 110883965 | Hypo | cancer_general | RBM15, LOC440600, BC069739 |
| chr1 | 111440961 | 111440999 | Hypo | cancer_general | CD53 | chr1 | 112084954 | 112084984 | Hypo | cancer_general | RAP1A |
| chr1 | 113166315 | 113166394 | Hypo | head_neck | CAPZA1, ST7L | chr1 | 114428007 | 114428160 | Hypo | head_neck | BCL2L15, AP4B1-AS1, AP4B1 |
| chr1 | 114448943 | 114448990 | Hypo | cancer_general | DCLRE1B, AP4B1 | chr1 | 115055395 | 115055425 | Hypo | cancer_general | DENND2C |
| chr1 | 115256514 | 115256552 | Hypo | literature | CSDE1, NRAS | chr1 | 115258729 | 115258772 | Hypo | literature | CSDE1, NRAS |
| chr1 | 116214104 | 116214318 | Hypo | cancer_general | VANGL1 | chr1 | 117901133 | 117901264 | Hypo | cancer_general | MAN1A2 |
| chr1 | 146551186 | 146551215 | Hypo | literature | TRNA_Pseudo, TRNA_His | chr1 | 150603138 | 150603170 | Hypo | cancer_general | ENSA |
| chr1 | 150941425 | 150941847 | Hypo | breast | CERS2, SETDB1 | chr1 | 150994849 | 150995152 | Hypo | ovarian | U6, PRUNE |
| chr1 | 151042405 | 151042496 | Hypo | cancer_general | MLLT11, GABPB2 | chr1 | 151169248 | 151170206 | Hypo | cancer_general | PIP5K1A, VPS72 |
| chr1 | 151253146 | 151253427 | Hypo | cancer_general | ZNF687, BC021024 | chr1 | 151300888 | 151300918 | Hypo | cancer_general | |
| chr1 | 151362640 | 151362779 | Hypo | colorectal | PSMB4 | chr1 | 153539476 | 153539637 | Hypo | cancer_general | S100A2 |
| chr1 | 153540096 | 153540154 | Hypo | cancer_general | S100A2 | chr1 | 153896746 | 153896800 | Hypo | cancer_general | DENND4B, GATAD2B |
| chr1 | 153937124 | 153937330 | Hypo | cancer_general | CREB3L4, JTB, SLC39A1, CRTC2 | chr1 | 153948791 | 153948823 | Hypo | cancer_general | RAB13, JTB, CREB3L4 |
| chr1 | 154156468 | 154156717 | Hypo | cancer_general | MIR190B, TPM3 | chr1 | 154491036 | 154491066 | Hypo | cancer_general | TDRD10 |
| chr1 | 154516810 | 154516845 | Hypo | cancer_general | UBE2Q1, TDRD10 | chr1 | 155161778 | 155162033 | Hypo | cancer_general | TRIM46, DM075093, MIR92B, THBS3, MUC1, AX746485 |
| chr1 | 155283218 | 155283248 | Hypo | breast | RUSC1-AS1, RUSC1, FDPS | chr1 | 155578375 | 155578921 | Hypo | cancer_general | MSTO1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 155617837 | 155611962 | Hypo | cancer_general | BC041646 | chr1 | 155653788 | 155653868 | Hypo | head_neck | YY1AP1, DAP3 |
| chr1 | 155826248 | 155826336 | Hypo | cancer_general | SYT11 | chr1 | 155874151 | 155874300 | Hypo | literature | KIAA0907, RIT1 |
| chr1 | 155874508 | 155874546 | Hypo | literature | KIAA0907, RIT1 | chr1 | 155954282 | 155954396 | Hypo | cancer_general | ARHGEF2 |
| chr1 | 156010377 | 156010548 | Hypo | lung, cancer_general | UBQLN4 | chr1 | 156017591 | 156017683 | Hypo | ovarian | LAMTOR2, UBQLN4 |
| chr1 | 156030286 | 156030621 | Hypo | cancer_general | RAB25, LAMTOR2, UBQLN4 | chr1 | 156432124 | 156432637 | Hypo | cancer_general | MEF2D |
| chr1 | 156838167 | 156838320 | Hypo | cancer_general | NTRK1 | chr1 | 157247347 | 157247388 | Hypo | cancer_general | |
| chr1 | 157458909 | 157458961 | Hypo | cancer_general | | chr1 | 157895413 | 157895443 | Hypo | cancer_general | AK057438 |
| chr1 | 158205040 | 158205070 | Hypo | cancer_general | | chr1 | 158245556 | 158245586 | Hypo | cancer_general | |
| chr1 | 158295829 | 158295935 | Hypo | cancer_general | CD1B | chr1 | 158318949 | 158318979 | Hypo | hepatobiliary | CD1E |
| chr1 | 158591699 | 158591947 | Hypo | cancer_general | SPTA1 | chr1 | 158669704 | 158669882 | Hypo | cancer_general | OR6K2 |
| chr1 | 158672678 | 158672678 | Hypo | cancer_general | OR6K2 | chr1 | 158687415 | 158687550 | Hypo | cancer_general | OR6K3 |
| chr1 | 158748648 | 158748771 | Hypo | cancer_general | OR6N2 | chr1 | 158760197 | 158760235 | Hypo | cancer_general | |
| chr1 | 158778060 | 158778152 | Hypo | cancer_general | | chr1 | 158815136 | 158815295 | Hypo | cancer_general | MNDA |
| chr1 | 158907635 | 158907665 | Hypo | cancer_general | PYHIN1 | chr1 | 159140357 | 159140386 | Hypo | literature | CADM3 |
| chr1 | 159187279 | 159187429 | Hypo | cancer_general | | chr1 | 159258862 | 159258891 | Hypo | literature | FCER1A |
| chr1 | 159337419 | 159337615 | Hypo | cancer_general | BC038194 | chr1 | 159409192 | 159409221 | Hypo | literature | OR10J1, BC038194 |
| chr1 | 160451043 | 160451202 | Hypo | cancer_general | SLAMF6 | chr1 | 160693934 | 160694102 | Hypo | cancer_general | F11R |
| chr1 | 160880758 | 160880788 | Hypo | cancer_general | | chr1 | 160986299 | 160986385 | Hypo | lung | USF1, ARHGAP30, TSTD1 |
| chr1 | 160992336 | 160992587 | Hypo | cancer_general | F11R | chr1 | 161007587 | 161007746 | Hypo | cancer_general | NIT1, DEDD, PFDN2 |
| chr1 | 161013554 | 161013677 | Hypo | blood | USF1, TSTD1, ARHGAP30 | chr1 | 161086730 | 161086813 | Hypo | cancer_general | |
| chr1 | 161122645 | 161122778 | Hypo | cancer_general | UFC1, USP21 | chr1 | 161359069 | 161359099 | Hypo | cancer_general | |
| chr1 | 161367577 | 161367701 | Hypo | lung, cancer_general | TRNA_Val | chr1 | 161368283 | 161368507 | Hypo | cancer_general | TRNA_Val |
| chr1 | 161442441 | 161442471 | Hypo | cancer_general | TRNA_Asp, TRNA_Glu, TRNA_Gly, TRNA_Leu | chr1 | 161466301 | 161466347 | Hypo | cancer_general | FCGR2A |
| chr1 | 161471657 | 161471779 | Hypo | lung | FCGR2A | chr1 | 162427088 | 162427153 | Hypo | lung | |
| chr1 | 162724401 | 162724430 | Hypo | literature | DDR2 | chr1 | 162729615 | 162729686 | Hypo | literature | |
| chr | 162748392 | 162748421 | Hypo | literature | AF268386, Metazoa_SRP, DDR2 | chr1 | 163393034 | 163393064 | Hypo | hepatobiliary | DDR2 |
| chr1 | 164428741 | 164428831 | Hypo | cancer_general | LOC100505795 | chr1 | 164518220 | 164518270 | Hypo | hepatobiliary | LMX1A |
| chr1 | 164730649 | 164730796 | Hypo | cancer_general, hepatobiliary | ADCY10 | chr1 | 165324305 | 165324357 | Hypo | cancer_general | BLZF1 |
| chr1 | 167823339 | 167823461 | Hypo | cancer_general, breast | | chr1 | 169355697 | 169355727 | Hypo | pancreas | CCDC181 |
| chr1 | 169838016 | 169838187 | Hypo | breast | Metazoa_SRP, SCYL3 | chr1 | 169930112 | 169930305 | Hypo | pancreas | KIFAP3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 170063947 | 170064218 | Hypo | cancer_general | | chr1 | 170629999 | 170630029 | Hypo | cancer_general | PRRX1 |
| chr1 | 171625525 | 171625561 | Hypo | cancer_general | | chr1 | 171665240 | 171665330 | Hypo | cancer_general | VAMP4 |
| chr1 | 175346381 | 175346551 | Hypo | cancer_general | | chr1 | 175388664 | 175388700 | Hypo | cancer_general | TNR |
| chr1 | 178063112 | 178063150 | Hypo | breast | MYOC | chr1 | 179046338 | 179046385 | Hypo | pancreas | FAM20B, TOR3A |
| chr1 | 179262226 | 179262256 | Hypo | cancer_general | TNR | chr1 | 180235730 | 180235760 | Hypo | cancer_general | LHX4, LOC100527964 |
| chr1 | 180882640 | 180882669 | Hypo | tcga | RASAL2, RASAL2-AS1 | chr1 | 180919682 | 180919718 | Hypo | breast | KIAA1614, AK056657 |
| chr1 | 180925271 | 180925402 | Hypo | cancer_general | SOAT1 | chr1 | 181014878 | 181014997 | Hypo | head_neck | MR1 |
| chr1 | 182807578 | 182807742 | Hypo | cancer_general | KIAA1614 | chr1 | 182862133 | 182862328 | Hypo | cancer_general, colorectal | SHCBP1L, DHX9 |
| chr1 | 183129382 | 183129737 | Hypo | cancer_general | AK056657, KIAA1614 | chr1 | 183462761 | 183463024 | Hypo | cancer_general | SMG7 |
| chr1 | 183627506 | 183627539 | Hypo | cancer_general | DHX9, NPL | chr1 | 184970783 | 184970847 | Hypo | cancer_general | |
| chr1 | 185073818 | 185073966 | Hypo | breast | APOBEC4, RGL1 | chr1 | 185076172 | 185076270 | Hypo | ovarian | RNF2 |
| chr1 | 185336061 | 185336095 | Hypo | cancer_general | RNF2 | chr1 | 186570930 | 186571030 | Hypo | hepatobiliary | |
| chr1 | 195732322 | 195732539 | Hypo | cancer_general | | chr1 | 197771547 | 197771893 | Hypo | cancer_general | |
| chr1 | 197888831 | 197888945 | Hypo | cancer_general | LHX9 | chr1 | 198124799 | 198124932 | Hypo | cancer_general | NEK7 |
| chr1 | 200047843 | 200047892 | Hypo | cancer_general | | chr1 | 200591054 | 200591225 | Hypo | cancer_general | KIF14 |
| chr1 | 201983113 | 201983200 | Hypo | cancer_general | ELF3, RNPEP | chr1 | 202081728 | 202081804 | Hypo | cancer_general | |
| chr1 | 202311820 | 202311901 | Hypo | cancer_general | UBE2T, PPP1R12B | chr1 | 202531939 | 202532087 | Hypo | breast | PPP1R12B |
| chr1 | 202856858 | 202856937 | Hypo | cancer_general | RABIF, KLHL12 | chr1 | 203298307 | 203298710 | Hypo | cancer_general | |
| chr1 | 203429564 | 203429594 | Hypo | cancer_general | | chr1 | 203681332 | 203681362 | Hypo | blood | ATP2B4 |
| chr1 | 204333609 | 204333668 | Hypo | cancer_general | LINC00628 | chr1 | 204478284 | 204478427 | Hypo | cancer_general | MDM4, TRNA_Lys |
| chr1 | 204499813 | 204499842 | Hypo | literature | MDM4 | chr1 | 204524704 | 204524744 | Hypo | head_neck | MDM4 |
| chr1 | 204531203 | 204531757 | Hypo | breast | MDM4 | chr1 | 206950282 | 206950328 | Hypo | cancer_general | IL10 |
| chr1 | 207200870 | 207200962 | Hypo | cancer_general | PFKFB2, C1orf116 | chr1 | 207227318 | 207227556 | Hypo | cancer_general | PFKFB2, YOD1 |
| chr1 | 207794579 | 207794609 | Hypo | cancer_general | CR1 | chr1 | 207833206 | 207833370 | Hypo | cancer_general | CR1L |
| chr1 | 209164972 | 209165091 | Hypo | cancer_general | | chr1 | 209604382 | 209604597 | Hypo | literature | MIR205, MIR205HG |
| chr1 | 209605386 | 209605415 | Hypo | literature | MIR205HG, MIR205 | chr1 | 211847706 | 211847787 | Hypo | cancer_general | NEK2 |
| chr1 | 212484610 | 212484816 | Hypo | ovarian | PPP2R5A | chr1 | 212963883 | 212964151 | Hypo | cancer_general | |
| chr1 | 213189937 | 213190065 | Hypo | cancer_general | ANGEL2 | chr1 | 217307369 | 217307654 | Hypo | pancreas, cancer_general | TATDN3, NSL1 |
| chr1 | 217309764 | 217309816 | Hypo | cancer_general | SPATA17, GPATCH2 | chr1 | 217311463 | 217311516 | Hypo | cancer_general | |
| chr1 | 217805158 | 217805395 | Hypo | cancer_general | | chr1 | 220132075 | 220132111 | Hypo | colorectal | EPRS |
| chr1 | 220636466 | 220636510 | Hypo | cancer_general | C1orf140 | chr1 | 220896508 | 220896568 | Hypo | cancer_general | |
| chr1 | 221510339 | 221510368 | Hypo | literature | | chr1 | 223894714 | 223894752 | Hypo | cancer_general | CAPN2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 223899470 | 223899500 | Hypo | cancer_general | CAPN2 | chr1 | 224267615 | 224267662 | Hypo | cancer_general | NVL |
| chr1 | 224400490 | 224400524 | Hypo | cancer_general | | chr1 | 224493975 | 224494083 | Hypo | lung | CNIH3 |
| chr1 | 224804831 | 224804910 | Hypo | cancer_general | CNIH3 | chr1 | 224805564 | 224805620 | Hypo | cancer_general | AK124056 |
| chr1 | 225118306 | 225118474 | Hypo | cancer_general | DNAH14 | chr1 | 225908076 | 225908184 | Hypo | cancer_general | BC033346, ACBD3 |
| chr1 | 226265194 | 226265257 | Hypo | cancer_general | BC032899, H3F3AP4, H3F3A | chr1 | 226384322 | 226384440 | Hypo | cancer_general | |
| chr1 | 226997660 | 226997719 | Hypo | hepatobiliary | | chr1 | 228201221 | 228201251 | Hypo | cancer_general | WNT3A |
| chr1 | 228461158 | 228461197 | Hypo | hepatobiliary | OBSCN | chr1 | 228528840 | 228529016 | Hypo | cancer_general | OBSCN |
| chr1 | 228558699 | 228559238 | Hypo | cancer_general | OBSCN | chr1 | 228693629 | 228693767 | Hypo | cancer_general | RNF187 |
| chr1 | 229476753 | 229476879 | Hypo | cancer_general | CCSAP | chr1 | 230404217 | 230404263 | Hypo | cancer_general | GALNT2 |
| chr1 | 231149928 | 231150098 | Hypo | cancer_general | FAM89A, MIR1182 | chr1 | 231475814 | 231476081 | Hypo | cancer_general | SPRTN, EXOC8 |
| chr1 | 233465473 | 233465503 | Hypo | cancer_general | KIAA1804 | chr1 | 234445373 | 234445403 | Hypo | cancer_general | MIR4671, SLC35F3 |
| chr1 | 234620866 | 234620979 | Hypo | ovarian | TARBP1 | chr1 | 234798171 | 234798201 | Hypo | cancer_general | BC032040 |
| chr1 | 234839889 | 234840058 | Hypo | ovarian | | chr1 | 234844955 | 234845079 | Hypo | cancer_general | |
| chr1 | 234845467 | 234845497 | Hypo | lung | | chr1 | 235266920 | 235266950 | Hypo | cancer_general | TOMM20 |
| chr1 | 235665663 | 235665736 | Hypo | cancer_general | B3GALNT2 | chr1 | 235669296 | 235669398 | Hypo | cancer_general | B3GALNT2 |
| chr1 | 237970760 | 237970826 | Hypo | cancer_general | RYR2 | chr1 | 238024448 | 238024477 | Hypo | literature | LOC100130331 |
| chr1 | 240118848 | 240118973 | Hypo | cancer_general | | chr1 | 240256663 | 240256780 | Hypo | pancreas | FMN2 |
| chr1 | 241052096 | 241052126 | Hypo | cancer_general | RGS7 | chr1 | 241052360 | 241052419 | Hypo | colorectal | RGS7 |
| chr1 | 241912749 | 241912778 | Hypo | literature | WDR64 | chr1 | 243859000 | 243859029 | Hypo | literature | |
| chr1 | 243921295 | 243921330 | Hypo | cancer_general | | chr1 | 244115072 | 244115212 | Hypo | cancer_general | LOC339529 |
| chr1 | 245032517 | 245032603 | Hypo | lung | HNRNPU | chr1 | 245135753 | 245136064 | Hypo | cancer_general | EFCAB2 |
| chr1 | 245494495 | 245494578 | Hypo | ovarian | KIF26B | chr1 | 245849914 | 245849944 | Hypo | hepatobiliary | KIF26B |
| chr1 | 246198078 | 246198203 | Hypo | breast | SMYD3 | chr1 | 246330309 | 246330409 | Hypo | cancer_general | SMYD3 |
| chr1 | 246488175 | 246488336 | Hypo | head_neck | SMYD3 | chr1 | 246654652 | 246654851 | Hypo | breast | SMYD3 |
| chr1 | 247284422 | 247284452 | Hypo | cancer_general | ZNF124, C1orf229 | chr1 | 247608784 | 247608814 | Hypo | hepatobiliary | OR2B11, NLRP3 |
| chr1 | 247684856 | 247684929 | Hypo | cancer_general | GCSAML-AS1, OR2C3, AK130400, GCSAML | chr1 | 247910678 | 247910780 | Hypo | cancer_general | OR1C1 |
| chr1 | 248002278 | 248002437 | Hypo | cancer_general | OR11L1 | chr1 | 248028015 | 248028202 | Hypo | cancer_general | TRIM58 |
| chr1 | 248074729 | 248074927 | Hypo | cancer_general | OR2T8 | chr1 | 248099751 | 248099809 | Typo | cancer_general | OR2L13 |
| chr1 | 248198552 | 248198721 | Hypo | cancer_general | OR2L2 | chr1 | 248328701 | 248328841 | Hypo | cancer_general | |
| chr1 | 248691575 | 248691616 | Hypo | cancer_general | OR2G6 | chr1 | 248860898 | 248861046 | Hypo | cancer_general | |
| chr1 | 249121600 | 249121704 | Hypo | cancer_general | MIR3124, SH3BP5L | chr4 | 488816 | 488875 | Hypo | breast | |
| chr4 | 512978 | 513008 | Hypo | head_neck | PIGG | chr4 | 513704 | 513734 | Hypo | head_neck | PIGG, ZNF721 |
| chr4 | 628572 | 629061 | Hypo | cancer_general | PDE6B | chr4 | 651196 | 651261 | Hypo | cancer_general | BC020343, PDE6B |
| chr4 | 678471 | 678501 | Hypo | cancer_general | MFSD7, MYL5 | chr4 | 718052 | 718112 | Hypo | colorectal | PCGF3 |
| chr4 | 718321 | 718456 | Hypo | colorectal | PCGF3 | chr4 | 829611 | 829641 | Hypo | cancer_general | CPLX1 |
| chr4 | 955367 | 955454 | Hypo | cancer_general | DGKQ, TMEM175 | chr4 | 955867 | 955919 | Hypo | cancer_general | DGKQ, TMEM175 |
| chr4 | 1008740 | 1008902 | Hypo | ovarian | FGFRL1 | chr4 | 1016127 | 1016252 | Hypo | cancer_general | FGFRL1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 1016586 | 1016747 | Hypo | cancer_general | FGFRL1 | chr4 | 1025928 | 1026074 | Hypo | cancer_general | FGFRL1 |
| chr4 | 1041763 | 1041926 | Hypo | cancer_general | AK124578 | chr4 | 1093536 | 1093675 | Hypo | pancreas | RNF212 |
| chr4 | 1189021 | 1189051 | Hypo | cancer_general | LOC100130872, AX747178 | chr4 | 1214894 | 1215162 | Hypo | ovarian | HV535487, HV535469, CTBP1 |
| chr4 | 1215415 | 1215451 | Hypo | ovarian | CTBP1, HV535487, HV535469 | chr4 | 1282515 | 1282545 | Hypo | ovarian | MAEA, C4orf42 |
| chr4 | 1331675 | 1331705 | Hypo | pancreas | UVSSA, MAEA | chr4 | 1336755 | 1336902 | Hypo | ovarian | UVSSA, MAEA |
| chr4 | 1338715 | 1338812 | Hypo | pancreas | UVSSA, MAEA | chr4 | 1339099 | 1339221 | Hypo | cancer_general | UVSSA, MAEA |
| chr4 | 1512368 | 1512398 | Hypo | cancer_general | AX748388 | chr4 | 1556419 | 1556609 | Hypo | cancer_general | LETM1, FGFR3 |
| chr4 | 1576484 | 1576528 | Hypo | cancer_general | SLBP, FAM53A | chr4 | 1616682 | 1617247 | Hypo | cancer_general | FGFR3 |
| chr4 | 1687080 | 1687110 | Hypo | cancer_general |  | chr4 | 1803550 | 1803582 | Hypo | literature | LETM1 |
| chr4 | 1806084 | 1806113 | Hypo | literature | LETM1, FGFR3 | chr4 | 1807355 | 1807384 | Hypo | literature | LETM1 |
| chr4 | 1962787 | 1962816 | Hypo | literature | WHSC1 | chr4 | 1993771 | 1994180 | Hypo | cancer_general | MIR943, NELFA |
| chr4 | 2066114 | 2066265 | Hypo | cancer_general | POLN, NAT8L | chr4 | 2305672 | 2305827 | Hypo | cancer_general | ZFYVE28 |
| chr4 | 2527907 | 2527937 | Hypo | cancer_general |  | chr4 | 2532556 | 2532586 | Hypo | cancer_general | MFSD10 |
| chr4 | 2540073 | 2540297 | Hypo | cancer_general |  | chr4 | 2926366 | 2926396 | Hypo | esophageal | GRK4 |
| chr4 | 2978968 | 2979145 | Hypo | cancer_general | GRK4 | chr4 | 3036118 | 3036148 | Hypo | lung | HGFAC |
| chr4 | 3217107 | 3217154 | Hypo | breast |  | chr4 | 3446991 | 3447021 | Hypo | cancer_general | NSG1, STX18 |
| chr4 | 3447816 | 3448015 | Hypo | cancer_general | HGFAC | chr4 | 4417568 | 4417603 | Hypo | cancer_general | MAN2B2 |
| chr4 | 5519950 | 5520092 | Hypo | cancer_general | C4orf6 | chr4 | 6628453 | 6628500 | Hypo | ovarian | BLOC1S4, MRFAP1L1 |
| chr4 | 6670184 | 6670214 | Hypo | cancer_general | LOC93622 | chr4 | 6719599 | 6719637 | Hypo | cancer_general | KIAA0232 |
| chr4 | 6748346 | 6748557 | Hypo | cancer_general |  | chr4 | 6839352 | 6839402 | Hypo | head_neck |  |
| chr4 | 6955114 | 6955144 | Hypo | cancer_general | AX747238, TBC1D14 | chr4 | 6957481 | 6957620 | Hypo | cancer_general |  |
| chr4 | 7038560 | 7038688 | Hypo | breast | CCDC96, TADA2B, LOC100129931, TBC1D14 | chr4 | 7647770 | 7647945 | Hypo | cancer_general |  |
| chr4 | 7758476 | 7758561 | Hypo | pancreas | AFAP1, AFAP1-AS1 | chr4 | 8429086 | 8429178 | Hypo | cancer_general | ACOX3 |
| chr4 | 8607813 | 8607932 | Hypo | cancer_general | CPZ | chr4 | 8608556 | 8608600 | Hypo | cancer_general | CPZ |
| chr4 | 9423273 | 9423354 | Hypo | cancer_general |  | chr4 | 10782701 | 10782741 | Hypo | cancer_general |  |
| chr4 | 13524957 | 13525008 | Hypo | pancreas | LOC285547 | chr4 | 17430691 | 17430832 | Hypo | cancer_general |  |
| chr4 | 26256826 | 26256867 | Hypo | hepatobiliary |  | chr4 | 38566328 | 38566418 | Hypo | head_neck |  |
| chr4 | 38673115 | 38673144 | Hypo | literature | FLJ13197, KLF3 | chr4 | 39816807 | 39817064 | Hypo | cancer_general | PDS5A |
| chr4 | 40910303 | 40910465 | Hypo | cancer_general | TRNA_Gln, APBB2 | chr4 | 41938449 | 41938479 | Hypo | cancer_general | TMEM33 |
| chr4 | 41993676 | 41993815 | Hypo | cancer_general | SLC30A9, DCAF4L1 | chr4 | 42155293 | 42155322 | Hypo | literature | BEND4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 42348266 | 42348331 | Hypo | ovarian | | chr4 | 44266683 | 44266780 | Hypo | cancer_general | KCTD8 |
| chr4 | 46067800 | 46067954 | Hypo | cancer_general | GABRG1 | chr4 | 46911535 | 46911564 | Hypo | literature | GABRA4 |
| chr4 | 47197142 | 47197270 | Hypo | cancer_general | GABRB1 | chr4 | 47914784 | 47914992 | Hypo | cancer_general | NFXL1, BC041434 |
| chr4 | 48848428 | 48848554 | Hypo | head_neck | OCIAD1 | chr4 | 55133613 | 55133642 | Hypo | literature | PDGFRA |
| chr4 | 55136787 | 55136816 | Hypo | literature | PDGFRA | chr4 | 55138657 | 55138686 | Hypo | literature | PDGFRA |
| chr4 | 55139691 | 55139720 | Hypo | literature | PDGFRA | chr4 | 55140731 | 55140784 | Hypo | literature | PDGFRA |
| chr4 | 55141015 | 55141050 | Hypo | literature | PDGFRA | chr4 | 55144105 | 55144134 | Hypo | literature | PDGFRA |
| chr4 | 55146554 | 55146583 | Hypo | literature | PDGFRA | chr4 | 55152075 | 55152140 | Hypo | literature | KIT, DL490879 |
| chr4 | 55589753 | 55589782 | Hypo | literature | DL490879, KIT | chr4 | 55592166 | 55592204 | Hypo | literature | KIT, DL490879 |
| chr4 | 55593417 | 55593675 | Hypo | literature | KIT, DL490879 | chr4 | 55594183 | 55594212 | Hypo | literature | KIT, DL490879 |
| chr4 | 55595504 | 55595614 | Hypo | literature | KIT, DL490879 | chr4 | 55599306 | 55599356 | Hypo | literature | REST |
| chr4 | 55968165 | 55968194 | Hypo | literature | KDR | chr4 | 56594679 | 56594720 | Hypo | hepatobiliary | REST |
| chr4 | 57017387 | 57017459 | Hypo | hepatobiliary | | chr4 | 57777437 | 57777595 | Hypo | ovarian | REST |
| chr4 | 57803498 | 57803558 | Hypo | pancreas | REST | chr4 | 57813490 | 57813763 | Hypo | ovarian | |
| chr4 | 73459699 | 73459762 | Hypo | cancer_general | EREG | chr4 | 74142341 | 74142434 | Hypo | ovarian | CDKL2 |
| chr4 | 75241080 | 75241435 | Hypo | cancer_general | | chr4 | 76554873 | 76554935 | Hypo | lung | |
| chr4 | 76912698 | 76912733 | Hypo | cancer_general | CXCL9, SDAD1 | chr4 | 79611132 | 79611294 | Hypo | cancer_general | LOC100505702 |
| chr4 | 79689651 | 79689732 | Hypo | colorectal | BMP2K | chr4 | 79861530 | 79861560 | Hypo | cancer_general | PAQR3 |
| chr4 | 80273120 | 80273150 | Hypo | hepatobiliary | | chr4 | 81188328 | 81188489 | Hypo | cancer_general | FGF5 |
| chr4 | 83323506 | 83323708 | Hypo | lung | | chr4 | 83343366 | 83343396 | Hypo | cancer_general | HNRPDL, ENOPH1 |
| chr4 | 83809740 | 83809787 | Hypo | cancer_general | THAP9-AS1, AK128593, SEC31A | chr4 | 83955171 | 83955201 | Hypo | cancer_general | COPS4 |
| chr4 | 83988361 | 83988511 | Hypo | cancer_general | COPS4 | chr4 | 90043517 | 90043547 | Hypo | cancer_general | TIGD2 |
| chr4 | 91079842 | 91079899 | Hypo | cancer_general | CCSER1 | chr4 | 95127590 | 95127717 | Hypo | cancer_general | SMARCAD1 |
| chr4 | 95128038 | 95128068 | Hypo | cancer_general | SMARCAD1 | chr4 | 95762672 | 95762896 | Hypo | cancer_general | BMPR1B |
| chr4 | 102332467 | 102332611 | Hypo | cancer_general | BANK1 | chr4 | 103929647 | 103929796 | Hypo | cancer_general | SLC9B1 |
| chr4 | 103930065 | 103930095 | Hypo | cancer_general | SLC9B1 | chr4 | 106335495 | 106335617 | Hypo | breast | PPA2 |
| chr4 | 110344202 | 110344294 | Hypo | cancer_general | SEC24B-AS1, AK058136 | chr4 | 110735672 | 110735702 | Hypo | cancer_general | GAR1 |
| chr4 | 113154896 | 113155129 | Hypo | cancer_general | AP1AR | chr4 | 113431900 | 113431930 | Hypo | pancreas | NEUROG2 |
| chr4 | 113559163 | 113559422 | Hypo | cancer_general | MIR302B, LARP7, C4orf21 | chr4 | 123664228 | 123664363 | Hypo | cancer_general | BBS12 |
| chr4 | 128967250 | 128967329 | Hypo | colorectal | | chr4 | 128968647 | 128968800 | Hypo | head_neck | LARP1B |
| chr4 | 128969310 | 128969382 | Hypo | head_neck | | chr4 | 128984386 | 128984464 | Hypo | cancer_general | PCDH10, BC040219 |
| chr4 | 130018134 | 130018266 | Hypo | cancer_general | SCLT1, C4orf33 | chr4 | 134073862 | 134073919 | Hypo | cancer_general | |
| chr4 | 144586035 | 144586088 | Hypo | cancer_general | FREM3 | chr4 | 146853951 | 146853981 | Hypo | head_neck | ZNF827 |
| chr4 | 151974287 | 151974510 | Hypo | pancreas | | chr4 | 152148807 | 152148836 | Hypo | literature | SH3D19 |
| chr4 | 153247273 | 153247386 | Hypo | literature | FBXW7 | chr4 | 153249362 | 153249398 | Hypo | literature | FBXW7 |
| chr4 | 153251894 | 153251923 | Hypo | literature | FBXW7 | chr4 | 153702668 | 153702702 | Hypo | cancer_general | ARFIP1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 154216241 | 154216357 | Hypo | cancer_general | | chr4 | 154374504 | 154374630 | Hypo | head_neck | GLRB |
| chr4 | 155665445 | 155665475 | Hypo | esophageal | LRAT, DQ266889 | chr4 | 158101782 | 158102020 | Hypo | cancer_general | |
| chr4 | 159063301 | 159063331 | Hypo | hepatobiliary | FAM198B | chr4 | 159149784 | 159149824 | Hypo | head_neck | TMEM144 |
| chr4 | 164819191 | 164819221 | Hypo | hepatobiliary | | chr4 | 170865234 | 170865287 | Hypo | cancer_general | LOC100506085 |
| chr4 | 171012375 | 171012409 | Hypo | cancer_general | AADAT | chr4 | 172132870 | 172133019 | Hypo | cancer_general | GALNT7, BC040577 |
| chr4 | 173953411 | 173953594 | Hypo | hepatobiliary | | chr4 | 174083164 | 174083431 | Hypo | hepatobiliary | GALNT7 |
| chr4 | 174124429 | 174124477 | Hypo | hepatobiliary | GALNT7 | chr4 | 174136704 | 174136734 | Hypo | hepatobiliary | GALNT7 |
| chr4 | 174224186 | 174224216 | Hypo | hepatobiliary | GALNT7 | chr4 | 178285756 | 178285879 | Hypo | head_neck | |
| chr4 | 183064874 | 183064966 | Hypo | pancreas | TENM3, MGC45800 | chr4 | 184375546 | 184375726 | Hypo | cancer_general | CDKN2AIP |
| chr4 | 184491996 | 184492042 | Hypo | cancer_general | | chr4 | 184921855 | 184922091 | Hypo | pancreas, cancer_general | STOX2 |
| chr19 | 403538 | 403809 | Hypo | cancer_general | C2CD4C | chr19 | 407189 | 407320 | Hypo | cancer_general | SHC2, C2CD4C |
| chr19 | 418225 | 418255 | Hypo | ovarian | SHC2, C2CD4C | chr19 | 468757 | 468787 | Hypo | cancer_general | ODF3L2, SHC2 |
| chr19 | 485165 | 485394 | Hypo | cancer_general | | chr19 | 549361 | 549451 | Hypo | cancer_general | GZMM, CDC34 |
| chr19 | 555608 | 555768 | Hypo | cancer_general | GZMM | chr19 | 570156 | 570194 | Hypo | esophageal | BSG |
| chr19 | 592589 | 592632 | Hypo | cancer_general | HCN2, BSG | chr19 | 593290 | 593462 | Hypo | cancer_general | HCN2, BSG |
| chr19 | 599214 | 599333 | Hypo | cancer_general | PRSS57, FSTL3 | chr19 | 607070 | 607110 | Hypo | head_neck | HCN2 |
| chr19 | 690888 | 690940 | Hypo | cancer_general | | chr19 | 752136 | 752462 | Hypo | cancer_general | MISP, PALM |
| chr19 | 869337 | 869394 | Hypo | pancreas | CFD, MED16 | chr19 | 883624 | 883791 | Hypo | cancer_general | MED16, U6 |
| chr19 | 884018 | 884162 | Hypo | cancer_general | U6, MED16 | chr19 | 891516 | 891723 | Hypo | cancer_general | U6, R3HDM4, MED16 |
| chr19 | 955757 | 956237 | Hypo | cancer_general | ARID3A, FLJ00277, TMEM259, GRIN3B, WDR18 | chr19 | 959128 | 959187 | Hypo | pancreas | ARID3A |
| chr19 | 1003305 | 1003384 | Hypo | cancer_general | FLJ00277, TMEM259, GRIN3B | chr19 | 1003669 | 1003734 | Hypo | cancer_general | FLJ00277, TMEM259, GRIN3B, WDR18 |
| chr19 | 1004915 | 1005441 | Hypo | cancer_general | | chr19 | 1030176 | 1030225 | Hypo | cancer_general | ABCA7, CNN2 |
| chr19 | 1047890 | 1047939 | Hypo | cancer_general | ABCA7 | chr19 | 1048348 | 1048465 | Hypo | ovarian | |
| chr19 | 1083314 | 1083437 | Hypo | cancer_general | POLR2E, HMHA1 | chr19 | 1156524 | 1156554 | Hypo | cancer_general | ABCA7 |
| chr19 | 1170185 | 1170230 | Hypo | cancer_general | | chr19 | 1171099 | 1171324 | Hypo | cancer_general | |
| chr19 | 1220422 | 1220610 | Hypo | literature | C19orf26, STK11 | chr19 | 1221981 | 1222010 | Hypo | literature | STK11, C19orf26 |
| chr19 | 1236474 | 1236678 | Hypo | cancer_general | ATP5D, C19orf26, STK11 | chr19 | 1274778 | 1274826 | Hypo | cancer_general | CIRBP-AS1, C19orf24, DL492057, CIRBP |
| chr19 | 1325788 | 1325889 | Hypo | cancer_general | | chr19 | 1330064 | 1330214 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 1496413 | 1496450 | Hypo | cancer_general | PCSK4, ADAMTSL5, REEP6 | chr19 | 1496654 | 1496694 | Hypo | cancer_general | ADAMTSL5, REEP6, PCSK4 |
| chr19 | 1525605 | 1525960 | Hypo | cancer_general | PLK5 | chr19 | 1527227 | 1527394 | Hypo | cancer_general | PLK5 |
| chr19 | 1547233 | 1547263 | Hypo | cancer_general | MEX3D | chr19 | 1689436 | 1689595 | Hypo | cancer_general | |
| chr19 | 1799466 | 1799516 | Hypo | cancer_general | ATP8B3 | chr19 | 1800032 | 1800300 | Hypo | cancer_general | ATP8B3 |
| chr19 | 1807970 | 1808413 | Hypo | cancer_general | MIR1909, ATP8B3, REXO1 | chr19 | 2155031 | 2155061 | Hypo | cancer_general | DOT1L |
| chr19 | 2274677 | 2274713 | Hypo | cancer_general | C19orf35, SPPL2B, OAZ1 | chr19 | 2330317 | 2330407 | Hypo | cancer_general | SPPL2B, LSM7 |
| chr19 | 2331413 | 2331443 | Hypo | cancer_general | SPPL2B, LSM7 | chr19 | 2413125 | 2413155 | Hypo | cancer_general | TMPRSS9 |
| chr19 | 2414257 | 2414337 | Hypo | cancer_general | TMPRSS9 | chr19 | 2513250 | 2513285 | Hypo | cancer_general | GNG7 |
| chr19 | 2642877 | 2642947 | Hypo | cancer_general | BC022568, GNG7 | chr19 | 2683911 | 2684080 | Hypo | cancer_general | |
| chr19 | 3041417 | 3041447 | Hypo | cancer_general | DKFZp434J194, GNA11 | chr19 | 3093571 | 3093818 | Hypo | cancer_general | GNA11 |
| chr19 | 3114998 | 3115027 | Hypo | literature | | chr19 | 3118927 | 3118956 | Hypo | literature | DKFZp434J194, GNA11 |
| chr19 | 3219512 | 3219565 | Hypo | cancer_general | CELF5, NCLN | chr19 | 3296613 | 3296670 | Hypo | cancer_general | CELF5 |
| chr19 | 3562128 | 3562797 | Hypo | cancer_general | MFSD12 | chr19 | 3570230 | 3570371 | Hypo | cancer_general | HMG20B |
| chr19 | 3578138 | 3578223 | Hypo | cancer_general | GIPC3, HMG20B | chr19 | 3716179 | 3716241 | Hypo | cancer_general | TJP3 |
| chr19 | 3718052 | 3718082 | Hypo | cancer_general | TJP3 | chr19 | 3778130 | 3778394 | Hypo | cancer_general | JA611290, MATK, RAX2 |
| chr19 | 3779277 | 3779435 | Hypo | cancer_general | JA611290, MATK, RAX2 | chr19 | 3821044 | 3821217 | Hypo | cancer_general | ZFR2 |
| chr19 | 3834572 | 3834641 | Hypo | hepatobiliary | ZFR2 | chr19 | 3855407 | 3855595 | Hypo | cancer_general | ZFR2 |
| chr19 | 3966686 | 3966755 | Hypo | cancer_general | EEF2, MIR637, DAPK3 | chr19 | 3994540 | 3994595 | Hypo | colorectal | |
| chr19 | 4054435 | 4054471 | Hypo | pancreas | ZBTB7A | chr19 | 4095471 | 4095514 | Hypo | cancer_general | MAP2K2 |
| chr19 | 4101087 | 4101116 | Hypo | literature | MAP2K2 | chr19 | 4110565 | 4110597 | Hypo | literature | MAP2K2 |
| chr19 | 4117526 | 4117630 | Hypo | literature | MAP2K2 | chr19 | 4160800 | 4160898 | Hypo | cancer_general | CREB3L3 |
| chr19 | 4195767 | 4195853 | Hypo | cancer_general | ANKRD24 | chr19 | 4311273 | 4311430 | Hypo | cancer_general | TMIGD2, FSD1 |
| chr19 | 4509338 | 4509440 | Hypo | cancer_general | PLIN4, HDGFRP2 | chr19 | 4548134 | 4548364 | Hypo | cancer_general | SEMA6B, LRG1, PLIN5 |
| chr19 | 4549454 | 4549565 | Hypo | cancer_general | SEMA6B, LRG1, PLIN5 | chr19 | 4550246 | 4550330 | Hypo | cancer_general | SEMA6B |
| chr19 | 4555896 | 4556112 | Hypo | cancer_general | SEMA6B | chr19 | 4557098 | 4557235 | Hypo | cancer_general | SEMA6B |
| chr19 | 4572332 | 4572459 | Hypo | cancer_general | | chr19 | 4670765 | 4670949 | Hypo | cancer_general | DPP9, LOC100131094, C19orf10 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 4789697 | 4789805 | Hypo | cancer_general | FEM1A, AK126532 | chr19 | 4790142 | 4790264 | Hypo | cancer_general | FEM1A, AK126532 |
| chr19 | 4835778 | 4835926 | Hypo | colorectal | PLIN3 | chr19 | 4910361 | 4910410 | Hypo | breast | ARRDC5, UHRF1, C19orf31 |
| chr19 | 5608519 | 5608569 | Hypo | cancer_general | SAFB2 | chr19 | 5676212 | 5676242 | Hypo | cancer_general | C19orf70, HSD11B1L |
| chr19 | 5759374 | 5759544 | Hypo | cancer_general | CATSPERD | chr19 | 5759744 | 5759774 | Hypo | cancer_general | CATSPERD |
| chr19 | 5767703 | 5767733 | Hypo | cancer_general | CATSPERD | chr19 | 5826179 | 5826209 | Hypo | cancer_general | FUT6, NRTN |
| chr19 | 5905517 | 5905547 | Hypo | cancer_general | CAPS, VMAC, NDUFA11 | chr19 | 5910356 | 5910492 | Hypo | cancer_general | CAPS, RANBP3, VMAC, NDUFA11 |
| chr19 | 5914761 | 5914791 | Hypo | cancer_general | RANBP3, CAPS, VMAC | chr19 | 5914992 | 5915060 | Hypo | cancer_general | RANBP3, CAPS, VMAC |
| chr19 | 6303268 | 6303298 | Hypo | cancer_general | ACER1 | chr19 | 6512913 | 6512943 | Hypo | cancer_general | EMR1 |
| chr19 | 6658279 | 6658422 | Hypo | cancer_general | TNFSF14 | chr19 | 6889423 | 6889574 | Hypo | cancer_general | C19orf45, PEX11G |
| chr19 | 7157547 | 7157628 | Hypo | lung | INSR | chr19 | 7554718 | 7554780 | Hypo | cancer_general | |
| chr19 | 7635387 | 7635552 | Hypo | cancer_general | PNPLA6 | chr19 | 7747205 | 7747234 | Hypo | tcga | FCER2, TRAPPC5, C19orf59 |
| chr19 | 7870346 | 7870387 | Hypo | cancer_general | | chr19 | 8391621 | 8391651 | Hypo | cancer_general | KANK3, RPS28, NDUFA7 |
| chr19 | 8554173 | 8554218 | Hypo | head_neck | PRAM1, DKFZp547H118, HNRNPM | chr19 | 8576914 | 8577000 | Hypo | lung | ZNF414, PRAM1, MYO1F |
| chr19 | 8579592 | 8579705 | Hypo | ovarian | MYO1F, ZNF414 | chr19 | 9239580 | 9239695 | Hypo | cancer_general | OR7G3 |
| chr19 | 9331918 | 9331955 | Hypo | hepatobiliary | OR7D4 | chr19 | 9937291 | 9937386 | Hypo | cancer_general | UBL5, PIN1, FBXL12 |
| chr19 | 10231077 | 10231242 | Hypo | cancer_general | P2RY11, EIF3G | chr19 | 10246506 | 10246566 | Hypo | lung | DNMT1 |
| chr19 | 10362045 | 10362182 | Hypo | cancer_general | MRPL4 | chr19 | 10600431 | 10600460 | Hypo | literature | KEAP1 |
| chr19 | 10602274 | 10602348 | Hypo | literature | KEAP1 | chr19 | 10602565 | 10602864 | Hypo | literature | KEAP1 |
| chr19 | 10610138 | 10610260 | Hypo | literature | KEAP1 | chr19 | 10621768 | 10621829 | Hypo | cancer_general | S1PR5, KEAP1 |
| chr19 | 10648372 | 10648546 | Hypo | cancer_general | ATG4D | chr19 | 10729811 | 10729899 | Hypo | cancer_general | SLC44A2 |
| chr19 | 10823678 | 10823721 | Hypo | colorectal | DNM2, MIR638, QTRT1 | chr19 | 10827675 | 10827705 | Hypo | cancer_general | DNM2, MIR638, QTRT1 |
| chr19 | 10851287 | 10851362 | Hypo | colorectal | | chr19 | 10955456 | 10955585 | Hypo | cancer_general | C19orf38, TMED1 |
| chr19 | 11063941 | 11063971 | Hypo | cancer_general | SMARCA4 | chr19 | 11134252 | 11134281 | Hypo | literature | SMARCA4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 11138507 | 11138536 | Hypo | literature | SMARCA4 | chr19 | 12147437 | 12147545 | Hypo | cancer_general | ZNF878, ZNF433, AX747405 |
| chr19 | 12205385 | 12205434 | Hypo | hepatobiliary | ZNF788 | chr19 | 12303495 | 12303551 | Hypo | breast | AX721123, AK022304, ZNF136 |
| chr19 | 12661175 | 12661221 | Hypo | cancer_general | ZNF564, ZNF709 | chr19 | 12846906 | 12847098 | Hypo | cancer_general | ASNA1, C19orf43 |
| chr19 | 12860307 | 12860433 | Hypo | cancer_general | BEST2, ASNA1 | chr19 | 12863412 | 12863520 | Hypo | cancer_general | ASNA1, BEST2 |
| chr19 | 13491305 | 13491340 | Hypo | esophageal | CACNA1A | chr19 | 13782965 | 13783028 | Hypo | hepatobiliary | |
| chr19 | 13903520 | 13903603 | Hypo | cancer_general | ZSWIM4 | chr19 | 13965838 | 13965965 | Hypo | cancer_general | |
| chr19 | 13988775 | 13988805 | Hypo | cancer_general | C19orf57, NANOS3, MIR181D, MIR181C | chr19 | 14085021 | 14085051 | Hypo | cancer_general | RFX1 |
| chr19 | 14181305 | 14181846 | Hypo | breast | LOC113230 | chr19 | 14324876 | 14324906 | Hypo | cancer_general | |
| chr19 | 14327101 | 14327158 | Hypo | cancer_general | | chr19 | 14334020 | 14334060 | Hypo | colorectal | |
| chr19 | 14411056 | 14411086 | Hypo | breast | | chr19 | 14663925 | 14664183 | Hypo | breast | TECR |
| chr19 | 14664479 | 14664561 | Hypo | cancer_general | TECR | chr19 | 14869496 | 14869526 | Hypo | cancer_general | EMR2 |
| chr19 | 15292384 | 15292499 | Hypo | cancer_general, literature | NOTCH3 | chr19 | 15519444 | 15519474 | Hypo | ovarian | AKAP8L |
| chr19 | 16766902 | 16766932 | Hypo | head_neck | TMEM38A, SMIM7 | chr19 | 17000570 | 17000599 | Hypo | literature | CPAMD8, F2RL3, SIN3B |
| chr19 | 17152333 | 17152363 | Hypo | cancer_general | HAUS8 | chr19 | 17335642 | 17335718 | Hypo | cancer_general | OCEL1, NR2F6, USE1 |
| chr19 | 17336042 | 17336111 | Hypo | cancer_general | OCEL1, NR2F6, USE1 | chr19 | 17359350 | 17359459 | Hypo | cancer_general | USHBP1, NR2F6 |
| chr19 | 17436061 | 17436203 | Hypo | head_neck | GTPBP3, ANO8, DDA1 | chr19 | 17446897 | 17447045 | Hypo | cancer_general | AK310794, GTPBP3, ANO8 |
| chr19 | 17759224 | 17759423 | Hypo | literature | UNC13A | chr19 | 17943423 | 17943452 | Hypo | literature | JAK3 |
| chr19 | 17945891 | 17945983 | Hypo | literature | JAK3 | chr19 | 17947991 | 17948023 | Hypo | literature | JAK3 |
| chr19 | 17949094 | 17949123 | Hypo | literature | JAK3 | chr19 | 18041069 | 18041203 | Hypo | cancer_general | CCDC124 |
| chr19 | 18057603 | 18057655 | Hypo | cancer_general | KCNN1, CCDC124 | chr19 | 18103711 | 18103741 | Hypo | cancer_general | ARRDC2, KCNN1 |
| chr19 | 18104472 | 18104606 | Hypo | cancer_general | ARRDC2, KCNN1 | chr19 | 18126412 | 18126442 | Hypo | ovarian | ARRDC2 |
| chr19 | 18271894 | 18271923 | Hypo | literature | PIK3R2, MAST3 | chr19 | 18278047 | 18278076 | Hypo | literature | IFI30, PIK3R2 |
| chr19 | 18300127 | 18300422 | Hypo | cancer_general | MPV17L2, RAB3A | chr19 | 18301007 | 18301037 | Hypo | cancer_general | RAB3A, MPV17L2 |
| chr19 | 18331031 | 18331136 | Hypo | cancer_general | PDE4C | chr19 | 18383211 | 18383351 | Hypo | cancer_general | JUND, MIR3188 |
| chr19 | 18488862 | 18488915 | Hypo | cancer_general | GDF15, MIR3189, PGPEP1 | chr19 | 18496000 | 18496030 | Hypo | head_neck | GDF15, MIR3189, LRRC25 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 18523115 | 18523145 | Hypo | cancer_general | SSBP4 | chr19 | 18633926 | 18633980 | Hypo | cancer_general | FKBP8, ELL |
| chr19 | 18681638 | 18681926 | Hypo | cancer_general | UBA52, DL491652, KXD1 | chr19 | 18856379 | 18856409 | Hypo | ovarian | CRTC1 |
| chr19 | 18872825 | 18872900 | Hypo | cancer_general | CRTC1 | chr19 | 18989821 | 18990281 | Hypo | cancer_general | CERS1, GDF1 |
| chr19 | 18994887 | 18995206 | Hypo | cancer_general | GDF1, CERS1 | chr19 | 19260030 | 19260101 | Hypo | literature | MEF2B, MEF2BNB-MEF2B |
| chr19 | 19261519 | 19261548 | Hypo | literature | MEF2B, MEF2BNB-MEF2B | chr19 | 19334831 | 19334915 | Hypo | cancer_general | NCAN |
| chr19 | 19489251 | 19489297 | Hypo | cancer_general | GATAD2A | chr19 | 19636877 | 19636907 | Hypo | ovarian | NDUFA13, YJEFN3 |
| chr19 | 19645834 | 19645925 | Hypo | cancer_general | CILP2, YJEFN3, NDUFA13 | chr19 | 19775308 | 19775472 | Hypo | cancer_general | ZNF101, ATP13A1 |
| chr19 | 21237609 | 21237655 | Hypo | hepatobiliary | ZNF430 | chr19 | 21239053 | 21239129 | Hypo | hepatobiliary | ZNF430 |
| chr19 | 21245066 | 21245152 | Hypo | hepatobiliary | ZNF430 | chr19 | 21265890 | 21265920 | Hypo | cancer_general | ZNF714 |
| chr19 | 21289719 | 21289749 | Hypo | hepatobiliary | ZNF714 | chr19 | 21290153 | 21290216 | Hypo | hepatobiliary | ZNF714 |
| chr19 | 21303863 | 21303993 | Hypo | hepatobiliary | AX746719, ZNF714 | chr19 | 21305707 | 21305737 | Hypo | hepatobiliary | AX746719, ZNF714 |
| chr19 | 21370382 | 21370479 | Hypo | hepatobiliary | ZNF431 | chr19 | 21512594 | 21512660 | Hypo | cancer_general | ZNF708 |
| chr19 | 21665258 | 21665288 | Hypo | cancer_general | LINC00664 | chr19 | 29505153 | 29505183 | Hypo | cancer_general | LOC100505835 |
| chr19 | 30130889 | 30130919 | Hypo | tcga | | chr19 | 30186141 | 30186278 | Hypo | lung | |
| chr19 | 30215753 | 30215782 | Hypo | cancer_general | C19orf12 | chr19 | 30252296 | 30252369 | Hypo | cancer_general | C19orf12 |
| chr19 | 30555329 | 30555376 | Hypo | cancer_general | | chr19 | 30562775 | 30563017 | Hypo | cancer_general | |
| chr19 | 30582601 | 30582649 | Hypo | cancer_general | | chr19 | 30637494 | 30637531 | Hypo | cancer_general | |
| chr19 | 30703436 | 30703469 | Hypo | cancer_general | | chr19 | 31804724 | 31804754 | Hypo | cancer_general | TSHZ3 |
| chr19 | 32364365 | 32364403 | Hypo | cancer_general | | chr19 | 32380872 | 32380961 | Hypo | cancer_general | |
| chr19 | 32516399 | 32516516 | Hypo | cancer_general | AK097493 | chr19 | 32835279 | 32835309 | Hypo | cancer_general | ZNF507 |
| chr19 | 32898335 | 32898490 | Hypo | cancer_general | LOC400684, DPY19L3 | chr19 | 33468018 | 33468055 | Hypo | breast | RHPN2, C19orf40, CEP89 |
| chr19 | 33571236 | 33571280 | Hypo | lung, cancer_general | GPATCH1 | chr19 | 34896324 | 34896360 | Hypo | cancer_general | GPI, PDCD2L |
| chr19 | 35616341 | 35616397 | Hypo | cancer_general | LGI4, FXYD3 | chr19 | 35781374 | 35781459 | Hypo | cancer_general | MAG, HAMP |
| chr19 | 35783136 | 35783231 | Hypo | cancer_general | MAG, HAMP | chr19 | 35797916 | 35797965 | Hypo | cancer_general | MAG |
| chr19 | 36194934 | 36194996 | Hypo | ovarian | ZBTB32 | chr19 | 36200805 | 36200847 | Hypo | cancer_general | ZBTB32, KMT2B |
| chr19 | 36222432 | 36222534 | Hypo | cancer_general | IGFLR1, KMT2B | chr19 | 36250029 | 36250134 | Hypo | cancer_general | HSPB6, LIN37, AL137752, C19orf55 |
| chr19 | 36264697 | 36264773 | Hypo | cancer_general | ARHGAP33, C19orf55 | chr19 | 36265053 | 36265186 | Hypo | cancer_general | C19orf55 |
| chr19 | 36410956 | 36411042 | Hypo | esophageal | | chr19 | 36413776 | 36413830 | Hypo | cancer_general | ARHGAP33 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 36531924 | 36531954 | Hypo | ovarian | BC071809, THAP8, CLIP3 | chr19 | 36707435 | 36707467 | Hypo | cancer_general | ZNF146, ZNF565 |
| chr19 | 37702003 | 37702169 | Hypo | cancer_general | ZNF383, ZNF585B | chr19 | 38441488 | 38441518 | Hypo | breast | SIPA1L3 |
| chr19 | 38481044 | 38481217 | Hypo | cancer_general | SIPA1L3 | chr19 | 38733924 | 38733954 | Hypo | cancer_general | PPP1R14A, SPINT2, |
| chr19 | 38736072 | 38736127 | Hypo | cancer_general | PPP1R14A | chr19 | 38747729 | 38747767 | Hypo | cancer_general | PPP1R14A, SPINT2 |
| chr19 | 38757128 | 38757308 | Hypo | cancer_general | PPP1R14A, SPINT2 | chr19 | 38782559 | 38782589 | Hypo | breast | SPINT2 |
| chr19 | 38789218 | 38789288 | Hypo | cancer_general | YIF1B, C19orf33, SPINT2 | chr19 | 38873935 | 38873965 | Hypo | cancer_general | GGN, SPRED3, PSMD8 |
| chr19 | 38905548 | 38905702 | Hypo | cancer_general | RASGRP4, FAM98C | chr19 | 38974232 | 38974262 | Hypo | cancer_general | RYR1 |
| chr19 | 39135294 | 39135454 | Hypo | cancer_general | ACTN4, EIF3K | chr19 | 39273027 | 39273062 | Hypo | ovarian | LGALS7B, LGALS7 |
| chr19 | 39290904 | 39290944 | Hypo | cancer_general | LGALS4, LGALS7B | chr19 | 39306433 | 39306545 | Hypo | colorectal | ECH1, HNRNPL, LGALS4 |
| chr19 | 39310469 | 39310584 | Hypo | colorectal | ECH1, LGALS4, HNRNPL | chr19 | 39650791 | 39650967 | Hypo | breast | PAK4 |
| chr19 | 39816936 | 39817085 | Hypo | cancer_general | BC110060, GMFG | chr19 | 39934694 | 39934784 | Hypo | cancer_general | SUPT5H, RPS16 |
| chr19 | 40210391 | 40210573 | Hypo | cancer_general | C19orf47 | chr19 | 40762943 | 40762972 | Hypo | literature | AKT2 |
| chr19 | 40829079 | 40829211 | Hypo | breast | | chr19 | 40829793 | 40830032 | Hypo | cancer_general, breast | C19orf47 |
| chr19 | 40902425 | 40902812 | Hypo | cancer_general | PRX, HIPK4 | chr19 | 40951175 | 40951357 | Hypo | cancer_general | BLVRB, SERTAD3 |
| chr19 | 40951679 | 40951762 | Hypo | cancer_general | BLVRB, SERTAD3 | chr19 | 40991013 | 40991139 | Hypo | cancer_general | SPTBN4 |
| chr19 | 41473190 | 41473242 | Hypo | cancer_general | TGFB1 | chr19 | 41694610 | 41694640 | Hypo | cancer_general | CYP2S1 |
| chr19 | 41846193 | 41846325 | Hypo | ovarian | | chr19 | 41881534 | 41881811 | Hypo | cancer_general | TMEM91, BCKDHA |
| chr19 | 41919917 | 41919971 | Hypo | pancreas | BCKDHA ATP1A3, | chr19 | 42408300 | 42408330 | Hypo | cancer_general | ARHGEF1 |
| chr19 | 42460961 | 42461113 | Hypo | colorectal | RABAC1 | chr19 | 42856453 | 42856483 | Hypo | lung | MEGF8 |
| chr19 | 42911568 | 42911598 | Hypo | esophageal | LIPE, LIPE-AS1 | chr19 | 44599783 | 44599883 | Hypo | cancer_general | LOC100379224, ZNF224, ZNF284 |
| chr19 | 45003211 | 45003323 | Hypo | cancer_general | CEACAM20, ZNF180 | chr19 | 45541556 | 45541679 | Hypo | cancer_general | CLASRP, RELB |
| chr19 | 45570401 | 45570450 | Hypo | breast | ZNF296, CLASRP | chr19 | 45574465 | 45574495 | Hypo | cancer_general | GEMIN7, CLASRP, ZNF296 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 45574773 | 45574888 | Hypo | breast | GEMIN7, ZNF296, CLASRP | chr19 | 45601380 | 45601410 | Hypo | cancer_general | PPP1R37, GEMIN7 |
| chr19 | 45678395 | 45678555 | Hypo | ovarian | BLOC1S3, TRAPPC6A | chr19 | 45810102 | 45810267 | Hypo | cancer_general | CKM |
| chr19 | 45835028 | 45835268 | Hypo | cancer_general | KLC3, CKM | chr19 | 45997528 | 45997584 | Hypo | cancer_general | PPM1N, RTN2 |
| chr19 | 46234803 | 46234887 | Hypo | cancer_general | LOC388553 | chr19 | 46404522 | 46404601 | Hypo | cancer_general | MYPOP |
| chr19 | 47200361 | 47200536 | Hypo | cancer_general | PRKD2 | chr19 | 47329748 | 47329867 | Hypo | cancer_general | SNAR-E |
| chr19 | 47358646 | 47358751 | Hypo | cancer_general | AP2S1 | chr19 | 47515017 | 47515047 | Hypo | cancer_general | NPAS1, ARHGAP35 |
| chr19 | 47618255 | 47618434 | Hypo | cancer_general | ZC3H4 | chr19 | 47976399 | 47976429 | Hypo | cancer_general | KPTN, SLC8A2 |
| chr19 | 48003607 | 48003714 | Hypo | cancer_general | NAPA, NAPA-AS1 | chr19 | 48082100 | 48082130 | Hypo | cancer_general |  |
| chr19 | 48108151 | 48108320 | Hypo | cancer_general | GLTSCR1 | chr19 | 48137171 | 48137307 | Hypo | cancer_general | GLTSCR1 |
| chr19 | 48151265 | 48151337 | Hypo | cancer_general | GLTSCR1 | chr19 | 48249451 | 48249602 | Hypo | cancer_general | GLTSCR2, SNORD23, EHD2 |
| chr19 | 48614843 | 48614873 | Hypo | cancer_general | LIG1, PLA2G4C | chr19 | 48771551 | 48771600 | Hypo | cancer_general | ZNF114 |
| chr19 | 48777059 | 48777121 | Hypo | cancer_general | ZNF114 | chr19 | 48800603 | 48800769 | Hypo | cancer_general | CCDC114, ZNF114 |
| chr19 | 48857725 | 48857831 | Hypo | cancer_general | Mir_324, SYNGR4, TMEM143 | chr19 | 48902848 | 48902878 | Hypo | cancer_general | GRIN2D, KDELR1 |
| chr19 | 49043242 | 49043272 | Hypo | cancer_general |  | chr19 | 49119229 | 49119259 | Hypo | cancer_general | SPACA4, FAM83E, RPL18, SPHK2 |
| chr19 | 49180462 | 49180558 | Hypo | cancer_general | NTN5 | chr19 | 49285456 | 49285593 | Hypo | cancer_general | PPP1R15A, TULP2, PLEKHA4 |
| chr19 | 49290711 | 49290844 | Hypo | cancer_general | BCAT2, Mir_324 | chr19 | 49375050 | 49375216 | Hypo | cancer_general |  |
| chr19 | 49402471 | 49402551 | Hypo | cancer_general | TULP2, NUCB1, Mir_324 | chr19 | 49498076 | 49498148 | Hypo | cancer_general | RUVBL2 |
| chr19 | 49590284 | 49590399 | Hypo | cancer_general | SNRNP70 | chr19 | 49628132 | 49628252 | Hypo | cancer_general | PPFIA3, C19orf73, Mir_324, LIN7B |
| chr19 | 49784869 | 49784935 | Hypo | cancer_general | SLC6A16 | chr19 | 49890887 | 49890929 | Hypo | cancer_general | CCDC155 |
| chr19 | 49997263 | 49997324 | Hypo | cancer_general | RPS11, SNORD34, SNORD32A, FLT3LG, SNORD35B, MIR150, SNORD35A, SNORD33, RPL13A | chr19 | 49998434 | 49998607 | Hypo | cancer_general | FLT3LG, SNORD35B, MIR150, SNORD34, RPL13A, RPS11, SNORD35A, SNORD33, SNORD32A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 50028397 | 50028530 | Hypo | cancer_general | RCN3, TRNA_Lys, FCGRT | chr19 | 50049718 | 50049953 | Hypo | cancer_general | NOSIP |
| chr19 | 50203173 | 50203203 | Hypo | cancer_general | ADM5, CPT1C | chr19 | 50216042 | 50216072 | Hypo | cancer_general | CPT1C |
| chr19 | 50243339 | 50243379 | Hypo | head_neck | TSKS | chr19 | 50304736 | 50304766 | Hypo | pancreas | AP2A1, FUZ |
| chr19 | 50319874 | 50319916 | Hypo | cancer_general | MED25, FUZ, AP2A1 | chr19 | 50320233 | 50320277 | Hypo | cancer_general | MED25, FUZ, AP2A1 |
| chr19 | 50353394 | 50353574 | Hypo | cancer_general | PTOV1, MIR4749, PTOV1-AS1 | chr19 | 50589044 | 50589079 | Hypo | ovarian | SNAR-A3 |
| chr19 | 50874895 | 50874933 | Hypo | cancer_general | NR1H2, NAPSA | chr19 | 50898558 | 50898727 | Hypo | colorectal | POLD1 |
| chr19 | 50938547 | 50938691 | Hypo | cancer_general | MYBPC2, SPIB | chr19 | 51304554 | 51304602 | Hypo | cancer_general | SNORD88C, SNORD88A, SNORD88B, C19orf48, ACPT |
| chr19 | 51715329 | 51715359 | Hypo | cancer_general | | chr19 | 52139210 | 52139326 | Hypo | cancer_general | SIGLEC14, SIGLEC5 |
| chr19 | 52391235 | 52391264 | Hypo | literature | | chr19 | 52715963 | 52715992 | Hypo | literature | PPP2R1A |
| chr19 | 53028928 | 53029035 | Hypo | cancer_general | ZNF649, ZNF577 | chr19 | 53204758 | 53204837 | Hypo | hepatobiliary | ZNF611 |
| chr19 | 53291021 | 53291081 | Hypo | cancer_general | ZNF808 | chr19 | 53398908 | 53399031 | Hypo | hepatobiliary | ZNF320 |
| chr19 | 53399814 | 53399848 | Hypo | cancer_general | ZNF28 ZNF320 | chr19 | 53436895 | 53437067 | Hypo | hepatobiliary | ZNF816-ZNF321P, ZNF321P |
| chr19 | 53446951 | 53447130 | Hypo | cancer_general | ZNF816, ZNF816-ZNF321P, ZNF321P | chr19 | 53688015 | 53688059 | Hypo | hepatobiliary | ZNF665 |
| chr19 | 53860082 | 53860151 | Hypo | hepatobiliary | ZNF525, ZNF765, ZNF845 | chr19 | 53873182 | 53873212 | Hypo | hepatobiliary | ZNF765, ZNF525 |
| chr19 | 54271479 | 54271509 | Hypo | hepatobiliary | MIR519A2, MIR516A2, MIR1283-2 | chr19 | 54850630 | 54850659 | Hypo | literature | LILRA4 |
| chr19 | 55728901 | 55729104 | Hypo | cancer_general | PTPRH, TMEM86B | chr19 | 55849550 | 55849638 | Hypo | cancer_general | SUV420H2, TMEM150B |
| chr19 | 56201643 | 56201938 | Hypo | ovarian | EPN1 | chr19 | 56340995 | 56341033 | Hypo | cancer_general | NLRP4, NLRP11 |
| chr19 | 56588656 | 56588780 | Hypo | cancer_general | ZNF787, ZNF587B, ZNF552 | chr19 | 56858084 | 56858227 | Hypo | cancer_general | ZNF552 |
| chr19 | 57323825 | 57323854 | Hypo | literature | PEG3-AS1, PEG3, ZIM2 | chr19 | 58316915 | 58317096 | Hypo | cancer_general | |
| chr19 | 58325075 | 58325282 | Hypo | cancer_general | ZNF587, ZNF587B, ZNF552 | chr19 | 58807869 | 58807931 | Hypo | ovarian | LOC113386, ZNF8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 58874735 | 58874987 | Hypo | cancer_general | BC023201, ZNF497, A1BG-AS1, A1BG, ZNF837 | chr19 | 58964180 | 58964266 | Hypo | cancer_general | ZNF324B |
| chr19 | 59054642 | 59054774 | Hypo | cancer_general | TRIM28, CHMP2A | AC160854.2_10710-13495 | 1027 | 1057 | Hypo | ovarian | |
| HPV18 | 111 | 140 | Hypo | virus | | HPV18 | 383 | 412 | Hypo | virus | |
| HPV18 | 655 | 684 | Hypo | virus | | HPV18 | 927 | 956 | Hypo | virus | |
| HPV18 | 1199 | 1228 | Hypo | virus | | HPV18 | 1471 | 1500 | Hypo | virus | |
| HPV18 | 1743 | 1772 | Hypo | virus | | HPV18 | 2015 | 2044 | Hypo | virus | |
| HPV18 | 2287 | 2316 | Hypo | virus | | HPV18 | 2559 | 2588 | Hypo | virus | |
| HPV18 | 2831 | 2860 | Hypo | virus | | HPV18 | 3103 | 3132 | Hypo | virus | |
| HPV18 | 3375 | 3404 | Hypo | virus | | HPV18 | 3647 | 3676 | Hypo | virus | |
| HPV18 | 3919 | 3948 | Hypo | virus | | HPV18 | 4191 | 4220 | Hypo | virus | |
| HPV18 | 4463 | 4492 | Hypo | virus | | HPV18 | 4735 | 4764 | Hypo | virus | |
| HPV18 | 5007 | 5036 | Hypo | virus | | HPV1 | 5279 | 5308 | Hypo | virus | |
| HPV18 | 5551 | 5580 | Hypo | virus | | HPV18 | 5823 | 5852 | Hypo | virus | |
| HPV18 | 6095 | 6124 | Hypo | virus | | HPV18 | 6367 | 6396 | Hypo | virus | |
| HPV18 | 6639 | 6668 | Hypo | virus | | HPV18 | 6911 | 6940 | Hypo | virus | |
| HPV18 | 7183 | 7212 | Hypo | virus | | HPV18 | 7455 | 7484 | Hypo | virus | |
| chr17 | 415134 | 415163 | Hypo | literature | VPS53 | chr17 | 556252 | 556282 | Hypo | head_neck | VPS53 FAM57A |
| chr17 | 617001 | 617064 | Hypo | cancer_general | VPS53 | chr17 | 631704 | 631734 | Hypo | head_neck | SCARF1 WDR81, MIR22, AF070569, MIR22HG |
| chr17 | 1136593 | 1136653 | Hypo | cancer_general | | chr17 | 1536116 | 1536146 | Hypo | head_neck | SRR, TSR1 |
| chr17 | 1545976 | 1546442 | Hypo | cancer_general | PRPF8, SCARF1, RILP | chr17 | 1623703 | 1623735 | Hypo | cancer_general | |
| chr17 | 2207718 | 2208063 | Hypo | cancer_general | SRR, SMG6 | chr17 | 2219952 | 2220319 | Hypo | cancer_general | |
| chr17 | 2220564 | 2221059 | Hypo | cancer_general | SRR, TSR1 SGSM2, MNT | chr17 | 2250051 | 2250081 | Hypo | cancer_general | SGSM2 |
| chr17 | 2278801 | 2278925 | Hypo | breast | | chr17 | 2496019 | 2496049 | Hypo | cancer_general | PAFAH1B1, DD413682 |
| chr17 | 2538269 | 2538337 | Hypo | cancer_general | PAFAH1B1 | chr17 | 2663898 | 2664032 | Hypo | cancer_general | RAP1GAP2 |
| chr17 | 2811362 | 2811392 | Hypo | hepatobiliary | RAP1GAP2 | chr17 | 2873476 | 2873551 | Hypo | hepatobiliary | |
| chr17 | 2950959 | 2951091 | Hypo | cancer_general | RAP1GAP2 | chr17 | 3657502 | 3657553 | Hypo | cancer_general | |
| chr17 | 3658849 | 3659011 | Hypo | cancer_general | | chr17 | 4693354 | 4693388 | Hyp | breast | |
| chr17 | 4698990 | 4699252 | Hypo | cancer_general | PSMB6, GLTPD2, BC150535, VMO1 | chr17 | 5167638 | 5167681 | Hypo | breast | PSMB6, GLTPD2, BC150535, VMO1, TM4SF5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 5168597 | 5168732 | Hypo | breast | | chr17 | 6470357 | 6470419 | Hypo | cancer_general | ACAP1 |
| chr17 | 7043422 | 7043595 | Hypo | cancer_general | | chr17 | 7242844 | 7242899 | Hypo | cancer_general | SENP3-EIF4A1, SNORA48, SNORD10, SNORA67, DD413682, SENP3, TNFSF13 |
| chr17 | 7368947 | 7369139 | Hypo | ovarian | ZBTB4, CHRNB1 | chr17 | 7471610 | 7471709 | Hypo | colorectal | |
| chr17 | 7488151 | 7488249 | Hypo | cancer_general | SOX15, CD68, DD413682, SNORA67, SNORD10, SNORA48, MPDU1, FXR2, SENP3-EIF4A1 | chr17 | 7572957 | 7573018 | Hypo | literature | HV941442, HV941444, HV941430, HV941433, HV941428, HV941434, HV941429, HV941478, HV941431, TP53, HV941486, HV941440 |
| chr17 | 7573968 | 7574028 | Hypo | literature | HV941486, HV941440, HV941478, HV941429, HV941442, HV941444, HV941430, HV941433, HV941428, HV941434, HV941431 | chr17 | 7576847 | 7577167 | Hypo | literature | HV941486, HV941429, HV941430, HV941434, TP53, HV941440, HV941478, HV941442, HV941444, HV941431, HV941433, HV941428 |
| chr17 | 7577504 | 7577604 | Hypo | literature | TP53, HV941478, HV941442, HV941444, HV941430, HV941486, HV941428, HV941433, HV941429, HV941440, HV941434, HV941431 | chr17 | 7578164 | 7578570 | Hypo | literature | HV941486, HV941434, HV941428, HV941440, HV941478, HV941442, HV941444, HV941429, HV941431, TP53, HV941430, HV941433 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 7579285 | 7579880 | Hypo | literature | TP53, HV941430, WRAP53, HV941478, HV941429, HV941428, HV941444, HV941440, HV941486, HV941434, HV941433, HV941431, HV941442 | chr17 | 7906832 | 7906861 | Hypo | tcga | GUCY2D |
| chr17 | 8104145 | 8104260 | Hypo | cancer_general | AURKB | chr17 | 8774623 | 8774653 | Hypo | cancer_general | PIK3R5, PIK3R6 |
| chr17 | 9790805 | 9790835 | Hypo | cancer_general | GLP2R | chr17 | 10599510 | 10599546 | Hypo | cancer_general | SCO1, ADPRM |
| chr17 | 11984693 | 11984722 | Hypo | literature | MIR744, MAP2K4 | chr17 | 11998944 | 11998973 | Hypo | literature | |
| chr17 | 12013726 | 12013755 | Hypo | literature | | chr17 | 12016550 | 12016630 | Hypo | literature | MYOCD |
| chr17 | 12028618 | 12028647 | Hypo | literature | | chr17 | 12659029 | 12659063 | Hypo | cancer_general | PIGL |
| chr17 | 15926819 | 15926849 | Hypo | head_neck | TTC19, NCOR1 | chr17 | 16119860 | 16120047 | Hypo | cancer_general | NCOR1 |
| chr17 | 16282251 | 16282300 | Hypo | cancer_general | UBB | chr17 | 16326144 | 16326216 | Hypo | head_neck | TRPV2 |
| chr17 | 16428708 | 16428738 | Hypo | head_neck | | chr17 | 17062574 | 17062763 | Hypo | head_neck | MPRIP |
| chr17 | 17117365 | 17117395 | Hypo | breast | FLCN, PLD6 | chr17 | 17123963 | 17123993 | Hypo | head_neck | FLCN, PLD6 |
| chr17 | 17719242 | 17719355 | Hypo | breast | MIR33B, SREBP-1, SREBF1 | chr17 | 18162844 | 18163325 | Hypo | cancer_general | FLII, SMCR7, DQ596932 |
| chr17 | 18817198 | 18817284 | Hypo | esophageal | PRPSAP2 | chr17 | 19769739 | 19769821 | Hypo | cancer_general | TRNA_Gly |
| chr17 | 19886035 | 19886221 | Hypo | head_neck | AKAP10 | chr17 | 20039589 | 20039676 | Hypo | hepatobiliary | SPECC1 |
| chr17 | 20081131 | 20081161 | Hypo | hepatobiliary | SPECC1 | chr17 | 20205055 | 20205181 | Hypo | hepatobiliary | SPECC1 |
| chr17 | 20238152 | 20238198 | Hypo | hepatobiliary | CCDC144CP | chr17 | 20468021 | 20468090 | Hypo | cancer_general | DQ584223 |
| chr17 | 20817755 | 20817917 | Hypo | cancer_general | | chr17 | 21003587 | 21003721 | Hypo | cancer_general | HP08942 |
| chr17 | 25620573 | 25620715 | Hypo | cancer_general | MIR4522, WSB1 | chr17 | 25676959 | 25676989 | Hypo | | |
| chr17 | 25680264 | 25680294 | Hypo | cancer_general | | chr17 | 25907750 | 25907780 | Hypo | cancer_general | KSR1 |
| chr17 | 26263183 | 26263322 | Hypo | cancer_general | | chr17 | 26927249 | 26927410 | Hypo | cancer_general | SGK494, SPAG5-AS1, SPAG5 |
| chr17 | 26961770 | 26961833 | Hypo | cancer_general, breast | KIAA0100 | chr17 | 27036492 | 27037023 | Hypo | cancer_general | RAB34, NARR, RPL23A, PROCA1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 27056577 | 27056857 | Hypo | cancer_general | SNORD42A, SNORD4A, SNORD42B, RPL23A, NEK8, TLCD1, SNORD4B | chr17 | 27081845 | 27081963 | Hypo | cancer_general | FAM222B, TRAF4 |
| chr17 | 27170162 | 27170460 | Hypo | cancer_general | FAM222B | chr17 | 27181180 | 27181371 | Hypo | lung | ERAL1, MIR451A, MIR451B, MIR144, MIR4732 |
| chr17 | 27686651 | 27686783 | Hypo | colorectal | | chr17 | 27716114 | 27716220 | Hypo | cancer_general | MIR4523, TAOK1 |
| chr17 | 27716436 | 27716642 | Hypo | cancer_general | MIR4523, TAOK1 | chr17 | 28112648 | 28112688 | Hypo | cancer_general | SSH2 |
| chr17 | 28112951 | 28113037 | Hypo | cancer_general | SSH2 | chr17 | 29232244 | 29232350 | Hypo | cancer_general | TEFM |
| chr17 | 29234283 | 29234313 | Hypo | literature | TEFM | chr17 | 29508761 | 29508790 | Hypo | literature | NF1 |
| chr17 | 29541527 | 29541556 | Hypo | literature | NF1 | chr17 | 29562732 | 29562761 | Hypo | literature | NF1 |
| chr17 | 30243768 | 30243907 | Hypo | cancer_general | | chr17 | 30250325 | 30250364 | Hypo | cancer_general | |
| chr17 | 30258469 | 30258499 | Hypo | head_neck | SUZ12 | chr17 | 30568137 | 30568174 | Hypo | breast | |
| chr17 | 30710818 | 30710888 | Hypo | cancer_general | ZNF207 | chr17 | 32386720 | 32386875 | Hypo | cancer_general | SLFN14 |
| chr17 | 33721211 | 33721349 | Hypo | cancer_general | | chr17 | 33877286 | 33877439 | Hypo | cancer_general | SNORA21, C17orf98, RPL23 |
| chr17 | 33917210 | 33917268 | Hypo | cancer_general | AP2B1 | chr17 | 37001415 | 37001921 | Hypo | cancer_general | FBXO47 |
| chr17 | 37011176 | 37011236 | Hypo | cancer_general | RPL23, TRNA_Cys, SNORA21 | chr17 | 37131789 | 37132028 | Hypo | cancer_general | |
| chr17 | 37181771 | 37181865 | Hypo | cancer_general | LRRC37A11P, ARL5C, TRNA_Cys, PLXDC1 | chr17 | 37192072 | 37192201 | Hypo | cancer_general | LRRC37A11P, STAC2, RPL19 |
| chr17 | 37312431 | 37312477 | Hypo | cancer_general | | chr17 | 37369180 | 37369210 | Hypo | cancer_general | |
| chr17 | 37484062 | 37484128 | Hypo | cancer_general | FBXL20 | chr17 | 37868190 | 37868294 | Hypo | literature | ERBB2 |
| chr17 | 37879568 | 37879615 | Hypo | literature | MIR4728, MIEN1, ERBB2 | chr17 | 37880205 | 37880276 | Hypo | literature | MIR4728, MIEN1, ERBB2 |
| chr17 | 37880971 | 37881018 | Hypo | literature | MIEN1, ERBB2, MIR4728 | chr17 | 37881318 | 37881631 | Hypo | literature | MIR4728, MIEN1, ERBB2 |
| chr17 | 38179397 | 38179430 | Hypo | cancer_general | MED24, SNORD124, CSF3 | chr17 | 38335459 | 38335533 | Hypo | cancer_general | RAPGEFL1, CASC3 |
| chr17 | 38380553 | 38380598 | Hypo | cancer_general | WIPF2 | chr17 | 38473104 | 38473180 | Hypo | literature | RARA |
| chr17 | 38574991 | 38575021 | Hypo | cancer_general | TOP2A | chr17 | 39682352 | 39682711 | Hypo | cancer_general | AK090604, KRT15, JUP, KRT19 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 39834201 | 39834287 | Hypo | cancer_general | | | | | | | |
| chr17 | 40897739 | 40897788 | Hypo | ovarian | RAMP2-AS1, BC047651, EZH1 | chr17 | 40474467 | 40474496 | Hypo | literature | STAT3, AK024535, AK092965 |
| chr17 | 41175146 | 41175331 | Hypo | cancer_general | RND2, VAT1, IFI35 | chr17 | 40975413 | 40975677 | Hypo | cancer_general | PSME3, BECN1 |
| chr17 | 41201163 | 41201192 | Hypo | literature | BRCA1 | chr17 | 41197714 | 41197743 | Hypo | literature | BRCA1 |
| chr17 | 41209064 | 41209114 | Hypo | literature | BRCA1 | chr17 | 41203073 | 41203102 | Hypo | literature | BRCA1 |
| chr17 | 41267731 | 41267775 | Hypo | literature | NBR2, BRCA1 | chr17 | 41215890 | 41215961 | Hypo | literature | BRCA1 |
| chr17 | 41278621 | 41278700 | Hypo | cancer_general | NBR2, BRCA1 | chr17 | 41276031 | 41276075 | Hypo | literature | BRCA1, NBR2 |
| chr17 | 41745825 | 41745855 | Hypo | cancer_general | MEOX1 | chr17 | 41651850 | 41651880 | Hypo | cancer_general | |
| chr17 | 42110423 | 42110561 | Hypo | head_neck | LSM12 | chr17 | 41791665 | 41791694 | Hypo | tcga | LSM12, G6PC3, AX746969 |
| chr17 | 42246452 | 42246521 | Hypo | cancer_general | ASB16, ASB16-AS1, C17orf65, C17orf53 | chr17 | 42142661 | 42142808 | Hypo | cancer_general | |
| chr17 | 42331412 | 42331659 | Hypo | cancer_general | SLC4A1 | chr17 | 42321590 | 42321674 | Hypo | cancer_general | SLC4A1 |
| chr17 | 42587249 | 42587355 | Hypo | cancer_general | CCDC43 | chr17 | 42580695 | 42580793 | Hypo | breast | DBF4B |
| chr17 | 42767947 | 42768198 | Hypo | cancer_general | CCDC103, FAM187A, AK124465, GFAP, EFTUD2 | chr17 | 42590091 | 42590224 | Hypo | cancer_general | GFAP |
| chr17 | 42975726 | 42975756 | Hypo | cancer_general | | chr17 | 42287481 | 42287616 | Hypo | cancer_general | KIF18B |
| | | | | | | chr17 | 43001891 | 43001946 | Hypo | cancer_general | |
| chr17 | 44897416 | 44897445 | Hypo | literature | WNT3 | chr17 | 45022106 | 45022140 | Hypo | cancer_general | GOSR2 |
| chr17 | 45187608 | 45187638 | Hypo | cancer_general | CDC27 | chr17 | 46567400 | 46567655 | Hypo | cancer_general | |
| chr17 | 46827420 | 46827539 | Hypo | cancer_general | | chr17 | 47657544 | 47657583 | Hypo | cancer_general | |
| chr17 | 48473056 | 48473236 | Hypo | cancer_general | | chr17 | 48589801 | 48589831 | Hypo | colorectal | |
| chr17 | 48612223 | 48612308 | Hypo | cancer_general | EPN3, SPATA20, MYCBPAP | chr17 | 48653128 | 48653158 | Hypo | cancer_general | |
| chr17 | 48799820 | 48799866 | Hypo | cancer_general | LUC7L3 | chr17 | 49229267 | 49229703 | Hypo | cancer_general | |
| chr17 | 53479184 | 53479316 | Hypo | colorectal | MMD | chr17 | 53814544 | 53814678 | Hypo | cancer_general | NXPH3 |
| chr17 | 55037326 | 55037626 | Hypo | cancer_general | COIL | chr17 | 56092600 | 56092736 | Hypo | cancer_general | MYCBPAP |
| chr17 | 56471121 | 56471167 | Hypo | colorectal | RNF43 | chr17 | 56743206 | 56743249 | Hypo | cancer_general | CACNA1G |
| chr17 | 57296865 | 57297129 | Hypo | cancer_general | GDPD1, SMG8 | chr17 | 57386255 | 57386735 | Hypo | cancer_general | |
| chr17 | 57787402 | 57787465 | Typo | cancer_general | VMP1, PTRH2 | chr17 | 57832475 | 57832607 | Hypo | cancer_general | NME1-NME2, NME1 |
| | | | | | | chr17 | | | Hypo | cancer_general | SRSF1 |
| | | | | | | chr17 | | | Hypo | cancer_general | TEX14 |
| | | | | | | chr17 | | | Hypo | cancer_general | VMP1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 59481657 | 59481694 | Hypo | esophageal | C17orf82, TBX2 | chr17 | 59924556 | 59924585 | Hypo | literature | TACO1, BC024682, DQ577731, DCAF7 |
| chr17 | 59937192 | 59937236 | Hypo | literature | INTS2 | chr17 | 61677374 | 61677404 | Hypo | cancer_general | SCN4A |
| chr17 | 61817576 | 61817955 | Hypo | cancer_general | STRADA, CCDC47 | chr17 | 62028596 | 62028790 | Hypo | cancer_general | SCN4A |
| chr17 | 64672366 | 64672544 | Hypo | cancer_general | MIR635, WIPI1, ARSG | chr17 | 65715296 | 65715493 | Hypo | cancer_general | NOL11 |
| chr17 | 66420718 | 66420837 | Hypo | lung | | chr17 | 67410305 | 67410397 | Hypo | cancer_general | MAP2K6 |
| chr17 | 70586165 | 70586272 | Hypo | cancer_general | LINC00511, LINC00673 | chr17 | 71229815 | 71229918 | Hypo | cancer_general | C17orf80, FAM104A |
| chr17 | 72236510 | 72236548 | Hypo | hepatobiliary | TTYH2 | chr17 | 72491378 | 72491531 | Hypo | ovarian | Metazoa_SRP, TRNA_Arg, JB153618, KCTD2, ATP5H |
| chr17 | 72862371 | 72862460 | Hypo | blood | FDXR, GRIN2C | chr17 | 73031637 | 73031935 | Hypo | cancer_general | |
| chr17 | 73115588 | 73115658 | Hypo | cancer_general | ARMC7 | chr17 | 73115884 | 73115914 | Hypo | cancer_general | ARMC7 |
| chr17 | 73128301 | 73128338 | Hypo | cancer_general | NT5C, ARMC7, HN1 | chr17 | 73147177 | 73147356 | Hypo | cancer_general | HN1 |
| chr17 | 73147774 | 73147992 | Hypo | cancer_general | HN1 | chr17 | 73215289 | 73215423 | Hypo | ovarian | NUP85 |
| chr17 | 73351981 | 73352086 | Hypo | breast | GRB2 | chr17 | 73545998 | 73546299 | Hypo | cancer_general | LLGL2 |
| chr17 | 73586015 | 73586418 | Hypo | cancer_general | MYO15B, RECQL5, SMIM5, SMIM6 | chr17 | 73608306 | 73608336 | Hypo | cancer_general | MYO15B |
| chr17 | 73636144 | 73636337 | Hypo | cancer_general | | chr17 | 73692986 | 73693122 | Hypo | cancer_general | SAP30BP |
| chr17 | 73782870 | 73782947 | Hypo | cancer_general | UNK, MIR4738, H3F3B | chr17 | 73808631 | 73808671 | Hypo | head_neck | UNK |
| chr17 | 73827213 | 73827243 | Hypo | esophageal | UNC13D, UNK | chr17 | 73901630 | 73901893 | Hypo | cancer_general | MRPL38, TRIM65, FBF1 |
| chr17 | 73904093 | 73904127 | Hypo | lung | FBF1, MRPL38 | chr17 | 74028346 | 74028413 | Hypo | cancer_general | SRP68, EVPL |
| chr17 | 74047797 | 74048063 | Hypo | cancer_general | SRP68 | chr17 | 74087118 | 74087185 | Hypo | head_neck | EXOC7, ZACN |
| chr17 | 74299798 | 74299899 | Hypo | cancer_general | PRPSAP1, QRICH2 | chr17 | 74390363 | 74390393 | Hypo | cancer_general | UBE2O, SPHK1 |
| chr17 | 74663258 | 74663288 | Hypo | head_neck | MXRA7 | chr17 | 74732944 | 74732973 | Hypo | literature | MFSD11, MIR636, SRSF2, METTL23 |
| chr17 | 75207514 | 75207630 | Hypo | blood | SEC14L1 | chr17 | 75207839 | 75207987 | Hypo | blood | SEC14L1 |
| chr17 | 75276054 | 75276083 | Hypo | literature | 9-Sep | chr17 | 75276413 | 75276442 | Hypo | literature | 9-Sep |
| chr17 | 75277348 | 75277659 | Hypo | literature | 9-Sep | chr17 | 75278020 | 75278049 | Hypo | literature | 9-Sep |
| chr17 | 75279105 | 75279134 | Hypo | literature | 9-Sep | chr17 | 75282025 | 75282154 | Hypo | literature | 9-Sep |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 75316368 | 75316397 | Hypo | literature | 9-Sep | chr17 | 75317170 | 75317199 | Hypo | literature | 9-Sep |
| chr17 | 75347755 | 75347784 | Hypo | literature | 9-Sep | chr17 | 75373312 | 75373341 | Hypo | literature | 9-Sep |
| chr17 | 75405827 | 75405856 | Hypo | literature | 9-Sep | chr17 | 75523142 | 75523272 | Hypo | cancer_general | BC040189 |
| chr17 | 75733978 | 75734244 | Hypo | lung, cancer_general | | chr17 | 75797111 | 75797179 | Hypo | cancer_general | |
| chr17 | 76021047 | 76021077 | Hypo | cancer_general | TNRC6C | chr17 | 76130124 | 76130153 | Hypo | literature | TMC8, TMC6 |
| chr17 | 76135783 | 76136001 | Hypo | lung, cancer_general | C17orf99, TMC8 | chr17 | 76137951 | 76138190 | Hypo | cancer_general | C17orf99, TMC8 |
| chr17 | 76138498 | 76138622 | Hypo | cancer_general | TMC8, C17orf99 | chr17 | 76187407 | 76187544 | Hypo | ovarian | TMC8, AFMID, TK1 |
| chr17 | 76207342 | 76207372 | Hypo | cancer_general | BIRC5, AFMID | chr17 | 76211302 | 76211506 | Hypo | cancer_general | EPR-1, BIRC5, AFMID |
| chr17 | 76404615 | 76404659 | Hypo | colorectal | PGS1 | chr17 | 76877177 | 76877212 | Hypo | hepatobiliary | LOC100653515, TIMP2 |
| chr17 | 76884417 | 76884447 | Hypo | hepatobiliary | LOC100653515, TIMP2 | chr17 | 76974447 | 76974499 | Hypo | cancer_general | LGALS3BP |
| chr17 | 76983518 | 76983669 | Hypo | cancer_general | CANT1, LGALS3BP | chr17 | 76984053 | 76984188 | Hypo | cancer_general | LGALS3BP, CANT1, DQ595190 |
| chr17 | 77070307 | 77070457 | Hypo | colorectal | ENGASE | chr17 | 77084518 | 77084727 | Hypo | ovarian | RBFOX3, ENGASE |
| chr17 | 77105055 | 77105198 | Hypo | cancer_general | RBFOX3 | chr17 | 77145129 | 77145242 | Hypo | cancer_general | RBFOX3 |
| chr17 | 77394706 | 77394850 | Hypo | ovarian | RBFOX3 | chr17 | 77825696 | 77825812 | Hypo | cancer_general | |
| chr17 | 77827114 | 77827201 | Hypo | cancer_general | TBC1D16 | chr17 | 77919429 | 77919477 | Hypo | pancreas | TBC1D16 |
| chr17 | 77924259 | 77924351 | Hypo | pancreas | SLC26A11, SGSH | chr17 | 78122158 | 78122190 | Hypo | cancer_general | EIF4A3 |
| chr17 | 78194821 | 78194861 | Hypo | pancreas | | chr17 | 78272278 | 78272313 | Hypo | breast | RNF213 |
| chr17 | 78447127 | 78447157 | Hypo | cancer_general | NPTX1, AX746631 | chr17 | 78518031 | 78518198 | Hypo | cancer_general | RPTOR |
| chr17 | 78599596 | 78599628 | Hypo | cancer_general | RPTOR | chr17 | 78667992 | 78668159 | Hypo | cancer_general | RPTOR |
| chr17 | 78874441 | 78874559 | Hypo | cancer_general | | chr17 | 78975667 | 78975758 | Hypo | cancer_general | AF258550, CHMP6 |
| chr17 | 78999625 | 78999654 | Hypo | literature | BAIAP2-AS1, BAIAP2 | chr17 | 79094182 | 79094245 | Hypo | cancer_general | MIR657, MIR3065, MIR338, AATK |
| chr17 | 79099770 | 79099799 | Hypo | literature | MIR1250, MIR338, MIR3065, MIR657, AATK | chr17 | 79626591 | 79626703 | Hypo | cancer_general | OXLD1, CCDC137, PDE6G |
| chr17 | 79626955 | 79626985 | Hypo | cancer_general | OXLD1, CCDC137, PDE6G | chr17 | 79769433 | 79769693 | Hypo | cancer_general | GCGR |
| chr17 | 79850445 | 79850537 | Hypo | cancer_general | ALYREF, ANAPC11, NPB | chr17 | 79896013 | 79896043 | Hypo | blood | MYADML2, PYCR1, MAFG-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 79939605 | 79939835 | Hypo | cancer_general | ASPSCR1 | chr17 | 79945037 | 79945074 | Hypo | breast | ASPSCR1 |
| chr17 | 80254266 | 80254296 | Hypo | cancer_general | BC033560 | chr17 | 80289234 | 80289310 | Hypo | cancer_general | SECTM1 |
| chr17 | 80289858 | 80289892 | Hypo | cancer_general | SECTM1 | chr17 | 80294282 | 80294427 | Hypo | cancer_general | SECTM1 |
| chr17 | 80394063 | 80394185 | Hypo | breast | HEXDC, C17orf62 | chr17 | 80479911 | 80479559 | Hypo | cancer_general | FOXK2 |
| chr17 | 80491572 | 80491602 | Hypo | head_neck | FOXK2 | chr17 | 80535382 | 80535487 | Hypo | colorectal | FOXK2 |
| chr17 | 80571380 | 80571776 | Hypo | lung | WDR45B, FOXK2 | chr17 | 80593754 | 80594107 | Hypo | cancer_general | WDR45B |
| chr17 | 80654983 | 80655013 | Hypo | cancer_general | RAB40B | chr17 | 80749152 | 80749276 | Hypo | ovarian | TBCD |
| chr17 | 80751650 | 80751714 | Hypo | breast | TBCD | chr17 | 80794259 | 80794288 | Hypo | literature | TBCD, ZNF750 |
| chr17 | 80797692 | 80798345 | Hypo | cancer_general | ZNF750, TBCD | chr17 | 80832305 | 80832411 | Hypo | cancer_general | |
| chr17 | 80832712 | 80832796 | Hypo | cancer_general | | chr17 | 80859239 | 80859269 | Hypo | head_neck | TBCD |
| chr17 | 81008618 | 81008826 | Hypo | cancer_general | | chr17 | 81033487 | 81033517 | Hypo | cancer_general | METRNL |
| chr17 | 81049023 | 81049023 | Hypo | cancer_general | METRNL | chr17 | 81049994 | 81050058 | Hypo | cancer_general | METRNL |
| chr20 | 291148 | 291373 | Hyper | liver_tcga, cancer_general | | chr20 | 590434 | 590502 | Hyper | cancer_general | TCF15 |
| chr20 | 590751 | 590868 | Hyper | cancer_general | TCF15 | chr20 | 592405 | 592449 | Hyper | cancer_general | TCF15 |
| chr20 | 644182 | 644787 | Hyper | cancer_general | SCRT2 | chr20 | 982749 | 982989 | Hyper | cancer_general | RSPO4 |
| chr20 | 1208855 | 1207034 | Hyper | blood | RAD21L1 | chr20 | 1783761 | 1784365 | Hyper | tcga, liver_tcga, cancer_general | |
| chr20 | 1874512 | 1874541 | Hyper | literature | SIRPA | chr20 | 1876110 | 1876176 | Hyper | esophageal | SIRPA |
| chr20 | 2539331 | 2539771 | Hyper | cancer_general | TMC2 | chr20 | 2668770 | 2668922 | Hyper | cancer_general | EBF4 |
| chr20 | 2780753 | 2781452 | Hyper | tcga, liver_tcga, cancer_general | CPXM1 | chr20 | 2781731 | 2781761 | Hyper | cancer_general | CPXM1 |
| chr20 | 2785659 | 2786060 | Hyper | cancer_general | TMEM239, C20orf141, AVP | chr20 | 3052583 | 3052836 | Hyper | cancer_general | OXT |
| chr20 | 3073488 | 3073899 | Hyper | cancer_general | | chr20 | 3220893 | 3220943 | Hyper | cancer_general | SLC4A11, C20orf194 |
| chr20 | 3229576 | 3229612 | Hyper | cancer_general | C20orf194, SLC4A11 | chr20 | 3389393 | 3389549 | Hyper | tcga | |
| chr20 | 3641733 | 3641937 | Hyper | cancer_general | ADAM33, AX748440, GFRA4 | chr20 | 3663020 | 3663174 | Hyper | cancer_general | ADAM33, SIGLEC1 |
| chr20 | 3762152 | 3762181 | Hyper | tcga | CENPB, CDC25B, SPEF1 | chr20 | 4229402 | 4229432 | Hyper | cancer_general | ADRA1D |
| chr20 | 4229786 | 4230600 | Hyper | esophageal, cancer_general | ADRA1D | chr20 | 4803070 | 4803650 | Hyper | tcga, cancer_general | RASSF2 |
| chr20 | 4803921 | 4804008 | Hyper | colorectal | RASSF2 | chr20 | 4804566 | 4804724 | Hyper | tcga | RASSF2 |
| chr20 | 5296172 | 5296900 | Hyper | cancer_general | AX746654, PROKR2 | chr20 | 5297206 | 5297603 | Hyper | cancer_general | AX746654, PROKR2 |
| chr20 | 6748925 | 6749036 | Hyper | blood | BMP2 | chr20 | 8112378 | 8112408 | Hyper | cancer_general | PLCB1 |
| chr20 | 8112739 | 8113022 | Hyper | tcga, cancer_general | PLCB1 | chr20 | 8113557 | 8113605 | Hyper | cancer_general | PLCB1 |
| chr20 | 9487385 | 9487997 | Hyper | cancer_general | LAMP5 | chr20 | 9488376 | 9488795 | Hyper | cancer_general | LAMP5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 9489070 | 9489214 | Hyper | cancer_general | LAMP5 | chr20 | 9489424 | 9489708 | Hyper | cancer_general | LAMP5 |
| chr20 | 9495271 | 9495509 | Hyper | cancer_general | LAMP5 | chr20 | 9496330 | 9496833 | Hyper | cancer_general | LAMP5 |
| chr20 | 9497035 | 9497109 | Hyper | cancer_general | LAMP5 | chr20 | 10198289 | 10198600 | Hyper | cancer_general | SNAP25 |
| chr20 | 10198915 | 10198945 | Hyper | cancer_general | SNAP25 | chr20 | 13200599 | 13200634 | Hyper | cancer_general | ISM1, AY927515 |
| chr20 | 17206513 | 17206747 | Hyper | cancer_general | PCSK2 | chr20 | 17207874 | 17207930 | Hyper | cancer_general | PCSK2 |
| chr20 | 17208585 | 17208620 | Hyper | cancer_general | PCSK2 | chr20 | 18039823 | 18039897 | Hyper | blood | OVOL2 |
| chr20 | 18073312 | 18073461 | Hyper | pancreas | | chr20 | 19739592 | 19739696 | Hyper | cancer_general | |
| chr20 | 20344498 | 20344559 | Hyper | cancer_general | C20orf26, INSM1 | chr20 | 20345686 | 20346106 | Hyper | cancer_general | INSM1, C20orf26 |
| chr20 | 20347460 | 20348154 | Hyper | cancer_general | INSM1, C20orf26 | chr20 | 20348526 | 20348605 | Hyper | esophageal | INSM1, C20orf26 |
| chr20 | 20349153 | 20349255 | Hyper | tcga, liver_tcga | | chr20 | 20349574 | 20349604 | Hyper | esophageal | |
| chr20 | 21080714 | 21082253 | Hyper | liver_tcga, cancer_general | | chr20 | 21082532 | 21082917 | Hyper | cancer_general | |
| chr20 | 21083421 | 21084361 | Hyper | cancer_general | | chr20 | 21085831 | 21085864 | Hyper | cancer_general | |
| chr20 | 21086176 | 21086451 | Hyper | cancer_general | | chr20 | 21086866 | 21087188 | Hyper | cancer_general | |
| chr20 | 21372174 | 21372725 | Hyper | cancer_general | NKX2-4, XRN2 | chr20 | 21376250 | 21378551 | Hyper | liver_tcga, cancer_general | NKX2-4, XRN2 |
| chr20 | 21486375 | 21486881 | Hyper | cancer_general | NKX2-2 | chr20 | 21487153 | 21487581 | Hyper | cancer_general | NKX2-2 |
| chr20 | 21488158 | 21488351 | Hyper | cancer_general | NKX2-2 | chr20 | 21489224 | 21489703 | Hyper | cancer_general | NKX2-2 |
| chr20 | 21490175 | 21491529 | Hyper | cancer_general | NKX2-2 | chr20 | 21492378 | 21492983 | Hyper | cancer_general | NKX2-2 |
| chr20 | 21493308 | 21494265 | Hyper | cancer_general | NKX2-2 | chr20 | 21494531 | 21494703 | Hyper | cancer_general | NKX2-2 |
| chr20 | 21495942 | 21495986 | Hyper | cancer_general | NKX2-2 | chr20 | 21496260 | 21496294 | Hyper | cancer_general | NKX2-2 |
| chr20 | 21496637 | 21497136 | Hyper | cancer_general | NKX2-2 | chr20 | 21497413 | 21498638 | Hyper | cancer_general | NKX2-2 |
| chr20 | 21499961 | 21500134 | Hyper | cancer_general | NKX2-2 | chr20 | 21501424 | 21501724 | Hyper | cancer_general | NKX2-2 |
| chr20 | 21502037 | 21502330 | Hyper | cancer_general | NKX2-2 | chr20 | 21502590 | 21503117 | Hyper | cancer_general | NKX2-2 |
| chr20 | 21503441 | 21503773 | Hyper | cancer_general, tcga | NKX2-2 | chr20 | 21682399 | 21682456 | Hyper | cancer_general | PAX1 |
| chr20 | 21683311 | 21683651 | Hyper | cancer_general | PAX1 | chr20 | 21686235 | 21686677 | Hyper | cancer_general | PAX1 |
| chr20 | 21687009 | 21687731 | Hyper | cancer_general | PAX1 | chr20 | 21689956 | 21690185 | Hyper | cancer_general | PAX1 |
| chr20 | 21694499 | 21694529 | Hyper | cancer_general | PAX1 | chr20 | 21695088 | 21695357 | Hyper | tcga, cancer_general | PAX1 |
| chr20 | 21748445 | 21748491 | Hyper | cancer_general | | chr20 | 22557396 | 22557675 | Hyper | cancer_general | FOXA2, LINC00261 |
| chr20 | 22557979 | 22558114 | Hyper | cancer_general | FOXA2, LINC00261 | chr20 | 22558637 | 22558669 | Hyper | cancer_general | FOXA2, LINC00261 |
| chr20 | 22559645 | 22559690 | Hyper | cancer_general | FOXA2, LINC00261 | chr20 | 22562721 | 22562840 | Hyper | cancer_general | LINC00261, FOXA2 |
| chr20 | 22563563 | 22563602 | Hyper | cancer_general | FOXA2, LINC00261 | chr20 | 22564235 | 22564265 | Hyper | cancer_general | FOXA2, LINC00261 |
| chr20 | 22566961 | 22566990 | Hyper | literature | | chr20 | 23015917 | 23015946 | Hyper | blood | BC045663, SSTR4 |
| chr20 | 23029110 | 23029151 | Hyper | cancer_general | THBD, AX747264 | chr20 | 23029387 | 23030357 | Hyper | literature | THBD, AX747264 |
| chr20 | 23031548 | 23031692 | Hyper | literature | THBD, AX747264 | chr20 | 24450231 | 24450513 | Hyper | literature, cancer_general | AX747264 |
| chr20 | 24450782 | 24451019 | Hyper | cancer_general | SYNDIG1 | chr20 | 24451450 | 24451592 | Hyper | tcga, cancer_general | SYNDIG1 |
| chr20 | 25058385 | 25058616 | Hyper | cancer_general | VSX1 | chr20 | 25061746 | 25062880 | Hyper | cancer_general | VSX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 25063780 | 25064458 | Hyper | cancer_general | VSX1 | chr20 | 25065179 | 25065395 | Hyper | cancer_general | VSX1 |
| chr20 | 25129384 | 25129464 | Hyper | cancer_general | LOC284798 | chr20 | 26188812 | 26189011 | Hyper | liver_tcga, cancer_general, literature | MIR663A, LOC284801 |
| chr20 | 26190313 | 26190361 | Hyper | liver_tcga, literature | MIR663A, LOC284801 | chr20 | 30582750 | 30582978 | Hyper | cancer_general | XKR7 |
| chr20 | 30639141 | 30639319 | Hyper | cancer_general, literature | HCK | chr20 | 30639632 | 30639847 | Hyper | cancer_general | HCK |
| chr20 | 30640106 | 30640270 | Hyper | tcga | HCK | chr20 | 30778024 | 30778313 | Hyper | tcga, liver_tcga, cancer_general | TSPY26P, PLAGL2 |
| chr20 | 34188617 | 34189391 | Hyper | cancer_general | FER1L4 | chr20 | 34189635 | 34189910 | Hyper | cancer_general | FER1L4 |
| chr20 | 36531799 | 36531910 | Hyper | colorectal | VSTM2L | chr20 | 36781324 | 36781354 | Hyper | cancer_general | TGM2, HV531029, HV530979, HV531015, HV531014, HV531011, HV531005 |
| chr20 | 37302697 | 37303343 | Hyper | cancer_general, tcga | | chr20 | 37351793 | 37352626 | Hyper | cancer_general | SLC32A1 |
| chr20 | 37353193 | 37353236 | Hyper | cancer_general | SLC32A1 | chr20 | 37353455 | 37353779 | Hyper | cancer_general | SLC32A1 |
| chr20 | 37354145 | 37355202 | Hyper | cancer_general | SLC32A1 | chr20 | 37355847 | 37357353 | Hyper | cancer_general | SLC32A1 |
| chr20 | 37357825 | 37358190 | Hyper | cancer_general | SLC32A1 | chr20 | 37434552 | 37434744 | Hyper | colorectal | PPP1R16B |
| chr20 | 37435104 | 37435218 | Hyper | tcga | PPP1R16B | chr20 | 37435461 | 37435860 | Hyper | colorectal | PPP1R16B |
| chr20 | 39316203 | 39316322 | Hyper | tcga | MAFB | chr20 | 39316893 | 39317392 | Hyper | cancer_general | MAFB |
| chr20 | 39317750 | 39318166 | Hyper | esophageal | MAFB | chr20 | 39318383 | 39318415 | Hyper | esophageal | MAFB |
| chr20 | 39319126 | 39319653 | Hyper | tcga, cancer_general | MAFB | chr20 | 39995146 | 39995813 | Hyper | cancer_general | EMILIN3, LPIN3 |
| chr20 | 40743859 | 40743888 | Hyper | literature | PTPRT | chr20 | 41817786 | 41818085 | Hyper | tcga, cancer_general | |
| chr20 | 41818567 | 41818914 | Hyper | cancer_general | | chr20 | 42136330 | 42136411 | Hyper | cancer_general | L3MBTL1 |
| chr20 | 42543754 | 42543853 | Hyper | cancer_general | TOX2 | chr20 | 42544091 | 42544984 | Hyper | cancer_general | TOX2 |
| chr20 | 42876525 | 42876575 | Hyper | cancer_general | GDAP1L1 | chr20 | 43438071 | 43438466 | Hyper | cancer_general | RIMS4 |
| chr20 | 43438982 | 43439022 | Hyper | cancer_general | RIMS4 | chr20 | 43439291 | 43439510 | Hyper | cancer_general | RIMS4 |
| chr20 | 44452731 | 44453063 | Hyper | lung, cancer_general | SNX21, TNNC2, UBE2C | chr20 | 44519077 | 44519107 | Hyper | cancer_general | PLTP, NEURL2, SPATA25, ZSWIM1, CTSA |
| chr20 | 44639181 | 44639496 | Hyper | cancer_general | MMP9 | chr20 | 44640338 | 44640367 | Hyper | literature | SLC12A5, MMP9 |
| chr20 | 44660750 | 44660877 | Hyper | cancer_general | SLC12A5 | chr20 | 44686190 | 44686762 | Hyper | cancer_general | NCOA5, SLC12A5 |
| chr20 | 44746484 | 44746781 | Hyper | tcga | CD40 | chr20 | 44803174 | 44803675 | Hyper | cancer_general | CDH22 |
| chr20 | 44875240 | 44875411 | Hyper | cancer_general | | chr20 | 44879801 | 44880076 | Hyper | cancer_general | |
| chr20 | 44937202 | 44937643 | Hyper | tcga, cancer_general | | chr20 | 44941518 | 44941661 | Hyper | cancer_general | |
| chr20 | 45142000 | 45142272 | Hyper | tcga, cancer_general | ZNF334 | chr20 | 45279854 | 45280302 | Hyper | cancer_general, tcga | SLC13A3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 45524523 | 45524553 | Hyper | cancer_general | EYA2 | chr20 | 47443729 | 47444282 | Hyper | cancer_general | |
| chr20 | 47934824 | 47935268 | Hyper | cancer_general | | chr20 | 47935495 | 47935567 | Hyper | cancer_general | PTGIS |
| chr20 | 47935928 | 47936027 | Hyper | cancer_general | | chr20 | 48184381 | 48184435 | Hyper | cancer_general | KCNG1 |
| chr20 | 49575909 | 49575939 | Hyper | cancer_general | MOCS3, DPM1 | chr20 | 49639777 | 49640157 | Hyper | tcga, cancer_general | |
| chr20 | 50384767 | 50384896 | Hyper | blood | ATP9A | chr20 | 50720437 | 50722193 | Hyper | tcga, cancer_general, liver_tcga | ZFP64 |
| chr20 | 50722598 | 50722821 | Hyper | cancer_general, liver_tcga | ZFP64 | chr20 | 51589766 | 51589908 | Hyper | cancer_general | TSHZ2 |
| chr20 | 52226337 | 52226366 | Hyper | literature | | chr20 | 52311483 | 52311602 | Hyper | pancreas | |
| chr20 | 52789445 | 52789475 | Hyper | cancer_general | CYP24A1 | chr20 | 52789853 | 52790155 | Hyper | tcga, liver_tcga, cancer_general | CYP24A1 |
| chr20 | 53092192 | 53092376 | Hyper | cancer_general | DOK5 | chr20 | 53093085 | 53093115 | Hyper | cancer_general | DOK5 |
| chr20 | 54578507 | 54578725 | Hyper | cancer_general | CBLN4 | chr20 | 54579892 | 54580323 | Hyper | cancer_general | CBLN4 |
| chr20 | 54580574 | 54580691 | Hyper | literature, cancer_general | CBLN4 | chr20 | 55200035 | 55200706 | Hyper | cancer_general | TFAP2C |
| chr20 | 55200922 | 55201092 | Hyper | cancer_general | TFAP2C | chr20 | 55201486 | 55201549 | Hyper | cancer_general | TFAP2C |
| chr20 | 55201764 | 55202626 | Hyper | cancer_general | TFAP2C | chr20 | 55202826 | 55203107 | Hyper | cancer_general | TFAP2C |
| chr20 | 55204322 | 55204604 | Hyper | cancer_general | TFAP2C | chr20 | 55204966 | 55205000 | Hyper | cancer_general | TFAP2C |
| chr20 | 55206056 | 55206393 | Hyper | cancer_general | TFAP2C | chr20 | 55206739 | 55206774 | Hyper | cancer_general | TFAP2C |
| chr20 | 55499496 | 55499709 | Hyper | cancer_general | | chr20 | 55500016 | 55500085 | Hyper | cancer_general | |
| chr20 | 55500410 | 55500949 | Hyper | cancer_general | | chr20 | 55841134 | 55841356 | Hyper | tcga | BC037891, BMP7 |
| chr20 | 55842096 | 55842189 | Hyper | cancer_general | BC037891, BMP7 | chr20 | 56803398 | 56803441 | Hyper | cancer_general | PPP4R1L |
| chr20 | 56803842 | 56803920 | Hyper | cancer_general | PPP4R1L | chr20 | 57089452 | 57089496 | Hyper | cancer_general | APCDD1L-AS1, APCDD1L |
| chr20 | 57089804 | 57090173 | Hyper | cancer_general | APCDD1L-AS1, APCDD1L | chr20 | 57224842 | 57225307 | Hyper | cancer_general | STX16 |
| chr20 | 57484406 | 57484445 | Hyper | literature | GNAS | chr20 | 58152637 | 58152714 | Hyper | cancer_general | PHACTR3 |
| chr20 | 58179809 | 58179854 | Hyper | cancer_general | PHACTR3 | chr20 | 58180099 | 58180414 | Hyper | cancer_general | PHACTR3 |
| chr20 | 58508887 | 58508943 | Hyper | liver_tcga | PPP1R3D, FAM217B | chr20 | 59804170 | 59804235 | Hyper | pancreas | |
| chr20 | 59826962 | 59827226 | Hyper | literature, cancer_general | CDH4 | chr20 | 59827795 | 59828446 | Hyper | literature, cancer_general | CDH4 |
| chr20 | 61340581 | 61340689 | Hyper | cancer_general | NTSR1 | chr20 | 61560418 | 61560922 | Hyper | cancer_general | GID8 |
| chr20 | 61585771 | 61586004 | Hyper | cancer_general | SLC17A9, GID8 | chr20 | 61636858 | 61636890 | Hyper | cancer_general | BHLHE23, LOC63930 |
| chr20 | 61637468 | 61638631 | Hyper | cancer_general | LOC63930, BHLHE23 | chr20 | 61703709 | 61703875 | Hyper | cancer_general | CDH4 |
| chr20 | 61734420 | 61734481 | Hyper | cancer_general | HAR1A, HAR1B | chr20 | 61747894 | 61747934 | Hyper | cancer_general | |
| chr20 | 61808181 | 61808270 | Hyper | cancer_general | MIR124-3 | chr20 | 61808485 | 61810089 | Hyper | tcga, cancer_general | MIR124-3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 61862380 | 61862452 | Hyper | cancer_general | BIRC7, MIR3196, NKAIN4 | chr20 | 61885247 | 61885462 | Hyper | tcga | FLJ16779, NKAIN4 |
| chr20 | 61885712 | 61885744 | Hyper | cancer_general | FLJ16779, NKAIN4 | chr20 | 61886068 | 61886258 | Hyper | cancer_general | FLJ16779, NKAIN4 |
| chr20 | 61886725 | 61886755 | Hyper | cancer_general | FLJ16779, NKAIN4 | chr20 | 62058700 | 62058786 | Hyper | cancer_general | KCNQ2 |
| chr20 | 62119339 | 62120171 | Hyper | cancer_general | EEF1A2 | chr20 | 62185386 | 62185444 | Hyper | tcga, liver_tcga | C20orf195, HELZ2, SRMS |
| chr20 | 62284487 | 62284615 | Hyper | liver_tcga | RTEL1, RTEL1-TNFRSF6B, STMN3 | chr20 | 62461349 | 62461475 | Hyper | cancer_general | BC002534, ZBTB46 |
| chr20 | 62680657 | 62680739 | Hyper | esophageal | TCEA2, SOX18, LINC00176 | chr20 | 62715014 | 62715069 | Hyper | esophageal | OPRL1, C20orf201, RGS19 |
| chr16 | 215416 | 216224 | Hyper | cancer_general | HBM, HBA2 | chr16 | 216676 | 217036 | Hyper | cancer_general | HBA2, HBA1, HBM |
| chr16 | 230265 | 230610 | Hyper | tcga, liver_tcga, cancer_general | LUC7L, HBA1, HBA2, HBQ1 | chr16 | 565492 | 565623 | Hyper | liver_tcga | RAB11FIP3 |
| chr16 | 1030302 | 1030655 | Hyper | tcga, cancer_general | SOX8, LMF1 | chr16 | 1122858 | 1122951 | Hyper | tcga | BC084558, SSTR5, SSTR5-AS1 |
| chr16 | 1203970 | 1204034 | Hyper | cancer_general | CACNA1H IGFALS, NUBP2, SPSB3 | chr16 | 1382901 | 1382940 | Hyper | cancer_general | BAIAP3 |
| chr16 | 1842490 | 1842519 | Hyper | liver_tcga | | chr16 | 2040914 | 2042160 | Hyper | cancer_general | ZNF598, SYNGR3, GFER, NOXO1 |
| chr16 | 2086831 | 2086860 | Hyper | liver_tcga | NTHL1, SLC9A3R2 | chr16 | 2106703 | 2106732 | Hyper | literature | TSC2, NTHL1 |
| chr16 | 2111966 | 2111995 | Hyper | literature | TSC2 | chr16 | 2120515 | 2120544 | Hyper | literature | TSC2 |
| chr16 | 2122243 | 2122272 | Hyper | literature | | chr16 | 2124205 | 2124348 | Hyper | literature | TSC2, |
| chr16 | 2126080 | 2126109 | Hyper | literature | TSC2 | chr16 | 2130361 | 2130390 | Hyper | literature | PKD1, MIR1225 |
| chr16 | 2132244 | 2132315 | Hyper | liver_tcga | TSC2, PKD1, MIR1225 | chr16 | 2135301 | 2135330 | Hyper | literature | PKD1, MIR1225, TSC2 |
| chr16 | 2136228 | 2136257 | Hyper | literature | TSC2, PKD1, MIR1225 | chr16 | 2136727 | 2136855 | Hyper | literature | PKD1, MIR1225, TSC2 |
| chr16 | 2140403 | 2140438 | Hyper | liver_tcga | PKD1, MIR1225, TSC2 | chr16 | 2287295 | 2287370 | Hyper | cancer_general | ECI1, DNASE1L2, E4F1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 2892542 | 2892729 | Hyper | cancer_general | PRSS22, PRSS30P | chr16 | 3017052 | 3017628 | Hyper | cancer_general | PAQR4, PKMYT1, KREMEN2 |
| chr16 | 3068171 | 3068201 | Hyper | cancer_general | TNFRSF12A, HCFC1R1, THOC6, CCDC64B, CLDN6, CLDN9 | chr16 | 3220566 | 3222239 | Hyper | cancer_general, tcga | TRNA_Pro, TRNA_Lys, TRNA_Pseudo |
| chr16 | 3225471 | 3225607 | Hyper | cancer_general | TRNA_Lys, TRNA_Pro, TRNA_Pseudo | chr16 | 3232739 | 3234452 | Hyper | liver_tcga, cancer_general | TRNA_Pro, TRNA_Lys, TRNA_Arg |
| chr16 | 3237857 | 3238546 | Hyper | liver_tcga, cancer_general | TRNA_Pro, TRNA_Lys, TRNA_Arg, TRNA_Pseudo | chr16 | 3238993 | 3239848 | Hyper | tcga, cancer_general | TRNA_Pro, TRNA_Lys, TRNA_Arg, TRNA_Pseudo |
| chr16 | 3241549 | 3241663 | Hyper | cancer_general | TRNA_Pseudo, TRNA_Lys, TRNA_Pro, TRNA_Arg | chr16 | 3241936 | 3241966 | Hyper | cancer_general | TRNA_Arg, TRNA_Pseudo, TRNA_Lys, TRNA_Pro |
| chr16 | 3355279 | 3355718 | Hyper | cancer_general | ZNF75A, TIGD7, ZNF263 | chr16 | 4431487 | 4431516 | Hyper | liver_tcga | VASN, CORO7-PAM16, CORO7 |
| chr16 | 4731638 | 4731718 | Hyper | liver_tcga | NUDT16L1, ANKS3 | chr16 | 4733166 | 4733195 | Hyper | liver_tcga | ANKS3, NUDT16L1 |
| chr16 | 4738567 | 4738680 | Hyper | liver_tcga | | chr16 | 4751554 | 4751583 | Hyper | liver_tcga | RBFOX1 |
| chr16 | 5037900 | 5038004 | Hyper | cancer_general | SEC14L5 | chr16 | 6069925 | 6070019 | Hyper | cancer_general | GRIN2A |
| chr16 | 7354634 | 7354664 | Hyper | cancer_general | RBFOX1 | chr16 | 9107184 | 9107213 | Hyper | cancer_general, liver_tcga, literature | GRIN2A |
| chr16 | 10274399 | 10274429 | Hyper | cancer_general | GRIN2A | chr16 | 10275308 | 10275392 | Hyper | cancer_general, tcga | GRIN2A |
| chr16 | 10275752 | 10275948 | Hyper | tcga | GRIN2A | chr16 | 10276360 | 10277437 | Hyper | cancer_general, tcga, colorectal | |
| chr16 | 10479815 | 10479980 | Hyper | cancer_general | ATF7IP2 | chr16 | 12994459 | 12994737 | Hyper | cancer_general, tcga | SHISA9 |
| chr16 | 12995062 | 12995593 | Hyper | cancer_general, tcga | SHISA9 | chr16 | 12995803 | 12996328 | Hyper | cancer_general | SHISA9 |
| chr16 | 12996617 | 12996720 | Hyper | cancer_general | SHISA9 | chr16 | 12996948 | 12997011 | Hyper | pancreas | SHISA9 |
| chr16 | 12997386 | 12997703 | Hyper | cancer_general | SHISA9 | chr16 | 14021974 | 14022003 | Hyper | literature | ERCC4 |
| chr16 | 14041504 | 14041533 | Hyper | literature | ERCC4 | chr16 | 14041795 | 14041824 | Hyper | literature | ERCC4 |
| chr16 | 14042062 | 14042091 | Hyper | literature | ERCC4 | chr16 | 15489599 | 15489808 | Hyper | tcga | MPV17L |
| chr16 | 19567202 | 19567449 | Hyper | cancer_general | C16orf62, CCP110 | chr16 | 19895125 | 19895155 | Hyper | cancer_general | GPRC5B |
| chr16 | 21831621 | 21831957 | Hyper | tcga | RRN3P1 | chr16 | 22824701 | 22825094 | Hyper | cancer_general | HS3ST2 |
| chr16 | 22825327 | 22826081 | Hyper | cancer_general | HS3ST2 | chr16 | 23313464 | 23313522 | Hyper | esophageal | SCNN1B |
| chr16 | 23313749 | 23313836 | Hyper | esophageal | SCNN1B | chr16 | 23706317 | 23706520 | Hyper | cancer_general | ERN2, PLK1 |
| chr16 | 23766097 | 23766130 | Hyper | tcga | CHP2 | chr16 | 23847309 | 23847956 | Hyper | liver_tcga, cancer_general | PRKCB |
| chr16 | 24267115 | 24267208 | Hyper | cancer_general | CACNG3 | chr16 | 24267485 | 24267578 | Hyper | cancer_general | CACNG3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 25702955 | 25702992 | Hyper | cancer_general | HS3ST4 | chr16 | 25703642 | 25704628 | Hyper | cancer_general, tcga | HS3ST4 |
| chr16 | 28074176 | 28074684 | Hyper | tcga, cancer_general | | chr16 | 28074959 | 28075197 | Hyper | tcga | |
| chr16 | 28891040 | 28891072 | Hyper | esophageal | SH2B1, PAT2A1, LOC100289092 | chr16 | 29888136 | 29888227 | Hyper | cancer_general | SEZ6L2, CDIPT-AS1 |
| chr16 | 29888624 | 29888658 | Hyper | cancer_general | SEZ6L2, CDIPT-AS1 | chr16 | 31227914 | 31228313 | Hyper | tcga, cancer_general | PYDC1, TRIM72 |
| chr16 | 31580560 | 31581036 | Hyper | literature, cancer_general | YBX3P1 | chr16 | 47177525 | 47177606 | Hyper | hepatobiliary | |
| chr16 | 48844792 | 48845125 | Hyper | cancer_general | | chr16 | 49309170 | 49309262 | Hyper | cancer_general | CBLN1 |
| chr16 | 49311523 | 49312299 | Hyper | cancer_general | CBLN1 | chr16 | 49313363 | 49313710 | Hyper | cancer_general | CBLN1 |
| chr16 | 49314022 | 49314118 | Hyper | cancer_general | CBLN1 | chr16 | 49314419 | 49314561 | Hyper | cancer_general | CBLN1 |
| chr16 | 49314784 | 49314837 | Hyper | cancer_general | CBLN1 | chr16 | 49315276 | 49315306 | Hyper | cancer_general | CBLN1 |
| chr16 | 49315919 | 49316580 | Hyper | cancer_general | CBLN1 | chr16 | 51183900 | 51184406 | Hyper | cancer_general | SALL1 |
| chr16 | 51184807 | 51185360 | Hyper | literature, cancer_general | SALL1 | chr16 | 51185844 | 51186280 | Hyper | tcga, cancer_general | SALL1 |
| chr16 | 51186592 | 51186939 | Hyper | cancer_general | SALL1 | chr16 | 51188682 | 51188711 | Hyper | literature | SALL1 |
| chr16 | 51189922 | 51190215 | Hyper | cancer_general | SALL1 | chr16 | 54318898 | 54318988 | Hyper | cancer_general | IRX3 |
| chr16 | 54319420 | 54319468 | Hyper | cancer_general | IRX3 | chr16 | 54321638 | 54321834 | Hyper | cancer_general | IRX3 |
| chr16 | 54324999 | 54325131 | Hyper | cancer_general | IRX3 | chr16 | 54628691 | 54628867 | Hyper | cancer_general | IRX5, CRNDE |
| chr16 | 54964948 | 54965114 | Hyper | blood | IRX5, CRNDE | chr16 | 54966830 | 54967403 | Hyper | liver_tcga, cancer_general | IRX5, CRNDE |
| chr16 | 54971060 | 54971090 | Hyper | cancer_general | IRX5, CRNDE | chr16 | 54971400 | 54971430 | Hyper | cancer_general | IRX6 |
| chr16 | 55090666 | 55090861 | Hyper | cancer_general | IRX6 | chr16 | 55357926 | 55358086 | Hyper | cancer_general | IRX6 |
| chr16 | 55358316 | 55358528 | Hyper | cancer_general | IRX6 | chr16 | 55358798 | 55359071 | Hyper | cancer_general | IRX6 |
| chr16 | 55363009 | 55363223 | Hyper | cancer_general | IRX6 | chr16 | 55364716 | 55364843 | Hyper | cancer_general | IRX6 |
| chr16 | 55365103 | 55365234 | Hyper | cancer_general | MMP2 | chr16 | 55404999 | 55405214 | Hyper | tcga | SLC6A2 |
| chr16 | 55512843 | 55512884 | Hyper | tcga, cancer_general | SLC6A2 | chr16 | 55689886 | 55689915 | Hyper | tcga | GNAO1, DKFZP434H168, LOC283856 |
| chr16 | 55690115 | 55690809 | Hyper | | | chr16 | 56224557 | 56224879 | Hyper | cancer_general | |
| chr16 | 56228370 | 56228581 | Hyper | cancer_general | DKFZP434H168, GNAO1, LOC283856 | chr16 | 56651094 | 56651275 | Hyper | cancer_general | MT1L, MT1M, MT1E, MT1A, MT2A |
| chr16 | 56659175 | 56659673 | Hyper | cancer_general | MT1E, MT1M, MT1JP, MT1L, MT1A | chr16 | 56672158 | 56672654 | Hyper | tcga, cancer_general | MT1A, MT1DP, MT1JP, MT1M |
| chr16 | 56709837 | 56710030 | Hyper | cancer_general | MT1G, MTE, MT1X, MT1IP, MT1H | chr16 | 57318379 | 57318412 | Hyper | blood | PLLP |
| chr16 | 58018634 | 58018845 | Hyper | cancer_general | ZNF319, TEPP | chr16 | 58019225 | 58019430 | Hyper | cancer_general | ZNF319, TEPP |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 58497221 | 58497409 | Hyper | literature | NDRG4 | chr16 | 58497752 | 58497829 | Hyper | literature | NDRG4 |
| chr16 | 58498175 | 58498204 | Hyper | literature | NDRG4 | chr16 | 58498570 | 58498724 | Hyper | literature | NDRG4 |
| chr16 | 58521708 | 58521737 | Hyper | literature | NDRG4 | chr16 | 58534666 | 58534695 | Hyper | literature | |
| chr16 | 62068463 | 62068517 | Hyper | cancer_general | | chr16 | 62068952 | 62068982 | Hyper | cancer_general | |
| chr16 | 62070743 | 62070773 | Hyper | cancer_general | | chr16 | 65154933 | 65155091 | Hyper | cancer_general | BEAN1 |
| chr16 | 65156385 | 65156489 | Hyper | cancer_general, tcga | CMTM2, CMTM1 | chr16 | 66461786 | 66461840 | Hyper | cancer_general | HSF4, NOL3, FBXL8, TRADD |
| chr16 | 66612882 | 66613369 | Hyper | cancer_general | | chr16 | 67197698 | 67197769 | Hyper | cancer_general | |
| chr16 | 67198009 | 67198039 | Hyper | cancer_general | HSF4, NOL3, FBXL8, TRADD | chr16 | 67198917 | 67198957 | Hyper | cancer_general | HSF4, FBXL8, TRADD, NOL3 |
| chr16 | 68481486 | 68481543 | Hyper | liver_tcga | SMPD3 | chr16 | 68482808 | 68482941 | Hyper | liver_tcga | SMPD3 |
| chr16 | 68544259 | 68544378 | Hyper | cancer_general | | chr16 | 68676408 | 68676984 | Hyper | cancer_general | CDH3 |
| chr16 | 68770966 | 68771298 | Hyper | literature, blood | CDH1 | chr16 | 68844158 | 68844187 | Hyper | literature | CDH1 |
| chr16 | 68846033 | 68846062 | Hyper | literature | CDH1 | chr16 | 68856078 | 68856107 | Hyper | literature | CDH1 |
| chr16 | 71460027 | 71460351 | Hyper | cancer_general | TRNA_Met | chr16 | 73100460 | 73100524 | Hyper | cancer_general | VAT1L |
| chr16 | 77468261 | 77468775 | Hyper | cancer_general | ADAMTS18 | chr16 | 77822589 | 77822874 | Hyper | cancer_general | MAF |
| chr16 | 78079969 | 78080054 | Hyper | cancer_general | | chr16 | 79623602 | 79623914 | Hyper | tcga, lung, cancer_general | |
| chr16 | 80837962 | 80838143 | Hyper | esophageal | CDYL2 | chr16 | 80966399 | 80966431 | Hyper | blood | |
| chr16 | 81946246 | 81946275 | Hyper | literature | PLCG2 | chr16 | 81962167 | 81962196 | Hyper | literature | PLCG2 |
| chr16 | 82660360 | 82660496 | Hyper | cancer_general, literature | CDH13 | chr16 | 82660712 | 82660741 | Hyper | literature | CDH13 |
| chr16 | 84402244 | 84402319 | Hyper | blood | ATP2C2 | chr16 | 84651793 | 84651822 | Hyper | liver_tcga | COTL1 |
| chr16 | 84853288 | 84853376 | Hyper | blood | CRISPLD2 | chr16 | 85932828 | 85932858 | Hyper | cancer_general | IRF8 |
| chr16 | 86320354 | 86320391 | Hyper | cancer_general | LOC146513 | chr16 | 86320755 | 86320800 | Hyper | cancer_general | LOC146513 |
| chr16 | 86321020 | 86321068 | Hyper | cancer_general | LOC146513 | chr16 | 86530947 | 86531046 | Hyper | cancer_general | FENDRR |
| chr16 | 86531310 | 86531573 | Hyper | cancer_general | FENDRR | chr16 | 86541591 | 86541968 | Hyper | cancer_general | FOXF1, FENDRR |
| chr16 | 86542373 | 86542457 | Hyper | cancer_general | FOXF1, FENDRR | chr16 | 86544191 | 86544972 | Hyper | cancer_general | FENDRR, FOXF1 |
| chr16 | 86599477 | 86599844 | Hyper | cancer_general | FOXC2, FLJ30679 | chr16 | 86600483 | 86600686 | Hyper | cancer_general | FLJ30679, FOXC2 |
| chr16 | 86600958 | 86601015 | Hyper | cancer_general | FOXC2 | chr16 | 86601286 | 86601539 | Hyper | cancer_general | FOXC2 |
| chr16 | 86601945 | 86602514 | Hyper | cancer_general | FOXC2, FOXL1 | chr16 | 86613052 | 86613108 | Hyper | tcga | FOXL1 |
| chr16 | 87525622 | 87525701 | Hyper | blood | BC131758 | chr16 | 87635103 | 87635133 | Hyper | cancer_general | JPH3 |
| chr16 | 87636518 | 87636907 | Hyper | cancer_general, tcga | JPH3 | chr16 | 88543428 | 88543458 | Hyper | liver_tcga | MIR5189, ZFPM1 |
| chr16 | 89007520 | 89007558 | Hyper | pancreas | CBFA2T3 | chr16 | 89007880 | 89007995 | Hyper | esophageal | CBFA2T3 |
| chr16 | 89008562 | 89008592 | Hyper | pancreas | CBFA2T3 | chr16 | 89267334 | 89267364 | Hyper | cancer_general | CDH15 |
| chr16 | 89267808 | 89267847 | Hyper | cancer_general | SLC22A31, CDH15 | JH636052.4 | 5118769 | 5118903 | Hyper | | SLC22A31 |
| EBV-B95-8 | 967 | 996 | Hyper | virus | | EBV-B95-8 | 3766 | 3795 | Hyper | virus | |
| EBV-B95-8 | 4234 | 4263 | Hyper | virus | | EBV-B95-8 | 5326 | 5355 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| EBV-B95-8 | 6553 | 6582 | Hyper | virus | | EBV-B95-8 | 8800 | 8829 | Hyper | virus | |
| EBV-B95-8 | 13471 | 13500 | Hyper | virus | | EBV-B95-8 | 46577 | 46606 | Hyper | virus | |
| EBV-B95-8 | 48222 | 48251 | Hyper | virus | | EBV-B95-8 | 52842 | 52871 | Hyper | virus | |
| EBV-B95-8 | 53561 | 53590 | Hyper | virus | | EBV-B95-8 | 54377 | 54406 | Hyper | virus | |
| EBV-B95-8 | 54778 | 54807 | Hyper | virus | | EBV-B95-8 | 55067 | 55096 | Hyper | virus | |
| EBV-B95-8 | 55893 | 55922 | Hyper | virus | | EBV-B95-8 | 56735 | 56764 | Hyper | virus | |
| EBV-B95-8 | 58227 | 58256 | Hyper | virus | | EBV-B95-8 | 58926 | 58955 | Hyper | virus | |
| EBV-B95-8 | 59581 | 59610 | Hyper | virus | | EBV-B95-8 | 60099 | 60128 | Hyper | virus | |
| EBV-B95-8 | 60877 | 60906 | Hyper | virus | | EBV-B95-8 | 61319 | 61348 | Hyper | virus | |
| EBV-B95-8 | 62302 | 62331 | Hyper | virus | | EBV-B95-8 | 62840 | 62869 | Hyper | virus | |
| EBV-B95-8 | 63178 | 63207 | Hyper | virus | | EBV-B95-8 | 63601 | 63630 | Hyper | virus | |
| EBV-B95-8 | 63935 | 63964 | Hyper | virus | | EBV-B95-8 | 64590 | 64619 | Hyper | virus | |
| EBV-B95-8 | 66726 | 66755 | Hyper | virus | | EBV-B95-8 | 67486 | 67515 | Hyper | virus | |
| EBV-B95-8 | 67857 | 67886 | Hyper | virus | | EBV-B95-8 | 69228 | 69257 | Hyper | virus | |
| EBV-B95-8 | 69798 | 69827 | Hyper | virus | | EBV-B95-8 | 70439 | 70468 | Hyper | virus | |
| EBV-B95-8 | 70839 | 70868 | Hyper | virus | | EBV-B95-8 | 71938 | 71967 | Hyper | virus | |
| EBV-B95-8 | 72204 | 72233 | Hyper | virus | | EBV-B95-8 | 72535 | 72564 | Hyper | virus | |
| EBV-B95-8 | 72983 | 73012 | Hyper | virus | | EBV-B95-8 | 73950 | 73979 | Hyper | virus | |
| EBV-B95-8 | 74304 | 74333 | Hyper | virus | | EBV-B95-8 | 74689 | 74718 | Hyper | virus | |
| EBV-B95-8 | 74978 | 75007 | Hyper | virus | | EBV-B95-8 | 75256 | 75285 | Hyper | virus | |
| EBV-B95-8 | 77784 | 77813 | Hyper | virus | | EBV-B95-8 | 79618 | 79647 | Hyper | virus | |
| EBV-B95-8 | 80289 | 80318 | Hyper | virus | | EBV-B95-8 | 80704 | 80733 | Hyper | virus | |
| EBV-B95-8 | 81198 | 81227 | Hyper | virus | | EBV-B95-8 | 81629 | 81658 | Hyper | virus | |
| EBV-B95-8 | 81888 | 81917 | Hyper | virus | | EBV-B95-8 | 82225 | 82254 | Hyper | virus | |
| EBV-B95-8 | 82703 | 82732 | Hyper | virus | | EBV-B95-8 | 83438 | 83467 | Hyper | virus | |
| EBV-B95-8 | 85345 | 85374 | Hyper | virus | | EBV-B95-8 | 86299 | 86328 | Hyper | virus | |
| EBV-B95-8 | 87104 | 87133 | Hyper | virus | | EBV-B95-8 | 89959 | 89988 | Hyper | virus | |
| EBV-B95-8 | 90915 | 90944 | Hyper | virus | | EBV-B95-8 | 92531 | 92560 | Hyper | virus | |
| EBV-B95-8 | 94071 | 94100 | Hyper | virus | | EBV-B95-8 | 94731 | 94760 | Hyper | virus | |
| EBV-B95-8 | 95084 | 95113 | Hyper | virus | | EBV-B95-8 | 97482 | 97511 | Hyper | virus | |
| EBV-B95-8 | 98245 | 98274 | Hyper | virus | | EBV-B95-8 | 99224 | 99253 | Hyper | virus | |
| EBV-B95-8 | 100235 | 100264 | Hyper | virus | | EBV-B95-8 | 101009 | 101038 | Hyper | virus | |
| EBV-B95-8 | 102716 | 102745 | Hyper | virus | | EBV-B95-8 | 104004 | 104033 | Hyper | virus | |
| EBV-B95-8 | 105019 | 105048 | Hyper | virus | | EBV-B95-8 | 105284 | 105313 | Hyper | virus | |
| EBV-B95-8 | 107231 | 107260 | Hyper | virus | | EBV-B95-8 | 108023 | 108052 | Hyper | virus | |
| EBV-B95-8 | 108370 | 108399 | Hyper | virus | | EBV-B95-8 | 109086 | 109115 | Hyper | virus | |
| EBV-B95-8 | 110250 | 110279 | Hyper | virus | | EBV-B95-8 | 110626 | 110655 | Hyper | virus | |
| EBV-B95-8 | 111690 | 111719 | Hyper | virus | | EBV-B95-8 | 112112 | 112141 | Hyper | virus | |
| EBV-B95-8 | 114429 | 114458 | Hyper | virus | | EBV-B95-8 | 114749 | 114778 | Hyper | virus | |
| EBV-B95-8 | 115006 | 115035 | Hyper | virus | | EBV-B95-8 | 115597 | 115626 | Hyper | virus | |
| EBV-B95-8 | 116382 | 116411 | Hyper | virus | | EBV-B95-8 | 116649 | 116678 | Hyper | virus | |
| EBV-B95-8 | 118647 | 118676 | Hyper | virus | | EBV-B95-8 | 119542 | 119571 | Hyper | virus | |
| EBV-B95-8 | 120350 | 120379 | Hyper | virus | | EBV-B95-8 | 121382 | 121411 | Hyper | virus | |
| EBV-B95-8 | 123037 | 123066 | Hyper | virus | | EBV-B95-8 | 123570 | 123599 | Hyper | virus | |
| EBV-B95-8 | 124913 | 124942 | Hyper | virus | | EBV-B95-8 | 125376 | 125405 | Hyper | virus | |
| EBV-B95-8 | 125805 | 125834 | Hyper | virus | | EBV-B95-8 | 126337 | 126366 | Hyper | virus | |
| EBV-B95-8 | 127493 | 127522 | Hyper | virus | | EBV-B95-8 | 127905 | 127934 | Hyper | virus | |
| EBV-B95-8 | 128805 | 128834 | Hyper | virus | | EBV-B95-8 | 130244 | 130273 | Hyper | virus | |
| EBV-B95-8 | 130690 | 130719 | Hyper | virus | | EBV-B95-8 | 131603 | 131632 | Hyper | virus | |
| EBV-B95-8 | 134325 | 134354 | Hyper | virus | | EBV-B95-8 | 135032 | 135061 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| EBV-B95-8 | 135599 | 135628 | Hyper | virus | | EBV-B95-8 | 136148 | 136177 | Hyper | virus | |
| EBV-B95-8 | 136680 | 136709 | Hyper | virus | | EBV-B95-8 | 137805 | 137834 | Hyper | virus | |
| EBV-B95-8 | 138375 | 138404 | Hyper | virus | | EBV-B95-8 | 139745 | 139774 | Hyper | virus | |
| EBV-B95-8 | 140610 | 140639 | Hyper | virus | | EBV-B95-8 | 141137 | 141166 | Hyper | virus | |
| EBV-B95-8 | 142290 | 142319 | Hyper | virus | | EBV-B95-8 | 142763 | 142792 | Hyper | virus | |
| EBV-B95-8 | 143078 | 143107 | Hyper | virus | | EBV-B95-8 | 144318 | 144347 | Hyper | virus | |
| EBV-B95-8 | 145216 | 145245 | Hyper | virus | | EBV-B95-8 | 145638 | 145667 | Hyper | virus | |
| EBV-B95-8 | 147044 | 147073 | Hyper | virus | | EBV-B95-8 | 148404 | 148433 | Hyper | virus | |
| EBV-B95-8 | 150099 | 150128 | Hyper | virus | | EBV-B95-8 | 150443 | 150472 | Hyper | virus | |
| EBV-B95-8 | 152230 | 152259 | Hyper | virus | | EBV-B95-8 | 153127 | 153156 | Hyper | virus | |
| EBV-B95-8 | 153468 | 153497 | Hyper | virus | | EBV-B95-8 | 153800 | 153829 | Hyper | virus | |
| EBV-B95-8 | 154204 | 154233 | Hyper | virus | | EBV-B95-8 | 156501 | 156530 | Hyper | virus | |
| EBV-B95-8 | 156773 | 156802 | Hyper | virus | | EBV-B95-8 | 157345 | 157374 | Hyper | virus | |
| EBV-B95-8 | 159211 | 159240 | Hyper | virus | | EBV-B95-8 | 159561 | 159590 | Hyper | virus | |
| EBV-B95-8 | 161193 | 161222 | Hyper | virus | | EBV-B95-8 | 161698 | 161727 | Hyper | virus | |
| EBV-B95-8 | 162343 | 162372 | Hyper | virus | | EBV-B95-8 | 163798 | 163827 | Hyper | virus | |
| EBV-B95-8 | 164471 | 164500 | Hyper | virus | | EBV-B95-8 | 165234 | 165263 | Hyper | virus | |
| EBV-B95-8 | 166280 | 166309 | Hyper | virus | | EBV-B95-8 | 167347 | 167376 | Hyper | virus | |
| EBV-B95-8 | 167600 | 167629 | Hyper | virus | | EBV-B95-8 | 167942 | 167971 | Hyper | virus | |
| EBV-B95-8 | 168551 | 168580 | Hyper | virus | | EBV-B95-8 | 171304 | 171333 | Hyper | virus | |
| HHV5-CINCY-TOWNE | 1181 | 1210 | Hyper | virus | | HHV5-CINCY-TOWNE | 1988 | 2017 | Hyper | virus | |
| HHV5-CINCY-TOWNE | 2389 | 2418 | Hyper | virus | | HHV5-CINCY-TOWNE | 3290 | 3319 | Hyper | virus | |
| HHV5-CINCY-TOWNE | 3665 | 3694 | Hyper | virus | | HHV5-CINCY-TOWNE | 4704 | 4733 | Hyper | virus | |
| HHV5-CINCY-TOWNE | 5400 | 5429 | Hyper | virus | | HHV5-CINCY-TOWNE | 7790 | 7819 | Hyper | virus | |
| HHV5-CINCY-TOWNE | 9656 | 9685 | Hyper | virus | | HHV5-CINCY-TOWNE | 10781 | 10810 | Hyper | virus | |
| HHV5-CINCY-TOWNE | 11109 | 11138 | Hyper | virus | | HHV5 CINCY-TOWNE | 12663 | 12692 | Hyper | virus | |
| HHV5-CINCY-TOWNE | 13688 | 13717 | Hyper | virus | | HHV5-CINCY-TOWNE | 14223 | 14252 | Hyper | virus | |
| HHV5-CINCY-TOWNE | 14911 | 14940 | Hyper | virus | | HHV5-CINCY-TOWNE | 15206 | 15235 | Hyper | virus | |
| HHV5-CINCY-TOWNE | 15938 | 15967 | Hyper | virus | | HHV5-CINCY-TOWNE | 16440 | 16469 | Hyper | virus | |
| HHV5-CINCY-TOWNE | 16884 | 16913 | Hyper | virus | | HHV5-CINCY-TOWNE | 17347 | 17376 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 17696 | 17725 | Hyper | virus | | HHV5-CINCY-TOWNE | 17958 | 17987 | Hyper | virus | |
| HHV5-CINCY-TOWNE | 18372 | 18401 | Hyper | virus | | HHV5-CINCY-TOWNE | 19417 | 19446 | Hyper | virus | |
| HHV5-CINCY-TOWNE | 19910 | 19939 | Hyper | virus | | HHV5-CINCY-TOWNE | 20248 | 20277 | Hyper | virus | |
| HHV5-CINCY-TOWNE | 20671 | 20700 | Hyper | virus | | HHV5-CINCY-TOWNE | 21899 | 21928 | Hyper | virus | |
| HHV5-CINCY-TOWNE | 22798 | 22827 | Hyper | virus | | HHV5-CINCY-TOWNE | 23095 | 23124 | Hyper | virus | |
| HHV5-CINCY-TOWNE | 26713 | 26742 | Hyper | virus | | HHV5-CINCY-TOWNE | 27211 | 27240 | Hyper | virus | |
| HHV5-CINCY-TOWNE | 29784 | 29813 | Hyper | virus | | HHV5-CINCY-TOWNE | 31141 | 31170 | Hyper | virus | |
| HHV5-CINCY-TOWNE | 32660 | 32689 | Hyper | virus | | HHV5-CINCY-TOWNE | 35651 | 35680 | Hyper | virus | |
| HHV5-CINCY-TOWNE | 36393 | 36422 | Hyper | virus | | HHV5-CINCY-TOWNE | 37224 | 37253 | Hyper | virus | |
| HHV5-CINCY-TOWNE | 37895 | 37924 | Hyper | virus | | HHV5-CINCY-TOWNE | 39244 | 39273 | Hyper | virus | |
| HHV5-CINCY-TOWNE | 43188 | 43217 | Hyper | virus | | HHV5-CINCY-TOWNE | 44447 | 44476 | Hyper | virus | |
| HHV5-CINCY-TOWNE | 44799 | 44828 | Hyper | virus | | HHV5-CINCY-TOWNE | 45394 | 45423 | Hyper | virus | |
| HHV5-CINCY-TOWNE | 46445 | 46474 | Hyper | virus | | HHV5-CINCY-TOWNE | 46944 | 46973 | Hyper | virus | |
| HHV5-CINCY-TOWNE | 47916 | 47945 | Hyper | virus | | HHV5-CINCY-TOWNE | 48504 | 48533 | Hyper | virus | |
| HHV5-CINCY-TOWNE | 49094 | 49123 | Hyper | virus | | HHV5-CINCY-TOWNE | 49903 | 49932 | Hyper | virus | |
| HHV5-CINCY-TOWNE | 50230 | 50259 | Hyper | virus | | HHV5-CINCY-TOWNE | 51421 | 51450 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 53772 | 53801 | Hyper | virus | | HHV5-CINCY-TOWNE | 55651 | 55680 | Hyper | virus | |
| HHV5-CINCY-TOWNE | 56380 | 56409 | Hyper | virus | | HHV5-CINCY-TOWNE | 57291 | 57320 | Hyper | virus | |
| HHV5-CINCY-TOWNE | 58491 | 58520 | Hyper | virus | | HHV5-CINCY-TOWNE | 59023 | 59052 | Hyper | virus | |
| HHV5-CINCY-TOWNE | 59792 | 59821 | Hyper | virus | | HHV5-CINCY-TOWNE | 60124 | 60153 | Hyper | virus | |
| HHV5-CINCY-TOWNE | 60392 | 60421 | Hyper | virus | | HHV5-CINCY-TOWNE | 60900 | 60929 | Hyper | virus | |
| HHV5-CINCY-TOWNE | 63894 | 63923 | Hyper | virus | | HHV5-CINCY-TOWNE | 65843 | 65872 | Hyper | virus | |
| HHV5-CINCY-TOWNE | 68089 | 68118 | Hyper | virus | | HHV5-CINCY-TOWNE | 72454 | 72483 | Hyper | virus | |
| HHV5-CINCY-TOWNE | 81185 | 81214 | Hyper | virus | | HHV5-CINCY-TOWNE | 84144 | 84173 | Hyper | virus | |
| HHV5-CINCY-TOWNE | 85524 | 85553 | Hyper | virus | | HHV5-CINCY-TOWNE | 85943 | 85972 | Hyper | virus | |
| HHV5-CINCY-TOWNE | 86889 | 86918 | Hyper | virus | | HHV5-CINCY-TOWNE | 87195 | 87224 | Hyper | virus | |
| HHV5-CINCY-TOWNE | 87455 | 87484 | Hyper | virus | | HHV5-CINCY-TOWNE | 87769 | 87798 | Hyper | virus | |
| HHV5-CINCY-TOWNE | 88564 | 88593 | Hyper | virus | | HHV5-CINCY-TOWNE | 93096 | 93125 | Hyper | virus | |
| HHV5-CINCY-TOWNE | 93776 | 93805 | Hyper | virus | | HHV5-CINCY-TOWNE | 97621 | 97650 | Hyper | virus | |
| HHV5-CINCY-TOWNE | 98737 | 98766 | Hyper | virus | | HHV5-CINCY-TOWNE | 99460 | 99489 | Hyper | virus | |
| HHV5-CINCY-TOWNE | 107540 | 107569 | Hyper | virus | | HHV5-CINCY-TOWNE | 108823 | 108852 | Hyper | virus | |
| HHV5-CINCY-TOWNE | 109725 | 109754 | Hyper | virus | | HHV5-CINCY-TOWNE | 112036 | 112065 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 112319 | 112348 | Hyper | virus | | HHV5-CINCY-TOWNE | 112595 | 112624 | Hyper | virus | |
| HHV5-CINCY-TOWNE | 112892 | 112921 | Hyper | virus | | HHV5-CINCY-TOWNE | 113194 | 113223 | Hyper | virus | |
| HHV5-CINCY-TOWNE | 113535 | 113564 | Hyper | virus | | HHV5-CINCY-TOWNE | 113927 | 113956 | Hyper | virus | |
| HHV5-CINCY-TOWNE | 114267 | 114296 | Hyper | virus | | HHV5-CINCY-TOWNE | 114593 | 114622 | Hyper | virus | |
| HHV5-CINCY-TOWNE | 114867 | 114896 | Hyper | virus | | HHV5-CINCY-TOWNE | 115177 | 115206 | Hyper | virus | |
| HHV5-CINCY-TOWNE | 115432 | 115461 | Hyper | virus | | HHV5-CINCY-TOWNE | 115685 | 115714 | Hyper | virus | |
| HHV5-CINCY-TOWNE | 115986 | 116015 | Hyper | virus | | HHV5-CINCY-TOWNE | 116382 | 116411 | Hyper | virus | |
| HHV5-CINCY-TOWNE | 116700 | 116729 | Hyper | virus | | HHV5-CINCY-TOWNE | 118193 | 118222 | Hyper | virus | |
| HHV5-CINCY-TOWNE | 118995 | 119024 | Hyper | virus | | HHV5-CINCY-TOWNE | 120028 | 120057 | Hyper | virus | |
| HHV5-CINCY-TOWNE | 121485 | 121514 | Hyper | virus | | HHV5-CINCY-TOWNE | 122199 | 122228 | Hyper | virus | |
| HHV5-CINCY-TOWNE | 122606 | 122635 | Hyper | virus | | HHV5-CINCY-TOWNE | 124559 | 124588 | Hyper | virus | |
| HHV5-CINCY-TOWNE | 125276 | 125305 | Hyper | virus | | HHV5-CINCY-TOWNE | 132497 | 132526 | Hyper | virus | |
| HHV5-CINCY-TOWNE | 135460 | 135489 | Hyper | virus | | HHV5-CINCY-TOWNE | 135730 | 135759 | Hyper | virus | |
| HHV5-CINCY-TOWNE | 137379 | 137408 | Hyper | virus | | HHV5-CINCY-TOWNE | 139067 | 139096 | Hyper | virus | |
| HHV5-CINCY-TOWNE | 139472 | 139501 | Hyper | virus | | HHV5-CINCY-TOWNE | 140147 | 140176 | Hyper | virus | |
| HHV5-CINCY-TOWNE | 140722 | 140751 | Hyper | virus | | HHV5-CINCY-TOWNE | 142023 | 142052 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 143692 | 143721 | Hyper | virus | | HHV5-CINCY-TOWNE | 144080 | 144109 | Hyper | virus | |
| HHV5-CINCY-TOWNE | 147310 | 147339 | Hyper | virus | | HHV5-CINCY-TOWNE | 149465 | 149494 | Hyper | virus | |
| HHV5-CINCY-TOWNE | 150359 | 150388 | Hyper | virus | | HHV5-CINCY-TOWNE | 151593 | 151622 | Hyper | virus | |
| HHV5-CINCY-TOWNE | 152153 | 152182 | Hyper | virus | | HHV5-CINCY-TOWNE | 154148 | 154177 | Hyper | virus | |
| HHV5-CINCY-TOWNE | 154610 | 154639 | Hyper | virus | | HHV5-CINCY-TOWNE | 157018 | 157047 | Hyper | virus | |
| HHV5-CINCY-TOWNE | 157367 | 157396 | Hyper | virus | | HHV5-CINCY-TOWNE | 169038 | 169067 | Hyper | virus | |
| HHV5-CINCY-TOWNE | 171503 | 171532 | Hyper | virus | | HHV5-CINCY-TOWNE | 175146 | 175175 | Hyper | virus | |
| HHV5-CINCY-TOWNE | 177553 | 177582 | Hyper | virus | | HHV5-CINCY-TOWNE | 182254 | 182283 | Hyper | virus | |
| HHV5-CINCY-TOWNE | 183115 | 183144 | Hyper | virus | | HHV5-CINCY-TOWNE | 184120 | 184149 | Hyper | virus | |
| HHV5-CINCY-TOWNE | 185558 | 185587 | Hyper | virus | | HHV5-CINCY-TOWNE | 186027 | 186056 | Hyper | virus | |
| HHV5-CINCY-TOWNE | 186435 | 186464 | Hyper | virus | | HHV5-CINCY-TOWNE | 186707 | 186736 | Hyper | virus | |
| HHV5-CINCY-TOWNE | 187115 | 187144 | Hyper | virus | | HHV5-CINCY-TOWNE | 187514 | 187543 | Hyper | virus | |
| HHV5-CINCY-TOWNE | 187859 | 187888 | Hyper | virus | | HHV5-CINCY-TOWNE | 188473 | 188502 | Hyper | virus | |
| HHV5-CINCY-TOWNE | 188768 | 188797 | Hyper | virus | | HHV5-CINCY-TOWNE | 189050 | 189079 | Hyper | virus | |
| HHV5-CINCY-TOWNE | 189302 | 189331 | Hyper | virus | | HHV5-CINCY-TOWNE | 189936 | 189965 | Hyper | virus | |
| HHV5-CINCY-TOWNE | 190655 | 190684 | Hyper | virus | | HHV5-CINCY-TOWNE | 190954 | 190983 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 191453 | 191482 | Hyper | virus | | HHV5-CINCY-TOWNE | 191882 | 191911 | Hyper | virus | |
| HHV5-CINCY-TOWNE | 192183 | 192212 | Hyper | virus | | HHV5-CINCY-TOWNE | 192541 | 192570 | Hyper | virus | |
| HHV5-CINCY-TOWNE | 193045 | 193074 | Hyper | virus | | HHV5-CINCY-TOWNE | 193325 | 193354 | Hyper | virus | |
| HHV5-CINCY-TOWNE | 193597 | 193626 | Hyper | virus | | HHV5-CINCY-TOWNE | 194165 | 194194 | Hyper | virus | |
| HHV5-CINCY-TOWNE | 194461 | 194490 | Hyper | virus | | HHV5-CINCY-TOWNE | 194848 | 194877 | Hyper | virus | |
| HHV5-CINCY-TOWNE | 195324 | 195353 | Hyper | virus | | HHV5-CINCY-TOWNE | 195651 | 195680 | Hyper | virus | |
| HHV5-CINCY-TOWNE | 196018 | 196047 | Hyper | virus | | HHV5-CINCY-TOWNE | 196343 | 196372 | Hyper | virus | |
| HHV5-CINCY-TOWNE | 196941 | 196970 | Hyper | virus | | HHV5-CINCY-TOWNE | 197218 | 197247 | Hyper | virus | |
| HHV5-CINCY-TOWNE | 198315 | 198344 | Hyper | virus | | HHV5-CINCY-TOWNE | 198792 | 198821 | Hyper | virus | |
| HHV5-CINCY-TOWNE | 199162 | 199191 | Hyper | virus | | HHV5-CINCY-TOWNE | 200113 | 200142 | Hyper | virus | |
| HHV5-CINCY-TOWNE | 200571 | 200600 | Hyper | virus | | HHV5-CINCY-TOWNE | 201373 | 201402 | Hyper | virus | |
| HHV5-CINCY-TOWNE | 201905 | 201934 | Hyper | virus | | HHV5-CINCY-TOWNE | 202264 | 202293 | Hyper | virus | |
| HHV5-CINCY-TOWNE | 202537 | 202566 | Hyper | virus | | HHV5-CINCY-TOWNE | 203319 | 203348 | Hyper | virus | |
| HHV5-CINCY-TOWNE | 203720 | 203749 | Hyper | virus | | HHV5-CINCY-TOWNE | 204008 | 204037 | Hyper | virus | |
| HHV5-CINCY-TOWNE | 206213 | 206242 | Hyper | virus | | HHV5-CINCY-TOWNE | 206735 | 206764 | Hyper | virus | |
| HHV5-CINCY-TOWNE | 211676 | 211705 | Hyper | virus | | HHV5-CINCY-TOWNE | 212340 | 212369 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 212609 | 212638 | Hyper | virus | | HHV5-CINCY-TOWNE | 213813 | 213842 | Hyper | virus | |
| HHV5-CINCY-TOWNE | 214695 | 214724 | Hyper | virus | | HHV5-CINCY-TOWNE | 214950 | 214979 | Hyper | virus | |
| HHV5-CINCY-TOWNE | 215930 | 215959 | Hyper | virus | | HHV5-CINCY-TOWNE | 216228 | 216257 | Hyper | virus | |
| HHV5-CINCY-TOWNE | 222672 | 222701 | Hyper | virus | | HHV5-CINCY-TOWNE | 223515 | 223544 | Hyper | virus | |
| HHV5-CINCY-TOWNE | 225150 | 225179 | Hyper | virus | | HHV5-CINCY-TOWNE | 226058 | 226087 | Hyper | virus | |
| HHV5-CINCY-TOWNE | 226887 | 226916 | Hyper | virus | | chr11 | 406876 | 406939 | Hyper | cancer_general | SIGIRR, PKP3 |
| chr11 | 407427 | 407463 | Hyper | cancer_general | SIGIRR, PKP3 | chr11 | 533451 | 533567 | Hyper | literature | LRRC56, HRAS |
| chr11 | 533859 | 533888 | Hyper | literature | LRRC56, HRAS | chr11 | 534273 | 534302 | Hyper | literature | LRRC56, HRAS |
| chr11 | 611099 | 611128 | Hyper | liver_tcga | IRF7, CDHR5, PHRF1 | chr11 | 611691 | 611791 | Hyper | liver_tcga | IRF7, CDHR5, PHRF1 |
| chr11 | 627074 | 627189 | Hyper | literature, cancer_general | SCT, CDHR5 | chr11 | 636644 | 636673 | Hyper | literature | DRD4, DEAF1, SCT |
| chr11 | 636895 | 637441 | Hyper | tcga, cancer_general | DEAF1, SCT, DRD4 | chr11 | 679692 | 679722 | Hyper | liver_tcga | DEAF1 |
| chr11 | 726417 | 726466 | Hyper | cancer_general | EPS8L2 | chr11 | 829543 | 829708 | Hyper | cancer_general | CD151, EFCAB4A, PNPLA2, JB050151 |
| chr11 | 830174 | 830265 | Hyper | cancer_general | EFCAB4A, PNPLA2, JB050151, CD151, POLR2L | chr11 | 1318403 | 1318432 | Hyper | liver_tcga | TOLLIP |
| chr11 | 1358291 | 1358332 | Hyper | cancer_general tcga, cancer_general | CTSD, IFITM10 | chr11 | 1411875 | 1411905 | Hyper | cancer_general tcga | BRSK2 |
| chr11 | 1770051 | 1770248 | Hyper | | | chr11 | 2291259 | 2291768 | Hyper | cancer_general, liver_tcga | ASCL2 |
| chr11 | 2291984 | 2292636 | Hyper | liver_tcga, cancer_general | ASCL2 | chr11 | 2402376 | 2402405 | Hyper | liver_tcga | CD81, BC019904 |
| chr11 | 2465350 | 2465491 | Hyper | liver_tcga | KCNQ1 | chr11 | 2466597 | 2466788 | Hyper | liver_tcga | KCNQ1 |
| chr11 | 2884103 | 2884309 | Hyper | liver_tcga | KCNQ1DN | chr11 | 3181913 | 3181942 | Hyper | liver_tcga | |
| chr11 | 4209105 | 4209134 | Hyper | tcga | LOC100506082, RRM1 | chr11 | 7273286 | 7273375 | Hyper | cancer_general | SYT9 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 7274215 | 7274245 | Hyper | cancer_general | SYT9 | chr11 | 7695432 | 7695528 | Hyper | liver_tcga | CYB5R2 |
| chr11 | 8040536 | 8040770 | Hyper | tcga | TUB, BC027619 | chr11 | 8103002 | 8103115 | Hyper | tcga | TUB |
| chr11 | 8189987 | 8190766 | Hyper | cancer_general | RIC3 | chr11 | 8284535 | 8284760 | Hyper | tcga | LMO1 |
| chr11 | 8289517 | 8289745 | Hyper | cancer_general | LMO1 | chr11 | 8290195 | 8290423 | Hyper | tcga, cancer_general | LMO1 |
| chr11 | 8615674 | 8615704 | Hyper | liver_tcga | KRT8P41, MIR5691, SCUBE2 | chr11 | 9025970 | 9026348 | Hyper | cancer_general | NRIP3 |
| chr11 | 9112446 | 9112741 | Hyper | cancer_general |  | chr11 | 12029957 | 12030272 | Hyper | liver_tcga, cancer_general | DKK3 |
| chr11 | 12030823 | 12030852 | Hyper | liver_tcga | DKK3 | chr11 | 12132524 | 12132559 | Hyper | blood | MICAL2 |
| chr11 | 12399040 | 12399222 | Hyper | blood | PARVA | chr11 | 12399727 | 12399791 | Hyper | blood | PARVA |
| chr11 | 12695481 | 12695611 | Hyper | blood | TEAD1, DD413619 | chr11 | 12696611 | 12696746 | Hyper | blood | TEAD1, DD413619 |
| chr11 | 13030566 | 13030890 | Hyper | tcga, liver_tcga | RASSF10 | chr11 | 13690121 | 13690157 | Hyper | liver_tcga | FAR1 |
| chr11 | 14316375 | 14316404 | Hyper | literature | RRAS2 | chr11 | 15136085 | 15136394 | Hyper | tcga, cancer_general | INSC |
| chr11 | 16628819 | 16628933 | Hyper | blood | ABCC8 | chr11 | 16632493 | 16632670 | Hyper | cancer_general | MYOD1 |
| chr11 | 17497492 | 17497685 | Hyper | cancer_general, literature, | MYOD1 | chr11 | 17740493 | 17740570 | Hyper | cancer_general | MYOD1 |
| chr11 | 17741679 | 17742445 | Hyper | cancer_general |  | chr11 | 17743742 | 17743775 | Hyper | cancer_general |  |
| chr11 | 18812614 | 18812653 | Hyper | cancer_general | PTPN5 | chr11 | 18813032 | 18813086 | Hyper | cancer_general | PTPN5 |
| chr11 | 18813451 | 18813558 | Hyper | cancer_general | PTPN5 | chr11 | 18813792 | 18813947 | Hyper | cancer_general | PTPN5 |
| chr11 | 19263848 | 19263878 | Hyper | cancer_general | E2F8 | chr11 | 19367102 | 19367330 | Hype | tcga, cancer_general | NAV2 |
| chr11 | 19735730 | 19735760 | Hyper | cancer_general | NAV2, LOC100126784 | chr11 | 20153718 | 20153764 | Hyper | cancer_general |  |
| chr11 | 20178066 | 20178305 | Hyper | cancer_general | DBX1 | chr11 | 20180279 | 20180793 | Hyper | cancer_general, literature, | DBX1 |
| chr11 | 20181213 | 20181254 | Hyper | cancer_general | DBX1 | chr11 | 20181701 | 20181993 | Hyper | cancer_general | DBX1 |
| chr11 | 20182864 | 20182959 | Hyper | cancer_general | DBX1 | chr11 | 20183251 | 20183421 | Hyper | cancer_general | DBX1 |
| chr11 | 20183674 | 20183773 | Hyper | cancer_general | DBX1 | chr11 | 20184569 | 20185410 | Hyper | tcga, cancer_general | DBX1 |
| chr11 | 20229058 | 20229550 | Hyper | cancer_general | TRNA | chr11 | 20229863 | 20230091 | Hyper | cancer_general | TRNA |
| chr11 | 20230398 | 20230464 | Hyper | cancer_general | TRNA | chr11 | 20618197 | 20619172 | Hyper | literature, cancer_general, tcga, liver_tcga | SLC6A5 |
| chr11 | 20619717 | 20619974 | Hyper | cancer_general | SLC6A5 | chr11 | 20621341 | 20621644 | Hyper | cancer_general | SLC6A5 |
| chr11 | 20622705 | 20623359 | Hyper | cancer_general | SLC6A5 | chr11 | 20690653 | 20690935 | Hyper | cancer_general | NELL1 |
| chr11 | 20691219 | 20691452 | Hyper | cancer_general | NELL1 | chr11 | 20691685 | 20691914 | Hyper | cancer_general | NELL1 |
| chr11 | 20692453 | 20692529 | Hyper | cancer_general | NELL1 | chr11 | 22215123 | 22215287 | Hyper | cancer_general | ANO5 |
| chr11 | 22362934 | 22363189 | Hyper | cancer_general | SLC17A6 | chr11 | 22364821 | 22364975 | Hyper | cancer_general | SLC17A6 |
| chr11 | 22365407 | 22365477 | Hyper | cancer_general | SLC17A6 | chr11 | 27742185 | 27742215 | Hyper | cancer_general |  |
| chr11 | 27743115 | 27743173 | Hyper | cancer_general |  | chr11 | 27743436 | 27743608 | Hyper | cancer_general |  |
| chr11 | 27744147 | 27744504 | Hyper | cancer_general |  | chr11 | 27744711 | 27744744 | Hyper | cancer_general |  |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 30037593 | 30037743 | Hyper | cancer_general | KCNA4 | chr11 | 30038689 | 30038739 | Hyper | cancer_general | KCNA4 |
| chr11 | 30605919 | 30606123 | Hyper | cancer_general | MPPED2 | chr11 | 30606763 | 30606864 | Hyper | cancer_general | MPPED2 |
| chr11 | 30607367 | 30607409 | Hyper | cancer_general | MPPED2 | chr11 | 31818458 | 31818652 | Hyper | cancer_general | PAX6 |
| chr11 | 31819302 | 31819833 | Hyper | cancer_general | PAX6 | chr11 | 31820045 | 31821025 | Hyper | cancer_general | PAX6 |
| chr11 | 31821297 | 31821778 | Hyper | cancer_general | PAX6 | chr11 | 31822325 | 31822393 | Hyper | cancer_general | PAX6 |
| chr11 | 31824300 | 31824355 | Hyper | cancer_general | PAX6 | chr11 | 31824564 | 31824680 | Hyper | cancer_general | PAX6 |
| chr11 | 31825017 | 31825280 | Hyper | cancer_general | PAX6 | chr11 | 31825696 | 31827204 | Hyper | cancer_general | PAX6 |
| chr11 | 31827438 | 31828123 | Hyper | cancer_general | DKFZp686K1684, RCN1, PAX6 | chr11 | 31833097 | 31833155 | Hyper | cancer_general | DKFZp686K1684, RCN1 |
| chr11 | 31835707 | 31835797 | Hyper | cancer_general | DKFZp686K1684, RCN1, PAX6 | chr11 | 31836046 | 31836470 | Hyper | cancer_general | DKFZp686K1684, RCN1 |
| chr11 | 31837019 | 31838392 | Hyper | cancer_general | DKFZp686K1684, RCN1, PAX6 | chr11 | 31838678 | 31839051 | Hyper | cancer_general | RCN1, DKFZp686K1684 |
| chr11 | 31839307 | 31840080 | Hyper | cancer_general | RCN1, DKFZp686K1684 | chr11 | 31840587 | 31840922 | Hyper | cancer_general | RCN1, DKFZp686K1684 |
| chr11 | 31841376 | 31842276 | Hyper | cancer_general | RCN1, DKFZp686K1684 | chr11 | 31846022 | 31846230 | Hyper | cancer_general | RCN1, DKFZp686K1684 |
| chr11 | 31846434 | 31846985 | Hyper | literature, cancer_general | RCN1, DKFZp686K1684 | chr11 | 31847250 | 31847925 | Hyper | cancer_general | RCN1, DKFZp686K1684 |
| chr11 | 31848472 | 31849300 | Hyper | cancer_general | RCN1, DKFZp686K1684 | chr11 | 32009104 | 32009160 | Hyper | cancer_general | RCN1 |
| chr11 | 32354844 | 32355197 | Hyper | cancer_general | | chr11 | 32448583 | 32448979 | Hyper | tcga, cancer_general | WT1-AS, WT1 |
| chr11 | 32455602 | 32455634 | Hyper | tcga, cancer_general | WT1-AS, WT1 | chr11 | 32455841 | 32456025 | Hyper | cancer_general | WT1-AS, WT1 |
| chr11 | 32456279 | 32457176 | Hyper | tcga, cancer_general | WT1-AS, WT1 | chr11 | 32457712 | 32458175 | Hyper | tcga, cancer_general | WT1-AS, WT1 |
| chr11 | 32458389 | 32458823 | Hyper | cancer_general | WT1, WT1-AS | chr11 | 32459684 | 32460071 | Hyper | cancer_general | WT1, WT1-AS |
| chr11 | 32460468 | 32460515 | Hyper | cancer_general | WT1-AS, WT1 | chr11 | 32460796 | 32460864 | Hyper | cancer_general | WT1, WT1-AS |
| chr11 | 33037467 | 33037556 | Hyper | blood | DEPDC7 | chr11 | 33890297 | 33890334 | Hyper | cancer_general | LMO2 |
| chr11 | 35547499 | 35547562 | Hyper | tcga | PAMR1 | chr11 | 35641683 | 35641718 | Hyper | cancer_general | FJX1 |
| chr11 | 43596513 | 43596608 | Hyper | cancer_general | MIR 129-2, JA715139, BC031305 | chr11 | 43600453 | 43600557 | Hyper | cancer_general | BC031305, MIR129-2, JA715139 |
| chr11 | 43601094 | 43601467 | Hyper | cancer_general | MIR129-2, JA715139, BC031305 | chr11 | 43602468 | 43603228 | Hyper | liver_tcga, literature, cancer_general | MIR 129-2, JA715139 |
| chr11 | 43603628 | 43604177 | Hyper | cancer_general | JA715139, MIR129-2 | chr11 | 44325688 | 44325747 | Hyper | cancer_general | ALX4 |
| chr11 | 44326137 | 44326184 | Hyper | cancer_general | ALX4 | chr11 | 44326439 | 44326481 | Hyper | cancer_general | ALX4 |
| chr11 | 44327252 | 44327413 | Hyper | tcga | ALX4 | chr11 | 44330656 | 44331711 | Hyper | cancer_general | ALX4 |
| chr11 | 44333052 | 44333081 | Hyper | literature | ALX4 | chr11 | 44333371 | 44333480 | Hyper | cancer_general | ALX4 |
| chr11 | 44337690 | 44338077 | Hyper | cancer_general | ALX4 | chr11 | 44338335 | 44338367 | Hyper | cancer_general | ALX4 |
| chr11 | 44340823 | 44340858 | Hyper | cancer_general | ALX4 | chr11 | 44341966 | 44342034 | Hyper | cancer_general | ALX4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 46316860 | 46317680 | Hyper | tcga, cancer_general | CREB3L1 | chr11 | 46313042 | 46413304 | Hyper | esophageal | AMBRA1, CHRM4, MDK |
| chr11 | 46940419 | 46940531 | Hyper | tcga | LRP4 | chr11 | 47209044 | 47209189 | Hyper | cancer_general | PACSIN3 YPEL4, MIR130A, AK096335 |
| chr11 | 57194355 | 57194509 | Hyper | tcga | SLC43A3 | chr11 | 57414633 | 57414663 | Hyper | pancreas | |
| chr11 | 58672746 | 58673064 | Hyper | cancer_general | AK294973 | chr11 | 59323596 | 59323729 | Hyper | cancer_general | TRNA_Val, TRNA_Lys, TRNA_Phe, U7, JB175310, TRNA_Leu, TRNA_Arg |
| chr11 | 59333405 | 59333541 | Hyper | cancer_general | TRNA_Phe, OSBP, JB175310, TRNA_Lys, U7 | chr11 | 60718668 | 60719163 | Hyper | cancer_general | SLC15A3 |
| chr11 | 61062822 | 61063138 | Hyper | tcga, cancer_general | DDB1, VWCE | chr11 | 61277002 | 61277220 | Hyper | liver_tcga, cancer_general | SYT7, LRRC10B, MIR4488 |
| chr11 | 61595086 | 61595262 | Hyper | cancer_general | FADS2 FTH1 | chr11 | 61596420 | 61596640 | Hyper | cancer_general | FADS2 |
| chr11 | 61723067 | 61723159 | Hyper | cancer_general | BEST1 | chr11 | 63767984 | 63768131 | Hyper | tcga, cancer_general | MACROD1, OTUB1 |
| chr11 | 63839478 | 63839528 | Hyper | liver_tcga | MACROD1 | chr11 | 64410723 | 64410759 | Hyper | esophageal | NRXN2 |
| chr11 | 64480429 | 64480593 | Hyper | cancer_general | | chr11 | 64480824 | 64481042 | Hyper | liver_tcga, cancer_general | |
| chr11 | 64490435 | 64490561 | Hyper | esophageal | RASGRP2 | chr11 | 64490792 | 64491159 | Hyper | esophageal | RASGRP2 NEAT1, FRMD8 |
| chr11 | 64739468 | 64739508 | Hyper | cancer_general | | chr11 | 65185548 | 65185728 | Hyper | cancer_general | |
| chr11 | 65405659 | 65405774 | Hyper | tcga | MIR4690, PCNXL3, SIPA1 | chr11 | 65409759 | 65409861 | Hyper | liver_tcga | MIR4489, SIPA1, MIR4690, PCNXL3 |
| chr11 | 65554041 | 65554410 | Hyper | liver_tcga | OVOL1, AP5B1 | chr11 | 65600810 | 65601640 | Hyper | liver_tcga, cancer_general | SNX32 |
| chr11 | 65779317 | 65779357 | Hyper | literature | EIF1AD, CST6, AX747517, CATSPER1, BANF1 | chr11 | 65816447 | 65816564 | Hyper | literature, cancer_general | GAL3ST3, SF3B2 |
| chr11 | 66188115 | 66188145 | Hyper | cancer_general | NPAS4 | chr11 | 66184873 | 66188974 | Hyper | cancer_general | NPAS4 |
| chr11 | 66725600 | 66725637 | Hyper | blood | | chr11 | 66790621 | 66790655 | Hyper | blood | SYT12 |
| chr11 | 67139422 | 67139546 | Hyper | liver_tcga | CLCF1, 7SK | chr11 | 67350180 | 67350340 | Hyper | literature | GSTP1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 67350961 | 67350990 | Hyper | literature | GSTP1 | chr11 | 68096034 | 68096179 | Hyper | tcga | LRP5 |
| chr11 | 68118716 | 68118745 | Hyper | liver_tcga | LRP5 | chr11 | 68153950 | 68154098 | Hyper | liver tcga | LRP5 |
| chr11 | 68181217 | 68181288 | Hyper | liver_tcga | LRP5 | chr11 | 69466004 | 69466042 | Hyper | literature | AK294004, ORAOV1, BC133018, CCND1 |
| chr11 | 69484356 | 69484454 | Hyper | head_neck | ORAOV1 | chr11 | 69516968 | 69517174 | Hyper | cancer_general | FGF19 |
| chr11 | 69518030 | 69518211 | Hyper | liver_tcga, cancer_general | FGF19 | chr11 | 69518530 | 69518718 | Hyper | tcga, liver_tcga | FGF19 |
| chr11 | 69588930 | 69589184 | Hyper | cancer_general | FGF4 | chr11 | 69589824 | 69589854 | Hyper | cancer_general | FGF4 |
| chr11 | 69590149 | 69590222 | Hyper | cancer_general | FGF4 | chr11 | 70211516 | 70211545 | Hyper | literature | PPFIA1, AK125463 |
| chr11 | 71318332 | 71318967 | Hyper | cancer_general | | chr11 | 71951639 | 71951738 | Hyper | cancer_general | PHOX2A, INPPL1 |
| chr11 | 71952340 | 71952541 | Hyper | cancer_general | PHOX2A, INPPL1 | chr11 | 71954612 | 71954642 | Hyper | cancer_general | INPPL1, PHOX2A |
| chr11 | 71955344 | 71955377 | Hyper | cancer_general | PHOX2A, INPPL1 | chr11 | 71956007 | 71956340 | Hyper | cancer_general | PHOX2A, INPPL1 |
| chr11 | 72432837 | 72432916 | Hyper | cancer_general | UCP2 | chr11 | 72929747 | 72929883 | Hyper | blood | P2RY2 |
| chr11 | 73694609 | 73694659 | Hyper | hepatobiliary | TPBGL | chr11 | 74394491 | 74394600 | Hyper | cancer_general | |
| chr11 | 74953265 | 74953422 | Hyper | cancer_general | ODZ4, TENM4 | chr11 | 75379252 | 75379895 | Hyper | cancer_general | MAP6 |
| chr11 | 78672917 | 78672964 | Hyper | cancer_general | FAM181B | chr11 | 79151173 | 79151216 | Hyper | tcga | |
| chr11 | 82444376 | 82445101 | Hyper | cancer_general | ME3 | chr11 | 86085742 | 86085968 | Hyper | literature, cancer_general | CCDC81 |
| chr11 | 86383167 | 86383710 | Hyper | literature, tcga | | chr11 | 88241705 | 88242618 | Hyper | tcga, cancer_general | GRM5, GRM5-AS1 |
| chr11 | 88799082 | 88799209 | Hyper | cancer_general | GRM5 | chr11 | 89867794 | 89867990 | Hyper | tcga, cancer_general | NAALAD2 |
| chr11 | 91957500 | 91957674 | Hyper | cancer_general | | chr11 | 91957974 | 91958230 | Hyper | tcga, cancer_general | |
| chr11 | 91958734 | 91959430 | Hyper | tcga, cancer_general | CCDC67 | chr11 | 91959899 | 91960045 | Hyper | cancer_general | |
| chr11 | 93063583 | 93063645 | Hyper | cancer_general | CCDC67 | chr11 | 93063870 | 93063948 | Hyper | liver_tcga, cancer_general | CCDC67 |
| chr11 | 94134086 | 94134853 | Hyper | tcga, cancer_general | GPR83 | chr11 | 94278456 | 94278603 | Hyper | liver_tcga | PIWIL4, FUT4 |
| chr11 | 94473600 | 94474139 | Hyper | tcga, colorectal, cancer_general | | chr11 | 94474356 | 94474385 | Hyper | tcga | |
| chr11 | 94502334 | 94502489 | Hyper | tcga, colorectal | AMOTL1 | chr11 | 94884130 | 94884160 | Hyper | head_neck | AK055250 |
| chr11 | 98891477 | 98891882 | Hyper | tcga, cancer_general | CNTN5 | chr11 | 100997649 | 100997981 | Hyper | cancer_general | LOC101054525, PGR |
| chr11 | 100998276 | 100998318 | Hyper | cancer_general | LOC101054525, PGR | chr11 | 100998667 | 100998747 | Hyper | cancer_general | LOC101054525, PGR |
| chr11 | 101453180 | 101453518 | Hyper | cancer_general | DCUN1D5 | chr11 | 101454190 | 101454490 | Hyper | cancer_general | DYNC2H1 |
| chr11 | 102962922 | 102963062 | Hyper | pancreas | | chr11 | 102980027 | 102980056 | Hyper | literature | GRIA4 |
| chr11 | 104034521 | 104034996 | Hyper | tcga, cancer_general | | chr11 | 105480755 | 105480806 | Hyper | cancer_general | |
| chr11 | 105481216 | 105481571 | Hyper | tcga, cancer_general | GRIA4 | chr11 | 106888308 | 106888429 | Hyper | cancer_general | GUCY1A2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 106888641 | 106888801 | Hyper | tcga, cancer_general | GUCY1A2 | chr11 | 107461623 | 107461653 | Hyper | esophageal | ELMOD1, LOC643923 |
| chr11 | 107462415 | 107462459 | Hyper | tcga | LOC643923, ELMOD1 | chr11 | 108236072 | 108236101 | Hyper | literature | C11orf65 |
| chr11 | 109292906 | 109293052 | Hyper | cancer_general | C11orf87 | chr11 | 109293720 | 109293847 | Hyper | cancer_general | C11orf87 |
| chr11 | 110166519 | 110166935 | Hyper | esophageal | | chr11 | 110582232 | 110582434 | Hyper | tcga | |
| chr11 | 110582895 | 110583050 | Hyper | tcga | | chr11 | 110583574 | 110583730 | Hyper | cancer_general | |
| chr11 | 111383183 | 111383682 | Hyper | cancer_general | MIR34B, MIR34C, C11orf88, BC021736, BTG4 | chr11 | 111411093 | 111412061 | Hyper | cancer_general | LAYN, C11orf88 |
| chr11 | 114113022 | 114113052 | Hyper | esophageal | ZBTB16 | chr11 | 115375120 | 115375177 | Hyper | cancer_general | CADM1 |
| chr11 | 115530134 | 115530604 | Hyper | cancer_general, tcga | | chr11 | 115630515 | 115630910 | Hyper | cancer_general | LINC00900 |
| chr11 | 115631307 | 115631364 | Hyper | cancer_general | LINC00900 | chr11 | 116147253 | 116147283 | Hyper | pancreas | DSCAML1 |
| chr11 | 116451023 | 116451190 | Hyper | tcga | | chr11 | 117296921 | 117297109 | Hyper | tcga | CBL |
| chr11 | 119148865 | 119148945 | Hyper | literature | CBL | chr11 | 119149236 | 119149265 | Hyper | literature | THY1, LOC10499227 |
| chr11 | 119292779 | 119292809 | Hyper | cancer_general | THY1, LOC10499227 | chr11 | 119293370 | 119293615 | Hyper | tcga | |
| chr11 | 119612227 | 119612399 | Hyper | cancer_general | | chr11 | 119612861 | 119613075 | Hyper | liver_tcga, cancer_general | |
| chr11 | 120039833 | 120039865 | Hyper | blood | | chr11 | 120435405 | 120435477 | Hyper | cancer_general | GRIK4 |
| chr11 | 120435800 | 120435830 | Hyper | cancer_general | GRIK4 | chr11 | 120894800 | 120895026 | Hyper | esophageal | TBCEL |
| chr11 | 122847265 | 122847696 | Hyper | cancer_general | BSX | chr11 | 122848079 | 122848591 | Hyper | cancer_general | BSX |
| chr11 | 122849301 | 122849331 | Hyper | cancer_general | BSX | chr11 | 122849642 | 122850163 | Hyper | cancer_general | BSX |
| chr11 | 122850424 | 122850536 | Hyper | cancer_general | BSX | chr11 | 122851177 | 122851209 | Hyper | cancer_general | BSX |
| chr11 | 122852438 | 122852475 | Hyper | cancer_general | BSX | chr11 | 122855008 | 122855043 | Hyper | tcga | |
| chr11 | 123066433 | 123066463 | Hyper | cancer_general | CLMP | chr11 | 123229058 | 123229422 | Hyper | tcga, cancer_general | |
| chr11 | 123300824 | 123302026 | Hyper | tcga, cancer_general | | chr11 | 124735437 | 124735482 | Hyper | cancer_general | ROBO3 |
| chr11 | 124736196 | 124736252 | Hyper | cancer_general | ROBO3 | chr11 | 124738777 | 124739088 | Hyper | cancer_general | ROBO3 |
| chr11 | 125035763 | 125036208 | Hyper | cancer_general | PKNOX2 | chr11 | 125036598 | 125036645 | Hyper | cancer_general | PKNOX2 |
| chr11 | 125773675 | 125774096 | Hyper | cancer_general, liver_tcga | DDX25, HYLS1, PUS3 | chr11 | 126870182 | 126870212 | Hyper | cancer_general | KIRREL3-AS3 |
| chr11 | 126870453 | 126870543 | Hyper | cancer_general | KIRREL3-AS3 | chr11 | 126873390 | 126873515 | Hyper | cancer_general | KIRREL3-AS3 |
| chr11 | 128391893 | 128392116 | Hyper | tcga | BC043517, ETS1 | chr11 | 128562892 | 128563730 | Hyper | tcga, cancer_general | FLI1, FLI1-AS1, AX747861 |
| chr11 | 128563940 | 128564329 | Hyper | tcga, cancer_general | FLI1, FLI1-AS1, AX747861 | chr11 | 128564740 | 128565379 | Hyper | cancer_general | FLI1-AS1, AX747861, FLI1 |
| chr11 | 129242876 | 129243587 | Hyper | cancer_general | BARX2 | chr11 | 129243849 | 129244603 | Hyper | cancer_general | BARX2 |
| chr11 | 129244893 | 129244923 | Hyper | cancer_general | BARX2 | chr11 | 129245673 | 129245810 | Hyper | blood | BARX2 |
| chr11 | 129246070 | 129246129 | Hyper | blood | BARX2 | chr11 | 130318960 | 130318997 | Hyper | blood | |
| chr11 | 130319527 | 130319613 | Hyper | cancer_general | ADAMTS15 | chr11 | 131564970 | 131565073 | Hyper | pancreas | ADAMTS15 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 131780469 | 131781271 | Hyper | tcga, cancer_general | NTM | chr11 | 132813489 | 132813949 | Hyper | tcga, cancer_general | |
| chr11 | 132864134 | 132864175 | Hyper | cancer_general | | chr11 | 132934123 | 132934176 | Hyper | cancer_general | |
| chr11 | 132952768 | 132953423 | Hyper | tcga, cancer_general | | chr11 | 133402206 | 133402260 | Hyper | cancer_general | |
| chr11 | 133825226 | 133825543 | Hyper | cancer_general | IGSF9B | chr11 | 133906783 | 133906918 | Hyper | cancer_general | LOC100128239 |
| chr11 | 133939002 | 133939177 | Hyper | cancer_general | JAM3 | chr11 | 134145703 | 134146393 | Hyper | liver_tcga, cancer_general, tcga | GLB1L3 |
| chr11 | 134146682 | 134146894 | Hyper | cancer_general | GLB1L3 | chr11 | 134201502 | 134201543 | Hyper | blood | GLB1L2 |
| chr11 | 134201841 | 134202084 | Hyper | blood, tcga, liver_tcga | GLB1L2 | chr11 | 134281365 | 134281509 | Hyper | cancer_general | LOC283177 |
| chrY | 2655316 | 2655346 | Hyper | cancer_general | SRY, RPS4Y1, XGPY2 | chrY | 14532822 | 14532852 | Hyper | head_neck | GYG2P1 |
| chrY | 14533556 | 14533613 | Hyper | head_neck | GYG2P1 | HPV18 | 111 | 140 | Hyper | virus | |
| HPV18 | 383 | 412 | Hyper | virus | | HPV18 | 655 | 684 | Hyper | virus | |
| HPV18 | 927 | 956 | Hyper | virus | | HPV18 | 1199 | 1228 | Hyper | virus | |
| HPV18 | 1471 | 1500 | Hyper | virus | | HPV18 | 1743 | 1772 | Hyper | virus | |
| HPV18 | 2015 | 2044 | Hyper | virus | | HPV18 | 2287 | 2316 | Hyper | virus | |
| HPV18 | 2559 | 2588 | Hyper | virus | | HPV18 | 2831 | 2860 | Hyper | virus | |
| HPV18 | 3103 | 3132 | Hyper | virus | | HPV18 | 3375 | 3404 | Hyper | virus | |
| HPV18 | 3647 | 3676 | Hyper | virus | | HPV18 | 3919 | 3948 | Hyper | virus | |
| HPV18 | 4191 | 4220 | Hyper | virus | | HPV18 | 4463 | 4492 | Hyper | virus | |
| HPV18 | 4735 | 4764 | Hyper | virus | | HPV18 | 5007 | 5036 | Hyper | virus | |
| HPV18 | 5279 | 5308 | Hyper | virus | | HPV18 | 5551 | 5580 | Hyper | virus | |
| HPV18 | 5823 | 5852 | Hyper | virus | | HPV18 | 6095 | 6124 | Hyper | virus | |
| HPV18 | 6367 | 6396 | Hyper | virus | | HPV18 | 6639 | 6668 | Hyper | virus | |
| HPV18 | 6911 | 6940 | Hyper | virus | | HPV18 | 7183 | 7212 | Hyper | virus | |
| HPV18 | 7455 | 7484 | Hyper | virus | | HBV | 111 | 140 | Hyper | virus | |
| HBV | 381 | 410 | Hyper | virus | | HBV | 651 | 680 | Hyper | virus | |
| HBV | 921 | 950 | Hyper | virus | | HBV | 1191 | 1220 | Hyper | virus | |
| HBV | 1461 | 1490 | Hyper | virus | | HBV | 1731 | 1760 | Hyper | virus | |
| HBV | 2001 | 2030 | Hyper | virus | | HBV | 2271 | 2300 | Hyper | virus | |
| HBV | 2541 | 2570 | Hyper | virus | | HBV | 2811 | 2840 | Hyper | virus | |
| chr18 | 499367 | 499482 | Hyper | cancer_general | COLEC12 | chr18 | 500046 | 500738 | Hyper | cancer_general | COLEC12 |
| chr18 | 904462 | 904648 | Hyper | cancer_general | ADCYAP1 | chr18 | 905000 | 905030 | Hyper | cancer_general | ADCYAP1 |
| chr18 | 905434 | 905642 | Hyper | cancer_general | ADCYAP1 | chr18 | 906871 | 906907 | Hyper | cancer_general | ADCYAP1 |
| chr18 | 907472 | 907594 | Hyper | cancer_general | ADCYAP1 | chr18 | 907912 | 907977 | Hyper | cancer_general | ADCYAP1 |
| chr18 | 908454 | 908589 | Hyper | cancer_general | ADCYAP1 | chr18 | 909120 | 909150 | Hyper | cancer_general | ADCYAP1 |
| chr18 | 909487 | 909587 | Hyper | cancer_general | ADCYAP1 | chr18 | 2906268 | 2906304 | Hyper | cancer_general | EMILIN2 |
| chr18 | 3499067 | 3499371 | Hyper | cancer_general | DLGAP1 | chr18 | 4453964 | 4454163 | Hyper | tcga | |
| chr18 | 4455074 | 4455181 | Hyper | cancer_general | C18orf42 | chr18 | 5196516 | 5196959 | Hyper | cancer_general | C18orf42 LINC00667, LINC00526, LOC339290 |
| chr18 | 5197202 | 5197347 | Hyper | cancer_general | | chr18 | 5237878 | 5238247 | Hyper | esophageal | |
| chr18 | 5543231 | 5543331 | Hyper | cancer_general | EPB41L3 | chr18 | 5543640 | 5543853 | Hyper | cancer_general | EPB41L3 |
| chr18 | 5628167 | 5628515 | Hyper | cancer_general | | chr18 | 5629774 | 5629984 | Hyper | cancer_general | |
| chr18 | 5630312 | 5630362 | Hyper | cancer_general | | chr18 | 5890619 | 5891317 | Hyper | cancer_general | TMEM200C |
| chr18 | 5895023 | 5895205 | Hyper | cancer_general | TMEM200C | chr18 | 5895975 | 5896085 | Hyper | tcga | TMEM200C |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 6729952 | 6729993 | Hyper | cancer_general | | chr18 | 7116924 | 7116981 | Hyper | cancer_general | LAMA1 |
| chr18 | 7117665 | 7117804 | Hyper | tcga | LAMA1 | chr18 | 7567783 | 7568291 | Hyper | tcga, cancer_general | PTPRM |
| chr18 | 8608748 | 8608968 | Hyper | cancer_general | RAB12 | chr18 | 9771586 | 9771753 | Hyper | cancer_general | RAB31 |
| chr18 | 11148969 | 11149045 | Hyper | cancer_general | | chr18 | 11149561 | 11149888 | Hyper | cancer_general | |
| chr18 | 11689190 | 11689220 | Hyper | esophageal | | chr18 | 11751637 | 11751676 | Hyper | cancer_general | GNAL |
| chr18 | 11751966 | 11752379 | Hyper | cancer_general | GNAL | chr18 | 11752700 | 11752730 | Hyper | cancer_general | GNAL |
| chr18 | 12254226 | 12254578 | Hyper | cancer_general, tcga | CIDEA | chr18 | 12307247 | 12307751 | Hyper | tcga, cancer_general | TUBB6 |
| chr18 | 12911384 | 12911476 | Hyper | cancer_general | | chr18 | 13824025 | 13824102 | Hyper | head_neck | MC5R |
| chr18 | 13868713 | 13868945 | Hyper | cancer_general | | chr18 | 15198110 | 15198248 | Hyper | cancer_general | |
| chr18 | 18822392 | 18823274 | Hyper | cancer_general | GREB1L | chr18 | 19750308 | 19750346 | Hyper | blood | GATA6, LOC100128893 |
| chr18 | 21269349 | 21269390 | Hyper | blood | LAMA3 | chr18 | 21269659 | 21269740 | Hyper | blood | LAMA3 |
| chr18 | 21719351 | 21719568 | Hyper | liver_tcga | CABYR, TTC39C | chr18 | 22929081 | 22930559 | Hyper | cancer_general, tcga | ZNF521 |
| chr18 | 22930790 | 22931178 | Hyper | cancer_general | ZNF521 | chr18 | 24127748 | 24128030 | Hyper | cancer_general | |
| chr18 | 24130809 | 24131187 | Hyper | cancer_general | | chr18 | 24764951 | 24765168 | Hyper | tcga | CHST9 |
| chr18 | 25755593 | 25755655 | Hyper | tcga | | chr18 | 25756010 | 25756040 | Hyper | cancer_general | |
| chr18 | 25756495 | 25756729 | Hyper | tcga, cancer_general | | chr18 | 25757187 | 25757452 | Hyper | tcga | |
| chr18 | 25757787 | 25757824 | Hyper | cancer_general | DSC3 | chr18 | 25758084 | 25758141 | Hyper | cancer_general | DSC3 |
| chr18 | 28620899 | 28621097 | Hyper | cancer_general | DSC3 | chr18 | 28621328 | 28621393 | Hyper | cancer_general | DSC3 |
| chr18 | 28621636 | 28621932 | Hyper | liver_tcga, cancer_general | | chr18 | 28622419 | 28622488 | Hyper | cancer_general | |
| chr18 | 30349740 | 30349781 | Hyper | cancer_general | KLHL14 | chr18 | 31020495 | 31020820 | Hyper | tcga, cancer_general | CCDC178 |
| chr18 | 31158093 | 31158158 | Hyper | cancer_general | ASXL3 | chr18 | 31739035 | 31739469 | Hyper | cancer_general | |
| chr18 | 31802132 | 31802167 | Hyper | cancer_general | | chr18 | 31802938 | 31802968 | Hyper | cancer_general | |
| chr18 | 31803438 | 31803472 | Hyper | cancer_general | | chr18 | 31902793 | 31902945 | Hyper | cancer_general | |
| chr18 | 32073885 | 32074086 | Hyper | cancer_general | DTNA | chr18 | 32557832 | 32557864 | Hyper | lung | MAPRE2 |
| chr18 | 32847565 | 32847642 | Hyper | liver_tcga | ZSCAN30 | chr18 | 33877683 | 33877754 | Hyper | head_neck | FHOD3 |
| chr18 | 34833596 | 34833859 | Hyper | cancer_general | CELF4 | chr18 | 35065072 | 35065438 | Hyper | esophageal | |
| chr18 | 35104666 | 35104882 | Hyper | tcga | | chr18 | 35144845 | 35145465 | Hyper | cancer_general | |
| chr18 | 35145968 | 35146241 | Hyper | tcga | | chr18 | 35147487 | 35147569 | Hyper | cancer_general | ST8SIA5 |
| chr18 | 43914211 | 43914278 | Hyper | tcga | C18orf23, RNF165 | chr18 | 44336034 | 44336697 | Hyper | cancer_general | |
| chr18 | 44336901 | 44336946 | Hyper | cancer_general | ST8SIA5 | chr18 | 44337174 | 44338074 | Hyper | cancer_general | ST8SIA5 |
| chr18 | 44773060 | 44773197 | Hyper | cancer_general | | chr18 | 44773592 | 44774153 | Hyper | cancer_general | |
| chr18 | 44774406 | 44774890 | Hyper | cancer_general | | chr18 | 44775380 | 44775554 | Hyper | cancer_general | |
| chr18 | 44776972 | 44777088 | Hyper | cancer_general | | chr18 | 44777301 | 44777331 | Hyper | cancer_general | |
| chr18 | 44777596 | 44777750 | Hyper | cancer_general | | chr18 | 44778049 | 44778326 | Hyper | cancer_general | |
| chr18 | 44781003 | 44781041 | Hyper | cancer_general | | chr18 | 44787781 | 44787846 | Hyper | cancer_general | |
| chr18 | 44788251 | 44788281 | Hyper | cancer_general | | chr18 | 44789474 | 44789514 | Hyper | cancer_general | |
| chr18 | 44789872 | 44789937 | Hyper | blood | | chr18 | 45058069 | 45058240 | Hyper | cancer_general | BC040860 |
| chr18 | 47720492 | 47720522 | Hyper | cancer_general | | chr18 | 48604773 | 48604802 | Hyper | literature | SMAD4 |
| chr18 | 49867303 | 49867399 | Hyper | cancer_general | DCC | chr18 | 49886634 | 49886664 | Hyper | cancer_general | DCC |
| chr18 | 52989009 | 52989220 | Hyper | cancer_general | TCF4 | chr18 | 52989741 | 52989882 | Hyper | cancer_general | TCF4 |
| chr18 | 53257137 | 53257204 | Hyper | cancer_general | TCF4 | chr18 | 53446970 | 53447816 | Hyper | tcga, liver_tcga, cancer_general | AK127787 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 54789070 | 54789256 | Hyper | cancer_general | | chr18 | 55019707 | 55019871 | Hyper | liver_tcga, cancer_general | ST8SIA3 |
| chr18 | 55020655 | 55020727 | Hyper | cancer_general | ST8SIA3 | chr18 | 55021078 | 55021242 | Hyper | cancer_general | ST8SIA3 |
| chr18 | 55103381 | 55103411 | Hyper | cancer_general | ONECUT2 | chr18 | 55103719 | 55103748 | Hyper | literature | ONECUT2 |
| chr18 | 55104808 | 55105140 | Hyper | cancer_general | ONECUT2 | chr18 | 55105728 | 55105830 | Hyper | cancer_general | ONECUT2 |
| chr18 | 55114480 | 55114644 | Hyper | cancer_general | ONECUT2 | chr18 | 56887076 | 56887424 | Hyper | cancer_general, tcga | GRP |
| chr18 | 56888554 | 56888623 | Hyper | cancer_general | GRP | chr18 | 56931541 | 56931583 | Hyper | cancer_general | RAX |
| chr18 | 56931967 | 56932107 | Hyper | cancer_general | RAX | chr18 | 56932352 | 56932637 | Hyper | cancer_general | RAX |
| chr18 | 56935010 | 56935319 | Hyper | cancer_general | RAX | chr18 | 56936004 | 56936074 | Hyper | cancer_general | RAX |
| chr18 | 56939113 | 56939174 | Hyper | cancer_general | RAX | chr18 | 56939423 | 56940722 | Hyper | cancer_general | RAX |
| chr18 | 56940955 | 56941788 | Hyper | cancer_general | RAX | chr18 | 57363706 | 57363743 | Hyper | cancer_general | CCBE1 |
| chr18 | 57364275 | 57364392 | Hyper | cancer_general | CCBE1 | chr18 | 57364658 | 57364691 | Hyper | pancreas | CCBE1 |
| chr18 | 59000988 | 59001022 | Hyper | cancer_general | CDH20 | chr18 | 59001301 | 59001740 | Hyper | cancer_general, tcga | CDH20 |
| chr18 | 60263547 | 60263895 | Hyper | cancer_general | DKFZp451A185 | chr18 | 60985498 | 60985732 | Hyper | liver_tcga, cancer_general | KDSR, BCL2 |
| chr18 | 67067558 | 67067907 | Hyper | tcga, cancer_general | DOK6 | chr18 | 67068152 | 67068203 | Hyper | cancer_general | DOK6 |
| chr18 | 67068442 | 67068471 | Hyper | tcga | DOK6 | chr18 | 67068715 | 67068811 | Hyper | tcga, cancer_general | DOK6 |
| chr18 | 67069216 | 67069246 | Hyper | cancer_general | DOK6 | chr18 | 70209148 | 70209205 | Hyper | cancer_general | CBLN2 |
| chr18 | 70209422 | 70209452 | Hyper | cancer_general | CBLN2 | chr18 | 70210418 | 70210508 | Hyper | tcga, cancer_general | CBLN2 |
| chr18 | 70211626 | 70211666 | Hyper | cancer_general | CBLN2 | chr18 | 70534282 | 70534969 | Hyper | cancer_general | NETO1 |
| chr18 | 70535373 | 70535582 | Hyper | cancer_general | NETO1 | chr18 | 70536010 | 70536604 | Hyper | cancer_general | NETO1 |
| chr18 | 70536833 | 70536871 | Hyper | cancer_general | NETO1 | chr18 | 70537188 | 70537218 | Hyper | cancer_general | NETO1 |
| chr18 | 73167585 | 73167832 | Hyper | cancer_general | GALR1 | chr18 | 73628019 | 73628068 | Hyper | cancer_general | |
| chr18 | 74961326 | 74962147 | Hyper | cancer_general, literature | GALR1 | chr18 | 74962250 | 74962652 | Hyper | cancer_general | GALR1 |
| chr18 | 74962970 | 74963599 | Hyper | cancer_general | | chr18 | 75362931 | 75362985 | Hyper | pancreas | |
| chr18 | 75612225 | 75612286 | Hyper | cancer_general | | chr18 | 76740079 | 76740285 | Hyper | liver_tcga | SALL3 |
| chr18 | 77548078 | 77548609 | Hyper | cancer_general | | chr18 | 77558082 | 77558358 | Hyper | cancer_general | |
| chr18 | 77558831 | 77558930 | Hyper | tcga | FOXD4, CBWD1 | chr18 | 78004993 | 78005051 | Hyper | blood | PARD6G |
| chr9 | 113433 | 113556 | Hyper | cancer_general | FOXD4, CBWD1, FOXD4 | chr9 | 113850 | 113885 | Hyper | cancer_general | FOXD4, CBWD1 |
| chr9 | 117884 | 118090 | Hyper | cancer_general | DMRT1 | chr9 | 841691 | 842230 | Hyper | cancer_general | DMRT1 |
| chr9 | 842558 | 842673 | Hyper | cancer_general | DMRT3, DMRT1 | chr9 | 969556 | 969586 | Hyper | cancer_general | DMRT3, DMRT1 |
| chr9 | 969799 | 969846 | Hyper | cancer_general | DMRT3, DMRT1 | chr9 | 970096 | 970225 | Hyper | cancer_general | DMRT3, DMRT1 |
| chr9 | 970495 | 970525 | Hyper | cancer_general | DMRT3, DMRT1 | chr9 | 970897 | 971572 | Hyper | cancer_general | DMRT1, DMRT3 |
| chr9 | 972307 | 972759 | Hyper | tcga, cancer_general | DMRT3, DMRT1 | chr9 | 973143 | 973289 | Hyper | cancer_general | DMRT3, DMRT1 |
| chr9 | 974514 | 974547 | Hyper | cancer_general | DMRT1, DMRT3 | chr9 | 975117 | 975167 | Hyper | cancer_general | DMRT3, DMRT1 |
| chr9 | 975783 | 976321 | Hyper | cancer_general | DMRT3, DMRT1 | chr9 | 976618 | 976961 | Hyper | tcga, cancer_general | DMRT3, DMRT1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 981797 | 981830 | Hyper | cancer_general | DMRT3 | chr9 | 1042402 | 1042986 | Hyper | tcga, cancer_general | DMRT2 |
| chr9 | 1051848 | 1052166 | Hyper | cancer_general | DMRT2 | chr9 | 3181752 | 3181869 | Hyper | literature | JAK2 |
| chr9 | 5070006 | 5070050 | Hyper | literature | JAK2 | chr9 | 5073756 | 5073788 | Hyper | literature | TRNA_Gln, JAK2 |
| chr9 | 5078346 | 5078375 | Hyper | literature | JAK2 | chr9 | 5089711 | 5089740 | Hyper | literature | |
| chr9 | 6412571 | 6412809 | Hyper | cancer_general | UHRF2 | chr9 | 6644297 | 6644554 | Hyper | cancer_general | GLDC |
| chr9 | 6645017 | 6645333 | Hyper | cancer_general | GLDC | chr9 | 6645625 | 6645700 | Hyper | cancer_general | GLDC |
| chr9 | 13278818 | 13278864 | Hyper | cancer_general | JAK2 | chr9 | 14312994 | 14313096 | Hyper | blood | NFIB |
| chr9 | 14313319 | 14313785 | Hyper | blood | NFIB | chr9 | 14347633 | 14347673 | Hyper | cancer_general | |
| chr9 | 14348314 | 14348452 | Hyper | cancer_general | | chr9 | 17906404 | 17906694 | Hyper | cancer_general | |
| chr9 | 17907004 | 17907061 | Hyper | cancer_general | | chr9 | 17907416 | 17907472 | Hyper | cancer_general | |
| chr9 | 19789107 | 19789301 | Hyper | cancer_general | SLC24A2 | chr9 | 21031734 | 21031836 | Hyper | cancer_general | PTPLAD2 |
| chr9 | 21402617 | 21403021 | Hyper | cancer_general | IFNA8 | chr9 | 21559294 | 21559381 | Hyper | blood | |
| chr9 | 21559665 | 21559702 | Hyper | blood | | chr9 | 21965057 | 21965757 | Hyper | lung, cancer_general | C9orf53, CDKN2A |
| chr9 | 21968218 | 21968475 | Hyper | literature, cancer_general | C9orf53, CDKN2A | chr9 | 21970959 | 21971220 | Hyper | literature, cancer_general | CDKN2A, C9orf53 |
| chr9 | 21973940 | 21974237 | Hyper | cancer_general | CDKN2A, C9orf53 | chr9 | 21974499 | 21974794 | Hyper | liver_tcga, literature, cancer_general | CDKN2A, C9orf53 |
| chr9 | 21994208 | 21994237 | Hyper | literature | CDKN2B-AS1, CDKN2B | chr9 | 21995297 | 21995326 | Hyper | literature | CDKN2B, CDKN2B-AS1 |
| chr9 | 21995720 | 21995749 | Hyper | literature | CDKN2B-AS1, CDKN2B | chr9 | 22006131 | 22006160 | Hyper | literature | CDKN2B, CDKN2B-AS1 |
| chr9 | 22008819 | 22008899 | Hyper | literature | CDKN2B, CDKN2B-AS1 | chr9 | 22447664 | 22447708 | Hyper | tcga | DMRTA1 |
| chr9 | 23822568 | 23822606 | Hyper | cancer_general | | chr9 | 23824561 | 23824591 | Hyper | cancer_general | |
| chr9 | 23831100 | 23831399 | Hyper | cancer_general | | chr9 | 29212170 | 29212294 | Hyper | cancer_general | |
| chr9 | 29213508 | 29213651 | Hyper | cancer_general | | chr9 | 29214030 | 29214144 | Hyper | cancer_general | |
| chr9 | 29214360 | 29214430 | Hyper | cancer_general | | chr9 | 29214681 | 29215086 | Hyper | cancer_general | |
| chr9 | 32782630 | 32783121 | Hyper | cancer_general | TMEM215 | chr9 | 32783346 | 32783657 | Hyper | cancer_general | TMEM215 |
| chr9 | 33524609 | 33524687 | Hyper | cancer_general | ANKRD18B | chr9 | 33676771 | 33676801 | Hyper | cancer_general | PTENP1 |
| chr9 | 33677360 | 33677415 | Hyper | cancer_general | PTENP1 | chr9 | 34589062 | 34589156 | Hyper | cancer_general | LOC415056, CNTFR |
| chr9 | 34809749 | 34809981 | Hyper | cancer_general | | chr9 | 35617291 | 35617337 | Hyper | tcga | CD72, MIR4667, TESK1 |
| chr9 | 35675539 | 35676180 | Hyper | tcga, cancer_general | HV781757, TPM2, CA9 | chr9 | 35844834 | 35844863 | Hyper | literature | TMEM8B |
| chr9 | 36037068 | 36037098 | Hyper | esophageal | RECK | chr9 | 36739755 | 36739980 | Hyper | cancer_general | |
| chr9 | 37002454 | 37003077 | Hyper | literature, cancer_general | PAX5 | chr9 | 37025564 | 37025783 | Hyper | literature, cancer_general | |
| chr9 | 37026146 | 37026622 | Hyper | cancer_general | PAX5 | chr9 | 37026831 | 37027412 | Hyper | tcga, colorectal, cancer_general | PAX5 |
| chr9 | 37027800 | 37027829 | Hyper | literature | PAX5 | chr9 | 37028944 | 37029119 | Hyper | cancer_general | PAX5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 37029534 | 37030655 | Hyper | cancer_general, literature | PAX5 | chr9 | 37034197 | 37034247 | Hyper | cancer_general | PAX5 |
| chr9 | 37034616 | 37034731 | Hyper | cancer_general, literature | PAX5 | chr9 | 37035366 | 37035734 | Hyper | literature, cancer_general | PAX5 |
| chr9 | 37036425 | 37036647 | Hyper | cancer_general | PAX5 | chr9 | 37037671 | 37038354 | Hyper | cancer_general | CR627148, AK308561 |
| chr9 | 38620530 | 38620725 | Hyper | blood | FAM201A, ANKRD18A | chr9 | 66455999 | 66456047 | Hyper | cancer_general | TRPM3 |
| chr9 | 71788952 | 71789757 | Hyper | cancer_general | TIP2, AK096834 | chr9 | 74061838 | 74062070 | Hyper | cancer_general | RORB |
| chr9 | 74764547 | 74764648 | Hyper | cancer_general | GDA | chr9 | 77112993 | 77113825 | Hyper | pancreas, cancer_general | RORB |
| chr9 | 77114745 | 77114851 | Hyper | cancer_general | RORB | chr9 | 77115210 | 77115447 | Hyper | cancer_general | RORB |
| chr9 | 77115657 | 77115687 | Hyper | cancer_general | RORB | chr9 | 79626876 | 79627370 | Hyper | cancer_general | FOXB2 |
| chr9 | 79628289 | 79628329 | Hyper | cancer_general | FOXB2 | chr9 | 79629095 | 79629471 | Hyper | cancer_general | FOXB2 |
| chr9 | 79629879 | 79630420 | Hyper | cancer_general | FOXB2 | chr9 | 79631192 | 79631335 | Hyper | cancer_general | FOXB2 |
| chr9 | 79631555 | 79631591 | Hyper | cancer_general | FOXB2 | chr9 | 79631865 | 79632182 | Hyper | cancer_general | FOXB2 |
| chr9 | 79632860 | 79632890 | Hyper | cancer_general | FOXB2 | chr9 | 79633397 | 79633904 | Hyper | tcga, cancer_general | FOXB2 |
| chr9 | 79634170 | 79636043 | Hyper | cancer_general | FOXB2 | chr9 | 79636258 | 79637274 | Hyper | cancer_general | FOXB2 |
| chr9 | 79637555 | 79638150 | Hyper | cancer_general | FOXB2 | chr9 | 80409473 | 80409502 | Hyper | literature | GNAQ |
| chr9 | 85677905 | 85677992 | Hyper | blood | RASEF | chr9 | 86152387 | 86152417 | Hyper | cancer_general | SLC28A3 |
| chr9 | 86755532 | 86755952 | Hyper | cancer_general | NTRK2 | chr9 | 86886706 | 86886736 | Hyper | cancer_general | NTRK2 |
| chr9 | 87283008 | 87283038 | Hyper | cancer_general | NTRK2 | chr9 | 87283677 | 87283709 | Hyper | cancer_general | INTRK2 |
| chr9 | 87284706 | 87284798 | Hyper | cancer_general | | chr9 | 87285279 | 87285472 | Hyper | cancer_general | |
| chr9 | 88137524 | 88137998 | Hyper | tcga, cancer_general | | chr9 | 89517699 | 89517835 | Hyper | cancer_general | |
| chr9 | 89560760 | 89560827 | Hyper | cancer_general | LOC100506834, GAS1 | chr9 | 89561063 | 89561109 | Hyper | cancer_general | LOC100506834, GAS1, C9orf47, S1PR3 |
| chr9 | 91150222 | 91150335 | Hyper | cancer_general | NXNL2 | chr9 | 91606004 | 91606058 | Hyper | cancer_general | SHC3 |
| chr9 | 91792357 | 91792387 | Hyper | cancer_general | SHC3 | chr9 | 91792776 | 91792907 | Hyper | cancer_general | ANKRD19P |
| chr9 | 91793177 | 91793526 | Hyper | lung, cancer_general | SHC3 | chr9 | 94183870 | 94183954 | Hyper | cancer_general | ANKRD19P |
| chr9 | 94712163 | 94712236 | Hyper | cancer_general | ROR2 | chr9 | 95569759 | 95569822 | Hyper | cancer_general | MIR4291 |
| chr9 | 95570247 | 95570434 | Hyper | cancer_general | ANKRD19P | chr9 | 95571617 | 95571760 | Hyper | cancer_general | BARX1 |
| chr9 | 95947130 | 95947296 | Hyper | cancer_general | WNK2 | chr9 | 96588804 | 96588885 | Hyper | cancer_general | BARX1 |
| chr9 | 96710377 | 96710407 | Hyper | cancer_general | BARX1 | chr9 | 96710647 | 96710991 | Hyper | cancer_general | BARX1 |
| chr9 | 96711258 | 96711617 | Hyper | cancer_general | BARX1 | chr9 | 96711975 | 96712005 | Hyper | tcga, cancer_general | |
| chr9 | 96713378 | 96713893 | Hyper | cancer_general | BARX1 | chr9 | 96715095 | 96715857 | Hyper | cancer_general | |
| chr9 | 96716837 | 96717466 | Hyper | cancer_general | JB148981, BARX1 | chr9 | 96717979 | 96718149 | Hyper | cancer_general | JB148981, BARX1 |
| chr9 | 96720803 | 96721802 | Hyper | lung, cancer_general | JB148981, BARX1 | chr9 | 96722445 | 96722786 | Hyper | cancer_general, lung | JB148981, BARX1 |
| chr9 | 96723093 | 96723202 | Hyper | cancer_general | BARX1, JB148981 | chr9 | 98111365 | 98112395 | Hyper | cancer_general | |
| chr9 | 98784772 | 98784802 | Hyper | cancer_general | LINC00092, C9orf102, ERCC6L2 | chr9 | 98789651 | 98790000 | Hyper | cancer_general | LINC00092, C9orf102 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 99146020 | 99146153 | Hyper | blood | ZNF367, SLC35D2 | chr9 | 99449135 | 99449451 | Hyper | liver_tcga, cancer_general | |
| chr9 | 99639621 | 99639942 | Hyper | cancer_general | LOC100132781, ZNF782 | chr9 | 99983140 | 99983170 | Hyper | cancer_general | |
| chr9 | 99983411 | 99983824 | Hyper | cancer_general | | chr9 | 99984026 | 99984242 | Hyper | cancer_general | |
| chr9 | 100503625 | 100503937 | Hyper | cancer_general | | chr9 | 100609991 | 100610218 | Hyper | cancer_general | FOXE1 |
| chr9 | 100610681 | 100611640 | Hyper | cancer_general | FOXE1 | chr9 | 100613828 | 100614325 | Hyper | cancer_general | FOXE1 |
| chr9 | 100614541 | 100616902 | Hyper | tcga, liver_tcga, cancer_general | FOXE1 | chr9 | 100617293 | 100617365 | Hyper | cancer_general | FOXE1 |
| chr9 | 100617682 | 100618055 | Hyper | cancer_general | FOXE1 | chr9 | 100619722 | 100620069 | Hyper | cancer_general | FOXE1 |
| chr9 | 100620330 | 100620783 | Hyper | cancer_general | FOXE1 | chr9 | 101469269 | 101469307 | Hyper | cancer_general | GABBR2 |
| chr9 | 101469603 | 101469796 | Hyper | cancer_general | GABBR2 | chr9 | 101470116 | 101470250 | Hyper | cancer_general | GABBR2 |
| chr9 | 101470968 | 101471071 | Hyper | cancer_general | GABBR2 | chr9 | 101471570 | 101471621 | Hyper | cancer_general | GABBR2 |
| chr9 | 101471860 | 101472009 | Hyper | tcga, cancer_general | | chr9 | 101705996 | 101706695 | Hyper | cancer_general | COL15A1 |
| chr9 | 104248579 | 104248623 | Hyper | cancer_general | TMEM246 | chr9 | 104249475 | 104249562 | Hyper | tcga | |
| chr9 | 104500625 | 104500774 | Hyper | cancer_general | | chr9 | 110228200 | 110228602 | Hyper | liver_tcga, cancer_general | |
| chr9 | 110251388 | 110251418 | Hyper | blood | KLF4 PALM2, Mir_548 | chr9 | 110252363 | 110252515 | Hyper | blood | KLF4 |
| chr9 | 112403170 | 112403200 | Hyper | cancer_general | | chr9 | 113341522 | 113341965 | Hyper | tcga, cancer_general | |
| chr9 | 113342299 | 113342340 | Hyper | cancer_general | PAPPA | chr9 | 115652966 | 115653425 | Hyper | cancer_general | SLC46A2 |
| chr9 | 118917024 | 118917079 | Hyper | cancer_general | | chr9 | 120175795 | 120175832 | Hyper | cancer_general | |
| chr9 | 120176104 | 120176151 | Hyper | cancer_general | | chr9 | 120176867 | 120176897 | Hyper | cancer_general | |
| chr9 | 120507409 | 120507439 | Hyper | cancer_general | DBC1 | chr9 | 122131481 | 122131642 | Hyper | cancer_general | DBC1 |
| chr9 | 122131880 | 122132227 | Hyper | tcga, liver_tcga | | chr9 | 123004898 | 123004928 | Hyper | esophageal | MIR147A |
| chr9 | 124535347 | 124535611 | Hyper | cancer_general | DAB2IP | chr9 | 126770257 | 126770298 | Hyper | cancer_general | LHX2, AK131516 |
| chr9 | 126771532 | 126771705 | Hyper | cancer_general | LHX2, AK131516 | chr9 | 126774517 | 126775144 | Hyper | cancer_general | LHX2, AK131516 |
| chr9 | 126775530 | 126775560 | Hyper | cancer_general | LHX2, AK131516 | chr9 | 126776044 | 126776119 | Hyper | cancer_general | AK131516, LHX2 |
| chr9 | 126777529 | 126777982 | Hyper | cancer_general | LHX2, AK131516 | chr9 | 126778329 | 126778496 | Hyper | cancer_general | AK131516, LHX2 |
| chr9 | 126779485 | 126780315 | Hyper | cancer_general | LHX2, AK131516 | chr9 | 126780811 | 126780898 | Hyper | cancer_general | LHX2, AK131516 |
| chr9 | 126783295 | 126783499 | Hyper | cancer_general | LHX2 | chr9 | 127212851 | 127213006 | Hyper | cancer_general | GPR144 |
| chr9 | 127265688 | 127266025 | Hyper | cancer_general | NR5A1 | chr9 | 127266387 | 127266534 | Hyper | cancer_general | NR5A1 |
| chr9 | 127920543 | 127920572 | Hyper | literature | PPP6C | chr9 | 128652200 | 128652232 | Hyper | cancer_general | PBX3 |
| chr9 | 129276718 | 129276820 | Hyper | cancer_general | | chr9 | 129372929 | 129373223 | Hyper | cancer_general | LMX1B |
| chr9 | 129376170 | 129376199 | Hyper | literature | LMX1B | chr9 | 129376889 | 129376918 | Hyper | literature | LMX1B |
| chr9 | 129377214 | 129377316 | Hyper | cancer_general | LMX1B | chr9 | 129377604 | 129378003 | Hyper | tcga, literature, cancer_general | LMX1B |
| chr9 | 129381111 | 129381180 | Hyper | cancer_general | LMX1B | chr9 | 129387434 | 129387464 | Hyper | cancer_general | LMX1B |
| chr9 | 129387800 | 129388200 | Hyper | cancer_general | LMX1B | chr9 | 129388996 | 129389192 | Hyper | cancer_general | LMX1B |
| chr9 | 129400986 | 129401195 | Hyper | cancer_general, breast | LMX1B | chr9 | 129445255 | 129445566 | Hyper | cancer_general | |
| chr9 | 129445783 | 129445813 | Hyper | cancer_general | LMX1B | chr9 | 129485841 | 129485923 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 130461642 | 130461742 | Hyper | cancer_general | C9orf17, BC032117, MIR3911, STXBP1 | chr9 | 130689626 | 130689749 | Hyper | liver_tcga | DPM2, PIP5KL1 |
| chr9 | 132382383 | 132383109 | Hyper | tcga, literature, cancer_general | NTMT1, C9orf50 | chr9 | 132804405 | 132804455 | Hyper | esophageal | FNBP1 |
| chr9 | 132804796 | 132804974 | Hyper | esophageal | FNBP1 | chr9 | 132805318 | 132805445 | Hyper | esophageal | FNBP1 |
| chr9 | 132805737 | 132805893 | Hyper | esophageal | FNBP1 | chr9 | 133308893 | 133308941 | Hyper | cancer_general | AK074396 |
| chr9 | 133534683 | 133534713 | Hyper | cancer_general | PRDM12 | chr9 | 133535734 | 133535839 | Hyper | cancer_general | PRDM12 |
| chr9 | 133536097 | 133536344 | Hyper | cancer_general | PRDM12 | chr9 | 133536778 | 133536869 | Hyper | tcga | PRDM12 |
| chr9 | 133537182 | 133537549 | Hyper | cancer_general | PRDM12 | chr9 | 133538169 | 133538728 | Hyper | cancer_general | PRDM12 |
| chr9 | 133539606 | 133539709 | Hyper | cancer_general | PRDM12 | chr9 | 133541059 | 133541192 | Hyper | cancer_general | PRDM12 |
| chr9 | 133541689 | 133542337 | Hyper | cancer_general | PRDM12 | chr9 | 133738343 | 133738372 | Hyper | literature | ABL1, AX748265 |
| chr9 | 133747505 | 133747534 | Hyper | literature | AX748265, ABL1 | chr9 | 134421797 | 134421835 | Hyper | blood | BARHL1, C9orfl71 |
| chr9 | 135037119 | 135037357 | Hyper | tcga | NTNG2 | chr9 | 135455407 | 135455585 | Hyper | cancer_general | BARHL1, C9orfl71 |
| chr9 | 135455996 | 135456065 | Hyper | cancer_general | BARHL1, C9orfl71 | chr9 | 135456496 | 135456526 | Hyper | cancer_general | BARHL1, C9orfl71 |
| chr9 | 135456897 | 135456932 | Hyper | cancer_general | BARHL1, C9orfl71 | chr9 | 135458477 | 135458597 | Hyper | cancer_general | DDX31, BARHL1 |
| chr9 | 135460001 | 135460176 | Hyper | cancer_general | BARHL1, DDX31 | chr9 | 135460869 | 135460899 | Hyper | cancer_general | DDX31, BARHL1 |
| chr9 | 135461511 | 135461773 | Hyper | cancer_general | DDX31, BARHL1 | chr9 | 135462048 | 135462967 | Hyper | cancer_general | DDX31, BARHL1 |
| chr9 | 135464798 | 135464918 | Hyper | cancer_general | ABRHL1 | chr9 | 135465948 | 135466132 | Hyper | cancer_general | DDX31, BARHL1 |
| chr9 | 135466344 | 135466660 | Hyper | cancer_general | DDX31, BARHL1 | chr9 | 135796801 | 135796830 | Hyper | literature | TSC1 |
| chr9 | 136474490 | 136474607 | Hyper | cancer_general | RXRA | chr9 | 137111397 | 137111426 | Hyper | liver_tcga | RXRA |
| chr9 | 137229892 | 137229921 | Hyper | liver_tcga |  | chr9 | 137299119 | 137299450 | Hyper | tcga, cancer_general |  |
| chr9 | 137533974 | 137534238 | Hyper | cancer_general | COL5A1 | chr9 | 137702189 | 137702222 | Hyper | esophageal | LOC101448202, COL5A1 |
| chr9 | 137979893 | 137980011 | Hyper | cancer_general | OLFM1 | chr9 | 137980258 | 137980288 | Hyper | cancer_general | OLFM1 |
| chr9 | 137980880 | 137980910 | Hyper | cancer_general | OLFM1 | chr9 | 138606307 | 138606372 | Hyper | cancer_general | KCNT1 |
| chr9 | 138606796 | 138606923 | Hyper | tcga | KCNT1 | chr9 | 139024723 | 139024782 | Hyper | cancer_general | LHX3, RBSG2 |
| chr9 | 139085228 | 139085360 | Hyper | cancer_general | RBSG2, LHX3 | chr9 | 139085924 | 139085978 | Hyper | cancer_general | QSOX2, LHX3, RBSG2 |
| chr9 | 139090500 | 139090578 | Hyper | cancer_general | QSOX2, LHX3, RBSG2 | chr9 | 139090793 | 139091369 | Hyper | cancer_general | QSOX2, LHX3, RBSG2 |
| chr9 | 139093681 | 139093890 | Hyper | cancer_general | QSOX2, LHX3, RBSG2 | chr9 | 139094705 | 139094873 | Hyper | cancer_general | QSOX2, LHX3, RBSG2 |
| chr9 | 139095340 | 139095485 | Hyper | cancer_general | QSOX2, LHX3, RBSG2 | chr9 | 139096650 | 139097006 | Hyper | cancer_general | LHX3, QSOX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 139399407 | 139399436 | Hyper | literature | NOTCH1 | chr9 | 139739236 | 139739300 | Hyper | cancer_general | PHPT1, MAMDC4, C9orf172, RABL6 |
| chr9 | 140024842 | 140025023 | Hyper | colorectal, cancer_general | GRIN1 | chr9 | 140032891 | 140032951 | Hyper | cancer_general | GRIN1 |
| chr9 | 140033426 | 140033642 | Hyper | cancer_general | GRIN1 | chr9 | 140033909 | 140034079 | Hyper | cancer_general | GRIN1 |
| chr9 | 140050969 | 140051354 | Hyper | liver_tcga, cancer_general | GRIN1 | chr9 | 140197122 | 140197263 | Hyper | hepatobiliary | NRARP, EXD3 |
| chr9 | 140771975 | 140772347 | Hyper | literature, cancer_general | CACNA1B, AK128414 | chr9 | 140772586 | 140773301 | Hyper | cancer_general | CACNA1B, AK128414 |
| chr19 | 462181 | 462269 | Hyper | blood | ODF3L2, SHC2 | chr19 | 591365 | 591416 | Hyper | cancer_general | HCN2, BSG |
| chr19 | 1220422 | 1220610 | Hyper | literature | C19orf26, STK11 | chr19 | 1221981 | 1222010 | Hyper | literature | C19orf26, STK11 |
| chr19 | 1308047 | 1308081 | Hyper | head_neck | EFNA2 | chr19 | 1401752 | 1401795 | Hyper | tcga | NDUFS7, DAZAP1, GAMT, KA126693 |
| chr19 | 1450319 | 1450390 | Hyper | cancer_general | APC2, RPS15 | chr19 | 1467423 | 1468188 | Hyper | cancer_general | C19orf25, APC2 |
| chr19 | 1524468 | 1524447 | Hyper | cancer_general | PLK5 | chr19 | 1754172 | 1754254 | Hyper | cancer_general | ONECUT3 |
| chr19 | 1754739 | 1754804 | Hyper | cancer_general | ONECUT3 | chr19 | 1757416 | 1757615 | Hyper | cancer_general | ONECUT3 |
| chr19 | 1762474 | 1762575 | Hyper | cancer_general | ONECUT3 | chr19 | 1764293 | 1764339 | Hyper | pancreas | ONECUT3 |
| chr19 | 1775076 | 1775239 | Hyper | head_neck | ATP8B3, ONECUT3 | chr19 | 1776376 | 1776534 | Hyper | pancreas, cancer general | ATP8B3, ONECUT3 |
| chr19 | 2135672 | 2135701 | Hyper | liver_tcga | JSRP1, MIR4321, AMH, SF3A2 | chr19 | 2251152 | 2251715 | Hyper | cancer_general | JSRP1, MIR4321, AMH, SF3A2 |
| chr19 | 2252066 | 2252658 | Hyper | tcga, cancer_general | JSRP1, MIR4321, AMH, SF3A2 | chr19 | 2252984 | 2253775 | Hyper | tcga, cancer_general | JSRP1, MIR4321, AMH, SF3A2 |
| chr19 | 2290253 | 2291034 | Hyper | tcga, cancer_general | SPPL2B, AX747191, LINGO3, C19orf35 | chr19 | 2302793 | 2302951 | Hyper | cancer_general | |
| chr19 | 3114998 | 3115027 | Hyper | literature | DKFZp434J194, GNA11 | chr19 | 3118927 | 3118956 | Hyper | literature | GNA11, DKFZp434J194 |
| chr19 | 3361139 | 3361388 | Hyper | tcga | NFIC | chr19 | 3659668 | 3659793 | Hyper | liver_tcga | PIP5K1C |
| chr19 | 3785649 | 3786260 | Hyper | tcga, liver_tcga, cancer_general | JA611290, MATK | chr19 | 3822111 | 3822203 | Hyper | tcga | ZFR2 |
| chr19 | 4101087 | 4101116 | Hyper | literature | MAP2K2 | chr19 | 4110565 | 4110597 | Hyper | literature | MAP2K2 |
| chr19 | 4117526 | 4117630 | Hyper | literature | MAP2K2 | chr19 | 4305057 | 4305086 | Hyper | literature | FSD1, TMIGD2 |
| chr19 | 4944145 | 4944174 | Hyper | liver_tcga | | chr19 | 5292812 | 5292844 | Hyper | pancreas | PTPRS |
| chr19 | 5338914 | 5339143 | Hyper | tcga, cancer_general | | chr19 | 6590325 | 6590478 | Hyper | cancer_general | CD70 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 7615996 | 7616025 | Hyper | liver_tcga | PNPLA6 | chr19 | 7746942 | 7747042 | Hyper | tcga | TRAPPC5, FCER2, C19orf59 |
| chr19 | 7795012 | 7795244 | Hyper | cancer_general | CD209, CLEC4G | chr19 | 7853028 | 7853157 | Hyper | cancer_general | CLEC4GP1 |
| chr19 | 7853361 | 7853460 | Hyper | cancer_general | CLEC4GP1 | chr19 | 8115235 | 8115276 | Hyper | cancer_general | CCL25 |
| chr19 | 9420142 | 9420240 | Hyper | esophageal | ZNF699 | chr19 | 9473564 | 9474056 | Hyper | liver_tcga, literature, cancer_general | ZNF177, ZNF559-ZNF177 |
| chr19 | 9517609 | 9517771 | Hyper | cancer_general | ZNF266 | chr19 | 9608895 | 9609036 | Hyper | cancer_general | ZNF560 |
| chr19 | 9609319 | 9609436 | Hyper | cancer_general, literature | ZNF560 | chr19 | 9903913 | 9904100 | Hyper | tcga, cancer_general | |
| chr19 | 10398209 | 10398285 | Hyper | cancer_general | ICAM4, ICAM1, ICAM5 | chr19 | 10405972 | 10406349 | Hyper | cancer_general | ZGLP1, FDX1L, ICAM5, ICAM4, ICAM1 |
| chr19 | 10406806 | 10407135 | Hyper | lung, cancer_general | ICAM1, LZGP1, FDX1L, ICAM5, ICAM4 | chr19 | 10527165 | 10527243 | Hyper | esophageal | PDE4A |
| chr19 | 10531419 | 10531512 | Hyper | tcga | PDE4A | chr19 | 10531964 | 10531994 | Hyper | cancer_general | PDE4A |
| chr19 | 10600431 | 10600460 | Hyper | literature | KEAP1 | chr19 | 10602274 | 10602348 | Hyper | literature | KEAP1 |
| chr19 | 10602565 | 10602864 | Hyper | literature | KEAP1 | chr19 | 10610138 | 10610260 | Hyper | literature | KEAP1 |
| chr19 | 10624751 | 10625465 | Hyper | cancer_general | S1PR5 | chr19 | 11134252 | 11134281 | Hyper | cancer_general | SMARCA4, RGL3, EPOR, SWSAP1 |
| chr19 | 11138507 | 11138536 | Hyper | literature | SMARCA4 | chr19 | 11492252 | 11492528 | Hyper | lung | |
| chr19 | 11591031 | 11591185 | Hyper | cancer_general | ZNF653, ELAVL3 | chr19 | 11592710 | 11592750 | Hyper | cancer_general | ELAVL3, ZNF653 |
| chr19 | 11593022 | 11593159 | Hyper | cancer_general | ZNF653, ELAVL3 | chr19 | 11689460 | 11689564 | Hyper | cancer_general | ACP5, BC039523 |
| chr19 | 11959912 | 11960077 | Hyper | cancer_general | ZNF439 | chr19 | 12163448 | 12163672 | Hyper | esophageal | ZNF878 |
| chr19 | 12163893 | 12163923 | Hyper | esophageal | ZNF878 | chr19 | 12175445 | 12175504 | Hyper | esophageal | ZNF844 |
| chr19 | 12175814 | 12176005 | Hyper | cancer_general | ZNF844 | chr19 | 12203028 | 12203744 | Hyper | liver_tcga, cancer_general | ZNF788 |
| chr19 | 12267019 | 12267667 | Hyper | tcga, cancer_general | ZNF136, ZNF625 | chr19 | 12305839 | 12306263 | Hyper | liver_tcga, literature, cancer_general | AX721123, ZNF136, AK023304 |
| chr19 | 12476492 | 12476556 | Hyper | esophageal | ZNF442 | chr19 | 12595109 | 12595307 | Hyper | esophageal | ZNF709 |
| chr19 | 12595845 | 12595896 | Hyper | esophageal | ZNF709 | chr19 | 12606381 | 12606511 | Hyper | esophageal | ZNF709 |
| chr19 | 12750987 | 12751056 | Hyper | cancer_general | MAN2B1 | chr19 | 12952000 | 12952139 | Hyper | cancer_general | RTBDN, MAST1 |
| chr19 | 12996169 | 12996280 | Hyper | pancreas | DNASE2, GCDH, KLF1 | chr19 | 13113454 | 13113668 | Hyper | liver_tcga | NFIX |
| chr19 | 13210225 | 13210316 | Hyper | cancer_general | TRMT1, LYL1, NFIX | chr19 | 13616696 | 13617256 | Hyper | cancer_general | CACNA1A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 13618288 | 13618381 | Hyper | cancer_general | CACNA1A | chr19 | 14584240 | 14584775 | Hyper | cancer_general | GIPC1, PTGER1, PKN1 |
| chr19 | 15090172 | 15090499 | Hyper | cancer_general | SLC1A6 | chr19 | 15121685 | 15121894 | Hyper | cancer_general | CCDC105 |
| chr19 | 15122120 | 15122238 | Hyper | tcga | CCDC105 | chr19 | 15288433 | 15288856 | Hyper | cancer_general | NOTCH3 |
| chr19 | 15342734 | 15343373 | Hyper | cancer_general, liver_tcga | BRD4, EPHX3 | chr19 | 15344107 | 15344325 | Hyper | cancer_general | BRD4, EPHX3 |
| chr19 | 15580685 | 15580714 | Hyper | literature | PGLYRP2, RASAL3 | chr19 | 16999599 | 16999782 | Hyper | literature | SIN3B, F2RL3, CPAMD8 |
| chr19 | 17007086 | 17007662 | Hyper | cancer_general | CPAMD8, F2RL3 | chr19 | 17008523 | 17008799 | Hyper | cancer_general, liver_tcga | CPAMD8, F2RL3 |
| chr19 | 17392641 | 17392866 | Hyper | tcga | ANKLE1, BABAM1 | chr19 | 17717286 | 17717315 | Hyper | literature | UNC13A |
| chr19 | 17791182 | 17791211 | Hyper | literature | UNC13A | chr19 | 17943423 | 17943452 | Hyper | literature | JAK3 |
| chr19 | 17945891 | 17945983 | Hyper | literature | JAK3 | chr19 | 17947991 | 17948023 | Hyper | literature | JAK3 |
| chr19 | 17949094 | 17949123 | Hyper | literature | JAK3 | chr19 | 17958490 | 17958839 | Hyper | tcga | JAK3 |
| chr19 | 17983537 | 17983834 | Hyper | cancer_general | SLC5A5 | chr19 | 18271894 | 18271923 | Hyper | literature | PIK3R2, MAST3 |
| chr19 | 18278047 | 18278076 | Hyper | literature | PIK3R2, IFI30 | chr19 | 18343439 | 18343569 | Hyper | cancer_general | PDE4C |
| chr19 | 18343921 | 18343963 | Hyper | cancer_general | PDE4C | chr19 | 18714552 | 18714675 | Hyper | cancer_general | TMEM59L, CRLF1 |
| chr19 | 18811560 | 18811804 | Hyper | tcga | CRTC1 | chr19 | 18899432 | 18899652 | Hyper | cancer_general | COMP, CRTC1 |
| chr19 | 18901828 | 18902095 | Hyper | tcga, cancer_general | COMP, CRTC1 | chr19 | 18980760 | 18980897 | Hyper | cancer_general | UPF1, CERS1, GDF1 |
| chr19 | 19260030 | 19260101 | Hyper | literature | MEF2B, MEF2BNB-MEF2B | chr19 | 19261519 | 19261548 | Hyper | literature | MEF2B, MEF2BNB-MEF2B |
| chr19 | 19651961 | 19652066 | Hyper | liver_tcga | CILP2, YJEFN3 | chr19 | 19729251 | 19729395 | Hyper | liver_tcga | LPAR2, PBX4 |
| chr19 | 19739172 | 19739428 | Hyper | tcga, liver_tcga | GMIP, LPAR2, PBX4 | chr19 | 20011955 | 20012149 | Hyper | liver_tcga, cancer_general | ZNF93, ZNF253 |
| chr19 | 20188693 | 20188872 | Hyper | cancer_general | ZNF90 | chr19 | 20189322 | 20189438 | Hyper | cancer_general | ZNF90 |
| chr19 | 21646407 | 21646437 | Hyper | cancer_general | CR627135 | chr19 | 21688814 | 21688912 | Hyper | esophageal | ZNF429, LINC00664 |
| chr19 | 21769300 | 21769444 | Hyper | tcga | BC033373, AX748435 | chr19 | 22018523 | 22018805 | Hyper | tcga | ZNF43 |
| chr19 | 22034198 | 22034813 | Hyper | cancer_general | ZNF43 | chr19 | 22610635 | 22610747 | Hyper | cancer_general | MEF2B |
| chr19 | 22715140 | 22715443 | Hyper | cancer_general | | chr19 | 23254189 | 23254219 | Hyper | cancer_general | |
| chr19 | 23257703 | 23258694 | Hyper | cancer_general | | chr19 | 23299748 | 23300080 | Hyper | tcga, cancer_general | |
| chr19 | 23432562 | 23432723 | Hyper | esophageal | AK023040, ZNF724P | chr19 | 23433143 | 23433296 | Hyper | esophageal | ZNF98 |
| chr19 | 23456615 | 23456881 | Hyper | esophageal | AK023040 | chr19 | 23598274 | 23598326 | Hyper | cancer_general | AK023040, ZNF724P, BC043213, AK022793 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 24154592 | 24154621 | Hyper | liver_tcga | | chr19 | 24216975 | 24217023 | Hyper | esophageal | ZNF254, AK092150, AK092080 |
| chr19 | 29284452 | 29284719 | Hyper | cancer_general | | chr19 | 30015934 | 30016712 | Hyper | cancer_general | VSTM2B, LOC284395 |
| chr19 | 30016914 | 30018608 | Hyper | cancer_general | VSTM2B, LOC284395 | chr19 | 30019145 | 30019838 | Hyper | tcga, cancer_general | VSTM2B, LOC284395 |
| chr19 | 30020093 | 30020473 | Hyper | cancer_general | VSTM2B, LOC284395 | chr19 | 30021125 | 30021193 | Hyper | cancer_general | VSTM2B, LOC284395 |
| chr19 | 30215542 | 30215571 | Hyper | tcga | C19orf12 | chr19 | 30713480 | 30713706 | Hyper | cancer_general | |
| chr19 | 30713909 | 30714047 | Hyper | cancer_general | | chr19 | 30714403 | 30714433 | Hyper | cancer_general | |
| chr19 | 30715402 | 30715766 | Hyper | cancer_general | | chr19 | 30716313 | 30716576 | Hyper | cancer_general | |
| chr19 | 30716812 | 30718149 | Hyper | tcga, cancer_general | | chr19 | 30718847 | 30718913 | Hyper | cancer_general | |
| chr19 | 30719449 | 30720067 | Hyper | tcga, cancer_general | | chr19 | 30865713 | 30866436 | Hyper | cancer_general, tcga | ZNF536 |
| chr19 | 31839765 | 31839873 | Hyper | cancer_general | TSHZ3 | chr19 | 31841937 | 31842389 | Hyper | tcga, cancer_general | TSHZ3 |
| chr19 | 31842596 | 31842646 | Hyper | cancer_general | TSHZ3 | chr19 | 32715673 | 32715741 | Hyper | cancer_general | |
| chr19 | 33167116 | 33167431 | Hyper | cancer_general | RGS9BP, ANKRD27 | chr19 | 33685544 | 33685581 | Hyper | esophageal | LRP3 |
| chr19 | 33792159 | 33792524 | Hyper | blood | CEBPA-AS1, CEBPA | chr19 | 33794675 | 33794760 | Hyper | tcga | CEBPA-AS1, CEBPA |
| chr19 | 34112288 | 34112320 | Hyper | cancer_general | CHST8 | chr19 | 34112524 | 34112973 | Hyper | cancer_general | CHST8 |
| chr19 | 34113349 | 34113587 | Hyper | cancer_general | CHST8 | chr19 | 34114006 | 34114113 | Hyper | cancer_general | CHST8 |
| chr19 | 34533139 | 34533169 | Hyper | head_neck | | chr19 | 34972464 | 34972494 | Hyper | blood | WTIP |
| chr19 | 34973225 | 34973255 | Hyper | cancer_general | WTIP | chr19 | 34973656 | 34973697 | Hyper | cancer_general | WTIP |
| chr19 | 34973932 | 34973965 | Hyper | pancreas | WTIP | chr19 | 35264085 | 35264119 | Hyper | esophageal | ZNF599 |
| chr19 | 35396013 | 35396370 | Hyper | cancer_general | LINC00904, BC031235 | chr19 | 36048595 | 36048771 | Hyper | cancer_general, liver_tcga | ATP4A |
| chr19 | 36049327 | 36049462 | Hyper | tcga | ATP4A | chr19 | 36334979 | 36335147 | Hyper | cancer_general | NPHS1 |
| chr19 | 36347892 | 36348048 | Hyper | tcga | KIRREL2 | chr19 | 36450106 | 36450372 | Hyper | tcga, cancer_general | |
| chr19 | 36523333 | 36523480 | Hyper | cancer_general | THAP8, CLIP3, BC071809 | chr19 | 36736027 | 36736057 | Hyper | cancer_general | ZNF146 |
| chr19 | 36736319 | 36736491 | Hyper | cancer_general | ZNF146 | chr19 | 36822324 | 36822892 | Hyper | cancer_general | ZFP14, LINC00665 ZFP82, LOC644189 |
| chr19 | 36909050 | 36909935 | Hyper | tcga, liver_tcga, cancer_general | LOC644189, ZFP82 | chr19 | 36912354 | 36912398 | Hyper | cancer_general | |
| chr19 | 37095665 | 37096575 | Hyper | tcga, literature, cancer_general | ZNF382, ZNF529 | chr19 | 37263532 | 37263584 | Hyper | esophageal | AX747375, BC024306, ZNF850 |
| chr19 | 37264222 | 37264421 | Hyper | cancer_general | BC024306, AX747375, ZNF850 | chr19 | 37288013 | 37288765 | Hyper | tcga, cancer_general | ZNF790-AS1 |
| chr19 | 37341761 | 37341962 | Hyper | esophageal | ZNF345, ZNF790 | chr19 | 37407127 | 37407443 | Hyper | cancer_general | ZNF568, ZNF829 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 37464048 | 37464696 | Hyper | tcga, cancer_general | ZNF568 | chr19 | 37569289 | 37569554 | Hyper | esophageal | ZNF420 |
| chr19 | 37808445 | 37808485 | Hyper | esophageal | HKR1 | chr19 | 37959858 | 37959963 | Hyper | cancer_general | ZNF570, ZNF569 |
| chr19 | 37997433 | 37998138 | Hyper | cancer_general, tcga | ZNF793 | chr19 | 38042365 | 38042693 | Hyper | cancer_general | ZNF571, ZNF540, ZNF571-AS1 |
| chr19 | 38085254 | 38086066 | Hyper | esophageal | ZNF540, ZNF571 | chr19 | 38146062 | 38146247 | Hyper | esophageal | ZFP30 |
| chr19 | 38146457 | 38146568 | Hyper | esophageal | ZFP30 | chr19 | 38182884 | 38183299 | Hyper | cancer_general, tcga, liver_tcga, literature | ZNF607 |
| chr19 | 38308080 | 38308466 | Hyper | cancer_general | LOC644554, LOC100631378 | chr19 | 38747159 | 38747582 | Hyper | tcga, cancer_general, liver_tcga | SPINT2, PPP1R14A |
| chr19 | 38755272 | 38755344 | Hyper | tcga, liver_tcga | SPINT2, PPP1R14A | chr19 | 39687663 | 39687844 | Hyper | cancer_general | SYCN, NCCRP1 |
| chr19 | 39754874 | 39755358 | Hyper | cancer_general | IFNL2, SELV, DLL3 | chr19 | 39993477 | 39993664 | Hyper | cancer_general | DLL3 |
| chr19 | 39997688 | 39997813 | Hyper | cancer_general | SELV, DLL3 | chr19 | 40006177 | 40006306 | Hyper | tcga | DLL3, SELV |
| chr19 | 40006576 | 40006639 | Hyper | cancer_general | SELV, DLL3 | chr19 | 40724000 | 40724263 | Hyper | cancer_general | CNTD2, TTC9B, MAP3K10 |
| chr19 | 40762943 | 40762972 | Hyper | literature | AKT2 | chr19 | 41018510 | 41019031 | Hyper | cancer_general, pancreas, liver_tcga | SPTBN4 |
| chr19 | 41025539 | 41025683 | Hyper | cancer_general | SPTBN4, SPTBN4, SHKBP1 | chr19 | 41059909 | 41060306 | Hyper | cancer_general | LTBP4 |
| chr19 | 41073587 | 41073677 | Hyper | cancer_general | | chr19 | 41119177 | 41119633 | Hyper | cancer_general | |
| chr19 | 41354666 | 41354722 | Hyper | cancer_general | CYP2A6 | chr19 | 41641831 | 41641886 | Hyper | cancer_general | DQ590318, CYP2F1 |
| chr19 | 41698787 | 41698920 | Hyper | blood | CYP2S1 | chr19 | 42028502 | 42028549 | Hyper | pancreas | |
| chr19 | 42827891 | 42828266 | Hyper | liver_tcga, literature, cancer_general | MEGF8, TMEM145 | chr19 | 44203830 | 44203877 | Hyper | cancer_general | |
| chr19 | 44405908 | 44406087 | Hyper | cancer_general | LOC100505715, ZNF229 | chr19 | 44905499 | 44905529 | Hyper | cancer_general | ZNF285 |
| chr19 | 44952282 | 44952881 | Hyper | tcga, cancer_general | | chr19 | 45300144 | 45300197 | Hyper | cancer_general | CBLC |
| chr19 | 45655393 | 45656363 | Hyper | cancer_general | TRAPPC6A, NKPD1, PPP1R37 | chr19 | 45656682 | 45656913 | Hyper | cancer_general | TRAPPC6A, NKPD1, PPP1R37 |
| chr19 | 45657212 | 45657284 | Hyper | cancer_general | TRAPPC6A, NKPD1, PPP1R37 | chr19 | 45889946 | 45889397 | Hyper | cancer_general | PPP1R13L |
| chr19 | 46002048 | 46002320 | Hyper | cancer_general | PPM1N, VASP, RTN2 | chr19 | 46379914 | 46380148 | Hyper | tcga | FOXA3, IRF2BP1 |
| chr19 | 46916725 | 46917075 | Hyper | literature, cancer_general | CCDC8 | chr19 | 46930129 | 46930200 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 46974552 | 46974700 | Hyper | literature, cancer_general | PPP5D1, PNMAL1 | chr19 | 46992718 | 46992866 | Hyper | cancer_general | PNMAL2, BC132841, PPP5D1 |
| chr19 | 46993164 | 46993388 | Hyper | cancer_general | PNMAL2, BC132841, PPP5D1 | chr19 | 46996501 | 46996918 | Hyper | tcga, literature, cancer_general | BC132841, PNMAL2, PPP5D1 |
| chr19 | 47152617 | 47153011 | Hyper | cancer_general | DACT3 | chr19 | 47776713 | 47776742 | Hyper | liver_tcga | PRR24, CCDC9 |
| chr19 | 47910482 | 47910517 | Hyper | cancer_general | MEIS3 | chr19 | 47933311 | 47933732 | Hyper | cancer_general | SLC8A2 |
| chr19 | 47951288 | 47951318 | Hyper | liver_tcga | SLC8A2 | chr19 | 48076642 | 48076672 | Hyper | cancer_general | |
| chr19 | 48918100 | 48918598 | Hyper | tcga, cancer_general | Mir_324, GRIN2D | chr19 | 49127373 | 49127674 | Hyper | cancer_general, liver_tcga | SPHK2, DBP, RPL18 |
| chr19 | 49256396 | 49256438 | Hyper | hepatobiliary | FGF21, FUT1, IZUMO1 | chr19 | 49399218 | 49399310 | Hyper | cancer_general | NUCB1, Mir_324, TULP2 |
| chr19 | 49575460 | 49575489 | Hyper | liver_tcga | KCNA7 | chr19 | 49646149 | 49646213 | Hyper | cancer_general | PPFIA3, HRC |
| chr19 | 49935736 | 49936174 | Hyper | cancer_general | LOC100507003, PTH2, SLC17A7 | chr19 | 49936864 | 49936894 | Hyper | cancer_general | SLC17A7, LOC100507003 |
| chr19 | 50316244 | 50316468 | Hyper | liver_tcga, colorectal | MED25, FUZ, AP2A1 | chr19 | 50553680 | 50553709 | Hyper | liver_tcga | FLJ26850, ZNF473 |
| chr19 | 50553997 | 50554510 | Hyper | liver_tcga, cancer_general | FLJ26850, ZNF473 | chr19 | 50816431 | 50816474 | Hyper | cancer_general | KCNC3, MYH14 |
| chr19 | 50833828 | 50833863 | Hyper | cancer_general | NAPSB, NR1H2, KCNC3 | chr19 | 51041149 | 51041189 | Hyper | head_neck | LRRC4B |
| chr19 | 51161225 | 51161255 | Hyper | cancer_general | SHANK1, C19orf81 | chr19 | 51162197 | 51162527 | Hyper | tcga, cancer_general | SHANK1, C19orf81 |
| chr19 | 51171219 | 51171278 | Hyper | cancer_general | SHANK1, C19orf81 | chr19 | 51171828 | 51171861 | Hyper | cancer_general | SHANK1, C19orf81 |
| chr19 | 51227719 | 51227785 | Hyper | cancer_general | CLEC11A, SHANK1 | chr19 | 51228049 | 51228079 | Hyper | pancreas | SHANK1, CLEC11A |
| chr19 | 51228308 | 51228507 | Hyper | cancer_general | CLEC11A, SHANK1 | chr19 | 51520423 | 51520453 | Hyper | cancer_general | KLK11, KLK10, KLK9 |
| chr19 | 51830845 | 51831128 | Hyper | cancer_general | VSIG10L, IGLON5 | chr19 | 51831360 | 51831390 | Hyper | cancer_general | VSIG10L, IGLON5 |
| chr19 | 51925127 | 51925272 | Hyper | liver_tcga | LOC100129083, SIGLEC10 | chr19 | 52097689 | 52097732 | Hyper | esophageal | FLJ30403, AX748312, ZNF175 |
| chr19 | 52207254 | 52207367 | Hyper | tcga, liver_tcga | LINC00085, HAS1 | chr19 | 52222523 | 52223131 | Hyper | cancer_general | HAS1 |
| chr19 | 52452316 | 52452447 | Hyper | liver_tcga | BC014606, ZNF613 | chr19 | 52552104 | 52552151 | Hyper | pancreas | ZNF432 |
| chr19 | 52715963 | 52715992 | Hyper | literature | PPP2R1A | chr19 | 52839588 | 52839938 | Hyper | tcga, cancer_general | ZNF610, AK097759 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 52872924 | 52873440 | Hyper | tcga, cancer_general | ZNF880, ZNF610 | chr19 | 52956805 | 52956848 | Hyper | cancer_general | ZNF578 |
| chr19 | 53031185 | 53031215 | Hyper | esophageal | ZNF808 | chr19 | 53073293 | 53073354 | Hyper | cancer_general | ZNF701 |
| chr19 | 53073563 | 53073987 | Hyper | cancer_general | ZNF701 | chr19 | 53141619 | 53141745 | Hyper | liver_tcga | |
| chr19 | 53193858 | 53193893 | Hyper | esophageal | | chr19 | 53194281 | 53194396 | Hyper | cancer_general | |
| chr19 | 53496649 | 53496846 | Hyper | tcga, liver_tcga | ZNF702P | chr19 | 53561668 | 53561733 | Hyper | cancer_general | ZNF160, ERVV-2 |
| chr19 | 53635952 | 53636091 | Hyper | tcga | ZNF347, ZNF415 | chr19 | 53661647 | 53661902 | Hyper | tcga, cancer_general | ZNF665, ZNF347 |
| chr19 | 53662174 | 53662694 | Hyper | tcga, cancer_general | ZNF665, NZF347 | chr19 | 53696414 | 53696580 | Hyper | cancer_general | ZNF665 |
| chr19 | 53700596 | 53700729 | Hyper | cancer_general | ZNF665 | chr19 | 53757895 | 53758247 | Hyper | tcga, cancer_general | ZNF677, VN1R2 |
| chr19 | 53811858 | 53811988 | Hyper | cancer_general | | chr19 | 53836936 | 53836975 | Hyper | esophageal | ZNF845 |
| chr19 | 53837377 | 53837432 | Hyper | esophageal | ZNF845 | chr19 | 53970501 | 53970725 | Hyper | tcga, cancer_general | ZNF813, ZNF761 |
| chr19 | 53970968 | 53971157 | Hyper | cancer_general | ZNF813, ZNF761 | chr19 | 54023887 | 54024196 | Hyper | tcga | ZNF331 |
| chr19 | 54024521 | 54024884 | Hyper | tcga, cancer_general | ZNF331 | chr19 | 54369555 | 54369681 | Hyper | liver_tcga | MYADM |
| chr19 | 54411125 | 54411168 | Hyper | cancer_general | CACNG7 | chr19 | 54411556 | 54411586 | Hyper | cancer_general | CACNG7 |
| chr19 | 54412873 | 54412985 | Hyper | cancer_general | CACNG7 | chr19 | 54445344 | 54445513 | Hyper | tcga, liver_tcga, cancer_general | CACNG7 |
| chr19 | 54481771 | 54481968 | Hyper | cancer_general | MIR935, ACCNG8 | chr19 | 54483173 | 54483546 | Hyper | cancer_general | MIR935, CACNG8 |
| chr19 | 54485403 | 54485823 | Hyper | liver_tcga, cancer_general | MIR935, CACNG6, CACNG8 | chr19 | 54976488 | 54976518 | Hyper | liver_tcga | CDC42EP5, LENG9, KIAA1932 |
| chr19 | 55598767 | 55598888 | Hyper | tcga | EPS8L1, PPP1R12C, Mir_324 | chr19 | 55629883 | 55630028 | Hyper | cancer_general | |
| chr19 | 56159273 | 56159499 | Hyper | tcga | CCDC106, U2AF2, ZNF581, ZNF580 | chr19 | 56189937 | 56189966 | Hyper | liver_tcga | EPN1, U2AF2 |
| chr19 | 56728678 | 56728976 | Hyper | cancer_general | ZSCANSA | chr19 | 56879501 | 56880008 | Hyper | tcga, cancer_general | ZNF542 |
| chr19 | 56904740 | 56905203 | Hyper | cancer_general, tcga | ZNF582-AS1, ZNF582 | chr19 | 56915320 | 56915428 | Hyper | cancer_general | ZNF583, ZNF582-AS1 |
| chr19 | 56988557 | 56988716 | Hyper | cancer_general | ZNF667-AS1, ZNF667 | chr19 | 56989528 | 56989754 | Hyper | tcga, cancer_general | ZNF667-AS1, ZNF667 |
| chr19 | 57050463 | 57050493 | Hyper | cancer_general | BX647249, ZFP28 | chr19 | 57149579 | 57149619 | Hyper | cancer_general | SMIM17 |
| chr19 | 57154885 | 57155017 | Hyper | cancer_general | SMIM17 | chr19 | 57182994 | 57183356 | Hyper | tcga, cancer_general | ZNF835 |
| chr19 | 57276656 | 57276700 | Hyper | cancer_general | BC036412, ZIM2, FJ997633 | chr19 | 57610855 | 57610985 | Hyper | tcga | |
| chr19 | 57617522 | 57618121 | Hyper | cancer_general | | chr19 | 57683148 | 57683295 | Hyper | cancer_general | DUXA |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 57862395 | 57862783 | Hyper | tcga, colorectal | ZNF304 | chr19 | 57863009 | 57863148 | Hyper | colorectal, cancer_general | ZNF304 |
| chr19 | 58011124 | 58011281 | Hyper | cancer_general | ZNF773, ZNF419 | chr19 | 58038805 | 58038969 | Hyper | cancer_general | ZNF549 |
| chr19 | 58095006 | 58095835 | Hyper | tcga, cancer_general | ZIK1, ZNF416 | chr19 | 58111632 | 58111783 | Hyper | tcga | AX721128, ZNF530, ZIK1 |
| chr19 | 58125544 | 58125881 | Hyper | tcga | ZNF134, ZNF211, AX721128, ZNF530 | chr19 | 58144494 | 58144701 | Hyper | head_neck | ZNF211 |
| chr19 | 58219839 | 58220832 | Hyper | liver_tcga, literature, cancer_general | ZNF154 | chr19 | 58238326 | 58239088 | Hyper | tcga, cancer_general | ZNF671 |
| chr19 | 58400079 | 58400175 | Hyper | cancer_general | ZNF814 | chr19 | 58400417 | 58400518 | Hyper | cancer_general | ZNF814 |
| chr19 | 58458754 | 58459201 | Hyper | tcga, cancer_general | ZNF256 | chr19 | 58514518 | 58514552 | Hyper | cancer_general | LOC100128398, ZNF606 |
| chr19 | 58520739 | 58520941 | Hyper | cancer_general | LOC100128398, ZNF606 | chr19 | 58545145 | 58545837 | Hyper | cancer_general, pancreas, literature, liver_tcga | ZSCAN1 |
| chr19 | 58570528 | 58570666 | Hyper | cancer_general | ZNF135, ZSCAN18, ZNF329 | chr19 | 58609254 | 58609854 | Hyper | tcga, cancer_general | ZSCAN18 |
| chr19 | 58629886 | 58629975 | Hyper | liver_tcga, literature | | chr19 | 58661894 | 58662094 | Hyper | cancer_general | |
| chr19 | 58666171 | 58666313 | Hyper | cancer_general | RPS5, MIR4754, LOC646862 | chr19 | 58740086 | 58740118 | Hyper | esophageal | ZNF544 |
| chr19 | 58907689 | 58908195 | Hyper | cancer_general | | chr19 | 58951271 | 58951916 | Hyper | cancer_general, tcga | ZNF132, DQ581862 |
| chr10 | 1651331 | 1651374 | Hyper | cancer_general | | chr10 | 1774858 | 1774887 | Hyper | literature | |
| chr10 | 1779417 | 1779744 | Hyper | tcga, cancer_general | | chr10 | 3109360 | 3109459 | Hyper | liver_tcga | |
| chr10 | 7449954 | 7451390 | Hyper | tcga, colorectal, cancer_general | SFMBT2 | chr10 | 7452227 | 7452777 | Hyper | tcga, cancer_general, colorectal | PFKP |
| chr10 | 7453313 | 7453930 | Hyper | tcga, colorectal, cancer_general | SFMBT2 | chr10 | 7708274 | 7708304 | Hyper | cancer_general | SFMBT2 |
| chr10 | 7708790 | 7709087 | Hyper | cancer_general, tcga | ITIH5 | chr10 | 7709723 | 7709752 | Hyper | literature | ITIH5 |
| chr10 | 8075930 | 8075971 | Hyper | cancer_general | GATA3-AS1, BC036297, GATA3 | chr10 | 8076338 | 8076487 | Hyper | cancer_general | ITIH5 |
| chr10 | 8076804 | 8077374 | Hyper | cancer_general | GATA3-AS1, BC036297, GATA3 | chr10 | 8077874 | 8078218 | Hyper | cancer_general | GATA3-AS1, BC036297 |
| chr10 | 8085039 | 8085721 | Hyper | cancer_general | | chr10 | 8085978 | 8086010 | Hyper | cancer_general | GATA3-AS1, BC036297, GATA3 |
| chr10 | 8091895 | 8092278 | Hyper | tcga, cancer_general | GATA3-AS1, BC036297, GATA3 | chr10 | 8093738 | 8093985 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 8095603 | 8095845 | Hyper | tcga, cancer_general | GATA3, BC036297, GATA3-AS1 | chr10 | 8096160 | 8096190 | Hyper | cancer_general | GATA3, BC036297, GATA3-AS1 |
| chr10 | 8096975 | 8097197 | Hyper | tcga, cancer_general | GATA3, BC036297, GATA3-AS1 | chr10 | 8097474 | 8097537 | Hyper | cancer_general | GATA3, BC036297, GATA3-AS1 |
| chr10 | 11059715 | 11060062 | Hyper | pancreas, liver_tcga, cancer_general | CELF2 | chr10 | 11206206 | 11206235 | Hyper | literature | CELF2 |
| chr10 | 11207179 | 11207276 | Hyper | cancer_general | CELF2 | chr10 | 12390825 | 12390995 | Hyper | esophageal | CAMK1D |
| chr10 | 12391870 | 12392327 | Hyper | esophageal | CAMK1D | chr10 | 13043386 | 13043425 | Hyper | cancer_general | AK311458 |
| chr10 | 13933005 | 13933035 | Hyper | cancer_general | FRMD4A | chr10 | 13933436 | 13934183 | Hyper | tcga, cancer_general | FRMD4A |
| chr10 | 15761292 | 15761671 | Hyper | cancer_general | ITGA8 | chr10 | 15762124 | 15762154 | Hyper | cancer_general | ITGA8 |
| chr10 | 16562086 | 16563909 | Hyper | literature, cancer_general | C1QL3 | chr10 | 17269628 | 17269789 | Hyper | literature | VIM, BC078172 |
| chr10 | 17270072 | 17270445 | Hyper | literature | VIM, BC078172 | chr10 | 17270991 | 17271625 | Hyper | tcga, liver_tcga, cancer_general, literature | VIM, BC078172 |
| chr10 | 17271914 | 17272233 | Hyper | tcga, literature | VIM, BC078172 | chr10 | 17272601 | 17272630 | Hyper | literature | VIM, BC078172 |
| chr10 | 17273172 | 17273201 | Hyper | literature | VIM, BC078172 | chr10 | 17496214 | 17496734 | Hyper | cancer_general | |
| chr10 | 18429245 | 18429287 | Hyper | cancer_general | CACNB2 | chr10 | 18429628 | 18429774 | Hyper | tcga | CACNB2 |
| chr10 | 21462533 | 21462607 | Hyper | blood | NEBL-AS1 | chr10 | 21462970 | 21463023 | Hyper | blood | NEBL-AS1 |
| chr10 | 21805217 | 21805277 | Hyper | cancer_general | AK303207, SKIDA1, AK055656 | chr10 | 22541638 | 22542265 | Hyper | tcga, liver_tcga, cancer_general | LOC100130992 |
| chr10 | 22624022 | 22625978 | Hyper | liver_tcga, cancer_general | COMMD3-BMI1, SPAG6, BMI1 | chr10 | 22633985 | 22634578 | Hyper | liver_tcga, cancer_general | SPAG6 |
| chr10 | 22764649 | 22765901 | Hyper | liver_tcga, cancer_general | | chr10 | 23216865 | 23216945 | Hyper | cancer_general | ARMC3 |
| chr10 | 23460355 | 23460471 | Hyper | cancer_general | SNORA40 | chr10 | 23461222 | 23461754 | Hyper | cancer_general | SNORA40 |
| chr10 | 23462059 | 23462910 | Hyper | cancer_general | SNORA40 | chr10 | 23463150 | 23464077 | Hyper | cancer_general | SNORA40 |
| chr10 | 23479876 | 23481086 | Hyper | cancer_general | PTF1A | chr10 | 23481321 | 23481515 | Hyper | cancer_general | PTF1A |
| chr10 | 23481936 | 23482445 | Hyper | cancer_general | PTF1A | chr10 | 23483828 | 23484618 | Hyper | cancer_general | PTF1A |
| chr10 | 23486264 | 23486328 | Hyper | cancer_general | PTF1A | chr10 | 23487742 | 23487978 | Hyper | cancer_general | PTF1A |
| chr10 | 23488393 | 23489158 | Hyper | cancer_general | KIAA1217 | chr10 | 23489409 | 23489439 | Hyper | cancer_general | PTF1A |
| chr10 | 23982438 | 23982820 | Hyper | cancer_general | KIAA1217 | chr10 | 23983194 | 23983247 | Hyper | cancer_general | KIAA1217 |
| chr10 | 23983481 | 23983700 | Hyper | tcga, cancer_general | | chr10 | 23984087 | 23984226 | Hyper | cancer_general | KIAA1217 |
| chr10 | 23984923 | 23984991 | Hyper | cancer_general | KIAA1217 | chr10 | 25464619 | 25464915 | Hyper | cancer_general | GPR158, GPR158-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 25465421 | 25465517 | Hyper | cancer_general | GPR158-AS1, GPR158 | chr10 | 26055811 | 26055841 | Hyper | cancer_general | |
| chr10 | 26223001 | 26223424 | Hyper | cancer_general | MYO3A | chr10 | 26224031 | 26224061 | Hyper | cancer_general | MYO3A |
| chr10 | 26500619 | 26500915 | Hyper | cancer_general | GAD2, MYO3A | chr10 | 26501539 | 26501589 | Hyper | cancer_general | GAD2, MYO3A |
| chr10 | 26503693 | 26503731 | Hyper | cancer_general | GAD2, MYO3A | chr10 | 26504114 | 26504159 | Hyper | cancer_general | GAD2, MYO3A |
| chr10 | 26504491 | 26505227 | Hyper | cancer_general | GAD2, OMY3A | chr10 | 26505440 | 26505705 | Hyper | cancer_general | GAD2, MYO3A |
| chr10 | 26506057 | 26506163 | Hyper | cancer_general | GAD2, MYO3A | chr10 | 26506373 | 26507400 | Hyper | cancer_general | GAD2, MYO3A |
| chr10 | 26681099 | 26681129 | Hyper | cancer_general | APBB1IP | chr10 | 26727098 | 26727368 | Hyper | cancer_general | APBB1IP |
| chr10 | 26727604 | 26727832 | Hyper | cancer_general | | chr10 | 27547946 | 27548484 | Hyper | cancer_general | AK125237, LRRC37A6P |
| chr10 | 28030892 | 28030925 | Hyper | cancer_general | MKX | chr10 | 28032966 | 28033020 | Hyper | cancer_general | MKX |
| chr10 | 28033410 | 28033481 | Hyper | cancer_general | MKX | chr10 | 28033770 | 28034341 | Hyper | cancer_general | MKX |
| chr10 | 28034575 | 28035300 | Hyper | tcga, cancer_general | MKX | chr10 | 28035615 | 28035782 | Hyper | tcga, cancer_general | MKX |
| chr10 | 28287373 | 28287557 | Hyper | tcga | | chr10 | 28287777 | 28288070 | Hyper | cancer_general | |
| chr10 | 28657255 | 28657343 | Hyper | literature | | chr10 | 28958086 | 28958129 | Hyper | cancer_general | BAMBI |
| chr10 | 29011047 | 29011162 | Hyper | cancer_general | | chr10 | 30025970 | 30026090 | Hyper | blood | |
| chr10 | 31073368 | 31073481 | Hyper | tcga | | chr10 | 33624166 | 33624230 | Hyper | blood | |
| chr10 | 33624492 | 33624560 | Hyper | blood | | chr10 | 35929150 | 35929528 | Hyper | cancer_general, liver_tcga, tcga | FZD8 |
| chr10 | 43250009 | 43250039 | Hyper | cancer_general | | chr10 | 43250406 | 43250886 | Hyper | cancer_general | |
| chr10 | 43428424 | 43428592 | Hyper | cancer_general | | chr10 | 43429004 | 43429100 | Hyper | cancer_general | |
| chr10 | 43429376 | 43429411 | Hyper | cancer_general | | chr10 | 43572685 | 43572734 | Hyper | cancer_general | RET |
| chr10 | 43600561 | 43600720 | Hyper | cancer_general, liver_tcga | RET | chr10 | 43609055 | 43609117 | Hyper | literature | RET |
| chr10 | 43609922 | 43609963 | Hyper | literature | RET | chr10 | 43613890 | 43613919 | Hyper | literature | RET |
| chr10 | 43614982 | 43615011 | Hyper | literature | RET | chr10 | 43615554 | 43615607 | Hyper | literature | RET |
| chr10 | 43617401 | 43617430 | Hyper | literature | RET | chr10 | 43697887 | 43698155 | Hyper | cancer_general, tcga | RASGEF1A |
| chr10 | 44879944 | 44880228 | Hyper | cancer_general | CXCL12 | chr10 | 44880869 | 44880915 | Hyper | cancer_general | CXCL12 |
| chr10 | 49731548 | 49731749 | Hyper | tcga, colorectal, cancer_general | | chr10 | 49732060 | 49732498 | Hyper | cancer_general, tcga | |
| chr10 | 50323222 | 50323258 | Hyper | cancer_general | FAM170B-AS1, VSTM4 | chr10 | 50603967 | 50604159 | Hyper | cancer_general | DRGX |
| chr10 | 50604608 | 50604645 | Hyper | cancer_general | DRGX | chr10 | 50605057 | 50605654 | Hyper | cancer_general | DRGX |
| chr10 | 50606027 | 50606433 | Hyper | cancer_general | DRGX | chr10 | 50817015 | 50817132 | Hyper | cancer_general | CHAT, SLC18A3 |
| chr10 | 50817858 | 50817935 | Hyper | cancer_general | SLC18A3, CHAT | chr10 | 50818382 | 50818432 | Hyper | cancer_general | CHAT, SLC18A3 |
| chr10 | 50818823 | 50819102 | Hyper | cancer_general | CHAT, SLC18A3 | chr10 | 50821472 | 50821701 | Hyper | cancer_general | CHAT, SLC18A3 |
| chr10 | 50887655 | 50887816 | Hyper | cancer_general | C10orf53 | chr10 | 50976880 | 50977048 | Hyper | cancer_general | OGDHL |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 52177545 | 52177575 | Hyper | pancreas | SGMS1 | chr10 | 54068526 | 54068610 | Hyper | cancer_general | DKK1, PRKG1-AS1 |
| chr10 | 54072982 | 54073020 | Hyper | cancer_general | DKK1, PRKG1-AS1 | chr10 | 54073265 | 54073295 | Hyper | cancer_general | DKK1, PRKG1-AS1 |
| chr10 | 54074744 | 54074789 | Hyper | cancer_general | DKK1, PRKG1-AS1 | chr10 | 57387429 | 57387796 | Hyper | literature, cancer_general | |
| chr10 | 57388325 | 57388510 | Hyper | cancer_general | | chr10 | 57390290 | 57390637 | Hyper | cancer_general | BICC1 |
| chr10 | 57391166 | 57391215 | Hyper | cancer_general | | chr10 | 60273130 | 60273294 | Hyper | cancer_general | PHYHIPL |
| chr10 | 60935887 | 60935996 | Hyper | cancer_general | PHYHIPL | chr10 | 60936524 | 60936732 | Hyper | cancer_general | BC041470, TMEM26 |
| chr10 | 60937073 | 60937103 | Hyper | cancer_general | PHYHIPL | chr10 | 63212324 | 63212701 | Hyper | cancer_general | |
| chr10 | 64575526 | 64575638 | Hyper | cancer_general | ADO, EGR2 | chr10 | 64578171 | 64578540 | Hyper | tcga, colorectal, cancer_general | EGR2, ADO |
| chr10 | 71327725 | 71327764 | Hyper | lung, cancer_general | NEUROG3 | chr10 | 71328773 | 71328821 | Hyper | cancer_general | NEUROG3 |
| chr10 | 71329079 | 71329118 | Hyper | cancer_general | NEUROG3 | chr10 | 71329544 | 71329618 | Hyper | cancer_general | NEUROG3 |
| chr10 | 71332052 | 71333018 | Hyper | tcga, cancer_general | NEUROG3 | chr10 | 72015150 | 72015339 | Hyper | cancer_general | NPFFR1 |
| chr10 | 72043638 | 72043894 | Hyper | cancer_general | NPFFR1 | chr10 | 72200102 | 72200138 | Hyper | cancer_general | NODAL, UNC5B, UNC5B-AS1 |
| chr10 | 72200354 | 72201285 | Hyper | cancer_general | NODAL | chr10 | 72973130 | 72973180 | Hyper | blood | |
| chr10 | 73156362 | 73156661 | Hyper | tcga | CDH23 | chr10 | 73847886 | 73848167 | Hyper | cancer_general, tcga | ASCC1, SPOCK2 |
| chr10 | 75407570 | 75407837 | Hyper | tcga, liver_tcga | SYNPO2L, MYOZ1 | chr10 | 77190039 | 77190068 | Hyper | literature | |
| chr10 | 77191224 | 77191368 | Hyper | cancer_general | ZCCHC24 | chr10 | 79396921 | 79397089 | Hyper | cancer_general | KCNMA1 |
| chr10 | 81154141 | 81154192 | Hyper | liver_tcga | DYDC1, DYDC2 | chr10 | 81664867 | 81664899 | Hyper | cancer_general | LOC100288974 |
| chr10 | 82117074 | 82117271 | Hyper | tcga | | chr10 | 83634261 | 83634499 | Hyper | tcga | NRG3 |
| chr10 | 83635515 | 83635545 | Hyper | cancer_general | NRG3 | chr10 | 85954425 | 85954457 | Hyper | pancreas | |
| chr10 | 88123438 | 88123467 | Hyper | tcga | | chr10 | 88123672 | 88123701 | Hyper | tcga | CDHR1, C10orf99 |
| chr10 | 88149363 | 88149601 | Hyper | cancer_general | | chr10 | 89624255 | 89624311 | Hyper | literature | PTEN, KLLN |
| chr10 | 89653788 | 89653859 | Hyper | literature | PTEN | chr10 | 89685272 | 89685322 | Hyper | literature | PTEN |
| chr10 | 89690790 | 89690819 | Hyper | literature | PTEN | chr10 | 89692776 | 89693015 | Hyper | literature | PTEN |
| chr10 | 89711861 | 89711992 | Hyper | literature | AK130076, PTEN | chr10 | 89717610 | 89717744 | Hyper | literature | AK130076, PTEN |
| chr10 | 89720790 | 89720885 | Hyper | literature | LIPA, CH25H | chr10 | 89725030 | 89725071 | Hyper | literature | LIPA, CH25H |
| chr10 | 90966708 | 90966865 | Hyper | cancer_general | | chr10 | 90967671 | 90968040 | Hyper | cancer_general | |
| chr10 | 91295029 | 91295067 | Hyper | cancer_general | HTR7 | chr10 | 91295531 | 91295725 | Hyper | cancer_general | |
| chr10 | 92617242 | 92617308 | Hyper | cancer_general | | chr10 | 93647216 | 93647300 | Hyper | liver_tcga | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 93647562 | 93647648 | Hyper | liver_tcga | | chr10 | 94450675 | 94450726 | Hyper | cancer_general | HHEX |
| chr10 | 94451448 | 94451653 | Hyper | cancer_general | HHEX | chr10 | 94826023 | 94826056 | Hyper | cancer_general | EXOC6, CYP26C1, CYP26A1 |
| chr10 | 94828163 | 94828498 | Hyper | cancer_general | CYP26A1, CYP26C1, EXOC6 | chr10 | 94828735 | 94828828 | Hyper | cancer_general | CYP26C1, EXOC6, CYP26A1 |
| chr10 | 94834413 | 94835047 | Hyper | tcga, liver_tcga, literature, cancer_general | CYP26A1, CYP26C1 | chr10 | 95360716 | 95360750 | Hyper | blood | RBP4 |
| chr10 | 99080262 | 99080447 | Hyper | cancer_general | FRAT1 MARVELD1 | chr10 | 99080862 | 99080984 | Hyper | cancer_general | FRAT1 |
| chr10 | 99474393 | 99474467 | Hyper | hepatobiliary | | chr10 | 99531219 | 99531430 | Hyper | tcga, cancer_general | SFRP5 |
| chr10 | 99789175 | 99789282 | Hyper | cancer_general | | chr10 | 99790261 | 99790318 | Hyper | cancer_general | |
| chr10 | 99790590 | 99790664 | Hyper | cancer_general | | chr10 | 99790947 | 99791161 | Hyper | cancer_general | |
| chr10 | 100991907 | 100992443 | Hyper | tcga, cancer_general | HPSE2 | chr10 | 100992882 | 100992916 | Hyper | cancer_general | HPSE2 |
| chr10 | 100993537 | 100994016 | Hyper | colorectal, cancer_general | HPSE2 | chr10 | 100996046 | 100996224 | Hyper | cancer_general | HPSE2 |
| chr10 | 101088995 | 101089439 | Hyper | cancer_general | CNNM1 | chr10 | 101089908 | 101090203 | Hyper | cancer_general | CNNM1 |
| chr10 | 101280204 | 101280485 | Hyper | cancer_general | DQ372722, chromosome 10 open reading frame 139 | chr10 | 101283464 | 101283658 | Hyper | tcga | DQ372722, chromosome 10 open reading frame 139, NKX2-3 |
| chr10 | 101290117 | 101291191 | Hyper | cancer_general | NKX2-3, chromosome 10 open reading frame 139, DQ372722 | chr10 | 101292297 | 101292919 | Hyper | cancer_general | NKX2-3, chromosome 10 open reading frame 139, DQ372722 |
| chr10 | 101293156 | 101293343 | Hyper | cancer_general | NKX2-3, chromosome 10 open reading frame 139, DQ372722 | chr10 | 101294756 | 101295586 | Hyper | cancer_general | NKX2-3, chromosome 10 open reading frame 139, DQ372722 |
| chr10 | 101296768 | 101296800 | Hyper | cancer_general | NKX2-3, chromosome 10 open reading frame 139, DQ372722 | chr10 | 101874886 | 101875138 | Hyper | literature, liver_tcga | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 102322230 | 102322260 | Hyper | cancer_general | HIF1AN | chr10 | 102419316 | 102419681 | Hyper | cancer_general | |
| chr10 | 102430699 | 102430761 | Hyper | cancer_general | | chr10 | 102473856 | 102473932 | Hyper | cancer_general | PAX2 |
| chr10 | 102483993 | 102484554 | Hyper | cancer_general | | chr10 | 102495508 | 102495741 | Hyper | cancer_general | PAX2 |
| chr10 | 102497273 | 102497708 | Typer | tcga, cancer_general | PAX2 | chr10 | 102498280 | 102498433 | Hyper | cancer_general | |
| chr10 | 102501359 | 102501389 | Hyper | cancer_general | PAX2 | chr10 | 102507509 | 102507605 | Hyper | cancer_general | PAX2 |
| chr10 | 102508996 | 102509285 | Hyper | cancer_general | PAX2 | chr10 | 102586505 | 102586822 | Hyper | cancer_general | |
| chr10 | 102589425 | 102589493 | Hyper | cancer_general | | chr10 | 102589786 | 102589915 | Hyper | cancer_general | |
| chr10 | 102590152 | 102590415 | Hyper | cancer_general | | chr10 | 102890941 | 102891582 | Hyper | tcga, cancer_general | TLX1, TLX1NB |
| chr10 | 102891823 | 102892025 | Hyper | cancer_general | TLX1, TLX1NB | chr10 | 102893624 | 102895289 | Hyper | liver_tcga, literature, cancer_general | TLX1, TLX1NB |
| chr10 | 102899173 | 102899601 | Hyper | cancer_general | TLX1, TLX1NB | chr10 | 102899807 | 102900575 | Hyper | liver_tcga, cancer_general | TLX1, TLX1NB |
| chr10 | 102906523 | 102906620 | Hyper | cancer_general | TLX1 | chr10 | 102975619 | 102975834 | Hyper | cancer_general | LBX1 |
| chr10 | 102976150 | 102976180 | Hyper | cancer_general | | chr10 | 102977051 | 102977412 | Hyper | cancer_general | LBX1, FLJ41350 |
| chr10 | 102983153 | 102983749 | Hyper | cancer_general | LBX1, FLJ41350 | chr10 | 102984407 | 102984516 | Hyper | cancer_general | LBX1, FLJ41350 |
| chr10 | 102985772 | 102985963 | Hyper | cancer_general | LBX1, FLJ41350 | chr10 | 102986534 | 102987558 | Hyper | lung, cancer_general | LBX1, FLJ41350 |
| chr10 | 102989629 | 102989659 | Hyper | cancer_general | LBX1 | chr10 | 102996116 | 102996638 | Hyper | cancer_general | FLJ41350, LBX1 |
| chr10 | 102997329 | 102997406 | Hyper | cancer_general | FLJ41350, LBX1 | chr10 | 102998576 | 102998828 | Hyper | cancer_general | FLJ41350, LBX1 |
| chr10 | 103043975 | 103044366 | Hyper | literature, cancer_general | MGEA5, FGF8, NPM3 | chr10 | 103432412 | 103432441 | Hyper | cancer_general | FBXW4 |
| chr10 | 103535622 | 103535789 | Hyper | tcga | PSD, FBXL15, NFKB2 | chr10 | 103536227 | 103536416 | Hyper | liver_tcga, cancer_general | NPM3, MGEA5, FGF8 |
| chr10 | 104170096 | 104170732 | Hyper | tcga, cancer_general | INA | chr10 | 105036542 | 105036863 | Hyper | liver_tcga, cancer_general | INA |
| chr10 | 105037223 | 105037830 | Hyper | liver_tcga, cancer_general | INA | chr10 | 106398644 | 106398886 | Hyper | cancer_general | SORCS3 |
| chr10 | 106399581 | 106400387 | Hyper | cancer_general | SORCS3 | chr10 | 106400970 | 106402325 | Hyper | tcga, cancer_general | SORCS3 |
| chr10 | 106402712 | 106402825 | Hyper | cancer_general | SORCS3 | chr10 | 108924045 | 108924095 | Hyper | cancer_general | |
| chr10 | 108924463 | 108924684 | Hyper | cancer_general | | chr10 | 110226258 | 110226304 | Hyper | cancer_general | |
| chr10 | 110671892 | 110672245 | Hyper | tcga, cancer_general | | chr10 | 112216789 | 112216927 | Hyper | cancer_general | |
| chr10 | 112403151 | 112403297 | Hyper | cancer_general | RBM20, Y_RNA | chr10 | 115804840 | 115805014 | Hyper | cancer_general | ADRB1 |
| chr10 | 116164248 | 116164341 | Hyper | blood | AFAP1L2 | chr10 | 116853875 | 116853908 | Hyper | esophageal | ATRNL1 |
| chr10 | 118030642 | 118030875 | Hyper | cancer_general | GFRA1 | chr10 | 118031302 | 118032547 | Hyper | tcga, cancer_general | GFRA1 |
| chr10 | 118032917 | 118033542 | Hyper | cancer_general | GFRA1 KIAA1598, ENO4 | chr10 | 118034138 | 118034168 | Hyper | cancer_general | GFRA1 KIAA1598 |
| chr10 | 118609305 | 118609390 | Hyper | esophageal | | chr10 | 118890980 | 118891104 | Hyper | lung, cancer_general | VAX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 118891517 | 118891774 | Hyper | cancer_general | VAX1, KIAA1598 | chr10 | 118892013 | 118893266 | Hyper | cancer_general | VAX1, KIAA1598 |
| chr10 | 118893582 | 118894283 | Hyper | tcga, cancer_general | VAX1, KIAA1598 | chr10 | 118896629 | 118896805 | Hyper | tcga, cancer_general | VAX1 |
| chr10 | 118897913 | 118897968 | Hyper | cancer_general | VAX1 | chr10 | 118899273 | 118899302 | Hyper | literature | VAX1 |
| chr10 | 118899511 | 118899957 | Hyper | cancer_general | VAX1 | chr10 | 118900166 | 118900498 | Hyper | cancer_general | VAX1 |
| chr10 | 118922143 | 118922208 | Hyper | cancer_general | MIR3663, BC039338 | chr10 | 118922721 | 118922901 | Hyper | cancer_general, tcga | MIR3663, BC039338 |
| chr10 | 118923138 | 118923259 | Hyper | cancer_general | MIR3663, BC039338 | chr10 | 118924604 | 118924896 | Hyper | cancer_general | MIR3663, BC039338 |
| chr10 | 118927086 | 118927296 | Hyper | cancer_general | MIR3663, BC039338 | chr10 | 118928548 | 118928727 | Hyper | cancer_general | MIR3663, BC039338 |
| chr10 | 119000662 | 119001304 | Hyper | cancer_general | SLC18A2 | chr10 | 119001534 | 119001564 | Hyper | cancer_general | SLC18A2 |
| chr10 | 119292277 | 119292320 | Hyper | cancer_general | EMX2, EMX2OS | chr10 | 119294352 | 119294461 | Hyper | cancer_general | EMX2, EMX2OS |
| chr10 | 119294847 | 119295245 | Hyper | cancer_general | EMX2OS, EMX2 | chr10 | 119296706 | 119296788 | Hyper | cancer_general | EMX2, EMX2OS |
| chr10 | 119297384 | 119297529 | Hyper | cancer_general | EMX2, EMX2OS | chr10 | 119301365 | 119301669 | Hyper | cancer_general | EMX2OS, EMX2 |
| chr10 | 119302141 | 119302266 | Hyper | cancer_general | EMX2, EMX2OS | chr10 | 119302962 | 119303174 | Hyper | cancer_general | EMX2, EMX2OS |
| chr10 | 119304363 | 119304393 | Hyper | cancer_general | EMX2, EMX2OS | chr10 | 119304896 | 119305109 | Hyper | cancer_general | EMX2, EMX2OS |
| chr10 | 119307022 | 119307052 | Hyper | cancer_general | EMX2, EMX2OS | chr10 | 119311867 | 119311897 | Hyper | cancer_general | EMX2, EMX2OS |
| chr10 | 119312751 | 119313193 | Hyper | cancer_general | EMX2OS, EMX2 | chr10 | 119590435 | 119590464 | Hyper | literature | PRLHR |
| chr10 | 120354243 | 120354273 | Hyper | cancer_general | PRLHR | chr10 | 120355548 | 120355614 | Hyper | cancer_general | PRLHR |
| chr10 | 122216896 | 122217083 | Hyper | tcga | PPAPDC1A | chr10 | 122708495 | 122708691 | Hyper | cancer_general | FGFR2 |
| chr10 | 122708992 | 122709022 | Hyper | cancer_general | | chr10 | 123256044 | 123256232 | Hyper | literature | FGFR2 |
| chr10 | 123258020 | 123258091 | Hyper | literature | FGFR2 | chr10 | 123274758 | 123274787 | Hyper | literature | FGFR2 |
| chr10 | 123279548 | 123279697 | Hyper | literature | FGFR2 | chr10 | 123357206 | 123357242 | Hyper | blood | FGFR2 |
| chr10 | 123357766 | 123357893 | Hyper | blood | FGFR2 | chr10 | 123922645 | 123923464 | Hyper | cancer_general | TACC2 |
| chr10 | 124893178 | 124893350 | Hyper | cancer_general | HMX3 | chr10 | 124893635 | 124893765 | Hyper | cancer_general | HMX3 |
| chr10 | 124893965 | 124894479 | Hyper | cancer_general | HMX3 | chr10 | 124894889 | 124894922 | Hyper | cancer_general | HMX3 |
| chr10 | 124895426 | 124896456 | Hyper | tcga, cancer_general | HMX3 | chr10 | 124896861 | 124896913 | Hyper | cancer_general | HMX3 |
| chr10 | 124897220 | 124897973 | Hyper | cancer_general | HMX2, HMX3 | chr10 | 124899035 | 124899116 | Hyper | cancer_general | HMX2, HMX3 |
| chr10 | 124899754 | 124899786 | Hyper | cancer_general | HMX2, HMX3 | chr10 | 124901892 | 124903238 | Hyper | cancer_general | HMX3, HMX2 |
| chr10 | 124904921 | 124905119 | Hyper | cancer_general | HMX2, HMX3 | chr10 | 124905481 | 124905511 | Hyper | cancer_general | BUB3, HMX3, HMX2 |
| chr10 | 124905911 | 124906174 | Hyper | cancer_general | HMX2, BUB3, HMX3 | chr10 | 124906436 | 124906544 | Hyper | cancer_general | HMX3, HMX2, BUB3 |
| chr10 | 124907312 | 124907534 | Hyper | cancer_general | HMX2, BUB3 | chr10 | 124908091 | 124908121 | Hyper | cancer_general | BUB3, HMX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 124909086 | 124909725 | Hyper | tcga, cancer_general | BUB3, HMX2 | chr10 | 124910363 | 124911048 | Hyper | cancer_general, lung | BUB3, HMX2 |
| chr10 | 125425515 | 125425547 | Hyper | cancer_general | GPR26 | chr10 | 125650866 | 125651348 | Hyper | cancer_general | CPXM2 |
| chr10 | 125851328 | 125851645 | Hyper | colorectal, cancer_general | CHST15 | chr10 | 125852299 | 125852524 | Hyper | colorectal | CHST15 |
| chr10 | 125882753 | 125853191 | Hyper | colorectal | CHST15 | chr10 | 126135927 | 126136065 | Hyper | cancer_general | NKX1-2 |
| chr10 | 126136506 | 126136723 | Hyper | tcga, cancer_general | NKX1-2 | chr10 | 126137181 | 126137405 | Hyper | cancer_general | NKX1-2 |
| chr10 | 128076561 | 128076630 | Hyper | cancer_general | ADAM12 | chr10 | 128077262 | 128077292 | Hyper | cancer_general | ADAM12 |
| chr10 | 128993904 | 128994446 | Hyper | tcga, cancer_general | FAM196A | chr10 | 128994727 | 128994903 | Hyper | pancreas, cancer_general | FAM196A |
| chr10 | 129534597 | 129535733 | Hyper | cancer_general | FOXI2, BC132944 | chr10 | 129536080 | 129536310 | Hyper | cancer_general | BC132944, FOXI2 |
| chr10 | 129948111 | 129948140 | Hyper | liver_tcga, pancreas, cancer_general |  | chr10 | 130085295 | 130085362 | Hyper | cancer_general | AK124226 |
| chr10 | 130338727 | 130338976 | Hyper | cancer_general |  | chr10 | 131757091 | 131757430 | Hyper | cancer_general | EBF3 |
| chr10 | 131757946 | 131758056 | Hyper | cancer_general | EBF3 | chr10 | 131761378 | 131761441 | Hyper | cancer_general | EBF3 |
| chr10 | 131761687 | 131761725 | Hyper | cancer_general | EBF3 | chr10 | 131762087 | 131762124 | Hyper | cancer_general | EBF3 |
| chr10 | 131762592 | 131762631 | Hyper | cancer_general | EBF3 | chr10 | 131762904 | 131762940 | Hyper | cancer_general | EBF3 |
| chr10 | 131763348 | 131763717 | Hyper | cancer_general | EBF3 | chr10 | 131767372 | 131767649 | Hyper | tcga, cancer_general | EBF3 |
| chr10 | 131768724 | 131769029 | Hyper | tcga, cancer_general | EBF3 | chr10 | 131769533 | 131770237 | Hyper | cancer_general | EBF3 |
| chr10 | 131770657 | 131770687 | Hyper | cancer_general | EBF3 | chr10 | 131770988 | 131771245 | Hyper | cancer_general | EBF3 |
| chr10 | 133109192 | 133109297 | Hyper | cancer_general |  | chr10 | 133109634 | 133109781 | Hyper | cancer_general |  |
| chr10 | 133110353 | 133110704 | Hyper | cancer_general |  | chr10 | 133794883 | 133795430 | Hyper | tcga, colorectal, cancer_general |  |
| chr10 | 133795682 | 133796221 | Hyper | cancer_general | BNIP3 | chr10 | 133849598 | 133850008 | Hyper | cancer_general, pancreas, cancer_general | BNIP3 |
| chr10 | 133850529 | 133850774 | Hyper | tcga, cancer_general |  | chr10 | 134000008 | 134000124 | Hyper | liver_tcga |  |
| chr10 | 134001097 | 134001260 | Hyper | tcga, cancer_general | DPYSL4, AL137551, JAKMIP3 | chr10 | 134121401 | 134121430 | Hyper | liver_tcga | DPYSL4, AL137551, JAKMIP3 STK32C |
| chr10 | 134598087 | 134598117 | Hyper | cancer_general | NKX6-2, INPP5A | chr10 | 134598336 | 134598530 | Hyper | liver_tcga, cancer_general | NKX6-2, INPP5A |
| chr10 | 134599062 | 134599482 | Hyper | liver_tcga, cancer_general | NKX6-2, INPP5A | chr10 | 134599808 | 134600998 | Hyper | liver_tcga, cancer_general | NKX6-2, INPP5A |
| chr10 | 134601556 | 134601798 | Hyper | cancer_general | NKX6-2, INPP5A | chr10 | 134602183 | 134602269 | Hyper | cancer_general | NKX6-2, INPP5A |
| chr10 | 134755757 | 134756183 | Hyper | tcga, esophageal, cancer_general | TTC40 | chr10 | 134901193 | 134901511 | Hyper | tcga | GPR123 |
| chr10 | 134902008 | 134902307 | Hyper | cancer_general | GPR123 | chr10 | 135043088 | 135043538 | Hyper | cancer_general | UTF1, VENTX |
| chr10 | 135043968 | 135044128 | Hyper | tcga, liver_tcga, cancer_general | VENTX, UTF1 | chr10 | 135044511 | 135044573 | Hyper | cancer_general | VENTX, UTF1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 135048782 | 135048939 | Hyper | cancer_general | VENTX, UTF1 | chr10 | 135050311 | 135050679 | Hyper | cancer_general, tcga | UTF1, VENTX |
| chr10 | 135121316 | 135121345 | Hyper | literature | ZNF511, PRAP1, TUBGCP2 | chr10 | 135121807 | 135122251 | Hyper | literature | ZNF511, PRAP1, TUBGCP2 |
| chr10 | 135122742 | 135122808 | Hyper | literature | PRAP1, ZNF511, TUBGCP2 | chr10 | 135139555 | 135139730 | Hyper | tcga | CALY, BC047942, PRAP1 |
| AC241851.2_88-34049 | | | | | | AC241851.2_88-34049 | | | | | |
| chr5 | 14729 | 14973 | Hyper | cancer_general | | chr5 | 15261 | 15350 | Hyper | cancer_general | |
| chr5 | 53849 | 53900 | Hyper | cancer_general | | chr5 | 92163 | 92399 | Hyper | cancer_general | |
| chr5 | 320840 | 320982 | Hyper | liver_tcga, literature, cancer_general | AHRR, PDCD6 | chr5 | 343912 | 343941 | Hyper | literature | AHRR |
| chr5 | 373872 | 374266 | Hyper | literature | AHRR | chr5 | 400186 | 400215 | Hyper | literature | AHRR |
| chr5 | 400502 | 400531 | Hyper | literature | AHRR | chr5 | 524337 | 524404 | Hyper | cancer_general | |
| chr5 | 528565 | 528685 | Hyper | tcga, liver_tcga, cancer_general | MIR4456 | chr5 | 1093660 | 1093797 | Hyper | liver_tcga | |
| chr5 | 1294630 | 1294767 | Hyper | cancer_general | TERT | chr5 | 1295031 | 1295662 | Hyper | cancer_general, literature | TERT |
| chr5 | 1445171 | 1445282 | Hyper | cancer_general | SLC6A3 | chr5 | 1445738 | 1445928 | Hyper | cancer_general | SLC6A3 |
| chr5 | 1446319 | 1446599 | Hyper | cancer_general | SLC6A3 | chr5 | 1874892 | 1875099 | Hyper | cancer_general | IRX4 |
| chr5 | 1875453 | 1875497 | Hyper | cancer_general | IRX4 | chr5 | 1875870 | 1876860 | Hyper | cancer_general | IRX4 |
| chr5 | 1877160 | 1877239 | Hyper | cancer_general | IRX4 | chr5 | 1878014 | 1878528 | Hyper | cancer_general | IRX4 |
| chr5 | 1878739 | 1879045 | Hyper | cancer_general | IRX4 | chr5 | 1879605 | 1879719 | Hyper | literature, cancer_general | IRX4 |
| chr5 | 1882294 | 1882605 | Hyper | cancer_general | IRX4 | chr5 | 1882844 | 1883089 | Hyper | cancer_general | IRX4 |
| chr5 | 1883515 | 1883820 | Hyper | cancer_general | IRX4 | chr5 | 1884178 | 1884237 | Hyper | cancer_general | IRX4 |
| chr5 | 1884557 | 1884698 | Hyper | cancer_general | IRX4 | chr5 | 1885158 | 1885458 | Hyper | cancer_general | IRX4 |
| chr5 | 1885985 | 1886192 | Hyper | cancer_general | IRX4 | chr5 | 1886542 | 1886581 | Hyper | cancer_general | IRX4 |
| chr5 | 1886812 | 1887737 | Hyper | cancer_general | IRX4 | chr5 | 1930786 | 1931754 | Hyper | pancreas, liver_tcga, cancer_general | |
| chr5 | 1952624 | 1952654 | Hyper | cancer_general | IRX2 | chr5 | 2038705 | 2038850 | Hyper | cancer_general | |
| chr5 | 2738848 | 2739422 | Hyper | cancer_general | | chr5 | 2739877 | 2741061 | Hyper | tcga, cancer_general | IRX2 |
| chr5 | 2743617 | 2743713 | Hyper | cancer_general | C5orf38, IRX2 | chr5 | 2748374 | 2748459 | Hyper | cancer_general | C5orf38, IRX2 |
| chr5 | 2749213 | 2749425 | Hyper | cancer_general | C5orf38 | chr5 | 2749699 | 2749729 | Hyper | cancer_general | C5orf38, IRX2 |
| chr5 | 2750435 | 2751368 | Hyper | cancer_general | C5orf38, IRX2 | chr5 | 2751694 | 2751894 | Hyper | liver_tcga, cancer_general | IRX2 |
| chr5 | 2752991 | 2753040 | Hyper | cancer_general | C5orf38, IRX2 | chr5 | 2754738 | 2754767 | Hyper | literature | IRX2, C5orf38 |
| chr5 | 2755323 | 2756388 | Hyper | tcga, cancer_general | C5orf38, IRX2 | chr5 | 2756599 | 2757427 | Hyper | cancer_general | C5orf38, IRX2 |
| chr5 | 3590405 | 3590760 | Hyper | cancer_general | IRX1 | chr5 | 3591354 | 3591388 | Hyper | cancer_general | IRX1 |
| chr5 | 3591857 | 3592037 | Hyper | cancer_general | IRX1 | chr5 | 3592728 | 3592881 | Hyper | cancer_general | IRX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 3594250 | 3594717 | Hyper | cancer_general | IRX1 | chr5 | 3595090 | 3595178 | Hyper | cancer_general | IRX1 |
| chr5 | 3595448 | 3595991 | Hyper | cancer_general, tcga, pancreas | IRX1 | chr5 | 3596192 | 3596221 | Hyper | liver_tcga, tcga | IRX1 |
| chr5 | 3596540 | 3596880 | Hyper | cancer_general | IRX1 | chr5 | 3597411 | 3597461 | Hyper | cancer_general | IRX1 |
| chr5 | 3599833 | 3599863 | Hyper | cancer_general | IRX1 | chr5 | 3600150 | 3600180 | Hyper | cancer_general | IRX1 |
| chr5 | 3600868 | 3600898 | Hyper | cancer_general | IRX1 | chr5 | 3602804 | 3603320 | Hyper | cancer_general | IRX1 |
| chr5 | 3606633 | 3606668 | Hyper | cancer_general | IRX1 | chr5 | 5139673 | 5139900 | Hyper | cancer_general | ADAMTS16, AK094462 |
| chr5 | 5140170 | 5140225 | Hyper | cancer_general | AK094462, ADAMTS16 | chr5 | 5140630 | 5140901 | Hyper | cancer_general | ADAMTS16, AK094462 |
| chr5 | 6448930 | 6449582 | Hyper | cancer_general, lung, cancer_general | UBE2QL1 | chr5 | 6383461 | 6583579 | Hyper | cancer_general | LOC255167 |
| chr5 | 6687277 | 6687431 | Hyper |  |  | chr5 | 6755789 | 6755843 | Hyper | liver_tcga | PAPD7 |
| chr5 | 7395263 | 7395538 | Hyper | tcga, cancer_general | ADCY2 | chr5 | 7850069 | 7850203 | Hyper | liver_tcga | FASTKD3, C5orf49 |
| chr5 | 7851015 | 7851121 | Hyper | cancer_general | FASTKD3, C5orf49 | chr5 | 9546612 | 9546648 | Hyper | cancer_general | SNORD123, LOC100505806 |
| chr5 | 10333688 | 10334132 | Hyper | lung, cancer_general | CTNND2 | chr5 | 10565021 | 10565607 | Hyper | cancer_general | ANKRD33B |
| chr5 | 11384906 | 11385363 | Hyper | cancer_general | CTNND2 | chr5 | 11903760 | 11904696 | Hyper | cancer_general | |
| chr5 | 11904896 | 11904943 | Hyper | cancer_general | FBXL7 | chr5 | 14872919 | 14873053 | Hyper | tcga | |
| chr5 | 15500748 | 15500927 | Hyper | tcga, cancer_general |  | chr5 | 16179049 | 16179141 | Hyper | cancer_general | MARCH11, BC043001 |
| chr5 | 16179516 | 16179713 | Hyper | cancer_general | BC043001, MARCH11 | chr5 | 16180047 | 16180260 | Hyper | liver_tcga, literature, cancer_general | BC043001, MARCH11 |
| chr5 | 16936354 | 16936514 | Hyper | tcga, liver_tcga | MYO10 | chr5 | 17217928 | 17217958 |  | cancer_general, pancreas | BASP1, LOC285696 |
| chr5 | 17218195 | 17218225 | Hyper | pancreas | BASP1, LOC285696 | chr5 | 17218943 | 17219018 | Hyper | cancer_general | LOC285696, BASP1 |
| chr5 | 22853443 | 22853508 | Hyper | cancer_general | CDH6 | chr5 | 31193937 | 31193989 | Hyper | cancer_general | CDH6 |
| chr5 | 31194375 | 31194641 | Hyper | cancer_general |  | chr5 | 31639684 | 31639960 | Hyper | tcga, cancer_general | PDZD2 |
| chr5 | 31855073 | 31855199 | Hyper | tcga | PDZD2 | chr5 | 32710331 | 32710470 | Hyper | cancer_general | NPR3 |
| chr5 | 32710802 | 32711531 | Hyper | tcga, cancer_general | NPR3 | chr5 | 32711826 | 32711870 | Hyper | cancer_general | NPR3 |
| chr5 | 32712077 | 32712491 | Hyper | cancer_general | NPR3 | chr5 | 32712764 | 32713304 | Hyper | tcga, cancer_general | NPR3 |
| chr5 | 33892083 | 33892115 | Hyper | cancer_general | U6, ADAMTS12 RXFP3, SLC45A2 | chr5 | 33892413 | 33892443 | Hyper | cancer_general | U6, ADAMTS12 SLC45A2, RXFP3 |
| chr5 | 33936156 | 33936336 | Hyper | tcga, cancer_general |  | chr5 | 33936599 | 33936663 | Hyper | cancer_general | |
| chr5 | 34656932 | 34657034 | Hyper | blood | RAI14 | chr5 | 35874560 | 35874589 | Hyper | literature | IL7R |
| chr5 | 37834684 | 37834714 | Hyper | cancer_general | GDNF-AS1, GDNF | chr5 | 37834943 | 37835125 | Hyper | literature | GDNF, GDNF-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 37836231 | 37836260 | Hyper | literature | GDNF-AS1, GDNF | chr5 | 37836649 | 37837992 | Hyper | cancer_general | GDNF-AS1, GDNF |
| chr5 | 37838548 | 37838885 | Hyper | tcga, cancer_general | GDNF-AS1, GDNF | chr5 | 37839780 | 37840125 | Hyper | cancer_general | GDNF-AS1, GDNF |
| chr5 | 37840381 | 37840853 | Hyper | tcga, cancer_general | GDNF-AS1, GDNF | chr5 | 38257485 | 38257606 | Hyper | tcga, cancer_general | EGFLAM |
| chr5 | 38257842 | 38257959 | Hyper | cancer_general | EGFLAM | chr5 | 38557070 | 38557400 | Hyper | tcga | MIR3650, LIFR, BC045578 |
| chr5 | 38845675 | 38846431 | Hyper | tcga, colorectal, cancer_general | OSMR | chr5 | 40681122 | 40681367 | Hyper | liver_tcga, cancer_general | PTGER4 |
| chr5 | 40681676 | 40682004 | Hyper | cancer_general | PTGER4 | chr5 | 42424822 | 42425060 | Hyper | cancer_general | GHR |
| chr5 | 42950980 | 42952441 | Hyper | tcga, cancer_general | | chr5 | 42991825 | 42992934 | Hyper | cancer_general | AK056817 |
| chr5 | 42993150 | 42994193 | Hyper | tcga, cancer_general | AK056817 | chr5 | 42994694 | 42994790 | Hyper | tcga, liver_tcga | AK056817 |
| chr5 | 42995115 | 42995153 | Hyper | cancer_general | AK056817 | chr5 | 43007936 | 43007966 | Hyper | breast | LOC648987 |
| chr5 | 43008202 | 43008562 | Hyper | tcga, cancer_general | LOC648987 | chr5 | 43017953 | 43018767 | Hyper | tcga, cancer_general | LOC648987 |
| chr5 | 43019238 | 43019347 | Hyper | cancer_general | LOC648987 | chr5 | 43019809 | 43019887 | Hyper | cancer_general | LOC648987 |
| chr5 | 43020146 | 43020294 | Hyper | tcga, breast | LOC648987 | chr5 | 43040544 | 43040635 | Hyper | tcga | LOC153684, DQ601842, ANXA2R |
| chr5 | 43040870 | 43040964 | Hyper | tcga, cancer_general | LOC153684, DQ601842, ANXA2R | chr5 | 43397002 | 43397246 | Hyper | cancer_general | CCL28 |
| chr5 | 44389766 | 44389852 | Hyper | cancer_general | FGF10 | chr5 | 45695186 | 45695533 | Hyper | cancer_general | HCN1 |
| chr5 | 45695906 | 45695947 | Hyper | cancer_general | HCN1 | chr5 | 45696336 | 45696439 | Hyper | cancer_general | HCN1 |
| chr5 | 49736592 | 49736685 | Hyper | cancer_general | | chr5 | 50262893 | 50263014 | Hyper | cancer_general | |
| chr5 | 50263568 | 50263641 | Hyper | cancer_general | | chr5 | 50264307 | 50264603 | Hyper | cancer_general | |
| chr5 | 50264820 | 50264850 | Hyper | lung | | chr5 | 50265325 | 50265429 | Hyper | cancer_general | |
| chr5 | 50265720 | 50265880 | Hyper | cancer_general | | chr5 | 50674152 | 50674188 | Hyper | cancer_general | |
| chr5 | 50674560 | 50674590 | Hyper | cancer_general | ISL1, LOC642366 | chr5 | 50675013 | 50675075 | Hyper | cancer_general | ISL1, LOC642366 |
| chr5 | 50678346 | 50678490 | Hyper | cancer_general | ISL1, LOC642366 | chr5 | 50695280 | 50695463 | Hyper | cancer_general | ISL1 |
| chr5 | 52084073 | 52084134 | Hyper | blood | PELO, ITGA1 | chr5 | 54179587 | 54179633 | Hyper | cancer_general | |
| chr5 | 54180063 | 54180093 | Hyper | cancer_general | CCNO, MCIDAS | chr5 | 54516371 | 54517017 | Hyper | liver_tcga, cancer_general | CCNO, MCIDAS |
| chr5 | 54518651 | 54519321 | Hyper | cancer_general | | chr5 | 54527304 | 54527343 | Hyper | cancer_general | CCNO, MCIDAS |
| chr5 | 56246546 | 56246575 | Hyper | literature | MIER3 | chr5 | 56247942 | 56247971 | Hyper | literature | MIER3 |
| chr5 | 56248218 | 56248257 | Hyper | literature | MIER3 | chr5 | 57878271 | 57878375 | Hyper | cancer_general | RAB3C |
| chr5 | 57878710 | 57878752 | Hyper | head_neck | RAB3C | chr5 | 59188291 | 59188327 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 59189055 | 59189206 | Hyper | liver_tcga, cancer_general | | chr5 | 59189863 | 59189948 | Hyper | cancer_general | |
| chr5 | 63254903 | 63255265 | Hyper | cancer_general | HTR1A | chr5 | 63256863 | 63256895 | Hyper | cancer_general | HTR1A |
| chr5 | 63257727 | 63257861 | Hyper | cancer_general | HTR1A | chr5 | 63802007 | 63802514 | Hyper | cancer_general | RGS7BP |
| chr5 | 63986488 | 63986807 | Hyper | cancer_general | FAM159B | chr5 | 67569803 | 67569832 | Hyper | literature | PIK3R1 |
| chr5 | 67588937 | 67589162 | Hyper | literature | PIK3R1 | chr5 | 67589598 | 67589627 | Hyper | literature | PIK3R1 |
| chr5 | 67590431 | 67590460 | Hyper | literature | PIK3R1 | chr5 | 67591068 | 67591157 | Hyper | literature | PIK3R1 |
| chr5 | 71014720 | 71014895 | Hyper | cancer_general | CARTPT | chr5 | 71015180 | 71015728 | Hyper | cancer_general | CARTPT |
| chr5 | 71403566 | 71403653 | Hyper | cancer_general | MAP1B | chr5 | 71403975 | 71404207 | Hyper | tcga | MAP1B |
| chr5 | 72416246 | 72416751 | Hyper | blood | TMEM171 | chr5 | 72526413 | 72526643 | Hyper | cancer_general | |
| chr5 | 72529289 | 72530609 | Hyper | cancer_general | | chr5 | 72594802 | 72595059 | Hyper | cancer_general | |
| chr5 | 72595542 | 72595788 | Hyper | cancer_general | | chr5 | 72599079 | 72599833 | Hyper | cancer_general | |
| chr5 | 72677672 | 72678319 | Hyper | cancer_general | | chr5 | 72715204 | 72715768 | Hyper | cancer_general | FOXD1 |
| chr5 | 72716102 | 72716180 | Hyper | cancer_general | | chr5 | 72732801 | 72732884 | Hyper | lung, cancer_general | |
| chr5 | 72733093 | 72733185 | Hyper | blood | FOXD1 | chr5 | 72740147 | 72740184 | Hyper | cancer_general | FOXD1 |
| chr5 | 72746680 | 72746710 | Hyper | cancer_general | FOXD1 | chr5 | 75377883 | 75378033 | Hyper | cancer_general | SV2C |
| chr5 | 75380163 | 75380193 | Hyper | cancer_general | SV2C | chr5 | 75380624 | 75380974 | Hyper | cancer_general | SV2C |
| chr5 | 76011285 | 76011337 | Hyper | cancer_general | F2R, NCRUPAR | chr5 | 76012576 | 76012605 | Hyper | liver_tcga | F2R, NCRUPAR |
| chr5 | 76249270 | 76250150 | Hyper | cancer_general | CRHBP | chr5 | 76250435 | 76250504 | Hyper | cancer_general | CRHBP |
| chr5 | 76506469 | 76506506 | Hyper | tcga | PDE8B | chr5 | 76507035 | 76507114 | Hyper | tcga | PDE8B |
| chr5 | 76923679 | 76924409 | Hyper | cancer_general | OTP | chr5 | 76924930 | 76924960 | Hyper | cancer_general | OTP |
| chr5 | 76925561 | 76925690 | Hyper | cancer_general | OTP | chr5 | 76928157 | 76928397 | Hyper | cancer_general | OTP |
| chr5 | 76928688 | 76928906 | Hyper | cancer_general | OTP | chr5 | 76932302 | 76932332 | Hyper | cancer_general | OTP |
| chr5 | 76932542 | 76933281 | Hyper | cancer_general | OTP | chr5 | 76934173 | 76934870 | Hyper | cancer_general | OTP |
| chr5 | 76936016 | 76936721 | Hyper | pancreas | OTP | chr5 | 76939420 | 76939774 | Hyper | cancer_general | OTP |
| chr5 | 76940340 | 76940374 | Hyper | cancer_general | | chr5 | 76941201 | 76941326 | Hyper | cancer_general | |
| chr5 | 77140527 | 77140711 | Hyper | cancer_general | | chr5 | 77147563 | 77148195 | Hyper | cancer_general | |
| chr5 | 77148498 | 77148712 | Hyper | cancer_general | | chr5 | 77263867 | 77269309 | Hyper | tcga, cancer_general | |
| chr5 | 77806057 | 77806128 | Hyper | cancer_general | LHFPL2 | chr5 | 78407651 | 78407840 | Hyper | cancer_general | BHMT |
| chr5 | 78408192 | 78408461 | Hyper | cancer_general | BHMT | chr5 | 79864898 | 79865078 | Hyper | cancer_general | ANKRD34B |
| chr5 | 79866062 | 79866414 | Hyper | cancer_general | | chr5 | 80255816 | 80256166 | Hyper | cancer_general, liver_tcga | RASGRF2 |
| chr5 | 80689543 | 80689735 | Hyper | cancer_general | ACOT12 | chr5 | 80690118 | 80690239 | Hyper | tcga, cancer_general | ACOT12 |
| chr5 | 82767429 | 82767793 | Hyper | cancer_general | VCAN | chr5 | 82768892 | 82769061 | Hyper | tcga, colorectal | VCAN |
| chr5 | 83679195 | 83679225 | Hyper | cancer_general | | chr5 | 83679681 | 83680340 | Hyper | tcga, cancer_general | |
| chr5 | 83680615 | 83680708 | Hyper | cancer_general | | chr5 | 87955460 | 87955797 | Hyper | cancer_general | |
| chr5 | 87956199 | 87956964 | Hyper | cancer_general | LINC00461, MIR9-2 | chr5 | 87962966 | 87963002 | Hyper | cancer_general | LINC00461, MIR9-2 |
| chr5 | 87963390 | 87963511 | Hyper | cancer_general | MIR9-2, LINC00461 | chr5 | 87967773 | 87968077 | Hyper | cancer_general | MIR9-2, LINC00461 |
| chr5 | 87968486 | 87968858 | Hyper | cancer_general | MIR9-2, LINC00461 | chr5 | 87970193 | 87970872 | Hyper | cancer_general | MIR9-2, LINC00461 |
| chr5 | 87974104 | 87974307 | Hyper | cancer_general | | chr5 | 87974868 | 87975023 | Hyper | cancer_general | |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr5 | 87976028 | 87976308 | Hyper | head_neck | | chr5 | 87976525 | 87976559 | Hyper | head_neck | |
| chr5 | 87979756 | 87979912 | Hyper | cancer_general | | chr5 | 87980142 | 87980250 | Hyper | cancer_general | |
| chr5 | 87980954 | 87981325 | Hyper | cancer_general | | chr5 | 87984532 | 87984657 | Hyper | cancer_general | |
| chr5 | 87983922 | 87985954 | Hyper | cancer_general | | chr5 | 87986210 | 87986281 | Hyper | cancer_general | |
| chr5 | 87988516 | 87988584 | Hyper | cancer_general | | chr5 | 87990408 | 87990452 | Hyper | cancer_general | |
| chr5 | 88183470 | 88186001 | Hyper | cancer_general, tcga | AL050132 | chr5 | 89854856 | 89854902 | Hyper | cancer_general | GPR98 |
| chr5 | 92939916 | 92940136 | Hyper | cancer_general | | chr5 | 94955681 | 94955919 | Hyper | cancer_general | GPR150 |
| chr5 | 94956935 | 94957000 | Hyper | cancer_general | GPR150 | chr5 | 95767894 | 95768384 | Hyper | cancer_general | PCSK1 |
| chr5 | 95768920 | 95769093 | Hyper | cancer_general | PCSK1 | chr5 | 100236682 | 100236757 | Hyper | cancer_general | ST8SIA4 |
| chr5 | 100238882 | 100239151 | Hyper | tcga, cancer_general | ST8SIA4 | chr5 | 101631487 | 101631533 | Hyper | cancer_general | SLCO4C1 |
| chr5 | 101632295 | 101632573 | Hyper | tcga | SLCO4C1 | chr5 | 107005983 | 107006186 | Hyper | blood | EFNA5 |
| chr5 | 112042904 | 112043289 | Hyper | literature | APC | chr5 | 112073358 | 112073516 | Hyper | liver_tcga, literature | APC |
| chr5 | 112170808 | 112170837 | Hyper | literature | APC | chr5 | 112175198 | 112175227 | Hyper | literature | APC |
| chr5 | 112175640 | 112175669 | Hyper | literature | APC | chr5 | 112258359 | 112258388 | Hyper | tcga | MCC |
| chr5 | 112258634 | 112258663 | Hyper | tcga | | chr5 | 112629427 | 112629674 | Hyper | cancer_general | KCNN2 |
| chr5 | 113391265 | 113392018 | Hyper | tcga, cancer_general | | chr5 | 113698567 | 113698783 | Hyper | cancer_general | |
| chr5 | 113699008 | 113699119 | Hyper | cancer_general | KCNN2 | chr5 | 114514960 | 114515671 | Hyper | cancer_general | TRIM36 |
| chr5 | 115151267 | 115152638 | Hyper | cancer_general, tcga | CDO1 | chr5 | 115297192 | 115297556 | Hyper | cancer_general | AQPEP, AX747550 |
| chr5 | 115297928 | 115298042 | Hyper | cancer_general | AQPEP, AX747550 | chr5 | 115298496 | 115298741 | Hyper | tcga, cancer_general | AQPEP |
| chr5 | 115298985 | 115299041 | Hyper | cancer_general | PRR16 | chr5 | 119799931 | 119799986 | Hyper | cancer_general | PRR16 |
| chr5 | 119801299 | 119801445 | Hyper | cancer_general | PRDM6 | chr5 | 121413537 | 121413590 | Hyper | blood | LOX |
| chr5 | 122422240 | 122422292 | Hyper | cancer_general | PRDM6 | chr5 | 122422616 | 122422651 | Hyper | cancer_general | PRDM6 |
| chr5 | 122423328 | 122423376 | Hyper | cancer_general | PRDM6 | chr5 | 122425128 | 122425168 | Hyper | cancer_general | PRDM6 |
| chr5 | 122431118 | 122431378 | Hyper | cancer_general | | chr5 | 126626283 | 126626738 | Hyper | cancer_general, tcga | MEGF10 |
| chr5 | 127872942 | 127872990 | Hyper | cancer_general | FBN2 | chr5 | 127873268 | 127873710 | Hyper | tcga, cancer_general | FBN2 |
| chr5 | 127874448 | 127874839 | Hyper | tcga, literature, cancer_general | FBN2 | chr5 | 128300680 | 128300794 | Hyper | cancer_general | SLC27A6 |
| chr5 | 128796081 | 128796244 | Hyper | cancer_general | ADAMTS19 | chr5 | 128796867 | 128796985 | Hyper | cancer_general | ADAMTS19 |
| chr5 | 128797344 | 128797386 | Hyper | cancer_general | ADAMTS19 | chr5 | 129240068 | 129240101 | Hyper | esophageal | CHSY3 |
| chr5 | 131992096 | 131992157 | Hyper | cancer_general | IL13, BC042122 | chr5 | 132947486 | 132947836 | Hyper | tcga, cancer_general | |
| chr5 | 134363309 | 134363338 | Hyper | liver_tcga | PITX1, LOC100996485 | chr5 | 134363876 | 134363973 | Hyper | liver_tcga | LOC100996485, PITX1 |
| chr5 | 134364195 | 134364513 | Hyper | liver_tcga, cancer_general | LOC100996485, PITX1 | chr5 | 134366718 | 134366788 | Hyper | cancer_general | LOC100996485, PITX1 |
| chr5 | 134367108 | 134367203 | Hyper | cancer_general | LOC100996485, PITX1 | chr5 | 134374447 | 134375210 | Hyper | cancer_general | LOC100996485, PITX1 |
| chr5 | 134376222 | 134376375 | Hyper | cancer_general | PITX1, LOC100996485 | chr5 | 134376697 | 134376824 | Hyper | cancer_general | LOC100996485, PITX1 |
| chr5 | 134385952 | 134386383 | Hyper | cancer_general | LOC100996485 | chr5 | 134735622 | 134735651 | Hyper | literature | |
| chr5 | 134825463 | 134825518 | Hyper | cancer_general | | chr5 | 134825889 | 134826006 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 134870446 | 134870515 | Hyper | cancer_general | NEUROG1 | chr5 | 134870780 | 134871196 | Hyper | cancer_general | NEUROG1 |
| chr5 | 134871601 | 134872049 | Hyper | cancer_general | NEUROG1 | chr5 | 134879478 | 134880501 | Hyper | cancer_general | NEUROG1 |
| chr5 | 134914627 | 134914748 | Hyper | tcga | CXCL14 | chr5 | 135265737 | 135265767 | Hyper | cancer_general | FBXL21 |
| chr5 | 135266114 | 135266672 | Hyper | cancer_general | FBXL21 | chr5 | 135528201 | 135528233 | Hyper | cancer_general | LOC389332, SMAD5 |
| chr5 | 136834050 | 136834506 | Hyper | tcga, cancer_general | SPOCK1 | chr5 | 136834720 | 136834826 | Hyper | cancer_general | SPOCK1 |
| chr5 | 137225092 | 137225297 | Hyper | liver_tcga, cancer_general | PKD2L2, MYOT | chr5 | 139045286 | 139045315 | Hyper | liver_tcga | CXXC5 |
| chr5 | 139047990 | 139048162 | Hyper | tcga, liver_tcga | CXXC5 | chr5 | 139056666 | 139056804 | Hyper | liver_tcga | CXXC5 |
| chr5 | 139227773 | 139227909 | Hyper | cancer_general | NRG2, PSD2 | chr5 | 139525728 | 139525758 | Hyper | cancer_general | |
| chr5 | 140174798 | 140174901 | Hyper | cancer_general | PCDHA3, PCDHA2, PCDHA1 | chr5 | 140187094 | 140187146 | Hyper | cancer_general | PCDHA4, PCDHA3, PCDHA2 |
| chr5 | 140305978 | 140306050 | Hyper | cancer_general | PCDHAC1, PCDHA13 | chr5 | 140306321 | 140306733 | Hyper | cancer_general | PCDHAC1, PCDHA13 |
| chr5 | 140346595 | 140346671 | Hyper | cancer_general | PCDHAC2 | chr5 | 140514891 | 140514921 | Hyper | cancer_general | PCDHB5, PCDHB4 |
| chr5 | 140604459 | 140604501 | Hyper | cancer_general | PCDHB18, PCDHB14, PCDHB13 | chr5 | 140613926 | 140614014 | Hyper | cancer_general | PCDHB18, PCDHB19P, PCDHB14 |
| chr5 | 140614314 | 140614383 | Hyper | cancer_general | PCDHB14, PCDHB19P, PCDHB18 | chr5 | 140683631 | 140683772 | Hyper | liver_tcga | SLC25A2 |
| chr5 | 140777328 | 140777487 | Hyper | cancer_general | PCDHGB5, PCDHGA9, PCDHGA8, PCDHGB4, PCDHGA7 | chr5 | 140787608 | 140787637 | Hyper | literature | |
| chr5 | 140797076 | 140797342 | Hyper | liver_tcga, cancer_general | PCDHGB8P, PCDHGA10, PCDHGB6, PCDHGA9, PCDHGB7, PCDHGA11 | chr5 | 140800479 | 140801246 | Hyper | cancer_general, liver_tcga | PCDHGA11, PCDHGB8P, PCDHGA12, PCDHGB7, PCDHGA10, PCDHGB6 |
| chr5 | 140811087 | 140811116 | Hyper | liver_tcga | PCDHGB8P, PCDHGA11, PCDHGB7, PCDHGA12 | chr5 | 140855598 | 140856622 | Hyper | cancer_general | PCDHGC4, PCDHGC3 |
| chr5 | 141031121 | 141031150 | Hyper | liver_tcga | ARAP3, FCHSD1 | chr5 | 141263035 | 141263236 | Hyper | tcga, cancer_general | BC127870, PCDH1 |
| chr5 | 141931340 | 141931539 | Hyper | cancer_general | | chr5 | 142784967 | 142785272 | Hyper | tcga | NR3C1 |
| chr5 | 145713645 | 145713896 | Hyper | cancer_general | POU4F3 | chr5 | 145717175 | 145717437 | Hyper | cancer_general | POU4F3 |
| chr5 | 145718802 | 145719925 | Hyper | cancer_general | POU4F3 | chr5 | 145720812 | 145720917 | Hyper | cancer_general | POU4F3 |
| chr5 | 145722116 | 145723027 | Hyper | cancer_general | POU4F3 | chr5 | 145724502 | 145724698 | Hyper | tcga, colorectal, cancer_general | POU4F3 |
| chr5 | 145725212 | 145725844 | Hyper | cancer_general | | chr5 | 146257332 | 146257602 | Hyper | cancer_general | PPP2R2B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 146889220 | 146889575 | Hyper | tcga, cancer_general | DPYSL3 | chr5 | 149503827 | 149503856 | Hyper | literature | PDGFRB |
| chr5 | 149682074 | 149682166 | Hyper | cancer_general | ARSI | chr5 | 150051101 | 150051667 | Hyper | cancer_general | MYOZ3 |
| chr5 | 150326159 | 150326188 | Hyper | literature | ZNF300P1 | chr5 | 150400123 | 150400203 | Hyper | cancer_general | TNIP1, GPX3 |
| chr5 | 151066442 | 151066474 | Hyper | cancer_general | BC039364, SPARC | chr5 | 151304371 | 151304401 | Hyper | cancer_general | |
| chr5 | 153852664 | 153852792 | Hyper | cancer_general | HAND1 | chr5 | 153853420 | 153853478 | Hyper | cancer_general | HAND1 |
| chr5 | 153854330 | 153854360 | Hyper | cancer_general | HAND1 | chr5 | 153855175 | 153855264 | Hyper | cancer_general | HAND1 |
| chr5 | 153855591 | 153855839 | Hyper | cancer_general | HAND1 | chr5 | 153856090 | 153856396 | Hyper | cancer_general | HAND1 |
| chr5 | 153856936 | 153856996 | Hyper | cancer_general | HAND1 | chr5 | 153857379 | 153857429 | Hyper | cancer_general | HAND1 |
| chr5 | 153858319 | 153858599 | Hyper | cancer_general | HAND1 | chr5 | 153859676 | 153859708 | Hyper | cancer_general | HAND1 |
| chr5 | 153862037 | 153862577 | Hyper | tcga, cancer_general | HAND1 | chr5 | 153863421 | 153863451 | Hyper | cancer_general | HAND1 |
| chr5 | 155107794 | 155107848 | Hyper | cancer_general | | chr5 | 155108097 | 155108526 | Hyper | tcga, cancer_general | |
| chr5 | 155108733 | 155108763 | Hyper | cancer_general | | chr5 | 157001739 | 157001843 | Hyper | cancer_general | ADAM19 |
| chr5 | 157098362 | 157098619 | Hyper | liver_tcga, cancer_general | C5orf52 | chr5 | 158478483 | 158478764 | Hyper | cancer_general | EBF1 |
| chr5 | 158524692 | 158524748 | Hyper | cancer_general | AK123543, EBF1 | chr5 | 158527443 | 158528069 | Hyper | tcga, liver_tcga, cancer_general | AK123543, EBF1 |
| chr5 | 159399095 | 159399233 | Hyper | cancer_general | TRNA_Leu, ADRA1B | chr5 | 160975724 | 160975754 | Hyper | cancer_general | GABRB2 |
| chr5 | 161274310 | 161274554 | Hyper | literature, cancer_general | GABRA1 | chr5 | 167956177 | 167956595 | Hyper | tcga, cancer_general | FBLL1, RARS |
| chr5 | 168727924 | 168727988 | Hyper | cancer_general | | chr5 | 169064327 | 169064805 | Hyper | tcga, liver_tcga, cancer_general | DOCK2 |
| chr5 | 170108287 | 170108372 | Hyper | cancer_general | KCNIP1 | chr5 | 170289444 | 170289498 | Hyper | pancreas | RANBP17 |
| chr5 | 170735154 | 170735206 | Hyper | cancer_general | TLX3, AX746723, RANBP17 | chr5 | 170735422 | 170735788 | Hyper | pancreas, cancer_general | TLX3, AX746723, RANBP17 |
| chr5 | 170736116 | 170737479 | Hyper | liver_tcga, cancer_general | TLX3, AX746723, RANBP17 | chr5 | 170737741 | 170739481 | Hyper | tcga, cancer_general | TLX3, AX746723 |
| chr5 | 170739823 | 170740027 | Hyper | cancer_general | TLX3, AX746723 | chr5 | 170740461 | 170741240 | Hyper | cancer_general | TLX3, AX746723 |
| chr5 | 170741465 | 170744128 | Hyper | cancer_general | TLX3, AX746723 | chr5 | 170744375 | 170744562 | Hyper | cancer_general | TLX3, AX746723 |
| chr5 | 170745389 | 170745480 | Hyper | cancer_general | TLX3, AX746723 | chr5 | 172655879 | 172656215 | Hyper | cancer_general | NKX2-5 |
| chr5 | 172659225 | 172659290 | Hyper | cancer_general | NKX2-5 | chr5 | 172659496 | 172659655 | Hyper | cancer_general | NKX2-5 |
| chr5 | 172659855 | 172660218 | Hyper | cancer_general | NKX2-5 | chr5 | 172660719 | 172661684 | Hyper | cancer_general | NKX2-5 |
| chr5 | 172664226 | 172664487 | Hyper | cancer_general | NKX2-5 | chr5 | 172665590 | 172665812 | Hyper | cancer_general | NKX2-5 |
| chr5 | 172670983 | 172671018 | Hyper | cancer_general | NKX2-5 | chr5 | 172671345 | 172671968 | Hyper | tcga, cancer_general | NKX2-5 |
| chr5 | 172754589 | 172754621 | Hyper | cancer_general | STC2 | chr5 | 172754832 | 172754931 | Hyper | cancer_general | STC2 |
| chr5 | 172755470 | 172755663 | Hyper | cancer_general | STC2 | chr5 | 172757048 | 172757111 | Hyper | cancer_general | STC2 |
| chr5 | 174115388 | 174115861 | Hyper | cancer_general | | chr5 | 174147523 | 174147596 | Hyper | cancer_general | MSX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 174150415 | 174150445 | Hyper | cancer_general | MSX2 | chr5 | 174158808 | 174159588 | Hyper | cancer_general | MSX2 |
| chr5 | 174162874 | 174162904 | Hyper | cancer_general | MSX2 | chr5 | 174220971 | 174221001 | Hyper | head_neck | |
| chr5 | 174870738 | 174870786 | Hyper | cancer_general | DRD1 | chr5 | 174871174 | 174871497 | Hyper | cancer_general | DRD1 |
| chr5 | 175085147 | 175085209 | Hyper | cancer_general | HRH2 | chr5 | 175083476 | 175085719 | Hyper | cancer_general | HRH2 |
| chr5 | 175223671 | 175223709 | Hyper | cancer_general | CPLX2 | chr5 | 175224016 | 175224271 | Hyper | cancer_general | CPLX2 |
| chr5 | 175298549 | 175298883 | Hyper | tcga | CPLX2 | chr5 | 175299294 | 175299396 | Hyper | cancer_general | CPLX2 |
| chr5 | 175300351 | 175300381 | Hyper | cancer_general | Hfb1, CPLX2 | chr5 | 175621390 | 175621501 | Hyper | cancer_general | |
| chr5 | 175792865 | 175793063 | Hyper | tcga, liver_tcga, cancer_general | KIAA1191, ARL10 | chr5 | 176023916 | 176024318 | Hyper | cancer_general | GPRIN1, CDHR2 |
| chr5 | 176046363 | 176046554 | Hyper | cancer_general | SNCB, MIR4281 | chr5 | 176107274 | 176107586 | Hyper | cancer_general | |
| chr5 | 176236721 | 176236898 | Hyper | cancer_general | UNC5A | chr5 | 176264805 | 176264915 | Hyper | cancer_general | UNC5A |
| chr5 | 176520166 | 176520195 | Hyper | literature | FGFR4 | chr5 | 176522400 | 176522566 | Hyper | literature | FGFR4 |
| chr5 | 176827656 | 176827685 | Hyper | literature | F12, PFN3, SLC34A1 | chr5 | 177411638 | 177412141 | Hyper | cancer_general | PROP1 |
| chr5 | 178003708 | 178003848 | Hyper | cancer_general | | chr5 | 178004325 | 178004374 | Hyper | cancer_general | ZNF454, ZFP2 |
| chr5 | 178016575 | 178017867 | Hyper | tcga, cancer_general | | chr5 | 178368074 | 178368383 | Hyper | cancer_general | |
| chr5 | 178421474 | 178421504 | Hyper | cancer_general | GRM6 | chr5 | 178421766 | 178422142 | Hyper | literature, cancer_general | GRM6 |
| chr5 | 178487107 | 178487398 | Hyper | tcga, cancer_general | ZNF354C | chr5 | 178771314 | 178771955 | Hyper | tcga, cancer_general | ADAMTS2 |
| chr5 | 178772205 | 178772272 | Hyper | cancer_general | ADAMTS2 | chr5 | 178772603 | 178772745 | Hyper | cancer_general | ADAMTS2 |
| chr5 | 178957637 | 178957944 | Hyper | tcga | AX747985 | chr5 | 179243984 | 179244277 | Hyper | cancer_general | SQSTM1 |
| chr5 | 179780104 | 179780144 | Hyper | cancer_general | GFPT2 | chr5 | 179780706 | 179780985 | Hyper | cancer_general | GFPT2 |
| chr5 | 179867486 | 179867548 | Hyper | tcga | | chr5 | 180017118 | 180017198 | Hyper | cancer_general | SCGB3A1 |
| chr5 | 180017608 | 180017933 | Hyper | tcga, cancer_general | SCGB3A1 | chr5 | 180018311 | 180018498 | Hyper | cancer_general | SCGB3A1 |
| chr5 | 180075846 | 180076317 | Hyper | cancer_general | FLT4 | chr5 | 180076567 | 180076602 | Hyper | cancer_general | FLT4 |
| chr5 | 180076804 | 180076996 | Hyper | tcga, cancer_general | FLT4 | chr5 | 180100915 | 180101332 | Hyper | tcga, cancer_general | DQ589679 |
| chr5 | 180527546 | 180527766 | Hyper | liver_tcga, cancer_general | TRNA_Val, TRNA_Leu | chr5 | 180594851 | 180595002 | Hyper | head_neck | TRNA_Val, TRNA_Leu, TRNA_Pseudo |
| chr5 | 180600858 | 180601218 | Hyper | cancer_general | TRNA_Leu, TRNA_Val, TRNA_Pseudo | chr14 | 21093454 | 21093631 | Hyper | cancer_general | TRNA_Pro, TRNA_Leu, TRNA_Thr |
| chr14 | 21100801 | 21100831 | Hyper | head_neck | TRNA_Pro, OR6S1, TRNA_Thr, TRNA_Leu | chr14 | 22005029 | 22005073 | Hyper | cancer_general | |
| chr14 | 23356044 | 23356384 | Hyper | tcga, liver_tcga | REM2, LRP10 | chr14 | 24045513 | 24045603 | Hyper | cancer_general | JPH4, AP1G2 |
| chr14 | 24640932 | 24641215 | Hyper | literature | REC8, IPO4, IRF9 | chr14 | 24803594 | 24804409 | Hyper | tcga, cancer_general, literature | ADCY4, RIPK3 |
| chr14 | 26674354 | 26674384 | Hyper | cancer_general | | chr14 | 26674699 | 26674729 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 27066562 | 27066785 | Hyper | tcga | NOVA1 | chr14 | 27067161 | 27067386 | Hyper | cancer_general | NOVA1 |
| chr14 | 29225531 | 29225561 | Hyper | cancer_general | FOXG1 | chr14 | 29226071 | 29226198 | Hyper | cancer_general | FOXG1 |
| chr14 | 29228654 | 29228778 | Hyper | cancer_general | FOXG1 | chr14 | 29229107 | 29229386 | Hyper | cancer_general | FOXG1 |
| chr14 | 29231071 | 29231217 | Hyper | cancer_general | FOXG1, C14orf23 | chr14 | 29231425 | 29231590 | Hyper | cancer_general | C14orf23, FOXG1 |
| chr14 | 29235003 | 29235356 | Hyper | cancer_general | FOXG1, BC034423, C14orf23 | chr14 | 29237063 | 29237107 | Hyper | cancer_general | FOXG1 |
| chr14 | 29242763 | 29242908 | Hyper | cancer_general | FOXG1, BC034423, C14orf23 | chr14 | 29243516 | 29243888 | Hyper | literature, cancer_general | BC034423, C14orf23, FOXG1 |
| chr14 | 29244224 | 29244308 | Hyper | cancer_general | BC034423, C14orf23, FOXG1 | chr14 | 29247689 | 29247740 | Hyper | cancer_general | BC034423, C14orf23, FOXG1 |
| chr14 | 29254575 | 29254713 | Hyper | cancer_general | BC034423, C14orf23 | chr14 | 31344346 | 31344549 | Hyper | cancer_general | COCH, LOC100506071 |
| chr14 | 33402462 | 33402762 | Hyper | cancer_general | NPAS3 | chr14 | 33403045 | 33403316 | Hyper | tcga, cancer_general | NPAS3 |
| chr14 | 33403866 | 33404418 | Hyper | cancer_general | NPAS3 | chr14 | 34420250 | 34420288 | Hyper | blood | EGLN3 |
| chr14 | 36003442 | 36003826 | Hyper | tcga, liver_tcga | RALGAPA1, INSM2 | chr14 | 36004063 | 36004493 | Hyper | cancer_general | RALGAPA1, INSM2 |
| chr14 | 36004711 | 36004983 | Hyper | cancer_general | INSM2, RALGAPA1 | chr14 | 36972803 | 36972912 | Hyper | cancer_general | SFTA3 |
| chr14 | 36973254 | 36973538 | Hyper | cancer_general | SFTA3 | chr14 | 36974294 | 36974982 | Hyper | tcga, cancer_general | SFTA3 |
| chr14 | 36975299 | 36975399 | Hyper | cancer_general | SFTA3 | chr14 | 36977645 | 36978009 | Hyper | cancer_general | NKX2-1, SFTA3 |
| chr14 | 36978548 | 36978578 | Hyper | cancer_general | NKX2-1, BX161496, SFTA3 | chr14 | 36979619 | 36979649 | Hyper | cancer_general | NKX2-1, BX161496, SFTA3 |
| chr14 | 36982927 | 36982969 | Hyper | cancer_general | NKX2-1, SFTA3, BX161496 | chr14 | 36983708 | 36984146 | Hyper | cancer_general | NKX2-1, BX161496, SFTA3 |
| chr14 | 36985841 | 36985871 | Hyper | cancer_general | BX161496, NKX2-1, SFTA3 | chr14 | 36986301 | 36986841 | Hyper | cancer_general | BX161496, NKX2-1, SFTA3 |
| chr14 | 36987168 | 36987685 | Hyper | cancer_general | BX161496, NKX2-1, SFTA3 | chr14 | 36987939 | 36988143 | Hyper | cancer_general | SFTA3, BX161496, NKX2-1 |
| chr14 | 36988428 | 36988460 | Hyper | tcga | NKX2-1, SFTA3, BX161496 | chr14 | 36990858 | 36991177 | Hyper | cancer_general | BX161496, NKX2-1, SFTA3 |
| chr14 | 36991532 | 36991613 | Hyper | cancer_general | BX161496, NKX2-1, SFTA3 | chr14 | 36991936 | 36992217 | Hyper | cancer_general | SFTA3, BX161496, NKX2-1 |
| chr14 | 36993473 | 36993956 | Hyper | cancer_general | BX161496, NKX2-1 | chr14 | 36994248 | 36994999 | Hyper | cancer_general | BX161496, NKX2-1 |
| chr14 | 37050752 | 37050794 | Hyper | cancer_general | NKX2-8 | chr14 | 37116105 | 37116381 | Hyper | cancer_general, lung | PAX9 |
| chr14 | 37117611 | 37117697 | Hyper | cancer_general | PAX9 | chr14 | 37123438 | 37124077 | Hyper | cancer_general | PAX9 |
| chr14 | 37124364 | 37124572 | Hyper | cancer_general | PAX9 | chr14 | 37124992 | 37125545 | Hyper | tcga, cancer_general | PAX9 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 37126241 | 37126297 | Hyper | cancer_general | PAX9 | chr14 | 37126566 | 37126897 | Hyper | cancer_general | PAX9 |
| chr14 | 37127281 | 37127311 | Hyper | cancer_general | PAX9 | chr14 | 37127655 | 37128027 | Hyper | cancer_general | PAX9 |
| chr14 | 37128553 | 37128723 | Hyper | literature, cancer_general | PAX9 | chr14 | 37130077 | 37130260 | Hyper | cancer_general | PAX9 |
| chr14 | 37132375 | 37132695 | Hyper | cancer_general | PAX9 | chr14 | 37133001 | 37133052 | Hyper | cancer_general | PAX9 |
| chr14 | 37135784 | 37136345 | Hyper | cancer_general | PAX9 | chr14 | 37136588 | 37136618 | Hyper | cancer_general | PAX9 |
| chr14 | 38060677 | 38060916 | Hyper | cancer_general | FOXA1 | chr14 | 38064401 | 38064549 | Hyper | blood | FOXA1 |
| chr14 | 38677519 | 38677548 | Hyper | tcga | SSTR1 | chr14 | 38677761 | 38677790 | Hyper | tcga | SSTR1 |
| chr14 | 38724294 | 38725258 | Hyper | literature, cancer_general | CLEC14A | chr14 | 38725521 | 38725764 | Hyper | tcga | CLEC14A |
| chr14 | 42074544 | 42074987 | Hyper | cancer_general | LRFN5 | chr14 | 42075588 | 42076212 | Hyper | tcga, cancer_general | LRFN5 |
| chr14 | 42076823 | 42076853 | Hyper | cancer_general | LRFN5 | chr14 | 42077230 | 42077268 | Hyper | cancer_general | LRFN5 |
| chr14 | 42077770 | 42077800 | Hyper | cancer_general | LRFN5 | chr14 | 42079289 | 42079328 | Hyper | cancer_general | LRFN5 |
| chr14 | 48143755 | 48144097 | Hyper | cancer_general | | chr14 | 48144298 | 48144401 | Hyper | cancer_general | |
| chr14 | 48144699 | 48145257 | Hyper | tcga, cancer_general | | chr14 | 51338730 | 51338972 | Hyper | cancer_general | ABHD12B |
| chr14 | 51560304 | 51561428 | Hyper | cancer_general | TRIM9 | chr14 | 51561765 | 51562012 | Hyper | esophageal | TRIM9 |
| chr14 | 52534648 | 52534791 | Hyper | tcga | NID2 | chr14 | 52535012 | 52536404 | Hyper | tcga, cancer_general, literature | NID2 |
| chr14 | 52734509 | 52734557 | Hyper | cancer_general | PTGDR | chr14 | 52734777 | 52735255 | Hyper | cancer_general | PTGDR |
| chr14 | 52781525 | 52781916 | Hyper | cancer_general | PTGER2 | chr14 | 54422651 | 54422925 | Hyper | liver_tcga, cancer_general | BMP4, MIR5580 |
| chr14 | 55595938 | 55595968 | Hyper | liver_tcga | LGALS3 | chr14 | 57260946 | 57261821 | Hyper | cancer_general | OTX2 |
| chr14 | 57262072 | 57262179 | Hyper | cancer_general | RTN1 | chr14 | 57264079 | 57265240 | Hyper | cancer_general | OTX2 |
| chr14 | 57270995 | 57271266 | Hyper | cancer_general | OTX2-AS1, OTX2 | chr14 | 57272009 | 57272067 | Hyper | cancer_general | OTX2-AS1, OTX2 |
| chr14 | 57274486 | 57275305 | Hyper | cancer_general | OTX2-AS1, OTX2 | chr14 | 57275596 | 57276104 | Hyper | cancer_general | OTX2-AS1, OTX2 |
| chr14 | 57276440 | 57276666 | Hyper | cancer_general | OTX2-AS1, OTX2 | chr14 | 57277920 | 57279657 | Hyper | literature, cancer_general | OTX2-AS1, OTX2 |
| chr14 | 57283314 | 57284659 | Hyper | cancer_general | OTX2-AS1 | chr14 | 58332297 | 58332403 | Hyper | cancer_general | LRRC9 |
| chr14 | 60097193 | 60097566 | Hyper | cancer_general | RTN1 | chr14 | 60386207 | 60386252 | Hyper | cancer_general | JB175233 |
| chr14 | 60386638 | 60386701 | Hyper | cancer_general | LRRC9 | chr14 | 60794635 | 60794667 | Hyper | cancer_general | SIX6 |
| chr14 | 60952166 | 60952959 | Hyper | cancer_general | C14orf39 | chr14 | 60973151 | 60973324 | Hyper | cancer_general | SIX6 |
| chr14 | 60973697 | 60974077 | Hyper | literature, cancer_general | SIX6 | chr14 | 60974368 | 60974403 | Hyper | cancer_general | |
| chr14 | 60975384 | 60976514 | Hyper | tcga, cancer_general | SIX6 | chr14 | 60976813 | 60976860 | Hyper | cancer_general | SIX6 |
| chr14 | 60977337 | 60978147 | Hyper | cancer_general | SIX6 | chr14 | 60981202 | 60981268 | Hyper | cancer_general | SIX6 |
| chr14 | 60981676 | 60981793 | Hyper | cancer_general | SIX6 | chr14 | 60982110 | 60982622 | Hyper | cancer_general | SIX6 |
| chr14 | 60982841 | 60982911 | Hyper | cancer_general | SIX6 | chr14 | 61104291 | 61104864 | Hyper | liver_tcga, cancer_general | SIX1 |
| chr14 | 61108620 | 61108996 | Hyper | liver_tcga, cancer_general | SIX1 | chr14 | 61109206 | 61109470 | Hyper | cancer_general | SIX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 6109839 | 6110243 | Hyper | liver_tga, cancer_general, literature | SIX1 | chr14 | 61114137 | 61114456 | Hyper | cancer_general | SIX1 |
| chr14 | 61115311 | 61115517 | Hyper | cancer_general | SIX1 | chr14 | 61118736 | 61118765 | Hyper | literature | SIX1 |
| chr14 | 61118965 | 61119136 | Hyper | cancer_general | SIX1 | chr14 | 61119536 | 61119639 | Hyper | cancer_general | SIX1 |
| chr14 | 61747300 | 61748033 | Hyper | blood | TMEM30B | chr14 | 62279578 | 62280006 | Hyper | cancer_general | |
| chr14 | 62583809 | 62583909 | Hyper | cancer_general | LINC00643 | chr14 | 63512100 | 63512291 | Hyper | cancer_general | KCNH5 |
| chr14 | 63512573 | 63512816 | Hyper | tcga, cancer_general | KCNH5 | chr14 | 63513124 | 63513154 | Hyper | cancer_general | KCNH5 |
| chr14 | 65008994 | 65009193 | Hyper | cancer_general | PPP1R36, HSPA2 | chr14 | 70014723 | 70014974 | Hyper | cancer_general, liver_tga | |
| chr14 | 70038490 | 70038635 | Hyper | liver_tga, cancer_general | CCDC177 | chr14 | 70038990 | 70039025 | Hyper | cancer_general | CCDC177 |
| chr14 | 70346136 | 70346491 | Hyper | tcga, cancer_general | SMOC1 | chr14 | 70654343 | 70654713 | Hyper | cancer_general | |
| chr14 | 70655530 | 70656090 | Hyper | cancer_general, tcga | | chr14 | 72398743 | 72399019 | Hyper | cancer_general | RGS6 |
| chr14 | 72399361 | 72399453 | Hyper | cancer_general | RGS6 | chr14 | 72399929 | 72400029 | Hyper | cancer_general | RGS6 |
| chr14 | 74706015 | 74706222 | Hyper | cancer_general | VSX2 | chr14 | 74706458 | 74707873 | Hyper | cancer_general | VSX2 |
| chr14 | 74708862 | 74708955 | Hyper | cancer_general | VSX2 | chr14 | 74892540 | 74892569 | Hyper | liver_tga | SYNDIG1L |
| chr14 | 74893074 | 74893113 | Hyper | cancer_general | SYNDIG1L | chr14 | 75078170 | 75078507 | Hyper | cancer_general | LTBP2 |
| chr14 | 75988341 | 75988370 | Hyper | literature | BATF | chr14 | 75988732 | 75988761 | Hyper | literature | BATF |
| chr14 | 76604682 | 76604716 | Hyper | cancer_general | ESRRB | chr14 | 76605072 | 76605376 | Hyper | cancer_general | ESRRB |
| chr14 | 76843461 | 76843504 | Hyper | cancer_general | VASH1 | chr14 | 76843742 | 76843953 | Hyper | cancer_general | ZDHHC22 |
| chr14 | 77228121 | 77228159 | Hyper | liver_tga | | chr14 | 77606907 | 77607236 | Hyper | tcga, cancer_general | |
| chr14 | 77737212 | 77737785 | Hyper | tcga, cancer_general | POMT2, MIR1260A, NGB | chr14 | 79745138 | 79745175 | Hyper | cancer_general | NRXN3 |
| chr14 | 85996479 | 85996608 | Hyper | cancer_general, tcga | FLRT2, BX248253 | chr14 | 85996851 | 85996906 | Hyper | cancer_general | FLRT2, BX248253 |
| chr14 | 85997821 | 85998006 | Hyper | cancer_general | BX248253, FLRT2 | chr14 | 85998288 | 85998683 | Hyper | tcga, cancer_general | FLRT2, BX248253 |
| chr14 | 85999569 | 85999613 | Hyper | cancer_general | BX248253, FLRT2 | chr14 | 86000270 | 86000511 | Hyper | cancer_general | |
| chr14 | 86000918 | 86001114 | Hyper | cancer_general | FLRT2, BX248253 | chr14 | 89817889 | 89818034 | Hyper | cancer_general | |
| chr14 | 90527714 | 90527758 | Hyper | cancer_general | KCNK13 | chr14 | 92789512 | 92789542 | Hyper | cancer_general | SLC24A4 |
| chr14 | 92789863 | 92790169 | Hyper | tcga, cancer_general | SLC24A4 | chr14 | 92790637 | 92790703 | Hyper | cancer_general | SLC24A4 |
| chr14 | 92979917 | 92979991 | Hyper | pancreas | RIN3 | chr14 | 93389542 | 93389776 | Hyper | liver_tga, cancer_general | CHGA |
| chr14 | 94254389 | 94254513 | Hyper | cancer_general | PRIMA1 | chr14 | 94405734 | 94405785 | Hyper | cancer_general | ASB2 |
| chr14 | 94889856 | 94889886 | Hyper | head_neck | | chr14 | 95234643 | 95235369 | Hyper | tcga, cancer_general, literature | GSC |
| chr14 | 95235989 | 95236111 | Hyper | cancer_general | GSC | chr14 | 95236524 | 95236553 | Hyper | literature | GSC |
| chr14 | 95236819 | 95236848 | Hyper | literature | GSC | chr14 | 95237622 | 95237651 | Hyper | literature | GSC |
| chr14 | 95239380 | 95239633 | Hyper | cancer_general | GSC | chr14 | 95240127 | 95240157 | Hyper | cancer_general | GSC |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 95240392 | 95240422 | Hyper | cancer_general | GSC | chr14 | 95557626 | 95557655 | Hyper | literature | DICER1 |
| chr14 | 95560448 | 95560477 | Hyper | literature | DICER1 | chr14 | 96342648 | 96342692 | Hyper | cancer_general | LINC00617 |
| chr14 | 96342897 | 96343133 | Hyper | tcga, cancer_general | LINC00617 | chr14 | 96343404 | 96343433 | Hyper | tcga | LINC00617 |
| chr14 | 96343643 | 96343701 | Hyper | cancer_general | LINC00617 | chr14 | 97059856 | 97059083 | Hyper | cancer_general | BC035096 |
| chr14 | 97499277 | 97499315 | Hyper | cancer_general | | chr14 | 97499706 | 97499944 | Hyper | cancer_general | |
| chr14 | 97685044 | 97685288 | Hyper | cancer_general | | chr14 | 97685707 | 97685959 | Hyper | cancer_general | |
| chr14 | 99584575 | 99584664 | Hyper | cancer_general | | chr14 | 99712321 | 99712394 | Hyper | tcga | BCL11B |
| chr14 | 99736151 | 99736183 | Hyper | cancer_general | BCL11B | chr14 | 99737398 | 99737462 | Hyper | blood | BCL11B |
| chr14 | 100437794 | 100437977 | Hyper | cancer_general | EVL | chr14 | 100438705 | 100438811 | Hyper | cancer_general | EVL |
| chr14 | 100793556 | 100793650 | Hyper | liver_tcga | WARS, SLC25A47 | chr14 | 101193242 | 101193286 | Hyper | cancer_general | DLK1 |
| chr14 | 101543868 | 101544235 | Hyper | tcga, cancer_general | BC148240, MEG9 | chr14 | 101923114 | 101923250 | Hyper | cancer_general | |
| chr14 | 101923600 | 101923738 | Hyper | cancer_general | | chr14 | 101923957 | 101924047 | Hyper | cancer_general | |
| chr14 | 101925049 | 101925901 | Hyper | tcga, cancer_general | | chr14 | 102026360 | 102026484 | Hyper | cancer_general | MIR1247, DIO3, DIO3AS, DIO3OS |
| chr14 | 102026797 | 102026967 | Hyper | tcga | DIO3, MIR1247, DIO3AS, DIO3OS | chr14 | 102031231 | 102031271 | Hyper | cancer_general | MIR1247, DIO3AS, DIO3OS, DIO3 |
| chr14 | 102031512 | 102031580 | Hyper | cancer_general | DIO3OS, DIO3, MIR1247, DIO3AS | chr14 | 102247912 | 102248214 | Hyper | cancer_general | PPP2R5C |
| chr14 | 103021391 | 103022003 | Hyper | cancer_general | LINC00605 | chr14 | 103394884 | 103395101 | Hyper | liver_tcga, cancer_general | CDC42BPB, AMN |
| chr14 | 103655226 | 103655601 | Hyper | cancer_general | | chr14 | 103674078 | 103674143 | Hyper | cancer_general | |
| chr14 | 103687082 | 103687219 | Hyper | cancer_general | | chr14 | 103739967 | 103740150 | Hyper | cancer_general | |
| chr14 | 103740358 | 103740430 | Hyper | cancer_general | | chr14 | 103745699 | 103745750 | Hyper | cancer_general | |
| chr14 | 104601737 | 104601832 | Hyper | cancer_general | KIF26A | chr14 | 104602033 | 104602063 | Hyper | cancer_general | KIF26A |
| chr14 | 104605032 | 104605114 | Hyper | cancer_general | KIF26A | chr14 | 105071298 | 105071396 | Hyper | tcga | TMEM179 |
| chr14 | 105239389 | 105239439 | Hyper | literature | AKT1 | chr14 | 105239793 | 105239825 | Hyper | literature | AKT1 |
| chr14 | 105241309 | 105241428 | Hyper | literature | AKT1 | chr14 | 105243032 | 105243064 | Hyper | literature | AKT1 |
| chr14 | 105246427 | 105246582 | Hyper | literature | AKT1 | chr14 | 105512063 | 105512395 | Hyper | ovarian | GPR132 |
| chr14 | 105714415 | 105715529 | Hyper | pancreas | BTBD6, BRF1 | chr14 | 105830630 | 105830859 | Hyper | liver_tcga | PACS2 |
| chr14 | 105963655 | 105963772 | Hyper | liver_tcga | C14orf80, CRIP1 | AEKP01168736.1_1-4752 | 1754 | 2287 | Hyper | cancer_general | |
| chr1 | 1475556 | 1476318 | Hyper | liver_tcga, cancer_general | SSU72, TMEM240, AX747755, ATAD3A | chr1 | 1688882 | 1689012 | Hyper | liver_tcga | NADK |
| chr1 | 1935274 | 1935459 | Hyper | tcga | AK054708, KIAA1751 | chr1 | 2165895 | 2165999 | Hyper | cancer_general | SKI |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 2375148 | 2375543 | Hyper | head_neck, cancer_general | | chr1 | 2472174 | 2472301 | Hyper | pancreas | LOC115110 |
| chr1 | 2706197 | 2706469 | Hyper | cancer_general | TTC34 | chr1 | 2984719 | 2984749 | Hyper | cancer_general | PRDM16, FLJ42875 |
| chr1 | 3567093 | 3568226 | Hyper | literature, cancer_general, liver_tcga | TP73, WRAP73 | chr1 | 3663532 | 3663562 | Hyper | colorectal | CCDC27, TP73-AS1 |
| chr1 | 3663874 | 3663921 | Hyper | esophageal | CCDC27, TP73-AS1 | chr1 | 4714018 | 4714345 | Hyper | literature, cancer_general | AJAP1 |
| chr1 | 4714741 | 4716701 | Hyper | cancer_general, tcga | AJAP1 | chr1 | 6304201 | 6304242 | Hyper | cancer_general | HES3, GPR153, C1orf211, ICMT |
| chr1 | 6480514 | 6480831 | Hyper | cancer_general | ESPN, MIR4252, HES2 | chr1 | 6501001 | 6501179 | Hyper | cancer_general | ESPN |
| chr1 | 6507678 | 6508126 | Hyper | tcga, breast | ESPN | chr1 | 7764641 | 7764737 | Hyper | liver_tcga | CAMTA1 |
| chr1 | 8085685 | 8085715 | Hyper | blood | ERRFI1 | chr1 | 8277374 | 8277760 | Hyper | tcga, cancer_general | |
| chr1 | 9324231 | 9324274 | Hyper | liver_tcga | H6PD | chr1 | 9527172 | 9527208 | Hyper | liver_tcga | C1orf200, PIK3CD |
| chr1 | 9712074 | 9712104 | Hyper | esophageal | C1orf200, PIK3CD | chr1 | 9712561 | 9713014 | Hyper | tcga, cancer_general | MTOR, EXOSC10 |
| chr1 | 10948552 | 10948582 | Hyper | cancer_general | | chr1 | 11169346 | 11169375 | Hyper | literature | |
| chr1 | 11174404 | 11174433 | Hyper | literature | MTOR | chr1 | 11181358 | 11181432 | Hyper | literature | MTOR |
| chr1 | 11182142 | 11182171 | Hyper | literature | MTOR | chr1 | 11188149 | 11188178 | Hyper | literature | MTOR |
| chr1 | 11210182 | 11210211 | Hyper | literature | MTOR-AS1, MTOR | chr1 | 11217215 | 11217337 | Hyper | literature | MTOR-AS1, MTOR |
| chr1 | 11249032 | 11249061 | Hyper | liver_tcga | ANGPTL7 | chr1 | 11538705 | 11538821 | Hyper | esophageal | PTCHD2 |
| chr1 | 11539175 | 11539205 | Hyper | esophageal | PTCHD2 | chr1 | 11539410 | 11539440 | Hyper | esophageal | PTCHD2 |
| chr1 | 11540129 | 11540238 | Hyper | cancer_general | PTCHD2 | chr1 | 11752476 | 11752511 | Hyper | cancer_general | DRAXIN |
| chr1 | 11959093 | 11959196 | Hyper | cancer_general | | chr1 | 12123243 | 12123640 | Hyper | tcga, cancer_general, colorectal | TNFRSF8 |
| chr1 | 12227685 | 12227941 | Hyper | tcga, cancer_general | TNFRSF1B | chr1 | 13839770 | 13839985 | Hyper | tcga, cancer_general | LRRC38 |
| chr1 | 13910436 | 13910714 | Hyper | tcga, cancer_general | PDPN | chr1 | 14026481 | 14026618 | Hyper | liver_tcga | PRDM2 |
| chr1 | 14925501 | 14926050 | Hyper | cancer_general | KAZN | chr1 | 15251120 | 15251211 | Hyper | blood | KAZN |
| chr1 | 15480593 | 15480892 | Hyper | blood | TMEM51-AS1, TMEM51 | chr1 | 16085356 | 16085656 | Hyper | tcga | FBLIM1 |
| chr1 | 16861522 | 16861552 | Hyper | cancer_general | AX747988, BC036435, TRNA_Asn | chr1 | 17445857 | 17445943 | Hyper | pancreas | PADI2 |
| chr1 | 18434449 | 18434520 | Hyper | cancer_general | IGSF21 | chr1 | 18437457 | 18437526 | Hyper | cancer_general | IGSF21 |
| chr1 | 18956211 | 18956304 | Hyper | cancer_general | PAX7 | chr1 | 18956574 | 18956655 | Hyper | cancer_general | PAX7 |
| chr1 | 18956856 | 18957246 | Hyper | literature, cancer_general | PAX7 | chr1 | 18957507 | 18957587 | Hyper | cancer_general | PAX7 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 18958033 | 18958381 | Hyper | tcga, cancer_general | PAX7 | chr1 | 18959440 | 18959550 | Hyper | cancer_general | PAX7 |
| chr1 | 18960897 | 18960990 | Hyper | cancer_general | PAX7 | chr1 | 18962727 | 18963135 | Hyper | cancer_general | PAX7 |
| chr1 | 18969625 | 18969819 | Hyper | cancer_general | PAX7 | chr1 | 18971852 | 18971929 | Hyper | cancer_general | PAX7 |
| chr1 | 18972130 | 18972160 | Hyper | cancer_general | PAX7 | chr1 | 19043563 | 19043678 | Hyper | cancer_general | PAX7 |
| chr1 | 19992349 | 19992432 | Hyper | cancer_general | NBL1, HTR6 | chr1 | 20618329 | 20618369 | Hyper | cancer_general | VWA5B1 |
| chr1 | 20693317 | 20693420 | Hyper | blood | LOC339505 | chr1 | 20879035 | 20879289 | Hyper | cancer_general | FAM43B |
| chr1 | 20879562 | 20879640 | Hyper | cancer_general | FAM43B | chr1 | 20879845 | 20879957 | Hyper | cancer_general | FAM43B |
| chr1 | 20880182 | 20880605 | Hyper | tcga, cancer_general | FAM43B | chr1 | 21044125 | 21044161 | Hyper | cancer_general | KIF17, SH2D5 |
| chr1 | 21058635 | 21058776 | Hyper | esophageal | SH2D5 | chr1 | 21835943 | 21836007 | Hyper | cancer_general | ALPL, ASAP3, TCEA3 |
| chr1 | 22140753 | 22141184 | Hyper | tcga, cancer_general, liver_tcga | LDLRAD2, HSPG2 | chr1 | 23748982 | 23749070 | Hyper | cancer_general | |
| chr1 | 23885070 | 23885100 | Hyper | breast | ID3 | chr1 | 25255823 | 25255934 | Hyper | tcga | RUNX3 |
| chr1 | 25256354 | 25256383 | Hyper | literature | RUNX3 | chr1 | 25256924 | 25257205 | Hyper | literature, cancer_general | RUNX3 |
| chr1 | 25257532 | 25257561 | Hyper | literature | RUNX3 | chr1 | 26551695 | 26551796 | Hyper | tcga | BC030768, CEP85 |
| chr1 | 26552086 | 26552130 | Hyper | cancer_general | CEP85, BC030768 | chr1 | 26737583 | 26737613 | Hyper | cancer_general | LIN28A |
| chr1 | 26737946 | 26738182 | Hyper | cancer_general | LIN28A | chr1 | 29450491 | 29450543 | Hyper | esophageal | TMEM200B, EPB41 |
| chr1 | 29586072 | 29586674 | Hyper | tcga, lung, cancer_general | PTPRU | chr1 | 29804947 | 29805094 | Hyper | cancer_general | |
| chr1 | 30815412 | 30815578 | Hyper | cancer_general | | chr1 | 32180397 | 32180427 | Hyper | head_neck | |
| chr1 | 32237584 | 32238507 | Hyper | tcga, cancer_general | | chr1 | 32410276 | 32410306 | Hyper | cancer_general | PTP4A2 |
| chr1 | 32410519 | 32410614 | Hyper | liver_tcga | PTP4A2 | chr1 | 32930458 | 32930558 | Hyper | tcga | ZBTB8A, ZBTB8B |
| chr1 | 33219567 | 33219596 | Hyper | liver_tcga | KIAA1522 | chr1 | 34628948 | 34628978 | Hyper | cancer_general | C1orf94 |
| chr1 | 34629469 | 34629728 | Hyper | cancer_general | C1orf94 | chr1 | 34630548 | 34630635 | Hyper | cancer_general | C1orf94 |
| chr1 | 34630859 | 34630978 | Hyper | cancer_general | C1orf94 | chr1 | 34631580 | 34631662 | Hyper | cancer_general | C1orf94 |
| chr1 | 34631933 | 34631963 | Hyper | cancer_general | GJA4, GJB3 | chr1 | 34642380 | 34642573 | Hyper | cancer_general | C1orf94 |
| chr1 | 35258637 | 35258714 | Hyper | cancer_general | | chr1 | 35351078 | 35351659 | Hyper | cancer_general | DLGAP3 |
| chr1 | 35395526 | 35395851 | Hyper | tcga | | chr1 | 36042679 | 36043489 | Hyper | tcga, cancer_general | TFAP2E, PSMB2 |
| chr1 | 36849009 | 36849038 | Hyper | liver_tcga | LSM10 | chr1 | 37498792 | 37499181 | Hyper | cancer_general | GRIK3 |
| chr1 | 37499460 | 37500153 | Hyper | cancer_general | GRIK3 | chr1 | 37500468 | 37500806 | Hyper | cancer_general | GRIK3 |
| chr1 | 37501072 | 37501102 | Hyper | cancer_general | GRIK3 | chr1 | 38100689 | 38100851 | Hyper | tcga, cancer_general | RSPO1 |
| chr1 | 38219712 | 38219795 | Hyper | cancer_general | EPHA10 | chr1 | 38230042 | 38230297 | Hyper | cancer_general | EPHA10 |
| chr1 | 38230779 | 38230859 | Hyper | literature, cancer_general | EPHA10 | chr1 | 38412504 | 38412832 | Hyper | tcga, cancer_general | SF3A3, INPP5B |
| chr1 | 38510178 | 38510217 | Hyper | tcga, cancer_general | POU3F1 | chr1 | 38510563 | 38510624 | Hyper | cancer_general | POU3F1 |
| chr1 | 38510854 | 38511119 | Hyper | cancer_general | POU3F1 | chr1 | 38511337 | 38511824 | Hyper | cancer_general, colorectal, cancer_general | POU3F1 |
| chr1 | 38512385 | 38512415 | Hyper | esophageal | POU3F1 | chr1 | 38513244 | 38513318 | Hyper | liver_tcga | POU3F1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 39269741 | 39270121 | Hyper | tcga, cancer_general | | chr1 | 40137898 | 40137984 | Hyper | tcga | HPCAL4, NT5C1A |
| chr1 | 40237141 | 40237203 | Hyper | cancer_general | OXCT2, BMP8B | chr1 | 40915590 | 40915620 | Hyper | esophageal | ZFP69B |
| chr1 | 41283958 | 41284463 | Hyper | cancer_general | KCNQ4 | chr1 | 41847583 | 41847702 | Hyper | cancer_general | |
| chr1 | 41848810 | 41848840 | Hyper | cancer_general | | chr1 | 43814994 | 43815023 | Hyper | literature | |
| chr1 | 44872448 | 44873706 | Hyper | tcga, cancer_general | RNF220 | chr1 | 44883121 | 44884197 | Hyper | tcga, cancer_general | CDC20, MPL RNF220 |
| chr1 | 45308592 | 45308625 | Hyper | liver_tcga | | chr1 | 46632876 | 46632923 | Hyper | cancer_general | TSPAN1 |
| chr1 | 46913837 | 46914283 | Hyper | tcga, cancer_general | EIF2B3, PTCH2 | chr1 | 46914656 | 46914686 | Hyper | cancer_general | LOC729041 |
| chr1 | 46932765 | 46932905 | Hyper | tcga | LOC729041 | chr1 | 46951207 | 46951739 | Hyper | liver_tcga, cancer_general | |
| chr1 | 46956454 | 46956603 | Hyper | cancer_general | KNCN, MKNK1-AS1 | chr1 | 46956823 | 46957171 | Hyper | cancer_general | |
| chr1 | 47009929 | 47010070 | Hyper | cancer_general | STIL, JA375062, TAL1 | chr1 | 47695122 | 47695422 | Hyper | cancer_general | STIL, JA375062, TAL1 |
| chr1 | 47696295 | 47696597 | Hyper | cancer_general | STIL, JA375062, TAL1 | chr1 | 47696821 | 47697110 | Hyper | cancer_general | STIL, JA375062, TAL1 |
| chr1 | 47697356 | 47697510 | Hyper | cancer_general, tcga | STIL, JA375062 | chr1 | 47697732 | 47698210 | Hyper | liver_tcga, literature, cancer_general | STIL, JA375062, TAL1 |
| chr1 | 47882063 | 47882322 | Hyper | liver_tcga, cancer_general | FOXE3 | chr1 | 47882769 | 47882803 | Hyper | cancer_general | FOXE3 |
| chr1 | 47909718 | 47910160 | Hyper | cancer_general | FOXD2, FOXD2-AS1 | chr1 | 47910523 | 47910914 | Hyper | liver_tcga, cancer_general | FOXD2 |
| chr1 | 47911335 | 47911508 | Hyper | liver_tcga | FOXD2 | chr1 | 47999050 | 47999163 | Hyper | liver_tcga | |
| chr1 | 48059078 | 48059243 | Hyper | cancer_general | | chr1 | 49242344 | 49242533 | Hyper | tcga | BEND5, AGBL4 |
| chr1 | 50513629 | 50513745 | Hyper | cancer_general | ELAVL4 | chr1 | 50799278 | 50799400 | Hyper | cancer_general | |
| chr1 | 50880911 | 50881302 | Hyper | liver_tcga, cancer_general | DMRTA2 | chr1 | 50881521 | 50882529 | Hyper | cancer_general | DMRTA2 |
| chr1 | 50882808 | 50883611 | Hyper | cancer_general | DMRTA2 | chr1 | 50883882 | 50884916 | Hyper | tcga, literature, cancer_general | DMRTA2 |
| chr1 | 50885336 | 50885366 | Hyper | cancer_general | DMRTA2 | chr1 | 50886188 | 50887284 | Hyper | literature, cancer_general | DMRTA2 |
| chr1 | 50888709 | 50888826 | Hyper | cancer_general, liver_tcga | DMRTA2 | chr1 | 50889104 | 50889510 | Hyper | liver_tcga, cancer_general | DMRTA2 |
| chr1 | 50889820 | 50890379 | Hyper | cancer_general | DMRTA2 | chr1 | 50890683 | 50891595 | Hyper | lung, cancer_general | DMRTA2 |
| chr1 | 50892153 | 50892351 | Hyper | cancer_general | DMRTA2 | chr1 | 50892607 | 50893877 | Hyper | tcga, esophageal, cancer_general | DMRTA2 |
| chr1 | 53019468 | 53019568 | Hyper | esophageal | ZCCHC11 | chr1 | 53068166 | 53068546 | Hyper | cancer_general | GPX7 |
| chr1 | 53098842 | 53099067 | Hyper | tcga | FAM159A | chr1 | 53308568 | 53309248 | Hyper | cancer_general | ZYG11A |
| chr1 | 53528374 | 53528439 | Hyper | cancer_general | PODN | chr1 | 54203516 | 54204399 | Hyper | cancer_general | GLIS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 55462673 | 55462703 | Hyper | cancer_general | BSND, ETMM61 | chr1 | 57888367 | 57888397 | Hyper | cancer_general | DAB1 |
| chr1 | 57888987 | 57889087 | Hyper | cancer_general | DAB1 | chr1 | 57889402 | 57889654 | Hyper | tcga, cancer_general | DAB1 |
| chr1 | 57890431 | 57890650 | Hyper | tcga, cancer_general | DAB1 | chr1 | 58715153 | 58715194 | Hyper | cancer_general | |
| chr1 | 58715475 | 58715993 | Hyper | tcga, cancer_general | | chr1 | 61519360 | 61519394 | Hyper | cancer_general | |
| chr1 | 62660740 | 62660861 | Hyper | liver_tcga | L1TD1 | chr1 | 63539509 | 63539887 | Hyper | tcga, cancer_general | |
| chr1 | 63785333 | 63786329 | Hyper | liver_tcga, literature, cancer_general | FOXD3 | chr1 | 63787031 | 63787063 | Hyper | cancer_general | FOXD3 |
| chr1 | 63787302 | 63787568 | Hyper | cancer_general | FOXD3 U7, | chr1 | 63788423 | 63788557 | Hyper | liver_tcga | FOXD3 U7, FOXD3 |
| chr1 | 63788788 | 63790278 | Hyper | liver_tcga, cancer_general | FOXD3 | chr1 | 63792561 | 63793072 | Hyper | cancer_general | FOXD3 U7, FOXD3 |
| chr1 | 63795263 | 63796277 | Hyper | cancer_general | FOXD3 | chr1 | 63796498 | 63796575 | Hyper | cancer_general | |
| chr1 | 64240026 | 64240118 | Hyper | blood | ROR1 | chr1 | 64240617 | 64240673 | Hyper | blood | ROR1 |
| chr1 | 64937330 | 64937542 | Hyper | tcga | CACHD1 | chr1 | 65303636 | 65303692 | Hyper | literature | JAK1, RAVER2 |
| chr1 | 65304227 | 65304256 | Hyper | literature | JAK1, RAVER2 | chr1 | 65305384 | 65305413 | Hyper | literature | JAK1, RAVER2 |
| chr1 | 65306926 | 65306955 | Hyper | literature | JAK1, RAVER2 | chr1 | 65309787 | 65309816 | Hyper | literature | JAK1 |
| chr1 | 65310487 | 65310531 | Hyper | literature | JAK1 | chr1 | 65311188 | 65311217 | Hyper | literature | JAK1 |
| chr1 | 65312331 | 65312432 | Hyper | literature | JAK1 | chr1 | 65731337 | 65731446 | Hyper | tcga, cancer_general | DNAJC6, AK123450 |
| chr1 | 65731649 | 65731752 | Hyper | tcga, cancer_general | DNAJC6, AK123450 | chr1 | 65990955 | 65991034 | Hyper | cancer_general | LEPR |
| chr1 | 65991446 | 65991779 | Hyper | tcga, cancer_general | LEPR | chr1 | 66258180 | 66258774 | Hyper | cancer_general, tcga | PDE4B |
| chr1 | 66259137 | 66259174 | Hyper | cancer_general | PDE4B | chr1 | 66998790 | 66999332 | Hyper | cancer_general | SGIP1 |
| chr1 | 66999636 | 66999673 | Hyper | cancer_general | SGIP1 | chr1 | 67218064 | 67218343 | Hyper | cancer_general | SGIP1, TCTEX1D1 |
| chr1 | 67390334 | 67390450 | Hyper | literature | MIER1, WDR78 | chr1 | 67391067 | 67391096 | Hyper | literature | MIER1, WDR78 |
| chr1 | 67773159 | 67773780 | Hyper | tcga, cancer_general, liver_tcga | IL12RB2 | chr1 | 70033609 | 70033916 | Hyper | tcga | LRRC7 |
| chr1 | 70034459 | 70034574 | Hyper | tcga, cancer_general | LRRC7 | chr1 | 70035088 | 70035537 | Hyper | cancer_general | LRRC7 |
| chr1 | 72749641 | 72749715 | Hyper | cancer_general | | chr1 | 75595798 | 75596384 | Hyper | cancer_general | LHX8, AK055631 |
| chr1 | 75596687 | 75597584 | Hyper | cancer_general | LHX8, AK055631 | chr1 | 75597923 | 75598179 | Hyper | cancer_general | LHX8, AK055631 |
| chr1 | 75598384 | 75598414 | Hyper | cancer_general | LHX8, AK055631 | chr1 | 75599427 | 75599621 | Hyper | cancer_general | LHX8, AK055631 |
| chr1 | 75600225 | 75600848 | Hyper | cancer_general | LHX8, AK055631 | chr1 | 75601058 | 75601428 | Hyper | cancer_general | LHX8, AK055631 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 75601983 | 75603052 | Hyper | tcga, cancer_general | LHX8, AK055631 | chr1 | 76080484 | 76080768 | Hyper | tcga, cancer_general | SLC44A5 |
| chr1 | 76082129 | 76082209 | Hyper | cancer_general | SLC44A5 | chr1 | 76540450 | 76540666 | Hyper | tcga, cancer_general | ST6GALNAC3 |
| chr1 | 77333058 | 77333088 | Hyper | cancer_general | ST6GALNAC5 | chr1 | 77333384 | 77333544 | Hyper | cancer_general | ST6GALNAC5 |
| chr1 | 77334030 | 77334762 | Hyper | tcga, cancer_general | ST6GALNAC5 | chr1 | 77747366 | 77747453 | Hyper | cancer_general | AK5 |
| chr1 | 77747939 | 77748235 | Hyper | tcga, cancer_general | AK5 | chr1 | 78511466 | 78512354 | Hyper | tcga, lung, cancer_general | GIPC2 |
| chr1 | 78957292 | 78957522 | Hyper | cancer_general | PTGFR | chr1 | 82267150 | 82267185 | Hyper | tcga | LPHN2 |
| chr1 | 82268573 | 82268815 | Hyper | tcga | LPHN2 | chr1 | 85358622 | 85358822 | Hyper | cancer_general | LPAR3 |
| chr1 | 85463349 | 85463378 | Hyper | liver_tcga | MCOLN2 | chr1 | 85725508 | 85725537 | Hyper | tcga | BCL10, C1orf52 |
| chr1 | 86621660 | 86622127 | Hyper | tcga, cancer_general | COL24A1 | chr1 | 86622526 | 86622751 | Hyper | cancer_general, tcga | COL24A1 |
| chr1 | 87617774 | 87617807 | Hyper | cancer_general | | chr1 | 90099997 | 90100084 | Hyper | tcga | FLJ27354, LRRC8C |
| chr1 | 90309292 | 90309490 | Hyper | ovarian | LRRC8D | chr1 | 91172012 | 91172677 | Hyper | cancer_general | BARHL2 |
| chr1 | 91177941 | 91178207 | Hyper | cancer_general | BARHL2 | chr1 | 91180075 | 91180306 | Hyper | lung, cancer_general | BARHL2 |
| chr1 | 91181932 | 91182132 | Hyper | cancer_general | BARHL2 | chr1 | 91182338 | 91183711 | Hyper | cancer_general, tcga, liver_tcga, literature | BARHL2 |
| chr1 | 91183951 | 91183986 | Hyper | cancer_general | BARHL2 | chr1 | 91184423 | 91184672 | Hyper | cancer_general | BARHL2 |
| chr1 | 91185190 | 91185707 | Hyper | cancer_general | BARHL2 | chr1 | 91188983 | 91189383 | Hyper | cancer_general | BARHL2 |
| chr1 | 91189688 | 91190380 | Hyper | cancer_general | BARHL2 | chr1 | 91190869 | 91191310 | Hyper | cancer_general | |
| chr1 | 91192274 | 91192671 | Hyper | cancer_general | | chr1 | 91194414 | 91194569 | Hyper | cancer_general | |
| chr1 | 91195117 | 91195390 | Hyper | cancer_general | | chr1 | 91195879 | 91196502 | Hyper | cancer_general | |
| chr1 | 91316261 | 91316313 | Hyper | cancer_general | | chr1 | 91316627 | 91316682 | Hyper | cancer_general | GFI1 |
| chr1 | 91869988 | 91870018 | Hyper | esophageal | HFM1 | chr1 | 92948324 | 92948597 | Hyper | cancer_general | GFI1 |
| chr1 | 92948841 | 92948976 | Hyper | cancer_general | GFI1 | chr1 | 92952145 | 92952655 | Hyper | tcga, cancer_general | |
| chr1 | 94147641 | 94147670 | Hyper | tcga | | chr1 | 95006795 | 95006902 | Hyper | blood | F3 |
| chr1 | 98510791 | 98511335 | Hyper | tcga, cancer_general | MIR2682, MIR137, MIR137HG | chr1 | 98511628 | 98511922 | Hyper | cancer_general | MIR2682, MIR137HG, MIR137 |
| chr1 | 98514225 | 98514255 | Hyper | cancer_general | MIR137HG, MIR137, MIR2682 | chr1 | 98515256 | 98515319 | Hyper | cancer_general | MIR2682, MIR137, MIR137HG |
| chr1 | 98519023 | 98519675 | Hyper | pancreas, tcga, cancer_general | MIR2682, MIR137HG, MIR137 | chr1 | 99469682 | 99469788 | Hyper | cancer_general | LOC100129620, LPPR5 |
| chr1 | 99470128 | 99470207 | Hyper | liver_tcga | LOC100129620, LPPR5 | chr1 | 99470785 | 99470847 | Hyper | cancer_general | LOC100129620, LPPR5 |
| chr1 | 101004456 | 101004737 | Hyper | cancer_general | GPR88 | chr1 | 101005071 | 101005144 | Hyper | cancer_general | GPR88 |
| chr1 | 101005360 | 101005675 | Hyper | cancer_general, tcga | GPR88 | chr1 | 101702504 | 101702616 | Hyper | tcga, cancer_general | S1PR1 |
| chr1 | 101703612 | 101703642 | Hyper | cancer_general | S1PR1 | chr1 | 103574508 | 103574537 | Hyper | cancer_general, literature | COL11A1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 107682735 | 107682977 | Hyper | tcga, cancer_general | NTNG1 | chr1 | 107683439 | 107683517 | Hyper | cancer_general | NTNG1 |
| chr1 | 107684240 | 107684439 | Hyper | tcga | NTNG1 | chr1 | 108507063 | 108507092 | Hyper | tcga | VAV3-AS1 |
| chr1 | 108507320 | 108507497 | Hyper | tcga, cancer_general | VAV3-AS1 | chr1 | 108507717 | 108507810 | Hyper | cancer_general | VAV3-AS1 |
| chr1 | 108508052 | 108508640 | Hyper | cancer_general, tcga | VAV3-AS1 | chr1 | 109203609 | 109203672 | Hyper | liver_tcga | HENMT1 |
| chr1 | 110610586 | 110612058 | Hyper | liver_tcga, cancer_general, literature | DQ574855, ALX3 | chr1 | 110612846 | 110613152 | Hyper | cancer_general | DQ574855, ALX3 |
| chr1 | 110626684 | 110627578 | Hyper | cancer_general | | chr1 | 110672889 | 110673233 | Hyper | cancer_general | |
| chr1 | 110692973 | 110694117 | Hyper | tcga, cancer_general | SLC6A17 | chr1 | 110754003 | 110754101 | Hyper | liver_tcga | |
| chr1 | 110754309 | 110754830 | Hyper | cancer_general | KCNC4 | chr1 | 111097906 | 111097936 | Hyper | cancer_general | KCNC4 |
| chr1 | 111098196 | 111098316 | Hyper | cancer_general | | chr1 | 111216763 | 111217982 | Hyper | liver_tcga, tcga, cancer_general | KCNA3 |
| chr1 | 111506007 | 111506212 | Hyper | cancer_general | LRIF1 | chr1 | 111813546 | 111813587 | Hyper | cancer_general | CHIAP2 |
| chr1 | 114695439 | 114695943 | Hyper | tcga, cancer_general | | chr1 | 114696210 | 114696712 | Hyper | tcga, cancer_general | |
| chr1 | 115256514 | 115256552 | Hyper | literature | CSDE1, NRAS | chr1 | 115258729 | 115258772 | Hyper | literature | NRAS, CSDE1 |
| chr1 | 115631867 | 115631915 | Hyper | pancreas | TSPAN2 | chr1 | 115632469 | 115632555 | Hyper | cancer_general | TSPAN2 |
| chr1 | 115880184 | 115880395 | Hyper | pancreas, cancer_general | | chr1 | 115880850 | 115881218 | Hyper | cancer_general | |
| chr1 | 116371139 | 116371201 | Hyper | cancer_general | NHLH2 | chr1 | 116380651 | 116381287 | Hyper | cancer_general | NHLH2 |
| chr1 | 116382387 | 116382478 | Hyper | cancer_general | NHLH2 | chr1 | 119522074 | 119522530 | Hyper | cancer_general | TBX15 |
| chr1 | 119522839 | 119522940 | Hyper | cancer_general | TBX15 | chr1 | 119527072 | 119527391 | Hyper | liver_tcga, cancer_general | TBX15 |
| chr1 | 119527623 | 119527652 | Hyper | liver_tcga | TBX15 | chr1 | 119528653 | 119529118 | Hyper | liver_tcga, cancer_general | TBX15 |
| chr1 | 119529804 | 119529839 | Hyper | cancer_general | TBX15 | chr1 | 119530100 | 119530725 | Hyper | liver_tcga, cancer_general | TBX15 |
| chr1 | 119531029 | 119531157 | Hyper | cancer_general | TBX15 | chr1 | 119532043 | 119532320 | Hyper | liver_tcga | TBX15 |
| chr1 | 119535816 | 119536377 | Hyper | cancer_general, liver_tcga | TBX15 | chr1 | 119542322 | 119542352 | Hyper | cancer_general | |
| chr1 | 119542997 | 119543230 | Hyper | cancer_general | | chr1 | 119543532 | 119544182 | Hyper | cancer_general | |
| chr1 | 119548823 | 119548853 | Hyper | liver_tcga | | chr1 | 119549058 | 119549929 | Hyper | liver_tcga | |
| chr1 | 119550155 | 119550278 | Hyper | cancer_general | | chr1 | 119550533 | 119550633 | Hyper | cancer_general | |
| chr1 | 119550904 | 119551269 | Hyper | cancer_general | | chr1 | 145075523 | 145075552 | Hyper | liver_tcga | |
| chr1 | 151693945 | 151694351 | Hyper | tcga, cancer_general | RIIAD1, CELF3 | chr1 | 151812413 | 151812442 | Hyper | liver_tcga | PDE4DIP THEM5, LOC100132111, C2CD4D, RORC |
| chr1 | 152009415 | 152009510 | Hyper | hepatobiliary | S100A11, AC2 | chr1 | 152085398 | 152085504 | Hyper | cancer_general | TCHH |
| chr1 | 152488150 | 152488197 | Hyper | cancer_general | CRCT1, LCE5A | chr1 | 153651965 | 153652379 | Hyper | tcga, liver_tcga, cancer_general | ILF2, NPR1, TRNA_Met |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 154127987 | 154128016 | Hyper | literature | TPM3, NUP210L | chr1 | 154298320 | 154298557 | Hyper | tcga | ATP8B2, AQP10 |
| chr1 | 154475153 | 154475531 | Hyper | cancer_general | TDRD10, SHE | chr1 | 155043331 | 155043657 | Hyper | breast | EFNA4, ADAM15, EFNA3 |
| chr1 | 155164415 | 155164455 | Hyper | hepatobiliary | TRIM46, MIR92B, THBS3, DM075093, MUC1, AX746485 | chr1 | 155874151 | 155874300 | Hyper | literature | KIAA0907, RIT1 |
| chr1 | 155874508 | 155874546 | Hyper | literature | KIAA0907, RIT1 | chr1 | 156215329 | 156215359 | Hyper | cancer_general | PAQR6, BGLAP, SMG5 |
| chr1 | 156215607 | 156215805 | Hyper | cancer_general | SMG5, PAQR6, BGLAP | chr1 | 156357993 | 156358508 | Hyper | cancer_general | RHBG |
| chr1 | 156390135 | 156390698 | Hyper | cancer_general | C1orf61, MIR9-1 | chr1 | 156405518 | 156406431 | Hyper | tcga, cancer_general | C1orf61 |
| chr1 | 156594974 | 156595021 | Hyper | cancer_general | HAPLN2 | chr1 | 156611889 | 156612119 | Hyper | cancer_general | BC005081, BCAN |
| chr1 | 156626589 | 156626658 | Hyper | cancer_general | BCAN | chr1 | 156626891 | 156627034 | Hyper | cancer_general | BCAN |
| chr1 | 156646278 | 156646307 | Hyper | literature | NES | chr1 | 156646593 | 156646647 | Hyper | cancer_general | NES |
| chr1 | 156814933 | 156815146 | Hyper | cancer_general | INSRR, NTRK1 | chr1 | 156815445 | 156815745 | Hyper | pancreas, cancer_general | INSRR, NTRK1 |
| chr1 | 156830269 | 156830348 | Hyper | tcga | NTRK1, INSRR | chr1 | 156863107 | 156863331 | Hyper | cancer_general | PEAR1 |
| chr1 | 156863662 | 156863724 | Hyper | cancer_general | PEAR1 | chr1 | 159158348 | 159158511 | Hyper | cancer_general | LOC100131825, CADM3 |
| chr1 | 161228659 | 161228891 | Hyper | tcga, cancer_general | PCP4L1 | chr1 | 161275564 | 161276026 | Hyper | cancer_general | SDHC, MPZ |
| chr1 | 161368993 | 161369405 | Hyper | head_neck | TRNA_Val FCGR3B, TRNA_Asn, TRNA_Glu, TRNA_Leu | chr1 | 161369859 | 161369945 | Hyper | head_neck | TRNA_Val |
| chr1 | 161591472 | 161591546 | Hyper | cancer_general | | chr1 | 162724401 | 162724430 | Hyper | literature | DDR2 |
| chr1 | 162729615 | 162729686 | Hyper | literature | DDR2 | chr1 | 162748392 | 162748421 | Hyper | literature | AF268386, Metazoa_SRP, DDR2 |
| chr1 | 162792306 | 162792533 | Hyper | cancer_general | C1orf110, HSD17B7 | chr1 | 164290615 | 164290689 | Hyper | cancer_general | |
| chr1 | 165086988 | 165087027 | Hyper | cancer_general | LMX1A | chr1 | 165205079 | 165205146 | Hyper | cancer_general | LMX1A |
| chr1 | 165321747 | 165321852 | Hyper | cancer_general | LMX1A | chr1 | 165323151 | 165323181 | Hyper | cancer_general | LMX1A |
| chr1 | 165324196 | 165324249 | Hyper | cancer_general | LMX1A | chr1 | 165324488 | 165324668 | Hyper | cancer_general | LMX1A |
| chr1 | 165325108 | 165325521 | Hyper | cancer_general | LMX1A | chr1 | 165325896 | 165325950 | Hyper | cancer_general | LMX1A |
| chr1 | 165326204 | 165326469 | Hyper | literature, cancer_general | | chr1 | 165414191 | 165414272 | Hyper | cancer_general | RXRG |
| chr1 | 166134247 | 166134306 | Hyper | tcga | | chr1 | 166134728 | 166134796 | Hyper | liver_tcga | TADA1 |
| chr1 | 166135193 | 166135281 | Hyper | liver_tcga | | chr1 | 166853563 | 166853592 | Hyper | cancer_general | |
| chr1 | 166890292 | 166890436 | Hyper | | ILDR2 | chr1 | 166916866 | 166917100 | Hyper | cancer_general | ILDR2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 167090617 | 167090757 | Hyper | liver_tga | DUSP27 | chr1 | 167599179 | 167599330 | Hyper | cancer_general | RCSD1 |
| chr1 | 167599616 | 167599844 | Hyper | tga, cancer_general | RCSD1 | chr1 | 169396376 | 169396923 | Hyper | cancer_general, literature | CCDC181 |
| chr1 | 170629540 | 170629569 | Hyper | literature | PRRX1 | chr1 | 170630055 | 170630084 | Hyper | liver_tga, literature | PRRX1 |
| chr1 | 170630456 | 170630810 | Hyper | literature, cancer_general, liver_tga | PRRX1 | chr1 | 170631084 | 170631163 | Hyper | cancer_general | PRRX1 |
| chr1 | 170631477 | 170631559 | Hyper | cancer_general | PRRX1 | chr1 | 170633607 | 170633637 | Hyper | esophageal | PRRX1 |
| chr1 | 170637666 | 170637796 | Hyper | cancer_general | PRRX1 | chr1 | 170640517 | 170640691 | Hyper | cancer_general | PRRX1 |
| chr1 | 171810200 | 171810972 | Hyper | liver_tga, cancer_general, literature | DNM3 | chr1 | 173638647 | 173639085 | Hyper | cancer_general | ANKRD45 |
| chr1 | 177133721 | 177133814 | Hyper | cancer_general | FAM5B | chr1 | 177140105 | 177140714 | Hyper | cancer_general | FAM5B |
| chr1 | 177150773 | 177150803 | Hyper | head_neck | FAM5B | chr1 | 179544967 | 179545098 | Hyper | cancer_general | |
| chr1 | 179712164 | 179713399 | Hyper | tga, cancer_general | FAM163A | chr1 | 180198061 | 180198209 | Hyper | cancer_general | LHX4 |
| chr1 | 180202424 | 180203016 | Hyper | cancer_general | LHX4 | chr1 | 180203413 | 180204924 | Hyper | tga, lung, cancer_general | LHX4 |
| chr1 | 180882576 | 180882695 | Hyper | tga | KIAA1614 | chr1 | 181287679 | 181287757 | Hyper | cancer_general | CACNA1E, Mir_544 |
| chr1 | 181288014 | 181288188 | Hyper | cancer_general | | chr1 | 181451407 | 181452120 | Hyper | cancer_general | Mir_544, CACNA1E |
| chr1 | 181452871 | 181452967 | Hyper | cancer_general | Mir_544, CACNA1E | chr1 | 181454873 | 181454912 | Hyper | cancer_general | LOC284648 |
| chr1 | 181455183 | 181455263 | Hyper | cancer_general | Mir_544, CACNA1E | chr1 | 182584048 | 182584613 | Hyper | pancreas | |
| chr1 | 182921839 | 182921868 | Hyper | liver_tga | SHCBP1L | chr1 | 183386150 | 183386288 | Hyper | cancer_general | |
| chr1 | 183386500 | 183386626 | Hyper | cancer_general | | chr1 | 183386838 | 183386964 | Hyper | cancer_general | |
| chr1 | 183387266 | 183387319 | Hyper | cancer_general | | chr1 | 183774244 | 183774363 | Hyper | blood | RGL1 |
| chr1 | 184005701 | 184005814 | Hyper | cancer_general | COLGALT2 | chr1 | 190444855 | 190444885 | Hyper | cancer_general | CR936711, FAM5C |
| chr1 | 190445181 | 190445276 | Hyper | cancer_general | CR936711, FAM5C | chr1 | 190447373 | 190447519 | Hyper | cancer_general | CR936711, FAM5C |
| chr1 | 196577628 | 196577858 | Hyper | tga, cancer_general | | chr1 | 196578101 | 196578150 | Hyper | cancer_general | |
| chr1 | 197879400 | 197880156 | Hyper | liver_tga, cancer_general | LHX9, C1orf53 | chr1 | 197882140 | 197882201 | Hyper | cancer_general | LHX9, C1orf53 |
| chr1 | 197882453 | 197882611 | Hyper | cancer_general | LHX9, C1orf53 | chr1 | 197887052 | 197887741 | Hyper | cancer_general | LHX9 |
| chr1 | 197888052 | 197888319 | Hyper | cancer_general | LHX9 | chr1 | 197888643 | 197889286 | Hyper | cancer_general | LHX9 |
| chr1 | 200009357 | 200009450 | Hyper | cancer_general | NR5A2 | chr1 | 200009750 | 200010114 | Hyper | cancer_general | NR5A2 |
| chr1 | 200011323 | 200012227 | Hyper | tga, cancer_general, lung | NR5A2 | chr1 | 201368582 | 201368727 | Hyper | blood | TNNI1, LAD1 |
| chr1 | 201476501 | 201476619 | Hyper | liver_tga | CSRP1 | chr1 | 202081571 | 202081641 | Hyper | pancreas | SYT2 |
| chr1 | 202183371 | 202183401 | Hyper | blood | LGR6 | chr1 | 202679215 | 202679518 | Hyper | tga, esophageal | |
| chr1 | 204499813 | 204499842 | Hyper | literature | MDM4 | chr1 | 204653561 | 204653807 | Hyper | cancer_general | |
| chr1 | 205312596 | 205312950 | Hyper | cancer_general | KLHDC8A | chr1 | 205424654 | 205424957 | Hyper | cancer_general | AK095633, MIR135B |
| chr1 | 205537663 | 205537772 | Hyper | cancer_general | MFSD4 | chr1 | 207669496 | 207670060 | Hyper | cancer_general | CR1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 207818394 | 207818493 | Hyper | liver_tcga | CR1L, CR1 | chr1 | 208084289 | 208084488 | Hyper | cancer_general | CD34 |
| chr1 | 209381132 | 209381165 | Hyper | esophageal | | chr1 | 209849170 | 209849199 | Hyper | tcga | G0S2 |
| chr1 | 209849430 | 209849459 | Hyper | tcga | G0S2 | chr1 | 210111146 | 210111176 | Hyper | cancer_general | SYT14 |
| chr1 | 210111388 | 210112140 | Hyper | tcga, cancer_general | SYT14 | chr1 | 213123871 | 213123979 | Hyper | hepatobiliary, tcga | VASH2 |
| chr1 | 213124653 | 213124910 | Hyper | liver_tcga, cancer_general | VASH2 | chr1 | 214156419 | 214156928 | Hyper | cancer_general | PROX1 |
| chr1 | 214158838 | 214158966 | Hyper | cancer_general | PROX1 | chr1 | 214160107 | 214160184 | Hyper | cancer_general | PROX1 |
| chr1 | 214360675 | 214360968 | Hyper | tcga, cancer_general | | chr1 | 214724531 | 214724561 | Hyper | blood | PTPN14 |
| chr1 | 215255094 | 215255799 | Hyper | cancer_general | KCNK2 | chr1 | 216897216 | 216897307 | Hyper | cancer_general | |
| chr1 | 217307486 | 217308274 | Hyper | cancer_general | | chr1 | 217309007 | 217309105 | Hyper | cancer_general | |
| chr1 | 217311265 | 217311839 | Hyper | liver_tcga | | chr1 | 217313042 | 217313747 | Hyper | cancer_general | |
| chr1 | 218520074 | 218520399 | Hyper | tcga, cancer_general | TGFB2, CLO728463, RRP15 | chr1 | 218520775 | 218520805 | Hyper | liver_tcga | TGFB2, LOC728463, RRP15 |
| chr1 | 219346992 | 219347035 | Hyper | ovarian | LYPLAL1, LOC643723 | chr1 | 219347394 | 219347472 | Hyper | ovarian | LYPLAL1, LOC643723 |
| chr1 | 220101145 | 220101385 | Hyper | tcga, cancer_general | SLC30A10, RNU5F-1 | chr1 | 220101683 | 220101712 | Hyper | tcga | SLC30A10, RNU5F-1 |
| chr1 | 220700814 | 220700897 | Hyper | cancer_general | MARK1 | chr1 | 221052038 | 221052492 | Hyper | cancer_general | HLX |
| chr1 | 221053610 | 221053862 | Hyper | cancer_general | HLX | chr1 | 221067506 | 221067688 | Hyper | cancer_general | HLX |
| chr1 | 221068156 | 221068185 | Hyper | liver_tcga | HLX | chr1 | 221068793 | 221069150 | Hyper | liver_tcga | |
| chr1 | 221737191 | 221737220 | Hyper | liver_tcga | | chr1 | 223302825 | 223302890 | Hyper | cancer_general | |
| chr1 | 223538344 | 223538641 | Hyper | tcga | SUSD4 | chr1 | 223936633 | 223937057 | Hyper | lung, cancer_general | CAPN2 |
| chr1 | 224363560 | 224363589 | Hyper | literature | DEGS1 | chr1 | 224528814 | 224528844 | Hyper | liver_tcga, cancer_general | |
| chr1 | 224803717 | 224803751 | Hyper | cancer_general | CNIH3 | chr1 | 224804097 | 224804791 | Hyper | liver_tcga, cancer_general | CNIH3 |
| chr1 | 224805131 | 224805808 | Hyper | cancer_general | CNIH3 | chr1 | 226411243 | 226411273 | Hyper | liver_tcga | LIN9, MIXL1 ITPKB |
| chr1 | 226411700 | 226411832 | Hyper | tcga, liver_tcga | LIN9, MIXL1 ITPKB | chr1 | 226814346 | 226814408 | Hyper | colorectal | |
| chr1 | 226925067 | 226925195 | Hyper | tcga, cancer_general | ZNF678 | chr1 | 227729780 | 227730075 | Hyper | cancer_general | WNT3A |
| chr1 | 227748700 | 227748733 | Hyper | liver_tcga, literature | WNT3A | chr1 | 228194428 | 228194490 | Hyper | tcga | WNT3A |
| chr1 | 228195377 | 228196349 | Hyper | tcga, cancer_general | WNT3A | chr1 | 228247998 | 228248027 | Hyper | liver_tcga | |
| chr1 | 228248302 | 228248332 | Hyper | cancer_general | | chr1 | 228345999 | 228346195 | Hyper | liver_tcga | IBA57, GJC2, GUK1 |
| chr1 | 228463311 | 228463706 | Hyper | cancer_general | OBSCN HIST3H3, TRIM17, TRIM11 | chr1 | 228566622 | 228566672 | Hyper | cancer_general | |
| chr1 | 228604022 | 228604254 | Hyper | tcga, cancer_general | | chr1 | 228633990 | 228634261 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 228645140 | 228645734 | Hyper | cancer_general, lung_tcga, liver_tcga | Histone3, HIST3H2A, HIST3H2BB, MIR4666A | chr1 | 228646032 | 228646238 | Hyper | tcga | MIR4666A, Histone3, HIST3H2BB, HIST3H2A |
| chr1 | 228651432 | 228651626 | Hyper | cancer_general | MIR4666A, HIST3H2BB, HIST3H2A, Histone3 | chr1 | 228651879 | 228652629 | Hyper | cancer_general | Histone3, MIR4666A, HIST3H2BB, HIST3H2A |
| chr1 | 228871865 | 228872003 | Hyper | blood | RHOU | chr1 | 229542838 | 229543139 | Hyper | cancer_general | ACTA1, NUP133 |
| chr1 | 229543553 | 229543603 | Hyper | liver_tcga | | chr1 | 229566753 | 229568204 | Hyper | cancer_general | |
| chr1 | 229569810 | 229569852 | Hyper | cancer_general | NUP133, ACTA1 | chr1 | 230561779 | 230561824 | Hyper | esophageal | PGBD5 |
| chr1 | 231297103 | 231297221 | Hyper | cancer_general | TRIM67 | chr1 | 231298595 | 231298772 | Hyper | tcga, liver_tcga | TRIM67 |
| chr1 | 232765195 | 232765301 | Hyper | blood | | chr1 | 233750082 | 233750302 | Hyper | blood | MIR4427, KCNK1 |
| chr1 | 234040247 | 234040319 | Hyper | cancer_general | SLC35F3 | chr1 | 234040750 | 234041064 | Hyper | tcga, cancer_general | SLC35F3 |
| chr1 | 234041400 | 234041624 | Hyper | cancer_general | SLC35F3 | chr1 | 234349988 | 234350100 | Hyper | tcga, cancer_general | SLC35F3, AK054726 |
| chr1 | 235813781 | 235814202 | Hyper | cancer_general, tcga, literature | | chr1 | 235814447 | 235814476 | Hyper | literature | LYST |
| chr1 | 236227637 | 236228096 | Hyper | cancer_general | AX747246, NID1 | chr1 | 236228582 | 236228789 | Hyper | tcga, cancer_general | AX747246, NID1 |
| chr1 | 236559176 | 236559271 | Hyper | cancer_general | EDARADD | chr1 | 236849457 | 236850142 | Hyper | cancer_general | ACTN2 |
| chr1 | 237205159 | 237205188 | Hyper | literature | RYR2 | chr1 | 237205434 | 237205478 | Hyper | cancer_general | RYR2 |
| chr1 | 237205687 | 237206735 | Hyper | tcga, cancer_general | RYR2 | chr1 | 239550594 | 239551193 | Hyper | cancer_general | CHRM3 |
| chr1 | 240161098 | 240161493 | Hyper | cancer_general | RPS7P5 | chr1 | 240254944 | 240255011 | Hyper | cancer_general | FMN2 |
| chr1 | 240255361 | 240255500 | Hyper | cancer_general | FMN2 | chr1 | 240255819 | 240256197 | Hyper | cancer_general | FMN2 |
| chr1 | 240256663 | 240256721 | Hyper | cancer_general | FMN2 | chr1 | 240775425 | 240775455 | Hyper | cancer_general | |
| chr1 | 241520296 | 241520345 | Hyper | tcga | | chr1 | 241520583 | 241520612 | Hyper | tcga | |
| chr1 | 241587034 | 241587113 | Hyper | cancer_general | | chr1 | 241587587 | 241587797 | Hyper | tcga, cancer_general | |
| chr1 | 242686734 | 242687688 | Hyper | tcga, cancer_general | PLD5 | chr1 | 242688184 | 242688259 | Hyper | cancer_general | PLD5 |
| chr1 | 242688477 | 242688695 | Hyper | cancer_general | PLD5 | chr1 | 243646610 | 243646673 | Hyper | cancer_general | AKT3 |
| chr1 | 243859000 | 243859029 | Hyper | literature | | chr1 | 244014221 | 244014376 | Hyper | esophageal | |
| chr1 | 244080672 | 244080702 | Hyper | cancer_general | LOC339529 | chr1 | 244080963 | 244081203 | Hyper | tcga | LOC339529 |
| chr1 | 244893214 | 244893315 | Hyper | cancer_general | | chr1 | 246952347 | 246952376 | Hyper | literature | LOC149134 |
| chr1 | 247496038 | 247496108 | Hyper | tcga | ZNF496 | chr1 | 248020479 | 248021349 | Hyper | liver_tcga, cancer_general | TRIM58 |
| chrX | 6145331 | 6145688 | Hyper | tcga, cancer_general | NLGN4X | chrX | 8698863 | 8698897 | Hyper | cancer_general | KAL1 |
| chrX | 8699504 | 8699566 | Hyper | cancer_general | KAL1 | chrX | 20148710 | 20148739 | Hyper | literature | SCARNA9L, EIF1AX |
| chrX | 47039370 | 47039399 | Hyper | literature | RBM10 | chrX | 47426106 | 47426144 | Hyper | literature | SYN1, ARAF |
| chrX | 47426780 | 47426821 | Hyper | literature | SYN1, ARAF | chrX | 50557045 | 50557075 | Hyper | liver_tcga | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chrX | 64626567 | 64626596 | Hyper | liver_tcga | AR | chrX | 66931448 | 66931477 | Hyper | literature | AR |
| chrX | 66937356 | 66937385 | Hyper | literature | | chrX | 66943529 | 66943567 | Hyper | literature | AR |
| chrX | 70339239 | 70339268 | Hyper | literature | | chrX | 100740260 | 100740289 | Hyper | liver_tcga | ARMCX4 |
| chrX | 101906099 | 101906128 | Hyper | liver_tcga | GPRASP1 | chrX | 102000609 | 102000758 | Hyper | liver_tcga | BHLHB9 |
| chrX | 134156560 | 134156680 | Hyper | liver_tcga | FAM127A, FAM127C | chrX | 136656563 | 136656592 | Hyper | liver_tcga | ZIC3 |
| HCV | 111 | 140 | Hyper | virus | | HCV | 374 | 403 | Hyper | virus | |
| HCV | 637 | 666 | Hyper | virus | | HCV | 900 | 929 | Hyper | virus | |
| HCV | 1163 | 1192 | Hyper | virus | | HCV | 1426 | 1455 | Hyper | virus | |
| HCV | 1689 | 1718 | Hyper | virus | | HCV | 1952 | 1981 | Hyper | virus | |
| HCV | 2215 | 2244 | Hyper | virus | | HCV | 2478 | 2507 | Hyper | virus | |
| HCV | 2741 | 2770 | Hyper | virus | | HCV | 3004 | 3033 | Hyper | virus | |
| HCV | 3267 | 3296 | Hyper | virus | | HCV | 3530 | 3559 | Hyper | virus | |
| HCV | 3793 | 3822 | Hyper | virus | | HCV | 4056 | 4085 | Hyper | virus | |
| HCV | 4319 | 4348 | Hyper | virus | | HCV | 4582 | 4611 | Hyper | virus | |
| HCV | 4845 | 4874 | Hyper | virus | | HCV | 5108 | 5137 | Hyper | virus | |
| HCV | 5371 | 5400 | Hyper | virus | | HCV | 5634 | 5663 | Hyper | virus | |
| HCV | 5897 | 5926 | Hyper | virus | | HCV | 6160 | 6189 | Hyper | virus | |
| HCV | 6423 | 6452 | Hyper | virus | | HCV | 6686 | 6715 | Hyper | virus | |
| HCV | 6949 | 6978 | Hyper | virus | | HCV | 7212 | 7241 | Hyper | virus | |
| HCV | 7475 | 7504 | Hyper | virus | | HCV | 7738 | 7767 | Hyper | virus | |
| HCV | 8001 | 8030 | Hyper | virus | | HCV | 8264 | 8293 | Hyper | virus | |
| HCV | 8527 | 8556 | Hyper | virus | | HCV | 8790 | 8819 | Hyper | virus | |
| HCV | 9053 | 9082 | Hyper | virus | | chr22 | 17081932 | 17082001 | Hyper | cancer_general | TPTEP1, CCT8L2 |
| chr22 | 17082566 | 17082595 | Hyper | liver_tcga | TPTEP1, CCT8L2 | chr22 | 17082943 | 17083003 | Hyper | cancer_general | TPTEP1, CCT8L2 |
| chr22 | 17083396 | 17083496 | Hyper | cancer_general, tcga | TPTEP1, CCT8L2 | chr22 | 17601086 | 17601368 | Hyper | cancer_general | BC021738, CECR6, IL17RA |
| chr22 | 17602511 | 17602624 | Hyper | cancer_general | IL17RA, BC021738, CECR6 | chr22 | 17850454 | 17850621 | Hyper | cancer_general | CECR2 |
| chr22 | 19017532 | 19017567 | Hyper | cancer_general | DGCR2, DGCR10, DGCR9 | chr22 | 19510799 | 19511567 | Hyper | liver_tcga, cancer_general | CLDN5, CDC45 |
| chr22 | 19511849 | 19512098 | Hyper | tcga, cancer_general | CLDN5, CDC45 | chr22 | 19702265 | 19702410 | Hyper | esophageal | SEPT5-GP1BB |
| chr22 | 19706171 | 19706677 | Hyper | cancer_general, tcga, lung | SEPT5-GP1BB | chr22 | 19742834 | 19742969 | Hyper | cancer_general | TBX1 |
| chr22 | 19748644 | 19748956 | Hyper | tcga, cancer_general | TBX1 | chr22 | 20792461 | 20792641 | Hyper | cancer_general, tcga | KLHL22, SCARF2 |
| chr22 | 21368587 | 21368617 | Hyper | esophageal | P2RX6, TUBA3FP, THAP7-AS1 | chr22 | 22005794 | 22006759 | Hyper | pancreas | MIR301B, MIR130B, SDF2L1 |
| chr22 | 22090595 | 22090742 | Hyper | cancer_general | YPEL1 | chr22 | 22862787 | 22863159 | Hyper | tcga, cancer_general | ZNF280A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 24145484 | 24145513 | Hyper | literature | SMARCB1 | chr22 | 24180687 | 24180766 | Hyper | cancer_general | AK096976, DERL3 |
| chr22 | 24820330 | 24820396 | Hyper | esophageal | ADORA2A, ADORA2A-AS1, EU036692, SPECC1L | chr22 | 25678748 | 25679337 | Hyper | cancer_general | BC040576 |
| chr22 | 25817107 | 25817180 | Hyper | cancer_general | | chr22 | 25817458 | 25817612 | Hyper | cancer_general | |
| chr22 | 27053194 | 27053250 | Hyper | liver_tcga | MIAT | chr22 | 28198569 | 28198605 | Hyper | cancer_general | MN1 |
| chr22 | 28838200 | 28838292 | Hyper | lung | | chr22 | 28838509 | 28838551 | Hyper | cancer_general | |
| chr22 | 28839122 | 28839263 | Hyper | tcga | | chr22 | 29091824 | 29091853 | Hyper | literature | CHEK2 |
| chr22 | 29876191 | 29876220 | Hyper | liver_tcga | KIAA0845, NEFH | chr22 | 29877223 | 29877299 | Hyper | cancer_general | KIAA0845, NEFH |
| chr22 | 30116904 | 30117162 | Hyper | tcga | ZMAT5, CABP7 | chr22 | 30476191 | 30476220 | Hyper | literature | HORMAD2 |
| chr22 | 30881582 | 30881612 | Hyper | head_neck | SEC14L4, SDC4P | chr22 | 30938521 | 30938584 | Hyper | cancer_general | SEC14L6 |
| chr22 | 31198492 | 31198637 | Hyper | blood | OSBP2 | chr22 | 31218510 | 31218540 | Hyper | cancer_general | OSBP2 |
| chr22 | 31218794 | 31218829 | Hyper | cancer_general | OSBP2 | chr22 | 31481130 | 31481332 | Hyper | tcga | SMTN |
| chr22 | 33197603 | 33197652 | Hyper | literature | TIMP3 | chr22 | 33453877 | 33454366 | Hyper | cancer_general | |
| chr22 | 35656581 | 35656610 | Hyper | liver_tcga | HMGXB4 | chr22 | 36681295 | 36681341 | Hyper | liver_tcga | MYH9 |
| chr22 | 37720961 | 37721163 | Hyper | tcga | CYTH4 | chr22 | 38220653 | 38221201 | Hyper | tcga, cancer_general | GCAT, ANKRD54, GALR3 |
| chr22 | 38477069 | 38477794 | Hyper | cancer_general | BAIAP2L2, SLC16A8, PICK1 | chr22 | 39784480 | 39784598 | Hyper | liver_tcga | |
| chr22 | 39853521 | 39853592 | Hyper | colorectal | MGAT3 | chr22 | 39954413 | 39954516 | Hyper | cancer_general | SHISA8 |
| chr22 | 40807034 | 40807063 | Hyper | liver_tcga | MKL1, SGSM3 | chr22 | 42310087 | 42310220 | Hyper | cancer_general | |
| chr22 | 42311521 | 42311587 | Hyper | cancer_general | TNFRSF13C, SHISA8 | chr22 | 42353611 | 42353892 | Hyper | cancer_general | LINC00634 |
| chr22 | 42679729 | 42679841 | Hyper | cancer_general | LOC388906 | chr22 | 43740084 | 43740128 | Hyper | cancer_general | |
| chr22 | 43808280 | 43808428 | Hyper | cancer_general | MPPED1 | chr22 | 44208418 | 44208448 | Hyper | esophageal | |
| chr22 | 44258366 | 44258506 | Hyper | cancer_general | SULT4A1 | chr22 | 44287650 | 44287696 | Hyper | cancer_general | PNPLA5 |
| chr22 | 45403086 | 45403133 | Hyper | cancer_general | PHF21B | chr22 | 45403478 | 45403714 | Hyper | tcga | PHF21B |
| chr22 | 45404197 | 45404433 | Hyper | tcga, cancer_general | PHF21B | chr22 | 45404994 | 45405061 | Hyper | cancer_general | PHF21B |
| chr22 | 45405318 | 45405418 | Hyper | tcga | PHF21B | chr22 | 45405620 | 45405768 | Hyper | liver_tcga | PHF21B |
| chr22 | 45406271 | 45406328 | Hyper | cancer_general | PHF21B | chr22 | 45719161 | 45719190 | Hyper | liver_tcga | DQ586951, FAM118A |
| chr22 | 46262452 | 46263809 | Hyper | tcga, cancer_general | | chr22 | 46276749 | 46276820 | Hyper | cancer_general | |
| chr22 | 46368029 | 46368059 | Hyper | cancer_general | WNT7B | chr22 | 46658791 | 46658846 | Hyper | cancer_general | TTC38, PKDREJ |
| chr22 | 46933089 | 46933237 | Hyper | liver_tcga | | chr22 | 48885031 | 48885061 | Hyper | cancer_general | FAM19A5 |
| chr22 | 48885296 | 48885901 | Hyper | cancer_general | FAM19A5 | chr22 | 48886659 | 48886849 | Hyper | cancer_general | FAM19A5 |
| chr22 | 48971130 | 48971748 | Hyper | cancer_general | FAM19A5 | chr22 | 48972144 | 48972657 | Hyper | tcga, cancer_general | FAM19A5 |
| chr22 | 50064721 | 50064944 | Hyper | tcga | MLC1 | chr22 | 50496841 | 50496918 | Hyper | cancer_general | MLC1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 50497147 | 50497287 | Hyper | cancer_general | MLC1 | chr22 | 50623672 | 50623815 | Hyper | literature, cancer_general | TRABD, PANX2 |
| chr22 | 50944093 | 50943262 | Hyper | head_neck | NCAPH2, LMF2 | chr22 | 51042278 | 51042810 | Hyper | cancer_general | MAPK8IP2 |
| chr22 | 51112150 | 51112232 | Hyper | tcga | SHANK3 | chr6 | 391173 | 392000 | Hyper | tcga, liver_tcga, cancer_general | IRF4 |
| chr6 | 392307 | 393650 | Hyper | liver_tcga, tcga, cancer_general | IRF4 | chr6 | 711142 | 711293 | Hyper | pancreas | AX747750 |
| chr6 | 1312000 | 1312096 | Hyper | blood | FOXQ1 | chr6 | 1312356 | 1312708 | Hyper | blood | FOXQ1 |
| chr6 | 1314088 | 1314118 | Hyper | blood | FOXQ1 | chr6 | 1378222 | 1379242 | Hyper | tcga, cancer_general | |
| chr6 | 1379584 | 1379614 | Hyper | cancer_general | | chr6 | 1379909 | 1379952 | Hyper | cancer_general | FOXF2 |
| chr6 | 1383677 | 1384644 | Hyper | cancer_general, tcga | FOXF2 | chr6 | 1385118 | 1385170 | Hyper | cancer_general | |
| chr6 | 1386071 | 1386112 | Hyper | cancer_general | FOXF2 | chr6 | 1389124 | 1389262 | Hyper | cancer_general | FOXF2 |
| chr6 | 1390241 | 1391035 | Hyper | tcga, cancer_general | FOXF2 | chr6 | 1391318 | 1391379 | Hyper | cancer_general | FOXF2 |
| chr6 | 1524199 | 1524283 | Hyper | cancer_general | GMDS, FOXC1 | chr6 | 1605387 | 1605454 | Hyper | cancer_general | FOXC1 |
| chr6 | 1614833 | 1615184 | Hyper | cancer_general | | chr6 | 1620672 | 1620701 | Hyper | liver_tcga | FOXC1, GMDS |
| chr6 | 1624977 | 1625818 | Hyper | liver_tcga, cancer_general | GMDS | chr6 | 3229029 | 3229059 | Hyper | cancer_general | AK096219, TUBB2A, TUBB2B |
| chr6 | 3229423 | 3229510 | Hyper | cancer_general | AK096219, TUBB2A, TUBB2B | chr6 | 3232010 | 3232260 | Hyper | tcga | AK096219, TUBB2A, TUBB2B |
| chr6 | 4775062 | 4775222 | Hyper | liver tcga | CDYL | chr6 | 5996952 | 5996989 | Hyper | cancer_general | NRN1 |
| chr6 | 5997802 | 5997832 | Hyper | cancer_general | NRN1 | chr6 | 6003287 | 6005417 | Hyper | tcga, cancer_general | NRN1 |
| chr6 | 6006374 | 6006419 | Hyper | cancer_general | NRN1 | chr6 | 6006674 | 6006883 | Hyper | cancer_general | NRN1 |
| chr6 | 6007593 | 6008277 | Hyper | cancer_general | NRN1 | chr6 | 7726334 | 7726363 | Hyper | literature | BMP6 |
| chr6 | 7726630 | 7726659 | Hyper | literature | BMP6 | chr6 | 7726952 | 7726981 | Hyper | literature | BMP6 |
| chr6 | 7727699 | 7728142 | Hyper | literature, cancer_general | BMP6 | chr6 | 7728849 | 7728941 | Hyper | literature, cancer_general | BMP6 |
| chr6 | 10381507 | 10382299 | Hyper | cancer_general | | chr6 | 10382722 | 10383049 | Hyper | cancer_general | |
| chr6 | 10383739 | 10383774 | Hyper | cancer_general | | chr6 | 10384950 | 10385939 | Hyper | cancer_general | |
| chr6 | 10386210 | 10386273 | Hyper | cancer_general | | chr6 | 10390023 | 10391187 | Hyper | cancer_general | TFAP2A |
| chr6 | 10410518 | 10410578 | Hyper | cancer_general | LOC100130275, TFAP2A | chr6 | 10411356 | 10411510 | Hyper | cancer_general | LOC100130275, TFAP2A |
| chr6 | 10415113 | 10415215 | Hyper | cancer_general | LOC100130275, TFAP2A | chr6 | 10415559 | 10415713 | Hyper | cancer_general | LOC100130275, TFAP2A |
| chr6 | 10416118 | 10416351 | Hyper | lung, cancer_general | LOC100130275, TFAP2A | chr6 | 10417158 | 10417557 | Hyper | cancer_general | LOC100130275, TFAP2A |
| chr6 | 10419086 | 10419506 | Hyper | cancer_general | LINC00518, LOC100130275, TFAP2A | chr6 | 10419744 | 10419941 | Hyper | cancer_general | LINC00518, LOC100130275 |
| chr6 | 10421053 | 10422635 | Hyper | literature, cancer_general | LINC00518, LOC100130275, TFAP2A | chr6 | 10423613 | 10423704 | Hyper | cancer_general | TFAP2A, LINC00518, LOC100130275 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 10425496 | 10426884 | Hyper | cancer_general | LINC00518, LOC100130275, TFAP2A | chr6 | 10881835 | 10882057 | Hyper | cancer_general | SYCP2L, GCM2 |
| chr6 | 10882321 | 10882350 | Hyper | literature | SYCP2L, GCM2 | chr6 | 10883008 | 10883038 | Hyper | cancer_general | SYCP2L, GCM2 |
| chr6 | 10883444 | 10883474 | Hyper | cancer_general | SYCP2L | chr6 | 10887078 | 10887686 | Hyper | cancer_general | SYCP2L, GCM2 |
| chr6 | 11044062 | 11044572 | Hyper | tcga, cancer_general | ELOVL2, ELOVL2-AS1 | chr6 | 12749899 | 12749976 | Hyper | cancer_general | PHACTR1 |
| chr6 | 12750210 | 12750255 | Hyper | cancer_general | PHACTR1 | chr6 | 17281417 | 17281534 | Hyper | cancer_general | RBM24 |
| chr6 | 19691638 | 19691841 | Hyper | cancer_general | | chr6 | 19692066 | 19692318 | Hyper | cancer_general, tcga | |
| chr6 | 19837064 | 19837140 | Hyper | cancer_general | ID4 | chr6 | 21664719 | 21664749 | Hyper | cancer_general | LINC00340 |
| chr6 | 21665004 | 21665043 | Hyper | cancer_general | LINC00340 | chr6 | 24358291 | 24358320 | Hyper | liver_tcga | KAAG1, DCDC2 |
| chr6 | 24360074 | 24360170 | Hyper | hepatobiliary | DCDC2, KAAG1 | chr6 | 24494679 | 24494766 | Hyper | cancer_general | ALDH5A1, GPLD1 |
| chr6 | 26034268 | 26034311 | Hyper | cancer_general | HIST1H2BB, HIST1H2AB, HIST1H3B, HIST1H4B | chr6 | 26184095 | 26184391 | Hyper | cancer_general | HIST1H4D, HIST1H2BE |
| chr6 | 26188696 | 26189393 | Hyper | cancer_general | HIST1H3F, HIST1H2AD, HIST1H2BE, HIST1H4D, HIST1H3D | chr6 | 26199137 | 26199167 | Hyper | pancreas | HIST1H2BF, HIST1H4E, HIST1H2AD, HIST1H3F, HIST1H4D |
| chr6 | 26199686 | 26199716 | Hyper | pancreas | HIST1H2BF, HIST1H4E, HIST1H2AD, HIST1H3F, HIST1H3D | chr6 | 26235223 | 26235623 | Hyper | tcga, liver_tcga | HIST1H3E, HIST1H3F, HIST1H4F, HIST1H1D |
| chr6 | 26240504 | 26241118 | Hyper | liver_tcga, cancer_general | HIST1H4G, HIST1H3F, HIST1H1D, HIST1H4F | chr6 | 26250468 | 26250826 | Hyper | liver_tcga, cancer_general | HIST1H4F, HIST1H2BH, HIST1H3F, HIST1H4G |
| chr6 | 26251054 | 26251182 | Hyper | cancer_general | HIST1H2BH, HIST1H3F, HIST1H4G | chr6 | 26251816 | 26252151 | Hyper | liver_tcga, cancer_general | HIST1H2BH, HIST1H3F, HIST1H4G |
| chr6 | 26271406 | 26271762 | Hyper | cancer_general | BC079832, HIST1H2BI, HIST1H4H, HIST1H3G | chr6 | 26271971 | 26272001 | Hyper | cancer_general | BC079832, HIST1H2BI, HIST1H4H, HIST1H3G |
| chr6 | 26272512 | 26272617 | Hyper | cancer_general | HIST1H2BI, HIST1H4H, BC079832, HIST1H3G | chr6 | 26273400 | 26273480 | Hyper | cancer_general | HIST1H3G, HIST1H4H, HIST1H2BI, BC079832 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 26284811 | 26284898 | Hyper | hepatobiliary | HIST1H4H, TRNA_Met | chr6 | 26327806 | 26327982 | Hyper | cancer_general | TRNA_Ser, TRNA_Arg, TRNA_Met, TRNA_Trp |
| chr6 | 26328294 | 26328457 | Hyper | cancer_general | TRNA_Arg, TRNA_Met, TRNA_Trp, TRNA_Ser | chr6 | 26332178 | 26332218 | Hyper | lung | TRNA_Trp, TRNA_Met, TRNA_Arg, TRNA_Ser |
| chr6 | 26501857 | 26502209 | Hyper | cancer_general | BTN1A1 | chr6 | 26550994 | 26551034 | Hyper | cancer_general | TRNA_Ile, TRNA_Pro, TRNA_Lys, HMGN4, TRNA_Ala |
| chr6 | 26577158 | 26577475 | Hyper | cancer_general | TRNA_Tyr, TRNA_Ala, BC033330 | chr6 | 26987967 | 26988166 | Hyper | blood | TRNA_Ile, LOC100270746, LINC00240 |
| chr6 | 27059783 | 27059848 | Hyper | cancer_general | TRNA_Ser, TRNA_Pro, TRNA_Val, TRNA_Ser, TRNA_Arg | chr6 | 27064682 | 27065198 | Hyper | cancer_general | TRNA_Ser, TRNA_Pro |
| chr6 | 27173528 | 27174181 | Hyper | tcga, cancer_general | | chr6 | 27182869 | 27182899 | Hyper | cancer_general | TRNA_Arg, TRNA_Val |
| chr6 | 27203269 | 27203363 | Hyper | cancer_general | TRNA_Val, TRNA_Ile, TRNA_Leu | chr6 | 27205300 | 27205441 | Hyper | cancer_general | TRNA_Ile, TRNA_Val |
| chr6 | 27205671 | 27206040 | Hyper | cancer_general | TRNA_Ile, TRNA_Val, TRNA_Leu, PRSS16 | chr6 | 27218951 | 27218980 | Hyper | liver_tcga | TRNA_Val, TRNA_Leu, PRSS16 |
| chr6 | 27228180 | 27228395 | Hyper | cancer_general | PRSS16 | chr6 | 27235876 | 27235905 | Hyper | literature | TRNA_Ile |
| chr6 | 27247636 | 27247724 | Hyper | cancer_general | TRNA_Val, TRNA_Pseudo, TRNA_Ile | chr6 | 27256097 | 27256173 | Hyper | cancer_general | TRNA_Val, TRNA_Pseudo, TRNA_Gln, TRNA_Ser |
| chr6 | 27256383 | 27256420 | Hyper | cancer_general | TRNA_Val, TRNA_Pseudo, TRNA_Gln, TRNA_Ser | chr6 | 27264332 | 27264364 | Hyper | cancer_general | TRNA_Thr, TRNA_Gln, TRNA_Pseudo, TRNA_Val, TRNA_Ser |
| chr6 | 27279845 | 27280012 | Hyper | cancer_general | POM121L2, TRNA_Thr | chr6 | 27463029 | 27463687 | Hyper | liver_tcga, cancer_general | TRNA_Ser, TRNA_Asp |
| chr6 | 27512761 | 27513487 | Hyper | cancer_general | TRNA_Ser, TRNA_Gln | chr6 | 27533822 | 27534341 | Hyper | cancer_general | TRNA_Arg |
| chr6 | 27559809 | 27560075 | Hyper | cancer_general | TRNA_Met, TRNA_Lys, TRNA_Asp | chr6 | 27573171 | 27573392 | Hyper | cancer_general | TRNA_Leu |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 27598738 | 27598860 | Hyper | cancer_general | TRNA_Ile | chr6 | 27599159 | 27599341 | Hyper | cancer_general | TRNA_Ile |
| chr6 | 27635265 | 27635434 | Hyper | cancer_general | TRNA_Ile, TRNA_Arg, TRNA_Ser, TRNA_Phe | chr6 | 27647712 | 27647896 | Hyper | liver_tcga, literature | TRNA_Thr, TRNA_Ile, TRNA_Ser, TRNA_Arg, TRNA_Val |
| chr6 | 27648912 | 27649134 | Hyper | cancer_general, literature | TRNA_Ser, TRNA_Val, TRNA_Thr, TRNA_Ile | chr6 | 27725187 | 27725308 | Hyper | liver_tcga | LOC100131289, TRNA_Val |
| chr6 | 27783039 | 27783068 | Hyper | liver_tcga | HIST1H2BI, HIST1H4I, HIST1H2BM, HIST1H2AJ, HIST1H3H | chr6 | 27799464 | 27799581 | Hyper | pancreas | HIST1H2AK, HIST1H2BN, HIST1H4K, BC016143, FKSG63, HIST1H4J |
| chr6 | 27834676 | 27834835 | Hyper | cancer_general | HIST1H3I, HIST1H4L, HIST1H1B, HIST1H2AL | chr6 | 27835047 | 27835417 | Hyper | cancer_general | HIST1H1B, HIST1H2AL, HIST1H3I, HIST1H4L |
| chr6 | 27839726 | 27840082 | Hyper | cancer_general | HIST1H4L, HIST1H3I, HIST1H1B, HIST1H2AL | chr6 | 27840543 | 27840617 | Hyper | cancer_general | HIST1H4L, HIST1H3I, HIST1H1B, HIST1H2AL |
| chr6 | 27841104 | 27841136 | Hyper | cancer_general | HIST1H4L, HIST1H3I, HIST1H1B, HIST1H2AL | chr6 | 27858515 | 27858637 | Hyper | liver_tcga, cancer_general | HIST1H2AM, HIST1H2BO, HIST1H3J |
| chr6 | 28175189 | 28176212 | Hyper | tcga, cancer_general | TRNA_Ser, TOB2P1 | chr6 | 28227076 | 28227141 | Hyper | literature | ZSCAN26, NKAPL, ZKSCAN4 |
| chr6 | 28303562 | 28303607 | Hyper | lung | ZSCAN31 | chr6 | 28303815 | 28304263 | Hyper | tcga, lung | ZSCAN31 |
| chr6 | 28367109 | 28367774 | Hyper | tcga, cancer_general | ZSCAN12 | chr6 | 28410976 | 28411353 | Hyper | cancer_general | ZSCAN23 |
| chr6 | 28414977 | 28415034 | Hyper | cancer_general | | chr6 | 28457608 | 28457638 | Hyper | cancer_general | TRNA_Thr |
| chr6 | 28457870 | 28458158 | Hyper | cancer_general | TRNA_Thr | chr6 | 28956323 | 28956719 | Hyper | liver_tcga | TRNA_Leu, ZNF311, TRNA_Glu, TRNA_Phe |
| chr6 | 30095418 | 30095570 | Hyper | liver_tcga | TRIM40, DQ580846 | chr6 | 30644680 | 30644798 | Hyper | liver_tcga | PPP1R18 |
| chr6 | 34113893 | 34113922 | Hyper | tcga | | chr6 | 35182493 | 35182522 | Hyper | liver_tcga | SCUBE3, AY927475 |
| chr6 | 35479613 | 35479642 | Hyper | literature | TULP1 | chr6 | 35992428 | 35992458 | Hyper | cancer_general | MAPK14, SLC26A8 |
| chr6 | 36252984 | 36253171 | Hyper | cancer_general | PNPLA1 | chr6 | 36808323 | 36808441 | Hyper | cancer_general | AK096023, CPNE5 |
| chr6 | 37664140 | 37664187 | Hyper | cancer_general | DNAH8 | chr6 | 37673320 | 37673611 | Hyper | tcga | KCNK17, KCNK16 |
| chr6 | 38683206 | 38683235 | Hyper | liver_tcga | | chr6 | 39281088 | 39281133 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 39281824 | 39281875 | Hyper | cancer_general | KCNK16, KCNK17 | chr6 | 39929863 | 39929892 | Hyper | literature | KIF6 |
| chr6 | 39760401 | 39760661 | Hyper | tcga | DAAM2 | chr6 | 40554653 | 40554699 | Hyper | cancer_general | LRFN2 |
| chr6 | 41337072 | 41337128 | Hyper | cancer_general | | chr6 | 41339263 | 41339838 | Hyper | cancer_general | |
| chr6 | 41340902 | 41341182 | Hyper | tcga, cancer_general | | chr6 | 41341501 | 41341549 | Hyper | cancer_general | |
| chr6 | 41342243 | 41342275 | Hyper | cancer_general | | chr6 | 41342807 | 41342837 | Hyper | cancer_general | |
| chr6 | 41605937 | 41606542 | Hyper | tcga, cancer_general | MDFI | chr6 | 42738966 | 42739049 | Hyper | liver_tcga | |
| chr6 | 42879554 | 42879718 | Hyper | cancer_general | PTCRA | chr6 | 42928321 | 42928454 | Hyper | blood | GNMT, BC040637, PEX6 |
| chr6 | 43211193 | 43211311 | Hyper | literature, liver_tcga | TTBK1 | chr6 | 43612825 | 43613067 | Hyper | cancer_general | RSPH9, MAD2L1BP |
| chr6 | 45388716 | 45388775 | Hyper | cancer_general | RUNX2 | chr6 | 46702982 | 46703123 | Hyper | liver_tcga | PLA2G7 |
| chr6 | 46703350 | 46703436 | Hyper | cancer_general | PLA2G7 | chr6 | 50674372 | 50674750 | Hyper | literature, cancer_general | TFAP2D |
| chr6 | 50681699 | 50681942 | Hyper | cancer_general | TFAP2D | chr6 | 50682319 | 50682386 | Hyper | cancer_general | TFAP2D |
| chr6 | 50682659 | 50683227 | Hyper | cancer_general | TFAP2D | chr6 | 50684939 | 50684969 | Hyper | cancer_general | TFAP2D |
| chr6 | 50689913 | 50690039 | Hyper | cancer_general | TFAP2D | chr6 | 50691065 | 50691095 | Hyper | lung | TFAP2D |
| chr6 | 50692083 | 50692481 | Hyper | cancer_general | TFAP2D | chr6 | 50787216 | 50788352 | Hyper | cancer_general | TFAP2B |
| chr6 | 50789374 | 50789404 | Hyper | cancer_general | TFAP2B | chr6 | 50791187 | 50791632 | Hyper | cancer_general, literature | TFAP2B |
| chr6 | 50793335 | 50793404 | Hyper | cancer_general | TFAP2B | chr6 | 50793728 | 50793882 | Hyper | cancer_general | TFAP2B |
| chr6 | 50794531 | 50794693 | Hyper | cancer_general | TFAP2B | chr6 | 50803834 | 50803867 | Hyper | cancer_general | TFAP2B |
| chr6 | 50804131 | 50804368 | Hyper | cancer_general | TFAP2B | chr6 | 50808681 | 50808854 | Hyper | cancer_general | TFAP2B |
| chr6 | 50810551 | 50810839 | Hyper | cancer_general | TFAP2B | chr6 | 50811062 | 50811488 | Hyper | cancer_general | TFAP2B |
| chr6 | 50813258 | 50813939 | Hyper | cancer_general | TFAP2B | chr6 | 50814569 | 50814599 | Hyper | cancer_general | TFAP2B |
| chr6 | 50817023 | 50817229 | Hyper | cancer_general | TFAP2B | chr6 | 50817905 | 50817935 | Hyper | cancer_general | TFAP2B |
| chr6 | 50818449 | 50818706 | Hyper | cancer_general | TFAP2B | chr6 | 50818920 | 50819000 | Hyper | cancer_general | TFAP2B |
| chr6 | 52227752 | 52227781 | Hyper | tcga | PAQR8 | chr6 | 52228008 | 52228037 | Hyper | tcga | PAQR8 |
| chr6 | 53212491 | 53213970 | Hyper | esophageal | | chr6 | 54711448 | 54711626 | Hyper | blood | FAM83B |
| chr6 | 55443691 | 55443946 | Hyper | cancer_general | HMGCLL1 | chr6 | 56112262 | 56112386 | Hyper | cancer_general | COL21A1 |
| chr6 | 56716332 | 56716410 | Hyper | cancer_general | | chr6 | 56818656 | 56818937 | Hyper | cancer_general | BEND6 |
| chr6 | 56819217 | 56819637 | Hyper | cancer_general, tcga, liver_tcga | BEND6 | chr6 | 56819897 | 56819926 | Hyper | liver_tcga | BEND6 |
| chr6 | 58147447 | 58147480 | Hyper | cancer_general | TRNA_Ile, TRNA_Ala | chr6 | 58147790 | 58147976 | Hyper | cancer_general | TRNA_Ala, TRNA_Ile |
| chr6 | 62995356 | 62996146 | Hyper | tcga, cancer_general | KHDRBS2 | chr6 | 62996443 | 62996489 | Hyper | cancer_general | KHDRBS2 |
| chr6 | 70992057 | 70992162 | Hyper | cancer_general | COL9A1 | chr6 | 70992415 | 70992560 | Hyper | cancer_general | COL9A1 |
| chr6 | 70992830 | 70993015 | Hyper | cancer_general | COL9A1 | chr6 | 71665638 | 71665723 | Hyper | esophageal | B3GAT2 |
| chr6 | 71666788 | 71666986 | Hyper | tcga, cancer_general | B3GAT2 | chr6 | 72129789 | 72129829 | Hyper | cancer_general | LINC00472 |
| chr6 | 72130107 | 72130464 | Hyper | cancer_general | LINC00472 | chr6 | 72596120 | 72596315 | Hyper | tcga, pancreas | RIMS1 |
| chr6 | 72596950 | 72596980 | Hyper | tcga, cancer_general | RIMS1 | chr6 | 73329784 | 73330126 | Hyper | cancer_general | KCNQ5 |
| chr6 | 73330834 | 73331304 | Hyper | tcga, cancer_general | KCNQ5 | chr6 | 73331515 | 73333122 | Hyper | cancer_general, colorectal, tcga | KCNQ5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 76059561 | 76059787 | Hyper | tcga | | chr6 | 78172177 | 78172572 | Hyper | tcga, literature, cancer_general | HTR1B |
| chr6 | 78173212 | 78173264 | Hyper | literature | HTR1B | chr6 | 78173696 | 78173984 | Hyper | tcga, | HTR1B |
| chr6 | 78176458 | 78176820 | Hyper | cancer_general, tcga | HTR1B | chr6 | 79620399 | 79620699 | Hyper | cancer_general | IRAK1BP1 |
| chr6 | 80656930 | 80657180 | Hyper | cancer_general | ELOVL4 | chr6 | 82463270 | 82463310 | Hyper | blood | FAM46A |
| chr6 | 84141298 | 84141412 | Hyper | pancreas | ME1 | chr6 | 84417436 | 84417778 | Hyper | cancer_general | SNAP91 |
| chr6 | 84418172 | 84418281 | Hyper | cancer_general | SNAP91 | chr6 | 84418644 | 84418803 | Hyper | cancer_general | SNAP91 |
| chr6 | 84419157 | 84419415 | Hyper | cancer_general | SNAP91 | chr6 | 84562873 | 84563242 | Hyper | cancer_general, tcga, liver_tcga | RIPPLY2, CYB5R4 |
| chr6 | 84563489 | 84563542 | Hyper | cancer_general | CYB5R4, RIPPLY2 | chr6 | 85472407 | 85473703 | Hyper | tcga, cancer_general | TBX18 |
| chr6 | 85473928 | 85474378 | Hyper | tcga, liver_tcga, cancer_general | TBX18 | chr6 | 85474594 | 85474736 | Hyper | cancer_general | TBX18 |
| chr6 | 85476233 | 85476285 | Hyper | cancer_general | TBX18 | chr6 | 85476998 | 85477028 | Hyper | cancer_general | TBX18 |
| chr6 | 85478514 | 85478724 | Hyper | cancer_general | TBX18 | chr6 | 85482530 | 85482822 | Hyper | cancer_general | TBX18 |
| chr6 | 85483345 | 85483375 | Hyper | cancer_general | TBX18 | chr6 | 85483635 | 85484920 | Hyper | cancer_general, tcga | TBX18 |
| chr6 | 87647114 | 87647143 | Hyper | literature | HTR1E | chr6 | 87862092 | 87862172 | Hyper | cancer_general | ZNF292 |
| chr6 | 88876963 | 88877437 | Hyper | cancer_general | | chr6 | 91320285 | 91320318 | Hyper | cancer_general | |
| chr6 | 91320949 | 91321295 | Hyper | tcga | | chr6 | 94126973 | 94127064 | Hyper | cancer_general | EPHA7 |
| chr6 | 94127455 | 94127544 | Hyper | cancer_general | EPHA7 | chr6 | 94128365 | 94128399 | Hyper | cancer_general | EPHA7 |
| chr6 | 94129219 | 94129257 | Hyper | tcga | EPHA7 | chr6 | 94129509 | 94129575 | Hyper | cancer_general | EPHA7 |
| chr6 | 96464100 | 96464204 | Hyper | cancer_general | FUT9 | chr6 | 99271926 | 99272810 | Hyper | cancer_general | POU3F2 |
| chr6 | 99273369 | 99273410 | Hyper | cancer_general | POU3F2 | chr6 | 99277180 | 99277330 | Hyper | cancer_general | POU3F2 |
| chr6 | 99279556 | 99279612 | Hyper | cancer_general | POU3F2 | chr6 | 99280557 | 99280744 | Hyper | cancer_general | POU3F2 |
| chr6 | 99281014 | 99281385 | Hyper | cancer_general | POU3F2 | chr6 | 99283512 | 99283582 | Hyper | cancer_general | POU3F2 |
| chr6 | 99290360 | 99290398 | Hyper | cancer_general | POU3F2 | chr6 | 99290657 | 99290693 | Hyper | cancer_general | POU3F2 |
| chr6 | 99291264 | 99291438 | Hyper | cancer_general | POU3F2 | chr6 | 99292252 | 99292417 | Hyper | cancer_general | POU3F2 |
| chr6 | 99295726 | 99296467 | Hyper | cancer_general | POU3F2 | chr6 | 99842067 | 99842258 | Hyper | tcga | PNISR, BC033061, COQ3 |
| chr6 | 100038682 | 100038964 | Hyper | cancer_general | PRDM13 | chr6 | 100039259 | 100039289 | Hyper | cancer_general | PRDM13 |
| chr6 | 100050754 | 100051971 | Hyper | cancer_general | PRDM13 | chr6 | 100053221 | 100053511 | Hyper | cancer_general | PRDM13 |
| chr6 | 100054866 | 100054917 | Hyper | cancer_general | PRDM13 | chr6 | 100061022 | 100061076 | Hyper | cancer_general | PRDM13 |
| chr6 | 100061311 | 100061419 | Hyper | cancer_general | PRDM13 | chr6 | 100061757 | 100061835 | Hyper | cancer_general | PRDM13 |
| chr6 | 100062178 | 100062586 | Hyper | cancer_general | PRDM13 | chr6 | 100062944 | 100063068 | Hyper | cancer_general | PRDM13 |
| chr6 | 100441364 | 100441966 | Hyper | cancer_general | MCHR2, LOC728012 | chr6 | 100903384 | 100903631 | Hyper | cancer_general | SIM1 |
| chr6 | 100904214 | 100904275 | Hyper | cancer_general | SIM1 | chr6 | 100905969 | 100906016 | Hyper | cancer_general | SIM1 |
| chr6 | 100911686 | 100911723 | Hyper | literature | SIM1 | chr6 | 100912070 | 100912119 | Hyper | cancer_general | SIM1 |
| chr6 | 100912421 | 100912480 | Hyper | cancer_general | SIM1 | chr6 | 100912919 | 100913149 | Hyper | liver_tcga, literature, cancer_general | SIM1 |
| chr6 | 100915101 | 100915205 | Hyper | liver_tcga, cancer_general | SIM1 | chr6 | 101840708 | 101840820 | Hyper | cancer_general | GRIK2 |
| chr6 | 101846782 | 101846811 | Hyper | literature | GRIK2 | chr6 | 101847185 | 101847215 | Hyper | cancer_general | GRIK2 |
| chr6 | 101850147 | 101850275 | Hyper | cancer_general | GRIK2 | chr6 | 101850570 | 101850600 | Hyper | cancer_general | GRIK2 |
| chr6 | 105388679 | 105388708 | Hyper | literature | LINC00577 | chr6 | 105388913 | 105389710 | Hyper | cancer_general | LINC00577 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 105400913 | 105401007 | Hyper | literature, cancer_general | LIN28B | chr6 | 105401620 | 105401874 | Hyper | cancer_general | LIN28B |
| chr6 | 105404574 | 105404674 | Hyper | cancer_general | LIN28B | chr6 | 105405656 | 105405772 | Hyper | cancer_general | LIN28B |
| chr6 | 105406098 | 105406128 | Hyper | cancer_general | LIN28B | chr6 | 105584264 | 105585554 | Hyper | tcga, cancer_general, liver_tcga | BVES-AS1, BVES |
| chr6 | 106429049 | 106429624 | Hyper | liver_tcga, cancer_general | | chr6 | 106434339 | 106434368 | Hyper | literature | |
| chr6 | 106441869 | 106442979 | Hyper | cancer_general | | chr6 | 106960908 | 106961023 | Hyper | cancer_general | AIM1 |
| chr6 | 107955952 | 107955982 | Hyper | cancer_general | SOBP | chr6 | 108435075 | 108435263 | Hyper | cancer_general | AF520419 |
| chr6 | 108436072 | 108436526 | Hyper | cancer_general | AF520419 | chr6 | 108438245 | 108438577 | Hyper | cancer_general | AF520419 |
| chr6 | 108440091 | 108440961 | Hyper | cancer_general | AF520419 | chr6 | 108479290 | 108479665 | Hyper | cancer_general | NR2E1, AF520419 |
| chr6 | 108484909 | 108485406 | Hyper | cancer_general | NR2E1, AF520419 | chr6 | 108485665 | 108485905 | Hyper | cancer_general | NR2E1, AF520419 |
| chr6 | 108486158 | 108486394 | Hyper | cancer_general | NR2E1, AF520419 | chr6 | 108487724 | 108488416 | Hyper | liver_tcga, cancer_general | NR2E1, AF520419 |
| chr6 | 108489385 | 108490633 | Hyper | liver_tcga, cancer_general | NR2E1 | chr6 | 108490978 | 108491423 | Hyper | cancer_general | NR2E1 |
| chr6 | 108492270 | 108492451 | Hyper | cancer_general | NR2E1 | chr6 | 108495681 | 108495951 | Hyper | cancer_general | NR2E1 |
| chr6 | 108496208 | 108496649 | Hyper | cancer_general | NR2E1 | chr6 | 108497494 | 108497881 | Hyper | tcga, liver_tcga, cancer_general | NR2E1 |
| chr6 | 110679123 | 110679414 | Hyper | cancer_general | METTL24 | chr6 | 110797678 | 110797708 | Hyper | cancer_general | SLC22A16 |
| chr6 | 110798007 | 110798036 | Hyper | literature | SLC35F1 | chr6 | 116783448 | 116783493 | Hyper | cancer_general | FAM26F |
| chr6 | 117086249 | 117086864 | Hyper | tcga, cancer_general | FAM162B | chr6 | 117585967 | 117586004 | Hyper | cancer_general | VGLL2 |
| chr6 | 117586802 | 117587169 | Hyper | tcga, cancer_general | VGLL2 | chr6 | 117587480 | 117587577 | Hyper | cancer_general | VGLL2 |
| chr6 | 117591161 | 117591191 | Hyper | cancer_general | VGLL2 | chr6 | 117591411 | 117591743 | Hyper | cancer_general | VGLL2 |
| chr6 | 118228102 | 118228151 | Hyper | cancer_general | SLC35F1 | chr6 | 118228747 | 118228828 | Hyper | cancer_general | SLC35F1 |
| chr6 | 118229154 | 118229383 | Hyper | cancer_general | SLC35F1 | chr6 | 118229626 | 118229818 | Hyper | tcga, cancer_general | SLC35F1 |
| chr6 | 118241228 | 118241500 | Hyper | tcga, cancer_general | SLC35F1 | chr6 | 121758672 | 121758994 | Hyper | tcga, cancer_general | GJA1 |
| chr6 | 123317029 | 123317589 | Hyper | cancer_general | CLVS2 | chr6 | 123317797 | 123317833 | Hyper | tcga | CLVS2 |
| chr6 | 124124432 | 124124466 | Hyper | cancer_general | NKAIN2 | chr6 | 124124860 | 124125016 | Hyper | tcga | NKAIN2 |
| chr6 | 125284131 | 125284175 | Hyper | cancer_general | Metazoa_SRP, RNF217, STL | chr6 | 126068092 | 126068178 | Hyper | lung, cancer_general | HEY2, BC036196 |
| chr6 | 127439379 | 127439453 | Hyper | cancer_general | RSPO3 | chr6 | 127439985 | 127440127 | Hyper | cancer_general, tcga | RSPO3 |
| chr6 | 127440331 | 127441123 | Hyper | colorectal, cancer_general | RSPO3 | chr6 | 127441554 | 127441762 | Hyper | cancer_general | RSPO3 |
| chr6 | 127442021 | 127442104 | Hyper | cancer_general | RSPO3 | chr6 | 127840501 | 127840681 | Hyper | cancer_general | TMEM200A |
| chr6 | 129204459 | 129204524 | Hyper | cancer_general | LAMA2 | chr6 | 130686534 | 130687057 | Hyper | tcga, cancer_general | |
| chr6 | 131602584 | 131602694 | Hyper | cancer_general | AKAP7 | chr6 | 132722078 | 132722196 | Hyper | liver_tcga, cancer_general | MOXD1 |
| chr6 | 133561740 | 133562070 | Hyper | cancer_general | EYA4 | chr6 | 133562374 | 133563058 | Hyper | cancer_general | EYA4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 133563327 | 133563918 | Hyper | tcga, cancer_general | EYA4 | chr6 | 134176549 | 134176579 | Hyper | cancer_general | MGC34034, BC041459 |
| chr6 | 134210528 | 134211367 | Hyper | cancer_general | AX747860, TCF21 | chr6 | 134213944 | 134214364 | Hyper | cancer_general | AX747860, TCF21 |
| chr6 | 134638950 | 134639003 | Hyper | cancer_general | SGK1 | chr6 | 137241928 | 137242205 | Hyper | cancer_general | SLC35D3, PEX7 |
| chr6 | 137243208 | 137243410 | Hyper | liver_tcga | PEX7, SLC35D3 | chr6 | 137244114 | 137244616 | Hyper | cancer_general | SLC35D3, PEX7 |
| chr6 | 137311158 | 137311380 | Hyper | cancer_general | IL20RA, NHEG1 | chr6 | 137809141 | 137811088 | Hyper | cancer_general | OLIG3 |
| chr6 | 137813787 | 137813895 | Hyper | cancer_general | OLIG3 | chr6 | 137814604 | 137814763 | Hyper | liver_tcga, cancer_general | OLIG3 |
| chr6 | 137815008 | 137815662 | Hyper | cancer_general | OLIG3 | chr6 | 137816472 | 137817351 | Hyper | cancer_general | OLIG3 |
| chr6 | 137818505 | 137819368 | Hyper | cancer_general | OLIG3 | chr6 | 146755567 | 146755649 | Hyper | cancer_general | ULBP1 |
| chr6 | 150284552 | 150284581 | Hyper | literature | ULBP1 | chr6 | 150285056 | 150286639 | Hyper | liver_tcga, literature, cancer_general, tcga | |
| chr6 | 150358970 | 150359407 | Hyper | tcga, cancer_general | | chr6 | 151561016 | 151561857 | Hyper | cancer_general, tcga | AKAP12 |
| chr6 | 151562066 | 151562563 | Hyper | cancer_general | AKAP12 | chr6 | 151815055 | 151815089 | Hyper | colorectal | CCDC170 |
| chr6 | 152419908 | 152419940 | Hyper | literature | ESR1 | chr6 | 152623015 | 152623493 | Hyper | lung, cancer_general | SYNE1 |
| chr6 | 152957895 | 152958076 | Hyper | cancer_general, tcga, colorectal | SYNE1 | chr6 | 153451236 | 153451500 | Hyper | cancer_general | RGS17 |
| chr6 | 153451890 | 153451968 | Hyper | cancer_general | RGS17 | chr6 | 153452232 | 153452320 | Hyper | liver_tcga | RGS17 |
| chr6 | 153452713 | 153452746 | Hyper | liver_tcga, literature | RGS17 | chr6 | 154360650 | 154360746 | Hyper | cancer_general | OPRM1 |
| chr6 | 155316235 | 155316265 | Hyper | cancer_general | | chr6 | 157556764 | 157557912 | Hyper | cancer_general | FNDC1 |
| chr6 | 159290823 | 159290852 | Hyper | liver_tcga | | chr6 | 159590048 | 159590986 | Hyper | cancer_general | FNDC1 |
| chr6 | 159654923 | 159655003 | Hyper | cancer_general | FNDC1 | chr6 | 161100361 | 161100390 | Hyper | literature | |
| chr6 | 161188513 | 161188543 | Hyper | cancer_general | | chr6 | 161352101 | 161352135 | Hyper | cancer_general | |
| chr6 | 163834314 | 163834637 | Hyper | colorectal | QKI, CAHM | chr6 | 163834857 | 163834938 | Hyper | tcga | QKI, CAHM |
| chr6 | 163836568 | 163836900 | Hyper | colorectal | QKI, CAHM | chr6 | 166074119 | 166074412 | Hyper | cancer_general | |
| chr6 | 166076788 | 166077021 | Hyper | cancer_general | | chr6 | 166077378 | 166077660 | Hyper | cancer_general | |
| chr6 | 166267582 | 166268082 | Hyper | cancer_general | AK090688 | chr6 | 166401254 | 166401307 | Hyper | cancer_general | LINC00602, LINC00473, AK090688 |
| chr6 | 166402240 | 166402546 | Hyper | cancer_general | LINC00473, AK090688, LINC00602 | chr6 | 166421911 | 166422185 | Hyper | cancer_general | |
| chr6 | 166579723 | 166580144 | Hyper | cancer_general | T | chr6 | 166580344 | 166582797 | Hyper | tcga, cancer_general, literature | T |
| chr6 | 168842847 | 168842944 | Hyper | cancer_general | SMOC2 | chr6 | 169653638 | 169653668 | Hyper | cancer_general | THBS2 |
| chr4 | 107711 | 107759 | Hyper | cancer_general | | chr4 | 206324 | 206353 | Hyper | literature | ZNF876P |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 330392 | 330708 | Hyper | tcga, cancer_general, liver_tcga | ZNF141 | chr4 | 331322 | 331352 | Hyper | esophageal | ZNF141 |
| chr4 | 568429 | 569914 | Hyper | cancer_general | | chr4 | 570966 | 571013 | Hyper | cancer_general | ATP5I, MYL5, PDE6B, BC020343 |
| chr4 | 571508 | 571689 | Hyper | cancer_general | | chr4 | 657521 | 657552 | Hyper | tcga | |
| chr4 | 682798 | 682919 | Hyper | cancer_general | MFSD7, MYL5 | chr4 | 995855 | 996357 | Hyper | cancer_general, tcga, liver_tcga | FGFRL1, SLC26A1, IDUA |
| chr4 | 996639 | 996708 | Hyper | cancer_general | IDUA, FGFRL1, SLC26A1 | chr4 | 1107494 | 1107585 | Hyper | liver_tcga | RNF212, TMED11P |
| chr4 | 1165379 | 1165470 | Hyper | cancer_general | SPON2 | chr4 | 1396578 | 1396835 | Hyper | liver_tcga, cancer_general | CRIPAK |
| chr4 | 1397396 | 1397495 | Hyper | cancer_general | CRIPAK | chr4 | 1398303 | 1398378 | Hyper | cancer_general | CRIPAK |
| chr4 | 1399723 | 1399768 | Hyper | liver_3842731tcga | CRIPAK | chr4 | 1400728 | 1400785 | Hyper | cancer_general | |
| chr4 | 1401711 | 1401743 | Hyper | cancer_general | LETM1, FGFR3 | chr4 | 1800153 | 1800191 | Hyper | liver_tcga | FGFR3 |
| chr4 | 1803550 | 1803582 | Hyper | literature | LETM1, FGFR3 | chr4 | 1806084 | 1806113 | Hyper | literature | LETM1, FGFR3 |
| chr4 | 1807355 | 1807384 | Hyper | literature | C4orf48 | chr4 | 1962787 | 1962816 | Hyper | literature | WHSC1 |
| chr4 | 2042106 | 2042556 | Hyper | cancer_general | RGS12 | chr4 | 2765862 | 2765910 | Hyper | cancer_general | TNIP2 |
| chr4 | 3371519 | 3371652 | Hyper | liver_3842731tcga | ADRA2C | chr4 | 3768833 | 3769342 | Hyper | cancer_general | ADRA2C |
| chr4 | 3769542 | 3769574 | Hyper | cancer_general | TMEM128, OTOP1 | chr4 | 3873694 | 3873769 | Hyper | cancer_general | OTOP1, TMEM128 |
| chr4 | 4228185 | 4228241 | Hyper | cancer_general | NSG1 | chr4 | 4229689 | 4229781 | Hyper | cancer_general | |
| chr4 | 4387533 | 4387627 | Hyper | cancer_general | MSX1 | chr4 | 4855102 | 4855171 | Hyper | cancer_general | MSX1 |
| chr4 | 4855371 | 4855433 | Hyper | literature | MSX1 | chr4 | 4860046 | 4860075 | Hyper | literature | MSX1 |
| chr4 | 4862769 | 4863110 | Hyper | tcga, cancer_general | MSX1 | chr4 | 4867698 | 4867886 | Hyper | cancer_general | MSX1 |
| chr4 | 4868566 | 4869087 | Hyper | cancer_general | MSX1 CYTL1 | chr4 | 4872088 | 4872167 | Hyper | cancer_general | MSX1 |
| chr4 | 4872777 | 4872850 | Hyper | literature | STK32B | chr4 | 4873427 | 4873528 | Hyper | tcga | MSX1 |
| chr4 | 5021188 | 5021217 | Hyper | cancer_general | EVC, EVC2 | chr4 | 5053070 | 5053518 | Hyper | tcga, cancer_general | STK32B |
| chr4 | 5053747 | 5054093 | Hyper | cancer_general | FLJ46481, CRMP1 | chr4 | 5709906 | 5710269 | Hyper | cancer_general | EVC, EVC2 |
| chr4 | 5712979 | 5713281 | Hyper | tcga | FLJ46481, CRMP1 | chr4 | 5889948 | 5890045 | Hyper | cancer_general | CRMP1, FLJ46481 |
| chr4 | 5890274 | 5890444 | Hyper | cancer_general | FLJ46481, CRMP1 | chr4 | 5891966 | 5892194 | Hyper | cancer_general, pancreas | FLJ46481, CRMP1 |
| chr4 | 5892750 | 5892780 | Hyper | liver_tcga, cancer_general | LOC285484, JAKMIP1 | chr4 | 5893981 | 5894347 | Hyper | cancer_general | FLJ46481, CRMP1 |
| chr4 | 5894676 | 5894787 | Hyper | cancer_general | | chr4 | 6200897 | 6201235 | Hyper | cancer_general | JAKMIP1, LOC285484 |
| chr4 | 6202103 | 6202276 | Hyper | cancer_general | | chr4 | 6247351 | 6247381 | Hyper | cancer_general | LOC285484 |
| chr4 | 6565004 | 6565042 | Hyper | cancer_general | HMX1 | chr4 | 8582549 | 8582579 | Hyper | cancer_general | CPZ, GPR78 |
| chr4 | 8858827 | 8859738 | Hyper | cancer_general | | chr4 | 8859974 | 8860553 | Hyper | cancer_general | HMX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 8861649 | 8862014 | Hyper | cancer_general | HMX1 | chr4 | 8862797 | 8862911 | Hyper | cancer_general | HMX1 |
| chr4 | 8863441 | 8863774 | Hyper | cancer_general | HMX1 | chr4 | 8864499 | 8864598 | Hyper | cancer_general | HMX1 |
| chr4 | 8864831 | 8865058 | Hyper | cancer_general | HMX1 | chr4 | 8868822 | 8869364 | Hyper | cancer_general | HMX1 |
| chr4 | 8869601 | 8869813 | Hyper | cancer_general | HMX1 | chr4 | 8873054 | 8873337 | Hyper | cancer_general | HMX1 |
| chr4 | 8873809 | 8873984 | Hyper | cancer_general | HMX1 | chr4 | 8874485 | 8874787 | Hyper | cancer_general | HMX1 |
| chr4 | 8875877 | 8875907 | Hyper | cancer_general | HMX1 | chr4 | 8893060 | 8893093 | Hyper | pancreas | |
| chr4 | 8893501 | 8893531 | Hyper | cancer_general | | chr4 | 8893794 | 8893931 | Hyper | cancer_general | |
| chr4 | 8894641 | 8895350 | Hyper | cancer_general | | chr4 | 8895554 | 8895584 | Hyper | cancer_general | |
| chr4 | 8895915 | 8896052 | Hyper | cancer_general | | chr4 | 9782992 | 9783412 | Hyper | literature, cancer general | DRD5 |
| chr4 | 10458395 | 10459121 | Hyper | cancer_general | ZNF518B | chr4 | 10462833 | 10463604 | Hyper | tcga, cancer_general | ZNF518B |
| chr4 | 11429506 | 11429633 | Hyper | cancer_general | | chr4 | 13524026 | 13524430 | Hyper | tcga, cancer_general | LOC285547 |
| chr4 | 13524665 | 13524775 | Hyper | cancer_general | LOC285547 | chr4 | 13537569 | 13537688 | Hyper | cancer_general | NKX3-2, LOC285547 |
| chr4 | 13540983 | 13541068 | Hyper | cancer_general | NKX3-2, LOC285548, LOC285547 | chr4 | 13541408 | 13541447 | Hyper | cancer_general | LOC285548, LOC285547, NKX3-2 |
| chr4 | 13543859 | 13544113 | Hyper | liver_tcga, cancer_general | LOC285548, NKX3-2 | chr4 | 13545563 | 13545760 | Hyper | liver_tcga, cancer_general | LOC285548, NKX3-2 |
| chr4 | 13546026 | 13546078 | Hyper | cancer_general | LOC285548, NKX3-2 | chr4 | 13548502 | 13548895 | Hyper | cancer_general | LOC285548, NKX3-2 |
| chr4 | 13549340 | 13549510 | Hyper | tcga | LOC285548, NKX3-2 | chr4 | 15780223 | 15780320 | Hyper | tcga, liver_tcga | CD38 |
| chr4 | 16084741 | 16085381 | Hyper | tcga, cancer_general | FAM184B | chr4 | 16085618 | 16085682 | Hyper | cancer_general | |
| chr4 | 17783003 | 17783600 | Hyper | tcga, cancer_general, liver_tcga | SLIT2 | chr4 | 20254693 | 20254723 | Hyper | cancer_general | SLIT2 |
| chr4 | 20255414 | 20255861 | Hyper | cancer_general | SLIT2 | chr4 | 20256152 | 20256340 | Hyper | cancer_general | SLIT2 |
| chr4 | 21950248 | 21950341 | Hyper | cancer_general | | chr4 | 24801809 | 24801985 | Hyper | cancer_general | CCDC149, SOD3 |
| chr4 | 24914638 | 24914668 | Hyper | blood | CCDC149 | chr4 | 25656815 | 25656879 | Hyper | tcga | SLC34A2 |
| chr4 | 25657437 | 25657477 | Hyper | cancer_general | SLC34A2 | chr4 | 27086432 | 27086462 | Hyper | cancer_general | PCDH7 |
| chr4 | 30722243 | 30722273 | Hyper | cancer_general | PCDH7 | chr4 | 30723811 | 30723862 | Hyper | cancer_general | KIAA1239, MIR4801 |
| chr4 | 30724249 | 30724372 | Hyper | cancer_general | PCDH7 | chr4 | 37245726 | 37245851 | Hyper | cancer_general | KIAA1239, MIR4801 |
| chr4 | 37246134 | 37246883 | Hyper | tcga, cancer_general | KIAA1239, MIR4801 | chr4 | 37247096 | 37247216 | Hyper | cancer_general | UCHL1, UCHL1-AS1 |
| chr4 | 40632773 | 40632802 | Hyper | literature | | chr4 | 41258716 | 41259176 | Hyper | liver_tcga, cancer_general | |
| chr4 | 41747009 | 41747133 | Hyper | cancer_general | PHOX2B | chr4 | 41747493 | 41747582 | Hyper | cancer_general | PHOX2B |
| chr4 | 41747958 | 41748296 | Hyper | cancer_general | PHOX2B | chr4 | 41748660 | 41748803 | Hyper | cancer_general | PHOX2B |
| chr4 | 41749033 | 41749063 | Hyper | cancer_general | PHOX2B | chr4 | 41749270 | 41749761 | Hyper | cancer_general | PHOX2B |
| chr4 | 41750223 | 41750504 | Hyper | lung, cancer_general | PHOX2B | chr4 | 41751870 | 41752006 | Hyper | cancer_general | PHOX2B |
| chr4 | 41752451 | 41752693 | Hyper | cancer_general | PHOX2B | chr4 | 41752968 | 41753398 | Hyper | cancer_general | PHOX2B |
| chr4 | 41753610 | 41754071 | Hyper | cancer_general | PHOX2B | chr4 | 41875430 | 41875902 | Hyper | cancer_general | BC025350 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 41880331 | 41880412 | Hyper | cancer_general | BC025350 | chr4 | 41881385 | 41881425 | Hyper | cancer_general | BC025350 |
| chr4 | 41882549 | 41882627 | Hyper | literature, cancer_general | BC025350 | chr4 | 41883091 | 41883302 | Hyper | cancer_general | BC025350 |
| chr4 | 41883510 | 41883610 | Hyper | cancer_general | BEND4 | chr4 | 42152908 | 42154025 | Hyper | liver_tcga, cancer_general, tcga | BEND4 |
| chr4 | 42154280 | 42154359 | Hyper | cancer_general | BEND4 | chr4 | 42154662 | 42154997 | Hyper | pancreas, cancer_general, literature | |
| chr4 | 42398842 | 42398872 | Hyper | lung | SHISA3 | chr4 | 42399137 | 42399191 | Hyper | cancer_general | SHISA3 |
| chr4 | 42399688 | 42399872 | Hyper | tcga, liver_tcga | SHISA3 | chr4 | 44449480 | 44449651 | Hyper | cancer_general | KCTD8 |
| chr4 | 44450263 | 44450375 | Hyper | cancer_general | KCTD8 | chr4 | 46391353 | 46391383 | Hyper | cancer_general | GABRA2 |
| chr4 | 46995161 | 46995835 | Hyper | tcga, cancer_general, liver_tcga | GABRA4 | chr4 | 47034908 | 47034938 | Hyper | cancer_general | GABRB1 |
| chr4 | 48485067 | 48486000 | Hyper | liver_tcga, cancer_general | SLC10A4, ZAR1 | chr4 | 48486356 | 48486389 | Hyper | cancer_general | ZAR1, SLC10A4 |
| chr4 | 48492181 | 48492433 | Hyper | tcga, liver_tcga, cancer_general | ZAR1, FRYL, SLC10A4 | chr4 | 48988109 | 48988335 | Hyper | tcga | CWH43 |
| chr4 | 53728495 | 53729056 | Hyper | tcga, cancer_general, liver_tcga | RASL11B | chr4 | 54966854 | 54967075 | Hyper | tcga, cancer_general | GSX2 |
| chr4 | 54967342 | 54967484 | Hyper | cancer_general | GSX2 | chr4 | 54969833 | 54970095 | Hyper | cancer_general | GSX2 |
| chr4 | 54970369 | 54970482 | Hyper | cancer_general | GSX2 | chr4 | 54975936 | 54976131 | Hyper | cancer_general | GSX2 |
| chr4 | 55093048 | 55093255 | Hyper | cancer_general | PDGFRA | chr4 | 55096239 | 55096344 | Hyper | cancer_general | PDGFRA |
| chr4 | 55097404 | 55097634 | Hyper | cancer_general | PDGFRA | chr4 | 55097973 | 55098373 | Hyper | tcga, cancer_general | PDGFRA |
| chr4 | 55098674 | 55098744 | Hyper | cancer_general | PDGFRA | chr4 | 55099016 | 55099062 | Hyper | cancer_general | PDGFRA |
| chr4 | 55133613 | 55133642 | Hyper | literature | PDGFRA | chr4 | 55136787 | 55136816 | Hyper | literature | PDGFRA |
| chr4 | 55138657 | 55138686 | Hyper | literature | PDGFRA | chr4 | 55139691 | 55139720 | Hyper | literature | PDGFRA |
| chr4 | 55140731 | 55140784 | Hyper | literature | PDGFRA | chr4 | 55141015 | 55141050 | Hyper | literature | PDGFRA |
| chr4 | 55144105 | 55144134 | Hyper | literature | PDGFRA | chr4 | 55146554 | 55146583 | Hyper | literature | PDGFRA |
| chr4 | 55152075 | 55152140 | Hyper | literature | PDGFRA | chr4 | 55524220 | 55524274 | Hyper | cancer_general | KIT |
| chr4 | 55589753 | 55589782 | Hyper | literature | DL490879, KIT | chr4 | 55592166 | 55592204 | Hyper | literature | DL490879, KIT |
| chr4 | 55593417 | 55593675 | Hyper | literature | KIT, DL490879 | chr4 | 55594183 | 55594212 | Hyper | literature | DL490879, KIT |
| chr4 | 55595504 | 55595614 | Hyper | literature | KIT, DL490879 | chr4 | 55599306 | 55599356 | Hyper | literature | KIT, DL490879 |
| chr4 | 55968165 | 55968194 | Hyper | literature | KDR | chr4 | 55991107 | 55991228 | Hyper | cancer_general | KDR |
| chr4 | 55992129 | 55992169 | Hyper | cancer_general | KDR | chr4 | 56659692 | 56660021 | Hyper | cancer_general | U6 |
| chr4 | 57371718 | 57371963 | Hyper | liver_tcga, cancer_general | ARL9, SRP72 | chr4 | 57372336 | 57372504 | Hyper | cancer_general | ARL9, SRP72 |
| chr4 | 57396946 | 57397264 | Hyper | cancer_general | THEGL, ARL9 | chr4 | 57521403 | 57522815 | Hyper | tcga, cancer_general | HOPX |
| chr4 | 57687720 | 57687782 | Hyper | esophageal | SPINK2 | chr4 | 57976033 | 57976185 | Hyper | liver_tcga, tcga | LOC255130, IGFBP7 |
| chr4 | 57976416 | 57976573 | Hyper | tcga, liver_tcga | IGFBP7, LOC255130 | chr4 | 58030191 | 58030524 | Hyper | esophageal | LOC255130 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 62066196 | 62066553 | Hyper | tcga | LPHN3 | chr4 | 62067511 | 62067624 | Hyper | cancer_general | LPHN3 |
| chr4 | 62068072 | 62068150 | Hyper | cancer_general | LPHN3 | chr4 | 66335130 | 66335443 | Hyper | tcga, cancer_general | LOC100144602, EPHA5 |
| chr4 | 66536171 | 66536323 | Hyper | tcga | LOC100144602, EPHA5 | chr4 | 74702479 | 74702516 | Hyper | cancer_general | CXCL6 |
| chr4 | 74735076 | 74735137 | Hyper | blood | CXCL1 | chr4 | 74809877 | 74809933 | Hyper | cancer_general | |
| chr4 | 75858573 | 75858629 | Hyper | esophageal | PARM1 | chr4 | 76555532 | 76555856 | Hyper | tcga, cancer_general, liver_tcga | CDKL2 |
| chr4 | 81106351 | 81106871 | Hyper | tcga, cancer_general | PRDM8 | chr4 | 81124277 | 81124662 | Hyper | cancer_general | PRDM8 |
| chr4 | 81187046 | 81187076 | Hyper | cancer_general | FGF5 | chr4 | 81187559 | 81187589 | Hyper | cancer_general | FGF5 |
| chr4 | 81188491 | 81188556 | Hyper | cancer_general | FGF5 | chr4 | 81189419 | 81189911 | Hyper | cancer_general | FGF5 |
| chr4 | 81951431 | 81951460 | Hyper | literature | BMP3 | chr4 | 81951941 | 81951970 | Hyper | literature | BMP3 |
| chr4 | 81952170 | 81952344 | Hyper | literature, cancer_general | BMP3 | chr4 | 82135873 | 82136056 | Hyper | cancer_general | PRKG2 |
| chr4 | 82136495 | 82136548 | Hyper | cancer_general | PRKG2 | chr4 | 82136807 | 82136837 | Hyper | cancer_general | PRKG2 |
| chr4 | 83720611 | 83720643 | Hyper | tcga | | chr4 | 84035907 | 84035936 | Hyper | literature | PLAC8 |
| chr4 | 85402377 | 85402511 | Hyper | cancer_general | | chr4 | 85402776 | 85403423 | Hyper | cancer_general | |
| chr4 | 85403913 | 85404693 | Hyper | cancer_general | | chr4 | 85414045 | 85414142 | Hyper | cancer_general | NKX6-1 |
| chr4 | 85414373 | 85414405 | Hyper | cancer_general | NKX6-1 | chr4 | 85414725 | 85414846 | Hyper | cancer_general | NKX6-1 |
| chr4 | 85417336 | 85417564 | Hyper | cancer_general | NKX6-1 | chr4 | 85417953 | 85418079 | Hyper | cancer_general | NKX6-1 |
| chr4 | 85418393 | 85418963 | Hyper | cancer_general | NKX6-1 | chr4 | 85420591 | 85420621 | Hyper | cancer_general | NKX6-1 |
| chr4 | 85422188 | 85422432 | Hyper | cancer_general | NKX6-1 | chr4 | 85422953 | 85423316 | Hyper | cancer_general | NKX6-1 |
| chr4 | 85424401 | 85424483 | Hyper | cancer_general | NKX6-1 | chr4 | 87515337 | 87515367 | Hyper | esophageal | PTPN13 |
| chr4 | 89378464 | 89378497 | Hyper | cancer_general | HERC5 | chr4 | 89378744 | 89378888 | Hyper | cancer_general | HERC5 |
| chr4 | 90757517 | 90757828 | Hyper | cancer_general, tcga | LOC644248, SNCA, LOC644248 | chr4 | 90758105 | 90758134 | Hyper | tcga | LOC644248, SNCA |
| chr4 | 90758776 | 90758883 | Hyper | liver_tcga, cancer_general | GRID2 | chr4 | 93224972 | 93225171 | Hyper | tcga | GRID2 |
| chr4 | 93226365 | 93227129 | Hyper | tcga, cancer_general | ATOH1 | chr4 | 94749725 | 94749755 | Hyper | blood | ATOH1 |
| chr4 | 94750982 | 94751140 | Hyper | tcga, cancer_general | ATOH1 | chr4 | 94751419 | 94751502 | Hyper | cancer_general | ATOH1 |
| chr4 | 94753415 | 94753445 | Hyper | cancer_general | ATOH1 | chr4 | 94755963 | 94756109 | Hyper | cancer_general | ATOH1 |
| chr4 | 96470752 | 96470782 | Hyper | cancer_general | UNC5C | chr4 | 101111246 | 101111504 | Hyper | cancer_general, tcga | DDIT4L |
| chr4 | 101111857 | 101111970 | Hyper | tcga, cancer_general | DDIT4L | chr4 | 102711731 | 102711787 | Hyper | cancer_general | BANK1 |
| chr4 | 102711994 | 102712065 | Hyper | cancer_general | BANK1 | chr4 | 107955311 | 107955826 | Hyper | cancer_general | DKK2 |
| chr4 | 107956676 | 107957086 | Hyper | tcga, cancer_general | DKK2 | chr4 | 107957373 | 107957466 | Hyper | cancer_general | DKK2 |
| chr4 | 109093101 | 109093168 | Hyper | tcga, cancer_general | LEF1-AS1 | chr4 | 109093405 | 109093506 | Hyper | cancer_general | LEF1-AS1 |
| chr4 | 110223090 | 110223980 | Hyper | liver_tcga, cancer_general | COL25A1 | chr4 | 111532632 | 111532961 | Hyper | cancer_general | PITX2 |
| chr4 | 111536288 | 111536693 | Hyper | cancer_general | PITX2 | chr4 | 111536960 | 111537042 | Hyper | cancer_general | PITX2 |
| chr4 | 111537407 | 111537497 | Hyper | cancer_general | PITX2 | chr4 | 111540199 | 111540360 | Hyper | liver_tcga, cancer_general | PITX2 |
| chr4 | 111542187 | 111542757 | Hyper | cancer_general | PITX2 | chr4 | 111543232 | 111543450 | Hyper | liver_tcga, literature, cancer_general | PITX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 111543661 | 111543735 | Hyper | cancer_general | PITX2 | chr4 | 111544381 | 111544583 | Hyper | cancer_general | PITX2 |
| chr4 | 111549800 | 111549830 | Hyper | cancer_general | PITX2 | chr4 | 111550618 | 111550834 | Hyper | cancer_general | PITX2 |
| chr4 | 111552118 | 111552148 | Hyper | cancer_general | PITX2 | chr4 | 111553099 | 111553450 | Hyper | cancer_general | PITX2 |
| chr4 | 111553916 | 111553951 | Hyper | cancer_general | PITX2 | chr4 | 111554950 | 111555343 | Hyper | cancer_general | |
| chr4 | 111557965 | 111558049 | Hyper | cancer_general | | chr4 | 111558551 | 111559233 | Hyper | literature, cancer_general | |
| chr4 | 111560249 | 111560636 | Hyper | cancer_general | NEUROG2 | chr4 | 111562576 | 111562648 | Hyper | cancer_general | NEUROG2 |
| chr4 | 113430640 | 113430672 | Hyper | cancer_general | NEUROG2 | chr4 | 113431834 | 113432573 | Hyper | cancer_general | NEUROG2 |
| chr4 | 113436216 | 113436287 | Hyper | cancer_general | NEUROG2 | chr4 | 113441592 | 113441733 | Hyper | cancer_general | NEUROG2 |
| chr4 | 113442098 | 113442525 | Hyper | cancer_general | | chr4 | 113444020 | 113444448 | Hyper | cancer_general | PRDM5 |
| chr4 | 178447399 | 178447458 | Hyper | cancer_general | 7SK, NDNF | chr4 | 121844063 | 121844206 | Hyper | cancer_general | |
| chr4 | 121992265 | 121992312 | Hyper | cancer_general | QRFPR | chr4 | 121993997 | 121994251 | Hyper | cancer_general | QRFPR |
| chr4 | 122301422 | 122301846 | Hyper | cancer_general | PP12613, TMEM155 | chr4 | 122302116 | 122302246 | Hyper | cancer_general | PP12613, TMEM155 |
| chr4 | 122685807 | 122685951 | Hyper | cancer_general | | chr4 | 122686209 | 122686507 | Hyper | tcga, liver_tcga, cancer_general | |
| chr4 | 122871294 | 122871334 | Hyper | cancer_general | FAT4 | chr4 | 122871573 | 122872000 | Hyper | cancer_general | FAT4 |
| chr4 | 126237310 | 126237611 | Hyper | tcga, cancer_general | | chr4 | 126238024 | 126238436 | Hyper | cancer_general, tcga | |
| chr4 | 128544048 | 128544161 | Hyper | cancer_general | INTU | chr4 | 128544646 | 128544789 | Hyper | cancer_general | INTU |
| chr4 | 134067881 | 134068004 | Hyper | cancer_general | PCDH10, BC040219 | chr4 | 134068577 | 134068791 | Hyper | tcga, cancer_general | PCDH10, BC040219 |
| chr4 | 134069289 | 134069318 | Hyper | literature | BC040219 | chr4 | 134069578 | 134069896 | Hyper | literature, cancer_general | PCDH10, BC040219 |
| chr4 | 134070374 | 134070403 | Hyper | literature | PCDH10 | chr4 | 134071648 | 134072967 | Hyper | literature, cancer_general | PCDH10, BC040219 |
| chr4 | 134073184 | 134073322 | Hyper | cancer_general | PCDH10, BC040219 | chr4 | 134073568 | 134073641 | Hyper | cancer_general | PCDH10, BC040219 |
| chr4 | 134074030 | 134074156 | Hyper | cancer_general | PCDH10, BC040219 | chr4 | 140200529 | 140201462 | Hyper | cancer_general | MGARP, NDUFC1 |
| chr4 | 140656643 | 140657089 | Hyper | cancer_general | MAML3 | chr4 | 141347942 | 141348151 | Hyper | cancer_general | CLGN |
| chr4 | 141418921 | 141419418 | Hyper | tcga, cancer_general | LOC152586 | chr4 | 141488870 | 141489128 | Hyper | cancer_general | UCP1 |
| chr4 | 142053130 | 142053160 | Hyper | cancer_general | RNF150 | chr4 | 142053520 | 142053734 | Hyper | tcga, cancer_general | RNF150 |
| chr4 | 142054239 | 142054460 | Hyper | tcga | RNF150 | chr4 | 143766796 | 143766930 | Hyper | cancer_general | HHIP, HHIP-AS1 |
| chr4 | 144622058 | 144622058 | Hyper | cancer_general, tcga | FREM3 | chr4 | 145568052 | 145568147 | Hyper | cancer_general | |
| chr4 | 145568459 | 145568741 | Hyper | cancer_general | HHIP, HHIP-AS1 | chr4 | 147558272 | 147558504 | Hyper | cancer_general | POU4F2 |
| chr4 | 147559321 | 147560617 | Hyper | tcga, cancer_general | POU4F2 | chr4 | 147560933 | 147562055 | Hyper | cancer_general | POU4F2 |
| chr4 | 147568636 | 147569060 | Hyper | cancer_general | POU4F2 | chr4 | 147569620 | 147569650 | Hyper | cancer_general | POU4F2 |
| chr4 | 147576177 | 147576639 | Hyper | cancer_general | | chr4 | 152246132 | 152246314 | Hyper | blood | |
| chr4 | 153247273 | 153247386 | Hyper | literature | FBXW7 | chr4 | 153249362 | 153249398 | Hyper | literature | FBXW7 |
| chr4 | 153251894 | 153251923 | Hyper | literature | FBXW7 | chr4 | 154709524 | 154710914 | Hyper | tcga, literature, cancer_general | SFRP2 |
| chr4 | 154712172 | 154712594 | Hyper | tcga, cancer_general | SFRP2 | chr4 | 154713500 | 154713530 | Hyper | cancer_general | SFRP2 |
| chr4 | 154713949 | 154714010 | Hyper | cancer_general | SFRP2 | chr4 | 155254166 | 155254196 | Hyper | cancer_general | DCHS2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 155411501 | 155412279 | Hyper | cancer_general | DCHS2 | chr4 | 155663209 | 155663647 | Hyper | cancer_general, tcga | LRAT, DQ266889 |
| chr4 | 156129153 | 156129183 | Hyper | cancer_general | NPY2R | chr4 | 156129451 | 156129495 | Hyper | cancer_general | NPY2R |
| chr4 | 156129746 | 156129797 | Hyper | cancer_general | NPY2R | chr4 | 156130047 | 156130297 | Hyper | cancer_general | NPY2R |
| chr4 | 156297416 | 156297556 | Hyper | colorectal, cancer_general | MAP9 | chr4 | 156297839 | 156298073 | Hyper | tcga, colorectal | MAP9 |
| chr4 | 156588311 | 156588401 | Hyper | tcga, cancer_general | GUCY1A3 | chr4 | 156589273 | 156589323 | Hyper | cancer_general | GUCY1A3 |
| chr4 | 156680257 | 156680532 | Hyper | cancer_general | GUCY1B3 | chr4 | 156681370 | 156681489 | Hyper | tcga | GUCY1B3 |
| chr4 | 158141576 | 158141606 | Hyper | cancer_general | GRIA2 | chr4 | 158142847 | 158142999 | Hyper | cancer_general | GRIA2 |
| chr4 | 158143443 | 158143564 | Hyper | cancer_general | GRIA2 | chr4 | 164252991 | 164253447 | Hyper | tcga, cancer_general | NPY1R, NPYY1 |
| chr4 | 165304515 | 165304578 | Hyper | cancer_general | | chr4 | 165305030 | 165305163 | Hyper | cancer_general | |
| chr4 | 166414834 | 166414921 | Hyper | lung, cancer_general | | chr4 | 166794771 | 166794909 | Hyper | tcga | TLL1 |
| chr4 | 166796011 | 166796212 | Hyper | cancer_general | TLL1 | chr4 | 168155109 | 168155269 | Hyper | tcga, cancer_general | |
| chr4 | 170947287 | 170947325 | Hyper | blood | BC031941 | chr4 | 172734168 | 172734203 | Hyper | cancer_general | |
| chr4 | 172734550 | 172734790 | Hyper | cancer_general | GALNTL6 | chr4 | 174429658 | 174429688 | Hyper | cancer_general | GALNTL6 |
| chr4 | 174430310 | 174431072 | Hyper | cancer_general | | chr4 | 174438567 | 174438744 | Hyper | cancer_general | HAND2 |
| chr4 | 174439822 | 174440257 | Hyper | literature, cancer_general | HAND2 | chr4 | 174440635 | 174440713 | Hyper | cancer_general | HAND2 |
| chr4 | 174443212 | 174443242 | Hyper | cancer_general | HAND2, NBLA00301 | chr4 | 174443563 | 174443934 | Hyper | tcga, cancer_general | HAND2, NBLA00301 |
| chr4 | 174444151 | 174444180 | Hyper | tcga | HAND2, NBLA00301 | chr4 | 174446486 | 174446525 | Hyper | cancer_general | HAND2, NBLA00301 |
| chr4 | 174446952 | 174447005 | Hyper | cancer_general | HAND2, NBLA00301 | chr4 | 174449950 | 174451482 | Hyper | tcga, cancer_general, literature | HAND2, NBLA00301 |
| chr4 | 174451855 | 174452098 | Hyper | cancer_general | NBLA00301, HAND2 | chr4 | 174459185 | 174459840 | Hyper | cancer_general | HAND2, NBLA00301 |
| chr4 | 174460186 | 174460221 | Hyper | cancer_general | NBLA00301, HAND2 | chr4 | 175132735 | 175132765 | Hyper | cancer_general | AK125257 |
| chr4 | 175133085 | 175133201 | Hyper | cancer_general | AK125257 | chr4 | 175134897 | 175135672 | Hyper | cancer_general | AK125257 |
| chr4 | 175135921 | 175136011 | Hyper | cancer_general | AK125257 | chr4 | 175138411 | 175138546 | Hyper | cancer_general | AK125257 |
| chr4 | 175138964 | 175139254 | Hyper | cancer_general | AK125257 | chr4 | 175139559 | 175139685 | Hyper | cancer_general | AK125257 |
| chr4 | 175750456 | 175750738 | Hyper | cancer_general | AK093264, BC034301, GLRA3 | chr4 | 176923424 | 176923558 | Hyper | tcga, cancer_general | |
| chr4 | 176987324 | 176987373 | Hyper | cancer_general | WDR17 | chr4 | 177713228 | 177713437 | Hyper | tcga, cancer_general | VEGFC |
| chr4 | 180979270 | 180979300 | Hyper | cancer_general | | chr4 | 180980297 | 180980356 | Hyper | cancer_general | |
| chr4 | 183063666 | 183063950 | Hyper | cancer_general | TENM3, MGC45800 | chr4 | 183064617 | 183064655 | Hyper | cancer_general | TENM3, MGC45800 |
| chr4 | 184019249 | 184019316 | Hyper | cancer_general | WWC2, WWC2-AS2 | chr4 | 184019692 | 184019736 | Hyper | blood | WWC2-AS2 |
| chr4 | 184020106 | 184020179 | Hyper | blood | WWC2, WWC2-AS2 | chr4 | 184644053 | 184644249 | Hyper | hepatobiliary | WWC2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 184718260 | 184718352 | Hyper | cancer_general | | chr4 | 184826238 | 184826493 | Hyper | cancer_general, tcga | STOX2 |
| chr4 | 184826938 | 184827237 | Hyper | tcga, cancer_general | STOX2 | chr4 | 185089696 | 185089797 | Hyper | head_neck | ENPP6 |
| chr4 | 185937333 | 185937889 | Hyper | cancer_general | HELT | chr4 | 185938497 | 185938564 | Hyper | cancer_general | HELT |
| chr4 | 185940338 | 185940460 | Hyper | cancer_general | HELT | chr4 | 185941585 | 185942760 | Hyper | cancer_general | HELT |
| chr4 | 187647073 | 187647457 | Hyper | blood | FAT1 | chr3 | 238536 | 239094 | Hyper | cancer_general | CHL1 |
| chr3 | 239622 | 240223 | Hyper | cancer_general | CHL1 | chr3 | 2140277 | 2140398 | Hyper | cancer_general | CNTN4 |
| chr3 | 3840498 | 3840758 | Hyper | liver_tcga, cancer_general | LRRN1, BC141932, SUMF1 | chr3 | 3841046 | 3841144 | Hyper | tcga, liver_tcga | LRRN1, BC141932, SUMF1 |
| chr3 | 3842679 | 3842731 | Hyper | tcga | SUMF1, BC141932, LRRN1 | | | | | | |
| chr3 | 6902288 | 6903353 | Hyper | cancer_general | GRM7 | chr3 | 5137960 | 5138019 | Hyper | pancreas | |
| chr3 | 8725296 | 8725348 | Hyper | esophageal | | chr3 | 6903425 | 6903463 | Hyper | cancer_general | GRM7 |
| | | | | | | chr3 | 8810136 | 8810220 | Hyper | cancer_general | Mir_548, OXTR |
| chr3 | 9178165 | 9178263 | Hyper | literature, tcga | SRGAP3 | chr3 | 9593979 | 9594015 | Hyper | cancer_general | LHFPL4 |
| chr3 | 9594263 | 9594382 | Hyper | liver_tcga | LHFPL4 | chr3 | 9595292 | 9595584 | Hyper | cancer_general | LHFPL4 |
| chr3 | 9904233 | 9904554 | Hyper | cancer_general | CIDEC | chr3 | 9957064 | 9957142 | Hyper | cancer_general | IL17RC, IL17RE |
| chr3 | 9957451 | 9957677 | Hyper | cancer_general | IL17RE, IL17RC | chr3 | 10183321 | 10183350 | Hyper | literature | VHL |
| chr3 | 10183706 | 10183782 | Hyper | literature | VHL | chr3 | 10191477 | 10191620 | Hyper | literature | VHL |
| chr3 | 10857987 | 10858019 | Hyper | cancer_general | SLC6A11 | chr3 | 11034264 | 11034359 | Hyper | tcga | SLC6A1 |
| chr3 | 11035070 | 11035330 | Hyper | cancer_general | SLC6A1 | chr3 | 12046405 | 12046632 | Hyper | tcga | SYN2 |
| chr3 | 12632309 | 12632401 | Hyper | literature | MKRN2, RAF1 | chr3 | 12645678 | 12645713 | Hyper | literature | RAF1 |
| chr3 | 12729424 | 12729454 | Hyper | esophageal | | chr3 | 12917606 | 12917655 | Hyper | cancer_general | DQ581328 |
| chr3 | 13323494 | 13323973 | Hyper | cancer_general | | chr3 | 13324358 | 13324433 | Hyper | cancer_general | |
| chr3 | 13324847 | 13324938 | Hyper | tcga, cancer_general | | chr3 | 13590416 | 13590863 | Hyper | cancer_general | FBLN2 |
| chr3 | 13679284 | 13679319 | Hyper | pancreas | | chr3 | 13921407 | 13921463 | Hyper | cancer_general | WNT7A |
| chr3 | 14851850 | 14851897 | Hyper | cancer_general | FGD5 | chr3 | 14852325 | 14852919 | Hyper | tcga | FGD5 |
| chr3 | 16554052 | 16554111 | Hyper | cancer_general | | chr3 | 16554347 | 16554633 | Hyper | tcga, cancer_general | |
| chr3 | 19189441 | 19189470 | Hyper | tcga | KCNH8 | chr3 | 19189694 | 19189765 | Hyper | tcga | KCNH8 |
| chr3 | 19190143 | 19190216 | Hyper | tcga | KCNH8 | chr3 | 22413665 | 22413694 | Hyper | tcga | ZNF385D |
| chr3 | 22413945 | 22413974 | Hyper | tcga | ZNF385D | chr3 | 24871002 | 24871245 | Hyper | tcga | |
| chr3 | 25469110 | 25469139 | Hyper | literature | RARB, LOC100130354 | chr3 | 25469377 | 25469406 | Hyper | literature | RARB, LOC100130354 |
| chr3 | 25469679 | 25469708 | Hyper | literature | LOC100130354, RARB | chr3 | 26664045 | 26664119 | Hyper | cancer_general | LRRC3B |
| chr3 | 26664389 | 26664755 | Hyper | tcga | LRRC3B | chr3 | 27754478 | 27754508 | Hyper | cancer_general | EOMES |
| chr3 | 27762336 | 27762650 | Hyper | cancer_general | EOMES | chr3 | 27762857 | 27762887 | Hyper | cancer_general | EOMES |
| chr3 | 27763566 | 27763595 | Hyper | liver_tcga | EOMES | chr3 | 27764457 | 27764503 | Hyper | cancer_general | EOMES |
| chr3 | 27765181 | 27765347 | Hyper | cancer_general | EOMES | chr3 | 27771497 | 27772004 | Hyper | cancer_general | EOMES |
| chr3 | 27772790 | 27772819 | Hyper | literature | EOMES | chr3 | 28610832 | 28617675 | Hyper | tcga, cancer_general | LINC00693, AX746710 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 32858353 | 32859693 | Hyper | tcga, cancer_general | TRIM71 | chr3 | 32860068 | 32860273 | Hyper | cancer_general | TRIM71 |
| chr3 | 33259904 | 33260776 | Hyper | tcga, cancer_general | SUSD5 | chr3 | 35680842 | 35680872 | Hyper | cancer_general | ARPP21 |
| chr3 | 36805815 | 36805863 | Hyper | cancer_general | | chr3 | 36806151 | 36806193 | Hyper | cancer_general | CTDSPL, BC040563 |
| chr3 | 37493519 | 37493621 | Hyper | esophageal | ITGA9 | chr3 | 37901923 | 37901953 | Hyper | blood | |
| chr3 | 38035767 | 38035989 | Hyper | cancer_general | VILL | chr3 | 38080685 | 38080925 | Hyper | cancer_general, liver_tcga | DLEC1, PLCD1 |
| chr3 | 38081148 | 38081271 | Hyper | cancer_general | DLEC1, PLCD1 | chr3 | 38182244 | 38182306 | Hyper | literature | MYD88, ACAA1 |
| chr3 | 38182626 | 38182655 | Hyper | literature | MYD88, ACAA1 | chr3 | 38690624 | 38690668 | Hyper | cancer_general | SCN5A |
| chr3 | 38691348 | 38691466 | Hyper | esophageal | SCN5A ENTPD3, ENTPD3-AS1 | chr3 | 39851772 | 39851814 | Hyper | cancer_general | MYRIP AK095242, AK311005, CTNNB1 |
| chr3 | 40428507 | 40428713 | Hyper | liver_tcga | | chr3 | 41266086 | 41266151 | Hyper | literature | |
| chr3 | 42814569 | 42814603 | Hyper | cancer_general | HIGD1A, CCDC13 | chr3 | 42947411 | 42947552 | Hyper | cancer_general | ZNF662 |
| chr3 | 44036260 | 44036330 | Hyper | cancer_general | | chr3 | 44036570 | 44036600 | Hyper | cancer_general | |
| chr3 | 44036820 | 44037203 | Hyper | tcga, cancer_general | | chr3 | 44037625 | 44037662 | Hyper | cancer_general | |
| chr3 | 44037874 | 44038646 | Hyper | cancer_general | | chr3 | 44039348 | 44040006 | Hyper | cancer_general | |
| chr3 | 44040511 | 44040553 | Hyper | cancer_general | | chr3 | 44040796 | 44041039 | Hyper | tcga, cancer_general | |
| chr3 | 44063434 | 44063872 | Hyper | cancer_general | ZKSCAN7 | chr3 | 44596479 | 44596509 | Hyper | cancer_general | ZKSCAN7 ZNF660, |
| chr3 | 44596716 | 44596809 | Hyper | cancer_general | | chr3 | 44626438 | 44626711 | Hyper | tcga, cancer_general | ZKSCAN7 |
| chr3 | 44726875 | 44727193 | Hyper | cancer_general | PTH1R | chr3 | 45187296 | 45187582 | Hyper | blood | CDCP1 |
| chr3 | 46924934 | 46924964 | Hyper | esophageal | | chr3 | 47144864 | 47144893 | Hyper | literature | |
| chr3 | 48693304 | 48694170 | Hyper | tcga, liver_tcga, cancer_general | | chr3 | 48698810 | 48699767 | Hyper | cancer_general, tcga | |
| chr3 | 49236845 | 49236874 | Hyper | literature | CCDC36, LOC646498 | chr3 | 49405953 | 49405982 | Hyper | literature | RHOA |
| chr3 | 49412883 | 49412987 | Hyper | literature | RHOA | chr3 | 49591832 | 49592076 | Hyper | esophageal | BSN, BSN-AS2 |
| chr3 | 49907093 | 49907130 | Hyper | esophageal | CAMKV | chr3 | 50243383 | 50243480 | Hyper | cancer_general | SLC38A3, GNAT1 |
| chr3 | 50374655 | 50374684 | Hyper | literature | RASSF1, TUSC2, AB209621, ZMYND10 | chr3 | 50374917 | 50374946 | Hyper | literature | AB209621, ZMYND10, NPRL2, RASSF1, TUSC2 |
| chr3 | 50375179 | 50375559 | Hyper | literature | TUSC2, AB209621, ZMYND10, NPRL2, RASSF1 | chr3 | 50377973 | 50378002 | Hyper | literature | AB209621, ZMYND10, NPRL2, RASSF1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 50378277 | 50378306 | Hyper | literature | AB209621, ZMYND10, NPRL2, CYB561D2, RASSF1 | chr3 | 50378512 | 50378541 | Hyper | literature | ZMYND10, NPRL2, CYB561D2, AB209621, RASSF1 PHF7, BAP1, DNAH1 |
| chr3 | 50402170 | 50402944 | Hyper | lung, cancer_general | Mir_324, TMEM115, CACNA2D2 | | | | | | |
| chr3 | 54155611 | 54155677 | Hyper | tcga | CACNA2D3 | chr3 | 54157381 | 54157450 | Hyper | cancer_general | CACNA2D3 |
| chr3 | 54157878 | 54157919 | Hyper | cancer_general | CACNA2D3 | chr3 | 55519219 | 55519253 | Hyper | esophageal | WNT5A |
| chr3 | 55523106 | 55523290 | Hyper | cancer_general | WNT5A | chr3 | 62304560 | 62304669 | Hyper | cancer_general | PTPRG-AS1, C3orf14 |
| chr3 | 62353371 | 62354049 | Hyper | cancer_general | FEZF2 | chr3 | 62354283 | 62354328 | Hyper | cancer_general | FEZF2 |
| chr3 | 62354625 | 62354914 | Hyper | cancer_general | FEZF2 | chr3 | 62354424 | 62354478 | Hyper | cancer_general | FEZF2 |
| chr3 | 62355774 | 62357347 | Hyper | cancer_general | FEZF2 | chr3 | 62357624 | 62357667 | Hyper | cancer_general | FEZF2 |
| chr3 | 62358161 | 62358194 | Hyper | cancer_general | FEZF2 | chr3 | 62358530 | 62358595 | Hyper | cancer_general | FEZF2 |
| chr3 | 62358858 | 62359011 | Hyper | cancer_general | FEZF2 | chr3 | 62359376 | 62359893 | Hyper | cancer_general | FEZF2 |
| chr3 | 62360302 | 62360560 | Hyper | cancer_general | FEZF2 | chr3 | 62362902 | 62363200 | Hyper | cancer_general | FEZF2 |
| chr3 | 62363626 | 62363693 | Hyper | cancer_general | FEZF2 | chr3 | 62363906 | 62364329 | Hyper | cancer_general | FEZF2 |
| chr3 | 62364702 | 62365154 | Hyper | cancer_general | FEZF2 | chr3 | 62861118 | 62861148 | Hyper | cancer_general | FEZF2 |
| chr3 | 63264139 | 63264169 | Hyper | cancer_general | SYNPR | chr3 | 68056904 | 68057145 | Hyper | liver_tcga, cancer_general | FAM19A1, AX747367 |
| chr3 | 68980931 | 68981113 | Hyper | cancer_general | | chr3 | 68981552 | 68981624 | Hyper | tcga, cancer_general | |
| chr3 | 69590939 | 69590969 | Hyper | cancer_general | | chr3 | 69591363 | 69592063 | Hyper | tcga, cancer_general | |
| chr3 | 71802518 | 71802622 | Hyper | tcga | GPR27, EIF4E3 | chr3 | 71803126 | 71803372 | Hyper | cancer_general | GPR27, EIF4E3 |
| chr3 | 71803643 | 71803821 | Hyper | cancer_general | GPR27, EIF4E3 | chr3 | 75956011 | 75956375 | Hyper | cancer_general | |
| chr3 | 79815522 | 79815557 | Hyper | cancer_general | EPHA6 | chr3 | 79816778 | 79817015 | Hyper | tcga, cancer_general | CADM2 |
| chr3 | 79817288 | 79817318 | Hyper | cancer_general | EPHA6 | chr3 | 85008553 | 85008708 | Hyper | cancer_general | |
| chr3 | 96532817 | 96532873 | Hyper | tcga | EPHA6 | chr3 | 96533383 | 96533458 | Hyper | cancer_general | EPHA6 |
| chr3 | 96534035 | 96534096 | Hyper | cancer_general | EPHA6 | chr3 | 98620891 | 98620980 | Hyper | esophageal | DCBLD2 |
| chr3 | 99594925 | 99595105 | Hyper | cancer_general | FILIP1L | chr3 | 101497841 | 101497996 | Hyper | liver_tcga, hepatobiliary | NXPE3 |
| chr3 | 112052203 | 112052419 | Hyper | tcga | CD200, BC041484 | chr3 | 117715549 | 117716473 | Hyper | cancer_general, tcga | FSTL1 |
| chr3 | 120004040 | 120004405 | Hyper | tcga, liver_tcga, cancer_general | | chr3 | 120169104 | 120169149 | Hyper | esophageal | |
| chr3 | 120169768 | 120169835 | Hyper | tcga | FSTL1 | chr3 | 120627317 | 120627453 | Hyper | cancer_general | STXBP5L |
| chr3 | 121902975 | 121903619 | Hyper | cancer_general | CASR | chr3 | 123167073 | 123167529 | Hyper | liver_tcga, cancer_general | |
| chr3 | 123167769 | 123167827 | Hyper | cancer_general | | chr3 | 124860671 | 124860700 | Hyper | literature | SLC12A8, MIR5092 |
| chr3 | 125898597 | 125899207 | Hyper | cancer_general | ALDH1L1-AS2, ALDH1L1 | chr3 | 125899525 | 125899962 | Hyper | cancer_general | ALDH1L1-AS2, ALDH1L1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 125932252 | 125932500 | Hyper | cancer_general | ALDH1L1-AS2 | chr3 | 126373520 | 126373704 | Hyper | blood | NUP210P1, TXNRD3 |
| chr3 | 126854699 | 126854796 | Hyper | cancer_general | RUVBL1, SEC61A1 | chr3 | 127634186 | 127634216 | Hyper | cancer_general | KBTBD12 |
| chr3 | 127794546 | 127794860 | Hyper | cancer_general |  | chr3 | 127795325 | 127795408 | Hyper | tcga | RUVBL1, SEC61A1 |
| chr3 | 128202447 | 128202477 | Hyper | cancer_general | GATA2 | chr3 | 128208903 | 128209232 | Hyper | cancer_general | GATA2 |
| chr3 | 128273993 | 128274611 | Hyper | tcga, pancreas, cancer_general |  | chr3 | 128417201 | 128417231 | Hyper | cancer_general |  |
| chr3 | 128720061 | 128720611 | Hyper | tcga, cancer_general | EFCC1, KIAA1257 | chr3 | 128720869 | 128721229 | Hyper | liver_tga, cancer_general | EFCC1, KIAA1257 |
| chr3 | 128764489 | 128764632 | Hyper | cancer_general | EFCC1 | chr3 | 129693108 | 129694299 | Hyper | liver_tcga, tcga, cancer_general | TRH |
| chr3 | 129694504 | 129694534 | Hyper | cancer_general | TRH | chr3 | 130064451 | 130064484 | Hyper | cancer_general | COL6A5 |
| chr3 | 130064818 | 130064848 | Hyper | cancer_general | COL6A5 | chr3 | 130236049 | 130236273 | Hyper | cancer_general |  |
| chr3 | 131754031 | 131754061 | Hyper | cancer_general |  | chr3 | 132757065 | 132757104 | Hyper | cancer_general | TMEM108 |
| chr3 | 133748140 | 133748245 | Hyper | blood | SLCO2A1 | chr3 | 133748481 | 133748576 | Hyper | blood | SLCO2A1 |
| chr3 | 134369646 | 134369855 | Hyper | tcga, cancer_general | KY | chr3 | 134514866 | 134514895 | Hyper | tcga | EPHB1 |
| chr3 | 134515128 | 134515369 | Hyper | cancer_general | EPHB1 | chr3 | 134515676 | 134516222 | Hyper | cancer_general | EPHB1 |
| chr3 | 136537642 | 136537730 | Hyper | cancer_general | SLC35G2 | chr3 | 136538585 | 136538815 | Hyper | tcga, cancer_general | SLC35G2 |
| chr3 | 136751641 | 136751809 | Hyper | tcga | SOX14 | chr3 | 137479233 | 137479302 | Hyper | cancer_general | SOX14 |
| chr3 | 137479601 | 137479687 | Hyper | cancer_general | SOX14 | chr3 | 137479980 | 137480764 | Hyper | cancer_general | SOX14 |
| chr3 | 137481170 | 137481315 | Hyper | cancer_general | BC038725, SOX14 | chr3 | 137481858 | 137482183 | Hyper | cancer_general | SOX14 |
| chr3 | 137483313 | 137483589 | Hyper | tcga, cancer_general | BC038725, SOX14 | chr3 | 137483848 | 137484002 | Hyper | cancer_general | BC038725, SOX14 |
| chr3 | 137484405 | 137484531 | Hyper | cancer_general | BC038725, SOX14 | chr3 | 137486029 | 137486310 | Hyper | cancer_general | BC038725, SOX14, |
| chr3 | 137486516 | 137486550 | Hyper | cancer_general | BC038725, SOX14 | chr3 | 137487964 | 137488021 | Hyper | cancer_general | BC038725, SOX14 |
| chr3 | 137488950 | 137491040 | Hyper | tcga, cancer_general | SOX14 | chr3 | 138067717 | 138067747 | Hyper | blood | MRAS |
| chr3 | 138153963 | 138153993 | Hyper | cancer_general | ESYT3 | chr3 | 138154340 | 138154377 | Hyper | cancer_general | ESYT3 |
| chr3 | 138374229 | 138374258 | Hyper | literature | PIK3CB | chr3 | 138655934 | 138656138 | Hyper | cancer_general | FOXL2, C3orf72, AK128202 |
| chr3 | 138656834 | 138656889 | Hyper | cancer_general | C3orf72, AK304483, AK128202, OFXL2 | chr3 | 138657414 | 138659099 | Hyper | tcga, cancer_general | AK128202, FOXL2, C3orf72, AK304483 |
| chr3 | 138662134 | 138662164 | Hyper | cancer_general | FOXL2, C3orf72, AK304483, AK128202 | chr3 | 138662382 | 138662448 | Hyper | cancer_general | FOXL2, C3orf72, AK304483, AK128202 |
| chr3 | 138662799 | 138662842 | Hyper | cancer_general | FOXL2, C3orf72, AK304483, AK128202 | chr3 | 138663613 | 138664165 | Hyper | cancer_general | C3orf72, AK304483, FOXL2, AK128202 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 138664408 | 138664489 | Hyper | cancer_general | AK304483, FOXL2, AK128202, C3orf72 | chr3 | 138664928 | 138665323 | Hyper | cancer_general | C3orf72, AK304483, FOXL2, AK128202 |
| chr3 | 138665562 | 138666294 | Hyper | cancer_general, liver_tcga, tcga | AK128202, C3orf72, AK304483, FOXL2 | chr3 | 138668742 | 138669387 | Hyper | cancer_general | AK128202, AK304483, C3orf72, FOXL2 |
| chr3 | 138679462 | 138679526 | Hyper | cancer_general | AK304483, C3orf72 | chr3 | 139258267 | 139258316 | Hyper | cancer_general | RBP1 |
| chr3 | 139653491 | 139653693 | Hyper | cancer_general | CLSTN2 | chr3 | 140769513 | 140769705 | Hyper | cancer_general | SPSB4 |
| chr3 | 140769908 | 140770829 | Hyper | tcga, pancreas, cancer_general | SPSB4 | chr3 | 140771305 | 140771335 | Hyper | cancer_general | SPSB4 |
| chr3 | 140771816 | 140771854 | Hyper | cancer_general | SPSB4 | chr3 | 141516389 | 141516719 | Hyper | cancer_general | GRK7 |
| chr3 | 142682273 | 142682392 | Hyper | tcga | PAQR9, KA093381 | chr3 | 142837980 | 142838370 | Hyper | tcga, cancer_general | CHST2 |
| chr3 | 142838621 | 142839036 | Hyper | tcga, cancer_general | CHST2 | chr3 | 142839539 | 142840236 | Hyper | tcga, colorectal, liver_tcga, cancer_general | CHST2 |
| chr3 | 145878665 | 145878695 | Hyper | blood | | chr3 | 147074457 | 147074487 | Hyper | cancer_general, liver_tcga, cancer_general | |
| chr3 | 147074974 | 147075006 | Hyper | cancer_general | | chr3 | 147077289 | 147077671 | Hyper | cancer_general | |
| chr3 | 147078959 | 147079188 | Hyper | cancer_general | | chr3 | 147087562 | 147087799 | Hyper | cancer_general | |
| chr3 | 147088440 | 147088523 | Hyper | cancer_general | | chr3 | 147088939 | 147089099 | Hyper | cancer_general | |
| chr3 | 147098431 | 147098470 | Hyper | cancer_general | ZIC4 | chr3 | 147105898 | 147106010 | Hyper | liver_tcga | ZIC4 |
| chr3 | 147108841 | 147109932 | Hyper | cancer_general | ZIC4 | chr3 | 147110145 | 147110683 | Hyper | cancer_general | ZIC4 |
| chr3 | 147110927 | 147111089 | Hyper | cancer_general | ZIC4 | chr3 | 147111545 | 147111674 | Hyper | literature, cancer_general | ZIC4 |
| chr3 | 147125697 | 147125726 | Hyper | literature | ZIC1, ZIC4 | chr3 | 147127037 | 147127067 | Hyper | cancer_general | ZIC1, ZIC4 |
| chr3 | 147127681 | 147127902 | Hyper | cancer_general | ZIC1, ZIC4 | chr3 | 147128287 | 147128326 | Hyper | cancer_general | ZIC1, ZIC4 |
| chr3 | 147136931 | 147137164 | Hyper | cancer_general | ZIC1 | chr3 | 147138768 | 147138856 | Hyper | cancer_general | ZIC1 |
| chr3 | 147139126 | 147139156 | Hyper | cancer_general | ZIC1 | chr3 | 147139374 | 147139528 | Hyper | cancer_general | ZIC1 |
| chr3 | 147142225 | 147142265 | Hyper | cancer_general | ZIC1 | chr3 | 148415427 | 148415644 | Hyper | cancer_general | AGTR1 |
| chr3 | 149374947 | 149375023 | Hyper | cancer_general | WWTR1-AS1, AK309441 | chr3 | 150802981 | 150803080 | Hyper | cancer_general | MED12L, CLRN1-AS1 |
| chr3 | 150804043 | 150804077 | Hyper | tcga | MED12L, CLRN1-AS1 | chr3 | 150804967 | 150805030 | Hyper | cancer_general | MED12L, CLRN1-AS1 |
| chr3 | 152553343 | 152553384 | Hyper | cancer_general | P2RY1 | chr3 | 152553658 | 152553725 | Hyper | tcga | P2RY1 |
| chr3 | 153838818 | 153838870 | Hyper | blood | ARHGEF26-AS1, ARHGEF26 | chr3 | 153839518 | 153840057 | Hyper | blood, cancer_general | ARHGEF26, ARHGEF26-AS1 |
| chr3 | 154146133 | 154146412 | Hyper | cancer_general | GPR149 | chr3 | 154146654 | 154146908 | Hyper | cancer_general | GPR149 |
| chr3 | 154797334 | 154797703 | Hyper | cancer_general, tcga, head_neck | MME | chr3 | 155463041 | 155463071 | Hyper | hepatobiliary | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 156008976 | 156009425 | Hyper | cancer_general | KCNAB1 | chr3 | 156534302 | 156534332 | Hyper | cancer_general | AK094480, LEKR1, AP2G4P4, LINC00886 |
| chr3 | 157155252 | 157155490 | Hyper | tcga, cancer_general | PTX3, VEPH1, Mir_584 | chr3 | 157155982 | 157156194 | Hyper | cancer_general, tcga | VEPH1, Mir_584, PTX3 |
| chr3 | 157812196 | 157812645 | Hyper | cancer_general | SHOX2 | chr3 | 157812912 | 157813070 | Hyper | cancer_general | SHOX2 |
| chr3 | 157813608 | 157813824 | Hyper | literature, cancer_general | SHOX2 | chr3 | 157814311 | 157814340 | Hyper | literature | SHOX2 |
| chr3 | 157815657 | 157815822 | Hyper | literature | SHOX2 | chr3 | 157820576 | 157820605 | Hyper | literature | SHOX2 |
| chr3 | 157821085 | 157821662 | Hyper | literature, cancer_general | RSRC1, SHOX2 | chr3 | 157821904 | 157822008 | Hyper | literature | RSRC1, SHOX2 |
| chr3 | 157823073 | 157823143 | Hyper | cancer_general | RSRC1, SHOX2 | chr3 | 157823464 | 157823493 | Hyper | literature | RSRC1, SHOX2 |
| chr3 | 157824133 | 157824231 | Hyper | literature | RSRC1, SHOX2 | chr3 | 157824495 | 157824871 | Hyper | literature, cancer_general | RSRC1, SHOX2 |
| chr3 | 157825176 | 157825408 | Hyper | cancer_general | RSRC1, SHOX2 | chr3 | 158288836 | 158288872 | Hyper | liver_tcga | MLF1, AK097794 |
| chr3 | 159756687 | 159756856 | Hyper | cancer_general |  | chr3 | 159944486 | 159944546 | Hyper | cancer_general | IFT80, C3orf80 |
| chr3 | 160168003 | 160168033 | Hyper | cancer_general |  | chr3 | 164912376 | 164912568 | Hyper | cancer_general | SLITRK3 |
| chr3 | 164912907 | 164913872 | Hyper | cancer_general |  | chr3 | 164914980 | 164915129 | Hyper | cancer_general | SLITRK3 |
| chr3 | 169376183 | 169376215 | Hyper | cancer_general | SLITRK3 | chr3 | 169376680 | 169376780 | Hyper | cancer_general |  |
| chr3 | 169378825 | 169379024 | Hyper | cancer_general |  | chr3 | 170136627 | 170136751 | Hyper | cancer_general | CLDN11 |
| chr3 | 170137667 | 170137772 | Hyper | cancer_general | CLDN11 | chr3 | 170302617 | 170302677 | Hyper | cancer_general | BC039437, SLC7A14 |
| chr3 | 170303087 | 170303129 | Hyper | cancer_general | BC039437, SLC7A14 | chr3 | 170303331 | 170303423 | Hyper | cancer_general | BC039437, SLC7A14 |
| chr3 | 170303639 | 170303844 | Hyper | liver_tcga, cancer_general | BC039437, SLC7A14 | chr3 | 1715127930 | 171527971 | Hyper | blood |  |
| chr3 | 172165443 | 172166627 | Hyper | cancer_general | GHSR, GU289929 | chr3 | 172166879 | 172167044 | Hyper | cancer_general | GHSR, GU289929 |
| chr3 | 172167297 | 172167327 | Hyper | cancer_general | GHSR, GU289929 | chr3 | 172167660 | 172167917 | Hyper | cancer_general | GU289929, GHSR |
| chr3 | 173115237 | 173115550 | Hyper | tcga | NLGN1 | chr3 | 173302542 | 173302684 | Hyper | cancer_general | NLGN1 |
| chr3 | 173302992 | 173303225 | Hyper | cancer_general | NLGN1 | chr3 | 178916711 | 178916959 | Hyper | literature | PIK3CA |
| chr3 | 178921537 | 178921568 | Hyper | literature | PIK3CA | chr3 | 178927966 | 178928094 | Hyper | literature | PIK3CA |
| chr3 | 178936059 | 178936111 | Hyper | literature | PIK3CA | chr3 | 178952004 | 178952105 | Hyper | literature | KCNMB3, PIK3CA |
| chr3 | 179168661 | 179169266 | Hyper | liver_tcga, colorectal, cancer_general | GNB4 | chr3 | 1797754178 | 179755372 | Hyper | cancer_general |  |
| chr3 | 180320256 | 180320294 | Hyper | esophageal | TTC14 | chr3 | 181413084 | 181413355 | Hyper | cancer_general | JA611300, SOX2-OT |
| chr3 | 181413742 | 181414330 | Hyper | tcga, cancer_general | JA611300, SOX2-OT | chr3 | 181420065 | 181420116 | Hyper | cancer_general | SOX2, JA611300, SOX2-OT |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 181420316 | 181420374 | Hyper | cancer_general | SOX2, JA611300, SOX2-OT | chr3 | 181421411 | 181422282 | Hyper | tcga, cancer_general | SOX2, JA611300, SOX2-OT |
| chr3 | 181422541 | 181422985 | Hyper | cancer_general | SOX2, JA611300, SOX2-OT | chr3 | 181428388 | 181428772 | Hyper | cancer_general | SOX2 |
| chr3 | 181430695 | 181430771 | Hyper | cancer_general | SOX2 | chr3 | 181437129 | 181437349 | Hyper | cancer_general | SOX2 |
| chr3 | 181438194 | 181438353 | Hyper | cancer_general | SOX2 | chr3 | 181440892 | 181441927 | Hyper | literature, cancer_general | SOX2 |
| chr3 | 181442145 | 181442410 | Hyper | lung, cancer_general | SOX2 | chr3 | 181443014 | 181443557 | Hyper | cancer_general | |
| chr3 | 181443760 | 181443861 | Hyper | cancer_general | | chr3 | 181444434 | 181445013 | Hyper | cancer_general | |
| chr3 | 181445369 | 181445464 | Hyper | cancer_general | | chr3 | 181445735 | 181445861 | Hyper | cancer_general | |
| chr3 | 183145412 | 183145618 | Hyper | literature, cancer_general | | chr3 | 183145931 | 183146025 | Hyper | literature | |
| chr3 | 183146397 | 183146435 | Hyper | literature | CHRD, THPO | chr3 | 183146648 | 183146677 | Hyper | literature | |
| chr3 | 184099417 | 184099446 | Hyper | literature | | chr3 | 184301734 | 184301772 | Hyper | cancer_general | EPHB3 |
| chr3 | 184319424 | 184319612 | Hyper | pancreas | | chr3 | 184319828 | 184319891 | Hyper | pancreas | |
| chr3 | 186078766 | 186078898 | Hyper | cancer_general | | chr3 | 186079204 | 186079331 | Hyper | cancer_general | |
| chr3 | 186080188 | 186080218 | Hyper | cancer_general | | chr3 | 186857152 | 186857607 | Hyper | tcga, cancer_general | |
| chr3 | 187387850 | 187388239 | Hyper | cancer_general | SST | chr3 | 192125828 | 192125858 | Hyper | cancer_general | FGF12 |
| chr3 | 192126146 | 192126863 | Hyper | cancer_general, tcga | FGF12 | chr3 | 192127354 | 192128074 | Hyper | cancer_general | FGF12 |
| chr3 | 192232097 | 192232175 | Hyper | cancer_general | FGF12 | chr3 | 192232452 | 192232570 | Hyper | cancer_general | FGF12 HRASLS, MGC2889 |
| chr3 | 192232834 | 192233150 | Hyper | cancer_general | FGF12 | chr3 | 192958725 | 192958968 | Hyper | liver_tcga | ATP13A3, GP5 |
| chr3 | 193776089 | 193776119 | Hyper | cancer_general | BC038368 | chr3 | 194120008 | 194120164 | Hyper | literature | AX746839, LINC00884 |
| chr3 | 194120934 | 194120963 | Hyper | literature | ATP13A3, GP5 | chr3 | 194208286 | 194208562 | Hyper | cancer_general | FAM43A |
| chr3 | 194407998 | 194408028 | Hyper | pancreas | FAM43A | chr3 | 194408375 | 194409021 | Hyper | liver_tcga, cancer_general, tcga | MFI2 |
| chr3 | 196255617 | 196255646 | Hyper | liver_tcga | BDH1 | chr3 | 196755958 | 196755987 | Hyper | liver_tcga | IQCG, RPL35A |
| chr3 | 197236945 | 197237111 | Hyper | hepatobiliary | | chr3 | 197677029 | 197677058 | Hyper | literature | LMLN, RPL35A |
| chr3 | 197686941 | 197687223 | Hyper | literature | LMLN, RPL35A FAM110C | chr3 | 197687694 | 197687723 | Hyper | literature | ACP1, SH3YL1 |
| chr2 | 46214 | 46450 | Hyper | blood | | chr2 | 264163 | 264204 | Hyper | liver_tcga | FAM150B |
| chr2 | 287580 | 287641 | Hyper | cancer_general | FAM150B | chr2 | 288404 | 288470 | Hyper | cancer_general | |
| chr2 | 468045 | 468078 | Hyper | cancer_general | | chr2 | 468299 | 468672 | Hyper | tcga, cancer_general | SNTG2 |
| chr2 | 945913 | 946000 | Hyper | cancer_general | SNTG2 | chr2 | 946208 | 946263 | Hyper | cancer_general | SNTG2 |
| chr2 | 946526 | 946610 | Hyper | cancer_general | SNTG2 | chr2 | 946896 | 947159 | Hyper | cancer_general | PXDN |
| chr2 | 1746614 | 1747210 | Hyper | cancer_general | PXDN | chr2 | 1747670 | 1748890 | Hyper | tcga, cancer_general | |
| chr2 | 3750947 | 3750977 | Hyper | liver_tcga | ALLC | chr2 | 3751335 | 3751439 | Hyper | cancer_general | ALLC |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 5831178 | 5831324 | Hyper | cancer_general | SOX11 | chr2 | 5831789 | 5831819 | Hyper | cancer_general | SOX11 |
| chr2 | 5832069 | 5832222 | Hyper | cancer_general | SOX11 | chr2 | 5832890 | 5834028 | Hyper | cancer_general, pancreas | SOX11 |
| chr2 | 5836085 | 5836253 | Hyper | cancer_general | SOX11 | chr2 | 5836548 | 5837071 | Hyper | tcga, cancer_general | SOX11 |
| chr2 | 5837278 | 5837414 | Hyper | cancer_general, pancreas, cancer_general | SOX11 | chr2 | 5866098 | 5866211 | Hyper | cancer_general | KLF11 |
| chr2 | 7571510 | 7571747 | Hyper | cancer_general | LOC100506274 | chr2 | 10182827 | 10182904 | Hyper | cancer_general | |
| chr2 | 10688874 | 10688904 | Hyper | cancer_general | LPIN1, NTSR2 | chr2 | 11052517 | 11052559 | Hyper | cancer_general | KCNF1 |
| chr2 | 11809957 | 11810117 | Hyper | cancer_general | | chr2 | 12858452 | 12858618 | Hyper | tcga, colorectal | TRIB2 |
| chr2 | 14772761 | 14772823 | Hyper | blood | FAM84A, AX747684 | chr2 | 14774281 | 14774567 | Hyper | blood | AX747684, FAM84A |
| chr2 | 17719688 | 17719812 | Hyper | cancer_general | VSNL1 | chr2 | 18059035 | 18059085 | Hyper | cancer_general | KCNS3 |
| chr2 | 18059781 | 18059841 | Hyper | pancreas | KCNS3 | chr2 | 19550214 | 19550244 | Hyper | cancer_general | OSR1, MIR4757 |
| chr2 | 19551322 | 19551366 | Hyper | cancer_general | OSR1, MIR4757 | chr2 | 19556318 | 19556672 | Hyper | cancer_general | OSR1, MIR4757 |
| chr2 | 19557068 | 19557098 | Hyper | cancer_general | OSR1, MIR4757 | chr2 | 19557685 | 19557727 | Hyper | blood | OSR1, MIR4757 |
| chr2 | 19558832 | 19558893 | Hyper | cancer_general | OSR1 | chr2 | 19561131 | 19561316 | Hyper | cancer_general | OSR1 |
| chr2 | 19561517 | 19561685 | Hyper | cancer_general | OSR1 | chr2 | 19563358 | 19563433 | Hyper | cancer_general | OSR1 |
| chr2 | 20068798 | 20068885 | Hyper | cancer_general | LINC00954 | chr2 | 20865636 | 20865927 | Hyper | tcga, cancer_general | GDF7 |
| chr2 | 25390994 | 25391212 | Hyper | cancer_general | POMC, EFR3B | chr2 | 25391684 | 25391725 | Hyper | cancer_general | POMC, EFR3B |
| chr2 | 25438821 | 25439465 | Hyper | tcga, liver_tcga, cancer_general | | chr2 | 26395447 | 26395556 | Hyper | liver_tcga | GAREML |
| chr2 | 26402030 | 26402060 | Hyper | cancer_general | GAREML | chr2 | 26407492 | 26408181 | Hyper | tcga, cancer_general | HADHA, GAREML |
| chr2 | 26521972 | 26522221 | Hyper | cancer_general | HADHB, GPR113 | chr2 | 26915763 | 26916259 | Hyper | cancer_general | KCNK3 |
| chr2 | 27070324 | 27070414 | Hyper | cancer_general | DPYSL5 | chr2 | 27071240 | 27071346 | Hyper | tcga | DPYSL5 |
| chr2 | 27072492 | 27072534 | Hyper | cancer_general | DPYSL5 | chr2 | 27072822 | 27072989 | Hyper | cancer_general | DPYSL5 |
| chr2 | 27665125 | 27665154 | Hyper | liver_tcga | KRTCAP3, IFT172, NRBP1 | chr2 | 27665506 | 27665711 | Hyper | liver_tcga | IFT172, KRTCAP3, NRBP1 |
| chr2 | 29033336 | 29033924 | Hyper | cancer_general | SPDYA, PPP1CB | chr2 | 29338084 | 29338969 | Hyper | colorectal, cancer_general | CLIP4 |
| chr2 | 29420483 | 29420512 | Hyper | literature | ALK | chr2 | 29432640 | 29432696 | Hyper | literature | ALK |
| chr2 | 29436844 | 29436888 | Hyper | literature | ALK | chr2 | 29443573 | 29443710 | Hyper | literature | ALK |
| chr2 | 29445198 | 29445482 | Hyper | literature | ALK | chr2 | 29446361 | 29446396 | Hyper | literature | ALK |
| chr2 | 30143304 | 30143492 | Hyper | cancer_general | | chr2 | 30144041 | 30144411 | Hyper | tcga, cancer_general | |
| chr2 | 30453714 | 30453941 | Hyper | cancer_general | LBH | chr2 | 31360306 | 31360831 | Hyper | colorectal | GALNT14 |
| chr2 | 31361089 | 31361118 | Hyper | tcga | GALNT14 | chr2 | 31361356 | 31361385 | Hyper | tcga | GALNT14 |
| chr2 | 31456682 | 31457039 | Hyper | tcga, esophageal, colorectal | EHD3, 5S_rRNA, CAPN14 | richr2 | 38302253 | 38302876 | Hyper | cancer_general | CYP1B1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 39187218 | 39187722 | Hyper | liver_tcga, cancer_general | LOC375196, ARHGEF33 | chr2 | 39893090 | 39893501 | Hyper | cancer_general | TMEM178A |
| chr2 | 39893972 | 39894059 | Hyper | Hyper | TMEM178A | chr2 | 40678603 | 40679620 | Hyper | tcga, cancer_general | SLC8A1 |
| chr2 | 42274595 | 42274633 | Hyper | tcga | PKDCC | chr2 | 42329431 | 42329666 | Hyper | tcga | |
| chr2 | 42720262 | 42720546 | Hyper | cancer_general | KCNG3, MTA3 | chr2 | 43019599 | 43019868 | Hyper | tcga | |
| chr2 | 43451909 | 43452327 | Hyper | lung | LOC100129726, THADA, ZFP36L2 | chr2 | 45028988 | 45029371 | Hyper | cancer_general | HAAO |
| chr2 | 45029682 | 45029712 | Hyper | cancer_general | SIX3 | chr2 | 45155125 | 45157711 | Hyper | cancer_general | SIX3 |
| chr2 | 45159956 | 45160267 | Hyper | cancer_general | SIX3 | chr2 | 45160596 | 45160634 | Hyper | cancer_general | SIX3 |
| chr2 | 45161663 | 45162112 | Hyper | cancer_general | SIX3 | chr2 | 45162394 | 45162481 | Hyper | cancer_general | SIX3 |
| chr2 | 45162751 | 45162913 | Hyper | cancer_general | SIX3 | chr2 | 45164663 | 45164693 | Hyper | cancer_general | SIX3 |
| chr2 | 45165564 | 45165594 | Hyper | cancer_general | SIX3 | chr2 | 45168803 | 45168833 | Hyper | cancer_general | SIX3 |
| chr2 | 45169446 | 45170029 | Hyper | liver_tcga, cancer_general | SIX3 | chr2 | 45171385 | 45171862 | Hyper | liver_tcga, cancer_general | SIX3 |
| chr2 | 45176601 | 45176768 | Hyper | cancer_general | SIX3 | chr2 | 45179620 | 45179650 | Hyper | cancer_general | SIX3 |
| chr2 | 45179939 | 45180203 | Hyper | cancer_general | SIX3 | chr2 | 45181520 | 45181672 | Hyper | cancer_general | SIX3 |
| chr2 | 45181887 | 45182001 | Hyper | cancer_general | SIX3 | chr2 | 45228618 | 45228730 | Hyper | cancer_general | SIX2 |
| chr2 | 45231320 | 45231396 | Hyper | cancer_general | SIX2 | chr2 | 45231805 | 45232131 | Hyper | tcga | SIX2 |
| chr2 | 45233385 | 45233586 | Hyper | tcga, cancer_general | SIX2 | chr2 | 45235594 | 45235926 | Hyper | cancer_general | SIX2 |
| chr2 | 45237673 | 45237795 | Hyper | cancer_general | SIX2 | chr2 | 45240548 | 45240784 | Hyper | liver_tcga, cancer_general | SIX2 |
| chr2 | 45241136 | 45241184 | Hyper | cancer_general | SIX2 | chr2 | 45395854 | 45395920 | Hyper | cancer_general | UNQ6975 |
| chr2 | 45396315 | 45396451 | Hyper | cancer_general | UNQ6975 | chr2 | 45396688 | 45396995 | Hyper | cancer_general | UNQ6975 |
| chr2 | 46526302 | 46526448 | Hyper | blood | EPAS1 | chr2 | 47748140 | 47748494 | Hyper | cancer_general | KCNK12 |
| chr2 | 47797043 | 47797818 | Hyper | tcga, cancer_general | KCNK12 | chr2 | 47798180 | 47798663 | Hyper | cancer_general | KCNK12 |
| chr2 | 47798954 | 47799109 | Hyper | cancer_general | KCNK12 | chr2 | 48982582 | 48982866 | Hyper | cancer_general | LHCGR |
| chr2 | 50573595 | 50573803 | Hyper | cancer_general | NRXN1 | chr2 | 50574121 | 50574859 | Hyper | tcga, cancer_general | NRXN1 |
| chr2 | 56149836 | 56149866 | Hyper | cancer_general | EFEMP1 | chr2 | 56150729 | 56151193 | Hyper | cancer_general | EFEMP1 |
| chr2 | 56410817 | 56410996 | Hyper | esophageal | CCDC85A, AK311113, AK295617 | chr2 | 56411691 | 56411733 | Hyper | tcga, esophageal | AK295617, CCDC85A, AK311113 |
| chr2 | 58656049 | 58656125 | Hyper | tcga, cancer_general | | chr2 | 60796587 | 60796646 | Hyper | cancer_general | |
| chr2 | 60797137 | 60797281 | Hyper | cancer_general | | chr2 | 62798343 | 62798386 | Hyper | cancer_general | |
| chr2 | 63275563 | 63275855 | Hyper | cancer_general | OTX1, LOC100132215 | chr2 | 63278962 | 63278992 | Hyper | cancer_general | |
| chr2 | 63280952 | 63281651 | Hyper | liver_tcga, cancer_general, tcga | OTX1, LOC100132215 | chr2 | 63282716 | 63282786 | Hyper | cancer_general | OTX1, LOC100132215 |
| chr2 | 63282998 | 63283027 | Hyper | literature | OTX1, LOC100132215 | chr2 | 63283952 | 63284146 | Hyper | liver_tcga, literature | OTX1, LOC100132215 |
| chr2 | 63284777 | 63284811 | Hyper | cancer_general | OTX1, LOC100132215 | chr2 | 63285081 | 63287368 | Hyper | liver_tcga, literature, cancer_general | OTX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 66652863 | 66652963 | Hyper | tcga | MEIS1, MEIS1-AS3 | chr2 | 66653238 | 66653496 | Hyper | cancer_general | MEIS1, EMIS1-AS3 |
| chr2 | 66653764 | 66653914 | Hyper | cancer_general | MEIS1, MEIS1-AS3 | chr2 | 66660650 | 66660888 | Hyper | tcga | MEIS1, AS3, MEIS1 |
| chr2 | 66662749 | 66662824 | Hyper | tcga | MEIS1, MEIS1-AS3 | chr2 | 66808525 | 66809361 | Hyper | tcga, cancer_general | MEIS1 |
| chr2 | 68546324 | 68546892 | Hyper | tcga, cancer_general | CNRIP1 | chr2 | 71503790 | 71503823 | Hyper | cancer_general | ZNF638 |
| chr2 | 71504103 | 71504148 | Hyper | cancer_general | ZNF638 | chr2 | 71680833 | 71680863 | Hyper | cancer_general | DYSF |
| chr2 | 71693374 | 71693593 | Hyper | tcga | DYSF | chr2 | 72374375 | 72374432 | Hyper | cancer_general | CYP26B1 |
| chr2 | 72374694 | 72374765 | Hyper | cancer_general | CYP26B1 | chr2 | 73145640 | 73145694 | Hyper | cancer_general | EMX1 |
| chr2 | 73145924 | 73146021 | Hyper | cancer_general | EMX1 | chr2 | 73147324 | 73148243 | Hyper | tcga, cancer_general | EMX1 |
| chr2 | 73150924 | 73150954 | Hyper | cancer_general | EMX1 | chr2 | 73151187 | 73151831 | Hyper | liver_tcga, cancer_general | EMX1 |
| chr2 | 73152683 | 73152754 | Hyper | cancer_general | EMX1 | chr2 | 73429523 | 73429614 | Hyper | cancer_general | NOTO |
| chr2 | 73429952 | 73430069 | Hyper | cancer_general | NOTO | chr2 | 73430322 | 73430743 | Hyper | cancer_general | NOTO |
| chr2 | 73518448 | 73518919 | Hyper | cancer_general | EGR4, U6, AK125051 | chr2 | 73519579 | 73519841 | Hyper | cancer_general | U6, EGR4, AK125051 |
| chr2 | 74426185 | 74426214 | Hyper | liver_tcga | MTHFD2 | chr2 | 74726744 | 74726774 | Hyper | cancer_general | LBX2-AS1, PCGF1, LBX2, TTC31 |
| chr2 | 74740852 | 74741387 | Hyper | liver_tcga, cancer_general | LBX2-AS1, TLX2, DQX1, PCGF1 | chr2 | 74741835 | 74741955 | Hyper | tcga, cancer_general | DQX1, TLX2, PCGF1, LBX2-AS1 |
| chr2 | 74742176 | 74743732 | Hyper | liver_tcga, cancer_general | LBX2, TLX2, PCGF1, LBX2-AS1 | chr2 | 74782081 | 74782271 | Hyper | liver_tcga, cancer_general | DOK1, MLAP, LOXL3 |
| chr2 | 75427040 | 75427114 | Hyper | cancer_general | CTNNA2, LRRTM1 | chr2 | 75427369 | 75427399 | Hyper | blood | EVA1A |
| chr2 | 75427930 | 75428177 | Hyper | cancer_general, tcga | CTNNA2, LRRTM1 | chr2 | 75720510 | 75720541 | Hyper | liver_tcga | |
| chr2 | 80529378 | 80529443 | Hyper | cancer_general | CTNNA2, LRRTM1 | chr2 | 80529662 | 80530022 | Hyper | cancer_general | CTNNA2, LRRTM1 |
| chr2 | 80530505 | 80530558 | Hyper | cancer_general | CTNNA2, LRRTM1 | chr2 | 80531725 | 80531755 | Hyper | cancer_general | CTNNA2, LRRTM1 |
| chr2 | 80549585 | 80549745 | Hyper | cancer_general | CTNNA2 | chr2 | 85107454 | 85107538 | Hyper | cancer_general | TRABD2A |
| chr2 | 85361317 | 85361609 | Hyper | cancer_general | TCF7L1 | chr2 | 86263223 | 86263270 | Hyper | liver_tcga | POLR1A |
| chr2 | 87016579 | 87016636 | Hyper | cancer_general | CD8A, RMND5A | chr2 | 87017796 | 87018396 | Hyper | cancer_general | RMND5A, CD8A |
| chr2 | 87036611 | 87036640 | Hyper | literature | CD8B | chr2 | 88751281 | 88751800 | Hyper | tcga, cancer_general | FOXI3 |
| chr2 | 88752055 | 88752285 | Hyper | liver_tcga, cancer_general | FOXI3 | chr2 | 88752603 | 88752785 | Hyper | cancer_general | FOXI3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 89064610 | 89065278 | Hyper | literature, cancer_general | ANKRD36BP2 | chr2 | 95663969 | 95664014 | Hyper | cancer_general | |
| chr2 | 95690747 | 95690793 | Hyper | literature, cancer_general | MAL | chr2 | 95691036 | 95691269 | Hyper | tcga, literature | MAL |
| chr2 | 95691530 | 95691769 | Hyper | literature, cancer_general | MAL | chr2 | 95691994 | 95692480 | Hyper | cancer_general, literature | MAL |
| chr2 | 96990898 | 96991316 | Hyper | literature, cancer_general | ITPRIPL1 | chr2 | 97193097 | 97193626 | Hyper | cancer_general | ARIDSA |
| chr2 | 98703323 | 98703475 | Hyper | liver_tcga | VWA3B | chr2 | 98703675 | 98703736 | Hyper | hepatobiliary | VWA3B |
| chr2 | 98962898 | 98962940 | Hyper | cancer_general | CNGA3 | chr2 | 98963329 | 98963599 | Hyper | cancer_general | CNGA3 |
| chr2 | 98963838 | 98964200 | Hyper | cancer_general | CNGA3 | chr2 | 98964596 | 98964645 | Hyper | cancer_general | CNGA3 |
| chr2 | 99439138 | 99439507 | Hyper | pancreas, cancer_general | KIAA1211L | chr2 | 99553391 | 99553656 | Hyper | tcga | KIAA1211L |
| chr2 | 100937836 | 100939155 | Hyper | tcga, colorectal, cancer_general | LONRF2 | chr2 | 101034242 | 101034293 | Hyper | tcga | CHST10 |
| chr2 | 101436632 | 101436708 | Hyper | blood | NPAS2 | chr2 | 101666893 | 101667004 | Hyper | liver_tcga | TBC1D8 |
| chr2 | 102091180 | 102091335 | Hyper | tcga | RFX8 | chr2 | 103236165 | 103236292 | Hyper | blood | SLC9A2 |
| chr2 | 105459081 | 105459518 | Hyper | cancer_general | LOC100506421 | chr2 | 105459908 | 105460599 | Hyper | cancer_general | LOC100506421 |
| chr2 | 105460921 | 105460951 | Hyper | cancer_general | LOC100506421 | chr2 | 105461187 | 105461243 | Hyper | cancer_general | LOC100506421 |
| chr2 | 105461564 | 105461896 | Hyper | cancer_general | LOC100506421 | chr2 | 105462165 | 105462222 | Hyper | cancer_general | POU3F3, LOC100506421 |
| chr2 | 105468791 | 105468908 | Hyper | cancer_general | LOC100506421, POU3F3 | chr2 | 105469645 | 105470091 | Hyper | cancer_general | POU3F3, LOC100506421 |
| chr2 | 105470350 | 105470840 | Hyper | tcga, literature, cancer_general, liver_tcga | POU3F3, LOC100506421 | chr2 | 105472231 | 105472845 | Hyper | cancer_general | AK095498, POU3F3, LOC100506421 |
| chr2 | 105473248 | 105473553 | Hyper | cancer_general | AK095498, POU3F3, LOC100506421 | chr2 | 105478762 | 105479089 | Hyper | cancer_general | AK095498, POU3F3 |
| chr2 | 105480530 | 105480595 | Hyper | cancer_general | AK095498, POU3F3 | chr2 | 105483655 | 105483719 | Hyper | cancer_general | AK095498 |
| chr2 | 105484450 | 105484522 | Hyper | cancer_general | AK095498 | chr2 | 105760981 | 105761037 | Hyper | cancer_general | |
| chr2 | 106681733 | 106681767 | Hyper | cancer_general | C2orf40 | chr2 | 106682012 | 106682098 | Hyper | cancer_general | C2orf40 |
| chr2 | 107103865 | 107103928 | Hyper | cancer_general | | chr2 | 107502600 | 107502815 | Hyper | tcga, cancer_general | ST6GAL2 |
| chr2 | 107503218 | 107503328 | Hyper | tcga, cancer_general | ST6GAL2 | chr2 | 107503532 | 107503561 | Hyper | tcga | ST6GAL2 |
| chr2 | 107503884 | 107504018 | Hyper | cancer_general | ST6GAL2 | chr2 | 109648080 | 109648222 | Hyper | tcga | SH3RF3, SH3RF3-AS1 |
| chr2 | 109745989 | 109746079 | Hyper | cancer_general | SH3RF3, SH3RF3-AS1 | chr2 | 109746289 | 109746477 | Hyper | cancer_general | SH3RF3, SH3RF3-AS1 |
| chr2 | 110370941 | 110371219 | Hyper | blood | SOWAHC | chr2 | 110873016 | 110873045 | Hyper | literature | NPHP1 |
| chr2 | 111875191 | 111875611 | Hyper | lung, cancer_general | AK125994, BCL2L11 | chr2 | 118876698 | 118876870 | Hyper | cancer_general | BCL2L11, AK125994 |
| chr2 | 112657033 | 112657092 | Hyper | cancer_general | MERTK | chr2 | 113594639 | 113594668 | Hyper | literature | IL1B |
| chr2 | 113931503 | 113931532 | Hyper | literature | PSD4 | chr2 | 114034892 | 114035180 | Hyper | cancer_general | PAX8 |
| chr2 | 114256978 | 114257137 | Hyper | cancer_general | FOXD4L1, CBWD2 | chr2 | 114261300 | 114261458 | Hyper | cancer_general | FOXD4L1, CBWD2 |
| chr2 | 115918661 | 115920534 | Hyper | tcga, cancer_general | LOC389023, DPP10 | chr2 | 118981151 | 118982497 | Hyper | cancer_general, tcga, lung | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 119067636 | 119068049 | Hyper | liver_tcga, cancer_general | | chr2 | 119532161 | 119532255 | Hyper | cancer_general | |
| chr2 | 119566239 | 119566272 | Hyper | tcga, cancer_general | EN1 | chr2 | 119591351 | 119591465 | Hyper | cancer_general | EN1 |
| chr2 | 119592588 | 119592777 | Hyper | cancer_general | | chr2 | 119592997 | 119593567 | Hyper | tcga, cancer_general | EN1 |
| chr2 | 119599926 | 119600031 | Hyper | cancer_general | EN1 | chr2 | 119600332 | 119600555 | Hyper | cancer_general | EN1 |
| chr2 | 119600949 | 119601061 | Hyper | cancer_general | EN1 | chr2 | 119602601 | 119603086 | Hyper | cancer_general | EN1 |
| chr2 | 119604032 | 119604158 | Hyper | cancer_general | EN1 | chr2 | 119604809 | 119604851 | Hyper | cancer_general | EN1 |
| chr2 | 119606135 | 119606558 | Hyper | cancer_general | EN1 | chr2 | 119606783 | 119606839 | Hyper | cancer_general | EN1 |
| chr2 | 119607176 | 119607411 | Hyper | cancer_general | EN1 | chr2 | 119607783 | 119607842 | Hyper | cancer_general | EN1 |
| chr2 | 119610844 | 119610969 | Hyper | cancer_general | EN1 | chr2 | 119611745 | 119611799 | Hyper | cancer_general | EN1 |
| chr2 | 119612324 | 119612354 | Hyper | cancer_general | EN1 | chr2 | 119614130 | 119614171 | Hyper | cancer_general | EN1 |
| chr2 | 119614780 | 119614852 | Hyper | cancer_general | EN1 | chr2 | 119615055 | 119615627 | Hyper | cancer_general | EN1 |
| chr2 | 119616155 | 119616582 | Hyper | cancer_general | | chr2 | 119616809 | 119616870 | Hyper | cancer_general | |
| chr2 | 119914720 | 119914752 | Hyper | cancer_general | C1QL2 | chr2 | 119916049 | 119916082 | Hyper | cancer_general | C1QL2 |
| chr2 | 119916299 | 119916595 | Hyper | tcga, cancer_general | C1QL2 | chr2 | 120281646 | 120281693 | Hyper | cancer_general | SCTR |
| chr2 | 120281923 | 120281953 | Hyper | cancer_general | SCTR | chr2 | 121200390 | 121200433 | Hyper | cancer_general | |
| chr2 | 121345081 | 121345111 | Hyper | cancer_general | | chr2 | 121411888 | 121412153 | Hyper | liver_tcga, literature | |
| chr2 | 122176232 | 122176293 | Hyper | liver_tcga | CLASP1 | chr2 | 124782333 | 124782458 | Hyper | cancer_general | CNTNAP5 |
| chr2 | 124782692 | 124783097 | Hyper | tcga, cancer_general | CNTNAP5 | chr2 | 127413918 | 127414036 | Hyper | cancer_general | GYPC |
| chr2 | 127783043 | 127783257 | Hyper | liver_tcga, cancer_general | | chr2 | 127863601 | 127863725 | Hyper | breast | BIN1 |
| chr2 | 127976467 | 127976672 | Hyper | cancer_general | CYP27C1 | chr2 | 128421866 | 128421947 | Hyper | cancer_general | |
| chr2 | 129494389 | 129494421 | Hyper | head_neck | | chr2 | 130763584 | 130763623 | Hyper | cancer_general | AK127124, AX746725 |
| chr2 | 130971321 | 130971520 | Hyper | liver_tcga, literature, cancer_general | | chr2 | 131594989 | 131595019 | Hyper | pancreas | |
| chr2 | 131673756 | 131673785 | Hyper | literature | ARHGEF4, AK127124, ARHGEF4 | chr2 | 131720852 | 131721253 | Hyper | cancer_general | ARHGEF4 |
| chr2 | 131721461 | 131721949 | Hyper | cancer_general | ARHGEF4 | chr2 | 131792260 | 131793131 | Hyper | cancer_general, tcga | ARHGEF4 |
| chr2 | 132088770 | 132088828 | Hyper | cancer_general | | chr2 | 132121661 | 132121829 | Hyper | tcga | TRNA, WTH3DI |
| chr2 | 132152361 | 132152495 | Hyper | cancer_general | LOC389043, TRNA_Pseudo | chr2 | 132182790 | 132183089 | Hyper | cancer_general | |
| chr2 | 132767457 | 132767707 | Hyper | cancer_general | | chr2 | 132795240 | 132795419 | Hyper | cancer_general | |
| chr2 | 132795670 | 132795728 | Hyper | cancer_general | | chr2 | 133014598 | 133014638 | Hyper | cancer_general | |
| chr2 | 133015275 | 133015323 | Hyper | cancer_general | JA668105, MIR663B, ANKRD30BL | chr2 | 133062326 | 133062389 | Hyper | cancer_general | ANKRD30BL, JA668105, MIR663B, AK094599 |
| chr2 | 133426249 | 133426279 | Hyper | cancer_general | NCKAP5, LYPD1 | chr2 | 133426637 | 133426674 | Hyper | cancer_general | LYPD1, NCKAP5 |
| chr2 | 137522445 | 137522475 | Hyper | cancer_general | THSD7B | chr2 | 137523825 | 137523855 | Hyper | tcga, cancer_general | THSD7B |
| chr2 | 139536937 | 139537145 | Hyper | cancer_general | NXPH2 | chr2 | 139537443 | 139537865 | Hyper | cancer_general | NXPH2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 142887871 | 142888066 | Hyper | tcga | GTDC1 | chr2 | 142888348 | 142888418 | Hyper | cancer_general | ZEB2_AS1_1, ZEB2-AS1, ZEB2_AS1_3, ZEB2_AS1_4, AK124806, ZEB2 |
| chr2 | 144694367 | 144695135 | Hyper | tcga, colorectal cancer_general | | chr2 | 145273404 | 145273751 | Hyper | cancer_general | ZEB2-AS1, ZEB2_AS1_3, ZEB2_AS1_4, AK124806, ZEB2 |
| chr2 | 145274186 | 145274455 | Hyper | tcga, cancer_general | AK124806, ZEB2, ZEB 2_AS1_1, ZEB2-AS1, ZEB2_AS1_3, ZEB2_AS1_4 | chr2 | 145274814 | 145275213 | Hyper | tcga, cancer_general | |
| chr2 | 145282119 | 145282149 | Hyper | pancreas | ZEB2_AS1_4, ZEB2_AS1_3, ZEB2-AS1, ZEB2_AS1_1 | | | | | | |
| chr2 | 149633744 | 149633965 | Hyper | cancer_general | JB137817, KIF5C | chr2 | 149633097 | 149633399 | Hyper | tcga, cancer_general | JB137817, KIF5C |
| chr2 | 151342903 | 151343277 | Hyper | blood | RND3 | chr2 | 149645496 | 149645894 | Hyper | cancer_general | JB137817, KIF5C |
| chr2 | 154334272 | 154334665 | Hyper | cancer_general | RPRM | chr2 | 154333535 | 154333567 | Hyper | cancer_general | RPRM |
| chr2 | 154728042 | 154728482 | Hyper | cancer_general, liver_tcga, tcga | GALNT13 | chr2 | 154335139 | 154335271 | Hyper | cancer_general | RPRM |
| | | | | | | chr2 | 154729044 | 154729240 | Hyper | tcga, cancer_general | GALNT13 |
| chr2 | 154729559 | 154729589 | Hyper | cancer_general | GALNT13 | chr2 | 155555038 | 155555361 | Hyper | tcga | KCNJ3 |
| chr2 | 157176592 | 157176717 | Hyper | cancer_general | NR4A2 | chr2 | 157177003 | 157178310 | Hyper | cancer_general | NR4A2 |
| chr2 | 157178646 | 157178731 | Hyper | liver_tcga | NR4A2 | chr2 | 160761070 | 160761556 | Hyper | tcga, liver_tcga | LY75 |
| chr2 | 162272989 | 162274338 | Hyper | lung, literature, cancer_general | TBR1 | chr2 | 162274717 | 162274866 | Hyper | cancer_general | TBR1 |
| chr2 | 162275146 | 162275802 | Hyper | tcga, cancer_general | TBR1 | chr2 | 162280003 | 162280956 | Hyper | liver_tcga, cancer_general | TBR1 |
| chr2 | 162283365 | 162284055 | Hyper | liver_tcga, cancer_general | TBR1 | chr2 | 164593096 | 164593137 | Hyper | cancer_general | FIGN |
| chr2 | 168150069 | 168150245 | Hyper | cancer_general | LOC440925, SP5, AK023515 | chr2 | 168150751 | 168150945 | Hyper | cancer_general | AK023515, LOC440925, SP5 |
| chr2 | 171570082 | 171570428 | Hyper | cancer_general | | chr2 | 171570684 | 171570733 | Hyper | cancer_general | |
| chr2 | 171571264 | 171571315 | Hyper | blood | AK023515, SP5, LOC440925 | chr2 | 171571889 | 171572068 | Hyper | blood | AK023515, SP5, LOC440925 |
| chr2 | 171670349 | 171670467 | Hyper | cancer_general | GAD1 | chr2 | 171671487 | 171671881 | Hyper | cancer_general | GAD1 |
| chr2 | 171673873 | 171673939 | Hyper | blood | GAD1 | chr2 | 171674739 | 171675066 | Hyper | liver_tcga, cancer_general | GAD1 |
| chr2 | 171675361 | 171675592 | Hyper | cancer_general | GAD1 | chr2 | 171676684 | 171676785 | Hyper | cancer_general | GAD1 |
| chr2 | 172945124 | 172945167 | Hyper | cancer_general | DLX1, METAP1D | chr2 | 172945896 | 172946211 | Hyper | cancer_general | DLX1, METAP1D |
| chr2 | 172947717 | 172948314 | Hyper | cancer_general | METAP1D, DLX1 | chr2 | 172948709 | 172948751 | Hyper | cancer_general | DLX1, METAP1D |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 172949186 | 172949711 | Hyper | cancer_general | DLX1, METAP1D | chr2 | 172951596 | 172951689 | Hyper | cancer_general | DLX1, METAP1D |
| chr2 | 172952521 | 172953046 | Hyper | cancer_general | DLX1, METAP1D | chr2 | 172955444 | 172955545 | Hyper | cancer_general | DLX2, DLX1, METAP1D |
| chr2 | 172957907 | 172958066 | Hyper | cancer_general | DLX2, DLX1 | chr2 | 172961398 | 172961598 | Hyper | cancer_general | DLX2, DLX1 |
| chr2 | 172964821 | 172965802 | Hyper | cancer_general | DLX2 | chr2 | 172966264 | 172966442 | Hyper | cancer_general | DLX2 |
| chr2 | 172972735 | 172973218 | Hyper | cancer_general | DLX2 | chr2 | 173099784 | 173099814 | Hyper | cancer_general | DLX2 |
| chr2 | 173100262 | 173100430 | Hyper | cancer_general |  | chr2 | 175190871 | 175192468 | Hyper | lung, cancer_general |  |
| chr2 | 175193268 | 175193823 | Hyper | lung, cancer_general | SP9, LOC285084 | chr2 | 175195831 | 175195861 | Hyper | cancer_general | SP9, LOC285084 |
| chr2 | 175196432 | 175196575 | Hyper | cancer_general | SP9, LOC285084 | chr2 | 175197089 | 175197119 | Hyper | cancer_general | SP9, LOC285084 |
| chr2 | 175198752 | 175198966 | Hyper | literature, cancer_general | 176971712LOC285084 | chr2 | 175199527 | 175199935 | Hyper | literature, cancer_general | SP9, LOC285084 |
| chr2 | 175200140 | 175202652 | Hyper | lung, cancer_general | SP9, LOC285084 | chr2 | 175204174 | 175204204 | Hyper | cancer_general | SP9, LOC285084, CIR1 |
| chr2 | 175204786 | 175205799 | Hyper | cancer_general | LOC285084, CIR1, SP9 | chr2 | 175206833 | 175207028 | Hyper | cancer_general | CIR1, SP9 |
| chr2 | 175207228 | 175207258 | Hyper | cancer_general | CIR1, SP9 | chr2 | 175207536 | 175207653 | Hyper | tcga | CIR1, SP9 |
| chr2 | 175208311 | 175209135 | Hyper | tcga | CIR1, SP9 | chr2 | 155547041 | 155547140 | Hyper | cancer_general | WIPF1 |
| chr2 | 155547384 | 155547413 | Hyper | cancer_general | WIPF1 | chr2 | 176940167 | 176940315 | Hyper | cancer_general | EVX2 |
| chr2 | 176943269 | 176943568 | Hyper | cancer_general | EVX2 | chr2 | 176943861 | 176943902 | Hyper | cancer_general | EVX2 |
| chr2 | 176944426 | 176945784 | Hyper | cancer_general | EVX2 | chr2 | 176946578 | 176947389 | Hyper | cancer_general | EVX2 |
| chr2 | 176947748 | 176947903 | Hyper | cancer_general | HOXD13, EVX2 | chr2 | 176948599 | 176948742 | Hyper | literature, cancer_general | HOXD13, EVX2 |
| chr2 | 176949045 | 176949075 | Hyper | cancer_general | HOXD13, EVX2 | chr2 | 176949695 | 176949869 | Hyper | cancer_general | HOXD13, EVX2 |
| chr2 | 176950142 | 176950258 | Hyper | cancer_general | HOXD13, EVX2 | chr2 | 176956558 | 176956640 | Hyper | literature, cancer_general | HOXD13, HOXD12, EVX2 |
| chr2 | 176956921 | 176957199 | Hyper | cancer_general | HOXD13, HOXD12, EVX2 | chr2 | 176957497 | 176957919 | Hyper | cancer_general | HOXD13, HOXD12, EVX2 |
| chr2 | 176958138 | 176958489 | Hyper | cancer_general | HOXD12, HOXD13, EVX2 | chr2 | 176959289 | 176959511 | Hyper | cancer_general | HOXD12, HOXD11, HOXD13 |
| chr2 | 176963448 | 176963522 | Hyper | cancer_general | HOXD12, HOXD11, HOXD13 | chr2 | 176964085 | 176964151 | Hyper | literature, cancer_general | HOXD11, HOXD13, HOXD12 |
| chr2 | 176964369 | 176965492 | Hyper | literature, cancer_general | HOXD12, HOXD11, HOXD13 | chr2 | 176969463 | 176969908 | Hyper | cancer_general | HOXD13, HOXD12, HOXD11 |
| chr2 | 176971628 | 176971712 | Hyper | pancreas | HOXD11, HOXD10, HOXD12 | chr2 | 176972557 | 176972586 | Hyper | liver_tcga | HOXD11, HOXD12, HOXD10 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 176976029 | 176976188 | Hyper | tcga, cancer_general | HOXD10, HOXD11 | chr2 | 176980750 | 176981506 | Hyper | cancer_general, literature | HOXD9, HOXD11, HOXD10 |
| chr2 | 176982584 | 176982627 | Hyper | cancer_general | HOXD10, HOXD11, HOXD9, AX747372 | chr2 | 176986715 | 176986848 | Hyper | cancer_general | AX747372, HOXD8, HOXD10, HOXD9 |
| chr2 | 176987057 | 176988304 | Hyper | cancer_general, literature | HOXD10, HOXD9, AX747372, HOXD8 | chr2 | 176993074 | 176993103 | Hyper | literature | BC047605, HOXD9, HOXD10, AX747372, HOXD8, HOXD-AS2 |
| chr2 | 176993547 | 176993855 | Hyper | tcga, literature, cancer_general | AX747372, HOXD9, HOXD10, HOXD8, HOXD-AS2, BC047605 | chr2 | 176994124 | 176994764 | Hyper | liver_tcga, cancer_general | AX747372, HOXD9, HOXD10, HOXD8, HOXD-AS2, BC047605 |
| chr2 | 176995072 | 176995668 | Hyper | cancer_general | HOXD8, AX747372, HOXD9, HOXD-AS2, BC047605 | chr2 | 177001102 | 177001976 | Hyper | tcga, lung, cancer_general | BC047605, HOXD-AS2, HOXD8, AX747372 |
| chr2 | 177004566 | 177004658 | Hyper | cancer_general | BC047605, HOXD-AS2, HOXD8 | chr2 | 177014981 | 177015010 | Hyper | literature | MIR10B, HOXD4, BC047605 |
| chr2 | 177027425 | 177027454 | Hyper | literature | HOXD3, HOXD4 | chr2 | 177030149 | 177030228 | Hyper | liver_tcga | HOXD3, HOXD-AS1 |
| chr2 | 177042984 | 177043515 | Hyper | tcga, cancer_general | HOXD1, HOXD-AS1, HOXD3 | chr2 | 177053276 | 177053816 | Hyper | cancer_general | HOXD1, HOXD-AS1 |
| chr2 | 177054113 | 177054351 | Hyper | cancer_general | HOXD1, HOXD-AS1 | chr2 | 177503048 | 177503077 | Hyper | literature | LOC375295 |
| chr2 | 177503581 | 177503610 | Hyper | literature | LOC375295 | chr2 | 178098791 | 178098967 | Hyper | literature | NFE2L2 |
| chr2 | 182321397 | 182321637 | Hyper | cancer_general | ITGA4 | chr2 | 182321839 | 182322170 | Hyper | cancer_general | ITGA4 |
| chr2 | 182322379 | 182323042 | Hyper | cancer_general | ITGA4 | chr2 | 182451522 | 182451551 | Hyper | literature | CERKL |
| chr2 | 182542903 | 182542933 | Hyper | cancer_general | NEUROD1 | chr2 | 182543321 | 182543418 | Hyper | cancer_general | NEUROD1 |
| chr2 | 182543764 | 182543925 | Hyper | cancer_general | NEUROD1 | chr2 | 182545211 | 182545275 | Hyper | cancer_general | NEUROD1 |
| chr2 | 182545539 | 182545694 | Hyper | cancer_general | NEUROD1 | chr2 | 182545986 | 182546085 | Hyper | cancer_general | NEUROD1 |
| chr2 | 182546435 | 182546465 | Hyper | cancer_general | NEUROD1 | chr2 | 182547385 | 182547613 | Hyper | cancer_general | NEUROD1 |
| chr2 | 182547937 | 182548161 | Hyper | cancer_general | NEUROD1 | chr2 | 182549088 | 182549134 | Hyper | cancer_general | NEUROD1 |
| chr2 | 182549337 | 182549454 | Hyper | cancer_general | NEUROD1 | chr2 | 182550094 | 182550124 | Hyper | cancer_general | NEUROD1 |
| chr2 | 182819048 | 182819216 | Hyper | cancer_general | NEUROD1 | chr2 | 183731294 | 183731524 | Hyper | cancer_general | FRZB |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 183731809 | 183732076 | Hyper | tcga, cancer_general, literature | FRZB | chr2 | 185462869 | 185462980 | Hyper | cancer_general | ZNF804A |
| chr2 | 185463193 | 185463817 | Hyper | tcga, cancer_general | ZNF804A | chr2 | 186603488 | 186603518 | Hyper | cancer_general | FSIP2, BC039382 |
| chr2 | 188419047 | 188419204 | Hyper | cancer_general | TFPI | chr2 | 189157427 | 189157688 | Hyper | cancer_general, blood | MIR561, GULP1 |
| chr2 | 190708790 | 190708819 | Hyper | literature | PMS1 | chr2 | 193059025 | 193060067 | Hyper | cancer_general, tcga | TMEFF2 |
| chr2 | 193060385 | 193060441 | Hyper | cancer_general | TMEFF2 | chr2 | 193060683 | 193060891 | Hyper | tcga, cancer_general | TMEFF2 |
| chr2 | 193061388 | 193061480 | Hyper | cancer_general | TMEFF2 | chr2 | 198267345 | 198267374 | Hyper | literature | SnR39B, SF3B1 |
| chr2 | 198650984 | 198651076 | Hyper | liver_tcga | BOLL | chr2 | 200326590 | 200326735 | Hyper | liver_tcga, literature | SATB2-AS1, AK056625, AK125157 |
| chr2 | 200327287 | 200327565 | Hyper | liver_tcga, cancer_general | AK125157, SATB2-AS1, AK056625 | chr2 | 200328747 | 200329668 | Hyper | cancer_general | SATB2-AS1, AK056625, AK125157 |
| chr2 | 200333775 | 200333834 | Hyper | cancer_general | AK056625, SATB2-AS1, AK125157 | chr2 | 200334976 | 200335952 | Hyper | cancer_general, liver_tcga | AK056625, SATB2-AS1 |
| chr2 | 201172444 | 201172480 | Hyper | blood | SPATS2L | chr2 | 201450556 | 201450707 | Hyper | cancer_general | AOX1, SGOL2 |
| chr2 | 201450947 | 201451040 | Hyper | tcga | SGOL2, AOX1 | chr2 | 202097078 | 202097143 | Hyper | literature | CASP8 |
| chr2 | 202098936 | 202098965 | Hyper | literature | CASP8 | chr2 | 202101190 | 202101219 | Hyper | literature | CASP8 |
| chr2 | 202122459 | 202122683 | Hyper | literature | CASP8 | chr2 | 202899862 | 202899891 | Hyper | liver_tcga | FZD7 |
| chr2 | 206551056 | 206551378 | Hyper | tcga, cancer_general | NRP2 | chr2 | 207139072 | 207139102 | Hyper | cancer_general | ZDBF2, BC028329 |
| chr2 | 207139347 | 207139605 | Hyper | liver_tcga, cancer_general | ZDBF2, BC028329 | chr2 | 207307528 | 207307562 | Hyper | cancer_general | ADAM23 |
| chr2 | 207308802 | 207308857 | Hyper | cancer_general | ADAM23 | chr2 | 207506691 | 207507181 | Hyper | cancer_general | DYTN, LOC200726 |
| chr2 | 208635534 | 208635774 | Hyper | tcga, cancer_general | FZD5 | chr2 | 208989208 | 208989382 | Hyper | liver_tcga, literature | CRYGD, LOC100507443, CRYGC |
| chr2 | 209113097 | 209113126 | Hyper | literature | IDH1-AS1, IDH1 | chr2 | 209271322 | 209271551 | Hyper | cancer_general | PTH2R |
| chr2 | 210636335 | 210636892 | Hyper | cancer_general, tcga | UNC80 | chr2 | 212248428 | 212248457 | Hyper | literature | ERBB4 |
| chr2 | 212288927 | 212288956 | Hyper | literature | ERBB4 | chr2 | 212295683 | 212295820 | Hyper | literature | ERBB4 |
| chr2 | 212530120 | 212530149 | Hyper | literature | ERBB4 | chr2 | 212537902 | 212537994 | Hyper | literature | ERBB4 |
| chr2 | 212566811 | 212566840 | Hyper | literature | ERBB4 | chr2 | 212578292 | 212578321 | Hyper | literature | ERBB4 |
| chr2 | 212587132 | 212587161 | Hyper | literature | ERBB4 | chr2 | 213401235 | 213401339 | Hyper | cancer_general | ERBB4 |
| chr2 | 213401613 | 213401947 | Hyper | cancer_general | ERBB4 | chr2 | 213403110 | 213403337 | Hyper | tcga, cancer_general | ERBB4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 215275823 | 215275852 | Hyper | literature | VWC2L | chr2 | 217559296 | 217559326 | Hyper | cancer_general | IGFBP5 |
| chr2 | 217559966 | 217559999 | Hyper | cancer_general | IGFBP5 | chr2 | 218770207 | 218770270 | Hyper | liver_tcga, tcga, cancer_general | TNS1 |
| chr2 | 218806147 | 218806302 | Hyper | cancer_general | TNS1 | chr2 | 219736151 | 219736691 | Hyper | | WNT10A, WNT6 |
| chr2 | 219828049 | 219828117 | Hyper | cancer_general | CDK5R2 | chr2 | 219847462 | 219847555 | Hyper | cancer_general | CRYBA2, FEV, LINC00608 |
| chr2 | 219848809 | 219849001 | Hyper | cancer_general | CRYBA2, FEV, LINC00608 | chr2 | 219857723 | 219857756 | Hyper | cancer_general | CRYBA2, FEV, MIR375, LOC100129175, CCDC108 |
| chr2 | 220173989 | 220174296 | Hyper | literature, cancer_general | | chr2 | 220196354 | 220196567 | Hyper | cancer_general | RESP18 |
| chr2 | 220223098 | 220223128 | Hyper | cancer_general | DES | chr2 | 220223648 | 220223703 | Hyper | cancer_general | |
| chr2 | 220283338 | 220283519 | Hyper | cancer_general | SPEG | chr2 | 220299588 | 220300059 | Hyper | cancer_general | SPEG, DES |
| chr2 | 220313621 | 220313692 | Hyper | cancer_general | GMPPA | chr2 | 220349029 | 220349706 | Hyper | cancer_general | |
| chr2 | 220361447 | 220361531 | Hyper | cancer_general | | chr2 | 220416379 | 220416513 | Hyper | cancer_general | CHPF, OBSL1, MIR3132, TMEM198 |
| chr2 | 220416848 | 220417649 | Hyper | liver_tcga, cancer_general | CHPF, OBSL1, MIR3132, TMEM198 | chr2 | 222435773 | 222435863 | Hyper | cancer_general | AX747413, EPHA4 |
| chr2 | 223155722 | 223156188 | Hyper | cancer_general | CCDC140, DD413687, PAX3 | chr2 | 223158730 | 223159453 | Hyper | cancer_general, lung | CCDC140, DD413687, PAX3 |
| chr2 | 223159823 | 223160065 | Hyper | tcga, cancer_general | CCDC140, DD413687, PAX3 | chr2 | 223160342 | 223160379 | Hyper | cancer_general | CCDC140, DD413687, PAX3 |
| chr2 | 223161247 | 223162063 | Hyper | tcga, cancer_general | CCDC140, DD413687, PAX3 | chr2 | 223162779 | 223163535 | Hyper | cancer_general | CCDC140, DD413687, PAX3 |
| chr2 | 223163768 | 223163954 | Hyper | cancer_general | CCDC140, DD413687, PAX3 | chr2 | 223164534 | 223164883 | Hyper | cancer_general, literature | CCDC140, DD413687, PAX3 |
| chr2 | 223165434 | 223165832 | Hyper | cancer_general, lung | DD413687, PAX3, CCDC140 | chr2 | 223166449 | 223166721 | Hyper | cancer_general | CCDC140, DD413687, PAX3 |
| chr2 | 223167389 | 223167573 | Hyper | cancer_general | PAX3, CCDC140, DD413687 | chr2 | 223168437 | 223168852 | Hyper | cancer_general | CCDC140, DD413687, PAX3 |
| chr2 | 223169640 | 223169864 | Hyper | lung, cancer_general | CCDC140, DD413687 | chr2 | 223170375 | 223170434 | Hyper | cancer_general | CCDC140, DD413687, PAX3 |
| chr2 | 223171109 | 223171180 | Hyper | cancer_general | CCDC140, DD413687, PAX3 | chr2 | 223172337 | 223172367 | Hyper | lung | CCDC140, DD413687, PAX3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 223172924 | 223173173 | Hyper | cancer_general | CCDC140, DD413687, PAX3 | chr2 | 223175663 | 223176181 | Hyper | cancer_general, lung | LOC440934, CCDC140 |
| chr2 | 223176456 | 223176983 | Hyper | cancer_general | LOC440934, CCDC140 | chr2 | 223177315 | 223177610 | Hyper | cancer_general | LOC440934, CCDC140 |
| chr2 | 224903260 | 224903440 | Hyper | esophageal | SERPINE2 | chr2 | 224903690 | 224903755 | Hyper | esophageal | SERPINE2 |
| chr2 | 224904108 | 224904237 | Hyper | esophageal | SERPINE2 | chr2 | 228029418 | 228029531 | Hyper | tcga, esophageal | COL4A3 |
| chr2 | 228736215 | 228736473 | Hyper | liver_tcga, cancer_general, tcga | DAW1 | chr2 | 229046107 | 229046503 | Hyper | cancer_general | SPHKAP |
| chr2 | 231693216 | 231693268 | Hyper | cancer_general | CAB39 | chr2 | 232394970 | 232395061 | Hyper | liver_tcga | NMUR1 |
| chr2 | 232479822 | 232479938 | Hyper | tcga | | chr2 | 232791704 | 232792012 | Hyper | tcga, cancer_general | NPPC |
| chr2 | 233350208 | 233351394 | Hyper | cancer_general | ECEL1 | chr2 | 233352025 | 233352853 | Hyper | cancer_general | ECEL1 |
| chr2 | 233498710 | 233499297 | Hyper | tcga, cancer_general | EFHD1 | chr2 | 233404545 | 233404575 | Hyper | cancer_general | ARL4C |
| chr2 | 235860746 | 235860808 | Hyper | blood | SH3BP4 | chr2 | 235861389 | 235861533 | Hyper | blood | SH3BP4 |
| chr2 | 236402771 | 236403013 | Hyper | blood | AGAP1 | chr2 | 236403270 | 236403736 | Hyper | blood | AGAP1 |
| chr2 | 236578362 | 236578677 | Hyper | blood | AGAP1 | chr2 | 237072413 | 237073030 | Hyper | tcga, cancer_general | GBX2 |
| chr2 | 237073354 | 237073414 | Hyper | cancer_general | GBX2 | chr2 | 237076725 | 237076815 | Hyper | liver_tcga | GBX2 |
| chr2 | 237077562 | 237077608 | Hyper | cancer_general | GBX2 | chr2 | 237077846 | 237078348 | Hyper | cancer_general | GBX2 |
| chr2 | 237080264 | 237080294 | Hyper | cancer_general | GBX2 | chr2 | 237081341 | 237081826 | Hyper | cancer_general | GBX2 |
| chr2 | 237082117 | 237082720 | Hyper | cancer_general | GBX2 | chr2 | 237086349 | 237086468 | Hyper | cancer_general | GBX2 |
| chr2 | 237145422 | 237145601 | Hyper | tcga, cancer_general | ASB18 | chr2 | 237416216 | 237416429 | Hyper | cancer_general | IQCA1 |
| chr2 | 238395291 | 238395356 | Hyper | cancer_general | MLPH | chr2 | 238395906 | 238395961 | Hyper | blood | MLPH |
| chr2 | 238535895 | 238536114 | Hyper | tcga | LRRFIP1 | chr2 | 238864644 | 238864913 | Hyper | cancer_general | LOC643387, HES6, LOC151174 |
| chr2 | 239072648 | 239072692 | Hyper | pancreas | FAM132B, ILKAP | chr2 | 239140025 | 239140249 | Hyper | cancer_general | |
| chr2 | 239149844 | 239149951 | Hyper | tcga | PER2, HES6, LOC643387, LOC151174 | chr2 | 239755164 | 239755194 | Hyper | cancer_general | TWIST2 |
| chr2 | 239755736 | 239755778 | Hyper | cancer_general | TWIST2 | chr2 | 239756373 | 239756648 | Hyper | cancer_general | TWIST2 |
| chr2 | 239757636 | 239757824 | Hyper | cancer_general | TWIST2 | chr2 | 239758078 | 239758144 | Hyper | cancer_general | TWIST2 |
| chr2 | 239758345 | 239758394 | Hyper | cancer_general | TWIST2 | chr2 | 241393200 | 241393469 | Hyper | cancer_general | MIR149, PP14571, GPC1 |
| chr2 | 241497411 | 241497554 | Hyper | liver_tcga | DUSP28, ANKMY1 | chr2 | 241758377 | 241758819 | Hyper | literature, cancer_general | KIF1A |
| chr2 | 241759597 | 241759694 | Hyper | cancer_general | KIF1A | chr2 | 241760149 | 241760178 | Hyper | literature | |
| chr2 | 241760494 | 241760523 | Hyper | literature | KIF1A | chr2 | 241771165 | 241771257 | Hyper | cancer_general | KIF1A |
| chr2 | 242549849 | 242549957 | Hyper | tcga | | HPV16 | 111 | 140 | Hyper | virus | |
| HPV16 | 367 | 396 | Hyper | virus | | HPV16 | 623 | 652 | Hyper | virus | |
| HPV16 | 879 | 908 | Hyper | virus | | HPV16 | 1135 | 1164 | Hyper | virus | |
| HPV16 | 1391 | 1420 | Hyper | virus | | HPV16 | 1647 | 1676 | Hyper | virus | |
| HPV16 | 1903 | 1932 | Hyper | virus | | HPV16 | 2159 | 2188 | Hyper | virus | |
| HPV16 | 2415 | 2444 | Hyper | virus | | HPV16 | 2671 | 2700 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HPV16 | 2927 | 2956 | Hyper | virus | | HPV16 | 3183 | 3212 | Hyper | virus | |
| HPV16 | 3439 | 3468 | Hyper | virus | | HPV16 | 3695 | 3724 | Hyper | virus | |
| HPV16 | 3951 | 3980 | Hyper | virus | | HPV16 | 4207 | 4236 | Hyper | virus | |
| HPV16 | 4463 | 4492 | Hyper | virus | | HPV16 | 4719 | 4748 | Hyper | virus | |
| HPV16 | 4975 | 5004 | Hyper | virus | | HPV16 | 5231 | 5260 | Hyper | virus | |
| HPV16 | 5487 | 5516 | Hyper | virus | | HPV16 | 5743 | 5772 | Hyper | virus | |
| HPV16 | 5999 | 6028 | Hyper | virus | | HPV16 | 6255 | 6284 | Hyper | virus | |
| HPV16 | 6511 | 6540 | Hyper | virus | | HPV16 | 6767 | 6796 | Hyper | virus | |
| HPV16 | 7023 | 7052 | Hyper | virus | | HPV16 | 7279 | 7308 | Hyper | virus | |
| HPV16 | 7535 | 7564 | Hyper | virus | | chr17 | 1082884 | 1083002 | Hyper | liver_tcga | SLC43A2 |
| chr17 | 1173996 | 1174413 | Hyper | cancer_general | TUSC5, BHLHA9 | chr17 | 1494550 | 1494613 | Hyper | pancreas | CLUH |
| chr17 | 1959468 | 1959520 | Hyper | cancer_general | MIR132, HIC1, SMG6, AX747853, MIR212 | chr17 | 2607905 | 2607986 | Hyper | liver_tcga | |
| chr17 | 3438914 | 3438959 | Hyper | cancer_general | TRPV3 | chr17 | 3658490 | 3658519 | Hyper | liver_tcga | KIF1C, CAMTA2, INCA1 |
| chr17 | 4544607 | 4544710 | Hyper | cancer_general | ALOX15 | chr17 | 4891276 | 4891305 | Hyper | tcga | ZNF232, ZFP3 |
| chr17 | 4891527 | 4891556 | Hyper | tcga | KIF1C, INCA1, CAMTA2, ZNF232, ZFP3 | chr17 | 5000428 | 5000790 | Hyper | cancer_general | |
| chr17 | 5001032 | 5001061 | Hyper | liver_tcga | SLC13A5 | chr17 | 5019637 | 5019761 | Hyper | liver_tcga | ZNF232, USP6 |
| chr17 | 6616637 | 6616686 | Hyper | cancer_general | FBXO39, XAF1 | chr17 | 6616911 | 6617192 | Hyper | liver_tcga, cancer_general | SLC13A5 |
| chr17 | 6679190 | 6679296 | Hyper | cancer_general | CHRNB1, FGF11, TMEM102 | chr17 | 6946107 | 6946141 | Hyper | cancer_general | SLC16A11, SLC16A13 |
| chr17 | 7348885 | 7348997 | Hyper | head_neck | | chr17 | 7555117 | 7555425 | Hyper | tcga | TP53, ATP1B2 |
| chr17 | 7572957 | 7573018 | Hyper | literature | HV941478, HV941442, HV941433, HV941434, HV941486, HV941440, HV941444, HV941430, HV941431, HV941428, TP53, HV941429 | chr17 | 7573968 | 7574028 | Hyper | literature | HV941428, HV941434, TP53, HV941478, HV941442, HV941444, HV941433, HV941486, HV941429, HV941440, HV941430, HV941431 |
| chr17 | 7576847 | 7577167 | Hyper | literature | HV941430, HV941431, HV941428, TP53, HV941429, | chr17 | 7577504 | 7577604 | Hyper | literature | HV941429, HV941440, HV941431, HV941478, TP53, HV941440, HV941478, HV941442, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 7578164 | 7578570 | Hyper | literature | HV941440, HV941478, HV941442, HV941433, HV941434, HV941486, HV941444 | chr17 | 7579285 | 7579880 | Hyper | literature | HV941430, HV941428, HV941433, HV941431, HV941444, HV941486, HV941434 |
| chr17 | 7906254 | 7906535 | Hyper | tcga, cancer_general | GUCY2D | | | | | | WRAP53, HV941442, HV941440, HV941429, HV941428, TP53, HV941430, HV941486, HV941434, HV941433, HV941431, HV941444, ARHGEF15 |
| chr17 | 8534493 | 8534582 | Hyper | esophageal | HV941478, HV941444, TP53, HV941429, HV941434, HV941440, HV941442, HV941430, HV941486, HV941428, HV941433, HV941431 | chr17 | 8230335 | 8230694 | Hyper | cancer_general, tcga | PIK3R5 |
| chr17 | 8906266 | 8906518 | Hyper | cancer_general | | chr17 | 8868620 | 8869385 | Hyper | cancer_general, tcga | |
| | | | | | | chr17 | 8906993 | 8907575 | Hyper | cancer_general | |
| chr17 | 8926060 | 8926263 | Hyper | tcga, cancer_general | NTN1 | chr17 | 10101084 | 10101984 | Hyper | cancer_general | SHISA6 |
| chr17 | 10102415 | 10102665 | Hyper | tcga, cancer_general | | chr17 | 11144167 | 11144320 | Hyper | literature | MIR744, MAP2K4 |
| chr17 | 11144926 | 11144989 | Hyper | cancer_general | SHISA6 | chr17 | 11984693 | 11984722 | Hyper | literature | |
| chr17 | 11998944 | 11998973 | Hyper | literature | | chr17 | 12013726 | 12013755 | Hyper | literature | |
| chr17 | 12016550 | 12016630 | Hyper | literature | | chr17 | 12028618 | 12028647 | Hyper | literature | |
| chr17 | 13503972 | 13504195 | Hyper | cancer_general | HS3ST3A1 | chr17 | 13504557 | 13504681 | Hyper | cancer_general | HS3ST3A1 |
| chr17 | 13504975 | 13505188 | Hyper | tcga, cancer_general | HS3ST3A1 | chr17 | 13505418 | 13505572 | Hyper | cancer_general, tcga | HS3ST3A1 |
| chr17 | 14201041 | 14201181 | Hyper | cancer_general | HS3ST3B1, MGC12916, HS3ST3B1 | chr17 | 14204212 | 14204242 | Hyper | cancer_general, esophageal | MGC12916, HS3ST3B1 |
| chr17 | 14204527 | 14204620 | Hyper | esophageal | MGC12916, HS3ST3B1 | chr17 | 15245050 | 15245139 | Hyper | cancer_general | TEKT3 |
| chr17 | 16284630 | 16285065 | Hyper | ovarian | UBB | chr17 | 16570699 | 16570794 | Hyper | cancer_general | TBC1D28, CCDC144B |
| chr17 | 17398404 | 17398440 | Hyper | pancreas | MED9, RASD1 | chr17 | 18538154 | 18538275 | Hyper | cancer_general | |
| chr17 | 26554634 | 26554705 | Hyper | cancer_general | PYY2 | chr17 | 27038649 | 27038900 | Hyper | cancer_general, tcga | RAB34, NARR, RPL23A, SNORD42B, PROCA1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 27044770 | 27044800 | Hyper | colorectal | SNORD42A, SNORD4B, NARR, RAB34, PROCA1, RPL23A, SNORD42B, SNORD4A, TLCD1 | chr17 | 27332453 | 27332660 | Hyper | cancer_general | SEZ6 |
| chr17 | 27940359 | 27940911 | Hyper | cancer_general | CORO6, ANKRD13B | chr17 | 28562701 | 28562765 | Hyper | cancer_general | SLC6A4 |
| chr17 | 29249717 | 29249930 | Hyper | cancer_general | ADAP2 | chr17 | 29298080 | 29298581 | Hyper | tcga, liver_tcga, hepatobiliary | DPRXP4, RNF135 |
| chr17 | 29508761 | 29508790 | Hyper | literature | NF1 | chr17 | 29541527 | 29541556 | Hyper | literature | NF1 |
| chr17 | 29562732 | 29562761 | Hyper | literature | NF1 | chr17 | 29718215 | 29718269 | Hyper | cancer_general | RAB11FIP4 |
| chr17 | 29719187 | 29719242 | Hyper | cancer_general | RAB11FIP4 | chr17 | 31618425 | 31619319 | Hyper | cancer_general | ASIC2 |
| chr17 | 31619951 | 31620026 | Hyper | cancer_general | ASIC2 | chr17 | 32484020 | 32484049 | Hyper | literature | TMEM132E, C17orf102 |
| chr17 | 32906379 | 32906636 | Hyper | tcga | TMEM132E, C17orf102 | chr17 | 32906987 | 32907146 | Hyper | tcga | TMEM132E, C17orf102 |
| chr17 | 32907652 | 32907753 | Hyper | cancer_general | TMEM132E, C17orf102, TMEM132E | chr17 | 32908132 | 32908374 | Hyper | colorectal, cancer_general | ZNF830, CCT6B |
| chr17 | 32908647 | 32908931 | Hyper | esophageal | CCT6B, ZNF830 | chr17 | 33288229 | 33288351 | Hyper | esophageal | SLFN11 |
| chr17 | 33288890 | 33288988 | Hyper | cancer_general | BC084573, LHX1 | chr17 | 33672916 | 33672986 | Hyper | cancer_general | BC084573, LHX1 |
| chr17 | 35165645 | 35165691 | Hyper | cancer_general | LHX1, BC084573 | chr17 | 35165986 | 35166016 | Hyper | cancer_general | BC084573, LHX1 |
| chr17 | 35285542 | 35285666 | Hyper | cancer_general | LHX1, BC084573 | chr17 | 35290388 | 35290655 | Hyper | cancer_general | LHX1, BC084573 |
| chr17 | 35291320 | 35291354 | Hyper | tcga, cancer_general | LHX1, BC084573 | chr17 | 35291829 | 35292626 | Hyper | literature | BC084573, LHX1 |
| chr17 | 35293704 | 35294154 | Hyper | cancer_general | AATF, LHX1 | chr17 | 35294461 | 35294505 | Hyper | cancer_general | AATF, LHX1, BC084573 |
| chr17 | 35295047 | 35295160 | Hyper | cancer_general | AATF, LHX1, BC084573 | chr17 | 35296143 | 35296292 | Hyper | cancer_general | BC084573, AATF, LHX1 |
| chr17 | 35296728 | 35296888 | Hyper | cancer_general, literature | LHX1, BC084573, AATF | chr17 | 35297619 | 35298153 | Hyper | cancer_general | AATF, LHX1, BC084573 |
| chr17 | 35299251 | 35300854 | Hyper | liver_tcga | SYNRG, DUSP14 | chr17 | 35303340 | 35303535 | Hyper | tcga, cancer_general | HNF1B |
| chr17 | 35872722 | 35872861 | Hyper | cancer_general | HNF1B | chr17 | 36103021 | 36103326 | Hyper | cancer_general | SRCIN1 |
| chr17 | 36103571 | 36103601 | Hyper | cancer_general | CACNB1, ARL5C | chr17 | 36104120 | 36104779 | Hyper | tcga | STAC2 |
| chr17 | 36105223 | 36105596 | Hyper | tcga, cancer_general | STAC2 | chr17 | 36715772 | 36715967 | Hyper | cancer_general | RPL19 |
| chr17 | 37321186 | 37321972 | Hyper | tcga, literature, cancer_general | NEUROD2 | chr17 | 37366337 | 37366552 | Hyper | literature | STAC2 |
| chr17 | 37381011 | 37381850 | Hyper | lung | | chr17 | 37382146 | 37382248 | Hyper | cancer_general | NEUROD2 |
| chr17 | 37757153 | 37757217 | Hyper | | | chr17 | 37760488 | 37760561 | | | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 37761997 | 37762334 | Hyper | cancer_general | NEUROD2 | chr17 | 37868190 | 37868294 | Hyper | literature | ERBB2 |
| chr17 | 37879568 | 37879615 | Hyper | literature | MIR4728, MIEN1, ERBB2 | chr17 | 37880205 | 37880276 | Hyper | literature | MIR4728, MIEN1, ERBB2 |
| chr17 | 37880971 | 37881018 | Hyper | literature | MIR4728, MIEN1, ERBB2 | chr17 | 37881318 | 37881631 | Hyper | literature | MIR4728, MIEN1, ERBB2 |
| chr17 | 38347560 | 38347624 | Hyper | cancer_general | RAPGEFL1 | chr17 | 38474363 | 38474502 | Hyper | literature | RARA |
| chr17 | 38497616 | 38497645 | Hyper | literature | RARA | chr17 | 38498083 | 38498112 | Hyper | literature | RARA, GJD3, |
| chr17 | 38504087 | 38504116 | Hyper | literature | RARA | chr17 | 38510555 | 38510584 | Hyper | liver_tcga | RARA |
| chr17 | 40332943 | 40333226 | Hyper | tcga, esophageal | HCRT, GHDC, KCNH4 | chr17 | 40400867 | 40401031 | Hyper | cancer_general | STAT5B |
| chr17 | 40464278 | 40464317 | Hyper | cancer_general | AK024535, STAT3, AK092965, STAT5A | chr17 | 40464517 | 40464607 | Hyper | cancer_general | AK024535, STAT3, AK092965, STAT5A |
| chr17 | 40474467 | 40474496 | Hyper | literature | AK092965, STAT3, AK024535 | chr17 | 40826197 | 40826226 | Hyper | liver_tcga | CNTNAP1, PLEKHH3, TUBG2, CCR10 |
| chr17 | 40837022 | 40837051 | Hyper | liver_tcga | PLEKHH3, CNTNAP1, CCR10 | chr17 | 40837287 | 40837383 | Hyper | liver_tcga | CCR10, PLEKHH3, CNTNAP1 |
| chr17 | 40838982 | 40839022 | Hyper | liver_tcga | CNTNAP1, CCR10, PLEKHH3 | chr17 | 41177394 | 41177459 | Hyper | tcga | RND2, VAT1 |
| chr17 | 41197714 | 41197743 | Hyper | literature | BRCA1 | chr17 | 41201163 | 41201192 | Hyper | literature | BRCA1 |
| chr17 | 41203073 | 41203102 | Hyper | literature | BRCA1 | chr17 | 41209064 | 41209114 | Hyper | literature | BRCA1 |
| chr17 | 41215890 | 41215961 | Hyper | literature | BRCA1 | chr17 | 41267731 | 41267775 | Hyper | literature | NBR2, BRCA1 |
| chr17 | 41276031 | 41276075 | Hyper | literature | BRCA1, NBR2 | chr17 | 41277259 | 41277721 | Hyper | literature | NBR2, BRCA1 |
| chr17 | 41791460 | 41791489 | Hyper | tcga | | chr17 | 42030329 | 42030756 | Hyper | liver_tcga, cancer_general | PYY |
| chr17 | 42061336 | 42061381 | Hyper | blood | | chr17 | 42082522 | 42082557 | Hyper | cancer_general | NAGS, TMEM101 |
| chr17 | 42084361 | 42084626 | Hyper | tcga | TMEM101, NAGS | chr17 | 42092190 | 42092220 | Hyper | breast | TMEM101, NAGS |
| chr17 | 42393842 | 42394024 | Hyper | cancer_general | SLC25A39, RUNDC3A, AK055254 | chr17 | 42402884 | 42402917 | Hyper | hepatobiliary | SLC25A39, RUNDC3A |
| chr17 | 42635295 | 42635760 | Hyper | tcga, cancer_general | FZD2 | chr17 | 42733711 | 42733884 | Hyper | cancer_general, liver_tcga | C17orf104 |
| chr17 | 42907564 | 42907951 | Hyper | esophageal, cancer_general | | chr17 | 43037399 | 43037429 | Hyper | cancer_general | C1QL1 |
| chr17 | 43044658 | 43044688 | Hyper | cancer_general | C1QL1 | chr17 | 43044999 | 43045116 | Hyper | liver_tcga, cancer_general | C1QL1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 43046260 | 43046385 | Hyper | tcga | C1QL1 | chr17 | 43047436 | 43047751 | Hyper | liver_tcga, cancer_general | C1QL1 |
| chr17 | 43339109 | 43339333 | Hyper | cancer_general | MAP3K14-AS1, MAP3K14, SPATA32 | chr17 | 43339609 | 43339899 | Hyper | cancer_general | MAP3K14, MAP3K14-AS1, SPATA32 |
| chr17 | 43974256 | 43974358 | Hyper | cancer_general | MAPT-IT1, MAPT | chr17 | 45331014 | 45331313 | Hyper | esophageal | ITGB3 |
| chr17 | 45810850 | 45811341 | Hyper | tcga, cancer_general | TBX21 | chr17 | 45867315 | 45867460 | Hyper | tcga | |
| chr17 | 46124991 | 46125061 | Hyper | colorectal | NFE2L1 | chr17 | 46619298 | 46619327 | Hyper | tcga | HOXB3, HOXB2, HOXB-AS1 |
| chr17 | 46619540 | 46619569 | Hyper | tcga | HOXB2, HOXB-AS1, HOXB3 | chr17 | 46620494 | 46621094 | Hyper | cancer_general | HOXB-AS1, HOXB3, HOXB2 |
| chr17 | 46621353 | 46621458 | Hyper | cancer_general | HOXB-AS1, HOXB3, HOXB2 | chr17 | 46621856 | 46621909 | Hyper | cancer_general | HOXB3, HOXB-AS1, HOXB2 |
| chr17 | 46655148 | 46655178 | Hyper | lung | MIR10A, HOXB4, HOXB3 | chr17 | 46655435 | 46656704 | Hyper | tcga, cancer_general, literature | MIR10A, HOXB4, HOXB3 |
| chr17 | 46659429 | 46659859 | Hyper | cancer_general | HOXB-AS3, HOXB5, MIR10A, HOXB4, HOXB3 | chr17 | 46663743 | 46663887 | Hyper | tcga, cancer_general | HOXB5, HOXB6, MIR10A, HOXB4, HOXB-AS3 |
| chr17 | 46674873 | 46674970 | Hyper | cancer_general | HOXB7, HOXB-AS3, HOXB6, HOXB5 | chr17 | 46675170 | 46675600 | Hyper | lung, cancer_general | HOXB7, HOXB-AS3, HOXB6, HOXB5 |
| chr17 | 46690467 | 46690664 | Hyper | cancer_general | HOXB9, HOXB8, HOXB7 | chr17 | 46691505 | 46691592 | Hyper | cancer_general | HOXB9, HOXB8, HOXB7 |
| chr17 | 46691805 | 46692110 | Hyper | tcga, lung, cancer_general | HOXB9, HOXB8, HOXB7 | chr17 | 46692439 | 46692606 | Hyper | tcga | HOXB9, HOXB8, HOXB7 |
| chr17 | 46710946 | 46711065 | Hyper | literature, cancer_general, tcga | MIR196A1, HOXB9 | chr17 | 46711281 | 46711375 | Hyper | tcga, literature, cancer_general | MIR196A1, HOXB9 |
| chr17 | 46713959 | 46714072 | Hyper | cancer_general | MIR196A1 | chr17 | 46795641 | 46797582 | Hyper | cancer_general | PRAC, HOXB-AS5, MIR3185, HOXB13 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 46799625 | 4679989 6 | Hyper | literature, cancer_general | HOXB-AS5, MIR3185, HOXB13, PRAC | chr17 | 46800601 | 46800668 | Hyper | cancer_general | MIR3185, HOXB13, HOXB-AS5, PRAC |
| chr17 | 46800961 | 46801416 | Hyper | lung, cancer_general | HOXB-AS5, PRAC, MIR3185, HOXB13 | chr17 | 46802459 | 46803286 | Hyper | cancer_general | HOXB13, MIR3185, HOXB-AS5, PRAC |
| chr17 | 46804107 | 46804428 | Hyper | cancer_general | HOXB13, MIR3185, HOXB-AS5 | chr17 | 46810416 | 46810958 | Hyper | cancer_general | HOXB-AS5, HOXB13, MIR3185 |
| chr17 | 46811354 | 46811541 | Hyper | cancer_general | HOXB13, MIR3185, HOXB-AS5 | chr17 | 46816282 | 46816877 | Hyper | cancer_general | |
| chr17 | 46824224 | 46825054 | Hyper | cancer_general | | chr17 | 46825284 | 46825514 | Hyper | cancer_general | |
| chr17 | 46826930 | 46827127 | Hyper | cancer_general | | chr17 | 46827330 | 46827756 | Hyper | cancer_general | |
| chr17 | 46829498 | 46829579 | Hyper | cancer_general | | chr17 | 46829979 | 46830110 | Hyper | cancer_general | TTLL6 |
| chr17 | 46831779 | 46832639 | Hyper | cancer_general | TTLL6 | chr17 | 47072805 | 47073465 | Hyper | cancer_general | IGF2BP1 |
| chr17 | 47073988 | 47074228 | Hyper | cancer_general | IGF2BP1 | chr17 | 47074561 | 47074895 | Hyper | cancer_general, tcga | IGF2BP1 |
| chr17 | 47075160 | 47075364 | Hyper | tcga, cancer_general | IGF2BP1 | chr17 | 47075715 | 47076055 | Hyper | tcga, cancer_general | IGF2BP1 |
| chr17 | 47574090 | 47574149 | Hyper | colorectal | NGFR | chr17 | 47865514 | 47865555 | Hyper | cancer_general | KAT7, FAM117A |
| chr17 | 47987525 | 47987619 | Hyper | cancer_general | DLX4 | chr17 | 47987930 | 47988114 | Hyper | cancer_general | DLX4 |
| chr17 | 48041152 | 48041320 | Hyper | cancer_general | DLX4 | chr17 | 48041672 | 48041721 | Hyper | cancer_general | DLX4 |
| chr17 | 48042039 | 48042069 | Hyper | cancer_general | DLX4 | chr17 | 48042435 | 48042956 | Hyper | cancer_general | DLX4 |
| chr17 | 48048952 | 48049059 | Hyper | cancer_general | DLX3 | chr17 | 48049307 | 48050526 | Hyper | cancer_general | DLX3 |
| chr17 | 48071020 | 48071050 | Hyper | esophageal | ACSF2, CHAD | chr17 | 48071791 | 48071894 | Hyper | liver_tcga, cancer_general | CACNA1G, CACNA1G-AS1, SPATA20 |
| chr17 | 48545804 | 48545950 | Hyper | liver_tcga | | chr17 | 48636581 | 48637136 | Hyper | cancer_general | |
| chr17 | 49027838 | 49027876 | Hyper | head_neck | CA10 | chr17 | 50235216 | 50235274 | Hyper | cancer_general | CA10 |
| chr17 | 50235631 | 50235952 | Hyper | cancer_general | HLF | chr17 | 51901004 | 51901034 | Hyper | esophageal | KIF2B |
| chr17 | 53341252 | 53341536 | Hyper | cancer_general | | chr17 | 53342876 | 53343089 | Hyper | cancer_general | HLF |
| chr17 | 53922649 | 53922790 | Hyper | cancer_general | | chr17 | 54674986 | 54675272 | Hyper | tcga, cancer_general | NOG |
| chr17 | 54755969 | 54756014 | Hyper | cancer_general | | chr17 | 55122813 | 55122842 | Hyper | literature | RNF126P1 |
| chr17 | 55213641 | 55213670 | Hyper | literature | MSX2P1, OR4D1 | chr17 | 55962573 | 55962841 | Hyper | liver_tcga | CUEDC1 |
| chr17 | 56234405 | 56234743 | Hyper | cancer_general | LPO | chr17 | 56326949 | 56326994 | Hyper | cancer_general | LPO |
| chr17 | 56327271 | 56327301 | Hyper | esophageal | LPO | chr17 | 56833127 | 56833221 | Hyper | cancer_general | PPM1E |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 56833707 | 56834075 | Hyper | tcga, esophageal | PPM1E | chr17 | 56834306 | 56834375 | Hyper | tcga | PPM1E |
| chr17 | 58216613 | 58217551 | Hyper | cancer_general | CA4 | chr17 | 58218765 | 58218993 | Hyper | cancer_general | CA4 |
| chr17 | 58227374 | 58227426 | Hyper | cancer_general | CA4 | chr17 | 58498697 | 58499314 | Hyper | tcga, cancer_general | C17orf64 |
| chr17 | 59474157 | 59474620 | Hyper | cancer_general | TBX2, BCAS3 | chr17 | 59474833 | 59475100 | Hyper | cancer_general | TBX2, BCAS3 |
| chr17 | 59475678 | 59476127 | Hyper | cancer_general | BCAS3, TBX2 | chr17 | 59476410 | 59476635 | Hyper | cancer_general | TBX2, BCAS3 |
| chr17 | 59478147 | 59478602 | Hyper | cancer_general | TBX2, BCAS3 | chr17 | 59488101 | 59488457 | Hyper | tcga | C17orf82, TBX2 |
| chr17 | 59528876 | 59530352 | Hyper | tcga, cancer_general | TBX4 | chr17 | 59531667 | 59532139 | Hyper | cancer_general | TBX4 |
| chr17 | 59533828 | 59534491 | Hyper | cancer_general | TBX4 | chr17 | 59534751 | 59534781 | Hyper | cancer_general | TBX4 |
| chr17 | 59535137 | 59535219 | Hyper | cancer_general | TBX4 | chr17 | 59539236 | 59539601 | Hyper | tcga, cancer_general, lung | TBX4 |
| chr17 | 59924556 | 59924585 | Hyper | literature | STRADA, LOC729683, LIMD2, MAP3K3 | chr17 | 59937192 | 59937236 | Hyper | literature | INTS2 |
| chr17 | 61778085 | 61778300 | Hyper | cancer_general | PLEKHM1P, LOC146880 | chr17 | 61926172 | 61926603 | Hyper | cancer_general | TCAM1P |
| chr17 | 62777335 | 62777450 | Hyper | hepatobiliary | | chr17 | 62777746 | 62777791 | Hyper | tcga | PLEKHM1P, LOC146880 |
| chr17 | 66596471 | 66596525 | Hyper | cancer_general | FAM20A | chr17 | 66596984 | 66597021 | Hyper | tcga | FAM20A |
| chr17 | 68164733 | 68164928 | Hyper | tcga, cancer_general | KCNJ2, KCNJ2-AS1 | chr17 | 70026543 | 70026667 | Hyper | cancer_general, breast | D43770 |
| chr17 | 70112916 | 70114517 | Hyper | cancer_general | AK094963, SOX9, AL833139 | chr17 | 70215683 | 70216585 | Hyper | cancer_general | |
| chr17 | 71641544 | 71641683 | Hyper | cancer_general | DNAI2 | chr17 | 71948439 | 71948863 | Hyper | cancer_general | KIF19 |
| chr17 | 72270286 | 72270415 | Hyper | cancer_general | KIF19 | chr17 | 72321933 | 72321975 | Hyper | cancer_general | BTBD17, KIF19 |
| chr17 | 72322363 | 72322604 | Hyper | cancer_general | | chr17 | 72353213 | 72353550 | Hyper | cancer_general, tcga | |
| chr17 | 72427853 | 72427999 | Hyper | blood | GPRC5C | chr17 | 72428344 | 72428381 | Hyper | blood | GPRC5C |
| chr17 | 72667337 | 72667565 | Hyper | cancer_general | RAB37 | chr17 | 72849010 | 72849079 | Hyper | cancer_general | FDXR, GRIN2C |
| chr17 | 72857038 | 72857368 | Hyper | cancer_general, tcga | FDXR, GRIN2C | chr17 | 72920796 | 72921032 | Hyper | cancer_general | USH1G, OTOP2 |
| chr17 | 73073684 | 73073954 | Hyper | tcga, cancer_general | SLC16A5 | chr17 | 73584821 | 73584883 | Hyper | cancer_general | MYO15B |
| chr17 | 73709838 | 73709955 | Hyper | cancer_general | ITGB4, SAP30BP | chr17 | 74070281 | 74070582 | Hyper | cancer_general | SRP68, GALR2, ZACN, EXOC7 |
| chr17 | 74071445 | 74071481 | Hyper | cancer_general | ZACN, EXOC7, GALR2, SRP68 | chr17 | 74071689 | 74071729 | Hyper | cancer_general | ZACN, EXOC7, GALR2, SRP68 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 74072941 | 74073036 | Hyper | cancer_general | ZACN, EXOC7, GALR2, SRP68 | chr17 | 74073269 | 74073433 | Hyper | cancer_general | SRP68, ZACN, EXOC7, GALR2 |
| chr17 | 74533844 | 74534310 | Hyper | tcga, liver_tcga, cancer_general | PRCD, CYGB | chr17 | 74581182 | 74581221 | Hyper | cancer_general | ST6GALNAC2 |
| chr17 | 74732944 | 74732973 | Hyper | literature | MFSD11, MIR636, SRSF2, METTL23 | chr17 | 74865053 | 74865192 | Hyper | tcga | MGAT5B, BC038218 |
| chr17 | 74865698 | 74866243 | Hyper | cancer_general | MGAT5B, BC038218 | chr17 | 75137660 | 75137887 | Hyper | tcga | SEC14L1 |
| chr17 | 75315512 | 75315681 | Hyper | literature | 9-Sep | chr17 | 75368735 | 75369238 | Hyper | literature, tcga, liver_tcga, cancer_general | 9-Sep |
| chr17 | 75369440 | 75369860 | Hyper | liver_tcga, literature, cancer_general | 9-Sep | chr17 | 75370269 | 75370316 | Hyper | literature, cancer_general | 9-Sep |
| chr17 | 75370596 | 75370625 | Hyper | liver_tcga, literature | 9-Sep | chr17 | 75385071 | 75385446 | Hyper | literature | MIR4316, SEPT9 |
| chr17 | 75417150 | 75417179 | Hyper | literature | 9-Sep | chr17 | 75524636 | 75525194 | Hyper | tcga, cancer_general | BC040189 |
| chr17 | 76125196 | 76125225 | Hyper | literature | TMC8, TMC6 | chr17 | 76126434 | 76126463 | Hyper | literature | TMC8, TMC6 |
| chr17 | 76128466 | 76128690 | Hyper | literature | TMC8, TMC6 | chr17 | 76130481 | 76130510 | Hyper | literature | TMC6 |
| chr17 | 76227849 | 76228357 | Hyper | tcga, cancer_general | TMEM235, EPR-1, BIRC5 | chr17 | 76921830 | 76921859 | Hyper | literature | TMC6 |
| chr17 | 77179113 | 77179278 | Hyper | cancer_general | RBFOX3 | chr17 | 77179630 | 77179792 | Hyper | tcga, cancer_general | RBFOX3 |
| chr17 | 77776827 | 77777056 | Hyper | cancer_general | CBX8 | chr17 | 77777585 | 77777961 | Hyper | tcga, cancer_general | CBX8 |
| chr17 | 77778943 | 77779179 | Hyper | cancer_general | CBX8 | chr17 | 77788841 | 77788969 | Hyper | cancer_general | TBC1D16, BC044939 |
| chr17 | 77789296 | 77789500 | Hyper | cancer_general |  | chr17 | 77899664 | 77899693 | Hyper | liver_tcga |  |
| chr17 | 78451931 | 78452051 | Hyper | cancer_general | NPTX1 | chr17 | 78452296 | 78452340 | Hyper | cancer_general | NPTX1 |
| chr17 | 78452681 | 78452833 | Hyper | cancer_general | NPTX1 | chr17 | 79058302 | 79058333 | Hyper | liver_tcga | BAIAP2 |
| chr17 | 79615176 | 79615356 | Hyper | cancer_general | PDE6G, TSPAN10 | chr17 | 79813409 | 79813507 | Hyper | liver_tcga | P4HB |
| chr17 | 80186260 | 80186289 | Hyper | literature | SLC16A3 | chr17 | 80197756 | 80197898 | Hyper | liver_tcga | CSNK1D, SLC16A3 |
| chr17 | 80329709 | 80330085 | Hyper | liver_tcga, cancer_general | UTS2R, AF075112, TEX19 | chr17 | 80394573 | 80394602 | Hyper | liver_tcga | C17orf62, HEXDC |
| chr17 | 80693317 | 80693554 | Hyper | blood | FN3K, FN3KRP | chr12 | 570090 | 570171 | Hyper | cancer_general | B4GALNT3 |
| chr12 | 1639135 | 1639222 | Hyper | cancer_general |  | chr12 | 2162554 | 2162817 | Hyper | cancer_general | CACNA1C |
| chr12 | 2163164 | 2163276 | Hyper | cancer_general | CACNA1C | chr12 | 2862068 | 2862225 | Hyper | cancer_general | LOC283440 |
| chr12 | 3371882 | 3371911 | Hyper | liver_tcga | TSPAN9 | chr12 | 3373533 | 3373666 | Hyper | liver_tcga | TSPAN9 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 3600315 | 3600345 | Hyper | cancer_general | AK125333, DQ579489, DQ583138, DQ596092, PRMT8 | chr12 | 3602270 | 3602879 | Hyper | cancer_general | PRMT8, AK125333, DQ579489 |
| chr12 | 3603100 | 3603156 | Hyper | cancer_general | PRMT8, AK125333 | chr12 | 3862254 | 3862298 | Hyper | pancreas | EFCAB4B |
| chr12 | 4274054 | 4274188 | Hyper | cancer_general | CCND2 | chr12 | 4378252 | 4378330 | Hyper | tcga | CCND2 |
| chr12 | 4381433 | 4382386 | Hyper | literature, pancreas | CCND2 | chr12 | 4382965 | 4382999 | Hyper | literature | CCND2 |
| chr12 | 4383492 | 4383784 | Hyper | literature | CCND2 | chr12 | 4384389 | 4384418 | Hyper | literature | CCND2 |
| chr12 | 4384736 | 4384902 | Hyper | literature | CCND2 | chr12 | 4918986 | 4919244 | Hyper | tcga | KCNA6 |
| chr12 | 5018073 | 5018692 | Hyper | tcga, cancer_general | KCNA1 | chr12 | 5019050 | 5020416 | Hyper | tcga, cancer_general | KCNA1 |
| chr12 | 5153039 | 5153520 | Hyper | tcga, cancer_general | KCNA5 | chr12 | 5541100 | 5541177 | Hyper | pancreas | NTF3 |
| chr12 | 5542325 | 5542439 | Hyper | literature | NTF3 | chr12 | 5542759 | 5542911 | Hyper | literature, tcga, cancer_general | NTF3 |
| chr12 | 6308743 | 6308772 | Hyper | literature | CD9 | chr12 | 6664508 | 6665384 | Hyper | cancer_general | NOP2, IFFO1 |
| chr12 | 8025631 | 8025660 | Hyper | literature | NANOGP1 | chr12 | 8171360 | 8171745 | Hyper | tcga, cancer_general | RIMKLB |
| chr12 | 8549178 | 8549208 | Hyper | esophageal | LINC00937 | chr12 | 8850658 | 8850744 | Hyper | esophageal | |
| chr12 | 11653449 | 11653479 | Hyper | cancer_general | | chr12 | 14133152 | 14133263 | Hyper | cancer_general | |
| chr12 | 14133619 | 14133881 | Hyper | cancer_general | | chr12 | 14135111 | 14135339 | Hyper | cancer_general | |
| chr12 | 15374258 | 15374291 | Hyper | blood | RERG | chr12 | 16500576 | 16500621 | Hyper | blood | MGST1 |
| chr12 | 19282333 | 19282363 | Hyper | cancer_general | PLEKHA5 | chr12 | 20521704 | 20521841 | Hyper | cancer_general | PDE3A |
| chr12 | 20522457 | 20522487 | Hyper | tcga, cancer_general | PDE3A | chr12 | 20522769 | 20522891 | Hyper | cancer_general | PDE3A |
| chr12 | 21680394 | 21680683 | Hyper | cancer_general | C12orf39, GYS2, GOLT1B | chr12 | 21810264 | 21810868 | Hyper | tcga, liver_tcga | LDHB |
| chr12 | 22093825 | 22094810 | Hyper | literature, cancer_general | ABCC9 | chr12 | 22095095 | 22095136 | Hyper | cancer_general | ABCC9 |
| chr12 | 22486799 | 22487473 | Hyper | cancer_general, tcga, liver_tcga | ST8SIA1 | chr12 | 24714909 | 24714938 | Hyper | tcga | LINC00477 |
| chr12 | 24715235 | 24715264 | Hyper | tcga | LINC00477 | chr12 | 24716033 | 24716218 | Hyper | tcga | LINC00477 |
| chr12 | 25055952 | 25056436 | Hyper | liver_tcga, literature, cancer_general | BCAT1 | chr12 | 25101592 | 25101660 | Hyper | cancer_general | |
| chr12 | 25101919 | 25102086 | Hyper | cancer_general | | chr12 | 25362824 | 25362853 | Hyper | literature | KRAS, LYRM5 |
| chr12 | 25368463 | 25368492 | Hyper | literature | KRAS | chr12 | 25378543 | 25378662 | Hyper | literature | KRAS |
| chr12 | 25380231 | 25380299 | Hyper | literature | KRAS | chr12 | 25398203 | 25398319 | Hyper | literature | DD157417, KRAS |
| chr12 | 28123996 | 28124247 | Hyper | tcga | PTHLH | chr12 | 28127767 | 28128302 | Hyper | tcga, cancer_general, lung | PTHLH |
| chr12 | 28128547 | 28129084 | Hyper | lung, cancer_general | PTHLH | chr12 | 29936016 | 29936048 | Hyper | cancer_general | TMTC1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 29936602 | 29936864 | Hyper | tcga, cancer_general | TMTC1 | chr12 | 29937331 | 29937374 | Hyper | cancer_general | TMTC1 |
| chr12 | 30322774 | 30323517 | Hyper | cancer_general |  | chr12 | 30975572 | 30976030 | Hyper | tcga, cancer_general |  |
| chr12 | 31079268 | 31079499 | Hyper | cancer_general | TSPAN11 | chr12 | 33591774 | 33591804 | Hyper | cancer_general | SYT10 |
| chr12 | 33592613 | 33592889 | Hyper | cancer_general | SYT10 | chr12 | 39299117 | 39299560 | Hyper | tcga, cancer_general | CPNE8 |
| chr12 | 39539353 | 39539436 | Hyper | cancer_general |  | chr12 | 40618404 | 40618470 | Hyper | cancer_general | LRRK2 |
| chr12 | 41086183 | 41086379 | Hyper | tcga | CNTN1 | chr12 | 41086784 | 41087106 | Hyper | cancer_general | CNTN1 |
| chr12 | 41582513 | 41582988 | Hyper | cancer_general | PDZRN4 | chr12 | 41583374 | 41583419 | Hyper | cancer_general | PDZRN4 |
| chr12 | 43944893 | 43945124 | Hyper | cancer_general |  | chr12 | 43945356 | 43945526 | Hyper | cancer_general |  |
| chr12 | 43945844 | 43946298 | Hyper | literature, cancer_general |  | chr12 | 45269504 | 45269624 | Hyper | tcga | NELL2 |
| chr12 | 45444118 | 45445258 | Hyper | cancer_general | DBX2 | chr12 | 46767650 | 46767697 | Hyper | tcga | SLC38A2 |
| chr12 | 47225381 | 47225579 | Hyper | cancer_general | SLC38A4 | chr12 | 48397195 | 48398070 | Hyper | cancer_general | COL2A1 |
| chr12 | 48398641 | 48398671 | Hyper | cancer_general | COL2A1 | chr12 | 48690674 | 48690929 | Hyper | tcga |  |
| chr12 | 49297802 | 49297915 | Hyper | cancer_general | CCDC65 | chr12 | 49366374 | 49366423 | Hyper | cancer_general |  |
| chr12 | 49374914 | 49375119 | Hyper | cancer_general | WNT1, WNT10B | chr12 | 49375325 | 49375529 | Hyper | cancer_general, tcga | WNT1, WNT10B |
| chr12 | 49390873 | 49391877 | Hyper | cancer_general | PRKAG1, DDN | chr12 | 49691049 | 49691078 | Hyper | liver_tcga | PRPH |
| chr12 | 49727049 | 49727127 | Hyper | cancer_general | TROAP, C1QL4 | chr12 | 49729728 | 49730090 | Hyper | cancer_general | C1QL4, TROAP |
| chr12 | 49759530 | 49759559 | Hyper | literature | SPATS2 | chr12 | 50297497 | 50298055 | Hyper | cancer_general, literature, liver_tcga | FAIM2, LOC283332, BC034605 |
| chr12 | 50355275 | 50355469 | Hyper | cancer_general | AQP6, AQP2, AQP5 | chr12 | 50426748 | 50426799 | Hyper | cancer_general | RACGAP1 |
| chr12 | 52262983 | 52263106 | Hyper | cancer_general, tcga, liver_tcga, cancer_general | GRASP, ACVR1B | chr12 | 52301280 | 52301367 | Hyper | cancer_general | ACVRL1 |
| chr12 | 52400831 | 52401537 | Hyper | liver_tcga, cancer_general |  | chr12 | 52408905 | 52409033 | Hyper | liver_tcga | NR4A1, GRASP |
| chr12 | 52627184 | 52627438 | Hyper | cancer_general | KRT7, LINC00592 | chr12 | 52652153 | 52652613 | Hyper | cancer_general | KRT121P, KRT86, KRT7 |
| chr12 | 53108089 | 53108218 | Hyper | cancer_general |  | chr12 | 53359345 | 53359563 | Hyper | cancer_general |  |
| chr12 | 54089093 | 54089511 | Hyper | cancer_general |  | chr12 | 54132252 | 54132329 | Hyper | cancer_general |  |
| chr12 | 54145843 | 54145895 | Hyper | cancer_general |  | chr12 | 54321250 | 54321628 | Hyper | literature, cancer_general | HOXC-AS5 |
| chr12 | 54322201 | 54322252 | Hyper | cancer_general | HOXC-AS5 | chr12 | 54324799 | 54324937 | Hyper | cancer_general | HOXC-AS5, HOXC13 |
| chr12 | 54329358 | 54329947 | Hyper | cancer_general | HOXC13, HOXC-AS5 | chr12 | 54331062 | 54331135 | Hyper | cancer_general | HOXC13, HOXC-AS5 |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr12 | 54332868 | 54333337 | Hyper | cancer_general | HOXC13, HOXC-AS5 | chr12 | 54338666 | 54339681 | Hyper | cancer_general | HOXC13, HOXC-AS5, HOXC12 |
| chr12 | 54343812 | 54343861 | Hyper | cancer_general | HOXC12, HOXC13 | chr12 | 54345611 | 54346032 | Hyper | cancer_general | HOXC12, HOXC13 |
| chr12 | 54348844 | 54349336 | Hyper | cancer_general | HOTAIR, HOXC12, HOXC13 | chr12 | 54354514 | 54354621 | Hyper | cancer_general | HOTAIR, HOTAIR_4, HOTAIR_5, HOXC12 |
| chr12 | 54354905 | 54355542 | Hyper | tcga, literature, cancer_general | HOTAIR, HOTAIR_4, HOTAIR_5, HOXC12 | chr12 | 54359960 | 54360084 | Hyper | cancer_general | HOTAIR, HOTAIR_4, HOTAIR_5, HOXC11, HOTAIR |
| chr12 | 54360608 | 54360649 | Hyper | cancer_general | HOTAIR_4, HOTAIR_5, HOXC11, HOTAIR | chr12 | 54377912 | 54378115 | Hyper | cancer_general | HOXC10, MIR196A2, HOXC11 |
| chr12 | 54379174 | 54379623 | Hyper | cancer_general | MIR196A2, HOXC10, HOXC11 | chr12 | 54379888 | 54380459 | Hyper | cancer_general | MIR196A2, HOXC10, HOXC11 |
| chr12 | 54387842 | 54387959 | Hyper | cancer_general | HOXC9, MIR196A2, HOXC10 | chr12 | 54388215 | 54388245 | Hyper | cancer_general | HOXC9, MIR196A2, HOXC10 |
| chr12 | 54391369 | 54391403 | Hyper | cancer_general | HOXC9, MIR196A2, HOXC10 | chr12 | 54393479 | 54393684 | Hyper | cancer_general | HOXC8, HOXC9, MIR196A2, HOXC10 |
| chr12 | 54393950 | 54394162 | Hyper | cancer_general | HOXC8, HOXC9, MIR196A2, HOXC10 | chr12 | 54394410 | 54394442 | Hyper | cancer_general | HOXC8, HOXC9, MIR196A2 |
| chr12 | 54398793 | 54398959 | Hyper | cancer_general | HOXC8, HOXC9 | chr12 | 54399616 | 54399646 | Hyper | head_neck | HOXC8, HOXC9 |
| chr12 | 54402690 | 54402796 | Hyper | cancer_general | HOXC8, HOXC6, HOXC4, HOXC5, HOXC9 | chr12 | 54403067 | 54403360 | Hyper | cancer_general | HOXC8, HOXC9, HOXC6, HOXC4, HOXC5 |
| chr12 | 54408411 | 54408726 | Hyper | cancer_general | HOXC6, HOXC4, HOXC5, HOXC8 | chr12 | 54409476 | 54409505 | Hyper | literature | HOXC6, HOXC4, HOXC5, HOXC8 |
| chr12 | 54423565 | 54423697 | Hyper | cancer_general | HOXC5, MIR615, HOXC6, HOXC4 | chr12 | 54424746 | 54424788 | Hyper | cancer_general | HOXC5, MIR615, HOXC6, HOXC4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 54425003 | 54425119 | Hyper | cancer_general | HOXC5, MIR615, HOXC6, HOXC4 | chr12 | 54447351 | 54447581 | Hyper | cancer_general | HOXC4, FLJ12825 |
| chr12 | 54447883 | 54447977 | Hyper | cancer_general | HOXC4, FLJ12825 | chr12 | 54520745 | 54520868 | Hyper | cancer_general | LOC400043 |
| chr12 | 54812238 | 54812359 | Hyper | cancer_general | ITGA5 | chr12 | 54942994 | 54943116 | Hyper | tcga | PDE1B, NCKAP1L |
| chr12 | 56478840 | 56478869 | Hyper | literature | ERBB3 | chr12 | 56481645 | 56481937 | Hyper | literature | ERBB3 |
| chr12 | 56486572 | 56486601 | Hyper | literature | ERBB3 | chr12 | 56490965 | 56490994 | Hyper | literature | ERBB3, PA2G4 |
| chr12 | 56491630 | 56491659 | Hyper | literature | PA2G4, ERBB3 | chr12 | 56492618 | 56492647 | Hyper | literature | PA2G4, ERBB3 |
| chr12 | 56873601 | 56873630 | Hyper | liver_tcga | BC059370, GLS2, SPRYD4 | chr12 | 56882240 | 56882380 | Hyper | blood | BC059370, GLS2 |
| chr12 | 57387303 | 57387332 | Hyper | liver_tcga | GPR182, ZBTB39 | chr12 | 57618574 | 57618979 | Hyper | tcga, cancer_general | SHMT2, NDUFA4L2, NXPH4 |
| chr12 | 57944081 | 57944117 | Hyper | cancer_general | KIF5A, DCTN2 | chr12 | 58021320 | 58021713 | Hyper | cancer_general, liver_tcga | BC073932, B4GALNT1, SLC26A10 |
| chr12 | 58021916 | 58022029 | Hyper | liver_tcga | B4GALNT1, SLC26A10 | chr12 | 58025646 | 58025873 | Hyper | cancer_general | JA611266, B4GALNT1, SLC26A10 |
| chr12 | 58145415 | 58145450 | Hyper | literature | DM110804, MARCH9, CDK4, TSPAN31 | chr12 | 59314159 | 59314189 | Hyper | blood | LRIG3 |
| chr12 | 62584838 | 62586017 | Hyper | tcga, cancer_general | FAM19A2 | chr12 | 62586252 | 62586281 | Hyper | tcga | FAM19A2 |
| chr12 | 63025574 | 63026160 | Hyper | tcga, cancer_general | | chr12 | 63543848 | 63544727 | Hyper | cancer_general | AVPR1A |
| chr12 | 63545313 | 63545343 | Hyper | cancer_general | AVPR1A | chr12 | 64061821 | 64062159 | Hyper | cancer_general | DPY19L2 |
| chr12 | 64062369 | 64062578 | Hyper | tcga, liver_tcga | DPY19L2 | chr12 | 64062921 | 64063096 | Hyper | cancer_general | DPY19L2 |
| chr12 | 64784092 | 64784252 | Hyper | cancer_general | | chr12 | 64784534 | 64784564 | Hyper | cancer_general | |
| chr12 | 65218102 | 65219156 | Hyper | tcga, cancer_general | TBC1D30 | chr12 | 65219376 | 65219784 | Hyper | cancer_general | TBC1D30 |
| chr12 | 65220205 | 65220350 | Hyper | cancer_general | TBC1D30 | chr12 | 65514863 | 65515596 | Hyper | cancer_general | WIF1 |
| chr12 | 66122800 | 66123519 | Hyper | cancer_general | IRAK3 | chr12 | 66135984 | 66136014 | Hyper | cancer_general | |
| chr12 | 66582827 | 66583137 | Hyper | liver_tcga, cancer_general | | chr12 | 69327259 | 69327463 | Hyper | cancer_general | CPM |
| chr12 | 72332641 | 72332696 | Hyper | lung | TPH2 | chr12 | 72665186 | 72665788 | Hyper | cancer_general | TRHDE-AS1, BC093903, TRHDE |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 72666115 | 72666211 | Hyper | cancer_general | BC093903, TRHDE-AS1, TRHDE | chr12 | 72666713 | 72667425 | Hyper | tcga, cancer_general | TRHDE-AS1, TRHDE, BC093903 |
| chr12 | 72667652 | 72667682 | Hyper | cancer_general | TRHDE, BC093903, TRHDE-AS1 | | | | | | |
| chr12 | 75602976 | 75603231 | Hyper | cancer_general | KCNC2 | chr12 | 75601264 | 75601910 | Hyper | cancer_general | KCNC2 |
| chr12 | 75728737 | 75728766 | Hyper | tcga | GLIPR1L1, CAPS2 | chr12 | 75728336 | 75728485 | Hyper | tcga, cancer_general | GLIPR1L1, CAPS2 |
| | | | | | | chr12 | 77719311 | 77719422 | Hyper | tcga | |
| chr12 | 79257222 | 79257351 | Hyper | pancreas | SYT1 | chr12 | 79258924 | 79258954 | Hyper | cancer_general | SYT1 |
| chr12 | 81102185 | 81102562 | Hyper | cancer_general, liver_tcga | MYF5, MYF6 | chr12 | 81107989 | 81108034 | Hyper | liver_tcga | MYF5, MYF6 |
| chr12 | 81471517 | 81472111 | Hyper | cancer_general | ACSS3 | chr12 | 85306519 | 85306578 | Hyper | cancer_general | SLC6A15 |
| chr12 | 85667272 | 85667731 | Hyper | cancer_general | ALX1 | chr12 | 85673206 | 85673235 | Hyper | literature | ALX1 |
| chr12 | 85673460 | 85674807 | Hyper | cancer_general | ALX1 | chr12 | 88973544 | 88973582 | Hyper | blood | U1 |
| chr12 | 88974159 | 88974253 | Hyper | blood | U1 | chr12 | 93966429 | 93966603 | Hyper | cancer_general | SOCS2, SOCS2-AS1 |
| chr12 | 93966998 | 93967239 | Hyper | cancer_general | SOCS2, SOCS2-AS1 | chr12 | 94543409 | 94543445 | Hyper | cancer_general | PLXNC1 |
| chr12 | 94543899 | 94543961 | Hyper | cancer_general | PLXNC1 | chr12 | 95267524 | 95267554 | Hyper | esophageal | USP44 |
| chr12 | 95267865 | 95267976 | Hyper | cancer_general | | chr12 | 95941868 | 95942978 | Hyper | cancer_general, liver_tcga, literature | |
| chr12 | 99288312 | 99289309 | Hyper | cancer_general, tcga | ANKS1B | chr12 | 101111029 | 101111061 | Hyper | cancer_general | ANO4 |
| chr12 | 101111373 | 101111479 | Hyper | cancer_general | ANO4 | chr12 | 103218495 | 103218595 | Hyper | cancer_general, tcga | LINC00485 |
| chr12 | 103350324 | 103350354 | Hyper | cancer_general | ASCL1 | chr12 | 103351564 | 103352681 | Hyper | cancer_general | ASCL1 |
| chr12 | 103358865 | 103358899 | Hyper | cancer_general | ASCL1 | chr12 | 103359556 | 103359586 | Hyper | cancer_general | ASCL1 |
| chr12 | 103889160 | 103889211 | Hyper | pancreas | C12orf42 | chr12 | 103889746 | 103889812 | Hyper | cancer_general | C12orf42 |
| chr12 | 104609417 | 104610100 | Hyper | tcga, cancer_general | TXNRD1 | chr12 | 104850505 | 104850592 | Hyper | colorectal | CHST11 |
| chr12 | 104851077 | 104851186 | Hyper | colorectal | CHST11 | chr12 | 104852032 | 104852508 | Hyper | cancer_general, tcga | CHST11 |
| chr12 | 105478323 | 105478419 | Hyper | liver_tcga, hepatobiliary | ALDH1L2 | chr12 | 106533852 | 106533881 | Hyper | literature | NUAK1 |
| chr12 | 106974353 | 106974383 | Hyper | cancer_general | LOC100287944, RFX4 | chr12 | 106976725 | 106976795 | Hyper | cancer_general | RFX4, LOC100287944 |
| chr12 | 106977321 | 106977497 | Hyper | cancer_general | RFX4, LOC100287944 | chr12 | 106979161 | 106979534 | Hyper | cancer_general | LOC100287944, RFX4 |
| chr12 | 106979799 | 106979995 | Hyper | cancer_general | RFX4, LOC100287944 | chr12 | 106980223 | 106980333 | Hyper | cancer_general | LOC100287944 |
| chr12 | 106980854 | 106981406 | Hyper | cancer_general | RFX4, LOC100287944 | chr12 | 107486550 | 107486672 | Hyper | blood | CRY1 |
| chr12 | 107487194 | 107487855 | Hyper | blood | CRY1 | chr12 | 107712273 | 107712303 | Hyper | blood | BTBD11 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 107713205 | 107713235 | Hyper | cancer_general | BTBD11 | chr12 | 107714866 | 107715153 | Hyper | cancer_general | BTBD11 |
| chr12 | 108168971 | 108169573 | Hyper | literature, cancer_general, liver_tcga | ASCL4 | chr12 | 108237466 | 108237586 | Hyper | cancer_general | |
| chr12 | 108238102 | 108238616 | Hyper | cancer_general, tcga | | chr12 | 108297411 | 108297466 | Hyper | cancer_general | LOC728739 |
| chr12 | 109639281 | 109639475 | Hyper | liver_tcga | ACACB | chr12 | 111127124 | 111127455 | Hyper | tcga, cancer_general | HVCN1 |
| chr12 | 111471177 | 111471559 | Hyper | tcga, literature, cancer_general | CUX2 | chr12 | 111471948 | 111472752 | Hyper | cancer_general, tcga | CUX2 |
| chr12 | 112888151 | 112888315 | Hyper | literature | PTPN11 | chr12 | 112910821 | 112910850 | Hyper | literature | PTPN11 |
| chr12 | 112915504 | 112915538 | Hyper | literature | PTPN11 | chr12 | 112926255 | 112926284 | Hyper | literature | PTPN11 |
| chr12 | 112926876 | 112926914 | Hyper | literature | PTPN11 | chr12 | 113012954 | 113013157 | Hyper | cancer_general | RPH3A |
| chr12 | 113541667 | 113542099 | Hyper | cancer_general | RASAL1, DTX1 | chr12 | 113592238 | 113592359 | Hyper | cancer_general | DDX54, CCDC42B |
| chr12 | 113900704 | 113900765 | Hyper | tcga | LHX5 | chr12 | 113901074 | 113901591 | Hyper | tcga, cancer_general | LHX5 |
| chr12 | 113902026 | 113902353 | Hyper | cancer_general | LHX5 | chr12 | 113903468 | 113903498 | Hyper | cancer_general | LHX5 |
| chr12 | 113904779 | 113905016 | Hyper | cancer_general | LHX5 | chr12 | 113908990 | 113909455 | Hyper | cancer_general | LHX5 |
| chr12 | 113909667 | 113909708 | Hyper | cancer_general | LHX5 | chr12 | 113913267 | 113914050 | Hyper | cancer_general | LHX5 |
| chr12 | 113916222 | 113916316 | Hyper | cancer_general | LHX5 | chr12 | 113916649 | 113916678 | Hyper | literature | LHX5 |
| chr12 | 113916972 | 113917012 | Hyper | cancer_general | LHX5 | chr12 | 113917232 | 113917310 | Hyper | cancer_general | LHX5 |
| chr12 | 113917775 | 113917890 | Hyper | cancer_general | LHX5 | chr12 | 114029408 | 114029660 | Hyper | tcga | LHX5 |
| chr12 | 114076029 | 114076093 | Hyper | cancer_general | | chr12 | 114833985 | 114834102 | Hyper | cancer_general | TBX5 |
| chr12 | 114838325 | 114838726 | Hyper | cancer_general | TBX5-AS1, TBX5 | chr12 | 114839104 | 114839147 | Hyper | cancer_general | TBX5-AS1, TBX5 |
| chr12 | 114841046 | 114841084 | Hyper | cancer_general | TBX5-AS1, TBX5 | chr12 | 114841425 | 114841493 | Hyper | cancer_general | TBX5-AS1, TBX5 |
| chr12 | 114843112 | 114843278 | Hyper | cancer_general | TBX5-AS1, TBX5 | chr12 | 114843545 | 114843660 | Hyper | cancer_general | TBX5-AS1, TBX5 |
| chr12 | 114844201 | 114844300 | Hyper | cancer_general | TBX5-AS1, TBX5 | chr12 | 114846715 | 114846768 | Hyper | cancer_general | TBX5-AS1, TBX5 |
| chr12 | 114846979 | 114847691 | Hyper | cancer_general | TBX5-AS1, TBX5 | chr12 | 114852040 | 114852082 | Hyper | cancer_general | TBX5-AS1, TBX5 |
| chr12 | 114852293 | 114852373 | Hyper | tcga | TBX5-AS1 | chr12 | 114877171 | 114877262 | Hyper | cancer_general | |
| chr12 | 114878550 | 114878584 | Hyper | cancer_general | | chr12 | 114878813 | 114879012 | Hyper | cancer_general | |
| chr12 | 114881634 | 114881764 | Hyper | cancer_general | | chr12 | 114882555 | 114882646 | Hyper | cancer_general | |
| chr12 | 114883473 | 114883535 | Hyper | cancer_general | | chr12 | 114885222 | 114885284 | Hyper | cancer_general | |
| chr12 | 114918594 | 114918717 | Hyper | cancer_general | | chr12 | 115136159 | 115136363 | Hyper | cancer_general | |
| chr12 | 116946086 | 116946548 | Hyper | tcga, cancer_general | | chr12 | 117798065 | 117798095 | Hyper | cancer_general | NOS1 |
| chr12 | 117798690 | 117798965 | Hyper | cancer_general | NOS1 | chr12 | 117799413 | 117799529 | Hyper | cancer_general | NOS1 |
| chr12 | 119212216 | 119212381 | Hyper | cancer_general | | chr12 | 119418594 | 119418847 | Hyper | cancer_general | SRRM4 |
| chr12 | 119419436 | 119419466 | Hyper | cancer_general | SRRM4 | chr12 | 119419720 | 119419899 | Hyper | cancer_general | SRRM4 |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr12 | 120032862 | 120033169 | Hyper | cancer_general | TMEM233, AF086288 | chr12 | 120535158 | 120535187 | Hyper | literature | RAB35, CCDC64 |
| chr12 | 120536625 | 120536654 | Hyper | literature | RAB35, CCDC64 | chr12 | 124246908 | 124246937 | Hyper | liver_tcga | DNAH10, ATP6V0A2 |
| chr12 | 124247208 | 124247237 | Hyper | liver_tcga | DNAH10, ATP6V0A2 | chr12 | 124865115 | 124865144 | Hyper | literature | NCOR2 |
| chr12 | 125533949 | 125534407 | Hyper | liver_tcga, cancer_general | | chr12 | 125670117 | 125670289 | Hyper | cancer_general | |
| chr12 | 126168554 | 126168620 | Hyper | cancer_general | | chr12 | 127210965 | 127211378 | Hyper | cancer_general | LINC00944 |
| chr12 | 127765158 | 127765432 | Hyper | cancer_general | | chr12 | 127940086 | 127940247 | Hyper | pancreas | |
| chr12 | 128751384 | 128751443 | Hyper | cancer_general | TMEM132C | chr12 | 128751821 | 128752240 | Hyper | cancer_general | TMEM132C |
| chr12 | 128752499 | 128752944 | Hyper | cancer_general | TMEM132C | chr12 | 128753210 | 128752240 | Hyper | cancer_general | TMEM132C |
| chr12 | 128850534 | 128850644 | Hyper | cancer_general | | chr12 | 129338003 | 129338816 | Hyper | cancer_general | GLT1D1 |
| chr12 | 129427424 | 129427557 | Hyper | pancreas, cancer_general | GLT1D1 | chr12 | 130387776 | 130387811 | Hyper | cancer_general | |
| chr12 | 130388410 | 130389152 | Hyper | cancer_general | | chr12 | 130589202 | 130589266 | Hyper | cancer_general | |
| chr12 | 130645233 | 130645627 | Hyper | cancer_general | FZD10, FZD10-AS1 | chr12 | 130646686 | 130648472 | Hyper | tcga, cancer_general | FZD10-AS1, FZD10 |
| chr12 | 131200379 | 131200645 | Hyper | tcga | RIMBP2 | chr12 | 131400816 | 131400919 | Hyper | cancer_general | |
| chr12 | 133195093 | 133195196 | Hyper | liver_tcga | LRCOL1, P2RX2, POLE | chr12 | 133463736 | 133463876 | Hyper | esophageal | CHFR |
| chr12 | 133464108 | 133464166 | Hyper | esophageal | CHFR | chr12 | 133464840 | 133465027 | Hyper | tcga | CHFR |
| chr12 | 133481389 | 133481655 | Hyper | liver_tcga, cancer_general | AK055957 | chr12 | 133484742 | 133485355 | Hyper | liver_tcga, cancer_general | AK055957 |
| chr12 | 133485557 | 133485847 | Hyper | cancer_general | AK055957 | chr12 | 133758048 | 133758107 | Hyper | esophageal | ZNF268 |
| chr8 | 686870 | 687316 | Hyper | tcga, cancer_general | ERICH1-AS1 | chr8 | 687745 | 688032 | Hyper | tcga, cancer_general | ERICH1-AS1 |
| chr8 | 688360 | 688390 | Hyper | cancer_general | ERICH1-AS1 | chr8 | 688985 | 689043 | Hyper | cancer_general | |
| chr8 | 1950097 | 1950134 | Hyper | tcga | KBTBD11 | chr8 | 4849141 | 4849177 | Hyper | cancer_general | |
| chr8 | 4849466 | 4849500 | Hyper | cancer_general | | chr8 | 4850247 | 4850516 | Hyper | cancer_general | |
| chr8 | 4851736 | 4851765 | Hyper | tcga | | chr8 | 4852021 | 4852118 | Hyper | tcga, cancer_general | |
| chr8 | 9756051 | 9756476 | Hype | cancer_general | LINC00599, AK091593, MIR124-1 | chr8 | 9760735 | 9761155 | Hyper | tcga, cancer_general | MIR124-1, AK091593, LINC00599 |
| chr8 | 9762586 | 9762864 | Hyper | cancer_general | MIR124-1, AK091593, LINC00599 | chr8 | 9763143 | 9763275 | Hyper | cancer_general | MIR124-1, AK091593, LINC00599 |
| chr8 | 9763895 | 9764214 | Hyper | cancer_general | MIR124-1, AK091593, LINC00599 | chr8 | 9764434 | 9764551 | Hyper | cancer_general | MIR124-1, AK091593, LINC00599 |
| chr8 | 10587589 | 10587783 | Hyper | tcga | BC043573, SOX7 | chr8 | 10588383 | 10588456 | Hyper | cancer_general | BC043573, SOX7 |
| chr8 | 11204479 | 11204509 | Hyper | cancer_general | BC038546, TDH | chr8 | 11204810 | 11204905 | Hyper | cancer_general | TDH, BC038546 |
| chr8 | 11536827 | 11536857 | Hyper | cancer_general | GATA4 | chr8 | 11537225 | 11537259 | Hyper | cancer_general | GATA4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 11554885 | 11554915 | Hyper | cancer_general | GATA4 | chr8 | 11555152 | 11555521 | Hyper | cancer_general | GATA4 |
| chr8 | 11559759 | 11560375 | Hyper | cancer_general | GATA4 | chr8 | 11560711 | 11560793 | Hyper | cancer_general | GATA4 |
| chr8 | 11561442 | 11562169 | Hyper | tcga, cancer_general | GATA4 | chr8 | 11562422 | 11562485 | Hyper | cancer_general | GATA4 |
| chr8 | 11562701 | 11562917 | Hyper | cancer_general | GATA4 | chr8 | 12990386 | 12990431 | Hyper | cancer_general | DLC1 |
| chr8 | 12990664 | 12990784 | Hyper | cancer_general | DLC1 | chr8 | 15094505 | 15094582 | Hyper | cancer_general | |
| chr8 | 15397735 | 15397845 | Hyper | cancer_general | TUSC3 | chr8 | 16884182 | 16884239 | Hyper | tcga | MICU3 |
| chr8 | 16885205 | 16885241 | Hyper | cancer_general | MICU3 | chr8 | 17271066 | 17271119 | Hyper | liver_tcga | |
| chr8 | 19797433 | 19797463 | Hyper | cancer_general | LPL | chr8 | 19797939 | 19798019 | Hyper | cancer_general | LPL |
| chr8 | 20160762 | 20160894 | Hyper | cancer_general | | chr8 | 22089409 | 22089560 | Hyper | cancer_general | PHYHIP |
| chr8 | 22562345 | 22562483 | Hyper | cancer_general | PEBP4 | chr8 | 22960648 | 22960723 | Hyper | cancer_general | TNFRSF10C, LOC254896 |
| chr8 | 23020951 | 23021107 | Hyper | tcga | TNFRSF10D | chr8 | 23260683 | 23260870 | Hyper | cancer_general | ENTPD4 |
| chr8 | 23559385 | 23560525 | Hyper | cancer_general | NKX2-6 | chr8 | 23563791 | 23564388 | Hyper | cancer_general | NKX2-6 |
| chr8 | 23564652 | 23565024 | Hyper | cancer_general | NKX2-6 | chr8 | 23566803 | 23567492 | Hyper | cancer_general | NKX2-6 |
| chr8 | 23571973 | 23571977 | Hyper | cancer_general | | chr8 | 23572377 | 23572554 | Hyper | cancer_general | NKX2-6 |
| chr8 | 23584078 | 23584760 | Hyper | tcga, cancer_general | | chr8 | 24770314 | 24770581 | Hyper | cancer_general | AK308605, NEFM |
| chr8 | 24771168 | 24771213 | Hyper | cancer_general | NEFM, AK308605 | chr8 | 24771431 | 24771562 | Hyper | literature, cancer_general | NEFM, AK308605 |
| chr8 | 24813188 | 24813287 | Hyper | cancer_general | NEFL | chr8 | 24813750 | 24814407 | Hyper | tcga | NEFL |
| chr8 | 24857776 | 24857808 | Hyper | cancer_general | | chr8 | 24858336 | 24858440 | Hyper | cancer_general | |
| chr8 | 24858856 | 24859161 | Hyper | tcga, cancer_general | | chr8 | 24859496 | 24859526 | Hyper | cancer_general | |
| chr8 | 25041746 | 25041864 | Hyper | blood | DOCK5 | chr8 | 25042534 | 25042567 | Hyper | blood | DOCK5 |
| chr8 | 25900408 | 25901317 | Hyper | cancer_general | EBF2 | chr8 | 25901540 | 25901765 | Hyper | cancer_general | EBF2 |
| chr8 | 25902146 | 25902176 | Hyper | cancer_general | EBF2 | chr8 | 25902619 | 25902649 | Hyper | cancer_general | EBF2 |
| chr8 | 25903662 | 25903854 | Hyper | cancer_general | EBF2 | chr8 | 25904157 | 25904191 | Hyper | cancer_general | EBF2 |
| chr8 | 25905096 | 25905126 | Hyper | cancer_general | EBF2 | chr8 | 25905762 | 25905811 | Hyper | cancer_general | EBF2 |
| chr8 | 25909197 | 25909597 | Hyper | cancer_general | | chr8 | 26372863 | 26372893 | Hyper | cancer_general | DPYSL2, PNMA2 |
| chr8 | 26723985 | 26724080 | Hyper | cancer_general | AK311558, ADRA1A | chr8 | 30243388 | 30243423 | Hyper | cancer_general | RBPMS, LOC100128750 |
| chr8 | 30769249 | 30769411 | Hyper | cancer_general | NRG1 | chr8 | 30770106 | 30770188 | Hyper | tcga | NRG1 |
| chr8 | 31496481 | 31496757 | Hyper | cancer_general | NRG1 | chr8 | 31497024 | 31497152 | Hyper | cancer_general | NRG1 |
| chr8 | 31497499 | 31497639 | Hyper | cancer_general | NRG1 | chr8 | 31498117 | 31498150 | Hyper | cancer_general | TTI2 |
| chr8 | 32406598 | 32406914 | Hyper | tcga, cancer_general | | chr8 | 33372069 | 33372125 | Hyper | cancer_general | |
| chr8 | 33457142 | 33457379 | Hyper | cancer_general | DUSP26 | chr8 | 35092985 | 35093054 | Hyper | cancer_general | UNC5D |
| chr8 | 35093951 | 35093981 | Hyper | cancer_general | UNC5D | chr8 | 37655454 | 37655517 | Hyper | cancer_general | GPR124 |
| chr8 | 37655810 | 37656081 | Hyper | cancer_general | GPR124 | chr8 | 37822796 | 37823423 | Hyper | tcga, cancer_general | ADRB3 |
| chr8 | 37823678 | 37823726 | Hyper | cancer_general | ADRB3 | chr8 | 38008234 | 38008557 | Hyper | cancer_general | STAR |
| chr8 | 38274835 | 38274864 | Hyper | literature | FGFR1, LETM2 | chr8 | 38323911 | 38323941 | Hyper | cancer_general | FGFR1 |
| chr8 | 38965121 | 38965386 | Hyper | liver_tcga | ADAM32 | chr8 | 41165865 | 41166723 | Hyper | cancer_general | |
| chr8 | 41166974 | 41167035 | Hyper | cancer_general | SFRP1 | chr8 | 41424760 | 41424842 | Hyper | cancer_general | |
| chr8 | 41624826 | 41624855 | Hyper | tcga | | chr8 | 41625112 | 41625141 | Hyper | tcga | |
| chr8 | 41733505 | 41733640 | Hyper | cancer_general | | chr8 | 41753593 | 41753761 | Hyper | cancer_general | SFRP1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 41754152 | 41754885 | Hyper | liver_tcga, cancer_general | | chr8 | 41755178 | 41755208 | Hyper | cancer_general | |
| chr8 | 48100155 | 48100443 | Hyper | tcga | LOC100287846 | | | | | | |
| chr8 | 49468669 | 49469127 | Hyper | tcga, liver_tcga, cancer_general | | chr8 | 49293364 | 49293614 | Hyper | tcga, cancer_general | |
| | | | | | | chr8 | 49783041 | 49783283 | Hyper | tcga | |
| chr8 | 50822179 | 50822308 | Hyper | cancer_general | SNTG1 | chr8 | 50822686 | 50822734 | Hyper | cancer_general | SNTG1 |
| chr8 | 50823452 | 50823562 | Hyper | cancer_general | SNTG1 | chr8 | 53477408 | 53477780 | Hyper | cancer_general | FAM150A |
| chr8 | 53478008 | 53478275 | Hyper | cancer_general, tcga | FAM150A | chr8 | 53478480 | 53478720 | Hyper | cancer_general, tcga | FAM150A |
| chr8 | 53851141 | 53851170 | Hyper | literature | NPBWR1 | chr8 | 53853811 | 53854509 | Hyper | tcga, colorectal, cancer_general | NPBWR1 |
| chr8 | 54163316 | 54164175 | Hyper | tcga, cancer_general | OPRK1 | chr8 | 54789278 | 54789310 | Hyper | cancer_general | RGS20 |
| chr8 | 54789632 | 54790077 | Hyper | cancer_general | RGS20 | chr8 | 54790291 | 54790855 | Hyper | cancer_general | RGS20 |
| chr8 | 54791809 | 54792237 | Hyper | cancer_general | RGS20 | chr8 | 54792634 | 54792760 | Hyper | cancer_general | RGS20 |
| chr8 | 54794217 | 54794327 | Hyper | cancer_general | RGS20 | chr8 | 54794713 | 54795196 | Hyper | cancer_general | RGS20 |
| chr8 | 55366188 | 55367641 | Hyper | tcga, cancer_general | SOX17 | chr8 | 55370113 | 55370858 | Hyper | literature, cancer_general | SOX17 |
| chr8 | 55371178 | 55372538 | Hyper | cancer_general | SOX17 | chr8 | 55379280 | 55379962 | Hyper | cancer_general | SOX17 |
| chr8 | 55382766 | 55383237 | Hyper | cancer_general | SOX17 | chr8 | 56013641 | 56013927 | Hyper | cancer_general | XKR4 |
| chr8 | 56014157 | 56014317 | Hyper | cancer_general | XKR4 | chr8 | 56014623 | 56014783 | Hyper | cancer_general | XKR4 |
| chr8 | 56015038 | 56015357 | Hyper | cancer_general | XKR4 | chr8 | 56015560 | 56015619 | Hyper | cancer_general | XKR4 |
| chr8 | 56015908 | 56015938 | Hyper | pancreas | XKR4 | chr8 | 57025692 | 57025943 | Hyper | cancer_general | MOS, SNORA3 |
| chr8 | 57026168 | 57026213 | Hyper | cancer_general | SNORA3, MOS | chr8 | 57026503 | 57026547 | Hyper | cancer_general | SNORA3, MOS |
| chr8 | 57069553 | 57070157 | Hyper | tcga, cancer_general, liver_tcga | PLAG1 | chr8 | 57358147 | 57359636 | Hyper | literature, cancer_general | AX747062, PENK |
| chr8 | 57359893 | 57359922 | Hyper | literature | PENK, AX747062 | chr8 | 57360570 | 57360791 | Hyper | literature, cancer_general | AX747062, PENK |
| chr8 | 58907698 | 58907835 | Hyper | cancer_general | FAM110B | chr8 | 60032680 | 60032738 | Hyper | cancer_general | TOX |
| chr8 | 62200502 | 62200776 | Hyper | cancer_general | CLVS1 | chr8 | 63161658 | 63161800 | Hyper | cancer_general | NKAIN3 |
| chr8 | 65281616 | 65281760 | Hyper | cancer_general | BX537900, MIR124-2, LOC100130155 | chr8 | 65281984 | 65283341 | Hyper | cancer_general, tcga | LOC100130155, BX537900, MIR124-2, RMI124-2 |
| chr8 | 65283799 | 65284094 | Hyper | cancer_general | LOC100130155, BX537900, MIR124-2 | chr8 | 65286056 | 65286366 | Hyper | cancer_general | BX537900, MIR124-2, LOC100130155 |
| chr8 | 65286682 | 65286753 | Hyper | cancer_general | LOC100130155, BX537900, MIR124-2 | chr8 | 65286963 | 65287251 | Hyper | cancer_general | BX537900, MIR124-2, LOC100130155 |
| chr8 | 65289123 | 65289241 | Hyper | cancer_general | BX537900, MIR124-2, LOC100130155 | chr8 | 65289614 | 65290798 | Hyper | literature, cancer_general | BX537900, MIR 124-2, LOC100130155 |
| chr8 | 65291034 | 65291284 | Hyper | cancer_general | MIR124-2, BX537900, LOC100130155 | chr8 | 65292185 | 65292727 | Hyper | cancer_general | BX537900, LOC100130155, MIR124-2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 65488271 | 65488322 | Hyper | cancer_general | BHLHE22, LOC401463 | chr8 | 65488661 | 65488697 | Hyper | cancer_general | BHLHE22, LOC401463 |
| chr8 | 65489099 | 65489129 | Hyper | cancer_general | BHLHE22, LOC401463 | chr8 | 65492712 | 65492979 | Hyper | tcga, cancer_general | BHLHE22, LOC401463 |
| chr8 | 65493195 | 65493433 | Hyper | cancer_general | BHLHE22, LOC401463 | chr8 | 65493658 | 65493751 | Hyper | cancer_general | BHLHE22, LOC401463 |
| chr8 | 65493961 | 65494193 | Hyper | cancer_general | BHLHE22, LOC401463 | chr8 | 65498566 | 65498841 | Hyper | cancer_general | CYP7B1, BHLHE22, LOC401463 |
| chr8 | 65499757 | 65500015 | Hyper | cancer_general | CYP7B1, BHLHE22, LOC401463 | chr8 | 65710938 | 65711046 | Hyper | head_neck | CYP7B1 |
| chr8 | 67025063 | 67025640 | Hyper | head_neck | TRNA_Ala, TRNA_Tyr | chr8 | 67025920 | 67026578 | Hyper | head_neck | TRNA_Tyr, TRNA_Ala |
| chr8 | 67026812 | 67026990 | Hyper | head_neck | TRNA_Ala, TRNA_Tyr | chr8 | 67344538 | 67344771 | Hyper | tcga, cancer_general | ADHFE1, RRS1, LOC100505676 |
| chr8 | 67873327 | 67875682 | Hyper | tcga, liver_tcga, cancer_general | TCF24 | chr8 | 67940624 | 67940875 | Hyper | cancer_general | |
| chr8 | 68864578 | 68864765 | Hyper | cancer_general | BC036055, PREX2 | chr8 | 69242905 | 69242988 | Hyper | tcga, cancer_general | C8orf34, LOC286189 |
| chr8 | 69243269 | 69243994 | Hyper | tcga, cancer_general | LOC286189, C8orf34 | chr8 | 69244370 | 69244500 | Hyper | cancer_general | C8orf34, LOC286189 |
| chr8 | 70744860 | 70744925 | Hyper | cancer_general | SLCOSA1 | chr8 | 70947760 | 70947658 | Hyper | cancer_general | |
| chr8 | 70981944 | 70983226 | Hyper | cancer_general, literature | PRDM14 | chr8 | 70983504 | 70984978 | Hyper | liver_tcga, cancer_general | PRDM14 |
| chr8 | 72273998 | 72274033 | Hyper | cancer_general | EYA1 | chr8 | 72460007 | 72460269 | Hyper | cancer_general | |
| chr8 | 72468569 | 72469574 | Hyper | tcga, cancer_general | | chr8 | 72471053 | 72471083 | Hyper | cancer_general | |
| chr8 | 72754394 | 72754609 | Hyper | cancer_general | LOC100132891, MSC | chr8 | 72754821 | 72755176 | Hyper | tcga, cancer_general | LOC100132891, MSC |
| chr8 | 72755666 | 72756896 | Hyper | cancer_general | MSC, LOC100132891 | chr8 | 72917335 | 72917446 | Hyper | tcga | LOC100132891 |
| chr8 | 72987600 | 72988036 | Hyper | cancer_general | TRPA1 | chr8 | 73163777 | 73164180 | Hyper | cancer_general | LOC392232 |
| chr8 | 73450064 | 73450100 | Hyper | cancer_general | KCNB2 | chr8 | 73450515 | 73450559 | Hyper | cancer_general | KCNB2 |
| chr8 | 75896574 | 75897337 | Hyper | tcga, cancer_general | CRISPLD1 | chr8 | 77585219 | 77585698 | Hyper | cancer_general | ZFHX4, ZFHX4-AS1 |
| chr8 | 77586175 | 77586278 | Hyper | cancer_general | ZFHX4, ZFHX4-AS1 | chr8 | 77586563 | 77586617 | Hyper | cancer_general | ZFHX4, ZFHX4-AS1 |
| chr8 | 77590239 | 77590466 | Hyper | cancer_general | ZFHX4, ZFHX4-AS1 | chr8 | 77593110 | 77593376 | Hyper | cancer_general | ZFHX4, ZFHX4-AS1 |
| chr8 | 77593889 | 77594124 | Hyper | cancer_general | ZFHX4, ZFHX4-AS1 | chr8 | 77594648 | 77594993 | Hyper | tcga, cancer_general | ZFHX4, ZFHX4-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 77595339 | 77595494 | Hyper | cancer_general | ZFHX4-AS1, ZFHX4 | chr8 | 79428297 | 79428401 | Hyper | cancer_general | PKIA |
| chr8 | 80523983 | 80524029 | Hyper | cancer_general | STMN2 | chr8 | 80524253 | 80524318 | Hyper | cancer_general | STMN2 |
| chr8 | 80524946 | 80525020 | Hyper | cancer_general | STMN2 | chr8 | 80525604 | 80525733 | Hyper | cancer_general, colorectal | STMN2 |
| chr8 | 80695902 | 80695932 | Hyper | cancer_general | AK055332 | chr8 | 80803673 | 80803872 | Hyper | cancer_general | |
| chr8 | 81398018 | 81398155 | Hyper | esophageal | ZBTB10, DJ031142 | chr8 | 81398428 | 81399496 | Hyper | esophageal | |
| chr8 | 81478185 | 81478350 | Hyper | cancer_general | RAIYL | chr8 | 85095482 | 85095668 | Hyper | cancer_general | ZBTB10, DJ031142 |
| chr8 | 85096583 | 85096805 | Hyper | cancer_general | CA3 | chr8 | 85097015 | 85097220 | Hyper | cancer_general | RAIYL |
| chr8 | 86350553 | 86350595 | Hyper | literature | | chr8 | 89339389 | 89339745 | Hyper | tcga, cancer_general | RAIYL |
| chr8 | 89340270 | 89340345 | Hyper | cancer_general | MMP16 | chr8 | 91094221 | 91094251 | Hyper | cancer_general | MMP16 |
| chr8 | 91803676 | 91803718 | Hyper | cancer_general | NECAB1 | chr8 | 91803991 | 91804253 | Hyper | cancer_general | Metazoa_SRP, CALB1 |
| chr8 | 91997046 | 91997947 | Hyper | tcga, cancer_general | TMEM55A, LOC100127983 | chr8 | 93114135 | 93114528 | Hyper | cancer_general, tcga | NECAB1 |
| chr8 | 95651098 | 95651218 | Hyper | liver_tcga | ESRP1, LOC100028748 | chr8 | 95651538 | 95651655 | Hyper | blood | ESRP1, LOC100028748 |
| chr8 | 97157085 | 97158066 | Hyper | tcga, cancer_general | GDF6 | chr8 | 97165644 | 97165676 | Hyper | cancer_general | GDF6 |
| chr8 | 97166425 | 97166455 | Hyper | cancer_general | GDF6 | chr8 | 97167178 | 97167223 | Hyper | cancer_general | GDF6 |
| chr8 | 97167811 | 97167855 | Hyper | pancreas | GDF6 | chr8 | 97169838 | 97170334 | Hyper | cancer_general, tcga | GDF6 |
| chr8 | 97170867 | 97170897 | Hyper | cancer_general | GDF6 | chr8 | 97171129 | 97172200 | Hyper | cancer_general | GDF6 |
| chr8 | 97172433 | 97173458 | Hyper | tcga, cancer_general | GDF6 | chr8 | 97173822 | 97173935 | Hyper | cancer_general | GDF6 |
| chr8 | 97506034 | 97506524 | Hyper | colorectal, cancer_general | SDC2 | chr8 | 97507115 | 97507284 | Hyper | colorectal, cancer_general | SDC2 |
| chr8 | 97507546 | 97507680 | Hyper | tcga | SDC2 | chr8 | 98289825 | 98290260 | Hyper | liver_tcga, cancer_general | TSPYL5 |
| chr8 | 99439104 | 99439133 | Hyper | liver_tcga | KCNS2 | chr8 | 99439382 | 99440354 | Hyper | literature, liver_tcga, cancer_general, tcga | KCNS2 |
| chr8 | 99951404 | 99951434 | Hyper | liver_tcga, cancer_general | OSR2 | chr8 | 99951836 | 99952815 | Hyper | cancer_general | OSR2 |
| chr8 | 99954490 | 99954727 | Hyper | cancer_general | OSR2 | chr8 | 99955180 | 99955327 | Hyper | cancer_general, tcga | OSR2 |
| chr8 | 99959429 | 99959549 | Hyper | liver_tcga | OSR2 | chr8 | 99960329 | 99960971 | Hyper | cancer_general | OSR2 |
| chr8 | 99961187 | 99961272 | Hyper | cancer_general | OSR2 | chr8 | 99961792 | 99961822 | Hyper | literature, liver_tcga, cancer_general | OSR2 |
| chr8 | 99985866 | 99987014 | Hyper | cancer_general | | chr8 | 101118241 | 101118577 | Hyper | cancer_general | |
| chr8 | 101661920 | 101661991 | Hyper | liver_tcga | SNX31 | chr8 | 101821973 | 101822047 | Hyper | liver_tcga, literature | |
| chr8 | 101920382 | 101920468 | Hyper | head_neck | | chr8 | 102504464 | 102504506 | Hyper | | GRHL2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 102505512 | 102505556 | Hyper | liver tcga | GRHL2 | chr8 | 102505797 | 102506000 | Hyper | liver tcga, blood | GRHL2 |
| chr8 | 104153202 | 104153246 | Hyper | cancer_general | BAALC, C8orf56, AK001351 | chr8 | 104153449 | 104153641 | Hyper | cancer_general | BAALC, C8orf56, AK001351 |
| chr8 | 104383700 | 104383985 | Hyper | liver_tcga, tcga | CTHRC1 | | | | | | |
| chr8 | 104513462 | 104513926 | Hyper | tcga, cancer_general | RIMS2 | chr8 | 104512123 | 104513186 | Hyper | tcga, liver_tcga, cancer_general | RIMS2 |
| chr8 | | | | | | chr8 | 105235369 | 105236054 | Hyper | tcga, cancer_general | |
| chr8 | 105478725 | 105479176 | Hyper | cancer_general | | chr8 | 105479404 | 105479464 | Hyper | cancer_general | |
| chr8 | 106331160 | 106331237 | Hyper | cancer_general | ZFPM2 | chr8 | 106332104 | 106332202 | Hyper | tcga | ZFPM2 |
| chr8 | 107282163 | 107282195 | Hyper | esophageal | OXR1 | chr8 | 107284038 | 107284075 | Hyper | cancer_general | OXR1 |
| chr8 | 108509543 | 108509697 | Hyper | lung, cancer_general | | chr8 | 109093679 | 109094180 | Hyper | cancer_general | RSPO2 |
| chr8 | 109094485 | 109094595 | Hyper | cancer_general | RSPO2 | chr8 | 109094840 | 109095932 | Hyper | tcga, cancer_general | RSPO2 |
| chr8 | 109799588 | 109799770 | Hyper | tcga | TMEM74 | chr8 | 110986443 | 110986682 | Hyper | cancer_general | KCNV1 |
| chr8 | 114444580 | 114445192 | Hyper | tcga, cancer_general | CSMD3 | chr8 | 114445763 | 114446068 | Hyper | cancer_general | CSMD3 |
| chr8 | 114446405 | 114446435 | Hyper | cancer_general | CSMD3 | chr8 | 114446931 | 114447368 | Hyper | cancer_general | CSMD3 |
| chr8 | 114449039 | 114449257 | Hyper | cancer_general | CSMD3 | chr8 | 114449550 | 114449602 | Hyper | cancer_general | CSMD3 |
| chr8 | 116660527 | 116660760 | Hyper | cancer_general | TRPS1 | chr8 | 117950438 | 117950468 | Hyper | cancer_general | AARD, AL832163 |
| chr8 | 117950783 | 117950914 | Hyper | cancer_general | AARD, AL832163 | chr8 | 120220116 | 120220145 | Hyper | literature | MAL2 |
| chr8 | 120220428 | 120220592 | Hyper | blood | MAL2 | chr8 | 120650979 | 120651008 | Hyper | literature | |
| chr8 | 120651221 | 120651412 | Hyper | literature | | chr8 | 121136879 | 121137748 | Hyper | tcga, cancer_general | COL14A1 |
| chr8 | 121823901 | 121823930 | Hyper | literature | | chr8 | 121824203 | 121824481 | Hyper | literature | |
| chr8 | 122651872 | 122651905 | Hyper | cancer_general | HAS2, HAS2-AS1 | chr8 | 124173246 | 124173501 | Hyper | tcga, cancer_general | TRNA_Met, WDR67 |
| chr8 | 127569621 | 127569676 | Hyper | blood | FAM84B | chr8 | 132052147 | 132053164 | Hyper | cancer_general | ADCY8 |
| chr8 | 132053715 | 132054749 | Hyper | cancer_general | ADCY8 | chr8 | 139508757 | 139509295 | Hyper | cancer_general | |
| chr8 | 139509741 | 139509928 | Hyper | cancer_general | KCNK9 | chr8 | 140714570 | 140714877 | Hyper | cancer_general | KCNK9 |
| chr8 | 140715090 | 140715120 | Hyper | cancer_general | KCNK9 | chr8 | 140715469 | 140715646 | Hyper | liver_tcga, cancer_general | KCNK9 |
| chr8 | 140715965 | 140716382 | Hyper | cancer_general | | chr8 | 142318155 | 142318184 | Hyper | liver_tcga | |
| chr8 | 142528400 | 142529004 | Hyper | cancer_general, tcga | | chr8 | 143532122 | 143532846 | Hyper | tcga, cancer_general | |
| chr8 | 143533611 | 143533906 | Hyper | cancer_general | | chr8 | 143592657 | 143592687 | Hyper | cancer_general | BAI1 |
| chr8 | 143858522 | 143858699 | Hyper | cancer_general | LYNX1, LY6D | chr8 | 143859322 | 143859361 | Hyper | cancer_general | LY6D, LYNX1 |
| chr8 | 144203653 | 144203708 | Hyper | ovarian | LY6H | chr8 | 144241250 | 144241287 | Hyper | cancer_general | LY6H |
| chr8 | 144241543 | 144241582 | Hyper | cancer_general | LY6H | chr8 | 144241871 | 144242356 | Hyper | tcga, cancer_general | LY6H |
| chr8 | 144328321 | 144328565 | Hyper | cancer_general | ZFP41 | chr8 | 144509325 | 144510529 | Hyper | cancer_general | MAFA, ZC3H3 |
| chr8 | 144511225 | 144511424 | Hyper | cancer_general | ZC3H3, MAFA | chr8 | 144512041 | 144512192 | Hyper | liver_tcga, cancer_general | ZC3H3, MAFA |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 144512473 | 144512503 | Hyper | blood | ZC3H3, MAFA | chr8 | 144601799 | 144601851 | Hyper | liver_tcga | ZC3H3 |
| chr8 | 144650594 | 144650730 | Hyper | liver_tcga | GSDMD, MROH6, NAPRT1 | chr8 | 145033304 | 145033333 | Hyper | liver_tcga | |
| chr8 | 145698347 | 145698379 | Hyper | cancer_general | CYHR1, FOXH1, KIFC2 | chr8 | 145806258 | 145806287 | Hyper | liver_tcga | ARHGAP39 |
| chr8 | 145925461 | 145925491 | Hyper | cancer_general | DQ588968 | chr8 | 145925947 | 145926089 | Hyper | liver_tcga | DQ588968 |
| chr13 | 20175911 | 20175941 | Hyper | hepatobiliary | | chr13 | 20735804 | 20736089 | Hyper | tcga | IL17D, AK05408, N6AMT2 |
| chr13 | 20875763 | 20875919 | Hyper | cancer_general | | chr13 | 21295926 | 21295955 | Hyper | liver_tcga | |
| chr13 | 21649636 | 21649775 | Hyper | cancer_general | | chr13 | 22243273 | 22243469 | Hyper | tcga, cancer_general | FGF9 |
| chr13 | 23489851 | 23489914 | Hyper | cancer_general | | chr13 | 23733447 | 23734020 | Hyper | cancer_general | |
| chr13 | 23734284 | 23734678 | Hyper | tcga, cancer_general | | chr13 | 24477643 | 24477906 | Hyper | cancer_general | ANKRD20A19P, C1QTNF9B |
| chr13 | 25115713 | 25115771 | Hyper | cancer_general | | chr13 | 25319856 | 25321350 | Hyper | cancer_general, tcga | |
| chr13 | 25321699 | 25321942 | Hyper | cancer_general | | chr13 | 25593042 | 25593242 | Hyper | tcga | BC022569, AMER2 |
| chr13 | 25621045 | 25621394 | Hyper | cancer_general | | chr13 | 25744716 | 25746000 | Hyper | tcga, cancer_general | ATP8A2 |
| chr13 | 25946205 | 25946411 | Hyper | tcga, cancer_general | ATP8A2 | chr13 | 25946620 | 25946796 | Hyper | cancer_general | |
| chr13 | 26042678 | 26043499 | Hyper | cancer_general | ATP8A2 | chr13 | 26625301 | 26625727 | Hyper | cancer_general, colorectal | SHISA2 |
| chr13 | 26626077 | 26626148 | Hyper | tcga | SHISA2 | chr13 | 27132407 | 27132445 | Hyper | tcga | WASF3 |
| chr13 | 27334211 | 27334563 | Hyper | cancer_general | GPR12 | chr13 | 27334772 | 27334894 | Hyper | cancer_general | GPR12 |
| chr13 | 28365705 | 28366122 | Hyper | colorectal, cancer_general | GSX1 | chr13 | 28366482 | 28366577 | Hyper | cancer_general | GSX1 |
| chr13 | 28367024 | 28367059 | Hyper | cancer_general | GSX1 | chr13 | 28367794 | 28368168 | Hyper | cancer_general | GSX1 |
| chr13 | 28368451 | 28368593 | Hyper | cancer_general | GSX1 | chr13 | 28368952 | 28369990 | Hyper | cancer_general | GSX1 |
| chr13 | 28370947 | 28371061 | Hyper | cancer_general | GSX1 | chr13 | 28394766 | 28394866 | Hyper | cancer_general | |
| chr13 | 28395501 | 28395553 | Hyper | cancer_general | | chr13 | 28395998 | 28396073 | Hyper | cancer_general | |
| chr13 | 28491793 | 28491946 | Hyper | cancer_general | PDX1 | chr13 | 28492244 | 28492553 | Hyper | cancer_general | PDX1 |
| chr13 | 28503042 | 28503074 | Hyper | cancer_general | PDX1 | chr13 | 28528534 | 28528748 | Hyper | cancer_general | CDX2, ATP5EP2 |
| chr13 | 28540745 | 28540927 | Hyper | cancer_general | CDX2 | chr13 | 28543212 | 28543242 | Hyper | cancer_general | PRHOXNB, CDX2 |
| chr13 | 28544397 | 28544903 | Hyper | cancer_general | PRHOXNB, CDX2, PRHOXNB | chr13 | 28549497 | 28550552 | Hyper | cancer_general | PRHOXNB, CDX2 |
| chr13 | 28551417 | 28551461 | Hyper | cancer_general | PRHOXNB, CDX2 | chr13 | 28551950 | 28552167 | Hyper | cancer_general | PRHOXNB, CDX2 |
| chr13 | 28552555 | 28552585 | Hyper | cancer_general | PRHOXNB, CDX2 | chr13 | 28552794 | 28552824 | Hyper | cancer_general | |
| chr13 | 28553030 | 28553138 | Hyper | literature | FLT3 | chr13 | 28589765 | 28589794 | Hyper | literature | FLT3 |
| chr13 | 28592605 | 28592658 | Hyper | literature | FLT3 | chr13 | 28601345 | 28601374 | Hyper | literature | FLT3 |
| chr13 | 28602326 | 28602355 | Hyper | literature | FLT3 | chr13 | 28608233 | 28608355 | Hyper | literature | FLT3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 28610123 | 28610152 | Hyper | literature | FLT3 | chr13 | 28674018 | 28674734 | Hyper | tcga, cancer_general | FLT3 |
| chr13 | 29067773 | 29068416 | Hyper | cancer_general | BC048278, FLT1 | chr13 | 29068926 | 29069065 | Hyper | cancer_general | BC048278, FLT1 |
| chr13 | 29106308 | 29107309 | Hyper | tcga, cancer_general | BC035084, FRY | chr13 | 32605034 | 32605966 | Hyper | pancreas | BC035084, FRY |
| chr13 | 33590822 | 33590949 | Hyper | cancer_general | KL | chr13 | 33591300 | 33591419 | Hyper | cancer_general | KL |
| chr13 | 33924666 | 33924790 | Hyper | cancer_general | NBEA, MIR548F5 | chr13 | 35517395 | 35517648 | Hyper | tcga | NBEA |
| chr13 | 36044829 | 36044930 | Hyper | cancer_general | NBEA, MIR548F5 | chr13 | 36045267 | 36045297 | Hyper | cancer_general | NBEA, MIR548F5 |
| chr13 | 36049995 | 36050025 | Hyper | pancreas | NBEA, MIR548F5 | chr13 | 36704939 | 36705055 | Hyper | cancer_general, tcga | |
| chr13 | 36705451 | 36705489 | Hyper | cancer_general | SPG20OS, SPG20 | chr13 | 36729093 | 36729125 | Hyper | cancer_general | SPG20OS, SPG20 |
| chr13 | 36920317 | 36920413 | Hyper | liver_tcga, colorectal, cancer_general | | chr13 | 36920628 | 36920785 | Hyper | tcga, cancer_general, colorectal | |
| chr13 | 37004771 | 37005129 | Hyper | cancer_general | CCNA1 | chr13 | 37005657 | 37006762 | Hyper | cancer_general | CCNA1 |
| chr13 | 37248063 | 37248319 | Hyper | tcga | SERTM1 | chr13 | 37248979 | 37249030 | Hyper | cancer_general | SERTM1 Mir_720, TRPC4 |
| chr13 | 37633989 | 37634018 | Hyper | literature | SUPT20H | chr13 | 38443618 | 38443827 | Hyper | cancer_general | |
| chr13 | 39261410 | 39261446 | Hyper | tcga | FREM2 | chr13 | 43148421 | 43148450 | Hyper | tcga | TNFSF11 EPSTI1 |
| chr13 | 43148669 | 43148698 | Hyper | tcga | TNFSF11 | chr13 | 43566247 | 43566647 | Hyper | tcga, cancer_general | |
| chr13 | 44947746 | 44948197 | Hyper | cancer_general | SERP2 | chr13 | 45150013 | 45150276 | Hyper | tcga, liver_tcga | TSC22D1-AS1, TSC22D1 |
| chr13 | 45885876 | 45885905 | Hyper | liver_tcga | KIAA0226L | chr13 | 46425548 | 46425584 | Hyper | cancer_general | SLAH3 |
| chr13 | 46961494 | 46961533 | Hyper | esophageal | HTR2A | chr13 | 46961952 | 46961982 | Hyper | esophageal | KIAA0226L |
| chr13 | 47468139 | 47468168 | Hyper | literature | | chr13 | 49794117 | 49795168 | Hyper | esophageal, cancer_general | MLNR |
| chr13 | 53312991 | 53313920 | Hyper | cancer_general | LECT1 | chr13 | 53419734 | 53419775 | Hyper | liver_tcga, cancer_general | PCDH8 |
| chr13 | 53420020 | 53420080 | Hyper | cancer_general | PCDH8 | chr13 | 53420385 | 53420720 | Hyper | cancer_general | PCDH8 |
| chr13 | 53421253 | 53421787 | Hyper | cancer_general | PCDH8 | chr13 | 53422315 | 53422362 | Hyper | cancer_general | PCDH8 |
| chr13 | 53423838 | 53423978 | Hyper | cancer_general | PCDH8 | chr13 | 58203602 | 58203644 | Hyper | cancer_general | PCDH17 |
| chr13 | 58203851 | 58204103 | Hyper | cancer_general | PCDH17 | chr13 | 58204350 | 58204393 | Hyper | tcga | PCDH17 |
| chr13 | 58206042 | 58206983 | Hyper | cancer_general | PCDH17 | chr13 | 58207462 | 58208020 | Hyper | cancer_general | PCDH17 |
| chr13 | 58208495 | 58208926 | Hyper | cancer_general | PCDH17 | chr13 | 67803735 | 67804074 | Hyper | tcga, cancer_general | PCDH9 |
| chr13 | 67804494 | 67804523 | Hyper | literature | PCDH9 | chr13 | 67805191 | 67805247 | Hyper | cancer_general | PCDH9 |
| chr13 | 70681626 | 70682071 | Hyper | cancer_general | ATXN8OS, KLHL1 | chr13 | 72439142 | 72439250 | Hyper | cancer_general | DACH1 |
| chr13 | 73336049 | 73336078 | Hyper | literature | DIS3, BORA | chr13 | 78492684 | 78492840 | Hyper | esophageal | RNF219-AS1, EDNRB |
| chr13 | 78493166 | 78493196 | Hyper | cancer_general | RNF219-AS1, EDNRB | chr13 | 78493455 | 78493809 | Hyper | cancer_general | RNF219-AS1, EDNRB |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 79168067 | 79168102 | Hyper | pancreas | POU4F1, RNF219-AS1 | chr13 | 79169818 | 79170884 | Hyper | literature, cancer_general | IRNF219-AS1, POU4F1 |
| chr13 | 79171118 | 79171196 | Hyper | cancer_general | POU4F1, RNF219-AS1 | chr13 | 79175770 | 79176783 | Hyper | liver_tcga, cancer_general | RNF219-AS1, POU4F1 |
| chr13 | 79176993 | 79177998 | Hyper | tcga, liver_tcga, cancer_general | POU4F1, RNF219-AS1 | chr13 | 79183406 | 79183485 | Hyper | cancer_general | RNF219-AS1, POU4F1, RNF219-AS1 |
| chr13 | 81229343 | 81229372 | Hyper | literature | SLITRK1 | chr13 | 84455236 | 84455292 | Hyper | cancer_general | SLITRK1 |
| chr13 | 84455581 | 84455715 | Hyper | cancer_general | SLITRK1 | chr13 | 84457491 | 84457521 | Hyper | cancer_general | SLITRK1 |
| chr13 | 88323579 | 88324207 | Hyper | tcga, cancer_general | SLITRK5 | chr13 | 88324516 | 88324611 | Hyper | colorectal, cancer_general | SLITRK5 |
| chr13 | 88325300 | 88325460 | Hyper | cancer_general | SLITRK5 | chr13 | 88325819 | 88326061 | Hyper | cancer_general | SLITRK5 |
| chr13 | 88326538 | 88327014 | Hyper | cancer_general, tcga | SLITRK5 | chr13 | 92050760 | 92050814 | Hyper | esophageal | GPC5 |
| chr13 | 92051139 | 92051168 | Hyper | tcga | GPC5 | chr13 | 92051374 | 92051529 | Hyper | tcga, cancer_general | GPC5 |
| chr13 | 93879288 | 93879375 | Hyper | tcga | GPC6 | chr13 | 93879670 | 93879700 | Hyper | cancer_general | GPC6 |
| chr13 | 93880089 | 93880856 | Hyper | tcga, colorectal, cancer_general | GPC6 | chr13 | 95357311 | 95357341 | Hyper | cancer_general | SOX21, AK055459 |
| chr13 | 95357574 | 95357775 | Hyper | cancer_general | SOX21, AK055459 | chr13 | 95358041 | 95358165 | Hyper | cancer_general | SOX21, AK055459 |
| chr13 | 95359747 | 95359803 | Hyper | cancer_general | SOX21, AK055459 | chr13 | 95360322 | 95360371 | Hyper | cancer_general | SOX21, AK055459 |
| chr13 | 95363210 | 95363429 | Hyper | liver_tcga | SOX21, AK055459 | chr13 | 95363796 | 95364196 | Hyper | tcga, cancer_general | AK055459, SOX21 |
| chr13 | 95364495 | 95364800 | Hyper | tcga, cancer_general, colorectal | AK055459, SOX21 | chr13 | 95620021 | 95620078 | Hyper | cancer_general, colorectal, cancer_general | SOX21 |
| chr13 | 95620647 | 95621011 | Hyper | cancer_general, tcga | | chr13 | 96204853 | 96205363 | Hyper | liver_tcga, cancer_general | CLDN10 |
| chr13 | 96296225 | 96296473 | Hyper | cancer_general | | chr13 | 96296693 | 96297137 | Hyper | tcga, cancer_general | |
| chr13 | 96743788 | 96744175 | Hyper | tcga, cancer_general | HS6ST3 | chr13 | 100547713 | 100547982 | Hyper | cancer_general | |
| chr13 | 100608257 | 100609055 | Hyper | cancer_general | ZIC5 | chr13 | 100621941 | 100622015 | Hyper | cancer_general | ZIC5 |
| chr13 | 100624316 | 100624348 | Hyper | cancer_general | ZIC2, ZIC5 | chr13 | 100624587 | 100624729 | Hyper | cancer_general | ZIC2, ZIC5 |
| chr13 | 100626929 | 100627009 | Hyper | cancer_general | ZIC2, ZIC5 | chr13 | 100627295 | 100627348 | Hyper | cancer_general | ZIC2, ZIC5 |
| chr13 | 100627688 | 100627717 | Hyper | liver_tcga | ZIC2, ZIC5 | chr13 | 100630169 | 100630430 | Hyper | liver_tcga | ZIC2, ZIC5 |
| chr13 | 100630630 | 100630997 | Hyper | cancer_general | ZIC5, ZIC2 | chr13 | 100633089 | 100633184 | Hyper | blood | ZIC2 |
| chr13 | 100634314 | 100634617 | Hyper | blood | ZIC2 | chr13 | 100635406 | 100635451 | Hyper | cancer_general | ZIC2 |
| chr13 | 100636167 | 100636238 | Hyper | cancer_general | ZIC2 | chr13 | 100637390 | 100637485 | Hyper | cancer_general | ZIC2 |
| chr13 | 100641282 | 100642201 | Hyper | cancer_general | ZIC2 | chr13 | 100643296 | 100643435 | Hyper | cancer_general | ZIC2 |
| chr13 | 100644055 | 100644212 | Hyper | cancer_general | ZIC2 | chr13 | 100649325 | 100649931 | Hyper | cancer_general | |
| chr13 | 102568454 | 102568484 | Hyper | cancer_general | FGF14 | chr13 | 102568856 | 102568994 | Hyper | tcga, cancer_general | FGF14 |
| chr13 | 102569203 | 102569542 | Hyper | cancer_general | FGF14 | chr13 | 103046721 | 103046995 | Hyper | cancer_general | FGF14-AS2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 103052347 | 103052574 | Hyper | tcga | FGF14-AS2 | chr13 | 103052892 | 103052940 | Hyper | cancer_general | FGF14-AS2 |
| chr13 | 103053394 | 103053496 | Hyper | tcga | FGF14-AS2 | chr13 | 105791875 | 105791904 | Hyper | literature | |
| chr13 | 107186855 | 107186884 | Hyper | liver_tcga | ARGLU1, EFNB2 | chr13 | 107187162 | 107187426 | Hyper | liver_tcga, tcga | |
| chr13 | 107187666 | 107187695 | Hyper | liver_tcga | ARGLU1, EFNB2 | chr13 | 107188241 | 107188430 | Hyper | tcga, liver_tcga | ARGLU1, EFNB2 |
| chr13 | 108518355 | 108518392 | Hyper | cancer_general | | chr13 | 108518813 | 108518933 | Hyper | cancer_general | |
| chr13 | 108519254 | 108519367 | Hyper | cancer_general | | chr13 | 108519737 | 108519894 | Hyper | tcga | |
| chr13 | 108520376 | 108520580 | Hyper | tcga, cancer_general | | chr13 | 108520979 | 108521076 | Hyper | cancer_general | |
| chr13 | 109147685 | 109148351 | Hyper | cancer_general | | chr13 | 109148783 | 109149185 | Hyper | tcga, cancer_general | |
| chr13 | 110958816 | 110958981 | Hyper | cancer_general | COL4A1, COL4A2 | chr13 | 110959220 | 110959255 | Hyper | cancer_general | COL4A2, COL4A1 |
| chr13 | 110959705 | 110959970 | Hyper | colorectal, cancer_general | COL4A2, COL4A1 | chr13 | 110960250 | 110960282 | Hyper | cancer_general | COL4A2, COL4A1 |
| chr13 | 110960541 | 110960603 | Hyper | cancer_general | COL4A2, COL4A1 | chr13 | 112707694 | 112707869 | Hyper | cancer_general | |
| chr13 | 112708088 | 112708513 | Hyper | cancer_general | | chr13 | 112709388 | 112709617 | Hyper | cancer_general | |
| chr13 | 112709883 | 112709928 | Hyper | cancer_general | | chr13 | 112710344 | 112710508 | Hyper | cancer_general | |
| chr13 | 112710759 | 112711776 | Hyper | cancer_general | | chr13 | 112712017 | 112713029 | Hyper | cancer_general | |
| chr13 | 112715370 | 112715642 | Hyper | cancer_general | | chr13 | 112715985 | 112716313 | Hyper | cancer_general | SOX1 |
| chr13 | 112716677 | 112716721 | Hyper | cancer_general | SOX1 | chr13 | 112717026 | 112717536 | Hyper | cancer_general | SOX1 |
| chr13 | 112717835 | 112717949 | Hyper | cancer_general | SOX1 | chr13 | 112720033 | 112720505 | Hyper | cancer_general | SOX1 |
| chr13 | 112720723 | 112720767 | Hyper | cancer_general | SOX1 | chr13 | 112721012 | 112721042 | Hyper | cancer_general | SOX1 |
| chr13 | 112721261 | 112722312 | Hyper | liver_tcga, literature, cancer_general | SOX1 | chr13 | 112724505 | 112724535 | Hyper | cancer_general | SOX1 |
| chr13 | 112726337 | 112726560 | Hyper | cancer_general | SOX1 | chr13 | 112727984 | 112728270 | Hyper | cancer_general | SOX1 |
| chr13 | 112758107 | 112758257 | Hyper | cancer_general | AK055145 | chr13 | 112758463 | 112758613 | Hyper | cancer_general | AK055145 |
| chr13 | 112758849 | 112759248 | Hyper | cancer_general | AK055145 | chr13 | 112759612 | 112759642 | Hyper | cancer_general | AK055145 |
| chr13 | 112759959 | 112760327 | Hyper | cancer_general | AK055145 | chr13 | 112760795 | 112761214 | Hyper | cancer_general | |
| chr13 | 113244509 | 113244595 | Hyper | pancreas | TUBGCP3 | chr13 | 114897194 | 114897240 | Hyper | hepatobiliary | |
| AC211950.2_11234-25326 | 129 | 257 | Hyper | cancer_general | | AC211950.2_11234-25326 | 13335 | 13445 | Hyper | cancer_general | |
| chr15 | 13743 | 13889 | Hyper | cancer_general | | chr15 | 23158397 | 23158489 | Hyper | cancer_general | |
| chr15 | 26107640 | 26107860 | Hyper | cancer_general | | chr15 | 26108096 | 26108701 | Hyper | tcga, cancer_general | |
| chr15 | 27018363 | 27018436 | Hyper | cancer_general | | chr15 | 27212887 | 27213172 | Hyper | cancer_general | GABRG3 |
| chr15 | 27216396 | 27216429 | Hyper | cancer_general | GABRG3 | chr15 | 27604062 | 27604139 | Hyper | cancer_general | GABRG3 |
| chr15 | 28341699 | 28342429 | Hyper | tcga, cancer_general | OCA2 | chr15 | 28344173 | 28344287 | Hyper | cancer_general | OCA2 |
| chr15 | 28352240 | 28353850 | Hyper | cancer_general, tcga | HERC2, OCA2 | chr15 | 29077284 | 29077383 | Hyper | cancer_general | LOC646278 |
| chr15 | 29130807 | 29131875 | Hyper | cancer_general | APBA2 | chr15 | 29396330 | 29396360 | Hyper | pancreas | APBA2 |
| chr15 | 29407777 | 29408001 | Hyper | tcga | FAM189A1 | chr15 | 29862502 | 29862282 | Hyper | tcga | |
| chr15 | 30115185 | 30115228 | Hyper | blood | TJP1 | chr15 | 31775596 | 31776121 | Hyper | cancer_general | OTUD7A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 32933918 | 32934018 | Hyper | liver_tcga, literature | SCG5, ARHGAP11A | chr15 | 33009747 | 33011348 | Hyper | tcga, liver_tcga, cancer_general | GREM1, AX747968 |
| chr15 | 33011601 | 33011633 | Hyper | cancer_general | GREM1, AX747968 | chr15 | 33487057 | 33487120 | Hyper | liver_tcga | FMN1 |
| chr15 | 33602801 | 33602886 | Hyper | cancer_general | RYR3 | chr15 | 33603194 | 33603624 | Hyper | cancer_general | RYR3 |
| chr15 | 34517058 | 34517334 | Hyper | esophageal | EMC4, SLC12A6 | chr15 | 34630420 | 34630449 | Hyper | tcga | NOP10, NUTM1, SLC12A6 |
| chr15 | 34729478 | 34729582 | Hyper | cancer_general | | chr15 | 34786504 | 34787304 | Hyper | cancer_general | AK092087, GJD2 |
| chr15 | 35046607 | 35046637 | Hyper | cancer_general | AK092087, GJD2 | chr15 | 35047034 | 35047133 | Hyper | cancer_general | AK092087, GJD2 |
| chr15 | 35087666 | 35087698 | Hyper | cancer_general | AK092087, ACTC1 | chr15 | 37180309 | 37180743 | Hyper | cancer_general | MEIS2, LOC145845 |
| chr15 | 37402974 | 37403238 | Hyper | lung, cancer_general | MEIS2 | chr15 | 40211819 | 40212190 | Hyper | cancer_general | GPR176 |
| chr15 | 40575630 | 40575744 | Hyper | tcga, cancer_general | PLCB2, ANKRD63, PAK6 | chr15 | 40675092 | 40675121 | Hyper | literature | KNSTRN |
| chr15 | 40763811 | 40763862 | Hyper | hepatobiliary | CHST14, BAHD1 | chr15 | 41787804 | 41787852 | Hyper | cancer_general | LTK, ITPKA |
| chr15 | 41804878 | 41805772 | Hyper | cancer_general | RPAP1, LTK, ITPKA | chr15 | 41913750 | 41913807 | Hyper | cancer_general | MGA |
| chr15 | 41952572 | 41952711 | Hyper | cancer_general | MGA | chr15 | 43810405 | 43810435 | Hyper | pancreas | MAP1A |
| chr15 | 45403636 | 45404130 | Hyper | cancer_general | DUOXA2, DUOXA1, DUOX2 | chr15 | 45404881 | 45405117 | Hyper | tcga | DUOXA2, DUOXA1, DUOX2 |
| chr15 | 45421385 | 45421435 | Hyper | cancer_general | DUOX1, DUOXA1 | chr15 | 45421950 | 45422095 | Hyper | liver_tcga | DUOX1, DUOXA1 |
| chr15 | 45427354 | 45427410 | Hyper | cancer_general | DUOXA1, DUOX1 | chr15 | 45427611 | 45427786 | Hyper | cancer_general | DUOX1, DUOXA1 |
| chr15 | 45479460 | 45479697 | Hyper | cancer_general | SHF | chr15 | 45493209 | 45493371 | Hyper | ovarian | TRNA, TRNA_His |
| chr15 | 45670462 | 45670879 | Hyper | colorectal | BC039389, GATM, GATM-AS1 | chr15 | 47476118 | 47476450 | Hyper | tcga | SEMA6D |
| chr15 | 47476868 | 47477018 | Hyper | tcga | SEMA6D | chr15 | 48483956 | 48483986 | Hyper | cancer_general | CTXN2, SLC12A1 |
| chr15 | 48936726 | 48937987 | Hyper | colorectal, cancer_general, tcga | FBN1 | chr15 | 48938212 | 48938510 | Hyper | cancer_general | FBN1 |
| chr15 | 51385913 | 51386181 | Hyper | cancer_general | TNFAIP8L3 | chr15 | 51634075 | 51634135 | Hyper | cancer_general | GLDN |
| chr15 | 51973646 | 51973934 | Hyper | tcga | SCG3 | chr15 | 53075809 | 53077361 | Hyper | cancer_general | ONECUT1 |
| chr15 | 53077655 | 53077731 | Hyper | cancer_general | ONECUT1 | chr15 | 53078064 | 53078236 | Hyper | cancer_general | ONECUT1 |
| chr15 | 53079340 | 53080082 | Hyper | cancer_general | ONECUT1 | chr15 | 53080337 | 53080606 | Hyper | cancer_general | ONECUT1 |
| chr15 | 53080935 | 53081025 | Hyper | cancer_general | ONECUT1 | chr15 | 53081306 | 53081677 | Hyper | cancer_general | ONECUT1 |
| chr15 | 53082443 | 53082491 | Hyper | esophageal | | chr15 | 53096816 | 53096891 | Hyper | cancer_general | |
| chr15 | 53097231 | 53097261 | Hyper | cancer_general | | chr15 | 53097634 | 53097974 | Hyper | tcga, cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 53098316 | 53098658 | Hyper | cancer_general | | chr15 | 54270498 | 54270707 | Hyper | tcga, cancer_general | PYGO1 |
| chr15 | 54270932 | 54270961 | Hyper | tcga | | chr15 | 55880879 | 55881011 | Hyper | tcga | ALDH1A2 |
| chr15 | 58357318 | 58357451 | Hyper | cancer_general | ALDH1A2 | chr15 | 58357733 | 58358200 | Hyper | cancer_general, liver_tcga | |
| chr15 | 59158809 | 59158901 | Hyper | pancreas | unknown, FAM63B | chr15 | 60287038 | 60287733 | Hyper | cancer_general | FOXB1 |
| chr15 | 60288786 | 60288844 | Hyper | cancer_general | FOXB1 | chr15 | 60289310 | 60289546 | Hyper | tcga, cancer_general | FOXB1 |
| chr15 | 60296122 | 60296209 | Hyper | cancer_general | FOXB1 | chr15 | 60296598 | 60297409 | Hyper | tcga, liver_tcga, cancer_general | FOXB1 |
| chr15 | 60297637 | 60298108 | Hyper | cancer_general | FOXB1 | chr15 | 61520916 | 61521014 | Hyper | tcga | C2CD4B |
| chr15 | 61521659 | 61521937 | Hyper | tcga | IGDCC4 | chr15 | 62456922 | 62456952 | Hyper | blood | MAP2K1 |
| chr15 | 65669859 | 65669899 | Hyper | esophageal | MAP2K1 | chr15 | 66727409 | 66727498 | Hyper | literature | SNAPC5, MAP2K1 |
| chr15 | 66729148 | 66729177 | Hyper | literature | | chr15 | 66774117 | 66774203 | Hyper | literature | |
| chr15 | 68112611 | 68112641 | Hyper | cancer_general | SKOR1 | chr15 | 68113868 | 68113898 | Hyper | cancer_general | SKOR1 |
| chr15 | 68114139 | 68114195 | Hyper | cancer_general | SKOR1 | chr15 | 68116369 | 68116621 | Hyper | cancer_general | SKOR1 |
| chr15 | 68117830 | 68118633 | Hyper | cancer_general | SKOR1 | chr15 | 68118886 | 68119218 | Hyper | cancer_general | SKOR1 |
| chr15 | 68119548 | 68120576 | Hyper | cancer_general | SKOR1 | chr15 | 68120827 | 68120857 | Hyper | cancer_general | SKOR1 |
| chr15 | 68121058 | 68122076 | Hyper | cancer_general | SKOR1 | chr15 | 68122643 | 68122673 | Hyper | cancer_general | SKOR1 |
| chr15 | 68125261 | 68125664 | Hyper | lung, cancer_general | SKOR1 | chr15 | 68127801 | 68128350 | Hyper | cancer_general | SKOR1 |
| chr15 | 68128594 | 68128688 | Hyper | pancreas | SKOR1 | chr15 | 68260519 | 68260709 | Hyper | liver_tcga | CELF6 |
| chr15 | 71055636 | 71055815 | Hyper | blood | | chr15 | 72612540 | 72612906 | Hyper | liver_tcga, hepatobiliary | |
| chr15 | 73660004 | 73660067 | Hyper | cancer_general | HCN4 | chr15 | 73661469 | 73661666 | Hyper | cancer_general, tcga | HCN4 |
| chr15 | 74045060 | 74045097 | Hyper | tcga | C15orf59 | chr15 | 74422006 | 74422146 | Hyper | cancer_general | ISLR2, LOC283731 |
| chr15 | 74422869 | 74423002 | Hyper | cancer_general | ISLR2, LOC283731 | chr15 | 74658151 | 74658587 | Hyper | tcga, cancer_general | BC013681, CYP11A1, LOC729739 |
| chr15 | 75251346 | 75251382 | Hyper | cancer_general | RPP25 | chr15 | 75251672 | 75251786 | Hyper | cancer_general | RPP25 |
| chr15 | 75471116 | 75471193 | Hyper | cancer_general | | chr15 | 76627508 | 76627826 | Hyper | liver_tcga, cancer_general | ISL2 |
| chr15 | 76629056 | 76629220 | Hyper | cancer_general | ISL2 | chr15 | 76629494 | 76629531 | Hyper | lung | ISL2 |
| chr15 | 76629814 | 76630847 | Hyper | cancer_general | SCAPER, ISL2 | chr15 | 76632257 | 76632423 | Hyper | cancer_general | SCAPER, ISL2 |
| chr15 | 76635120 | 76635197 | Hyper | cancer_general | SCAPER, ISL2 | chr15 | 76635530 | 76635560 | Hyper | cancer_general | SCAPER, ISL2 |
| chr15 | 76638472 | 76638719 | Hyper | cancer_general | SCAPER, ISL2 | chr15 | 78111154 | 78111210 | Hyper | cancer_general | |
| chr15 | 78556819 | 78557108 | Hyper | tcga, liver_tcga | DNAJA4 | chr15 | 78632727 | 78632823 | Hyper | cancer_general | CRABP1 |
| chr15 | 78912281 | 78912401 | Hyper | cancer_general | CHRNB4, AX748237, CHRNA3 | chr15 | 78912623 | 78912653 | Hyper | cancer_general | CHRNB4, AX748237, CHRNA3 |
| chr15 | 78912912 | 78913170 | Hyper | tcga, cancer_general | CHRNB4, AX748237, CHRNA3 | chr15 | 78913535 | 78913651 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 79104217 | 79104246 | Hyper | tcga | ADAMTS7 | chr15 | 79104466 | 79104495 | Hyper | tcga | ADAMTS7 |
| chr15 | 79381705 | 79382571 | Hyper | cancer_general | | chr15 | 79382786 | 79383257 | Hyper | cancer_general | MIR184, LOC729911 |
| chr15 | 79383947 | 79383977 | Hyper | colorectal | | chr15 | 79502211 | 79502360 | Hyper | cancer_general | |
| chr15 | 79575278 | 79575474 | Hyper | cancer_general | ANKRD34C | chr15 | 79576145 | 79576277 | Hyper | cancer_general | ANKRD34C |
| chr15 | 79724126 | 79724240 | Hyper | cancer_general | KIAA1024 | chr15 | 79724502 | 79725140 | Hyper | tcga, cancer_general | KIAA1024 |
| chr15 | 79725422 | 79725539 | Hyper | cancer_general | KIAA1024 | chr15 | 81071827 | 81071867 | Hyper | blood | KIAA1199 |
| chr15 | 82336879 | 82336972 | Hyper | cancer_general | MEX3B | chr15 | 82340070 | 82340157 | Hyper | cancer_general | MEX3B |
| chr15 | 83315336 | 83315393 | Hyper | cancer_general | LOC283692 | chr15 | 83316251 | 83317087 | Hyper | cancer_general | LOC283692 |
| chr15 | 83349234 | 83349686 | Hyper | cancer_general | AP3B2 | chr15 | 83378212 | 83378370 | Hyper | esophageal | LOC338963, AP3B2 |
| chr15 | 83776255 | 83776785 | Hyper | liver_tcga, colorectal, cancer_general | TM6SF1 | chr15 | 83875648 | 83875901 | Hyper | liver_tcga, cancer_general | HDGFRP3 |
| chr15 | 83877055 | 83877149 | Hyper | tcga | HDGFRP3 | chr15 | 83952198 | 83952736 | Hyper | tcga, cancer_general | BNC1 |
| chr15 | 83953102 | 83953903 | Hyper | tcga, cancer_general | BNC1 | chr15 | 83954380 | 83954409 | Hyper | literature | BNC1 |
| chr15 | 84115747 | 84115966 | Hyper | cancer_general | SH3GL3 | chr15 | 84116905 | 84116949 | Hyper | tcga | SH3GL3 |
| chr15 | 84322851 | 84323037 | Hyper | cancer_general | ADAMTSL3 | chr15 | 84748578 | 84749260 | Hyper | cancer_general | EFTUD1P1 |
| chr15 | 88798688 | 88798791 | Hyper | cancer_general | NTRK3, NTRK3-AS1 | chr15 | 88799537 | 88800317 | Hyper | cancer_general, tcga | NTRK3-AS1, NTRK3 |
| chr15 | 88800541 | 88801103 | Hyper | cancer_general | NTRK3-AS1, NTRK3 | chr15 | 89149169 | 89149448 | Hyper | cancer_general | MIR1179, MIR7-2, MIR3529, AK054749 |
| chr15 | 89248753 | 89248907 | Hyper | tcga, cancer_general | ACAN | chr15 | 89346050 | 89346393 | Hyper | cancer_general | ACAN |
| chr15 | 89346670 | 89346943 | Hyper | cancer_general | | chr15 | 89903484 | 89903814 | Hyper | cancer_general | MIR9-3, LINC00925 |
| chr15 | 89910521 | 89910748 | Hyper | cancer_general | MIR9-3, LINC00925 | chr15 | 89911087 | 89911186 | Hyper | cancer_general | MIR9-3, LINC00925 |
| chr15 | 89913750 | 89913780 | Hyper | cancer_general | MIR9-3, LINC00925 | chr15 | 89914231 | 89914895 | Hyper | cancer_general | LINC00925, MIR9-3 |
| chr15 | 89915240 | 89915369 | Hyper | cancer_general | LINC00925, MIR9-3 | chr15 | 89920809 | 89920901 | Hyper | literature | LINC00925, MIR9-3 |
| chr15 | 89921956 | 89922006 | Hyper | cancer_general | LINC00925 | chr15 | 89922211 | 89922546 | Hyper | cancer_general | LINC00925 |
| chr15 | 89942755 | 89942945 | Hyper | cancer_general | AK054710, LINC00925 | chr15 | 89943410 | 89943706 | Hyper | pancreas, liver_tcga, tcga | AK054710, LINC00925 |
| chr15 | 89949410 | 89949942 | Hyper | cancer_general | AK054710, LINC00925 | chr15 | 89950236 | 89951113 | Hyper | cancer_general | AK054710, LINC00925 |
| chr15 | 89951400 | 89951801 | Hyper | cancer_general | AK054710, LINC00925 | chr15 | 89952153 | 89953055 | Hyper | literature, cancer_general | |
| chr15 | 89954197 | 89954335 | Hyper | cancer_general | LINC00928, RHCG | chr15 | 89956364 | 89956450 | Hyper | cancer_general | |
| chr15 | 90039563 | 90039711 | Hyper | cancer_general | | chr15 | 90631823 | 90631948 | Hyper | literature | IDH2 |
| chr15 | 91643360 | 91643586 | Hyper | esophageal | SV2B | chr15 | 92936290 | 92936322 | Hyper | cancer_general | ST8SIA2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 92937153 | 92937374 | Hyper | cancer_general, tcga | ST8SIA2 | chr15 | 92937927 | 92938309 | Hyper | tcga, cancer_general | ST8SIA2 |
| chr15 | 93631739 | 93632014 | Hyper | tcga, cancer_general | | chr15 | 93632660 | 93633233 | Hyper | cancer_general, tcga | |
| chr15 | 95388568 | 95388616 | Hyper | cancer_general | LOC440311 | chr15 | 96874362 | 96874514 | Hyper | blood | NR2F2, MIR1469, NR2F2-AS1 |
| chr15 | 96889154 | 96889183 | Hyper | tcga | NR2F2 | chr15 | 96889401 | 96889430 | Hyper | tcga | NR2F2 |
| chr15 | 96897934 | 96898010 | Hyper | cancer_general | | chr15 | 96911559 | 96911710 | Hyper | cancer_general | |
| chr15 | 96952696 | 96953209 | Hyper | tcga, cancer_general | | chr15 | 96959730 | 96959976 | Hyper | cancer_general | |
| chr15 | 96960376 | 96960409 | Hyper | cancer_general | ARRDC4 | chr15 | 96960732 | 96960826 | Hyper | cancer_general, tcga, cancer_general | |
| chr15 | 98504114 | 98504144 | Hyper | blood | | chr15 | 98836178 | 98836393 | Hyper | | |
| chr15 | 98964786 | 98965138 | Hyper | esophageal | | chr15 | 99193206 | 99193480 | Hyper | blood, tcga, liver_tcga | IGF1R |
| chr15 | 99193914 | 99194186 | Hyper | tcga, liver_tcga | IGF1R | chr15 | 100913423 | 100913880 | Hyper | cancer_general | |
| chr15 | 101389973 | 101139023 | Hyper | liver_tcga | LOC145757 | chr15 | 101420521 | 101420610 | Hyper | cancer_general | ALDH1A3 |
| chr15 | 101420945 | 101420989 | Hyper | cancer_general | ALDH1A3 | chr15 | 101513607 | 101513754 | Hyper | tcga | LRRK1 |
| chr15 | 102286533 | 102286563 | Hyper | cancer_general | DQ593864, DQ588428, DQ593627, DQ588362, DQ578285, DQ597461, DQ582666, DQ593630, DQ582294, DQ588439, BC101079, DQ596486, DQ597703, DQ585237, DQ588452, DQ586526, DQ576888, DQ582460, DQ586138, DQ578289, DQ593624, DQ593353, DQ571896, DQ588425, DQ597539, DQ575740, DQ595661 | chr21 | 22370332 | 22370458 | Hyper | | NCAM2 |
| chr21 | 22370688 | 22370718 | Hyper | cancer_general | NCAM2 | chr21 | 26934368 | 26934786 | Hyper | tcga, liver_tcga, cancer_general | MIR155HG |
| chr21 | 27011773 | 27011807 | Hyper | tcga | JAM2 | chr21 | 27012373 | 27012431 | Hyper | colorectal | JAM2 |
| chr21 | 27944995 | 27945081 | Hyper | cancer_general | CYYR1 | chr21 | 27945398 | 27945427 | Hyper | tcga | CYYR1 |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr21 | 27945693 | 27945722 | Hyper | tcga | CYYR1 | chr21 | 28216585 | 28217690 | Hyper | cancer_general | ADAMTS1 |
| chr21 | 28218774 | 28219045 | Hyper | cancer_general, tcga | ADAMTS1 | chr21 | 28338836 | 28338887 | Hyper | cancer_general | |
| chr21 | 28339247 | 28339501 | Hyper | tcga, cancer_general | | chr21 | 28339892 | 28340318 | Hyper | tcga, cancer_general | |
| chr21 | 31311404 | 31311553 | Hyper | cancer_general | | chr21 | 31311944 | 31312105 | Hyper | tcga, cancer_general | |
| chr21 | 31312313 | 31312445 | Hyper | tcga, cancer_general | | chr21 | 33244921 | 33245040 | Hyper | esophageal | HUNK |
| chr21 | 33245683 | 33245718 | Hyper | esophageal | HUNK | chr21 | 33246009 | 33246190 | Hyper | esophageal | HUNK |
| chr21 | 33785288 | 33785325 | Hyper | blood | EVA1C | chr21 | 34392171 | 34392566 | Hyper | cancer_general, tcga | OLIG2 |
| chr21 | 34395302 | 34396269 | Hyper | tcga, cancer_general | OLIG2 | chr21 | 34396795 | 34397037 | Hyper | cancer_general | OLIG2 |
| chr21 | 34398070 | 34398634 | Hyper | tcga, cancer_general | OLIG2 | chr21 | 34399333 | 34400258 | Hyper | cancer_general | OLIG2 |
| chr21 | 34401185 | 34401392 | Hyper | cancer_general | OLIG2 | chr21 | 34442547 | 34442665 | Hyper | cancer_general | OLIG1 |
| chr21 | 34443103 | 34443262 | Hyper | cancer_general | OLIG1 | chr21 | 34443509 | 34443686 | Hyper | cancer_general | OLIG1 |
| chr21 | 34443893 | 34443956 | Hyper | cancer_general | OLIG1 | chr21 | 34444163 | 34444598 | Hyper | tcga, cancer_general | OLIG1 |
| chr21 | 36041468 | 36041697 | Hyper | cancer_general | CLIC6 | chr21 | 36041985 | 36042238 | Hyper | cancer_general | CLIC6 |
| chr21 | 36042658 | 36042861 | Hyper | cancer_general | CLIC6 | chr21 | 36064457 | 36064683 | Hyper | cancer_general | SIM2 |
| chr21 | 38064966 | 38065737 | Hyper | cancer_general | SIM2 | chr21 | 38065955 | 38066112 | Hyper | cancer_general | SIM2 |
| chr21 | 38067203 | 38067233 | Hyper | cancer_general | SIM2 | chr21 | 38068178 | 38068289 | Hyper | cancer_general | SIM2 |
| chr21 | 38068565 | 38068783 | Hyper | cancer_general | SIM2 | chr21 | 38069093 | 38069203 | Hyper | cancer_general | SIM2 |
| chr21 | 38069459 | 38069496 | Hyper | cancer_general | SIM2 | chr21 | 38069825 | 38070162 | Hyper | cancer_general, tcga | SIM2 |
| chr21 | 38070705 | 38070765 | Hyper | blood | SIM2 | chr21 | 38071791 | 38071905 | Hyper | blood | SIM2 |
| chr21 | 38073007 | 38073070 | Hyper | cancer_general | SIM2 | chr21 | 38073300 | 38073860 | Hyper | cancer_general | SIM2 |
| chr21 | 38076854 | 38077152 | Hyper | tcga, cancer_general | SIM2 | chr21 | 38078415 | 38078487 | Hyper | cancer_general | SIM2 |
| chr21 | 38079988 | 38080684 | Hyper | cancer_general | SIM2 | chr21 | 38081085 | 38081207 | Hyper | tcga | SIM2 |
| chr21 | 38081445 | 38081835 | Hyper | cancer_general | SIM2 | chr21 | 38082042 | 38082072 | Hyper | cancer_general | SIM2 |
| chr21 | 38082315 | 38082345 | Hyper | cancer_general | SIM2 | chr21 | 38082930 | 38083196 | Hyper | cancer_general | SIM2 |
| chr21 | 38119904 | 38120312 | Hyper | cancer_general | HLCS | chr21 | 39047776 | 39047838 | Hyper | head_neck | KCNJ6 |
| chr21 | 39870612 | 39870641 | Hyper | literature | ERG | chr21 | 40033619 | 40033648 | Hyper | literature | ERG |
| chr21 | 40033877 | 40033906 | Hyper | literature | ERG | chr21 | 40984685 | 40984900 | Hyper | tcga | B3GALT5, C21orf88 |
| chr21 | 43186698 | 43186889 | Hyper | blood | RIPK4 | chr21 | 44494891 | 44495155 | Hyper | tcga, cancer_general | CBS |
| chr21 | 44514762 | 44514791 | Hyper | literature | U2AF1 | chr21 | 44524441 | 44524470 | Hyper | literature | U2AF1 |
| chr21 | 44847591 | 44847622 | Hyper | tcga | SIK1 | chr21 | 45148615 | 45148758 | Hyper | cancer_general | PDXK |
| chr21 | 45717477 | 45717548 | Hyper | head_neck | PFKL, AIRE | chr21 | 46125933 | 46126721 | Hyper | cancer_general | KRTAP10-12 |
| chr21 | 46127039 | 46127094 | Hyper | cancer_general | KRTAP10-12 | chr21 | 46127542 | 46127692 | Hyper | cancer_general | KRTAP10-12 |
| chr21 | 46128902 | 46128938 | Hyper | cancer_general | | chr21 | 46129444 | 46129485 | Hyper | cancer_general | KRTAP10-12 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr21 | 46825825 | 46826067 | Hyper | tcga | COL18A1-AS2, COL18A1 | chr21 | 47010243 | 47010451 | Hyper | cancer_general | |
| chr21 | 47062544 | 47062825 | Hyper | cancer_general | PCBP3 | chr21 | 47063538 | 47063962 | Hyper | cancer_general | PCBP3 |
| chr21 | 47064250 | 47064377 | Hyper | cancer_general | PCBP3 | chr21 | 47518776 | 47518814 | Hyper | cancer_general | COL6A2 |
| chr21 | 47717560 | 47717589 | Hyper | liver_tcga | C21orf58, YBEY | chr7 | 329805 | 329838 | Hyper | cancer_general | LOC100288524 |
| chr7 | 556928 | 556983 | Hyper | blood | FLJ44511, PDGFA | chr7 | 751816 | 751874 | Hyper | liver_tcga, cancer_general | |
| chr7 | 752120 | 752221 | Hyper | liver_tcga, cancer_general | | chr7 | 922050 | 922235 | Hyper | liver_tcga | GET4, SUN1 |
| chr7 | 927933 | 927986 | Hyper | liver_tcga | ADAP1, GET4 | chr7 | 1263761 | 1263960 | Hyper | cancer_general | UNCX |
| chr7 | 1268318 | 1268366 | Hyper | cancer_general | UNCX | chr7 | 1269305 | 1269808 | Hyper | cancer_general | UNCX |
| chr7 | 1270406 | 1270440 | Hyper | cancer_general | UNCX | chr7 | 1273167 | 1273330 | Hyper | cancer_general | UNCX |
| chr7 | 1274641 | 1274677 | Hyper | cancer_general | UNCX | chr7 | 1275008 | 1275038 | Hyper | cancer_general | UNCX |
| chr7 | 1275579 | 1275680 | Hyper | cancer_general | UNCX | chr7 | 1277817 | 1277865 | Hyper | cancer_general | UNCX |
| chr7 | 1279099 | 1279129 | Hyper | cancer_general | UNCX | chr7 | 1279965 | 1279995 | Hyper | cancer_general | UNCX |
| chr7 | 1281131 | 1281232 | Hyper | cancer_general | UNCX | chr7 | 1281493 | 1281555 | Hyper | cancer_general | UNCX |
| chr7 | 1282042 | 1282150 | Hyper | cancer_general | UNCX | chr7 | 1282506 | 1282644 | Hyper | cancer_general | UNCX |
| chr7 | 1286244 | 1286338 | Hyper | cancer_general | UNCX | chr7 | 1286810 | 1286858 | Hyper | cancer_general | UNCX |
| chr7 | 1288582 | 1288753 | Hyper | cancer_general | | chr7 | 1709138 | 1709235 | Hyper | cancer_general | ELFN1 |
| chr7 | 1709474 | 1709594 | Hyper | cancer_general | | chr7 | 1748514 | 1748766 | Hyper | liver_tcga | CARD11 |
| chr7 | 2728068 | 2728165 | Hyper | cancer_general, colorectal | AMZ1 | chr7 | 2979480 | 2979512 | Hyper | literature | |
| chr7 | 2985518 | 2985547 | Hyper | literature | CARD11 | chr7 | 3083318 | 3083352 | Hyper | tcga | CARD11 |
| chr7 | 3340444 | 3340473 | Hyper | liver_tcga | SDK1 | chr7 | 3340964 | 3340993 | Hyper | liver_tcga | SDK1 |
| chr7 | 3341489 | 3341597 | Hyper | liver_tcga, cancer_general | SDK1 | chr7 | 4922550 | 4922722 | Hyper | tcga | MMD2 |
| chr7 | 4923072 | 4923397 | Hyper | liver_tcga, cancer_general, tcga | MMD2 | chr7 | 4998201 | 4998388 | Hyper | cancer_general | MMD2 |
| chr7 | 4998698 | 4998736 | Hyper | cancer_general | MMD2 | chr7 | 5111528 | 5111669 | Hyper | liver_tcga | RBAKDN, RBAK, RBAK-RBAKDN |
| chr7 | 5632939 | 5633100 | Hyper | tcga | FSCN1 | chr7 | 6045612 | 6045641 | Hyper | literature | AIMP2, PMS2 |
| chr7 | 6414386 | 6414415 | Hyper | literature | RAC1 | chr7 | 6426878 | 6426907 | Hyper | literature | RAC1 |
| chr7 | 6543150 | 6543216 | Hyper | hepatobiliary | GRID2IP | chr7 | 6566413 | 6566663 | Hyper | tcga | |
| chr7 | 6570959 | 6571130 | Hyper | tcga | | chr7 | 6576137 | 6576367 | Hyper | tcga | |
| chr7 | 6703555 | 6703959 | Hyper | liver_tcga, cancer_general | AK123300 | chr7 | 8473070 | 8473674 | Hyper | cancer_general | NXPH1 |
| chr7 | 8473956 | 8474562 | Hyper | cancer_general | NXPH1 | chr7 | 8474814 | 8475057 | Hyper | cancer_general | NXPH1 |
| chr7 | 8480640 | 8481159 | Hyper | literature, cancer_general | NXPH1 | chr7 | 8481642 | 8481833 | Hyper | cancer_general | NXPH1 |
| chr7 | 8482056 | 8482921 | Hyper | literature, cancer_general | NXPH1 | chr7 | 8483147 | 8483950 | Hyper | cancer_general | NXPH1 |
| chr7 | 12151440 | 12151678 | Hyper | cancer_general | | chr7 | 12443317 | 12443403 | Hyper | cancer_general | VWDE |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 12443841 | 12443871 | Hyper | cancer_general | VWDE | chr7 | 12610339 | 12610476 | Hyper | blood | SCIN, BC075797 |
| chr7 | 15725983 | 15726081 | Hyper | cancer_general | BX538274, MEOX2 | chr7 | 15726634 | 15727077 | Hyper | tcga, cancer_general | BX538274, MEOX2 |
| chr7 | 15727290 | 15727320 | Hyper | cancer_general | BX538274, MEOX2 | chr7 | 19145808 | 19146249 | Hyper | cancer_general | TWIST1 |
| chr7 | 19146502 | 19146558 | Hyper | cancer_general | TWIST1 | chr7 | 19147122 | 19147798 | Hyper | tcga, cancer_general | TWIST1 |
| chr7 | 19152002 | 19152349 | Hyper | tcga, cancer_general | TWIST1 | chr7 | 19155791 | 19155820 | Hyper | literature | TWIST1 |
| chr7 | 19156070 | 19156916 | Hyper | tcga, literature, cancer_general | TWIST1 | chr7 | 19157144 | 19158015 | Hyper | tcga, literature, cancer_general | TWIST1 |
| chr7 | 19158632 | 19158735 | Hyper | literature | TWIST1 | chr7 | 19184058 | 19184255 | Hyper | cancer_general | BC043576, FERD3L |
| chr7 | 19813284 | 19813313 | Hyper | literature | TMEM196 | chr7 | 20816252 | 20816447 | Hyper | cancer_general | SP8 |
| chr7 | 20817380 | 20817410 | Hyper | cancer_general | SP8 | chr7 | 20818130 | 20818362 | Hyper | cancer_general | SP8 |
| chr7 | 20823292 | 20823432 | Hyper | cancer_general | SP8 | chr7 | 20823904 | 20824946 | Hyper | cancer_general, literature, tcga | SP8 |
| chr7 | 20825379 | 20825559 | Hyper | literature | SP8 | chr7 | 20826113 | 20826202 | Hyper | literature | SP8 |
| chr7 | 20826884 | 20827199 | Hyper | pancreas, literature | SP8 | chr7 | 20830670 | 20830700 | Hyper | cancer_general | SP8 |
| chr7 | 20833167 | 20833322 | Hyper | cancer_general | SP8 | chr7 | 21582593 | 21582868 | Hyper | cancer_general | DNAH11 |
| chr7 | 21583263 | 21583326 | Hyper | cancer_general | DNAH11 | chr7 | 22539833 | 22539909 | Hyper | cancer_general | STEAP1B |
| chr7 | 22589356 | 22589870 | Hyper | cancer_general | | chr7 | 23287253 | 23287624 | Hyper | cancer_general, tcga | GPNMB |
| chr7 | 24323763 | 24323939 | Hyper | liver_tcga | NPY | chr7 | 24796478 | 24796567 | Hyper | cancer_general, tcga | DFNA5 |
| chr7 | 25892510 | 25892588 | Hyper | cancer_general | | chr7 | 25896521 | 25896864 | Hyper | cancer_general | HOXA1, HOTAIRM1 |
| chr7 | 25897133 | 25897246 | Hyper | tcga, pancreas | | chr7 | 27127863 | 27127898 | Hyper | cancer_general | HOXA2, AK291164, HOXA3, HOTAIRM1, HOXA1 |
| chr7 | 27135327 | 27135794 | Hyper | tcga, cancer_general | HOTAIRM1, HOXA2, AK291164, HOXA1 | chr7 | 27136013 | 27136790 | Hyper | tcga, lung, cancer_general | HOXA2, AK291164, HOXA3, HOTAIRM1, HOXA1 |
| chr7 | 27138381 | 27138410 | Hyper | literature | HOXA2, AK291164, HOXA3, HOTAIRM1, HOXA1 | chr7 | 27187535 | 27187570 | Hyper | cancer_general | HOXA7, DQ655986, HOXA-AS3, HOXA6, HOXA5 |
| chr7 | 27190591 | 27191226 | Hyper | tcga, liver_tcga, cancer_general | HOXA5, HOXA7, DQ655986, HOXA-AS3, HOXA6 | chr7 | 27192061 | 27192098 | Hyper | cancer_general | HOXA7, HOXA9, HOXA10-HOXA9, DQ655986, HOXA-AS3, HOXA6, HOXA5 |

TABLE 11-continued

| chr | Start | Stop | Hypo/hyper | classification | annotation |
|---|---|---|---|---|---|
| chr7 | 27195462 | 27196839 | Hyper | tcga, cancer_general, lung | DQ655986, HOXA-AS3, HOXA6, HOXA9, HOXA10-HOXA9, HOXA7 |
| chr7 | 27204487 | 27205395 | Hyper | literature, cancer_general, liver_tcga, tcga | HOXA10-HOXA9, HOXA7, HOXA-AS4, MIR196B, HOXA10 |
| chr7 | 27205678 | 27206058 | Hyper | cancer_general | HOXA10, HOXA10-HOXA9, OHXA9, HOXA7, HOXA-AS4, MIR196B |
| chr7 | 27208187 | 27208285 | Hyper | liver_tcga | HOXA-AS4, MIR196B, HOXA10-HOXA9, HOXA10, HOXA9 |
| chr7 | 27209462 | 27209582 | Hyper | liver_tcga | HOXA-AS4, HOXA10-HOXA9, HOXA10, MIR196B |
| chr7 | 27209789 | 27209828 | Hyper | liver_tcga | HOXA10, MIR196B, HOXA-AS4, HOXA10-HOXA9, HOXA9 |
| chr7 | 27212499 | 27212899 | Hyper | cancer_general | HOXA11, HOXA10, MIR196B, HOXA-AS4, HOXA10-HOXA9 |
| chr7 | 27213172 | 27214310 | Hyper | tcga, literature, cancer_general | HOXA11, HOXA10, MIR 196B, HOXA-AS4, HOXA10-HOXA9, HOXA9 |
| chr7 | 27217042 | 27217071 | Hyper | liver_tcga | HOXA11, HOXA11-AS, LOC402470, HOXA11 |
| chr7 | 27223114 | 27223151 | Hyper | cancer_general | HOXA11-AS, LOC402470, HOXA11, HOXA10 |
| chr7 | 27223601 | 27223696 | Hyper | cancer_general | HOXA10, HOXA11-AS, LOC402470, HOXA11 | 27224069 | 27224609 | Hyper | cancer_general | HOXA11, HOXA10, HOXA11-AS, LOC402470 |
| chr7 | 27225035 | 27225092 | Hyper | cancer_general | LOC402470, HOXA11, HOXA11-AS, HOXA11, HOXA10 | 27225447 | 27225543 | Hyper | liver_tcga, literature | HOXA11, HOXA10, HOXA11-AS, LOC402470, HOXA11-AS, HOXA11, HOXA10 |

TABLE 11-continued

| chr | Start | Stop | Hypo/hyper | classification | annotation |
|---|---|---|---|---|---|
| chr7 | 27227874 | 27227953 | Hyper | cancer_general | LOC402470, HOXA11-AS, HOXA11, HOXA10, HOXA13 |
| chr7 | 27231476 | 27231505 | Hyper | liver_tcga | HOXA11-AS, HOXA11, HOXA13, HOTTIP, LOC402470 |
| chr7 | 27231818 | 27231894 | Hyper | liver_tcga | LOC402470, HOXA11-AS, HOXA11, HOXA13, HOTTIP |
| chr7 | 27232289 | 27232962 | Hyper | liver_tcga, cancer_general | HOXA13, HOTTIP, LOC402470, HOXA11-AS, HOXA11 |
| chr7 | 27233410 | 27233454 | Hyper | liver_tcga | HOXA13, HOTTIP, LOC402470, HOXA11-AS, HOXA11 |
| chr7 | 27238887 | 27238917 | Hyper | cancer_general | HOTTIP, HOXA13, LOC402470, HOXA11-AS |
| chr7 | 27239177 | 27239234 | Hyper | cancer_general | HOTTIP, HOXA13 |
| chr7 | 27240230 | 27240381 | Hyper | cancer_general | HOTTIP, HOXA13 |
| chr7 | 27244515 | 27245310 | Hyper | cancer_general | HOTTIP, HOXA13 |
| chr7 | 27252380 | 27252410 | Hyper | cancer_general | HOTTIP |
| chr7 | 27260092 | 27260122 | Hyper | liver_tcga |  |
| chr7 | 27264875 | 27265325 | Hyper | cancer_general | EVX1 |
| chr7 | 27265538 | 27265584 | Hyper | cancer_general | EVX1 |
| chr7 | 27275513 | 27275543 | Hyper | blood | EVX1 |
| chr7 | 27279915 | 27279453 | Hyper | cancer_general | EVX1 |
| chr7 | 27281329 | 27281360 | Hyper | literature | EVX1 |
| chr7 | 27282089 | 27283013 | Hyper | cancer_general | EVX1 |
| chr7 | 27283351 | 27283627 | Hyper | cancer_general | EVX1 |
| chr7 | 27285522 | 27286248 | Hyper | tcga, cancer_general |  |
| chr7 | 27288946 | 27289449 | Hyper | cancer_general |  |
| chr7 | 27291143 | 27291851 | Hyper | literature, cancer_general | EVX1 |
| chr7 | 28449276 | 28450015 | Hyper | tcga, colorectal, cancer_general | CREB5, BC087859 |
| chr7 | 28995657 | 28995978 | Hyper | blood | DQ601810, TRIL |
| chr7 | 28996457 | 28996495 | Hyper | cancer_general, blood | DQ601810, TRIL |
| chr7 | 28996840 | 28996916 | Hyper | liver_tcga, cancer_general | DQ601810, TRIL |
| chr7 | 28997136 | 28997625 | Hyper | cancer_general, liver_tcga | DQ601810, TRIL |
| chr7 | 28998053 | 28998119 | Hyper | cancer_general | DQ601810, TRIL |
| chr7 | 30029702 | 30029822 | Hyper | tcga | SCRN1 |
| chr7 | 30721280 | 30721902 | Hyper | tcga, cancer_general | CRHR2 |
| chr7 | 30722290 | 30722375 | Hyper | liver_tcga, cancer_general | CRHR2 |
| chr7 | 31093003 | 31093133 | Hyper | cancer_general | ADCYAP1R1 |
| chr7 | 31232909 | 31232939 | Hyper | blood |  |
| chr7 | 31375965 | 31376135 | Hyper | cancer_general | NEUROD6 |
| chr7 | 32110698 | 32110772 | Hyper | cancer_general |  |
| chr7 | 32337807 | 32337837 | Hyper | cancer_general |  |
| chr7 | 32338088 | 32338410 | Hyper | tcga, cancer_general |  |
| chr7 | 32338900 | 32338930 | Hyper | cancer_general | FKBP9 |
| chr7 | 32467461 | 32468062 | Hyper | cancer_general |  |
| chr7 | 32997124 | 32997454 | Hyper | blood |  |
| chr7 | 33943459 | 33943759 | Hyper | cancer_general | BMPER |
| chr7 | 35225809 | 35225876 | Hyper | cancer_general |  |
| chr7 | 35226193 | 35226765 | Hyper | tcga, cancer_general |  |
| chr7 | 35292970 | 35293293 | Hyper | cancer_general | TBX20 |
| chr7 | 35293654 | 35294141 | Hyper | cancer_general, literature, liver_tcga | TBX20 |
| chr7 | 35294502 | 35294536 | Hyper | cancer_general | TBX20 |
| chr7 | 35295104 | 35295134 | Hyper | cancer_general | TBX20 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 35295908 | 35295944 | Hyper | cancer_general | TBX20 | chr7 | 35296935 | 35298032 | Hyper | cancer_general | TBX20 |
| chr7 | 35300951 | 35301948 | Hyper | cancer_general, literature | TBX20 | chr7 | 35494353 | 35494440 | Hyper | cancer_general | |
| chr7 | 37487164 | 37487826 | Hyper | tcga, cancer_general | | chr7 | 37488257 | 37488578 | Hyper | cancer_general | |
| chr7 | 37488920 | 37488992 | Hyper | cancer_general | EPDR1, SFRP4 | chr7 | 37955878 | 37955979 | Hyper | cancer_general | EPDR1, SFRP4 |
| chr7 | 37956271 | 37956439 | Hyper | cancer_general | EPDR1, SFRP4 | chr7 | 37960301 | 37960335 | Hyper | cancer_general | EPDR1, SFRP4 |
| chr7 | 38670357 | 38671015 | Hyper | tcga, cancer_general | | chr7 | 39015542 | 39015981 | Hyper | cancer_general | POU6F2, AK023033 |
| chr7 | 39649223 | 39649457 | Hyper | liver_tcga, literature | LOC646999 | chr7 | 39872836 | 39873015 | Hyper | tcga | |
| chr7 | 41739663 | 41739879 | Hyper | pancreas, tcga | INHBA-AS1, INHBA | chr7 | 41982690 | 41982874 | Hyper | esophageal | |
| chr7 | 42267647 | 42267677 | Hyper | cancer_general | GLI3 | chr7 | 42276346 | 42276634 | Hyper | cancer_general | GLI3 |
| chr7 | 42533118 | 42533296 | Hyper | tcga | | chr7 | 43152109 | 43152700 | Hyper | cancer_general | HECW1, AX748020 |
| chr7 | 43152957 | 43153237 | Hyper | cancer_general, tcga | AX748020, HECW1 | chr7 | 44143980 | 44144010 | Hyper | liver_tcga | AEBP1, MIR4649 |
| chr7 | 44163926 | 44163989 | Hyper | tcga | POLD2, AEBP1 | chr7 | 44364838 | 44364903 | Hyper | colorectal | CAMK2B |
| chr7 | 45613785 | 45613898 | Hyper | cancer_general | ADCY1 | chr7 | 45614341 | 45614474 | Hyper | cancer_general | ADCY1 |
| chr7 | 45614738 | 45614809 | Hyper | cancer_general | ADCY1 | chr7 | 45615440 | 45615495 | Hyper | cancer_general | ADCY1 |
| chr7 | 45960743 | 45960794 | Hyper | cancer_general | IGFBP3 | chr7 | 45961146 | 45961176 | Hyper | cancer_general | IGFBP3 |
| chr7 | 45961508 | 45961576 | Hyper | cancer_general | IGFBP3 | chr7 | 45961833 | 45961888 | Hyper | cancer_general | IGFBP3 |
| chr7 | 49812820 | 49813994 | Hyper | liver_tcga, literature, cancer_general | VWC2 | chr7 | 49814531 | 49814795 | Hyper | tcga, cancer_general | VWC2 |
| chr7 | 49815101 | 49815765 | Hyper | tcga, literature, cancer_general | VWC2 | chr7 | 50343263 | 50343401 | Hyper | cancer_general | IKZF1 |
| chr7 | 50343698 | 50343994 | Hyper | cancer_general | IKZF1 | chr7 | 50344226 | 50344491 | Hyper | cancer_general | IKZF1 |
| chr7 | 50860226 | 50861121 | Hyper | blood | | chr7 | 51383754 | 51383790 | Hyper | blood | COBL |
| chr7 | 51384327 | 51384440 | Hyper | blood | COBL | chr7 | 51384915 | 51384951 | Hyper | blood | COBL |
| chr7 | 52156231 | 52156261 | Hyper | cancer_general | | chr7 | 54609852 | 54610153 | Hyper | esophageal, cancer_general | VSTM2A |
| chr7 | 54612418 | 54612730 | Hyper | cancer_general | VSTM2A | chr7 | 55086473 | 55086601 | Hyper | blood | EGFR |
| chr7 | 55086983 | 55087533 | Hyper | blood | EGFR | chr7 | 55209976 | 55210005 | Hyper | literature | EGFR |
| chr7 | 55211065 | 55211094 | Hyper | literature | EGFR | chr7 | 55221729 | 55221836 | Hyper | literature | EGFR |
| chr7 | 55223589 | 55223636 | Hyper | literature | EGFR | chr7 | 55227993 | 55228022 | Hyper | literature | EGFR |
| chr7 | 55233028 | 55233123 | Hyper | literature | EGFR | chr7 | 55241663 | 55241737 | Hyper | literature | EGFR-AS1, EGFR |
| chr7 | 55242419 | 55242493 | Hyper | literature | EGFR-AS1, EGFR | chr7 | 55248975 | 55249085 | Hyper | literature | EGFR-AS1, EGFR |
| chr7 | 55259404 | 55259547 | Hyper | literature | EGFR, EGFR-AS1 | chr7 | 55260469 | 55260498 | Hyper | literature | EGFR, EGFR-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 55268867 | 55268896 | Hyper | literature | GU228584, EGFR | chr7 | 64349026 | 64349056 | Hyper | cancer_general | ZNF273, AK097702 |
| chr7 | 64349331 | 64349470 | Hyper | cancer_general | AK097702, ZNF273 | chr7 | 64700283 | 64700329 | Hyper | cancer_general | |
| chr7 | 64712364 | 64712510 | Hyper | cancer_general, tcga | | chr7 | 64974382 | 64974422 | Hyper | cancer_general | |
| chr7 | 65037609 | 65037734 | Hyper | cancer_general | | chr7 | 65508995 | 65509043 | Hyper | cancer_general | |
| chr7 | 65878743 | 65878793 | Hyper | cancer_general | AUTS2 | chr7 | 69062519 | 69062635 | Hyper | tcga | AUTS2 |
| chr7 | 69064590 | 69065045 | Hyper | tcga, colorectal | WBSCR17 | chr7 | 70596436 | 70596688 | Hyper | cancer_general | WBSCR17 |
| chr7 | 70596942 | 70597105 | Hyper | tcga, cancer_general | | chr7 | 70597406 | 70597451 | Hyper | cancer_general | WBSCR17 |
| chr7 | 70597835 | 70598387 | Hyper | cancer_general | WBSCR17 | chr7 | 71217108 | 71217332 | Hyper | cancer_general | MAGI2-AS3 |
| chr7 | 71800676 | 71801899 | Hyper | cancer_general | RHBDD2 | chr7 | 71802410 | 71802637 | Hyper | cancer_general | MAGI2-AS3 |
| chr7 | 75511201 | 75511298 | Hyper | liver_tcga | | chr7 | 79081792 | 79081821 | Hyper | tcga | |
| chr7 | 79082023 | 79082218 | Hyper | tcga, cancer_general | MAGI2-AS3 | chr7 | 79083093 | 79083177 | Hyper | cancer_general | MAGI2-AS3 |
| chr7 | 79083392 | 79083834 | Hyper | cancer_general | MAGI2-AS3 | chr7 | 80548257 | 80548403 | Hyper | blood | SEMA3C |
| chr7 | 82072350 | 82072503 | Hyper | cancer_general | SEMA3D | chr7 | 82073495 | 82073533 | Hyper | blood | |
| chr7 | 84815141 | 84815375 | Hyper | tcga | | chr7 | 84815744 | 84815954 | Hyper | cancer_general, tcga | SEMA3D |
| chr7 | 86273208 | 86273541 | Hyper | cancer_general | GRM3 | chr7 | 86274117 | 86274457 | Hyper | cancer_general | GRM3 |
| chr7 | 87104816 | 87105412 | Hyper | tcga, esophageal | ABCB4 | chr7 | 87229537 | 87230433 | Hyper | tcga, cancer_general | ABCB1 |
| chr7 | 87257012 | 87257047 | Hyper | cancer_general | RUNDC3B, ABCB1 | chr7 | 87257931 | 87258054 | Hyper | esophageal | |
| chr7 | 87563370 | 87563614 | Hyper | esophageal | ADAM22 | chr7 | 87563829 | 87563890 | Hyper | esophageal | RUNDC3B, ABCB1 |
| chr7 | 88387982 | 88388183 | Hyper | cancer_general | ZNF804B | chr7 | 88388540 | 88388636 | Hyper | tcga | ADAM22 |
| chr7 | 88388879 | 88389356 | Hyper | tcga, cancer_general | ZNF804B | chr7 | 89747996 | 89748340 | Hyper | cancer_general | ZNF804B DPY19L2P4 |
| chr7 | 89950183 | 89950810 | Hyper | cancer_general, tcga | C7orf63 | chr7 | 90226269 | 90226464 | Hyper | tcga, colorectal | CDK14 |
| chr7 | 90895012 | 90895097 | Hyper | tcga | FZD1 | chr7 | 92466152 | 92466400 | Hyper | tcga | CDK6 |
| chr7 | 93203708 | 93203756 | Hyper | cancer_general | | chr7 | 93204332 | 93204492 | Hyper | tcga | CDK6 |
| chr7 | 93519351 | 93520137 | Hyper | liver_tcga, cancer_general | TFPI2 | chr7 | 93551323 | 93551425 | Hyper | cancer_general | GNG11 |
| chr7 | 94284302 | 94284873 | Hyper | cancer_general | PEG10, SGCE | chr7 | 96619560 | 96619603 | Hyper | cancer_general | DLX6-AS1 |
| chr7 | 96621715 | 96621811 | Hyper | cancer_general | DLX6-AS1 | chr7 | 96622107 | 96622349 | Hyper | cancer_general | DLX6-AS1 |
| chr7 | 96622694 | 96622723 | Hyper | literature | DLX6-AS1 | chr7 | 96625537 | 96625720 | Hyper | cancer_general | DLX6, DLX6-AS1 |
| chr7 | 96625998 | 96626051 | Hyper | cancer_general | DLX6, DLX6-AS1 | chr7 | 96631579 | 96631680 | Hyper | liver_tcga | DLX6, DLX6-AS1 |
| chr7 | 96634645 | 96634928 | Hyper | tcga | DLX6, DLX6-AS1 | chr7 | 96635345 | 96635473 | Hyper | cancer_general | DLX6-AS1, DLX6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 96635733 | 96636645 | Hyper | tcga, cancer_general | DLX6, DLX6-AS1 | chr7 | 96639318 | 96639348 | Hyper | cancer_general | DLX6-AS1, DLX6 |
| chr7 | 96646662 | 96647131 | Hyper | cancer_general | DLX5, DLX6, DLX6-AS1 | chr7 | 96647809 | 96648219 | Hyper | cancer_general | DLX6-AS1, DLX5, DLX6 |
| chr7 | 96649955 | 96650192 | Hyper | liver_tcga, cancer_general | DLX5, DLX6, DLX6-AS1 | chr7 | 96650884 | 96651151 | Hyper | cancer_general | DLX5 |
| chr7 | 96651472 | 96651502 | Hyper | cancer_general | DLX5 | chr7 | 96652144 | 96652174 | Hyper | cancer_general | DLX5 |
| chr7 | 96653507 | 96653993 | Hyper | cancer_general | DLX5 | chr7 | 97361098 | 97361781 | Hyper | cancer_general, literature | TAC1 |
| chr7 | 97362292 | 97362607 | Hyper | cancer_general | TAC1 | chr7 | 98245885 | 98246868 | Hyper | literature, cancer_general | NPTX2 |
| chr7 | 98247126 | 98247656 | Hyper | cancer_general | NPTX2 | chr7 | 99177742 | 99177870 | Hyper | cancer_general | ZNF655 STAG3, GPC2, GAL3ST4 |
| chr7 | 99595194 | 99595337 | Hyper | cancer_general | | chr7 | 99775192 | 99775558 | Hype | tcga, liver_tcga | |
| chr7 | 100091210 | 100091378 | Hyper | cancer_general, literature | NYAP1 | chr7 | 100318505 | 100318575 | Hyper | cancer_general | EPO |
| chr7 | 100320690 | 100320719 | Hyper | literature | EPO | chr7 | 100547037 | 100547073 | Hyper | cancer_general | MUC3A, MUC3B |
| chr7 | 100609750 | 100609780 | Hyper | pancreas | MUC12, MUC3B, AK096803, AK057259, MUC3A | chr7 | 100808466 | 100808502 | Hyper | pancreas | AP1S1, NAT16, VGF, MIR4653 |
| chr7 | 100809436 | 100809521 | Hyper | tcga | MIR4653, AP1S1, NAT16, VGF | chr7 | 100823436 | 100823497 | Hyper | cancer_general | NAT16 |
| chr7 | 101005968 | 101005998 | Hyper | cancer_general | COL26A1 | chr7 | 101558399 | 101558698 | Hyper | liver_tcga | CUX1 |
| chr7 | 103085876 | 103086474 | Hyper | liver_tcga, cancer_general | | chr7 | 103629059 | 103630125 | Hyper | tcga, cancer_general | |
| chr7 | 103630475 | 103630824 | Hyper | tcga, cancer_general | | chr7 | 103969217 | 103969341 | Hyper | cancer_general | JB175200, LHFPL3 |
| chr7 | 103969694 | 103969794 | Hyper | cancer_general | JB175200, LHFPL3 | chr7 | 106685282 | 106685345 | Hyper | esophageal | PRKAR2B |
| chr7 | 107301494 | 107301640 | Hyper | cancer_general | SLC26A4, SLC26A4-AS1 | chr7 | 108095329 | 108095362 | Hyper | cancer_general | NRCAM |
| chr7 | 108095686 | 108096055 | Hyper | tcga, colorectal | NRCAM | chr7 | 108097172 | 108097491 | Hyper | tcga, cancer_general | NRCAM |
| chr7 | 112726558 | 112726614 | Hyper | cancer_general | GPR85 | chr7 | 113722810 | 113723439 | Hyper | lung, cancer_general | FOXP2 |
| chr7 | 113724956 | 113725081 | Hyper | cancer_general | FOXP2 | chr7 | 113726509 | 113726539 | Hyper | esophageal | FOXP2 |
| chr7 | 113727442 | 113727486 | Hyper | cancer_general | FOXP2 | chr7 | 113727722 | 113727781 | Hyper | cancer_general | FOXP2 |
| chr7 | 115117552 | 115117647 | Hyper | cancer_general | | chr7 | 116140252 | 116140356 | Hyper | tcga | CAV2 |
| chr7 | 116412008 | 116412058 | Hyper | literature | | chr7 | 116415100 | 116415129 | Hyper | literature | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 116417443 | 116417496 | Hyper | literature | | chr7 | 116422067 | 116422132 | Hyper | literature | WNT2 |
| chr7 | 116423399 | 116423488 | Hyper | literature | | chr7 | 116962893 | 116963476 | Hyper | liver_tcga, cancer_general, tcga | |
| chr7 | 117119381 | 117120271 | Hyper | liver_tcga, literature, cancer_general | CFTR | chr7 | 117513675 | 117513849 | Hyper | blood | CTTNBP2 |
| chr7 | 119913561 | 119913785 | Hyper | tcga | KCND2 | chr7 | 120969672 | 120969800 | Hyper | cancer_general | WNT16 |
| chr7 | 121513523 | 121513709 | Hyper | tcga | PTPRZ1 | chr7 | 121939677 | 121940448 | Hyper | liver_tcga, literature, cancer_general | FEZF1, FEZF1-AS1 |
| chr7 | 121940935 | 121941052 | Hyper | cancer_general | FEZF1, FEZF1-AS1 | chr7 | 121941881 | 121942170 | Hyper | cancer_general | FEZF1-AS1, FEZF1 |
| chr7 | 121944001 | 121944166 | Hyper | cancer_general | FEZF1-AS1, FEZF1 | chr7 | 121945822 | 121945920 | Hyper | blood | FEZF1-AS1, FEZF1 |
| chr7 | 121946478 | 121947406 | Hyper | cancer_general | FEZF1-AS1, FEZF1 | chr7 | 121950137 | 121951069 | Hyper | cancer_general | CADPS2, FEZF1-AS1, FEZF1 |
| chr7 | 121951877 | 121952169 | Hyper | cancer_general | CADPS2, FEZF1-AS1, FEZF1 | chr7 | 121956486 | 121956567 | Hyper | cancer_general | CADPS2, FEZF1-AS1, FEZF1 |
| chr7 | 121956830 | 121957331 | Hyper | cancer_general | CADPS2, FEZF1-AS1, FEZF1 | chr7 | 122526833 | 122526873 | Hyper | blood | |
| chr7 | 123173150 | 123173244 | Hyper | cancer_general | IQUB, NDUFA5 | chr7 | 123672048 | 123672086 | Hyper | cancer_general | EU233817, TMEM229A, L13779, BC041947 |
| chr7 | 124404415 | 124404522 | Hyper | cancer_general | GPR37 | chr7 | 126891220 | 126891250 | Hyper | cancer_general | |
| chr7 | 126891504 | 126891593 | Hyper | cancer_general | | chr7 | 126894076 | 126894197 | Hyper | esophageal | |
| chr7 | 127744122 | 127744631 | Hyper | cancer_general | | chr7 | 127806634 | 127806664 | Hyper | cancer_general | |
| chr7 | 127807817 | 127807846 | Hyper | tcga | | chr7 | 127808047 | 127808792 | Hyper | tcga, cancer_general | |
| chr7 | 127841505 | 127841704 | Hyper | cancer_general | MIR129-1 PRRT4, RBM28 | chr7 | 127881254 | 127881283 | Hyper | literature | LEP |
| chr7 | 127991826 | 127992135 | Hyper | cancer_general | | chr7 | 128337467 | 128337921 | Hyper | cancer_general | |
| chr7 | 128470897 | 128471032 | Hyper | cancer_general | FLNC, CCDC136 | chr7 | 128828195 | 128828272 | Hyper | cancer_general | SMO |
| chr7 | 129418057 | 129418428 | Hyper | pancreas, cancer_general | MIR183, MIR96, MIR182 | chr7 | 129422160 | 129423418 | Hyper | cancer_general | MIR183, MIR96 |
| chr7 | 129423834 | 129424034 | Hyper | lung, cancer_general | | chr7 | 129424655 | 129425887 | Hyper | cancer_general | MIR183 |
| chr7 | 129426195 | 129426236 | Hyper | cancer_general | MIR183, MIR96 | chr7 | 131242738 | 131242824 | Hyper | cancer_general | PODXL |
| chr7 | 131514824 | 131514854 | Hyper | cancer_general | | chr7 | 132261272 | 132261432 | Hyper | tcga | PLXNA4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 134143164 | 134143475 | Hyper | cancer_general | AKR1B1 | chr7 | 134143807 | 134144132 | Hyper | tcga, liver_tcga, colorectal, cancer_general | AKR1B1 |
| chr7 | 136553311 | 136554366 | Hyper | cancer_general | CHRM2 | chr7 | 136554638 | 136554966 | Hyper | cancer_general | CHRM2 |
| chr7 | 136555235 | 136555412 | Hyper | cancer_general | CHRM2 | chr7 | 136555681 | 136556091 | Hyper | tcga, cancer_general | CHRM2 |
| chr7 | 137028481 | 137028524 | Hyper | cancer_general | | chr7 | 137531158 | 137532337 | Hyper | tcga, cancer_general | DGKI |
| chr7 | 138720785 | 138720909 | Hyper | liver_tcga | ZC3HAV1L, ZC3HAV1 | chr7 | 139167617 | 139167744 | Hyper | cancer_general | KLRG2 |
| chr7 | 139168042 | 139168379 | Hyper | cancer_general | KLRG2 | chr7 | 139208772 | 139208979 | Hyper | liver_tcga, cancer_general | CLEC2L |
| chr7 | 139930051 | 139930270 | Hyper | tcga, liver_tcga | DENND2A | chr7 | 140218053 | 140218082 | Hyper | tcga | DENND2A |
| chr7 | 140339934 | 140339982 | Hyper | cancer_general | BRAF | chr7 | 140453121 | 140453167 | Hyper | literature | BRAF |
| chr7 | 140477779 | 140477868 | Hyper | literature | | chr7 | 140481381 | 140481431 | Hyper | literature | BRAF |
| chr7 | 140772795 | 140773228 | Hyper | tcga, cancer_general | TMEM178B | chr7 | 140773563 | 140773750 | Hyper | tcga | TMEM178B |
| chr7 | 143042634 | 143042798 | Hyper | liver_tcga | FAM131B | chr7 | 143579739 | 143580069 | Hyper | cancer_general | FAM115A |
| chr7 | 145812992 | 145813082 | Hyper | cancer_general | CNTNAP2 | chr7 | 145813412 | 145813494 | Hyper | liver_tcga | CNTNAP2 |
| chr7 | 145813891 | 145814166 | Hyper | tcga, cancer_general | CNTNAP2 | chr7 | 148508712 | 148508741 | Hyper | literature | EZH2 |
| chr7 | 149112058 | 149112416 | Hyper | literature, cancer_general | TRNA_Cys | chr7 | 149119948 | 149120073 | Hyper | cancer_general | ZNF777, TRNA_Cys, ATP6V0E2-AS1, ZNF862, DQ590227, ATP6V0E2 |
| chr7 | 149411541 | 149412304 | Hyper | colorectal | TRNA_Cys, KRBA1 | chr7 | 149570368 | 149570406 | Hyper | esophageal | |
| chr7 | 149744505 | 149744560 | Hyper | cancer_general | AL162052 | chr7 | 149917248 | 149917336 | Hyper | liver_tcga, cancer_general | |
| chr7 | 149918119 | 149918149 | Hyper | literature | | chr7 | 150038883 | 150038912 | Hyper | literature | RARRES2, LRRC61, ZBED6CL |
| chr7 | 150716169 | 150716305 | Hyper | cancer_general | ABCB8, ATG9B | chr7 | 150748192 | 150748406 | Hyper | cancer_general | CDK5, SLC4A2, ASIC3, ABCB8 |
| chr7 | 151106451 | 151107004 | Hyper | cancer_general | WDR86-AS1, WDR86 | chr7 | 151107486 | 151107651 | Hyper | cancer_general | WDR86-AS1, WDR86 |
| chr7 | 151188034 | 151188063 | Hyper | literature | RHEB | chr7 | 152133406 | 152133436 | Hyper | liver_tcga | FABP5P3, KMT2C |
| chr7 | 152622621 | 152622697 | Hyper | cancer_general | DPP6 | chr7 | 152623016 | 152623057 | Hyper | cancer_general | |
| chr7 | 153583595 | 153584069 | Hyper | cancer_general | DPP6 | chr7 | 153584389 | 153584623 | Hyper | literature, cancer_general | DPP6 |
| chr7 | 153584848 | 153585206 | Hyper | cancer_general | DPP6 | chr7 | 153585418 | 153585606 | Hyper | cancer_general | DPP6 |
| chr7 | 153749720 | 153750115 | Hyper | cancer_general | DPP6, AK127966 | chr7 | 154862046 | 154862266 | Hyper | cancer_general | LOC100128264, HTR5A |
| chr7 | 155164454 | 155165562 | Hyper | tcga, cancer_general | BC150495 | chr7 | 155165875 | 155166784 | Hyper | cancer_general | BC150495 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 155167034 | 155167909 | Hyper | tcga, cancer_general | BC150495 | chr7 | 155174656 | 155174788 | Hyper | cancer_general | BC150495 |
| chr7 | 155241318 | 155242049 | Hyper | cancer_general | EN2 | chr7 | 155242729 | 155243102 | Hyper | cancer_general | EN2 |
| chr7 | 155243346 | 155243561 | Hyper | cancer_general | EN2 | chr7 | 155243825 | 155243895 | Hyper | cancer_general | EN2 |
| chr7 | 155244180 | 155244361 | Hyper | cancer_general | EN2 | chr7 | 155246886 | 155247584 | Hyper | cancer_general | EN2 |
| chr7 | 155248913 | 155248943 | Hyper | cancer_general | EN2 | chr7 | 155249512 | 155249565 | Hyper | cancer_general | EN2 |
| chr7 | 155249925 | 155250011 | Hyper | cancer_general | EN2 | chr7 | 155250283 | 155250355 | Hyper | cancer_general | EN2 |
| chr7 | 155250787 | 155250996 | Hyper | cancer_general | EN2 | chr7 | 155251701 | 155251939 | Hyper | cancer_general | EN2 |
| chr7 | 155252247 | 155252490 | Hyper | cancer_general | EN2 | chr7 | 155252862 | 155253041 | Hyper | tcga | EN2 |
| chr7 | 155254848 | 155255324 | Hyper | cancer_general | EN2 | chr7 | 155256237 | 155256312 | Hyper | cancer_general | EN2 |
| chr7 | 155257040 | 155257189 | Hyper | cancer_general | EN2 | chr7 | 155258193 | 155258487 | Hyper | cancer_general | EN2 |
| chr7 | 155258949 | 155260137 | Hyper | tcga, cancer_general | EN2 | chr7 | 155260880 | 155261210 | Hyper | cancer_general, tcga | EN2 |
| chr7 | 155301838 | 155301931 | Hyper | cancer_general | CNPY1 | chr7 | 155302328 | 155303335 | Hyper | tcga, cancer_general | CNPY1 |
| chr7 | 155325796 | 155325872 | Hyper | cancer_general | CNPY1 | chr7 | 155326169 | 155326527 | Hyper | cancer_general | CNPY1 |
| chr7 | 155580165 | 155580211 | Hyper | cancer_general | RBM33 | chr7 | 155600629 | 155600723 | Hyper | cancer_general | SHH |
| chr7 | 155602751 | 155602805 | Hyper | blood | SHH | chr7 | 156409144 | 156409347 | Hyper | cancer_general | |
| chr7 | 156409665 | 156409802 | Hyper | cancer_general | | chr7 | 156701846 | 156701908 | Hyper | cancer_general | |
| chr7 | 156794153 | 156794235 | Hyper | cancer_general | MNX1, LOC645249 | chr7 | 156794443 | 156794485 | Hyper | cancer_general | MNX1, LOC645249 |
| chr7 | 156794998 | 156795914 | Hyper | cancer_general | MNX1, LOC645249 | chr7 | 156796534 | 156799467 | Hyper | cancer_general, tcga | MNX1, LOC645249 |
| chr7 | 156800999 | 156801029 | Hyper | cancer_general | LOC645249, MNX1 | chr7 | 156801403 | 156801601 | Hyper | lung, cancer_general | LOC64524 |
| chr7 | 156808858 | 156809199 | Hyper | cancer_general | LOC645249, MNX1 | chr7 | 156809983 | 156811436 | Hyper | cancer_general | MNX19, LOC645249, MNX1 |
| chr7 | 156812852 | 156815092 | Hyper | tcga, cancer_general | LOC645249, MNX1 | chr7 | 156871168 | 156871297 | Hyper | cancer_general | |
| chr7 | 157361605 | 157361635 | Hyper | cancer_general, liver_tcga | MIR153-2, PTPRN2 | chr7 | 157476879 | 157477272 | Hyper | cancer_general | |
| chr7 | 157477473 | 157477914 | Hyper | cancer_general | | chr7 | 157481130 | 157481160 | Hyper | pancreas | |
| chr7 | 157481364 | 157481756 | Hyper | cancer_general | | chr7 | 157481969 | 157482168 | Hyper | cancer_general | |
| chr7 | 157482492 | 157482667 | Hyper | cancer_general | | chr7 | 157483320 | 157483538 | Hyper | tcga, cancer_general | |
| chr7 | 157484877 | 157485277 | Hyper | cancer_general | | chr7 | 157485527 | 157485705 | Hyper | cancer_general | WDR60 |
| chr7 | 157485976 | 157486503 | Hyper | cancer_general | | chr7 | 158673836 | 158673942 | Hyper | liver_tcga | VIPR2 |
| chr7 | 158936492 | 158936880 | Hyper | cancer_general, liver_tcga | VIPR2 | chr7 | 158937158 | 158937624 | Hyper | liver_tcga, cancer_general, tcga | |
| chr7 | 158938210 | 158938399 | Hyper | cancer_general | VIPR2 | HCMV-AD169 | 17724 | 17753 | Hyper | virus | |
| HCMV-AD169 | 18691 | 18720 | Hyper | virus | | HCMV-AD169 | 23851 | 23880 | Hyper | virus | |
| HCMV-AD169 | 27296 | 27325 | Hyper | virus | | HCMV-AD169 | 42909 | 42938 | Hyper | virus | |
| HCMV-AD169 | 57909 | 57938 | Hyper | virus | | HCMV-AD169 | 68427 | 68456 | Hyper | virus | |
| HCMV-AD169 | 76862 | 76891 | Hyper | virus | | HCMV-AD169 | 78956 | 78985 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HCMV-AD169 | 81188 | 81217 | Hyper | virus | | HCMV-AD169 | 84448 | 84477 | Hyper | virus | |
| HCMV-AD169 | 88920 | 88949 | Hyper | virus | | HCMV-AD169 | 99889 | 99918 | Hyper | virus | |
| HCMV-AD169 | 101238 | 101267 | Hyper | virus | | HCMV-AD169 | 108021 | 108050 | Hyper | virus | |
| HCMV-AD169 | 114824 | 114853 | Hyper | virus | | HCMV-AD169 | 128011 | 128040 | Hyper | virus | |
| HCMV-AD169 | 129567 | 129596 | Hyper | virus | | HCMV-AD169 | 149187 | 149216 | Hyper | virus | |
| HCMV-AD169 | 162299 | 162328 | Hyper | virus | | HCMV-AD169 | 169250 | 169279 | Hyper | virus | |
| HCMV-AD169 | 171221 | 171250 | Hyper | virus | | HCMV-AD169 | 172561 | 172590 | Hyper | virus | |
| HCMV-AD169 | 177053 | 177082 | Hyper | virus | | HCMV-AD169 | 193060 | 193089 | Hyper | virus | |
| HCMV-AD169 | 193858 | 193887 | Hyper | virus | | HCMV-AD169 | 194176 | 194205 | Hyper | virus | |
| HCMV-AD169 | 195222 | 195251 | Hyper | virus | | HCMV-AD169 | 196060 | 196089 | Hyper | virus | |
| HCMV-AD169 | 196817 | 196846 | Hyper | virus | | HCMV-AD169 | 199152 | 199181 | Hyper | virus | |
| HCMV-AD169 | 199906 | 199935 | Hyper | virus | | HCMV-AD169 | 201145 | 201174 | Hyper | virus | |
| HCMV-AD169 | 204433 | 204462 | Hyper | virus | | HCMV-AD169 | 207682 | 207711 | Hyper | virus | |
| HCMV-AD169 | 209510 | 209539 | Hyper | virus | | HCMV-AD169 | 210069 | 210098 | Hyper | virus | |
| HCMV-AD169 | 212133 | 212162 | Hyper | virus | | HCMV-AD169 | 212591 | 212620 | Hyper | virus | |
| HCMV-AD169 | 214453 | 214482 | Hyper | virus | | HCMV-AD169 | 220316 | 220345 | Hyper | virus | |
| GL000225.1 | 37720 | 37842 | Hyper | esophageal | | MCV-R17b | 111 | 140 | Hyper | virus | |
| MCV-R17b | 368 | 397 | Hyper | virus | | MCV-R17b | 625 | 654 | Hyper | virus | |
| MCV-R17b | 882 | 911 | Hyper | virus | | MCV-R17b | 1139 | 1168 | Hyper | virus | |
| MCV-R17b | 1396 | 1425 | Hyper | virus | | MCV-R17b | 1653 | 1682 | Hyper | virus | |
| MCV-R17b | 1910 | 1939 | Hyper | virus | | MCV-R17b | 2167 | 2196 | Hyper | virus | |
| MCV-R17b | 2424 | 2453 | Hyper | virus | | MCV-R17b | 2681 | 2710 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| MCV-R17b | 2938 | 2967 | Hyper | virus | | MCV-R17b | 3195 | 3224 | Hyper | virus | |
| MCV-R17b | 3452 | 3481 | Hyper | virus | | MCV-R17b | 3709 | 3738 | Hyper | virus | |
| MCV-R17b | 3966 | 3995 | Hyper | virus | | MCV-R17b | 4223 | 4252 | Hyper | virus | |
| MCV-R17b | 4480 | 4509 | Hyper | virus | | MCV-R17b | 4737 | 4766 | Hyper | virus | |
| MCV-R17b | 4994 | 5023 | Hyper | virus | | | | | | | |

TABLE 12

Pan Cancer #2

| chr | start | end | chr | start | end | chr | start | end |
|---|---|---|---|---|---|---|---|---|
| chr1 | 715373 | 715447 | chr1 | 898654 | 898690 | chr1 | 913532 | 913955 |
| chr1 | 1047531 | 1047647 | chr1 | 1080583 | 1080824 | chr1 | 1095420 | 1095459 |
| chr1 | 1146734 | 1146818 | chr1 | 1218737 | 1218820 | chr1 | 1223512 | 1223652 |
| chr1 | 1235813 | 1236078 | chr1 | 1253330 | 1253386 | chr1 | 1267014 | 1267151 |
| chr1 | 1267462 | 1267699 | chr1 | 1267906 | 1268158 | chr1 | 1281214 | 1281244 |
| chr1 | 1341668 | 1341743 | chr1 | 1436043 | 1436211 | chr1 | 1473125 | 1473207 |
| chr1 | 1475556 | 1475643 | chr1 | 1476255 | 1476318 | chr1 | 1483186 | 1483363 |
| chr1 | 1547129 | 1547348 | chr1 | 1563193 | 1563223 | chr1 | 1688882 | 1689012 |
| chr1 | 1805049 | 1805089 | chr1 | 1856436 | 1856466 | chr1 | 1857847 | 1857909 |
| chr1 | 1874744 | 1874787 | chr1 | 1910415 | 1910445 | chr1 | 1923457 | 1923521 |
| chr1 | 1935274 | 1935459 | chr1 | 1974848 | 1974925 | chr1 | 2066490 | 2066679 |
| chr1 | 2125216 | 2125483 | chr1 | 2165895 | 2165999 | chr1 | 2263169 | 2263263 |
| chr1 | 2267552 | 2267690 | chr1 | 2304327 | 2304389 | chr1 | 2307925 | 2307955 |
| chr1 | 2308376 | 2308636 | chr1 | 2309868 | 2309953 | chr1 | 2331363 | 2331437 |
| chr1 | 2336397 | 2336427 | chr1 | 2375148 | 2375543 | chr1 | 2397001 | 2397031 |
| chr1 | 2428331 | 2428385 | chr1 | 2472174 | 2472301 | chr1 | 2507063 | 2507183 |
| chr1 | 2514330 | 2514376 | chr1 | 2521024 | 2521063 | chr1 | 2706308 | 2706334 |
| chr1 | 2830155 | 2830185 | chr1 | 2866038 | 2866068 | chr1 | 2984719 | 2984749 |
| chr1 | 3102653 | 3102779 | chr1 | 3158823 | 3158962 | chr1 | 3182883 | 3182917 |
| chr1 | 3183415 | 3183455 | chr1 | 3322090 | 3322170 | chr1 | 3567093 | 3567344 |
| chr1 | 3567738 | 3567850 | chr1 | 3567883 | 3568226 | chr1 | 3601850 | 3601946 |
| chr1 | 3607081 | 3607236 | chr1 | 3659550 | 3659642 | chr1 | 3659672 | 3659716 |
| chr1 | 3663532 | 3663562 | chr1 | 3663874 | 3663921 | chr1 | 3664461 | 3664741 |
| chr1 | 3683686 | 3683818 | chr1 | 3700384 | 3700414 | chr1 | 3733551 | 3733581 |
| chr1 | 4111061 | 4111231 | chr1 | 4401433 | 4401463 | chr1 | 4714018 | 4714074 |
| chr1 | 4714164 | 4714345 | chr1 | 4715428 | 4715539 | chr1 | 4715575 | 4716701 |
| chr1 | 5919973 | 5920071 | chr1 | 5920650 | 5920710 | chr1 | 5924296 | 5924431 |
| chr1 | 5924851 | 5924984 | chr1 | 5926596 | 5926645 | chr1 | 5933086 | 5933144 |
| chr1 | 5934925 | 5935061 | chr1 | 5940517 | 5940547 | chr1 | 5940945 | 5941132 |
| chr1 | 5944299 | 5944449 | chr1 | 5944962 | 5945001 | chr1 | 5945348 | 5945435 |
| chr1 | 5947258 | 5947288 | chr1 | 5949491 | 5949575 | chr1 | 5950965 | 5951039 |
| chr1 | 5957473 | 5957503 | chr1 | 5967237 | 5967267 | chr1 | 5969001 | 5969283 |
| chr1 | 5972104 | 5972134 | chr1 | 5972878 | 5972922 | chr1 | 6021621 | 6021651 |
| chr1 | 6025872 | 6025950 | chr1 | 6036766 | 6036796 | chr1 | 6056157 | 6056201 |
| chr1 | 6056506 | 6056651 | chr1 | 6059910 | 6059974 | chr1 | 6166353 | 6166469 |
| chr1 | 6171763 | 6171810 | chr1 | 6186511 | 6186546 | chr1 | 6280243 | 6280273 |
| chr1 | 6284828 | 6284858 | chr1 | 6304201 | 6304242 | chr1 | 6360593 | 6360634 |
| chr1 | 6410456 | 6410486 | chr1 | 6446131 | 6446308 | chr1 | 6480514 | 6480831 |
| chr1 | 6501055 | 6501179 | chr1 | 6507678 | 6508126 | chr1 | 6672227 | 6672351 |
| chr1 | 6713914 | 6714041 | chr1 | 6714348 | 6714378 | chr1 | 6776304 | 6776388 |
| chr1 | 7764641 | 7764737 | chr1 | 7973843 | 7973948 | chr1 | 8085685 | 8085715 |
| chr1 | 8549986 | 8550078 | chr1 | 9324231 | 9324274 | chr1 | 9402465 | 9402616 |
| chr1 | 9527172 | 9527208 | chr1 | 9601954 | 9601984 | chr1 | 9712074 | 9712104 |
| chr1 | 9712561 | 9713014 | chr1 | 9722138 | 9722215 | chr1 | 9795995 | 9796196 |
| chr1 | 9865110 | 9865140 | chr1 | 9867157 | 9867316 | chr1 | 10091888 | 10092060 |
| chr1 | 10095469 | 10095845 | chr1 | 10123736 | 10123928 | chr1 | 10166521 | 10166551 |
| chr1 | 10491694 | 10491724 | chr1 | 10948552 | 10948582 | chr1 | 11169346 | 11169375 |
| chr1 | 11174404 | 11174433 | chr1 | 11181358 | 11181432 | chr1 | 11182142 | 11182171 |
| chr1 | 11188149 | 11188178 | chr1 | 11210182 | 11210211 | chr1 | 11217215 | 11217337 |
| chr1 | 11249032 | 11249061 | chr1 | 11538775 | 11538821 | chr1 | 11539175 | 11539205 |
| chr1 | 11539410 | 11539440 | chr1 | 11540129 | 11540178 | chr1 | 11591719 | 11591826 |
| chr1 | 11752476 | 11752511 | chr1 | 11886250 | 11886280 | chr1 | 11936748 | 11936778 |
| chr1 | 11959093 | 11959196 | chr1 | 12041374 | 12041525 | chr1 | 12123243 | 12123553 |
| chr1 | 12227685 | 12227941 | chr1 | 12251443 | 12251958 | chr1 | 12460299 | 12460356 |
| chr1 | 13910436 | 13910714 | chr1 | 13984525 | 13984742 | chr1 | 14026481 | 14026618 |
| chr1 | 14032304 | 14032347 | chr1 | 14097878 | 14098015 | chr1 | 14128478 | 14128588 |
| chr1 | 14149749 | 14149867 | chr1 | 14730425 | 14730472 | chr1 | 14746206 | 14746245 |
| chr1 | 14925501 | 14926050 | chr1 | 15128565 | 15128595 | chr1 | 15251120 | 15251211 |
| chr1 | 15480593 | 15480892 | chr1 | 16474413 | 16474576 | chr1 | 16475031 | 16475207 |
| chr1 | 16861522 | 16861552 | chr1 | 17445857 | 17445943 | chr1 | 17757538 | 17757570 |
| chr1 | 17787472 | 17787502 | chr1 | 18437457 | 18437526 | chr1 | 18956211 | 18956304 |
| chr1 | 18956574 | 18956610 | chr1 | 18956856 | 18957246 | chr1 | 18957507 | 18957587 |
| chr1 | 18958033 | 18958228 | chr1 | 18958359 | 18958381 | chr1 | 18959456 | 18959550 |
| chr1 | 18960897 | 18960990 | chr1 | 18962727 | 18963135 | chr1 | 18969625 | 18969819 |
| chr1 | 18971852 | 18971929 | chr1 | 18972130 | 18972160 | chr1 | 19043563 | 19043678 |
| chr1 | 19980747 | 19980858 | chr1 | 19992418 | 19992432 | chr1 | 20127338 | 20127471 |
| chr1 | 20248109 | 20248141 | chr1 | 20492168 | 20492298 | chr1 | 20618329 | 20618369 |
| chr1 | 20693317 | 20693420 | chr1 | 20879035 | 20879228 | chr1 | 20879256 | 20879289 |
| chr1 | 20879562 | 20879640 | chr1 | 20879845 | 20879957 | chr1 | 20880182 | 20880605 |
| chr1 | 21026117 | 21026225 | chr1 | 21042894 | 21042924 | chr1 | 21044125 | 21044161 |
| chr1 | 21050471 | 21050511 | chr1 | 21058635 | 21058776 | chr1 | 21573283 | 21573362 |
| chr1 | 21573668 | 21574203 | chr1 | 21713716 | 21713792 | chr1 | 21835943 | 21836007 |
| chr1 | 22140753 | 22141184 | chr1 | 22141326 | 22141355 | chr1 | 22222711 | 22222793 |
| chr1 | 22927410 | 22927482 | chr1 | 23347997 | 23348043 | chr1 | 23449766 | 23449859 |
| chr1 | 23748982 | 23749070 | chr1 | 23885070 | 23885100 | chr1 | 24104000 | 24104062 |
| chr1 | 24161782 | 24161882 | chr1 | 24740603 | 24740829 | chr1 | 25255921 | 25255934 |

TABLE 12-continued

Pan Cancer #2

| chr | start | end | chr | start | end | chr | start | end |
|---|---|---|---|---|---|---|---|---|
| chr1 | 25256354 | 25256383 | chr1 | 25257157 | 25257205 | chr1 | 25257490 | 25257529 |
| chr1 | 25257532 | 25257561 | chr1 | 25257916 | 25258250 | chr1 | 25919307 | 25919337 |
| chr1 | 26183522 | 26183579 | chr1 | 26467523 | 26467630 | chr1 | 26551729 | 26551796 |
| chr1 | 26552086 | 26552130 | chr1 | 26737583 | 26737613 | chr1 | 26737946 | 26738182 |
| chr1 | 26917724 | 26917816 | chr1 | 26963625 | 26963789 | chr1 | 27190175 | 27190278 |
| chr1 | 27332448 | 27332673 | chr1 | 27340252 | 27340412 | chr1 | 27724058 | 27724093 |
| chr1 | 27844518 | 27844548 | chr1 | 28558539 | 28558571 | chr1 | 28726724 | 28726812 |
| chr1 | 28727177 | 28727324 | chr1 | 28727894 | 28728020 | chr1 | 29047659 | 29048643 |
| chr1 | 29060250 | 29060311 | chr1 | 29065131 | 29065211 | chr1 | 29450491 | 29450543 |
| chr1 | 29586072 | 29586674 | chr1 | 29804947 | 29805094 | chr1 | 30351554 | 30351742 |
| chr1 | 30815412 | 30815416 | chr1 | 30815455 | 30815578 | chr1 | 31863186 | 31863216 |
| chr1 | 32180397 | 32180427 | chr1 | 32237639 | 32238507 | chr1 | 32410276 | 32410306 |
| chr1 | 32410519 | 32410614 | chr1 | 32533211 | 32533653 | chr1 | 32705488 | 32705550 |
| chr1 | 32756498 | 32756581 | chr1 | 32930458 | 32930558 | chr1 | 32938720 | 32938750 |
| chr1 | 33163605 | 33163786 | chr1 | 33219567 | 33219596 | chr1 | 34628948 | 34628978 |
| chr1 | 34629469 | 34629728 | chr1 | 34630548 | 34630635 | chr1 | 34630859 | 34630978 |
| chr1 | 34631580 | 34631662 | chr1 | 34631933 | 34631963 | chr1 | 34642380 | 34642489 |
| chr1 | 35258637 | 35258714 | chr1 | 35351078 | 35351659 | chr1 | 35395526 | 35395851 |
| chr1 | 35586911 | 35586962 | chr1 | 35664625 | 35664746 | chr1 | 36042679 | 36043489 |
| chr1 | 36236269 | 36236299 | chr1 | 36334925 | 36335053 | chr1 | 36563479 | 36563522 |
| chr1 | 36849009 | 36849038 | chr1 | 37498792 | 37498844 | chr1 | 37498889 | 37499181 |
| chr1 | 37499460 | 37499682 | chr1 | 37500014 | 37500153 | chr1 | 37500468 | 37500574 |
| chr1 | 37500603 | 37500806 | chr1 | 37501072 | 37501102 | chr1 | 38060267 | 38060317 |
| chr1 | 38100689 | 38100851 | chr1 | 38219712 | 38219795 | chr1 | 38230042 | 38230242 |
| chr1 | 38230283 | 38230297 | chr1 | 38230779 | 38230859 | chr1 | 38398213 | 38398348 |
| chr1 | 38412504 | 38412832 | chr1 | 38510178 | 38510217 | chr1 | 38510563 | 38510624 |
| chr1 | 38510854 | 38511119 | chr1 | 38511337 | 38511799 | chr1 | 38511822 | 38511824 |
| chr1 | 38512385 | 38512415 | chr1 | 38513244 | 38513318 | chr1 | 39269741 | 39270121 |
| chr1 | 39416980 | 39417182 | chr1 | 40072633 | 40072680 | chr1 | 40137898 | 40137984 |
| chr1 | 40237141 | 40237203 | chr1 | 40349545 | 40349647 | chr1 | 40625371 | 40625401 |
| chr1 | 40708443 | 40708578 | chr1 | 40915590 | 40915620 | chr1 | 41283958 | 41284463 |
| chr1 | 41847583 | 41847702 | chr1 | 41848810 | 41848840 | chr1 | 41915253 | 41915283 |
| chr1 | 41967342 | 41967418 | chr1 | 41991640 | 41991702 | chr1 | 43188741 | 43188874 |
| chr1 | 43400336 | 43400386 | chr1 | 43478202 | 43478255 | chr1 | 43814994 | 43815023 |
| chr1 | 43834741 | 43834922 | chr1 | 43842664 | 43842779 | chr1 | 44068774 | 44068804 |
| chr1 | 44109845 | 44109959 | chr1 | 44310283 | 44310324 | chr1 | 44494137 | 44494169 |
| chr1 | 44726912 | 44727268 | chr1 | 44872448 | 44872722 | chr1 | 44872924 | 44873172 |
| chr1 | 44873510 | 44873706 | chr1 | 44883121 | 44883214 | chr1 | 44884122 | 44884122 |
| chr1 | 45240427 | 45240514 | chr1 | 45308154 | 45308262 | chr1 | 45308592 | 45308625 |
| chr1 | 45645870 | 45645998 | chr1 | 45768429 | 45768504 | chr1 | 46077719 | 46077805 |
| chr1 | 46347598 | 46347689 | chr1 | 46632876 | 46632923 | chr1 | 46744657 | 46744733 |
| chr1 | 46913837 | 46913876 | chr1 | 46914193 | 46914245 | chr1 | 46914656 | 46914686 |
| chr1 | 46932765 | 46932905 | chr1 | 46951207 | 46951317 | chr1 | 46951645 | 46951739 |
| chr1 | 46956454 | 46956603 | chr1 | 46956823 | 46957171 | chr1 | 47009929 | 47010035 |
| chr1 | 47035373 | 47035403 | chr1 | 47078736 | 47078782 | chr1 | 47695122 | 47695422 |
| chr1 | 47696295 | 47696520 | chr1 | 47696821 | 47696964 | chr1 | 47697017 | 47697110 |
| chr1 | 47697356 | 47697510 | chr1 | 47697732 | 47697946 | chr1 | 47698007 | 47698210 |
| chr1 | 47788247 | 47788348 | chr1 | 47882063 | 47882322 | chr1 | 47882769 | 47882803 |
| chr1 | 47909718 | 47910160 | chr1 | 47910523 | 47910624 | chr1 | 47910749 | 47910914 |
| chr1 | 47911424 | 47911508 | chr1 | 47999090 | 47999163 | chr1 | 48059078 | 48059243 |
| chr1 | 49242344 | 49242533 | chr1 | 50513629 | 50513745 | chr1 | 50799278 | 50799316 |
| chr1 | 50799394 | 50799400 | chr1 | 50880932 | 50881302 | chr1 | 50881427 | 50881956 |
| chr1 | 50882144 | 50882529 | chr1 | 50882808 | 50883611 | chr1 | 50883882 | 50883976 |
| chr1 | 50884021 | 50884352 | chr1 | 50884691 | 50884887 | chr1 | 50885336 | 50885366 |
| chr1 | 50886188 | 50887084 | chr1 | 50887176 | 50887284 | chr1 | 50888709 | 50888795 |
| chr1 | 50889124 | 50889510 | chr1 | 50889820 | 50890379 | chr1 | 50890796 | 50891595 |
| chr1 | 50892153 | 50892283 | chr1 | 50892337 | 50892351 | chr1 | 50892607 | 50893422 |
| chr1 | 50893519 | 50893877 | chr1 | 51424099 | 51424224 | chr1 | 51763252 | 51763298 |
| chr1 | 52832687 | 52832820 | chr1 | 53019468 | 53019568 | chr1 | 53068166 | 53068546 |
| chr1 | 53098842 | 53099067 | chr1 | 53129154 | 53129244 | chr1 | 53192045 | 53192075 |
| chr1 | 53308568 | 53308607 | chr1 | 53308908 | 53309248 | chr1 | 53528374 | 53528439 |
| chr1 | 53705647 | 53705701 | chr1 | 54203829 | 54204399 | chr1 | 54586626 | 54586736 |
| chr1 | 54837089 | 54837119 | chr1 | 54877027 | 54877451 | chr1 | 55231115 | 55231177 |
| chr1 | 55462673 | 55462703 | chr1 | 57888367 | 57888397 | chr1 | 57888987 | 57889087 |
| chr1 | 57889402 | 57889654 | chr1 | 57890431 | 57890650 | chr1 | 58715153 | 58715194 |
| chr1 | 58715475 | 58715854 | chr1 | 58715979 | 58715993 | chr1 | 61519360 | 61519394 |
| chr1 | 61541602 | 61541718 | chr1 | 62189908 | 62189987 | chr1 | 62660740 | 62660768 |
| chr1 | 62660786 | 62660861 | chr1 | 62793237 | 62793267 | chr1 | 63539509 | 63539887 |
| chr1 | 63785619 | 63785766 | chr1 | 63786079 | 63786329 | chr1 | 63787031 | 63787063 |
| chr1 | 63787302 | 63787568 | chr1 | 63788423 | 63788557 | chr1 | 63788920 | 63789496 |
| chr1 | 63789729 | 63789791 | chr1 | 63789850 | 63789912 | chr1 | 63790253 | 63790278 |
| chr1 | 63792561 | 63792648 | chr1 | 63792798 | 63793072 | chr1 | 63795263 | 63796277 |
| chr1 | 63796498 | 63796575 | chr1 | 64240026 | 64240118 | chr1 | 64240617 | 64240673 |
| chr1 | 64734652 | 64734694 | chr1 | 64937330 | 64937542 | chr1 | 65303636 | 65303692 |
| chr1 | 65304227 | 65304256 | chr1 | 65305384 | 65305413 | chr1 | 65306926 | 65306955 |
| chr1 | 65309787 | 65309816 | chr1 | 65310487 | 65310531 | chr1 | 65311188 | 65311217 |

TABLE 12-continued

Pan Cancer #2

| chr | start | end | chr | start | end | chr | start | end |
|---|---|---|---|---|---|---|---|---|
| chr1 | 65312331 | 65312432 | chr1 | 65731337 | 65731446 | chr1 | 65990955 | 65991018 |
| chr1 | 65991446 | 65991560 | chr1 | 65991606 | 65991757 | chr1 | 66258180 | 66258650 |
| chr1 | 66258672 | 66258774 | chr1 | 66259137 | 66259174 | chr1 | 66998790 | 66999332 |
| chr1 | 66999636 | 66999673 | chr1 | 67218064 | 67218343 | chr1 | 67390334 | 67390450 |
| chr1 | 67391067 | 67391096 | chr1 | 67669791 | 67669853 | chr1 | 67773159 | 67773780 |
| chr1 | 70033609 | 70033916 | chr1 | 70034459 | 70034574 | chr1 | 70035088 | 70035537 |
| chr1 | 70599012 | 70599169 | chr1 | 70672778 | 70672878 | chr1 | 72749641 | 72749699 |
| chr1 | 75595819 | 75595990 | chr1 | 75596136 | 75596384 | chr1 | 75596687 | 75596858 |
| chr1 | 75596930 | 75597584 | chr1 | 75597923 | 75598179 | chr1 | 75598384 | 75598414 |
| chr1 | 75599427 | 75599621 | chr1 | 75600225 | 75600848 | chr1 | 75600925 | 75601118 |
| chr1 | 75601188 | 75601428 | chr1 | 75601983 | 75603052 | chr1 | 76080484 | 76080768 |
| chr1 | 76082129 | 76082209 | chr1 | 76354624 | 76354754 | chr1 | 76540450 | 76540666 |
| chr1 | 77333058 | 77333088 | chr1 | 77333384 | 77333433 | chr1 | 77334169 | 77334385 |
| chr1 | 77334409 | 77334756 | chr1 | 77747366 | 77747453 | chr1 | 77747939 | 77748235 |
| chr1 | 78463647 | 78463677 | chr1 | 78511466 | 78512354 | chr1 | 78957292 | 78957522 |
| chr1 | 82267150 | 82267185 | chr1 | 82268573 | 82268815 | chr1 | 84944491 | 84944568 |
| chr1 | 85358752 | 85358822 | chr1 | 85463349 | 85463378 | chr1 | 85725508 | 85725537 |
| chr1 | 85725639 | 85725668 | chr1 | 86296345 | 86296375 | chr1 | 86621660 | 86622127 |
| chr1 | 86622526 | 86622551 | chr1 | 86860608 | 86860949 | chr1 | 87617774 | 87617807 |
| chr1 | 89394066 | 89394163 | chr1 | 90099997 | 90100084 | chr1 | 90309292 | 90309490 |
| chr1 | 91172012 | 91172677 | chr1 | 91177941 | 91178207 | chr1 | 91180075 | 91180306 |
| chr1 | 91181932 | 91182132 | chr1 | 91182338 | 91183195 | chr1 | 91183251 | 91183610 |
| chr1 | 91183951 | 91183986 | chr1 | 91184423 | 91184672 | chr1 | 91185190 | 91185308 |
| chr1 | 91185348 | 91185707 | chr1 | 91188983 | 91189383 | chr1 | 91189688 | 91190380 |
| chr1 | 91190869 | 91190948 | chr1 | 91190985 | 91191234 | chr1 | 91191290 | 91191310 |
| chr1 | 91192274 | 91192576 | chr1 | 91194414 | 91194569 | chr1 | 91195117 | 91195390 |
| chr1 | 91195879 | 91196194 | chr1 | 91196226 | 91196502 | chr1 | 91316261 | 91316313 |
| chr1 | 91316627 | 91316682 | chr1 | 91869988 | 91870018 | chr1 | 92948324 | 92948597 |
| chr1 | 92948841 | 92948976 | chr1 | 92952291 | 92952655 | chr1 | 94147641 | 94147670 |
| chr1 | 94147816 | 94147845 | chr1 | 94343568 | 94343744 | chr1 | 94911234 | 94911328 |
| chr1 | 95006795 | 95006902 | chr1 | 97185262 | 97185609 | chr1 | 98510791 | 98511335 |
| chr1 | 98511628 | 98511922 | chr1 | 98514225 | 98514255 | chr1 | 98515142 | 98515191 |
| chr1 | 98515256 | 98515319 | chr1 | 98519023 | 98519675 | chr1 | 99469682 | 99469696 |
| chr1 | 99469760 | 99469788 | chr1 | 99470785 | 99470847 | chr1 | 100239507 | 100239544 |
| chr1 | 100310827 | 100310979 | chr1 | 100437068 | 100437172 | chr1 | 101004456 | 101004737 |
| chr1 | 101005071 | 101005144 | chr1 | 101005360 | 101005675 | chr1 | 101702504 | 101702616 |
| chr1 | 101703612 | 101703642 | chr1 | 103574508 | 103574537 | chr1 | 107682735 | 107682977 |
| chr1 | 107683439 | 107683517 | chr1 | 107684240 | 107684439 | chr1 | 108507063 | 108507076 |
| chr1 | 108507320 | 108507375 | chr1 | 108507495 | 108507497 | chr1 | 108507717 | 108507810 |
| chr1 | 108508052 | 108508640 | chr1 | 108722798 | 108722828 | chr1 | 109203609 | 109203672 |
| chr1 | 109585463 | 109585632 | chr1 | 109595405 | 109595534 | chr1 | 109631549 | 109631682 |
| chr1 | 109644226 | 109644336 | chr1 | 110610586 | 110610897 | chr1 | 110611046 | 110611276 |
| chr1 | 110611435 | 110611513 | chr1 | 110611654 | 110611965 | chr1 | 110626684 | 110627578 |
| chr1 | 110672889 | 110673233 | chr1 | 110692973 | 110693496 | chr1 | 110693737 | 110694117 |
| chr1 | 110754003 | 110754101 | chr1 | 110754309 | 110754356 | chr1 | 110883542 | 110883965 |
| chr1 | 111097906 | 111097936 | chr1 | 111098196 | 111098316 | chr1 | 111216763 | 111216972 |
| chr1 | 111217195 | 111217891 | chr1 | 111217924 | 111217982 | chr1 | 111440961 | 111440999 |
| chr1 | 111506007 | 111506212 | chr1 | 111813546 | 111813587 | chr1 | 112084954 | 112084984 |
| chr1 | 113166315 | 113166394 | chr1 | 114428007 | 114428160 | chr1 | 114448943 | 114448990 |
| chr1 | 114695439 | 114695736 | chr1 | 114695943 | 114695983 | chr1 | 114696350 | 114696463 |
| chr1 | 114696541 | 114696712 | chr1 | 115055395 | 115055425 | chr1 | 115256514 | 115256552 |
| chr1 | 115258729 | 115258772 | chr1 | 115631867 | 115631915 | chr1 | 115632469 | 115632555 |
| chr1 | 115880184 | 115880395 | chr1 | 115880873 | 115881042 | chr1 | 116214104 | 116214318 |
| chr1 | 116371139 | 116371201 | chr1 | 116380651 | 116381287 | chr1 | 116382387 | 116382478 |
| chr1 | 117901133 | 117901264 | chr1 | 119522074 | 119522434 | chr1 | 119522839 | 119522853 |
| chr1 | 119522926 | 119522940 | chr1 | 119527237 | 119527391 | chr1 | 119527623 | 119527652 |
| chr1 | 119528653 | 119529118 | chr1 | 119529804 | 119529839 | chr1 | 119530100 | 119530148 |
| chr1 | 119530202 | 119530507 | chr1 | 119530554 | 119530725 | chr1 | 119531029 | 119531157 |
| chr1 | 119532318 | 119532320 | chr1 | 119535908 | 119536377 | chr1 | 119542322 | 119542352 |
| chr1 | 119543070 | 119543214 | chr1 | 119543532 | 119544182 | chr1 | 119548823 | 119548853 |
| chr1 | 119549058 | 119549734 | chr1 | 119549915 | 119549929 | chr1 | 119550155 | 119550278 |
| chr1 | 119550533 | 119550633 | chr1 | 119551014 | 119551269 | chr1 | 146551186 | 146551215 |
| chr1 | 150603138 | 150603170 | chr1 | 150941425 | 150941847 | chr1 | 150994849 | 150995152 |
| chr1 | 151042405 | 151042496 | chr1 | 151169248 | 151170206 | chr1 | 151253146 | 151253427 |
| chr1 | 151300888 | 151300918 | chr1 | 151362640 | 151362779 | chr1 | 151693945 | 151694351 |
| chr1 | 151812413 | 151812442 | chr1 | 152009415 | 152009510 | chr1 | 152085398 | 152085504 |
| chr1 | 152488150 | 152488197 | chr1 | 153539476 | 153539637 | chr1 | 153540096 | 153540154 |
| chr1 | 153651965 | 153652379 | chr1 | 153896746 | 153896800 | chr1 | 153937124 | 153937330 |
| chr1 | 153948791 | 153948823 | chr1 | 154127987 | 154128016 | chr1 | 154156468 | 154156717 |
| chr1 | 154298320 | 154298557 | chr1 | 154475372 | 154475531 | chr1 | 154491036 | 154491066 |
| chr1 | 154516810 | 154516845 | chr1 | 155043331 | 155043657 | chr1 | 155161778 | 155162033 |
| chr1 | 155164415 | 155164455 | chr1 | 155283218 | 155283248 | chr1 | 155578375 | 155578921 |
| chr1 | 155617837 | 155617962 | chr1 | 155653788 | 155653868 | chr1 | 155826248 | 155826336 |
| chr1 | 155874151 | 155874300 | chr1 | 155874508 | 155874546 | chr1 | 155954282 | 155954396 |
| chr1 | 156010377 | 156010548 | chr1 | 156017591 | 156017683 | chr1 | 156030286 | 156030621 |
| chr1 | 156215329 | 156215359 | chr1 | 156215607 | 156215805 | chr1 | 156357993 | 156358508 |

TABLE 12-continued

Pan Cancer #2

| chr | start | end | chr | start | end | chr | start | end |
|---|---|---|---|---|---|---|---|---|
| chr1 | 156390135 | 156390698 | chr1 | 156405635 | 156406070 | chr1 | 156406105 | 156406431 |
| chr1 | 156432124 | 156432637 | chr1 | 156594974 | 156595021 | chr1 | 156611889 | 156611943 |
| chr1 | 156611994 | 156612119 | chr1 | 156626589 | 156626658 | chr1 | 156626891 | 156627018 |
| chr1 | 156646278 | 156646307 | chr1 | 156646593 | 156646596 | chr1 | 156646635 | 156646647 |
| chr1 | 156814933 | 156814952 | chr1 | 156815031 | 156815146 | chr1 | 156815445 | 156815745 |
| chr1 | 156830269 | 156830348 | chr1 | 156838167 | 156838320 | chr1 | 156863107 | 156863331 |
| chr1 | 156863662 | 156863724 | chr1 | 157247347 | 157247388 | chr1 | 157458909 | 157458961 |
| chr1 | 157895413 | 157895443 | chr1 | 158205040 | 158205070 | chr1 | 158245556 | 158245586 |
| chr1 | 158295829 | 158295935 | chr1 | 158318949 | 158318979 | chr1 | 158591699 | 158591947 |
| chr1 | 158669704 | 158669882 | chr1 | 158672648 | 158672678 | chr1 | 158687415 | 158687550 |
| chr1 | 158748648 | 158748771 | chr1 | 158760197 | 158760235 | chr1 | 158778060 | 158778152 |
| chr1 | 158815136 | 158815295 | chr1 | 158907635 | 158907665 | chr1 | 159140357 | 159140386 |
| chr1 | 159158348 | 159158368 | chr1 | 159158472 | 159158511 | chr1 | 159187279 | 159187429 |
| chr1 | 159258862 | 159258891 | chr1 | 159337419 | 159337615 | chr1 | 159409192 | 159409221 |
| chr1 | 160451043 | 160451202 | chr1 | 160693934 | 160694102 | chr1 | 160880758 | 160880788 |
| chr1 | 160986299 | 160986385 | chr1 | 160992336 | 160992587 | chr1 | 161007587 | 161007746 |
| chr1 | 161013554 | 161013677 | chr1 | 161086730 | 161086813 | chr1 | 161122645 | 161122778 |
| chr1 | 161228659 | 161228891 | chr1 | 161275564 | 161275578 | chr1 | 161275640 | 161276026 |
| chr1 | 161359069 | 161359099 | chr1 | 161367577 | 161367701 | chr1 | 161368283 | 161368507 |
| chr1 | 161368993 | 161369405 | chr1 | 161369859 | 161369945 | chr1 | 161442441 | 161442471 |
| chr1 | 161466301 | 161466347 | chr1 | 161471657 | 161471779 | chr1 | 161591472 | 161591546 |
| chr1 | 162427088 | 162427153 | chr1 | 162724401 | 162724430 | chr1 | 162729615 | 162729686 |
| chr1 | 162748392 | 162748421 | chr1 | 162792306 | 162792533 | chr1 | 163393034 | 163393064 |
| chr1 | 164290615 | 164290671 | chr1 | 164428741 | 164428831 | chr1 | 164518220 | 164518270 |
| chr1 | 164730649 | 164730796 | chr1 | 165086988 | 165087027 | chr1 | 165205079 | 165205146 |
| chr1 | 165321747 | 165321786 | chr1 | 165323151 | 165323181 | chr1 | 165324196 | 165324249 |
| chr1 | 165324305 | 165324357 | chr1 | 165324488 | 165324668 | chr1 | 165325108 | 165325356 |
| chr1 | 165325395 | 165325521 | chr1 | 165325896 | 165325950 | chr1 | 165326204 | 165326204 |
| chr1 | 165326297 | 165326469 | chr1 | 165414191 | 165414272 | chr1 | 166134247 | 166134306 |
| chr1 | 166134728 | 166134796 | chr1 | 166135193 | 166135281 | chr1 | 166853563 | 166853592 |
| chr1 | 166890292 | 166890436 | chr1 | 166916866 | 166916920 | chr1 | 166916937 | 166916949 |
| chr1 | 167090617 | 167090757 | chr1 | 167599179 | 167599330 | chr1 | 167599616 | 167599844 |
| chr1 | 167823339 | 167823461 | chr1 | 169355697 | 169355727 | chr1 | 169396376 | 169396688 |
| chr1 | 169396731 | 169396923 | chr1 | 169838016 | 169838187 | chr1 | 169930112 | 169930305 |
| chr1 | 170063947 | 170064218 | chr1 | 170629540 | 170629569 | chr1 | 170629999 | 170630029 |
| chr1 | 170630456 | 170630810 | chr1 | 170631084 | 170631163 | chr1 | 170631477 | 170631559 |
| chr1 | 170633607 | 170633637 | chr1 | 170637666 | 170637796 | chr1 | 170640517 | 170640624 |
| chr1 | 170640665 | 170640691 | chr1 | 171625525 | 171625561 | chr1 | 171665240 | 171665330 |
| chr1 | 171810200 | 171810972 | chr1 | 173638647 | 173639085 | chr1 | 175346381 | 175346551 |
| chr1 | 175388664 | 175388700 | chr1 | 177133721 | 177133814 | chr1 | 177140105 | 177140173 |
| chr1 | 177140305 | 177140714 | chr1 | 177150773 | 177150803 | chr1 | 178063112 | 178063150 |
| chr1 | 179046338 | 179046385 | chr1 | 179262226 | 179262256 | chr1 | 179544967 | 179545098 |
| chr1 | 179712164 | 179712338 | chr1 | 179712411 | 179712553 | chr1 | 179712568 | 179712733 |
| chr1 | 179712831 | 179713174 | chr1 | 180198061 | 180198209 | chr1 | 180202649 | 180203016 |
| chr1 | 180203413 | 180203607 | chr1 | 180203634 | 180204619 | chr1 | 180204898 | 180204924 |
| chr1 | 180235730 | 180235760 | chr1 | 180882576 | 180882695 | chr1 | 180919682 | 180919718 |
| chr1 | 180925271 | 180925402 | chr1 | 181014878 | 181014997 | chr1 | 181287679 | 181287757 |
| chr1 | 181288014 | 181288188 | chr1 | 181451407 | 181452120 | chr1 | 181452871 | 181452967 |
| chr1 | 181454873 | 181454912 | chr1 | 181455183 | 181455263 | chr1 | 182584048 | 182584339 |
| chr1 | 182584404 | 182584613 | chr1 | 182807578 | 182807742 | chr1 | 182862133 | 182862328 |
| chr1 | 182921839 | 182921868 | chr1 | 183129382 | 183129737 | chr1 | 183386150 | 183386288 |
| chr1 | 183386599 | 183386626 | chr1 | 183386947 | 183386964 | chr1 | 183387266 | 183387319 |
| chr1 | 183462761 | 183463024 | chr1 | 183627506 | 183627539 | chr1 | 183774244 | 183774363 |
| chr1 | 184005701 | 184005814 | chr1 | 184970783 | 184970847 | chr1 | 185073818 | 185073966 |
| chr1 | 185076172 | 185076270 | chr1 | 185336061 | 185336095 | chr1 | 186570930 | 186571030 |
| chr1 | 190444855 | 190444885 | chr1 | 190445181 | 190445276 | chr1 | 190447389 | 190447519 |
| chr1 | 195732322 | 195732539 | chr1 | 196577628 | 196577858 | chr1 | 196578101 | 196578150 |
| chr1 | 197771547 | 197771893 | chr1 | 197879400 | 197879660 | chr1 | 197879717 | 197880156 |
| chr1 | 197882140 | 197882201 | chr1 | 197882453 | 197882611 | chr1 | 197887052 | 197887066 |
| chr1 | 197887147 | 197887456 | chr1 | 197887707 | 197887741 | chr1 | 197888052 | 197888121 |
| chr1 | 197888181 | 197888319 | chr1 | 197888643 | 197889286 | chr1 | 198124799 | 198124932 |
| chr1 | 200009357 | 200009450 | chr1 | 200009750 | 200010114 | chr1 | 200011323 | 200012227 |
| chr1 | 200478843 | 200478932 | chr1 | 200591054 | 200591225 | chr1 | 201368582 | 201368727 |
| chr1 | 201476501 | 201476619 | chr1 | 201983113 | 201983200 | chr1 | 202081571 | 202081641 |
| chr1 | 202081728 | 202081804 | chr1 | 202183371 | 202183401 | chr1 | 202311820 | 202311901 |
| chr1 | 202531939 | 202532087 | chr1 | 202679215 | 202679518 | chr1 | 202856858 | 202856937 |
| chr1 | 203298307 | 203298710 | chr1 | 203429564 | 203429594 | chr1 | 203681332 | 203681362 |
| chr1 | 204333609 | 204333668 | chr1 | 204478284 | 204478427 | chr1 | 204499813 | 204499842 |
| chr1 | 204524704 | 204524744 | chr1 | 204531203 | 204531757 | chr1 | 204653561 | 204653595 |
| chr1 | 204653793 | 204653807 | chr1 | 205312596 | 205312911 | chr1 | 205424654 | 205424957 |
| chr1 | 205537663 | 205537772 | chr1 | 206950282 | 206950328 | chr1 | 207200870 | 207200962 |
| chr1 | 207227318 | 207227556 | chr1 | 207669496 | 207669787 | chr1 | 207669829 | 207670060 |
| chr1 | 207794579 | 207794609 | chr1 | 207818394 | 207818396 | chr1 | 207818434 | 207818493 |
| chr1 | 207833206 | 207833370 | chr1 | 208084289 | 208084488 | chr1 | 209164972 | 209165091 |
| chr1 | 209381132 | 209381165 | chr1 | 209604382 | 209604597 | chr1 | 209605386 | 209605415 |
| chr1 | 209849170 | 209849199 | chr1 | 209849430 | 209849459 | chr1 | 210111146 | 210111176 |

TABLE 12-continued

Pan Cancer #2

| chr | start | end | chr | start | end | chr | start | end |
|---|---|---|---|---|---|---|---|---|
| chr1 | 210111388 | 210111421 | chr1 | 210111797 | 210111922 | chr1 | 210112037 | 210112140 |
| chr1 | 211847706 | 211847787 | chr1 | 212484610 | 212484816 | chr1 | 212963883 | 212964151 |
| chr1 | 213123871 | 213123979 | chr1 | 213124669 | 213124910 | chr1 | 213189937 | 213190065 |
| chr1 | 214156419 | 214156928 | chr1 | 214158838 | 214158910 | chr1 | 214160107 | 214160184 |
| chr1 | 214360675 | 214360858 | chr1 | 214360927 | 214360968 | chr1 | 214724531 | 214724561 |
| chr1 | 215255094 | 215255799 | chr1 | 216897216 | 216897307 | chr1 | 217307385 | 217308274 |
| chr1 | 217309007 | 217309105 | chr1 | 217309764 | 217309816 | chr1 | 217311265 | 217311839 |
| chr1 | 217313042 | 217313042 | chr1 | 217313069 | 217313747 | chr1 | 217805158 | 217805395 |
| chr1 | 218520096 | 218520291 | chr1 | 218520310 | 218520399 | chr1 | 218520775 | 218520805 |
| chr1 | 219346992 | 219347035 | chr1 | 219347394 | 219347472 | chr1 | 220101145 | 220101210 |
| chr1 | 220101371 | 220101385 | chr1 | 220101683 | 220101712 | chr1 | 220132075 | 220132111 |
| chr1 | 220636466 | 220636510 | chr1 | 220700814 | 220700897 | chr1 | 220896508 | 220896568 |
| chr1 | 221052038 | 221052492 | chr1 | 221053051 | 221053862 | chr1 | 221067506 | 221067688 |
| chr1 | 221068156 | 221068185 | chr1 | 221068793 | 221069150 | chr1 | 221510339 | 221510368 |
| chr1 | 221737191 | 221737220 | chr1 | 223302825 | 223302890 | chr1 | 223538344 | 223538641 |
| chr1 | 223894714 | 223894752 | chr1 | 223899470 | 223899500 | chr1 | 223936633 | 223936752 |
| chr1 | 223936996 | 223937057 | chr1 | 224267615 | 224267662 | chr1 | 224363560 | 224363589 |
| chr1 | 224400490 | 224400524 | chr1 | 224493975 | 224494083 | chr1 | 224528814 | 224528844 |
| chr1 | 224803717 | 224803751 | chr1 | 224804097 | 224804295 | chr1 | 224804396 | 224804686 |
| chr1 | 224804847 | 224804910 | chr1 | 224805198 | 224805751 | chr1 | 225118306 | 225118474 |
| chr1 | 225908076 | 225908184 | chr1 | 226265194 | 226265257 | chr1 | 226384322 | 226384440 |
| chr1 | 226411247 | 226411273 | chr1 | 226411700 | 226411832 | chr1 | 226814346 | 226814408 |
| chr1 | 226925067 | 226925195 | chr1 | 226997660 | 226997719 | chr1 | 227729830 | 227730075 |
| chr1 | 227748700 | 227748733 | chr1 | 228195377 | 228196349 | chr1 | 228201221 | 228201251 |
| chr1 | 228247998 | 228248027 | chr1 | 228248302 | 228248332 | chr1 | 228345999 | 228346195 |
| chr1 | 228461158 | 228461197 | chr1 | 228463311 | 228463706 | chr1 | 228528840 | 228529016 |
| chr1 | 228558699 | 228559238 | chr1 | 228566622 | 228566672 | chr1 | 228604124 | 228604254 |
| chr1 | 228633990 | 228634261 | chr1 | 228645140 | 228645243 | chr1 | 228645306 | 228645734 |
| chr1 | 228646032 | 228646238 | chr1 | 228651432 | 228651626 | chr1 | 228651879 | 228651901 |
| chr1 | 228652207 | 228652452 | chr1 | 228652509 | 228652629 | chr1 | 228693629 | 228693767 |
| chr1 | 228871865 | 228872003 | chr1 | 229476753 | 229476879 | chr1 | 229542838 | 229542952 |
| chr1 | 229543553 | 229543603 | chr1 | 229566753 | 229567276 | chr1 | 229567370 | 229567992 |
| chr1 | 229568158 | 229568204 | chr1 | 229569810 | 229569852 | chr1 | 230404217 | 230404263 |
| chr1 | 230561779 | 230561824 | chr1 | 231149928 | 231150098 | chr1 | 231297103 | 231297221 |
| chr1 | 231298595 | 231298707 | chr1 | 231475814 | 231476081 | chr1 | 232765195 | 232765301 |
| chr1 | 233465473 | 233465503 | chr1 | 233750082 | 233750302 | chr1 | 234040247 | 234040319 |
| chr1 | 234040886 | 234040973 | chr1 | 234041416 | 234041624 | chr1 | 234349988 | 234350100 |
| chr1 | 234445373 | 234445403 | chr1 | 234620866 | 234620979 | chr1 | 234798171 | 234798201 |
| chr1 | 234839889 | 234840058 | chr1 | 234844955 | 234845079 | chr1 | 234845467 | 234845497 |
| chr1 | 235266920 | 235266950 | chr1 | 235665663 | 235665736 | chr1 | 235669296 | 235669398 |
| chr1 | 235813781 | 235813796 | chr1 | 235814010 | 235814202 | chr1 | 235814447 | 235814476 |
| chr1 | 236227637 | 236227743 | chr1 | 236227770 | 236227920 | chr1 | 236228022 | 236228096 |
| chr1 | 236228582 | 236228623 | chr1 | 236228706 | 236228789 | chr1 | 236559176 | 236559206 |
| chr1 | 236559257 | 236559271 | chr1 | 236849457 | 236849505 | chr1 | 237205159 | 237205188 |
| chr1 | 237206102 | 237206265 | chr1 | 237206512 | 237206735 | chr1 | 237970760 | 237970826 |
| chr1 | 238024448 | 238024477 | chr1 | 239550594 | 239551193 | chr1 | 240118848 | 240118973 |
| chr1 | 240161123 | 240161380 | chr1 | 240254944 | 240255011 | chr1 | 240255361 | 240255500 |
| chr1 | 240255819 | 240256158 | chr1 | 240256663 | 240256780 | chr1 | 240775425 | 240775455 |
| chr1 | 241052096 | 241052126 | chr1 | 241052360 | 241052419 | chr1 | 241520296 | 241520345 |
| chr1 | 241520583 | 241520612 | chr1 | 241587034 | 241587113 | chr1 | 241587587 | 241587797 |
| chr1 | 241912749 | 241912778 | chr1 | 242686734 | 242687688 | chr1 | 242688184 | 242688243 |
| chr1 | 242688477 | 242688695 | chr1 | 243646610 | 243646673 | chr1 | 243859000 | 243859029 |
| chr1 | 243921295 | 243921330 | chr1 | 244014221 | 244014376 | chr1 | 244080672 | 244080702 |
| chr1 | 244080963 | 244081061 | chr1 | 244081078 | 244081203 | chr1 | 244115072 | 244115212 |
| chr1 | 244893214 | 244893315 | chr1 | 245032517 | 245032603 | chr1 | 245135753 | 245136064 |
| chr1 | 245494495 | 245494578 | chr1 | 245849914 | 245849944 | chr1 | 246198078 | 246198203 |
| chr1 | 246330309 | 246330409 | chr1 | 246488175 | 246488336 | chr1 | 246654652 | 246654851 |
| chr1 | 247284422 | 247284452 | chr1 | 247496038 | 247496057 | chr1 | 247608784 | 247608814 |
| chr1 | 247684856 | 247684929 | chr1 | 247910678 | 247910780 | chr1 | 248002278 | 248002437 |
| chr1 | 248020516 | 248020630 | chr1 | 248020957 | 248021349 | chr1 | 248028015 | 248028202 |
| chr1 | 248074729 | 248074927 | chr1 | 248099751 | 248099809 | chr1 | 248198552 | 248198721 |
| chr1 | 248328701 | 248328841 | chr1 | 248691575 | 248691616 | chr1 | 248860898 | 248861046 |
| chr1 | 249121600 | 249121704 | chr2 | 46214 | 46450 | chr2 | 142427 | 142468 |
| chr2 | 264163 | 264204 | chr2 | 287580 | 287641 | chr2 | 288404 | 288470 |
| chr2 | 468424 | 468672 | chr2 | 496228 | 496380 | chr2 | 602657 | 602687 |
| chr2 | 720836 | 720894 | chr2 | 875961 | 875991 | chr2 | 945913 | 946000 |
| chr2 | 946208 | 946217 | chr2 | 946526 | 946566 | chr2 | 946917 | 947043 |
| chr2 | 947127 | 947159 | chr2 | 1652837 | 1653230 | chr2 | 1670168 | 1670216 |
| chr2 | 1746614 | 1747032 | chr2 | 1747670 | 1748007 | chr2 | 1748397 | 1748890 |
| chr2 | 2321773 | 2321802 | chr2 | 2336413 | 2336442 | chr2 | 2646900 | 2646930 |
| chr2 | 2672620 | 2672732 | chr2 | 2844720 | 2844750 | chr2 | 2893165 | 2893195 |
| chr2 | 3259989 | 3260103 | chr2 | 4019911 | 4020036 | chr2 | 4050752 | 4050781 |
| chr2 | 5831178 | 5831204 | chr2 | 5831238 | 5831324 | chr2 | 5831789 | 5831819 |
| chr2 | 5833283 | 5833432 | chr2 | 5833500 | 5833639 | chr2 | 5833735 | 5834028 |
| chr2 | 5836085 | 5836253 | chr2 | 5836548 | 5836574 | chr2 | 5836622 | 5836744 |
| chr2 | 5836828 | 5836991 | chr2 | 5837353 | 5837414 | chr2 | 5866098 | 5866211 |

TABLE 12-continued

Pan Cancer #2

| chr | start | end | chr | start | end | chr | start | end |
|---|---|---|---|---|---|---|---|---|
| chr2 | 7062891 | 7062959 | chr2 | 7164467 | 7164788 | chr2 | 7236859 | 7236974 |
| chr2 | 7571577 | 7571747 | chr2 | 8735932 | 8736064 | chr2 | 8835493 | 8835523 |
| chr2 | 9090685 | 9090760 | chr2 | 9134404 | 9134493 | chr2 | 9192356 | 9192402 |
| chr2 | 9289969 | 9290114 | chr2 | 9960734 | 9960764 | chr2 | 10115730 | 10115772 |
| chr2 | 10152798 | 10153325 | chr2 | 10154266 | 10154564 | chr2 | 10154930 | 10155298 |
| chr2 | 10156116 | 10156389 | chr2 | 10182827 | 10182904 | chr2 | 10369155 | 10369242 |
| chr2 | 10408398 | 10408459 | chr2 | 10688874 | 10688904 | chr2 | 11052517 | 11052559 |
| chr2 | 11142174 | 11142315 | chr2 | 11356651 | 11356762 | chr2 | 11672746 | 11672775 |
| chr2 | 11809957 | 11810115 | chr2 | 11903450 | 11903480 | chr2 | 12246114 | 12246217 |
| chr2 | 12297534 | 12297564 | chr2 | 12858452 | 12858618 | chr2 | 13557899 | 13558057 |
| chr2 | 14772761 | 14772823 | chr2 | 14774281 | 14774567 | chr2 | 15579989 | 15580019 |
| chr2 | 17719688 | 17719812 | chr2 | 18059035 | 18059085 | chr2 | 18059781 | 18059841 |
| chr2 | 19550214 | 19550244 | chr2 | 19551322 | 19551366 | chr2 | 19556318 | 19556672 |
| chr2 | 19557068 | 19557098 | chr2 | 19557685 | 19557727 | chr2 | 19558832 | 19558893 |
| chr2 | 19561131 | 19561316 | chr2 | 19561524 | 19561685 | chr2 | 19563358 | 19563433 |
| chr2 | 20068798 | 20068885 | chr2 | 20442433 | 20442498 | chr2 | 20641988 | 20642081 |
| chr2 | 20642541 | 20642648 | chr2 | 20710145 | 20710324 | chr2 | 20865636 | 20865927 |
| chr2 | 22404181 | 22404227 | chr2 | 24318290 | 24318357 | chr2 | 25029252 | 25029300 |
| chr2 | 25374762 | 25374804 | chr2 | 25390994 | 25391212 | chr2 | 25391684 | 25391725 |
| chr2 | 25438821 | 25438871 | chr2 | 25439139 | 25439465 | chr2 | 25439727 | 25439915 |
| chr2 | 25600736 | 25600804 | chr2 | 25928094 | 25928166 | chr2 | 26372967 | 26372997 |
| chr2 | 26395447 | 26395556 | chr2 | 26402030 | 26402060 | chr2 | 26407744 | 26407921 |
| chr2 | 26521972 | 26522221 | chr2 | 26915763 | 26916066 | chr2 | 26916089 | 26916259 |
| chr2 | 27070324 | 27070414 | chr2 | 27071240 | 27071346 | chr2 | 27072492 | 27072534 |
| chr2 | 27072822 | 27072989 | chr2 | 27271699 | 27272218 | chr2 | 27356168 | 27356198 |
| chr2 | 27433532 | 27433601 | chr2 | 27543012 | 27543074 | chr2 | 27578243 | 27578396 |
| chr2 | 27648172 | 27648294 | chr2 | 27665125 | 27665154 | chr2 | 27665506 | 27665711 |
| chr2 | 27764046 | 27764168 | chr2 | 27887525 | 27887555 | chr2 | 29033336 | 29033697 |
| chr2 | 29091592 | 29091838 | chr2 | 29338310 | 29338747 | chr2 | 29338810 | 29338969 |
| chr2 | 29420483 | 29420512 | chr2 | 29432640 | 29432696 | chr2 | 29436844 | 29436888 |
| chr2 | 29443573 | 29443710 | chr2 | 29445198 | 29445482 | chr2 | 29446361 | 29446396 |
| chr2 | 30143304 | 30143322 | chr2 | 30143383 | 30143492 | chr2 | 30144041 | 30144150 |
| chr2 | 30144175 | 30144411 | chr2 | 30368444 | 30368586 | chr2 | 30453785 | 30453941 |
| chr2 | 30514753 | 30514783 | chr2 | 31360306 | 31360589 | chr2 | 31360631 | 31360755 |
| chr2 | 31360804 | 31360831 | chr2 | 31361089 | 31361118 | chr2 | 31361356 | 31361385 |
| chr2 | 31456682 | 31457039 | chr2 | 32275196 | 32275303 | chr2 | 32504169 | 32504378 |
| chr2 | 32580386 | 32580476 | chr2 | 38302370 | 38302876 | chr2 | 38365525 | 38365748 |
| chr2 | 38551124 | 38551390 | chr2 | 38594819 | 38594874 | chr2 | 38727561 | 38727707 |
| chr2 | 38762382 | 38762412 | chr2 | 38953573 | 38953603 | chr2 | 38983213 | 38983333 |
| chr2 | 39187218 | 39187237 | chr2 | 39187544 | 39187722 | chr2 | 39893090 | 39893501 |
| chr2 | 39893972 | 39894059 | chr2 | 40678603 | 40679604 | chr2 | 41789816 | 41789853 |
| chr2 | 42274595 | 42274633 | chr2 | 42329431 | 42329444 | chr2 | 42329494 | 42329666 |
| chr2 | 42720262 | 42720446 | chr2 | 43019599 | 43019868 | chr2 | 43388330 | 43388529 |
| chr2 | 43451909 | 43452327 | chr2 | 43824133 | 43824353 | chr2 | 44226958 | 44226988 |
| chr2 | 44227193 | 44227223 | chr2 | 44497708 | 44497875 | chr2 | 44809187 | 44809217 |
| chr2 | 45028988 | 45029058 | chr2 | 45029184 | 45029371 | chr2 | 45029682 | 45029712 |
| chr2 | 45155125 | 45155210 | chr2 | 45155356 | 45156811 | chr2 | 45156833 | 45157711 |
| chr2 | 45159956 | 45160267 | chr2 | 45160596 | 45160634 | chr2 | 45161663 | 45162112 |
| chr2 | 45162394 | 45162481 | chr2 | 45162751 | 45162913 | chr2 | 45164663 | 45164693 |
| chr2 | 45165564 | 45165594 | chr2 | 45168803 | 45168833 | chr2 | 45169446 | 45170029 |
| chr2 | 45171385 | 45171563 | chr2 | 45171837 | 45171862 | chr2 | 45176601 | 45176768 |
| chr2 | 45179620 | 45179650 | chr2 | 45179939 | 45180203 | chr2 | 45181520 | 45181672 |
| chr2 | 45181887 | 45182001 | chr2 | 45228627 | 45228730 | chr2 | 45231320 | 45231396 |
| chr2 | 45231805 | 45232131 | chr2 | 45233385 | 45233586 | chr2 | 45235594 | 45235926 |
| chr2 | 45237673 | 45237795 | chr2 | 45240548 | 45240630 | chr2 | 45240764 | 45240784 |
| chr2 | 45241136 | 45241168 | chr2 | 45395854 | 45395920 | chr2 | 45396315 | 45396451 |
| chr2 | 45396688 | 45396995 | chr2 | 46526302 | 46526448 | chr2 | 47193930 | 47194136 |
| chr2 | 47200591 | 47200621 | chr2 | 47249725 | 47249848 | chr2 | 47597455 | 47598620 |
| chr2 | 47599589 | 47599753 | chr2 | 47748140 | 47748494 | chr2 | 47797043 | 47797818 |
| chr2 | 47798180 | 47798663 | chr2 | 47798954 | 47799032 | chr2 | 48629615 | 48629685 |
| chr2 | 48636504 | 48636669 | chr2 | 48648878 | 48648940 | chr2 | 48982582 | 48982700 |
| chr2 | 48982754 | 48982866 | chr2 | 50573595 | 50573638 | chr2 | 50573692 | 50573865 |
| chr2 | 50574121 | 50574355 | chr2 | 50574402 | 50574684 | chr2 | 50574739 | 50574859 |
| chr2 | 54322431 | 54322576 | chr2 | 55289011 | 55289296 | chr2 | 55612770 | 55612800 |
| chr2 | 55669261 | 55669454 | chr2 | 56149836 | 56149866 | chr2 | 56150729 | 56151193 |
| chr2 | 56410817 | 56410996 | chr2 | 56411691 | 56411733 | chr2 | 58552519 | 58552689 |
| chr2 | 58656049 | 58656125 | chr2 | 59400384 | 59400424 | chr2 | 60416280 | 60416494 |
| chr2 | 60706759 | 60706804 | chr2 | 60796587 | 60796646 | chr2 | 60797137 | 60797281 |
| chr2 | 61135032 | 61135137 | chr2 | 61232163 | 61232232 | chr2 | 61242732 | 61242802 |
| chr2 | 61395039 | 61395069 | chr2 | 61556203 | 61556239 | chr2 | 61656393 | 61656423 |
| chr2 | 61992076 | 61992289 | chr2 | 62798343 | 62798386 | chr2 | 63278962 | 63278992 |
| chr2 | 63280952 | 63281651 | chr2 | 63282716 | 63282786 | chr2 | 63283014 | 63283027 |
| chr2 | 63283952 | 63284146 | chr2 | 63284777 | 63284811 | chr2 | 63285081 | 63286047 |
| chr2 | 63286359 | 63286584 | chr2 | 63286694 | 63286747 | chr2 | 63287083 | 63287368 |
| chr2 | 65251310 | 65251340 | chr2 | 65779892 | 65779983 | chr2 | 66652863 | 66652963 |
| chr2 | 66653238 | 66653496 | chr2 | 66653764 | 66653914 | chr2 | 66660650 | 66660888 |

TABLE 12-continued

Pan Cancer #2

| chr | start | end | chr | start | end | chr | start | end |
|---|---|---|---|---|---|---|---|---|
| chr2 | 66662749 | 66662824 | chr2 | 66808525 | 66808633 | chr2 | 66808727 | 66809361 |
| chr2 | 67625453 | 67625770 | chr2 | 67626102 | 67626257 | chr2 | 68287707 | 68287799 |
| chr2 | 68546324 | 68546516 | chr2 | 68546553 | 68546892 | chr2 | 68559261 | 68559365 |
| chr2 | 68672853 | 68672938 | chr2 | 69027024 | 69027053 | chr2 | 69975443 | 69975523 |
| chr2 | 70058262 | 70058292 | chr2 | 70367670 | 70367710 | chr2 | 70418528 | 70418627 |
| chr2 | 70427556 | 70427646 | chr2 | 70430997 | 70431160 | chr2 | 71355019 | 71355117 |
| chr2 | 71355768 | 71355961 | chr2 | 71503790 | 71503823 | chr2 | 71504103 | 71504148 |
| chr2 | 71680833 | 71680863 | chr2 | 71693374 | 71693593 | chr2 | 72374375 | 72374432 |
| chr2 | 72374714 | 72374765 | chr2 | 73145640 | 73145694 | chr2 | 73145924 | 73146021 |
| chr2 | 73147324 | 73147527 | chr2 | 73147967 | 73148066 | chr2 | 73148175 | 73148243 |
| chr2 | 73150924 | 73150954 | chr2 | 73151187 | 73151831 | chr2 | 73152740 | 73152754 |
| chr2 | 73416356 | 73416535 | chr2 | 73429523 | 73429614 | chr2 | 73429977 | 73430069 |
| chr2 | 73430322 | 73430372 | chr2 | 73430443 | 73430743 | chr2 | 73440206 | 73440293 |
| chr2 | 73518448 | 73518919 | chr2 | 73519579 | 73519841 | chr2 | 74010528 | 74010773 |
| chr2 | 74153198 | 74153227 | chr2 | 74350410 | 74350497 | chr2 | 74426185 | 74426214 |
| chr2 | 74454074 | 74454261 | chr2 | 74647864 | 74648007 | chr2 | 74679047 | 74679123 |
| chr2 | 74726744 | 74726774 | chr2 | 74740852 | 74741387 | chr2 | 74741835 | 74741844 |
| chr2 | 74741873 | 74741955 | chr2 | 74742325 | 74742647 | chr2 | 74742694 | 74743144 |
| chr2 | 74782081 | 74782087 | chr2 | 74782219 | 74782271 | chr2 | 74874865 | 74874903 |
| chr2 | 75427040 | 75427114 | chr2 | 75427369 | 75427399 | chr2 | 75427930 | 75428177 |
| chr2 | 75720510 | 75720541 | chr2 | 79347459 | 79347546 | chr2 | 80529378 | 80529443 |
| chr2 | 80529662 | 80529908 | chr2 | 80529986 | 80530022 | chr2 | 80530505 | 80530558 |
| chr2 | 80531725 | 80531755 | chr2 | 80549585 | 80549745 | chr2 | 85107454 | 85107538 |
| chr2 | 85361467 | 85361528 | chr2 | 85838101 | 85838299 | chr2 | 86191145 | 86191309 |
| chr2 | 86263223 | 86263270 | chr2 | 86423330 | 86423592 | chr2 | 86783725 | 86783755 |
| chr2 | 86791221 | 86791251 | chr2 | 87016579 | 87016636 | chr2 | 87017796 | 87018396 |
| chr2 | 87036611 | 87036640 | chr2 | 88469312 | 88469483 | chr2 | 88751281 | 88751419 |
| chr2 | 88751461 | 88751800 | chr2 | 88752055 | 88752285 | chr2 | 88752603 | 88752785 |
| chr2 | 88990189 | 88990264 | chr2 | 89064800 | 89064975 | chr2 | 89065129 | 89065278 |
| chr2 | 89252535 | 89252679 | chr2 | 95663969 | 95664014 | chr2 | 95690747 | 95690793 |
| chr2 | 95691036 | 95691269 | chr2 | 95691530 | 95691769 | chr2 | 95691994 | 95692480 |
| chr2 | 95941678 | 95941812 | chr2 | 96070057 | 96070165 | chr2 | 96974486 | 96974516 |
| chr2 | 96990898 | 96991316 | chr2 | 97126702 | 97126832 | chr2 | 97193252 | 97193626 |
| chr2 | 97427515 | 97428093 | chr2 | 98581819 | 98581849 | chr2 | 98703323 | 98703475 |
| chr2 | 98703675 | 98703736 | chr2 | 98962898 | 98962900 | chr2 | 98963329 | 98963599 |
| chr2 | 98963869 | 98964200 | chr2 | 98964596 | 98964645 | chr2 | 99439369 | 99439507 |
| chr2 | 99553391 | 99553656 | chr2 | 99796259 | 99796330 | chr2 | 99798646 | 99799153 |
| chr2 | 100618451 | 100618480 | chr2 | 100937836 | 100938209 | chr2 | 100938330 | 100938544 |
| chr2 | 100938575 | 100938809 | chr2 | 100938985 | 100939155 | chr2 | 101009832 | 101009927 |
| chr2 | 101034242 | 101034293 | chr2 | 101186368 | 101186458 | chr2 | 101436632 | 101436708 |
| chr2 | 101666893 | 101667004 | chr2 | 101834977 | 101835057 | chr2 | 102091180 | 102091335 |
| chr2 | 103236165 | 103236292 | chr2 | 105459081 | 105459151 | chr2 | 105459908 | 105460599 |
| chr2 | 105460921 | 105460951 | chr2 | 105461187 | 105461243 | chr2 | 105461564 | 105461667 |
| chr2 | 105461700 | 105461896 | chr2 | 105462165 | 105462222 | chr2 | 105468791 | 105468908 |
| chr2 | 105469645 | 105469856 | chr2 | 105469881 | 105470091 | chr2 | 105470350 | 105470840 |
| chr2 | 105472231 | 105472425 | chr2 | 105472713 | 105472845 | chr2 | 105473248 | 105473553 |
| chr2 | 105478762 | 105479089 | chr2 | 105483655 | 105483719 | chr2 | 105484450 | 105484522 |
| chr2 | 105488437 | 105488496 | chr2 | 105760981 | 105761037 | chr2 | 105937344 | 105937498 |
| chr2 | 106060615 | 106060792 | chr2 | 106681733 | 106681767 | chr2 | 106682012 | 106682098 |
| chr2 | 106730223 | 106730256 | chr2 | 106959368 | 106959568 | chr2 | 106959916 | 106959988 |
| chr2 | 107103865 | 107103928 | chr2 | 107502600 | 107502729 | chr2 | 107503532 | 107503561 |
| chr2 | 107503884 | 107504018 | chr2 | 108364897 | 108364940 | chr2 | 109335133 | 109335166 |
| chr2 | 109648080 | 109648222 | chr2 | 109745989 | 109746079 | chr2 | 109746289 | 109746387 |
| chr2 | 109746463 | 109746477 | chr2 | 110015080 | 110015110 | chr2 | 110370941 | 110371219 |
| chr2 | 110873016 | 110873045 | chr2 | 111544817 | 111544997 | chr2 | 111875191 | 111875611 |
| chr2 | 112657033 | 112657092 | chr2 | 112817735 | 112817765 | chr2 | 113227024 | 113227225 |
| chr2 | 113594639 | 113594668 | chr2 | 113803960 | 113803990 | chr2 | 113931503 | 113931532 |
| chr2 | 114256978 | 114257137 | chr2 | 114261300 | 114261458 | chr2 | 114461746 | 114461879 |
| chr2 | 114470022 | 114470201 | chr2 | 114515528 | 114515618 | chr2 | 114634867 | 114634988 |
| chr2 | 115918661 | 115918892 | chr2 | 115919338 | 115919424 | chr2 | 115919831 | 115920534 |
| chr2 | 118380865 | 118380904 | chr2 | 118981151 | 118981856 | chr2 | 118981946 | 118982147 |
| chr2 | 118982254 | 118982497 | chr2 | 119067636 | 119068049 | chr2 | 119532161 | 119532255 |
| chr2 | 119566239 | 119566272 | chr2 | 119591351 | 119591465 | chr2 | 119592588 | 119592777 |
| chr2 | 119592997 | 119593567 | chr2 | 119599926 | 119600031 | chr2 | 119600332 | 119600555 |
| chr2 | 119600570 | 119600747 | chr2 | 119600949 | 119600952 | chr2 | 119600996 | 119601061 |
| chr2 | 119602601 | 119602629 | chr2 | 119602829 | 119603086 | chr2 | 119604032 | 119604158 |
| chr2 | 119604809 | 119604851 | chr2 | 119606135 | 119606499 | chr2 | 119606783 | 119606839 |
| chr2 | 119607176 | 119607411 | chr2 | 119610844 | 119610939 | chr2 | 119611745 | 119611799 |
| chr2 | 119612324 | 119612354 | chr2 | 119614130 | 119614171 | chr2 | 119614780 | 119614852 |
| chr2 | 119615055 | 119615627 | chr2 | 119616155 | 119616551 | chr2 | 119616809 | 119616870 |
| chr2 | 119914720 | 119914752 | chr2 | 119916525 | 119916595 | chr2 | 120281646 | 120281693 |
| chr2 | 120281939 | 120281953 | chr2 | 120769511 | 120769746 | chr2 | 120825608 | 120825769 |
| chr2 | 120980068 | 120980098 | chr2 | 120980353 | 120980395 | chr2 | 121200390 | 121200433 |
| chr2 | 121345081 | 121345111 | chr2 | 121411888 | 121412153 | chr2 | 122176232 | 122176293 |
| chr2 | 122495267 | 122495413 | chr2 | 122809705 | 122809801 | chr2 | 124782333 | 124782458 |
| chr2 | 124782692 | 124783097 | chr2 | 127412291 | 127412386 | chr2 | 127413970 | 127413995 |

TABLE 12-continued

Pan Cancer #2

| chr | start | end | chr | start | end | chr | start | end |
|---|---|---|---|---|---|---|---|---|
| chr2 | 127423220 | 127423350 | chr2 | 127429010 | 127429044 | chr2 | 127438633 | 127438663 |
| chr2 | 127783043 | 127783257 | chr2 | 127863601 | 127863725 | chr2 | 127976467 | 127976672 |
| chr2 | 128421891 | 128421947 | chr2 | 128616617 | 128616838 | chr2 | 128680057 | 128680087 |
| chr2 | 128847677 | 128847723 | chr2 | 129174888 | 129174918 | chr2 | 129494389 | 129494421 |
| chr2 | 130763584 | 130763623 | chr2 | 130937868 | 130937898 | chr2 | 130971149 | 130971321 |
| chr2 | 131084953 | 131085013 | chr2 | 131477785 | 131477936 | chr2 | 131594989 | 131595019 |
| chr2 | 131673756 | 131673785 | chr2 | 131720852 | 131721098 | chr2 | 131721461 | 131721584 |
| chr2 | 131721867 | 131721949 | chr2 | 131792260 | 131792519 | chr2 | 131792532 | 131792746 |
| chr2 | 131792921 | 131793131 | chr2 | 132088786 | 132088828 | chr2 | 132121661 | 132121829 |
| chr2 | 132152361 | 132152495 | chr2 | 132182790 | 132183089 | chr2 | 132208115 | 132208278 |
| chr2 | 132767457 | 132767707 | chr2 | 132795261 | 132795403 | chr2 | 132795670 | 132795728 |
| chr2 | 133014598 | 133014638 | chr2 | 133015275 | 133015323 | chr2 | 133062362 | 133062389 |
| chr2 | 133426249 | 133426279 | chr2 | 133426637 | 133426674 | chr2 | 136287358 | 136287390 |
| chr2 | 137522445 | 137522475 | chr2 | 137523825 | 137523855 | chr2 | 139536937 | 139537145 |
| chr2 | 139537443 | 139537822 | chr2 | 139537851 | 139537865 | chr2 | 142887871 | 142888066 |
| chr2 | 142888348 | 142888418 | chr2 | 143569561 | 143569694 | chr2 | 144129765 | 144129795 |
| chr2 | 144299758 | 144299788 | chr2 | 144694367 | 144694514 | chr2 | 144694554 | 144695135 |
| chr2 | 145273404 | 145273751 | chr2 | 145274186 | 145274455 | chr2 | 145274814 | 145275213 |
| chr2 | 145282119 | 145282149 | chr2 | 148776809 | 148777035 | chr2 | 149633097 | 149633399 |
| chr2 | 149633744 | 149633965 | chr2 | 149645496 | 149645894 | chr2 | 151342903 | 151343277 |
| chr2 | 152248836 | 152248983 | chr2 | 154333535 | 154333567 | chr2 | 154334272 | 154334665 |
| chr2 | 154335185 | 154335271 | chr2 | 154728245 | 154728440 | chr2 | 154729083 | 154729240 |
| chr2 | 154729559 | 154729589 | chr2 | 155555038 | 155555361 | chr2 | 157176592 | 157176717 |
| chr2 | 157177003 | 157178310 | chr2 | 157178646 | 157178731 | chr2 | 160761070 | 160761556 |
| chr2 | 161253293 | 161253455 | chr2 | 162166600 | 162166632 | chr2 | 162272989 | 162273314 |
| chr2 | 162273383 | 162274338 | chr2 | 162274717 | 162274866 | chr2 | 162275146 | 162275226 |
| chr2 | 162275311 | 162275437 | chr2 | 162275473 | 162275802 | chr2 | 162280153 | 162280415 |
| chr2 | 162280741 | 162280956 | chr2 | 162283365 | 162283602 | chr2 | 162283783 | 162284055 |
| chr2 | 164593096 | 164593137 | chr2 | 166929478 | 166929613 | chr2 | 168150069 | 168150245 |
| chr2 | 168150751 | 168150945 | chr2 | 170255970 | 170256139 | chr2 | 170282981 | 170283080 |
| chr2 | 170373281 | 170373413 | chr2 | 170551730 | 170551942 | chr2 | 170681880 | 170682422 |
| chr2 | 171570182 | 171570189 | chr2 | 171570684 | 171570733 | chr2 | 171571264 | 171571315 |
| chr2 | 171571889 | 171572068 | chr2 | 171670349 | 171670446 | chr2 | 171671487 | 171671789 |
| chr2 | 171671800 | 171671881 | chr2 | 171673873 | 171673939 | chr2 | 171674739 | 171675066 |
| chr2 | 171675361 | 171675382 | chr2 | 171675523 | 171675592 | chr2 | 171676684 | 171676785 |
| chr2 | 171822428 | 171822480 | chr2 | 171839017 | 171839047 | chr2 | 172367021 | 172367125 |
| chr2 | 172411136 | 172411166 | chr2 | 172945124 | 172945167 | chr2 | 172945896 | 172946211 |
| chr2 | 172947717 | 172947913 | chr2 | 172948184 | 172948314 | chr2 | 172948709 | 172948751 |
| chr2 | 172949186 | 172949282 | chr2 | 172949349 | 172949711 | chr2 | 172952521 | 172952881 |
| chr2 | 172952993 | 172953046 | chr2 | 172955472 | 172955545 | chr2 | 172957907 | 172958066 |
| chr2 | 172961398 | 172961598 | chr2 | 172964821 | 172964888 | chr2 | 172965296 | 172965298 |
| chr2 | 172965648 | 172965762 | chr2 | 172966264 | 172966442 | chr2 | 172972735 | 172972890 |
| chr2 | 172972931 | 172973218 | chr2 | 173099784 | 173099814 | chr2 | 173100262 | 173100430 |
| chr2 | 173422685 | 173422734 | chr2 | 174148058 | 174148157 | chr2 | 175111870 | 175112092 |
| chr2 | 175190871 | 175191972 | chr2 | 175192085 | 175192468 | chr2 | 175193268 | 175193644 |
| chr2 | 175193809 | 175193823 | chr2 | 175195831 | 175195858 | chr2 | 175196432 | 175196575 |
| chr2 | 175197089 | 175197119 | chr2 | 175198752 | 175198766 | chr2 | 175198846 | 175198966 |
| chr2 | 175199527 | 175199554 | chr2 | 175199922 | 175199935 | chr2 | 175200140 | 175200440 |
| chr2 | 175200710 | 175200852 | chr2 | 175200917 | 175201182 | chr2 | 175201360 | 175201541 |
| chr2 | 175201776 | 175201828 | chr2 | 175202127 | 175202245 | chr2 | 175202569 | 175202600 |
| chr2 | 175202634 | 175202652 | chr2 | 175204174 | 175204204 | chr2 | 175204786 | 175204946 |
| chr2 | 175205588 | 175205799 | chr2 | 175206833 | 175206905 | chr2 | 175206961 | 175207028 |
| chr2 | 175207228 | 175207258 | chr2 | 175207536 | 175207653 | chr2 | 175208311 | 175208868 |
| chr2 | 175208997 | 175209135 | chr2 | 175261402 | 175261432 | chr2 | 175383935 | 175383965 |
| chr2 | 175547041 | 175547140 | chr2 | 175547384 | 175547413 | chr2 | 176940167 | 176940315 |
| chr2 | 176943269 | 176943568 | chr2 | 176943861 | 176943902 | chr2 | 176944457 | 176944846 |
| chr2 | 176945138 | 176945268 | chr2 | 176945582 | 176945784 | chr2 | 176946578 | 176946867 |
| chr2 | 176947285 | 176947389 | chr2 | 176947764 | 176947903 | chr2 | 176948599 | 176948742 |
| chr2 | 176949045 | 176949075 | chr2 | 176949695 | 176949869 | chr2 | 176950142 | 176950258 |
| chr2 | 176956558 | 176956599 | chr2 | 176956921 | 176957199 | chr2 | 176957577 | 176957628 |
| chr2 | 176957915 | 176957919 | chr2 | 176958138 | 176958489 | chr2 | 176959289 | 176959511 |
| chr2 | 176963448 | 176963522 | chr2 | 176964085 | 176964149 | chr2 | 176964390 | 176964767 |
| chr2 | 176965265 | 176965492 | chr2 | 176969463 | 176969613 | chr2 | 176969677 | 176969908 |
| chr2 | 176971628 | 176971651 | chr2 | 176976029 | 176976188 | chr2 | 176980750 | 176980937 |
| chr2 | 176981377 | 176981506 | chr2 | 176982584 | 176982627 | chr2 | 176986715 | 176986848 |
| chr2 | 176987057 | 176987224 | chr2 | 176987971 | 176988103 | chr2 | 176988155 | 176988304 |
| chr2 | 176993074 | 176993103 | chr2 | 176993547 | 176993855 | chr2 | 176994031 | 176994379 |
| chr2 | 176994498 | 176994621 | chr2 | 176995072 | 176995269 | chr2 | 176995332 | 176995668 |
| chr2 | 177001102 | 177001695 | chr2 | 177001782 | 177001976 | chr2 | 177004566 | 177004658 |
| chr2 | 177014981 | 177015010 | chr2 | 177027425 | 177027438 | chr2 | 177030149 | 177030226 |
| chr2 | 177042984 | 177042998 | chr2 | 177043267 | 177043515 | chr2 | 177053276 | 177053434 |
| chr2 | 177053619 | 177053702 | chr2 | 177054113 | 177054351 | chr2 | 177503048 | 177503077 |
| chr2 | 177503581 | 177503610 | chr2 | 177872600 | 177872629 | chr2 | 178098791 | 178098967 |
| chr2 | 178973003 | 178973042 | chr2 | 179303534 | 179303727 | chr2 | 179316860 | 179317057 |
| chr2 | 182202233 | 182202291 | chr2 | 182321397 | 182321637 | chr2 | 182322039 | 182322170 |
| chr2 | 182322400 | 182323042 | chr2 | 182451522 | 182451551 | chr2 | 182542903 | 182542933 |

TABLE 12-continued

Pan Cancer #2

| chr | start | end | chr | start | end | chr | start | end |
|---|---|---|---|---|---|---|---|---|
| chr2 | 182543321 | 182543418 | chr2 | 182543764 | 182543925 | chr2 | 182545211 | 182545275 |
| chr2 | 182545539 | 182545694 | chr2 | 182546002 | 182546085 | chr2 | 182546435 | 182546465 |
| chr2 | 182547385 | 182547387 | chr2 | 182547438 | 182547613 | chr2 | 182548062 | 182548161 |
| chr2 | 182549088 | 182549134 | chr2 | 182549337 | 182549454 | chr2 | 182550094 | 182550124 |
| chr2 | 182819048 | 182819216 | chr2 | 183251240 | 183251303 | chr2 | 183731294 | 183731331 |
| chr2 | 183731467 | 183731524 | chr2 | 183731809 | 183732076 | chr2 | 185462869 | 185462980 |
| chr2 | 185463193 | 185463817 | chr2 | 186603488 | 186603518 | chr2 | 188419047 | 188419204 |
| chr2 | 189157427 | 189157688 | chr2 | 190708790 | 190708819 | chr2 | 193059025 | 193059317 |
| chr2 | 193059345 | 193059548 | chr2 | 193059662 | 193060067 | chr2 | 193060385 | 193060441 |
| chr2 | 193060683 | 193060891 | chr2 | 193061388 | 193061480 | chr2 | 197793125 | 197793267 |
| chr2 | 198238409 | 198238439 | chr2 | 198267345 | 198267374 | chr2 | 198456480 | 198456719 |
| chr2 | 198651002 | 198651076 | chr2 | 200326590 | 200326735 | chr2 | 200327424 | 200327451 |
| chr2 | 200329030 | 200329393 | chr2 | 200329433 | 200329668 | chr2 | 200333801 | 200333834 |
| chr2 | 200334976 | 200335451 | chr2 | 200335592 | 200335952 | chr2 | 200818892 | 200819130 |
| chr2 | 201156690 | 201156804 | chr2 | 201172444 | 201172480 | chr2 | 201450556 | 201450707 |
| chr2 | 201451014 | 201451040 | chr2 | 201693680 | 201693718 | chr2 | 202097078 | 202097143 |
| chr2 | 202098936 | 202098965 | chr2 | 202101198 | 202101219 | chr2 | 202122459 | 202122683 |
| chr2 | 202477462 | 202477621 | chr2 | 202899862 | 202899891 | chr2 | 203484608 | 203484646 |
| chr2 | 203498452 | 203498489 | chr2 | 203880390 | 203880492 | chr2 | 204194588 | 204194725 |
| chr2 | 206551072 | 206551362 | chr2 | 207022702 | 207022802 | chr2 | 207139072 | 207139102 |
| chr2 | 207139347 | 207139605 | chr2 | 207307548 | 207307562 | chr2 | 207308802 | 207308857 |
| chr2 | 207506691 | 207507181 | chr2 | 208574821 | 208574917 | chr2 | 208588311 | 208588341 |
| chr2 | 208635534 | 208635774 | chr2 | 208662170 | 208662376 | chr2 | 208662672 | 208662710 |
| chr2 | 208989294 | 208989382 | chr2 | 209094739 | 209094845 | chr2 | 209113097 | 209113126 |
| chr2 | 209225237 | 209225275 | chr2 | 209271322 | 209271336 | chr2 | 210636335 | 210636381 |
| chr2 | 210636430 | 210636689 | chr2 | 210636738 | 210636876 | chr2 | 212248428 | 212248457 |
| chr2 | 212288927 | 212288956 | chr2 | 212295683 | 212295820 | chr2 | 212530120 | 212530149 |
| chr2 | 212537902 | 212537994 | chr2 | 212566811 | 212566840 | chr2 | 212578292 | 212578321 |
| chr2 | 212587132 | 212587161 | chr2 | 213401235 | 213401339 | chr2 | 213401613 | 213401947 |
| chr2 | 213403110 | 213403337 | chr2 | 215275823 | 215275852 | chr2 | 215276310 | 215276339 |
| chr2 | 217396039 | 217396069 | chr2 | 217448294 | 217448441 | chr2 | 217559296 | 217559326 |
| chr2 | 217559966 | 217559999 | chr2 | 218770207 | 218770270 | chr2 | 218806147 | 218806302 |
| chr2 | 219276888 | 219276918 | chr2 | 219736151 | 219736691 | chr2 | 219828049 | 219828117 |
| chr2 | 219847462 | 219847555 | chr2 | 219848809 | 219848891 | chr2 | 219848926 | 219849001 |
| chr2 | 219857723 | 219857737 | chr2 | 220080510 | 220081033 | chr2 | 220173989 | 220174036 |
| chr2 | 220174060 | 220174296 | chr2 | 220196354 | 220196567 | chr2 | 220223098 | 220223128 |
| chr2 | 220223648 | 220223699 | chr2 | 220283363 | 220283519 | chr2 | 220299588 | 220299634 |
| chr2 | 220299886 | 220300059 | chr2 | 220349055 | 220349706 | chr2 | 220361447 | 220361466 |
| chr2 | 220416379 | 220416513 | chr2 | 220416848 | 220417649 | chr2 | 221853201 | 221853352 |
| chr2 | 222285828 | 222285858 | chr2 | 222310068 | 222310105 | chr2 | 222435773 | 222435863 |
| chr2 | 223155722 | 223156188 | chr2 | 223158730 | 223159453 | chr2 | 223159869 | 223160065 |
| chr2 | 223160342 | 223160379 | chr2 | 223161247 | 223161684 | chr2 | 223161807 | 223162063 |
| chr2 | 223162779 | 223162890 | chr2 | 223162929 | 223163224 | chr2 | 223163473 | 223163535 |
| chr2 | 223163768 | 223163954 | chr2 | 223164534 | 223164883 | chr2 | 223165434 | 223165832 |
| chr2 | 223166294 | 223166408 | chr2 | 223166449 | 223166721 | chr2 | 223167389 | 223167573 |
| chr2 | 223168437 | 223168831 | chr2 | 223169640 | 223169864 | chr2 | 223170375 | 223170434 |
| chr2 | 223171109 | 223171180 | chr2 | 223172337 | 223172367 | chr2 | 223172924 | 223173173 |
| chr2 | 223175663 | 223175694 | chr2 | 223175746 | 223176181 | chr2 | 223176456 | 223176511 |
| chr2 | 223176720 | 223176983 | chr2 | 223177315 | 223177610 | chr2 | 224661521 | 224661701 |
| chr2 | 224903260 | 224903440 | chr2 | 224903690 | 224903755 | chr2 | 224904108 | 224904237 |
| chr2 | 225464038 | 225464068 | chr2 | 228029418 | 228029531 | chr2 | 228411020 | 228411050 |
| chr2 | 228466625 | 228466777 | chr2 | 228638272 | 228638302 | chr2 | 228735680 | 228735736 |
| chr2 | 228736215 | 228736295 | chr2 | 228736336 | 228736473 | chr2 | 229046107 | 229046503 |
| chr2 | 230795535 | 230795565 | chr2 | 231576609 | 231576643 | chr2 | 232330451 | 232330481 |
| chr2 | 232394970 | 232395021 | chr2 | 232395055 | 232395061 | chr2 | 232479822 | 232479938 |
| chr2 | 232506220 | 232506294 | chr2 | 232506605 | 232506635 | chr2 | 232522844 | 232522874 |
| chr2 | 232544500 | 232544530 | chr2 | 232546736 | 232546842 | chr2 | 232791704 | 232792012 |
| chr2 | 232827168 | 232827349 | chr2 | 233073078 | 233073223 | chr2 | 233220227 | 233220382 |
| chr2 | 233350208 | 233350539 | chr2 | 233350844 | 233351278 | chr2 | 233352102 | 233352451 |
| chr2 | 233352507 | 233352762 | chr2 | 233352776 | 233352853 | chr2 | 233498710 | 233498873 |
| chr2 | 233498896 | 233499297 | chr2 | 233750525 | 233750555 | chr2 | 234776483 | 234776553 |
| chr2 | 235404551 | 235404575 | chr2 | 235860746 | 235860808 | chr2 | 235861389 | 235861533 |
| chr2 | 236402771 | 236403013 | chr2 | 236403270 | 236403736 | chr2 | 236444269 | 236444298 |
| chr2 | 236578362 | 236578677 | chr2 | 236877262 | 236877399 | chr2 | 237072642 | 237073014 |
| chr2 | 237073354 | 237073414 | chr2 | 237076725 | 237076815 | chr2 | 237077562 | 237077608 |
| chr2 | 237077846 | 237078348 | chr2 | 237080264 | 237080294 | chr2 | 237081341 | 237081426 |
| chr2 | 237081537 | 237081553 | chr2 | 237082344 | 237082720 | chr2 | 237086349 | 237086468 |
| chr2 | 237145422 | 237145601 | chr2 | 237416216 | 237416429 | chr2 | 238395291 | 238395356 |
| chr2 | 238395906 | 238395961 | chr2 | 238535895 | 238535984 | chr2 | 238536005 | 238536114 |
| chr2 | 238864727 | 238864913 | chr2 | 239031722 | 239031780 | chr2 | 239051198 | 239051228 |
| chr2 | 239140139 | 239140249 | chr2 | 239149844 | 239149951 | chr2 | 239265496 | 239265787 |
| chr2 | 239482485 | 239482519 | chr2 | 239705305 | 239705337 | chr2 | 239755164 | 239755194 |
| chr2 | 239756373 | 239756462 | chr2 | 239756488 | 239756607 | chr2 | 239756634 | 239756648 |
| chr2 | 239757636 | 239757730 | chr2 | 239758126 | 239758144 | chr2 | 239758345 | 239758394 |
| chr2 | 239957330 | 239957448 | chr2 | 240167575 | 240167605 | chr2 | 240168811 | 240169051 |
| chr2 | 240319920 | 240320012 | chr2 | 240582379 | 240582524 | chr2 | 240619459 | 240619604 |

TABLE 12-continued

Pan Cancer #2

| chr | start | end | chr | start | end | chr | start | end |
|---|---|---|---|---|---|---|---|---|
| chr2 | 240658227 | 240658421 | chr2 | 240658667 | 240658697 | chr2 | 240812243 | 240812374 |
| chr2 | 241095604 | 241095772 | chr2 | 241393200 | 241393469 | chr2 | 241497411 | 241497554 |
| chr2 | 241541932 | 241542357 | chr2 | 241545001 | 241545031 | chr2 | 241758377 | 241758819 |
| chr2 | 241759597 | 241759694 | chr2 | 241760149 | 241760178 | chr2 | 241760494 | 241760523 |
| chr2 | 241771165 | 241771257 | chr2 | 241865194 | 241865346 | chr2 | 242009391 | 242009421 |
| chr2 | 242021784 | 242021892 | chr2 | 242314494 | 242314524 | chr2 | 242523907 | 242524147 |
| chr2 | 242549849 | 242549957 | chr2 | 242554549 | 242554579 | chr2 | 242636726 | 242636812 |
| chr2 | 242640015 | 242640045 | chr2 | 242716723 | 242716760 | chr2 | 242756144 | 242756297 |
| chr2 | 242832984 | 242833159 | chr2 | 242833558 | 242833588 | chr2 | 242833797 | 242833863 |
| chr2 | 242836495 | 242836640 | chr2 | 242925496 | 242925641 | chr3 | 238536 | 238715 |
| chr3 | 239007 | 239094 | chr3 | 239622 | 239868 | chr3 | 240110 | 240223 |
| chr3 | 2140277 | 2140398 | chr3 | 3167720 | 3167750 | chr3 | 3840498 | 3840758 |
| chr3 | 3841046 | 3841144 | chr3 | 3842679 | 3842731 | chr3 | 5137960 | 5138019 |
| chr3 | 5165885 | 5165915 | chr3 | 6902288 | 6902353 | chr3 | 6903425 | 6903463 |
| chr3 | 8725296 | 8725348 | chr3 | 8810152 | 8810220 | chr3 | 9593979 | 9594015 |
| chr3 | 9594263 | 9594382 | chr3 | 9595396 | 9595502 | chr3 | 9904233 | 9904554 |
| chr3 | 9924238 | 9924534 | chr3 | 9941469 | 9941669 | chr3 | 9957064 | 9957142 |
| chr3 | 9957451 | 9957677 | chr3 | 10027432 | 10027548 | chr3 | 10182839 | 10183212 |
| chr3 | 10183321 | 10183350 | chr3 | 10183706 | 10183782 | chr3 | 10184304 | 10184333 |
| chr3 | 10191477 | 10191620 | chr3 | 11034264 | 11034359 | chr3 | 11035070 | 11035330 |
| chr3 | 12046405 | 12046632 | chr3 | 12586149 | 12586179 | chr3 | 12632309 | 12632401 |
| chr3 | 12645678 | 12645713 | chr3 | 12673006 | 12673036 | chr3 | 12729424 | 12729454 |
| chr3 | 12870826 | 12870856 | chr3 | 12917606 | 12917655 | chr3 | 12926053 | 12926102 |
| chr3 | 12977067 | 12977144 | chr3 | 13171814 | 13171844 | chr3 | 13323494 | 13323973 |
| chr3 | 13324420 | 13324433 | chr3 | 13324847 | 13324938 | chr3 | 13590448 | 13590640 |
| chr3 | 13679172 | 13679349 | chr3 | 13921407 | 13921463 | chr3 | 14851850 | 14851897 |
| chr3 | 14852325 | 14852919 | chr3 | 15123848 | 15123992 | chr3 | 15780510 | 15780638 |
| chr3 | 16554052 | 16554111 | chr3 | 16554347 | 16554633 | chr3 | 17001303 | 17001333 |
| chr3 | 17735273 | 17735340 | chr3 | 19189441 | 19189470 | chr3 | 19189694 | 19189765 |
| chr3 | 19190143 | 19190216 | chr3 | 20070714 | 20070903 | chr3 | 22413665 | 22413694 |
| chr3 | 22413960 | 22413974 | chr3 | 23964882 | 23965019 | chr3 | 24871002 | 24871176 |
| chr3 | 25469110 | 25469139 | chr3 | 25469377 | 25469406 | chr3 | 25469679 | 25469708 |
| chr3 | 26664045 | 26664119 | chr3 | 26664389 | 26664755 | chr3 | 27754478 | 27754508 |
| chr3 | 27762336 | 27762650 | chr3 | 27762857 | 27762887 | chr3 | 27763566 | 27763595 |
| chr3 | 27764457 | 27764471 | chr3 | 27765181 | 27765347 | chr3 | 27771497 | 27772004 |
| chr3 | 27772790 | 27772819 | chr3 | 28616832 | 28617675 | chr3 | 31494108 | 31494138 |
| chr3 | 32708277 | 32708405 | chr3 | 32858353 | 32858958 | chr3 | 32859256 | 32859284 |
| chr3 | 32859418 | 32859693 | chr3 | 32860068 | 32860273 | chr3 | 33259904 | 33260776 |
| chr3 | 35680842 | 35680872 | chr3 | 36805815 | 36805863 | chr3 | 36806179 | 36806193 |
| chr3 | 36984378 | 36984425 | chr3 | 37276385 | 37276490 | chr3 | 37493519 | 37493621 |
| chr3 | 37901923 | 37901953 | chr3 | 38030618 | 38030782 | chr3 | 38032331 | 38032361 |
| chr3 | 38035774 | 38035989 | chr3 | 38080685 | 38080925 | chr3 | 38081154 | 38081271 |
| chr3 | 38182244 | 38182306 | chr3 | 38182626 | 38182655 | chr3 | 38208158 | 38208226 |
| chr3 | 38690624 | 38690668 | chr3 | 39851772 | 39851814 | chr3 | 40202174 | 40202255 |
| chr3 | 40428507 | 40428713 | chr3 | 41266086 | 41266151 | chr3 | 42222730 | 42222847 |
| chr3 | 42329346 | 42329511 | chr3 | 42640855 | 42640964 | chr3 | 42814569 | 42814603 |
| chr3 | 42852329 | 42852359 | chr3 | 42947411 | 42947552 | chr3 | 43735604 | 43735634 |
| chr3 | 44036260 | 44036330 | chr3 | 44036570 | 44036600 | chr3 | 44036820 | 44037203 |
| chr3 | 44037625 | 44037662 | chr3 | 44037874 | 44038646 | chr3 | 44039348 | 44040006 |
| chr3 | 44040511 | 44040553 | chr3 | 44040796 | 44041039 | chr3 | 44063434 | 44063872 |
| chr3 | 44596479 | 44596509 | chr3 | 44596716 | 44596809 | chr3 | 44626438 | 44626711 |
| chr3 | 44726875 | 44727193 | chr3 | 45187296 | 45187327 | chr3 | 46924934 | 46924964 |
| chr3 | 47144864 | 47144893 | chr3 | 47352704 | 47352734 | chr3 | 47521062 | 47521178 |
| chr3 | 47555760 | 47555790 | chr3 | 47830060 | 47830148 | chr3 | 47831601 | 47831819 |
| chr3 | 48227765 | 48227870 | chr3 | 48236476 | 48236724 | chr3 | 48693304 | 48693700 |
| chr3 | 48693852 | 48694154 | chr3 | 48698251 | 48698431 | chr3 | 48698810 | 48699010 |
| chr3 | 48699377 | 48699767 | chr3 | 48978413 | 48978479 | chr3 | 49142883 | 49142913 |
| chr3 | 49196747 | 49196831 | chr3 | 49236845 | 49236874 | chr3 | 49405953 | 49405982 |
| chr3 | 49412883 | 49412987 | chr3 | 49591832 | 49592076 | chr3 | 49907093 | 49907130 |
| chr3 | 49939931 | 49940398 | chr3 | 50072827 | 50072925 | chr3 | 50243383 | 50243480 |
| chr3 | 50374655 | 50374684 | chr3 | 50374917 | 50374946 | chr3 | 50375179 | 50375559 |
| chr3 | 50377973 | 50378002 | chr3 | 50378277 | 50378306 | chr3 | 50378512 | 50378541 |
| chr3 | 50395506 | 50395536 | chr3 | 50402170 | 50402944 | chr3 | 50575616 | 50575658 |
| chr3 | 50968445 | 50968511 | chr3 | 52352194 | 52352326 | chr3 | 52442062 | 52442091 |
| chr3 | 52552556 | 52552661 | chr3 | 52553469 | 52553499 | chr3 | 53032733 | 53033524 |
| chr3 | 53253306 | 53253599 | chr3 | 53382392 | 53382565 | chr3 | 53480528 | 53480683 |
| chr3 | 54155611 | 54155677 | chr3 | 54157381 | 54157450 | chr3 | 54157878 | 54157919 |
| chr3 | 54583435 | 54583465 | chr3 | 55519219 | 55519253 | chr3 | 55523106 | 55523290 |
| chr3 | 55603443 | 55603632 | chr3 | 57437452 | 57437482 | chr3 | 57529094 | 57529218 |
| chr3 | 58153446 | 58153608 | chr3 | 62304567 | 62304669 | chr3 | 62353371 | 62354049 |
| chr3 | 62354283 | 62354328 | chr3 | 62354625 | 62354792 | chr3 | 62354900 | 62354914 |
| chr3 | 62355424 | 62355478 | chr3 | 62355774 | 62356219 | chr3 | 62356367 | 62356644 |
| chr3 | 62356793 | 62357192 | chr3 | 62357279 | 62357347 | chr3 | 62357624 | 62357667 |
| chr3 | 62358530 | 62358595 | chr3 | 62358858 | 62359011 | chr3 | 62359376 | 62359893 |
| chr3 | 62360302 | 62360560 | chr3 | 62362902 | 62362916 | chr3 | 62363099 | 62363200 |
| chr3 | 62363626 | 62363693 | chr3 | 62363906 | 62364176 | chr3 | 62364280 | 62364329 |

TABLE 12-continued

Pan Cancer #2

| chr | start | end | chr | start | end | chr | start | end |
|---|---|---|---|---|---|---|---|---|
| chr3 | 62364702 | 62365154 | chr3 | 62861118 | 62861148 | chr3 | 63264139 | 63264169 |
| chr3 | 63719169 | 63719303 | chr3 | 66053446 | 66053613 | chr3 | 68056904 | 68057145 |
| chr3 | 68980931 | 68981113 | chr3 | 68981552 | 68981624 | chr3 | 69590939 | 69590969 |
| chr3 | 69591363 | 69591414 | chr3 | 69591780 | 69591977 | chr3 | 69740944 | 69740990 |
| chr3 | 69937703 | 69937848 | chr3 | 70661011 | 70661079 | chr3 | 71802518 | 71802622 |
| chr3 | 71803126 | 71803372 | chr3 | 71803643 | 71803783 | chr3 | 73045340 | 73045583 |
| chr3 | 75956027 | 75956375 | chr3 | 79815522 | 79815557 | chr3 | 79816778 | 79817015 |
| chr3 | 79817288 | 79817318 | chr3 | 85008553 | 85008708 | chr3 | 88247941 | 88248049 |
| chr3 | 93698033 | 93698063 | chr3 | 96532817 | 96532873 | chr3 | 96533383 | 96533458 |
| chr3 | 96534035 | 96534096 | chr3 | 98313191 | 98313253 | chr3 | 98618182 | 98618376 |
| chr3 | 98620891 | 98620980 | chr3 | 99594925 | 99595105 | chr3 | 100228688 | 100228768 |
| chr3 | 101094160 | 101094190 | chr3 | 101230678 | 101231070 | chr3 | 101331792 | 101331861 |
| chr3 | 101354294 | 101354442 | chr3 | 101397240 | 101397358 | chr3 | 101406823 | 101407190 |
| chr3 | 101411545 | 101411666 | chr3 | 101497841 | 101497996 | chr3 | 101645019 | 101645181 |
| chr3 | 105015466 | 105015519 | chr3 | 105684885 | 105684987 | chr3 | 106936157 | 106936336 |
| chr3 | 112052252 | 112052419 | chr3 | 112185933 | 112185975 | chr3 | 113557333 | 113557363 |
| chr3 | 113847911 | 113847941 | chr3 | 115502232 | 115502390 | chr3 | 115512319 | 115512448 |
| chr3 | 117715549 | 117716123 | chr3 | 117716214 | 117716473 | chr3 | 120004080 | 120004405 |
| chr3 | 120004468 | 120004497 | chr3 | 120169104 | 120169149 | chr3 | 120169768 | 120169835 |
| chr3 | 120627317 | 120627453 | chr3 | 121215241 | 121215271 | chr3 | 121657197 | 121657515 |
| chr3 | 121741545 | 121741598 | chr3 | 121902991 | 121903218 | chr3 | 121903324 | 121903619 |
| chr3 | 122162036 | 122162117 | chr3 | 122162890 | 122163054 | chr3 | 122234242 | 122234538 |
| chr3 | 122573688 | 122573826 | chr3 | 122702288 | 122702451 | chr3 | 123167301 | 123167529 |
| chr3 | 123167769 | 123167827 | chr3 | 124410075 | 124410157 | chr3 | 125417341 | 125417424 |
| chr3 | 125898597 | 125899207 | chr3 | 125899525 | 125899962 | chr3 | 125932252 | 125932500 |
| chr3 | 126157586 | 126157663 | chr3 | 126261929 | 126262000 | chr3 | 126373520 | 126373704 |
| chr3 | 126854699 | 126854796 | chr3 | 127534814 | 127534897 | chr3 | 127634186 | 127634216 |
| chr3 | 127794546 | 127794860 | chr3 | 127795325 | 127795408 | chr3 | 128056383 | 128056497 |
| chr3 | 128202447 | 128202477 | chr3 | 128208903 | 128209232 | chr3 | 128273993 | 128274051 |
| chr3 | 128274309 | 128274611 | chr3 | 128384991 | 128385132 | chr3 | 128417201 | 128417231 |
| chr3 | 128599405 | 128599477 | chr3 | 128720061 | 128720142 | chr3 | 128720164 | 128720346 |
| chr3 | 128720419 | 128720533 | chr3 | 128720567 | 128720611 | chr3 | 128720869 | 128721229 |
| chr3 | 128764489 | 128764606 | chr3 | 128786496 | 128786526 | chr3 | 129008841 | 129009004 |
| chr3 | 129047978 | 129048008 | chr3 | 129372419 | 129372546 | chr3 | 129693108 | 129693199 |
| chr3 | 129693305 | 129693498 | chr3 | 129693955 | 129694299 | chr3 | 130064451 | 130064484 |
| chr3 | 130064818 | 130064848 | chr3 | 130236049 | 130236063 | chr3 | 130236174 | 130236273 |
| chr3 | 130502167 | 130502197 | chr3 | 130519901 | 130520077 | chr3 | 131754031 | 131754061 |
| chr3 | 132757065 | 132757104 | chr3 | 133217784 | 133217999 | chr3 | 133748140 | 133748245 |
| chr3 | 133748481 | 133748576 | chr3 | 133970381 | 133970474 | chr3 | 134369646 | 134369855 |
| chr3 | 134514866 | 134514895 | chr3 | 134515128 | 134515369 | chr3 | 134515676 | 134516222 |
| chr3 | 136016868 | 136016942 | chr3 | 136537642 | 136537730 | chr3 | 136538585 | 136538815 |
| chr3 | 136582883 | 136582951 | chr3 | 136751641 | 136751809 | chr3 | 137479233 | 137479302 |
| chr3 | 137479601 | 137479687 | chr3 | 137479980 | 137480764 | chr3 | 137481170 | 137481315 |
| chr3 | 137481858 | 137481872 | chr3 | 137481936 | 137482183 | chr3 | 137483313 | 137483437 |
| chr3 | 137483514 | 137483589 | chr3 | 137483848 | 137484002 | chr3 | 137484405 | 137484531 |
| chr3 | 137486029 | 137486310 | chr3 | 137486516 | 137486550 | chr3 | 137487964 | 137488003 |
| chr3 | 137488950 | 137489698 | chr3 | 137489876 | 137491040 | chr3 | 137892691 | 137892721 |
| chr3 | 137894374 | 137894415 | chr3 | 138058859 | 138058897 | chr3 | 138067717 | 138067747 |
| chr3 | 138153963 | 138153993 | chr3 | 138318827 | 138318918 | chr3 | 138374229 | 138374258 |
| chr3 | 138635369 | 138635507 | chr3 | 138655934 | 138656138 | chr3 | 138656834 | 138656889 |
| chr3 | 138657414 | 138657494 | chr3 | 138657618 | 138658296 | chr3 | 138658704 | 138658863 |
| chr3 | 138659081 | 138659099 | chr3 | 138662134 | 138662164 | chr3 | 138662282 | 138662296 |
| chr3 | 138662382 | 138662448 | chr3 | 138662799 | 138662842 | chr3 | 138663613 | 138663727 |
| chr3 | 138664142 | 138664165 | chr3 | 138664928 | 138665323 | chr3 | 138665562 | 138666294 |
| chr3 | 138668758 | 138669108 | chr3 | 138669141 | 138669387 | chr3 | 139258267 | 139258316 |
| chr3 | 139653491 | 139653693 | chr3 | 140769513 | 140769705 | chr3 | 140769908 | 140770301 |
| chr3 | 140770408 | 140770589 | chr3 | 140770644 | 140770829 | chr3 | 140771305 | 140771335 |
| chr3 | 140771816 | 140771854 | chr3 | 141174349 | 141174606 | chr3 | 141363466 | 141363496 |
| chr3 | 141481651 | 141482073 | chr3 | 141516389 | 141516719 | chr3 | 141657032 | 141657079 |
| chr3 | 141832939 | 141833015 | chr3 | 141835935 | 141836077 | chr3 | 142159804 | 142159841 |
| chr3 | 142537638 | 142537779 | chr3 | 142682273 | 142682392 | chr3 | 142718283 | 142718358 |
| chr3 | 142791151 | 142791255 | chr3 | 142837980 | 142838318 | chr3 | 142838621 | 142838646 |
| chr3 | 142838877 | 142839036 | chr3 | 142839563 | 142839688 | chr3 | 142839784 | 142839901 |
| chr3 | 142839945 | 142840127 | chr3 | 142840222 | 142840236 | chr3 | 142896156 | 142896214 |
| chr3 | 143280343 | 143280373 | chr3 | 143614462 | 143614504 | chr3 | 145735852 | 145735882 |
| chr3 | 145878665 | 145878695 | chr3 | 146187946 | 146187978 | chr3 | 147074457 | 147074487 |
| chr3 | 147074974 | 147075006 | chr3 | 147077289 | 147077671 | chr3 | 147078959 | 147079188 |
| chr3 | 147087562 | 147087799 | chr3 | 147088440 | 147088523 | chr3 | 147088939 | 147089099 |
| chr3 | 147098431 | 147098470 | chr3 | 147105898 | 147106010 | chr3 | 147108841 | 147109765 |
| chr3 | 147110229 | 147110683 | chr3 | 147110927 | 147111089 | chr3 | 147125697 | 147125726 |
| chr3 | 147127037 | 147127067 | chr3 | 147127681 | 147127902 | chr3 | 147136931 | 147137000 |
| chr3 | 147137076 | 147137164 | chr3 | 147138768 | 147138856 | chr3 | 147139374 | 147139528 |
| chr3 | 148415427 | 148415644 | chr3 | 148523213 | 148523297 | chr3 | 148803120 | 148803276 |
| chr3 | 149374947 | 149375023 | chr3 | 150237792 | 150237822 | chr3 | 150802981 | 150802999 |
| chr3 | 150803026 | 150803080 | chr3 | 150804043 | 150804077 | chr3 | 150804967 | 150805030 |
| chr3 | 152107022 | 152107052 | chr3 | 152553343 | 152553384 | chr3 | 152553658 | 152553725 |

TABLE 12-continued

Pan Cancer #2

| chr | start | end | chr | start | end | chr | start | end |
|---|---|---|---|---|---|---|---|---|
| chr3 | 152707390 | 152707460 | chr3 | 152877666 | 152877696 | chr3 | 153838818 | 153838870 |
| chr3 | 153839518 | 153839952 | chr3 | 154146133 | 154146394 | chr3 | 154146654 | 154146908 |
| chr3 | 154797334 | 154797703 | chr3 | 155456372 | 155456630 | chr3 | 155461030 | 155461195 |
| chr3 | 155463041 | 155463071 | chr3 | 156007772 | 156007801 | chr3 | 156008976 | 156009299 |
| chr3 | 156009319 | 156009425 | chr3 | 157155252 | 157155490 | chr3 | 157155982 | 157156194 |
| chr3 | 157812196 | 157812257 | chr3 | 157812437 | 157812645 | chr3 | 157812912 | 157813070 |
| chr3 | 157813670 | 157813824 | chr3 | 157814311 | 157814340 | chr3 | 157815657 | 157815822 |
| chr3 | 157820576 | 157820605 | chr3 | 157821537 | 157821662 | chr3 | 157821904 | 157822008 |
| chr3 | 157823073 | 157823119 | chr3 | 157823139 | 157823143 | chr3 | 157823464 | 157823493 |
| chr3 | 157824133 | 157824146 | chr3 | 157824212 | 157824231 | chr3 | 157824495 | 157824871 |
| chr3 | 157825176 | 157825408 | chr3 | 158319235 | 158319359 | chr3 | 159756687 | 159756856 |
| chr3 | 159944486 | 159944546 | chr3 | 164912376 | 164912568 | chr3 | 164912907 | 164913872 |
| chr3 | 164914980 | 164915129 | chr3 | 169376183 | 169376215 | chr3 | 169376680 | 169376780 |
| chr3 | 169378825 | 169379024 | chr3 | 169539898 | 169540679 | chr3 | 169541070 | 169541102 |
| chr3 | 170136627 | 170136751 | chr3 | 170302617 | 170302677 | chr3 | 170303087 | 170303129 |
| chr3 | 170303380 | 170303423 | chr3 | 170303639 | 170303844 | chr3 | 170602030 | 170602133 |
| chr3 | 171193088 | 171193311 | chr3 | 171527930 | 171527971 | chr3 | 171529811 | 171529958 |
| chr3 | 172165443 | 172165784 | chr3 | 172165867 | 172166512 | chr3 | 172166879 | 172166893 |
| chr3 | 172167000 | 172167044 | chr3 | 172167297 | 172167327 | chr3 | 172167660 | 172167917 |
| chr3 | 172342101 | 172342147 | chr3 | 172355895 | 172356038 | chr3 | 172383550 | 172383600 |
| chr3 | 172425382 | 172425717 | chr3 | 172469925 | 172470036 | chr3 | 173115237 | 173115550 |
| chr3 | 173162817 | 173162847 | chr3 | 173302542 | 173302668 | chr3 | 173302992 | 173303225 |
| chr3 | 176710106 | 176710241 | chr3 | 176872357 | 176872443 | chr3 | 178861259 | 178861447 |
| chr3 | 178916711 | 178916959 | chr3 | 178921537 | 178921568 | chr3 | 178927966 | 178928094 |
| chr3 | 178936059 | 178936111 | chr3 | 178952004 | 178952105 | chr3 | 179168661 | 179169266 |
| chr3 | 179367874 | 179367920 | chr3 | 179754178 | 179754192 | chr3 | 179754239 | 179754759 |
| chr3 | 179754804 | 179754872 | chr3 | 179755087 | 179755372 | chr3 | 180320256 | 180320294 |
| chr3 | 181413742 | 181414330 | chr3 | 181420065 | 181420116 | chr3 | 181420316 | 181420374 |
| chr3 | 181421411 | 181422282 | chr3 | 181422541 | 181422985 | chr3 | 181428388 | 181428772 |
| chr3 | 181430695 | 181430771 | chr3 | 181437129 | 181437349 | chr3 | 181438194 | 181438353 |
| chr3 | 181440892 | 181441927 | chr3 | 181442145 | 181442410 | chr3 | 181443014 | 181443557 |
| chr3 | 181443760 | 181443861 | chr3 | 181444108 | 181444236 | chr3 | 181444434 | 181444524 |
| chr3 | 181444613 | 181444948 | chr3 | 181444989 | 181445013 | chr3 | 181445369 | 181445464 |
| chr3 | 181445800 | 181445861 | chr3 | 182815811 | 182816027 | chr3 | 182895956 | 182896144 |
| chr3 | 182911545 | 182911574 | chr3 | 183109854 | 183109883 | chr3 | 183145412 | 183145618 |
| chr3 | 183145931 | 183146025 | chr3 | 183146397 | 183146435 | chr3 | 183146648 | 183146677 |
| chr3 | 183183523 | 183183659 | chr3 | 183208370 | 183208469 | chr3 | 183217676 | 183217706 |
| chr3 | 183647996 | 183648026 | chr3 | 183728793 | 183728952 | chr3 | 183870824 | 183870858 |
| chr3 | 183872490 | 183872524 | chr3 | 183965599 | 183965907 | chr3 | 184018038 | 184018136 |
| chr3 | 184031686 | 184031746 | chr3 | 184057254 | 184057557 | chr3 | 184099417 | 184099446 |
| chr3 | 184319470 | 184319612 | chr3 | 184319828 | 184319842 | chr3 | 184319874 | 184319891 |
| chr3 | 185001696 | 185001919 | chr3 | 185271296 | 185271764 | chr3 | 185275856 | 185275886 |
| chr3 | 185303247 | 185303277 | chr3 | 185363074 | 185363261 | chr3 | 185629516 | 185629546 |
| chr3 | 185643324 | 185643405 | chr3 | 185658513 | 185658543 | chr3 | 185668237 | 185668311 |
| chr3 | 186078766 | 186078898 | chr3 | 186079204 | 186079331 | chr3 | 186080188 | 186080218 |
| chr3 | 186287130 | 186287270 | chr3 | 186857152 | 186857607 | chr3 | 186914705 | 186914734 |
| chr3 | 187387850 | 187387920 | chr3 | 187388007 | 187388239 | chr3 | 192125828 | 192125828 |
| chr3 | 192126146 | 192126710 | chr3 | 192126787 | 192126863 | chr3 | 192127354 | 192127372 |
| chr3 | 192127557 | 192127730 | chr3 | 192127937 | 192128074 | chr3 | 192232097 | 192232175 |
| chr3 | 192232452 | 192232570 | chr3 | 192232895 | 192232951 | chr3 | 192233095 | 192233150 |
| chr3 | 192958725 | 192958968 | chr3 | 193312128 | 193312347 | chr3 | 193419702 | 193419732 |
| chr3 | 193548637 | 193548835 | chr3 | 193776089 | 193776119 | chr3 | 194048751 | 194048919 |
| chr3 | 194120008 | 194120164 | chr3 | 194120812 | 194120841 | chr3 | 194120934 | 194120963 |
| chr3 | 194208468 | 194208562 | chr3 | 194407998 | 194408028 | chr3 | 194408375 | 194408768 |
| chr3 | 194408839 | 194409021 | chr3 | 194981816 | 194981913 | chr3 | 195095450 | 195095543 |
| chr3 | 195184022 | 195184140 | chr3 | 195409773 | 195409813 | chr3 | 195536733 | 195536848 |
| chr3 | 195538217 | 195538353 | chr3 | 195587032 | 195587118 | chr3 | 195601239 | 195601312 |
| chr3 | 195602330 | 195602576 | chr3 | 195639755 | 195639785 | chr3 | 195648794 | 195649004 |
| chr3 | 195834581 | 195834611 | chr3 | 196046790 | 196046830 | chr3 | 196065342 | 196065583 |
| chr3 | 196069743 | 196070340 | chr3 | 196255617 | 196255631 | chr3 | 196263303 | 196263471 |
| chr3 | 196344683 | 196344796 | chr3 | 196387295 | 196387415 | chr3 | 196387628 | 196387665 |
| chr3 | 196388383 | 196388581 | chr3 | 196433946 | 196434104 | chr3 | 196440510 | 196440676 |
| chr3 | 196667872 | 196668080 | chr3 | 196728418 | 196728448 | chr3 | 196731155 | 196731313 |
| chr3 | 196755958 | 196755987 | chr3 | 197209019 | 197209048 | chr3 | 197236945 | 197237111 |
| chr3 | 197247047 | 197247110 | chr3 | 197278926 | 197278988 | chr3 | 197313997 | 197314107 |
| chr3 | 197326860 | 197327042 | chr3 | 197330060 | 197330147 | chr3 | 197466364 | 197466540 |
| chr3 | 197616707 | 197616861 | chr3 | 197677029 | 197677058 | chr3 | 197685788 | 197686085 |
| chr3 | 197686495 | 197686524 | chr3 | 197686941 | 197687223 | chr3 | 197687694 | 197687723 |
| chr4 | 206324 | 206353 | chr4 | 331322 | 331352 | chr4 | 488816 | 488875 |
| chr4 | 512978 | 513008 | chr4 | 513704 | 513734 | chr4 | 568429 | 568652 |
| chr4 | 569048 | 569115 | chr4 | 569275 | 569435 | chr4 | 569461 | 569732 |
| chr4 | 570966 | 571013 | chr4 | 571508 | 571689 | chr4 | 628572 | 629061 |
| chr4 | 651196 | 651261 | chr4 | 657521 | 657552 | chr4 | 678471 | 678501 |
| chr4 | 718052 | 718112 | chr4 | 718321 | 718456 | chr4 | 829611 | 829641 |
| chr4 | 955367 | 955454 | chr4 | 955867 | 955919 | chr4 | 995876 | 995993 |
| chr4 | 996101 | 996174 | chr4 | 1008740 | 1008902 | chr4 | 1016127 | 1016252 |

TABLE 12-continued

Pan Cancer #2

| chr | start | end | chr | start | end | chr | start | end |
|---|---|---|---|---|---|---|---|---|
| chr4 | 1016586 | 1016747 | chr4 | 1025928 | 1026074 | chr4 | 1041763 | 1041926 |
| chr4 | 1093536 | 1093675 | chr4 | 1107494 | 1107585 | chr4 | 1165450 | 1165470 |
| chr4 | 1189021 | 1189051 | chr4 | 1214894 | 1215162 | chr4 | 1215415 | 1215451 |
| chr4 | 1282515 | 1282545 | chr4 | 1331675 | 1331705 | chr4 | 1336755 | 1336902 |
| chr4 | 1338715 | 1338812 | chr4 | 1339099 | 1339221 | chr4 | 1396578 | 1396696 |
| chr4 | 1397396 | 1397495 | chr4 | 1398303 | 1398378 | chr4 | 1399723 | 1399768 |
| chr4 | 1401711 | 1401743 | chr4 | 1512368 | 1512398 | chr4 | 1556419 | 1556609 |
| chr4 | 1576484 | 1576528 | chr4 | 1616682 | 1617247 | chr4 | 1687080 | 1687110 |
| chr4 | 1800153 | 1800191 | chr4 | 1803550 | 1803582 | chr4 | 1806084 | 1806113 |
| chr4 | 1807355 | 1807384 | chr4 | 1962787 | 1962816 | chr4 | 1993771 | 1994180 |
| chr4 | 2042106 | 2042122 | chr4 | 2042169 | 2042258 | chr4 | 2066114 | 2066265 |
| chr4 | 2305672 | 2305827 | chr4 | 2527907 | 2527937 | chr4 | 2532556 | 2532586 |
| chr4 | 2540073 | 2540297 | chr4 | 2765862 | 2765910 | chr4 | 2926366 | 2926396 |
| chr4 | 2978968 | 2979145 | chr4 | 3036118 | 3036148 | chr4 | 3217107 | 3217154 |
| chr4 | 3371519 | 3371652 | chr4 | 3446991 | 3447021 | chr4 | 3447816 | 3448015 |
| chr4 | 3768833 | 3768949 | chr4 | 3768995 | 3769189 | chr4 | 3769560 | 3769574 |
| chr4 | 3873694 | 3873769 | chr4 | 4228189 | 4228241 | chr4 | 4229689 | 4229781 |
| chr4 | 4387533 | 4387627 | chr4 | 4417568 | 4417603 | chr4 | 4855102 | 4855171 |
| chr4 | 4855371 | 4855433 | chr4 | 4860046 | 4860075 | chr4 | 4862769 | 4863110 |
| chr4 | 4867698 | 4867886 | chr4 | 4868566 | 4868792 | chr4 | 4868829 | 4868999 |
| chr4 | 4872088 | 4872167 | chr4 | 4872777 | 4872850 | chr4 | 4873427 | 4873528 |
| chr4 | 5021188 | 5021217 | chr4 | 5053070 | 5053518 | chr4 | 5053747 | 5054093 |
| chr4 | 5519950 | 5520092 | chr4 | 5709906 | 5709984 | chr4 | 5712979 | 5713231 |
| chr4 | 5889948 | 5890045 | chr4 | 5890274 | 5890444 | chr4 | 5891966 | 5892081 |
| chr4 | 5892110 | 5892194 | chr4 | 5892750 | 5892780 | chr4 | 5893981 | 5894082 |
| chr4 | 6200897 | 6201235 | chr4 | 6202103 | 6202276 | chr4 | 6247351 | 6247381 |
| chr4 | 6565004 | 6565042 | chr4 | 6628453 | 6628500 | chr4 | 6670184 | 6670214 |
| chr4 | 6719599 | 6719637 | chr4 | 6748346 | 6748557 | chr4 | 6839352 | 6839402 |
| chr4 | 6955114 | 6955144 | chr4 | 6957470 | 6957620 | chr4 | 7038560 | 7038688 |
| chr4 | 7647770 | 7647945 | chr4 | 7758476 | 7758561 | chr4 | 8429086 | 8429178 |
| chr4 | 8582549 | 8582579 | chr4 | 8607813 | 8607932 | chr4 | 8608556 | 8608600 |
| chr4 | 8858827 | 8859047 | chr4 | 8859382 | 8859738 | chr4 | 8860398 | 8860553 |
| chr4 | 8861649 | 8861752 | chr4 | 8861919 | 8862014 | chr4 | 8862797 | 8862811 |
| chr4 | 8863441 | 8863526 | chr4 | 8864499 | 8864598 | chr4 | 8864831 | 8865058 |
| chr4 | 8868822 | 8868845 | chr4 | 8868932 | 8869270 | chr4 | 8869601 | 8869813 |
| chr4 | 8873054 | 8873072 | chr4 | 8873809 | 8873984 | chr4 | 8874485 | 8874534 |
| chr4 | 8874773 | 8874787 | chr4 | 8875877 | 8875907 | chr4 | 8893060 | 8893093 |
| chr4 | 8893501 | 8893531 | chr4 | 8893816 | 8893931 | chr4 | 8894641 | 8894957 |
| chr4 | 8895232 | 8895350 | chr4 | 8895554 | 8895584 | chr4 | 8895965 | 8896052 |
| chr4 | 9423273 | 9423354 | chr4 | 9782992 | 9783095 | chr4 | 9783126 | 9783412 |
| chr4 | 10458395 | 10459121 | chr4 | 10462833 | 10463047 | chr4 | 10463073 | 10463604 |
| chr4 | 10782701 | 10782741 | chr4 | 11429506 | 11429633 | chr4 | 13524026 | 13524251 |
| chr4 | 13524665 | 13524775 | chr4 | 13524957 | 13524971 | chr4 | 13537569 | 13537688 |
| chr4 | 13540983 | 13541068 | chr4 | 13546026 | 13546078 | chr4 | 13548502 | 13548589 |
| chr4 | 13548635 | 13548895 | chr4 | 13549340 | 13549510 | chr4 | 15780223 | 15780320 |
| chr4 | 16084741 | 16084818 | chr4 | 16085167 | 16085301 | chr4 | 16085352 | 16085381 |
| chr4 | 16085675 | 16085682 | chr4 | 17430691 | 17430832 | chr4 | 17783003 | 17783480 |
| chr4 | 20254693 | 20254723 | chr4 | 20255525 | 20255861 | chr4 | 20256152 | 20256285 |
| chr4 | 21950248 | 21950295 | chr4 | 24801868 | 24801985 | chr4 | 24914638 | 24914668 |
| chr4 | 25656815 | 25656879 | chr4 | 25657437 | 25657477 | chr4 | 26256826 | 26256867 |
| chr4 | 27086432 | 27086462 | chr4 | 30722243 | 30722273 | chr4 | 30723856 | 30723862 |
| chr4 | 30724249 | 30724372 | chr4 | 37245837 | 37245851 | chr4 | 37246134 | 37246360 |
| chr4 | 37246490 | 37246699 | chr4 | 37247096 | 37247216 | chr4 | 38566328 | 38566418 |
| chr4 | 38673115 | 38673144 | chr4 | 39816807 | 39817064 | chr4 | 40632773 | 40632802 |
| chr4 | 40910303 | 40910465 | chr4 | 41258716 | 41258788 | chr4 | 41259086 | 41259176 |
| chr4 | 41747009 | 41747133 | chr4 | 41747493 | 41747582 | chr4 | 41747958 | 41748011 |
| chr4 | 41748144 | 41748296 | chr4 | 41748660 | 41748766 | chr4 | 41749033 | 41749063 |
| chr4 | 41749270 | 41749761 | chr4 | 41750223 | 41750504 | chr4 | 41751870 | 41752006 |
| chr4 | 41752451 | 41752693 | chr4 | 41752798 | 41753398 | chr4 | 41753610 | 41753916 |
| chr4 | 41754031 | 41754071 | chr4 | 41875430 | 41875902 | chr4 | 41880331 | 41880412 |
| chr4 | 41881385 | 41881425 | chr4 | 41883091 | 41883302 | chr4 | 41883510 | 41883610 |
| chr4 | 41938449 | 41938479 | chr4 | 41993676 | 41993815 | chr4 | 42152962 | 42153411 |
| chr4 | 42153533 | 42153632 | chr4 | 42153882 | 42154025 | chr4 | 42154280 | 42154359 |
| chr4 | 42154662 | 42154997 | chr4 | 42155293 | 42155322 | chr4 | 42348266 | 42348331 |
| chr4 | 42398842 | 42398872 | chr4 | 42399137 | 42399191 | chr4 | 42399688 | 42399872 |
| chr4 | 44266683 | 44266780 | chr4 | 44449480 | 44449569 | chr4 | 46067800 | 46067954 |
| chr4 | 46391353 | 46391383 | chr4 | 46911535 | 46911564 | chr4 | 46995161 | 46995835 |
| chr4 | 47034908 | 47034938 | chr4 | 47197142 | 47197270 | chr4 | 47914784 | 47914992 |
| chr4 | 48485067 | 48485288 | chr4 | 48485590 | 48486000 | chr4 | 48486356 | 48486389 |
| chr4 | 48492181 | 48492433 | chr4 | 48848428 | 48848554 | chr4 | 48988109 | 48988335 |
| chr4 | 53728495 | 53729056 | chr4 | 54966854 | 54967075 | chr4 | 54967342 | 54967484 |
| chr4 | 54969833 | 54970095 | chr4 | 54970369 | 54970482 | chr4 | 54975991 | 54976115 |
| chr4 | 55093048 | 55093255 | chr4 | 55096239 | 55096344 | chr4 | 55097404 | 55097634 |
| chr4 | 55097973 | 55098092 | chr4 | 55098198 | 55098373 | chr4 | 55098674 | 55098744 |
| chr4 | 55099016 | 55099062 | chr4 | 55133613 | 55133642 | chr4 | 55136787 | 55136816 |
| chr4 | 55138657 | 55138686 | chr4 | 55139691 | 55139720 | chr4 | 55140731 | 55140784 |

TABLE 12-continued

| \multicolumn{9}{c|}{Pan Cancer #2} |
| chr | start | end | chr | start | end | chr | start | end |
| --- | --- | --- | --- | --- | --- | --- | --- | --- |
| chr4 | 55141015 | 55141050 | chr4 | 55144105 | 55144134 | chr4 | 55146554 | 55146583 |
| chr4 | 55152075 | 55152140 | chr4 | 55524220 | 55524274 | chr4 | 55589753 | 55589782 |
| chr4 | 55592166 | 55592204 | chr4 | 55593417 | 55593675 | chr4 | 55594183 | 55594212 |
| chr4 | 55595504 | 55595614 | chr4 | 55599306 | 55599356 | chr4 | 55968165 | 55968194 |
| chr4 | 55991107 | 55991228 | chr4 | 55992153 | 55992169 | chr4 | 56594679 | 56594720 |
| chr4 | 56659692 | 56659866 | chr4 | 56659935 | 56660021 | chr4 | 57017387 | 57017459 |
| chr4 | 57371718 | 57371963 | chr4 | 57372336 | 57372504 | chr4 | 57396946 | 57397264 |
| chr4 | 57521506 | 57521663 | chr4 | 57521701 | 57522382 | chr4 | 57522420 | 57522815 |
| chr4 | 57687720 | 57687782 | chr4 | 57777437 | 57777595 | chr4 | 57803498 | 57803558 |
| chr4 | 57813490 | 57813763 | chr4 | 57976033 | 57976185 | chr4 | 57976416 | 57976573 |
| chr4 | 58030191 | 58030524 | chr4 | 62066196 | 62066553 | chr4 | 62067511 | 62067624 |
| chr4 | 62068072 | 62068150 | chr4 | 66535130 | 66535314 | chr4 | 66535351 | 66535443 |
| chr4 | 66536171 | 66536323 | chr4 | 73459699 | 73459762 | chr4 | 74142341 | 74142434 |
| chr4 | 74702479 | 74702516 | chr4 | 74735076 | 74735137 | chr4 | 74809877 | 74809933 |
| chr4 | 75241080 | 75241435 | chr4 | 75858573 | 75858629 | chr4 | 76554873 | 76554935 |
| chr4 | 76555532 | 76555856 | chr4 | 76912698 | 76912733 | chr4 | 79611132 | 79611294 |
| chr4 | 79689651 | 79689732 | chr4 | 79861530 | 79861560 | chr4 | 80273120 | 80273150 |
| chr4 | 81106351 | 81106871 | chr4 | 81124277 | 81124662 | chr4 | 81187046 | 81187076 |
| chr4 | 81187559 | 81187589 | chr4 | 81188385 | 81188489 | chr4 | 81188491 | 81188556 |
| chr4 | 81189419 | 81189660 | chr4 | 81189714 | 81189911 | chr4 | 81951431 | 81951460 |
| chr4 | 81951941 | 81951970 | chr4 | 81952170 | 81952311 | chr4 | 82135873 | 82135887 |
| chr4 | 82135920 | 82136056 | chr4 | 82136495 | 82136548 | chr4 | 82136807 | 82136837 |
| chr4 | 83323506 | 83323708 | chr4 | 83343366 | 83343396 | chr4 | 83720611 | 83720643 |
| chr4 | 83809740 | 83809787 | chr4 | 83955171 | 83955201 | chr4 | 83988361 | 83988511 |
| chr4 | 84035907 | 84035936 | chr4 | 85402377 | 85402511 | chr4 | 85402776 | 85403423 |
| chr4 | 85403913 | 85403927 | chr4 | 85404112 | 85404140 | chr4 | 85404225 | 85404475 |
| chr4 | 85404650 | 85404693 | chr4 | 85414045 | 85414113 | chr4 | 85414725 | 85414846 |
| chr4 | 85417336 | 85417564 | chr4 | 85417953 | 85418079 | chr4 | 85418522 | 85418582 |
| chr4 | 85420591 | 85420621 | chr4 | 85422188 | 85422432 | chr4 | 85422973 | 85423316 |
| chr4 | 85424401 | 85424483 | chr4 | 87515337 | 87515367 | chr4 | 89378464 | 89378497 |
| chr4 | 89378744 | 89378766 | chr4 | 89378832 | 89378888 | chr4 | 90043517 | 90043547 |
| chr4 | 90757517 | 90757828 | chr4 | 90758105 | 90758134 | chr4 | 90758776 | 90758883 |
| chr4 | 91079842 | 91079899 | chr4 | 93224972 | 93225171 | chr4 | 93226365 | 93226703 |
| chr4 | 93226729 | 93227129 | chr4 | 94749725 | 94749755 | chr4 | 94750982 | 94751140 |
| chr4 | 94751419 | 94751502 | chr4 | 94753415 | 94753445 | chr4 | 94756002 | 94756109 |
| chr4 | 95127590 | 95127717 | chr4 | 95128038 | 95128068 | chr4 | 95762672 | 95762896 |
| chr4 | 96470752 | 96470782 | chr4 | 101111246 | 101111504 | chr4 | 101111857 | 101111970 |
| chr4 | 102332467 | 102332611 | chr4 | 102711731 | 102711787 | chr4 | 103929647 | 103929796 |
| chr4 | 103930065 | 103930095 | chr4 | 106335495 | 106335617 | chr4 | 107955311 | 107955826 |
| chr4 | 107956676 | 107957086 | chr4 | 107957373 | 107957466 | chr4 | 109093101 | 109093168 |
| chr4 | 109093405 | 109093506 | chr4 | 110223090 | 110223427 | chr4 | 110223579 | 110223980 |
| chr4 | 110344202 | 110344294 | chr4 | 110735672 | 110735702 | chr4 | 111532705 | 111532961 |
| chr4 | 111536288 | 111536505 | chr4 | 111536562 | 111536693 | chr4 | 111536960 | 111536974 |
| chr4 | 111537407 | 111537497 | chr4 | 111540199 | 111540360 | chr4 | 111542474 | 111542757 |
| chr4 | 111543232 | 111543345 | chr4 | 111543404 | 111543450 | chr4 | 111543661 | 111543695 |
| chr4 | 111543721 | 111543735 | chr4 | 111544381 | 111544583 | chr4 | 111549800 | 111549830 |
| chr4 | 111550618 | 111550834 | chr4 | 111552118 | 111552148 | chr4 | 111553099 | 111553450 |
| chr4 | 111553916 | 111553951 | chr4 | 111554950 | 111554964 | chr4 | 111555194 | 111555343 |
| chr4 | 111557965 | 111558049 | chr4 | 111558551 | 111559233 | chr4 | 111560249 | 111560636 |
| chr4 | 111562576 | 111562648 | chr4 | 113154896 | 113155129 | chr4 | 113430640 | 113430672 |
| chr4 | 113431834 | 113431854 | chr4 | 113431916 | 113432154 | chr4 | 113432227 | 113432503 |
| chr4 | 113432519 | 113432573 | chr4 | 113436216 | 113436287 | chr4 | 113441592 | 113441733 |
| chr4 | 113442098 | 113442185 | chr4 | 113442247 | 113442525 | chr4 | 113444020 | 113444448 |
| chr4 | 113559163 | 113559422 | chr4 | 117847399 | 117847458 | chr4 | 121844063 | 121844206 |
| chr4 | 121992265 | 121992312 | chr4 | 121993997 | 121994251 | chr4 | 122301422 | 122301712 |
| chr4 | 122302116 | 122302246 | chr4 | 122685807 | 122685890 | chr4 | 122686209 | 122686507 |
| chr4 | 122871294 | 122871334 | chr4 | 122871573 | 122872000 | chr4 | 123664228 | 123664363 |
| chr4 | 126237310 | 126237611 | chr4 | 126238024 | 126238436 | chr4 | 128544048 | 128544161 |
| chr4 | 128544646 | 128544789 | chr4 | 128967250 | 128967329 | chr4 | 128968647 | 128968800 |
| chr4 | 128969310 | 128969382 | chr4 | 128984386 | 128984464 | chr4 | 130018134 | 130018266 |
| chr4 | 134067881 | 134068004 | chr4 | 134068577 | 134068791 | chr4 | 134069289 | 134069318 |
| chr4 | 134069578 | 134069896 | chr4 | 134070374 | 134070403 | chr4 | 134071648 | 134072610 |
| chr4 | 134072677 | 134072967 | chr4 | 134073184 | 134073322 | chr4 | 134073568 | 134073641 |
| chr4 | 134073862 | 134073919 | chr4 | 134074030 | 134074156 | chr4 | 140200529 | 140201156 |
| chr4 | 140201193 | 140201462 | chr4 | 140656643 | 140656666 | chr4 | 140656858 | 140657089 |
| chr4 | 141347942 | 141348151 | chr4 | 141418921 | 141419418 | chr4 | 141488870 | 141489128 |
| chr4 | 142053130 | 142053160 | chr4 | 142053520 | 142053734 | chr4 | 142054239 | 142054460 |
| chr4 | 143766796 | 143766930 | chr4 | 144586035 | 144586088 | chr4 | 144621336 | 144621439 |
| chr4 | 144621515 | 144621896 | chr4 | 144621982 | 144622058 | chr4 | 145568052 | 145568147 |
| chr4 | 145568459 | 145568741 | chr4 | 146853951 | 146853981 | chr4 | 147558272 | 147558381 |
| chr4 | 147558477 | 147558504 | chr4 | 147559321 | 147560078 | chr4 | 147560134 | 147560418 |
| chr4 | 147560460 | 147560617 | chr4 | 147560933 | 147561145 | chr4 | 147561360 | 147561949 |
| chr4 | 147562000 | 147562055 | chr4 | 147568636 | 147569060 | chr4 | 147569620 | 147569650 |
| chr4 | 147576177 | 147576201 | chr4 | 147576330 | 147576639 | chr4 | 151974287 | 151974510 |
| chr4 | 152148807 | 152148836 | chr4 | 152246132 | 152246314 | chr4 | 153247273 | 153247386 |
| chr4 | 153249362 | 153249398 | chr4 | 153251894 | 153251923 | chr4 | 153702668 | 153702702 |

TABLE 12-continued

Pan Cancer #2

| chr | start | end | chr | start | end | chr | start | end |
|---|---|---|---|---|---|---|---|---|
| chr4 | 154216241 | 154216357 | chr4 | 154374504 | 154374630 | chr4 | 154709524 | 154709610 |
| chr4 | 154709759 | 154710617 | chr4 | 154710729 | 154710914 | chr4 | 154712172 | 154712594 |
| chr4 | 154713500 | 154713530 | chr4 | 154713949 | 154714010 | chr4 | 155254166 | 155254196 |
| chr4 | 155411851 | 155412279 | chr4 | 155663209 | 155663647 | chr4 | 155665445 | 155665475 |
| chr4 | 156129153 | 156129183 | chr4 | 156129451 | 156129495 | chr4 | 156129746 | 156129797 |
| chr4 | 156130047 | 156130297 | chr4 | 156297416 | 156297556 | chr4 | 156297942 | 156298073 |
| chr4 | 156588311 | 156588401 | chr4 | 156589273 | 156589323 | chr4 | 156680257 | 156680532 |
| chr4 | 156681370 | 156681489 | chr4 | 158101782 | 158102020 | chr4 | 158141576 | 158141606 |
| chr4 | 158142847 | 158142999 | chr4 | 158143443 | 158143465 | chr4 | 159063301 | 159063331 |
| chr4 | 159149784 | 159149824 | chr4 | 164252991 | 164253447 | chr4 | 164819191 | 164819221 |
| chr4 | 165304515 | 165304578 | chr4 | 165305060 | 165305163 | chr4 | 166414834 | 166414921 |
| chr4 | 166794771 | 166794909 | chr4 | 166796118 | 166796212 | chr4 | 168155109 | 168155269 |
| chr4 | 170865234 | 170865287 | chr4 | 170947287 | 170947325 | chr4 | 171012375 | 171012409 |
| chr4 | 172132870 | 172133019 | chr4 | 172734189 | 172734203 | chr4 | 172734592 | 172734790 |
| chr4 | 173953411 | 173953594 | chr4 | 174083164 | 174083431 | chr4 | 174124429 | 174124477 |
| chr4 | 174136704 | 174136734 | chr4 | 174224186 | 174224216 | chr4 | 174429658 | 174429688 |
| chr4 | 174430310 | 174430553 | chr4 | 174430794 | 174431072 | chr4 | 174438567 | 174438744 |
| chr4 | 174439822 | 174440257 | chr4 | 174440635 | 174440713 | chr4 | 174443212 | 174443242 |
| chr4 | 174443563 | 174443934 | chr4 | 174446508 | 174446525 | chr4 | 174446952 | 174447005 |
| chr4 | 174449950 | 174450726 | chr4 | 174450752 | 174451482 | chr4 | 174451855 | 174452098 |
| chr4 | 174459185 | 174459374 | chr4 | 174459528 | 174459840 | chr4 | 174460186 | 174460221 |
| chr4 | 175132735 | 175132765 | chr4 | 175133085 | 175133201 | chr4 | 175134897 | 175135672 |
| chr4 | 175135921 | 175136011 | chr4 | 175138411 | 175138546 | chr4 | 175138964 | 175139254 |
| chr4 | 175139559 | 175139685 | chr4 | 175750456 | 175750738 | chr4 | 176923424 | 176923558 |
| chr4 | 176987324 | 176987373 | chr4 | 177713228 | 177713437 | chr4 | 178285756 | 178285879 |
| chr4 | 180979270 | 180979300 | chr4 | 180980297 | 180980356 | chr4 | 183063666 | 183063950 |
| chr4 | 183064617 | 183064655 | chr4 | 183064874 | 183064966 | chr4 | 184019249 | 184019316 |
| chr4 | 184019692 | 184019736 | chr4 | 184020106 | 184020179 | chr4 | 184375546 | 184375726 |
| chr4 | 184491996 | 184492042 | chr4 | 184644053 | 184644249 | chr4 | 184718260 | 184718352 |
| chr4 | 184826238 | 184826493 | chr4 | 184826938 | 184827237 | chr4 | 184921855 | 184922091 |
| chr4 | 185089696 | 185089797 | chr4 | 185937333 | 185937889 | chr4 | 185938497 | 185938564 |
| chr4 | 185940338 | 185940460 | chr4 | 185941585 | 185942472 | chr4 | 185942492 | 185942760 |
| chr4 | 187647073 | 187647457 | chr5 | 53849 | 53898 | chr5 | 92163 | 92399 |
| chr5 | 230673 | 230709 | chr5 | 303272 | 303301 | chr5 | 320840 | 320982 |
| chr5 | 343916 | 343941 | chr5 | 373363 | 373392 | chr5 | 373872 | 374266 |
| chr5 | 400186 | 400215 | chr5 | 400502 | 400531 | chr5 | 415870 | 415899 |
| chr5 | 481012 | 481121 | chr5 | 491335 | 491536 | chr5 | 524337 | 524404 |
| chr5 | 538758 | 538806 | chr5 | 554299 | 554538 | chr5 | 554871 | 554900 |
| chr5 | 555158 | 555285 | chr5 | 555965 | 555995 | chr5 | 677889 | 678006 |
| chr5 | 909204 | 909304 | chr5 | 912806 | 912835 | chr5 | 1034600 | 1034653 |
| chr5 | 1059523 | 1059556 | chr5 | 1093660 | 1093797 | chr5 | 1117778 | 1118270 |
| chr5 | 1131217 | 1131378 | chr5 | 1136590 | 1136845 | chr5 | 1193381 | 1193521 |
| chr5 | 1193880 | 1193944 | chr5 | 1221197 | 1221307 | chr5 | 1259524 | 1259558 |
| chr5 | 1271339 | 1271396 | chr5 | 1294630 | 1294767 | chr5 | 1295031 | 1295442 |
| chr5 | 1295605 | 1295662 | chr5 | 1445171 | 1445255 | chr5 | 1445738 | 1445759 |
| chr5 | 1445841 | 1445928 | chr5 | 1446319 | 1446369 | chr5 | 1446443 | 1446599 |
| chr5 | 1747022 | 1747098 | chr5 | 1779526 | 1779556 | chr5 | 1787378 | 1787418 |
| chr5 | 1874892 | 1875099 | chr5 | 1875453 | 1875497 | chr5 | 1875870 | 1876306 |
| chr5 | 1876638 | 1876860 | chr5 | 1877195 | 1877239 | chr5 | 1878014 | 1878028 |
| chr5 | 1878224 | 1878528 | chr5 | 1878831 | 1879045 | chr5 | 1879605 | 1879661 |
| chr5 | 1879690 | 1879719 | chr5 | 1882420 | 1882605 | chr5 | 1882844 | 1882921 |
| chr5 | 1883515 | 1883616 | chr5 | 1884178 | 1884237 | chr5 | 1884557 | 1884698 |
| chr5 | 1885158 | 1885458 | chr5 | 1885985 | 1886076 | chr5 | 1886542 | 1886581 |
| chr5 | 1886812 | 1886841 | chr5 | 1886998 | 1887145 | chr5 | 1887547 | 1887581 |
| chr5 | 1887656 | 1887737 | chr5 | 1930786 | 1931004 | chr5 | 1931065 | 1931286 |
| chr5 | 1931445 | 1931576 | chr5 | 1931618 | 1931754 | chr5 | 1950794 | 1950960 |
| chr5 | 1952624 | 1952638 | chr5 | 2038705 | 2038850 | chr5 | 2225439 | 2225469 |
| chr5 | 2324383 | 2324413 | chr5 | 2367718 | 2367892 | chr5 | 2541487 | 2541611 |
| chr5 | 2738848 | 2739129 | chr5 | 2739211 | 2739354 | chr5 | 2739877 | 2740300 |
| chr5 | 2740431 | 2740664 | chr5 | 2743617 | 2743659 | chr5 | 2743699 | 2743713 |
| chr5 | 2748374 | 2748459 | chr5 | 2749213 | 2749406 | chr5 | 2749699 | 2749729 |
| chr5 | 2750435 | 2750516 | chr5 | 2750655 | 2750769 | chr5 | 2751855 | 2751894 |
| chr5 | 2752991 | 2753040 | chr5 | 2753048 | 2753078 | chr5 | 2754738 | 2754767 |
| chr5 | 2755323 | 2756388 | chr5 | 2756599 | 2756602 | chr5 | 2756674 | 2757427 |
| chr5 | 3031879 | 3032018 | chr5 | 3152146 | 3152176 | chr5 | 3325042 | 3325272 |
| chr5 | 3590405 | 3590657 | chr5 | 3591354 | 3591388 | chr5 | 3591857 | 3592037 |
| chr5 | 3592728 | 3592881 | chr5 | 3594250 | 3594519 | chr5 | 3595090 | 3595178 |
| chr5 | 3595850 | 3595991 | chr5 | 3596556 | 3596724 | chr5 | 3596825 | 3596880 |
| chr5 | 3597411 | 3597461 | chr5 | 3600150 | 3600180 | chr5 | 3602804 | 3603320 |
| chr5 | 3674053 | 3674224 | chr5 | 4144367 | 4144516 | chr5 | 5139754 | 5139900 |
| chr5 | 5140170 | 5140225 | chr5 | 5140630 | 5140757 | chr5 | 5140850 | 5140901 |
| chr5 | 6228617 | 6228790 | chr5 | 6448930 | 6449582 | chr5 | 6482458 | 6482620 |
| chr5 | 6583461 | 6583579 | chr5 | 6687277 | 6687431 | chr5 | 6755789 | 6755843 |
| chr5 | 7395263 | 7395393 | chr5 | 7395434 | 7395538 | chr5 | 7851015 | 7851121 |
| chr5 | 9546612 | 9546648 | chr5 | 10249098 | 10249127 | chr5 | 10333688 | 10334132 |
| chr5 | 10565021 | 10565227 | chr5 | 10565263 | 10565607 | chr5 | 10616516 | 10616550 |

TABLE 12-continued

Pan Cancer #2

| chr | start | end | chr | start | end | chr | start | end |
|---|---|---|---|---|---|---|---|---|
| chr5 | 11384965 | 11385363 | chr5 | 11903822 | 11904173 | chr5 | 11904196 | 11904379 |
| chr5 | 11904456 | 11904696 | chr5 | 11904896 | 11904943 | chr5 | 14872919 | 14873053 |
| chr5 | 15500748 | 15500927 | chr5 | 16179049 | 16179141 | chr5 | 16179555 | 16179713 |
| chr5 | 16180183 | 16180260 | chr5 | 16466784 | 16467120 | chr5 | 16793851 | 16794008 |
| chr5 | 16845452 | 16845619 | chr5 | 16936354 | 16936514 | chr5 | 16968118 | 16968148 |
| chr5 | 17095895 | 17095927 | chr5 | 17203012 | 17203177 | chr5 | 17218195 | 17218225 |
| chr5 | 17218986 | 17219018 | chr5 | 17311046 | 17311076 | chr5 | 17512114 | 17512144 |
| chr5 | 18034335 | 18034365 | chr5 | 22853443 | 22853508 | chr5 | 23011928 | 23011958 |
| chr5 | 31193937 | 31193989 | chr5 | 31194375 | 31194641 | chr5 | 31572285 | 31572344 |
| chr5 | 31639684 | 31639960 | chr5 | 31691477 | 31691652 | chr5 | 31855073 | 31855199 |
| chr5 | 31879243 | 31879282 | chr5 | 32042283 | 32042419 | chr5 | 32314345 | 32314379 |
| chr5 | 32333032 | 32333111 | chr5 | 32446143 | 32446274 | chr5 | 32710331 | 32710470 |
| chr5 | 32710802 | 32711531 | chr5 | 32711826 | 32711870 | chr5 | 32712077 | 32712101 |
| chr5 | 32712290 | 32712491 | chr5 | 32712764 | 32713304 | chr5 | 33234280 | 33234411 |
| chr5 | 33298005 | 33298076 | chr5 | 33509607 | 33509776 | chr5 | 33892083 | 33892115 |
| chr5 | 33892413 | 33892443 | chr5 | 33936156 | 33936336 | chr5 | 33936486 | 33936516 |
| chr5 | 33936599 | 33936663 | chr5 | 34656932 | 34657034 | chr5 | 35874586 | 35874589 |
| chr5 | 35939832 | 35939861 | chr5 | 37376644 | 37376674 | chr5 | 37834684 | 37834714 |
| chr5 | 37835015 | 37835125 | chr5 | 37836231 | 37836260 | chr5 | 37836649 | 37837992 |
| chr5 | 37838548 | 37838885 | chr5 | 37839808 | 37840125 | chr5 | 37840530 | 37840853 |
| chr5 | 38257485 | 38257606 | chr5 | 38257842 | 38257908 | chr5 | 38257945 | 38257959 |
| chr5 | 38557070 | 38557400 | chr5 | 38845675 | 38846164 | chr5 | 39281800 | 39281943 |
| chr5 | 39343181 | 39343348 | chr5 | 40681122 | 40681227 | chr5 | 40681262 | 40681367 |
| chr5 | 40681676 | 40681839 | chr5 | 40775147 | 40775313 | chr5 | 42260050 | 42260453 |
| chr5 | 42424822 | 42425060 | chr5 | 42931966 | 42931996 | chr5 | 42950796 | 42951311 |
| chr5 | 42951420 | 42952111 | chr5 | 42991825 | 42992241 | chr5 | 42992376 | 42992597 |
| chr5 | 42992783 | 42992934 | chr5 | 42993150 | 42994193 | chr5 | 42994694 | 42994790 |
| chr5 | 42995115 | 42995153 | chr5 | 43007936 | 43007966 | chr5 | 43008202 | 43008562 |
| chr5 | 43017953 | 43018176 | chr5 | 43018327 | 43018767 | chr5 | 43019238 | 43019347 |
| chr5 | 43019809 | 43019887 | chr5 | 43020146 | 43020294 | chr5 | 43040544 | 43040635 |
| chr5 | 43040870 | 43040964 | chr5 | 43215538 | 43215738 | chr5 | 43397002 | 43397229 |
| chr5 | 43402678 | 43403084 | chr5 | 43558065 | 43558099 | chr5 | 44389782 | 44389852 |
| chr5 | 45695186 | 45695239 | chr5 | 45695314 | 45695533 | chr5 | 45695906 | 45695947 |
| chr5 | 45696336 | 45696439 | chr5 | 49736592 | 49736685 | chr5 | 50262893 | 50263014 |
| chr5 | 50263568 | 50263641 | chr5 | 50264307 | 50264603 | chr5 | 50264820 | 50264850 |
| chr5 | 50265325 | 50265429 | chr5 | 50265721 | 50265880 | chr5 | 50674152 | 50674188 |
| chr5 | 50674560 | 50674590 | chr5 | 50675013 | 50675075 | chr5 | 50678346 | 50678490 |
| chr5 | 50695351 | 50695463 | chr5 | 52084073 | 52084134 | chr5 | 52887899 | 52888024 |
| chr5 | 54179610 | 54179633 | chr5 | 54180063 | 54180093 | chr5 | 54516371 | 54516680 |
| chr5 | 54516832 | 54517017 | chr5 | 54518651 | 54519288 | chr5 | 54527323 | 54527343 |
| chr5 | 56077938 | 56078065 | chr5 | 56246546 | 56246575 | chr5 | 56247942 | 56247971 |
| chr5 | 56248218 | 56248257 | chr5 | 56467399 | 56467666 | chr5 | 57878271 | 57878375 |
| chr5 | 57878710 | 57878752 | chr5 | 59188291 | 59188327 | chr5 | 59189055 | 59189057 |
| chr5 | 59189189 | 59189206 | chr5 | 59189863 | 59189948 | chr5 | 63254903 | 63255242 |
| chr5 | 63256863 | 63256895 | chr5 | 63257727 | 63257861 | chr5 | 63802007 | 63802304 |
| chr5 | 63802340 | 63802514 | chr5 | 63986488 | 63986527 | chr5 | 63986570 | 63986807 |
| chr5 | 65181732 | 65181778 | chr5 | 67569803 | 67569832 | chr5 | 67588937 | 67589162 |
| chr5 | 67589598 | 67589627 | chr5 | 67590431 | 67590460 | chr5 | 67591068 | 67591157 |
| chr5 | 68391042 | 68391336 | chr5 | 71014720 | 71014895 | chr5 | 71015180 | 71015728 |
| chr5 | 71106820 | 71107027 | chr5 | 71403566 | 71403653 | chr5 | 71403975 | 71404207 |
| chr5 | 72416246 | 72416751 | chr5 | 72526413 | 72526414 | chr5 | 72526492 | 72526643 |
| chr5 | 72528434 | 72528464 | chr5 | 72529289 | 72529825 | chr5 | 72529890 | 72530609 |
| chr5 | 72594802 | 72594836 | chr5 | 72594868 | 72595016 | chr5 | 72595047 | 72595059 |
| chr5 | 72595542 | 72595721 | chr5 | 72595774 | 72595788 | chr5 | 72599079 | 72599441 |
| chr5 | 72599463 | 72599833 | chr5 | 72677775 | 72677825 | chr5 | 72677998 | 72678028 |
| chr5 | 72715204 | 72715347 | chr5 | 72715591 | 72715695 | chr5 | 72715731 | 72715768 |
| chr5 | 72716102 | 72716180 | chr5 | 72732870 | 72732884 | chr5 | 72733093 | 72733185 |
| chr5 | 72740147 | 72740184 | chr5 | 72746680 | 72746683 | chr5 | 74061571 | 74061786 |
| chr5 | 74991793 | 74991908 | chr5 | 75377883 | 75378033 | chr5 | 75380163 | 75380193 |
| chr5 | 75380624 | 75380974 | chr5 | 76011285 | 76011337 | chr5 | 76012576 | 76012605 |
| chr5 | 76249270 | 76249670 | chr5 | 76249696 | 76249906 | chr5 | 76249945 | 76250150 |
| chr5 | 76250435 | 76250504 | chr5 | 76327468 | 76327697 | chr5 | 76506469 | 76506506 |
| chr5 | 76507035 | 76507114 | chr5 | 76923679 | 76924023 | chr5 | 76924087 | 76924299 |
| chr5 | 76924930 | 76924960 | chr5 | 76925561 | 76925690 | chr5 | 76928157 | 76928397 |
| chr5 | 76928688 | 76928906 | chr5 | 76932302 | 76932332 | chr5 | 76932542 | 76933265 |
| chr5 | 76934173 | 76934653 | chr5 | 76934677 | 76934870 | chr5 | 76936016 | 76936721 |
| chr5 | 76939436 | 76939774 | chr5 | 76940340 | 76940374 | chr5 | 76941201 | 76941326 |
| chr5 | 77140527 | 77140711 | chr5 | 77147563 | 77147649 | chr5 | 77147873 | 77148195 |
| chr5 | 77148498 | 77148712 | chr5 | 77268367 | 77269237 | chr5 | 77269264 | 77269309 |
| chr5 | 77655342 | 77655388 | chr5 | 78005726 | 78005913 | chr5 | 78039632 | 78039673 |
| chr5 | 78407651 | 78407840 | chr5 | 78408192 | 78408274 | chr5 | 78408298 | 78408461 |
| chr5 | 78910189 | 78910332 | chr5 | 79554097 | 79554169 | chr5 | 79563425 | 79563643 |
| chr5 | 79598681 | 79598836 | chr5 | 79783240 | 79783421 | chr5 | 79864898 | 79865078 |
| chr5 | 79866100 | 79866414 | chr5 | 79947584 | 79947707 | chr5 | 80255816 | 80256074 |
| chr5 | 80689543 | 80689735 | chr5 | 80690118 | 80690239 | chr5 | 82168369 | 82168480 |
| chr5 | 82767429 | 82767793 | chr5 | 82768892 | 82769061 | chr5 | 83679195 | 83679225 |

TABLE 12-continued

Pan Cancer #2

| chr | start | end | chr | start | end | chr | start | end |
|---|---|---|---|---|---|---|---|---|
| chr5 | 83679681 | 83680340 | chr5 | 83680615 | 83680664 | chr5 | 83680694 | 83680708 |
| chr5 | 86414242 | 86414297 | chr5 | 87955460 | 87955664 | chr5 | 87956199 | 87956662 |
| chr5 | 87956680 | 87956964 | chr5 | 87962966 | 87963002 | chr5 | 87963390 | 87963511 |
| chr5 | 87967773 | 87968077 | chr5 | 87968486 | 87968685 | chr5 | 87968773 | 87968858 |
| chr5 | 87970193 | 87970872 | chr5 | 87974104 | 87974307 | chr5 | 87974868 | 87975023 |
| chr5 | 87976028 | 87976308 | chr5 | 87976525 | 87976559 | chr5 | 87979756 | 87979912 |
| chr5 | 87980142 | 87980250 | chr5 | 87980954 | 87981325 | chr5 | 87984532 | 87984657 |
| chr5 | 87985922 | 87985954 | chr5 | 87986210 | 87986281 | chr5 | 87986547 | 87986581 |
| chr5 | 87988516 | 87988584 | chr5 | 87990408 | 87990452 | chr5 | 88185470 | 88186001 |
| chr5 | 89854856 | 89854902 | chr5 | 94889396 | 94889434 | chr5 | 94955681 | 94955919 |
| chr5 | 94956935 | 94957000 | chr5 | 94982042 | 94982225 | chr5 | 95767894 | 95768384 |
| chr5 | 95768920 | 95769093 | chr5 | 96114587 | 96114632 | chr5 | 100236682 | 100236757 |
| chr5 | 100238882 | 100239119 | chr5 | 100239135 | 100239151 | chr5 | 101631487 | 101631533 |
| chr5 | 101632295 | 101632573 | chr5 | 107005983 | 107006186 | chr5 | 111987744 | 111987818 |
| chr5 | 112042844 | 112042873 | chr5 | 112042904 | 112043289 | chr5 | 112073358 | 112073516 |
| chr5 | 112170808 | 112170837 | chr5 | 112175198 | 112175227 | chr5 | 112175640 | 112175669 |
| chr5 | 112258359 | 112258388 | chr5 | 112258634 | 112258663 | chr5 | 112340666 | 112340704 |
| chr5 | 112629427 | 112629674 | chr5 | 113391265 | 113392018 | chr5 | 113698567 | 113698583 |
| chr5 | 113698670 | 113698783 | chr5 | 113699008 | 113699119 | chr5 | 114515010 | 114515579 |
| chr5 | 114515611 | 114515671 | chr5 | 115151267 | 115151357 | chr5 | 115151650 | 115152384 |
| chr5 | 115152617 | 115152638 | chr5 | 115154758 | 115154825 | chr5 | 115176039 | 115176228 |
| chr5 | 115297192 | 115297292 | chr5 | 115297377 | 115297556 | chr5 | 115297928 | 115297985 |
| chr5 | 115298496 | 115298581 | chr5 | 115298985 | 115299041 | chr5 | 116143271 | 116143325 |
| chr5 | 119799931 | 119799986 | chr5 | 119801299 | 119801445 | chr5 | 120399966 | 120400129 |
| chr5 | 121413537 | 121413590 | chr5 | 122422240 | 122422292 | chr5 | 122422616 | 122422651 |
| chr5 | 122423328 | 122423376 | chr5 | 122425128 | 122425168 | chr5 | 122431118 | 122431378 |
| chr5 | 124128410 | 124128497 | chr5 | 126231644 | 126231674 | chr5 | 126245097 | 126245133 |
| chr5 | 126626283 | 126626738 | chr5 | 127088743 | 127088773 | chr5 | 127872942 | 127872990 |
| chr5 | 127873553 | 127873710 | chr5 | 127874447 | 127874477 | chr5 | 127874706 | 127874839 |
| chr5 | 128300680 | 128300694 | chr5 | 128300713 | 128300794 | chr5 | 128796081 | 128796244 |
| chr5 | 128796867 | 128796985 | chr5 | 128797344 | 128797386 | chr5 | 129240068 | 129240101 |
| chr5 | 130153448 | 130153623 | chr5 | 131134159 | 131134203 | chr5 | 131992096 | 131992157 |
| chr5 | 132947486 | 132947836 | chr5 | 133820008 | 133820040 | chr5 | 133968996 | 133969192 |
| chr5 | 134364195 | 134364289 | chr5 | 134366718 | 134366788 | chr5 | 134367108 | 134367203 |
| chr5 | 134374447 | 134374505 | chr5 | 134374792 | 134375210 | chr5 | 134376222 | 134376375 |
| chr5 | 134376732 | 134376824 | chr5 | 134385952 | 134386167 | chr5 | 134386185 | 134386383 |
| chr5 | 134582864 | 134582894 | chr5 | 134735622 | 134735651 | chr5 | 134825463 | 134825518 |
| chr5 | 134825913 | 134826006 | chr5 | 134870446 | 134870515 | chr5 | 134870780 | 134870926 |
| chr5 | 134871601 | 134872049 | chr5 | 134879478 | 134880022 | chr5 | 134880049 | 134880501 |
| chr5 | 134914627 | 134914748 | chr5 | 135265737 | 135265767 | chr5 | 135266114 | 135266128 |
| chr5 | 135266578 | 135266672 | chr5 | 135528201 | 135528233 | chr5 | 136834050 | 136834050 |
| chr5 | 136834290 | 136834506 | chr5 | 136834720 | 136834826 | chr5 | 137225092 | 137225297 |
| chr5 | 137404150 | 137404180 | chr5 | 137912037 | 137912148 | chr5 | 138196197 | 138196408 |
| chr5 | 138273817 | 138273854 | chr5 | 139045286 | 139045315 | chr5 | 139047990 | 139048162 |
| chr5 | 139056666 | 139056804 | chr5 | 139227773 | 139227909 | chr5 | 139454108 | 139454202 |
| chr5 | 139525728 | 139525758 | chr5 | 139779555 | 139779871 | chr5 | 140174798 | 140174839 |
| chr5 | 140187094 | 140187146 | chr5 | 140305978 | 140306050 | chr5 | 140306445 | 140306619 |
| chr5 | 140306675 | 140306733 | chr5 | 140346595 | 140346671 | chr5 | 140514891 | 140514921 |
| chr5 | 140604459 | 140604501 | chr5 | 140613926 | 140614014 | chr5 | 140614314 | 140614328 |
| chr5 | 140683631 | 140683772 | chr5 | 140777347 | 140777487 | chr5 | 140787623 | 140787637 |
| chr5 | 140797076 | 140797278 | chr5 | 140797328 | 140797342 | chr5 | 140800479 | 140800964 |
| chr5 | 140801035 | 140801246 | chr5 | 140855598 | 140856458 | chr5 | 140856547 | 140856622 |
| chr5 | 141031121 | 141031150 | chr5 | 141263035 | 141263142 | chr5 | 141931340 | 141931354 |
| chr5 | 141931425 | 141931539 | chr5 | 142784967 | 142785272 | chr5 | 145713645 | 145713896 |
| chr5 | 145717175 | 145717196 | chr5 | 145717249 | 145717437 | chr5 | 145718802 | 145719753 |
| chr5 | 145719835 | 145719925 | chr5 | 145720812 | 145720917 | chr5 | 145722116 | 145722466 |
| chr5 | 145722561 | 145723027 | chr5 | 145724502 | 145724698 | chr5 | 145725694 | 145725844 |
| chr5 | 146257332 | 146257602 | chr5 | 146889332 | 146889575 | chr5 | 147003444 | 147003536 |
| chr5 | 147326357 | 147326510 | chr5 | 149503827 | 149503856 | chr5 | 149682074 | 149682166 |
| chr5 | 150029147 | 150029245 | chr5 | 150051101 | 150051667 | chr5 | 150326159 | 150326188 |
| chr5 | 150400123 | 150400203 | chr5 | 151066442 | 151066474 | chr5 | 151304371 | 151304401 |
| chr5 | 153852664 | 153852792 | chr5 | 153853420 | 153853478 | chr5 | 153854330 | 153854360 |
| chr5 | 153855175 | 153855264 | chr5 | 153855658 | 153855839 | chr5 | 153856149 | 153856396 |
| chr5 | 153856936 | 153856996 | chr5 | 153857379 | 153857429 | chr5 | 153858319 | 153858599 |
| chr5 | 153859676 | 153859708 | chr5 | 153862037 | 153862179 | chr5 | 153862219 | 153862577 |
| chr5 | 153863421 | 153863451 | chr5 | 154030048 | 154030160 | chr5 | 154061801 | 154061894 |
| chr5 | 154209926 | 154209987 | chr5 | 154318148 | 154318329 | chr5 | 155107794 | 155107848 |
| chr5 | 155108161 | 155108267 | chr5 | 155108356 | 155108526 | chr5 | 155108733 | 155108763 |
| chr5 | 156485385 | 156485415 | chr5 | 156558444 | 156558689 | chr5 | 156655170 | 156655200 |
| chr5 | 156874257 | 156874308 | chr5 | 157001739 | 157001843 | chr5 | 157078419 | 157078449 |
| chr5 | 157098362 | 157098619 | chr5 | 157673799 | 157673964 | chr5 | 158478513 | 158478704 |
| chr5 | 158524692 | 158524748 | chr5 | 158524865 | 158524925 | chr5 | 158527443 | 158528069 |
| chr5 | 158612981 | 158613074 | chr5 | 159399095 | 159399099 | chr5 | 159437197 | 159437235 |
| chr5 | 160975724 | 160975754 | chr5 | 161274310 | 161274554 | chr5 | 166865449 | 166865616 |
| chr5 | 167956177 | 167956266 | chr5 | 167956414 | 167956595 | chr5 | 168233396 | 168233482 |
| chr5 | 168727924 | 168727927 | chr5 | 169064327 | 169064805 | chr5 | 169366082 | 169366201 |

TABLE 12-continued

Pan Cancer #2

| chr | start | end | chr | start | end | chr | start | end |
|---|---|---|---|---|---|---|---|---|
| chr5 | 169532927 | 169533012 | chr5 | 170108287 | 170108372 | chr5 | 170735154 | 170735206 |
| chr5 | 170735731 | 170735788 | chr5 | 170736116 | 170736163 | chr5 | 170736716 | 170736830 |
| chr5 | 170737282 | 170737479 | chr5 | 170737741 | 170737863 | chr5 | 170737936 | 170738689 |
| chr5 | 170738824 | 170739481 | chr5 | 170739823 | 170740027 | chr5 | 170740461 | 170740477 |
| chr5 | 170740575 | 170741240 | chr5 | 170741465 | 170742275 | chr5 | 170742387 | 170742599 |
| chr5 | 170742673 | 170743479 | chr5 | 170743647 | 170744128 | chr5 | 170744375 | 170744562 |
| chr5 | 170745389 | 170745480 | chr5 | 171352123 | 171352153 | chr5 | 172354043 | 172354118 |
| chr5 | 172485539 | 172485586 | chr5 | 172655879 | 172656215 | chr5 | 172659225 | 172659290 |
| chr5 | 172659496 | 172659655 | chr5 | 172659855 | 172660025 | chr5 | 172660142 | 172660218 |
| chr5 | 172660719 | 172661000 | chr5 | 172661127 | 172661684 | chr5 | 172664226 | 172664487 |
| chr5 | 172665590 | 172665812 | chr5 | 172670983 | 172671018 | chr5 | 172671345 | 172671481 |
| chr5 | 172671640 | 172671968 | chr5 | 172672477 | 172672663 | chr5 | 172754589 | 172754621 |
| chr5 | 172754832 | 172754931 | chr5 | 172755470 | 172755562 | chr5 | 172755595 | 172755663 |
| chr5 | 172757048 | 172757111 | chr5 | 174115388 | 174115861 | chr5 | 174147523 | 174147596 |
| chr5 | 174150415 | 174150445 | chr5 | 174159300 | 174159588 | chr5 | 174162874 | 174162904 |
| chr5 | 174220971 | 174221001 | chr5 | 174870738 | 174870786 | chr5 | 174871174 | 174871497 |
| chr5 | 174921456 | 174921629 | chr5 | 175085147 | 175085209 | chr5 | 175085525 | 175085719 |
| chr5 | 175223671 | 175223709 | chr5 | 175298549 | 175298883 | chr5 | 175299294 | 175299396 |
| chr5 | 175300351 | 175300381 | chr5 | 175621390 | 175621501 | chr5 | 175790961 | 175790991 |
| chr5 | 175792865 | 175792931 | chr5 | 175792998 | 175793063 | chr5 | 175831257 | 175831326 |
| chr5 | 175876388 | 175876504 | chr5 | 175971447 | 175971615 | chr5 | 175978889 | 175978976 |
| chr5 | 176024006 | 176024318 | chr5 | 176046363 | 176046554 | chr5 | 176107274 | 176107484 |
| chr5 | 176107518 | 176107586 | chr5 | 176236721 | 176236898 | chr5 | 176264805 | 176264915 |
| chr5 | 176295786 | 176295892 | chr5 | 176520166 | 176520195 | chr5 | 176522400 | 176522566 |
| chr5 | 176764100 | 176764169 | chr5 | 176827656 | 176827685 | chr5 | 177020093 | 177020153 |
| chr5 | 177031167 | 177031197 | chr5 | 177408292 | 177408443 | chr5 | 177411638 | 177412141 |
| chr5 | 177512244 | 177512377 | chr5 | 177556807 | 177557022 | chr5 | 177579824 | 177580065 |
| chr5 | 177644565 | 177644601 | chr5 | 177713376 | 177713468 | chr5 | 178004325 | 178004374 |
| chr5 | 178016682 | 178016983 | chr5 | 178017520 | 178017867 | chr5 | 178151333 | 178151363 |
| chr5 | 178368074 | 178368121 | chr5 | 178487107 | 178487303 | chr5 | 178487342 | 178487398 |
| chr5 | 178576356 | 178576499 | chr5 | 178655753 | 178655871 | chr5 | 178771314 | 178771630 |
| chr5 | 178771724 | 178771859 | chr5 | 178772205 | 178772272 | chr5 | 178772603 | 178772729 |
| chr5 | 178781548 | 178781577 | chr5 | 178955527 | 178955656 | chr5 | 178957637 | 178957944 |
| chr5 | 178969722 | 178969752 | chr5 | 178978946 | 178978976 | chr5 | 179060235 | 179060655 |
| chr5 | 179098595 | 179098633 | chr5 | 179214113 | 179214196 | chr5 | 179217377 | 179217447 |
| chr5 | 179270584 | 179270748 | chr5 | 179553207 | 179553237 | chr5 | 179780104 | 179780144 |
| chr5 | 179780706 | 179780985 | chr5 | 179867486 | 179867548 | chr5 | 180017118 | 180017198 |
| chr5 | 180017608 | 180017933 | chr5 | 180018485 | 180018498 | chr5 | 180030654 | 180030700 |
| chr5 | 180047440 | 180047606 | chr5 | 180075846 | 180075857 | chr5 | 180076054 | 180076317 |
| chr5 | 180076567 | 180076602 | chr5 | 180076804 | 180076996 | chr5 | 180101016 | 180101167 |
| chr5 | 180101252 | 180101332 | chr5 | 180326126 | 180326156 | chr5 | 180454232 | 180454334 |
| chr5 | 180527546 | 180527698 | chr5 | 180594851 | 180595002 | chr5 | 180600858 | 180601218 |
| chr5 | 180612346 | 180612376 | chr5 | 180629320 | 180629350 | chr5 | 180636016 | 180636205 |
| chr6 | 373148 | 373290 | chr6 | 391173 | 391899 | chr6 | 392410 | 392433 |
| chr6 | 392588 | 392958 | chr6 | 393125 | 393472 | chr6 | 711142 | 711293 |
| chr6 | 1312000 | 1312096 | chr6 | 1312595 | 1312708 | chr6 | 1314088 | 1314100 |
| chr6 | 1378222 | 1378475 | chr6 | 1379584 | 1379614 | chr6 | 1379909 | 1379952 |
| chr6 | 1383677 | 1383708 | chr6 | 1383860 | 1384179 | chr6 | 1384626 | 1384644 |
| chr6 | 1385118 | 1385170 | chr6 | 1386071 | 1386112 | chr6 | 1389124 | 1389262 |
| chr6 | 1390241 | 1390405 | chr6 | 1390424 | 1390758 | chr6 | 1390956 | 1391035 |
| chr6 | 1391318 | 1391379 | chr6 | 1524199 | 1524283 | chr6 | 1605387 | 1605454 |
| chr6 | 1620672 | 1620701 | chr6 | 1624977 | 1625818 | chr6 | 2986688 | 2986718 |
| chr6 | 3053299 | 3053386 | chr6 | 3229029 | 3229059 | chr6 | 3229423 | 3229510 |
| chr6 | 3232010 | 3232260 | chr6 | 3247675 | 3247704 | chr6 | 3285229 | 3285513 |
| chr6 | 3405645 | 3405713 | chr6 | 4775062 | 4775222 | chr6 | 4836002 | 4836458 |
| chr6 | 4951247 | 4951390 | chr6 | 5359500 | 5359539 | chr6 | 5783325 | 5783496 |
| chr6 | 5996952 | 5996989 | chr6 | 5997802 | 5997832 | chr6 | 6003287 | 6003528 |
| chr6 | 6004350 | 6004743 | chr6 | 6004837 | 6005417 | chr6 | 6006374 | 6006419 |
| chr6 | 6006674 | 6006883 | chr6 | 6007593 | 6008277 | chr6 | 6367086 | 6367271 |
| chr6 | 6753803 | 6753839 | chr6 | 7726334 | 7726363 | chr6 | 7726630 | 7726659 |
| chr6 | 7726952 | 7726981 | chr6 | 7727699 | 7727768 | chr6 | 7728087 | 7728142 |
| chr6 | 7728849 | 7728941 | chr6 | 7731054 | 7731083 | chr6 | 7892314 | 7892412 |
| chr6 | 8014600 | 8014772 | chr6 | 10381507 | 10381592 | chr6 | 10381695 | 10381968 |
| chr6 | 10382722 | 10383049 | chr6 | 10383739 | 10383774 | chr6 | 10384950 | 10384974 |
| chr6 | 10385280 | 10385939 | chr6 | 10386210 | 10386273 | chr6 | 10390023 | 10391187 |
| chr6 | 10410518 | 10410578 | chr6 | 10411356 | 10411510 | chr6 | 10415113 | 10415215 |
| chr6 | 10415559 | 10415713 | chr6 | 10416118 | 10416351 | chr6 | 10417158 | 10417529 |
| chr6 | 10419086 | 10419439 | chr6 | 10419477 | 10419506 | chr6 | 10419744 | 10419941 |
| chr6 | 10421053 | 10421451 | chr6 | 10421549 | 10422635 | chr6 | 10423613 | 10423704 |
| chr6 | 10425630 | 10425789 | chr6 | 10425839 | 10426884 | chr6 | 10542836 | 10542977 |
| chr6 | 10734917 | 10735045 | chr6 | 10881835 | 10882057 | chr6 | 10882321 | 10882350 |
| chr6 | 10883008 | 10883022 | chr6 | 10883444 | 10883474 | chr6 | 10887078 | 10887686 |
| chr6 | 11044062 | 11044572 | chr6 | 12288517 | 12288681 | chr6 | 12749899 | 12749940 |
| chr6 | 13797690 | 13797736 | chr6 | 14687918 | 14688084 | chr6 | 14986483 | 14986522 |
| chr6 | 15513780 | 15513981 | chr6 | 16197030 | 16197112 | chr6 | 16729595 | 16729624 |
| chr6 | 17281417 | 17281534 | chr6 | 17666654 | 17666707 | chr6 | 17750276 | 17750306 |

TABLE 12-continued

Pan Cancer #2

| chr | start | end | chr | start | end | chr | start | end |
|---|---|---|---|---|---|---|---|---|
| chr6 | 18035867 | 18036015 | chr6 | 19691638 | 19691841 | chr6 | 19692143 | 19692318 |
| chr6 | 19837064 | 19837140 | chr6 | 19892448 | 19892627 | chr6 | 21664719 | 21664749 |
| chr6 | 21665004 | 21665043 | chr6 | 22172209 | 22172305 | chr6 | 22172536 | 22172566 |
| chr6 | 24358291 | 24358320 | chr6 | 24360074 | 24360170 | chr6 | 24494679 | 24494766 |
| chr6 | 24647342 | 24647599 | chr6 | 24662439 | 24662469 | chr6 | 26034268 | 26034311 |
| chr6 | 26184095 | 26184391 | chr6 | 26188696 | 26189393 | chr6 | 26189859 | 26189991 |
| chr6 | 26199137 | 26199167 | chr6 | 26199686 | 26199716 | chr6 | 26214514 | 26214648 |
| chr6 | 26235223 | 26235623 | chr6 | 26240504 | 26241118 | chr6 | 26250468 | 26250826 |
| chr6 | 26251054 | 26251182 | chr6 | 26251816 | 26252098 | chr6 | 26252141 | 26252151 |
| chr6 | 26254617 | 26254647 | chr6 | 26260956 | 26260986 | chr6 | 26271406 | 26271762 |
| chr6 | 26271971 | 26272001 | chr6 | 26272512 | 26272617 | chr6 | 26273400 | 26273418 |
| chr6 | 26284811 | 26284898 | chr6 | 26327806 | 26327982 | chr6 | 26328294 | 26328457 |
| chr6 | 26332178 | 26332218 | chr6 | 26501950 | 26502209 | chr6 | 26550994 | 26551034 |
| chr6 | 26577158 | 26577475 | chr6 | 26987967 | 26988166 | chr6 | 27059783 | 27059848 |
| chr6 | 27064682 | 27065198 | chr6 | 27173528 | 27173546 | chr6 | 27173633 | 27174181 |
| chr6 | 27182869 | 27182899 | chr6 | 27203269 | 27203336 | chr6 | 27205300 | 27205441 |
| chr6 | 27205671 | 27205836 | chr6 | 27205914 | 27206040 | chr6 | 27218951 | 27218980 |
| chr6 | 27228180 | 27228186 | chr6 | 27228290 | 27228395 | chr6 | 27235876 | 27235905 |
| chr6 | 27247636 | 27247724 | chr6 | 27256097 | 27256173 | chr6 | 27256383 | 27256420 |
| chr6 | 27264332 | 27264364 | chr6 | 27279845 | 27280012 | chr6 | 27441812 | 27441842 |
| chr6 | 27463029 | 27463687 | chr6 | 27512761 | 27512883 | chr6 | 27512995 | 27513487 |
| chr6 | 27533822 | 27534341 | chr6 | 27559809 | 27560075 | chr6 | 27573171 | 27573392 |
| chr6 | 27598738 | 27598860 | chr6 | 27599159 | 27599341 | chr6 | 27635265 | 27635434 |
| chr6 | 27647712 | 27647735 | chr6 | 27647891 | 27647896 | chr6 | 27648912 | 27649134 |
| chr6 | 27783039 | 27783052 | chr6 | 27799464 | 27799581 | chr6 | 27834676 | 27834835 |
| chr6 | 27835047 | 27835096 | chr6 | 27835378 | 27835417 | chr6 | 27839726 | 27840082 |
| chr6 | 27840543 | 27840617 | chr6 | 27841104 | 27841136 | chr6 | 27858515 | 27858637 |
| chr6 | 28175189 | 28176212 | chr6 | 28227076 | 28227141 | chr6 | 28303562 | 28303607 |
| chr6 | 28303815 | 28304263 | chr6 | 28367309 | 28367346 | chr6 | 28367491 | 28367774 |
| chr6 | 28410976 | 28411087 | chr6 | 28411152 | 28411353 | chr6 | 28414977 | 28414991 |
| chr6 | 28457608 | 28457638 | chr6 | 28457870 | 28458158 | chr6 | 28956323 | 28956511 |
| chr6 | 28956660 | 28956719 | chr6 | 30095233 | 30095262 | chr6 | 30095418 | 30095570 |
| chr6 | 30130804 | 30130895 | chr6 | 30644680 | 30644798 | chr6 | 32374147 | 32374176 |
| chr6 | 32374739 | 32374768 | chr6 | 32376051 | 32376080 | chr6 | 33161275 | 33161342 |
| chr6 | 33632930 | 33633000 | chr6 | 33636388 | 33636418 | chr6 | 33955505 | 33955731 |
| chr6 | 34113872 | 34113957 | chr6 | 34170970 | 34171061 | chr6 | 34219930 | 34219972 |
| chr6 | 34396431 | 34396542 | chr6 | 34535802 | 34535832 | chr6 | 34714803 | 34714896 |
| chr6 | 34724047 | 34724228 | chr6 | 35150041 | 35150080 | chr6 | 35182493 | 35182522 |
| chr6 | 35470285 | 35470399 | chr6 | 35479613 | 35479642 | chr6 | 35992428 | 35992458 |
| chr6 | 36165662 | 36165692 | chr6 | 36178031 | 36178301 | chr6 | 36252984 | 36253171 |
| chr6 | 36313883 | 36313913 | chr6 | 36392273 | 36392323 | chr6 | 36406316 | 36406370 |
| chr6 | 36808323 | 36808441 | chr6 | 37024559 | 37024589 | chr6 | 37392127 | 37392189 |
| chr6 | 37545401 | 37545495 | chr6 | 37664140 | 37664187 | chr6 | 37673320 | 37673611 |
| chr6 | 37776410 | 37776440 | chr6 | 37776703 | 37776735 | chr6 | 38683212 | 38683235 |
| chr6 | 39281088 | 39281133 | chr6 | 39281824 | 39281875 | chr6 | 39329863 | 39329892 |
| chr6 | 39508464 | 39508493 | chr6 | 39760401 | 39760661 | chr6 | 40554653 | 40554699 |
| chr6 | 41273881 | 41273942 | chr6 | 41337072 | 41337128 | chr6 | 41339263 | 41339558 |
| chr6 | 41339602 | 41339838 | chr6 | 41340902 | 41341182 | chr6 | 41341501 | 41341549 |
| chr6 | 41342243 | 41342275 | chr6 | 41342807 | 41342837 | chr6 | 41605937 | 41605951 |
| chr6 | 41606038 | 41606356 | chr6 | 41606528 | 41606542 | chr6 | 41773520 | 41773903 |
| chr6 | 41774459 | 41774576 | chr6 | 42062143 | 42062346 | chr6 | 42090977 | 42091027 |
| chr6 | 42111015 | 42111051 | chr6 | 42711893 | 42711923 | chr6 | 42738966 | 42739049 |
| chr6 | 42773440 | 42773622 | chr6 | 42846662 | 42846705 | chr6 | 42879554 | 42879568 |
| chr6 | 42879622 | 42879718 | chr6 | 42928321 | 42928454 | chr6 | 42990166 | 42990485 |
| chr6 | 43119019 | 43119580 | chr6 | 43211193 | 43211311 | chr6 | 43424297 | 43424470 |
| chr6 | 43425152 | 43425207 | chr6 | 43425479 | 43425509 | chr6 | 43478676 | 43478745 |
| chr6 | 43612825 | 43612898 | chr6 | 43613053 | 43613067 | chr6 | 43639548 | 43639710 |
| chr6 | 43748463 | 43748616 | chr6 | 44240914 | 44241108 | chr6 | 44695763 | 44695795 |
| chr6 | 45388716 | 45388775 | chr6 | 46702982 | 46703123 | chr6 | 46703350 | 46703436 |
| chr6 | 47473194 | 47473287 | chr6 | 47590439 | 47590604 | chr6 | 49590555 | 49590786 |
| chr6 | 49765146 | 49765202 | chr6 | 50674372 | 50674750 | chr6 | 50681699 | 50681942 |
| chr6 | 50682319 | 50682338 | chr6 | 50682659 | 50682683 | chr6 | 50682712 | 50682940 |
| chr6 | 50682992 | 50683227 | chr6 | 50684939 | 50684969 | chr6 | 50689913 | 50690039 |
| chr6 | 50691065 | 50691095 | chr6 | 50692083 | 50692212 | chr6 | 50692300 | 50692481 |
| chr6 | 50787216 | 50787876 | chr6 | 50787950 | 50788352 | chr6 | 50789374 | 50789404 |
| chr6 | 50791187 | 50791494 | chr6 | 50791551 | 50791632 | chr6 | 50793335 | 50793404 |
| chr6 | 50793728 | 50793882 | chr6 | 50794531 | 50794693 | chr6 | 50803834 | 50803867 |
| chr6 | 50804131 | 50804368 | chr6 | 50808681 | 50808854 | chr6 | 50810551 | 50810713 |
| chr6 | 50811062 | 50811488 | chr6 | 50813258 | 50813939 | chr6 | 50814569 | 50814599 |
| chr6 | 50817023 | 50817229 | chr6 | 50817905 | 50817935 | chr6 | 50818449 | 50818706 |
| chr6 | 50818920 | 50819000 | chr6 | 52227752 | 52227781 | chr6 | 52228008 | 52228037 |
| chr6 | 52344375 | 52344405 | chr6 | 52763812 | 52763982 | chr6 | 52928742 | 52928776 |
| chr6 | 52929051 | 52929233 | chr6 | 53052723 | 53052859 | chr6 | 53212491 | 53213970 |
| chr6 | 55443691 | 55443946 | chr6 | 56112262 | 56112386 | chr6 | 56716390 | 56716410 |
| chr6 | 56818656 | 56818937 | chr6 | 56819217 | 56819637 | chr6 | 56819897 | 56819926 |
| chr6 | 57694587 | 57694617 | chr6 | 58147447 | 58147480 | chr6 | 58147790 | 58147976 |

TABLE 12-continued

Pan Cancer #2

| chr | start | end | chr | start | end | chr | start | end |
|---|---|---|---|---|---|---|---|---|
| chr6 | 62995356 | 62995874 | chr6 | 62996078 | 62996146 | chr6 | 62996443 | 62996489 |
| chr6 | 70992137 | 70992162 | chr6 | 70992415 | 70992560 | chr6 | 70992830 | 70993015 |
| chr6 | 71090933 | 71090963 | chr6 | 71665638 | 71665723 | chr6 | 71666788 | 71666986 |
| chr6 | 72129789 | 72129829 | chr6 | 72130191 | 72130464 | chr6 | 72596120 | 72596315 |
| chr6 | 72596950 | 72596980 | chr6 | 73329784 | 73330126 | chr6 | 73330834 | 73331304 |
| chr6 | 73331515 | 73331850 | chr6 | 73331876 | 73333122 | chr6 | 73980676 | 73980722 |
| chr6 | 73982025 | 73982058 | chr6 | 74097722 | 74097763 | chr6 | 75995789 | 75995819 |
| chr6 | 76059561 | 76059787 | chr6 | 78172177 | 78172275 | chr6 | 78172323 | 78172572 |
| chr6 | 78173212 | 78173264 | chr6 | 78173696 | 78173725 | chr6 | 78173772 | 78173984 |
| chr6 | 78176458 | 78176820 | chr6 | 79620475 | 79620699 | chr6 | 80656930 | 80657180 |
| chr6 | 82463270 | 82463310 | chr6 | 82958615 | 82958917 | chr6 | 83546464 | 83546498 |
| chr6 | 84141298 | 84141412 | chr6 | 84417436 | 84417700 | chr6 | 84418261 | 84418281 |
| chr6 | 84418644 | 84418788 | chr6 | 84419157 | 84419415 | chr6 | 84562873 | 84563242 |
| chr6 | 84563489 | 84563542 | chr6 | 85050415 | 85050504 | chr6 | 85472407 | 85473703 |
| chr6 | 85473928 | 85474378 | chr6 | 85474594 | 85474736 | chr6 | 85476233 | 85476285 |
| chr6 | 85476998 | 85477028 | chr6 | 85478514 | 85478724 | chr6 | 85482530 | 85482822 |
| chr6 | 85483345 | 85483375 | chr6 | 85483760 | 85483931 | chr6 | 85484558 | 85484625 |
| chr6 | 85484717 | 85484920 | chr6 | 86302413 | 86302614 | chr6 | 87647114 | 87647143 |
| chr6 | 87862092 | 87862172 | chr6 | 88518712 | 88518742 | chr6 | 88876963 | 88877421 |
| chr6 | 89672213 | 89672376 | chr6 | 91320285 | 91320318 | chr6 | 91320949 | 91321295 |
| chr6 | 94126973 | 94127064 | chr6 | 94127455 | 94127544 | chr6 | 94128365 | 94128399 |
| chr6 | 94129219 | 94129257 | chr6 | 94129509 | 94129575 | chr6 | 96464100 | 96464204 |
| chr6 | 97412429 | 97412529 | chr6 | 97930083 | 97930113 | chr6 | 99271926 | 99272810 |
| chr6 | 99273369 | 99273410 | chr6 | 99277180 | 99277330 | chr6 | 99279556 | 99279612 |
| chr6 | 99280557 | 99280744 | chr6 | 99281014 | 99281036 | chr6 | 99281068 | 99281385 |
| chr6 | 99283512 | 99283582 | chr6 | 99290360 | 99290398 | chr6 | 99291264 | 99291341 |
| chr6 | 99292252 | 99292417 | chr6 | 99295726 | 99295863 | chr6 | 99296062 | 99296364 |
| chr6 | 99296408 | 99296467 | chr6 | 99396456 | 99396609 | chr6 | 99842067 | 99842258 |
| chr6 | 99842336 | 99842382 | chr6 | 100038682 | 100038706 | chr6 | 100038786 | 100038964 |
| chr6 | 100039275 | 100039289 | chr6 | 100050754 | 100050810 | chr6 | 100050859 | 100051108 |
| chr6 | 100051360 | 100051507 | chr6 | 100051772 | 100051971 | chr6 | 100053221 | 100053511 |
| chr6 | 100054866 | 100054917 | chr6 | 100061022 | 100061076 | chr6 | 100061311 | 100061419 |
| chr6 | 100062178 | 100062586 | chr6 | 100062944 | 100063068 | chr6 | 100135425 | 100135583 |
| chr6 | 100441498 | 100441737 | chr6 | 100441762 | 100441966 | chr6 | 100903384 | 100903404 |
| chr6 | 100903561 | 100903631 | chr6 | 100904214 | 100904275 | chr6 | 100905969 | 100906016 |
| chr6 | 100911686 | 100911723 | chr6 | 100912070 | 100912119 | chr6 | 100912421 | 100912445 |
| chr6 | 100912466 | 100912480 | chr6 | 100912919 | 100913050 | chr6 | 100915101 | 100915205 |
| chr6 | 101840708 | 101840820 | chr6 | 101846782 | 101846789 | chr6 | 101847185 | 101847215 |
| chr6 | 101850147 | 101850275 | chr6 | 105388679 | 105388708 | chr6 | 105389510 | 105389710 |
| chr6 | 105400913 | 105401007 | chr6 | 105401620 | 105401874 | chr6 | 105404574 | 105404674 |
| chr6 | 105405656 | 105405772 | chr6 | 105406098 | 105406128 | chr6 | 105584264 | 105584319 |
| chr6 | 105584367 | 105585554 | chr6 | 105821423 | 105821453 | chr6 | 106429049 | 106429475 |
| chr6 | 106429590 | 106429624 | chr6 | 106434339 | 106434368 | chr6 | 106441869 | 106442979 |
| chr6 | 106731509 | 106731597 | chr6 | 106960908 | 106961023 | chr6 | 107075651 | 107075704 |
| chr6 | 107562769 | 107562859 | chr6 | 108181556 | 108181721 | chr6 | 108280292 | 108280352 |
| chr6 | 108435075 | 108435263 | chr6 | 108436072 | 108436526 | chr6 | 108438261 | 108438577 |
| chr6 | 108440091 | 108440644 | chr6 | 108440745 | 108440961 | chr6 | 108479290 | 108479665 |
| chr6 | 108484909 | 108485406 | chr6 | 108485665 | 108485905 | chr6 | 108486158 | 108486394 |
| chr6 | 108487724 | 108488416 | chr6 | 108489662 | 108489808 | chr6 | 108490067 | 108490245 |
| chr6 | 108490297 | 108490514 | chr6 | 108490538 | 108490633 | chr6 | 108490978 | 108491000 |
| chr6 | 108491108 | 108491423 | chr6 | 108492270 | 108492451 | chr6 | 108495681 | 108495817 |
| chr6 | 108495916 | 108495951 | chr6 | 108496208 | 108496649 | chr6 | 108497494 | 108497796 |
| chr6 | 108497827 | 108497881 | chr6 | 109057882 | 109057928 | chr6 | 109058799 | 109058861 |
| chr6 | 110437721 | 110437751 | chr6 | 110679123 | 110679414 | chr6 | 110797678 | 110797708 |
| chr6 | 110798007 | 110798036 | chr6 | 110848558 | 110848682 | chr6 | 113852508 | 113852634 |
| chr6 | 116783448 | 116783493 | chr6 | 117000853 | 117001032 | chr6 | 117086249 | 117086639 |
| chr6 | 117585967 | 117586004 | chr6 | 117586847 | 117587169 | chr6 | 117587480 | 117587577 |
| chr6 | 117591161 | 117591191 | chr6 | 117591411 | 117591596 | chr6 | 117591684 | 117591743 |
| chr6 | 118228102 | 118228151 | chr6 | 118228747 | 118228828 | chr6 | 118229154 | 118229383 |
| chr6 | 118229626 | 118229818 | chr6 | 118241228 | 118241308 | chr6 | 118241395 | 118241500 |
| chr6 | 119254629 | 119254678 | chr6 | 119483052 | 119483082 | chr6 | 121758672 | 121758994 |
| chr6 | 121797231 | 121797265 | chr6 | 123317073 | 123317589 | chr6 | 123317797 | 123317833 |
| chr6 | 124124432 | 124124466 | chr6 | 124124860 | 124125016 | chr6 | 125284131 | 125284175 |
| chr6 | 126068092 | 126068178 | chr6 | 127439379 | 127439453 | chr6 | 127439985 | 127440127 |
| chr6 | 127440331 | 127440962 | chr6 | 127441031 | 127441123 | chr6 | 127441554 | 127441762 |
| chr6 | 127442021 | 127442070 | chr6 | 127442090 | 127442104 | chr6 | 127840501 | 127840681 |
| chr6 | 129204459 | 129204524 | chr6 | 130686534 | 130687057 | chr6 | 131602584 | 131602694 |
| chr6 | 132722078 | 132722141 | chr6 | 132722158 | 132722196 | chr6 | 133561740 | 133562070 |
| chr6 | 133562374 | 133562436 | chr6 | 133562675 | 133563058 | chr6 | 133563327 | 133563918 |
| chr6 | 134067194 | 134067471 | chr6 | 134176232 | 134176299 | chr6 | 134176549 | 134176579 |
| chr6 | 134210528 | 134211018 | chr6 | 134211112 | 134211367 | chr6 | 134213944 | 134213987 |
| chr6 | 134214077 | 134214364 | chr6 | 134589500 | 134589767 | chr6 | 134638950 | 134639003 |
| chr6 | 137241928 | 137242205 | chr6 | 137243208 | 137243410 | chr6 | 137244114 | 137244148 |
| chr6 | 137244236 | 137244465 | chr6 | 137311158 | 137311380 | chr6 | 137366354 | 137366383 |
| chr6 | 137809141 | 137809365 | chr6 | 137809446 | 137809916 | chr6 | 137810033 | 137811088 |
| chr6 | 137813787 | 137813895 | chr6 | 137814604 | 137814618 | chr6 | 137814654 | 137814763 |

TABLE 12-continued

Pan Cancer #2

| chr | start | end | chr | start | end | chr | start | end |
|---|---|---|---|---|---|---|---|---|
| chr6 | 137815008 | 137815170 | chr6 | 137815225 | 137815662 | chr6 | 137816472 | 137817351 |
| chr6 | 137818505 | 137818598 | chr6 | 137818619 | 137819368 | chr6 | 146755567 | 146755649 |
| chr6 | 149868348 | 149868387 | chr6 | 150183760 | 150183874 | chr6 | 150284552 | 150284581 |
| chr6 | 150285056 | 150285368 | chr6 | 150285545 | 150285885 | chr6 | 150286100 | 150286639 |
| chr6 | 150358970 | 150359192 | chr6 | 151561016 | 151561340 | chr6 | 151561369 | 151561857 |
| chr6 | 151562066 | 151562563 | chr6 | 151650396 | 151650453 | chr6 | 151815055 | 151815089 |
| chr6 | 152419908 | 152419940 | chr6 | 152623015 | 152623493 | chr6 | 152957895 | 152958076 |
| chr6 | 153451236 | 153451500 | chr6 | 153451890 | 153451968 | chr6 | 153452232 | 153452320 |
| chr6 | 153452713 | 153452746 | chr6 | 154360650 | 154360746 | chr6 | 154970558 | 154970676 |
| chr6 | 155316257 | 155316265 | chr6 | 155569208 | 155569305 | chr6 | 157037549 | 157037677 |
| chr6 | 157266063 | 157266109 | chr6 | 157502438 | 157502561 | chr6 | 157506082 | 157506112 |
| chr6 | 157556764 | 157557296 | chr6 | 157637455 | 157637500 | chr6 | 159211558 | 159211701 |
| chr6 | 159228187 | 159228217 | chr6 | 159290823 | 159290852 | chr6 | 159419589 | 159419717 |
| chr6 | 159590048 | 159590086 | chr6 | 159590155 | 159590761 | chr6 | 159590972 | 159590986 |
| chr6 | 159654923 | 159655003 | chr6 | 161100361 | 161100390 | chr6 | 161188513 | 161188543 |
| chr6 | 161352101 | 161352135 | chr6 | 161645992 | 161646255 | chr6 | 161780056 | 161780139 |
| chr6 | 163602842 | 163602872 | chr6 | 163834314 | 163834382 | chr6 | 163834406 | 163834532 |
| chr6 | 163834857 | 163834901 | chr6 | 163836568 | 163836900 | chr6 | 164114396 | 164114524 |
| chr6 | 164179636 | 164179668 | chr6 | 164183602 | 164183632 | chr6 | 164196971 | 164197003 |
| chr6 | 164215532 | 164215633 | chr6 | 164228294 | 164228363 | chr6 | 164246015 | 164246143 |
| chr6 | 164283254 | 164283377 | chr6 | 164314289 | 164314443 | chr6 | 164322666 | 164322775 |
| chr6 | 166074119 | 166074412 | chr6 | 166076788 | 166077021 | chr6 | 166077378 | 166077632 |
| chr6 | 166267582 | 166267891 | chr6 | 166401254 | 166401307 | chr6 | 166402240 | 166402546 |
| chr6 | 166421911 | 166422185 | chr6 | 166579723 | 166580144 | chr6 | 166580344 | 166582797 |
| chr6 | 166944367 | 166944403 | chr6 | 167202601 | 167202801 | chr6 | 167835129 | 167835171 |
| chr6 | 168719983 | 168720019 | chr6 | 168842847 | 168842944 | chr6 | 168858122 | 168858296 |
| chr6 | 168972472 | 168972502 | chr6 | 169002054 | 169002084 | chr6 | 169653638 | 169653668 |
| chr6 | 170047467 | 170047499 | chr6 | 170240639 | 170240714 | chr6 | 170264728 | 170264761 |
| chr6 | 170475105 | 170475267 | chr6 | 170494286 | 170494315 | chr6 | 170894820 | 170894912 |
| chr7 | 68930 | 68960 | chr7 | 329805 | 329838 | chr7 | 369494 | 369536 |
| chr7 | 369844 | 369980 | chr7 | 389663 | 389693 | chr7 | 409826 | 409892 |
| chr7 | 427454 | 427484 | chr7 | 431386 | 431492 | chr7 | 497782 | 497934 |
| chr7 | 503811 | 503936 | chr7 | 551599 | 551697 | chr7 | 556928 | 556983 |
| chr7 | 564237 | 564271 | chr7 | 578922 | 579020 | chr7 | 579827 | 579857 |
| chr7 | 752120 | 752221 | chr7 | 842331 | 842414 | chr7 | 907656 | 907709 |
| chr7 | 915058 | 915087 | chr7 | 922050 | 922235 | chr7 | 927933 | 927986 |
| chr7 | 1016343 | 1016373 | chr7 | 1022224 | 1022254 | chr7 | 1030172 | 1030283 |
| chr7 | 1054579 | 1054696 | chr7 | 1086199 | 1086319 | chr7 | 1195270 | 1195364 |
| chr7 | 1263761 | 1263960 | chr7 | 1268318 | 1268366 | chr7 | 1269305 | 1269463 |
| chr7 | 1269553 | 1269808 | chr7 | 1270406 | 1270440 | chr7 | 1273167 | 1273330 |
| chr7 | 1274641 | 1274677 | chr7 | 1275579 | 1275680 | chr7 | 1277817 | 1277865 |
| chr7 | 1279099 | 1279129 | chr7 | 1279965 | 1279995 | chr7 | 1281131 | 1281232 |
| chr7 | 1281493 | 1281555 | chr7 | 1282042 | 1282150 | chr7 | 1282506 | 1282644 |
| chr7 | 1288582 | 1288753 | chr7 | 1308351 | 1308497 | chr7 | 1325810 | 1325882 |
| chr7 | 1416020 | 1416131 | chr7 | 1423632 | 1423677 | chr7 | 1459041 | 1459191 |
| chr7 | 1503417 | 1503596 | chr7 | 1547311 | 1547394 | chr7 | 1598639 | 1598697 |
| chr7 | 1607386 | 1607465 | chr7 | 1607971 | 1608001 | chr7 | 1611443 | 1611522 |
| chr7 | 1615390 | 1615444 | chr7 | 1627404 | 1627434 | chr7 | 1641774 | 1641923 |
| chr7 | 1681189 | 1681239 | chr7 | 1688977 | 1689146 | chr7 | 1690745 | 1690851 |
| chr7 | 1709138 | 1709235 | chr7 | 1709474 | 1709561 | chr7 | 1733166 | 1733378 |
| chr7 | 1735223 | 1735354 | chr7 | 1748514 | 1748766 | chr7 | 1775831 | 1775861 |
| chr7 | 1778875 | 1778914 | chr7 | 1783551 | 1783623 | chr7 | 1786514 | 1786899 |
| chr7 | 1787166 | 1787324 | chr7 | 1800882 | 1800912 | chr7 | 1970842 | 1970872 |
| chr7 | 2109874 | 2109904 | chr7 | 2163332 | 2163467 | chr7 | 2208670 | 2208800 |
| chr7 | 2232963 | 2233056 | chr7 | 2233292 | 2233414 | chr7 | 2238118 | 2238235 |
| chr7 | 2300787 | 2300899 | chr7 | 2361190 | 2361434 | chr7 | 2473452 | 2473605 |
| chr7 | 2565919 | 2566041 | chr7 | 2566600 | 2566630 | chr7 | 2595825 | 2595943 |
| chr7 | 2659340 | 2659370 | chr7 | 2720013 | 2720140 | chr7 | 2728068 | 2728165 |
| chr7 | 2979480 | 2979512 | chr7 | 2985518 | 2985547 | chr7 | 3033658 | 3033688 |
| chr7 | 3083331 | 3083352 | chr7 | 3283704 | 3283894 | chr7 | 3340444 | 3340473 |
| chr7 | 3341570 | 3341597 | chr7 | 4215324 | 4215384 | chr7 | 4657806 | 4657857 |
| chr7 | 4856984 | 4857048 | chr7 | 4922550 | 4922706 | chr7 | 4923328 | 4923397 |
| chr7 | 4998201 | 4998388 | chr7 | 5111528 | 5111669 | chr7 | 5262433 | 5262592 |
| chr7 | 5397777 | 5397938 | chr7 | 5603717 | 5603947 | chr7 | 5632939 | 5633100 |
| chr7 | 5648107 | 5648393 | chr7 | 6045612 | 6045641 | chr7 | 6059024 | 6059182 |
| chr7 | 6060590 | 6060634 | chr7 | 6099217 | 6099334 | chr7 | 6124585 | 6124714 |
| chr7 | 6188610 | 6189061 | chr7 | 6307943 | 6308066 | chr7 | 6414386 | 6414415 |
| chr7 | 6426878 | 6426907 | chr7 | 6443279 | 6443376 | chr7 | 6443826 | 6443856 |
| chr7 | 6484445 | 6484545 | chr7 | 6524573 | 6524744 | chr7 | 6524977 | 6525012 |
| chr7 | 6525477 | 6525606 | chr7 | 6543150 | 6543216 | chr7 | 6560235 | 6560345 |
| chr7 | 6566413 | 6566663 | chr7 | 6570959 | 6571130 | chr7 | 6576137 | 6576367 |
| chr7 | 6703555 | 6703869 | chr7 | 6703916 | 6703959 | chr7 | 7015498 | 7015673 |
| chr7 | 7605441 | 7605822 | chr7 | 8343630 | 8343724 | chr7 | 8391475 | 8391573 |
| chr7 | 8473070 | 8473455 | chr7 | 8473480 | 8473674 | chr7 | 8473956 | 8474241 |
| chr7 | 8474516 | 8474562 | chr7 | 8474814 | 8475057 | chr7 | 8480640 | 8481159 |
| chr7 | 8481642 | 8481833 | chr7 | 8482056 | 8482297 | chr7 | 8482670 | 8482824 |

TABLE 12-continued

Pan Cancer #2

| chr | start | end | chr | start | end | chr | start | end |
|---|---|---|---|---|---|---|---|---|
| chr7 | 8482885 | 8482921 | chr7 | 8483147 | 8483950 | chr7 | 12151440 | 12151472 |
| chr7 | 12151524 | 12151678 | chr7 | 12443317 | 12443403 | chr7 | 12443841 | 12443871 |
| chr7 | 12610339 | 12610476 | chr7 | 12751410 | 12751496 | chr7 | 12776779 | 12776811 |
| chr7 | 15725983 | 15726081 | chr7 | 15726634 | 15727077 | chr7 | 15727290 | 15727320 |
| chr7 | 19145808 | 19145893 | chr7 | 19146032 | 19146184 | chr7 | 19146238 | 19146249 |
| chr7 | 19146502 | 19146558 | chr7 | 19147122 | 19147798 | chr7 | 19152224 | 19152349 |
| chr7 | 19155791 | 19155820 | chr7 | 19156126 | 19156132 | chr7 | 19156304 | 19156745 |
| chr7 | 19157144 | 19157566 | chr7 | 19157634 | 19158015 | chr7 | 19158632 | 19158735 |
| chr7 | 19184058 | 19184255 | chr7 | 19813284 | 19813313 | chr7 | 20089670 | 20089700 |
| chr7 | 20183238 | 20183283 | chr7 | 20816252 | 20816447 | chr7 | 20817380 | 20817410 |
| chr7 | 20818130 | 20818362 | chr7 | 20823292 | 20823330 | chr7 | 20823383 | 20823432 |
| chr7 | 20823920 | 20824143 | chr7 | 20824476 | 20824819 | chr7 | 20824836 | 20824946 |
| chr7 | 20825379 | 20825559 | chr7 | 20826113 | 20826202 | chr7 | 20826884 | 20827199 |
| chr7 | 20830670 | 20830700 | chr7 | 20833167 | 20833322 | chr7 | 21403615 | 21403645 |
| chr7 | 21582593 | 21582640 | chr7 | 21582792 | 21582868 | chr7 | 21583263 | 21583277 |
| chr7 | 21583304 | 21583326 | chr7 | 22539833 | 22539909 | chr7 | 22589356 | 22589870 |
| chr7 | 22824965 | 22825009 | chr7 | 23253573 | 23253671 | chr7 | 23287253 | 23287350 |
| chr7 | 23287533 | 23287624 | chr7 | 23526549 | 23526698 | chr7 | 23578703 | 23578857 |
| chr7 | 24323763 | 24323939 | chr7 | 24580644 | 24580806 | chr7 | 24796478 | 24796567 |
| chr7 | 25132558 | 25132726 | chr7 | 25133492 | 25133650 | chr7 | 25165921 | 25166061 |
| chr7 | 25896521 | 25896864 | chr7 | 25897133 | 25897246 | chr7 | 26194906 | 26195024 |
| chr7 | 26283775 | 26283954 | chr7 | 27127863 | 27127898 | chr7 | 27135327 | 27135770 |
| chr7 | 27136013 | 27136790 | chr7 | 27138381 | 27138410 | chr7 | 27184015 | 27184190 |
| chr7 | 27190591 | 27191226 | chr7 | 27192061 | 27192098 | chr7 | 27195462 | 27195601 |
| chr7 | 27195867 | 27195892 | chr7 | 27196153 | 27196839 | chr7 | 27204487 | 27204769 |
| chr7 | 27205266 | 27205395 | chr7 | 27205678 | 27205789 | chr7 | 27208187 | 27208285 |
| chr7 | 27209462 | 27209582 | chr7 | 27212499 | 27212899 | chr7 | 27213189 | 27214261 |
| chr7 | 27217042 | 27217071 | chr7 | 27223114 | 27223151 | chr7 | 27223601 | 27223696 |
| chr7 | 27224069 | 27224609 | chr7 | 27225025 | 27225057 | chr7 | 27225447 | 27225483 |
| chr7 | 27227874 | 27227953 | chr7 | 27231476 | 27231505 | chr7 | 27231818 | 27231894 |
| chr7 | 27232289 | 27232962 | chr7 | 27233410 | 27233454 | chr7 | 27238887 | 27238917 |
| chr7 | 27239226 | 27239234 | chr7 | 27240230 | 27240381 | chr7 | 27244515 | 27244610 |
| chr7 | 27244798 | 27245310 | chr7 | 27245668 | 27245795 | chr7 | 27252380 | 27252410 |
| chr7 | 27260092 | 27260100 | chr7 | 27264875 | 27265325 | chr7 | 27265538 | 27265584 |
| chr7 | 27275513 | 27275543 | chr7 | 27279238 | 27279368 | chr7 | 27281329 | 27281360 |
| chr7 | 27282089 | 27283013 | chr7 | 27283351 | 27283627 | chr7 | 27285621 | 27285913 |
| chr7 | 27285980 | 27286098 | chr7 | 27286171 | 27286248 | chr7 | 27288946 | 27289100 |
| chr7 | 27289170 | 27289449 | chr7 | 27291315 | 27291851 | chr7 | 28110701 | 28110828 |
| chr7 | 28238339 | 28238444 | chr7 | 28449276 | 28449290 | chr7 | 28449659 | 28449781 |
| chr7 | 28449858 | 28450015 | chr7 | 28989065 | 28989159 | chr7 | 28995657 | 28995978 |
| chr7 | 28996457 | 28996495 | chr7 | 28996840 | 28996916 | chr7 | 28997136 | 28997625 |
| chr7 | 28998053 | 28998119 | chr7 | 30029702 | 30029822 | chr7 | 30029923 | 30029952 |
| chr7 | 30030307 | 30030337 | chr7 | 30721280 | 30721902 | chr7 | 30722290 | 30722375 |
| chr7 | 30857157 | 30857292 | chr7 | 31093003 | 31093133 | chr7 | 31232909 | 31232939 |
| chr7 | 31375965 | 31376135 | chr7 | 32110704 | 32110772 | chr7 | 32337807 | 32337837 |
| chr7 | 32338088 | 32338217 | chr7 | 32338284 | 32338410 | chr7 | 32338900 | 32338930 |
| chr7 | 32467461 | 32467655 | chr7 | 32467947 | 32468062 | chr7 | 32997124 | 32997454 |
| chr7 | 33167928 | 33168030 | chr7 | 33725803 | 33725938 | chr7 | 33943459 | 33943759 |
| chr7 | 35225809 | 35225833 | chr7 | 35226193 | 35226522 | chr7 | 35226557 | 35226765 |
| chr7 | 35292970 | 35293086 | chr7 | 35293183 | 35293293 | chr7 | 35294032 | 35294141 |
| chr7 | 35294502 | 35294536 | chr7 | 35295104 | 35295105 | chr7 | 35295908 | 35295944 |
| chr7 | 35296935 | 35297004 | chr7 | 35297138 | 35297353 | chr7 | 35297471 | 35298016 |
| chr7 | 35300951 | 35301008 | chr7 | 35301102 | 35301948 | chr7 | 37352957 | 37353062 |
| chr7 | 37487164 | 37487453 | chr7 | 37487756 | 37487826 | chr7 | 37488257 | 37488578 |
| chr7 | 37488920 | 37488992 | chr7 | 37907440 | 37907470 | chr7 | 37955878 | 37955979 |
| chr7 | 37956271 | 37956439 | chr7 | 37960301 | 37960335 | chr7 | 38588471 | 38588501 |
| chr7 | 38670357 | 38670663 | chr7 | 38670957 | 38671015 | chr7 | 39015542 | 39015981 |
| chr7 | 39649223 | 39649253 | chr7 | 39649444 | 39649457 | chr7 | 39872836 | 39873015 |
| chr7 | 41739663 | 41739879 | chr7 | 41982690 | 41982874 | chr7 | 42267647 | 42267677 |
| chr7 | 42276346 | 42276634 | chr7 | 42377468 | 42377497 | chr7 | 42533257 | 42533296 |
| chr7 | 43152109 | 43152207 | chr7 | 43152414 | 43152700 | chr7 | 43152957 | 43153199 |
| chr7 | 43153230 | 43153237 | chr7 | 43817999 | 43818119 | chr7 | 44083283 | 44083416 |
| chr7 | 44097690 | 44097876 | chr7 | 44151398 | 44151428 | chr7 | 44151795 | 44151933 |
| chr7 | 44163926 | 44163989 | chr7 | 44364838 | 44364903 | chr7 | 44740467 | 44740672 |
| chr7 | 44835037 | 44835384 | chr7 | 44912004 | 44912034 | chr7 | 45026942 | 45027045 |
| chr7 | 45038532 | 45038655 | chr7 | 45046874 | 45046982 | chr7 | 45525402 | 45525432 |
| chr7 | 45613785 | 45613813 | chr7 | 45613858 | 45613898 | chr7 | 45614341 | 45614474 |
| chr7 | 45614738 | 45614809 | chr7 | 45614929 | 45615020 | chr7 | 45615440 | 45615495 |
| chr7 | 45960743 | 45960794 | chr7 | 45961146 | 45961176 | chr7 | 45961508 | 45961576 |
| chr7 | 45961833 | 45961888 | chr7 | 47515359 | 47515405 | chr7 | 47704289 | 47704359 |
| chr7 | 49654508 | 49654538 | chr7 | 49812820 | 49813017 | chr7 | 49813810 | 49813994 |
| chr7 | 49814531 | 49814750 | chr7 | 49815117 | 49815249 | chr7 | 49815657 | 49815765 |
| chr7 | 49819674 | 49819703 | chr7 | 50294451 | 50294481 | chr7 | 50343263 | 50343401 |
| chr7 | 50343975 | 50343994 | chr7 | 50344226 | 50344491 | chr7 | 50365076 | 50365137 |
| chr7 | 50438618 | 50438648 | chr7 | 50441145 | 50441285 | chr7 | 50560588 | 50560637 |
| chr7 | 50860226 | 50861102 | chr7 | 51383754 | 51383790 | chr7 | 51384327 | 51384440 |

TABLE 12-continued

Pan Cancer #2

| chr | start | end | chr | start | end | chr | start | end |
|---|---|---|---|---|---|---|---|---|
| chr7 | 51384915 | 51384951 | chr7 | 52156231 | 52156261 | chr7 | 54609852 | 54609951 |
| chr7 | 54609992 | 54610153 | chr7 | 54612418 | 54612730 | chr7 | 55086473 | 55086601 |
| chr7 | 55086983 | 55087533 | chr7 | 55209976 | 55210005 | chr7 | 55211065 | 55211094 |
| chr7 | 55221729 | 55221836 | chr7 | 55223589 | 55223636 | chr7 | 55227993 | 55228022 |
| chr7 | 55233028 | 55233123 | chr7 | 55241663 | 55241737 | chr7 | 55242419 | 55242493 |
| chr7 | 55248975 | 55249085 | chr7 | 55259404 | 55259547 | chr7 | 55260469 | 55260498 |
| chr7 | 55268867 | 55268896 | chr7 | 55410019 | 55410126 | chr7 | 55506288 | 55506348 |
| chr7 | 56018123 | 56018286 | chr7 | 56031716 | 56031869 | chr7 | 63667431 | 63667460 |
| chr7 | 64330411 | 64330470 | chr7 | 64330734 | 64330833 | chr7 | 64349042 | 64349056 |
| chr7 | 64349331 | 64349470 | chr7 | 64700283 | 64700329 | chr7 | 64712364 | 64712510 |
| chr7 | 64713317 | 64713449 | chr7 | 64974382 | 64974422 | chr7 | 65037609 | 65037734 |
| chr7 | 65508995 | 65509043 | chr7 | 65510006 | 65510096 | chr7 | 65878743 | 65878793 |
| chr7 | 65879649 | 65879883 | chr7 | 65880359 | 65880405 | chr7 | 66204493 | 66204617 |
| chr7 | 66206923 | 66206953 | chr7 | 66214923 | 66214961 | chr7 | 67579765 | 67579911 |
| chr7 | 68204793 | 68204948 | chr7 | 69062519 | 69062635 | chr7 | 69064590 | 69064771 |
| chr7 | 69064834 | 69065045 | chr7 | 69352121 | 69352272 | chr7 | 69897780 | 69897827 |
| chr7 | 70596454 | 70596688 | chr7 | 70597406 | 70597451 | chr7 | 70597835 | 70597871 |
| chr7 | 70597991 | 70598123 | chr7 | 70598170 | 70598387 | chr7 | 70990312 | 70990342 |
| chr7 | 71217108 | 71217332 | chr7 | 71438424 | 71438454 | chr7 | 71603924 | 71604082 |
| chr7 | 71800676 | 71800756 | chr7 | 71800934 | 71801104 | chr7 | 71802410 | 71802522 |
| chr7 | 71802578 | 71802637 | chr7 | 71871203 | 71871245 | chr7 | 75511201 | 75511298 |
| chr7 | 76033151 | 76033289 | chr7 | 77129743 | 77129907 | chr7 | 77308664 | 77308899 |
| chr7 | 77309437 | 77309511 | chr7 | 77324362 | 77324593 | chr7 | 79081792 | 79081821 |
| chr7 | 79082023 | 79082218 | chr7 | 79083392 | 79083834 | chr7 | 80548257 | 80548403 |
| chr7 | 82072350 | 82072503 | chr7 | 82073495 | 82073533 | chr7 | 84815141 | 84815226 |
| chr7 | 84815744 | 84815954 | chr7 | 86273208 | 86273541 | chr7 | 86274258 | 86274457 |
| chr7 | 87104816 | 87105430 | chr7 | 87229537 | 87230433 | chr7 | 87257012 | 87257047 |
| chr7 | 87257931 | 87258054 | chr7 | 87563370 | 87563614 | chr7 | 87563829 | 87563890 |
| chr7 | 87706818 | 87706877 | chr7 | 87825098 | 87825137 | chr7 | 88387982 | 88388167 |
| chr7 | 88388540 | 88388660 | chr7 | 88388879 | 88388901 | chr7 | 88389047 | 88389356 |
| chr7 | 89747996 | 89748340 | chr7 | 89950183 | 89950810 | chr7 | 90226269 | 90226464 |
| chr7 | 90269263 | 90269563 | chr7 | 90797539 | 90797568 | chr7 | 90895012 | 90895097 |
| chr7 | 92466152 | 92466400 | chr7 | 92554253 | 92554452 | chr7 | 92689705 | 92689818 |
| chr7 | 93203708 | 93203756 | chr7 | 93204332 | 93204492 | chr7 | 93220696 | 93220826 |
| chr7 | 93519351 | 93519765 | chr7 | 93519855 | 93520137 | chr7 | 93551323 | 93551425 |
| chr7 | 94138158 | 94138315 | chr7 | 94284302 | 94284873 | chr7 | 96619560 | 96619603 |
| chr7 | 96621715 | 96621811 | chr7 | 96622107 | 96622349 | chr7 | 96622694 | 96622723 |
| chr7 | 96625537 | 96625720 | chr7 | 96625998 | 96626051 | chr7 | 96627013 | 96627048 |
| chr7 | 96631579 | 96631680 | chr7 | 96634645 | 96634928 | chr7 | 96635345 | 96635451 |
| chr7 | 96635733 | 96635971 | chr7 | 96636034 | 96636645 | chr7 | 96639318 | 96639348 |
| chr7 | 96646662 | 96647131 | chr7 | 96647809 | 96648219 | chr7 | 96649955 | 96650094 |
| chr7 | 96650884 | 96651076 | chr7 | 96651137 | 96651151 | chr7 | 96651469 | 96651537 |
| chr7 | 96652144 | 96652174 | chr7 | 96653507 | 96653819 | chr7 | 96653863 | 96653993 |
| chr7 | 97361098 | 97361422 | chr7 | 97361521 | 97361781 | chr7 | 97362292 | 97362607 |
| chr7 | 97490474 | 97490508 | chr7 | 97580497 | 97580648 | chr7 | 97600104 | 97600224 |
| chr7 | 97839654 | 97839684 | chr7 | 97869290 | 97869391 | chr7 | 97869614 | 97869644 |
| chr7 | 98197206 | 98197242 | chr7 | 98245885 | 98246078 | chr7 | 98246305 | 98246507 |
| chr7 | 98246534 | 98246868 | chr7 | 98247126 | 98247656 | chr7 | 98966786 | 98966916 |
| chr7 | 98969875 | 98969928 | chr7 | 98971509 | 98971549 | chr7 | 99035152 | 99035191 |
| chr7 | 99104258 | 99104388 | chr7 | 99177742 | 99177870 | chr7 | 99591579 | 99591762 |
| chr7 | 99595194 | 99595335 | chr7 | 99642049 | 99642100 | chr7 | 99751578 | 99751630 |
| chr7 | 99775192 | 99775558 | chr7 | 99934913 | 99934943 | chr7 | 100088183 | 100088312 |
| chr7 | 100179889 | 100179927 | chr7 | 100241592 | 100241697 | chr7 | 100295321 | 100295424 |
| chr7 | 100318505 | 100318575 | chr7 | 100320690 | 100320719 | chr7 | 100547037 | 100547073 |
| chr7 | 100609750 | 100609780 | chr7 | 100808466 | 100808502 | chr7 | 100809436 | 100809521 |
| chr7 | 100823436 | 100823497 | chr7 | 101005968 | 101005998 | chr7 | 101241993 | 101242023 |
| chr7 | 101475790 | 101475858 | chr7 | 101558399 | 101558698 | chr7 | 101585887 | 101585917 |
| chr7 | 101627741 | 101627787 | chr7 | 101707502 | 101707532 | chr7 | 102091406 | 102091534 |
| chr7 | 102801710 | 102801804 | chr7 | 103085876 | 103086474 | chr7 | 103629059 | 103629794 |
| chr7 | 103630054 | 103630082 | chr7 | 103630475 | 103630824 | chr7 | 103969217 | 103969341 |
| chr7 | 103969694 | 103969794 | chr7 | 105279467 | 105279671 | chr7 | 106622834 | 106622961 |
| chr7 | 106685282 | 106685345 | chr7 | 106797774 | 106797804 | chr7 | 107301494 | 107301640 |
| chr7 | 107483694 | 107483918 | chr7 | 108095329 | 108095362 | chr7 | 108095781 | 108096055 |
| chr7 | 108097172 | 108097491 | chr7 | 111202993 | 111203260 | chr7 | 112726558 | 112726614 |
| chr7 | 113722810 | 113723283 | chr7 | 113723339 | 113723439 | chr7 | 113724956 | 113725081 |
| chr7 | 113726509 | 113726539 | chr7 | 113727442 | 113727486 | chr7 | 113727754 | 113727781 |
| chr7 | 115117552 | 115117647 | chr7 | 116140252 | 116140356 | chr7 | 116412008 | 116412058 |
| chr7 | 116415100 | 116415129 | chr7 | 116417443 | 116417496 | chr7 | 116422067 | 116422132 |
| chr7 | 116423399 | 116423488 | chr7 | 116962893 | 116963146 | chr7 | 116963331 | 116963476 |
| chr7 | 117119381 | 117120271 | chr7 | 117513675 | 117513849 | chr7 | 119913561 | 119913785 |
| chr7 | 120969672 | 120969800 | chr7 | 121513523 | 121513709 | chr7 | 121939677 | 121940244 |
| chr7 | 121940434 | 121940448 | chr7 | 121940935 | 121941052 | chr7 | 121941881 | 121942170 |
| chr7 | 121945822 | 121945920 | chr7 | 121946478 | 121946982 | chr7 | 121947098 | 121947406 |
| chr7 | 121950137 | 121950264 | chr7 | 121950429 | 121950552 | chr7 | 121950995 | 121951069 |
| chr7 | 121951877 | 121952010 | chr7 | 121952044 | 121952169 | chr7 | 121956486 | 121956567 |
| chr7 | 121956955 | 121957076 | chr7 | 121957254 | 121957331 | chr7 | 122526833 | 122526873 |

TABLE 12-continued

Pan Cancer #2

| chr | start | end | chr | start | end | chr | start | end |
|---|---|---|---|---|---|---|---|---|
| chr7 | 123173150 | 123173244 | chr7 | 123175689 | 123175899 | chr7 | 123672048 | 123672086 |
| chr7 | 124404415 | 124404497 | chr7 | 125082621 | 125082698 | chr7 | 126891220 | 126891250 |
| chr7 | 126891504 | 126891593 | chr7 | 126894076 | 126894197 | chr7 | 127371129 | 127371249 |
| chr7 | 127615921 | 127615951 | chr7 | 127744122 | 127744631 | chr7 | 127806634 | 127806664 |
| chr7 | 127807817 | 127807846 | chr7 | 127808047 | 127808792 | chr7 | 127841626 | 127841704 |
| chr7 | 127991826 | 127991922 | chr7 | 127992045 | 127992135 | chr7 | 128097059 | 128097089 |
| chr7 | 128337467 | 128337594 | chr7 | 128337788 | 128337921 | chr7 | 128470897 | 128471032 |
| chr7 | 128486036 | 128486138 | chr7 | 128528749 | 128528779 | chr7 | 128529023 | 128529053 |
| chr7 | 128828195 | 128828272 | chr7 | 129229456 | 129229631 | chr7 | 129418057 | 129418428 |
| chr7 | 129422160 | 129422968 | chr7 | 129423126 | 129423418 | chr7 | 129423834 | 129424034 |
| chr7 | 129424655 | 129425887 | chr7 | 129426195 | 129426236 | chr7 | 129483356 | 129483449 |
| chr7 | 129794593 | 129794721 | chr7 | 129800243 | 129800434 | chr7 | 129844226 | 129844493 |
| chr7 | 131041515 | 131041596 | chr7 | 131242738 | 131242824 | chr7 | 131514824 | 131514854 |
| chr7 | 132261272 | 132261432 | chr7 | 134143164 | 134143475 | chr7 | 134143807 | 134144132 |
| chr7 | 134918503 | 134918637 | chr7 | 136553311 | 136554025 | chr7 | 136554104 | 136554366 |
| chr7 | 136554638 | 136554966 | chr7 | 136555235 | 136555412 | chr7 | 136555681 | 136555841 |
| chr7 | 136556013 | 136556091 | chr7 | 136969053 | 136969083 | chr7 | 137028481 | 137028524 |
| chr7 | 137531158 | 137531211 | chr7 | 137531263 | 137531888 | chr7 | 137531909 | 137532187 |
| chr7 | 138042221 | 138042288 | chr7 | 138720785 | 138720909 | chr7 | 139167617 | 139167744 |
| chr7 | 139168115 | 139168379 | chr7 | 139208772 | 139208979 | chr7 | 139878250 | 139878296 |
| chr7 | 139930051 | 139930270 | chr7 | 139939160 | 139939318 | chr7 | 140027008 | 140027079 |
| chr7 | 140096812 | 140096882 | chr7 | 140097126 | 140097196 | chr7 | 140180094 | 140180444 |
| chr7 | 140218053 | 140218082 | chr7 | 140218123 | 140218352 | chr7 | 140219405 | 140219435 |
| chr7 | 140339952 | 140339982 | chr7 | 140453121 | 140453167 | chr7 | 140477779 | 140477868 |
| chr7 | 140481381 | 140481431 | chr7 | 140772795 | 140773228 | chr7 | 140773563 | 140773750 |
| chr7 | 142785612 | 142785728 | chr7 | 143042634 | 143042798 | chr7 | 143579739 | 143580069 |
| chr7 | 144712934 | 144713064 | chr7 | 145812992 | 145813082 | chr7 | 145813412 | 145813494 |
| chr7 | 145813946 | 145814166 | chr7 | 148224541 | 148224686 | chr7 | 148508712 | 148508741 |
| chr7 | 148640171 | 148640250 | chr7 | 148846434 | 148846180 | chr7 | 148846434 | 148846644 |
| chr7 | 148851143 | 148851234 | chr7 | 148883821 | 148883973 | chr7 | 149109648 | 149109785 |
| chr7 | 149112058 | 149112248 | chr7 | 149119948 | 149120073 | chr7 | 149411541 | 149411727 |
| chr7 | 149411835 | 149412304 | chr7 | 149570368 | 149570406 | chr7 | 149744505 | 149744560 |
| chr7 | 149917322 | 149917336 | chr7 | 149918119 | 149918149 | chr7 | 150038883 | 150038912 |
| chr7 | 150049604 | 150049718 | chr7 | 150069098 | 150069346 | chr7 | 150069679 | 150069820 |
| chr7 | 150070021 | 150070058 | chr7 | 150081236 | 150081308 | chr7 | 150716169 | 150716305 |
| chr7 | 150748192 | 150748406 | chr7 | 150753942 | 150753981 | chr7 | 150870816 | 150870889 |
| chr7 | 151001356 | 151001435 | chr7 | 151106451 | 151106565 | chr7 | 151106590 | 151106988 |
| chr7 | 151107486 | 151107651 | chr7 | 151188034 | 151188063 | chr7 | 151298870 | 151299029 |
| chr7 | 151423571 | 151423639 | chr7 | 151591667 | 151591705 | chr7 | 152133406 | 152133436 |
| chr7 | 152622621 | 152622697 | chr7 | 152913656 | 152913826 | chr7 | 153583632 | 153584069 |
| chr7 | 153584389 | 153584623 | chr7 | 153584848 | 153585206 | chr7 | 153585602 | 153585606 |
| chr7 | 153633796 | 153633942 | chr7 | 153749720 | 153750042 | chr7 | 154561150 | 154561189 |
| chr7 | 154708275 | 154708338 | chr7 | 154862046 | 154862266 | chr7 | 154926351 | 154926397 |
| chr7 | 155164454 | 155165562 | chr7 | 155165875 | 155166784 | chr7 | 155167034 | 155167089 |
| chr7 | 155167175 | 155167660 | chr7 | 155167834 | 155167909 | chr7 | 155174656 | 155174788 |
| chr7 | 155241318 | 155242049 | chr7 | 155242729 | 155243102 | chr7 | 155243346 | 155243533 |
| chr7 | 155243825 | 155243895 | chr7 | 155244180 | 155244361 | chr7 | 155246886 | 155247479 |
| chr7 | 155248913 | 155248943 | chr7 | 155249512 | 155249565 | chr7 | 155249925 | 155250011 |
| chr7 | 155250283 | 155250303 | chr7 | 155250324 | 155250355 | chr7 | 155250787 | 155250996 |
| chr7 | 155251701 | 155251854 | chr7 | 155251891 | 155251939 | chr7 | 155252247 | 155252261 |
| chr7 | 155252317 | 155252490 | chr7 | 155252862 | 155253041 | chr7 | 155254848 | 155255324 |
| chr7 | 155256269 | 155256312 | chr7 | 155257040 | 155257189 | chr7 | 155258193 | 155258487 |
| chr7 | 155258949 | 155259077 | chr7 | 155259120 | 155259622 | chr7 | 155259834 | 155259957 |
| chr7 | 155260039 | 155260137 | chr7 | 155260880 | 155260890 | chr7 | 155261071 | 155261210 |
| chr7 | 155301838 | 155301931 | chr7 | 155302328 | 155302895 | chr7 | 155302964 | 155303335 |
| chr7 | 155325796 | 155325872 | chr7 | 155326169 | 155326527 | chr7 | 155363304 | 155363417 |
| chr7 | 155580182 | 155580211 | chr7 | 155580846 | 155580876 | chr7 | 155581330 | 155581553 |
| chr7 | 155581765 | 155581980 | chr7 | 155582277 | 155582340 | chr7 | 155600629 | 155600723 |
| chr7 | 155602751 | 155602805 | chr7 | 155877196 | 155877283 | chr7 | 156259192 | 156259221 |
| chr7 | 156409144 | 156409347 | chr7 | 156409728 | 156409802 | chr7 | 156701846 | 156701908 |
| chr7 | 156707963 | 156708093 | chr7 | 156744619 | 156744713 | chr7 | 156779336 | 156779366 |
| chr7 | 156794153 | 156794235 | chr7 | 156794443 | 156794485 | chr7 | 156794998 | 156795354 |
| chr7 | 156795402 | 156795635 | chr7 | 156795900 | 156795914 | chr7 | 156796534 | 156796739 |
| chr7 | 156797006 | 156798434 | chr7 | 156798527 | 156799146 | chr7 | 156799291 | 156799467 |
| chr7 | 156800999 | 156801029 | chr7 | 156801403 | 156801601 | chr7 | 156808858 | 156809199 |
| chr7 | 156809983 | 156810521 | chr7 | 156810598 | 156810800 | chr7 | 156811303 | 156811436 |
| chr7 | 156812852 | 156813825 | chr7 | 156813987 | 156814707 | chr7 | 156814784 | 156815092 |
| chr7 | 156832223 | 156832402 | chr7 | 156832848 | 156833162 | chr7 | 156871283 | 156871297 |
| chr7 | 156880531 | 156880561 | chr7 | 157085373 | 157085487 | chr7 | 157085963 | 157086082 |
| chr7 | 157262815 | 157263018 | chr7 | 157263294 | 157263471 | chr7 | 157335172 | 157335202 |
| chr7 | 157361605 | 157361635 | chr7 | 157476879 | 157476973 | chr7 | 157476995 | 157477272 |
| chr7 | 157477473 | 157477488 | chr7 | 157477711 | 157477819 | chr7 | 157481130 | 157481160 |
| chr7 | 157481534 | 157481549 | chr7 | 157481969 | 157482073 | chr7 | 157482492 | 157482667 |
| chr7 | 157483320 | 157483538 | chr7 | 157484877 | 157485277 | chr7 | 157485527 | 157485601 |
| chr7 | 157485650 | 157485705 | chr7 | 157485976 | 157486081 | chr7 | 157486205 | 157486414 |
| chr7 | 157486476 | 157486503 | chr7 | 157584178 | 157584208 | chr7 | 157588586 | 157588791 |

TABLE 12-continued

Pan Cancer #2

| chr | start | end | chr | start | end | chr | start | end |
|---|---|---|---|---|---|---|---|---|
| chr7 | 157606706 | 157606736 | chr7 | 157690056 | 157690086 | chr7 | 158059762 | 158059794 |
| chr7 | 158065832 | 158065970 | chr7 | 158198597 | 158198648 | chr7 | 158298861 | 158299036 |
| chr7 | 158673836 | 158673942 | chr7 | 158741193 | 158741267 | chr7 | 158799762 | 158799791 |
| chr7 | 158936492 | 158936880 | chr7 | 158937203 | 158937374 | chr7 | 158937577 | 158937624 |
| chr7 | 158938210 | 158938399 | chr8 | 686870 | 686884 | chr8 | 687163 | 687217 |
| chr8 | 687838 | 687975 | chr8 | 1085573 | 1085603 | chr8 | 1325465 | 1325606 |
| chr8 | 1444165 | 1444205 | chr8 | 1950097 | 1950134 | chr8 | 4849141 | 4849177 |
| chr8 | 4849466 | 4849500 | chr8 | 4850247 | 4850322 | chr8 | 4850419 | 4850516 |
| chr8 | 4851736 | 4851749 | chr8 | 4852021 | 4852118 | chr8 | 8640024 | 8640100 |
| chr8 | 8681258 | 8681353 | chr8 | 8748422 | 8748713 | chr8 | 8748919 | 8748956 |
| chr8 | 9722850 | 9722896 | chr8 | 9756051 | 9756283 | chr8 | 9760735 | 9761155 |
| chr8 | 9762586 | 9762689 | chr8 | 9762752 | 9762864 | chr8 | 9763143 | 9763275 |
| chr8 | 9763895 | 9764049 | chr8 | 9764196 | 9764214 | chr8 | 9764434 | 9764551 |
| chr8 | 10587589 | 10587602 | chr8 | 10652917 | 10653017 | chr8 | 10980452 | 10980589 |
| chr8 | 11204479 | 11204509 | chr8 | 11204810 | 11204905 | chr8 | 11536827 | 11536857 |
| chr8 | 11537225 | 11537259 | chr8 | 11554885 | 11554915 | chr8 | 11555152 | 11555166 |
| chr8 | 11555474 | 11555521 | chr8 | 11559759 | 11559794 | chr8 | 11560068 | 11560375 |
| chr8 | 11560711 | 11560793 | chr8 | 11561442 | 11562169 | chr8 | 11562422 | 11562485 |
| chr8 | 11562701 | 11562917 | chr8 | 11700190 | 11700284 | chr8 | 11705960 | 11706136 |
| chr8 | 11706580 | 11706613 | chr8 | 11726469 | 11726975 | chr8 | 11790579 | 11790653 |
| chr8 | 12990386 | 12990431 | chr8 | 12990664 | 12990784 | chr8 | 13319931 | 13319961 |
| chr8 | 15094505 | 15094566 | chr8 | 16884182 | 16884239 | chr8 | 16885205 | 16885241 |
| chr8 | 17271091 | 17271119 | chr8 | 19797433 | 19797463 | chr8 | 19797939 | 19798019 |
| chr8 | 20375563 | 20375592 | chr8 | 21876649 | 21876819 | chr8 | 22089409 | 22089560 |
| chr8 | 22101641 | 22101699 | chr8 | 22458657 | 22458687 | chr8 | 22562345 | 22562483 |
| chr8 | 22960648 | 22960723 | chr8 | 23020951 | 23021107 | chr8 | 23260683 | 23260870 |
| chr8 | 23423923 | 23423974 | chr8 | 23559385 | 23559601 | chr8 | 23559666 | 23560525 |
| chr8 | 23563791 | 23564023 | chr8 | 23564193 | 23564388 | chr8 | 23564652 | 23564668 |
| chr8 | 23564703 | 23565024 | chr8 | 23566854 | 23566895 | chr8 | 23566901 | 23567213 |
| chr8 | 23567312 | 23567492 | chr8 | 23571681 | 23571973 | chr8 | 23572377 | 23572554 |
| chr8 | 23584094 | 23584400 | chr8 | 23584582 | 23584760 | chr8 | 24770314 | 24770361 |
| chr8 | 24770414 | 24770581 | chr8 | 24771431 | 24771562 | chr8 | 24813188 | 24813287 |
| chr8 | 24813750 | 24813893 | chr8 | 24814011 | 24814407 | chr8 | 24857776 | 24857808 |
| chr8 | 24858336 | 24858440 | chr8 | 24858856 | 24859161 | chr8 | 24859496 | 24859526 |
| chr8 | 25041746 | 25041864 | chr8 | 25042534 | 25042567 | chr8 | 25900408 | 25900692 |
| chr8 | 25900781 | 25901317 | chr8 | 25901540 | 25901765 | chr8 | 25902146 | 25902176 |
| chr8 | 25902619 | 25902649 | chr8 | 25903662 | 25903854 | chr8 | 25904157 | 25904191 |
| chr8 | 25905096 | 25905126 | chr8 | 25905762 | 25905811 | chr8 | 25909197 | 25909597 |
| chr8 | 26372863 | 26372893 | chr8 | 26723985 | 26724080 | chr8 | 28266438 | 28266484 |
| chr8 | 28737884 | 28738023 | chr8 | 30243388 | 30243423 | chr8 | 30475450 | 30475480 |
| chr8 | 30769249 | 30769411 | chr8 | 30770106 | 30770109 | chr8 | 30770158 | 30770188 |
| chr8 | 31044103 | 31044133 | chr8 | 31496481 | 31496757 | chr8 | 31497024 | 31497152 |
| chr8 | 31497499 | 31497639 | chr8 | 32406598 | 32406914 | chr8 | 33372069 | 33372125 |
| chr8 | 33457142 | 33457379 | chr8 | 35093037 | 35093054 | chr8 | 35093951 | 35093973 |
| chr8 | 37655476 | 37655517 | chr8 | 37655810 | 37655990 | chr8 | 37656050 | 37656081 |
| chr8 | 37755922 | 37755952 | chr8 | 37822796 | 37823423 | chr8 | 37906396 | 37906513 |
| chr8 | 37961793 | 37961902 | chr8 | 38008234 | 38008557 | chr8 | 38020213 | 38020272 |
| chr8 | 38032345 | 38032827 | chr8 | 38256378 | 38256412 | chr8 | 38262472 | 38262502 |
| chr8 | 38274835 | 38274864 | chr8 | 38323911 | 38323941 | chr8 | 38965322 | 38965386 |
| chr8 | 39172082 | 39172134 | chr8 | 41165865 | 41165918 | chr8 | 41166001 | 41166151 |
| chr8 | 41166267 | 41166679 | chr8 | 41166974 | 41166988 | chr8 | 41167026 | 41167035 |
| chr8 | 41424760 | 41424842 | chr8 | 41624826 | 41624855 | chr8 | 41625112 | 41625141 |
| chr8 | 41700639 | 41700751 | chr8 | 41711325 | 41711447 | chr8 | 41733505 | 41733640 |
| chr8 | 41753593 | 41753752 | chr8 | 41754152 | 41754885 | chr8 | 41755178 | 41755208 |
| chr8 | 41910270 | 41910339 | chr8 | 42082721 | 42082874 | chr8 | 42147392 | 42147521 |
| chr8 | 42293604 | 42293722 | chr8 | 42350324 | 42350492 | chr8 | 42749816 | 42750012 |
| chr8 | 47093246 | 47093276 | chr8 | 47334619 | 47334678 | chr8 | 48044710 | 48044753 |
| chr8 | 48100155 | 48100443 | chr8 | 49293364 | 49293524 | chr8 | 49293581 | 49293614 |
| chr8 | 49468669 | 49469127 | chr8 | 49572029 | 49572058 | chr8 | 49783041 | 49783283 |
| chr8 | 49836145 | 49836174 | chr8 | 49959230 | 49959260 | chr8 | 50822179 | 50822308 |
| chr8 | 50822686 | 50822734 | chr8 | 50823452 | 50823562 | chr8 | 52230518 | 52230548 |
| chr8 | 53322495 | 53322524 | chr8 | 53477408 | 53477736 | chr8 | 53478008 | 53478275 |
| chr8 | 53478480 | 53478720 | chr8 | 53851141 | 53851170 | chr8 | 53853811 | 53854509 |
| chr8 | 54163316 | 54163349 | chr8 | 54163674 | 54164126 | chr8 | 54698973 | 54699103 |
| chr8 | 54789278 | 54789310 | chr8 | 54789632 | 54789805 | chr8 | 54790023 | 54790077 |
| chr8 | 54790291 | 54790855 | chr8 | 54791898 | 54791945 | chr8 | 54792185 | 54792237 |
| chr8 | 54792634 | 54792670 | chr8 | 54792702 | 54792760 | chr8 | 54794217 | 54794327 |
| chr8 | 54794713 | 54794780 | chr8 | 54794827 | 54794949 | chr8 | 54795140 | 54795196 |
| chr8 | 55366188 | 55366367 | chr8 | 55366952 | 55367641 | chr8 | 55370113 | 55370432 |
| chr8 | 55370568 | 55370713 | chr8 | 55370836 | 55370858 | chr8 | 55371178 | 55371375 |
| chr8 | 55371440 | 55371724 | chr8 | 55371994 | 55372067 | chr8 | 55372417 | 55372538 |
| chr8 | 55379296 | 55379456 | chr8 | 55383183 | 55383237 | chr8 | 55826087 | 55826117 |
| chr8 | 56013641 | 56013892 | chr8 | 56014157 | 56014184 | chr8 | 56014623 | 56014743 |
| chr8 | 56015038 | 56015052 | chr8 | 56015186 | 56015357 | chr8 | 56015560 | 56015619 |
| chr8 | 56015908 | 56015938 | chr8 | 56542925 | 56543064 | chr8 | 57025776 | 57025943 |
| chr8 | 57026168 | 57026213 | chr8 | 57026503 | 57026547 | chr8 | 57069553 | 57069737 |

TABLE 12-continued

Pan Cancer #2

| chr | start | end | chr | start | end | chr | start | end |
|---|---|---|---|---|---|---|---|---|
| chr8 | 57069851 | 57070157 | chr8 | 57358465 | 57358661 | chr8 | 57358807 | 57359091 |
| chr8 | 57359260 | 57359636 | chr8 | 57359893 | 57359922 | chr8 | 57360211 | 57360240 |
| chr8 | 57360570 | 57360625 | chr8 | 57360770 | 57360791 | chr8 | 58105946 | 58106115 |
| chr8 | 58117004 | 58117079 | chr8 | 58130364 | 58130574 | chr8 | 58907698 | 58907835 |
| chr8 | 59058941 | 59059343 | chr8 | 59747186 | 59747318 | chr8 | 60032680 | 60032738 |
| chr8 | 61777575 | 61777699 | chr8 | 61789974 | 61790004 | chr8 | 62033879 | 62034059 |
| chr8 | 62200502 | 62200776 | chr8 | 62763403 | 62763433 | chr8 | 63161658 | 63161800 |
| chr8 | 65281616 | 65281760 | chr8 | 65281984 | 65282004 | chr8 | 65282333 | 65282440 |
| chr8 | 65282713 | 65282944 | chr8 | 65283042 | 65283341 | chr8 | 65283799 | 65284094 |
| chr8 | 65286056 | 65286066 | chr8 | 65286682 | 65286753 | chr8 | 65286963 | 65287251 |
| chr8 | 65289123 | 65289241 | chr8 | 65289614 | 65290681 | chr8 | 65291034 | 65291284 |
| chr8 | 65292185 | 65292727 | chr8 | 65488271 | 65488322 | chr8 | 65488661 | 65488697 |
| chr8 | 65489099 | 65489129 | chr8 | 65492712 | 65492979 | chr8 | 65493195 | 65493433 |
| chr8 | 65494077 | 65494193 | chr8 | 65498566 | 65498841 | chr8 | 65499757 | 65500015 |
| chr8 | 65710938 | 65711046 | chr8 | 66548717 | 66548800 | chr8 | 66560323 | 66560545 |
| chr8 | 67025063 | 67025640 | chr8 | 67025920 | 67026578 | chr8 | 67026812 | 67026990 |
| chr8 | 67344538 | 67344701 | chr8 | 67580735 | 67580829 | chr8 | 67873327 | 67873421 |
| chr8 | 67873799 | 67874050 | chr8 | 67874165 | 67874672 | chr8 | 67874756 | 67875682 |
| chr8 | 67940624 | 67940875 | chr8 | 68864578 | 68864765 | chr8 | 69242905 | 69242988 |
| chr8 | 69243285 | 69243902 | chr8 | 69243964 | 69243994 | chr8 | 69244370 | 69244500 |
| chr8 | 70744860 | 70744925 | chr8 | 70946760 | 70946914 | chr8 | 70947091 | 70947658 |
| chr8 | 70982263 | 70982566 | chr8 | 70982851 | 70983226 | chr8 | 70983504 | 70983869 |
| chr8 | 70984017 | 70984292 | chr8 | 70984344 | 70984661 | chr8 | 70984745 | 70984978 |
| chr8 | 71017156 | 71017195 | chr8 | 71308096 | 71308126 | chr8 | 71447529 | 71447559 |
| chr8 | 72273998 | 72274033 | chr8 | 72468569 | 72469574 | chr8 | 72470399 | 72470441 |
| chr8 | 72471053 | 72471083 | chr8 | 72754491 | 72754609 | chr8 | 72754821 | 72755176 |
| chr8 | 72755666 | 72755814 | chr8 | 72756656 | 72756896 | chr8 | 72917335 | 72917428 |
| chr8 | 72987600 | 72988036 | chr8 | 73163860 | 73164180 | chr8 | 73450064 | 73450100 |
| chr8 | 73450515 | 73450559 | chr8 | 74759819 | 74759463 | chr8 | 74759819 | 74759966 |
| chr8 | 74889486 | 74889592 | chr8 | 75896574 | 75897337 | chr8 | 76316329 | 76316452 |
| chr8 | 77585219 | 77585698 | chr8 | 77586175 | 77586278 | chr8 | 77586563 | 77586617 |
| chr8 | 77590239 | 77590466 | chr8 | 77593110 | 77593376 | chr8 | 77593889 | 77594124 |
| chr8 | 77594648 | 77594674 | chr8 | 77594758 | 77594993 | chr8 | 77595339 | 77595494 |
| chr8 | 79428297 | 79428401 | chr8 | 80523983 | 80524029 | chr8 | 80524253 | 80524318 |
| chr8 | 80524946 | 80525020 | chr8 | 80525604 | 80525733 | chr8 | 80695902 | 80695932 |
| chr8 | 80803673 | 80803872 | chr8 | 80894529 | 80894594 | chr8 | 80998526 | 80998601 |
| chr8 | 81128658 | 81128782 | chr8 | 81398018 | 81398155 | chr8 | 81398428 | 81399496 |
| chr8 | 81414643 | 81414831 | chr8 | 81478185 | 81478350 | chr8 | 82243813 | 82243843 |
| chr8 | 82902963 | 82902993 | chr8 | 84932902 | 84932942 | chr8 | 85095482 | 85095668 |
| chr8 | 85096583 | 85096772 | chr8 | 85097063 | 85097220 | chr8 | 86131760 | 86131850 |
| chr8 | 86350553 | 86350566 | chr8 | 86405788 | 86405818 | chr8 | 86406716 | 86406849 |
| chr8 | 86436621 | 86436651 | chr8 | 86495193 | 86495287 | chr8 | 86544756 | 86544959 |
| chr8 | 89339389 | 89339745 | chr8 | 89340274 | 89340345 | chr8 | 90702972 | 90703034 |
| chr8 | 90913079 | 90913653 | chr8 | 91094221 | 91094251 | chr8 | 91411537 | 91411567 |
| chr8 | 91803676 | 91803718 | chr8 | 91804065 | 91804253 | chr8 | 91997046 | 91997508 |
| chr8 | 91997528 | 91997947 | chr8 | 92083523 | 92083751 | chr8 | 93114135 | 93114241 |
| chr8 | 93114307 | 93114528 | chr8 | 94684190 | 94684560 | chr8 | 95485999 | 95486029 |
| chr8 | 95651098 | 95651218 | chr8 | 95651538 | 95651655 | chr8 | 96038540 | 96038580 |
| chr8 | 96219863 | 96219901 | chr8 | 96285420 | 96285553 | chr8 | 97157085 | 97157209 |
| chr8 | 97157667 | 97157897 | chr8 | 97158022 | 97158066 | chr8 | 97165644 | 97165676 |
| chr8 | 97166425 | 97166455 | chr8 | 97167178 | 97167223 | chr8 | 97167811 | 97167855 |
| chr8 | 97169838 | 97169955 | chr8 | 97170054 | 97170334 | chr8 | 97170867 | 97170897 |
| chr8 | 97171129 | 97171264 | chr8 | 97171318 | 97171958 | chr8 | 97172019 | 97172200 |
| chr8 | 97172433 | 97172739 | chr8 | 97172822 | 97173458 | chr8 | 97173822 | 97173863 |
| chr8 | 97173921 | 97173935 | chr8 | 97339846 | 97340195 | chr8 | 97506034 | 97506048 |
| chr8 | 97506178 | 97506407 | chr8 | 97506448 | 97506524 | chr8 | 97507115 | 97507284 |
| chr8 | 97507546 | 97507680 | chr8 | 98289825 | 98289867 | chr8 | 98289923 | 98290260 |
| chr8 | 98744202 | 98744325 | chr8 | 98786343 | 98786387 | chr8 | 98786918 | 98786972 |
| chr8 | 99234962 | 99235037 | chr8 | 99439104 | 99439133 | chr8 | 99439382 | 99440354 |
| chr8 | 99951404 | 99951434 | chr8 | 99951836 | 99952143 | chr8 | 99952199 | 99952303 |
| chr8 | 99952533 | 99952815 | chr8 | 99954490 | 99954562 | chr8 | 99954679 | 99954727 |
| chr8 | 99955180 | 99955327 | chr8 | 99959429 | 99959549 | chr8 | 99960329 | 99960497 |
| chr8 | 99960922 | 99960971 | chr8 | 99961781 | 99961822 | chr8 | 99985866 | 99986043 |
| chr8 | 99986226 | 99986526 | chr8 | 99986792 | 99987014 | chr8 | 100117651 | 100117765 |
| chr8 | 101118241 | 101118490 | chr8 | 101169625 | 101169659 | chr8 | 101661920 | 101661991 |
| chr8 | 101726865 | 101726945 | chr8 | 101736027 | 101736202 | chr8 | 101821973 | 101822047 |
| chr8 | 101920382 | 101920468 | chr8 | 102504464 | 102504506 | chr8 | 102505512 | 102505556 |
| chr8 | 102505797 | 102505985 | chr8 | 103575128 | 103575296 | chr8 | 103629590 | 103629882 |
| chr8 | 104153202 | 104153246 | chr8 | 104153449 | 104153561 | chr8 | 104383700 | 104383985 |
| chr8 | 104512123 | 104513186 | chr8 | 104513462 | 104513926 | chr8 | 105235369 | 105235501 |
| chr8 | 105235644 | 105235803 | chr8 | 105236054 | 105236054 | chr8 | 105478725 | 105478779 |
| chr8 | 105479404 | 105479464 | chr8 | 106301844 | 106301978 | chr8 | 106331160 | 106331237 |
| chr8 | 106332104 | 106332202 | chr8 | 106434115 | 106434145 | chr8 | 107282163 | 107282195 |
| chr8 | 107284038 | 107284075 | chr8 | 108509543 | 108509697 | chr8 | 109093679 | 109094180 |
| chr8 | 109094485 | 109094595 | chr8 | 109094840 | 109095436 | chr8 | 109095506 | 109095932 |
| chr8 | 109500408 | 109500507 | chr8 | 109799588 | 109799739 | chr8 | 110275006 | 110275040 |

TABLE 12-continued

Pan Cancer #2

| chr | start | end | chr | start | end | chr | start | end |
|---|---|---|---|---|---|---|---|---|
| chr8 | 110406028 | 110406243 | chr8 | 110592198 | 110592228 | chr8 | 110704001 | 110704144 |
| chr8 | 110986443 | 110986682 | chr8 | 111133092 | 111133257 | chr8 | 114444580 | 114445192 |
| chr8 | 114445763 | 114446068 | chr8 | 114446405 | 114446435 | chr8 | 114446931 | 114447368 |
| chr8 | 114449039 | 114449257 | chr8 | 114449550 | 114449602 | chr8 | 115516296 | 115516440 |
| chr8 | 116660527 | 116660571 | chr8 | 116660616 | 116660760 | chr8 | 117950438 | 117950468 |
| chr8 | 117950783 | 117950914 | chr8 | 118532128 | 118532292 | chr8 | 119043568 | 119043732 |
| chr8 | 120219912 | 120219941 | chr8 | 120220116 | 120220145 | chr8 | 120220428 | 120220592 |
| chr8 | 120650979 | 120651008 | chr8 | 120651221 | 120651412 | chr8 | 120844095 | 120844285 |
| chr8 | 120845586 | 120845807 | chr8 | 121136879 | 121137748 | chr8 | 121823901 | 121823930 |
| chr8 | 121824203 | 121824481 | chr8 | 121825455 | 121825484 | chr8 | 122068889 | 122068919 |
| chr8 | 122346689 | 122346719 | chr8 | 122346940 | 122347052 | chr8 | 122651872 | 122651905 |
| chr8 | 123695532 | 123695660 | chr8 | 124014063 | 124014111 | chr8 | 124055236 | 124055336 |
| chr8 | 124173246 | 124173501 | chr8 | 124332846 | 124332875 | chr8 | 124427887 | 124428082 |
| chr8 | 125411827 | 125411857 | chr8 | 125452366 | 125452541 | chr8 | 126007690 | 126008051 |
| chr8 | 126044442 | 126044563 | chr8 | 127354106 | 127354261 | chr8 | 127569621 | 127569676 |
| chr8 | 128403354 | 128403383 | chr8 | 128745542 | 128745633 | chr8 | 128808002 | 128808077 |
| chr8 | 128872385 | 128872415 | chr8 | 128889324 | 128889422 | chr8 | 128893019 | 128893049 |
| chr8 | 128931133 | 128931261 | chr8 | 128964114 | 128964309 | chr8 | 129356009 | 129356039 |
| chr8 | 130369244 | 130369364 | chr8 | 132052147 | 132052299 | chr8 | 132052399 | 132052515 |
| chr8 | 132052590 | 132053164 | chr8 | 132053715 | 132054583 | chr8 | 132054594 | 132054785 |
| chr8 | 133360080 | 133360194 | chr8 | 133686745 | 133687107 | chr8 | 135301097 | 135301142 |
| chr8 | 139508757 | 139508946 | chr8 | 139509741 | 139509928 | chr8 | 140714570 | 140714877 |
| chr8 | 140715090 | 140715094 | chr8 | 140715469 | 140715587 | chr8 | 140715965 | 140716021 |
| chr8 | 140716340 | 140716382 | chr8 | 140755383 | 140755550 | chr8 | 140834237 | 140834321 |
| chr8 | 140963292 | 140963362 | chr8 | 141054845 | 141054875 | chr8 | 141159919 | 141159949 |
| chr8 | 141588056 | 141588132 | chr8 | 141596886 | 141597022 | chr8 | 141614252 | 141614287 |
| chr8 | 142210914 | 142211043 | chr8 | 142265206 | 142265339 | chr8 | 142282078 | 142282202 |
| chr8 | 142292552 | 142292774 | chr8 | 142318155 | 142318184 | chr8 | 142361233 | 142361487 |
| chr8 | 142367368 | 142367790 | chr8 | 142444600 | 142444752 | chr8 | 142528400 | 142528402 |
| chr8 | 142528455 | 142528606 | chr8 | 142528671 | 142528781 | chr8 | 142528835 | 142528961 |
| chr8 | 142535343 | 142535496 | chr8 | 142568598 | 142568652 | chr8 | 142632436 | 142632465 |
| chr8 | 142694847 | 142694953 | chr8 | 142984512 | 142984666 | chr8 | 143082777 | 143082810 |
| chr8 | 143089030 | 143089100 | chr8 | 143105244 | 143105377 | chr8 | 143368318 | 143368469 |
| chr8 | 143509457 | 143509594 | chr8 | 143532122 | 143532509 | chr8 | 143532542 | 143532846 |
| chr8 | 143533611 | 143533640 | chr8 | 143533709 | 143533906 | chr8 | 143557980 | 143558080 |
| chr8 | 143558472 | 143558604 | chr8 | 143587331 | 143587382 | chr8 | 143592664 | 143592687 |
| chr8 | 143611232 | 143611262 | chr8 | 143621980 | 143622096 | chr8 | 143702052 | 143702101 |
| chr8 | 143819384 | 143819428 | chr8 | 143858522 | 143858699 | chr8 | 143859338 | 143859361 |
| chr8 | 143876928 | 143876958 | chr8 | 143993974 | 143994165 | chr8 | 144069546 | 144069651 |
| chr8 | 144190378 | 144190432 | chr8 | 144203653 | 144203708 | chr8 | 144203977 | 144204021 |
| chr8 | 144226174 | 144226204 | chr8 | 144238822 | 144238901 | chr8 | 144241250 | 144241287 |
| chr8 | 144241871 | 144242356 | chr8 | 144303562 | 144303592 | chr8 | 144328321 | 144328565 |
| chr8 | 144330193 | 144330380 | chr8 | 144344293 | 144344442 | chr8 | 144347397 | 144347740 |
| chr8 | 144359977 | 144360076 | chr8 | 144360394 | 144360453 | chr8 | 144361758 | 144361823 |
| chr8 | 144372323 | 144372503 | chr8 | 144382679 | 144382775 | chr8 | 144421487 | 144421517 |
| chr8 | 144509325 | 144510529 | chr8 | 144511225 | 144511424 | chr8 | 144512041 | 144512192 |
| chr8 | 144512473 | 144512503 | chr8 | 144557003 | 144557088 | chr8 | 144601799 | 144601851 |
| chr8 | 144617065 | 144617347 | chr8 | 144650594 | 144650730 | chr8 | 144668566 | 144668667 |
| chr8 | 144668909 | 144668972 | chr8 | 145033304 | 145033333 | chr8 | 145218226 | 145218301 |
| chr8 | 145223902 | 145224061 | chr8 | 145753571 | 145753547 | chr8 | 145758572 | 145758692 |
| chr8 | 145806258 | 145806271 | chr8 | 145918683 | 145918835 | chr8 | 145925461 | 145925491 |
| chr8 | 145925947 | 145926068 | chr8 | 146013617 | 146013647 | chr8 | 146079215 | 146079379 |
| chr8 | 146175120 | 146175269 | chr8 | 146176756 | 146176795 | chr9 | 113433 | 113512 |
| chr9 | 113550 | 113556 | chr9 | 113850 | 113885 | chr9 | 117884 | 117959 |
| chr9 | 841691 | 842031 | chr9 | 842208 | 842230 | chr9 | 842611 | 842673 |
| chr9 | 969556 | 969586 | chr9 | 969788 | 969846 | chr9 | 970096 | 970104 |
| chr9 | 970186 | 970225 | chr9 | 970495 | 970525 | chr9 | 970897 | 970911 |
| chr9 | 970993 | 971338 | chr9 | 972307 | 972759 | chr9 | 973184 | 973289 |
| chr9 | 974514 | 974547 | chr9 | 975117 | 975167 | chr9 | 975783 | 976321 |
| chr9 | 976618 | 976689 | chr9 | 976912 | 976961 | chr9 | 981797 | 981830 |
| chr9 | 1042402 | 1042500 | chr9 | 1042616 | 1042986 | chr9 | 1051905 | 1052166 |
| chr9 | 2115824 | 2115981 | chr9 | 3181752 | 3181869 | chr9 | 5070006 | 5070050 |
| chr9 | 5073756 | 5073788 | chr9 | 5078346 | 5078371 | chr9 | 5089711 | 5089740 |
| chr9 | 5153325 | 5153380 | chr9 | 6182901 | 6182931 | chr9 | 6412571 | 6412809 |
| chr9 | 6644297 | 6644367 | chr9 | 6644540 | 6644554 | chr9 | 6645017 | 6645333 |
| chr9 | 6645625 | 6645700 | chr9 | 6756353 | 6756623 | chr9 | 13278818 | 13278864 |
| chr9 | 14312994 | 14313096 | chr9 | 14313319 | 14313785 | chr9 | 14347633 | 14347673 |
| chr9 | 14348314 | 14348452 | chr9 | 14884008 | 14884061 | chr9 | 17906404 | 17906432 |
| chr9 | 17906461 | 17906694 | chr9 | 17907004 | 17907061 | chr9 | 17907451 | 17907472 |
| chr9 | 19789107 | 19789301 | chr9 | 20199955 | 20199985 | chr9 | 21031734 | 21031836 |
| chr9 | 21402617 | 21403021 | chr9 | 21559294 | 21559381 | chr9 | 21559665 | 21559702 |
| chr9 | 21965057 | 21965424 | chr9 | 21965570 | 21965757 | chr9 | 21968218 | 21968433 |
| chr9 | 21968457 | 21968475 | chr9 | 21970959 | 21971154 | chr9 | 21971185 | 21971220 |
| chr9 | 21973940 | 21974076 | chr9 | 21974182 | 21974237 | chr9 | 21974499 | 21974794 |
| chr9 | 21994208 | 21994237 | chr9 | 21995297 | 21995326 | chr9 | 21995720 | 21995749 |
| chr9 | 22006131 | 22006152 | chr9 | 22008819 | 22008899 | chr9 | 22447664 | 22447708 |

TABLE 12-continued

Pan Cancer #2

| chr | start | end | chr | start | end | chr | start | end |
|---|---|---|---|---|---|---|---|---|
| chr9 | 23822568 | 23822606 | chr9 | 23824561 | 23824591 | chr9 | 23831100 | 23831370 |
| chr9 | 29212170 | 29212170 | chr9 | 29212211 | 29212294 | chr9 | 29213508 | 29213651 |
| chr9 | 29214030 | 29214144 | chr9 | 29214360 | 29214430 | chr9 | 29214681 | 29215086 |
| chr9 | 32782630 | 32782935 | chr9 | 32783084 | 32783121 | chr9 | 32783346 | 32783419 |
| chr9 | 32783591 | 32783657 | chr9 | 33000470 | 33000512 | chr9 | 33524609 | 33524687 |
| chr9 | 33676771 | 33676801 | chr9 | 33677360 | 33677415 | chr9 | 34136792 | 34136903 |
| chr9 | 34224348 | 34224474 | chr9 | 34372805 | 34372983 | chr9 | 34589062 | 34589156 |
| chr9 | 35617291 | 35617337 | chr9 | 35675539 | 35675647 | chr9 | 35675838 | 35676180 |
| chr9 | 35844834 | 35844863 | chr9 | 36036323 | 36036353 | chr9 | 36037068 | 36037098 |
| chr9 | 36167272 | 36167544 | chr9 | 36196920 | 36197005 | chr9 | 36318375 | 36318410 |
| chr9 | 36433491 | 36433629 | chr9 | 36739812 | 36739980 | chr9 | 36832204 | 36832343 |
| chr9 | 37002454 | 37002517 | chr9 | 37002819 | 37003077 | chr9 | 37025564 | 37025783 |
| chr9 | 37026146 | 37026351 | chr9 | 37026434 | 37026622 | chr9 | 37026831 | 37027271 |
| chr9 | 37027325 | 37027412 | chr9 | 37027800 | 37027829 | chr9 | 37028944 | 37029119 |
| chr9 | 37029534 | 37030655 | chr9 | 37034197 | 37034247 | chr9 | 37034616 | 37034731 |
| chr9 | 37035366 | 37035734 | chr9 | 37036425 | 37036647 | chr9 | 37037671 | 37038354 |
| chr9 | 37119301 | 37119331 | chr9 | 37467670 | 37467898 | chr9 | 37593684 | 37593795 |
| chr9 | 37697404 | 37697438 | chr9 | 38620530 | 38620725 | chr9 | 38646763 | 38646839 |
| chr9 | 66455999 | 66456047 | chr9 | 71200632 | 71200662 | chr9 | 71500847 | 71500886 |
| chr9 | 71584152 | 71584254 | chr9 | 71734816 | 71735024 | chr9 | 71788952 | 71789260 |
| chr9 | 71789453 | 71789757 | chr9 | 72435189 | 72435317 | chr9 | 73032801 | 73032831 |
| chr9 | 74061838 | 74062070 | chr9 | 74210499 | 74210654 | chr9 | 74764547 | 74764648 |
| chr9 | 77112993 | 77113340 | chr9 | 77113559 | 77113708 | chr9 | 77113806 | 77113825 |
| chr9 | 77114745 | 77114851 | chr9 | 77115210 | 77115447 | chr9 | 77115657 | 77115687 |
| chr9 | 77823177 | 77823315 | chr9 | 79197119 | 79197149 | chr9 | 79231003 | 79231033 |
| chr9 | 79626876 | 79627370 | chr9 | 79628289 | 79628329 | chr9 | 79629208 | 79629471 |
| chr9 | 79629879 | 79630420 | chr9 | 79631192 | 79631335 | chr9 | 79631555 | 79631591 |
| chr9 | 79631865 | 79632182 | chr9 | 79632860 | 79632890 | chr9 | 79633397 | 79633904 |
| chr9 | 79634170 | 79635448 | chr9 | 79635746 | 79636043 | chr9 | 79636258 | 79637274 |
| chr9 | 79637555 | 79637888 | chr9 | 79638137 | 79638244 | chr9 | 80303132 | 80303171 |
| chr9 | 80409473 | 80409502 | chr9 | 80833933 | 80834011 | chr9 | 85372494 | 85372596 |
| chr9 | 85677905 | 85677992 | chr9 | 86152387 | 86152417 | chr9 | 86578079 | 86578366 |
| chr9 | 86755532 | 86755952 | chr9 | 86886706 | 86886736 | chr9 | 87283008 | 87283038 |
| chr9 | 87283677 | 87283709 | chr9 | 87284706 | 87284798 | chr9 | 87285279 | 87285472 |
| chr9 | 88137524 | 88137725 | chr9 | 88137875 | 88137998 | chr9 | 88694345 | 88694438 |
| chr9 | 89560760 | 89560827 | chr9 | 89561063 | 89561109 | chr9 | 90907408 | 90907438 |
| chr9 | 90937357 | 90937387 | chr9 | 91150222 | 91150335 | chr9 | 91606004 | 91606058 |
| chr9 | 91792357 | 91792387 | chr9 | 91792776 | 91792907 | chr9 | 91793177 | 91793526 |
| chr9 | 91914276 | 91914306 | chr9 | 92053911 | 92053949 | chr9 | 93698029 | 93698133 |
| chr9 | 94183870 | 94183954 | chr9 | 94572641 | 94572743 | chr9 | 94686919 | 94686957 |
| chr9 | 95417551 | 95417651 | chr9 | 95560810 | 95560840 | chr9 | 95569759 | 95569822 |
| chr9 | 95570247 | 95570434 | chr9 | 95571617 | 95571760 | chr9 | 95761687 | 95761828 |
| chr9 | 95947130 | 95947296 | chr9 | 96230296 | 96230334 | chr9 | 96573748 | 96573869 |
| chr9 | 96588858 | 96588885 | chr9 | 96710377 | 96710407 | chr9 | 96710647 | 96710991 |
| chr9 | 96711258 | 96711446 | chr9 | 96711535 | 96711617 | chr9 | 96711975 | 96712005 |
| chr9 | 96713378 | 96713893 | chr9 | 96715095 | 96715372 | chr9 | 96715688 | 96715857 |
| chr9 | 96716905 | 96717427 | chr9 | 96717450 | 96717466 | chr9 | 96717979 | 96718149 |
| chr9 | 96720803 | 96720885 | chr9 | 96721103 | 96721467 | chr9 | 96721689 | 96721802 |
| chr9 | 96722445 | 96722547 | chr9 | 96723093 | 96723159 | chr9 | 96723171 | 96723202 |
| chr9 | 96856991 | 96857144 | chr9 | 97020978 | 97021126 | chr9 | 97845915 | 97845947 |
| chr9 | 98076746 | 98076776 | chr9 | 98111365 | 98111560 | chr9 | 98111895 | 98112157 |
| chr9 | 98112344 | 98112395 | chr9 | 98784772 | 98784802 | chr9 | 98789651 | 98790000 |
| chr9 | 99146020 | 99146153 | chr9 | 99259362 | 99259405 | chr9 | 99449135 | 99449451 |
| chr9 | 99450020 | 99450142 | chr9 | 99639621 | 99639942 | chr9 | 99983140 | 99983170 |
| chr9 | 99983411 | 99983824 | chr9 | 99984026 | 99984057 | chr9 | 99984108 | 99984242 |
| chr9 | 100397821 | 100398016 | chr9 | 100503625 | 100503937 | chr9 | 100609991 | 100610134 |
| chr9 | 100610201 | 100610218 | chr9 | 100610681 | 100610816 | chr9 | 100611125 | 100611640 |
| chr9 | 100613828 | 100613999 | chr9 | 100614193 | 100614325 | chr9 | 100614541 | 100616035 |
| chr9 | 100616271 | 100616468 | chr9 | 100617293 | 100617365 | chr9 | 100617682 | 100618055 |
| chr9 | 100619722 | 100620069 | chr9 | 100620330 | 100620783 | chr9 | 100818295 | 100818437 |
| chr9 | 100835828 | 100835870 | chr9 | 101469269 | 101469307 | chr9 | 101469603 | 101469796 |
| chr9 | 101470116 | 101470250 | chr9 | 101470968 | 101471071 | chr9 | 101471570 | 101471621 |
| chr9 | 101471860 | 101472009 | chr9 | 101705996 | 101706195 | chr9 | 101706313 | 101706695 |
| chr9 | 103174620 | 103174730 | chr9 | 104248579 | 104248623 | chr9 | 104249475 | 104249562 |
| chr9 | 104500625 | 104500774 | chr9 | 106998039 | 106998134 | chr9 | 110126074 | 110126247 |
| chr9 | 110228200 | 110228602 | chr9 | 110251388 | 110251418 | chr9 | 110252363 | 110252515 |
| chr9 | 111894386 | 111894520 | chr9 | 112403170 | 112403200 | chr9 | 112403364 | 112403394 |
| chr9 | 113341522 | 113341621 | chr9 | 113341680 | 113341847 | chr9 | 113341927 | 113341965 |
| chr9 | 113342299 | 113342340 | chr9 | 114247454 | 114247578 | chr9 | 115067932 | 115068106 |
| chr9 | 115087567 | 115087597 | chr9 | 115478932 | 115479250 | chr9 | 115566363 | 115566583 |
| chr9 | 115652966 | 115653425 | chr9 | 116633883 | 116633987 | chr9 | 117050981 | 117051030 |
| chr9 | 118917024 | 118917079 | chr9 | 119603412 | 119603535 | chr9 | 120175795 | 120175832 |
| chr9 | 120176104 | 120176151 | chr9 | 120176867 | 120176897 | chr9 | 122131497 | 122131642 |
| chr9 | 122131880 | 122132025 | chr9 | 122132052 | 122132227 | chr9 | 123004898 | 123004928 |
| chr9 | 123295355 | 123295463 | chr9 | 124535347 | 124535611 | chr9 | 124749865 | 124749953 |
| chr9 | 124751485 | 124751515 | chr9 | 125676633 | 125676753 | chr9 | 125704789 | 125704835 |

TABLE 12-continued

Pan Cancer #2

| chr | start | end | chr | start | end | chr | start | end |
|---|---|---|---|---|---|---|---|---|
| chr9 | 126133778 | 126133856 | chr9 | 126154304 | 126154575 | chr9 | 126349038 | 126349104 |
| chr9 | 126770257 | 126770298 | chr9 | 126771532 | 126771705 | chr9 | 126774517 | 126774619 |
| chr9 | 126775530 | 126775560 | chr9 | 126776044 | 126776098 | chr9 | 126777529 | 126777746 |
| chr9 | 126777974 | 126777982 | chr9 | 126778359 | 126778496 | chr9 | 126779485 | 126780043 |
| chr9 | 126780285 | 126780315 | chr9 | 126780811 | 126780898 | chr9 | 126783295 | 126783499 |
| chr9 | 127212851 | 127213006 | chr9 | 127265876 | 127266025 | chr9 | 127266387 | 127266534 |
| chr9 | 127605297 | 127605327 | chr9 | 127630125 | 127630205 | chr9 | 127853274 | 127853304 |
| chr9 | 127920543 | 127920572 | chr9 | 128136065 | 128136095 | chr9 | 128635180 | 128635210 |
| chr9 | 128652200 | 128652232 | chr9 | 128759852 | 128759954 | chr9 | 129276718 | 129276820 |
| chr9 | 129372929 | 129373037 | chr9 | 129376170 | 129376199 | chr9 | 129376889 | 129376918 |
| chr9 | 129377214 | 129377316 | chr9 | 129377604 | 129377635 | chr9 | 129377773 | 129377959 |
| chr9 | 129387434 | 129387464 | chr9 | 129387848 | 129388200 | chr9 | 129388719 | 129388753 |
| chr9 | 129388996 | 129389192 | chr9 | 129400986 | 129401195 | chr9 | 129445255 | 129445566 |
| chr9 | 129445783 | 129445813 | chr9 | 129517783 | 129517821 | chr9 | 130248419 | 130248449 |
| chr9 | 130325967 | 130325997 | chr9 | 130461687 | 130461742 | chr9 | 130675509 | 130675615 |
| chr9 | 130689631 | 130689667 | chr9 | 130689742 | 130689749 | chr9 | 130694413 | 130694468 |
| chr9 | 130694809 | 130694948 | chr9 | 131177975 | 131178094 | chr9 | 131417698 | 131417940 |
| chr9 | 131542193 | 131542267 | chr9 | 131580038 | 131580257 | chr9 | 131607517 | 131607547 |
| chr9 | 131607770 | 131607800 | chr9 | 131854231 | 131854328 | chr9 | 131854564 | 131854732 |
| chr9 | 132373058 | 132373091 | chr9 | 132382635 | 132383109 | chr9 | 132383347 | 132383376 |
| chr9 | 132402840 | 132402883 | chr9 | 132403149 | 132403216 | chr9 | 132559377 | 132559456 |
| chr9 | 132804405 | 132804455 | chr9 | 132804796 | 132804974 | chr9 | 132805318 | 132805445 |
| chr9 | 132805737 | 132805893 | chr9 | 132815175 | 132815205 | chr9 | 132881814 | 132881844 |
| chr9 | 133308893 | 133308941 | chr9 | 133534683 | 133534713 | chr9 | 133535734 | 133535839 |
| chr9 | 133536097 | 133536119 | chr9 | 133536150 | 133536344 | chr9 | 133536778 | 133536869 |
| chr9 | 133537182 | 133537549 | chr9 | 133538169 | 133538728 | chr9 | 133539606 | 133539709 |
| chr9 | 133541059 | 133541192 | chr9 | 133541689 | 133542337 | chr9 | 133605601 | 133605631 |
| chr9 | 133738343 | 133738372 | chr9 | 133747505 | 133747534 | chr9 | 133773766 | 133773923 |
| chr9 | 133927347 | 133927481 | chr9 | 133928256 | 133928266 | chr9 | 134126670 | 134126741 |
| chr9 | 134191085 | 134191218 | chr9 | 134207916 | 134208048 | chr9 | 134421797 | 134421835 |
| chr9 | 134717313 | 134717367 | chr9 | 135037119 | 135037287 | chr9 | 135037334 | 135037357 |
| chr9 | 135073463 | 135073506 | chr9 | 135135114 | 135135247 | chr9 | 135231073 | 135231158 |
| chr9 | 135455407 | 135455585 | chr9 | 135455996 | 135456023 | chr9 | 135456476 | 135456544 |
| chr9 | 135456897 | 135456932 | chr9 | 135458477 | 135458597 | chr9 | 135460001 | 135460176 |
| chr9 | 135460869 | 135460899 | chr9 | 135461511 | 135461773 | chr9 | 135462048 | 135462077 |
| chr9 | 135462648 | 135462967 | chr9 | 135464798 | 135464918 | chr9 | 135465948 | 135466064 |
| chr9 | 135466118 | 135466132 | chr9 | 135466344 | 135466660 | chr9 | 135548238 | 135548313 |
| chr9 | 135590218 | 135590334 | chr9 | 135796801 | 135796830 | chr9 | 135865090 | 135865161 |
| chr9 | 135898911 | 135899124 | chr9 | 136474490 | 136474591 | chr9 | 137002646 | 137002692 |
| chr9 | 137111397 | 137111426 | chr9 | 137229892 | 137229921 | chr9 | 137299119 | 137299450 |
| chr9 | 137299670 | 137299699 | chr9 | 137534066 | 137534238 | chr9 | 137575915 | 137575945 |
| chr9 | 137656958 | 137657128 | chr9 | 137667327 | 137667357 | chr9 | 137702189 | 137702222 |
| chr9 | 137718901 | 137719001 | chr9 | 137722087 | 137722209 | chr9 | 137979893 | 137980011 |
| chr9 | 137980258 | 137980288 | chr9 | 137980880 | 137980910 | chr9 | 138265123 | 138265251 |
| chr9 | 138474557 | 138474590 | chr9 | 138563059 | 138563280 | chr9 | 138606821 | 138606923 |
| chr9 | 138627636 | 138627893 | chr9 | 138634047 | 138634159 | chr9 | 138659800 | 138659905 |
| chr9 | 138660943 | 138661012 | chr9 | 138661648 | 138661870 | chr9 | 138666455 | 138666558 |
| chr9 | 138826382 | 138826412 | chr9 | 138880711 | 138880875 | chr9 | 138991798 | 138991828 |
| chr9 | 139000566 | 139000642 | chr9 | 139012272 | 139012411 | chr9 | 139024750 | 139024782 |
| chr9 | 139045653 | 139045683 | chr9 | 139047532 | 139047633 | chr9 | 139085228 | 139085350 |
| chr9 | 139090500 | 139090551 | chr9 | 139091072 | 139091369 | chr9 | 139093773 | 139093890 |
| chr9 | 139094705 | 139094732 | chr9 | 139095340 | 139095485 | chr9 | 139096650 | 139097006 |
| chr9 | 139111268 | 139111298 | chr9 | 139269039 | 139269121 | chr9 | 139399407 | 139399436 |
| chr9 | 139421955 | 139421985 | chr9 | 139477862 | 139478020 | chr9 | 139698925 | 139699051 |
| chr9 | 139704008 | 139704279 | chr9 | 139859041 | 139859268 | chr9 | 139888945 | 139888980 |
| chr9 | 140015209 | 140015241 | chr9 | 140024842 | 140024918 | chr9 | 140024957 | 140025023 |
| chr9 | 140030498 | 140030528 | chr9 | 140031944 | 140032082 | chr9 | 140032891 | 140032951 |
| chr9 | 140033001 | 140033092 | chr9 | 140033426 | 140033490 | chr9 | 140033619 | 140033626 |
| chr9 | 140033909 | 140034079 | chr9 | 140050969 | 140051096 | chr9 | 140051220 | 140051354 |
| chr9 | 140127883 | 140128080 | chr9 | 140137310 | 140137488 | chr9 | 140197122 | 140197263 |
| chr9 | 140205394 | 140205519 | chr9 | 140245877 | 140245998 | chr9 | 140332708 | 140333018 |
| chr9 | 140382557 | 140382596 | chr9 | 140392454 | 140392484 | chr9 | 140397029 | 140397097 |
| chr9 | 140498318 | 140498394 | chr9 | 140507256 | 140507419 | chr9 | 140704046 | 140704131 |
| chr9 | 140709046 | 140709174 | chr9 | 140727471 | 140727511 | chr9 | 140727845 | 140727930 |
| chr9 | 140769943 | 140769973 | chr9 | 140771975 | 140772347 | chr9 | 140772586 | 140772593 |
| chr9 | 140772757 | 140773301 | chr10 | 524754 | 524784 | chr10 | 833307 | 833386 |
| chr10 | 978878 | 978933 | chr10 | 1080377 | 1080513 | chr10 | 1120778 | 1120937 |
| chr10 | 1577394 | 1577424 | chr10 | 1585111 | 1585239 | chr10 | 1651360 | 1651374 |
| chr10 | 1708327 | 1708478 | chr10 | 1774858 | 1774887 | chr10 | 1779417 | 1779744 |
| chr10 | 3109360 | 3109459 | chr10 | 3197004 | 3197113 | chr10 | 3285585 | 3285698 |
| chr10 | 3330499 | 3330618 | chr10 | 3641378 | 3641413 | chr10 | 3678597 | 3678637 |
| chr10 | 3895410 | 3895452 | chr10 | 4599917 | 4599965 | chr10 | 5530764 | 5530975 |
| chr10 | 5765021 | 5765059 | chr10 | 5855154 | 5855184 | chr10 | 5875140 | 5875396 |
| chr10 | 6003402 | 6003855 | chr10 | 6042309 | 6042571 | chr10 | 6162159 | 6162225 |
| chr10 | 6167619 | 6167742 | chr10 | 6206142 | 6206217 | chr10 | 6372343 | 6372373 |
| chr10 | 6513976 | 6514006 | chr10 | 6577643 | 6577673 | chr10 | 6586721 | 6586847 |

TABLE 12-continued

Pan Cancer #2

| chr | start | end | chr | start | end | chr | start | end |
|---|---|---|---|---|---|---|---|---|
| chr10 | 6963079 | 6963111 | chr10 | 6984463 | 6984639 | chr10 | 7205733 | 7205787 |
| chr10 | 7212745 | 7213064 | chr10 | 7213505 | 7213535 | chr10 | 7216059 | 7216089 |
| chr10 | 7236211 | 7236245 | chr10 | 7255730 | 7255821 | chr10 | 7323283 | 7323313 |
| chr10 | 7334737 | 7334767 | chr10 | 7363436 | 7363466 | chr10 | 7371678 | 7371708 |
| chr10 | 7414544 | 7414588 | chr10 | 7424626 | 7424687 | chr10 | 7436090 | 7436209 |
| chr10 | 7449954 | 7450189 | chr10 | 7450491 | 7451390 | chr10 | 7452227 | 7452777 |
| chr10 | 7453313 | 7453656 | chr10 | 7453903 | 7453930 | chr10 | 7708274 | 7708304 |
| chr10 | 7708790 | 7708856 | chr10 | 7708955 | 7709087 | chr10 | 7709723 | 7709752 |
| chr10 | 8055681 | 8055764 | chr10 | 8075930 | 8075944 | chr10 | 8076341 | 8076487 |
| chr10 | 8076804 | 8077374 | chr10 | 8077874 | 8078218 | chr10 | 8085039 | 8085721 |
| chr10 | 8085978 | 8086010 | chr10 | 8091895 | 8092278 | chr10 | 8093738 | 8093824 |
| chr10 | 8093860 | 8093963 | chr10 | 8095603 | 8095845 | chr10 | 8096160 | 8096190 |
| chr10 | 8096975 | 8097197 | chr10 | 8097474 | 8097537 | chr10 | 11059933 | 11060062 |
| chr10 | 11206206 | 11206235 | chr10 | 11207179 | 11207276 | chr10 | 11700918 | 11701075 |
| chr10 | 12390825 | 12390995 | chr10 | 12391870 | 12392327 | chr10 | 12554417 | 12554501 |
| chr10 | 13043386 | 13043425 | chr10 | 13140861 | 13141020 | chr10 | 13715208 | 13715401 |
| chr10 | 13933005 | 13933035 | chr10 | 13933436 | 13933538 | chr10 | 13933597 | 13933934 |
| chr10 | 13933983 | 13934125 | chr10 | 13934169 | 13934183 | chr10 | 14393819 | 14393893 |
| chr10 | 14966129 | 14966212 | chr10 | 15002784 | 15003006 | chr10 | 15140484 | 15140526 |
| chr10 | 15761292 | 15761671 | chr10 | 15762124 | 15762154 | chr10 | 16175687 | 16175801 |
| chr10 | 16562369 | 16562672 | chr10 | 16562710 | 16563664 | chr10 | 16563691 | 16563909 |
| chr10 | 16564087 | 16564116 | chr10 | 16564537 | 16564566 | chr10 | 17269259 | 17269288 |
| chr10 | 17269628 | 17269789 | chr10 | 17270072 | 17270445 | chr10 | 17270991 | 17271254 |
| chr10 | 17271444 | 17271625 | chr10 | 17271914 | 17272233 | chr10 | 17272601 | 17272630 |
| chr10 | 17273172 | 17273201 | chr10 | 17275584 | 17275613 | chr10 | 17277741 | 17277770 |
| chr10 | 17429165 | 17429622 | chr10 | 17496545 | 17496734 | chr10 | 17503402 | 17503520 |
| chr10 | 17509450 | 17509503 | chr10 | 18429628 | 18429774 | chr10 | 21101525 | 21101555 |
| chr10 | 21462533 | 21462607 | chr10 | 21462970 | 21463023 | chr10 | 21728064 | 21728124 |
| chr10 | 21805217 | 21805277 | chr10 | 22047635 | 22047635 | chr10 | 22541638 | 22541850 |
| chr10 | 22542025 | 22542249 | chr10 | 22567093 | 22567322 | chr10 | 22624022 | 22624305 |
| chr10 | 22624562 | 22625120 | chr10 | 22625383 | 22625782 | chr10 | 22625812 | 22625978 |
| chr10 | 22633985 | 22634174 | chr10 | 22634325 | 22634578 | chr10 | 22764649 | 22765791 |
| chr10 | 22765821 | 22765901 | chr10 | 23216865 | 23216945 | chr10 | 23460355 | 23460471 |
| chr10 | 23461222 | 23461754 | chr10 | 23462059 | 23462462 | chr10 | 23462486 | 23462614 |
| chr10 | 23462635 | 23462910 | chr10 | 23463267 | 23463853 | chr10 | 23463888 | 23464077 |
| chr10 | 23479876 | 23480696 | chr10 | 23480904 | 23481049 | chr10 | 23481321 | 23481515 |
| chr10 | 23481936 | 23482232 | chr10 | 23482289 | 23482445 | chr10 | 23483828 | 23484618 |
| chr10 | 23486264 | 23486328 | chr10 | 23487742 | 23487978 | chr10 | 23488393 | 23489158 |
| chr10 | 23489409 | 23489439 | chr10 | 23982438 | 23982820 | chr10 | 23983194 | 23983247 |
| chr10 | 23983618 | 23983700 | chr10 | 23984087 | 23984226 | chr10 | 23984923 | 23984991 |
| chr10 | 24988589 | 24988619 | chr10 | 25464619 | 25464915 | chr10 | 25465421 | 25465517 |
| chr10 | 26055811 | 26055841 | chr10 | 26223001 | 26223205 | chr10 | 26224031 | 26224061 |
| chr10 | 26500619 | 26500870 | chr10 | 26501539 | 26501589 | chr10 | 26503693 | 26503731 |
| chr10 | 26504114 | 26504143 | chr10 | 26504491 | 26504883 | chr10 | 26505009 | 26505227 |
| chr10 | 26505442 | 26505617 | chr10 | 26506057 | 26506163 | chr10 | 26506373 | 26506618 |
| chr10 | 26506903 | 26507400 | chr10 | 26681099 | 26681129 | chr10 | 26727098 | 26727368 |
| chr10 | 26727604 | 26727816 | chr10 | 26747051 | 26747159 | chr10 | 26803853 | 26803883 |
| chr10 | 26816766 | 26816938 | chr10 | 26931897 | 26931926 | chr10 | 27547946 | 27548331 |
| chr10 | 27548401 | 27548484 | chr10 | 27794496 | 27794588 | chr10 | 27846637 | 27846816 |
| chr10 | 28030892 | 28030925 | chr10 | 28032966 | 28033020 | chr10 | 28033410 | 28033481 |
| chr10 | 28033770 | 28034186 | chr10 | 28034327 | 28034341 | chr10 | 28034874 | 28035300 |
| chr10 | 28035615 | 28035782 | chr10 | 28287373 | 28287557 | chr10 | 28287777 | 28288070 |
| chr10 | 28657255 | 28657343 | chr10 | 28958086 | 28958129 | chr10 | 28964745 | 28964800 |
| chr10 | 29011047 | 29011162 | chr10 | 30026077 | 30026090 | chr10 | 30848200 | 30848230 |
| chr10 | 31073368 | 31073481 | chr10 | 31892922 | 31893079 | chr10 | 32499044 | 32499176 |
| chr10 | 32672459 | 32672489 | chr10 | 33233313 | 33233361 | chr10 | 33624166 | 33624230 |
| chr10 | 33624492 | 33624560 | chr10 | 35929334 | 35929528 | chr10 | 37051865 | 37051895 |
| chr10 | 38078948 | 38079105 | chr10 | 43186151 | 43186181 | chr10 | 43250009 | 43250039 |
| chr10 | 43250406 | 43250779 | chr10 | 43250855 | 43250886 | chr10 | 43428424 | 43428576 |
| chr10 | 43429067 | 43429100 | chr10 | 43429376 | 43429411 | chr10 | 43572685 | 43572734 |
| chr10 | 43600561 | 43600720 | chr10 | 43609055 | 43609117 | chr10 | 43609922 | 43609963 |
| chr10 | 43613890 | 43613919 | chr10 | 43614982 | 43615011 | chr10 | 43615554 | 43615607 |
| chr10 | 43617401 | 43617430 | chr10 | 43697887 | 43698086 | chr10 | 43698115 | 43698155 |
| chr10 | 43858343 | 43858470 | chr10 | 43905877 | 43906023 | chr10 | 44434176 | 44434206 |
| chr10 | 44879944 | 44880228 | chr10 | 44880869 | 44880915 | chr10 | 49652977 | 49653080 |
| chr10 | 49731548 | 49731749 | chr10 | 49732060 | 49732087 | chr10 | 49732156 | 49732498 |
| chr10 | 50323222 | 50323258 | chr10 | 50340119 | 50340149 | chr10 | 50507557 | 50507619 |
| chr10 | 50603967 | 50604159 | chr10 | 50604608 | 50604645 | chr10 | 50605057 | 50605654 |
| chr10 | 50606027 | 50606433 | chr10 | 50748131 | 50748350 | chr10 | 50817015 | 50817132 |
| chr10 | 50817858 | 50817872 | chr10 | 50818382 | 50818432 | chr10 | 50818987 | 50819102 |
| chr10 | 50821472 | 50821701 | chr10 | 50887655 | 50887753 | chr10 | 50887790 | 50887816 |
| chr10 | 50977034 | 50977048 | chr10 | 52177545 | 52177575 | chr10 | 53107427 | 53107563 |
| chr10 | 54068526 | 54068610 | chr10 | 54072982 | 54073020 | chr10 | 54073265 | 54073295 |
| chr10 | 54074744 | 54074789 | chr10 | 57387429 | 57387796 | chr10 | 57388325 | 57388510 |
| chr10 | 57390290 | 57390637 | chr10 | 57391166 | 57391215 | chr10 | 60273130 | 60273278 |
| chr10 | 60935887 | 60935996 | chr10 | 60936524 | 60936729 | chr10 | 60937073 | 60937103 |

TABLE 12-continued

Pan Cancer #2

| chr | start | end | chr | start | end | chr | start | end |
|---|---|---|---|---|---|---|---|---|
| chr10 | 63212324 | 63212701 | chr10 | 63669223 | 63669344 | chr10 | 64575526 | 64575638 |
| chr10 | 64578171 | 64578540 | chr10 | 65262111 | 65262304 | chr10 | 69578459 | 69578588 |
| chr10 | 69589153 | 69589407 | chr10 | 70167678 | 70167708 | chr10 | 70232345 | 70232485 |
| chr10 | 70275831 | 70275979 | chr10 | 70314814 | 70315148 | chr10 | 70565410 | 70565489 |
| chr10 | 70586494 | 70586540 | chr10 | 71084981 | 71085116 | chr10 | 71327725 | 71327764 |
| chr10 | 71328773 | 71328821 | chr10 | 71329079 | 71329118 | chr10 | 71329544 | 71329618 |
| chr10 | 71332052 | 71333018 | chr10 | 72015150 | 72015339 | chr10 | 72043779 | 72043894 |
| chr10 | 72200118 | 72200138 | chr10 | 72200354 | 72200771 | chr10 | 72201285 | 72201285 |
| chr10 | 72200825 | 72201285 | chr10 | 73156362 | 73156661 | chr10 | 73157867 | 73158027 |
| chr10 | 72973130 | 72973180 | chr10 | 75386789 | 75386893 | chr10 | 75388129 | 75388173 |
| chr10 | 75384100 | 75384130 | chr10 | 75488953 | 75489125 | chr10 | 77190039 | 77190068 |
| chr10 | 75407570 | 75407837 | chr10 | 79396921 | 79397089 | chr10 | 81023884 | 81023914 |
| chr10 | 77191224 | 77191368 | chr10 | 81664867 | 81664899 | chr10 | 81860447 | 81860568 |
| chr10 | 81154141 | 81154192 | chr10 | 82117074 | 82117271 | chr10 | 83634261 | 83634361 |
| chr10 | 81966737 | 81966828 | chr10 | 83635531 | 83635545 | chr10 | 85792257 | 85792287 |
| chr10 | 83634467 | 83634499 | chr10 | 88123672 | 88123701 | chr10 | 88149363 | 88149601 |
| chr10 | 85954425 | 85954457 | chr10 | 88684005 | 88684034 | chr10 | 88698834 | 88698914 |
| chr10 | 88304914 | 88304944 | chr10 | 89653788 | 89653859 | chr10 | 89685272 | 89685322 |
| chr10 | 89624255 | 89624311 | chr10 | 89692776 | 89693015 | chr10 | 89711861 | 89711992 |
| chr10 | 89690790 | 89690819 | chr10 | 89720790 | 89720885 | chr10 | 89725030 | 89725071 |
| chr10 | 89717610 | 89717744 | chr10 | 90968040 | 90968117 | chr10 | 91295029 | 91295067 |
| chr10 | 90966708 | 90966865 | chr10 | 92617242 | 92617308 | chr10 | 93647216 | 93647300 |
| chr10 | 91295585 | 91295725 | chr10 | 94062288 | 94062318 | chr10 | 94450675 | 94450726 |
| chr10 | 93647562 | 93647648 | chr10 | 94826023 | 94826056 | chr10 | 94828194 | 94828498 |
| chr10 | 94451448 | 94451602 | chr10 | 94834413 | 94835047 | chr10 | 95360716 | 95360750 |
| chr10 | 94828735 | 94828828 | chr10 | 98129822 | 98130033 | chr10 | 98528023 | 98528107 |
| chr10 | 96304020 | 96304329 | chr10 | 99051122 | 99051253 | chr10 | 99080262 | 99080447 |
| chr10 | 98558129 | 98558200 | chr10 | 99161398 | 99161560 | chr10 | 99474393 | 99474467 |
| chr10 | 99080862 | 99080930 | chr10 | 99531230 | 99531430 | chr10 | 99789175 | 99789282 |
| chr10 | 99481747 | 99481905 | chr10 | 99790590 | 99790664 | chr10 | 99790947 | 99791161 |
| chr10 | 99790261 | 99790318 | chr10 | 100992222 | 100992443 | chr10 | 100992882 | 100992916 |
| chr10 | 100991907 | 100992190 | chr10 | 100996046 | 100996224 | chr10 | 101088995 | 101089439 |
| chr10 | 100993537 | 100994016 | chr10 | 101280204 | 101280485 | chr10 | 101283464 | 101283658 |
| chr10 | 101089908 | 101090203 | chr10 | 101290180 | 101291142 | chr10 | 101292297 | 101292919 |
| chr10 | 101290117 | 101290160 | chr10 | 101294756 | 101295586 | chr10 | 101296768 | 101296800 |
| chr10 | 101293156 | 101293343 | chr10 | 101492942 | 101493074 | chr10 | 101874886 | 101875138 |
| chr10 | 101363207 | 101363418 | chr10 | 102322230 | 102322260 | chr10 | 102419400 | 102419681 |
| chr10 | 101988223 | 101988404 | chr10 | 102473856 | 102473932 | chr10 | 102483993 | 102484245 |
| chr10 | 102430699 | 102430761 | chr10 | 102495508 | 102495741 | chr10 | 102497273 | 102497708 |
| chr10 | 102484270 | 102484554 | chr10 | 102501359 | 102501389 | chr10 | 102507509 | 102507535 |
| chr10 | 102498280 | 102498433 | chr10 | 102589425 | 102589493 | chr10 | 102589786 | 102589915 |
| chr10 | 102508996 | 102509285 | chr10 | 102890941 | 102891582 | chr10 | 102891823 | 102891955 |
| chr10 | 102590152 | 102590415 | chr10 | 102894091 | 102895289 | chr10 | 102899173 | 102899601 |
| chr10 | 102893624 | 102893951 | chr10 | 102900263 | 102900575 | chr10 | 102906525 | 102906620 |
| chr10 | 102899807 | 102899855 | chr10 | 102976150 | 102976180 | chr10 | 102977051 | 102977412 |
| chr10 | 102975619 | 102975834 | chr10 | 102983435 | 102983749 | chr10 | 102984513 | 102984516 |
| chr10 | 102983153 | 102983379 | chr10 | 102986534 | 102986952 | chr10 | 102987207 | 102987558 |
| chr10 | 102985772 | 102985963 | chr10 | 102996116 | 102996480 | chr10 | 102996597 | 102996638 |
| chr10 | 102989629 | 102989659 | chr10 | 102998576 | 102998828 | chr10 | 103043975 | 103044227 |
| chr10 | 102997329 | 102997406 | chr10 | 103325743 | 103325773 | chr10 | 103425950 | 103426174 |
| chr10 | 103044301 | 103044366 | chr10 | 103535622 | 103535770 | chr10 | 103536227 | 103536256 |
| chr10 | 103432412 | 103432441 | chr10 | 103579635 | 103579713 | chr10 | 103814668 | 103814754 |
| chr10 | 103536300 | 103536416 | chr10 | 104170096 | 104170262 | chr10 | 104170408 | 104170732 |
| chr10 | 103930034 | 103930161 | chr10 | 105036701 | 105036863 | chr10 | 105037223 | 105037830 |
| chr10 | 105036542 | 105036658 | chr10 | 105155285 | 105155481 | chr10 | 105413627 | 105413784 |
| chr10 | 105126957 | 105127076 | chr10 | 105527028 | 105527057 | chr10 | 106398644 | 106398687 |
| chr10 | 105420861 | 105420891 | chr10 | 106399581 | 106400387 | chr10 | 106401323 | 106401432 |
| chr10 | 106398826 | 106398886 | chr10 | 106402272 | 106402325 | chr10 | 106402712 | 106402825 |
| chr10 | 106401511 | 106402190 | chr10 | 108924045 | 108924059 | chr10 | 110671930 | 110672245 |
| chr10 | 108469972 | 108470093 | chr10 | 112403151 | 112403297 | chr10 | 112440378 | 112440408 |
| chr10 | 111216789 | 111216803 | chr10 | 115925505 | 115925552 | chr10 | 116164248 | 116164341 |
| chr10 | 115804840 | 115805014 | chr10 | 116853875 | 116853908 | chr10 | 118030642 | 118030705 |
| chr10 | 116331126 | 116331156 | chr10 | 118031625 | 118032229 | chr10 | 118032413 | 118032547 |
| chr10 | 118031302 | 118031548 | chr10 | 118034143 | 118034168 | chr10 | 118609305 | 118609390 |
| chr10 | 118032917 | 118033542 | chr10 | 118891517 | 118891661 | chr10 | 118891716 | 118891774 |
| chr10 | 118890980 | 118891104 | chr10 | 118892518 | 118893266 | chr10 | 118893680 | 118893825 |
| chr10 | 118892013 | 118892456 | chr10 | 118896629 | 118896805 | chr10 | 118897913 | 118897968 |
| chr10 | 118894035 | 118894071 | chr10 | 118899583 | 118899602 | chr10 | 118899893 | 118899957 |
| chr10 | 118899273 | 118899302 | chr10 | 118900324 | 118900498 | chr10 | 118922143 | 118922208 |
| chr10 | 118900166 | 118900244 | chr10 | 118923138 | 118923259 | chr10 | 118924604 | 118924896 |
| chr10 | 118922721 | 118922901 | chr10 | 118928548 | 118928727 | chr10 | 119000690 | 119001154 |
| chr10 | 118927086 | 118927296 | chr10 | 119294352 | 119294461 | chr10 | 119294847 | 119294897 |
| chr10 | 119001534 | 119001564 | chr10 | 119296756 | 119296788 | chr10 | 119297384 | 119297529 |
| chr10 | 119294909 | 119295245 | chr10 | 119302141 | 119302155 | chr10 | 119302222 | 119302266 |
| chr10 | 119301365 | 119301427 | chr10 | 119304363 | 119304393 | chr10 | 119304896 | 119304985 |
| chr10 | 119302962 | 119303174 | chr10 | 119307022 | 119307052 | chr10 | 119311867 | 119311897 |
| chr10 | 119305062 | 119305109 | | | | | | |

TABLE 12-continued

Pan Cancer #2

| chr | start | end | chr | start | end | chr | start | end |
|---|---|---|---|---|---|---|---|---|
| chr10 | 119312751 | 119313193 | chr10 | 119590435 | 119590464 | chr10 | 119807026 | 119807056 |
| chr10 | 120354243 | 120354273 | chr10 | 120355548 | 120355614 | chr10 | 120707028 | 120707111 |
| chr10 | 120800789 | 120800835 | chr10 | 120841558 | 120841590 | chr10 | 120937014 | 120937139 |
| chr10 | 121267480 | 121267626 | chr10 | 121307542 | 121307572 | chr10 | 122216896 | 122217083 |
| chr10 | 122708495 | 122708691 | chr10 | 122708992 | 122709022 | chr10 | 123256044 | 123256232 |
| chr10 | 123258020 | 123258091 | chr10 | 123274758 | 123274787 | chr10 | 123279548 | 123279697 |
| chr10 | 123357206 | 123357242 | chr10 | 123357766 | 123357893 | chr10 | 123667184 | 123667222 |
| chr10 | 123688711 | 123688741 | chr10 | 123922645 | 123922682 | chr10 | 124893178 | 124893192 |
| chr10 | 124893238 | 124893350 | chr10 | 124893635 | 124893765 | chr10 | 124893965 | 124894479 |
| chr10 | 124894889 | 124894922 | chr10 | 124895426 | 124895695 | chr10 | 124895833 | 124896456 |
| chr10 | 124897220 | 124897973 | chr10 | 124899035 | 124899116 | chr10 | 124899754 | 124899786 |
| chr10 | 124901892 | 124902046 | chr10 | 124902139 | 124902568 | chr10 | 124902608 | 124903238 |
| chr10 | 124904921 | 124905119 | chr10 | 124905481 | 124905511 | chr10 | 124905920 | 124906174 |
| chr10 | 124906436 | 124906544 | chr10 | 124907312 | 124907534 | chr10 | 124908091 | 124908121 |
| chr10 | 124909086 | 124909114 | chr10 | 124909253 | 124909537 | chr10 | 124909674 | 124909725 |
| chr10 | 124910363 | 124910454 | chr10 | 124910709 | 124911048 | chr10 | 125425515 | 125425547 |
| chr10 | 125527754 | 125527784 | chr10 | 125650866 | 125651162 | chr10 | 125851328 | 125851645 |
| chr10 | 125852299 | 125852497 | chr10 | 125852753 | 125853191 | chr10 | 126101966 | 126102095 |
| chr10 | 126135927 | 126136065 | chr10 | 126136506 | 126136723 | chr10 | 126137181 | 126137405 |
| chr10 | 126198949 | 126199077 | chr10 | 126697789 | 126698107 | chr10 | 126782965 | 126783048 |
| chr10 | 126828994 | 126829024 | chr10 | 127406313 | 127406386 | chr10 | 127693923 | 127693959 |
| chr10 | 128076561 | 128076630 | chr10 | 128993904 | 128994446 | chr10 | 128994727 | 128994903 |
| chr10 | 129379338 | 129379367 | chr10 | 129534993 | 129535446 | chr10 | 129535696 | 129535733 |
| chr10 | 129536080 | 129536223 | chr10 | 129536259 | 129536310 | chr10 | 129888804 | 129888885 |
| chr10 | 129948111 | 129948140 | chr10 | 130085356 | 130085362 | chr10 | 130203435 | 130203480 |
| chr10 | 130338727 | 130338768 | chr10 | 130338804 | 130338976 | chr10 | 130577764 | 130577794 |
| chr10 | 131348513 | 131348793 | chr10 | 131647903 | 131647933 | chr10 | 131761378 | 131761441 |
| chr10 | 131761687 | 131761725 | chr10 | 131762087 | 131762124 | chr10 | 131762592 | 131762631 |
| chr10 | 131762904 | 131762940 | chr10 | 131763633 | 131763717 | chr10 | 131767372 | 131767503 |
| chr10 | 131767543 | 131767649 | chr10 | 131768724 | 131769029 | chr10 | 131769533 | 131770237 |
| chr10 | 131770657 | 131770687 | chr10 | 131770988 | 131771093 | chr10 | 131936451 | 131936626 |
| chr10 | 131937355 | 131937428 | chr10 | 132000973 | 132001015 | chr10 | 132001252 | 132001556 |
| chr10 | 133109192 | 133109260 | chr10 | 133110554 | 133110704 | chr10 | 133794883 | 133795241 |
| chr10 | 133795313 | 133795430 | chr10 | 133795682 | 133795883 | chr10 | 133795976 | 133796058 |
| chr10 | 133849598 | 133850008 | chr10 | 133850529 | 133850774 | chr10 | 133951602 | 133952025 |
| chr10 | 133979059 | 133979089 | chr10 | 134000008 | 134000052 | chr10 | 134000109 | 134000124 |
| chr10 | 134001140 | 134001260 | chr10 | 134016203 | 134016388 | chr10 | 134022845 | 134022875 |
| chr10 | 134039087 | 134039117 | chr10 | 134092153 | 134092202 | chr10 | 134095594 | 134095833 |
| chr10 | 134119401 | 134119447 | chr10 | 134121401 | 134121430 | chr10 | 134273064 | 134273156 |
| chr10 | 134301095 | 134301212 | chr10 | 134481320 | 134481433 | chr10 | 134491021 | 134491114 |
| chr10 | 134499773 | 134499803 | chr10 | 134593329 | 134593416 | chr10 | 134598087 | 134598090 |
| chr10 | 134598368 | 134598530 | chr10 | 134599432 | 134599482 | chr10 | 134599808 | 134600016 |
| chr10 | 134600038 | 134600998 | chr10 | 134601556 | 134601715 | chr10 | 134602183 | 134602269 |
| chr10 | 134607970 | 134608183 | chr10 | 134665147 | 134665202 | chr10 | 134679129 | 134679265 |
| chr10 | 134690559 | 134690617 | chr10 | 134693587 | 134693709 | chr10 | 134699872 | 134699909 |
| chr10 | 134733221 | 134733275 | chr10 | 134733497 | 134733617 | chr10 | 134738378 | 134738642 |
| chr10 | 134755773 | 134756183 | chr10 | 134788083 | 134788251 | chr10 | 134794271 | 134794342 |
| chr10 | 134796012 | 134796042 | chr10 | 134896060 | 134896092 | chr10 | 134901193 | 134901511 |
| chr10 | 134902008 | 134902124 | chr10 | 134902188 | 134902307 | chr10 | 134916714 | 134916774 |
| chr10 | 134941145 | 134941178 | chr10 | 134942802 | 134943114 | chr10 | 134943445 | 134943542 |
| chr10 | 134944742 | 134944772 | chr10 | 134959217 | 134959391 | chr10 | 135002063 | 135002156 |
| chr10 | 135014963 | 135015132 | chr10 | 135017049 | 135017129 | chr10 | 135018032 | 135018070 |
| chr10 | 135018825 | 135018960 | chr10 | 135020801 | 135020893 | chr10 | 135023470 | 135023500 |
| chr10 | 135043088 | 135043538 | chr10 | 135043968 | 135044128 | chr10 | 135044555 | 135044573 |
| chr10 | 135048782 | 135048939 | chr10 | 135050311 | 135050679 | chr10 | 135076368 | 135076503 |
| chr10 | 135121316 | 135121345 | chr10 | 135121807 | 135122251 | chr10 | 135122742 | 135122808 |
| chr10 | 135122991 | 135123020 | chr10 | 135139555 | 135139730 | chr10 | 135153956 | 135154001 |
| chr11 | 232863 | 233062 | chr11 | 392576 | 392720 | chr11 | 394815 | 394968 |
| chr11 | 406876 | 406939 | chr11 | 407427 | 407463 | chr11 | 505732 | 505869 |
| chr11 | 518400 | 518430 | chr11 | 526389 | 526419 | chr11 | 533451 | 533567 |
| chr11 | 533859 | 533888 | chr11 | 534273 | 534302 | chr11 | 548731 | 548800 |
| chr11 | 611099 | 611128 | chr11 | 611691 | 611791 | chr11 | 636644 | 636673 |
| chr11 | 636895 | 636906 | chr11 | 637162 | 637263 | chr11 | 637350 | 637441 |
| chr11 | 679692 | 679722 | chr11 | 726417 | 726466 | chr11 | 763323 | 763686 |
| chr11 | 775261 | 775291 | chr11 | 829543 | 829708 | chr11 | 830174 | 830243 |
| chr11 | 850555 | 850823 | chr11 | 861612 | 861657 | chr11 | 863062 | 863092 |
| chr11 | 1006077 | 1006107 | chr11 | 1027540 | 1027574 | chr11 | 1029238 | 1029403 |
| chr11 | 1030215 | 1030296 | chr11 | 1080391 | 1080454 | chr11 | 1081667 | 1081715 |
| chr11 | 1214665 | 1214917 | chr11 | 1215899 | 1215999 | chr11 | 1229945 | 1229975 |
| chr11 | 1244381 | 1244465 | chr11 | 1250889 | 1250924 | chr11 | 1251183 | 1251351 |
| chr11 | 1263602 | 1263644 | chr11 | 1274085 | 1274189 | chr11 | 1318403 | 1318432 |
| chr11 | 1358291 | 1358332 | chr11 | 1374959 | 1375003 | chr11 | 1411875 | 1411905 |
| chr11 | 1430714 | 1430794 | chr11 | 1464280 | 1464428 | chr11 | 1469228 | 1469379 |
| chr11 | 1471920 | 1472058 | chr11 | 1868081 | 1868237 | chr11 | 1946130 | 1946160 |
| chr11 | 1957391 | 1957530 | chr11 | 1959077 | 1959187 | chr11 | 2040107 | 2040148 |
| chr11 | 2209907 | 2210278 | chr11 | 2226048 | 2226078 | chr11 | 2278708 | 2278839 |

TABLE 12-continued

Pan Cancer #2

| chr | start | end | chr | start | end | chr | start | end |
|---|---|---|---|---|---|---|---|---|
| chr11 | 2291259 | 2291493 | chr11 | 2291984 | 2292057 | chr11 | 2292106 | 2292359 |
| chr11 | 2292392 | 2292636 | chr11 | 2402376 | 2402405 | chr11 | 2437991 | 2438144 |
| chr11 | 2465350 | 2465447 | chr11 | 2465462 | 2465491 | chr11 | 2466597 | 2466788 |
| chr11 | 2884103 | 2884143 | chr11 | 2884159 | 2884309 | chr11 | 3027425 | 3027562 |
| chr11 | 3169665 | 3169835 | chr11 | 3181913 | 3181942 | chr11 | 3182104 | 3182133 |
| chr11 | 3511446 | 3511501 | chr11 | 3767205 | 3767284 | chr11 | 4038082 | 4038176 |
| chr11 | 4095819 | 4095864 | chr11 | 4209105 | 4209134 | chr11 | 4209382 | 4209411 |
| chr11 | 5641077 | 5641140 | chr11 | 5993897 | 5994029 | chr11 | 6497192 | 6497222 |
| chr11 | 7274215 | 7274245 | chr11 | 7695432 | 7695528 | chr11 | 8040536 | 8040563 |
| chr11 | 8040582 | 8040770 | chr11 | 8103002 | 8103115 | chr11 | 8189987 | 8190766 |
| chr11 | 8284535 | 8284760 | chr11 | 8289517 | 8289745 | chr11 | 8290195 | 8290423 |
| chr11 | 8615674 | 8615704 | chr11 | 9025970 | 9026348 | chr11 | 9112446 | 9112585 |
| chr11 | 9112640 | 9112741 | chr11 | 9405392 | 9405752 | chr11 | 10509678 | 10509807 |
| chr11 | 10811151 | 10811224 | chr11 | 10815867 | 10815998 | chr11 | 12029957 | 12030272 |
| chr11 | 12030823 | 12030852 | chr11 | 12132524 | 12132559 | chr11 | 12399040 | 12399222 |
| chr11 | 12399727 | 12399791 | chr11 | 12695481 | 12695495 | chr11 | 12695573 | 12695611 |
| chr11 | 12696611 | 12696746 | chr11 | 13030566 | 13030890 | chr11 | 13690121 | 13690157 |
| chr11 | 13711492 | 13711529 | chr11 | 14316375 | 14316404 | chr11 | 14543250 | 14543304 |
| chr11 | 14866247 | 14866285 | chr11 | 15136085 | 15136394 | chr11 | 16628819 | 16628933 |
| chr11 | 16632514 | 16632670 | chr11 | 17497492 | 17497520 | chr11 | 17497546 | 17497685 |
| chr11 | 17740493 | 17740570 | chr11 | 17741679 | 17741889 | chr11 | 17741953 | 17742445 |
| chr11 | 17743742 | 17743775 | chr11 | 18100096 | 18100259 | chr11 | 18812614 | 18812653 |
| chr11 | 18813032 | 18813086 | chr11 | 18813451 | 18813542 | chr11 | 18813792 | 18813947 |
| chr11 | 19263848 | 19263878 | chr11 | 19367102 | 19367134 | chr11 | 19367268 | 19367330 |
| chr11 | 19735730 | 19735760 | chr11 | 20153718 | 20153764 | chr11 | 20178094 | 20178305 |
| chr11 | 20180279 | 20180793 | chr11 | 20181213 | 20181254 | chr11 | 20181725 | 20181993 |
| chr11 | 20182864 | 20182959 | chr11 | 20183251 | 20183421 | chr11 | 20183674 | 20183773 |
| chr11 | 20184569 | 20185410 | chr11 | 20229058 | 20229550 | chr11 | 20229863 | 20230091 |
| chr11 | 20230398 | 20230464 | chr11 | 20408241 | 20408341 | chr11 | 20618197 | 20618392 |
| chr11 | 20618423 | 20618924 | chr11 | 20619717 | 20619974 | chr11 | 20621341 | 20621644 |
| chr11 | 20622705 | 20622792 | chr11 | 20623259 | 20623359 | chr11 | 20690653 | 20690877 |
| chr11 | 20691219 | 20691379 | chr11 | 20691432 | 20691452 | chr11 | 20691748 | 20691914 |
| chr11 | 20692453 | 20692529 | chr11 | 22215123 | 22215287 | chr11 | 22362934 | 22363189 |
| chr11 | 22364821 | 22364975 | chr11 | 22365407 | 22365477 | chr11 | 27742185 | 27742215 |
| chr11 | 27743115 | 27743173 | chr11 | 27743436 | 27743608 | chr11 | 27744147 | 27744504 |
| chr11 | 27744711 | 27744744 | chr11 | 30037593 | 30037743 | chr11 | 30038689 | 30038739 |
| chr11 | 30605919 | 30606123 | chr11 | 30606796 | 30606864 | chr11 | 30607367 | 30607409 |
| chr11 | 31760124 | 31760235 | chr11 | 31818458 | 31818512 | chr11 | 31818571 | 31818652 |
| chr11 | 31819302 | 31819833 | chr11 | 31820045 | 31820360 | chr11 | 31820461 | 31821025 |
| chr11 | 31821297 | 31821778 | chr11 | 31822325 | 31822393 | chr11 | 31824300 | 31824355 |
| chr11 | 31824564 | 31824680 | chr11 | 31825017 | 31825280 | chr11 | 31825696 | 31825754 |
| chr11 | 31825833 | 31826070 | chr11 | 31826107 | 31826303 | chr11 | 31826409 | 31826732 |
| chr11 | 31827114 | 31827204 | chr11 | 31827438 | 31827519 | chr11 | 31827598 | 31828123 |
| chr11 | 31833097 | 31833155 | chr11 | 31835707 | 31835797 | chr11 | 31836046 | 31836470 |
| chr11 | 31837019 | 31837512 | chr11 | 31837542 | 31838392 | chr11 | 31838678 | 31839051 |
| chr11 | 31839307 | 31839945 | chr11 | 31840042 | 31840080 | chr11 | 31840603 | 31840710 |
| chr11 | 31840769 | 31840922 | chr11 | 31841376 | 31842088 | chr11 | 31842175 | 31842276 |
| chr11 | 31846022 | 31846230 | chr11 | 31846434 | 31846985 | chr11 | 31847250 | 31847301 |
| chr11 | 31847371 | 31847712 | chr11 | 31847770 | 31847872 | chr11 | 31847896 | 31847925 |
| chr11 | 31848472 | 31848602 | chr11 | 31848723 | 31849300 | chr11 | 32009104 | 32009126 |
| chr11 | 32354844 | 32354959 | chr11 | 32355000 | 32355197 | chr11 | 32448583 | 32448893 |
| chr11 | 32455602 | 32455634 | chr11 | 32455841 | 32456025 | chr11 | 32456279 | 32456445 |
| chr11 | 32456759 | 32457176 | chr11 | 32457712 | 32458175 | chr11 | 32458389 | 32458823 |
| chr11 | 32459684 | 32460071 | chr11 | 32460468 | 32460515 | chr11 | 32460796 | 32460864 |
| chr11 | 33037467 | 33037556 | chr11 | 33264773 | 33264935 | chr11 | 33277455 | 33277485 |
| chr11 | 33318780 | 33318945 | chr11 | 33858324 | 33858463 | chr11 | 33890297 | 33890334 |
| chr11 | 33993984 | 33994014 | chr11 | 34535093 | 34535123 | chr11 | 35547499 | 35547562 |
| chr11 | 35641683 | 35641718 | chr11 | 35684958 | 35685131 | chr11 | 43596513 | 43596608 |
| chr11 | 43600453 | 43600557 | chr11 | 43601094 | 43601467 | chr11 | 43602468 | 43603036 |
| chr11 | 43603077 | 43603228 | chr11 | 43603628 | 43604145 | chr11 | 44325688 | 44325747 |
| chr11 | 44326137 | 44326184 | chr11 | 44327252 | 44327413 | chr11 | 44330878 | 44331439 |
| chr11 | 44331483 | 44331711 | chr11 | 44333052 | 44333081 | chr11 | 44333371 | 44333461 |
| chr11 | 44333477 | 44333480 | chr11 | 44337533 | 44337571 | chr11 | 44337727 | 44337861 |
| chr11 | 44337883 | 44338057 | chr11 | 44338335 | 44338367 | chr11 | 44340823 | 44340858 |
| chr11 | 44341966 | 44342034 | chr11 | 46227561 | 46227654 | chr11 | 46316896 | 46317355 |
| chr11 | 46317408 | 46317680 | chr11 | 46413042 | 46413304 | chr11 | 46866293 | 46866510 |
| chr11 | 46940419 | 46940531 | chr11 | 46959190 | 46959251 | chr11 | 47209044 | 47209189 |
| chr11 | 47260168 | 47260258 | chr11 | 47358926 | 47359237 | chr11 | 47363557 | 47363625 |
| chr11 | 47372828 | 47373002 | chr11 | 47478438 | 47478500 | chr11 | 47485995 | 47486141 |
| chr11 | 57194355 | 57194509 | chr11 | 57235406 | 57235436 | chr11 | 57414663 | 57414663 |
| chr11 | 57437157 | 57437234 | chr11 | 57500982 | 57501068 | chr11 | 58672746 | 58673064 |
| chr11 | 59323596 | 59323729 | chr11 | 59329086 | 59329240 | chr11 | 59333405 | 59333541 |
| chr11 | 59841403 | 59841533 | chr11 | 60718668 | 60718853 | chr11 | 60718977 | 60719163 |
| chr11 | 60927079 | 60927319 | chr11 | 61049694 | 61049736 | chr11 | 61058283 | 61058341 |
| chr11 | 61062822 | 61063023 | chr11 | 61063062 | 61063138 | chr11 | 61148730 | 61148768 |
| chr11 | 61154806 | 61154836 | chr11 | 61277002 | 61277119 | chr11 | 61536985 | 61537014 |

TABLE 12-continued

Pan Cancer #2

| chr | start | end | chr | start | end | chr | start | end |
|---|---|---|---|---|---|---|---|---|
| chr11 | 61595086 | 61595262 | chr11 | 61596420 | 61596640 | chr11 | 61664655 | 61664770 |
| chr11 | 61666106 | 61666136 | chr11 | 61811996 | 61812151 | chr11 | 61880361 | 61880398 |
| chr11 | 62370720 | 62370750 | chr11 | 62440509 | 62440588 | chr11 | 62484517 | 62484547 |
| chr11 | 62497600 | 62497630 | chr11 | 62555752 | 62555782 | chr11 | 63202941 | 63203091 |
| chr11 | 63431856 | 63431918 | chr11 | 63432139 | 63432218 | chr11 | 63609824 | 63610013 |
| chr11 | 63641072 | 63641256 | chr11 | 63839478 | 63839528 | chr11 | 63849394 | 63849426 |
| chr11 | 63934498 | 63934619 | chr11 | 64105954 | 64106108 | chr11 | 64120879 | 64120909 |
| chr11 | 64140397 | 64140427 | chr11 | 64410723 | 64410759 | chr11 | 64480429 | 64480593 |
| chr11 | 64480824 | 64481042 | chr11 | 64490435 | 64490561 | chr11 | 64490792 | 64490806 |
| chr11 | 64490826 | 64491159 | chr11 | 64578577 | 64578743 | chr11 | 64739468 | 64739508 |
| chr11 | 64796439 | 64796571 | chr11 | 64809584 | 64809906 | chr11 | 64903331 | 64903361 |
| chr11 | 64950292 | 64950374 | chr11 | 65091272 | 65091369 | chr11 | 65185548 | 65185728 |
| chr11 | 65364470 | 65364557 | chr11 | 65405659 | 65405774 | chr11 | 65409759 | 65409861 |
| chr11 | 65448943 | 65449022 | chr11 | 65478376 | 65478611 | chr11 | 65510941 | 65511172 |
| chr11 | 65511392 | 65511522 | chr11 | 65554043 | 65554410 | chr11 | 65600810 | 65601640 |
| chr11 | 65778952 | 65778981 | chr11 | 65779317 | 65779357 | chr11 | 65816447 | 65816519 |
| chr11 | 65816561 | 65816564 | chr11 | 65891131 | 65891227 | chr11 | 66114279 | 66114331 |
| chr11 | 66138094 | 66138260 | chr11 | 66188115 | 66188145 | chr11 | 66188473 | 66188484 |
| chr11 | 66188571 | 66188783 | chr11 | 66188853 | 66188974 | chr11 | 66324254 | 66324447 |
| chr11 | 66454424 | 66454454 | chr11 | 66511223 | 66511431 | chr11 | 66513217 | 66513646 |
| chr11 | 66557543 | 66557710 | chr11 | 66625207 | 66625240 | chr11 | 66649028 | 66649058 |
| chr11 | 66658224 | 66658290 | chr11 | 66725600 | 66725637 | chr11 | 66790621 | 66790655 |
| chr11 | 67072239 | 67072396 | chr11 | 67139422 | 67139460 | chr11 | 67139535 | 67139546 |
| chr11 | 67210017 | 67210057 | chr11 | 67248321 | 67248458 | chr11 | 67350180 | 67350340 |
| chr11 | 67350961 | 67350990 | chr11 | 67462643 | 67462833 | chr11 | 67764187 | 67764254 |
| chr11 | 67781196 | 67781564 | chr11 | 67797202 | 67797420 | chr11 | 67918044 | 67918145 |
| chr11 | 67999703 | 67999866 | chr11 | 68096034 | 68096179 | chr11 | 68118716 | 68118745 |
| chr11 | 68153950 | 68154098 | chr11 | 68181217 | 68181288 | chr11 | 68221758 | 68222056 |
| chr11 | 68409558 | 68409588 | chr11 | 68804776 | 68804770 | chr11 | 69192566 | 69192784 |
| chr11 | 69280561 | 69280633 | chr11 | 69466004 | 69466042 | chr11 | 69484356 | 69484454 |
| chr11 | 69516968 | 69517174 | chr11 | 69518030 | 69518211 | chr11 | 69518530 | 69518718 |
| chr11 | 69588930 | 69589184 | chr11 | 69589824 | 69589854 | chr11 | 69590149 | 69590222 |
| chr11 | 70211516 | 70211545 | chr11 | 71192746 | 71192889 | chr11 | 71318332 | 71318809 |
| chr11 | 71318953 | 71318967 | chr11 | 71647544 | 71647574 | chr11 | 71792437 | 71792496 |
| chr11 | 71863650 | 71863785 | chr11 | 71951639 | 71951738 | chr11 | 71952340 | 71952416 |
| chr11 | 71952459 | 71952541 | chr11 | 71954612 | 71954642 | chr11 | 71955344 | 71955377 |
| chr11 | 71956007 | 71956340 | chr11 | 72413980 | 72414010 | chr11 | 72432837 | 72432916 |
| chr11 | 72475677 | 72475711 | chr11 | 72532348 | 72532378 | chr11 | 72929747 | 72929883 |
| chr11 | 73072907 | 73072953 | chr11 | 73310367 | 73310441 | chr11 | 73481055 | 73481085 |
| chr11 | 73561763 | 73561798 | chr11 | 73685698 | 73685845 | chr11 | 73694609 | 73694659 |
| chr11 | 74246487 | 74246521 | chr11 | 74394491 | 74394600 | chr11 | 74953265 | 74953336 |
| chr11 | 75379283 | 75379895 | chr11 | 75459486 | 75459775 | chr11 | 75858210 | 75858240 |
| chr11 | 75859012 | 75859053 | chr11 | 76293588 | 76293618 | chr11 | 76371738 | 76372077 |
| chr11 | 76594692 | 76594722 | chr11 | 77533964 | 77534145 | chr11 | 78672917 | 78672964 |
| chr11 | 79151173 | 79151216 | chr11 | 82444376 | 82445101 | chr11 | 82998001 | 82998121 |
| chr11 | 85709169 | 85709254 | chr11 | 86085742 | 86085861 | chr11 | 86085932 | 86085968 |
| chr11 | 86383167 | 86383710 | chr11 | 88241705 | 88241975 | chr11 | 88242131 | 88242274 |
| chr11 | 88242359 | 88242618 | chr11 | 88799082 | 88799209 | chr11 | 89052235 | 89052282 |
| chr11 | 89867794 | 89867990 | chr11 | 91957500 | 91957674 | chr11 | 91957974 | 91958230 |
| chr11 | 91958734 | 91959326 | chr11 | 91959375 | 91959430 | chr11 | 91959899 | 91960045 |
| chr11 | 93063583 | 93063645 | chr11 | 93063870 | 93063948 | chr11 | 93911651 | 93911800 |
| chr11 | 94134086 | 94134463 | chr11 | 94134683 | 94134853 | chr11 | 94275794 | 94275951 |
| chr11 | 94278456 | 94278603 | chr11 | 94473600 | 94473768 | chr11 | 94473803 | 94474139 |
| chr11 | 94474356 | 94474385 | chr11 | 94502334 | 94502489 | chr11 | 94884130 | 94884160 |
| chr11 | 96517902 | 96517932 | chr11 | 98891477 | 98891882 | chr11 | 100997649 | 100997981 |
| chr11 | 100998276 | 100998318 | chr11 | 100998667 | 100998744 | chr11 | 101453180 | 101453518 |
| chr11 | 101723359 | 101723455 | chr11 | 102158378 | 102158427 | chr11 | 102961347 | 102961649 |
| chr11 | 102962922 | 102963062 | chr11 | 102980027 | 102980056 | chr11 | 104034521 | 104034996 |
| chr11 | 105480755 | 105480786 | chr11 | 105481216 | 105481571 | chr11 | 106888308 | 106888429 |
| chr11 | 106888641 | 106888801 | chr11 | 107461623 | 107461653 | chr11 | 107462415 | 107462459 |
| chr11 | 108236072 | 108236101 | chr11 | 108603233 | 108603263 | chr11 | 109292906 | 109293052 |
| chr11 | 109293720 | 109293763 | chr11 | 110166519 | 110166935 | chr11 | 110582232 | 110582434 |
| chr11 | 110582895 | 110583028 | chr11 | 110583044 | 110583050 | chr11 | 110583574 | 110583730 |
| chr11 | 111383183 | 111383531 | chr11 | 111383558 | 111383682 | chr11 | 111411093 | 111411581 |
| chr11 | 111411822 | 111412061 | chr11 | 111783548 | 111783577 | chr11 | 111976911 | 111976941 |
| chr11 | 114113022 | 114113052 | chr11 | 115375120 | 115375177 | chr11 | 115530222 | 115530604 |
| chr11 | 115630531 | 115630910 | chr11 | 115631307 | 115631364 | chr11 | 116147253 | 116147283 |
| chr11 | 116451023 | 116451190 | chr11 | 116976126 | 116976156 | chr11 | 116984568 | 116984665 |
| chr11 | 117017686 | 117017773 | chr11 | 117055950 | 117056073 | chr11 | 117296921 | 117297109 |
| chr11 | 118724458 | 118724605 | chr11 | 118991033 | 118991079 | chr11 | 119148865 | 119148945 |
| chr11 | 119149236 | 119149265 | chr11 | 119292779 | 119292809 | chr11 | 119293370 | 119293615 |
| chr11 | 119612227 | 119612267 | chr11 | 119612324 | 119612399 | chr11 | 119612861 | 119613075 |
| chr11 | 120008105 | 120008504 | chr11 | 120039833 | 120039865 | chr11 | 120367948 | 120368008 |
| chr11 | 120435405 | 120435477 | chr11 | 120435800 | 120435830 | chr11 | 120894800 | 120895026 |
| chr11 | 120998701 | 120998825 | chr11 | 121152057 | 121152203 | chr11 | 122847265 | 122847696 |
| chr11 | 122848079 | 122848312 | chr11 | 122848369 | 122848591 | chr11 | 122849301 | 122849331 |

TABLE 12-continued

Pan Cancer #2

| chr | start | end | chr | start | end | chr | start | end |
|---|---|---|---|---|---|---|---|---|
| chr11 | 122849642 | 122850123 | chr11 | 122850149 | 122850163 | chr11 | 122850424 | 122850536 |
| chr11 | 122851177 | 122851209 | chr11 | 122852438 | 122852475 | chr11 | 122855008 | 122855043 |
| chr11 | 122895443 | 122895485 | chr11 | 122961054 | 122961219 | chr11 | 123066433 | 123066463 |
| chr11 | 123229058 | 123229406 | chr11 | 123300824 | 123301028 | chr11 | 123301083 | 123302026 |
| chr11 | 123963874 | 123963994 | chr11 | 124735437 | 124735482 | chr11 | 124736196 | 124736252 |
| chr11 | 124738777 | 124739088 | chr11 | 125035763 | 125036208 | chr11 | 125220500 | 125220643 |
| chr11 | 125755612 | 125755710 | chr11 | 125758604 | 125758660 | chr11 | 125773675 | 125774060 |
| chr11 | 126870182 | 126870212 | chr11 | 126870453 | 126870500 | chr11 | 126870525 | 126870543 |
| chr11 | 126873390 | 126873515 | chr11 | 128391893 | 128392116 | chr11 | 128562892 | 128563185 |
| chr11 | 128563337 | 128563730 | chr11 | 128563940 | 128564329 | chr11 | 128564740 | 128564876 |
| chr11 | 128564992 | 128565379 | chr11 | 128657892 | 128657970 | chr11 | 129242876 | 129243241 |
| chr11 | 129243305 | 129243587 | chr11 | 129243849 | 129244300 | chr11 | 129244441 | 129244603 |
| chr11 | 129244893 | 129244923 | chr11 | 129245673 | 129245810 | chr11 | 129246070 | 129246129 |
| chr11 | 129907552 | 129907714 | chr11 | 129931742 | 129931851 | chr11 | 130318960 | 130318997 |
| chr11 | 130319527 | 130319613 | chr11 | 130343061 | 130343100 | chr11 | 130359769 | 130359915 |
| chr11 | 130781550 | 130781781 | chr11 | 130785487 | 130785622 | chr11 | 130854324 | 130854490 |
| chr11 | 131522763 | 131522947 | chr11 | 131564970 | 131565073 | chr11 | 131766715 | 131766960 |
| chr11 | 131780877 | 131781078 | chr11 | 132484215 | 132484404 | chr11 | 132813489 | 132813757 |
| chr11 | 132813908 | 132813949 | chr11 | 132864134 | 132864175 | chr11 | 132934123 | 132934176 |
| chr11 | 132952768 | 132953050 | chr11 | 132953233 | 132953423 | chr11 | 133231739 | 133231832 |
| chr11 | 133402206 | 133402260 | chr11 | 133792055 | 133792214 | chr11 | 133825226 | 133825543 |
| chr11 | 133906783 | 133906918 | chr11 | 133939002 | 133939177 | chr11 | 134145703 | 134146393 |
| chr11 | 134146682 | 134146894 | chr11 | 134201502 | 134201543 | chr11 | 134201841 | 134202084 |
| chr11 | 134281365 | 134281509 | chr12 | 570090 | 570171 | chr12 | 1639135 | 1639222 |
| chr12 | 1650475 | 1650577 | chr12 | 2046104 | 2046134 | chr12 | 2162554 | 2162817 |
| chr12 | 2163164 | 2163276 | chr12 | 2403658 | 2403714 | chr12 | 2566053 | 2566247 |
| chr12 | 2595199 | 2595339 | chr12 | 2862068 | 2862142 | chr12 | 2964465 | 2964577 |
| chr12 | 3371882 | 3371911 | chr12 | 3373533 | 3373666 | chr12 | 3600315 | 3600345 |
| chr12 | 3602270 | 3602716 | chr12 | 3602865 | 3602879 | chr12 | 3603100 | 3603156 |
| chr12 | 3862254 | 3862298 | chr12 | 4213973 | 4214157 | chr12 | 4231674 | 4231767 |
| chr12 | 4274054 | 4274188 | chr12 | 4274271 | 4274409 | chr12 | 4323835 | 4323912 |
| chr12 | 4362436 | 4362471 | chr12 | 4378252 | 4378330 | chr12 | 4379357 | 4379491 |
| chr12 | 4381433 | 4382386 | chr12 | 4382965 | 4382999 | chr12 | 4383492 | 4383784 |
| chr12 | 4384389 | 4384418 | chr12 | 4384736 | 4384902 | chr12 | 4392883 | 4392922 |
| chr12 | 4405589 | 4405619 | chr12 | 4431271 | 4431301 | chr12 | 4554801 | 4554831 |
| chr12 | 4919145 | 4919213 | chr12 | 4919239 | 4919244 | chr12 | 5018073 | 5018692 |
| chr12 | 5019085 | 5019742 | chr12 | 5019794 | 5020313 | chr12 | 5153039 | 5153286 |
| chr12 | 5153358 | 5153460 | chr12 | 5541100 | 5541177 | chr12 | 5542325 | 5542439 |
| chr12 | 5542759 | 5542911 | chr12 | 5840200 | 5840363 | chr12 | 6308743 | 6308772 |
| chr12 | 6473721 | 6473762 | chr12 | 6483615 | 6483756 | chr12 | 6664508 | 6664522 |
| chr12 | 6678158 | 6678203 | chr12 | 7403914 | 7404060 | chr12 | 7559160 | 7559307 |
| chr12 | 8025635 | 8025660 | chr12 | 8036526 | 8036634 | chr12 | 8122523 | 8122628 |
| chr12 | 8127036 | 8127140 | chr12 | 8127565 | 8127595 | chr12 | 8139203 | 8139233 |
| chr12 | 8163573 | 8163603 | chr12 | 8171360 | 8171745 | chr12 | 8180999 | 8181065 |
| chr12 | 8549178 | 8549208 | chr12 | 8808599 | 8808709 | chr12 | 8850658 | 8850744 |
| chr12 | 8975182 | 8975361 | chr12 | 9916313 | 9916343 | chr12 | 10085916 | 10085948 |
| chr12 | 10363278 | 10363607 | chr12 | 10772771 | 10772896 | chr12 | 11653449 | 11653463 |
| chr12 | 12456859 | 12456889 | chr12 | 12504616 | 12504850 | chr12 | 12848390 | 12848556 |
| chr12 | 13036048 | 13036078 | chr12 | 13055966 | 13055996 | chr12 | 14133152 | 14133263 |
| chr12 | 14133619 | 14133881 | chr12 | 14135111 | 14135339 | chr12 | 14719937 | 14719967 |
| chr12 | 14818824 | 14818867 | chr12 | 15374258 | 15374291 | chr12 | 16500576 | 16500621 |
| chr12 | 19282333 | 19282363 | chr12 | 20521704 | 20521841 | chr12 | 20522457 | 20522487 |
| chr12 | 20522769 | 20522891 | chr12 | 21680394 | 21680683 | chr12 | 21810264 | 21810868 |
| chr12 | 21833068 | 21833265 | chr12 | 22093825 | 22094268 | chr12 | 22094578 | 22094810 |
| chr12 | 22486799 | 22486881 | chr12 | 22487134 | 22487473 | chr12 | 22698063 | 22698110 |
| chr12 | 23229390 | 23229420 | chr12 | 24714909 | 24714938 | chr12 | 24715235 | 24715264 |
| chr12 | 24716033 | 24716218 | chr12 | 25056243 | 25056436 | chr12 | 25101592 | 25101660 |
| chr12 | 25101919 | 25101997 | chr12 | 25102010 | 25102086 | chr12 | 25362824 | 25362853 |
| chr12 | 25368463 | 25368492 | chr12 | 25378543 | 25378662 | chr12 | 25380231 | 25380299 |
| chr12 | 25398203 | 25398319 | chr12 | 26178334 | 26178376 | chr12 | 27114515 | 27114639 |
| chr12 | 27176441 | 27176539 | chr12 | 27494550 | 27494580 | chr12 | 28123996 | 28124247 |
| chr12 | 28127767 | 28128302 | chr12 | 28128547 | 28129084 | chr12 | 29936016 | 29936048 |
| chr12 | 29936602 | 29936642 | chr12 | 29936662 | 29936831 | chr12 | 29937331 | 29937374 |
| chr12 | 30322774 | 30322924 | chr12 | 30323015 | 30323439 | chr12 | 30323503 | 30323517 |
| chr12 | 30975572 | 30975959 | chr12 | 31079268 | 31079367 | chr12 | 31079418 | 31079499 |
| chr12 | 31316012 | 31316362 | chr12 | 31366306 | 31366336 | chr12 | 32086716 | 32086982 |
| chr12 | 32340317 | 32340534 | chr12 | 32831622 | 32831652 | chr12 | 33591774 | 33591804 |
| chr12 | 33592613 | 33592847 | chr12 | 34494888 | 34494918 | chr12 | 34502733 | 34502803 |
| chr12 | 39299117 | 39299560 | chr12 | 39539353 | 39539436 | chr12 | 40618404 | 40618470 |
| chr12 | 41086183 | 41086379 | chr12 | 41086784 | 41087106 | chr12 | 41582513 | 41582988 |
| chr12 | 41583374 | 41583419 | chr12 | 43945110 | 43945124 | chr12 | 43945356 | 43945379 |
| chr12 | 43945417 | 43945526 | chr12 | 43946203 | 43946298 | chr12 | 45269504 | 45269624 |
| chr12 | 45444118 | 45444681 | chr12 | 45444715 | 45445258 | chr12 | 46767650 | 46767697 |
| chr12 | 47225381 | 47225476 | chr12 | 47225551 | 47225579 | chr12 | 47629349 | 47629379 |
| chr12 | 48397195 | 48398070 | chr12 | 48398641 | 48398671 | chr12 | 48690674 | 48690880 |
| chr12 | 49035233 | 49035414 | chr12 | 49074601 | 49074843 | chr12 | 49297802 | 49297915 |

TABLE 12-continued

Pan Cancer #2

| chr | start | end | chr | start | end | chr | start | end |
|---|---|---|---|---|---|---|---|---|
| chr12 | 49366374 | 49366423 | chr12 | 49374914 | 49375026 | chr12 | 49375116 | 49375119 |
| chr12 | 49375325 | 49375529 | chr12 | 49390873 | 49391104 | chr12 | 49391147 | 49391877 |
| chr12 | 49515852 | 49515920 | chr12 | 49657705 | 49657901 | chr12 | 49691049 | 49691078 |
| chr12 | 49727092 | 49727127 | chr12 | 49729728 | 49730090 | chr12 | 49759530 | 49759559 |
| chr12 | 49989786 | 49989816 | chr12 | 50297497 | 50297554 | chr12 | 50297974 | 50298055 |
| chr12 | 50426748 | 50426799 | chr12 | 50507349 | 50507522 | chr12 | 50673944 | 50674096 |
| chr12 | 50897763 | 50898273 | chr12 | 51400044 | 51400091 | chr12 | 51420874 | 51421271 |
| chr12 | 51421556 | 51421586 | chr12 | 51441284 | 51441368 | chr12 | 51565269 | 51565548 |
| chr12 | 51625514 | 51625587 | chr12 | 51930708 | 51930862 | chr12 | 52262983 | 52263106 |
| chr12 | 52301280 | 52301305 | chr12 | 52400831 | 52401537 | chr12 | 52408905 | 52409033 |
| chr12 | 52627273 | 52627438 | chr12 | 52652153 | 52652219 | chr12 | 52652600 | 52652613 |
| chr12 | 53108089 | 53108218 | chr12 | 53359386 | 53359563 | chr12 | 53763427 | 53763885 |
| chr12 | 53766833 | 53766964 | chr12 | 53834392 | 53834475 | chr12 | 53885346 | 53885651 |
| chr12 | 54089093 | 54089511 | chr12 | 54132252 | 54132329 | chr12 | 54145843 | 54145857 |
| chr12 | 54145881 | 54145895 | chr12 | 54321250 | 54321628 | chr12 | 54322201 | 54322252 |
| chr12 | 54324799 | 54324937 | chr12 | 54329358 | 54329478 | chr12 | 54329605 | 54329947 |
| chr12 | 54331062 | 54331135 | chr12 | 54332868 | 54333337 | chr12 | 54338666 | 54338817 |
| chr12 | 54338979 | 54339681 | chr12 | 54343812 | 54343829 | chr12 | 54345611 | 54345658 |
| chr12 | 54345966 | 54346032 | chr12 | 54348844 | 54349079 | chr12 | 54349256 | 54349336 |
| chr12 | 54354514 | 54354621 | chr12 | 54354905 | 54355086 | chr12 | 54359960 | 54360084 |
| chr12 | 54360608 | 54360649 | chr12 | 54377912 | 54377946 | chr12 | 54377978 | 54378115 |
| chr12 | 54379174 | 54379623 | chr12 | 54379888 | 54379930 | chr12 | 54379959 | 54380459 |
| chr12 | 54387842 | 54387959 | chr12 | 54388215 | 54388245 | chr12 | 54391400 | 54391403 |
| chr12 | 54393479 | 54393684 | chr12 | 54393950 | 54394162 | chr12 | 54394410 | 54394418 |
| chr12 | 54398889 | 54398959 | chr12 | 54399616 | 54399646 | chr12 | 54402690 | 54402796 |
| chr12 | 54403067 | 54403360 | chr12 | 54408411 | 54408726 | chr12 | 54409476 | 54409505 |
| chr12 | 54423616 | 54423697 | chr12 | 54424746 | 54424748 | chr12 | 54425032 | 54425119 |
| chr12 | 54447351 | 54447581 | chr12 | 54447899 | 54447977 | chr12 | 54520745 | 54520868 |
| chr12 | 54613463 | 54613615 | chr12 | 54719808 | 54720232 | chr12 | 54812238 | 54812359 |
| chr12 | 54894048 | 54894173 | chr12 | 54922624 | 54922803 | chr12 | 54942994 | 54943116 |
| chr12 | 55480923 | 55481067 | chr12 | 55561202 | 55561354 | chr12 | 56231108 | 56231148 |
| chr12 | 56400463 | 56400591 | chr12 | 56478840 | 56478869 | chr12 | 56481645 | 56481937 |
| chr12 | 56486572 | 56486601 | chr12 | 56490965 | 56490994 | chr12 | 56491630 | 56491659 |
| chr12 | 56492618 | 56492647 | chr12 | 56558381 | 56558519 | chr12 | 56653281 | 56653369 |
| chr12 | 56873601 | 56873630 | chr12 | 56882240 | 56882380 | chr12 | 57174355 | 57174452 |
| chr12 | 57359920 | 57359950 | chr12 | 57387303 | 57387332 | chr12 | 57559869 | 57559925 |
| chr12 | 57618574 | 57618710 | chr12 | 57881127 | 57881383 | chr12 | 57944081 | 57944117 |
| chr12 | 57983314 | 57983348 | chr12 | 58021320 | 58021458 | chr12 | 58021916 | 58022029 |
| chr12 | 58025646 | 58025733 | chr12 | 58025870 | 58025873 | chr12 | 58145415 | 58145450 |
| chr12 | 59314159 | 59314189 | chr12 | 62584838 | 62585012 | chr12 | 62585031 | 62586017 |
| chr12 | 62586252 | 62586281 | chr12 | 62603907 | 62603937 | chr12 | 62858444 | 62858575 |
| chr12 | 63025574 | 63026160 | chr12 | 63326618 | 63326648 | chr12 | 63543848 | 63544401 |
| chr12 | 63544499 | 63544599 | chr12 | 63545313 | 63545343 | chr12 | 64028352 | 64028382 |
| chr12 | 64061821 | 64062159 | chr12 | 64062369 | 64062578 | chr12 | 64062921 | 64063096 |
| chr12 | 64783185 | 64783308 | chr12 | 64784108 | 64784252 | chr12 | 64784534 | 64784564 |
| chr12 | 65218102 | 65218550 | chr12 | 65218901 | 65219156 | chr12 | 65219376 | 65219527 |
| chr12 | 65219606 | 65219784 | chr12 | 65220205 | 65220350 | chr12 | 65514863 | 65515596 |
| chr12 | 65516360 | 65516455 | chr12 | 65557212 | 65557376 | chr12 | 65561778 | 65562086 |
| chr12 | 66122800 | 66122995 | chr12 | 66123381 | 66123519 | chr12 | 66135984 | 66136014 |
| chr12 | 66582827 | 66583137 | chr12 | 68433260 | 68433321 | chr12 | 68964473 | 68964503 |
| chr12 | 68978322 | 68978576 | chr12 | 69327259 | 69327463 | chr12 | 69754451 | 69754729 |
| chr12 | 69964176 | 69964264 | chr12 | 70087493 | 70087568 | chr12 | 70698883 | 70699050 |
| chr12 | 72332641 | 72332696 | chr12 | 72665186 | 72665788 | chr12 | 72666713 | 72666807 |
| chr12 | 72666998 | 72667425 | chr12 | 72667652 | 72667792 | chr12 | 75601379 | 75601499 |
| chr12 | 75601696 | 75601910 | chr12 | 75602976 | 75603231 | chr12 | 75728336 | 75728485 |
| chr12 | 75728737 | 75728766 | chr12 | 77719311 | 77719422 | chr12 | 79257222 | 79257351 |
| chr12 | 81102185 | 81102455 | chr12 | 81102513 | 81102562 | chr12 | 81107997 | 81108034 |
| chr12 | 81471517 | 81471614 | chr12 | 81471754 | 81472111 | chr12 | 85306519 | 85306572 |
| chr12 | 85667272 | 85667731 | chr12 | 85673206 | 85673235 | chr12 | 85673460 | 85674807 |
| chr12 | 88973544 | 88973582 | chr12 | 88974159 | 88974253 | chr12 | 89915009 | 89915043 |
| chr12 | 93476304 | 93476342 | chr12 | 93966429 | 93966603 | chr12 | 93966998 | 93967215 |
| chr12 | 94543409 | 94543445 | chr12 | 94543899 | 94543961 | chr12 | 94544022 | 94544052 |
| chr12 | 94852412 | 94852506 | chr12 | 95216830 | 95216960 | chr12 | 95267524 | 95267554 |
| chr12 | 95267865 | 95267976 | chr12 | 95822981 | 95823011 | chr12 | 95866563 | 95866609 |
| chr12 | 95942965 | 95942978 | chr12 | 96880822 | 96881029 | chr12 | 98948200 | 98948295 |
| chr12 | 98949938 | 98949972 | chr12 | 98961066 | 98961241 | chr12 | 98986343 | 98986491 |
| chr12 | 99288312 | 99288407 | chr12 | 99288622 | 99288936 | chr12 | 99289162 | 99289309 |
| chr12 | 100595495 | 100595558 | chr12 | 101025380 | 101025410 | chr12 | 101111029 | 101111061 |
| chr12 | 101111373 | 101111479 | chr12 | 102457208 | 102457238 | chr12 | 103218495 | 103218595 |
| chr12 | 103351564 | 103351985 | chr12 | 103352052 | 103352154 | chr12 | 103352171 | 103352282 |
| chr12 | 103352314 | 103352681 | chr12 | 103358865 | 103358899 | chr12 | 103359556 | 103359586 |
| chr12 | 103889160 | 103889211 | chr12 | 103889789 | 103889812 | chr12 | 104506691 | 104506783 |
| chr12 | 104609417 | 104609796 | chr12 | 104671030 | 104671064 | chr12 | 104671699 | 104671761 |
| chr12 | 104684181 | 104684258 | chr12 | 104696376 | 104696502 | chr12 | 104850505 | 104850536 |
| chr12 | 104850578 | 104850592 | chr12 | 104851077 | 104851186 | chr12 | 104852032 | 104852508 |
| chr12 | 105017109 | 105017228 | chr12 | 105478323 | 105478419 | chr12 | 106533852 | 106533881 |

TABLE 12-continued

Pan Cancer #2

| chr | start | end | chr | start | end | chr | start | end |
|---|---|---|---|---|---|---|---|---|
| chr12 | 106974353 | 106974383 | chr12 | 106976725 | 106976779 | chr12 | 106977321 | 106977497 |
| chr12 | 106979161 | 106979534 | chr12 | 106979799 | 106979995 | chr12 | 106980223 | 106980333 |
| chr12 | 106980912 | 106981406 | chr12 | 107486550 | 107486672 | chr12 | 107487194 | 107487855 |
| chr12 | 107712273 | 107712303 | chr12 | 107713205 | 107713235 | chr12 | 107714866 | 107715153 |
| chr12 | 108080498 | 108080553 | chr12 | 108168971 | 108169413 | chr12 | 108169550 | 108169573 |
| chr12 | 108237466 | 108237524 | chr12 | 108238102 | 108238513 | chr12 | 108297411 | 108297466 |
| chr12 | 109488519 | 109488686 | chr12 | 109639281 | 109639475 | chr12 | 110353414 | 110353451 |
| chr12 | 110507084 | 110507207 | chr12 | 110717541 | 110717710 | chr12 | 110840344 | 110840404 |
| chr12 | 110854243 | 110854288 | chr12 | 110887179 | 110887209 | chr12 | 110983706 | 110983736 |
| chr12 | 111127124 | 111127455 | chr12 | 111143726 | 111143756 | chr12 | 111471177 | 111471559 |
| chr12 | 111471948 | 111471959 | chr12 | 111472059 | 111472195 | chr12 | 111472357 | 111472671 |
| chr12 | 111763122 | 111763152 | chr12 | 112547662 | 112547692 | chr12 | 112574734 | 112574995 |
| chr12 | 112792829 | 112792944 | chr12 | 112825760 | 112825896 | chr12 | 112888151 | 112888315 |
| chr12 | 112910821 | 112910850 | chr12 | 112915509 | 112915538 | chr12 | 112926255 | 112926284 |
| chr12 | 112926876 | 112926914 | chr12 | 113012954 | 113013157 | chr12 | 113541667 | 113542099 |
| chr12 | 113592238 | 113592359 | chr12 | 113795506 | 113795657 | chr12 | 113900753 | 113900765 |
| chr12 | 113901074 | 113901158 | chr12 | 113901408 | 113901591 | chr12 | 113902042 | 113902353 |
| chr12 | 113903468 | 113903498 | chr12 | 113904779 | 113905016 | chr12 | 113908990 | 113909314 |
| chr12 | 113909329 | 113909455 | chr12 | 113913267 | 113913681 | chr12 | 113913884 | 113914050 |
| chr12 | 113916222 | 113916316 | chr12 | 113916649 | 113916678 | chr12 | 113916972 | 113917012 |
| chr12 | 113917232 | 113917310 | chr12 | 113917775 | 113917890 | chr12 | 114029408 | 114029660 |
| chr12 | 114076029 | 114076093 | chr12 | 114337763 | 114337793 | chr12 | 114833985 | 114834102 |
| chr12 | 114838369 | 114838726 | chr12 | 114839104 | 114839147 | chr12 | 114841046 | 114841084 |
| chr12 | 114841425 | 114841493 | chr12 | 114843112 | 114843186 | chr12 | 114843261 | 114843278 |
| chr12 | 114843545 | 114843660 | chr12 | 114844201 | 114844300 | chr12 | 114846715 | 114846768 |
| chr12 | 114847043 | 114847436 | chr12 | 114847578 | 114847691 | chr12 | 114852040 | 114852082 |
| chr12 | 114852293 | 114852373 | chr12 | 114877171 | 114877262 | chr12 | 114878550 | 114878584 |
| chr12 | 114878813 | 114879012 | chr12 | 114881634 | 114881764 | chr12 | 114882555 | 114882646 |
| chr12 | 114883473 | 114883535 | chr12 | 114918594 | 114918717 | chr12 | 115136359 | 115136363 |
| chr12 | 116946086 | 116946199 | chr12 | 116946251 | 116946548 | chr12 | 117474065 | 117474198 |
| chr12 | 117526330 | 117526368 | chr12 | 117798065 | 117798095 | chr12 | 117799413 | 117799529 |
| chr12 | 118860397 | 118860654 | chr12 | 118920764 | 118920804 | chr12 | 119212319 | 119212381 |
| chr12 | 119418594 | 119418847 | chr12 | 119419436 | 119419466 | chr12 | 119419720 | 119419899 |
| chr12 | 120032862 | 120033169 | chr12 | 120148142 | 120148248 | chr12 | 120148923 | 120148962 |
| chr12 | 120535158 | 120535187 | chr12 | 120536625 | 120536654 | chr12 | 120885215 | 120885245 |
| chr12 | 120971686 | 120971716 | chr12 | 121622546 | 121622576 | chr12 | 122108464 | 122108601 |
| chr12 | 122192723 | 122192843 | chr12 | 122278388 | 122278580 | chr12 | 122285067 | 122285108 |
| chr12 | 122473581 | 122473611 | chr12 | 122940449 | 122940479 | chr12 | 123129129 | 123129550 |
| chr12 | 123211316 | 123211390 | chr12 | 123233646 | 123233846 | chr12 | 123410210 | 123410240 |
| chr12 | 123942025 | 123942189 | chr12 | 124117199 | 124117289 | chr12 | 124246908 | 124246937 |
| chr12 | 124247208 | 124247237 | chr12 | 124393560 | 124393604 | chr12 | 124397464 | 124397618 |
| chr12 | 124865115 | 124865144 | chr12 | 125009276 | 125009306 | chr12 | 125533949 | 125534407 |
| chr12 | 125589840 | 125589872 | chr12 | 125670117 | 125670260 | chr12 | 126168554 | 126168620 |
| chr12 | 127211317 | 127211378 | chr12 | 127765158 | 127765432 | chr12 | 127940086 | 127940247 |
| chr12 | 128751384 | 128751443 | chr12 | 128751821 | 128751877 | chr12 | 128752115 | 128752240 |
| chr12 | 128752499 | 128752944 | chr12 | 128753210 | 128753240 | chr12 | 128850534 | 128850644 |
| chr12 | 129338588 | 129338816 | chr12 | 129427424 | 129427557 | chr12 | 129447299 | 129447450 |
| chr12 | 130037653 | 130037778 | chr12 | 130387797 | 130387811 | chr12 | 130388410 | 130388434 |
| chr12 | 130389013 | 130389152 | chr12 | 130589202 | 130589266 | chr12 | 130645233 | 130645627 |
| chr12 | 130646946 | 130647115 | chr12 | 130647574 | 130647908 | chr12 | 130647951 | 130648069 |
| chr12 | 130821371 | 130821621 | chr12 | 130968621 | 130968654 | chr12 | 131200379 | 131200645 |
| chr12 | 131400816 | 131400919 | chr12 | 131403032 | 131403125 | chr12 | 131513345 | 131513403 |
| chr12 | 132102173 | 132102202 | chr12 | 132169288 | 132169442 | chr12 | 132221689 | 132222076 |
| chr12 | 132332910 | 132332940 | chr12 | 132333434 | 132333597 | chr12 | 132348651 | 132348684 |
| chr12 | 132423516 | 132423854 | chr12 | 132643233 | 132643279 | chr12 | 132986495 | 132986581 |
| chr12 | 133002792 | 133003231 | chr12 | 133172907 | 133173021 | chr12 | 133195093 | 133195196 |
| chr12 | 133199738 | 133199784 | chr12 | 133262698 | 133262926 | chr12 | 133280578 | 133280682 |
| chr12 | 133463736 | 133463876 | chr12 | 133464108 | 133464166 | chr12 | 133464840 | 133465027 |
| chr12 | 133481490 | 133481655 | chr12 | 133484742 | 133484852 | chr12 | 133485162 | 133485347 |
| chr12 | 133485557 | 133485689 | chr12 | 133485816 | 133485847 | chr12 | 133758048 | 133758107 |
| chr13 | 20175911 | 20175941 | chr13 | 20451144 | 20451360 | chr13 | 20735804 | 20736089 |
| chr13 | 21649636 | 21649775 | chr13 | 21713233 | 21713513 | chr13 | 22243273 | 22243469 |
| chr13 | 23489851 | 23489914 | chr13 | 23653789 | 23653813 | chr13 | 23733447 | 23734020 |
| chr13 | 23734284 | 23734297 | chr13 | 24099683 | 24099713 | chr13 | 24477643 | 24477906 |
| chr13 | 25115713 | 25115771 | chr13 | 25319856 | 25319904 | chr13 | 25320388 | 25320539 |
| chr13 | 25320614 | 25321028 | chr13 | 25321113 | 25321350 | chr13 | 25321699 | 25321942 |
| chr13 | 25593062 | 25593242 | chr13 | 25621045 | 25621205 | chr13 | 25621264 | 25621394 |
| chr13 | 25668799 | 25668829 | chr13 | 25744716 | 25744734 | chr13 | 25745301 | 25745594 |
| chr13 | 25745727 | 25746000 | chr13 | 25946301 | 25946411 | chr13 | 25946620 | 25946673 |
| chr13 | 26042678 | 26042707 | chr13 | 26042769 | 26043170 | chr13 | 26043341 | 26043499 |
| chr13 | 26340608 | 26340755 | chr13 | 26625301 | 26625656 | chr13 | 27334211 | 27334563 |
| chr13 | 27334772 | 27334894 | chr13 | 27699893 | 27699981 | chr13 | 28239909 | 28240164 |
| chr13 | 28365705 | 28366122 | chr13 | 28366482 | 28366577 | chr13 | 28367024 | 28367038 |
| chr13 | 28367794 | 28367945 | chr13 | 28368154 | 28368168 | chr13 | 28368451 | 28368593 |
| chr13 | 28368952 | 28369070 | chr13 | 28369162 | 28369990 | chr13 | 28370947 | 28371061 |
| chr13 | 28394766 | 28394866 | chr13 | 28395501 | 28395553 | chr13 | 28395998 | 28396073 |

TABLE 12-continued

Pan Cancer #2

| chr | start | end | chr | start | end | chr | start | end |
|---|---|---|---|---|---|---|---|---|
| chr13 | 28491793 | 28491946 | chr13 | 28492244 | 28492553 | chr13 | 28503042 | 28503074 |
| chr13 | 28528534 | 28528748 | chr13 | 28540745 | 28540927 | chr13 | 28543212 | 28543242 |
| chr13 | 28544397 | 28544584 | chr13 | 28544666 | 28544903 | chr13 | 28549497 | 28549891 |
| chr13 | 28550240 | 28550552 | chr13 | 28551417 | 28551461 | chr13 | 28551950 | 28552167 |
| chr13 | 28552794 | 28552824 | chr13 | 28553030 | 28553138 | chr13 | 28589765 | 28589794 |
| chr13 | 28592605 | 28592658 | chr13 | 28601345 | 28601374 | chr13 | 28602326 | 28602355 |
| chr13 | 28608233 | 28608355 | chr13 | 28610123 | 28610152 | chr13 | 28674018 | 28674226 |
| chr13 | 28674721 | 28674734 | chr13 | 28706016 | 28706140 | chr13 | 29067773 | 29068416 |
| chr13 | 29068926 | 29068985 | chr13 | 29068994 | 29069065 | chr13 | 29106308 | 29106814 |
| chr13 | 29106899 | 29107063 | chr13 | 29107253 | 29107309 | chr13 | 29112395 | 29112444 |
| chr13 | 30141688 | 30141718 | chr13 | 30707569 | 30707599 | chr13 | 31185432 | 31185548 |
| chr13 | 31742953 | 31743177 | chr13 | 32605034 | 32605324 | chr13 | 32605443 | 32605623 |
| chr13 | 32605675 | 32605966 | chr13 | 33591300 | 33591419 | chr13 | 33924666 | 33924790 |
| chr13 | 35517410 | 35517648 | chr13 | 36044829 | 36044930 | chr13 | 36049995 | 36050025 |
| chr13 | 36269480 | 36269509 | chr13 | 36541300 | 36541329 | chr13 | 36553399 | 36553428 |
| chr13 | 36588100 | 36588129 | chr13 | 36704939 | 36705055 | chr13 | 36705451 | 36705489 |
| chr13 | 36909206 | 36909236 | chr13 | 36920317 | 36920386 | chr13 | 36920628 | 36920785 |
| chr13 | 37004771 | 37005129 | chr13 | 37005900 | 37006062 | chr13 | 37006434 | 37006657 |
| chr13 | 37006734 | 37006762 | chr13 | 37248063 | 37248148 | chr13 | 37248295 | 37248319 |
| chr13 | 37248979 | 37248993 | chr13 | 37633989 | 37634018 | chr13 | 37643942 | 37644005 |
| chr13 | 38402239 | 38402268 | chr13 | 38443618 | 38443715 | chr13 | 39261410 | 39261446 |
| chr13 | 40000498 | 40000528 | chr13 | 41346048 | 41346088 | chr13 | 41496324 | 41496478 |
| chr13 | 41884500 | 41884688 | chr13 | 43148669 | 43148698 | chr13 | 43566247 | 43566647 |
| chr13 | 43620862 | 43621006 | chr13 | 44947746 | 44948197 | chr13 | 45150013 | 45150276 |
| chr13 | 45885876 | 45885905 | chr13 | 45905088 | 45905242 | chr13 | 46425548 | 46425554 |
| chr13 | 46425576 | 46425584 | chr13 | 46649031 | 46649141 | chr13 | 46660839 | 46660869 |
| chr13 | 46961494 | 46961533 | chr13 | 46961952 | 46961982 | chr13 | 47407767 | 47407796 |
| chr13 | 47468139 | 47468168 | chr13 | 47472315 | 47472344 | chr13 | 47526030 | 47526182 |
| chr13 | 48478576 | 48478605 | chr13 | 48667877 | 48667907 | chr13 | 49794117 | 49794925 |
| chr13 | 50266473 | 50266573 | chr13 | 50367946 | 50368123 | chr13 | 50421504 | 50421696 |
| chr13 | 50639705 | 50639799 | chr13 | 52270145 | 52270175 | chr13 | 52565068 | 52565194 |
| chr13 | 52580318 | 52580369 | chr13 | 53312991 | 53313313 | chr13 | 53313513 | 53313612 |
| chr13 | 53313678 | 53313920 | chr13 | 53419734 | 53419775 | chr13 | 53420020 | 53420020 |
| chr13 | 53423838 | 53423978 | chr13 | 55146522 | 55146551 | chr13 | 55373897 | 55373926 |
| chr13 | 55628658 | 55628687 | chr13 | 56762456 | 56762485 | chr13 | 57714539 | 57714568 |
| chr13 | 58203602 | 58203644 | chr13 | 58203851 | 58204103 | chr13 | 58204350 | 58204393 |
| chr13 | 58206042 | 58206231 | chr13 | 58206453 | 58206771 | chr13 | 58206862 | 58206983 |
| chr13 | 58207568 | 58207813 | chr13 | 58207892 | 58208020 | chr13 | 58208495 | 58208926 |
| chr13 | 58892774 | 58892803 | chr13 | 59531686 | 59531715 | chr13 | 62132346 | 62132375 |
| chr13 | 64650200 | 64650229 | chr13 | 65532258 | 65532287 | chr13 | 66697959 | 66698124 |
| chr13 | 67196371 | 67196400 | chr13 | 67197158 | 67197187 | chr13 | 67803735 | 67804074 |
| chr13 | 67804494 | 67804523 | chr13 | 67805191 | 67805247 | chr13 | 68488923 | 68488952 |
| chr13 | 68682015 | 68682044 | chr13 | 68745282 | 68745311 | chr13 | 69796842 | 69796871 |
| chr13 | 70681626 | 70681777 | chr13 | 70681867 | 70682071 | chr13 | 71498386 | 71498415 |
| chr13 | 72439142 | 72439250 | chr13 | 73184723 | 73184752 | chr13 | 73336049 | 73336078 |
| chr13 | 73619660 | 73619784 | chr13 | 76440730 | 76440760 | chr13 | 76869421 | 76869450 |
| chr13 | 77553779 | 77553809 | chr13 | 78492684 | 78492840 | chr13 | 78493166 | 78493196 |
| chr13 | 78493455 | 78493809 | chr13 | 79168067 | 79168102 | chr13 | 79169850 | 79170113 |
| chr13 | 79170348 | 79170383 | chr13 | 79170468 | 79170884 | chr13 | 79171118 | 79171196 |
| chr13 | 79175770 | 79175943 | chr13 | 79176709 | 79176125 | chr13 | 79176277 | 79176420 |
| chr13 | 79176609 | 79176783 | chr13 | 79176993 | 79177184 | chr13 | 79177306 | 79177622 |
| chr13 | 79177886 | 79177998 | chr13 | 79183406 | 79183423 | chr13 | 79693095 | 79693124 |
| chr13 | 79993101 | 79993142 | chr13 | 81229343 | 81229372 | chr13 | 84455236 | 84455292 |
| chr13 | 84455581 | 84455715 | chr13 | 84457491 | 84457521 | chr13 | 87731371 | 87731400 |
| chr13 | 88323579 | 88323830 | chr13 | 88323868 | 88324207 | chr13 | 88324516 | 88324518 |
| chr13 | 88325300 | 88325460 | chr13 | 88325819 | 88326061 | chr13 | 88326538 | 88326707 |
| chr13 | 88326937 | 88327014 | chr13 | 88629123 | 88629152 | chr13 | 88788883 | 88788912 |
| chr13 | 88997906 | 88997935 | chr13 | 89815436 | 89815465 | chr13 | 90015503 | 90015532 |
| chr13 | 90015897 | 90015926 | chr13 | 91755723 | 91755837 | chr13 | 91948489 | 91948519 |
| chr13 | 92050760 | 92050814 | chr13 | 92051139 | 92051168 | chr13 | 92051374 | 92051513 |
| chr13 | 93859304 | 93859333 | chr13 | 93879288 | 93879375 | chr13 | 93879670 | 93879700 |
| chr13 | 93880089 | 93880216 | chr13 | 93880534 | 93880737 | chr13 | 93880794 | 93880856 |
| chr13 | 94107209 | 94107238 | chr13 | 95086172 | 95086172 | chr13 | 95357311 | 95357341 |
| chr13 | 95357574 | 95357775 | chr13 | 95358041 | 95358165 | chr13 | 95359747 | 95359803 |
| chr13 | 95360322 | 95360371 | chr13 | 95363210 | 95363429 | chr13 | 95363796 | 95363959 |
| chr13 | 95364065 | 95364196 | chr13 | 95364495 | 95364800 | chr13 | 95620021 | 95620078 |
| chr13 | 95620647 | 95620781 | chr13 | 95620854 | 95621011 | chr13 | 96031705 | 96031815 |
| chr13 | 96177285 | 96177315 | chr13 | 96204923 | 96205363 | chr13 | 96296225 | 96296345 |
| chr13 | 96296373 | 96296473 | chr13 | 96296841 | 96296949 | chr13 | 96296992 | 96297137 |
| chr13 | 96743788 | 96744175 | chr13 | 97761876 | 97761925 | chr13 | 99851676 | 99851706 |
| chr13 | 100547713 | 100547893 | chr13 | 100608462 | 100608804 | chr13 | 100608839 | 100609055 |
| chr13 | 100621941 | 100622015 | chr13 | 100624324 | 100624348 | chr13 | 100624587 | 100624729 |
| chr13 | 100626929 | 100627009 | chr13 | 100627295 | 100627348 | chr13 | 100627688 | 100627717 |
| chr13 | 100630169 | 100630298 | chr13 | 100630329 | 100630430 | chr13 | 100630630 | 100630997 |
| chr13 | 100633089 | 100633184 | chr13 | 100634314 | 100634617 | chr13 | 100635406 | 100635451 |
| chr13 | 100636167 | 100636238 | chr13 | 100637390 | 100637485 | chr13 | 100641282 | 100641408 |

TABLE 12-continued

Pan Cancer #2

| chr | start | end | chr | start | end | chr | start | end |
|---|---|---|---|---|---|---|---|---|
| chr13 | 100642120 | 100642201 | chr13 | 100643296 | 100643435 | chr13 | 100644055 | 100644179 |
| chr13 | 100649325 | 100649575 | chr13 | 100649800 | 100649884 | chr13 | 102197373 | 102197408 |
| chr13 | 102568454 | 102568484 | chr13 | 102569313 | 102569542 | chr13 | 103046721 | 103046995 |
| chr13 | 103052347 | 103052574 | chr13 | 103052892 | 103052940 | chr13 | 103053394 | 103053496 |
| chr13 | 103821419 | 103821448 | chr13 | 105484285 | 105484314 | chr13 | 105791875 | 105791904 |
| chr13 | 107186855 | 107186884 | chr13 | 107187162 | 107187426 | chr13 | 107187666 | 107187695 |
| chr13 | 107188241 | 107188430 | chr13 | 107827301 | 107827331 | chr13 | 108518813 | 108518933 |
| chr13 | 108519254 | 108519367 | chr13 | 108519737 | 108519745 | chr13 | 108520376 | 108520534 |
| chr13 | 108520979 | 108521076 | chr13 | 108816328 | 108816383 | chr13 | 108869613 | 108869830 |
| chr13 | 109147685 | 109147862 | chr13 | 109148155 | 109148278 | chr13 | 109148783 | 109149185 |
| chr13 | 110434451 | 110434593 | chr13 | 110958816 | 110958981 | chr13 | 110959753 | 110959970 |
| chr13 | 110960541 | 110960603 | chr13 | 111278255 | 111278426 | chr13 | 111363787 | 111363972 |
| chr13 | 112272991 | 112273088 | chr13 | 112707694 | 112707869 | chr13 | 112708308 | 112708513 |
| chr13 | 112709388 | 112709617 | chr13 | 112709883 | 112709928 | chr13 | 112710360 | 112710475 |
| chr13 | 112710759 | 112711293 | chr13 | 112711376 | 112711776 | chr13 | 112712017 | 112713029 |
| chr13 | 112715370 | 112715642 | chr13 | 112715985 | 112716313 | chr13 | 112716677 | 112716721 |
| chr13 | 112717026 | 112717242 | chr13 | 112717323 | 112717536 | chr13 | 112717835 | 112717949 |
| chr13 | 112720033 | 112720505 | chr13 | 112720723 | 112720767 | chr13 | 112721012 | 112721026 |
| chr13 | 112722129 | 112722220 | chr13 | 112722275 | 112722312 | chr13 | 112724505 | 112724535 |
| chr13 | 112726436 | 112726560 | chr13 | 112727984 | 112728200 | chr13 | 112758107 | 112758257 |
| chr13 | 112758274 | 112758372 | chr13 | 112758496 | 112758613 | chr13 | 112759112 | 112759248 |
| chr13 | 112759612 | 112759642 | chr13 | 112760007 | 112760327 | chr13 | 112760795 | 112761214 |
| chr13 | 113244509 | 113244595 | chr13 | 113598618 | 113598851 | chr13 | 113938542 | 113938603 |
| chr13 | 113985679 | 113986053 | chr13 | 114055983 | 114056137 | chr13 | 114060064 | 114060333 |
| chr13 | 114074768 | 114074853 | chr13 | 114082984 | 114083014 | chr13 | 114123168 | 114123291 |
| chr13 | 114189737 | 114189809 | chr13 | 114221622 | 114221652 | chr13 | 114304565 | 114304927 |
| chr13 | 114479404 | 114479434 | chr13 | 114498017 | 114498260 | chr13 | 114568046 | 114568076 |
| chr13 | 114748342 | 114748638 | chr13 | 114766270 | 114766300 | chr13 | 114780561 | 114781061 |
| chr13 | 114807617 | 114807815 | chr13 | 114855655 | 114855669 | chr13 | 114862308 | 114862363 |
| chr13 | 114897194 | 114897240 | chr13 | 114961823 | 114961933 | chr14 | 21093454 | 21093631 |
| chr14 | 21100748 | 21100778 | chr14 | 21100801 | 21100831 | chr14 | 22005029 | 22005073 |
| chr14 | 23234956 | 23235032 | chr14 | 23356044 | 23356384 | chr14 | 23400315 | 23400354 |
| chr14 | 23426755 | 23426785 | chr14 | 23701644 | 23701737 | chr14 | 23706727 | 23706765 |
| chr14 | 24562744 | 24562774 | chr14 | 24641010 | 24641215 | chr14 | 24803594 | 24804122 |
| chr14 | 25071566 | 25071612 | chr14 | 25155907 | 25155985 | chr14 | 26674354 | 26674384 |
| chr14 | 26674699 | 26674729 | chr14 | 27066562 | 27066785 | chr14 | 27067373 | 27067386 |
| chr14 | 29225531 | 29225561 | chr14 | 29226071 | 29226198 | chr14 | 29228654 | 29228778 |
| chr14 | 29229107 | 29229386 | chr14 | 29231071 | 29231185 | chr14 | 29231425 | 29231590 |
| chr14 | 29235003 | 29235308 | chr14 | 29235342 | 29235356 | chr14 | 29237063 | 29237066 |
| chr14 | 29242763 | 29242908 | chr14 | 29243516 | 29243669 | chr14 | 29243731 | 29243888 |
| chr14 | 29244224 | 29244308 | chr14 | 29247689 | 29247740 | chr14 | 29254612 | 29254713 |
| chr14 | 31027323 | 31027367 | chr14 | 31344346 | 31344549 | chr14 | 31925554 | 31925724 |
| chr14 | 32597620 | 32597657 | chr14 | 33402462 | 33402762 | chr14 | 33403045 | 33403316 |
| chr14 | 33403866 | 33404418 | chr14 | 34269897 | 34270004 | chr14 | 34420250 | 34420288 |
| chr14 | 35023111 | 35023322 | chr14 | 35024446 | 35024546 | chr14 | 35389907 | 35389943 |
| chr14 | 36003442 | 36003826 | chr14 | 36004081 | 36004493 | chr14 | 36004711 | 36004734 |
| chr14 | 36004822 | 36004921 | chr14 | 36972803 | 36972912 | chr14 | 36973455 | 36973538 |
| chr14 | 36974294 | 36974927 | chr14 | 36974968 | 36974982 | chr14 | 36975299 | 36975399 |
| chr14 | 36977645 | 36977929 | chr14 | 36977975 | 36978009 | chr14 | 36978548 | 36978578 |
| chr14 | 36979619 | 36979649 | chr14 | 36982927 | 36982969 | chr14 | 36983708 | 36984146 |
| chr14 | 36985841 | 36985871 | chr14 | 36986301 | 36986471 | chr14 | 36987302 | 36987685 |
| chr14 | 36987939 | 36988143 | chr14 | 36988428 | 36988460 | chr14 | 36990858 | 36991032 |
| chr14 | 36991095 | 36991177 | chr14 | 36991532 | 36991613 | chr14 | 36991989 | 36992163 |
| chr14 | 36992222 | 36992417 | chr14 | 36993473 | 36993487 | chr14 | 36993694 | 36993956 |
| chr14 | 36994248 | 36994999 | chr14 | 37050752 | 37050794 | chr14 | 37116105 | 37116294 |
| chr14 | 37117611 | 37117697 | chr14 | 37123438 | 37124077 | chr14 | 37124482 | 37124572 |
| chr14 | 37124992 | 37125545 | chr14 | 37126241 | 37126297 | chr14 | 37126566 | 37126713 |
| chr14 | 37127281 | 37127311 | chr14 | 37127655 | 37127779 | chr14 | 37128553 | 37128723 |
| chr14 | 37130077 | 37130260 | chr14 | 37132375 | 37132553 | chr14 | 37132603 | 37132695 |
| chr14 | 37133001 | 37133052 | chr14 | 37135784 | 37136017 | chr14 | 37136295 | 37136345 |
| chr14 | 37136588 | 37136618 | chr14 | 38060677 | 38060916 | chr14 | 38064401 | 38064549 |
| chr14 | 38677519 | 38677548 | chr14 | 38677761 | 38677790 | chr14 | 38724294 | 38724525 |
| chr14 | 38724979 | 38725258 | chr14 | 38725521 | 38725764 | chr14 | 39579800 | 39579830 |
| chr14 | 42074544 | 42074586 | chr14 | 42074669 | 42074987 | chr14 | 42075588 | 42076043 |
| chr14 | 42076106 | 42076212 | chr14 | 42076823 | 42076853 | chr14 | 42077230 | 42077268 |
| chr14 | 42077770 | 42077800 | chr14 | 42079289 | 42079328 | chr14 | 45602514 | 45602576 |
| chr14 | 48143798 | 48143957 | chr14 | 48144359 | 48144401 | chr14 | 48144699 | 48144763 |
| chr14 | 48145237 | 48145257 | chr14 | 50233426 | 50233459 | chr14 | 50333754 | 50333994 |
| chr14 | 50334254 | 50334355 | chr14 | 50355854 | 50355924 | chr14 | 50681598 | 50681859 |
| chr14 | 50777663 | 50777714 | chr14 | 51338730 | 51338731 | chr14 | 51560304 | 51560713 |
| chr14 | 51560771 | 51561428 | chr14 | 51561765 | 51562012 | chr14 | 51829264 | 51829396 |
| chr14 | 51955509 | 51955538 | chr14 | 52534648 | 52534791 | chr14 | 52535012 | 52535026 |
| chr14 | 52535056 | 52535263 | chr14 | 52535335 | 52536104 | chr14 | 52536343 | 52536404 |
| chr14 | 52734509 | 52734557 | chr14 | 52734777 | 52735001 | chr14 | 52735045 | 52735255 |
| chr14 | 52765920 | 52766075 | chr14 | 52781525 | 52781916 | chr14 | 54422651 | 54422925 |
| chr14 | 55370202 | 55370235 | chr14 | 55595938 | 55595968 | chr14 | 55668368 | 55668526 |

TABLE 12-continued

Pan Cancer #2

| chr | start | end | chr | start | end | chr | start | end |
|---|---|---|---|---|---|---|---|---|
| chr14 | 55765285 | 55765714 | chr14 | 55823079 | 55823218 | chr14 | 57045520 | 57045739 |
| chr14 | 57260946 | 57261094 | chr14 | 57261175 | 57261407 | chr14 | 57261466 | 57261821 |
| chr14 | 57262072 | 57262179 | chr14 | 57264079 | 57264645 | chr14 | 57264765 | 57264806 |
| chr14 | 57265148 | 57265240 | chr14 | 57270936 | 57270971 | chr14 | 57271154 | 57271266 |
| chr14 | 57272009 | 57272067 | chr14 | 57274486 | 57275049 | chr14 | 57275211 | 57275305 |
| chr14 | 57275596 | 57275685 | chr14 | 57276074 | 57276104 | chr14 | 57276440 | 57276666 |
| chr14 | 57277920 | 57278762 | chr14 | 57278838 | 57279564 | chr14 | 57279643 | 57279657 |
| chr14 | 57283314 | 57283408 | chr14 | 57283446 | 57284036 | chr14 | 57284071 | 57284659 |
| chr14 | 58332297 | 58332403 | chr14 | 58857094 | 58857355 | chr14 | 58893052 | 58893183 |
| chr14 | 59770326 | 59770452 | chr14 | 60097193 | 60097246 | chr14 | 60097407 | 60097566 |
| chr14 | 60386207 | 60386252 | chr14 | 60386638 | 60386701 | chr14 | 60794635 | 60794667 |
| chr14 | 60952196 | 60952419 | chr14 | 60952517 | 60952632 | chr14 | 60952730 | 60952959 |
| chr14 | 60973151 | 60973324 | chr14 | 60973697 | 60974007 | chr14 | 60974368 | 60974403 |
| chr14 | 60975384 | 60975888 | chr14 | 60976075 | 60976514 | chr14 | 60976813 | 60976860 |
| chr14 | 60977337 | 60977712 | chr14 | 60977880 | 60978147 | chr14 | 60981202 | 60981268 |
| chr14 | 60981676 | 60981793 | chr14 | 60982110 | 60982367 | chr14 | 60982574 | 60982622 |
| chr14 | 60982841 | 60982911 | chr14 | 61104291 | 61104556 | chr14 | 61104624 | 61104864 |
| chr14 | 61108620 | 61108996 | chr14 | 61109206 | 61109470 | chr14 | 61109839 | 61110243 |
| chr14 | 61114137 | 61114456 | chr14 | 61115311 | 61115517 | chr14 | 61118743 | 61118765 |
| chr14 | 61118965 | 61119136 | chr14 | 61119536 | 61119639 | chr14 | 61747389 | 61747527 |
| chr14 | 61747583 | 61748033 | chr14 | 62106242 | 62106242 | chr14 | 62279578 | 62279852 |
| chr14 | 62279899 | 62280006 | chr14 | 62583809 | 62583869 | chr14 | 63512100 | 63512291 |
| chr14 | 63512573 | 63512708 | chr14 | 63512741 | 63512816 | chr14 | 63513124 | 63513154 |
| chr14 | 64107335 | 64107600 | chr14 | 64222413 | 64222488 | chr14 | 65005696 | 65005833 |
| chr14 | 65008998 | 65009193 | chr14 | 65233339 | 65233464 | chr14 | 66498931 | 66498975 |
| chr14 | 67585164 | 67585413 | chr14 | 67886378 | 67886606 | chr14 | 68334928 | 68335108 |
| chr14 | 69014044 | 69014110 | chr14 | 69866541 | 69866706 | chr14 | 69867022 | 69867196 |
| chr14 | 70014723 | 70014974 | chr14 | 70038990 | 70039025 | chr14 | 70346136 | 70346491 |
| chr14 | 70654343 | 70654713 | chr14 | 70655889 | 70655889 | chr14 | 70655920 | 70656090 |
| chr14 | 72398743 | 72399019 | chr14 | 72399452 | 72399453 | chr14 | 72399929 | 72400029 |
| chr14 | 73167750 | 73167899 | chr14 | 73175026 | 73175148 | chr14 | 73178807 | 73178865 |
| chr14 | 73180208 | 73180314 | chr14 | 73226952 | 73227005 | chr14 | 73231266 | 73231414 |
| chr14 | 73236095 | 73236178 | chr14 | 73318471 | 73318629 | chr14 | 73333249 | 73333396 |
| chr14 | 73602250 | 73602389 | chr14 | 73604570 | 73604718 | chr14 | 73855616 | 73855646 |
| chr14 | 73956853 | 73956913 | chr14 | 74529109 | 74529139 | chr14 | 74706015 | 74706222 |
| chr14 | 74706941 | 74707544 | chr14 | 74707573 | 74707747 | chr14 | 74707792 | 74707873 |
| chr14 | 74708862 | 74708955 | chr14 | 74892540 | 74892569 | chr14 | 74893074 | 74893113 |
| chr14 | 75078170 | 75078242 | chr14 | 75760311 | 75760347 | chr14 | 75988341 | 75988370 |
| chr14 | 75988732 | 75988761 | chr14 | 76128674 | 76128842 | chr14 | 76604682 | 76604716 |
| chr14 | 76605072 | 76605376 | chr14 | 76843742 | 76843953 | chr14 | 77228121 | 77228159 |
| chr14 | 77606922 | 77607236 | chr14 | 77737212 | 77737814 | chr14 | 79745138 | 79745175 |
| chr14 | 85996479 | 85996608 | chr14 | 85996892 | 85996906 | chr14 | 85997821 | 85997925 |
| chr14 | 85998288 | 85998574 | chr14 | 85998630 | 85998683 | chr14 | 85999597 | 85999613 |
| chr14 | 86000270 | 86000511 | chr14 | 86000918 | 86001114 | chr14 | 88457599 | 88457685 |
| chr14 | 89817889 | 89818034 | chr14 | 90527714 | 90527758 | chr14 | 90983328 | 90983360 |
| chr14 | 91691163 | 91691306 | chr14 | 91691696 | 91691822 | chr14 | 91766154 | 91766450 |
| chr14 | 91780382 | 91780512 | chr14 | 91801036 | 91801164 | chr14 | 92507578 | 92507792 |
| chr14 | 92789512 | 92789542 | chr14 | 92789960 | 92790098 | chr14 | 92790637 | 92790703 |
| chr14 | 92979917 | 92979991 | chr14 | 93155061 | 93155315 | chr14 | 93389557 | 93389693 |
| chr14 | 93389713 | 93389776 | chr14 | 93571193 | 93571326 | chr14 | 93706752 | 93706782 |
| chr14 | 94254389 | 94254458 | chr14 | 94254499 | 94254513 | chr14 | 94405734 | 94405785 |
| chr14 | 94603542 | 94603670 | chr14 | 94889856 | 94889870 | chr14 | 95233705 | 95233765 |
| chr14 | 95234643 | 95234710 | chr14 | 95235026 | 95235369 | chr14 | 95235989 | 95236111 |
| chr14 | 95236524 | 95236553 | chr14 | 95236819 | 95236848 | chr14 | 95237622 | 95237642 |
| chr14 | 95239422 | 95239633 | chr14 | 95240127 | 95240157 | chr14 | 95240227 | 95240341 |
| chr14 | 95240392 | 95240422 | chr14 | 95557626 | 95557655 | chr14 | 95560448 | 95560477 |
| chr14 | 95740035 | 95740116 | chr14 | 96053974 | 96054020 | chr14 | 96342897 | 96343133 |
| chr14 | 96343404 | 96343433 | chr14 | 96343668 | 96343701 | chr14 | 97045354 | 97045431 |
| chr14 | 97058944 | 97059083 | chr14 | 97499277 | 97499315 | chr14 | 97499847 | 97499849 |
| chr14 | 97685044 | 97685288 | chr14 | 97685707 | 97685959 | chr14 | 99584575 | 99584664 |
| chr14 | 99712321 | 99712394 | chr14 | 99736151 | 99736183 | chr14 | 99737398 | 99737462 |
| chr14 | 100148073 | 100148230 | chr14 | 100437794 | 100437949 | chr14 | 100438705 | 100438811 |
| chr14 | 100643350 | 100643481 | chr14 | 100793556 | 100793650 | chr14 | 100843765 | 100843912 |
| chr14 | 101250109 | 101250272 | chr14 | 101506231 | 101506260 | chr14 | 101543868 | 101544235 |
| chr14 | 101923114 | 101923250 | chr14 | 101923600 | 101923686 | chr14 | 101924031 | 101924047 |
| chr14 | 101925049 | 101925071 | chr14 | 101925656 | 101925901 | chr14 | 102026360 | 102026484 |
| chr14 | 102026797 | 102026967 | chr14 | 102031236 | 102031271 | chr14 | 102031512 | 102031580 |
| chr14 | 102247912 | 102248214 | chr14 | 102418607 | 102418637 | chr14 | 102521602 | 102521758 |
| chr14 | 102529325 | 102529419 | chr14 | 102530007 | 102530234 | chr14 | 102530500 | 102530530 |
| chr14 | 102564464 | 102564605 | chr14 | 102682077 | 102682149 | chr14 | 102772607 | 102772695 |
| chr14 | 102973169 | 102973268 | chr14 | 103021391 | 103022003 | chr14 | 103394884 | 103395101 |
| chr14 | 103477643 | 103477794 | chr14 | 103655226 | 103655601 | chr14 | 103674078 | 103674079 |
| chr14 | 103687082 | 103687219 | chr14 | 103739967 | 103740150 | chr14 | 103740358 | 103740430 |
| chr14 | 103745699 | 103745750 | chr14 | 104160060 | 104160134 | chr14 | 104202705 | 104202759 |
| chr14 | 104355204 | 104355273 | chr14 | 104386476 | 104387067 | chr14 | 104547785 | 104547909 |
| chr14 | 104571985 | 104572116 | chr14 | 104601737 | 104601832 | chr14 | 104602033 | 104602063 |

TABLE 12-continued

Pan Cancer #2

| chr | start | end | chr | start | end | chr | start | end |
|---|---|---|---|---|---|---|---|---|
| chr14 | 104605032 | 104605114 | chr14 | 104620411 | 104620554 | chr14 | 104627664 | 104627759 |
| chr14 | 104645126 | 104645188 | chr14 | 104646317 | 104646491 | chr14 | 104647257 | 104647287 |
| chr14 | 104682545 | 104682656 | chr14 | 104862860 | 104863026 | chr14 | 104897228 | 104897294 |
| chr14 | 105071298 | 105071396 | chr14 | 105157485 | 105157554 | chr14 | 105239389 | 105239439 |
| chr14 | 105239793 | 105239825 | chr14 | 105241309 | 105241428 | chr14 | 105243032 | 105243064 |
| chr14 | 105246427 | 105246582 | chr14 | 105512063 | 105512395 | chr14 | 105658349 | 105658425 |
| chr14 | 105714258 | 105714334 | chr14 | 105714415 | 105714441 | chr14 | 105715248 | 105715392 |
| chr14 | 105830630 | 105830859 | chr14 | 105963655 | 105963772 | chr15 | 22822348 | 22822488 |
| chr15 | 23035709 | 23035781 | chr15 | 23158397 | 23158489 | chr15 | 23162337 | 23162372 |
| chr15 | 23273146 | 23273330 | chr15 | 23692316 | 23692453 | chr15 | 26107640 | 26107743 |
| chr15 | 26107846 | 26107860 | chr15 | 26108096 | 26108326 | chr15 | 26108549 | 26108701 |
| chr15 | 27212887 | 27213172 | chr15 | 27604062 | 27604123 | chr15 | 28341699 | 28342019 |
| chr15 | 28344173 | 28344187 | chr15 | 28344224 | 28344287 | chr15 | 28352240 | 28352421 |
| chr15 | 29077284 | 29077383 | chr15 | 29130807 | 29131047 | chr15 | 29131533 | 29131630 |
| chr15 | 29131756 | 29131875 | chr15 | 29396330 | 29396360 | chr15 | 29407777 | 29407813 |
| chr15 | 29407867 | 29408001 | chr15 | 29452432 | 29452462 | chr15 | 29862502 | 29862582 |
| chr15 | 30115185 | 30115228 | chr15 | 31455370 | 31455485 | chr15 | 31775596 | 31775637 |
| chr15 | 31775679 | 31775782 | chr15 | 32933918 | 32934018 | chr15 | 33009747 | 33009761 |
| chr15 | 33009822 | 33010675 | chr15 | 33010721 | 33011348 | chr15 | 33011601 | 33011633 |
| chr15 | 33487057 | 33487120 | chr15 | 33602801 | 33602886 | chr15 | 33603194 | 33603608 |
| chr15 | 33879242 | 33879272 | chr15 | 34517058 | 34517334 | chr15 | 34630439 | 34630449 |
| chr15 | 34630515 | 34630544 | chr15 | 34630818 | 34630865 | chr15 | 34729478 | 34729582 |
| chr15 | 34786504 | 34786943 | chr15 | 34787233 | 34787304 | chr15 | 34879708 | 34879866 |
| chr15 | 35046607 | 35046608 | chr15 | 35047034 | 35047133 | chr15 | 35087666 | 35087698 |
| chr15 | 35310631 | 35310868 | chr15 | 37180309 | 37180743 | chr15 | 37402974 | 37403086 |
| chr15 | 37403116 | 37403238 | chr15 | 40211819 | 40212190 | chr15 | 40575630 | 40575744 |
| chr15 | 40671495 | 40671620 | chr15 | 40675092 | 40675121 | chr15 | 40763811 | 40763862 |
| chr15 | 40782219 | 40782249 | chr15 | 40856224 | 40856254 | chr15 | 40877650 | 40877714 |
| chr15 | 41165245 | 41165700 | chr15 | 41541874 | 41541874 | chr15 | 41693679 | 41693794 |
| chr15 | 41708225 | 41708305 | chr15 | 41732398 | 41732471 | chr15 | 41804878 | 41805772 |
| chr15 | 41835548 | 41835720 | chr15 | 41913750 | 41913807 | chr15 | 41952572 | 41952711 |
| chr15 | 42749733 | 42749899 | chr15 | 42866975 | 42867049 | chr15 | 43551059 | 43551196 |
| chr15 | 43810405 | 43810435 | chr15 | 44037568 | 44037699 | chr15 | 45403636 | 45403680 |
| chr15 | 45403799 | 45403999 | chr15 | 45404103 | 45404130 | chr15 | 45404898 | 45405117 |
| chr15 | 45421385 | 45421435 | chr15 | 45421998 | 45422095 | chr15 | 45427370 | 45427410 |
| chr15 | 45427611 | 45427719 | chr15 | 45427772 | 45427786 | chr15 | 45444061 | 45444141 |
| chr15 | 45479460 | 45479516 | chr15 | 45493209 | 45493371 | chr15 | 45670462 | 45670838 |
| chr15 | 46021437 | 46021467 | chr15 | 47476118 | 47476239 | chr15 | 47476291 | 47476419 |
| chr15 | 47476877 | 47476980 | chr15 | 47477013 | 47477018 | chr15 | 48483956 | 48483986 |
| chr15 | 48936726 | 48937645 | chr15 | 48937710 | 48937987 | chr15 | 48938212 | 48938510 |
| chr15 | 50450454 | 50450574 | chr15 | 50464583 | 50464622 | chr15 | 51146606 | 51146636 |
| chr15 | 51385913 | 51386181 | chr15 | 51634075 | 51634135 | chr15 | 51973646 | 51973694 |
| chr15 | 51973764 | 51973934 | chr15 | 52000818 | 52000937 | chr15 | 53075809 | 53075864 |
| chr15 | 53075986 | 53077000 | chr15 | 53077066 | 53077361 | chr15 | 53077655 | 53077731 |
| chr15 | 53078064 | 53078236 | chr15 | 53079340 | 53079677 | chr15 | 53079718 | 53079891 |
| chr15 | 53079971 | 53080082 | chr15 | 53080337 | 53080606 | chr15 | 53080935 | 53080990 |
| chr15 | 53081399 | 53081677 | chr15 | 53082443 | 53082491 | chr15 | 53096816 | 53096891 |
| chr15 | 53097231 | 53097261 | chr15 | 53097778 | 53097906 | chr15 | 53098382 | 53098658 |
| chr15 | 54270498 | 54270707 | chr15 | 54270932 | 54270961 | chr15 | 54642236 | 54642352 |
| chr15 | 55452761 | 55452993 | chr15 | 55610440 | 55610698 | chr15 | 55699089 | 55699164 |
| chr15 | 55806758 | 55806900 | chr15 | 55880891 | 55881011 | chr15 | 56832508 | 56832546 |
| chr15 | 58357800 | 58357819 | chr15 | 59158488 | 59158537 | chr15 | 59158781 | 59158901 |
| chr15 | 59950198 | 59950363 | chr15 | 60084984 | 60085014 | chr15 | 60287038 | 60287585 |
| chr15 | 60287644 | 60288733 | chr15 | 60288786 | 60288844 | chr15 | 60289310 | 60289546 |
| chr15 | 60296122 | 60296209 | chr15 | 60296598 | 60296617 | chr15 | 60296861 | 60296923 |
| chr15 | 60297152 | 60297409 | chr15 | 60297637 | 60297826 | chr15 | 60297942 | 60298108 |
| chr15 | 60705106 | 60705204 | chr15 | 61520916 | 61521014 | chr15 | 61521659 | 61521937 |
| chr15 | 62456922 | 62456952 | chr15 | 64109724 | 64109788 | chr15 | 64618655 | 64618813 |
| chr15 | 64649481 | 64649553 | chr15 | 65118954 | 65118984 | chr15 | 65119265 | 65119295 |
| chr15 | 65119499 | 65119632 | chr15 | 65436137 | 65436213 | chr15 | 65669859 | 65669899 |
| chr15 | 65685591 | 65685708 | chr15 | 65823926 | 65824103 | chr15 | 65826189 | 65826359 |
| chr15 | 65862004 | 65862121 | chr15 | 66113240 | 66113270 | chr15 | 66649915 | 66649945 |
| chr15 | 66727409 | 66727498 | chr15 | 66729148 | 66729177 | chr15 | 66774117 | 66774203 |
| chr15 | 66789220 | 66789321 | chr15 | 66963816 | 66963871 | chr15 | 67146145 | 67146431 |
| chr15 | 67545536 | 67545566 | chr15 | 68112611 | 68112641 | chr15 | 68113868 | 68113898 |
| chr15 | 68114139 | 68114195 | chr15 | 68116369 | 68116621 | chr15 | 68117830 | 68118633 |
| chr15 | 68118930 | 68119174 | chr15 | 68119579 | 68120352 | chr15 | 68120827 | 68120857 |
| chr15 | 68121150 | 68121957 | chr15 | 68122643 | 68122673 | chr15 | 68125261 | 68125664 |
| chr15 | 68127801 | 68128350 | chr15 | 68128594 | 68128688 | chr15 | 68260519 | 68260709 |
| chr15 | 71055636 | 71055815 | chr15 | 72411929 | 72412176 | chr15 | 72612540 | 72612906 |
| chr15 | 72743741 | 72743796 | chr15 | 72979757 | 72979873 | chr15 | 73660004 | 73660067 |
| chr15 | 73661469 | 73661666 | chr15 | 74045075 | 74045097 | chr15 | 74422006 | 74422146 |
| chr15 | 74422869 | 74423002 | chr15 | 74658151 | 74658396 | chr15 | 74658502 | 74658587 |
| chr15 | 74686021 | 74686051 | chr15 | 74818772 | 74818806 | chr15 | 74903896 | 74903926 |
| chr15 | 74906463 | 74906493 | chr15 | 75205413 | 75205481 | chr15 | 75251346 | 75251382 |
| chr15 | 75251672 | 75251786 | chr15 | 75412459 | 75412714 | chr15 | 76627508 | 76627536 |

TABLE 12-continued

Pan Cancer #2

| chr | start | end | chr | start | end | chr | start | end |
|---|---|---|---|---|---|---|---|---|
| chr15 | 76627576 | 76627826 | chr15 | 76629163 | 76629220 | chr15 | 76629494 | 76629531 |
| chr15 | 76629814 | 76630124 | chr15 | 76630520 | 76630847 | chr15 | 76638472 | 76638496 |
| chr15 | 77448873 | 77449001 | chr15 | 78111196 | 78111210 | chr15 | 78501806 | 78501942 |
| chr15 | 78556819 | 78557108 | chr15 | 78595791 | 78596218 | chr15 | 78632727 | 78632823 |
| chr15 | 78859435 | 78859603 | chr15 | 78912281 | 78912371 | chr15 | 78912623 | 78912653 |
| chr15 | 78912912 | 78913027 | chr15 | 78913095 | 78913170 | chr15 | 78913535 | 78913651 |
| chr15 | 79104217 | 79104246 | chr15 | 79104466 | 79104495 | chr15 | 79151898 | 79152007 |
| chr15 | 79381705 | 79381745 | chr15 | 79382099 | 79382571 | chr15 | 79382786 | 79383257 |
| chr15 | 79383947 | 79383977 | chr15 | 79502211 | 79502360 | chr15 | 79575278 | 79575474 |
| chr15 | 79576145 | 79576277 | chr15 | 79724502 | 79724560 | chr15 | 79724607 | 79724792 |
| chr15 | 79724864 | 79725140 | chr15 | 79725422 | 79725539 | chr15 | 80216803 | 80216884 |
| chr15 | 81071827 | 81071867 | chr15 | 82336879 | 82336972 | chr15 | 82340070 | 82340157 |
| chr15 | 83314048 | 83314106 | chr15 | 83315336 | 83315393 | chr15 | 83316251 | 83317087 |
| chr15 | 83349234 | 83349611 | chr15 | 83349672 | 83349686 | chr15 | 83378212 | 83378370 |
| chr15 | 83622512 | 83622565 | chr15 | 83655843 | 83655934 | chr15 | 83776255 | 83776306 |
| chr15 | 83776333 | 83776716 | chr15 | 83776769 | 83776785 | chr15 | 83866523 | 83866559 |
| chr15 | 83875648 | 83875665 | chr15 | 83875706 | 83875901 | chr15 | 83877055 | 83877149 |
| chr15 | 83953884 | 83953903 | chr15 | 83954380 | 83954409 | chr15 | 84115747 | 84115853 |
| chr15 | 84115932 | 84115966 | chr15 | 84116905 | 84116949 | chr15 | 84322994 | 84323037 |
| chr15 | 84711204 | 84711367 | chr15 | 84748578 | 84748619 | chr15 | 84748679 | 84749260 |
| chr15 | 85142994 | 85143054 | chr15 | 85886518 | 85886604 | chr15 | 86002524 | 86002690 |
| chr15 | 88798725 | 88798791 | chr15 | 88799537 | 88800301 | chr15 | 88800541 | 88801008 |
| chr15 | 88801089 | 88801103 | chr15 | 89149169 | 89149448 | chr15 | 89248753 | 89248907 |
| chr15 | 89346050 | 89346326 | chr15 | 89346347 | 89346393 | chr15 | 89346670 | 89346793 |
| chr15 | 89346882 | 89346943 | chr15 | 89903484 | 89903814 | chr15 | 89910521 | 89910748 |
| chr15 | 89911087 | 89911186 | chr15 | 89913750 | 89913780 | chr15 | 89914231 | 89914449 |
| chr15 | 89914867 | 89914895 | chr15 | 89915240 | 89915369 | chr15 | 89921956 | 89922006 |
| chr15 | 89922500 | 89922546 | chr15 | 89942755 | 89942945 | chr15 | 89943410 | 89943706 |
| chr15 | 89949617 | 89949942 | chr15 | 89950236 | 89950736 | chr15 | 89951082 | 89951113 |
| chr15 | 89951466 | 89951801 | chr15 | 89952153 | 89952452 | chr15 | 89952700 | 89953055 |
| chr15 | 89954197 | 89954335 | chr15 | 89956423 | 89956450 | chr15 | 90039563 | 90039711 |
| chr15 | 90631823 | 90631948 | chr15 | 90667461 | 90667586 | chr15 | 90703262 | 90703345 |
| chr15 | 90755916 | 90756079 | chr15 | 91643360 | 91643586 | chr15 | 92936290 | 92936322 |
| chr15 | 92937153 | 92937374 | chr15 | 92937927 | 92938060 | chr15 | 92938123 | 92938293 |
| chr15 | 93158592 | 93158739 | chr15 | 93350668 | 93350698 | chr15 | 93364552 | 93364624 |
| chr15 | 93631739 | 93632014 | chr15 | 93632660 | 93633233 | chr15 | 94347602 | 94347632 |
| chr15 | 96874362 | 96874514 | chr15 | 96889154 | 96889183 | chr15 | 96889401 | 96889430 |
| chr15 | 96897934 | 96898010 | chr15 | 96911559 | 96911691 | chr15 | 96952696 | 96953098 |
| chr15 | 96953132 | 96953209 | chr15 | 96959730 | 96959960 | chr15 | 96960376 | 96960409 |
| chr15 | 96960732 | 96960826 | chr15 | 97006372 | 97006533 | chr15 | 98504114 | 98504144 |
| chr15 | 98634851 | 98634949 | chr15 | 98776762 | 98776792 | chr15 | 98836178 | 98836393 |
| chr15 | 98964786 | 98965138 | chr15 | 99193206 | 99193480 | chr15 | 99193914 | 99194186 |
| chr15 | 99254040 | 99254208 | chr15 | 99295692 | 99295749 | chr15 | 99346861 | 99347040 |
| chr15 | 99354999 | 99355041 | chr15 | 99453230 | 99453440 | chr15 | 99456299 | 99456329 |
| chr15 | 99497059 | 99497132 | chr15 | 100274325 | 100274385 | chr15 | 100339980 | 100340010 |
| chr15 | 100913423 | 100913595 | chr15 | 101420521 | 101420610 | chr15 | 101420972 | 101420989 |
| chr15 | 101818327 | 101818357 | chr15 | 102115873 | 102115905 | chr15 | 102193587 | 102193713 |
| chr15 | 102286533 | 102286563 | chr16 | 93831 | 93932 | chr16 | 142649 | 142783 |
| chr16 | 189744 | 189933 | chr16 | 199886 | 199943 | chr16 | 215416 | 215872 |
| chr16 | 215913 | 216224 | chr16 | 216676 | 217036 | chr16 | 230265 | 230315 |
| chr16 | 230497 | 230610 | chr16 | 232136 | 232166 | chr16 | 280323 | 280395 |
| chr16 | 318104 | 318227 | chr16 | 318498 | 318763 | chr16 | 337599 | 337659 |
| chr16 | 410377 | 410407 | chr16 | 565492 | 565623 | chr16 | 571714 | 571959 |
| chr16 | 611385 | 611520 | chr16 | 611969 | 612260 | chr16 | 612869 | 613037 |
| chr16 | 667141 | 667297 | chr16 | 667547 | 667622 | chr16 | 667876 | 668074 |
| chr16 | 672730 | 672806 | chr16 | 677972 | 678084 | chr16 | 700299 | 700329 |
| chr16 | 726626 | 726990 | chr16 | 731488 | 731610 | chr16 | 735205 | 735594 |
| chr16 | 740791 | 740914 | chr16 | 741376 | 741601 | chr16 | 762523 | 762694 |
| chr16 | 837361 | 837460 | chr16 | 845955 | 845985 | chr16 | 882484 | 882588 |
| chr16 | 895093 | 895166 | chr16 | 943481 | 943553 | chr16 | 1018120 | 1018150 |
| chr16 | 1019640 | 1019685 | chr16 | 1030444 | 1030655 | chr16 | 1052587 | 1052627 |
| chr16 | 1102927 | 1102957 | chr16 | 1116661 | 1116691 | chr16 | 1122858 | 1122946 |
| chr16 | 1129011 | 1129140 | chr16 | 1155162 | 1155212 | chr16 | 1186809 | 1186850 |
| chr16 | 1204003 | 1204034 | chr16 | 1217307 | 1217503 | chr16 | 1218034 | 1218090 |
| chr16 | 1228804 | 1228916 | chr16 | 1229970 | 1230142 | chr16 | 1248604 | 1248675 |
| chr16 | 1267925 | 1268120 | chr16 | 1271546 | 1271646 | chr16 | 1312526 | 1312611 |
| chr16 | 1323976 | 1324061 | chr16 | 1382901 | 1382940 | chr16 | 1394502 | 1394596 |
| chr16 | 1397454 | 1397484 | chr16 | 1407370 | 1407846 | chr16 | 1408210 | 1408240 |
| chr16 | 1428508 | 1428873 | chr16 | 1466425 | 1466455 | chr16 | 1469334 | 1469527 |
| chr16 | 1491567 | 1491613 | chr16 | 1523925 | 1523971 | chr16 | 1704656 | 1704800 |
| chr16 | 1729868 | 1730022 | chr16 | 1730306 | 1730597 | chr16 | 1741853 | 1742079 |
| chr16 | 1750769 | 1750907 | chr16 | 1842490 | 1842519 | chr16 | 1993818 | 1993848 |
| chr16 | 2029072 | 2029137 | chr16 | 2040914 | 2040960 | chr16 | 2040981 | 2041512 |
| chr16 | 2041582 | 2042160 | chr16 | 2042875 | 2042905 | chr16 | 2086831 | 2086860 |
| chr16 | 2106703 | 2106732 | chr16 | 2111966 | 2111995 | chr16 | 2120515 | 2120544 |
| chr16 | 2122243 | 2122272 | chr16 | 2124205 | 2124348 | chr16 | 2126080 | 2126109 |

TABLE 12-continued

Pan Cancer #2

| chr | start | end | chr | start | end | chr | start | end |
|---|---|---|---|---|---|---|---|---|
| chr16 | 2128577 | 2129581 | chr16 | 2130361 | 2130390 | chr16 | 2132244 | 2132315 |
| chr16 | 2135301 | 2135330 | chr16 | 2136228 | 2136257 | chr16 | 2136727 | 2136855 |
| chr16 | 2140403 | 2140438 | chr16 | 2141909 | 2141972 | chr16 | 2142546 | 2142628 |
| chr16 | 2213313 | 2213343 | chr16 | 2232745 | 2233003 | chr16 | 2234726 | 2235020 |
| chr16 | 2275129 | 2275182 | chr16 | 2281249 | 2281314 | chr16 | 2287295 | 2287370 |
| chr16 | 2466225 | 2466307 | chr16 | 2485858 | 2485917 | chr16 | 2508414 | 2508453 |
| chr16 | 2531069 | 2531177 | chr16 | 2731530 | 2731560 | chr16 | 2764377 | 2764470 |
| chr16 | 2770122 | 2770602 | chr16 | 2818101 | 2818156 | chr16 | 2892542 | 2892602 |
| chr16 | 2892627 | 2892729 | chr16 | 2956451 | 2956670 | chr16 | 2974601 | 2974650 |
| chr16 | 3017157 | 3017430 | chr16 | 3068171 | 3068201 | chr16 | 3151127 | 3151186 |
| chr16 | 3211708 | 3212019 | chr16 | 3220591 | 3220892 | chr16 | 3221142 | 3221700 |
| chr16 | 3221787 | 3222239 | chr16 | 3225471 | 3225607 | chr16 | 3232739 | 3233016 |
| chr16 | 3233199 | 3233330 | chr16 | 3233435 | 3234103 | chr16 | 3234165 | 3234452 |
| chr16 | 3237857 | 3238546 | chr16 | 3238993 | 3239848 | chr16 | 3241549 | 3241663 |
| chr16 | 3241936 | 3241966 | chr16 | 3269249 | 3269350 | chr16 | 3284117 | 3284147 |
| chr16 | 3355279 | 3355718 | chr16 | 3492583 | 3492675 | chr16 | 3598920 | 3598953 |
| chr16 | 3696694 | 3696724 | chr16 | 3802981 | 3803074 | chr16 | 3950127 | 3950279 |
| chr16 | 4264529 | 4264694 | chr16 | 4303144 | 4303174 | chr16 | 4310735 | 4310847 |
| chr16 | 4431126 | 4431189 | chr16 | 4431487 | 4431516 | chr16 | 4731638 | 4731718 |
| chr16 | 4733166 | 4733195 | chr16 | 4738567 | 4738680 | chr16 | 4751554 | 4751583 |
| chr16 | 4783226 | 4783375 | chr16 | 4846136 | 4846514 | chr16 | 4887144 | 4887244 |
| chr16 | 5037900 | 5038004 | chr16 | 5541116 | 5541158 | chr16 | 6035056 | 6035208 |
| chr16 | 6069941 | 6070019 | chr16 | 7354634 | 7354657 | chr16 | 7382499 | 7382534 |
| chr16 | 7525361 | 7525531 | chr16 | 8781032 | 8781177 | chr16 | 8870353 | 8870383 |
| chr16 | 9009860 | 9009989 | chr16 | 10274399 | 10274429 | chr16 | 10275308 | 10275392 |
| chr16 | 10275752 | 10275948 | chr16 | 10276360 | 10277050 | chr16 | 10277072 | 10277437 |
| chr16 | 10479815 | 10479980 | chr16 | 11242000 | 11242138 | chr16 | 11427659 | 11427732 |
| chr16 | 11490632 | 11490662 | chr16 | 11923005 | 11923035 | chr16 | 12011258 | 12011325 |
| chr16 | 12011940 | 12012073 | chr16 | 12066767 | 12066806 | chr16 | 12210772 | 12210896 |
| chr16 | 12211279 | 12211416 | chr16 | 12530169 | 12530199 | chr16 | 12971776 | 12971934 |
| chr16 | 12994459 | 12994737 | chr16 | 12995062 | 12995593 | chr16 | 12995803 | 12995803 |
| chr16 | 12996074 | 12996328 | chr16 | 12996617 | 12996720 | chr16 | 12996948 | 12997011 |
| chr16 | 12997386 | 12997703 | chr16 | 14021974 | 14022003 | chr16 | 14041504 | 14041533 |
| chr16 | 14041795 | 14041824 | chr16 | 14042062 | 14042091 | chr16 | 14189998 | 14190069 |
| chr16 | 14724632 | 14724736 | chr16 | 14725842 | 14726005 | chr16 | 15489599 | 15489808 |
| chr16 | 15708247 | 15708309 | chr16 | 15738905 | 15739042 | chr16 | 15820825 | 15820865 |
| chr16 | 16868746 | 16868905 | chr16 | 18163245 | 18163352 | chr16 | 18802250 | 18802680 |
| chr16 | 18950928 | 18951018 | chr16 | 19430908 | 19430949 | chr16 | 19531564 | 19531699 |
| chr16 | 19567202 | 19567449 | chr16 | 19895125 | 19895155 | chr16 | 21541606 | 21541636 |
| chr16 | 21665540 | 21665570 | chr16 | 21666641 | 21666771 | chr16 | 21674664 | 21674777 |
| chr16 | 21831621 | 21831957 | chr16 | 21839328 | 21839470 | chr16 | 22300599 | 22300637 |
| chr16 | 22326397 | 22326427 | chr16 | 22824701 | 22825076 | chr16 | 22825327 | 22825469 |
| chr16 | 22825886 | 22826081 | chr16 | 23313464 | 23313522 | chr16 | 23313780 | 23313836 |
| chr16 | 23706412 | 23706520 | chr16 | 23766097 | 23766130 | chr16 | 23847311 | 23847511 |
| chr16 | 23847789 | 23847874 | chr16 | 23847934 | 23847956 | chr16 | 24127251 | 24127338 |
| chr16 | 24172241 | 24172271 | chr16 | 24180710 | 24180760 | chr16 | 24267115 | 24267144 |
| chr16 | 24267485 | 24267578 | chr16 | 24415106 | 24415176 | chr16 | 25266537 | 25266573 |
| chr16 | 25542301 | 25542452 | chr16 | 25551107 | 25551264 | chr16 | 25702955 | 25702992 |
| chr16 | 25703642 | 25704122 | chr16 | 25704390 | 25704628 | chr16 | 25921574 | 25921604 |
| chr16 | 26302585 | 26302619 | chr16 | 26664739 | 26664775 | chr16 | 27207774 | 27207852 |
| chr16 | 27459938 | 27460074 | chr16 | 27749857 | 27750033 | chr16 | 27961122 | 27961254 |
| chr16 | 28074176 | 28074254 | chr16 | 28074418 | 28074684 | chr16 | 28074959 | 28075197 |
| chr16 | 28093825 | 28093866 | chr16 | 28224516 | 28224546 | chr16 | 28491774 | 28491924 |
| chr16 | 28560309 | 28560381 | chr16 | 28823157 | 28823459 | chr16 | 28850998 | 28851028 |
| chr16 | 28877839 | 28877883 | chr16 | 28891040 | 28891072 | chr16 | 29119008 | 29119058 |
| chr16 | 29153284 | 29153356 | chr16 | 29244900 | 29244997 | chr16 | 29830871 | 29831078 |
| chr16 | 29888624 | 29888658 | chr16 | 29936211 | 29936272 | chr16 | 30017330 | 30017447 |
| chr16 | 30065485 | 30065525 | chr16 | 30085867 | 30085995 | chr16 | 30116285 | 30116315 |
| chr16 | 30124691 | 30124861 | chr16 | 30169925 | 30170103 | chr16 | 30388542 | 30388574 |
| chr16 | 30402082 | 30402112 | chr16 | 30609373 | 30609408 | chr16 | 30639693 | 30639735 |
| chr16 | 30804321 | 30804472 | chr16 | 30826334 | 30826509 | chr16 | 30907010 | 30907148 |
| chr16 | 31227914 | 31228313 | chr16 | 31384593 | 31384623 | chr16 | 31446830 | 31447096 |
| chr16 | 31498008 | 31498165 | chr16 | 31500504 | 31500673 | chr16 | 31580560 | 31581036 |
| chr16 | 46569239 | 46569474 | chr16 | 46721567 | 46721707 | chr16 | 46803280 | 46803355 |
| chr16 | 47177525 | 47177606 | chr16 | 48450544 | 48450574 | chr16 | 48641663 | 48641693 |
| chr16 | 48642149 | 48642179 | chr16 | 48845120 | 48845125 | chr16 | 49309170 | 49309262 |
| chr16 | 49311523 | 49311989 | chr16 | 49312033 | 49312299 | chr16 | 49313363 | 49313710 |
| chr16 | 49314022 | 49314118 | chr16 | 49314419 | 49314561 | chr16 | 49314784 | 49314821 |
| chr16 | 49315276 | 49315306 | chr16 | 49315919 | 49316315 | chr16 | 49316509 | 49316580 |
| chr16 | 49638060 | 49638090 | chr16 | 50335767 | 50335797 | chr16 | 51183964 | 51184406 |
| chr16 | 51184807 | 51184957 | chr16 | 51185055 | 51185291 | chr16 | 51185844 | 51185964 |
| chr16 | 51186026 | 51186280 | chr16 | 51186596 | 51186939 | chr16 | 51188697 | 51188711 |
| chr16 | 51189922 | 51190037 | chr16 | 51190122 | 51190215 | chr16 | 53447826 | 53448002 |
| chr16 | 53467271 | 53467395 | chr16 | 53563622 | 53563654 | chr16 | 54128645 | 54128713 |
| chr16 | 54318898 | 54318988 | chr16 | 54319420 | 54319468 | chr16 | 54321638 | 54321818 |
| chr16 | 54324999 | 54325131 | chr16 | 54628691 | 54628867 | chr16 | 54964948 | 54965114 |

TABLE 12-continued

Pan Cancer #2

| chr | start | end | chr | start | end | chr | start | end |
|---|---|---|---|---|---|---|---|---|
| chr16 | 54966830 | 54967264 | chr16 | 54971400 | 54971430 | chr16 | 55090666 | 55090861 |
| chr16 | 55357926 | 55357940 | chr16 | 55357992 | 55358086 | chr16 | 55358316 | 55358350 |
| chr16 | 55358798 | 55359071 | chr16 | 55363009 | 55363223 | chr16 | 55364716 | 55364843 |
| chr16 | 55365103 | 55365218 | chr16 | 55404999 | 55405214 | chr16 | 55689886 | 55689915 |
| chr16 | 55690115 | 55690379 | chr16 | 55690454 | 55690576 | chr16 | 55690762 | 55690809 |
| chr16 | 56224557 | 56224832 | chr16 | 56228370 | 56228416 | chr16 | 56228578 | 56228581 |
| chr16 | 56651094 | 56651123 | chr16 | 56651239 | 56651275 | chr16 | 56659175 | 56659673 |
| chr16 | 56672158 | 56672172 | chr16 | 56672222 | 56672385 | chr16 | 56672514 | 56672654 |
| chr16 | 56672656 | 56672685 | chr16 | 56709837 | 56709892 | chr16 | 56709950 | 56710030 |
| chr16 | 57222663 | 57222709 | chr16 | 57318379 | 57318412 | chr16 | 57326422 | 57326613 |
| chr16 | 57935454 | 57935605 | chr16 | 58018634 | 58018845 | chr16 | 58019225 | 58019430 |
| chr16 | 58120795 | 58120961 | chr16 | 58427501 | 58427542 | chr16 | 58497221 | 58497335 |
| chr16 | 58497752 | 58497829 | chr16 | 58498175 | 58498204 | chr16 | 58498570 | 58498724 |
| chr16 | 58521708 | 58521737 | chr16 | 58534666 | 58534695 | chr16 | 58545487 | 58545516 |
| chr16 | 58550489 | 58550519 | chr16 | 58969757 | 58969792 | chr16 | 62068463 | 62068517 |
| chr16 | 62068952 | 62068982 | chr16 | 62070743 | 62070773 | chr16 | 65154933 | 65155091 |
| chr16 | 65156385 | 65156489 | chr16 | 66461786 | 66461840 | chr16 | 66612882 | 66613095 |
| chr16 | 66613335 | 66613369 | chr16 | 66863917 | 66863959 | chr16 | 67197698 | 67197769 |
| chr16 | 67198009 | 67198039 | chr16 | 67198917 | 67198957 | chr16 | 67241204 | 67241234 |
| chr16 | 67313865 | 67313895 | chr16 | 67850955 | 67850985 | chr16 | 67871102 | 67871134 |
| chr16 | 68481486 | 68481543 | chr16 | 68482808 | 68482941 | chr16 | 68544259 | 68544378 |
| chr16 | 68676408 | 68676604 | chr16 | 68676842 | 68676984 | chr16 | 68770755 | 68771298 |
| chr16 | 68844158 | 68844187 | chr16 | 68846033 | 68846062 | chr16 | 68856078 | 68856107 |
| chr16 | 68876782 | 68876996 | chr16 | 69026784 | 69026814 | chr16 | 69564118 | 69564200 |
| chr16 | 69969260 | 69969290 | chr16 | 70489585 | 70489681 | chr16 | 70595535 | 70595700 |
| chr16 | 70794492 | 70794633 | chr16 | 71460027 | 71460088 | chr16 | 71460271 | 71460351 |
| chr16 | 71507759 | 71507791 | chr16 | 71677557 | 71677661 | chr16 | 71715779 | 71715809 |
| chr16 | 71918889 | 71919024 | chr16 | 72957763 | 72957795 | chr16 | 74886148 | 74886268 |
| chr16 | 74901594 | 74901659 | chr16 | 75019751 | 75019781 | chr16 | 75549798 | 75549836 |
| chr16 | 76008985 | 76009154 | chr16 | 77247440 | 77247470 | chr16 | 77468261 | 77468457 |
| chr16 | 77822589 | 77822874 | chr16 | 78079969 | 78080054 | chr16 | 79623602 | 79623616 |
| chr16 | 79623798 | 79623914 | chr16 | 80837962 | 80838143 | chr16 | 80966399 | 80966431 |
| chr16 | 81564199 | 81564229 | chr16 | 81929362 | 81929392 | chr16 | 81946246 | 81946275 |
| chr16 | 81962167 | 81962196 | chr16 | 82660360 | 82660496 | chr16 | 82660712 | 82660741 |
| chr16 | 84074836 | 84074871 | chr16 | 84153364 | 84153394 | chr16 | 84402244 | 84402319 |
| chr16 | 84519974 | 84520010 | chr16 | 84651793 | 84651822 | chr16 | 84823626 | 84823656 |
| chr16 | 84853288 | 84853376 | chr16 | 85075434 | 85075553 | chr16 | 85317850 | 85317882 |
| chr16 | 85485747 | 85485855 | chr16 | 85497445 | 85497475 | chr16 | 85517345 | 85517521 |
| chr16 | 85651520 | 85651550 | chr16 | 85678639 | 85678761 | chr16 | 85684308 | 85684457 |
| chr16 | 85699689 | 85699921 | chr16 | 85834460 | 85834495 | chr16 | 85932828 | 85932858 |
| chr16 | 86320354 | 86320391 | chr16 | 86320755 | 86320800 | chr16 | 86321020 | 86321068 |
| chr16 | 86530947 | 86530992 | chr16 | 86531017 | 86531046 | chr16 | 86531375 | 86531480 |
| chr16 | 86531528 | 86531573 | chr16 | 86541591 | 86541968 | chr16 | 86542373 | 86542457 |
| chr16 | 86544191 | 86544557 | chr16 | 86571984 | 86572014 | chr16 | 86599481 | 86599844 |
| chr16 | 86600483 | 86600686 | chr16 | 86600958 | 86601015 | chr16 | 86601286 | 86601539 |
| chr16 | 86602038 | 86602514 | chr16 | 86878150 | 86878180 | chr16 | 87092439 | 87092553 |
| chr16 | 87525622 | 87525701 | chr16 | 87635103 | 87635133 | chr16 | 87636627 | 87636907 |
| chr16 | 87714272 | 87714381 | chr16 | 87723735 | 87724098 | chr16 | 88007072 | 88007108 |
| chr16 | 88106322 | 88106398 | chr16 | 88164401 | 88164468 | chr16 | 88498241 | 88498760 |
| chr16 | 88504058 | 88504315 | chr16 | 88506346 | 88506526 | chr16 | 88512427 | 88512529 |
| chr16 | 88543428 | 88543458 | chr16 | 88550263 | 88550483 | chr16 | 88603696 | 88603760 |
| chr16 | 88623960 | 88624167 | chr16 | 88711337 | 88711507 | chr16 | 88757466 | 88757496 |
| chr16 | 88879949 | 88880124 | chr16 | 88883238 | 88883377 | chr16 | 88941058 | 88941141 |
| chr16 | 88942119 | 88942160 | chr16 | 88943559 | 88944024 | chr16 | 88945815 | 88945995 |
| chr16 | 88955249 | 88955368 | chr16 | 88956230 | 88956399 | chr16 | 88957350 | 88957857 |
| chr16 | 88958397 | 88958431 | chr16 | 88963277 | 88963763 | chr16 | 88966303 | 88966588 |
| chr16 | 88968709 | 88968789 | chr16 | 88978024 | 88978072 | chr16 | 88993078 | 88993230 |
| chr16 | 88999617 | 88999647 | chr16 | 89000168 | 89000204 | chr16 | 89001094 | 89001124 |
| chr16 | 89007520 | 89007558 | chr16 | 89007880 | 89007995 | chr16 | 89008562 | 89008592 |
| chr16 | 89047717 | 89047747 | chr16 | 89072503 | 89072774 | chr16 | 89086109 | 89086197 |
| chr16 | 89107675 | 89107732 | chr16 | 89109385 | 89109415 | chr16 | 89120038 | 89120319 |
| chr16 | 89120708 | 89120864 | chr16 | 89138016 | 89138060 | chr16 | 89220327 | 89220398 |
| chr16 | 89220655 | 89220922 | chr16 | 89240843 | 89240873 | chr16 | 89254653 | 89254830 |
| chr16 | 89267334 | 89267364 | chr16 | 89267808 | 89267824 | chr16 | 89558610 | 89558703 |
| chr16 | 89575728 | 89575861 | chr16 | 89584136 | 89584417 | chr16 | 89676025 | 89676197 |
| chr16 | 89883972 | 89884185 | chr16 | 89884966 | 89885142 | chr16 | 89900124 | 89900180 |
| chr16 | 89900455 | 89900526 | chr16 | 90115428 | 90115458 | chr17 | 415134 | 415163 |
| chr17 | 556252 | 556282 | chr17 | 617001 | 617064 | chr17 | 631704 | 631734 |
| chr17 | 1082884 | 1083002 | chr17 | 1136593 | 1136653 | chr17 | 1174274 | 1174361 |
| chr17 | 1174385 | 1174413 | chr17 | 1494550 | 1494613 | chr17 | 1536116 | 1536146 |
| chr17 | 1545976 | 1546442 | chr17 | 1623703 | 1623735 | chr17 | 1959468 | 1959520 |
| chr17 | 2207718 | 2208063 | chr17 | 2219952 | 2220319 | chr17 | 2220564 | 2221059 |
| chr17 | 2250051 | 2250081 | chr17 | 2278801 | 2278925 | chr17 | 2496019 | 2496049 |
| chr17 | 2538269 | 2538337 | chr17 | 2607905 | 2607986 | chr17 | 2663898 | 2664032 |
| chr17 | 2811362 | 2811392 | chr17 | 2873476 | 2873551 | chr17 | 2950959 | 2951091 |
| chr17 | 3438914 | 3438937 | chr17 | 3657502 | 3657553 | chr17 | 3658490 | 3658519 |

TABLE 12-continued

Pan Cancer #2

| chr | start | end | chr | start | end | chr | start | end |
|---|---|---|---|---|---|---|---|---|
| chr17 | 3658849 | 3659011 | chr17 | 4544607 | 4544710 | chr17 | 4693354 | 4693388 |
| chr17 | 4698990 | 4699252 | chr17 | 4891276 | 4891305 | chr17 | 4891527 | 4891556 |
| chr17 | 5000428 | 5000790 | chr17 | 5019637 | 5019662 | chr17 | 5019738 | 5019761 |
| chr17 | 5167638 | 5167681 | chr17 | 5168597 | 5168732 | chr17 | 6470357 | 6470419 |
| chr17 | 6616637 | 6616686 | chr17 | 6616911 | 6617173 | chr17 | 6679190 | 6679296 |
| chr17 | 6946107 | 6946141 | chr17 | 7043422 | 7043595 | chr17 | 7242844 | 7242899 |
| chr17 | 7348885 | 7348997 | chr17 | 7368947 | 7369139 | chr17 | 7471610 | 7471709 |
| chr17 | 7488151 | 7488249 | chr17 | 7555117 | 7555425 | chr17 | 7572957 | 7573018 |
| chr17 | 7573968 | 7574028 | chr17 | 7576847 | 7577167 | chr17 | 7577504 | 7577604 |
| chr17 | 7578164 | 7578570 | chr17 | 7579285 | 7579880 | chr17 | 7906254 | 7906535 |
| chr17 | 7906832 | 7906861 | chr17 | 8104145 | 8104260 | chr17 | 8230335 | 8230694 |
| chr17 | 8534493 | 8534582 | chr17 | 8774623 | 8774653 | chr17 | 8868620 | 8868667 |
| chr17 | 8868815 | 8869385 | chr17 | 8906266 | 8906518 | chr17 | 8906993 | 8907575 |
| chr17 | 8926060 | 8926263 | chr17 | 9790805 | 9790835 | chr17 | 10101084 | 10101109 |
| chr17 | 10101132 | 10101447 | chr17 | 10102415 | 10102665 | chr17 | 10599510 | 10599546 |
| chr17 | 11144926 | 11144989 | chr17 | 11984693 | 11984722 | chr17 | 11998944 | 11998973 |
| chr17 | 12013726 | 12013755 | chr17 | 12016503 | 12016630 | chr17 | 12028618 | 12028647 |
| chr17 | 12659029 | 12659063 | chr17 | 13504195 | 13504195 | chr17 | 13504557 | 13504681 |
| chr17 | 13505002 | 13505188 | chr17 | 13505418 | 13505572 | chr17 | 14201041 | 14201181 |
| chr17 | 14204212 | 14204242 | chr17 | 14204527 | 14204620 | chr17 | 15245050 | 15245139 |
| chr17 | 15926819 | 15926849 | chr17 | 16119860 | 16120047 | chr17 | 16282251 | 16282300 |
| chr17 | 16284630 | 16285065 | chr17 | 16326144 | 16326216 | chr17 | 16428708 | 16428738 |
| chr17 | 16570699 | 16570794 | chr17 | 17062574 | 17062763 | chr17 | 17117365 | 17117395 |
| chr17 | 17123963 | 17123993 | chr17 | 17398404 | 17398440 | chr17 | 17719242 | 17719355 |
| chr17 | 18162844 | 18163325 | chr17 | 18538154 | 18538275 | chr17 | 18817198 | 18817284 |
| chr17 | 19769739 | 19769821 | chr17 | 19886035 | 19886221 | chr17 | 20039589 | 20039676 |
| chr17 | 20081131 | 20081161 | chr17 | 20205055 | 20205181 | chr17 | 20238152 | 20238198 |
| chr17 | 20468021 | 20468090 | chr17 | 20817755 | 20817917 | chr17 | 21003587 | 21003721 |
| chr17 | 25620573 | 25620715 | chr17 | 25676879 | 25676989 | chr17 | 25680264 | 25680294 |
| chr17 | 25907750 | 25907780 | chr17 | 26263183 | 26263322 | chr17 | 26554634 | 26554705 |
| chr17 | 26927249 | 26927410 | chr17 | 26961770 | 26961833 | chr17 | 27036492 | 27037023 |
| chr17 | 27038649 | 27038685 | chr17 | 27056577 | 27056857 | chr17 | 27081845 | 27081963 |
| chr17 | 27170162 | 27170460 | chr17 | 27181180 | 27181371 | chr17 | 27332453 | 27332660 |
| chr17 | 27686651 | 27686783 | chr17 | 27716114 | 27716220 | chr17 | 27716436 | 27716642 |
| chr17 | 27940591 | 27940911 | chr17 | 28112648 | 28112688 | chr17 | 28112951 | 28113037 |
| chr17 | 28562701 | 28562765 | chr17 | 29232244 | 29232350 | chr17 | 29234283 | 29234313 |
| chr17 | 29249717 | 29249930 | chr17 | 29298080 | 29298581 | chr17 | 29508761 | 29508790 |
| chr17 | 29541527 | 29541556 | chr17 | 29562732 | 29562761 | chr17 | 29718215 | 29718269 |
| chr17 | 29719187 | 29719242 | chr17 | 30243768 | 30243907 | chr17 | 30250325 | 30250364 |
| chr17 | 30258469 | 30258499 | chr17 | 30568137 | 30568174 | chr17 | 30710818 | 30710888 |
| chr17 | 31618425 | 31619319 | chr17 | 31619951 | 31620026 | chr17 | 32386720 | 32386875 |
| chr17 | 32484020 | 32484049 | chr17 | 32906379 | 32906555 | chr17 | 32906599 | 32906636 |
| chr17 | 32906987 | 32907146 | chr17 | 32907652 | 32907753 | chr17 | 32908132 | 32908146 |
| chr17 | 32908171 | 32908374 | chr17 | 32908647 | 32908931 | chr17 | 33288229 | 33288351 |
| chr17 | 33288890 | 33288988 | chr17 | 33672916 | 33672986 | chr17 | 33721211 | 33721349 |
| chr17 | 33877286 | 33877439 | chr17 | 33917210 | 33917268 | chr17 | 35165645 | 35165691 |
| chr17 | 35165986 | 35166016 | chr17 | 35285542 | 35285666 | chr17 | 35290388 | 35290655 |
| chr17 | 35291320 | 35291354 | chr17 | 35291829 | 35291898 | chr17 | 35291921 | 35292626 |
| chr17 | 35293704 | 35294154 | chr17 | 35294461 | 35294505 | chr17 | 35295047 | 35295160 |
| chr17 | 35296143 | 35296292 | chr17 | 35296728 | 35296888 | chr17 | 35297619 | 35298153 |
| chr17 | 35299251 | 35299443 | chr17 | 35299601 | 35299965 | chr17 | 35300261 | 35300712 |
| chr17 | 35300813 | 35300854 | chr17 | 35303340 | 35303535 | chr17 | 35872722 | 35872861 |
| chr17 | 36103021 | 36103326 | chr17 | 36103571 | 36103601 | chr17 | 36104218 | 36104550 |
| chr17 | 36104644 | 36104779 | chr17 | 36105223 | 36105349 | chr17 | 36105459 | 36105596 |
| chr17 | 36715772 | 36715967 | chr17 | 37001415 | 37001921 | chr17 | 37011176 | 37011236 |
| chr17 | 37131789 | 37132028 | chr17 | 37181771 | 37181865 | chr17 | 37192072 | 37192201 |
| chr17 | 37312431 | 37312477 | chr17 | 37321186 | 37321624 | chr17 | 37321788 | 37321972 |
| chr17 | 37366337 | 37366552 | chr17 | 37369180 | 37369210 | chr17 | 37381011 | 37381429 |
| chr17 | 37381571 | 37381726 | chr17 | 37381826 | 37381850 | chr17 | 37382146 | 37382248 |
| chr17 | 37484062 | 37484128 | chr17 | 37757153 | 37757217 | chr17 | 37760488 | 37760561 |
| chr17 | 37761997 | 37762334 | chr17 | 37868190 | 37868294 | chr17 | 37879568 | 37879615 |
| chr17 | 37880205 | 37880276 | chr17 | 37880971 | 37881018 | chr17 | 37881318 | 37881631 |
| chr17 | 38179397 | 38179430 | chr17 | 38335459 | 38335533 | chr17 | 38347560 | 38347615 |
| chr17 | 38380553 | 38380598 | chr17 | 38474363 | 38474502 | chr17 | 38497616 | 38497645 |
| chr17 | 38498083 | 38498112 | chr17 | 38504087 | 38504116 | chr17 | 38510555 | 38510584 |
| chr17 | 38574991 | 38575021 | chr17 | 39682352 | 39682711 | chr17 | 39834201 | 39834287 |
| chr17 | 40332943 | 40333226 | chr17 | 40400867 | 40401031 | chr17 | 40464278 | 40464317 |
| chr17 | 40464517 | 40464607 | chr17 | 40474467 | 40474496 | chr17 | 40826197 | 40826226 |
| chr17 | 40837022 | 40837051 | chr17 | 40837287 | 40837383 | chr17 | 40838982 | 40839022 |
| chr17 | 40897739 | 40897788 | chr17 | 40975413 | 40975677 | chr17 | 41175146 | 41175331 |
| chr17 | 41177394 | 41177459 | chr17 | 41197714 | 41197743 | chr17 | 41201163 | 41201192 |
| chr17 | 41203073 | 41203102 | chr17 | 41209064 | 41209114 | chr17 | 41215890 | 41215961 |
| chr17 | 41267731 | 41267775 | chr17 | 41276031 | 41276075 | chr17 | 41277259 | 41277721 |
| chr17 | 41278621 | 41278700 | chr17 | 41651850 | 41651880 | chr17 | 41745825 | 41745855 |
| chr17 | 41791460 | 41791489 | chr17 | 41791665 | 41791694 | chr17 | 42030329 | 42030750 |
| chr17 | 42061336 | 42061381 | chr17 | 42082522 | 42082557 | chr17 | 42084361 | 42084626 |

TABLE 12-continued

Pan Cancer #2

| chr | start | end | chr | start | end | chr | start | end |
|---|---|---|---|---|---|---|---|---|
| chr17 | 42092190 | 42092220 | chr17 | 42110423 | 42110561 | chr17 | 42142661 | 42142808 |
| chr17 | 42246452 | 42246521 | chr17 | 42321590 | 42321674 | chr17 | 42331412 | 42331659 |
| chr17 | 42393842 | 42394024 | chr17 | 42402884 | 42402917 | chr17 | 42580695 | 42580793 |
| chr17 | 42587249 | 42587355 | chr17 | 42590091 | 42590224 | chr17 | 42635295 | 42635760 |
| chr17 | 42733711 | 42733884 | chr17 | 42767947 | 42768198 | chr17 | 42787481 | 42787616 |
| chr17 | 42907564 | 42907630 | chr17 | 42907655 | 42907951 | chr17 | 42975726 | 42975756 |
| chr17 | 43001891 | 43001946 | chr17 | 43044658 | 43044688 | chr17 | 43045039 | 43045116 |
| chr17 | 43046260 | 43046385 | chr17 | 43339109 | 43339333 | chr17 | 43339609 | 43339899 |
| chr17 | 43974256 | 43974358 | chr17 | 44897416 | 44897445 | chr17 | 45022106 | 45022140 |
| chr17 | 45187608 | 45187638 | chr17 | 45331014 | 45331313 | chr17 | 45810850 | 45811341 |
| chr17 | 45867315 | 45867460 | chr17 | 46125007 | 46125061 | chr17 | 46567400 | 46567655 |
| chr17 | 46619540 | 46619569 | chr17 | 46620494 | 46621094 | chr17 | 46621353 | 46621458 |
| chr17 | 46621856 | 46621909 | chr17 | 46655148 | 46655178 | chr17 | 46655451 | 46655998 |
| chr17 | 46656058 | 46656704 | chr17 | 46659429 | 46659859 | chr17 | 46663743 | 46663824 |
| chr17 | 46663856 | 46663887 | chr17 | 46674873 | 46674970 | chr17 | 46675170 | 46675600 |
| chr17 | 46690467 | 46690664 | chr17 | 46691505 | 46691592 | chr17 | 46691805 | 46691818 |
| chr17 | 46691988 | 46692110 | chr17 | 46692439 | 46692606 | chr17 | 46710946 | 46710989 |
| chr17 | 46713959 | 46714072 | chr17 | 46795641 | 46796373 | chr17 | 46796499 | 46796637 |
| chr17 | 46796850 | 46797213 | chr17 | 46797275 | 46797582 | chr17 | 46799625 | 46799896 |
| chr17 | 46800601 | 46800668 | chr17 | 46800961 | 46801047 | chr17 | 46801109 | 46801416 |
| chr17 | 46802459 | 46802911 | chr17 | 46802994 | 46803286 | chr17 | 46804107 | 46804428 |
| chr17 | 46810416 | 46810958 | chr17 | 46811354 | 46811499 | chr17 | 46816282 | 46816877 |
| chr17 | 46824224 | 46824275 | chr17 | 46824359 | 46825054 | chr17 | 46825284 | 46825514 |
| chr17 | 46826930 | 46827127 | chr17 | 46827330 | 46827501 | chr17 | 46827626 | 46827756 |
| chr17 | 46829498 | 46829579 | chr17 | 46829979 | 46830110 | chr17 | 46831779 | 46832325 |
| chr17 | 46832490 | 46832639 | chr17 | 47072805 | 47073028 | chr17 | 47073104 | 47073327 |
| chr17 | 47073389 | 47073465 | chr17 | 47073988 | 47074228 | chr17 | 47074561 | 47074895 |
| chr17 | 47075160 | 47075364 | chr17 | 47075715 | 47075734 | chr17 | 47075880 | 47076055 |
| chr17 | 47574090 | 47574149 | chr17 | 47657514 | 47657583 | chr17 | 47865514 | 47865555 |
| chr17 | 47987525 | 47987619 | chr17 | 47987930 | 47988114 | chr17 | 48041152 | 48041320 |
| chr17 | 48041672 | 48041721 | chr17 | 48042039 | 48042069 | chr17 | 48042435 | 48042647 |
| chr17 | 48042751 | 48042956 | chr17 | 48048952 | 48049059 | chr17 | 48049307 | 48050526 |
| chr17 | 48071020 | 48071050 | chr17 | 48071807 | 48071894 | chr17 | 48473056 | 48473236 |
| chr17 | 48545804 | 48545950 | chr17 | 48589801 | 48589831 | chr17 | 48612223 | 48612308 |
| chr17 | 48636581 | 48637136 | chr17 | 48653128 | 48653158 | chr17 | 48799820 | 48799866 |
| chr17 | 49027838 | 49027876 | chr17 | 49229267 | 49229703 | chr17 | 50235216 | 50235258 |
| chr17 | 50235631 | 50235952 | chr17 | 51901004 | 51901034 | chr17 | 53341252 | 53341536 |
| chr17 | 53342876 | 53343089 | chr17 | 53479184 | 53479316 | chr17 | 53814544 | 53814678 |
| chr17 | 53922649 | 53922790 | chr17 | 54674986 | 54675272 | chr17 | 54755969 | 54755990 |
| chr17 | 55037326 | 55037626 | chr17 | 55122813 | 55122842 | chr17 | 55213641 | 55213670 |
| chr17 | 55962573 | 55962841 | chr17 | 56092600 | 56092736 | chr17 | 56234405 | 56234743 |
| chr17 | 56326949 | 56326994 | chr17 | 56327271 | 56327301 | chr17 | 56471121 | 56471167 |
| chr17 | 56743206 | 56743249 | chr17 | 56833127 | 56833221 | chr17 | 56833707 | 56834000 |
| chr17 | 56834020 | 56834075 | chr17 | 56834306 | 56834375 | chr17 | 57296865 | 57297129 |
| chr17 | 57386255 | 57386735 | chr17 | 57787402 | 57787465 | chr17 | 57832475 | 57832607 |
| chr17 | 58216613 | 58216836 | chr17 | 58216866 | 58217298 | chr17 | 58217357 | 58217551 |
| chr17 | 58218765 | 58218993 | chr17 | 58227374 | 58227397 | chr17 | 58498697 | 58499314 |
| chr17 | 59474157 | 59474246 | chr17 | 59474833 | 59475100 | chr17 | 59475678 | 59476127 |
| chr17 | 59476410 | 59476635 | chr17 | 59478147 | 59478602 | chr17 | 59481657 | 59481678 |
| chr17 | 59488101 | 59488423 | chr17 | 59528876 | 59529150 | chr17 | 59529254 | 59529264 |
| chr17 | 59529844 | 59530352 | chr17 | 59531667 | 59532017 | chr17 | 59533875 | 59534405 |
| chr17 | 59534751 | 59534781 | chr17 | 59535137 | 59535219 | chr17 | 59539236 | 59539601 |
| chr17 | 59924556 | 59924585 | chr17 | 59937192 | 59937236 | chr17 | 61677374 | 61677404 |
| chr17 | 61778235 | 61778248 | chr17 | 61817576 | 61817955 | chr17 | 61926172 | 61926324 |
| chr17 | 61926508 | 61926603 | chr17 | 62028596 | 62028790 | chr17 | 62777335 | 62777450 |
| chr17 | 62777746 | 62777791 | chr17 | 64672366 | 64672544 | chr17 | 65715296 | 65715493 |
| chr17 | 66420718 | 66420837 | chr17 | 66596471 | 66596525 | chr17 | 66596984 | 66597021 |
| chr17 | 67410305 | 67410397 | chr17 | 68164733 | 68164928 | chr17 | 70026543 | 70026667 |
| chr17 | 70112916 | 70113566 | chr17 | 70113648 | 70114018 | chr17 | 70114153 | 70114517 |
| chr17 | 70215683 | 70216306 | chr17 | 70216393 | 70216585 | chr17 | 70586165 | 70586272 |
| chr17 | 71229815 | 71229918 | chr17 | 71641544 | 71641683 | chr17 | 71948439 | 71948863 |
| chr17 | 72236510 | 72236548 | chr17 | 72270286 | 72270415 | chr17 | 72321933 | 72321975 |
| chr17 | 72322363 | 72322557 | chr17 | 72353259 | 72353417 | chr17 | 72353450 | 72353550 |
| chr17 | 72427853 | 72427999 | chr17 | 72428344 | 72428381 | chr17 | 72491378 | 72491531 |
| chr17 | 72667337 | 72667481 | chr17 | 72849010 | 72849079 | chr17 | 72857038 | 72857368 |
| chr17 | 72862371 | 72862460 | chr17 | 72920796 | 72921032 | chr17 | 73031637 | 73031935 |
| chr17 | 73115588 | 73115658 | chr17 | 73115884 | 73115914 | chr17 | 73128301 | 73128338 |
| chr17 | 73147177 | 73147356 | chr17 | 73147774 | 73147992 | chr17 | 73215289 | 73215423 |
| chr17 | 73351981 | 73352086 | chr17 | 73545998 | 73546299 | chr17 | 73586015 | 73586418 |
| chr17 | 73608306 | 73608336 | chr17 | 73636144 | 73636337 | chr17 | 73692986 | 73693122 |
| chr17 | 73709838 | 73709955 | chr17 | 73782870 | 73782947 | chr17 | 73808631 | 73808671 |
| chr17 | 73827213 | 73827243 | chr17 | 73901630 | 73901893 | chr17 | 73904093 | 73904127 |
| chr17 | 74028346 | 74028413 | chr17 | 74047797 | 74048063 | chr17 | 74070281 | 74070479 |
| chr17 | 74071445 | 74071481 | chr17 | 74071689 | 74071729 | chr17 | 74072999 | 74073036 |
| chr17 | 74073269 | 74073433 | chr17 | 74087118 | 74087185 | chr17 | 74299798 | 74299899 |
| chr17 | 74390363 | 74390393 | chr17 | 74533844 | 74534310 | chr17 | 74581182 | 74581221 |

TABLE 12-continued

Pan Cancer #2

| chr | start | end | chr | start | end | chr | start | end |
|---|---|---|---|---|---|---|---|---|
| chr17 | 74663258 | 74663288 | chr17 | 74732944 | 74732973 | chr17 | 74865053 | 74865192 |
| chr17 | 74865698 | 74866243 | chr17 | 75137660 | 75137887 | chr17 | 75207514 | 75207630 |
| chr17 | 75207839 | 75207987 | chr17 | 75276054 | 75276083 | chr17 | 75276413 | 75276442 |
| chr17 | 75277348 | 75277659 | chr17 | 75278020 | 75278049 | chr17 | 75279105 | 75279134 |
| chr17 | 75282025 | 75282154 | chr17 | 75315512 | 75315681 | chr17 | 75316368 | 75316397 |
| chr17 | 75317170 | 75317199 | chr17 | 75347755 | 75347784 | chr17 | 75368735 | 75369238 |
| chr17 | 75369440 | 75369457 | chr17 | 75369493 | 75369860 | chr17 | 75370269 | 75370316 |
| chr17 | 75370596 | 75370625 | chr17 | 75373312 | 75373341 | chr17 | 75385071 | 75385446 |
| chr17 | 75405827 | 75405856 | chr17 | 75417150 | 75417179 | chr17 | 75523142 | 75523272 |
| chr17 | 75524636 | 75525194 | chr17 | 75733978 | 75734244 | chr17 | 75797111 | 75797179 |
| chr17 | 76021047 | 76021077 | chr17 | 76125196 | 76125225 | chr17 | 76126434 | 76126463 |
| chr17 | 76128466 | 76128663 | chr17 | 76130124 | 76130153 | chr17 | 76130481 | 76130510 |
| chr17 | 76135783 | 76136001 | chr17 | 76137951 | 76138190 | chr17 | 76138498 | 76138622 |
| chr17 | 76187407 | 76187544 | chr17 | 76207342 | 76207372 | chr17 | 76211302 | 76211506 |
| chr17 | 76227849 | 76228161 | chr17 | 76228214 | 76228357 | chr17 | 76404615 | 76404659 |
| chr17 | 76877177 | 76877212 | chr17 | 76884417 | 76884447 | chr17 | 76974447 | 76974499 |
| chr17 | 76983518 | 76983669 | chr17 | 76984053 | 76984188 | chr17 | 77070307 | 77070457 |
| chr17 | 77084518 | 77084727 | chr17 | 77105055 | 77105198 | chr17 | 77145129 | 77145242 |
| chr17 | 77179113 | 77179278 | chr17 | 77179630 | 77179776 | chr17 | 77394706 | 77394850 |
| chr17 | 77776827 | 77776995 | chr17 | 77777053 | 77777056 | chr17 | 77777585 | 77777903 |
| chr17 | 77777944 | 77777961 | chr17 | 77778943 | 77779179 | chr17 | 77789474 | 77789500 |
| chr17 | 77825696 | 77825812 | chr17 | 77827114 | 77827201 | chr17 | 77899664 | 77899693 |
| chr17 | 77919429 | 77919477 | chr17 | 77924259 | 77924351 | chr17 | 78122158 | 78122190 |
| chr17 | 78194821 | 78194861 | chr17 | 78272278 | 78272313 | chr17 | 78447127 | 78447157 |
| chr17 | 78451931 | 78451953 | chr17 | 78452296 | 78452340 | chr17 | 78452681 | 78452833 |
| chr17 | 78518031 | 78518198 | chr17 | 78599596 | 78599628 | chr17 | 78667992 | 78668159 |
| chr17 | 78874441 | 78874559 | chr17 | 78975667 | 78975758 | chr17 | 78999625 | 78999654 |
| chr17 | 79058302 | 79058333 | chr17 | 79094182 | 79094245 | chr17 | 79099770 | 79099799 |
| chr17 | 79626591 | 79626703 | chr17 | 79626985 | 79626985 | chr17 | 79769433 | 79769693 |
| chr17 | 79813409 | 79813507 | chr17 | 79850445 | 79850537 | chr17 | 79896013 | 79896043 |
| chr17 | 79939605 | 79939835 | chr17 | 79945037 | 79945074 | chr17 | 80186260 | 80186289 |
| chr17 | 80197756 | 80197898 | chr17 | 80254266 | 80254296 | chr17 | 80289234 | 80289310 |
| chr17 | 80289858 | 80289892 | chr17 | 80294282 | 80294427 | chr17 | 80329709 | 80330000 |
| chr17 | 80394063 | 80394185 | chr17 | 80394573 | 80394602 | chr17 | 80479311 | 80479559 |
| chr17 | 80491572 | 80491602 | chr17 | 80535382 | 80535487 | chr17 | 80571380 | 80571776 |
| chr17 | 80593754 | 80594107 | chr17 | 80654983 | 80655013 | chr17 | 80693317 | 80693554 |
| chr17 | 80749152 | 80749276 | chr17 | 80751650 | 80751714 | chr17 | 80794259 | 80794288 |
| chr17 | 80797692 | 80798345 | chr17 | 80832305 | 80832411 | chr17 | 80832712 | 80832796 |
| chr17 | 80859239 | 80859269 | chr17 | 81008618 | 81008826 | chr17 | 81033487 | 81033517 |
| chr17 | 81048993 | 81049023 | chr17 | 81049994 | 81050058 | chr18 | 147543 | 147613 |
| chr18 | 499367 | 499482 | chr18 | 500046 | 500738 | chr18 | 597548 | 597578 |
| chr18 | 697854 | 697901 | chr18 | 904462 | 904648 | chr18 | 905000 | 905030 |
| chr18 | 905434 | 905615 | chr18 | 906871 | 906907 | chr18 | 907472 | 907594 |
| chr18 | 907912 | 907977 | chr18 | 908454 | 908589 | chr18 | 909487 | 909587 |
| chr18 | 2755770 | 2755878 | chr18 | 2906268 | 2906304 | chr18 | 3214441 | 3214825 |
| chr18 | 3215042 | 3215256 | chr18 | 3499067 | 3499371 | chr18 | 4453964 | 4454163 |
| chr18 | 5133207 | 5133343 | chr18 | 5196576 | 5196959 | chr18 | 5197202 | 5197271 |
| chr18 | 5197330 | 5197347 | chr18 | 5237878 | 5238247 | chr18 | 5628167 | 5628515 |
| chr18 | 5629774 | 5629825 | chr18 | 5630312 | 5630362 | chr18 | 5895023 | 5895205 |
| chr18 | 5895975 | 5896085 | chr18 | 6729952 | 6729993 | chr18 | 6908056 | 6908243 |
| chr18 | 7117665 | 7117804 | chr18 | 7567783 | 7568291 | chr18 | 8608748 | 8608837 |
| chr18 | 8608902 | 8608968 | chr18 | 8612252 | 8612282 | chr18 | 9771586 | 9771753 |
| chr18 | 9868137 | 9868174 | chr18 | 9912767 | 9912797 | chr18 | 10251324 | 10251432 |
| chr18 | 10589096 | 10589348 | chr18 | 10733492 | 10733605 | chr18 | 11148969 | 11149045 |
| chr18 | 11149561 | 11149759 | chr18 | 11149780 | 11149888 | chr18 | 11401654 | 11401817 |
| chr18 | 11689190 | 11689220 | chr18 | 11752128 | 11752379 | chr18 | 11752700 | 11752730 |
| chr18 | 11942728 | 11942838 | chr18 | 11979677 | 11979860 | chr18 | 12254305 | 12254578 |
| chr18 | 12277243 | 12277273 | chr18 | 12307247 | 12307505 | chr18 | 12307603 | 12307751 |
| chr18 | 12375483 | 12375597 | chr18 | 12375923 | 12376129 | chr18 | 12890152 | 12890278 |
| chr18 | 12948993 | 12949023 | chr18 | 13132080 | 13132246 | chr18 | 13824025 | 13824102 |
| chr18 | 13826393 | 13826536 | chr18 | 13868713 | 13868919 | chr18 | 15198110 | 15198248 |
| chr18 | 18822392 | 18823274 | chr18 | 19191525 | 19191585 | chr18 | 19750308 | 19750346 |
| chr18 | 20911541 | 20911571 | chr18 | 21035222 | 21035252 | chr18 | 21269349 | 21269390 |
| chr18 | 21269659 | 21269740 | chr18 | 21719351 | 21719568 | chr18 | 21719938 | 21720064 |
| chr18 | 22929081 | 22929095 | chr18 | 22929187 | 22929718 | chr18 | 22929927 | 22930559 |
| chr18 | 22930790 | 22931178 | chr18 | 23686462 | 23686618 | chr18 | 24127748 | 24128030 |
| chr18 | 24130809 | 24130946 | chr18 | 24131099 | 24131187 | chr18 | 24764951 | 24765168 |
| chr18 | 25755593 | 25755655 | chr18 | 25756010 | 25756040 | chr18 | 25756495 | 25756729 |
| chr18 | 25757187 | 25757452 | chr18 | 25757787 | 25757824 | chr18 | 25758129 | 25758141 |
| chr18 | 28620899 | 28620955 | chr18 | 28621034 | 28621097 | chr18 | 28621328 | 28621393 |
| chr18 | 28621636 | 28621932 | chr18 | 28622419 | 28622488 | chr18 | 29413805 | 29413839 |
| chr18 | 29719775 | 29720012 | chr18 | 30349740 | 30349781 | chr18 | 31020495 | 31020510 |
| chr18 | 31158093 | 31158158 | chr18 | 31739035 | 31739469 | chr18 | 31802132 | 31802167 |
| chr18 | 31802938 | 31802968 | chr18 | 31803438 | 31803472 | chr18 | 31902793 | 31902945 |
| chr18 | 32073908 | 32074086 | chr18 | 32557832 | 32557864 | chr18 | 32847598 | 32847642 |
| chr18 | 32957803 | 32957839 | chr18 | 33078363 | 33078662 | chr18 | 33877683 | 33877754 |

TABLE 12-continued

Pan Cancer #2

| chr | start | end | chr | start | end | chr | start | end |
|---|---|---|---|---|---|---|---|---|
| chr18 | 35065072 | 35065145 | chr18 | 35144845 | 35144936 | chr18 | 35144969 | 35145465 |
| chr18 | 35145968 | 35146036 | chr18 | 35146062 | 35146241 | chr18 | 35147487 | 35147569 |
| chr18 | 43546048 | 43546134 | chr18 | 43914211 | 43914278 | chr18 | 44259903 | 44259990 |
| chr18 | 44336034 | 44336449 | chr18 | 44337174 | 44337617 | chr18 | 44337650 | 44337841 |
| chr18 | 44773060 | 44773116 | chr18 | 44773592 | 44773966 | chr18 | 44774406 | 44774890 |
| chr18 | 44775380 | 44775554 | chr18 | 44776972 | 44777088 | chr18 | 44777301 | 44777331 |
| chr18 | 44777596 | 44777750 | chr18 | 44778049 | 44778326 | chr18 | 44781003 | 44781041 |
| chr18 | 44787781 | 44787846 | chr18 | 44788251 | 44788281 | chr18 | 44789474 | 44789514 |
| chr18 | 44789872 | 44789937 | chr18 | 45058069 | 45058240 | chr18 | 46142662 | 46142809 |
| chr18 | 47720492 | 47720522 | chr18 | 48604773 | 48604802 | chr18 | 48636211 | 48636320 |
| chr18 | 49867303 | 49867399 | chr18 | 49868634 | 49868664 | chr18 | 51771058 | 51771128 |
| chr18 | 52989009 | 52989220 | chr18 | 52989741 | 52989882 | chr18 | 53257137 | 53257204 |
| chr18 | 53446970 | 53447474 | chr18 | 53447799 | 53447816 | chr18 | 53989796 | 53989877 |
| chr18 | 54789070 | 54789256 | chr18 | 55019707 | 55019775 | chr18 | 55020655 | 55020698 |
| chr18 | 55021078 | 55021242 | chr18 | 55103381 | 55103411 | chr18 | 55104808 | 55105140 |
| chr18 | 55105728 | 55105830 | chr18 | 55114480 | 55114644 | chr18 | 55426948 | 55426978 |
| chr18 | 55850845 | 55850987 | chr18 | 56483918 | 56483958 | chr18 | 56815734 | 56816107 |
| chr18 | 56887076 | 56887424 | chr18 | 56888554 | 56888623 | chr18 | 56931541 | 56931583 |
| chr18 | 56931967 | 56932107 | chr18 | 56932352 | 56932637 | chr18 | 56935010 | 56935319 |
| chr18 | 56936004 | 56936074 | chr18 | 56939113 | 56939174 | chr18 | 56939423 | 56939651 |
| chr18 | 56939764 | 56940170 | chr18 | 56940566 | 56940722 | chr18 | 56940955 | 56941244 |
| chr18 | 56941558 | 56941788 | chr18 | 57363706 | 57363743 | chr18 | 57364658 | 57364691 |
| chr18 | 59000988 | 59001022 | chr18 | 59001301 | 59001343 | chr18 | 59001498 | 59001740 |
| chr18 | 60263661 | 60263895 | chr18 | 60557729 | 60557759 | chr18 | 60985498 | 60985532 |
| chr18 | 60985593 | 60985732 | chr18 | 61143911 | 61143975 | chr18 | 67067558 | 67067907 |
| chr18 | 67068715 | 67068811 | chr18 | 67069216 | 67069246 | chr18 | 70209148 | 70209205 |
| chr18 | 70210418 | 70210508 | chr18 | 70211626 | 70211666 | chr18 | 70534282 | 70534315 |
| chr18 | 70534428 | 70534731 | chr18 | 70535373 | 70535554 | chr18 | 70535576 | 70535582 |
| chr18 | 70536010 | 70536083 | chr18 | 70536604 | 70536604 | chr18 | 70536833 | 70536871 |
| chr18 | 70537188 | 70537218 | chr18 | 72845833 | 72845863 | chr18 | 73167585 | 73167832 |
| chr18 | 73628019 | 73628068 | chr18 | 74501144 | 74501183 | chr18 | 74755508 | 74755590 |
| chr18 | 74961326 | 74961955 | chr18 | 74962019 | 74962147 | chr18 | 74962970 | 74963545 |
| chr18 | 75335093 | 75335123 | chr18 | 75339231 | 75339340 | chr18 | 75362931 | 75362985 |
| chr18 | 75551271 | 75551301 | chr18 | 75612225 | 75612286 | chr18 | 75999404 | 75999434 |
| chr18 | 76239541 | 76239616 | chr18 | 76501479 | 76501509 | chr18 | 76653631 | 76653661 |
| chr18 | 76686249 | 76686279 | chr18 | 76689735 | 76689765 | chr18 | 76740102 | 76740223 |
| chr18 | 77050480 | 77050678 | chr18 | 77143346 | 77143376 | chr18 | 77167824 | 77167854 |
| chr18 | 77181355 | 77181409 | chr18 | 77194936 | 77194978 | chr18 | 77205532 | 77205638 |
| chr18 | 77285897 | 77286028 | chr18 | 77300326 | 77300483 | chr18 | 77309533 | 77309563 |
| chr18 | 77312866 | 77312927 | chr18 | 77329727 | 77330017 | chr18 | 77371430 | 77371547 |
| chr18 | 77459762 | 77459877 | chr18 | 77512225 | 77512255 | chr18 | 77543249 | 77543481 |
| chr18 | 77543700 | 77543824 | chr18 | 77548352 | 77548609 | chr18 | 77550206 | 77550367 |
| chr18 | 77558082 | 77558358 | chr18 | 77558831 | 77558930 | chr18 | 77576934 | 77577043 |
| chr18 | 77636591 | 77636621 | chr18 | 77698881 | 77698919 | chr18 | 78004993 | 78005051 |
| chr19 | 403538 | 403809 | chr19 | 407189 | 407320 | chr19 | 418225 | 418255 |
| chr19 | 462181 | 462269 | chr19 | 468757 | 468787 | chr19 | 485165 | 485394 |
| chr19 | 549361 | 549451 | chr19 | 555608 | 555768 | chr19 | 570156 | 570194 |
| chr19 | 591365 | 591416 | chr19 | 592589 | 592632 | chr19 | 593290 | 593462 |
| chr19 | 599214 | 599333 | chr19 | 607070 | 607110 | chr19 | 690888 | 690940 |
| chr19 | 752136 | 752462 | chr19 | 869337 | 869394 | chr19 | 883624 | 883791 |
| chr19 | 884018 | 884162 | chr19 | 891516 | 891723 | chr19 | 955757 | 956237 |
| chr19 | 959128 | 959187 | chr19 | 1003305 | 1003384 | chr19 | 1003669 | 1003734 |
| chr19 | 1004915 | 1005441 | chr19 | 1030176 | 1030225 | chr19 | 1047890 | 1047939 |
| chr19 | 1048348 | 1048465 | chr19 | 1083314 | 1083437 | chr19 | 1156524 | 1156554 |
| chr19 | 1170185 | 1170230 | chr19 | 1171099 | 1171324 | chr19 | 1220422 | 1220610 |
| chr19 | 1221981 | 1222010 | chr19 | 1236474 | 1236678 | chr19 | 1274778 | 1274826 |
| chr19 | 1308047 | 1308081 | chr19 | 1325788 | 1325889 | chr19 | 1330064 | 1330214 |
| chr19 | 1401752 | 1401795 | chr19 | 1450319 | 1450390 | chr19 | 1496413 | 1496450 |
| chr19 | 1496654 | 1496694 | chr19 | 1524443 | 1524447 | chr19 | 1525605 | 1525960 |
| chr19 | 1527227 | 1527394 | chr19 | 1547233 | 1547263 | chr19 | 1689436 | 1689595 |
| chr19 | 1754172 | 1754193 | chr19 | 1754225 | 1754254 | chr19 | 1754739 | 1754804 |
| chr19 | 1757416 | 1757615 | chr19 | 1762474 | 1762505 | chr19 | 1764293 | 1764339 |
| chr19 | 1775076 | 1775239 | chr19 | 1776376 | 1776534 | chr19 | 1799466 | 1799516 |
| chr19 | 1800032 | 1800300 | chr19 | 1807970 | 1808413 | chr19 | 2135672 | 2135701 |
| chr19 | 2155031 | 2155061 | chr19 | 2251152 | 2251234 | chr19 | 2251611 | 2251715 |
| chr19 | 2252589 | 2252658 | chr19 | 2252984 | 2253735 | chr19 | 2274677 | 2274713 |
| chr19 | 2290253 | 2290271 | chr19 | 2290631 | 2290867 | chr19 | 2302793 | 2302951 |
| chr19 | 2330317 | 2330407 | chr19 | 2331413 | 2331443 | chr19 | 2413125 | 2413155 |
| chr19 | 2414257 | 2414337 | chr19 | 2513250 | 2513285 | chr19 | 2642877 | 2642947 |
| chr19 | 2683911 | 2684080 | chr19 | 3041417 | 3041447 | chr19 | 3093571 | 3093818 |
| chr19 | 3114998 | 3115027 | chr19 | 3118927 | 3118956 | chr19 | 3219512 | 3219565 |
| chr19 | 3296613 | 3296670 | chr19 | 3361139 | 3361388 | chr19 | 3562128 | 3562797 |
| chr19 | 3570230 | 3570371 | chr19 | 3578138 | 3578223 | chr19 | 3659668 | 3659793 |
| chr19 | 3716179 | 3716241 | chr19 | 3718052 | 3718082 | chr19 | 3778130 | 3778394 |
| chr19 | 3779277 | 3779435 | chr19 | 3785649 | 3785835 | chr19 | 3785865 | 3786220 |
| chr19 | 3821044 | 3821217 | chr19 | 3822135 | 3822203 | chr19 | 3834572 | 3834641 |

TABLE 12-continued

Pan Cancer #2

| chr | start | end | chr | start | end | chr | start | end |
|---|---|---|---|---|---|---|---|---|
| chr19 | 3855407 | 3855595 | chr19 | 3966686 | 3966755 | chr19 | 3994540 | 3994595 |
| chr19 | 4054435 | 4054471 | chr19 | 4095471 | 4095514 | chr19 | 4101087 | 4101116 |
| chr19 | 4110565 | 4110597 | chr19 | 4117526 | 4117630 | chr19 | 4160800 | 4160898 |
| chr19 | 4195767 | 4195853 | chr19 | 4305057 | 4305086 | chr19 | 4311273 | 4311430 |
| chr19 | 4509338 | 4509440 | chr19 | 4548134 | 4548364 | chr19 | 4549454 | 4549565 |
| chr19 | 4550246 | 4550330 | chr19 | 4555896 | 4556112 | chr19 | 4557098 | 4557235 |
| chr19 | 4572332 | 4572459 | chr19 | 4670765 | 4670949 | chr19 | 4789697 | 4789805 |
| chr19 | 4790142 | 4790264 | chr19 | 4835778 | 4835926 | chr19 | 4910361 | 4910410 |
| chr19 | 4944145 | 4944174 | chr19 | 5292812 | 5292844 | chr19 | 5338914 | 5339143 |
| chr19 | 5608519 | 5608569 | chr19 | 5676212 | 5676242 | chr19 | 5759374 | 5759544 |
| chr19 | 5759744 | 5759774 | chr19 | 5767703 | 5767733 | chr19 | 5826179 | 5826209 |
| chr19 | 5905517 | 5905547 | chr19 | 5910356 | 5910492 | chr19 | 5914761 | 5914791 |
| chr19 | 5914992 | 5915060 | chr19 | 6303268 | 6303298 | chr19 | 6512913 | 6512943 |
| chr19 | 6590325 | 6590478 | chr19 | 6658279 | 6658422 | chr19 | 6889423 | 6889574 |
| chr19 | 7157547 | 7157628 | chr19 | 7554718 | 7554780 | chr19 | 7615996 | 7616025 |
| chr19 | 7635387 | 7635552 | chr19 | 7746942 | 7747042 | chr19 | 7747205 | 7747234 |
| chr19 | 7795012 | 7795244 | chr19 | 7853028 | 7853157 | chr19 | 7853361 | 7853460 |
| chr19 | 7870346 | 7870387 | chr19 | 8115235 | 8115276 | chr19 | 8391621 | 8391651 |
| chr19 | 8554173 | 8554218 | chr19 | 8576914 | 8577000 | chr19 | 8579592 | 8579705 |
| chr19 | 9239580 | 9239695 | chr19 | 9331918 | 9331955 | chr19 | 9420142 | 9420240 |
| chr19 | 9473564 | 9473597 | chr19 | 9473869 | 9474056 | chr19 | 9517609 | 9517771 |
| chr19 | 9608895 | 9609036 | chr19 | 9609319 | 9609436 | chr19 | 9903913 | 9904100 |
| chr19 | 9937291 | 9937386 | chr19 | 10231077 | 10231242 | chr19 | 10246506 | 10246566 |
| chr19 | 10362045 | 10362182 | chr19 | 10398209 | 10398285 | chr19 | 10405972 | 10406159 |
| chr19 | 10406279 | 10406349 | chr19 | 10406806 | 10407029 | chr19 | 10407045 | 10407135 |
| chr19 | 10527165 | 10527243 | chr19 | 10531419 | 10531512 | chr19 | 10531964 | 10531994 |
| chr19 | 10600431 | 10600460 | chr19 | 10602274 | 10602348 | chr19 | 10602565 | 10602864 |
| chr19 | 10610138 | 10610260 | chr19 | 10621768 | 10621829 | chr19 | 10624751 | 10624852 |
| chr19 | 10624966 | 10625465 | chr19 | 10648372 | 10648546 | chr19 | 10729811 | 10729899 |
| chr19 | 10823678 | 10823721 | chr19 | 10827675 | 10827705 | chr19 | 10851287 | 10851362 |
| chr19 | 10955456 | 10955585 | chr19 | 11063941 | 11063971 | chr19 | 11134252 | 11134281 |
| chr19 | 11138507 | 11138536 | chr19 | 11492252 | 11492528 | chr19 | 11591031 | 11591185 |
| chr19 | 11592710 | 11592750 | chr19 | 11593022 | 11593159 | chr19 | 11689460 | 11689564 |
| chr19 | 11959912 | 11960077 | chr19 | 12147437 | 12147545 | chr19 | 12163448 | 12163672 |
| chr19 | 12163893 | 12163923 | chr19 | 12175445 | 12175504 | chr19 | 12175814 | 12176005 |
| chr19 | 12203028 | 12203744 | chr19 | 12205385 | 12205434 | chr19 | 12267019 | 12267667 |
| chr19 | 12303495 | 12303551 | chr19 | 12305839 | 12306193 | chr19 | 12306230 | 12306263 |
| chr19 | 12476492 | 12476556 | chr19 | 12595109 | 12595307 | chr19 | 12595845 | 12595896 |
| chr19 | 12606381 | 12606511 | chr19 | 12661175 | 12661221 | chr19 | 12750987 | 12751056 |
| chr19 | 12846906 | 12847098 | chr19 | 12860307 | 12860433 | chr19 | 12863412 | 12863520 |
| chr19 | 12952000 | 12952139 | chr19 | 12996169 | 12996280 | chr19 | 13113454 | 13113668 |
| chr19 | 13491305 | 13491340 | chr19 | 13616696 | 13616956 | chr19 | 13617159 | 13617256 |
| chr19 | 13618288 | 13618381 | chr19 | 13782965 | 13783028 | chr19 | 13903520 | 13903603 |
| chr19 | 13965838 | 13965965 | chr19 | 13988775 | 13988805 | chr19 | 14085021 | 14085051 |
| chr19 | 14181305 | 14181846 | chr19 | 14324876 | 14324906 | chr19 | 14327101 | 14327158 |
| chr19 | 14334020 | 14334060 | chr19 | 14411056 | 14411086 | chr19 | 14584240 | 14584412 |
| chr19 | 14584537 | 14584775 | chr19 | 14663925 | 14664183 | chr19 | 14664479 | 14664561 |
| chr19 | 14869496 | 14869526 | chr19 | 15090172 | 15090499 | chr19 | 15121685 | 15121894 |
| chr19 | 15122120 | 15122238 | chr19 | 15288433 | 15288856 | chr19 | 15292384 | 15292499 |
| chr19 | 15342734 | 15343373 | chr19 | 15344107 | 15344130 | chr19 | 15519444 | 15519474 |
| chr19 | 16766902 | 16766932 | chr19 | 16999599 | 16999782 | chr19 | 17000570 | 17000599 |
| chr19 | 17007086 | 17007388 | chr19 | 17007447 | 17007662 | chr19 | 17008586 | 17008698 |
| chr19 | 17152333 | 17152363 | chr19 | 17335642 | 17335718 | chr19 | 17336042 | 17336111 |
| chr19 | 17359350 | 17359459 | chr19 | 17392641 | 17392866 | chr19 | 17436061 | 17436203 |
| chr19 | 17446897 | 17447045 | chr19 | 17717286 | 17717315 | chr19 | 17759224 | 17759423 |
| chr19 | 17791182 | 17791211 | chr19 | 17943423 | 17943452 | chr19 | 17945891 | 17945983 |
| chr19 | 17947991 | 17948023 | chr19 | 17949094 | 17949123 | chr19 | 17958490 | 17958839 |
| chr19 | 17983537 | 17983665 | chr19 | 18041069 | 18041203 | chr19 | 18057603 | 18057655 |
| chr19 | 18103711 | 18103741 | chr19 | 18104472 | 18104606 | chr19 | 18126412 | 18126442 |
| chr19 | 18271894 | 18271923 | chr19 | 18278047 | 18278076 | chr19 | 18300127 | 18300422 |
| chr19 | 18301007 | 18301037 | chr19 | 18331031 | 18331136 | chr19 | 18343439 | 18343569 |
| chr19 | 18343921 | 18343963 | chr19 | 18383211 | 18383351 | chr19 | 18488862 | 18488915 |
| chr19 | 18496000 | 18496030 | chr19 | 18523115 | 18523145 | chr19 | 18633926 | 18633980 |
| chr19 | 18681638 | 18681926 | chr19 | 18714552 | 18714580 | chr19 | 18811560 | 18811804 |
| chr19 | 18856379 | 18856409 | chr19 | 18872825 | 18872900 | chr19 | 18899432 | 18899652 |
| chr19 | 18901828 | 18902095 | chr19 | 18989821 | 18990281 | chr19 | 18994887 | 18995206 |
| chr19 | 19260030 | 19260101 | chr19 | 19261519 | 19261548 | chr19 | 19334831 | 19334915 |
| chr19 | 19489251 | 19489297 | chr19 | 19636877 | 19636907 | chr19 | 19645834 | 19645925 |
| chr19 | 19651991 | 19652066 | chr19 | 19729251 | 19729395 | chr19 | 19739172 | 19739428 |
| chr19 | 19775308 | 19775472 | chr19 | 20011955 | 20012149 | chr19 | 20188693 | 20188872 |
| chr19 | 20189322 | 20189438 | chr19 | 21237609 | 21237655 | chr19 | 21239053 | 21239129 |
| chr19 | 21245066 | 21245152 | chr19 | 21265890 | 21265920 | chr19 | 21289719 | 21289749 |
| chr19 | 21290153 | 21290216 | chr19 | 21303863 | 21303993 | chr19 | 21305707 | 21305737 |
| chr19 | 21370382 | 21370479 | chr19 | 21512594 | 21512660 | chr19 | 21646407 | 21646437 |
| chr19 | 21665258 | 21665288 | chr19 | 21688814 | 21688912 | chr19 | 21769300 | 21769374 |
| chr19 | 22018523 | 22018805 | chr19 | 22034198 | 22034421 | chr19 | 22034447 | 22034813 |

TABLE 12-continued

Pan Cancer #2

| chr | start | end | chr | start | end | chr | start | end |
|---|---|---|---|---|---|---|---|---|
| chr19 | 22610635 | 22610700 | chr19 | 22715140 | 22715443 | chr19 | 23254189 | 23254219 |
| chr19 | 23257703 | 23258007 | chr19 | 23258306 | 23258694 | chr19 | 23299748 | 23300080 |
| chr19 | 23432562 | 23432723 | chr19 | 23433143 | 23433296 | chr19 | 23456615 | 23456881 |
| chr19 | 23598274 | 23598326 | chr19 | 24154592 | 24154621 | chr19 | 24216975 | 24217023 |
| chr19 | 29284452 | 29284575 | chr19 | 29505153 | 29505183 | chr19 | 30015934 | 30015962 |
| chr19 | 30016025 | 30016712 | chr19 | 30016914 | 30016928 | chr19 | 30017452 | 30017509 |
| chr19 | 30017578 | 30017721 | chr19 | 30017766 | 30018608 | chr19 | 30019145 | 30019610 |
| chr19 | 30019661 | 30019838 | chr19 | 30020093 | 30020473 | chr19 | 30130889 | 30130919 |
| chr19 | 30186141 | 30186278 | chr19 | 30215542 | 30215571 | chr19 | 30215753 | 30215782 |
| chr19 | 30252296 | 30252369 | chr19 | 30555329 | 30555376 | chr19 | 30562775 | 30563017 |
| chr19 | 30582601 | 30582649 | chr19 | 30637494 | 30637531 | chr19 | 30703436 | 30703469 |
| chr19 | 30713480 | 30713592 | chr19 | 30713686 | 30713706 | chr19 | 30713909 | 30714047 |
| chr19 | 30714403 | 30714433 | chr19 | 30715402 | 30715766 | chr19 | 30716313 | 30716576 |
| chr19 | 30716953 | 30718149 | chr19 | 30718847 | 30718913 | chr19 | 30719449 | 30720067 |
| chr19 | 30865713 | 30866024 | chr19 | 31804724 | 31804754 | chr19 | 31839838 | 31839873 |
| chr19 | 31841937 | 31842389 | chr19 | 32364365 | 32364403 | chr19 | 32380872 | 32380961 |
| chr19 | 32516399 | 32516516 | chr19 | 32715673 | 32715741 | chr19 | 32835279 | 32835309 |
| chr19 | 32898335 | 32898490 | chr19 | 33167116 | 33167431 | chr19 | 33468018 | 33468055 |
| chr19 | 33571236 | 33571280 | chr19 | 33685544 | 33685581 | chr19 | 33792159 | 33792524 |
| chr19 | 33794675 | 33794744 | chr19 | 34112524 | 34112729 | chr19 | 34113367 | 34113587 |
| chr19 | 34114006 | 34114049 | chr19 | 34533139 | 34533169 | chr19 | 34896324 | 34896360 |
| chr19 | 34973243 | 34973255 | chr19 | 34973656 | 34973697 | chr19 | 34973932 | 34973965 |
| chr19 | 35264085 | 35264119 | chr19 | 35396251 | 35396370 | chr19 | 35616341 | 35616397 |
| chr19 | 35781374 | 35781459 | chr19 | 35783136 | 35783231 | chr19 | 35797916 | 35797965 |
| chr19 | 36048595 | 36048771 | chr19 | 36049327 | 36049367 | chr19 | 36049397 | 36049462 |
| chr19 | 36194934 | 36194996 | chr19 | 36200805 | 36200847 | chr19 | 36222432 | 36222534 |
| chr19 | 36250029 | 36250134 | chr19 | 36264697 | 36264773 | chr19 | 36265053 | 36265186 |
| chr19 | 36334979 | 36335147 | chr19 | 36347892 | 36348048 | chr19 | 36410956 | 36411042 |
| chr19 | 36413776 | 36413830 | chr19 | 36450106 | 36450295 | chr19 | 36523333 | 36523480 |
| chr19 | 36531924 | 36531954 | chr19 | 36707435 | 36707467 | chr19 | 36736027 | 36736057 |
| chr19 | 36736319 | 36736491 | chr19 | 36822324 | 36822466 | chr19 | 36822558 | 36822892 |
| chr19 | 36909050 | 36909348 | chr19 | 36909624 | 36909935 | chr19 | 37095665 | 37095812 |
| chr19 | 37096488 | 37096575 | chr19 | 37263532 | 37263584 | chr19 | 37264222 | 37264421 |
| chr19 | 37288013 | 37288424 | chr19 | 37288607 | 37288765 | chr19 | 37341761 | 37341962 |
| chr19 | 37407127 | 37407443 | chr19 | 37464048 | 37464567 | chr19 | 37464667 | 37464696 |
| chr19 | 37569289 | 37569554 | chr19 | 37702003 | 37702169 | chr19 | 37808445 | 37808485 |
| chr19 | 37959874 | 37959963 | chr19 | 37997433 | 37998138 | chr19 | 38042365 | 38042693 |
| chr19 | 38085254 | 38086066 | chr19 | 38146062 | 38146247 | chr19 | 38146457 | 38146568 |
| chr19 | 38182884 | 38182959 | chr19 | 38183112 | 38183299 | chr19 | 38308080 | 38308336 |
| chr19 | 38308395 | 38308466 | chr19 | 38441488 | 38441518 | chr19 | 38481044 | 38481217 |
| chr19 | 38733924 | 38733954 | chr19 | 38736072 | 38736127 | chr19 | 38747159 | 38747582 |
| chr19 | 38747729 | 38747767 | chr19 | 38755272 | 38755344 | chr19 | 38757128 | 38757308 |
| chr19 | 38782559 | 38782589 | chr19 | 38789218 | 38789288 | chr19 | 38873935 | 38873965 |
| chr19 | 38905548 | 38905702 | chr19 | 38974232 | 38974262 | chr19 | 39135294 | 39135454 |
| chr19 | 39273027 | 39273062 | chr19 | 39290904 | 39290944 | chr19 | 39306433 | 39306545 |
| chr19 | 39310469 | 39310584 | chr19 | 39650791 | 39650967 | chr19 | 39687756 | 39687844 |
| chr19 | 39754874 | 39755232 | chr19 | 39755265 | 39755358 | chr19 | 39816936 | 39817085 |
| chr19 | 39934694 | 39934784 | chr19 | 39993477 | 39993656 | chr19 | 39997688 | 39997732 |
| chr19 | 39997749 | 39997813 | chr19 | 40006187 | 40006306 | chr19 | 40006576 | 40006639 |
| chr19 | 40210391 | 40210573 | chr19 | 40724000 | 40724263 | chr19 | 40762943 | 40762972 |
| chr19 | 40829079 | 40829211 | chr19 | 40829793 | 40830032 | chr19 | 40902425 | 40902812 |
| chr19 | 40951175 | 40951357 | chr19 | 40951679 | 40951762 | chr19 | 40991013 | 40991139 |
| chr19 | 41018510 | 41019031 | chr19 | 41025539 | 41025683 | chr19 | 41059909 | 41060306 |
| chr19 | 41073587 | 41073677 | chr19 | 41119177 | 41119276 | chr19 | 41119371 | 41119408 |
| chr19 | 41354666 | 41354722 | chr19 | 41473190 | 41473242 | chr19 | 41641831 | 41641886 |
| chr19 | 41694610 | 41694640 | chr19 | 41698787 | 41698920 | chr19 | 41846193 | 41846325 |
| chr19 | 41881534 | 41881811 | chr19 | 41919917 | 41919971 | chr19 | 42028502 | 42028549 |
| chr19 | 42408300 | 42408330 | chr19 | 42460961 | 42461113 | chr19 | 42827982 | 42828084 |
| chr19 | 42856453 | 42856483 | chr19 | 42911568 | 42911598 | chr19 | 44203830 | 44203877 |
| chr19 | 44405908 | 44406087 | chr19 | 44599783 | 44599883 | chr19 | 44905499 | 44905529 |
| chr19 | 44952282 | 44952881 | chr19 | 45003211 | 45003323 | chr19 | 45300144 | 45300197 |
| chr19 | 45541556 | 45541679 | chr19 | 45570401 | 45570450 | chr19 | 45574465 | 45574495 |
| chr19 | 45574773 | 45574888 | chr19 | 45601380 | 45601410 | chr19 | 45655400 | 45655556 |
| chr19 | 45655648 | 45656363 | chr19 | 45656682 | 45656742 | chr19 | 45656791 | 45656913 |
| chr19 | 45657212 | 45657284 | chr19 | 45678395 | 45678555 | chr19 | 45810102 | 45810267 |
| chr19 | 45835028 | 45835268 | chr19 | 45888946 | 45889224 | chr19 | 45889316 | 45889397 |
| chr19 | 45997528 | 45997584 | chr19 | 46002048 | 46002320 | chr19 | 46234803 | 46234887 |
| chr19 | 46379914 | 46380148 | chr19 | 46404522 | 46404601 | chr19 | 46916725 | 46916987 |
| chr19 | 46917061 | 46917075 | chr19 | 46930129 | 46930200 | chr19 | 46974552 | 46974608 |
| chr19 | 46992718 | 46992866 | chr19 | 46993164 | 46993260 | chr19 | 46993282 | 46993388 |
| chr19 | 46996501 | 46996514 | chr19 | 46996578 | 46996838 | chr19 | 47152978 | 47152990 |
| chr19 | 47200361 | 47200536 | chr19 | 47329748 | 47329867 | chr19 | 47358646 | 47358751 |
| chr19 | 47515017 | 47515047 | chr19 | 47618255 | 47618434 | chr19 | 47776713 | 47776742 |
| chr19 | 47933311 | 47933732 | chr19 | 47951288 | 47951318 | chr19 | 47976399 | 47976429 |
| chr19 | 48003607 | 48003714 | chr19 | 48076642 | 48076672 | chr19 | 48082100 | 48082130 |
| chr19 | 48108151 | 48108320 | chr19 | 48137171 | 48137307 | chr19 | 48151265 | 48151337 |

TABLE 12-continued

Pan Cancer #2

| chr | start | end | chr | start | end | chr | start | end |
|---|---|---|---|---|---|---|---|---|
| chr19 | 48249451 | 48249602 | chr19 | 48614843 | 48614873 | chr19 | 48771551 | 48771600 |
| chr19 | 48777059 | 48777121 | chr19 | 48800603 | 48800769 | chr19 | 48857725 | 48857831 |
| chr19 | 48902848 | 48902878 | chr19 | 48918100 | 48918598 | chr19 | 49043242 | 49043272 |
| chr19 | 49119229 | 49119259 | chr19 | 49127373 | 49127674 | chr19 | 49180462 | 49180558 |
| chr19 | 49256396 | 49256438 | chr19 | 49285456 | 49285593 | chr19 | 49290711 | 49290844 |
| chr19 | 49375050 | 49375216 | chr19 | 49399218 | 49399310 | chr19 | 49402471 | 49402551 |
| chr19 | 49498076 | 49498148 | chr19 | 49575460 | 49575474 | chr19 | 49590284 | 49590399 |
| chr19 | 49628132 | 49628252 | chr19 | 49784869 | 49784935 | chr19 | 49890887 | 49890929 |
| chr19 | 49935736 | 49936174 | chr19 | 49936864 | 49936894 | chr19 | 49997263 | 49997324 |
| chr19 | 49998434 | 49998607 | chr19 | 50028397 | 50028530 | chr19 | 50049718 | 50049953 |
| chr19 | 50203173 | 50203203 | chr19 | 50216042 | 50216072 | chr19 | 50243339 | 50243379 |
| chr19 | 50304736 | 50304766 | chr19 | 50316244 | 50316468 | chr19 | 50319874 | 50319916 |
| chr19 | 50320233 | 50320277 | chr19 | 50353394 | 50353574 | chr19 | 50553680 | 50553709 |
| chr19 | 50553997 | 50554510 | chr19 | 50589044 | 50589079 | chr19 | 50816431 | 50816474 |
| chr19 | 50833828 | 50833863 | chr19 | 50874895 | 50874933 | chr19 | 50898558 | 50898727 |
| chr19 | 50938547 | 50938691 | chr19 | 51041149 | 51041189 | chr19 | 51161225 | 51161255 |
| chr19 | 51162197 | 51162253 | chr19 | 51162428 | 51162527 | chr19 | 51171219 | 51171275 |
| chr19 | 51171828 | 51171860 | chr19 | 51227719 | 51227785 | chr19 | 51228049 | 51228079 |
| chr19 | 51228369 | 51228507 | chr19 | 51304554 | 51304602 | chr19 | 51520423 | 51520453 |
| chr19 | 51715329 | 51715359 | chr19 | 51830845 | 51831002 | chr19 | 51831121 | 51831128 |
| chr19 | 51831360 | 51831390 | chr19 | 51925127 | 51925272 | chr19 | 52097689 | 52097732 |
| chr19 | 52139210 | 52139326 | chr19 | 52207254 | 52207367 | chr19 | 52222523 | 52222923 |
| chr19 | 52391235 | 52391264 | chr19 | 52452316 | 52452335 | chr19 | 52552104 | 52552119 |
| chr19 | 52715963 | 52715992 | chr19 | 52839588 | 52839717 | chr19 | 52839742 | 52839938 |
| chr19 | 52872924 | 52873440 | chr19 | 52956805 | 52956848 | chr19 | 53028928 | 53029035 |
| chr19 | 53031185 | 53031215 | chr19 | 53073314 | 53073354 | chr19 | 53073563 | 53073772 |
| chr19 | 53073820 | 53073987 | chr19 | 53141648 | 53141745 | chr19 | 53193858 | 53193893 |
| chr19 | 53194281 | 53194396 | chr19 | 53204758 | 53204837 | chr19 | 53291021 | 53291081 |
| chr19 | 53398908 | 53399031 | chr19 | 53399804 | 53399848 | chr19 | 53436895 | 53437067 |
| chr19 | 53446951 | 53447130 | chr19 | 53496649 | 53496786 | chr19 | 53496814 | 53496846 |
| chr19 | 53561668 | 53561733 | chr19 | 53635952 | 53636091 | chr19 | 53661647 | 53661902 |
| chr19 | 53662174 | 53662694 | chr19 | 53688015 | 53688059 | chr19 | 53696414 | 53696580 |
| chr19 | 53700596 | 53700729 | chr19 | 53757895 | 53758247 | chr19 | 53811858 | 53811988 |
| chr19 | 53836954 | 53836975 | chr19 | 53837377 | 53837432 | chr19 | 53860082 | 53860151 |
| chr19 | 53873182 | 53873212 | chr19 | 53970501 | 53970725 | chr19 | 53970968 | 53971039 |
| chr19 | 53971110 | 53971157 | chr19 | 54023887 | 54024196 | chr19 | 54024521 | 54024884 |
| chr19 | 54271479 | 54271509 | chr19 | 54369555 | 54369681 | chr19 | 54411125 | 54411168 |
| chr19 | 54411556 | 54411586 | chr19 | 54412873 | 54412985 | chr19 | 54481771 | 54481968 |
| chr19 | 54483173 | 54483305 | chr19 | 54483365 | 54483546 | chr19 | 54485403 | 54485646 |
| chr19 | 54485673 | 54485823 | chr19 | 54850630 | 54850659 | chr19 | 55598811 | 55598888 |
| chr19 | 55629883 | 55630028 | chr19 | 55728901 | 55729104 | chr19 | 55849550 | 55849638 |
| chr19 | 56159273 | 56159499 | chr19 | 56189937 | 56189966 | chr19 | 56201643 | 56201938 |
| chr19 | 56340995 | 56341033 | chr19 | 56588656 | 56588780 | chr19 | 56728678 | 56728788 |
| chr19 | 56858084 | 56858227 | chr19 | 56879501 | 56880008 | chr19 | 56904740 | 56905203 |
| chr19 | 56915320 | 56915428 | chr19 | 56988557 | 56988663 | chr19 | 56989528 | 56989625 |
| chr19 | 56989697 | 56989754 | chr19 | 57050463 | 57050493 | chr19 | 57149579 | 57149619 |
| chr19 | 57154885 | 57155017 | chr19 | 57182994 | 57183126 | chr19 | 57276656 | 57276700 |
| chr19 | 57323825 | 57323854 | chr19 | 57610896 | 57610985 | chr19 | 57617522 | 57617715 |
| chr19 | 57617832 | 57618121 | chr19 | 57683148 | 57683162 | chr19 | 57683240 | 57683295 |
| chr19 | 57862395 | 57862783 | chr19 | 58011124 | 58011281 | chr19 | 58038924 | 58038969 |
| chr19 | 58095006 | 58095835 | chr19 | 58111632 | 58111783 | chr19 | 58125544 | 58125881 |
| chr19 | 58144494 | 58144701 | chr19 | 58219839 | 58220392 | chr19 | 58220516 | 58220832 |
| chr19 | 58238326 | 58238738 | chr19 | 58238988 | 58239088 | chr19 | 58316915 | 58317096 |
| chr19 | 58325075 | 58325282 | chr19 | 58400079 | 58400175 | chr19 | 58400417 | 58400518 |
| chr19 | 58458754 | 58458890 | chr19 | 58458979 | 58459201 | chr19 | 58514518 | 58514552 |
| chr19 | 58520739 | 58520941 | chr19 | 58545145 | 58545387 | chr19 | 58545578 | 58545589 |
| chr19 | 58545652 | 58545837 | chr19 | 58609254 | 58609359 | chr19 | 58609473 | 58609525 |
| chr19 | 58609713 | 58609854 | chr19 | 58629975 | 58629975 | chr19 | 58661894 | 58662094 |
| chr19 | 58666171 | 58666313 | chr19 | 58740086 | 58740118 | chr19 | 58807869 | 58807931 |
| chr19 | 58874735 | 58874987 | chr19 | 58951271 | 58951400 | chr19 | 58951526 | 58951916 |
| chr19 | 58964180 | 58964266 | chr19 | 59054642 | 59054774 | chr20 | 118577 | 118751 |
| chr20 | 291148 | 291162 | chr20 | 291221 | 291373 | chr20 | 304259 | 304408 |
| chr20 | 400007 | 400087 | chr20 | 401153 | 401183 | chr20 | 401591 | 401756 |
| chr20 | 523146 | 523193 | chr20 | 590434 | 590502 | chr20 | 592405 | 592449 |
| chr20 | 644182 | 644351 | chr20 | 644407 | 644787 | chr20 | 799104 | 799247 |
| chr20 | 799458 | 799706 | chr20 | 982749 | 982798 | chr20 | 982892 | 982989 |
| chr20 | 1094560 | 1094682 | chr20 | 1197670 | 1197711 | chr20 | 1206855 | 1207034 |
| chr20 | 1783761 | 1784305 | chr20 | 1876110 | 1876176 | chr20 | 1975357 | 1975386 |
| chr20 | 2539331 | 2539771 | chr20 | 2645540 | 2645795 | chr20 | 2668770 | 2668922 |
| chr20 | 2780753 | 2781452 | chr20 | 2781731 | 2781761 | chr20 | 2785659 | 2785866 |
| chr20 | 2785956 | 2786060 | chr20 | 3027758 | 3027931 | chr20 | 3052583 | 3052836 |
| chr20 | 3073561 | 3073899 | chr20 | 3154172 | 3154204 | chr20 | 3204870 | 3204952 |
| chr20 | 3220893 | 3220943 | chr20 | 3229576 | 3229612 | chr20 | 3641774 | 3641937 |
| chr20 | 3663020 | 3663174 | chr20 | 3762152 | 3762181 | chr20 | 3762407 | 3762436 |
| chr20 | 3858389 | 3858632 | chr20 | 3996688 | 3996726 | chr20 | 4040710 | 4040871 |
| chr20 | 4061323 | 4061452 | chr20 | 4085057 | 4085087 | chr20 | 4229402 | 4229432 |

TABLE 12-continued

Pan Cancer #2

| chr | start | end | chr | start | end | chr | start | end |
|---|---|---|---|---|---|---|---|---|
| chr20 | 4229786 | 4230600 | chr20 | 4803070 | 4803650 | chr20 | 4803921 | 4804008 |
| chr20 | 4804566 | 4804732 | chr20 | 5025228 | 5025258 | chr20 | 5106720 | 5106750 |
| chr20 | 5296172 | 5296900 | chr20 | 5297226 | 5297418 | chr20 | 5433047 | 5433085 |
| chr20 | 5610356 | 5610386 | chr20 | 6022797 | 6023045 | chr20 | 6023268 | 6023351 |
| chr20 | 6748925 | 6749036 | chr20 | 7980362 | 7980392 | chr20 | 8112378 | 8112408 |
| chr20 | 8112739 | 8113022 | chr20 | 8113557 | 8113605 | chr20 | 9487385 | 9487719 |
| chr20 | 9487789 | 9487997 | chr20 | 9488376 | 9488848 | chr20 | 9489070 | 9489214 |
| chr20 | 9489424 | 9489708 | chr20 | 9495271 | 9495509 | chr20 | 9496330 | 9496530 |
| chr20 | 9496581 | 9496833 | chr20 | 9497035 | 9497109 | chr20 | 10198289 | 10198600 |
| chr20 | 10198941 | 10198945 | chr20 | 13200599 | 13200634 | chr20 | 14447971 | 14448144 |
| chr20 | 16554749 | 16555030 | chr20 | 17206513 | 17206747 | chr20 | 17207874 | 17207930 |
| chr20 | 17208585 | 17208620 | chr20 | 18039823 | 18039897 | chr20 | 18073183 | 18073276 |
| chr20 | 18073312 | 18073461 | chr20 | 18448982 | 18449076 | chr20 | 18489463 | 18489658 |
| chr20 | 19128288 | 19128473 | chr20 | 19739613 | 19739696 | chr20 | 19928306 | 19928461 |
| chr20 | 20344498 | 20344559 | chr20 | 20347460 | 20347709 | chr20 | 20347737 | 20348154 |
| chr20 | 20348526 | 20348605 | chr20 | 20349153 | 20349255 | chr20 | 20349574 | 20349604 |
| chr20 | 21080714 | 21080956 | chr20 | 21081029 | 21081844 | chr20 | 21082095 | 21082123 |
| chr20 | 21082216 | 21082253 | chr20 | 21082532 | 21082917 | chr20 | 21083421 | 21084361 |
| chr20 | 21085831 | 21085864 | chr20 | 21086195 | 21086451 | chr20 | 21086866 | 21087188 |
| chr20 | 21372174 | 21372192 | chr20 | 21372295 | 21372725 | chr20 | 21376250 | 21376336 |
| chr20 | 21376703 | 21376733 | chr20 | 21376877 | 21377128 | chr20 | 21377474 | 21377640 |
| chr20 | 21377738 | 21378551 | chr20 | 21486375 | 21486659 | chr20 | 21486786 | 21486881 |
| chr20 | 21487153 | 21487581 | chr20 | 21488158 | 21488351 | chr20 | 21489240 | 21489446 |
| chr20 | 21489622 | 21489703 | chr20 | 21490175 | 21490762 | chr20 | 21490815 | 21491345 |
| chr20 | 21492378 | 21492409 | chr20 | 21492508 | 21492825 | chr20 | 21493308 | 21493993 |
| chr20 | 21494531 | 21494703 | chr20 | 21495942 | 21495986 | chr20 | 21496260 | 21496294 |
| chr20 | 21496684 | 21497136 | chr20 | 21497413 | 21498638 | chr20 | 21499961 | 21500134 |
| chr20 | 21501445 | 21501724 | chr20 | 21502037 | 21502144 | chr20 | 21502590 | 21502699 |
| chr20 | 21502838 | 21503117 | chr20 | 21503455 | 21503773 | chr20 | 21682399 | 21682456 |
| chr20 | 21683311 | 21683651 | chr20 | 21685385 | 21685526 | chr20 | 21686235 | 21686677 |
| chr20 | 21687009 | 21687382 | chr20 | 21689956 | 21690185 | chr20 | 21694499 | 21694529 |
| chr20 | 21695088 | 21695273 | chr20 | 21695306 | 21695357 | chr20 | 21748445 | 21748491 |
| chr20 | 22401392 | 22401421 | chr20 | 22557396 | 22557675 | chr20 | 22557979 | 22558114 |
| chr20 | 22558637 | 22558669 | chr20 | 22559645 | 22559690 | chr20 | 22562721 | 22562840 |
| chr20 | 22563563 | 22563602 | chr20 | 22564235 | 22564265 | chr20 | 22566961 | 22566990 |
| chr20 | 23015917 | 23015946 | chr20 | 23029110 | 23029151 | chr20 | 23029589 | 23030085 |
| chr20 | 23030292 | 23030357 | chr20 | 23031548 | 23031692 | chr20 | 23138383 | 23138444 |
| chr20 | 23406698 | 23406830 | chr20 | 24450231 | 24450513 | chr20 | 24450820 | 24451019 |
| chr20 | 24451450 | 24451592 | chr20 | 24505190 | 24505252 | chr20 | 24726701 | 24726825 |
| chr20 | 25058385 | 25058616 | chr20 | 25061746 | 25061788 | chr20 | 25061979 | 25062311 |
| chr20 | 25062511 | 25062645 | chr20 | 25062708 | 25062817 | chr20 | 25062871 | 25062880 |
| chr20 | 25063780 | 25063906 | chr20 | 25064258 | 25064458 | chr20 | 25065179 | 25065395 |
| chr20 | 25086082 | 25086275 | chr20 | 25223141 | 25223277 | chr20 | 25230509 | 25230799 |
| chr20 | 25334513 | 25334650 | chr20 | 25344027 | 25344118 | chr20 | 26188812 | 26188961 |
| chr20 | 26190313 | 26190361 | chr20 | 29832911 | 29833090 | chr20 | 29914002 | 29914139 |
| chr20 | 29956013 | 29956042 | chr20 | 29956570 | 29956599 | chr20 | 30101523 | 30101743 |
| chr20 | 30162296 | 30162459 | chr20 | 30174561 | 30174645 | chr20 | 30186068 | 30186165 |
| chr20 | 30201236 | 30201360 | chr20 | 30280423 | 30280509 | chr20 | 30297090 | 30297217 |
| chr20 | 30468319 | 30468349 | chr20 | 30582750 | 30582978 | chr20 | 30639141 | 30639319 |
| chr20 | 30639632 | 30639847 | chr20 | 30640106 | 30640270 | chr20 | 30778024 | 30778313 |
| chr20 | 31035471 | 31035518 | chr20 | 31115683 | 31115799 | chr20 | 31151769 | 31151799 |
| chr20 | 31207211 | 31207283 | chr20 | 31282734 | 31282903 | chr20 | 32301797 | 32301953 |
| chr20 | 32450248 | 32450427 | chr20 | 32701064 | 32701320 | chr20 | 32716914 | 32716949 |
| chr20 | 32768669 | 32768728 | chr20 | 32893006 | 32893125 | chr20 | 33540284 | 33540550 |
| chr20 | 33547485 | 33547585 | chr20 | 33574914 | 33574992 | chr20 | 34041981 | 34042087 |
| chr20 | 34148020 | 34148254 | chr20 | 34188617 | 34188631 | chr20 | 34188748 | 34189088 |
| chr20 | 34189167 | 34189391 | chr20 | 34189680 | 34189910 | chr20 | 35640448 | 35640561 |
| chr20 | 35742487 | 35742607 | chr20 | 35892604 | 35892746 | chr20 | 36183184 | 36183340 |
| chr20 | 36531799 | 36531910 | chr20 | 36781324 | 36781354 | chr20 | 37302697 | 37303343 |
| chr20 | 37351793 | 37352515 | chr20 | 37352607 | 37352626 | chr20 | 37353193 | 37353236 |
| chr20 | 37353455 | 37353718 | chr20 | 37354145 | 37354831 | chr20 | 37354994 | 37355202 |
| chr20 | 37355847 | 37356042 | chr20 | 37356169 | 37356827 | chr20 | 37357216 | 37357353 |
| chr20 | 37357825 | 37358190 | chr20 | 37434552 | 37434721 | chr20 | 37434737 | 37434744 |
| chr20 | 37435104 | 37435218 | chr20 | 37435488 | 37435860 | chr20 | 39316203 | 39316322 |
| chr20 | 39316984 | 39317392 | chr20 | 39317750 | 39318166 | chr20 | 39318383 | 39318415 |
| chr20 | 39319126 | 39319203 | chr20 | 39319515 | 39319653 | chr20 | 39995146 | 39995813 |
| chr20 | 40500546 | 40500638 | chr20 | 40515378 | 40515504 | chr20 | 40743859 | 40743888 |
| chr20 | 41817786 | 41817915 | chr20 | 41818008 | 41818085 | chr20 | 41818567 | 41818748 |
| chr20 | 41818805 | 41818914 | chr20 | 42136330 | 42136411 | chr20 | 42218429 | 42218664 |
| chr20 | 42281425 | 42281455 | chr20 | 42543754 | 42543853 | chr20 | 42544091 | 42544533 |
| chr20 | 42544728 | 42544984 | chr20 | 42852751 | 42852915 | chr20 | 42876525 | 42876575 |
| chr20 | 43438071 | 43438085 | chr20 | 43438335 | 43438466 | chr20 | 43438982 | 43439022 |
| chr20 | 43439291 | 43439510 | chr20 | 43952174 | 43952302 | chr20 | 44003765 | 44003811 |
| chr20 | 44452731 | 44453063 | chr20 | 44519077 | 44519107 | chr20 | 44601547 | 44601716 |
| chr20 | 44602074 | 44602364 | chr20 | 44639181 | 44639496 | chr20 | 44640338 | 44640367 |
| chr20 | 44660750 | 44660877 | chr20 | 44686423 | 44686614 | chr20 | 44686628 | 44686762 |

TABLE 12-continued

Pan Cancer #2

| chr | start | end | chr | start | end | chr | start | end |
|---|---|---|---|---|---|---|---|---|
| chr20 | 44746484 | 44746781 | chr20 | 44803174 | 44803675 | chr20 | 44875240 | 44875411 |
| chr20 | 44880041 | 44880076 | chr20 | 44937202 | 44937411 | chr20 | 44937426 | 44937643 |
| chr20 | 44941518 | 44941661 | chr20 | 45142000 | 45142038 | chr20 | 45142152 | 45142272 |
| chr20 | 45279854 | 45279981 | chr20 | 45280040 | 45280344 | chr20 | 45280344 | 45280428 |
| chr20 | 45337804 | 45337945 | chr20 | 45524523 | 45524553 | chr20 | 47247239 | 47247450 |
| chr20 | 47274032 | 47274062 | chr20 | 47296109 | 47296231 | chr20 | 47443729 | 47443936 |
| chr20 | 47443945 | 47444282 | chr20 | 47450370 | 47450490 | chr20 | 47815615 | 47815711 |
| chr20 | 47835328 | 47835358 | chr20 | 47905426 | 47905603 | chr20 | 47934824 | 47935268 |
| chr20 | 47935495 | 47935567 | chr20 | 47935928 | 47936027 | chr20 | 48184381 | 48184435 |
| chr20 | 48695665 | 48696227 | chr20 | 48768118 | 48768148 | chr20 | 48774527 | 48774569 |
| chr20 | 49204179 | 49204449 | chr20 | 49261803 | 49262104 | chr20 | 49323924 | 49324125 |
| chr20 | 49350910 | 49351041 | chr20 | 49351564 | 49351649 | chr20 | 49358137 | 49358396 |
| chr20 | 49377755 | 49378043 | chr20 | 49381140 | 49381240 | chr20 | 49575909 | 49575939 |
| chr20 | 49639777 | 49639856 | chr20 | 49639883 | 49639996 | chr20 | 49640095 | 49640157 |
| chr20 | 49969348 | 49969515 | chr20 | 50160756 | 50160905 | chr20 | 50383224 | 50383423 |
| chr20 | 50384767 | 50384896 | chr20 | 50602134 | 50602264 | chr20 | 50693423 | 50693468 |
| chr20 | 50720437 | 50721200 | chr20 | 50721235 | 50721670 | chr20 | 50721989 | 50722193 |
| chr20 | 50722598 | 50722821 | chr20 | 51589766 | 51589908 | chr20 | 52226337 | 52226366 |
| chr20 | 52311463 | 52311728 | chr20 | 52401713 | 52401775 | chr20 | 52789445 | 52789475 |
| chr20 | 52789853 | 52789948 | chr20 | 52790082 | 52790155 | chr20 | 53092192 | 53092376 |
| chr20 | 53093085 | 53093115 | chr20 | 54522432 | 54522631 | chr20 | 54578507 | 54578725 |
| chr20 | 54579892 | 54579958 | chr20 | 54580070 | 54580323 | chr20 | 54580622 | 54580691 |
| chr20 | 55008041 | 55008194 | chr20 | 55071563 | 55071717 | chr20 | 55200035 | 55200310 |
| chr20 | 55200616 | 55200706 | chr20 | 55200922 | 55201092 | chr20 | 55201764 | 55202068 |
| chr20 | 55202359 | 55202626 | chr20 | 55202826 | 55203107 | chr20 | 55204322 | 55204604 |
| chr20 | 55204966 | 55205000 | chr20 | 55206294 | 55206393 | chr20 | 55206739 | 55206774 |
| chr20 | 55499496 | 55499709 | chr20 | 55500016 | 55500085 | chr20 | 55500441 | 55500720 |
| chr20 | 55693527 | 55693662 | chr20 | 55841134 | 55841356 | chr20 | 55842096 | 55842189 |
| chr20 | 55959212 | 55959250 | chr20 | 56766160 | 56766190 | chr20 | 56803398 | 56803441 |
| chr20 | 56803842 | 56803920 | chr20 | 56998280 | 56998337 | chr20 | 57089452 | 57089459 |
| chr20 | 57090104 | 57090173 | chr20 | 57224842 | 57225079 | chr20 | 57225219 | 57225307 |
| chr20 | 57484406 | 57484445 | chr20 | 58179809 | 58179854 | chr20 | 58180214 | 58180402 |
| chr20 | 58508887 | 58508943 | chr20 | 59525138 | 59525300 | chr20 | 59804170 | 59804235 |
| chr20 | 59826192 | 59826221 | chr20 | 59826962 | 59826977 | chr20 | 59828341 | 59828407 |
| chr20 | 59880433 | 59880477 | chr20 | 59910175 | 59910346 | chr20 | 59973028 | 59973072 |
| chr20 | 60202594 | 60202624 | chr20 | 60235333 | 60235526 | chr20 | 60238381 | 60238472 |
| chr20 | 60238877 | 60238980 | chr20 | 60243944 | 60244107 | chr20 | 60329584 | 60329738 |
| chr20 | 60333880 | 60333969 | chr20 | 60359849 | 60359879 | chr20 | 60375036 | 60375070 |
| chr20 | 60439634 | 60439755 | chr20 | 60453925 | 60454091 | chr20 | 60477306 | 60477537 |
| chr20 | 60485374 | 60485425 | chr20 | 60503030 | 60503060 | chr20 | 60545561 | 60545792 |
| chr20 | 60620122 | 60620557 | chr20 | 60772853 | 60773878 | chr20 | 60789965 | 60790124 |
| chr20 | 60816241 | 60816271 | chr20 | 60892164 | 60892222 | chr20 | 60926019 | 60926049 |
| chr20 | 60970953 | 60970983 | chr20 | 60983859 | 60984010 | chr20 | 60984341 | 60984465 |
| chr20 | 61288068 | 61288156 | chr20 | 61288463 | 61288534 | chr20 | 61294693 | 61294857 |
| chr20 | 61340581 | 61340689 | chr20 | 61412313 | 61412438 | chr20 | 61505851 | 61506330 |
| chr20 | 61532546 | 61532605 | chr20 | 61560418 | 61560460 | chr20 | 61560529 | 61560922 |
| chr20 | 61585771 | 61585922 | chr20 | 61585990 | 61586004 | chr20 | 61636876 | 61636890 |
| chr20 | 61637468 | 61637648 | chr20 | 61637736 | 61637956 | chr20 | 61638221 | 61638469 |
| chr20 | 61638535 | 61638631 | chr20 | 61703710 | 61703761 | chr20 | 61703846 | 61703875 |
| chr20 | 61714591 | 61714621 | chr20 | 61734420 | 61734481 | chr20 | 61747894 | 61747934 |
| chr20 | 61763598 | 61763628 | chr20 | 61765285 | 61765425 | chr20 | 61808181 | 61808270 |
| chr20 | 61808667 | 61809005 | chr20 | 61809219 | 61809631 | chr20 | 61809841 | 61810089 |
| chr20 | 61823170 | 61823339 | chr20 | 61862380 | 61862452 | chr20 | 61885247 | 61885462 |
| chr20 | 61886068 | 61886203 | chr20 | 61886257 | 61886258 | chr20 | 61886725 | 61886755 |
| chr20 | 61974191 | 61974354 | chr20 | 61980860 | 61980975 | chr20 | 62031173 | 62031234 |
| chr20 | 62032058 | 62032095 | chr20 | 62037559 | 62037598 | chr20 | 62046227 | 62046421 |
| chr20 | 62058700 | 62058786 | chr20 | 62090524 | 62090778 | chr20 | 62097666 | 62097695 |
| chr20 | 62115047 | 62115266 | chr20 | 62119339 | 62119618 | chr20 | 62119923 | 62120171 |
| chr20 | 62126118 | 62126429 | chr20 | 62157157 | 62157307 | chr20 | 62165631 | 62165762 |
| chr20 | 62167554 | 62167584 | chr20 | 62170179 | 62170209 | chr20 | 62172945 | 62173055 |
| chr20 | 62185386 | 62185444 | chr20 | 62260818 | 62260905 | chr20 | 62261532 | 62261562 |
| chr20 | 62284487 | 62284615 | chr20 | 62314848 | 62314955 | chr20 | 62321206 | 62321341 |
| chr20 | 62321638 | 62321881 | chr20 | 62340372 | 62340442 | chr20 | 62383218 | 62383289 |
| chr20 | 62391938 | 62391968 | chr20 | 62461349 | 62461475 | chr20 | 62488293 | 62488350 |
| chr20 | 62497836 | 62497920 | chr20 | 62631351 | 62631593 | chr20 | 62680657 | 62680739 |
| chr20 | 62715014 | 62715069 | chr20 | 62786577 | 62786726 | chr20 | 62795643 | 62795672 |
| chr21 | 19274828 | 19274858 | chr21 | 22370332 | 22370458 | chr21 | 22370688 | 22370718 |
| chr21 | 26934368 | 26934786 | chr21 | 27011773 | 27011807 | chr21 | 27012373 | 27012431 |
| chr21 | 27944995 | 27945081 | chr21 | 27945693 | 27945722 | chr21 | 28216634 | 28217690 |
| chr21 | 28218774 | 28219045 | chr21 | 28338836 | 28338887 | chr21 | 28339247 | 28339501 |
| chr21 | 28339892 | 28340048 | chr21 | 28340063 | 28340318 | chr21 | 31015201 | 31015231 |
| chr21 | 31056850 | 31056927 | chr21 | 31311404 | 31311553 | chr21 | 31312080 | 31312105 |
| chr21 | 31312313 | 31312445 | chr21 | 32253745 | 32253774 | chr21 | 33043985 | 33044051 |
| chr21 | 33244921 | 33245040 | chr21 | 33245683 | 33245718 | chr21 | 33246009 | 33246190 |
| chr21 | 33627549 | 33627649 | chr21 | 33721756 | 33721824 | chr21 | 33785288 | 33785325 |
| chr21 | 33983236 | 33983488 | chr21 | 34392206 | 34392403 | chr21 | 34392437 | 34392566 |

TABLE 12-continued

Pan Cancer #2

| chr | start | end | chr | start | end | chr | start | end |
|---|---|---|---|---|---|---|---|---|
| chr21 | 34395302 | 34396269 | chr21 | 34396795 | 34397091 | chr21 | 34398070 | 34398634 |
| chr21 | 34398933 | 34399258 | chr21 | 34399442 | 34400104 | chr21 | 34400232 | 34400258 |
| chr21 | 34401185 | 34401392 | chr21 | 34442595 | 34442665 | chr21 | 34443103 | 34443262 |
| chr21 | 34443509 | 34443686 | chr21 | 34443893 | 34443956 | chr21 | 34444163 | 34444362 |
| chr21 | 34444445 | 34444598 | chr21 | 34469746 | 34469844 | chr21 | 35051159 | 35051231 |
| chr21 | 36041985 | 36042028 | chr21 | 36042092 | 36042238 | chr21 | 36042658 | 36042861 |
| chr21 | 37527928 | 37527958 | chr21 | 37758570 | 37758652 | chr21 | 37775034 | 37775141 |
| chr21 | 38064457 | 38064683 | chr21 | 38064966 | 38065522 | chr21 | 38065955 | 38066112 |
| chr21 | 38067203 | 38067233 | chr21 | 38068178 | 38068229 | chr21 | 38068647 | 38068783 |
| chr21 | 38069093 | 38069203 | chr21 | 38069459 | 38069496 | chr21 | 38069854 | 38070162 |
| chr21 | 38070705 | 38070765 | chr21 | 38071791 | 38071905 | chr21 | 38073007 | 38073070 |
| chr21 | 38073300 | 38073525 | chr21 | 38073616 | 38073860 | chr21 | 38078415 | 38078487 |
| chr21 | 38079988 | 38080062 | chr21 | 38080175 | 38080386 | chr21 | 38080551 | 38080684 |
| chr21 | 38081085 | 38081192 | chr21 | 38081666 | 38081835 | chr21 | 38082042 | 38082072 |
| chr21 | 38082315 | 38082345 | chr21 | 38082930 | 38083196 | chr21 | 38092179 | 38092221 |
| chr21 | 38119904 | 38120312 | chr21 | 38638422 | 38638526 | chr21 | 38935478 | 38935549 |
| chr21 | 39047776 | 39047838 | chr21 | 39870612 | 39870641 | chr21 | 40033618 | 40033648 |
| chr21 | 40033877 | 40033906 | chr21 | 40034756 | 40034785 | chr21 | 40984685 | 40984900 |
| chr21 | 42596911 | 42597043 | chr21 | 42617963 | 42617995 | chr21 | 42649172 | 42649202 |
| chr21 | 43186698 | 43186889 | chr21 | 43240082 | 43240112 | chr21 | 43256565 | 43256603 |
| chr21 | 43376373 | 43376403 | chr21 | 43393528 | 43393713 | chr21 | 43485279 | 43485348 |
| chr21 | 43786683 | 43786713 | chr21 | 43991463 | 43991493 | chr21 | 44250815 | 44250855 |
| chr21 | 44283581 | 44283774 | chr21 | 44494941 | 44495155 | chr21 | 44514762 | 44514791 |
| chr21 | 44524441 | 44524470 | chr21 | 44837088 | 44837213 | chr21 | 44847591 | 44847622 |
| chr21 | 44866603 | 44866711 | chr21 | 44886709 | 44886870 | chr21 | 45118492 | 45118644 |
| chr21 | 45131875 | 45131905 | chr21 | 45148615 | 45148758 | chr21 | 45195149 | 45195319 |
| chr21 | 45271643 | 45271688 | chr21 | 45273717 | 45273913 | chr21 | 45277332 | 45277513 |
| chr21 | 45290014 | 45290044 | chr21 | 45508617 | 45508647 | chr21 | 45521343 | 45521438 |
| chr21 | 45621533 | 45621573 | chr21 | 45717477 | 45717548 | chr21 | 45791079 | 45791109 |
| chr21 | 45847832 | 45847973 | chr21 | 46036642 | 46036767 | chr21 | 46125933 | 46126427 |
| chr21 | 46126567 | 46126721 | chr21 | 46127039 | 46127094 | chr21 | 46127542 | 46127692 |
| chr21 | 46128902 | 46128938 | chr21 | 46129444 | 46129485 | chr21 | 46193414 | 46193542 |
| chr21 | 46257116 | 46257273 | chr21 | 46310428 | 46310491 | chr21 | 46318286 | 46318343 |
| chr21 | 46319156 | 46319459 | chr21 | 46359187 | 46359248 | chr21 | 46452374 | 46452539 |
| chr21 | 46677734 | 46677796 | chr21 | 46825825 | 46826067 | chr21 | 46847654 | 46847684 |
| chr21 | 46863658 | 46863708 | chr21 | 46925780 | 46925925 | chr21 | 46926459 | 46926565 |
| chr21 | 46935739 | 46935936 | chr21 | 47010409 | 47010451 | chr21 | 47062753 | 47062825 |
| chr21 | 47063538 | 47063962 | chr21 | 47064250 | 47064377 | chr21 | 47404174 | 47404325 |
| chr21 | 47504861 | 47504895 | chr21 | 47518776 | 47518814 | chr21 | 47717560 | 47717589 |
| chr21 | 47746270 | 47746393 | chr22 | 17081932 | 17081935 | chr22 | 17082989 | 17083003 |
| chr22 | 17083396 | 17083410 | chr22 | 17601086 | 17601133 | chr22 | 17601260 | 17601368 |
| chr22 | 17602511 | 17602624 | chr22 | 17850454 | 17850621 | chr22 | 18009969 | 18010121 |
| chr22 | 18110495 | 18110593 | chr22 | 18328127 | 18328268 | chr22 | 18340822 | 18340868 |
| chr22 | 18627328 | 18627537 | chr22 | 19017532 | 19017567 | chr22 | 19117564 | 19117594 |
| chr22 | 19136907 | 19136936 | chr22 | 19137859 | 19137888 | chr22 | 19138109 | 19138138 |
| chr22 | 19510799 | 19510946 | chr22 | 19511142 | 19511455 | chr22 | 19511542 | 19511567 |
| chr22 | 19511849 | 19511875 | chr22 | 19702265 | 19702410 | chr22 | 19706171 | 19706677 |
| chr22 | 19742834 | 19742969 | chr22 | 19748644 | 19748908 | chr22 | 20229079 | 20229239 |
| chr22 | 20792482 | 20792641 | chr22 | 20864642 | 20864672 | chr22 | 20940868 | 20940898 |
| chr22 | 21042829 | 21043014 | chr22 | 21153867 | 21154000 | chr22 | 21270750 | 21270834 |
| chr22 | 21276140 | 21276261 | chr22 | 21299605 | 21299635 | chr22 | 21304771 | 21305007 |
| chr22 | 21368587 | 21368617 | chr22 | 21977314 | 21977347 | chr22 | 21982792 | 21982972 |
| chr22 | 22005794 | 22006759 | chr22 | 22023273 | 22023451 | chr22 | 22058203 | 22058238 |
| chr22 | 22201344 | 22201568 | chr22 | 22862787 | 22862862 | chr22 | 22901105 | 22901455 |
| chr22 | 23791402 | 23791432 | chr22 | 23801459 | 23801610 | chr22 | 23991201 | 23991272 |
| chr22 | 24145484 | 24145513 | chr22 | 24179940 | 24179982 | chr22 | 24180687 | 24180766 |
| chr22 | 24560375 | 24560526 | chr22 | 24820330 | 24820396 | chr22 | 25678748 | 25678868 |
| chr22 | 25679043 | 25679249 | chr22 | 25679268 | 25679337 | chr22 | 25817107 | 25817180 |
| chr22 | 25817458 | 25817612 | chr22 | 27053194 | 27053250 | chr22 | 28198569 | 28198605 |
| chr22 | 28371649 | 28371679 | chr22 | 28838200 | 28838292 | chr22 | 28838509 | 28838551 |
| chr22 | 28839122 | 28839263 | chr22 | 29076592 | 29076622 | chr22 | 29091824 | 29091853 |
| chr22 | 29445752 | 29445923 | chr22 | 29876191 | 29876220 | chr22 | 29877223 | 29877299 |
| chr22 | 29977614 | 29977863 | chr22 | 30084358 | 30084388 | chr22 | 30090739 | 30090769 |
| chr22 | 30116904 | 30117146 | chr22 | 30158330 | 30158639 | chr22 | 30476197 | 30476220 |
| chr22 | 30784196 | 30784278 | chr22 | 30881582 | 30881612 | chr22 | 30938543 | 30938584 |
| chr22 | 31198492 | 31198637 | chr22 | 31218510 | 31218540 | chr22 | 31218794 | 31218829 |
| chr22 | 31481130 | 31481332 | chr22 | 32061344 | 32061374 | chr22 | 32748936 | 32748966 |
| chr22 | 32868720 | 32868837 | chr22 | 33197603 | 33197652 | chr22 | 33453877 | 33454074 |
| chr22 | 33454194 | 33454258 | chr22 | 33454346 | 33454366 | chr22 | 35079219 | 35079345 |
| chr22 | 35656581 | 35656610 | chr22 | 35768531 | 35768719 | chr22 | 35848358 | 35848670 |
| chr22 | 35938746 | 35939000 | chr22 | 36567866 | 36567896 | chr22 | 36681295 | 36681341 |
| chr22 | 36855297 | 36855335 | chr22 | 36855568 | 36855598 | chr22 | 36880362 | 36880462 |
| chr22 | 36902291 | 36902381 | chr22 | 37302073 | 37302103 | chr22 | 37720961 | 37721163 |
| chr22 | 38002684 | 38002733 | chr22 | 38087310 | 38087367 | chr22 | 38182815 | 38182981 |
| chr22 | 38199769 | 38199894 | chr22 | 38220653 | 38221201 | chr22 | 38477069 | 38477131 |
| chr22 | 38477297 | 38477794 | chr22 | 38507316 | 38507346 | chr22 | 38592856 | 38593076 |

TABLE 12-continued

Pan Cancer #2

| chr | start | end | chr | start | end | chr | start | end |
|---|---|---|---|---|---|---|---|---|
| chr22 | 38639229 | 38639259 | chr22 | 38874215 | 38874362 | chr22 | 39094890 | 39094964 |
| chr22 | 39098022 | 39098064 | chr22 | 39112502 | 39112584 | chr22 | 39784480 | 39784598 |
| chr22 | 39830355 | 39830457 | chr22 | 39853521 | 39853592 | chr22 | 39932499 | 39932563 |
| chr22 | 39954429 | 39954516 | chr22 | 40042627 | 40042743 | chr22 | 40075157 | 40075302 |
| chr22 | 40226345 | 40226389 | chr22 | 40767753 | 40767936 | chr22 | 40807034 | 40807063 |
| chr22 | 40895978 | 40896029 | chr22 | 41048732 | 41049109 | chr22 | 41217105 | 41217405 |
| chr22 | 41634393 | 41634542 | chr22 | 41637064 | 41637129 | chr22 | 41648414 | 41648444 |
| chr22 | 41657233 | 41657350 | chr22 | 41690119 | 41690149 | chr22 | 41839432 | 41839498 |
| chr22 | 42068010 | 42068172 | chr22 | 42096002 | 42096190 | chr22 | 42310087 | 42310220 |
| chr22 | 42311521 | 42311587 | chr22 | 42343416 | 42343676 | chr22 | 42353611 | 42353892 |
| chr22 | 42667358 | 42667432 | chr22 | 42916449 | 42916479 | chr22 | 43012543 | 43012877 |
| chr22 | 43083130 | 43083166 | chr22 | 43434441 | 43434477 | chr22 | 43540672 | 43540702 |
| chr22 | 43740084 | 43740128 | chr22 | 43808280 | 43808428 | chr22 | 44208418 | 44208448 |
| chr22 | 44258366 | 44258506 | chr22 | 44287650 | 44287696 | chr22 | 44455707 | 44455740 |
| chr22 | 45087614 | 45087649 | chr22 | 45088602 | 45088743 | chr22 | 45135939 | 45135979 |
| chr22 | 45252427 | 45252463 | chr22 | 45277292 | 45277322 | chr22 | 45313416 | 45313446 |
| chr22 | 45403086 | 45403133 | chr22 | 45403478 | 45403714 | chr22 | 45404197 | 45404433 |
| chr22 | 45404994 | 45405010 | chr22 | 45405047 | 45405061 | chr22 | 45405318 | 45405418 |
| chr22 | 45405620 | 45405768 | chr22 | 45406271 | 45406328 | chr22 | 45593643 | 45593715 |
| chr22 | 45604184 | 45604343 | chr22 | 45719161 | 45719190 | chr22 | 46262452 | 46263051 |
| chr22 | 46263512 | 46263623 | chr22 | 46263744 | 46263809 | chr22 | 46276749 | 46276820 |
| chr22 | 46438085 | 46438217 | chr22 | 46455833 | 46455905 | chr22 | 46599623 | 46599725 |
| chr22 | 46931260 | 46931332 | chr22 | 46933089 | 46933237 | chr22 | 47005080 | 47005154 |
| chr22 | 47023044 | 47023191 | chr22 | 47054686 | 47054716 | chr22 | 47193335 | 47193371 |
| chr22 | 47395475 | 47395505 | chr22 | 47525846 | 47525885 | chr22 | 47584867 | 47585024 |
| chr22 | 48027626 | 48027655 | chr22 | 48885530 | 48885837 | chr22 | 48886659 | 48886849 |
| chr22 | 48931881 | 48932027 | chr22 | 48971533 | 48971679 | chr22 | 48972220 | 48972465 |
| chr22 | 49852617 | 49852647 | chr22 | 49979646 | 49979757 | chr22 | 50001699 | 50001882 |
| chr22 | 50002787 | 50002819 | chr22 | 50003204 | 50003234 | chr22 | 50010113 | 50010258 |
| chr22 | 50010461 | 50010585 | chr22 | 50031691 | 50031721 | chr22 | 50064760 | 50064944 |
| chr22 | 50149431 | 50149470 | chr22 | 50251536 | 50251582 | chr22 | 50467005 | 50467035 |
| chr22 | 50467876 | 50468105 | chr22 | 50497147 | 50497182 | chr22 | 50497214 | 50497287 |
| chr22 | 50623672 | 50623714 | chr22 | 50623742 | 50623815 | chr22 | 50768840 | 50768876 |
| chr22 | 50899293 | 50899672 | chr22 | 50939073 | 50939111 | chr22 | 50943093 | 50943262 |
| chr22 | 50986016 | 50986045 | chr22 | 51042278 | 51042404 | chr22 | 51042458 | 51042565 |
| chr22 | 51112150 | 51112232 | chrX | 3631506 | 3631633 | chrX | 3746612 | 3746642 |
| chrX | 6145331 | 6145688 | chrX | 8698863 | 8698897 | chrX | 8699504 | 8699566 |
| chrX | 15807465 | 15807693 | chrX | 20148710 | 20148739 | chrX | 20160594 | 20160914 |
| chrX | 44730179 | 44730271 | chrX | 47039370 | 47039399 | chrX | 47426106 | 47426144 |
| chrX | 47426780 | 47426821 | chrX | 50557075 | 50557075 | chrX | 66931448 | 66931477 |
| chrX | 66937356 | 66937385 | chrX | 66943529 | 66943567 | chrX | 70339239 | 70339268 |
| chrX | 100228394 | 100228431 | chrX | 100740260 | 100740289 | chrX | 101906099 | 101906220 |
| chrX | 102000609 | 102000758 | chrX | 134156560 | 134156680 | chrX | 136656563 | 136656592 |
| chrY | 2655316 | 2655346 | chrY | 3446305 | 3446441 | chrY | 3838889 | 3838919 |
| chrY | 3968100 | 3968132 | chrY | 13316007 | 13316132 | chrY | 14532822 | 14532852 |
| chrY | 14533556 | 14533613 | chrY | 21204734 | 21205113 | chrY | 22530026 | 22530073 |
| MCV-R17b | 111 | 140 | MCV-R17b | 368 | 397 | MCV-R17b | 625 | 654 |
| MCV-R17b | 882 | 911 | MCV-R17b | 1139 | 1168 | MCV-R17b | 1396 | 1425 |
| MCV-R17b | 1653 | 1682 | MCV-R17b | 1910 | 1939 | MCV-R17b | 2167 | 2196 |
| MCV-R17b | 2424 | 2453 | MCV-R17b | 2681 | 2710 | MCV-R17b | 2938 | 2967 |
| MCV-R17b | 3195 | 3224 | MCV-R17b | 3452 | 3481 | MCV-R17b | 3709 | 3738 |
| MCV-R17b | 3966 | 3995 | MCV-R17b | 4223 | 4252 | MCV-R17b | 4480 | 4509 |
| MCV-R17b | 4737 | 4766 | MCV-R17b | 4994 | 5023 | AC160854.2_10710-13495 | 1027 | 1057 |
| AC211950.2_11234-25326 | 129 | 257 | AC211950.2_11234-25326 | 13335 | 13445 | AC211950.2_11234-25326 | 13743 | 13889 |
| AC241851.2_88-34049 | 14729 | 14973 | AC241851.2_88-34049 | 15261 | 15350 | AEKP01168736.1_1-4752 | 1754 | 2287 |
| EBV-B95-8 | 967 | 996 | EBV-B95-8 | 3766 | 3795 | EBV-B95-8 | 4234 | 4263 |
| EBV-B95-8 | 5326 | 5355 | EBV-B95-8 | 6553 | 6582 | EBV-B95-8 | 8800 | 8829 |
| EBV-B95-8 | 13471 | 13500 | EBV-B95-8 | 46577 | 46606 | EBV-B95-8 | 48222 | 48251 |
| EBV-B95-8 | 52842 | 52871 | EBV-B95-8 | 53561 | 53590 | EBV-B95-8 | 54377 | 54406 |
| EBV-B95-8 | 54778 | 54807 | EBV-B95-8 | 55067 | 55096 | EBV-B95-8 | 55893 | 55922 |
| EBV-B95-8 | 56735 | 56764 | EBV-B95-8 | 58227 | 58256 | EBV-B95-8 | 58926 | 58955 |
| EBV-B95-8 | 59581 | 59610 | EBV-B95-8 | 60099 | 60128 | EBV-B95-8 | 60877 | 60906 |
| EBV-B95-8 | 61319 | 61348 | EBV-B95-8 | 62302 | 62331 | EBV-B95-8 | 62840 | 62869 |
| EBV-B95-8 | 63178 | 63207 | EBV-B95-8 | 63601 | 63630 | EBV-B95-8 | 63935 | 63964 |
| EBV-B95-8 | 64590 | 64619 | EBV-B95-8 | 66726 | 66755 | EBV-B95-8 | 67486 | 67515 |
| EBV-B95-8 | 67857 | 67886 | EBV-B95-8 | 69228 | 69257 | EBV-B95-8 | 69798 | 69827 |
| EBV-B95-8 | 70439 | 70468 | EBV-B95-8 | 70839 | 70868 | EBV-B95-8 | 71938 | 71967 |
| EBV-B95-8 | 72204 | 72233 | EBV-B95-8 | 72535 | 72564 | EBV-B95-8 | 72983 | 73012 |
| EBV-B95-8 | 73950 | 73979 | EBV-B95-8 | 74304 | 74333 | EBV-B95-8 | 74689 | 74718 |
| EBV-B95-8 | 74978 | 75007 | EBV-B95-8 | 75256 | 75285 | EBV-B95-8 | 77784 | 77813 |
| EBV-B95-8 | 79618 | 79647 | EBV-B95-8 | 80289 | 80318 | EBV-B95-8 | 80704 | 80733 |
| EBV-B95-8 | 81198 | 81227 | EBV-B95-8 | 81629 | 81658 | EBV-B95-8 | 81888 | 81917 |
| EBV-B95-8 | 82225 | 82254 | EBV-B95-8 | 82703 | 82732 | EBV-B95-8 | 83438 | 83467 |

TABLE 12-continued

Pan Cancer #2

| chr | start | end | chr | start | end | chr | start | end |
|---|---|---|---|---|---|---|---|---|
| EBV-B95-8 | 85345 | 85374 | EBV-B95-8 | 86299 | 86328 | EBV-B95-8 | 87104 | 87133 |
| EBV-B95-8 | 89959 | 89988 | EBV-B95-8 | 90915 | 90944 | EBV-B95-8 | 92531 | 92560 |
| EBV-B95-8 | 94071 | 94100 | EBV-B95-8 | 94731 | 94760 | EBV-B95-8 | 95084 | 95113 |
| EBV-B95-8 | 97482 | 97511 | EBV-B95-8 | 98245 | 98274 | EBV-B95-8 | 99224 | 99253 |
| EBV-B95-8 | 100235 | 100264 | EBV-B95-8 | 101009 | 101038 | EBV-B95-8 | 102716 | 102745 |
| EBV-B95-8 | 104004 | 104033 | EBV-B95-8 | 105019 | 105048 | EBV-B95-8 | 105284 | 105313 |
| EBV-B95-8 | 107231 | 107260 | EBV-B95-8 | 108023 | 108052 | EBV-B95-8 | 108370 | 108399 |
| EBV-B95-8 | 109086 | 109115 | EBV-B95-8 | 110250 | 110279 | EBV-B95-8 | 110626 | 110655 |
| EBV-B95-8 | 111690 | 111719 | EBV-B95-8 | 112112 | 112141 | EBV-B95-8 | 114429 | 114458 |
| EBV-B95-8 | 114749 | 114778 | EBV-B95-8 | 115006 | 115035 | EBV-B95-8 | 115597 | 115626 |
| EBV-B95-8 | 116382 | 116411 | EBV-B95-8 | 116649 | 116678 | EBV-B95-8 | 118647 | 118676 |
| EBV-B95-8 | 119542 | 119571 | EBV-B95-8 | 120350 | 120379 | EBV-B95-8 | 121382 | 121411 |
| EBV-B95-8 | 123037 | 123066 | EBV-B95-8 | 123570 | 123599 | EBV-B95-8 | 124913 | 124942 |
| EBV-B95-8 | 125376 | 125405 | EBV-B95-8 | 125805 | 125834 | EBV-B95-8 | 126337 | 126366 |
| EBV-B95-8 | 127493 | 127522 | EBV-B95-8 | 127905 | 127934 | EBV-B95-8 | 128805 | 128834 |
| EBV-B95-8 | 130244 | 130273 | EBV-B95-8 | 130690 | 130719 | EBV-B95-8 | 131603 | 131632 |
| EBV-B95-8 | 134325 | 134354 | EBV-B95-8 | 135032 | 135061 | EBV-B95-8 | 135599 | 135628 |
| EBV-B95-8 | 136148 | 136177 | EBV-B95-8 | 136680 | 136709 | EBV-B95-8 | 137805 | 137834 |
| EBV-B95-8 | 138375 | 138404 | EBV-B95-8 | 139745 | 139774 | EBV-B95-8 | 140610 | 140639 |
| EBV-B95-8 | 141137 | 141166 | EBV-B95-8 | 142290 | 142319 | EBV-B95-8 | 142763 | 142792 |
| EBV-B95-8 | 143078 | 143107 | EBV-B95-8 | 144318 | 144347 | EBV-B95-8 | 145216 | 145245 |
| EBV-B95-8 | 145638 | 145667 | EBV-B95-8 | 147044 | 147073 | EBV-B95-8 | 148404 | 148433 |
| EBV-B95-8 | 150099 | 150128 | EBV-B95-8 | 150443 | 150472 | EBV-B95-8 | 152230 | 152259 |
| EBV-B95-8 | 153127 | 153156 | EBV-B95-8 | 153468 | 153497 | EBV-B95-8 | 153800 | 153829 |
| EBV-B95-8 | 154204 | 154233 | EBV-B95-8 | 156501 | 156530 | EBV-B95-8 | 156773 | 156802 |
| EBV-B95-8 | 157345 | 157374 | EBV-B95-8 | 159211 | 159240 | EBV-B95-8 | 159561 | 159590 |
| EBV-B95-8 | 161193 | 161222 | EBV-B95-8 | 161698 | 161727 | EBV-B95-8 | 162343 | 162372 |
| EBV-B95-8 | 163798 | 163827 | EBV-B95-8 | 164471 | 164500 | EBV-B95-8 | 165234 | 165263 |
| EBV-B95-8 | 166280 | 166309 | EBV-B95-8 | 167347 | 167376 | EBV-B95-8 | 167600 | 167629 |
| EBV-B95-8 | 167942 | 167971 | EBV-B95-8 | 168551 | 168580 | EBV-B95-8 | 171304 | 171333 |
| GL000225.1 | 37720 | 37842 | GL000231.1 | 12576 | 12717 | HBV | 111 | 140 |
| HBV | 381 | 410 | HBV | 651 | 680 | HBV | 921 | 950 |
| HBV | 1191 | 1220 | HBV | 1461 | 1490 | HBV | 1731 | 1760 |
| HBV | 2001 | 2030 | HBV | 2271 | 2300 | HBV | 2541 | 2570 |
| HBV | 2811 | 2840 | HCMV-AD169 | 17724 | 17753 | HCMV-AD169 | 18691 | 18720 |
| HCMV-AD169 | 23851 | 23880 | HCMV-AD169 | 27296 | 27325 | HCMV-AD169 | 42909 | 42938 |
| HCMV-AD169 | 57909 | 57938 | HCMV-AD169 | 68427 | 68456 | HCMV-AD169 | 76862 | 76891 |
| HCMV-AD169 | 78956 | 78985 | HCMV-AD169 | 81188 | 81217 | HCMV-AD169 | 84448 | 84477 |
| HCMV-AD169 | 88920 | 88949 | HCMV-AD169 | 99889 | 99918 | HCMV-AD169 | 101238 | 101267 |
| HCMV-AD169 | 108021 | 108050 | HCMV-AD169 | 114824 | 114853 | HCMV-AD169 | 128011 | 128040 |
| HCMV-AD169 | 129567 | 129596 | HCMV-AD169 | 149187 | 149216 | HCMV-AD169 | 162299 | 162328 |
| HCMV-AD169 | 169250 | 169279 | HCMV-AD169 | 171221 | 171250 | HCMV-AD169 | 172561 | 172590 |
| HCMV-AD169 | 177053 | 177082 | HCMV-AD169 | 193060 | 193089 | HCMV-AD169 | 193858 | 193887 |
| HCMV-AD169 | 194176 | 194205 | HCMV-AD169 | 195222 | 195251 | HCMV-AD169 | 196060 | 196089 |
| HCMV-AD169 | 196817 | 196846 | HCMV-AD169 | 199152 | 199181 | HCMV-AD169 | 199906 | 199935 |
| HCMV-AD169 | 201145 | 201174 | HCMV-AD169 | 204433 | 204462 | HCMV-AD169 | 207682 | 207711 |
| HCMV-AD169 | 209510 | 209539 | HCMV-AD169 | 210069 | 210098 | HCMV-AD169 | 212133 | 212162 |
| HCMV-AD169 | 212591 | 212620 | HCMV-AD169 | 214453 | 214482 | HCMV-AD169 | 220316 | 220345 |
| HCV | 111 | 140 | HCV | 374 | 403 | HCV | 637 | 666 |
| HCV | 900 | 929 | HCV | 1163 | 1192 | HCV | 1426 | 1455 |
| HCV | 1689 | 1718 | HCV | 1952 | 1981 | HCV | 2215 | 2244 |
| HCV | 2478 | 2507 | HCV | 2741 | 2770 | HCV | 3004 | 3033 |
| HCV | 3267 | 3296 | HCV | 3530 | 3559 | HCV | 3793 | 3822 |
| HCV | 4056 | 4085 | HCV | 4319 | 4348 | HCV | 4582 | 4611 |
| HCV | 4845 | 4874 | HCV | 5108 | 5137 | HCV | 5371 | 5400 |
| HCV | 5634 | 5663 | HCV | 5897 | 5926 | HCV | 6160 | 6189 |
| HCV | 6423 | 6452 | HCV | 6686 | 6715 | HCV | 6949 | 6978 |
| HCV | 7212 | 7241 | HCV | 7475 | 7504 | HCV | 7738 | 7767 |
| HCV | 8001 | 8030 | HCV | 8264 | 8293 | HCV | 8527 | 8556 |
| HCV | 8790 | 8819 | HCV | 9053 | 9082 | HHV5-CINCY-TOWNE | 1181 | 1210 |
| HHV5-CINCY-TOWNE | 1988 | 2017 | HHV5-CINCY-TOWNE | 2389 | 2418 | HHV5-CINCY-TOWNE | 3290 | 3319 |
| HHV5-CINCY-TOWNE | 3665 | 3694 | HHV5-CINCY-TOWNE | 4704 | 4733 | HHV5-CINCY-TOWNE | 5400 | 5429 |
| HHV5-CINCY-TOWNE | 7790 | 7819 | HHV5-CINCY-TOWNE | 9656 | 9685 | HHV5-CINCY-TOWNE | 10781 | 10810 |
| HHV5-CINCY-TOWNE | 11109 | 11138 | HHV5-CINCY-TOWNE | 12663 | 12692 | HHV5-CINCY-TOWNE | 13688 | 13717 |
| HHV5-CINCY-TOWNE | 14223 | 14252 | HHV5-CINCY-TOWNE | 14911 | 14940 | HHV5-CINCY-TOWNE | 15206 | 15235 |
| HHV5-CINCY-TOWNE | 15938 | 15967 | HHV5-CINCY-TOWNE | 16440 | 16469 | HHV5-CINCY-TOWNE | 16884 | 16913 |
| HHV5-CINCY-TOWNE | 17347 | 17376 | HHV5-CINCY-TOWNE | 17696 | 17725 | HHV5-CINCY-TOWNE | 17958 | 17987 |
| HHV5-CINCY-TOWNE | 18372 | 18401 | HHV5-CINCY-TOWNE | 19417 | 19446 | HHV5-CINCY-TOWNE | 19910 | 19939 |
| HHV5-CINCY-TOWNE | 20248 | 20277 | HHV5-CINCY-TOWNE | 20671 | 20700 | HHV5-CINCY-TOWNE | 21899 | 21928 |
| HHV5-CINCY-TOWNE | 22798 | 22827 | HHV5-CINCY-TOWNE | 23095 | 23124 | HHV5-CINCY-TOWNE | 26713 | 26742 |
| HHV5-CINCY-TOWNE | 27211 | 27240 | HHV5-CINCY-TOWNE | 29784 | 29813 | HHV5-CINCY-TOWNE | 31141 | 31170 |
| HHV5-CINCY-TOWNE | 32660 | 32689 | HHV5-CINCY-TOWNE | 35651 | 35680 | HHV5-CINCY-TOWNE | 36393 | 36422 |
| HHV5-CINCY-TOWNE | 37224 | 37253 | HHV5-CINCY-TOWNE | 37895 | 37924 | HHV5-CINCY-TOWNE | 39244 | 39273 |
| HHV5-CINCY-TOWNE | 43188 | 43217 | HHV5-CINCY-TOWNE | 44447 | 44476 | HHV5-CINCY-TOWNE | 44799 | 44828 |
| HHV5-CINCY-TOWNE | 45394 | 45423 | HHV5-CINCY-TOWNE | 46445 | 46474 | HHV5-CINCY-TOWNE | 46944 | 46973 |
| HHV5-CINCY-TOWNE | 47916 | 47945 | HHV5-CINCY-TOWNE | 48504 | 48533 | HHV5-CINCY-TOWNE | 49094 | 49123 |

TABLE 12-continued

Pan Cancer #2

| chr | start | end | chr | start | end | chr | start | end |
|---|---|---|---|---|---|---|---|---|
| HHV5-CINCY-TOWNE | 49903 | 49932 | HHV5-CINCY-TOWNE | 50230 | 50259 | HHV5-CINCY-TOWNE | 51421 | 51450 |
| HHV5-CINCY-TOWNE | 53772 | 53801 | HHV5-CINCY-TOWNE | 55651 | 55680 | HHV5-CINCY-TOWNE | 56380 | 56409 |
| HHV5-CINCY-TOWNE | 57291 | 57320 | HHV5-CINCY-TOWNE | 58491 | 58520 | HHV5-CINCY-TOWNE | 59023 | 59052 |
| HHV5-CINCY-TOWNE | 59792 | 59821 | HHV5-CINCY-TOWNE | 60124 | 60153 | HHV5-CINCY-TOWNE | 60392 | 60421 |
| HHV5-CINCY-TOWNE | 60900 | 60929 | HHV5-CINCY-TOWNE | 63894 | 63923 | HHV5-CINCY-TOWNE | 65843 | 65872 |
| HHV5-CINCY-TOWNE | 68089 | 68118 | HHV5-CINCY-TOWNE | 72454 | 72483 | HHV5-CINCY-TOWNE | 81185 | 81214 |
| HHV5-CINCY-TOWNE | 84144 | 84173 | HHV5-CINCY-TOWNE | 85524 | 85553 | HHV5-CINCY-TOWNE | 85943 | 85972 |
| HHV5-CINCY-TOWNE | 86889 | 86918 | HHV5-CINCY-TOWNE | 87195 | 87224 | HHV5-CINCY-TOWNE | 87455 | 87484 |
| HHV5-CINCY-TOWNE | 87769 | 87798 | HHV5-CINCY-TOWNE | 88564 | 88593 | HHV5-CINCY-TOWNE | 93096 | 93125 |
| HHV5-CINCY-TOWNE | 93776 | 93805 | HHV5-CINCY-TOWNE | 97621 | 97650 | HHV5-CINCY-TOWNE | 98737 | 98766 |
| HHV5-CINCY-TOWNE | 99460 | 99489 | HHV5-CINCY-TOWNE | 107540 | 107569 | HHV5-CINCY-TOWNE | 108823 | 108852 |
| HHV5-CINCY-TOWNE | 109725 | 109754 | HHV5-CINCY-TOWNE | 112036 | 112065 | HHV5-CINCY-TOWNE | 112319 | 112348 |
| HHV5-CINCY-TOWNE | 112595 | 112624 | HHV5-CINCY-TOWNE | 112892 | 112921 | HHV5-CINCY-TOWNE | 113194 | 113223 |
| HHV5-CINCY-TOWNE | 113535 | 113564 | HHV5-CINCY-TOWNE | 113927 | 113956 | HHV5-CINCY-TOWNE | 114267 | 114296 |
| HHV5-CINCY-TOWNE | 114593 | 114622 | HHV5-CINCY-TOWNE | 114867 | 114896 | HHV5-CINCY-TOWNE | 115177 | 115206 |
| HHV5-CINCY-TOWNE | 115432 | 115461 | HHV5-CINCY-TOWNE | 115685 | 115714 | HHV5-CINCY-TOWNE | 115986 | 116015 |
| HHV5-CINCY-TOWNE | 116382 | 116411 | HHV5-CINCY-TOWNE | 116700 | 116729 | HHV5-CINCY-TOWNE | 118193 | 118222 |
| HHV5-CINCY-TOWNE | 118995 | 119024 | HHV5-CINCY-TOWNE | 120028 | 120057 | HHV5-CINCY-TOWNE | 121485 | 121514 |
| HHV5-CINCY-TOWNE | 122199 | 122228 | HHV5-CINCY-TOWNE | 122606 | 122635 | HHV5-CINCY-TOWNE | 124559 | 124588 |
| HHV5-CINCY-TOWNE | 125276 | 125305 | HHV5-CINCY-TOWNE | 132497 | 132526 | HHV5-CINCY-TOWNE | 135460 | 135489 |
| HHV5-CINCY-TOWNE | 135730 | 135759 | HHV5-CINCY-TOWNE | 137379 | 137408 | HHV5-CINCY-TOWNE | 139067 | 139096 |
| HHV5-CINCY-TOWNE | 139472 | 139501 | HHV5-CINCY-TOWNE | 140147 | 140176 | HHV5-CINCY-TOWNE | 140722 | 140751 |
| HHV5-CINCY-TOWNE | 142023 | 142052 | HHV5-CINCY-TOWNE | 143692 | 143721 | HHV5-CINCY-TOWNE | 144080 | 144109 |
| HHV5-CINCY-TOWNE | 147310 | 147339 | HHV5-CINCY-TOWNE | 149465 | 149494 | HHV5-CINCY-TOWNE | 150359 | 150388 |
| HHV5-CINCY-TOWNE | 151593 | 151622 | HHV5-CINCY-TOWNE | 152153 | 152182 | HHV5-CINCY-TOWNE | 154148 | 154177 |
| HHV5-CINCY-TOWNE | 154610 | 154639 | HHV5-CINCY-TOWNE | 157018 | 157047 | HHV5-CINCY-TOWNE | 157367 | 157396 |
| HHV5-CINCY-TOWNE | 169038 | 169067 | HHV5-CINCY-TOWNE | 171503 | 171532 | HHV5-CINCY-TOWNE | 175146 | 175175 |
| HHV5-CINCY-TOWNE | 177553 | 177582 | HHV5-CINCY-TOWNE | 182254 | 182283 | HHV5-CINCY-TOWNE | 183115 | 183144 |
| HHV5-CINCY-TOWNE | 184120 | 184149 | HHV5-CINCY-TOWNE | 185558 | 185587 | HHV5-CINCY-TOWNE | 186027 | 186056 |
| HHV5-CINCY-TOWNE | 186435 | 186464 | HHV5-CINCY-TOWNE | 186707 | 186736 | HHV5-CINCY-TOWNE | 187115 | 187144 |
| HHV5-CINCY-TOWNE | 187514 | 187543 | HHV5-CINCY-TOWNE | 187859 | 187888 | HHV5-CINCY-TOWNE | 188473 | 188502 |
| HHV5-CINCY-TOWNE | 188768 | 188797 | HHV5-CINCY-TOWNE | 189050 | 189079 | HHV5-CINCY-TOWNE | 189302 | 189331 |
| HHV5-CINCY-TOWNE | 189936 | 189965 | HHV5-CINCY-TOWNE | 190655 | 190684 | HHV5-CINCY-TOWNE | 190954 | 190983 |
| HHV5-CINCY-TOWNE | 191453 | 191482 | HHV5-CINCY-TOWNE | 191882 | 191911 | HHV5-CINCY-TOWNE | 192183 | 192212 |
| HHV5-CINCY-TOWNE | 192541 | 192570 | HHV5-CINCY-TOWNE | 193045 | 193074 | HHV5-CINCY-TOWNE | 193325 | 193354 |
| HHV5-CINCY-TOWNE | 193597 | 193626 | HHV5-CINCY-TOWNE | 194165 | 194194 | HHV5-CINCY-TOWNE | 194461 | 194490 |
| HHV5-CINCY-TOWNE | 194848 | 194877 | HHV5-CINCY-TOWNE | 195324 | 195353 | HHV5-CINCY-TOWNE | 195651 | 195680 |
| HHV5-CINCY-TOWNE | 196018 | 196047 | HHV5-CINCY-TOWNE | 196343 | 196372 | HHV5-CINCY-TOWNE | 196941 | 196970 |
| HHV5-CINCY-TOWNE | 197218 | 197247 | HHV5-CINCY-TOWNE | 198315 | 198344 | HHV5-CINCY-TOWNE | 198792 | 198821 |
| HHV5-CINCY-TOWNE | 199162 | 199191 | HHV5-CINCY-TOWNE | 200113 | 200142 | HHV5-CINCY-TOWNE | 200571 | 200600 |
| HHV5-CINCY-TOWNE | 201373 | 201402 | HHV5-CINCY-TOWNE | 201905 | 201934 | HHV5-CINCY-TOWNE | 202264 | 202293 |
| HHV5-CINCY-TOWNE | 202537 | 202566 | HHV5-CINCY-TOWNE | 203319 | 203348 | HHV5-CINCY-TOWNE | 203720 | 203749 |
| HHV5-CINCY-TOWNE | 204008 | 204037 | HHV5-CINCY-TOWNE | 206213 | 206242 | HHV5-CINCY-TOWNE | 206735 | 206764 |
| HHV5-CINCY-TOWNE | 211676 | 211705 | HHV5-CINCY-TOWNE | 212340 | 212369 | HHV5-CINCY-TOWNE | 212609 | 212638 |
| HHV5-CINCY-TOWNE | 213813 | 213842 | HHV5-CINCY-TOWNE | 214695 | 214724 | HHV5-CINCY-TOWNE | 214950 | 214979 |
| HHV5-CINCY-TOWNE | 215930 | 215959 | HHV5-CINCY-TOWNE | 216228 | 216257 | HHV5-CINCY-TOWNE | 222672 | 222701 |
| HHV5-CINCY-TOWNE | 223515 | 223544 | HHV5-CINCY-TOWNE | 225150 | 225179 | HHV5-CINCY-TOWNE | 226058 | 226087 |
| HHV5-CINCY-TOWNE | 226887 | 226916 | HPV16 | 111 | 140 | HPV16 | 367 | 396 |
| HPV16 | 623 | 652 | HPV16 | 879 | 908 | HPV16 | 1135 | 1164 |
| HPV16 | 1391 | 1420 | HPV16 | 1647 | 1676 | HPV16 | 1903 | 1932 |
| HPV16 | 2159 | 2188 | HPV16 | 2415 | 2444 | HPV16 | 2671 | 2700 |
| HPV16 | 2927 | 2956 | HPV16 | 3183 | 3212 | HPV16 | 3439 | 3468 |
| HPV16 | 3695 | 3724 | HPV16 | 3951 | 3980 | HPV16 | 4207 | 4236 |
| HPV16 | 4463 | 4492 | HPV16 | 4719 | 4748 | HPV16 | 4975 | 5004 |
| HPV16 | 5231 | 5260 | HPV16 | 5487 | 5516 | HPV16 | 5743 | 5772 |
| HPV16 | 5999 | 6028 | HPV16 | 6255 | 6284 | HPV16 | 6511 | 6540 |
| HPV16 | 6767 | 6796 | HPV16 | 7023 | 7052 | HPV16 | 7279 | 7308 |
| HPV16 | 7535 | 7564 | HPV18 | 111 | 140 | HPV18 | 383 | 412 |
| HPV18 | 655 | 684 | HPV18 | 927 | 956 | HPV18 | 1199 | 1228 |
| HPV18 | 1471 | 1500 | HPV18 | 1743 | 1772 | HPV18 | 2015 | 2044 |
| HPV18 | 2287 | 2316 | HPV18 | 2559 | 2588 | HPV18 | 2831 | 2860 |
| HPV18 | 3103 | 3132 | HPV18 | 3375 | 3404 | HPV18 | 3647 | 3676 |
| HPV18 | 3919 | 3948 | HPV18 | 4191 | 4220 | HPV18 | 4463 | 4492 |
| HPV18 | 4735 | 4764 | HPV18 | 5007 | 5036 | HPV18 | 5279 | 5308 |
| HPV18 | 5551 | 5580 | HPV18 | 5823 | 5852 | HPV18 | 6095 | 6124 |
| HPV18 | 6367 | 6396 | HPV18 | 6639 | 6668 | HPV18 | 6911 | 6940 |
| HPV18 | 7183 | 7212 | HPV18 | 7455 | 7484 | | | |

TABLE 13

Pan Cancer #3

| chr | start | end | chr | start | end | chr | start | end |
|---|---|---|---|---|---|---|---|---|
| chr1 | 898654 | 898690 | chr1 | 913532 | 913955 | chr1 | 1047531 | 1047619 |
| chr1 | 1080583 | 1080824 | chr1 | 1146734 | 1146818 | chr1 | 1218737 | 1218779 |
| chr1 | 1223512 | 1223612 | chr1 | 1235813 | 1236078 | chr1 | 1267014 | 1267151 |
| chr1 | 1267462 | 1267699 | chr1 | 1267906 | 1268158 | chr1 | 1281214 | 1281244 |
| chr1 | 1341706 | 1341743 | chr1 | 1473125 | 1473207 | chr1 | 1475556 | 1475643 |
| chr1 | 1476255 | 1476318 | chr1 | 1483186 | 1483363 | chr1 | 1563193 | 1563223 |
| chr1 | 1688882 | 1689012 | chr1 | 1805049 | 1805069 | chr1 | 1856436 | 1856466 |
| chr1 | 1857847 | 1857909 | chr1 | 1874744 | 1874787 | chr1 | 1910415 | 1910445 |
| chr1 | 1923489 | 1923521 | chr1 | 1935274 | 1935459 | chr1 | 1974848 | 1974925 |
| chr1 | 2066490 | 2066679 | chr1 | 2125216 | 2125483 | chr1 | 2165895 | 2165999 |
| chr1 | 2263169 | 2263263 | chr1 | 2267552 | 2267690 | chr1 | 2304327 | 2304389 |
| chr1 | 2307925 | 2307955 | chr1 | 2308376 | 2308636 | chr1 | 2309868 | 2309953 |
| chr1 | 2331363 | 2331437 | chr1 | 2336397 | 2336427 | chr1 | 2375148 | 2375543 |
| chr1 | 2397001 | 2397031 | chr1 | 2428331 | 2428385 | chr1 | 2472174 | 2472301 |
| chr1 | 2507063 | 2507183 | chr1 | 2514330 | 2514353 | chr1 | 2521024 | 2521063 |
| chr1 | 2706308 | 2706334 | chr1 | 2830155 | 2830185 | chr1 | 2866038 | 2866068 |
| chr1 | 2984719 | 2984749 | chr1 | 3102653 | 3102779 | chr1 | 3158823 | 3158962 |
| chr1 | 3182883 | 3182917 | chr1 | 3322090 | 3322170 | chr1 | 3567093 | 3567344 |
| chr1 | 3567738 | 3567850 | chr1 | 3567883 | 3568226 | chr1 | 3601850 | 3601946 |
| chr1 | 3607081 | 3607236 | chr1 | 3659550 | 3659642 | chr1 | 3659672 | 3659716 |
| chr1 | 3663532 | 3663562 | chr1 | 3663874 | 3663921 | chr1 | 3664481 | 3664741 |
| chr1 | 3683722 | 3683818 | chr1 | 3700384 | 3700414 | chr1 | 3733551 | 3733581 |
| chr1 | 4111086 | 4111231 | chr1 | 4401433 | 4401463 | chr1 | 4714018 | 4714074 |
| chr1 | 4714164 | 4714345 | chr1 | 4715428 | 4715539 | chr1 | 4715575 | 4716701 |
| chr1 | 5919973 | 5920071 | chr1 | 5920650 | 5920710 | chr1 | 5924296 | 5924431 |
| chr1 | 5924851 | 5924984 | chr1 | 5926596 | 5926645 | chr1 | 5933086 | 5933144 |
| chr1 | 5934925 | 5935061 | chr1 | 5940517 | 5940547 | chr1 | 5940945 | 5941132 |
| chr1 | 5944299 | 5944449 | chr1 | 5945348 | 5945435 | chr1 | 5947258 | 5947288 |
| chr1 | 5949491 | 5949575 | chr1 | 5950965 | 5951039 | chr1 | 5957473 | 5957503 |
| chr1 | 5967237 | 5967267 | chr1 | 5969001 | 5969283 | chr1 | 5972104 | 5972134 |
| chr1 | 5972878 | 5972922 | chr1 | 6021621 | 6021651 | chr1 | 6025872 | 6025950 |
| chr1 | 6036766 | 6036796 | chr1 | 6056157 | 6056201 | chr1 | 6056506 | 6056651 |
| chr1 | 6059910 | 6059974 | chr1 | 6166353 | 6166469 | chr1 | 6171763 | 6171810 |
| chr1 | 6186511 | 6186546 | chr1 | 6280243 | 6280273 | chr1 | 6284828 | 6284858 |
| chr1 | 6304201 | 6304242 | chr1 | 6360593 | 6360634 | chr1 | 6410456 | 6410486 |
| chr1 | 6446131 | 6446308 | chr1 | 6480514 | 6480831 | chr1 | 6501055 | 6501179 |
| chr1 | 6507678 | 6508126 | chr1 | 6713914 | 6714041 | chr1 | 6714348 | 6714378 |
| chr1 | 7764641 | 7764737 | chr1 | 8085685 | 8085715 | chr1 | 9324231 | 9324274 |
| chr1 | 9402465 | 9402616 | chr1 | 9527172 | 9527208 | chr1 | 9712074 | 9712104 |
| chr1 | 9712561 | 9713014 | chr1 | 9795995 | 9796196 | chr1 | 9867157 | 9867316 |
| chr1 | 10091888 | 10091914 | chr1 | 10166521 | 10166551 | chr1 | 10948552 | 10948582 |
| chr1 | 11169346 | 11169375 | chr1 | 11174404 | 11174433 | chr1 | 11181358 | 11181432 |
| chr1 | 11182142 | 11182171 | chr1 | 11188149 | 11188178 | chr1 | 11210182 | 11210211 |
| chr1 | 11217215 | 11217337 | chr1 | 11249032 | 11249061 | chr1 | 11538705 | 11538821 |
| chr1 | 11539175 | 11539205 | chr1 | 11539410 | 11539440 | chr1 | 11540129 | 11540178 |
| chr1 | 11591719 | 11591826 | chr1 | 11752476 | 11752511 | chr1 | 11886250 | 11886280 |
| chr1 | 11936748 | 11936778 | chr1 | 11959093 | 11959196 | chr1 | 12041510 | 12041525 |
| chr1 | 12123243 | 12123553 | chr1 | 12227685 | 12227941 | chr1 | 12251443 | 12251958 |
| chr1 | 12460299 | 12460356 | chr1 | 13910436 | 13910714 | chr1 | 14026481 | 14026618 |
| chr1 | 14097878 | 14097977 | chr1 | 14128478 | 14128588 | chr1 | 14149749 | 14149867 |
| chr1 | 14730425 | 14730472 | chr1 | 14925501 | 14926050 | chr1 | 15128565 | 15128595 |
| chr1 | 15251120 | 15251211 | chr1 | 15480593 | 15480892 | chr1 | 16475031 | 16475207 |
| chr1 | 16861522 | 16861552 | chr1 | 17445857 | 17445943 | chr1 | 18437457 | 18437526 |
| chr1 | 18956211 | 18956304 | chr1 | 18956574 | 18956610 | chr1 | 18956856 | 18957246 |
| chr1 | 18957507 | 18957587 | chr1 | 18958033 | 18958228 | chr1 | 18958359 | 18958381 |
| chr1 | 18959456 | 18959550 | chr1 | 18960897 | 18960990 | chr1 | 18962727 | 18963135 |
| chr1 | 18969625 | 18969819 | chr1 | 18971852 | 18971929 | chr1 | 18972130 | 18972160 |
| chr1 | 19043563 | 19043678 | chr1 | 19992418 | 19992432 | chr1 | 20127435 | 20127471 |
| chr1 | 20248109 | 20248141 | chr1 | 20618329 | 20618369 | chr1 | 20693317 | 20693420 |
| chr1 | 20879035 | 20879228 | chr1 | 20879256 | 20879289 | chr1 | 20879562 | 20879640 |
| chr1 | 20879845 | 20879957 | chr1 | 20880182 | 20880605 | chr1 | 21026117 | 21026225 |
| chr1 | 21042894 | 21042924 | chr1 | 21044125 | 21044161 | chr1 | 21050471 | 21050511 |
| chr1 | 21058635 | 21058776 | chr1 | 21573668 | 21574203 | chr1 | 21835943 | 21836007 |
| chr1 | 22140753 | 22141184 | chr1 | 22141326 | 22141355 | chr1 | 22222711 | 22222793 |
| chr1 | 22927410 | 22927482 | chr1 | 23748982 | 23749070 | chr1 | 23885070 | 23885100 |
| chr1 | 25255921 | 25255934 | chr1 | 25256354 | 25256383 | chr1 | 25257157 | 25257205 |
| chr1 | 25257490 | 25257529 | chr1 | 25257532 | 25257561 | chr1 | 25257916 | 25258250 |
| chr1 | 25919307 | 25919337 | chr1 | 26467523 | 26467547 | chr1 | 26551729 | 26551796 |
| chr1 | 26552086 | 26552130 | chr1 | 26737583 | 26737613 | chr1 | 26737946 | 26738182 |
| chr1 | 26917724 | 26917740 | chr1 | 27190175 | 27190278 | chr1 | 27332448 | 27332673 |
| chr1 | 27844518 | 27844548 | chr1 | 29048601 | 29048643 | chr1 | 29450491 | 29450543 |
| chr1 | 29586072 | 29586674 | chr1 | 29804947 | 29805094 | chr1 | 30351554 | 30351742 |
| chr1 | 30815412 | 30815416 | chr1 | 30815455 | 30815578 | chr1 | 31863186 | 31863216 |
| chr1 | 32180397 | 32180427 | chr1 | 32237639 | 32238507 | chr1 | 32410276 | 32410306 |
| chr1 | 32410519 | 32410614 | chr1 | 32705488 | 32705550 | chr1 | 32756498 | 32756540 |
| chr1 | 32930458 | 32930558 | chr1 | 32938720 | 32938750 | chr1 | 33219567 | 33219596 |

TABLE 13-continued

Pan Cancer #3

| chr | start | end | chr | start | end | chr | start | end |
|---|---|---|---|---|---|---|---|---|
| chr1 | 34628948 | 34628978 | chr1 | 34629469 | 34629728 | chr1 | 34630548 | 34630635 |
| chr1 | 34630859 | 34630978 | chr1 | 34631580 | 34631662 | chr1 | 34631933 | 34631963 |
| chr1 | 34642380 | 34642489 | chr1 | 35258637 | 35258714 | chr1 | 35351078 | 35351659 |
| chr1 | 35395526 | 35395851 | chr1 | 35664716 | 35664746 | chr1 | 36042679 | 36043489 |
| chr1 | 36563479 | 36563522 | chr1 | 36849009 | 36849038 | chr1 | 37498792 | 37498844 |
| chr1 | 37498889 | 37499181 | chr1 | 37499460 | 37499682 | chr1 | 37500014 | 37500153 |
| chr1 | 37500468 | 37500574 | chr1 | 37500603 | 37500806 | chr1 | 37501072 | 37501102 |
| chr1 | 38100689 | 38100851 | chr1 | 38219712 | 38219795 | chr1 | 38230042 | 38230242 |
| chr1 | 38230283 | 38230297 | chr1 | 38230779 | 38230859 | chr1 | 38398311 | 38398348 |
| chr1 | 38412504 | 38412832 | chr1 | 38510178 | 38510217 | chr1 | 38510563 | 38510624 |
| chr1 | 38510854 | 38511119 | chr1 | 38511337 | 38511799 | chr1 | 38511822 | 38511824 |
| chr1 | 38512385 | 38512415 | chr1 | 38513244 | 38513318 | chr1 | 39269741 | 39270121 |
| chr1 | 40137898 | 40137984 | chr1 | 40237141 | 40237203 | chr1 | 40349626 | 40349647 |
| chr1 | 40708443 | 40708481 | chr1 | 40915590 | 40915620 | chr1 | 41283958 | 41284463 |
| chr1 | 41847583 | 41847702 | chr1 | 41848810 | 41848840 | chr1 | 41915253 | 41915283 |
| chr1 | 41967342 | 41967418 | chr1 | 41991640 | 41991702 | chr1 | 43400336 | 43400386 |
| chr1 | 43814994 | 43815023 | chr1 | 43834741 | 43834832 | chr1 | 43842664 | 43842679 |
| chr1 | 44068774 | 44068804 | chr1 | 44494137 | 44494153 | chr1 | 44726912 | 44727268 |
| chr1 | 44872448 | 44872722 | chr1 | 44872924 | 44873172 | chr1 | 44873510 | 44873706 |
| chr1 | 44883121 | 44883214 | chr1 | 44883752 | 44884122 | chr1 | 45308238 | 45308262 |
| chr1 | 45308592 | 45308625 | chr1 | 46632876 | 46632923 | chr1 | 46744657 | 46744733 |
| chr1 | 46913837 | 46913876 | chr1 | 46913887 | 46914245 | chr1 | 46914656 | 46914686 |
| chr1 | 46932765 | 46932905 | chr1 | 46951207 | 46951317 | chr1 | 46951645 | 46951739 |
| chr1 | 46956454 | 46956603 | chr1 | 46956823 | 46957171 | chr1 | 47009929 | 47010035 |
| chr1 | 47035373 | 47035403 | chr1 | 47078736 | 47078782 | chr1 | 47695122 | 47695422 |
| chr1 | 47696295 | 47696520 | chr1 | 47696821 | 47696964 | chr1 | 47696987 | 47697110 |
| chr1 | 47697356 | 47697510 | chr1 | 47697732 | 47697946 | chr1 | 47698007 | 47698210 |
| chr1 | 47788328 | 47788348 | chr1 | 47882063 | 47882322 | chr1 | 47882769 | 47882803 |
| chr1 | 47909718 | 47910160 | chr1 | 47910523 | 47910624 | chr1 | 47910749 | 47910914 |
| chr1 | 47911424 | 47911508 | chr1 | 47999050 | 47999163 | chr1 | 48059078 | 48059243 |
| chr1 | 49242344 | 49242533 | chr1 | 50513629 | 50513745 | chr1 | 50799278 | 50799316 |
| chr1 | 50799394 | 50799400 | chr1 | 50880932 | 50881302 | chr1 | 50881427 | 50881956 |
| chr1 | 50882144 | 50882529 | chr1 | 50882808 | 50883611 | chr1 | 50883882 | 50883976 |
| chr1 | 50884021 | 50884352 | chr1 | 50884691 | 50884887 | chr1 | 50885336 | 50885366 |
| chr1 | 50886188 | 50887084 | chr1 | 50887176 | 50887284 | chr1 | 50888709 | 50888795 |
| chr1 | 50889124 | 50889510 | chr1 | 50889820 | 50890379 | chr1 | 50890796 | 50891595 |
| chr1 | 50892153 | 50892283 | chr1 | 50892337 | 50892351 | chr1 | 50892607 | 50893422 |
| chr1 | 50893519 | 50893877 | chr1 | 51763252 | 51763298 | chr1 | 52832687 | 52832724 |
| chr1 | 53019468 | 53019568 | chr1 | 53068166 | 53068546 | chr1 | 53098842 | 53099067 |
| chr1 | 53192045 | 53192075 | chr1 | 53308568 | 53308607 | chr1 | 53308908 | 53309248 |
| chr1 | 53528374 | 53528439 | chr1 | 53705674 | 53705701 | chr1 | 54203829 | 54204399 |
| chr1 | 54586626 | 54586736 | chr1 | 54837089 | 54837119 | chr1 | 55462673 | 55462703 |
| chr1 | 57888367 | 57888397 | chr1 | 57888987 | 57889087 | chr1 | 57889402 | 57889654 |
| chr1 | 57890431 | 57890650 | chr1 | 58715153 | 58715194 | chr1 | 58715475 | 58715854 |
| chr1 | 58715979 | 58715993 | chr1 | 61519360 | 61519394 | chr1 | 62660740 | 62660768 |
| chr1 | 62660786 | 62660861 | chr1 | 62793237 | 62793267 | chr1 | 63539509 | 63539887 |
| chr1 | 63785619 | 63785766 | chr1 | 63786079 | 63786329 | chr1 | 63787031 | 63787063 |
| chr1 | 63787302 | 63787568 | chr1 | 63788423 | 63788557 | chr1 | 63788920 | 63789496 |
| chr1 | 63789729 | 63789791 | chr1 | 63789850 | 63789912 | chr1 | 63790253 | 63790278 |
| chr1 | 63792561 | 63792648 | chr1 | 63792798 | 63793072 | chr1 | 63795263 | 63796277 |
| chr1 | 63796498 | 63796575 | chr1 | 64240026 | 64240118 | chr1 | 64240617 | 64240673 |
| chr1 | 64734652 | 64734673 | chr1 | 64937330 | 64937542 | chr1 | 65303636 | 65303692 |
| chr1 | 65304227 | 65304256 | chr1 | 65305384 | 65305413 | chr1 | 65306926 | 65306955 |
| chr1 | 65309787 | 65309816 | chr1 | 65310487 | 65310531 | chr1 | 65311188 | 65311217 |
| chr1 | 65312331 | 65312432 | chr1 | 65731337 | 65731446 | chr1 | 65990955 | 65991018 |
| chr1 | 65991446 | 65991560 | chr1 | 65991606 | 65991757 | chr1 | 66258180 | 66258650 |
| chr1 | 66258672 | 66258774 | chr1 | 66259137 | 66259174 | chr1 | 66998790 | 66999332 |
| chr1 | 66999636 | 66999673 | chr1 | 67218064 | 67218343 | chr1 | 67390334 | 67390450 |
| chr1 | 67391067 | 67391096 | chr1 | 67773159 | 67773780 | chr1 | 70033609 | 70033916 |
| chr1 | 70034459 | 70034574 | chr1 | 70035088 | 70035537 | chr1 | 70599151 | 70599169 |
| chr1 | 70672858 | 70672878 | chr1 | 72749641 | 72749699 | chr1 | 75595819 | 75595990 |
| chr1 | 75596136 | 75596384 | chr1 | 75596687 | 75596858 | chr1 | 75596930 | 75597584 |
| chr1 | 75597923 | 75598179 | chr1 | 75598384 | 75598414 | chr1 | 75599427 | 75599621 |
| chr1 | 75600225 | 75600848 | chr1 | 75600925 | 75601118 | chr1 | 75601188 | 75601428 |
| chr1 | 75601983 | 75603052 | chr1 | 76080484 | 76080768 | chr1 | 76082129 | 76082209 |
| chr1 | 76354719 | 76354754 | chr1 | 76540450 | 76540666 | chr1 | 77333058 | 77333088 |
| chr1 | 77333384 | 77333433 | chr1 | 77334169 | 77334385 | chr1 | 77334409 | 77334756 |
| chr1 | 77747366 | 77747453 | chr1 | 77747939 | 77748235 | chr1 | 78511466 | 78512354 |
| chr1 | 78957292 | 78957522 | chr1 | 82267150 | 82267185 | chr1 | 82268573 | 82268815 |
| chr1 | 84944530 | 84944568 | chr1 | 85358752 | 85358822 | chr1 | 85463349 | 85463378 |
| chr1 | 85725508 | 85725537 | chr1 | 85725639 | 85725668 | chr1 | 86621660 | 86622127 |
| chr1 | 86622526 | 86622551 | chr1 | 86860809 | 86860949 | chr1 | 87617774 | 87617807 |
| chr1 | 90099997 | 90100084 | chr1 | 90309292 | 90309490 | chr1 | 91172012 | 91172677 |
| chr1 | 91177941 | 91178207 | chr1 | 91180075 | 91180306 | chr1 | 91181932 | 91182132 |
| chr1 | 91182338 | 91183195 | chr1 | 91183251 | 91183610 | chr1 | 91183951 | 91183986 |
| chr1 | 91184423 | 91184672 | chr1 | 91185190 | 91185308 | chr1 | 91185348 | 91185707 |

TABLE 13-continued

Pan Cancer #3

| chr | start | end | chr | start | end | chr | start | end |
|---|---|---|---|---|---|---|---|---|
| chr1 | 91188983 | 91189383 | chr1 | 91189688 | 91190380 | chr1 | 91190869 | 91190948 |
| chr1 | 91190985 | 91191234 | chr1 | 91191290 | 91191310 | chr1 | 91192274 | 91192576 |
| chr1 | 91194414 | 91194569 | chr1 | 91195117 | 91195390 | chr1 | 91195879 | 91196194 |
| chr1 | 91196226 | 91196502 | chr1 | 91316261 | 91316313 | chr1 | 91316627 | 91316682 |
| chr1 | 91869988 | 91870018 | chr1 | 92948324 | 92948597 | chr1 | 92948841 | 92948976 |
| chr1 | 92952145 | 92952655 | chr1 | 94147641 | 94147670 | chr1 | 94147816 | 94147845 |
| chr1 | 94343568 | 94343596 | chr1 | 95006795 | 95006902 | chr1 | 97185262 | 97185406 |
| chr1 | 98510791 | 98511335 | chr1 | 98511628 | 98511922 | chr1 | 98514225 | 98514255 |
| chr1 | 98515142 | 98515191 | chr1 | 98515256 | 98515319 | chr1 | 98519023 | 98519675 |
| chr1 | 99469682 | 99469696 | chr1 | 99469760 | 99469788 | chr1 | 99470785 | 99470847 |
| chr1 | 100437150 | 100437172 | chr1 | 101004456 | 101004737 | chr1 | 101005071 | 101005144 |
| chr1 | 101005360 | 101005675 | chr1 | 101702504 | 101702616 | chr1 | 101703612 | 101703642 |
| chr1 | 103574508 | 103574537 | chr1 | 107682735 | 107682977 | chr1 | 107683439 | 107683517 |
| chr1 | 107684240 | 107684439 | chr1 | 108507063 | 108507076 | chr1 | 108507320 | 108507375 |
| chr1 | 108507495 | 108507497 | chr1 | 108507717 | 108507810 | chr1 | 108508052 | 108508640 |
| chr1 | 109203609 | 109203672 | chr1 | 109585463 | 109585488 | chr1 | 109631646 | 109631682 |
| chr1 | 109644251 | 109644336 | chr1 | 110610586 | 110610897 | chr1 | 110611046 | 110611276 |
| chr1 | 110611435 | 110611513 | chr1 | 110611654 | 110611965 | chr1 | 110626684 | 110627578 |
| chr1 | 110672889 | 110673233 | chr1 | 110692973 | 110693496 | chr1 | 110693737 | 110694117 |
| chr1 | 110754003 | 110754101 | chr1 | 110754309 | 110754356 | chr1 | 110883542 | 110883965 |
| chr1 | 111097906 | 111097936 | chr1 | 111098196 | 111098316 | chr1 | 111216763 | 111216972 |
| chr1 | 111217195 | 111217891 | chr1 | 111217924 | 111217982 | chr1 | 111506007 | 111506212 |
| chr1 | 111813546 | 111813587 | chr1 | 112084954 | 112084984 | chr1 | 114428007 | 114428084 |
| chr1 | 114448967 | 114448990 | chr1 | 114695439 | 114695736 | chr1 | 114695800 | 114695943 |
| chr1 | 114696350 | 114696463 | chr1 | 114696541 | 114696712 | chr1 | 115256514 | 115256552 |
| chr1 | 115258729 | 115258772 | chr1 | 115631867 | 115631915 | chr1 | 115632469 | 115632555 |
| chr1 | 115880184 | 115880395 | chr1 | 115880873 | 115881042 | chr1 | 116214104 | 116214318 |
| chr1 | 116371139 | 116371201 | chr1 | 116380651 | 116381287 | chr1 | 116382387 | 116382478 |
| chr1 | 119522074 | 119522434 | chr1 | 119522839 | 119522853 | chr1 | 119522926 | 119522940 |
| chr1 | 119527237 | 119527391 | chr1 | 119527623 | 119527652 | chr1 | 119528653 | 119529118 |
| chr1 | 119529804 | 119529839 | chr1 | 119530100 | 119530148 | chr1 | 119530202 | 119530507 |
| chr1 | 119530554 | 119530725 | chr1 | 119531029 | 119531157 | chr1 | 119532318 | 119532320 |
| chr1 | 119535908 | 119536377 | chr1 | 119542322 | 119542352 | chr1 | 119543070 | 119543214 |
| chr1 | 119543532 | 119544182 | chr1 | 119548823 | 119548853 | chr1 | 119549058 | 119549734 |
| chr1 | 119549915 | 119549929 | chr1 | 119550155 | 119550278 | chr1 | 119550533 | 119550633 |
| chr1 | 119551014 | 119551269 | chr1 | 150603138 | 150603154 | chr1 | 150941425 | 150941756 |
| chr1 | 151169637 | 151169757 | chr1 | 151170057 | 151170206 | chr1 | 151300888 | 151300918 |
| chr1 | 151362740 | 151362779 | chr1 | 151693945 | 151694351 | chr1 | 151812413 | 151812442 |
| chr1 | 152009415 | 152009510 | chr1 | 152085398 | 152085504 | chr1 | 152488150 | 152488197 |
| chr1 | 153539476 | 153539637 | chr1 | 153540096 | 153540154 | chr1 | 153651965 | 153652379 |
| chr1 | 153937124 | 153937167 | chr1 | 154127987 | 154128016 | chr1 | 154298320 | 154298557 |
| chr1 | 154475372 | 154475531 | chr1 | 154516810 | 154516845 | chr1 | 155043331 | 155043657 |
| chr1 | 155161778 | 155162033 | chr1 | 155164415 | 155164455 | chr1 | 155283218 | 155283248 |
| chr1 | 155578888 | 155578921 | chr1 | 155826292 | 155826336 | chr1 | 155874151 | 155874300 |
| chr1 | 155874508 | 155874546 | chr1 | 155954282 | 155954396 | chr1 | 156010523 | 156010548 |
| chr1 | 156215329 | 156215359 | chr1 | 156215607 | 156215805 | chr1 | 156357993 | 156358508 |
| chr1 | 156390135 | 156390698 | chr1 | 156405635 | 156406070 | chr1 | 156406105 | 156406431 |
| chr1 | 156432124 | 156432321 | chr1 | 156594974 | 156595021 | chr1 | 156611889 | 156611943 |
| chr1 | 156611994 | 156612119 | chr1 | 156626589 | 156626658 | chr1 | 156626891 | 156627018 |
| chr1 | 156646278 | 156646307 | chr1 | 156646593 | 156646596 | chr1 | 156646635 | 156646647 |
| chr1 | 156814933 | 156814952 | chr1 | 156815031 | 156815146 | chr1 | 156815445 | 156815745 |
| chr1 | 156830269 | 156830348 | chr1 | 156838167 | 156838320 | chr1 | 156863107 | 156863331 |
| chr1 | 156863662 | 156863724 | chr1 | 157247368 | 157247388 | chr1 | 157458909 | 157458935 |
| chr1 | 157895413 | 157895443 | chr1 | 158669704 | 158669882 | chr1 | 158687415 | 158687550 |
| chr1 | 159140357 | 159140386 | chr1 | 159158348 | 159158368 | chr1 | 159158472 | 159158511 |
| chr1 | 159187279 | 159187429 | chr1 | 159258862 | 159258891 | chr1 | 159337517 | 159337615 |
| chr1 | 159409192 | 159409221 | chr1 | 160693934 | 160693958 | chr1 | 160992336 | 160992372 |
| chr1 | 161007587 | 161007746 | chr1 | 161086730 | 161086772 | chr1 | 161228659 | 161228891 |
| chr1 | 161275564 | 161275578 | chr1 | 161275640 | 161276026 | chr1 | 161368993 | 161369405 |
| chr1 | 161369859 | 161369945 | chr1 | 161442441 | 161442471 | chr1 | 161466301 | 161466324 |
| chr1 | 161471748 | 161471779 | chr1 | 161591472 | 161591546 | chr1 | 162724401 | 162724430 |
| chr1 | 162729615 | 162729686 | chr1 | 162748392 | 162748421 | chr1 | 162792306 | 162792533 |
| chr1 | 163393034 | 163393064 | chr1 | 164290615 | 164290671 | chr1 | 164730649 | 164730693 |
| chr1 | 165086988 | 165087027 | chr1 | 165205079 | 165205146 | chr1 | 165321747 | 165321786 |
| chr1 | 165323151 | 165323181 | chr1 | 165324196 | 165324249 | chr1 | 165324305 | 165324357 |
| chr1 | 165324488 | 165324668 | chr1 | 165325108 | 165325356 | chr1 | 165325395 | 165325521 |
| chr1 | 165325896 | 165325950 | chr1 | 165326204 | 165326204 | chr1 | 165326297 | 165326469 |
| chr1 | 165414191 | 165414272 | chr1 | 166134247 | 166134306 | chr1 | 166134728 | 166134796 |
| chr1 | 166135193 | 166135281 | chr1 | 166853563 | 166853592 | chr1 | 166890292 | 166890436 |
| chr1 | 166916866 | 166916920 | chr1 | 166916937 | 166916949 | chr1 | 167090617 | 167090757 |
| chr1 | 167599179 | 167599330 | chr1 | 167599616 | 167599844 | chr1 | 167823370 | 167823461 |
| chr1 | 169396376 | 169396688 | chr1 | 169396731 | 169396923 | chr1 | 169838016 | 169838187 |
| chr1 | 169930112 | 169930305 | chr1 | 170629540 | 170629569 | chr1 | 170629999 | 170630029 |
| chr1 | 170630456 | 170630810 | chr1 | 170631084 | 170631163 | chr1 | 170631477 | 170631559 |
| chr1 | 170633607 | 170633637 | chr1 | 170637666 | 170637796 | chr1 | 170640517 | 170640624 |
| chr1 | 170640665 | 170640691 | chr1 | 171625525 | 171625543 | chr1 | 171810200 | 171810972 |

TABLE 13-continued

Pan Cancer #3

| chr | start | end | chr | start | end | chr | start | end |
|---|---|---|---|---|---|---|---|---|
| chr1 | 173638647 | 173639085 | chr1 | 175346381 | 175346551 | chr1 | 175388664 | 175388682 |
| chr1 | 177133721 | 177133814 | chr1 | 177140105 | 177140173 | chr1 | 177140305 | 177140714 |
| chr1 | 177150773 | 177150803 | chr1 | 178063112 | 178063150 | chr1 | 179544967 | 179545098 |
| chr1 | 179712164 | 179712338 | chr1 | 179712411 | 179712553 | chr1 | 179712568 | 179712733 |
| chr1 | 179712831 | 179713174 | chr1 | 180198061 | 180198209 | chr1 | 180202649 | 180203016 |
| chr1 | 180203413 | 180203607 | chr1 | 180203634 | 180204619 | chr1 | 180204898 | 180204924 |
| chr1 | 180235730 | 180235760 | chr1 | 180882576 | 180882695 | chr1 | 180919682 | 180919718 |
| chr1 | 180925271 | 180925402 | chr1 | 181287679 | 181287757 | chr1 | 181288014 | 181288188 |
| chr1 | 181451407 | 181452120 | chr1 | 181452871 | 181452967 | chr1 | 181454873 | 181454912 |
| chr1 | 181455183 | 181455263 | chr1 | 182584048 | 182584339 | chr1 | 182584404 | 182584613 |
| chr1 | 182807578 | 182807660 | chr1 | 182921839 | 182921868 | chr1 | 183129382 | 183129530 |
| chr1 | 183386150 | 183386288 | chr1 | 183386599 | 183386626 | chr1 | 183386947 | 183386964 |
| chr1 | 183387266 | 183387319 | chr1 | 183462983 | 183463024 | chr1 | 183774244 | 183774363 |
| chr1 | 184005701 | 184005814 | chr1 | 185073818 | 185073966 | chr1 | 186570930 | 186570950 |
| chr1 | 190444855 | 190444885 | chr1 | 190445181 | 190445276 | chr1 | 190447389 | 190447519 |
| chr1 | 195732322 | 195732521 | chr1 | 196577628 | 196577858 | chr1 | 196578101 | 196578150 |
| chr1 | 197879400 | 197879660 | chr1 | 197879717 | 197880156 | chr1 | 197882140 | 197882201 |
| chr1 | 197882453 | 197882611 | chr1 | 197887052 | 197887066 | chr1 | 197887147 | 197887456 |
| chr1 | 197887707 | 197887741 | chr1 | 197888052 | 197888121 | chr1 | 197888181 | 197888319 |
| chr1 | 197888643 | 197889286 | chr1 | 200009357 | 200009450 | chr1 | 200009750 | 200010114 |
| chr1 | 200011323 | 200012227 | chr1 | 200591054 | 200591080 | chr1 | 201368582 | 201368727 |
| chr1 | 201476501 | 201476619 | chr1 | 201983113 | 201983200 | chr1 | 202081766 | 202081804 |
| chr1 | 202183371 | 202183401 | chr1 | 202531939 | 202532087 | chr1 | 202679215 | 202679518 |
| chr1 | 203298307 | 203298449 | chr1 | 203429564 | 203429594 | chr1 | 203681332 | 203681362 |
| chr1 | 204333609 | 204333668 | chr1 | 204478326 | 204478427 | chr1 | 204499813 | 204499842 |
| chr1 | 204524704 | 204524724 | chr1 | 204531203 | 204531540 | chr1 | 204531600 | 204531757 |
| chr1 | 204653561 | 204653595 | chr1 | 204653793 | 204653807 | chr1 | 205312596 | 205312911 |
| chr1 | 205424654 | 205424957 | chr1 | 205537663 | 205537772 | chr1 | 207200870 | 207200962 |
| chr1 | 207227527 | 207227556 | chr1 | 207669496 | 207669787 | chr1 | 207669829 | 207670060 |
| chr1 | 207818394 | 207818396 | chr1 | 207818434 | 207818493 | chr1 | 208084289 | 208084488 |
| chr1 | 209381132 | 209381165 | chr1 | 209604382 | 209604597 | chr1 | 209605386 | 209605415 |
| chr1 | 209849170 | 209849199 | chr1 | 209849430 | 209849459 | chr1 | 210111146 | 210111176 |
| chr1 | 210111388 | 210111421 | chr1 | 210111797 | 210111922 | chr1 | 210112037 | 210112140 |
| chr1 | 211847706 | 211847787 | chr1 | 212963883 | 212963987 | chr1 | 213123871 | 213123979 |
| chr1 | 213124669 | 213124910 | chr1 | 214156419 | 214156928 | chr1 | 214158838 | 214158910 |
| chr1 | 214160107 | 214160184 | chr1 | 214360675 | 214360858 | chr1 | 214360927 | 214360968 |
| chr1 | 214724531 | 214724561 | chr1 | 215255094 | 215255799 | chr1 | 216897216 | 216897307 |
| chr1 | 217307385 | 217308274 | chr1 | 217309007 | 217309105 | chr1 | 217309764 | 217309816 |
| chr1 | 217311265 | 217311839 | chr1 | 217313042 | 217313042 | chr1 | 217313069 | 217313747 |
| chr1 | 217805158 | 217805247 | chr1 | 218520096 | 218520291 | chr1 | 218520310 | 218520399 |
| chr1 | 218520775 | 218520805 | chr1 | 219346992 | 219347035 | chr1 | 219347394 | 219347472 |
| chr1 | 220101145 | 220101210 | chr1 | 220101371 | 220101385 | chr1 | 220101683 | 220101712 |
| chr1 | 220132075 | 220132111 | chr1 | 220636466 | 220636510 | chr1 | 220700814 | 220700897 |
| chr1 | 221052038 | 221052492 | chr1 | 221053610 | 221053862 | chr1 | 221067506 | 221067688 |
| chr1 | 221068156 | 221068185 | chr1 | 221068793 | 221069150 | chr1 | 221510339 | 221510368 |
| chr1 | 221737191 | 221737220 | chr1 | 223302825 | 223302890 | chr1 | 223538344 | 223538641 |
| chr1 | 223936633 | 223936752 | chr1 | 223936996 | 223937057 | chr1 | 224363560 | 224363589 |
| chr1 | 224400490 | 224400524 | chr1 | 224493975 | 224493999 | chr1 | 224528814 | 224528844 |
| chr1 | 224803717 | 224803751 | chr1 | 224804097 | 224804295 | chr1 | 224804396 | 224804686 |
| chr1 | 224804847 | 224804910 | chr1 | 224805198 | 224805751 | chr1 | 226411247 | 226411273 |
| chr1 | 226411700 | 226411832 | chr1 | 226814346 | 226814408 | chr1 | 226925067 | 226925195 |
| chr1 | 226997660 | 226997719 | chr1 | 227729830 | 227730075 | chr1 | 227748700 | 227748733 |
| chr1 | 228195377 | 228196349 | chr1 | 228201221 | 228201251 | chr1 | 228247998 | 228248027 |
| chr1 | 228248302 | 228248332 | chr1 | 228345999 | 228346195 | chr1 | 228461158 | 228461197 |
| chr1 | 228463311 | 228463706 | chr1 | 228528840 | 228529016 | chr1 | 228558699 | 228559238 |
| chr1 | 228566622 | 228566672 | chr1 | 228604124 | 228604254 | chr1 | 228633990 | 228634261 |
| chr1 | 228645140 | 228645243 | chr1 | 228645306 | 228645734 | chr1 | 228646195 | 228646238 |
| chr1 | 228651432 | 228651626 | chr1 | 228651879 | 228651901 | chr1 | 228652224 | 228652452 |
| chr1 | 228652509 | 228652629 | chr1 | 228871865 | 228872003 | chr1 | 229542838 | 229542952 |
| chr1 | 229543553 | 229543603 | chr1 | 229566753 | 229567276 | chr1 | 229567370 | 229567992 |
| chr1 | 229568158 | 229568204 | chr1 | 229569810 | 229569852 | chr1 | 230404217 | 230404263 |
| chr1 | 230561779 | 230561824 | chr1 | 231297103 | 231297221 | chr1 | 231298595 | 231298707 |
| chr1 | 232765195 | 232765301 | chr1 | 233465473 | 233465503 | chr1 | 233750082 | 233750302 |
| chr1 | 234040247 | 234040319 | chr1 | 234040886 | 234040973 | chr1 | 234041416 | 234041624 |
| chr1 | 234349988 | 234350100 | chr1 | 234445373 | 234445403 | chr1 | 234620866 | 234620979 |
| chr1 | 234798171 | 234798201 | chr1 | 234839889 | 234840058 | chr1 | 234844955 | 234845079 |
| chr1 | 234845467 | 234845497 | chr1 | 235665700 | 235665736 | chr1 | 235813781 | 235813796 |
| chr1 | 235814010 | 235814202 | chr1 | 235814447 | 235814476 | chr1 | 236227637 | 236227743 |
| chr1 | 236227770 | 236227920 | chr1 | 236228022 | 236228096 | chr1 | 236228582 | 236228623 |
| chr1 | 236228706 | 236228789 | chr1 | 236559176 | 236559206 | chr1 | 236559257 | 236559271 |
| chr1 | 236849457 | 236849505 | chr1 | 237205159 | 237205188 | chr1 | 237206102 | 237206265 |
| chr1 | 237206512 | 237206735 | chr1 | 238024448 | 238024477 | chr1 | 239550594 | 239551193 |
| chr1 | 240118848 | 240118973 | chr1 | 240161123 | 240161380 | chr1 | 240254944 | 240255011 |
| chr1 | 240255361 | 240255500 | chr1 | 240255819 | 240256158 | chr1 | 240256663 | 240256721 |
| chr1 | 240775425 | 240775455 | chr1 | 241052096 | 241052126 | chr1 | 241520296 | 241520345 |
| chr1 | 241520583 | 241520612 | chr1 | 241587034 | 241587113 | chr1 | 241587587 | 241587797 |

TABLE 13-continued

Pan Cancer #3

| chr | start | end | chr | start | end | chr | start | end |
|---|---|---|---|---|---|---|---|---|
| chr1 | 241912749 | 241912778 | chr1 | 242686734 | 242687688 | chr1 | 242688184 | 242688243 |
| chr1 | 242688477 | 242688695 | chr1 | 243646610 | 243646673 | chr1 | 243859000 | 243859029 |
| chr1 | 244014221 | 244014376 | chr1 | 244080672 | 244080702 | chr1 | 244080963 | 244081061 |
| chr1 | 244081078 | 244081203 | chr1 | 244893214 | 244893295 | chr1 | 245032517 | 245032603 |
| chr1 | 245135753 | 245135849 | chr1 | 245494495 | 245494578 | chr1 | 245849914 | 245849944 |
| chr1 | 246198078 | 246198203 | chr1 | 246330309 | 246330409 | chr1 | 246488175 | 246488316 |
| chr1 | 247496038 | 247496057 | chr1 | 247608784 | 247608814 | chr1 | 248002278 | 248002358 |
| chr1 | 248020516 | 248020630 | chr1 | 248020957 | 248021349 | chr1 | 248028015 | 248028202 |
| chr1 | 248074729 | 248074768 | chr1 | 248074828 | 248074927 | chr1 | 248099751 | 248099809 |
| chr1 | 248328701 | 248328841 | chr1 | 249121622 | 249121704 | chr2 | 46214 | 46450 |
| chr2 | 264163 | 264204 | chr2 | 287580 | 287641 | chr2 | 288404 | 288470 |
| chr2 | 468424 | 468672 | chr2 | 496228 | 496380 | chr2 | 602657 | 602687 |
| chr2 | 720836 | 720894 | chr2 | 875961 | 875991 | chr2 | 945913 | 946000 |
| chr2 | 946208 | 946217 | chr2 | 946526 | 946566 | chr2 | 946917 | 947043 |
| chr2 | 947127 | 947159 | chr2 | 1652837 | 1653230 | chr2 | 1670168 | 1670216 |
| chr2 | 1746614 | 1747032 | chr2 | 1747670 | 1748007 | chr2 | 1748397 | 1748890 |
| chr2 | 2321773 | 2321802 | chr2 | 2336413 | 2336442 | chr2 | 2646900 | 2646930 |
| chr2 | 2672620 | 2672732 | chr2 | 2844720 | 2844750 | chr2 | 2893165 | 2893195 |
| chr2 | 3259989 | 3260103 | chr2 | 4019911 | 4020036 | chr2 | 4050752 | 4050781 |
| chr2 | 5831178 | 5831204 | chr2 | 5831238 | 5831324 | chr2 | 5831789 | 5831819 |
| chr2 | 5833283 | 5833432 | chr2 | 5833500 | 5833639 | chr2 | 5833735 | 5834028 |
| chr2 | 5836085 | 5836253 | chr2 | 5836548 | 5836574 | chr2 | 5836622 | 5836744 |
| chr2 | 5836828 | 5836991 | chr2 | 5837353 | 5837414 | chr2 | 5866098 | 5866211 |
| chr2 | 7164467 | 7164788 | chr2 | 7571577 | 7571747 | chr2 | 8735932 | 8736064 |
| chr2 | 9134404 | 9134493 | chr2 | 9192356 | 9192379 | chr2 | 9289969 | 9290114 |
| chr2 | 9960734 | 9960764 | chr2 | 10115730 | 10115751 | chr2 | 10153062 | 10153325 |
| chr2 | 10154930 | 10155024 | chr2 | 10155264 | 10155298 | chr2 | 10156313 | 10156389 |
| chr2 | 10182827 | 10182904 | chr2 | 10369155 | 10369242 | chr2 | 10408398 | 10408459 |
| chr2 | 10688874 | 10688904 | chr2 | 11052517 | 11052559 | chr2 | 11142275 | 11142315 |
| chr2 | 11672746 | 11672775 | chr2 | 11809957 | 11810115 | chr2 | 11903450 | 11903480 |
| chr2 | 12246114 | 12246196 | chr2 | 12858452 | 12858618 | chr2 | 14772761 | 14772823 |
| chr2 | 14774281 | 14774567 | chr2 | 17719688 | 17719812 | chr2 | 18059035 | 18059085 |
| chr2 | 18059781 | 18059841 | chr2 | 19550214 | 19550244 | chr2 | 19551322 | 19551366 |
| chr2 | 19556318 | 19556672 | chr2 | 19557068 | 19557098 | chr2 | 19557685 | 19557727 |
| chr2 | 19558832 | 19558893 | chr2 | 19561131 | 19561316 | chr2 | 19561524 | 19561685 |
| chr2 | 19563358 | 19563433 | chr2 | 20068798 | 20068885 | chr2 | 20442466 | 20442498 |
| chr2 | 20642625 | 20642648 | chr2 | 20865636 | 20865927 | chr2 | 25374762 | 25374804 |
| chr2 | 25391013 | 25391212 | chr2 | 25391684 | 25391725 | chr2 | 25438821 | 25438871 |
| chr2 | 25439139 | 25439383 | chr2 | 25600736 | 25600804 | chr2 | 26372967 | 26372997 |
| chr2 | 26395447 | 26395556 | chr2 | 26402030 | 26402060 | chr2 | 26407744 | 26407921 |
| chr2 | 26521972 | 26522127 | chr2 | 26915763 | 26916066 | chr2 | 26916089 | 26916259 |
| chr2 | 27070324 | 27070414 | chr2 | 27071240 | 27071346 | chr2 | 27072492 | 27072534 |
| chr2 | 27072822 | 27072989 | chr2 | 27356168 | 27356198 | chr2 | 27578380 | 27578396 |
| chr2 | 27665125 | 27665154 | chr2 | 27665506 | 27665711 | chr2 | 27887525 | 27887555 |
| chr2 | 29033336 | 29033697 | chr2 | 29091592 | 29091625 | chr2 | 29338159 | 29338747 |
| chr2 | 29338810 | 29338969 | chr2 | 29420483 | 29420512 | chr2 | 29432640 | 29432696 |
| chr2 | 29436844 | 29436888 | chr2 | 29443573 | 29443710 | chr2 | 29445198 | 29445482 |
| chr2 | 29446361 | 29446396 | chr2 | 30143304 | 30143322 | chr2 | 30143383 | 30143492 |
| chr2 | 30144041 | 30144150 | chr2 | 30144175 | 30144411 | chr2 | 30453785 | 30453941 |
| chr2 | 31360306 | 31360589 | chr2 | 31360631 | 31360755 | chr2 | 31360804 | 31360831 |
| chr2 | 31361089 | 31361118 | chr2 | 31361356 | 31361385 | chr2 | 31456682 | 31457039 |
| chr2 | 32504334 | 32504378 | chr2 | 32580386 | 32580431 | chr2 | 38302370 | 38302876 |
| chr2 | 38365727 | 38365748 | chr2 | 38551124 | 38551167 | chr2 | 38727561 | 38727707 |
| chr2 | 38762382 | 38762412 | chr2 | 39187218 | 39187237 | chr2 | 39187544 | 39187722 |
| chr2 | 39893090 | 39893501 | chr2 | 39893972 | 39894059 | chr2 | 40678603 | 40678872 |
| chr2 | 40678932 | 40679604 | chr2 | 42274595 | 42274633 | chr2 | 42329431 | 42329444 |
| chr2 | 42329494 | 42329666 | chr2 | 42720262 | 42720446 | chr2 | 43019599 | 43019868 |
| chr2 | 43451909 | 43452327 | chr2 | 43824133 | 43824153 | chr2 | 44497708 | 44497875 |
| chr2 | 44809187 | 44809217 | chr2 | 45028988 | 45029058 | chr2 | 45029184 | 45029371 |
| chr2 | 45029682 | 45029712 | chr2 | 45155125 | 45155210 | chr2 | 45155356 | 45156811 |
| chr2 | 45156833 | 45157711 | chr2 | 45159956 | 45160267 | chr2 | 45160596 | 45160634 |
| chr2 | 45161663 | 45162112 | chr2 | 45162394 | 45162481 | chr2 | 45162751 | 45162913 |
| chr2 | 45164663 | 45164693 | chr2 | 45165564 | 45165594 | chr2 | 45168803 | 45168833 |
| chr2 | 45169446 | 45170029 | chr2 | 45171385 | 45171563 | chr2 | 45171837 | 45171862 |
| chr2 | 45176601 | 45176768 | chr2 | 45179620 | 45179650 | chr2 | 45179939 | 45180203 |
| chr2 | 45181520 | 45181672 | chr2 | 45181887 | 45182001 | chr2 | 45228627 | 45228730 |
| chr2 | 45231320 | 45231396 | chr2 | 45231805 | 45232131 | chr2 | 45233385 | 45233586 |
| chr2 | 45235594 | 45235926 | chr2 | 45237673 | 45237795 | chr2 | 45240548 | 45240630 |
| chr2 | 45240764 | 45240784 | chr2 | 45241136 | 45241168 | chr2 | 45395854 | 45395920 |
| chr2 | 45396315 | 45396451 | chr2 | 45396688 | 45396995 | chr2 | 46526302 | 46526448 |
| chr2 | 47193930 | 47194093 | chr2 | 47200591 | 47200621 | chr2 | 47249725 | 47249848 |
| chr2 | 47598278 | 47598518 | chr2 | 47598578 | 47598620 | chr2 | 47748140 | 47748494 |
| chr2 | 47797043 | 47797818 | chr2 | 47798180 | 47798663 | chr2 | 47798954 | 47799032 |
| chr2 | 48636504 | 48636647 | chr2 | 48982582 | 48982700 | chr2 | 48982754 | 48982866 |
| chr2 | 50573595 | 50573638 | chr2 | 50573692 | 50573865 | chr2 | 50574121 | 50574355 |
| chr2 | 50574402 | 50574684 | chr2 | 50574739 | 50574859 | chr2 | 55289094 | 55289274 |

TABLE 13-continued

Pan Cancer #3

| chr | start | end | chr | start | end | chr | start | end |
|---|---|---|---|---|---|---|---|---|
| chr2 | 56149836 | 56149866 | chr2 | 56150729 | 56151193 | chr2 | 56410817 | 56410996 |
| chr2 | 56411691 | 56411733 | chr2 | 58656049 | 58656125 | chr2 | 60706759 | 60706804 |
| chr2 | 60796587 | 60796617 | chr2 | 60797137 | 60797281 | chr2 | 61135115 | 61135137 |
| chr2 | 62798343 | 62798386 | chr2 | 63278962 | 63278992 | chr2 | 63280952 | 63281651 |
| chr2 | 63282716 | 63282786 | chr2 | 63283014 | 63283027 | chr2 | 63283952 | 63284146 |
| chr2 | 63284777 | 63284811 | chr2 | 63285081 | 63286047 | chr2 | 63286359 | 63286584 |
| chr2 | 63286694 | 63286747 | chr2 | 63287083 | 63287368 | chr2 | 65251310 | 65251340 |
| chr2 | 66652863 | 66652963 | chr2 | 66653238 | 66653496 | chr2 | 66653764 | 66653914 |
| chr2 | 66660650 | 66660888 | chr2 | 66662749 | 66662824 | chr2 | 66808525 | 66808633 |
| chr2 | 66808727 | 66809361 | chr2 | 67625453 | 67625492 | chr2 | 67625732 | 67625770 |
| chr2 | 67626102 | 67626257 | chr2 | 68287783 | 68287799 | chr2 | 68546324 | 68546516 |
| chr2 | 68546553 | 68546892 | chr2 | 68559343 | 68559365 | chr2 | 68672853 | 68672938 |
| chr2 | 69027024 | 69027053 | chr2 | 70418608 | 70418627 | chr2 | 71355038 | 71355117 |
| chr2 | 71503790 | 71503823 | chr2 | 71504103 | 71504148 | chr2 | 71680833 | 71680863 |
| chr2 | 71693374 | 71693593 | chr2 | 72374375 | 72374432 | chr2 | 72374714 | 72374765 |
| chr2 | 73145640 | 73145694 | chr2 | 73145924 | 73146021 | chr2 | 73147324 | 73147527 |
| chr2 | 73147967 | 73148066 | chr2 | 73148175 | 73148243 | chr2 | 73150924 | 73150954 |
| chr2 | 73151187 | 73151831 | chr2 | 73152740 | 73152754 | chr2 | 73416356 | 73416386 |
| chr2 | 73429523 | 73429614 | chr2 | 73429977 | 73430069 | chr2 | 73430322 | 73430372 |
| chr2 | 73430443 | 73430743 | chr2 | 73440250 | 73440293 | chr2 | 73518448 | 73518919 |
| chr2 | 73519579 | 73519841 | chr2 | 74010528 | 74010621 | chr2 | 74153198 | 74153227 |
| chr2 | 74426185 | 74426214 | chr2 | 74454074 | 74454261 | chr2 | 74647864 | 74647906 |
| chr2 | 74726744 | 74726774 | chr2 | 74740852 | 74741387 | chr2 | 74741835 | 74741844 |
| chr2 | 74741873 | 74741955 | chr2 | 74742325 | 74742647 | chr2 | 74742694 | 74743144 |
| chr2 | 74782081 | 74782087 | chr2 | 74782219 | 74782271 | chr2 | 75427040 | 75427114 |
| chr2 | 75427369 | 75427399 | chr2 | 75427930 | 75428177 | chr2 | 75720510 | 75720541 |
| chr2 | 79347459 | 79347546 | chr2 | 80529378 | 80529443 | chr2 | 80529662 | 80529908 |
| chr2 | 80529986 | 80530022 | chr2 | 80530505 | 80530558 | chr2 | 80531725 | 80531755 |
| chr2 | 80549585 | 80549745 | chr2 | 85107454 | 85107538 | chr2 | 85361467 | 85361528 |
| chr2 | 86263223 | 86263270 | chr2 | 86791221 | 86791251 | chr2 | 87016579 | 87016636 |
| chr2 | 87017796 | 87018396 | chr2 | 87036611 | 87036640 | chr2 | 88469312 | 88469398 |
| chr2 | 88751281 | 88751419 | chr2 | 88751461 | 88751800 | chr2 | 88752055 | 88752285 |
| chr2 | 88752603 | 88752785 | chr2 | 88990189 | 88990264 | chr2 | 89064806 | 89064975 |
| chr2 | 89065129 | 89065278 | chr2 | 95663969 | 95664014 | chr2 | 95690747 | 95690793 |
| chr2 | 95691036 | 95691269 | chr2 | 95691530 | 95691769 | chr2 | 95691994 | 95692480 |
| chr2 | 95941678 | 95941812 | chr2 | 96070057 | 96070081 | chr2 | 96990898 | 96991316 |
| chr2 | 97193252 | 97193626 | chr2 | 97427515 | 97428093 | chr2 | 98703323 | 98703475 |
| chr2 | 98703675 | 98703736 | chr2 | 98962898 | 98962900 | chr2 | 98963329 | 98963599 |
| chr2 | 98963869 | 98964200 | chr2 | 98964596 | 98964645 | chr2 | 99439369 | 99439507 |
| chr2 | 99553391 | 99553656 | chr2 | 99796295 | 99796330 | chr2 | 99798646 | 99798750 |
| chr2 | 99799050 | 99799153 | chr2 | 100618451 | 100618480 | chr2 | 100937836 | 100938209 |
| chr2 | 100938330 | 100938544 | chr2 | 100938575 | 100938809 | chr2 | 100938985 | 100939155 |
| chr2 | 101009832 | 101009927 | chr2 | 101034242 | 101034293 | chr2 | 101436632 | 101436708 |
| chr2 | 101666893 | 101667004 | chr2 | 102091180 | 102091335 | chr2 | 103236165 | 103236292 |
| chr2 | 105459081 | 105459151 | chr2 | 105459908 | 105460599 | chr2 | 105460921 | 105460951 |
| chr2 | 105461187 | 105461243 | chr2 | 105461564 | 105461667 | chr2 | 105461700 | 105461896 |
| chr2 | 105462165 | 105462222 | chr2 | 105468791 | 105468908 | chr2 | 105469645 | 105469856 |
| chr2 | 105469881 | 105470091 | chr2 | 105470350 | 105470840 | chr2 | 105472231 | 105472425 |
| chr2 | 105472713 | 105472845 | chr2 | 105473248 | 105473521 | chr2 | 105478762 | 105479089 |
| chr2 | 105483655 | 105483719 | chr2 | 105484450 | 105484522 | chr2 | 105488437 | 105488496 |
| chr2 | 105760981 | 105761009 | chr2 | 105937344 | 105937498 | chr2 | 106060615 | 106060792 |
| chr2 | 106681733 | 106681767 | chr2 | 106682012 | 106682098 | chr2 | 106730223 | 106730256 |
| chr2 | 106959368 | 106959568 | chr2 | 106959916 | 106959988 | chr2 | 107103865 | 107103928 |
| chr2 | 107502600 | 107502729 | chr2 | 107503532 | 107503561 | chr2 | 107503884 | 107504018 |
| chr2 | 109335133 | 109335166 | chr2 | 109648080 | 109648222 | chr2 | 109745989 | 109746079 |
| chr2 | 109746289 | 109746387 | chr2 | 109746463 | 109746477 | chr2 | 110015080 | 110015110 |
| chr2 | 110370941 | 110371219 | chr2 | 110873016 | 110873045 | chr2 | 111544817 | 111544847 |
| chr2 | 111875191 | 111875611 | chr2 | 112657033 | 112657092 | chr2 | 113227125 | 113227225 |
| chr2 | 113594639 | 113594668 | chr2 | 113931503 | 113931532 | chr2 | 114256978 | 114257137 |
| chr2 | 114261300 | 114261458 | chr2 | 114470172 | 114470201 | chr2 | 115918661 | 115918892 |
| chr2 | 115919338 | 115919424 | chr2 | 115919831 | 115920534 | chr2 | 118981151 | 118981856 |
| chr2 | 118981946 | 118982147 | chr2 | 118982254 | 118982497 | chr2 | 119067636 | 119068049 |
| chr2 | 119532161 | 119532255 | chr2 | 119566239 | 119566272 | chr2 | 119591351 | 119591465 |
| chr2 | 119592588 | 119592777 | chr2 | 119592997 | 119593567 | chr2 | 119599926 | 119600031 |
| chr2 | 119600332 | 119600555 | chr2 | 119600570 | 119600747 | chr2 | 119600949 | 119600952 |
| chr2 | 119600996 | 119601061 | chr2 | 119602601 | 119602629 | chr2 | 119602829 | 119603086 |
| chr2 | 119604032 | 119604158 | chr2 | 119604809 | 119604851 | chr2 | 119606135 | 119606499 |
| chr2 | 119606783 | 119606839 | chr2 | 119607176 | 119607411 | chr2 | 119610844 | 119610939 |
| chr2 | 119611745 | 119611799 | chr2 | 119612324 | 119612354 | chr2 | 119614130 | 119614171 |
| chr2 | 119614780 | 119614852 | chr2 | 119615055 | 119615627 | chr2 | 119616155 | 119616551 |
| chr2 | 119616809 | 119616870 | chr2 | 119914720 | 119914752 | chr2 | 119916525 | 119916595 |
| chr2 | 120281646 | 120281693 | chr2 | 120281939 | 120281953 | chr2 | 120980068 | 120980098 |
| chr2 | 120980353 | 120980395 | chr2 | 121200390 | 121200433 | chr2 | 121345081 | 121345111 |
| chr2 | 121411888 | 121412153 | chr2 | 122176232 | 122176293 | chr2 | 122495310 | 122495413 |
| chr2 | 122809783 | 122809801 | chr2 | 124782333 | 124782458 | chr2 | 124782692 | 124783097 |
| chr2 | 127413970 | 127413995 | chr2 | 127423220 | 127423350 | chr2 | 127429010 | 127429044 |

TABLE 13-continued

Pan Cancer #3

| chr | start | end | chr | start | end | chr | start | end |
|---|---|---|---|---|---|---|---|---|
| chr2 | 127438633 | 127438663 | chr2 | 127783043 | 127783257 | chr2 | 127863601 | 127863725 |
| chr2 | 127976467 | 127976672 | chr2 | 128421891 | 128421947 | chr2 | 128616617 | 128616638 |
| chr2 | 128847700 | 128847723 | chr2 | 129494389 | 129494421 | chr2 | 130763584 | 130763623 |
| chr2 | 130971149 | 130971321 | chr2 | 131477785 | 131477936 | chr2 | 131594989 | 131595019 |
| chr2 | 131673756 | 131673785 | chr2 | 131720852 | 131721098 | chr2 | 131721461 | 131721584 |
| chr2 | 131721867 | 131721949 | chr2 | 131792260 | 131792519 | chr2 | 131792532 | 131792746 |
| chr2 | 131792921 | 131793131 | chr2 | 132088786 | 132088828 | chr2 | 132121661 | 132121829 |
| chr2 | 132152361 | 132152495 | chr2 | 132182790 | 132183089 | chr2 | 132208257 | 132208278 |
| chr2 | 132767457 | 132767492 | chr2 | 133014598 | 133014638 | chr2 | 133015299 | 133015323 |
| chr2 | 133062362 | 133062389 | chr2 | 133426249 | 133426279 | chr2 | 133426637 | 133426674 |
| chr2 | 136287374 | 136287390 | chr2 | 137522445 | 137522475 | chr2 | 137523825 | 137523855 |
| chr2 | 139536937 | 139537145 | chr2 | 139537443 | 139537822 | chr2 | 139537851 | 139537865 |
| chr2 | 142887871 | 142888066 | chr2 | 142888348 | 142888418 | chr2 | 144694367 | 144694514 |
| chr2 | 144694554 | 144695135 | chr2 | 145273404 | 145273751 | chr2 | 145274186 | 145274455 |
| chr2 | 145274814 | 145275213 | chr2 | 145282119 | 145282149 | chr2 | 148776809 | 148776892 |
| chr2 | 149633097 | 149633399 | chr2 | 149633744 | 149633965 | chr2 | 149645496 | 149645894 |
| chr2 | 151342903 | 151343277 | chr2 | 154333535 | 154333567 | chr2 | 154334272 | 154334665 |
| chr2 | 154335185 | 154335271 | chr2 | 154728245 | 154728440 | chr2 | 154729083 | 154729240 |
| chr2 | 154729559 | 154729589 | chr2 | 155555038 | 155555361 | chr2 | 157176592 | 157176717 |
| chr2 | 157177003 | 157178310 | chr2 | 157178646 | 157178731 | chr2 | 160761070 | 160761556 |
| chr2 | 161253374 | 161253455 | chr2 | 162272989 | 162273314 | chr2 | 162273383 | 162274338 |
| chr2 | 162274717 | 162274866 | chr2 | 162275146 | 162275226 | chr2 | 162275311 | 162275437 |
| chr2 | 162275473 | 162275802 | chr2 | 162280153 | 162280415 | chr2 | 162280741 | 162280956 |
| chr2 | 162283365 | 162283602 | chr2 | 162283783 | 162284055 | chr2 | 164593096 | 164593137 |
| chr2 | 168150069 | 168150245 | chr2 | 168150751 | 168150945 | chr2 | 170282981 | 170283080 |
| chr2 | 170551730 | 170551866 | chr2 | 170681880 | 170681911 | chr2 | 170682151 | 170682331 |
| chr2 | 171570182 | 171570189 | chr2 | 171570684 | 171570733 | chr2 | 171571264 | 171571315 |
| chr2 | 171571889 | 171572068 | chr2 | 171670349 | 171670446 | chr2 | 171671487 | 171671789 |
| chr2 | 171671800 | 171671881 | chr2 | 171673873 | 171673939 | chr2 | 171674739 | 171675066 |
| chr2 | 171675361 | 171675382 | chr2 | 171675523 | 171675592 | chr2 | 171676684 | 171676785 |
| chr2 | 171822428 | 171822480 | chr2 | 172367021 | 172367125 | chr2 | 172411136 | 172411166 |
| chr2 | 172945124 | 172945167 | chr2 | 172945896 | 172946211 | chr2 | 172947717 | 172947913 |
| chr2 | 172948184 | 172948314 | chr2 | 172948709 | 172948751 | chr2 | 172949186 | 172949282 |
| chr2 | 172949349 | 172949711 | chr2 | 172952521 | 172952881 | chr2 | 172952993 | 172953046 |
| chr2 | 172955472 | 172955545 | chr2 | 172957907 | 172958066 | chr2 | 172961398 | 172961598 |
| chr2 | 172964821 | 172964888 | chr2 | 172965296 | 172965298 | chr2 | 172965648 | 172965762 |
| chr2 | 172966264 | 172966442 | chr2 | 172972735 | 172972890 | chr2 | 172972931 | 172973218 |
| chr2 | 173099784 | 173099814 | chr2 | 173100262 | 173100430 | chr2 | 173422685 | 173422734 |
| chr2 | 174148138 | 174148157 | chr2 | 175190871 | 175191972 | chr2 | 175192085 | 175192468 |
| chr2 | 175193268 | 175193644 | chr2 | 175193809 | 175193823 | chr2 | 175195831 | 175195858 |
| chr2 | 175196432 | 175196575 | chr2 | 175197089 | 175197119 | chr2 | 175198752 | 175198766 |
| chr2 | 175198846 | 175198966 | chr2 | 175199527 | 175199554 | chr2 | 175199922 | 175199935 |
| chr2 | 175200140 | 175200440 | chr2 | 175200710 | 175200852 | chr2 | 175200917 | 175201182 |
| chr2 | 175201360 | 175201541 | chr2 | 175201776 | 175201828 | chr2 | 175202127 | 175202245 |
| chr2 | 175202569 | 175202600 | chr2 | 175202634 | 175202652 | chr2 | 175204174 | 175204204 |
| chr2 | 175204786 | 175204946 | chr2 | 175205588 | 175205799 | chr2 | 175206833 | 175206905 |
| chr2 | 175206961 | 175207028 | chr2 | 175207228 | 175207258 | chr2 | 175207536 | 175207653 |
| chr2 | 175208311 | 175208868 | chr2 | 175208997 | 175209135 | chr2 | 175547041 | 175547140 |
| chr2 | 175547384 | 175547413 | chr2 | 176940167 | 176940315 | chr2 | 176943269 | 176943568 |
| chr2 | 176943861 | 176943902 | chr2 | 176944457 | 176944846 | chr2 | 176945138 | 176945268 |
| chr2 | 176945582 | 176945784 | chr2 | 176946578 | 176946867 | chr2 | 176947285 | 176947389 |
| chr2 | 176947764 | 176947903 | chr2 | 176948599 | 176948742 | chr2 | 176949045 | 176949075 |
| chr2 | 176949695 | 176949869 | chr2 | 176950142 | 176950258 | chr2 | 176956558 | 176956599 |
| chr2 | 176956921 | 176957199 | chr2 | 176957577 | 176957628 | chr2 | 176957915 | 176957919 |
| chr2 | 176958138 | 176958489 | chr2 | 176959289 | 176959511 | chr2 | 176963448 | 176963522 |
| chr2 | 176964085 | 176964149 | chr2 | 176964390 | 176964767 | chr2 | 176965265 | 176965492 |
| chr2 | 176969463 | 176969613 | chr2 | 176969677 | 176969908 | chr2 | 176971628 | 176971651 |
| chr2 | 176976029 | 176976188 | chr2 | 176980750 | 176980937 | chr2 | 176981377 | 176981506 |
| chr2 | 176982584 | 176982627 | chr2 | 176986715 | 176986848 | chr2 | 176987057 | 176987224 |
| chr2 | 176987971 | 176988103 | chr2 | 176988155 | 176988304 | chr2 | 176993074 | 176993103 |
| chr2 | 176993547 | 176993855 | chr2 | 176994031 | 176994379 | chr2 | 176994498 | 176994621 |
| chr2 | 176995072 | 176995269 | chr2 | 176995332 | 176995668 | chr2 | 177001102 | 177001695 |
| chr2 | 177001782 | 177001976 | chr2 | 177004566 | 177004658 | chr2 | 177014981 | 177015010 |
| chr2 | 177027425 | 177027438 | chr2 | 177030149 | 177030226 | chr2 | 177042984 | 177042998 |
| chr2 | 177043267 | 177043515 | chr2 | 177053276 | 177053434 | chr2 | 177053619 | 177053702 |
| chr2 | 177054113 | 177054351 | chr2 | 177503048 | 177503077 | chr2 | 177503581 | 177503610 |
| chr2 | 178098791 | 178098967 | chr2 | 178973003 | 178973042 | chr2 | 179303691 | 179303727 |
| chr2 | 179317019 | 179317057 | chr2 | 182321397 | 182321637 | chr2 | 182322039 | 182322170 |
| chr2 | 182322400 | 182323042 | chr2 | 182451522 | 182451551 | chr2 | 182542903 | 182542933 |
| chr2 | 182543321 | 182543418 | chr2 | 182543764 | 182543925 | chr2 | 182545211 | 182545275 |
| chr2 | 182545539 | 182545694 | chr2 | 182546002 | 182546085 | chr2 | 182546435 | 182546465 |
| chr2 | 182547385 | 182547387 | chr2 | 182547438 | 182547613 | chr2 | 182548062 | 182548161 |
| chr2 | 182549088 | 182549134 | chr2 | 182549337 | 182549454 | chr2 | 182550094 | 182550124 |
| chr2 | 182819048 | 182819216 | chr2 | 183731294 | 183731331 | chr2 | 183731467 | 183731524 |
| chr2 | 183731809 | 183732076 | chr2 | 185462869 | 185462980 | chr2 | 185463193 | 185463817 |
| chr2 | 186603488 | 186603518 | chr2 | 188419047 | 188419204 | chr2 | 189157427 | 189157688 |

TABLE 13-continued

Pan Cancer #3

| chr | start | end | chr | start | end | chr | start | end |
|---|---|---|---|---|---|---|---|---|
| chr2 | 190708790 | 190708819 | chr2 | 193059025 | 193059317 | chr2 | 193059345 | 193059548 |
| chr2 | 193059662 | 193060067 | chr2 | 193060385 | 193060441 | chr2 | 193060683 | 193060891 |
| chr2 | 193061388 | 193061480 | chr2 | 198267345 | 198267374 | chr2 | 198456570 | 198456690 |
| chr2 | 198651002 | 198651076 | chr2 | 200326590 | 200326735 | chr2 | 200327424 | 200327451 |
| chr2 | 200329030 | 200329393 | chr2 | 200329433 | 200329668 | chr2 | 200333801 | 200333834 |
| chr2 | 200334976 | 200335451 | chr2 | 200335592 | 200335952 | chr2 | 201172444 | 201172480 |
| chr2 | 201450556 | 201450707 | chr2 | 201451014 | 201451040 | chr2 | 202097078 | 202097143 |
| chr2 | 202098936 | 202098965 | chr2 | 202101190 | 202101219 | chr2 | 202122459 | 202122683 |
| chr2 | 202899862 | 202899891 | chr2 | 203484608 | 203484627 | chr2 | 203880471 | 203880492 |
| chr2 | 206551072 | 206551362 | chr2 | 207139072 | 207139102 | chr2 | 207139347 | 207139605 |
| chr2 | 207307548 | 207307562 | chr2 | 207308802 | 207308857 | chr2 | 207506691 | 207507181 |
| chr2 | 208588311 | 208588341 | chr2 | 208635534 | 208635774 | chr2 | 208662170 | 208662213 |
| chr2 | 208989294 | 208989382 | chr2 | 209113097 | 209113126 | chr2 | 209225237 | 209225275 |
| chr2 | 209271322 | 209271336 | chr2 | 210636335 | 210636381 | chr2 | 210636430 | 210636689 |
| chr2 | 210636738 | 210636876 | chr2 | 212248428 | 212248457 | chr2 | 212288927 | 212288956 |
| chr2 | 212295683 | 212295820 | chr2 | 212530120 | 212530149 | chr2 | 212537902 | 212537994 |
| chr2 | 212566811 | 212566840 | chr2 | 212578292 | 212578321 | chr2 | 212587132 | 212587161 |
| chr2 | 213401235 | 213401339 | chr2 | 213401613 | 213401947 | chr2 | 213403110 | 213403337 |
| chr2 | 215275823 | 215275852 | chr2 | 215276310 | 215276339 | chr2 | 217448294 | 217448441 |
| chr2 | 217559296 | 217559326 | chr2 | 217559966 | 217559999 | chr2 | 218770207 | 218770270 |
| chr2 | 218806147 | 218806302 | chr2 | 219736151 | 219736691 | chr2 | 219828049 | 219828117 |
| chr2 | 219847462 | 219847555 | chr2 | 219848809 | 219848891 | chr2 | 219848936 | 219849001 |
| chr2 | 219857723 | 219857737 | chr2 | 220080510 | 220081033 | chr2 | 220173989 | 220174036 |
| chr2 | 220174060 | 220174296 | chr2 | 220196354 | 220196567 | chr2 | 220223098 | 220223128 |
| chr2 | 220223648 | 220223699 | chr2 | 220283363 | 220283519 | chr2 | 220299588 | 220299634 |
| chr2 | 220299886 | 220300059 | chr2 | 220349055 | 220349706 | chr2 | 220361447 | 220361466 |
| chr2 | 220416379 | 220416513 | chr2 | 220416848 | 220417649 | chr2 | 222435773 | 222435863 |
| chr2 | 223155722 | 223156188 | chr2 | 223158730 | 223159453 | chr2 | 223159869 | 223160065 |
| chr2 | 223160342 | 223160379 | chr2 | 223161247 | 223161684 | chr2 | 223161807 | 223162063 |
| chr2 | 223162779 | 223162890 | chr2 | 223162929 | 223163224 | chr2 | 223163473 | 223163535 |
| chr2 | 223163768 | 223163954 | chr2 | 223164534 | 223164883 | chr2 | 223165434 | 223165832 |
| chr2 | 223166294 | 223166408 | chr2 | 223166449 | 223166721 | chr2 | 223167389 | 223167573 |
| chr2 | 223168437 | 223168831 | chr2 | 223169640 | 223169864 | chr2 | 223170375 | 223170434 |
| chr2 | 223171109 | 223171180 | chr2 | 223172337 | 223172367 | chr2 | 223172924 | 223173173 |
| chr2 | 223175922 | 223176181 | chr2 | 223176456 | 223176511 | chr2 | 223176720 | 223176983 |
| chr2 | 223177315 | 223177610 | chr2 | 224661671 | 224661701 | chr2 | 224903260 | 224903440 |
| chr2 | 224903690 | 224903755 | chr2 | 224904108 | 224904237 | chr2 | 228029418 | 228029531 |
| chr2 | 228466761 | 228466777 | chr2 | 228735680 | 228735736 | chr2 | 228736215 | 228736295 |
| chr2 | 228736336 | 228736473 | chr2 | 229046107 | 229046503 | chr2 | 230795535 | 230795565 |
| chr2 | 232394970 | 232395021 | chr2 | 232395055 | 232395061 | chr2 | 232479822 | 232479938 |
| chr2 | 232522844 | 232522874 | chr2 | 232791704 | 232792012 | chr2 | 233350208 | 233350539 |
| chr2 | 233350844 | 233351278 | chr2 | 233352102 | 233352451 | chr2 | 233352507 | 233352762 |
| chr2 | 233352776 | 233352853 | chr2 | 233498710 | 233498873 | chr2 | 233498896 | 233499297 |
| chr2 | 233750525 | 233750555 | chr2 | 235404551 | 235404575 | chr2 | 235860746 | 235860808 |
| chr2 | 235861389 | 235861533 | chr2 | 236402771 | 236403013 | chr2 | 236403270 | 236403736 |
| chr2 | 236444269 | 236444298 | chr2 | 236578362 | 236578677 | chr2 | 236877262 | 236877399 |
| chr2 | 237072642 | 237073014 | chr2 | 237073354 | 237073414 | chr2 | 237076725 | 237076815 |
| chr2 | 237077562 | 237077608 | chr2 | 237077846 | 237078348 | chr2 | 237080264 | 237080294 |
| chr2 | 237081341 | 237081426 | chr2 | 237081537 | 237081553 | chr2 | 237082344 | 237082720 |
| chr2 | 237086349 | 237086468 | chr2 | 237145422 | 237145601 | chr2 | 237416216 | 237416429 |
| chr2 | 238395291 | 238395356 | chr2 | 238395906 | 238395961 | chr2 | 238535895 | 238535984 |
| chr2 | 238536005 | 238536114 | chr2 | 238864727 | 238864913 | chr2 | 239031722 | 239031780 |
| chr2 | 239051198 | 239051228 | chr2 | 239140139 | 239140249 | chr2 | 239149844 | 239149951 |
| chr2 | 239265702 | 239265787 | chr2 | 239482485 | 239482519 | chr2 | 239705305 | 239705337 |
| chr2 | 239755164 | 239755194 | chr2 | 239756373 | 239756462 | chr2 | 239756488 | 239756607 |
| chr2 | 239756634 | 239756648 | chr2 | 239757636 | 239757730 | chr2 | 239758126 | 239758144 |
| chr2 | 239758345 | 239758394 | chr2 | 239957330 | 239957448 | chr2 | 240167575 | 240167605 |
| chr2 | 240168811 | 240169051 | chr2 | 240319920 | 240320012 | chr2 | 240582379 | 240582524 |
| chr2 | 240619459 | 240619604 | chr2 | 240658227 | 240658421 | chr2 | 240658667 | 240658697 |
| chr2 | 241095604 | 241095772 | chr2 | 241393200 | 241393469 | chr2 | 241497411 | 241497554 |
| chr2 | 241541932 | 241542357 | chr2 | 241545001 | 241545031 | chr2 | 241758377 | 241758819 |
| chr2 | 241759597 | 241759694 | chr2 | 241760149 | 241760178 | chr2 | 241760494 | 241760523 |
| chr2 | 241771165 | 241771257 | chr2 | 241865194 | 241865346 | chr2 | 242009391 | 242009421 |
| chr2 | 242021784 | 242021892 | chr2 | 242523907 | 242524147 | chr2 | 242549849 | 242549957 |
| chr2 | 242554549 | 242554579 | chr2 | 242716723 | 242716760 | chr2 | 242756144 | 242756297 |
| chr2 | 242832984 | 242833159 | chr2 | 242833558 | 242833588 | chr2 | 242833797 | 242833863 |
| chr2 | 242836495 | 242836640 | chr2 | 242925496 | 242925641 | chr3 | 238536 | 238715 |
| chr3 | 239007 | 239094 | chr3 | 239622 | 239868 | chr3 | 240110 | 240223 |
| chr3 | 2140277 | 2140398 | chr3 | 3840498 | 3840758 | chr3 | 3841046 | 3841144 |
| chr3 | 3842679 | 3842731 | chr3 | 5137960 | 5138019 | chr3 | 6902288 | 6902353 |
| chr3 | 6903425 | 6903463 | chr3 | 8810152 | 8810220 | chr3 | 9593979 | 9594015 |
| chr3 | 9594263 | 9594382 | chr3 | 9595396 | 9595502 | chr3 | 9904233 | 9904554 |
| chr3 | 9941469 | 9941509 | chr3 | 9957064 | 9957142 | chr3 | 9957451 | 9957677 |
| chr3 | 10182839 | 10182996 | chr3 | 10183321 | 10183350 | chr3 | 10183706 | 10183782 |
| chr3 | 10184304 | 10184333 | chr3 | 10191477 | 10191620 | chr3 | 11034264 | 11034359 |
| chr3 | 11035070 | 11035330 | chr3 | 12046405 | 12046632 | chr3 | 12632309 | 12632401 |

TABLE 13-continued

Pan Cancer #3

| chr | start | end | chr | start | end | chr | start | end |
|---|---|---|---|---|---|---|---|---|
| chr3 | 12645678 | 12645713 | chr3 | 12729424 | 12729454 | chr3 | 12917606 | 12917655 |
| chr3 | 12926053 | 12926102 | chr3 | 12977067 | 12977144 | chr3 | 13323494 | 13323973 |
| chr3 | 13324420 | 13324433 | chr3 | 13324847 | 13324938 | chr3 | 13590448 | 13590640 |
| chr3 | 13679172 | 13679349 | chr3 | 13921407 | 13921463 | chr3 | 14851850 | 14851897 |
| chr3 | 14852325 | 14852919 | chr3 | 15123848 | 15123992 | chr3 | 16554052 | 16554111 |
| chr3 | 16554347 | 16554633 | chr3 | 17001303 | 17001333 | chr3 | 19189441 | 19189470 |
| chr3 | 19189694 | 19189765 | chr3 | 19190143 | 19190216 | chr3 | 20070714 | 20070869 |
| chr3 | 22413665 | 22413694 | chr3 | 22413960 | 22413974 | chr3 | 23964981 | 23965019 |
| chr3 | 24871002 | 24871176 | chr3 | 25469110 | 25469139 | chr3 | 25469377 | 25469406 |
| chr3 | 25469679 | 25469708 | chr3 | 26664045 | 26664119 | chr3 | 26664389 | 26664755 |
| chr3 | 27754478 | 27754508 | chr3 | 27762336 | 27762650 | chr3 | 27762857 | 27762887 |
| chr3 | 27763566 | 27763595 | chr3 | 27764457 | 27764471 | chr3 | 27765181 | 27765347 |
| chr3 | 27771497 | 27772004 | chr3 | 27772790 | 27772819 | chr3 | 28616832 | 28617675 |
| chr3 | 31494108 | 31494138 | chr3 | 32858353 | 32858958 | chr3 | 32859256 | 32859284 |
| chr3 | 32859418 | 32859693 | chr3 | 32860068 | 32860273 | chr3 | 33259904 | 33260776 |
| chr3 | 35680842 | 35680872 | chr3 | 36805815 | 36805863 | chr3 | 36806179 | 36806193 |
| chr3 | 36984378 | 36984402 | chr3 | 37493519 | 37493621 | chr3 | 37901923 | 37901953 |
| chr3 | 38030618 | 38030782 | chr3 | 38032331 | 38032361 | chr3 | 38035774 | 38035989 |
| chr3 | 38080685 | 38080925 | chr3 | 38081154 | 38081271 | chr3 | 38182244 | 38182306 |
| chr3 | 38182626 | 38182655 | chr3 | 38690624 | 38690668 | chr3 | 39851772 | 39851814 |
| chr3 | 40428507 | 40428713 | chr3 | 41266086 | 41266151 | chr3 | 42222730 | 42222759 |
| chr3 | 42640855 | 42640880 | chr3 | 42814569 | 42814603 | chr3 | 42947411 | 42947552 |
| chr3 | 44036260 | 44036330 | chr3 | 44036570 | 44036600 | chr3 | 44036820 | 44037203 |
| chr3 | 44037625 | 44037662 | chr3 | 44037874 | 44038646 | chr3 | 44039348 | 44040006 |
| chr3 | 44040511 | 44040553 | chr3 | 44040796 | 44041039 | chr3 | 44063434 | 44063872 |
| chr3 | 44596479 | 44596509 | chr3 | 44596716 | 44596809 | chr3 | 44626438 | 44626711 |
| chr3 | 44726875 | 44727193 | chr3 | 45187296 | 45187327 | chr3 | 46924934 | 46924964 |
| chr3 | 47144864 | 47144893 | chr3 | 48227765 | 48227788 | chr3 | 48236476 | 48236570 |
| chr3 | 48693304 | 48693700 | chr3 | 48693852 | 48694154 | chr3 | 48698251 | 48698431 |
| chr3 | 48698810 | 48699010 | chr3 | 48699377 | 48699767 | chr3 | 49236845 | 49236874 |
| chr3 | 49405953 | 49405982 | chr3 | 49412883 | 49412987 | chr3 | 49591832 | 49592076 |
| chr3 | 49907093 | 49907130 | chr3 | 49939931 | 49940398 | chr3 | 50072827 | 50072846 |
| chr3 | 50243383 | 50243480 | chr3 | 50374655 | 50374684 | chr3 | 50374917 | 50374946 |
| chr3 | 50375179 | 50375559 | chr3 | 50377973 | 50378002 | chr3 | 50378277 | 50378306 |
| chr3 | 50378512 | 50378541 | chr3 | 50395506 | 50395536 | chr3 | 50402170 | 50402944 |
| chr3 | 50575616 | 50575637 | chr3 | 50968445 | 50968511 | chr3 | 52442062 | 52442091 |
| chr3 | 52552556 | 52552661 | chr3 | 52553469 | 52553499 | chr3 | 53032733 | 53033524 |
| chr3 | 54155611 | 54155677 | chr3 | 54157381 | 54157450 | chr3 | 54157878 | 54157919 |
| chr3 | 55519219 | 55519253 | chr3 | 55523106 | 55523290 | chr3 | 55603443 | 55603632 |
| chr3 | 58153446 | 58153608 | chr3 | 62304567 | 62304669 | chr3 | 62353371 | 62354049 |
| chr3 | 62354283 | 62354328 | chr3 | 62354625 | 62354792 | chr3 | 62354900 | 62354914 |
| chr3 | 62355424 | 62355478 | chr3 | 62355774 | 62356219 | chr3 | 62356302 | 62356644 |
| chr3 | 62356793 | 62357192 | chr3 | 62357279 | 62357347 | chr3 | 62357624 | 62357667 |
| chr3 | 62358530 | 62358595 | chr3 | 62358858 | 62359011 | chr3 | 62359376 | 62359893 |
| chr3 | 62360302 | 62360560 | chr3 | 62362902 | 62362916 | chr3 | 62363099 | 62363200 |
| chr3 | 62363626 | 62363693 | chr3 | 62363906 | 62364176 | chr3 | 62364280 | 62364329 |
| chr3 | 62364702 | 62365154 | chr3 | 62861118 | 62861148 | chr3 | 63264139 | 63264169 |
| chr3 | 66053446 | 66053470 | chr3 | 68056904 | 68057145 | chr3 | 68980931 | 68981113 |
| chr3 | 68981552 | 68981624 | chr3 | 69590939 | 69590969 | chr3 | 69591363 | 69591414 |
| chr3 | 69591780 | 69591977 | chr3 | 69740967 | 69740990 | chr3 | 69937703 | 69937848 |
| chr3 | 71802518 | 71802622 | chr3 | 71803126 | 71803372 | chr3 | 71803643 | 71803783 |
| chr3 | 73045492 | 73045583 | chr3 | 75956027 | 75956375 | chr3 | 79815522 | 79815557 |
| chr3 | 79816778 | 79817015 | chr3 | 79817288 | 79817318 | chr3 | 85008553 | 85008708 |
| chr3 | 88248025 | 88248049 | chr3 | 96532817 | 96532873 | chr3 | 96533383 | 96533458 |
| chr3 | 96534035 | 96534096 | chr3 | 98620891 | 98620980 | chr3 | 99594925 | 99595105 |
| chr3 | 101230678 | 101230694 | chr3 | 101230934 | 101231070 | chr3 | 101397240 | 101397329 |
| chr3 | 101497841 | 101497996 | chr3 | 106936157 | 106936336 | chr3 | 112052252 | 112052419 |
| chr3 | 115512319 | 115512354 | chr3 | 117715549 | 117715651 | chr3 | 117715771 | 117716123 |
| chr3 | 117716214 | 117716473 | chr3 | 120004080 | 120004405 | chr3 | 120004468 | 120004497 |
| chr3 | 120169104 | 120169149 | chr3 | 120169768 | 120169835 | chr3 | 120627317 | 120627453 |
| chr3 | 121902991 | 121903218 | chr3 | 121903324 | 121903619 | chr3 | 122234242 | 122234270 |
| chr3 | 122702288 | 122702430 | chr3 | 123167301 | 123167529 | chr3 | 123167769 | 123167827 |
| chr3 | 125898597 | 125899207 | chr3 | 125899525 | 125899962 | chr3 | 125932252 | 125932500 |
| chr3 | 126157586 | 126157663 | chr3 | 126261929 | 126262000 | chr3 | 126373520 | 126373704 |
| chr3 | 126854699 | 126854796 | chr3 | 127534814 | 127534897 | chr3 | 127634186 | 127634216 |
| chr3 | 127794546 | 127794860 | chr3 | 127795325 | 127795408 | chr3 | 128056383 | 128056497 |
| chr3 | 128202447 | 128202477 | chr3 | 128208903 | 128209232 | chr3 | 128273993 | 128274051 |
| chr3 | 128274309 | 128274611 | chr3 | 128417201 | 128417231 | chr3 | 128720061 | 128720142 |
| chr3 | 128720164 | 128720346 | chr3 | 128720419 | 128720533 | chr3 | 128720567 | 128720611 |
| chr3 | 128720869 | 128721229 | chr3 | 128764489 | 128764606 | chr3 | 129693108 | 129693199 |
| chr3 | 129693305 | 129693498 | chr3 | 129694299 | 129694299 | chr3 | 130064451 | 130064484 |
| chr3 | 130064818 | 130064848 | chr3 | 130236049 | 130236063 | chr3 | 130236174 | 130236273 |
| chr3 | 130519901 | 130519929 | chr3 | 131754031 | 131754061 | chr3 | 132757065 | 132757104 |
| chr3 | 133217922 | 133217999 | chr3 | 133748140 | 133748245 | chr3 | 133748481 | 133748576 |
| chr3 | 134369646 | 134369855 | chr3 | 134514866 | 134514895 | chr3 | 134515128 | 134515369 |
| chr3 | 134515676 | 134516222 | chr3 | 136016868 | 136016942 | chr3 | 136537642 | 136537730 |

TABLE 13-continued

| Pan Cancer #3 | | | | | | | | |
|---|---|---|---|---|---|---|---|---|
| chr | start | end | chr | start | end | chr | start | end |
| chr3 | 136538585 | 136538815 | chr3 | 136582917 | 136582951 | chr3 | 136751641 | 136751809 |
| chr3 | 137479233 | 137479302 | chr3 | 137479601 | 137479687 | chr3 | 137479980 | 137480764 |
| chr3 | 137481170 | 137481315 | chr3 | 137481858 | 137481872 | chr3 | 137481936 | 137482183 |
| chr3 | 137483313 | 137483437 | chr3 | 137483514 | 137483589 | chr3 | 137483848 | 137484002 |
| chr3 | 137484405 | 137484531 | chr3 | 137486029 | 137486310 | chr3 | 137486516 | 137486550 |
| chr3 | 137487964 | 137488003 | chr3 | 137488950 | 137489698 | chr3 | 137489876 | 137491040 |
| chr3 | 138067717 | 138067747 | chr3 | 138153963 | 138153993 | chr3 | 138374229 | 138374258 |
| chr3 | 138655934 | 138656138 | chr3 | 138656834 | 138656889 | chr3 | 138657414 | 138657494 |
| chr3 | 138657618 | 138658296 | chr3 | 138658704 | 138658863 | chr3 | 138659081 | 138659099 |
| chr3 | 138662134 | 138662164 | chr3 | 138662282 | 138662296 | chr3 | 138662382 | 138662448 |
| chr3 | 138662799 | 138662842 | chr3 | 138663613 | 138663727 | chr3 | 138664142 | 138664165 |
| chr3 | 138664928 | 138665323 | chr3 | 138665562 | 138665718 | chr3 | 138665778 | 138666294 |
| chr3 | 138668758 | 138669108 | chr3 | 138669141 | 138669387 | chr3 | 139258267 | 139258316 |
| chr3 | 139653491 | 139653693 | chr3 | 140769513 | 140769705 | chr3 | 140769908 | 140770301 |
| chr3 | 140770408 | 140770589 | chr3 | 140770644 | 140770829 | chr3 | 140771305 | 140771335 |
| chr3 | 140771816 | 140771854 | chr3 | 141174349 | 141174606 | chr3 | 141481982 | 141482073 |
| chr3 | 141516389 | 141516719 | chr3 | 141657032 | 141657079 | chr3 | 141836036 | 141836077 |
| chr3 | 142537638 | 142537779 | chr3 | 142682273 | 142682392 | chr3 | 142791151 | 142791173 |
| chr3 | 142837980 | 142838318 | chr3 | 142838621 | 142838646 | chr3 | 142838877 | 142839036 |
| chr3 | 142839563 | 142839688 | chr3 | 142839784 | 142839901 | chr3 | 142839945 | 142840127 |
| chr3 | 142840222 | 142840236 | chr3 | 142896156 | 142896214 | chr3 | 143280343 | 143280373 |
| chr3 | 145878665 | 145878695 | chr3 | 146187946 | 146187978 | chr3 | 147074457 | 147074487 |
| chr3 | 147074974 | 147075006 | chr3 | 147077289 | 147077671 | chr3 | 147078959 | 147079188 |
| chr3 | 147087562 | 147087799 | chr3 | 147088440 | 147088523 | chr3 | 147088939 | 147089099 |
| chr3 | 147098431 | 147098470 | chr3 | 147105898 | 147106010 | chr3 | 147108841 | 147109765 |
| chr3 | 147110229 | 147110683 | chr3 | 147110927 | 147111089 | chr3 | 147125697 | 147125726 |
| chr3 | 147127037 | 147127067 | chr3 | 147127681 | 147127902 | chr3 | 147136931 | 147137000 |
| chr3 | 147137076 | 147137164 | chr3 | 147138768 | 147138856 | chr3 | 147139374 | 147139528 |
| chr3 | 148415427 | 148415644 | chr3 | 148523213 | 148523255 | chr3 | 148803258 | 148803276 |
| chr3 | 149374947 | 149375023 | chr3 | 150802981 | 150802999 | chr3 | 150803026 | 150803080 |
| chr3 | 150804043 | 150804077 | chr3 | 150804967 | 150805030 | chr3 | 152553343 | 152553384 |
| chr3 | 152553658 | 152553725 | chr3 | 152877666 | 152877696 | chr3 | 153838818 | 153838870 |
| chr3 | 153839518 | 153839952 | chr3 | 154146133 | 154146394 | chr3 | 154146654 | 154146908 |
| chr3 | 154797334 | 154797703 | chr3 | 155461030 | 155461053 | chr3 | 155463041 | 155463071 |
| chr3 | 156007772 | 156007801 | chr3 | 156008976 | 156009299 | chr3 | 156009319 | 156009425 |
| chr3 | 157155252 | 157155490 | chr3 | 157155982 | 157156194 | chr3 | 157812196 | 157812257 |
| chr3 | 157812437 | 157812645 | chr3 | 157812912 | 157813070 | chr3 | 157813670 | 157813824 |
| chr3 | 157814311 | 157814340 | chr3 | 157815657 | 157815822 | chr3 | 157820576 | 157820605 |
| chr3 | 157821537 | 157821662 | chr3 | 157821904 | 157822008 | chr3 | 157823073 | 157823119 |
| chr3 | 157823139 | 157823143 | chr3 | 157823464 | 157823493 | chr3 | 157824133 | 157824146 |
| chr3 | 157824212 | 157824231 | chr3 | 157824495 | 157824871 | chr3 | 157825176 | 157825408 |
| chr3 | 159756687 | 159756856 | chr3 | 159944486 | 159944546 | chr3 | 164912376 | 164912456 |
| chr3 | 164912907 | 164913872 | chr3 | 164914980 | 164915129 | chr3 | 169376183 | 169376215 |
| chr3 | 169376680 | 169376780 | chr3 | 169378825 | 169379024 | chr3 | 169539898 | 169540679 |
| chr3 | 169541070 | 169541102 | chr3 | 170136627 | 170136751 | chr3 | 170302617 | 170302677 |
| chr3 | 170303087 | 170303129 | chr3 | 170303380 | 170303423 | chr3 | 170303639 | 170303844 |
| chr3 | 171527930 | 171527971 | chr3 | 172165443 | 172165784 | chr3 | 172165867 | 172166512 |
| chr3 | 172166879 | 172166893 | chr3 | 172167000 | 172167044 | chr3 | 172167297 | 172167327 |
| chr3 | 172167660 | 172167917 | chr3 | 172355895 | 172355997 | chr3 | 172425382 | 172425400 |
| chr3 | 172425700 | 172425717 | chr3 | 172469925 | 172469951 | chr3 | 173115237 | 173115550 |
| chr3 | 173302542 | 173302668 | chr3 | 173302992 | 173303225 | chr3 | 176710106 | 176710144 |
| chr3 | 178861413 | 178861447 | chr3 | 178916711 | 178916959 | chr3 | 178921537 | 178921568 |
| chr3 | 178927966 | 178928094 | chr3 | 178936059 | 178936111 | chr3 | 178952004 | 178952105 |
| chr3 | 179168661 | 179169266 | chr3 | 179367897 | 179367920 | chr3 | 179754178 | 179754192 |
| chr3 | 179754239 | 179754759 | chr3 | 179754804 | 179754872 | chr3 | 179755087 | 179755372 |
| chr3 | 180320256 | 180320294 | chr3 | 181413742 | 181414330 | chr3 | 181420065 | 181420116 |
| chr3 | 181420316 | 181420374 | chr3 | 181421411 | 181422282 | chr3 | 181422541 | 181422985 |
| chr3 | 181428388 | 181428772 | chr3 | 181430695 | 181430771 | chr3 | 181437129 | 181437349 |
| chr3 | 181438194 | 181438353 | chr3 | 181440892 | 181441927 | chr3 | 181442145 | 181442410 |
| chr3 | 181443014 | 181443557 | chr3 | 181443760 | 181443861 | chr3 | 181444108 | 181444236 |
| chr3 | 181444434 | 181444524 | chr3 | 181444613 | 181444754 | chr3 | 181444814 | 181444948 |
| chr3 | 181444989 | 181445013 | chr3 | 181445369 | 181445464 | chr3 | 181445800 | 181445861 |
| chr3 | 182816009 | 182816027 | chr3 | 182895956 | 182895990 | chr3 | 182911545 | 182911574 |
| chr3 | 183109854 | 183109883 | chr3 | 183145412 | 183145618 | chr3 | 183145931 | 183146025 |
| chr3 | 183146397 | 183146435 | chr3 | 183146648 | 183146677 | chr3 | 183217676 | 183217706 |
| chr3 | 183647996 | 183648026 | chr3 | 183728813 | 183728952 | chr3 | 183965599 | 183965633 |
| chr3 | 184018038 | 184018136 | chr3 | 184031686 | 184031746 | chr3 | 184057526 | 184057557 |
| chr3 | 184099417 | 184099446 | chr3 | 184319470 | 184319612 | chr3 | 184319828 | 184319842 |
| chr3 | 184319874 | 184319891 | chr3 | 185001898 | 185001919 | chr3 | 185271296 | 185271380 |
| chr3 | 185303247 | 185303277 | chr3 | 185363074 | 185363261 | chr3 | 185643324 | 185643405 |
| chr3 | 186078766 | 186078898 | chr3 | 186079204 | 186079331 | chr3 | 186080188 | 186080218 |
| chr3 | 186857152 | 186857607 | chr3 | 186914705 | 186914734 | chr3 | 187387850 | 187387920 |
| chr3 | 187388007 | 187388239 | chr3 | 192125828 | 192125828 | chr3 | 192126146 | 192126710 |
| chr3 | 192126787 | 192126863 | chr3 | 192127354 | 192127372 | chr3 | 192127557 | 192127730 |
| chr3 | 192127937 | 192128074 | chr3 | 192232097 | 192232175 | chr3 | 192232452 | 192232570 |
| chr3 | 192232850 | 192232951 | chr3 | 192233095 | 192233150 | chr3 | 192958725 | 192958968 |

TABLE 13-continued

Pan Cancer #3

| chr | start | end | chr | start | end | chr | start | end |
|---|---|---|---|---|---|---|---|---|
| chr3 | 193312128 | 193312208 | chr3 | 193419702 | 193419732 | chr3 | 193548637 | 193548835 |
| chr3 | 193776089 | 193776119 | chr3 | 194048751 | 194048919 | chr3 | 194120008 | 194120164 |
| chr3 | 194120812 | 194120841 | chr3 | 194120934 | 194120963 | chr3 | 194208468 | 194208562 |
| chr3 | 194407998 | 194408028 | chr3 | 194408375 | 194408768 | chr3 | 194408839 | 194409021 |
| chr3 | 194981816 | 194981895 | chr3 | 195095450 | 195095467 | chr3 | 195095527 | 195095543 |
| chr3 | 195536733 | 195536848 | chr3 | 195538315 | 195538353 | chr3 | 195587032 | 195587118 |
| chr3 | 195601239 | 195601312 | chr3 | 195602363 | 195602576 | chr3 | 195648794 | 195648899 |
| chr3 | 196046702 | 196046736 | chr3 | 196065342 | 196065583 | chr3 | 196069892 | 196070192 |
| chr3 | 196255617 | 196255631 | chr3 | 196344683 | 196344710 | chr3 | 196387295 | 196387415 |
| chr3 | 196387628 | 196387665 | chr3 | 196388383 | 196388581 | chr3 | 196440510 | 196440593 |
| chr3 | 196728418 | 196728448 | chr3 | 196731155 | 196731313 | chr3 | 196755958 | 196755987 |
| chr3 | 197209019 | 197209048 | chr3 | 197236945 | 197237111 | chr3 | 197247047 | 197247110 |
| chr3 | 197278926 | 197278988 | chr3 | 197327011 | 197327042 | chr3 | 197330104 | 197330147 |
| chr3 | 197616707 | 197616861 | chr3 | 197677029 | 197677058 | chr3 | 197685788 | 197685817 |
| chr3 | 197686057 | 197686085 | chr3 | 197686495 | 197686524 | chr3 | 197686941 | 197687223 |
| chr3 | 197687694 | 197687723 | chr4 | 206324 | 206353 | chr4 | 331322 | 331352 |
| chr4 | 512978 | 513008 | chr4 | 513704 | 513734 | chr4 | 568429 | 568652 |
| chr4 | 569048 | 569115 | chr4 | 569275 | 569435 | chr4 | 569461 | 569732 |
| chr4 | 570966 | 571013 | chr4 | 571508 | 571689 | chr4 | 628572 | 628787 |
| chr4 | 651196 | 651261 | chr4 | 657521 | 657552 | chr4 | 678471 | 678501 |
| chr4 | 718052 | 718112 | chr4 | 718321 | 718359 | chr4 | 829611 | 829641 |
| chr4 | 955367 | 955454 | chr4 | 955867 | 955919 | chr4 | 995876 | 995993 |
| chr4 | 996101 | 996174 | chr4 | 1008740 | 1008902 | chr4 | 1016127 | 1016252 |
| chr4 | 1016586 | 1016747 | chr4 | 1025928 | 1026074 | chr4 | 1041763 | 1041926 |
| chr4 | 1093536 | 1093675 | chr4 | 1107494 | 1107585 | chr4 | 1165450 | 1165470 |
| chr4 | 1189021 | 1189051 | chr4 | 1214894 | 1215162 | chr4 | 1215415 | 1215451 |
| chr4 | 1282515 | 1282545 | chr4 | 1331675 | 1331705 | chr4 | 1336755 | 1336902 |
| chr4 | 1338715 | 1338812 | chr4 | 1339099 | 1339130 | chr4 | 1396578 | 1396696 |
| chr4 | 1397396 | 1397495 | chr4 | 1398303 | 1398378 | chr4 | 1399723 | 1399768 |
| chr4 | 1401711 | 1401743 | chr4 | 1512368 | 1512398 | chr4 | 1556419 | 1556609 |
| chr4 | 1576484 | 1576528 | chr4 | 1616682 | 1617247 | chr4 | 1687080 | 1687110 |
| chr4 | 1800153 | 1800191 | chr4 | 1803550 | 1803582 | chr4 | 1806084 | 1806113 |
| chr4 | 1807355 | 1807384 | chr4 | 1962787 | 1962816 | chr4 | 1993771 | 1994180 |
| chr4 | 2042106 | 2042122 | chr4 | 2042169 | 2042258 | chr4 | 2066114 | 2066265 |
| chr4 | 2305672 | 2305827 | chr4 | 2527907 | 2527937 | chr4 | 2540215 | 2540297 |
| chr4 | 2765862 | 2765910 | chr4 | 2926366 | 2926396 | chr4 | 2978968 | 2979145 |
| chr4 | 3036118 | 3036148 | chr4 | 3217107 | 3217154 | chr4 | 3371519 | 3371652 |
| chr4 | 3446991 | 3447021 | chr4 | 3447816 | 3448015 | chr4 | 3768833 | 3768949 |
| chr4 | 3768995 | 3769189 | chr4 | 3769560 | 3769574 | chr4 | 3873694 | 3873769 |
| chr4 | 4228189 | 4228241 | chr4 | 4229689 | 4229781 | chr4 | 4387533 | 4387627 |
| chr4 | 4417568 | 4417603 | chr4 | 4855102 | 4855171 | chr4 | 4855371 | 4855433 |
| chr4 | 4860046 | 4860075 | chr4 | 4862769 | 4863110 | chr4 | 4867698 | 4867886 |
| chr4 | 4868566 | 4868792 | chr4 | 4868829 | 4868999 | chr4 | 4872088 | 4872167 |
| chr4 | 4872777 | 4872850 | chr4 | 4873427 | 4873528 | chr4 | 5021188 | 5021217 |
| chr4 | 5053070 | 5053518 | chr4 | 5053747 | 5054093 | chr4 | 5709906 | 5709984 |
| chr4 | 5712979 | 5713231 | chr4 | 5889948 | 5890045 | chr4 | 5890274 | 5890444 |
| chr4 | 5891966 | 5892081 | chr4 | 5892110 | 5892194 | chr4 | 5892750 | 5892780 |
| chr4 | 5893981 | 5894082 | chr4 | 6200897 | 6201235 | chr4 | 6202103 | 6202276 |
| chr4 | 6247351 | 6247381 | chr4 | 6565004 | 6565042 | chr4 | 6670184 | 6670214 |
| chr4 | 6748346 | 6748557 | chr4 | 6957481 | 6957620 | chr4 | 7647770 | 7647945 |
| chr4 | 7758476 | 7758561 | chr4 | 8582549 | 8582579 | chr4 | 8607813 | 8607932 |
| chr4 | 8608556 | 8608600 | chr4 | 8858827 | 8859047 | chr4 | 8859382 | 8859738 |
| chr4 | 8860398 | 8860553 | chr4 | 8861649 | 8861752 | chr4 | 8861919 | 8862014 |
| chr4 | 8862797 | 8862811 | chr4 | 8863441 | 8863526 | chr4 | 8864499 | 8864598 |
| chr4 | 8864831 | 8865058 | chr4 | 8868822 | 8868845 | chr4 | 8868932 | 8869270 |
| chr4 | 8869601 | 8869813 | chr4 | 8873054 | 8873072 | chr4 | 8873809 | 8873984 |
| chr4 | 8874485 | 8874534 | chr4 | 8874773 | 8874787 | chr4 | 8875877 | 8875907 |
| chr4 | 8893060 | 8893093 | chr4 | 8893501 | 8893531 | chr4 | 8893816 | 8893931 |
| chr4 | 8894641 | 8894957 | chr4 | 8895232 | 8895350 | chr4 | 8895554 | 8895584 |
| chr4 | 8895965 | 8896052 | chr4 | 9423273 | 9423314 | chr4 | 9782992 | 9783095 |
| chr4 | 9783126 | 9783412 | chr4 | 10458395 | 10459121 | chr4 | 10462833 | 10463047 |
| chr4 | 10463073 | 10463604 | chr4 | 11429506 | 11429633 | chr4 | 13524026 | 13524251 |
| chr4 | 13524665 | 13524775 | chr4 | 13524957 | 13524971 | chr4 | 13537569 | 13537688 |
| chr4 | 13540983 | 13541068 | chr4 | 13546026 | 13546078 | chr4 | 13548502 | 13548589 |
| chr4 | 13548635 | 13548895 | chr4 | 13549340 | 13549510 | chr4 | 15780223 | 15780320 |
| chr4 | 16084741 | 16084818 | chr4 | 16085167 | 16085301 | chr4 | 16085352 | 16085381 |
| chr4 | 16085675 | 16085682 | chr4 | 17783003 | 17783480 | chr4 | 20254693 | 20254723 |
| chr4 | 20255525 | 20255861 | chr4 | 20256152 | 20256285 | chr4 | 21950248 | 21950295 |
| chr4 | 24801868 | 24801985 | chr4 | 24914638 | 24914668 | chr4 | 25656815 | 25656879 |
| chr4 | 25657437 | 25657477 | chr4 | 27086432 | 27086462 | chr4 | 30722243 | 30722273 |
| chr4 | 30723856 | 30723862 | chr4 | 30724249 | 30724372 | chr4 | 37245833 | 37245851 |
| chr4 | 37246134 | 37246360 | chr4 | 37246490 | 37246699 | chr4 | 37247096 | 37247216 |
| chr4 | 38566373 | 38566418 | chr4 | 38673115 | 38673144 | chr4 | 40632773 | 40632802 |
| chr4 | 40910303 | 40910465 | chr4 | 41258716 | 41258788 | chr4 | 41259086 | 41259176 |
| chr4 | 41747009 | 41747133 | chr4 | 41747493 | 41747582 | chr4 | 41747958 | 41747977 |
| chr4 | 41748144 | 41748296 | chr4 | 41748660 | 41748766 | chr4 | 41749033 | 41749063 |

TABLE 13-continued

Pan Cancer #3

| chr | start | end | chr | start | end | chr | start | end |
|---|---|---|---|---|---|---|---|---|
| chr4 | 41749270 | 41749761 | chr4 | 41750223 | 41750504 | chr4 | 41751870 | 41752006 |
| chr4 | 41752451 | 41752693 | chr4 | 41752968 | 41753398 | chr4 | 41753610 | 41753916 |
| chr4 | 41754031 | 41754071 | chr4 | 41875430 | 41875902 | chr4 | 41880331 | 41880412 |
| chr4 | 41881385 | 41881425 | chr4 | 41883091 | 41883302 | chr4 | 41883510 | 41883610 |
| chr4 | 41993716 | 41993815 | chr4 | 42152962 | 42153411 | chr4 | 42153533 | 42153632 |
| chr4 | 42153882 | 42154025 | chr4 | 42154280 | 42154359 | chr4 | 42154662 | 42154997 |
| chr4 | 42155293 | 42155322 | chr4 | 42348266 | 42348331 | chr4 | 42398842 | 42398872 |
| chr4 | 42399137 | 42399191 | chr4 | 42399688 | 42399872 | chr4 | 44449480 | 44449569 |
| chr4 | 46391353 | 46391383 | chr4 | 46911535 | 46911564 | chr4 | 46995161 | 46995835 |
| chr4 | 47034908 | 47034938 | chr4 | 48485067 | 48485288 | chr4 | 48485590 | 48486000 |
| chr4 | 48486356 | 48486389 | chr4 | 48492181 | 48492433 | chr4 | 48848428 | 48848461 |
| chr4 | 48988109 | 48988335 | chr4 | 53728495 | 53729056 | chr4 | 54966854 | 54967075 |
| chr4 | 54967342 | 54967484 | chr4 | 54969833 | 54970095 | chr4 | 54970349 | 54970482 |
| chr4 | 54975991 | 54976115 | chr4 | 55093048 | 55093255 | chr4 | 55096239 | 55096344 |
| chr4 | 55097404 | 55097634 | chr4 | 55097973 | 55098092 | chr4 | 55098198 | 55098373 |
| chr4 | 55098674 | 55098744 | chr4 | 55099039 | 55099062 | chr4 | 55133613 | 55133642 |
| chr4 | 55136787 | 55136816 | chr4 | 55138657 | 55138686 | chr4 | 55139691 | 55139720 |
| chr4 | 55140731 | 55140784 | chr4 | 55141015 | 55141050 | chr4 | 55144105 | 55144134 |
| chr4 | 55146554 | 55146583 | chr4 | 55152075 | 55152140 | chr4 | 55524220 | 55524274 |
| chr4 | 55589753 | 55589782 | chr4 | 55592166 | 55592204 | chr4 | 55593417 | 55593675 |
| chr4 | 55594183 | 55594212 | chr4 | 55595504 | 55595614 | chr4 | 55599306 | 55599356 |
| chr4 | 55968165 | 55968194 | chr4 | 55991107 | 55991228 | chr4 | 55992153 | 55992169 |
| chr4 | 56659692 | 56659866 | chr4 | 56659935 | 56660021 | chr4 | 57017423 | 57017459 |
| chr4 | 57371718 | 57371963 | chr4 | 57372336 | 57372504 | chr4 | 57396946 | 57397264 |
| chr4 | 57521506 | 57521663 | chr4 | 57521701 | 57522382 | chr4 | 57522420 | 57522815 |
| chr4 | 57687720 | 57687782 | chr4 | 57777437 | 57777595 | chr4 | 57803528 | 57803558 |
| chr4 | 57976033 | 57976185 | chr4 | 57976416 | 57976573 | chr4 | 58030191 | 58030524 |
| chr4 | 62066196 | 62066553 | chr4 | 62067511 | 62067624 | chr4 | 62068072 | 62068150 |
| chr4 | 66535130 | 66535314 | chr4 | 66535351 | 66535443 | chr4 | 66536171 | 66536323 |
| chr4 | 74702479 | 74702516 | chr4 | 74735076 | 74735137 | chr4 | 74809877 | 74809933 |
| chr4 | 75241348 | 75241435 | chr4 | 75858573 | 75858629 | chr4 | 76555532 | 76555856 |
| chr4 | 76912716 | 76912733 | chr4 | 79611273 | 79611294 | chr4 | 79689651 | 79689732 |
| chr4 | 81106351 | 81106871 | chr4 | 81124277 | 81124662 | chr4 | 81187046 | 81187076 |
| chr4 | 81187559 | 81187589 | chr4 | 81188385 | 81188489 | chr4 | 81188491 | 81188556 |
| chr4 | 81189419 | 81189660 | chr4 | 81189714 | 81189911 | chr4 | 81951431 | 81951460 |
| chr4 | 81951941 | 81951970 | chr4 | 81952170 | 81952311 | chr4 | 82135873 | 82135887 |
| chr4 | 82135920 | 82136056 | chr4 | 82136495 | 82136548 | chr4 | 82136807 | 82136837 |
| chr4 | 83323506 | 83323708 | chr4 | 83720611 | 83720643 | chr4 | 84035907 | 84035936 |
| chr4 | 85402377 | 85402511 | chr4 | 85402776 | 85403423 | chr4 | 85403913 | 85403927 |
| chr4 | 85404112 | 85404140 | chr4 | 85404225 | 85404475 | chr4 | 85404650 | 85404693 |
| chr4 | 85414045 | 85414113 | chr4 | 85414725 | 85414846 | chr4 | 85417336 | 85417564 |
| chr4 | 85417953 | 85418079 | chr4 | 85418522 | 85418582 | chr4 | 85420591 | 85420621 |
| chr4 | 85422188 | 85422432 | chr4 | 85422973 | 85423316 | chr4 | 85424401 | 85424483 |
| chr4 | 87515337 | 87515367 | chr4 | 89378464 | 89378497 | chr4 | 89378744 | 89378766 |
| chr4 | 89378832 | 89378888 | chr4 | 90757517 | 90757828 | chr4 | 90758105 | 90758134 |
| chr4 | 90758776 | 90758883 | chr4 | 93224972 | 93225171 | chr4 | 93226365 | 93226703 |
| chr4 | 93226729 | 93227129 | chr4 | 94749725 | 94749755 | chr4 | 94750982 | 94751140 |
| chr4 | 94751419 | 94751502 | chr4 | 94753415 | 94753445 | chr4 | 94756002 | 94756109 |
| chr4 | 95127590 | 95127684 | chr4 | 96470752 | 96470782 | chr4 | 101111246 | 101111504 |
| chr4 | 101111857 | 101111970 | chr4 | 102711731 | 102711787 | chr4 | 106335495 | 106335526 |
| chr4 | 107955311 | 107955826 | chr4 | 107956676 | 107957086 | chr4 | 107957373 | 107957466 |
| chr4 | 109093101 | 109093168 | chr4 | 109093405 | 109093506 | chr4 | 110223090 | 110223427 |
| chr4 | 110223579 | 110223980 | chr4 | 110344278 | 110344294 | chr4 | 111532705 | 111532961 |
| chr4 | 111536288 | 111536505 | chr4 | 111536562 | 111536693 | chr4 | 111536960 | 111536974 |
| chr4 | 111537407 | 111537497 | chr4 | 111540199 | 111540360 | chr4 | 111542474 | 111542757 |
| chr4 | 111543232 | 111543345 | chr4 | 111543404 | 111543450 | chr4 | 111543661 | 111543695 |
| chr4 | 111543721 | 111543735 | chr4 | 111544381 | 111544583 | chr4 | 111549800 | 111549830 |
| chr4 | 111550618 | 111550834 | chr4 | 111552118 | 111552148 | chr4 | 111553099 | 111553450 |
| chr4 | 111553916 | 111553951 | chr4 | 111554950 | 111554964 | chr4 | 111555194 | 111555343 |
| chr4 | 111557965 | 111558049 | chr4 | 111558551 | 111559233 | chr4 | 111560249 | 111560636 |
| chr4 | 111562576 | 111562648 | chr4 | 113154896 | 113155043 | chr4 | 113430640 | 113430672 |
| chr4 | 113431834 | 113431854 | chr4 | 113431916 | 113432154 | chr4 | 113432227 | 113432503 |
| chr4 | 113432519 | 113432573 | chr4 | 113436216 | 113436287 | chr4 | 113441592 | 113441733 |
| chr4 | 113442098 | 113442185 | chr4 | 113442247 | 113442525 | chr4 | 113444020 | 113444448 |
| chr4 | 117847399 | 117847458 | chr4 | 121844063 | 121844206 | chr4 | 121992265 | 121992312 |
| chr4 | 121993997 | 121994251 | chr4 | 122301422 | 122301712 | chr4 | 122302116 | 122302246 |
| chr4 | 122685807 | 122685890 | chr4 | 122686209 | 122686507 | chr4 | 122871294 | 122871334 |
| chr4 | 122871573 | 122872000 | chr4 | 123664228 | 123664363 | chr4 | 126237310 | 126237611 |
| chr4 | 126238024 | 126238436 | chr4 | 128544048 | 128544161 | chr4 | 128544646 | 128544789 |
| chr4 | 128967290 | 128967329 | chr4 | 134067881 | 134068004 | chr4 | 134068577 | 134068791 |
| chr4 | 134069289 | 134069318 | chr4 | 134069578 | 134069896 | chr4 | 134070374 | 134070403 |
| chr4 | 134071648 | 134072610 | chr4 | 134072677 | 134072967 | chr4 | 134073184 | 134073322 |
| chr4 | 134073568 | 134073641 | chr4 | 134073862 | 134073919 | chr4 | 134074030 | 134074156 |
| chr4 | 140200529 | 140201156 | chr4 | 140201193 | 140201462 | chr4 | 140656643 | 140656666 |
| chr4 | 140656858 | 140657089 | chr4 | 141347942 | 141348151 | chr4 | 141418921 | 141419418 |
| chr4 | 141488870 | 141489128 | chr4 | 142053130 | 142053160 | chr4 | 142053520 | 142053734 |

TABLE 13-continued

Pan Cancer #3

| chr | start | end | chr | start | end | chr | start | end |
|---|---|---|---|---|---|---|---|---|
| chr4 | 142054239 | 142054460 | chr4 | 143766796 | 143766930 | chr4 | 144621336 | 144621439 |
| chr4 | 144621515 | 144621896 | chr4 | 144621982 | 144622058 | chr4 | 145568052 | 145568147 |
| chr4 | 145568459 | 145568741 | chr4 | 146853951 | 146853981 | chr4 | 147558272 | 147558381 |
| chr4 | 147558477 | 147558504 | chr4 | 147559321 | 147560078 | chr4 | 147560134 | 147560418 |
| chr4 | 147560460 | 147560617 | chr4 | 147560933 | 147561145 | chr4 | 147561360 | 147561949 |
| chr4 | 147562000 | 147562055 | chr4 | 147568636 | 147569060 | chr4 | 147569620 | 147569650 |
| chr4 | 147576177 | 147576201 | chr4 | 147576330 | 147576639 | chr4 | 151974287 | 151974489 |
| chr4 | 152148807 | 152148836 | chr4 | 152246132 | 152246314 | chr4 | 153247273 | 153247386 |
| chr4 | 153249362 | 153249398 | chr4 | 153251894 | 153251923 | chr4 | 153702685 | 153702702 |
| chr4 | 154216241 | 154216357 | chr4 | 154709524 | 154709610 | chr4 | 154709759 | 154710617 |
| chr4 | 154710729 | 154710914 | chr4 | 154712172 | 154712594 | chr4 | 154713500 | 154713530 |
| chr4 | 154713949 | 154714010 | chr4 | 155254166 | 155254196 | chr4 | 155411851 | 155412279 |
| chr4 | 155663209 | 155663647 | chr4 | 155665445 | 155665475 | chr4 | 156129153 | 156129183 |
| chr4 | 156129451 | 156129495 | chr4 | 156129746 | 156129797 | chr4 | 156130047 | 156130297 |
| chr4 | 156297416 | 156297556 | chr4 | 156297942 | 156298073 | chr4 | 156588311 | 156588401 |
| chr4 | 156589273 | 156589323 | chr4 | 156680257 | 156680532 | chr4 | 156681370 | 156681489 |
| chr4 | 158141576 | 158141606 | chr4 | 158142847 | 158142999 | chr4 | 158143443 | 158143465 |
| chr4 | 164252991 | 164253447 | chr4 | 165304515 | 165304578 | chr4 | 165305060 | 165305163 |
| chr4 | 166414834 | 166414921 | chr4 | 166794771 | 166794909 | chr4 | 166796118 | 166796212 |
| chr4 | 168155109 | 168155269 | chr4 | 170865261 | 170865287 | chr4 | 170947287 | 170947325 |
| chr4 | 172734189 | 172734203 | chr4 | 172734592 | 172734790 | chr4 | 174083164 | 174083208 |
| chr4 | 174136704 | 174136734 | chr4 | 174429658 | 174429688 | chr4 | 174430310 | 174430553 |
| chr4 | 174430794 | 174431072 | chr4 | 174438567 | 174438744 | chr4 | 174439822 | 174440257 |
| chr4 | 174440635 | 174440713 | chr4 | 174443212 | 174443242 | chr4 | 174443563 | 174443934 |
| chr4 | 174446508 | 174446525 | chr4 | 174446952 | 174447005 | chr4 | 174449950 | 174450726 |
| chr4 | 174450752 | 174451482 | chr4 | 174451855 | 174452098 | chr4 | 174459185 | 174459374 |
| chr4 | 174459528 | 174459840 | chr4 | 174460186 | 174460221 | chr4 | 175132735 | 175132765 |
| chr4 | 175133085 | 175133201 | chr4 | 175134897 | 175135672 | chr4 | 175135921 | 175136011 |
| chr4 | 175138411 | 175138546 | chr4 | 175138964 | 175139254 | chr4 | 175139559 | 175139685 |
| chr4 | 175750456 | 175750738 | chr4 | 176923424 | 176923558 | chr4 | 176987324 | 176987373 |
| chr4 | 177713228 | 177713437 | chr4 | 178285756 | 178285788 | chr4 | 180979270 | 180979300 |
| chr4 | 180980297 | 180980356 | chr4 | 183063666 | 183063950 | chr4 | 183064617 | 183064655 |
| chr4 | 183064874 | 183064966 | chr4 | 184019249 | 184019316 | chr4 | 184019692 | 184019736 |
| chr4 | 184020106 | 184020179 | chr4 | 184375696 | 184375726 | chr4 | 184644053 | 184644249 |
| chr4 | 184718260 | 184718352 | chr4 | 184826238 | 184826493 | chr4 | 184826938 | 184827237 |
| chr4 | 184921855 | 184922091 | chr4 | 185089696 | 185089797 | chr4 | 185937333 | 185937889 |
| chr4 | 185938497 | 185938564 | chr4 | 185940338 | 185940460 | chr4 | 185941585 | 185942472 |
| chr4 | 185942492 | 185942760 | chr4 | 187647073 | 187647457 | chr5 | 53849 | 53898 |
| chr5 | 92163 | 92399 | chr5 | 303272 | 303301 | chr5 | 320840 | 320982 |
| chr5 | 343916 | 343941 | chr5 | 373363 | 373392 | chr5 | 373872 | 374266 |
| chr5 | 400186 | 400215 | chr5 | 400502 | 400531 | chr5 | 415870 | 415899 |
| chr5 | 481012 | 481037 | chr5 | 491335 | 491536 | chr5 | 524337 | 524404 |
| chr5 | 538758 | 538806 | chr5 | 554299 | 554538 | chr5 | 554871 | 554900 |
| chr5 | 555192 | 555285 | chr5 | 555965 | 555995 | chr5 | 677889 | 678006 |
| chr5 | 909204 | 909304 | chr5 | 912806 | 912835 | chr5 | 1034600 | 1034653 |
| chr5 | 1059523 | 1059556 | chr5 | 1093660 | 1093797 | chr5 | 1131217 | 1131378 |
| chr5 | 1193381 | 1193521 | chr5 | 1193880 | 1193944 | chr5 | 1221197 | 1221307 |
| chr5 | 1271339 | 1271396 | chr5 | 1294630 | 1294767 | chr5 | 1295031 | 1295442 |
| chr5 | 1295605 | 1295662 | chr5 | 1445171 | 1445255 | chr5 | 1445738 | 1445759 |
| chr5 | 1445841 | 1445928 | chr5 | 1446319 | 1446369 | chr5 | 1446443 | 1446599 |
| chr5 | 1747022 | 1747098 | chr5 | 1779526 | 1779556 | chr5 | 1787378 | 1787418 |
| chr5 | 1874892 | 1875099 | chr5 | 1875453 | 1875497 | chr5 | 1875870 | 1876306 |
| chr5 | 1876638 | 1876860 | chr5 | 1877195 | 1877239 | chr5 | 1878014 | 1878028 |
| chr5 | 1878224 | 1878528 | chr5 | 1878831 | 1879045 | chr5 | 1879605 | 1879661 |
| chr5 | 1879690 | 1879719 | chr5 | 1882420 | 1882605 | chr5 | 1882844 | 1882921 |
| chr5 | 1883515 | 1883616 | chr5 | 1884178 | 1884237 | chr5 | 1884557 | 1884698 |
| chr5 | 1885158 | 1885458 | chr5 | 1885985 | 1886076 | chr5 | 1886542 | 1886581 |
| chr5 | 1886812 | 1886841 | chr5 | 1886998 | 1887145 | chr5 | 1887547 | 1887581 |
| chr5 | 1887656 | 1887737 | chr5 | 1930786 | 1931004 | chr5 | 1931065 | 1931286 |
| chr5 | 1931445 | 1931576 | chr5 | 1931618 | 1931754 | chr5 | 1950794 | 1950960 |
| chr5 | 1952624 | 1952638 | chr5 | 2038705 | 2038850 | chr5 | 2225439 | 2225469 |
| chr5 | 2324383 | 2324413 | chr5 | 2541487 | 2541611 | chr5 | 2738848 | 2739129 |
| chr5 | 2739211 | 2739354 | chr5 | 2739877 | 2740300 | chr5 | 2740431 | 2740664 |
| chr5 | 2743617 | 2743659 | chr5 | 2743699 | 2743713 | chr5 | 2748374 | 2748459 |
| chr5 | 2749213 | 2749406 | chr5 | 2749699 | 2749729 | chr5 | 2750435 | 2750516 |
| chr5 | 2750655 | 2750769 | chr5 | 2751855 | 2751894 | chr5 | 2752991 | 2753040 |
| chr5 | 2753048 | 2753078 | chr5 | 2754738 | 2754767 | chr5 | 2755323 | 2756388 |
| chr5 | 2756599 | 2756602 | chr5 | 2756674 | 2757427 | chr5 | 3031879 | 3032018 |
| chr5 | 3152146 | 3152176 | chr5 | 3325042 | 3325272 | chr5 | 3590405 | 3590657 |
| chr5 | 3591354 | 3591388 | chr5 | 3591857 | 3592037 | chr5 | 3592728 | 3592881 |
| chr5 | 3594250 | 3594519 | chr5 | 3595090 | 3595178 | chr5 | 3595850 | 3595991 |
| chr5 | 3596556 | 3596724 | chr5 | 3596825 | 3596880 | chr5 | 3597411 | 3597461 |
| chr5 | 3600150 | 3600180 | chr5 | 3602804 | 3603320 | chr5 | 3674053 | 3674224 |
| chr5 | 4144367 | 4144516 | chr5 | 5139754 | 5139900 | chr5 | 5140170 | 5140225 |
| chr5 | 5140630 | 5140757 | chr5 | 5140850 | 5140901 | chr5 | 6228617 | 6228790 |
| chr5 | 6448930 | 6449582 | chr5 | 6482458 | 6482620 | chr5 | 6583461 | 6583579 |

TABLE 13-continued

Pan Cancer #3

| chr | start | end | chr | start | end | chr | start | end |
|---|---|---|---|---|---|---|---|---|
| chr5 | 6687277 | 6687431 | chr5 | 6755789 | 6755843 | chr5 | 7395263 | 7395393 |
| chr5 | 7395434 | 7395538 | chr5 | 7851015 | 7851121 | chr5 | 9546612 | 9546648 |
| chr5 | 10249098 | 10249127 | chr5 | 10333688 | 10334132 | chr5 | 10565021 | 10565227 |
| chr5 | 10565263 | 10565607 | chr5 | 11384965 | 11385363 | chr5 | 11903822 | 11904173 |
| chr5 | 11904196 | 11904379 | chr5 | 11904456 | 11904696 | chr5 | 11904896 | 11904943 |
| chr5 | 14872919 | 14873053 | chr5 | 15500748 | 15500927 | chr5 | 16179049 | 16179141 |
| chr5 | 16179555 | 16179713 | chr5 | 16180183 | 16180260 | chr5 | 16466784 | 16466802 |
| chr5 | 16467042 | 16467120 | chr5 | 16845452 | 16845476 | chr5 | 16845536 | 16845619 |
| chr5 | 16936354 | 16936514 | chr5 | 17203035 | 17203177 | chr5 | 17218195 | 17218225 |
| chr5 | 17218986 | 17219018 | chr5 | 17512114 | 17512144 | chr5 | 22853443 | 22853508 |
| chr5 | 31193937 | 31193989 | chr5 | 31194375 | 31194641 | chr5 | 31639684 | 31639960 |
| chr5 | 31691565 | 31691652 | chr5 | 31855073 | 31855199 | chr5 | 32710331 | 32710470 |
| chr5 | 32710802 | 32710957 | chr5 | 32711017 | 32711531 | chr5 | 32711826 | 32711870 |
| chr5 | 32712077 | 32712101 | chr5 | 32712290 | 32712491 | chr5 | 32712764 | 32713304 |
| chr5 | 33298005 | 33298076 | chr5 | 33892083 | 33892115 | chr5 | 33892413 | 33892443 |
| chr5 | 33936156 | 33936336 | chr5 | 33936486 | 33936516 | chr5 | 33936599 | 33936663 |
| chr5 | 34656932 | 34657034 | chr5 | 35874560 | 35874589 | chr5 | 35939832 | 35939861 |
| chr5 | 37834684 | 37834714 | chr5 | 37835015 | 37835125 | chr5 | 37836231 | 37836260 |
| chr5 | 37836649 | 37837992 | chr5 | 37838548 | 37838885 | chr5 | 37839808 | 37840125 |
| chr5 | 37840530 | 37840853 | chr5 | 38257485 | 38257606 | chr5 | 38257842 | 38257908 |
| chr5 | 38257945 | 38257959 | chr5 | 38557070 | 38557400 | chr5 | 38845675 | 38846164 |
| chr5 | 39343181 | 39343205 | chr5 | 40681122 | 40681227 | chr5 | 40681262 | 40681367 |
| chr5 | 40681676 | 40681839 | chr5 | 40775147 | 40775313 | chr5 | 42424822 | 42425060 |
| chr5 | 42950980 | 42951311 | chr5 | 42951420 | 42952111 | chr5 | 42991825 | 42992241 |
| chr5 | 42992376 | 42992597 | chr5 | 42992783 | 42992934 | chr5 | 42993312 | 42993552 |
| chr5 | 42993852 | 42994193 | chr5 | 42994694 | 42994790 | chr5 | 42995115 | 42995153 |
| chr5 | 43007936 | 43007966 | chr5 | 43008202 | 43008472 | chr5 | 43017953 | 43018176 |
| chr5 | 43018327 | 43018690 | chr5 | 43019238 | 43019347 | chr5 | 43019809 | 43019887 |
| chr5 | 43020146 | 43020294 | chr5 | 43040544 | 43040635 | chr5 | 43040870 | 43040964 |
| chr5 | 43215538 | 43215578 | chr5 | 43397002 | 43397229 | chr5 | 44389782 | 44389852 |
| chr5 | 45695186 | 45695239 | chr5 | 45695314 | 45695533 | chr5 | 45695906 | 45695947 |
| chr5 | 45696336 | 45696439 | chr5 | 49736592 | 49736685 | chr5 | 50262893 | 50263014 |
| chr5 | 50263568 | 50263641 | chr5 | 50264307 | 50264603 | chr5 | 50264820 | 50264850 |
| chr5 | 50265325 | 50265429 | chr5 | 50265721 | 50265880 | chr5 | 50674152 | 50674188 |
| chr5 | 50674560 | 50674590 | chr5 | 50675013 | 50675075 | chr5 | 50678346 | 50678490 |
| chr5 | 50695351 | 50695463 | chr5 | 52084073 | 52084134 | chr5 | 54179610 | 54179633 |
| chr5 | 54180063 | 54180093 | chr5 | 54516371 | 54516680 | chr5 | 54516832 | 54517017 |
| chr5 | 54518651 | 54519288 | chr5 | 54527323 | 54527343 | chr5 | 56246546 | 56246575 |
| chr5 | 56247942 | 56247971 | chr5 | 56248218 | 56248257 | chr5 | 57878271 | 57878375 |
| chr5 | 57878710 | 57878752 | chr5 | 59188291 | 59188327 | chr5 | 59189055 | 59189057 |
| chr5 | 59189189 | 59189206 | chr5 | 59189863 | 59189948 | chr5 | 63254903 | 63255242 |
| chr5 | 63256863 | 63256895 | chr5 | 63257727 | 63257861 | chr5 | 63802007 | 63802304 |
| chr5 | 63802340 | 63802514 | chr5 | 63986488 | 63986527 | chr5 | 63986570 | 63986807 |
| chr5 | 67569803 | 67569832 | chr5 | 67588937 | 67589162 | chr5 | 67589598 | 67589627 |
| chr5 | 67590431 | 67590460 | chr5 | 67591068 | 67591157 | chr5 | 68391309 | 68391336 |
| chr5 | 71014720 | 71014895 | chr5 | 71015180 | 71015728 | chr5 | 71106820 | 71106984 |
| chr5 | 71403566 | 71403653 | chr5 | 71403975 | 71404207 | chr5 | 72416246 | 72416751 |
| chr5 | 72526413 | 72526414 | chr5 | 72526492 | 72526643 | chr5 | 72528434 | 72528464 |
| chr5 | 72529289 | 72529825 | chr5 | 72529890 | 72530609 | chr5 | 72594802 | 72594836 |
| chr5 | 72594868 | 72595016 | chr5 | 72595047 | 72595059 | chr5 | 72595555 | 72595721 |
| chr5 | 72595774 | 72595788 | chr5 | 72599079 | 72599441 | chr5 | 72599463 | 72599833 |
| chr5 | 72677775 | 72677825 | chr5 | 72677998 | 72678028 | chr5 | 72715204 | 72715347 |
| chr5 | 72715591 | 72715695 | chr5 | 72715731 | 72715768 | chr5 | 72716102 | 72716180 |
| chr5 | 72732870 | 72732884 | chr5 | 72733093 | 72733185 | chr5 | 72740147 | 72740184 |
| chr5 | 72746680 | 72746683 | chr5 | 75377883 | 75378033 | chr5 | 75380163 | 75380193 |
| chr5 | 75380624 | 75380974 | chr5 | 76011285 | 76011337 | chr5 | 76012576 | 76012605 |
| chr5 | 76249270 | 76249670 | chr5 | 76249696 | 76249906 | chr5 | 76249945 | 76250150 |
| chr5 | 76250435 | 76250504 | chr5 | 76506469 | 76506506 | chr5 | 76507035 | 76507114 |
| chr5 | 76923679 | 76924023 | chr5 | 76924087 | 76924299 | chr5 | 76924930 | 76924960 |
| chr5 | 76925561 | 76925690 | chr5 | 76928157 | 76928397 | chr5 | 76928688 | 76928906 |
| chr5 | 76932302 | 76932332 | chr5 | 76932542 | 76933265 | chr5 | 76934173 | 76934653 |
| chr5 | 76934677 | 76934870 | chr5 | 76936016 | 76936039 | chr5 | 76936099 | 76936721 |
| chr5 | 76939436 | 76939774 | chr5 | 76940340 | 76940374 | chr5 | 76941201 | 76941326 |
| chr5 | 77140527 | 77140711 | chr5 | 77147563 | 77147649 | chr5 | 77147873 | 77148195 |
| chr5 | 77148498 | 77148695 | chr5 | 77268367 | 77269237 | chr5 | 77269264 | 77269309 |
| chr5 | 78407651 | 78407840 | chr5 | 78408192 | 78408274 | chr5 | 78408298 | 78408461 |
| chr5 | 78910231 | 78910332 | chr5 | 79598681 | 79598759 | chr5 | 79783240 | 79783271 |
| chr5 | 79864898 | 79865078 | chr5 | 79866100 | 79866414 | chr5 | 79947584 | 79947707 |
| chr5 | 80255816 | 80256074 | chr5 | 80689543 | 80689735 | chr5 | 80690118 | 80690239 |
| chr5 | 82767429 | 82767793 | chr5 | 82768892 | 82769061 | chr5 | 83679195 | 83679225 |
| chr5 | 83679681 | 83680340 | chr5 | 83680615 | 83680664 | chr5 | 83680694 | 83680708 |
| chr5 | 87955460 | 87955664 | chr5 | 87956199 | 87956662 | chr5 | 87956680 | 87956964 |
| chr5 | 87962966 | 87963002 | chr5 | 87963390 | 87963511 | chr5 | 87967773 | 87968077 |
| chr5 | 87968486 | 87968685 | chr5 | 87968773 | 87968858 | chr5 | 87970193 | 87970872 |
| chr5 | 87974104 | 87974307 | chr5 | 87974868 | 87975023 | chr5 | 87976028 | 87976308 |
| chr5 | 87976525 | 87976559 | chr5 | 87979756 | 87979834 | chr5 | 87979894 | 87979912 |

TABLE 13-continued

Pan Cancer #3

| chr | start | end | chr | start | end | chr | start | end |
|---|---|---|---|---|---|---|---|---|
| chr5 | 87980142 | 87980250 | chr5 | 87980954 | 87981325 | chr5 | 87984532 | 87984657 |
| chr5 | 87985922 | 87985954 | chr5 | 87986210 | 87986281 | chr5 | 87986547 | 87986581 |
| chr5 | 87988516 | 87988584 | chr5 | 87990408 | 87990452 | chr5 | 88185470 | 88186001 |
| chr5 | 89854856 | 89854902 | chr5 | 94955681 | 94955919 | chr5 | 94956935 | 94957000 |
| chr5 | 94982134 | 94982225 | chr5 | 95767894 | 95768384 | chr5 | 95768920 | 95769093 |
| chr5 | 96114587 | 96114632 | chr5 | 100236682 | 100236757 | chr5 | 100238882 | 100239119 |
| chr5 | 100239135 | 100239151 | chr5 | 101631487 | 101631533 | chr5 | 101632295 | 101632573 |
| chr5 | 107005983 | 107006186 | chr5 | 111987781 | 111987818 | chr5 | 112042844 | 112042873 |
| chr5 | 112042904 | 112043289 | chr5 | 112073358 | 112073516 | chr5 | 112170808 | 112170837 |
| chr5 | 112175198 | 112175227 | chr5 | 112175640 | 112175669 | chr5 | 112258359 | 112258388 |
| chr5 | 112258634 | 112258663 | chr5 | 112629427 | 112629674 | chr5 | 113391265 | 113392018 |
| chr5 | 113698567 | 113698583 | chr5 | 113698670 | 113698783 | chr5 | 113699008 | 113699119 |
| chr5 | 114515010 | 114515579 | chr5 | 114515611 | 114515671 | chr5 | 115151267 | 115151357 |
| chr5 | 115151650 | 115152384 | chr5 | 115152617 | 115152638 | chr5 | 115297192 | 115297292 |
| chr5 | 115297377 | 115297556 | chr5 | 115297928 | 115297985 | chr5 | 115298496 | 115298581 |
| chr5 | 115298985 | 115299041 | chr5 | 119799931 | 119799986 | chr5 | 119801299 | 119801445 |
| chr5 | 121413537 | 121413590 | chr5 | 122422240 | 122422292 | chr5 | 122422616 | 122422651 |
| chr5 | 122423328 | 122423376 | chr5 | 122425128 | 122425168 | chr5 | 122431118 | 122431378 |
| chr5 | 124128454 | 124128497 | chr5 | 126626283 | 126626738 | chr5 | 127872942 | 127872990 |
| chr5 | 127873553 | 127873710 | chr5 | 127874448 | 127874477 | chr5 | 127874706 | 127874839 |
| chr5 | 128300680 | 128300694 | chr5 | 128300713 | 128300794 | chr5 | 128796081 | 128796244 |
| chr5 | 128796867 | 128796985 | chr5 | 128797344 | 128797386 | chr5 | 129240068 | 129240101 |
| chr5 | 131992096 | 131992157 | chr5 | 132947486 | 132947836 | chr5 | 133820024 | 133820040 |
| chr5 | 134364195 | 134364234 | chr5 | 134366718 | 134366788 | chr5 | 134367108 | 134367203 |
| chr5 | 134374447 | 134374505 | chr5 | 134374792 | 134375210 | chr5 | 134376222 | 134376375 |
| chr5 | 134376732 | 134376824 | chr5 | 134385952 | 134386167 | chr5 | 134386185 | 134386383 |
| chr5 | 134582864 | 134582894 | chr5 | 134735622 | 134735651 | chr5 | 134825463 | 134825518 |
| chr5 | 134825913 | 134826006 | chr5 | 134870446 | 134870515 | chr5 | 134870780 | 134870926 |
| chr5 | 134871601 | 134872049 | chr5 | 134879478 | 134879990 | chr5 | 134880110 | 134880501 |
| chr5 | 134914627 | 134914748 | chr5 | 135265737 | 135265767 | chr5 | 135266114 | 135266128 |
| chr5 | 135266578 | 135266672 | chr5 | 135528201 | 135528233 | chr5 | 136834050 | 136834050 |
| chr5 | 136834290 | 136834506 | chr5 | 136834720 | 136834826 | chr5 | 137225092 | 137225297 |
| chr5 | 137912123 | 137912148 | chr5 | 138196197 | 138196213 | chr5 | 138196393 | 138196408 |
| chr5 | 138273817 | 138273854 | chr5 | 139045286 | 139045315 | chr5 | 139047990 | 139048162 |
| chr5 | 139056666 | 139056804 | chr5 | 139227773 | 139227909 | chr5 | 139525728 | 139525758 |
| chr5 | 139779833 | 139779871 | chr5 | 140174798 | 140174839 | chr5 | 140187094 | 140187146 |
| chr5 | 140305978 | 140306050 | chr5 | 140306445 | 140306619 | chr5 | 140306675 | 140306733 |
| chr5 | 140346595 | 140346671 | chr5 | 140514891 | 140514921 | chr5 | 140604459 | 140604501 |
| chr5 | 140613926 | 140614014 | chr5 | 140614314 | 140614328 | chr5 | 140683631 | 140683772 |
| chr5 | 140777328 | 140777487 | chr5 | 140787623 | 140787637 | chr5 | 140797076 | 140797278 |
| chr5 | 140797328 | 140797342 | chr5 | 140800479 | 140800964 | chr5 | 140801035 | 140801246 |
| chr5 | 140855598 | 140856458 | chr5 | 140856547 | 140856622 | chr5 | 141031121 | 141031150 |
| chr5 | 141263035 | 141263142 | chr5 | 141931340 | 141931354 | chr5 | 141931425 | 141931539 |
| chr5 | 142784967 | 142785272 | chr5 | 145713645 | 145713896 | chr5 | 145717175 | 145717196 |
| chr5 | 145717249 | 145717437 | chr5 | 145718802 | 145719753 | chr5 | 145719835 | 145719925 |
| chr5 | 145720812 | 145720917 | chr5 | 145722116 | 145722466 | chr5 | 145722561 | 145723027 |
| chr5 | 145724502 | 145724698 | chr5 | 145725694 | 145725844 | chr5 | 146257332 | 146257602 |
| chr5 | 146889332 | 146889575 | chr5 | 149503827 | 149503856 | chr5 | 149682074 | 149682166 |
| chr5 | 150029147 | 150029245 | chr5 | 150051101 | 150051667 | chr5 | 150326159 | 150326188 |
| chr5 | 150400123 | 150400203 | chr5 | 151066442 | 151066474 | chr5 | 151304371 | 151304401 |
| chr5 | 153852664 | 153852792 | chr5 | 153853420 | 153853478 | chr5 | 153854330 | 153854360 |
| chr5 | 153855175 | 153855264 | chr5 | 153855658 | 153855839 | chr5 | 153856149 | 153856396 |
| chr5 | 153856936 | 153856996 | chr5 | 153857379 | 153857429 | chr5 | 153858319 | 153858599 |
| chr5 | 153859676 | 153859708 | chr5 | 153862037 | 153862179 | chr5 | 153862219 | 153862599 |
| chr5 | 153863421 | 153863451 | chr5 | 154030048 | 154030074 | chr5 | 154209926 | 154209987 |
| chr5 | 154318148 | 154318179 | chr5 | 155107794 | 155107848 | chr5 | 155108161 | 155108267 |
| chr5 | 155108356 | 155108526 | chr5 | 155108733 | 155108763 | chr5 | 156558444 | 156558477 |
| chr5 | 156655170 | 156655200 | chr5 | 156874257 | 156874308 | chr5 | 157001739 | 157001843 |
| chr5 | 157078419 | 157078449 | chr5 | 157098362 | 157098619 | chr5 | 157673799 | 157673964 |
| chr5 | 158478513 | 158478764 | chr5 | 158524692 | 158524748 | chr5 | 158524865 | 158524925 |
| chr5 | 158527443 | 158528069 | chr5 | 159399095 | 159399099 | chr5 | 160975724 | 160975754 |
| chr5 | 161274310 | 161274554 | chr5 | 166865449 | 166865473 | chr5 | 167956177 | 167956266 |
| chr5 | 167956414 | 167956595 | chr5 | 168233396 | 168233482 | chr5 | 168727924 | 168727927 |
| chr5 | 169064327 | 169064805 | chr5 | 169532927 | 169533012 | chr5 | 170108287 | 170108372 |
| chr5 | 170735154 | 170735206 | chr5 | 170735731 | 170735788 | chr5 | 170736116 | 170736163 |
| chr5 | 170736716 | 170736830 | chr5 | 170737282 | 170737479 | chr5 | 170737771 | 170737863 |
| chr5 | 170737936 | 170738689 | chr5 | 170738824 | 170739481 | chr5 | 170739823 | 170740027 |
| chr5 | 170740461 | 170740477 | chr5 | 170740575 | 170741031 | chr5 | 170741507 | 170742275 |
| chr5 | 170742387 | 170742599 | chr5 | 170742673 | 170742827 | chr5 | 170743127 | 170743479 |
| chr5 | 170743647 | 170744128 | chr5 | 170744375 | 170744562 | chr5 | 170745389 | 170745480 |
| chr5 | 171352123 | 171352153 | chr5 | 172354043 | 172354118 | chr5 | 172655879 | 172656215 |
| chr5 | 172659225 | 172659290 | chr5 | 172659496 | 172659655 | chr5 | 172659855 | 172660025 |
| chr5 | 172660142 | 172660218 | chr5 | 172660719 | 172661000 | chr5 | 172661127 | 172661684 |
| chr5 | 172664226 | 172664487 | chr5 | 172665590 | 172665812 | chr5 | 172670983 | 172671018 |
| chr5 | 172671345 | 172671481 | chr5 | 172671640 | 172671968 | chr5 | 172672477 | 172672663 |
| chr5 | 172754589 | 172754621 | chr5 | 172754832 | 172754931 | chr5 | 172755470 | 172755562 |

TABLE 13-continued

Pan Cancer #3

| chr | start | end | chr | start | end | chr | start | end |
|---|---|---|---|---|---|---|---|---|
| chr5 | 172755595 | 172755663 | chr5 | 172757048 | 172757111 | chr5 | 174115388 | 174115861 |
| chr5 | 174147523 | 174147596 | chr5 | 174150415 | 174150445 | chr5 | 174159300 | 174159588 |
| chr5 | 174162874 | 174162904 | chr5 | 174220971 | 174221001 | chr5 | 174870738 | 174870786 |
| chr5 | 174871174 | 174871497 | chr5 | 174921456 | 174921483 | chr5 | 175085147 | 175085209 |
| chr5 | 175085525 | 175085719 | chr5 | 175223671 | 175223709 | chr5 | 175298549 | 175298883 |
| chr5 | 175299294 | 175299396 | chr5 | 175300351 | 175300381 | chr5 | 175621390 | 175621501 |
| chr5 | 175792865 | 175792931 | chr5 | 175792998 | 175793063 | chr5 | 175831257 | 175831326 |
| chr5 | 175971447 | 175971471 | chr5 | 176024006 | 176024318 | chr5 | 176046363 | 176046554 |
| chr5 | 176107274 | 176107484 | chr5 | 176107518 | 176107586 | chr5 | 176236721 | 176236898 |
| chr5 | 176264805 | 176264915 | chr5 | 176295786 | 176295892 | chr5 | 176520166 | 176520195 |
| chr5 | 176522400 | 176522566 | chr5 | 176764100 | 176764169 | chr5 | 176827656 | 176827685 |
| chr5 | 177031167 | 177031197 | chr5 | 177408292 | 177408443 | chr5 | 177411638 | 177412141 |
| chr5 | 177713376 | 177713468 | chr5 | 178004325 | 178004374 | chr5 | 178016682 | 178016983 |
| chr5 | 178017520 | 178017867 | chr5 | 178368074 | 178368121 | chr5 | 178487107 | 178487303 |
| chr5 | 178487342 | 178487398 | chr5 | 178576356 | 178576499 | chr5 | 178655753 | 178655871 |
| chr5 | 178771314 | 178771630 | chr5 | 178771724 | 178771859 | chr5 | 178772205 | 178772272 |
| chr5 | 178772603 | 178772729 | chr5 | 178781548 | 178781577 | chr5 | 178957637 | 178957944 |
| chr5 | 179214113 | 179214196 | chr5 | 179270726 | 179270748 | chr5 | 179780104 | 179780144 |
| chr5 | 179780706 | 179780985 | chr5 | 179867486 | 179867548 | chr5 | 180017118 | 180017198 |
| chr5 | 180017608 | 180017933 | chr5 | 180018485 | 180018498 | chr5 | 180047440 | 180047606 |
| chr5 | 180075846 | 180075857 | chr5 | 180076054 | 180076317 | chr5 | 180076567 | 180076602 |
| chr5 | 180076804 | 180076996 | chr5 | 180101016 | 180101167 | chr5 | 180101252 | 180101332 |
| chr5 | 180326126 | 180326156 | chr5 | 180527546 | 180527698 | chr5 | 180594851 | 180594927 |
| chr5 | 180594987 | 180595002 | chr5 | 180600858 | 180601068 | chr5 | 180601128 | 180601218 |
| chr6 | 373148 | 373290 | chr6 | 391173 | 391899 | chr6 | 392410 | 392433 |
| chr6 | 392588 | 392958 | chr6 | 393125 | 393472 | chr6 | 711142 | 711293 |
| chr6 | 1312000 | 1312096 | chr6 | 1312595 | 1312708 | chr6 | 1314088 | 1314100 |
| chr6 | 1378222 | 1378475 | chr6 | 1379584 | 1379614 | chr6 | 1379909 | 1379952 |
| chr6 | 1383677 | 1383708 | chr6 | 1383860 | 1384179 | chr6 | 1384626 | 1384644 |
| chr6 | 1385118 | 1385170 | chr6 | 1386071 | 1386112 | chr6 | 1389124 | 1389262 |
| chr6 | 1390241 | 1390405 | chr6 | 1390424 | 1390758 | chr6 | 1390956 | 1391035 |
| chr6 | 1391318 | 1391379 | chr6 | 1524199 | 1524283 | chr6 | 1605387 | 1605454 |
| chr6 | 1620672 | 1620701 | chr6 | 1624977 | 1625068 | chr6 | 1625128 | 1625818 |
| chr6 | 3053299 | 3053386 | chr6 | 3229029 | 3229059 | chr6 | 3229423 | 3229510 |
| chr6 | 3232010 | 3232260 | chr6 | 3247675 | 3247704 | chr6 | 3285222 | 3285513 |
| chr6 | 3405645 | 3405713 | chr6 | 4775062 | 4775222 | chr6 | 4836440 | 4836458 |
| chr6 | 4951247 | 4951390 | chr6 | 5783325 | 5783496 | chr6 | 5996952 | 5996989 |
| chr6 | 5997802 | 5997832 | chr6 | 6003287 | 6003528 | chr6 | 6004350 | 6004743 |
| chr6 | 6004837 | 6005417 | chr6 | 6006374 | 6006419 | chr6 | 6006674 | 6006883 |
| chr6 | 6007593 | 6008277 | chr6 | 6367086 | 6367271 | chr6 | 6753803 | 6753839 |
| chr6 | 7726334 | 7726363 | chr6 | 7726630 | 7726659 | chr6 | 7726952 | 7726981 |
| chr6 | 7727699 | 7727768 | chr6 | 7728087 | 7728142 | chr6 | 7728849 | 7728941 |
| chr6 | 7731054 | 7731083 | chr6 | 7892314 | 7892412 | chr6 | 10381507 | 10381592 |
| chr6 | 10381695 | 10381968 | chr6 | 10382722 | 10383049 | chr6 | 10383739 | 10383774 |
| chr6 | 10384950 | 10384974 | chr6 | 10385280 | 10385939 | chr6 | 10386210 | 10386273 |
| chr6 | 10390023 | 10391187 | chr6 | 10410518 | 10410578 | chr6 | 10411356 | 10411510 |
| chr6 | 10415113 | 10415215 | chr6 | 10415559 | 10415713 | chr6 | 10416118 | 10416351 |
| chr6 | 10417158 | 10417529 | chr6 | 10419086 | 10419439 | chr6 | 10419477 | 10419506 |
| chr6 | 10419744 | 10419941 | chr6 | 10421053 | 10421451 | chr6 | 10421549 | 10422635 |
| chr6 | 10423613 | 10423704 | chr6 | 10425630 | 10425789 | chr6 | 10425839 | 10426884 |
| chr6 | 10542836 | 10542977 | chr6 | 10881856 | 10882057 | chr6 | 10882321 | 10882350 |
| chr6 | 10883008 | 10883022 | chr6 | 10887078 | 10887686 | chr6 | 11044062 | 11044572 |
| chr6 | 12288517 | 12288681 | chr6 | 12749899 | 12749940 | chr6 | 15513780 | 15513981 |
| chr6 | 16197030 | 16197112 | chr6 | 16729595 | 16729624 | chr6 | 17281417 | 17281534 |
| chr6 | 18035867 | 18036015 | chr6 | 19691638 | 19691841 | chr6 | 19692143 | 19692318 |
| chr6 | 19837064 | 19837140 | chr6 | 19892478 | 19892627 | chr6 | 21664719 | 21664749 |
| chr6 | 21665004 | 21665043 | chr6 | 24358291 | 24358320 | chr6 | 24360074 | 24360170 |
| chr6 | 24494679 | 24494766 | chr6 | 24647342 | 24647381 | chr6 | 26184363 | 26184391 |
| chr6 | 26188715 | 26189393 | chr6 | 26189955 | 26189991 | chr6 | 26199137 | 26199167 |
| chr6 | 26199686 | 26199716 | chr6 | 26214611 | 26214648 | chr6 | 26235223 | 26235623 |
| chr6 | 26240504 | 26241118 | chr6 | 26250468 | 26250826 | chr6 | 26251054 | 26251182 |
| chr6 | 26251816 | 26251954 | chr6 | 26252074 | 26252098 | chr6 | 26252141 | 26252151 |
| chr6 | 26271406 | 26271762 | chr6 | 26271971 | 26272001 | chr6 | 26272512 | 26272617 |
| chr6 | 26273400 | 26273418 | chr6 | 26284811 | 26284898 | chr6 | 26327806 | 26327982 |
| chr6 | 26328294 | 26328457 | chr6 | 26332178 | 26332218 | chr6 | 26501950 | 26502209 |
| chr6 | 26550994 | 26551034 | chr6 | 26577158 | 26577475 | chr6 | 26987967 | 26988166 |
| chr6 | 27059783 | 27059848 | chr6 | 27064682 | 27065198 | chr6 | 27173528 | 27173546 |
| chr6 | 27173633 | 27173855 | chr6 | 27173915 | 27174181 | chr6 | 27182869 | 27182899 |
| chr6 | 27203269 | 27203286 | chr6 | 27205300 | 27205441 | chr6 | 27205671 | 27205836 |
| chr6 | 27205914 | 27206040 | chr6 | 27218951 | 27218980 | chr6 | 27228180 | 27228186 |
| chr6 | 27228290 | 27228395 | chr6 | 27235876 | 27235905 | chr6 | 27247636 | 27247724 |
| chr6 | 27256097 | 27256173 | chr6 | 27256383 | 27256420 | chr6 | 27264332 | 27264364 |
| chr6 | 27279845 | 27280012 | chr6 | 27463029 | 27463687 | chr6 | 27512761 | 27512883 |
| chr6 | 27512995 | 27513487 | chr6 | 27533822 | 27534341 | chr6 | 27559809 | 27560075 |
| chr6 | 27573171 | 27573392 | chr6 | 27598738 | 27598860 | chr6 | 27599159 | 27599341 |
| chr6 | 27635265 | 27635434 | chr6 | 27647712 | 27647735 | chr6 | 27647891 | 27647896 |

TABLE 13-continued

Pan Cancer #3

| chr | start | end | chr | start | end | chr | start | end |
|---|---|---|---|---|---|---|---|---|
| chr6 | 27648933 | 27649134 | chr6 | 27783039 | 27783052 | chr6 | 27799464 | 27799581 |
| chr6 | 27834676 | 27834835 | chr6 | 27835047 | 27835096 | chr6 | 27835378 | 27835417 |
| chr6 | 27839726 | 27840082 | chr6 | 27840543 | 27840617 | chr6 | 27841104 | 27841136 |
| chr6 | 27858515 | 27858637 | chr6 | 28175189 | 28176212 | chr6 | 28227076 | 28227141 |
| chr6 | 28303562 | 28303607 | chr6 | 28303815 | 28304263 | chr6 | 28367109 | 28367346 |
| chr6 | 28367491 | 28367774 | chr6 | 28410976 | 28411087 | chr6 | 28411152 | 28411353 |
| chr6 | 28414977 | 28414991 | chr6 | 28457608 | 28457638 | chr6 | 28457870 | 28458158 |
| chr6 | 28956323 | 28956511 | chr6 | 28956660 | 28956719 | chr6 | 30095233 | 30095262 |
| chr6 | 30095418 | 30095570 | chr6 | 30130804 | 30130895 | chr6 | 30644680 | 30644798 |
| chr6 | 32374147 | 32374176 | chr6 | 32374739 | 32374768 | chr6 | 32376051 | 32376080 |
| chr6 | 33161275 | 33161342 | chr6 | 33632930 | 33633000 | chr6 | 33636388 | 33636418 |
| chr6 | 33955505 | 33955731 | chr6 | 34113872 | 34113957 | chr6 | 34170970 | 34170986 |
| chr6 | 34171046 | 34171061 | chr6 | 34219930 | 34219951 | chr6 | 34396517 | 34396542 |
| chr6 | 34714803 | 34714820 | chr6 | 34724198 | 34724228 | chr6 | 35150041 | 35150080 |
| chr6 | 35182493 | 35182522 | chr6 | 35479613 | 35479642 | chr6 | 35992428 | 35992458 |
| chr6 | 36165662 | 36165692 | chr6 | 36178031 | 36178301 | chr6 | 36252984 | 36253171 |
| chr6 | 36313883 | 36313913 | chr6 | 36808323 | 36808441 | chr6 | 37024559 | 37024589 |
| chr6 | 37664140 | 37664187 | chr6 | 37673320 | 37673611 | chr6 | 37776410 | 37776440 |
| chr6 | 37776719 | 37776735 | chr6 | 38683212 | 38683235 | chr6 | 39281088 | 39281133 |
| chr6 | 39281824 | 39281875 | chr6 | 39329863 | 39329892 | chr6 | 39508464 | 39508493 |
| chr6 | 39760401 | 39760661 | chr6 | 40554653 | 40554699 | chr6 | 41337072 | 41337128 |
| chr6 | 41339263 | 41339558 | chr6 | 41339602 | 41339838 | chr6 | 41340902 | 41341182 |
| chr6 | 41341501 | 41341549 | chr6 | 41342243 | 41342275 | chr6 | 41342807 | 41342837 |
| chr6 | 41605937 | 41605951 | chr6 | 41606038 | 41606356 | chr6 | 41606528 | 41606542 |
| chr6 | 41773520 | 41773903 | chr6 | 41774459 | 41774576 | chr6 | 42738966 | 42739049 |
| chr6 | 42773440 | 42773471 | chr6 | 42846662 | 42846705 | chr6 | 42879554 | 42879568 |
| chr6 | 42879622 | 42879718 | chr6 | 42928321 | 42928454 | chr6 | 43211193 | 43211311 |
| chr6 | 43424444 | 43424470 | chr6 | 43425479 | 43425509 | chr6 | 43478676 | 43478745 |
| chr6 | 43612825 | 43612898 | chr6 | 43613053 | 43613067 | chr6 | 43639548 | 43639710 |
| chr6 | 43748463 | 43748616 | chr6 | 44240914 | 44241108 | chr6 | 44695763 | 44695795 |
| chr6 | 45388716 | 45388775 | chr6 | 46702982 | 46703123 | chr6 | 46703350 | 46703436 |
| chr6 | 47590582 | 47590604 | chr6 | 50674372 | 50674750 | chr6 | 50681699 | 50681851 |
| chr6 | 50681911 | 50681942 | chr6 | 50682319 | 50682338 | chr6 | 50682659 | 50682683 |
| chr6 | 50682712 | 50682940 | chr6 | 50682992 | 50683227 | chr6 | 50684939 | 50684969 |
| chr6 | 50689913 | 50690039 | chr6 | 50691065 | 50691095 | chr6 | 50692083 | 50692212 |
| chr6 | 50692300 | 50692481 | chr6 | 50787216 | 50787876 | chr6 | 50787950 | 50788352 |
| chr6 | 50789374 | 50789404 | chr6 | 50791187 | 50791494 | chr6 | 50791551 | 50791632 |
| chr6 | 50793335 | 50793404 | chr6 | 50793728 | 50793882 | chr6 | 50794531 | 50794693 |
| chr6 | 50803834 | 50803867 | chr6 | 50804131 | 50804368 | chr6 | 50808681 | 50808854 |
| chr6 | 50810551 | 50810713 | chr6 | 50811062 | 50811488 | chr6 | 50813258 | 50813939 |
| chr6 | 50814569 | 50814599 | chr6 | 50817023 | 50817229 | chr6 | 50817905 | 50817935 |
| chr6 | 50818449 | 50818706 | chr6 | 50818920 | 50819000 | chr6 | 52227752 | 52227781 |
| chr6 | 52228008 | 52228037 | chr6 | 52344375 | 52344405 | chr6 | 53212491 | 53213970 |
| chr6 | 55443691 | 55443946 | chr6 | 56112262 | 56112386 | chr6 | 56716390 | 56716410 |
| chr6 | 56818656 | 56818937 | chr6 | 56819217 | 56819637 | chr6 | 56819897 | 56819926 |
| chr6 | 58147447 | 58147480 | chr6 | 58147790 | 58147976 | chr6 | 62995356 | 62995874 |
| chr6 | 62996078 | 62996146 | chr6 | 62996443 | 62996489 | chr6 | 70992137 | 70992162 |
| chr6 | 70992415 | 70992560 | chr6 | 70992830 | 70993015 | chr6 | 71665638 | 71665723 |
| chr6 | 71666788 | 71666986 | chr6 | 72129789 | 72129829 | chr6 | 72130191 | 72130464 |
| chr6 | 72596120 | 72596315 | chr6 | 72596950 | 72596980 | chr6 | 73329784 | 73330126 |
| chr6 | 73330834 | 73331304 | chr6 | 73331515 | 73331850 | chr6 | 73331876 | 73333099 |
| chr6 | 73980699 | 73980722 | chr6 | 76059561 | 76059787 | chr6 | 78172177 | 78172275 |
| chr6 | 78172323 | 78172572 | chr6 | 78173212 | 78173264 | chr6 | 78173696 | 78173725 |
| chr6 | 78173772 | 78173984 | chr6 | 78176458 | 78176820 | chr6 | 79620475 | 79620699 |
| chr6 | 80656930 | 80657180 | chr6 | 82463270 | 82463310 | chr6 | 82958615 | 82958646 |
| chr6 | 84141298 | 84141412 | chr6 | 84417436 | 84417700 | chr6 | 84418261 | 84418281 |
| chr6 | 84418644 | 84418788 | chr6 | 84419157 | 84419415 | chr6 | 84562873 | 84563242 |
| chr6 | 84563489 | 84563542 | chr6 | 85050460 | 85050504 | chr6 | 85472407 | 85473703 |
| chr6 | 85473928 | 85474378 | chr6 | 85474594 | 85474736 | chr6 | 85476233 | 85476285 |
| chr6 | 85476998 | 85477028 | chr6 | 85478514 | 85478724 | chr6 | 85482530 | 85482796 |
| chr6 | 85483345 | 85483375 | chr6 | 85483760 | 85483931 | chr6 | 85484558 | 85484625 |
| chr6 | 85484717 | 85484920 | chr6 | 86302413 | 86302454 | chr6 | 87647114 | 87647143 |
| chr6 | 87862092 | 87862172 | chr6 | 88876963 | 88877421 | chr6 | 91320285 | 91320318 |
| chr6 | 91320949 | 91321295 | chr6 | 94126973 | 94127064 | chr6 | 94127455 | 94127544 |
| chr6 | 94128365 | 94128399 | chr6 | 94129219 | 94129257 | chr6 | 94129509 | 94129575 |
| chr6 | 96464100 | 96464204 | chr6 | 99271926 | 99272810 | chr6 | 99273369 | 99273410 |
| chr6 | 99277180 | 99277330 | chr6 | 99279556 | 99279612 | chr6 | 99280557 | 99280759 |
| chr6 | 99281014 | 99281036 | chr6 | 99281068 | 99281385 | chr6 | 99283512 | 99283582 |
| chr6 | 99290360 | 99290398 | chr6 | 99291264 | 99291341 | chr6 | 99292252 | 99292417 |
| chr6 | 99295726 | 99295863 | chr6 | 99296062 | 99296364 | chr6 | 99296408 | 99296467 |
| chr6 | 99396456 | 99396473 | chr6 | 99842067 | 99842163 | chr6 | 99842359 | 99842382 |
| chr6 | 100038682 | 100038706 | chr6 | 100038786 | 100038964 | chr6 | 100039275 | 100039289 |
| chr6 | 100050754 | 100050810 | chr6 | 100050859 | 100051108 | chr6 | 100051360 | 100051507 |
| chr6 | 100051772 | 100051971 | chr6 | 100053221 | 100053511 | chr6 | 100054866 | 100054917 |
| chr6 | 100061022 | 100061076 | chr6 | 100061311 | 100061419 | chr6 | 100062178 | 100062586 |
| chr6 | 100062944 | 100063068 | chr6 | 100441498 | 100441737 | chr6 | 100441762 | 100441966 |

TABLE 13-continued

| Pan Cancer #3 | | | | | | | | |
|---|---|---|---|---|---|---|---|---|
| chr | start | end | chr | start | end | chr | start | end |
| chr6 | 100903384 | 100903404 | chr6 | 100903561 | 100903631 | chr6 | 100904214 | 100904275 |
| chr6 | 100905969 | 100906016 | chr6 | 100911686 | 100911723 | chr6 | 100912070 | 100912119 |
| chr6 | 100912421 | 100912445 | chr6 | 100912466 | 100912480 | chr6 | 100912919 | 100913050 |
| chr6 | 100915101 | 100915205 | chr6 | 101840708 | 101840820 | chr6 | 101846782 | 101846789 |
| chr6 | 101847185 | 101847215 | chr6 | 101850147 | 101850275 | chr6 | 105388679 | 105388708 |
| chr6 | 105389510 | 105389710 | chr6 | 105400913 | 105401007 | chr6 | 105401620 | 105401874 |
| chr6 | 105404574 | 105404674 | chr6 | 105405656 | 105405772 | chr6 | 105406098 | 105406128 |
| chr6 | 105584264 | 105584319 | chr6 | 105584367 | 105585554 | chr6 | 105821423 | 105821453 |
| chr6 | 106429049 | 106429475 | chr6 | 106429590 | 106429624 | chr6 | 106434339 | 106434368 |
| chr6 | 106441869 | 106442979 | chr6 | 106731553 | 106731597 | chr6 | 106960908 | 106961023 |
| chr6 | 107562814 | 107562859 | chr6 | 108280322 | 108280352 | chr6 | 108435075 | 108435263 |
| chr6 | 108436072 | 108436526 | chr6 | 108438261 | 108438577 | chr6 | 108440091 | 108440644 |
| chr6 | 108440745 | 108440961 | chr6 | 108479290 | 108479665 | chr6 | 108484909 | 108485406 |
| chr6 | 108485665 | 108485905 | chr6 | 108486158 | 108486394 | chr6 | 108487724 | 108488416 |
| chr6 | 108489662 | 108489808 | chr6 | 108490067 | 108490245 | chr6 | 108490297 | 108490514 |
| chr6 | 108490538 | 108490633 | chr6 | 108490978 | 108491000 | chr6 | 108491108 | 108491423 |
| chr6 | 108492270 | 108492451 | chr6 | 108495681 | 108495817 | chr6 | 108495916 | 108495951 |
| chr6 | 108496208 | 108496649 | chr6 | 108497494 | 108497796 | chr6 | 108497827 | 108497881 |
| chr6 | 110437721 | 110437751 | chr6 | 110679123 | 110679414 | chr6 | 110797678 | 110797708 |
| chr6 | 110798007 | 110798036 | chr6 | 116783448 | 116783493 | chr6 | 117086249 | 117086639 |
| chr6 | 117585967 | 117586004 | chr6 | 117586847 | 117587169 | chr6 | 117587480 | 117587577 |
| chr6 | 117591161 | 117591191 | chr6 | 117591411 | 117591596 | chr6 | 117591684 | 117591743 |
| chr6 | 118228102 | 118228151 | chr6 | 118228747 | 118228828 | chr6 | 118229154 | 118229383 |
| chr6 | 118229626 | 118229818 | chr6 | 118241228 | 118241308 | chr6 | 118241395 | 118241500 |
| chr6 | 119254654 | 119254678 | chr6 | 121758672 | 121758994 | chr6 | 123317073 | 123317589 |
| chr6 | 123317797 | 123317833 | chr6 | 124124432 | 124124466 | chr6 | 124124860 | 124125016 |
| chr6 | 125284131 | 125284175 | chr6 | 126068092 | 126068178 | chr6 | 127439379 | 127439453 |
| chr6 | 127439985 | 127440127 | chr6 | 127440331 | 127440962 | chr6 | 127441031 | 127441123 |
| chr6 | 127441554 | 127441762 | chr6 | 127442021 | 127442070 | chr6 | 127442090 | 127442104 |
| chr6 | 127840501 | 127840681 | chr6 | 129204459 | 129204524 | chr6 | 130686534 | 130687057 |
| chr6 | 131602584 | 131602694 | chr6 | 132722078 | 132722141 | chr6 | 132722158 | 132722196 |
| chr6 | 133561740 | 133562070 | chr6 | 133562374 | 133562436 | chr6 | 133562675 | 133563058 |
| chr6 | 133563327 | 133563918 | chr6 | 134067453 | 134067471 | chr6 | 134176232 | 134176299 |
| chr6 | 134176549 | 134176579 | chr6 | 134210528 | 134211018 | chr6 | 134211112 | 134211367 |
| chr6 | 134213944 | 134213987 | chr6 | 134214077 | 134214364 | chr6 | 134589500 | 134589604 |
| chr6 | 134638950 | 134639003 | chr6 | 137241928 | 137242205 | chr6 | 137243208 | 137243410 |
| chr6 | 137244114 | 137244148 | chr6 | 137244236 | 137244465 | chr6 | 137311158 | 137311380 |
| chr6 | 137366354 | 137366383 | chr6 | 137809141 | 137809365 | chr6 | 137809446 | 137809916 |
| chr6 | 137810033 | 137811088 | chr6 | 137813787 | 137813895 | chr6 | 137814604 | 137814618 |
| chr6 | 137814654 | 137814763 | chr6 | 137815008 | 137815170 | chr6 | 137815225 | 137815662 |
| chr6 | 137816472 | 137817351 | chr6 | 137818505 | 137818598 | chr6 | 137818619 | 137819368 |
| chr6 | 146755567 | 146755649 | chr6 | 149868368 | 149868387 | chr6 | 150284552 | 150284581 |
| chr6 | 150285056 | 150285368 | chr6 | 150285545 | 150285885 | chr6 | 150286100 | 150286639 |
| chr6 | 150358970 | 150359192 | chr6 | 151561016 | 151561340 | chr6 | 151561369 | 151561857 |
| chr6 | 151562066 | 151562563 | chr6 | 151815055 | 151815089 | chr6 | 152419908 | 152419940 |
| chr6 | 152623015 | 152623493 | chr6 | 152957895 | 152958076 | chr6 | 153451236 | 153451500 |
| chr6 | 153451890 | 153451968 | chr6 | 153452232 | 153452320 | chr6 | 153452713 | 153452746 |
| chr6 | 154360650 | 154360746 | chr6 | 154970558 | 154970587 | chr6 | 155316257 | 155316265 |
| chr6 | 155569208 | 155569305 | chr6 | 157502438 | 157502561 | chr6 | 157506082 | 157506112 |
| chr6 | 157556764 | 157557296 | chr6 | 159290823 | 159290852 | chr6 | 159590048 | 159590086 |
| chr6 | 159590155 | 159590761 | chr6 | 159590972 | 159590986 | chr6 | 159654923 | 159655003 |
| chr6 | 161100361 | 161100390 | chr6 | 161188513 | 161188543 | chr6 | 161352101 | 161352135 |
| chr6 | 161780098 | 161780139 | chr6 | 163602842 | 163602872 | chr6 | 163834314 | 163834382 |
| chr6 | 163834406 | 163834532 | chr6 | 163834857 | 163834901 | chr6 | 163836568 | 163836900 |
| chr6 | 164179652 | 164179668 | chr6 | 164196987 | 164197003 | chr6 | 164228294 | 164228363 |
| chr6 | 164246109 | 164246143 | chr6 | 164283254 | 164283377 | chr6 | 164314289 | 164314443 |
| chr6 | 164322666 | 164322775 | chr6 | 166074119 | 166074412 | chr6 | 166076788 | 166077021 |
| chr6 | 166077378 | 166077632 | chr6 | 166267582 | 166267891 | chr6 | 166401254 | 166401307 |
| chr6 | 166402240 | 166402546 | chr6 | 166421911 | 166422185 | chr6 | 166579723 | 166580144 |
| chr6 | 166580344 | 166582797 | chr6 | 166944367 | 166944403 | chr6 | 167835129 | 167835171 |
| chr6 | 168719983 | 168720019 | chr6 | 168842847 | 168842944 | chr6 | 168858122 | 168858296 |
| chr6 | 168972472 | 168972502 | chr6 | 169002054 | 169002084 | chr6 | 169653638 | 169653668 |
| chr6 | 170047467 | 170047499 | chr6 | 170240639 | 170240714 | chr6 | 170264708 | 170264761 |
| chr6 | 170475105 | 170475267 | chr6 | 170494286 | 170494315 | chr6 | 170894820 | 170894836 |
| chr7 | 68930 | 68960 | chr7 | 329805 | 329838 | chr7 | 369844 | 369980 |
| chr7 | 389663 | 389693 | chr7 | 409826 | 409892 | chr7 | 427454 | 427484 |
| chr7 | 431386 | 431492 | chr7 | 497782 | 497934 | chr7 | 503811 | 503936 |
| chr7 | 551599 | 551697 | chr7 | 556928 | 556983 | chr7 | 564237 | 564271 |
| chr7 | 578922 | 579020 | chr7 | 579827 | 579857 | chr7 | 752120 | 752221 |
| chr7 | 907656 | 907709 | chr7 | 915058 | 915087 | chr7 | 922050 | 922235 |
| chr7 | 927933 | 927986 | chr7 | 1022224 | 1022254 | chr7 | 1030172 | 1030283 |
| chr7 | 1054579 | 1054696 | chr7 | 1086199 | 1086319 | chr7 | 1195270 | 1195364 |
| chr7 | 1263761 | 1263960 | chr7 | 1268318 | 1268366 | chr7 | 1269305 | 1269463 |
| chr7 | 1269553 | 1269808 | chr7 | 1270406 | 1270440 | chr7 | 1273167 | 1273330 |
| chr7 | 1274641 | 1274677 | chr7 | 1275579 | 1275680 | chr7 | 1277817 | 1277865 |
| chr7 | 1279099 | 1279129 | chr7 | 1279965 | 1279995 | chr7 | 1281131 | 1281232 |

TABLE 13-continued

Pan Cancer #3

| chr | start | end | chr | start | end | chr | start | end |
|---|---|---|---|---|---|---|---|---|
| chr7 | 1281493 | 1281555 | chr7 | 1282042 | 1282150 | chr7 | 1282506 | 1282644 |
| chr7 | 1288582 | 1288753 | chr7 | 1308351 | 1308497 | chr7 | 1325810 | 1325882 |
| chr7 | 1416020 | 1416131 | chr7 | 1423632 | 1423677 | chr7 | 1459041 | 1459191 |
| chr7 | 1503417 | 1503596 | chr7 | 1547311 | 1547394 | chr7 | 1598639 | 1598697 |
| chr7 | 1607386 | 1607465 | chr7 | 1607971 | 1608001 | chr7 | 1615390 | 1615444 |
| chr7 | 1627404 | 1627434 | chr7 | 1641774 | 1641923 | chr7 | 1681189 | 1681239 |
| chr7 | 1688977 | 1689122 | chr7 | 1690745 | 1690851 | chr7 | 1709138 | 1709235 |
| chr7 | 1709474 | 1709561 | chr7 | 1733166 | 1733378 | chr7 | 1748514 | 1748766 |
| chr7 | 1775831 | 1775861 | chr7 | 1778875 | 1778914 | chr7 | 1783551 | 1783623 |
| chr7 | 1786514 | 1786899 | chr7 | 1787166 | 1787324 | chr7 | 1800882 | 1800912 |
| chr7 | 1970842 | 1970872 | chr7 | 2109874 | 2109904 | chr7 | 2163332 | 2163467 |
| chr7 | 2208670 | 2208808 | chr7 | 2232963 | 2233056 | chr7 | 2233292 | 2233414 |
| chr7 | 2238118 | 2238235 | chr7 | 2300787 | 2300813 | chr7 | 2473452 | 2473605 |
| chr7 | 2565919 | 2566041 | chr7 | 2566600 | 2566630 | chr7 | 2720013 | 2720140 |
| chr7 | 2728068 | 2728165 | chr7 | 2979480 | 2979512 | chr7 | 2985518 | 2985547 |
| chr7 | 3033658 | 3033688 | chr7 | 3083331 | 3083352 | chr7 | 3283704 | 3283894 |
| chr7 | 3340444 | 3340473 | chr7 | 3341570 | 3341597 | chr7 | 4215324 | 4215384 |
| chr7 | 4856984 | 4857048 | chr7 | 4922550 | 4922706 | chr7 | 4923328 | 4923397 |
| chr7 | 4998201 | 4998388 | chr7 | 5111528 | 5111669 | chr7 | 5262433 | 5262562 |
| chr7 | 5397777 | 5397938 | chr7 | 5632939 | 5633100 | chr7 | 5648107 | 5648393 |
| chr7 | 6059103 | 6059182 | chr7 | 6060590 | 6060612 | chr7 | 6099217 | 6099246 |
| chr7 | 6124620 | 6124714 | chr7 | 6188610 | 6189061 | chr7 | 6414386 | 6414415 |
| chr7 | 6426878 | 6426907 | chr7 | 6443279 | 6443376 | chr7 | 6443826 | 6443856 |
| chr7 | 6524573 | 6524599 | chr7 | 6524977 | 6525012 | chr7 | 6525477 | 6525512 |
| chr7 | 6543150 | 6543216 | chr7 | 6560235 | 6560345 | chr7 | 6566413 | 6566663 |
| chr7 | 6570959 | 6571130 | chr7 | 6576137 | 6576367 | chr7 | 6703555 | 6703869 |
| chr7 | 6703916 | 6703959 | chr7 | 7605662 | 7605822 | chr7 | 8473070 | 8473455 |
| chr7 | 8473480 | 8473674 | chr7 | 8473956 | 8474241 | chr7 | 8474516 | 8474562 |
| chr7 | 8474814 | 8475057 | chr7 | 8480640 | 8481159 | chr7 | 8481642 | 8481833 |
| chr7 | 8482056 | 8482297 | chr7 | 8482670 | 8482824 | chr7 | 8482885 | 8482921 |
| chr7 | 8483147 | 8483950 | chr7 | 12151440 | 12151472 | chr7 | 12151524 | 12151678 |
| chr7 | 12443317 | 12443403 | chr7 | 12443841 | 12443871 | chr7 | 12610339 | 12610476 |
| chr7 | 15725983 | 15726081 | chr7 | 15726634 | 15727077 | chr7 | 15727290 | 15727320 |
| chr7 | 19145808 | 19145893 | chr7 | 19146032 | 19146184 | chr7 | 19146238 | 19146249 |
| chr7 | 19146502 | 19146558 | chr7 | 19147122 | 19147798 | chr7 | 19152224 | 19152349 |
| chr7 | 19155791 | 19155820 | chr7 | 19156126 | 19156132 | chr7 | 19156304 | 19156643 |
| chr7 | 19156703 | 19156745 | chr7 | 19157144 | 19157566 | chr7 | 19157634 | 19158015 |
| chr7 | 19158632 | 19158735 | chr7 | 19184058 | 19184255 | chr7 | 19813284 | 19813313 |
| chr7 | 20816252 | 20816447 | chr7 | 20817380 | 20817410 | chr7 | 20818130 | 20818276 |
| chr7 | 20823292 | 20823330 | chr7 | 20823383 | 20823432 | chr7 | 20823920 | 20824143 |
| chr7 | 20824476 | 20824819 | chr7 | 20824836 | 20824946 | chr7 | 20825379 | 20825559 |
| chr7 | 20826113 | 20826202 | chr7 | 20826884 | 20827199 | chr7 | 20830670 | 20830700 |
| chr7 | 20833167 | 20833322 | chr7 | 21582593 | 21582640 | chr7 | 21582792 | 21582868 |
| chr7 | 21583263 | 21583277 | chr7 | 21583304 | 21583326 | chr7 | 22539833 | 22539909 |
| chr7 | 22589356 | 22589870 | chr7 | 23287253 | 23287350 | chr7 | 23287533 | 23287624 |
| chr7 | 23578780 | 23578857 | chr7 | 24323763 | 24323939 | chr7 | 24580785 | 24580806 |
| chr7 | 24796478 | 24796567 | chr7 | 25132702 | 25132726 | chr7 | 25896521 | 25896603 |
| chr7 | 25896663 | 25896864 | chr7 | 25897133 | 25897246 | chr7 | 27127863 | 27127898 |
| chr7 | 27135327 | 27135770 | chr7 | 27136013 | 27136790 | chr7 | 27138381 | 27138410 |
| chr7 | 27184015 | 27184190 | chr7 | 27190591 | 27191226 | chr7 | 27192061 | 27192098 |
| chr7 | 27195462 | 27195601 | chr7 | 27195867 | 27195892 | chr7 | 27196153 | 27196839 |
| chr7 | 27204487 | 27204769 | chr7 | 27205266 | 27205395 | chr7 | 27205678 | 27205789 |
| chr7 | 27208187 | 27208285 | chr7 | 27209462 | 27209582 | chr7 | 27212499 | 27212899 |
| chr7 | 27213189 | 27214261 | chr7 | 27217042 | 27217071 | chr7 | 27223114 | 27223151 |
| chr7 | 27223601 | 27223696 | chr7 | 27224069 | 27224609 | chr7 | 27225035 | 27225057 |
| chr7 | 27225447 | 27225483 | chr7 | 27227874 | 27227953 | chr7 | 27231476 | 27231505 |
| chr7 | 27231818 | 27231894 | chr7 | 27232289 | 27232962 | chr7 | 27233410 | 27233454 |
| chr7 | 27238887 | 27238917 | chr7 | 27239226 | 27239234 | chr7 | 27240230 | 27240381 |
| chr7 | 27244515 | 27244610 | chr7 | 27244798 | 27245310 | chr7 | 27245668 | 27245795 |
| chr7 | 27252380 | 27252410 | chr7 | 27260092 | 27260100 | chr7 | 27264875 | 27265325 |
| chr7 | 27265538 | 27265584 | chr7 | 27275513 | 27275543 | chr7 | 27279238 | 27279368 |
| chr7 | 27281329 | 27281360 | chr7 | 27282089 | 27283013 | chr7 | 27283351 | 27283627 |
| chr7 | 27285621 | 27285913 | chr7 | 27285980 | 27286098 | chr7 | 27286171 | 27286248 |
| chr7 | 27288946 | 27289100 | chr7 | 27289170 | 27289449 | chr7 | 27291315 | 27291851 |
| chr7 | 28110701 | 28110828 | chr7 | 28449276 | 28449290 | chr7 | 28449659 | 28449781 |
| chr7 | 28449858 | 28450015 | chr7 | 28995657 | 28995978 | chr7 | 28996457 | 28996495 |
| chr7 | 28996840 | 28996916 | chr7 | 28997136 | 28997625 | chr7 | 28998053 | 28998119 |
| chr7 | 30029702 | 30029822 | chr7 | 30029923 | 30029952 | chr7 | 30721280 | 30721902 |
| chr7 | 30722290 | 30722375 | chr7 | 30857157 | 30857292 | chr7 | 31093003 | 31093133 |
| chr7 | 31232909 | 31232939 | chr7 | 31375965 | 31376135 | chr7 | 32110704 | 32110772 |
| chr7 | 32337807 | 32337837 | chr7 | 32338088 | 32338217 | chr7 | 32338284 | 32338410 |
| chr7 | 32338900 | 32338930 | chr7 | 32467461 | 32467655 | chr7 | 32467947 | 32468062 |
| chr7 | 32997124 | 32997454 | chr7 | 33167928 | 33167949 | chr7 | 33725803 | 33725938 |
| chr7 | 33943459 | 33943759 | chr7 | 35225809 | 35225833 | chr7 | 35226193 | 35226522 |
| chr7 | 35226557 | 35226765 | chr7 | 35292970 | 35293086 | chr7 | 35293183 | 35293293 |
| chr7 | 35294032 | 35294141 | chr7 | 35294502 | 35294536 | chr7 | 35295104 | 35295105 |

TABLE 13-continued

Pan Cancer #3

| chr | start | end | chr | start | end | chr | start | end |
|---|---|---|---|---|---|---|---|---|
| chr7 | 35295908 | 35295944 | chr7 | 35296935 | 35297004 | chr7 | 35297138 | 35297353 |
| chr7 | 35297471 | 35298016 | chr7 | 35300951 | 35301008 | chr7 | 35301102 | 35301948 |
| chr7 | 37487164 | 37487255 | chr7 | 37487375 | 37487453 | chr7 | 37487756 | 37487826 |
| chr7 | 37488257 | 37488578 | chr7 | 37488920 | 37488992 | chr7 | 37907440 | 37907470 |
| chr7 | 37955878 | 37955979 | chr7 | 37956271 | 37956439 | chr7 | 37960301 | 37960335 |
| chr7 | 38588471 | 38588501 | chr7 | 38670357 | 38670663 | chr7 | 38670957 | 38671015 |
| chr7 | 39015542 | 39015981 | chr7 | 39649223 | 39649253 | chr7 | 39649444 | 39649457 |
| chr7 | 39872836 | 39873015 | chr7 | 41739663 | 41739879 | chr7 | 41982690 | 41982874 |
| chr7 | 42267647 | 42267677 | chr7 | 42276346 | 42276634 | chr7 | 42377468 | 42377497 |
| chr7 | 42533257 | 42533296 | chr7 | 43152109 | 43152207 | chr7 | 43152414 | 43152700 |
| chr7 | 43152957 | 43153199 | chr7 | 43153230 | 43153237 | chr7 | 44097690 | 44097876 |
| chr7 | 44151398 | 44151428 | chr7 | 44151795 | 44151933 | chr7 | 44163926 | 44163989 |
| chr7 | 44364838 | 44364903 | chr7 | 44740630 | 44740672 | chr7 | 44835121 | 44835384 |
| chr7 | 45038532 | 45038564 | chr7 | 45046874 | 45046982 | chr7 | 45613785 | 45613813 |
| chr7 | 45613858 | 45613898 | chr7 | 45614341 | 45614474 | chr7 | 45614738 | 45614809 |
| chr7 | 45614929 | 45615020 | chr7 | 45615440 | 45615495 | chr7 | 45960743 | 45960794 |
| chr7 | 45961146 | 45961176 | chr7 | 45961508 | 45961576 | chr7 | 45961833 | 45961888 |
| chr7 | 47515359 | 47515405 | chr7 | 47704324 | 47704359 | chr7 | 49812820 | 49813017 |
| chr7 | 49813810 | 49813994 | chr7 | 49814531 | 49814750 | chr7 | 49815117 | 49815249 |
| chr7 | 49815657 | 49815765 | chr7 | 49819674 | 49819703 | chr7 | 50294451 | 50294481 |
| chr7 | 50343263 | 50343401 | chr7 | 50343975 | 50343994 | chr7 | 50344226 | 50344491 |
| chr7 | 50365076 | 50365107 | chr7 | 50438618 | 50438648 | chr7 | 50441145 | 50441285 |
| chr7 | 50560588 | 50560637 | chr7 | 50860226 | 50861102 | chr7 | 51383754 | 51383790 |
| chr7 | 51384327 | 51384440 | chr7 | 51384915 | 51384951 | chr7 | 52156231 | 52156261 |
| chr7 | 54609852 | 54609951 | chr7 | 54609992 | 54610153 | chr7 | 54612418 | 54612730 |
| chr7 | 55086473 | 55086601 | chr7 | 55086983 | 55087533 | chr7 | 55209976 | 55210005 |
| chr7 | 55211065 | 55211094 | chr7 | 55221729 | 55221836 | chr7 | 55223589 | 55223636 |
| chr7 | 55227993 | 55228022 | chr7 | 55233028 | 55233123 | chr7 | 55241663 | 55241737 |
| chr7 | 55242419 | 55242493 | chr7 | 55248975 | 55249085 | chr7 | 55259404 | 55259547 |
| chr7 | 55260469 | 55260498 | chr7 | 55268867 | 55268896 | chr7 | 55410019 | 55410126 |
| chr7 | 55506288 | 55506348 | chr7 | 56018123 | 56018205 | chr7 | 56031793 | 56031869 |
| chr7 | 63667431 | 63667460 | chr7 | 64330411 | 64330470 | chr7 | 64330734 | 64330833 |
| chr7 | 64349042 | 64349056 | chr7 | 64349331 | 64349470 | chr7 | 64700283 | 64700329 |
| chr7 | 64712364 | 64712510 | chr7 | 64974382 | 64974402 | chr7 | 65037609 | 65037702 |
| chr7 | 65508995 | 65509043 | chr7 | 65878743 | 65878793 | chr7 | 66214942 | 66214961 |
| chr7 | 68204793 | 68204931 | chr7 | 69062519 | 69062635 | chr7 | 69064590 | 69064771 |
| chr7 | 69064834 | 69065045 | chr7 | 69897780 | 69897827 | chr7 | 70596454 | 70596688 |
| chr7 | 70597406 | 70597451 | chr7 | 70597835 | 70597871 | chr7 | 70597995 | 70598123 |
| chr7 | 70598170 | 70598387 | chr7 | 71217108 | 71217332 | chr7 | 71603924 | 71604082 |
| chr7 | 71800676 | 71800756 | chr7 | 71800934 | 71801104 | chr7 | 71802410 | 71802522 |
| chr7 | 71802578 | 71802637 | chr7 | 71871203 | 71871245 | chr7 | 75511201 | 75511298 |
| chr7 | 76033250 | 76033289 | chr7 | 77129885 | 77129907 | chr7 | 77324362 | 77324448 |
| chr7 | 79081792 | 79081821 | chr7 | 79082023 | 79082218 | chr7 | 79083392 | 79083834 |
| chr7 | 80548257 | 80548403 | chr7 | 82072350 | 82072503 | chr7 | 82073495 | 82073533 |
| chr7 | 84815141 | 84815226 | chr7 | 84815744 | 84815954 | chr7 | 86273208 | 86273541 |
| chr7 | 86274258 | 86274457 | chr7 | 87104816 | 87105430 | chr7 | 87229537 | 87230433 |
| chr7 | 87257012 | 87257047 | chr7 | 87257963 | 87258054 | chr7 | 87563370 | 87563614 |
| chr7 | 87563829 | 87563890 | chr7 | 87825102 | 87825137 | chr7 | 88387982 | 88388167 |
| chr7 | 88388540 | 88388660 | chr7 | 88388879 | 88388901 | chr7 | 88389047 | 88389356 |
| chr7 | 89747996 | 89748340 | chr7 | 89950183 | 89950810 | chr7 | 90226269 | 90226464 |
| chr7 | 90895012 | 90895097 | chr7 | 92466152 | 92466400 | chr7 | 92689705 | 92689792 |
| chr7 | 93203708 | 93203756 | chr7 | 93204332 | 93204492 | chr7 | 93519351 | 93519765 |
| chr7 | 93519855 | 93520137 | chr7 | 93551323 | 93551425 | chr7 | 94284302 | 94284873 |
| chr7 | 96619560 | 96619603 | chr7 | 96621715 | 96621811 | chr7 | 96622107 | 96622349 |
| chr7 | 96622694 | 96622723 | chr7 | 96625537 | 96625720 | chr7 | 96625998 | 96626051 |
| chr7 | 96627013 | 96627048 | chr7 | 96631579 | 96631680 | chr7 | 96634645 | 96634928 |
| chr7 | 96635345 | 96635379 | chr7 | 96635439 | 96635451 | chr7 | 96635733 | 96635971 |
| chr7 | 96636034 | 96636645 | chr7 | 96639318 | 96639348 | chr7 | 96646662 | 96647131 |
| chr7 | 96647809 | 96648219 | chr7 | 96649955 | 96650094 | chr7 | 96650884 | 96651076 |
| chr7 | 96651137 | 96651151 | chr7 | 96651469 | 96651537 | chr7 | 96652144 | 96652174 |
| chr7 | 96653507 | 96653819 | chr7 | 96653863 | 96653993 | chr7 | 97361098 | 97361422 |
| chr7 | 97361521 | 97361781 | chr7 | 97362292 | 97362607 | chr7 | 97600104 | 97600194 |
| chr7 | 97869614 | 97869644 | chr7 | 98197224 | 98197242 | chr7 | 98245885 | 98246078 |
| chr7 | 98246305 | 98246507 | chr7 | 98246534 | 98246868 | chr7 | 98247126 | 98247656 |
| chr7 | 98966786 | 98966881 | chr7 | 98971529 | 98971549 | chr7 | 99104258 | 99104293 |
| chr7 | 99177742 | 99177870 | chr7 | 99591731 | 99591762 | chr7 | 99595194 | 99595335 |
| chr7 | 99751578 | 99751630 | chr7 | 99775192 | 99775558 | chr7 | 100088183 | 100088312 |
| chr7 | 100179889 | 100179927 | chr7 | 100295403 | 100295424 | chr7 | 100318505 | 100318575 |
| chr7 | 100320690 | 100320719 | chr7 | 100547037 | 100547073 | chr7 | 100609750 | 100609780 |
| chr7 | 100808466 | 100808502 | chr7 | 100809436 | 100809521 | chr7 | 100823436 | 100823497 |
| chr7 | 101005968 | 101005998 | chr7 | 101241993 | 101242023 | chr7 | 101475790 | 101475858 |
| chr7 | 101558399 | 101558698 | chr7 | 101627741 | 101627787 | chr7 | 101707502 | 101707532 |
| chr7 | 103085876 | 103086474 | chr7 | 103629059 | 103629794 | chr7 | 103630054 | 103630082 |
| chr7 | 103630475 | 103630824 | chr7 | 103969217 | 103969341 | chr7 | 103969694 | 103969794 |
| chr7 | 105279467 | 105279671 | chr7 | 106622834 | 106622961 | chr7 | 106685282 | 106685345 |
| chr7 | 106797774 | 106797804 | chr7 | 107301494 | 107301640 | chr7 | 107483694 | 107483918 |

TABLE 13-continued

| | | Pan Cancer #3 | | | | | | |
|---|---|---|---|---|---|---|---|---|
| chr | start | end | chr | start | end | chr | start | end |
| chr7 | 108095329 | 108095362 | chr7 | 108095781 | 108096055 | chr7 | 108097172 | 108097491 |
| chr7 | 111202993 | 111203097 | chr7 | 112726558 | 112726614 | chr7 | 113722810 | 113723283 |
| chr7 | 113723339 | 113723439 | chr7 | 113724956 | 113725081 | chr7 | 113726509 | 113726539 |
| chr7 | 113727442 | 113727486 | chr7 | 113727754 | 113727781 | chr7 | 115117552 | 115117647 |
| chr7 | 116140252 | 116140356 | chr7 | 116412008 | 116412058 | chr7 | 116415100 | 116415129 |
| chr7 | 116417443 | 116417496 | chr7 | 116422067 | 116422132 | chr7 | 116423399 | 116423488 |
| chr7 | 116962893 | 116963146 | chr7 | 116963331 | 116963476 | chr7 | 117119381 | 117120271 |
| chr7 | 117513675 | 117513849 | chr7 | 119913561 | 119913785 | chr7 | 120969672 | 120969800 |
| chr7 | 121513523 | 121513709 | chr7 | 121939677 | 121940244 | chr7 | 121940434 | 121940448 |
| chr7 | 121940935 | 121941052 | chr7 | 121941881 | 121942170 | chr7 | 121945822 | 121945920 |
| chr7 | 121946478 | 121946982 | chr7 | 121947098 | 121947406 | chr7 | 121950137 | 121950264 |
| chr7 | 121950429 | 121950552 | chr7 | 121950995 | 121951069 | chr7 | 121951877 | 121952010 |
| chr7 | 121952044 | 121952169 | chr7 | 121956486 | 121956567 | chr7 | 121956955 | 121957076 |
| chr7 | 121957254 | 121957331 | chr7 | 122526833 | 122526873 | chr7 | 123173150 | 123173244 |
| chr7 | 123672048 | 123672086 | chr7 | 124404415 | 124404497 | chr7 | 126891220 | 126891250 |
| chr7 | 126891504 | 126891593 | chr7 | 126894076 | 126894197 | chr7 | 127371129 | 127371249 |
| chr7 | 127615921 | 127615951 | chr7 | 127744122 | 127744631 | chr7 | 127806634 | 127806664 |
| chr7 | 127807817 | 127807846 | chr7 | 127808047 | 127808792 | chr7 | 127841626 | 127841704 |
| chr7 | 127991826 | 127991922 | chr7 | 127992045 | 127992135 | chr7 | 128097059 | 128097089 |
| chr7 | 128337467 | 128337544 | chr7 | 128337788 | 128337921 | chr7 | 128470897 | 128471032 |
| chr7 | 128486036 | 128486138 | chr7 | 128528749 | 128528779 | chr7 | 128529023 | 128529053 |
| chr7 | 128828195 | 128828272 | chr7 | 129229604 | 129229631 | chr7 | 129418057 | 129418428 |
| chr7 | 129422160 | 129422968 | chr7 | 129423126 | 129423418 | chr7 | 129424655 | 129425887 |
| chr7 | 129426195 | 129426236 | chr7 | 129483356 | 129483449 | chr7 | 129794593 | 129794721 |
| chr7 | 129800243 | 129800434 | chr7 | 129844450 | 129844493 | chr7 | 131041515 | 131041596 |
| chr7 | 131242738 | 131242824 | chr7 | 131514824 | 131514854 | chr7 | 132261272 | 132261432 |
| chr7 | 134143164 | 134143475 | chr7 | 134143807 | 134144132 | chr7 | 134918503 | 134918637 |
| chr7 | 136553311 | 136554025 | chr7 | 136554104 | 136554366 | chr7 | 136554638 | 136554966 |
| chr7 | 136555235 | 136555412 | chr7 | 136555681 | 136555841 | chr7 | 136556013 | 136556091 |
| chr7 | 136969053 | 136969083 | chr7 | 137028481 | 137028524 | chr7 | 137531158 | 137531211 |
| chr7 | 137531263 | 137531888 | chr7 | 137531909 | 137532187 | chr7 | 138042221 | 138042288 |
| chr7 | 138720785 | 138720909 | chr7 | 139167617 | 139167744 | chr7 | 139168115 | 139168379 |
| chr7 | 139208772 | 139208979 | chr7 | 139930051 | 139930270 | chr7 | 139939160 | 139939318 |
| chr7 | 140027008 | 140027079 | chr7 | 140180179 | 140180299 | chr7 | 140218053 | 140218082 |
| chr7 | 140218123 | 140218352 | chr7 | 140219405 | 140219435 | chr7 | 140339952 | 140339982 |
| chr7 | 140453121 | 140453167 | chr7 | 140477779 | 140477868 | chr7 | 140481381 | 140481431 |
| chr7 | 140772795 | 140773228 | chr7 | 140773563 | 140773750 | chr7 | 143042634 | 143042798 |
| chr7 | 143579739 | 143580069 | chr7 | 145812992 | 145813082 | chr7 | 145813412 | 145813494 |
| chr7 | 145813946 | 145814166 | chr7 | 148224584 | 148224686 | chr7 | 148508712 | 148508741 |
| chr7 | 148640211 | 148640250 | chr7 | 148846138 | 148846180 | chr7 | 148851143 | 148851234 |
| chr7 | 149112058 | 149112248 | chr7 | 149119948 | 149120073 | chr7 | 149411541 | 149411727 |
| chr7 | 149411835 | 149412304 | chr7 | 149570368 | 149570406 | chr7 | 149744505 | 149744560 |
| chr7 | 149917322 | 149917336 | chr7 | 149918119 | 149918149 | chr7 | 150038883 | 150038912 |
| chr7 | 150049604 | 150049631 | chr7 | 150069098 | 150069346 | chr7 | 150069679 | 150069820 |
| chr7 | 150070021 | 150070058 | chr7 | 150081236 | 150081308 | chr7 | 150716169 | 150716305 |
| chr7 | 150748192 | 150748406 | chr7 | 150753942 | 150753981 | chr7 | 150870816 | 150870889 |
| chr7 | 151106451 | 151106565 | chr7 | 151106590 | 151106988 | chr7 | 151107486 | 151107651 |
| chr7 | 151188034 | 151188063 | chr7 | 151298870 | 151299029 | chr7 | 151423571 | 151423639 |
| chr7 | 151591667 | 151591705 | chr7 | 152133406 | 152133436 | chr7 | 152622621 | 152622697 |
| chr7 | 152913656 | 152913801 | chr7 | 153583632 | 153584069 | chr7 | 153584389 | 153584623 |
| chr7 | 153584848 | 153585206 | chr7 | 153585602 | 153585606 | chr7 | 153633899 | 153633942 |
| chr7 | 153749720 | 153750042 | chr7 | 154561150 | 154561189 | chr7 | 154708275 | 154708338 |
| chr7 | 154862046 | 154862266 | chr7 | 155164454 | 155165562 | chr7 | 155165875 | 155166784 |
| chr7 | 155167034 | 155167089 | chr7 | 155167175 | 155167660 | chr7 | 155167834 | 155167909 |
| chr7 | 155174656 | 155174788 | chr7 | 155241318 | 155242049 | chr7 | 155242729 | 155243102 |
| chr7 | 155243346 | 155243533 | chr7 | 155243825 | 155243895 | chr7 | 155244180 | 155244361 |
| chr7 | 155246886 | 155247479 | chr7 | 155248913 | 155248943 | chr7 | 155249512 | 155249565 |
| chr7 | 155249925 | 155250011 | chr7 | 155250283 | 155250303 | chr7 | 155250324 | 155250355 |
| chr7 | 155250787 | 155250996 | chr7 | 155251701 | 155251854 | chr7 | 155251891 | 155251939 |
| chr7 | 155252247 | 155252261 | chr7 | 155252317 | 155252490 | chr7 | 155252862 | 155253041 |
| chr7 | 155254848 | 155255324 | chr7 | 155256269 | 155256312 | chr7 | 155257040 | 155257189 |
| chr7 | 155258193 | 155258487 | chr7 | 155258949 | 155259077 | chr7 | 155259120 | 155259622 |
| chr7 | 155259834 | 155259957 | chr7 | 155260039 | 155260137 | chr7 | 155260880 | 155260890 |
| chr7 | 155261071 | 155261210 | chr7 | 155301838 | 155301931 | chr7 | 155302328 | 155302895 |
| chr7 | 155302964 | 155303335 | chr7 | 155325796 | 155325872 | chr7 | 155326169 | 155326527 |
| chr7 | 155363304 | 155363417 | chr7 | 155580182 | 155580211 | chr7 | 155580846 | 155580876 |
| chr7 | 155581330 | 155581553 | chr7 | 155581765 | 155581980 | chr7 | 155582277 | 155582340 |
| chr7 | 155600629 | 155600723 | chr7 | 155602751 | 155602805 | chr7 | 156259192 | 156259221 |
| chr7 | 156409144 | 156409347 | chr7 | 156409728 | 156409802 | chr7 | 156701846 | 156701908 |
| chr7 | 156744696 | 156744713 | chr7 | 156794464 | 156794485 | chr7 | 156794998 | 156795354 |
| chr7 | 156795402 | 156795635 | chr7 | 156795900 | 156795914 | chr7 | 156796534 | 156796739 |
| chr7 | 156797006 | 156798434 | chr7 | 156798527 | 156799146 | chr7 | 156799291 | 156799467 |
| chr7 | 156800999 | 156801029 | chr7 | 156801403 | 156801601 | chr7 | 156808858 | 156809199 |
| chr7 | 156809983 | 156810521 | chr7 | 156810598 | 156810800 | chr7 | 156811303 | 156811436 |
| chr7 | 156812852 | 156813825 | chr7 | 156813987 | 156814707 | chr7 | 156814784 | 156815092 |
| chr7 | 156832223 | 156832402 | chr7 | 156832848 | 156833162 | chr7 | 156871283 | 156871297 |

TABLE 13-continued

Pan Cancer #3

| chr | start | end | chr | start | end | chr | start | end |
|---|---|---|---|---|---|---|---|---|
| chr7 | 156880531 | 156880561 | chr7 | 157085373 | 157085487 | chr7 | 157085963 | 157086082 |
| chr7 | 157262815 | 157263018 | chr7 | 157263294 | 157263471 | chr7 | 157335172 | 157335202 |
| chr7 | 157361605 | 157361635 | chr7 | 157476879 | 157476973 | chr7 | 157476995 | 157477272 |
| chr7 | 157477473 | 157477488 | chr7 | 157477711 | 157477819 | chr7 | 157481130 | 157481160 |
| chr7 | 157481534 | 157481549 | chr7 | 157481969 | 157482073 | chr7 | 157482492 | 157482667 |
| chr7 | 157483320 | 157483538 | chr7 | 157484877 | 157485277 | chr7 | 157485527 | 157485601 |
| chr7 | 157485650 | 157485705 | chr7 | 157485976 | 157486081 | chr7 | 157486205 | 157486414 |
| chr7 | 157486476 | 157486503 | chr7 | 157584178 | 157584208 | chr7 | 157588586 | 157588791 |
| chr7 | 157606706 | 157606736 | chr7 | 157690056 | 157690086 | chr7 | 158059762 | 158059794 |
| chr7 | 158065832 | 158065970 | chr7 | 158298861 | 158299036 | chr7 | 158673836 | 158673942 |
| chr7 | 158741193 | 158741267 | chr7 | 158799762 | 158799791 | chr7 | 158936492 | 158936880 |
| chr7 | 158937203 | 158937374 | chr7 | 158937577 | 158937624 | chr7 | 158938210 | 158938399 |
| chr8 | 686870 | 686884 | chr8 | 687163 | 687217 | chr8 | 687838 | 687975 |
| chr8 | 1085573 | 1085603 | chr8 | 1444165 | 1444205 | chr8 | 1950097 | 1950134 |
| chr8 | 4849141 | 4849177 | chr8 | 4849466 | 4849500 | chr8 | 4850247 | 4850322 |
| chr8 | 4850419 | 4850516 | chr8 | 4851736 | 4851749 | chr8 | 4852021 | 4852118 |
| chr8 | 8681258 | 8681353 | chr8 | 8748422 | 8748713 | chr8 | 8748919 | 8748956 |
| chr8 | 9722850 | 9722896 | chr8 | 9756051 | 9756283 | chr8 | 9760735 | 9761155 |
| chr8 | 9762586 | 9762689 | chr8 | 9762752 | 9762864 | chr8 | 9763143 | 9763275 |
| chr8 | 9763895 | 9764049 | chr8 | 9764196 | 9764214 | chr8 | 9764434 | 9764551 |
| chr8 | 10587589 | 10587602 | chr8 | 10652917 | 10652937 | chr8 | 10980452 | 10980491 |
| chr8 | 11204479 | 11204509 | chr8 | 11204810 | 11204905 | chr8 | 11536827 | 11536857 |
| chr8 | 11537225 | 11537259 | chr8 | 11554885 | 11554915 | chr8 | 11555152 | 11555166 |
| chr8 | 11555474 | 11555521 | chr8 | 11559759 | 11559794 | chr8 | 11560068 | 11560375 |
| chr8 | 11560711 | 11560793 | chr8 | 11561442 | 11562169 | chr8 | 11562422 | 11562485 |
| chr8 | 11562701 | 11562917 | chr8 | 11705960 | 11706136 | chr8 | 11706580 | 11706613 |
| chr8 | 11726469 | 11726512 | chr8 | 12990386 | 12990431 | chr8 | 12990664 | 12990784 |
| chr8 | 13319931 | 13319961 | chr8 | 15094505 | 15094566 | chr8 | 16884182 | 16884239 |
| chr8 | 16885205 | 16885241 | chr8 | 17271091 | 17271119 | chr8 | 19797433 | 19797463 |
| chr8 | 19797939 | 19798019 | chr8 | 20375563 | 20375592 | chr8 | 22089409 | 22089560 |
| chr8 | 22458657 | 22458687 | chr8 | 22562345 | 22562483 | chr8 | 22960648 | 22960723 |
| chr8 | 23020951 | 23021107 | chr8 | 23260683 | 23260870 | chr8 | 23423923 | 23423974 |
| chr8 | 23559385 | 23559601 | chr8 | 23559666 | 23560525 | chr8 | 23563791 | 23564023 |
| chr8 | 23564193 | 23564388 | chr8 | 23564652 | 23564668 | chr8 | 23564703 | 23565024 |
| chr8 | 23566803 | 23566854 | chr8 | 23566901 | 23567213 | chr8 | 23567312 | 23567492 |
| chr8 | 23571681 | 23571973 | chr8 | 23572377 | 23572554 | chr8 | 23584094 | 23584400 |
| chr8 | 23584582 | 23584760 | chr8 | 24770314 | 24770361 | chr8 | 24770414 | 24770581 |
| chr8 | 24771431 | 24771562 | chr8 | 24813188 | 24813287 | chr8 | 24813750 | 24813893 |
| chr8 | 24814011 | 24814407 | chr8 | 24857776 | 24857808 | chr8 | 24858336 | 24858440 |
| chr8 | 24858856 | 24859161 | chr8 | 24859496 | 24859526 | chr8 | 25041746 | 25041864 |
| chr8 | 25042534 | 25042567 | chr8 | 25900408 | 25900692 | chr8 | 25900781 | 25901317 |
| chr8 | 25901540 | 25901765 | chr8 | 25902146 | 25902176 | chr8 | 25902619 | 25902649 |
| chr8 | 25903662 | 25903854 | chr8 | 25904157 | 25904191 | chr8 | 25905096 | 25905126 |
| chr8 | 25905762 | 25905811 | chr8 | 25909197 | 25909597 | chr8 | 26372863 | 26372893 |
| chr8 | 26723985 | 26724080 | chr8 | 30243388 | 30243423 | chr8 | 30475450 | 30475480 |
| chr8 | 30769249 | 30769411 | chr8 | 30770106 | 30770109 | chr8 | 30770158 | 30770188 |
| chr8 | 31496481 | 31496757 | chr8 | 31497024 | 31497152 | chr8 | 31497499 | 31497639 |
| chr8 | 32406598 | 32406914 | chr8 | 33372069 | 33372125 | chr8 | 33457142 | 33457379 |
| chr8 | 35093037 | 35093054 | chr8 | 35093951 | 35093973 | chr8 | 37655476 | 37655517 |
| chr8 | 37655810 | 37655990 | chr8 | 37656050 | 37656081 | chr8 | 37822796 | 37823423 |
| chr8 | 37961878 | 37961902 | chr8 | 38008234 | 38008557 | chr8 | 38020213 | 38020272 |
| chr8 | 38274835 | 38274864 | chr8 | 38323911 | 38323941 | chr8 | 38965322 | 38965386 |
| chr8 | 39172082 | 39172134 | chr8 | 41165865 | 41165918 | chr8 | 41166001 | 41166151 |
| chr8 | 41166267 | 41166679 | chr8 | 41166974 | 41166988 | chr8 | 41167026 | 41167035 |
| chr8 | 41424760 | 41424842 | chr8 | 41624826 | 41624855 | chr8 | 41625112 | 41625141 |
| chr8 | 41700665 | 41700751 | chr8 | 41711416 | 41711447 | chr8 | 41733505 | 41733640 |
| chr8 | 41753593 | 41753752 | chr8 | 41754152 | 41754885 | chr8 | 41755178 | 41755208 |
| chr8 | 41910270 | 41910339 | chr8 | 42082721 | 42082798 | chr8 | 42147392 | 42147521 |
| chr8 | 42293633 | 42293722 | chr8 | 42350468 | 42350492 | chr8 | 42749974 | 42750012 |
| chr8 | 47093246 | 47093276 | chr8 | 47334619 | 47334678 | chr8 | 48044710 | 48044753 |
| chr8 | 48100155 | 48100443 | chr8 | 49293364 | 49293524 | chr8 | 49293581 | 49293614 |
| chr8 | 49468669 | 49469127 | chr8 | 49572029 | 49572058 | chr8 | 49783041 | 49783283 |
| chr8 | 49836145 | 49836174 | chr8 | 49959230 | 49959260 | chr8 | 50822179 | 50822308 |
| chr8 | 50822686 | 50822734 | chr8 | 50823452 | 50823562 | chr8 | 53322495 | 53322524 |
| chr8 | 53477408 | 53477736 | chr8 | 53478008 | 53478275 | chr8 | 53478480 | 53478720 |
| chr8 | 53851141 | 53851170 | chr8 | 53853811 | 53854509 | chr8 | 54163316 | 54163349 |
| chr8 | 54163674 | 54164126 | chr8 | 54789278 | 54789310 | chr8 | 54789632 | 54789805 |
| chr8 | 54790023 | 54790077 | chr8 | 54790291 | 54790855 | chr8 | 54791898 | 54791945 |
| chr8 | 54792185 | 54792237 | chr8 | 54792634 | 54792670 | chr8 | 54792702 | 54792760 |
| chr8 | 54794217 | 54794327 | chr8 | 54794713 | 54794780 | chr8 | 54794827 | 54794949 |
| chr8 | 54795140 | 54795165 | chr8 | 55366188 | 55366367 | chr8 | 55366952 | 55367641 |
| chr8 | 55370113 | 55370432 | chr8 | 55370568 | 55370713 | chr8 | 55370836 | 55370858 |
| chr8 | 55371178 | 55371375 | chr8 | 55371440 | 55371724 | chr8 | 55371994 | 55372067 |
| chr8 | 55372417 | 55372538 | chr8 | 55379296 | 55379456 | chr8 | 55383183 | 55383237 |
| chr8 | 56013641 | 56013892 | chr8 | 56014157 | 56014184 | chr8 | 56014623 | 56014743 |
| chr8 | 56015038 | 56015052 | chr8 | 56015186 | 56015357 | chr8 | 56015560 | 56015619 |

TABLE 13-continued

| Pan Cancer #3 | | | | | | | |
|---|---|---|---|---|---|---|---|
| chr | start | end | chr | start | end | chr | start | end |
| chr8 | 56015908 | 56015938 | chr8 | 57025776 | 57025943 | chr8 | 57026168 | 57026213 |
| chr8 | 57026503 | 57026547 | chr8 | 57069553 | 57069737 | chr8 | 57069851 | 57070157 |
| chr8 | 57358465 | 57358661 | chr8 | 57358807 | 57359091 | chr8 | 57359260 | 57359636 |
| chr8 | 57359893 | 57359922 | chr8 | 57360211 | 57360240 | chr8 | 57360570 | 57360625 |
| chr8 | 57360770 | 57360791 | chr8 | 58105946 | 58106115 | chr8 | 58117004 | 58117079 |
| chr8 | 58130364 | 58130574 | chr8 | 58907698 | 58907835 | chr8 | 59058941 | 59059343 |
| chr8 | 59747186 | 59747318 | chr8 | 60032680 | 60032738 | chr8 | 61777575 | 61777699 |
| chr8 | 61789974 | 61790004 | chr8 | 62034029 | 62034059 | chr8 | 62200502 | 62200776 |
| chr8 | 63161658 | 63161800 | chr8 | 65281616 | 65281760 | chr8 | 65281984 | 65282004 |
| chr8 | 65282333 | 65282440 | chr8 | 65282713 | 65282944 | chr8 | 65283042 | 65283341 |
| chr8 | 65283799 | 65284094 | chr8 | 65286056 | 65286066 | chr8 | 65286682 | 65286753 |
| chr8 | 65286963 | 65287251 | chr8 | 65289123 | 65289241 | chr8 | 65289614 | 65290681 |
| chr8 | 65291034 | 65291284 | chr8 | 65292185 | 65292727 | chr8 | 65488271 | 65488322 |
| chr8 | 65488661 | 65488697 | chr8 | 65489099 | 65489129 | chr8 | 65492712 | 65492979 |
| chr8 | 65493195 | 65493433 | chr8 | 65494077 | 65494193 | chr8 | 65498566 | 65498584 |
| chr8 | 65498644 | 65498841 | chr8 | 65499757 | 65500015 | chr8 | 65710938 | 65711046 |
| chr8 | 66548717 | 66548759 | chr8 | 66560524 | 66560545 | chr8 | 67025063 | 67025640 |
| chr8 | 67025920 | 67026429 | chr8 | 67026489 | 67026578 | chr8 | 67026812 | 67026990 |
| chr8 | 67344538 | 67344701 | chr8 | 67873327 | 67873421 | chr8 | 67873799 | 67874050 |
| chr8 | 67874165 | 67874672 | chr8 | 67874756 | 67875682 | chr8 | 67940624 | 67940875 |
| chr8 | 68864578 | 68864765 | chr8 | 69242905 | 69242988 | chr8 | 69243285 | 69243902 |
| chr8 | 69243964 | 69243994 | chr8 | 69244370 | 69244500 | chr8 | 70744860 | 70744925 |
| chr8 | 70946760 | 70946914 | chr8 | 70947091 | 70947658 | chr8 | 70982263 | 70982566 |
| chr8 | 70982851 | 70983226 | chr8 | 70983504 | 70983869 | chr8 | 70984017 | 70984292 |
| chr8 | 70984344 | 70984661 | chr8 | 70984745 | 70984978 | chr8 | 71308096 | 71308126 |
| chr8 | 71447529 | 71447559 | chr8 | 72273998 | 72274033 | chr8 | 72468569 | 72469574 |
| chr8 | 72470399 | 72470441 | chr8 | 72471053 | 72471083 | chr8 | 72754491 | 72754609 |
| chr8 | 72754821 | 72755176 | chr8 | 72755666 | 72755814 | chr8 | 72756656 | 72756896 |
| chr8 | 72917335 | 72917428 | chr8 | 72987600 | 72988036 | chr8 | 73163860 | 73164180 |
| chr8 | 73450064 | 73450100 | chr8 | 73450515 | 73450559 | chr8 | 74759385 | 74759463 |
| chr8 | 74759819 | 74759863 | chr8 | 75896574 | 75897337 | chr8 | 76316329 | 76316452 |
| chr8 | 77585219 | 77585698 | chr8 | 77586175 | 77586278 | chr8 | 77586563 | 77586617 |
| chr8 | 77590239 | 77590466 | chr8 | 77593110 | 77593376 | chr8 | 77593889 | 77594124 |
| chr8 | 77594648 | 77594674 | chr8 | 77594758 | 77594993 | chr8 | 77595339 | 77595494 |
| chr8 | 79428297 | 79428401 | chr8 | 80523983 | 80524029 | chr8 | 80524253 | 80524318 |
| chr8 | 80524946 | 80525020 | chr8 | 80525604 | 80525733 | chr8 | 80695902 | 80695932 |
| chr8 | 80803673 | 80803872 | chr8 | 81398018 | 81398155 | chr8 | 81398428 | 81399496 |
| chr8 | 81414737 | 81414831 | chr8 | 81478185 | 81478350 | chr8 | 85095482 | 85095668 |
| chr8 | 85096583 | 85096724 | chr8 | 85097063 | 85097220 | chr8 | 86350553 | 86350566 |
| chr8 | 86406813 | 86406849 | chr8 | 86436621 | 86436651 | chr8 | 86544756 | 86544798 |
| chr8 | 89339389 | 89339745 | chr8 | 89340274 | 89340345 | chr8 | 90913516 | 90913653 |
| chr8 | 91094221 | 91094251 | chr8 | 91803676 | 91803718 | chr8 | 91804065 | 91804253 |
| chr8 | 91997046 | 91997508 | chr8 | 91997528 | 91997947 | chr8 | 92083523 | 92083667 |
| chr8 | 93114135 | 93114241 | chr8 | 93114307 | 93114528 | chr8 | 95485999 | 95486029 |
| chr8 | 95651098 | 95651218 | chr8 | 95651538 | 95651655 | chr8 | 96219882 | 96219901 |
| chr8 | 96285420 | 96285457 | chr8 | 97157085 | 97157209 | chr8 | 97157667 | 97157897 |
| chr8 | 97158022 | 97158066 | chr8 | 97165644 | 97165676 | chr8 | 97166425 | 97166455 |
| chr8 | 97167178 | 97167223 | chr8 | 97167811 | 97167855 | chr8 | 97169838 | 97169955 |
| chr8 | 97170054 | 97170334 | chr8 | 97170867 | 97170897 | chr8 | 97171129 | 97171264 |
| chr8 | 97171318 | 97171958 | chr8 | 97172019 | 97172200 | chr8 | 97172433 | 97172739 |
| chr8 | 97172822 | 97173458 | chr8 | 97173822 | 97173863 | chr8 | 97173921 | 97173935 |
| chr8 | 97339846 | 97340195 | chr8 | 97506034 | 97506048 | chr8 | 97506178 | 97506407 |
| chr8 | 97506448 | 97506524 | chr8 | 97507115 | 97507284 | chr8 | 97507546 | 97507680 |
| chr8 | 98289825 | 98289867 | chr8 | 98289923 | 98290260 | chr8 | 98744202 | 98744234 |
| chr8 | 99234962 | 99235037 | chr8 | 99439104 | 99439133 | chr8 | 99439382 | 99440354 |
| chr8 | 99951404 | 99951434 | chr8 | 99951836 | 99952143 | chr8 | 99952199 | 99952303 |
| chr8 | 99952533 | 99952815 | chr8 | 99954490 | 99954562 | chr8 | 99954679 | 99954727 |
| chr8 | 99955180 | 99955327 | chr8 | 99959429 | 99959549 | chr8 | 99960329 | 99960497 |
| chr8 | 99960922 | 99960971 | chr8 | 99961792 | 99961822 | chr8 | 99985866 | 99986043 |
| chr8 | 99986226 | 99986526 | chr8 | 99986792 | 99987014 | chr8 | 101118241 | 101118490 |
| chr8 | 101661920 | 101661991 | chr8 | 101821973 | 101822047 | chr8 | 101920382 | 101920468 |
| chr8 | 102504464 | 102504506 | chr8 | 102505512 | 102505556 | chr8 | 102505797 | 102505985 |
| chr8 | 103629856 | 103629882 | chr8 | 104153202 | 104153246 | chr8 | 104153449 | 104153561 |
| chr8 | 104383700 | 104383985 | chr8 | 104512123 | 104513186 | chr8 | 104513462 | 104513926 |
| chr8 | 105235369 | 105235501 | chr8 | 105235644 | 105235803 | chr8 | 105235864 | 105236054 |
| chr8 | 105478725 | 105478779 | chr8 | 105479404 | 105479464 | chr8 | 106331160 | 106331237 |
| chr8 | 106332104 | 106332202 | chr8 | 107282163 | 107282195 | chr8 | 107284038 | 107284075 |
| chr8 | 108509543 | 108509697 | chr8 | 109093679 | 109094180 | chr8 | 109094485 | 109094595 |
| chr8 | 109094840 | 109095436 | chr8 | 109095506 | 109095932 | chr8 | 109799588 | 109799739 |
| chr8 | 110275006 | 110275023 | chr8 | 110406028 | 110406106 | chr8 | 110592198 | 110592228 |
| chr8 | 110704001 | 110704144 | chr8 | 110986443 | 110986682 | chr8 | 114444580 | 114445192 |
| chr8 | 114445763 | 114446068 | chr8 | 114446405 | 114446435 | chr8 | 114446931 | 114447368 |
| chr8 | 114449039 | 114449257 | chr8 | 114449550 | 114449602 | chr8 | 116660527 | 116660571 |
| chr8 | 116660616 | 116660760 | chr8 | 117950438 | 117950468 | chr8 | 117950783 | 117950914 |
| chr8 | 118532128 | 118532150 | chr8 | 120219912 | 120219941 | chr8 | 120220116 | 120220145 |
| chr8 | 120220428 | 120220592 | chr8 | 120650979 | 120651008 | chr8 | 120651221 | 120651412 |

TABLE 13-continued

Pan Cancer #3

| chr | start | end | chr | start | end | chr | start | end |
|---|---|---|---|---|---|---|---|---|
| chr8 | 120844095 | 120844130 | chr8 | 121136879 | 121137748 | chr8 | 121823901 | 121823930 |
| chr8 | 121824203 | 121824481 | chr8 | 121825455 | 121825484 | chr8 | 122347026 | 122347052 |
| chr8 | 122651872 | 122651905 | chr8 | 123695532 | 123695660 | chr8 | 124055236 | 124055256 |
| chr8 | 124173246 | 124173501 | chr8 | 124332846 | 124332875 | chr8 | 125411827 | 125411857 |
| chr8 | 125452366 | 125452394 | chr8 | 126007961 | 126008051 | chr8 | 126044442 | 126044563 |
| chr8 | 127569621 | 127569676 | chr8 | 128403354 | 128403383 | chr8 | 128745542 | 128745618 |
| chr8 | 128808002 | 128808077 | chr8 | 128872385 | 128872415 | chr8 | 128889324 | 128889422 |
| chr8 | 128931133 | 128931261 | chr8 | 130369274 | 130369364 | chr8 | 132052147 | 132052299 |
| chr8 | 132052399 | 132052515 | chr8 | 132052590 | 132053164 | chr8 | 132053715 | 132054583 |
| chr8 | 132054594 | 132054785 | chr8 | 133686745 | 133686836 | chr8 | 139508757 | 139508946 |
| chr8 | 139509741 | 139509928 | chr8 | 140714570 | 140714877 | chr8 | 140715090 | 140715094 |
| chr8 | 140715469 | 140715587 | chr8 | 140715965 | 140716021 | chr8 | 140716340 | 140716354 |
| chr8 | 140755383 | 140755550 | chr8 | 140834237 | 140834321 | chr8 | 140963292 | 140963362 |
| chr8 | 141054845 | 141054875 | chr8 | 141159919 | 141159949 | chr8 | 141588056 | 141588132 |
| chr8 | 141596886 | 141597022 | chr8 | 141614252 | 141614287 | chr8 | 142265206 | 142265243 |
| chr8 | 142282078 | 142282202 | chr8 | 142292552 | 142292774 | chr8 | 142318155 | 142318184 |
| chr8 | 142361233 | 142361487 | chr8 | 142367368 | 142367790 | chr8 | 142444600 | 142444752 |
| chr8 | 142528400 | 142528402 | chr8 | 142528455 | 142528606 | chr8 | 142528671 | 142528781 |
| chr8 | 142528835 | 142528961 | chr8 | 142535343 | 142535496 | chr8 | 142568598 | 142568652 |
| chr8 | 142632436 | 142632465 | chr8 | 142694847 | 142694953 | chr8 | 142984512 | 142984666 |
| chr8 | 143082777 | 143082810 | chr8 | 143089030 | 143089100 | chr8 | 143105244 | 143105377 |
| chr8 | 143368318 | 143368469 | chr8 | 143509457 | 143509594 | chr8 | 143532122 | 143532509 |
| chr8 | 143532542 | 143532846 | chr8 | 143533611 | 143533640 | chr8 | 143533709 | 143533906 |
| chr8 | 143557980 | 143558080 | chr8 | 143558472 | 143558604 | chr8 | 143587331 | 143587382 |
| chr8 | 143592664 | 143592687 | chr8 | 143611232 | 143611262 | chr8 | 143621980 | 143622096 |
| chr8 | 143702052 | 143702101 | chr8 | 143819384 | 143819406 | chr8 | 143858522 | 143858699 |
| chr8 | 143859338 | 143859361 | chr8 | 143876928 | 143876958 | chr8 | 143993974 | 143994165 |
| chr8 | 144069546 | 144069651 | chr8 | 144190378 | 144190432 | chr8 | 144203653 | 144203708 |
| chr8 | 144203977 | 144204021 | chr8 | 144226174 | 144226204 | chr8 | 144238822 | 144238901 |
| chr8 | 144241250 | 144241287 | chr8 | 144241871 | 144242356 | chr8 | 144303562 | 144303592 |
| chr8 | 144328321 | 144328565 | chr8 | 144330287 | 144330380 | chr8 | 144344293 | 144344442 |
| chr8 | 144347719 | 144347740 | chr8 | 144359977 | 144360076 | chr8 | 144360394 | 144360453 |
| chr8 | 144361758 | 144361823 | chr8 | 144372473 | 144372503 | chr8 | 144382679 | 144382697 |
| chr8 | 144421487 | 144421517 | chr8 | 144509325 | 144510529 | chr8 | 144511225 | 144511424 |
| chr8 | 144512041 | 144512192 | chr8 | 144512473 | 144512503 | chr8 | 144557003 | 144557088 |
| chr8 | 144601799 | 144601851 | chr8 | 144617065 | 144617206 | chr8 | 144650594 | 144650730 |
| chr8 | 144668566 | 144668667 | chr8 | 144668909 | 144668972 | chr8 | 145033304 | 145033333 |
| chr8 | 145218226 | 145218301 | chr8 | 145223902 | 145224061 | chr8 | 145753517 | 145753547 |
| chr8 | 145758572 | 145758692 | chr8 | 145806258 | 145806271 | chr8 | 145925461 | 145925491 |
| chr8 | 145925947 | 145926068 | chr8 | 146013617 | 146013647 | chr8 | 146079215 | 146079297 |
| chr9 | 113433 | 113512 | chr9 | 113550 | 113556 | chr9 | 113850 | 113885 |
| chr9 | 117884 | 117959 | chr9 | 841691 | 842031 | chr9 | 842208 | 842230 |
| chr9 | 842611 | 842673 | chr9 | 969556 | 969586 | chr9 | 969788 | 969846 |
| chr9 | 970096 | 970104 | chr9 | 970186 | 970225 | chr9 | 970495 | 970525 |
| chr9 | 970897 | 970911 | chr9 | 970993 | 971175 | chr9 | 972307 | 972759 |
| chr9 | 973184 | 973289 | chr9 | 974514 | 974547 | chr9 | 975117 | 975167 |
| chr9 | 975783 | 976321 | chr9 | 976618 | 976689 | chr9 | 976912 | 976961 |
| chr9 | 981797 | 981830 | chr9 | 1042402 | 1042500 | chr9 | 1042616 | 1042986 |
| chr9 | 1051905 | 1052166 | chr9 | 2115824 | 2115981 | chr9 | 3181752 | 3181869 |
| chr9 | 5070006 | 5070050 | chr9 | 5073756 | 5073788 | chr9 | 5078346 | 5078375 |
| chr9 | 5089711 | 5089740 | chr9 | 6412571 | 6412809 | chr9 | 6644297 | 6644367 |
| chr9 | 6644540 | 6644554 | chr9 | 6645017 | 6645333 | chr9 | 6645625 | 6645700 |
| chr9 | 6756353 | 6756458 | chr9 | 13278818 | 13278864 | chr9 | 14312994 | 14313096 |
| chr9 | 14313319 | 14313785 | chr9 | 14347633 | 14347673 | chr9 | 14348314 | 14348452 |
| chr9 | 17906404 | 17906432 | chr9 | 17906461 | 17906694 | chr9 | 17907004 | 17907061 |
| chr9 | 17907451 | 17907472 | chr9 | 19789107 | 19789301 | chr9 | 21031734 | 21031836 |
| chr9 | 21402617 | 21403021 | chr9 | 21559294 | 21559381 | chr9 | 21559665 | 21559702 |
| chr9 | 21965057 | 21965424 | chr9 | 21965570 | 21965757 | chr9 | 21968218 | 21968433 |
| chr9 | 21968457 | 21968475 | chr9 | 21970959 | 21971154 | chr9 | 21971185 | 21971220 |
| chr9 | 21974182 | 21974237 | chr9 | 21974499 | 21974794 | chr9 | 21994208 | 21994237 |
| chr9 | 21995297 | 21995326 | chr9 | 21995720 | 21995749 | chr9 | 22006131 | 22006152 |
| chr9 | 22008819 | 22008899 | chr9 | 22447664 | 22447708 | chr9 | 23822568 | 23822606 |
| chr9 | 23824561 | 23824591 | chr9 | 23831100 | 23831370 | chr9 | 29212170 | 29212170 |
| chr9 | 29212211 | 29212294 | chr9 | 29213508 | 29213651 | chr9 | 29214030 | 29214144 |
| chr9 | 29214360 | 29214430 | chr9 | 29214681 | 29215086 | chr9 | 32782630 | 32782935 |
| chr9 | 32783084 | 32783121 | chr9 | 32783346 | 32783419 | chr9 | 32783591 | 32783657 |
| chr9 | 33524609 | 33524687 | chr9 | 33676771 | 33676801 | chr9 | 33677360 | 33677415 |
| chr9 | 34224348 | 34224474 | chr9 | 34372805 | 34372983 | chr9 | 34589062 | 34589156 |
| chr9 | 35617291 | 35617337 | chr9 | 35675539 | 35675647 | chr9 | 35675838 | 35676180 |
| chr9 | 35844834 | 35844863 | chr9 | 36037068 | 36037098 | chr9 | 36318375 | 36318393 |
| chr9 | 36739812 | 36739980 | chr9 | 36832204 | 36832343 | chr9 | 37002454 | 37002517 |
| chr9 | 37002819 | 37003077 | chr9 | 37025564 | 37025783 | chr9 | 37026146 | 37026351 |
| chr9 | 37026434 | 37026622 | chr9 | 37026831 | 37027271 | chr9 | 37027325 | 37027412 |
| chr9 | 37027800 | 37027829 | chr9 | 37028944 | 37029119 | chr9 | 37029534 | 37030655 |
| chr9 | 37034197 | 37034247 | chr9 | 37034616 | 37034731 | chr9 | 37035366 | 37035734 |
| chr9 | 37036425 | 37036647 | chr9 | 37037671 | 37038354 | chr9 | 37467610 | 37467634 |

TABLE 13-continued

Pan Cancer #3

| chr | start | end | chr | start | end | chr | start | end |
|---|---|---|---|---|---|---|---|---|
| chr9 | 38620530 | 38620725 | chr9 | 66456023 | 66456047 | chr9 | 71200632 | 71200662 |
| chr9 | 71734816 | 71734920 | chr9 | 71788952 | 71789260 | chr9 | 71789453 | 71789757 |
| chr9 | 73032801 | 73032831 | chr9 | 74061838 | 74062070 | chr9 | 74210499 | 74210517 |
| chr9 | 74764547 | 74764648 | chr9 | 77112993 | 77113340 | chr9 | 77113559 | 77113708 |
| chr9 | 77113806 | 77113825 | chr9 | 77114745 | 77114851 | chr9 | 77115210 | 77115447 |
| chr9 | 77115657 | 77115687 | chr9 | 79231003 | 79231033 | chr9 | 79626876 | 79627370 |
| chr9 | 79628289 | 79628329 | chr9 | 79629208 | 79629471 | chr9 | 79629879 | 79630420 |
| chr9 | 79631192 | 79631335 | chr9 | 79631555 | 79631591 | chr9 | 79631865 | 79632182 |
| chr9 | 79632860 | 79632890 | chr9 | 79633397 | 79633904 | chr9 | 79634170 | 79634987 |
| chr9 | 79635047 | 79635448 | chr9 | 79635746 | 79636043 | chr9 | 79636258 | 79637274 |
| chr9 | 79637643 | 79637888 | chr9 | 79638137 | 79638244 | chr9 | 80409473 | 80409502 |
| chr9 | 80833933 | 80834011 | chr9 | 85677905 | 85677992 | chr9 | 86152387 | 86152417 |
| chr9 | 86578079 | 86578103 | chr9 | 86755532 | 86755952 | chr9 | 86886706 | 86886736 |
| chr9 | 87283008 | 87283038 | chr9 | 87283677 | 87283709 | chr9 | 87284706 | 87284798 |
| chr9 | 87285279 | 87285472 | chr9 | 88137524 | 88137725 | chr9 | 88137875 | 88137998 |
| chr9 | 88694345 | 88694438 | chr9 | 89560760 | 89560827 | chr9 | 89561063 | 89561109 |
| chr9 | 91150222 | 91150335 | chr9 | 91606004 | 91606058 | chr9 | 91792357 | 91792387 |
| chr9 | 91792776 | 91792907 | chr9 | 91793177 | 91793526 | chr9 | 93698029 | 93698051 |
| chr9 | 94183870 | 94183954 | chr9 | 94572641 | 94572743 | chr9 | 95417551 | 95417651 |
| chr9 | 95560810 | 95560840 | chr9 | 95569759 | 95569822 | chr9 | 95570247 | 95570434 |
| chr9 | 95571617 | 95571659 | chr9 | 95571719 | 95571760 | chr9 | 95947130 | 95947296 |
| chr9 | 96588858 | 96588885 | chr9 | 96710377 | 96710407 | chr9 | 96710647 | 96710991 |
| chr9 | 96711258 | 96711446 | chr9 | 96711535 | 96711617 | chr9 | 96711975 | 96712005 |
| chr9 | 96713378 | 96713893 | chr9 | 96715095 | 96715372 | chr9 | 96715688 | 96715857 |
| chr9 | 96716905 | 96717427 | chr9 | 96717450 | 96717466 | chr9 | 96717979 | 96718149 |
| chr9 | 96720803 | 96720885 | chr9 | 96721103 | 96721467 | chr9 | 96721689 | 96721802 |
| chr9 | 96722445 | 96722547 | chr9 | 96723093 | 96723159 | chr9 | 96723171 | 96723202 |
| chr9 | 97845915 | 97845947 | chr9 | 98111365 | 98111560 | chr9 | 98111895 | 98112157 |
| chr9 | 98112344 | 98112395 | chr9 | 98784772 | 98784802 | chr9 | 98789651 | 98790000 |
| chr9 | 99146020 | 99146153 | chr9 | 99259362 | 99259405 | chr9 | 99449135 | 99449451 |
| chr9 | 99639621 | 99639942 | chr9 | 99983140 | 99983170 | chr9 | 99983411 | 99983738 |
| chr9 | 99983798 | 99983824 | chr9 | 99984026 | 99984044 | chr9 | 100397979 | 100398016 |
| chr9 | 100503625 | 100503937 | chr9 | 100609991 | 100610134 | chr9 | 100610201 | 100610218 |
| chr9 | 100610681 | 100610816 | chr9 | 100611125 | 100611640 | chr9 | 100613828 | 100613999 |
| chr9 | 100614193 | 100614325 | chr9 | 100614541 | 100616035 | chr9 | 100616271 | 100616468 |
| chr9 | 100617293 | 100617365 | chr9 | 100617682 | 100618055 | chr9 | 100619722 | 100620069 |
| chr9 | 100620330 | 100620783 | chr9 | 100818336 | 100818437 | chr9 | 100835849 | 100835870 |
| chr9 | 101469269 | 101469307 | chr9 | 101469603 | 101469796 | chr9 | 101470116 | 101470250 |
| chr9 | 101470990 | 101471071 | chr9 | 101471570 | 101471621 | chr9 | 101471860 | 101472009 |
| chr9 | 101705996 | 101706195 | chr9 | 101706313 | 101706695 | chr9 | 103174705 | 103174730 |
| chr9 | 104248579 | 104248623 | chr9 | 104249475 | 104249562 | chr9 | 104500625 | 104500774 |
| chr9 | 110126074 | 110126247 | chr9 | 110228200 | 110228602 | chr9 | 110251388 | 110251418 |
| chr9 | 110252363 | 110252515 | chr9 | 112403170 | 112403200 | chr9 | 112403364 | 112403394 |
| chr9 | 113341522 | 113341621 | chr9 | 113341680 | 113341847 | chr9 | 113341927 | 113341965 |
| chr9 | 113342299 | 113342340 | chr9 | 115067932 | 115067959 | chr9 | 115478932 | 115478971 |
| chr9 | 115652966 | 115653425 | chr9 | 116633883 | 116633905 | chr9 | 117050981 | 117051156 |
| chr9 | 118917024 | 118917079 | chr9 | 120175795 | 120175832 | chr9 | 120176104 | 120176151 |
| chr9 | 120176867 | 120176897 | chr9 | 122131497 | 122131642 | chr9 | 122131880 | 122132025 |
| chr9 | 122132052 | 122132227 | chr9 | 123004898 | 123004928 | chr9 | 123295355 | 123295463 |
| chr9 | 124535347 | 124535611 | chr9 | 124749865 | 124749953 | chr9 | 124751485 | 124751515 |
| chr9 | 125676723 | 125676753 | chr9 | 126133778 | 126133856 | chr9 | 126154304 | 126154575 |
| chr9 | 126349038 | 126349104 | chr9 | 126770257 | 126770298 | chr9 | 126771532 | 126771705 |
| chr9 | 126774517 | 126774619 | chr9 | 126775530 | 126775560 | chr9 | 126776044 | 126776098 |
| chr9 | 126777529 | 126777746 | chr9 | 126777974 | 126777982 | chr9 | 126778359 | 126778496 |
| chr9 | 126779485 | 126780043 | chr9 | 126780285 | 126780315 | chr9 | 126780811 | 126780898 |
| chr9 | 126783295 | 126783499 | chr9 | 127212851 | 127213006 | chr9 | 127265876 | 127266025 |
| chr9 | 127266387 | 127266534 | chr9 | 127920543 | 127920572 | chr9 | 128635180 | 128635210 |
| chr9 | 128652200 | 128652232 | chr9 | 128759852 | 128759954 | chr9 | 129276718 | 129276820 |
| chr9 | 129372929 | 129373037 | chr9 | 129376170 | 129376199 | chr9 | 129376889 | 129376918 |
| chr9 | 129377214 | 129377316 | chr9 | 129377604 | 129377635 | chr9 | 129377773 | 129377959 |
| chr9 | 129387434 | 129387464 | chr9 | 129387848 | 129388200 | chr9 | 129388719 | 129388753 |
| chr9 | 129388996 | 129389192 | chr9 | 129400986 | 129401195 | chr9 | 129445255 | 129445566 |
| chr9 | 129445783 | 129445813 | chr9 | 129517783 | 129517821 | chr9 | 130248419 | 130248449 |
| chr9 | 130461687 | 130461742 | chr9 | 130675509 | 130675592 | chr9 | 130689631 | 130689667 |
| chr9 | 130689742 | 130689749 | chr9 | 131580038 | 131580118 | chr9 | 131607517 | 131607547 |
| chr9 | 131607770 | 131607800 | chr9 | 131854231 | 131854328 | chr9 | 131854708 | 131854732 |
| chr9 | 132373058 | 132373091 | chr9 | 132382635 | 132383109 | chr9 | 132383376 | 132383376 |
| chr9 | 132402840 | 132402883 | chr9 | 132403149 | 132403216 | chr9 | 132559377 | 132559417 |
| chr9 | 132804405 | 132804455 | chr9 | 132804796 | 132804974 | chr9 | 132805318 | 132805445 |
| chr9 | 132805737 | 132805893 | chr9 | 132881814 | 132881844 | chr9 | 133308893 | 133308941 |
| chr9 | 133534683 | 133534713 | chr9 | 133535734 | 133535839 | chr9 | 133536097 | 133536119 |
| chr9 | 133536150 | 133536344 | chr9 | 133536778 | 133536869 | chr9 | 133537182 | 133537549 |
| chr9 | 133538169 | 133538728 | chr9 | 133539606 | 133539709 | chr9 | 133541059 | 133541192 |
| chr9 | 133541689 | 133542337 | chr9 | 133738343 | 133738372 | chr9 | 133747505 | 133747534 |
| chr9 | 133773766 | 133773923 | chr9 | 133927347 | 133927481 | chr9 | 133928236 | 133928266 |
| chr9 | 134126670 | 134126741 | chr9 | 134191085 | 134191218 | chr9 | 134207916 | 134208012 |

TABLE 13-continued

Pan Cancer #3

| chr | start | end | chr | start | end | chr | start | end |
|---|---|---|---|---|---|---|---|---|
| chr9 | 134421797 | 134421835 | chr9 | 134717313 | 134717367 | chr9 | 135037119 | 135037287 |
| chr9 | 135037334 | 135037357 | chr9 | 135073463 | 135073506 | chr9 | 135455407 | 135455585 |
| chr9 | 135455996 | 135456023 | chr9 | 135456476 | 135456544 | chr9 | 135456897 | 135456915 |
| chr9 | 135458477 | 135458597 | chr9 | 135460001 | 135460176 | chr9 | 135460869 | 135460899 |
| chr9 | 135461511 | 135461773 | chr9 | 135462048 | 135462077 | chr9 | 135462648 | 135462967 |
| chr9 | 135464798 | 135464918 | chr9 | 135465948 | 135466064 | chr9 | 135466118 | 135466132 |
| chr9 | 135466344 | 135466660 | chr9 | 135548238 | 135548276 | chr9 | 135796801 | 135796830 |
| chr9 | 135865090 | 135865161 | chr9 | 135898911 | 135899124 | chr9 | 136474490 | 136474591 |
| chr9 | 137111397 | 137111426 | chr9 | 137229892 | 137229921 | chr9 | 137299119 | 137299450 |
| chr9 | 137299670 | 137299699 | chr9 | 137534066 | 137534238 | chr9 | 137575915 | 137575945 |
| chr9 | 137656958 | 137657128 | chr9 | 137667327 | 137667357 | chr9 | 137702189 | 137702222 |
| chr9 | 137718901 | 137719001 | chr9 | 137722087 | 137722209 | chr9 | 137979893 | 137980011 |
| chr9 | 137980258 | 137980288 | chr9 | 137980880 | 137980910 | chr9 | 138265123 | 138265251 |
| chr9 | 138563059 | 138563280 | chr9 | 138606821 | 138606923 | chr9 | 138627636 | 138627893 |
| chr9 | 138634047 | 138634159 | chr9 | 138659800 | 138659905 | chr9 | 138660943 | 138661012 |
| chr9 | 138661648 | 138661870 | chr9 | 138666455 | 138666558 | chr9 | 138880711 | 138880875 |
| chr9 | 138991798 | 138991828 | chr9 | 139000566 | 139000642 | chr9 | 139012272 | 139012411 |
| chr9 | 139024750 | 139024782 | chr9 | 139045653 | 139045683 | chr9 | 139047532 | 139047633 |
| chr9 | 139085228 | 139085350 | chr9 | 139090500 | 139090551 | chr9 | 139091072 | 139091369 |
| chr9 | 139093773 | 139093890 | chr9 | 139094705 | 139094732 | chr9 | 139095340 | 139095485 |
| chr9 | 139096650 | 139097006 | chr9 | 139111268 | 139111298 | chr9 | 139269039 | 139269121 |
| chr9 | 139399407 | 139399436 | chr9 | 139421955 | 139421985 | chr9 | 139477862 | 139478020 |
| chr9 | 139698925 | 139699051 | chr9 | 139704084 | 139704279 | chr9 | 139859041 | 139859268 |
| chr9 | 139888945 | 139888980 | chr9 | 140024842 | 140024918 | chr9 | 140024957 | 140025023 |
| chr9 | 140030498 | 140030528 | chr9 | 140031944 | 140031983 | chr9 | 140032891 | 140032951 |
| chr9 | 140033001 | 140033092 | chr9 | 140033426 | 140033490 | chr9 | 140033619 | 140033626 |
| chr9 | 140033909 | 140034079 | chr9 | 140050969 | 140051096 | chr9 | 140051220 | 140051354 |
| chr9 | 140127883 | 140128080 | chr9 | 140137310 | 140137339 | chr9 | 140197122 | 140197263 |
| chr9 | 140205394 | 140205519 | chr9 | 140245877 | 140245998 | chr9 | 140332708 | 140333018 |
| chr9 | 140382557 | 140382596 | chr9 | 140392454 | 140392484 | chr9 | 140397029 | 140397097 |
| chr9 | 140507256 | 140507419 | chr9 | 140704046 | 140704131 | chr9 | 140709046 | 140709174 |
| chr9 | 140727471 | 140727511 | chr9 | 140727845 | 140727930 | chr9 | 140769943 | 140769973 |
| chr9 | 140771975 | 140772347 | chr9 | 140772586 | 140772593 | chr9 | 140772757 | 140773301 |
| chr10 | 524754 | 524784 | chr10 | 833307 | 833386 | chr10 | 978878 | 978933 |
| chr10 | 1080415 | 1080513 | chr10 | 1120778 | 1120937 | chr10 | 1577394 | 1577424 |
| chr10 | 1585145 | 1585239 | chr10 | 1651360 | 1651374 | chr10 | 1708327 | 1708478 |
| chr10 | 1774858 | 1774887 | chr10 | 1779417 | 1779744 | chr10 | 3109360 | 3109459 |
| chr10 | 3197004 | 3197113 | chr10 | 3285672 | 3285698 | chr10 | 3330499 | 3330618 |
| chr10 | 3641378 | 3641396 | chr10 | 3678617 | 3678637 | chr10 | 3895410 | 3895452 |
| chr10 | 4599917 | 4599965 | chr10 | 5530764 | 5530975 | chr10 | 5855154 | 5855184 |
| chr10 | 5875140 | 5875358 | chr10 | 6003402 | 6003855 | chr10 | 6042309 | 6042571 |
| chr10 | 6162159 | 6162225 | chr10 | 6206142 | 6206217 | chr10 | 6372343 | 6372373 |
| chr10 | 6513976 | 6514006 | chr10 | 6577643 | 6577673 | chr10 | 6984463 | 6984639 |
| chr10 | 7205733 | 7205787 | chr10 | 7212745 | 7213064 | chr10 | 7213505 | 7213535 |
| chr10 | 7216059 | 7216089 | chr10 | 7236211 | 7236245 | chr10 | 7255730 | 7255821 |
| chr10 | 7323283 | 7323313 | chr10 | 7371678 | 7371708 | chr10 | 7414544 | 7414588 |
| chr10 | 7424626 | 7424687 | chr10 | 7436180 | 7436209 | chr10 | 7449954 | 7450189 |
| chr10 | 7450491 | 7451390 | chr10 | 7452227 | 7452777 | chr10 | 7453313 | 7453656 |
| chr10 | 7453903 | 7453930 | chr10 | 7708274 | 7708304 | chr10 | 7708790 | 7708856 |
| chr10 | 7708955 | 7709087 | chr10 | 7709723 | 7709752 | chr10 | 8055681 | 8055764 |
| chr10 | 8075930 | 8075944 | chr10 | 8076341 | 8076487 | chr10 | 8076804 | 8077374 |
| chr10 | 8077874 | 8078218 | chr10 | 8085039 | 8085721 | chr10 | 8085978 | 8086010 |
| chr10 | 8091895 | 8092278 | chr10 | 8093738 | 8093824 | chr10 | 8093860 | 8093963 |
| chr10 | 8095603 | 8095845 | chr10 | 8096160 | 8096190 | chr10 | 8096975 | 8097197 |
| chr10 | 8097474 | 8097537 | chr10 | 11059933 | 11060062 | chr10 | 11206206 | 11206235 |
| chr10 | 11207179 | 11207276 | chr10 | 11700918 | 11701075 | chr10 | 12390825 | 12390995 |
| chr10 | 12391870 | 12392327 | chr10 | 13043386 | 13043425 | chr10 | 13141001 | 13141020 |
| chr10 | 13715208 | 13715401 | chr10 | 13933005 | 13933035 | chr10 | 13933436 | 13933538 |
| chr10 | 13933597 | 13933934 | chr10 | 13933983 | 13934125 | chr10 | 13934169 | 13934183 |
| chr10 | 14393819 | 14393893 | chr10 | 14966129 | 14966212 | chr10 | 15140505 | 15140526 |
| chr10 | 15761292 | 15761671 | chr10 | 15762124 | 15762154 | chr10 | 16562369 | 16562672 |
| chr10 | 16562710 | 16563664 | chr10 | 16563691 | 16563909 | chr10 | 16564087 | 16564116 |
| chr10 | 16564537 | 16564566 | chr10 | 17269259 | 17269288 | chr10 | 17269786 | 17269789 |
| chr10 | 17270072 | 17270445 | chr10 | 17270991 | 17271254 | chr10 | 17271444 | 17271625 |
| chr10 | 17271914 | 17272233 | chr10 | 17272601 | 17272630 | chr10 | 17273172 | 17273201 |
| chr10 | 17275584 | 17275613 | chr10 | 17277741 | 17277770 | chr10 | 17429165 | 17429244 |
| chr10 | 17429544 | 17429622 | chr10 | 17496545 | 17496734 | chr10 | 18429628 | 18429774 |
| chr10 | 21101525 | 21101555 | chr10 | 21462533 | 21462607 | chr10 | 21462970 | 21463023 |
| chr10 | 21805217 | 21805277 | chr10 | 22047336 | 22047635 | chr10 | 22541638 | 22541850 |
| chr10 | 22542025 | 22542249 | chr10 | 22624022 | 22624305 | chr10 | 22624562 | 22625120 |
| chr10 | 22625383 | 22625782 | chr10 | 22625812 | 22625978 | chr10 | 22633985 | 22634174 |
| chr10 | 22634325 | 22634578 | chr10 | 22764649 | 22765791 | chr10 | 22765821 | 22765901 |
| chr10 | 23216865 | 23216945 | chr10 | 23460355 | 23460471 | chr10 | 23461222 | 23461754 |
| chr10 | 23462059 | 23462462 | chr10 | 23462486 | 23462614 | chr10 | 23462635 | 23462910 |
| chr10 | 23463267 | 23463853 | chr10 | 23463888 | 23464077 | chr10 | 23479876 | 23480696 |
| chr10 | 23480904 | 23481049 | chr10 | 23481321 | 23481515 | chr10 | 23481936 | 23482232 |

TABLE 13-continued

Pan Cancer #3

| chr | start | end | chr | start | end | chr | start | end |
|---|---|---|---|---|---|---|---|---|
| chr10 | 23482289 | 23482445 | chr10 | 23483828 | 23484618 | chr10 | 23486264 | 23486328 |
| chr10 | 23487742 | 23487978 | chr10 | 23488393 | 23489158 | chr10 | 23489409 | 23489439 |
| chr10 | 23982438 | 23982820 | chr10 | 23983194 | 23983247 | chr10 | 23983618 | 23983700 |
| chr10 | 23984087 | 23984226 | chr10 | 23984923 | 23984991 | chr10 | 24988589 | 24988619 |
| chr10 | 25464619 | 25464915 | chr10 | 25465421 | 25465517 | chr10 | 26055811 | 26055841 |
| chr10 | 26223001 | 26223205 | chr10 | 26224031 | 26224061 | chr10 | 26500619 | 26500870 |
| chr10 | 26501539 | 26501589 | chr10 | 26503693 | 26503731 | chr10 | 26504114 | 26504143 |
| chr10 | 26504491 | 26504883 | chr10 | 26505009 | 26505227 | chr10 | 26505442 | 26505617 |
| chr10 | 26506057 | 26506163 | chr10 | 26506373 | 26506618 | chr10 | 26506903 | 26507400 |
| chr10 | 26681099 | 26681129 | chr10 | 26727098 | 26727368 | chr10 | 26727604 | 26727816 |
| chr10 | 26747051 | 26747075 | chr10 | 26816912 | 26816938 | chr10 | 26931897 | 26931926 |
| chr10 | 27547946 | 27548331 | chr10 | 27548401 | 27548484 | chr10 | 27794496 | 27794512 |
| chr10 | 27846637 | 27846727 | chr10 | 28030892 | 28030925 | chr10 | 28032966 | 28033020 |
| chr10 | 28033410 | 28033481 | chr10 | 28033770 | 28034186 | chr10 | 28034327 | 28034341 |
| chr10 | 28034874 | 28035300 | chr10 | 28035615 | 28035782 | chr10 | 28287373 | 28287557 |
| chr10 | 28287777 | 28288070 | chr10 | 28657255 | 28657343 | chr10 | 28958086 | 28958129 |
| chr10 | 29011047 | 29011162 | chr10 | 30026077 | 30026090 | chr10 | 30848200 | 30848230 |
| chr10 | 31073368 | 31073481 | chr10 | 31892922 | 31893079 | chr10 | 32499044 | 32499176 |
| chr10 | 33233313 | 33233361 | chr10 | 33624166 | 33624230 | chr10 | 33624492 | 33624560 |
| chr10 | 35929334 | 35929528 | chr10 | 43186151 | 43186181 | chr10 | 43250009 | 43250039 |
| chr10 | 43250406 | 43250779 | chr10 | 43250855 | 43250886 | chr10 | 43428424 | 43428576 |
| chr10 | 43429067 | 43429100 | chr10 | 43429376 | 43429411 | chr10 | 43572685 | 43572734 |
| chr10 | 43600561 | 43600720 | chr10 | 43609055 | 43609117 | chr10 | 43609922 | 43609963 |
| chr10 | 43613890 | 43613919 | chr10 | 43614982 | 43615011 | chr10 | 43615554 | 43615607 |
| chr10 | 43617401 | 43617430 | chr10 | 43697887 | 43698086 | chr10 | 43698115 | 43698155 |
| chr10 | 43858343 | 43858437 | chr10 | 44879944 | 44880228 | chr10 | 44880869 | 44880915 |
| chr10 | 49652977 | 49653080 | chr10 | 49731548 | 49731749 | chr10 | 49732060 | 49732087 |
| chr10 | 49732156 | 49732498 | chr10 | 50323222 | 50323258 | chr10 | 50340119 | 50340149 |
| chr10 | 50507557 | 50507619 | chr10 | 50603967 | 50604159 | chr10 | 50604608 | 50604645 |
| chr10 | 50605057 | 50605654 | chr10 | 50606027 | 50606433 | chr10 | 50817015 | 50817132 |
| chr10 | 50817858 | 50817872 | chr10 | 50818382 | 50818432 | chr10 | 50818987 | 50819102 |
| chr10 | 50821472 | 50821701 | chr10 | 50887655 | 50887753 | chr10 | 50887790 | 50887816 |
| chr10 | 50977034 | 50977048 | chr10 | 52177545 | 52177575 | chr10 | 53107427 | 53107525 |
| chr10 | 54068526 | 54068610 | chr10 | 54072982 | 54073020 | chr10 | 54073265 | 54073295 |
| chr10 | 54074744 | 54074789 | chr10 | 57387429 | 57387796 | chr10 | 57388325 | 57388510 |
| chr10 | 57390290 | 57390637 | chr10 | 57391166 | 57391215 | chr10 | 60273130 | 60273278 |
| chr10 | 60935887 | 60935996 | chr10 | 60936524 | 60936729 | chr10 | 60937073 | 60937103 |
| chr10 | 63212324 | 63212701 | chr10 | 64575526 | 64575638 | chr10 | 64578171 | 64578540 |
| chr10 | 65262111 | 65262148 | chr10 | 70232445 | 70232485 | chr10 | 70275831 | 70275875 |
| chr10 | 70315131 | 70315148 | chr10 | 70586517 | 70586540 | chr10 | 71327725 | 71327764 |
| chr10 | 71328773 | 71328821 | chr10 | 71329079 | 71329118 | chr10 | 71329544 | 71329618 |
| chr10 | 71332052 | 71333018 | chr10 | 72015150 | 72015339 | chr10 | 72043779 | 72043894 |
| chr10 | 72200118 | 72200138 | chr10 | 72200354 | 72200771 | chr10 | 72200825 | 72201285 |
| chr10 | 72973130 | 72973180 | chr10 | 73156362 | 73156661 | chr10 | 73157867 | 73158027 |
| chr10 | 75407570 | 75407837 | chr10 | 75488953 | 75488979 | chr10 | 77190039 | 77190068 |
| chr10 | 77191224 | 77191368 | chr10 | 79396921 | 79397089 | chr10 | 81023884 | 81023914 |
| chr10 | 81154141 | 81154192 | chr10 | 81664867 | 81664899 | chr10 | 82117074 | 82117271 |
| chr10 | 83634261 | 83634361 | chr10 | 83634467 | 83634499 | chr10 | 83635531 | 83635545 |
| chr10 | 85954425 | 85954457 | chr10 | 88123672 | 88123701 | chr10 | 88149363 | 88149601 |
| chr10 | 88304914 | 88304944 | chr10 | 88684005 | 88684034 | chr10 | 89624255 | 89624311 |
| chr10 | 89653788 | 89653859 | chr10 | 89685272 | 89685322 | chr10 | 89690790 | 89690819 |
| chr10 | 89692776 | 89693015 | chr10 | 89711861 | 89711992 | chr10 | 89717610 | 89717744 |
| chr10 | 89720790 | 89720885 | chr10 | 89725030 | 89725071 | chr10 | 90966708 | 90966865 |
| chr10 | 90967671 | 90968040 | chr10 | 91295029 | 91295067 | chr10 | 91295585 | 91295617 |
| chr10 | 92617242 | 92617308 | chr10 | 93647216 | 93647300 | chr10 | 93647562 | 93647648 |
| chr10 | 94450675 | 94450726 | chr10 | 94451448 | 94451602 | chr10 | 94826023 | 94826056 |
| chr10 | 94828194 | 94828498 | chr10 | 94828735 | 94828828 | chr10 | 94834413 | 94835047 |
| chr10 | 95360716 | 95360750 | chr10 | 96304115 | 96304235 | chr10 | 98129822 | 98130033 |
| chr10 | 99080262 | 99080447 | chr10 | 99080862 | 99080930 | chr10 | 99474393 | 99474467 |
| chr10 | 99481826 | 99481905 | chr10 | 99531219 | 99531430 | chr10 | 99789175 | 99789282 |
| chr10 | 99790261 | 99790318 | chr10 | 99790590 | 99790664 | chr10 | 99790947 | 99791161 |
| chr10 | 100991907 | 100991935 | chr10 | 100992055 | 100992190 | chr10 | 100992222 | 100992443 |
| chr10 | 100992882 | 100992916 | chr10 | 100993537 | 100994016 | chr10 | 100996046 | 100996224 |
| chr10 | 101088995 | 101089439 | chr10 | 101089908 | 101090203 | chr10 | 101280204 | 101280485 |
| chr10 | 101283464 | 101283658 | chr10 | 101290117 | 101290160 | chr10 | 101290180 | 101291142 |
| chr10 | 101292297 | 101292919 | chr10 | 101293156 | 101293343 | chr10 | 101294756 | 101295586 |
| chr10 | 101296768 | 101296800 | chr10 | 101874886 | 101875138 | chr10 | 102322230 | 102322260 |
| chr10 | 102419400 | 102419681 | chr10 | 102430699 | 102430761 | chr10 | 102473856 | 102473932 |
| chr10 | 102483993 | 102484245 | chr10 | 102484270 | 102484554 | chr10 | 102495508 | 102495741 |
| chr10 | 102497273 | 102497708 | chr10 | 102498280 | 102498433 | chr10 | 102501359 | 102501389 |
| chr10 | 102507509 | 102507535 | chr10 | 102508996 | 102509285 | chr10 | 102589425 | 102589493 |
| chr10 | 102589786 | 102589915 | chr10 | 102590152 | 102590415 | chr10 | 102890941 | 102891582 |
| chr10 | 102891823 | 102891955 | chr10 | 102893624 | 102893951 | chr10 | 102894091 | 102895289 |
| chr10 | 102899173 | 102899601 | chr10 | 102899807 | 102899855 | chr10 | 102900263 | 102900575 |
| chr10 | 102906525 | 102906620 | chr10 | 102975619 | 102975834 | chr10 | 102976150 | 102976180 |
| chr10 | 102977051 | 102977412 | chr10 | 102983153 | 102983379 | chr10 | 102983435 | 102983749 |

TABLE 13-continued

Pan Cancer #3

| chr | start | end | chr | start | end | chr | start | end |
|---|---|---|---|---|---|---|---|---|
| chr10 | 102984513 | 102984516 | chr10 | 102985772 | 102985963 | chr10 | 102986534 | 102986952 |
| chr10 | 102987207 | 102987558 | chr10 | 102989629 | 102989659 | chr10 | 102996116 | 102996480 |
| chr10 | 102996597 | 102996638 | chr10 | 102997329 | 102997406 | chr10 | 102998576 | 102998828 |
| chr10 | 103043975 | 103044227 | chr10 | 103044301 | 103044366 | chr10 | 103425950 | 103426174 |
| chr10 | 103432412 | 103432441 | chr10 | 103535622 | 103535770 | chr10 | 103536227 | 103536256 |
| chr10 | 103536300 | 103536416 | chr10 | 103579674 | 103579713 | chr10 | 103930128 | 103930161 |
| chr10 | 104170096 | 104170262 | chr10 | 104170408 | 104170732 | chr10 | 105036542 | 105036658 |
| chr10 | 105036701 | 105036863 | chr10 | 105037223 | 105037830 | chr10 | 105127047 | 105127076 |
| chr10 | 105155323 | 105155481 | chr10 | 105413627 | 105413784 | chr10 | 105420861 | 105420891 |
| chr10 | 105527028 | 105527057 | chr10 | 106398644 | 106398687 | chr10 | 106398826 | 106398886 |
| chr10 | 106399581 | 106400387 | chr10 | 106401323 | 106401432 | chr10 | 106401511 | 106402190 |
| chr10 | 106402272 | 106402325 | chr10 | 106402712 | 106402825 | chr10 | 108924045 | 108924059 |
| chr10 | 110671930 | 110672245 | chr10 | 111216789 | 111216803 | chr10 | 112403151 | 112403297 |
| chr10 | 112440378 | 112440408 | chr10 | 115804840 | 115805014 | chr10 | 116164248 | 116164341 |
| chr10 | 116331126 | 116331156 | chr10 | 116853875 | 116853908 | chr10 | 118030642 | 118030705 |
| chr10 | 118031302 | 118031548 | chr10 | 118031625 | 118032229 | chr10 | 118032413 | 118032547 |
| chr10 | 118032917 | 118033140 | chr10 | 118033260 | 118033542 | chr10 | 118034143 | 118034168 |
| chr10 | 118609305 | 118609390 | chr10 | 118890980 | 118891104 | chr10 | 118891517 | 118891661 |
| chr10 | 118891716 | 118891774 | chr10 | 118892013 | 118892456 | chr10 | 118892518 | 118893266 |
| chr10 | 118893680 | 118893825 | chr10 | 118894035 | 118894071 | chr10 | 118896629 | 118896805 |
| chr10 | 118897913 | 118897968 | chr10 | 118899273 | 118899302 | chr10 | 118899583 | 118899602 |
| chr10 | 118899893 | 118899957 | chr10 | 118900166 | 118900244 | chr10 | 118900324 | 118900498 |
| chr10 | 118922143 | 118922208 | chr10 | 118922721 | 118922901 | chr10 | 118923138 | 118923259 |
| chr10 | 118924604 | 118924896 | chr10 | 118927086 | 118927296 | chr10 | 118928548 | 118928727 |
| chr10 | 119000690 | 119001154 | chr10 | 119001534 | 119001564 | chr10 | 119294352 | 119294461 |
| chr10 | 119294847 | 119294897 | chr10 | 119294909 | 119295245 | chr10 | 119296756 | 119296788 |
| chr10 | 119297384 | 119297529 | chr10 | 119301365 | 119301427 | chr10 | 119302141 | 119302155 |
| chr10 | 119302222 | 119302266 | chr10 | 119302962 | 119303174 | chr10 | 119304363 | 119304393 |
| chr10 | 119304896 | 119304985 | chr10 | 119305062 | 119305109 | chr10 | 119307022 | 119307052 |
| chr10 | 119311867 | 119311897 | chr10 | 119312751 | 119313193 | chr10 | 119590435 | 119590464 |
| chr10 | 119807026 | 119807056 | chr10 | 120354243 | 120354273 | chr10 | 120355548 | 120355614 |
| chr10 | 120800789 | 120800835 | chr10 | 120841558 | 120841574 | chr10 | 121267480 | 121267523 |
| chr10 | 122216896 | 122217083 | chr10 | 122708495 | 122708691 | chr10 | 122708992 | 122709022 |
| chr10 | 123256044 | 123256232 | chr10 | 123258020 | 123258091 | chr10 | 123274758 | 123274787 |
| chr10 | 123279548 | 123279697 | chr10 | 123357206 | 123357242 | chr10 | 123357766 | 123357893 |
| chr10 | 123922645 | 123922682 | chr10 | 124893178 | 124893192 | chr10 | 124893238 | 124893350 |
| chr10 | 124893635 | 124893765 | chr10 | 124893965 | 124894479 | chr10 | 124894889 | 124894922 |
| chr10 | 124895426 | 124895695 | chr10 | 124895833 | 124896456 | chr10 | 124897220 | 124897657 |
| chr10 | 124897957 | 124897973 | chr10 | 124899035 | 124899116 | chr10 | 124899754 | 124899786 |
| chr10 | 124901892 | 124902046 | chr10 | 124902139 | 124902568 | chr10 | 124902608 | 124903238 |
| chr10 | 124904921 | 124905119 | chr10 | 124905481 | 124905511 | chr10 | 124905920 | 124906174 |
| chr10 | 124906436 | 124906544 | chr10 | 124907312 | 124907534 | chr10 | 124908091 | 124908121 |
| chr10 | 124909086 | 124909114 | chr10 | 124909253 | 124909537 | chr10 | 124909674 | 124909725 |
| chr10 | 124910363 | 124910454 | chr10 | 124910709 | 124911048 | chr10 | 125425515 | 125425547 |
| chr10 | 125650866 | 125651162 | chr10 | 125851328 | 125851645 | chr10 | 125852299 | 125852497 |
| chr10 | 125852753 | 125853191 | chr10 | 126101966 | 126102001 | chr10 | 126135927 | 126136065 |
| chr10 | 126136506 | 126136723 | chr10 | 126137181 | 126137405 | chr10 | 126198949 | 126199077 |
| chr10 | 126697828 | 126698107 | chr10 | 126782965 | 126783048 | chr10 | 126828994 | 126829024 |
| chr10 | 128076561 | 128076630 | chr10 | 128993904 | 128994446 | chr10 | 128994727 | 128994903 |
| chr10 | 129379338 | 129379367 | chr10 | 129534993 | 129535446 | chr10 | 129535696 | 129535733 |
| chr10 | 129536080 | 129536223 | chr10 | 129536259 | 129536310 | chr10 | 129888804 | 129888885 |
| chr10 | 129948111 | 129948140 | chr10 | 130085356 | 130085362 | chr10 | 130203435 | 130203480 |
| chr10 | 130338727 | 130338768 | chr10 | 130338804 | 130338976 | chr10 | 130577764 | 130577794 |
| chr10 | 131348513 | 131348713 | chr10 | 131647903 | 131647933 | chr10 | 131761378 | 131761441 |
| chr10 | 131761687 | 131761725 | chr10 | 131762087 | 131762124 | chr10 | 131762592 | 131762631 |
| chr10 | 131762904 | 131762940 | chr10 | 131763633 | 131763717 | chr10 | 131767372 | 131767503 |
| chr10 | 131767543 | 131767649 | chr10 | 131768724 | 131769029 | chr10 | 131769533 | 131770237 |
| chr10 | 131770657 | 131770687 | chr10 | 131770988 | 131771093 | chr10 | 131936599 | 131936626 |
| chr10 | 131937392 | 131937428 | chr10 | 132001252 | 132001556 | chr10 | 133109192 | 133109260 |
| chr10 | 133110554 | 133110704 | chr10 | 133794883 | 133795241 | chr10 | 133795313 | 133795430 |
| chr10 | 133795682 | 133795883 | chr10 | 133795976 | 133796058 | chr10 | 133849598 | 133850008 |
| chr10 | 133850529 | 133850774 | chr10 | 133951602 | 133952025 | chr10 | 133979059 | 133979089 |
| chr10 | 134000008 | 134000052 | chr10 | 134000109 | 134000124 | chr10 | 134001140 | 134001260 |
| chr10 | 134016203 | 134016388 | chr10 | 134022845 | 134022875 | chr10 | 134039087 | 134039117 |
| chr10 | 134095594 | 134095833 | chr10 | 134119401 | 134119447 | chr10 | 134121401 | 134121430 |
| chr10 | 134273064 | 134273156 | chr10 | 134301095 | 134301212 | chr10 | 134481320 | 134481433 |
| chr10 | 134491021 | 134491114 | chr10 | 134499773 | 134499803 | chr10 | 134593329 | 134593416 |
| chr10 | 134598087 | 134598090 | chr10 | 134598368 | 134598530 | chr10 | 134599432 | 134599482 |
| chr10 | 134599808 | 134600016 | chr10 | 134600038 | 134600998 | chr10 | 134601556 | 134601715 |
| chr10 | 134602183 | 134602269 | chr10 | 134607970 | 134608183 | chr10 | 134665147 | 134665202 |
| chr10 | 134679129 | 134679265 | chr10 | 134690559 | 134690617 | chr10 | 134693587 | 134693709 |
| chr10 | 134699872 | 134699909 | chr10 | 134733221 | 134733275 | chr10 | 134733497 | 134733617 |
| chr10 | 134738378 | 134738642 | chr10 | 134755773 | 134756183 | chr10 | 134788083 | 134788251 |
| chr10 | 134796012 | 134796042 | chr10 | 134896060 | 134896092 | chr10 | 134901193 | 134901511 |
| chr10 | 134902008 | 134902124 | chr10 | 134902188 | 134902307 | chr10 | 134916714 | 134916774 |
| chr10 | 134941145 | 134941178 | chr10 | 134942840 | 134943114 | chr10 | 134943445 | 134943542 |

TABLE 13-continued

Pan Cancer #3

| chr | start | end | chr | start | end | chr | start | end |
|---|---|---|---|---|---|---|---|---|
| chr10 | 134944742 | 134944772 | chr10 | 135002063 | 135002156 | chr10 | 135014963 | 135015132 |
| chr10 | 135017049 | 135017129 | chr10 | 135018032 | 135018070 | chr10 | 135018825 | 135018960 |
| chr10 | 135020801 | 135020893 | chr10 | 135023470 | 135023500 | chr10 | 135043088 | 135043538 |
| chr10 | 135043968 | 135044128 | chr10 | 135044555 | 135044573 | chr10 | 135048782 | 135048939 |
| chr10 | 135050311 | 135050679 | chr10 | 135076368 | 135076503 | chr10 | 135121316 | 135121345 |
| chr10 | 135121807 | 135122251 | chr10 | 135122742 | 135122808 | chr10 | 135122991 | 135123020 |
| chr10 | 135139555 | 135139730 | chr10 | 135153956 | 135154001 | chr11 | 232863 | 233062 |
| chr11 | 392576 | 392720 | chr11 | 394815 | 394968 | chr11 | 406876 | 406939 |
| chr11 | 407427 | 407463 | chr11 | 526389 | 526419 | chr11 | 533451 | 533567 |
| chr11 | 533859 | 533888 | chr11 | 534273 | 534302 | chr11 | 548766 | 548800 |
| chr11 | 611099 | 611128 | chr11 | 611691 | 611791 | chr11 | 636644 | 636673 |
| chr11 | 636895 | 636906 | chr11 | 637162 | 637263 | chr11 | 637350 | 637441 |
| chr11 | 679692 | 679722 | chr11 | 726417 | 726466 | chr11 | 763323 | 763686 |
| chr11 | 775261 | 775291 | chr11 | 829543 | 829708 | chr11 | 830174 | 830243 |
| chr11 | 850555 | 850823 | chr11 | 863062 | 863092 | chr11 | 1006077 | 1006107 |
| chr11 | 1027540 | 1027574 | chr11 | 1029238 | 1029403 | chr11 | 1030215 | 1030296 |
| chr11 | 1080391 | 1080454 | chr11 | 1081667 | 1081715 | chr11 | 1214665 | 1214917 |
| chr11 | 1215899 | 1215999 | chr11 | 1229945 | 1229975 | chr11 | 1244381 | 1244465 |
| chr11 | 1250889 | 1250924 | chr11 | 1251183 | 1251351 | chr11 | 1263602 | 1263644 |
| chr11 | 1274085 | 1274189 | chr11 | 1318403 | 1318432 | chr11 | 1358291 | 1358332 |
| chr11 | 1374959 | 1375003 | chr11 | 1411875 | 1411905 | chr11 | 1430714 | 1430794 |
| chr11 | 1464280 | 1464428 | chr11 | 1469228 | 1469379 | chr11 | 1471920 | 1472058 |
| chr11 | 1868081 | 1868237 | chr11 | 1946130 | 1946160 | chr11 | 1957391 | 1957530 |
| chr11 | 1959077 | 1959187 | chr11 | 2040107 | 2040148 | chr11 | 2209907 | 2210278 |
| chr11 | 2226048 | 2226078 | chr11 | 2278708 | 2278839 | chr11 | 2291259 | 2291493 |
| chr11 | 2291984 | 2292057 | chr11 | 2292106 | 2292359 | chr11 | 2292392 | 2292636 |
| chr11 | 2402376 | 2402405 | chr11 | 2437991 | 2438144 | chr11 | 2465350 | 2465447 |
| chr11 | 2465462 | 2465491 | chr11 | 2466597 | 2466788 | chr11 | 2884103 | 2884143 |
| chr11 | 2884159 | 2884309 | chr11 | 3169665 | 3169835 | chr11 | 3181913 | 3181942 |
| chr11 | 3182104 | 3182133 | chr11 | 3767205 | 3767245 | chr11 | 4095819 | 4095864 |
| chr11 | 4209105 | 4209134 | chr11 | 4209382 | 4209411 | chr11 | 5993897 | 5993933 |
| chr11 | 7274215 | 7274245 | chr11 | 7695432 | 7695528 | chr11 | 8040536 | 8040563 |
| chr11 | 8040582 | 8040770 | chr11 | 8103002 | 8103115 | chr11 | 8189987 | 8190766 |
| chr11 | 8284535 | 8284760 | chr11 | 8289517 | 8289745 | chr11 | 8290195 | 8290423 |
| chr11 | 8615674 | 8615704 | chr11 | 9025970 | 9026348 | chr11 | 9112446 | 9112585 |
| chr11 | 9112640 | 9112741 | chr11 | 9405392 | 9405542 | chr11 | 10509678 | 10509807 |
| chr11 | 10811151 | 10811188 | chr11 | 10815867 | 10815903 | chr11 | 12029957 | 12030272 |
| chr11 | 12030823 | 12030852 | chr11 | 12132524 | 12132559 | chr11 | 12399040 | 12399222 |
| chr11 | 12399727 | 12399791 | chr11 | 12695481 | 12695495 | chr11 | 12695573 | 12695611 |
| chr11 | 12696611 | 12696746 | chr11 | 13030566 | 13030890 | chr11 | 13690121 | 13690157 |
| chr11 | 14316375 | 14316404 | chr11 | 15136085 | 15136394 | chr11 | 16628819 | 16628933 |
| chr11 | 16632514 | 16632670 | chr11 | 17497492 | 17497520 | chr11 | 17497546 | 17497685 |
| chr11 | 17740493 | 17740570 | chr11 | 17741679 | 17741889 | chr11 | 17741953 | 17742445 |
| chr11 | 17743742 | 17743775 | chr11 | 18100096 | 18100118 | chr11 | 18812614 | 18812653 |
| chr11 | 18813032 | 18813086 | chr11 | 18813451 | 18813542 | chr11 | 18813792 | 18813947 |
| chr11 | 19263848 | 19263878 | chr11 | 19367102 | 19367134 | chr11 | 19367268 | 19367330 |
| chr11 | 19735730 | 19735760 | chr11 | 20153718 | 20153764 | chr11 | 20178094 | 20178305 |
| chr11 | 20180279 | 20180793 | chr11 | 20181213 | 20181254 | chr11 | 20181725 | 20181993 |
| chr11 | 20182864 | 20182959 | chr11 | 20183251 | 20183421 | chr11 | 20183674 | 20183773 |
| chr11 | 20184569 | 20185410 | chr11 | 20229274 | 20229550 | chr11 | 20229863 | 20230091 |
| chr11 | 20230398 | 20230464 | chr11 | 20618197 | 20618392 | chr11 | 20618423 | 20618924 |
| chr11 | 20619717 | 20619974 | chr11 | 20621341 | 20621644 | chr11 | 20622705 | 20622792 |
| chr11 | 20623259 | 20623359 | chr11 | 20690653 | 20690877 | chr11 | 20691219 | 20691379 |
| chr11 | 20691432 | 20691452 | chr11 | 20691748 | 20691914 | chr11 | 20692453 | 20692529 |
| chr11 | 22215123 | 22215287 | chr11 | 22362934 | 22363189 | chr11 | 22364821 | 22364975 |
| chr11 | 22365407 | 22365477 | chr11 | 27742185 | 27742215 | chr11 | 27743115 | 27743173 |
| chr11 | 27743436 | 27743608 | chr11 | 27744147 | 27744504 | chr11 | 27744711 | 27744744 |
| chr11 | 30037593 | 30037743 | chr11 | 30038689 | 30038739 | chr11 | 30605919 | 30606123 |
| chr11 | 30606796 | 30606864 | chr11 | 30607367 | 30607409 | chr11 | 31818458 | 31818512 |
| chr11 | 31818571 | 31818652 | chr11 | 31819302 | 31819508 | chr11 | 31819568 | 31819833 |
| chr11 | 31820045 | 31820360 | chr11 | 31820461 | 31821025 | chr11 | 31821297 | 31821778 |
| chr11 | 31822325 | 31822393 | chr11 | 31824300 | 31824355 | chr11 | 31824564 | 31824680 |
| chr11 | 31825017 | 31825280 | chr11 | 31825696 | 31825754 | chr11 | 31825833 | 31826070 |
| chr11 | 31826107 | 31826303 | chr11 | 31826409 | 31826732 | chr11 | 31827114 | 31827204 |
| chr11 | 31827438 | 31827519 | chr11 | 31827598 | 31828123 | chr11 | 31833097 | 31833155 |
| chr11 | 31835707 | 31835797 | chr11 | 31836046 | 31836470 | chr11 | 31837019 | 31837512 |
| chr11 | 31837542 | 31838392 | chr11 | 31838678 | 31839051 | chr11 | 31839307 | 31839945 |
| chr11 | 31840042 | 31840080 | chr11 | 31840603 | 31840710 | chr11 | 31840769 | 31840922 |
| chr11 | 31841376 | 31842088 | chr11 | 31842175 | 31842276 | chr11 | 31846022 | 31846230 |
| chr11 | 31846434 | 31846985 | chr11 | 31847250 | 31847301 | chr11 | 31847371 | 31847712 |
| chr11 | 31847770 | 31847872 | chr11 | 31847896 | 31847925 | chr11 | 31848472 | 31848602 |
| chr11 | 31848723 | 31849300 | chr11 | 32009104 | 32009126 | chr11 | 32354844 | 32354959 |
| chr11 | 32355000 | 32355197 | chr11 | 32448583 | 32448893 | chr11 | 32455602 | 32455634 |
| chr11 | 32455841 | 32456025 | chr11 | 32456279 | 32456445 | chr11 | 32456759 | 32457176 |
| chr11 | 32457712 | 32458175 | chr11 | 32458389 | 32458823 | chr11 | 32459684 | 32460071 |
| chr11 | 32460468 | 32460515 | chr11 | 32460796 | 32460864 | chr11 | 33037467 | 33037556 |

TABLE 13-continued

Pan Cancer #3

| chr | start | end | chr | start | end | chr | start | end |
|---|---|---|---|---|---|---|---|---|
| chr11 | 33858424 | 33858463 | chr11 | 33890297 | 33890334 | chr11 | 33993984 | 33994014 |
| chr11 | 34535093 | 34535123 | chr11 | 35547499 | 35547562 | chr11 | 35641683 | 35641718 |
| chr11 | 35684958 | 35685131 | chr11 | 43596513 | 43596608 | chr11 | 43600453 | 43600557 |
| chr11 | 43601094 | 43601467 | chr11 | 43602468 | 43603036 | chr11 | 43603077 | 43603228 |
| chr11 | 43603628 | 43604145 | chr11 | 44325688 | 44325747 | chr11 | 44326137 | 44326184 |
| chr11 | 44327252 | 44327413 | chr11 | 44330878 | 44331439 | chr11 | 44331483 | 44331711 |
| chr11 | 44333052 | 44333081 | chr11 | 44333371 | 44333461 | chr11 | 44333477 | 44333480 |
| chr11 | 44337533 | 44337571 | chr11 | 44337727 | 44337861 | chr11 | 44337883 | 44338057 |
| chr11 | 44338335 | 44338367 | chr11 | 44340823 | 44340858 | chr11 | 44341966 | 44342034 |
| chr11 | 46316896 | 46317355 | chr11 | 46317408 | 46317680 | chr11 | 46413042 | 46413304 |
| chr11 | 46866492 | 46866510 | chr11 | 46940419 | 46940531 | chr11 | 47209044 | 47209189 |
| chr11 | 47358926 | 47359237 | chr11 | 47363557 | 47363625 | chr11 | 47372828 | 47373002 |
| chr11 | 47485995 | 47486141 | chr11 | 57194355 | 57194509 | chr11 | 57235406 | 57235436 |
| chr11 | 57414663 | 57414663 | chr11 | 57437196 | 57437234 | chr11 | 57501025 | 57501068 |
| chr11 | 58672746 | 58673064 | chr11 | 59323596 | 59323729 | chr11 | 59329223 | 59329240 |
| chr11 | 59333405 | 59333541 | chr11 | 60718668 | 60718853 | chr11 | 60718977 | 60719163 |
| chr11 | 61049694 | 61049736 | chr11 | 61058283 | 61058341 | chr11 | 61062822 | 61063023 |
| chr11 | 61063062 | 61063138 | chr11 | 61148730 | 61148749 | chr11 | 61277002 | 61277119 |
| chr11 | 61536985 | 61537014 | chr11 | 61595086 | 61595262 | chr11 | 61596420 | 61596640 |
| chr11 | 61664655 | 61664770 | chr11 | 61666106 | 61666136 | chr11 | 62370720 | 62370750 |
| chr11 | 62440549 | 62440588 | chr11 | 62484517 | 62484547 | chr11 | 63609979 | 63610013 |
| chr11 | 63641072 | 63641104 | chr11 | 63839478 | 63839528 | chr11 | 63849394 | 63849426 |
| chr11 | 63934589 | 63934619 | chr11 | 64105954 | 64106031 | chr11 | 64120879 | 64120909 |
| chr11 | 64140397 | 64140427 | chr11 | 64410723 | 64410759 | chr11 | 64480429 | 64480593 |
| chr11 | 64480824 | 64481042 | chr11 | 64490435 | 64490561 | chr11 | 64490792 | 64490806 |
| chr11 | 64490826 | 64491159 | chr11 | 64578577 | 64578600 | chr11 | 64739468 | 64739508 |
| chr11 | 64809865 | 64809906 | chr11 | 64950292 | 64950374 | chr11 | 65091291 | 65091369 |
| chr11 | 65185548 | 65185728 | chr11 | 65405659 | 65405774 | chr11 | 65409759 | 65409861 |
| chr11 | 65478524 | 65478611 | chr11 | 65511027 | 65511172 | chr11 | 65511392 | 65511522 |
| chr11 | 65554043 | 65554410 | chr11 | 65600810 | 65601640 | chr11 | 65778952 | 65778981 |
| chr11 | 65779317 | 65779357 | chr11 | 65816447 | 65816519 | chr11 | 65816561 | 65816564 |
| chr11 | 66114279 | 66114331 | chr11 | 66188115 | 66188145 | chr11 | 66188473 | 66188484 |
| chr11 | 66188571 | 66188783 | chr11 | 66188853 | 66188974 | chr11 | 66454424 | 66454454 |
| chr11 | 66511223 | 66511327 | chr11 | 66513217 | 66513252 | chr11 | 66513552 | 66513646 |
| chr11 | 66625207 | 66625240 | chr11 | 66649028 | 66649058 | chr11 | 66658257 | 66658290 |
| chr11 | 66725600 | 66725637 | chr11 | 66790621 | 66790655 | chr11 | 67072239 | 67072396 |
| chr11 | 67139422 | 67139460 | chr11 | 67139535 | 67139546 | chr11 | 67210017 | 67210057 |
| chr11 | 67248420 | 67248458 | chr11 | 67350961 | 67350990 | chr11 | 67462643 | 67462833 |
| chr11 | 67764187 | 67764254 | chr11 | 67781196 | 67781564 | chr11 | 67797202 | 67797281 |
| chr11 | 68096034 | 68096179 | chr11 | 68118716 | 68118745 | chr11 | 68153950 | 68154098 |
| chr11 | 68181217 | 68181288 | chr11 | 68409558 | 68409588 | chr11 | 68804728 | 68804776 |
| chr11 | 69192566 | 69192784 | chr11 | 69280561 | 69280633 | chr11 | 69466004 | 69466042 |
| chr11 | 69484356 | 69484454 | chr11 | 69516968 | 69517174 | chr11 | 69518030 | 69518211 |
| chr11 | 69518530 | 69518718 | chr11 | 69588930 | 69589184 | chr11 | 69589824 | 69589854 |
| chr11 | 69590149 | 69590222 | chr11 | 70211516 | 70211545 | chr11 | 71192746 | 71192889 |
| chr11 | 71318332 | 71318809 | chr11 | 71318953 | 71318967 | chr11 | 71951639 | 71951738 |
| chr11 | 71952340 | 71952416 | chr11 | 71952459 | 71952541 | chr11 | 71954612 | 71954642 |
| chr11 | 71955344 | 71955377 | chr11 | 71956007 | 71956340 | chr11 | 72413980 | 72414010 |
| chr11 | 72432837 | 72432916 | chr11 | 72475677 | 72475711 | chr11 | 72532348 | 72532378 |
| chr11 | 72929747 | 72929883 | chr11 | 73072907 | 73072953 | chr11 | 73310367 | 73310441 |
| chr11 | 73685698 | 73685845 | chr11 | 73694609 | 73694659 | chr11 | 74394491 | 74394600 |
| chr11 | 74953265 | 74953336 | chr11 | 75379283 | 75379895 | chr11 | 75459486 | 75459571 |
| chr11 | 75858210 | 75858240 | chr11 | 76371738 | 76372077 | chr11 | 78672917 | 78672964 |
| chr11 | 79151173 | 79151216 | chr11 | 82444376 | 82445101 | chr11 | 82998001 | 82998031 |
| chr11 | 86085742 | 86085861 | chr11 | 86085932 | 86085968 | chr11 | 86383167 | 86383710 |
| chr11 | 88241705 | 88241975 | chr11 | 88242131 | 88242274 | chr11 | 88242359 | 88242618 |
| chr11 | 88799082 | 88799209 | chr11 | 89867794 | 89867990 | chr11 | 91957500 | 91957674 |
| chr11 | 91957974 | 91958230 | chr11 | 91958734 | 91959326 | chr11 | 91959355 | 91959430 |
| chr11 | 91959899 | 91960045 | chr11 | 93063583 | 93063645 | chr11 | 93063870 | 93063948 |
| chr11 | 93911651 | 93911800 | chr11 | 94134086 | 94134463 | chr11 | 94134683 | 94134853 |
| chr11 | 94275794 | 94275813 | chr11 | 94278456 | 94278603 | chr11 | 94473600 | 94473768 |
| chr11 | 94473803 | 94474139 | chr11 | 94474356 | 94474385 | chr11 | 94502334 | 94502489 |
| chr11 | 94884130 | 94884160 | chr11 | 98891477 | 98891882 | chr11 | 100997644 | 100997981 |
| chr11 | 100998276 | 100998318 | chr11 | 100998667 | 100998744 | chr11 | 101453180 | 101453518 |
| chr11 | 102961347 | 102961378 | chr11 | 102962922 | 102963062 | chr11 | 102980027 | 102980056 |
| chr11 | 104034521 | 104034996 | chr11 | 105480755 | 105480786 | chr11 | 105481216 | 105481571 |
| chr11 | 106888308 | 106888429 | chr11 | 106888641 | 106888801 | chr11 | 107461623 | 107461653 |
| chr11 | 107462415 | 107462459 | chr11 | 108236072 | 108236101 | chr11 | 108603233 | 108603263 |
| chr11 | 109292906 | 109293052 | chr11 | 109293720 | 109293763 | chr11 | 110166519 | 110166935 |
| chr11 | 110582232 | 110582434 | chr11 | 110582895 | 110583028 | chr11 | 110583044 | 110583050 |
| chr11 | 110583574 | 110583730 | chr11 | 111383183 | 111383531 | chr11 | 111383558 | 111383682 |
| chr11 | 111411093 | 111411581 | chr11 | 111411822 | 111412061 | chr11 | 111783548 | 111783577 |
| chr11 | 114113022 | 114113052 | chr11 | 115375120 | 115375177 | chr11 | 115530222 | 115530604 |
| chr11 | 115630531 | 115630910 | chr11 | 115631307 | 115631364 | chr11 | 116147253 | 116147283 |
| chr11 | 116451023 | 116451190 | chr11 | 117056042 | 117056073 | chr11 | 117296921 | 117297109 |
| chr11 | 118991056 | 118991079 | chr11 | 119148865 | 119148945 | chr11 | 119149236 | 119149265 |

TABLE 13-continued

Pan Cancer #3

| chr | start | end | chr | start | end | chr | start | end |
|---|---|---|---|---|---|---|---|---|
| chr11 | 119292779 | 119292809 | chr11 | 119293370 | 119293615 | chr11 | 119612227 | 119612267 |
| chr11 | 119612324 | 119612399 | chr11 | 119612998 | 119613075 | chr11 | 120008105 | 120008504 |
| chr11 | 120039833 | 120039865 | chr11 | 120435405 | 120435477 | chr11 | 120435800 | 120435830 |
| chr11 | 120894800 | 120895026 | chr11 | 120998701 | 120998825 | chr11 | 122847265 | 122847696 |
| chr11 | 122848079 | 122848312 | chr11 | 122848369 | 122848591 | chr11 | 122849301 | 122849331 |
| chr11 | 122849783 | 122850123 | chr11 | 122850149 | 122850163 | chr11 | 122850424 | 122850536 |
| chr11 | 122851177 | 122851209 | chr11 | 122852438 | 122852475 | chr11 | 122855008 | 122855043 |
| chr11 | 122961137 | 122961219 | chr11 | 123066433 | 123066463 | chr11 | 123229058 | 123229406 |
| chr11 | 123300824 | 123301028 | chr11 | 123301083 | 123302026 | chr11 | 124735437 | 124735482 |
| chr11 | 124736196 | 124736252 | chr11 | 124738777 | 124739088 | chr11 | 125035763 | 125036208 |
| chr11 | 125220500 | 125220643 | chr11 | 125755612 | 125755710 | chr11 | 125773675 | 125774060 |
| chr11 | 126870182 | 126870212 | chr11 | 126870453 | 126870500 | chr11 | 126870525 | 126870543 |
| chr11 | 126873390 | 126873515 | chr11 | 128391893 | 128392116 | chr11 | 128562892 | 128563185 |
| chr11 | 128563337 | 128563730 | chr11 | 128563940 | 128564329 | chr11 | 128564740 | 128564876 |
| chr11 | 128564992 | 128565379 | chr11 | 128657931 | 128657970 | chr11 | 129242876 | 129243241 |
| chr11 | 129243305 | 129243587 | chr11 | 129243926 | 129244300 | chr11 | 129244441 | 129244603 |
| chr11 | 129245673 | 129245810 | chr11 | 129246070 | 129246129 | chr11 | 130318960 | 130318997 |
| chr11 | 130319527 | 130319613 | chr11 | 130343061 | 130343100 | chr11 | 130359769 | 130359812 |
| chr11 | 130359872 | 130359915 | chr11 | 130781550 | 130781781 | chr11 | 130785487 | 130785622 |
| chr11 | 131522763 | 131522947 | chr11 | 131564970 | 131565073 | chr11 | 131766868 | 131766960 |
| chr11 | 131780877 | 131781078 | chr11 | 132484215 | 132484404 | chr11 | 132813489 | 132813757 |
| chr11 | 132813908 | 132813949 | chr11 | 132864134 | 132864175 | chr11 | 132934123 | 132934176 |
| chr11 | 132952768 | 132953050 | chr11 | 132953233 | 132953423 | chr11 | 133231739 | 133231832 |
| chr11 | 133402206 | 133402260 | chr11 | 133792055 | 133792214 | chr11 | 133825226 | 133825543 |
| chr11 | 133906783 | 133906918 | chr11 | 133939002 | 133939177 | chr11 | 134145703 | 134146393 |
| chr11 | 134146682 | 134146894 | chr11 | 134201502 | 134201543 | chr11 | 134201841 | 134202084 |
| chr11 | 134281365 | 134281509 | chr12 | 570090 | 570171 | chr12 | 1639135 | 1639222 |
| chr12 | 2046104 | 2046134 | chr12 | 2162554 | 2162817 | chr12 | 2163164 | 2163276 |
| chr12 | 2403658 | 2403714 | chr12 | 2566053 | 2566247 | chr12 | 2595199 | 2595339 |
| chr12 | 2862068 | 2862142 | chr12 | 2964465 | 2964577 | chr12 | 3371882 | 3371911 |
| chr12 | 3373533 | 3373666 | chr12 | 3600315 | 3600345 | chr12 | 3602270 | 3602716 |
| chr12 | 3602865 | 3602879 | chr12 | 3603100 | 3603156 | chr12 | 3862254 | 3862298 |
| chr12 | 4214005 | 4214157 | chr12 | 4274054 | 4274188 | chr12 | 4274271 | 4274409 |
| chr12 | 4362436 | 4362471 | chr12 | 4378252 | 4378330 | chr12 | 4379357 | 4379491 |
| chr12 | 4381433 | 4382386 | chr12 | 4382965 | 4382999 | chr12 | 4383492 | 4383784 |
| chr12 | 4384389 | 4384418 | chr12 | 4384736 | 4384902 | chr12 | 4392883 | 4392922 |
| chr12 | 4405589 | 4405619 | chr12 | 4554801 | 4554831 | chr12 | 4919145 | 4919213 |
| chr12 | 4919239 | 4919244 | chr12 | 5018073 | 5018692 | chr12 | 5019085 | 5019742 |
| chr12 | 5019794 | 5020313 | chr12 | 5153039 | 5153286 | chr12 | 5153358 | 5153460 |
| chr12 | 5541100 | 5541177 | chr12 | 5542325 | 5542439 | chr12 | 5542759 | 5542911 |
| chr12 | 5840200 | 5840363 | chr12 | 6308743 | 6308772 | chr12 | 6483615 | 6483756 |
| chr12 | 6664508 | 6664522 | chr12 | 7559160 | 7559307 | chr12 | 8025635 | 8025660 |
| chr12 | 8127118 | 8127140 | chr12 | 8171360 | 8171745 | chr12 | 8808599 | 8808684 |
| chr12 | 8850658 | 8850744 | chr12 | 8975182 | 8975361 | chr12 | 10085916 | 10085932 |
| chr12 | 10363278 | 10363323 | chr12 | 10772771 | 10772896 | chr12 | 11653449 | 11653463 |
| chr12 | 12504823 | 12504850 | chr12 | 12848390 | 12848556 | chr12 | 14133152 | 14133263 |
| chr12 | 14133619 | 14133881 | chr12 | 14135111 | 14135339 | chr12 | 14818824 | 14818867 |
| chr12 | 15374258 | 15374291 | chr12 | 16500576 | 16500621 | chr12 | 19282333 | 19282363 |
| chr12 | 20521704 | 20521841 | chr12 | 20522457 | 20522487 | chr12 | 20522769 | 20522891 |
| chr12 | 21680394 | 21680683 | chr12 | 21810264 | 21810868 | chr12 | 21833068 | 21833107 |
| chr12 | 22093825 | 22094268 | chr12 | 22094578 | 22094810 | chr12 | 22486799 | 22486881 |
| chr12 | 22487134 | 22487473 | chr12 | 22698087 | 22698110 | chr12 | 24714909 | 24714938 |
| chr12 | 24715235 | 24715264 | chr12 | 24716033 | 24716218 | chr12 | 25056243 | 25056436 |
| chr12 | 25101592 | 25101660 | chr12 | 25101919 | 25101997 | chr12 | 25102010 | 25102086 |
| chr12 | 25362824 | 25362853 | chr12 | 25368463 | 25368492 | chr12 | 25378543 | 25378662 |
| chr12 | 25380231 | 25380299 | chr12 | 25398203 | 25398319 | chr12 | 27176520 | 27176539 |
| chr12 | 27494550 | 27494580 | chr12 | 28123996 | 28124247 | chr12 | 28127767 | 28128302 |
| chr12 | 28128547 | 28129084 | chr12 | 29936016 | 29936048 | chr12 | 29936602 | 29936642 |
| chr12 | 29936662 | 29936831 | chr12 | 29937331 | 29937374 | chr12 | 30322774 | 30322924 |
| chr12 | 30323015 | 30323439 | chr12 | 30323503 | 30323517 | chr12 | 30975572 | 30975959 |
| chr12 | 31079268 | 31079367 | chr12 | 31079418 | 31079499 | chr12 | 31316012 | 31316037 |
| chr12 | 32340317 | 32340336 | chr12 | 33591774 | 33591804 | chr12 | 33592613 | 33592847 |
| chr12 | 34494888 | 34494918 | chr12 | 34502733 | 34502803 | chr12 | 39299117 | 39299560 |
| chr12 | 39539353 | 39539436 | chr12 | 40618404 | 40618470 | chr12 | 41086183 | 41086379 |
| chr12 | 41086784 | 41087106 | chr12 | 41582513 | 41582988 | chr12 | 41583374 | 41583419 |
| chr12 | 43945110 | 43945124 | chr12 | 43945356 | 43945379 | chr12 | 43945417 | 43945526 |
| chr12 | 43946203 | 43946298 | chr12 | 45269504 | 45269624 | chr12 | 45444118 | 45444681 |
| chr12 | 45444715 | 45445258 | chr12 | 46767650 | 46767697 | chr12 | 47225381 | 47225476 |
| chr12 | 47225551 | 47225579 | chr12 | 47629349 | 47629379 | chr12 | 48397195 | 48398070 |
| chr12 | 48398641 | 48398671 | chr12 | 48690674 | 48690880 | chr12 | 49297802 | 49297915 |
| chr12 | 49366374 | 49366423 | chr12 | 49374914 | 49375026 | chr12 | 49375116 | 49375119 |
| chr12 | 49375325 | 49375529 | chr12 | 49390873 | 49391104 | chr12 | 49391147 | 49391877 |
| chr12 | 49657705 | 49657743 | chr12 | 49691049 | 49691078 | chr12 | 49727092 | 49727127 |
| chr12 | 49729728 | 49730090 | chr12 | 49759530 | 49759559 | chr12 | 49989786 | 49989816 |
| chr12 | 50297497 | 50297554 | chr12 | 50297974 | 50298055 | chr12 | 50426748 | 50426799 |
| chr12 | 51421133 | 51421271 | chr12 | 51421556 | 51421586 | chr12 | 51565469 | 51565548 |

TABLE 13-continued

Pan Cancer #3

| chr | start | end | chr | start | end | chr | start | end |
|---|---|---|---|---|---|---|---|---|
| chr12 | 51930708 | 51930785 | chr12 | 52262983 | 52263106 | chr12 | 52301280 | 52301305 |
| chr12 | 52400831 | 52401537 | chr12 | 52408905 | 52409033 | chr12 | 52627273 | 52627438 |
| chr12 | 52652153 | 52652219 | chr12 | 52652600 | 52652613 | chr12 | 53108089 | 53108218 |
| chr12 | 53359386 | 53359563 | chr12 | 54089093 | 54089511 | chr12 | 54132252 | 54132329 |
| chr12 | 54145843 | 54145857 | chr12 | 54145881 | 54145895 | chr12 | 54321250 | 54321628 |
| chr12 | 54322201 | 54322252 | chr12 | 54324799 | 54324937 | chr12 | 54329358 | 54329478 |
| chr12 | 54329605 | 54329947 | chr12 | 54331062 | 54331135 | chr12 | 54332868 | 54333337 |
| chr12 | 54338666 | 54338817 | chr12 | 54338979 | 54339681 | chr12 | 54343812 | 54343829 |
| chr12 | 54345611 | 54345658 | chr12 | 54345966 | 54346032 | chr12 | 54348844 | 54349079 |
| chr12 | 54349256 | 54349336 | chr12 | 54354514 | 54354621 | chr12 | 54354905 | 54355086 |
| chr12 | 54359960 | 54360084 | chr12 | 54360608 | 54360649 | chr12 | 54377912 | 54377946 |
| chr12 | 54377978 | 54378115 | chr12 | 54379174 | 54379623 | chr12 | 54379888 | 54379930 |
| chr12 | 54379959 | 54380459 | chr12 | 54387842 | 54387959 | chr12 | 54388215 | 54388245 |
| chr12 | 54391400 | 54391403 | chr12 | 54393479 | 54393684 | chr12 | 54393950 | 54394162 |
| chr12 | 54394410 | 54394418 | chr12 | 54398889 | 54398959 | chr12 | 54399616 | 54399646 |
| chr12 | 54402690 | 54402796 | chr12 | 54403067 | 54403360 | chr12 | 54408411 | 54408726 |
| chr12 | 54409476 | 54409505 | chr12 | 54423616 | 54423697 | chr12 | 54424746 | 54424748 |
| chr12 | 54425032 | 54425119 | chr12 | 54447351 | 54447581 | chr12 | 54447899 | 54447977 |
| chr12 | 54520745 | 54520868 | chr12 | 54720200 | 54720232 | chr12 | 54812238 | 54812359 |
| chr12 | 54922714 | 54922803 | chr12 | 54942994 | 54943116 | chr12 | 56231108 | 56231148 |
| chr12 | 56478840 | 56478869 | chr12 | 56481645 | 56481937 | chr12 | 56486572 | 56486601 |
| chr12 | 56490965 | 56490994 | chr12 | 56491630 | 56491659 | chr12 | 56492618 | 56492647 |
| chr12 | 56558381 | 56558519 | chr12 | 56873601 | 56873630 | chr12 | 56882240 | 56882380 |
| chr12 | 57387303 | 57387332 | chr12 | 57559869 | 57559925 | chr12 | 57618574 | 57618710 |
| chr12 | 57881127 | 57881345 | chr12 | 57944081 | 57944117 | chr12 | 58021320 | 58021458 |
| chr12 | 58021916 | 58022029 | chr12 | 58025646 | 58025733 | chr12 | 58025870 | 58025873 |
| chr12 | 58145415 | 58145450 | chr12 | 59314159 | 59314189 | chr12 | 62584838 | 62585012 |
| chr12 | 62585031 | 62586017 | chr12 | 62586252 | 62586281 | chr12 | 62858540 | 62858575 |
| chr12 | 63025574 | 63026160 | chr12 | 63543848 | 63544401 | chr12 | 63544499 | 63544599 |
| chr12 | 63545313 | 63545343 | chr12 | 64061821 | 64062159 | chr12 | 64062369 | 64062578 |
| chr12 | 64062921 | 64063096 | chr12 | 64783185 | 64783308 | chr12 | 64784108 | 64784252 |
| chr12 | 64784534 | 64784564 | chr12 | 65218102 | 65218550 | chr12 | 65218901 | 65219156 |
| chr12 | 65219376 | 65219527 | chr12 | 65219606 | 65219784 | chr12 | 65220205 | 65220350 |
| chr12 | 65514863 | 65515596 | chr12 | 65516378 | 65516455 | chr12 | 65557212 | 65557234 |
| chr12 | 65562052 | 65562086 | chr12 | 66122800 | 66122995 | chr12 | 66123381 | 66123519 |
| chr12 | 66135984 | 66136014 | chr12 | 66582827 | 66583137 | chr12 | 69327259 | 69327463 |
| chr12 | 69754451 | 69754470 | chr12 | 69754590 | 69754710 | chr12 | 69964176 | 69964264 |
| chr12 | 70087493 | 70087568 | chr12 | 72332641 | 72332696 | chr12 | 72665186 | 72665788 |
| chr12 | 72666713 | 72666807 | chr12 | 72666998 | 72667425 | chr12 | 72667652 | 72667682 |
| chr12 | 75601379 | 75601499 | chr12 | 75601696 | 75601910 | chr12 | 75602976 | 75603231 |
| chr12 | 75728336 | 75728485 | chr12 | 75728737 | 75728766 | chr12 | 77719311 | 77719422 |
| chr12 | 79257222 | 79257351 | chr12 | 81102185 | 81102455 | chr12 | 81102513 | 81102562 |
| chr12 | 81107997 | 81108034 | chr12 | 81471517 | 81471614 | chr12 | 81471754 | 81472111 |
| chr12 | 85306519 | 85306549 | chr12 | 85667272 | 85667731 | chr12 | 85673206 | 85673235 |
| chr12 | 85673460 | 85674807 | chr12 | 88973544 | 88973582 | chr12 | 88974159 | 88974253 |
| chr12 | 93966429 | 93966603 | chr12 | 93966998 | 93967215 | chr12 | 94543409 | 94543445 |
| chr12 | 94543899 | 94543961 | chr12 | 94544022 | 94544052 | chr12 | 94852489 | 94852506 |
| chr12 | 95267524 | 95267554 | chr12 | 95267865 | 95267976 | chr12 | 95942965 | 95942978 |
| chr12 | 99288312 | 99288407 | chr12 | 99288622 | 99288936 | chr12 | 99289162 | 99289309 |
| chr12 | 101025380 | 101025410 | chr12 | 101111029 | 101111061 | chr12 | 101111373 | 101111479 |
| chr12 | 103218495 | 103218595 | chr12 | 103351564 | 103351985 | chr12 | 103352052 | 103352154 |
| chr12 | 103352171 | 103352282 | chr12 | 103352314 | 103352681 | chr12 | 103358865 | 103358899 |
| chr12 | 103359556 | 103359586 | chr12 | 103889160 | 103889211 | chr12 | 103889789 | 103889812 |
| chr12 | 104609417 | 104609796 | chr12 | 104684181 | 104684220 | chr12 | 104850505 | 104850536 |
| chr12 | 104850578 | 104850592 | chr12 | 104851077 | 104851186 | chr12 | 104852032 | 104852508 |
| chr12 | 105017109 | 105017199 | chr12 | 105478323 | 105478419 | chr12 | 106533852 | 106533881 |
| chr12 | 106974353 | 106974383 | chr12 | 106976725 | 106976779 | chr12 | 106977321 | 106977497 |
| chr12 | 106979161 | 106979534 | chr12 | 106979799 | 106979995 | chr12 | 106980223 | 106980333 |
| chr12 | 106980912 | 106981406 | chr12 | 107486550 | 107486672 | chr12 | 107487194 | 107487855 |
| chr12 | 107712273 | 107712303 | chr12 | 107713205 | 107713235 | chr12 | 107714866 | 107715153 |
| chr12 | 108168971 | 108169413 | chr12 | 108169550 | 108169573 | chr12 | 108237466 | 108237524 |
| chr12 | 108238102 | 108238513 | chr12 | 108297411 | 108297466 | chr12 | 109488519 | 109488543 |
| chr12 | 109639281 | 109639475 | chr12 | 110353414 | 110353451 | chr12 | 110717541 | 110717710 |
| chr12 | 110983706 | 110983736 | chr12 | 111127124 | 111127455 | chr12 | 111471177 | 111471559 |
| chr12 | 111471948 | 111471959 | chr12 | 111472059 | 111472195 | chr12 | 111472357 | 111472671 |
| chr12 | 111763122 | 111763152 | chr12 | 112574734 | 112574775 | chr12 | 112888151 | 112888315 |
| chr12 | 112910821 | 112910850 | chr12 | 112915509 | 112915538 | chr12 | 112926255 | 112926284 |
| chr12 | 112926876 | 112926914 | chr12 | 113012954 | 113013157 | chr12 | 113541667 | 113542099 |
| chr12 | 113592238 | 113592359 | chr12 | 113900753 | 113900765 | chr12 | 113901074 | 113901158 |
| chr12 | 113901408 | 113901591 | chr12 | 113902042 | 113902353 | chr12 | 113903468 | 113903498 |
| chr12 | 113904779 | 113905016 | chr12 | 113908990 | 113909314 | chr12 | 113909329 | 113909455 |
| chr12 | 113913267 | 113913681 | chr12 | 113913884 | 113914050 | chr12 | 113916222 | 113916316 |
| chr12 | 113916649 | 113916678 | chr12 | 113916972 | 113917012 | chr12 | 113917232 | 113917310 |
| chr12 | 113917775 | 113917890 | chr12 | 114029408 | 114029660 | chr12 | 114076029 | 114076093 |
| chr12 | 114337763 | 114337793 | chr12 | 114833985 | 114834102 | chr12 | 114838369 | 114838726 |
| chr12 | 114839104 | 114839147 | chr12 | 114841046 | 114841084 | chr12 | 114841425 | 114841493 |

TABLE 13-continued

Pan Cancer #3

| chr | start | end | chr | start | end | chr | start | end |
|---|---|---|---|---|---|---|---|---|
| chr12 | 114843112 | 114843186 | chr12 | 114843261 | 114843278 | chr12 | 114843545 | 114843660 |
| chr12 | 114844201 | 114844300 | chr12 | 114846715 | 114846768 | chr12 | 114847043 | 114847436 |
| chr12 | 114847578 | 114847691 | chr12 | 114852040 | 114852082 | chr12 | 114852293 | 114852373 |
| chr12 | 114877171 | 114877262 | chr12 | 114878550 | 114878584 | chr12 | 114878813 | 114879012 |
| chr12 | 114881634 | 114881764 | chr12 | 114882555 | 114882646 | chr12 | 114883473 | 114883535 |
| chr12 | 114918594 | 114918717 | chr12 | 115136159 | 115136363 | chr12 | 116946086 | 116946199 |
| chr12 | 116946251 | 116946548 | chr12 | 117474065 | 117474198 | chr12 | 117798065 | 117798095 |
| chr12 | 117799413 | 117799529 | chr12 | 118860397 | 118860436 | chr12 | 119212319 | 119212381 |
| chr12 | 119418594 | 119418847 | chr12 | 119419436 | 119419466 | chr12 | 119419720 | 119419899 |
| chr12 | 120032862 | 120033169 | chr12 | 120148142 | 120148248 | chr12 | 120148923 | 120148962 |
| chr12 | 120535158 | 120535187 | chr12 | 120536625 | 120536654 | chr12 | 120885215 | 120885245 |
| chr12 | 121622546 | 121622576 | chr12 | 122192723 | 122192843 | chr12 | 122278484 | 122278580 |
| chr12 | 122285067 | 122285108 | chr12 | 122473581 | 122473611 | chr12 | 123129129 | 123129160 |
| chr12 | 123233806 | 123233846 | chr12 | 124246908 | 124246937 | chr12 | 124247208 | 124247237 |
| chr12 | 124393560 | 124393604 | chr12 | 124397464 | 124397618 | chr12 | 124865115 | 124865144 |
| chr12 | 125009276 | 125009306 | chr12 | 125533949 | 125534407 | chr12 | 125589840 | 125589872 |
| chr12 | 125670117 | 125670260 | chr12 | 126168554 | 126168620 | chr12 | 127211317 | 127211378 |
| chr12 | 127765158 | 127765432 | chr12 | 127940086 | 127940247 | chr12 | 128751384 | 128751443 |
| chr12 | 128751821 | 128751877 | chr12 | 128752115 | 128752240 | chr12 | 128752499 | 128752944 |
| chr12 | 128753210 | 128753240 | chr12 | 128850534 | 128850644 | chr12 | 129338588 | 129338816 |
| chr12 | 130037653 | 130037778 | chr12 | 130387797 | 130387811 | chr12 | 130388410 | 130388434 |
| chr12 | 130389013 | 130389152 | chr12 | 130589202 | 130589266 | chr12 | 130645233 | 130645627 |
| chr12 | 130646946 | 130647115 | chr12 | 130647574 | 130647908 | chr12 | 130647951 | 130648069 |
| chr12 | 130821371 | 130821621 | chr12 | 130968621 | 130968654 | chr12 | 131200379 | 131200645 |
| chr12 | 131400816 | 131400919 | chr12 | 131403032 | 131403125 | chr12 | 131513345 | 131513403 |
| chr12 | 132102173 | 132102202 | chr12 | 132169288 | 132169365 | chr12 | 132221689 | 132222076 |
| chr12 | 132333434 | 132333456 | chr12 | 132333516 | 132333597 | chr12 | 132348651 | 132348684 |
| chr12 | 132423595 | 132423854 | chr12 | 132643233 | 132643279 | chr12 | 132986495 | 132986581 |
| chr12 | 133002792 | 133003231 | chr12 | 133172907 | 133173021 | chr12 | 133195093 | 133195196 |
| chr12 | 133199738 | 133199784 | chr12 | 133280578 | 133280682 | chr12 | 133463736 | 133463876 |
| chr12 | 133464108 | 133464166 | chr12 | 133464840 | 133464934 | chr12 | 133464994 | 133465027 |
| chr12 | 133481490 | 133481655 | chr12 | 133484742 | 133484852 | chr12 | 133485162 | 133485347 |
| chr12 | 133485557 | 133485689 | chr12 | 133485816 | 133485847 | chr12 | 133758048 | 133758107 |
| chr13 | 20175911 | 20175941 | chr13 | 20735804 | 20736089 | chr13 | 21649636 | 21649775 |
| chr13 | 22243273 | 22243469 | chr13 | 23489851 | 23489914 | chr13 | 23653797 | 23653813 |
| chr13 | 23733447 | 23734020 | chr13 | 23734284 | 23734297 | chr13 | 24477643 | 24477906 |
| chr13 | 25115713 | 25115771 | chr13 | 25319856 | 25319904 | chr13 | 25320388 | 25320539 |
| chr13 | 25320614 | 25321028 | chr13 | 25321113 | 25321350 | chr13 | 25321699 | 25321942 |
| chr13 | 25593062 | 25593242 | chr13 | 25621045 | 25621205 | chr13 | 25621264 | 25621394 |
| chr13 | 25744716 | 25744734 | chr13 | 25745301 | 25745594 | chr13 | 25745727 | 25746000 |
| chr13 | 25946301 | 25946411 | chr13 | 25946620 | 25946673 | chr13 | 26042678 | 26042707 |
| chr13 | 26042769 | 26043170 | chr13 | 26043341 | 26043499 | chr13 | 26340608 | 26340755 |
| chr13 | 26625301 | 26625656 | chr13 | 27334211 | 27334563 | chr13 | 27334772 | 27334894 |
| chr13 | 28239909 | 28240164 | chr13 | 28365705 | 28366122 | chr13 | 28366482 | 28366577 |
| chr13 | 28367024 | 28367038 | chr13 | 28367794 | 28367945 | chr13 | 28368154 | 28368168 |
| chr13 | 28368451 | 28368593 | chr13 | 28368952 | 28369070 | chr13 | 28369162 | 28369891 |
| chr13 | 28369951 | 28369990 | chr13 | 28370947 | 28371061 | chr13 | 28394766 | 28394866 |
| chr13 | 28395501 | 28395553 | chr13 | 28395998 | 28396073 | chr13 | 28491793 | 28491946 |
| chr13 | 28492244 | 28492553 | chr13 | 28503042 | 28503074 | chr13 | 28528534 | 28528748 |
| chr13 | 28540745 | 28540927 | chr13 | 28543212 | 28543242 | chr13 | 28544397 | 28544584 |
| chr13 | 28544666 | 28544903 | chr13 | 28549497 | 28549891 | chr13 | 28550240 | 28550552 |
| chr13 | 28551417 | 28551461 | chr13 | 28551950 | 28552167 | chr13 | 28552794 | 28552824 |
| chr13 | 28553030 | 28553138 | chr13 | 28589765 | 28589794 | chr13 | 28592605 | 28592658 |
| chr13 | 28601345 | 28601374 | chr13 | 28602326 | 28602355 | chr13 | 28608233 | 28608355 |
| chr13 | 28610123 | 28610152 | chr13 | 28674018 | 28674226 | chr13 | 28674721 | 28674734 |
| chr13 | 29067773 | 29068416 | chr13 | 29068926 | 29068985 | chr13 | 29068994 | 29069065 |
| chr13 | 29106308 | 29106814 | chr13 | 29106899 | 29107063 | chr13 | 29107253 | 29107309 |
| chr13 | 29112420 | 29112444 | chr13 | 30141688 | 30141718 | chr13 | 30707569 | 30707599 |
| chr13 | 31742953 | 31743177 | chr13 | 32605034 | 32605324 | chr13 | 32605443 | 32605623 |
| chr13 | 32605675 | 32605966 | chr13 | 33591300 | 33591419 | chr13 | 33924666 | 33924790 |
| chr13 | 35517410 | 35517648 | chr13 | 36044829 | 36044930 | chr13 | 36049995 | 36050025 |
| chr13 | 36269480 | 36269509 | chr13 | 36553399 | 36553428 | chr13 | 36704939 | 36705055 |
| chr13 | 36705451 | 36705489 | chr13 | 36909206 | 36909236 | chr13 | 36920317 | 36920386 |
| chr13 | 36920628 | 36920785 | chr13 | 37004771 | 37005129 | chr13 | 37005900 | 37006062 |
| chr13 | 37006434 | 37006657 | chr13 | 37006734 | 37006762 | chr13 | 37248063 | 37248148 |
| chr13 | 37248295 | 37248319 | chr13 | 37248979 | 37248993 | chr13 | 37633989 | 37634018 |
| chr13 | 37643942 | 37644005 | chr13 | 38443618 | 38443715 | chr13 | 39261410 | 39261446 |
| chr13 | 41884500 | 41884534 | chr13 | 43148669 | 43148698 | chr13 | 43566247 | 43566647 |
| chr13 | 44947746 | 44948197 | chr13 | 45150013 | 45150276 | chr13 | 45885876 | 45885905 |
| chr13 | 45905236 | 45905264 | chr13 | 46425548 | 46425554 | chr13 | 46425576 | 46425584 |
| chr13 | 46660839 | 46660869 | chr13 | 46961494 | 46961533 | chr13 | 46961699 | 46961982 |
| chr13 | 47468139 | 47468168 | chr13 | 47472315 | 47472344 | chr13 | 47526166 | 47526182 |
| chr13 | 48478576 | 48478605 | chr13 | 48667877 | 48667907 | chr13 | 49794117 | 49794925 |
| chr13 | 50421504 | 50421696 | chr13 | 50639782 | 50639799 | chr13 | 52580344 | 52580369 |
| chr13 | 53312991 | 53313313 | chr13 | 53313513 | 53313612 | chr13 | 53313678 | 53313920 |
| chr13 | 53419734 | 53419775 | chr13 | 53420020 | 53420020 | chr13 | 53423838 | 53423978 |

TABLE 13-continued

Pan Cancer #3

| chr | start | end | chr | start | end | chr | start | end |
|---|---|---|---|---|---|---|---|---|
| chr13 | 57714539 | 57714568 | chr13 | 58203602 | 58203644 | chr13 | 58203851 | 58204103 |
| chr13 | 58204350 | 58204393 | chr13 | 58206042 | 58206231 | chr13 | 58206453 | 58206771 |
| chr13 | 58206862 | 58206983 | chr13 | 58207568 | 58207813 | chr13 | 58207892 | 58208020 |
| chr13 | 58208495 | 58208926 | chr13 | 62132346 | 62132375 | chr13 | 64650200 | 64650229 |
| chr13 | 65532258 | 65532287 | chr13 | 67803735 | 67804074 | chr13 | 67804494 | 67804523 |
| chr13 | 67805191 | 67805247 | chr13 | 70681626 | 70681777 | chr13 | 70681867 | 70682071 |
| chr13 | 71498386 | 71498415 | chr13 | 72439142 | 72439250 | chr13 | 73336049 | 73336078 |
| chr13 | 73619660 | 73619752 | chr13 | 78492684 | 78492840 | chr13 | 78493166 | 78493196 |
| chr13 | 78493455 | 78493809 | chr13 | 79168067 | 79168102 | chr13 | 79169850 | 79170113 |
| chr13 | 79170348 | 79170383 | chr13 | 79170468 | 79170884 | chr13 | 79171118 | 79171196 |
| chr13 | 79175770 | 79175943 | chr13 | 79176078 | 79176125 | chr13 | 79176277 | 79176420 |
| chr13 | 79176609 | 79176783 | chr13 | 79176993 | 79177184 | chr13 | 79177306 | 79177622 |
| chr13 | 79177886 | 79177998 | chr13 | 79183406 | 79183423 | chr13 | 81229343 | 81229372 |
| chr13 | 84455236 | 84455292 | chr13 | 84455581 | 84455715 | chr13 | 84457491 | 84457521 |
| chr13 | 87731371 | 87731400 | chr13 | 88323579 | 88323830 | chr13 | 88323868 | 88324207 |
| chr13 | 88324516 | 88324518 | chr13 | 88325300 | 88325460 | chr13 | 88325819 | 88326061 |
| chr13 | 88326538 | 88326707 | chr13 | 88326937 | 88327014 | chr13 | 88788883 | 88788912 |
| chr13 | 88997906 | 88997935 | chr13 | 89815436 | 89815465 | chr13 | 90015503 | 90015532 |
| chr13 | 91755723 | 91755750 | chr13 | 91948489 | 91948519 | chr13 | 92050760 | 92050814 |
| chr13 | 92051139 | 92051168 | chr13 | 92051374 | 92051513 | chr13 | 93879288 | 93879375 |
| chr13 | 93879670 | 93879700 | chr13 | 93880089 | 93880216 | chr13 | 93880534 | 93880737 |
| chr13 | 93880794 | 93880856 | chr13 | 95086143 | 95086172 | chr13 | 95357311 | 95357341 |
| chr13 | 95357574 | 95357775 | chr13 | 95358041 | 95358165 | chr13 | 95359747 | 95359803 |
| chr13 | 95360322 | 95360371 | chr13 | 95363210 | 95363429 | chr13 | 95363796 | 95363959 |
| chr13 | 95364065 | 95364196 | chr13 | 95364495 | 95364800 | chr13 | 95620021 | 95620078 |
| chr13 | 95620647 | 95620781 | chr13 | 95620854 | 95621011 | chr13 | 96031705 | 96031730 |
| chr13 | 96204923 | 96205363 | chr13 | 96296225 | 96296345 | chr13 | 96296373 | 96296473 |
| chr13 | 96296841 | 96296949 | chr13 | 96296992 | 96297137 | chr13 | 96743788 | 96744175 |
| chr13 | 97761876 | 97761925 | chr13 | 99851676 | 99851706 | chr13 | 100547713 | 100547893 |
| chr13 | 100608462 | 100608536 | chr13 | 100608596 | 100608804 | chr13 | 100608839 | 100609055 |
| chr13 | 100621941 | 100622015 | chr13 | 100624324 | 100624348 | chr13 | 100624587 | 100624729 |
| chr13 | 100626929 | 100627009 | chr13 | 100627295 | 100627348 | chr13 | 100627688 | 100627717 |
| chr13 | 100630169 | 100630298 | chr13 | 100630329 | 100630430 | chr13 | 100630630 | 100630997 |
| chr13 | 100633089 | 100633184 | chr13 | 100634314 | 100634617 | chr13 | 100635406 | 100635451 |
| chr13 | 100636167 | 100636238 | chr13 | 100637390 | 100637485 | chr13 | 100641282 | 100641408 |
| chr13 | 100642120 | 100642201 | chr13 | 100643296 | 100643435 | chr13 | 100644055 | 100644179 |
| chr13 | 100649325 | 100649575 | chr13 | 100649800 | 100649884 | chr13 | 102568454 | 102568484 |
| chr13 | 102569313 | 102569542 | chr13 | 103046721 | 103046995 | chr13 | 103052347 | 103052574 |
| chr13 | 103052892 | 103052940 | chr13 | 103053394 | 103053496 | chr13 | 105484285 | 105484314 |
| chr13 | 105791875 | 105791904 | chr13 | 107186855 | 107186884 | chr13 | 107187162 | 107187426 |
| chr13 | 107187666 | 107187695 | chr13 | 107188241 | 107188430 | chr13 | 108518813 | 108518933 |
| chr13 | 108519254 | 108519367 | chr13 | 108519737 | 108519745 | chr13 | 108520376 | 108520534 |
| chr13 | 108520979 | 108521076 | chr13 | 109147685 | 109147862 | chr13 | 109148155 | 109148278 |
| chr13 | 109148783 | 109149185 | chr13 | 110434451 | 110434593 | chr13 | 110958816 | 110958981 |
| chr13 | 110959753 | 110959970 | chr13 | 110960541 | 110960603 | chr13 | 111278255 | 111278426 |
| chr13 | 111363880 | 111363972 | chr13 | 112272991 | 112273088 | chr13 | 112707694 | 112707869 |
| chr13 | 112708308 | 112708513 | chr13 | 112709388 | 112709617 | chr13 | 112709883 | 112709928 |
| chr13 | 112710360 | 112710475 | chr13 | 112710759 | 112711293 | chr13 | 112711376 | 112711776 |
| chr13 | 112712017 | 112713029 | chr13 | 112715370 | 112715642 | chr13 | 112715985 | 112716313 |
| chr13 | 112716677 | 112716721 | chr13 | 112717026 | 112717242 | chr13 | 112717323 | 112717536 |
| chr13 | 112717835 | 112717949 | chr13 | 112720033 | 112720505 | chr13 | 112720723 | 112720767 |
| chr13 | 112721012 | 112721026 | chr13 | 112722129 | 112722220 | chr13 | 112722275 | 112722312 |
| chr13 | 112724505 | 112724535 | chr13 | 112726436 | 112726560 | chr13 | 112727984 | 112728200 |
| chr13 | 112758107 | 112758257 | chr13 | 112758274 | 112758372 | chr13 | 112758496 | 112758613 |
| chr13 | 112759112 | 112759248 | chr13 | 112759612 | 112759642 | chr13 | 112760007 | 112760327 |
| chr13 | 112760795 | 112761214 | chr13 | 113598618 | 113598851 | chr13 | 113985679 | 113985956 |
| chr13 | 114055983 | 114056137 | chr13 | 114060064 | 114060333 | chr13 | 114074768 | 114074853 |
| chr13 | 114082984 | 114083014 | chr13 | 114123168 | 114123291 | chr13 | 114189737 | 114189809 |
| chr13 | 114221622 | 114221652 | chr13 | 114304565 | 114304927 | chr13 | 114479404 | 114479454 |
| chr13 | 114498017 | 114498260 | chr13 | 114748342 | 114748638 | chr13 | 114766270 | 114766300 |
| chr13 | 114780561 | 114781061 | chr13 | 114807617 | 114807815 | chr13 | 114855635 | 114855669 |
| chr13 | 114862308 | 114862368 | chr13 | 114897194 | 114897217 | chr13 | 114961823 | 114961933 |
| chr14 | 21093454 | 21093543 | chr14 | 21093603 | 21093631 | chr14 | 21100748 | 21100778 |
| chr14 | 21100801 | 21100831 | chr14 | 22005029 | 22005073 | chr14 | 23234956 | 23234994 |
| chr14 | 23356044 | 23356384 | chr14 | 23706727 | 23706765 | chr14 | 24641010 | 24641215 |
| chr14 | 24803594 | 24804122 | chr14 | 26674354 | 26674384 | chr14 | 26674699 | 26674729 |
| chr14 | 27066562 | 27066704 | chr14 | 27066764 | 27066785 | chr14 | 27067373 | 27067386 |
| chr14 | 29225531 | 29225561 | chr14 | 29226071 | 29226198 | chr14 | 29228654 | 29228778 |
| chr14 | 29229107 | 29229386 | chr14 | 29231071 | 29231185 | chr14 | 29231425 | 29231590 |
| chr14 | 29235003 | 29235308 | chr14 | 29235342 | 29235356 | chr14 | 29237063 | 29237066 |
| chr14 | 29242763 | 29242908 | chr14 | 29243516 | 29243669 | chr14 | 29243731 | 29243888 |
| chr14 | 29244224 | 29244308 | chr14 | 29247689 | 29247740 | chr14 | 29254612 | 29254713 |
| chr14 | 31344346 | 31344549 | chr14 | 31925639 | 31925724 | chr14 | 32597620 | 32597657 |
| chr14 | 33402462 | 33402762 | chr14 | 33403045 | 33403316 | chr14 | 33403866 | 33404418 |
| chr14 | 34269897 | 34270004 | chr14 | 34420250 | 34420288 | chr14 | 35023187 | 35023322 |
| chr14 | 35024446 | 35024466 | chr14 | 35389907 | 35389943 | chr14 | 36003442 | 36003826 |

TABLE 13-continued

Pan Cancer #3

| chr | start | end | chr | start | end | chr | start | end |
|---|---|---|---|---|---|---|---|---|
| chr14 | 36004081 | 36004493 | chr14 | 36004711 | 36004734 | chr14 | 36004822 | 36004921 |
| chr14 | 36972803 | 36972912 | chr14 | 36973455 | 36973538 | chr14 | 36974294 | 36974927 |
| chr14 | 36974968 | 36974982 | chr14 | 36975299 | 36975399 | chr14 | 36977645 | 36977929 |
| chr14 | 36977975 | 36978009 | chr14 | 36978548 | 36978578 | chr14 | 36979619 | 36979649 |
| chr14 | 36982927 | 36982969 | chr14 | 36983708 | 36984146 | chr14 | 36985841 | 36985871 |
| chr14 | 36986301 | 36986471 | chr14 | 36987302 | 36987685 | chr14 | 36987939 | 36988143 |
| chr14 | 36988428 | 36988460 | chr14 | 36990858 | 36991032 | chr14 | 36991095 | 36991177 |
| chr14 | 36991532 | 36991613 | chr14 | 36991989 | 36992163 | chr14 | 36992222 | 36992417 |
| chr14 | 36993473 | 36993487 | chr14 | 36993694 | 36993956 | chr14 | 36994248 | 36994999 |
| chr14 | 37050752 | 37050794 | chr14 | 37116105 | 37116294 | chr14 | 37117611 | 37117697 |
| chr14 | 37123438 | 37124077 | chr14 | 37124482 | 37124572 | chr14 | 37124992 | 37125545 |
| chr14 | 37126241 | 37126297 | chr14 | 37126566 | 37126713 | chr14 | 37127281 | 37127311 |
| chr14 | 37127655 | 37127779 | chr14 | 37128553 | 37128723 | chr14 | 37130077 | 37130260 |
| chr14 | 37132375 | 37132553 | chr14 | 37132603 | 37132695 | chr14 | 37133001 | 37133052 |
| chr14 | 37135784 | 37136017 | chr14 | 37136295 | 37136345 | chr14 | 37136588 | 37136618 |
| chr14 | 38060677 | 38060916 | chr14 | 38064401 | 38064549 | chr14 | 38677519 | 38677548 |
| chr14 | 38677761 | 38677790 | chr14 | 38724294 | 38724525 | chr14 | 38724979 | 38725258 |
| chr14 | 38725521 | 38725764 | chr14 | 39579800 | 39579830 | chr14 | 42074544 | 42074586 |
| chr14 | 42074669 | 42074987 | chr14 | 42075588 | 42076043 | chr14 | 42076106 | 42076212 |
| chr14 | 42076823 | 42076853 | chr14 | 42077230 | 42077268 | chr14 | 42077770 | 42077800 |
| chr14 | 42079289 | 42079328 | chr14 | 48143798 | 48143957 | chr14 | 48144359 | 48144401 |
| chr14 | 48144699 | 48144763 | chr14 | 48145237 | 48145257 | chr14 | 50333964 | 50333994 |
| chr14 | 50334335 | 50334355 | chr14 | 51338730 | 51338731 | chr14 | 51560304 | 51560713 |
| chr14 | 51560771 | 51561428 | chr14 | 51561765 | 51562012 | chr14 | 51955509 | 51955538 |
| chr14 | 52534648 | 52534791 | chr14 | 52535012 | 52535026 | chr14 | 52535056 | 52535263 |
| chr14 | 52535335 | 52536104 | chr14 | 52536343 | 52536404 | chr14 | 52734509 | 52734557 |
| chr14 | 52734777 | 52735001 | chr14 | 52735045 | 52735255 | chr14 | 52781525 | 52781916 |
| chr14 | 54422651 | 54422925 | chr14 | 55370202 | 55370219 | chr14 | 55595938 | 55595968 |
| chr14 | 55765285 | 55765714 | chr14 | 55823079 | 55823179 | chr14 | 57045520 | 57045739 |
| chr14 | 57260946 | 57261094 | chr14 | 57261175 | 57261407 | chr14 | 57261466 | 57261821 |
| chr14 | 57262072 | 57262179 | chr14 | 57264079 | 57264645 | chr14 | 57264765 | 57264806 |
| chr14 | 57265148 | 57265240 | chr14 | 57270936 | 57270971 | chr14 | 57271154 | 57271266 |
| chr14 | 57272009 | 57272067 | chr14 | 57274486 | 57275049 | chr14 | 57275211 | 57275305 |
| chr14 | 57275596 | 57275685 | chr14 | 57276074 | 57276104 | chr14 | 57276440 | 57276666 |
| chr14 | 57277920 | 57278762 | chr14 | 57278838 | 57279564 | chr14 | 57279643 | 57279657 |
| chr14 | 57283314 | 57283408 | chr14 | 57283446 | 57284036 | chr14 | 57284071 | 57284659 |
| chr14 | 58332297 | 58332403 | chr14 | 59770326 | 59770359 | chr14 | 60097193 | 60097246 |
| chr14 | 60097407 | 60097566 | chr14 | 60386207 | 60386252 | chr14 | 60386638 | 60386701 |
| chr14 | 60794635 | 60794667 | chr14 | 60952196 | 60952419 | chr14 | 60952517 | 60952632 |
| chr14 | 60952730 | 60952959 | chr14 | 60973151 | 60973324 | chr14 | 60973697 | 60974007 |
| chr14 | 60974368 | 60974403 | chr14 | 60975384 | 60975888 | chr14 | 60976075 | 60976514 |
| chr14 | 60976813 | 60976860 | chr14 | 60977337 | 60977712 | chr14 | 60977880 | 60978147 |
| chr14 | 60981202 | 60981268 | chr14 | 60981676 | 60981793 | chr14 | 60982110 | 60982367 |
| chr14 | 60982574 | 60982622 | chr14 | 60982841 | 60982911 | chr14 | 61104291 | 61104556 |
| chr14 | 61104624 | 61104864 | chr14 | 61108620 | 61108996 | chr14 | 61109206 | 61109470 |
| chr14 | 61109839 | 61110243 | chr14 | 61114137 | 61114456 | chr14 | 61115311 | 61115517 |
| chr14 | 61118743 | 61118765 | chr14 | 61118965 | 61119136 | chr14 | 61119536 | 61119639 |
| chr14 | 61747389 | 61747527 | chr14 | 61747583 | 61748033 | chr14 | 62279578 | 62279852 |
| chr14 | 62279899 | 62280006 | chr14 | 62583809 | 62583869 | chr14 | 63512100 | 63512291 |
| chr14 | 63512573 | 63512708 | chr14 | 63512741 | 63512816 | chr14 | 63513124 | 63513154 |
| chr14 | 64222413 | 64222451 | chr14 | 65005795 | 65005833 | chr14 | 65008998 | 65009193 |
| chr14 | 65233339 | 65233464 | chr14 | 67585164 | 67585199 | chr14 | 67886582 | 67886606 |
| chr14 | 69014044 | 69014110 | chr14 | 69866541 | 69866564 | chr14 | 69867022 | 69867196 |
| chr14 | 70014723 | 70014974 | chr14 | 70038990 | 70039025 | chr14 | 70346136 | 70346491 |
| chr14 | 70654378 | 70654713 | chr14 | 70655530 | 70655889 | chr14 | 70655920 | 70656090 |
| chr14 | 72398743 | 72399019 | chr14 | 72399452 | 72399453 | chr14 | 72399929 | 72400029 |
| chr14 | 73167750 | 73167899 | chr14 | 73175026 | 73175148 | chr14 | 73178807 | 73178865 |
| chr14 | 73180208 | 73180314 | chr14 | 73236095 | 73236137 | chr14 | 73318471 | 73318629 |
| chr14 | 73333249 | 73333293 | chr14 | 73602350 | 73602389 | chr14 | 74706015 | 74706222 |
| chr14 | 74706941 | 74707544 | chr14 | 74707573 | 74707747 | chr14 | 74707792 | 74707873 |
| chr14 | 74708862 | 74708955 | chr14 | 74892540 | 74892569 | chr14 | 74893074 | 74893113 |
| chr14 | 75078170 | 75078242 | chr14 | 75760311 | 75760329 | chr14 | 75988341 | 75988370 |
| chr14 | 75988732 | 75988761 | chr14 | 76128674 | 76128698 | chr14 | 76604682 | 76604716 |
| chr14 | 76605072 | 76605376 | chr14 | 76843742 | 76843953 | chr14 | 77228121 | 77228159 |
| chr14 | 77606922 | 77607236 | chr14 | 77737212 | 77737814 | chr14 | 79745138 | 79745175 |
| chr14 | 85996479 | 85996608 | chr14 | 85996892 | 85996906 | chr14 | 85997821 | 85997925 |
| chr14 | 85998288 | 85998574 | chr14 | 85998630 | 85998683 | chr14 | 85999597 | 85999613 |
| chr14 | 86000270 | 86000511 | chr14 | 86000918 | 86001114 | chr14 | 89817889 | 89818034 |
| chr14 | 90527714 | 90527758 | chr14 | 90983328 | 90983360 | chr14 | 91691163 | 91691306 |
| chr14 | 91691789 | 91691822 | chr14 | 91766154 | 91766450 | chr14 | 91780382 | 91780512 |
| chr14 | 91801036 | 91801164 | chr14 | 92507655 | 92507792 | chr14 | 92789512 | 92789542 |
| chr14 | 92789960 | 92790098 | chr14 | 92790637 | 92790703 | chr14 | 92979917 | 92979991 |
| chr14 | 93155061 | 93155315 | chr14 | 93389557 | 93389693 | chr14 | 93389713 | 93389776 |
| chr14 | 93571193 | 93571326 | chr14 | 93706752 | 93706782 | chr14 | 94254389 | 94254458 |
| chr14 | 94254499 | 94254513 | chr14 | 94405734 | 94405785 | chr14 | 94603542 | 94603670 |
| chr14 | 94889856 | 94889870 | chr14 | 95233705 | 95233765 | chr14 | 95234643 | 95234710 |

TABLE 13-continued

Pan Cancer #3

| chr | start | end | chr | start | end | chr | start | end |
|---|---|---|---|---|---|---|---|---|
| chr14 | 95235026 | 95235369 | chr14 | 95235989 | 95236111 | chr14 | 95236524 | 95236553 |
| chr14 | 95236819 | 95236848 | chr14 | 95237622 | 95237642 | chr14 | 95239422 | 95239633 |
| chr14 | 95240127 | 95240157 | chr14 | 95240227 | 95240341 | chr14 | 95240392 | 95240422 |
| chr14 | 95557626 | 95557655 | chr14 | 95560448 | 95560477 | chr14 | 95740095 | 95740116 |
| chr14 | 96342897 | 96343133 | chr14 | 96343404 | 96343433 | chr14 | 96343668 | 96343701 |
| chr14 | 97045354 | 97045431 | chr14 | 97058944 | 97059083 | chr14 | 97499277 | 97499315 |
| chr14 | 97499847 | 97499849 | chr14 | 97685044 | 97685288 | chr14 | 97685707 | 97685959 |
| chr14 | 99584575 | 99584664 | chr14 | 99712321 | 99712394 | chr14 | 99736151 | 99736183 |
| chr14 | 99737398 | 99737462 | chr14 | 100437794 | 100437949 | chr14 | 100438705 | 100438811 |
| chr14 | 100643350 | 100643481 | chr14 | 100793556 | 100793650 | chr14 | 101250109 | 101250272 |
| chr14 | 101506231 | 101506260 | chr14 | 101543868 | 101544235 | chr14 | 101923114 | 101923250 |
| chr14 | 101923600 | 101923686 | chr14 | 101924031 | 101924047 | chr14 | 101925049 | 101925071 |
| chr14 | 101925656 | 101925901 | chr14 | 102026360 | 102026484 | chr14 | 102026797 | 102026967 |
| chr14 | 102031236 | 102031271 | chr14 | 102031512 | 102031580 | chr14 | 102247912 | 102248214 |
| chr14 | 102418607 | 102418637 | chr14 | 102521602 | 102521758 | chr14 | 102530007 | 102530234 |
| chr14 | 102530500 | 102530530 | chr14 | 102564464 | 102564505 | chr14 | 102682077 | 102682149 |
| chr14 | 102973169 | 102973268 | chr14 | 103021391 | 103022003 | chr14 | 103394884 | 103395101 |
| chr14 | 103477643 | 103477779 | chr14 | 103655226 | 103655601 | chr14 | 103674078 | 103674079 |
| chr14 | 103687082 | 103687219 | chr14 | 103739967 | 103740150 | chr14 | 103740358 | 103740430 |
| chr14 | 103745699 | 103745750 | chr14 | 104160060 | 104160134 | chr14 | 104202705 | 104202759 |
| chr14 | 104547785 | 104547909 | chr14 | 104571985 | 104572116 | chr14 | 104601737 | 104601832 |
| chr14 | 104602033 | 104602063 | chr14 | 104605032 | 104605114 | chr14 | 104620411 | 104620554 |
| chr14 | 104627664 | 104627759 | chr14 | 104645126 | 104645188 | chr14 | 104646317 | 104646491 |
| chr14 | 104647257 | 104647287 | chr14 | 104682545 | 104682656 | chr14 | 104862860 | 104863026 |
| chr14 | 105071298 | 105071396 | chr14 | 105157485 | 105157554 | chr14 | 105239389 | 105239439 |
| chr14 | 105239793 | 105239825 | chr14 | 105241309 | 105241428 | chr14 | 105243032 | 105243064 |
| chr14 | 105246427 | 105246582 | chr14 | 105512063 | 105512395 | chr14 | 105658349 | 105658425 |
| chr14 | 105714258 | 105714334 | chr14 | 105714415 | 105714441 | chr14 | 105715248 | 105715392 |
| chr14 | 105830630 | 105830859 | chr14 | 105963655 | 105963772 | chr15 | 22822348 | 22822388 |
| chr15 | 23158397 | 23158489 | chr15 | 23692316 | 23692415 | chr15 | 26107640 | 26107743 |
| chr15 | 26107846 | 26107860 | chr15 | 26108096 | 26108326 | chr15 | 26108549 | 26108701 |
| chr15 | 27212887 | 27213172 | chr15 | 27604062 | 27604123 | chr15 | 28341699 | 28342019 |
| chr15 | 28344173 | 28344187 | chr15 | 28344224 | 28344287 | chr15 | 28352240 | 28352421 |
| chr15 | 29077284 | 29077383 | chr15 | 29130807 | 29131047 | chr15 | 29131533 | 29131630 |
| chr15 | 29131756 | 29131875 | chr15 | 29396330 | 29396360 | chr15 | 29407777 | 29407813 |
| chr15 | 29407867 | 29408001 | chr15 | 29862502 | 29862582 | chr15 | 30115185 | 30115228 |
| chr15 | 31455370 | 31455485 | chr15 | 31775596 | 31775637 | chr15 | 31775679 | 31775782 |
| chr15 | 32933918 | 32934018 | chr15 | 33009747 | 33009761 | chr15 | 33009822 | 33010675 |
| chr15 | 33010721 | 33011348 | chr15 | 33011601 | 33011633 | chr15 | 33487057 | 33487120 |
| chr15 | 33602801 | 33602886 | chr15 | 33603194 | 33603608 | chr15 | 33879242 | 33879272 |
| chr15 | 34517058 | 34517334 | chr15 | 34630439 | 34630449 | chr15 | 34630515 | 34630544 |
| chr15 | 34729478 | 34729582 | chr15 | 34786504 | 34786943 | chr15 | 34787233 | 34787304 |
| chr15 | 35046607 | 35046608 | chr15 | 35047034 | 35047133 | chr15 | 35087666 | 35087698 |
| chr15 | 37180309 | 37180743 | chr15 | 37402974 | 37403086 | chr15 | 37403116 | 37403238 |
| chr15 | 40211819 | 40212190 | chr15 | 40575630 | 40575744 | chr15 | 40671588 | 40671620 |
| chr15 | 40675092 | 40675121 | chr15 | 40763811 | 40763862 | chr15 | 40782219 | 40782249 |
| chr15 | 41165245 | 41165700 | chr15 | 41804878 | 41805772 | chr15 | 41835694 | 41835720 |
| chr15 | 41913750 | 41913807 | chr15 | 41952572 | 41952711 | chr15 | 42749733 | 42749899 |
| chr15 | 43551059 | 43551196 | chr15 | 43810405 | 43810435 | chr15 | 44037568 | 44037604 |
| chr15 | 45403636 | 45403680 | chr15 | 45403799 | 45403999 | chr15 | 45404103 | 45404130 |
| chr15 | 45404898 | 45405117 | chr15 | 45421385 | 45421435 | chr15 | 45421998 | 45422095 |
| chr15 | 45427370 | 45427410 | chr15 | 45427611 | 45427719 | chr15 | 45427772 | 45427786 |
| chr15 | 45444061 | 45444141 | chr15 | 45479460 | 45479516 | chr15 | 45493209 | 45493371 |
| chr15 | 45670462 | 45670838 | chr15 | 46021437 | 46021467 | chr15 | 47476118 | 47476239 |
| chr15 | 47476291 | 47476419 | chr15 | 47476877 | 47476980 | chr15 | 47477013 | 47477018 |
| chr15 | 48483956 | 48483986 | chr15 | 48936726 | 48937645 | chr15 | 48937710 | 48937987 |
| chr15 | 48938212 | 48938510 | chr15 | 51385913 | 51386181 | chr15 | 51634075 | 51634135 |
| chr15 | 51973646 | 51973694 | chr15 | 51973764 | 51973934 | chr15 | 53075809 | 53075864 |
| chr15 | 53075986 | 53077000 | chr15 | 53077066 | 53077361 | chr15 | 53077655 | 53077731 |
| chr15 | 53078064 | 53078236 | chr15 | 53079340 | 53079677 | chr15 | 53079718 | 53079891 |
| chr15 | 53079971 | 53080082 | chr15 | 53080337 | 53080606 | chr15 | 53080935 | 53080990 |
| chr15 | 53081399 | 53081677 | chr15 | 53082443 | 53082491 | chr15 | 53096816 | 53096891 |
| chr15 | 53097231 | 53097261 | chr15 | 53097778 | 53097906 | chr15 | 53098382 | 53098658 |
| chr15 | 54270498 | 54270707 | chr15 | 54270932 | 54270961 | chr15 | 55452967 | 55452993 |
| chr15 | 55699089 | 55699127 | chr15 | 55806758 | 55806859 | chr15 | 55880891 | 55881011 |
| chr15 | 58357800 | 58357819 | chr15 | 59158488 | 59158537 | chr15 | 59950341 | 59950363 |
| chr15 | 60287038 | 60287585 | chr15 | 60287644 | 60287733 | chr15 | 60288786 | 60288844 |
| chr15 | 60289310 | 60289546 | chr15 | 60296122 | 60296209 | chr15 | 60296598 | 60296617 |
| chr15 | 60296861 | 60296923 | chr15 | 60297152 | 60297409 | chr15 | 60297637 | 60297826 |
| chr15 | 60297942 | 60298108 | chr15 | 61520916 | 61521014 | chr15 | 61521659 | 61521937 |
| chr15 | 62456922 | 62456952 | chr15 | 65669859 | 65669899 | chr15 | 65685591 | 65685708 |
| chr15 | 65862033 | 65862121 | chr15 | 66727409 | 66727498 | chr15 | 66729148 | 66729177 |
| chr15 | 66774117 | 66774203 | chr15 | 66963816 | 66963871 | chr15 | 68112611 | 68112641 |
| chr15 | 68113868 | 68113898 | chr15 | 68114139 | 68114195 | chr15 | 68116369 | 68116621 |
| chr15 | 68117830 | 68118633 | chr15 | 68118930 | 68119174 | chr15 | 68119579 | 68120352 |
| chr15 | 68120827 | 68120857 | chr15 | 68121150 | 68121957 | chr15 | 68122643 | 68122673 |

TABLE 13-continued

Pan Cancer #3

| chr | start | end | chr | start | end | chr | start | end |
|---|---|---|---|---|---|---|---|---|
| chr15 | 68125261 | 68125664 | chr15 | 68127801 | 68128350 | chr15 | 68128594 | 68128688 |
| chr15 | 68260519 | 68260709 | chr15 | 71055636 | 71055815 | chr15 | 72412083 | 72412176 |
| chr15 | 72612540 | 72612906 | chr15 | 72743741 | 72743796 | chr15 | 73660004 | 73660067 |
| chr15 | 73661469 | 73661666 | chr15 | 74045075 | 74045097 | chr15 | 74422006 | 74422146 |
| chr15 | 74422869 | 74423002 | chr15 | 74658151 | 74658396 | chr15 | 74658502 | 74658587 |
| chr15 | 74686021 | 74686051 | chr15 | 74818772 | 74818789 | chr15 | 74903896 | 74903926 |
| chr15 | 75251346 | 75251382 | chr15 | 75251672 | 75251786 | chr15 | 76627508 | 76627536 |
| chr15 | 76627576 | 76627826 | chr15 | 76629163 | 76629220 | chr15 | 76629494 | 76629531 |
| chr15 | 76629814 | 76630124 | chr15 | 76630520 | 76630847 | chr15 | 76638472 | 76638496 |
| chr15 | 77448967 | 77449001 | chr15 | 78111196 | 78111210 | chr15 | 78501806 | 78501942 |
| chr15 | 78556819 | 78557108 | chr15 | 78596065 | 78596218 | chr15 | 78632727 | 78632823 |
| chr15 | 78912281 | 78912371 | chr15 | 78912623 | 78912653 | chr15 | 78912912 | 78913027 |
| chr15 | 78913095 | 78913170 | chr15 | 78913535 | 78913651 | chr15 | 79104217 | 79104246 |
| chr15 | 79104466 | 79104495 | chr15 | 79381705 | 79381745 | chr15 | 79382099 | 79382571 |
| chr15 | 79382786 | 79383257 | chr15 | 79383947 | 79383977 | chr15 | 79502211 | 79502360 |
| chr15 | 79575278 | 79575474 | chr15 | 79576145 | 79576277 | chr15 | 79724502 | 79724560 |
| chr15 | 79724607 | 79724792 | chr15 | 79724864 | 79725140 | chr15 | 79725422 | 79725539 |
| chr15 | 81071827 | 81071867 | chr15 | 82336879 | 82336972 | chr15 | 82340070 | 82340157 |
| chr15 | 83315336 | 83315393 | chr15 | 83316251 | 83317087 | chr15 | 83349234 | 83349611 |
| chr15 | 83349672 | 83349686 | chr15 | 83378212 | 83378370 | chr15 | 83776255 | 83776306 |
| chr15 | 83776333 | 83776716 | chr15 | 83776769 | 83776785 | chr15 | 83866523 | 83866541 |
| chr15 | 83875648 | 83875665 | chr15 | 83875706 | 83875901 | chr15 | 83877055 | 83877149 |
| chr15 | 83953884 | 83953903 | chr15 | 83954380 | 83954409 | chr15 | 84115747 | 84115853 |
| chr15 | 84115932 | 84115966 | chr15 | 84116905 | 84116949 | chr15 | 84322994 | 84323037 |
| chr15 | 84748578 | 84748619 | chr15 | 84748679 | 84749260 | chr15 | 85143024 | 85143054 |
| chr15 | 88798725 | 88798791 | chr15 | 88799537 | 88800301 | chr15 | 88800541 | 88801008 |
| chr15 | 88801089 | 88801103 | chr15 | 89149169 | 89149448 | chr15 | 89248753 | 89248907 |
| chr15 | 89346050 | 89346326 | chr15 | 89346347 | 89346393 | chr15 | 89346670 | 89346793 |
| chr15 | 89346882 | 89346943 | chr15 | 89903484 | 89903814 | chr15 | 89910521 | 89910748 |
| chr15 | 89911087 | 89911186 | chr15 | 89913750 | 89913780 | chr15 | 89914231 | 89914449 |
| chr15 | 89914867 | 89914895 | chr15 | 89915240 | 89915369 | chr15 | 89921956 | 89922006 |
| chr15 | 89922500 | 89922546 | chr15 | 89942755 | 89942945 | chr15 | 89943410 | 89943706 |
| chr15 | 89949617 | 89949942 | chr15 | 89950236 | 89950736 | chr15 | 89951082 | 89951113 |
| chr15 | 89951466 | 89951801 | chr15 | 89952153 | 89952452 | chr15 | 89952700 | 89953055 |
| chr15 | 89954197 | 89954335 | chr15 | 89956423 | 89956450 | chr15 | 90039563 | 90039711 |
| chr15 | 90631823 | 90631948 | chr15 | 90755916 | 90756079 | chr15 | 91643360 | 91643586 |
| chr15 | 92936290 | 92936322 | chr15 | 92937153 | 92937374 | chr15 | 92937927 | 92938060 |
| chr15 | 92938123 | 92938293 | chr15 | 93158592 | 93158739 | chr15 | 93631739 | 93632014 |
| chr15 | 93632660 | 93633233 | chr15 | 94347602 | 94347632 | chr15 | 96874362 | 96874514 |
| chr15 | 96889154 | 96889183 | chr15 | 96889401 | 96889430 | chr15 | 96897934 | 96898010 |
| chr15 | 96911559 | 96911691 | chr15 | 96952696 | 96953098 | chr15 | 96953132 | 96953209 |
| chr15 | 96959730 | 96959960 | chr15 | 96960376 | 96960409 | chr15 | 96960732 | 96960826 |
| chr15 | 97006372 | 97006533 | chr15 | 98504114 | 98504144 | chr15 | 98836178 | 98836393 |
| chr15 | 98964786 | 98965138 | chr15 | 99193206 | 99193480 | chr15 | 99193914 | 99194186 |
| chr15 | 99453230 | 99453440 | chr15 | 99456299 | 99456329 | chr15 | 99497059 | 99497132 |
| chr15 | 100913423 | 100913595 | chr15 | 101420521 | 101420610 | chr15 | 101420972 | 101420989 |
| chr15 | 101818327 | 101818357 | chr16 | 93831 | 93932 | chr16 | 142649 | 142783 |
| chr16 | 215416 | 215872 | chr16 | 215913 | 216224 | chr16 | 216676 | 217036 |
| chr16 | 230265 | 230315 | chr16 | 230497 | 230610 | chr16 | 318104 | 318227 |
| chr16 | 318498 | 318763 | chr16 | 337599 | 337659 | chr16 | 410377 | 410407 |
| chr16 | 565492 | 565623 | chr16 | 571714 | 571959 | chr16 | 611385 | 611520 |
| chr16 | 611969 | 612260 | chr16 | 612869 | 613037 | chr16 | 667141 | 667297 |
| chr16 | 667547 | 667585 | chr16 | 667876 | 668074 | chr16 | 672768 | 672806 |
| chr16 | 677972 | 678084 | chr16 | 700299 | 700329 | chr16 | 726626 | 726990 |
| chr16 | 731488 | 731610 | chr16 | 735205 | 735594 | chr16 | 740883 | 740914 |
| chr16 | 741376 | 741519 | chr16 | 762669 | 762694 | chr16 | 837361 | 837460 |
| chr16 | 845955 | 845985 | chr16 | 882566 | 882588 | chr16 | 895093 | 895166 |
| chr16 | 943481 | 943553 | chr16 | 1018120 | 1018150 | chr16 | 1019640 | 1019685 |
| chr16 | 1030444 | 1030655 | chr16 | 1052587 | 1052627 | chr16 | 1102927 | 1102957 |
| chr16 | 1116661 | 1116691 | chr16 | 1122858 | 1122946 | chr16 | 1129011 | 1129140 |
| chr16 | 1155162 | 1155212 | chr16 | 1204003 | 1204034 | chr16 | 1217307 | 1217503 |
| chr16 | 1218034 | 1218090 | chr16 | 1228804 | 1228916 | chr16 | 1230056 | 1230142 |
| chr16 | 1248604 | 1248675 | chr16 | 1267925 | 1268120 | chr16 | 1271546 | 1271646 |
| chr16 | 1312526 | 1312611 | chr16 | 1323976 | 1324061 | chr16 | 1382901 | 1382940 |
| chr16 | 1394502 | 1394596 | chr16 | 1397454 | 1397484 | chr16 | 1407370 | 1407518 |
| chr16 | 1407818 | 1407846 | chr16 | 1408210 | 1408240 | chr16 | 1428508 | 1428873 |
| chr16 | 1491567 | 1491613 | chr16 | 1704656 | 1704800 | chr16 | 1730306 | 1730597 |
| chr16 | 1741853 | 1742079 | chr16 | 1750769 | 1750907 | chr16 | 1842490 | 1842519 |
| chr16 | 2029072 | 2029137 | chr16 | 2040914 | 2040960 | chr16 | 2040981 | 2041512 |
| chr16 | 2041582 | 2042160 | chr16 | 2042875 | 2042905 | chr16 | 2086831 | 2086860 |
| chr16 | 2106703 | 2106732 | chr16 | 2111966 | 2111995 | chr16 | 2120515 | 2120544 |
| chr16 | 2122243 | 2122272 | chr16 | 2124205 | 2124348 | chr16 | 2126080 | 2126109 |
| chr16 | 2128577 | 2129581 | chr16 | 2130361 | 2130390 | chr16 | 2132244 | 2132315 |
| chr16 | 2135301 | 2135330 | chr16 | 2136228 | 2136257 | chr16 | 2136727 | 2136855 |
| chr16 | 2140403 | 2140438 | chr16 | 2141909 | 2141972 | chr16 | 2142546 | 2142628 |
| chr16 | 2213313 | 2213343 | chr16 | 2232745 | 2232784 | chr16 | 2234726 | 2235020 |

TABLE 13-continued

Pan Cancer #3

| chr | start | end | chr | start | end | chr | start | end |
|---|---|---|---|---|---|---|---|---|
| chr16 | 2281249 | 2281314 | chr16 | 2287295 | 2287370 | chr16 | 2485858 | 2485917 |
| chr16 | 2531069 | 2531177 | chr16 | 2764377 | 2764470 | chr16 | 2770122 | 2770512 |
| chr16 | 2818101 | 2818156 | chr16 | 2892542 | 2892602 | chr16 | 2892627 | 2892729 |
| chr16 | 2974601 | 2974650 | chr16 | 3017157 | 3017430 | chr16 | 3068171 | 3068201 |
| chr16 | 3151127 | 3151186 | chr16 | 3211708 | 3211744 | chr16 | 3211804 | 3211984 |
| chr16 | 3220591 | 3220892 | chr16 | 3221142 | 3221700 | chr16 | 3221787 | 3222239 |
| chr16 | 3225471 | 3225607 | chr16 | 3232739 | 3233016 | chr16 | 3233199 | 3233330 |
| chr16 | 3233435 | 3234103 | chr16 | 3234196 | 3234452 | chr16 | 3237857 | 3238022 |
| chr16 | 3238142 | 3238546 | chr16 | 3238993 | 3239631 | chr16 | 3239691 | 3239848 |
| chr16 | 3241549 | 3241663 | chr16 | 3241936 | 3241966 | chr16 | 3355279 | 3355718 |
| chr16 | 3598920 | 3598953 | chr16 | 3696694 | 3696724 | chr16 | 3802981 | 3803074 |
| chr16 | 3950263 | 3950279 | chr16 | 4264529 | 4264694 | chr16 | 4310735 | 4310847 |
| chr16 | 4431126 | 4431189 | chr16 | 4431487 | 4431516 | chr16 | 4731638 | 4731718 |
| chr16 | 4733166 | 4733195 | chr16 | 4738567 | 4738680 | chr16 | 4751554 | 4751583 |
| chr16 | 4846136 | 4846415 | chr16 | 4887144 | 4887164 | chr16 | 5037900 | 5038004 |
| chr16 | 5541116 | 5541158 | chr16 | 6069941 | 6070019 | chr16 | 7354634 | 7354657 |
| chr16 | 7382499 | 7382534 | chr16 | 8781032 | 8781135 | chr16 | 8870353 | 8870383 |
| chr16 | 9009860 | 9009989 | chr16 | 10274399 | 10274429 | chr16 | 10275308 | 10275392 |
| chr16 | 10275752 | 10275948 | chr16 | 10276360 | 10277050 | chr16 | 10277072 | 10277409 |
| chr16 | 10479815 | 10479980 | chr16 | 11242000 | 11242138 | chr16 | 11427659 | 11427732 |
| chr16 | 11490632 | 11490662 | chr16 | 12210772 | 12210896 | chr16 | 12211279 | 12211416 |
| chr16 | 12530169 | 12530199 | chr16 | 12971776 | 12971934 | chr16 | 12994459 | 12994737 |
| chr16 | 12995062 | 12995593 | chr16 | 12995803 | 12995803 | chr16 | 12996074 | 12996328 |
| chr16 | 12996617 | 12996720 | chr16 | 12996948 | 12997011 | chr16 | 12997386 | 12997703 |
| chr16 | 14021974 | 14022003 | chr16 | 14041504 | 14041533 | chr16 | 14041795 | 14041824 |
| chr16 | 14042062 | 14042091 | chr16 | 14725842 | 14725864 | chr16 | 15489599 | 15489808 |
| chr16 | 15739004 | 15739042 | chr16 | 15820825 | 15820865 | chr16 | 18802465 | 18802680 |
| chr16 | 18950973 | 18951018 | chr16 | 19531564 | 19531601 | chr16 | 19567202 | 19567449 |
| chr16 | 19895125 | 19895155 | chr16 | 21666641 | 21666771 | chr16 | 21831621 | 21831957 |
| chr16 | 21839328 | 21839369 | chr16 | 22326397 | 22326427 | chr16 | 22824701 | 22825076 |
| chr16 | 22825327 | 22825469 | chr16 | 22825886 | 22826081 | chr16 | 23313464 | 23313522 |
| chr16 | 23313780 | 23313836 | chr16 | 23706412 | 23706520 | chr16 | 23766097 | 23766130 |
| chr16 | 23847311 | 23847511 | chr16 | 23847789 | 23847874 | chr16 | 23847934 | 23847956 |
| chr16 | 24127295 | 24127338 | chr16 | 24172241 | 24172271 | chr16 | 24180710 | 24180760 |
| chr16 | 24267115 | 24267144 | chr16 | 24267485 | 24267578 | chr16 | 25266537 | 25266573 |
| chr16 | 25542437 | 25542452 | chr16 | 25702955 | 25702992 | chr16 | 25703685 | 25704122 |
| chr16 | 25704390 | 25704628 | chr16 | 25921574 | 25921604 | chr16 | 26664757 | 26664775 |
| chr16 | 27459938 | 27460074 | chr16 | 27749857 | 27750033 | chr16 | 28074176 | 28074254 |
| chr16 | 28074418 | 28074684 | chr16 | 28074959 | 28075197 | chr16 | 28877839 | 28877883 |
| chr16 | 28891040 | 28891072 | chr16 | 29119008 | 29119058 | chr16 | 29153284 | 29153320 |
| chr16 | 29244900 | 29244997 | chr16 | 29830871 | 29831078 | chr16 | 29888624 | 29888658 |
| chr16 | 30017330 | 30017447 | chr16 | 30116285 | 30116315 | chr16 | 30124691 | 30124861 |
| chr16 | 30804457 | 30804472 | chr16 | 30826362 | 30826509 | chr16 | 30907010 | 30907049 |
| chr16 | 30907109 | 30907148 | chr16 | 31227914 | 31228313 | chr16 | 31384593 | 31384623 |
| chr16 | 31446873 | 31447096 | chr16 | 31498008 | 31498087 | chr16 | 31500544 | 31500673 |
| chr16 | 31580560 | 31581036 | chr16 | 46721567 | 46721707 | chr16 | 47177525 | 47177606 |
| chr16 | 48641663 | 48641693 | chr16 | 48845120 | 48845125 | chr16 | 49309170 | 49309262 |
| chr16 | 49311523 | 49311989 | chr16 | 49312033 | 49312299 | chr16 | 49313363 | 49313710 |
| chr16 | 49314022 | 49314118 | chr16 | 49314419 | 49314561 | chr16 | 49314784 | 49314821 |
| chr16 | 49315276 | 49315306 | chr16 | 49315919 | 49316315 | chr16 | 49316509 | 49316580 |
| chr16 | 49638060 | 49638090 | chr16 | 50335767 | 50335797 | chr16 | 51183964 | 51184406 |
| chr16 | 51184807 | 51184957 | chr16 | 51185055 | 51185291 | chr16 | 51185844 | 51185964 |
| chr16 | 51186026 | 51186280 | chr16 | 51186596 | 51186939 | chr16 | 51188697 | 51188711 |
| chr16 | 51189922 | 51190037 | chr16 | 51190122 | 51190215 | chr16 | 53467363 | 53467395 |
| chr16 | 53563622 | 53563654 | chr16 | 54128645 | 54128713 | chr16 | 54318898 | 54318988 |
| chr16 | 54319420 | 54319468 | chr16 | 54321638 | 54321818 | chr16 | 54324999 | 54325131 |
| chr16 | 54628691 | 54628867 | chr16 | 54964948 | 54965114 | chr16 | 54966830 | 54967264 |
| chr16 | 54971400 | 54971430 | chr16 | 55090666 | 55090861 | chr16 | 55357926 | 55357940 |
| chr16 | 55357992 | 55358086 | chr16 | 55358316 | 55358350 | chr16 | 55358798 | 55359071 |
| chr16 | 55363009 | 55363223 | chr16 | 55364716 | 55364843 | chr16 | 55365103 | 55365218 |
| chr16 | 55404999 | 55405214 | chr16 | 55689886 | 55689915 | chr16 | 55690115 | 55690379 |
| chr16 | 55690454 | 55690576 | chr16 | 55690762 | 55690809 | chr16 | 56224557 | 56224832 |
| chr16 | 56228370 | 56228416 | chr16 | 56228578 | 56228581 | chr16 | 56651094 | 56651123 |
| chr16 | 56651239 | 56651275 | chr16 | 56659175 | 56659673 | chr16 | 56672158 | 56672172 |
| chr16 | 56672222 | 56672385 | chr16 | 56672514 | 56672654 | chr16 | 56672656 | 56672685 |
| chr16 | 56709837 | 56709892 | chr16 | 56709950 | 56710030 | chr16 | 57222686 | 57222709 |
| chr16 | 57318379 | 57318412 | chr16 | 57935454 | 57935605 | chr16 | 58018634 | 58018845 |
| chr16 | 58019225 | 58019430 | chr16 | 58120795 | 58120961 | chr16 | 58497221 | 58497335 |
| chr16 | 58497752 | 58497829 | chr16 | 58498175 | 58498204 | chr16 | 58498570 | 58498724 |
| chr16 | 58521708 | 58521737 | chr16 | 58534666 | 58534695 | chr16 | 58545487 | 58545516 |
| chr16 | 58550489 | 58550519 | chr16 | 58969757 | 58969792 | chr16 | 62068463 | 62068517 |
| chr16 | 62068952 | 62068982 | chr16 | 62070743 | 62070773 | chr16 | 65154933 | 65155091 |
| chr16 | 65156385 | 65156489 | chr16 | 66461786 | 66461840 | chr16 | 66612882 | 66613095 |
| chr16 | 66613335 | 66613369 | chr16 | 67197698 | 67197769 | chr16 | 67198009 | 67198039 |
| chr16 | 67198917 | 67198957 | chr16 | 67241204 | 67241234 | chr16 | 67313865 | 67313895 |
| chr16 | 68481486 | 68481543 | chr16 | 68482808 | 68482941 | chr16 | 68544259 | 68544378 |

TABLE 13-continued

Pan Cancer #3

| chr | start | end | chr | start | end | chr | start | end |
|---|---|---|---|---|---|---|---|---|
| chr16 | 68676408 | 68676604 | chr16 | 68676842 | 68676984 | chr16 | 68770835 | 68771298 |
| chr16 | 68844158 | 68844187 | chr16 | 68846033 | 68846062 | chr16 | 68856078 | 68856107 |
| chr16 | 68876782 | 68876859 | chr16 | 69969260 | 69969290 | chr16 | 70595535 | 70595700 |
| chr16 | 70794492 | 70794633 | chr16 | 71460027 | 71460088 | chr16 | 71460271 | 71460351 |
| chr16 | 71507775 | 71507791 | chr16 | 71715779 | 71715809 | chr16 | 72957763 | 72957795 |
| chr16 | 75019751 | 75019781 | chr16 | 77247440 | 77247470 | chr16 | 77468261 | 77468457 |
| chr16 | 77822589 | 77822874 | chr16 | 78079969 | 78080054 | chr16 | 79623602 | 79623616 |
| chr16 | 79623798 | 79623914 | chr16 | 80837962 | 80838143 | chr16 | 80966399 | 80966431 |
| chr16 | 81564199 | 81564229 | chr16 | 81929362 | 81929392 | chr16 | 81946246 | 81946275 |
| chr16 | 81962167 | 81962196 | chr16 | 82660360 | 82660496 | chr16 | 82660712 | 82660741 |
| chr16 | 84074836 | 84074871 | chr16 | 84153364 | 84153394 | chr16 | 84402244 | 84402319 |
| chr16 | 84519974 | 84520010 | chr16 | 84651793 | 84651822 | chr16 | 84823626 | 84823656 |
| chr16 | 84853288 | 84853376 | chr16 | 85075434 | 85075553 | chr16 | 85317850 | 85317882 |
| chr16 | 85485747 | 85485855 | chr16 | 85497445 | 85497475 | chr16 | 85517345 | 85517521 |
| chr16 | 85651520 | 85651550 | chr16 | 85678639 | 85678761 | chr16 | 85684308 | 85684457 |
| chr16 | 85699689 | 85699921 | chr16 | 85932828 | 85932858 | chr16 | 86320354 | 86320391 |
| chr16 | 86320755 | 86320800 | chr16 | 86321020 | 86321068 | chr16 | 86530947 | 86530992 |
| chr16 | 86531017 | 86531046 | chr16 | 86531375 | 86531480 | chr16 | 86531528 | 86531573 |
| chr16 | 86541591 | 86541968 | chr16 | 86542373 | 86542457 | chr16 | 86544191 | 86544557 |
| chr16 | 86571984 | 86572014 | chr16 | 86599481 | 86599844 | chr16 | 86600483 | 86600686 |
| chr16 | 86600958 | 86601015 | chr16 | 86601286 | 86601539 | chr16 | 86602038 | 86602514 |
| chr16 | 87092439 | 87092553 | chr16 | 87525622 | 87525701 | chr16 | 87635103 | 87635133 |
| chr16 | 87636627 | 87636907 | chr16 | 87714272 | 87714381 | chr16 | 87723735 | 87724098 |
| chr16 | 88007072 | 88007090 | chr16 | 88106322 | 88106398 | chr16 | 88164401 | 88164468 |
| chr16 | 88498241 | 88498760 | chr16 | 88504058 | 88504315 | chr16 | 88506346 | 88506526 |
| chr16 | 88512427 | 88512529 | chr16 | 88543428 | 88543458 | chr16 | 88550263 | 88550483 |
| chr16 | 88603696 | 88603760 | chr16 | 88623960 | 88624167 | chr16 | 88711337 | 88711507 |
| chr16 | 88757466 | 88757496 | chr16 | 88879949 | 88880097 | chr16 | 88883238 | 88883377 |
| chr16 | 88941058 | 88941141 | chr16 | 88942119 | 88942160 | chr16 | 88943559 | 88944024 |
| chr16 | 88945815 | 88945995 | chr16 | 88955249 | 88955368 | chr16 | 88956230 | 88956399 |
| chr16 | 88957350 | 88957857 | chr16 | 88958397 | 88958431 | chr16 | 88963277 | 88963763 |
| chr16 | 88966303 | 88966588 | chr16 | 88968709 | 88968789 | chr16 | 88978024 | 88978072 |
| chr16 | 88993078 | 88993230 | chr16 | 88999617 | 88999647 | chr16 | 89000168 | 89000204 |
| chr16 | 89001094 | 89001124 | chr16 | 89007520 | 89007558 | chr16 | 89007880 | 89007995 |
| chr16 | 89008562 | 89008592 | chr16 | 89047717 | 89047747 | chr16 | 89072503 | 89072774 |
| chr16 | 89086109 | 89086197 | chr16 | 89107675 | 89107732 | chr16 | 89109385 | 89109415 |
| chr16 | 89120038 | 89120319 | chr16 | 89120708 | 89120864 | chr16 | 89138016 | 89138060 |
| chr16 | 89220327 | 89220398 | chr16 | 89220655 | 89220922 | chr16 | 89240843 | 89240873 |
| chr16 | 89254653 | 89254742 | chr16 | 89267334 | 89267364 | chr16 | 89267808 | 89267824 |
| chr16 | 89558610 | 89558703 | chr16 | 89584337 | 89584417 | chr16 | 89883972 | 89884185 |
| chr16 | 89884966 | 89884994 | chr16 | 89885114 | 89885142 | chr16 | 89900124 | 89900180 |
| chr16 | 89900455 | 89900526 | chr17 | 415134 | 415163 | chr17 | 556252 | 556282 |
| chr17 | 617001 | 617033 | chr17 | 1082884 | 1083002 | chr17 | 1174274 | 1174361 |
| chr17 | 1174385 | 1174413 | chr17 | 1494550 | 1494613 | chr17 | 1536116 | 1536146 |
| chr17 | 1545976 | 1545999 | chr17 | 1546299 | 1546442 | chr17 | 1623703 | 1623735 |
| chr17 | 1959468 | 1959520 | chr17 | 2207801 | 2207981 | chr17 | 2208041 | 2208063 |
| chr17 | 2220962 | 2221059 | chr17 | 2250051 | 2250081 | chr17 | 2278801 | 2278925 |
| chr17 | 2607905 | 2607986 | chr17 | 2663935 | 2664032 | chr17 | 3438914 | 3438937 |
| chr17 | 3657502 | 3657553 | chr17 | 3658490 | 3658519 | chr17 | 3658849 | 3658930 |
| chr17 | 3658990 | 3659011 | chr17 | 4544607 | 4544710 | chr17 | 4693354 | 4693388 |
| chr17 | 4699211 | 4699252 | chr17 | 4891276 | 4891305 | chr17 | 4891527 | 4891556 |
| chr17 | 5000428 | 5000790 | chr17 | 5019637 | 5019662 | chr17 | 5019738 | 5019761 |
| chr17 | 6616637 | 6616686 | chr17 | 6616911 | 6617173 | chr17 | 6679190 | 6679296 |
| chr17 | 6946107 | 6946141 | chr17 | 7348885 | 7348997 | chr17 | 7368947 | 7369139 |
| chr17 | 7471610 | 7471630 | chr17 | 7555117 | 7555425 | chr17 | 7572957 | 7573018 |
| chr17 | 7573968 | 7574028 | chr17 | 7576847 | 7577167 | chr17 | 7577504 | 7577604 |
| chr17 | 7578164 | 7578570 | chr17 | 7579285 | 7579880 | chr17 | 7906254 | 7906535 |
| chr17 | 7906832 | 7906861 | chr17 | 8104145 | 8104173 | chr17 | 8230335 | 8230694 |
| chr17 | 8534493 | 8534582 | chr17 | 8774623 | 8774653 | chr17 | 8868620 | 8868667 |
| chr17 | 8868815 | 8869385 | chr17 | 8906266 | 8906518 | chr17 | 8906993 | 8907575 |
| chr17 | 8926060 | 8926263 | chr17 | 10101084 | 10101109 | chr17 | 10101132 | 10101447 |
| chr17 | 10102415 | 10102665 | chr17 | 11144926 | 11144989 | chr17 | 11984693 | 11984722 |
| chr17 | 11998944 | 11998973 | chr17 | 12013726 | 12013755 | chr17 | 12016550 | 12016630 |
| chr17 | 12028618 | 12028647 | chr17 | 13504195 | 13504195 | chr17 | 13504557 | 13504681 |
| chr17 | 13505002 | 13505188 | chr17 | 13505418 | 13505572 | chr17 | 14201041 | 14201181 |
| chr17 | 14204212 | 14204242 | chr17 | 14204527 | 14204620 | chr17 | 15245050 | 15245139 |
| chr17 | 16282251 | 16282300 | chr17 | 16284630 | 16285065 | chr17 | 16326144 | 16326216 |
| chr17 | 16570699 | 16570794 | chr17 | 17062574 | 17062763 | chr17 | 17117365 | 17117395 |
| chr17 | 17123963 | 17123993 | chr17 | 17398404 | 17398440 | chr17 | 17719242 | 17719355 |
| chr17 | 18163055 | 18163325 | chr17 | 18538185 | 18538275 | chr17 | 18817198 | 18817241 |
| chr17 | 20238152 | 20238175 | chr17 | 20468021 | 20468090 | chr17 | 20817896 | 20817917 |
| chr17 | 25620573 | 25620715 | chr17 | 25676959 | 25676989 | chr17 | 25680264 | 25680294 |
| chr17 | 25907750 | 25907780 | chr17 | 26263183 | 26263223 | chr17 | 26554634 | 26554705 |
| chr17 | 26961770 | 26961833 | chr17 | 27036998 | 27037023 | chr17 | 27038649 | 27038685 |
| chr17 | 27056837 | 27056857 | chr17 | 27170162 | 27170191 | chr17 | 27181276 | 27181371 |
| chr17 | 27332453 | 27332660 | chr17 | 27716114 | 27716137 | chr17 | 27716197 | 27716220 |

TABLE 13-continued

Pan Cancer #3

| chr | start | end | chr | start | end | chr | start | end |
|---|---|---|---|---|---|---|---|---|
| chr17 | 27940591 | 27940911 | chr17 | 28562701 | 28562765 | chr17 | 29232244 | 29232267 |
| chr17 | 29249717 | 29249930 | chr17 | 29298080 | 29298581 | chr17 | 29508761 | 29508790 |
| chr17 | 29541527 | 29541556 | chr17 | 29562732 | 29562761 | chr17 | 29718215 | 29718269 |
| chr17 | 29719187 | 29719242 | chr17 | 30243768 | 30243907 | chr17 | 30250325 | 30250345 |
| chr17 | 30568137 | 30568174 | chr17 | 31618425 | 31619319 | chr17 | 31619951 | 31620026 |
| chr17 | 32484020 | 32484049 | chr17 | 32906379 | 32906555 | chr17 | 32906599 | 32906636 |
| chr17 | 32906987 | 32907146 | chr17 | 32907652 | 32907753 | chr17 | 32908132 | 32908146 |
| chr17 | 32908171 | 32908374 | chr17 | 32908647 | 32908931 | chr17 | 33288229 | 33288351 |
| chr17 | 33288890 | 33288988 | chr17 | 33672916 | 33672986 | chr17 | 33877286 | 33877303 |
| chr17 | 33917239 | 33917268 | chr17 | 35165645 | 35165691 | chr17 | 35165986 | 35166016 |
| chr17 | 35285542 | 35285666 | chr17 | 35290388 | 35290655 | chr17 | 35291320 | 35291354 |
| chr17 | 35291829 | 35291898 | chr17 | 35291921 | 35292626 | chr17 | 35293704 | 35294154 |
| chr17 | 35294461 | 35294505 | chr17 | 35295047 | 35295160 | chr17 | 35296143 | 35296292 |
| chr17 | 35296728 | 35296888 | chr17 | 35297619 | 35298153 | chr17 | 35299251 | 35299443 |
| chr17 | 35299601 | 35299965 | chr17 | 35300261 | 35300712 | chr17 | 35300813 | 35300854 |
| chr17 | 35303340 | 35303535 | chr17 | 35872722 | 35872861 | chr17 | 36103021 | 36103326 |
| chr17 | 36103571 | 36103601 | chr17 | 36104218 | 36104550 | chr17 | 36104644 | 36104779 |
| chr17 | 36105223 | 36105349 | chr17 | 36105459 | 36105596 | chr17 | 36715772 | 36715967 |
| chr17 | 37192167 | 37192201 | chr17 | 37321186 | 37321624 | chr17 | 37321788 | 37321972 |
| chr17 | 37366337 | 37366552 | chr17 | 37369180 | 37369210 | chr17 | 37381011 | 37381429 |
| chr17 | 37381571 | 37381726 | chr17 | 37381826 | 37381850 | chr17 | 37382146 | 37382248 |
| chr17 | 37484095 | 37484128 | chr17 | 37757153 | 37757217 | chr17 | 37760488 | 37760561 |
| chr17 | 37761997 | 37762334 | chr17 | 37868190 | 37868294 | chr17 | 37879568 | 37879615 |
| chr17 | 37880205 | 37880276 | chr17 | 37880971 | 37881018 | chr17 | 37881318 | 37881631 |
| chr17 | 38179397 | 38179430 | chr17 | 38347560 | 38347615 | chr17 | 38474363 | 38474502 |
| chr17 | 38497616 | 38497645 | chr17 | 38498083 | 38498112 | chr17 | 38504087 | 38504116 |
| chr17 | 38510555 | 38510584 | chr17 | 39682502 | 39682711 | chr17 | 40332943 | 40333226 |
| chr17 | 40400867 | 40401031 | chr17 | 40464278 | 40464317 | chr17 | 40464517 | 40464607 |
| chr17 | 40474467 | 40474496 | chr17 | 40826197 | 40826226 | chr17 | 40837022 | 40837051 |
| chr17 | 40837287 | 40837383 | chr17 | 40838982 | 40839022 | chr17 | 40975575 | 40975677 |
| chr17 | 41177394 | 41177459 | chr17 | 41197714 | 41197743 | chr17 | 41201163 | 41201192 |
| chr17 | 41203073 | 41203102 | chr17 | 41209064 | 41209114 | chr17 | 41215890 | 41215961 |
| chr17 | 41267731 | 41267775 | chr17 | 41276031 | 41276075 | chr17 | 41277259 | 41277721 |
| chr17 | 41278621 | 41278700 | chr17 | 41651850 | 41651880 | chr17 | 41791460 | 41791489 |
| chr17 | 41791665 | 41791694 | chr17 | 42030329 | 42030750 | chr17 | 42061336 | 42061381 |
| chr17 | 42082522 | 42082557 | chr17 | 42084361 | 42084626 | chr17 | 42092190 | 42092220 |
| chr17 | 42331626 | 42331659 | chr17 | 42393842 | 42394024 | chr17 | 42402884 | 42402917 |
| chr17 | 42580695 | 42580793 | chr17 | 42587332 | 42587355 | chr17 | 42635295 | 42635760 |
| chr17 | 42733711 | 42733884 | chr17 | 42787579 | 42787616 | chr17 | 42907564 | 42907630 |
| chr17 | 42907655 | 42907951 | chr17 | 43001891 | 43001946 | chr17 | 43044658 | 43044688 |
| chr17 | 43045039 | 43045116 | chr17 | 43046260 | 43046385 | chr17 | 43339109 | 43339333 |
| chr17 | 43339609 | 43339899 | chr17 | 43974256 | 43974358 | chr17 | 44897416 | 44897445 |
| chr17 | 45331014 | 45331313 | chr17 | 45810850 | 45811341 | chr17 | 45867315 | 45867460 |
| chr17 | 46125007 | 46125061 | chr17 | 46567618 | 46567655 | chr17 | 46619540 | 46619569 |
| chr17 | 46620494 | 46621094 | chr17 | 46621353 | 46621458 | chr17 | 46621856 | 46621909 |
| chr17 | 46655148 | 46655178 | chr17 | 46655451 | 46655998 | chr17 | 46656058 | 46656704 |
| chr17 | 46659429 | 46659859 | chr17 | 46663743 | 46663824 | chr17 | 46663856 | 46663887 |
| chr17 | 46674873 | 46674970 | chr17 | 46675170 | 46675600 | chr17 | 46690467 | 46690664 |
| chr17 | 46691505 | 46691592 | chr17 | 46691805 | 46691818 | chr17 | 46691988 | 46692110 |
| chr17 | 46692439 | 46692606 | chr17 | 46710946 | 46710989 | chr17 | 46713959 | 46714072 |
| chr17 | 46795641 | 46796373 | chr17 | 46796499 | 46796637 | chr17 | 46796850 | 46797213 |
| chr17 | 46797275 | 46797582 | chr17 | 46799625 | 46799896 | chr17 | 46800601 | 46800668 |
| chr17 | 46800961 | 46801047 | chr17 | 46801109 | 46801416 | chr17 | 46802459 | 46802911 |
| chr17 | 46802994 | 46803286 | chr17 | 46804107 | 46804428 | chr17 | 46810416 | 46810958 |
| chr17 | 46811354 | 46811499 | chr17 | 46816282 | 46816730 | chr17 | 46824224 | 46824275 |
| chr17 | 46824359 | 46825054 | chr17 | 46825284 | 46825514 | chr17 | 46826930 | 46827127 |
| chr17 | 46827330 | 46827501 | chr17 | 46827626 | 46827756 | chr17 | 46829498 | 46829579 |
| chr17 | 46829979 | 46830110 | chr17 | 46831779 | 46832325 | chr17 | 46832490 | 46832639 |
| chr17 | 47072805 | 47073028 | chr17 | 47073104 | 47073327 | chr17 | 47073389 | 47073465 |
| chr17 | 47073988 | 47074228 | chr17 | 47074561 | 47074895 | chr17 | 47075160 | 47075364 |
| chr17 | 47075715 | 47075734 | chr17 | 47075880 | 47076055 | chr17 | 47574090 | 47574149 |
| chr17 | 47657544 | 47657583 | chr17 | 47865514 | 47865555 | chr17 | 47987525 | 47987619 |
| chr17 | 47987930 | 47988114 | chr17 | 48041152 | 48041320 | chr17 | 48041672 | 48041721 |
| chr17 | 48042039 | 48042069 | chr17 | 48042435 | 48042647 | chr17 | 48042751 | 48042956 |
| chr17 | 48048952 | 48049059 | chr17 | 48049307 | 48050526 | chr17 | 48071020 | 48071050 |
| chr17 | 48071807 | 48071894 | chr17 | 48473206 | 48473236 | chr17 | 48545804 | 48545950 |
| chr17 | 48589801 | 48589831 | chr17 | 48612223 | 48612308 | chr17 | 48636581 | 48637136 |
| chr17 | 48653128 | 48653158 | chr17 | 48799843 | 48799866 | chr17 | 49027838 | 49027876 |
| chr17 | 49229485 | 49229605 | chr17 | 50235216 | 50235258 | chr17 | 50235631 | 50235952 |
| chr17 | 51901004 | 51901034 | chr17 | 53341252 | 53341536 | chr17 | 53342876 | 53343089 |
| chr17 | 53922649 | 53922790 | chr17 | 54674986 | 54675272 | chr17 | 54755969 | 54755990 |
| chr17 | 55122813 | 55122842 | chr17 | 55213641 | 55213670 | chr17 | 55962573 | 55962841 |
| chr17 | 56092600 | 56092638 | chr17 | 56234405 | 56234743 | chr17 | 56326949 | 56326994 |
| chr17 | 56327271 | 56327301 | chr17 | 56471121 | 56471144 | chr17 | 56833127 | 56833221 |
| chr17 | 56833707 | 56834000 | chr17 | 56834020 | 56834075 | chr17 | 56834306 | 56834375 |
| chr17 | 57297027 | 57297129 | chr17 | 58216613 | 58216836 | chr17 | 58216866 | 58217298 |

TABLE 13-continued

Pan Cancer #3

| chr | start | end | chr | start | end | chr | start | end |
|---|---|---|---|---|---|---|---|---|
| chr17 | 58217357 | 58217551 | chr17 | 58218765 | 58218993 | chr17 | 58227374 | 58227397 |
| chr17 | 58498697 | 58499314 | chr17 | 59474157 | 59474246 | chr17 | 59474833 | 59475100 |
| chr17 | 59475678 | 59476023 | chr17 | 59476083 | 59476127 | chr17 | 59476410 | 59476635 |
| chr17 | 59478147 | 59478602 | chr17 | 59481657 | 59481678 | chr17 | 59488101 | 59488423 |
| chr17 | 59528876 | 59529150 | chr17 | 59529254 | 59529264 | chr17 | 59529844 | 59530352 |
| chr17 | 59531667 | 59532017 | chr17 | 59533875 | 59534405 | chr17 | 59534751 | 59534781 |
| chr17 | 59535137 | 59535219 | chr17 | 59539236 | 59539601 | chr17 | 59924556 | 59924585 |
| chr17 | 59937192 | 59937236 | chr17 | 61778235 | 61778248 | chr17 | 61817856 | 61817955 |
| chr17 | 61926172 | 61926324 | chr17 | 61926508 | 61926603 | chr17 | 62028596 | 62028790 |
| chr17 | 62777335 | 62777450 | chr17 | 62777746 | 62777791 | chr17 | 64672366 | 64672544 |
| chr17 | 66420718 | 66420748 | chr17 | 66596471 | 66596525 | chr17 | 66596984 | 66597021 |
| chr17 | 67410381 | 67410397 | chr17 | 68164733 | 68164928 | chr17 | 70026543 | 70026667 |
| chr17 | 70112916 | 70113566 | chr17 | 70113648 | 70114018 | chr17 | 70114153 | 70114517 |
| chr17 | 70215683 | 70216306 | chr17 | 70216393 | 70216585 | chr17 | 71641544 | 71641683 |
| chr17 | 71948439 | 71948863 | chr17 | 72270286 | 72270415 | chr17 | 72321933 | 72321975 |
| chr17 | 72322363 | 72322557 | chr17 | 72353213 | 72353259 | chr17 | 72353417 | 72353550 |
| chr17 | 72427853 | 72427999 | chr17 | 72428344 | 72428381 | chr17 | 72491378 | 72491395 |
| chr17 | 72667337 | 72667481 | chr17 | 72849010 | 72849079 | chr17 | 72857038 | 72857368 |
| chr17 | 72862371 | 72862460 | chr17 | 72920796 | 72921032 | chr17 | 73031637 | 73031666 |
| chr17 | 73115884 | 73115914 | chr17 | 73215289 | 73215386 | chr17 | 73545998 | 73546299 |
| chr17 | 73586015 | 73586418 | chr17 | 73608306 | 73608336 | chr17 | 73636144 | 73636337 |
| chr17 | 73808631 | 73808671 | chr17 | 73827213 | 73827243 | chr17 | 74028346 | 74028413 |
| chr17 | 74047797 | 74048020 | chr17 | 74070372 | 74070479 | chr17 | 74071445 | 74071481 |
| chr17 | 74071689 | 74071729 | chr17 | 74072999 | 74073036 | chr17 | 74073269 | 74073433 |
| chr17 | 74087118 | 74087185 | chr17 | 74390363 | 74390393 | chr17 | 74533844 | 74534310 |
| chr17 | 74581182 | 74581221 | chr17 | 74732944 | 74732973 | chr17 | 74865053 | 74865192 |
| chr17 | 74865698 | 74866243 | chr17 | 75137660 | 75137887 | chr17 | 75207514 | 75207630 |
| chr17 | 75207839 | 75207987 | chr17 | 75276054 | 75276083 | chr17 | 75276413 | 75276442 |
| chr17 | 75277348 | 75277659 | chr17 | 75278020 | 75278049 | chr17 | 75279105 | 75279134 |
| chr17 | 75282025 | 75282154 | chr17 | 75315512 | 75315681 | chr17 | 75316368 | 75316397 |
| chr17 | 75317170 | 75317199 | chr17 | 75347755 | 75347784 | chr17 | 75368735 | 75369238 |
| chr17 | 75369440 | 75369457 | chr17 | 75369493 | 75369860 | chr17 | 75370269 | 75370316 |
| chr17 | 75370596 | 75370625 | chr17 | 75373312 | 75373341 | chr17 | 75385071 | 75385446 |
| chr17 | 75405827 | 75405856 | chr17 | 75417150 | 75417179 | chr17 | 75523142 | 75523272 |
| chr17 | 75524636 | 75525194 | chr17 | 75733978 | 75734244 | chr17 | 75797111 | 75797179 |
| chr17 | 76125196 | 76125225 | chr17 | 76126434 | 76126463 | chr17 | 76128466 | 76128663 |
| chr17 | 76130124 | 76130153 | chr17 | 76130481 | 76130510 | chr17 | 76137951 | 76138190 |
| chr17 | 76138498 | 76138622 | chr17 | 76187407 | 76187506 | chr17 | 76207342 | 76207372 |
| chr17 | 76227849 | 76228161 | chr17 | 76228214 | 76228357 | chr17 | 76404615 | 76404659 |
| chr17 | 76877177 | 76877212 | chr17 | 76974447 | 76974499 | chr17 | 77084518 | 77084727 |
| chr17 | 77105055 | 77105198 | chr17 | 77145129 | 77145242 | chr17 | 77179113 | 77179278 |
| chr17 | 77179630 | 77179776 | chr17 | 77394706 | 77394850 | chr17 | 77776827 | 77776995 |
| chr17 | 77777053 | 77777056 | chr17 | 77777585 | 77777903 | chr17 | 77777944 | 77777961 |
| chr17 | 77778943 | 77779179 | chr17 | 77789474 | 77789500 | chr17 | 77825696 | 77825812 |
| chr17 | 77899664 | 77899693 | chr17 | 77919429 | 77919477 | chr17 | 77924259 | 77924351 |
| chr17 | 78122174 | 78122190 | chr17 | 78194821 | 78194861 | chr17 | 78272278 | 78272313 |
| chr17 | 78447127 | 78447157 | chr17 | 78451931 | 78451953 | chr17 | 78452296 | 78452340 |
| chr17 | 78452681 | 78452833 | chr17 | 78518175 | 78518198 | chr17 | 78599596 | 78599628 |
| chr17 | 78667992 | 78668159 | chr17 | 78874441 | 78874559 | chr17 | 78999625 | 78999654 |
| chr17 | 79058302 | 79058333 | chr17 | 79094182 | 79094245 | chr17 | 79099770 | 79099799 |
| chr17 | 79626617 | 79626703 | chr17 | 79769433 | 79769693 | chr17 | 79813409 | 79813507 |
| chr17 | 79896013 | 79896043 | chr17 | 79945037 | 79945074 | chr17 | 80186260 | 80186289 |
| chr17 | 80197756 | 80197898 | chr17 | 80254266 | 80254296 | chr17 | 80289234 | 80289310 |
| chr17 | 80329709 | 80330000 | chr17 | 80394063 | 80394185 | chr17 | 80394573 | 80394602 |
| chr17 | 80479345 | 80479525 | chr17 | 80491572 | 80491602 | chr17 | 80535382 | 80535487 |
| chr17 | 80571380 | 80571776 | chr17 | 80654983 | 80655013 | chr17 | 80693317 | 80693554 |
| chr17 | 80749244 | 80749276 | chr17 | 80751650 | 80751714 | chr17 | 80794259 | 80794288 |
| chr17 | 80797692 | 80798345 | chr17 | 80832305 | 80832411 | chr17 | 80832712 | 80832796 |
| chr17 | 80859239 | 80859269 | chr17 | 81008618 | 81008826 | chr17 | 81033487 | 81033517 |
| chr17 | 81048993 | 81049023 | chr17 | 81049994 | 81050058 | chr18 | 499367 | 499482 |
| chr18 | 500046 | 500738 | chr18 | 904462 | 904648 | chr18 | 905000 | 905030 |
| chr18 | 905434 | 905615 | chr18 | 906871 | 906907 | chr18 | 907472 | 907594 |
| chr18 | 907912 | 907977 | chr18 | 908454 | 908589 | chr18 | 909487 | 909587 |
| chr18 | 2755854 | 2755878 | chr18 | 2906268 | 2906304 | chr18 | 3214441 | 3214543 |
| chr18 | 3215042 | 3215256 | chr18 | 3499067 | 3499371 | chr18 | 4453964 | 4454163 |
| chr18 | 5133207 | 5133343 | chr18 | 5196576 | 5196959 | chr18 | 5197202 | 5197271 |
| chr18 | 5197330 | 5197347 | chr18 | 5237878 | 5238247 | chr18 | 5628167 | 5628515 |
| chr18 | 5629774 | 5629825 | chr18 | 5630312 | 5630362 | chr18 | 5895023 | 5895205 |
| chr18 | 5895975 | 5896085 | chr18 | 6729952 | 6729993 | chr18 | 6908056 | 6908090 |
| chr18 | 7117665 | 7117804 | chr18 | 7567783 | 7568291 | chr18 | 8608748 | 8608837 |
| chr18 | 8608902 | 8608968 | chr18 | 8612252 | 8612282 | chr18 | 9771586 | 9771753 |
| chr18 | 9912767 | 9912797 | chr18 | 10251324 | 10251348 | chr18 | 10589096 | 10589348 |
| chr18 | 11148969 | 11149045 | chr18 | 11149561 | 11149759 | chr18 | 11149780 | 11149888 |
| chr18 | 11401654 | 11401817 | chr18 | 11689190 | 11689220 | chr18 | 11752128 | 11752379 |
| chr18 | 11752700 | 11752730 | chr18 | 11942728 | 11942753 | chr18 | 12254305 | 12254578 |
| chr18 | 12277243 | 12277273 | chr18 | 12307247 | 12307505 | chr18 | 12307603 | 12307751 |

TABLE 13-continued

Pan Cancer #3

| chr | start | end | chr | start | end | chr | start | end |
|---|---|---|---|---|---|---|---|---|
| chr18 | 12376086 | 12376129 | chr18 | 13132080 | 13132223 | chr18 | 13824025 | 13824102 |
| chr18 | 13826393 | 13826536 | chr18 | 13868713 | 13868919 | chr18 | 15198149 | 15198248 |
| chr18 | 18822392 | 18823274 | chr18 | 19750308 | 19750346 | chr18 | 20911541 | 20911571 |
| chr18 | 21269349 | 21269390 | chr18 | 21269659 | 21269740 | chr18 | 21719351 | 21719568 |
| chr18 | 22929081 | 22929095 | chr18 | 22929187 | 22929718 | chr18 | 22929927 | 22930559 |
| chr18 | 22930790 | 22931178 | chr18 | 23686462 | 23686540 | chr18 | 24127748 | 24128030 |
| chr18 | 24130809 | 24130946 | chr18 | 24131099 | 24131187 | chr18 | 24764951 | 24765168 |
| chr18 | 25755593 | 25755655 | chr18 | 25756010 | 25756040 | chr18 | 25756495 | 25756729 |
| chr18 | 25757187 | 25757452 | chr18 | 25757787 | 25757824 | chr18 | 25758129 | 25758141 |
| chr18 | 28620899 | 28620955 | chr18 | 28621034 | 28621097 | chr18 | 28621328 | 28621393 |
| chr18 | 28621636 | 28621932 | chr18 | 28622419 | 28622488 | chr18 | 30349740 | 30349781 |
| chr18 | 31020495 | 31020510 | chr18 | 31158093 | 31158158 | chr18 | 31739035 | 31739469 |
| chr18 | 31802132 | 31802167 | chr18 | 31802938 | 31802968 | chr18 | 31803438 | 31803472 |
| chr18 | 31902793 | 31902945 | chr18 | 32073908 | 32074086 | chr18 | 32557832 | 32557864 |
| chr18 | 32847598 | 32847642 | chr18 | 32957803 | 32957821 | chr18 | 33078363 | 33078393 |
| chr18 | 33078633 | 33078662 | chr18 | 33877683 | 33877754 | chr18 | 35065072 | 35065145 |
| chr18 | 35144845 | 35144936 | chr18 | 35144969 | 35145465 | chr18 | 35145985 | 35146036 |
| chr18 | 35146062 | 35146241 | chr18 | 35147487 | 35147569 | chr18 | 43914211 | 43914278 |
| chr18 | 44259903 | 44259990 | chr18 | 44336034 | 44336449 | chr18 | 44337444 | 44337617 |
| chr18 | 44337650 | 44337841 | chr18 | 44773060 | 44773116 | chr18 | 44773592 | 44773966 |
| chr18 | 44774406 | 44774890 | chr18 | 44775380 | 44775554 | chr18 | 44776972 | 44777088 |
| chr18 | 44777301 | 44777331 | chr18 | 44777596 | 44777750 | chr18 | 44778049 | 44778326 |
| chr18 | 44781003 | 44781041 | chr18 | 44787781 | 44787846 | chr18 | 44788251 | 44788281 |
| chr18 | 44789474 | 44789514 | chr18 | 44789872 | 44789937 | chr18 | 45058069 | 45058240 |
| chr18 | 46142662 | 46142809 | chr18 | 47720492 | 47720522 | chr18 | 48604773 | 48604802 |
| chr18 | 48636211 | 48636320 | chr18 | 49867303 | 49867399 | chr18 | 52989009 | 52989220 |
| chr18 | 52989741 | 52989882 | chr18 | 53257137 | 53257204 | chr18 | 53446970 | 53447474 |
| chr18 | 53447799 | 53447816 | chr18 | 53989796 | 53989877 | chr18 | 54789070 | 54789256 |
| chr18 | 55019707 | 55019775 | chr18 | 55020655 | 55020698 | chr18 | 55021078 | 55021242 |
| chr18 | 55103381 | 55103411 | chr18 | 55104808 | 55105140 | chr18 | 55105728 | 55105830 |
| chr18 | 55114480 | 55114644 | chr18 | 55850845 | 55850987 | chr18 | 56483918 | 56483938 |
| chr18 | 56815734 | 56815891 | chr18 | 56887076 | 56887424 | chr18 | 56888554 | 56888623 |
| chr18 | 56931541 | 56931583 | chr18 | 56931967 | 56932107 | chr18 | 56932352 | 56932375 |
| chr18 | 56935010 | 56935319 | chr18 | 56936004 | 56936074 | chr18 | 56939113 | 56939174 |
| chr18 | 56939423 | 56939651 | chr18 | 56939764 | 56940170 | chr18 | 56940566 | 56940722 |
| chr18 | 56940955 | 56941244 | chr18 | 56941558 | 56941788 | chr18 | 57363706 | 57363743 |
| chr18 | 57364658 | 57364691 | chr18 | 59000988 | 59001022 | chr18 | 59001301 | 59001343 |
| chr18 | 59001498 | 59001740 | chr18 | 60263661 | 60263895 | chr18 | 60985498 | 60985532 |
| chr18 | 60985593 | 60985732 | chr18 | 61143911 | 61143975 | chr18 | 67067558 | 67067907 |
| chr18 | 67068715 | 67068811 | chr18 | 67069216 | 67069246 | chr18 | 70209148 | 70209205 |
| chr18 | 70210418 | 70210508 | chr18 | 70211626 | 70211666 | chr18 | 70534282 | 70534315 |
| chr18 | 70534428 | 70534731 | chr18 | 70535373 | 70535554 | chr18 | 70535576 | 70535582 |
| chr18 | 70536010 | 70536083 | chr18 | 70536188 | 70536604 | chr18 | 70536833 | 70536871 |
| chr18 | 70537188 | 70537218 | chr18 | 72845833 | 72845863 | chr18 | 73167585 | 73167832 |
| chr18 | 73628019 | 73628068 | chr18 | 74501144 | 74501183 | chr18 | 74755508 | 74755590 |
| chr18 | 74961326 | 74961955 | chr18 | 74962019 | 74962147 | chr18 | 74962970 | 74963545 |
| chr18 | 75335093 | 75335123 | chr18 | 75339231 | 75339340 | chr18 | 75362931 | 75362985 |
| chr18 | 75551271 | 75551301 | chr18 | 75612225 | 75612286 | chr18 | 75999404 | 75999434 |
| chr18 | 76239541 | 76239616 | chr18 | 76501479 | 76501509 | chr18 | 76653631 | 76653661 |
| chr18 | 76686249 | 76686279 | chr18 | 76740102 | 76740223 | chr18 | 77143346 | 77143376 |
| chr18 | 77167824 | 77167854 | chr18 | 77181355 | 77181409 | chr18 | 77194936 | 77194978 |
| chr18 | 77205532 | 77205638 | chr18 | 77285897 | 77286028 | chr18 | 77300326 | 77300483 |
| chr18 | 77309533 | 77309563 | chr18 | 77312866 | 77312927 | chr18 | 77329727 | 77330017 |
| chr18 | 77371430 | 77371547 | chr18 | 77459762 | 77459877 | chr18 | 77543249 | 77543335 |
| chr18 | 77543700 | 77543824 | chr18 | 77548352 | 77548609 | chr18 | 77550206 | 77550367 |
| chr18 | 77558082 | 77558358 | chr18 | 77558831 | 77558930 | chr18 | 77576934 | 77577043 |
| chr18 | 77636591 | 77636621 | chr18 | 78004993 | 78005051 | chr19 | 403538 | 403809 |
| chr19 | 407189 | 407320 | chr19 | 418225 | 418255 | chr19 | 462181 | 462269 |
| chr19 | 468757 | 468787 | chr19 | 485165 | 485394 | chr19 | 549361 | 549451 |
| chr19 | 555608 | 555628 | chr19 | 570156 | 570175 | chr19 | 591365 | 591416 |
| chr19 | 592589 | 592632 | chr19 | 593290 | 593376 | chr19 | 599214 | 599333 |
| chr19 | 752136 | 752359 | chr19 | 869337 | 869394 | chr19 | 883624 | 883791 |
| chr19 | 884018 | 884162 | chr19 | 891516 | 891620 | chr19 | 955757 | 956237 |
| chr19 | 959128 | 959158 | chr19 | 1003305 | 1003384 | chr19 | 1003669 | 1003734 |
| chr19 | 1004915 | 1005441 | chr19 | 1030176 | 1030225 | chr19 | 1047890 | 1047915 |
| chr19 | 1083314 | 1083437 | chr19 | 1156524 | 1156554 | chr19 | 1170185 | 1170230 |
| chr19 | 1171099 | 1171324 | chr19 | 1220422 | 1220610 | chr19 | 1221981 | 1222010 |
| chr19 | 1236474 | 1236678 | chr19 | 1274778 | 1274826 | chr19 | 1308047 | 1308081 |
| chr19 | 1325788 | 1325889 | chr19 | 1401752 | 1401795 | chr19 | 1450319 | 1450390 |
| chr19 | 1496413 | 1496450 | chr19 | 1496654 | 1496674 | chr19 | 1524443 | 1524447 |
| chr19 | 1525605 | 1525960 | chr19 | 1527227 | 1527311 | chr19 | 1754172 | 1754193 |
| chr19 | 1754225 | 1754254 | chr19 | 1754739 | 1754804 | chr19 | 1757416 | 1757615 |
| chr19 | 1762474 | 1762505 | chr19 | 1764293 | 1764339 | chr19 | 1775076 | 1775239 |
| chr19 | 1776376 | 1776534 | chr19 | 1800032 | 1800300 | chr19 | 1807970 | 1808413 |
| chr19 | 2135672 | 2135701 | chr19 | 2251152 | 2251234 | chr19 | 2251611 | 2251715 |
| chr19 | 2252589 | 2252658 | chr19 | 2252984 | 2253735 | chr19 | 2274677 | 2274695 |

TABLE 13-continued

Pan Cancer #3

| chr | start | end | chr | start | end | chr | start | end |
|---|---|---|---|---|---|---|---|---|
| chr19 | 2290253 | 2290271 | chr19 | 2290631 | 2290867 | chr19 | 2302793 | 2302951 |
| chr19 | 2331413 | 2331443 | chr19 | 2513250 | 2513285 | chr19 | 2642877 | 2642947 |
| chr19 | 2683911 | 2684056 | chr19 | 3041417 | 3041447 | chr19 | 3114998 | 3115027 |
| chr19 | 3118927 | 3118956 | chr19 | 3219539 | 3219565 | chr19 | 3296613 | 3296670 |
| chr19 | 3361139 | 3361388 | chr19 | 3562223 | 3562583 | chr19 | 3578138 | 3578223 |
| chr19 | 3659668 | 3659793 | chr19 | 3778130 | 3778394 | chr19 | 3779277 | 3779435 |
| chr19 | 3785649 | 3785835 | chr19 | 3785865 | 3786220 | chr19 | 3821044 | 3821217 |
| chr19 | 3822135 | 3822203 | chr19 | 3834572 | 3834641 | chr19 | 3855407 | 3855595 |
| chr19 | 3966686 | 3966755 | chr19 | 3994540 | 3994568 | chr19 | 4054435 | 4054471 |
| chr19 | 4095471 | 4095514 | chr19 | 4101087 | 4101116 | chr19 | 4110565 | 4110597 |
| chr19 | 4117526 | 4117630 | chr19 | 4305057 | 4305086 | chr19 | 4311273 | 4311412 |
| chr19 | 4548134 | 4548364 | chr19 | 4550246 | 4550330 | chr19 | 4555896 | 4556112 |
| chr19 | 4557098 | 4557235 | chr19 | 4670765 | 4670857 | chr19 | 4789697 | 4789721 |
| chr19 | 4910361 | 4910410 | chr19 | 4944145 | 4944174 | chr19 | 5292812 | 5292844 |
| chr19 | 5338914 | 5339143 | chr19 | 5608519 | 5608569 | chr19 | 5676212 | 5676242 |
| chr19 | 5759744 | 5759774 | chr19 | 5826179 | 5826209 | chr19 | 5910356 | 5910454 |
| chr19 | 5914761 | 5914791 | chr19 | 5914992 | 5915060 | chr19 | 6590325 | 6590478 |
| chr19 | 6658279 | 6658422 | chr19 | 6889423 | 6889439 | chr19 | 7157588 | 7157628 |
| chr19 | 7554718 | 7554749 | chr19 | 7615996 | 7616025 | chr19 | 7635530 | 7635552 |
| chr19 | 7746942 | 7747042 | chr19 | 7747205 | 7747234 | chr19 | 7795012 | 7795244 |
| chr19 | 7853028 | 7853157 | chr19 | 7853361 | 7853460 | chr19 | 8115235 | 8115276 |
| chr19 | 8554173 | 8554218 | chr19 | 8576914 | 8577000 | chr19 | 9420142 | 9420240 |
| chr19 | 9473564 | 9473597 | chr19 | 9473869 | 9474056 | chr19 | 9517609 | 9517771 |
| chr19 | 9608895 | 9609036 | chr19 | 9609319 | 9609436 | chr19 | 9903913 | 9904067 |
| chr19 | 9937369 | 9937386 | chr19 | 10231220 | 10231242 | chr19 | 10246506 | 10246566 |
| chr19 | 10362045 | 10362084 | chr19 | 10398209 | 10398285 | chr19 | 10405972 | 10406159 |
| chr19 | 10406279 | 10406349 | chr19 | 10406806 | 10407029 | chr19 | 10407045 | 10407135 |
| chr19 | 10527165 | 10527243 | chr19 | 10531419 | 10531512 | chr19 | 10531964 | 10531994 |
| chr19 | 10600431 | 10600460 | chr19 | 10602274 | 10602348 | chr19 | 10602565 | 10602864 |
| chr19 | 10610138 | 10610260 | chr19 | 10624751 | 10624852 | chr19 | 10624966 | 10625465 |
| chr19 | 10823678 | 10823721 | chr19 | 11134252 | 11134281 | chr19 | 11138507 | 11138536 |
| chr19 | 11492252 | 11492528 | chr19 | 11591031 | 11591185 | chr19 | 11592710 | 11592750 |
| chr19 | 11593022 | 11593159 | chr19 | 11689460 | 11689564 | chr19 | 11959912 | 11960077 |
| chr19 | 12147437 | 12147461 | chr19 | 12163448 | 12163672 | chr19 | 12163893 | 12163923 |
| chr19 | 12175445 | 12175504 | chr19 | 12175814 | 12176005 | chr19 | 12203028 | 12203656 |
| chr19 | 12267019 | 12267667 | chr19 | 12305839 | 12306193 | chr19 | 12306230 | 12306263 |
| chr19 | 12476492 | 12476556 | chr19 | 12595109 | 12595307 | chr19 | 12595845 | 12595896 |
| chr19 | 12606381 | 12606511 | chr19 | 12750987 | 12751056 | chr19 | 12863412 | 12863520 |
| chr19 | 12952000 | 12952139 | chr19 | 12996169 | 12996280 | chr19 | 13113454 | 13113668 |
| chr19 | 13616696 | 13616956 | chr19 | 13617159 | 13617256 | chr19 | 13618288 | 13618381 |
| chr19 | 13965932 | 13965965 | chr19 | 14085021 | 14085051 | chr19 | 14181305 | 14181846 |
| chr19 | 14584240 | 14584412 | chr19 | 14584537 | 14584775 | chr19 | 14663925 | 14664183 |
| chr19 | 14664479 | 14664561 | chr19 | 15090172 | 15090499 | chr19 | 15121685 | 15121894 |
| chr19 | 15122120 | 15122238 | chr19 | 15288433 | 15288856 | chr19 | 15292384 | 15292499 |
| chr19 | 15342734 | 15343373 | chr19 | 15344107 | 15344130 | chr19 | 16766902 | 16766932 |
| chr19 | 16999599 | 16999782 | chr19 | 17000570 | 17000599 | chr19 | 17007086 | 17007388 |
| chr19 | 17007447 | 17007662 | chr19 | 17008586 | 17008698 | chr19 | 17359350 | 17359459 |
| chr19 | 17392641 | 17392866 | chr19 | 17436061 | 17436203 | chr19 | 17717286 | 17717315 |
| chr19 | 17759224 | 17759423 | chr19 | 17791182 | 17791211 | chr19 | 17943423 | 17943452 |
| chr19 | 17945891 | 17945983 | chr19 | 17947991 | 17948023 | chr19 | 17949094 | 17949123 |
| chr19 | 17958490 | 17958839 | chr19 | 17983537 | 17983665 | chr19 | 18041166 | 18041203 |
| chr19 | 18103711 | 18103741 | chr19 | 18104472 | 18104509 | chr19 | 18271894 | 18271923 |
| chr19 | 18278047 | 18278076 | chr19 | 18331031 | 18331136 | chr19 | 18343439 | 18343569 |
| chr19 | 18343921 | 18343963 | chr19 | 18383251 | 18383351 | chr19 | 18714552 | 18714580 |
| chr19 | 18811560 | 18811804 | chr19 | 18856379 | 18856409 | chr19 | 18872825 | 18872900 |
| chr19 | 18899432 | 18899652 | chr19 | 18901828 | 18902095 | chr19 | 18989821 | 18990281 |
| chr19 | 18994887 | 18995206 | chr19 | 19260030 | 19260101 | chr19 | 19261519 | 19261548 |
| chr19 | 19334831 | 19334915 | chr19 | 19636877 | 19636907 | chr19 | 19645834 | 19645925 |
| chr19 | 19651991 | 19652066 | chr19 | 19729251 | 19729395 | chr19 | 19739172 | 19739428 |
| chr19 | 20011955 | 20011992 | chr19 | 20012052 | 20012149 | chr19 | 20188723 | 20188872 |
| chr19 | 20189410 | 20189438 | chr19 | 21646407 | 21646437 | chr19 | 21688814 | 21688893 |
| chr19 | 21769300 | 21769374 | chr19 | 22018523 | 22018724 | chr19 | 22034356 | 22034421 |
| chr19 | 22034447 | 22034813 | chr19 | 22610635 | 22610700 | chr19 | 22715140 | 22715443 |
| chr19 | 23254189 | 23254219 | chr19 | 23257779 | 23258007 | chr19 | 23258306 | 23258559 |
| chr19 | 23258679 | 23258694 | chr19 | 23299748 | 23299824 | chr19 | 23433143 | 23433296 |
| chr19 | 23456615 | 23456881 | chr19 | 23598300 | 23598326 | chr19 | 24154592 | 24154621 |
| chr19 | 24216975 | 24217023 | chr19 | 29284452 | 29284575 | chr19 | 29505153 | 29505183 |
| chr19 | 30015934 | 30015962 | chr19 | 30016025 | 30016712 | chr19 | 30016914 | 30016928 |
| chr19 | 30017452 | 30017509 | chr19 | 30017578 | 30017721 | chr19 | 30017766 | 30018608 |
| chr19 | 30019145 | 30019610 | chr19 | 30019661 | 30019838 | chr19 | 30020093 | 30020473 |
| chr19 | 30186141 | 30186240 | chr19 | 30215542 | 30215571 | chr19 | 30215753 | 30215782 |
| chr19 | 30252296 | 30252333 | chr19 | 30555329 | 30555376 | chr19 | 30562775 | 30563017 |
| chr19 | 30582601 | 30582649 | chr19 | 30637494 | 30637531 | chr19 | 30703436 | 30703469 |
| chr19 | 30713480 | 30713592 | chr19 | 30713686 | 30713706 | chr19 | 30713909 | 30714047 |
| chr19 | 30714403 | 30714433 | chr19 | 30715402 | 30715766 | chr19 | 30716313 | 30716576 |
| chr19 | 30716953 | 30718149 | chr19 | 30718847 | 30718913 | chr19 | 30719449 | 30720067 |

TABLE 13-continued

Pan Cancer #3

| chr | start | end | chr | start | end | chr | start | end |
|---|---|---|---|---|---|---|---|---|
| chr19 | 30865713 | 30866024 | chr19 | 31804724 | 31804754 | chr19 | 31839838 | 31839873 |
| chr19 | 31841937 | 31842389 | chr19 | 32364365 | 32364403 | chr19 | 32380872 | 32380961 |
| chr19 | 32516399 | 32516516 | chr19 | 32715673 | 32715741 | chr19 | 32898335 | 32898490 |
| chr19 | 33167116 | 33167431 | chr19 | 33468018 | 33468055 | chr19 | 33685544 | 33685581 |
| chr19 | 33792159 | 33792524 | chr19 | 33794675 | 33794744 | chr19 | 34112524 | 34112729 |
| chr19 | 34113367 | 34113587 | chr19 | 34114006 | 34114049 | chr19 | 34533139 | 34533169 |
| chr19 | 34973243 | 34973255 | chr19 | 34973656 | 34973697 | chr19 | 35264085 | 35264119 |
| chr19 | 35396251 | 35396370 | chr19 | 35616341 | 35616397 | chr19 | 35781374 | 35781459 |
| chr19 | 35783136 | 35783231 | chr19 | 35797916 | 35797965 | chr19 | 36048595 | 36048771 |
| chr19 | 36049327 | 36049367 | chr19 | 36049397 | 36049462 | chr19 | 36222432 | 36222534 |
| chr19 | 36250029 | 36250134 | chr19 | 36334979 | 36335147 | chr19 | 36347892 | 36348048 |
| chr19 | 36450106 | 36450295 | chr19 | 36523333 | 36523480 | chr19 | 36736027 | 36736057 |
| chr19 | 36736319 | 36736491 | chr19 | 36822324 | 36822466 | chr19 | 36822558 | 36822892 |
| chr19 | 36909073 | 36909348 | chr19 | 36909624 | 36909935 | chr19 | 37095665 | 37095812 |
| chr19 | 37096488 | 37096575 | chr19 | 37263532 | 37263584 | chr19 | 37264222 | 37264421 |
| chr19 | 37288209 | 37288424 | chr19 | 37288607 | 37288765 | chr19 | 37341761 | 37341962 |
| chr19 | 37407127 | 37407443 | chr19 | 37464048 | 37464567 | chr19 | 37464667 | 37464696 |
| chr19 | 37569289 | 37569554 | chr19 | 37702086 | 37702169 | chr19 | 37808445 | 37808485 |
| chr19 | 37959874 | 37959963 | chr19 | 37997433 | 37998138 | chr19 | 38042365 | 38042693 |
| chr19 | 38085254 | 38086066 | chr19 | 38146062 | 38146247 | chr19 | 38146457 | 38146568 |
| chr19 | 38182884 | 38182959 | chr19 | 38183112 | 38183299 | chr19 | 38308080 | 38308336 |
| chr19 | 38308395 | 38308466 | chr19 | 38441488 | 38441518 | chr19 | 38481044 | 38481217 |
| chr19 | 38747159 | 38747491 | chr19 | 38747748 | 38747767 | chr19 | 38755272 | 38755344 |
| chr19 | 38782559 | 38782589 | chr19 | 38789218 | 38789288 | chr19 | 38873935 | 38873965 |
| chr19 | 38905548 | 38905702 | chr19 | 38974232 | 38974262 | chr19 | 39135434 | 39135454 |
| chr19 | 39306433 | 39306545 | chr19 | 39650791 | 39650967 | chr19 | 39687756 | 39687844 |
| chr19 | 39754874 | 39755232 | chr19 | 39755265 | 39755358 | chr19 | 39816936 | 39817085 |
| chr19 | 39993477 | 39993656 | chr19 | 39997688 | 39997732 | chr19 | 39997749 | 39997813 |
| chr19 | 40006187 | 40006306 | chr19 | 40006576 | 40006639 | chr19 | 40724000 | 40724263 |
| chr19 | 40762943 | 40762972 | chr19 | 40829079 | 40829211 | chr19 | 40829793 | 40830032 |
| chr19 | 40902425 | 40902812 | chr19 | 40951175 | 40951206 | chr19 | 40951679 | 40951762 |
| chr19 | 41018510 | 41019031 | chr19 | 41025539 | 41025683 | chr19 | 41059909 | 41060306 |
| chr19 | 41073587 | 41073677 | chr19 | 41119177 | 41119276 | chr19 | 41119371 | 41119408 |
| chr19 | 41354666 | 41354722 | chr19 | 41641831 | 41641886 | chr19 | 41698787 | 41698920 |
| chr19 | 41919917 | 41919971 | chr19 | 42028502 | 42028549 | chr19 | 42408300 | 42408330 |
| chr19 | 42460961 | 42461113 | chr19 | 42827982 | 42828084 | chr19 | 42856453 | 42856483 |
| chr19 | 42911568 | 42911598 | chr19 | 44203830 | 44203877 | chr19 | 44405908 | 44406087 |
| chr19 | 44599783 | 44599803 | chr19 | 44905499 | 44905529 | chr19 | 44952282 | 44952881 |
| chr19 | 45003211 | 45003323 | chr19 | 45300144 | 45300197 | chr19 | 45570401 | 45570450 |
| chr19 | 45574465 | 45574495 | chr19 | 45574773 | 45574888 | chr19 | 45601380 | 45601410 |
| chr19 | 45655400 | 45655556 | chr19 | 45655648 | 45656363 | chr19 | 45656682 | 45656742 |
| chr19 | 45656791 | 45656913 | chr19 | 45657212 | 45657284 | chr19 | 45810102 | 45810267 |
| chr19 | 45835238 | 45835268 | chr19 | 45888946 | 45889224 | chr19 | 45889316 | 45889397 |
| chr19 | 45997528 | 45997584 | chr19 | 46002048 | 46002320 | chr19 | 46234845 | 46234887 |
| chr19 | 46379914 | 46380148 | chr19 | 46404522 | 46404601 | chr19 | 46916725 | 46916987 |
| chr19 | 46917061 | 46917075 | chr19 | 46930129 | 46930200 | chr19 | 46974552 | 46974608 |
| chr19 | 46992718 | 46992866 | chr19 | 46993164 | 46993260 | chr19 | 46993282 | 46993388 |
| chr19 | 46996501 | 46996514 | chr19 | 46996578 | 46996838 | chr19 | 47152978 | 47152990 |
| chr19 | 47200361 | 47200536 | chr19 | 47776713 | 47776742 | chr19 | 47933311 | 47933732 |
| chr19 | 47951288 | 47951318 | chr19 | 48003607 | 48003714 | chr19 | 48076642 | 48076672 |
| chr19 | 48137171 | 48137307 | chr19 | 48151265 | 48151337 | chr19 | 48614843 | 48614873 |
| chr19 | 48771551 | 48771600 | chr19 | 48800603 | 48800769 | chr19 | 48857808 | 48857831 |
| chr19 | 48902848 | 48902878 | chr19 | 48918100 | 48918379 | chr19 | 49119229 | 49119259 |
| chr19 | 49127373 | 49127674 | chr19 | 49180462 | 49180558 | chr19 | 49256396 | 49256438 |
| chr19 | 49399218 | 49399310 | chr19 | 49402471 | 49402551 | chr19 | 49575460 | 49575474 |
| chr19 | 49890887 | 49890908 | chr19 | 49935736 | 49936174 | chr19 | 49936864 | 49936894 |
| chr19 | 50028397 | 50028530 | chr19 | 50049718 | 50049746 | chr19 | 50216042 | 50216072 |
| chr19 | 50243339 | 50243379 | chr19 | 50304736 | 50304766 | chr19 | 50316244 | 50316468 |
| chr19 | 50353394 | 50353574 | chr19 | 50553680 | 50553709 | chr19 | 50553997 | 50554510 |
| chr19 | 50816431 | 50816474 | chr19 | 50833828 | 50833863 | chr19 | 50898558 | 50898583 |
| chr19 | 50938547 | 50938691 | chr19 | 51041149 | 51041189 | chr19 | 51161225 | 51161255 |
| chr19 | 51162197 | 51162253 | chr19 | 51162428 | 51162527 | chr19 | 51171219 | 51171275 |
| chr19 | 51171828 | 51171860 | chr19 | 51227719 | 51227785 | chr19 | 51228049 | 51228079 |
| chr19 | 51228369 | 51228507 | chr19 | 51304554 | 51304602 | chr19 | 51520423 | 51520453 |
| chr19 | 51715329 | 51715359 | chr19 | 51830845 | 51831002 | chr19 | 51831121 | 51831128 |
| chr19 | 51831360 | 51831390 | chr19 | 51925127 | 51925272 | chr19 | 52097689 | 52097732 |
| chr19 | 52207254 | 52207367 | chr19 | 52222523 | 52222923 | chr19 | 52391235 | 52391264 |
| chr19 | 52452316 | 52452335 | chr19 | 52552104 | 52552119 | chr19 | 52715963 | 52715992 |
| chr19 | 52839588 | 52839717 | chr19 | 52839742 | 52839938 | chr19 | 52872942 | 52873440 |
| chr19 | 52956805 | 52956848 | chr19 | 53028928 | 53028952 | chr19 | 53031185 | 53031215 |
| chr19 | 53073563 | 53073772 | chr19 | 53073820 | 53073987 | chr19 | 53141648 | 53141745 |
| chr19 | 53193858 | 53193893 | chr19 | 53194281 | 53194396 | chr19 | 53204758 | 53204798 |
| chr19 | 53496649 | 53496786 | chr19 | 53496814 | 53496846 | chr19 | 53561668 | 53561733 |
| chr19 | 53635952 | 53636091 | chr19 | 53661647 | 53661865 | chr19 | 53662194 | 53662694 |
| chr19 | 53696414 | 53696580 | chr19 | 53700596 | 53700693 | chr19 | 53757895 | 53758247 |
| chr19 | 53811858 | 53811988 | chr19 | 53836954 | 53836975 | chr19 | 53837377 | 53837432 |

TABLE 13-continued

Pan Cancer #3

| chr | start | end | chr | start | end | chr | start | end |
|---|---|---|---|---|---|---|---|---|
| chr19 | 53970501 | 53970643 | chr19 | 53970968 | 53971039 | chr19 | 53971110 | 53971157 |
| chr19 | 54023887 | 54024196 | chr19 | 54024521 | 54024553 | chr19 | 54024613 | 54024884 |
| chr19 | 54369555 | 54369681 | chr19 | 54411125 | 54411168 | chr19 | 54411556 | 54411586 |
| chr19 | 54412873 | 54412985 | chr19 | 54481771 | 54481968 | chr19 | 54483173 | 54483305 |
| chr19 | 54483365 | 54483546 | chr19 | 54485403 | 54485646 | chr19 | 54485673 | 54485823 |
| chr19 | 54850630 | 54850659 | chr19 | 55598811 | 55598888 | chr19 | 55629883 | 55630028 |
| chr19 | 56159273 | 56159499 | chr19 | 56189937 | 56189966 | chr19 | 56201643 | 56201938 |
| chr19 | 56588656 | 56588780 | chr19 | 56728678 | 56728788 | chr19 | 56879501 | 56880008 |
| chr19 | 56904740 | 56905203 | chr19 | 56915320 | 56915428 | chr19 | 56988557 | 56988663 |
| chr19 | 56989528 | 56989625 | chr19 | 56989697 | 56989754 | chr19 | 57050463 | 57050493 |
| chr19 | 57149579 | 57149619 | chr19 | 57154885 | 57155017 | chr19 | 57182994 | 57183126 |
| chr19 | 57276656 | 57276700 | chr19 | 57323825 | 57323854 | chr19 | 57610896 | 57610985 |
| chr19 | 57617522 | 57617715 | chr19 | 57617832 | 57618121 | chr19 | 57683148 | 57683162 |
| chr19 | 57683240 | 57683295 | chr19 | 57862395 | 57862783 | chr19 | 58011124 | 58011281 |
| chr19 | 58038924 | 58038969 | chr19 | 58095006 | 58095835 | chr19 | 58111632 | 58111783 |
| chr19 | 58125544 | 58125881 | chr19 | 58144494 | 58144701 | chr19 | 58219916 | 58220392 |
| chr19 | 58220516 | 58220832 | chr19 | 58238326 | 58238738 | chr19 | 58238988 | 58239088 |
| chr19 | 58400079 | 58400175 | chr19 | 58400417 | 58400518 | chr19 | 58458754 | 58458890 |
| chr19 | 58458979 | 58459201 | chr19 | 58514518 | 58514552 | chr19 | 58520739 | 58520941 |
| chr19 | 58545145 | 58545387 | chr19 | 58545578 | 58545589 | chr19 | 58545652 | 58545837 |
| chr19 | 58609254 | 58609359 | chr19 | 58609473 | 58609525 | chr19 | 58609713 | 58609854 |
| chr19 | 58629975 | 58629975 | chr19 | 58661894 | 58662094 | chr19 | 58666171 | 58666313 |
| chr19 | 58740086 | 58740118 | chr19 | 58874831 | 58874951 | chr19 | 58951271 | 58951400 |
| chr19 | 58951526 | 58951916 | chr19 | 58964180 | 58964266 | chr20 | 118577 | 118751 |
| chr20 | 291148 | 291162 | chr20 | 291221 | 291373 | chr20 | 400007 | 400087 |
| chr20 | 401153 | 401183 | chr20 | 401591 | 401756 | chr20 | 590434 | 590502 |
| chr20 | 592405 | 592449 | chr20 | 644182 | 644351 | chr20 | 644407 | 644787 |
| chr20 | 799104 | 799146 | chr20 | 982749 | 982798 | chr20 | 982892 | 982989 |
| chr20 | 1094651 | 1094682 | chr20 | 1206855 | 1207034 | chr20 | 1783761 | 1784305 |
| chr20 | 1876110 | 1876176 | chr20 | 1975357 | 1975386 | chr20 | 2539331 | 2539771 |
| chr20 | 2668770 | 2668922 | chr20 | 2780753 | 2780773 | chr20 | 2780893 | 2781452 |
| chr20 | 2781731 | 2781761 | chr20 | 2785659 | 2785866 | chr20 | 2785956 | 2786060 |
| chr20 | 3027758 | 3027785 | chr20 | 3052583 | 3052836 | chr20 | 3073561 | 3073899 |
| chr20 | 3154172 | 3154204 | chr20 | 3204870 | 3204952 | chr20 | 3220893 | 3220943 |
| chr20 | 3229576 | 3229612 | chr20 | 3641774 | 3641937 | chr20 | 3663020 | 3663174 |
| chr20 | 3762152 | 3762181 | chr20 | 3762407 | 3762436 | chr20 | 4040731 | 4040871 |
| chr20 | 4085057 | 4085087 | chr20 | 4229402 | 4229432 | chr20 | 4229786 | 4230600 |
| chr20 | 4803070 | 4803650 | chr20 | 4803921 | 4804008 | chr20 | 4804566 | 4804732 |
| chr20 | 5296172 | 5296900 | chr20 | 5297226 | 5297418 | chr20 | 5610356 | 5610386 |
| chr20 | 6022797 | 6023045 | chr20 | 6023268 | 6023310 | chr20 | 6748925 | 6749036 |
| chr20 | 7980362 | 7980392 | chr20 | 8112378 | 8112408 | chr20 | 8112739 | 8113022 |
| chr20 | 8113557 | 8113605 | chr20 | 9487385 | 9487719 | chr20 | 9487789 | 9487997 |
| chr20 | 9488376 | 9488848 | chr20 | 9489070 | 9489214 | chr20 | 9489424 | 9489708 |
| chr20 | 9495271 | 9495509 | chr20 | 9496330 | 9496530 | chr20 | 9496581 | 9496833 |
| chr20 | 9497035 | 9497109 | chr20 | 10198289 | 10198600 | chr20 | 10198941 | 10198945 |
| chr20 | 13200599 | 13200634 | chr20 | 16555010 | 16555030 | chr20 | 17206513 | 17206747 |
| chr20 | 17207874 | 17207930 | chr20 | 17208585 | 17208620 | chr20 | 18039823 | 18039897 |
| chr20 | 18073417 | 18073461 | chr20 | 18448999 | 18449076 | chr20 | 19739613 | 19739696 |
| chr20 | 19928306 | 19928461 | chr20 | 20344498 | 20344559 | chr20 | 20347460 | 20347709 |
| chr20 | 20347737 | 20348154 | chr20 | 20348526 | 20348605 | chr20 | 20349153 | 20349255 |
| chr20 | 20349574 | 20349604 | chr20 | 21080714 | 21080956 | chr20 | 21081029 | 21081844 |
| chr20 | 21082095 | 21082123 | chr20 | 21082216 | 21082253 | chr20 | 21082532 | 21082917 |
| chr20 | 21083421 | 21084361 | chr20 | 21085831 | 21085864 | chr20 | 21086195 | 21086451 |
| chr20 | 21086866 | 21087188 | chr20 | 21372174 | 21372192 | chr20 | 21372295 | 21372725 |
| chr20 | 21376250 | 21376336 | chr20 | 21376703 | 21376733 | chr20 | 21376877 | 21377128 |
| chr20 | 21377474 | 21377640 | chr20 | 21377738 | 21378551 | chr20 | 21486375 | 21486659 |
| chr20 | 21486786 | 21486881 | chr20 | 21487153 | 21487307 | chr20 | 21487367 | 21487581 |
| chr20 | 21488158 | 21488351 | chr20 | 21489240 | 21489446 | chr20 | 21489622 | 21489703 |
| chr20 | 21490175 | 21490762 | chr20 | 21490815 | 21491345 | chr20 | 21492378 | 21492409 |
| chr20 | 21492508 | 21492825 | chr20 | 21493308 | 21493993 | chr20 | 21494531 | 21494703 |
| chr20 | 21495942 | 21495986 | chr20 | 21496260 | 21496294 | chr20 | 21496684 | 21497136 |
| chr20 | 21497413 | 21498638 | chr20 | 21499961 | 21500134 | chr20 | 21501445 | 21501724 |
| chr20 | 21502037 | 21502144 | chr20 | 21502590 | 21502699 | chr20 | 21502838 | 21503117 |
| chr20 | 21503455 | 21503773 | chr20 | 21682399 | 21682456 | chr20 | 21683311 | 21683651 |
| chr20 | 21685385 | 21685526 | chr20 | 21686235 | 21686677 | chr20 | 21687009 | 21687382 |
| chr20 | 21689956 | 21690185 | chr20 | 21694499 | 21694529 | chr20 | 21695088 | 21695273 |
| chr20 | 21695306 | 21695357 | chr20 | 21748445 | 21748491 | chr20 | 22401392 | 22401421 |
| chr20 | 22557396 | 22557675 | chr20 | 22557979 | 22558114 | chr20 | 22558637 | 22558669 |
| chr20 | 22559645 | 22559690 | chr20 | 22562721 | 22562840 | chr20 | 22563563 | 22563602 |
| chr20 | 22564235 | 22564265 | chr20 | 22566961 | 22566990 | chr20 | 23015917 | 23015946 |
| chr20 | 23029110 | 23029151 | chr20 | 23029589 | 23030085 | chr20 | 23030292 | 23030357 |
| chr20 | 23031548 | 23031692 | chr20 | 24450231 | 24450513 | chr20 | 24450820 | 24451019 |
| chr20 | 24451450 | 24451592 | chr20 | 24726701 | 24726825 | chr20 | 25058385 | 25058616 |
| chr20 | 25061746 | 25061788 | chr20 | 25061979 | 25062311 | chr20 | 25062511 | 25062645 |
| chr20 | 25062708 | 25062817 | chr20 | 25062871 | 25062880 | chr20 | 25063780 | 25063906 |
| chr20 | 25063994 | 25064458 | chr20 | 25065179 | 25065395 | chr20 | 25223141 | 25223277 |

TABLE 13-continued

Pan Cancer #3

| chr | start | end | chr | start | end | chr | start | end |
|---|---|---|---|---|---|---|---|---|
| chr20 | 25230509 | 25230534 | chr20 | 25230774 | 25230799 | chr20 | 25334513 | 25334650 |
| chr20 | 26188812 | 26188961 | chr20 | 26190313 | 26190361 | chr20 | 29956013 | 29956042 |
| chr20 | 29956570 | 29956599 | chr20 | 30101723 | 30101743 | chr20 | 30297090 | 30297184 |
| chr20 | 30582750 | 30582978 | chr20 | 30639141 | 30639319 | chr20 | 30639632 | 30639847 |
| chr20 | 30640106 | 30640270 | chr20 | 30778024 | 30778313 | chr20 | 31035471 | 31035518 |
| chr20 | 31115683 | 31115799 | chr20 | 31151769 | 31151799 | chr20 | 31207211 | 31207283 |
| chr20 | 31282879 | 31282903 | chr20 | 32301797 | 32301953 | chr20 | 32450398 | 32450427 |
| chr20 | 33547565 | 33547585 | chr20 | 33574914 | 33574992 | chr20 | 34041981 | 34042004 |
| chr20 | 34148020 | 34148254 | chr20 | 34188617 | 34188631 | chr20 | 34188748 | 34189088 |
| chr20 | 34189167 | 34189391 | chr20 | 34189680 | 34189910 | chr20 | 35742487 | 35742607 |
| chr20 | 36531799 | 36531910 | chr20 | 36781324 | 36781354 | chr20 | 37302697 | 37303343 |
| chr20 | 37351793 | 37352515 | chr20 | 37352607 | 37352626 | chr20 | 37353193 | 37353236 |
| chr20 | 37353455 | 37353718 | chr20 | 37354145 | 37354831 | chr20 | 37354994 | 37355202 |
| chr20 | 37355847 | 37356042 | chr20 | 37356169 | 37356827 | chr20 | 37357216 | 37357353 |
| chr20 | 37357825 | 37358190 | chr20 | 37434552 | 37434721 | chr20 | 37434737 | 37434744 |
| chr20 | 37435104 | 37435218 | chr20 | 37435488 | 37435860 | chr20 | 39316203 | 39316322 |
| chr20 | 39316984 | 39317392 | chr20 | 39317750 | 39318166 | chr20 | 39318383 | 39318415 |
| chr20 | 39319126 | 39319203 | chr20 | 39319515 | 39319653 | chr20 | 39995146 | 39995813 |
| chr20 | 40743859 | 40743888 | chr20 | 41817786 | 41817915 | chr20 | 41818008 | 41818085 |
| chr20 | 41818567 | 41818748 | chr20 | 41818805 | 41818914 | chr20 | 42136330 | 42136411 |
| chr20 | 42218577 | 42218664 | chr20 | 42543754 | 42543853 | chr20 | 42544091 | 42544533 |
| chr20 | 42544728 | 42544984 | chr20 | 42852751 | 42852773 | chr20 | 42876525 | 42876575 |
| chr20 | 43438071 | 43438085 | chr20 | 43438335 | 43438466 | chr20 | 43438982 | 43439022 |
| chr20 | 43439291 | 43439510 | chr20 | 44003765 | 44003811 | chr20 | 44452731 | 44453063 |
| chr20 | 44519077 | 44519107 | chr20 | 44602074 | 44602099 | chr20 | 44602339 | 44602364 |
| chr20 | 44639181 | 44639496 | chr20 | 44640338 | 44640367 | chr20 | 44660750 | 44660877 |
| chr20 | 44686423 | 44686614 | chr20 | 44686628 | 44686762 | chr20 | 44746484 | 44746781 |
| chr20 | 44803174 | 44803675 | chr20 | 44875240 | 44875411 | chr20 | 44880041 | 44880076 |
| chr20 | 44937202 | 44937411 | chr20 | 44937426 | 44937643 | chr20 | 44941518 | 44941661 |
| chr20 | 45142000 | 45142038 | chr20 | 45142152 | 45142272 | chr20 | 45279854 | 45279981 |
| chr20 | 45280040 | 45280302 | chr20 | 45280344 | 45280428 | chr20 | 45337804 | 45337945 |
| chr20 | 45524523 | 45524553 | chr20 | 47247239 | 47247450 | chr20 | 47274032 | 47274062 |
| chr20 | 47296109 | 47296231 | chr20 | 47443729 | 47443936 | chr20 | 47443945 | 47444282 |
| chr20 | 47905426 | 47905603 | chr20 | 47934824 | 47935268 | chr20 | 47935495 | 47935567 |
| chr20 | 47935928 | 47936027 | chr20 | 48184381 | 48184435 | chr20 | 49204179 | 49204449 |
| chr20 | 49261803 | 49262104 | chr20 | 49358357 | 49358396 | chr20 | 49377899 | 49378043 |
| chr20 | 49381160 | 49381240 | chr20 | 49575909 | 49575939 | chr20 | 49639777 | 49639856 |
| chr20 | 49639883 | 49639996 | chr20 | 49640095 | 49640157 | chr20 | 49969348 | 49969515 |
| chr20 | 50160801 | 50160905 | chr20 | 50383384 | 50383423 | chr20 | 50384767 | 50384896 |
| chr20 | 50720437 | 50721200 | chr20 | 50721235 | 50721670 | chr20 | 50721989 | 50722035 |
| chr20 | 50722095 | 50722193 | chr20 | 50722598 | 50722821 | chr20 | 51589766 | 51589908 |
| chr20 | 52226337 | 52226366 | chr20 | 52311463 | 52311513 | chr20 | 52789445 | 52789475 |
| chr20 | 52789853 | 52789948 | chr20 | 52790082 | 52790155 | chr20 | 53092192 | 53092376 |
| chr20 | 53093085 | 53093115 | chr20 | 54578507 | 54578725 | chr20 | 54579892 | 54579958 |
| chr20 | 54580070 | 54580323 | chr20 | 54580622 | 54580691 | chr20 | 55008041 | 55008194 |
| chr20 | 55071640 | 55071717 | chr20 | 55200035 | 55200310 | chr20 | 55200616 | 55200706 |
| chr20 | 55200922 | 55201092 | chr20 | 55201764 | 55202068 | chr20 | 55202359 | 55202626 |
| chr20 | 55202826 | 55203107 | chr20 | 55204322 | 55204604 | chr20 | 55204966 | 55205000 |
| chr20 | 55206294 | 55206393 | chr20 | 55206739 | 55206774 | chr20 | 55499496 | 55499709 |
| chr20 | 55500016 | 55500085 | chr20 | 55500441 | 55500720 | chr20 | 55693527 | 55693625 |
| chr20 | 55841134 | 55841356 | chr20 | 55842096 | 55842189 | chr20 | 56766160 | 56766190 |
| chr20 | 56803398 | 56803441 | chr20 | 56803842 | 56803920 | chr20 | 57089452 | 57089459 |
| chr20 | 57090104 | 57090173 | chr20 | 57224842 | 57225079 | chr20 | 57225219 | 57225307 |
| chr20 | 57484406 | 57484445 | chr20 | 58179809 | 58179854 | chr20 | 58180214 | 58180402 |
| chr20 | 58508887 | 58508943 | chr20 | 59804170 | 59804235 | chr20 | 59826192 | 59826221 |
| chr20 | 59826962 | 59826977 | chr20 | 59828341 | 59828407 | chr20 | 59880433 | 59880477 |
| chr20 | 59910175 | 59910346 | chr20 | 59973028 | 59973072 | chr20 | 60202594 | 60202624 |
| chr20 | 60235333 | 60235526 | chr20 | 60238381 | 60238472 | chr20 | 60238877 | 60238980 |
| chr20 | 60243944 | 60244107 | chr20 | 60329584 | 60329661 | chr20 | 60333880 | 60333969 |
| chr20 | 60359849 | 60359879 | chr20 | 60375036 | 60375070 | chr20 | 60439634 | 60439755 |
| chr20 | 60453925 | 60454091 | chr20 | 60477306 | 60477537 | chr20 | 60485374 | 60485425 |
| chr20 | 60503030 | 60503060 | chr20 | 60545561 | 60545792 | chr20 | 60620122 | 60620557 |
| chr20 | 60772853 | 60773878 | chr20 | 60789965 | 60790124 | chr20 | 60892164 | 60892222 |
| chr20 | 60926019 | 60926049 | chr20 | 60970953 | 60970983 | chr20 | 60983859 | 60984010 |
| chr20 | 60984341 | 60984465 | chr20 | 61288068 | 61288156 | chr20 | 61288463 | 61288534 |
| chr20 | 61294693 | 61294857 | chr20 | 61340581 | 61340689 | chr20 | 61412313 | 61412438 |
| chr20 | 61505881 | 61506330 | chr20 | 61532546 | 61532605 | chr20 | 61560418 | 61560460 |
| chr20 | 61560529 | 61560922 | chr20 | 61585771 | 61585922 | chr20 | 61585990 | 61586004 |
| chr20 | 61636876 | 61636890 | chr20 | 61637468 | 61637648 | chr20 | 61637736 | 61637956 |
| chr20 | 61638221 | 61638469 | chr20 | 61638535 | 61638631 | chr20 | 61703710 | 61703761 |
| chr20 | 61703846 | 61703875 | chr20 | 61714591 | 61714621 | chr20 | 61734420 | 61734481 |
| chr20 | 61747894 | 61747934 | chr20 | 61763598 | 61763628 | chr20 | 61765285 | 61765425 |
| chr20 | 61808181 | 61808270 | chr20 | 61808667 | 61809005 | chr20 | 61809219 | 61809631 |
| chr20 | 61809841 | 61810089 | chr20 | 61823170 | 61823195 | chr20 | 61862380 | 61862452 |
| chr20 | 61885247 | 61885462 | chr20 | 61886068 | 61886203 | chr20 | 61886257 | 61886258 |
| chr20 | 61886725 | 61886755 | chr20 | 61974191 | 61974354 | chr20 | 61980860 | 61980975 |

TABLE 13-continued

Pan Cancer #3

| chr | start | end | chr | start | end | chr | start | end |
|---|---|---|---|---|---|---|---|---|
| chr20 | 62031173 | 62031234 | chr20 | 62032058 | 62032095 | chr20 | 62037559 | 62037598 |
| chr20 | 62046227 | 62046421 | chr20 | 62058700 | 62058786 | chr20 | 62090524 | 62090621 |
| chr20 | 62097666 | 62097695 | chr20 | 62115187 | 62115266 | chr20 | 62119339 | 62119618 |
| chr20 | 62119923 | 62120171 | chr20 | 62126118 | 62126429 | chr20 | 62157229 | 62157307 |
| chr20 | 62165631 | 62165762 | chr20 | 62167554 | 62167584 | chr20 | 62170179 | 62170209 |
| chr20 | 62172945 | 62173055 | chr20 | 62185386 | 62185444 | chr20 | 62260862 | 62260905 |
| chr20 | 62284487 | 62284615 | chr20 | 62314848 | 62314955 | chr20 | 62321206 | 62321341 |
| chr20 | 62321638 | 62321881 | chr20 | 62340321 | 62340442 | chr20 | 62383218 | 62383289 |
| chr20 | 62461349 | 62461475 | chr20 | 62488293 | 62488350 | chr20 | 62631442 | 62631562 |
| chr20 | 62680657 | 62680739 | chr20 | 62715014 | 62715069 | chr20 | 62786577 | 62786726 |
| chr20 | 62795643 | 62795672 | chr21 | 22370332 | 22370458 | chr21 | 22370688 | 22370718 |
| chr21 | 26934368 | 26934786 | chr21 | 27011773 | 27011807 | chr21 | 27012373 | 27012431 |
| chr21 | 27944995 | 27945081 | chr21 | 27945693 | 27945722 | chr21 | 28216634 | 28217690 |
| chr21 | 28218774 | 28219045 | chr21 | 28338836 | 28338887 | chr21 | 28339247 | 28339501 |
| chr21 | 28339892 | 28340048 | chr21 | 28340063 | 28340318 | chr21 | 31015201 | 31015231 |
| chr21 | 31311404 | 31311553 | chr21 | 31312080 | 31312105 | chr21 | 31312313 | 31312409 |
| chr21 | 32253745 | 32253774 | chr21 | 33043985 | 33044051 | chr21 | 33244921 | 33245040 |
| chr21 | 33245683 | 33245718 | chr21 | 33246009 | 33246190 | chr21 | 33627549 | 33627569 |
| chr21 | 33721756 | 33721824 | chr21 | 33785288 | 33785325 | chr21 | 33983236 | 33983332 |
| chr21 | 34392206 | 34392403 | chr21 | 34392437 | 34392566 | chr21 | 34395302 | 34396269 |
| chr21 | 34396795 | 34397091 | chr21 | 34398070 | 34398634 | chr21 | 34398933 | 34399258 |
| chr21 | 34399442 | 34400104 | chr21 | 34400232 | 34400258 | chr21 | 34401185 | 34401392 |
| chr21 | 34442595 | 34442665 | chr21 | 34443103 | 34443262 | chr21 | 34443509 | 34443686 |
| chr21 | 34443893 | 34443956 | chr21 | 34444163 | 34444362 | chr21 | 34444445 | 34444598 |
| chr21 | 35051195 | 35051231 | chr21 | 36041985 | 36042028 | chr21 | 36042092 | 36042238 |
| chr21 | 36042658 | 36042861 | chr21 | 37527928 | 37527958 | chr21 | 37758570 | 37758611 |
| chr21 | 37775034 | 37775141 | chr21 | 38064457 | 38064683 | chr21 | 38064966 | 38065522 |
| chr21 | 38065955 | 38066112 | chr21 | 38067203 | 38067233 | chr21 | 38068178 | 38068229 |
| chr21 | 38068647 | 38068783 | chr21 | 38069093 | 38069203 | chr21 | 38069459 | 38069496 |
| chr21 | 38069854 | 38070162 | chr21 | 38070705 | 38070765 | chr21 | 38071791 | 38071905 |
| chr21 | 38073007 | 38073070 | chr21 | 38073300 | 38073525 | chr21 | 38073616 | 38073860 |
| chr21 | 38078415 | 38078487 | chr21 | 38079988 | 38080062 | chr21 | 38080175 | 38080386 |
| chr21 | 38080551 | 38080684 | chr21 | 38081085 | 38081192 | chr21 | 38081666 | 38081835 |
| chr21 | 38082042 | 38082072 | chr21 | 38082930 | 38083196 | chr21 | 38092179 | 38092221 |
| chr21 | 38119904 | 38120312 | chr21 | 38638504 | 38638526 | chr21 | 38935478 | 38935549 |
| chr21 | 39047776 | 39047838 | chr21 | 39870612 | 39870641 | chr21 | 40033619 | 40033648 |
| chr21 | 40033877 | 40033906 | chr21 | 40034756 | 40034785 | chr21 | 40984685 | 40984900 |
| chr21 | 42617963 | 42617995 | chr21 | 42649172 | 42649202 | chr21 | 43186698 | 43186889 |
| chr21 | 43240082 | 43240112 | chr21 | 43256565 | 43256603 | chr21 | 43376373 | 43376403 |
| chr21 | 43393528 | 43393713 | chr21 | 43485279 | 43485348 | chr21 | 43786683 | 43786713 |
| chr21 | 43991463 | 43991493 | chr21 | 44283581 | 44283774 | chr21 | 44494941 | 44495155 |
| chr21 | 44514762 | 44514791 | chr21 | 44524441 | 44524470 | chr21 | 44837088 | 44837213 |
| chr21 | 44847591 | 44847622 | chr21 | 44866603 | 44866711 | chr21 | 44886709 | 44886870 |
| chr21 | 45148615 | 45148758 | chr21 | 45195149 | 45195319 | chr21 | 45271643 | 45271688 |
| chr21 | 45273717 | 45273913 | chr21 | 45290014 | 45290044 | chr21 | 45508617 | 45508647 |
| chr21 | 45521343 | 45521438 | chr21 | 45717477 | 45717548 | chr21 | 45791079 | 45791109 |
| chr21 | 45847832 | 45847973 | chr21 | 46036642 | 46036767 | chr21 | 46125967 | 46126267 |
| chr21 | 46126387 | 46126427 | chr21 | 46126567 | 46126721 | chr21 | 46127039 | 46127094 |
| chr21 | 46127542 | 46127692 | chr21 | 46128902 | 46128938 | chr21 | 46129444 | 46129485 |
| chr21 | 46193414 | 46193542 | chr21 | 46257116 | 46257273 | chr21 | 46310428 | 46310491 |
| chr21 | 46318286 | 46318343 | chr21 | 46319156 | 46319459 | chr21 | 46359187 | 46359248 |
| chr21 | 46452374 | 46452539 | chr21 | 46677734 | 46677796 | chr21 | 46825825 | 46826067 |
| chr21 | 46847654 | 46847684 | chr21 | 46863658 | 46863708 | chr21 | 46925780 | 46925925 |
| chr21 | 46926459 | 46926565 | chr21 | 46935739 | 46935936 | chr21 | 47010409 | 47010451 |
| chr21 | 47062753 | 47062825 | chr21 | 47063538 | 47063962 | chr21 | 47064250 | 47064377 |
| chr21 | 47404174 | 47404325 | chr21 | 47504861 | 47504895 | chr21 | 47518776 | 47518814 |
| chr21 | 47717560 | 47717589 | chr21 | 47746270 | 47746393 | chr22 | 17081932 | 17081935 |
| chr22 | 17082989 | 17083003 | chr22 | 17083396 | 17083410 | chr22 | 17601086 | 17601133 |
| chr22 | 17601260 | 17601368 | chr22 | 17602511 | 17602624 | chr22 | 17850454 | 17850621 |
| chr22 | 18009985 | 18010105 | chr22 | 18328127 | 18328268 | chr22 | 18340822 | 18340868 |
| chr22 | 18627328 | 18627433 | chr22 | 19017532 | 19017567 | chr22 | 19117564 | 19117594 |
| chr22 | 19136907 | 19136936 | chr22 | 19137859 | 19137888 | chr22 | 19138109 | 19138138 |
| chr22 | 19510799 | 19510946 | chr22 | 19511142 | 19511455 | chr22 | 19511542 | 19511567 |
| chr22 | 19511849 | 19511875 | chr22 | 19702265 | 19702410 | chr22 | 19706171 | 19706677 |
| chr22 | 19742834 | 19742969 | chr22 | 19748644 | 19748908 | chr22 | 20229079 | 20229239 |
| chr22 | 20792482 | 20792641 | chr22 | 20940868 | 20940898 | chr22 | 21153867 | 21154000 |
| chr22 | 21299605 | 21299635 | chr22 | 21304979 | 21305007 | chr22 | 21368587 | 21368617 |
| chr22 | 21977314 | 21977347 | chr22 | 21982792 | 21982972 | chr22 | 22005794 | 22006759 |
| chr22 | 22058203 | 22058238 | chr22 | 22862787 | 22862862 | chr22 | 22901105 | 22901455 |
| chr22 | 23791402 | 23791432 | chr22 | 23801459 | 23801610 | chr22 | 23991237 | 23991272 |
| chr22 | 24145484 | 24145513 | chr22 | 24179940 | 24179982 | chr22 | 24180687 | 24180766 |
| chr22 | 24560375 | 24560526 | chr22 | 24820330 | 24820396 | chr22 | 25678748 | 25678868 |
| chr22 | 25679043 | 25679249 | chr22 | 25679268 | 25679337 | chr22 | 25817107 | 25817180 |
| chr22 | 25817458 | 25817612 | chr22 | 27053194 | 27053250 | chr22 | 28198569 | 28198605 |
| chr22 | 28371649 | 28371679 | chr22 | 28838200 | 28838292 | chr22 | 28838509 | 28838551 |
| chr22 | 28839122 | 28839263 | chr22 | 29091824 | 29091853 | chr22 | 29445752 | 29445923 |

TABLE 13-continued

Pan Cancer #3

| chr | start | end | chr | start | end | chr | start | end |
|---|---|---|---|---|---|---|---|---|
| chr22 | 29876191 | 29876220 | chr22 | 29877223 | 29877299 | chr22 | 29977649 | 29977769 |
| chr22 | 30084358 | 30084388 | chr22 | 30090739 | 30090769 | chr22 | 30116904 | 30117146 |
| chr22 | 30158330 | 30158365 | chr22 | 30476197 | 30476220 | chr22 | 30881582 | 30881612 |
| chr22 | 30938543 | 30938584 | chr22 | 31198492 | 31198637 | chr22 | 31218510 | 31218540 |
| chr22 | 31218794 | 31218829 | chr22 | 31481130 | 31481332 | chr22 | 32748936 | 32748966 |
| chr22 | 33197603 | 33197652 | chr22 | 33453877 | 33454074 | chr22 | 33454194 | 33454258 |
| chr22 | 33454346 | 33454366 | chr22 | 35656581 | 35656610 | chr22 | 35848358 | 35848670 |
| chr22 | 35938746 | 35939000 | chr22 | 36681295 | 36681341 | chr22 | 36855568 | 36855598 |
| chr22 | 36902291 | 36902381 | chr22 | 37720961 | 37721163 | chr22 | 38087310 | 38087367 |
| chr22 | 38199769 | 38199894 | chr22 | 38220653 | 38221201 | chr22 | 38477069 | 38477131 |
| chr22 | 38477297 | 38477794 | chr22 | 38507316 | 38507346 | chr22 | 38592936 | 38593076 |
| chr22 | 38639229 | 38639259 | chr22 | 38874215 | 38874259 | chr22 | 39112502 | 39112584 |
| chr22 | 39784480 | 39784598 | chr22 | 39830355 | 39830457 | chr22 | 39853521 | 39853592 |
| chr22 | 39932499 | 39932563 | chr22 | 39954429 | 39954516 | chr22 | 40042627 | 40042743 |
| chr22 | 40075157 | 40075302 | chr22 | 40226367 | 40226389 | chr22 | 40807034 | 40807063 |
| chr22 | 41048732 | 41048951 | chr22 | 41634393 | 41634542 | chr22 | 41637064 | 41637129 |
| chr22 | 41648414 | 41648444 | chr22 | 41657233 | 41657350 | chr22 | 42096002 | 42096190 |
| chr22 | 42310087 | 42310220 | chr22 | 42311521 | 42311587 | chr22 | 42353611 | 42353892 |
| chr22 | 42667358 | 42667432 | chr22 | 43012543 | 43012560 | chr22 | 43012860 | 43012877 |
| chr22 | 43083130 | 43083148 | chr22 | 43434441 | 43434477 | chr22 | 43740084 | 43740128 |
| chr22 | 43808280 | 43808428 | chr22 | 44208418 | 44208448 | chr22 | 44258366 | 44258506 |
| chr22 | 44287650 | 44287696 | chr22 | 44455707 | 44455740 | chr22 | 45087632 | 45087649 |
| chr22 | 45088602 | 45088743 | chr22 | 45135939 | 45135979 | chr22 | 45252445 | 45252463 |
| chr22 | 45277292 | 45277322 | chr22 | 45313416 | 45313446 | chr22 | 45403086 | 45403133 |
| chr22 | 45403478 | 45403714 | chr22 | 45404197 | 45404433 | chr22 | 45404994 | 45405010 |
| chr22 | 45405047 | 45405061 | :hr22 | 45405318 | 45405418 | chr22 | 45405620 | 45405768 |
| chr22 | 45406271 | 45406328 | chr22 | 45593643 | 45593715 | chr22 | 45604184 | 45604343 |
| chr22 | 45719161 | 45719190 | chr22 | 46262452 | 46263051 | chr22 | 46263512 | 46263623 |
| chr22 | 46263744 | 46263809 | chr22 | 46276749 | 46276820 | chr22 | 46438085 | 46438121 |
| chr22 | 46599623 | 46599725 | chr22 | 46931260 | 46931332 | chr22 | 46933089 | 46933237 |
| chr22 | 47005080 | 47005154 | chr22 | 47023044 | 47023191 | chr22 | 47054686 | 47054716 |
| chr22 | 47193335 | 47193371 | chr22 | 47395475 | 47395505 | chr22 | 47525846 | 47525885 |
| chr22 | 47584867 | 47585024 | chr22 | 48027626 | 48027655 | chr22 | 48885530 | 48885837 |
| chr22 | 48886659 | 48886849 | chr22 | 48931881 | 48932027 | chr22 | 48971533 | 48971679 |
| chr22 | 48972220 | 48972465 | chr22 | 49852617 | 49852647 | chr22 | 49979646 | 49979757 |
| chr22 | 50001699 | 50001882 | chr22 | 50002787 | 50002819 | chr22 | 50003204 | 50003234 |
| chr22 | 50010113 | 50010258 | chr22 | 50010461 | 50010585 | chr22 | 50031691 | 50031721 |
| chr22 | 50064760 | 50064944 | chr22 | 50149431 | 50149470 | chr22 | 50467005 | 50467035 |
| chr22 | 50497147 | 50497182 | chr22 | 50497214 | 50497287 | chr22 | 50623672 | 50623714 |
| chr22 | 50623742 | 50623815 | chr22 | 50899293 | 50899672 | chr22 | 50939073 | 50939111 |
| chr22 | 50943093 | 50943262 | chr22 | 50986016 | 50986045 | chr22 | 51042278 | 51042404 |
| chr22 | 51042458 | 51042565 | chr22 | 51112150 | 51112232 | chrX | 3631506 | 3631633 |
| chrX | 3746612 | 3746642 | chrX | 6145331 | 6145688 | chrX | 8698863 | 8698897 |
| chrX | 8699504 | 8699566 | chrX | 20148710 | 20148739 | chrX | 47039370 | 47039399 |
| chrX | 47426106 | 47426144 | chrX | 47426780 | 47426821 | chrX | 50557075 | 50557075 |
| chrX | 66931448 | 66931477 | chrX | 66937356 | 66937385 | chrX | 66943529 | 66943567 |
| chrX | 70339239 | 70339268 | chrX | 100740260 | 100740289 | chrX | 101906099 | 101906120 |
| chrX | 102000609 | 102000758 | chrX | 134156560 | 134156680 | chrX | 136656563 | 136656592 |
| chrY | 2655316 | 2655346 | chrY | 3446305 | 3446343 | chrY | 13316007 | 13316132 |
| chrY | 14532822 | 14532852 | chrY | 14533556 | 14533613 | chrY | 21204734 | 21205113 |

TABLE 14

Pan Cancer #4

| chr | start | end | chr | start | end | chr | start | end |
|---|---|---|---|---|---|---|---|---|
| chr1 | 898633 | 898792 | chr1 | 913445 | 914044 | chr1 | 1080495 | 1080914 |
| chr1 | 1146657 | 1146896 | chr1 | 1218688 | 1218779 | chr1 | 1223433 | 1223595 |
| chr1 | 1235811 | 1236156 | chr1 | 1266957 | 1267233 | chr1 | 1267372 | 1267791 |
| chr1 | 1267823 | 1268242 | chr1 | 1341738 | 1341826 | chr1 | 1475458 | 1476417 |
| chr1 | 1483096 | 1483139 | chr1 | 1563119 | 1563298 | chr1 | 1856362 | 1856471 |
| chr1 | 1857759 | 1857811 | chr1 | 1874647 | 1874877 | chr1 | 1910341 | 1910465 |
| chr1 | 1935188 | 1935547 | chr1 | 1974768 | 1974802 | chr1 | 2066406 | 2066756 |
| chr1 | 2125141 | 2125560 | chr1 | 2263067 | 2263366 | chr1 | 2267472 | 2267771 |
| chr1 | 2304239 | 2304478 | chr1 | 2307851 | 2307970 | chr1 | 2308023 | 2308030 |
| chr1 | 2308297 | 2308716 | chr1 | 2309792 | 2309994 | chr1 | 2331281 | 2331500 |
| chr1 | 2336323 | 2336440 | chr1 | 2375047 | 2375646 | chr1 | 2396927 | 2397106 |
| chr1 | 2428239 | 2428478 | chr1 | 2472089 | 2472388 | chr1 | 2506974 | 2507150 |
| chr1 | 2520925 | 2521062 | chr1 | 2706094 | 2706552 | chr1 | 2830081 | 2830147 |
| chr1 | 2865964 | 2866143 | chr1 | 2984645 | 2984824 | chr1 | 3102567 | 3102866 |
| chr1 | 3182781 | 3182874 | chr1 | 3182942 | 3183020 | chr1 | 3322011 | 3322250 |
| chr1 | 3567062 | 3568320 | chr1 | 3601749 | 3602030 | chr1 | 3606995 | 3607339 |

TABLE 14-continued

Pan Cancer #4

| chr | start | end | chr | start | end | chr | start | end |
|---|---|---|---|---|---|---|---|---|
| chr1 | 3659530 | 3659769 | chr1 | 3663458 | 3663637 | chr1 | 3663779 | 3664018 |
| chr1 | 3664606 | 3664781 | chr1 | 3683723 | 3683902 | chr1 | 4111087 | 4111323 |
| chr1 | 4713943 | 4714422 | chr1 | 4714642 | 4716744 | chr1 | 6166262 | 6166561 |
| chr1 | 6171668 | 6171907 | chr1 | 6186410 | 6186649 | chr1 | 6280169 | 6280348 |
| chr1 | 6304103 | 6304342 | chr1 | 6360495 | 6360728 | chr1 | 6446041 | 6446400 |
| chr1 | 6480434 | 6480913 | chr1 | 6500911 | 6501262 | chr1 | 6507603 | 6508202 |
| chr1 | 7764540 | 7764775 | chr1 | 8277298 | 8277837 | chr1 | 9712017 | 9712179 |
| chr1 | 9712459 | 9713096 | chr1 | 10166481 | 10166626 | chr1 | 10948478 | 10948657 |
| chr1 | 11538796 | 11538913 | chr1 | 11539101 | 11539280 | chr1 | 11539336 | 11539515 |
| chr1 | 11540035 | 11540334 | chr1 | 11591712 | 11591863 | chr1 | 11752375 | 11752614 |
| chr1 | 11936674 | 11936779 | chr1 | 11958996 | 11959295 | chr1 | 12041511 | 12041630 |
| chr1 | 12123143 | 12123742 | chr1 | 12227604 | 12227805 | chr1 | 12251342 | 12252059 |
| chr1 | 13839669 | 13840088 | chr1 | 13910336 | 13910815 | chr1 | 14026401 | 14026700 |
| chr1 | 14730390 | 14730502 | chr1 | 14925417 | 14926136 | chr1 | 15251113 | 15251316 |
| chr1 | 15480854 | 15480983 | chr1 | 16085267 | 16085746 | chr1 | 16474984 | 16475299 |
| chr1 | 16861448 | 16861627 | chr1 | 17445781 | 17446011 | chr1 | 18434366 | 18434605 |
| chr1 | 18437373 | 18437612 | chr1 | 18956114 | 18956353 | chr1 | 18956383 | 18956408 |
| chr1 | 18956496 | 18956735 | chr1 | 18956782 | 18957321 | chr1 | 18957428 | 18957667 |
| chr1 | 18957938 | 18958477 | chr1 | 18959346 | 18959645 | chr1 | 18960795 | 18961094 |
| chr1 | 18962648 | 18963231 | chr1 | 18969543 | 18969902 | chr1 | 18971772 | 18972011 |
| chr1 | 18972056 | 18972170 | chr1 | 19043472 | 19043771 | chr1 | 19992272 | 19992511 |
| chr1 | 20127444 | 20127555 | chr1 | 20618230 | 20618469 | chr1 | 20878953 | 20879372 |
| chr1 | 20879482 | 20879721 | chr1 | 20879752 | 20880051 | chr1 | 20880095 | 20880694 |
| chr1 | 21026082 | 21026253 | chr1 | 21042820 | 21042999 | chr1 | 21044024 | 21044263 |
| chr1 | 21573736 | 21574215 | chr1 | 21835856 | 21836095 | chr1 | 22140674 | 22141393 |
| chr1 | 22927327 | 22927566 | chr1 | 23748907 | 23749146 | chr1 | 23884996 | 23885088 |
| chr1 | 25255845 | 25256029 | chr1 | 25256280 | 25256459 | chr1 | 25256826 | 25257305 |
| chr1 | 25257391 | 25257464 | chr1 | 26551597 | 26551896 | chr1 | 26551989 | 26552228 |
| chr1 | 26737509 | 26737688 | chr1 | 26737855 | 26738274 | chr1 | 27190078 | 27190377 |
| chr1 | 27844444 | 27844623 | chr1 | 29450398 | 29450637 | chr1 | 29585984 | 29586763 |
| chr1 | 29804872 | 29805171 | chr1 | 30351469 | 30351828 | chr1 | 30815328 | 30815675 |
| chr1 | 31863112 | 31863130 | chr1 | 32180323 | 32180502 | chr1 | 32237507 | 32238586 |
| chr1 | 32410202 | 32410381 | chr1 | 32410418 | 32410717 | chr1 | 32705425 | 32705639 |
| chr1 | 32756421 | 32756519 | chr1 | 32930524 | 32930658 | chr1 | 34628874 | 34629053 |
| chr1 | 34629390 | 34629809 | chr1 | 34630473 | 34630712 | chr1 | 34630770 | 34631069 |
| chr1 | 34631502 | 34631741 | chr1 | 34631859 | 34631892 | chr1 | 34632023 | 34632038 |
| chr1 | 34642298 | 34642657 | chr1 | 35258557 | 35258796 | chr1 | 35350980 | 35351759 |
| chr1 | 35395450 | 35395929 | chr1 | 35664721 | 35664836 | chr1 | 36042605 | 36043564 |
| chr1 | 36563382 | 36563621 | chr1 | 37498718 | 37499257 | chr1 | 37499358 | 37500257 |
| chr1 | 37500368 | 37500907 | chr1 | 37500998 | 37501107 | chr1 | 38100591 | 38100787 |
| chr1 | 38219635 | 38219874 | chr1 | 38229961 | 38230380 | chr1 | 38230700 | 38230937 |
| chr1 | 38398356 | 38398431 | chr1 | 38510079 | 38510258 | chr1 | 38510475 | 38510774 |
| chr1 | 38510778 | 38511197 | chr1 | 38511252 | 38511911 | chr1 | 38512311 | 38512490 |
| chr1 | 38513162 | 38513229 | chr1 | 39269662 | 39270201 | chr1 | 40137822 | 40138061 |
| chr1 | 40237053 | 40237281 | chr1 | 40349627 | 40349746 | chr1 | 41284058 | 41284541 |
| chr1 | 41847494 | 41847793 | chr1 | 41848778 | 41848915 | chr1 | 41967261 | 41967360 |
| chr1 | 41991552 | 41991791 | chr1 | 43834653 | 43834807 | chr1 | 44068700 | 44068879 |
| chr1 | 44726821 | 44727360 | chr1 | 44872358 | 44873797 | chr1 | 44883030 | 44884289 |
| chr1 | 45308239 | 45308358 | chr1 | 45308655 | 45308729 | chr1 | 46632781 | 46633020 |
| chr1 | 46913761 | 46914360 | chr1 | 46914582 | 46914641 | chr1 | 46932686 | 46932842 |
| chr1 | 46951114 | 46951833 | chr1 | 46956380 | 46956679 | chr1 | 46956728 | 46957246 |
| chr1 | 47009851 | 47010150 | chr1 | 47695033 | 47695512 | chr1 | 47696207 | 47696686 |
| chr1 | 47696727 | 47697206 | chr1 | 47697254 | 47697613 | chr1 | 47697642 | 47698301 |
| chr1 | 47881984 | 47882403 | chr1 | 47882667 | 47882906 | chr1 | 47909640 | 47910239 |
| chr1 | 47910420 | 47911019 | chr1 | 47911243 | 47911365 | chr1 | 48058982 | 48059341 |
| chr1 | 49242260 | 49242619 | chr1 | 50513541 | 50513837 | chr1 | 50799190 | 50799489 |
| chr1 | 50880808 | 50882625 | chr1 | 50882731 | 50883690 | chr1 | 50883800 | 50884999 |
| chr1 | 50885262 | 50885441 | chr1 | 50886107 | 50887366 | chr1 | 50888619 | 50888918 |
| chr1 | 50889008 | 50889607 | chr1 | 50889741 | 50890460 | chr1 | 50890600 | 50891565 |
| chr1 | 50892073 | 50892432 | chr1 | 50892523 | 50893962 | chr1 | 51763181 | 51763395 |
| chr1 | 52832605 | 52832712 | chr1 | 53068087 | 53068626 | chr1 | 53098746 | 53099165 |
| chr1 | 53308489 | 53309328 | chr1 | 53528288 | 53528527 | chr1 | 53705675 | 53705794 |
| chr1 | 54203419 | 54204498 | chr1 | 54586532 | 54586851 | chr1 | 55462599 | 55462778 |
| chr1 | 57888293 | 57888472 | chr1 | 57888888 | 57889187 | chr1 | 57889319 | 57889738 |
| chr1 | 57890332 | 57890671 | chr1 | 58715055 | 58715294 | chr1 | 58715375 | 58716094 |
| chr1 | 61519265 | 61519497 | chr1 | 62793169 | 62793342 | chr1 | 63539429 | 63539968 |
| chr1 | 63785232 | 63786431 | chr1 | 63786928 | 63787167 | chr1 | 63787226 | 63787645 |
| chr1 | 63788341 | 63788640 | chr1 | 63788694 | 63790373 | chr1 | 63792458 | 63793171 |
| chr1 | 63795265 | 63796370 | chr1 | 63796418 | 63796584 | chr1 | 64240031 | 64240222 |
| chr1 | 64240526 | 64240765 | chr1 | 64734554 | 64734669 | chr1 | 64937227 | 64937401 |
| chr1 | 65731243 | 65731542 | chr1 | 65731552 | 65731851 | chr1 | 65990876 | 65991115 |
| chr1 | 65991344 | 65991883 | chr1 | 66258088 | 66258867 | chr1 | 66259037 | 66259276 |
| chr1 | 66998702 | 66999412 | chr1 | 66999536 | 66999772 | chr1 | 67217965 | 67218424 |
| chr1 | 67390243 | 67390542 | chr1 | 67390993 | 67391172 | chr1 | 67773081 | 67773860 |
| chr1 | 70033524 | 70033709 | chr1 | 70033829 | 70034003 | chr1 | 70034368 | 70034667 |
| chr1 | 70035014 | 70035526 | chr1 | 70599152 | 70599260 | chr1 | 70672859 | 70672978 |

TABLE 14-continued

| Pan Cancer #4 | | | | | | | | |
|---|---|---|---|---|---|---|---|---|
| chr | start | end | chr | start | end | chr | start | end |
| chr1 | 72749635 | 72749798 | chr1 | 75595702 | 75596479 | chr1 | 75596597 | 75597668 |
| chr1 | 75597842 | 75598261 | chr1 | 75598310 | 75598489 | chr1 | 75599345 | 75599704 |
| chr1 | 75600148 | 75601513 | chr1 | 75601889 | 75603148 | chr1 | 76080387 | 76080866 |
| chr1 | 76082050 | 76082289 | chr1 | 76354731 | 76354839 | chr1 | 76540398 | 76540757 |
| chr1 | 77332984 | 77333163 | chr1 | 77333285 | 77333625 | chr1 | 77333947 | 77334846 |
| chr1 | 77747291 | 77747530 | chr1 | 77747848 | 77748327 | chr1 | 78511371 | 78512450 |
| chr1 | 78957198 | 78957617 | chr1 | 82268586 | 82268904 | chr1 | 84944531 | 84944650 |
| chr1 | 85358543 | 85358902 | chr1 | 85463275 | 85463454 | chr1 | 86621565 | 86622024 |
| chr1 | 86622112 | 86622224 | chr1 | 86622430 | 86622831 | chr1 | 86860815 | 86861049 |
| chr1 | 87617672 | 87617911 | chr1 | 90309344 | 90309571 | chr1 | 91171926 | 91172765 |
| chr1 | 91177865 | 91178284 | chr1 | 91179982 | 91180401 | chr1 | 91181853 | 91182212 |
| chr1 | 91182246 | 91182969 | chr1 | 91183001 | 91183805 | chr1 | 91183850 | 91184080 |
| chr1 | 91184339 | 91184758 | chr1 | 91185126 | 91185809 | chr1 | 91188891 | 91189483 |
| chr1 | 91189585 | 91190484 | chr1 | 91190791 | 91191390 | chr1 | 91192174 | 91192773 |
| chr1 | 91194446 | 91194672 | chr1 | 91195015 | 91195494 | chr1 | 91195802 | 91196581 |
| chr1 | 91316168 | 91316407 | chr1 | 91316536 | 91316775 | chr1 | 91869914 | 91870093 |
| chr1 | 92948236 | 92948701 | chr1 | 92948760 | 92949059 | chr1 | 92952071 | 92952632 |
| chr1 | 94343486 | 94343596 | chr1 | 97185167 | 97185357 | chr1 | 98510704 | 98511423 |
| chr1 | 98511536 | 98512015 | chr1 | 98514151 | 98514330 | chr1 | 98515048 | 98515408 |
| chr1 | 98518930 | 98519769 | chr1 | 99469586 | 99469885 | chr1 | 99470049 | 99470288 |
| chr1 | 99470697 | 99470924 | chr1 | 100437184 | 100437270 | chr1 | 101004358 | 101004837 |
| chr1 | 101004989 | 101005228 | chr1 | 101005279 | 101005758 | chr1 | 101702411 | 101702710 |
| chr1 | 101703538 | 101703717 | chr1 | 107682647 | 107683066 | chr1 | 107683359 | 107683598 |
| chr1 | 107684161 | 107684520 | chr1 | 108506989 | 108507168 | chr1 | 108507230 | 108507589 |
| chr1 | 108507615 | 108507914 | chr1 | 108507957 | 108508671 | chr1 | 109203582 | 109203761 |
| chr1 | 109585369 | 109585472 | chr1 | 109631647 | 109631766 | chr1 | 109644252 | 109644413 |
| chr1 | 110610483 | 110612162 | chr1 | 110612760 | 110613239 | chr1 | 110626592 | 110627671 |
| chr1 | 110672792 | 110673331 | chr1 | 110692886 | 110694205 | chr1 | 110754040 | 110754202 |
| chr1 | 110754211 | 110754930 | chr1 | 110883455 | 110884054 | chr1 | 111097832 | 111098011 |
| chr1 | 111098107 | 111098406 | chr1 | 111216684 | 111218063 | chr1 | 111505931 | 111506290 |
| chr1 | 111813448 | 111813687 | chr1 | 112084880 | 112085059 | chr1 | 114448981 | 114449087 |
| chr1 | 114695362 | 114696021 | chr1 | 114696132 | 114696299 | chr1 | 114696335 | 114696791 |
| chr1 | 115256441 | 115256620 | chr1 | 115258659 | 115258838 | chr1 | 115631842 | 115632011 |
| chr1 | 115632393 | 115632632 | chr1 | 115880081 | 115880500 | chr1 | 115880765 | 115881304 |
| chr1 | 116214002 | 116214132 | chr1 | 116214207 | 116214421 | chr1 | 116371051 | 116371290 |
| chr1 | 116380550 | 116381389 | chr1 | 116382294 | 116382583 | chr1 | 119521973 | 119522121 |
| chr1 | 119522200 | 119522632 | chr1 | 119522741 | 119523039 | chr1 | 119526993 | 119527472 |
| chr1 | 119527549 | 119527728 | chr1 | 119528557 | 119529216 | chr1 | 119529703 | 119529942 |
| chr1 | 119530024 | 119530743 | chr1 | 119530944 | 119531243 | chr1 | 119531943 | 119532177 |
| chr1 | 119535738 | 119535857 | chr1 | 119536058 | 119536457 | chr1 | 119542248 | 119542427 |
| chr1 | 119542905 | 119543324 | chr1 | 119543438 | 119544277 | chr1 | 119548749 | 119548928 |
| chr1 | 119548955 | 119549017 | chr1 | 119549032 | 119549034 | chr1 | 119550068 | 119550367 |
| chr1 | 119550434 | 119550733 | chr1 | 119550818 | 119551357 | chr1 | 150603035 | 150603141 |
| chr1 | 151169649 | 151169757 | chr1 | 151170069 | 151170297 | chr1 | 151300814 | 151300933 |
| chr1 | 151693849 | 151694448 | chr1 | 152085302 | 152085601 | chr1 | 152488055 | 152488294 |
| chr1 | 153539382 | 153539681 | chr1 | 153540006 | 153540245 | chr1 | 153651873 | 153652274 |
| chr1 | 153937048 | 153937167 | chr1 | 154298230 | 154298562 | chr1 | 154475073 | 154475612 |
| chr1 | 154516709 | 154516926 | chr1 | 155043313 | 155043734 | chr1 | 155161767 | 155161886 |
| chr1 | 155578918 | 155579008 | chr1 | 155826303 | 155826412 | chr1 | 155954190 | 155954391 |
| chr1 | 156010529 | 156010643 | chr1 | 156215255 | 156215434 | chr1 | 156215527 | 156215886 |
| chr1 | 156357892 | 156358611 | chr1 | 156390058 | 156390777 | chr1 | 156405436 | 156406515 |
| chr1 | 156432076 | 156432315 | chr1 | 156594879 | 156595118 | chr1 | 156611795 | 156612214 |
| chr1 | 156626505 | 156626744 | chr1 | 156626814 | 156627113 | chr1 | 156646516 | 156646740 |
| chr1 | 156814831 | 156815250 | chr1 | 156815356 | 156815835 | chr1 | 156830190 | 156830429 |
| chr1 | 156838078 | 156838424 | chr1 | 156863010 | 156863429 | chr1 | 156863574 | 156863808 |
| chr1 | 157247369 | 157247487 | chr1 | 157458816 | 157458935 | chr1 | 157895339 | 157895518 |
| chr1 | 158669614 | 158669973 | chr1 | 158687334 | 158687633 | chr1 | 159158251 | 159158588 |
| chr1 | 159187205 | 159187390 | chr1 | 160693839 | 160693957 | chr1 | 160992253 | 160992363 |
| chr1 | 161007615 | 161007847 | chr1 | 161228566 | 161228971 | chr1 | 161275466 | 161276125 |
| chr1 | 161442367 | 161442546 | chr1 | 161471751 | 161471868 | chr1 | 161591390 | 161591444 |
| chr1 | 161591549 | 161591629 | chr1 | 162792211 | 162792630 | chr1 | 164290533 | 164290772 |
| chr1 | 165086889 | 165087114 | chr1 | 165204994 | 165205233 | chr1 | 165321651 | 165321950 |
| chr1 | 165324104 | 165324758 | chr1 | 165325016 | 165325615 | chr1 | 165325804 | 165326043 |
| chr1 | 165326128 | 165326547 | chr1 | 165414124 | 165414352 | chr1 | 166134158 | 166134397 |
| chr1 | 166134643 | 166134882 | chr1 | 166135118 | 166135357 | chr1 | 166853551 | 166853668 |
| chr1 | 166916774 | 166917193 | chr1 | 167599076 | 167599435 | chr1 | 167599521 | 167599940 |
| chr1 | 167823371 | 167823524 | chr1 | 169396291 | 169397010 | chr1 | 170629466 | 170629513 |
| chr1 | 170629925 | 170630151 | chr1 | 170630364 | 170630903 | chr1 | 170631005 | 170631244 |
| chr1 | 170631399 | 170631638 | chr1 | 170633533 | 170633712 | chr1 | 170637582 | 170637881 |
| chr1 | 170640425 | 170640784 | chr1 | 171625443 | 171625543 | chr1 | 171810113 | 171811066 |
| chr1 | 173638567 | 173639153 | chr1 | 175346411 | 175346646 | chr1 | 175388563 | 175388692 |
| chr1 | 177133619 | 177133918 | chr1 | 177140021 | 177140790 | chr1 | 177150699 | 177150878 |
| chr1 | 179544884 | 179545183 | chr1 | 179712063 | 179713502 | chr1 | 180197986 | 180198285 |
| chr1 | 180202331 | 180203110 | chr1 | 180203355 | 180205009 | chr1 | 180235656 | 180235835 |
| chr1 | 180882487 | 180882518 | chr1 | 180925188 | 180925289 | chr1 | 180925330 | 180925487 |
| chr1 | 181287599 | 181287838 | chr1 | 181287922 | 181288281 | chr1 | 181451315 | 181452214 |

TABLE 14-continued

Pan Cancer #4

| chr | start | end | chr | start | end | chr | start | end |
|---|---|---|---|---|---|---|---|---|
| chr1 | 181452770 | 181453069 | chr1 | 181454774 | 181455013 | chr1 | 181455104 | 181455343 |
| chr1 | 182584084 | 182584623 | chr1 | 182807488 | 182807607 | chr1 | 183129301 | 183129530 |
| chr1 | 183386070 | 183386369 | chr1 | 183386414 | 183386713 | chr1 | 183386752 | 183387051 |
| chr1 | 183387174 | 183387413 | chr1 | 183462984 | 183463103 | chr1 | 183774155 | 183774454 |
| chr1 | 184005609 | 184005908 | chr1 | 185073803 | 185074028 | chr1 | 190444781 | 190444892 |
| chr1 | 190445080 | 190445379 | chr1 | 190447297 | 190447596 | chr1 | 195732240 | 195732521 |
| chr1 | 196577628 | 196577953 | chr1 | 196578007 | 196578246 | chr1 | 197879307 | 197879546 |
| chr1 | 197879607 | 197880258 | chr1 | 197882052 | 197882291 | chr1 | 197882353 | 197882581 |
| chr1 | 197886978 | 197887817 | chr1 | 197887977 | 197888396 | chr1 | 197888546 | 197889385 |
| chr1 | 200009312 | 200009551 | chr1 | 200009665 | 200010202 | chr1 | 200011236 | 200012191 |
| chr1 | 201368752 | 201368805 | chr1 | 201983038 | 201983277 | chr1 | 202081790 | 202081886 |
| chr1 | 202183343 | 202183476 | chr1 | 202679128 | 202679607 | chr1 | 203298210 | 203298441 |
| chr1 | 203429530 | 203429649 | chr1 | 204333520 | 204333660 | chr1 | 204653475 | 204653894 |
| chr1 | 205312504 | 205313043 | chr1 | 205424577 | 205425046 | chr1 | 205537569 | 205537868 |
| chr1 | 207200767 | 207201066 | chr1 | 207669419 | 207670138 | chr1 | 207818295 | 207818424 |
| chr1 | 208084210 | 208084569 | chr1 | 209381030 | 209381269 | chr1 | 210111072 | 210111251 |
| chr1 | 210111285 | 210112244 | chr1 | 211847683 | 211847862 | chr1 | 212963808 | 212963979 |
| chr1 | 213123776 | 213124075 | chr1 | 213124573 | 213124992 | chr1 | 214156345 | 214157004 |
| chr1 | 214158753 | 214159052 | chr1 | 214160028 | 214160266 | chr1 | 214360583 | 214361062 |
| chr1 | 214724457 | 214724588 | chr1 | 215254998 | 215255897 | chr1 | 216897142 | 216897321 |
| chr1 | 217307273 | 217307311 | chr1 | 217307368 | 217308360 | chr1 | 217308907 | 217309206 |
| chr1 | 217309671 | 217309910 | chr1 | 217311163 | 217311942 | chr1 | 217312946 | 217313827 |
| chr1 | 217805068 | 217805236 | chr1 | 218520021 | 218520477 | chr1 | 218520701 | 218520740 |
| chr1 | 219347112 | 219347134 | chr1 | 219347314 | 219347553 | chr1 | 220101056 | 220101475 |
| chr1 | 220101609 | 220101788 | chr1 | 220132115 | 220132213 | chr1 | 220636429 | 220636548 |
| chr1 | 220700737 | 220700976 | chr1 | 221051936 | 221052595 | chr1 | 221053527 | 221053946 |
| chr1 | 221067418 | 221067777 | chr1 | 223302739 | 223302978 | chr1 | 223538254 | 223538670 |
| chr1 | 223936546 | 223937145 | chr1 | 224400388 | 224400627 | chr1 | 224528740 | 224528919 |
| chr1 | 224803668 | 224803854 | chr1 | 224803995 | 224804991 | chr1 | 224805051 | 224805890 |
| chr1 | 226411169 | 226411348 | chr1 | 226411617 | 226411916 | chr1 | 226924982 | 226925281 |
| chr1 | 227729689 | 227730168 | chr1 | 228194340 | 228194579 | chr1 | 228195294 | 228196433 |
| chr1 | 228201147 | 228201326 | chr1 | 228247924 | 228247961 | chr1 | 228248228 | 228248407 |
| chr1 | 228463210 | 228463809 | chr1 | 228528749 | 228529108 | chr1 | 228558623 | 228559329 |
| chr1 | 228566528 | 228566618 | chr1 | 228566637 | 228566767 | chr1 | 228603929 | 228604348 |
| chr1 | 228633887 | 228634354 | chr1 | 228645048 | 228645827 | chr1 | 228646196 | 228646315 |
| chr1 | 228651350 | 228651709 | chr1 | 228651805 | 228651924 | chr1 | 228652243 | 228652704 |
| chr1 | 229542750 | 229543229 | chr1 | 229543459 | 229543612 | chr1 | 229566670 | 229566942 |
| chr1 | 229567012 | 229568289 | chr1 | 229569712 | 229569951 | chr1 | 230404150 | 230404360 |
| chr1 | 230561683 | 230561922 | chr1 | 231297013 | 231297312 | chr1 | 231298505 | 231298864 |
| chr1 | 232765226 | 232765398 | chr1 | 233750126 | 233750402 | chr1 | 234040224 | 234040403 |
| chr1 | 234040668 | 234041147 | chr1 | 234041303 | 234041716 | chr1 | 234349895 | 234350194 |
| chr1 | 234445299 | 234445478 | chr1 | 234620965 | 234621073 | chr1 | 234844947 | 234845167 |
| chr1 | 235813693 | 235814292 | chr1 | 236227538 | 236228197 | chr1 | 236228507 | 236228866 |
| chr1 | 236559075 | 236559374 | chr1 | 236849381 | 236850220 | chr1 | 237205085 | 237205098 |
| chr1 | 237205157 | 237205264 | chr1 | 237205337 | 237205576 | chr1 | 237205612 | 237206811 |
| chr1 | 239550505 | 239551284 | chr1 | 240118762 | 240119061 | chr1 | 240160997 | 240161571 |
| chr1 | 240254859 | 240255098 | chr1 | 240255282 | 240255581 | chr1 | 240255739 | 240256278 |
| chr1 | 240256573 | 240256872 | chr1 | 240775351 | 240775530 | chr1 | 241052047 | 241052201 |
| chr1 | 241520202 | 241520441 | chr1 | 241520509 | 241520632 | chr1 | 241520685 | 241520688 |
| chr1 | 241587013 | 241587194 | chr1 | 241587513 | 241587872 | chr1 | 242686642 | 242687781 |
| chr1 | 242688103 | 242688342 | chr1 | 242688377 | 242688773 | chr1 | 243646523 | 243646762 |
| chr1 | 244014160 | 244014479 | chr1 | 244080598 | 244080777 | chr1 | 244080874 | 244080883 |
| chr1 | 244893136 | 244893255 | chr1 | 245135670 | 245135849 | chr1 | 245494418 | 245494631 |
| chr1 | 246330402 | 246330509 | chr1 | 246488077 | 246488316 | chr1 | 248002191 | 248002310 |
| chr1 | 248020405 | 248021424 | chr1 | 248027930 | 248028289 | chr1 | 248074658 | 248074768 |
| chr1 | 248074838 | 248075008 | chr1 | 248099661 | 248099900 | chr1 | 248328674 | 248328921 |
| chr1 | 249121623 | 249121738 | chr2 | 287492 | 287731 | chr2 | 288318 | 288557 |
| chr2 | 467943 | 468182 | chr2 | 468217 | 468756 | chr2 | 496125 | 496465 |
| chr2 | 720748 | 720985 | chr2 | 875887 | 876066 | chr2 | 945838 | 946077 |
| chr2 | 946117 | 946356 | chr2 | 946449 | 946688 | chr2 | 946819 | 947238 |
| chr2 | 1653023 | 1653262 | chr2 | 1746523 | 1747302 | chr2 | 1747591 | 1748906 |
| chr2 | 2844646 | 2844676 | chr2 | 2844802 | 2844825 | chr2 | 3750873 | 3751052 |
| chr2 | 3751238 | 3751537 | chr2 | 5831102 | 5831401 | chr2 | 5831715 | 5831894 |
| chr2 | 5831967 | 5832326 | chr2 | 5832800 | 5834119 | chr2 | 5835990 | 5836349 |
| chr2 | 5836451 | 5837170 | chr2 | 5837197 | 5837496 | chr2 | 5866006 | 5866305 |
| chr2 | 7164389 | 7164704 | chr2 | 7571420 | 7571828 | chr2 | 9134330 | 9134569 |
| chr2 | 9960660 | 9960839 | chr2 | 10115632 | 10115739 | chr2 | 10153063 | 10153168 |
| chr2 | 10153229 | 10153422 | chr2 | 10154909 | 10155024 | chr2 | 10155269 | 10155384 |
| chr2 | 10156334 | 10156493 | chr2 | 10182747 | 10182986 | chr2 | 10408310 | 10408347 |
| chr2 | 10688800 | 10688979 | chr2 | 11052419 | 11052658 | chr2 | 11809858 | 11810217 |
| chr2 | 12246027 | 12246196 | chr2 | 12858356 | 12858715 | chr2 | 14772673 | 14772888 |
| chr2 | 14774475 | 14774664 | chr2 | 17719601 | 17719900 | chr2 | 18058941 | 18059180 |
| chr2 | 18059692 | 18059931 | chr2 | 19550140 | 19550319 | chr2 | 19551225 | 19551464 |
| chr2 | 19556226 | 19556765 | chr2 | 19556994 | 19557173 | chr2 | 19558744 | 19558983 |
| chr2 | 19561045 | 19561404 | chr2 | 19561422 | 19561781 | chr2 | 19563277 | 19563516 |
| chr2 | 20068723 | 20068962 | chr2 | 20442485 | 20442586 | chr2 | 20642626 | 20642745 |

TABLE 14-continued

| | | Pan Cancer #4 | | | | | | |
|---|---|---|---|---|---|---|---|---|
| chr | start | end | chr | start | end | chr | start | end |
| chr2 | 20865560 | 20866022 | chr2 | 25391060 | 25391313 | chr2 | 25391586 | 25391825 |
| chr2 | 25438724 | 25439356 | chr2 | 26372893 | 26373072 | chr2 | 26395353 | 26395652 |
| chr2 | 26401956 | 26402135 | chr2 | 26407418 | 26408085 | chr2 | 26521960 | 26522079 |
| chr2 | 26915682 | 26916341 | chr2 | 27070250 | 27070489 | chr2 | 27071144 | 27071443 |
| chr2 | 27072394 | 27072633 | chr2 | 27072727 | 27073086 | chr2 | 27578410 | 27578500 |
| chr2 | 27887451 | 27887630 | chr2 | 29033261 | 29034020 | chr2 | 29337988 | 29339067 |
| chr2 | 30143219 | 30143578 | chr2 | 30143957 | 30144496 | chr2 | 30453619 | 30454038 |
| chr2 | 31360210 | 31360929 | chr2 | 31361015 | 31361118 | chr2 | 31361194 | 31361194 |
| chr2 | 31361282 | 31361461 | chr2 | 31456606 | 31457131 | chr2 | 32504335 | 32504449 |
| chr2 | 38302176 | 38302955 | chr2 | 38365728 | 38365847 | chr2 | 39187141 | 39187800 |
| chr2 | 39892997 | 39893596 | chr2 | 39893897 | 39894136 | chr2 | 40678513 | 40678872 |
| chr2 | 40678945 | 40679712 | chr2 | 42274495 | 42274734 | chr2 | 42329340 | 42329759 |
| chr2 | 42720185 | 42720644 | chr2 | 43019525 | 43019944 | chr2 | 43451819 | 43452418 |
| chr2 | 43824034 | 43824132 | chr2 | 44497613 | 44497842 | chr2 | 45028911 | 45029450 |
| chr2 | 45029637 | 45029787 | chr2 | 45155039 | 45157783 | chr2 | 45159873 | 45160352 |
| chr2 | 45160496 | 45160735 | chr2 | 45161589 | 45162188 | chr2 | 45162319 | 45162558 |
| chr2 | 45162653 | 45163012 | chr2 | 45164589 | 45164768 | chr2 | 45165490 | 45165669 |
| chr2 | 45168857 | 45168908 | chr2 | 45169349 | 45170128 | chr2 | 45171295 | 45171954 |
| chr2 | 45176506 | 45176865 | chr2 | 45179546 | 45179725 | chr2 | 45179862 | 45180156 |
| chr2 | 45181417 | 45181776 | chr2 | 45181795 | 45182094 | chr2 | 45231239 | 45231478 |
| chr2 | 45231754 | 45232208 | chr2 | 45233307 | 45233666 | chr2 | 45235491 | 45236030 |
| chr2 | 45237585 | 45237884 | chr2 | 45240457 | 45240876 | chr2 | 45241041 | 45241280 |
| chr2 | 45395768 | 45396007 | chr2 | 45396234 | 45396533 | chr2 | 45396603 | 45397082 |
| chr2 | 46526226 | 46526331 | chr2 | 47193958 | 47194077 | chr2 | 47200517 | 47200696 |
| chr2 | 47249735 | 47249914 | chr2 | 47598298 | 47598477 | chr2 | 47598579 | 47598698 |
| chr2 | 47748048 | 47748587 | chr2 | 47796952 | 47797911 | chr2 | 47798093 | 47798752 |
| chr2 | 47798853 | 47799212 | chr2 | 48982485 | 48982964 | chr2 | 50573520 | 50573924 |
| chr2 | 50574041 | 50574940 | chr2 | 55289095 | 55289274 | chr2 | 56149762 | 56149941 |
| chr2 | 56150632 | 56151256 | chr2 | 56410918 | 56411087 | chr2 | 56411593 | 56411832 |
| chr2 | 58655968 | 58656207 | chr2 | 60706663 | 60706902 | chr2 | 60796498 | 60796617 |
| chr2 | 60797060 | 60797359 | chr2 | 61135116 | 61135235 | chr2 | 62798248 | 62798485 |
| chr2 | 63275470 | 63275949 | chr2 | 63278888 | 63279067 | chr2 | 63280853 | 63281752 |
| chr2 | 63282632 | 63282871 | chr2 | 63282924 | 63283053 | chr2 | 63283870 | 63284229 |
| chr2 | 63284675 | 63284914 | chr2 | 63284996 | 63287412 | chr2 | 66652937 | 66653063 |
| chr2 | 66653158 | 66653577 | chr2 | 66653690 | 66653989 | chr2 | 66660560 | 66660791 |
| chr2 | 66808447 | 66809453 | chr2 | 67625373 | 67625492 | chr2 | 67625733 | 67625852 |
| chr2 | 67626153 | 67626332 | chr2 | 68546249 | 68546968 | chr2 | 68559344 | 68559463 |
| chr2 | 68672777 | 68672956 | chr2 | 70418720 | 70418722 | chr2 | 71355039 | 71355218 |
| chr2 | 71503688 | 71503927 | chr2 | 71504007 | 71504246 | chr2 | 71680759 | 71680938 |
| chr2 | 71693423 | 71693694 | chr2 | 72374295 | 72374524 | chr2 | 72374611 | 72374850 |
| chr2 | 73145548 | 73145787 | chr2 | 73145824 | 73146123 | chr2 | 73147245 | 73148313 |
| chr2 | 73150850 | 73151029 | chr2 | 73151098 | 73151929 | chr2 | 73152600 | 73152839 |
| chr2 | 73429420 | 73429719 | chr2 | 73429862 | 73430161 | chr2 | 73430234 | 73430818 |
| chr2 | 73440271 | 73440370 | chr2 | 73518355 | 73519014 | chr2 | 73519501 | 73519920 |
| chr2 | 74010442 | 74010621 | chr2 | 74453989 | 74454348 | chr2 | 74726670 | 74726849 |
| chr2 | 74740761 | 74741480 | chr2 | 74741746 | 74742045 | chr2 | 74742085 | 74743824 |
| chr2 | 74781997 | 74782356 | chr2 | 75426958 | 75426980 | chr2 | 75427295 | 75427474 |
| chr2 | 75427845 | 75428264 | chr2 | 80529292 | 80529520 | chr2 | 80529573 | 80530112 |
| chr2 | 80530413 | 80530652 | chr2 | 80531651 | 80531830 | chr2 | 80549486 | 80549845 |
| chr2 | 85107377 | 85107616 | chr2 | 85361224 | 85361703 | chr2 | 87016489 | 87016728 |
| chr2 | 87017707 | 87018313 | chr2 | 88469219 | 88469398 | chr2 | 88751182 | 88751901 |
| chr2 | 88751961 | 88752380 | chr2 | 88752515 | 88752874 | chr2 | 88990108 | 88990347 |
| chr2 | 89064525 | 89065364 | chr2 | 95663873 | 95664112 | chr2 | 95690654 | 95690890 |
| chr2 | 95690944 | 95691363 | chr2 | 95691441 | 95691860 | chr2 | 95691908 | 95692567 |
| chr2 | 95941596 | 95941895 | chr2 | 96990808 | 96991399 | chr2 | 97193003 | 97193722 |
| chr2 | 97427415 | 97428194 | chr2 | 98703220 | 98703491 | chr2 | 98962800 | 98963039 |
| chr2 | 98963255 | 98963674 | chr2 | 98963750 | 98964289 | chr2 | 98964502 | 98964741 |
| chr2 | 99439054 | 99439593 | chr2 | 99553333 | 99553632 | chr2 | 99553723 | 99553734 |
| chr2 | 99796327 | 99796415 | chr2 | 99798571 | 99798746 | chr2 | 99799229 | 99799230 |
| chr2 | 100937747 | 100939246 | chr2 | 101009731 | 101010030 | chr2 | 101034149 | 101034388 |
| chr2 | 101436638 | 101436790 | chr2 | 102091079 | 102091335 | chr2 | 103236080 | 103236277 |
| chr2 | 105459001 | 105459600 | chr2 | 105459805 | 105460604 | chr2 | 105460847 | 105461026 |
| chr2 | 105461096 | 105461335 | chr2 | 105461461 | 105462000 | chr2 | 105462075 | 105462314 |
| chr2 | 105468701 | 105469000 | chr2 | 105469569 | 105470168 | chr2 | 105470266 | 105470925 |
| chr2 | 105472149 | 105472928 | chr2 | 105473162 | 105473521 | chr2 | 105478687 | 105479166 |
| chr2 | 105480444 | 105480683 | chr2 | 105483568 | 105483807 | chr2 | 105484367 | 105484480 |
| chr2 | 105488348 | 105488527 | chr2 | 105760890 | 105761004 | chr2 | 106060525 | 106060884 |
| chr2 | 106681644 | 106681870 | chr2 | 106681936 | 106682175 | chr2 | 106730137 | 106730316 |
| chr2 | 106959289 | 106959648 | chr2 | 106959833 | 106960072 | chr2 | 107103778 | 107104017 |
| chr2 | 107502499 | 107502918 | chr2 | 107503124 | 107503423 | chr2 | 107503458 | 107503637 |
| chr2 | 107503802 | 107504101 | chr2 | 109335091 | 109335722 | chr2 | 109648002 | 109648301 |
| chr2 | 109745915 | 109746154 | chr2 | 109746204 | 109746563 | chr2 | 111875279 | 111875518 |
| chr2 | 111876621 | 111876964 | chr2 | 112656944 | 112657123 | chr2 | 114034797 | 114035276 |
| chr2 | 114256879 | 114257238 | chr2 | 114261200 | 114261559 | chr2 | 115918579 | 115920618 |
| chr2 | 118981075 | 118982574 | chr2 | 119067545 | 119068143 | chr2 | 119532059 | 119532358 |
| chr2 | 119566137 | 119566376 | chr2 | 119591259 | 119591558 | chr2 | 119592666 | 119592863 |

TABLE 14-continued

| Pan Cancer #4 | | | | | | | | |
|---|---|---|---|---|---|---|---|---|
| chr | start | end | chr | start | end | chr | start | end |
| chr2 | 119592923 | 119593642 | chr2 | 119599830 | 119600129 | chr2 | 119600235 | 119600839 |
| chr2 | 119600856 | 119600957 | chr2 | 119602515 | 119603174 | chr2 | 119603946 | 119604093 |
| chr2 | 119604154 | 119604245 | chr2 | 119604711 | 119604933 | chr2 | 119606048 | 119606283 |
| chr2 | 119606625 | 119606647 | chr2 | 119606692 | 119606931 | chr2 | 119607085 | 119607504 |
| chr2 | 119607694 | 119607933 | chr2 | 119610758 | 119611057 | chr2 | 119611653 | 119611892 |
| chr2 | 119612250 | 119612429 | chr2 | 119614047 | 119614271 | chr2 | 119614697 | 119614936 |
| chr2 | 119614952 | 119615719 | chr2 | 119616070 | 119616669 | chr2 | 119616721 | 119616960 |
| chr2 | 119914617 | 119914856 | chr2 | 119915947 | 119916186 | chr2 | 119916208 | 119916687 |
| chr2 | 120281556 | 120281790 | chr2 | 120281849 | 120282028 | chr2 | 120979994 | 120980173 |
| chr2 | 120980255 | 120980494 | chr2 | 121200303 | 121200532 | chr2 | 121345007 | 121345169 |
| chr2 | 121411987 | 121412231 | chr2 | 122495323 | 122495490 | chr2 | 124782247 | 124782546 |
| chr2 | 124782596 | 124783195 | chr2 | 127413828 | 127413908 | chr2 | 127423136 | 127423434 |
| chr2 | 127428910 | 127429147 | chr2 | 127438559 | 127438738 | chr2 | 127782953 | 127783360 |
| chr2 | 127863514 | 127863813 | chr2 | 127976391 | 127976750 | chr2 | 128421788 | 128422027 |
| chr2 | 128616519 | 128616628 | chr2 | 128847701 | 128847799 | chr2 | 130763485 | 130763724 |
| chr2 | 130971056 | 130971355 | chr2 | 131477742 | 131478023 | chr2 | 131594915 | 131595094 |
| chr2 | 131720754 | 131721353 | chr2 | 131721376 | 131722035 | chr2 | 131792157 | 131793236 |
| chr2 | 132088680 | 132088919 | chr2 | 132121566 | 132121823 | chr2 | 132152279 | 132152578 |
| chr2 | 132182701 | 132183180 | chr2 | 132767373 | 132767492 | chr2 | 133014571 | 133014678 |
| chr2 | 133015300 | 133015419 | chr2 | 133062239 | 133062478 | chr2 | 133426175 | 133426354 |
| chr2 | 133426561 | 133426776 | chr2 | 137522371 | 137522550 | chr2 | 137523751 | 137523759 |
| chr2 | 139536863 | 139537221 | chr2 | 139537355 | 139537954 | chr2 | 142887816 | 142888149 |
| chr2 | 142888264 | 142888503 | chr2 | 144694272 | 144695231 | chr2 | 145273369 | 145273848 |
| chr2 | 145274112 | 145274531 | chr2 | 145274715 | 145275314 | chr2 | 145282045 | 145282224 |
| chr2 | 148776713 | 148776876 | chr2 | 149633009 | 149633488 | chr2 | 149633646 | 149634065 |
| chr2 | 149645413 | 149645995 | chr2 | 151342979 | 151343218 | chr2 | 154333432 | 154333671 |
| chr2 | 154334170 | 154334769 | chr2 | 154335056 | 154335355 | chr2 | 154727963 | 154728442 |
| chr2 | 154728963 | 154729322 | chr2 | 154729485 | 154729664 | chr2 | 155555064 | 155555440 |
| chr2 | 157176506 | 157176805 | chr2 | 157176908 | 157178407 | chr2 | 157178637 | 157178809 |
| chr2 | 160760984 | 160761454 | chr2 | 161253375 | 161253554 | chr2 | 162272983 | 162274182 |
| chr2 | 162274220 | 162274414 | chr2 | 162274748 | 162274942 | chr2 | 162275055 | 162275887 |
| chr2 | 162279911 | 162281050 | chr2 | 162283291 | 162284130 | chr2 | 164592998 | 164593237 |
| chr2 | 168149978 | 168150337 | chr2 | 168150669 | 168151028 | chr2 | 170282882 | 170283178 |
| chr2 | 170551654 | 170551866 | chr2 | 170681792 | 170681909 | chr2 | 170682152 | 170682329 |
| chr2 | 171569986 | 171570525 | chr2 | 171570590 | 171570829 | chr2 | 171571171 | 171571342 |
| chr2 | 171571379 | 171571410 | chr2 | 171571800 | 171571997 | chr2 | 171670259 | 171670558 |
| chr2 | 171671385 | 171671984 | chr2 | 171674001 | 171674026 | chr2 | 171674664 | 171675143 |
| chr2 | 171675268 | 171675687 | chr2 | 171676590 | 171676885 | chr2 | 171822419 | 171822574 |
| chr2 | 172366939 | 172367178 | chr2 | 172411062 | 172411241 | chr2 | 172945027 | 172945266 |
| chr2 | 172945821 | 172946294 | chr2 | 172947684 | 172948406 | chr2 | 172948813 | 172948850 |
| chr2 | 172949090 | 172949809 | chr2 | 172951494 | 172951754 | chr2 | 172952425 | 172952640 |
| chr2 | 172952685 | 172953144 | chr2 | 172955346 | 172955645 | chr2 | 172957808 | 172958157 |
| chr2 | 172961319 | 172961678 | chr2 | 172964743 | 172965882 | chr2 | 172966174 | 172966533 |
| chr2 | 172972648 | 172973307 | chr2 | 173099710 | 173099889 | chr2 | 173100167 | 173100506 |
| chr2 | 173422651 | 173422770 | chr2 | 175190771 | 175192550 | chr2 | 175193187 | 175193906 |
| chr2 | 175195785 | 175195936 | chr2 | 175196355 | 175196371 | chr2 | 175196426 | 175196654 |
| chr2 | 175197015 | 175197194 | chr2 | 175198650 | 175198987 | chr2 | 175199432 | 175200012 |
| chr2 | 175200093 | 175202746 | chr2 | 175204100 | 175204279 | chr2 | 175204694 | 175205893 |
| chr2 | 175206752 | 175207111 | chr2 | 175207154 | 175207333 | chr2 | 175207446 | 175207745 |
| chr2 | 175208214 | 175209218 | chr2 | 175546942 | 175547241 | chr2 | 175547310 | 175547489 |
| chr2 | 176940092 | 176940391 | chr2 | 176943180 | 176943659 | chr2 | 176943763 | 176943863 |
| chr2 | 176943995 | 176944002 | chr2 | 176944326 | 176945885 | chr2 | 176946475 | 176947494 |
| chr2 | 176947647 | 176948006 | chr2 | 176948522 | 176948821 | chr2 | 176948971 | 176949150 |
| chr2 | 176949603 | 176949962 | chr2 | 176950051 | 176950350 | chr2 | 176956480 | 176956719 |
| chr2 | 176956821 | 176957300 | chr2 | 176957409 | 176957768 | chr2 | 176957829 | 176958008 |
| chr2 | 176958045 | 176958584 | chr2 | 176959191 | 176959589 | chr2 | 176963366 | 176963605 |
| chr2 | 176963999 | 176964238 | chr2 | 176964272 | 176965591 | chr2 | 176969387 | 176969984 |
| chr2 | 176972611 | 176972662 | chr2 | 176975946 | 176976289 | chr2 | 176980649 | 176981592 |
| chr2 | 176982487 | 176982726 | chr2 | 176986633 | 176986932 | chr2 | 176986962 | 176988401 |
| chr2 | 176993000 | 176993082 | chr2 | 176993462 | 176994741 | chr2 | 176994813 | 176994864 |
| chr2 | 176994981 | 176995712 | chr2 | 177001000 | 177001058 | chr2 | 177001118 | 177002079 |
| chr2 | 177004463 | 177004762 | chr2 | 177042891 | 177043610 | chr2 | 177053187 | 177053906 |
| chr2 | 177054023 | 177054442 | chr2 | 177502981 | 177503153 | chr2 | 178972904 | 178973143 |
| chr2 | 179317039 | 179317139 | chr2 | 182321308 | 182321727 | chr2 | 182321736 | 182322275 |
| chr2 | 182322292 | 182323131 | chr2 | 182542829 | 182543008 | chr2 | 182543221 | 182543413 |
| chr2 | 182543666 | 182544025 | chr2 | 182545124 | 182545363 | chr2 | 182545438 | 182545797 |
| chr2 | 182545887 | 182546179 | chr2 | 182546361 | 182546540 | chr2 | 182547290 | 182547709 |
| chr2 | 182547840 | 182548259 | chr2 | 182548992 | 182549231 | chr2 | 182549247 | 182549546 |
| chr2 | 182550020 | 182550199 | chr2 | 182819031 | 182819312 | chr2 | 183731200 | 183731619 |
| chr2 | 183731734 | 183732153 | chr2 | 185462776 | 185463075 | chr2 | 185463116 | 185463895 |
| chr2 | 166603414 | 186603593 | chr2 | 188418947 | 188419178 | chr2 | 189157513 | 189157692 |
| chr2 | 193058947 | 193060146 | chr2 | 193060294 | 193060533 | chr2 | 193060608 | 193060967 |
| chr2 | 193061341 | 193061580 | chr2 | 198456572 | 198456690 | chr2 | 200326551 | 200326730 |
| chr2 | 200326765 | 200326813 | chr2 | 200327187 | 200327666 | chr2 | 200328669 | 200329748 |
| chr2 | 200333686 | 200333925 | chr2 | 200334895 | 200335308 | chr2 | 200335363 | 200336034 |
| chr2 | 201450453 | 201450812 | chr2 | 201450845 | 201451144 | chr2 | 202096992 | 202097231 |

TABLE 14-continued

| | | Pan Cancer #4 | | | | | | |
|---|---|---|---|---|---|---|---|---|
| chr | start | end | chr | start | end | chr | start | end |
| chr2 | 202899788 | 202899967 | chr2 | 206550978 | 206551457 | chr2 | 207138998 | 207139177 |
| chr2 | 207139267 | 207139686 | chr2 | 207307426 | 207307665 | chr2 | 207308711 | 207308950 |
| chr2 | 207506612 | 207507266 | chr2 | 208635519 | 208635864 | chr2 | 209113024 | 209113202 |
| chr2 | 209225137 | 209225376 | chr2 | 209271228 | 209271441 | chr2 | 210636255 | 210636974 |
| chr2 | 213401138 | 213401437 | chr2 | 213401511 | 213402050 | chr2 | 213403015 | 213403434 |
| chr2 | 217559222 | 217559401 | chr2 | 218806046 | 218806405 | chr2 | 219736062 | 219736705 |
| chr2 | 219827964 | 219827975 | chr2 | 219847360 | 219847659 | chr2 | 219848726 | 219849085 |
| chr2 | 219857648 | 219857860 | chr2 | 220080582 | 220080941 | chr2 | 220173904 | 220174383 |
| chr2 | 220196266 | 220196671 | chr2 | 220223024 | 220223203 | chr2 | 220223557 | 220223796 |
| chr2 | 220283250 | 220283609 | chr2 | 220299495 | 220300154 | chr2 | 220313696 | 220313777 |
| chr2 | 220348949 | 220349788 | chr2 | 220361370 | 220361609 | chr2 | 220416297 | 220416596 |
| chr2 | 220416770 | 220417729 | chr2 | 222435699 | 222435857 | chr2 | 223155678 | 223156277 |
| chr2 | 223158648 | 223159542 | chr2 | 223159735 | 223160154 | chr2 | 223160242 | 223160481 |
| chr2 | 223161173 | 223161352 | chr2 | 223161452 | 223162165 | chr2 | 223162678 | 223163637 |
| chr2 | 223163682 | 223164034 | chr2 | 223164440 | 223164979 | chr2 | 223165334 | 223165933 |
| chr2 | 223166190 | 223166825 | chr2 | 223167302 | 223167661 | chr2 | 223168346 | 223168945 |
| chr2 | 223169543 | 223169962 | chr2 | 223170286 | 223170525 | chr2 | 223171026 | 223171265 |
| chr2 | 223172263 | 223172356 | chr2 | 223172959 | 223173259 | chr2 | 223176018 | 223176282 |
| chr2 | 223176361 | 223177080 | chr2 | 223177224 | 223177703 | chr2 | 228029326 | 228029625 |
| chr2 | 228466762 | 228466881 | chr2 | 228735702 | 228735828 | chr2 | 228736135 | 228736554 |
| chr2 | 229046024 | 229046605 | chr2 | 230795461 | 230795640 | chr2 | 231693123 | 231693362 |
| chr2 | 232394867 | 232395166 | chr2 | 232791619 | 232792098 | chr2 | 233350112 | 233351491 |
| chr2 | 233351930 | 233352949 | chr2 | 233498615 | 233499394 | chr2 | 233750451 | 233750630 |
| chr2 | 235404471 | 235404590 | chr2 | 235860803 | 235860897 | chr2 | 236402683 | 236402901 |
| chr2 | 236403060 | 236403102 | chr2 | 236403174 | 236403419 | chr2 | 236403779 | 236403833 |
| chr2 | 236877188 | 236877367 | chr2 | 237072333 | 237073112 | chr2 | 237073265 | 237073504 |
| chr2 | 237076651 | 237076833 | chr2 | 237077466 | 237077685 | chr2 | 237077815 | 237078054 |
| chr2 | 237078097 | 237078427 | chr2 | 237080190 | 237080369 | chr2 | 237081255 | 237081914 |
| chr2 | 237082030 | 237082809 | chr2 | 237086291 | 237086559 | chr2 | 237145333 | 237145692 |
| chr2 | 237416114 | 237416504 | chr2 | 238395205 | 238395444 | chr2 | 238395815 | 238395988 |
| chr2 | 238535796 | 238536215 | chr2 | 238864570 | 238864989 | chr2 | 239051124 | 239051303 |
| chr2 | 239072551 | 239072790 | chr2 | 239139928 | 239140347 | chr2 | 239265703 | 239265881 |
| chr2 | 239482400 | 239482622 | chr2 | 239705202 | 239705364 | chr2 | 239755090 | 239755269 |
| chr2 | 239755638 | 239755877 | chr2 | 239756347 | 239756786 | chr2 | 239757551 | 239757910 |
| chr2 | 239757992 | 239758231 | chr2 | 239758251 | 239758490 | chr2 | 239957240 | 239957539 |
| chr2 | 240168722 | 240169141 | chr2 | 240319908 | 240320087 | chr2 | 240582303 | 240582448 |
| chr2 | 240619443 | 240619682 | chr2 | 240658145 | 240658504 | chr2 | 240658593 | 240658772 |
| chr2 | 241095576 | 241095868 | chr2 | 241393126 | 241393545 | chr2 | 241542045 | 241542344 |
| chr2 | 241544927 | 241545106 | chr2 | 241758299 | 241758898 | chr2 | 241759497 | 241759796 |
| chr2 | 241760075 | 241760254 | chr2 | 241760420 | 241760599 | chr2 | 241771062 | 241771361 |
| chr2 | 241865091 | 241865450 | chr2 | 242009317 | 242009496 | chr2 | 242021689 | 242021916 |
| chr2 | 242523873 | 242524172 | chr2 | 242549754 | 242549772 | chr2 | 242549918 | 242550053 |
| chr2 | 242554475 | 242554654 | chr2 | 242756042 | 242756401 | chr2 | 242832893 | 242833252 |
| chr2 | 242833484 | 242833663 | chr2 | 242833711 | 242833930 | chr2 | 242836419 | 242836718 |
| chr2 | 242925420 | 242925719 | chr3 | 238456 | 239175 | chr3 | 239534 | 240313 |
| chr3 | 2140189 | 2140488 | chr3 | 3840419 | 3840838 | chr3 | 3840946 | 3841245 |
| chr3 | 3842586 | 3842689 | chr3 | 5137871 | 5138109 | chr3 | 6902228 | 6902441 |
| chr3 | 6903500 | 6903564 | chr3 | 8810059 | 8810298 | chr3 | 9178065 | 9178281 |
| chr3 | 9593878 | 9594117 | chr3 | 9594286 | 9594473 | chr3 | 9595199 | 9595678 |
| chr3 | 9904155 | 9904634 | chr3 | 9941391 | 9941509 | chr3 | 9956984 | 9957223 |
| chr3 | 9957355 | 9957774 | chr3 | 10182757 | 10182917 | chr3 | 10183247 | 10183426 |
| chr3 | 10183632 | 10183811 | chr3 | 10857884 | 10858123 | chr3 | 11034163 | 11034462 |
| chr3 | 11034991 | 11035410 | chr3 | 12046310 | 12046727 | chr3 | 12917512 | 12917751 |
| chr3 | 12976987 | 12977150 | chr3 | 13323405 | 13324064 | chr3 | 13324277 | 13324516 |
| chr3 | 13324744 | 13325023 | chr3 | 13590341 | 13590940 | chr3 | 13679082 | 13679441 |
| chr3 | 13921316 | 13921555 | chr3 | 14851755 | 14851994 | chr3 | 14852233 | 14853012 |
| chr3 | 16553963 | 16554202 | chr3 | 16554251 | 16554730 | chr3 | 17001229 | 17001341 |
| chr3 | 19189367 | 19189546 | chr3 | 19189611 | 19189850 | chr3 | 19190061 | 19190253 |
| chr3 | 22413591 | 22413770 | chr3 | 22413871 | 22414050 | chr3 | 24870915 | 24870925 |
| chr3 | 24870982 | 24871281 | chr3 | 25469303 | 25469482 | chr3 | 25469605 | 25469784 |
| chr3 | 26663963 | 26664202 | chr3 | 26664303 | 26664842 | chr3 | 27754404 | 27754583 |
| chr3 | 27762260 | 27762733 | chr3 | 27762783 | 27762962 | chr3 | 27763492 | 27763671 |
| chr3 | 27764421 | 27764600 | chr3 | 27765085 | 27765274 | chr3 | 27771422 | 27772081 |
| chr3 | 28616745 | 28617764 | chr3 | 32858274 | 32859773 | chr3 | 32859992 | 32860351 |
| chr3 | 33259801 | 33260876 | chr3 | 35680768 | 35680947 | chr3 | 36805720 | 36805959 |
| chr3 | 36806053 | 36806292 | chr3 | 37493429 | 37493720 | chr3 | 37901952 | 37902028 |
| chr3 | 38030610 | 38030789 | chr3 | 38032257 | 38032436 | chr3 | 38035669 | 38036088 |
| chr3 | 38080596 | 38081015 | chr3 | 38081061 | 38081360 | chr3 | 38690527 | 38690766 |
| chr3 | 38691316 | 38691557 | chr3 | 39851674 | 39851913 | chr3 | 41266012 | 41266239 |
| chr3 | 42222640 | 42222737 | chr3 | 42640761 | 42640874 | chr3 | 42814467 | 42814706 |
| chr3 | 42947333 | 42947632 | chr3 | 44036176 | 44036415 | chr3 | 44036496 | 44036755 |
| chr3 | 44036743 | 44037282 | chr3 | 44037525 | 44037764 | chr3 | 44037781 | 44038740 |
| chr3 | 44039265 | 44040097 | chr3 | 44040413 | 44040652 | chr3 | 44040709 | 44041128 |
| chr3 | 44063354 | 44063953 | chr3 | 44596405 | 44596584 | chr3 | 44596614 | 44596913 |
| chr3 | 44626336 | 44626815 | chr3 | 44726855 | 44727274 | chr3 | 45187222 | 45187461 |
| chr3 | 46924905 | 46925039 | chr3 | 48227686 | 48227788 | chr3 | 48236391 | 48236553 |

TABLE 14-continued

Pan Cancer #4

| chr | start | end | chr | start | end | chr | start | end |
|---|---|---|---|---|---|---|---|---|
| chr3 | 48693228 | 48694247 | chr3 | 48698723 | 48699859 | chr3 | 49906993 | 49907232 |
| chr3 | 49939836 | 49940495 | chr3 | 50243283 | 50243582 | chr3 | 50374581 | 50374760 |
| chr3 | 50374843 | 50375022 | chr3 | 50375104 | 50375639 | chr3 | 50395432 | 50395611 |
| chr3 | 50402078 | 50403037 | chr3 | 50575518 | 50575635 | chr3 | 52552500 | 52552739 |
| chr3 | 52553395 | 52553537 | chr3 | 53032708 | 53033609 | chr3 | 54155525 | 54155764 |
| chr3 | 54157297 | 54157536 | chr3 | 54157780 | 54158006 | chr3 | 55519117 | 55519228 |
| chr3 | 55523019 | 55523318 | chr3 | 62353291 | 62354130 | chr3 | 62354187 | 62354426 |
| chr3 | 62354531 | 62355010 | chr3 | 62355332 | 62355571 | chr3 | 62355692 | 62357431 |
| chr3 | 62357527 | 62357766 | chr3 | 62358059 | 62358178 | chr3 | 62358444 | 62358683 |
| chr3 | 62358758 | 62359115 | chr3 | 62359276 | 62359995 | chr3 | 62360222 | 62360641 |
| chr3 | 62362812 | 62363206 | chr3 | 62363541 | 62363780 | chr3 | 62363819 | 62364418 |
| chr3 | 62364659 | 62365205 | chr3 | 62861044 | 62861223 | chr3 | 63264065 | 63264135 |
| chr3 | 63264158 | 63264244 | chr3 | 68056816 | 68057235 | chr3 | 68980843 | 68981202 |
| chr3 | 68981469 | 68981708 | chr3 | 69590865 | 69591044 | chr3 | 69591264 | 69592163 |
| chr3 | 69741004 | 69741087 | chr3 | 69937792 | 69937926 | chr3 | 71802489 | 71802720 |
| chr3 | 71803040 | 71803459 | chr3 | 71803553 | 71803912 | chr3 | 73045525 | 73045672 |
| chr3 | 75955924 | 75956463 | chr3 | 79815421 | 79815660 | chr3 | 79816688 | 79817099 |
| chr3 | 79817214 | 79817393 | chr3 | 85008452 | 85008811 | chr3 | 88248026 | 88248142 |
| chr3 | 96532726 | 96532965 | chr3 | 96533302 | 96533541 | chr3 | 96533947 | 96534186 |
| chr3 | 98620817 | 98621056 | chr3 | 99594836 | 99595195 | chr3 | 101230575 | 101230641 |
| chr3 | 101230942 | 101231174 | chr3 | 101397150 | 101397304 | chr3 | 106936068 | 106936294 |
| chr3 | 112052411 | 112052521 | chr3 | 117715472 | 117715643 | chr3 | 117715772 | 117716551 |
| chr3 | 120003954 | 120004438 | chr3 | 120169683 | 120169922 | chr3 | 120627319 | 120627535 |
| chr3 | 121902878 | 121903717 | chr3 | 122234151 | 122234246 | chr3 | 122702194 | 122702430 |
| chr3 | 123166972 | 123167631 | chr3 | 123167679 | 123167918 | chr3 | 125898567 | 125899292 |
| chr3 | 125899445 | 125899706 | chr3 | 125899740 | 125899979 | chr3 | 125932169 | 125932586 |
| chr3 | 126373433 | 126373619 | chr3 | 126373669 | 126373792 | chr3 | 126854599 | 126854898 |
| chr3 | 127534879 | 127534976 | chr3 | 127634112 | 127634291 | chr3 | 127794464 | 127794943 |
| chr3 | 127795248 | 127795253 | chr3 | 128202373 | 128202552 | chr3 | 128208829 | 128209308 |
| chr3 | 128273913 | 128274692 | chr3 | 128417127 | 128417306 | chr3 | 128719977 | 128720696 |
| chr3 | 128720780 | 128721319 | chr3 | 128764472 | 128764711 | chr3 | 129693075 | 129694391 |
| chr3 | 129694430 | 129694609 | chr3 | 130064351 | 130064588 | chr3 | 130064744 | 130064923 |
| chr3 | 130235952 | 130236298 | chr3 | 130519821 | 130519929 | chr3 | 131753957 | 131754136 |
| chr3 | 132756966 | 132757205 | chr3 | 133217923 | 133218102 | chr3 | 133748044 | 133748206 |
| chr3 | 133748552 | 133748679 | chr3 | 134369572 | 134369931 | chr3 | 134514792 | 134514879 |
| chr3 | 134514960 | 134514971 | chr3 | 134515040 | 134515459 | chr3 | 134515590 | 134516309 |
| chr3 | 136537567 | 136537806 | chr3 | 136538520 | 136538910 | chr3 | 136582941 | 136583037 |
| chr3 | 136751546 | 136751833 | chr3 | 137479149 | 137479388 | chr3 | 137479525 | 137479764 |
| chr3 | 137479893 | 137480847 | chr3 | 137481094 | 137481393 | chr3 | 137481782 | 137482261 |
| chr3 | 137483212 | 137483319 | chr3 | 137483570 | 137483691 | chr3 | 137483746 | 137484105 |
| chr3 | 137484319 | 137484618 | chr3 | 137485931 | 137486390 | chr3 | 137486429 | 137486653 |
| chr3 | 137487874 | 137488113 | chr3 | 137488856 | 137491135 | chr3 | 138153889 | 138154068 |
| chr3 | 138154240 | 138154479 | chr3 | 138655857 | 138656216 | chr3 | 138656743 | 138656982 |
| chr3 | 138657347 | 138659187 | chr3 | 138662060 | 138662535 | chr3 | 138662705 | 138662941 |
| chr3 | 138663611 | 138664249 | chr3 | 138664330 | 138664569 | chr3 | 138664827 | 138665426 |
| chr3 | 138665479 | 138665718 | chr3 | 138665779 | 138666378 | chr3 | 138668646 | 138669485 |
| chr3 | 138679375 | 138679614 | chr3 | 139258173 | 139258412 | chr3 | 139653413 | 139653772 |
| chr3 | 140769430 | 140769789 | chr3 | 140769830 | 140770909 | chr3 | 140771231 | 140771410 |
| chr3 | 140771716 | 140771955 | chr3 | 141174269 | 141174688 | chr3 | 141481983 | 141482162 |
| chr3 | 141516315 | 141516794 | chr3 | 142682184 | 142682483 | chr3 | 142791076 | 142791173 |
| chr3 | 142837906 | 142838445 | chr3 | 142838530 | 142839129 | chr3 | 142839439 | 142840338 |
| chr3 | 142896066 | 142896305 | chr3 | 145878591 | 145878641 | chr3 | 146187843 | 146188069 |
| chr3 | 147074871 | 147075110 | chr3 | 147077211 | 147077640 | chr3 | 147078865 | 147079284 |
| chr3 | 147087472 | 147087891 | chr3 | 147088363 | 147088542 | chr3 | 147088840 | 147089136 |
| chr3 | 147098332 | 147098571 | chr3 | 147105805 | 147106104 | chr3 | 147108758 | 147110017 |
| chr3 | 147110055 | 147110774 | chr3 | 147110835 | 147111188 | chr3 | 147111461 | 147111734 |
| chr3 | 147126963 | 147127142 | chr3 | 147127583 | 147128002 | chr3 | 147128188 | 147128420 |
| chr3 | 147136839 | 147137258 | chr3 | 147138694 | 147138932 | chr3 | 147139052 | 147139231 |
| chr3 | 147139272 | 147139631 | chr3 | 147142126 | 147142365 | chr3 | 148415327 | 148415746 |
| chr3 | 148803259 | 148803370 | chr3 | 149374866 | 149375105 | chr3 | 150802882 | 150803181 |
| chr3 | 150803941 | 150804180 | chr3 | 150804880 | 150805119 | chr3 | 152553245 | 152553484 |
| chr3 | 152553573 | 152553807 | chr3 | 152877592 | 152877703 | chr3 | 153838725 | 153838964 |
| chr3 | 153839429 | 153839559 | chr3 | 153839641 | 153840148 | chr3 | 154146034 | 154146513 |
| chr3 | 154146572 | 154146991 | chr3 | 154797250 | 154797289 | chr3 | 154797377 | 154797789 |
| chr3 | 156008943 | 156009501 | chr3 | 156534228 | 156534407 | chr3 | 157155164 | 157155523 |
| chr3 | 157155922 | 157156298 | chr3 | 157812122 | 157812721 | chr3 | 157812812 | 157813171 |
| chr3 | 157813507 | 157813926 | chr3 | 157815787 | 157815920 | chr3 | 157820502 | 157820681 |
| chr3 | 157820985 | 157821764 | chr3 | 157821939 | 157822106 | chr3 | 157822989 | 157823228 |
| chr3 | 157823390 | 157823569 | chr3 | 157824052 | 157824332 | chr3 | 157824414 | 157824953 |
| chr3 | 157825083 | 157825491 | chr3 | 158288801 | 158288974 | chr3 | 159756593 | 159756952 |
| chr3 | 159944397 | 159944636 | chr3 | 160167929 | 160168146 | chr3 | 164912329 | 164912568 |
| chr3 | 164912827 | 164913960 | chr3 | 164914906 | 164915205 | chr3 | 169376080 | 169376319 |
| chr3 | 169376581 | 169376878 | chr3 | 169378746 | 169379105 | chr3 | 169539810 | 169540704 |
| chr3 | 169540967 | 169541134 | chr3 | 170136540 | 170136839 | chr3 | 170137571 | 170137585 |
| chr3 | 170137624 | 170137803 | chr3 | 170302528 | 170302767 | chr3 | 170302989 | 170303527 |
| chr3 | 170303563 | 170303922 | chr3 | 171527953 | 171528071 | chr3 | 172165356 | 172166725 |

TABLE 14-continued

Pan Cancer #4

| chr | start | end | chr | start | end | chr | start | end |
|---|---|---|---|---|---|---|---|---|
| chr3 | 172166783 | 172167142 | chr3 | 172167223 | 172167402 | chr3 | 172167580 | 172167995 |
| chr3 | 172355818 | 172355888 | chr3 | 172355903 | 172355997 | chr3 | 172425281 | 172425382 |
| chr3 | 172425701 | 172425802 | chr3 | 172469837 | 172469951 | chr3 | 173115155 | 173115634 |
| chr3 | 173302464 | 173302763 | chr3 | 173302900 | 173303319 | chr3 | 178861414 | 178861533 |
| chr3 | 178916788 | 178916967 | chr3 | 178921465 | 178921644 | chr3 | 178935968 | 178936205 |
| chr3 | 178951997 | 178952176 | chr3 | 179168582 | 179169354 | chr3 | 179754086 | 179755465 |
| chr3 | 181413068 | 181413460 | chr3 | 181413647 | 181414426 | chr3 | 181419972 | 181420211 |
| chr3 | 181420226 | 181420465 | chr3 | 181421308 | 181422387 | chr3 | 181422464 | 181423063 |
| chr3 | 181428311 | 181428850 | chr3 | 181430614 | 181430853 | chr3 | 181437030 | 181437449 |
| chr3 | 181438095 | 181438454 | chr3 | 181440811 | 181442010 | chr3 | 181442069 | 181442488 |
| chr3 | 181442927 | 181443646 | chr3 | 181443662 | 181443961 | chr3 | 181444023 | 181444322 |
| chr3 | 181444335 | 181444754 | chr3 | 181444828 | 181445114 | chr3 | 181445268 | 181445567 |
| chr3 | 181445649 | 181445948 | chr3 | 182816010 | 182816129 | chr3 | 182895871 | 182895990 |
| chr3 | 183145336 | 183145695 | chr3 | 183145829 | 183146128 | chr3 | 183146297 | 183146536 |
| chr3 | 183146574 | 183146753 | chr3 | 183648036 | 183648101 | chr3 | 183728814 | 183728926 |
| chr3 | 183965514 | 183965625 | chr3 | 184017964 | 184018237 | chr3 | 184031615 | 184031734 |
| chr3 | 184057527 | 184057636 | chr3 | 184301634 | 184301873 | chr3 | 184319741 | 184319980 |
| chr3 | 185001908 | 185002018 | chr3 | 185271201 | 185271380 | chr3 | 185303173 | 185303352 |
| chr3 | 185362989 | 185363348 | chr3 | 185643246 | 185643485 | chr3 | 186078683 | 186078982 |
| chr3 | 186079119 | 186079412 | chr3 | 186080114 | 186080293 | chr3 | 186857051 | 186857710 |
| chr3 | 187387776 | 187388315 | chr3 | 192125754 | 192125903 | chr3 | 192126056 | 192126955 |
| chr3 | 192127265 | 192128164 | chr3 | 192232017 | 192232256 | chr3 | 192232362 | 192232437 |
| chr3 | 192232478 | 192232661 | chr3 | 192232753 | 192233232 | chr3 | 192958830 | 192959057 |
| chr3 | 193312046 | 193312165 | chr3 | 193419628 | 193419745 | chr3 | 193548557 | 193548797 |
| chr3 | 193548842 | 193548916 | chr3 | 193776015 | 193776194 | chr3 | 194048731 | 194049015 |
| chr3 | 194208185 | 194208664 | chr3 | 194407924 | 194407936 | chr3 | 194408055 | 194408103 |
| chr3 | 194408279 | 194409118 | chr3 | 195536642 | 195536828 | chr3 | 195538330 | 195538435 |
| chr3 | 195586956 | 195587195 | chr3 | 195601157 | 195601363 | chr3 | 195602364 | 195602435 |
| chr3 | 195648720 | 195648899 | chr3 | 196069893 | 196070192 | chr3 | 196255543 | 196255722 |
| chr3 | 196387206 | 196387505 | chr3 | 196387528 | 196387767 | chr3 | 196388303 | 196388662 |
| chr3 | 196731055 | 196731133 | chr3 | 196731197 | 196731414 | chr3 | 196755893 | 196756063 |
| chr3 | 197327025 | 197327131 | chr3 | 197616633 | 197616812 | chr3 | 197676955 | 197677134 |
| chr3 | 197685698 | 197685817 | chr3 | 197686060 | 197686177 | chr3 | 197686891 | 197687310 |
| chr4 | 107616 | 107855 | chr4 | 330311 | 330790 | chr4 | 331308 | 331416 |
| chr4 | 568333 | 570012 | chr4 | 570931 | 571110 | chr4 | 571420 | 571779 |
| chr4 | 628488 | 628770 | chr4 | 651110 | 651348 | chr4 | 657570 | 657657 |
| chr4 | 678397 | 678576 | chr4 | 682710 | 683009 | chr4 | 718082 | 718202 |
| chr4 | 718240 | 718321 | chr4 | 829537 | 829716 | chr4 | 955292 | 955531 |
| chr4 | 955774 | 956013 | chr4 | 995777 | 996436 | chr4 | 996555 | 996794 |
| chr4 | 1008642 | 1008806 | chr4 | 1016041 | 1016340 | chr4 | 1016533 | 1016787 |
| chr4 | 1025852 | 1026151 | chr4 | 1093457 | 1093558 | chr4 | 1165276 | 1165575 |
| chr4 | 1188947 | 1189126 | chr4 | 1282441 | 1282620 | chr4 | 1331636 | 1331780 |
| chr4 | 1338615 | 1338891 | chr4 | 1339023 | 1339130 | chr4 | 1396498 | 1396917 |
| chr4 | 1397297 | 1397596 | chr4 | 1398222 | 1398461 | chr4 | 1399627 | 1399652 |
| chr4 | 1400638 | 1400877 | chr4 | 1401608 | 1401847 | chr4 | 1512294 | 1512473 |
| chr4 | 1556335 | 1556603 | chr4 | 1576387 | 1576626 | chr4 | 1616606 | 1617173 |
| chr4 | 1687006 | 1687185 | chr4 | 1803447 | 1803686 | chr4 | 1806010 | 1806089 |
| chr4 | 1807281 | 1807460 | chr4 | 1993677 | 1994276 | chr4 | 2042117 | 2042631 |
| chr4 | 2066011 | 2066370 | chr4 | 2305571 | 2305930 | chr4 | 2527903 | 2528012 |
| chr4 | 2540247 | 2540395 | chr4 | 2765767 | 2766006 | chr4 | 2926292 | 2926471 |
| chr4 | 2978878 | 2979094 | chr4 | 3446917 | 3447096 | chr4 | 3447737 | 3448096 |
| chr4 | 3768759 | 3769418 | chr4 | 3769439 | 3769678 | chr4 | 3873613 | 3873852 |
| chr4 | 4228094 | 4228333 | chr4 | 4229586 | 4229885 | chr4 | 4387431 | 4387730 |
| chr4 | 4417467 | 4417706 | chr4 | 4855018 | 4855257 | chr4 | 4855283 | 4855522 |
| chr4 | 4862671 | 4863210 | chr4 | 4867613 | 4867864 | chr4 | 4867924 | 4867972 |
| chr4 | 4868468 | 4869187 | chr4 | 4872009 | 4872248 | chr4 | 4872695 | 4872934 |
| chr4 | 4873329 | 4873580 | chr4 | 5052995 | 5053594 | chr4 | 5053651 | 5054190 |
| chr4 | 5709819 | 5710358 | chr4 | 5712891 | 5713370 | chr4 | 5889848 | 5890147 |
| chr4 | 5890180 | 5890539 | chr4 | 5891871 | 5892290 | chr4 | 5892676 | 5892791 |
| chr4 | 5893898 | 5894434 | chr4 | 5894583 | 5894882 | chr4 | 6200797 | 6201336 |
| chr4 | 6202011 | 6202370 | chr4 | 6247277 | 6247456 | chr4 | 6564904 | 6565143 |
| chr4 | 6670110 | 6670289 | chr4 | 6748251 | 6748662 | chr4 | 6957489 | 6957701 |
| chr4 | 7647679 | 7648038 | chr4 | 7758402 | 7758581 | chr4 | 8582475 | 8582654 |
| chr4 | 8607724 | 8608023 | chr4 | 8608459 | 8608698 | chr4 | 8858804 | 8859823 |
| chr4 | 8859875 | 8860654 | chr4 | 8861563 | 8862102 | chr4 | 8862705 | 8863004 |
| chr4 | 8863339 | 8863878 | chr4 | 8864434 | 8864699 | chr4 | 8864736 | 8865155 |
| chr4 | 8868734 | 8869453 | chr4 | 8869498 | 8869917 | chr4 | 8872957 | 8873436 |
| chr4 | 8873718 | 8874077 | chr4 | 8874397 | 8874812 | chr4 | 8875803 | 8875982 |
| chr4 | 8893427 | 8893606 | chr4 | 8893714 | 8894013 | chr4 | 8894547 | 8895446 |
| chr4 | 8895480 | 8895659 | chr4 | 8895835 | 8896134 | chr4 | 9423195 | 9423281 |
| chr4 | 9782942 | 9783502 | chr4 | 10458309 | 10459208 | chr4 | 10462740 | 10463636 |
| chr4 | 11429482 | 11429720 | chr4 | 13523929 | 13524528 | chr4 | 13524571 | 13524872 |
| chr4 | 13537492 | 13537779 | chr4 | 13540907 | 13541146 | chr4 | 13541309 | 13541548 |
| chr4 | 13543777 | 13544196 | chr4 | 13545483 | 13545842 | chr4 | 13545933 | 13546172 |
| chr4 | 13548404 | 13548999 | chr4 | 13549246 | 13549605 | chr4 | 15780123 | 15780422 |
| chr4 | 16084642 | 16085481 | chr4 | 16085531 | 16085770 | chr4 | 17782913 | 17783692 |

TABLE 14-continued

Pan Cancer #4

| chr | start | end | chr | start | end | chr | start | end |
|---|---|---|---|---|---|---|---|---|
| chr4 | 20254619 | 20254798 | chr4 | 20255339 | 20255938 | chr4 | 20256067 | 20256426 |
| chr4 | 21950146 | 21950445 | chr4 | 24801718 | 24802077 | chr4 | 24914564 | 24914743 |
| chr4 | 25656728 | 25656893 | chr4 | 25657338 | 25657577 | chr4 | 27086358 | 27086537 |
| chr4 | 30724162 | 30724461 | chr4 | 37245640 | 37245939 | chr4 | 37246060 | 37246959 |
| chr4 | 37247007 | 37247306 | chr4 | 40910205 | 40910563 | chr4 | 41258624 | 41259276 |
| chr4 | 41746922 | 41747221 | chr4 | 41747419 | 41747658 | chr4 | 41747858 | 41747977 |
| chr4 | 41748038 | 41748397 | chr4 | 41748583 | 41748882 | chr4 | 41748976 | 41749138 |
| chr4 | 41749187 | 41749846 | chr4 | 41750125 | 41750604 | chr4 | 41751789 | 41751990 |
| chr4 | 41752363 | 41752782 | chr4 | 41752884 | 41753483 | chr4 | 41753512 | 41754171 |
| chr4 | 41875337 | 41875891 | chr4 | 41881286 | 41881517 | chr4 | 41882469 | 41882682 |
| chr4 | 41882988 | 41883407 | chr4 | 41883411 | 41883710 | chr4 | 41993731 | 41993896 |
| chr4 | 42152808 | 42154127 | chr4 | 42154201 | 42154440 | chr4 | 42154561 | 42155100 |
| chr4 | 42398768 | 42398947 | chr4 | 42399045 | 42399284 | chr4 | 42399601 | 42399960 |
| chr4 | 44449387 | 44449746 | chr4 | 44450170 | 44450469 | chr4 | 46995079 | 46995918 |
| chr4 | 47034834 | 47035013 | chr4 | 48485152 | 48486104 | chr4 | 48486254 | 48486493 |
| chr4 | 48492100 | 48492517 | chr4 | 48988013 | 48988229 | chr4 | 48988380 | 48988432 |
| chr4 | 53728417 | 53729087 | chr4 | 54966756 | 54967175 | chr4 | 54967264 | 54967563 |
| chr4 | 54969832 | 54970174 | chr4 | 54970277 | 54970576 | chr4 | 54975855 | 54976214 |
| chr4 | 55092973 | 55093332 | chr4 | 55096143 | 55096363 | chr4 | 55096441 | 55096442 |
| chr4 | 55097315 | 55097554 | chr4 | 55097709 | 55097729 | chr4 | 55097874 | 55098473 |
| chr4 | 55098590 | 55098769 | chr4 | 55099040 | 55099159 | chr4 | 55524138 | 55524367 |
| chr4 | 55991019 | 55991270 | chr4 | 55992030 | 55992269 | chr4 | 56659618 | 56660097 |
| chr4 | 57371632 | 57372051 | chr4 | 57372241 | 57372600 | chr4 | 57396866 | 57397345 |
| chr4 | 57521300 | 57522908 | chr4 | 57687632 | 57687871 | chr4 | 57777338 | 57777577 |
| chr4 | 57803529 | 57803613 | chr4 | 57975930 | 57976289 | chr4 | 57976316 | 57976675 |
| chr4 | 62066106 | 62066645 | chr4 | 62067419 | 62067718 | chr4 | 62067992 | 62068231 |
| chr4 | 66535048 | 66535527 | chr4 | 66536068 | 66536427 | chr4 | 74702379 | 74702608 |
| chr4 | 74809786 | 74810025 | chr4 | 75241349 | 75241528 | chr4 | 75858482 | 75858611 |
| chr4 | 76555455 | 76555934 | chr4 | 76912717 | 76912836 | chr4 | 79689573 | 79689812 |
| chr4 | 81106252 | 81106669 | chr4 | 81124201 | 81124740 | chr4 | 81186972 | 81187151 |
| chr4 | 81187485 | 81187664 | chr4 | 81188230 | 81188644 | chr4 | 81189336 | 81189995 |
| chr4 | 81951357 | 81951536 | chr4 | 81951938 | 81952046 | chr4 | 81952078 | 81952437 |
| chr4 | 82135786 | 82136145 | chr4 | 82136403 | 82136642 | chr4 | 82136733 | 82136912 |
| chr4 | 83323428 | 83323677 | chr4 | 85402681 | 85403425 | chr4 | 85403824 | 85404783 |
| chr4 | 85413977 | 85414244 | chr4 | 85414270 | 85414509 | chr4 | 85414637 | 85414936 |
| chr4 | 85417241 | 85417474 | chr4 | 85417517 | 85417660 | chr4 | 85417873 | 85418166 |
| chr4 | 85418319 | 85419038 | chr4 | 85422101 | 85422520 | chr4 | 85422866 | 85423405 |
| chr4 | 85424323 | 85424562 | chr4 | 87515263 | 87515442 | chr4 | 89378362 | 89378601 |
| chr4 | 89378667 | 89378966 | chr4 | 90757439 | 90757913 | chr4 | 90758031 | 90758210 |
| chr4 | 90758681 | 90758980 | chr4 | 93225163 | 93225252 | chr4 | 93226367 | 93226606 |
| chr4 | 93226719 | 93226958 | chr4 | 94750882 | 94751241 | chr4 | 94751342 | 94751581 |
| chr4 | 94753341 | 94753520 | chr4 | 94755887 | 94756186 | chr4 | 95127560 | 95127679 |
| chr4 | 96470678 | 96470857 | chr4 | 101111166 | 101111585 | chr4 | 101111765 | 101112058 |
| chr4 | 107955210 | 107955929 | chr4 | 107956582 | 107957181 | chr4 | 107957271 | 107957570 |
| chr4 | 109093016 | 109093255 | chr4 | 109093307 | 109093606 | chr4 | 110222996 | 110224075 |
| chr4 | 111532558 | 111533037 | chr4 | 111536192 | 111536791 | chr4 | 111536882 | 111537121 |
| chr4 | 111537356 | 111537572 | chr4 | 111540101 | 111540460 | chr4 | 111542113 | 111542570 |
| chr4 | 111542728 | 111542832 | chr4 | 111543132 | 111543551 | chr4 | 111543579 | 111543807 |
| chr4 | 111544303 | 111544662 | chr4 | 111549726 | 111549905 | chr4 | 111550517 | 111550930 |
| chr4 | 111552044 | 111552223 | chr4 | 111553006 | 111553545 | chr4 | 111553815 | 111554054 |
| chr4 | 111554864 | 111555447 | chr4 | 111557888 | 111558127 | chr4 | 111558473 | 111559312 |
| chr4 | 111560174 | 111560713 | chr4 | 111562493 | 111562732 | chr4 | 113154804 | 113155043 |
| chr4 | 113430537 | 113430776 | chr4 | 113431755 | 113432654 | chr4 | 113436133 | 113436372 |
| chr4 | 113441514 | 113441813 | chr4 | 113442013 | 113442612 | chr4 | 113444003 | 113444534 |
| chr4 | 117847310 | 117847549 | chr4 | 121843986 | 121844285 | chr4 | 121992170 | 121992409 |
| chr4 | 121993915 | 121994334 | chr4 | 122301405 | 122301934 | chr4 | 122302032 | 122302331 |
| chr4 | 122685744 | 122686029 | chr4 | 122686119 | 122686598 | chr4 | 122871195 | 122871434 |
| chr4 | 122871488 | 122872087 | chr4 | 123664147 | 123664249 | chr4 | 126237252 | 126237491 |
| chr4 | 126237552 | 126237701 | chr4 | 126237931 | 126237851 | chr4 | 128543956 | 128544255 |
| chr4 | 128544569 | 128544868 | chr4 | 134067794 | 134068093 | chr4 | 134068475 | 134068894 |
| chr4 | 134069215 | 134069394 | chr4 | 134069498 | 134069977 | chr4 | 134070300 | 134070479 |
| chr4 | 134071559 | 134073058 | chr4 | 134073104 | 134073403 | chr4 | 134073486 | 134073725 |
| chr4 | 134073772 | 134073789 | chr4 | 134073944 | 134074243 | chr4 | 140200427 | 140201566 |
| chr4 | 140656567 | 140657166 | chr4 | 141347925 | 141348227 | chr4 | 141418841 | 141419500 |
| chr4 | 141488790 | 141489159 | chr4 | 142053155 | 142053235 | chr4 | 142053418 | 142053837 |
| chr4 | 142054141 | 142054560 | chr4 | 143766714 | 143767013 | chr4 | 144621248 | 144622147 |
| chr4 | 145567951 | 145568250 | chr4 | 145568361 | 145568745 | chr4 | 146853937 | 146854056 |
| chr4 | 147558179 | 147558598 | chr4 | 147559220 | 147560659 | chr4 | 147560835 | 147562154 |
| chr4 | 147568549 | 147569148 | chr4 | 147569546 | 147569685 | chr4 | 147569697 | 147569725 |
| chr4 | 147576079 | 147576738 | chr4 | 152246058 | 152246237 | chr4 | 152246398 | 152246403 |
| chr4 | 153249297 | 153249476 | chr4 | 153702690 | 153702805 | chr4 | 154216277 | 154216449 |
| chr4 | 154709440 | 154710639 | chr4 | 154710701 | 154710999 | chr4 | 154712084 | 154712683 |
| chr4 | 154713426 | 154713605 | chr4 | 154713861 | 154714085 | chr4 | 155254092 | 155254271 |
| chr4 | 155411411 | 155411786 | chr4 | 155411930 | 155412370 | chr4 | 155663129 | 155663728 |
| chr4 | 155665371 | 155665550 | chr4 | 156129079 | 156129258 | chr4 | 156129354 | 156129593 |
| chr4 | 156129653 | 156129892 | chr4 | 156129963 | 156130382 | chr4 | 156297337 | 156297636 |

TABLE 14-continued

| Pan Cancer #4 | | | | | | | | |
|---|---|---|---|---|---|---|---|---|
| chr | start | end | chr | start | end | chr | start | end |
| chr4 | 156297747 | 156298130 | chr4 | 156588237 | 156588245 | chr4 | 156588364 | 156588476 |
| chr4 | 156589179 | 156589203 | chr4 | 156589259 | 156589418 | chr4 | 156680156 | 156680485 |
| chr4 | 156680596 | 156680635 | chr4 | 156681281 | 156681465 | chr4 | 158141502 | 158141681 |
| chr4 | 158142744 | 158143101 | chr4 | 158143355 | 158143646 | chr4 | 164252890 | 164253549 |
| chr4 | 165304428 | 165304667 | chr4 | 165304948 | 165305247 | chr4 | 166414817 | 166414996 |
| chr4 | 166794691 | 166794990 | chr4 | 166795933 | 166796292 | chr4 | 168155010 | 168155369 |
| chr4 | 170865262 | 170865381 | chr4 | 170947187 | 170947426 | chr4 | 172734067 | 172734306 |
| chr4 | 172734461 | 172734880 | chr4 | 174429584 | 174429763 | chr4 | 174430212 | 174431171 |
| chr4 | 174438477 | 174438627 | chr4 | 174439741 | 174440340 | chr4 | 174440555 | 174440794 |
| chr4 | 174443138 | 174443317 | chr4 | 174443480 | 174444019 | chr4 | 174444077 | 174444256 |
| chr4 | 174446387 | 174446595 | chr4 | 174449847 | 174451586 | chr4 | 174451768 | 174452187 |
| chr4 | 174459094 | 174459747 | chr4 | 174459770 | 174459933 | chr4 | 174460085 | 174460309 |
| chr4 | 175132661 | 175132840 | chr4 | 175132994 | 175133293 | chr4 | 175134806 | 175135765 |
| chr4 | 175135847 | 175136086 | chr4 | 175138419 | 175138629 | chr4 | 175138870 | 175139349 |
| chr4 | 175139473 | 175139772 | chr4 | 175750358 | 175750805 | chr4 | 176923342 | 176923641 |
| chr4 | 176987230 | 176987448 | chr4 | 177713154 | 177713513 | chr4 | 180979196 | 180979375 |
| chr4 | 180980208 | 180980447 | chr4 | 183063573 | 183064048 | chr4 | 183064517 | 183064756 |
| chr4 | 183064771 | 183065070 | chr4 | 184019164 | 184019403 | chr4 | 184019595 | 184019834 |
| chr4 | 184020043 | 184020263 | chr4 | 184375709 | 184375816 | chr4 | 184718157 | 184718456 |
| chr4 | 184826157 | 184826576 | chr4 | 184826976 | 184827328 | chr4 | 184921806 | 184922165 |
| chr4 | 185089598 | 185089897 | chr4 | 185937252 | 185937971 | chr4 | 185938412 | 185938651 |
| chr4 | 185940250 | 185940549 | chr4 | 185941484 | 185942863 | chr5 | 53756 | 53995 |
| chr5 | 92072 | 92210 | chr5 | 320762 | 321061 | chr5 | 343957 | 344017 |
| chr5 | 373976 | 374369 | chr5 | 400112 | 400291 | chr5 | 480918 | 481037 |
| chr5 | 491257 | 491616 | chr5 | 524252 | 524491 | chr5 | 528502 | 528775 |
| chr5 | 538663 | 538902 | chr5 | 554212 | 554569 | chr5 | 554812 | 554916 |
| chr5 | 555193 | 555372 | chr5 | 555891 | 556070 | chr5 | 677799 | 678098 |
| chr5 | 1034508 | 1034747 | chr5 | 1131130 | 1131478 | chr5 | 1193302 | 1193465 |
| chr5 | 1193793 | 1194032 | chr5 | 1221103 | 1221402 | chr5 | 1294550 | 1294849 |
| chr5 | 1294928 | 1295767 | chr5 | 1445078 | 1445369 | chr5 | 1445654 | 1446013 |
| chr5 | 1446220 | 1446699 | chr5 | 1746941 | 1747180 | chr5 | 1874877 | 1875176 |
| chr5 | 1875356 | 1875595 | chr5 | 1875796 | 1876935 | chr5 | 1877081 | 1877320 |
| chr5 | 1877912 | 1878631 | chr5 | 1878653 | 1879090 | chr5 | 1879513 | 1879812 |
| chr5 | 1882211 | 1882690 | chr5 | 1882758 | 1883177 | chr5 | 1883429 | 1883908 |
| chr5 | 1884089 | 1884328 | chr5 | 1884479 | 1884778 | chr5 | 1885069 | 1885548 |
| chr5 | 1885910 | 1886269 | chr5 | 1886443 | 1886682 | chr5 | 1886736 | 1887815 |
| chr5 | 1930701 | 1931840 | chr5 | 1950698 | 1951057 | chr5 | 1952550 | 1952729 |
| chr5 | 2038629 | 2038928 | chr5 | 2324309 | 2324488 | chr5 | 2541400 | 2541699 |
| chr5 | 2738746 | 2739525 | chr5 | 2739780 | 2741139 | chr5 | 2743516 | 2743815 |
| chr5 | 2748298 | 2748537 | chr5 | 2749110 | 2749529 | chr5 | 2749625 | 2749804 |
| chr5 | 2750617 | 2751456 | chr5 | 2751615 | 2751974 | chr5 | 2752897 | 2753153 |
| chr5 | 2754664 | 2754703 | chr5 | 2754804 | 2754843 | chr5 | 2755227 | 2756486 |
| chr5 | 2756504 | 2757523 | chr5 | 3031800 | 3032099 | chr5 | 3324948 | 3325367 |
| chr5 | 3590314 | 3590853 | chr5 | 3591252 | 3591491 | chr5 | 3591768 | 3592127 |
| chr5 | 3592626 | 3592961 | chr5 | 3594155 | 3594814 | chr5 | 3595015 | 3595254 |
| chr5 | 3595361 | 3596080 | chr5 | 3596118 | 3596297 | chr5 | 3596441 | 3596980 |
| chr5 | 3597317 | 3597556 | chr5 | 3599759 | 3599938 | chr5 | 3600076 | 3600255 |
| chr5 | 3600794 | 3600973 | chr5 | 3602712 | 3603422 | chr5 | 3606532 | 3606771 |
| chr5 | 3673960 | 3674256 | chr5 | 4144300 | 4144592 | chr5 | 5139578 | 5139997 |
| chr5 | 5140079 | 5140318 | chr5 | 5140527 | 5141006 | chr5 | 6228525 | 6228650 |
| chr5 | 6448837 | 6449676 | chr5 | 6583371 | 6583670 | chr5 | 6687175 | 6687528 |
| chr5 | 7395162 | 7395641 | chr5 | 7850181 | 7850286 | chr5 | 7850919 | 7851218 |
| chr5 | 9546511 | 9546750 | chr5 | 10333611 | 10334210 | chr5 | 10564925 | 10565704 |
| chr5 | 11384806 | 11385465 | chr5 | 11903659 | 11904798 | chr5 | 11904801 | 11905040 |
| chr5 | 15500659 | 15501018 | chr5 | 16178946 | 16179245 | chr5 | 16179436 | 16179795 |
| chr5 | 16179945 | 16180364 | chr5 | 16466683 | 16466796 | chr5 | 16467097 | 16467216 |
| chr5 | 16936255 | 16936402 | chr5 | 16936500 | 16936614 | chr5 | 17203036 | 17203266 |
| chr5 | 17217854 | 17218033 | chr5 | 17218121 | 17218300 | chr5 | 17218862 | 17219101 |
| chr5 | 17512040 | 17512192 | chr5 | 22853425 | 22853596 | chr5 | 31193844 | 31194083 |
| chr5 | 31194299 | 31194511 | chr5 | 31639583 | 31640008 | chr5 | 31691580 | 31691745 |
| chr5 | 31854987 | 31855286 | chr5 | 32710252 | 32710551 | chr5 | 32710718 | 32710957 |
| chr5 | 32711024 | 32711617 | chr5 | 32711729 | 32711968 | chr5 | 32711985 | 32712584 |
| chr5 | 32712675 | 32712943 | chr5 | 33298097 | 33298295 | chr5 | 33891980 | 33892219 |
| chr5 | 33892339 | 33892518 | chr5 | 33936067 | 33936751 | chr5 | 34656834 | 34657042 |
| chr5 | 37834610 | 37834789 | chr5 | 37834855 | 37834900 | chr5 | 37836572 | 37838071 |
| chr5 | 37838448 | 37838987 | chr5 | 37839684 | 37840223 | chr5 | 37840288 | 37840843 |
| chr5 | 38257397 | 38257696 | chr5 | 38257752 | 38258051 | chr5 | 38556996 | 38557076 |
| chr5 | 38557188 | 38557427 | chr5 | 38845574 | 38845955 | chr5 | 38846219 | 38846533 |
| chr5 | 39343086 | 39343201 | chr5 | 40681036 | 40681455 | chr5 | 40681601 | 40682080 |
| chr5 | 42424732 | 42425151 | chr5 | 42950902 | 42952445 | chr5 | 42991751 | 42993010 |
| chr5 | 42993313 | 42993547 | chr5 | 42993853 | 42994272 | chr5 | 42994593 | 42994892 |
| chr5 | 42995015 | 42995254 | chr5 | 43007862 | 43008041 | chr5 | 43008113 | 43008472 |
| chr5 | 43017851 | 43018690 | chr5 | 43019144 | 43019424 | chr5 | 43019729 | 43019968 |
| chr5 | 43040768 | 43041067 | chr5 | 43215459 | 43215562 | chr5 | 43396915 | 43397334 |
| chr5 | 44389705 | 44389929 | chr5 | 45695091 | 45695630 | chr5 | 45695823 | 45696047 |
| chr5 | 45696239 | 45696538 | chr5 | 49736497 | 49736789 | chr5 | 50262842 | 50263104 |

TABLE 14-continued

Pan Cancer #4

| chr | start | end | chr | start | end | chr | start | end |
|---|---|---|---|---|---|---|---|---|
| chr5 | 50263486 | 50263725 | chr5 | 50264216 | 50264695 | chr5 | 50264746 | 50264925 |
| chr5 | 50265228 | 50265527 | chr5 | 50265621 | 50265960 | chr5 | 50674051 | 50674290 |
| chr5 | 50674486 | 50674557 | chr5 | 50674638 | 50674665 | chr5 | 50674925 | 50675164 |
| chr5 | 50678269 | 50678273 | chr5 | 50678373 | 50678552 | chr5 | 50695193 | 50695540 |
| chr5 | 54179491 | 54179730 | chr5 | 54179989 | 54180168 | chr5 | 54516275 | 54517114 |
| chr5 | 54518577 | 54519406 | chr5 | 54527226 | 54527444 | chr5 | 56248119 | 56248358 |
| chr5 | 57878174 | 57878473 | chr5 | 57878612 | 57878775 | chr5 | 57878811 | 57878851 |
| chr5 | 59188293 | 59188429 | chr5 | 59188952 | 59189311 | chr5 | 59189787 | 59190026 |
| chr5 | 63254815 | 63255354 | chr5 | 63257645 | 63257944 | chr5 | 63801932 | 63802591 |
| chr5 | 63986409 | 63986888 | chr5 | 67591197 | 67591233 | chr5 | 68391320 | 68391429 |
| chr5 | 71014629 | 71014988 | chr5 | 71015095 | 71015814 | chr5 | 71403491 | 71403730 |
| chr5 | 71403882 | 71404158 | chr5 | 72416170 | 72416262 | chr5 | 72526319 | 72526738 |
| chr5 | 72528360 | 72528539 | chr5 | 72529200 | 72530699 | chr5 | 72594722 | 72595141 |
| chr5 | 72595456 | 72595875 | chr5 | 72598977 | 72599936 | chr5 | 72677577 | 72678416 |
| chr5 | 72715160 | 72715846 | chr5 | 72716022 | 72716239 | chr5 | 72732724 | 72732963 |
| chr5 | 72732990 | 72733268 | chr5 | 72740047 | 72740286 | chr5 | 72746606 | 72746785 |
| chr5 | 75377809 | 75378108 | chr5 | 75380089 | 75380268 | chr5 | 75380530 | 75381006 |
| chr5 | 76011192 | 76011431 | chr5 | 76012504 | 76012681 | chr5 | 76249176 | 76250250 |
| chr5 | 76250351 | 76250590 | chr5 | 76506369 | 76506608 | chr5 | 76506956 | 76507195 |
| chr5 | 76923601 | 76924494 | chr5 | 76924856 | 76925018 | chr5 | 76925477 | 76925776 |
| chr5 | 76928070 | 76928487 | chr5 | 76928588 | 76929007 | chr5 | 76932228 | 76932407 |
| chr5 | 76932463 | 76933362 | chr5 | 76934073 | 76934972 | chr5 | 76935937 | 76936039 |
| chr5 | 76936100 | 76936819 | chr5 | 76939328 | 76939867 | chr5 | 76940241 | 76940477 |
| chr5 | 76941115 | 76941414 | chr5 | 77140440 | 77140799 | chr5 | 77147520 | 77148214 |
| chr5 | 77148396 | 77148669 | chr5 | 77268278 | 77269408 | chr5 | 77806123 | 77806213 |
| chr5 | 78407567 | 78407926 | chr5 | 78408118 | 78408537 | chr5 | 79783152 | 79783256 |
| chr5 | 79864809 | 79865168 | chr5 | 79865969 | 79866508 | chr5 | 79947497 | 79947796 |
| chr5 | 80255722 | 80256261 | chr5 | 80689499 | 80689819 | chr5 | 80690030 | 80690278 |
| chr5 | 82767342 | 82767881 | chr5 | 82768798 | 82769157 | chr5 | 83679121 | 83679300 |
| chr5 | 83679592 | 83680431 | chr5 | 83680592 | 83680812 | chr5 | 87955360 | 87955455 |
| chr5 | 87955502 | 87955899 | chr5 | 87956103 | 87957062 | chr5 | 87962865 | 87963006 |
| chr5 | 87963365 | 87963601 | chr5 | 87967686 | 87968165 | chr5 | 87968411 | 87968942 |
| chr5 | 87970114 | 87970953 | chr5 | 87974027 | 87974386 | chr5 | 87974767 | 87975126 |
| chr5 | 87976104 | 87976408 | chr5 | 87976423 | 87976662 | chr5 | 87979655 | 87979779 |
| chr5 | 87979900 | 87980014 | chr5 | 87980047 | 87980079 | chr5 | 87980322 | 87980346 |
| chr5 | 87980871 | 87981341 | chr5 | 87985819 | 87986058 | chr5 | 87986127 | 87986154 |
| chr5 | 87986233 | 87986366 | chr5 | 87986445 | 87986472 | chr5 | 87988431 | 87988670 |
| chr5 | 87990311 | 87990530 | chr5 | 88185377 | 88186087 | chr5 | 89854760 | 89854999 |
| chr5 | 92939817 | 92940236 | chr5 | 94955591 | 94956010 | chr5 | 94956849 | 94957088 |
| chr5 | 94982143 | 94982314 | chr5 | 95767856 | 95768035 | chr5 | 95768068 | 95768427 |
| chr5 | 95768828 | 95769173 | chr5 | 100236601 | 100236840 | chr5 | 100238808 | 100239167 |
| chr5 | 101631391 | 101631630 | chr5 | 107005906 | 107006265 | chr5 | 111987788 | 111987901 |
| chr5 | 112043011 | 112043367 | chr5 | 112073328 | 112073567 | chr5 | 112175566 | 112175730 |
| chr5 | 112629342 | 112629359 | chr5 | 112629394 | 112629761 | chr5 | 113391163 | 113391218 |
| chr5 | 113391284 | 113392122 | chr5 | 113698466 | 113698885 | chr5 | 113698915 | 113699203 |
| chr5 | 114514867 | 114515754 | chr5 | 115151174 | 115152733 | chr5 | 115297105 | 115297644 |
| chr5 | 115297836 | 115298135 | chr5 | 115298410 | 115298829 | chr5 | 115298894 | 115299133 |
| chr5 | 119799840 | 119800079 | chr5 | 119801223 | 119801522 | chr5 | 121413445 | 121413684 |
| chr5 | 122422161 | 122422386 | chr5 | 122422516 | 122422754 | chr5 | 122423233 | 122423452 |
| chr5 | 122425029 | 122425268 | chr5 | 122431039 | 122431458 | chr5 | 124128503 | 124128754 |
| chr5 | 126626256 | 126626795 | chr5 | 127872847 | 127873086 | chr5 | 127873190 | 127873789 |
| chr5 | 127874345 | 127874944 | chr5 | 128300588 | 128300887 | chr5 | 128795984 | 128796343 |
| chr5 | 128796777 | 128797076 | chr5 | 128797246 | 128797485 | chr5 | 129239966 | 129240205 |
| chr5 | 131992008 | 131992247 | chr5 | 132947392 | 132947931 | chr5 | 133820025 | 133820136 |
| chr5 | 134363235 | 134363320 | chr5 | 134364026 | 134364075 | chr5 | 134364115 | 134364205 |
| chr5 | 134364295 | 134364594 | chr5 | 134366634 | 134366873 | chr5 | 134367007 | 134367306 |
| chr5 | 134374370 | 134375309 | chr5 | 134376120 | 134376474 | chr5 | 134376612 | 134376911 |
| chr5 | 134385869 | 134386466 | chr5 | 134582953 | 134582969 | chr5 | 134825372 | 134825611 |
| chr5 | 134825799 | 134826098 | chr5 | 134870362 | 134870601 | chr5 | 134870689 | 134871288 |
| chr5 | 134871526 | 134872125 | chr5 | 134879391 | 134879973 | chr5 | 134880154 | 134880590 |
| chr5 | 134914539 | 134914838 | chr5 | 135265664 | 135265842 | chr5 | 135266034 | 135266753 |
| chr5 | 135528098 | 135528337 | chr5 | 136834009 | 136834608 | chr5 | 136834624 | 136834923 |
| chr5 | 137225016 | 137225268 | chr5 | 138273717 | 138273845 | chr5 | 139047897 | 139048256 |
| chr5 | 139227692 | 139227991 | chr5 | 139525654 | 139525833 | chr5 | 139779840 | 139779953 |
| chr5 | 140174701 | 140174994 | chr5 | 140187003 | 140187240 | chr5 | 140305895 | 140306134 |
| chr5 | 140306228 | 140306827 | chr5 | 140346514 | 140346753 | chr5 | 140514817 | 140514996 |
| chr5 | 140604361 | 140604596 | chr5 | 140613851 | 140614089 | chr5 | 140614230 | 140614469 |
| chr5 | 140777354 | 140777588 | chr5 | 140797000 | 140797419 | chr5 | 140800384 | 140801343 |
| chr5 | 140811013 | 140811138 | chr5 | 140855515 | 140856710 | chr5 | 141031047 | 141031205 |
| chr5 | 141262957 | 141263316 | chr5 | 141931261 | 141931585 | chr5 | 142784881 | 142785305 |
| chr5 | 145713562 | 145713981 | chr5 | 145717097 | 145717516 | chr5 | 145718714 | 145720024 |
| chr5 | 145720763 | 145720942 | chr5 | 145722033 | 145723112 | chr5 | 145724421 | 145724780 |
| chr5 | 145725109 | 145725948 | chr5 | 146257258 | 146257677 | chr5 | 146889129 | 146889668 |
| chr5 | 149681971 | 149682270 | chr5 | 150051025 | 150051744 | chr5 | 150400044 | 150400283 |
| chr5 | 151066339 | 151066578 | chr5 | 151304297 | 151304476 | chr5 | 153852579 | 153852878 |
| chr5 | 153853330 | 153853569 | chr5 | 153855101 | 153855340 | chr5 | 153855506 | 153855925 |

TABLE 14-continued

| Pan Cancer #4 | | | | | | | | |
|---|---|---|---|---|---|---|---|---|
| chr | start | end | chr | start | end | chr | start | end |
| chr5 | 153856004 | 153856483 | chr5 | 153856847 | 153857086 | chr5 | 153857285 | 153857524 |
| chr5 | 153858220 | 153858699 | chr5 | 153859573 | 153859812 | chr5 | 153861948 | 153862667 |
| chr5 | 153863347 | 153863526 | chr5 | 154209838 | 154210070 | chr5 | 154318060 | 154318178 |
| chr5 | 155107702 | 155107941 | chr5 | 155108042 | 155108612 | chr5 | 155108659 | 155108838 |
| chr5 | 156874164 | 156874403 | chr5 | 157001643 | 157001941 | chr5 | 157078345 | 157078524 |
| chr5 | 157098282 | 157098701 | chr5 | 158478385 | 158478864 | chr5 | 158524601 | 158524837 |
| chr5 | 158527367 | 158528146 | chr5 | 159399015 | 159399314 | chr5 | 160975650 | 160975829 |
| chr5 | 161274223 | 161274358 | chr5 | 161274506 | 161274642 | chr5 | 166865354 | 166865462 |
| chr5 | 167956087 | 167956560 | chr5 | 167956601 | 167956686 | chr5 | 168233320 | 168233559 |
| chr5 | 168727837 | 168728076 | chr5 | 169064237 | 169064887 | chr5 | 169532851 | 169533090 |
| chr5 | 170108211 | 170108450 | chr5 | 170289352 | 170289395 | chr5 | 170735061 | 170735300 |
| chr5 | 170735336 | 170735875 | chr5 | 170736019 | 170737578 | chr5 | 170737779 | 170739571 |
| chr5 | 170739746 | 170740058 | chr5 | 170740091 | 170740105 | chr5 | 170740391 | 170741031 |
| chr5 | 170741508 | 170742827 | chr5 | 170743151 | 170744207 | chr5 | 170744290 | 170744649 |
| chr5 | 170745286 | 170745560 | chr5 | 172655778 | 172656317 | chr5 | 172659314 | 172659378 |
| chr5 | 172659397 | 172659756 | chr5 | 172659768 | 172660307 | chr5 | 172660633 | 172661228 |
| chr5 | 172661368 | 172661772 | chr5 | 172664148 | 172664565 | chr5 | 172665492 | 172665911 |
| chr5 | 172670882 | 172671121 | chr5 | 172671268 | 172671926 | chr5 | 172672391 | 172672406 |
| chr5 | 172672593 | 172672750 | chr5 | 172754486 | 172754725 | chr5 | 172754733 | 172755032 |
| chr5 | 172755388 | 172755745 | chr5 | 172756961 | 172757200 | chr5 | 174115296 | 174115690 |
| chr5 | 174115864 | 174115955 | chr5 | 174147441 | 174147680 | chr5 | 174150341 | 174150520 |
| chr5 | 174158719 | 174159669 | chr5 | 174162800 | 174162945 | chr5 | 174220897 | 174221036 |
| chr5 | 174870643 | 174870882 | chr5 | 174871097 | 174871576 | chr5 | 174921381 | 174921483 |
| chr5 | 175085059 | 175085298 | chr5 | 175085389 | 175085808 | chr5 | 175223571 | 175223810 |
| chr5 | 175223935 | 175224354 | chr5 | 175298507 | 175299886 | chr5 | 175299196 | 175299495 |
| chr5 | 175300277 | 175300456 | chr5 | 175621297 | 175621596 | chr5 | 175792785 | 175793144 |
| chr5 | 176023818 | 176024350 | chr5 | 176046280 | 176046639 | chr5 | 176107191 | 176107670 |
| chr5 | 176236631 | 176236990 | chr5 | 176264711 | 176264998 | chr5 | 176764020 | 176764255 |
| chr5 | 177031093 | 177031272 | chr5 | 177408416 | 177408548 | chr5 | 177411561 | 177412210 |
| chr5 | 177713273 | 177713572 | chr5 | 178003629 | 178003928 | chr5 | 178004231 | 178004470 |
| chr5 | 178016513 | 178017971 | chr5 | 178367990 | 178368462 | chr5 | 178421400 | 178421579 |
| chr5 | 178421685 | 178422099 | chr5 | 178422167 | 178422224 | chr5 | 178487023 | 178487493 |
| chr5 | 178576382 | 178576578 | chr5 | 178655663 | 178655962 | chr5 | 178771216 | 178772055 |
| chr5 | 178772120 | 178772359 | chr5 | 178772525 | 178772824 | chr5 | 178957552 | 178958023 |
| chr5 | 179214036 | 179214275 | chr5 | 179243892 | 179244371 | chr5 | 179780005 | 179780244 |
| chr5 | 179780607 | 179781086 | chr5 | 179867405 | 179867637 | chr5 | 180017039 | 180017278 |
| chr5 | 180017532 | 180018011 | chr5 | 180018226 | 180018585 | chr5 | 180047646 | 180047703 |
| chr5 | 180075753 | 180076412 | chr5 | 180076466 | 180076945 | chr5 | 180076721 | 180077080 |
| chr5 | 180100825 | 180101410 | chr5 | 180326052 | 180326231 | chr5 | 180527447 | 180527866 |
| chr5 | 180600769 | 180601030 | chr5 | 180601129 | 180601308 | chr6 | 391089 | 392097 |
| chr6 | 392230 | 393729 | chr6 | 711039 | 711392 | chr6 | 1311899 | 1312095 |
| chr6 | 1312680 | 1312802 | chr6 | 1314014 | 1314150 | chr6 | 1378133 | 1379332 |
| chr6 | 1379510 | 1379689 | chr6 | 1379812 | 1380051 | chr6 | 1383598 | 1384731 |
| chr6 | 1385025 | 1385264 | chr6 | 1386020 | 1386212 | chr6 | 1389044 | 1389343 |
| chr6 | 1390159 | 1391118 | chr6 | 1391230 | 1391469 | chr6 | 1524122 | 1524361 |
| chr6 | 1605302 | 1605541 | chr6 | 1614740 | 1615279 | chr6 | 1624940 | 1625059 |
| chr6 | 1625129 | 1625779 | chr6 | 3053237 | 3053463 | chr6 | 3228955 | 3229134 |
| chr6 | 3229348 | 3229587 | chr6 | 3231926 | 3232029 | chr6 | 3285129 | 3285608 |
| chr6 | 3405599 | 3405778 | chr6 | 4775080 | 4775322 | chr6 | 4836441 | 4836545 |
| chr6 | 4951178 | 4951469 | chr6 | 5783232 | 5783457 | chr6 | 5996852 | 5997091 |
| chr6 | 5997728 | 5997907 | chr6 | 6003213 | 6005450 | chr6 | 6006278 | 6006498 |
| chr6 | 6006600 | 6006959 | chr6 | 6007516 | 6007772 | chr6 | 6007833 | 6008355 |
| chr6 | 6367000 | 6367218 | chr6 | 7726260 | 7726439 | chr6 | 7726556 | 7726735 |
| chr6 | 7726878 | 7727057 | chr6 | 7727622 | 7728221 | chr6 | 7728746 | 7729045 |
| chr6 | 10381428 | 10382383 | chr6 | 10382648 | 10383126 | chr6 | 10383638 | 10383877 |
| chr6 | 10384876 | 10386015 | chr6 | 10386123 | 10386357 | chr6 | 10389946 | 10391265 |
| chr6 | 10410429 | 10410668 | chr6 | 10411254 | 10411613 | chr6 | 10415015 | 10415314 |
| chr6 | 10415457 | 10415816 | chr6 | 10416039 | 10416445 | chr6 | 10417059 | 10417658 |
| chr6 | 10418997 | 10419596 | chr6 | 10419664 | 10420023 | chr6 | 10420975 | 10421171 |
| chr6 | 10421253 | 10422714 | chr6 | 10425411 | 10426970 | chr6 | 10881857 | 10882156 |
| chr6 | 10882247 | 10882426 | chr6 | 10882934 | 10883113 | chr6 | 10886993 | 10887772 |
| chr6 | 11043988 | 11044647 | chr6 | 12288420 | 12288779 | chr6 | 12749819 | 12750058 |
| chr6 | 12750114 | 12750353 | chr6 | 16196952 | 16197191 | chr6 | 17281327 | 17281351 |
| chr6 | 18035792 | 18036091 | chr6 | 19691621 | 19691920 | chr6 | 19691983 | 19692280 |
| chr6 | 19836983 | 19837222 | chr6 | 21664905 | 21665144 | chr6 | 24494604 | 24494843 |
| chr6 | 24647262 | 24647371 | chr6 | 26184364 | 26184476 | chr6 | 26188754 | 26189495 |
| chr6 | 26189956 | 26190075 | chr6 | 26199099 | 26199242 | chr6 | 26199612 | 26199791 |
| chr6 | 26214613 | 26214731 | chr6 | 26235124 | 26235437 | chr6 | 26240532 | 26241201 |
| chr6 | 26250378 | 26250917 | chr6 | 26250969 | 26251261 | chr6 | 26251715 | 26251940 |
| chr6 | 26252075 | 26252180 | chr6 | 26271315 | 26271854 | chr6 | 26271897 | 26272076 |
| chr6 | 26272416 | 26272715 | chr6 | 26273381 | 26273560 | chr6 | 26284786 | 26284975 |
| chr6 | 26327725 | 26328074 | chr6 | 26328206 | 26328505 | chr6 | 26332079 | 26332318 |
| chr6 | 26501764 | 26502296 | chr6 | 26550895 | 26551134 | chr6 | 26577078 | 26577557 |
| chr6 | 26987930 | 26988169 | chr6 | 27059697 | 27059936 | chr6 | 27064581 | 27065300 |
| chr6 | 27173436 | 27173855 | chr6 | 27173925 | 27174275 | chr6 | 27182856 | 27182974 |
| chr6 | 27203167 | 27203286 | chr6 | 27205240 | 27205359 | chr6 | 27205420 | 27205521 |

TABLE 14-continued

Pan Cancer #4

| chr | start | end | chr | start | end | chr | start | end |
|---|---|---|---|---|---|---|---|---|
| chr6 | 27205587 | 27206126 | chr6 | 27228079 | 27228498 | chr6 | 27247561 | 27247800 |
| chr6 | 27256016 | 27256255 | chr6 | 27256283 | 27256522 | chr6 | 27264344 | 27264468 |
| chr6 | 27279750 | 27280109 | chr6 | 27462939 | 27463778 | chr6 | 27512675 | 27513574 |
| chr6 | 27533723 | 27534442 | chr6 | 27559775 | 27560074 | chr6 | 27573073 | 27573492 |
| chr6 | 27598650 | 27598949 | chr6 | 27599071 | 27599427 | chr6 | 27635171 | 27635530 |
| chr6 | 27647625 | 27647984 | chr6 | 27648934 | 27649153 | chr6 | 27834577 | 27834936 |
| chr6 | 27834963 | 27835502 | chr6 | 27839635 | 27840174 | chr6 | 27840461 | 27840668 |
| chr6 | 27841002 | 27841240 | chr6 | 27858427 | 27858726 | chr6 | 28175105 | 28176301 |
| chr6 | 28303466 | 28303571 | chr6 | 28303847 | 28304339 | chr6 | 28367023 | 28367862 |
| chr6 | 28410896 | 28411435 | chr6 | 28414887 | 28415126 | chr6 | 28457534 | 28457713 |
| chr6 | 28457775 | 28458254 | chr6 | 33955409 | 33955828 | chr6 | 34170869 | 34170986 |
| chr6 | 34171049 | 34171166 | chr6 | 34396518 | 34396631 | chr6 | 34724210 | 34724318 |
| chr6 | 35149942 | 35150181 | chr6 | 35479539 | 35479718 | chr6 | 35992354 | 35992533 |
| chr6 | 36165588 | 36165767 | chr6 | 36252899 | 36253258 | chr6 | 36313887 | 36313988 |
| chr6 | 36808233 | 36808532 | chr6 | 37024485 | 37024664 | chr6 | 37664045 | 37664284 |
| chr6 | 37673227 | 37673573 | chr6 | 37776336 | 37776455 | chr6 | 37776737 | 37776839 |
| chr6 | 39281005 | 39281231 | chr6 | 39281731 | 39281970 | chr6 | 39329789 | 39329968 |
| chr6 | 39760322 | 39760663 | chr6 | 40554557 | 40554796 | chr6 | 41336981 | 41337220 |
| chr6 | 41339162 | 41339941 | chr6 | 41340803 | 41341282 | chr6 | 41341406 | 41341645 |
| chr6 | 41342140 | 41342370 | chr6 | 41342733 | 41342912 | chr6 | 41605851 | 41606630 |
| chr6 | 41773485 | 41773844 | chr6 | 42773364 | 42773471 | chr6 | 42846625 | 42846729 |
| chr6 | 42879457 | 42879756 | chr6 | 42928239 | 42928460 | chr6 | 43211113 | 43211402 |
| chr6 | 43424445 | 43424564 | chr6 | 43425407 | 43425524 | chr6 | 43478592 | 43478821 |
| chr6 | 43612737 | 43613156 | chr6 | 43639525 | 43639809 | chr6 | 43748380 | 43748619 |
| chr6 | 44240961 | 44241191 | chr6 | 44695775 | 44695899 | chr6 | 45388701 | 45388866 |
| chr6 | 46702904 | 46703203 | chr6 | 46703274 | 46703513 | chr6 | 50674292 | 50674831 |
| chr6 | 50681612 | 50681851 | chr6 | 50681912 | 50682031 | chr6 | 50682234 | 50682473 |
| chr6 | 50682584 | 50683303 | chr6 | 50684865 | 50685044 | chr6 | 50689827 | 50690126 |
| chr6 | 50690991 | 50691170 | chr6 | 50691983 | 50692582 | chr6 | 50787125 | 50788444 |
| chr6 | 50789300 | 50789479 | chr6 | 50791111 | 50791708 | chr6 | 50793251 | 50793490 |
| chr6 | 50793626 | 50793850 | chr6 | 50794525 | 50794792 | chr6 | 50803732 | 50803971 |
| chr6 | 50804041 | 50804446 | chr6 | 50808589 | 50808845 | chr6 | 50810456 | 50810935 |
| chr6 | 50810976 | 50811575 | chr6 | 50813200 | 50814019 | chr6 | 50814495 | 50814674 |
| chr6 | 50816947 | 50817306 | chr6 | 50817831 | 50817841 | chr6 | 50818369 | 50818788 |
| chr6 | 50818841 | 50819080 | chr6 | 52227678 | 52227857 | chr6 | 52227934 | 52227964 |
| chr6 | 52344301 | 52344480 | chr6 | 53212553 | 53213932 | chr6 | 55443610 | 55444029 |
| chr6 | 56112175 | 56112474 | chr6 | 56716252 | 56716491 | chr6 | 56818618 | 56819037 |
| chr6 | 56819128 | 56819727 | chr6 | 56819823 | 56820002 | chr6 | 58147345 | 58147619 |
| chr6 | 58147764 | 58148058 | chr6 | 62995272 | 62996231 | chr6 | 62996347 | 62996586 |
| chr6 | 70991961 | 70992260 | chr6 | 70992339 | 70992638 | chr6 | 70992744 | 70993103 |
| chr6 | 71665562 | 71665801 | chr6 | 71666708 | 71667066 | chr6 | 72129690 | 72129929 |
| chr6 | 72130017 | 72130556 | chr6 | 72596039 | 72596398 | chr6 | 72596876 | 72597055 |
| chr6 | 73329686 | 73330225 | chr6 | 73330740 | 73331399 | chr6 | 73331420 | 73333099 |
| chr6 | 78172096 | 78172675 | chr6 | 78173119 | 78173295 | chr6 | 78173610 | 78174080 |
| chr6 | 78176370 | 78176607 | chr6 | 78176693 | 78176909 | chr6 | 79620310 | 79620789 |
| chr6 | 80656846 | 80657265 | chr6 | 82958527 | 82958646 | chr6 | 84417343 | 84417877 |
| chr6 | 84418078 | 84418377 | chr6 | 84418545 | 84418904 | chr6 | 84419077 | 84419496 |
| chr6 | 84562789 | 84563328 | chr6 | 84563397 | 84563636 | chr6 | 85472306 | 85473805 |
| chr6 | 85473854 | 85474453 | chr6 | 85474516 | 85474767 | chr6 | 85474795 | 85474815 |
| chr6 | 85476140 | 85476379 | chr6 | 85476924 | 85477103 | chr6 | 85478440 | 85478557 |
| chr6 | 85478615 | 85478799 | chr6 | 85482437 | 85482796 | chr6 | 85483271 | 85483450 |
| chr6 | 85483559 | 85484998 | chr6 | 86302335 | 86302422 | chr6 | 87647130 | 87647219 |
| chr6 | 87862013 | 87862252 | chr6 | 88876871 | 88877530 | chr6 | 91320191 | 91320422 |
| chr6 | 91320853 | 91321390 | chr6 | 94126870 | 94127169 | chr6 | 94127381 | 94127620 |
| chr6 | 94128340 | 94128502 | chr6 | 94129119 | 94129358 | chr6 | 94129423 | 94129662 |
| chr6 | 96464003 | 96464293 | chr6 | 99271829 | 99272908 | chr6 | 99273271 | 99273510 |
| chr6 | 99277106 | 99277201 | chr6 | 99277262 | 99277405 | chr6 | 99279465 | 99279704 |
| chr6 | 99280472 | 99280831 | chr6 | 99280931 | 99281470 | chr6 | 99283428 | 99283667 |
| chr6 | 99290260 | 99290499 | chr6 | 99290556 | 99290738 | chr6 | 99291191 | 99291300 |
| chr6 | 99292156 | 99292515 | chr6 | 99295648 | 99296547 | chr6 | 99396354 | 99396473 |
| chr6 | 100038584 | 100039063 | chr6 | 100039185 | 100039364 | chr6 | 100050674 | 100052053 |
| chr6 | 100053191 | 100053606 | chr6 | 100054773 | 100055012 | chr6 | 100060930 | 100061169 |
| chr6 | 100061216 | 100061515 | chr6 | 100061677 | 100061916 | chr6 | 100062083 | 100062682 |
| chr6 | 100062857 | 100063156 | chr6 | 100441276 | 100442055 | chr6 | 100903299 | 100903718 |
| chr6 | 100904126 | 100904365 | chr6 | 100905936 | 100906113 | chr6 | 100911976 | 100912215 |
| chr6 | 100912332 | 100912571 | chr6 | 100912825 | 100913244 | chr6 | 100915004 | 100915303 |
| chr6 | 101840615 | 101840914 | chr6 | 101847215 | 101847290 | chr6 | 101850062 | 101850314 |
| chr6 | 101850496 | 101850675 | chr6 | 105388605 | 105388784 | chr6 | 105388833 | 105389792 |
| chr6 | 105400811 | 105401110 | chr6 | 105401538 | 105401908 | chr6 | 105404475 | 105404774 |
| chr6 | 105405565 | 105405864 | chr6 | 105406024 | 105406203 | chr6 | 105584190 | 105585629 |
| chr6 | 106428948 | 106429704 | chr6 | 106434265 | 106434371 | chr6 | 106441795 | 106443054 |
| chr6 | 106960817 | 106961116 | chr6 | 107955878 | 107956057 | chr6 | 108280341 | 108280442 |
| chr6 | 108434990 | 108435327 | chr6 | 108435970 | 108436629 | chr6 | 108438142 | 108438612 |
| chr6 | 108440017 | 108441036 | chr6 | 108479209 | 108479748 | chr6 | 108484829 | 108485274 |
| chr6 | 108485419 | 108485488 | chr6 | 108485576 | 108485995 | chr6 | 108486067 | 108486486 |
| chr6 | 108487701 | 108488520 | chr6 | 108489290 | 108490729 | chr6 | 108490902 | 108491501 |

TABLE 14-continued

| | | Pan Cancer #4 | | | | | | |
|---|---|---|---|---|---|---|---|---|
| chr | start | end | chr | start | end | chr | start | end |
| chr6 | 108492182 | 108492541 | chr6 | 108495607 | 108496026 | chr6 | 108496130 | 108496729 |
| chr6 | 108497419 | 108497958 | chr6 | 110679030 | 110679509 | chr6 | 110797604 | 110797783 |
| chr6 | 110797933 | 110798047 | chr6 | 116783418 | 116783591 | chr6 | 117086168 | 117086947 |
| chr6 | 117585867 | 117586106 | chr6 | 117586717 | 117586781 | chr6 | 117587028 | 117587256 |
| chr6 | 117587380 | 117587387 | chr6 | 117587449 | 117587679 | chr6 | 117591087 | 117591266 |
| chr6 | 117591308 | 117591847 | chr6 | 118228008 | 118228247 | chr6 | 118228669 | 118228908 |
| chr6 | 118229060 | 118229479 | chr6 | 118229543 | 118229902 | chr6 | 118241125 | 118241604 |
| chr6 | 119254661 | 119254774 | chr6 | 121758594 | 121759048 | chr6 | 123316950 | 123317669 |
| chr6 | 123317696 | 123317935 | chr6 | 124124330 | 124124569 | chr6 | 124124759 | 124125118 |
| chr6 | 125284034 | 125284273 | chr6 | 126068016 | 126068255 | chr6 | 127439297 | 127439536 |
| chr6 | 127439907 | 127440206 | chr6 | 127440248 | 127441207 | chr6 | 127441479 | 127441838 |
| chr6 | 127441944 | 127442183 | chr6 | 127840412 | 127840771 | chr6 | 129204373 | 129204612 |
| chr6 | 130686437 | 130687156 | chr6 | 131602689 | 131602789 | chr6 | 132721988 | 132722287 |
| chr6 | 133561666 | 133562145 | chr6 | 133562297 | 133563136 | chr6 | 133563234 | 133564013 |
| chr6 | 134067456 | 134067573 | chr6 | 134176147 | 134176149 | chr6 | 134210439 | 134211458 |
| chr6 | 134213855 | 134214454 | chr6 | 134589425 | 134589586 | chr6 | 134638858 | 134639095 |
| chr6 | 137241828 | 137242307 | chr6 | 137243130 | 137243342 | chr6 | 137243367 | 137243489 |
| chr6 | 137244036 | 137244695 | chr6 | 137311060 | 137311479 | chr6 | 137366280 | 137366459 |
| chr6 | 137809066 | 137811165 | chr6 | 137813692 | 137813991 | chr6 | 137814505 | 137814864 |
| chr6 | 137814916 | 137815755 | chr6 | 137816373 | 137817377 | chr6 | 137818428 | 137819447 |
| chr6 | 146755489 | 146755728 | chr6 | 149868369 | 149868478 | chr6 | 150284574 | 150284657 |
| chr6 | 150284979 | 150286718 | chr6 | 150358890 | 150359489 | chr6 | 151560928 | 151561947 |
| chr6 | 151561986 | 151562645 | chr6 | 151814953 | 151815192 | chr6 | 152622925 | 152623584 |
| chr6 | 152957807 | 152958166 | chr6 | 153451159 | 153451578 | chr6 | 153451810 | 153452049 |
| chr6 | 153452157 | 153452396 | chr6 | 153452611 | 153452850 | chr6 | 154360549 | 154360848 |
| chr6 | 154970468 | 154970587 | chr6 | 155316161 | 155316340 | chr6 | 155569193 | 155569407 |
| chr6 | 157502364 | 157502543 | chr6 | 157506008 | 157506187 | chr6 | 157556755 | 157557954 |
| chr6 | 159589948 | 159591087 | chr6 | 159654844 | 159655083 | chr6 | 161100422 | 161100466 |
| chr6 | 161188439 | 161188618 | chr6 | 161351999 | 161352238 | chr6 | 161780141 | 161780218 |
| chr6 | 163834237 | 163834716 | chr6 | 163834779 | 163834907 | chr6 | 163834988 | 163835018 |
| chr6 | 163836465 | 163837004 | chr6 | 164179653 | 164179772 | chr6 | 164196997 | 164197107 |
| chr6 | 164228212 | 164228449 | chr6 | 164246123 | 164246229 | chr6 | 164283167 | 164283370 |
| chr6 | 164314286 | 164314525 | chr6 | 164322572 | 164322871 | chr6 | 166074027 | 166074506 |
| chr6 | 166076696 | 166077115 | chr6 | 166077280 | 166077759 | chr6 | 166267503 | 166268162 |
| chr6 | 166401162 | 166401401 | chr6 | 166402154 | 166402633 | chr6 | 166421831 | 166422288 |
| chr6 | 166579636 | 166580234 | chr6 | 166580252 | 166582891 | chr6 | 166944266 | 166944505 |
| chr6 | 167835031 | 167835270 | chr6 | 168719882 | 168720121 | chr6 | 168842760 | 168843046 |
| chr6 | 168858030 | 168858389 | chr6 | 169653564 | 169653743 | chr6 | 170240691 | 170240797 |
| chr6 | 170264630 | 170264865 | chr6 | 170475007 | 170475366 | chr7 | 329703 | 329942 |
| chr7 | 369763 | 370062 | chr7 | 389589 | 389768 | chr7 | 409740 | 409872 |
| chr7 | 409887 | 409979 | chr7 | 431290 | 431589 | chr7 | 497679 | 498006 |
| chr7 | 503725 | 504024 | chr7 | 551499 | 551778 | chr7 | 557008 | 557076 |
| chr7 | 578836 | 579121 | chr7 | 751726 | 751965 | chr7 | 752022 | 752321 |
| chr7 | 907582 | 907761 | chr7 | 914984 | 915163 | chr7 | 1022150 | 1022329 |
| chr7 | 1030079 | 1030378 | chr7 | 1054489 | 1054780 | chr7 | 1086110 | 1086409 |
| chr7 | 1263682 | 1264041 | chr7 | 1269228 | 1269687 | chr7 | 1270304 | 1270543 |
| chr7 | 1273070 | 1273429 | chr7 | 1274540 | 1274779 | chr7 | 1274934 | 1275113 |
| chr7 | 1275481 | 1275780 | chr7 | 1277722 | 1277961 | chr7 | 1279136 | 1279204 |
| chr7 | 1279891 | 1280070 | chr7 | 1281033 | 1281332 | chr7 | 1281405 | 1281644 |
| chr7 | 1281947 | 1282246 | chr7 | 1282426 | 1282725 | chr7 | 1286142 | 1286441 |
| chr7 | 1286715 | 1286954 | chr7 | 1288489 | 1288848 | chr7 | 1308275 | 1308574 |
| chr7 | 1325727 | 1325966 | chr7 | 1415941 | 1416226 | chr7 | 1423536 | 1423740 |
| chr7 | 1458967 | 1459183 | chr7 | 1503328 | 1503687 | chr7 | 1547234 | 1547413 |
| chr7 | 1598549 | 1598788 | chr7 | 1607307 | 1607546 | chr7 | 1607897 | 1608076 |
| chr7 | 1641700 | 1641999 | chr7 | 1681095 | 1681334 | chr7 | 1688883 | 1689101 |
| chr7 | 1690649 | 1690801 | chr7 | 1690903 | 1690948 | chr7 | 1709038 | 1709337 |
| chr7 | 1709385 | 1709684 | chr7 | 1733066 | 1733482 | chr7 | 1775757 | 1775936 |
| chr7 | 1783468 | 1783470 | chr7 | 1786438 | 1786916 | chr7 | 1787066 | 1787425 |
| chr7 | 1800808 | 1800987 | chr7 | 1970776 | 1970947 | chr7 | 2163251 | 2163496 |
| chr7 | 2208635 | 2208889 | chr7 | 2232861 | 2233154 | chr7 | 2233204 | 2233503 |
| chr7 | 2238051 | 2238327 | chr7 | 2300694 | 2300803 | chr7 | 2473350 | 2473614 |
| chr7 | 2473624 | 2473709 | chr7 | 2565961 | 2566130 | chr7 | 2566526 | 2566705 |
| chr7 | 2719928 | 2720227 | chr7 | 2727968 | 2728267 | chr7 | 3033584 | 3033763 |
| chr7 | 3083216 | 3083455 | chr7 | 3283620 | 3283978 | chr7 | 3340370 | 3340549 |
| chr7 | 3340890 | 3341069 | chr7 | 3341394 | 3341693 | chr7 | 4215235 | 4215469 |
| chr7 | 4856897 | 4857136 | chr7 | 4922460 | 4922816 | chr7 | 4922996 | 4923475 |
| chr7 | 4998116 | 4998475 | chr7 | 4998598 | 4998837 | chr7 | 5262472 | 5262648 |
| chr7 | 5632841 | 5633200 | chr7 | 5648011 | 5648490 | chr7 | 6060493 | 6060556 |
| chr7 | 6099127 | 6099234 | chr7 | 6124621 | 6124740 | chr7 | 6188652 | 6188831 |
| chr7 | 6188926 | 6189165 | chr7 | 6443198 | 6443478 | chr7 | 6443752 | 6443794 |
| chr7 | 6443871 | 6443931 | chr7 | 6524492 | 6524599 | chr7 | 6524936 | 6525055 |
| chr7 | 6543064 | 6543303 | chr7 | 6560141 | 6560440 | chr7 | 6566329 | 6566748 |
| chr7 | 6570866 | 6571225 | chr7 | 6576043 | 6576185 | chr7 | 6703458 | 6704057 |
| chr7 | 7605665 | 7605902 | chr7 | 8472995 | 8473762 | chr7 | 8473870 | 8474649 |
| chr7 | 8474727 | 8475146 | chr7 | 8480647 | 8481126 | chr7 | 8481228 | 8481260 |
| chr7 | 8481559 | 8481918 | chr7 | 8481980 | 8482999 | chr7 | 8483070 | 8484029 |

TABLE 14-continued

Pan Cancer #4

| chr | start | end | chr | start | end | chr | start | end |
|---|---|---|---|---|---|---|---|---|
| chr7 | 12151350 | 12151769 | chr7 | 12443241 | 12443480 | chr7 | 12443767 | 12443806 |
| chr7 | 12610259 | 12610317 | chr7 | 12610539 | 12610558 | chr7 | 15725883 | 15726182 |
| chr7 | 15726557 | 15727156 | chr7 | 15727216 | 15727395 | chr7 | 19145730 | 19146329 |
| chr7 | 19146411 | 19146650 | chr7 | 19147041 | 19147880 | chr7 | 19152069 | 19152368 |
| chr7 | 19155865 | 19155896 | chr7 | 19155984 | 19156643 | chr7 | 19156705 | 19157003 |
| chr7 | 19157041 | 19158120 | chr7 | 19183978 | 19184337 | chr7 | 19813210 | 19813350 |
| chr7 | 20816175 | 20816530 | chr7 | 20817306 | 20817332 | chr7 | 20817452 | 20817485 |
| chr7 | 20818037 | 20818276 | chr7 | 20823213 | 20823512 | chr7 | 20823826 | 20825025 |
| chr7 | 20825290 | 20825363 | chr7 | 20826803 | 20826939 | chr7 | 20827224 | 20827282 |
| chr7 | 20830596 | 20830775 | chr7 | 20833066 | 20833425 | chr7 | 21582492 | 21582971 |
| chr7 | 21583176 | 21583415 | chr7 | 22539752 | 22539991 | chr7 | 22589254 | 22589973 |
| chr7 | 23287170 | 23287709 | chr7 | 23578824 | 23578943 | chr7 | 24324002 | 24324031 |
| chr7 | 24580786 | 24580905 | chr7 | 24796404 | 24796643 | chr7 | 25892430 | 25892669 |
| chr7 | 25896424 | 25896603 | chr7 | 25896675 | 25896963 | chr7 | 27127919 | 27128001 |
| chr7 | 27135232 | 27135891 | chr7 | 27135923 | 27136868 | chr7 | 27190490 | 27191329 |
| chr7 | 27195483 | 27196742 | chr7 | 27204402 | 27205481 | chr7 | 27205599 | 27206138 |
| chr7 | 27209413 | 27209672 | chr7 | 27209690 | 27209772 | chr7 | 27212400 | 27212999 |
| chr7 | 27213082 | 27214401 | chr7 | 27223031 | 27223253 | chr7 | 27223500 | 27223799 |
| chr7 | 27223980 | 27224699 | chr7 | 27224945 | 27225184 | chr7 | 27227795 | 27228034 |
| chr7 | 27232207 | 27233046 | chr7 | 27238813 | 27238992 | chr7 | 27239087 | 27239326 |
| chr7 | 27240127 | 27240423 | chr7 | 27244446 | 27245393 | chr7 | 27245583 | 27245733 |
| chr7 | 27252306 | 27252485 | chr7 | 27264801 | 27265400 | chr7 | 27265442 | 27265678 |
| chr7 | 27275439 | 27275532 | chr7 | 27279015 | 27279554 | chr7 | 27282012 | 27283091 |
| chr7 | 27283250 | 27283662 | chr7 | 27285436 | 27286249 | chr7 | 27288869 | 27289528 |
| chr7 | 27291048 | 27291947 | chr7 | 28449197 | 28450096 | chr7 | 28995579 | 28996058 |
| chr7 | 28996357 | 28996596 | chr7 | 28996759 | 28996998 | chr7 | 28997052 | 28997711 |
| chr7 | 28997967 | 28998206 | chr7 | 30721202 | 30721981 | chr7 | 30722214 | 30722453 |
| chr7 | 31092919 | 31093218 | chr7 | 31375899 | 31376230 | chr7 | 32110616 | 32110855 |
| chr7 | 32337733 | 32337912 | chr7 | 32338010 | 32338489 | chr7 | 32338826 | 32339005 |
| chr7 | 32467373 | 32468151 | chr7 | 32997050 | 32997463 | chr7 | 33943370 | 33943849 |
| chr7 | 35225724 | 35225963 | chr7 | 35226090 | 35226811 | chr7 | 35292893 | 35293372 |
| chr7 | 35293569 | 35294228 | chr7 | 35294400 | 35294639 | chr7 | 35295030 | 35295182 |
| chr7 | 35295807 | 35296000 | chr7 | 35296855 | 35298114 | chr7 | 35300851 | 35302050 |
| chr7 | 35494278 | 35494517 | chr7 | 37487076 | 37487251 | chr7 | 37487376 | 37487915 |
| chr7 | 37488179 | 37488658 | chr7 | 37488837 | 37489076 | chr7 | 37907366 | 37907545 |
| chr7 | 37955780 | 37956079 | chr7 | 37956176 | 37956535 | chr7 | 37960199 | 37960438 |
| chr7 | 38670267 | 38671106 | chr7 | 39015463 | 39016062 | chr7 | 42267573 | 42267752 |
| chr7 | 42276251 | 42276730 | chr7 | 42533028 | 42533387 | chr7 | 43152016 | 43152795 |
| chr7 | 43152858 | 43153337 | chr7 | 44097656 | 44097895 | chr7 | 44143906 | 44144085 |
| chr7 | 44151324 | 44151503 | chr7 | 44151715 | 44151857 | chr7 | 44164017 | 44164078 |
| chr7 | 44364752 | 44364991 | chr7 | 44835122 | 44835467 | chr7 | 45038447 | 45038564 |
| chr7 | 45613693 | 45613992 | chr7 | 45614259 | 45614558 | chr7 | 45614655 | 45615061 |
| chr7 | 45615536 | 45615588 | chr7 | 45960650 | 45960889 | chr7 | 45961072 | 45961251 |
| chr7 | 45961423 | 45961630 | chr7 | 45961656 | 45961662 | chr7 | 45961742 | 45961981 |
| chr7 | 49812718 | 49814097 | chr7 | 49814454 | 49814873 | chr7 | 49815014 | 49815848 |
| chr7 | 50294460 | 50294556 | chr7 | 50343183 | 50343396 | chr7 | 50343607 | 50344086 |
| chr7 | 50344150 | 50344569 | chr7 | 50364988 | 50365069 | chr7 | 50438544 | 50438723 |
| chr7 | 50560494 | 50560733 | chr7 | 50860135 | 50860393 | chr7 | 50860980 | 50861214 |
| chr7 | 51384235 | 51384534 | chr7 | 51384814 | 51385006 | chr7 | 54609764 | 54610243 |
| chr7 | 54612335 | 54612814 | chr7 | 55086481 | 55086687 | chr7 | 55086899 | 55087618 |
| chr7 | 55409933 | 55410223 | chr7 | 56018026 | 56018205 | chr7 | 56031847 | 56031966 |
| chr7 | 64330322 | 64330561 | chr7 | 64330635 | 64330645 | chr7 | 64348952 | 64349131 |
| chr7 | 64349318 | 64349551 | chr7 | 64700198 | 64700426 | chr7 | 64712288 | 64712587 |
| chr7 | 64974283 | 64974402 | chr7 | 65037592 | 65037702 | chr7 | 65508900 | 65509124 |
| chr7 | 66214974 | 66215062 | chr7 | 68204692 | 68204931 | chr7 | 69062428 | 69062727 |
| chr7 | 69064489 | 69065148 | chr7 | 69897685 | 69897924 | chr7 | 70596353 | 70596772 |
| chr7 | 70596845 | 70597204 | chr7 | 70597310 | 70597368 | chr7 | 70597395 | 70597549 |
| chr7 | 70597752 | 70597754 | chr7 | 70597780 | 70598471 | chr7 | 71217011 | 71217366 |
| chr7 | 71800599 | 71801978 | chr7 | 71802315 | 71802396 | chr7 | 71802457 | 71802734 |
| chr7 | 71871105 | 71871157 | chr7 | 76033251 | 76033364 | chr7 | 77324278 | 77324397 |
| chr7 | 79081718 | 79081897 | chr7 | 79081942 | 79081969 | chr7 | 79082070 | 79082301 |
| chr7 | 79083016 | 79083255 | chr7 | 79083314 | 79083913 | chr7 | 82072248 | 82072607 |
| chr7 | 84815049 | 84815135 | chr7 | 84815252 | 84815468 | chr7 | 84815670 | 84816029 |
| chr7 | 86273108 | 86273645 | chr7 | 86274018 | 86274547 | chr7 | 87104725 | 87105445 |
| chr7 | 87229446 | 87230525 | chr7 | 87256911 | 87257150 | chr7 | 87257964 | 87258143 |
| chr7 | 88387904 | 88388130 | chr7 | 88388190 | 88388263 | chr7 | 88388439 | 88388738 |
| chr7 | 88388789 | 88389389 | chr7 | 89747928 | 89748438 | chr7 | 89950108 | 89950813 |
| chr7 | 90226188 | 90226547 | chr7 | 90894936 | 90895175 | chr7 | 92466078 | 92466486 |
| chr7 | 92689613 | 92689774 | chr7 | 93203613 | 93203852 | chr7 | 93204233 | 93204592 |
| chr7 | 93519265 | 93520224 | chr7 | 93551225 | 93551524 | chr7 | 94284277 | 94284978 |
| chr7 | 96619499 | 96619678 | chr7 | 96621614 | 96621913 | chr7 | 96622019 | 96622438 |
| chr7 | 96625472 | 96625809 | chr7 | 96625906 | 96626145 | chr7 | 96631614 | 96631780 |
| chr7 | 96634577 | 96634996 | chr7 | 96635260 | 96635379 | chr7 | 96635440 | 96635559 |
| chr7 | 96635650 | 96636729 | chr7 | 96646568 | 96647227 | chr7 | 96647715 | 96648314 |
| chr7 | 96649965 | 96650284 | chr7 | 96650809 | 96651228 | chr7 | 96651384 | 96651584 |
| chr7 | 96652070 | 96652249 | chr7 | 96653421 | 96654080 | chr7 | 97361021 | 97361860 |

TABLE 14-continued

Pan Cancer #4

| chr | start | end | chr | start | end | chr | start | end |
|---|---|---|---|---|---|---|---|---|
| chr7 | 97362211 | 97362690 | chr7 | 97600015 | 97600194 | chr7 | 97869540 | 97869719 |
| chr7 | 98245808 | 98246947 | chr7 | 98247032 | 98247751 | chr7 | 98971530 | 98971649 |
| chr7 | 99104174 | 99104293 | chr7 | 99177657 | 99177956 | chr7 | 99591732 | 99591851 |
| chr7 | 99595184 | 99595416 | chr7 | 99751485 | 99751553 | chr7 | 99775118 | 99775297 |
| chr7 | 100088099 | 100088398 | chr7 | 100091115 | 100091474 | chr7 | 100179789 | 100180017 |
| chr7 | 100318421 | 100318660 | chr7 | 100808365 | 100808596 | chr7 | 100809360 | 100809599 |
| chr7 | 100823348 | 100823587 | chr7 | 101005901 | 101006073 | chr7 | 101241919 | 101242098 |
| chr7 | 101475705 | 101475944 | chr7 | 101627683 | 101627884 | chr7 | 101707428 | 101707535 |
| chr7 | 103085786 | 103086565 | chr7 | 103628963 | 103630222 | chr7 | 103630381 | 103630920 |
| chr7 | 103969130 | 103969429 | chr7 | 103969595 | 103969894 | chr7 | 105279390 | 105279749 |
| chr7 | 106685195 | 106685434 | chr7 | 106797700 | 106797856 | chr7 | 107301418 | 107301717 |
| chr7 | 107483597 | 107484016 | chr7 | 108095227 | 108095466 | chr7 | 108095602 | 108096141 |
| chr7 | 108097093 | 108097572 | chr7 | 112726529 | 112726706 | chr7 | 113722736 | 113723515 |
| chr7 | 113724870 | 113725169 | chr7 | 113726435 | 113726614 | chr7 | 113727345 | 113727584 |
| chr7 | 113727633 | 113727872 | chr7 | 115117451 | 115117750 | chr7 | 116140155 | 116140268 |
| chr7 | 116962796 | 116963575 | chr7 | 117119347 | 117120366 | chr7 | 119913464 | 119913837 |
| chr7 | 120969587 | 120969886 | chr7 | 121513457 | 121513796 | chr7 | 121939584 | 121940543 |
| chr7 | 121940845 | 121941144 | chr7 | 121941807 | 121942266 | chr7 | 121943905 | 121944264 |
| chr7 | 121945722 | 121946021 | chr7 | 121946403 | 121947482 | chr7 | 121950034 | 121951029 |
| chr7 | 121951784 | 121952256 | chr7 | 121956408 | 121956647 | chr7 | 121956650 | 121957411 |
| chr7 | 123173048 | 123173327 | chr7 | 123671948 | 123672187 | chr7 | 124404320 | 124404619 |
| chr7 | 126891146 | 126891325 | chr7 | 126891430 | 126891669 | chr7 | 127371055 | 127371234 |
| chr7 | 127615847 | 127616026 | chr7 | 127744048 | 127744707 | chr7 | 127806560 | 127806739 |
| chr7 | 127807743 | 127807922 | chr7 | 127807971 | 127808822 | chr7 | 127841426 | 127841785 |
| chr7 | 127991742 | 127992221 | chr7 | 128096988 | 128097164 | chr7 | 128337365 | 128337543 |
| chr7 | 128337605 | 128338023 | chr7 | 128470816 | 128471115 | chr7 | 128486020 | 128486237 |
| chr7 | 128528729 | 128528854 | chr7 | 128528949 | 128529128 | chr7 | 128828115 | 128828354 |
| chr7 | 129229605 | 129229724 | chr7 | 129418168 | 129418513 | chr7 | 129422070 | 129423509 |
| chr7 | 129424552 | 129425991 | chr7 | 129426215 | 129426336 | chr7 | 129794508 | 129794807 |
| chr7 | 129800223 | 129800462 | chr7 | 131041437 | 131041676 | chr7 | 131242662 | 131242901 |
| chr7 | 131514750 | 131514929 | chr7 | 132261173 | 132261532 | chr7 | 134143081 | 134143560 |
| chr7 | 134143731 | 134144209 | chr7 | 134918421 | 134918720 | chr7 | 136553316 | 136553495 |
| chr7 | 136553556 | 136554469 | chr7 | 136554563 | 136555042 | chr7 | 136555145 | 136555504 |
| chr7 | 136555587 | 136556186 | chr7 | 137028402 | 137028623 | chr7 | 137531153 | 137532438 |
| chr7 | 138042136 | 138042315 | chr7 | 139167532 | 139167831 | chr7 | 139167942 | 139168481 |
| chr7 | 139208697 | 139208888 | chr7 | 139930070 | 139930371 | chr7 | 139939060 | 139939314 |
| chr7 | 140026925 | 140027043 | chr7 | 140180180 | 140180298 | chr7 | 140339839 | 140339905 |
| chr7 | 140339966 | 140340078 | chr7 | 140453048 | 140453247 | chr7 | 140772713 | 140773312 |
| chr7 | 140773478 | 140773837 | chr7 | 143042537 | 143042896 | chr7 | 143579665 | 143580144 |
| chr7 | 145812918 | 145813157 | chr7 | 145813334 | 145813573 | chr7 | 145813790 | 145814269 |
| chr7 | 148224592 | 148224711 | chr7 | 148640242 | 148640331 | chr7 | 148846061 | 148846279 |
| chr7 | 149111968 | 149112226 | chr7 | 149112287 | 149112507 | chr7 | 149119862 | 149120161 |
| chr7 | 149411444 | 149412403 | chr7 | 149744414 | 149744653 | chr7 | 149917173 | 149917412 |
| chr7 | 149918045 | 149918224 | chr7 | 150049512 | 150049626 | chr7 | 150069013 | 150069432 |
| chr7 | 150069601 | 150069662 | chr7 | 150069837 | 150069900 | chr7 | 150069921 | 150070160 |
| chr7 | 150081153 | 150081354 | chr7 | 150716088 | 150716387 | chr7 | 150748090 | 150748509 |
| chr7 | 150753843 | 150754082 | chr7 | 150870734 | 150870973 | chr7 | 151106369 | 151107088 |
| chr7 | 151107390 | 151107749 | chr7 | 151591567 | 151591806 | chr7 | 152622540 | 152622779 |
| chr7 | 152622918 | 152623157 | chr7 | 153583503 | 153584162 | chr7 | 153584297 | 153584546 |
| chr7 | 153584694 | 153584716 | chr7 | 153584758 | 153585233 | chr7 | 153585333 | 153585692 |
| chr7 | 153749619 | 153750218 | chr7 | 154561051 | 154561290 | chr7 | 154708188 | 154708355 |
| chr7 | 154861947 | 154862366 | chr7 | 155164379 | 155165638 | chr7 | 155165791 | 155166870 |
| chr7 | 155166933 | 155167992 | chr7 | 155174573 | 155174872 | chr7 | 155241235 | 155242134 |
| chr7 | 155242647 | 155243186 | chr7 | 155243245 | 155243684 | chr7 | 155243741 | 155243980 |
| chr7 | 155244092 | 155244451 | chr7 | 155246786 | 155247685 | chr7 | 155248839 | 155249018 |
| chr7 | 155249420 | 155249659 | chr7 | 155249849 | 155250088 | chr7 | 155250200 | 155250439 |
| chr7 | 155250713 | 155251072 | chr7 | 155251611 | 155252030 | chr7 | 155252160 | 155252579 |
| chr7 | 155252773 | 155253132 | chr7 | 155254765 | 155255416 | chr7 | 155256216 | 155256395 |
| chr7 | 155256986 | 155257265 | chr7 | 155258101 | 155258580 | chr7 | 155258854 | 155260233 |
| chr7 | 155260806 | 155261285 | chr7 | 155301736 | 155302035 | chr7 | 155302267 | 155303432 |
| chr7 | 155325720 | 155325954 | chr7 | 155326079 | 155326618 | chr7 | 155363212 | 155363511 |
| chr7 | 155580069 | 155580308 | chr7 | 155580772 | 155580882 | chr7 | 155581243 | 155581652 |
| chr7 | 155581664 | 155581962 | chr7 | 155582190 | 155582369 | chr7 | 155600527 | 155600825 |
| chr7 | 155602726 | 155602898 | chr7 | 156409214 | 156409426 | chr7 | 156409585 | 156409884 |
| chr7 | 156701758 | 156701997 | chr7 | 156744697 | 156744816 | chr7 | 156794465 | 156794579 |
| chr7 | 156794922 | 156795996 | chr7 | 156796442 | 156799561 | chr7 | 156800925 | 156801104 |
| chr7 | 156801323 | 156801682 | chr7 | 156808760 | 156809299 | chr7 | 156809953 | 156811520 |
| chr7 | 156812773 | 156815170 | chr7 | 156832194 | 156832493 | chr7 | 156832766 | 156833245 |
| chr7 | 156871084 | 156871383 | chr7 | 156880457 | 156880636 | chr7 | 157085281 | 157085580 |
| chr7 | 157085874 | 157086173 | chr7 | 157262738 | 157263097 | chr7 | 157263204 | 157263563 |
| chr7 | 157361531 | 157361710 | chr7 | 157476790 | 157477376 | chr7 | 157477395 | 157477994 |
| chr7 | 157481289 | 157481860 | chr7 | 157481890 | 157482249 | chr7 | 157482401 | 157482760 |
| chr7 | 157483220 | 157483639 | chr7 | 157484778 | 157485377 | chr7 | 157485437 | 157485796 |
| chr7 | 157485881 | 157486600 | chr7 | 157584104 | 157584283 | chr7 | 157588510 | 157588869 |
| chr7 | 157606632 | 157606811 | chr7 | 157690145 | 157690161 | chr7 | 158059659 | 158059898 |
| chr7 | 158936420 | 158936956 | chr7 | 158937062 | 158937721 | chr7 | 158938126 | 158938485 |

TABLE 14-continued

| | | | | Pan Cancer #4 | | | | |
|---|---|---|---|---|---|---|---|---|
| chr | start | end | chr | start | end | chr | start | end |
| chr8 | 686794 | 687393 | chr8 | 687650 | 688129 | chr8 | 688286 | 688465 |
| chr8 | 688895 | 689134 | chr8 | 1085559 | 1085678 | chr8 | 4849040 | 4849279 |
| chr8 | 4849364 | 4849603 | chr8 | 4850173 | 4850592 | chr8 | 4851662 | 4851686 |
| chr8 | 4851722 | 4851841 | chr8 | 4851921 | 4852220 | chr8 | 8748329 | 8748808 |
| chr8 | 8748819 | 8749058 | chr8 | 9722754 | 9722993 | chr8 | 9755965 | 9756564 |
| chr8 | 9760646 | 9761245 | chr8 | 9762487 | 9762965 | chr8 | 9763060 | 9763359 |
| chr8 | 9763816 | 9764295 | chr8 | 9764344 | 9764643 | chr8 | 10587507 | 10587866 |
| chr8 | 10588301 | 10588540 | chr8 | 11204405 | 11204584 | chr8 | 11204709 | 11205008 |
| chr8 | 11536753 | 11536932 | chr8 | 11537123 | 11537362 | chr8 | 11554886 | 11554990 |
| chr8 | 11555068 | 11555605 | chr8 | 11559678 | 11559792 | chr8 | 11559920 | 11560457 |
| chr8 | 11560633 | 11560872 | chr8 | 11561357 | 11562256 | chr8 | 11562335 | 11562574 |
| chr8 | 11562600 | 11563019 | chr8 | 11705869 | 11706228 | chr8 | 11726393 | 11726505 |
| chr8 | 12990409 | 12990529 | chr8 | 12990575 | 12990874 | chr8 | 13319857 | 13319937 |
| chr8 | 15094425 | 15094664 | chr8 | 15397641 | 15397940 | chr8 | 16884239 | 16884331 |
| chr8 | 16885104 | 16885343 | chr8 | 17270974 | 17271213 | chr8 | 19797396 | 19797538 |
| chr8 | 19797860 | 19798099 | chr8 | 20160679 | 20160978 | chr8 | 22089428 | 22089665 |
| chr8 | 22562265 | 22562564 | chr8 | 22960567 | 22960806 | chr8 | 23021083 | 23021209 |
| chr8 | 23260598 | 23260957 | chr8 | 23423830 | 23424009 | chr8 | 23559296 | 23560615 |
| chr8 | 23563712 | 23564480 | chr8 | 23564697 | 23565108 | chr8 | 23566729 | 23567568 |
| chr8 | 23571588 | 23572067 | chr8 | 23572334 | 23572646 | chr8 | 23584000 | 23584839 |
| chr8 | 24770239 | 24770658 | chr8 | 24771072 | 24771311 | chr8 | 24771348 | 24771647 |
| chr8 | 24813089 | 24813388 | chr8 | 24813660 | 24814499 | chr8 | 24857673 | 24857912 |
| chr8 | 24858239 | 24858538 | chr8 | 24858770 | 24859249 | chr8 | 24859422 | 24859601 |
| chr8 | 25041656 | 25041955 | chr8 | 25042636 | 25042671 | chr8 | 25900324 | 25901403 |
| chr8 | 25901444 | 25901863 | chr8 | 25902072 | 25902251 | chr8 | 25902545 | 25902640 |
| chr8 | 25903579 | 25903938 | chr8 | 25904055 | 25904294 | chr8 | 25905022 | 25905201 |
| chr8 | 25905668 | 25905907 | chr8 | 25909098 | 25909697 | chr8 | 26372789 | 26372968 |
| chr8 | 26723884 | 26724183 | chr8 | 30243289 | 30243526 | chr8 | 30769151 | 30769510 |
| chr8 | 30770028 | 30770267 | chr8 | 31496380 | 31496859 | chr8 | 31496939 | 31497176 |
| chr8 | 31497420 | 31497719 | chr8 | 31498015 | 31498254 | chr8 | 32406517 | 32406996 |
| chr8 | 33371978 | 33372217 | chr8 | 33457052 | 33457471 | chr8 | 35092906 | 35093140 |
| chr8 | 35093877 | 35094056 | chr8 | 37655367 | 37655606 | chr8 | 37655707 | 37656186 |
| chr8 | 37822721 | 37823500 | chr8 | 37823583 | 37823805 | chr8 | 37961879 | 37961998 |
| chr8 | 38008157 | 38008636 | chr8 | 38323837 | 38324016 | chr8 | 38965450 | 38965464 |
| chr8 | 41165785 | 41166804 | chr8 | 41166886 | 41167125 | chr8 | 41424682 | 41424921 |
| chr8 | 41624752 | 41624931 | chr8 | 41625038 | 41625217 | chr8 | 41733424 | 41733723 |
| chr8 | 41753498 | 41753857 | chr8 | 41754070 | 41754969 | chr8 | 41755104 | 41755283 |
| chr8 | 41910186 | 41910425 | chr8 | 42147417 | 42147596 | chr8 | 42749996 | 42750094 |
| chr8 | 47093172 | 47093351 | chr8 | 47334530 | 47334694 | chr8 | 48100075 | 48100539 |
| chr8 | 49293280 | 49293699 | chr8 | 49468571 | 49469228 | chr8 | 49571955 | 49572134 |
| chr8 | 49782953 | 49783235 | chr8 | 49959156 | 49959335 | chr8 | 50822095 | 50822394 |
| chr8 | 50822591 | 50822830 | chr8 | 50823358 | 50823677 | chr8 | 53477325 | 53477864 |
| chr8 | 53477933 | 53478352 | chr8 | 53478391 | 53478744 | chr8 | 53853711 | 53854552 |
| chr8 | 54163240 | 54164256 | chr8 | 54789175 | 54789414 | chr8 | 54789556 | 54790155 |
| chr8 | 54790214 | 54790883 | chr8 | 54791724 | 54792323 | chr8 | 54792548 | 54792847 |
| chr8 | 54794123 | 54794422 | chr8 | 54794626 | 54795165 | chr8 | 55366106 | 55367725 |
| chr8 | 55370037 | 55370936 | chr8 | 55371079 | 55372638 | chr8 | 55379202 | 55380041 |
| chr8 | 55382673 | 55383332 | chr8 | 56013545 | 56014024 | chr8 | 56014058 | 56014417 |
| chr8 | 56014524 | 56014883 | chr8 | 56014959 | 56015438 | chr8 | 56015471 | 56015710 |
| chr8 | 56015834 | 56015893 | chr8 | 57025609 | 57026026 | chr8 | 57026072 | 57026311 |
| chr8 | 57026406 | 57026644 | chr8 | 57069473 | 57070245 | chr8 | 57358053 | 57359732 |
| chr8 | 57360472 | 57360891 | chr8 | 58105852 | 58106211 | chr8 | 58116923 | 58117162 |
| chr8 | 58130290 | 58130649 | chr8 | 58907618 | 58907917 | chr8 | 59058934 | 59059233 |
| chr8 | 59747274 | 59747402 | chr8 | 60032590 | 60032890 | chr8 | 61777488 | 61777622 |
| chr8 | 61789900 | 61790076 | chr8 | 62200414 | 62200879 | chr8 | 63161580 | 63161879 |
| chr8 | 65281539 | 65281778 | chr8 | 65281884 | 65283443 | chr8 | 65283708 | 65284187 |
| chr8 | 65285972 | 65286451 | chr8 | 65286599 | 65286838 | chr8 | 65286868 | 65287229 |
| chr8 | 65289033 | 65289332 | chr8 | 65289517 | 65290450 | chr8 | 65290570 | 65290896 |
| chr8 | 65290950 | 65291369 | chr8 | 65292097 | 65292102 | chr8 | 65292180 | 65292816 |
| chr8 | 65488178 | 65488417 | chr8 | 65488618 | 65488799 | chr8 | 65489025 | 65489204 |
| chr8 | 65492637 | 65493056 | chr8 | 65493105 | 65493524 | chr8 | 65493556 | 65493855 |
| chr8 | 65493868 | 65493969 | chr8 | 65494048 | 65494287 | chr8 | 65498465 | 65498550 |
| chr8 | 65498645 | 65498910 | chr8 | 65498926 | 65499149 | chr8 | 65499677 | 65500096 |
| chr8 | 65710868 | 65711142 | chr8 | 66548640 | 66548749 | chr8 | 67024963 | 67025365 |
| chr8 | 67344446 | 67344865 | chr8 | 67873246 | 67875697 | chr8 | 67940548 | 67940960 |
| chr8 | 68864493 | 68864852 | chr8 | 69242828 | 69243007 | chr8 | 69243183 | 69243971 |
| chr8 | 69244286 | 69244585 | chr8 | 70744774 | 70745013 | chr8 | 70946670 | 70947742 |
| chr8 | 70981866 | 70983305 | chr8 | 70983402 | 70985081 | chr8 | 72273897 | 72274136 |
| chr8 | 72459929 | 72460348 | chr8 | 72468473 | 72469664 | chr8 | 72470301 | 72470540 |
| chr8 | 72471037 | 72471158 | chr8 | 72754293 | 72754712 | chr8 | 72754730 | 72755240 |
| chr8 | 72755592 | 72756971 | chr8 | 72917268 | 72917541 | chr8 | 72987519 | 72988118 |
| chr8 | 73163680 | 73164261 | chr8 | 73449963 | 73450202 | chr8 | 73450418 | 73450657 |
| chr8 | 74759411 | 74759565 | chr8 | 74759744 | 74759863 | chr8 | 75896477 | 75897436 |
| chr8 | 76316242 | 76316541 | chr8 | 77585130 | 77585789 | chr8 | 77586078 | 77586377 |
| chr8 | 77586471 | 77586710 | chr8 | 77590144 | 77590563 | chr8 | 77593075 | 77593453 |
| chr8 | 77593798 | 77594217 | chr8 | 77594552 | 77595091 | chr8 | 77595238 | 77595594 |

TABLE 14-continued

Pan Cancer #4

| chr | start | end | chr | start | end | chr | start | end |
|---|---|---|---|---|---|---|---|---|
| chr8 | 79428200 | 79428499 | chr8 | 80523887 | 80524126 | chr8 | 80524167 | 80524406 |
| chr8 | 80524864 | 80525103 | chr8 | 80525520 | 80525819 | chr8 | 80695842 | 80696007 |
| chr8 | 80803594 | 80803953 | chr8 | 81478089 | 81478448 | chr8 | 85095396 | 85095755 |
| chr8 | 85096485 | 85096721 | chr8 | 85096785 | 85096904 | chr8 | 85096939 | 85097298 |
| chr8 | 86350455 | 86350633 | chr8 | 86406814 | 86406933 | chr8 | 86436547 | 86436726 |
| chr8 | 86544681 | 86544798 | chr8 | 89339298 | 89339837 | chr8 | 89340189 | 89340428 |
| chr8 | 90913517 | 90913756 | chr8 | 91094161 | 91094326 | chr8 | 91803578 | 91803817 |
| chr8 | 91803913 | 91804332 | chr8 | 91996958 | 91998037 | chr8 | 92083443 | 92083622 |
| chr8 | 93114033 | 93114632 | chr8 | 95651240 | 95651308 | chr8 | 95651448 | 95651599 |
| chr8 | 95651637 | 95651747 | chr8 | 96219911 | 96220002 | chr8 | 97157007 | 97158146 |
| chr8 | 97165541 | 97165780 | chr8 | 97166351 | 97166530 | chr8 | 97167082 | 97167321 |
| chr8 | 97169757 | 97170416 | chr8 | 97170793 | 97170972 | chr8 | 97171036 | 97172295 |
| chr8 | 97172347 | 97173546 | chr8 | 97173730 | 97173991 | chr8 | 97339752 | 97340291 |
| chr8 | 97505950 | 97506609 | chr8 | 97507021 | 97507380 | chr8 | 97507464 | 97507763 |
| chr8 | 98289744 | 98290343 | chr8 | 99439030 | 99439209 | chr8 | 99439299 | 99440438 |
| chr8 | 99951330 | 99951509 | chr8 | 99951757 | 99952896 | chr8 | 99954400 | 99954819 |
| chr8 | 99955105 | 99955394 | chr8 | 99960231 | 99961070 | chr8 | 99961111 | 99961350 |
| chr8 | 99961718 | 99961897 | chr8 | 99985781 | 99987020 | chr8 | 101118140 | 101118679 |
| chr8 | 101661837 | 101662000 | chr8 | 101821891 | 101822130 | chr8 | 102505458 | 102505654 |
| chr8 | 102505720 | 102506079 | chr8 | 103629857 | 103629961 | chr8 | 104153105 | 104153344 |
| chr8 | 104153366 | 104153725 | chr8 | 104512026 | 104513025 | chr8 | 104513365 | 104514005 |
| chr8 | 105235293 | 105236132 | chr8 | 105478632 | 105479281 | chr8 | 105479315 | 105479531 |
| chr8 | 106331080 | 106331319 | chr8 | 106332004 | 106332286 | chr8 | 107282060 | 107282299 |
| chr8 | 107283938 | 107284177 | chr8 | 108509441 | 108509734 | chr8 | 109093601 | 109094260 |
| chr8 | 109094391 | 109094690 | chr8 | 109094757 | 109096016 | chr8 | 109799500 | 109799859 |
| chr8 | 110274904 | 110275021 | chr8 | 110405946 | 110406106 | chr8 | 110592245 | 110592303 |
| chr8 | 110703924 | 110704029 | chr8 | 110704098 | 110704223 | chr8 | 110986354 | 110986773 |
| chr8 | 114444497 | 114444640 | chr8 | 114444709 | 114445276 | chr8 | 114445677 | 114446101 |
| chr8 | 114446851 | 114447450 | chr8 | 114448939 | 114449358 | chr8 | 114449457 | 114449698 |
| chr8 | 116660435 | 116660854 | chr8 | 117950364 | 117950543 | chr8 | 117950700 | 117950999 |
| chr8 | 120220390 | 120220629 | chr8 | 120844011 | 120844126 | chr8 | 121136805 | 121137824 |
| chr8 | 121823827 | 121824006 | chr8 | 121824103 | 121824582 | chr8 | 121825512 | 121825560 |
| chr8 | 122651770 | 122652009 | chr8 | 123695447 | 123695746 | chr8 | 124055137 | 124055235 |
| chr8 | 124173165 | 124173544 | chr8 | 125452275 | 125452394 | chr8 | 126044494 | 126044653 |
| chr8 | 128745443 | 128745618 | chr8 | 128872311 | 128872490 | chr8 | 128889224 | 128889483 |
| chr8 | 128931157 | 128931336 | chr8 | 130369290 | 130369454 | chr8 | 132052057 | 132053256 |
| chr8 | 132053633 | 132054876 | chr8 | 133686658 | 133686836 | chr8 | 139508668 | 139509386 |
| chr8 | 139509656 | 139510015 | chr8 | 140714485 | 140714964 | chr8 | 140715016 | 140715195 |
| chr8 | 140715379 | 140715738 | chr8 | 140715875 | 140716348 | chr8 | 140834160 | 140834399 |
| chr8 | 140963208 | 140963447 | chr8 | 141159845 | 141160024 | chr8 | 141587975 | 141588214 |
| chr8 | 141596805 | 141597104 | chr8 | 142292454 | 142292808 | chr8 | 142361151 | 142361430 |
| chr8 | 142367673 | 142367879 | chr8 | 142444648 | 142444827 | chr8 | 142528313 | 142529092 |
| chr8 | 142535241 | 142535587 | chr8 | 142568506 | 142568745 | chr8 | 142694751 | 142695030 |
| chr8 | 142984437 | 142984736 | chr8 | 143088946 | 143089153 | chr8 | 143105162 | 143105461 |
| chr8 | 143509377 | 143509676 | chr8 | 143532035 | 143532934 | chr8 | 143533520 | 143533999 |
| chr8 | 143557881 | 143558172 | chr8 | 143558389 | 143558668 | chr8 | 143587238 | 143587477 |
| chr8 | 143592583 | 143592762 | chr8 | 143621889 | 143622188 | chr8 | 143701978 | 143702157 |
| chr8 | 143819303 | 143819406 | chr8 | 143858435 | 143858791 | chr8 | 143859223 | 143859454 |
| chr8 | 143876854 | 143877033 | chr8 | 143993891 | 143994250 | chr8 | 144069457 | 144069749 |
| chr8 | 144190286 | 144190525 | chr8 | 144203601 | 144203801 | chr8 | 144203880 | 144204020 |
| chr8 | 144226100 | 144226279 | chr8 | 144238743 | 144238982 | chr8 | 144241150 | 144241389 |
| chr8 | 144241444 | 144241683 | chr8 | 144241785 | 144242381 | chr8 | 144303488 | 144303667 |
| chr8 | 144328234 | 144328653 | chr8 | 144330288 | 144330467 | chr8 | 144344219 | 144344518 |
| chr8 | 144359928 | 144360177 | chr8 | 144360305 | 144360544 | chr8 | 144361672 | 144361911 |
| chr8 | 144372474 | 144372583 | chr8 | 144509238 | 144510617 | chr8 | 144511146 | 144511505 |
| chr8 | 144511938 | 144512297 | chr8 | 144512399 | 144512466 | chr8 | 144650791 | 144650812 |
| chr8 | 144668532 | 144668767 | chr8 | 144668822 | 144669061 | chr8 | 145698244 | 145698483 |
| chr8 | 145753443 | 145753622 | chr8 | 145758483 | 145758782 | chr8 | 145806184 | 145806350 |
| chr8 | 145925387 | 145925566 | chr8 | 145925869 | 145926070 | chr8 | 146013543 | 146013722 |
| chr8 | 146079134 | 146079297 | chr9 | 113346 | 113645 | chr9 | 113749 | 113988 |
| chr9 | 117808 | 118167 | chr9 | 841602 | 842244 | chr9 | 842545 | 842766 |
| chr9 | 969482 | 969661 | chr9 | 969685 | 969943 | chr9 | 970012 | 970311 |
| chr9 | 970421 | 970600 | chr9 | 970816 | 971175 | chr9 | 971435 | 971655 |
| chr9 | 972204 | 972863 | chr9 | 973067 | 973366 | chr9 | 975248 | 975262 |
| chr9 | 975693 | 976412 | chr9 | 976521 | 977047 | chr9 | 981695 | 981934 |
| chr9 | 1042305 | 1043076 | chr9 | 1051768 | 1052247 | chr9 | 3181662 | 3181961 |
| chr9 | 6412497 | 6412900 | chr9 | 6644217 | 6644636 | chr9 | 6644936 | 6645415 |
| chr9 | 6645544 | 6645783 | chr9 | 6756279 | 6756429 | chr9 | 13278722 | 13278961 |
| chr9 | 14312943 | 14313182 | chr9 | 14347534 | 14347759 | chr9 | 14348234 | 14348533 |
| chr9 | 17906310 | 17906789 | chr9 | 17906914 | 17907153 | chr9 | 17907325 | 17907564 |
| chr9 | 19789025 | 19789381 | chr9 | 21031636 | 21031924 | chr9 | 21402520 | 21403119 |
| chr9 | 21559219 | 21559446 | chr9 | 21559678 | 21559804 | chr9 | 21964958 | 21965857 |
| chr9 | 21968138 | 21968557 | chr9 | 21970881 | 21971282 | chr9 | 21974164 | 21974329 |
| chr9 | 21974408 | 21974887 | chr9 | 21994134 | 21994313 | chr9 | 21995223 | 21995402 |
| chr9 | 21995646 | 21995825 | chr9 | 22006057 | 22006236 | chr9 | 22447567 | 22447772 |
| chr9 | 23822468 | 23822707 | chr9 | 23824487 | 23824666 | chr9 | 23831023 | 23831490 |

TABLE 14-continued

| | | Pan Cancer #4 | | | | | | |
|---|---|---|---|---|---|---|---|---|
| chr | start | end | chr | start | end | chr | start | end |
| chr9 | 29212083 | 29212382 | chr9 | 29213431 | 29213730 | chr9 | 29213938 | 29214237 |
| chr9 | 29214276 | 29214515 | chr9 | 29214585 | 29215184 | chr9 | 32782547 | 32783206 |
| chr9 | 32783263 | 32783742 | chr9 | 33524529 | 33524768 | chr9 | 33676697 | 33676876 |
| chr9 | 33677269 | 33677508 | chr9 | 34224262 | 34224497 | chr9 | 34372761 | 34373000 |
| chr9 | 34588960 | 34589259 | chr9 | 34809656 | 34810075 | chr9 | 35617195 | 35617434 |
| chr9 | 35675441 | 35676233 | chr9 | 36036994 | 36037173 | chr9 | 36318274 | 36318389 |
| chr9 | 36739659 | 36740078 | chr9 | 37002394 | 37003113 | chr9 | 37025465 | 37025884 |
| chr9 | 37026055 | 37026714 | chr9 | 37026733 | 37027512 | chr9 | 37027726 | 37027905 |
| chr9 | 37028870 | 37029049 | chr9 | 37029436 | 37030755 | chr9 | 37034163 | 37034342 |
| chr9 | 37034525 | 37034824 | chr9 | 37035427 | 37035820 | chr9 | 37036327 | 37036746 |
| chr9 | 37037594 | 37038433 | chr9 | 37467521 | 37467634 | chr9 | 38620642 | 38620808 |
| chr9 | 66456024 | 66456117 | chr9 | 71200618 | 71200720 | chr9 | 71734803 | 71734920 |
| chr9 | 71788876 | 71789512 | chr9 | 71789608 | 71789835 | chr9 | 73032727 | 73032835 |
| chr9 | 74061745 | 74062164 | chr9 | 74764449 | 74764748 | chr9 | 77112900 | 77113919 |
| chr9 | 77114649 | 77114948 | chr9 | 77115120 | 77115539 | chr9 | 77115583 | 77115587 |
| chr9 | 79626794 | 79627453 | chr9 | 79628190 | 79628429 | chr9 | 79629014 | 79629499 |
| chr9 | 79629533 | 79629553 | chr9 | 79629791 | 79630510 | chr9 | 79631115 | 79631414 |
| chr9 | 79631454 | 79631693 | chr9 | 79631785 | 79632264 | chr9 | 79632786 | 79632965 |
| chr9 | 79633322 | 79633981 | chr9 | 79634088 | 79634987 | chr9 | 79635048 | 79636066 |
| chr9 | 79636103 | 79636127 | chr9 | 79636167 | 79636642 | chr9 | 79636717 | 79637366 |
| chr9 | 79637644 | 79638336 | chr9 | 86152313 | 86152492 | chr9 | 86755443 | 86756042 |
| chr9 | 86886632 | 86886811 | chr9 | 87282934 | 87283113 | chr9 | 87283574 | 87283813 |
| chr9 | 87284603 | 87284902 | chr9 | 87285203 | 87285556 | chr9 | 88137487 | 88138091 |
| chr9 | 89517623 | 89517917 | chr9 | 89560675 | 89560914 | chr9 | 89560967 | 89561206 |
| chr9 | 91150130 | 91150429 | chr9 | 91605912 | 91606151 | chr9 | 91792283 | 91792462 |
| chr9 | 91792693 | 91792992 | chr9 | 91793083 | 91793622 | chr9 | 93697942 | 93698051 |
| chr9 | 94183793 | 94184032 | chr9 | 94572543 | 94572703 | chr9 | 94712081 | 94712320 |
| chr9 | 95417452 | 95417747 | chr9 | 95560736 | 95560915 | chr9 | 95569672 | 95569911 |
| chr9 | 95570162 | 95570521 | chr9 | 95571540 | 95571659 | chr9 | 95571753 | 95571839 |
| chr9 | 95947121 | 95947360 | chr9 | 96588726 | 96588965 | chr9 | 96710303 | 96710482 |
| chr9 | 96710582 | 96711089 | chr9 | 96711169 | 96711708 | chr9 | 96711901 | 96712080 |
| chr9 | 96713277 | 96713996 | chr9 | 96714997 | 96715068 | chr9 | 96715135 | 96715794 |
| chr9 | 96716763 | 96717542 | chr9 | 96717885 | 96718244 | chr9 | 96720752 | 96721903 |
| chr9 | 96722477 | 96722886 | chr9 | 96722999 | 96723298 | chr9 | 98111281 | 98112472 |
| chr9 | 98784698 | 98784877 | chr9 | 98789557 | 98790096 | chr9 | 99449054 | 99449487 |
| chr9 | 99639543 | 99640022 | chr9 | 99983066 | 99983245 | chr9 | 99983319 | 99983704 |
| chr9 | 99983799 | 99983918 | chr9 | 99983925 | 99984004 | chr9 | 100503542 | 100504021 |
| chr9 | 100609970 | 100610315 | chr9 | 100610603 | 100611731 | chr9 | 100613748 | 100614407 |
| chr9 | 100614463 | 100616682 | chr9 | 100616743 | 100616982 | chr9 | 100617210 | 100617449 |
| chr9 | 100617600 | 100618139 | chr9 | 100619627 | 100620166 | chr9 | 100620228 | 100620862 |
| chr9 | 100818337 | 100818516 | chr9 | 100835850 | 100835969 | chr9 | 101469169 | 101469408 |
| chr9 | 101469511 | 101469880 | chr9 | 101470034 | 101470333 | chr9 | 101470991 | 101471170 |
| chr9 | 101471477 | 101471716 | chr9 | 101471786 | 101472030 | chr9 | 101705897 | 101706796 |
| chr9 | 103174718 | 103174825 | chr9 | 104248482 | 104248721 | chr9 | 104249400 | 104249632 |
| chr9 | 104500551 | 104500850 | chr9 | 110126159 | 110126338 | chr9 | 110228102 | 110228701 |
| chr9 | 110251381 | 110251493 | chr9 | 110252260 | 110252548 | chr9 | 110252548 | 110252619 |
| chr9 | 112403096 | 112403275 | chr9 | 112403290 | 112403469 | chr9 | 113341445 | 113342044 |
| chr9 | 113342201 | 113342428 | chr9 | 115067840 | 115067945 | chr9 | 115478852 | 115478971 |
| chr9 | 115652867 | 115653526 | chr9 | 116633786 | 116633905 | chr9 | 117050887 | 117051126 |
| chr9 | 118916933 | 118917172 | chr9 | 120175695 | 120175934 | chr9 | 120176009 | 120176248 |
| chr9 | 120176793 | 120176972 | chr9 | 120507335 | 120507514 | chr9 | 122131383 | 122131742 |
| chr9 | 122131785 | 122132320 | chr9 | 123295404 | 123295559 | chr9 | 124751411 | 124751590 |
| chr9 | 125676724 | 125676798 | chr9 | 126133698 | 126133937 | chr9 | 126154201 | 126154651 |
| chr9 | 126349070 | 126349191 | chr9 | 126770159 | 126770398 | chr9 | 126771440 | 126771799 |
| chr9 | 126774442 | 126775221 | chr9 | 126775456 | 126775620 | chr9 | 126775963 | 126776202 |
| chr9 | 126777488 | 126778086 | chr9 | 126778301 | 126778593 | chr9 | 126779391 | 126780406 |
| chr9 | 126780736 | 126780975 | chr9 | 126783321 | 126783577 | chr9 | 127212750 | 127213109 |
| chr9 | 127265588 | 127266127 | chr9 | 127266372 | 127266611 | chr9 | 128652097 | 128652336 |
| chr9 | 128759764 | 128760053 | chr9 | 129276620 | 129276919 | chr9 | 129372837 | 129373316 |
| chr9 | 129376096 | 129376275 | chr9 | 129376815 | 129376892 | chr9 | 129376932 | 129376994 |
| chr9 | 129377116 | 129377415 | chr9 | 129377505 | 129378104 | chr9 | 129381027 | 129381266 |
| chr9 | 129387421 | 129387539 | chr9 | 129387701 | 129388300 | chr9 | 129388639 | 129388878 |
| chr9 | 129388915 | 129389274 | chr9 | 129400912 | 129401271 | chr9 | 129445232 | 129445651 |
| chr9 | 129445709 | 129445888 | chr9 | 129485763 | 129486002 | chr9 | 130248345 | 130248524 |
| chr9 | 130461543 | 130461842 | chr9 | 130689539 | 130689742 | chr9 | 131579939 | 131580104 |
| chr9 | 131607443 | 131607622 | chr9 | 131607696 | 131607875 | chr9 | 131854131 | 131854430 |
| chr9 | 132382297 | 132383116 | chr9 | 132402743 | 132402962 | chr9 | 132403064 | 132403303 |
| chr9 | 132559298 | 132559413 | chr9 | 132805270 | 132805449 | chr9 | 132805750 | 132805989 |
| chr9 | 133308798 | 133309037 | chr9 | 133534609 | 133534788 | chr9 | 133535638 | 133535937 |
| chr9 | 133536012 | 133536431 | chr9 | 133536675 | 133536974 | chr9 | 133537097 | 133537636 |
| chr9 | 133538090 | 133538809 | chr9 | 133539509 | 133539808 | chr9 | 133540977 | 133541276 |
| chr9 | 133541594 | 133542433 | chr9 | 133773666 | 133774025 | chr9 | 133927265 | 133927564 |
| chr9 | 133928162 | 133928341 | chr9 | 134191003 | 134191302 | chr9 | 134207833 | 134207997 |
| chr9 | 134421818 | 134421936 | chr9 | 134717221 | 134717434 | chr9 | 135037029 | 135037448 |
| chr9 | 135455317 | 135455676 | chr9 | 135455912 | 135456151 | chr9 | 135456391 | 135456630 |
| chr9 | 135456796 | 135456915 | chr9 | 135458388 | 135458687 | chr9 | 135459920 | 135460269 |

TABLE 14-continued

| Pan Cancer #4 | | | | | | | | |
|---|---|---|---|---|---|---|---|---|
| chr | start | end | chr | start | end | chr | start | end |
| chr9 | 135460795 | 135460819 | chr9 | 135461455 | 135461852 | chr9 | 135461969 | 135463048 |
| chr9 | 135464709 | 135465008 | chr9 | 135465861 | 135466220 | chr9 | 135466263 | 135466742 |
| chr9 | 135548157 | 135548265 | chr9 | 135865007 | 135865246 | chr9 | 135898809 | 135899211 |
| chr9 | 136474400 | 136474699 | chr9 | 137299018 | 137299555 | chr9 | 137299596 | 137299671 |
| chr9 | 137533897 | 137534316 | chr9 | 137656864 | 137657223 | chr9 | 137667253 | 137667432 |
| chr9 | 137718802 | 137719101 | chr9 | 137721999 | 137722197 | chr9 | 137979803 | 137980102 |
| chr9 | 137980184 | 137980363 | chr9 | 137980806 | 137980985 | chr9 | 138265038 | 138265337 |
| chr9 | 138562961 | 138563377 | chr9 | 138606221 | 138606460 | chr9 | 138606711 | 138606850 |
| chr9 | 138606927 | 138607010 | chr9 | 138627556 | 138627925 | chr9 | 138633954 | 138634253 |
| chr9 | 138659704 | 138660003 | chr9 | 138660859 | 138661098 | chr9 | 138661550 | 138661969 |
| chr9 | 138666358 | 138666657 | chr9 | 138880882 | 138880973 | chr9 | 138991833 | 138991903 |
| chr9 | 139000485 | 139000724 | chr9 | 139012193 | 139012492 | chr9 | 139024634 | 139024873 |
| chr9 | 139045579 | 139045758 | chr9 | 139047494 | 139047733 | chr9 | 139085145 | 139085444 |
| chr9 | 139085832 | 139086071 | chr9 | 139090420 | 139090659 | chr9 | 139090692 | 139091471 |
| chr9 | 139093607 | 139093966 | chr9 | 139094610 | 139094969 | chr9 | 139095264 | 139095563 |
| chr9 | 139096559 | 139097098 | chr9 | 139111194 | 139111373 | chr9 | 139268961 | 139268987 |
| chr9 | 139421881 | 139422060 | chr9 | 139698839 | 139699138 | chr9 | 139704085 | 139704384 |
| chr9 | 139739149 | 139739388 | chr9 | 139858946 | 139859365 | chr9 | 139888844 | 139889083 |
| chr9 | 140024754 | 140025113 | chr9 | 140030424 | 140030603 | chr9 | 140032802 | 140033050 |
| chr9 | 140033192 | 140033197 | chr9 | 140033325 | 140033744 | chr9 | 140033815 | 140034174 |
| chr9 | 140050893 | 140051432 | chr9 | 140127803 | 140128162 | chr9 | 140137220 | 140137334 |
| chr9 | 140205346 | 140205607 | chr9 | 140245789 | 140246084 | chr9 | 140332624 | 140333103 |
| chr9 | 140382472 | 140382697 | chr9 | 140392380 | 140392559 | chr9 | 140396944 | 140397183 |
| chr9 | 140507207 | 140507506 | chr9 | 140708961 | 140709260 | chr9 | 140727429 | 140727611 |
| chr9 | 140727769 | 140728008 | chr9 | 140769913 | 140770048 | chr9 | 140771969 | 140772431 |
| chr9 | 140772495 | 140773394 | chr10 | 524680 | 524770 | chr10 | 833228 | 833419 |
| chr10 | 978787 | 979026 | chr10 | 1585208 | 1585325 | chr10 | 1708551 | 1708583 |
| chr10 | 1779342 | 1779821 | chr10 | 3285686 | 3285792 | chr10 | 3330410 | 3330696 |
| chr10 | 3641277 | 3641396 | chr10 | 3678618 | 3678737 | chr10 | 3895312 | 3895551 |
| chr10 | 4599822 | 4600061 | chr10 | 5530673 | 5531080 | chr10 | 5875059 | 5875345 |
| chr10 | 6003386 | 6003625 | chr10 | 6042233 | 6042592 | chr10 | 6162073 | 6162302 |
| chr10 | 6577569 | 6577748 | chr10 | 6984626 | 6984731 | chr10 | 7205641 | 7205880 |
| chr10 | 7212666 | 7213145 | chr10 | 7213532 | 7213610 | chr10 | 7215985 | 7216164 |
| chr10 | 7236109 | 7236348 | chr10 | 7255627 | 7255659 | chr10 | 7414447 | 7414686 |
| chr10 | 7424552 | 7424731 | chr10 | 7449863 | 7451482 | chr10 | 7452143 | 7452862 |
| chr10 | 7453233 | 7454012 | chr10 | 7708311 | 7708379 | chr10 | 7708700 | 7709090 |
| chr10 | 7709649 | 7709807 | chr10 | 8075843 | 8076071 | chr10 | 8076264 | 8076563 |
| chr10 | 8076730 | 8077449 | chr10 | 8077790 | 8078316 | chr10 | 8084961 | 8085800 |
| chr10 | 8085875 | 8086114 | chr10 | 8091818 | 8092099 | chr10 | 8093653 | 8094072 |
| chr10 | 8095515 | 8095774 | chr10 | 8095842 | 8095934 | chr10 | 8096086 | 8096265 |
| chr10 | 8096877 | 8097296 | chr10 | 8097387 | 8097626 | chr10 | 11059620 | 11060159 |
| chr10 | 11207079 | 11207378 | chr10 | 11700861 | 11701100 | chr10 | 13043287 | 13043526 |
| chr10 | 13141002 | 13141106 | chr10 | 13715462 | 13715485 | chr10 | 13933361 | 13934260 |
| chr10 | 14966052 | 14966291 | chr10 | 15140509 | 15140625 | chr10 | 15761213 | 15761752 |
| chr10 | 15762050 | 15762211 | chr10 | 16562009 | 16563988 | chr10 | 16564013 | 16564127 |
| chr10 | 17270131 | 17270529 | chr10 | 17270889 | 17271728 | chr10 | 17271835 | 17272313 |
| chr10 | 17272527 | 17272706 | chr10 | 17429082 | 17429244 | chr10 | 17429562 | 17429724 |
| chr10 | 17496115 | 17496834 | chr10 | 18429147 | 18429386 | chr10 | 18429552 | 18429851 |
| chr10 | 21462526 | 21462690 | chr10 | 21805128 | 21805367 | chr10 | 22047362 | 22047601 |
| chr10 | 22541563 | 22542342 | chr10 | 22623924 | 22626420 | chr10 | 22633902 | 22634672 |
| chr10 | 22764556 | 22765991 | chr10 | 23216786 | 23217025 | chr10 | 23460264 | 23460552 |
| chr10 | 23461129 | 23461848 | chr10 | 23461976 | 23462995 | chr10 | 23463075 | 23464154 |
| chr10 | 23479793 | 23481171 | chr10 | 23481239 | 23481598 | chr10 | 23481862 | 23482521 |
| chr10 | 23483744 | 23484703 | chr10 | 23486177 | 23486416 | chr10 | 23487651 | 23488070 |
| chr10 | 23488297 | 23489256 | chr10 | 23489335 | 23489514 | chr10 | 23982360 | 23982899 |
| chr10 | 23983102 | 23983341 | chr10 | 23983382 | 23983801 | chr10 | 23984008 | 23984307 |
| chr10 | 23984838 | 23985066 | chr10 | 24988575 | 24988641 | chr10 | 25464528 | 25464910 |
| chr10 | 25465320 | 25465619 | chr10 | 26055737 | 26055916 | chr10 | 26222916 | 26223513 |
| chr10 | 26223957 | 26224136 | chr10 | 26500528 | 26501007 | chr10 | 26501445 | 26501668 |
| chr10 | 26503593 | 26503832 | chr10 | 26504018 | 26504257 | chr10 | 26504410 | 26505309 |
| chr10 | 26505364 | 26505783 | chr10 | 26505961 | 26506260 | chr10 | 26506288 | 26507427 |
| chr10 | 26681025 | 26681204 | chr10 | 26727024 | 26727443 | chr10 | 26727509 | 26727928 |
| chr10 | 26747074 | 26747074 | chr10 | 26816913 | 26817032 | chr10 | 27547856 | 27548575 |
| chr10 | 27794394 | 27794512 | chr10 | 27846608 | 27846719 | chr10 | 28030790 | 28031029 |
| chr10 | 28032874 | 28033113 | chr10 | 28033327 | 28033566 | chr10 | 28033667 | 28034446 |
| chr10 | 28034489 | 28035388 | chr10 | 28035520 | 28035879 | chr10 | 28287286 | 28287481 |
| chr10 | 28287693 | 28288164 | chr10 | 28957989 | 28958226 | chr10 | 29010956 | 29011239 |
| chr10 | 30025881 | 30026180 | chr10 | 31073276 | 31073541 | chr10 | 31892822 | 31893181 |
| chr10 | 32499021 | 32499260 | chr10 | 33233249 | 33233457 | chr10 | 33624079 | 33624318 |
| chr10 | 33624407 | 33624550 | chr10 | 33624621 | 33624646 | chr10 | 35929070 | 35929609 |
| chr10 | 43249935 | 43250114 | chr10 | 43250317 | 43250976 | chr10 | 43428329 | 43428688 |
| chr10 | 43428903 | 43429202 | chr10 | 43429275 | 43429514 | chr10 | 43572591 | 43572830 |
| chr10 | 43600462 | 43600733 | chr10 | 43615462 | 43615639 | chr10 | 43697812 | 43698092 |
| chr10 | 43698199 | 43698231 | chr10 | 43858258 | 43858437 | chr10 | 44879847 | 44880326 |
| chr10 | 44880773 | 44881012 | chr10 | 49652880 | 49653179 | chr10 | 49731470 | 49731829 |
| chr10 | 49731980 | 49732579 | chr10 | 50323162 | 50323360 | chr10 | 50340179 | 50340224 |

TABLE 14-continued

Pan Cancer #4

| chr | start | end | chr | start | end | chr | start | end |
|---|---|---|---|---|---|---|---|---|
| chr10 | 50507469 | 50507708 | chr10 | 50603884 | 50604243 | chr10 | 50604508 | 50604747 |
| chr10 | 50604967 | 50604979 | chr10 | 50605053 | 50605746 | chr10 | 50605931 | 50606530 |
| chr10 | 50816972 | 50817224 | chr10 | 50817778 | 50818017 | chr10 | 50818288 | 50818527 |
| chr10 | 50818724 | 50819203 | chr10 | 50821378 | 50821797 | chr10 | 50887557 | 50887916 |
| chr10 | 50976785 | 50977144 | chr10 | 54068449 | 54068688 | chr10 | 54072882 | 54073121 |
| chr10 | 54073191 | 54073370 | chr10 | 54074648 | 54074887 | chr10 | 57387344 | 57387883 |
| chr10 | 57388239 | 57388598 | chr10 | 57390195 | 57390734 | chr10 | 57391072 | 57391311 |
| chr10 | 60273033 | 60273392 | chr10 | 60935793 | 60936091 | chr10 | 60936449 | 60936808 |
| chr10 | 60936999 | 60937178 | chr10 | 63212244 | 63212783 | chr10 | 64575433 | 64575732 |
| chr10 | 64578189 | 64578626 | chr10 | 71327627 | 71327865 | chr10 | 71328678 | 71328917 |
| chr10 | 71328980 | 71329219 | chr10 | 71329462 | 71329633 | chr10 | 71331966 | 71332650 |
| chr10 | 71332686 | 71333105 | chr10 | 72015070 | 72015425 | chr10 | 72043557 | 72043976 |
| chr10 | 72200001 | 72200240 | chr10 | 72200251 | 72201390 | chr10 | 72973124 | 72973275 |
| chr10 | 73156273 | 73156465 | chr10 | 73156550 | 73156752 | chr10 | 73157768 | 73158049 |
| chr10 | 73847788 | 73848267 | chr10 | 75407495 | 75407782 | chr10 | 75488860 | 75488975 |
| chr10 | 77191147 | 77191446 | chr10 | 79396826 | 79397185 | chr10 | 81023964 | 81023989 |
| chr10 | 81664764 | 81665003 | chr10 | 82116994 | 82117283 | chr10 | 83634171 | 83634234 |
| chr10 | 83635441 | 83635620 | chr10 | 85954322 | 85954561 | chr10 | 88149273 | 88149692 |
| chr10 | 89692817 | 89692996 | chr10 | 89717584 | 89717763 | chr10 | 90966608 | 90966967 |
| chr10 | 90967587 | 90968126 | chr10 | 91294929 | 91295168 | chr10 | 91295449 | 91295808 |
| chr10 | 92617156 | 92617395 | chr10 | 93647139 | 93647378 | chr10 | 93647486 | 93647725 |
| chr10 | 94450582 | 94450806 | chr10 | 94451372 | 94451587 | chr10 | 94825999 | 94826160 |
| chr10 | 94828062 | 94828601 | chr10 | 94828633 | 94828932 | chr10 | 94834311 | 94835088 |
| chr10 | 96304116 | 96304200 | chr10 | 98129719 | 98130138 | chr10 | 99080176 | 99080535 |
| chr10 | 99080774 | 99081061 | chr10 | 99531116 | 99531535 | chr10 | 99789080 | 99789379 |
| chr10 | 99790171 | 99790410 | chr10 | 99790508 | 99790747 | chr10 | 99790845 | 99791258 |
| chr10 | 100991863 | 100991935 | chr10 | 100992056 | 100992535 | chr10 | 100992780 | 100992822 |
| chr10 | 100993448 | 100994107 | chr10 | 100995956 | 100996315 | chr10 | 101088918 | 101089517 |
| chr10 | 101089817 | 101090296 | chr10 | 101280106 | 101280569 | chr10 | 101283382 | 101283577 |
| chr10 | 101290028 | 101291284 | chr10 | 101292254 | 101292998 | chr10 | 101293071 | 101293430 |
| chr10 | 101294662 | 101295681 | chr10 | 101296665 | 101296892 | chr10 | 101874886 | 101875222 |
| chr10 | 102322156 | 102322335 | chr10 | 102419230 | 102419769 | chr10 | 102430611 | 102430850 |
| chr10 | 102473775 | 102474014 | chr10 | 102483915 | 102484632 | chr10 | 102495416 | 102495717 |
| chr10 | 102497192 | 102497791 | chr10 | 102498178 | 102498537 | chr10 | 102501285 | 102501464 |
| chr10 | 102507408 | 102507707 | chr10 | 102508902 | 102509381 | chr10 | 102586425 | 102586904 |
| chr10 | 102589340 | 102589579 | chr10 | 102589702 | 102590001 | chr10 | 102590075 | 102590494 |
| chr10 | 102890843 | 102891682 | chr10 | 102891745 | 102892104 | chr10 | 102893528 | 102895366 |
| chr10 | 102899088 | 102899687 | chr10 | 102899712 | 102900671 | chr10 | 102906423 | 102906667 |
| chr10 | 102975518 | 102975937 | chr10 | 102976963 | 102977502 | chr10 | 102983062 | 102983841 |
| chr10 | 102984313 | 102984612 | chr10 | 102985689 | 102986048 | chr10 | 102986447 | 102987646 |
| chr10 | 102989555 | 102989734 | chr10 | 102996018 | 102996737 | chr10 | 102997249 | 102997488 |
| chr10 | 102998493 | 102998912 | chr10 | 103043872 | 103044471 | chr10 | 103535527 | 103535586 |
| chr10 | 103535634 | 103535886 | chr10 | 103536143 | 103536502 | chr10 | 103579718 | 103579794 |
| chr10 | 103930133 | 103930248 | chr10 | 104169995 | 104170834 | chr10 | 105036464 | 105036943 |
| chr10 | 105037138 | 105037917 | chr10 | 105127048 | 105127156 | chr10 | 105155378 | 105155563 |
| chr10 | 105413527 | 105413886 | chr10 | 106398556 | 106398975 | chr10 | 106399505 | 106400464 |
| chr10 | 106400869 | 106402428 | chr10 | 106402620 | 106402919 | chr10 | 108923951 | 108924190 |
| chr10 | 108924365 | 108924784 | chr10 | 110226162 | 110226401 | chr10 | 110671800 | 110672339 |
| chr10 | 111216709 | 111217008 | chr10 | 112403075 | 112403374 | chr10 | 112440312 | 112440483 |
| chr10 | 115804748 | 115805107 | chr10 | 116164146 | 116164445 | chr10 | 116331052 | 116331231 |
| chr10 | 116853773 | 116854012 | chr10 | 118030550 | 118030969 | chr10 | 118031206 | 118032645 |
| chr10 | 118032841 | 118033140 | chr10 | 118033261 | 118033620 | chr10 | 118034064 | 118034243 |
| chr10 | 118890893 | 118891192 | chr10 | 118891437 | 118891854 | chr10 | 118891938 | 118893360 |
| chr10 | 118893484 | 118894383 | chr10 | 118896538 | 118896942 | chr10 | 118897822 | 118898061 |
| chr10 | 118899199 | 118899378 | chr10 | 118899435 | 118900034 | chr10 | 118900063 | 118900602 |
| chr10 | 118922061 | 118922296 | chr10 | 118922632 | 118922900 | chr10 | 118922944 | 118922991 |
| chr10 | 118923050 | 118923349 | chr10 | 118924511 | 118924990 | chr10 | 118927012 | 118927371 |
| chr10 | 118928459 | 118928614 | chr10 | 119000564 | 119001403 | chr10 | 119001460 | 119001639 |
| chr10 | 119292187 | 119292419 | chr10 | 119294258 | 119294557 | chr10 | 119294747 | 119295346 |
| chr10 | 119296628 | 119296867 | chr10 | 119297308 | 119297607 | chr10 | 119301278 | 119301757 |
| chr10 | 119302055 | 119302080 | chr10 | 119302859 | 119303278 | chr10 | 119304289 | 119304468 |
| chr10 | 119304794 | 119305213 | chr10 | 119306948 | 119307127 | chr10 | 119311793 | 119311830 |
| chr10 | 119311905 | 119311972 | chr10 | 119312673 | 119313272 | chr10 | 119806952 | 119807131 |
| chr10 | 120354169 | 120354348 | chr10 | 120355462 | 120355701 | chr10 | 120841455 | 120841563 |
| chr10 | 122216811 | 122217170 | chr10 | 122708479 | 122708773 | chr10 | 123357681 | 123357757 |
| chr10 | 123922546 | 123923565 | chr10 | 124893085 | 124893444 | chr10 | 124893551 | 124893850 |
| chr10 | 124893863 | 124894582 | chr10 | 124894787 | 124895026 | chr10 | 124895342 | 124896561 |
| chr10 | 124896768 | 124897007 | chr10 | 124897118 | 124897657 | chr10 | 124897958 | 124898056 |
| chr10 | 124898957 | 124899196 | chr10 | 124899651 | 124899890 | chr10 | 124901816 | 124903315 |
| chr10 | 124904841 | 124905200 | chr10 | 124905407 | 124905586 | chr10 | 124905834 | 124906186 |
| chr10 | 124907214 | 124907633 | chr10 | 124908017 | 124908196 | chr10 | 124908987 | 124909769 |
| chr10 | 124910287 | 124911126 | chr10 | 125425412 | 125425651 | chr10 | 125650778 | 125651437 |
| chr10 | 125851248 | 125851727 | chr10 | 125852203 | 125852622 | chr10 | 125852673 | 125853272 |
| chr10 | 126135847 | 126136146 | chr10 | 126136406 | 126136810 | chr10 | 126137145 | 126137503 |
| chr10 | 126198864 | 126199163 | chr10 | 126697829 | 126698125 | chr10 | 128076477 | 128076716 |
| chr10 | 128077188 | 128077367 | chr10 | 128993816 | 128994535 | chr10 | 128994636 | 128994995 |

TABLE 14-continued

| Pan Cancer #4 | | | | | | | | |
|---|---|---|---|---|---|---|---|---|
| chr | start | end | chr | start | end | chr | start | end |
| chr10 | 129534562 | 129535825 | chr10 | 129535986 | 129536405 | chr10 | 129888774 | 129888965 |
| chr10 | 129948037 | 129948216 | chr10 | 130085210 | 130085449 | chr10 | 130203339 | 130203578 |
| chr10 | 130338713 | 130339062 | chr10 | 130577690 | 130577869 | chr10 | 131647829 | 131648008 |
| chr10 | 131756992 | 131757531 | chr10 | 131757852 | 131758151 | chr10 | 131761291 | 131761530 |
| chr10 | 131761587 | 131761826 | chr10 | 131761987 | 131762226 | chr10 | 131762493 | 131762732 |
| chr10 | 131762803 | 131763042 | chr10 | 131763264 | 131763803 | chr10 | 131767343 | 131767522 |
| chr10 | 131768638 | 131769117 | chr10 | 131769436 | 131770335 | chr10 | 131770583 | 131770762 |
| chr10 | 131770908 | 131771327 | chr10 | 131936600 | 131936719 | chr10 | 131937393 | 131937512 |
| chr10 | 132001196 | 132001615 | chr10 | 133109096 | 133109395 | chr10 | 133109559 | 133109858 |
| chr10 | 133110260 | 133110799 | chr10 | 133794798 | 133795517 | chr10 | 133795593 | 133796312 |
| chr10 | 133849561 | 133850103 | chr10 | 133850443 | 133850862 | chr10 | 133951515 | 133952107 |
| chr10 | 133979076 | 133979164 | chr10 | 133999917 | 134000216 | chr10 | 134001000 | 134001359 |
| chr10 | 134016117 | 134016476 | chr10 | 134022771 | 134022950 | chr10 | 134095505 | 134095924 |
| chr10 | 134272961 | 134272970 | chr10 | 134301005 | 134301304 | chr10 | 134481228 | 134481527 |
| chr10 | 134598013 | 134598192 | chr10 | 134598254 | 134598613 | chr10 | 134598973 | 134599572 |
| chr10 | 134599714 | 134601053 | chr10 | 134601468 | 134601887 | chr10 | 134602107 | 134602346 |
| chr10 | 134607868 | 134608284 | chr10 | 134665056 | 134665295 | chr10 | 134679326 | 134679347 |
| chr10 | 134690469 | 134690636 | chr10 | 134693499 | 134693798 | chr10 | 134699772 | 134700011 |
| chr10 | 134733129 | 134733368 | chr10 | 134733408 | 134733707 | chr10 | 134738301 | 134738720 |
| chr10 | 134755743 | 134756270 | chr10 | 134787988 | 134788194 | chr10 | 134795938 | 134796117 |
| chr10 | 134901113 | 134901592 | chr10 | 134901919 | 134902352 | chr10 | 134916625 | 134916864 |
| chr10 | 134941043 | 134941282 | chr10 | 134942738 | 134943216 | chr10 | 134943461 | 134943644 |
| chr10 | 134944668 | 134944847 | chr10 | 135001961 | 135002260 | chr10 | 135014869 | 135015228 |
| chr10 | 135016972 | 135017209 | chr10 | 135017932 | 135018148 | chr10 | 135018744 | 135019043 |
| chr10 | 135020698 | 135020988 | chr10 | 135023396 | 135023575 | chr10 | 135043080 | 135043613 |
| chr10 | 135043869 | 135044228 | chr10 | 135044423 | 135044662 | chr10 | 135048742 | 135049041 |
| chr10 | 135050226 | 135050765 | chr10 | 135076308 | 135076586 | chr10 | 135121730 | 135122131 |
| chr10 | 135139464 | 135139805 | chr11 | 232816 | 233115 | chr11 | 392560 | 392739 |
| chr11 | 394713 | 395072 | chr11 | 406789 | 407028 | chr11 | 407326 | 407565 |
| chr11 | 626983 | 627282 | chr11 | 636821 | 637000 | chr11 | 637100 | 637528 |
| chr11 | 726323 | 726562 | chr11 | 763236 | 763775 | chr11 | 829453 | 829806 |
| chr11 | 830071 | 830370 | chr11 | 850480 | 850899 | chr11 | 862988 | 863167 |
| chr11 | 1027438 | 1027676 | chr11 | 1029142 | 1029501 | chr11 | 1030137 | 1030376 |
| chr11 | 1080304 | 1080416 | chr11 | 1081572 | 1081811 | chr11 | 1214582 | 1215001 |
| chr11 | 1215800 | 1216099 | chr11 | 1229871 | 1230050 | chr11 | 1244304 | 1244543 |
| chr11 | 1250788 | 1251027 | chr11 | 1251088 | 1251447 | chr11 | 1263504 | 1263743 |
| chr11 | 1273988 | 1274287 | chr11 | 1358284 | 1358432 | chr11 | 1374862 | 1375101 |
| chr11 | 1411801 | 1411980 | chr11 | 1430635 | 1430874 | chr11 | 1464205 | 1464504 |
| chr11 | 1469125 | 1469484 | chr11 | 1471840 | 1472139 | chr11 | 1769971 | 1770330 |
| chr11 | 1867980 | 1868339 | chr11 | 1946056 | 1946235 | chr11 | 1957312 | 1957611 |
| chr11 | 1958983 | 1959282 | chr11 | 2040009 | 2040248 | chr11 | 2209824 | 2210363 |
| chr11 | 2225974 | 2226153 | chr11 | 2278625 | 2278924 | chr11 | 2291185 | 2291844 |
| chr11 | 2291891 | 2292730 | chr11 | 2437889 | 2438246 | chr11 | 2465323 | 2465571 |
| chr11 | 2466514 | 2466873 | chr11 | 2884027 | 2884121 | chr11 | 2884158 | 2884386 |
| chr11 | 3169689 | 3169930 | chr11 | 4209031 | 4209210 | chr11 | 7273212 | 7273451 |
| chr11 | 7274141 | 7274320 | chr11 | 8040444 | 8040863 | chr11 | 8102910 | 8103209 |
| chr11 | 8189898 | 8190857 | chr11 | 8284466 | 8284858 | chr11 | 8289436 | 8289841 |
| chr11 | 8290100 | 8290515 | chr11 | 8615600 | 8615779 | chr11 | 9025890 | 9026429 |
| chr11 | 9112372 | 9112834 | chr11 | 9405310 | 9405542 | chr11 | 10509594 | 10509893 |
| chr11 | 10811069 | 10811188 | chr11 | 10815784 | 10815896 | chr11 | 12029876 | 12030355 |
| chr11 | 12030749 | 12030928 | chr11 | 12132423 | 12132662 | chr11 | 12398952 | 12399145 |
| chr11 | 12399181 | 12399311 | chr11 | 12695397 | 12695696 | chr11 | 12696530 | 12696764 |
| chr11 | 13030489 | 13030792 | chr11 | 13030862 | 13030968 | chr11 | 15136001 | 15136480 |
| chr11 | 16628727 | 16628998 | chr11 | 16632403 | 16632752 | chr11 | 17497410 | 17497769 |
| chr11 | 17740413 | 17740652 | chr11 | 17741583 | 17741685 | chr11 | 17741718 | 17742542 |
| chr11 | 17743640 | 17743874 | chr11 | 18812515 | 18812754 | chr11 | 18812940 | 18813179 |
| chr11 | 18813356 | 18813655 | chr11 | 18813691 | 18814050 | chr11 | 19263774 | 19263953 |
| chr11 | 19367007 | 19367426 | chr11 | 19735656 | 19735835 | chr11 | 20153622 | 20153861 |
| chr11 | 20177977 | 20178396 | chr11 | 20180244 | 20180896 | chr11 | 20181115 | 20181354 |
| chr11 | 20181608 | 20182087 | chr11 | 20182763 | 20183062 | chr11 | 20183157 | 20183211 |
| chr11 | 20183313 | 20183516 | chr11 | 20183575 | 20183852 | chr11 | 20184481 | 20185500 |
| chr11 | 20229275 | 20229634 | chr11 | 20229811 | 20230110 | chr11 | 20230312 | 20230551 |
| chr11 | 20618116 | 20619255 | chr11 | 20619637 | 20620056 | chr11 | 20621460 | 20621733 |
| chr11 | 20622613 | 20623452 | chr11 | 20690555 | 20691034 | chr11 | 20691127 | 20691546 |
| chr11 | 20691591 | 20692010 | chr11 | 20692372 | 20692611 | chr11 | 22215026 | 22215385 |
| chr11 | 22362853 | 22363272 | chr11 | 22364719 | 22365078 | chr11 | 22365323 | 22365562 |
| chr11 | 27742111 | 27742290 | chr11 | 27743025 | 27743272 | chr11 | 27743343 | 27743702 |
| chr11 | 27744057 | 27744596 | chr11 | 27744609 | 27744832 | chr11 | 30037596 | 30037818 |
| chr11 | 30038595 | 30038834 | chr11 | 30605946 | 30606201 | chr11 | 30606665 | 30606964 |
| chr11 | 30607269 | 30607508 | chr11 | 31818376 | 31818674 | chr11 | 31819221 | 31819508 |
| chr11 | 31819569 | 31819928 | chr11 | 31819966 | 31821105 | chr11 | 31821209 | 31821860 |
| chr11 | 31822240 | 31822479 | chr11 | 31824209 | 31824448 | chr11 | 31824473 | 31824772 |
| chr11 | 31824940 | 31825359 | chr11 | 31825611 | 31827290 | chr11 | 31827362 | 31828142 |
| chr11 | 31833007 | 31833232 | chr11 | 31835633 | 31835872 | chr11 | 31835959 | 31836517 |
| chr11 | 31836927 | 31838486 | chr11 | 31838596 | 31839135 | chr11 | 31839215 | 31840174 |
| chr11 | 31840486 | 31841025 | chr11 | 31841287 | 31842366 | chr11 | 31845947 | 31845991 |

TABLE 14-continued

Pan Cancer #4

| chr | start | end | chr | start | end | chr | start | end |
|---|---|---|---|---|---|---|---|---|
| chr11 | 31846078 | 31846306 | chr11 | 31846351 | 31847070 | chr11 | 31847169 | 31848008 |
| chr11 | 31848377 | 31849177 | chr11 | 32009013 | 32009252 | chr11 | 32354816 | 32355291 |
| chr11 | 32448482 | 32449081 | chr11 | 32455499 | 32455738 | chr11 | 32455754 | 32456113 |
| chr11 | 32456189 | 32457268 | chr11 | 32457615 | 32458274 | chr11 | 32458307 | 32458860 |
| chr11 | 32459609 | 32459971 | chr11 | 32460118 | 32460148 | chr11 | 32460373 | 32460612 |
| chr11 | 32460711 | 32460950 | chr11 | 33037393 | 33037632 | chr11 | 33858439 | 33858544 |
| chr11 | 33890197 | 33890436 | chr11 | 33993910 | 33993979 | chr11 | 34535019 | 34535198 |
| chr11 | 35547412 | 35547651 | chr11 | 35641582 | 35641718 | chr11 | 35684866 | 35685225 |
| chr11 | 43596412 | 43596693 | chr11 | 43600416 | 43600655 | chr11 | 43601012 | 43601551 |
| chr11 | 43602369 | 43603328 | chr11 | 43603544 | 43604263 | chr11 | 44325599 | 44325838 |
| chr11 | 44326042 | 44326281 | chr11 | 44326341 | 44326580 | chr11 | 44330555 | 44331814 |
| chr11 | 44332978 | 44333157 | chr11 | 44333466 | 44333576 | chr11 | 44337564 | 44338154 |
| chr11 | 44338232 | 44338471 | chr11 | 44340722 | 44340808 | chr11 | 44341881 | 44342120 |
| chr11 | 46316761 | 46317780 | chr11 | 47208968 | 47209267 | chr11 | 47358895 | 47359314 |
| chr11 | 57194253 | 57194612 | chr11 | 57235332 | 57235511 | chr11 | 57437215 | 57437316 |
| chr11 | 57501032 | 57501145 | chr11 | 58672666 | 58673145 | chr11 | 59323514 | 59323551 |
| chr11 | 59323780 | 59323813 | chr11 | 59329224 | 59329343 | chr11 | 59333344 | 59333623 |
| chr11 | 60718587 | 60719246 | chr11 | 61049596 | 61049756 | chr11 | 61058193 | 61058432 |
| chr11 | 61062741 | 61063220 | chr11 | 61276902 | 61277321 | chr11 | 61594995 | 61595354 |
| chr11 | 61596321 | 61596740 | chr11 | 61664564 | 61664863 | chr11 | 61666032 | 61666211 |
| chr11 | 61722964 | 61723262 | chr11 | 62370646 | 62370825 | chr11 | 62440550 | 62440690 |
| chr11 | 63609981 | 63610099 | chr11 | 63641023 | 63641104 | chr11 | 63767909 | 63768208 |
| chr11 | 63849298 | 63849530 | chr11 | 63934600 | 63934709 | chr11 | 64105852 | 64106031 |
| chr11 | 64120805 | 64120984 | chr11 | 64140323 | 64140502 | chr11 | 64410622 | 64410861 |
| chr11 | 64480332 | 64480691 | chr11 | 64480724 | 64481143 | chr11 | 64578481 | 64578600 |
| chr11 | 64739369 | 64739608 | chr11 | 64809866 | 64809965 | chr11 | 64950214 | 64950438 |
| chr11 | 65091311 | 65091471 | chr11 | 65185459 | 65185818 | chr11 | 65405568 | 65405597 |
| chr11 | 65478529 | 65478644 | chr11 | 65511077 | 65511256 | chr11 | 65511332 | 65511571 |
| chr11 | 65553957 | 65554195 | chr11 | 65600716 | 65601735 | chr11 | 65779218 | 65779457 |
| chr11 | 65816357 | 65816656 | chr11 | 66188041 | 66188220 | chr11 | 66188395 | 66189054 |
| chr11 | 66454350 | 66454529 | chr11 | 66511148 | 66511327 | chr11 | 66513133 | 66513252 |
| chr11 | 66513554 | 66513732 | chr11 | 66625105 | 66625344 | chr11 | 66648954 | 66649133 |
| chr11 | 66658258 | 66658365 | chr11 | 66790519 | 66790758 | chr11 | 67072139 | 67072449 |
| chr11 | 67209918 | 67210157 | chr11 | 67350887 | 67351066 | chr11 | 67462559 | 67462918 |
| chr11 | 67764102 | 67764341 | chr11 | 67781387 | 67781650 | chr11 | 67797102 | 67797281 |
| chr11 | 68096026 | 68096257 | chr11 | 68409507 | 68409663 | chr11 | 68804647 | 68804872 |
| chr11 | 69192466 | 69192885 | chr11 | 69280478 | 69280717 | chr11 | 69465962 | 69466143 |
| chr11 | 69516896 | 69517251 | chr11 | 69517942 | 69518301 | chr11 | 69518445 | 69518708 |
| chr11 | 69588848 | 69589267 | chr11 | 69589750 | 69589929 | chr11 | 69590067 | 69590306 |
| chr11 | 71192669 | 71192921 | chr11 | 71318231 | 71319070 | chr11 | 71951540 | 71951815 |
| chr11 | 71952262 | 71952621 | chr11 | 71954538 | 71954717 | chr11 | 71955242 | 71955481 |
| chr11 | 71955905 | 71956444 | chr11 | 72432759 | 72432997 | chr11 | 72475581 | 72475814 |
| chr11 | 72532274 | 72532453 | chr11 | 72929666 | 72929731 | chr11 | 73072871 | 73073050 |
| chr11 | 73310285 | 73310445 | chr11 | 74394397 | 74394696 | chr11 | 74953165 | 74953524 |
| chr11 | 75379155 | 75379994 | chr11 | 75459452 | 75459564 | chr11 | 76371639 | 76372178 |
| chr11 | 78672822 | 78673061 | chr11 | 79151076 | 79151315 | chr11 | 82444290 | 82445189 |
| chr11 | 86085657 | 86086065 | chr11 | 86383080 | 86383186 | chr11 | 88241623 | 88242702 |
| chr11 | 88798997 | 88799296 | chr11 | 91957408 | 91957767 | chr11 | 91957893 | 91958312 |
| chr11 | 91958633 | 91959532 | chr11 | 91959901 | 91960122 | chr11 | 93063495 | 93063734 |
| chr11 | 93063790 | 93064029 | chr11 | 94133991 | 94134950 | chr11 | 94275701 | 94275813 |
| chr11 | 94473511 | 94473997 | chr11 | 94474399 | 94474401 | chr11 | 94502273 | 94502592 |
| chr11 | 94884070 | 94884235 | chr11 | 98891381 | 98891980 | chr11 | 100997579 | 100998085 |
| chr11 | 100998178 | 100998417 | chr11 | 100998588 | 100998827 | chr11 | 101453080 | 101453619 |
| chr11 | 101454101 | 101454580 | chr11 | 102961259 | 102961378 | chr11 | 102979953 | 102980132 |
| chr11 | 104034430 | 104035089 | chr11 | 105480662 | 105480901 | chr11 | 105481125 | 105481604 |
| chr11 | 106888220 | 106888519 | chr11 | 106888542 | 106888901 | chr11 | 107461549 | 107461728 |
| chr11 | 107462318 | 107462557 | chr11 | 108603286 | 108603338 | chr11 | 109292830 | 109293129 |
| chr11 | 109293635 | 109293934 | chr11 | 110582154 | 110582513 | chr11 | 110582794 | 110583153 |
| chr11 | 110583473 | 110583832 | chr11 | 111383104 | 111383763 | chr11 | 111411019 | 111412147 |
| chr11 | 114112948 | 114113127 | chr11 | 115375030 | 115375269 | chr11 | 115530040 | 115530662 |
| chr11 | 115630414 | 115631013 | chr11 | 115631217 | 115631456 | chr11 | 116451226 | 116451287 |
| chr11 | 119292705 | 119292884 | chr11 | 119293284 | 119293703 | chr11 | 119612134 | 119612493 |
| chr11 | 119612999 | 119613178 | chr11 | 120008006 | 120008605 | chr11 | 120039730 | 120039969 |
| chr11 | 120435322 | 120435561 | chr11 | 120435726 | 120435905 | chr11 | 120998614 | 120998913 |
| chr11 | 122847182 | 122847781 | chr11 | 122847976 | 122848695 | chr11 | 122849808 | 122850263 |
| chr11 | 122850331 | 122850630 | chr11 | 122851074 | 122851313 | chr11 | 122852338 | 122852577 |
| chr11 | 122854907 | 122855136 | chr11 | 123066359 | 123066538 | chr11 | 123228971 | 123229510 |
| chr11 | 123300736 | 123300955 | chr11 | 123301016 | 123302115 | chr11 | 124735341 | 124735580 |
| chr11 | 124736105 | 124736344 | chr11 | 124738694 | 124739125 | chr11 | 124739149 | 124739173 |
| chr11 | 125035687 | 125036286 | chr11 | 125036503 | 125036742 | chr11 | 125220423 | 125220722 |
| chr11 | 125755512 | 125755727 | chr11 | 125773587 | 125774186 | chr11 | 126870108 | 126870628 |
| chr11 | 126870379 | 126870618 | chr11 | 126873304 | 126873603 | chr11 | 128562802 | 128563818 |
| chr11 | 128563879 | 128564405 | chr11 | 128564641 | 128565480 | chr11 | 128657933 | 128658051 |
| chr11 | 129242783 | 129243643 | chr11 | 129243944 | 129244646 | chr11 | 129245747 | 129245892 |
| chr11 | 129245981 | 129246046 | chr11 | 130318860 | 130319099 | chr11 | 130319451 | 130319690 |
| chr11 | 130785406 | 130785705 | chr11 | 131522676 | 131522960 | chr11 | 131564873 | 131565101 |

TABLE 14-continued

Pan Cancer #4

| chr | start | end | chr | start | end | chr | start | end |
|---|---|---|---|---|---|---|---|---|
| chr11 | 131766899 | 131767048 | chr11 | 131780391 | 131781350 | chr11 | 132484279 | 132484490 |
| chr11 | 132813545 | 132814049 | chr11 | 132864036 | 132864275 | chr11 | 132934031 | 132934270 |
| chr11 | 132952677 | 132953003 | chr11 | 132953064 | 132953423 | chr11 | 133231637 | 133231930 |
| chr11 | 133402114 | 133402353 | chr11 | 133825146 | 133825625 | chr11 | 133906702 | 133907001 |
| chr11 | 133938911 | 133939270 | chr11 | 134145629 | 134146468 | chr11 | 134146579 | 134146998 |
| chr11 | 134201404 | 134201640 | chr11 | 134201754 | 134202173 | chr11 | 134281288 | 134281543 |
| chr12 | 570012 | 570251 | chr12 | 1639060 | 1639299 | chr12 | 2162477 | 2162896 |
| chr12 | 2163071 | 2163370 | chr12 | 2403649 | 2403806 | chr12 | 2565971 | 2566330 |
| chr12 | 2861968 | 2862327 | chr12 | 2964372 | 2964671 | chr12 | 3600241 | 3600420 |
| chr12 | 3602186 | 3602965 | chr12 | 3603009 | 3603061 | chr12 | 4214010 | 4214245 |
| chr12 | 4273972 | 4274490 | chr12 | 4362362 | 4362541 | chr12 | 4378172 | 4378411 |
| chr12 | 4379275 | 4379574 | chr12 | 4381341 | 4382480 | chr12 | 4382863 | 4383102 |
| chr12 | 4383399 | 4383878 | chr12 | 4384315 | 4384494 | chr12 | 4392801 | 4393023 |
| chr12 | 4405515 | 4405694 | chr12 | 4554727 | 4554906 | chr12 | 5017994 | 5018773 |
| chr12 | 5018954 | 5020513 | chr12 | 5152951 | 5153610 | chr12 | 5541020 | 5541259 |
| chr12 | 5542233 | 5542532 | chr12 | 5542656 | 5543015 | chr12 | 5840126 | 5840305 |
| chr12 | 6483537 | 6483836 | chr12 | 6664407 | 6665486 | chr12 | 7559085 | 7559384 |
| chr12 | 8127119 | 8127238 | chr12 | 8171284 | 8171823 | chr12 | 8808505 | 8808640 |
| chr12 | 8850582 | 8850818 | chr12 | 8975096 | 8975452 | chr12 | 10085826 | 10085932 |
| chr12 | 10363204 | 10363319 | chr12 | 11653375 | 11653554 | chr12 | 12848294 | 12848653 |
| chr12 | 14133059 | 14133358 | chr12 | 14133541 | 14133902 | chr12 | 14135016 | 14135354 |
| chr12 | 15374156 | 15374395 | chr12 | 16500480 | 16500685 | chr12 | 20521624 | 20521923 |
| chr12 | 20522383 | 20522562 | chr12 | 20522681 | 20522860 | chr12 | 20522976 | 20522980 |
| chr12 | 21680300 | 21680779 | chr12 | 21810395 | 21810956 | chr12 | 21832988 | 21833095 |
| chr12 | 22093749 | 22094888 | chr12 | 22094997 | 22095236 | chr12 | 22486717 | 22487556 |
| chr12 | 22698102 | 22698207 | chr12 | 24714835 | 24715014 | chr12 | 24715161 | 24715340 |
| chr12 | 24715947 | 24716306 | chr12 | 25055865 | 25056524 | chr12 | 25101507 | 25101746 |
| chr12 | 25101824 | 25102183 | chr12 | 25380187 | 25380366 | chr12 | 25398165 | 25398404 |
| chr12 | 28127676 | 28128395 | chr12 | 28128457 | 28129176 | chr12 | 29935913 | 29936152 |
| chr12 | 29936524 | 29936777 | chr12 | 29936792 | 29936943 | chr12 | 29937234 | 29937473 |
| chr12 | 30322697 | 30323596 | chr12 | 30975472 | 30976015 | chr12 | 31079179 | 31079594 |
| chr12 | 32340225 | 32340336 | chr12 | 33591700 | 33591879 | chr12 | 33592512 | 33592991 |
| chr12 | 34494814 | 34494993 | chr12 | 34502649 | 34502888 | chr12 | 39299040 | 39299815 |
| chr12 | 39299269 | 39299639 | chr12 | 39539276 | 39539515 | chr12 | 40618318 | 40618557 |
| chr12 | 41086102 | 41086461 | chr12 | 41086706 | 41087185 | chr12 | 41582422 | 41583081 |
| chr12 | 41583278 | 41583471 | chr12 | 43944800 | 43945219 | chr12 | 43945262 | 43945621 |
| chr12 | 43945742 | 43946401 | chr12 | 45269415 | 45269714 | chr12 | 45444029 | 45444920 |
| chr12 | 45445062 | 45445348 | chr12 | 46767555 | 46767558 | chr12 | 47225301 | 47225660 |
| chr12 | 47629275 | 47629307 | chr12 | 47629398 | 47629454 | chr12 | 48397154 | 48398173 |
| chr12 | 48398567 | 48398746 | chr12 | 49297770 | 49298009 | chr12 | 49366280 | 49366519 |
| chr12 | 49374838 | 49375197 | chr12 | 49375248 | 49375607 | chr12 | 49390776 | 49391975 |
| chr12 | 49657624 | 49657722 | chr12 | 49690975 | 49691154 | chr12 | 49726969 | 49727208 |
| chr12 | 49729640 | 49730179 | chr12 | 50297417 | 50298136 | chr12 | 50355193 | 50355552 |
| chr12 | 50426672 | 50426894 | chr12 | 51421134 | 51421373 | chr12 | 51421482 | 51421661 |
| chr12 | 51565470 | 51565562 | chr12 | 51930615 | 51930785 | chr12 | 52262896 | 52263195 |
| chr12 | 52301205 | 52301444 | chr12 | 52400735 | 52401616 | chr12 | 52627102 | 52627381 |
| chr12 | 52652054 | 52652713 | chr12 | 53108005 | 53108304 | chr12 | 53359245 | 53359664 |
| chr12 | 54089004 | 54089602 | chr12 | 54132172 | 54132411 | chr12 | 54145750 | 54145989 |
| chr12 | 54321170 | 54321709 | chr12 | 54322108 | 54322302 | chr12 | 54324719 | 54325018 |
| chr12 | 54329264 | 54330007 | chr12 | 54330980 | 54331219 | chr12 | 54332774 | 54333433 |
| chr12 | 54338589 | 54339668 | chr12 | 54343718 | 54343955 | chr12 | 54345523 | 54346122 |
| chr12 | 54348761 | 54349420 | chr12 | 54354419 | 54354718 | chr12 | 54354805 | 54355575 |
| chr12 | 54359873 | 54360172 | chr12 | 54360510 | 54360729 | chr12 | 54377835 | 54378194 |
| chr12 | 54379100 | 54379699 | chr12 | 54379785 | 54380486 | chr12 | 54387752 | 54388051 |
| chr12 | 54388141 | 54388320 | chr12 | 54391267 | 54391506 | chr12 | 54393403 | 54393762 |
| chr12 | 54393847 | 54394266 | chr12 | 54394307 | 54394546 | chr12 | 54398697 | 54399056 |
| chr12 | 54399542 | 54399721 | chr12 | 54402654 | 54402812 | chr12 | 54402975 | 54403454 |
| chr12 | 54408330 | 54408809 | chr12 | 54424670 | 54424887 | chr12 | 54424912 | 54425211 |
| chr12 | 54447340 | 54447519 | chr12 | 54447781 | 54448080 | chr12 | 54520658 | 54520957 |
| chr12 | 54720221 | 54720320 | chr12 | 54812150 | 54812449 | chr12 | 54942906 | 54943191 |
| chr12 | 56882365 | 56882460 | chr12 | 57559778 | 57559914 | chr12 | 57618478 | 57619077 |
| chr12 | 57881046 | 57881345 | chr12 | 57943980 | 57944219 | chr12 | 58021218 | 58021817 |
| chr12 | 58021824 | 58022093 | chr12 | 58025551 | 58025970 | chr12 | 62584739 | 62586118 |
| chr12 | 62586178 | 62586357 | chr12 | 63025615 | 63026257 | chr12 | 63543749 | 63544828 |
| chr12 | 63545239 | 63545418 | chr12 | 64061721 | 64062260 | chr12 | 64062295 | 64062654 |
| chr12 | 64062830 | 64063189 | chr12 | 64783098 | 64783322 | chr12 | 64784007 | 64784352 |
| chr12 | 64784460 | 64784639 | chr12 | 65218000 | 65219259 | chr12 | 65219281 | 65219859 |
| chr12 | 65220129 | 65220428 | chr12 | 65514781 | 65515620 | chr12 | 65516379 | 65516558 |
| chr12 | 65557115 | 65557234 | chr12 | 65562064 | 65562172 | chr12 | 66122711 | 66123610 |
| chr12 | 66135910 | 66136089 | chr12 | 66582743 | 66583222 | chr12 | 69327182 | 69327541 |
| chr12 | 69754351 | 69754470 | chr12 | 69754600 | 69754767 | chr12 | 69964101 | 69964340 |
| chr12 | 70087412 | 70087651 | chr12 | 72332550 | 72332789 | chr12 | 72665167 | 72665526 |
| chr12 | 72665566 | 72665877 | chr12 | 72666014 | 72666313 | chr12 | 72666620 | 72667519 |
| chr12 | 72667578 | 72667757 | chr12 | 75601168 | 75602007 | chr12 | 75602895 | 75603314 |
| chr12 | 75728262 | 75728561 | chr12 | 77719218 | 77719517 | chr12 | 79257138 | 79257437 |
| chr12 | 79258850 | 79259029 | chr12 | 81102105 | 81102603 | chr12 | 81107921 | 81108100 |

TABLE 14-continued

Pan Cancer #4

| chr | start | end | chr | start | end | chr | start | end |
|---|---|---|---|---|---|---|---|---|
| chr12 | 81471425 | 81472204 | chr12 | 85306430 | 85306549 | chr12 | 85667173 | 85667832 |
| chr12 | 85673132 | 85673311 | chr12 | 85673385 | 85674884 | chr12 | 88974346 | 88974356 |
| chr12 | 93966337 | 93966696 | chr12 | 93966910 | 93967329 | chr12 | 94543308 | 94543547 |
| chr12 | 94543811 | 94544080 | chr12 | 95267450 | 95267629 | chr12 | 95267772 | 95268000 |
| chr12 | 95941794 | 95943053 | chr12 | 99288212 | 99289411 | chr12 | 101025306 | 101025485 |
| chr12 | 101110926 | 101111165 | chr12 | 101111277 | 101111576 | chr12 | 103218396 | 103218655 |
| chr12 | 103350250 | 103350429 | chr12 | 103351464 | 103352783 | chr12 | 103358763 | 103359002 |
| chr12 | 103359482 | 103359661 | chr12 | 103889086 | 103889306 | chr12 | 103889660 | 103889899 |
| chr12 | 104609340 | 104610179 | chr12 | 104850430 | 104850669 | chr12 | 104850983 | 104851282 |
| chr12 | 104851941 | 104852600 | chr12 | 105478222 | 105478457 | chr12 | 106974279 | 106974458 |
| chr12 | 106976641 | 106976880 | chr12 | 106977394 | 106977589 | chr12 | 106979079 | 106979618 |
| chr12 | 106979718 | 106980077 | chr12 | 106980129 | 106980428 | chr12 | 106980771 | 106981490 |
| chr12 | 107486462 | 107486673 | chr12 | 107487114 | 107487945 | chr12 | 107712199 | 107712378 |
| chr12 | 107713131 | 107713310 | chr12 | 107714771 | 107715250 | chr12 | 108168883 | 108169662 |
| chr12 | 108237377 | 108237676 | chr12 | 108238034 | 108238719 | chr12 | 108297320 | 108297559 |
| chr12 | 110353315 | 110353553 | chr12 | 110717447 | 110717806 | chr12 | 111127079 | 111127438 |
| chr12 | 111471099 | 111471638 | chr12 | 111471871 | 111472511 | chr12 | 111472572 | 111472830 |
| chr12 | 111763136 | 111763227 | chr12 | 113012877 | 113013236 | chr12 | 113541644 | 113542183 |
| chr12 | 113592150 | 113592449 | chr12 | 113900616 | 113900855 | chr12 | 113900974 | 113901693 |
| chr12 | 113901951 | 113902429 | chr12 | 113903394 | 113903573 | chr12 | 113904689 | 113905108 |
| chr12 | 113908894 | 113909553 | chr12 | 113909569 | 113909808 | chr12 | 113913180 | 113914139 |
| chr12 | 113916147 | 113916266 | chr12 | 113916327 | 113916419 | chr12 | 113916575 | 113916754 |
| chr12 | 113916873 | 113917112 | chr12 | 113917212 | 113917391 | chr12 | 113917684 | 113917983 |
| chr12 | 114029325 | 114029509 | chr12 | 114029546 | 114029744 | chr12 | 114075942 | 114076177 |
| chr12 | 114337849 | 114337868 | chr12 | 114833895 | 114834194 | chr12 | 114838227 | 114838826 |
| chr12 | 114840946 | 114841185 | chr12 | 114843016 | 114843375 | chr12 | 114843454 | 114843753 |
| chr12 | 114844102 | 114844401 | chr12 | 114846623 | 114846862 | chr12 | 114846886 | 114847741 |
| chr12 | 114851969 | 114852181 | chr12 | 114852214 | 114852268 | chr12 | 114877068 | 114877367 |
| chr12 | 114878448 | 114878687 | chr12 | 114878734 | 114879093 | chr12 | 114881550 | 114881849 |
| chr12 | 114882488 | 114882727 | chr12 | 114883385 | 114883554 | chr12 | 114885134 | 114885373 |
| chr12 | 114918513 | 114918806 | chr12 | 115136153 | 115136441 | chr12 | 116945988 | 116946647 |
| chr12 | 117473983 | 117474282 | chr12 | 117797999 | 117798170 | chr12 | 117798589 | 117799068 |
| chr12 | 117799322 | 117799621 | chr12 | 118860317 | 118860436 | chr12 | 119212120 | 119212479 |
| chr12 | 119418512 | 119418931 | chr12 | 119419362 | 119419541 | chr12 | 119419631 | 119419920 |
| chr12 | 120032777 | 120033256 | chr12 | 120148125 | 120148345 | chr12 | 120148824 | 120149063 |
| chr12 | 120885155 | 120885274 | chr12 | 121622472 | 121622591 | chr12 | 122192885 | 122192933 |
| chr12 | 122284969 | 122285189 | chr12 | 123129041 | 123129139 | chr12 | 123233818 | 123233926 |
| chr12 | 124393463 | 124393702 | chr12 | 124397514 | 124397693 | chr12 | 125009254 | 125009381 |
| chr12 | 125533851 | 125534508 | chr12 | 125670024 | 125670383 | chr12 | 126168468 | 126168707 |
| chr12 | 127210933 | 127211472 | chr12 | 127765066 | 127765535 | chr12 | 127939988 | 127940189 |
| chr12 | 127940271 | 127940347 | chr12 | 128751295 | 128751534 | chr12 | 128751732 | 128752331 |
| chr12 | 128752423 | 128753022 | chr12 | 128753136 | 128753315 | chr12 | 128850442 | 128850739 |
| chr12 | 129337901 | 129338919 | chr12 | 130037571 | 130037866 | chr12 | 130387716 | 130387914 |
| chr12 | 130388332 | 130389231 | chr12 | 130589116 | 130589354 | chr12 | 130645131 | 130645730 |
| chr12 | 130646590 | 130647179 | chr12 | 130647263 | 130648569 | chr12 | 130821287 | 130821706 |
| chr12 | 130968586 | 130968758 | chr12 | 131200303 | 131200649 | chr12 | 131400719 | 131401018 |
| chr12 | 131402943 | 131403229 | chr12 | 131513255 | 131513494 | chr12 | 132169246 | 132169357 |
| chr12 | 132221614 | 132222153 | chr12 | 132333337 | 132333418 | chr12 | 132333517 | 132333696 |
| chr12 | 132348549 | 132348788 | chr12 | 132423596 | 132423829 | chr12 | 132643371 | 132643376 |
| chr12 | 132986419 | 132986658 | chr12 | 133002713 | 133003312 | chr12 | 133194996 | 133195295 |
| chr12 | 133199642 | 133199797 | chr12 | 133463657 | 133463956 | chr12 | 133464018 | 133464074 |
| chr12 | 133464755 | 133464920 | chr12 | 133481333 | 133481732 | chr12 | 133484660 | 133485439 |
| chr12 | 133485463 | 133485942 | chr12 | 133757959 | 133758198 | chr13 | 20735708 | 20736187 |
| chr13 | 20875662 | 20876021 | chr13 | 21649557 | 21649856 | chr13 | 22243192 | 22243551 |
| chr13 | 23489764 | 23490003 | chr13 | 23733355 | 23734124 | chr13 | 23734182 | 23734781 |
| chr13 | 24477566 | 24477985 | chr13 | 25115623 | 25115852 | chr13 | 25319764 | 25321443 |
| chr13 | 25321612 | 25322031 | chr13 | 25592963 | 25593201 | chr13 | 25620951 | 25621490 |
| chr13 | 25744639 | 25746054 | chr13 | 25946129 | 25946488 | chr13 | 25946529 | 25946888 |
| chr13 | 26042580 | 26043590 | chr13 | 26625215 | 26625814 | chr13 | 26625994 | 26626233 |
| chr13 | 27132307 | 27132546 | chr13 | 27334118 | 27334657 | chr13 | 27334684 | 27334983 |
| chr13 | 28239896 | 28240195 | chr13 | 28365615 | 28366181 | chr13 | 28366381 | 28366680 |
| chr13 | 28366923 | 28367162 | chr13 | 28367712 | 28368251 | chr13 | 28368373 | 28368672 |
| chr13 | 28368872 | 28369891 | chr13 | 28369952 | 28370071 | chr13 | 28370855 | 28371154 |
| chr13 | 28394667 | 28394966 | chr13 | 28395408 | 28395647 | chr13 | 28395917 | 28396156 |
| chr13 | 28491694 | 28492050 | chr13 | 28492160 | 28492639 | chr13 | 28528432 | 28528851 |
| chr13 | 28540657 | 28541016 | chr13 | 28543138 | 28543317 | chr13 | 28544321 | 28544980 |
| chr13 | 28549396 | 28550655 | chr13 | 28551320 | 28551559 | chr13 | 28551850 | 28552269 |
| chr13 | 28552481 | 28552660 | chr13 | 28552720 | 28552899 | chr13 | 28552935 | 28553234 |
| chr13 | 28673927 | 28674826 | chr13 | 29067676 | 29068515 | chr13 | 29068847 | 29069146 |
| chr13 | 29106217 | 29107409 | chr13 | 30707495 | 30707674 | chr13 | 31742856 | 31743242 |
| chr13 | 32605033 | 32605212 | chr13 | 32605357 | 32605596 | chr13 | 32605642 | 32606001 |
| chr13 | 33590737 | 33591036 | chr13 | 33591211 | 33591510 | chr13 | 33924579 | 33924812 |
| chr13 | 36045193 | 36045372 | chr13 | 36704848 | 36705147 | chr13 | 36705351 | 36705590 |
| chr13 | 36729006 | 36729229 | chr13 | 36920216 | 36920515 | chr13 | 36920528 | 36920887 |
| chr13 | 37004681 | 37004992 | chr13 | 37005581 | 37006840 | chr13 | 37247982 | 37248316 |
| chr13 | 37248886 | 37249125 | chr13 | 37633915 | 37634094 | chr13 | 37643855 | 37644094 |

TABLE 14-continued

Pan Cancer #4

| chr | start | end | chr | start | end | chr | start | end |
|---|---|---|---|---|---|---|---|---|
| chr13 | 38443544 | 38443796 | chr13 | 39261309 | 39261472 | chr13 | 43566148 | 43566678 |
| chr13 | 44947643 | 44948302 | chr13 | 45885802 | 45885981 | chr13 | 45905243 | 45905356 |
| chr13 | 46425447 | 46425686 | chr13 | 46660850 | 46660944 | chr13 | 46961395 | 46961634 |
| chr13 | 47468065 | 47468244 | chr13 | 47526167 | 47526286 | chr13 | 48667803 | 48667982 |
| chr13 | 49794034 | 49795273 | chr13 | 53312917 | 53313996 | chr13 | 53419636 | 53419875 |
| chr13 | 53419931 | 53420170 | chr13 | 53420284 | 53420823 | chr13 | 53421161 | 53421164 |
| chr13 | 53421288 | 53421880 | chr13 | 53422220 | 53422459 | chr13 | 53423759 | 53424058 |
| chr13 | 58203504 | 58203743 | chr13 | 58203768 | 58204187 | chr13 | 58204253 | 58204492 |
| chr13 | 58205944 | 58207083 | chr13 | 58207382 | 58208101 | chr13 | 58208412 | 58209011 |
| chr13 | 67804144 | 67804175 | chr13 | 67804420 | 67804599 | chr13 | 67805100 | 67805339 |
| chr13 | 70681550 | 70682149 | chr13 | 72439047 | 72439109 | chr13 | 73619573 | 73619698 |
| chr13 | 78492724 | 78492942 | chr13 | 78493092 | 78493271 | chr13 | 78493363 | 78493902 |
| chr13 | 79169722 | 79170981 | chr13 | 79171038 | 79171277 | chr13 | 79175678 | 79176877 |
| chr13 | 79176897 | 79178096 | chr13 | 79183327 | 79183566 | chr13 | 84455499 | 84455798 |
| chr13 | 88323504 | 88324283 | chr13 | 88324415 | 88324714 | chr13 | 88325201 | 88325560 |
| chr13 | 88325731 | 88326140 | chr13 | 88326447 | 88327106 | chr13 | 88997832 | 88997951 |
| chr13 | 91948415 | 91948594 | chr13 | 92050668 | 92050843 | chr13 | 92051065 | 92051244 |
| chr13 | 92051273 | 92051632 | chr13 | 93879213 | 93879452 | chr13 | 93879596 | 93879775 |
| chr13 | 93879994 | 93880953 | chr13 | 95357237 | 95357416 | chr13 | 95357496 | 95357855 |
| chr13 | 95357954 | 95358253 | chr13 | 95359656 | 95359895 | chr13 | 95360228 | 95360467 |
| chr13 | 95363111 | 95363530 | chr13 | 95363697 | 95364296 | chr13 | 95364409 | 95364888 |
| chr13 | 95619931 | 95620170 | chr13 | 95620560 | 95621099 | chr13 | 96031611 | 96031725 |
| chr13 | 96204779 | 96205438 | chr13 | 96296297 | 96296559 | chr13 | 96296616 | 96297215 |
| chr13 | 96743713 | 96744212 | chr13 | 99851662 | 99851748 | chr13 | 100547770 | 100548009 |
| chr13 | 100608177 | 100608536 | chr13 | 100608597 | 100609136 | chr13 | 100621859 | 100622098 |
| chr13 | 100624213 | 100624452 | chr13 | 100624509 | 100624766 | chr13 | 100624801 | 100624808 |
| chr13 | 100626905 | 100627084 | chr13 | 100627203 | 100627442 | chr13 | 100630545 | 100631084 |
| chr13 | 100634227 | 100634382 | chr13 | 100635310 | 100635549 | chr13 | 100636084 | 100636323 |
| chr13 | 100637289 | 100637588 | chr13 | 100641203 | 100642282 | chr13 | 100643217 | 100643516 |
| chr13 | 100643955 | 100644314 | chr13 | 100649334 | 100650018 | chr13 | 102568380 | 102568559 |
| chr13 | 102568776 | 102569075 | chr13 | 102569104 | 102569643 | chr13 | 103046619 | 103047098 |
| chr13 | 103052252 | 103052671 | chr13 | 103052797 | 103053036 | chr13 | 103053296 | 103053509 |
| chr13 | 107186781 | 107186960 | chr13 | 107187085 | 107187242 | chr13 | 108518298 | 108518494 |
| chr13 | 108518724 | 108519017 | chr13 | 108519162 | 108519461 | chr13 | 108519637 | 108519996 |
| chr13 | 108520370 | 108520658 | chr13 | 108520879 | 108520969 | chr13 | 109147599 | 109148438 |
| chr13 | 109148685 | 109149115 | chr13 | 109149164 | 109149284 | chr13 | 110434373 | 110434672 |
| chr13 | 110958720 | 110959079 | chr13 | 110959119 | 110959358 | chr13 | 110959629 | 110960048 |
| chr13 | 110960147 | 110960386 | chr13 | 110960453 | 110960692 | chr13 | 111278225 | 111278521 |
| chr13 | 111363885 | 111364060 | chr13 | 112272891 | 112273102 | chr13 | 112707603 | 112707962 |
| chr13 | 112708002 | 112708601 | chr13 | 112709408 | 112709647 | chr13 | 112709713 | 112709713 |
| chr13 | 112709787 | 112710026 | chr13 | 112710247 | 112710606 | chr13 | 112710669 | 112711868 |
| chr13 | 112711924 | 112713123 | chr13 | 112715267 | 112715746 | chr13 | 112715910 | 112716389 |
| chr13 | 112716695 | 112716814 | chr13 | 112716982 | 112717611 | chr13 | 112717743 | 112718042 |
| chr13 | 112719940 | 112720599 | chr13 | 112720626 | 112720865 | chr13 | 112720938 | 112721117 |
| chr13 | 112721158 | 112722417 | chr13 | 112724431 | 112724610 | chr13 | 112726240 | 112726659 |
| chr13 | 112727888 | 112728367 | chr13 | 112758033 | 112758750 | chr13 | 112758750 | 112759349 |
| chr13 | 112759538 | 112759717 | chr13 | 112759874 | 112760413 | chr13 | 112760755 | 112761305 |
| chr13 | 113598526 | 113598877 | chr13 | 113985597 | 113985956 | chr13 | 114055881 | 114056240 |
| chr13 | 114059990 | 114060409 | chr13 | 114074692 | 114074931 | chr13 | 114123081 | 114123358 |
| chr13 | 114189654 | 114189732 | chr13 | 114221548 | 114221655 | chr13 | 114304637 | 114305016 |
| chr13 | 114479330 | 114479509 | chr13 | 114497930 | 114498349 | chr13 | 114748251 | 114748730 |
| chr13 | 114780482 | 114781141 | chr13 | 114807537 | 114807896 | chr13 | 114855533 | 114855772 |
| chr13 | 114862381 | 114862458 | chr13 | 114961729 | 114962028 | chr14 | 21093364 | 21093531 |
| chr14 | 21093604 | 21093723 | chr14 | 21100674 | 21100906 | chr14 | 22004932 | 22005171 |
| chr14 | 23356162 | 23356341 | chr14 | 23706666 | 23706845 | chr14 | 24045439 | 24045678 |
| chr14 | 24803493 | 24804512 | chr14 | 26674280 | 26674459 | chr14 | 26674625 | 26674703 |
| chr14 | 27066520 | 27066699 | chr14 | 27067065 | 27067427 | chr14 | 29225457 | 29225636 |
| chr14 | 29225986 | 29226285 | chr14 | 29228567 | 29228866 | chr14 | 29229008 | 29229487 |
| chr14 | 29230995 | 29231229 | chr14 | 29231329 | 29231688 | chr14 | 29234911 | 29235450 |
| chr14 | 29236966 | 29237205 | chr14 | 29242687 | 29242707 | chr14 | 29243433 | 29243972 |
| chr14 | 29244147 | 29244383 | chr14 | 29247596 | 29247835 | chr14 | 29254495 | 29254794 |
| chr14 | 31344269 | 31344628 | chr14 | 31925640 | 31925804 | chr14 | 32597619 | 32597759 |
| chr14 | 33402373 | 33402852 | chr14 | 33402942 | 33403029 | chr14 | 33403125 | 33403424 |
| chr14 | 33403783 | 33404502 | chr14 | 34420150 | 34420389 | chr14 | 35023188 | 35023427 |
| chr14 | 35024347 | 35024454 | chr14 | 36003471 | 36003904 | chr14 | 36003979 | 36004578 |
| chr14 | 36004608 | 36005087 | chr14 | 36972709 | 36973008 | chr14 | 36973157 | 36973636 |
| chr14 | 36974421 | 36975058 | chr14 | 36975200 | 36975499 | chr14 | 36977558 | 36978077 |
| chr14 | 36978474 | 36978653 | chr14 | 36979657 | 36979724 | chr14 | 36982829 | 36983068 |
| chr14 | 36983628 | 36984227 | chr14 | 36985767 | 36985946 | chr14 | 36986212 | 36986931 |
| chr14 | 36987068 | 36987787 | chr14 | 36987862 | 36988221 | chr14 | 36988449 | 36988564 |
| chr14 | 36990779 | 36991258 | chr14 | 36991501 | 36991693 | chr14 | 36991848 | 36992507 |
| chr14 | 36993386 | 36994045 | chr14 | 36994145 | 36995104 | chr14 | 37116026 | 37116483 |
| chr14 | 37117535 | 37117745 | chr14 | 37123339 | 37124178 | chr14 | 37124289 | 37124648 |
| chr14 | 37124910 | 37125629 | chr14 | 37126150 | 37126389 | chr14 | 37126463 | 37127002 |
| chr14 | 37127207 | 37127386 | chr14 | 37127572 | 37128111 | chr14 | 37128459 | 37128818 |
| chr14 | 37129990 | 37130349 | chr14 | 37132296 | 37132775 | chr14 | 37132908 | 37133147 |

TABLE 14-continued

Pan Cancer #4

| chr | start | end | chr | start | end | chr | start | end |
|---|---|---|---|---|---|---|---|---|
| chr14 | 37135706 | 37135868 | chr14 | 37135922 | 37136425 | chr14 | 37136514 | 37136693 |
| chr14 | 38060588 | 38061007 | chr14 | 38677445 | 38677581 | chr14 | 38724207 | 38725346 |
| chr14 | 38725434 | 38725560 | chr14 | 42074467 | 42074944 | chr14 | 42075023 | 42075066 |
| chr14 | 42075511 | 42076290 | chr14 | 42076749 | 42076905 | chr14 | 42077130 | 42077369 |
| chr14 | 42077696 | 42077804 | chr14 | 42079190 | 42079429 | chr14 | 48143657 | 48144196 |
| chr14 | 48144201 | 48144500 | chr14 | 48144619 | 48145158 | chr14 | 48145219 | 48145338 |
| chr14 | 50333976 | 50334084 | chr14 | 50334336 | 50334455 | chr14 | 51338642 | 51339061 |
| chr14 | 51560207 | 51561526 | chr14 | 51561680 | 51562099 | chr14 | 52534571 | 52534870 |
| chr14 | 52534929 | 52536488 | chr14 | 52734414 | 52734653 | chr14 | 52734687 | 52735346 |
| chr14 | 52781422 | 52782021 | chr14 | 54422549 | 54423028 | chr14 | 55370100 | 55370219 |
| chr14 | 55596008 | 55596043 | chr14 | 55765207 | 55765686 | chr14 | 57045445 | 57045840 |
| chr14 | 57260845 | 57261924 | chr14 | 57261977 | 57262276 | chr14 | 57264001 | 57265320 |
| chr14 | 57270854 | 57271333 | chr14 | 57271919 | 57272158 | chr14 | 57274387 | 57275406 |
| chr14 | 57275521 | 57276180 | chr14 | 57276344 | 57276763 | chr14 | 57277830 | 57279712 |
| chr14 | 57283238 | 57284737 | chr14 | 58332201 | 58332494 | chr14 | 60097111 | 60097650 |
| chr14 | 60386111 | 60386350 | chr14 | 60386551 | 60386790 | chr14 | 60794532 | 60794771 |
| chr14 | 60952084 | 60953039 | chr14 | 60973157 | 60973418 | chr14 | 60973618 | 60974157 |
| chr14 | 60974273 | 60974506 | chr14 | 60975290 | 60976609 | chr14 | 60976718 | 60976957 |
| chr14 | 60977263 | 60978222 | chr14 | 60981116 | 60981355 | chr14 | 60981586 | 60981885 |
| chr14 | 60982007 | 60982726 | chr14 | 60982757 | 60982996 | chr14 | 61104189 | 61104952 |
| chr14 | 61108539 | 61108904 | chr14 | 61109031 | 61109078 | chr14 | 61109129 | 61109548 |
| chr14 | 61109742 | 61110341 | chr14 | 61114058 | 61114537 | chr14 | 61115235 | 61115594 |
| chr14 | 61118688 | 61118841 | chr14 | 61118872 | 61119227 | chr14 | 61747277 | 61747816 |
| chr14 | 61748002 | 61748117 | chr14 | 62279493 | 62280092 | chr14 | 62583710 | 62584009 |
| chr14 | 63512217 | 63512376 | chr14 | 63512486 | 63512905 | chr14 | 63513050 | 63513229 |
| chr14 | 64222332 | 64222450 | chr14 | 65005803 | 65005915 | chr14 | 65008915 | 65009274 |
| chr14 | 65233253 | 65233552 | chr14 | 67886583 | 67886702 | chr14 | 69013958 | 69014195 |
| chr14 | 69866930 | 69867289 | chr14 | 70014640 | 70015059 | chr14 | 70038414 | 70038713 |
| chr14 | 70038889 | 70039101 | chr14 | 70346045 | 70346584 | chr14 | 70654379 | 70654798 |
| chr14 | 70655451 | 70656170 | chr14 | 72398642 | 72399121 | chr14 | 72399258 | 72399557 |
| chr14 | 72399830 | 72400129 | chr14 | 73167676 | 73167975 | chr14 | 73174938 | 73175237 |
| chr14 | 73178717 | 73178956 | chr14 | 73180112 | 73180336 | chr14 | 73318371 | 73318730 |
| chr14 | 73333174 | 73333256 | chr14 | 73602351 | 73602470 | chr14 | 74705940 | 74706299 |
| chr14 | 74706357 | 74707976 | chr14 | 74708760 | 74709059 | chr14 | 74892472 | 74892645 |
| chr14 | 74892975 | 74893191 | chr14 | 75078070 | 75078609 | chr14 | 75760210 | 75760329 |
| chr14 | 76604580 | 76604819 | chr14 | 76604985 | 76605464 | chr14 | 76843364 | 76843603 |
| chr14 | 76843639 | 76844058 | chr14 | 77228021 | 77228107 | chr14 | 77606833 | 77607312 |
| chr14 | 77737110 | 77737685 | chr14 | 79745088 | 79745271 | chr14 | 85996395 | 85996904 |
| chr14 | 85996760 | 85996999 | chr14 | 85997735 | 85998094 | chr14 | 85998468 | 85998786 |
| chr14 | 85999472 | 85999711 | chr14 | 86000182 | 86000574 | chr14 | 86000886 | 86001196 |
| chr14 | 89817813 | 89818112 | chr14 | 90527617 | 90527856 | chr14 | 90983225 | 90983385 |
| chr14 | 91691167 | 91691385 | chr14 | 91766189 | 91766542 | chr14 | 92789438 | 92789617 |
| chr14 | 92789777 | 92790256 | chr14 | 92790551 | 92790790 | chr14 | 92979835 | 92980074 |
| chr14 | 93154979 | 93155385 | chr14 | 93389450 | 93389869 | chr14 | 93706678 | 93706857 |
| chr14 | 94254302 | 94254601 | chr14 | 94405641 | 94405880 | chr14 | 95233616 | 95233646 |
| chr14 | 95234557 | 95235456 | chr14 | 95235939 | 95236200 | chr14 | 95236450 | 95236498 |
| chr14 | 95239298 | 95239717 | chr14 | 95240053 | 95240268 | chr14 | 95240410 | 95240497 |
| chr14 | 96342551 | 96342790 | chr14 | 96342806 | 96343225 | chr14 | 96343330 | 96343509 |
| chr14 | 96343553 | 96343792 | chr14 | 97045327 | 97045506 | chr14 | 97058761 | 97059180 |
| chr14 | 97499257 | 97499416 | chr14 | 97499616 | 97500035 | chr14 | 97684957 | 97685376 |
| chr14 | 97685624 | 97686038 | chr14 | 99584501 | 99584740 | chr14 | 99736048 | 99736213 |
| chr14 | 100437707 | 100438066 | chr14 | 100438609 | 100438908 | chr14 | 100643267 | 100643566 |
| chr14 | 101193145 | 101193384 | chr14 | 101250012 | 101250371 | chr14 | 101543783 | 101544270 |
| chr14 | 101923033 | 101923332 | chr14 | 101923520 | 101923819 | chr14 | 101923883 | 101924122 |
| chr14 | 101924966 | 101925985 | chr14 | 102026273 | 102026572 | chr14 | 102026703 | 102027062 |
| chr14 | 102031132 | 102031371 | chr14 | 102031434 | 102031666 | chr14 | 102247824 | 102248303 |
| chr14 | 102418533 | 102418652 | chr14 | 102521501 | 102521860 | chr14 | 102529912 | 102530178 |
| chr14 | 102530426 | 102530605 | chr14 | 102564386 | 102564502 | chr14 | 102681994 | 102682233 |
| chr14 | 103021308 | 103022087 | chr14 | 103394784 | 103395203 | chr14 | 103477540 | 103477771 |
| chr14 | 103655154 | 103655684 | chr14 | 103673992 | 103673994 | chr14 | 103674069 | 103674231 |
| chr14 | 103687002 | 103687301 | chr14 | 103739880 | 103740239 | chr14 | 103740275 | 103740514 |
| chr14 | 103745606 | 103745845 | chr14 | 104159978 | 104160160 | chr14 | 104202624 | 104202852 |
| chr14 | 104547814 | 104547993 | chr14 | 104571902 | 104572201 | chr14 | 104601657 | 104601935 |
| chr14 | 104601959 | 104602138 | chr14 | 104604954 | 104605193 | chr14 | 104620334 | 104620633 |
| chr14 | 104627564 | 104627862 | chr14 | 104645048 | 104645277 | chr14 | 104646225 | 104646584 |
| chr14 | 104647183 | 104647362 | chr14 | 104682452 | 104682751 | chr14 | 104862764 | 104863123 |
| chr14 | 105071198 | 105071340 | chr14 | 105157401 | 105157640 | chr14 | 105241220 | 105241267 |
| chr14 | 105246463 | 105246642 | chr14 | 105511960 | 105512463 | chr14 | 105658268 | 105658507 |
| chr14 | 105714177 | 105714690 | chr14 | 105714906 | 105715565 | chr15 | 22822269 | 22822384 |
| chr15 | 23158294 | 23158593 | chr15 | 26107541 | 26107960 | chr15 | 26108010 | 26108789 |
| chr15 | 27018281 | 27018520 | chr15 | 27212791 | 27213277 | chr15 | 27216294 | 27216533 |
| chr15 | 27603982 | 27604057 | chr15 | 28341615 | 28342514 | chr15 | 28344081 | 28344380 |
| chr15 | 28352156 | 28352935 | chr15 | 29077185 | 29077484 | chr15 | 29130712 | 29131971 |
| chr15 | 29407680 | 29408099 | chr15 | 29862423 | 29862537 | chr15 | 31455297 | 31455578 |
| chr15 | 31775500 | 31776216 | chr15 | 33009649 | 33011448 | chr15 | 33011498 | 33011737 |
| chr15 | 33486970 | 33487209 | chr15 | 33602725 | 33602964 | chr15 | 33603110 | 33603709 |

TABLE 14-continued

Pan Cancer #4

| chr | start | end | chr | start | end | chr | start | end |
|---|---|---|---|---|---|---|---|---|
| chr15 | 33879168 | 33879347 | chr15 | 34630346 | 34630525 | chr15 | 34729381 | 34729680 |
| chr15 | 34786425 | 34787384 | chr15 | 35046935 | 35047234 | chr15 | 35087563 | 35087802 |
| chr15 | 37180227 | 37180241 | chr15 | 37180414 | 37180826 | chr15 | 37402898 | 37403316 |
| chr15 | 40211736 | 40212275 | chr15 | 40575538 | 40575837 | chr15 | 41165152 | 41165751 |
| chr15 | 41787709 | 41787948 | chr15 | 41804786 | 41805865 | chr15 | 41835732 | 41835814 |
| chr15 | 41913660 | 41913899 | chr15 | 41952493 | 41952792 | chr15 | 43810472 | 43810510 |
| chr15 | 44037485 | 44037604 | chr15 | 45403554 | 45404213 | chr15 | 45404833 | 45405209 |
| chr15 | 45421291 | 45421530 | chr15 | 45421874 | 45421947 | chr15 | 45427263 | 45427502 |
| chr15 | 45427520 | 45427879 | chr15 | 45479371 | 45479789 | chr15 | 45670503 | 45670971 |
| chr15 | 47476794 | 47477093 | chr15 | 48483882 | 48483963 | chr15 | 48936639 | 48938077 |
| chr15 | 48938122 | 48938601 | chr15 | 51385838 | 51386257 | chr15 | 51633986 | 51634225 |
| chr15 | 51973695 | 51974030 | chr15 | 53075716 | 53077455 | chr15 | 53077574 | 53077813 |
| chr15 | 53077971 | 53078320 | chr15 | 53079262 | 53080161 | chr15 | 53080263 | 53080682 |
| chr15 | 53080861 | 53081100 | chr15 | 53081223 | 53081702 | chr15 | 53082348 | 53082587 |
| chr15 | 53096735 | 53096974 | chr15 | 53097157 | 53097336 | chr15 | 53097535 | 53098074 |
| chr15 | 53098218 | 53098757 | chr15 | 54270424 | 54270783 | chr15 | 54270858 | 54271025 |
| chr15 | 55452972 | 55453087 | chr15 | 55699008 | 55699127 | chr15 | 55880796 | 55881095 |
| chr15 | 58357236 | 58357535 | chr15 | 58357638 | 58358297 | chr15 | 59158454 | 59158616 |
| chr15 | 59950343 | 59950461 | chr15 | 60286937 | 60287780 | chr15 | 60288703 | 60288935 |
| chr15 | 60289229 | 60289638 | chr15 | 60296047 | 60296286 | chr15 | 60296495 | 60297514 |
| chr15 | 60297544 | 60298203 | chr15 | 61520816 | 61521115 | chr15 | 61521559 | 61521676 |
| chr15 | 61521713 | 61522038 | chr15 | 62456848 | 62457019 | chr15 | 65669760 | 65669999 |
| chr15 | 65862054 | 65862213 | chr15 | 66963725 | 66963823 | chr15 | 66963928 | 66963964 |
| chr15 | 68112537 | 68112716 | chr15 | 68113794 | 68113973 | chr15 | 68114048 | 68114287 |
| chr15 | 68116286 | 68116682 | chr15 | 68117753 | 68118712 | chr15 | 68118783 | 68118784 |
| chr15 | 68118799 | 68119322 | chr15 | 68119463 | 68120662 | chr15 | 68120753 | 68120932 |
| chr15 | 68120968 | 68122167 | chr15 | 68122569 | 68122748 | chr15 | 68125164 | 68125763 |
| chr15 | 68127717 | 68128436 | chr15 | 68128492 | 68128597 | chr15 | 68260435 | 68260735 |
| chr15 | 71055770 | 71055906 | chr15 | 72412113 | 72412265 | chr15 | 72743650 | 72743859 |
| chr15 | 73659917 | 73660156 | chr15 | 73661476 | 73661748 | chr15 | 74044960 | 74045199 |
| chr15 | 74421927 | 74422226 | chr15 | 74422787 | 74423012 | chr15 | 74658070 | 74658595 |
| chr15 | 74686082 | 74686126 | chr15 | 74818670 | 74818789 | chr15 | 74903822 | 74904001 |
| chr15 | 75251245 | 75251484 | chr15 | 75251580 | 75251879 | chr15 | 75471036 | 75471275 |
| chr15 | 76627515 | 76627907 | chr15 | 76628959 | 76629314 | chr15 | 76629588 | 76629633 |
| chr15 | 76629732 | 76630931 | chr15 | 76632161 | 76632520 | chr15 | 76635040 | 76635279 |
| chr15 | 76635456 | 76635635 | chr15 | 76638387 | 76638806 | chr15 | 77448976 | 77449087 |
| chr15 | 78501725 | 78502024 | chr15 | 78556795 | 78557034 | chr15 | 78557110 | 78557204 |
| chr15 | 78596066 | 78596245 | chr15 | 78632626 | 78632925 | chr15 | 78912192 | 78912491 |
| chr15 | 78912549 | 78912728 | chr15 | 78912832 | 78913251 | chr15 | 78913444 | 78913683 |
| chr15 | 79104143 | 79104159 | chr15 | 79381709 | 79382648 | chr15 | 79382693 | 79383268 |
| chr15 | 79383873 | 79384052 | chr15 | 79502137 | 79502381 | chr15 | 79575197 | 79575556 |
| chr15 | 79576062 | 79576361 | chr15 | 79724034 | 79724333 | chr15 | 79724402 | 79725241 |
| chr15 | 79725332 | 79725584 | chr15 | 82336777 | 82337076 | chr15 | 82339995 | 82340234 |
| chr15 | 83315246 | 83315474 | chr15 | 83316160 | 83317162 | chr15 | 83349131 | 83349790 |
| chr15 | 83378112 | 83378164 | chr15 | 83378186 | 83378471 | chr15 | 83776161 | 83776880 |
| chr15 | 83875571 | 83875985 | chr15 | 83876953 | 83877252 | chr15 | 83952108 | 83952862 |
| chr15 | 83953024 | 83953983 | chr15 | 84115648 | 84116067 | chr15 | 84116808 | 84116995 |
| chr15 | 84322765 | 84323124 | chr15 | 84748500 | 84749339 | chr15 | 85143052 | 85143144 |
| chr15 | 88798591 | 88798890 | chr15 | 88799448 | 88800407 | chr15 | 88800463 | 88801182 |
| chr15 | 89149070 | 89149489 | chr15 | 89248651 | 89249103 | chr15 | 89345953 | 89346492 |
| chr15 | 89346568 | 89347047 | chr15 | 89903410 | 89903889 | chr15 | 89910426 | 89910845 |
| chr15 | 89910988 | 89911287 | chr15 | 89913676 | 89913855 | chr15 | 89914144 | 89914983 |
| chr15 | 89915156 | 89915455 | chr15 | 89921862 | 89922101 | chr15 | 89922110 | 89922649 |
| chr15 | 89942671 | 89943030 | chr15 | 89943319 | 89943798 | chr15 | 89949317 | 89950036 |
| chr15 | 89950154 | 89951215 | chr15 | 89951302 | 89951901 | chr15 | 89952065 | 89953144 |
| chr15 | 89954122 | 89954416 | chr15 | 89956288 | 89956527 | chr15 | 90039488 | 90039787 |
| chr15 | 90755819 | 90756144 | chr15 | 91643264 | 91643683 | chr15 | 92936281 | 92936426 |
| chr15 | 92937115 | 92937474 | chr15 | 92937849 | 92938388 | chr15 | 93631638 | 93632117 |
| chr15 | 93632558 | 93633337 | chr15 | 94347588 | 94347707 | chr15 | 95388473 | 95388712 |
| chr15 | 96874259 | 96874416 | chr15 | 96889374 | 96889506 | chr15 | 96897853 | 96898092 |
| chr15 | 96911456 | 96911815 | chr15 | 96952594 | 96953313 | chr15 | 96959644 | 96960063 |
| chr15 | 96960428 | 96960513 | chr15 | 96960630 | 96960907 | chr15 | 97006274 | 97006623 |
| chr15 | 98504040 | 98504219 | chr15 | 98836077 | 98836407 | chr15 | 98965179 | 98965232 |
| chr15 | 99193106 | 99193345 | chr15 | 99193350 | 99193583 | chr15 | 99193873 | 99194172 |
| chr15 | 99456272 | 99456404 | chr15 | 100913332 | 100913982 | chr15 | 101420447 | 101420686 |
| chr15 | 101420848 | 101421087 | chr15 | 101513532 | 101513831 | chr16 | 142567 | 142775 |
| chr16 | 215341 | 216300 | chr16 | 216587 | 217070 | chr16 | 230229 | 230708 |
| chr16 | 318040 | 318316 | chr16 | 318422 | 318841 | chr16 | 337510 | 337749 |
| chr16 | 410303 | 410482 | chr16 | 611304 | 611603 | chr16 | 611876 | 612355 |
| chr16 | 612774 | 613133 | chr16 | 667040 | 667349 | chr16 | 667382 | 667399 |
| chr16 | 667466 | 667561 | chr16 | 677879 | 677993 | chr16 | 700225 | 700404 |
| chr16 | 726539 | 727078 | chr16 | 731400 | 731699 | chr16 | 735131 | 735670 |
| chr16 | 740888 | 741003 | chr16 | 741280 | 741507 | chr16 | 837262 | 837561 |
| chr16 | 845881 | 846060 | chr16 | 882567 | 882686 | chr16 | 895011 | 895250 |
| chr16 | 943398 | 943637 | chr16 | 1018046 | 1018225 | chr16 | 1030210 | 1030749 |
| chr16 | 1052488 | 1052727 | chr16 | 1103032 | 1103032 | chr16 | 1116721 | 1116766 |

TABLE 14-continued

Pan Cancer #4

| chr | start | end | chr | start | end | chr | start | end |
|---|---|---|---|---|---|---|---|---|
| chr16 | 1128927 | 1129226 | chr16 | 1155068 | 1155307 | chr16 | 1203883 | 1204122 |
| chr16 | 1217226 | 1217583 | chr16 | 1217943 | 1218182 | chr16 | 1228711 | 1229010 |
| chr16 | 1230057 | 1230236 | chr16 | 1248521 | 1248760 | chr16 | 1267844 | 1268203 |
| chr16 | 1271447 | 1271746 | chr16 | 1312450 | 1312689 | chr16 | 1323900 | 1324139 |
| chr16 | 1382862 | 1383041 | chr16 | 1394400 | 1394579 | chr16 | 1397380 | 1397559 |
| chr16 | 1407366 | 1407485 | chr16 | 1407819 | 1407938 | chr16 | 1428422 | 1428961 |
| chr16 | 1491471 | 1491694 | chr16 | 1730213 | 1730692 | chr16 | 1741757 | 1742176 |
| chr16 | 2028986 | 2029225 | chr16 | 2040818 | 2042257 | chr16 | 2106629 | 2106741 |
| chr16 | 2128503 | 2128682 | chr16 | 2129033 | 2129332 | chr16 | 2141835 | 2142014 |
| chr16 | 2142468 | 2142707 | chr16 | 2213239 | 2213396 | chr16 | 2232665 | 2232784 |
| chr16 | 2234634 | 2235113 | chr16 | 2281163 | 2281402 | chr16 | 2287214 | 2287453 |
| chr16 | 2531136 | 2531255 | chr16 | 2764275 | 2764574 | chr16 | 2770033 | 2770512 |
| chr16 | 2818018 | 2818249 | chr16 | 2892457 | 2892816 | chr16 | 3016951 | 3017730 |
| chr16 | 3068097 | 3068276 | chr16 | 3151038 | 3151264 | chr16 | 3211625 | 3211742 |
| chr16 | 3211805 | 3211982 | chr16 | 3220474 | 3222325 | chr16 | 3225390 | 3225689 |
| chr16 | 3232697 | 3234121 | chr16 | 3234197 | 3234541 | chr16 | 3237783 | 3238022 |
| chr16 | 3238164 | 3238622 | chr16 | 3238912 | 3239631 | chr16 | 3239692 | 3239931 |
| chr16 | 3241517 | 3241756 | chr16 | 3241862 | 3241981 | chr16 | 3355200 | 3355799 |
| chr16 | 3598818 | 3599057 | chr16 | 3696620 | 3696799 | chr16 | 3802932 | 3803171 |
| chr16 | 4264433 | 4264792 | chr16 | 4431039 | 4431213 | chr16 | 4846061 | 4846415 |
| chr16 | 5037803 | 5038102 | chr16 | 5541026 | 5541257 | chr16 | 6069989 | 6070122 |
| chr16 | 7354560 | 7354739 | chr16 | 8780956 | 8781135 | chr16 | 8870279 | 8870458 |
| chr16 | 9009781 | 9010075 | chr16 | 10274325 | 10274504 | chr16 | 10275231 | 10275470 |
| chr16 | 10275671 | 10276030 | chr16 | 10276270 | 10277409 | chr16 | 10479719 | 10480078 |
| chr16 | 12530095 | 12530274 | chr16 | 12971812 | 12972035 | chr16 | 12994359 | 12994838 |
| chr16 | 12994969 | 12995688 | chr16 | 12995707 | 12996426 | chr16 | 12996520 | 12996819 |
| chr16 | 12996861 | 12997100 | chr16 | 12997306 | 12997785 | chr16 | 14725745 | 14725864 |
| chr16 | 15489851 | 15489884 | chr16 | 15820726 | 15820965 | chr16 | 18802486 | 18802725 |
| chr16 | 18950987 | 18951093 | chr16 | 19567117 | 19567536 | chr16 | 19895051 | 19895230 |
| chr16 | 21831520 | 21832052 | chr16 | 21839250 | 21839348 | chr16 | 22824599 | 22825198 |
| chr16 | 22825225 | 22826184 | chr16 | 23313374 | 23313613 | chr16 | 23313674 | 23313913 |
| chr16 | 23706240 | 23706599 | chr16 | 23765995 | 23766098 | chr16 | 23766133 | 23766234 |
| chr16 | 23847214 | 23848053 | chr16 | 24267013 | 24267312 | chr16 | 24267383 | 24267594 |
| chr16 | 25266436 | 25266675 | chr16 | 25702855 | 25703094 | chr16 | 25703686 | 25704705 |
| chr16 | 26664758 | 26664853 | chr16 | 27460002 | 27460156 | chr16 | 28074101 | 28074760 |
| chr16 | 28074869 | 28075288 | chr16 | 29118954 | 29119133 | chr16 | 29153201 | 29153254 |
| chr16 | 29244800 | 29245099 | chr16 | 29830796 | 29831155 | chr16 | 29888045 | 29888332 |
| chr16 | 29888549 | 29888761 | chr16 | 30017240 | 30017539 | chr16 | 30116211 | 30116390 |
| chr16 | 30124597 | 30124949 | chr16 | 30804458 | 30804575 | chr16 | 30826363 | 30826570 |
| chr16 | 30906930 | 30907049 | chr16 | 30907123 | 30907229 | chr16 | 31227815 | 31228402 |
| chr16 | 31446904 | 31447173 | chr16 | 31497971 | 31498087 | chr16 | 31500460 | 31500759 |
| chr16 | 31580469 | 31581058 | chr16 | 46721556 | 46721787 | chr16 | 47177447 | 47177686 |
| chr16 | 48844690 | 48845229 | chr16 | 49309067 | 49309366 | chr16 | 49311432 | 49312391 |
| chr16 | 49313268 | 49313807 | chr16 | 49313921 | 49314220 | chr16 | 49314341 | 49314640 |
| chr16 | 49314692 | 49314931 | chr16 | 49315202 | 49315381 | chr16 | 49315831 | 49316670 |
| chr16 | 49637986 | 49638165 | chr16 | 50335693 | 50335872 | chr16 | 51183824 | 51184483 |
| chr16 | 51184725 | 51185444 | chr16 | 51185763 | 51186362 | chr16 | 51186497 | 51187036 |
| chr16 | 51189848 | 51190309 | chr16 | 53563519 | 53563734 | chr16 | 54318824 | 54318838 |
| chr16 | 54318855 | 54319063 | chr16 | 54319325 | 54319564 | chr16 | 54321557 | 54321916 |
| chr16 | 54324960 | 54325199 | chr16 | 54628600 | 54628959 | chr16 | 54964875 | 54965211 |
| chr16 | 54966728 | 54967388 | chr16 | 54970986 | 54971165 | chr16 | 54971326 | 54971505 |
| chr16 | 55090585 | 55090944 | chr16 | 55357827 | 55358186 | chr16 | 55358213 | 55358632 |
| chr16 | 55358696 | 55359175 | chr16 | 55362907 | 55363326 | chr16 | 55364631 | 55364930 |
| chr16 | 55365020 | 55365319 | chr16 | 55404898 | 55405317 | chr16 | 55512745 | 55512984 |
| chr16 | 55689812 | 55689991 | chr16 | 55690013 | 55690912 | chr16 | 56224479 | 56224958 |
| chr16 | 56228271 | 56228686 | chr16 | 56651006 | 56651365 | chr16 | 56659095 | 56659754 |
| chr16 | 56672077 | 56672761 | chr16 | 56709755 | 56710114 | chr16 | 57222710 | 57222806 |
| chr16 | 57935476 | 57935655 | chr16 | 58018531 | 58018950 | chr16 | 58019149 | 58019508 |
| chr16 | 58120875 | 58121058 | chr16 | 58497136 | 58497495 | chr16 | 58497672 | 58497911 |
| chr16 | 58498101 | 58498280 | chr16 | 58498468 | 58498809 | chr16 | 58521634 | 58521813 |
| chr16 | 58550415 | 58550587 | chr16 | 58969669 | 58969895 | chr16 | 62068387 | 62068610 |
| chr16 | 62068923 | 62069057 | chr16 | 62070669 | 62070848 | chr16 | 65154833 | 65155192 |
| chr16 | 65156288 | 65156587 | chr16 | 66461694 | 66461933 | chr16 | 66612797 | 66613359 |
| chr16 | 67197615 | 67197854 | chr16 | 67197935 | 67198114 | chr16 | 67198818 | 67199057 |
| chr16 | 67241130 | 67241309 | chr16 | 67313791 | 67313970 | chr16 | 68544170 | 68544409 |
| chr16 | 68676307 | 68677086 | chr16 | 68770847 | 68771086 | chr16 | 68771167 | 68771402 |
| chr16 | 68876728 | 68876847 | chr16 | 70595543 | 70595782 | chr16 | 71459950 | 71460429 |
| chr16 | 71715705 | 71715884 | chr16 | 72957660 | 72957899 | chr16 | 73100373 | 73100612 |
| chr16 | 75019677 | 75019856 | chr16 | 77247366 | 77247545 | chr16 | 77468182 | 77468878 |
| chr16 | 77822493 | 77822972 | chr16 | 78079893 | 78080132 | chr16 | 79623729 | 79623968 |
| chr16 | 80838052 | 80838173 | chr16 | 80966296 | 80966535 | chr16 | 81929288 | 81929467 |
| chr16 | 82660279 | 82660578 | chr16 | 82660638 | 82660817 | chr16 | 84074767 | 84074946 |
| chr16 | 84153290 | 84153469 | chr16 | 84402163 | 84402402 | chr16 | 84853274 | 84853452 |
| chr16 | 85075418 | 85075644 | chr16 | 85317747 | 85317879 | chr16 | 85485652 | 85485951 |
| chr16 | 85517254 | 85517613 | chr16 | 85678551 | 85678850 | chr16 | 85684234 | 85684533 |
| chr16 | 85699596 | 85699925 | chr16 | 85932754 | 85932933 | chr16 | 86320254 | 86320493 |

TABLE 14-continued

| Pan Cancer #4 | | | | | | | | |
|---|---|---|---|---|---|---|---|---|
| chr | start | end | chr | start | end | chr | start | end |
| chr16 | 86320659 | 86320898 | chr16 | 86320925 | 86321147 | chr16 | 86530848 | 86531147 |
| chr16 | 86531233 | 86531652 | chr16 | 86541537 | 86541956 | chr16 | 86542296 | 86542535 |
| chr16 | 86544103 | 86545062 | chr16 | 86599392 | 86599931 | chr16 | 86600406 | 86600765 |
| chr16 | 86600868 | 86601107 | chr16 | 86601204 | 86601623 | chr16 | 86601871 | 86602590 |
| chr16 | 86612961 | 86613017 | chr16 | 87092347 | 87092646 | chr16 | 87635029 | 87635208 |
| chr16 | 87636444 | 87636983 | chr16 | 87714178 | 87714477 | chr16 | 87723648 | 87724187 |
| chr16 | 88164316 | 88164555 | chr16 | 88498142 | 88498861 | chr16 | 88503978 | 88504397 |
| chr16 | 88506265 | 88506616 | chr16 | 88512329 | 88512628 | chr16 | 88603617 | 88603848 |
| chr16 | 88623885 | 88624165 | chr16 | 88757428 | 88757571 | chr16 | 88879858 | 88880097 |
| chr16 | 88883159 | 88883458 | chr16 | 88940981 | 88941220 | chr16 | 88942021 | 88942239 |
| chr16 | 88943463 | 88944122 | chr16 | 88945726 | 88946085 | chr16 | 88955160 | 88955459 |
| chr16 | 88956136 | 88956495 | chr16 | 88957374 | 88957934 | chr16 | 88958295 | 88958534 |
| chr16 | 88963191 | 88963850 | chr16 | 88966207 | 88966686 | chr16 | 88968630 | 88968869 |
| chr16 | 88977929 | 88978168 | chr16 | 88992975 | 88993334 | chr16 | 88999543 | 88999557 |
| chr16 | 88999574 | 88999693 | chr16 | 89000127 | 89000306 | chr16 | 89001020 | 89001139 |
| chr16 | 89007420 | 89007659 | chr16 | 89007789 | 89007879 | chr16 | 89008488 | 89008667 |
| chr16 | 89047643 | 89047822 | chr16 | 89072400 | 89072879 | chr16 | 89086034 | 89086273 |
| chr16 | 89107585 | 89107824 | chr16 | 89109345 | 89109490 | chr16 | 89119940 | 89120419 |
| chr16 | 89120607 | 89120963 | chr16 | 89137919 | 89138158 | chr16 | 89220244 | 89220483 |
| chr16 | 89220580 | 89220999 | chr16 | 89254563 | 89254742 | chr16 | 89267260 | 89267439 |
| chr16 | 89267709 | 89267948 | chr16 | 89558549 | 89558807 | chr16 | 89883930 | 89884289 |
| chr16 | 89884875 | 89884989 | chr16 | 89885115 | 89885229 | chr16 | 89900033 | 89900272 |
| chr16 | 89900372 | 89900611 | chr17 | 616914 | 617026 | chr17 | 1082923 | 1083093 |
| chr17 | 1173906 | 1174505 | chr17 | 1536129 | 1536221 | chr17 | 1546312 | 1546539 |
| chr17 | 1623600 | 1623779 | chr17 | 1959375 | 1959614 | chr17 | 2207848 | 2207967 |
| chr17 | 2208042 | 2208147 | chr17 | 2220974 | 2221142 | chr17 | 2249977 | 2250096 |
| chr17 | 3438818 | 3439057 | chr17 | 3658751 | 3658930 | chr17 | 3658991 | 3659110 |
| chr17 | 4544510 | 4544809 | chr17 | 4699212 | 4699331 | chr17 | 4891237 | 4891381 |
| chr17 | 5000340 | 5000879 | chr17 | 5000958 | 5001137 | chr17 | 6616543 | 6616782 |
| chr17 | 6616813 | 6617191 | chr17 | 6679220 | 6679393 | chr17 | 6946113 | 6946244 |
| chr17 | 7348792 | 7349070 | chr17 | 7368864 | 7369223 | chr17 | 7555099 | 7555338 |
| chr17 | 7573915 | 7574094 | chr17 | 7576923 | 7577222 | chr17 | 7577423 | 7577662 |
| chr17 | 7578078 | 7578557 | chr17 | 7906156 | 7906514 | chr17 | 8104071 | 8104173 |
| chr17 | 8230246 | 8230785 | chr17 | 8774685 | 8774728 | chr17 | 8868524 | 8869483 |
| chr17 | 8906183 | 8906602 | chr17 | 8906895 | 8907674 | chr17 | 8925983 | 8926201 |
| chr17 | 10100995 | 10102074 | chr17 | 10102331 | 10102750 | chr17 | 11144218 | 11144424 |
| chr17 | 11144839 | 11145078 | chr17 | 13503875 | 13504294 | chr17 | 13504470 | 13504769 |
| chr17 | 13504873 | 13505292 | chr17 | 13505316 | 13505675 | chr17 | 14200962 | 14201261 |
| chr17 | 14204138 | 14204317 | chr17 | 14204425 | 14204724 | chr17 | 15244976 | 15245215 |
| chr17 | 16282157 | 16282396 | chr17 | 16570674 | 16570897 | chr17 | 17062513 | 17062752 |
| chr17 | 17123889 | 17124068 | chr17 | 17398520 | 17398542 | chr17 | 18163094 | 18163415 |
| chr17 | 18538207 | 18538365 | chr17 | 20817897 | 20817998 | chr17 | 25620495 | 25620794 |
| chr17 | 25676885 | 25677004 | chr17 | 25680190 | 25680276 | chr17 | 25907676 | 25907855 |
| chr17 | 26263104 | 26263214 | chr17 | 26554551 | 26554790 | chr17 | 26961721 | 26961922 |
| chr17 | 27038568 | 27038985 | chr17 | 27044696 | 27044875 | chr17 | 27056846 | 27056957 |
| chr17 | 27170072 | 27170182 | chr17 | 27181284 | 27181456 | chr17 | 27332378 | 27332537 |
| chr17 | 27716018 | 27716134 | chr17 | 27716198 | 27716314 | chr17 | 27940276 | 27940995 |
| chr17 | 28562614 | 28562853 | chr17 | 29232148 | 29232267 | chr17 | 29249615 | 29250034 |
| chr17 | 29298002 | 29298463 | chr17 | 29718123 | 29718362 | chr17 | 29719096 | 29719335 |
| chr17 | 30243689 | 30243988 | chr17 | 30250242 | 30250345 | chr17 | 31618333 | 31619412 |
| chr17 | 31619870 | 31620109 | chr17 | 32483946 | 32484125 | chr17 | 32906299 | 32906718 |
| chr17 | 32906888 | 32907112 | chr17 | 32907136 | 32907247 | chr17 | 32907554 | 32907853 |
| chr17 | 32908044 | 32908463 | chr17 | 32908550 | 32909029 | chr17 | 33672832 | 33673071 |
| chr17 | 33877184 | 33877303 | chr17 | 33917240 | 33917350 | chr17 | 35165549 | 35165788 |
| chr17 | 35165912 | 35166091 | chr17 | 35285455 | 35285754 | chr17 | 35290313 | 35290732 |
| chr17 | 35291242 | 35291457 | chr17 | 35291749 | 35292708 | chr17 | 35293630 | 35294229 |
| chr17 | 35294364 | 35294603 | chr17 | 35294955 | 35295254 | chr17 | 35296069 | 35296368 |
| chr17 | 35296629 | 35296988 | chr17 | 35297527 | 35298246 | chr17 | 35299154 | 35300953 |
| chr17 | 35303259 | 35303618 | chr17 | 36102935 | 36103414 | chr17 | 36103497 | 36103676 |
| chr17 | 36104031 | 36104870 | chr17 | 36105141 | 36105680 | chr17 | 37192168 | 37192281 |
| chr17 | 37321100 | 37322010 | chr17 | 37366236 | 37366655 | chr17 | 37369106 | 37369285 |
| chr17 | 37380922 | 37381941 | chr17 | 37382048 | 37382347 | chr17 | 37757066 | 37757305 |
| chr17 | 37760406 | 37760645 | chr17 | 37761897 | 37762436 | chr17 | 37879697 | 37879712 |
| chr17 | 38179295 | 38179348 | chr17 | 38179492 | 38179534 | chr17 | 38347473 | 38347712 |
| chr17 | 38497542 | 38497721 | chr17 | 38498009 | 38498188 | chr17 | 39682550 | 39682729 |
| chr17 | 40332846 | 40333268 | chr17 | 40400770 | 40401109 | chr17 | 40464179 | 40464418 |
| chr17 | 40464443 | 40464627 | chr17 | 40975576 | 40975754 | chr17 | 41278542 | 41278621 |
| chr17 | 41651776 | 41651887 | chr17 | 41791386 | 41791565 | chr17 | 41791591 | 41791599 |
| chr17 | 42030244 | 42030843 | chr17 | 42061240 | 42061479 | chr17 | 42082421 | 42082660 |
| chr17 | 42092116 | 42092295 | chr17 | 42331637 | 42331746 | chr17 | 42393780 | 42394113 |
| chr17 | 42402782 | 42402984 | chr17 | 42587336 | 42587675 | chr17 | 42635199 | 42635844 |
| chr17 | 42733619 | 42733978 | chr17 | 42787580 | 42787699 | chr17 | 42907489 | 42908028 |
| chr17 | 43001800 | 43002029 | chr17 | 43037408 | 43037504 | chr17 | 43044584 | 43044763 |
| chr17 | 43044909 | 43045208 | chr17 | 43047355 | 43047834 | chr17 | 43339012 | 43339431 |
| chr17 | 43339546 | 43339994 | chr17 | 43974158 | 43974457 | chr17 | 45331345 | 45331404 |
| chr17 | 45810767 | 45811426 | chr17 | 45867239 | 45867538 | chr17 | 46124907 | 46125146 |

TABLE 14-continued

Pan Cancer #4

| chr | start | end | chr | start | end | chr | start | end |
|---|---|---|---|---|---|---|---|---|
| chr17 | 46619224 | 46619224 | chr17 | 46620405 | 46621184 | chr17 | 46621257 | 46621535 |
| chr17 | 46621764 | 46622003 | chr17 | 46655074 | 46655253 | chr17 | 46655351 | 46656531 |
| chr17 | 46659345 | 46659944 | chr17 | 46663666 | 46663928 | chr17 | 46674831 | 46675072 |
| chr17 | 46675086 | 46675685 | chr17 | 46690387 | 46690746 | chr17 | 46691430 | 46691669 |
| chr17 | 46691719 | 46692198 | chr17 | 46692344 | 46692509 | chr17 | 46710857 | 46711156 |
| chr17 | 46711179 | 46711213 | chr17 | 46711240 | 46711478 | chr17 | 46713934 | 46714166 |
| chr17 | 46795563 | 46796545 | chr17 | 46796606 | 46797662 | chr17 | 46799522 | 46800001 |
| chr17 | 46800516 | 46800755 | chr17 | 46800860 | 46801418 | chr17 | 46802364 | 46803286 |
| chr17 | 46804029 | 46804508 | chr17 | 46810328 | 46811047 | chr17 | 46811269 | 46811628 |
| chr17 | 46816191 | 46816730 | chr17 | 46824218 | 46825149 | chr17 | 46825190 | 46825609 |
| chr17 | 46826897 | 46827196 | chr17 | 46827244 | 46827843 | chr17 | 46829420 | 46829659 |
| chr17 | 46829898 | 46830195 | chr17 | 46831700 | 46832719 | chr17 | 47072716 | 47073555 |
| chr17 | 47073899 | 47074318 | chr17 | 47074459 | 47074489 | chr17 | 47074597 | 47074998 |
| chr17 | 47075083 | 47075442 | chr17 | 47075616 | 47076155 | chr17 | 47574001 | 47574240 |
| chr17 | 47657445 | 47657684 | chr17 | 47865416 | 47865655 | chr17 | 47987423 | 47987722 |
| chr17 | 47987843 | 47988202 | chr17 | 48041057 | 48041416 | chr17 | 48041578 | 48041817 |
| chr17 | 48041965 | 48042144 | chr17 | 48042337 | 48043056 | chr17 | 48048857 | 48049156 |
| chr17 | 48049228 | 48050607 | chr17 | 48070946 | 48071125 | chr17 | 48071694 | 48071957 |
| chr17 | 48612147 | 48612386 | chr17 | 48636500 | 48637219 | chr17 | 48653054 | 48653233 |
| chr17 | 48799847 | 48799963 | chr17 | 49229486 | 49229601 | chr17 | 50235126 | 50235365 |
| chr17 | 50235625 | 50236032 | chr17 | 51900930 | 51901109 | chr17 | 53341155 | 53341557 |
| chr17 | 53342774 | 53343193 | chr17 | 53922571 | 53922870 | chr17 | 54674890 | 54675369 |
| chr17 | 54755873 | 54756112 | chr17 | 56092519 | 56092620 | chr17 | 56234305 | 56234844 |
| chr17 | 56326853 | 56327092 | chr17 | 56327197 | 56327376 | chr17 | 56833025 | 56833324 |
| chr17 | 56833622 | 56834161 | chr17 | 56834222 | 56834461 | chr17 | 57297028 | 57297207 |
| chr17 | 58216513 | 58217652 | chr17 | 58218670 | 58219089 | chr17 | 58227281 | 58227520 |
| chr17 | 58498657 | 58499396 | chr17 | 59474060 | 59474719 | chr17 | 59474758 | 59475177 |
| chr17 | 59475604 | 59476023 | chr17 | 59476084 | 59476203 | chr17 | 59476314 | 59476733 |
| chr17 | 59478046 | 59478705 | chr17 | 59488010 | 59488549 | chr17 | 59528775 | 59530454 |
| chr17 | 59531574 | 59532233 | chr17 | 59533741 | 59534580 | chr17 | 59534677 | 59534856 |
| chr17 | 59535059 | 59535298 | chr17 | 59539150 | 59539689 | chr17 | 61777984 | 61778403 |
| chr17 | 61817858 | 61818036 | chr17 | 61926149 | 61926688 | chr17 | 62777244 | 62777543 |
| chr17 | 62777650 | 62777889 | chr17 | 64672276 | 64672635 | chr17 | 66596379 | 66596618 |
| chr17 | 66596884 | 66597123 | chr17 | 67410389 | 67410501 | chr17 | 68164667 | 68164906 |
| chr17 | 70026473 | 70026755 | chr17 | 70112818 | 70114617 | chr17 | 70215595 | 70216674 |
| chr17 | 71641465 | 71641761 | chr17 | 71948352 | 71948951 | chr17 | 72270202 | 72270501 |
| chr17 | 72321844 | 72322074 | chr17 | 72322275 | 72322694 | chr17 | 72353113 | 72353531 |
| chr17 | 72427777 | 72427963 | chr17 | 72428244 | 72428483 | chr17 | 72667242 | 72667661 |
| chr17 | 72848926 | 72849165 | chr17 | 72856964 | 72857443 | chr17 | 72920705 | 72921124 |
| chr17 | 73031547 | 73031619 | chr17 | 73073610 | 73073876 | chr17 | 73545910 | 73546120 |
| chr17 | 73584733 | 73584972 | chr17 | 73585918 | 73586517 | chr17 | 73608232 | 73608411 |
| chr17 | 73636062 | 73636421 | chr17 | 74028261 | 74028461 | chr17 | 74047755 | 74047994 |
| chr17 | 74070386 | 74070672 | chr17 | 74071344 | 74071583 | chr17 | 74071590 | 74071825 |
| chr17 | 74072840 | 74073139 | chr17 | 74073172 | 74073531 | chr17 | 74390289 | 74390468 |
| chr17 | 74533808 | 74534407 | chr17 | 74581083 | 74581322 | chr17 | 74864974 | 74865273 |
| chr17 | 74865612 | 74866331 | chr17 | 75207765 | 75207944 | chr17 | 75368658 | 75369317 |
| chr17 | 75369351 | 75369950 | chr17 | 75370174 | 75370413 | chr17 | 75370522 | 75370701 |
| chr17 | 75385122 | 75385301 | chr17 | 75523058 | 75523354 | chr17 | 75524556 | 75525275 |
| chr17 | 75733902 | 75734108 | chr17 | 75797121 | 75797265 | chr17 | 76125122 | 76125301 |
| chr17 | 76137862 | 76138281 | chr17 | 76138525 | 76138710 | chr17 | 76227774 | 76228433 |
| chr17 | 76404662 | 76404757 | chr17 | 76921756 | 76921934 | chr17 | 76974354 | 76974582 |
| chr17 | 77084488 | 77084667 | chr17 | 77104978 | 77105277 | chr17 | 77145037 | 77145336 |
| chr17 | 77179017 | 77179376 | chr17 | 77179532 | 77179891 | chr17 | 77776733 | 77777152 |
| chr17 | 77777504 | 77778043 | chr17 | 77778852 | 77779136 | chr17 | 77788756 | 77789055 |
| chr17 | 77789219 | 77789578 | chr17 | 77825605 | 77825858 | chr17 | 77899590 | 77899634 |
| chr17 | 78122175 | 78122294 | chr17 | 78447053 | 78447213 | chr17 | 78451842 | 78452141 |
| chr17 | 78452199 | 78452438 | chr17 | 78452578 | 78452937 | chr17 | 78518204 | 78518295 |
| chr17 | 78599493 | 78599732 | chr17 | 78667897 | 78668256 | chr17 | 78874418 | 78874650 |
| chr17 | 79094095 | 79094334 | chr17 | 79099696 | 79099875 | chr17 | 79615087 | 79615446 |
| chr17 | 79626656 | 79626797 | chr17 | 79769354 | 79769773 | chr17 | 80254258 | 80254371 |
| chr17 | 80289153 | 80289392 | chr17 | 80329628 | 80330167 | chr17 | 80394659 | 80394678 |
| chr17 | 80479366 | 80479525 | chr17 | 80535286 | 80535469 | chr17 | 80654909 | 80655088 |
| chr17 | 80693343 | 80693582 | chr17 | 80797600 | 80798459 | chr17 | 80832209 | 80832508 |
| chr17 | 80832635 | 80832874 | chr17 | 81008543 | 81008902 | chr17 | 81033413 | 81033592 |
| chr17 | 81048919 | 81049098 | chr17 | 81049943 | 81050146 | chr18 | 499454 | 499575 |
| chr18 | 499947 | 500842 | chr18 | 904376 | 904735 | chr18 | 904926 | 905105 |
| chr18 | 905359 | 905718 | chr18 | 906770 | 907009 | chr18 | 907384 | 907683 |
| chr18 | 907826 | 908065 | chr18 | 908373 | 908607 | chr18 | 909046 | 909225 |
| chr18 | 909388 | 909687 | chr18 | 2755855 | 2755974 | chr18 | 2906167 | 2906406 |
| chr18 | 3215032 | 3215271 | chr18 | 3498980 | 3499447 | chr18 | 4453885 | 4454244 |
| chr18 | 4454979 | 4455278 | chr18 | 5133126 | 5133405 | chr18 | 5196439 | 5197038 |
| chr18 | 5197126 | 5197425 | chr18 | 5543132 | 5543431 | chr18 | 5543606 | 5543957 |
| chr18 | 5628072 | 5628611 | chr18 | 5629700 | 5630059 | chr18 | 5630218 | 5630457 |
| chr18 | 5890519 | 5891418 | chr18 | 5894935 | 5895294 | chr18 | 5895881 | 5896180 |
| chr18 | 6729881 | 6730093 | chr18 | 7116858 | 7117073 | chr18 | 7117586 | 7117885 |
| chr18 | 7567708 | 7568367 | chr18 | 8608649 | 8609062 | chr18 | 8612178 | 8612357 |

TABLE 14-continued

Pan Cancer #4

| chr | start | end | chr | start | end | chr | start | end |
|---|---|---|---|---|---|---|---|---|
| chr18 | 9771621 | 9771850 | chr18 | 9912693 | 9912872 | chr18 | 10589013 | 10589432 |
| chr18 | 11148888 | 11149127 | chr18 | 11149486 | 11149965 | chr18 | 11401557 | 11401846 |
| chr18 | 11751538 | 11751777 | chr18 | 11751874 | 11752473 | chr18 | 11752626 | 11752805 |
| chr18 | 11942634 | 11942746 | chr18 | 12254133 | 12254672 | chr18 | 12307170 | 12307829 |
| chr18 | 12376133 | 12376206 | chr18 | 12911281 | 12911408 | chr18 | 13824125 | 13824184 |
| chr18 | 13826316 | 13826615 | chr18 | 13868620 | 13869039 | chr18 | 15198162 | 15198269 |
| chr18 | 18822294 | 18823060 | chr18 | 18823101 | 18823373 | chr18 | 19750286 | 19750447 |
| chr18 | 20911467 | 20911646 | chr18 | 21269344 | 21269490 | chr18 | 21269581 | 21269763 |
| chr18 | 22928981 | 22930660 | chr18 | 22930715 | 22931254 | chr18 | 23686388 | 23686507 |
| chr18 | 24127650 | 24128129 | chr18 | 24130729 | 24131267 | chr18 | 24764851 | 24765252 |
| chr18 | 25755505 | 25755744 | chr18 | 25755936 | 25756115 | chr18 | 25756542 | 25756822 |
| chr18 | 25757151 | 25757530 | chr18 | 25757687 | 25757926 | chr18 | 25757994 | 25758233 |
| chr18 | 28620819 | 28621178 | chr18 | 28621242 | 28621274 | chr18 | 28621383 | 28621481 |
| chr18 | 28621545 | 28622024 | chr18 | 28622335 | 28622574 | chr18 | 30349642 | 30349872 |
| chr18 | 31020419 | 31020898 | chr18 | 31158007 | 31158049 | chr18 | 31738953 | 31739552 |
| chr18 | 31802031 | 31802270 | chr18 | 31802864 | 31803043 | chr18 | 31803336 | 31803575 |
| chr18 | 31902690 | 31902944 | chr18 | 32073807 | 32074166 | chr18 | 32557847 | 32557968 |
| chr18 | 32957702 | 32957813 | chr18 | 33078274 | 33078393 | chr18 | 33078634 | 33078753 |
| chr18 | 33877784 | 33877839 | chr18 | 34833519 | 34833938 | chr18 | 35064986 | 35065525 |
| chr18 | 35104565 | 35104984 | chr18 | 35144766 | 35145545 | chr18 | 35146023 | 35146322 |
| chr18 | 35147409 | 35147648 | chr18 | 43914126 | 43914365 | chr18 | 44259911 | 44260067 |
| chr18 | 44335999 | 44336786 | chr18 | 44336805 | 44337044 | chr18 | 44337445 | 44338164 |
| chr18 | 44772980 | 44773279 | chr18 | 44773574 | 44774233 | chr18 | 44774319 | 44774804 |
| chr18 | 44775309 | 44775647 | chr18 | 44776881 | 44777180 | chr18 | 44777227 | 44777406 |
| chr18 | 44777512 | 44777853 | chr18 | 44777949 | 44778411 | chr18 | 44780903 | 44781142 |
| chr18 | 44787695 | 44787934 | chr18 | 44788177 | 44788356 | chr18 | 44789375 | 44789614 |
| chr18 | 44789786 | 44790025 | chr18 | 45057993 | 45058335 | chr18 | 46142587 | 46142715 |
| chr18 | 49867202 | 49867483 | chr18 | 52988906 | 52989316 | chr18 | 52989723 | 52989962 |
| chr18 | 53257052 | 53257291 | chr18 | 53446884 | 53447903 | chr18 | 53989718 | 53989828 |
| chr18 | 53989876 | 53989957 | chr18 | 54788984 | 54789343 | chr18 | 55019610 | 55019918 |
| chr18 | 55020572 | 55020811 | chr18 | 55020981 | 55021340 | chr18 | 55103307 | 55103486 |
| chr18 | 55103645 | 55103824 | chr18 | 55104744 | 55105244 | chr18 | 55105630 | 55105929 |
| chr18 | 55114441 | 55114740 | chr18 | 55850767 | 55851066 | chr18 | 56483824 | 56483938 |
| chr18 | 56815757 | 56815876 | chr18 | 56886981 | 56887517 | chr18 | 56888470 | 56888709 |
| chr18 | 56931460 | 56931682 | chr18 | 56931888 | 56932187 | chr18 | 56932256 | 56932375 |
| chr18 | 56934926 | 56935405 | chr18 | 56935920 | 56936159 | chr18 | 56939025 | 56939264 |
| chr18 | 56939324 | 56940823 | chr18 | 56940863 | 56941882 | chr18 | 57363606 | 57363845 |
| chr18 | 57364185 | 57364484 | chr18 | 57364556 | 57364795 | chr18 | 59000886 | 59001125 |
| chr18 | 59001222 | 59001821 | chr18 | 60263452 | 60263991 | chr18 | 60985417 | 60985825 |
| chr18 | 67067464 | 67068003 | chr18 | 67068059 | 67068298 | chr18 | 67068368 | 67068547 |
| chr18 | 67068614 | 67068913 | chr18 | 67069142 | 67069321 | chr18 | 70209058 | 70209297 |
| chr18 | 70209348 | 70209527 | chr18 | 70210483 | 70210583 | chr18 | 70211527 | 70211766 |
| chr18 | 70534207 | 70534686 | chr18 | 70534769 | 70535046 | chr18 | 70535299 | 70535658 |
| chr18 | 70535918 | 70536697 | chr18 | 70536733 | 70536972 | chr18 | 70537230 | 70537293 |
| chr18 | 73167500 | 73167919 | chr18 | 73627925 | 73628153 | chr18 | 74501045 | 74501267 |
| chr18 | 74755430 | 74755577 | chr18 | 74961264 | 74962247 | chr18 | 74962452 | 74962751 |
| chr18 | 74962896 | 74963675 | chr18 | 75339137 | 75339436 | chr18 | 75362839 | 75363078 |
| chr18 | 75551197 | 75551376 | chr18 | 75612137 | 75612376 | chr18 | 75999330 | 75999509 |
| chr18 | 76239460 | 76239699 | chr18 | 76501405 | 76501584 | chr18 | 76653557 | 76653736 |
| chr18 | 76686175 | 76686354 | chr18 | 77143365 | 77143451 | chr18 | 77167752 | 77167929 |
| chr18 | 77181263 | 77181502 | chr18 | 77194838 | 77195077 | chr18 | 77205436 | 77205735 |
| chr18 | 77285814 | 77286113 | chr18 | 77309459 | 77309638 | chr18 | 77312784 | 77313017 |
| chr18 | 77329633 | 77330101 | chr18 | 77371350 | 77371589 | chr18 | 77543156 | 77543335 |
| chr18 | 77543673 | 77543912 | chr18 | 77547985 | 77548700 | chr18 | 77550108 | 77550647 |
| chr18 | 77557981 | 77558460 | chr18 | 77558732 | 77559031 | chr18 | 77576853 | 77577139 |
| chr18 | 77636517 | 77636696 | chr18 | 78005004 | 78005142 | chr19 | 403435 | 403888 |
| chr19 | 407106 | 407405 | chr19 | 462106 | 462235 | chr19 | 468683 | 468862 |
| chr19 | 485071 | 485490 | chr19 | 549287 | 549526 | chr19 | 555509 | 555625 |
| chr19 | 591272 | 591511 | chr19 | 592492 | 592654 | chr19 | 593197 | 593325 |
| chr19 | 599125 | 599424 | chr19 | 752060 | 752359 | chr19 | 869247 | 869363 |
| chr19 | 883529 | 883888 | chr19 | 883941 | 884240 | chr19 | 891441 | 891616 |
| chr19 | 955668 | 956327 | chr19 | 1003226 | 1003465 | chr19 | 1003583 | 1003822 |
| chr19 | 1004819 | 1005528 | chr19 | 1030082 | 1030309 | chr19 | 1047796 | 1047915 |
| chr19 | 1083392 | 1083526 | chr19 | 1156450 | 1156629 | chr19 | 1170089 | 1170328 |
| chr19 | 1171003 | 1171422 | chr19 | 1220349 | 1220696 | chr19 | 1236397 | 1236631 |
| chr19 | 1274683 | 1274922 | chr19 | 1308066 | 1308184 | chr19 | 1325714 | 1325989 |
| chr19 | 1401655 | 1401894 | chr19 | 1450236 | 1450475 | chr19 | 1467327 | 1468286 |
| chr19 | 1496313 | 1496552 | chr19 | 1496555 | 1496672 | chr19 | 1524289 | 1524528 |
| chr19 | 1525530 | 1526053 | chr19 | 1527132 | 1527307 | chr19 | 1754094 | 1754333 |
| chr19 | 1754653 | 1754892 | chr19 | 1757337 | 1757696 | chr19 | 1762376 | 1762675 |
| chr19 | 1764197 | 1764374 | chr19 | 1775037 | 1775338 | chr19 | 1776276 | 1776635 |
| chr19 | 1799957 | 1800376 | chr19 | 1807893 | 1808492 | chr19 | 2251075 | 2251794 |
| chr19 | 2251973 | 2252752 | chr19 | 2252901 | 2253860 | chr19 | 2274576 | 2274692 |
| chr19 | 2290165 | 2291124 | chr19 | 2302693 | 2303052 | chr19 | 2331339 | 2331518 |
| chr19 | 2513149 | 2513388 | chr19 | 2683817 | 2684046 | chr19 | 3041486 | 3041522 |
| chr19 | 3219555 | 3219659 | chr19 | 3296523 | 3296762 | chr19 | 3361055 | 3361474 |

TABLE 14-continued

Pan Cancer #4

| chr | start | end | chr | start | end | chr | start | end |
|---|---|---|---|---|---|---|---|---|
| chr19 | 3562249 | 3562583 | chr19 | 3578062 | 3578301 | chr19 | 3778053 | 3778472 |
| chr19 | 3779177 | 3779536 | chr19 | 3785566 | 3786345 | chr19 | 3820952 | 3821311 |
| chr19 | 3822008 | 3822307 | chr19 | 3855322 | 3855681 | chr19 | 4054334 | 4054463 |
| chr19 | 4054540 | 4054573 | chr19 | 4311173 | 4311350 | chr19 | 4548040 | 4548459 |
| chr19 | 4550169 | 4550408 | chr19 | 4555813 | 4556214 | chr19 | 4557018 | 4557317 |
| chr19 | 4670678 | 4670857 | chr19 | 5292709 | 5292948 | chr19 | 5338820 | 5339239 |
| chr19 | 5759670 | 5759789 | chr19 | 5826175 | 5826284 | chr19 | 5910275 | 5910429 |
| chr19 | 5914687 | 5914866 | chr19 | 5914907 | 5915146 | chr19 | 6590244 | 6590582 |
| chr19 | 7794919 | 7795338 | chr19 | 7852944 | 7853243 | chr19 | 7853262 | 7853561 |
| chr19 | 8115149 | 8115376 | chr19 | 8576838 | 8577077 | chr19 | 9473555 | 9474140 |
| chr19 | 9517511 | 9517870 | chr19 | 9608817 | 9609116 | chr19 | 9609229 | 9609528 |
| chr19 | 9903828 | 9904054 | chr19 | 9937370 | 9937489 | chr19 | 10231221 | 10231331 |
| chr19 | 10361965 | 10362076 | chr19 | 10398128 | 10398367 | chr19 | 10405892 | 10406431 |
| chr19 | 10406798 | 10407211 | chr19 | 10527085 | 10527282 | chr19 | 10531317 | 10531616 |
| chr19 | 10531890 | 10532069 | chr19 | 10624659 | 10625558 | chr19 | 10823581 | 10823708 |
| chr19 | 11590929 | 11591288 | chr19 | 11592611 | 11592850 | chr19 | 11592942 | 11593241 |
| chr19 | 11689363 | 11689662 | chr19 | 11959816 | 11960175 | chr19 | 12163452 | 12163770 |
| chr19 | 12163819 | 12163998 | chr19 | 12175356 | 12175595 | chr19 | 12175731 | 12176090 |
| chr19 | 12202937 | 12203638 | chr19 | 12266924 | 12267763 | chr19 | 12305754 | 12306351 |
| chr19 | 12476405 | 12476465 | chr19 | 12476501 | 12476644 | chr19 | 12606297 | 12606556 |
| chr19 | 12750903 | 12751142 | chr19 | 12863329 | 12863616 | chr19 | 12951921 | 12952220 |
| chr19 | 12996076 | 12996375 | chr19 | 13210122 | 13210421 | chr19 | 13616617 | 13617336 |
| chr19 | 13618186 | 13618485 | chr19 | 13965933 | 13966022 | chr19 | 14181217 | 14181682 |
| chr19 | 14584149 | 14584868 | chr19 | 15090097 | 15090576 | chr19 | 15121611 | 15121970 |
| chr19 | 15122030 | 15122314 | chr19 | 15288346 | 15288945 | chr19 | 15292293 | 15292592 |
| chr19 | 15342635 | 15343411 | chr19 | 15344007 | 15344426 | chr19 | 17006991 | 17007764 |
| chr19 | 17008422 | 17008884 | chr19 | 17392545 | 17392964 | chr19 | 17717212 | 17717391 |
| chr19 | 17759145 | 17759504 | chr19 | 17791108 | 17791287 | chr19 | 17958396 | 17958935 |
| chr19 | 17983447 | 17983910 | chr19 | 18041167 | 18041286 | chr19 | 18103637 | 18103816 |
| chr19 | 18104390 | 18104493 | chr19 | 18271871 | 18271999 | chr19 | 18330935 | 18331234 |
| chr19 | 18343355 | 18343654 | chr19 | 18343823 | 18344062 | chr19 | 18383252 | 18383431 |
| chr19 | 18714465 | 18714764 | chr19 | 18811473 | 18811771 | chr19 | 18899333 | 18899718 |
| chr19 | 18901753 | 18902172 | chr19 | 18980680 | 18980979 | chr19 | 18989722 | 18990360 |
| chr19 | 18994808 | 18995227 | chr19 | 19334769 | 19334993 | chr19 | 19645776 | 19646015 |
| chr19 | 19651865 | 19652164 | chr19 | 20011908 | 20011992 | chr19 | 20012053 | 20012172 |
| chr19 | 20188746 | 20188865 | chr19 | 20189411 | 20189530 | chr19 | 21646333 | 21646512 |
| chr19 | 21769223 | 21769522 | chr19 | 22018429 | 22018724 | chr19 | 22034402 | 22034896 |
| chr19 | 22610542 | 22610827 | chr19 | 22715053 | 22715532 | chr19 | 23254115 | 23254294 |
| chr19 | 23257780 | 23258559 | chr19 | 23258680 | 23258799 | chr19 | 23299705 | 23299784 |
| chr19 | 23433104 | 23433223 | chr19 | 23598358 | 23598420 | chr19 | 24154518 | 24154697 |
| chr19 | 24216940 | 24217119 | chr19 | 29284377 | 29284796 | chr19 | 29505081 | 29505258 |
| chr19 | 30015844 | 30016803 | chr19 | 30016832 | 30018691 | chr19 | 30019043 | 30019942 |
| chr19 | 30020014 | 30020553 | chr19 | 30021040 | 30021279 | chr19 | 30215468 | 30215572 |
| chr19 | 30252214 | 30252330 | chr19 | 30555254 | 30555473 | chr19 | 30562687 | 30562831 |
| chr19 | 30637413 | 30637633 | chr19 | 30713384 | 30713803 | chr19 | 30713829 | 30714128 |
| chr19 | 30714425 | 30714508 | chr19 | 30715315 | 30715854 | chr19 | 30716236 | 30716655 |
| chr19 | 30716732 | 30718231 | chr19 | 30718761 | 30718934 | chr19 | 30719369 | 30720134 |
| chr19 | 30865626 | 30866525 | chr19 | 31804650 | 31804829 | chr19 | 31839670 | 31839969 |
| chr19 | 31841834 | 31842072 | chr19 | 31842116 | 31842493 | chr19 | 31842502 | 31842741 |
| chr19 | 32364265 | 32364504 | chr19 | 32516309 | 32516495 | chr19 | 32715588 | 32715827 |
| chr19 | 32898350 | 32898589 | chr19 | 33167035 | 33167514 | chr19 | 33467984 | 33468157 |
| chr19 | 33685493 | 33685683 | chr19 | 33792412 | 33792612 | chr19 | 33794599 | 33794838 |
| chr19 | 34112185 | 34112424 | chr19 | 34112450 | 34113049 | chr19 | 34113259 | 34113678 |
| chr19 | 34113911 | 34114210 | chr19 | 34972390 | 34972569 | chr19 | 34973151 | 34973330 |
| chr19 | 34973558 | 34973797 | chr19 | 35263983 | 35264092 | chr19 | 35395923 | 35396462 |
| chr19 | 35616250 | 35616489 | chr19 | 35781298 | 35781537 | chr19 | 35797822 | 35798061 |
| chr19 | 36048504 | 36048863 | chr19 | 36049246 | 36049497 | chr19 | 36222334 | 36222567 |
| chr19 | 36249933 | 36250232 | chr19 | 36334884 | 36335243 | chr19 | 36347791 | 36348147 |
| chr19 | 36450030 | 36450449 | chr19 | 36523258 | 36523557 | chr19 | 36735953 | 36736132 |
| chr19 | 36736226 | 36736585 | chr19 | 36822249 | 36822968 | chr19 | 36909074 | 36910028 |
| chr19 | 36912257 | 36912496 | chr19 | 37095591 | 37096660 | chr19 | 37263439 | 37263678 |
| chr19 | 37264143 | 37264487 | chr19 | 37288237 | 37288869 | chr19 | 37341683 | 37342042 |
| chr19 | 37407046 | 37407525 | chr19 | 37463953 | 37464792 | chr19 | 37569394 | 37569573 |
| chr19 | 37702087 | 37702265 | chr19 | 37959762 | 37960061 | chr19 | 37997337 | 37998206 |
| chr19 | 38042290 | 38042769 | chr19 | 38085160 | 38085759 | chr19 | 38085958 | 38086110 |
| chr19 | 38145976 | 38146335 | chr19 | 38146364 | 38146663 | chr19 | 38182793 | 38183392 |
| chr19 | 38308031 | 38308543 | chr19 | 38480952 | 38481190 | chr19 | 38747072 | 38747448 |
| chr19 | 38755189 | 38755422 | chr19 | 38782485 | 38782664 | chr19 | 38789223 | 38789373 |
| chr19 | 38873861 | 38874040 | chr19 | 38905446 | 38905805 | chr19 | 38974158 | 38974337 |
| chr19 | 39135435 | 39135554 | chr19 | 39687575 | 39687934 | chr19 | 39754787 | 39755446 |
| chr19 | 39816862 | 39817161 | chr19 | 39993392 | 39993532 | chr19 | 39997602 | 39997901 |
| chr19 | 40006093 | 40006392 | chr19 | 40006489 | 40006728 | chr19 | 40723923 | 40724342 |
| chr19 | 40829768 | 40830123 | chr19 | 40902350 | 40902779 | chr19 | 40951087 | 40951197 |
| chr19 | 40951602 | 40951841 | chr19 | 41018456 | 41019131 | chr19 | 41025462 | 41025761 |
| chr19 | 41059832 | 41060408 | chr19 | 41073513 | 41073752 | chr19 | 41119097 | 41119735 |
| chr19 | 41354575 | 41354814 | chr19 | 41641740 | 41641979 | chr19 | 42028407 | 42028646 |

TABLE 14-continued

Pan Cancer #4

| chr | start | end | chr | start | end | chr | start | end |
|---|---|---|---|---|---|---|---|---|
| chr19 | 42408226 | 42408405 | chr19 | 42827810 | 42828349 | chr19 | 42856486 | 42856558 |
| chr19 | 44203735 | 44203962 | chr19 | 44405819 | 44406178 | chr19 | 44599691 | 44599803 |
| chr19 | 44905425 | 44905604 | chr19 | 44952193 | 44952909 | chr19 | 45003142 | 45003417 |
| chr19 | 45300052 | 45300291 | chr19 | 45570307 | 45570546 | chr19 | 45574391 | 45574570 |
| chr19 | 45574682 | 45574782 | chr19 | 45574837 | 45574981 | chr19 | 45655309 | 45656448 |
| chr19 | 45656589 | 45657008 | chr19 | 45657129 | 45657368 | chr19 | 45810006 | 45810345 |
| chr19 | 45835239 | 45835353 | chr19 | 45888843 | 45889484 | chr19 | 45997437 | 45997676 |
| chr19 | 46001945 | 46002424 | chr19 | 46234853 | 46234965 | chr19 | 46379822 | 46380241 |
| chr19 | 46404448 | 46404682 | chr19 | 46916631 | 46917170 | chr19 | 46930046 | 46930278 |
| chr19 | 46974477 | 46974776 | chr19 | 46992643 | 46992942 | chr19 | 46993067 | 46993486 |
| chr19 | 46996509 | 46996748 | chr19 | 46996775 | 46997010 | chr19 | 47152515 | 47153114 |
| chr19 | 47200270 | 47200629 | chr19 | 47910405 | 47910620 | chr19 | 47933223 | 47933822 |
| chr19 | 48003512 | 48003747 | chr19 | 48076568 | 48076747 | chr19 | 48137090 | 48137187 |
| chr19 | 48137247 | 48137389 | chr19 | 48151189 | 48151421 | chr19 | 48614769 | 48614851 |
| chr19 | 48771496 | 48771636 | chr19 | 48800507 | 48800866 | chr19 | 48857809 | 48857917 |
| chr19 | 48902834 | 48902953 | chr19 | 48918040 | 48918339 | chr19 | 49119155 | 49119334 |
| chr19 | 49127285 | 49127764 | chr19 | 49180431 | 49180610 | chr19 | 49399126 | 49399414 |
| chr19 | 49575386 | 49575565 | chr19 | 49646062 | 49646294 | chr19 | 49890810 | 49890908 |
| chr19 | 49935656 | 49936255 | chr19 | 49936790 | 49936969 | chr19 | 50028455 | 50028614 |
| chr19 | 50049635 | 50049746 | chr19 | 50215991 | 50216147 | chr19 | 50316147 | 50316566 |
| chr19 | 50353305 | 50353664 | chr19 | 50553917 | 50554516 | chr19 | 50816339 | 50816573 |
| chr19 | 50833750 | 50833966 | chr19 | 50938470 | 50938769 | chr19 | 51161151 | 51161330 |
| chr19 | 51162123 | 51162602 | chr19 | 51171130 | 51171369 | chr19 | 51227633 | 51227872 |
| chr19 | 51227975 | 51228154 | chr19 | 51228229 | 51228588 | chr19 | 51304487 | 51304666 |
| chr19 | 51520349 | 51520528 | chr19 | 51830748 | 51831227 | chr19 | 51831286 | 51831465 |
| chr19 | 52097592 | 52097831 | chr19 | 52207162 | 52207461 | chr19 | 52222438 | 52223192 |
| chr19 | 52552089 | 52552248 | chr19 | 52839494 | 52839634 | chr19 | 52839700 | 52840033 |
| chr19 | 52872943 | 52873542 | chr19 | 52956708 | 52956947 | chr19 | 53028835 | 53028952 |
| chr19 | 53031202 | 53031290 | chr19 | 53073476 | 53074075 | chr19 | 53141533 | 53141832 |
| chr19 | 53193757 | 53193996 | chr19 | 53194190 | 53194366 | chr19 | 53496630 | 53496928 |
| chr19 | 53561582 | 53561821 | chr19 | 53635873 | 53636168 | chr19 | 53661566 | 53661865 |
| chr19 | 53662195 | 53662722 | chr19 | 53696318 | 53696677 | chr19 | 53700514 | 53700693 |
| chr19 | 53757802 | 53758341 | chr19 | 53811774 | 53811986 | chr19 | 53836837 | 53836952 |
| chr19 | 53970464 | 53970636 | chr19 | 53970884 | 53971243 | chr19 | 54023803 | 54024282 |
| chr19 | 54024434 | 54024553 | chr19 | 54024619 | 54024973 | chr19 | 54411032 | 54411267 |
| chr19 | 54411482 | 54411661 | chr19 | 54412780 | 54413079 | chr19 | 54445250 | 54445609 |
| chr19 | 54481691 | 54482050 | chr19 | 54483091 | 54483630 | chr19 | 54485442 | 54485913 |
| chr19 | 56159350 | 56159596 | chr19 | 56201573 | 56201812 | chr19 | 56588806 | 56588868 |
| chr19 | 56728588 | 56729067 | chr19 | 56879426 | 56880075 | chr19 | 56904643 | 56905302 |
| chr19 | 56915225 | 56915524 | chr19 | 56988458 | 56988817 | chr19 | 56989432 | 56989851 |
| chr19 | 57050389 | 57050568 | chr19 | 57149480 | 57149719 | chr19 | 57154802 | 57155101 |
| chr19 | 57182906 | 57183423 | chr19 | 57276559 | 57276798 | chr19 | 57610771 | 57611067 |
| chr19 | 57617433 | 57618212 | chr19 | 57683078 | 57683372 | chr19 | 57862330 | 57862859 |
| chr19 | 57862930 | 57863229 | chr19 | 58011040 | 58011383 | chr19 | 58038708 | 58039067 |
| chr19 | 58094912 | 58095931 | chr19 | 58111529 | 58111888 | chr19 | 58125444 | 58125983 |
| chr19 | 58144419 | 58144778 | chr19 | 58219924 | 58220583 | chr19 | 58238234 | 58239187 |
| chr19 | 58399978 | 58400277 | chr19 | 58400319 | 58400618 | chr19 | 58458679 | 58459278 |
| chr19 | 58514416 | 58514655 | chr19 | 58520661 | 58521020 | chr19 | 58545042 | 58545843 |
| chr19 | 58570448 | 58570747 | chr19 | 58609299 | 58609944 | chr19 | 58629812 | 58630026 |
| chr19 | 58661815 | 58662174 | chr19 | 58666093 | 58666392 | chr19 | 58739983 | 58740222 |
| chr19 | 58874834 | 58874951 | chr19 | 58907613 | 58908272 | chr19 | 58951175 | 58952014 |
| chr19 | 58964105 | 58964283 | chr20 | 291052 | 291453 | chr20 | 399928 | 400167 |
| chr20 | 401079 | 401258 | chr20 | 401495 | 401854 | chr20 | 590349 | 590588 |
| chr20 | 590661 | 590960 | chr20 | 592323 | 592547 | chr20 | 644096 | 644875 |
| chr20 | 799030 | 799146 | chr20 | 982660 | 983079 | chr20 | 1206766 | 1207125 |
| chr20 | 1783674 | 1784453 | chr20 | 2539252 | 2539851 | chr20 | 2668670 | 2669026 |
| chr20 | 2780654 | 2780747 | chr20 | 2780894 | 2781553 | chr20 | 2781657 | 2781836 |
| chr20 | 2785561 | 2786160 | chr20 | 3027666 | 3027780 | chr20 | 3052501 | 3052920 |
| chr20 | 3073395 | 3073994 | chr20 | 3204792 | 3205031 | chr20 | 3220799 | 3221038 |
| chr20 | 3229475 | 3229714 | chr20 | 3641656 | 3642015 | chr20 | 3662918 | 3663277 |
| chr20 | 4084983 | 4085146 | chr20 | 4229328 | 4229507 | chr20 | 4229684 | 4230684 |
| chr20 | 4802971 | 4803750 | chr20 | 4803846 | 4804053 | chr20 | 5296095 | 5296986 |
| chr20 | 5297106 | 5297705 | chr20 | 6022813 | 6023067 | chr20 | 6748832 | 6749131 |
| chr20 | 8112304 | 8112483 | chr20 | 8112642 | 8113121 | chr20 | 8113462 | 8113701 |
| chr20 | 9487302 | 9488032 | chr20 | 9488287 | 9488613 | chr20 | 9488650 | 9488934 |
| chr20 | 9488993 | 9489249 | chr20 | 9489377 | 9489796 | chr20 | 9495181 | 9495600 |
| chr20 | 9496253 | 9496912 | chr20 | 9496953 | 9497074 | chr20 | 10198206 | 10198685 |
| chr20 | 10198841 | 10199020 | chr20 | 13200498 | 13200737 | chr20 | 16555037 | 16555130 |
| chr20 | 17206434 | 17206840 | chr20 | 17207783 | 17208022 | chr20 | 17208484 | 17208723 |
| chr20 | 18039741 | 18039980 | chr20 | 19739495 | 19739794 | chr20 | 19928211 | 19928450 |
| chr20 | 20344410 | 20344649 | chr20 | 20345597 | 20346196 | chr20 | 20347358 | 20348257 |
| chr20 | 20348447 | 20348686 | chr20 | 20349055 | 20349354 | chr20 | 20349500 | 20349679 |
| chr20 | 21080615 | 21082354 | chr20 | 21082456 | 21082995 | chr20 | 21083322 | 21084461 |
| chr20 | 21085729 | 21085968 | chr20 | 21086075 | 21086554 | chr20 | 21086808 | 21087267 |
| chr20 | 21372091 | 21372810 | chr20 | 21376172 | 21378631 | chr20 | 21486299 | 21486958 |
| chr20 | 21487068 | 21487276 | chr20 | 21487368 | 21487667 | chr20 | 21488076 | 21488435 |

TABLE 14-continued

Pan Cancer #4

| chr | start | end | chr | start | end | chr | start | end |
|---|---|---|---|---|---|---|---|---|
| chr20 | 21489135 | 21489794 | chr20 | 21490099 | 21491632 | chr20 | 21492292 | 21493071 |
| chr20 | 21493218 | 21494357 | chr20 | 21494438 | 21494797 | chr20 | 21495845 | 21496084 |
| chr20 | 21496158 | 21496397 | chr20 | 21496558 | 21497217 | chr20 | 21497337 | 21498716 |
| chr20 | 21500019 | 21500228 | chr20 | 21501294 | 21501814 | chr20 | 21501945 | 21502424 |
| chr20 | 21502495 | 21503214 | chr20 | 21503490 | 21503877 | chr20 | 21682309 | 21682548 |
| chr20 | 21683213 | 21683751 | chr20 | 21685592 | 21685606 | chr20 | 21686157 | 21686756 |
| chr20 | 21686921 | 21687820 | chr20 | 21689862 | 21690137 | chr20 | 21694425 | 21694604 |
| chr20 | 21695014 | 21695391 | chr20 | 21748349 | 21748588 | chr20 | 22557301 | 22557776 |
| chr20 | 22557898 | 22558197 | chr20 | 22558534 | 22558773 | chr20 | 22559549 | 22559788 |
| chr20 | 22562632 | 22562931 | chr20 | 22563690 | 22563703 | chr20 | 22564161 | 22564291 |
| chr20 | 23015843 | 23015942 | chr20 | 23029012 | 23029251 | chr20 | 23029303 | 23030442 |
| chr20 | 23031471 | 23031729 | chr20 | 24450133 | 24450612 | chr20 | 24450692 | 24451111 |
| chr20 | 24451372 | 24451671 | chr20 | 25058292 | 25058711 | chr20 | 25061654 | 25062973 |
| chr20 | 25063700 | 25064539 | chr20 | 25065078 | 25065497 | chr20 | 25129345 | 25129544 |
| chr20 | 25230415 | 25230513 | chr20 | 25230775 | 25230894 | chr20 | 26188813 | 26189092 |
| chr20 | 26190218 | 26190432 | chr20 | 30101724 | 30101833 | chr20 | 30582655 | 30583074 |
| chr20 | 30639051 | 30639410 | chr20 | 30639531 | 30639570 | chr20 | 30639603 | 30639950 |
| chr20 | 30640009 | 30640368 | chr20 | 30777930 | 30778339 | chr20 | 31115592 | 31115891 |
| chr20 | 31151695 | 31151874 | chr20 | 32301800 | 32302039 | chr20 | 32450399 | 32450518 |
| chr20 | 33547579 | 33547685 | chr20 | 33574834 | 33574981 | chr20 | 34041903 | 34042004 |
| chr20 | 34147928 | 34148347 | chr20 | 34188525 | 34189484 | chr20 | 34189534 | 34190013 |
| chr20 | 36531706 | 36532005 | chr20 | 36781250 | 36781429 | chr20 | 37302601 | 37303440 |
| chr20 | 37351701 | 37352720 | chr20 | 37353096 | 37353335 | chr20 | 37353378 | 37353857 |
| chr20 | 37354045 | 37355304 | chr20 | 37355761 | 37357440 | chr20 | 37357739 | 37358278 |
| chr20 | 37434469 | 37434828 | chr20 | 37435012 | 37435311 | chr20 | 37435362 | 37435961 |
| chr20 | 39316114 | 39316413 | chr20 | 39316814 | 39317473 | chr20 | 39317659 | 39318138 |
| chr20 | 39319031 | 39319750 | chr20 | 39995061 | 39995900 | chr20 | 41817697 | 41818176 |
| chr20 | 41818472 | 41819011 | chr20 | 42136252 | 42136491 | chr20 | 42218593 | 42218757 |
| chr20 | 42543655 | 42543954 | chr20 | 42543999 | 42545459 | chr20 | 42876457 | 42876670 |
| chr20 | 43437970 | 43438569 | chr20 | 43438883 | 43439122 | chr20 | 43439192 | 43439611 |
| chr20 | 44452628 | 44453152 | chr20 | 44519003 | 44519182 | chr20 | 44601980 | 44602069 |
| chr20 | 44639100 | 44639579 | chr20 | 44640264 | 44640443 | chr20 | 44660665 | 44660964 |
| chr20 | 44686087 | 44686866 | chr20 | 44803096 | 44803755 | chr20 | 44875147 | 44875506 |
| chr20 | 44879700 | 44880179 | chr20 | 44937124 | 44937369 | chr20 | 44937444 | 44937723 |
| chr20 | 44941441 | 44941740 | chr20 | 45141897 | 45142331 | chr20 | 45279779 | 45280491 |
| chr20 | 45337726 | 45338025 | chr20 | 45524449 | 45524628 | chr20 | 47247136 | 47247407 |
| chr20 | 47274032 | 47274137 | chr20 | 47296021 | 47296320 | chr20 | 47443647 | 47444366 |
| chr20 | 47905336 | 47905687 | chr20 | 47934747 | 47935346 | chr20 | 47935412 | 47935651 |
| chr20 | 47935829 | 47936128 | chr20 | 48184289 | 48184528 | chr20 | 49204105 | 49204524 |
| chr20 | 49261715 | 49262194 | chr20 | 49358363 | 49358477 | chr20 | 49377912 | 49378139 |
| chr20 | 49381177 | 49381340 | chr20 | 49575835 | 49575938 | chr20 | 49575988 | 49576014 |
| chr20 | 49639698 | 49640237 | chr20 | 50383399 | 50383504 | chr20 | 50384683 | 50384982 |
| chr20 | 50720356 | 50722021 | chr20 | 50722096 | 50722201 | chr20 | 50722609 | 50722908 |
| chr20 | 51589688 | 51589987 | chr20 | 52311387 | 52311505 | chr20 | 52789371 | 52789550 |
| chr20 | 52789765 | 52790244 | chr20 | 53092165 | 53092464 | chr20 | 53093011 | 53093190 |
| chr20 | 54578407 | 54578826 | chr20 | 54579809 | 54580408 | chr20 | 54580484 | 54580783 |
| chr20 | 55199952 | 55200791 | chr20 | 55200828 | 55201187 | chr20 | 55201399 | 55201638 |
| chr20 | 55201686 | 55202705 | chr20 | 55202728 | 55203207 | chr20 | 55204224 | 55204703 |
| chr20 | 55204864 | 55205103 | chr20 | 55205956 | 55206495 | chr20 | 55499394 | 55499813 |
| chr20 | 55499932 | 55500171 | chr20 | 55500321 | 55501040 | chr20 | 55693446 | 55693610 |
| chr20 | 55841036 | 55841455 | chr20 | 55841994 | 55842293 | chr20 | 56766086 | 56766203 |
| chr20 | 56803301 | 56803540 | chr20 | 56803762 | 56804001 | chr20 | 57089355 | 57089594 |
| chr20 | 57089720 | 57090259 | chr20 | 57224746 | 57225405 | chr20 | 58152557 | 58152796 |
| chr20 | 58179713 | 58179952 | chr20 | 58180018 | 58180497 | chr20 | 58508796 | 58509005 |
| chr20 | 59804233 | 59804323 | chr20 | 59826885 | 59827304 | chr20 | 59827702 | 59828541 |
| chr20 | 59880480 | 59880575 | chr20 | 59910084 | 59910441 | chr20 | 59972951 | 59973170 |
| chr20 | 60202541 | 60202699 | chr20 | 60235251 | 60235610 | chr20 | 60238278 | 60238574 |
| chr20 | 60238780 | 60239079 | chr20 | 60243860 | 60244206 | chr20 | 60329482 | 60329661 |
| chr20 | 60359835 | 60359954 | chr20 | 60374934 | 60375173 | chr20 | 60439546 | 60439845 |
| chr20 | 60453829 | 60454186 | chr20 | 60477213 | 60477632 | chr20 | 60485281 | 60485480 |
| chr20 | 60502956 | 60503135 | chr20 | 60620233 | 60620412 | chr20 | 60772886 | 60773905 |
| chr20 | 60789866 | 60790225 | chr20 | 60925945 | 60926124 | chr20 | 60970879 | 60971058 |
| chr20 | 60983756 | 60984115 | chr20 | 60984356 | 60984553 | chr20 | 61287993 | 61288232 |
| chr20 | 61288380 | 61288619 | chr20 | 61294596 | 61294955 | chr20 | 61340486 | 61340785 |
| chr20 | 61412227 | 61412451 | chr20 | 61505882 | 61506421 | chr20 | 61532457 | 61532696 |
| chr20 | 61560341 | 61561000 | chr20 | 61585679 | 61585823 | chr20 | 61585900 | 61586079 |
| chr20 | 61636755 | 61636994 | chr20 | 61637391 | 61638710 | chr20 | 61703613 | 61703792 |
| chr20 | 61714683 | 61714696 | chr20 | 61734332 | 61734571 | chr20 | 61747795 | 61748034 |
| chr20 | 61763524 | 61763703 | chr20 | 61765251 | 61765490 | chr20 | 61808107 | 61808346 |
| chr20 | 61808388 | 61810187 | chr20 | 61823076 | 61823195 | chr20 | 61862297 | 61862460 |
| chr20 | 61885146 | 61885565 | chr20 | 61885609 | 61885848 | chr20 | 61885984 | 61886343 |
| chr20 | 61886651 | 61886830 | chr20 | 61974094 | 61974453 | chr20 | 61980769 | 61981068 |
| chr20 | 62031085 | 62031324 | chr20 | 62031958 | 62032197 | chr20 | 62037460 | 62037699 |
| chr20 | 62046145 | 62046504 | chr20 | 62058624 | 62058859 | chr20 | 62090442 | 62090621 |
| chr20 | 62097763 | 62097771 | chr20 | 62115188 | 62115367 | chr20 | 62119246 | 62120252 |
| chr20 | 62126035 | 62126514 | chr20 | 62157232 | 62157349 | chr20 | 62165548 | 62165847 |

TABLE 14-continued

Pan Cancer #4

| chr | start | end | chr | start | end | chr | start | end |
|---|---|---|---|---|---|---|---|---|
| chr20 | 62167480 | 62167659 | chr20 | 62170105 | 62170284 | chr20 | 62172851 | 62173150 |
| chr20 | 62185296 | 62185535 | chr20 | 62321125 | 62321424 | chr20 | 62321551 | 62321970 |
| chr20 | 62340233 | 62340423 | chr20 | 62383135 | 62383374 | chr20 | 62461263 | 62461562 |
| chr20 | 62488263 | 62488442 | chr20 | 62680682 | 62680818 | chr20 | 62714923 | 62714946 |
| chr20 | 62715097 | 62715162 | chr21 | 22370246 | 22370545 | chr21 | 22370614 | 22370793 |
| chr21 | 26934278 | 26934877 | chr21 | 27011671 | 27011910 | chr21 | 27012283 | 27012522 |
| chr21 | 27944919 | 27945158 | chr21 | 27945324 | 27945503 | chr21 | 27945619 | 27945798 |
| chr21 | 28216509 | 28217768 | chr21 | 28218671 | 28218815 | chr21 | 28218877 | 28219150 |
| chr21 | 28338743 | 28338848 | chr21 | 28339165 | 28339584 | chr21 | 28339806 | 28340405 |
| chr21 | 31015127 | 31015306 | chr21 | 31311330 | 31311629 | chr21 | 31311846 | 31312205 |
| chr21 | 31312230 | 31312259 | chr21 | 31312305 | 31312409 | chr21 | 33244901 | 33245131 |
| chr21 | 33245582 | 33245593 | chr21 | 33245716 | 33245821 | chr21 | 33245921 | 33245955 |
| chr21 | 33246038 | 33246280 | chr21 | 33627450 | 33627569 | chr21 | 33721671 | 33721910 |
| chr21 | 33983153 | 33983320 | chr21 | 34392070 | 34392669 | chr21 | 34395217 | 34396356 |
| chr21 | 34396707 | 34396870 | chr21 | 34396903 | 34397178 | chr21 | 34397993 | 34398712 |
| chr21 | 34398847 | 34400346 | chr21 | 34401110 | 34401469 | chr21 | 34442457 | 34442696 |
| chr21 | 34443004 | 34443363 | chr21 | 34443419 | 34443778 | chr21 | 34443806 | 34444045 |
| chr21 | 34444082 | 34444681 | chr21 | 36041374 | 36041793 | chr21 | 36041903 | 36042322 |
| chr21 | 36042581 | 36042940 | chr21 | 37527854 | 37528033 | chr21 | 37758492 | 37758611 |
| chr21 | 37774963 | 37775238 | chr21 | 38064415 | 38064714 | chr21 | 38064917 | 38065832 |
| chr21 | 38065855 | 38066214 | chr21 | 38067247 | 38067308 | chr21 | 38068092 | 38068384 |
| chr21 | 38068465 | 38068871 | chr21 | 38069125 | 38069298 | chr21 | 38069359 | 38069598 |
| chr21 | 38069725 | 38070144 | chr21 | 38070616 | 38070855 | chr21 | 38071699 | 38071781 |
| chr21 | 38071933 | 38071998 | chr21 | 38072920 | 38073159 | chr21 | 38073221 | 38073940 |
| chr21 | 38076764 | 38077243 | chr21 | 38078332 | 38078571 | chr21 | 38079887 | 38080786 |
| chr21 | 38081112 | 38081296 | chr21 | 38081371 | 38081910 | chr21 | 38081968 | 38082011 |
| chr21 | 38082854 | 38083258 | chr21 | 38092081 | 38092320 | chr21 | 38119809 | 38120408 |
| chr21 | 38638505 | 38638624 | chr21 | 38935395 | 38935601 | chr21 | 39047688 | 39047889 |
| chr21 | 40984719 | 40984898 | chr21 | 43376299 | 43376478 | chr21 | 43786609 | 43786788 |
| chr21 | 43991389 | 43991568 | chr21 | 44283611 | 44283850 | chr21 | 44494814 | 44495233 |
| chr21 | 44837002 | 44837245 | chr21 | 44837296 | 44837301 | chr21 | 44847488 | 44847727 |
| chr21 | 44866508 | 44866807 | chr21 | 45148538 | 45148837 | chr21 | 45195115 | 45195414 |
| chr21 | 45273636 | 45273995 | chr21 | 45508543 | 45508662 | chr21 | 45791005 | 45791184 |
| chr21 | 46036556 | 46036855 | chr21 | 46126009 | 46126267 | chr21 | 46126388 | 46126807 |
| chr21 | 46126948 | 46127187 | chr21 | 46127468 | 46127628 | chr21 | 46128801 | 46129040 |
| chr21 | 46129346 | 46129585 | chr21 | 46257016 | 46257375 | chr21 | 46310341 | 46310580 |
| chr21 | 46318196 | 46318435 | chr21 | 46319069 | 46319548 | chr21 | 46359099 | 46359338 |
| chr21 | 46452278 | 46452637 | chr21 | 46677646 | 46677885 | chr21 | 46825737 | 46825823 |
| chr21 | 46863675 | 46863803 | chr21 | 46925704 | 46925999 | chr21 | 46926363 | 46926662 |
| chr21 | 46935727 | 46936018 | chr21 | 47010168 | 47010527 | chr21 | 47062446 | 47062925 |
| chr21 | 47063451 | 47064050 | chr21 | 47064165 | 47064464 | chr21 | 47404071 | 47404429 |
| chr21 | 47504759 | 47504994 | chr21 | 47518676 | 47518915 | chr21 | 47717486 | 47717541 |
| chr21 | 47717623 | 47717665 | chr21 | 47746183 | 47746482 | chr22 | 17081848 | 17082087 |
| chr22 | 17082492 | 17082671 | chr22 | 17082854 | 17083093 | chr22 | 17083297 | 17083596 |
| chr22 | 17600988 | 17601467 | chr22 | 17602419 | 17602718 | chr22 | 17850359 | 17850718 |
| chr22 | 18009986 | 18010085 | chr22 | 18328049 | 18328348 | chr22 | 19017431 | 19017670 |
| chr22 | 19117490 | 19117669 | chr22 | 19510704 | 19511663 | chr22 | 19511765 | 19512184 |
| chr22 | 19706119 | 19706754 | chr22 | 19742753 | 19743052 | chr22 | 19748561 | 19749040 |
| chr22 | 20792372 | 20792689 | chr22 | 21153919 | 21154084 | chr22 | 21304980 | 21305098 |
| chr22 | 21368513 | 21368692 | chr22 | 21977249 | 21977451 | chr22 | 21982708 | 21983062 |
| chr22 | 22006004 | 22006243 | chr22 | 22058102 | 22058341 | chr22 | 22090520 | 22090819 |
| chr22 | 22862704 | 22863243 | chr22 | 22901011 | 22901550 | chr22 | 23791328 | 23791507 |
| chr22 | 23801388 | 23801567 | chr22 | 24180608 | 24180847 | chr22 | 24560283 | 24560522 |
| chr22 | 24820244 | 24820483 | chr22 | 25678654 | 25679433 | chr22 | 25817025 | 25817264 |
| chr22 | 25817356 | 25817715 | chr22 | 28198468 | 28198601 | chr22 | 28371575 | 28371754 |
| chr22 | 28838105 | 28838396 | chr22 | 28838411 | 28838524 | chr22 | 29091752 | 29091929 |
| chr22 | 29445659 | 29446018 | chr22 | 29876117 | 29876189 | chr22 | 29877142 | 29877381 |
| chr22 | 29977650 | 29977755 | chr22 | 30116824 | 30117240 | chr22 | 30158246 | 30158365 |
| chr22 | 30938434 | 30938673 | chr22 | 31198416 | 31198715 | chr22 | 31218436 | 31218615 |
| chr22 | 31218693 | 31218932 | chr22 | 31481052 | 31481411 | chr22 | 32748862 | 32749041 |
| chr22 | 33197509 | 33197748 | chr22 | 33453802 | 33454452 | chr22 | 35848275 | 35848476 |
| chr22 | 36902217 | 36902456 | chr22 | 38199683 | 38199982 | chr22 | 38220568 | 38221287 |
| chr22 | 38476983 | 38477882 | chr22 | 38592953 | 38593132 | chr22 | 38639155 | 38639304 |
| chr22 | 39784390 | 39784599 | chr22 | 39830257 | 39830492 | chr22 | 39853438 | 39853677 |
| chr22 | 39932459 | 39932638 | chr22 | 39954323 | 39954615 | chr22 | 40042536 | 40042835 |
| chr22 | 40075089 | 40075328 | chr22 | 40226368 | 40226487 | chr22 | 41048414 | 41048593 |
| chr22 | 41048654 | 41048951 | chr22 | 41634334 | 41634639 | chr22 | 41636999 | 41637217 |
| chr22 | 41657217 | 41657442 | chr22 | 42095992 | 42096276 | chr22 | 42310005 | 42310304 |
| chr22 | 42311435 | 42311674 | chr22 | 42353530 | 42353992 | chr22 | 42667276 | 42667501 |
| chr22 | 42679636 | 42679935 | chr22 | 43012441 | 43012560 | chr22 | 43012883 | 43012980 |
| chr22 | 43083029 | 43083145 | chr22 | 43434340 | 43434579 | chr22 | 43739987 | 43740226 |
| chr22 | 43808205 | 43808502 | chr22 | 44208422 | 44208523 | chr22 | 44258287 | 44258586 |
| chr22 | 44287554 | 44287793 | chr22 | 44455605 | 44455844 | chr22 | 45088524 | 45088823 |
| chr22 | 45135840 | 45136079 | chr22 | 45277218 | 45277397 | chr22 | 45402991 | 45403230 |
| chr22 | 45404106 | 45404525 | chr22 | 45404909 | 45405148 | chr22 | 45405219 | 45405518 |
| chr22 | 45405545 | 45405803 | chr22 | 45406181 | 45406420 | chr22 | 45593572 | 45593799 |

TABLE 14-continued

Pan Cancer #4

| chr | start | end | chr | start | end | chr | start | end |
|---|---|---|---|---|---|---|---|---|
| chr22 | 45604107 | 45604444 | chr22 | 46262352 | 46263911 | chr22 | 46367955 | 46368134 |
| chr22 | 46438002 | 46438112 | chr22 | 46658700 | 46658939 | chr22 | 46931177 | 46931336 |
| chr22 | 46933014 | 46933104 | chr22 | 47004998 | 47005237 | chr22 | 47023028 | 47023267 |
| chr22 | 47054612 | 47054700 | chr22 | 47193234 | 47193473 | chr22 | 47525747 | 47525986 |
| chr22 | 48027582 | 48027731 | chr22 | 48884957 | 48885136 | chr22 | 48885210 | 48885989 |
| chr22 | 48886575 | 48886934 | chr22 | 48931805 | 48932104 | chr22 | 48971050 | 48971829 |
| chr22 | 48972042 | 48972761 | chr22 | 49852543 | 49852722 | chr22 | 49979553 | 49979835 |
| chr22 | 50001612 | 50001912 | chr22 | 50002684 | 50002911 | chr22 | 50003130 | 50003309 |
| chr22 | 50010037 | 50010336 | chr22 | 50010374 | 50010673 | chr22 | 50031617 | 50031796 |
| chr22 | 50149332 | 50149548 | chr22 | 50466931 | 50467045 | chr22 | 50496761 | 50497000 |
| chr22 | 50497068 | 50497367 | chr22 | 50623595 | 50623894 | chr22 | 50899214 | 50899753 |
| chr22 | 50943082 | 50943358 | chr22 | 51042185 | 51042881 | chr22 | 51112072 | 51112311 |
| chrX | 3746538 | 3746717 | chrX | 6145241 | 6145780 | chrX | 8698761 | 8699000 |
| chrX | 8699416 | 8699655 | chrX | 136656489 | 136656534 | AC211950.2_11234-25326 | 181 | 343 |
| AC211950.2_11234-25326 | 13241 | 13420 | AC211950.2_11234-25326 | 13667 | 13966 | AC241851.2_88-34049 | 15187 | 15426 |
| AEKP011687 36.1_1-4752 | 1662 | 1781 | AEKP01168 736.1_1-4752 | 1874 | 2381 | JH636052.4 | 5118687 | 5118986 |
| NW_001838 016.1_818233-828058 | 6095 | 6142 | | | | | | |

TABLE 15

Pan-cancer #5

| chr | start | end | chr | start | end | chr | start | end |
|---|---|---|---|---|---|---|---|---|
| chr1 | 898633 | 898792 | chr1 | 913445 | 914044 | chr1 | 1080495 | 1080914 |
| chr1 | 1146657 | 1146896 | chr1 | 1218688 | 1218779 | chr1 | 1223433 | 1223595 |
| chr1 | 1235811 | 1236156 | chr1 | 1266957 | 1267233 | chr1 | 1267372 | 1267791 |
| chr1 | 1267823 | 1268242 | chr1 | 1341738 | 1341826 | chr1 | 1475458 | 1475644 |
| chr1 | 1476255 | 1476417 | chr1 | 1483096 | 1483139 | chr1 | 1563119 | 1563298 |
| chr1 | 1856362 | 1856471 | chr1 | 1857759 | 1857811 | chr1 | 1874647 | 1874891 |
| chr1 | 1910341 | 1910465 | chr1 | 1935188 | 1935207 | chr1 | 1935232 | 1935289 |
| chr1 | 1935291 | 1935547 | chr1 | 1974768 | 1974802 | chr1 | 2066406 | 2066756 |
| chr1 | 2125141 | 2125560 | chr1 | 2263067 | 2263366 | chr1 | 2267472 | 2267771 |
| chr1 | 2304239 | 2304478 | chr1 | 2307851 | 2307970 | chr1 | 2308023 | 2308030 |
| chr1 | 2308297 | 2308716 | chr1 | 2309792 | 2309994 | chr1 | 2331281 | 2331500 |
| chr1 | 2336323 | 2336440 | chr1 | 2375047 | 2375646 | chr1 | 2396927 | 2397106 |
| chr1 | 2428239 | 2428478 | chr1 | 2472089 | 2472388 | chr1 | 2506974 | 2507150 |
| chr1 | 2520925 | 2521062 | chr1 | 2706308 | 2706335 | chr1 | 2830081 | 2830147 |
| chr1 | 2865964 | 2866143 | chr1 | 2984645 | 2984824 | chr1 | 3102567 | 3102856 |
| chr1 | 3182781 | 3182874 | chr1 | 3182942 | 3183020 | chr1 | 3322011 | 3322250 |
| chr1 | 3567062 | 3567345 | chr1 | 3567738 | 3567851 | chr1 | 3567883 | 3568320 |
| chr1 | 3601749 | 3602030 | chr1 | 3659530 | 3659643 | chr1 | 3659672 | 3659769 |
| chr1 | 3663458 | 3663637 | chr1 | 3663779 | 3664018 | chr1 | 3664606 | 3664781 |
| chr1 | 3683723 | 3683902 | chr1 | 4111087 | 4111323 | chr1 | 4713943 | 4714075 |
| chr1 | 4714164 | 4714362 | chr1 | 4715428 | 4715540 | chr1 | 4715575 | 4716537 |
| chr1 | 4716539 | 4716744 | chr1 | 6166262 | 6166561 | chr1 | 6171668 | 6171907 |
| chr1 | 6186410 | 6186649 | chr1 | 6280169 | 6280348 | chr1 | 6304103 | 6304342 |
| chr1 | 6446041 | 6446400 | chr1 | 6480434 | 6480913 | chr1 | 6500911 | 6500988 |
| chr1 | 6501055 | 6501262 | chr1 | 6507603 | 6508202 | chr1 | 7764540 | 7764775 |
| chr1 | 8277776 | 8277837 | chr1 | 9712017 | 9712179 | chr1 | 9712459 | 9713096 |
| chr1 | 10166481 | 10166626 | chr1 | 10948478 | 10948657 | chr1 | 11538796 | 11538913 |
| chr1 | 11539101 | 11539280 | chr1 | 11539336 | 11539515 | chr1 | 11540040 | 11540179 |
| chr1 | 11591712 | 11591863 | chr1 | 11752375 | 11752614 | chr1 | 11936674 | 11936779 |
| chr1 | 11958996 | 11959295 | chr1 | 12041511 | 12041630 | chr1 | 12123143 | 12123554 |
| chr1 | 12227604 | 12227805 | chr1 | 12251342 | 12252059 | chr1 | 13839669 | 13839769 |
| chr1 | 13910336 | 13910698 | chr1 | 13910700 | 13910757 | chr1 | 13910794 | 13910815 |
| chr1 | 14026401 | 14026700 | chr1 | 14730390 | 14730502 | chr1 | 14925417 | 14926136 |
| chr1 | 15251113 | 15251316 | chr1 | 15480854 | 15480983 | chr1 | 16085267 | 16085288 |
| chr1 | 16474484 | 16475299 | chr1 | 16861448 | 16861627 | chr1 | 17445781 | 17446011 |
| chr1 | 18437373 | 18437431 | chr1 | 18437433 | 18437612 | chr1 | 18956114 | 18956353 |
| chr1 | 18956383 | 18956408 | chr1 | 18956496 | 18956611 | chr1 | 18956782 | 18957321 |
| chr1 | 18957428 | 18957667 | chr1 | 18957938 | 18958229 | chr1 | 18958359 | 18958477 |
| chr1 | 18959346 | 18959390 | chr1 | 18959456 | 18959645 | chr1 | 18960795 | 18961094 |
| chr1 | 18962648 | 18963231 | chr1 | 18969543 | 18969902 | chr1 | 18971772 | 18972011 |
| chr1 | 18972056 | 18972170 | chr1 | 19043472 | 19043743 | chr1 | 19043757 | 19043771 |
| chr1 | 19992272 | 19992313 | chr1 | 19992433 | 19992511 | chr1 | 20127444 | 20127555 |
| chr1 | 20618230 | 20618469 | chr1 | 20878953 | 20879029 | chr1 | 20879031 | 20879229 |
| chr1 | 20879256 | 20879372 | chr1 | 20879482 | 20879721 | chr1 | 20879752 | 20880051 |

TABLE 15-continued

Pan-cancer #5

| chr | start | end | chr | start | end | chr | start | end |
|---|---|---|---|---|---|---|---|---|
| chr1 | 20880095 | 20880694 | chr1 | 21026082 | 21026253 | chr1 | 21042820 | 21042999 |
| chr1 | 21044024 | 21044263 | chr1 | 21573736 | 21574215 | chr1 | 21835856 | 21836095 |
| chr1 | 22140674 | 22141014 | chr1 | 22141016 | 22141393 | chr1 | 22927327 | 22927566 |
| chr1 | 23748907 | 23749146 | chr1 | 23884996 | 23885088 | chr1 | 25255921 | 25256029 |
| chr1 | 25256280 | 25256459 | chr1 | 25257157 | 25257305 | chr1 | 25257391 | 25257464 |
| chr1 | 26551597 | 26551625 | chr1 | 26551729 | 26551896 | chr1 | 26551989 | 26552228 |
| chr1 | 26737509 | 26737688 | chr1 | 26737855 | 26737883 | chr1 | 26737908 | 26738274 |
| chr1 | 27190078 | 27190377 | chr1 | 27844444 | 27844623 | chr1 | 29450398 | 29450637 |
| chr1 | 29585984 | 29586763 | chr1 | 29804872 | 29805171 | chr1 | 30351469 | 30351828 |
| chr1 | 30815328 | 30815417 | chr1 | 30815455 | 30815675 | chr1 | 31863112 | 31863130 |
| chr1 | 32180323 | 32180502 | chr1 | 32237507 | 32237546 | chr1 | 32237639 | 32238586 |
| chr1 | 32410202 | 32410364 | chr1 | 32705425 | 32705639 | chr1 | 32756421 | 32756519 |
| chr1 | 32930524 | 32930658 | chr1 | 34628874 | 34629053 | chr1 | 34629390 | 34629809 |
| chr1 | 34630473 | 34630712 | chr1 | 34630770 | 34631069 | chr1 | 34631502 | 34631741 |
| chr1 | 34631872 | 34631892 | chr1 | 34632023 | 34632038 | chr1 | 34642298 | 34642490 |
| chr1 | 35258557 | 35258796 | chr1 | 35350980 | 35351759 | chr1 | 35395450 | 35395541 |
| chr1 | 35395543 | 35395929 | chr1 | 35664721 | 35664836 | chr1 | 36042605 | 36043564 |
| chr1 | 36563382 | 36563621 | chr1 | 37498718 | 37498845 | chr1 | 37498889 | 37499257 |
| chr1 | 37499358 | 37499683 | chr1 | 37500014 | 37500257 | chr1 | 37500368 | 37500441 |
| chr1 | 37500443 | 37500575 | chr1 | 37500603 | 37500907 | chr1 | 37500998 | 37501107 |
| chr1 | 38100591 | 38100787 | chr1 | 38219635 | 38219874 | chr1 | 38229961 | 38230243 |
| chr1 | 38230283 | 38230380 | chr1 | 38230700 | 38230937 | chr1 | 38398356 | 38398431 |
| chr1 | 38510079 | 38510258 | chr1 | 38510475 | 38510714 | chr1 | 38510778 | 38510933 |
| chr1 | 38510935 | 38511197 | chr1 | 38511252 | 38511800 | chr1 | 38511822 | 38511911 |
| chr1 | 38512311 | 38512490 | chr1 | 38513162 | 38513229 | chr1 | 39269662 | 39270201 |
| chr1 | 40137822 | 40138061 | chr1 | 40237053 | 40237281 | chr1 | 40349627 | 40349746 |
| chr1 | 41284058 | 41284541 | chr1 | 41847494 | 41847793 | chr1 | 41848778 | 41848889 |
| chr1 | 41967261 | 41967360 | chr1 | 41991552 | 41991791 | chr1 | 43834653 | 43834807 |
| chr1 | 44068700 | 44068879 | chr1 | 44726821 | 44727360 | chr1 | 44872358 | 44872723 |
| chr1 | 44872924 | 44873064 | chr1 | 44873066 | 44873173 | chr1 | 44873510 | 44873797 |
| chr1 | 44883030 | 44883215 | chr1 | 44883752 | 44884123 | chr1 | 44884204 | 44884289 |
| chr1 | 45308239 | 45308358 | chr1 | 45308655 | 45308729 | chr1 | 46632781 | 46633020 |
| chr1 | 46913761 | 46913877 | chr1 | 46913887 | 46914246 | chr1 | 46914286 | 46914360 |
| chr1 | 46914582 | 46914641 | chr1 | 46932686 | 46932842 | chr1 | 46951114 | 46951318 |
| chr1 | 46951645 | 46951833 | chr1 | 46956380 | 46956616 | chr1 | 46956728 | 46956839 |
| chr1 | 46956841 | 46957246 | chr1 | 47009851 | 47009886 | chr1 | 47009911 | 47010036 |
| chr1 | 47010105 | 47010150 | chr1 | 47695033 | 47695512 | chr1 | 47696207 | 47696521 |
| chr1 | 47696621 | 47696686 | chr1 | 47696727 | 47696965 | chr1 | 47696987 | 47697206 |
| chr1 | 47697254 | 47697255 | chr1 | 47697280 | 47697613 | chr1 | 47697642 | 47697947 |
| chr1 | 47698007 | 47698301 | chr1 | 47881984 | 47882265 | chr1 | 47882267 | 47882403 |
| chr1 | 47882697 | 47882906 | chr1 | 47909640 | 47910239 | chr1 | 47910420 | 47910625 |
| chr1 | 47910749 | 47911019 | chr1 | 47911243 | 47911335 | chr1 | 48058982 | 48059341 |
| chr1 | 49242260 | 49242359 | chr1 | 49242361 | 49242513 | chr1 | 49242515 | 49242619 |
| chr1 | 50513541 | 50513837 | chr1 | 50799190 | 50799317 | chr1 | 50799394 | 50799489 |
| chr1 | 50880932 | 50881317 | chr1 | 50881427 | 50881957 | chr1 | 50882144 | 50882625 |
| chr1 | 50882731 | 50883690 | chr1 | 50883800 | 50883977 | chr1 | 50884021 | 50884353 |
| chr1 | 50884691 | 50884888 | chr1 | 50885262 | 50885441 | chr1 | 50886107 | 50887085 |
| chr1 | 50887176 | 50887366 | chr1 | 50888619 | 50888796 | chr1 | 50889124 | 50889607 |
| chr1 | 50889741 | 50890460 | chr1 | 50890600 | 50890649 | chr1 | 50890796 | 50891565 |
| chr1 | 50892073 | 50892284 | chr1 | 50892337 | 50892432 | chr1 | 50892523 | 50893149 |
| chr1 | 50893151 | 50893423 | chr1 | 50893519 | 50893962 | chr1 | 51763181 | 51763395 |
| chr1 | 52832605 | 52832712 | chr1 | 53068087 | 53068181 | chr1 | 53068183 | 53068626 |
| chr1 | 53098746 | 53099053 | chr1 | 53099055 | 53099165 | chr1 | 53308489 | 53308608 |
| chr1 | 53308908 | 53309328 | chr1 | 53528288 | 53528527 | chr1 | 53705675 | 53705794 |
| chr1 | 54203419 | 54203422 | chr1 | 54203829 | 54204498 | chr1 | 54586532 | 54586831 |
| chr1 | 55462599 | 55462778 | chr1 | 57888293 | 57888472 | chr1 | 57888888 | 57889035 |
| chr1 | 57889037 | 57889187 | chr1 | 57889319 | 57889604 | chr1 | 57889606 | 57889738 |
| chr1 | 57890332 | 57890671 | chr1 | 58715055 | 58715294 | chr1 | 58715375 | 58715532 |
| chr1 | 58715784 | 58715855 | chr1 | 58715979 | 58716094 | chr1 | 61519265 | 61519405 |
| chr1 | 61519473 | 61519497 | chr1 | 62793169 | 62793342 | chr1 | 63539429 | 63539968 |
| chr1 | 63785232 | 63785293 | chr1 | 63785619 | 63785767 | chr1 | 63786079 | 63786431 |
| chr1 | 63786928 | 63787167 | chr1 | 63787226 | 63787249 | chr1 | 63787283 | 63787645 |
| chr1 | 63788341 | 63788640 | chr1 | 63788694 | 63788767 | chr1 | 63788920 | 63789497 |
| chr1 | 63789729 | 63789792 | chr1 | 63789850 | 63789913 | chr1 | 63790253 | 63790373 |
| chr1 | 63792458 | 63792649 | chr1 | 63792798 | 63793171 | chr1 | 63795265 | 63795934 |
| chr1 | 63795936 | 63796370 | chr1 | 63796418 | 63796584 | chr1 | 64240031 | 64240222 |
| chr1 | 64240533 | 64240765 | chr1 | 64734554 | 64734669 | chr1 | 64937227 | 64937401 |
| chr1 | 65731243 | 65731506 | chr1 | 65731782 | 65731851 | chr1 | 65990876 | 65991019 |
| chr1 | 65991344 | 65991561 | chr1 | 65991606 | 65991758 | chr1 | 65991784 | 65991883 |
| chr1 | 66258088 | 66258651 | chr1 | 66258672 | 66258760 | chr1 | 66258762 | 66258867 |
| chr1 | 66259621 | 66259276 | chr1 | 66998702 | 66999412 | chr1 | 66999536 | 66999206 |
| chr1 | 67217965 | 67218424 | chr1 | 67390243 | 67390542 | chr1 | 67390993 | 67391172 |
| chr1 | 67773081 | 67773860 | chr1 | 70033524 | 70033709 | chr1 | 70033829 | 70034003 |
| chr1 | 70034368 | 70034491 | chr1 | 70034493 | 70034667 | chr1 | 70035014 | 70035208 |
| chr1 | 70035210 | 70035526 | chr1 | 70599152 | 70599260 | chr1 | 70672859 | 70672978 |
| chr1 | 72749635 | 72749700 | chr1 | 72749732 | 72749798 | chr1 | 75595702 | 75595759 |

TABLE 15-continued

Pan-cancer #5

| chr | start | end | chr | start | end | chr | start | end |
|---|---|---|---|---|---|---|---|---|
| chr1 | 75595819 | 75595991 | chr1 | 75596136 | 75596479 | chr1 | 75596597 | 75596859 |
| chr1 | 75596930 | 75597668 | chr1 | 75597842 | 75598261 | chr1 | 75598310 | 75598489 |
| chr1 | 75599345 | 75599704 | chr1 | 75600148 | 75600685 | chr1 | 75600687 | 75601119 |
| chr1 | 75601188 | 75601276 | chr1 | 75601278 | 75601513 | chr1 | 75601889 | 75603148 |
| chr1 | 76080387 | 76080727 | chr1 | 76080729 | 76080866 | chr1 | 76082050 | 76082289 |
| chr1 | 76354731 | 76354839 | chr1 | 76540398 | 76540574 | chr1 | 76540576 | 76540757 |
| chr1 | 77332984 | 77333159 | chr1 | 77333161 | 77333163 | chr1 | 77333285 | 77333434 |
| chr1 | 77333580 | 77333625 | chr1 | 77334169 | 77334386 | chr1 | 77334409 | 77334757 |
| chr1 | 77334796 | 77334846 | chr1 | 77747291 | 77747382 | chr1 | 77747384 | 77747530 |
| chr1 | 77747848 | 77748327 | chr1 | 78511371 | 78511856 | chr1 | 78511858 | 78512450 |
| chr1 | 78957198 | 78957617 | chr1 | 82268586 | 82268904 | chr1 | 84944531 | 84944650 |
| chr1 | 85358543 | 85358593 | chr1 | 85358752 | 85358902 | chr1 | 85463275 | 85463454 |
| chr1 | 86621565 | 86622024 | chr1 | 86622112 | 86622113 | chr1 | 86622115 | 86622224 |
| chr1 | 86622430 | 86622552 | chr1 | 86622813 | 86622831 | chr1 | 86860815 | 86861049 |
| chr1 | 87617672 | 87617911 | chr1 | 90309344 | 90309571 | chr1 | 91171926 | 91172765 |
| chr1 | 91177865 | 91178284 | chr1 | 91179982 | 91180401 | chr1 | 91181853 | 91182212 |
| chr1 | 91182246 | 91182969 | chr1 | 91183001 | 91183196 | chr1 | 91183251 | 91183519 |
| chr1 | 91183521 | 91183611 | chr1 | 91183776 | 91183805 | chr1 | 91183850 | 91184080 |
| chr1 | 91184339 | 91184413 | chr1 | 91184415 | 91184758 | chr1 | 91185126 | 91185309 |
| chr1 | 91185348 | 91185809 | chr1 | 91188891 | 91189483 | chr1 | 91189585 | 91190484 |
| chr1 | 91190791 | 91190949 | chr1 | 91190985 | 91191001 | chr1 | 91191003 | 91191235 |
| chr1 | 91191290 | 91191390 | chr1 | 91192174 | 91192577 | chr1 | 91192682 | 91192773 |
| chr1 | 91194446 | 91194672 | chr1 | 91195015 | 91195494 | chr1 | 91195802 | 91196195 |
| chr1 | 91196226 | 91196581 | chr1 | 91316168 | 91316407 | chr1 | 91316536 | 91316775 |
| chr1 | 91869914 | 91870093 | chr1 | 92948236 | 92948701 | chr1 | 92948760 | 92949059 |
| chr1 | 92952071 | 92952632 | chr1 | 94343486 | 94343596 | chr1 | 97185167 | 97185357 |
| chr1 | 98510704 | 98511031 | chr1 | 98511033 | 98511423 | chr1 | 98511536 | 98512015 |
| chr1 | 98514151 | 98514330 | chr1 | 98515048 | 98515087 | chr1 | 98515089 | 98515408 |
| chr1 | 98518930 | 98519661 | chr1 | 98519663 | 98519769 | chr1 | 99469586 | 99469697 |
| chr1 | 99469760 | 99469885 | chr1 | 99470049 | 99470062 | chr1 | 99470212 | 99470288 |
| chr1 | 99470697 | 99470924 | chr1 | 100437184 | 100437270 | chr1 | 101004358 | 101004817 |
| chr1 | 101004989 | 101005228 | chr1 | 101005279 | 101005758 | chr1 | 101702411 | 101702602 |
| chr1 | 101702604 | 101702710 | chr1 | 101703538 | 101703717 | chr1 | 107682647 | 107683066 |
| chr1 | 107683359 | 107683598 | chr1 | 107684161 | 107684520 | chr1 | 108506989 | 108507077 |
| chr1 | 108507149 | 108507168 | chr1 | 108507230 | 108507376 | chr1 | 108507495 | 108507589 |
| chr1 | 108507658 | 108507914 | chr1 | 108507957 | 108508207 | chr1 | 108508209 | 108508548 |
| chr1 | 108508550 | 108508671 | chr1 | 109203582 | 109203761 | chr1 | 109585369 | 109585472 |
| chr1 | 109631647 | 109631766 | chr1 | 109644252 | 109644413 | chr1 | 110610483 | 110610898 |
| chr1 | 110611046 | 110611277 | chr1 | 110611435 | 110611514 | chr1 | 110611654 | 110611794 |
| chr1 | 110626791 | 110627671 | chr1 | 110672792 | 110673082 | chr1 | 110673084 | 110673331 |
| chr1 | 110692886 | 110693497 | chr1 | 110693737 | 110694205 | chr1 | 110754040 | 110754202 |
| chr1 | 110754211 | 110754357 | chr1 | 110754872 | 110754930 | chr1 | 110883455 | 110884054 |
| chr1 | 111097832 | 111098011 | chr1 | 111098107 | 111098406 | chr1 | 111216684 | 111216973 |
| chr1 | 111217195 | 111217575 | chr1 | 111217577 | 111217712 | chr1 | 111217714 | 111217892 |
| chr1 | 111217924 | 111218063 | chr1 | 111505931 | 111506290 | chr1 | 111813448 | 111813687 |
| chr1 | 112084880 | 112085059 | chr1 | 114448981 | 114449087 | chr1 | 114695362 | 114695695 |
| chr1 | 114695697 | 114695737 | chr1 | 114695800 | 114696021 | chr1 | 114696132 | 114696183 |
| chr1 | 114696350 | 114696464 | chr1 | 114696541 | 114696791 | chr1 | 115256441 | 115256620 |
| chr1 | 115258659 | 115258838 | chr1 | 115631842 | 115632011 | chr1 | 115632393 | 115632632 |
| chr1 | 115880081 | 115880207 | chr1 | 115880209 | 115880500 | chr1 | 115880765 | 115880795 |
| chr1 | 115880873 | 115881043 | chr1 | 115881249 | 115881304 | chr1 | 116214002 | 116214132 |
| chr1 | 116214207 | 116214421 | chr1 | 116371051 | 116371187 | chr1 | 116371189 | 116371290 |
| chr1 | 116380550 | 116381389 | chr1 | 116382294 | 116382583 | chr1 | 119521979 | 119522121 |
| chr1 | 119522200 | 119522435 | chr1 | 119522566 | 119522632 | chr1 | 119522741 | 119522854 |
| chr1 | 119522926 | 119523039 | chr1 | 119527237 | 119527472 | chr1 | 119527549 | 119527728 |
| chr1 | 119528557 | 119529216 | chr1 | 119529703 | 119529912 | chr1 | 119530024 | 119530149 |
| chr1 | 119530202 | 119530508 | chr1 | 119530554 | 119530600 | chr1 | 119530602 | 119530743 |
| chr1 | 119530944 | 119531243 | chr1 | 119531943 | 119531997 | chr1 | 119536058 | 119536457 |
| chr1 | 119542905 | 119542994 | chr1 | 119543070 | 119543215 | chr1 | 119543274 | 119543324 |
| chr1 | 119543438 | 119544277 | chr1 | 119548749 | 119548928 | chr1 | 119548955 | 119549017 |
| chr1 | 119549032 | 119549735 | chr1 | 119549915 | 119550034 | chr1 | 119550068 | 119550367 |
| chr1 | 119550434 | 119550721 | chr1 | 119551014 | 119551357 | chr1 | 150603035 | 150603141 |
| chr1 | 151169649 | 151169757 | chr1 | 151170069 | 151170297 | chr1 | 151300814 | 151300933 |
| chr1 | 151693849 | 151694448 | chr1 | 152085302 | 152085601 | chr1 | 152488055 | 152488294 |
| chr1 | 153539382 | 153539681 | chr1 | 153540006 | 153540245 | chr1 | 153651873 | 153652472 |
| chr1 | 153937048 | 153937167 | chr1 | 154298254 | 154298562 | chr1 | 154475372 | 154475612 |
| chr1 | 154516709 | 154516926 | chr1 | 155043313 | 155043734 | chr1 | 155578918 | 155579008 |
| chr1 | 155826303 | 155826412 | chr1 | 155954190 | 155954391 | chr1 | 156010529 | 156010643 |
| chr1 | 156215255 | 156215434 | chr1 | 156215527 | 156215886 | chr1 | 156357892 | 156358611 |
| chr1 | 156390058 | 156390777 | chr1 | 156405635 | 156406071 | chr1 | 156406105 | 156406515 |
| chr1 | 156432076 | 156432315 | chr1 | 156594879 | 156595053 | chr1 | 156595081 | 156595118 |
| chr1 | 156611795 | 156611944 | chr1 | 156611994 | 156612214 | chr1 | 156626505 | 156626744 |
| chr1 | 156626814 | 156627019 | chr1 | 156627084 | 156627113 | chr1 | 156646516 | 156646597 |
| chr1 | 156646635 | 156646740 | chr1 | 156814831 | 156814953 | chr1 | 156815031 | 156815240 |
| chr1 | 156815356 | 156815835 | chr1 | 156830190 | 156830192 | chr1 | 156830266 | 156830429 |
| chr1 | 156838078 | 156838424 | chr1 | 156863062 | 156863429 | chr1 | 156863641 | 156863808 |

TABLE 15-continued

Pan-cancer #5

| chr | start | end | chr | start | end | chr | start | end |
|---|---|---|---|---|---|---|---|---|
| chr1 | 157247369 | 157247487 | chr1 | 157458816 | 157458935 | chr1 | 157895339 | 157895518 |
| chr1 | 158669614 | 158669973 | chr1 | 158687334 | 158687633 | chr1 | 159158251 | 159158369 |
| chr1 | 159158472 | 159158588 | chr1 | 159187205 | 159187390 | chr1 | 160693839 | 160693957 |
| chr1 | 160992253 | 160992363 | chr1 | 161007615 | 161007847 | chr1 | 161228566 | 161228971 |
| chr1 | 161275466 | 161275579 | chr1 | 161275640 | 161276125 | chr1 | 161442367 | 161442546 |
| chr1 | 161471751 | 161471868 | chr1 | 161591390 | 161591444 | chr1 | 161591549 | 161591629 |
| chr1 | 162792211 | 162792630 | chr1 | 164290533 | 164290672 | chr1 | 164290724 | 164290772 |
| chr1 | 165086889 | 165087114 | chr1 | 165204994 | 165205233 | chr1 | 165321651 | 165321787 |
| chr1 | 165321943 | 165321950 | chr1 | 165324104 | 165324758 | chr1 | 165325016 | 165325357 |
| chr1 | 165325395 | 165325615 | chr1 | 165325804 | 165326043 | chr1 | 165326128 | 165326205 |
| chr1 | 165326297 | 165326547 | chr1 | 165414124 | 165414352 | chr1 | 166134158 | 166134282 |
| chr1 | 166134284 | 166134397 | chr1 | 166134643 | 166134882 | chr1 | 166135118 | 166135357 |
| chr1 | 166853551 | 166853578 | chr1 | 166853580 | 166853668 | chr1 | 166916774 | 166916921 |
| chr1 | 166916937 | 166916950 | chr1 | 166917125 | 166917193 | chr1 | 167599076 | 167599435 |
| chr1 | 167599521 | 167599940 | chr1 | 167823371 | 167823524 | chr1 | 169396291 | 169396635 |
| chr1 | 169396637 | 169396689 | chr1 | 169396731 | 169397010 | chr1 | 170629466 | 170629513 |
| chr1 | 170630364 | 170630602 | chr1 | 170630604 | 170630903 | chr1 | 170631005 | 170631244 |
| chr1 | 170631399 | 170631638 | chr1 | 170633533 | 170633712 | chr1 | 170637582 | 170637881 |
| chr1 | 170640425 | 170640625 | chr1 | 170640665 | 170640784 | chr1 | 171625443 | 171625543 |
| chr1 | 171810113 | 171811066 | chr1 | 173638567 | 173639153 | chr1 | 175346411 | 175346646 |
| chr1 | 175388563 | 175388682 | chr1 | 177133690 | 177133918 | chr1 | 177140021 | 177140145 |
| chr1 | 177140147 | 177140174 | chr1 | 177140305 | 177140790 | chr1 | 177150699 | 177150878 |
| chr1 | 179544884 | 179545091 | chr1 | 179545093 | 179545183 | chr1 | 179712063 | 179712339 |
| chr1 | 179712411 | 179712554 | chr1 | 179712568 | 179712591 | chr1 | 179712593 | 179712734 |
| chr1 | 179712831 | 179713175 | chr1 | 180197986 | 180198285 | chr1 | 180202331 | 180202395 |
| chr1 | 180202649 | 180203110 | chr1 | 180203355 | 180203608 | chr1 | 180203634 | 180204221 |
| chr1 | 180204223 | 180204620 | chr1 | 180204898 | 180205009 | chr1 | 180235656 | 180235835 |
| chr1 | 180882487 | 180882518 | chr1 | 180925188 | 180925289 | chr1 | 180925330 | 180925487 |
| chr1 | 181287599 | 181287838 | chr1 | 181287922 | 181288281 | chr1 | 181451315 | 181452214 |
| chr1 | 181452770 | 181452986 | chr1 | 181453051 | 181453069 | chr1 | 181454774 | 181455013 |
| chr1 | 181455104 | 181455343 | chr1 | 182584084 | 182584340 | chr1 | 182584404 | 182584623 |
| chr1 | 182807488 | 182807607 | chr1 | 183129301 | 183129530 | chr1 | 183386070 | 183386319 |
| chr1 | 183386599 | 183386713 | chr1 | 183386752 | 183386827 | chr1 | 183386947 | 183387051 |
| chr1 | 183387174 | 183387413 | chr1 | 183462984 | 183463103 | chr1 | 183774155 | 183774454 |
| chr1 | 184005609 | 184005908 | chr1 | 185073803 | 185074028 | chr1 | 190444781 | 190444892 |
| chr1 | 190445080 | 190445197 | chr1 | 190445199 | 190445379 | chr1 | 190447297 | 190447300 |
| chr1 | 190447389 | 190447596 | chr1 | 195732240 | 195732521 | chr1 | 196577628 | 196577953 |
| chr1 | 196578007 | 196578246 | chr1 | 197879307 | 197879546 | chr1 | 197879607 | 197879661 |
| chr1 | 197879717 | 197880258 | chr1 | 197882052 | 197882291 | chr1 | 197882353 | 197882581 |
| chr1 | 197886978 | 197887067 | chr1 | 197887147 | 197887457 | chr1 | 197887707 | 197887817 |
| chr1 | 197887977 | 197888122 | chr1 | 197888181 | 197888396 | chr1 | 197888546 | 197889385 |
| chr1 | 200009312 | 200009551 | chr1 | 200010202 | 200010665 | chr1 | 200011236 | 200011684 |
| chr1 | 200011686 | 200012191 | chr1 | 201368752 | 201368805 | chr1 | 201983038 | 201983277 |
| chr1 | 202081790 | 202081886 | chr1 | 202183343 | 202183476 | chr1 | 202679128 | 202679607 |
| chr1 | 203298210 | 203298441 | chr1 | 203429530 | 203429649 | chr1 | 204333520 | 204333660 |
| chr1 | 204653475 | 204653596 | chr1 | 204653793 | 204653894 | chr1 | 205312504 | 205312912 |
| chr1 | 205312962 | 205313043 | chr1 | 205424577 | 205425046 | chr1 | 205537569 | 205537587 |
| chr1 | 207200767 | 207201066 | chr1 | 207669419 | 207669788 | chr1 | 207669829 | 207670138 |
| chr1 | 207818295 | 207818397 | chr1 | 208084210 | 208084569 | chr1 | 209381030 | 209381269 |
| chr1 | 210111072 | 210111211 | chr1 | 210111422 | 210111923 | chr1 | 210111797 | 210111923 |
| chr1 | 210112037 | 210112244 | chr1 | 211847683 | 211847862 | chr1 | 212963808 | 212963979 |
| chr1 | 213123776 | 213124075 | chr1 | 213124573 | 213124623 | chr1 | 213124669 | 213124992 |
| chr1 | 214156395 | 214157004 | chr1 | 214158753 | 214158911 | chr1 | 214159037 | 214159052 |
| chr1 | 214160028 | 214160266 | chr1 | 214360583 | 214360753 | chr1 | 214360755 | 214360859 |
| chr1 | 214360927 | 214361062 | chr1 | 214724457 | 214724588 | chr1 | 215254998 | 215255897 |
| chr1 | 216897142 | 216897321 | chr1 | 217307385 | 217308360 | chr1 | 217308907 | 217309206 |
| chr1 | 217309671 | 217309910 | chr1 | 217311163 | 217311942 | chr1 | 217312946 | 217313043 |
| chr1 | 217313069 | 217313827 | chr1 | 217805068 | 217805236 | chr1 | 218520021 | 218520063 |
| chr1 | 218520096 | 218520292 | chr1 | 218520310 | 218520477 | chr1 | 218520701 | 218520740 |
| chr1 | 219347112 | 219347134 | chr1 | 219347314 | 219347553 | chr1 | 220101056 | 220101211 |
| chr1 | 220101371 | 220101475 | chr1 | 220101609 | 220101613 | chr1 | 220101675 | 220101788 |
| chr1 | 220636429 | 220636548 | chr1 | 220700737 | 220700976 | chr1 | 221051936 | 221052595 |
| chr1 | 221053527 | 221053946 | chr1 | 221067418 | 221067777 | chr1 | 223302739 | 223302978 |
| chr1 | 223538254 | 223538670 | chr1 | 223936546 | 223936753 | chr1 | 223936996 | 223937145 |
| chr1 | 224400388 | 224400627 | chr1 | 224528740 | 224528919 | chr1 | 224803668 | 224803854 |
| chr1 | 224803995 | 224804296 | chr1 | 224804396 | 224804687 | chr1 | 224804847 | 224804991 |
| chr1 | 224805051 | 224805116 | chr1 | 224805198 | 224805752 | chr1 | 224805849 | 224805890 |
| chr1 | 226411169 | 226411224 | chr1 | 226411247 | 226411348 | chr1 | 226411617 | 226411916 |
| chr1 | 226924982 | 226925281 | chr1 | 227729830 | 227730168 | chr1 | 228194340 | 228194411 |
| chr1 | 228194571 | 228194579 | chr1 | 228195294 | 228196433 | chr1 | 228201147 | 228201326 |
| chr1 | 228247924 | 228247961 | chr1 | 228248228 | 228248407 | chr1 | 228463210 | 228463809 |
| chr1 | 228528749 | 228529108 | chr1 | 228558623 | 228559329 | chr1 | 228566548 | 228566618 |
| chr1 | 228566637 | 228566767 | chr1 | 228604124 | 228604348 | chr1 | 228633887 | 228633920 |
| chr1 | 228633922 | 228633950 | chr1 | 228633984 | 228634354 | chr1 | 228645048 | 228645244 |
| chr1 | 228645306 | 228645827 | chr1 | 228646196 | 228646315 | chr1 | 228651350 | 228651709 |
| chr1 | 228651805 | 228651902 | chr1 | 228652243 | 228652453 | chr1 | 228652509 | 228652704 |

TABLE 15-continued

Pan-cancer #5

| chr | start | end | chr | start | end | chr | start | end |
|---|---|---|---|---|---|---|---|---|
| chr1 | 229542750 | 229542953 | chr1 | 229543221 | 229543229 | chr1 | 229543459 | 229543612 |
| chr1 | 229566670 | 229566942 | chr1 | 229567012 | 229567277 | chr1 | 229567370 | 229567993 |
| chr1 | 229568158 | 229568289 | chr1 | 229569712 | 229569951 | chr1 | 230404150 | 230404360 |
| chr1 | 230561683 | 230561922 | chr1 | 231297013 | 231297103 | chr1 | 231297105 | 231297312 |
| chr1 | 231298505 | 231298651 | chr1 | 231298653 | 231298708 | chr1 | 232765226 | 232765398 |
| chr1 | 233750126 | 233750402 | chr1 | 234040224 | 234040403 | chr1 | 234040886 | 234040974 |
| chr1 | 234041303 | 234041361 | chr1 | 234041416 | 234041659 | chr1 | 234349895 | 234350051 |
| chr1 | 234350053 | 234350194 | chr1 | 234445299 | 234445478 | chr1 | 234620965 | 234621073 |
| chr1 | 234844947 | 234845167 | chr1 | 235813693 | 235813797 | chr1 | 235814010 | 235814292 |
| chr1 | 236227538 | 236227744 | chr1 | 236227770 | 236227921 | chr1 | 236228022 | 236228197 |
| chr1 | 236228507 | 236228624 | chr1 | 236228706 | 236228866 | chr1 | 236559075 | 236559207 |
| chr1 | 236559257 | 236559374 | chr1 | 236849381 | 236849506 | chr1 | 236850198 | 236850220 |
| chr1 | 237205085 | 237205098 | chr1 | 237205157 | 237205174 | chr1 | 237205176 | 237205224 |
| chr1 | 237206102 | 237206266 | chr1 | 237206512 | 237206811 | chr1 | 239550505 | 239551284 |
| chr1 | 240118762 | 240119061 | chr1 | 240160997 | 240161086 | chr1 | 240161123 | 240161381 |
| chr1 | 240161547 | 240161571 | chr1 | 240254859 | 240255098 | chr1 | 240255282 | 240255486 |
| chr1 | 240255488 | 240255581 | chr1 | 240255739 | 240256159 | chr1 | 240256625 | 240256872 |
| chr1 | 240775379 | 240775530 | chr1 | 241052047 | 241052201 | chr1 | 241520202 | 241520441 |
| chr1 | 241520509 | 241520632 | chr1 | 241520685 | 241520688 | chr1 | 241587013 | 241587194 |
| chr1 | 241587513 | 241587609 | chr1 | 241587611 | 241587872 | chr1 | 242686642 | 242687781 |
| chr1 | 242688103 | 242688244 | chr1 | 242688278 | 242688342 | chr1 | 242688377 | 242688773 |
| chr1 | 243646523 | 243646762 | chr1 | 244014160 | 244014479 | chr1 | 244080598 | 244080777 |
| chr1 | 244080874 | 244080883 | chr1 | 244893136 | 244893255 | chr1 | 245135670 | 245135849 |
| chr1 | 245494418 | 245494631 | chr1 | 246330402 | 246330509 | chr1 | 246488077 | 246488316 |
| chr1 | 248002191 | 248002310 | chr1 | 248020405 | 248020449 | chr1 | 248020516 | 248020631 |
| chr1 | 248020957 | 248021424 | chr1 | 248027930 | 248028289 | chr1 | 248074658 | 248074768 |
| chr1 | 248074838 | 248075008 | chr1 | 248099661 | 248099900 | chr1 | 248328674 | 248328921 |
| chr1 | 249121623 | 249121738 | chr2 | 287492 | 287731 | chr2 | 288318 | 288557 |
| chr2 | 468116 | 468182 | chr2 | 468217 | 468234 | chr2 | 468424 | 468756 |
| chr2 | 496125 | 496465 | chr2 | 720748 | 720985 | chr2 | 875887 | 876066 |
| chr2 | 945838 | 946010 | chr2 | 946012 | 946077 | chr2 | 946117 | 946218 |
| chr2 | 946290 | 946356 | chr2 | 946449 | 946567 | chr2 | 946917 | 947044 |
| chr2 | 947127 | 947238 | chr2 | 1653023 | 1653262 | chr2 | 1746523 | 1747033 |
| chr2 | 1747591 | 1748008 | chr2 | 1748397 | 1748906 | chr2 | 2844646 | 2844676 |
| chr2 | 2844802 | 2844825 | chr2 | 5831102 | 5831205 | chr2 | 5831238 | 5831401 |
| chr2 | 5831715 | 5831894 | chr2 | 5831967 | 5832048 | chr2 | 5832284 | 5832326 |
| chr2 | 5832800 | 5832847 | chr2 | 5833283 | 5833433 | chr2 | 5833500 | 5833640 |
| chr2 | 5833735 | 5834119 | chr2 | 5835990 | 5836349 | chr2 | 5836451 | 5836575 |
| chr2 | 5836622 | 5836745 | chr2 | 5836828 | 5836992 | chr2 | 5837353 | 5837468 |
| chr2 | 5866006 | 5866305 | chr2 | 7164389 | 7164704 | chr2 | 7571420 | 7571477 |
| chr2 | 7571577 | 7571828 | chr2 | 9134330 | 9134569 | chr2 | 9960660 | 9960839 |
| chr2 | 10115632 | 10115739 | chr2 | 10153063 | 10153168 | chr2 | 10153229 | 10153422 |
| chr2 | 10154909 | 10155024 | chr2 | 10155269 | 10155384 | chr2 | 10156334 | 10156493 |
| chr2 | 10182747 | 10182986 | chr2 | 10408310 | 10408347 | chr2 | 10688800 | 10688931 |
| chr2 | 11052419 | 11052658 | chr2 | 11809858 | 11810116 | chr2 | 11810147 | 11810217 |
| chr2 | 12246020 | 12246196 | chr2 | 12858356 | 12858715 | chr2 | 14772673 | 14772888 |
| chr2 | 14774475 | 14774664 | chr2 | 17719601 | 17719900 | chr2 | 18058941 | 18059180 |
| chr2 | 18059692 | 18059931 | chr2 | 19550140 | 19550319 | chr2 | 19551225 | 19551449 |
| chr2 | 19556245 | 19556765 | chr2 | 19556994 | 19557173 | chr2 | 19558744 | 19558983 |
| chr2 | 19561045 | 19561404 | chr2 | 19561422 | 19561473 | chr2 | 19561524 | 19561781 |
| chr2 | 19563277 | 19563516 | chr2 | 20068723 | 20068962 | chr2 | 20442485 | 20442586 |
| chr2 | 20642626 | 20642745 | chr2 | 20865560 | 20865847 | chr2 | 20865849 | 20866022 |
| chr2 | 25391060 | 25391313 | chr2 | 25391586 | 25391825 | chr2 | 25438724 | 25438872 |
| chr2 | 25439139 | 25439356 | chr2 | 26372893 | 26373072 | chr2 | 26395353 | 26395458 |
| chr2 | 26395460 | 26395652 | chr2 | 26401956 | 26402135 | chr2 | 26407744 | 26407922 |
| chr2 | 26521960 | 26522079 | chr2 | 26915682 | 26916067 | chr2 | 26916089 | 26916341 |
| chr2 | 27070250 | 27070489 | chr2 | 27071144 | 27071443 | chr2 | 27072394 | 27072633 |
| chr2 | 27072727 | 27073086 | chr2 | 27578410 | 27578500 | chr2 | 27887451 | 27887630 |
| chr2 | 29033261 | 29033698 | chr2 | 29337988 | 29338052 | chr2 | 29338159 | 29338722 |
| chr2 | 29338810 | 29339067 | chr2 | 30143219 | 30143323 | chr2 | 30143383 | 30143578 |
| chr2 | 30143957 | 30144151 | chr2 | 30144175 | 30144496 | chr2 | 30453619 | 30453654 |
| chr2 | 30453785 | 30454038 | chr2 | 31360210 | 31360590 | chr2 | 31360631 | 31360693 |
| chr2 | 31360695 | 31360756 | chr2 | 31360804 | 31360929 | chr2 | 31361015 | 31361118 |
| chr2 | 31361194 | 31361194 | chr2 | 31361282 | 31361461 | chr2 | 31456606 | 31457131 |
| chr2 | 32504335 | 32504449 | chr2 | 38302176 | 38302188 | chr2 | 38302370 | 38302901 |
| chr2 | 38302949 | 38302955 | chr2 | 38365728 | 38365847 | chr2 | 39187141 | 39187238 |
| chr2 | 39187545 | 39187800 | chr2 | 39892997 | 39893596 | chr2 | 39893897 | 39894136 |
| chr2 | 40678513 | 40678872 | chr2 | 40678945 | 40679086 | chr2 | 40679088 | 40679519 |
| chr2 | 40679521 | 40679605 | chr2 | 40679689 | 40679712 | chr2 | 42274495 | 42274734 |
| chr2 | 42329340 | 42329445 | chr2 | 42329494 | 42329759 | chr2 | 42720185 | 42720447 |
| chr2 | 43019525 | 43019944 | chr2 | 43451819 | 43451846 | chr2 | 43451892 | 43452418 |
| chr2 | 43824034 | 43824132 | chr2 | 44497613 | 44497842 | chr2 | 45028911 | 45029059 |
| chr2 | 45029184 | 45029450 | chr2 | 45029637 | 45029779 | chr2 | 45155039 | 45155211 |
| chr2 | 45155356 | 45155991 | chr2 | 45155993 | 45156812 | chr2 | 45156833 | 45157783 |
| chr2 | 45159873 | 45160352 | chr2 | 45160496 | 45160735 | chr2 | 45161598 | 45162036 |
| chr2 | 45162038 | 45162188 | chr2 | 45162319 | 45162558 | chr2 | 45162653 | 45163012 |

TABLE 15-continued

Pan-cancer #5

| chr | start | end | chr | start | end | chr | start | end |
|---|---|---|---|---|---|---|---|---|
| chr2 | 45164589 | 45164608 | chr2 | 45164657 | 45164768 | chr2 | 45165490 | 45165669 |
| chr2 | 45168857 | 45168908 | chr2 | 45169349 | 45169548 | chr2 | 45169550 | 45170123 |
| chr2 | 45171295 | 45171564 | chr2 | 45171837 | 45171954 | chr2 | 45176506 | 45176865 |
| chr2 | 45179546 | 45179725 | chr2 | 45179862 | 45180156 | chr2 | 45181417 | 45181776 |
| chr2 | 45181795 | 45182094 | chr2 | 45231245 | 45231478 | chr2 | 45231754 | 45232208 |
| chr2 | 45233307 | 45233666 | chr2 | 45235491 | 45236030 | chr2 | 45237585 | 45237689 |
| chr2 | 45237691 | 45237884 | chr2 | 45240491 | 45240631 | chr2 | 45240764 | 45240876 |
| chr2 | 45241041 | 45241169 | chr2 | 45241233 | 45241280 | chr2 | 45395768 | 45396007 |
| chr2 | 45396234 | 45396533 | chr2 | 45396603 | 45397082 | chr2 | 46526226 | 46526331 |
| chr2 | 47193958 | 47194077 | chr2 | 47200517 | 47200696 | chr2 | 47249735 | 47249914 |
| chr2 | 47598298 | 47598477 | chr2 | 47598579 | 47598698 | chr2 | 47748048 | 47748587 |
| chr2 | 47796952 | 47797488 | chr2 | 47797490 | 47797911 | chr2 | 47798093 | 47798752 |
| chr2 | 47798853 | 47799033 | chr2 | 47799124 | 47799212 | chr2 | 48982485 | 48982701 |
| chr2 | 48982754 | 48982964 | chr2 | 50573520 | 50573639 | chr2 | 50573692 | 50573924 |
| chr2 | 50574041 | 50574356 | chr2 | 50574402 | 50574685 | chr2 | 50574739 | 50574940 |
| chr2 | 55289095 | 55289274 | chr2 | 56149762 | 56149941 | chr2 | 56150682 | 56151256 |
| chr2 | 56410918 | 56411087 | chr2 | 56411593 | 56411832 | chr2 | 58655968 | 58656207 |
| chr2 | 60706663 | 60706902 | chr2 | 60796498 | 60796617 | chr2 | 60797060 | 60797359 |
| chr2 | 61135116 | 61135235 | chr2 | 62798248 | 62798447 | chr2 | 63275470 | 63275509 |
| chr2 | 63275878 | 63275949 | chr2 | 63278888 | 63279022 | chr2 | 63280853 | 63281752 |
| chr2 | 63282632 | 63282867 | chr2 | 63283014 | 63283053 | chr2 | 63283870 | 63284229 |
| chr2 | 63284675 | 63284914 | chr2 | 63284996 | 63285799 | chr2 | 63286359 | 63286585 |
| chr2 | 63286694 | 63286748 | chr2 | 63287083 | 63287412 | chr2 | 66652937 | 66653063 |
| chr2 | 66653158 | 66653254 | chr2 | 66653256 | 66653577 | chr2 | 66653690 | 66653934 |
| chr2 | 66660560 | 66660791 | chr2 | 66808447 | 66808634 | chr2 | 66808727 | 66809453 |
| chr2 | 67625373 | 67625492 | chr2 | 67625733 | 67625852 | chr2 | 67626153 | 67626332 |
| chr2 | 68546250 | 68546517 | chr2 | 68546553 | 68546968 | chr2 | 68559344 | 68559463 |
| chr2 | 68672777 | 68672956 | chr2 | 70418609 | 70418722 | chr2 | 71355039 | 71355218 |
| chr2 | 71503688 | 71503927 | chr2 | 71504000 | 71504246 | chr2 | 71680759 | 71680938 |
| chr2 | 71693423 | 71693694 | chr2 | 72374295 | 72374524 | chr2 | 72374611 | 72374690 |
| chr2 | 72374714 | 72374850 | chr2 | 73145548 | 73145787 | chr2 | 73145824 | 73146123 |
| chr2 | 73147245 | 73147528 | chr2 | 73147967 | 73148067 | chr2 | 73148175 | 73148313 |
| chr2 | 73150850 | 73151029 | chr2 | 73151098 | 73151884 | chr2 | 73152600 | 73152679 |
| chr2 | 73152740 | 73152839 | chr2 | 73429420 | 73429719 | chr2 | 73429862 | 73429923 |
| chr2 | 73429977 | 73430161 | chr2 | 73430234 | 73430373 | chr2 | 73430443 | 73430818 |
| chr2 | 73440271 | 73440370 | chr2 | 73518355 | 73519014 | chr2 | 73519501 | 73519920 |
| chr2 | 74010442 | 74010621 | chr2 | 74453989 | 74454348 | chr2 | 74726670 | 74726849 |
| chr2 | 74740761 | 74741136 | chr2 | 74741138 | 74741480 | chr2 | 74741746 | 74741845 |
| chr2 | 74741873 | 74742045 | chr2 | 74742085 | 74742151 | chr2 | 74742325 | 74742648 |
| chr2 | 74742694 | 74743145 | chr2 | 74743767 | 74743824 | chr2 | 74781997 | 74782088 |
| chr2 | 74782219 | 74782356 | chr2 | 75426958 | 75426980 | chr2 | 75427295 | 75427474 |
| chr2 | 75427845 | 75428264 | chr2 | 80529292 | 80529520 | chr2 | 80529573 | 80529909 |
| chr2 | 80529986 | 80530112 | chr2 | 80530413 | 80530587 | chr2 | 80530623 | 80530652 |
| chr2 | 80531651 | 80531830 | chr2 | 80549486 | 80549845 | chr2 | 85107377 | 85107616 |
| chr2 | 85361224 | 85361310 | chr2 | 85361467 | 85361529 | chr2 | 85361629 | 85361703 |
| chr2 | 87016489 | 87016509 | chr2 | 87016576 | 87016728 | chr2 | 87017707 | 87018313 |
| chr2 | 88469219 | 88469398 | chr2 | 88751182 | 88751420 | chr2 | 88751461 | 88751816 |
| chr2 | 88751961 | 88752380 | chr2 | 88752515 | 88752874 | chr2 | 88990108 | 88990347 |
| chr2 | 89064806 | 89064976 | chr2 | 89065129 | 89065364 | chr2 | 95663873 | 95664112 |
| chr2 | 95690654 | 95690890 | chr2 | 95690944 | 95691363 | chr2 | 95691441 | 95691500 |
| chr2 | 95691502 | 95691860 | chr2 | 95691908 | 95692567 | chr2 | 95941596 | 95941895 |
| chr2 | 96990808 | 96991399 | chr2 | 97193003 | 97193064 | chr2 | 97193252 | 97193722 |
| chr2 | 97427415 | 97428194 | chr2 | 98703220 | 98703491 | chr2 | 98962800 | 98962900 |
| chr2 | 98962974 | 98963039 | chr2 | 98963255 | 98963408 | chr2 | 98963410 | 98963674 |
| chr2 | 98963750 | 98963826 | chr2 | 98963869 | 98964289 | chr2 | 98964502 | 98964741 |
| chr2 | 99439369 | 99439593 | chr2 | 99553333 | 99553632 | chr2 | 99796327 | 99796415 |
| chr2 | 99798571 | 99798746 | chr2 | 99799229 | 99799230 | chr2 | 100937747 | 100938210 |
| chr2 | 100938330 | 100938545 | chr2 | 100938575 | 100938799 | chr2 | 100938801 | 100938810 |
| chr2 | 100938985 | 100939246 | chr2 | 101010030 | 101010792 | chr2 | 101034149 | 101034388 |
| chr2 | 101436638 | 101436790 | chr2 | 102091079 | 102091335 | chr2 | 103236080 | 103236277 |
| chr2 | 105459001 | 105459152 | chr2 | 105459903 | 105460263 | chr2 | 105460265 | 105460604 |
| chr2 | 105460847 | 105461026 | chr2 | 105461164 | 105461335 | chr2 | 105461556 | 105461668 |
| chr2 | 105461700 | 105462000 | chr2 | 105462075 | 105462314 | chr2 | 105468701 | 105469000 |
| chr2 | 105469569 | 105469857 | chr2 | 105469881 | 105470168 | chr2 | 105470266 | 105470561 |
| chr2 | 105470563 | 105470925 | chr2 | 105472149 | 105472426 | chr2 | 105472713 | 105472928 |
| chr2 | 105473162 | 105473521 | chr2 | 105478687 | 105479054 | chr2 | 105479056 | 105479166 |
| chr2 | 105480630 | 105480683 | chr2 | 105483568 | 105483807 | chr2 | 105484367 | 105484480 |
| chr2 | 105488348 | 105488527 | chr2 | 105760890 | 105761004 | chr2 | 106060525 | 106060884 |
| chr2 | 106681644 | 106681870 | chr2 | 106681936 | 106681983 | chr2 | 106681985 | 106682175 |
| chr2 | 106730137 | 106730316 | chr2 | 106959289 | 106959648 | chr2 | 106959833 | 106960072 |
| chr2 | 107103778 | 107104017 | chr2 | 107502519 | 107502730 | chr2 | 107502866 | 107502908 |
| chr2 | 107503422 | 107503423 | chr2 | 107503458 | 107503637 | chr2 | 107503802 | 107504101 |
| chr2 | 109335091 | 109335264 | chr2 | 109648002 | 109648301 | chr2 | 109745915 | 109746154 |
| chr2 | 109746204 | 109746388 | chr2 | 109746463 | 109746563 | chr2 | 111875279 | 111875518 |
| chr2 | 112656944 | 112657123 | chr2 | 114256879 | 114257238 | chr2 | 114261200 | 114261559 |
| chr2 | 115918579 | 115918893 | chr2 | 115919338 | 115919425 | chr2 | 115919831 | 115920612 |

TABLE 15-continued

Pan-cancer #5

| chr | start | end | chr | start | end | chr | start | end |
|---|---|---|---|---|---|---|---|---|
| chr2 | 115920614 | 115920618 | chr2 | 118981075 | 118981857 | chr2 | 118981946 | 118982148 |
| chr2 | 118982254 | 118982574 | chr2 | 119067552 | 119068143 | chr2 | 119532059 | 119532358 |
| chr2 | 119566137 | 119566376 | chr2 | 119591259 | 119591558 | chr2 | 119592666 | 119592863 |
| chr2 | 119592923 | 119593464 | chr2 | 119593466 | 119593642 | chr2 | 119599830 | 119600129 |
| chr2 | 119600235 | 119600839 | chr2 | 119600856 | 119600953 | chr2 | 119602515 | 119602630 |
| chr2 | 119602829 | 119603174 | chr2 | 119603946 | 119604093 | chr2 | 119604154 | 119604245 |
| chr2 | 119604711 | 119604933 | chr2 | 119606048 | 119606283 | chr2 | 119606631 | 119606647 |
| chr2 | 119606692 | 119606931 | chr2 | 119607443 | 119607504 | chr2 | 119607848 | 119607933 |
| chr2 | 119610758 | 119610940 | chr2 | 119610999 | 119611057 | chr2 | 119611653 | 119611892 |
| chr2 | 119612250 | 119612429 | chr2 | 119614047 | 119614271 | chr2 | 119614697 | 119614936 |
| chr2 | 119614952 | 119615719 | chr2 | 119616070 | 119616552 | chr2 | 119616782 | 119616960 |
| chr2 | 119914617 | 119914856 | chr2 | 119916525 | 119916687 | chr2 | 120281556 | 120281790 |
| chr2 | 120281849 | 120281901 | chr2 | 120281939 | 120282028 | chr2 | 120979994 | 120980173 |
| chr2 | 120980255 | 120980494 | chr2 | 121200303 | 121200532 | chr2 | 121345007 | 121345169 |
| chr2 | 121411987 | 121412231 | chr2 | 122495323 | 122495490 | chr2 | 124782289 | 124782546 |
| chr2 | 124782596 | 124783195 | chr2 | 127423136 | 127423434 | chr2 | 127428910 | 127429147 |
| chr2 | 127438559 | 127438738 | chr2 | 127782953 | 127783168 | chr2 | 127783170 | 127783360 |
| chr2 | 127863514 | 127863813 | chr2 | 127976391 | 127976750 | chr2 | 128421788 | 128421850 |
| chr2 | 128421891 | 128422027 | chr2 | 128616519 | 128616628 | chr2 | 128847701 | 128847799 |
| chr2 | 130763485 | 130763677 | chr2 | 130971063 | 130971355 | chr2 | 131477742 | 131478023 |
| chr2 | 131594915 | 131594922 | chr2 | 131595094 | 131595970 | chr2 | 131720787 | 131721099 |
| chr2 | 131721438 | 131721585 | chr2 | 131721867 | 131722035 | chr2 | 131792157 | 131792520 |
| chr2 | 131792532 | 131792747 | chr2 | 131792921 | 131793154 | chr2 | 131793188 | 131793236 |
| chr2 | 132088786 | 132088919 | chr2 | 132121566 | 132121618 | chr2 | 132121652 | 132121676 |
| chr2 | 132121678 | 132121823 | chr2 | 132152279 | 132152578 | chr2 | 132182701 | 132183180 |
| chr2 | 132767373 | 132767492 | chr2 | 133014571 | 133014662 | chr2 | 133015300 | 133015419 |
| chr2 | 133062239 | 133062299 | chr2 | 133062362 | 133062478 | chr2 | 133426175 | 133426354 |
| chr2 | 133426561 | 133426776 | chr2 | 137522371 | 137522550 | chr2 | 137523751 | 137523759 |
| chr2 | 139536863 | 139537221 | chr2 | 139537935 | 139537823 | chr2 | 139537851 | 139537954 |
| chr2 | 142887816 | 142887886 | chr2 | 142887888 | 142888149 | chr2 | 142888264 | 142888503 |
| chr2 | 144694272 | 144694515 | chr2 | 144694554 | 144695231 | chr2 | 145273369 | 145273848 |
| chr2 | 145274112 | 145274511 | chr2 | 145274715 | 145274975 | chr2 | 145274977 | 145275314 |
| chr2 | 145282045 | 145282224 | chr2 | 148776713 | 148776876 | chr2 | 149633009 | 149633488 |
| chr2 | 149633646 | 149634065 | chr2 | 149645413 | 149645559 | chr2 | 149645561 | 149645995 |
| chr2 | 151342979 | 151343218 | chr2 | 154333432 | 154333671 | chr2 | 154334170 | 154334450 |
| chr2 | 154334452 | 154334769 | chr2 | 154335185 | 154335355 | chr2 | 154727963 | 154727992 |
| chr2 | 154728245 | 154728441 | chr2 | 154729083 | 154729316 | chr2 | 154729485 | 154729664 |
| chr2 | 155555064 | 155555440 | chr2 | 157176805 | 157176908 | chr2 | 157178158 | 157178165 |
| chr2 | 157178167 | 157178407 | chr2 | 157178637 | 157178809 | chr2 | 160760984 | 160761454 |
| chr2 | 161253375 | 161253554 | chr2 | 162272983 | 162273315 | chr2 | 162273383 | 162274182 |
| chr2 | 162274220 | 162274414 | chr2 | 162274748 | 162274942 | chr2 | 162275055 | 162275227 |
| chr2 | 162275311 | 162275438 | chr2 | 162275473 | 162275887 | chr2 | 162280153 | 162280416 |
| chr2 | 162280741 | 162281050 | chr2 | 162283291 | 162283603 | chr2 | 162283783 | 162284130 |
| chr2 | 164592998 | 164593221 | chr2 | 164593223 | 164593237 | chr2 | 168149978 | 168149991 |
| chr2 | 168149993 | 168150337 | chr2 | 168150669 | 168151028 | chr2 | 170282882 | 170283178 |
| chr2 | 170551654 | 170551866 | chr2 | 170681792 | 170681909 | chr2 | 170682152 | 170682329 |
| chr2 | 171569986 | 171570062 | chr2 | 171570182 | 171570190 | chr2 | 171570471 | 171570525 |
| chr2 | 171570590 | 171570829 | chr2 | 171571171 | 171571342 | chr2 | 171571379 | 171571410 |
| chr2 | 171571800 | 171571997 | chr2 | 171670259 | 171670447 | chr2 | 171670472 | 171670558 |
| chr2 | 171671385 | 171671790 | chr2 | 171671800 | 171671984 | chr2 | 171674001 | 171674026 |
| chr2 | 171674664 | 171675143 | chr2 | 171675268 | 171675383 | chr2 | 171675523 | 171675687 |
| chr2 | 171676590 | 171676787 | chr2 | 171676858 | 171676885 | chr2 | 171822419 | 171822574 |
| chr2 | 172366939 | 172367178 | chr2 | 172411062 | 172411241 | chr2 | 172945027 | 172945266 |
| chr2 | 172945642 | 172946294 | chr2 | 172947684 | 172947914 | chr2 | 172948184 | 172948406 |
| chr2 | 172948813 | 172948850 | chr2 | 172949090 | 172949283 | chr2 | 172949349 | 172949809 |
| chr2 | 172951494 | 172951543 | chr2 | 172952425 | 172952640 | chr2 | 172952685 | 172952882 |
| chr2 | 172952993 | 172953096 | chr2 | 172953125 | 172953144 | chr2 | 172955346 | 172955403 |
| chr2 | 172955472 | 172955645 | chr2 | 172957808 | 172958157 | chr2 | 172961319 | 172961678 |
| chr2 | 172964743 | 172964889 | chr2 | 172965296 | 172965299 | chr2 | 172965648 | 172965763 |
| chr2 | 172966174 | 172966533 | chr2 | 172972648 | 172972891 | chr2 | 172972931 | 172973307 |
| chr2 | 173099710 | 173099889 | chr2 | 173100167 | 173100506 | chr2 | 173422651 | 173422770 |
| chr2 | 175190771 | 175191973 | chr2 | 175192085 | 175192550 | chr2 | 175193187 | 175193377 |
| chr2 | 175193379 | 175193645 | chr2 | 175193809 | 175193906 | chr2 | 175195785 | 175195859 |
| chr2 | 175196355 | 175196371 | chr2 | 175196426 | 175196654 | chr2 | 175197015 | 175197194 |
| chr2 | 175199432 | 175199555 | chr2 | 175199922 | 175200012 | chr2 | 175200093 | 175200441 |
| chr2 | 175200710 | 175200853 | chr2 | 175200917 | 175201183 | chr2 | 175201360 | 175201542 |
| chr2 | 175201776 | 175201829 | chr2 | 175202127 | 175202246 | chr2 | 175202569 | 175202601 |
| chr2 | 175202634 | 175202746 | chr2 | 175204100 | 175204279 | chr2 | 175204694 | 175204947 |
| chr2 | 175206752 | 175206906 | chr2 | 175206961 | 175207111 | chr2 | 175207154 | 175207333 |
| chr2 | 175207446 | 175207745 | chr2 | 175208214 | 175208869 | chr2 | 175208997 | 175209218 |
| chr2 | 175546942 | 175547241 | chr2 | 175547310 | 175547489 | chr2 | 176940092 | 176940391 |
| chr2 | 176943180 | 176943659 | chr2 | 176943763 | 176943863 | chr2 | 176943995 | 176944002 |
| chr2 | 176944326 | 176944405 | chr2 | 176944457 | 176944847 | chr2 | 176945138 | 176945269 |
| chr2 | 176945582 | 176945885 | chr2 | 176946475 | 176946868 | chr2 | 176947285 | 176947494 |
| chr2 | 176947647 | 176947654 | chr2 | 176947764 | 176947940 | chr2 | 176947942 | 176948006 |
| chr2 | 176948522 | 176948821 | chr2 | 176948971 | 176949150 | chr2 | 176949603 | 176949962 |

TABLE 15-continued

Pan-cancer #5

| chr | start | end | chr | start | end | chr | start | end |
|---|---|---|---|---|---|---|---|---|
| chr2 | 176950075 | 176950350 | chr2 | 176956929 | 176957300 | chr2 | 176957409 | 176957415 |
| chr2 | 176957577 | 176957629 | chr2 | 176957915 | 176958008 | chr2 | 176958045 | 176958584 |
| chr2 | 176959191 | 176959589 | chr2 | 176963366 | 176963605 | chr2 | 176963999 | 176964150 |
| chr2 | 176964180 | 176964238 | chr2 | 176964272 | 176964334 | chr2 | 176964390 | 176964768 |
| chr2 | 176965265 | 176965591 | chr2 | 176969387 | 176969614 | chr2 | 176969677 | 176969984 |
| chr2 | 176975946 | 176976289 | chr2 | 176980649 | 176980938 | chr2 | 176981377 | 176981592 |
| chr2 | 176982518 | 176982726 | chr2 | 176986712 | 176986932 | chr2 | 176986962 | 176987215 |
| chr2 | 176993462 | 176994380 | chr2 | 176994498 | 176994622 | chr2 | 176995071 | 176995270 |
| chr2 | 176995332 | 176995712 | chr2 | 177001000 | 177001058 | chr2 | 177001118 | 177001263 |
| chr2 | 177001265 | 177001696 | chr2 | 177001782 | 177002079 | chr2 | 177004463 | 177004498 |
| chr2 | 177004556 | 177004762 | chr2 | 177042914 | 177042999 | chr2 | 177043267 | 177043610 |
| chr2 | 177053187 | 177053435 | chr2 | 177053619 | 177053703 | chr2 | 177054023 | 177054442 |
| chr2 | 177502981 | 177503153 | chr2 | 178972904 | 178973143 | chr2 | 179317039 | 179317139 |
| chr2 | 182321308 | 182321727 | chr2 | 182321736 | 182321838 | chr2 | 182322039 | 182322192 |
| chr2 | 182322400 | 182323131 | chr2 | 182542829 | 182542864 | chr2 | 182542866 | 182543008 |
| chr2 | 182543221 | 182543413 | chr2 | 182543666 | 182544025 | chr2 | 182545124 | 182545363 |
| chr2 | 182545438 | 182545797 | chr2 | 182545887 | 182545948 | chr2 | 182546002 | 182546179 |
| chr2 | 182546361 | 182546535 | chr2 | 182547290 | 182547388 | chr2 | 182547438 | 182547709 |
| chr2 | 182547840 | 182547932 | chr2 | 182548062 | 182548259 | chr2 | 182548992 | 182549026 |
| chr2 | 182549038 | 182549231 | chr2 | 182549247 | 182549546 | chr2 | 182550054 | 182550199 |
| chr2 | 182819031 | 182819312 | chr2 | 183731200 | 183731332 | chr2 | 183731467 | 183731619 |
| chr2 | 183731734 | 183732153 | chr2 | 185462776 | 185463075 | chr2 | 185463116 | 185463895 |
| chr2 | 186603414 | 186603593 | chr2 | 188418947 | 188419178 | chr2 | 189157513 | 189157692 |
| chr2 | 193058947 | 193059318 | chr2 | 193059345 | 193059549 | chr2 | 193059662 | 193059717 |
| chr2 | 193059719 | 193060146 | chr2 | 193060294 | 193060533 | chr2 | 193060608 | 193060967 |
| chr2 | 193061341 | 193061580 | chr2 | 198456572 | 198456690 | chr2 | 200326551 | 200326730 |
| chr2 | 200326765 | 200326813 | chr2 | 200327187 | 200327254 | chr2 | 200327424 | 200327452 |
| chr2 | 200327576 | 200327666 | chr2 | 200328669 | 200328685 | chr2 | 200329030 | 200329394 |
| chr2 | 200329433 | 200329748 | chr2 | 200333686 | 200333759 | chr2 | 200333801 | 200333925 |
| chr2 | 200334895 | 200335308 | chr2 | 200335363 | 200335452 | chr2 | 200335592 | 200336034 |
| chr2 | 201450453 | 201450743 | chr2 | 201450745 | 201450812 | chr2 | 201450845 | 201450922 |
| chr2 | 201451014 | 201451144 | chr2 | 202096992 | 202097231 | chr2 | 202899788 | 202899967 |
| chr2 | 206550978 | 206551015 | chr2 | 206551072 | 206551363 | chr2 | 206551451 | 206551457 |
| chr2 | 207138998 | 207139155 | chr2 | 207139267 | 207139686 | chr2 | 207307426 | 207307478 |
| chr2 | 207307548 | 207307665 | chr2 | 207308711 | 207308950 | chr2 | 207506612 | 207507266 |
| chr2 | 208635519 | 208635864 | chr2 | 209113024 | 209113202 | chr2 | 209225137 | 209225376 |
| chr2 | 209271228 | 209271337 | chr2 | 210636255 | 210636382 | chr2 | 210636430 | 210636690 |
| chr2 | 210636738 | 210636877 | chr2 | 210636934 | 210636974 | chr2 | 213401138 | 213401437 |
| chr2 | 213401511 | 213401565 | chr2 | 213401567 | 213402050 | chr2 | 213403015 | 213403434 |
| chr2 | 217559222 | 217559401 | chr2 | 218806046 | 218806405 | chr2 | 219736062 | 219736705 |
| chr2 | 219827964 | 219827975 | chr2 | 219847360 | 219847659 | chr2 | 219848726 | 219848892 |
| chr2 | 219848936 | 219849085 | chr2 | 219857648 | 219857738 | chr2 | 219857781 | 219857860 |
| chr2 | 220080582 | 220080941 | chr2 | 220173904 | 220174037 | chr2 | 220174060 | 220174383 |
| chr2 | 220196266 | 220196671 | chr2 | 220223024 | 220223203 | chr2 | 220223557 | 220223700 |
| chr2 | 220223795 | 220223796 | chr2 | 220283250 | 220283290 | chr2 | 220283363 | 220283609 |
| chr2 | 220299495 | 220299635 | chr2 | 220299886 | 220300154 | chr2 | 220348949 | 220348984 |
| chr2 | 220349055 | 220349788 | chr2 | 220361370 | 220361467 | chr2 | 220416297 | 220416596 |
| chr2 | 220416770 | 220417729 | chr2 | 222435699 | 222435857 | chr2 | 223155678 | 223156277 |
| chr2 | 223158648 | 223159542 | chr2 | 223159735 | 223159806 | chr2 | 223159869 | 223160154 |
| chr2 | 223160251 | 223160481 | chr2 | 223161173 | 223161352 | chr2 | 223161452 | 223161685 |
| chr2 | 223161807 | 223162165 | chr2 | 223162678 | 223162891 | chr2 | 223162929 | 223163225 |
| chr2 | 223163473 | 223163637 | chr2 | 223163682 | 223163809 | chr2 | 223163811 | 223164034 |
| chr2 | 223164440 | 223164617 | chr2 | 223165334 | 223165503 | chr2 | 223166190 | 223166226 |
| chr2 | 223166294 | 223166825 | chr2 | 223167302 | 223167661 | chr2 | 223168346 | 223168832 |
| chr2 | 223168917 | 223168945 | chr2 | 223169543 | 223169962 | chr2 | 223170286 | 223170525 |
| chr2 | 223171026 | 223171265 | chr2 | 223172959 | 223173259 | chr2 | 223176018 | 223176282 |
| chr2 | 223176361 | 223176512 | chr2 | 223176720 | 223177080 | chr2 | 223177245 | 223177703 |
| chr2 | 228029326 | 228029351 | chr2 | 228029373 | 228029625 | chr2 | 228466762 | 228466881 |
| chr2 | 228735702 | 228735828 | chr2 | 228736135 | 228736296 | chr2 | 228736336 | 228736554 |
| chr2 | 229046024 | 229046605 | chr2 | 230795461 | 230795640 | chr2 | 232394867 | 232395022 |
| chr2 | 232395055 | 232395166 | chr2 | 232791619 | 232792098 | chr2 | 233350112 | 233350540 |
| chr2 | 233350844 | 233351279 | chr2 | 233351416 | 233351491 | chr2 | 233351930 | 233352007 |
| chr2 | 233352102 | 233352452 | chr2 | 233352507 | 233352763 | chr2 | 233352776 | 233352949 |
| chr2 | 233498615 | 233498874 | chr2 | 233498896 | 233499345 | chr2 | 233499386 | 233499394 |
| chr2 | 233750451 | 233750630 | chr2 | 235404471 | 235404533 | chr2 | 235404551 | 235404590 |
| chr2 | 235860803 | 235860897 | chr2 | 236402683 | 236402901 | chr2 | 236403060 | 236403102 |
| chr2 | 236403174 | 236403419 | chr2 | 236403779 | 236403833 | chr2 | 236877188 | 236877367 |
| chr2 | 237072642 | 237072998 | chr2 | 237073000 | 237073015 | chr2 | 237073057 | 237073112 |
| chr2 | 237073265 | 237073496 | chr2 | 237076657 | 237076833 | chr2 | 237077466 | 237077685 |
| chr2 | 237077815 | 237078054 | chr2 | 237078097 | 237078427 | chr2 | 237080190 | 237080369 |
| chr2 | 237081255 | 237081427 | chr2 | 237081537 | 237081554 | chr2 | 237082344 | 237082809 |
| chr2 | 237086291 | 237086398 | chr2 | 237086400 | 237086559 | chr2 | 237145333 | 237145437 |
| chr2 | 237145439 | 237145692 | chr2 | 237416114 | 237416504 | chr2 | 238395205 | 238395444 |
| chr2 | 238395815 | 238395988 | chr2 | 238535876 | 238535985 | chr2 | 238536005 | 238536215 |
| chr2 | 238864570 | 238864631 | chr2 | 238864727 | 238864989 | chr2 | 239051124 | 239051303 |
| chr2 | 239140139 | 239140347 | chr2 | 239265703 | 239265881 | chr2 | 239482400 | 239482622 |

TABLE 15-continued

Pan-cancer #5

| chr | start | end | chr | start | end | chr | start | end |
|---|---|---|---|---|---|---|---|---|
| chr2 | 239705202 | 239705364 | chr2 | 239755090 | 239755198 | chr2 | 239755638 | 239755654 |
| chr2 | 239756347 | 239756463 | chr2 | 239756488 | 239756586 | chr2 | 239757551 | 239757731 |
| chr2 | 239757899 | 239757910 | chr2 | 239757992 | 239758061 | chr2 | 239758126 | 239758231 |
| chr2 | 239758251 | 239758490 | chr2 | 239957240 | 239957539 | chr2 | 240168722 | 240169141 |
| chr2 | 240319908 | 240320087 | chr2 | 240582303 | 240582448 | chr2 | 240619443 | 240619682 |
| chr2 | 240658145 | 240658504 | chr2 | 240658593 | 240658772 | chr2 | 241095576 | 241095868 |
| chr2 | 241393126 | 241393167 | chr2 | 241393199 | 241393545 | chr2 | 241542045 | 241542344 |
| chr2 | 241544927 | 241545106 | chr2 | 241758299 | 241758898 | chr2 | 241759497 | 241759796 |
| chr2 | 241760075 | 241760254 | chr2 | 241760420 | 241760599 | chr2 | 241771062 | 241771361 |
| chr2 | 241865091 | 241865450 | chr2 | 242009317 | 242009496 | chr2 | 242021689 | 242021916 |
| chr2 | 242523873 | 242524172 | chr2 | 242549754 | 242549772 | chr2 | 242549918 | 242550053 |
| chr2 | 242554475 | 242554654 | chr2 | 242756042 | 242756401 | chr2 | 242832893 | 242833252 |
| chr2 | 242833484 | 242833663 | chr2 | 242833711 | 242833930 | chr2 | 242836419 | 242836718 |
| chr2 | 242925420 | 242925719 | chr3 | 238456 | 238716 | chr3 | 239007 | 239126 |
| chr3 | 239159 | 239175 | chr3 | 239534 | 239869 | chr3 | 240110 | 240313 |
| chr3 | 2140189 | 2140435 | chr3 | 3840419 | 3840838 | chr3 | 3840946 | 3841245 |
| chr3 | 3842586 | 3842689 | chr3 | 5137871 | 5138109 | chr3 | 6902228 | 6902441 |
| chr3 | 6903500 | 6903564 | chr3 | 8810152 | 8810298 | chr3 | 9178065 | 9178130 |
| chr3 | 9593878 | 9594117 | chr3 | 9594286 | 9594473 | chr3 | 9595199 | 9595199 |
| chr3 | 9595396 | 9595503 | chr3 | 9595599 | 9595678 | chr3 | 9904155 | 9904634 |
| chr3 | 9941391 | 9941509 | chr3 | 9956984 | 9957223 | chr3 | 9957355 | 9957774 |
| chr3 | 10182757 | 10182917 | chr3 | 10183247 | 10183396 | chr3 | 10183632 | 10183811 |
| chr3 | 10858055 | 10858123 | chr3 | 11034163 | 11034462 | chr3 | 11034991 | 11035353 |
| chr3 | 11035383 | 11035410 | chr3 | 12046310 | 12046353 | chr3 | 12046378 | 12046727 |
| chr3 | 12917751 | 12917751 | chr3 | 12976987 | 12977150 | chr3 | 13323405 | 13324029 |
| chr3 | 13324277 | 13324348 | chr3 | 13324420 | 13324516 | chr3 | 13324744 | 13325023 |
| chr3 | 13590341 | 13590414 | chr3 | 13590448 | 13590641 | chr3 | 13679082 | 13679441 |
| chr3 | 13921316 | 13921555 | chr3 | 14851755 | 14851994 | chr3 | 14852233 | 14852659 |
| chr3 | 14852661 | 14853012 | chr3 | 16553963 | 16554202 | chr3 | 16554251 | 16554466 |
| chr3 | 16554468 | 16554730 | chr3 | 17001229 | 17001341 | chr3 | 19189367 | 19189546 |
| chr3 | 19189611 | 19189850 | chr3 | 19190061 | 19190253 | chr3 | 22413591 | 22413770 |
| chr3 | 22413871 | 22413911 | chr3 | 22413960 | 22414050 | chr3 | 24870915 | 24870925 |
| chr3 | 24870982 | 24871177 | chr3 | 24871246 | 24871281 | chr3 | 25469303 | 25469402 |
| chr3 | 25469404 | 25469482 | chr3 | 25469605 | 25469784 | chr3 | 26663963 | 26664202 |
| chr3 | 26664303 | 26664842 | chr3 | 27754404 | 27754583 | chr3 | 27762260 | 27762733 |
| chr3 | 27762783 | 27762962 | chr3 | 27763492 | 27763671 | chr3 | 27764421 | 27764472 |
| chr3 | 27764596 | 27764600 | chr3 | 27765085 | 27765362 | chr3 | 27765401 | 27765444 |
| chr3 | 27771422 | 27772081 | chr3 | 28616745 | 28617764 | chr3 | 32858274 | 32858959 |
| chr3 | 32859256 | 32859285 | chr3 | 32859418 | 32859773 | chr3 | 32859992 | 32860306 |
| chr3 | 33259801 | 33260876 | chr3 | 35680815 | 35680947 | chr3 | 36805720 | 36805959 |
| chr3 | 36806053 | 36806130 | chr3 | 36806179 | 36806292 | chr3 | 37493429 | 37493720 |
| chr3 | 37901952 | 37902028 | chr3 | 38030610 | 38030789 | chr3 | 38032257 | 38032436 |
| chr3 | 38035774 | 38036088 | chr3 | 38080596 | 38081009 | chr3 | 38081154 | 38081286 |
| chr3 | 38081339 | 38081360 | chr3 | 38690527 | 38690766 | chr3 | 38691469 | 38691557 |
| chr3 | 39851674 | 39851913 | chr3 | 41266012 | 41266239 | chr3 | 42222640 | 42222737 |
| chr3 | 42640761 | 42640874 | chr3 | 42814467 | 42814706 | chr3 | 42947333 | 42947762 |
| chr3 | 44036176 | 44036415 | chr3 | 44036496 | 44036675 | chr3 | 44036743 | 44037128 |
| chr3 | 44037130 | 44037282 | chr3 | 44037525 | 44037764 | chr3 | 44037781 | 44038740 |
| chr3 | 44039265 | 44040026 | chr3 | 44040057 | 44040097 | chr3 | 44040413 | 44040652 |
| chr3 | 44040709 | 44041128 | chr3 | 44063354 | 44063953 | chr3 | 44596405 | 44596584 |
| chr3 | 44596614 | 44596913 | chr3 | 44626336 | 44626538 | chr3 | 44626540 | 44626815 |
| chr3 | 44726855 | 44727069 | chr3 | 44727071 | 44727274 | chr3 | 45187222 | 45187328 |
| chr3 | 46924905 | 46925039 | chr3 | 48227686 | 48227788 | chr3 | 48236391 | 48236553 |
| chr3 | 48693228 | 48693701 | chr3 | 48693852 | 48693882 | chr3 | 48693884 | 48694155 |
| chr3 | 48694227 | 48694247 | chr3 | 48698723 | 48699011 | chr3 | 48699377 | 48699859 |
| chr3 | 49906993 | 49907232 | chr3 | 49939836 | 49940495 | chr3 | 50243283 | 50243582 |
| chr3 | 50374581 | 50374760 | chr3 | 50374843 | 50375022 | chr3 | 50375104 | 50375639 |
| chr3 | 50395432 | 50395611 | chr3 | 50402078 | 50403037 | chr3 | 50575518 | 50575635 |
| chr3 | 52552500 | 52552739 | chr3 | 52553395 | 52553537 | chr3 | 53032708 | 53033609 |
| chr3 | 54155525 | 54155764 | chr3 | 54157297 | 54157536 | chr3 | 54157780 | 54158006 |
| chr3 | 55519117 | 55519228 | chr3 | 55523019 | 55523318 | chr3 | 62353291 | 62354130 |
| chr3 | 62354187 | 62354385 | chr3 | 62354531 | 62354793 | chr3 | 62354900 | 62355010 |
| chr3 | 62355332 | 62355571 | chr3 | 62355692 | 62356220 | chr3 | 62356367 | 62356645 |
| chr3 | 62356793 | 62357193 | chr3 | 62357279 | 62357431 | chr3 | 62357527 | 62357671 |
| chr3 | 62357736 | 62357766 | chr3 | 62358059 | 62358117 | chr3 | 62358444 | 62358683 |
| chr3 | 62358758 | 62359115 | chr3 | 62359276 | 62359392 | chr3 | 62359394 | 62359995 |
| chr3 | 62360222 | 62360641 | chr3 | 62362817 | 62362917 | chr3 | 62363099 | 62363206 |
| chr3 | 62363541 | 62363780 | chr3 | 62363819 | 62364177 | chr3 | 62364280 | 62364418 |
| chr3 | 62364659 | 62365205 | chr3 | 62861044 | 62861142 | chr3 | 62861144 | 62861223 |
| chr3 | 63264065 | 63264135 | chr3 | 63264158 | 63264244 | chr3 | 68056816 | 68057235 |
| chr3 | 68980843 | 68980947 | chr3 | 68980949 | 68981202 | chr3 | 68981469 | 68981708 |
| chr3 | 69590865 | 69591044 | chr3 | 69591311 | 69591415 | chr3 | 69591780 | 69591978 |
| chr3 | 69592069 | 69592163 | chr3 | 69741004 | 69741087 | chr3 | 69937792 | 69937926 |
| chr3 | 71802489 | 71802594 | chr3 | 71802596 | 71802720 | chr3 | 71803040 | 71803459 |
| chr3 | 71803553 | 71803558 | chr3 | 71803560 | 71803784 | chr3 | 71803827 | 71803912 |
| chr3 | 73045525 | 73045672 | chr3 | 75955924 | 75955997 | chr3 | 75956027 | 75956463 |

TABLE 15-continued

Pan-cancer #5

| chr | start | end | chr | start | end | chr | start | end |
|---|---|---|---|---|---|---|---|---|
| chr3 | 79815421 | 79815660 | chr3 | 79816688 | 79817099 | chr3 | 79817214 | 79817393 |
| chr3 | 85008452 | 85008726 | chr3 | 85008803 | 85008811 | chr3 | 88248026 | 88248142 |
| chr3 | 96532726 | 96532965 | chr3 | 96533302 | 96533541 | chr3 | 96533947 | 96534186 |
| chr3 | 98620817 | 98621056 | chr3 | 99594836 | 99595195 | chr3 | 101230575 | 101230641 |
| chr3 | 101230942 | 101231174 | chr3 | 101397150 | 101397302 | chr3 | 106936068 | 106936294 |
| chr3 | 112052411 | 112052521 | chr3 | 117715472 | 117715643 | chr3 | 117715772 | 117716124 |
| chr3 | 117716214 | 117716312 | chr3 | 117716314 | 117716551 | chr3 | 120003954 | 120004036 |
| chr3 | 120004080 | 120004438 | chr3 | 120169683 | 120169922 | chr3 | 120627319 | 120627535 |
| chr3 | 121902878 | 121902950 | chr3 | 121902991 | 121903219 | chr3 | 121903324 | 121903717 |
| chr3 | 122234151 | 122234246 | chr3 | 122702194 | 122702430 | chr3 | 123166972 | 123167006 |
| chr3 | 123167301 | 123167631 | chr3 | 123167679 | 123167918 | chr3 | 125898567 | 125899292 |
| chr3 | 125899445 | 125899706 | chr3 | 125899740 | 125899925 | chr3 | 125899927 | 125899979 |
| chr3 | 125932169 | 125932586 | chr3 | 126373433 | 126373619 | chr3 | 126373669 | 126373792 |
| chr3 | 126854599 | 126854898 | chr3 | 127534879 | 127534976 | chr3 | 127634112 | 127634291 |
| chr3 | 127794464 | 127794943 | chr3 | 127795248 | 127795253 | chr3 | 128202373 | 128202552 |
| chr3 | 128208829 | 128209308 | chr3 | 128273913 | 128274052 | chr3 | 128274309 | 128274655 |
| chr3 | 128417127 | 128417306 | chr3 | 128719977 | 128720143 | chr3 | 128720164 | 128720347 |
| chr3 | 128720419 | 128720534 | chr3 | 128720567 | 128720696 | chr3 | 128720780 | 128720884 |
| chr3 | 128720886 | 128721319 | chr3 | 128764472 | 128764607 | chr3 | 129693075 | 129693200 |
| chr3 | 129693305 | 129693499 | chr3 | 129693955 | 129694347 | chr3 | 130064351 | 130064588 |
| chr3 | 130064781 | 130064923 | chr3 | 130235952 | 130236064 | chr3 | 130236174 | 130236298 |
| chr3 | 130519821 | 130519929 | chr3 | 131753957 | 131754136 | chr3 | 132756966 | 132757205 |
| chr3 | 133217923 | 133218102 | chr3 | 133748044 | 133748206 | chr3 | 133748552 | 133748679 |
| chr3 | 134369572 | 134369919 | chr3 | 134369921 | 134369931 | chr3 | 134514792 | 134514879 |
| chr3 | 134514960 | 134514971 | chr3 | 134515040 | 134515459 | chr3 | 134515590 | 134516309 |
| chr3 | 136537567 | 136537806 | chr3 | 136538520 | 136538910 | chr3 | 136582941 | 136583037 |
| chr3 | 136751546 | 136751833 | chr3 | 137479149 | 137479388 | chr3 | 137479525 | 137479764 |
| chr3 | 137479893 | 137480847 | chr3 | 137481094 | 137481393 | chr3 | 137481782 | 137481873 |
| chr3 | 137481936 | 137482261 | chr3 | 137483212 | 137483319 | chr3 | 137483570 | 137483691 |
| chr3 | 137483746 | 137484026 | chr3 | 137484085 | 137484105 | chr3 | 137484319 | 137484618 |
| chr3 | 137485931 | 137486390 | chr3 | 137486429 | 137486653 | chr3 | 137487874 | 137488004 |
| chr3 | 137488091 | 137488113 | chr3 | 137488856 | 137489699 | chr3 | 137489876 | 137491135 |
| chr3 | 138153889 | 138154068 | chr3 | 138154240 | 138154277 | chr3 | 138655857 | 138656216 |
| chr3 | 138656743 | 138656982 | chr3 | 138657347 | 138657495 | chr3 | 138657618 | 138658297 |
| chr3 | 138658704 | 138658864 | chr3 | 138659081 | 138659187 | chr3 | 138662060 | 138662180 |
| chr3 | 138662282 | 138662535 | chr3 | 138662705 | 138662941 | chr3 | 138663611 | 138663728 |
| chr3 | 138664142 | 138664249 | chr3 | 138664330 | 138664383 | chr3 | 138664827 | 138665336 |
| chr3 | 138665397 | 138665426 | chr3 | 138665479 | 138665528 | chr3 | 138665540 | 138665718 |
| chr3 | 138665779 | 138666378 | chr3 | 138668646 | 138668685 | chr3 | 138668758 | 138669109 |
| chr3 | 138669141 | 138669485 | chr3 | 138679566 | 138679614 | chr3 | 139258173 | 139258412 |
| chr3 | 139653413 | 139653573 | chr3 | 139653575 | 139653772 | chr3 | 140769430 | 140769789 |
| chr3 | 140769830 | 140770302 | chr3 | 140770408 | 140770590 | chr3 | 140770644 | 140770683 |
| chr3 | 140770685 | 140770909 | chr3 | 140771231 | 140771410 | chr3 | 140771716 | 140771955 |
| chr3 | 141174269 | 141174688 | chr3 | 141481983 | 141482162 | chr3 | 141516315 | 141516794 |
| chr3 | 142682184 | 142682483 | chr3 | 142791076 | 142791173 | chr3 | 142837906 | 142838319 |
| chr3 | 142838530 | 142838647 | chr3 | 142838877 | 142839073 | chr3 | 142839439 | 142839526 |
| chr3 | 142839563 | 142839578 | chr3 | 142839580 | 142839689 | chr3 | 142839784 | 142839902 |
| chr3 | 142839945 | 142839991 | chr3 | 142839993 | 142840128 | chr3 | 142840222 | 142840338 |
| chr3 | 142896066 | 142896305 | chr3 | 145878591 | 145878641 | chr3 | 146187843 | 146188069 |
| chr3 | 147074871 | 147075110 | chr3 | 147077211 | 147077366 | chr3 | 147078865 | 147079284 |
| chr3 | 147087472 | 147087891 | chr3 | 147088363 | 147088542 | chr3 | 147088840 | 147089136 |
| chr3 | 147098332 | 147098571 | chr3 | 147105805 | 147106104 | chr3 | 147108758 | 147109766 |
| chr3 | 147110011 | 147110017 | chr3 | 147110055 | 147110115 | chr3 | 147110229 | 147110774 |
| chr3 | 147110835 | 147111188 | chr3 | 147111703 | 147111734 | chr3 | 147126963 | 147127142 |
| chr3 | 147127677 | 147127913 | chr3 | 147136839 | 147137001 | chr3 | 147137076 | 147137258 |
| chr3 | 147138694 | 147138932 | chr3 | 147139272 | 147139631 | chr3 | 147142126 | 147142152 |
| chr3 | 148415327 | 148415746 | chr3 | 148803259 | 148803370 | chr3 | 149374866 | 149375105 |
| chr3 | 150802882 | 150803000 | chr3 | 150803026 | 150803181 | chr3 | 150803941 | 150804180 |
| chr3 | 150804880 | 150804896 | chr3 | 150804937 | 150805119 | chr3 | 152553245 | 152553484 |
| chr3 | 152553573 | 152553807 | chr3 | 152877592 | 152877703 | chr3 | 153838725 | 153838964 |
| chr3 | 153839429 | 153839559 | chr3 | 153839641 | 153839953 | chr3 | 154146034 | 154146395 |
| chr3 | 154146489 | 154146513 | chr3 | 154146572 | 154146991 | chr3 | 154797250 | 154797289 |
| chr3 | 154797377 | 154797778 | chr3 | 156008943 | 156009300 | chr3 | 156009319 | 156009501 |
| chr3 | 156534393 | 156534407 | chr3 | 157155164 | 157155523 | chr3 | 157155922 | 157156298 |
| chr3 | 157812122 | 157812258 | chr3 | 157812437 | 157812721 | chr3 | 157812812 | 157813171 |
| chr3 | 157813507 | 157813605 | chr3 | 157813670 | 157813926 | chr3 | 157815787 | 157815920 |
| chr3 | 157820502 | 157820681 | chr3 | 157821537 | 157821764 | chr3 | 157821939 | 157822106 |
| chr3 | 157823012 | 157823120 | chr3 | 157823139 | 157823228 | chr3 | 157823390 | 157823569 |
| chr3 | 157824052 | 157824147 | chr3 | 157824212 | 157824332 | chr3 | 157824414 | 157824909 |
| chr3 | 157825083 | 157825491 | chr3 | 158288801 | 158288819 | chr3 | 158288887 | 158288974 |
| chr3 | 159756593 | 159756952 | chr3 | 159944397 | 159944636 | chr3 | 160167929 | 160167989 |
| chr3 | 160168071 | 160168108 | chr3 | 164912329 | 164912568 | chr3 | 164912827 | 164913960 |
| chr3 | 164914906 | 164915205 | chr3 | 169376080 | 169376319 | chr3 | 169376581 | 169376878 |
| chr3 | 169539810 | 169540704 | chr3 | 169540967 | 169541134 | chr3 | 170136540 | 170136839 |
| chr3 | 170302528 | 170302767 | chr3 | 170302989 | 170303143 | chr3 | 170303380 | 170303495 |
| chr3 | 170303563 | 170303922 | chr3 | 171527953 | 171528071 | chr3 | 172165356 | 172165785 |

TABLE 15-continued

Pan-cancer #5

| chr | start | end | chr | start | end | chr | start | end |
|---|---|---|---|---|---|---|---|---|
| chr3 | 172165867 | 172166234 | chr3 | 172166236 | 172166513 | chr3 | 172166673 | 172166725 |
| chr3 | 172166783 | 172166894 | chr3 | 172167000 | 172167142 | chr3 | 172167223 | 172167402 |
| chr3 | 172167596 | 172167995 | chr3 | 172355818 | 172355888 | chr3 | 172355903 | 172355997 |
| chr3 | 172425281 | 172425382 | chr3 | 172425701 | 172425802 | chr3 | 172469837 | 172469951 |
| chr3 | 173115155 | 173115634 | chr3 | 173302464 | 173302669 | chr3 | 173302735 | 173302763 |
| chr3 | 173302900 | 173303319 | chr3 | 178861414 | 178861533 | chr3 | 178916788 | 178916967 |
| chr3 | 178921465 | 178921644 | chr3 | 178935968 | 178936205 | chr3 | 178951997 | 178952176 |
| chr3 | 179168582 | 179169354 | chr3 | 179754086 | 179754193 | chr3 | 179754239 | 179754483 |
| chr3 | 179754485 | 179754760 | chr3 | 179754804 | 179754873 | chr3 | 179755087 | 179755465 |
| chr3 | 181413068 | 181413069 | chr3 | 181413422 | 181413460 | chr3 | 181413647 | 181414426 |
| chr3 | 181419972 | 181420211 | chr3 | 181420226 | 181420465 | chr3 | 181421308 | 181422387 |
| chr3 | 181422464 | 181423063 | chr3 | 181428311 | 181428850 | chr3 | 181430614 | 181430853 |
| chr3 | 181437030 | 181437299 | chr3 | 181437301 | 181437449 | chr3 | 181438095 | 181438454 |
| chr3 | 181440811 | 181442010 | chr3 | 181442069 | 181442426 | chr3 | 181442964 | 181443550 |
| chr3 | 181444051 | 181444322 | chr3 | 181444335 | 181444525 | chr3 | 181444613 | 181444754 |
| chr3 | 181444828 | 181444949 | chr3 | 181444989 | 181444989 | chr3 | 181444991 | 181445114 |
| chr3 | 181445268 | 181445567 | chr3 | 181445649 | 181445725 | chr3 | 181445800 | 181445948 |
| chr3 | 182816010 | 182816129 | chr3 | 182895871 | 182895990 | chr3 | 183145336 | 183145695 |
| chr3 | 183145829 | 183146128 | chr3 | 183146297 | 183146536 | chr3 | 183146574 | 183146753 |
| chr3 | 183648036 | 183648101 | chr3 | 183728814 | 183728926 | chr3 | 183965514 | 183965625 |
| chr3 | 184017964 | 184018237 | chr3 | 184031615 | 184031734 | chr3 | 184057527 | 184057636 |
| chr3 | 184301634 | 184301671 | chr3 | 184319741 | 184319843 | chr3 | 184319874 | 184319980 |
| chr3 | 185001908 | 185002018 | chr3 | 185271201 | 185271380 | chr3 | 185303173 | 185303352 |
| chr3 | 185362989 | 185363348 | chr3 | 185643246 | 185643485 | chr3 | 186078683 | 186078982 |
| chr3 | 186079119 | 186079412 | chr3 | 186080114 | 186080245 | chr3 | 186080247 | 186080293 |
| chr3 | 186857051 | 186857710 | chr3 | 187387776 | 187387921 | chr3 | 187388007 | 187388315 |
| chr3 | 192125754 | 192125829 | chr3 | 192126116 | 192126711 | chr3 | 192126787 | 192126849 |
| chr3 | 192126851 | 192126955 | chr3 | 192127265 | 192127373 | chr3 | 192127557 | 192127731 |
| chr3 | 192127937 | 192128164 | chr3 | 192232077 | 192232256 | chr3 | 192232079 | 192232256 |
| chr3 | 192232362 | 192232437 | chr3 | 192232478 | 192232661 | chr3 | 192232753 | 192232819 |
| chr3 | 192232850 | 192232952 | chr3 | 192233095 | 192233232 | chr3 | 192958830 | 192959057 |
| chr3 | 193312046 | 193312165 | chr3 | 193419628 | 193419745 | chr3 | 193548557 | 193548797 |
| chr3 | 193548842 | 193548916 | chr3 | 193776015 | 193776194 | chr3 | 194048731 | 194049015 |
| chr3 | 194208185 | 194208258 | chr3 | 194208468 | 194208664 | chr3 | 194407924 | 194407936 |
| chr3 | 194408055 | 194408103 | chr3 | 194408279 | 194408769 | chr3 | 194408839 | 194409118 |
| chr3 | 195536642 | 195536828 | chr3 | 195538330 | 195538435 | chr3 | 195586956 | 195587195 |
| chr3 | 195601157 | 195601363 | chr3 | 195602364 | 195602435 | chr3 | 195648720 | 195648899 |
| chr3 | 196069893 | 196070192 | chr3 | 196255543 | 196255632 | chr3 | 196387206 | 196387505 |
| chr3 | 196387528 | 196387767 | chr3 | 196388303 | 196388662 | chr3 | 196731055 | 196731133 |
| chr3 | 196731197 | 196731414 | chr3 | 196755893 | 196756063 | chr3 | 197327025 | 197327131 |
| chr3 | 197616633 | 197616812 | chr3 | 197676955 | 197677134 | chr3 | 197685698 | 197685817 |
| chr3 | 197686060 | 197686177 | chr3 | 197687190 | 197687310 | chr4 | 330716 | 330790 |
| chr4 | 331308 | 331416 | chr4 | 568333 | 568653 | chr4 | 569048 | 569116 |
| chr4 | 569275 | 569436 | chr4 | 569461 | 569733 | chr4 | 570931 | 571110 |
| chr4 | 571420 | 571779 | chr4 | 628488 | 628770 | chr4 | 651110 | 651348 |
| chr4 | 657570 | 657657 | chr4 | 678397 | 678576 | chr4 | 718082 | 718202 |
| chr4 | 718240 | 718321 | chr4 | 829537 | 829716 | chr4 | 955292 | 955531 |
| chr4 | 955774 | 956013 | chr4 | 995876 | 995994 | chr4 | 996101 | 996175 |
| chr4 | 1008642 | 1008806 | chr4 | 1016332 | 1016340 | chr4 | 1016533 | 1016787 |
| chr4 | 1025852 | 1026151 | chr4 | 1093457 | 1093558 | chr4 | 1165276 | 1165287 |
| chr4 | 1165450 | 1165575 | chr4 | 1188947 | 1189126 | chr4 | 1282441 | 1282620 |
| chr4 | 1331636 | 1331780 | chr4 | 1338615 | 1338891 | chr4 | 1339023 | 1339130 |
| chr4 | 1396498 | 1396593 | chr4 | 1396595 | 1396697 | chr4 | 1397297 | 1397596 |
| chr4 | 1398222 | 1398247 | chr4 | 1398264 | 1398461 | chr4 | 1399627 | 1399633 |
| chr4 | 1401643 | 1401847 | chr4 | 1512294 | 1512473 | chr4 | 1556335 | 1556603 |
| chr4 | 1576387 | 1576626 | chr4 | 1616606 | 1617173 | chr4 | 1687006 | 1687185 |
| chr4 | 1803447 | 1803686 | chr4 | 1806010 | 1806089 | chr4 | 1807281 | 1807460 |
| chr4 | 1993677 | 1994276 | chr4 | 2042117 | 2042123 | chr4 | 2042169 | 2042259 |
| chr4 | 2066011 | 2066370 | chr4 | 2305571 | 2305930 | chr4 | 2527903 | 2528012 |
| chr4 | 2540247 | 2540395 | chr4 | 2765767 | 2766006 | chr4 | 2926292 | 2926471 |
| chr4 | 2978878 | 2979094 | chr4 | 3446917 | 3447096 | chr4 | 3447737 | 3448096 |
| chr4 | 3768759 | 3768950 | chr4 | 3768995 | 3769190 | chr4 | 3769560 | 3769665 |
| chr4 | 3873613 | 3873852 | chr4 | 4228094 | 4228168 | chr4 | 4228189 | 4228333 |
| chr4 | 4229586 | 4229885 | chr4 | 4387431 | 4387730 | chr4 | 4417467 | 4417706 |
| chr4 | 4855018 | 4855192 | chr4 | 4855231 | 4855257 | chr4 | 4855283 | 4855522 |
| chr4 | 4862671 | 4863210 | chr4 | 4867613 | 4867864 | chr4 | 4867924 | 4867972 |
| chr4 | 4868468 | 4868793 | chr4 | 4868829 | 4869000 | chr4 | 4869132 | 4869187 |
| chr4 | 4872009 | 4872032 | chr4 | 4872060 | 4872248 | chr4 | 4872695 | 4872934 |
| chr4 | 4873329 | 4873580 | chr4 | 5052995 | 5053594 | chr4 | 5053651 | 5054190 |
| chr4 | 5709819 | 5709985 | chr4 | 5712891 | 5713232 | chr4 | 5713327 | 5713370 |
| chr4 | 5889848 | 5890147 | chr4 | 5890180 | 5890539 | chr4 | 5891871 | 5892082 |
| chr4 | 5892110 | 5892251 | chr4 | 5892676 | 5892791 | chr4 | 5893898 | 5894083 |
| chr4 | 5894600 | 5894633 | chr4 | 5894813 | 5894882 | chr4 | 6200797 | 6201293 |
| chr4 | 6202011 | 6202370 | chr4 | 6247277 | 6247456 | chr4 | 6564904 | 6565143 |
| chr4 | 6670110 | 6670289 | chr4 | 6748251 | 6748662 | chr4 | 6957489 | 6957701 |
| chr4 | 7647679 | 7648038 | chr4 | 7758402 | 7758581 | chr4 | 8582475 | 8582619 |

TABLE 15-continued

Pan-cancer #5

| chr | start | end | chr | start | end | chr | start | end |
|---|---|---|---|---|---|---|---|---|
| chr4 | 8607724 | 8608023 | chr4 | 8608459 | 8608698 | chr4 | 8858804 | 8859048 |
| chr4 | 8859382 | 8859823 | chr4 | 8859875 | 8859938 | chr4 | 8860398 | 8860654 |
| chr4 | 8861606 | 8861753 | chr4 | 8861919 | 8862102 | chr4 | 8862705 | 8862812 |
| chr4 | 8863339 | 8863527 | chr4 | 8863857 | 8863878 | chr4 | 8864434 | 8864683 |
| chr4 | 8864764 | 8865155 | chr4 | 8868734 | 8868846 | chr4 | 8868932 | 8869271 |
| chr4 | 8869369 | 8869453 | chr4 | 8869498 | 8869917 | chr4 | 8872957 | 8873073 |
| chr4 | 8873774 | 8874077 | chr4 | 8874397 | 8874535 | chr4 | 8874773 | 8874812 |
| chr4 | 8875803 | 8875982 | chr4 | 8893427 | 8893606 | chr4 | 8893714 | 8893726 |
| chr4 | 8893816 | 8894013 | chr4 | 8894547 | 8894958 | chr4 | 8895232 | 8895446 |
| chr4 | 8895480 | 8895659 | chr4 | 8895965 | 8896098 | chr4 | 8896118 | 8896134 |
| chr4 | 9423195 | 9423281 | chr4 | 9782942 | 9783096 | chr4 | 9783126 | 9783424 |
| chr4 | 9783501 | 9783502 | chr4 | 10458309 | 10459208 | chr4 | 10462740 | 10463048 |
| chr4 | 10463073 | 10463256 | chr4 | 10463258 | 10463636 | chr4 | 11429482 | 11429720 |
| chr4 | 13523929 | 13524252 | chr4 | 13524571 | 13524872 | chr4 | 13537492 | 13537779 |
| chr4 | 13540946 | 13541146 | chr4 | 13541309 | 13541348 | chr4 | 13545941 | 13546172 |
| chr4 | 13548404 | 13548590 | chr4 | 13548635 | 13548999 | chr4 | 13549246 | 13549605 |
| chr4 | 15780123 | 15780422 | chr4 | 16084642 | 16084819 | chr4 | 16085167 | 16085180 |
| chr4 | 16085182 | 16085302 | chr4 | 16085352 | 16085481 | chr4 | 16085531 | 16085602 |
| chr4 | 16085675 | 16085770 | chr4 | 17782913 | 17783294 | chr4 | 17783296 | 17783322 |
| chr4 | 17783324 | 17783481 | chr4 | 17783610 | 17783692 | chr4 | 20254619 | 20254774 |
| chr4 | 20255339 | 20255368 | chr4 | 20255525 | 20255938 | chr4 | 20256067 | 20256286 |
| chr4 | 20256383 | 20256426 | chr4 | 21950146 | 21950155 | chr4 | 21950157 | 21950296 |
| chr4 | 24801868 | 24802053 | chr4 | 24914564 | 24914743 | chr4 | 25656728 | 25656893 |
| chr4 | 25657338 | 25657365 | chr4 | 25657367 | 25657414 | chr4 | 25657416 | 25657577 |
| chr4 | 27086358 | 27086537 | chr4 | 30724162 | 30724461 | chr4 | 37245837 | 37245939 |
| chr4 | 37246060 | 37246361 | chr4 | 37246490 | 37246700 | chr4 | 37247016 | 37247238 |
| chr4 | 37247294 | 37247306 | chr4 | 40910205 | 40910563 | chr4 | 41258624 | 41258789 |
| chr4 | 41259086 | 41259276 | chr4 | 41746922 | 41747221 | chr4 | 41747419 | 41747658 |
| chr4 | 41747889 | 41747977 | chr4 | 41748144 | 41748397 | chr4 | 41748583 | 41748767 |
| chr4 | 41748857 | 41748882 | chr4 | 41748976 | 41749138 | chr4 | 41749187 | 41749846 |
| chr4 | 41750125 | 41750604 | chr4 | 41751789 | 41751990 | chr4 | 41752363 | 41752782 |
| chr4 | 41752884 | 41753483 | chr4 | 41753512 | 41753712 | chr4 | 41753714 | 41753803 |
| chr4 | 41753805 | 41753917 | chr4 | 41754031 | 41754171 | chr4 | 41875337 | 41875891 |
| chr4 | 41881286 | 41881517 | chr4 | 41882469 | 41882533 | chr4 | 41882652 | 41882682 |
| chr4 | 41882988 | 41883407 | chr4 | 41883411 | 41883710 | chr4 | 41993731 | 41993896 |
| chr4 | 42152962 | 42153412 | chr4 | 42153533 | 42153633 | chr4 | 42153882 | 42154127 |
| chr4 | 42154201 | 42154385 | chr4 | 42154387 | 42154440 | chr4 | 42154561 | 42155100 |
| chr4 | 42398768 | 42398947 | chr4 | 42399045 | 42399284 | chr4 | 42399601 | 42399960 |
| chr4 | 44449387 | 44449570 | chr4 | 44449653 | 44449743 | chr4 | 44450170 | 44450177 |
| chr4 | 46995079 | 46995821 | chr4 | 46995823 | 46995918 | chr4 | 47034834 | 47035013 |
| chr4 | 48485152 | 48485289 | chr4 | 48485590 | 48486104 | chr4 | 48486254 | 48486493 |
| chr4 | 48492100 | 48492517 | chr4 | 48988013 | 48988229 | chr4 | 48988380 | 48988432 |
| chr4 | 53728417 | 53729087 | chr4 | 54966756 | 54967175 | chr4 | 54967264 | 54967563 |
| chr4 | 54969832 | 54970174 | chr4 | 54970277 | 54970576 | chr4 | 54975855 | 54975932 |
| chr4 | 54975991 | 54976116 | chr4 | 54976171 | 54976214 | chr4 | 55092973 | 55093332 |
| chr4 | 55096143 | 55096363 | chr4 | 55096441 | 55096442 | chr4 | 55097315 | 55097554 |
| chr4 | 55097709 | 55097729 | chr4 | 55097874 | 55098093 | chr4 | 55098198 | 55098473 |
| chr4 | 55098590 | 55098769 | chr4 | 55099040 | 55099159 | chr4 | 55524138 | 55524367 |
| chr4 | 55991019 | 55991270 | chr4 | 55992030 | 55992090 | chr4 | 55992153 | 55992269 |
| chr4 | 56659618 | 56659867 | chr4 | 56659935 | 56660097 | chr4 | 57371632 | 57371868 |
| chr4 | 57371870 | 57372051 | chr4 | 57372241 | 57372600 | chr4 | 57396866 | 57397345 |
| chr4 | 57521300 | 57521396 | chr4 | 57521506 | 57521664 | chr4 | 57521701 | 57522383 |
| chr4 | 57522420 | 57522908 | chr4 | 57687632 | 57687871 | chr4 | 57777338 | 57777577 |
| chr4 | 57803529 | 57803613 | chr4 | 57975930 | 57976289 | chr4 | 57976316 | 57976675 |
| chr4 | 62066134 | 62066645 | chr4 | 62067419 | 62067718 | chr4 | 62067992 | 62068202 |
| chr4 | 66535048 | 66535315 | chr4 | 66535351 | 66535483 | chr4 | 66536068 | 66536427 |
| chr4 | 74702379 | 74702448 | chr4 | 74702450 | 74702608 | chr4 | 74809786 | 74810025 |
| chr4 | 75241349 | 75241528 | chr4 | 75858482 | 75858611 | chr4 | 76555455 | 76555547 |
| chr4 | 76555549 | 76555934 | chr4 | 76912717 | 76912836 | chr4 | 79689573 | 79689812 |
| chr4 | 81106252 | 81106663 | chr4 | 81106665 | 81106669 | chr4 | 81124201 | 81124740 |
| chr4 | 81186972 | 81187151 | chr4 | 81187485 | 81187664 | chr4 | 81188230 | 81188316 |
| chr4 | 81188385 | 81188644 | chr4 | 81189336 | 81189661 | chr4 | 81189714 | 81189995 |
| chr4 | 81951357 | 81951536 | chr4 | 81951938 | 81952046 | chr4 | 81952078 | 81952312 |
| chr4 | 81952364 | 81952437 | chr4 | 82135786 | 82135888 | chr4 | 82135920 | 82136145 |
| chr4 | 82136403 | 82136642 | chr4 | 82136733 | 82136912 | chr4 | 83323428 | 83323677 |
| chr4 | 85402748 | 85403425 | chr4 | 85403824 | 85403928 | chr4 | 85404112 | 85404141 |
| chr4 | 85404225 | 85404476 | chr4 | 85404650 | 85404783 | chr4 | 85413977 | 85414114 |
| chr4 | 85414149 | 85414244 | chr4 | 85414270 | 85414337 | chr4 | 85414458 | 85414509 |
| chr4 | 85414637 | 85414936 | chr4 | 85417241 | 85417474 | chr4 | 85417517 | 85417660 |
| chr4 | 85417873 | 85418166 | chr4 | 85418319 | 85418370 | chr4 | 85418522 | 85418583 |
| chr4 | 85422101 | 85422520 | chr4 | 85422866 | 85422929 | chr4 | 85422973 | 85423052 |
| chr4 | 85424323 | 85424562 | chr4 | 87515263 | 87515442 | chr4 | 89378362 | 89378601 |
| chr4 | 89378667 | 89378767 | chr4 | 89378832 | 89378966 | chr4 | 90757439 | 90757913 |
| chr4 | 90758031 | 90758210 | chr4 | 90758681 | 90758980 | chr4 | 93225163 | 93225252 |
| chr4 | 93226367 | 93226380 | chr4 | 93226382 | 93226606 | chr4 | 93226729 | 93226958 |
| chr4 | 94750882 | 94751241 | chr4 | 94751342 | 94751581 | chr4 | 94753341 | 94753520 |

TABLE 15-continued

Pan-cancer #5

| chr | start | end | chr | start | end | chr | start | end |
|---|---|---|---|---|---|---|---|---|
| chr4 | 94756002 | 94756186 | chr4 | 95127560 | 95127679 | chr4 | 96470678 | 96470857 |
| chr4 | 101111166 | 101111585 | chr4 | 101111765 | 101111872 | chr4 | 101111874 | 101112058 |
| chr4 | 107955210 | 107955929 | chr4 | 107956582 | 107957181 | chr4 | 107957271 | 107957362 |
| chr4 | 107957364 | 107957570 | chr4 | 109093016 | 109093255 | chr4 | 109093307 | 109093606 |
| chr4 | 110222996 | 110223428 | chr4 | 110223579 | 110223598 | chr4 | 110223600 | 110223967 |
| chr4 | 110223969 | 110224075 | chr4 | 111532705 | 111533037 | chr4 | 111536192 | 111536506 |
| chr4 | 111536562 | 111536791 | chr4 | 111536882 | 111536975 | chr4 | 111537067 | 111537121 |
| chr4 | 111537356 | 111537572 | chr4 | 111540187 | 111540460 | chr4 | 111542474 | 111542570 |
| chr4 | 111542728 | 111542832 | chr4 | 111543132 | 111543346 | chr4 | 111543404 | 111543551 |
| chr4 | 111543579 | 111543696 | chr4 | 111543721 | 111543807 | chr4 | 111544303 | 111544662 |
| chr4 | 111549726 | 111549905 | chr4 | 111550517 | 111550930 | chr4 | 111552044 | 111552223 |
| chr4 | 111553006 | 111553545 | chr4 | 111553815 | 111554054 | chr4 | 111554864 | 111554965 |
| chr4 | 111555194 | 111555447 | chr4 | 111557888 | 111558127 | chr4 | 111558499 | 111559312 |
| chr4 | 111560174 | 111560713 | chr4 | 111562493 | 111562732 | chr4 | 113154804 | 113155043 |
| chr4 | 113430537 | 113430776 | chr4 | 113431755 | 113431855 | chr4 | 113431916 | 113432155 |
| chr4 | 113432227 | 113432504 | chr4 | 113432519 | 113432654 | chr4 | 113436133 | 113436372 |
| chr4 | 113441514 | 113441813 | chr4 | 113442013 | 113442186 | chr4 | 113442247 | 113442612 |
| chr4 | 113444003 | 113444295 | chr4 | 113444297 | 113444534 | chr4 | 117847310 | 117847459 |
| chr4 | 117847470 | 117847549 | chr4 | 121843986 | 121844285 | chr4 | 121992170 | 121992409 |
| chr4 | 121993915 | 121994334 | chr4 | 122301405 | 122301713 | chr4 | 122302032 | 122302331 |
| chr4 | 122685794 | 122685891 | chr4 | 122686119 | 122686453 | chr4 | 122686455 | 122686598 |
| chr4 | 122871195 | 122871434 | chr4 | 122871488 | 122872087 | chr4 | 123664147 | 123664249 |
| chr4 | 126237252 | 126237491 | chr4 | 126237552 | 126237701 | chr4 | 126237931 | 126238511 |
| chr4 | 128543956 | 128544255 | chr4 | 128544569 | 128544868 | chr4 | 134067794 | 134068093 |
| chr4 | 134068475 | 134068777 | chr4 | 134068779 | 134068894 | chr4 | 134069215 | 134069394 |
| chr4 | 134069498 | 134069977 | chr4 | 134070300 | 134070369 | chr4 | 134070371 | 134070479 |
| chr4 | 134071559 | 134072611 | chr4 | 134072677 | 134073058 | chr4 | 134073128 | 134073403 |
| chr4 | 134073486 | 134073725 | chr4 | 134073772 | 134073789 | chr4 | 134073944 | 134074243 |
| chr4 | 140200427 | 140201157 | chr4 | 140201193 | 140201566 | chr4 | 140657000 | 140657166 |
| chr4 | 141347925 | 141348227 | chr4 | 141418841 | 141419500 | chr4 | 141488790 | 141489159 |
| chr4 | 142053155 | 142053235 | chr4 | 142053418 | 142053837 | chr4 | 142054141 | 142054254 |
| chr4 | 142054256 | 142054560 | chr4 | 143766714 | 143767013 | chr4 | 144621248 | 144621440 |
| chr4 | 144621515 | 144621897 | chr4 | 144621982 | 144622147 | chr4 | 145567951 | 145568250 |
| chr4 | 145568361 | 145568745 | chr4 | 146853937 | 146854056 | chr4 | 147558179 | 147558382 |
| chr4 | 147558477 | 147558598 | chr4 | 147559220 | 147560079 | chr4 | 147560134 | 147560419 |
| chr4 | 147560460 | 147560659 | chr4 | 147560835 | 147561146 | chr4 | 147561360 | 147561950 |
| chr4 | 147562000 | 147562154 | chr4 | 147568549 | 147569148 | chr4 | 147569546 | 147569685 |
| chr4 | 147569764 | 147569725 | chr4 | 147576079 | 147576202 | chr4 | 147576330 | 147576738 |
| chr4 | 152246058 | 152246237 | chr4 | 152246398 | 152246403 | chr4 | 153249297 | 153249476 |
| chr4 | 153702690 | 153702805 | chr4 | 154216277 | 154216449 | chr4 | 154709440 | 154709611 |
| chr4 | 154709759 | 154709828 | chr4 | 154709830 | 154710598 | chr4 | 154710600 | 154710618 |
| chr4 | 154710729 | 154710999 | chr4 | 154712084 | 154712683 | chr4 | 154713426 | 154713605 |
| chr4 | 154713861 | 154714085 | chr4 | 155254092 | 155254271 | chr4 | 155411411 | 155411494 |
| chr4 | 155411930 | 155412370 | chr4 | 155663476 | 155663728 | chr4 | 155665371 | 155665550 |
| chr4 | 156129079 | 156129258 | chr4 | 156129354 | 156129387 | chr4 | 156129444 | 156129593 |
| chr4 | 156129653 | 156129892 | chr4 | 156129963 | 156130382 | chr4 | 156297337 | 156297636 |
| chr4 | 156297942 | 156298130 | chr4 | 156588237 | 156588245 | chr4 | 156588364 | 156588476 |
| chr4 | 156589179 | 156589203 | chr4 | 156589259 | 156589418 | chr4 | 156680156 | 156680485 |
| chr4 | 156680596 | 156680635 | chr4 | 156681281 | 156681465 | chr4 | 158141502 | 158141657 |
| chr4 | 158142744 | 158143101 | chr4 | 158143355 | 158143466 | chr4 | 158143610 | 158143654 |
| chr4 | 164252890 | 164253207 | chr4 | 164253209 | 164253549 | chr4 | 165304428 | 165304667 |
| chr4 | 165304948 | 165305024 | chr4 | 165305060 | 165305247 | chr4 | 166414897 | 166414996 |
| chr4 | 166794691 | 166794990 | chr4 | 166795933 | 166795993 | chr4 | 166796118 | 166796292 |
| chr4 | 168155010 | 168155124 | chr4 | 168155261 | 168155369 | chr4 | 170865262 | 170865381 |
| chr4 | 170947187 | 170947426 | chr4 | 172734067 | 172734148 | chr4 | 172734189 | 172734276 |
| chr4 | 172734278 | 172734306 | chr4 | 172734592 | 172734860 | chr4 | 174429584 | 174429763 |
| chr4 | 174430212 | 174430554 | chr4 | 174430794 | 174431171 | chr4 | 174438477 | 174438627 |
| chr4 | 174439744 | 174440340 | chr4 | 174440555 | 174440794 | chr4 | 174443138 | 174443317 |
| chr4 | 174443480 | 174444019 | chr4 | 174444199 | 174444256 | chr4 | 174446508 | 174446595 |
| chr4 | 174449847 | 174450408 | chr4 | 174450410 | 174450727 | chr4 | 174450752 | 174451586 |
| chr4 | 174451768 | 174452187 | chr4 | 174459094 | 174459375 | chr4 | 174459528 | 174459747 |
| chr4 | 174459770 | 174459933 | chr4 | 174460085 | 174460309 | chr4 | 175132661 | 175132840 |
| chr4 | 175132994 | 175133293 | chr4 | 175134806 | 175135765 | chr4 | 175135847 | 175136086 |
| chr4 | 175138419 | 175138629 | chr4 | 175138870 | 175139349 | chr4 | 175139473 | 175139772 |
| chr4 | 175750358 | 175750805 | chr4 | 176923342 | 176923641 | chr4 | 176987230 | 176987313 |
| chr4 | 176987315 | 176987448 | chr4 | 177713154 | 177713513 | chr4 | 180979196 | 180979375 |
| chr4 | 180980208 | 180980447 | chr4 | 183063573 | 183063973 | chr4 | 183063995 | 183064048 |
| chr4 | 183064517 | 183064756 | chr4 | 183064771 | 183065070 | chr4 | 184019164 | 184019403 |
| chr4 | 184019595 | 184019834 | chr4 | 184020043 | 184020263 | chr4 | 184375709 | 184375816 |
| chr4 | 184718157 | 184718456 | chr4 | 184826157 | 184826576 | chr4 | 184826976 | 184827328 |
| chr4 | 184921806 | 184922165 | chr4 | 185089598 | 185089897 | chr4 | 185937252 | 185937971 |
| chr4 | 185938412 | 185938651 | chr4 | 185940250 | 185940549 | chr4 | 185941484 | 185942473 |
| chr4 | 185942492 | 185942863 | chr5 | 53756 | 53899 | chr5 | 92072 | 92210 |
| chr5 | 320762 | 321061 | chr5 | 343957 | 344017 | chr5 | 373976 | 374369 |
| chr5 | 400112 | 400291 | chr5 | 480918 | 481037 | chr5 | 491257 | 491616 |
| chr5 | 524252 | 524491 | chr5 | 538663 | 538902 | chr5 | 554212 | 554569 |

TABLE 15-continued

Pan-cancer #5

| chr | start | end | chr | start | end | chr | start | end |
|---|---|---|---|---|---|---|---|---|
| chr5 | 554812 | 554916 | chr5 | 555193 | 555372 | chr5 | 555891 | 556070 |
| chr5 | 677799 | 678098 | chr5 | 1034508 | 1034747 | chr5 | 1131130 | 1131478 |
| chr5 | 1193302 | 1193465 | chr5 | 1193793 | 1194032 | chr5 | 1221103 | 1221402 |
| chr5 | 1294550 | 1294849 | chr5 | 1294928 | 1295443 | chr5 | 1295605 | 1295724 |
| chr5 | 1295759 | 1295767 | chr5 | 1445078 | 1445256 | chr5 | 1445654 | 1445760 |
| chr5 | 1445841 | 1446013 | chr5 | 1446237 | 1446370 | chr5 | 1446443 | 1446699 |
| chr5 | 1746941 | 1747180 | chr5 | 1874877 | 1875176 | chr5 | 1875356 | 1875595 |
| chr5 | 1875796 | 1876307 | chr5 | 1876638 | 1876921 | chr5 | 1877090 | 1877103 |
| chr5 | 1877195 | 1877320 | chr5 | 1877912 | 1878029 | chr5 | 1878224 | 1878577 |
| chr5 | 1878831 | 1879090 | chr5 | 1879513 | 1879662 | chr5 | 1879690 | 1879812 |
| chr5 | 1882420 | 1882690 | chr5 | 1882758 | 1882922 | chr5 | 1883132 | 1883177 |
| chr5 | 1883429 | 1883617 | chr5 | 1883880 | 1883908 | chr5 | 1884089 | 1884328 |
| chr5 | 1884479 | 1884778 | chr5 | 1885069 | 1885548 | chr5 | 1885910 | 1886077 |
| chr5 | 1886443 | 1886682 | chr5 | 1886736 | 1886842 | chr5 | 1886998 | 1887146 |
| chr5 | 1887547 | 1887582 | chr5 | 1887656 | 1887815 | chr5 | 1930701 | 1931005 |
| chr5 | 1931065 | 1931287 | chr5 | 1931445 | 1931577 | chr5 | 1931618 | 1931840 |
| chr5 | 1950698 | 1951057 | chr5 | 1952550 | 1952639 | chr5 | 1952724 | 1952729 |
| chr5 | 2038629 | 2038863 | chr5 | 2324309 | 2324488 | chr5 | 2541400 | 2541699 |
| chr5 | 2738746 | 2739130 | chr5 | 2739211 | 2739355 | chr5 | 2739780 | 2739803 |
| chr5 | 2739861 | 2740301 | chr5 | 2740431 | 2740665 | chr5 | 2741123 | 2741139 |
| chr5 | 2743516 | 2743660 | chr5 | 2743699 | 2743815 | chr5 | 2748298 | 2748490 |
| chr5 | 2749110 | 2749407 | chr5 | 2749625 | 2749777 | chr5 | 2750655 | 2750770 |
| chr5 | 2751855 | 2751974 | chr5 | 2752897 | 2753153 | chr5 | 2754664 | 2754703 |
| chr5 | 2754804 | 2754807 | chr5 | 2755227 | 2756486 | chr5 | 2756504 | 2756603 |
| chr5 | 2756674 | 2757523 | chr5 | 3031800 | 3032099 | chr5 | 3324948 | 3325367 |
| chr5 | 3590314 | 3590658 | chr5 | 3590804 | 3590853 | chr5 | 3591252 | 3591491 |
| chr5 | 3591768 | 3592127 | chr5 | 3592643 | 3592961 | chr5 | 3594155 | 3594520 |
| chr5 | 3594778 | 3594814 | chr5 | 3595056 | 3595254 | chr5 | 3595361 | 3595369 |
| chr5 | 3595850 | 3596080 | chr5 | 3596556 | 3596725 | chr5 | 3596825 | 3596980 |
| chr5 | 3597317 | 3597556 | chr5 | 3600076 | 3600255 | chr5 | 3602717 | 3603422 |
| chr5 | 3606712 | 3606771 | chr5 | 3673960 | 3674256 | chr5 | 4144300 | 4144592 |
| chr5 | 5139578 | 5139621 | chr5 | 5139754 | 5139997 | chr5 | 5140079 | 5140318 |
| chr5 | 5140528 | 5140758 | chr5 | 5140850 | 5141006 | chr5 | 6228525 | 6228650 |
| chr5 | 6448837 | 6449676 | chr5 | 6583371 | 6583670 | chr5 | 6687175 | 6687528 |
| chr5 | 7395162 | 7395394 | chr5 | 7395434 | 7395641 | chr5 | 7850251 | 7850286 |
| chr5 | 7850919 | 7851218 | chr5 | 9546511 | 9546750 | chr5 | 10333611 | 10334210 |
| chr5 | 10564925 | 10565228 | chr5 | 10565263 | 10565263 | chr5 | 10565265 | 10565704 |
| chr5 | 11384965 | 11385067 | chr5 | 11385069 | 11385465 | chr5 | 11903659 | 11903725 |
| chr5 | 11903822 | 11904114 | chr5 | 11904116 | 11904174 | chr5 | 11904196 | 11904380 |
| chr5 | 11904456 | 11904798 | chr5 | 11904801 | 11905040 | chr5 | 15500659 | 15500689 |
| chr5 | 15500736 | 15500833 | chr5 | 15500835 | 15501018 | chr5 | 16178946 | 16179153 |
| chr5 | 16179555 | 16179795 | chr5 | 16180183 | 16180321 | chr5 | 16466683 | 16466796 |
| chr5 | 16467097 | 16467216 | chr5 | 16936255 | 16936402 | chr5 | 16936500 | 16936614 |
| chr5 | 17203036 | 17203266 | chr5 | 17217854 | 17217865 | chr5 | 17217992 | 17218033 |
| chr5 | 17218121 | 17218300 | chr5 | 17218862 | 17218934 | chr5 | 17218986 | 17219101 |
| chr5 | 17512040 | 17512192 | chr5 | 22853425 | 22853596 | chr5 | 31193844 | 31194083 |
| chr5 | 31194312 | 31194511 | chr5 | 31639583 | 31640008 | chr5 | 31691580 | 31691745 |
| chr5 | 31854987 | 31855286 | chr5 | 32710252 | 32710551 | chr5 | 32710718 | 32710957 |
| chr5 | 32711024 | 32711429 | chr5 | 32711431 | 32711617 | chr5 | 32711729 | 32711968 |
| chr5 | 32711985 | 32712102 | chr5 | 32712290 | 32712584 | chr5 | 32712675 | 32712943 |
| chr5 | 33298097 | 33298101 | chr5 | 33891980 | 33892219 | chr5 | 33892339 | 33892518 |
| chr5 | 33936067 | 33936232 | chr5 | 33936234 | 33936362 | chr5 | 33936364 | 33936751 |
| chr5 | 34656834 | 34657042 | chr5 | 37834610 | 37834737 | chr5 | 37836572 | 37838071 |
| chr5 | 37838448 | 37838987 | chr5 | 37839684 | 37839736 | chr5 | 37839808 | 37840075 |
| chr5 | 37840077 | 37840220 | chr5 | 37840288 | 37840363 | chr5 | 37840530 | 37840843 |
| chr5 | 38257397 | 38257541 | chr5 | 38257543 | 38257696 | chr5 | 38257752 | 38257909 |
| chr5 | 38257945 | 38258051 | chr5 | 38556996 | 38557076 | chr5 | 38557188 | 38557427 |
| chr5 | 38845574 | 38845955 | chr5 | 38846469 | 38846533 | chr5 | 39343086 | 39343201 |
| chr5 | 40681036 | 40681228 | chr5 | 40681262 | 40681455 | chr5 | 40681601 | 40681840 |
| chr5 | 40682070 | 40682080 | chr5 | 42424732 | 42425151 | chr5 | 42950902 | 42951312 |
| chr5 | 42951420 | 42952112 | chr5 | 42991751 | 42992242 | chr5 | 42992376 | 42992555 |
| chr5 | 42992557 | 42992598 | chr5 | 42992783 | 42993010 | chr5 | 42993313 | 42993547 |
| chr5 | 42993853 | 42994272 | chr5 | 42994593 | 42994892 | chr5 | 42995073 | 42995254 |
| chr5 | 43007862 | 43008041 | chr5 | 43008113 | 43008472 | chr5 | 43017851 | 43018177 |
| chr5 | 43018327 | 43018690 | chr5 | 43019144 | 43019424 | chr5 | 43019729 | 43019968 |
| chr5 | 43040768 | 43041067 | chr5 | 43215459 | 43215562 | chr5 | 43396915 | 43397230 |
| chr5 | 43397306 | 43397334 | chr5 | 44389782 | 44389929 | chr5 | 45695091 | 45695240 |
| chr5 | 45695314 | 45695608 | chr5 | 45695823 | 45695964 | chr5 | 45696239 | 45696455 |
| chr5 | 45696457 | 45696465 | chr5 | 45696467 | 45696538 | chr5 | 49736497 | 49736789 |
| chr5 | 50262842 | 50263104 | chr5 | 50263486 | 50263725 | chr5 | 50264216 | 50264695 |
| chr5 | 50264746 | 50264925 | chr5 | 50265228 | 50265527 | chr5 | 50265621 | 50265672 |
| chr5 | 50265721 | 50265960 | chr5 | 50674051 | 50674290 | chr5 | 50674486 | 50674557 |
| chr5 | 50674638 | 50674665 | chr5 | 50674925 | 50675164 | chr5 | 50678269 | 50678273 |
| chr5 | 50678373 | 50678552 | chr5 | 50695193 | 50695241 | chr5 | 50695351 | 50695540 |
| chr5 | 54179491 | 54179537 | chr5 | 54179539 | 54179558 | chr5 | 54179610 | 54179730 |
| chr5 | 54179989 | 54180168 | chr5 | 54516275 | 54516681 | chr5 | 54516832 | 54517114 |

TABLE 15-continued

Pan-cancer #5

| chr | start | end | chr | start | end | chr | start | end |
|---|---|---|---|---|---|---|---|---|
| chr5 | 54518577 | 54518633 | chr5 | 54519134 | 54519289 | chr5 | 54519383 | 54519406 |
| chr5 | 54527323 | 54527444 | chr5 | 56248119 | 56248358 | chr5 | 57878174 | 57878473 |
| chr5 | 57878612 | 57878775 | chr5 | 57878811 | 57878851 | chr5 | 59188293 | 59188429 |
| chr5 | 59188952 | 59189058 | chr5 | 59189189 | 59189311 | chr5 | 59189787 | 59190026 |
| chr5 | 63254815 | 63255243 | chr5 | 63255316 | 63255354 | chr5 | 63257645 | 63257944 |
| chr5 | 63801932 | 63802272 | chr5 | 63802274 | 63802305 | chr5 | 63802340 | 63802591 |
| chr5 | 63986409 | 63986528 | chr5 | 63986570 | 63986888 | chr5 | 67591197 | 67591233 |
| chr5 | 68391320 | 68391429 | chr5 | 71014629 | 71014979 | chr5 | 71015095 | 71015814 |
| chr5 | 71403491 | 71403730 | chr5 | 71403882 | 71404158 | chr5 | 72416170 | 72416262 |
| chr5 | 72526319 | 72526415 | chr5 | 72526492 | 72526738 | chr5 | 72528360 | 72528539 |
| chr5 | 72529200 | 72529826 | chr5 | 72529890 | 72530699 | chr5 | 72594722 | 72594837 |
| chr5 | 72594868 | 72595017 | chr5 | 72595047 | 72595141 | chr5 | 72595456 | 72595722 |
| chr5 | 72595774 | 72595875 | chr5 | 72598977 | 72598983 | chr5 | 72599060 | 72599442 |
| chr5 | 72599463 | 72599936 | chr5 | 72677775 | 72677826 | chr5 | 72677998 | 72678029 |
| chr5 | 72678366 | 72678416 | chr5 | 72715160 | 72715348 | chr5 | 72715591 | 72715696 |
| chr5 | 72715731 | 72715846 | chr5 | 72716022 | 72716239 | chr5 | 72732870 | 72732910 |
| chr5 | 72733013 | 72733268 | chr5 | 72740047 | 72740286 | chr5 | 72746606 | 72746684 |
| chr5 | 72746730 | 72746785 | chr5 | 75377860 | 75378108 | chr5 | 75380089 | 75380268 |
| chr5 | 75380530 | 75381006 | chr5 | 76011192 | 76011431 | chr5 | 76012504 | 76012681 |
| chr5 | 76249176 | 76249671 | chr5 | 76249696 | 76249907 | chr5 | 76249945 | 76250250 |
| chr5 | 76250351 | 76250590 | chr5 | 76506369 | 76506608 | chr5 | 76506956 | 76507195 |
| chr5 | 76923601 | 76924024 | chr5 | 76924087 | 76924300 | chr5 | 76924417 | 76924494 |
| chr5 | 76924856 | 76925018 | chr5 | 76925477 | 76925776 | chr5 | 76928070 | 76928487 |
| chr5 | 76928588 | 76929007 | chr5 | 76932228 | 76932407 | chr5 | 76932463 | 76933266 |
| chr5 | 76934073 | 76934654 | chr5 | 76934677 | 76934972 | chr5 | 76935937 | 76936039 |
| chr5 | 76936100 | 76936819 | chr5 | 76939436 | 76939867 | chr5 | 76940241 | 76940477 |
| chr5 | 76941115 | 76941414 | chr5 | 77140440 | 77140799 | chr5 | 77147520 | 77147650 |
| chr5 | 77147873 | 77148214 | chr5 | 77148396 | 77148669 | chr5 | 77268278 | 77268734 |
| chr5 | 77268736 | 77269238 | chr5 | 77269264 | 77269408 | chr5 | 78407567 | 78407926 |
| chr5 | 78408118 | 78408275 | chr5 | 78408298 | 78408537 | chr5 | 79783152 | 79783256 |
| chr5 | 79864809 | 79865168 | chr5 | 79866100 | 79866508 | chr5 | 79947497 | 79947796 |
| chr5 | 80255722 | 80256075 | chr5 | 80689499 | 80689795 | chr5 | 80690030 | 80690278 |
| chr5 | 82767342 | 82767881 | chr5 | 82768798 | 82769157 | chr5 | 83679121 | 83679300 |
| chr5 | 83679592 | 83679643 | chr5 | 83679645 | 83680431 | chr5 | 83680592 | 83680665 |
| chr5 | 83680694 | 83680812 | chr5 | 87955360 | 87955455 | chr5 | 87955502 | 87955665 |
| chr5 | 87955840 | 87955899 | chr5 | 87956103 | 87956663 | chr5 | 87956680 | 87957062 |
| chr5 | 87962865 | 87963006 | chr5 | 87963365 | 87963601 | chr5 | 87967686 | 87968165 |
| chr5 | 87968411 | 87968686 | chr5 | 87968773 | 87968942 | chr5 | 87970114 | 87970114 |
| chr5 | 87970116 | 87970953 | chr5 | 87974027 | 87974386 | chr5 | 87974767 | 87975126 |
| chr5 | 87976104 | 87976408 | chr5 | 87976423 | 87976662 | chr5 | 87979655 | 87979779 |
| chr5 | 87979900 | 87980014 | chr5 | 87980047 | 87980079 | chr5 | 87980322 | 87980346 |
| chr5 | 87980871 | 87981341 | chr5 | 87985819 | 87986058 | chr5 | 87986127 | 87986154 |
| chr5 | 87986233 | 87986366 | chr5 | 87986445 | 87986472 | chr5 | 87988431 | 87988670 |
| chr5 | 87990311 | 87990530 | chr5 | 88185377 | 88185387 | chr5 | 88185389 | 88186087 |
| chr5 | 89854760 | 89854999 | chr5 | 92939817 | 92939837 | chr5 | 92940178 | 92940236 |
| chr5 | 94955759 | 94956010 | chr5 | 94956849 | 94957088 | chr5 | 94982143 | 94982314 |
| chr5 | 95767856 | 95768035 | chr5 | 95768068 | 95768427 | chr5 | 95768828 | 95769173 |
| chr5 | 100236601 | 100236840 | chr5 | 100238808 | 100238977 | chr5 | 100238979 | 100239022 |
| chr5 | 100239024 | 100239120 | chr5 | 100239135 | 100239167 | chr5 | 101631391 | 101631630 |
| chr5 | 107005090 | 107006265 | chr5 | 111987788 | 111987901 | chr5 | 112043011 | 112043367 |
| chr5 | 112073328 | 112073567 | chr5 | 112175566 | 112175730 | chr5 | 112629342 | 112629359 |
| chr5 | 112629394 | 112629761 | chr5 | 113391163 | 113391218 | chr5 | 113391284 | 113391774 |
| chr5 | 113391776 | 113392122 | chr5 | 113698466 | 113698584 | chr5 | 113698670 | 113698844 |
| chr5 | 113698952 | 113699203 | chr5 | 114515010 | 114515580 | chr5 | 114515611 | 114515728 |
| chr5 | 115151174 | 115151358 | chr5 | 115151650 | 115152385 | chr5 | 115152617 | 115152733 |
| chr5 | 115297105 | 115297293 | chr5 | 115297377 | 115297644 | chr5 | 115297836 | 115297986 |
| chr5 | 115298410 | 115298582 | chr5 | 115298782 | 115298829 | chr5 | 115298894 | 115299133 |
| chr5 | 119799840 | 119800079 | chr5 | 119801223 | 119801522 | chr5 | 121413445 | 121413684 |
| chr5 | 122422161 | 122422315 | chr5 | 122422516 | 122422754 | chr5 | 122423233 | 122423432 |
| chr5 | 122425029 | 122425268 | chr5 | 122431039 | 122431458 | chr5 | 124128503 | 124128574 |
| chr5 | 126626256 | 126626298 | chr5 | 126626300 | 126626795 | chr5 | 127872847 | 127873086 |
| chr5 | 127873553 | 127873789 | chr5 | 127874345 | 127874478 | chr5 | 127874706 | 127874944 |
| chr5 | 128300588 | 128300695 | chr5 | 128300713 | 128300874 | chr5 | 128795984 | 128796097 |
| chr5 | 128796099 | 128796343 | chr5 | 128796777 | 128797076 | chr5 | 128797246 | 128797485 |
| chr5 | 129239966 | 129240205 | chr5 | 131992008 | 131992247 | chr5 | 132947392 | 132947931 |
| chr5 | 133820025 | 133820136 | chr5 | 134366634 | 134366873 | chr5 | 134367007 | 134367266 |
| chr5 | 134367285 | 134367306 | chr5 | 134374304 | 134374506 | chr5 | 134374792 | 134375309 |
| chr5 | 134376120 | 134376474 | chr5 | 134376732 | 134376911 | chr5 | 134385869 | 134386168 |
| chr5 | 134386185 | 134386466 | chr5 | 134582953 | 134582969 | chr5 | 134825372 | 134825611 |
| chr5 | 134825913 | 134826098 | chr5 | 134870362 | 134870601 | chr5 | 134870689 | 134870927 |
| chr5 | 134871269 | 134872125 | chr5 | 134879391 | 134879973 | chr5 | 134914539 | 134914838 |
| chr5 | 135265664 | 135265842 | chr5 | 135266034 | 135266129 | chr5 | 135266578 | 135266753 |
| chr5 | 135528098 | 135528337 | chr5 | 136834009 | 136834051 | chr5 | 136834290 | 136834492 |
| chr5 | 136834494 | 136834608 | chr5 | 136834624 | 136834664 | chr5 | 136834707 | 136834881 |
| chr5 | 136834913 | 136834923 | chr5 | 137225092 | 137225268 | chr5 | 138273717 | 138273845 |
| chr5 | 139047897 | 139048256 | chr5 | 139227705 | 139227991 | chr5 | 139525654 | 139525833 |

TABLE 15-continued

Pan-cancer #5

| chr | start | end | chr | start | end | chr | start | end |
|---|---|---|---|---|---|---|---|---|
| chr5 | 139779840 | 139779953 | chr5 | 140174701 | 140174840 | chr5 | 140174938 | 140174994 |
| chr5 | 140187003 | 140187240 | chr5 | 140305895 | 140306134 | chr5 | 140306445 | 140306620 |
| chr5 | 140306675 | 140306787 | chr5 | 140346514 | 140346753 | chr5 | 140514817 | 140514996 |
| chr5 | 140604361 | 140604596 | chr5 | 140613851 | 140614089 | chr5 | 140614230 | 140614329 |
| chr5 | 140614384 | 140614469 | chr5 | 140777354 | 140777588 | chr5 | 140797000 | 140797279 |
| chr5 | 140797328 | 140797419 | chr5 | 140800384 | 140800965 | chr5 | 140801035 | 140801343 |
| chr5 | 140811136 | 140811138 | chr5 | 140855515 | 140856459 | chr5 | 140856547 | 140856710 |
| chr5 | 141031047 | 141031205 | chr5 | 141262957 | 141263143 | chr5 | 141263261 | 141263316 |
| chr5 | 141931261 | 141931355 | chr5 | 141931425 | 141931585 | chr5 | 142784881 | 142785305 |
| chr5 | 145713562 | 145713981 | chr5 | 145717097 | 145717197 | chr5 | 145717249 | 145717516 |
| chr5 | 145718714 | 145719754 | chr5 | 145719835 | 145719937 | chr5 | 145720019 | 145720024 |
| chr5 | 145720763 | 145720942 | chr5 | 145722033 | 145722467 | chr5 | 145722561 | 145723112 |
| chr5 | 145724421 | 145724780 | chr5 | 145725109 | 145725188 | chr5 | 145725694 | 145725948 |
| chr5 | 146257258 | 146257484 | chr5 | 146257486 | 146257677 | chr5 | 146889129 | 146889183 |
| chr5 | 146889332 | 146889538 | chr5 | 146889540 | 146889668 | chr5 | 149681971 | 149682270 |
| chr5 | 150051025 | 150051744 | chr5 | 150400044 | 150400283 | chr5 | 151066339 | 151066578 |
| chr5 | 151304297 | 151304476 | chr5 | 153852579 | 153852878 | chr5 | 153853387 | 153853569 |
| chr5 | 153855101 | 153855340 | chr5 | 153855658 | 153855925 | chr5 | 153856149 | 153856483 |
| chr5 | 153856847 | 153857086 | chr5 | 153857285 | 153857524 | chr5 | 153858220 | 153858699 |
| chr5 | 153859573 | 153859812 | chr5 | 153861948 | 153862180 | chr5 | 153862219 | 153862667 |
| chr5 | 153863347 | 153863417 | chr5 | 153863419 | 153863526 | chr5 | 154209838 | 154210070 |
| chr5 | 154318060 | 154318178 | chr5 | 155107702 | 155107941 | chr5 | 155108042 | 155108084 |
| chr5 | 155108161 | 155108268 | chr5 | 155108356 | 155108612 | chr5 | 155108659 | 155108838 |
| chr5 | 156874164 | 156874403 | chr5 | 157001643 | 157001941 | chr5 | 157078345 | 157078524 |
| chr5 | 157098282 | 157098701 | chr5 | 158478385 | 158478466 | chr5 | 158478513 | 158478864 |
| chr5 | 158524641 | 158524837 | chr5 | 158527367 | 158527817 | chr5 | 158527819 | 158528146 |
| chr5 | 159399015 | 159399100 | chr5 | 160975650 | 160975829 | chr5 | 161274223 | 161274358 |
| chr5 | 161274506 | 161274642 | chr5 | 166865354 | 166865462 | chr5 | 167956087 | 167956267 |
| chr5 | 167956414 | 167956560 | chr5 | 167956601 | 167956686 | chr5 | 168233320 | 168233559 |
| chr5 | 168727837 | 168727928 | chr5 | 168727995 | 168728076 | chr5 | 169064237 | 169064530 |
| chr5 | 169064532 | 169064887 | chr5 | 169532851 | 169533090 | chr5 | 170108211 | 170108450 |
| chr5 | 170735061 | 170735300 | chr5 | 170735731 | 170735875 | chr5 | 170736019 | 170736164 |
| chr5 | 170736716 | 170736831 | chr5 | 170737282 | 170737578 | chr5 | 170737779 | 170737864 |
| chr5 | 170737936 | 170738690 | chr5 | 170738824 | 170739571 | chr5 | 170739746 | 170740058 |
| chr5 | 170740091 | 170740105 | chr5 | 170740391 | 170740478 | chr5 | 170740575 | 170740673 |
| chr5 | 170740675 | 170741031 | chr5 | 170741508 | 170742276 | chr5 | 170742387 | 170742600 |
| chr5 | 170742673 | 170742827 | chr5 | 170743151 | 170743480 | chr5 | 170743647 | 170744207 |
| chr5 | 170744290 | 170744649 | chr5 | 170745286 | 170745560 | chr5 | 172656317 | 172656317 |
| chr5 | 172659314 | 172659378 | chr5 | 172659397 | 172659756 | chr5 | 172659768 | 172660026 |
| chr5 | 172660142 | 172660307 | chr5 | 172660633 | 172661001 | chr5 | 172661127 | 172661228 |
| chr5 | 172661368 | 172661772 | chr5 | 172664148 | 172664567 | chr5 | 172665492 | 172665911 |
| chr5 | 172670882 | 172671121 | chr5 | 172671268 | 172671482 | chr5 | 172671640 | 172671926 |
| chr5 | 172672391 | 172672406 | chr5 | 172672593 | 172672750 | chr5 | 172754486 | 172754725 |
| chr5 | 172754733 | 172754963 | chr5 | 172754986 | 172755032 | chr5 | 172755421 | 172755563 |
| chr5 | 172755595 | 172755745 | chr5 | 172756961 | 172757200 | chr5 | 174115296 | 174115690 |
| chr5 | 174115864 | 174115955 | chr5 | 174147441 | 174147680 | chr5 | 174150341 | 174150520 |
| chr5 | 174159300 | 174159669 | chr5 | 174162800 | 174162945 | chr5 | 174220897 | 174221036 |
| chr5 | 174870643 | 174870882 | chr5 | 174871097 | 174871576 | chr5 | 174921381 | 174921483 |
| chr5 | 175085059 | 175085298 | chr5 | 175085525 | 175085808 | chr5 | 175223571 | 175223748 |
| chr5 | 175223935 | 175223950 | chr5 | 175298706 | 175298986 | chr5 | 175299196 | 175299495 |
| chr5 | 175300277 | 175300456 | chr5 | 175621297 | 175621596 | chr5 | 175792785 | 175792932 |
| chr5 | 175792998 | 175793144 | chr5 | 176023818 | 176023882 | chr5 | 176024006 | 176024350 |
| chr5 | 176046280 | 176046639 | chr5 | 176107191 | 176107485 | chr5 | 176107518 | 176107670 |
| chr5 | 176236631 | 176236990 | chr5 | 176264711 | 176264998 | chr5 | 176764020 | 176764255 |
| chr5 | 177031093 | 177031272 | chr5 | 177408416 | 177408548 | chr5 | 177411561 | 177412210 |
| chr5 | 177713273 | 177713572 | chr5 | 178003629 | 178003662 | chr5 | 178004286 | 178004398 |
| chr5 | 178016513 | 178016571 | chr5 | 178016682 | 178016984 | chr5 | 178017520 | 178017571 |
| chr5 | 178017573 | 178017971 | chr5 | 178367990 | 178368122 | chr5 | 178368415 | 178368462 |
| chr5 | 178421400 | 178421423 | chr5 | 178422167 | 178422224 | chr5 | 178487023 | 178487304 |
| chr5 | 178487342 | 178487493 | chr5 | 178576382 | 178576578 | chr5 | 178655663 | 178655962 |
| chr5 | 178771216 | 178771631 | chr5 | 178771724 | 178771781 | chr5 | 178771783 | 178771860 |
| chr5 | 178771968 | 178772055 | chr5 | 178772120 | 178772359 | chr5 | 178772525 | 178772730 |
| chr5 | 178772779 | 178772824 | chr5 | 178958023 | 178958123 | chr5 | 179214036 | 179214275 |
| chr5 | 179244321 | 179244371 | chr5 | 179780005 | 179780013 | chr5 | 179780036 | 179780244 |
| chr5 | 179780607 | 179781086 | chr5 | 179867405 | 179867637 | chr5 | 180017039 | 180017278 |
| chr5 | 180017532 | 180017689 | chr5 | 180017691 | 180018011 | chr5 | 180018485 | 180018585 |
| chr5 | 180047646 | 180047703 | chr5 | 180075753 | 180075858 | chr5 | 180076054 | 180076412 |
| chr5 | 180076533 | 180076705 | chr5 | 180076721 | 180077080 | chr5 | 180100825 | 180100874 |
| chr5 | 180101016 | 180101168 | chr5 | 180101252 | 180101410 | chr5 | 180326052 | 180326231 |
| chr5 | 180527447 | 180527699 | chr5 | 180527794 | 180527866 | chr5 | 180600769 | 180601030 |
| chr5 | 180601129 | 180601308 | chr6 | 391089 | 391743 | chr6 | 391745 | 391764 |
| chr6 | 391766 | 391900 | chr6 | 392410 | 392434 | chr6 | 392588 | 392959 |
| chr6 | 393125 | 393239 | chr6 | 393241 | 393473 | chr6 | 711039 | 711392 |
| chr6 | 1311899 | 1312095 | chr6 | 1312680 | 1312802 | chr6 | 1314014 | 1314101 |
| chr6 | 1378133 | 1378476 | chr6 | 1379268 | 1379332 | chr6 | 1379510 | 1379689 |
| chr6 | 1379812 | 1380051 | chr6 | 1383598 | 1383709 | chr6 | 1383860 | 1383982 |

TABLE 15-continued

Pan-cancer #5

| chr | start | end | chr | start | end | chr | start | end |
|---|---|---|---|---|---|---|---|---|
| chr6 | 1383984 | 1384180 | chr6 | 1384626 | 1384731 | chr6 | 1385025 | 1385264 |
| chr6 | 1386020 | 1386212 | chr6 | 1389044 | 1389275 | chr6 | 1390159 | 1390361 |
| chr6 | 1390363 | 1390406 | chr6 | 1390424 | 1390759 | chr6 | 1390956 | 1391118 |
| chr6 | 1391230 | 1391469 | chr6 | 1524122 | 1524361 | chr6 | 1605302 | 1605541 |
| chr6 | 1615243 | 1615279 | chr6 | 1624940 | 1625059 | chr6 | 1625129 | 1625779 |
| chr6 | 3053237 | 3053463 | chr6 | 3228955 | 3229134 | chr6 | 3229348 | 3229587 |
| chr6 | 3231926 | 3232029 | chr6 | 3285129 | 3285608 | chr6 | 3405599 | 3405778 |
| chr6 | 4775080 | 4775322 | chr6 | 4836441 | 4836545 | chr6 | 4951178 | 4951469 |
| chr6 | 5783232 | 5783457 | chr6 | 5996852 | 5997091 | chr6 | 5997728 | 5997907 |
| chr6 | 6003213 | 6003529 | chr6 | 6004350 | 6004744 | chr6 | 6004837 | 6005450 |
| chr6 | 6006278 | 6006498 | chr6 | 6006600 | 6006959 | chr6 | 6007516 | 6007670 |
| chr6 | 6007672 | 6007772 | chr6 | 6007833 | 6008355 | chr6 | 6367000 | 6367218 |
| chr6 | 7726260 | 7726439 | chr6 | 7726556 | 7726735 | chr6 | 7726878 | 7727057 |
| chr6 | 7727622 | 7727769 | chr6 | 7728087 | 7728221 | chr6 | 7728746 | 7729045 |
| chr6 | 10381428 | 10381593 | chr6 | 10381695 | 10381969 | chr6 | 10382322 | 10382383 |
| chr6 | 10382648 | 10383126 | chr6 | 10383638 | 10383877 | chr6 | 10384876 | 10384975 |
| chr6 | 10385280 | 10386015 | chr6 | 10386123 | 10386357 | chr6 | 10389946 | 10391216 |
| chr6 | 10410429 | 10410668 | chr6 | 10411254 | 10411613 | chr6 | 10415015 | 10415314 |
| chr6 | 10415457 | 10415816 | chr6 | 10416039 | 10416399 | chr6 | 10417059 | 10417530 |
| chr6 | 10418997 | 10419440 | chr6 | 10419477 | 10419596 | chr6 | 10419664 | 10420002 |
| chr6 | 10420975 | 10421171 | chr6 | 10421253 | 10421452 | chr6 | 10421549 | 10422714 |
| chr6 | 10425411 | 10425478 | chr6 | 10425630 | 10425790 | chr6 | 10425839 | 10426970 |
| chr6 | 10881857 | 10882156 | chr6 | 10882247 | 10882426 | chr6 | 10882934 | 10883023 |
| chr6 | 10886993 | 10887185 | chr6 | 10887187 | 10887772 | chr6 | 11043988 | 11044106 |
| chr6 | 11044108 | 11044541 | chr6 | 11044543 | 11044647 | chr6 | 12288420 | 12288779 |
| chr6 | 12749819 | 12749941 | chr6 | 16196952 | 16197191 | chr6 | 17281327 | 17281327 |
| chr6 | 17281329 | 17281351 | chr6 | 18035792 | 18036091 | chr6 | 19691621 | 19691920 |
| chr6 | 19691983 | 19691997 | chr6 | 19692143 | 19692280 | chr6 | 19836983 | 19837064 |
| chr6 | 19837141 | 19837205 | chr6 | 21665144 | 21665613 | chr6 | 24494604 | 24494843 |
| chr6 | 24647262 | 24647371 | chr6 | 26184364 | 26184476 | chr6 | 26188754 | 26189234 |
| chr6 | 26189236 | 26189495 | chr6 | 26199099 | 26199242 | chr6 | 26199612 | 26199791 |
| chr6 | 26214613 | 26214731 | chr6 | 26235124 | 26235437 | chr6 | 26240532 | 26241201 |
| chr6 | 26250378 | 26250685 | chr6 | 26250687 | 26250917 | chr6 | 26250969 | 26251261 |
| chr6 | 26251715 | 26251940 | chr6 | 26252075 | 26252099 | chr6 | 26252141 | 26252180 |
| chr6 | 26271315 | 26271816 | chr6 | 26271818 | 26271854 | chr6 | 26271897 | 26272076 |
| chr6 | 26272416 | 26272715 | chr6 | 26273381 | 26273419 | chr6 | 26273515 | 26273560 |
| chr6 | 26284786 | 26284975 | chr6 | 26327725 | 26328074 | chr6 | 26328206 | 26328505 |
| chr6 | 26332079 | 26332318 | chr6 | 26501764 | 26501841 | chr6 | 26501950 | 26502296 |
| chr6 | 26550895 | 26551059 | chr6 | 26551084 | 26551134 | chr6 | 26577078 | 26577557 |
| chr6 | 26987930 | 26988169 | chr6 | 27059697 | 27059936 | chr6 | 27064581 | 27064769 |
| chr6 | 27064771 | 27065003 | chr6 | 27065005 | 27065300 | chr6 | 27173436 | 27173547 |
| chr6 | 27173633 | 27173855 | chr6 | 27173925 | 27174275 | chr6 | 27182856 | 27182974 |
| chr6 | 27203167 | 27203286 | chr6 | 27205240 | 27205359 | chr6 | 27205420 | 27205521 |
| chr6 | 27205587 | 27205837 | chr6 | 27205914 | 27206126 | chr6 | 27228079 | 27228187 |
| chr6 | 27228290 | 27228498 | chr6 | 27247561 | 27247800 | chr6 | 27256016 | 27256255 |
| chr6 | 27256283 | 27256522 | chr6 | 27264344 | 27264468 | chr6 | 27279750 | 27280109 |
| chr6 | 27462939 | 27463778 | chr6 | 27512675 | 27512884 | chr6 | 27512995 | 27513574 |
| chr6 | 27533723 | 27534442 | chr6 | 27559775 | 27560074 | chr6 | 27573073 | 27573492 |
| chr6 | 27598650 | 27598949 | chr6 | 27599071 | 27599427 | chr6 | 27635171 | 27635530 |
| chr6 | 27647625 | 27647736 | chr6 | 27647891 | 27647984 | chr6 | 27648934 | 27649153 |
| chr6 | 27834577 | 27834863 | chr6 | 27834905 | 27834936 | chr6 | 27834963 | 27835097 |
| chr6 | 27835378 | 27835502 | chr6 | 27839635 | 27840174 | chr6 | 27840461 | 27840668 |
| chr6 | 27841002 | 27841240 | chr6 | 27858427 | 27858726 | chr6 | 28175105 | 28176301 |
| chr6 | 28303466 | 28303571 | chr6 | 28303847 | 28304339 | chr6 | 28367023 | 28367279 |
| chr6 | 28367281 | 28367347 | chr6 | 28367491 | 28367571 | chr6 | 28367573 | 28367862 |
| chr6 | 28410896 | 28411030 | chr6 | 28411032 | 28411088 | chr6 | 28411152 | 28411435 |
| chr6 | 28414887 | 28414992 | chr6 | 28415092 | 28415126 | chr6 | 28457534 | 28457713 |
| chr6 | 28457775 | 28458254 | chr6 | 33955409 | 33955828 | chr6 | 34170869 | 34170986 |
| chr6 | 34171049 | 34171166 | chr6 | 34396518 | 34396631 | chr6 | 34724210 | 34724318 |
| chr6 | 35149942 | 35150181 | chr6 | 35992410 | 35992533 | chr6 | 36165588 | 36165767 |
| chr6 | 36252899 | 36253258 | chr6 | 36313887 | 36313988 | chr6 | 36808233 | 36808532 |
| chr6 | 37024485 | 37024664 | chr6 | 37664045 | 37664284 | chr6 | 37673227 | 37673573 |
| chr6 | 37776339 | 37776455 | chr6 | 37776737 | 37776839 | chr6 | 39281005 | 39281231 |
| chr6 | 39281731 | 39281970 | chr6 | 39329789 | 39329968 | chr6 | 39760322 | 39760663 |
| chr6 | 40554557 | 40554796 | chr6 | 41336981 | 41337220 | chr6 | 41339162 | 41339559 |
| chr6 | 41339602 | 41339941 | chr6 | 41340803 | 41341282 | chr6 | 41341406 | 41341604 |
| chr6 | 41342140 | 41342370 | chr6 | 41342733 | 41342912 | chr6 | 41605851 | 41605952 |
| chr6 | 41606038 | 41606357 | chr6 | 41606528 | 41606630 | chr6 | 41773485 | 41773844 |
| chr6 | 42773364 | 42773471 | chr6 | 42846625 | 42846729 | chr6 | 42879457 | 42879569 |
| chr6 | 42879622 | 42879756 | chr6 | 42928239 | 42928460 | chr6 | 43211113 | 43211402 |
| chr6 | 43424445 | 43424564 | chr6 | 43425407 | 43425524 | chr6 | 43478592 | 43478821 |
| chr6 | 43612737 | 43612899 | chr6 | 43613053 | 43613156 | chr6 | 43639525 | 43639809 |
| chr6 | 43748380 | 43748619 | chr6 | 44240961 | 44241191 | chr6 | 44695775 | 44695899 |
| chr6 | 45388701 | 45388866 | chr6 | 46702904 | 46703203 | chr6 | 46703274 | 46703513 |
| chr6 | 50674292 | 50674831 | chr6 | 50681612 | 50681851 | chr6 | 50681912 | 50682031 |
| chr6 | 50682234 | 50682339 | chr6 | 50682449 | 50682473 | chr6 | 50682584 | 50682684 |

TABLE 15-continued

Pan-cancer #5

| chr | start | end | chr | start | end | chr | start | end |
|---|---|---|---|---|---|---|---|---|
| chr6 | 50682712 | 50682941 | chr6 | 50682992 | 50683303 | chr6 | 50684865 | 50685044 |
| chr6 | 50689827 | 50690126 | chr6 | 50690991 | 50691170 | chr6 | 50691983 | 50692213 |
| chr6 | 50692300 | 50692582 | chr6 | 50787125 | 50787877 | chr6 | 50787950 | 50788444 |
| chr6 | 50789300 | 50789479 | chr6 | 50791111 | 50791495 | chr6 | 50791551 | 50791708 |
| chr6 | 50793251 | 50793490 | chr6 | 50793626 | 50793850 | chr6 | 50794525 | 50794792 |
| chr6 | 50803732 | 50803971 | chr6 | 50804041 | 50804446 | chr6 | 50808589 | 50808845 |
| chr6 | 50810456 | 50810714 | chr6 | 50810976 | 50811575 | chr6 | 50813200 | 50814019 |
| chr6 | 50814495 | 50814674 | chr6 | 50816947 | 50817306 | chr6 | 50817831 | 50817841 |
| chr6 | 50818369 | 50818788 | chr6 | 50818841 | 50819080 | chr6 | 52227678 | 52227857 |
| chr6 | 52227934 | 52227964 | chr6 | 52344301 | 52344480 | chr6 | 53212553 | 53213932 |
| chr6 | 55443610 | 55444029 | chr6 | 56112175 | 56112474 | chr6 | 56716252 | 56716300 |
| chr6 | 56716390 | 56716491 | chr6 | 56818618 | 56819037 | chr6 | 56819128 | 56819727 |
| chr6 | 56819823 | 56820002 | chr6 | 58147345 | 58147511 | chr6 | 58147764 | 58148058 |
| chr6 | 62995272 | 62995875 | chr6 | 62996078 | 62996130 | chr6 | 62996132 | 62996214 |
| chr6 | 62996216 | 62996231 | chr6 | 62996347 | 62996586 | chr6 | 70991961 | 70992049 |
| chr6 | 70992137 | 70992260 | chr6 | 70992339 | 70992638 | chr6 | 70992744 | 70993103 |
| chr6 | 71665562 | 71665801 | chr6 | 71666708 | 71667066 | chr6 | 72129690 | 72129850 |
| chr6 | 72129927 | 72129929 | chr6 | 72130017 | 72130045 | chr6 | 72130191 | 72130499 |
| chr6 | 72596039 | 72596135 | chr6 | 72596137 | 72596398 | chr6 | 72596876 | 72597055 |
| chr6 | 73329686 | 73330225 | chr6 | 73330740 | 73331114 | chr6 | 73331116 | 73331238 |
| chr6 | 73331240 | 73331399 | chr6 | 73331420 | 73331851 | chr6 | 73331876 | 73333099 |
| chr6 | 78172096 | 78172276 | chr6 | 78172323 | 78172675 | chr6 | 78173119 | 78173227 |
| chr6 | 78173229 | 78173295 | chr6 | 78173610 | 78173726 | chr6 | 78173772 | 78174080 |
| chr6 | 78176370 | 78176607 | chr6 | 78176693 | 78176909 | chr6 | 79620310 | 79620342 |
| chr6 | 79620475 | 79620685 | chr6 | 79620687 | 79620789 | chr6 | 80656846 | 80657265 |
| chr6 | 82958527 | 82958646 | chr6 | 84417343 | 84417701 | chr6 | 84418261 | 84418377 |
| chr6 | 84418545 | 84418724 | chr6 | 84418726 | 84418789 | chr6 | 84419077 | 84419202 |
| chr6 | 84419204 | 84419329 | chr6 | 84419331 | 84419496 | chr6 | 84562789 | 84562930 |
| chr6 | 84562932 | 84563285 | chr6 | 84563417 | 84563636 | chr6 | 85472306 | 85473805 |
| chr6 | 85473854 | 85474453 | chr6 | 85474516 | 85474767 | chr6 | 85474795 | 85474815 |
| chr6 | 85476140 | 85476379 | chr6 | 85476924 | 85477103 | chr6 | 85478440 | 85478557 |
| chr6 | 85478615 | 85478799 | chr6 | 85482437 | 85482796 | chr6 | 85483271 | 85483450 |
| chr6 | 85483760 | 85483932 | chr6 | 85484558 | 85484626 | chr6 | 85484717 | 85484998 |
| chr6 | 86302335 | 86302422 | chr6 | 87647130 | 87647219 | chr6 | 87862013 | 87862252 |
| chr6 | 88876871 | 88877064 | chr6 | 88877066 | 88877422 | chr6 | 88877475 | 88877530 |
| chr6 | 91320191 | 91320422 | chr6 | 91320853 | 91321390 | chr6 | 94126870 | 94127066 |
| chr6 | 94127086 | 94127169 | chr6 | 94127381 | 94127620 | chr6 | 94128340 | 94128502 |
| chr6 | 94129119 | 94129358 | chr6 | 94129423 | 94129627 | chr6 | 94129629 | 94129662 |
| chr6 | 96464003 | 96464293 | chr6 | 99271829 | 99272908 | chr6 | 99273271 | 99273510 |
| chr6 | 99277106 | 99277201 | chr6 | 99277262 | 99277405 | chr6 | 99279465 | 99279704 |
| chr6 | 99280472 | 99280831 | chr6 | 99280931 | 99281037 | chr6 | 99281068 | 99281470 |
| chr6 | 99283428 | 99283667 | chr6 | 99290260 | 99290473 | chr6 | 99290710 | 99290738 |
| chr6 | 99291191 | 99291342 | chr6 | 99292156 | 99292515 | chr6 | 99295648 | 99295864 |
| chr6 | 99296062 | 99296365 | chr6 | 99296408 | 99296547 | chr6 | 99396354 | 99396473 |
| chr6 | 100038584 | 100038707 | chr6 | 100038786 | 100039063 | chr6 | 100039275 | 100039364 |
| chr6 | 100050674 | 100050811 | chr6 | 100050859 | 100051109 | chr6 | 100051360 | 100051508 |
| chr6 | 100051772 | 100052053 | chr6 | 100053191 | 100053606 | chr6 | 100054773 | 100055012 |
| chr6 | 100060930 | 100061169 | chr6 | 100061216 | 100061515 | chr6 | 100061677 | 100061697 |
| chr6 | 100062083 | 100062682 | chr6 | 100062857 | 100063156 | chr6 | 100441276 | 100441308 |
| chr6 | 100441498 | 100441738 | chr6 | 100441762 | 100442055 | chr6 | 100903299 | 100903405 |
| chr6 | 100903561 | 100903718 | chr6 | 100904126 | 100904365 | chr6 | 100905936 | 100906113 |
| chr6 | 100911976 | 100912215 | chr6 | 100912332 | 100912446 | chr6 | 100912466 | 100912571 |
| chr6 | 100912825 | 100913051 | chr6 | 101840615 | 101840914 | chr6 | 101850062 | 101850314 |
| chr6 | 101850394 | 101850539 | chr6 | 105388605 | 105388717 | chr6 | 105389510 | 105389792 |
| chr6 | 105400811 | 105401110 | chr6 | 105401538 | 105401908 | chr6 | 105404475 | 105404774 |
| chr6 | 105405565 | 105405864 | chr6 | 105406024 | 105406203 | chr6 | 105584190 | 105584216 |
| chr6 | 105584218 | 105584320 | chr6 | 105584367 | 105584551 | chr6 | 105584553 | 105585629 |
| chr6 | 106428948 | 106429476 | chr6 | 106429590 | 106429704 | chr6 | 106434265 | 106434371 |
| chr6 | 106441795 | 106443054 | chr6 | 106960817 | 106961116 | chr6 | 108280341 | 108280442 |
| chr6 | 108434990 | 108435327 | chr6 | 108435970 | 108436629 | chr6 | 108438142 | 108438157 |
| chr6 | 108438261 | 108438612 | chr6 | 108440017 | 108440645 | chr6 | 108440745 | 108441036 |
| chr6 | 108479209 | 108479748 | chr6 | 108484829 | 108485274 | chr6 | 108485419 | 108485488 |
| chr6 | 108485576 | 108485995 | chr6 | 108486067 | 108486486 | chr6 | 108487701 | 108488520 |
| chr6 | 108489662 | 108489809 | chr6 | 108490067 | 108490246 | chr6 | 108490297 | 108490515 |
| chr6 | 108490538 | 108490729 | chr6 | 108490902 | 108491001 | chr6 | 108491108 | 108491501 |
| chr6 | 108492182 | 108492541 | chr6 | 108495607 | 108495818 | chr6 | 108495916 | 108496026 |
| chr6 | 108496130 | 108496466 | chr6 | 108497419 | 108497467 | chr6 | 110679030 | 110679400 |
| chr6 | 110679402 | 110679509 | chr6 | 110797604 | 110797783 | chr6 | 110797977 | 110798047 |
| chr6 | 116783418 | 116783591 | chr6 | 117086168 | 117086479 | chr6 | 117086481 | 117086640 |
| chr6 | 117086903 | 117086947 | chr6 | 117585867 | 117586106 | chr6 | 117587028 | 117587256 |
| chr6 | 117587380 | 117587387 | chr6 | 117587449 | 117587679 | chr6 | 117591087 | 117591266 |
| chr6 | 117591308 | 117591597 | chr6 | 117591684 | 117591847 | chr6 | 118228008 | 118228232 |
| chr6 | 118228669 | 118228869 | chr6 | 118228871 | 118228908 | chr6 | 118229060 | 118229390 |
| chr6 | 118229417 | 118229479 | chr6 | 118229543 | 118229573 | chr6 | 118229617 | 118229732 |
| chr6 | 118229734 | 118229902 | chr6 | 118241125 | 118241309 | chr6 | 118241395 | 118241604 |
| chr6 | 119254661 | 119254774 | chr6 | 121758594 | 121758980 | chr6 | 121758982 | 121759048 |

TABLE 15-continued

Pan-cancer #5

| chr | start | end | chr | start | end | chr | start | end |
|---|---|---|---|---|---|---|---|---|
| chr6 | 123316950 | 123317007 | chr6 | 123317073 | 123317669 | chr6 | 123317696 | 123317714 |
| chr6 | 123317716 | 123317935 | chr6 | 124124330 | 124124569 | chr6 | 124124759 | 124125118 |
| chr6 | 125284034 | 125284273 | chr6 | 126068016 | 126068022 | chr6 | 126068069 | 126068255 |
| chr6 | 127439322 | 127439536 | chr6 | 127439907 | 127440206 | chr6 | 127440248 | 127440510 |
| chr6 | 127440512 | 127440963 | chr6 | 127441031 | 127441207 | chr6 | 127441479 | 127441838 |
| chr6 | 127441944 | 127442071 | chr6 | 127442090 | 127442183 | chr6 | 127840412 | 127840771 |
| chr6 | 129204373 | 129204612 | chr6 | 130686437 | 130687156 | chr6 | 131602689 | 131602789 |
| chr6 | 132721988 | 132722142 | chr6 | 132722158 | 132722287 | chr6 | 133561967 | 133562145 |
| chr6 | 132562349 | 133562437 | chr6 | 133562675 | 133563095 | chr6 | 133563234 | 133564013 |
| chr6 | 134067456 | 134067573 | chr6 | 134176147 | 134176149 | chr6 | 134210558 | 134211019 |
| chr6 | 134211112 | 134211458 | chr6 | 134213855 | 134213988 | chr6 | 134214077 | 134214454 |
| chr6 | 134589425 | 134589586 | chr6 | 134638858 | 134639095 | chr6 | 137241828 | 137242062 |
| chr6 | 137242064 | 137242307 | chr6 | 137243130 | 137243342 | chr6 | 137243367 | 137243489 |
| chr6 | 137244036 | 137244149 | chr6 | 137244236 | 137244466 | chr6 | 137311060 | 137311479 |
| chr6 | 137366280 | 137366459 | chr6 | 137809066 | 137809366 | chr6 | 137809446 | 137809917 |
| chr6 | 137810033 | 137811165 | chr6 | 137813692 | 137813991 | chr6 | 137814505 | 137814619 |
| chr6 | 137814654 | 137814864 | chr6 | 137814916 | 137815171 | chr6 | 137815225 | 137815755 |
| chr6 | 137816373 | 137817377 | chr6 | 137818428 | 137818599 | chr6 | 137818619 | 137819267 |
| chr6 | 137819269 | 137819447 | chr6 | 146755489 | 146755728 | chr6 | 149868369 | 149868478 |
| chr6 | 150284574 | 150284657 | chr6 | 150284979 | 150285369 | chr6 | 150285545 | 150285886 |
| chr6 | 150286100 | 150286718 | chr6 | 150358890 | 150358985 | chr6 | 150358987 | 150359193 |
| chr6 | 150359439 | 150359489 | chr6 | 151560928 | 151561341 | chr6 | 151561369 | 151561947 |
| chr6 | 151561986 | 151561992 | chr6 | 151562057 | 151562645 | chr6 | 151814953 | 151815192 |
| chr6 | 152622925 | 152623584 | chr6 | 152957816 | 152957999 | chr6 | 152958001 | 152958166 |
| chr6 | 153451175 | 153451578 | chr6 | 153451810 | 153452049 | chr6 | 153452157 | 153452396 |
| chr6 | 153452611 | 153452755 | chr6 | 153452789 | 153452850 | chr6 | 154360549 | 154360848 |
| chr6 | 154970468 | 154970587 | chr6 | 155316161 | 155316221 | chr6 | 155316257 | 155316340 |
| chr6 | 155569193 | 155569407 | chr6 | 157502364 | 157502543 | chr6 | 157506008 | 157506187 |
| chr6 | 157556755 | 157557297 | chr6 | 159589948 | 159590087 | chr6 | 159590155 | 159590762 |
| chr6 | 159590972 | 159591087 | chr6 | 159654844 | 159655083 | chr6 | 161188439 | 161188618 |
| chr6 | 161351999 | 161352146 | chr6 | 161352199 | 161352238 | chr6 | 161780141 | 161780218 |
| chr6 | 163834237 | 163834383 | chr6 | 163834406 | 163834533 | chr6 | 163834711 | 163834716 |
| chr6 | 163834779 | 163834902 | chr6 | 163834988 | 163835018 | chr6 | 163836465 | 163837004 |
| chr6 | 164179653 | 164179772 | chr6 | 164196997 | 164197107 | chr6 | 164228212 | 164228449 |
| chr6 | 164246123 | 164246229 | chr6 | 164283167 | 164283370 | chr6 | 164314286 | 164314525 |
| chr6 | 164322572 | 164322871 | chr6 | 166074027 | 166074506 | chr6 | 166076696 | 166077115 |
| chr6 | 166077280 | 166077633 | chr6 | 166077669 | 166077759 | chr6 | 166267503 | 166267892 |
| chr6 | 166401162 | 166401401 | chr6 | 166402154 | 166402633 | chr6 | 166421831 | 166421992 |
| chr6 | 166421994 | 166422288 | chr6 | 166579636 | 166580234 | chr6 | 166580252 | 166582393 |
| chr6 | 166582395 | 166582827 | chr6 | 166944266 | 166944505 | chr6 | 167835031 | 167835270 |
| chr6 | 168719890 | 168720121 | chr6 | 168842760 | 168843046 | chr6 | 168858030 | 168858389 |
| chr6 | 169653564 | 169653743 | chr6 | 170240691 | 170240797 | chr6 | 170240630 | 170240865 |
| chr6 | 170475007 | 170475366 | chr7 | 329765 | 329942 | chr7 | 369763 | 370062 |
| chr7 | 389589 | 389768 | chr7 | 409740 | 409872 | chr7 | 409887 | 409979 |
| chr7 | 431290 | 431589 | chr7 | 497679 | 498006 | chr7 | 503725 | 504024 |
| chr7 | 551499 | 551778 | chr7 | 557008 | 557076 | chr7 | 578836 | 579121 |
| chr7 | 751726 | 751765 | chr7 | 752022 | 752149 | chr7 | 752151 | 752306 |
| chr7 | 907582 | 907761 | chr7 | 1022150 | 1022329 | chr7 | 1030079 | 1030378 |
| chr7 | 1054489 | 1054780 | chr7 | 1086110 | 1086409 | chr7 | 1263682 | 1264041 |
| chr7 | 1269228 | 1269464 | chr7 | 1269553 | 1269887 | chr7 | 1270304 | 1270543 |
| chr7 | 1273070 | 1273388 | chr7 | 1274540 | 1274779 | chr7 | 1275046 | 1275113 |
| chr7 | 1275481 | 1275682 | chr7 | 1275734 | 1275780 | chr7 | 1277722 | 1277961 |
| chr7 | 1279136 | 1279204 | chr7 | 1279891 | 1280070 | chr7 | 1281033 | 1281332 |
| chr7 | 1281405 | 1281644 | chr7 | 1281947 | 1282246 | chr7 | 1282426 | 1282725 |
| chr7 | 1286715 | 1286754 | chr7 | 1286887 | 1286954 | chr7 | 1288489 | 1288848 |
| chr7 | 1308275 | 1308574 | chr7 | 1325727 | 1325966 | chr7 | 1415941 | 1416226 |
| chr7 | 1423536 | 1423740 | chr7 | 1458967 | 1459183 | chr7 | 1503328 | 1503687 |
| chr7 | 1547234 | 1547413 | chr7 | 1598549 | 1598788 | chr7 | 1607307 | 1607546 |
| chr7 | 1607897 | 1608076 | chr7 | 1641700 | 1641999 | chr7 | 1681095 | 1681334 |
| chr7 | 1688883 | 1689101 | chr7 | 1690649 | 1690801 | chr7 | 1690903 | 1690948 |
| chr7 | 1709038 | 1709337 | chr7 | 1709385 | 1709562 | chr7 | 1709618 | 1709684 |
| chr7 | 1733066 | 1733482 | chr7 | 1775757 | 1775936 | chr7 | 1783468 | 1783470 |
| chr7 | 1786438 | 1786916 | chr7 | 1787066 | 1787425 | chr7 | 1800808 | 1800987 |
| chr7 | 1970776 | 1970947 | chr7 | 2163251 | 2163496 | chr7 | 2208635 | 2208889 |
| chr7 | 2232861 | 2233154 | chr7 | 2233204 | 2233503 | chr7 | 2238051 | 2238327 |
| chr7 | 2300694 | 2300803 | chr7 | 2565961 | 2566130 | chr7 | 2566526 | 2566705 |
| chr7 | 2719928 | 2720227 | chr7 | 2727968 | 2728267 | chr7 | 3033584 | 3033763 |
| chr7 | 3083216 | 3083288 | chr7 | 3083331 | 3083333 | chr7 | 3083335 | 3083338 |
| chr7 | 3083340 | 3083455 | chr7 | 3283620 | 3283978 | chr7 | 3340370 | 3340549 |
| chr7 | 3341394 | 3341409 | chr7 | 3341570 | 3341693 | chr7 | 4215235 | 4215469 |
| chr7 | 4856897 | 4857136 | chr7 | 4922460 | 4922707 | chr7 | 4923328 | 4923475 |
| chr7 | 4998116 | 4998475 | chr7 | 4998771 | 4998837 | chr7 | 5262472 | 5262648 |
| chr7 | 5632841 | 5633200 | chr7 | 5648011 | 5648490 | chr7 | 6060493 | 6060556 |
| chr7 | 6099127 | 6099234 | chr7 | 6124621 | 6124740 | chr7 | 6188652 | 6188831 |
| chr7 | 6188926 | 6189165 | chr7 | 6443198 | 6443478 | chr7 | 6443752 | 6443794 |
| chr7 | 6443871 | 6443931 | chr7 | 6524492 | 6524599 | chr7 | 6524936 | 6525055 |

TABLE 15-continued

Pan-cancer #5

| chr | start | end | chr | start | end | chr | start | end |
|---|---|---|---|---|---|---|---|---|
| chr7 | 6543064 | 6543303 | chr7 | 6560141 | 6560440 | chr7 | 6566329 | 6566748 |
| chr7 | 6570901 | 6571225 | chr7 | 6576043 | 6576185 | chr7 | 6703458 | 6703708 |
| chr7 | 6703710 | 6703803 | chr7 | 6703805 | 6703870 | chr7 | 6703916 | 6704057 |
| chr7 | 7605665 | 7605902 | chr7 | 8472995 | 8473456 | chr7 | 8473480 | 8473762 |
| chr7 | 8473870 | 8474242 | chr7 | 8474516 | 8474649 | chr7 | 8474727 | 8475146 |
| chr7 | 8480647 | 8481126 | chr7 | 8481228 | 8481260 | chr7 | 8481559 | 8481918 |
| chr7 | 8481980 | 8482298 | chr7 | 8482670 | 8482825 | chr7 | 8482885 | 8482999 |
| chr7 | 8483070 | 8484029 | chr7 | 12151350 | 12151473 | chr7 | 12151524 | 12151769 |
| chr7 | 12443241 | 12443480 | chr7 | 12443767 | 12443806 | chr7 | 12610259 | 12610317 |
| chr7 | 12610539 | 12610558 | chr7 | 15725883 | 15726182 | chr7 | 15726557 | 15727156 |
| chr7 | 15727216 | 15727395 | chr7 | 19145730 | 19145894 | chr7 | 19146032 | 19146185 |
| chr7 | 19146238 | 19146329 | chr7 | 19146411 | 19146650 | chr7 | 19147041 | 19147880 |
| chr7 | 19152224 | 19152368 | chr7 | 19155865 | 19155896 | chr7 | 19155984 | 19156062 |
| chr7 | 19156126 | 19156133 | chr7 | 19156304 | 19156643 | chr7 | 19156705 | 19156746 |
| chr7 | 19157056 | 19157193 | chr7 | 19157195 | 19157263 | chr7 | 19157265 | 19157567 |
| chr7 | 19157634 | 19158099 | chr7 | 19183978 | 19184337 | chr7 | 19813210 | 19813350 |
| chr7 | 20816175 | 20816530 | chr7 | 20817306 | 20817332 | chr7 | 20817452 | 20817485 |
| chr7 | 20818037 | 20818276 | chr7 | 20823213 | 20823331 | chr7 | 20823383 | 20823512 |
| chr7 | 20823826 | 20823879 | chr7 | 20823920 | 20824144 | chr7 | 20824476 | 20824820 |
| chr7 | 20824836 | 20825025 | chr7 | 20825290 | 20825363 | chr7 | 20826803 | 20826939 |
| chr7 | 20827224 | 20827282 | chr7 | 20830596 | 20830775 | chr7 | 20833066 | 20833425 |
| chr7 | 21582492 | 21582641 | chr7 | 21582792 | 21582971 | chr7 | 21583176 | 21583278 |
| chr7 | 21583304 | 21583415 | chr7 | 22539752 | 22539991 | chr7 | 22589254 | 22589973 |
| chr7 | 23287170 | 23287351 | chr7 | 23287533 | 23287709 | chr7 | 23578824 | 23578943 |
| chr7 | 24324002 | 24324028 | chr7 | 24580786 | 24580905 | chr7 | 24796404 | 24796643 |
| chr7 | 25892430 | 25892431 | chr7 | 25892609 | 25892669 | chr7 | 25896424 | 25896603 |
| chr7 | 25896675 | 25896963 | chr7 | 27127919 | 27128001 | chr7 | 27135232 | 27135771 |
| chr7 | 27135980 | 27136424 | chr7 | 27136426 | 27136868 | chr7 | 27190490 | 27191329 |
| chr7 | 27195483 | 27195602 | chr7 | 27195867 | 27195893 | chr7 | 27196153 | 27196153 |
| chr7 | 27196155 | 27196286 | chr7 | 27196288 | 27196742 | chr7 | 27204402 | 27204770 |
| chr7 | 27205266 | 27205381 | chr7 | 27205383 | 27205481 | chr7 | 27205599 | 27205790 |
| chr7 | 27206083 | 27206138 | chr7 | 27209413 | 27209672 | chr7 | 27209690 | 27209772 |
| chr7 | 27212400 | 27212984 | chr7 | 27213189 | 27213984 | chr7 | 27213986 | 27214262 |
| chr7 | 27214330 | 27214401 | chr7 | 27223031 | 27223193 | chr7 | 27223222 | 27223253 |
| chr7 | 27223500 | 27223799 | chr7 | 27223980 | 27224699 | chr7 | 27224945 | 27225058 |
| chr7 | 27227795 | 27228034 | chr7 | 27232207 | 27233046 | chr7 | 27238813 | 27238992 |
| chr7 | 27239087 | 27239173 | chr7 | 27239226 | 27239326 | chr7 | 27240127 | 27240423 |
| chr7 | 27244446 | 27244611 | chr7 | 27244798 | 27245393 | chr7 | 27245583 | 27245733 |
| chr7 | 27252306 | 27252485 | chr7 | 27264801 | 27265400 | chr7 | 27265442 | 27265678 |
| chr7 | 27275467 | 27275532 | chr7 | 27279238 | 27279369 | chr7 | 27279454 | 27279554 |
| chr7 | 27282012 | 27283091 | chr7 | 27283250 | 27283295 | chr7 | 27285436 | 27285519 |
| chr7 | 27285621 | 27285825 | chr7 | 27288869 | 27288945 | chr7 | 27289446 | 27289528 |
| chr7 | 27291048 | 27291119 | chr7 | 27291315 | 27291947 | chr7 | 28449197 | 28449291 |
| chr7 | 28449659 | 28449782 | chr7 | 28449858 | 28450096 | chr7 | 28995579 | 28996058 |
| chr7 | 28996357 | 28996596 | chr7 | 28996759 | 28996998 | chr7 | 28997052 | 28997485 |
| chr7 | 28997487 | 28997646 | chr7 | 28997677 | 28997711 | chr7 | 28997967 | 28998206 |
| chr7 | 30721202 | 30721943 | chr7 | 30722214 | 30722453 | chr7 | 31092919 | 31093218 |
| chr7 | 31375899 | 31376230 | chr7 | 32110616 | 32110650 | chr7 | 32110652 | 32110692 |
| chr7 | 32110704 | 32110855 | chr7 | 32337733 | 32337912 | chr7 | 32338044 | 32338218 |
| chr7 | 32338274 | 32338489 | chr7 | 32338826 | 32339005 | chr7 | 32467373 | 32467656 |
| chr7 | 32467947 | 32468151 | chr7 | 32997050 | 32997463 | chr7 | 33943370 | 33943849 |
| chr7 | 35225724 | 35225834 | chr7 | 35226090 | 35226523 | chr7 | 35226557 | 35226610 |
| chr7 | 35226612 | 35226811 | chr7 | 35292893 | 35293087 | chr7 | 35293183 | 35293372 |
| chr7 | 35294032 | 35294228 | chr7 | 35294400 | 35294639 | chr7 | 35295030 | 35295106 |
| chr7 | 35295807 | 35296000 | chr7 | 35296855 | 35297005 | chr7 | 35297138 | 35297354 |
| chr7 | 35297471 | 35298017 | chr7 | 35300851 | 35301009 | chr7 | 35301102 | 35302050 |
| chr7 | 35494278 | 35494333 | chr7 | 35494470 | 35494517 | chr7 | 37487076 | 37487251 |
| chr7 | 37487376 | 37487454 | chr7 | 37487756 | 37487915 | chr7 | 37488179 | 37488658 |
| chr7 | 37488837 | 37489076 | chr7 | 37907366 | 37907545 | chr7 | 37955780 | 37956079 |
| chr7 | 37956176 | 37956535 | chr7 | 37960199 | 37960438 | chr7 | 38670267 | 38670664 |
| chr7 | 38670957 | 38670985 | chr7 | 38670987 | 38671106 | chr7 | 39015463 | 39016062 |
| chr7 | 42267573 | 42267712 | chr7 | 42276251 | 42276730 | chr7 | 42533028 | 42533081 |
| chr7 | 42533224 | 42533387 | chr7 | 43152016 | 43152208 | chr7 | 43152414 | 43152795 |
| chr7 | 43152858 | 43153200 | chr7 | 43153230 | 43153337 | chr7 | 44097656 | 44097895 |
| chr7 | 44143906 | 44143942 | chr7 | 44144030 | 44144085 | chr7 | 44151324 | 44151503 |
| chr7 | 44151715 | 44151857 | chr7 | 44164017 | 44164078 | chr7 | 44364752 | 44364991 |
| chr7 | 44835122 | 44835467 | chr7 | 45038447 | 45038564 | chr7 | 45613693 | 45613814 |
| chr7 | 45613858 | 45613992 | chr7 | 45614259 | 45614558 | chr7 | 45614655 | 45615061 |
| chr7 | 45615536 | 45615588 | chr7 | 45960650 | 45960889 | chr7 | 45961072 | 45961251 |
| chr7 | 45961423 | 45961630 | chr7 | 45961656 | 45961662 | chr7 | 45961742 | 45961981 |
| chr7 | 49812718 | 49813018 | chr7 | 49813810 | 49814093 | chr7 | 49814454 | 49814751 |
| chr7 | 49815117 | 49815250 | chr7 | 49815657 | 49815848 | chr7 | 50294460 | 50294556 |
| chr7 | 50343183 | 50343482 | chr7 | 50343975 | 50344086 | chr7 | 50344150 | 50344294 |
| chr7 | 50344296 | 50344331 | chr7 | 50344333 | 50344569 | chr7 | 50364988 | 50365069 |
| chr7 | 50438544 | 50438723 | chr7 | 50560494 | 50560733 | chr7 | 50860135 | 50860393 |
| chr7 | 50860980 | 50861103 | chr7 | 50861128 | 50861214 | chr7 | 51384235 | 51384534 |

TABLE 15-continued

Pan-cancer #5

| chr | start | end | chr | start | end | chr | start | end |
|---|---|---|---|---|---|---|---|---|
| chr7 | 51384814 | 51385006 | chr7 | 54609764 | 54609952 | chr7 | 54609992 | 54610022 |
| chr7 | 54610024 | 54610243 | chr7 | 54612335 | 54612814 | chr7 | 55086481 | 55086687 |
| chr7 | 55086899 | 55087618 | chr7 | 55409933 | 55410223 | chr7 | 56018026 | 56018205 |
| chr7 | 56031847 | 56031966 | chr7 | 64330322 | 64330561 | chr7 | 64330635 | 64330645 |
| chr7 | 64348952 | 64348968 | chr7 | 64349042 | 64349131 | chr7 | 64349318 | 64349551 |
| chr7 | 64700198 | 64700426 | chr7 | 64712288 | 64712587 | chr7 | 64974283 | 64974402 |
| chr7 | 65037592 | 65037702 | chr7 | 65508900 | 65509124 | chr7 | 66214974 | 66215062 |
| chr7 | 68204692 | 68204931 | chr7 | 69062428 | 69062727 | chr7 | 69064489 | 69064772 |
| chr7 | 69064834 | 69065148 | chr7 | 69897685 | 69897924 | chr7 | 70596353 | 70596416 |
| chr7 | 70596454 | 70596711 | chr7 | 70597368 | 70597368 | chr7 | 70597395 | 70597549 |
| chr7 | 70597752 | 70597754 | chr7 | 70597780 | 70597872 | chr7 | 70597991 | 70598124 |
| chr7 | 70598170 | 70598471 | chr7 | 71217011 | 71217320 | chr7 | 71217322 | 71217366 |
| chr7 | 71800599 | 71800757 | chr7 | 71800934 | 71801105 | chr7 | 71802315 | 71802347 |
| chr7 | 71802390 | 71802396 | chr7 | 71802457 | 71802523 | chr7 | 71802578 | 71802734 |
| chr7 | 71871105 | 71871157 | chr7 | 76033251 | 76033364 | chr7 | 77324278 | 77324397 |
| chr7 | 79081718 | 79081897 | chr7 | 79081942 | 79081969 | chr7 | 79082070 | 79082301 |
| chr7 | 79083016 | 79083035 | chr7 | 79083191 | 79083255 | chr7 | 79083314 | 79083913 |
| chr7 | 82072248 | 82072562 | chr7 | 84815049 | 84815135 | chr7 | 84815397 | 84815468 |
| chr7 | 84815670 | 84816029 | chr7 | 86273108 | 86273645 | chr7 | 86274018 | 86274117 |
| chr7 | 86274258 | 86274547 | chr7 | 87104725 | 87105445 | chr7 | 87229446 | 87230189 |
| chr7 | 87230191 | 87230344 | chr7 | 87230525 | 87230525 | chr7 | 87256911 | 87257074 |
| chr7 | 87257076 | 87257150 | chr7 | 87257964 | 87258143 | chr7 | 88387904 | 88388130 |
| chr7 | 88388247 | 88388263 | chr7 | 88388439 | 88388646 | chr7 | 88388648 | 88388738 |
| chr7 | 88388789 | 88388902 | chr7 | 88389047 | 88389389 | chr7 | 89747928 | 89748294 |
| chr7 | 89748296 | 89748438 | chr7 | 89950108 | 89950813 | chr7 | 90226188 | 90226284 |
| chr7 | 90226286 | 90226547 | chr7 | 90894936 | 90895027 | chr7 | 90895029 | 90895175 |
| chr7 | 92466078 | 92466486 | chr7 | 92689613 | 92689774 | chr7 | 93203613 | 93203852 |
| chr7 | 93204299 | 93204592 | chr7 | 93519265 | 93519766 | chr7 | 93519855 | 93520024 |
| chr7 | 93520026 | 93520224 | chr7 | 93551225 | 93551524 | chr7 | 94284277 | 94284978 |
| chr7 | 96619499 | 96619678 | chr7 | 96621614 | 96621913 | chr7 | 96622019 | 96622438 |
| chr7 | 96625472 | 96625809 | chr7 | 96625906 | 96626145 | chr7 | 96631614 | 96631780 |
| chr7 | 96634577 | 96634996 | chr7 | 96635260 | 96635379 | chr7 | 96635440 | 96635452 |
| chr7 | 96635487 | 96635559 | chr7 | 96635650 | 96635972 | chr7 | 96636034 | 96636729 |
| chr7 | 96646568 | 96647227 | chr7 | 96647715 | 96648314 | chr7 | 96650809 | 96651077 |
| chr7 | 96651137 | 96651228 | chr7 | 96651384 | 96651584 | chr7 | 96652070 | 96652249 |
| chr7 | 96653421 | 96653820 | chr7 | 96653863 | 96654080 | chr7 | 97361021 | 97361423 |
| chr7 | 97361521 | 97361860 | chr7 | 97362211 | 97362690 | chr7 | 97600015 | 97600194 |
| chr7 | 97869540 | 97869719 | chr7 | 98245857 | 98246079 | chr7 | 98246305 | 98246508 |
| chr7 | 98246534 | 98246947 | chr7 | 98247032 | 98247751 | chr7 | 98971530 | 98971649 |
| chr7 | 99104174 | 99104293 | chr7 | 99177657 | 99177663 | chr7 | 99177695 | 99177956 |
| chr7 | 99591732 | 99591851 | chr7 | 99595184 | 99595336 | chr7 | 99751485 | 99751553 |
| chr7 | 99775118 | 99775297 | chr7 | 100088099 | 100088398 | chr7 | 100091115 | 100091181 |
| chr7 | 100179789 | 100180017 | chr7 | 100318467 | 100318660 | chr7 | 100808365 | 100808596 |
| chr7 | 100809360 | 100809599 | chr7 | 100823348 | 100823351 | chr7 | 100823381 | 100823587 |
| chr7 | 101005901 | 101006073 | chr7 | 101241919 | 101242098 | chr7 | 101475705 | 101475944 |
| chr7 | 101627683 | 101627884 | chr7 | 101707428 | 101707535 | chr7 | 103085786 | 103086565 |
| chr7 | 103628963 | 103629795 | chr7 | 103630054 | 103630083 | chr7 | 103630381 | 103630549 |
| chr7 | 103630551 | 103630920 | chr7 | 103969130 | 103969166 | chr7 | 103969168 | 103969429 |
| chr7 | 103969595 | 103969679 | chr7 | 103969694 | 103969894 | chr7 | 105279390 | 105279749 |
| chr7 | 106685195 | 106685434 | chr7 | 106797700 | 106797856 | chr7 | 107301418 | 107301717 |
| chr7 | 107483597 | 107484016 | chr7 | 108095227 | 108095466 | chr7 | 108095781 | 108096141 |
| chr7 | 108097093 | 108097572 | chr7 | 112726529 | 112726538 | chr7 | 112726540 | 112726706 |
| chr7 | 113722736 | 113723284 | chr7 | 113723339 | 113723515 | chr7 | 113724870 | 113725169 |
| chr7 | 113726435 | 113726614 | chr7 | 113727345 | 113727584 | chr7 | 113727755 | 113727872 |
| chr7 | 115117451 | 115117750 | chr7 | 116140155 | 116140268 | chr7 | 116962796 | 116963147 |
| chr7 | 116963331 | 116963575 | chr7 | 117119347 | 117120366 | chr7 | 119913464 | 119913837 |
| chr7 | 120969587 | 120969886 | chr7 | 121513457 | 121513796 | chr7 | 121939584 | 121940245 |
| chr7 | 121940434 | 121940543 | chr7 | 121940845 | 121941144 | chr7 | 121941807 | 121942266 |
| chr7 | 121943905 | 121943989 | chr7 | 121944177 | 121944264 | chr7 | 121945722 | 121946021 |
| chr7 | 121946403 | 121946983 | chr7 | 121947098 | 121947482 | chr7 | 121950034 | 121950265 |
| chr7 | 121950429 | 121950553 | chr7 | 121950995 | 121951029 | chr7 | 121951784 | 121952011 |
| chr7 | 121952044 | 121952256 | chr7 | 121956408 | 121956582 | chr7 | 121956955 | 121957077 |
| chr7 | 121957254 | 121957256 | chr7 | 121957411 | 121957411 | chr7 | 123173048 | 123173327 |
| chr7 | 123671948 | 123672187 | chr7 | 124404320 | 124404498 | chr7 | 124404544 | 124404619 |
| chr7 | 126891146 | 126891325 | chr7 | 126891430 | 126891669 | chr7 | 127371055 | 127371234 |
| chr7 | 127615847 | 127616026 | chr7 | 127744048 | 127744210 | chr7 | 127744212 | 127744707 |
| chr7 | 127806560 | 127806739 | chr7 | 127807922 | 127807922 | chr7 | 127808791 | 127808822 |
| chr7 | 127841426 | 127841497 | chr7 | 127841626 | 127841785 | chr7 | 127991742 | 127991743 |
| chr7 | 127991788 | 127991923 | chr7 | 127992045 | 127992221 | chr7 | 128096988 | 128097164 |
| chr7 | 128337365 | 128337543 | chr7 | 128337788 | 128338023 | chr7 | 128470816 | 128471057 |
| chr7 | 128486020 | 128486237 | chr7 | 128528729 | 128528854 | chr7 | 128528949 | 128529128 |
| chr7 | 128828115 | 128828354 | chr7 | 129229605 | 129229724 | chr7 | 129418168 | 129418513 |
| chr7 | 129422116 | 129422969 | chr7 | 129423126 | 129423509 | chr7 | 129424552 | 129425991 |
| chr7 | 129426215 | 129426336 | chr7 | 129794508 | 129794807 | chr7 | 129800223 | 129800462 |
| chr7 | 131041437 | 131041676 | chr7 | 131242662 | 131242901 | chr7 | 131514750 | 131514929 |
| chr7 | 132261173 | 132261208 | chr7 | 132261257 | 132261505 | chr7 | 134143081 | 134143560 |

TABLE 15-continued

Pan-cancer #5

| chr | start | end | chr | start | end | chr | start | end |
|---|---|---|---|---|---|---|---|---|
| chr7 | 134143731 | 134143971 | chr7 | 134143973 | 134144055 | chr7 | 134144057 | 134144209 |
| chr7 | 134918421 | 134918720 | chr7 | 136553316 | 136553495 | chr7 | 136553556 | 136554026 |
| chr7 | 136554104 | 136554469 | chr7 | 136554563 | 136554581 | chr7 | 136554626 | 136555001 |
| chr7 | 136555145 | 136555504 | chr7 | 136555587 | 136555842 | chr7 | 136556013 | 136556186 |
| chr7 | 137028402 | 137028623 | chr7 | 137531153 | 137531212 | chr7 | 137531263 | 137531889 |
| chr7 | 137531909 | 137532188 | chr7 | 137532374 | 137532438 | chr7 | 138042136 | 138042315 |
| chr7 | 139167532 | 139167827 | chr7 | 139168115 | 139168481 | chr7 | 139208697 | 139208888 |
| chr7 | 139930070 | 139930371 | chr7 | 139939304 | 139939314 | chr7 | 140026925 | 140027043 |
| chr7 | 140180180 | 140180298 | chr7 | 140339839 | 140339868 | chr7 | 140339966 | 140340078 |
| chr7 | 140453048 | 140453227 | chr7 | 140772717 | 140773312 | chr7 | 140773478 | 140773837 |
| chr7 | 143042537 | 143042896 | chr7 | 143579665 | 143579665 | chr7 | 143579667 | 143579951 |
| chr7 | 143579953 | 143580144 | chr7 | 145812918 | 145813008 | chr7 | 145813010 | 145813157 |
| chr7 | 145813334 | 145813391 | chr7 | 145813404 | 145813573 | chr7 | 145813946 | 145814269 |
| chr7 | 148224592 | 148224711 | chr7 | 148640242 | 148640331 | chr7 | 148846061 | 148846279 |
| chr7 | 149111968 | 149112226 | chr7 | 149112421 | 149112507 | chr7 | 149119862 | 149120124 |
| chr7 | 149411444 | 149411728 | chr7 | 149411835 | 149412403 | chr7 | 149744462 | 149744653 |
| chr7 | 149917322 | 149917412 | chr7 | 149918045 | 149918191 | chr7 | 150049512 | 150049626 |
| chr7 | 150069013 | 150069432 | chr7 | 150069601 | 150069662 | chr7 | 150069837 | 150069900 |
| chr7 | 150069921 | 150070160 | chr7 | 150081153 | 150081354 | chr7 | 150716088 | 150716387 |
| chr7 | 150748090 | 150748509 | chr7 | 150753843 | 150754082 | chr7 | 150870734 | 150870973 |
| chr7 | 151106369 | 151106566 | chr7 | 151106989 | 151107637 | chr7 | 151107396 | 151107637 |
| chr7 | 151107639 | 151107749 | chr7 | 151591567 | 151591806 | chr7 | 152622546 | 152622779 |
| chr7 | 153583503 | 153583530 | chr7 | 153583632 | 153584162 | chr7 | 153584297 | 153584546 |
| chr7 | 153584694 | 153584716 | chr7 | 153584758 | 153585233 | chr7 | 153585333 | 153585396 |
| chr7 | 153585602 | 153585692 | chr7 | 153750043 | 153750345 | chr7 | 154561051 | 154561290 |
| chr7 | 154708188 | 154708355 | chr7 | 154861947 | 154862030 | chr7 | 154862032 | 154862366 |
| chr7 | 155164379 | 155165638 | chr7 | 155165791 | 155166870 | chr7 | 155166933 | 155167038 |
| chr7 | 155167040 | 155167090 | chr7 | 155167175 | 155167661 | chr7 | 155167834 | 155167844 |
| chr7 | 155167846 | 155167992 | chr7 | 155174573 | 155174872 | chr7 | 155241235 | 155241490 |
| chr7 | 155241492 | 155242134 | chr7 | 155242700 | 155243186 | chr7 | 155243245 | 155243534 |
| chr7 | 155243756 | 155243980 | chr7 | 155244092 | 155244451 | chr7 | 155246859 | 155247480 |
| chr7 | 155247651 | 155247685 | chr7 | 155248839 | 155249018 | chr7 | 155249420 | 155249659 |
| chr7 | 155249849 | 155250088 | chr7 | 155250200 | 155250304 | chr7 | 155250324 | 155250439 |
| chr7 | 155250713 | 155251072 | chr7 | 155251662 | 155251855 | chr7 | 155251891 | 155252030 |
| chr7 | 155252160 | 155252262 | chr7 | 155252317 | 155252579 | chr7 | 155252773 | 155253132 |
| chr7 | 155254765 | 155255416 | chr7 | 155256216 | 155256233 | chr7 | 155256269 | 155256395 |
| chr7 | 155256986 | 155257265 | chr7 | 155258101 | 155258580 | chr7 | 155258854 | 155258864 |
| chr7 | 155258915 | 155259078 | chr7 | 155259120 | 155259623 | chr7 | 155259834 | 155259845 |
| chr7 | 155259847 | 155259958 | chr7 | 155260039 | 155260233 | chr7 | 155260806 | 155260891 |
| chr7 | 155261071 | 155261285 | chr7 | 155301736 | 155302035 | chr7 | 155302267 | 155302896 |
| chr7 | 155302964 | 155303432 | chr7 | 155325720 | 155325954 | chr7 | 155326079 | 155326618 |
| chr7 | 155363212 | 155363511 | chr7 | 155580308 | 155580745 | chr7 | 155580772 | 155580882 |
| chr7 | 155581243 | 155581652 | chr7 | 155581664 | 155581962 | chr7 | 155582190 | 155582369 |
| chr7 | 155600527 | 155600825 | chr7 | 155602726 | 155602898 | chr7 | 156409214 | 156409426 |
| chr7 | 156409728 | 156409884 | chr7 | 156701794 | 156701997 | chr7 | 156744697 | 156744816 |
| chr7 | 156794465 | 156794579 | chr7 | 156794922 | 156795355 | chr7 | 156795402 | 156795636 |
| chr7 | 156795900 | 156795996 | chr7 | 156796442 | 156796740 | chr7 | 156797006 | 156798435 |
| chr7 | 156798527 | 156799147 | chr7 | 156799291 | 156799561 | chr7 | 156800925 | 156801104 |
| chr7 | 156801323 | 156801682 | chr7 | 156808760 | 156809299 | chr7 | 156809953 | 156810522 |
| chr7 | 156810598 | 156810801 | chr7 | 156811303 | 156811520 | chr7 | 156812773 | 156813826 |
| chr7 | 156813987 | 156814230 | chr7 | 156815096 | 156815170 | chr7 | 156832194 | 156832493 |
| chr7 | 156832766 | 156833245 | chr7 | 156871084 | 156871153 | chr7 | 156871283 | 156871383 |
| chr7 | 156880457 | 156880636 | chr7 | 157085281 | 157085580 | chr7 | 157085874 | 157086173 |
| chr7 | 157262738 | 157262097 | chr7 | 157262204 | 157263563 | chr7 | 157361531 | 157361653 |
| chr7 | 157476790 | 157476974 | chr7 | 157476995 | 157477376 | chr7 | 157477395 | 157477489 |
| chr7 | 157477711 | 157477820 | chr7 | 157481534 | 157481550 | chr7 | 157481760 | 157481860 |
| chr7 | 157481890 | 157482074 | chr7 | 157482201 | 157482249 | chr7 | 157482401 | 157482508 |
| chr7 | 157482510 | 157482760 | chr7 | 157483220 | 157483639 | chr7 | 157484778 | 157485377 |
| chr7 | 157485437 | 157485602 | chr7 | 157485650 | 157485796 | chr7 | 157485881 | 157486082 |
| chr7 | 157486205 | 157486415 | chr7 | 157486476 | 157486600 | chr7 | 157584104 | 157584283 |
| chr7 | 157588510 | 157588869 | chr7 | 157606632 | 157606811 | chr7 | 157690145 | 157690161 |
| chr7 | 158059659 | 158059898 | chr7 | 158936420 | 158936956 | chr7 | 158937062 | 158937091 |
| chr7 | 158937203 | 158937375 | chr7 | 158937577 | 158937610 | chr7 | 158937612 | 158937721 |
| chr7 | 158938132 | 158938485 | chr8 | 686794 | 686885 | chr8 | 687163 | 687218 |
| chr8 | 687838 | 687976 | chr8 | 1085559 | 1085678 | chr8 | 4849040 | 4849263 |
| chr8 | 4849364 | 4849603 | chr8 | 4850173 | 4850323 | chr8 | 4850419 | 4850592 |
| chr8 | 4851662 | 4851686 | chr8 | 4851722 | 4851750 | chr8 | 4851781 | 4851841 |
| chr8 | 4851921 | 4852220 | chr8 | 8748329 | 8748808 | chr8 | 8748819 | 8749058 |
| chr8 | 9722754 | 9722993 | chr8 | 9755973 | 9756284 | chr8 | 9756487 | 9756564 |
| chr8 | 9760646 | 9761245 | chr8 | 9762487 | 9762690 | chr8 | 9762752 | 9762965 |
| chr8 | 9763060 | 9763359 | chr8 | 9763816 | 9764050 | chr8 | 9764196 | 9764295 |
| chr8 | 9764344 | 9764643 | chr8 | 10587507 | 10587603 | chr8 | 11204405 | 11204584 |
| chr8 | 11204709 | 11205008 | chr8 | 11536753 | 11536932 | chr8 | 11537157 | 11537362 |
| chr8 | 11554886 | 11554990 | chr8 | 11555068 | 11555167 | chr8 | 11555474 | 11555605 |
| chr8 | 11559707 | 11559792 | chr8 | 11560068 | 11560457 | chr8 | 11560633 | 11560872 |
| chr8 | 11561357 | 11561724 | chr8 | 11561726 | 11562196 | chr8 | 11562236 | 11562256 |

TABLE 15-continued

Pan-cancer #5

| chr | start | end | chr | start | end | chr | start | end |
|---|---|---|---|---|---|---|---|---|
| chr8 | 11562335 | 11562574 | chr8 | 11562600 | 11563019 | chr8 | 11705869 | 11706228 |
| chr8 | 11726393 | 11726505 | chr8 | 12990409 | 12990529 | chr8 | 12990575 | 12990874 |
| chr8 | 13319857 | 13319937 | chr8 | 15094425 | 15094567 | chr8 | 15094646 | 15094664 |
| chr8 | 15397641 | 15397660 | chr8 | 16884239 | 16884331 | chr8 | 16885104 | 16885343 |
| chr8 | 17271091 | 17271213 | chr8 | 19797396 | 19797538 | chr8 | 19797860 | 19798099 |
| chr8 | 20160679 | 20160710 | chr8 | 22089428 | 22089665 | chr8 | 22562487 | 22562564 |
| chr8 | 22960567 | 22960806 | chr8 | 23021083 | 23021131 | chr8 | 23021193 | 23021209 |
| chr8 | 23260598 | 23260957 | chr8 | 23423830 | 23424009 | chr8 | 23559296 | 23559602 |
| chr8 | 23559666 | 23560615 | chr8 | 23563712 | 23564024 | chr8 | 23564193 | 23564480 |
| chr8 | 23564703 | 23565108 | chr8 | 23566729 | 23566855 | chr8 | 23566901 | 23567214 |
| chr8 | 23567312 | 23567568 | chr8 | 23571588 | 23572029 | chr8 | 23572031 | 23572067 |
| chr8 | 23572334 | 23572646 | chr8 | 23584000 | 23584017 | chr8 | 23584094 | 23584401 |
| chr8 | 23584582 | 23584839 | chr8 | 24770239 | 24770362 | chr8 | 24770414 | 24770658 |
| chr8 | 24771072 | 24771125 | chr8 | 24771350 | 24771575 | chr8 | 24771633 | 24771647 |
| chr8 | 24813089 | 24813388 | chr8 | 24813660 | 24813894 | chr8 | 24814011 | 24814499 |
| chr8 | 24857673 | 24857912 | chr8 | 24858239 | 24858538 | chr8 | 24858770 | 24859249 |
| chr8 | 24859422 | 24859601 | chr8 | 25041656 | 25041955 | chr8 | 25042636 | 25042671 |
| chr8 | 25900324 | 25900693 | chr8 | 25900781 | 25901017 | chr8 | 25901019 | 25901403 |
| chr8 | 25901444 | 25901863 | chr8 | 25902072 | 25902251 | chr8 | 25902545 | 25902640 |
| chr8 | 25903579 | 25903938 | chr8 | 25904055 | 25904294 | chr8 | 25905022 | 25905201 |
| chr8 | 25905696 | 25905907 | chr8 | 25909098 | 25909599 | chr8 | 25909601 | 25909697 |
| chr8 | 26372789 | 26372968 | chr8 | 26723884 | 26724183 | chr8 | 30243289 | 30243526 |
| chr8 | 30769151 | 30769510 | chr8 | 30770028 | 30770110 | chr8 | 30770158 | 30770267 |
| chr8 | 31496380 | 31496859 | chr8 | 31496939 | 31497042 | chr8 | 31497044 | 31497176 |
| chr8 | 31497420 | 31497719 | chr8 | 32406517 | 32406928 | chr8 | 32406930 | 32406996 |
| chr8 | 33371978 | 33372217 | chr8 | 33457052 | 33457471 | chr8 | 35093037 | 35093140 |
| chr8 | 35093877 | 35093974 | chr8 | 35094036 | 35094056 | chr8 | 37655367 | 37655376 |
| chr8 | 37655476 | 37655606 | chr8 | 37655707 | 37655991 | chr8 | 37656050 | 37656186 |
| chr8 | 37822721 | 37823409 | chr8 | 37823411 | 37823475 | chr8 | 37823477 | 37823500 |
| chr8 | 37823790 | 37823805 | chr8 | 37961879 | 37961998 | chr8 | 38008157 | 38008636 |
| chr8 | 38323837 | 38324016 | chr8 | 38965450 | 38965464 | chr8 | 41165785 | 41165919 |
| chr8 | 41166001 | 41166152 | chr8 | 41166267 | 41166680 | chr8 | 41166746 | 41166804 |
| chr8 | 41166886 | 41166989 | chr8 | 41167026 | 41167125 | chr8 | 41424682 | 41424921 |
| chr8 | 41624752 | 41624931 | chr8 | 41625038 | 41625217 | chr8 | 41733424 | 41733654 |
| chr8 | 41733685 | 41733723 | chr8 | 41753498 | 41753753 | chr8 | 41753771 | 41753857 |
| chr8 | 41754070 | 41754181 | chr8 | 41754183 | 41754969 | chr8 | 41755104 | 41755283 |
| chr8 | 41910186 | 41910425 | chr8 | 42147417 | 42147596 | chr8 | 42749996 | 42750094 |
| chr8 | 47093172 | 47093351 | chr8 | 47334530 | 47334694 | chr8 | 48100075 | 48100539 |
| chr8 | 49293280 | 49293525 | chr8 | 49293581 | 49293699 | chr8 | 49468571 | 49468828 |
| chr8 | 49468830 | 49469228 | chr8 | 49571955 | 49572134 | chr8 | 49782953 | 49783235 |
| chr8 | 49959156 | 49959335 | chr8 | 50822095 | 50822358 | chr8 | 50822591 | 50822830 |
| chr8 | 50823358 | 50823657 | chr8 | 53477325 | 53477737 | chr8 | 53477945 | 53478352 |
| chr8 | 53478391 | 53478454 | chr8 | 53478456 | 53478744 | chr8 | 53853711 | 53854552 |
| chr8 | 54163240 | 54163350 | chr8 | 54163674 | 54164127 | chr8 | 54789175 | 54789414 |
| chr8 | 54789556 | 54789806 | chr8 | 54790023 | 54790155 | chr8 | 54790214 | 54790883 |
| chr8 | 54791724 | 54791782 | chr8 | 54791898 | 54791946 | chr8 | 54792185 | 54792323 |
| chr8 | 54792548 | 54792671 | chr8 | 54792702 | 54792847 | chr8 | 54794123 | 54794422 |
| chr8 | 54794626 | 54794781 | chr8 | 54794827 | 54794950 | chr8 | 54795140 | 54795165 |
| chr8 | 55366106 | 55366368 | chr8 | 55366952 | 55367725 | chr8 | 55370037 | 55370336 |
| chr8 | 55370338 | 55370423 | chr8 | 55370425 | 55370433 | chr8 | 55370568 | 55370714 |
| chr8 | 55370836 | 55370936 | chr8 | 55371173 | 55371376 | chr8 | 55371440 | 55371725 |
| chr8 | 55371994 | 55372068 | chr8 | 55372417 | 55372638 | chr8 | 55379202 | 55379231 |
| chr8 | 55379296 | 55379457 | chr8 | 55380037 | 55380041 | chr8 | 55382673 | 55382673 |
| chr8 | 55383183 | 55383332 | chr8 | 56013545 | 56013893 | chr8 | 56014012 | 56014024 |
| chr8 | 56014058 | 56014185 | chr8 | 56014377 | 56014417 | chr8 | 56014524 | 56014744 |
| chr8 | 56015035 | 56015053 | chr8 | 56015186 | 56015438 | chr8 | 56015471 | 56015662 |
| chr8 | 56015834 | 56015893 | chr8 | 57025609 | 57025620 | chr8 | 57025776 | 57026028 |
| chr8 | 57026072 | 57026311 | chr8 | 57026502 | 57026644 | chr8 | 57069473 | 57069738 |
| chr8 | 57069851 | 57070013 | chr8 | 57070015 | 57070245 | chr8 | 57358053 | 57358147 |
| chr8 | 57358465 | 57358662 | chr8 | 57358807 | 57359092 | chr8 | 57359260 | 57359732 |
| chr8 | 57360472 | 57360626 | chr8 | 57360770 | 57360891 | chr8 | 58105852 | 58106211 |
| chr8 | 58116923 | 58117162 | chr8 | 58130290 | 58130649 | chr8 | 58907618 | 58907821 |
| chr8 | 58907823 | 58907917 | chr8 | 59058934 | 59059233 | chr8 | 59747274 | 59747402 |
| chr8 | 60032590 | 60032829 | chr8 | 61777488 | 61777622 | chr8 | 61789900 | 61790076 |
| chr8 | 62200414 | 62200879 | chr8 | 63161580 | 63161879 | chr8 | 65281539 | 65281778 |
| chr8 | 65281884 | 65282005 | chr8 | 65282333 | 65282441 | chr8 | 65283708 | 65284187 |
| chr8 | 65285972 | 65286067 | chr8 | 65286371 | 65286451 | chr8 | 65286599 | 65286838 |
| chr8 | 65286868 | 65287229 | chr8 | 65289033 | 65289332 | chr8 | 65289517 | 65290450 |
| chr8 | 65290570 | 65290682 | chr8 | 65290950 | 65291369 | chr8 | 65292572 | 65292816 |
| chr8 | 65488178 | 65488417 | chr8 | 65488618 | 65488799 | chr8 | 65489025 | 65489065 |
| chr8 | 65489067 | 65489204 | chr8 | 65492637 | 65493056 | chr8 | 65493105 | 65493524 |
| chr8 | 65493556 | 65493579 | chr8 | 65493807 | 65493855 | chr8 | 65493868 | 65493955 |
| chr8 | 65494077 | 65494101 | chr8 | 65494103 | 65494287 | chr8 | 65498465 | 65498550 |
| chr8 | 65498645 | 65498910 | chr8 | 65498926 | 65498944 | chr8 | 65499677 | 65500096 |
| chr8 | 65710868 | 65711084 | chr8 | 66548640 | 66548749 | chr8 | 67024963 | 67025365 |
| chr8 | 67344446 | 67344665 | chr8 | 67344667 | 67344702 | chr8 | 67344810 | 67344865 |

TABLE 15-continued

Pan-cancer #5

| chr | start | end | chr | start | end | chr | start | end |
|---|---|---|---|---|---|---|---|---|
| chr8 | 67873246 | 67873422 | chr8 | 67873799 | 67873799 | chr8 | 67873801 | 67874051 |
| chr8 | 67874165 | 67874673 | chr8 | 67874756 | 67874858 | chr8 | 67874860 | 67875261 |
| chr8 | 67875263 | 67875441 | chr8 | 67875443 | 67875697 | chr8 | 67940548 | 67940960 |
| chr8 | 68864546 | 68864852 | chr8 | 69242828 | 69243007 | chr8 | 69243285 | 69243486 |
| chr8 | 69243488 | 69243903 | chr8 | 69243964 | 69243971 | chr8 | 69244286 | 69244510 |
| chr8 | 69244512 | 69244585 | chr8 | 70744774 | 70745013 | chr8 | 70946670 | 70946915 |
| chr8 | 70947091 | 70947742 | chr8 | 70981866 | 70981880 | chr8 | 70982263 | 70982285 |
| chr8 | 70982287 | 70982567 | chr8 | 70982851 | 70983305 | chr8 | 70983402 | 70983870 |
| chr8 | 70984017 | 70984293 | chr8 | 70984344 | 70984662 | chr8 | 70984745 | 70985081 |
| chr8 | 72273897 | 72274136 | chr8 | 72468473 | 72469664 | chr8 | 72470301 | 72470540 |
| chr8 | 72471037 | 72471158 | chr8 | 72754293 | 72754361 | chr8 | 72754491 | 72754712 |
| chr8 | 72754730 | 72755240 | chr8 | 72755592 | 72755815 | chr8 | 72756656 | 72756812 |
| chr8 | 72756814 | 72756971 | chr8 | 72917268 | 72917429 | chr8 | 72917516 | 72917541 |
| chr8 | 72987519 | 72987916 | chr8 | 72987918 | 72988118 | chr8 | 73163860 | 73164261 |
| chr8 | 73450027 | 73450202 | chr8 | 73450418 | 73450657 | chr8 | 74759411 | 74759565 |
| chr8 | 74759744 | 74759863 | chr8 | 75896477 | 75896836 | chr8 | 75896838 | 75897297 |
| chr8 | 75897299 | 75897436 | chr8 | 76316242 | 76316541 | chr8 | 77585130 | 77585789 |
| chr8 | 77586078 | 77586377 | chr8 | 77586471 | 77586710 | chr8 | 77590144 | 77590563 |
| chr8 | 77593075 | 77593233 | chr8 | 77593235 | 77593453 | chr8 | 77593798 | 77594217 |
| chr8 | 77594552 | 77594595 | chr8 | 77594597 | 77594675 | chr8 | 77594758 | 77595091 |
| chr8 | 77595238 | 77595594 | chr8 | 79428200 | 79428499 | chr8 | 80523887 | 80524126 |
| chr8 | 80524167 | 80524406 | chr8 | 80524864 | 80525103 | chr8 | 80525520 | 80525819 |
| chr8 | 80695842 | 80696007 | chr8 | 80803594 | 80803953 | chr8 | 81478089 | 81478448 |
| chr8 | 85095396 | 85095498 | chr8 | 85095500 | 85095755 | chr8 | 85096485 | 85096721 |
| chr8 | 85096853 | 85096904 | chr8 | 85096939 | 85097003 | chr8 | 85097063 | 85097249 |
| chr8 | 86350455 | 86350567 | chr8 | 86406814 | 86406933 | chr8 | 86436547 | 86436726 |
| chr8 | 86544681 | 86544798 | chr8 | 89339298 | 89339837 | chr8 | 89340189 | 89340237 |
| chr8 | 89340274 | 89340428 | chr8 | 90913517 | 90913756 | chr8 | 91094161 | 91094326 |
| chr8 | 91803578 | 91803720 | chr8 | 91804065 | 91804332 | chr8 | 91996958 | 91997509 |
| chr8 | 91997528 | 91998037 | chr8 | 92083443 | 92083622 | chr8 | 93114033 | 93114150 |
| chr8 | 93114152 | 93114242 | chr8 | 93114307 | 93114632 | chr8 | 95651240 | 95651269 |
| chr8 | 95651448 | 95651599 | chr8 | 95651637 | 95651747 | chr8 | 96219911 | 96220002 |
| chr8 | 97157167 | 97157210 | chr8 | 97157667 | 97157898 | chr8 | 97158022 | 97158146 |
| chr8 | 97165541 | 97165780 | chr8 | 97166351 | 97166530 | chr8 | 97167082 | 97167321 |
| chr8 | 97169757 | 97169920 | chr8 | 97169922 | 97169956 | chr8 | 97170054 | 97170338 |
| chr8 | 97170378 | 97170416 | chr8 | 97170793 | 97170972 | chr8 | 97171036 | 97171265 |
| chr8 | 97171318 | 97171959 | chr8 | 97172019 | 97172295 | chr8 | 97172347 | 97172740 |
| chr8 | 97172822 | 97172961 | chr8 | 97172963 | 97173526 | chr8 | 97173528 | 97173546 |
| chr8 | 97173730 | 97173864 | chr8 | 97173921 | 97173991 | chr8 | 97339752 | 97340291 |
| chr8 | 97505950 | 97506049 | chr8 | 97506178 | 97506408 | chr8 | 97506448 | 97506609 |
| chr8 | 97507021 | 97507380 | chr8 | 97507464 | 97507763 | chr8 | 98289744 | 98289868 |
| chr8 | 98289923 | 98290343 | chr8 | 99439030 | 99439209 | chr8 | 99439299 | 99440438 |
| chr8 | 99951330 | 99951509 | chr8 | 99951757 | 99952144 | chr8 | 99952199 | 99952304 |
| chr8 | 99952533 | 99952896 | chr8 | 99954400 | 99954563 | chr8 | 99954679 | 99954819 |
| chr8 | 99955105 | 99955394 | chr8 | 99960231 | 99960498 | chr8 | 99960922 | 99961070 |
| chr8 | 99961111 | 99961174 | chr8 | 99961718 | 99961897 | chr8 | 99985781 | 99986044 |
| chr8 | 99986226 | 99986527 | chr8 | 99986792 | 99987020 | chr8 | 101118140 | 101118491 |
| chr8 | 101118659 | 101118679 | chr8 | 101661837 | 101662000 | chr8 | 101821891 | 101822130 |
| chr8 | 102505458 | 102505654 | chr8 | 102505720 | 102505986 | chr8 | 103629857 | 103629961 |
| chr8 | 104153105 | 104153344 | chr8 | 104153366 | 104153562 | chr8 | 104153682 | 104153911 |
| chr8 | 104512026 | 104513285 | chr8 | 104513365 | 104513909 | chr8 | 104513911 | 104514005 |
| chr8 | 105235293 | 105235502 | chr8 | 105235644 | 105235804 | chr8 | 105235864 | 105236132 |
| chr8 | 105478632 | 105478780 | chr8 | 105479248 | 105479281 | chr8 | 105479315 | 105479531 |
| chr8 | 106331084 | 106331257 | chr8 | 106332004 | 106332286 | chr8 | 107282060 | 107282299 |
| chr8 | 107283938 | 107284054 | chr8 | 107284056 | 107284177 | chr8 | 108509441 | 108509734 |
| chr8 | 109093601 | 109094260 | chr8 | 109094391 | 109094690 | chr8 | 109094757 | 109095437 |
| chr8 | 109095506 | 109095568 | chr8 | 109095570 | 109095974 | chr8 | 109799500 | 109799740 |
| chr8 | 110274904 | 110275021 | chr8 | 110405946 | 110406106 | chr8 | 110592245 | 110592303 |
| chr8 | 110703924 | 110704029 | chr8 | 110704098 | 110704223 | chr8 | 110986354 | 110986773 |
| chr8 | 114444497 | 114444640 | chr8 | 114444709 | 114445276 | chr8 | 114445677 | 114446101 |
| chr8 | 114446851 | 114447346 | chr8 | 114447348 | 114447450 | chr8 | 114448939 | 114449358 |
| chr8 | 114449457 | 114449688 | chr8 | 116660435 | 116660572 | chr8 | 116660616 | 116660854 |
| chr8 | 117950364 | 117950543 | chr8 | 117950700 | 117950999 | chr8 | 120220390 | 120220606 |
| chr8 | 120844011 | 120844126 | chr8 | 121136805 | 121137824 | chr8 | 121823827 | 121824006 |
| chr8 | 121824103 | 121824582 | chr8 | 121825512 | 121825560 | chr8 | 122651770 | 122652009 |
| chr8 | 123695447 | 123695746 | chr8 | 124055137 | 124055235 | chr8 | 124173165 | 124173544 |
| chr8 | 125452275 | 125452394 | chr8 | 126044494 | 126044653 | chr8 | 128745443 | 128745618 |
| chr8 | 128872311 | 128872490 | chr8 | 128889224 | 128889483 | chr8 | 128931157 | 128931336 |
| chr8 | 130369290 | 130369454 | chr8 | 132052057 | 132052300 | chr8 | 132052399 | 132052516 |
| chr8 | 132052590 | 132053256 | chr8 | 132053633 | 132054584 | chr8 | 132054594 | 132054876 |
| chr8 | 133686658 | 133686836 | chr8 | 139508668 | 139508947 | chr8 | 139509656 | 139509671 |
| chr8 | 139509694 | 139510015 | chr8 | 140714485 | 140714964 | chr8 | 140715016 | 140715095 |
| chr8 | 140715379 | 140715588 | chr8 | 140715700 | 140715738 | chr8 | 140715875 | 140716022 |
| chr8 | 140716340 | 140716348 | chr8 | 140834160 | 140834399 | chr8 | 140963208 | 140963447 |
| chr8 | 141159845 | 141160024 | chr8 | 141587975 | 141588214 | chr8 | 141596805 | 141597104 |
| chr8 | 142292454 | 142292808 | chr8 | 142361151 | 142361430 | chr8 | 142367673 | 142367879 |

TABLE 15-continued

Pan-cancer #5

| chr | start | end | chr | start | end | chr | start | end |
|---|---|---|---|---|---|---|---|---|
| chr8 | 142444648 | 142444827 | chr8 | 142528313 | 142528403 | chr8 | 142528455 | 142528607 |
| chr8 | 142528671 | 142528782 | chr8 | 142528835 | 142528962 | chr8 | 142529028 | 142529092 |
| chr8 | 142535241 | 142535587 | chr8 | 142568506 | 142568745 | chr8 | 142694751 | 142695030 |
| chr8 | 142984437 | 142984736 | chr8 | 143088946 | 143089153 | chr8 | 143105162 | 143105461 |
| chr8 | 143509377 | 143509607 | chr8 | 143509629 | 143509676 | chr8 | 143532035 | 143532510 |
| chr8 | 143532542 | 143532934 | chr8 | 143533520 | 143533641 | chr8 | 143533709 | 143533999 |
| chr8 | 143557881 | 143558172 | chr8 | 143558389 | 143558688 | chr8 | 143587238 | 143587477 |
| chr8 | 143592664 | 143592762 | chr8 | 143621889 | 143622188 | chr8 | 143701978 | 143702157 |
| chr8 | 143819303 | 143819406 | chr8 | 143858435 | 143858791 | chr8 | 143859223 | 143859281 |
| chr8 | 143859338 | 143859454 | chr8 | 143876854 | 143877033 | chr8 | 143993891 | 143994250 |
| chr8 | 144069457 | 144069749 | chr8 | 144190286 | 144190525 | chr8 | 144203601 | 144203801 |
| chr8 | 144203880 | 144204020 | chr8 | 144226100 | 144226279 | chr8 | 144238743 | 144238982 |
| chr8 | 144241150 | 144241389 | chr8 | 144241444 | 144241522 | chr8 | 144241584 | 144241683 |
| chr8 | 144241785 | 144242381 | chr8 | 144303488 | 144303667 | chr8 | 144328234 | 144328653 |
| chr8 | 144330288 | 144330467 | chr8 | 144344219 | 144344518 | chr8 | 144359928 | 144360177 |
| chr8 | 144360305 | 144360544 | chr8 | 144361672 | 144361911 | chr8 | 144372474 | 144372583 |
| chr8 | 144509238 | 144510617 | chr8 | 144511146 | 144511505 | chr8 | 144511938 | 144512297 |
| chr8 | 144512399 | 144512466 | chr8 | 144650791 | 144650812 | chr8 | 144668532 | 144668767 |
| chr8 | 144668822 | 144669061 | chr8 | 145753443 | 145753622 | chr8 | 145758483 | 145758782 |
| chr8 | 145806184 | 145806272 | chr8 | 145925387 | 145925429 | chr8 | 145925459 | 145925566 |
| chr8 | 145925869 | 145926069 | chr8 | 146013543 | 146013722 | chr8 | 146079134 | 146079297 |
| chr9 | 113346 | 113513 | chr9 | 113550 | 113645 | chr9 | 113749 | 113988 |
| chr9 | 117808 | 117960 | chr9 | 118140 | 118167 | chr9 | 841602 | 841850 |
| chr9 | 841852 | 842032 | chr9 | 842208 | 842244 | chr9 | 842611 | 842748 |
| chr9 | 969482 | 969615 | chr9 | 969685 | 969943 | chr9 | 970012 | 970105 |
| chr9 | 970186 | 970311 | chr9 | 970421 | 970600 | chr9 | 970816 | 970912 |
| chr9 | 970993 | 971175 | chr9 | 971639 | 971655 | chr9 | 972204 | 972863 |
| chr9 | 973184 | 973366 | chr9 | 975248 | 975262 | chr9 | 975693 | 976412 |
| chr9 | 976521 | 976690 | chr9 | 976912 | 977047 | chr9 | 981695 | 981934 |
| chr9 | 1042305 | 1042501 | chr9 | 1042616 | 1043076 | chr9 | 1051905 | 1052247 |
| chr9 | 3181662 | 3181961 | chr9 | 6412497 | 6412900 | chr9 | 6644217 | 6644368 |
| chr9 | 6644540 | 6644636 | chr9 | 6644936 | 6645415 | chr9 | 6645544 | 6645783 |
| chr9 | 6756279 | 6756429 | chr9 | 13278722 | 13278961 | chr9 | 14312943 | 14313182 |
| chr9 | 14347534 | 14347759 | chr9 | 14348234 | 14348533 | chr9 | 17906310 | 17906433 |
| chr9 | 17906461 | 17906789 | chr9 | 17906914 | 17907153 | chr9 | 17907325 | 17907371 |
| chr9 | 17907451 | 17907564 | chr9 | 19789025 | 19789381 | chr9 | 21031636 | 21031924 |
| chr9 | 21402520 | 21403119 | chr9 | 21559219 | 21559446 | chr9 | 21559678 | 21559804 |
| chr9 | 21964958 | 21965425 | chr9 | 21965570 | 21965857 | chr9 | 21968138 | 21968434 |
| chr9 | 21968457 | 21968557 | chr9 | 21970881 | 21971155 | chr9 | 21971185 | 21971282 |
| chr9 | 21974182 | 21974329 | chr9 | 21974408 | 21974887 | chr9 | 21994134 | 21994313 |
| chr9 | 21995223 | 21995402 | chr9 | 21995646 | 21995825 | chr9 | 22006057 | 22006153 |
| chr9 | 22006228 | 22006236 | chr9 | 22447567 | 22447772 | chr9 | 23822468 | 23822707 |
| chr9 | 23824487 | 23824666 | chr9 | 23831023 | 23831371 | chr9 | 23831451 | 23831490 |
| chr9 | 29212083 | 29212171 | chr9 | 29212211 | 29212382 | chr9 | 29213431 | 29213730 |
| chr9 | 29213938 | 29214237 | chr9 | 29214276 | 29214515 | chr9 | 29214585 | 29215184 |
| chr9 | 32782547 | 32782936 | chr9 | 32783084 | 32783206 | chr9 | 32783263 | 32783420 |
| chr9 | 32783591 | 32783742 | chr9 | 33524529 | 33524768 | chr9 | 33676697 | 33676876 |
| chr9 | 33677269 | 33677508 | chr9 | 34224262 | 34224497 | chr9 | 34372761 | 34373000 |
| chr9 | 34588960 | 34589259 | chr9 | 35617195 | 35617434 | chr9 | 35675441 | 35675648 |
| chr9 | 35675838 | 35676233 | chr9 | 36036994 | 36037173 | chr9 | 36318274 | 36318389 |
| chr9 | 36739812 | 36740078 | chr9 | 37002394 | 37002518 | chr9 | 37002819 | 37003113 |
| chr9 | 37025465 | 37025884 | chr9 | 37026055 | 37026352 | chr9 | 37026434 | 37026714 |
| chr9 | 37026733 | 37027272 | chr9 | 37027325 | 37027384 | chr9 | 37027386 | 37027512 |
| chr9 | 37027726 | 37027905 | chr9 | 37028870 | 37029049 | chr9 | 37029436 | 37030755 |
| chr9 | 37034163 | 37034342 | chr9 | 37034525 | 37034824 | chr9 | 37035427 | 37035820 |
| chr9 | 37036327 | 37036746 | chr9 | 37037594 | 37038433 | chr9 | 37467521 | 37467634 |
| chr9 | 38620642 | 38620808 | chr9 | 66456024 | 66456117 | chr9 | 71200618 | 71200720 |
| chr9 | 71734803 | 71734920 | chr9 | 71788876 | 71789261 | chr9 | 71789453 | 71789512 |
| chr9 | 71789608 | 71789835 | chr9 | 73032727 | 73032835 | chr9 | 74061745 | 74061759 |
| chr9 | 74061788 | 74062164 | chr9 | 74764449 | 74764748 | chr9 | 77112900 | 77113341 |
| chr9 | 77113559 | 77113709 | chr9 | 77113806 | 77113919 | chr9 | 77114649 | 77114948 |
| chr9 | 77115120 | 77115539 | chr9 | 77115583 | 77115587 | chr9 | 79626794 | 79627453 |
| chr9 | 79628190 | 79628429 | chr9 | 79629208 | 79629499 | chr9 | 79629533 | 79629553 |
| chr9 | 79629791 | 79630491 | chr9 | 79631115 | 79631414 | chr9 | 79631454 | 79631693 |
| chr9 | 79631785 | 79632264 | chr9 | 79632786 | 79632965 | chr9 | 79633322 | 79633737 |
| chr9 | 79633739 | 79633981 | chr9 | 79634088 | 79634987 | chr9 | 79635048 | 79635449 |
| chr9 | 79635746 | 79636066 | chr9 | 79636103 | 79636127 | chr9 | 79636167 | 79636642 |
| chr9 | 79636717 | 79637366 | chr9 | 79637644 | 79637889 | chr9 | 79638137 | 79638336 |
| chr9 | 86152313 | 86152372 | chr9 | 86152382 | 86152492 | chr9 | 86755443 | 86756042 |
| chr9 | 86886632 | 86886811 | chr9 | 87282934 | 87283113 | chr9 | 87283574 | 87283813 |
| chr9 | 87284603 | 87284902 | chr9 | 87285273 | 87285533 | chr9 | 87285555 | 87285759 |
| chr9 | 88137487 | 88137726 | chr9 | 88137875 | 88138091 | chr9 | 89517623 | 89517655 |
| chr9 | 89517861 | 89517917 | chr9 | 89560675 | 89560914 | chr9 | 89560967 | 89561206 |
| chr9 | 91150130 | 91150429 | chr9 | 91605912 | 91606151 | chr9 | 91792283 | 91792462 |
| chr9 | 91792693 | 91792992 | chr9 | 91793083 | 91793622 | chr9 | 93697942 | 93698051 |
| chr9 | 94183793 | 94184032 | chr9 | 94572543 | 94572703 | chr9 | 94712295 | 94712320 |

TABLE 15-continued

Pan-cancer #5

| chr | start | end | chr | start | end | chr | start | end |
|---|---|---|---|---|---|---|---|---|
| chr9 | 95417452 | 95417747 | chr9 | 95560736 | 95560915 | chr9 | 95569672 | 95569911 |
| chr9 | 95570162 | 95570521 | chr9 | 95571540 | 95571659 | chr9 | 95571753 | 95571839 |
| chr9 | 95947121 | 95947360 | chr9 | 96588726 | 96588740 | chr9 | 96588858 | 96588965 |
| chr9 | 96710303 | 96710482 | chr9 | 96710582 | 96711089 | chr9 | 96711169 | 96711447 |
| chr9 | 96711535 | 96711708 | chr9 | 96711901 | 96712080 | chr9 | 96713277 | 96713996 |
| chr9 | 96714997 | 96715068 | chr9 | 96715135 | 96715373 | chr9 | 96715688 | 96715794 |
| chr9 | 96716763 | 96716824 | chr9 | 96716905 | 96717428 | chr9 | 96717450 | 96717542 |
| chr9 | 96717885 | 96718244 | chr9 | 96720752 | 96720886 | chr9 | 96721103 | 96721468 |
| chr9 | 96721689 | 96721903 | chr9 | 96722477 | 96722548 | chr9 | 96722863 | 96722886 |
| chr9 | 96722999 | 96723160 | chr9 | 96723171 | 96723298 | chr9 | 98111281 | 98111561 |
| chr9 | 98111895 | 98112158 | chr9 | 98112344 | 98112472 | chr9 | 98784698 | 98784877 |
| chr9 | 98789557 | 98790013 | chr9 | 98790084 | 98790096 | chr9 | 99449054 | 99449487 |
| chr9 | 99639543 | 99640022 | chr9 | 99983066 | 99983245 | chr9 | 99983319 | 99983704 |
| chr9 | 99983799 | 99983918 | chr9 | 99983925 | 99984004 | chr9 | 100503542 | 100504021 |
| chr9 | 100609970 | 100610135 | chr9 | 100610201 | 100610315 | chr9 | 100610603 | 100610817 |
| chr9 | 100611125 | 100611731 | chr9 | 100613748 | 100614000 | chr9 | 100614193 | 100614407 |
| chr9 | 100614463 | 100615201 | chr9 | 100615203 | 100616036 | chr9 | 100616271 | 100616469 |
| chr9 | 100617286 | 100617449 | chr9 | 100617600 | 100618139 | chr9 | 100619627 | 100620166 |
| chr9 | 100620228 | 100620862 | chr9 | 100818337 | 100818516 | chr9 | 100835850 | 100835969 |
| chr9 | 101469169 | 101469408 | chr9 | 101469521 | 101469880 | chr9 | 101470034 | 101470333 |
| chr9 | 101470991 | 101471170 | chr9 | 101471477 | 101471553 | chr9 | 101471555 | 101471716 |
| chr9 | 101471786 | 101472030 | chr9 | 101705897 | 101706041 | chr9 | 101706043 | 101706196 |
| chr9 | 101706313 | 101706796 | chr9 | 103174718 | 103174825 | chr9 | 104248482 | 104248650 |
| chr9 | 104248698 | 104248721 | chr9 | 104249400 | 104249632 | chr9 | 104500551 | 104500850 |
| chr9 | 110126159 | 110126338 | chr9 | 110228102 | 110228701 | chr9 | 110251381 | 110251493 |
| chr9 | 110252260 | 110252455 | chr9 | 110252548 | 110252619 | chr9 | 112403096 | 112403275 |
| chr9 | 112403290 | 112403301 | chr9 | 112403303 | 112403469 | chr9 | 113341445 | 113341622 |
| chr9 | 113341680 | 113341848 | chr9 | 113341927 | 113342044 | chr9 | 113342201 | 113342428 |
| chr9 | 115067840 | 115067945 | chr9 | 115478852 | 115478971 | chr9 | 115652867 | 115653526 |
| chr9 | 116633786 | 116633905 | chr9 | 117050887 | 117051126 | chr9 | 118916933 | 118917172 |
| chr9 | 120175695 | 120175934 | chr9 | 120176009 | 120176248 | chr9 | 120176793 | 120176972 |
| chr9 | 120507467 | 120507514 | chr9 | 122131383 | 122131439 | chr9 | 122131497 | 122131742 |
| chr9 | 122131785 | 122132026 | chr9 | 122132052 | 122132320 | chr9 | 123295404 | 123295559 |
| chr9 | 124751411 | 124751590 | chr9 | 125676724 | 125676798 | chr9 | 126133698 | 126133937 |
| chr9 | 126154201 | 126154651 | chr9 | 126349070 | 126349191 | chr9 | 126770159 | 126770398 |
| chr9 | 126771440 | 126771799 | chr9 | 126774460 | 126774620 | chr9 | 126775456 | 126775620 |
| chr9 | 126775963 | 126776099 | chr9 | 126777488 | 126777747 | chr9 | 126777974 | 126778086 |
| chr9 | 126778359 | 126778593 | chr9 | 126779391 | 126780044 | chr9 | 126780285 | 126780406 |
| chr9 | 126780736 | 126780975 | chr9 | 126783321 | 126783577 | chr9 | 127212750 | 127213109 |
| chr9 | 127265588 | 127265610 | chr9 | 127265876 | 127266127 | chr9 | 127266372 | 127266588 |
| chr9 | 128652097 | 128652336 | chr9 | 128759764 | 128760053 | chr9 | 129276620 | 129276919 |
| chr9 | 129372837 | 129373038 | chr9 | 129373251 | 129373316 | chr9 | 129376096 | 129376275 |
| chr9 | 129376815 | 129376892 | chr9 | 129376932 | 129376994 | chr9 | 129377116 | 129377352 |
| chr9 | 129377593 | 129377636 | chr9 | 129377773 | 129377960 | chr9 | 129378025 | 129378104 |
| chr9 | 129381027 | 129381084 | chr9 | 129387421 | 129387539 | chr9 | 129387701 | 129387749 |
| chr9 | 129387848 | 129388300 | chr9 | 129388639 | 129388754 | chr9 | 129388817 | 129388878 |
| chr9 | 129388915 | 129389274 | chr9 | 129400912 | 129401271 | chr9 | 129445232 | 129445651 |
| chr9 | 129445709 | 129445888 | chr9 | 129485763 | 129485772 | chr9 | 130248345 | 130248524 |
| chr9 | 130461543 | 130461571 | chr9 | 130461687 | 130461842 | chr9 | 130689631 | 130689668 |
| chr9 | 130689724 | 130689742 | chr9 | 131579939 | 131580104 | chr9 | 131607443 | 131607622 |
| chr9 | 131607696 | 131607875 | chr9 | 131854131 | 131854430 | chr9 | 132382297 | 132382355 |
| chr9 | 132382635 | 132383116 | chr9 | 132402743 | 132402982 | chr9 | 132403064 | 132403303 |
| chr9 | 132559298 | 132559413 | chr9 | 132805270 | 132805449 | chr9 | 132805750 | 132805989 |
| chr9 | 133308798 | 133309037 | chr9 | 133534609 | 133534788 | chr9 | 133535707 | 133535934 |
| chr9 | 133536012 | 133536120 | chr9 | 133536150 | 133536345 | chr9 | 133536347 | 133536431 |
| chr9 | 133536675 | 133536974 | chr9 | 133537097 | 133537636 | chr9 | 133538090 | 133538809 |
| chr9 | 133539511 | 133539808 | chr9 | 133540977 | 133541276 | chr9 | 133541594 | 133542433 |
| chr9 | 133773666 | 133774025 | chr9 | 133927265 | 133927564 | chr9 | 133928162 | 133928341 |
| chr9 | 134191003 | 134191302 | chr9 | 134207833 | 134207997 | chr9 | 134421818 | 134421936 |
| chr9 | 134717221 | 134717434 | chr9 | 135037029 | 135037288 | chr9 | 135037334 | 135037448 |
| chr9 | 135455317 | 135455676 | chr9 | 135455912 | 135456024 | chr9 | 135456080 | 135456151 |
| chr9 | 135456391 | 135456630 | chr9 | 135456796 | 135456915 | chr9 | 135458388 | 135458440 |
| chr9 | 135458457 | 135458687 | chr9 | 135459920 | 135460269 | chr9 | 135460795 | 135460819 |
| chr9 | 135461455 | 135461852 | chr9 | 135461969 | 135462078 | chr9 | 135462648 | 135463048 |
| chr9 | 135464709 | 135465008 | chr9 | 135465861 | 135466065 | chr9 | 135466118 | 135466220 |
| chr9 | 135466263 | 135466742 | chr9 | 135548157 | 135548265 | chr9 | 135865007 | 135865246 |
| chr9 | 135898809 | 135899211 | chr9 | 136474432 | 136474592 | chr9 | 137299018 | 137299555 |
| chr9 | 137299596 | 137299677 | chr9 | 137533897 | 137533967 | chr9 | 137534066 | 137534316 |
| chr9 | 137656864 | 137657223 | chr9 | 137667253 | 137667432 | chr9 | 137718802 | 137719101 |
| chr9 | 137721999 | 137722197 | chr9 | 137979803 | 137980102 | chr9 | 137980217 | 137980363 |
| chr9 | 137980806 | 137980985 | chr9 | 138265038 | 138265337 | chr9 | 138562961 | 138563377 |
| chr9 | 138606221 | 138606249 | chr9 | 138606711 | 138606774 | chr9 | 138606821 | 138606850 |
| chr9 | 138606927 | 138607010 | chr9 | 138627556 | 138627925 | chr9 | 138633954 | 138634253 |
| chr9 | 138659704 | 138660003 | chr9 | 138660859 | 138661098 | chr9 | 138661550 | 138661969 |
| chr9 | 138666358 | 138666657 | chr9 | 138880882 | 138880973 | chr9 | 138991833 | 138991903 |
| chr9 | 139000485 | 139000724 | chr9 | 139012193 | 139012492 | chr9 | 139024750 | 139024873 |

TABLE 15-continued

Pan-cancer #5

| chr | start | end | chr | start | end | chr | start | end |
|---|---|---|---|---|---|---|---|---|
| chr9 | 139045579 | 139045758 | chr9 | 139047494 | 139047733 | chr9 | 139085145 | 139085351 |
| chr9 | 139085373 | 139085444 | chr9 | 139085986 | 139086071 | chr9 | 139090420 | 139090552 |
| chr9 | 139090587 | 139090659 | chr9 | 139090692 | 139090742 | chr9 | 139091072 | 139091471 |
| chr9 | 139093773 | 139093923 | chr9 | 139094610 | 139094733 | chr9 | 139095264 | 139095563 |
| chr9 | 139096559 | 139097098 | chr9 | 139111194 | 139111373 | chr9 | 139268961 | 139268987 |
| chr9 | 139421881 | 139422060 | chr9 | 139698839 | 139699138 | chr9 | 139704085 | 139704384 |
| chr9 | 139858946 | 139859365 | chr9 | 139888844 | 139889083 | chr9 | 140024754 | 140024771 |
| chr9 | 140024787 | 140024919 | chr9 | 140024957 | 140025113 | chr9 | 140030424 | 140030603 |
| chr9 | 140032802 | 140033050 | chr9 | 140033192 | 140033197 | chr9 | 140033325 | 140033491 |
| chr9 | 140033619 | 140033627 | chr9 | 140033815 | 140034174 | chr9 | 140050893 | 140051097 |
| chr9 | 140051220 | 140051432 | chr9 | 140127803 | 140128162 | chr9 | 140137220 | 140137334 |
| chr9 | 140205346 | 140205607 | chr9 | 140245789 | 140246084 | chr9 | 140332624 | 140333103 |
| chr9 | 140382472 | 140382697 | chr9 | 140392380 | 140392559 | chr9 | 140396944 | 140397183 |
| chr9 | 140507207 | 140507506 | chr9 | 140708961 | 140709260 | chr9 | 140727429 | 140727611 |
| chr9 | 140727769 | 140728008 | chr9 | 140769913 | 140770048 | chr9 | 140771969 | 140772431 |
| chr9 | 140772495 | 140772594 | chr9 | 140772757 | 140773394 | chr10 | 524680 | 524770 |
| chr10 | 833228 | 833419 | chr10 | 978787 | 979026 | chr10 | 1585208 | 1585325 |
| chr10 | 1708551 | 1708583 | chr10 | 1779342 | 1779821 | chr10 | 3285686 | 3285792 |
| chr10 | 3330410 | 3330696 | chr10 | 3641277 | 3641396 | chr10 | 3678618 | 3678737 |
| chr10 | 3895312 | 3895551 | chr10 | 4599822 | 4600061 | chr10 | 5530673 | 5531080 |
| chr10 | 5875059 | 5875345 | chr10 | 6003386 | 6003625 | chr10 | 6042233 | 6042592 |
| chr10 | 6162073 | 6162302 | chr10 | 6577569 | 6577748 | chr10 | 6984626 | 6984731 |
| chr10 | 7205641 | 7205880 | chr10 | 7212666 | 7213145 | chr10 | 7213532 | 7213610 |
| chr10 | 7215985 | 7216164 | chr10 | 7236109 | 7236348 | chr10 | 7255627 | 7255659 |
| chr10 | 7414427 | 7414686 | chr10 | 7424552 | 7424731 | chr10 | 7449863 | 7450190 |
| chr10 | 7450491 | 7451482 | chr10 | 7452143 | 7452862 | chr10 | 7453233 | 7453657 |
| chr10 | 7453903 | 7454012 | chr10 | 7708311 | 7708379 | chr10 | 7708700 | 7708857 |
| chr10 | 7708955 | 7709090 | chr10 | 7709649 | 7709807 | chr10 | 8075843 | 8075945 |
| chr10 | 8076054 | 8076071 | chr10 | 8076341 | 8076563 | chr10 | 8076730 | 8077449 |
| chr10 | 8077790 | 8078316 | chr10 | 8085600 | 8085800 | chr10 | 8085875 | 8086114 |
| chr10 | 8091818 | 8092099 | chr10 | 8093653 | 8093825 | chr10 | 8093860 | 8093964 |
| chr10 | 8095515 | 8095774 | chr10 | 8095842 | 8095934 | chr10 | 8096086 | 8096265 |
| chr10 | 8096877 | 8097296 | chr10 | 8097387 | 8097588 | chr10 | 11059620 | 11059664 |
| chr10 | 11059933 | 11060158 | chr10 | 11207079 | 11207378 | chr10 | 11700861 | 11701100 |
| chr10 | 13043287 | 13043526 | chr10 | 13141002 | 13141106 | chr10 | 13715462 | 13715485 |
| chr10 | 13933361 | 13933539 | chr10 | 13933597 | 13933935 | chr10 | 13933983 | 13933996 |
| chr10 | 13933998 | 13934126 | chr10 | 13934169 | 13934260 | chr10 | 14966052 | 14966291 |
| chr10 | 15140509 | 15140625 | chr10 | 15761213 | 15761752 | chr10 | 15762050 | 15762211 |
| chr10 | 16562009 | 16562043 | chr10 | 16562369 | 16562626 | chr10 | 16562628 | 16562673 |
| chr10 | 16562710 | 16563665 | chr10 | 16563691 | 16563988 | chr10 | 16564013 | 16564127 |
| chr10 | 17270131 | 17270529 | chr10 | 17270889 | 17271255 | chr10 | 17271444 | 17271519 |
| chr10 | 17271521 | 17271728 | chr10 | 17271835 | 17272313 | chr10 | 17272527 | 17272706 |
| chr10 | 17429082 | 17429244 | chr10 | 17429562 | 17429724 | chr10 | 17496545 | 17496834 |
| chr10 | 18429147 | 18429149 | chr10 | 18429552 | 18429749 | chr10 | 18429751 | 18429851 |
| chr10 | 21462526 | 21462690 | chr10 | 21805128 | 21805367 | chr10 | 22047362 | 22047601 |
| chr10 | 22541563 | 22541851 | chr10 | 22542025 | 22542250 | chr10 | 22623924 | 22624306 |
| chr10 | 22624562 | 22625121 | chr10 | 22625383 | 22625783 | chr10 | 22625812 | 22626080 |
| chr10 | 22633902 | 22634175 | chr10 | 22634325 | 22634432 | chr10 | 22634434 | 22634439 |
| chr10 | 22634441 | 22634655 | chr10 | 22764556 | 22765590 | chr10 | 23216786 | 23216843 |
| chr10 | 23216845 | 23217025 | chr10 | 23460264 | 23460552 | chr10 | 23461129 | 23461848 |
| chr10 | 23461976 | 23462463 | chr10 | 23462486 | 23462615 | chr10 | 23462635 | 23462995 |
| chr10 | 23463267 | 23463854 | chr10 | 23463888 | 23464154 | chr10 | 23479793 | 23480697 |
| chr10 | 23480904 | 23481050 | chr10 | 23481304 | 23481385 | chr10 | 23481387 | 23481598 |
| chr10 | 23481862 | 23482233 | chr10 | 23482289 | 23482521 | chr10 | 23483744 | 23484703 |
| chr10 | 23486177 | 23486416 | chr10 | 23487651 | 23488070 | chr10 | 23488343 | 23489256 |
| chr10 | 23489335 | 23489514 | chr10 | 23982360 | 23982899 | chr10 | 23983102 | 23983341 |
| chr10 | 23983618 | 23983801 | chr10 | 23984008 | 23984307 | chr10 | 23984842 | 23985066 |
| chr10 | 24988575 | 24988641 | chr10 | 25464528 | 25464910 | chr10 | 25465320 | 25465350 |
| chr10 | 25465352 | 25465619 | chr10 | 26055737 | 26055916 | chr10 | 26222916 | 26223100 |
| chr10 | 26223102 | 26223206 | chr10 | 26223426 | 26223513 | chr10 | 26223957 | 26224136 |
| chr10 | 26500528 | 26500871 | chr10 | 26501445 | 26501668 | chr10 | 26503593 | 26503832 |
| chr10 | 26504018 | 26504144 | chr10 | 26504191 | 26504257 | chr10 | 26504410 | 26504884 |
| chr10 | 26505009 | 26505236 | chr10 | 26505442 | 26505503 | chr10 | 26505510 | 26505618 |
| chr10 | 26505714 | 26505783 | chr10 | 26505961 | 26506260 | chr10 | 26506288 | 26506353 |
| chr10 | 26506355 | 26506619 | chr10 | 26506903 | 26507427 | chr10 | 26681025 | 26681204 |
| chr10 | 26727024 | 26727443 | chr10 | 26727509 | 26727817 | chr10 | 26727868 | 26727928 |
| chr10 | 26746956 | 26747074 | chr10 | 26816913 | 26817032 | chr10 | 27547856 | 27548332 |
| chr10 | 27548401 | 27548575 | chr10 | 27794394 | 27794512 | chr10 | 27846608 | 27846719 |
| chr10 | 28030790 | 28031029 | chr10 | 28032874 | 28033113 | chr10 | 28033327 | 28033566 |
| chr10 | 28033667 | 28034091 | chr10 | 28034093 | 28034187 | chr10 | 28034327 | 28034446 |
| chr10 | 28034489 | 28034556 | chr10 | 28034874 | 28035388 | chr10 | 28035520 | 28035879 |
| chr10 | 28287286 | 28287318 | chr10 | 28287366 | 28287481 | chr10 | 28287693 | 28288164 |
| chr10 | 28957989 | 28957995 | chr10 | 28958044 | 28958226 | chr10 | 29010956 | 29011239 |
| chr10 | 30026077 | 30026180 | chr10 | 31073276 | 31073541 | chr10 | 31892822 | 31893181 |
| chr10 | 32499021 | 32499260 | chr10 | 33233249 | 33233457 | chr10 | 33624079 | 33624318 |
| chr10 | 33624407 | 33624550 | chr10 | 33624621 | 33624646 | chr10 | 35929334 | 35929609 |

TABLE 15-continued

Pan-cancer #5

| chr | start | end | chr | start | end | chr | start | end |
|---|---|---|---|---|---|---|---|---|
| chr10 | 43249935 | 43250114 | chr10 | 43250317 | 43250780 | chr10 | 43250855 | 43250976 |
| chr10 | 43428329 | 43428577 | chr10 | 43428637 | 43428688 | chr10 | 43428903 | 43428977 |
| chr10 | 43429067 | 43429197 | chr10 | 43429275 | 43429514 | chr10 | 43572591 | 43572830 |
| chr10 | 43600551 | 43600733 | chr10 | 43615462 | 43615639 | chr10 | 43697812 | 43698087 |
| chr10 | 43698199 | 43698231 | chr10 | 43858258 | 43858437 | chr10 | 44879847 | 44880326 |
| chr10 | 44880773 | 44881012 | chr10 | 49652880 | 49653179 | chr10 | 49731470 | 49731829 |
| chr10 | 49731980 | 49732088 | chr10 | 49732156 | 49732315 | chr10 | 49732317 | 49732579 |
| chr10 | 50323162 | 50323360 | chr10 | 50340179 | 50340224 | chr10 | 50507469 | 50507708 |
| chr10 | 50603884 | 50604243 | chr10 | 50604508 | 50604747 | chr10 | 50604967 | 50604979 |
| chr10 | 50605053 | 50605746 | chr10 | 50605931 | 50606530 | chr10 | 50816972 | 50817224 |
| chr10 | 50817778 | 50817810 | chr10 | 50817812 | 50817873 | chr10 | 50818288 | 50818527 |
| chr10 | 50818987 | 50819203 | chr10 | 50821378 | 50821797 | chr10 | 50887557 | 50887616 |
| chr10 | 50887618 | 50887754 | chr10 | 50887790 | 50887916 | chr10 | 50977034 | 50977144 |
| chr10 | 54068449 | 54068688 | chr10 | 54072882 | 54073121 | chr10 | 54073191 | 54073370 |
| chr10 | 54074648 | 54074887 | chr10 | 57387344 | 57387883 | chr10 | 57388239 | 57388598 |
| chr10 | 57390195 | 57390734 | chr10 | 57391072 | 57391311 | chr10 | 60273033 | 60273279 |
| chr10 | 60273347 | 60273392 | chr10 | 60935793 | 60936091 | chr10 | 60936449 | 60936730 |
| chr10 | 60937042 | 60937178 | chr10 | 63212244 | 63212783 | chr10 | 64575433 | 64575732 |
| chr10 | 64578189 | 64578626 | chr10 | 71327627 | 71327865 | chr10 | 71328678 | 71328917 |
| chr10 | 71328980 | 71329002 | chr10 | 71329077 | 71329219 | chr10 | 71329462 | 71329633 |
| chr10 | 71331966 | 71332650 | chr10 | 71333105 | 71333150 | chr10 | 72015070 | 72015425 |
| chr10 | 72043779 | 72043976 | chr10 | 72200001 | 72200065 | chr10 | 72200118 | 72200240 |
| chr10 | 72200251 | 72200772 | chr10 | 72200825 | 72201390 | chr10 | 72973124 | 72973275 |
| chr10 | 73156347 | 73156465 | chr10 | 73156550 | 73156752 | chr10 | 73157768 | 73158049 |
| chr10 | 73847788 | 73847792 | chr10 | 73848209 | 73848267 | chr10 | 75407495 | 75407782 |
| chr10 | 75488860 | 75488975 | chr10 | 77191147 | 77191446 | chr10 | 79396826 | 79397185 |
| chr10 | 81023964 | 81023989 | chr10 | 81664764 | 81665003 | chr10 | 82116994 | 82117283 |
| chr10 | 83634171 | 83634234 | chr10 | 83635441 | 83635499 | chr10 | 83635531 | 83635620 |
| chr10 | 85954322 | 85954561 | chr10 | 88149273 | 88149692 | chr10 | 89692817 | 89692996 |
| chr10 | 89717584 | 89717763 | chr10 | 90966608 | 90966967 | chr10 | 90967587 | 90968126 |
| chr10 | 91294929 | 91295168 | chr10 | 91295449 | 91295492 | chr10 | 91295585 | 91295808 |
| chr10 | 92617156 | 92617395 | chr10 | 93647139 | 93647378 | chr10 | 93647486 | 93647648 |
| chr10 | 93647650 | 93647725 | chr10 | 94450582 | 94450806 | chr10 | 94451372 | 94451587 |
| chr10 | 94825999 | 94826160 | chr10 | 94828062 | 94828125 | chr10 | 94828194 | 94828601 |
| chr10 | 94828633 | 94828932 | chr10 | 94834311 | 94835088 | chr10 | 96304116 | 96304200 |
| chr10 | 98129719 | 98130138 | chr10 | 99080176 | 99080535 | chr10 | 99080774 | 99080931 |
| chr10 | 99080990 | 99081061 | chr10 | 99531116 | 99531535 | chr10 | 99789080 | 99789379 |
| chr10 | 99790171 | 99790340 | chr10 | 99790508 | 99790747 | chr10 | 99790918 | 99791258 |
| chr10 | 100991863 | 100991935 | chr10 | 100992056 | 100992191 | chr10 | 100992222 | 100992535 |
| chr10 | 100992780 | 100992822 | chr10 | 100993448 | 100993938 | chr10 | 100993940 | 100994107 |
| chr10 | 100995956 | 100996315 | chr10 | 101088918 | 101089517 | chr10 | 101089817 | 101090296 |
| chr10 | 101280106 | 101280569 | chr10 | 101283382 | 101283577 | chr10 | 101290028 | 101290161 |
| chr10 | 101290180 | 101290699 | chr10 | 101290701 | 101291143 | chr10 | 101291231 | 101291284 |
| chr10 | 101292254 | 101292998 | chr10 | 101293071 | 101293430 | chr10 | 101294662 | 101295400 |
| chr10 | 101295402 | 101295681 | chr10 | 101296665 | 101296717 | chr10 | 101296738 | 101296892 |
| chr10 | 101874886 | 101875222 | chr10 | 102322156 | 102322335 | chr10 | 102419230 | 102419267 |
| chr10 | 102419400 | 102419769 | chr10 | 102430611 | 102430850 | chr10 | 102473775 | 102474014 |
| chr10 | 102483915 | 102484232 | chr10 | 102484234 | 102484246 | chr10 | 102484270 | 102484632 |
| chr10 | 102495416 | 102495717 | chr10 | 102497253 | 102497298 | chr10 | 102497300 | 102497791 |
| chr10 | 102498178 | 102498537 | chr10 | 102501285 | 102501464 | chr10 | 102507408 | 102507536 |
| chr10 | 102508902 | 102509381 | chr10 | 102589340 | 102589579 | chr10 | 102589702 | 102590001 |
| chr10 | 102590075 | 102590494 | chr10 | 102890843 | 102891019 | chr10 | 102891021 | 102891682 |
| chr10 | 102891745 | 102891956 | chr10 | 102892091 | 102892104 | chr10 | 102893528 | 102893952 |
| chr10 | 102894091 | 102895366 | chr10 | 102899088 | 102899687 | chr10 | 102899712 | 102899856 |
| chr10 | 102900263 | 102900671 | chr10 | 102906423 | 102906470 | chr10 | 102906525 | 102906667 |
| chr10 | 102975518 | 102975937 | chr10 | 102976963 | 102977502 | chr10 | 102983088 | 102983380 |
| chr10 | 102983435 | 102983841 | chr10 | 102984313 | 102984371 | chr10 | 102984513 | 102984612 |
| chr10 | 102985689 | 102986048 | chr10 | 102986447 | 102986953 | chr10 | 102987207 | 102987646 |
| chr10 | 102989555 | 102989734 | chr10 | 102996018 | 102996481 | chr10 | 102996597 | 102996737 |
| chr10 | 102997282 | 102997488 | chr10 | 102998493 | 102998912 | chr10 | 103043925 | 103044228 |
| chr10 | 103044301 | 103044471 | chr10 | 103535527 | 103535586 | chr10 | 103535634 | 103535771 |
| chr10 | 103535842 | 103535886 | chr10 | 103536143 | 103536257 | chr10 | 103536300 | 103536502 |
| chr10 | 103579718 | 103579794 | chr10 | 103930133 | 103930248 | chr10 | 104169995 | 104170263 |
| chr10 | 104170408 | 104170513 | chr10 | 104170515 | 104170801 | chr10 | 105036464 | 105036659 |
| chr10 | 105036701 | 105036863 | chr10 | 105036865 | 105036883 | chr10 | 105036894 | 105036943 |
| chr10 | 105037138 | 105037892 | chr10 | 105127048 | 105127156 | chr10 | 105155378 | 105155563 |
| chr10 | 105413527 | 105413886 | chr10 | 106398556 | 106398688 | chr10 | 106398826 | 106398975 |
| chr10 | 106399505 | 106400464 | chr10 | 106400869 | 106400918 | chr10 | 106401323 | 106401433 |
| chr10 | 106401511 | 106402191 | chr10 | 106402272 | 106402428 | chr10 | 106402620 | 106402919 |
| chr10 | 108923951 | 108924060 | chr10 | 108924365 | 108924366 | chr10 | 108924368 | 108924401 |
| chr10 | 108924770 | 108924784 | chr10 | 110226162 | 110226169 | chr10 | 110671800 | 110671884 |
| chr10 | 110671930 | 110672339 | chr10 | 111216709 | 111216804 | chr10 | 112403075 | 112403374 |
| chr10 | 112440312 | 112440483 | chr10 | 115804748 | 115805107 | chr10 | 116164146 | 116164445 |
| chr10 | 116331052 | 116331231 | chr10 | 116853773 | 116854012 | chr10 | 118030550 | 118030706 |
| chr10 | 118031206 | 118031549 | chr10 | 118031625 | 118031864 | chr10 | 118031866 | 118032230 |
| chr10 | 118032413 | 118032645 | chr10 | 118032841 | 118033140 | chr10 | 118033261 | 118033620 |

TABLE 15-continued

Pan-cancer #5

| chr | start | end | chr | start | end | chr | start | end |
|---|---|---|---|---|---|---|---|---|
| chr10 | 118034143 | 118034243 | chr10 | 118890893 | 118891134 | chr10 | 118891180 | 118891192 |
| chr10 | 118891437 | 118891662 | chr10 | 118891716 | 118891854 | chr10 | 118891938 | 118892457 |
| chr10 | 118892518 | 118893360 | chr10 | 118893484 | 118893581 | chr10 | 118893680 | 118893826 |
| chr10 | 118894035 | 118894072 | chr10 | 118896538 | 118896897 | chr10 | 118897822 | 118897847 |
| chr10 | 118897849 | 118898061 | chr10 | 118899199 | 118899378 | chr10 | 118899583 | 118899603 |
| chr10 | 118899893 | 118900034 | chr10 | 118900063 | 118900245 | chr10 | 118900324 | 118900602 |
| chr10 | 118922061 | 118922296 | chr10 | 118922632 | 118922900 | chr10 | 118922944 | 118922991 |
| chr10 | 118923050 | 118923349 | chr10 | 118924511 | 118924990 | chr10 | 118927012 | 118927371 |
| chr10 | 118928459 | 118928614 | chr10 | 119000564 | 119000592 | chr10 | 119000690 | 119001155 |
| chr10 | 119001329 | 119001403 | chr10 | 119001460 | 119001639 | chr10 | 119292324 | 119292419 |
| chr10 | 119294258 | 119294557 | chr10 | 119294747 | 119294898 | chr10 | 119294909 | 119295346 |
| chr10 | 119296628 | 119296644 | chr10 | 119296756 | 119296867 | chr10 | 119297308 | 119297607 |
| chr10 | 119301278 | 119301428 | chr10 | 119302055 | 119302080 | chr10 | 119302859 | 119303278 |
| chr10 | 119304289 | 119304468 | chr10 | 119304794 | 119304829 | chr10 | 119304851 | 119304986 |
| chr10 | 119305062 | 119305213 | chr10 | 119306948 | 119307127 | chr10 | 119311793 | 119311830 |
| chr10 | 119311905 | 119311972 | chr10 | 119312673 | 119313272 | chr10 | 119806952 | 119807131 |
| chr10 | 120354169 | 120354330 | chr10 | 120355462 | 120355701 | chr10 | 120841455 | 120841563 |
| chr10 | 122216811 | 122217170 | chr10 | 122708479 | 122708773 | chr10 | 123357681 | 123357757 |
| chr10 | 123922546 | 123922683 | chr10 | 123923518 | 123923565 | chr10 | 124893085 | 124893193 |
| chr10 | 124893238 | 124893444 | chr10 | 124893551 | 124893850 | chr10 | 124893863 | 124894582 |
| chr10 | 124894871 | 124895026 | chr10 | 124895342 | 124895696 | chr10 | 124895833 | 124896533 |
| chr10 | 124896938 | 124897007 | chr10 | 124897118 | 124897657 | chr10 | 124897958 | 124898056 |
| chr10 | 124898957 | 124899196 | chr10 | 124899651 | 124899890 | chr10 | 124901816 | 124902047 |
| chr10 | 124902139 | 124902569 | chr10 | 124902608 | 124903315 | chr10 | 124904841 | 124905200 |
| chr10 | 124905407 | 124905586 | chr10 | 124905834 | 124905880 | chr10 | 124905920 | 124906186 |
| chr10 | 124907214 | 124907633 | chr10 | 124908017 | 124908196 | chr10 | 124908987 | 124909115 |
| chr10 | 124909253 | 124909538 | chr10 | 124909674 | 124909769 | chr10 | 124910287 | 124910455 |
| chr10 | 124910709 | 124911126 | chr10 | 125425412 | 125425612 | chr10 | 125650778 | 125651163 |
| chr10 | 125651373 | 125651437 | chr10 | 125851248 | 125851727 | chr10 | 125852203 | 125852498 |
| chr10 | 125852541 | 125852622 | chr10 | 125852673 | 125853272 | chr10 | 126135878 | 126136146 |
| chr10 | 126136406 | 126136810 | chr10 | 126137145 | 126137503 | chr10 | 126198864 | 126199163 |
| chr10 | 126697829 | 126698125 | chr10 | 128076477 | 128076716 | chr10 | 128077188 | 128077241 |
| chr10 | 128993816 | 128994529 | chr10 | 128994636 | 128994995 | chr10 | 129534562 | 129534546 |
| chr10 | 129534993 | 129535447 | chr10 | 129535696 | 129535825 | chr10 | 129535986 | 129536224 |
| chr10 | 129536259 | 129536405 | chr10 | 129888774 | 129888965 | chr10 | 129948037 | 129948216 |
| chr10 | 130085210 | 130085276 | chr10 | 130085356 | 130085449 | chr10 | 130203339 | 130203578 |
| chr10 | 130338713 | 130338769 | chr10 | 130338804 | 130339062 | chr10 | 130577690 | 130577869 |
| chr10 | 131647829 | 131648008 | chr10 | 131756992 | 131757051 | chr10 | 131757852 | 131757853 |
| chr10 | 131761291 | 131761530 | chr10 | 131761587 | 131761826 | chr10 | 131761987 | 131762226 |
| chr10 | 131762493 | 131762732 | chr10 | 131762803 | 131763042 | chr10 | 131763264 | 131763337 |
| chr10 | 131763633 | 131763803 | chr10 | 131767343 | 131767504 | chr10 | 131768638 | 131768928 |
| chr10 | 131768930 | 131769117 | chr10 | 131769436 | 131770335 | chr10 | 131770583 | 131770762 |
| chr10 | 131770908 | 131771094 | chr10 | 131771282 | 131771302 | chr10 | 131936600 | 131936719 |
| chr10 | 131937393 | 131937512 | chr10 | 132001196 | 132001615 | chr10 | 133109096 | 133109261 |
| chr10 | 133110554 | 133110799 | chr10 | 133794798 | 133795242 | chr10 | 133795313 | 133795517 |
| chr10 | 133795593 | 133795884 | chr10 | 133795976 | 133796059 | chr10 | 133796302 | 133796312 |
| chr10 | 133849561 | 133850103 | chr10 | 133850443 | 133850862 | chr10 | 133951515 | 133952107 |
| chr10 | 133979076 | 133979164 | chr10 | 133999917 | 134000053 | chr10 | 134000109 | 134000124 |
| chr10 | 134000126 | 134000216 | chr10 | 134001140 | 134001359 | chr10 | 134016117 | 134016476 |
| chr10 | 134022771 | 134022950 | chr10 | 134095505 | 134095924 | chr10 | 134272961 | 134272970 |
| chr10 | 134301005 | 134301304 | chr10 | 134481228 | 134481527 | chr10 | 134598013 | 134598091 |
| chr10 | 134598368 | 134598534 | chr10 | 134598973 | 134599022 | chr10 | 134599432 | 134599546 |
| chr10 | 134599714 | 134600017 | chr10 | 134600038 | 134601053 | chr10 | 134601468 | 134601716 |
| chr10 | 134602128 | 134602346 | chr10 | 134607868 | 134608284 | chr10 | 134665056 | 134665295 |
| chr10 | 134679326 | 134679347 | chr10 | 134690469 | 134690636 | chr10 | 134693499 | 134693798 |
| chr10 | 134699772 | 134700011 | chr10 | 134733129 | 134733368 | chr10 | 134733408 | 134733707 |
| chr10 | 134738301 | 134738720 | chr10 | 134755773 | 134756270 | chr10 | 134787988 | 134788194 |
| chr10 | 134795938 | 134796117 | chr10 | 134901113 | 134901294 | chr10 | 134901296 | 134901592 |
| chr10 | 134901919 | 134902125 | chr10 | 134902188 | 134902352 | chr10 | 134916625 | 134916864 |
| chr10 | 134941043 | 134941282 | chr10 | 134942738 | 134943216 | chr10 | 134943461 | 134943644 |
| chr10 | 134944668 | 134944847 | chr10 | 135001961 | 135002260 | chr10 | 135014869 | 135015228 |
| chr10 | 135016972 | 135017209 | chr10 | 135017932 | 135018148 | chr10 | 135018744 | 135019043 |
| chr10 | 135020698 | 135020988 | chr10 | 135023396 | 135023575 | chr10 | 135043080 | 135043613 |
| chr10 | 135043869 | 135044228 | chr10 | 135044555 | 135044662 | chr10 | 135048742 | 135049041 |
| chr10 | 135050226 | 135050355 | chr10 | 135050357 | 135050765 | chr10 | 135076308 | 135076586 |
| chr10 | 135121730 | 135122131 | chr10 | 135139464 | 135139805 | chr11 | 232816 | 233115 |
| chr11 | 392560 | 392739 | chr11 | 394713 | 395072 | chr11 | 406789 | 407028 |
| chr11 | 407326 | 407565 | chr11 | 636821 | 636907 | chr11 | 637162 | 637264 |
| chr11 | 637350 | 637528 | chr11 | 726323 | 726562 | chr11 | 763236 | 763775 |
| chr11 | 829453 | 829533 | chr11 | 850480 | 850899 | chr11 | 862988 | 863167 |
| chr11 | 1027438 | 1027676 | chr11 | 1029142 | 1029501 | chr11 | 1030137 | 1030376 |
| chr11 | 1080304 | 1080416 | chr11 | 1081572 | 1081811 | chr11 | 1214582 | 1215001 |
| chr11 | 1215800 | 1216099 | chr11 | 1229871 | 1230050 | chr11 | 1244304 | 1244543 |
| chr11 | 1250788 | 1251027 | chr11 | 1251088 | 1251447 | chr11 | 1263504 | 1263743 |
| chr11 | 1273988 | 1274287 | chr11 | 1358284 | 1358387 | chr11 | 1374862 | 1375101 |
| chr11 | 1411842 | 1411980 | chr11 | 1430635 | 1430874 | chr11 | 1464205 | 1464504 |

TABLE 15-continued

Pan-cancer #5

| chr | start | end | chr | start | end | chr | start | end |
|---|---|---|---|---|---|---|---|---|
| chr11 | 1469125 | 1469484 | chr11 | 1471840 | 1472139 | chr11 | 1770263 | 1770330 |
| chr11 | 1867980 | 1868339 | chr11 | 1946056 | 1946235 | chr11 | 1957312 | 1957611 |
| chr11 | 1958983 | 1959282 | chr11 | 2040009 | 2040248 | chr11 | 2209824 | 2210363 |
| chr11 | 2225974 | 2226153 | chr11 | 2278625 | 2278924 | chr11 | 2291185 | 2291494 |
| chr11 | 2291801 | 2291844 | chr11 | 2291891 | 2291925 | chr11 | 2291945 | 2292058 |
| chr11 | 2292106 | 2292360 | chr11 | 2292392 | 2292730 | chr11 | 2437889 | 2438246 |
| chr11 | 2465323 | 2465448 | chr11 | 2465462 | 2465571 | chr11 | 2466514 | 2466873 |
| chr11 | 2884027 | 2884121 | chr11 | 2884159 | 2884386 | chr11 | 3169689 | 3169930 |
| chr11 | 4209031 | 4209210 | chr11 | 7273212 | 7273260 | chr11 | 7274141 | 7274320 |
| chr11 | 8040444 | 8040551 | chr11 | 8040553 | 8040564 | chr11 | 8040582 | 8040776 |
| chr11 | 8102910 | 8103209 | chr11 | 8189898 | 8190857 | chr11 | 8284466 | 8284858 |
| chr11 | 8289436 | 8289841 | chr11 | 8290100 | 8290515 | chr11 | 8615600 | 8615779 |
| chr11 | 9025890 | 9026429 | chr11 | 9112372 | 9112586 | chr11 | 9112640 | 9112834 |
| chr11 | 9405310 | 9405542 | chr11 | 10509594 | 10509893 | chr11 | 10811069 | 10811188 |
| chr11 | 10815784 | 10815896 | chr11 | 12029876 | 12030272 | chr11 | 12030274 | 12030355 |
| chr11 | 12030749 | 12030928 | chr11 | 12132423 | 12132662 | chr11 | 12398952 | 12399145 |
| chr11 | 12399181 | 12399311 | chr11 | 12695397 | 12695496 | chr11 | 12695573 | 12695696 |
| chr11 | 12696530 | 12696764 | chr11 | 13030489 | 13030792 | chr11 | 13030862 | 13030919 |
| chr11 | 15136001 | 15136456 | chr11 | 15136458 | 15136480 | chr11 | 16628727 | 16628998 |
| chr11 | 16632403 | 16632428 | chr11 | 16632514 | 16632752 | chr11 | 17497410 | 17497521 |
| chr11 | 17497546 | 17497769 | chr11 | 17740413 | 17740652 | chr11 | 17741583 | 17741685 |
| chr11 | 17741718 | 17741890 | chr11 | 17741953 | 17742484 | chr11 | 17742519 | 17742542 |
| chr11 | 17743640 | 17743874 | chr11 | 18812515 | 18812754 | chr11 | 18812940 | 18813179 |
| chr11 | 18813356 | 18813543 | chr11 | 18813610 | 18813655 | chr11 | 18813691 | 18814050 |
| chr11 | 19263774 | 19263953 | chr11 | 19367007 | 19367135 | chr11 | 19367268 | 19367426 |
| chr11 | 19735656 | 19735835 | chr11 | 20153622 | 20153861 | chr11 | 20178094 | 20178396 |
| chr11 | 20180244 | 20180896 | chr11 | 20181115 | 20181354 | chr11 | 20181608 | 20181644 |
| chr11 | 20181725 | 20182087 | chr11 | 20182763 | 20183062 | chr11 | 20183157 | 20183211 |
| chr11 | 20183313 | 20183516 | chr11 | 20183575 | 20183852 | chr11 | 20184481 | 20185500 |
| chr11 | 20229275 | 20229634 | chr11 | 20229811 | 20230110 | chr11 | 20230312 | 20230551 |
| chr11 | 20618116 | 20618393 | chr11 | 20618423 | 20618925 | chr11 | 20619220 | 20619255 |
| chr11 | 20619637 | 20620056 | chr11 | 20621460 | 20621733 | chr11 | 20622613 | 20622793 |
| chr11 | 20623259 | 20623452 | chr11 | 20690555 | 20690878 | chr11 | 20690983 | 20691034 |
| chr11 | 20691127 | 20691161 | chr11 | 20691163 | 20691380 | chr11 | 20691432 | 20691546 |
| chr11 | 20691591 | 20691616 | chr11 | 20691748 | 20692010 | chr11 | 20692372 | 20692611 |
| chr11 | 22215026 | 22215385 | chr11 | 22362853 | 22363272 | chr11 | 22364719 | 22365078 |
| chr11 | 22365323 | 22365562 | chr11 | 27742111 | 27742290 | chr11 | 27743025 | 27743261 |
| chr11 | 27743343 | 27743702 | chr11 | 27744057 | 27744557 | chr11 | 27744559 | 27744596 |
| chr11 | 27744609 | 27744832 | chr11 | 30037596 | 30037752 | chr11 | 30038595 | 30038834 |
| chr11 | 30605946 | 30606026 | chr11 | 30606028 | 30606161 | chr11 | 30606665 | 30606755 |
| chr11 | 30606796 | 30606964 | chr11 | 30607269 | 30607508 | chr11 | 31818376 | 31818513 |
| chr11 | 31818571 | 31818674 | chr11 | 31819221 | 31819508 | chr11 | 31819569 | 31819928 |
| chr11 | 31819966 | 31820361 | chr11 | 31820461 | 31821105 | chr11 | 31821209 | 31821388 |
| chr11 | 31821390 | 31821860 | chr11 | 31822240 | 31822479 | chr11 | 31824209 | 31824448 |
| chr11 | 31824473 | 31824772 | chr11 | 31824940 | 31824964 | chr11 | 31826043 | 31826071 |
| chr11 | 31826107 | 31826304 | chr11 | 31826409 | 31826733 | chr11 | 31827114 | 31827290 |
| chr11 | 31827362 | 31827520 | chr11 | 31827598 | 31828142 | chr11 | 31833007 | 31833232 |
| chr11 | 31835633 | 31835872 | chr11 | 31835959 | 31836517 | chr11 | 31837355 | 31837513 |
| chr11 | 31837542 | 31838486 | chr11 | 31838596 | 31839135 | chr11 | 31839215 | 31839946 |
| chr11 | 31840042 | 31840174 | chr11 | 31840879 | 31841025 | chr11 | 31841775 | 31842089 |
| chr11 | 31842175 | 31842366 | chr11 | 31845947 | 31845991 | chr11 | 31846078 | 31846306 |
| chr11 | 31846351 | 31847070 | chr11 | 31847169 | 31847302 | chr11 | 31847371 | 31847713 |
| chr11 | 31847770 | 31847873 | chr11 | 31847896 | 31848008 | chr11 | 31848377 | 31848603 |
| chr11 | 31848718 | 31849177 | chr11 | 32009013 | 32009127 | chr11 | 32354816 | 32354960 |
| chr11 | 32355000 | 32355291 | chr11 | 32448482 | 32448894 | chr11 | 32455499 | 32455738 |
| chr11 | 32455754 | 32456113 | chr11 | 32456189 | 32456446 | chr11 | 32456759 | 32456912 |
| chr11 | 32456914 | 32457199 | chr11 | 32457220 | 32457268 | chr11 | 32457615 | 32458274 |
| chr11 | 32458307 | 32458860 | chr11 | 32459609 | 32459971 | chr11 | 32460118 | 32460148 |
| chr11 | 32460465 | 32460586 | chr11 | 32460711 | 32460908 | chr11 | 33037393 | 33037632 |
| chr11 | 33858439 | 33858544 | chr11 | 33890197 | 33890436 | chr11 | 33993910 | 33993979 |
| chr11 | 34535019 | 34535198 | chr11 | 35547412 | 35547651 | chr11 | 35641582 | 35641718 |
| chr11 | 35684866 | 35685225 | chr11 | 43596412 | 43596693 | chr11 | 43600416 | 43600655 |
| chr11 | 43601012 | 43601551 | chr11 | 43602369 | 43602847 | chr11 | 43602849 | 43603037 |
| chr11 | 43603077 | 43603328 | chr11 | 43603544 | 43604146 | chr11 | 43604241 | 43604263 |
| chr11 | 44325599 | 44325770 | chr11 | 44326042 | 44326281 | chr11 | 44326341 | 44326350 |
| chr11 | 44326516 | 44326580 | chr11 | 44330555 | 44330609 | chr11 | 44330878 | 44330958 |
| chr11 | 44330960 | 44331440 | chr11 | 44331483 | 44331814 | chr11 | 44332978 | 44333157 |
| chr11 | 44333477 | 44333576 | chr11 | 44337564 | 44337629 | chr11 | 44337727 | 44337862 |
| chr11 | 44337883 | 44338058 | chr11 | 44338087 | 44338154 | chr11 | 44338232 | 44338471 |
| chr11 | 44340722 | 44340808 | chr11 | 44341881 | 44342120 | chr11 | 46316761 | 46316833 |
| chr11 | 46316896 | 46317356 | chr11 | 46317408 | 46317780 | chr11 | 47208968 | 47209267 |
| chr11 | 47358895 | 47359314 | chr11 | 57194253 | 57194612 | chr11 | 57235332 | 57235511 |
| chr11 | 57437215 | 57437316 | chr11 | 57501032 | 57501145 | chr11 | 58672666 | 58673145 |
| chr11 | 59323514 | 59323551 | chr11 | 59323780 | 59323813 | chr11 | 59329224 | 59329343 |
| chr11 | 59333344 | 59333623 | chr11 | 60718587 | 60718854 | chr11 | 60718977 | 60719246 |
| chr11 | 61049596 | 61049756 | chr11 | 61058193 | 61058432 | chr11 | 61062741 | 61063024 |

TABLE 15-continued

Pan-cancer #5

| chr | start | end | chr | start | end | chr | start | end |
|---|---|---|---|---|---|---|---|---|
| chr11 | 61063062 | 61063220 | chr11 | 61276902 | 61277120 | chr11 | 61594995 | 61595354 |
| chr11 | 61596321 | 61596740 | chr11 | 61664564 | 61664863 | chr11 | 61666032 | 61666211 |
| chr11 | 61722964 | 61722987 | chr11 | 62370646 | 62370825 | chr11 | 62440550 | 62440669 |
| chr11 | 63609981 | 63610099 | chr11 | 63641023 | 63641104 | chr11 | 63849298 | 63849530 |
| chr11 | 63934600 | 63934709 | chr11 | 64105852 | 64106031 | chr11 | 64120805 | 64120984 |
| chr11 | 64140323 | 64140502 | chr11 | 64410622 | 64410861 | chr11 | 64480380 | 64480691 |
| chr11 | 64480724 | 64481143 | chr11 | 64578481 | 64578600 | chr11 | 64739369 | 64739608 |
| chr11 | 64809866 | 64809965 | chr11 | 64950214 | 64950438 | chr11 | 65091311 | 65091471 |
| chr11 | 65185459 | 65185818 | chr11 | 65405568 | 65405597 | chr11 | 65478529 | 65478644 |
| chr11 | 65511077 | 65511256 | chr11 | 65511332 | 65511571 | chr11 | 65554043 | 65554195 |
| chr11 | 65600716 | 65600846 | chr11 | 65600848 | 65601735 | chr11 | 65779218 | 65779457 |
| chr11 | 65816357 | 65816520 | chr11 | 65816561 | 65816656 | chr11 | 66188041 | 66188220 |
| chr11 | 66188395 | 66188485 | chr11 | 66188571 | 66188784 | chr11 | 66188853 | 66189054 |
| chr11 | 66454350 | 66454529 | chr11 | 66511148 | 66511327 | chr11 | 66513133 | 66513252 |
| chr11 | 66513554 | 66513732 | chr11 | 66625105 | 66625344 | chr11 | 66648954 | 66649133 |
| chr11 | 66658258 | 66658365 | chr11 | 66790519 | 66790758 | chr11 | 67072139 | 67072489 |
| chr11 | 67209918 | 67210157 | chr11 | 67350887 | 67350961 | chr11 | 67350991 | 67351066 |
| chr11 | 67462559 | 67462918 | chr11 | 67764102 | 67764341 | chr11 | 67781387 | 67781650 |
| chr11 | 67797102 | 67797281 | chr11 | 68096026 | 68096257 | chr11 | 68409507 | 68409663 |
| chr11 | 68804647 | 68804872 | chr11 | 69192466 | 69192885 | chr11 | 69280478 | 69280717 |
| chr11 | 69465962 | 69466143 | chr11 | 69516896 | 69517251 | chr11 | 69517942 | 69518197 |
| chr11 | 69518199 | 69518301 | chr11 | 69518445 | 69518708 | chr11 | 69588848 | 69589267 |
| chr11 | 69589750 | 69589929 | chr11 | 69590067 | 69590113 | chr11 | 69590115 | 69590306 |
| chr11 | 71192669 | 71192921 | chr11 | 71318231 | 71318810 | chr11 | 71318953 | 71319070 |
| chr11 | 71951540 | 71951815 | chr11 | 71952262 | 71952417 | chr11 | 71952459 | 71952621 |
| chr11 | 71954538 | 71954717 | chr11 | 71955242 | 71955481 | chr11 | 71955905 | 71956444 |
| chr11 | 72432759 | 72432997 | chr11 | 72475581 | 72475814 | chr11 | 72532274 | 72532453 |
| chr11 | 72929666 | 72929731 | chr11 | 73072871 | 73073050 | chr11 | 73310285 | 73310445 |
| chr11 | 74394397 | 74394696 | chr11 | 74953165 | 74953337 | chr11 | 74953490 | 74953524 |
| chr11 | 75379155 | 75379249 | chr11 | 75379283 | 75379994 | chr11 | 75459452 | 75459564 |
| chr11 | 76371639 | 76372178 | chr11 | 78672822 | 78673061 | chr11 | 79151076 | 79151315 |
| chr11 | 82444290 | 82445189 | chr11 | 86085657 | 86085862 | chr11 | 86085932 | 86086065 |
| chr11 | 86383089 | 86383186 | chr11 | 88241623 | 88241976 | chr11 | 88242131 | 88242275 |
| chr11 | 88242359 | 88242624 | chr11 | 88798997 | 88799296 | chr11 | 91957408 | 91957767 |
| chr11 | 91957893 | 91957989 | chr11 | 91957991 | 91958312 | chr11 | 91958633 | 91959327 |
| chr11 | 91959355 | 91959532 | chr11 | 91959901 | 91960122 | chr11 | 93063495 | 93063734 |
| chr11 | 93063790 | 93064029 | chr11 | 94133991 | 94134464 | chr11 | 94134683 | 94134950 |
| chr11 | 94275701 | 94275813 | chr11 | 94473511 | 94473671 | chr11 | 94473673 | 94473769 |
| chr11 | 94473803 | 94473997 | chr11 | 94474399 | 94474401 | chr11 | 94502273 | 94502552 |
| chr11 | 94884070 | 94884235 | chr11 | 98891381 | 98891980 | chr11 | 100997579 | 100998085 |
| chr11 | 100998178 | 100998417 | chr11 | 100998588 | 100998745 | chr11 | 101453080 | 101453538 |
| chr11 | 101454511 | 101454580 | chr11 | 102961259 | 102961378 | chr11 | 102979953 | 102980132 |
| chr11 | 104034430 | 104034754 | chr11 | 104034756 | 104035089 | chr11 | 105480662 | 105480787 |
| chr11 | 105480859 | 105480901 | chr11 | 105481125 | 105481317 | chr11 | 105481319 | 105481319 |
| chr11 | 105481321 | 105481322 | chr11 | 105481324 | 105481604 | chr11 | 106888220 | 106888519 |
| chr11 | 106888542 | 106888901 | chr11 | 107461549 | 107461728 | chr11 | 107462318 | 107462557 |
| chr11 | 108603286 | 108603338 | chr11 | 109292830 | 109292830 | chr11 | 109292892 | 109293129 |
| chr11 | 109293635 | 109293764 | chr11 | 109293874 | 109293934 | chr11 | 110582154 | 110582420 |
| chr11 | 110582422 | 110582513 | chr11 | 110582794 | 110583029 | chr11 | 110583044 | 110583153 |
| chr11 | 110583473 | 110583832 | chr11 | 111383104 | 111383515 | chr11 | 111383517 | 111383552 |
| chr11 | 111383558 | 111383763 | chr11 | 111411019 | 111411199 | chr11 | 111411201 | 111411582 |
| chr11 | 111411822 | 111412147 | chr11 | 114112948 | 114113127 | chr11 | 115375030 | 115375269 |
| chr11 | 115530040 | 115530096 | chr11 | 115530222 | 115530590 | chr11 | 115530592 | 115530662 |
| chr11 | 115630414 | 115630474 | chr11 | 115630531 | 115630629 | chr11 | 115630631 | 115630889 |
| chr11 | 115630891 | 115631013 | chr11 | 115631217 | 115631456 | chr11 | 116451226 | 116451287 |
| chr11 | 119292705 | 119292884 | chr11 | 119293284 | 119293320 | chr11 | 119293353 | 119293385 |
| chr11 | 119293387 | 119293703 | chr11 | 119612134 | 119612268 | chr11 | 119612324 | 119612493 |
| chr11 | 119612999 | 119613178 | chr11 | 120008006 | 120008605 | chr11 | 120039730 | 120039969 |
| chr11 | 120435322 | 120435561 | chr11 | 120435726 | 120435905 | chr11 | 120998614 | 120998913 |
| chr11 | 122847182 | 122847781 | chr11 | 122847976 | 122848313 | chr11 | 122848369 | 122848695 |
| chr11 | 122849808 | 122850124 | chr11 | 122850149 | 122850263 | chr11 | 122850331 | 122850630 |
| chr11 | 122851074 | 122851313 | chr11 | 122852338 | 122852577 | chr11 | 122854907 | 122855029 |
| chr11 | 122855031 | 122855136 | chr11 | 123066359 | 123066538 | chr11 | 123228971 | 123229180 |
| chr11 | 123229182 | 123229407 | chr11 | 123229462 | 123229510 | chr11 | 123300736 | 123300955 |
| chr11 | 123301016 | 123301029 | chr11 | 123301083 | 123302115 | chr11 | 124735341 | 124735352 |
| chr11 | 124735375 | 124735580 | chr11 | 124736105 | 124736344 | chr11 | 124738694 | 124739125 |
| chr11 | 124739149 | 124739173 | chr11 | 125036286 | 125036344 | chr11 | 125036721 | 125036742 |
| chr11 | 125220423 | 125220722 | chr11 | 125755512 | 125755727 | chr11 | 125773587 | 125774061 |
| chr11 | 125774123 | 125774186 | chr11 | 126870108 | 126870287 | chr11 | 126870379 | 126870429 |
| chr11 | 126870431 | 126870501 | chr11 | 126870525 | 126870618 | chr11 | 126873304 | 126873603 |
| chr11 | 128562802 | 128563186 | chr11 | 128563337 | 128563818 | chr11 | 128563879 | 128564405 |
| chr11 | 128564641 | 128564874 | chr11 | 128564876 | 128564877 | chr11 | 128564992 | 128565480 |
| chr11 | 128657933 | 128658051 | chr11 | 129242783 | 129243242 | chr11 | 129243305 | 129243643 |
| chr11 | 129243944 | 129244301 | chr11 | 129244441 | 129244646 | chr11 | 129245747 | 129245892 |
| chr11 | 129245981 | 129246046 | chr11 | 130318860 | 130319099 | chr11 | 130319451 | 130319690 |
| chr11 | 130785406 | 130785705 | chr11 | 131522676 | 131522960 | chr11 | 131564873 | 131565101 |

TABLE 15-continued

Pan-cancer #5

| chr | start | end | chr | start | end | chr | start | end |
|---|---|---|---|---|---|---|---|---|
| chr11 | 131766899 | 131767048 | chr11 | 131780877 | 131781079 | chr11 | 131781294 | 131781350 |
| chr11 | 132484279 | 132484490 | chr11 | 132813545 | 132813758 | chr11 | 132813908 | 132814049 |
| chr11 | 132864036 | 132864275 | chr11 | 132934031 | 132934139 | chr11 | 132934141 | 132934270 |
| chr11 | 132952677 | 132953003 | chr11 | 132953233 | 132953423 | chr11 | 133231637 | 133231930 |
| chr11 | 133402114 | 133402353 | chr11 | 133825146 | 133825519 | chr11 | 133825521 | 133825625 |
| chr11 | 133906702 | 133907001 | chr11 | 133938911 | 133939064 | chr11 | 133939066 | 133939270 |
| chr11 | 134145629 | 134146427 | chr11 | 134146445 | 134146468 | chr11 | 134146579 | 134146676 |
| chr11 | 134146678 | 134146998 | chr11 | 134201404 | 134201640 | chr11 | 134201754 | 134202173 |
| chr11 | 134281288 | 134281543 | chr12 | 570012 | 570251 | chr12 | 1639060 | 1639299 |
| chr12 | 2162477 | 2162896 | chr12 | 2163071 | 2163370 | chr12 | 2403649 | 2403806 |
| chr12 | 2565971 | 2566330 | chr12 | 2861968 | 2862143 | chr12 | 2862268 | 2862327 |
| chr12 | 2964372 | 2964671 | chr12 | 3600241 | 3600420 | chr12 | 3602186 | 3602717 |
| chr12 | 3602865 | 3602965 | chr12 | 3603009 | 3603061 | chr12 | 4214010 | 4214245 |
| chr12 | 4274002 | 4274420 | chr12 | 4274475 | 4274490 | chr12 | 4362362 | 4362541 |
| chr12 | 4378172 | 4378411 | chr12 | 4379275 | 4379574 | chr12 | 4381341 | 4382480 |
| chr12 | 4382863 | 4383102 | chr12 | 4383399 | 4383878 | chr12 | 4384315 | 4384494 |
| chr12 | 4392801 | 4393023 | chr12 | 4405515 | 4405694 | chr12 | 4554727 | 4554906 |
| chr12 | 5017994 | 5018773 | chr12 | 5018954 | 5019035 | chr12 | 5019085 | 5019743 |
| chr12 | 5019794 | 5020314 | chr12 | 5020441 | 5020513 | chr12 | 5152951 | 5153287 |
| chr12 | 5153358 | 5153461 | chr12 | 5541020 | 5541259 | chr12 | 5542233 | 5542532 |
| chr12 | 5542656 | 5543015 | chr12 | 5840126 | 5840305 | chr12 | 6483537 | 6483836 |
| chr12 | 6664407 | 6664523 | chr12 | 7559085 | 7559384 | chr12 | 8127119 | 8127238 |
| chr12 | 8171284 | 8171823 | chr12 | 8808505 | 8808640 | chr12 | 8850582 | 8850818 |
| chr12 | 8975096 | 8975452 | chr12 | 10085826 | 10085932 | chr12 | 10363204 | 10363319 |
| chr12 | 11653375 | 11653464 | chr12 | 11653510 | 11653554 | chr12 | 12848294 | 12848653 |
| chr12 | 14133059 | 14133358 | chr12 | 14133541 | 14133960 | chr12 | 14135016 | 14135354 |
| chr12 | 15374156 | 15374395 | chr12 | 16500480 | 16500685 | chr12 | 20521624 | 20521923 |
| chr12 | 20522383 | 20522562 | chr12 | 20522681 | 20522860 | chr12 | 20522976 | 20522980 |
| chr12 | 21680300 | 21680779 | chr12 | 21810730 | 21810956 | chr12 | 21832988 | 21833095 |
| chr12 | 22093749 | 22093960 | chr12 | 22093962 | 22094269 | chr12 | 22094578 | 22094888 |
| chr12 | 22094997 | 22095048 | chr12 | 22095182 | 22095236 | chr12 | 22486717 | 22486882 |
| chr12 | 22487134 | 22487459 | chr12 | 22487461 | 22487556 | chr12 | 22698102 | 22698207 |
| chr12 | 24714835 | 24715014 | chr12 | 24715161 | 24715340 | chr12 | 24715947 | 24716204 |
| chr12 | 24716206 | 24716306 | chr12 | 25056243 | 25056524 | chr12 | 25101507 | 25101746 |
| chr12 | 25101824 | 25101998 | chr12 | 25102010 | 25102183 | chr12 | 25380187 | 25380366 |
| chr12 | 25398165 | 25398404 | chr12 | 28127676 | 28128395 | chr12 | 28128457 | 28129176 |
| chr12 | 29935913 | 29936152 | chr12 | 29936543 | 29936643 | chr12 | 29936662 | 29936777 |
| chr12 | 29936792 | 29936832 | chr12 | 29937234 | 29937343 | chr12 | 29937345 | 29937402 |
| chr12 | 30322697 | 30322925 | chr12 | 30323015 | 30323440 | chr12 | 30323503 | 30323596 |
| chr12 | 30975472 | 30975960 | chr12 | 31079179 | 31079368 | chr12 | 31079418 | 31079594 |
| chr12 | 32340225 | 32340336 | chr12 | 33591700 | 33591879 | chr12 | 33592512 | 33592642 |
| chr12 | 33592644 | 33592848 | chr12 | 33592933 | 33592991 | chr12 | 34494814 | 34494993 |
| chr12 | 34502649 | 34502888 | chr12 | 39299040 | 39299185 | chr12 | 39299269 | 39299639 |
| chr12 | 39539284 | 39539515 | chr12 | 40618318 | 40618557 | chr12 | 41086102 | 41086227 |
| chr12 | 41086229 | 41086461 | chr12 | 41086706 | 41087185 | chr12 | 41582422 | 41583081 |
| chr12 | 41583278 | 41583471 | chr12 | 43944800 | 43944881 | chr12 | 43945110 | 43945219 |
| chr12 | 43945262 | 43945380 | chr12 | 43945417 | 43945621 | chr12 | 43945742 | 43945781 |
| chr12 | 43946203 | 43946401 | chr12 | 45269417 | 45269714 | chr12 | 45444029 | 45444682 |
| chr12 | 45444715 | 45444895 | chr12 | 45444897 | 45444920 | chr12 | 45445062 | 45445348 |
| chr12 | 47225301 | 47225303 | chr12 | 47225320 | 47225477 | chr12 | 47225551 | 47225660 |
| chr12 | 47629275 | 47629307 | chr12 | 47629398 | 47629454 | chr12 | 48397154 | 48398173 |
| chr12 | 48398567 | 48398746 | chr12 | 49297770 | 49298009 | chr12 | 49366280 | 49366519 |
| chr12 | 49374838 | 49375027 | chr12 | 49375116 | 49375197 | chr12 | 49375248 | 49375607 |
| chr12 | 49390824 | 49391105 | chr12 | 49391147 | 49391975 | chr12 | 49657624 | 49657722 |
| chr12 | 49690975 | 49691154 | chr12 | 49727092 | 49727208 | chr12 | 49729640 | 49730179 |
| chr12 | 50297417 | 50297555 | chr12 | 50297974 | 50298136 | chr12 | 50426672 | 50426894 |
| chr12 | 51421134 | 51421373 | chr12 | 51421482 | 51421661 | chr12 | 51565470 | 51565562 |
| chr12 | 51930615 | 51930785 | chr12 | 52262896 | 52263195 | chr12 | 52301205 | 52301306 |
| chr12 | 52400735 | 52400907 | chr12 | 52400909 | 52401539 | chr12 | 52401606 | 52401616 |
| chr12 | 52627273 | 52627381 | chr12 | 52652054 | 52652220 | chr12 | 52652600 | 52652713 |
| chr12 | 53108005 | 53108304 | chr12 | 53359245 | 53359316 | chr12 | 53359386 | 53359664 |
| chr12 | 54089004 | 54089602 | chr12 | 54132172 | 54132411 | chr12 | 54145750 | 54145858 |
| chr12 | 54145881 | 54145989 | chr12 | 54321170 | 54321709 | chr12 | 54322108 | 54322302 |
| chr12 | 54324719 | 54325018 | chr12 | 54329264 | 54329479 | chr12 | 54329605 | 54330007 |
| chr12 | 54330980 | 54331219 | chr12 | 54332774 | 54333433 | chr12 | 54338589 | 54338818 |
| chr12 | 54338979 | 54339668 | chr12 | 54343718 | 54343830 | chr12 | 54345523 | 54345659 |
| chr12 | 54345966 | 54346122 | chr12 | 54348761 | 54349080 | chr12 | 54349256 | 54349420 |
| chr12 | 54354419 | 54354694 | chr12 | 54354815 | 54355087 | chr12 | 54355571 | 54355575 |
| chr12 | 54359873 | 54360172 | chr12 | 54360510 | 54360729 | chr12 | 54377835 | 54377947 |
| chr12 | 54377978 | 54378194 | chr12 | 54379100 | 54379699 | chr12 | 54379785 | 54379931 |
| chr12 | 54379959 | 54380486 | chr12 | 54387752 | 54388051 | chr12 | 54388141 | 54388320 |
| chr12 | 54391267 | 54391324 | chr12 | 54391400 | 54391506 | chr12 | 54393403 | 54393460 |
| chr12 | 54393462 | 54393724 | chr12 | 54393847 | 54394266 | chr12 | 54394307 | 54394419 |
| chr12 | 54394467 | 54394546 | chr12 | 54398697 | 54398786 | chr12 | 54398889 | 54399056 |
| chr12 | 54399542 | 54399721 | chr12 | 54402654 | 54402812 | chr12 | 54402975 | 54403454 |
| chr12 | 54408330 | 54408809 | chr12 | 54424670 | 54424749 | chr12 | 54425032 | 54425141 |

TABLE 15-continued

Pan-cancer #5

| chr | start | end | chr | start | end | chr | start | end |
|---|---|---|---|---|---|---|---|---|
| chr12 | 54447781 | 54447833 | chr12 | 54447899 | 54448080 | chr12 | 54520658 | 54520957 |
| chr12 | 54720221 | 54720320 | chr12 | 54812150 | 54812449 | chr12 | 54942906 | 54943191 |
| chr12 | 56882365 | 56882460 | chr12 | 57559778 | 57559914 | chr12 | 57618478 | 57618711 |
| chr12 | 57881046 | 57881345 | chr12 | 57943980 | 57944219 | chr12 | 58021218 | 58021459 |
| chr12 | 58021714 | 58021817 | chr12 | 58021824 | 58022093 | chr12 | 58025551 | 58025734 |
| chr12 | 58025870 | 58025970 | chr12 | 62584739 | 62585013 | chr12 | 62585031 | 62586118 |
| chr12 | 62586178 | 62586357 | chr12 | 63025615 | 63026257 | chr12 | 63543754 | 63544402 |
| chr12 | 63544499 | 63544600 | chr12 | 63544729 | 63544828 | chr12 | 63545239 | 63545418 |
| chr12 | 64061721 | 64062260 | chr12 | 64062295 | 64062498 | chr12 | 64062500 | 64062526 |
| chr12 | 64062528 | 64062654 | chr12 | 64062830 | 64063189 | chr12 | 64783098 | 64783322 |
| chr12 | 64784007 | 64784081 | chr12 | 64784108 | 64784352 | chr12 | 64784460 | 64784639 |
| chr12 | 65218320 | 65218551 | chr12 | 65218901 | 65219259 | chr12 | 65219281 | 65219528 |
| chr12 | 65219606 | 65219880 | chr12 | 65220129 | 65220428 | chr12 | 65514781 | 65515620 |
| chr12 | 65516379 | 65516558 | chr12 | 65557115 | 65557234 | chr12 | 65562064 | 65562172 |
| chr12 | 66122711 | 66122996 | chr12 | 66123381 | 66123610 | chr12 | 66135910 | 66136089 |
| chr12 | 66582743 | 66583048 | chr12 | 66583050 | 66583222 | chr12 | 69327182 | 69327541 |
| chr12 | 69754351 | 69754470 | chr12 | 69754600 | 69754710 | chr12 | 69964101 | 69964340 |
| chr12 | 70087412 | 70087651 | chr12 | 72332550 | 72332789 | chr12 | 72665167 | 72665526 |
| chr12 | 72665566 | 72665771 | chr12 | 72665773 | 72665877 | chr12 | 72666014 | 72666032 |
| chr12 | 72666620 | 72666808 | chr12 | 72666998 | 72667386 | chr12 | 72667388 | 72667519 |
| chr12 | 72667578 | 72667757 | chr12 | 75601168 | 75601231 | chr12 | 75601379 | 75601500 |
| chr12 | 75601696 | 75602007 | chr12 | 75602895 | 75603314 | chr12 | 75728262 | 75728561 |
| chr12 | 77719218 | 77719517 | chr12 | 79257138 | 79257437 | chr12 | 79258850 | 79258879 |
| chr12 | 79258966 | 79259029 | chr12 | 81102136 | 81102456 | chr12 | 81102513 | 81102603 |
| chr12 | 81107921 | 81107932 | chr12 | 81107997 | 81108100 | chr12 | 81471425 | 81471615 |
| chr12 | 81471754 | 81472204 | chr12 | 85306430 | 85306549 | chr12 | 85667173 | 85667832 |
| chr12 | 85673132 | 85673311 | chr12 | 85673385 | 85673915 | chr12 | 85673917 | 85674884 |
| chr12 | 88974346 | 88974356 | chr12 | 93966337 | 93966696 | chr12 | 93966910 | 93967216 |
| chr12 | 93967275 | 93967329 | chr12 | 94543308 | 94543547 | chr12 | 94543811 | 94543947 |
| chr12 | 94543949 | 94544080 | chr12 | 95267450 | 95267629 | chr12 | 95267772 | 95268000 |
| chr12 | 95941794 | 95941795 | chr12 | 95942965 | 95943053 | chr12 | 99288212 | 99288408 |
| chr12 | 99288622 | 99288937 | chr12 | 99288962 | 99288962 | chr12 | 99289162 | 99289411 |
| chr12 | 101025306 | 101025485 | chr12 | 101110926 | 101111165 | chr12 | 101111277 | 101111576 |
| chr12 | 103218396 | 103218655 | chr12 | 103350250 | 103350304 | chr12 | 103350384 | 103350429 |
| chr12 | 103351464 | 103351986 | chr12 | 103352052 | 103352155 | chr12 | 103352171 | 103352267 |
| chr12 | 103352269 | 103352283 | chr12 | 103352314 | 103352783 | chr12 | 103358763 | 103359002 |
| chr12 | 103359482 | 103359572 | chr12 | 103359574 | 103359661 | chr12 | 103889086 | 103889306 |
| chr12 | 103889660 | 103889714 | chr12 | 103889789 | 103889899 | chr12 | 104609340 | 104609526 |
| chr12 | 104609528 | 104609797 | chr12 | 104610163 | 104610179 | chr12 | 104850430 | 104850537 |
| chr12 | 104850578 | 104850669 | chr12 | 104850983 | 104851282 | chr12 | 104851941 | 104852151 |
| chr12 | 104852153 | 104852439 | chr12 | 104852441 | 104852446 | chr12 | 104852448 | 104852600 |
| chr12 | 105478222 | 105478457 | chr12 | 106974279 | 106974458 | chr12 | 106976641 | 106976780 |
| chr12 | 106976843 | 106976880 | chr12 | 106977394 | 106977589 | chr12 | 106979079 | 106979590 |
| chr12 | 106979718 | 106979874 | chr12 | 106979876 | 106980077 | chr12 | 106980129 | 106980428 |
| chr12 | 106980912 | 106981490 | chr12 | 107486462 | 107486673 | chr12 | 107487114 | 107487945 |
| chr12 | 107712199 | 107712378 | chr12 | 107713131 | 107713310 | chr12 | 107714771 | 107715250 |
| chr12 | 108168883 | 108169414 | chr12 | 108169550 | 108169662 | chr12 | 108237377 | 108237525 |
| chr12 | 108237661 | 108237676 | chr12 | 108238034 | 108238514 | chr12 | 108238684 | 108238719 |
| chr12 | 108297320 | 108297559 | chr12 | 110353315 | 110353553 | chr12 | 110717447 | 110717806 |
| chr12 | 111127079 | 111127438 | chr12 | 111471099 | 111471309 | chr12 | 111471611 | 111471638 |
| chr12 | 111471871 | 111471960 | chr12 | 111472059 | 111472196 | chr12 | 111472357 | 111472511 |
| chr12 | 111472572 | 111472672 | chr12 | 111763136 | 111763227 | chr12 | 113012877 | 113013236 |
| chr12 | 113541644 | 113542183 | chr12 | 113592150 | 113592449 | chr12 | 113900616 | 113900678 |
| chr12 | 113900753 | 113900855 | chr12 | 113900974 | 113901159 | chr12 | 113901408 | 113901693 |
| chr12 | 113901951 | 113902018 | chr12 | 113902042 | 113902429 | chr12 | 113903394 | 113903573 |
| chr12 | 113904689 | 113905108 | chr12 | 113908894 | 113909315 | chr12 | 113909329 | 113909503 |
| chr12 | 113909535 | 113909553 | chr12 | 113909569 | 113909657 | chr12 | 113909718 | 113909808 |
| chr12 | 113913180 | 113913682 | chr12 | 113913884 | 113913887 | chr12 | 113913889 | 113914139 |
| chr12 | 113916147 | 113916266 | chr12 | 113916327 | 113916419 | chr12 | 113916575 | 113916754 |
| chr12 | 113916873 | 113917112 | chr12 | 113917212 | 113917391 | chr12 | 113917684 | 113917701 |
| chr12 | 113917731 | 113917983 | chr12 | 114029325 | 114029509 | chr12 | 114029546 | 114029744 |
| chr12 | 114075942 | 114076177 | chr12 | 114337849 | 114337868 | chr12 | 114833895 | 114834173 |
| chr12 | 114838227 | 114838312 | chr12 | 114838369 | 114838826 | chr12 | 114840946 | 114841185 |
| chr12 | 114843016 | 114843187 | chr12 | 114843261 | 114843375 | chr12 | 114843454 | 114843753 |
| chr12 | 114844102 | 114844401 | chr12 | 114846623 | 114846862 | chr12 | 114846886 | 114846947 |
| chr12 | 114847043 | 114847164 | chr12 | 114847166 | 114847437 | chr12 | 114847578 | 114847741 |
| chr12 | 114851969 | 114852181 | chr12 | 114852214 | 114852268 | chr12 | 114877068 | 114877367 |
| chr12 | 114878448 | 114878594 | chr12 | 114878809 | 114879093 | chr12 | 114881550 | 114881849 |
| chr12 | 114882488 | 114882727 | chr12 | 114883385 | 114883554 | chr12 | 114885134 | 114885184 |
| chr12 | 114885372 | 114885373 | chr12 | 114918513 | 114918806 | chr12 | 115136153 | 115136441 |
| chr12 | 116945988 | 116946200 | chr12 | 116946251 | 116946647 | chr12 | 117473983 | 117474282 |
| chr12 | 117797999 | 117798170 | chr12 | 117799331 | 117799621 | chr12 | 118860317 | 118860436 |
| chr12 | 119212120 | 119212200 | chr12 | 119212319 | 119212479 | chr12 | 119418512 | 119418931 |
| chr12 | 119419369 | 119419541 | chr12 | 119419631 | 119419920 | chr12 | 120032777 | 120033256 |
| chr12 | 120148125 | 120148345 | chr12 | 120148824 | 120149063 | chr12 | 120885155 | 120885274 |
| chr12 | 121622472 | 121622591 | chr12 | 122192885 | 122192933 | chr12 | 122284969 | 122285189 |

TABLE 15-continued

Pan-cancer #5

| chr | start | end | chr | start | end | chr | start | end |
|---|---|---|---|---|---|---|---|---|
| chr12 | 123129041 | 123129139 | chr12 | 123233818 | 123233926 | chr12 | 124393463 | 124393702 |
| chr12 | 124397514 | 124397693 | chr12 | 125009254 | 125009381 | chr12 | 125533851 | 125534508 |
| chr12 | 125670024 | 125670261 | chr12 | 125670335 | 125670383 | chr12 | 126168468 | 126168707 |
| chr12 | 127210933 | 127210935 | chr12 | 127211317 | 127211472 | chr12 | 127765066 | 127765535 |
| chr12 | 127939988 | 127940189 | chr12 | 127940271 | 127940347 | chr12 | 128751295 | 128751534 |
| chr12 | 128751732 | 128751878 | chr12 | 128752115 | 128752331 | chr12 | 128752423 | 128753022 |
| chr12 | 128753136 | 128753315 | chr12 | 128850442 | 128850630 | chr12 | 128850632 | 128850739 |
| chr12 | 129337901 | 129337910 | chr12 | 129338588 | 129338826 | chr12 | 129338852 | 129338919 |
| chr12 | 130037571 | 130037866 | chr12 | 130387797 | 130387914 | chr12 | 130388332 | 130388435 |
| chr12 | 130389013 | 130389231 | chr12 | 130589116 | 130589354 | chr12 | 130645131 | 130645730 |
| chr12 | 130646590 | 130646654 | chr12 | 130646946 | 130647116 | chr12 | 130647574 | 130647909 |
| chr12 | 130647951 | 130648070 | chr12 | 130821287 | 130821706 | chr12 | 130968586 | 130968758 |
| chr12 | 131200303 | 131200649 | chr12 | 131400719 | 131401018 | chr12 | 131402943 | 131403229 |
| chr12 | 131513255 | 131513494 | chr12 | 132169246 | 132169357 | chr12 | 132221614 | 132222153 |
| chr12 | 132333337 | 132333418 | chr12 | 132333517 | 132333696 | chr12 | 132348549 | 132348788 |
| chr12 | 132423596 | 132423829 | chr12 | 132643371 | 132643376 | chr12 | 132986419 | 132986658 |
| chr12 | 133002713 | 133003312 | chr12 | 133194996 | 133195061 | chr12 | 133195063 | 133195229 |
| chr12 | 133199642 | 133199797 | chr12 | 133463657 | 133463956 | chr12 | 133464018 | 133464074 |
| chr12 | 133464755 | 133464920 | chr12 | 133481333 | 133481383 | chr12 | 133481490 | 133481520 |
| chr12 | 133481522 | 133481732 | chr12 | 133484660 | 133484853 | chr12 | 133485162 | 133485348 |
| chr12 | 133485463 | 133485690 | chr12 | 133485816 | 133485942 | chr12 | 133757959 | 133758198 |
| chr13 | 20735708 | 20736187 | chr13 | 21649557 | 21649856 | chr13 | 22243192 | 22243551 |
| chr13 | 23489764 | 23490003 | chr13 | 23733355 | 23734124 | chr13 | 23734182 | 23734298 |
| chr13 | 24477566 | 24477985 | chr13 | 25115623 | 25115648 | chr13 | 25115694 | 25115852 |
| chr13 | 25319764 | 25319905 | chr13 | 25320109 | 25320390 | chr13 | 25320388 | 25320540 |
| chr13 | 25320614 | 25321029 | chr13 | 25321113 | 25321443 | chr13 | 25321612 | 25322031 |
| chr13 | 25592963 | 25593040 | chr13 | 25593062 | 25593201 | chr13 | 25620951 | 25620954 |
| chr13 | 25620956 | 25621206 | chr13 | 25621264 | 25621490 | chr13 | 25744639 | 25744735 |
| chr13 | 25745301 | 25745595 | chr13 | 25745727 | 25746054 | chr13 | 25946301 | 25946488 |
| chr13 | 25946529 | 25946674 | chr13 | 25946802 | 25946888 | chr13 | 26042580 | 26042708 |
| chr13 | 26042769 | 26043171 | chr13 | 26043341 | 26043590 | chr13 | 26625267 | 26625657 |
| chr13 | 27132307 | 27132310 | chr13 | 27334118 | 27334657 | chr13 | 27334684 | 27334723 |
| chr13 | 27334725 | 27334983 | chr13 | 28239896 | 28240195 | chr13 | 28365615 | 28366181 |
| chr13 | 28366381 | 28366602 | chr13 | 28366665 | 28366680 | chr13 | 28366923 | 28367039 |
| chr13 | 28367712 | 28367946 | chr13 | 28368154 | 28368251 | chr13 | 28368373 | 28368672 |
| chr13 | 28368872 | 28369071 | chr13 | 28369162 | 28369891 | chr13 | 28369952 | 28370071 |
| chr13 | 28370855 | 28371154 | chr13 | 28394667 | 28394966 | chr13 | 28395408 | 28395647 |
| chr13 | 28395917 | 28396156 | chr13 | 28491694 | 28492050 | chr13 | 28492160 | 28492425 |
| chr13 | 28492427 | 28492639 | chr13 | 28528432 | 28528851 | chr13 | 28540657 | 28541016 |
| chr13 | 28543138 | 28543317 | chr13 | 28544321 | 28544585 | chr13 | 28544666 | 28544980 |
| chr13 | 28549396 | 28549892 | chr13 | 28550240 | 28550655 | chr13 | 28551320 | 28551549 |
| chr13 | 28551850 | 28552269 | chr13 | 28552660 | 28552660 | chr13 | 28552720 | 28552899 |
| chr13 | 28552935 | 28553234 | chr13 | 28673927 | 28674227 | chr13 | 28674721 | 28674826 |
| chr13 | 29067676 | 29068515 | chr13 | 29068847 | 29068986 | chr13 | 29068994 | 29069146 |
| chr13 | 29106217 | 29106422 | chr13 | 29106424 | 29106815 | chr13 | 29106899 | 29107064 |
| chr13 | 29107253 | 29107409 | chr13 | 30707495 | 30707674 | chr13 | 31742856 | 31743242 |
| chr13 | 32605033 | 32605212 | chr13 | 32605443 | 32605596 | chr13 | 32605675 | 32606001 |
| chr13 | 33591211 | 33591510 | chr13 | 33924579 | 33924812 | chr13 | 36704848 | 36705147 |
| chr13 | 36705351 | 36705446 | chr13 | 36705448 | 36705566 | chr13 | 36920216 | 36920224 |
| chr13 | 36920267 | 36920332 | chr13 | 36920334 | 36920387 | chr13 | 36920465 | 36920515 |
| chr13 | 36920528 | 36920887 | chr13 | 37004681 | 37004992 | chr13 | 37005581 | 37005581 |
| chr13 | 37005900 | 37006063 | chr13 | 37006434 | 37006658 | chr13 | 37006734 | 37006840 |
| chr13 | 37247982 | 37248149 | chr13 | 37248295 | 37248305 | chr13 | 37248307 | 37248316 |
| chr13 | 37248886 | 37249125 | chr13 | 37249040 | 37249125 | chr13 | 37633915 | 37634094 |
| chr13 | 37643855 | 37644094 | chr13 | 38443544 | 38443634 | chr13 | 38443636 | 38443716 |
| chr13 | 39261309 | 39261472 | chr13 | 43566148 | 43566652 | chr13 | 44947643 | 44947700 |
| chr13 | 44947726 | 44948302 | chr13 | 45885802 | 45885981 | chr13 | 45905243 | 45905356 |
| chr13 | 46425447 | 46425555 | chr13 | 46425576 | 46425654 | chr13 | 46660850 | 46660944 |
| chr13 | 46961395 | 46961634 | chr13 | 47468065 | 47468244 | chr13 | 47526167 | 47526286 |
| chr13 | 48667803 | 48667982 | chr13 | 49794034 | 49794926 | chr13 | 53312917 | 53313314 |
| chr13 | 53313513 | 53313529 | chr13 | 53313531 | 53313613 | chr13 | 53313678 | 53313950 |
| chr13 | 53419636 | 53419729 | chr13 | 53419731 | 53419875 | chr13 | 53419931 | 53420021 |
| chr13 | 53421827 | 53421880 | chr13 | 53422220 | 53422252 | chr13 | 53422433 | 53422459 |
| chr13 | 53423759 | 53424058 | chr13 | 58203504 | 58203743 | chr13 | 58203768 | 58204187 |
| chr13 | 58204253 | 58204492 | chr13 | 58205944 | 58206232 | chr13 | 58206453 | 58206772 |
| chr13 | 58206862 | 58207083 | chr13 | 58207382 | 58207401 | chr13 | 58207568 | 58207814 |
| chr13 | 58207892 | 58208101 | chr13 | 58208412 | 58209011 | chr13 | 67804144 | 67804175 |
| chr13 | 67804420 | 67804531 | chr13 | 67805100 | 67805286 | chr13 | 70681550 | 70681778 |
| chr13 | 70681867 | 70682149 | chr13 | 72439047 | 72439109 | chr13 | 73619573 | 73619698 |
| chr13 | 78492724 | 78492942 | chr13 | 78493092 | 78493271 | chr13 | 78493363 | 78493902 |
| chr13 | 79169850 | 79170114 | chr13 | 79170348 | 79170384 | chr13 | 79170468 | 79170981 |
| chr13 | 79171038 | 79171277 | chr13 | 79175678 | 79175944 | chr13 | 79176078 | 79176126 |
| chr13 | 79176277 | 79176421 | chr13 | 79176609 | 79176877 | chr13 | 79176897 | 79177185 |
| chr13 | 79177306 | 79177623 | chr13 | 79177886 | 79178096 | chr13 | 79183327 | 79183424 |
| chr13 | 84455499 | 84455798 | chr13 | 88323504 | 88323831 | chr13 | 88323868 | 88324169 |
| chr13 | 88324171 | 88324283 | chr13 | 88324415 | 88324519 | chr13 | 88325201 | 88325560 |

TABLE 15-continued

Pan-cancer #5

| chr | start | end | chr | start | end | chr | start | end |
|---|---|---|---|---|---|---|---|---|
| chr13 | 88325731 | 88326140 | chr13 | 88326447 | 88326708 | chr13 | 88326937 | 88327106 |
| chr13 | 88997832 | 88997951 | chr13 | 91948415 | 91948594 | chr13 | 92050668 | 92050843 |
| chr13 | 92051065 | 92051244 | chr13 | 92051273 | 92051400 | chr13 | 92051402 | 92051514 |
| chr13 | 93879213 | 93879303 | chr13 | 93879305 | 93879452 | chr13 | 93879596 | 93879775 |
| chr13 | 93879994 | 93880217 | chr13 | 93880534 | 93880738 | chr13 | 93880794 | 93880842 |
| chr13 | 93880844 | 93880953 | chr13 | 95357237 | 95357416 | chr13 | 95357496 | 95357855 |
| chr13 | 95357954 | 95358253 | chr13 | 95359656 | 95359895 | chr13 | 95360228 | 95360467 |
| chr13 | 95363111 | 95363452 | chr13 | 95363494 | 95363530 | chr13 | 95363697 | 95363960 |
| chr13 | 95364065 | 95364291 | chr13 | 95364409 | 95364675 | chr13 | 95364677 | 95364888 |
| chr13 | 95619931 | 95620170 | chr13 | 95620560 | 95620782 | chr13 | 95620854 | 95621099 |
| chr13 | 96031611 | 96031725 | chr13 | 96204923 | 96205438 | chr13 | 96296297 | 96296346 |
| chr13 | 96296373 | 96296556 | chr13 | 96296841 | 96296950 | chr13 | 96296992 | 96297215 |
| chr13 | 96743713 | 96743895 | chr13 | 96744212 | 96744263 | chr13 | 99851662 | 99851748 |
| chr13 | 100547770 | 100547894 | chr13 | 100608462 | 100608536 | chr13 | 100608597 | 100608805 |
| chr13 | 100608839 | 100609136 | chr13 | 100621859 | 100622031 | chr13 | 100624213 | 100624233 |
| chr13 | 100624324 | 100624452 | chr13 | 100624509 | 100624715 | chr13 | 100626905 | 100626925 |
| chr13 | 100630545 | 100631084 | chr13 | 100634227 | 100634382 | chr13 | 100635310 | 100635330 |
| chr13 | 100635399 | 100635518 | chr13 | 100636084 | 100636111 | chr13 | 100636131 | 100636323 |
| chr13 | 100637289 | 100637588 | chr13 | 100642151 | 100642282 | chr13 | 100643955 | 100644170 |
| chr13 | 100649334 | 100649576 | chr13 | 100649800 | 100649885 | chr13 | 100649945 | 100650018 |
| chr13 | 102568380 | 102568559 | chr13 | 102569313 | 102569643 | chr13 | 103046619 | 103047053 |
| chr13 | 103047055 | 103047098 | chr13 | 103052252 | 103052468 | chr13 | 103052470 | 103052671 |
| chr13 | 103052797 | 103052828 | chr13 | 103052830 | 103053036 | chr13 | 103053296 | 103053509 |
| chr13 | 107186781 | 107186960 | chr13 | 107187085 | 107187242 | chr13 | 108518298 | 108518354 |
| chr13 | 108518445 | 108518494 | chr13 | 108518724 | 108519017 | chr13 | 108519162 | 108519461 |
| chr13 | 108519637 | 108519746 | chr13 | 108519902 | 108519996 | chr13 | 108520370 | 108520535 |
| chr13 | 108520916 | 108520945 | chr13 | 108520947 | 108520969 | chr13 | 109147599 | 109147863 |
| chr13 | 109148155 | 109148279 | chr13 | 109148377 | 109148438 | chr13 | 109148685 | 109149115 |
| chr13 | 109149164 | 109149284 | chr13 | 110434374 | 110434672 | chr13 | 110958720 | 110958977 |
| chr13 | 110958979 | 110959054 | chr13 | 110959629 | 110959649 | chr13 | 110959753 | 110960048 |
| chr13 | 110960345 | 110960386 | chr13 | 110960453 | 110960692 | chr13 | 111278225 | 111278521 |
| chr13 | 111363885 | 111364060 | chr13 | 112272891 | 112273102 | chr13 | 112707603 | 112707962 |
| chr13 | 112708002 | 112708005 | chr13 | 112708308 | 112708601 | chr13 | 112709408 | 112709647 |
| chr13 | 112709713 | 112709713 | chr13 | 112709787 | 112710026 | chr13 | 112710247 | 112710253 |
| chr13 | 112710360 | 112710476 | chr13 | 112710669 | 112710823 | chr13 | 112710825 | 112711294 |
| chr13 | 112711376 | 112711868 | chr13 | 112711924 | 112713123 | chr13 | 112715267 | 112715719 |
| chr13 | 112715910 | 112716389 | chr13 | 112716695 | 112716814 | chr13 | 112716982 | 112717243 |
| chr13 | 112717323 | 112717611 | chr13 | 112717743 | 112718042 | chr13 | 112719940 | 112720599 |
| chr13 | 112720626 | 112720865 | chr13 | 112720938 | 112721027 | chr13 | 112722129 | 112722221 |
| chr13 | 112722275 | 112722403 | chr13 | 112724431 | 112724610 | chr13 | 112726240 | 112726293 |
| chr13 | 112726436 | 112726659 | chr13 | 112727962 | 112728201 | chr13 | 112728336 | 112728367 |
| chr13 | 112758033 | 112758373 | chr13 | 112758496 | 112758688 | chr13 | 112759112 | 112759349 |
| chr13 | 112759538 | 112759717 | chr13 | 112760007 | 112760413 | chr13 | 112760755 | 112761305 |
| chr13 | 113598526 | 113598877 | chr13 | 113985597 | 113985956 | chr13 | 114055881 | 114056240 |
| chr13 | 114059990 | 114060409 | chr13 | 114074692 | 114074931 | chr13 | 114123081 | 114123358 |
| chr13 | 114189654 | 114189732 | chr13 | 114221548 | 114221655 | chr13 | 114304637 | 114305016 |
| chr13 | 114479330 | 114479509 | chr13 | 114497930 | 114498349 | chr13 | 114748251 | 114748730 |
| chr13 | 114780482 | 114781141 | chr13 | 114807537 | 114807896 | chr13 | 114855533 | 114855772 |
| chr13 | 114862381 | 114862458 | chr13 | 114961729 | 114962028 | chr14 | 21093364 | 21093531 |
| chr14 | 21093604 | 21093723 | chr14 | 21100674 | 21100906 | chr14 | 22004932 | 22004993 |
| chr14 | 22004995 | 22005171 | chr14 | 23356162 | 23356341 | chr14 | 23706666 | 23706845 |
| chr14 | 24803493 | 24803917 | chr14 | 24803919 | 24804123 | chr14 | 24804425 | 24804512 |
| chr14 | 26674280 | 26674459 | chr14 | 26674625 | 26674703 | chr14 | 27066520 | 27066699 |
| chr14 | 27067065 | 27067157 | chr14 | 27067373 | 27067427 | chr14 | 29225457 | 29225636 |
| chr14 | 29225986 | 29226285 | chr14 | 29228567 | 29228866 | chr14 | 29229008 | 29229249 |
| chr14 | 29229251 | 29229487 | chr14 | 29230995 | 29231186 | chr14 | 29231329 | 29231688 |
| chr14 | 29234911 | 29235309 | chr14 | 29235342 | 29235450 | chr14 | 29236966 | 29237067 |
| chr14 | 29237140 | 29237205 | chr14 | 29242687 | 29242707 | chr14 | 29243433 | 29243670 |
| chr14 | 29243731 | 29243972 | chr14 | 29244147 | 29244383 | chr14 | 29247596 | 29247835 |
| chr14 | 29254612 | 29254794 | chr14 | 31344269 | 31344628 | chr14 | 31925640 | 31925804 |
| chr14 | 32597619 | 32597759 | chr14 | 33402373 | 33402512 | chr14 | 33402514 | 33402852 |
| chr14 | 33402942 | 33403019 | chr14 | 33403125 | 33403421 | chr14 | 33403783 | 33404502 |
| chr14 | 34420150 | 34420347 | chr14 | 35023188 | 35023427 | chr14 | 35024347 | 35024454 |
| chr14 | 36003471 | 36003904 | chr14 | 36004081 | 36004578 | chr14 | 36004608 | 36004735 |
| chr14 | 36004822 | 36004922 | chr14 | 36005012 | 36005087 | chr14 | 36972709 | 36973008 |
| chr14 | 36973157 | 36973222 | chr14 | 36973455 | 36973636 | chr14 | 36974421 | 36974800 |
| chr14 | 36974802 | 36974928 | chr14 | 36975058 | 36975058 | chr14 | 36975200 | 36975229 |
| chr14 | 36975281 | 36975499 | chr14 | 36977558 | 36977930 | chr14 | 36977975 | 36978097 |
| chr14 | 36978474 | 36978653 | chr14 | 36979657 | 36979724 | chr14 | 36982870 | 36983068 |
| chr14 | 36983674 | 36984227 | chr14 | 36985767 | 36985946 | chr14 | 36986212 | 36986472 |
| chr14 | 36987302 | 36987787 | chr14 | 36987862 | 36988221 | chr14 | 36988449 | 36988564 |
| chr14 | 36990779 | 36991033 | chr14 | 36991095 | 36991258 | chr14 | 36991501 | 36991693 |
| chr14 | 36991989 | 36992164 | chr14 | 36992222 | 36992507 | chr14 | 36993386 | 36993488 |
| chr14 | 36993694 | 36994045 | chr14 | 36994145 | 36995009 | chr14 | 36995011 | 36995104 |
| chr14 | 37116026 | 37116295 | chr14 | 37117535 | 37117697 | chr14 | 37123339 | 37124178 |
| chr14 | 37124482 | 37124648 | chr14 | 37124910 | 37125629 | chr14 | 37126150 | 37126389 |

TABLE 15-continued

Pan-cancer #5

| chr | start | end | chr | start | end | chr | start | end |
|---|---|---|---|---|---|---|---|---|
| chr14 | 37126463 | 37126714 | chr14 | 37126965 | 37127002 | chr14 | 37127207 | 37127386 |
| chr14 | 37127572 | 37127780 | chr14 | 37129990 | 37130349 | chr14 | 37132296 | 37132554 |
| chr14 | 37132603 | 37132775 | chr14 | 37132908 | 37133147 | chr14 | 37135740 | 37135868 |
| chr14 | 37135922 | 37136018 | chr14 | 37136295 | 37136425 | chr14 | 37136514 | 37136693 |
| chr14 | 38060588 | 38060917 | chr14 | 38677445 | 38677581 | chr14 | 38724207 | 38724526 |
| chr14 | 38724979 | 38725346 | chr14 | 38725455 | 38725560 | chr14 | 42074467 | 42074587 |
| chr14 | 42074669 | 42074944 | chr14 | 42075023 | 42075066 | chr14 | 42075511 | 42075810 |
| chr14 | 42075812 | 42076044 | chr14 | 42076106 | 42076290 | chr14 | 42076749 | 42076928 |
| chr14 | 42077130 | 42077368 | chr14 | 42077696 | 42077804 | chr14 | 42079190 | 42079429 |
| chr14 | 48143657 | 48143719 | chr14 | 48143798 | 48143958 | chr14 | 48144359 | 48144500 |
| chr14 | 48144619 | 48144764 | chr14 | 48145237 | 48145338 | chr14 | 50333976 | 50334084 |
| chr14 | 50334336 | 50334455 | chr14 | 51338642 | 51338732 | chr14 | 51339048 | 51339061 |
| chr14 | 51560207 | 51560714 | chr14 | 51560771 | 51561293 | chr14 | 51561295 | 51561526 |
| chr14 | 51561680 | 51562099 | chr14 | 52534571 | 52534870 | chr14 | 52534929 | 52535027 |
| chr14 | 52535056 | 52535264 | chr14 | 52535335 | 52535425 | chr14 | 52535427 | 52535758 |
| chr14 | 52535760 | 52535973 | chr14 | 52535975 | 52536066 | chr14 | 52536068 | 52536105 |
| chr14 | 52536343 | 52536488 | chr14 | 52734414 | 52734525 | chr14 | 52734527 | 52734653 |
| chr14 | 52734687 | 52735002 | chr14 | 52735045 | 52735346 | chr14 | 52781422 | 52782021 |
| chr14 | 54422549 | 54422925 | chr14 | 54422927 | 54423028 | chr14 | 55370100 | 55370219 |
| chr14 | 55596008 | 55596043 | chr14 | 55765207 | 55765686 | chr14 | 57045445 | 57045840 |
| chr14 | 57260845 | 57261095 | chr14 | 57261175 | 57261408 | chr14 | 57261466 | 57261880 |
| chr14 | 57261977 | 57262276 | chr14 | 57264001 | 57264646 | chr14 | 57264765 | 57264807 |
| chr14 | 57265148 | 57265320 | chr14 | 57270854 | 57270972 | chr14 | 57271154 | 57271333 |
| chr14 | 57271919 | 57272114 | chr14 | 57274387 | 57274739 | chr14 | 57274741 | 57275050 |
| chr14 | 57275211 | 57275406 | chr14 | 57275521 | 57275686 | chr14 | 57276074 | 57276180 |
| chr14 | 57276344 | 57276763 | chr14 | 57277830 | 57278763 | chr14 | 57278838 | 57279565 |
| chr14 | 57279643 | 57279712 | chr14 | 57283238 | 57283409 | chr14 | 57283446 | 57284037 |
| chr14 | 57284071 | 57284737 | chr14 | 58332201 | 58332494 | chr14 | 60097111 | 60097247 |
| chr14 | 60097407 | 60097650 | chr14 | 60386111 | 60386350 | chr14 | 60386551 | 60386743 |
| chr14 | 60794532 | 60794771 | chr14 | 60952196 | 60952420 | chr14 | 60952517 | 60952633 |
| chr14 | 60952730 | 60953039 | chr14 | 60973157 | 60973418 | chr14 | 60973618 | 60974008 |
| chr14 | 60974078 | 60974157 | chr14 | 60974273 | 60974506 | chr14 | 60975290 | 60975889 |
| chr14 | 60976075 | 60976609 | chr14 | 60976803 | 60976957 | chr14 | 60977263 | 60977713 |
| chr14 | 60977880 | 60978222 | chr14 | 60981116 | 60981355 | chr14 | 60981586 | 60981813 |
| chr14 | 60982007 | 60982368 | chr14 | 60982574 | 60982726 | chr14 | 60982757 | 60982996 |
| chr14 | 61104242 | 61104557 | chr14 | 61104624 | 61104952 | chr14 | 61108539 | 61108904 |
| chr14 | 61109031 | 61109078 | chr14 | 61109129 | 61109548 | chr14 | 61109742 | 61110341 |
| chr14 | 61114058 | 61114537 | chr14 | 61115235 | 61115594 | chr14 | 61118743 | 61118841 |
| chr14 | 61118872 | 61119227 | chr14 | 61747389 | 61747528 | chr14 | 61747583 | 61747816 |
| chr14 | 61748002 | 61748117 | chr14 | 62279520 | 62279623 | chr14 | 62279625 | 62279853 |
| chr14 | 62279899 | 62280092 | chr14 | 62583710 | 62583870 | chr14 | 62583919 | 62584009 |
| chr14 | 63512064 | 63512376 | chr14 | 63512486 | 63512709 | chr14 | 63512741 | 63512905 |
| chr14 | 63513050 | 63513229 | chr14 | 64222332 | 64222450 | chr14 | 65005803 | 65005915 |
| chr14 | 65008915 | 65008975 | chr14 | 65008998 | 65009274 | chr14 | 65233253 | 65233552 |
| chr14 | 67886583 | 67886702 | chr14 | 69013958 | 69014195 | chr14 | 69866930 | 69867289 |
| chr14 | 70014640 | 70015059 | chr14 | 70346045 | 70346584 | chr14 | 70654379 | 70654597 |
| chr14 | 70654599 | 70654639 | chr14 | 70654641 | 70654798 | chr14 | 70655451 | 70655890 |
| chr14 | 70655920 | 70656170 | chr14 | 72398642 | 72399121 | chr14 | 72399452 | 72399557 |
| chr14 | 72399830 | 72400129 | chr14 | 73167676 | 73167975 | chr14 | 73174938 | 73175237 |
| chr14 | 73178717 | 73178956 | chr14 | 73180112 | 73180336 | chr14 | 73318371 | 73318730 |
| chr14 | 73333174 | 73333256 | chr14 | 73602351 | 73602470 | chr14 | 74705940 | 74706299 |
| chr14 | 74706357 | 74706397 | chr14 | 74706941 | 74707545 | chr14 | 74707573 | 74707748 |
| chr14 | 74707792 | 74707911 | chr14 | 74707913 | 74707976 | chr14 | 74708760 | 74709059 |
| chr14 | 74892272 | 74892645 | chr14 | 74892975 | 74893191 | chr14 | 75078070 | 75078243 |
| chr14 | 75760210 | 75760329 | chr14 | 76604580 | 76604819 | chr14 | 76604985 | 76605464 |
| chr14 | 76843364 | 76843386 | chr14 | 76843733 | 76844058 | chr14 | 77228021 | 77228107 |
| chr14 | 77606833 | 77606856 | chr14 | 77606922 | 77607312 | chr14 | 77737110 | 77737146 |
| chr14 | 77737148 | 77737685 | chr14 | 79745088 | 79745277 | chr14 | 85996395 | 85996694 |
| chr14 | 85996760 | 85996796 | chr14 | 85996892 | 85996999 | chr14 | 85997735 | 85997926 |
| chr14 | 85998468 | 85998575 | chr14 | 85998630 | 85998786 | chr14 | 85999472 | 85999532 |
| chr14 | 85999597 | 85999711 | chr14 | 86000182 | 86000574 | chr14 | 86000886 | 86001196 |
| chr14 | 89817813 | 89818112 | chr14 | 90527617 | 90527856 | chr14 | 90983225 | 90983385 |
| chr14 | 91691167 | 91691385 | chr14 | 91766189 | 91766542 | chr14 | 92789438 | 92789617 |
| chr14 | 92789777 | 92789822 | chr14 | 92789960 | 92790099 | chr14 | 92790551 | 92790790 |
| chr14 | 92979835 | 92980074 | chr14 | 93154979 | 93155385 | chr14 | 93389450 | 93389458 |
| chr14 | 93389557 | 93389694 | chr14 | 93389713 | 93389869 | chr14 | 93706678 | 93706857 |
| chr14 | 94254302 | 94254459 | chr14 | 94254499 | 94254601 | chr14 | 94405641 | 94405880 |
| chr14 | 95233616 | 95233646 | chr14 | 95234557 | 95234711 | chr14 | 95235026 | 95235383 |
| chr14 | 95235939 | 95236200 | chr14 | 95236450 | 95236598 | chr14 | 95239298 | 95239349 |
| chr14 | 95239422 | 95239717 | chr14 | 95240053 | 95240268 | chr14 | 95240410 | 95240497 |
| chr14 | 96342551 | 96342631 | chr14 | 96342880 | 96343225 | chr14 | 96343330 | 96343435 |
| chr14 | 96343668 | 96343792 | chr14 | 97045327 | 97045506 | chr14 | 97058761 | 97058818 |
| chr14 | 97058944 | 97059180 | chr14 | 97499257 | 97499416 | chr14 | 97499616 | 97499627 |
| chr14 | 97499847 | 97499850 | chr14 | 97499971 | 97500035 | chr14 | 97684957 | 97685297 |
| chr14 | 97685624 | 97686038 | chr14 | 99584501 | 99584740 | chr14 | 99736048 | 99736213 |
| chr14 | 100437707 | 100437950 | chr14 | 100438018 | 100438066 | chr14 | 100438609 | 100438908 |

TABLE 15-continued

Pan-cancer #5

| chr | start | end | chr | start | end | chr | start | end |
|---|---|---|---|---|---|---|---|---|
| chr14 | 100643267 | 100643566 | chr14 | 101193145 | 101193147 | chr14 | 101250012 | 101250371 |
| chr14 | 101543783 | 101544270 | chr14 | 101923033 | 101923332 | chr14 | 101923520 | 101923687 |
| chr14 | 101924031 | 101924122 | chr14 | 101924966 | 101925072 | chr14 | 101925656 | 101925705 |
| chr14 | 101925707 | 101925985 | chr14 | 102026273 | 102026572 | chr14 | 102026703 | 102027062 |
| chr14 | 102031132 | 102031194 | chr14 | 102031236 | 102031371 | chr14 | 102031434 | 102031450 |
| chr14 | 102031508 | 102031666 | chr14 | 102247824 | 102248303 | chr14 | 102418533 | 102418652 |
| chr14 | 102521501 | 102521860 | chr14 | 102529912 | 102530178 | chr14 | 102530426 | 102530605 |
| chr14 | 102564386 | 102564502 | chr14 | 102681994 | 102682233 | chr14 | 103021308 | 103022087 |
| chr14 | 103394784 | 103395203 | chr14 | 103477540 | 103477771 | chr14 | 103655154 | 103655568 |
| chr14 | 103655570 | 103655684 | chr14 | 103673992 | 103673994 | chr14 | 103674069 | 103674080 |
| chr14 | 103674216 | 103674231 | chr14 | 103687002 | 103687301 | chr14 | 103739885 | 103740239 |
| chr14 | 103740275 | 103740437 | chr14 | 103745606 | 103745845 | chr14 | 104159978 | 104160160 |
| chr14 | 104202624 | 104202852 | chr14 | 104547814 | 104547993 | chr14 | 104571902 | 104572201 |
| chr14 | 104601657 | 104601873 | chr14 | 104601964 | 104602138 | chr14 | 104604954 | 104605193 |
| chr14 | 104620334 | 104620633 | chr14 | 104627564 | 104627862 | chr14 | 104645048 | 104645277 |
| chr14 | 104646225 | 104646584 | chr14 | 104647183 | 104647362 | chr14 | 104682452 | 104682751 |
| chr14 | 104862764 | 104863123 | chr14 | 105071198 | 105071340 | chr14 | 105157401 | 105157640 |
| chr14 | 105241220 | 105241267 | chr14 | 105246463 | 105246642 | chr14 | 105511960 | 105512463 |
| chr14 | 105658268 | 105658507 | chr14 | 105714177 | 105714442 | chr14 | 105715248 | 105715393 |
| chr14 | 105715539 | 105715565 | chr15 | 22822269 | 22822384 | chr15 | 23158294 | 23158593 |
| chr15 | 26107541 | 26107744 | chr15 | 26107846 | 26107960 | chr15 | 26108010 | 26108327 |
| chr15 | 26108549 | 26108789 | chr15 | 27018281 | 27018329 | chr15 | 27212791 | 27213270 |
| chr15 | 27603982 | 27604057 | chr15 | 28341615 | 28341980 | chr15 | 28341982 | 28342020 |
| chr15 | 28344081 | 28344188 | chr15 | 28344224 | 28344350 | chr15 | 28352156 | 28352422 |
| chr15 | 29077185 | 29077394 | chr15 | 29077429 | 29077484 | chr15 | 29130712 | 29131048 |
| chr15 | 29131533 | 29131631 | chr15 | 29131756 | 29131971 | chr15 | 29407680 | 29407814 |
| chr15 | 29407867 | 29408099 | chr15 | 29862423 | 29862537 | chr15 | 31455297 | 31455578 |
| chr15 | 31775500 | 31775638 | chr15 | 31775679 | 31775783 | chr15 | 31776146 | 31776190 |
| chr15 | 33009649 | 33009762 | chr15 | 33009822 | 33010399 | chr15 | 33010401 | 33010676 |
| chr15 | 33010721 | 33011166 | chr15 | 33011168 | 33011448 | chr15 | 33011498 | 33011737 |
| chr15 | 33486970 | 33487209 | chr15 | 33602725 | 33602964 | chr15 | 33603110 | 33603609 |
| chr15 | 33603648 | 33603709 | chr15 | 33879168 | 33879347 | chr15 | 34630346 | 34630389 |
| chr15 | 34630439 | 34630525 | chr15 | 34729381 | 34729680 | chr15 | 34786425 | 34786944 |
| chr15 | 34787233 | 34787384 | chr15 | 35046935 | 35047149 | chr15 | 35087563 | 35087802 |
| chr15 | 37180227 | 37180241 | chr15 | 37180414 | 37180826 | chr15 | 37402898 | 37403087 |
| chr15 | 37403116 | 37403316 | chr15 | 40211736 | 40212275 | chr15 | 40575538 | 40575837 |
| chr15 | 41165152 | 41165751 | chr15 | 41804786 | 41805865 | chr15 | 41835732 | 41835814 |
| chr15 | 41913660 | 41913899 | chr15 | 41952493 | 41952792 | chr15 | 43810472 | 43810510 |
| chr15 | 44037485 | 44037604 | chr15 | 45403554 | 45403681 | chr15 | 45403799 | 45404000 |
| chr15 | 45404103 | 45404213 | chr15 | 45404833 | 45404833 | chr15 | 45404898 | 45405209 |
| chr15 | 45421291 | 45421530 | chr15 | 45421874 | 45421947 | chr15 | 45427263 | 45427341 |
| chr15 | 45427370 | 45427502 | chr15 | 45427520 | 45427720 | chr15 | 45427772 | 45427879 |
| chr15 | 45479371 | 45479517 | chr15 | 45479775 | 45479789 | chr15 | 45670503 | 45670839 |
| chr15 | 45670933 | 45670971 | chr15 | 47476794 | 47476806 | chr15 | 47476877 | 47476981 |
| chr15 | 47477013 | 47477093 | chr15 | 48483907 | 48483963 | chr15 | 48936639 | 48937213 |
| chr15 | 48937215 | 48937646 | chr15 | 48937710 | 48938077 | chr15 | 48938122 | 48938347 |
| chr15 | 48938349 | 48938601 | chr15 | 51385838 | 51386257 | chr15 | 51633986 | 51634151 |
| chr15 | 51634175 | 51634225 | chr15 | 51973695 | 51973695 | chr15 | 51973764 | 51974030 |
| chr15 | 53075740 | 53075865 | chr15 | 53075986 | 53077001 | chr15 | 53077066 | 53077455 |
| chr15 | 53077574 | 53077813 | chr15 | 53077971 | 53078320 | chr15 | 53079262 | 53079678 |
| chr15 | 53079718 | 53079892 | chr15 | 53079971 | 53080161 | chr15 | 53080263 | 53080620 |
| chr15 | 53080861 | 53080991 | chr15 | 53081055 | 53081100 | chr15 | 53081223 | 53081297 |
| chr15 | 53081399 | 53081702 | chr15 | 53082348 | 53082587 | chr15 | 53096735 | 53096974 |
| chr15 | 53097157 | 53097336 | chr15 | 53097535 | 53097569 | chr15 | 53097778 | 53097907 |
| chr15 | 53098382 | 53098757 | chr15 | 54270424 | 54270783 | chr15 | 54270858 | 54271025 |
| chr15 | 55452972 | 55453087 | chr15 | 55699008 | 55699127 | chr15 | 55880891 | 55881044 |
| chr15 | 55881046 | 55881095 | chr15 | 58357800 | 58357820 | chr15 | 59158454 | 59158616 |
| chr15 | 59950343 | 59950461 | chr15 | 60286937 | 60287586 | chr15 | 60287644 | 60287780 |
| chr15 | 60288703 | 60288935 | chr15 | 60289229 | 60289638 | chr15 | 60296047 | 60296286 |
| chr15 | 60296495 | 60296618 | chr15 | 60296861 | 60296924 | chr15 | 60297152 | 60297514 |
| chr15 | 60297544 | 60297827 | chr15 | 60297942 | 60298203 | chr15 | 61520816 | 61521115 |
| chr15 | 61521559 | 61521621 | chr15 | 61521657 | 61521676 | chr15 | 61521713 | 61522038 |
| chr15 | 62456848 | 62456966 | chr15 | 62457009 | 62457019 | chr15 | 65669760 | 65669999 |
| chr15 | 65862054 | 65862213 | chr15 | 66963725 | 66963823 | chr15 | 66963928 | 66963964 |
| chr15 | 68112537 | 68112716 | chr15 | 68113794 | 68113973 | chr15 | 68114048 | 68114287 |
| chr15 | 68116286 | 68116682 | chr15 | 68117753 | 68118712 | chr15 | 68118783 | 68118784 |
| chr15 | 68118799 | 68118876 | chr15 | 68118930 | 68119175 | chr15 | 68119579 | 68120353 |
| chr15 | 68120631 | 68120662 | chr15 | 68120753 | 68120932 | chr15 | 68121150 | 68121958 |
| chr15 | 68122569 | 68122748 | chr15 | 68125164 | 68125763 | chr15 | 68127717 | 68128436 |
| chr15 | 68128492 | 68128597 | chr15 | 68260435 | 68260735 | chr15 | 71055770 | 71055906 |
| chr15 | 72412113 | 72412263 | chr15 | 72743650 | 72743859 | chr15 | 73659917 | 73660156 |
| chr15 | 73661476 | 73661748 | chr15 | 74044960 | 74045023 | chr15 | 74045075 | 74045199 |
| chr15 | 74421927 | 74421954 | chr15 | 74421980 | 74422226 | chr15 | 74422787 | 74423012 |
| chr15 | 74658070 | 74658397 | chr15 | 74658502 | 74658553 | chr15 | 74658555 | 74658595 |
| chr15 | 74686082 | 74686126 | chr15 | 74818670 | 74818789 | chr15 | 74903822 | 74904001 |
| chr15 | 75251245 | 75251414 | chr15 | 75251479 | 75251484 | chr15 | 75251580 | 75251879 |

TABLE 15-continued

Pan-cancer #5

| chr | start | end | chr | start | end | chr | start | end |
| --- | --- | --- | --- | --- | --- | --- | --- | --- |
| chr15 | 75471218 | 75471275 | chr15 | 76627515 | 76627537 | chr15 | 76627576 | 76627907 |
| chr15 | 76628959 | 76629026 | chr15 | 76629163 | 76629314 | chr15 | 76629588 | 76629633 |
| chr15 | 76629732 | 76630095 | chr15 | 76630097 | 76630125 | chr15 | 76630520 | 76630931 |
| chr15 | 76632518 | 76632520 | chr15 | 76635040 | 76635110 | chr15 | 76635576 | 76635635 |
| chr15 | 76638387 | 76638497 | chr15 | 77448976 | 77449087 | chr15 | 78501725 | 78502024 |
| chr15 | 78556795 | 78557034 | chr15 | 78557110 | 78557204 | chr15 | 78596066 | 78596245 |
| chr15 | 78632626 | 78632669 | chr15 | 78632684 | 78632925 | chr15 | 78912192 | 78912372 |
| chr15 | 78912442 | 78912491 | chr15 | 78912549 | 78912728 | chr15 | 78912832 | 78913028 |
| chr15 | 78913095 | 78913251 | chr15 | 78913444 | 78913470 | chr15 | 78913481 | 78913683 |
| chr15 | 79104143 | 79104159 | chr15 | 79381709 | 79381746 | chr15 | 79382099 | 79382648 |
| chr15 | 79382693 | 79382998 | chr15 | 79383000 | 79383268 | chr15 | 79383873 | 79384052 |
| chr15 | 79502137 | 79502381 | chr15 | 79575197 | 79575556 | chr15 | 79576062 | 79576361 |
| chr15 | 79724034 | 79724120 | chr15 | 79724402 | 79724561 | chr15 | 79724607 | 79724793 |
| chr15 | 79724864 | 79725241 | chr15 | 79725332 | 79725584 | chr15 | 82336777 | 82337076 |
| chr15 | 82339995 | 82340234 | chr15 | 83315246 | 83315474 | chr15 | 83316232 | 83316640 |
| chr15 | 83316642 | 83317162 | chr15 | 83349131 | 83349612 | chr15 | 83349672 | 83349790 |
| chr15 | 83378112 | 83378164 | chr15 | 83378186 | 83378471 | chr15 | 83776161 | 83776269 |
| chr15 | 83776271 | 83776307 | chr15 | 83776333 | 83776717 | chr15 | 83776769 | 83776880 |
| chr15 | 83875571 | 83875666 | chr15 | 83875706 | 83875985 | chr15 | 83876953 | 83877252 |
| chr15 | 83952108 | 83952113 | chr15 | 83952769 | 83952827 | chr15 | 83953024 | 83953049 |
| chr15 | 84115648 | 84115811 | chr15 | 84115813 | 84115854 | chr15 | 84115932 | 84116067 |
| chr15 | 84116829 | 84116995 | chr15 | 84322994 | 84323124 | chr15 | 84748500 | 84748620 |
| chr15 | 84748679 | 84749339 | chr15 | 85143052 | 85143144 | chr15 | 88798591 | 88798654 |
| chr15 | 88798725 | 88798890 | chr15 | 88799448 | 88799999 | chr15 | 88800001 | 88800302 |
| chr15 | 88800463 | 88801004 | chr15 | 88801006 | 88801009 | chr15 | 88801089 | 88801182 |
| chr15 | 89149070 | 89149489 | chr15 | 89248651 | 89249010 | chr15 | 89345953 | 89346327 |
| chr15 | 89346347 | 89346492 | chr15 | 89346568 | 89346794 | chr15 | 89346882 | 89347047 |
| chr15 | 89903410 | 89903889 | chr15 | 89910426 | 89910845 | chr15 | 89910988 | 89911287 |
| chr15 | 89913676 | 89913855 | chr15 | 89914144 | 89914450 | chr15 | 89914867 | 89914983 |
| chr15 | 89915156 | 89915455 | chr15 | 89921862 | 89922038 | chr15 | 89922500 | 89922649 |
| chr15 | 89942671 | 89943030 | chr15 | 89943319 | 89943775 | chr15 | 89949317 | 89949410 |
| chr15 | 89949617 | 89950036 | chr15 | 89950154 | 89950737 | chr15 | 89951082 | 89951215 |
| chr15 | 89951302 | 89951377 | chr15 | 89951466 | 89951901 | chr15 | 89952065 | 89952453 |
| chr15 | 89952700 | 89953144 | chr15 | 89954122 | 89954416 | chr15 | 89956288 | 89956354 |
| chr15 | 89956423 | 89956527 | chr15 | 90039488 | 90039787 | chr15 | 90755819 | 90756144 |
| chr15 | 91643264 | 91643683 | chr15 | 92936281 | 92936426 | chr15 | 92937115 | 92937474 |
| chr15 | 92937849 | 92938061 | chr15 | 92938123 | 92938294 | chr15 | 92938316 | 92938388 |
| chr15 | 93631638 | 93632117 | chr15 | 93632558 | 93632730 | chr15 | 93632732 | 93633337 |
| chr15 | 94347588 | 94347707 | chr15 | 95388666 | 95388712 | chr15 | 96874259 | 96874416 |
| chr15 | 96889374 | 96889506 | chr15 | 96897853 | 96898092 | chr15 | 96911456 | 96911692 |
| chr15 | 96911764 | 96911815 | chr15 | 96952594 | 96953099 | chr15 | 96953132 | 96953313 |
| chr15 | 96959720 | 96959961 | chr15 | 96960428 | 96960513 | chr15 | 96960630 | 96960907 |
| chr15 | 97006274 | 97006623 | chr15 | 98504040 | 98504219 | chr15 | 98836077 | 98836477 |
| chr15 | 98965179 | 98965232 | chr15 | 99193106 | 99193345 | chr15 | 99193350 | 99193583 |
| chr15 | 99193873 | 99194172 | chr15 | 99456272 | 99456404 | chr15 | 100913332 | 100913596 |
| chr15 | 101420447 | 101420665 | chr15 | 101420848 | 101420860 | chr15 | 101420972 | 101421087 |
| chr15 | 101513806 | 101513831 | chr16 | 142567 | 142775 | chr16 | 215341 | 215873 |
| chr16 | 215913 | 215960 | chr16 | 215962 | 216300 | chr16 | 216587 | 217070 |
| chr16 | 230229 | 230316 | chr16 | 230497 | 230708 | chr16 | 318040 | 318316 |
| chr16 | 318422 | 318444 | chr16 | 337510 | 337749 | chr16 | 410303 | 410482 |
| chr16 | 611304 | 611603 | chr16 | 611876 | 612355 | chr16 | 612774 | 613133 |
| chr16 | 667466 | 667561 | chr16 | 677879 | 677993 | chr16 | 700225 | 700404 |
| chr16 | 726539 | 727078 | chr16 | 731400 | 731699 | chr16 | 735131 | 735670 |
| chr16 | 740888 | 741003 | chr16 | 741280 | 741507 | chr16 | 837262 | 837561 |
| chr16 | 845881 | 846060 | chr16 | 882567 | 882686 | chr16 | 895011 | 895250 |
| chr16 | 943398 | 943637 | chr16 | 1018046 | 1018225 | chr16 | 1030210 | 1030271 |
| chr16 | 1030444 | 1030749 | chr16 | 1052488 | 1052727 | chr16 | 1103032 | 1103032 |
| chr16 | 1116721 | 1116766 | chr16 | 1128927 | 1129226 | chr16 | 1155068 | 1155307 |
| chr16 | 1203883 | 1203963 | chr16 | 1204003 | 1204111 | chr16 | 1217226 | 1217583 |
| chr16 | 1217943 | 1218182 | chr16 | 1228711 | 1229010 | chr16 | 1230057 | 1230236 |
| chr16 | 1248521 | 1248760 | chr16 | 1267844 | 1268203 | chr16 | 1271447 | 1271746 |
| chr16 | 1312450 | 1312689 | chr16 | 1323900 | 1324139 | chr16 | 1382862 | 1383041 |
| chr16 | 1394400 | 1394579 | chr16 | 1397380 | 1397559 | chr16 | 1407366 | 1407485 |
| chr16 | 1407819 | 1407938 | chr16 | 1428422 | 1428961 | chr16 | 1491471 | 1491694 |
| chr16 | 1730213 | 1730692 | chr16 | 1741757 | 1742176 | chr16 | 2028986 | 2029225 |
| chr16 | 2040818 | 2040961 | chr16 | 2040981 | 2040981 | chr16 | 2040983 | 2041513 |
| chr16 | 2041582 | 2042257 | chr16 | 2106629 | 2106741 | chr16 | 2128503 | 2128682 |
| chr16 | 2129033 | 2129332 | chr16 | 2141835 | 2142014 | chr16 | 2142468 | 2142707 |
| chr16 | 2213239 | 2213396 | chr16 | 2232665 | 2232784 | chr16 | 2234634 | 2235113 |
| chr16 | 2281163 | 2281402 | chr16 | 2287231 | 2287453 | chr16 | 2531136 | 2531255 |
| chr16 | 2764275 | 2764574 | chr16 | 2770033 | 2770512 | chr16 | 2818018 | 2818249 |
| chr16 | 2892457 | 2892603 | chr16 | 2892627 | 2892797 | chr16 | 3017157 | 3017431 |
| chr16 | 3068097 | 3068276 | chr16 | 3151038 | 3151264 | chr16 | 3211625 | 3211742 |
| chr16 | 3211805 | 3211982 | chr16 | 3220474 | 3220557 | chr16 | 3220591 | 3220893 |
| chr16 | 3221142 | 3221701 | chr16 | 3221787 | 3222325 | chr16 | 3225390 | 3225689 |
| chr16 | 3232697 | 3233017 | chr16 | 3233199 | 3233331 | chr16 | 3233435 | 3234104 |

TABLE 15-continued

Pan-cancer #5

| chr | start | end | chr | start | end | chr | start | end |
|---|---|---|---|---|---|---|---|---|
| chr16 | 3234197 | 3234541 | chr16 | 3237783 | 3238022 | chr16 | 3238164 | 3238622 |
| chr16 | 3238912 | 3239631 | chr16 | 3239692 | 3239931 | chr16 | 3241517 | 3241756 |
| chr16 | 3241862 | 3241981 | chr16 | 3355200 | 3355234 | chr16 | 3355251 | 3355799 |
| chr16 | 3598818 | 3599057 | chr16 | 3696620 | 3696799 | chr16 | 3802932 | 3803171 |
| chr16 | 4264433 | 4264792 | chr16 | 4431039 | 4431213 | chr16 | 4846061 | 4846415 |
| chr16 | 5037803 | 5038102 | chr16 | 5541026 | 5541257 | chr16 | 6069989 | 6070122 |
| chr16 | 7354560 | 7354658 | chr16 | 7354700 | 7354739 | chr16 | 8780956 | 8781135 |
| chr16 | 8870279 | 8870458 | chr16 | 9009781 | 9010075 | chr16 | 10274325 | 10274504 |
| chr16 | 10275231 | 10275470 | chr16 | 10275671 | 10276030 | chr16 | 10276270 | 10276799 |
| chr16 | 10276801 | 10277051 | chr16 | 10277072 | 10277409 | chr16 | 10479719 | 10479966 |
| chr16 | 10479968 | 10480078 | chr16 | 12971812 | 12972035 | chr16 | 12994359 | 12994838 |
| chr16 | 12994969 | 12995688 | chr16 | 12995707 | 12995804 | chr16 | 12996074 | 12996426 |
| chr16 | 12996520 | 12996819 | chr16 | 12996861 | 12997100 | chr16 | 12997306 | 12997785 |
| chr16 | 14725745 | 14725864 | chr16 | 15489851 | 15489884 | chr16 | 15820726 | 15820965 |
| chr16 | 18802486 | 18802725 | chr16 | 18950987 | 18951093 | chr16 | 19567117 | 19567536 |
| chr16 | 19895051 | 19895125 | chr16 | 19895156 | 19895230 | chr16 | 21831520 | 21832052 |
| chr16 | 21839250 | 21839348 | chr16 | 22824599 | 22825077 | chr16 | 22825158 | 22825198 |
| chr16 | 22825225 | 22825470 | chr16 | 22825886 | 22826184 | chr16 | 23313374 | 23313613 |
| chr16 | 23313674 | 23313739 | chr16 | 23313780 | 23313913 | chr16 | 23706240 | 23706287 |
| chr16 | 23706412 | 23706599 | chr16 | 23765995 | 23766098 | chr16 | 23766133 | 23766234 |
| chr16 | 23847311 | 23847325 | chr16 | 23847489 | 23847512 | chr16 | 23847789 | 23847816 |
| chr16 | 23847818 | 23847875 | chr16 | 23847934 | 23848003 | chr16 | 23848005 | 23848053 |
| chr16 | 24267013 | 24267145 | chr16 | 24267221 | 24267312 | chr16 | 24267383 | 24267594 |
| chr16 | 25266436 | 25266675 | chr16 | 25702855 | 25703094 | chr16 | 25703686 | 25704123 |
| chr16 | 25704390 | 25704705 | chr16 | 26664758 | 26664853 | chr16 | 27460002 | 27460156 |
| chr16 | 28074101 | 28074255 | chr16 | 28074418 | 28074760 | chr16 | 28074869 | 28074937 |
| chr16 | 28074956 | 28075288 | chr16 | 29118954 | 29119133 | chr16 | 29153201 | 29153254 |
| chr16 | 29244800 | 29245099 | chr16 | 29830796 | 29831155 | chr16 | 29888549 | 29888761 |
| chr16 | 30017240 | 30017539 | chr16 | 30116211 | 30116390 | chr16 | 30124597 | 30124949 |
| chr16 | 30804458 | 30804575 | chr16 | 30826363 | 30826570 | chr16 | 30906930 | 30907049 |
| chr16 | 30907123 | 30907229 | chr16 | 31228310 | 31228402 | chr16 | 31446904 | 31447173 |
| chr16 | 31497971 | 31498087 | chr16 | 31500460 | 31500759 | chr16 | 31580469 | 31580739 |
| chr16 | 46721556 | 46721787 | chr16 | 47177447 | 47177686 | chr16 | 48845120 | 48845229 |
| chr16 | 49309067 | 49309366 | chr16 | 49311432 | 49311990 | chr16 | 49312033 | 49312391 |
| chr16 | 49313268 | 49313807 | chr16 | 49313921 | 49314220 | chr16 | 49314341 | 49314640 |
| chr16 | 49314692 | 49314822 | chr16 | 49315202 | 49315381 | chr16 | 49315831 | 49316316 |
| chr16 | 49316509 | 49316670 | chr16 | 49637986 | 49638165 | chr16 | 50335693 | 50335872 |
| chr16 | 51183964 | 51184431 | chr16 | 51184725 | 51184958 | chr16 | 51185055 | 51185292 |
| chr16 | 51185763 | 51185965 | chr16 | 51186026 | 51186329 | chr16 | 51186591 | 51187036 |
| chr16 | 51189848 | 51190038 | chr16 | 51190122 | 51190309 | chr16 | 53563519 | 53563734 |
| chr16 | 54318855 | 54319063 | chr16 | 54319325 | 54319564 | chr16 | 54321557 | 54321819 |
| chr16 | 54321908 | 54321916 | chr16 | 54324960 | 54325199 | chr16 | 54628600 | 54628959 |
| chr16 | 54964875 | 54965211 | chr16 | 54966728 | 54967265 | chr16 | 54970986 | 54971007 |
| chr16 | 54971326 | 54971505 | chr16 | 55090585 | 55090944 | chr16 | 55357827 | 55357941 |
| chr16 | 55357992 | 55358186 | chr16 | 55358213 | 55358351 | chr16 | 55358567 | 55358632 |
| chr16 | 55358785 | 55359175 | chr16 | 55362963 | 55363326 | chr16 | 55364631 | 55364930 |
| chr16 | 55365020 | 55365219 | chr16 | 55404898 | 55405200 | chr16 | 55405202 | 55405317 |
| chr16 | 55512745 | 55512763 | chr16 | 55512936 | 55512984 | chr16 | 55689853 | 55689901 |
| chr16 | 55689903 | 55689991 | chr16 | 55690013 | 55690380 | chr16 | 55690454 | 55690577 |
| chr16 | 55690762 | 55690912 | chr16 | 56224479 | 56224782 | chr16 | 56224784 | 56224793 |
| chr16 | 56224795 | 56224833 | chr16 | 56224881 | 56224958 | chr16 | 56228271 | 56228417 |
| chr16 | 56228578 | 56228686 | chr16 | 56651006 | 56651124 | chr16 | 56651239 | 56651365 |
| chr16 | 56659095 | 56659754 | chr16 | 56672077 | 56672173 | chr16 | 56672222 | 56672386 |
| chr16 | 56672514 | 56672761 | chr16 | 56709755 | 56709893 | chr16 | 56709950 | 56710114 |
| chr16 | 57222710 | 57222806 | chr16 | 57935476 | 57935655 | chr16 | 58018531 | 58018950 |
| chr16 | 58019149 | 58019508 | chr16 | 58120875 | 58121058 | chr16 | 58497136 | 58497336 |
| chr16 | 58497470 | 58497495 | chr16 | 58497672 | 58497911 | chr16 | 58498101 | 58498280 |
| chr16 | 58498468 | 58498585 | chr16 | 58498587 | 58498809 | chr16 | 58521634 | 58521813 |
| chr16 | 58550415 | 58550587 | chr16 | 58969669 | 58969895 | chr16 | 62068387 | 62068610 |
| chr16 | 62068923 | 62069057 | chr16 | 62070669 | 62070848 | chr16 | 65154833 | 65155192 |
| chr16 | 65156288 | 65156587 | chr16 | 66461694 | 66461933 | chr16 | 66612797 | 66613096 |
| chr16 | 66613335 | 66613359 | chr16 | 67197615 | 67197854 | chr16 | 67197935 | 67198114 |
| chr16 | 67198218 | 67199057 | chr16 | 67241130 | 67241309 | chr16 | 67313791 | 67313970 |
| chr16 | 68544170 | 68544409 | chr16 | 68676307 | 68676605 | chr16 | 68676842 | 68677086 |
| chr16 | 68770847 | 68771086 | chr16 | 68771167 | 68771402 | chr16 | 68876728 | 68876847 |
| chr16 | 70595543 | 70595782 | chr16 | 71459957 | 71460089 | chr16 | 71460271 | 71460429 |
| chr16 | 71715705 | 71715884 | chr16 | 72957660 | 72957899 | chr16 | 73100576 | 73100612 |
| chr16 | 75019677 | 75019856 | chr16 | 77247366 | 77247545 | chr16 | 77468182 | 77468458 |
| chr16 | 77822493 | 77822589 | chr16 | 77822875 | 77822972 | chr16 | 78079893 | 78080132 |
| chr16 | 79623798 | 79623968 | chr16 | 80838052 | 80838173 | chr16 | 80966296 | 80966535 |
| chr16 | 82660499 | 82660578 | chr16 | 82660638 | 82660727 | chr16 | 82660729 | 82660817 |
| chr16 | 84074767 | 84074946 | chr16 | 84153290 | 84153469 | chr16 | 84402163 | 84402402 |
| chr16 | 84853274 | 84853452 | chr16 | 85075418 | 85075644 | chr16 | 85317747 | 85317879 |
| chr16 | 85485652 | 85485951 | chr16 | 85517254 | 85517613 | chr16 | 85678551 | 85678850 |
| chr16 | 85684234 | 85684533 | chr16 | 85699596 | 85699925 | chr16 | 85932754 | 85932933 |
| chr16 | 86320254 | 86320489 | chr16 | 86320491 | 86320493 | chr16 | 86320659 | 86320898 |

TABLE 15-continued

Pan-cancer #5

| chr | start | end | chr | start | end | chr | start | end |
|---|---|---|---|---|---|---|---|---|
| chr16 | 86320925 | 86321147 | chr16 | 86530848 | 86530993 | chr16 | 86531017 | 86531147 |
| chr16 | 86531233 | 86531289 | chr16 | 86531375 | 86531481 | chr16 | 86531528 | 86531652 |
| chr16 | 86541537 | 86541956 | chr16 | 86542296 | 86542535 | chr16 | 86544103 | 86544558 |
| chr16 | 86545060 | 86545062 | chr16 | 86599481 | 86599931 | chr16 | 86600406 | 86600765 |
| chr16 | 86600868 | 86601107 | chr16 | 86601204 | 86601623 | chr16 | 86602038 | 86602590 |
| chr16 | 87092347 | 87092646 | chr16 | 87635029 | 87635208 | chr16 | 87636444 | 87636491 |
| chr16 | 87636627 | 87636782 | chr16 | 87636784 | 87636983 | chr16 | 87714178 | 87714477 |
| chr16 | 87723648 | 87724187 | chr16 | 88164316 | 88164555 | chr16 | 88498142 | 88498861 |
| chr16 | 88503978 | 88504397 | chr16 | 88506265 | 88506616 | chr16 | 88512329 | 88512628 |
| chr16 | 88603617 | 88603848 | chr16 | 88623885 | 88624165 | chr16 | 88757428 | 88757571 |
| chr16 | 88879858 | 88880097 | chr16 | 88883159 | 88883458 | chr16 | 88940981 | 88941220 |
| chr16 | 88942021 | 88942239 | chr16 | 88943463 | 88944122 | chr16 | 88945726 | 88946085 |
| chr16 | 88955160 | 88955459 | chr16 | 88956136 | 88956495 | chr16 | 88957374 | 88957934 |
| chr16 | 88958295 | 88958534 | chr16 | 88963191 | 88963850 | chr16 | 88966207 | 88966686 |
| chr16 | 88968630 | 88968869 | chr16 | 88977929 | 88978168 | chr16 | 88992975 | 88993334 |
| chr16 | 88999543 | 88999557 | chr16 | 88999574 | 88999693 | chr16 | 89000127 | 89000306 |
| chr16 | 89001020 | 89001139 | chr16 | 89007420 | 89007659 | chr16 | 89007789 | 89007879 |
| chr16 | 89008488 | 89008667 | chr16 | 89047643 | 89047822 | chr16 | 89072400 | 89072879 |
| chr16 | 89086034 | 89086273 | chr16 | 89107585 | 89107824 | chr16 | 89109345 | 89109490 |
| chr16 | 89119940 | 89120419 | chr16 | 89120607 | 89120963 | chr16 | 89137919 | 89138158 |
| chr16 | 89220244 | 89220483 | chr16 | 89220580 | 89220999 | chr16 | 89254563 | 89254742 |
| chr16 | 89267260 | 89267439 | chr16 | 89267709 | 89267825 | chr16 | 89558549 | 89558807 |
| chr16 | 89883930 | 89884289 | chr16 | 89884875 | 89884989 | chr16 | 89885115 | 89885229 |
| chr16 | 89900033 | 89900272 | chr16 | 89900372 | 89900611 | chr17 | 616914 | 617026 |
| chr17 | 1082923 | 1083093 | chr17 | 1174274 | 1174362 | chr17 | 1174385 | 1174505 |
| chr17 | 1536129 | 1536221 | chr17 | 1546312 | 1546539 | chr17 | 1623600 | 1623779 |
| chr17 | 1959437 | 1959614 | chr17 | 2207848 | 2207967 | chr17 | 2208042 | 2208147 |
| chr17 | 2220974 | 2221142 | chr17 | 2249977 | 2250096 | chr17 | 3438818 | 3438938 |
| chr17 | 3439030 | 3439057 | chr17 | 3658751 | 3658930 | chr17 | 3658991 | 3659110 |
| chr17 | 4544510 | 4544809 | chr17 | 4699212 | 4699331 | chr17 | 4891237 | 4891381 |
| chr17 | 5000340 | 5000879 | chr17 | 6616543 | 6616782 | chr17 | 6616813 | 6616883 |
| chr17 | 6616885 | 6617174 | chr17 | 6679220 | 6679393 | chr17 | 6946113 | 6946153 |
| chr17 | 6946176 | 6946244 | chr17 | 7348792 | 7349070 | chr17 | 7368864 | 7369223 |
| chr17 | 7555099 | 7555338 | chr17 | 7573915 | 7574094 | chr17 | 7576923 | 7577222 |
| chr17 | 7577423 | 7577662 | chr17 | 7578078 | 7578557 | chr17 | 7906156 | 7906514 |
| chr17 | 8104071 | 8104173 | chr17 | 8230246 | 8230350 | chr17 | 8230352 | 8230785 |
| chr17 | 8774685 | 8774728 | chr17 | 8868524 | 8868668 | chr17 | 8868815 | 8869213 |
| chr17 | 8869215 | 8869483 | chr17 | 8906183 | 8906602 | chr17 | 8906895 | 8907213 |
| chr17 | 8907215 | 8907674 | chr17 | 8925983 | 8926201 | chr17 | 10100995 | 10101110 |
| chr17 | 10101132 | 10101448 | chr17 | 10102331 | 10102750 | chr17 | 11144839 | 11144852 |
| chr17 | 11144923 | 11145078 | chr17 | 13503875 | 13503945 | chr17 | 13504195 | 13504294 |
| chr17 | 13504470 | 13504769 | chr17 | 13505002 | 13505292 | chr17 | 13505316 | 13505675 |
| chr17 | 14200962 | 14201261 | chr17 | 14204138 | 14204317 | chr17 | 14204425 | 14204724 |
| chr17 | 15244988 | 15245215 | chr17 | 16282157 | 16282396 | chr17 | 16570674 | 16570897 |
| chr17 | 17062513 | 17062752 | chr17 | 17123889 | 17124068 | chr17 | 17398520 | 17398542 |
| chr17 | 18163094 | 18163415 | chr17 | 18538207 | 18538360 | chr17 | 20817897 | 20817998 |
| chr17 | 25620495 | 25620794 | chr17 | 25676885 | 25677004 | chr17 | 25680190 | 25680276 |
| chr17 | 25907676 | 25907855 | chr17 | 26263104 | 26263214 | chr17 | 26554551 | 26554753 |
| chr17 | 26961721 | 26961922 | chr17 | 27038568 | 27038686 | chr17 | 27038907 | 27038985 |
| chr17 | 27044696 | 27044744 | chr17 | 27056846 | 27056957 | chr17 | 27170072 | 27170182 |
| chr17 | 27181284 | 27181456 | chr17 | 27332378 | 27332737 | chr17 | 27716018 | 27716134 |
| chr17 | 27716198 | 27716314 | chr17 | 27940276 | 27940338 | chr17 | 27940591 | 27940995 |
| chr17 | 28562614 | 28562853 | chr17 | 29232148 | 29232267 | chr17 | 29249615 | 29249961 |
| chr17 | 29250020 | 29250034 | chr17 | 29298002 | 29298184 | chr17 | 29298186 | 29298463 |
| chr17 | 29718123 | 29718362 | chr17 | 29719096 | 29719247 | chr17 | 29719290 | 29719335 |
| chr17 | 30243689 | 30243988 | chr17 | 30250242 | 30250345 | chr17 | 31618333 | 31618409 |
| chr17 | 31618411 | 31619412 | chr17 | 31619870 | 31620109 | chr17 | 32483946 | 32484125 |
| chr17 | 32906299 | 32906556 | chr17 | 32906599 | 32906718 | chr17 | 32906888 | 32907112 |
| chr17 | 32907136 | 32907247 | chr17 | 32907554 | 32907705 | chr17 | 32907707 | 32907805 |
| chr17 | 32908044 | 32908147 | chr17 | 32908171 | 32908463 | chr17 | 32908550 | 32909029 |
| chr17 | 33672832 | 33673071 | chr17 | 33877184 | 33877303 | chr17 | 33917240 | 33917350 |
| chr17 | 35165549 | 35165788 | chr17 | 35165912 | 35166091 | chr17 | 35285455 | 35285754 |
| chr17 | 35290313 | 35290732 | chr17 | 35291242 | 35291457 | chr17 | 35291749 | 35291899 |
| chr17 | 35291921 | 35292708 | chr17 | 35293630 | 35294229 | chr17 | 35294364 | 35294481 |
| chr17 | 35294483 | 35294491 | chr17 | 35294493 | 35294603 | chr17 | 35294955 | 35295254 |
| chr17 | 35296069 | 35296368 | chr17 | 35296629 | 35296988 | chr17 | 35297527 | 35298246 |
| chr17 | 35299154 | 35299444 | chr17 | 35299601 | 35299966 | chr17 | 35300261 | 35300713 |
| chr17 | 35300813 | 35300953 | chr17 | 35303259 | 35303618 | chr17 | 36102935 | 36103289 |
| chr17 | 36103291 | 36103414 | chr17 | 36103497 | 36103676 | chr17 | 36104031 | 36104035 |
| chr17 | 36104218 | 36104551 | chr17 | 36104644 | 36104870 | chr17 | 36105141 | 36105350 |
| chr17 | 36105459 | 36105680 | chr17 | 37192168 | 37192281 | chr17 | 37321100 | 37321625 |
| chr17 | 37321788 | 37322010 | chr17 | 37366236 | 37366655 | chr17 | 37369106 | 37369285 |
| chr17 | 37380922 | 37381430 | chr17 | 37381571 | 37381727 | chr17 | 37381826 | 37381941 |
| chr17 | 37382048 | 37382347 | chr17 | 37757066 | 37757305 | chr17 | 37760406 | 37760645 |
| chr17 | 37761897 | 37762436 | chr17 | 37879697 | 37879712 | chr17 | 38179295 | 38179348 |
| chr17 | 38179492 | 38179534 | chr17 | 38347473 | 38347616 | chr17 | 38497542 | 38497721 |

TABLE 15-continued

Pan-cancer #5

| chr | start | end | chr | start | end | chr | start | end |
|---|---|---|---|---|---|---|---|---|
| chr17 | 38498009 | 38498188 | chr17 | 39682550 | 39682729 | chr17 | 40332846 | 40333268 |
| chr17 | 40400770 | 40401109 | chr17 | 40464179 | 40464418 | chr17 | 40464443 | 40464627 |
| chr17 | 40975576 | 40975754 | chr17 | 41278542 | 41278693 | chr17 | 41651776 | 41651887 |
| chr17 | 41791413 | 41791565 | chr17 | 41791591 | 41791599 | chr17 | 42030244 | 42030751 |
| chr17 | 42030780 | 42030843 | chr17 | 42061240 | 42061479 | chr17 | 42082421 | 42082660 |
| chr17 | 42092116 | 42092187 | chr17 | 42092189 | 42092295 | chr17 | 42331637 | 42331746 |
| chr17 | 42393780 | 42394113 | chr17 | 42402782 | 42402984 | chr17 | 42587336 | 42587452 |
| chr17 | 42635199 | 42635844 | chr17 | 42733619 | 42733978 | chr17 | 42787580 | 42787699 |
| chr17 | 42907489 | 42907631 | chr17 | 42907655 | 42908028 | chr17 | 43001800 | 43002029 |
| chr17 | 43044584 | 43044763 | chr17 | 43045039 | 43045208 | chr17 | 43047355 | 43047404 |
| chr17 | 43047753 | 43047834 | chr17 | 43339012 | 43339408 | chr17 | 43339546 | 43339994 |
| chr17 | 43974158 | 43974400 | chr17 | 45331345 | 45331404 | chr17 | 45810767 | 45811426 |
| chr17 | 45867239 | 45867538 | chr17 | 46124907 | 46124970 | chr17 | 46125007 | 46125146 |
| chr17 | 46619224 | 46619224 | chr17 | 46620405 | 46621184 | chr17 | 46621257 | 46621535 |
| chr17 | 46621764 | 46622003 | chr17 | 46655074 | 46655253 | chr17 | 46655351 | 46655394 |
| chr17 | 46655396 | 46655419 | chr17 | 46655451 | 46655561 | chr17 | 46655563 | 46655999 |
| chr17 | 46656058 | 46656531 | chr17 | 46659385 | 46659926 | chr17 | 46663666 | 46663825 |
| chr17 | 46663856 | 46663928 | chr17 | 46674831 | 46675072 | chr17 | 46675086 | 46675685 |
| chr17 | 46690430 | 46690705 | chr17 | 46691430 | 46691669 | chr17 | 46691719 | 46691819 |
| chr17 | 46691988 | 46692198 | chr17 | 46692344 | 46692509 | chr17 | 46710857 | 46710990 |
| chr17 | 46713934 | 46714130 | chr17 | 46714132 | 46714166 | chr17 | 46795563 | 46796374 |
| chr17 | 46796499 | 46796545 | chr17 | 46796606 | 46796638 | chr17 | 46796850 | 46797214 |
| chr17 | 46797275 | 46797662 | chr17 | 46799522 | 46800001 | chr17 | 46800516 | 46800755 |
| chr17 | 46800860 | 46801048 | chr17 | 46801109 | 46801418 | chr17 | 46802364 | 46802912 |
| chr17 | 46802994 | 46803286 | chr17 | 46804029 | 46804508 | chr17 | 46810328 | 46811047 |
| chr17 | 46811269 | 46811500 | chr17 | 46811595 | 46811628 | chr17 | 46816191 | 46816730 |
| chr17 | 46824218 | 46824276 | chr17 | 46824359 | 46824915 | chr17 | 46824917 | 46825149 |
| chr17 | 46825190 | 46825609 | chr17 | 46826897 | 46827196 | chr17 | 46827244 | 46827502 |
| chr17 | 46827626 | 46827843 | chr17 | 46829420 | 46829659 | chr17 | 46829898 | 46830136 |
| chr17 | 46830190 | 46830195 | chr17 | 46831700 | 46832326 | chr17 | 46832490 | 46832719 |
| chr17 | 47072716 | 47073029 | chr17 | 47073104 | 47073328 | chr17 | 47073389 | 47073555 |
| chr17 | 47073899 | 47074318 | chr17 | 47074459 | 47074489 | chr17 | 47074597 | 47074998 |
| chr17 | 47075083 | 47075442 | chr17 | 47075616 | 47075735 | chr17 | 47075880 | 47076155 |
| chr17 | 47574001 | 47574240 | chr17 | 47657445 | 47657684 | chr17 | 47865416 | 47865655 |
| chr17 | 47987423 | 47987722 | chr17 | 47987843 | 47988202 | chr17 | 48041057 | 48041416 |
| chr17 | 48041578 | 48041817 | chr17 | 48041965 | 48042141 | chr17 | 48042337 | 48042648 |
| chr17 | 48042751 | 48043056 | chr17 | 48048857 | 48049156 | chr17 | 48049228 | 48050607 |
| chr17 | 48070946 | 48071125 | chr17 | 48071694 | 48071705 | chr17 | 48071807 | 48071957 |
| chr17 | 48612147 | 48612386 | chr17 | 48636500 | 48637219 | chr17 | 48653054 | 48653233 |
| chr17 | 48799847 | 48799963 | chr17 | 49229486 | 49229601 | chr17 | 50235126 | 50235259 |
| chr17 | 50235625 | 50236032 | chr17 | 51900930 | 51901109 | chr17 | 53341155 | 53341557 |
| chr17 | 53342774 | 53343031 | chr17 | 53343193 | 53343933 | chr17 | 53922571 | 53922870 |
| chr17 | 54674890 | 54675137 | chr17 | 54675139 | 54675369 | chr17 | 54755873 | 54755991 |
| chr17 | 56092519 | 56092620 | chr17 | 56234305 | 56234844 | chr17 | 56326853 | 56327092 |
| chr17 | 56327197 | 56327376 | chr17 | 56833025 | 56833324 | chr17 | 56833622 | 56834001 |
| chr17 | 56834020 | 56834161 | chr17 | 56834222 | 56834461 | chr17 | 57297028 | 57297207 |
| chr17 | 58216566 | 58216837 | chr17 | 58216866 | 58217299 | chr17 | 58217357 | 58217652 |
| chr17 | 58218670 | 58219089 | chr17 | 58227281 | 58227398 | chr17 | 58498657 | 58498977 |
| chr17 | 58498979 | 58499396 | chr17 | 59474060 | 59474247 | chr17 | 59474758 | 59475177 |
| chr17 | 59475604 | 59476023 | chr17 | 59476084 | 59476203 | chr17 | 59476314 | 59476733 |
| chr17 | 59478046 | 59478705 | chr17 | 59488010 | 59488424 | chr17 | 59528775 | 59529151 |
| chr17 | 59529254 | 59529265 | chr17 | 59529844 | 59530454 | chr17 | 59531574 | 59532018 |
| chr17 | 59533741 | 59533768 | chr17 | 59533875 | 59534406 | chr17 | 59534557 | 59534580 |
| chr17 | 59534677 | 59534856 | chr17 | 59535059 | 59535298 | chr17 | 59539150 | 59539689 |
| chr17 | 61777984 | 61778074 | chr17 | 61778235 | 61778249 | chr17 | 61817858 | 61818036 |
| chr17 | 61926149 | 61926325 | chr17 | 61926508 | 61926625 | chr17 | 62777244 | 62777543 |
| chr17 | 62777650 | 62777889 | chr17 | 64672276 | 64672635 | chr17 | 66596379 | 66596618 |
| chr17 | 66596884 | 66597123 | chr17 | 67410389 | 67410501 | chr17 | 68164667 | 68164906 |
| chr17 | 70026473 | 70026755 | chr17 | 70112818 | 70113567 | chr17 | 70113678 | 70114019 |
| chr17 | 70114153 | 70114617 | chr17 | 70215595 | 70216307 | chr17 | 70216393 | 70216674 |
| chr17 | 71641465 | 71641761 | chr17 | 71948352 | 71948951 | chr17 | 72270202 | 72270501 |
| chr17 | 72321844 | 72322074 | chr17 | 72322275 | 72322558 | chr17 | 72322612 | 72322694 |
| chr17 | 72353148 | 72353260 | chr17 | 72353417 | 72353531 | chr17 | 72427777 | 72427963 |
| chr17 | 72428244 | 72428483 | chr17 | 72667242 | 72667482 | chr17 | 72848926 | 72849165 |
| chr17 | 72856964 | 72857443 | chr17 | 72920705 | 72921124 | chr17 | 73031547 | 73031619 |
| chr17 | 73073610 | 73073684 | chr17 | 73545910 | 73546120 | chr17 | 73584938 | 73584972 |
| chr17 | 73585919 | 73586517 | chr17 | 73608232 | 73608411 | chr17 | 73636062 | 73636421 |
| chr17 | 74028261 | 74028461 | chr17 | 74047755 | 74047994 | chr17 | 74070386 | 74070480 |
| chr17 | 74071344 | 74071583 | chr17 | 74071590 | 74071825 | chr17 | 74072999 | 74073139 |
| chr17 | 74073172 | 74073531 | chr17 | 74390289 | 74390468 | chr17 | 74533808 | 74534363 |
| chr17 | 74534388 | 74534407 | chr17 | 74581083 | 74581322 | chr17 | 74864974 | 74865068 |
| chr17 | 74865070 | 74865273 | chr17 | 74865612 | 74866331 | chr17 | 75207765 | 75207944 |
| chr17 | 75368658 | 75368902 | chr17 | 75368904 | 75369091 | chr17 | 75369093 | 75369317 |
| chr17 | 75369351 | 75369458 | chr17 | 75369493 | 75369950 | chr17 | 75370186 | 75370413 |
| chr17 | 75370522 | 75370701 | chr17 | 75385122 | 75385301 | chr17 | 75523058 | 75523354 |
| chr17 | 75524556 | 75525004 | chr17 | 75525006 | 75525275 | chr17 | 75733902 | 75734108 |

TABLE 15-continued

Pan-cancer #5

| chr | start | end | chr | start | end | chr | start | end |
|---|---|---|---|---|---|---|---|---|
| chr17 | 75797121 | 75797265 | chr17 | 76125122 | 76125301 | chr17 | 76137862 | 76138281 |
| chr17 | 76138525 | 76138710 | chr17 | 76227774 | 76228162 | chr17 | 76228214 | 76228433 |
| chr17 | 76404662 | 76404757 | chr17 | 76921756 | 76921806 | chr17 | 76921860 | 76921934 |
| chr17 | 76974354 | 76974582 | chr17 | 77084488 | 77084667 | chr17 | 77104978 | 77105277 |
| chr17 | 77145037 | 77145336 | chr17 | 77179017 | 77179064 | chr17 | 77179082 | 77179330 |
| chr17 | 77179618 | 77179709 | chr17 | 77179711 | 77179777 | chr17 | 77179800 | 77179891 |
| chr17 | 77776733 | 77776996 | chr17 | 77777053 | 77777152 | chr17 | 77777504 | 77777649 |
| chr17 | 77777651 | 77777904 | chr17 | 77777944 | 77778043 | chr17 | 77778852 | 77779136 |
| chr17 | 77789474 | 77789528 | chr17 | 77825605 | 77825858 | chr17 | 77899590 | 77899634 |
| chr17 | 78122175 | 78122294 | chr17 | 78447053 | 78447213 | chr17 | 78451842 | 78451954 |
| chr17 | 78452109 | 78452141 | chr17 | 78452199 | 78452438 | chr17 | 78452578 | 78452937 |
| chr17 | 78518204 | 78518295 | chr17 | 78599493 | 78599732 | chr17 | 78667897 | 78668256 |
| chr17 | 78874418 | 78874650 | chr17 | 79094095 | 79094334 | chr17 | 79099696 | 79099875 |
| chr17 | 79615087 | 79615136 | chr17 | 79615435 | 79615446 | chr17 | 79626656 | 79626797 |
| chr17 | 79769354 | 79769773 | chr17 | 80254258 | 80254371 | chr17 | 80289153 | 80289392 |
| chr17 | 80329628 | 80330001 | chr17 | 80330165 | 80330167 | chr17 | 80394659 | 80394678 |
| chr17 | 80479366 | 80479525 | chr17 | 80535286 | 80535469 | chr17 | 80654909 | 80655088 |
| chr17 | 80693343 | 80693582 | chr17 | 80797600 | 80798439 | chr17 | 80832209 | 80832508 |
| chr17 | 80832635 | 80832874 | chr17 | 81008543 | 81008902 | chr17 | 81033413 | 81033592 |
| chr17 | 81048919 | 81049098 | chr17 | 81049943 | 81050146 | chr18 | 499454 | 499575 |
| chr18 | 499947 | 500842 | chr18 | 904376 | 904735 | chr18 | 904926 | 905105 |
| chr18 | 905359 | 905616 | chr18 | 905693 | 905718 | chr18 | 906770 | 907009 |
| chr18 | 907384 | 907683 | chr18 | 907826 | 908065 | chr18 | 908373 | 908607 |
| chr18 | 909046 | 909085 | chr18 | 909184 | 909225 | chr18 | 909388 | 909687 |
| chr18 | 2755855 | 2755974 | chr18 | 2906167 | 2906406 | chr18 | 3215032 | 3215271 |
| chr18 | 3498980 | 3499447 | chr18 | 4453885 | 4454244 | chr18 | 4454979 | 4455031 |
| chr18 | 4455259 | 4455272 | chr18 | 5133126 | 5133405 | chr18 | 5196576 | 5197038 |
| chr18 | 5197126 | 5197272 | chr18 | 5197330 | 5197425 | chr18 | 5543132 | 5543158 |
| chr18 | 5543431 | 5543431 | chr18 | 5543900 | 5543957 | chr18 | 5628072 | 5628611 |
| chr18 | 5629700 | 5629826 | chr18 | 5630218 | 5630457 | chr18 | 5891337 | 5891418 |
| chr18 | 5894935 | 5894946 | chr18 | 5895018 | 5895294 | chr18 | 5895881 | 5896180 |
| chr18 | 6729881 | 6730093 | chr18 | 7116858 | 7116883 | chr18 | 7117060 | 7117073 |
| chr18 | 7117616 | 7117885 | chr18 | 7567708 | 7568367 | chr18 | 8608649 | 8608838 |
| chr18 | 8608902 | 8609062 | chr18 | 8612178 | 8612357 | chr18 | 9771621 | 9771850 |
| chr18 | 9912693 | 9912872 | chr18 | 10589013 | 10589432 | chr18 | 11148888 | 11149094 |
| chr18 | 11149116 | 11149127 | chr18 | 11149486 | 11149760 | chr18 | 11149780 | 11149965 |
| chr18 | 11401557 | 11401846 | chr18 | 11751538 | 11751632 | chr18 | 11752128 | 11752473 |
| chr18 | 11752641 | 11752805 | chr18 | 11942634 | 11942746 | chr18 | 12254133 | 12254147 |
| chr18 | 12254305 | 12254672 | chr18 | 12307603 | 12307829 | chr18 | 12376133 | 12376206 |
| chr18 | 13824125 | 13824184 | chr18 | 13826316 | 13826615 | chr18 | 13868620 | 13868920 |
| chr18 | 13868947 | 13869039 | chr18 | 15198162 | 15198269 | chr18 | 18822294 | 18823060 |
| chr18 | 18823101 | 18823373 | chr18 | 19750286 | 19750447 | chr18 | 20911467 | 20911646 |
| chr18 | 21269344 | 21269490 | chr18 | 21269581 | 21269763 | chr18 | 22928981 | 22929096 |
| chr18 | 22929187 | 22929719 | chr18 | 22929927 | 22930283 | chr18 | 22930285 | 22930660 |
| chr18 | 22930715 | 22931254 | chr18 | 23686388 | 23686507 | chr18 | 24127650 | 24128129 |
| chr18 | 24130729 | 24130947 | chr18 | 24131099 | 24131267 | chr18 | 24764851 | 24765188 |
| chr18 | 24765231 | 24765252 | chr18 | 25755556 | 25755744 | chr18 | 25755936 | 25756115 |
| chr18 | 25756542 | 25756822 | chr18 | 25757151 | 25757438 | chr18 | 25757440 | 25757530 |
| chr18 | 25757687 | 25757926 | chr18 | 25758129 | 25758233 | chr18 | 28620819 | 28620956 |
| chr18 | 28621034 | 28621178 | chr18 | 28621242 | 28621274 | chr18 | 28621383 | 28621481 |
| chr18 | 28621545 | 28622024 | chr18 | 28622335 | 28622574 | chr18 | 30349642 | 30349872 |
| chr18 | 31020419 | 31020511 | chr18 | 31158007 | 31158049 | chr18 | 31738953 | 31739552 |
| chr18 | 31802031 | 31802270 | chr18 | 31802864 | 31803043 | chr18 | 31803336 | 31803575 |
| chr18 | 31902690 | 31902944 | chr18 | 32073807 | 32073831 | chr18 | 32073908 | 32074166 |
| chr18 | 32557847 | 32557882 | chr18 | 32557884 | 32557968 | chr18 | 32957702 | 32957813 |
| chr18 | 33078274 | 33078393 | chr18 | 33078634 | 33078753 | chr18 | 33877784 | 33877839 |
| chr18 | 34833519 | 34833554 | chr18 | 35064986 | 35065146 | chr18 | 35065517 | 35065525 |
| chr18 | 35104935 | 35104984 | chr18 | 35144766 | 35144937 | chr18 | 35144969 | 35145545 |
| chr18 | 35146023 | 35146037 | chr18 | 35146062 | 35146322 | chr18 | 35147409 | 35147648 |
| chr18 | 43914156 | 43914226 | chr18 | 43914228 | 43914365 | chr18 | 44259911 | 44260067 |
| chr18 | 44335999 | 44336450 | chr18 | 44337013 | 44337044 | chr18 | 44337445 | 44337618 |
| chr18 | 44337650 | 44337842 | chr18 | 44338099 | 44338164 | chr18 | 44772980 | 44773117 |
| chr18 | 44773574 | 44773967 | chr18 | 44774202 | 44774233 | chr18 | 44774319 | 44774804 |
| chr18 | 44775309 | 44775647 | chr18 | 44776881 | 44777180 | chr18 | 44777227 | 44777406 |
| chr18 | 44777512 | 44777792 | chr18 | 44777949 | 44778411 | chr18 | 44780903 | 44781142 |
| chr18 | 44787695 | 44787934 | chr18 | 44788177 | 44788356 | chr18 | 44789375 | 44789614 |
| chr18 | 44789786 | 44790025 | chr18 | 45057993 | 45058293 | chr18 | 45058308 | 45058335 |
| chr18 | 46142587 | 46142715 | chr18 | 49867202 | 49867483 | chr18 | 52988906 | 52989155 |
| chr18 | 52989157 | 52989316 | chr18 | 52989723 | 52989962 | chr18 | 53257052 | 53257291 |
| chr18 | 53446884 | 53447475 | chr18 | 53447799 | 53447903 | chr18 | 53989718 | 53989828 |
| chr18 | 53989876 | 53989957 | chr18 | 54788984 | 54789343 | chr18 | 55019610 | 55019776 |
| chr18 | 55020572 | 55020699 | chr18 | 55020805 | 55020811 | chr18 | 55020981 | 55021340 |
| chr18 | 55103307 | 55103414 | chr18 | 55103762 | 55103824 | chr18 | 55104744 | 55105244 |
| chr18 | 55105630 | 55105929 | chr18 | 55114441 | 55114740 | chr18 | 55850767 | 55851066 |
| chr18 | 56483824 | 56483938 | chr18 | 56815757 | 56815876 | chr18 | 56886981 | 56887469 |
| chr18 | 56887503 | 56887517 | chr18 | 56888470 | 56888656 | chr18 | 56888687 | 56888709 |

TABLE 15-continued

Pan-cancer #5

| chr | start | end | chr | start | end | chr | start | end |
|---|---|---|---|---|---|---|---|---|
| chr18 | 56931460 | 56931682 | chr18 | 56931888 | 56932187 | chr18 | 56932256 | 56932375 |
| chr18 | 56934926 | 56935405 | chr18 | 56935920 | 56936159 | chr18 | 56939025 | 56939264 |
| chr18 | 56939324 | 56939652 | chr18 | 56939764 | 56940171 | chr18 | 56940566 | 56940823 |
| chr18 | 56940863 | 56941245 | chr18 | 56941558 | 56941882 | chr18 | 57363606 | 57363845 |
| chr18 | 57364449 | 57364484 | chr18 | 57364556 | 57364795 | chr18 | 59000886 | 59001125 |
| chr18 | 59001222 | 59001344 | chr18 | 59001498 | 59001821 | chr18 | 60263452 | 60263544 |
| chr18 | 60263661 | 60263991 | chr18 | 60985417 | 60985533 | chr18 | 60985593 | 60985732 |
| chr18 | 60985734 | 60985825 | chr18 | 67067464 | 67067893 | chr18 | 67067895 | 67067971 |
| chr18 | 67067996 | 67068003 | chr18 | 67068059 | 67068114 | chr18 | 67068614 | 67068913 |
| chr18 | 67069142 | 67069321 | chr18 | 70209102 | 70209297 | chr18 | 70209348 | 70209386 |
| chr18 | 70209494 | 70209527 | chr18 | 70210483 | 70210583 | chr18 | 70211527 | 70211766 |
| chr18 | 70534207 | 70534316 | chr18 | 70534428 | 70534686 | chr18 | 70535299 | 70535555 |
| chr18 | 70535576 | 70535658 | chr18 | 70535918 | 70536084 | chr18 | 70536188 | 70536697 |
| chr18 | 70536733 | 70536972 | chr18 | 70537230 | 70537293 | chr18 | 73167500 | 73167919 |
| chr18 | 73627925 | 73628153 | chr18 | 74501045 | 74501267 | chr18 | 74755430 | 74755577 |
| chr18 | 74961264 | 74961737 | chr18 | 74961739 | 74961956 | chr18 | 74962019 | 74962171 |
| chr18 | 74962210 | 74962247 | chr18 | 74962693 | 74962751 | chr18 | 74962896 | 74963546 |
| chr18 | 75339137 | 75339436 | chr18 | 75362839 | 75363078 | chr18 | 75551197 | 75551376 |
| chr18 | 75612137 | 75612376 | chr18 | 75999330 | 75999509 | chr18 | 76239460 | 76239699 |
| chr18 | 76501405 | 76501584 | chr18 | 76653557 | 76653736 | chr18 | 76686175 | 76686354 |
| chr18 | 77143365 | 77143451 | chr18 | 77167752 | 77167929 | chr18 | 77181263 | 77181502 |
| chr18 | 77194838 | 77195077 | chr18 | 77205436 | 77205735 | chr18 | 77285814 | 77286113 |
| chr18 | 77309459 | 77309638 | chr18 | 77312784 | 77313017 | chr18 | 77329633 | 77330101 |
| chr18 | 77371350 | 77371589 | chr18 | 77543156 | 77543335 | chr18 | 77543673 | 77543912 |
| chr18 | 77547985 | 77548048 | chr18 | 77548352 | 77548700 | chr18 | 77550108 | 77550467 |
| chr18 | 77557981 | 77558397 | chr18 | 77558417 | 77558460 | chr18 | 77558732 | 77559031 |
| chr18 | 77576853 | 77577139 | chr18 | 77636517 | 77636696 | chr18 | 78005004 | 78005142 |
| chr19 | 403435 | 403888 | chr19 | 407106 | 407405 | chr19 | 462106 | 462235 |
| chr19 | 468683 | 468862 | chr19 | 485071 | 485490 | chr19 | 549287 | 549526 |
| chr19 | 555509 | 555625 | chr19 | 591272 | 591511 | chr19 | 592492 | 592654 |
| chr19 | 593197 | 593325 | chr19 | 599125 | 599424 | chr19 | 752060 | 752359 |
| chr19 | 869247 | 869363 | chr19 | 883529 | 883888 | chr19 | 883941 | 884240 |
| chr19 | 891441 | 891616 | chr19 | 955668 | 956327 | chr19 | 1003226 | 1003465 |
| chr19 | 1003583 | 1003822 | chr19 | 1004819 | 1005528 | chr19 | 1030082 | 1030309 |
| chr19 | 1047796 | 1047915 | chr19 | 1083392 | 1083526 | chr19 | 1156450 | 1156629 |
| chr19 | 1170089 | 1170328 | chr19 | 1171003 | 1171422 | chr19 | 1220349 | 1220696 |
| chr19 | 1236397 | 1236631 | chr19 | 1274683 | 1274922 | chr19 | 1308066 | 1308184 |
| chr19 | 1325714 | 1325989 | chr19 | 1401655 | 1401894 | chr19 | 1450236 | 1450475 |
| chr19 | 1496313 | 1496552 | chr19 | 1496555 | 1496672 | chr19 | 1524443 | 1524528 |
| chr19 | 1525530 | 1526053 | chr19 | 1527132 | 1527307 | chr19 | 1754094 | 1754194 |
| chr19 | 1754225 | 1754333 | chr19 | 1754653 | 1754892 | chr19 | 1757337 | 1757696 |
| chr19 | 1762376 | 1762506 | chr19 | 1762628 | 1762675 | chr19 | 1764197 | 1764374 |
| chr19 | 1775037 | 1775338 | chr19 | 1776276 | 1776635 | chr19 | 1807893 | 1808492 |
| chr19 | 2251075 | 2251235 | chr19 | 2251611 | 2251794 | chr19 | 2252589 | 2252752 |
| chr19 | 2252901 | 2253736 | chr19 | 2253781 | 2253860 | chr19 | 2274576 | 2274692 |
| chr19 | 2290165 | 2290272 | chr19 | 2290631 | 2290868 | chr19 | 2302693 | 2303052 |
| chr19 | 2331339 | 2331518 | chr19 | 2513149 | 2513388 | chr19 | 2683817 | 2684046 |
| chr19 | 3041486 | 3041522 | chr19 | 3219555 | 3219659 | chr19 | 3296523 | 3296762 |
| chr19 | 3361055 | 3361374 | chr19 | 3361376 | 3361474 | chr19 | 3562249 | 3562583 |
| chr19 | 3578062 | 3578301 | chr19 | 3778053 | 3778472 | chr19 | 3779177 | 3779536 |
| chr19 | 3785566 | 3785836 | chr19 | 3785865 | 3786221 | chr19 | 3820952 | 3821311 |
| chr19 | 3822008 | 3822110 | chr19 | 3822135 | 3822307 | chr19 | 3855322 | 3855681 |
| chr19 | 4054334 | 4054463 | chr19 | 4054540 | 4054573 | chr19 | 4311173 | 4311350 |
| chr19 | 4548016 | 4548459 | chr19 | 4550169 | 4550408 | chr19 | 4555813 | 4556214 |
| chr19 | 4557018 | 4557317 | chr19 | 4670678 | 4670857 | chr19 | 5292709 | 5292948 |
| chr19 | 5338820 | 5338851 | chr19 | 5338901 | 5339239 | chr19 | 5759670 | 5759789 |
| chr19 | 5826175 | 5826284 | chr19 | 5910275 | 5910429 | chr19 | 5914687 | 5914866 |
| chr19 | 5914907 | 5915146 | chr19 | 6590244 | 6590582 | chr19 | 7794919 | 7795338 |
| chr19 | 7852944 | 7853243 | chr19 | 7853262 | 7853471 | chr19 | 7853544 | 7853561 |
| chr19 | 8115149 | 8115376 | chr19 | 8576838 | 8577077 | chr19 | 9473939 | 9474140 |
| chr19 | 9517511 | 9517791 | chr19 | 9608817 | 9609116 | chr19 | 9609229 | 9609528 |
| chr19 | 9903828 | 9904054 | chr19 | 9937370 | 9937489 | chr19 | 10231221 | 10231331 |
| chr19 | 10361965 | 10362076 | chr19 | 10398128 | 10398367 | chr19 | 10405892 | 10406160 |
| chr19 | 10406279 | 10406431 | chr19 | 10406798 | 10407030 | chr19 | 10407045 | 10407211 |
| chr19 | 10527085 | 10527282 | chr19 | 10531317 | 10531616 | chr19 | 10531890 | 10532069 |
| chr19 | 10624740 | 10624853 | chr19 | 10624966 | 10625558 | chr19 | 10823581 | 10823708 |
| chr19 | 11590929 | 11591288 | chr19 | 11592611 | 11592850 | chr19 | 11592942 | 11593241 |
| chr19 | 11689363 | 11689662 | chr19 | 11959816 | 11960175 | chr19 | 12163452 | 12163770 |
| chr19 | 12163819 | 12163998 | chr19 | 12175356 | 12175595 | chr19 | 12175731 | 12176090 |
| chr19 | 12202937 | 12203349 | chr19 | 12203351 | 12203638 | chr19 | 12266924 | 12267308 |
| chr19 | 12267310 | 12267763 | chr19 | 12305754 | 12306194 | chr19 | 12306230 | 12306303 |
| chr19 | 12306305 | 12306351 | chr19 | 12476405 | 12476465 | chr19 | 12476501 | 12476644 |
| chr19 | 12606297 | 12606556 | chr19 | 12750903 | 12751142 | chr19 | 12863329 | 12863616 |
| chr19 | 12951921 | 12952129 | chr19 | 12952131 | 12952220 | chr19 | 12996076 | 12996375 |
| chr19 | 13616617 | 13616957 | chr19 | 13617159 | 13617336 | chr19 | 13618186 | 13618485 |
| chr19 | 13965933 | 13966022 | chr19 | 14181217 | 14181682 | chr19 | 14584168 | 14584413 |

TABLE 15-continued

Pan-cancer #5

| chr | start | end | chr | start | end | chr | start | end |
|---|---|---|---|---|---|---|---|---|
| chr19 | 14584537 | 14584868 | chr19 | 15090097 | 15090576 | chr19 | 15121611 | 15121970 |
| chr19 | 15122030 | 15122314 | chr19 | 15288346 | 15288945 | chr19 | 15292293 | 15292592 |
| chr19 | 15342635 | 15343411 | chr19 | 15344007 | 15344131 | chr19 | 15344418 | 15344426 |
| chr19 | 17006991 | 17007389 | chr19 | 17007447 | 17007764 | chr19 | 17008422 | 17008519 |
| chr19 | 17008586 | 17008699 | chr19 | 17008821 | 17008884 | chr19 | 17392545 | 17392964 |
| chr19 | 17717212 | 17717391 | chr19 | 17759145 | 17759504 | chr19 | 17791108 | 17791287 |
| chr19 | 17958396 | 17958935 | chr19 | 17983447 | 17983666 | chr19 | 17983840 | 17983910 |
| chr19 | 18041167 | 18041286 | chr19 | 18103637 | 18103816 | chr19 | 18104390 | 18104493 |
| chr19 | 18271871 | 18271999 | chr19 | 18330935 | 18331234 | chr19 | 18343355 | 18343654 |
| chr19 | 18343880 | 18344062 | chr19 | 18383252 | 18383431 | chr19 | 18714465 | 18714581 |
| chr19 | 18811473 | 18811771 | chr19 | 18899333 | 18899718 | chr19 | 18901753 | 18902172 |
| chr19 | 18980680 | 18980718 | chr19 | 18980912 | 18980979 | chr19 | 18989722 | 18990360 |
| chr19 | 18994808 | 18995227 | chr19 | 19334769 | 19334993 | chr19 | 19645776 | 19646015 |
| chr19 | 19651991 | 19652164 | chr19 | 20011908 | 20011992 | chr19 | 20012053 | 20012172 |
| chr19 | 20188746 | 20188865 | chr19 | 20189411 | 20189530 | chr19 | 21646333 | 21646512 |
| chr19 | 21769223 | 21769375 | chr19 | 22018429 | 22018724 | chr19 | 22034402 | 22034418 |
| chr19 | 22034420 | 22034422 | chr19 | 22034447 | 22034896 | chr19 | 22610542 | 22610701 |
| chr19 | 22715053 | 22715532 | chr19 | 23254115 | 23254294 | chr19 | 23257780 | 23258008 |
| chr19 | 23258306 | 23258559 | chr19 | 23258680 | 23258799 | chr19 | 23299705 | 23299784 |
| chr19 | 23433104 | 23433223 | chr19 | 23598358 | 23598420 | chr19 | 24154518 | 24154697 |
| chr19 | 24216940 | 24217119 | chr19 | 29284377 | 29284576 | chr19 | 29505081 | 29505258 |
| chr19 | 30015844 | 30015963 | chr19 | 30016025 | 30016803 | chr19 | 30016832 | 30016929 |
| chr19 | 30017452 | 30017510 | chr19 | 30017578 | 30017722 | chr19 | 30017766 | 30018691 |
| chr19 | 30019043 | 30019529 | chr19 | 30019531 | 30019611 | chr19 | 30019661 | 30019931 |
| chr19 | 30020014 | 30020553 | chr19 | 30021253 | 30021279 | chr19 | 30215468 | 30215572 |
| chr19 | 30252214 | 30252330 | chr19 | 30555254 | 30555473 | chr19 | 30562687 | 30562831 |
| chr19 | 30637413 | 30637633 | chr19 | 30713384 | 30713593 | chr19 | 30713686 | 30713803 |
| chr19 | 30713829 | 30714128 | chr19 | 30714425 | 30714508 | chr19 | 30715315 | 30715854 |
| chr19 | 30716236 | 30716655 | chr19 | 30716732 | 30716770 | chr19 | 30716953 | 30718231 |
| chr19 | 30718761 | 30718934 | chr19 | 30719369 | 30720134 | chr19 | 30865626 | 30866025 |
| chr19 | 30866453 | 30866525 | chr19 | 31804650 | 31804829 | chr19 | 31839838 | 31839928 |
| chr19 | 31839942 | 31839969 | chr19 | 31841834 | 31842072 | chr19 | 31842116 | 31842481 |
| chr19 | 32364265 | 32364504 | chr19 | 32516309 | 32516495 | chr19 | 32715588 | 32715827 |
| chr19 | 32898350 | 32898589 | chr19 | 33167035 | 33167488 | chr19 | 33167497 | 33167514 |
| chr19 | 33467984 | 33468157 | chr19 | 33685493 | 33685683 | chr19 | 33792412 | 33792612 |
| chr19 | 33794599 | 33794745 | chr19 | 33794780 | 33794838 | chr19 | 34112185 | 34112287 |
| chr19 | 34112327 | 34112424 | chr19 | 34112450 | 34112730 | chr19 | 34113259 | 34113303 |
| chr19 | 34113367 | 34113398 | chr19 | 34113400 | 34113678 | chr19 | 34113911 | 34114050 |
| chr19 | 34972523 | 34972569 | chr19 | 34973243 | 34973330 | chr19 | 34973558 | 34973644 |
| chr19 | 34973646 | 34973797 | chr19 | 35263983 | 35264092 | chr19 | 35395923 | 35395949 |
| chr19 | 35396251 | 35396462 | chr19 | 35616250 | 35616489 | chr19 | 35781298 | 35781537 |
| chr19 | 35797822 | 35798061 | chr19 | 36048504 | 36048863 | chr19 | 36049246 | 36049368 |
| chr19 | 36049397 | 36049497 | chr19 | 36222334 | 36222567 | chr19 | 36249933 | 36250232 |
| chr19 | 36334884 | 36335243 | chr19 | 36347791 | 36348147 | chr19 | 36450030 | 36450296 |
| chr19 | 36523258 | 36523557 | chr19 | 36735953 | 36736132 | chr19 | 36736226 | 36736296 |
| chr19 | 36736315 | 36736585 | chr19 | 36822249 | 36822467 | chr19 | 36822558 | 36822968 |
| chr19 | 36909074 | 36909349 | chr19 | 36909624 | 36910028 | chr19 | 36912257 | 36912350 |
| chr19 | 36912481 | 36912496 | chr19 | 37095591 | 37095813 | chr19 | 37096488 | 37096660 |
| chr19 | 37263439 | 37263678 | chr19 | 37264143 | 37264487 | chr19 | 37288237 | 37288425 |
| chr19 | 37288607 | 37288705 | chr19 | 37288707 | 37288869 | chr19 | 37341683 | 37342042 |
| chr19 | 37407046 | 37407152 | chr19 | 37407154 | 37407374 | chr19 | 37407376 | 37407525 |
| chr19 | 37463953 | 37464568 | chr19 | 37464667 | 37464792 | chr19 | 37569394 | 37569573 |
| chr19 | 37702087 | 37702265 | chr19 | 37959762 | 37959801 | chr19 | 37959874 | 37960061 |
| chr19 | 37997337 | 37997991 | chr19 | 37998206 | 37998206 | chr19 | 38042357 | 38042769 |
| chr19 | 38085160 | 38085759 | chr19 | 38085958 | 38086110 | chr19 | 38145976 | 38146335 |
| chr19 | 38146364 | 38146663 | chr19 | 38182793 | 38182960 | chr19 | 38183112 | 38183259 |
| chr19 | 38183261 | 38183262 | chr19 | 38183264 | 38183392 | chr19 | 38308031 | 38308337 |
| chr19 | 38308395 | 38308543 | chr19 | 38480952 | 38481190 | chr19 | 38747072 | 38747078 |
| chr19 | 38747107 | 38747201 | chr19 | 38747203 | 38747448 | chr19 | 38755189 | 38755422 |
| chr19 | 38782485 | 38782664 | chr19 | 38789223 | 38789373 | chr19 | 38873861 | 38874040 |
| chr19 | 38905446 | 38905805 | chr19 | 38974158 | 38974337 | chr19 | 39135435 | 39135554 |
| chr19 | 39687575 | 39687647 | chr19 | 39687756 | 39687934 | chr19 | 39754787 | 39755233 |
| chr19 | 39755265 | 39755446 | chr19 | 39816862 | 39817161 | chr19 | 39993392 | 39993469 |
| chr19 | 39993712 | 39993751 | chr19 | 39997602 | 39997733 | chr19 | 39997749 | 39997901 |
| chr19 | 40006093 | 40006161 | chr19 | 40006187 | 40006392 | chr19 | 40006499 | 40006728 |
| chr19 | 40723923 | 40724342 | chr19 | 40829768 | 40830123 | chr19 | 40902350 | 40902779 |
| chr19 | 40951087 | 40951197 | chr19 | 40951602 | 40951841 | chr19 | 41018456 | 41019063 |
| chr19 | 41019076 | 41019131 | chr19 | 41025462 | 41025761 | chr19 | 41059832 | 41060385 |
| chr19 | 41073513 | 41073752 | chr19 | 41119097 | 41119277 | chr19 | 41119371 | 41119409 |
| chr19 | 41119670 | 41119735 | chr19 | 41354576 | 41354814 | chr19 | 41641740 | 41641979 |
| chr19 | 42028407 | 42028646 | chr19 | 42408226 | 42408405 | chr19 | 42827810 | 42827820 |
| chr19 | 42827982 | 42828085 | chr19 | 42828317 | 42828349 | chr19 | 42856486 | 42856558 |
| chr19 | 44203735 | 44203962 | chr19 | 44405819 | 44405924 | chr19 | 44405926 | 44406178 |
| chr19 | 44599691 | 44599803 | chr19 | 44905425 | 44905604 | chr19 | 44952193 | 44952618 |
| chr19 | 44952620 | 44952665 | chr19 | 44952667 | 44952909 | chr19 | 45003142 | 45003417 |
| chr19 | 45300052 | 45300291 | chr19 | 45570307 | 45570546 | chr19 | 45574391 | 45574570 |

TABLE 15-continued

Pan-cancer #5

| chr | start | end | chr | start | end | chr | start | end |
|---|---|---|---|---|---|---|---|---|
| chr19 | 45574682 | 45574782 | chr19 | 45574837 | 45574981 | chr19 | 45655309 | 45655349 |
| chr19 | 45655400 | 45655557 | chr19 | 45655648 | 45656448 | chr19 | 45656589 | 45656743 |
| chr19 | 45656791 | 45657008 | chr19 | 45657129 | 45657368 | chr19 | 45810006 | 45810345 |
| chr19 | 45835239 | 45835353 | chr19 | 45888843 | 45889225 | chr19 | 45889316 | 45889484 |
| chr19 | 45997437 | 45997676 | chr19 | 46001945 | 46002353 | chr19 | 46234853 | 46234965 |
| chr19 | 46379822 | 46379858 | chr19 | 46379894 | 46380241 | chr19 | 46404448 | 46404682 |
| chr19 | 46916631 | 46916988 | chr19 | 46917061 | 46917170 | chr19 | 46930046 | 46930278 |
| chr19 | 46974477 | 46974567 | chr19 | 46974569 | 46974609 | chr19 | 46992643 | 46992942 |
| chr19 | 46993067 | 46993261 | chr19 | 46993282 | 46993486 | chr19 | 46996509 | 46996515 |
| chr19 | 46996578 | 46996748 | chr19 | 46996775 | 46996839 | chr19 | 47152978 | 47152991 |
| chr19 | 47200270 | 47200629 | chr19 | 47910559 | 47910584 | chr19 | 47933223 | 47933822 |
| chr19 | 48003512 | 48003747 | chr19 | 48076568 | 48076747 | chr19 | 48137090 | 48137187 |
| chr19 | 48137247 | 48137389 | chr19 | 48151189 | 48151421 | chr19 | 48614769 | 48614851 |
| chr19 | 48771496 | 48771636 | chr19 | 48800507 | 48800866 | chr19 | 48857809 | 48857917 |
| chr19 | 48902834 | 48902953 | chr19 | 48918040 | 48918339 | chr19 | 49119155 | 49119334 |
| chr19 | 49127285 | 49127764 | chr19 | 49180431 | 49180610 | chr19 | 49399126 | 49399414 |
| chr19 | 49575386 | 49575475 | chr19 | 49646062 | 49646116 | chr19 | 49646246 | 49646294 |
| chr19 | 49890810 | 49890908 | chr19 | 49935656 | 49936255 | chr19 | 49936828 | 49936969 |
| chr19 | 50028531 | 50028614 | chr19 | 50049635 | 50049746 | chr19 | 50215991 | 50216147 |
| chr19 | 50316147 | 50316566 | chr19 | 50353305 | 50353664 | chr19 | 50553917 | 50554516 |
| chr19 | 50816339 | 50816573 | chr19 | 50833750 | 50833966 | chr19 | 50938470 | 50938769 |
| chr19 | 51161151 | 51161330 | chr19 | 51162123 | 51162254 | chr19 | 51162428 | 51162602 |
| chr19 | 51171130 | 51171276 | chr19 | 51227633 | 51227872 | chr19 | 51227975 | 51228154 |
| chr19 | 51228229 | 51228269 | chr19 | 51228369 | 51228588 | chr19 | 51304487 | 51304666 |
| chr19 | 51520349 | 51520528 | chr19 | 51830748 | 51831003 | chr19 | 51831121 | 51831227 |
| chr19 | 51831286 | 51831465 | chr19 | 52097592 | 52097831 | chr19 | 52207162 | 52207461 |
| chr19 | 52222438 | 52222924 | chr19 | 52223143 | 52223192 | chr19 | 52552089 | 52552120 |
| chr19 | 52552234 | 52552248 | chr19 | 52839494 | 52839634 | chr19 | 52839700 | 52839718 |
| chr19 | 52839742 | 52839924 | chr19 | 52839926 | 52840033 | chr19 | 52872943 | 52873106 |
| chr19 | 52873108 | 52873534 | chr19 | 52956708 | 52956947 | chr19 | 53028835 | 53028952 |
| chr19 | 53031202 | 53031290 | chr19 | 53073476 | 53073773 | chr19 | 53073820 | 53073865 |
| chr19 | 53073867 | 53074075 | chr19 | 53141533 | 53141619 | chr19 | 53141648 | 53141832 |
| chr19 | 53193757 | 53193996 | chr19 | 53194190 | 53194366 | chr19 | 53496630 | 53496787 |
| chr19 | 53496814 | 53496928 | chr19 | 53561582 | 53561821 | chr19 | 53635873 | 53636108 |
| chr19 | 53636110 | 53636168 | chr19 | 53661566 | 53661865 | chr19 | 53662195 | 53662722 |
| chr19 | 53696318 | 53696649 | chr19 | 53696651 | 53696677 | chr19 | 53700514 | 53700693 |
| chr19 | 53757802 | 53758341 | chr19 | 53811774 | 53811986 | chr19 | 53836837 | 53836912 |
| chr19 | 53970464 | 53970636 | chr19 | 53970884 | 53971040 | chr19 | 53971110 | 53971243 |
| chr19 | 54023803 | 54023999 | chr19 | 54024001 | 54024282 | chr19 | 54024434 | 54024553 |
| chr19 | 54024619 | 54024973 | chr19 | 54411032 | 54411267 | chr19 | 54411482 | 54411661 |
| chr19 | 54412809 | 54412992 | chr19 | 54413009 | 54413079 | chr19 | 54445250 | 54445297 |
| chr19 | 54445559 | 54445609 | chr19 | 54481691 | 54482050 | chr19 | 54483091 | 54483188 |
| chr19 | 54483190 | 54483306 | chr19 | 54483365 | 54483532 | chr19 | 54483534 | 54483630 |
| chr19 | 54485442 | 54485647 | chr19 | 54485673 | 54485913 | chr19 | 56159350 | 56159596 |
| chr19 | 56201573 | 56201812 | chr19 | 56588806 | 56588868 | chr19 | 56728588 | 56728603 |
| chr19 | 56728659 | 56728789 | chr19 | 56879475 | 56879554 | chr19 | 56879556 | 56879645 |
| chr19 | 56879647 | 56879994 | chr19 | 56879996 | 56880075 | chr19 | 56904643 | 56904704 |
| chr19 | 56904724 | 56904997 | chr19 | 56904999 | 56905302 | chr19 | 56915225 | 56915524 |
| chr19 | 56988458 | 56988664 | chr19 | 56989502 | 56989626 | chr19 | 56989697 | 56989851 |
| chr19 | 57050429 | 57050568 | chr19 | 57149480 | 57149719 | chr19 | 57154802 | 57155101 |
| chr19 | 57182906 | 57183127 | chr19 | 57183374 | 57183423 | chr19 | 57276559 | 57276798 |
| chr19 | 57610771 | 57610828 | chr19 | 57610896 | 57611067 | chr19 | 57617433 | 57617716 |
| chr19 | 57617832 | 57618170 | chr19 | 57683078 | 57683163 | chr19 | 57683240 | 57683372 |
| chr19 | 57862330 | 57862638 | chr19 | 57862640 | 57862859 | chr19 | 57862930 | 57862958 |
| chr19 | 57863222 | 57863229 | chr19 | 58011040 | 58011345 | chr19 | 58011347 | 58011383 |
| chr19 | 58038924 | 58039067 | chr19 | 58094925 | 58095468 | chr19 | 58095470 | 58095931 |
| chr19 | 58111529 | 58111888 | chr19 | 58125444 | 58125983 | chr19 | 58144419 | 58144778 |
| chr19 | 58219924 | 58220393 | chr19 | 58220516 | 58220883 | chr19 | 58238234 | 58238739 |
| chr19 | 58238988 | 58239012 | chr19 | 58239014 | 58239187 | chr19 | 58399978 | 58400277 |
| chr19 | 58400319 | 58400618 | chr19 | 58458679 | 58458891 | chr19 | 58458979 | 58459278 |
| chr19 | 58514416 | 58514655 | chr19 | 58520661 | 58521020 | chr19 | 58545042 | 58545388 |
| chr19 | 58545578 | 58545590 | chr19 | 58545652 | 58545843 | chr19 | 58609299 | 58609360 |
| chr19 | 58609473 | 58609526 | chr19 | 58609713 | 58609744 | chr19 | 58609746 | 58609944 |
| chr19 | 58629812 | 58629864 | chr19 | 58629975 | 58630026 | chr19 | 58661815 | 58662174 |
| chr19 | 58666093 | 58666392 | chr19 | 58739983 | 58740222 | chr19 | 58874834 | 58874951 |
| chr19 | 58907613 | 58907637 | chr19 | 58951175 | 58951401 | chr19 | 58951526 | 58951599 |
| chr19 | 58951601 | 58951778 | chr19 | 58951780 | 58952014 | chr19 | 58964105 | 58964283 |
| chr20 | 291052 | 291163 | chr20 | 291221 | 291453 | chr20 | 399928 | 400167 |
| chr20 | 401079 | 401258 | chr20 | 401495 | 401854 | chr20 | 590349 | 590588 |
| chr20 | 592323 | 592547 | chr20 | 644553 | 644826 | chr20 | 799030 | 799146 |
| chr20 | 982660 | 982799 | chr20 | 982892 | 983079 | chr20 | 1206766 | 1207125 |
| chr20 | 1783674 | 1784306 | chr20 | 2539252 | 2539552 | chr20 | 2539554 | 2539851 |
| chr20 | 2668670 | 2669026 | chr20 | 2780654 | 2780747 | chr20 | 2780894 | 2781122 |
| chr20 | 2781124 | 2781553 | chr20 | 2781657 | 2781836 | chr20 | 2785561 | 2785867 |
| chr20 | 2785956 | 2786160 | chr20 | 3027666 | 3027780 | chr20 | 3052501 | 3052692 |
| chr20 | 3052694 | 3052920 | chr20 | 3073561 | 3073994 | chr20 | 3204792 | 3205031 |

TABLE 15-continued

Pan-cancer #5

| chr | start | end | chr | start | end | chr | start | end |
|---|---|---|---|---|---|---|---|---|
| chr20 | 3220799 | 3221038 | chr20 | 3229475 | 3229480 | chr20 | 3229527 | 3229714 |
| chr20 | 3641774 | 3642015 | chr20 | 3662918 | 3663277 | chr20 | 4084983 | 4085146 |
| chr20 | 4229328 | 4229507 | chr20 | 4229684 | 4230684 | chr20 | 4802971 | 4803750 |
| chr20 | 4803846 | 4804053 | chr20 | 5296095 | 5296986 | chr20 | 5297226 | 5297419 |
| chr20 | 5297673 | 5297705 | chr20 | 6022813 | 6023052 | chr20 | 6748832 | 6749131 |
| chr20 | 8112304 | 8112483 | chr20 | 8112642 | 8113121 | chr20 | 8113462 | 8113701 |
| chr20 | 9487302 | 9487720 | chr20 | 9487789 | 9488032 | chr20 | 9488329 | 9488613 |
| chr20 | 9488650 | 9488934 | chr20 | 9488993 | 9489249 | chr20 | 9489377 | 9489796 |
| chr20 | 9495181 | 9495572 | chr20 | 9495574 | 9495600 | chr20 | 9496253 | 9496531 |
| chr20 | 9496581 | 9496912 | chr20 | 9496953 | 9497074 | chr20 | 10198206 | 10198685 |
| chr20 | 10198941 | 10199020 | chr20 | 13200498 | 13200737 | chr20 | 16555037 | 16555130 |
| chr20 | 17206434 | 17206840 | chr20 | 17207783 | 17208022 | chr20 | 17208484 | 17208657 |
| chr20 | 18039741 | 18039980 | chr20 | 19739495 | 19739566 | chr20 | 19739613 | 19739794 |
| chr20 | 19928211 | 19928450 | chr20 | 20344410 | 20344649 | chr20 | 20345597 | 20345631 |
| chr20 | 20346167 | 20346176 | chr20 | 20347358 | 20347710 | chr20 | 20347737 | 20348222 |
| chr20 | 20348447 | 20348686 | chr20 | 20349055 | 20349354 | chr20 | 20349500 | 20349679 |
| chr20 | 21080615 | 21080957 | chr20 | 21081029 | 21081845 | chr20 | 21082095 | 21082124 |
| chr20 | 21082216 | 21082354 | chr20 | 21082456 | 21082995 | chr20 | 21083322 | 21084461 |
| chr20 | 21085768 | 21085968 | chr20 | 21086075 | 21086152 | chr20 | 21086195 | 21086554 |
| chr20 | 21086808 | 21087267 | chr20 | 21372091 | 21372193 | chr20 | 21372295 | 21372810 |
| chr20 | 21376172 | 21376337 | chr20 | 21376703 | 21376734 | chr20 | 21376877 | 21377129 |
| chr20 | 21377474 | 21377641 | chr20 | 21377738 | 21378631 | chr20 | 21486299 | 21486660 |
| chr20 | 21486786 | 21486917 | chr20 | 21486955 | 21486958 | chr20 | 21487068 | 21487276 |
| chr20 | 21487368 | 21487667 | chr20 | 21488076 | 21488435 | chr20 | 21489135 | 21489159 |
| chr20 | 21489240 | 21489447 | chr20 | 21489622 | 21489794 | chr20 | 21490099 | 21490763 |
| chr20 | 21490815 | 21491346 | chr20 | 21491617 | 21491632 | chr20 | 21492309 | 21492410 |
| chr20 | 21492508 | 21492826 | chr20 | 21492991 | 21493071 | chr20 | 21493218 | 21493994 |
| chr20 | 21494438 | 21494797 | chr20 | 21495845 | 21496084 | chr20 | 21496158 | 21496397 |
| chr20 | 21496684 | 21497217 | chr20 | 21497337 | 21498716 | chr20 | 21500019 | 21500228 |
| chr20 | 21501294 | 21501360 | chr20 | 21501445 | 21501814 | chr20 | 21501945 | 21502145 |
| chr20 | 21502495 | 21502700 | chr20 | 21502838 | 21503174 | chr20 | 21503490 | 21503877 |
| chr20 | 21682309 | 21682329 | chr20 | 21682362 | 21682548 | chr20 | 21683213 | 21683751 |
| chr20 | 21685592 | 21685606 | chr20 | 21686157 | 21686293 | chr20 | 21686295 | 21686756 |
| chr20 | 21686921 | 21687383 | chr20 | 21687756 | 21687820 | chr20 | 21689862 | 21690137 |
| chr20 | 21694425 | 21694604 | chr20 | 21695014 | 21695274 | chr20 | 21695306 | 21695391 |
| chr20 | 21748349 | 21748588 | chr20 | 22557301 | 22557776 | chr20 | 22557898 | 22558197 |
| chr20 | 22558534 | 22558773 | chr20 | 22559549 | 22559676 | chr20 | 22559678 | 22559788 |
| chr20 | 22562632 | 22562886 | chr20 | 22563690 | 22563703 | chr20 | 22564161 | 22564291 |
| chr20 | 23015843 | 23015942 | chr20 | 23029012 | 23029232 | chr20 | 23029589 | 23030086 |
| chr20 | 23030292 | 23030442 | chr20 | 23031471 | 23031729 | chr20 | 24450133 | 24450612 |
| chr20 | 24450692 | 24450704 | chr20 | 24450820 | 24451084 | chr20 | 24451086 | 24451111 |
| chr20 | 24451372 | 24451671 | chr20 | 25058292 | 25058711 | chr20 | 25061654 | 25061789 |
| chr20 | 25061979 | 25062312 | chr20 | 25062511 | 25062646 | chr20 | 25062708 | 25062818 |
| chr20 | 25062871 | 25062973 | chr20 | 25063700 | 25063907 | chr20 | 25063994 | 25064539 |
| chr20 | 25065078 | 25065207 | chr20 | 25065209 | 25065497 | chr20 | 25129465 | 25129520 |
| chr20 | 25129522 | 25129544 | chr20 | 25230415 | 25230513 | chr20 | 25230775 | 25230894 |
| chr20 | 26188813 | 26188962 | chr20 | 26190218 | 26190432 | chr20 | 30101724 | 30101833 |
| chr20 | 30582655 | 30583074 | chr20 | 30639051 | 30639410 | chr20 | 30639531 | 30639570 |
| chr20 | 30639603 | 30639950 | chr20 | 30640009 | 30640256 | chr20 | 30640258 | 30640368 |
| chr20 | 30777930 | 30778339 | chr20 | 31115592 | 31115891 | chr20 | 31151695 | 31151874 |
| chr20 | 32301800 | 32302039 | chr20 | 32450399 | 32450518 | chr20 | 33547579 | 33547685 |
| chr20 | 33574834 | 33574981 | chr20 | 34041903 | 34042004 | chr20 | 34147928 | 34148347 |
| chr20 | 34188525 | 34188632 | chr20 | 34188748 | 34189089 | chr20 | 34189167 | 34189484 |
| chr20 | 34189622 | 34190013 | chr20 | 36531706 | 36532005 | chr20 | 36781250 | 36781429 |
| chr20 | 37302601 | 37303440 | chr20 | 37351701 | 37352516 | chr20 | 37352607 | 37352720 |
| chr20 | 37353096 | 37353335 | chr20 | 37353378 | 37353719 | chr20 | 37353807 | 37353857 |
| chr20 | 37354045 | 37354832 | chr20 | 37354994 | 37355304 | chr20 | 37355761 | 37356043 |
| chr20 | 37356169 | 37356828 | chr20 | 37357216 | 37357440 | chr20 | 37357739 | 37358278 |
| chr20 | 37434489 | 37434722 | chr20 | 37434737 | 37434828 | chr20 | 37435012 | 37435311 |
| chr20 | 37435362 | 37435370 | chr20 | 37435488 | 37435716 | chr20 | 37435718 | 37435961 |
| chr20 | 39316114 | 39316413 | chr20 | 39316814 | 39316853 | chr20 | 39316984 | 39317034 |
| chr20 | 39317036 | 39317473 | chr20 | 39317659 | 39318138 | chr20 | 39319031 | 39319204 |
| chr20 | 39319515 | 39319750 | chr20 | 39995061 | 39995546 | chr20 | 39995548 | 39995900 |
| chr20 | 41817697 | 41817916 | chr20 | 41818008 | 41818176 | chr20 | 41818472 | 41818749 |
| chr20 | 41818805 | 41819011 | chr20 | 42136252 | 42136491 | chr20 | 42218593 | 42218757 |
| chr20 | 42543655 | 42543954 | chr20 | 42543999 | 42544534 | chr20 | 42544728 | 42545078 |
| chr20 | 42876457 | 42876670 | chr20 | 43437970 | 43438086 | chr20 | 43438335 | 43438569 |
| chr20 | 43438883 | 43439122 | chr20 | 43439192 | 43439219 | chr20 | 43439248 | 43439611 |
| chr20 | 44452666 | 44453152 | chr20 | 44519003 | 44519182 | chr20 | 44601980 | 44602069 |
| chr20 | 44639100 | 44639579 | chr20 | 44640264 | 44640288 | chr20 | 44640313 | 44640443 |
| chr20 | 44660615 | 44660964 | chr20 | 44686423 | 44686615 | chr20 | 44686628 | 44686866 |
| chr20 | 44803096 | 44803126 | chr20 | 44803173 | 44803755 | chr20 | 44879700 | 44879791 |
| chr20 | 44880041 | 44880167 | chr20 | 44937124 | 44937369 | chr20 | 44937444 | 44937723 |
| chr20 | 44941441 | 44941740 | chr20 | 45141897 | 45142039 | chr20 | 45142152 | 45142244 |
| chr20 | 45142246 | 45142331 | chr20 | 45279779 | 45279982 | chr20 | 45280040 | 45280491 |
| chr20 | 45337726 | 45338025 | chr20 | 45524449 | 45524628 | chr20 | 47247136 | 47247407 |

TABLE 15-continued

Pan-cancer #5

| chr | start | end | chr | start | end | chr | start | end |
|---|---|---|---|---|---|---|---|---|
| chr20 | 47274032 | 47274137 | chr20 | 47296021 | 47296320 | chr20 | 47443647 | 47443937 |
| chr20 | 47443945 | 47444241 | chr20 | 47444243 | 47444366 | chr20 | 47905336 | 47905687 |
| chr20 | 47934747 | 47934987 | chr20 | 47934989 | 47935346 | chr20 | 47935412 | 47935651 |
| chr20 | 47935829 | 47936128 | chr20 | 48184289 | 48184292 | chr20 | 48184329 | 48184528 |
| chr20 | 49204105 | 49204524 | chr20 | 49261715 | 49262194 | chr20 | 49358363 | 49358477 |
| chr20 | 49377912 | 49378139 | chr20 | 49381177 | 49381340 | chr20 | 49575835 | 49575938 |
| chr20 | 49575988 | 49576014 | chr20 | 49639698 | 49639857 | chr20 | 49639883 | 49639997 |
| chr20 | 49640095 | 49640237 | chr20 | 50383399 | 50383504 | chr20 | 50384683 | 50384982 |
| chr20 | 50720356 | 50721201 | chr20 | 50721235 | 50721671 | chr20 | 50721989 | 50722021 |
| chr20 | 50722096 | 50722201 | chr20 | 50722609 | 50722908 | chr20 | 51589688 | 51589987 |
| chr20 | 52311387 | 52311505 | chr20 | 52789371 | 52789550 | chr20 | 52789765 | 52789949 |
| chr20 | 52790082 | 52790244 | chr20 | 53092165 | 53092233 | chr20 | 53092235 | 53092334 |
| chr20 | 53092336 | 53092464 | chr20 | 53093011 | 53093190 | chr20 | 54578407 | 54578826 |
| chr20 | 54579809 | 54579959 | chr20 | 54580070 | 54580408 | chr20 | 54580484 | 54580522 |
| chr20 | 54580622 | 54580783 | chr20 | 55199952 | 55200311 | chr20 | 55200616 | 55200791 |
| chr20 | 55200828 | 55201187 | chr20 | 55201451 | 55201452 | chr20 | 55201581 | 55201638 |
| chr20 | 55201686 | 55202069 | chr20 | 55202359 | 55202705 | chr20 | 55202728 | 55203207 |
| chr20 | 55204224 | 55204703 | chr20 | 55204864 | 55205103 | chr20 | 55206294 | 55206430 |
| chr20 | 55206464 | 55206495 | chr20 | 55499394 | 55499813 | chr20 | 55499932 | 55500171 |
| chr20 | 55500441 | 55500670 | chr20 | 55500672 | 55500721 | chr20 | 55693446 | 55693610 |
| chr20 | 55841036 | 55841455 | chr20 | 55842056 | 55842293 | chr20 | 56766206 | 56766203 |
| chr20 | 56803301 | 56803540 | chr20 | 56803762 | 56804001 | chr20 | 57089355 | 57089460 |
| chr20 | 57090104 | 57090259 | chr20 | 57224799 | 57225080 | chr20 | 57225219 | 57225405 |
| chr20 | 58152557 | 58152559 | chr20 | 58152776 | 58152796 | chr20 | 58179713 | 58179952 |
| chr20 | 58180214 | 58180403 | chr20 | 58180471 | 58180497 | chr20 | 58508796 | 58509005 |
| chr20 | 59804233 | 59804323 | chr20 | 59826885 | 59826978 | chr20 | 59828341 | 59828408 |
| chr20 | 59880480 | 59880575 | chr20 | 59910084 | 59910441 | chr20 | 59972951 | 59973170 |
| chr20 | 60202541 | 60202699 | chr20 | 60235251 | 60235610 | chr20 | 60238278 | 60238574 |
| chr20 | 60238780 | 60239079 | chr20 | 60243860 | 60244206 | chr20 | 60329482 | 60329661 |
| chr20 | 60359835 | 60359954 | chr20 | 60374934 | 60375173 | chr20 | 60439546 | 60439845 |
| chr20 | 60453829 | 60454186 | chr20 | 60477213 | 60477632 | chr20 | 60485281 | 60485480 |
| chr20 | 60502956 | 60503135 | chr20 | 60620233 | 60620412 | chr20 | 60772886 | 60773905 |
| chr20 | 60789866 | 60790225 | chr20 | 60925945 | 60926124 | chr20 | 60970879 | 60971058 |
| chr20 | 60983756 | 60984115 | chr20 | 60984356 | 60984553 | chr20 | 61287993 | 61288232 |
| chr20 | 61288380 | 61288619 | chr20 | 61294596 | 61294955 | chr20 | 61340486 | 61340785 |
| chr20 | 61412227 | 61412451 | chr20 | 61505882 | 61506421 | chr20 | 61532457 | 61532696 |
| chr20 | 61560341 | 61560461 | chr20 | 61560529 | 61561000 | chr20 | 61636755 | 61636779 |
| chr20 | 61636876 | 61636994 | chr20 | 61637391 | 61637649 | chr20 | 61637736 | 61637957 |
| chr20 | 61638221 | 61638470 | chr20 | 61638535 | 61638710 | chr20 | 61703710 | 61703762 |
| chr20 | 61703846 | 61703972 | chr20 | 61714683 | 61714696 | chr20 | 61734332 | 61734571 |
| chr20 | 61747795 | 61748034 | chr20 | 61763524 | 61763703 | chr20 | 61765251 | 61765490 |
| chr20 | 61808107 | 61808346 | chr20 | 61808667 | 61808888 | chr20 | 61808890 | 61809006 |
| chr20 | 61809219 | 61809557 | chr20 | 61809559 | 61809632 | chr20 | 61809841 | 61810135 |
| chr20 | 61810160 | 61810187 | chr20 | 61823076 | 61823195 | chr20 | 61862297 | 61862460 |
| chr20 | 61885196 | 61885291 | chr20 | 61885293 | 61885551 | chr20 | 61885778 | 61885848 |
| chr20 | 61885984 | 61886204 | chr20 | 61886257 | 61886343 | chr20 | 61886651 | 61886830 |
| chr20 | 61974094 | 61974453 | chr20 | 61980769 | 61981068 | chr20 | 62031085 | 62031324 |
| chr20 | 62031958 | 62032197 | chr20 | 62037460 | 62037699 | chr20 | 62046145 | 62046504 |
| chr20 | 62058624 | 62058859 | chr20 | 62090442 | 62090621 | chr20 | 62097763 | 62097771 |
| chr20 | 62115188 | 62115367 | chr20 | 62119246 | 62119619 | chr20 | 62119923 | 62120252 |
| chr20 | 62126035 | 62126514 | chr20 | 62157232 | 62157349 | chr20 | 62165548 | 62165847 |
| chr20 | 62167480 | 62167659 | chr20 | 62170105 | 62170284 | chr20 | 62172851 | 62173150 |
| chr20 | 62185296 | 62185535 | chr20 | 62321125 | 62321424 | chr20 | 62321551 | 62321970 |
| chr20 | 62340233 | 62340423 | chr20 | 62383135 | 62383374 | chr20 | 62461263 | 62461562 |
| chr20 | 62488263 | 62488442 | chr20 | 62680682 | 62680818 | chr20 | 62714923 | 62714946 |
| chr20 | 62715097 | 62715162 | chr21 | 22370246 | 22370347 | chr21 | 22370349 | 22370476 |
| chr21 | 22370614 | 22370733 | chr21 | 22370735 | 22370793 | chr21 | 26934278 | 26934877 |
| chr21 | 27011671 | 27011910 | chr21 | 27012283 | 27012522 | chr21 | 27944919 | 27945148 |
| chr21 | 27945619 | 27945798 | chr21 | 28216509 | 28216583 | chr21 | 28216634 | 28217768 |
| chr21 | 28218671 | 28218815 | chr21 | 28218877 | 28219150 | chr21 | 28338743 | 28338848 |
| chr21 | 28339165 | 28339584 | chr21 | 28339806 | 28339907 | chr21 | 28339909 | 28340049 |
| chr21 | 28340063 | 28340405 | chr21 | 31015127 | 31015306 | chr21 | 31311387 | 31311629 |
| chr21 | 31311846 | 31311920 | chr21 | 31312080 | 31312205 | chr21 | 31312230 | 31312259 |
| chr21 | 31312305 | 31312409 | chr21 | 33244901 | 33245131 | chr21 | 33245582 | 33245593 |
| chr21 | 33245716 | 33245821 | chr21 | 33245921 | 33245955 | chr21 | 33246038 | 33246280 |
| chr21 | 33627450 | 33627569 | chr21 | 33721671 | 33721910 | chr21 | 33983153 | 33983320 |
| chr21 | 34392070 | 34392168 | chr21 | 34392206 | 34392404 | chr21 | 34392437 | 34392669 |
| chr21 | 34395217 | 34396356 | chr21 | 34396707 | 34396870 | chr21 | 34396903 | 34397178 |
| chr21 | 34397993 | 34398131 | chr21 | 34398133 | 34398199 | chr21 | 34398201 | 34398222 |
| chr21 | 34398224 | 34398712 | chr21 | 34398847 | 34399259 | chr21 | 34399442 | 34400105 |
| chr21 | 34400232 | 34400346 | chr21 | 34401110 | 34401469 | chr21 | 34442595 | 34442696 |
| chr21 | 34443004 | 34443363 | chr21 | 34443419 | 34443778 | chr21 | 34443806 | 34444045 |
| chr21 | 34444082 | 34444363 | chr21 | 34444445 | 34444681 | chr21 | 36041934 | 36042029 |
| chr21 | 36042092 | 36042170 | chr21 | 36042172 | 36042322 | chr21 | 36042581 | 36042940 |
| chr21 | 37527854 | 37528033 | chr21 | 37758492 | 37758611 | chr21 | 37774963 | 37775238 |
| chr21 | 38064415 | 38064714 | chr21 | 38064917 | 38065523 | chr21 | 38065800 | 38065832 |

TABLE 15-continued

Pan-cancer #5

| chr | start | end | chr | start | end | chr | start | end |
|---|---|---|---|---|---|---|---|---|
| chr21 | 38065855 | 38066214 | chr21 | 38067247 | 38067308 | chr21 | 38068092 | 38068230 |
| chr21 | 38068647 | 38068871 | chr21 | 38069125 | 38069298 | chr21 | 38069359 | 38069598 |
| chr21 | 38069725 | 38069806 | chr21 | 38069854 | 38070144 | chr21 | 38070616 | 38070855 |
| chr21 | 38071699 | 38071781 | chr21 | 38071933 | 38071998 | chr21 | 38072920 | 38073159 |
| chr21 | 38073240 | 38073526 | chr21 | 38073616 | 38073940 | chr21 | 38077207 | 38077243 |
| chr21 | 38078332 | 38078571 | chr21 | 38079887 | 38080063 | chr21 | 38080175 | 38080387 |
| chr21 | 38080551 | 38080786 | chr21 | 38081112 | 38081193 | chr21 | 38081666 | 38081910 |
| chr21 | 38081968 | 38082011 | chr21 | 38082854 | 38083258 | chr21 | 38092081 | 38092320 |
| chr21 | 38119809 | 38120408 | chr21 | 38638505 | 38638624 | chr21 | 38935395 | 38935601 |
| chr21 | 39047688 | 39047889 | chr21 | 40984719 | 40984898 | chr21 | 43376299 | 43376478 |
| chr21 | 43786609 | 43786788 | chr21 | 43991389 | 43991568 | chr21 | 44283611 | 44283850 |
| chr21 | 44494941 | 44494997 | chr21 | 44494999 | 44495233 | chr21 | 44837002 | 44837245 |
| chr21 | 44837296 | 44837301 | chr21 | 44847488 | 44847606 | chr21 | 44847608 | 44847727 |
| chr21 | 44866508 | 44866807 | chr21 | 45148538 | 45148837 | chr21 | 45195115 | 45195414 |
| chr21 | 45273636 | 45273995 | chr21 | 45508543 | 45508662 | chr21 | 45791005 | 45791184 |
| chr21 | 46036556 | 46036855 | chr21 | 46126388 | 46126428 | chr21 | 46126567 | 46126807 |
| chr21 | 46126948 | 46127187 | chr21 | 46127468 | 46127628 | chr21 | 46128801 | 46129040 |
| chr21 | 46129346 | 46129585 | chr21 | 46257016 | 46257375 | chr21 | 46310341 | 46310580 |
| chr21 | 46318196 | 46318435 | chr21 | 46319069 | 46319548 | chr21 | 46359099 | 46359338 |
| chr21 | 46452278 | 46452637 | chr21 | 46677646 | 46677885 | chr21 | 46825737 | 46825823 |
| chr21 | 46863675 | 46863803 | chr21 | 46925704 | 46925999 | chr21 | 46926363 | 46926662 |
| chr21 | 46935727 | 46936018 | chr21 | 47010409 | 47010527 | chr21 | 47062753 | 47062925 |
| chr21 | 47063451 | 47064050 | chr21 | 47064165 | 47064464 | chr21 | 47404071 | 47404429 |
| chr21 | 47504759 | 47504994 | chr21 | 47518676 | 47518866 | chr21 | 47518888 | 47518915 |
| chr21 | 47717486 | 47717541 | chr21 | 47717623 | 47717665 | chr21 | 47746183 | 47746482 |
| chr22 | 17081848 | 17081936 | chr22 | 17082069 | 17082087 | chr22 | 17082492 | 17082524 |
| chr22 | 17082854 | 17082894 | chr22 | 17082989 | 17083062 | chr22 | 17083297 | 17083411 |
| chr22 | 17083525 | 17083596 | chr22 | 17600988 | 17601134 | chr22 | 17601260 | 17601467 |
| chr22 | 17602419 | 17602718 | chr22 | 17850359 | 17850718 | chr22 | 18009986 | 18010085 |
| chr22 | 18328049 | 18328348 | chr22 | 19017431 | 19017670 | chr22 | 19117490 | 19117669 |
| chr22 | 19510704 | 19510947 | chr22 | 19511142 | 19511456 | chr22 | 19511542 | 19511663 |
| chr22 | 19511765 | 19511876 | chr22 | 19706119 | 19706365 | chr22 | 19706367 | 19706754 |
| chr22 | 19742753 | 19742758 | chr22 | 19742789 | 19743052 | chr22 | 19748561 | 19748909 |
| chr22 | 19748961 | 19749040 | chr22 | 20792482 | 20792689 | chr22 | 21153919 | 21154084 |
| chr22 | 21304980 | 21305098 | chr22 | 21368513 | 21368692 | chr22 | 21977249 | 21977451 |
| chr22 | 21982708 | 21983062 | chr22 | 22006004 | 22006243 | chr22 | 22058102 | 22058341 |
| chr22 | 22090520 | 22090528 | chr22 | 22862704 | 22862863 | chr22 | 22863220 | 22863243 |
| chr22 | 22901011 | 22901550 | chr22 | 23791328 | 23791507 | chr22 | 23801388 | 23801567 |
| chr22 | 24180608 | 24180847 | chr22 | 24560283 | 24560522 | chr22 | 24820244 | 24820483 |
| chr22 | 25678654 | 25678869 | chr22 | 25679043 | 25679250 | chr22 | 25679268 | 25679433 |
| chr22 | 25817025 | 25817264 | chr22 | 25817356 | 25817715 | chr22 | 28198468 | 28198601 |
| chr22 | 28371575 | 28371754 | chr22 | 28838105 | 28838396 | chr22 | 28838411 | 28838524 |
| chr22 | 29091752 | 29091929 | chr22 | 29445659 | 29446018 | chr22 | 29876117 | 29876189 |
| chr22 | 29877142 | 29877381 | chr22 | 29977650 | 29977755 | chr22 | 30116824 | 30117147 |
| chr22 | 30158246 | 30158365 | chr22 | 30938434 | 30938507 | chr22 | 30938543 | 30938673 |
| chr22 | 31198416 | 31198715 | chr22 | 31218436 | 31218615 | chr22 | 31218693 | 31218932 |
| chr22 | 31481052 | 31481411 | chr22 | 32748862 | 32749041 | chr22 | 33197509 | 33197748 |
| chr22 | 33453802 | 33454075 | chr22 | 33454194 | 33454259 | chr22 | 33454346 | 33454452 |
| chr22 | 35848275 | 35848476 | chr22 | 36902217 | 36902456 | chr22 | 38199683 | 38199982 |
| chr22 | 38220568 | 38221287 | chr22 | 38476983 | 38477132 | chr22 | 38477297 | 38477882 |
| chr22 | 38592953 | 38593132 | chr22 | 38639155 | 38639308 | chr22 | 39784390 | 39784599 |
| chr22 | 39830257 | 39830492 | chr22 | 39853438 | 39853590 | chr22 | 39853592 | 39853657 |
| chr22 | 39932459 | 39932638 | chr22 | 39954323 | 39954400 | chr22 | 39954429 | 39954615 |
| chr22 | 40042536 | 40042835 | chr22 | 40075089 | 40075328 | chr22 | 40226368 | 40226487 |
| chr22 | 41048654 | 41048951 | chr22 | 41634334 | 41634618 | chr22 | 41636999 | 41637217 |
| chr22 | 41657217 | 41657442 | chr22 | 42095992 | 42096276 | chr22 | 42310005 | 42310304 |
| chr22 | 42311435 | 42311674 | chr22 | 42353530 | 42353992 | chr22 | 42667276 | 42667501 |
| chr22 | 42679917 | 42679935 | chr22 | 43012441 | 43012560 | chr22 | 43012883 | 43012980 |
| chr22 | 43083029 | 43083145 | chr22 | 43434340 | 43434579 | chr22 | 43739987 | 43740226 |
| chr22 | 43808205 | 43808502 | chr22 | 44208422 | 44208523 | chr22 | 44258287 | 44258586 |
| chr22 | 44287554 | 44287793 | chr22 | 44455605 | 44455844 | chr22 | 45088524 | 45088823 |
| chr22 | 45135840 | 45136079 | chr22 | 45277218 | 45277397 | chr22 | 45402991 | 45403230 |
| chr22 | 45404106 | 45404525 | chr22 | 45404909 | 45405011 | chr22 | 45405047 | 45405148 |
| chr22 | 45405219 | 45405432 | chr22 | 45405477 | 45405518 | chr22 | 45405545 | 45405627 |
| chr22 | 45405629 | 45405803 | chr22 | 45406181 | 45406420 | chr22 | 45593572 | 45593799 |
| chr22 | 45604107 | 45604444 | chr22 | 46262368 | 46263052 | chr22 | 46263512 | 46263624 |
| chr22 | 46263744 | 46263911 | chr22 | 46367955 | 46367987 | chr22 | 46368103 | 46368124 |
| chr22 | 46438002 | 46438112 | chr22 | 46658700 | 46658743 | chr22 | 46931177 | 46931336 |
| chr22 | 46933014 | 46933104 | chr22 | 47004998 | 47005237 | chr22 | 47023028 | 47023267 |
| chr22 | 47054612 | 47054700 | chr22 | 47193234 | 47193473 | chr22 | 47525747 | 47525986 |
| chr22 | 48027681 | 48027731 | chr22 | 48884960 | 48884960 | chr22 | 48885530 | 48885838 |
| chr22 | 48885908 | 48885989 | chr22 | 48886575 | 48886934 | chr22 | 48931805 | 48932104 |
| chr22 | 48971533 | 48971680 | chr22 | 48971759 | 48971829 | chr22 | 48972042 | 48972136 |
| chr22 | 48972220 | 48972466 | chr22 | 49852543 | 49852722 | chr22 | 49979553 | 49979835 |
| chr22 | 50001612 | 50001912 | chr22 | 50002684 | 50002911 | chr22 | 50003130 | 50003309 |
| chr22 | 50010037 | 50010336 | chr22 | 50010374 | 50010673 | chr22 | 50031617 | 50031796 |

TABLE 15-continued

Pan-cancer #5

| chr | start | end | chr | start | end | chr | start | end |
|---|---|---|---|---|---|---|---|---|
| chr22 | 50149332 | 50149548 | chr22 | 50466931 | 50467045 | chr22 | 50496972 | 50497000 |
| chr22 | 50497068 | 50497183 | chr22 | 50497214 | 50497367 | chr22 | 50623613 | 50623715 |
| chr22 | 50623742 | 50623894 | chr22 | 50899214 | 50899753 | chr22 | 50943082 | 50943358 |
| chr22 | 51042185 | 51042405 | chr22 | 51042458 | 51042566 | chr22 | 51112072 | 51112311 |
| chrX | 3746538 | 3746717 | chrX | 6145241 | 6145720 | chrX | 8698761 | 8699000 |
| chrX | 8699416 | 8699655 | chrX | 136656523 | 136656534 | AC211950.2_11234-25326 | 181 | 343 |
| AC211950.2_11234-25326 | 13241 | 13420 | AC211950.2_11234-25326 | 13667 | 13966 | AC241851.2_88-34049 | 15187 | 15426 |
| AEKP01168736.1_1-4752 | 1662 | 1781 | AEKP01168736.1_1-4752 | 1874 | 2381 | JH636052.4 | 5118687 | 5118986 |
| NW_001838016.1_818233-828058 | 6095 | 6142 | | | | | | |

TABLE 16

Blood Cancer

| chr | start | end | chr | start | end | chr | start | end |
|---|---|---|---|---|---|---|---|---|
| chr1 | 15251121 | 15251211 | chr1 | 15480854 | 15480892 | chr1 | 64240031 | 64240118 |
| chr1 | 64240618 | 64240673 | chr1 | 183774245 | 183774363 | chr1 | 202183372 | 202183401 |
| chr1 | 214724532 | 214724561 | chr1 | 232765226 | 232765301 | chr1 | 233750126 | 233750302 |
| chr2 | 14772762 | 14772823 | chr2 | 14774475 | 14774567 | chr2 | 46526303 | 46526331 |
| chr2 | 75427370 | 75427399 | chr2 | 101436638 | 101436708 | chr2 | 103236166 | 103236277 |
| chr2 | 151342979 | 151343218 | chr2 | 171571265 | 171571315 | chr2 | 171571890 | 171571997 |
| chr2 | 189157513 | 189157617 | chr2 | 235860803 | 235860808 | chr2 | 236402772 | 236402901 |
| chr2 | 236403271 | 236403419 | chr2 | 238395907 | 238395961 | chr3 | 37901952 | 37901953 |
| chr3 | 45187297 | 45187328 | chr3 | 126373521 | 126373619 | chr3 | 126373669 | 126373704 |
| chr3 | 133748141 | 133748206 | chr3 | 133748552 | 133748576 | chr3 | 153838819 | 153838870 |
| chr3 | 153839519 | 153839559 | chr3 | 153839641 | 153839775 | chr3 | 171527953 | 171527971 |
| chr4 | 24914639 | 24914668 | chr4 | 152246133 | 152246237 | chr4 | 170947288 | 170947325 |
| chr4 | 184019693 | 184019736 | chr4 | 184020107 | 184020179 | chr5 | 34656933 | 34657034 |
| chr5 | 72416247 | 72416262 | chr5 | 72733094 | 72733185 | chr5 | 107005984 | 107006186 |
| chr5 | 121413538 | 121413590 | chr6 | 1312001 | 1312095 | chr6 | 1312680 | 1312708 |
| chr6 | 1314089 | 1314101 | chr6 | 26987968 | 26988166 | chr6 | 42928322 | 42928454 |
| chr7 | 27275514 | 27275532 | chr7 | 28995658 | 28995978 | chr7 | 28996458 | 28996495 |
| chr7 | 32997125 | 32997454 | chr7 | 50860227 | 50860393 | chr7 | 50860980 | 50861103 |
| chr7 | 51384328 | 51384440 | chr7 | 51384916 | 51384951 | chr7 | 55086481 | 55086601 |
| chr7 | 55086984 | 55087533 | chr7 | 121945823 | 121945920 | chr7 | 155602752 | 155602805 |
| chr8 | 25041747 | 25041864 | chr8 | 95651539 | 95651599 | chr8 | 95651637 | 95651655 |
| chr8 | 102505798 | 102505934 | chr8 | 120220429 | 120220592 | chr9 | 14312995 | 14313096 |
| chr9 | 21559295 | 21559381 | chr9 | 21559678 | 21559702 | chr9 | 38620642 | 38620725 |
| chr9 | 110251389 | 110251418 | chr9 | 110252364 | 110252455 | chr9 | 134421818 | 134421835 |
| chr10 | 21462534 | 21462607 | chr10 | 30026077 | 30026090 | chr10 | 33624167 | 33624230 |
| chr10 | 33624493 | 33624550 | chr10 | 72973131 | 72973180 | chr10 | 116164249 | 116164341 |
| chr11 | 12132525 | 12132559 | chr11 | 12399041 | 12399145 | chr11 | 12399181 | 12399222 |
| chr11 | 12695482 | 12695496 | chr11 | 12695573 | 12695611 | chr11 | 12696612 | 12696746 |
| chr11 | 16628820 | 16628933 | chr11 | 33037468 | 33037556 | chr11 | 66790622 | 66790655 |
| chr11 | 120039834 | 120039865 | chr11 | 129245747 | 129245810 | chr11 | 130318961 | 130318997 |
| chr11 | 134201503 | 134201543 | chr11 | 134201842 | 134202084 | chr12 | 16500577 | 16500621 |
| chr12 | 56882365 | 56882380 | chr12 | 107486551 | 107486672 | chr12 | 107487195 | 107487855 |
| chr12 | 107712274 | 107712303 | chr13 | 100634315 | 100634382 | chr14 | 34420251 | 34420288 |
| chr14 | 61747389 | 61747528 | chr14 | 61747583 | 61747816 | chr14 | 61748002 | 61748033 |
| chr15 | 62456923 | 62456952 | chr15 | 71055770 | 71055815 | chr15 | 96874363 | 96874416 |
| chr15 | 98504115 | 98504144 | chr15 | 99193207 | 99193345 | chr15 | 99193350 | 99193465 |
| chr16 | 54964949 | 54965114 | chr16 | 68771167 | 68771298 | chr16 | 80966400 | 80966431 |
| chr16 | 84402245 | 84402319 | chr16 | 84853289 | 84853376 | chr17 | 42061337 | 42061381 |
| chr17 | 72427854 | 72427963 | chr17 | 72428345 | 72428381 | chr17 | 75207840 | 75207944 |
| chr17 | 80693343 | 80693554 | chr18 | 19750309 | 19750346 | chr18 | 21269350 | 21269390 |
| chr18 | 21269660 | 21269740 | chr18 | 78005004 | 78005051 | chr19 | 462182 | 462235 |
| chr19 | 33792412 | 33792524 | chr20 | 1206856 | 1207034 | chr20 | 6748926 | 6749036 |
| chr20 | 18039824 | 18039897 | chr20 | 22564236 | 22564265 | chr20 | 50384768 | 50384896 |
| chr21 | 38070706 | 38070765 | chr22 | 31198493 | 31198637 | | | |

TABLE 17

Breast Cancer

| chr | start | end | chr | start | end | chr | start | end |
|---|---|---|---|---|---|---|---|---|
| chr1 | 2336398 | 2336427 | chr1 | 2521025 | 2521062 | chr1 | 6507964 | 6508126 |
| chr1 | 21573736 | 21574203 | chr1 | 23885071 | 23885088 | chr1 | 155043332 | 155043657 |
| chr1 | 167823371 | 167823461 | chr1 | 185073819 | 185073966 | chr2 | 44497709 | 44497842 |
| chr2 | 61135116 | 61135137 | chr2 | 127863602 | 127863725 | chr3 | 12977068 | 12977144 |
| chr3 | 183728814 | 183728926 | chr5 | 43007937 | 43007966 | chr5 | 176764101 | 176764169 |
| chr6 | 41773521 | 41773844 | chr6 | 43748464 | 43748616 | chr7 | 907657 | 907709 |
| chr7 | 6188652 | 6188831 | chr7 | 6188926 | 6189061 | chr7 | 55410020 | 55410126 |
| chr7 | 127371130 | 127371234 | chr7 | 129800244 | 129800434 | chr7 | 131041516 | 131041596 |
| chr7 | 134918504 | 134918637 | chr8 | 61777576 | 61777622 | chr8 | 142367673 | 142367790 |
| chr8 | 144668567 | 144668667 | chr8 | 144668910 | 144668972 | chr9 | 34224349 | 34224474 |
| chr9 | 34372806 | 34372983 | chr9 | 129401098 | 129401195 | chr9 | 139888946 | 139888980 |
| chr10 | 6003403 | 6003625 | chr10 | 22047362 | 22047601 | chr11 | 232864 | 233062 |
| chr11 | 63641073 | 63641104 | chr12 | 110353415 | 110353451 | chr13 | 28239910 | 28240164 |
| chr14 | 102564465 | 102564502 | chr16 | 3802982 | 3803074 | chr16 | 85699690 | 85699921 |
| chr17 | 26961771 | 26961833 | chr17 | 42092191 | 42092220 | chr17 | 70026544 | 70026667 |
| chr18 | 74755509 | 74755577 | chr19 | 14181306 | 14181682 | chr19 | 33468019 | 33468055 |
| chr19 | 38782560 | 38782589 | chr19 | 40829794 | 40830032 | chr19 | 45570402 | 45570450 |
| chr19 | 45574774 | 45574782 | chr19 | 45574837 | 45574888 | chr20 | 6022813 | 6023045 |
| chr20 | 32301800 | 32301953 | chr20 | 60620233 | 60620412 | chr20 | 60772886 | 60773878 |
| chr21 | 37775035 | 37775141 | chr21 | 46935740 | 46935936 | chr22 | 21977315 | 21977347 |
| chr22 | 23801460 | 23801567 | chr22 | 24560376 | 24560522 | chr22 | 39830356 | 39830457 |
| chr22 | 41657234 | 41657350 | | | | | | |

TABLE 18

Colorectal Cancer

| chr | start | end | chr | start | end | chr | start | end |
|---|---|---|---|---|---|---|---|---|
| chr1 | 3659551 | 3659643 | chr1 | 3659672 | 3659716 | chr1 | 3663533 | 3663562 |
| chr1 | 12123244 | 12123276 | chr1 | 38511662 | 38511757 | chr2 | 12858453 | 12858499 |
| chr2 | 29338159 | 29338748 | chr2 | 29338810 | 29338969 | chr2 | 31360307 | 31360590 |
| chr2 | 31360631 | 31360693 | chr2 | 31360695 | 31360756 | chr2 | 31360804 | 31360831 |
| chr2 | 31456893 | 31457039 | chr2 | 100937837 | 100938164 | chr2 | 100938481 | 100938545 |
| chr2 | 100938575 | 100938799 | chr2 | 100938801 | 100938810 | chr2 | 100938985 | 100939155 |
| chr2 | 144694753 | 144695135 | chr2 | 172367022 | 172367125 | chr2 | 241542045 | 241542344 |
| chr3 | 142791152 | 142791173 | chr3 | 142839563 | 142839578 | chr3 | 142839580 | 142839607 |
| chr3 | 179168977 | 179169016 | chr4 | 718082 | 718112 | chr4 | 79689652 | 79689732 |
| chr4 | 156297417 | 156297556 | chr4 | 156297980 | 156298073 | chr5 | 38845676 | 38845705 |
| chr5 | 82769015 | 82769061 | chr5 | 111987788 | 111987818 | chr5 | 146257500 | 146257602 |
| chr6 | 73331516 | 73331851 | chr6 | 73331876 | 73332169 | chr6 | 73332392 | 73332674 |
| chr6 | 73332987 | 73333099 | chr6 | 127440332 | 127440510 | chr6 | 127440512 | 127440524 |
| chr6 | 151815056 | 151815089 | chr6 | 152957954 | 152957995 | chr6 | 163834315 | 163834383 |
| chr6 | 163834406 | 163834533 | chr6 | 163836569 | 163836900 | chr7 | 2728069 | 2728108 |
| chr7 | 28449277 | 28449291 | chr7 | 44364839 | 44364903 | chr7 | 69064591 | 69064772 |
| chr7 | 69064834 | 69064858 | chr7 | 76033251 | 76033289 | chr7 | 90226290 | 90226363 |
| chr7 | 106797775 | 106797804 | chr7 | 107483695 | 107483918 | chr7 | 134143808 | 134143908 |
| chr7 | 140027009 | 140027043 | chr7 | 149411542 | 149411728 | chr7 | 149411835 | 149412304 |
| chr7 | 150069099 | 150069346 | chr7 | 150070022 | 150070058 | chr8 | 53853998 | 53854027 |
| chr8 | 80803674 | 80803831 | chr8 | 97507150 | 97507246 | chr8 | 143533745 | 143533774 |
| chr9 | 37026964 | 37026993 | chr9 | 93698030 | 93698051 | chr9 | 140024843 | 140024919 |
| chr9 | 140024957 | 140025023 | chr10 | 3641379 | 3641396 | chr10 | 7450525 | 7450567 |
| chr10 | 7452350 | 7452550 | chr10 | 7453492 | 7453521 | chr10 | 49731643 | 49731749 |
| chr10 | 64578319 | 64578355 | chr10 | 101089410 | 101089439 | chr10 | 125851516 | 125851645 |
| chr10 | 125852300 | 125852498 | chr10 | 125852754 | 125853191 | chr10 | 133795401 | 133795430 |
| chr11 | 2040108 | 2040148 | chr11 | 3169689 | 3169835 | chr11 | 94275795 | 94275813 |
| chr11 | 94473683 | 94473769 | chr11 | 94473803 | 94473984 | chr11 | 94502453 | 94502489 |
| chr12 | 104850506 | 104850537 | chr12 | 104850578 | 104850592 | chr12 | 104851078 | 104851186 |
| chr13 | 26625302 | 26625502 | chr13 | 28366066 | 28366122 | chr13 | 36920350 | 36920379 |
| chr13 | 36920629 | 36920769 | chr13 | 73619661 | 73619698 | chr13 | 95364499 | 95364528 |
| chr13 | 95364771 | 95364800 | chr13 | 95620022 | 95620057 | chr13 | 110959797 | 110959860 |
| chr15 | 45670503 | 45670839 | chr15 | 48937059 | 48937095 | chr15 | 48937428 | 48937664 |
| chr15 | 48937710 | 48937987 | chr15 | 79383948 | 79383977 | chr15 | 83776497 | 83776596 |
| chr16 | 10276758 | 10276799 | chr16 | 10276801 | 10276841 | chr16 | 71715780 | 71715809 |
| chr17 | 32908287 | 32908371 | chr17 | 46125007 | 46125061 | chr17 | 47574091 | 47574149 |
| chr17 | 80535383 | 80535469 | chr19 | 3578139 | 3578223 | chr19 | 10823679 | 10823708 |
| chr19 | 50316245 | 50316330 | chr19 | 57862640 | 57862783 | chr20 | 4803922 | 4804008 |
| chr20 | 33547579 | 33547585 | chr20 | 36531800 | 36531910 | chr20 | 37434553 | 37434722 |
| chr20 | 37434737 | 37434744 | chr20 | 39317088 | 39317196 | chr21 | 27012374 | 27012431 |
| chr21 | 45508618 | 45508647 | chr22 | 39853522 | 39853590 | chr22 | 39853592 | 39853592 |

TABLE 19

Esophageal Cancer

| chr | start | end | chr | start | end | chr | start | end |
|---|---|---|---|---|---|---|---|---|
| chr1 | 3663875 | 3663921 | chr1 | 9712075 | 9712104 | chr1 | 11538796 | 11538821 |
| chr1 | 11539176 | 11539205 | chr1 | 11539411 | 11539440 | chr1 | 29450492 | 29450543 |
| chr1 | 38512386 | 38512415 | chr1 | 53068387 | 53068425 | chr1 | 91869989 | 91870018 |
| chr1 | 170633608 | 170633637 | chr1 | 202679216 | 202679327 | chr1 | 209381133 | 209381165 |
| chr1 | 230561780 | 230561824 | chr1 | 244014222 | 244014376 | chr2 | 31456683 | 31456712 |
| chr2 | 56410918 | 56410996 | chr2 | 56411692 | 56411733 | chr2 | 228029471 | 228029500 |
| chr3 | 37493520 | 37493621 | chr3 | 46924935 | 46924964 | chr3 | 49907094 | 49907130 |
| chr3 | 55519220 | 55519228 | chr3 | 98620892 | 98620980 | chr4 | 331323 | 331352 |
| chr4 | 57687721 | 57687782 | chr4 | 75858574 | 75858611 | chr4 | 87515338 | 87515367 |
| chr4 | 155665446 | 155665475 | chr5 | 129240069 | 129240101 | chr6 | 53212553 | 53213932 |
| chr6 | 71665639 | 71665723 | chr6 | 168719984 | 168720019 | chr7 | 409827 | 409872 |
| chr7 | 409887 | 409892 | chr7 | 54609992 | 54610006 | chr7 | 87104817 | 87105101 |
| chr7 | 87257964 | 87258054 | chr7 | 106685283 | 106685345 | chr7 | 113726510 | 113726539 |
| chr8 | 107282164 | 107282195 | chr8 | 110704002 | 110704029 | chr8 | 110704098 | 110704144 |
| chr9 | 21974208 | 21974237 | chr9 | 36037069 | 36037098 | chr9 | 112403365 | 112403394 |
| chr9 | 132805319 | 132805445 | chr9 | 132805750 | 132805893 | chr10 | 116853876 | 116853908 |
| chr10 | 134755905 | 134755934 | chr11 | 20618293 | 20618322 | chr11 | 20618527 | 20618556 |
| chr11 | 64410724 | 64410759 | chr11 | 107461624 | 107461653 | chr11 | 114113023 | 114113052 |
| chr12 | 8850659 | 8850744 | chr12 | 95267525 | 95267554 | chr12 | 133463737 | 133463876 |
| chr12 | 133758049 | 133758107 | chr13 | 46961495 | 46961533 | chr13 | 49794118 | 49794179 |
| chr13 | 78492724 | 78492748 | chr13 | 92050761 | 92050814 | chr14 | 51561766 | 51562012 |
| chr15 | 53082444 | 53082491 | chr15 | 65669860 | 65669899 | chr15 | 83378213 | 83378370 |
| chr15 | 91643361 | 91643586 | chr16 | 23313465 | 23313522 | chr16 | 23313780 | 23313836 |
| chr16 | 80838052 | 80838143 | chr17 | 14204213 | 14204242 | chr17 | 14204528 | 14204620 |
| chr17 | 40333045 | 40333226 | chr17 | 42907565 | 42907630 | chr17 | 48071021 | 48071050 |
| chr17 | 51901005 | 51901034 | chr17 | 56327272 | 56327301 | chr17 | 56833708 | 56833953 |
| chr19 | 10527166 | 10527243 | chr19 | 12163452 | 12163672 | chr19 | 12163894 | 12163923 |
| chr19 | 12175446 | 12175504 | chr19 | 12476501 | 12476556 | chr19 | 12606382 | 12606511 |
| chr19 | 23433144 | 23433223 | chr19 | 24216976 | 24217023 | chr19 | 33685545 | 33685581 |
| chr19 | 35264086 | 35264092 | chr19 | 37263533 | 37263584 | chr19 | 37341762 | 37341962 |
| chr19 | 37569394 | 37569554 | chr19 | 38085255 | 38085759 | chr19 | 38085958 | 38086066 |
| chr19 | 38146063 | 38146247 | chr19 | 38146458 | 38146568 | chr19 | 52097690 | 52097732 |
| chr19 | 53031202 | 53031215 | chr19 | 53193859 | 53193893 | chr19 | 58740087 | 58740118 |
| chr20 | 4230571 | 4230600 | chr20 | 20348527 | 20348605 | chr20 | 20349575 | 20349604 |
| chr20 | 39317751 | 39318138 | chr20 | 62680682 | 62680739 | chr21 | 33244922 | 33245040 |
| chr21 | 33245716 | 33245718 | chr21 | 33246038 | 33246190 | chr22 | 21368588 | 21368617 |
| chr22 | 24820331 | 24820396 | chr22 | 44208422 | 44208448 | | | |

TABLE 20

Head and Neck Cancer

| chr | start | end | chr | start | end | chr | start | end |
|---|---|---|---|---|---|---|---|---|
| chr1 | 898655 | 898690 | chr1 | 1856437 | 1856466 | chr1 | 1910416 | 1910445 |
| chr1 | 2375149 | 2375355 | chr1 | 10166522 | 10166551 | chr1 | 32180398 | 32180427 |
| chr1 | 97185263 | 97185357 | chr1 | 177150774 | 177150803 | chr1 | 246488176 | 246488316 |
| chr3 | 154797384 | 154797416 | chr4 | 146853952 | 146853981 | chr4 | 185089697 | 185089797 |
| chr5 | 57878711 | 57878752 | chr5 | 87976104 | 87976308 | chr5 | 87976526 | 87976559 |
| chr5 | 174220972 | 174221001 | chr7 | 44097691 | 44097876 | chr8 | 67025064 | 67025365 |
| chr9 | 140709047 | 140709174 | chr9 | 140727472 | 140727511 | chr9 | 140727846 | 140727930 |
| chr10 | 524755 | 524770 | chr11 | 392577 | 392720 | chr11 | 1027541 | 1027574 |
| chr11 | 66454425 | 66454454 | chr11 | 94884131 | 94884160 | chr12 | 54399617 | 54399646 |
| chr13 | 114807745 | 114807815 | chr14 | 21100749 | 21100778 | chr14 | 21100802 | 21100831 |
| chr16 | 1397455 | 1397484 | chr16 | 2128578 | 2128682 | chr16 | 2129033 | 2129332 |
| chr16 | 88757467 | 88757496 | chr17 | 1536129 | 1536146 | chr17 | 7348886 | 7348997 |
| chr17 | 17062575 | 17062752 | chr17 | 17123964 | 17123993 | chr18 | 32557847 | 32557864 |
| chr18 | 74501145 | 74501183 | chr19 | 1308066 | 1308081 | chr19 | 1775077 | 1775239 |
| chr19 | 58144495 | 58144701 | chr21 | 39047777 | 39047838 | chr21 | 44283611 | 44283774 |
| chr22 | 36902292 | 36902381 | chr22 | 42096003 | 42096190 | chr22 | 47023045 | 47023191 |
| chr22 | 47054687 | 47054700 | chr22 | 50943094 | 50943262 | chrX | 3746613 | 3746642 |

TABLE 21

Hepatobiliary Cancer

| chr | start | end | chr | start | end | chr | start | end |
|---|---|---|---|---|---|---|---|---|
| chr1 | 213123890 | 213123919 | chr2 | 1653023 | 1653230 | chr5 | 17512115 | 17512144 |
| chr6 | 26284812 | 26284898 | chr7 | 6543151 | 6543216 | chr7 | 64330412 | 64330470 |
| chr10 | 7213532 | 7213535 | chr10 | 7424627 | 7424687 | chr11 | 68409559 | 68409588 |

TABLE 21-continued

Hepatobiliary Cancer

| chr | start | end | chr | start | end | chr | start | end |
|---|---|---|---|---|---|---|---|---|
| chr12 | 105478324 | 105478359 | chr15 | 99456300 | 99456329 | chr16 | 47177526 | 47177606 |
| chr16 | 88942120 | 88942160 | chr17 | 29298081 | 29298184 | chr17 | 29298186 | 29298463 |
| chr17 | 42402885 | 42402917 | chr17 | 62777336 | 62777450 | chr18 | 77309534 | 77309563 |
| chr22 | 40075158 | 40075302 | | | | | | |

TABLE 22

Lung Cancer

| chr | start | end | chr | start | end | chr | start | end |
|---|---|---|---|---|---|---|---|---|
| chr1 | 12251874 | 12251958 | chr1 | 29586244 | 29586563 | chr1 | 50891347 | 50891376 |
| chr1 | 78511638 | 78511718 | chr1 | 91180277 | 91180306 | chr1 | 156010529 | 156010548 |
| chr1 | 161471751 | 161471779 | chr1 | 180204063 | 180204092 | chr1 | 200012190 | 200012191 |
| chr1 | 223936996 | 223937014 | chr1 | 228645141 | 228645244 | chr1 | 228645306 | 228645536 |
| chr2 | 43451910 | 43452327 | chr2 | 55289095 | 55289274 | chr2 | 106060616 | 106060792 |
| chr2 | 111875279 | 111875518 | chr2 | 118981668 | 118981738 | chr2 | 162272990 | 162273057 |
| chr2 | 175192104 | 175192136 | chr2 | 175193269 | 175193324 | chr2 | 175200141 | 175200170 |
| chr2 | 177001532 | 177001561 | chr2 | 223158970 | 223158999 | chr2 | 223165435 | 223165503 |
| chr2 | 223169835 | 223169864 | chr2 | 223176152 | 223176181 | chr2 | 230795536 | 230795565 |
| chr2 | 236877263 | 236877367 | chr2 | 242523908 | 242523985 | chr3 | 50402318 | 50402944 |
| chr3 | 181442377 | 181442410 | chr3 | 184057527 | 184057557 | chr4 | 3446992 | 3447021 |
| chr4 | 41750224 | 41750262 | chr4 | 42398843 | 42398872 | chr4 | 83323507 | 83323677 |
| chr4 | 166414897 | 166414921 | chr5 | 6687381 | 6687431 | chr5 | 10333726 | 10333762 |
| chr5 | 43215539 | 43215562 | chr5 | 50264821 | 50264850 | chr6 | 10416119 | 10416148 |
| chr6 | 18035868 | 18036015 | chr6 | 26332179 | 26332218 | chr6 | 28303563 | 28303571 |
| chr6 | 28303847 | 28304263 | chr6 | 50691066 | 50691095 | chr6 | 126068093 | 126068158 |
| chr6 | 152623016 | 152623493 | chr6 | 154970559 | 154970587 | chr7 | 2238119 | 2238235 |
| chr7 | 5262472 | 5262562 | chr7 | 27136761 | 27136790 | chr7 | 27195483 | 27195492 |
| chr7 | 113722940 | 113722969 | chr7 | 156801417 | 156801446 | chr8 | 108509544 | 108509650 |
| chr8 | 128931157 | 128931261 | chr8 | 142292553 | 142292774 | chr9 | 21965102 | 21965372 |
| chr9 | 21965686 | 21965757 | chr9 | 96721121 | 96721275 | chr9 | 96722477 | 96722548 |
| chr9 | 126349070 | 126349104 | chr10 | 3678618 | 3678637 | chr10 | 71327726 | 71327755 |
| chr10 | 102986586 | 102986758 | chr10 | 118890981 | 118891010 | chr10 | 124910364 | 124910439 |
| chr10 | 131937393 | 131937428 | chr11 | 67781387 | 67781564 | chr12 | 28127931 | 28127997 |
| chr12 | 28128620 | 28129054 | chr12 | 64783186 | 64783308 | chr12 | 72332642 | 72332696 |
| chr12 | 117474066 | 117474125 | chr14 | 37124038 | 37124067 | chr14 | 55765286 | 55765686 |
| chr14 | 73318472 | 73318629 | chr14 | 91691167 | 91691306 | chr14 | 91766189 | 91766450 |
| chr14 | 102682120 | 102682149 | chr15 | 37402975 | 37403087 | chr15 | 37403116 | 37403127 |
| chr15 | 65862054 | 65862121 | chr15 | 68125459 | 68125496 | chr16 | 142650 | 142775 |
| chr16 | 667548 | 667561 | chr16 | 677973 | 677993 | chr16 | 1407819 | 1407846 |
| chr16 | 2281250 | 2281314 | chr16 | 30907011 | 30907049 | chr16 | 30907123 | 30907148 |
| chr16 | 79623805 | 79623854 | chr16 | 85517346 | 85517388 | chr17 | 27181284 | 27181371 |
| chr17 | 37757154 | 37757217 | chr17 | 46655149 | 46655178 | chr17 | 46675420 | 46675449 |
| chr17 | 46691988 | 46692022 | chr17 | 46801219 | 46801277 | chr17 | 59539492 | 59539601 |
| chr17 | 75733979 | 75734108 | chr18 | 31902794 | 31902944 | chr18 | 55850846 | 55850987 |
| chr18 | 77550281 | 77550367 | chr19 | 8576915 | 8577000 | chr19 | 10407091 | 10407120 |
| chr20 | 44452732 | 44453063 | chr22 | 18328128 | 18328268 | chr22 | 19706634 | 19706677 |
| chr22 | 22058204 | 22058238 | chr22 | 28838201 | 28838292 | chr22 | 29445753 | 29445923 |

TABLE 23

Ovarian Cancer

| chr | start | end | chr | start | end | chr | start | end |
|---|---|---|---|---|---|---|---|---|
| chr1 | 2331364 | 2331437 | chr1 | 90309344 | 90309490 | chr1 | 219347395 | 219347472 |
| chr1 | 234620965 | 234620979 | chr1 | 245494496 | 245494578 | chr2 | 47200592 | 47200621 |
| chr2 | 47249735 | 47249848 | chr2 | 178973004 | 178973042 | chr2 | 209225238 | 209225275 |
| chr2 | 220080582 | 220080941 | chr2 | 240319921 | 240320012 | chr3 | 193419703 | 193419732 |
| chr4 | 1008741 | 1008806 | chr4 | 1282516 | 1282545 | chr4 | 57777438 | 57777577 |
| chr6 | 43639549 | 43639710 | chr7 | 127615922 | 127615951 | chr7 | 138042222 | 138042288 |
| chr7 | 140180180 | 140180298 | chr8 | 59058942 | 59059233 | chr8 | 141596887 | 141597022 |
| chr8 | 143558473 | 143558604 | chr8 | 144203654 | 144203708 | chr8 | 144303563 | 144303592 |
| chr10 | 135018033 | 135018070 | chr11 | 66658258 | 66658290 | chr11 | 120998702 | 120998825 |
| chr14 | 105512064 | 105512395 | chr16 | 4431127 | 4431189 | chr17 | 7368948 | 7369139 |
| chr17 | 77084519 | 77084667 | chr19 | 56201644 | 56201812 | chr22 | 46931261 | 46931332 |

TABLE 24

Pancreatic Cancer

| chr | start | end | chr | start | end | Chr | start | end |
|---|---|---|---|---|---|---|---|---|
| chr1 | 2472175 | 2472301 | chr1 | 6186512 | 6186546 | chr1 | 16475032 | 16475207 |
| chr1 | 17445858 | 17445943 | chr1 | 53705675 | 53705701 | chr1 | 62793238 | 62793267 |
| chr1 | 91182806 | 91182835 | chr1 | 98515143 | 98515191 | chr1 | 98519024 | 98519056 |
| chr1 | 115631868 | 115631915 | chr1 | 115880364 | 115880395 | chr1 | 156815693 | 156815745 |
| chr1 | 182584084 | 182584340 | chr1 | 182584404 | 182584613 | chr1 | 217307385 | 217307437 |
| chr1 | 240256664 | 240256780 | chr2 | 5833900 | 5833932 | chr2 | 7164468 | 7164704 |
| chr2 | 7571718 | 7571747 | chr2 | 18059782 | 18059841 | chr2 | 47193958 | 47193960 |
| chr2 | 99439478 | 99439507 | chr2 | 131594990 | 131595019 | chr2 | 145282120 | 145282149 |
| chr2 | 171822429 | 171822480 | chr3 | 5137961 | 5138019 | chr3 | 13679285 | 13679319 |
| chr3 | 38030619 | 38030782 | chr3 | 140770070 | 140770099 | chr3 | 152877667 | 152877696 |
| chr3 | 184319829 | 184319843 | chr3 | 184319874 | 184319891 | chr3 | 195601240 | 195601312 |
| chr3 | 195602364 | 195602435 | chr4 | 1093537 | 1093558 | chr4 | 1331676 | 1331705 |
| chr4 | 5892136 | 5892194 | chr4 | 7758477 | 7758561 | chr4 | 42154663 | 42154697 |
| chr4 | 57803529 | 57803558 | chr4 | 113431916 | 113431930 | chr4 | 183064875 | 183064966 |
| chr4 | 184921856 | 184921885 | chr5 | 1930991 | 1931005 | chr5 | 2753049 | 2753078 |
| chr5 | 3595850 | 3595876 | chr5 | 17218196 | 17218225 | chr5 | 76940341 | 76940374 |
| chr5 | 138273818 | 138273845 | chr6 | 711143 | 711293 | chr6 | 26199138 | 26199167 |
| chr6 | 26199687 | 26199716 | chr6 | 52344376 | 52344405 | chr6 | 72596273 | 72596315 |
| chr7 | 1970843 | 1970872 | chr7 | 20826885 | 20826939 | chr7 | 45614930 | 45615020 |
| chr7 | 100808467 | 100808502 | chr8 | 41166306 | 41166374 | chr9 | 77113806 | 77113825 |
| chr9 | 135456477 | 135456544 | chr9 | 140033002 | 140033050 | chr10 | 73157868 | 73158027 |
| chr10 | 85954426 | 85954457 | chr10 | 128994871 | 128994903 | chr10 | 130338728 | 130338761 |
| chr10 | 133849599 | 133849628 | chr11 | 27744451 | 27744480 | chr11 | 131564971 | 131565073 |
| chr12 | 4274272 | 4274409 | chr12 | 4379358 | 4379491 | chr12 | 4382007 | 4382162 |
| chr12 | 5541101 | 5541177 | chr12 | 79257223 | 79257351 | chr12 | 94544023 | 94544052 |
| chr12 | 101025381 | 101025410 | chr12 | 103889161 | 103889211 | chr12 | 127940087 | 127940189 |
| chr13 | 32605035 | 32605212 | chr13 | 32605443 | 32605596 | chr13 | 32605675 | 32605966 |
| chr14 | 32597621 | 32597657 | chr14 | 69014045 | 69014110 | chr14 | 92979918 | 92979991 |
| chr14 | 105714416 | 105714442 | chr14 | 105715248 | 105715393 | chr15 | 68128595 | 68128597 |
| chr15 | 74818773 | 74818789 | chr15 | 89943411 | 89943440 | chr16 | 12996949 | 12997011 |
| chr16 | 89007521 | 89007558 | chr16 | 89008563 | 89008592 | chr18 | 3215043 | 3215256 |
| chr18 | 57364659 | 57364691 | chr18 | 75362932 | 75362985 | chr19 | 869338 | 869363 |
| chr19 | 1764294 | 1764339 | chr19 | 1776505 | 1776534 | chr19 | 4054436 | 4054463 |
| chr19 | 5292813 | 5292844 | chr19 | 12996170 | 12996280 | chr19 | 41018717 | 41018746 |
| chr19 | 42028503 | 42028549 | chr19 | 51228050 | 51228079 | chr19 | 52552105 | 52552120 |
| chr20 | 52311464 | 52311505 | chr20 | 59804233 | 59804235 | chr20 | 62321824 | 62321881 |
| chr22 | 22006004 | 22006243 | chr22 | 41634394 | 41634423 | | | |

Example 4

Cancer Assay Panel (TCGA)

A panel capable of detecting the presence and/or stage of cancer generally (i.e., cancer vs non-cancer) was generated. The panel includes probes configured to hybridize to a modified fragment obtained from processing of the cfDNA molecules, wherein each of the cfDNA molecules corresponds to or is derived from one or more genomic regions in Table 11. The genomic regions in Table 11 were identified using the techniques described in the remainder of this document, as well as by targeting viral sequences/genomes, data set from the Cancer Genome Atlas (TCGA) which is developed as a result of the collaboration between the National Cancer Institute (NCI) and the National Human Genome Research Institute (NHGRI). The data set provides comprehensive, multi-dimensional maps of the key genomic changes in 33 types of cancer.

Table 11 lists the genomic regions in the following column format, starting from the left-most column: chromosome on which the target genomic region is located, start and stop position of the target genomic region, whether the target genomic region is hypermethylated or hypomethylated, and an annotation (if known) of any gene located within 10,000 bp of the targeted region of the genome. The chromosome numbers and the start and stop positions are provided relative to a known human reference genome, hg19. The sequence of the human reference genome, hg19, is available from Genome Reference Consortium with a reference number, GRCh37/hg19, and also available from Genome Browser provided by Santa Cruz Genomics Institute.

Generally, a probe is designed overlap with any of the CpG sites included within the start/stop ranges of the targeted regions (e.g., anomalous fragments) included in Table 11.

To identify genomic regions for use in the targeted panel from TCGA, 450K Illumina array TCGA data for BRCA (breast cancer), COAD (colon adenocarcinoma), LIHC (liver hepatocellular carcinoma), LUAD (lung adenocarcinoma), and LUSC (lung squamous cell carcinoma) was used. Since TCGA array data are at CpG site levels, they are prone to result in false positives. To avoid false positives, CpG sites were converted into 350 bp bins across the genome. Beta values of each bin was calculated as the mean of CpG beta values in that bin. The below table summarizes number of bins (bin count) having different ranges of mean CpG values (CpG/bin).

| CpG/bin | 1 | 2...5 | 6...10 | 11...16 | 16...20 | 20...25 |
|---|---|---|---|---|---|---|
| bin count | 220424 | 83644 | 6354 | 271 | 30 | 3 |

Bins with less than 2 CpGs were excluded from the analysis. Next, bins were selected with beta difference of >0.95 between normal and cancer tissues. For LIHC (Liver Hepatocellular Carcinoma) analysis 0.9 was used as the threshold. Those of skill in the art will appreciate that other thresholds for each of the parameters above may be used to select which CpG sites to target.

Total number of bins under analysis and the number of selected bins for each cancer type are summarized below. As indicated in the below table, more than 50% of the targeted genomic regions identified by this analysis overlap with the genomic regions selected using CCGA data set as provided in Example 3. However, 3459 CpG sites were in new genomic regions, which were not identified from the study using CCGA.

| Cancer Type | All bins count | Selected bins on low noise regions |
|---|---|---|
| BRCA | 2622 | 314 |
| COAD | 3282 | 779 |
| LIHC | 649 | 109 |
| LUAD | 3308 | 334 |
| LUSC | 2110 | 130 |
| Total size (Mbp) | 2.54 | 0.66 |
| Non_overlapping with CCGA targets | | 0.26 |

Additional liver specific markers were also added to the target genomic regions. To select these markers, 49 HCC (Hepatocellular Carcinoma) Tumor/Normal pairs were used from TCGA liver methylation dataset, by Illumina Infinium 450K array. A differential methylation analysis was performed on individual CpGs on the M value and hypermethylated CpGs with fold change >8 were selected. Only hypermethylated CpGs were selected in this version since they are more relevant in gene expression regulation. The clustered CpGs (defined by selected CpGs within 150 bp of another selected CpG) were combined into clusters, and expanded singletons into regions with a maximum length of 300 bp, provided all CpGs within the cluster or region are concordantly and significantly hypermethylated (mean fold change >4, minimum fold change >2).

Table 11 also includes some regions that have been reported in literature to be associated with different types of cancer. Other regions, such as SEPT9 and SHOX2, were also included in Table 11.

Table 11 also includes some target regions able to detect common driver mutations as well. To this end, regions studied in the Cohen et al, 2018 paper (Cohen et al., Detection and localization of surgically resectable cancers with a multi-analyte blood test, Science, 2018) are also included, as well as all protein variants in the oncoKB set.

Regarding the selection of viral sequences for inclusion in Table 11, for each cancer mentioned above, a model was fit with all possible combinations of viruses for diagnosis. Models within 10% of the top score were stored. All viruses that were present in any top model for any cancer were kept. This eliminated JCV-PLYCG and HPV8-ZM130, and kept HBV and HCV.

Five hundred sites were partitioned across the viral genomes. Sites were allocated to mirror the proportion of top models in which each virus was included. Within the genome of each virus, sites were distributed at intervals of not less than 250 bp. Sites were proposed with probability proportional to the CCGA data set read distribution. This distribution was chosen as a proxy for both uniqueness relative to human (specificity) and conservation across viral strains (sensitivity). Each proposed site was rejected if it was within 250 bp of an existing site, otherwise it was accepted. However, if the number of sites was sufficient to span the genome, sampling was uniform and any excess sites were allocated to other genomes. Reallocation of sites to other genomes was performed such that the final result was as close to the target allocation as possible.

Example 5

Performance of an Assay Panel for Diagnosis of Cancer

Performance of a panel described herein was evaluated by applying the binary rank score L2-regularized kernel logistic regression classifier, as described herein (see, e.g., FIG. 6A; see also PCT/US2019/022122 and U.S. Ser. No. 16/352, 602), to distinguish cancer sample from non-cancer samples utilizing three computationally distinct processes: (1) analysis of WGBS data ("Mscore.testV1"), (2) analysis of WGBS data with 10-fold cross-validation ("Mscore.testV1.cv"), and (3) analysis of WGBS data computationally filtered to limit classification to sequence reads of cfDNA molecules derived from the targeting genomic regions listed in Table 12 ("Mscore.testV1.cv.panel"). The sequence reads evaluated utilizing all three processes were obtained from the CCGA study described herein.

Figures 14A, 14B:
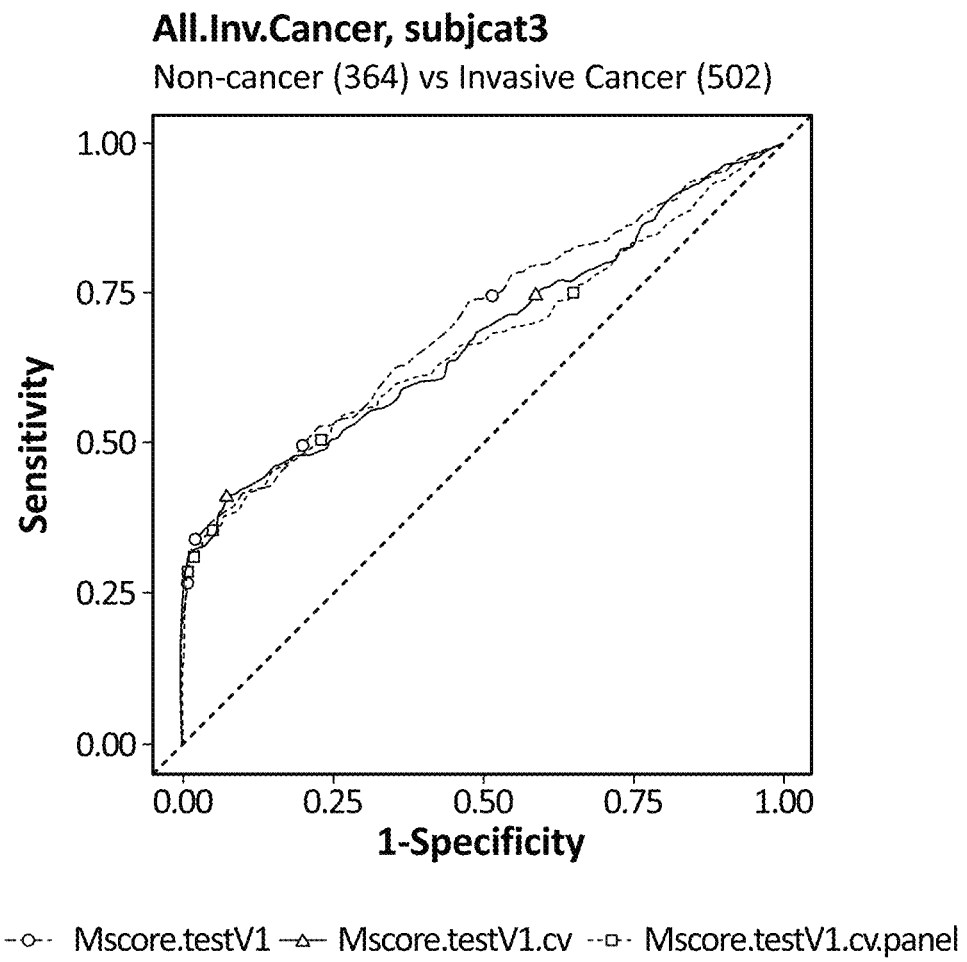
FIG. 14A shows sensitivity at 95% specificity of a cancer classifier applied to three different sources of data—Mscore.testV1, Mscore.testV1.cv, and Mscore.testV1.cv.panel.
FIG. 14B shows Receiver-Operator Characteristic (ROC) curves for performance analysis of the cancer classifier on the three different data sets.

Output scores were pooled and used to construct a Receiver operator characteristic (ROC) curve for performance analysis and to estimate sensitivity and specificity. Non-cancer samples were used to estimate specificity after correcting interfering signal. The relationship between sensitivity and specificity is depicted by receiver operator characteristic curves provided in FIG. 14B and sensitivity at 95% specificity for each data set is provided in FIG. 14A.

The data show high specificity of the classifier regardless of the computational approach used. The area under the curve (AUC) values and the sensitivity at 95% specificity were similar across the three computationally distinct processes. This result shows that the classifier is as effective in diagnosing cancer when analysis is restricted to targeted genomic regions, selected as described herein, as it is with unfiltered WGBS data. There was essentially no loss in performance when the analysis was restricted sequence reads of cfDNA molecules derived from targeted genomic regions listed in Table 12. By using targeted sequence reads obtained from use of the panel rather than entire nucleic acids sequencing, the panel-based method can increase sequencing depth of the target regions and lower costs compared to WGBS while providing similar degrees of sensitivity and specificity.

Example 6

Diagnosis of Cancer Using Cancer Assay Panel

Blood samples are collected from a group of individuals previously diagnosed with cancer, and another group of individuals without cancer. cfDNAs are extracted from the blood samples and treated with bisulfite to convert unmethylated cytosines to uracils. The bisulfite treated samples are applied to the cancer assay panel designed as provided herein. Unbound cfDNAs are washed and cfDNAs bound to the probes are collected. The collected cfDNAs are amplified and sequenced. The sequencing data confirm that the probes specifically enrich cfDNAs having methylation patterns indicative of cancer and samples from the cancer group include significantly more of the differentially methylated cfDNAs compared to the non-cancer group.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment, thereby providing a framework for various possibilities of described embodiments to function together.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While various specific embodiments have been illustrated and described, the above specification is not restrictive. It will be appreciated that various changes can be made without departing from the spirit and scope of the description(s). Many variations will become apparent to those skilled in the art upon review of this specification.

What is claimed is:

1. A method comprising:
   a) processing a sample comprising a plurality of DNA molecules to obtain converted DNA molecules comprising uracils at positions of unmethylated cytosines in the plurality of DNA molecules, wherein the plurality of DNA molecules comprises cell-free DNA (cfDNA) fragments;
   b) combining the converted DNA molecules with a bait set comprising at least 1,000 different oligonucleotide probes; and
   c) isolating converted DNA molecules hybridized to one or more of the at least 1,000 different oligonucleotide probes from unbound converted DNA molecules;
   wherein each probe of the at least 1,000 different oligonucleotide probes comprises a nucleic acid sequence that is either:
   (1) a first sequence that is identical to the sequence of at least 45 contiguous nucleotides within a target genomic region, or
   (2) a second sequence that varies with respect to the sequence of at least 45 contiguous nucleotides within the target genomic region by one or more transitions, wherein each respective transition of the one or more transitions occurs at a nucleotide corresponding to a CpG site in the target genomic region;
   wherein the at least 1,000 different oligonucleotide probes comprise at least 500 pairs of oligonucleotide probes;
   wherein each pair of the at least 500 pairs of oligonucleotide probes comprises two different oligonucleotide probes tiled with respect to the same target genomic region; and
   wherein the two different oligonucleotides probes of each pair of the at least 500 pairs of oligonucleotide probes comprise (i) an identical overlapping sequence comprising 30 contiguous nucleotides of the first or second sequence, and (ii) a different non-overlapping sequence of 15 contiguous nucleotides of the first or second sequence.

2. The method of claim 1, wherein the processing the plurality of DNA molecules comprises contacting the plurality of DNA molecules with bisulfate.

3. The method of claim 1, wherein each of the at least 1,000 different oligonucleotide probes comprises an affinity tag.

4. The method of claim 1, wherein the target genomic region comprises at least five CpG dinucleotides, and at least 80% of the at least five CpG dinucleotides are either methylated or unmethylated in an individual with cancer.

5. The method of claim 1, wherein the bait set comprises pairs of oligonucleotide probes for at least 500 target genomic regions.

6. The method of claim 5, wherein the at least 500 target genomic regions are selected from Table 11, Table 12, Table 13, Table 14 or Table 15 as follows:

TABLE 11

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 147543 | 147613 | Hypo | cancer_general | — | chr18 | 597548 | 597578 | Hypo | cancer_general | CLUL1 |
| chr18 | 697854 | 697901 | Hypo | cancer_general | ENOSF1 | chr18 | 2755770 | 2755878 | Hypo | cancer_general | SMCHD1 |
| chr18 | 3214441 | 3214825 | Hypo | pancreas | MYOM1 | chr18 | 3215042 | 3215256 | Hypo | pancreas | MYOM1 |
| chr18 | 5133207 | 5133343 | Hypo | cancer_general | — | chr18 | 6908056 | 6908243 | Hypo | esophageal | ARHGAP28 |
| chr18 | 8612252 | 8612282 | Hypo | cancer_general | RAB12 | chr18 | 9868137 | 9868174 | Hypo | cancer_general | — |
| chr18 | 9912767 | 9912797 | Hypo | cancer_general | VAPA | chr18 | 10251324 | 10251432 | Hypo | cancer_general | AX747048 |
| chr18 | 10589096 | 10589348 | Hypo | cancer_general | — | chr18 | 10733492 | 10733605 | Hypo | cancer_general | PIEZO2 |
| chr18 | 11401654 | 11401817 | Hypo | cancer_general | — | chr18 | 11942728 | 11942838 | Hypo | cancer_general | — |
| chr18 | 11979677 | 11979860 | Hypo | cancer_general | IMPA2 | chr18 | 12277243 | 12277273 | Hypo | hepatobiliary | CIDEA |
| chr18 | 12375483 | 12375597 | Hypo | cancer_general | AFG3L2 | chr18 | 12375923 | 12376129 | Hypo | cancer_general | AFG3L2 |
| chr18 | 12890152 | 12890278 | Hypo | cancer_general | PTPN2 | chr18 | 12948993 | 12949023 | Hypo | cancer_general | SEH1L |
| chr18 | 13132080 | 13132246 | Hypo | ovarian | CEP192 | chr18 | 13826393 | 13826536 | Hypo | cancer_general | MC5R |
| chr18 | 19191525 | 19191585 | Hypo | cancer_general | SNRPD1 | chr18 | 20911541 | 20911571 | Hypo | cancer_general | TMEM241 |
| chr18 | 21035222 | 21035252 | Hypo | cancer_general | RIOK3 | chr18 | 21719938 | 21720064 | Hypo | cancer_general | CABYR, TTC39C |
| chr18 | 23686462 | 23686618 | Hypo | cancer_general | — | chr18 | 29413805 | 29413839 | Hypo | breast | TRAPPC8 |
| chr18 | 29719775 | 29720012 | Hypo | cancer_general | RNF138 | chr18 | 32957803 | 32957839 | Hypo | cancer_general | ZNF396 |
| chr18 | 33078363 | 33078662 | Hypo | cancer_general | INO80C | chr18 | 43546048 | 43546134 | Hypo | cancer_general | EPG5 |
| chr18 | 44259903 | 44259990 | Hypo | cancer_general | STRSIA5, AK095045 | chr18 | 46142662 | 46142809 | Hypo | cancer_general | CTIF |
| chr18 | 48604773 | 48604802 | Hypo | literature | SMAD4 | chr18 | 48636211 | 48636320 | Hypo | cancer_general | — |
| chr18 | 51771058 | 51771128 | Hypo | cancer_general | — | chr18 | 53989796 | 53989877 | Hypo | cancer_general | — |
| chr18 | 55426948 | 55426978 | Hypo | cancer_general | — | chr18 | 55850845 | 55850987 | Hypo | lung, cancer_general | NEDD4L |
| chr18 | 56483918 | 56483958 | Hypo | cancer_general | — | chr18 | 56815734 | 56816107 | Hypo | cancer_general | SEC11C, AK311213 |
| chr18 | 60557729 | 60557759 | Hypo | cancer_general | PHLPP1 | chr18 | 61143911 | 61143975 | Hypo | literature | SERPINB5 |
| chr18 | 72845833 | 72845863 | Hypo | cancer_general | — | chr18 | 74501144 | 74501183 | Hypo | head_neck | LOC100131655 |
| chr18 | 74755508 | 74755590 | Hypo | breast | MBP | chr18 | 75335093 | 75335123 | Hypo | cancer_general | — |
| chr18 | 75339231 | 75339340 | Hypo | cancer_general | — | chr18 | 75551271 | 75551301 | Hypo | cancer_general | — |
| chr18 | 75999404 | 75999434 | Hypo | cancer_general | — | chr18 | 76239541 | 76239616 | Hypo | cancer_general | — |
| chr18 | 76501479 | 76501509 | Hypo | cancer_general | — | chr18 | 76653631 | 76653661 | Hypo | cancer_general | — |
| chr18 | 76686249 | 76686279 | Hypo | hepatobiliary | — | chr18 | 76689735 | 76689765 | Hypo | cancer_general | — |
| chr18 | 77050480 | 77050678 | Hypo | colorectal | ATP9B | chr18 | 77143346 | 77143376 | Hypo | cancer_general | ATP9B |
| chr18 | 77167824 | 77167854 | Hypo | cancer_general | NFATC1 | chr18 | 77181355 | 77181409 | Hypo | cancer_general | NFATC1 |
| chr18 | 77194936 | 77194978 | Hypo | cancer_general | NFATC1 | chr18 | 77205532 | 77205638 | Hypo | cancer_general | NFATC1 |
| chr18 | 77285897 | 77286028 | Hypo | cancer_general | — | chr18 | 77300326 | 77300483 | Hypo | cancer_general | — |
| chr18 | 77309533 | 77309563 | Hypo | cancer_general | — | chr18 | 77312866 | 77312927 | Hypo | cancer_general | — |
| chr18 | 77329727 | 77330017 | Hypo | cancer_general | CTDP1 | chr18 | 77371430 | 77371547 | Hypo | cancer_general | CTDP1 |
| chr18 | 77459762 | 77459877 | Hypo | cancer_general | — | chr18 | 77512225 | 77512255 | Hypo | cancer_general | — |
| chr18 | 77543249 | 77543481 | Hypo | cancer_general | — | chr18 | 77543700 | 77543824 | Hypo | cancer_general | — |
| chr18 | 77550206 | 77550367 | Hypo | lung, cancer_general | — | chr18 | 77576934 | 77577043 | Hypo | cancer_general | — |
| chr18 | 77636591 | 77636621 | Hypo | cancer_general | KCNG2 | chr18 | 77698881 | 77698919 | Hypo | breast | — |
| HCV | 111 | 140 | Hypo | virus | — | HCV | 374 | 403 | Hypo | virus | — |
| HCV | 637 | 666 | Hypo | virus | — | HCV | 900 | 929 | Hypo | virus | — |
| HCV | 1163 | 1192 | Hypo | virus | — | HCV | 1426 | 1455 | Hypo | virus | — |
| HCV | 1689 | 1718 | Hypo | virus | — | HCV | 1952 | 1981 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HCV | 2215 | 2244 | Hypo | virus | — | HCV | 2478 | 2507 | Hypo | virus | — |
| HCV | 2741 | 2770 | Hypo | virus | — | HCV | 3004 | 3033 | Hypo | virus | — |
| HCV | 3267 | 3296 | Hypo | virus | — | HCV | 3530 | 3559 | Hypo | virus | — |
| HCV | 3793 | 3822 | Hypo | virus | — | HCV | 4056 | 4085 | Hypo | virus | — |
| HCV | 4319 | 4348 | Hypo | virus | — | HCV | 4582 | 4611 | Hypo | virus | — |
| HCV | 4845 | 4874 | Hypo | virus | — | HCV | 5108 | 5137 | Hypo | virus | — |
| HCV | 5371 | 5400 | Hypo | virus | — | HCV | 5634 | 5663 | Hypo | virus | — |
| HCV | 5897 | 5926 | Hypo | virus | — | HCV | 6160 | 6189 | Hypo | virus | — |
| HCV | 6423 | 6452 | Hypo | virus | — | HCV | 6686 | 6715 | Hypo | virus | — |
| HCV | 6949 | 6978 | Hypo | virus | — | HCV | 7212 | 7241 | Hypo | virus | — |
| HCV | 7475 | 7504 | Hypo | virus | — | HCV | 7738 | 7767 | Hypo | virus | — |
| HCV | 8001 | 8030 | Hypo | virus | — | HCV | 8264 | 8293 | Hypo | virus | — |
| HCV | 8527 | 8556 | Hypo | virus | — | HCV | 8790 | 8819 | Hypo | virus | — |
| HCV | 9053 | 9082 | Hypo | virus | — | chr8 | 1085573 | 1085603 | Hypo | cancer_general | DLGAP2 |
| chr8 | 1325465 | 1325606 | Hypo | cancer_general | — | chr8 | 1444052 | 1444205 | Hypo | cancer_general | MFHAS1 |
| chr8 | 8640024 | 8640100 | Hypo | cancer_general | MFHAS1 | chr8 | 8681258 | 8681353 | Hypo | blood | MFHAS1 |
| chr8 | 8748422 | 8748713 | Hypo | cancer_general | MFHAS1 | chr8 | 8748919 | 8748956 | Hypo | cancer_general | CTSB, FDFT1 |
| chr8 | 9722850 | 9722896 | Hypo | cancer_general | C8orfl5 | chr8 | 10652917 | 10653017 | Hypo | ovarian | CTSB, FDFT1 |
| chr8 | 10980452 | 10980589 | Hypo | cancer_general | FDFT1, CTSB | chr8 | 11700190 | 11700284 | Hypo | head_neck | TRNA_Pseudo |
| chr8 | 11705960 | 11706136 | Hypo | cancer_general | FDFT1, CTSB | chr8 | 11706580 | 11706613 | Hypo | cancer_general | — |
| chr8 | 11726469 | 11726975 | Hypo | cancer_general | — | chr8 | 11790579 | 11790653 | Hypo | cancer_general | — |
| chr8 | 13319931 | 13319961 | Hypo | literature | — | chr8 | 20375563 | 20375592 | Hypo | literature | MIR320A, POLR3D |
| chr8 | 21876649 | 21876819 | Hypo | cancer_general | NPM2 | chr8 | 22101641 | 22101699 | Hypo | cancer_general | SLC25A37, AF116693, FP15737 |
| chr8 | 22458657 | 22458687 | Hypo | head_neck | KIAA1967, C8orf58, PDLIM2 | chr8 | 23423923 | 23423974 | Hypo | cancer_general | HMBOX1, INTS9 |
| chr8 | 28266438 | 28266484 | Hypo | breast | — | chr8 | 28737884 | 28738023 | Hypo | head_neck | — |
| chr8 | 30475450 | 30475480 | Hypo | breast | GTF2E2 | chr8 | 31044103 | 31044133 | Hypo | ovarian | EIF4EBP1 |
| chr8 | 37755922 | 37755952 | Hypo | cancer_general | — | chr8 | 37906396 | 37906513 | Hypo | head_neck | LSM1 |
| chr8 | 37961793 | 37961902 | Hypo | cancer_general | ASH2L, BAG4, LSM1 | chr8 | 38020213 | 38020272 | Hypo | head_neck | LETM2 |
| chr8 | 38032345 | 38032827 | Hypo | cancer_general | FGFR1, LETM2 | chr8 | 38256378 | 38256412 | Hypo | cancer_general | FGFR1, LETM2 |
| chr8 | 38262472 | 38262502 | Hypo | pancreas | ADAM5 | chr8 | 38274835 | 38274864 | Hypo | literature | SFRP1 |
| chr8 | 39172082 | 39172134 | Hypo | literature | — | chr8 | 41166305 | 41166374 | Hypo | pancreas | — |
| chr8 | 41700639 | 41700751 | Hypo | cancer_general | KAT6A | chr8 | 41711325 | 41711447 | Hypo | cancer_general | SLC20A2 |
| chr8 | 41910270 | 41910339 | Hypo | cancer_general | IKBKB | chr8 | 42082721 | 42082874 | Hypo | pancreas | MIR4469, HOOK3, RNF170 |
| chr8 | 42147392 | 42147521 | Hypo | cancer_general | SLC20A2 | chr8 | 42293604 | 42293722 | Hypo | breast | — |
| chr8 | 42350324 | 42350492 | Hypo | breast | — | chr8 | 42749816 | 42750012 | Hypo | cancer_general | — |
| chr8 | 47093246 | 47093276 | Hypo | cancer_general | — | chr8 | 47334619 | 47334678 | Hypo | cancer_general | — |
| chr8 | 48044710 | 48044753 | Hypo | ovarian | — | chr8 | 49572029 | 49572058 | Hypo | literature | C8orf22 |
| chr8 | 49836145 | 49836174 | Hypo | literature | SNAI2 | chr8 | 49959230 | 49959260 | Hypo | cancer_general | ST18 |
| chr8 | 52230518 | 52230548 | Hypo | cancer_general | PXDNL | chr8 | 53322495 | 53322524 | Hypo | literature | — |
| chr8 | 54698973 | 54699103 | Hypo | breast | ATP6V1H | chr8 | 55826087 | 55826117 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 56542925 | 56543064 | Hypo | literature | — | chr8 | 57360211 | 57360240 | Hypo | literature | AX747062, PENK |
| chr8 | 58105946 | 58106115 | Hypo | cancer_general | — | chr8 | 58117004 | 58117079 | Hypo | cancer_general | — |
| chr8 | 58130364 | 58130574 | Hypo | cancer_general | LOC100507651 | chr8 | 59058941 | 59059343 | Hypo | ovarian | FAM110B |
| chr8 | 59747186 | 59747318 | Hypo | cancer_general | TOX | chr8 | 61775575 | 61777699 | Hypo | breast | — |
| chr8 | 61789974 | 61790004 | Hypo | cancer_general | — | chr8 | 62033879 | 62034059 | Hypo | cancer_general | MTFR1, ARMC1 |
| chr8 | 62763403 | 62763433 | Hypo | cancer_general | — | chr8 | 66548717 | 66548800 | Hypo | cancer_general | C8orf44-SGK3, VCPIP1, C8orf44 |
| chr8 | 66560323 | 66560545 | Hypo | cancer_general | MTFR1 | chr8 | 67580735 | 67580829 | Hypo | cancer_general | — |
| chr8 | 71017156 | 71017195 | Hypo | cancer_general | NCOA2 | chr8 | 71308096 | 71308126 | Hypo | cancer_general | — |
| chr8 | 71447529 | 71447559 | Hypo | cancer_general | UBE2W | chr8 | 72470399 | 72470441 | Hypo | cancer_general | — |
| chr8 | 74759306 | 74759463 | Hypo | cancer_general | TCEB1, TMEM70 | chr8 | 74759819 | 74759966 | Hypo | cancer_general | UBE2W |
| chr8 | 74889486 | 74889592 | Hypo | cancer_general | TPD52, MRPS28 | chr8 | 76316329 | 76316452 | Hypo | cancer_general | HNF4G |
| chr8 | 80894529 | 80894594 | Hypo | cancer_general | — | chr8 | 80998526 | 80998601 | Hypo | lung | TPD52 |
| chr8 | 81128658 | 81128782 | Hypo | breast | — | chr8 | 81414643 | 81414831 | Hypo | colorectal | ZBTB10 |
| chr8 | 82243813 | 82243843 | Hypo | cancer_general | — | chr8 | 82902963 | 82902993 | Hypo | cancer_general | — |
| chr8 | 84932902 | 84932942 | Hypo | cancer_general | — | chr8 | 86131760 | 86131850 | Hypo | cancer_general | E2F5, CA13, AB209185, C8orf59 |
| chr8 | 86405788 | 86405818 | Hypo | lung | — | chr8 | 86406716 | 86406849 | Hypo | cancer_general | — |
| chr8 | 86436621 | 86436651 | Hypo | cancer_general | — | chr8 | 86495193 | 86495287 | Hypo | cancer_general | — |
| chr8 | 86544756 | 86544959 | Hypo | cancer_general | — | chr8 | 90702972 | 90703034 | Hypo | cancer_general | — |
| chr8 | 90913079 | 90913653 | Hypo | cancer_general | OSGIN2 | chr8 | 91411537 | 91411567 | Hypo | cancer_general | — |
| chr8 | 92083523 | 92083751 | Hypo | cancer_general | OTUD6B, BC067244 | chr8 | 94684190 | 94684560 | Hypo | cancer_general | LINC00535 |
| chr8 | 95485999 | 95486029 | Hypo | cancer_general | RAD54B C8orf69 | chr8 | 96038540 | 96038580 | Hypo | cancer_general | NDUFAF6 C8orf37, TRNA_Ser, LOC100616530 |
| chr8 | 96219863 | 96219901 | Hypo | cancer_general | — | chr8 | 96285420 | 96285553 | Hypo | ovarian | |
| chr8 | 97339846 | 97340195 | Hypo | cancer_general | PTDSS1 | chr8 | 98744202 | 98744325 | Hypo | cancer_general | MTDH |
| chr8 | 98786343 | 98786387 | Hypo | ovarian | LAPTM4B | chr8 | 98786918 | 98786972 | Hypo | ovarian | LAPTM4B |
| chr8 | 99234962 | 99235037 | Hypo | breast | NIPAL2 | chr8 | 99951939 | 99951939 | Hypo | cancer_general | OSR2 |
| chr8 | 100117651 | 100117765 | Hypo | breast | VPS13B | chr8 | 101169625 | 101169659 | Hypo | cancer_general | SPAG1, POLR2K |
| chr8 | 101726865 | 101726945 | Hypo | lung | PABPC1 | chr8 | 101736027 | 101736202 | Hypo | cancer_general | PABPC1 |
| chr8 | 103575128 | 103575296 | Hypo | pancreas | ODF1 | chr8 | 103629590 | 103629882 | Hypo | cancer_general | — |
| chr8 | 106301844 | 106301978 | Hypo | cancer_general | — | chr8 | 106434115 | 106434145 | Hypo | cancer_general | ZFPM2 |
| chr8 | 109500408 | 109500507 | Hypo | lung | EMC2 | chr8 | 110275006 | 110275040 | Hypo | cancer_general | NUDCD1 |
| chr8 | 110406028 | 110406243 | Hypo | cancer_general | PKHD1L1 | chr8 | 110592198 | 110592228 | Hypo | cancer_general | SYBU |
| chr8 | 110704001 | 110704144 | Hypo | esophageal | — | chr8 | 111133092 | 111133257 | Hypo | cancer_general | — |
| chr8 | 115516296 | 115516440 | Hypo | cancer_general | EXT1 | chr8 | 118532128 | 118532292 | Hypo | literature | MED30 |
| chr8 | 119043568 | 119043732 | Hypo | cancer_general | DSCC1, TAF2 | chr8 | 120219912 | 120219941 | Hypo | cancer_general | MAL2 |
| chr8 | 120844095 | 120844285 | Hypo | cancer_general | — | chr8 | 120845586 | 120845807 | Hypo | cancer_general | DSCC1, TAF2 |
| chr8 | 121825455 | 121825484 | Hypo | literature | — | chr8 | 122068889 | 122068919 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 122346689 | 122346719 | Hypo | cancer_general | — | chr8 | 122346940 | 122347052 | Hypo | cancer_general | — |
| chr8 | 123695532 | 123695660 | Hypo | cancer_general | — | chr8 | 124014063 | 124014111 | Hypo | lung | ATAD2 |
| chr8 | 124055236 | 124055336 | Hypo | cancer_general | DERL1 | chr8 | 124332846 | 124332875 | Hypo | literature | — |
| chr8 | 124427887 | 124428082 | Hypo | cancer_general | WDYHV1 | chr8 | 125411827 | 125411857 | Hypo | head_neck | — |
| chr8 | 125452366 | 125452541 | Hypo | cancer_general | — | chr8 | 126007690 | 126008051 | Hypo | ovarian | SQLE |
| chr8 | 126044442 | 126044563 | Hypo | cancer_general | KIAA0196, SQLE | chr8 | 127354106 | 127354261 | Hypo | cancer_general | — |
| chr8 | 128403354 | 128403383 | Hypo | literature | DQ515899, DQ515898, LOC727677 | chr8 | 128745542 | 128745633 | Hypo | cancer_general | MYC, HV975509, BC042052 |
| chr8 | 128808002 | 128808077 | Hypo | literature | MIR1204, PVT1, MYC | chr8 | 128872385 | 128872415 | Hypo | cancer_general | — |
| chr8 | 128889324 | 128889422 | Hypo | cancer_general | — | chr8 | 128893019 | 128893049 | Hypo | ovarian | PVT1 |
| chr8 | 128931133 | 128931261 | Hypo | lung | PVT1 | chr8 | 128964114 | 128964309 | Hypo | breast | MIR1205, TMEM75, PVT1 |
| chr8 | 129356009 | 129356039 | Hypo | cancer_general | — | chr8 | 130369244 | 130369364 | Hypo | cancer_general | CCDC26 |
| chr8 | 132054727 | 132054785 | Hypo | cancer_general | ADCY8 | chr8 | 133360080 | 133360194 | Hypo | cancer_general | KCNQ3 |
| chr8 | 133686745 | 133687107 | Hypo | cancer_general | LRRC6 | chr8 | 135301097 | 135301142 | Hypo | cancer_general | — |
| chr8 | 140755383 | 140755550 | Hypo | breast | TRAPPC9 | chr8 | 140834237 | 140834321 | Hypo | cancer_general | TRAPPC9 |
| chr8 | 140963292 | 140963362 | Hypo | cancer_general | TRAPPC9 | chr8 | 141054845 | 141054875 | Hypo | cancer_general | TRAPPC9 |
| chr8 | 141159919 | 141159949 | Hypo | cancer_general | — | chr8 | 141588056 | 141588132 | Hypo | cancer_general | AGO2 |
| chr8 | 141596886 | 141597022 | Hypo | ovarian | AGO2 | chr8 | 141614252 | 141614287 | Hypo | breast | AGO2 |
| chr8 | 142210914 | 142211043 | Hypo | lung | DENND3, SLC45A4 | chr8 | 142265206 | 142265339 | Hypo | ovarian | — |
| chr8 | 142282078 | 142282202 | Hypo | hepatobiliary | — | chr8 | 142292552 | 142292774 | Hypo | cancer_general, lung | — |
| chr8 | 142361233 | 142361487 | Hypo | cancer_general | GPR20, LOC731779 | chr8 | 142367368 | 142367790 | Hypo | breast | GPR20 |
| chr8 | 142444600 | 142444752 | Hypo | cancer_general | MROH5, PTP4A3 | chr8 | 142535343 | 142535496 | Hypo | cancer_general | — |
| chr8 | 142568598 | 142568652 | Hypo | cancer_general | — | chr8 | 142632436 | 142632465 | Hypo | literature | — |
| chr8 | 142694847 | 142694953 | Hypo | cancer_general | — | chr8 | 142984512 | 142984666 | Hypo | cancer_general | — |
| chr8 | 143082777 | 143082810 | Hypo | cancer_general | — | chr8 | 143089030 | 143089100 | Hypo | pancreas | TSNARE1 |
| chr8 | 143105244 | 143105377 | Hypo | cancer_general | — | chr8 | 143368318 | 143368469 | Hypo | cancer_general | BAI1 |
| chr8 | 143509457 | 143509594 | Hypo | ovarian | BAI1 | chr8 | 143557980 | 143558080 | Hypo | cancer_general | BAI1 |
| chr8 | 143558472 | 143558604 | Hypo | hepatobiliary | BAI1 | chr8 | 143587331 | 143587382 | Hypo | cancer_general | BAI1 |
| chr8 | 143611232 | 143611262 | Hypo | cancer_general | ARC | chr8 | 143621980 | 143622096 | Hypo | cancer_general | SLURP1, THEM6 |
| chr8 | 143702052 | 143702101 | Hypo | cancer_general | — | chr8 | 143819384 | 143819428 | Hypo | cancer_general | — |
| chr8 | 143876928 | 143876958 | Hypo | cancer_general | LY6D | chr8 | 143993974 | 143994165 | Hypo | cancer_general | CYP11B2 |
| chr8 | 144069546 | 144069651 | Hypo | cancer_general | CDC42P3, LOC100133669 | chr8 | 144190378 | 144190432 | Hypo | cancer_general | — |
| chr8 | 144203977 | 144204021 | Hypo | cancer_general | — | chr8 | 144226174 | 144226204 | Hypo | cancer_general | — |
| chr8 | 144238822 | 144238901 | Hypo | cancer_general | LY6H | chr8 | 144303562 | 144303592 | Hypo | ovarian | GPIHBP1 |
| chr8 | 144330193 | 144330380 | Hypo | cancer_general | ZFP41 | chr8 | 144344293 | 144344442 | Hypo | cancer_general | GLI4 |
| chr8 | 144347397 | 144347740 | Hypo | cancer_general | GLI4 | chr8 | 144359977 | 144360076 | Hypo | cancer_general | GLI4 |
| chr8 | 144360394 | 144360453 | Hypo | cancer_general | GLI4 | chr8 | 144361758 | 144361823 | Hypo | cancer_general | — |
| chr8 | 144372323 | 144372503 | Hypo | cancer_general | ZNF696 | chr8 | 144382679 | 144382775 | Hypo | cancer_general | TOP1MT, ZNF696 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 144421487 | 144421517 | Hypo | blood | TOP1MT | chr8 | 144557003 | 144557088 | Hypo | head_neck | ZC3H3 |
| chr8 | 144617065 | 144617347 | Hypo | ovarian | ZC3H3 | chr8 | 144668566 | 144668667 | Hypo | breast | BC034020, EEF1D, NAPRT1 |
| chr8 | 144668909 | 144668972 | Hypo | breast | BC034020, EEF1D, NAPRT1 | chr8 | 145218226 | 145218301 | Hypo | blood | MROH1 |
| chr8 | 145223902 | 145224061 | Hypo | ovarian | MROH1 | chr8 | 145753517 | 145753547 | Hypo | cancer_general | DQ579335, LRRC14, ARHGAP39, C8orf82, LRRC24 |
| chr8 | 145758572 | 145758692 | Hypo | cancer_general | ARHGAP39, C8orf82, LRRC24 | chr8 | 145918683 | 145918835 | Hypo | cancer_general | ARHGAP39 |
| chr8 | 146013617 | 146013647 | Hypo | cancer_general | RPL8, DL491750, ZNF34 | chr8 | 146079215 | 146079379 | Hypo | cancer_general | COMMD5 |
| chr8 | 146175120 | 146175269 | Hypo | cancer_general | ZNF16 | chr8 | 146176756 | 146176795 | Hypo | cancer_general | ZNF16 |
| chr21 | 19274828 | 19274858 | Hypo | cancer_general | CHODL | chr21 | 31015201 | 31015231 | Hypo | cancer_general | GRIK1 |
| chr21 | 31056850 | 31056927 | Hypo | hepatobiliary | GRIK1 | chr21 | 32253745 | 32253774 | Hypo | literature | KRTAP11-1 |
| chr21 | 33043985 | 33044051 | Hypo | breast | SOD1, SCAF4 | chr21 | 33627549 | 33627649 | Hypo | cancer_general | — |
| chr21 | 33721756 | 33721824 | Hypo | cancer_general | URB1 | chr21 | 33983236 | 33983488 | Hypo | cancer_general | C21orf59 |
| chr21 | 34397024 | 34397091 | Hypo | cancer_general | OLIG2 | chr21 | 34469746 | 34469844 | Hypo | cancer_general | — |
| chr21 | 35051159 | 35051231 | Hypo | cancer_general | ITSN1 | chr21 | 37527928 | 37527958 | Hypo | cancer_general | DOPEY2, CBR3-AS1, CBR3 |
| chr21 | 37758570 | 37758652 | Hypo | cancer_general | CHAF1B | chr21 | 37775034 | 37775141 | Hypo | cancer_general, breast | CHAF1B |
| chr21 | 38092179 | 38092221 | Hypo | cancer_general | SIM2 | chr21 | 38638422 | 38638526 | Hypo | cancer_general | DSCR3 |
| chr21 | 38935478 | 38935549 | Hypo | literature | — | chr21 | 40034756 | 40034785 | Hypo | literature | ERG |
| chr21 | 42596911 | 42597043 | Hypo | hepatobiliary | — | chr21 | 42617963 | 42617995 | Hypo | hepatobiliary | BACE2 |
| chr21 | 42649172 | 42649202 | Hypo | hepatobiliary | BACE2 | chr21 | 43240082 | 43240112 | Hypo | ovarian | PRDM15 |
| chr21 | 43256565 | 43256603 | Hypo | blood | PRDM15 | chr21 | 43376373 | 43376403 | Hypo | cancer_general | — |
| chr21 | 43393528 | 43393713 | Hypo | pancreas | — | chr21 | 43485279 | 43485348 | Hypo | head_neck | AX748362, UMODL1 |
| chr21 | 43786683 | 43786713 | Hypo | cancer_general | TMPRSS3, TFF1 | chr21 | 43991463 | 43991493 | Hypo | cancer_general | SLC37A1 |
| chr21 | 44250815 | 44250855 | Hypo | cancer_general | — | chr21 | 44283581 | 44283774 | Hypo | head_neck | WDR4 |
| chr21 | 44514762 | 44514791 | Hypo | literature | U2AF1 | chr21 | 44524441 | 44524470 | Hypo | literature | U2AF1 |
| chr21 | 44837088 | 44837213 | Hypo | cancer_general | SIK1 | chr21 | 44866603 | 44866711 | Hypo | cancer_general | LINC00319 |
| chr21 | 44886709 | 44886870 | Hypo | breast | LINC00313 | chr21 | 45118492 | 45118644 | Hypo | esophageal | RRP1B |
| chr21 | 45131875 | 45131905 | Hypo | cancer_general | PDXK | chr21 | 45195149 | 45195319 | Hypo | cancer_general | CSTB |
| chr21 | 45271643 | 45271688 | Hypo | cancer_general | — | chr21 | 45273717 | 45273913 | Hypo | cancer_general | — |
| chr21 | 45277332 | 45277513 | Hypo | cancer_general | AGPAT3 | chr21 | 45290014 | 45290044 | Hypo | head_neck | AGPAT3 |
| chr21 | 45508617 | 45508647 | Hypo | colorectal | TRAPPC10 | chr21 | 45521343 | 45521438 | Hypo | breast | PWP2, TRAPPC10 |
| chr21 | 45621533 | 45621573 | Hypo | breast | — | chr21 | 45791079 | 45791109 | Hypo | cancer_general | TRPM2 |
| chr21 | 45847832 | 45847973 | Hypo | cancer_general | TRPM2 | chr21 | 46036642 | 46036767 | Hypo | cancer_general | KRTAP10-8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr21 | 46199414 | 46199542 | Hypo | cancer_general | UBE2G2 | chr21 | 46257116 | 46257273 | Hypo | cancer_general | ITGB2 |
| chr21 | 46310428 | 46310491 | Hypo | cancer_general | ITGB2 | chr21 | 46318286 | 46318343 | Hypo | cancer_general | FAM207A, C21orf67, ITGB2-AS1 |
| chr21 | 46319156 | 46319459 | Hypo | cancer_general | ITGB2 | chr21 | 46359187 | 46359248 | Hypo | cancer_general | — |
| chr21 | 46452374 | 46452539 | Hypo | cancer_general | — | chr21 | 46677734 | 46677796 | Hypo | cancer_general | POFUT2, C21orf89 |
| chr21 | 46847654 | 46847684 | Hypo | pancreas | COL18A1-AS1 | chr21 | 46863658 | 46863708 | Hypo | cancer_general | — |
| chr21 | 46925780 | 46925925 | Hypo | breast | COL18A1, SLC19A1 | chr21 | 46926459 | 46926565 | Hypo | cancer_general | SLC19A1, COL18A1 |
| chr21 | 46935739 | 46935936 | Hypo | breast | SLC19A1, COL18A1 | chr21 | 47404174 | 47404325 | Hypo | cancer_general | COL6A1 |
| chr21 | 47504861 | 47504895 | Hypo | cancer_general | — | chr21 | 47746270 | 47746393 | Hypo | cancer_general | PCNT, BC031638, C21orf58 |
| chr11 | 232863 | 233062 | Hypo | breast | PSMD13, SIRT3 | chr11 | 392576 | 392720 | Hypo | head_neck | PKP3 |
| chr11 | 394815 | 394968 | Hypo | cancer_general | PKP3 | chr11 | 505732 | 505869 | Hypo | cancer_general | RNH1 |
| chr11 | 518400 | 518430 | Hypo | cancer_general | — | chr11 | 526389 | 526419 | Hypo | cancer_general | HRAS |
| chr11 | 533451 | 533567 | Hypo | literature | LRRC56, HRAS | chr11 | 533859 | 533888 | Hypo | literature | LRRC56, HRAS |
| chr11 | 534273 | 534302 | Hypo | literature | LRRC56, HRAS | chr11 | 548731 | 548800 | Hypo | lung | C11orf35, AX748330, LRRC56 |
| chr11 | 763323 | 763686 | Hypo | cancer_general | BC048998, PDDC1, TALDO1 | chr11 | 775261 | 775291 | Hypo | pancreas | NS3BP, PDDC1, BC048998 |
| chr11 | 850555 | 850823 | Hypo | cancer_general | TSPAN4, POLR2L, AK126635 | chr11 | 861612 | 861657 | Hypo | cancer_general | CHID1, AK126635, TSPAN4 |
| chr11 | 863062 | 863092 | Hypo | cancer_general | CHID1, AK126635, TSPAN4 | chr11 | 1006077 | 1006107 | Hypo | cancer_general | MUC6 |
| chr11 | 1027540 | 1027574 | Hypo | head_neck | MUC6 | chr11 | 1029238 | 1029403 | Hypo | cancer_general | MUC6 |
| chr11 | 1030215 | 1030296 | Hypo | cancer_general | MUC6 | chr11 | 1080391 | 1080454 | Hypo | cancer_general | MUC2 |
| chr11 | 1081667 | 1081715 | Hypo | cancer_general | MUC2 | chr11 | 1214665 | 1214917 | Hypo | cancer_general | MUC5AC, MUC5B |
| chr11 | 1215899 | 1215999 | Hypo | cancer_general | MUC5AC, MUC5B | chr11 | 1229945 | 1229975 | Hypo | cancer_general | MUC5AC, MUC5B |
| chr11 | 1244381 | 1244465 | Hypo | cancer_general | MUC5B | chr11 | 1250889 | 1250924 | Hypo | cancer_general | MUC5B |
| chr11 | 1251183 | 1251351 | Hypo | cancer_general | MUC5B | chr11 | 1263602 | 1263644 | Hypo | cancer_general | MUC5B |
| chr11 | 1274085 | 1274189 | Hypo | cancer_general | MUC5B | chr11 | 1374959 | 1375003 | Hypo | cancer_general | — |
| chr11 | 1430714 | 1430794 | Hypo | cancer_general | BRSK2 | chr11 | 1464280 | 1464428 | Hypo | cancer_general | BRSK2 |
| chr11 | 1469228 | 1469379 | Hypo | cancer_general | BRSK2 | chr11 | 1471920 | 1472058 | Hypo | cancer_general | BRSK2 |
| chr11 | 1868081 | 1868237 | Hypo | cancer_general | TNN2, LSP1 | chr11 | 1946130 | 1946160 | Hypo | cancer_general | TNNT3 |
| chr11 | 1957391 | 1957530 | Hypo | cancer_general | TNNT3 | chr11 | 1959077 | 1959187 | Hypo | cancer_general | MRPL23, TNNT3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 2040107 | 2040148 | Hypo | colorectal | — | chr11 | 2209907 | 2210278 | Hypo | cancer_general | — |
| chr11 | 2226048 | 2226078 | Hypo | cancer_general | — | chr11 | 2278708 | 2278839 | Hypo | cancer_general | — |
| chr11 | 2437991 | 2438144 | Hypo | cancer_general | TRPM5 | chr11 | 3027425 | 3027562 | Hypo | head_neck | CARS |
| chr11 | 3169665 | 3169835 | Hypo | colorectal | — | chr11 | 3182104 | 3182133 | Hypo | tcga | — |
| chr11 | 3511446 | 3511501 | Hypo | hepatobiliary | — | chr11 | 3767205 | 3767284 | Hypo | cancer_general | NUP98 |
| chr11 | 4038082 | 4038176 | Hypo | cancer_general | — | chr11 | 4095819 | 4095864 | Hypo | ovarian | STIM1 |
| chr11 | 4209382 | 4209411 | Hypo | tcga | RRM1, LOC100506082 | chr11 | 5641077 | 5641140 | Hypo | lung | TRIM34, TRIM6, TRIM6-TRIM34 |
| chr11 | 5993897 | 5994029 | Hypo | cancer_general | OR56A5 | chr11 | 6497192 | 6497222 | Hypo | cancer_general | ARFIP2, TIMM10B, TRIM3 |
| chr11 | 9405392 | 9405752 | Hypo | cancer_general | IPO7 | chr11 | 10509678 | 10509807 | Hypo | cancer_general | AMPD3 |
| chr11 | 10811151 | 10811224 | Hypo | cancer_general | EIF4G2, CTR9 | chr11 | 10815867 | 10815998 | Hypo | cancer_general | EIF4G2, SNORD97 |
| chr11 | 13711492 | 13711529 | Hypo | hepatobiliary | FAR1 | chr11 | 14316375 | 14316404 | Hypo | literature | RRAS2 |
| chr11 | 14543250 | 14543304 | Hypo | cancer_general | PSMA1 | chr11 | 14866247 | 14866285 | Hypo | cancer_general | PDE3B |
| chr11 | 17741679 | 17741708 | Hypo | literature | MYOD1 | chr11 | 18100096 | 18100259 | Hypo | breast | SAAL1 |
| chr11 | 20408219 | 20408341 | Hypo | cancer_general | PRMT3 | chr11 | 20618292 | 20618322 | Hypo | esophageal | SLC6A5 |
| chr11 | 20618526 | 20618556 | Hypo | esophageal | SLC6A5 | chr11 | 31760124 | 31760235 | Hypo | ovarian | ELP4 |
| chr11 | 33264773 | 33264935 | Hypo | head_neck | HIPK3 | chr11 | 33277455 | 33277485 | Hypo | cancer_general | HIPK3 |
| chr11 | 33318780 | 33318945 | Hypo | pancreas | — | chr11 | 33858324 | 33858463 | Hypo | cancer_general | ELF5 |
| chr11 | 33993984 | 33994014 | Hypo | cancer_general | — | chr11 | 34535093 | 34535123 | Hypo | cancer_general | ALX4 |
| chr11 | 35684958 | 35685131 | Hypo | cancer_general | TRIM44 | chr11 | 44337533 | 44337571 | Hypo | cancer_general | LRP4-AS1 |
| chr11 | 46227561 | 46227654 | Hypo | cancer_general | — | chr11 | 46866293 | 46866510 | Hypo | cancer_general | NR1H3, DDB2, ACP2 |
| chr11 | 46959190 | 46959251 | Hypo | cancer_general | C11orf49 | chr11 | 47260168 | 47260258 | Hypo | breast | |
| chr11 | 47358926 | 47359237 | Hypo | cancer_general | MYBPC3 SP11, SLC39A13, MYBPC3 | chr11 | 47363557 | 47363625 | Hypo | head_neck | MYBPC3 CELF1, RAPSN |
| chr11 | 47372828 | 47373002 | Hypo | pancreas | | chr11 | 47478438 | 47478500 | Hypo | breast | |
| chr11 | 47485995 | 47486141 | Hypo | lung | CELF1 CLP1, ZDHHC5 | chr11 | 57235406 | 57235436 | Hypo | cancer_general | RTN4RL2 TMX2, C11orf31, BTBD18, TMX2-CTNND1 |
| chr11 | 57437157 | 57437234 | Hypo | cancer_general | | chr11 | 57500982 | 57501068 | Hypo | cancer_general | |
| chr11 | 59329086 | 59329240 | Hypo | cancer_general | TRNA_Lys, U7, TRNA_Leu, JB175310, TRNA_Phe | chr11 | 59841403 | 59841533 | Hypo | cancer_general | MS4A3 |
| chr11 | 60927079 | 60927319 | Hypo | cancer_general | VPS37C DDB1, VWCE | chr11 | 61049694 | 61049736 | Hypo | cancer_general | VWCE |
| chr11 | 61058283 | 61058341 | Hypo | cancer_general | | chr11 | 61148730 | 61148768 | Hypo | colorectal | — |
| chr11 | 61154806 | 61154836 | Hypo | cancer_general | TMEM216 RAB3IL1, FADS3 | chr11 | 61536985 | 61537014 | Hypo | literature | MYRF |
| chr11 | 61664655 | 61664770 | Hypo | cancer_general | | chr11 | 61666106 | 61666136 | Hypo | cancer_general | RAB3IL1, FADS3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 61811996 | 61812151 | Hypo | cancer_general | — | chr11 | 61880361 | 61880398 | Hypo | cancer_general | UBXN1, C11orf83, C11orf48, METTL12, SNORA57 |
| chr11 | 62370720 | 62370750 | Hypo | cancer_general | EML3, ROM1, MTA2 | chr11 | 62440509 | 62440588 | Hypo | cancer_general | TTC9C, HNRNPUL2 |
| chr11 | 62484517 | 62484547 | Hypo | breast | HNRNPUL2, GNG3 | chr11 | 62497600 | 62497630 | Hypo | cancer_general | — |
| chr11 | 62555752 | 62555782 | Hypo | cancer_general | NXF1, TMEM179B, TAF6L, TMEM223 | chr11 | 63202941 | 63203091 | Hypo | cancer_general | — |
| chr11 | 63431856 | 63431918 | Hypo | ovarian | ATL3 | chr11 | 63432139 | 63432218 | Hypo | ovarian | ATL3 |
| chr11 | 63609824 | 63610013 | Hypo | cancer_general | MARK2 | chr11 | 63641072 | 63641256 | Hypo | breast | MARK2 |
| chr11 | 63849394 | 63849426 | Hypo | cancer_general | MACROD1 | chr11 | 63934498 | 63934619 | Hypo | cancer_general | — |
| chr11 | 64105954 | 64106108 | Hypo | cancer_general | CCDC88B | chr11 | 64120879 | 64120909 | Hypo | cancer_general | RPS6KA4, CCDC88B |
| chr11 | 64140397 | 64140427 | Hypo | cancer_general | MIR1237, RPS6KA4 | chr11 | 64578577 | 64578743 | Hypo | cancer_general | MEN1, MAP4K2 |
| chr11 | 64796439 | 64796571 | Hypo | cancer_general | ARL2-SNX15, ARL2 | chr11 | 64809584 | 64809906 | Hypo | cancer_general | NAALADL1, SAC3D1, ARL2-SNX15 |
| chr11 | 64903331 | 64903361 | Hypo | cancer_general | SYVN1, MRPL49 | chr11 | 64950292 | 64950374 | Hypo | cancer_general | CAPN1, SPDYC |
| chr11 | 65091272 | 65091369 | Hypo | cancer_general | DPF2, CDC42EP2 | chr11 | 65364470 | 65364557 | Hypo | blood | MAP3K11, KCNK7, EHBP1L1 |
| chr11 | 65448943 | 65449022 | Hypo | cancer_general | — | chr11 | 65478376 | 65478611 | Hypo | cancer_general | KAT5, RNASEH2C |
| chr11 | 65510941 | 65511172 | Hypo | cancer_general | EIF1AD, AX747517, CST6, CATSPER1, BANF1 | chr11 | 65511392 | 65511522 | Hypo | cancer_general | — |
| chr11 | 65778952 | 65778981 | Hypo | literature | | chr11 | 65891131 | 65891227 | Hypo | cancer_general | PACS1 |
| chr11 | 66114279 | 66114331 | Hypo | cancer_general | TRNA_Ser, B3GNT1, BRMS1 | chr11 | 66138094 | 66138260 | Hypo | cancer_general | SLC29A2, AX747485 |
| chr11 | 66324254 | 66324447 | Hypo | cancer_general | CTSF, ACTN3 | chr11 | 66454424 | 66454454 | Hypo | head_neck | SPTBN2, RBM4B |
| chr11 | 66511223 | 66511431 | Hypo | cancer_general | C11orf80 | chr11 | 66513217 | 66513646 | Hypo | cancer_general | C11orf80 |
| chr11 | 66557543 | 66557710 | Hypo | cancer_general | C11orf80 | chr11 | 66625207 | 66625240 | Hypo | cancer_general | LRFN4, PC |
| chr11 | 66649028 | 66649058 | Hypo | cancer_general | — | chr11 | 66658224 | 66658290 | Hypo | ovarian | — |
| chr11 | 67072239 | 67072396 | Hypo | cancer_general | SSH3, ANKRD13D, AK057681 | chr11 | 67210017 | 67210057 | Hypo | cancer_general | GPR152, CABP4, CORO1B, PTPRCAP, RPS6KB2 |
| chr11 | 67248321 | 67248458 | Hypo | cancer_general | AIP | chr11 | 67462643 | 67462833 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 67764187 | 67764254 | Hypo | cancer_general | UNC93B1 | chr11 | 67781196 | 67781564 | Hypo | lung | ALDH3B1, UNC93B1 |
| chr11 | 67797202 | 67797420 | Hypo | cancer_general | ALDH3B1, NDUFS8, MIR4691, TCIRG1 | chr11 | 67918044 | 67918145 | Hypo | pancreas | SUV420H1 |
| chr11 | 67999703 | 67999866 | Hypo | cancer_general | — | chr11 | 68221758 | 68222056 | Hypo | cancer_general | PPP6R3, LRP5 |
| chr11 | 68409558 | 68409588 | Hypo | hepatobiliary | — | chr11 | 68804728 | 68804776 | Hypo | cancer_general | — |
| chr11 | 69192566 | 69192784 | Hypo | cancer_general | — | chr11 | 69280561 | 69280633 | Hypo | cancer_general | — |
| chr11 | 69466004 | 69466042 | Hypo | literature | BC133018, CCND1, AK294004, ORAOV1 | chr11 | 71192746 | 71192889 | Hypo | cancer_general | NADSYN1 |
| chr11 | 71647544 | 71647574 | Hypo | pancreas | RNF121, LOC100133315 | chr11 | 71792437 | 71792496 | Hypo | cancer_general | MIR3165, NUMA1, LRTOMT |
| chr11 | 71863650 | 71863785 | Hypo | cancer_general | — | chr11 | 72413980 | 72414010 | Hypo | ovarian | BC150585, ARAP1 |
| chr11 | 72475677 | 72475711 | Hypo | cancer_general | STARD10 | chr11 | 72532348 | 72532378 | Hypo | cancer_general | ATG16L2 |
| chr11 | 73072907 | 73072953 | Hypo | cancer_general | ARHGEF17 | chr11 | 73310367 | 73310441 | Hypo | cancer_general | FAM168A |
| chr11 | 73481055 | 73481085 | Hypo | ovarian | RAB6A UCP2, DNAJB13 | chr11 | 73561763 | 73561798 | Hypo | ovarian | MRPL48 |
| chr11 | 73685698 | 73685845 | Hypo | ovarian | LOC283214 | chr11 | 74246487 | 74246521 | Hypo | cancer_general | — |
| chr11 | 75459486 | 75459775 | Hypo | cancer_general | UVRAG | chr11 | 75858210 | 75858240 | Hypo | colorectal | UVRAG |
| chr11 | 75859012 | 75859053 | Hypo | colorectal | LRRC32 | chr11 | 76293588 | 76293618 | Hypo | head_neck | — |
| chr11 | 76371738 | 76372077 | Hypo | cancer_general | AAMDC, RSF1 | chr11 | 76594692 | 76594722 | Hypo | ovarian | ACER3 |
| chr11 | 77533964 | 77534145 | Hypo | cancer_general | PICALM | chr11 | 82998001 | 82998121 | Hypo | cancer_general | BC070093, CCDC90B |
| chr11 | 85709169 | 85709254 | Hypo | ovarian | PANX1 | chr11 | 89052235 | 89052282 | Hypo | cancer_general | NOX4 |
| chr11 | 93911651 | 93911800 | Hypo | colorectal | — | chr11 | 94275794 | 94275951 | Hypo | colorectal | PIWIL4, FUT4 |
| chr11 | 96517902 | 96517932 | Hypo | cancer_general | — | chr11 | 101723359 | 101723455 | Hypo | cancer_general | — |
| chr11 | 102158378 | 102158427 | Hypo | ovarian | C11orf65 | chr11 | 102961347 | 102961649 | Hypo | cancer_general | DCUN1D5 |
| chr11 | 108236072 | 108236101 | Hypo | literature | HSPB2, HSPB2-C11orf52, CRYAB | chr11 | 108603233 | 108603263 | Hypo | cancer_general | DDX10 |
| chr11 | 111783548 | 111783577 | Hypo | literature | | chr11 | 111976911 | 111976941 | Hypo | pancreas | — |
| chr11 | 116976126 | 116976156 | Hypo | cancer_general | — | chr11 | 116984568 | 116984665 | Hypo | cancer_general | — |
| chr11 | 117017686 | 117017773 | Hypo | ovarian | PAFAH1B2, AB231710, AB231711 | chr11 | 117055950 | 117056073 | Hypo | cancer_general | PAFAH1B2, SIDT2 |
| chr11 | 118724458 | 118724605 | Hypo | colorectal | — | chr11 | 118991033 | 118991079 | Hypo | cancer_general | HINFP, C2CD2L |
| chr11 | 119148865 | 119148945 | Hypo | literature | CBL | chr11 | 119149236 | 119149265 | Hypo | literature | CBL |
| chr11 | 120008105 | 120008504 | Hypo | cancer_general | TRIM29 | chr11 | 120367948 | 120368008 | Hypo | ovarian | — |
| chr11 | 120998701 | 120998825 | Hypo | ovarian | TECTA | chr11 | 121152057 | 121152203 | Hypo | cancer_general | — |
| chr11 | 122895443 | 122895485 | Hypo | cancer_general | LOC341056 | chr11 | 122961054 | 122961219 | Hypo | cancer_general | CLMP |
| chr11 | 123963874 | 123963994 | Hypo | cancer_general | — | chr11 | 125220500 | 125220643 | Hypo | cancer_general | PKNOX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 125755612 | 125755710 | Hypo | cancer_general | HYLS1, PUS3 | chr11 | 125758604 | 125758660 | Hypo | cancer_general | PUS3, HYLS1 |
| chr11 | 128657892 | 128657970 | Hypo | cancer_general | — | chr11 | 129907552 | 129907714 | Hypo | cancer_general | — |
| chr11 | 129931742 | 129931851 | Hypo | cancer_general | APLP2 | chr11 | 130343061 | 130343100 | Hypo | hepatobiliary | ADAMTS15 |
| chr11 | 130359769 | 130359915 | Hypo | cancer_general | — | chr11 | 130781550 | 130781781 | Hypo | ovarian | SNX19 |
| chr11 | 130785487 | 130785622 | Hypo | cancer_general | SNX19 | chr11 | 130854324 | 130854490 | Hypo | cancer_general | — |
| chr11 | 131522763 | 131522947 | Hypo | cancer_general | — | chr11 | 131766715 | 131766960 | Hypo | cancer_general | AK056505 |
| chr11 | 132484215 | 132484404 | Hypo | cancer_general | — | chr11 | 133231739 | 133231832 | Hypo | cancer_general | SDHA |
| chr11 | 133792055 | 133792214 | Hypo | hepatobiliary | IGSF9B | chr5 | 230673 | 230709 | Hypo | breast | AHRR |
| chr5 | 303272 | 303301 | Hypo | literature | AHRR, PDCD6 | chr5 | 373363 | 373392 | Hypo | literature | — |
| chr5 | 415870 | 415899 | Hypo | literature | AHRR | chr5 | 481012 | 481121 | Hypo | cancer_general | SLC9A3, PP7080, AK023178, FLJ00157, BC013821 |
| chr5 | 491335 | 491536 | Hypo | cancer_general | — | chr5 | 538758 | 538806 | Hypo | cancer_general | MIR4456 |
| chr5 | 554299 | 554538 | Hypo | cancer_general | — | chr5 | 554871 | 554900 | Hypo | literature | — |
| chr5 | 555158 | 555285 | Hypo | cancer_general | — | chr5 | 555965 | 555995 | Hypo | cancer_general | — |
| chr5 | 677889 | 678006 | Hypo | literature | TPPP | chr5 | 909204 | 909304 | Hypo | head_neck | TRIP13 |
| chr5 | 912806 | 912835 | Hypo | literature | TRIP13 | chr5 | 1034600 | 1034653 | Hypo | cancer_general | NKD2 |
| chr5 | 1059523 | 1059556 | Hypo | blood | MIR4635, SLC12A7 | chr5 | 1117778 | 1118270 | Hypo | cancer_general | — |
| chr5 | 1131217 | 1131378 | Hypo | cancer_general | — | chr5 | 1136590 | 1136845 | Hypo | head_neck | — |
| chr5 | 1193381 | 1193521 | Hypo | cancer_general | SLC6A19 | chr5 | 1193880 | 1193944 | Hypo | cancer_general | SLC6A19 |
| chr5 | 1221197 | 1221307 | Hypo | cancer_general | SLC6A19, SLC6A18 | chr5 | 1259524 | 1259558 | Hypo | hepatobiliary | TERT |
| chr5 | 1271339 | 1271396 | Hypo | hepatobiliary | TERT | chr5 | 1295214 | 1295265 | Hypo | literature | TERT |
| chr5 | 1747022 | 1747098 | Hypo | cancer_general | — | chr5 | 1779526 | 1779556 | Hypo | hepatobiliary | — |
| chr5 | 1787378 | 1787418 | Hypo | cancer_general | — | chr5 | 1950794 | 1950960 | Hypo | cancer_general | — |
| chr5 | 2225439 | 2225469 | Hypo | lung | — | chr5 | 2324383 | 2324413 | Hypo | cancer_general | — |
| chr5 | 2367718 | 2367892 | Hypo | cancer_general | — | chr5 | 2541487 | 2541611 | Hypo | cancer_general | — |
| chr5 | 2753048 | 2753078 | Hypo | pancreas | C5orf38, IRX2 | chr5 | 3031879 | 3032018 | Hypo | cancer_general | — |
| chr5 | 3152146 | 3152176 | Hypo | hepatobiliary | — | chr5 | 3325042 | 3325272 | Hypo | cancer_general | — |
| chr5 | 3674053 | 3674224 | Hypo | cancer_general | — | chr5 | 4144367 | 4144516 | Hypo | cancer_general | UBE2QL1 |
| chr5 | 6228617 | 6228790 | Hypo | cancer_general | — | chr5 | 6482458 | 6482620 | Hypo | cancer_general | ANKRD33B |
| chr5 | 10249098 | 10249127 | Hypo | literature | CCT5, FAM173B | chr5 | 10616516 | 10616550 | Hypo | cancer_general | — |
| chr5 | 16466784 | 16467120 | Hypo | cancer_general | FAM134B, ZNF622 | chr5 | 16793851 | 16794008 | Hypo | hepatobiliary | MYO10 |
| chr5 | 16845452 | 16845619 | Hypo | hepatobiliary | MYO10 | chr5 | 16968118 | 16968148 | Hypo | hepatobiliary | — |
| chr5 | 17095895 | 17095927 | Hypo | hepatobiliary | — | chr5 | 17203012 | 17203177 | Hypo | cancer_general | LOC285696 |
| chr5 | 17311046 | 17311076 | Hypo | hepatobiliary | — | chr5 | 17512114 | 17512144 | Hypo | hepatobiliary | — |
| chr5 | 18034335 | 18034365 | Hypo | cancer_general | — | chr5 | 23011928 | 23011958 | Hypo | cancer_general | — |
| chr5 | 31572285 | 31572344 | Hypo | hepatobiliary | — | chr5 | 31691477 | 31691652 | Hypo | cancer_general | PDZD2 |
| chr5 | 31879243 | 31879282 | Hypo | hepatobiliary | PDZD2 | chr5 | 32042283 | 32042419 | Hypo | lung | — |
| chr5 | 32314345 | 32314379 | Hypo | cancer_general | MTMR12 | chr5 | 32333032 | 32333111 | Hypo | colorectal | — |
| chr5 | 32446143 | 32446274 | Hypo | cancer_general | ZFR | chr5 | 33234280 | 33234411 | Hypo | cancer_general | — |
| chr5 | 33298005 | 33298076 | Hypo | cancer_general | — | chr5 | 33509607 | 33509776 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 33936486 | 33936516 | Hypo | cancer_general | SLC45A2, RXFP3 | chr5 | 35874560 | 35874589 | Hypo | literature | IL7R |
| chr5 | 35939832 | 35939861 | Hypo | literature | CAPSL | chr5 | 37376644 | 37376674 | Hypo | cancer_general | WDR70, NUP155 |
| chr5 | 39281800 | 39281943 | Hypo | lung | C9 | chr5 | 39343181 | 39343348 | Hypo | cancer_general, esophageal, cancer_general | C9 |
| chr5 | 40775147 | 40775313 | Hypo | cancer_general | PRKAA1 | chr5 | 42260050 | 42260453 | Hypo | | |
| chr5 | 42931966 | 42931996 | Hypo | cancer_general | — | chr5 | 43215538 | 43215738 | Hypo | lung, cancer_general | NIM1 |
| chr5 | 43402678 | 43403084 | Hypo | cancer_general | CCL28 | chr5 | 43558065 | 43558099 | Hypo | cancer_general | PAIP1 |
| chr5 | 52887899 | 52888047 | Hypo | cancer_general | NDUFS4 | chr5 | 56077938 | 56078065 | Hypo | cancer_general | — |
| chr5 | 56467666 | 56467666 | Hypo | cancer_general | GPBP1 | chr5 | 65181732 | 65181778 | Hypo | cancer_general | — |
| chr5 | 67569803 | 67569832 | Hypo | literature | PIK3R1 | chr5 | 67588937 | 67589162 | Hypo | literature | PIK3R1 |
| chr5 | 67589598 | 67589627 | Hypo | literature | PIK3R1 | chr5 | 67590431 | 67590460 | Hypo | literature | PIK3R1 |
| chr5 | 67591068 | 67591157 | Hypo | literature | PIK3R1 | chr5 | 68391042 | 68391336 | Hypo | cancer_general | SLC30A5 |
| chr5 | 71106820 | 71107027 | Hypo | head_neck | — | chr5 | 72528434 | 72528464 | Hypo | cancer_general | — |
| chr5 | 74061571 | 74061786 | Hypo | cancer_general | NSA2, GFM2 | chr5 | 74991793 | 74991908 | Hypo | cancer_general | POC5 |
| chr5 | 76327468 | 76327697 | Hypo | cancer_general | AGGF1 | chr5 | 77655342 | 77655388 | Hypo | cancer_general | SCAMP1, BC039455 |
| chr5 | 78005726 | 78005913 | Hypo | cancer_general | — | chr5 | 78039632 | 78039673 | Hypo | head_neck | — |
| chr5 | 78910189 | 78910332 | Hypo | cancer_general | PAPD4 | chr5 | 79954097 | 79954169 | Hypo | colorectal | SERINC5 |
| chr5 | 79563425 | 79563643 | Hypo | cancer_general | — | chr5 | 79598681 | 79598836 | Hypo | cancer_general | LOC644936 |
| chr5 | 79783240 | 79783421 | Hypo | cancer_general | ZFYVE16, FAM151B | chr5 | 79947584 | 79947707 | Hypo | cancer_general | DHFR, MSH3, MTRNR2L2 |
| chr5 | 82168369 | 82168480 | Hypo | colorectal | — | chr5 | 86414242 | 86414297 | Hypo | cancer_general | BC034940, MIR4280 |
| chr5 | 87986547 | 87986581 | Hypo | pancreas | — | chr5 | 94889396 | 94889434 | Hypo | cancer_general | ARSK, TTC37 |
| chr5 | 94982042 | 94982225 | Hypo | cancer_general | RFESD, SPATA9 | chr5 | 96114587 | 96114632 | Hypo | breast | ERAP1, CAST |
| chr5 | 111987744 | 111987818 | Hypo | colorectal | — | chr5 | 112042844 | 112042873 | Hypo | literature | APC |
| chr5 | 112170808 | 112170837 | Hypo | literature | APC | chr5 | 112175198 | 112175227 | Hypo | literature | APC |
| chr5 | 112175640 | 112175669 | Hypo | literature | APC | chr5 | 112340666 | 112340704 | Hypo | head_neck | DCP2 |
| chr5 | 115154758 | 115154825 | Hypo | cancer_general | ATG12, CDO1 | chr5 | 115176039 | 115176228 | Hypo | cancer_general | ATG12, AP3S1 |
| chr5 | 116143271 | 116143325 | Hypo | hepatobiliary | — | chr5 | 120399966 | 120400129 | Hypo | cancer_general | — |
| chr5 | 124128410 | 124128497 | Hypo | colorectal | — | chr5 | 126231644 | 126231674 | Hypo | ovarian | 3-Mar |
| chr5 | 126245097 | 126245133 | Hypo | pancreas | 3-Mar | chr5 | 127088743 | 127088773 | Hypo | cancer_general | ARSK, TTC37 (LOC728637, ACSL6, FNIP1) |
| chr5 | 130153448 | 130153623 | Hypo | cancer_general | — | chr5 | 131134159 | 131134203 | Hypo | ovarian | LOC728637, ACSL6, FNIP1 |
| chr5 | 133820008 | 133820040 | Hypo | cancer_general | LOC340073, LOC100996485 | chr5 | 133968996 | 133969192 | Hypo | cancer_general | SAR1B |
| chr5 | 134582864 | 134582894 | Hypo | cancer_general | LOC100996485 | chr5 | 137404150 | 137404180 | Hypo | cancer_general | — |
| chr5 | 137912037 | 137912148 | Hypo | ovarian | — | chr5 | 138196197 | 138196408 | Hypo | head_neck | — |
| chr5 | 138273817 | 138273854 | Hypo | pancreas | SIL1, CTNNA1 | chr5 | 139454108 | 139454202 | Hypo | ovarian | LRRTM2, CTNNA1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 139779555 | 139779871 | Hypo | cancer_general | ANKHD1, ANKHD1-EIF4EBP3, BC030152 | chr5 | 147003444 | 147003536 | Hypo | cancer_general | JAKMIP2, JAKMIP2-AS1 |
| chr5 | 147326357 | 147326510 | Hypo | cancer_general | SYNPO | chr5 | 149503827 | 149503856 | Hypo | literature | PDGFRB |
| chr5 | 150029147 | 150029245 | Hypo | ovarian | — | chr5 | 154030048 | 154030160 | Hypo | cancer_general | — |
| chr5 | 154061801 | 154061894 | Hypo | cancer_general | MRPL22, GEMIN5 | chr5 | 154209926 | 154209987 | Hypo | cancer_general | FAXDC2 |
| chr5 | 154318148 | 154318329 | Hypo | cancer_general | | chr5 | 156485385 | 156485415 | Hypo | cancer_general | HAVCR1 |
| chr5 | 156558444 | 156558689 | Hypo | cancer_general | MED7 | chr5 | 156655170 | 156655200 | Hypo | cancer_general | ITK |
| chr5 | 156874257 | 156874308 | Hypo | cancer_general | ADAM19 | chr5 | 157078419 | 157078449 | Hypo | cancer_general | SOX30 |
| chr5 | 157673799 | 157673964 | Hypo | cancer_general | | chr5 | 158524865 | 158524925 | Hypo | cancer_general | AK123543, EBF1 |
| chr5 | 158612981 | 158613074 | Hypo | lung, cancer_general | RNF145 | chr5 | 159437197 | 159437235 | Hypo | cancer_general | TTC1 |
| chr5 | 166865449 | 166865616 | Hypo | cancer_general | TENM2 | chr5 | 168233396 | 168233482 | Hypo | cancer_general | SLIT3 |
| chr5 | 169366082 | 169366201 | Hypo | cancer_general | FAM196B, DOCK2 | chr5 | 169532927 | 169533012 | Hypo | cancer_general | FOXI1 |
| chr5 | 171352123 | 171352153 | Hypo | head_neck | FBXW11 | chr5 | 172354043 | 172354118 | Hypo | ovarian | ERGIC1 |
| chr5 | 172485539 | 172485586 | Hypo | cancer_general | CREBRF, Y_RNA | chr5 | 172672477 | 172672663 | Hypo | cancer_general | — |
| chr5 | 174159104 | 174159134 | Hypo | cancer_general | MSX2 ARL10, KIAA1191 | chr5 | 174921456 | 174921629 | Hypo | cancer_general | SFXN1 |
| chr5 | 175790961 | 175790991 | Hypo | ovarian | | chr5 | 175831257 | 175831326 | Hypo | cancer_general | CLTB |
| chr5 | 175876388 | 175876504 | Hypo | cancer_general | FAF2 | chr5 | 175971447 | 175971615 | Hypo | cancer_general | CDHR2 |
| chr5 | 175978889 | 175978976 | Hypo | cancer_general | CDHR2 | chr5 | 176295786 | 176295892 | Hypo | hepatobiliary | UNC5A |
| chr5 | 176520166 | 176520195 | Hypo | literature | FGFR4 | chr5 | 176522400 | 176522566 | Hypo | literature | FGFR4 |
| chr5 | 176764100 | 176764169 | Hypo | breast | LMAN2 | chr5 | 177020093 | 177020153 | Hypo | cancer_general | B4GALT7, TMED9 |
| chr5 | 177031167 | 177031197 | Hypo | cancer_general | B4GALT7, TMED9 | chr5 | 177408292 | 177408443 | Hypo | cancer_general | — |
| chr5 | 177512244 | 177512377 | Hypo | cancer_general | — | chr5 | 177556807 | 177557022 | Hypo | cancer_general | AK127224, N4BP3, RMND5B |
| chr5 | 177579824 | 177580065 | Hypo | cancer_general | NHP2, RMND5B | chr5 | 177644565 | 177644601 | Hypo | colorectal | AGXT2L2, HNRNPAB |
| chr5 | 177713376 | 177713468 | Hypo | cancer_general | — | chr5 | 178151333 | 178151363 | Hypo | hepatobiliary | ZNF354A |
| chr5 | 178576356 | 178576499 | Hypo | cancer_general | ADAMTS2 | chr5 | 178655753 | 178655871 | Hypo | cancer_general | ADAMTS2 |
| chr5 | 178781548 | 178781577 | Hypo | literature | ADAMTS2 | chr5 | 178955527 | 178955656 | Hypo | cancer_general | AX747985 |
| chr5 | 178969722 | 178969752 | Hypo | cancer_general | RUFY1 | chr5 | 178978946 | 178978976 | Hypo | cancer_general | RUFY1 |
| chr5 | 179060235 | 179060655 | Hypo | cancer_general | C5orf60 | chr5 | 179098595 | 179098633 | Hypo | cancer_general | CBY3 |
| chr5 | 179214113 | 179214196 | Hypo | cancer_general | LTC4S, MAML1 | chr5 | 179217377 | 179217447 | Hypo | esophageal | LTC4S, MGAT4B, MIR1229 |
| chr5 | 179270584 | 179270748 | Hypo | ovarian | AK095057, C5orf45, SQSTM1 | chr5 | 179553207 | 179553237 | Hypo | cancer_general | RASGEF1C |
| chr5 | 180030654 | 180030700 | Hypo | cancer_general | FLT4 | chr5 | 180047440 | 180047606 | Hypo | cancer_general | FLT4 |
| chr5 | 180326126 | 180326156 | Hypo | cancer_general | BTNL8 | chr5 | 180454232 | 180454334 | Hypo | cancer_general | — |

TABLE 11-continued

| chr | Start | Stop | Hypo/hyper | classification | annotation |
|---|---|---|---|---|---|
| chr5 | 180612346 | 180612376 | Hypo | cancer_general | TRNA_Leu, TRNA_Val, TRNA_Pro, TRNA_Thr, TRIM7 |
| chr5 | 180636016 | 180636205 | Hypo | cancer_general | TRNA_Ala, TRIM7, TRNA_Val, TRNA_Lys |
| HPV16 | 111 | 140 | Hypo | virus | — |
| HPV16 | 623 | 652 | Hypo | virus | — |
| HPV16 | 1135 | 1164 | Hypo | virus | — |
| HPV16 | 1647 | 1676 | Hypo | virus | — |
| HPV16 | 2159 | 2188 | Hypo | virus | — |
| HPV16 | 2671 | 2700 | Hypo | virus | — |
| HPV16 | 3183 | 3212 | Hypo | virus | — |
| HPV16 | 3695 | 3724 | Hypo | virus | — |
| HPV16 | 4207 | 4236 | Hypo | virus | — |
| HPV16 | 4719 | 4748 | Hypo | virus | — |
| HPV16 | 5231 | 5260 | Hypo | virus | — |
| HPV16 | 5743 | 5772 | Hypo | virus | — |
| HPV16 | 6255 | 6284 | Hypo | virus | — |
| HPV16 | 6767 | 6796 | Hypo | virus | — |
| HPV16 | 7279 | 7308 | Hypo | virus | — |
| chr13 | 20451144 | 20451360 | Hypo | cancer_general | — |
| chr13 | 23653781 | 23653813 | Hypo | hepatobiliary | PABPC3 |
| chr13 | 25668799 | 25668829 | Hypo | cancer_general | USP12 |
| chr13 | 27699893 | 27699981 | Hypo | cancer_general | FLT3 |
| chr13 | 28589765 | 28589794 | Hypo | literature | FLT3 |
| chr13 | 28601345 | 28601374 | Hypo | literature | FLT3 |
| chr13 | 28608233 | 28608355 | Hypo | literature | PAN3-AS1, PAN3 |
| chr13 | 28706016 | 28706140 | Hypo | cancer_general | — |
| chr13 | 30141688 | 30141718 | Hypo | cancer_general | SLC7A1 |
| chr13 | 31185432 | 31185548 | Hypo | blood | USPL1 |
| chr13 | 36269480 | 36269509 | Hypo | literature | — |
| chr13 | 36553399 | 36553428 | Hypo | literature | — |
| chr13 | 36909206 | 36909236 | Hypo | hepatobiliary | SPG20 |
| chr13 | 38402239 | 38402268 | Hypo | literature | TRPC4 |
| chr13 | 41346048 | 41346088 | Hypo | cancer_general | MRPS31 |
| chr13 | 41884500 | 41884688 | Hypo | cancer_general | NAA16 |
| chr13 | 45905088 | 45905264 | Hypo | cancer_general | TPT1, SNORA31, DL489966, D28408 |
| chr13 | 46660839 | 46660869 | Hypo | cancer_general | CPB2, CPB2-AS1 |
| chr13 | 47472315 | 47472344 | Hypo | literature | HTR2A |
| chr13 | 48478576 | 48478605 | Hypo | literature | — |
| chr5 | 180629320 | 180629350 | Hypo | cancer_general | TRIM7, TRNA_Ala, TRNA_Lys |
| JH636052.4 | 2022736 | 2022766 | Hypo | cancer_general | — |
| HPV16 | 367 | 396 | Hypo | virus | — |
| HPV16 | 879 | 908 | Hypo | virus | — |
| HPV16 | 1391 | 1420 | Hypo | virus | — |
| HPV16 | 1903 | 1932 | Hypo | virus | — |
| HPV16 | 2415 | 2444 | Hypo | virus | — |
| HPV16 | 2927 | 2956 | Hypo | virus | — |
| HPV16 | 3439 | 3468 | Hypo | virus | — |
| HPV16 | 3951 | 3980 | Hypo | virus | — |
| HPV16 | 4463 | 4492 | Hypo | virus | — |
| HPV16 | 4975 | 5004 | Hypo | virus | — |
| HPV16 | 5487 | 5516 | Hypo | virus | — |
| HPV16 | 5999 | 6028 | Hypo | virus | — |
| HPV16 | 6511 | 6540 | Hypo | virus | — |
| HPV16 | 7023 | 7052 | Hypo | virus | — |
| HPV16 | 7535 | 7564 | Hypo | virus | — |
| chr13 | 21713233 | 21713513 | Hypo | cancer_general | SAP18 |
| chr13 | 24099683 | 24099713 | Hypo | hepatobiliary | — |
| chr13 | 26340608 | 26340755 | Hypo | cancer_general | ATP8A2 |
| chr13 | 28239909 | 28240164 | Hypo | breast | — |
| chr13 | 28592605 | 28592658 | Hypo | literature | FLT3 |
| chr13 | 28602326 | 28602355 | Hypo | literature | FLT3 |
| chr13 | 28610123 | 28610152 | Hypo | literature | FLT3 |
| chr13 | 29112395 | 29112444 | Hypo | hepatobiliary | — |
| chr13 | 30707569 | 30707599 | Hypo | cancer_general | HSPH1 |
| chr13 | 31742953 | 31743177 | Hypo | cancer_general | — |
| chr13 | 36541300 | 36541329 | Hypo | literature | — |
| chr13 | 36588100 | 36588129 | Hypo | literature | — |
| chr13 | 37643942 | 37644005 | Hypo | cancer_general | LHFP |
| chr13 | 40000498 | 40000528 | Hypo | hepatobiliary | ELF1, SUGT1P3 |
| chr13 | 41496324 | 41496478 | Hypo | cancer_general | DNAJC15, CPB2, CPB2-AS1 |
| chr13 | 43620862 | 43621006 | Hypo | colorectal | — |
| chr13 | 46649031 | 46649141 | Hypo | pancreas | — |
| chr13 | 47407767 | 47407796 | Hypo | literature | HTR2A |
| chr13 | 47526030 | 47526182 | Hypo | cancer_general | — |
| chr13 | 48667877 | 48667907 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 50266473 | 50266573 | Hypo | cancer_general | KPNA3, EBPL | chr13 | 50367946 | 50368123 | Hypo | cancer_general | KPNA3 |
| chr13 | 50421504 | 50421696 | Hypo | esophageal | — | chr13 | 50639705 | 50639799 | Hypo | head_neck | DLEU2 |
| chr13 | 52270175 | 52270175 | Hypo | cancer_general | WDFY2 | chr13 | 52265068 | 52565194 | Hypo | cancer_general | — |
| chr13 | 52580318 | 52580369 | Hypo | cancer_general | UTP14C, ALG11 | chr13 | 55146522 | 55146551 | Hypo | literature | — |
| chr13 | 55373897 | 55373926 | Hypo | literature | — | chr13 | 55628658 | 55628687 | Hypo | literature | PRR20D |
| chr13 | 56762456 | 56762485 | Hypo | literature | — | chr13 | 57714539 | 57714568 | Hypo | literature | — |
| chr13 | 58892774 | 58892803 | Hypo | literature | — | chr13 | 59531686 | 59531715 | Hypo | literature | — |
| chr13 | 62132346 | 62132375 | Hypo | literature | — | chr13 | 64650200 | 64650229 | Hypo | literature | — |
| chr13 | 65532258 | 65532287 | Hypo | literature | — | chr13 | 66697959 | 66698124 | Hypo | hepatobiliary | — |
| chr13 | 67196371 | 67196400 | Hypo | literature | U7 | chr13 | 67197158 | 67197187 | Hypo | literature | U7 |
| chr13 | 68488923 | 68488952 | Hypo | literature | — | chr13 | 68682015 | 68682044 | Hypo | literature | — |
| chr13 | 68745282 | 68745311 | Hypo | literature | — | chr13 | 69796842 | 69796871 | Hypo | literature | — |
| chr13 | 71498386 | 71498415 | Hypo | literature | — | chr13 | 73184723 | 73184752 | Hypo | literature | — |
| chr13 | 73336049 | 73336078 | Hypo | literature | DIS3, BORA | chr13 | 73619660 | 73619784 | Hypo | colorectal | KLF5 |
| chr13 | 76440730 | 76440760 | Hypo | colorectal | C13orf45, AK123459 | chr13 | 76869421 | 76869450 | Hypo | literature | — |
| chr13 | 77553779 | 77553809 | Hypo | cancer_general | — | chr13 | 79693095 | 79693124 | Hypo | literature | — |
| chr13 | 79993101 | 79993142 | Hypo | lung | RBM26-AS1 | chr13 | 87731371 | 87731400 | Hypo | literature | — |
| chr13 | 88629123 | 88629152 | Hypo | literature | — | chr13 | 88788883 | 88788912 | Hypo | cancer_general | — |
| chr13 | 88997906 | 88997935 | Hypo | literature | — | chr13 | 89815436 | 89815465 | Hypo | literature | — |
| chr13 | 90015503 | 90015532 | Hypo | literature | — | chr13 | 90015897 | 90015926 | Hypo | literature | — |
| chr13 | 91755723 | 91755837 | Hypo | hepatobiliary | — | chr13 | 91948489 | 91948519 | Hypo | cancer_general | GPC6 |
| chr13 | 93859304 | 93859333 | Hypo | literature | — | chr13 | 94107209 | 94107238 | Hypo | literature | — |
| chr13 | 95086143 | 95086172 | Hypo | literature | DCT | chr13 | 96031705 | 96031815 | Hypo | cancer_general | — |
| chr13 | 96177285 | 96177315 | Hypo | head_neck | CLDN10-AS1, CLDN10 | chr13 | 97761876 | 97761925 | Hypo | pancreas | — |
| chr13 | 99851676 | 99851706 | Hypo | cancer_general | UBAC2-AS1, UBAC2, 7SK | chr13 | 102197373 | 102197408 | Hypo | cancer_general | ITGBL1 |
| chr13 | 103821419 | 103821448 | Hypo | literature | FAM155A | chr13 | 105484285 | 105484314 | Hypo | literature | — |
| chr13 | 107827301 | 107827331 | Hypo | hepatobiliary | ABHD13, LIG4 | chr13 | 108816328 | 108816383 | Hypo | cancer_general | — |
| chr13 | 108869613 | 108869830 | Hypo | cancer_general | CARKD | chr13 | 110434451 | 110434593 | Hypo | cancer_general | IRS2 |
| chr13 | 111278255 | 111278426 | Hypo | cancer_general | — | chr13 | 111363787 | 111363972 | Hypo | cancer_general | ING1, DJ031140, CARS2 |
| chr13 | 112272991 | 112273088 | Hypo | cancer_general | — | chr13 | 112712499 | 112712582 | Hypo | cancer_general | SOX1 |
| chr13 | 112758274 | 112758426 | Hypo | cancer_general | AK055145 | chr13 | 113598618 | 113598851 | Hypo | cancer_general | BC035340 |
| chr13 | 113938542 | 113938603 | Hypo | cancer_general | — | chr13 | 113985679 | 113986053 | Hypo | cancer_general | GRTP1, LAMP1 |
| chr13 | 114055983 | 114056137 | Hypo | literature, cancer_general | — | chr13 | 114060064 | 114060333 | Hypo | cancer_general | — |
| chr13 | 114074768 | 114074853 | Hypo | cancer_general | ADPRHL1 | chr13 | 114082984 | 114083014 | Hypo | breast | ADPRHL1 |
| chr13 | 114123168 | 114123291 | Hypo | cancer_general | DCUN1D2 | chr13 | 114189737 | 114189809 | Hypo | colorectal | TMCO3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 114221622 | 114221652 | Hypo | cancer_general | — | chr13 | 114304565 | 114304927 | Hypo | cancer_general | ATP4B, TFDP1 |
| chr13 | 114479404 | 114479434 | Hypo | cancer_general | TMEM255B | chr13 | 114498017 | 114498260 | Hypo | cancer_general | TMEM255B |
| chr13 | 114568046 | 114568076 | Hypo | cancer_general | LOC100506394 | chr13 | 114748342 | 114748638 | Hypo | cancer_general | RASA3 |
| chr13 | 114766270 | 114766300 | Hypo | ovarian | RASA3 | chr13 | 114780561 | 114781061 | Hypo | cancer_general | RASA3 |
| chr13 | 114807617 | 114807815 | Hypo | head_neck, cancer_general | RASA3 | chr13 | 114855635 | 114855669 | Hypo | cancer_general | — |
| EBV-B95-8 | 114862308 | 114862368 | Hypo | cancer_general | — | chr13 | 114961823 | 114961933 | Hypo | cancer_general | — |
| EBV-B95-8 | 967 | 996 | Hypo | virus | — | EBV-B95-8 | 3766 | 3795 | Hypo | virus | — |
| EBV-B95-8 | 4234 | 4263 | Hypo | virus | — | EBV-B95-8 | 5326 | 5355 | Hypo | virus | — |
| EBV-B95-8 | 6553 | 6582 | Hypo | virus | — | EBV-B95-8 | 8800 | 8829 | Hypo | virus | — |
| EBV-B95-8 | 13471 | 13500 | Hypo | virus | — | EBV-B95-8 | 46577 | 46606 | Hypo | virus | — |
| EBV-B95-8 | 48222 | 48251 | Hypo | virus | — | EBV-B95-8 | 52842 | 52871 | Hypo | virus | — |
| EBV-B95-8 | 53561 | 53590 | Hypo | virus | — | EBV-B95-8 | 54377 | 54406 | Hypo | virus | — |
| EBV-B95-8 | 54778 | 54807 | Hypo | virus | — | EBV-B95-8 | 55067 | 55096 | Hypo | virus | — |
| EBV-B95-8 | 55893 | 55922 | Hypo | virus | — | EBV-B95-8 | 56735 | 56764 | Hypo | virus | — |
| EBV-B95-8 | 58227 | 58256 | Hypo | virus | — | EBV-B95-8 | 58926 | 58955 | Hypo | virus | — |
| EBV-B95-8 | 59581 | 59610 | Hypo | virus | — | EBV-B95-8 | 60099 | 60128 | Hypo | virus | — |
| EBV-B95-8 | 60877 | 60906 | Hypo | virus | — | EBV-B95-8 | 61319 | 61348 | Hypo | virus | — |
| EBV-B95-8 | 62302 | 62331 | Hypo | virus | — | EBV-B95-8 | 62840 | 62869 | Hypo | virus | — |
| EBV-B95-8 | 63178 | 63207 | Hypo | virus | — | EBV-B95-8 | 63601 | 63630 | Hypo | virus | — |
| EBV-B95-8 | 63935 | 63964 | Hypo | virus | — | EBV-B95-8 | 64590 | 64619 | Hypo | virus | — |
| EBV-B95-8 | 66726 | 66755 | Hypo | virus | — | EBV-B95-8 | 67486 | 67515 | Hypo | virus | — |
| EBV-B95-8 | 67857 | 67886 | Hypo | virus | — | EBV-B95-8 | 69228 | 69257 | Hypo | virus | — |
| EBV-B95-8 | 69798 | 69827 | Hypo | virus | — | EBV-B95-8 | 70439 | 70468 | Hypo | virus | — |
| EBV-B95-8 | 70839 | 70868 | Hypo | virus | — | EBV-B95-8 | 71938 | 71967 | Hypo | virus | — |
| EBV-B95-8 | 72204 | 72233 | Hypo | virus | — | EBV-B95-8 | 72535 | 72564 | Hypo | virus | — |
| EBV-B95-8 | 72983 | 73012 | Hypo | virus | — | EBV-B95-8 | 73950 | 73979 | Hypo | virus | — |
| EBV-B95-8 | 74304 | 74333 | Hypo | virus | — | EBV-B95-8 | 74689 | 74718 | Hypo | virus | — |
| EBV-B95-8 | 74978 | 75007 | Hypo | virus | — | EBV-B95-8 | 75256 | 75285 | Hypo | virus | — |
| EBV-B95-8 | 77784 | 77813 | Hypo | virus | — | EBV-B95-8 | 79618 | 79647 | Hypo | virus | — |
| EBV-B95-8 | 80289 | 80318 | Hypo | virus | — | EBV-B95-8 | 80704 | 80733 | Hypo | virus | — |
| EBV-B95-8 | 81198 | 81227 | Hypo | virus | — | EBV-B95-8 | 81629 | 81658 | Hypo | virus | — |
| EBV-B95-8 | 81888 | 81917 | Hypo | virus | — | EBV-B95-8 | 82225 | 82254 | Hypo | virus | — |
| EBV-B95-8 | 82703 | 82732 | Hypo | virus | — | EBV-B95-8 | 83438 | 83467 | Hypo | virus | — |
| EBV-B95-8 | 85345 | 85374 | Hypo | virus | — | EBV-B95-8 | 86299 | 86328 | Hypo | virus | — |
| EBV-B95-8 | 87104 | 87133 | Hypo | virus | — | EBV-B95-8 | 89959 | 89988 | Hypo | virus | — |
| EBV-B95-8 | 90915 | 90944 | Hypo | virus | — | EBV-B95-8 | 92531 | 92560 | Hypo | virus | — |
| EBV-B95-8 | 94071 | 94100 | Hypo | virus | — | EBV-B95-8 | 94731 | 94760 | Hypo | virus | — |
| EBV-B95-8 | 95084 | 95113 | Hypo | virus | — | EBV-B95-8 | 97482 | 97511 | Hypo | virus | — |
| EBV-B95-8 | 98245 | 98274 | Hypo | virus | — | EBV-B95-8 | 99224 | 99253 | Hypo | virus | — |
| EBV-B95-8 | 100235 | 100264 | Hypo | virus | — | EBV-B95-8 | 101009 | 101038 | Hypo | virus | — |
| EBV-B95-8 | 102716 | 102745 | Hypo | virus | — | EBV-B95-8 | 104004 | 104033 | Hypo | virus | — |
| EBV-B95-8 | 105019 | 105048 | Hypo | virus | — | EBV-B95-8 | 105284 | 105313 | Hypo | virus | — |
| EBV-B95-8 | 107231 | 107260 | Hypo | virus | — | EBV-B95-8 | 108023 | 108052 | Hypo | virus | — |
| EBV-B95-8 | 108370 | 108399 | Hypo | virus | — | EBV-B95-8 | 109086 | 109115 | Hypo | virus | — |
| EBV-B95-8 | 110250 | 110279 | Hypo | virus | — | EBV-B95-8 | 110626 | 110655 | Hypo | virus | — |
| EBV-B95-8 | 111690 | 111719 | Hypo | virus | — | EBV-B95-8 | 112112 | 112141 | Hypo | virus | — |
| EBV-B95-8 | 114429 | 114458 | Hypo | virus | — | EBV-B95-8 | 114749 | 114778 | Hypo | virus | — |
| EBV-B95-8 | 115006 | 115035 | Hypo | virus | — | EBV-B95-8 | 115597 | 115626 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| EBV-B95-8 | 116382 | 116411 | Hypo | virus | — | EBV-B95-8 | 116649 | 116678 | Hypo | virus | — |
| EBV-B95-8 | 118647 | 118676 | Hypo | virus | — | EBV-B95-8 | 119542 | 119571 | Hypo | virus | — |
| EBV-B95-8 | 120350 | 120379 | Hypo | virus | — | EBV-B95-8 | 121382 | 121411 | Hypo | virus | — |
| EBV-B95-8 | 123037 | 123066 | Hypo | virus | — | EBV-B95-8 | 123570 | 123599 | Hypo | virus | — |
| EBV-B95-8 | 124913 | 124942 | Hypo | virus | — | EBV-B95-8 | 125376 | 125405 | Hypo | virus | — |
| EBV-B95-8 | 125805 | 125834 | Hypo | virus | — | EBV-B95-8 | 126337 | 126366 | Hypo | virus | — |
| EBV-B95-8 | 127493 | 127522 | Hypo | virus | — | EBV-B95-8 | 127905 | 127934 | Hypo | virus | — |
| EBV-B95-8 | 128805 | 128834 | Hypo | virus | — | EBV-B95-8 | 130244 | 130273 | Hypo | virus | — |
| EBV-B95-8 | 130690 | 130719 | Hypo | virus | — | EBV-B95-8 | 131603 | 131632 | Hypo | virus | — |
| EBV-B95-8 | 134325 | 134354 | Hypo | virus | — | EBV-B95-8 | 135032 | 135061 | Hypo | virus | — |
| EBV-B95-8 | 135599 | 135628 | Hypo | virus | — | EBV-B95-8 | 136148 | 136177 | Hypo | virus | — |
| EBV-B95-8 | 136680 | 136709 | Hypo | virus | — | EBV-B95-8 | 137805 | 137834 | Hypo | virus | — |
| EBV-B95-8 | 138375 | 138404 | Hypo | virus | — | EBV-B95-8 | 139745 | 139774 | Hypo | virus | — |
| EBV-B95-8 | 140610 | 140639 | Hypo | virus | — | EBV-B95-8 | 141137 | 141166 | Hypo | virus | — |
| EBV-B95-8 | 142290 | 142319 | Hypo | virus | — | EBV-B95-8 | 142763 | 142792 | Hypo | virus | — |
| EBV-B95-8 | 143078 | 143107 | Hypo | virus | — | EBV-B95-8 | 144318 | 144347 | Hypo | virus | — |
| EBV-B95-8 | 145216 | 145245 | Hypo | virus | — | EBV-B95-8 | 145638 | 145667 | Hypo | virus | — |
| EBV-B95-8 | 147044 | 147073 | Hypo | virus | — | EBV-B95-8 | 148404 | 148433 | Hypo | virus | — |
| EBV-B95-8 | 150099 | 150128 | Hypo | virus | — | EBV-B95-8 | 150443 | 150472 | Hypo | virus | — |
| EBV-B95-8 | 152230 | 152259 | Hypo | virus | — | EBV-B95-8 | 153127 | 153156 | Hypo | virus | — |
| EBV-B95-8 | 153468 | 153497 | Hypo | virus | — | EBV-B95-8 | 153800 | 153829 | Hypo | virus | — |
| EBV-B95-8 | 154204 | 154233 | Hypo | virus | — | EBV-B95-8 | 156501 | 156530 | Hypo | virus | — |
| EBV-B95-8 | 156773 | 156802 | Hypo | virus | — | EBV-B95-8 | 157345 | 157374 | Hypo | virus | — |
| EBV-B95-8 | 159211 | 159240 | Hypo | virus | — | EBV-B95-8 | 159561 | 159590 | Hypo | virus | — |
| EBV-B95-8 | 161193 | 161222 | Hypo | virus | — | EBV-B95-8 | 161698 | 161727 | Hypo | virus | — |
| EBV-B95-8 | 162343 | 162372 | Hypo | virus | — | EBV-B95-8 | 163798 | 163827 | Hypo | virus | — |
| EBV-B95-8 | 164471 | 164500 | Hypo | virus | — | EBV-B95-8 | 165234 | 165263 | Hypo | virus | — |
| EBV-B95-8 | 166280 | 166309 | Hypo | virus | — | EBV-B95-8 | 167347 | 167376 | Hypo | virus | — |
| EBV-B95-8 | 167600 | 167629 | Hypo | virus | — | EBV-B95-8 | 167942 | 167971 | Hypo | virus | — |
| EBV-B95-8 | 168551 | 168580 | Hypo | virus | — | EBV-B95-8 | 171304 | 171333 | Hypo | virus | — |
| HBV | 111 | 140 | Hypo | virus | — | HBV | 381 | 410 | Hypo | virus | — |
| HBV | 651 | 680 | Hypo | virus | — | HBV | 921 | 950 | Hypo | virus | — |
| HBV | 1191 | 1220 | Hypo | virus | — | HBV | 1461 | 1490 | Hypo | virus | — |
| HBV | 1731 | 1760 | Hypo | virus | — | HBV | 2001 | 2030 | Hypo | virus | — |
| HBV | 2271 | 2300 | Hypo | virus | — | HBV | 2541 | 2570 | Hypo | virus | — |
| HBV | 2811 | 2840 | Hypo | virus | — | chrX | 3631506 | 3631633 | Hypo | breast | PRKX INE2, CA5B, ZRSR2 |
| chrX | 3746612 | 3746642 | Hypo | head_neck | TRNA_Ile, LOC389906 | chrX | 15807465 | 15807693 | Hypo | cancer_general | RPS6KA3, SCARNA9L, EIF1AX |
| chrX | 20148710 | 20148739 | Hypo | literature | SCARNA9L, EIF1AX | chrX | 20160594 | 20160914 | Hypo | cancer_general | RBM10 |
| chrX | 44730179 | 44730271 | Hypo | cancer_general | KDM6A | chrX | 47039370 | 47039399 | Hypo | literature | SYN1, ARAF |
| chrX | 47426106 | 47426144 | Hypo | literature | SYN1, ARAF | chrX | 47426780 | 47426821 | Hypo | literature | AR |
| chrX | 66931448 | 66931477 | Hypo | literature | AR | chrX | 66937356 | 66937385 | Hypo | literature | AR |
| chrX | 66943529 | 66943567 | Hypo | literature | AR | chrX | 70339239 | 70339268 | Hypo | literature | MED12, IL2RG |
| chrX | 100228394 | 100228431 | Hypo | head_neck | ARL13A | chr15 | 22822348 | 22822488 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 23035709 | 23035781 | Hypo | cancer_general | NIPA1, NIPA2 | chr15 | 23162337 | 23162372 | Hypo | cancer_general | — |
| chr15 | 23273146 | 23273330 | Hypo | cancer_general | HERC2P2, JB175342, DQ572979 | chr15 | 23692316 | 23692453 | Hypo | cancer_general | LOC283685, GOLGA6L2 |
| chr15 | 29452432 | 29452462 | Hypo | hepatobiliary | FAM189A1 | chr15 | 31455370 | 31455485 | Hypo | cancer_general | NOP10, NUTM1, SLC12A6 |
| chr15 | 33879242 | 33879272 | Hypo | cancer_general | RYR3 | chr15 | 34630515 | 34630544 | Hypo | tcga | |
| chr15 | 34630818 | 34630865 | Hypo | cancer_general | NOP10, NUTM1, SLC12A6 | chr15 | 34879708 | 34879866 | Hypo | cancer_general | — |
| chr15 | 35310631 | 35310868 | Hypo | literature | KNSTRN RPUSD2, C15orf57 | chr15 | 40671495 | 40671620 | Hypo | ovarian | KNSTRN, DISP2 |
| chr15 | 40675092 | 40675121 | Hypo | literature | | chr15 | 40782219 | 40782249 | Hypo | breast | |
| chr15 | 40856224 | 40856254 | Hypo | cancer_general | | chr15 | 40877650 | 40877714 | Hypo | cancer_general | TRNA_Ser, CASC5 |
| chr15 | 41165245 | 41165700 | Hypo | cancer_general | RHOV | chr15 | 41541844 | 41541874 | Hypo | cancer_general | CHP1 |
| chr15 | 41693679 | 41693794 | Hypo | cancer_general | NDUFAF1 | chr15 | 41708225 | 41708305 | Hypo | cancer_general | RTF1 |
| chr15 | 41732398 | 41732471 | Hypo | breast | RTF1 | chr15 | 41835548 | 41835720 | Hypo | cancer_general | |
| chr15 | 42749733 | 42749899 | Hypo | literature | ZNF106 | chr15 | 42866975 | 42867049 | Hypo | cancer_general | STARD9, HAUS2 |
| chr15 | 43551059 | 43551196 | Hypo | esophageal | | chr15 | 44037568 | 44037699 | Hypo | cancer_general | PDIA3, CATSPER2P1 |
| chr15 | 45444061 | 45444141 | Hypo | ovarian | DUOX1 | chr15 | 46021437 | 46021467 | Hypo | pancreas | |
| chr15 | 50450454 | 50450574 | Hypo | head_neck | | chr15 | 50464583 | 50464622 | Hypo | cancer_general | SLC27A2 |
| chr15 | 51146606 | 51146636 | Hypo | cancer_general | AK091906 | chr15 | 52000818 | 52000937 | Hypo | cancer_general | SCG3 |
| chr15 | 54642236 | 54642352 | Hypo | literature, cancer_general | UNC13C | chr15 | 55452761 | 55452993 | Hypo | cancer_general | |
| chr15 | 55610440 | 55610698 | Hypo | cancer_general | PIGB, HP06981 | chr15 | 55699089 | 55699164 | Hypo | cancer_general | FLJ27352, DYX1C1, DYX1C1-CCPG1 |
| chr15 | 55806758 | 55806900 | Hypo | cancer_general | DYX1C1, unknown, FAM63B | chr15 | 56832508 | 56832546 | Hypo | cancer_general | BC037892 |
| chr15 | 59158488 | 59158537 | Hypo | cancer_general | | chr15 | 59158781 | 59158848 | Hypo | cancer_general | FAM63B, unknown |
| chr15 | 59950198 | 59950363 | Hypo | cancer_general | BNIP2, GTF2A2 | chr15 | 60084984 | 60085014 | Hypo | cancer_general | |
| chr15 | 60705106 | 60705204 | Hypo | breast | NARG2 | chr15 | 64109724 | 64109788 | Hypo | cancer_general | HERC1 |
| chr15 | 64618655 | 64618813 | Hypo | cancer_general | CSNK1G1 | chr15 | 64649481 | 64649553 | Hypo | cancer_general | KIAA0101, CSNK1G1 |
| chr15 | 65118954 | 65118984 | Hypo | cancer_general | PIF1 | chr15 | 65119265 | 65119295 | Hypo | cancer_general | PIF1 |
| chr15 | 65119499 | 65119632 | Hypo | cancer_general | PIF1 | chr15 | 65436137 | 65436213 | Hypo | ovarian | CLPX, PDCD7 |
| chr15 | 65685591 | 65685708 | Hypo | cancer_general | IGDCC4 | chr15 | 65823926 | 65824103 | Hypo | cancer_general | PTPLAD1 |
| chr15 | 65826189 | 65826359 | Hypo | cancer_general | PTPLAD1 | chr15 | 65862004 | 65862121 | Hypo | lung, cancer_general | VWA9, PTPLAD1 |
| chr15 | 66113240 | 66113270 | Hypo | head_neck | MAP2K1 | chr15 | 66649915 | 66649945 | Hypo | cancer_general | |
| chr15 | 66727409 | 66727498 | Hypo | literature | | chr15 | 66729148 | 66729177 | Hypo | literature | MAP2K1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 66774117 | 66774203 | Hypo | literature | SNAPC5, MAP2K1 | chr15 | 66789220 | 66789321 | Hypo | cancer_general | SNAPC5, MAP2K1, RPL4, SNORD18C, SNORD18B, SNORD16, SNORD18A, ZWILCH |
| chr15 | 66963816 | 66963871 | Hypo | cancer_general | hCG_2003567 | chr15 | 67146145 | 67146431 | Hypo | cancer_general | BX538221 |
| chr15 | 67545536 | 67545566 | Hypo | cancer_general | IQCH, AAGAB | chr15 | 72411929 | 72412176 | Hypo | cancer_general | SENP8, MYO9A |
| chr15 | 72743741 | 72743796 | Hypo | cancer_general | — | chr15 | 72979757 | 72979873 | Hypo | cancer_general | HIGD2B, BBS4 |
| chr15 | 74686021 | 74686051 | Hypo | cancer_general | — | chr15 | 74818772 | 74818806 | Hypo | pancreas | — |
| chr15 | 74903896 | 74903926 | Hypo | cancer_general | AK095335, CLK3 | chr15 | 74906463 | 74906493 | Hypo | cancer_general | CLK3, AK095335 |
| chr15 | 75205413 | 75205481 | Hypo | cancer_general | COX5A, FAM219B | chr15 | 75412459 | 75412714 | Hypo | cancer_general | — |
| chr15 | 77448873 | 77449001 | Hypo | cancer_general | PEAK1 | chr15 | 78501806 | 78501942 | Hypo | cancer_general | ACSBG1 |
| chr15 | 78595791 | 78596218 | Hypo | cancer_general | WDR61 | chr15 | 78859435 | 78859603 | Hypo | cancer_general | CHRNA5 |
| chr15 | 79151898 | 79152007 | Hypo | cancer_general | TRNA_Lys | chr15 | 80216803 | 80216884 | Hypo | cancer_general | C15orf37, ST20 |
| chr15 | 83314048 | 83314106 | Hypo | cancer_general | LOC283692 | chr15 | 83622512 | 83622565 | Hypo | ovarian | BC044934, HOMER2 |
| chr15 | 83655843 | 83655934 | Hypo | cancer_general | C15orf40, FAM103A1, BC044934 | chr15 | 83866523 | 83866559 | Hypo | cancer_general | HDGFRP3 |
| chr15 | 84711204 | 84711367 | Hypo | cancer_general | — | chr15 | 85142994 | 85143054 | Hypo | cancer_general | ZSCAN2 |
| chr15 | 85886518 | 85886604 | Hypo | cancer_general | — | chr15 | 86002524 | 86002690 | Hypo | cancer_general | AKAP13 |
| chr15 | 90631823 | 90631948 | Hypo | literature | IDH2 | chr15 | 90667461 | 90667586 | Hypo | colorectal | — |
| chr15 | 90703262 | 90703345 | Hypo | cancer_general | — | chr15 | 90755916 | 90756079 | Hypo | cancer_general | SEMA4B |
| chr15 | 93158592 | 93158739 | Hypo | cancer_general | FAM174B, DQ589911, DQ571124, DQ574028, DQ593762 | chr15 | 93350668 | 93350698 | Hypo | lung | — |
| chr15 | 93364552 | 93364624 | Hypo | cancer_general | — | chr15 | 94347602 | 94347632 | Hypo | cancer_general | BC037497 |
| chr15 | 97006372 | 97006533 | Hypo | cancer_general | — | chr15 | 98634851 | 98634949 | Hypo | cancer_general | — |
| chr15 | 98776762 | 98776792 | Hypo | cancer_general | — | chr15 | 99254040 | 99254208 | Hypo | hepatobiliary | IGF1R |
| chr15 | 99295692 | 99295749 | Hypo | cancer_general | IGF1R | chr15 | 99346861 | 99347040 | Hypo | cancer_general, pancreas | — |
| chr15 | 99354999 | 99355041 | Hypo | cancer_general | — | chr15 | 99453230 | 99453440 | Hypo | hepatobiliary | IGF1R |
| chr15 | 99456299 | 99456329 | Hypo | hepatobiliary | IGF1R | chr15 | 99497059 | 99497132 | Hypo | hepatobiliary | IGF1R, AF020763 |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr15 | 100274325 | 100274385 | Hypo | cancer_general | LYSMD4 | chr15 | 100339980 | 100340010 | Hypo | ovarian | DJ031154, DQ590616, DQ571121, DQ575742, DQ595494, DNM1P46, DQ575741 |
| chr15 | 101818327 | 101818357 | Hypo | cancer_general | VIMP, SNRPA1 | chr15 | 102115873 | 102115905 | Hypo | cancer_general | — |
| chr15 | 102193587 | 102193713 | Hypo | cancer_general | TARSL2, TM2D3 | NW_001838016.1_818233-828058 | 6174 | 6313 | Hypo | cancer_general | — |
| chr12 | 1650475 | 1650577 | Hypo | cancer_general | — | chr12 | 2046104 | 2046134 | Hypo | cancer_general | DCP1B, LINC00940 |
| chr12 | 2403658 | 2403714 | Hypo | cancer_general | CACNA1C-IT3 | chr12 | 2566053 | 2566247 | Hypo | cancer_general | — |
| chr12 | 2595199 | 2595339 | Hypo | cancer_general | — | chr12 | 2964465 | 2964577 | Hypo | cancer_general | FOXM1, LOC100507424 |
| chr12 | 4213973 | 4214157 | Hypo | cancer_general | — | chr12 | 4231674 | 4231767 | Hypo | cancer_general | — |
| chr12 | 4274271 | 4274409 | Hypo | pancreas | — | chr12 | 4323835 | 4323912 | Hypo | cancer_general | — |
| chr12 | 4362436 | 4362471 | Hypo | cancer_general | — | chr12 | 4379357 | 4379491 | Hypo | pancreas | CCND2 |
| chr12 | 4392883 | 4392922 | Hypo | cancer_general | CCND2 | chr12 | 4405589 | 4405619 | Hypo | cancer_general | CCND2 |
| chr12 | 4431271 | 4431301 | Hypo | cancer_general | C12orf5 | chr12 | 4554801 | 4554831 | Hypo | cancer_general | FGF6 |
| chr12 | 5840200 | 5840363 | Hypo | cancer_general | ANO2 | chr12 | 6473721 | 6473762 | Hypo | cancer_general | SCNN1A |
| chr12 | 6483615 | 6483756 | Hypo | cancer_general | LITBR, SCNN1A | chr12 | 6678158 | 6678203 | Hypo | cancer_general | CHD4, AK096395, NOP2 |
| chr12 | 7403914 | 7404060 | Hypo | cancer_general | NANOGP1 | chr12 | 7559160 | 7559307 | Hypo | cancer_general | CD163L1 |
| chr12 | 8036526 | 8036634 | Hypo | cancer_general | — | chr12 | 8122523 | 8122628 | Hypo | cancer_general | — |
| chr12 | 8127036 | 8127140 | Hypo | cancer_general | — | chr12 | 8127565 | 8127595 | Hypo | hepatobiliary | — |
| chr12 | 8139203 | 8139233 | Hypo | cancer_general | FOXJ2 | chr12 | 8163573 | 8163603 | Hypo | cancer_general | — |
| chr12 | 8180999 | 8181065 | Hypo | ovarian | A2ML1 | chr12 | 8808599 | 8808709 | Hypo | cancer_general | MFAP5 |
| chr12 | 8975182 | 8975361 | Hypo | cancer_general | CLEC2A | chr12 | 9916313 | 9916343 | Hypo | cancer_general | CD69 |
| chr12 | 10085916 | 10085948 | Hypo | cancer_general | STYK1, MAGOHB | chr12 | 10363278 | 10363607 | Hypo | cancer_general | GABARAPL1 |
| chr12 | 10772771 | 10772896 | Hypo | hepatobiliary | LOH12CR2, LOH12CR1 | chr12 | 12456859 | 12456889 | Hypo | pancreas | — |
| chr12 | 12504616 | 12504850 | Hypo | cancer_general | GPRC5A, RPL13AP20 | chr12 | 12848390 | 12848556 | Hypo | cancer_general | GPR19 |
| chr12 | 13036048 | 13036078 | Hypo | cancer_general | PLBD1 | chr12 | 13055966 | 13055996 | Hypo | pancreas | GPRC5A |
| chr12 | 14719937 | 14719967 | Hypo | cancer_general | — | chr12 | 14818824 | 14818867 | Hypo | cancer_general | GUCY2C |
| chr12 | 21833068 | 21833265 | Hypo | cancer_general | AK094733 | chr12 | 22698063 | 22698110 | Hypo | cancer_general | C2CD5 |
| chr12 | 23229390 | 23229420 | Hypo | cancer_general | — | chr12 | 25362824 | 25362853 | Hypo | literature | LYRM5, KRAS |
| chr12 | 25368463 | 25368492 | Hypo | literature | KRAS | chr12 | 25378543 | 25378662 | Hypo | literature | KRAS |
| chr12 | 25380231 | 25380299 | Hypo | literature | KRAS | chr12 | 25398203 | 25398319 | Hypo | literature | DD157417, KRAS |
| chr12 | 26178334 | 26178376 | Hypo | cancer_general | RASSF8 | chr12 | 27114515 | 27114639 | Hypo | ovarian | TM7SF3, FGFR1OP2 |
| chr12 | 27176441 | 27176539 | Hypo | cancer_general | MED21, TM7SF3 | chr12 | 27494550 | 27494580 | Hypo | pancreas | ARNTL2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 31316012 | 31316362 | Hypo | cancer_general | OVOS2 | chr12 | 31366306 | 31366336 | Hypo | cancer_general | OVOS2 |
| chr12 | 32086716 | 32086982 | Hypo | cancer_general | — | chr12 | 32340317 | 32340534 | Hypo | cancer_general | BICD1 |
| chr12 | 32831622 | 32831652 | Hypo | cancer_general | DNM1L | chr12 | 34494888 | 34494918 | Hypo | cancer_general | — |
| chr12 | 34502733 | 34502803 | Hypo | cancer_general | — | chr12 | 43944952 | 43944991 | Hypo | cancer_general | — |
| chr12 | 47629349 | 47629379 | Hypo | breast | PCED1B | chr12 | 49035233 | 49035414 | Hypo | head_neck | TUBA1A, TUBA1B |
| chr12 | 49074601 | 49074843 | Hypo | cancer_general | CCNT1 | chr12 | 49915852 | 49915920 | Hypo | cancer_general | FAM186B |
| chr12 | 49657705 | 49657901 | Hypo | cancer_general | D28390, TUBA1C | chr12 | 49989786 | 49989816 | Hypo | ovarian | — |
| chr12 | 50507349 | 50507522 | Hypo | cancer_general | COX14, GPD1 | chr12 | 50673944 | 50674096 | Hypo | pancreas | — |
| chr12 | 50897763 | 50898273 | Hypo | cancer_general | DIP2B | chr12 | 51400044 | 51400091 | Hypo | cancer_general | U7, SLC11A2 |
| chr12 | 51420874 | 51421271 | Hypo | cancer_general | LETMD1 | chr12 | 51421556 | 51421586 | Hypo | cancer_general | — |
| chr12 | 51441284 | 51441368 | Hypo | cancer_general | DAZAP2 | chr12 | 51565269 | 51565548 | Hypo | cancer_general | — |
| chr12 | 51625514 | 51625587 | Hypo | ovarian | — | chr12 | 51930708 | 51930862 | Hypo | cancer_general | — |
| chr12 | 53763427 | 53763885 | Hypo | cancer_general | PRR13, PCBP2, AMHR2 | chr12 | 53766833 | 53766964 | Hypo | cancer_general | SP1 |
| chr12 | 53834392 | 53834475 | Hypo | cancer_general | — | chr12 | 53885346 | 53885651 | Hypo | cancer_general | TARBP2, MAP3K12 |
| chr12 | 54613463 | 54613615 | Hypo | cancer_general | — | chr12 | 54719808 | 54720232 | Hypo | cancer_general | COPZ1 |
| chr12 | 54894048 | 54894173 | Hypo | lung | NCKAP1L | chr12 | 54922624 | 54922803 | Hypo | cancer_general | NCKAP1L |
| chr12 | 55480923 | 55481067 | Hypo | cancer_general | — | chr12 | 55561202 | 55561354 | Hypo | cancer_general | — |
| chr12 | 56231108 | 56231148 | Hypo | cancer_general | AX747140, DNAJC14, MMP19 | chr12 | 56400463 | 56400591 | Hypo | cancer_general | SUOX, RAB5B |
| chr12 | 56478840 | 56478869 | Hypo | literature | ERBB3 | chr12 | 56481645 | 56481937 | Hypo | literature | ERBB3 |
| chr12 | 56486572 | 56486601 | Hypo | literature | ERBB3 | chr12 | 56490965 | 56490994 | Hypo | literature | ERBB3, PA2G4 |
| chr12 | 56491630 | 56491659 | Hypo | literature | ERBB3, PA2G4 | chr12 | 56492618 | 56492647 | Hypo | literature | PA2G4, ERBB3 |
| chr12 | 56558381 | 56558519 | Hypo | ovarian | SMARCC2, MYL6, MYL6B | chr12 | 56653281 | 56653369 | Hypo | ovarian | COQ10A, ANKRD52 |
| chr12 | 57174355 | 57174452 | Hypo | cancer_general | HSD17B6 LRP1 | chr12 | 57359920 | 57359950 | Hypo | cancer_general | RDH16 MARS, ARHGAP9 |
| chr12 | 57559869 | 57559925 | Hypo | cancer_general | — | chr12 | 57881127 | 57881383 | Hypo | cancer_general | — |
| chr12 | 57983314 | 57983348 | Hypo | ovarian | PIP4K2C, BC033961, KIF5A | chr12 | 58145415 | 58145450 | Hypo | literature | CDK4, TSPAN31, DM110804, MARCH9 |
| chr12 | 62603907 | 62603937 | Hypo | ovarian | Y_RNA, AK024134, PPM1H | chr12 | 62858444 | 62858575 | Hypo | ovarian | MON2 |
| chr12 | 63326618 | 63326648 | Hypo | cancer_general | — | chr12 | 64028352 | 64028382 | Hypo | cancer_general | DPY19L2 |
| chr12 | 64783185 | 64783308 | Hypo | lung | LEMD3 | chr12 | 65516360 | 65516455 | Hypo | cancer_general | WIF1 |
| chr12 | 65557212 | 65557376 | Hypo | cancer_general | — | chr12 | 65561778 | 65562086 | Hypo | colorectal, cancer_general | LEMD3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 68433260 | 68433321 | Hypo | colorectal | — | chr12 | 68964473 | 68964503 | Hypo | ovarian | YEATS4, E02193, LYZ |
| chr12 | 68978322 | 68978576 | Hypo | cancer_general | — | chr12 | 69754451 | 69754729 | Hypo | cancer_general | |
| chr12 | 69964176 | 69964264 | Hypo | cancer_general | FRS2 | chr12 | 70087493 | 70087568 | Hypo | cancer_general | BEST3 |
| chr12 | 70698883 | 70699050 | Hypo | cancer_general | CNOT2 | chr12 | 85667353 | 85667465 | Hypo | cancer_general | ALX1 |
| chr12 | 89915009 | 89915043 | Hypo | cancer_general | POC1B-GALNT4, GALNT4, POC1B | chr12 | 93476304 | 93476342 | Hypo | breast | LOC643339 |
| chr12 | 94544022 | 94544052 | Hypo | pancreas | PLXNC1 | chr12 | 94852412 | 94852506 | Hypo | cancer_general | CCDC41-AS1, CCDC41 |
| chr12 | 95216830 | 95216960 | Hypo | cancer_general | — | chr12 | 95822981 | 95823011 | Hypo | cancer_general | |
| chr12 | 95866563 | 95866609 | Hypo | cancer_general | METAP2 | chr12 | 96880822 | 96881029 | Hypo | cancer_general | C12orf55 |
| chr12 | 98948200 | 98948295 | Hypo | cancer_general | — | chr12 | 98949938 | 98949972 | Hypo | ovarian | |
| chr12 | 98961066 | 98961241 | Hypo | cancer_general | — | chr12 | 99886343 | 99886491 | Hypo | cancer_general | SLC25A3, SNORA53 |
| chr12 | 100595495 | 100595558 | Hypo | cancer_general | AX746635, ACTR6 | chr12 | 101025380 | 101025410 | Hypo | pancreas | GAS2L3 |
| chr12 | 102457208 | 102457238 | Hypo | cancer_general | CCDC53 | chr12 | 104506691 | 104506783 | Hypo | pancreas | NFYB, HCFC2 |
| chr12 | 104671030 | 104671064 | Hypo | cancer_general | TXNRD1 | chr12 | 104671699 | 104671761 | Hypo | cancer_general | TXNRD1 |
| chr12 | 104684181 | 104684258 | Hypo | lung | TXNRD1 | chr12 | 104696376 | 104696502 | Hypo | cancer_general | EID3, TXNRD1 |
| chr12 | 105017109 | 105017228 | Hypo | colorectal | — | chr12 | 108080498 | 108080553 | Hypo | cancer_general | PWP1 |
| chr12 | 109488519 | 109488686 | Hypo | lung | USP30-AS1, USP30 | chr12 | 110353414 | 110353451 | Hypo | breast | TCHP |
| chr12 | 110507084 | 110507207 | Hypo | cancer_general | C12orf76 | chr12 | 110717541 | 110717710 | Hypo | cancer_general | ATP2A2, JA611269 |
| chr12 | 110840344 | 110840404 | Hypo | cancer_general | ANAPC7 | chr12 | 110854243 | 110854288 | Hypo | cancer_general | — |
| chr12 | 110887179 | 110887209 | Hypo | cancer_general | GPN3, ARPC3 | chr12 | 110983706 | 110983736 | Hypo | lung | PPTC7 |
| chr12 | 111143726 | 111143756 | Hypo | cancer_general | — | chr12 | 111763122 | 111763152 | Hypo | cancer_general | — |
| chr12 | 112547662 | 112547692 | Hypo | cancer_general | — | chr12 | 112574734 | 112574995 | Hypo | lung | TRAFD1 |
| chr12 | 112792829 | 112792944 | Hypo | breast | — | chr12 | 112825760 | 112825896 | Hypo | cancer_general | — |
| chr12 | 112888151 | 112888315 | Hypo | literature | PTPN11 | chr12 | 112910821 | 112910850 | Hypo | literature | PTPN11 |
| chr12 | 112915509 | 112915538 | Hypo | literature | PTPN11 | chr12 | 112926255 | 112926284 | Hypo | literature | PTPN11 |
| chr12 | 112926876 | 112926914 | Hypo | cancer_general | PTPN11 | chr12 | 113795506 | 113795657 | Hypo | cancer_general | PLBD2 |
| chr12 | 114337763 | 114337793 | Hypo | lung | RBM19 | chr12 | 117474065 | 117474198 | Hypo | lung, cancer_general | TESC, AK055849, FBXW8 |
| chr12 | 117526330 | 117526368 | Hypo | cancer_general | TESC | chr12 | 118860397 | 118860654 | Hypo | cancer_general | SUDS3 |
| chr12 | 118920764 | 118920804 | Hypo | cancer_general | — | chr12 | 120148142 | 120148248 | Hypo | cancer_general | MIR1178, CIT |
| chr12 | 120148923 | 120148962 | Hypo | cancer_general | MIR1178, CIT | chr12 | 120535158 | 120535187 | Hypo | literature | RAB35, CCDC64 |
| chr12 | 120536625 | 120536654 | Hypo | literature | CCDC64, RAB35 | chr12 | 120885215 | 120885245 | Hypo | cancer_general | GATC, TRIAP1, COX6A1 |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr12 | 120971686 | 120971716 | Hypo | cancer_general | RNF10, COQ5 | chr12 | 121622546 | 121622576 | Hypo | cancer_general | P2RX7 |
| chr12 | 122108464 | 122108601 | Hypo | head_neck | MORN3 | chr12 | 122192723 | 122192843 | Hypo | breast | TMEM120B |
| chr12 | 122278388 | 122278580 | Hypo | cancer_general | HPD, SETD1B | chr12 | 122285067 | 122285108 | Hypo | cancer_general | HPD |
| chr12 | 122473581 | 122473611 | Hypo | cancer_general | BCL7A | chr12 | 122940449 | 122940479 | Hypo | colorectal | HCAR1, HCAR3 |
| chr12 | 123129129 | 123129550 | Hypo | cancer_general | HCAR1 | chr12 | 123211316 | 123211390 | Hypo | pancreas | |
| chr12 | 123233646 | 123233846 | Hypo | cancer_general | DENR | chr12 | 123410210 | 123410240 | Hypo | cancer_general | ABCB9 |
| chr12 | 123942025 | 123942189 | Hypo | cancer_general | SNRNP35 | chr12 | 124117199 | 124117289 | Hypo | cancer_general | EIF2B1, GTF2H3 |
| chr12 | 124393560 | 124393604 | Hypo | cancer_general | — | chr12 | 124397464 | 124397618 | Hypo | cancer_general | AACS |
| chr12 | 125009276 | 125009306 | Hypo | cancer_general | — | chr12 | 125589840 | 125589872 | Hypo | esophageal | |
| chr12 | 129447299 | 129447450 | Hypo | cancer_general | GLT1D1 | chr12 | 130037653 | 130037778 | Hypo | cancer_general | RIMBP2 |
| chr12 | 130821371 | 130821621 | Hypo | cancer_general | PIWIL1 | chr12 | 130968621 | 130968654 | Hypo | cancer_general | AX748157, GPR133 |
| chr12 | 131403032 | 131403125 | Hypo | cancer_general | — | chr12 | 131513345 | 131513403 | Hypo | cancer_general | |
| chr12 | 132102173 | 132102202 | Hypo | literature | SFSWAP | chr12 | 132169288 | 132169442 | Hypo | cancer_general | MMP17 |
| chr12 | 132221689 | 132222076 | Hypo | cancer_general | MMP17 | chr12 | 132332910 | 132332940 | Hypo | cancer_general | |
| chr12 | 132333434 | 132333597 | Hypo | cancer_general | PUS1 | chr12 | 132348651 | 132348684 | Hypo | cancer_general | NOC4L |
| chr12 | 132423516 | 132423854 | Hypo | cancer_general | — | chr12 | 132643233 | 132643279 | Hypo | head_neck | |
| chr12 | 132986495 | 132986581 | Hypo | cancer_general | LRCOL1 | chr12 | 133002792 | 133003231 | Hypo | cancer_general | |
| chr12 | 133172907 | 133173021 | Hypo | cancer_general | — | chr12 | 133199738 | 133199784 | Hypo | cancer_general | P2RX2, POLE |
| chr12 | 133262698 | 133262926 | Hypo | cancer_general | PXMP2, PGAM5, POLE | chr12 | 133280578 | 133280682 | Hypo | ovarian | PGAM5, PXMP2 |
| chr6 | 373148 | 373290 | Hypo | cancer_general | — | chr6 | 2986688 | 2986718 | Hypo | cancer_general | NQO2, DKFZP686I15217 |
| chr6 | 3053299 | 3053386 | Hypo | cancer_general | SLC22A23, AX746991 | chr6 | 3247675 | 3247704 | Hypo | literature | AK096219 |
| chr6 | 3285222 | 3285513 | Hypo | cancer_general | | chr6 | 3405645 | 3405713 | Hypo | cancer_general | SLC22A23 |
| chr6 | 4836002 | 4836458 | Hypo | cancer_general | CDYL | chr6 | 4951247 | 4951390 | Hypo | cancer_general | CDYL |
| chr6 | 5359500 | 5359539 | Hypo | breast | FARS2 | chr6 | 5783325 | 5783496 | Hypo | cancer_general | — |
| chr6 | 6367086 | 6367271 | Hypo | cancer_general | LY86-AS1 | chr6 | 6753803 | 6753839 | Hypo | colorectal | — |
| chr6 | 7731054 | 7731083 | Hypo | literature | BMP6 | chr6 | 7892314 | 7892412 | Hypo | ovarian | |
| chr6 | 8014600 | 8014772 | Hypo | head_neck | BLOC1S5, EEF1E1-MUTED | chr6 | 10390384 | 10390447 | Hypo | cancer_general | TXNDC5, BLOC1S5-TXNDC5 TEAP2A |
| chr6 | 10542836 | 10542977 | Hypo | colorectal | GCNT2 | chr6 | 10734917 | 10735045 | Hypo | cancer_general | TMEM14C |
| chr6 | 12288517 | 12288681 | Hypo | cancer_general | EDN1 | chr6 | 13797690 | 13797736 | Hypo | cancer_general | MCUR1 |
| chr6 | 14687918 | 14688084 | Hypo | cancer_general | — | chr6 | 14986483 | 14986522 | Hypo | cancer_general | — |
| chr6 | 15513780 | 15513981 | Hypo | ovarian | DTNBP1, JARID2 | chr6 | 16197030 | 16197112 | Hypo | cancer_general | — |
| chr6 | 16729595 | 16729624 | Hypo | literature | ATXN1 | chr6 | 17666654 | 17666707 | Hypo | breast | NUP153 |
| chr6 | 17750276 | 17750306 | Hypo | cancer_general | KIF13A | chr6 | 18035867 | 18036015 | Hypo | lung | — |
| chr6 | 19892448 | 19892627 | Hypo | cancer_general | — | chr6 | 22172209 | 22172305 | Hypo | hepatobiliary | LINC00340 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 22172536 | 22172566 | Hypo | hepatobiliary | LINC00340 | chr6 | 24647342 | 24647599 | Hypo | cancer_general | TDP2, KIAA0319 |
| chr6 | 24662439 | 24662469 | Hypo | cancer_general | ACOT13, TDP2 | chr6 | 26189859 | 26189991 | Hypo | cancer_general | HIST1H3D, HIST1H3F, HIST1H2AD, HIST1H2BF, HIST1H4D, HIST1H2BE |
| chr6 | 26214514 | 26214648 | Hypo | cancer_general | HIST1H2BG, HIST1H2AE, HIST1H3F, HIST1H4E | chr6 | 26254617 | 26254647 | Hypo | cancer_general | HIST1H2BH, HIST1H3F, HIST1H4G |
| chr6 | 26260956 | 26260986 | Hypo | esophageal | HIST1H2BH | chr6 | 27441812 | 27441842 | Hypo | cancer_general | TRNA_Ser, TRNA_Asp, ZNF184 |
| chr6 | 30095233 | 30095262 | Hypo | literature | TRIM40, DQ580846 | chr6 | 30130804 | 30130895 | Hypo | literature | TRIM15, TRIM10 |
| chr6 | 32374147 | 32374176 | Hypo | literature | BTNL2 | chr6 | 32374739 | 32374768 | Hypo | literature | BTNL2 |
| chr6 | 32376051 | 32376080 | Hypo | literature | BTNL2 | chr6 | 33161275 | 33161342 | Hypo | literature | RXRB, JA611279, SLC39A7, COL11A2 |
| chr6 | 33633930 | 33633000 | Hypo | hepatobiliary | ITPR3 | chr6 | 33636388 | 33636418 | Hypo | hepatobiliary | ITPR3 |
| chr6 | 33955505 | 33955731 | Hypo | cancer_general | — | chr6 | 34113872 | 34113957 | Hypo | tcga | — |
| chr6 | 34170970 | 34171061 | Hypo | cancer_general | — | chr6 | 34219930 | 34219972 | Hypo | cancer_general | C6orf1, HMGA1 |
| chr6 | 34396431 | 34396542 | Hypo | cancer_general | RPS10 | chr6 | 34535802 | 34535832 | Hypo | cancer_general | SNRPC |
| chr6 | 34714803 | 34714896 | Hypo | lung | SNRPC | chr6 | 34724047 | 34724228 | Hypo | cancer_general | TULP1, TEAD3 |
| chr6 | 35150041 | 35150080 | Hypo | cancer_general | — | chr6 | 35470285 | 35470399 | Hypo | cancer_general | BRPF3 |
| chr6 | 36165662 | 36165692 | Hypo | cancer_general | BRPF3, BC042825 | chr6 | 36178031 | 36178301 | Hypo | colorectal | |
| chr6 | 36313883 | 36313913 | Hypo | cancer_general | ETV7, C6orf222 | chr6 | 36392273 | 36392323 | Hypo | cancer_general | PXT1 |
| chr6 | 36406316 | 36406370 | Hypo | cancer_general | KCTD20, PXT1 | chr6 | 37024559 | 37024589 | Hypo | cancer_general | — |
| chr6 | 37392127 | 37392189 | Hypo | cancer_general | FTSJD2 | chr6 | 37545401 | 37545495 | Hypo | cancer_general | — |
| chr6 | 37776410 | 37776440 | Hypo | cancer_general | — | chr6 | 37776703 | 37776735 | Hypo | cancer_general | — |
| chr6 | 39508464 | 39508493 | Hypo | literature | KIF6 | chr6 | 41273881 | 41273942 | Hypo | cancer_general | USP49 |
| chr6 | 41773520 | 41773903 | Hypo | breast | USP49 | chr6 | 41774459 | 41774576 | Hypo | breast | C6orf132 |
| chr6 | 42062143 | 42062346 | Hypo | cancer_general | C6orf132 | chr6 | 42090977 | 42091027 | Hypo | cancer_general | TBCC |
| chr6 | 42111015 | 42111051 | Hypo | cancer_general | C6orf132 | chr6 | 42711893 | 42711923 | Hypo | cancer_general | RPL7L1, DQ581019 |
| chr6 | 42773440 | 42773622 | Hypo | cancer_general | GLTSCR1L | chr6 | 42846662 | 42846705 | Hypo | cancer_general | PTK7 |
| chr6 | 42990166 | 42990485 | Hypo | cancer_general | RRP36, KLHDC3, MEA1 | chr6 | 43119019 | 43119580 | Hypo | colorectal, cancer_general | |
| chr6 | 43424297 | 43424470 | Hypo | cancer_general | DLK2, ABCC10 | chr6 | 43425152 | 43425207 | Hypo | cancer_general | ABCC10, DLK2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 43425479 | 43425509 | Hypo | cancer_general | DLK2, ABCC10 | chr6 | 43478676 | 43478745 | Hypo | cancer_general | YIPF3, POLR1C, LRRC73, TJAP1 |
| chr6 | 43639548 | 43639710 | Hypo | ovarian | MRPS18A, RSPH9 | chr6 | 43748463 | 43748616 | Hypo | breast | HV983065, VEGFA |
| chr6 | 44240914 | 44241108 | Hypo | cancer_general | TCTE1, SPATS1, TMEM151B, NFKBIE | chr6 | 44695763 | 44695795 | Hypo | cancer_general | BX647715 |
| chr6 | 47473194 | 47473287 | Hypo | cancer_general | CD2AP | chr6 | 47590439 | 47590604 | Hypo | breast | CD2AP |
| chr6 | 49590555 | 49590786 | Hypo | cancer_general | RHAG | chr6 | 49765146 | 49765202 | Hypo | cancer_general | — |
| chr6 | 52344375 | 52344405 | Hypo | pancreas | EFHC1 | chr6 | 52763812 | 52763982 | Hypo | colorectal | GSTA3 |
| chr6 | 52928742 | 52928776 | Hypo | cancer_general | FBXO9, ICK | chr6 | 52929051 | 52929233 | Hypo | cancer_general | ICK, FBXO9 |
| chr6 | 53052723 | 53052859 | Hypo | cancer_general | — | chr6 | 57694587 | 57694617 | Hypo | cancer_general | — |
| chr6 | 58147523 | 58147594 | Hypo | cancer_general | TRNA_Ile, TRNA_Ala | chr6 | 71090933 | 71090963 | Hypo | ovarian | — |
| chr6 | 73980676 | 73980722 | Hypo | hepatobiliary | C6orf147, AL832252, BC031876, KHDC1 | chr6 | 73982025 | 73982058 | Hypo | hepatobiliary | C6orf147, AL832252, BC031876, KHDC1 |
| chr6 | 74097722 | 74097763 | Hypo | ovarian | DDX43 | chr6 | 75995789 | 75995819 | Hypo | cancer_general | FILIP1, LOC100506804, TMEM30A |
| chr6 | 82958615 | 82958917 | Hypo | cancer_general | IBTK | chr6 | 83546464 | 83546498 | Hypo | cancer_general | SNX14 |
| chr6 | 85050415 | 85050504 | Hypo | cancer_general | — | chr6 | 86302413 | 86302614 | Hypo | cancer_general | RNGTT |
| chr6 | 88518712 | 88518742 | Hypo | colorectal | AY927641 | chr6 | 89672213 | 89672376 | Hypo | cancer_general | AK091365 |
| chr6 | 97412429 | 97412529 | Hypo | esophageal | KLHL32 | chr6 | 97930083 | 97930113 | Hypo | hepatobiliary | PNISR, BC033061, COQ3 |
| chr6 | 99396456 | 99396609 | Hypo | cancer_general | — | chr6 | 99842336 | 99842382 | Hypo | tcga | |
| chr6 | 100050765 | 100050815 | Hypo | cancer_general | PRDM13 | chr6 | 100135425 | 100135583 | Hypo | cancer_general | ATG5 |
| chr6 | 105821423 | 105821453 | Hypo | cancer_general | PREP | chr6 | 106731509 | 106731597 | Hypo | ovarian | PDSS2 |
| chr6 | 107075651 | 107075704 | Hypo | cancer_general | QRSL1, RTN4P1 | chr6 | 107562769 | 107562859 | Hypo | cancer_general | |
| chr6 | 108181556 | 108181721 | Hypo | cancer_general | SEC63 | chr6 | 108280292 | 108280352 | Hypo | cancer_general | SEC63 |
| chr6 | 109057882 | 109057928 | Hypo | pancreas | — | chr6 | 109058799 | 109058861 | Hypo | pancreas | — |
| chr6 | 110437721 | 110437751 | Hypo | cancer_general | WASF1 | chr6 | 110448558 | 110448682 | Hypo | ovarian | |
| chr6 | 113852508 | 113852634 | Hypo | cancer_general | — | chr6 | 117000853 | 117001032 | Hypo | cancer_general | KPNA5, AX746765 |
| chr6 | 119254629 | 119254678 | Hypo | cancer_general | MCM9 | chr6 | 119483052 | 119483082 | Hypo | cancer_general | — |
| chr6 | 121797231 | 121797265 | Hypo | hepatobiliary | MGC34034, BC041459 | chr6 | 134067194 | 134067471 | Hypo | cancer_general | BC041459 |
| chr6 | 134176232 | 134176299 | Hypo | cancer_general | IL20RA | chr6 | 134589500 | 134589767 | Hypo | cancer_general | SGK1 |
| chr6 | 137366354 | 137366383 | Hypo | literature | LOC100652739, LRP11 | chr6 | 149868348 | 149868387 | Hypo | cancer_general | PPIL4 |
| chr6 | 150183760 | 150183874 | Hypo | cancer_general | | chr6 | 151650396 | 151650453 | Hypo | cancer_general | AKAP12 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 152419908 | 152419940 | Hypo | literature | ESR1 | chr6 | 154970558 | 154970676 | Hypo | lung | — |
| chr6 | 155569208 | 155569305 | Hypo | cancer_general | AB075492, AK022993, TFB1M, TIAM2 | chr6 | 157037549 | 157037677 | Hypo | cancer_general | — |
| chr6 | 157266063 | 157266109 | Hypo | breast | ARID1B | | | | | | |
| chr6 | 157506082 | 157506112 | Hypo | cancer_general | — | chr6 | 157502438 | 157502561 | Hypo | cancer_general | — |
| chr6 | 159211558 | 159211701 | Hypo | pancreas | AX747826, EZR | chr6 | 157637455 | 157637500 | Hypo | cancer_general | — |
| | | | | | | chr6 | 159228187 | 159228217 | Hypo | cancer_general | AX747826, EZR |
| chr6 | 159419589 | 159419717 | Hypo | cancer_general | RSPH3 | chr6 | 161645992 | 161646255 | Hypo | cancer_general | — |
| chr6 | 161780056 | 161780139 | Hypo | cancer_general | PARK2 | chr6 | 163602842 | 163602872 | Hypo | esophageal | — |
| chr6 | 164114396 | 164114524 | Hypo | cancer_general | AK093114 | chr6 | 164179636 | 164179668 | Hypo | cancer_general | AK311212, AK296276 |
| chr6 | 164183602 | 164183632 | Hypo | cancer_general | AK093114 | chr6 | 164196971 | 164197003 | Hypo | cancer_general | AK093114 |
| chr6 | 164215532 | 164215633 | Hypo | cancer_general | — | chr6 | 164228294 | 164228363 | Hypo | cancer_general | AK093114 |
| chr6 | 164246015 | 164246143 | Hypo | cancer_general | — | chr6 | 164283254 | 164283377 | Hypo | cancer_general | — |
| chr6 | 164314289 | 164314443 | Hypo | cancer_general | — | chr6 | 164322666 | 164322775 | Hypo | cancer_general | — |
| chr6 | 166944367 | 166944403 | Hypo | cancer_general | — | chr6 | 167202601 | 167202801 | Hypo | cancer_general | — |
| chr6 | 167835129 | 167835171 | Hypo | cancer_general | — | chr6 | 168719983 | 168720019 | Hypo | esophageal | DACT2 |
| chr6 | 168858122 | 168858296 | Hypo | cancer_general | SMOC2 | chr6 | 168972472 | 168972502 | Hypo | hepatobiliary | SMOC2 |
| chr6 | 169002054 | 169002084 | Hypo | esophageal | SMOC2 | chr6 | 170047467 | 170047499 | Hypo | lung | WDR27 |
| chr6 | 170240639 | 170240714 | Hypo | cancer_general | — | chr6 | 170264728 | 170264761 | Hypo | cancer_general | — |
| chr6 | 170475105 | 170475267 | Hypo | cancer_general | — | chr6 | 170494286 | 170494315 | Hypo | literature | — |
| chr6 | 170894820 | 170894912 | Hypo | cancer_general | PDCD2 | chr9 | 969788 | 969820 | Hypo | cancer_general | DMRT3, DMRT1 |
| chr9 | 2115824 | 2115981 | Hypo | breast | SMARCA2 | chr9 | 5070006 | 5070050 | Hypo | literature | JAK2 |
| chr9 | 5073756 | 5073788 | Hypo | literature | JAK2 | chr9 | 5078346 | 5078375 | Hypo | literature | JAK2 |
| chr9 | 5089711 | 5089740 | Hypo | literature | TRNA_Gln, JAK2 | chr9 | 5153325 | 5153380 | Hypo | cancer_general | — |
| chr9 | 6182901 | 6182931 | Hypo | cancer_general | — | chr9 | 6756353 | 6756623 | Hypo | cancer_general | KDM4C |
| chr9 | 14884008 | 14884061 | Hypo | hepatobiliary | — | chr9 | 20199955 | 20199985 | Hypo | hepatobiliary | — |
| chr9 | 21970966 | 21971220 | Hypo | literature | CDKN2A, C9orf53 | chr9 | 21974207 | 21974237 | Hypo | esophageal | CDKN2A, C9orf53 |
| chr9 | 21974663 | 21974794 | Hypo | literature | CDKN2A, C9orf53 | chr9 | 22006131 | 22006160 | Hypo | literature | CDKN2B, CDKN2B-AS1 |
| chr9 | 22008819 | 22008899 | Hypo | literature | CDKN2B, CDKN2B-AS1 | chr9 | 33000470 | 33000512 | Hypo | cancer_general | APTX |
| chr9 | 34136792 | 34136903 | Hypo | head_neck | DQ585850, DQ594696, DQ597117, DQ587955, DQ574810 | chr9 | 34224348 | 34224474 | Hypo | breast | UBAP1, KIF24 |
| chr9 | 34372805 | 34372983 | Hypo | breast | C9orf24, KIAA1161 | chr9 | 36036323 | 36036353 | Hypo | ovarian | RECK |
| chr9 | 36167272 | 36167544 | Hypo | cancer_general | CCIN, GLIPR2 | chr9 | 36196920 | 36197005 | Hypo | ovarian | CLTA |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 36318375 | 36318410 | Hypo | cancer_general | — | chr9 | 36433491 | 36433629 | Hypo | cancer_general | — |
| chr9 | 36832204 | 36832343 | Hypo | cancer_general | PAX5, MIR4475 | chr9 | 37119301 | 37119331 | Hypo | head_neck | ZCCHC7 |
| chr9 | 37467610 | 37467898 | Hypo | cancer_general | — | chr9 | 37593684 | 37593795 | Hypo | cancer_general | TOMM5 |
| chr9 | 37697404 | 37697438 | Hypo | cancer_general | FRMPD1 | chr9 | 38646763 | 38646839 | Hypo | cancer_general | — |
| chr9 | 71200632 | 71200662 | Hypo | cancer_general | — | chr9 | 71500847 | 71500886 | Hypo | hepatobiliary | — |
| chr9 | 71584152 | 71584254 | Hypo | hepatobiliary | AK057188 | chr9 | 71734816 | 71735024 | Hypo | cancer_general | TJP2 |
| chr9 | 72435189 | 72435317 | Hypo | cancer_general | BC039385, C9orf135, LOC494558 | chr9 | 73032801 | 73032831 | Hypo | cancer_general | KLF9 |
| chr9 | 74210499 | 74210654 | Hypo | cancer_general | — | chr9 | 77823177 | 77823315 | Hypo | cancer_general | — |
| chr9 | 79197119 | 79197149 | Hypo | hepatobiliary | — | chr9 | 79231003 | 79231033 | Hypo | cancer_general | PRUNE2 |
| chr9 | 79638138 | 79638244 | Hypo | cancer_general | FOXB2 | chr9 | 80303132 | 80303171 | Hypo | cancer_general | — |
| chr9 | 80409473 | 80409502 | Hypo | literature | GNAQ | chr9 | 80833933 | 80834011 | Hypo | lung | C9orf64, HNRNPK, MIR7-1 |
| chr9 | 85372494 | 85372596 | Hypo | cancer_general | — | chr9 | 86578079 | 86578366 | Hypo | ovarian | — |
| chr9 | 88694345 | 88694438 | Hypo | cancer_general | GOLM1 | chr9 | 90907408 | 90907438 | Hypo | hepatobiliary | — |
| chr9 | 90937357 | 90937387 | Hypo | ovarian | — | chr9 | 91914276 | 91914306 | Hypo | cancer_general | — |
| chr9 | 92053911 | 92053949 | Hypo | cancer_general | SEMA4D | chr9 | 93698029 | 93698133 | Hypo | colorectal | — |
| chr9 | 94572641 | 94572743 | Hypo | cancer_general | ROR2 | chr9 | 94686919 | 94686957 | Hypo | hepatobiliary | ROR2 |
| chr9 | 95417551 | 95417651 | Hypo | cancer_general | FGD3 | chr9 | 95560810 | 95560840 | Hypo | cancer_general | FAM120A |
| chr9 | 95761687 | 95761828 | Hypo | cancer_general | MIR4291 | chr9 | 96230296 | 96230334 | Hypo | cancer_general | PTPDC1 |
| chr9 | 96573748 | 96573869 | Hypo | cancer_general | ZNF169 | chr9 | 96857144 | 96857144 | Hypo | cancer_general | MIR23B, MIR3074 |
| chr9 | 97020978 | 97021126 | Hypo | cancer_general | — | chr9 | 97845915 | 97845947 | Hypo | head_neck | CDC14B, HABP4 |
| chr9 | 98076746 | 98076776 | Hypo | cancer_general | FANCC | chr9 | 99259362 | 99259405 | Hypo | ovarian | NCBP1, TSTD2 |
| chr9 | 99450020 | 99450142 | Hypo | lung | — | chr9 | 100397821 | 100398016 | Hypo | cancer_general | TRIM14, NANS |
| chr9 | 100818295 | 100818437 | Hypo | cancer_general | NANS | chr9 | 100835828 | 100835870 | Hypo | cancer_general | — |
| chr9 | 103174620 | 103174730 | Hypo | cancer_general | — | chr9 | 106998039 | 106998134 | Hypo | head_neck | FRRS1L, AL390170 |
| chr9 | 110126074 | 110126247 | Hypo | cancer_general | — | chr9 | 111894386 | 111894520 | Hypo | colorectal | KIAA0368 |
| chr9 | 112403364 | 112403394 | Hypo | esophageal | Mir_548, PALM2 | chr9 | 114247454 | 114247578 | Hypo | cancer_general | — |
| chr9 | 115067932 | 115068106 | Hypo | cancer_general | INIP | chr9 | 115087567 | 115087597 | Hypo | cancer_general | SNX30 |
| chr9 | 115478932 | 115479250 | Hypo | cancer_general | ZNF618 | chr9 | 115566363 | 115566583 | Hypo | cancer_general | — |
| chr9 | 116633883 | 116633987 | Hypo | head_neck | — | chr9 | 117050981 | 117051030 | Hypo | cancer_general | — |
| chr9 | 119603412 | 119603535 | Hypo | ovarian | TTLL11 | chr9 | 123295355 | 123295463 | Hypo | cancer_general | CDK5RAP2 |
| chr9 | 124749865 | 124749953 | Hypo | cancer_general | ZBTB26, ZBTB6 | chr9 | 124751485 | 124751515 | Hypo | cancer_general | TTLL11 |
| chr9 | 125676633 | 125676753 | Hypo | cancer_general | DENND1A, CRB2 | chr9 | 125704789 | 125704835 | Hypo | cancer_general | RABGAP1 |
| chr9 | 126133778 | 126133856 | Hypo | cancer_general | DENND1A ARPC5L, RPL35, WDR38 | chr9 | 126154304 | 126154575 | Hypo | cancer_general | DENND1A |
| chr9 | 126349038 | 126349104 | Hypo | lung | | chr9 | 127605297 | 127605327 | Hypo | head_neck | — |
| chr9 | 127630125 | 127630205 | Hypo | cancer_general | | chr9 | 127853274 | 127853304 | Hypo | breast | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 127920543 | 127920572 | Hypo | literature | PPP6C | chr9 | 128136065 | 128136095 | Hypo | cancer_general | GAPVD1 |
| chr9 | 128635180 | 128635210 | Hypo | ovarian | PBX3 | chr9 | 128759852 | 128759954 | Hypo | cancer_general | — |
| chr9 | 129388719 | 129388796 | Hypo | cancer_general | LMX1B | chr9 | 129517783 | 129517821 | Hypo | colorectal | — |
| chr9 | 130248419 | 130248449 | Hypo | cancer_general | AX747547, LRSAM1 | chr9 | 130325967 | 130325997 | Hypo | cancer_general | FAM129B |
| chr9 | 130675509 | 130675615 | Hypo | cancer_general | PIP5KL1, ST6GALNAC4 | chr9 | 130694413 | 130694468 | Hypo | cancer_general | DPM2, FAM102A, PIP5KL1 |
| chr9 | 130694809 | 130694948 | Hypo | cancer_general | DPM2, FAM102A, PIP5KL1 | chr9 | 131177975 | 131178094 | Hypo | cancer_general | CERCAM |
| chr9 | 131417698 | 131417940 | Hypo | cancer_general | — | chr9 | 131542193 | 131542267 | Hypo | head_neck | TBC1D13, ZER1 |
| chr9 | 131580038 | 131580257 | Hypo | cancer_general | ENDOG, C9orf114, TBC1D13 | chr9 | 131607517 | 131607547 | Hypo | cancer_general | CCBL1 |
| chr9 | 131607770 | 131607800 | Hypo | cancer_general | CCBL1 | chr9 | 131854231 | 131854328 | Hypo | cancer_general | CRAT, DOLPP1 |
| chr9 | 131854564 | 131854732 | Hypo | cancer_general | CRAT, DOLPP1 | chr9 | 132373058 | 132373091 | Hypo | breast | C9orf50 |
| chr9 | 132383347 | 132383376 | Hypo | literature | C9orf50, NTMT1 | chr9 | 132402840 | 132402883 | Hypo | cancer_general | ASB6, NTMT1 |
| chr9 | 132403149 | 132403216 | Hypo | cancer_general | ASB6, NTMT1 | chr9 | 132559377 | 132559456 | Hypo | cancer_general | TOR1B |
| chr9 | 132815175 | 132815205 | Hypo | cancer_general | Mir_562, FNBP1, GPR107 | chr9 | 132881814 | 132881844 | Hypo | cancer_general | — |
| chr9 | 133605601 | 133605631 | Hypo | cancer_general | ABL1 | chr9 | 133738343 | 133738372 | Hypo | literature | AX748265, ABL1 |
| chr9 | 133747505 | 133747534 | Hypo | literature | AX748265, ABL1 | chr9 | 133773766 | 133773923 | Hypo | cancer_general | FIBCD1, QRFP |
| chr9 | 133927347 | 133927481 | Hypo | cancer_general | LAMC3 | chr9 | 133928236 | 133928266 | Hypo | cancer_general | LAMC3 |
| chr9 | 134126670 | 134126741 | Hypo | colorectal, cancer_general | FAM78A | chr9 | 134191085 | 134191218 | Hypo | cancer_general | PPAPDC3 |
| chr9 | 134207916 | 134208048 | Hypo | cancer_general | — | chr9 | 134717313 | 134717367 | Hypo | cancer_general | SETX |
| chr9 | 135073463 | 135073506 | Hypo | hepatobiliary | NTNG2 | chr9 | 135135114 | 135135247 | Hypo | cancer_general | BARHL1, C9orfl71 |
| chr9 | 135231073 | 135231158 | Hypo | cancer_general | — | chr9 | 135456476 | 135456544 | Hypo | pancreas | — |
| chr9 | 135548238 | 135548313 | Hypo | cancer_general | GTF3C4, DDX31 | chr9 | 135590218 | 135590334 | Hypo | cancer_general | — |
| chr9 | 135796801 | 135796830 | Hypo | literature | TSC1 | chr9 | 135865090 | 135865161 | Hypo | cancer_general | GFI1B |
| chr9 | 135898911 | 135899124 | Hypo | cancer_general | GTF3C5 | chr9 | 137002646 | 137002692 | Hypo | cancer_general | WDR5 |
| chr9 | 137299670 | 137299699 | Hypo | tcga | RXRA | chr9 | 137575915 | 137575945 | Hypo | cancer_general | COL5A1 |
| chr9 | 137656958 | 137657128 | Hypo | cancer_general | COL5A1 | chr9 | 137667327 | 137667357 | Hypo | cancer_general | COL5A1 |
| chr9 | 137718901 | 137719001 | Hypo | cancer_general | LOC101448202, COL5A1 | chr9 | 137722087 | 137722209 | Hypo | cancer_general | LOC101448202, COL5A1 |
| chr9 | 138265123 | 138265251 | Hypo | cancer_general | — | chr9 | 138474557 | 138474590 | Hypo | cancer_general | LOC100130954 |
| chr9 | 138563059 | 138563280 | Hypo | cancer_general | LCN9 | chr9 | 138627636 | 138627893 | Hypo | cancer_general | KCNT1 |
| chr9 | 138634047 | 138634159 | Hypo | cancer_general | KCNT1 | chr9 | 138659800 | 138659905 | Hypo | cancer_general | KCNT1 |
| chr9 | 138660943 | 138661012 | Hypo | literature | KCNT1 | chr9 | 138661648 | 138661870 | Hypo | cancer_general | KCNT1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 138666455 | 138666558 | Hypo | cancer_general | KCNT1 | chr9 | 138826382 | 138826412 | Hypo | head_neck | UBAC1 |
| chr9 | 138880711 | 138880875 | Hypo | cancer_general | — | chr9 | 138991798 | 138991828 | Hypo | esophageal | NACC2 |
| chr9 | 139000566 | 139000642 | Hypo | cancer_general | C9orf69 | chr9 | 139012272 | 139012411 | Hypo | cancer_general | C9orf69 |
| chr9 | 139045653 | 139045683 | Hypo | cancer_general | — | chr9 | 139047532 | 139047633 | Hypo | cancer_general | — |
| chr9 | 139111268 | 139111298 | Hypo | cancer_general | QSOX2 | chr9 | 139269039 | 139269121 | Hypo | breast | SNAPC4, CARD9 |
| chr9 | 139399407 | 139399436 | Hypo | literature | NOTCH1 | chr9 | 139421955 | 139421985 | Hypo | cancer_general | MIR4673 |
| chr9 | 139477862 | 139478020 | Hypo | head_neck | — | chr9 | 139698925 | 139699051 | Hypo | cancer_general | RABL6, KIAA1984-AS1, KIAA1984 |
| chr9 | 139704008 | 139704279 | Hypo | cancer_general | RABL6, KIAA1984-AS1, KIAA1984 | chr9 | 139859041 | 139859268 | Hypo | cancer_general | LCN12 |
| chr9 | 139888945 | 139888980 | Hypo | breast | CLIC3, C9orf142, LCNL1 | chr9 | 140015209 | 140015241 | Hypo | ovarian | DPP7 |
| chr9 | 140030498 | 140030528 | Hypo | cancer_general | GRIN1 | chr9 | 140031944 | 140032082 | Hypo | cancer_general | GRIN1 |
| chr9 | 140033001 | 140033092 | Hypo | pancreas | GRIN1 | chr9 | 140127883 | 140128080 | Hypo | cancer_general | FAM166A, SLC34A3, RNF224, C9orf69, AK128153, TUBB4B, TUBB2C |
| chr9 | 140137310 | 140137488 | Hypo | cancer_general | FAM166A, LOC100129722, C9orf173, TUBB2C, TUBB4B, SLC34A3 | chr9 | 140205394 | 140205519 | Hypo | cancer_general | EXD3, NRARP |
| chr9 | 140245877 | 140245998 | Hypo | cancer_general | EXD3 | chr9 | 140332708 | 140333018 | Hypo | cancer_general | NSMF, ENTPD8, NOXA1 |
| chr9 | 140382557 | 140382596 | Hypo | cancer_general | PNPLA7 | chr9 | 140392454 | 140392484 | Hypo | cancer_general | — |
| chr9 | 140397029 | 140397097 | Hypo | cancer_general | — | chr9 | 140498318 | 140498394 | Hypo | cancer_general | ARRDC1 |
| chr9 | 140507256 | 140507419 | Hypo | cancer_general | ARRDC1, C9orf37, EHMT1 | chr9 | 140704046 | 140704131 | Hypo | ovarian | EHMT1 |
| chr9 | 140709046 | 140709174 | Hypo | head_neck | EHMT1 | chr9 | 140727471 | 140727511 | Hypo | head_neck | MIR602, EHMT1 |
| chr9 | 140727845 | 140727930 | Hypo | head_neck | MIR602, EHMT1 | chr9 | 140769943 | 140769973 | Hypo | cancer_general | CACNA1B, AK128414 |
| chr16 | 93831 | 93932 | Hypo | head_neck | POLR3K, SNRNP25 | chr16 | 142649 | 142783 | Hypo | lung | NPRL3, MPG |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 189744 | 189933 | Hypo | cancer_general | NPRL3 | chr16 | 199886 | 199943 | Hypo | cancer_general | HBZ |
| chr16 | 232136 | 232166 | Hypo | cancer_general | HBQ1, HBA1, HBA2, LUC7L | chr16 | 280323 | 280395 | Hypo | cancer_general | ITFG3, LUC7L |
| chr16 | 318104 | 318227 | Hypo | cancer_general | RGS11, ITFG3 | chr16 | 318498 | 318763 | Hypo | cancer_general | RGS11, ITFG3 |
| chr16 | 337599 | 337659 | Hypo | cancer_general | AXIN1, PDIA2, ARHGDIG | chr16 | 410377 | 410407 | Hypo | cancer_general | AXIN1, MRPL28 |
| chr16 | 571714 | 571959 | Hypo | cancer_general | LINC00235, SOLH, RAB11FIP3 | chr16 | 611385 | 611520 | Hypo | cancer_general | NHLRC4, PIGQ, C16orf11, SOLH |
| chr16 | 611969 | 612260 | Hypo | cancer_general | NHLRC4, PIGQ, C16orf11, SOLH | chr16 | 612869 | 613037 | Hypo | cancer_general | NHLRC4, PIGQ, C16orf11, SOLH |
| chr16 | 667141 | 667297 | Hypo | lung | RAB40C | chr16 | 667547 | 667622 | Hypo | lung | RAB40C, WFIKKN1, AK128777 |
| chr16 | 667876 | 668074 | Hypo | lung | RAB40C | chr16 | 672730 | 672806 | Hypo | head_neck | RAB40C, AK128777 |
| chr16 | 677972 | 678084 | Hypo | lung | AK301549, RAB40C, AK128777, WFIKKN1, C16orf13, TRNA_Gly, TRNA | chr16 | 700299 | 700329 | Hypo | cancer_general | WDR90, FAM195A |
| chr16 | 726626 | 726990 | Hypo | cancer_general | STUB1, JMJD8, WDR24, RHBDL1, RHOT2, WDR90 | chr16 | 731488 | 731610 | Hypo | cancer_general | STUB1, RHBDL1, RHOT2, JMJD8, WDR24 |
| chr16 | 735205 | 735594 | Hypo | cancer_general | FBXL16, WDR24, JMJD8, STUB1, RHBDL1 | chr16 | 740791 | 740914 | Hypo | cancer_general | STUB1, FBXL16, WDR24, JMJD8 |
| chr16 | 741376 | 741601 | Hypo | cancer_general | STUB1, FBXL16, WDR24, JMJD8 | chr16 | 762523 | 762694 | Hypo | cancer_general | METRN, AL360260, FAM173A, CCDC78 |
| chr16 | 837361 | 837460 | Hypo | cancer_general | CHTF18, RPUSD1 | chr16 | 845955 | 845985 | Hypo | cancer_general | GNG13, PRR25, CHTF18, RPUSD1 |
| chr16 | 882484 | 882588 | Hypo | cancer_general | — | chr16 | 895093 | 895166 | Hypo | cancer_general | LMF1 |
| chr16 | 943481 | 943553 | Hypo | cancer_general | LMF1 | chr16 | 1018120 | 1018150 | Hypo | cancer_general | LMF1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 1019640 | 1019685 | Hypo | ovarian | LMF1 | chr16 | 1052587 | 1052627 | Hypo | cancer_general | SSTR5, |
| chr16 | 1102927 | 1102957 | Hypo | cancer_general | — | chr16 | 1116661 | 1116691 | Hypo | cancer_general | SSTR5-AS1 |
| chr16 | 1129011 | 1129140 | Hypo | cancer_general | C1QTNF8, SSTR5, BC084558, SSTR5-AS1 | chr16 | 1155162 | 1155212 | Hypo | cancer_general | C1QTNF8 |
| chr16 | 1186809 | 1186850 | Hypo | cancer_general | — | chr16 | 1217307 | 1217503 | Hypo | cancer_general | CACNA1H |
| chr16 | 1218034 | 1218090 | Hypo | cancer_general | CACNA1H | chr16 | 1228804 | 1228916 | Hypo | cancer_general | CACNA1H |
| chr16 | 1229970 | 1230142 | Hypo | cancer_general | CACNA1H | chr16 | 1248604 | 1248675 | Hypo | cancer_general | CACNA1H |
| chr16 | 1267925 | 1268120 | Hypo | cancer_general | TPSG1, TPSB2, CACNA1H | chr16 | 1271546 | 1271646 | Hypo | cancer_general | TPSB2, CACNA1H, TPSG1 |
| chr16 | 1312526 | 1312611 | Hypo | cancer_general | TPSD1 | chr16 | 1323976 | 1324061 | Hypo | cancer_general | BAIAP3, TSR3, GNPTG |
| chr16 | 1394502 | 1394596 | Hypo | cancer_general | TSR3, GNPTG, BAIAP3 | chr16 | 1397454 | 1397484 | Hypo | head_neck | UNKL, GNPTG, TSR3, BAIAP3 |
| chr16 | 1407370 | 1407846 | Hypo | lung, cancer_general | UNKL, GNPTG, TSR3, BAIAP3 | chr16 | 1408210 | 1408240 | Hypo | cancer_general | UNKL, C16orf91 |
| chr16 | 1428508 | 1428873 | Hypo | cancer_general | UNKL | chr16 | 1466425 | 1466455 | Hypo | cancer_general | CLCN7, CCDC154 |
| chr16 | 1469334 | 1469527 | Hypo | cancer_general | C16orf91, UNKL | chr16 | 1491567 | 1491613 | Hypo | cancer_general | CRAMP1L HN1L, CRAMP1L |
| chr16 | 1523925 | 1523971 | Hypo | cancer_general | CLCN7 | chr16 | 1704656 | 1704800 | Hypo | breast | MAPK8IP3, HN1L |
| chr16 | 1729868 | 1730022 | Hypo | cancer_general | CRAMP1L, HN1L | chr16 | 1730306 | 1730597 | Hypo | cancer_general | GFER, NOXO1, TBL3 |
| chr16 | 1741853 | 1742079 | Hypo | cancer_general | HN1L | chr16 | 1750769 | 1750907 | Hypo | head_neck | TSC2, NTHL1 |
| chr16 | 1993818 | 1993848 | Hypo | cancer_general | CRAMP1L RPL3L, MSRB1 | chr16 | 2029072 | 2029137 | Hypo | cancer_general | |
| chr16 | 2042875 | 2042905 | Hypo | head_neck | ZNF598, SYNGR3, GFER | chr16 | 2106703 | 2106732 | Hypo | literature | |
| chr16 | 2111966 | 2111995 | Hypo | literature | TSC2 | chr16 | 2120515 | 2120544 | Hypo | literature | TSC2 |
| chr16 | 2122243 | 2122272 | Hypo | literature | — | chr16 | 2124205 | 2124348 | Hypo | literature | PKD1, TSC2 |
| chr16 | 2126080 | 2126109 | Hypo | literature | TSC2 | chr16 | 2128577 | 2129581 | Hypo | head_neck | TSC2 |
| chr16 | 2130361 | 2130390 | Hypo | literature | TSC2, PKD1, MIR1225 | chr16 | 2135301 | 2135330 | Hypo | literature | PKD1, MIR1225, TSC2 |
| chr16 | 2136228 | 2136257 | Hypo | literature | PKD1, MIR1225, TSC2 | chr16 | 2136727 | 2136855 | Hypo | literature | PKD1, MIR1225, TSC2 |
| chr16 | 2141909 | 2141972 | Hypo | cancer_general | PKD1, MIR1225, TSC2 | chr16 | 2142546 | 2142628 | Hypo | cancer_general | PKD1, MIR1225, TSC2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 2213313 | 2213343 | Hypo | cancer_general | TRAF7, SNORD60, RAB26 | chr16 | 2232745 | 2233003 | Hypo | cancer_general | CASKIN1, TRAF7 |
| chr16 | 2234726 | 2235020 | Hypo | cancer_general | CASKIN1, TRAF7 | chr16 | 2275129 | 2275182 | Hypo | cancer_general | E4F1 |
| chr16 | 2281249 | 2281314 | Hypo | lung | E4F1, DNASEIL2, ECI1 | chr16 | 2466225 | 2466307 | Hypo | cancer_general | — |
| chr16 | 2485858 | 2485917 | Hypo | head_neck | CCNF | chr16 | 2508414 | 2508453 | Hypo | lung | C16orf59, CCNF |
| chr16 | 2531069 | 2531177 | Hypo | cancer_general | TBC1D24, NTN3 | chr16 | 2731530 | 2731560 | Hypo | cancer_general | KCTD5, ERVK13-1 |
| chr16 | 2764377 | 2764470 | Hypo | cancer_general | PRSS27, KCTD5 | chr16 | 2770122 | 2770602 | Hypo | cancer_general | PRSS27 |
| chr16 | 2818101 | 2818156 | Hypo | cancer_general | TCEB2, SRRM2 | chr16 | 2956451 | 2956670 | Hypo | cancer_general | FLYWCH1, FLYWCH2 |
| chr16 | 2974601 | 2974650 | Hypo | head_neck | FLYWCH1 | chr16 | 3151127 | 3151186 | Hypo | cancer_general | ZNF205-AS1, ZSCAN10 |
| chr16 | 3211708 | 3212019 | Hypo | cancer_general | TRNA_Lys, TRNA_Pseudo, TRNA_Pro, TRNA_Arg | chr16 | 3269249 | 3269350 | Hypo | cancer_general | ZNF200, OR1F2P |
| chr16 | 3284117 | 3284147 | Hypo | esophageal | MEFV, ZNF200 | chr16 | 3492583 | 3492675 | Hypo | cancer_general | NAA60, ZNF597 |
| chr16 | 3598920 | 3598953 | Hypo | cancer_general | NLRC3 | chr16 | 3696694 | 3696724 | Hypo | cancer_general | DNASE1 |
| chr16 | 3802981 | 3803074 | Hypo | breast | CREBBP | chr16 | 3950127 | 3950279 | Hypo | cancer_general | — |
| chr16 | 4264529 | 4264694 | Hypo | cancer_general | SRL | chr16 | 4303144 | 4303174 | Hypo | cancer_general | TFAP4, LOC100507501 |
| chr16 | 4310735 | 4310847 | Hypo | cancer_general | TFAP4, LOC100507501 | chr16 | 4431126 | 4431189 | Hypo | ovarian | VASN, CORO7-PAM16, CORO7 |
| chr16 | 4783226 | 4783375 | Hypo | cancer_general | C16orf71, ANKS3 | chr16 | 4846136 | 4846514 | Hypo | cancer_general | GLYR1, LOC440335, SEPT12, ROGDI |
| chr16 | 4887144 | 4887244 | Hypo | breast | UBN1, GLYR1 | chr16 | 5541116 | 5541158 | Hypo | cancer_general | BC108660 |
| chr16 | 6035056 | 6035208 | Hypo | cancer_general | RBFOX1 | chr16 | 7382499 | 7382534 | Hypo | literature | RBFOX1 |
| chr16 | 7525361 | 7525531 | Hypo | cancer_general | ABAT | chr16 | 8781032 | 8781177 | Hypo | cancer_general | ABAT |
| chr16 | 8870353 | 8870383 | Hypo | cancer_general | CLEC16A | chr16 | 9009860 | 9009989 | Hypo | cancer_general | USP7 |
| chr16 | 11242000 | 11242138 | Hypo | blood | — | chr16 | 11427659 | 11427732 | Hypo | cancer_general | — |
| chr16 | 11490632 | 11490662 | Hypo | cancer_general | — | chr16 | 11923005 | 11923035 | Hypo | cancer_general | RSL1D1, BCAR4 |
| chr16 | 12011258 | 12011325 | Hypo | cancer_general | GSPT1, SNX29, TNFRSF17 | chr16 | 12011940 | 12012073 | Hypo | cancer_general | GSPT1 |
| chr16 | 12066767 | 12066806 | Hypo | cancer_general | SNX29 | chr16 | 12210772 | 12210896 | Hypo | head_neck | SNX29 |
| chr16 | 12211279 | 12211416 | Hypo | head_neck | SNX29 | chr16 | 12530169 | 12530199 | Hypo | cancer_general | — |
| chr16 | 12971776 | 12971934 | Hypo | cancer_general | — | chr16 | 14021974 | 14022003 | Hypo | literature | ERCC4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 14041504 | 14041533 | Hypo | literature | ERCC4 | chr16 | 14041795 | 14041824 | Hypo | literature | ERCC4 |
| chr16 | 14042062 | 14042091 | Hypo | literature | ERCC4 | chr16 | 14189948 | 14190069 | Hypo | cancer_general | MKL2 |
| chr16 | 14724632 | 14724736 | Hypo | cancer_general | BFAR, PARN | chr16 | 14725842 | 14726005 | Hypo | cancer_general | BFAR, PARN |
| chr16 | 15708247 | 15708309 | Hypo | pancreas | KIAA0430 | chr16 | 15738905 | 15739042 | Hypo | cancer_general | KIAA0430, NDE1, MIR484 |
| chr16 | 15820825 | 15820865 | Hypo | cancer_general | AX747846, MYH11 | chr16 | 16868746 | 16868905 | Hypo | cancer_general | — |
| chr16 | 18163245 | 18163352 | Hypo | cancer_general | — | chr16 | 18802250 | 18802680 | Hypo | cancer_general | ARL6IP1, RPS15A |
| chr16 | 18950928 | 18951018 | Hypo | cancer_general | GDE1, CCP110 | chr16 | 19430908 | 19430949 | Hypo | cancer_general | TMC5 |
| chr16 | 19531564 | 19531697 | Hypo | cancer_general | | chr16 | 21541606 | 21541636 | Hypo | cancer_general | SLC7A5P2 |
| chr16 | 21665540 | 21665570 | Hypo | head_neck | IGSF6 | chr16 | 21666641 | 21666771 | Hypo | head_neck | IGSF6 |
| chr16 | 21674664 | 21674777 | Hypo | ovarian | — | chr16 | 21839328 | 21839470 | Hypo | cancer_general | RRN3P1, LOC23117, LOC100132247 |
| chr16 | 22300599 | 22300637 | Hypo | cancer_general | TRNA_Leu, TRNA, POLR3E, EEF2K | chr16 | 22326397 | 22326427 | Hypo | head_neck | POLR3E |
| chr16 | 24127251 | 24127338 | Hypo | cancer_general | PRKCB | chr16 | 24172241 | 24172271 | Hypo | cancer_general | PRKCB |
| chr16 | 24180710 | 24180760 | Hypo | cancer_general | PRKCB | chr16 | 24415106 | 24415176 | Hypo | cancer_general | — |
| chr16 | 25266537 | 25266573 | Hypo | cancer_general | ZKSCAN2 | chr16 | 25542301 | 25542452 | Hypo | cancer_general | — |
| chr16 | 25551107 | 25551264 | Hypo | cancer_general | — | chr16 | 25921574 | 25921604 | Hypo | cancer_general | HS3ST4 |
| chr16 | 26302585 | 26302619 | Hypo | cancer_general | — | chr16 | 26664739 | 26664775 | Hypo | cancer_general | — |
| chr16 | 27207774 | 27207852 | Hypo | head_neck | KDM8 | chr16 | 27459938 | 27460074 | Hypo | cancer_general | IL21R-AS1, IL21R |
| chr16 | 27749857 | 27750033 | Hypo | breast | — | chr16 | 27961122 | 27961254 | Hypo | cancer_general | XPO6 |
| chr16 | 28093825 | 28093866 | Hypo | cancer_general | — | chr16 | 28224516 | 28224546 | Hypo | ovarian | CCDC101, NUPR1 |
| chr16 | 28491774 | 28491924 | Hypo | colorectal | CLN3 | chr16 | 28560309 | 28560381 | Hypo | cancer_general | |
| chr16 | 28823157 | 28823459 | Hypo | cancer_general | AK125489 | chr16 | 28850998 | 28851028 | Hypo | breast | ATXN2L, TUFM, MIR4721, SH2B1 |
| chr16 | 28877839 | 28877883 | Hypo | esophageal | SH2B1 | chr16 | 29119008 | 29119058 | Hypo | cancer_general | AK075019, RRN3P2 |
| chr16 | 29153284 | 29153356 | Hypo | cancer_general | — | chr16 | 29244900 | 29244997 | Hypo | cancer_general | — |
| chr16 | 29830871 | 29831078 | Hypo | cancer_general | BC029255, PAGR1, PRRT2, AK097472, AB209061, MAZ, MVP | chr16 | 29936211 | 29936272 | Hypo | cancer_general | KCTD13, ASPHD1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 30017330 | 30017447 | Hypo | cancer_general | DOC2A, INO80E | chr16 | 30065485 | 30065525 | Hypo | cancer_general | ALDOA |
| chr16 | 30085867 | 30085995 | Hypo | cancer_general | PPP4C, ALDOA | chr16 | 30116285 | 30116315 | Hypo | cancer_general | MAPK3, GDPD3, AK097453, YPEL3 |
| chr16 | 30124691 | 30124861 | Hypo | cancer_general | MAPK3, GDPD3, AK097453 | chr16 | 30169925 | 30170103 | Hypo | cancer_general | — |
| chr16 | 30388542 | 30388574 | Hypo | cancer_general | SEPT1, ZNF48, MYLPF, TBC1D10B | chr16 | 30402082 | 30402112 | Hypo | cancer_general | ZNF48, SEPT1 |
| chr16 | 30609373 | 30609408 | Hypo | cancer_general | ZNF689 | chr16 | 30639693 | 30639735 | Hypo | cancer_general | — |
| chr16 | 30804321 | 30804472 | Hypo | cancer_general | ZNF629 | chr16 | 30826334 | 30826509 | Hypo | cancer_general | — |
| chr16 | 30907010 | 30907148 | Hypo | lung | BC073928, CTF1, MIR762, BCL7C | chr16 | 31384593 | 31384623 | Hypo | cancer_general | ITGAX |
| chr16 | 31446830 | 31447096 | Hypo | cancer_general | ZNF843, COX6A2, ITGAD | chr16 | 31498008 | 31498165 | Hypo | cancer_general | C16orf58, SLC5A2, TGFB1I1, BC054514 |
| chr16 | 31500544 | 31500673 | Hypo | cancer_general | SLC5A2, C16orf58, BC054514 | chr16 | 46569239 | 46569474 | Hypo | cancer_general | — |
| chr16 | 46721567 | 46721707 | Hypo | cancer_general | ORC6, VPS35 | chr16 | 46803280 | 46803355 | Hypo | lung | — |
| chr16 | 48450544 | 48450574 | Hypo | head_neck | — | chr16 | 48641663 | 48641693 | Hypo | cancer_general | N4BP1 |
| chr16 | 48642149 | 48642179 | Hypo | cancer_general | N4BP1 | chr16 | 49314810 | 49314840 | Hypo | cancer_general | CBLN1 |
| chr16 | 49638060 | 49638090 | Hypo | cancer_general | ZNF423 | chr16 | 50335767 | 50335797 | Hypo | cancer_general | ADCY7 |
| chr16 | 53447826 | 53448002 | Hypo | cancer_general | — | chr16 | 53467271 | 53467395 | Hypo | cancer_general | RBL2, U6 |
| chr16 | 53563622 | 53563654 | Hypo | cancer_general | — | chr16 | 54128645 | 54128713 | Hypo | breast | FTO |
| chr16 | 56672656 | 56672685 | Hypo | tcga | MT1A, MT1JP, MT1M, MT1DP | chr16 | 57222663 | 57222709 | Hypo | cancer_general | RSPRY1 |
| chr16 | 57326422 | 57326613 | Hypo | cancer_general | PLLP, TRNA_Leu | chr16 | 57935454 | 57935605 | Hypo | cancer_general | CNGB1 |
| chr16 | 58120795 | 58120961 | Hypo | cancer_general | — | chr16 | 58427501 | 58427542 | Hypo | cancer_general | GINS3 |
| chr16 | 58545487 | 58545516 | Hypo | literature | SETD6, CNOT1, NDRG4 | chr16 | 58550489 | 58550519 | Hypo | cancer_general | NDRG4, CNOT1, SETD6 |
| chr16 | 58969757 | 58969792 | Hypo | cancer_general | AK057513 | chr16 | 66863917 | 66863959 | Hypo | cancer_general | NAE1 |
| chr16 | 67241204 | 67241234 | Hypo | cancer_general | LRRC29, MIR328, ELMO3, E2F4 | chr16 | 67313865 | 67313895 | Hypo | cancer_general | KCTD19, PLEKHG4 |
| chr16 | 67850955 | 67850985 | Hypo | cancer_general | TSNAXIP1 | chr16 | 67871102 | 67871134 | Hypo | cancer_general | NUTF2, CENPT, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 68770755 | 68770974 | Hypo | cancer_general | CDH1 | chr16 | 68844158 | 68844187 | Hypo | literature | TSNAXIP1, THAP11 |
| chr16 | 68846033 | 68846062 | Hypo | literature | CDH1 | chr16 | 68856078 | 68856107 | Hypo | literature | CDH1 |
| chr16 | 68876782 | 68876996 | Hypo | cancer_general | TANGO6, CDH1 | chr16 | 69026784 | 69026814 | Hypo | cancer_general | TANGO6 |
| chr16 | 69564118 | 69564200 | Hypo | cancer_general | — | chr16 | 69969260 | 69969290 | Hypo | breast | MIR140, WWP2 |
| chr16 | 70489585 | 70489681 | Hypo | cancer_general | FUK | chr16 | 70595535 | 70595700 | Hypo | cancer_general | ZNF19, AK123826, ZNF23 |
| chr16 | 70794492 | 70794633 | Hypo | cancer_general | BC033164, VAC14-AS1 | chr16 | 71507759 | 71507791 | Hypo | cancer_general | |
| chr16 | 71677557 | 71677661 | Hypo | breast | KIAA0931, PHLPP2, MARVELD3 | chr16 | 71715779 | 71715809 | Hypo | colorectal | PHLPP2, TRNA_Gln |
| chr16 | 71918889 | 71919024 | Hypo | cancer_general | IST1, ZNF821 | chr16 | 72957763 | 72957795 | Hypo | cancer_general | — |
| chr16 | 74886148 | 74886268 | Hypo | cancer_general | — | chr16 | 74901594 | 74901659 | Hypo | cancer_general | WDR59 |
| chr16 | 75019751 | 75019781 | Hypo | cancer_general | — | chr16 | 75549798 | 75549836 | Hypo | cancer_general | |
| chr16 | 76008985 | 76009154 | Hypo | hepatobiliary | — | chr16 | 77247440 | 77247470 | Hypo | cancer_general | SYCE1L |
| chr16 | 81564199 | 81564229 | Hypo | cancer_general | CMIP | chr16 | 81929362 | 81929392 | Hypo | breast | PLCG2 |
| chr16 | 81946246 | 81946275 | Hypo | literature | PLCG2 | chr16 | 81962167 | 81962196 | Hypo | literature | PLCG2 |
| chr16 | 84074836 | 84074871 | Hypo | cancer_general | SLC38A8 | chr16 | 84153364 | 84153394 | Hypo | cancer_general | MBTPS1, HSDL1 |
| chr16 | 84519974 | 84520010 | Hypo | hepatobiliary | TLDC1 | chr16 | 84823626 | 84823656 | Hypo | breast | |
| chr16 | 85075434 | 85075553 | Hypo | cancer_general | KIAA0513 | chr16 | 85317850 | 85317882 | Hypo | cancer_general | LINC00311 |
| chr16 | 85485747 | 85485855 | Hypo | cancer_general | — | chr16 | 85497445 | 85497475 | Hypo | cancer_general | |
| chr16 | 85517345 | 85517521 | Hypo | lung, cancer_general | — | chr16 | 85651520 | 85651550 | Hypo | cancer_general | GSE1 |
| chr16 | 85678639 | 85678761 | Hypo | cancer_general | GSE1 | chr16 | 85684308 | 85684457 | Hypo | cancer_general | GSE1 |
| chr16 | 85699689 | 85699921 | Hypo | breast | GSE1 | chr16 | 85834460 | 85834495 | Hypo | cancer_general | COX4I1, EMC8 |
| chr16 | 86571984 | 86572014 | Hypo | pancreas | MTHFSD | chr16 | 86878150 | 86878180 | Hypo | cancer_general | — |
| chr16 | 87092439 | 87092553 | Hypo | cancer_general | FLJ00104, hCG_1980662 | chr16 | 87714272 | 87714381 | Hypo | cancer_general | |
| chr16 | 87723735 | 87724098 | Hypo | cancer_general | | chr16 | 88007072 | 88007108 | Hypo | head_neck | BANP |
| chr16 | 88106322 | 88106398 | Hypo | breast | BANP | chr16 | 88164401 | 88164468 | Hypo | cancer_general | — |
| chr16 | 88498241 | 88498760 | Hypo | cancer_general | ZNF469 | chr16 | 88504058 | 88504315 | Hypo | cancer_general | ZNF469 |
| chr16 | 88506346 | 88506526 | Hypo | cancer_general | ZNF469 | chr16 | 88512427 | 88512529 | Hypo | cancer_general | ZFPM1, ZNF469 |
| chr16 | 88550263 | 88550483 | Hypo | cancer_general | — | chr16 | 88603696 | 88603760 | Hypo | cancer_general | |
| chr16 | 88623960 | 88624167 | Hypo | cancer_general | C16orf85 | chr16 | 88711337 | 88711507 | Hypo | hepatobiliary | BC033739, MVD, BC028224, IL17C, CYBA |
| chr16 | 88757466 | 88757496 | Hypo | head_neck | RNF166, SNAI3 | chr16 | 88879949 | 88880124 | Hypo | cancer_general | GALNS, APRT, CDT1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 88883238 | 88883377 | Hypo | cancer_general | GALNS, APRT, CDT1 | chr16 | 88941058 | 88941141 | Hypo | cancer_general | CBFA2T3, PABPN1L |
| chr16 | 88942119 | 88942160 | Hypo | hepatobiliary | PABPN1L, CBFA2T3 | chr16 | 88943559 | 88944024 | Hypo | cancer_general | CBFA2T3 |
| chr16 | 88945815 | 88945995 | Hypo | cancer_general | CBFA2T3 | chr16 | 88955249 | 88955368 | Hypo | cancer_general | CBFA2T3 |
| chr16 | 88956230 | 88956399 | Hypo | cancer_general | CBFA2T3 | chr16 | 88957350 | 88957857 | Hypo | cancer_general | CBFA2T3 |
| chr16 | 88958397 | 88958431 | Hypo | cancer_general | CBFA2T3 | chr16 | 88963277 | 88963763 | Hypo | cancer_general | CBFA2T3 |
| chr16 | 88966303 | 88966588 | Hypo | cancer_general | CBFA2T3 | chr16 | 88968709 | 88968789 | Hypo | cancer_general | CBFA2T3 |
| chr16 | 88978024 | 88978072 | Hypo | cancer_general | CBFA2T3 | chr16 | 88993078 | 88993230 | Hypo | cancer_general | CBFA2T3 |
| chr16 | 88999617 | 88999647 | Hypo | cancer_general | CBFA2T3 | chr16 | 89000168 | 89000204 | Hypo | cancer_general | CBFA2T3 |
| chr16 | 89001094 | 89001124 | Hypo | cancer_general | CBFA2T3 | chr16 | 89047217 | 89047747 | Hypo | cancer_general | CBFA2T3 |
| chr16 | 89072503 | 89072774 | Hypo | cancer_general | — | chr16 | 89086109 | 89086197 | Hypo | cancer_general | — |
| chr16 | 89107675 | 89107732 | Hypo | cancer_general | AK055272 | chr16 | 89109385 | 89109415 | Hypo | cancer_general | AK055272 |
| chr16 | 89120038 | 89120319 | Hypo | cancer_general | AK055272 | chr16 | 89120708 | 89120864 | Hypo | cancer_general | AK055272 |
| chr16 | 89138016 | 89138060 | Hypo | cancer_general | — | chr16 | 89220327 | 89220398 | Hypo | cancer_general | LINC00304, ACSF3 |
| chr16 | 89220655 | 89220922 | Hypo | cancer_general | LINC00304, ACSF3 | chr16 | 89240843 | 89240873 | Hypo | head_neck | CDH15, LOC400558 |
| chr16 | 89254653 | 89254830 | Hypo | cancer_general | SLC22A31, CDH15 | chr16 | 89558610 | 89558703 | Hypo | cancer_general | — |
| chr16 | 89575728 | 89575861 | Hypo | cancer_general | SPG7 | chr16 | 89584136 | 89584417 | Hypo | head_neck | SPG7 |
| chr16 | 89676025 | 89676197 | Hypo | cancer_general | DPEP1 | chr16 | 89883972 | 89884185 | Hypo | cancer_general | FANCA |
| chr16 | 89884966 | 89885142 | Hypo | cancer_general | SPIRE2, FANCA | chr16 | 89900124 | 89900180 | Hypo | cancer_general | SPIRE2 |
| chr16 | 89900455 | 89900526 | Hypo | cancer_general | SPIRE2 | chr16 | 90115428 | 90115458 | Hypo | cancer_general | LOC100130015, AK127378, PRDM7 |
| chr2 | 142427 | 142468 | Hypo | cancer_general | — | chr2 | 496228 | 496380 | Hypo | cancer_general | — |
| chr2 | 602657 | 602687 | Hypo | cancer_general | — | chr2 | 720836 | 720894 | Hypo | cancer_general | — |
| chr2 | 875961 | 875991 | Hypo | cancer_general | — | chr2 | 1652837 | 1653230 | Hypo | hepatobiliary | PXDN |
| chr2 | 1670168 | 1670216 | Hypo | hepatobiliary | PXDN | chr2 | 2321773 | 2321802 | Hypo | literature | LOC730811 |
| chr2 | 2336413 | 2336442 | Hypo | literature | LOC730811 | chr2 | 2646900 | 2646930 | Hypo | cancer_general | — |
| chr2 | 2672620 | 2672732 | Hypo | cancer_general | AK095310 | chr2 | 2844720 | 2844750 | Hypo | cancer_general | — |
| chr2 | 2893165 | 2893195 | Hypo | cancer_general | LOC100505964 | chr2 | 3259989 | 3260103 | Hypo | pancreas | TSSC1 |
| chr2 | 4019911 | 4020036 | Hypo | cancer_general | RNF144A, RNF144A-AS1 | chr2 | 4050752 | 4050781 | Hypo | literature | — |
| chr2 | 7062891 | 7062959 | Hypo | cancer_general | — | chr2 | 7164467 | 7164788 | Hypo | pancreas | — |
| chr2 | 7236859 | 7236974 | Hypo | breast | — | chr2 | 8735932 | 8736064 | Hypo | ovarian | — |
| chr2 | 8835493 | 8835523 | Hypo | cancer_general | — | chr2 | 9090685 | 9090760 | Hypo | hepatobiliary | MBOAT2 |
| chr2 | 9134404 | 9134493 | Hypo | breast | MBOAT2 | chr2 | 9192356 | 9192402 | Hypo | hepatobiliary | — |
| chr2 | 9289969 | 9290114 | Hypo | cancer_general | — | chr2 | 9960734 | 9960764 | Hypo | cancer_general | — |
| chr2 | 10115730 | 10115772 | Hypo | cancer_general | — | chr2 | 10152798 | 10153325 | Hypo | cancer_general | — |
| chr2 | 10154266 | 10154564 | Hypo | cancer_general | — | chr2 | 10154930 | 10155298 | Hypo | cancer_general | — |
| chr2 | 10156116 | 10156389 | Hypo | cancer_general | — | chr2 | 10369155 | 10369242 | Hypo | pancreas | — |
| chr2 | 10408398 | 10408459 | Hypo | cancer_general | — | chr2 | 11142174 | 11142315 | Hypo | cancer_general | GREB1, MIR4429 |
| chr2 | 11356651 | 11356762 | Hypo | ovarian | ROCK2 | chr2 | 11672746 | 11672775 | Hypo | literature | — |
| chr2 | 11903450 | 11903480 | Hypo | pancreas | LPIN1 | chr2 | 12246114 | 12246217 | Hypo | cancer_general | — |

TABLE 11-continued

| chr | Start | Stop | Hypo/hyper | Classification | annotation |
|---|---|---|---|---|---|
| chr2 | 12297534 | 12297564 | Hypo | cancer_general | — |
| chr2 | 15579989 | 15580019 | Hypo | cancer_general | — |
| chr2 | 20641988 | 20642081 | Hypo | cancer_general | RHOB |
| chr2 | 20710145 | 20710324 | Hypo | cancer_general | — |
| chr2 | 24318290 | 24318357 | Hypo | cancer_general | — |
| chr2 | 25374762 | 25374804 | Hypo | cancer_general | POMC, EFR3B |
| chr2 | 25600736 | 25600804 | Hypo | head_neck | DTNB |
| chr2 | 26372967 | 26372997 | Hypo | cancer_general | — |
| chr2 | 27356168 | 27356198 | Hypo | ovarian | C2orf53, PREB, AK074615, ABHD1 |
| chr2 | 27543012 | 27543074 | Hypo | lung | GTF3C2, MPV17 |
| chr2 | 27648172 | 27648294 | Hypo | cancer_general | NRBP1 |
| chr2 | 27887525 | 27887555 | Hypo | cancer_general | SLC4A1AP, SUPT7L |
| chr2 | 29420483 | 29420512 | Hypo | literature | ALK |
| chr2 | 29436844 | 29436888 | Hypo | literature | ALK |
| chr2 | 29445198 | 29445482 | Hypo | literature | ALK |
| chr2 | 30368444 | 30368586 | Hypo | cancer_general | YPEL5 |
| chr2 | 32275196 | 32275303 | Hypo | cancer_general | — |
| chr2 | 32580386 | 32580476 | Hypo | colorectal | BIRC6 |
| chr2 | 38551124 | 38551390 | Hypo | ovarian | ATL2 |
| chr2 | 38727561 | 38727707 | Hypo | breast | — |
| chr2 | 38953573 | 38953603 | Hypo | cancer_general | GALM |
| chr2 | 41789816 | 41789853 | Hypo | hepatobiliary | — |
| chr2 | 43824133 | 43824353 | Hypo | cancer_general | THADA |
| chr2 | 44227193 | 44227223 | Hypo | head_neck | LRPPRC |
| chr2 | 44809187 | 44809217 | Hypo | ovarian | — |
| chr2 | 47200591 | 47200621 | Hypo | ovarian | TTC7A |
| chr2 | 47597455 | 47598620 | Hypo | cancer_general | MIR559, EPCAM |
| chr2 | 48629615 | 48629685 | Hypo | cancer_general | — |
| chr2 | 48648878 | 48648940 | Hypo | cancer_general | — |
| chr2 | 54322431 | 54322576 | Hypo | lung | — |
| chr2 | 55612770 | 55612800 | Hypo | colorectal | — |
| chr2 | 58552519 | 58552689 | Hypo | cancer_general | — |
| chr2 | 60416280 | 60416494 | Hypo | cancer_general | — |
| chr2 | 61135032 | 61135137 | Hypo | breast | REL |
| chr2 | 13557899 | 13558057 | Hypo | hepatobiliary | PUM2 |
| chr2 | 20442433 | 20442498 | Hypo | cancer_general | RHOB |
| chr2 | 20642541 | 20642648 | Hypo | cancer_general | — |
| chr2 | 22404181 | 22404227 | Hypo | cancer_general | CENPO |
| chr2 | 25029252 | 25029300 | Hypo | cancer_general | — |
| chr2 | 25439727 | 25439915 | Hypo | cancer_general | — |
| chr2 | 25928094 | 25928166 | Hypo | head_neck | Y_RNA |
| chr2 | 27271699 | 27272218 | Hypo | cancer_general | TMEM214, TRNA, TRNA_Tyr, TRNA_Ala, AGBL5 |
| chr2 | 27433532 | 27433601 | Hypo | cancer_general | ATRAID, CAD, SLC5A6 |
| chr2 | 27578243 | 27578396 | Hypo | cancer_general | EIF2B4 |
| chr2 | 27764046 | 27764168 | Hypo | cancer_general | — |
| chr2 | 29091592 | 29091838 | Hypo | cancer_general | TRMT61B |
| chr2 | 29432640 | 29432696 | Hypo | literature | ALK |
| chr2 | 29443573 | 29443710 | Hypo | literature | ALK |
| chr2 | 29446181 | 29446396 | Hypo | literature | ALK |
| chr2 | 30514753 | 30514783 | Hypo | hepatobiliary | YIPF4 |
| chr2 | 32504169 | 32504378 | Hypo | cancer_general | CYP1B1-AS1 |
| chr2 | 38365525 | 38365748 | Hypo | cancer_general | ATL2 |
| chr2 | 38594819 | 38594874 | Hypo | breast | — |
| chr2 | 38762382 | 38762412 | Hypo | colorectal | — |
| chr2 | 38983213 | 38983333 | Hypo | head_neck | GEMIN6, SRSF7 |
| chr2 | 43388330 | 43388529 | Hypo | colorectal, cancer_general | — |
| chr2 | 44226958 | 44226988 | Hypo | head_neck | LRPPRC |
| chr2 | 44497708 | 44497875 | Hypo | breast | SLC3A1 |
| chr2 | 47193930 | 47194136 | Hypo | pancreas, cancer_general | TTC7A |
| chr2 | 47249725 | 47249848 | Hypo | ovarian | — |
| chr2 | 47599589 | 47599753 | Hypo | cancer_general | TTC7A |
| chr2 | 48636504 | 48636669 | Hypo | cancer_general | MIR559, EPCAM |
| chr2 | 50573802 | 50573865 | Hypo | cancer_general | NRXN1 |
| chr2 | 55289011 | 55289296 | Hypo | lung | — |
| chr2 | 55669261 | 55669454 | Hypo | cancer_general | — |
| chr2 | 59400384 | 59400424 | Hypo | cancer_general | — |
| chr2 | 60706759 | 60706804 | Hypo | cancer_general | — |
| chr2 | 61232163 | 61232232 | Hypo | cancer_general | BCL11A, PUS10, 5S_rRNA |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 61242732 | 61242802 | Hypo | cancer_general | PEX13, PUS10 | chr2 | 61395039 | 61395069 | Hypo | cancer_general | C2orf74, AHSA2 |
| chr2 | 61556203 | 61556239 | Hypo | cancer_general | | chr2 | 61656393 | 61656423 | Hypo | breast | |
| chr2 | 61992076 | 61992289 | Hypo | cancer_general | | chr2 | 65251310 | 65251340 | Hypo | head_neck | SLC1A4 |
| chr2 | 65779892 | 65779983 | Hypo | cancer_general | FLJ16124 | chr2 | 67625453 | 67625770 | Hypo | cancer_general | ETAA1 |
| chr2 | 67626102 | 67626257 | Hypo | cancer_general | ETAA1 | chr2 | 68287707 | 68287799 | Hypo | head_neck | C1D |
| chr2 | 68559261 | 68559365 | Hypo | cancer_general | | chr2 | 68672853 | 68672938 | Hypo | cancer_general | |
| chr2 | 69027024 | 69027053 | Hypo | literature | ARHGAP25 | chr2 | 69975443 | 69975523 | Hypo | pancreas | ANXA4 |
| chr2 | 70058262 | 70058292 | Hypo | cancer_general | GMCL1 | chr2 | 70367670 | 70367710 | Hypo | lung | C2orf42 |
| chr2 | 70418528 | 70418627 | Hypo | cancer_general | C2orf42 | chr2 | 70427556 | 70427646 | Hypo | lung | TIA1, C2orf42 |
| chr2 | 70430997 | 70431160 | Hypo | cancer_general | TIA1 | chr2 | 71355019 | 71355117 | Hypo | cancer_general | MPHOSPH10, MCEE |
| chr2 | 71355768 | 71355961 | Hypo | cancer_general | MPHOSPH10, MCEE | chr2 | 73147353 | 73147383 | Hypo | cancer_general | EMX1 |
| chr2 | 73416356 | 73416535 | Hypo | lung | | chr2 | 73440206 | 73440293 | Hypo | cancer_general | SMYD5, NOTO |
| chr2 | 74010528 | 74010773 | Hypo | cancer_general | C2orf78, DUSP11 | chr2 | 74153198 | 74153227 | Hypo | literature | DGUOK, ACTG2 |
| chr2 | 74350410 | 74350497 | Hypo | cancer_general | | chr2 | 74454074 | 74454261 | Hypo | cancer_general | SLC4A5 |
| chr2 | 74647864 | 74648007 | Hypo | cancer_general | WDR54, RTKN, DQ588163, C20orf81 | chr2 | 74679047 | 74679123 | Hypo | cancer_general | INO80B, INO80B-WBP1, WBP1, MOGS, RTKN |
| chr2 | 74874865 | 74874903 | Hypo | cancer_general | SEMA4F | chr2 | 79347459 | 79347546 | Hypo | literature | REG1A |
| chr2 | 85838101 | 85838299 | Hypo | cancer_general | C2orf68, TMEM150A, USP39 | chr2 | 86191145 | 86191309 | Hypo | cancer_general | |
| chr2 | 86423330 | 86423592 | Hypo | cancer_general | MRPL35, MIR4779, IMMT | chr2 | 86783725 | 86783755 | Hypo | cancer_general | RNF103-CHMP3, CHMP3 |
| chr2 | 86791221 | 86791251 | Hypo | ovarian | RNF103-CHMP3, CHMP3 | chr2 | 88469312 | 88469483 | Hypo | cancer_general | THNSL2 |
| chr2 | 88990189 | 88990264 | Hypo | cancer_general | RPIA | chr2 | 89252535 | 89252679 | Hypo | cancer_general | |
| chr2 | 95941678 | 95941812 | Hypo | ovarian | PROM2 | chr2 | 96070057 | 96070165 | Hypo | breast | FAHD2A |
| chr2 | 96974486 | 96974516 | Hypo | lung | | chr2 | 97126702 | 97126832 | Hypo | head_neck | |
| chr2 | 97427515 | 97428093 | Hypo | cancer_general | CNNM4 | chr2 | 97581819 | 97581849 | Hypo | colorectal | TMEM131 |
| chr2 | 99796259 | 99796330 | Hypo | cancer_general | MRPL30, MITD1 | chr2 | 99798646 | 99799153 | Hypo | cancer_general | MRPL30, MITD1 |
| chr2 | 100618451 | 100618480 | Hypo | literature | AFF3 | chr2 | 101009832 | 101009927 | Hypo | cancer_general | CHST10 |
| chr2 | 101186368 | 101186458 | Hypo | ovarian | PDCL3 | chr2 | 101834977 | 101835057 | Hypo | cancer_general | |
| chr2 | 105488437 | 105488496 | Hypo | cancer_general | AK095498 | chr2 | 105937344 | 105937498 | Hypo | cancer_general | TGFBRAP1 |
| chr2 | 106060615 | 106060792 | Hypo | lung | | chr2 | 106730223 | 106730256 | Hypo | cancer_general | UXS1 |
| chr2 | 106959368 | 106959568 | Hypo | cancer_general | | chr2 | 106959916 | 106959988 | Hypo | cancer_general | |
| chr2 | 108364897 | 108364940 | Hypo | cancer_general | | chr2 | 109335133 | 109335166 | Hypo | cancer_general | RANBP2 |
| chr2 | 110015080 | 110015110 | Hypo | ovarian | | chr2 | 111544817 | 111544997 | Hypo | cancer_general | ACOXL |
| chr2 | 112817735 | 112817765 | Hypo | colorectal | TMEM87B | chr2 | 113227024 | 113227225 | Hypo | esophageal | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 113803960 | 113803990 | Hypo | cancer_general | IL36B | chr2 | 144461746 | 114461879 | Hypo | colorectal | SLC35F5 |
| chr2 | 114470022 | 114470201 | Hypo | ovarian | SLC35F5, MIR4782 | chr2 | 114515528 | 114515618 | Hypo | cancer_general | SLC35F5 |
| chr2 | 114634867 | 114634988 | Hypo | cancer_general | — | chr2 | 118380865 | 118380904 | Hypo | pancreas | — |
| chr2 | 119600570 | 119600747 | Hypo | cancer_general | EN1 | chr2 | 120769511 | 120769746 | Hypo | cancer_general | EPB41L5 |
| chr2 | 120825608 | 120825769 | Hypo | lung | EPB41L5 | chr2 | 120980068 | 120980098 | Hypo | cancer_general | TMEM185B |
| chr2 | 120980353 | 120980395 | Hypo | cancer_general | TMEM185B | chr2 | 122495267 | 122495413 | Hypo | cancer_general | MKI67IP |
| chr2 | 122809705 | 122809801 | Hypo | cancer_general | — | chr2 | 127412297 | 127412386 | Hypo | cancer_general | GYPC |
| chr2 | 127423220 | 127423350 | Hypo | cancer_general | GYPC | chr2 | 127429010 | 127429044 | Hypo | cancer_general | GYPC |
| chr2 | 127438633 | 127438663 | Hypo | cancer_general | GYPC | chr2 | 128616617 | 128616838 | Hypo | cancer_general | AMMECR1L, POLR2D |
| chr2 | 128680057 | 128680087 | Hypo | cancer_general | — | chr2 | 128847677 | 128847723 | Hypo | cancer_general | UGGT1 |
| chr2 | 129174888 | 129174918 | Hypo | cancer_general | — | chr2 | 130937868 | 130937898 | Hypo | cancer_general | MZT2B, FLJ14346, SMPD4 |
| chr2 | 131084953 | 131085013 | Hypo | cancer_general | TRNA_Glu | chr2 | 131477785 | 131477936 | Hypo | cancer_general | GPR148 |
| chr2 | 132208115 | 132208278 | Hypo | cancer_general | LOC401010 | chr2 | 136287358 | 136287390 | Hypo | cancer_general | R3HDM1, ZRANB3 |
| chr2 | 143569561 | 143569694 | Hypo | cancer_general | — | chr2 | 144129765 | 144129795 | Hypo | cancer_general | ARHGAP15 |
| chr2 | 144299758 | 144299788 | Hypo | cancer_general | ARHGAP15 | chr2 | 148776809 | 148777035 | Hypo | cancer_general | MBD5, ORC4 |
| chr2 | 152248836 | 152248983 | Hypo | cancer_general | PSMD14 | chr2 | 161253293 | 161253455 | Hypo | cancer_general | RBMS1 |
| chr2 | 162166600 | 162166632 | Hypo | cancer_general | — | chr2 | 166929478 | 166929613 | Hypo | cancer_general | BC051759, SCN1A |
| chr2 | 170255970 | 170256139 | Hypo | cancer_general | KLHL41 | chr2 | 170282981 | 170283080 | Hypo | cancer_general | — |
| chr2 | 170373281 | 170373413 | Hypo | lung | | chr2 | 170551730 | 170551942 | Hypo | cancer_general, literature | PHOSPHO2, PHOSPHO2-KLHL23, CCDC173 |
| chr2 | 170681880 | 170682422 | Hypo | cancer_general | UBR3, METTL5 | chr2 | 171822428 | 171822480 | Hypo | pancreas | GORASP2 |
| chr2 | 171839017 | 171839047 | Hypo | cancer_general | TLK1 | chr2 | 172367021 | 172367125 | Hypo | colorectal | — |
| chr2 | 172411136 | 172411166 | Hypo | cancer_general | CYBRD1 | chr2 | 172973111 | 172973141 | Hypo | cancer_general | DLX2 |
| chr2 | 173422685 | 173422734 | Hypo | cancer_general | PDK1 | chr2 | 174148058 | 174148157 | Hypo | head_neck | MLK7-AS1 |
| chr2 | 175111870 | 175112092 | Hypo | cancer_general | OLA1 | chr2 | 175261402 | 175261432 | Hypo | cancer_general | SCRN3, CIR1 |
| chr2 | 175383935 | 175383965 | Hypo | cancer_general | — | chr2 | 176987367 | 176987397 | Hypo | pancreas | HOXD9, AX747372, HOXD8, HOXD10 |
| chr2 | 176994031 | 176994136 | Hypo | cancer_general | HOXD9, HOXD10, HOXD8, HOXD-AS2, BC047605, AX747372 | chr2 | 177872600 | 177872629 | Hypo | literature | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 178098791 | 178098967 | Hypo | literature | NFE2L2 | chr2 | 178973003 | 178973042 | Hypo | ovarian | RBM45 |
| chr2 | 179303534 | 179303727 | Hypo | cancer_general | AX747806, PRKRA, BX538254, MIR548N | chr2 | 179316860 | 179317057 | Hypo | cancer_general | DFNB59 |
| chr2 | 182202233 | 182202291 | Hypo | cancer_general |  | chr2 | 183251240 | 183251303 | Hypo | hepatobiliary | PDE1A |
| chr2 | 190708790 | 190708819 | Hypo | literature | PMS1 | chr2 | 197793125 | 197793267 | Hypo | cancer_general | PGAP1 |
| chr2 | 198238409 | 198238439 | Hypo | cancer_general |  | chr2 | 198267345 | 198267374 | Hypo | literature | SnR39B, SF3B1 |
| chr2 | 198456480 | 198456719 | Hypo | cancer_general | RFTN2 | chr2 | 200818892 | 200819130 | Hypo | cancer_general | C2orf47, TYW5 |
| chr2 | 201156690 | 201156804 | Hypo | ovarian |  | chr2 | 201693680 | 201693718 | Hypo | colorectal | BZW1 |
| chr2 | 202477462 | 202477621 | Hypo | cancer_general | TMEM237, ALS2CR11 | chr2 | 203484608 | 203484646 | Hypo | cancer_general |  |
| chr2 | 203498452 | 203498489 | Hypo | ovarian | FAM117B | chr2 | 203880390 | 203880492 | Hypo | cancer_general | NBEAL1 |
| chr2 | 204194588 | 204194725 | Hypo | cancer_general | ABI2 | chr2 | 207022702 | 207022802 | Hypo | cancer_general | EEF1B2, SNORD51, SNORA41, NDUFS1 |
| chr2 | 208574821 | 208574917 | Hypo | cancer_general | CCNYL1 | chr2 | 208588311 | 208588341 | Hypo | cancer_general | CCNYL1 |
| chr2 | 208662170 | 208662376 | Hypo | lung |  | chr2 | 208662672 | 208662710 | Hypo | lung |  |
| chr2 | 209094739 | 209094845 | Hypo | cancer_general | IDH1 | chr2 | 209113097 | 209113126 | Hypo | literature | IDH1-AS1, IDH1 |
| chr2 | 209225237 | 209225275 | Hypo | ovarian | PTH2R | chr2 | 212248428 | 212248457 | Hypo | literature | ERBB4 |
| chr2 | 212288927 | 212288956 | Hypo | literature | ERBB4 | chr2 | 212295683 | 212295820 | Hypo | literature | ERBB4 |
| chr2 | 212530120 | 212530149 | Hypo | literature | ERBB4 | chr2 | 212537902 | 212537994 | Hypo | literature | ERBB4 |
| chr2 | 212566811 | 212566840 | Hypo | literature | ERBB4 | chr2 | 212578292 | 212578321 | Hypo | literature | ERBB4 |
| chr2 | 212587132 | 212587161 | Hypo | literature | ERBB4 | chr2 | 215276310 | 215276339 | Hypo | literature | VWC2L |
| chr2 | 217396039 | 217396069 | Hypo | ovarian | VIL1, MIR26B, CTDSP1 | chr2 | 217448294 | 1217448441 | Hypo | esophageal | ABCB6, ZFAND2B, ATG9A |
| chr2 | 219276888 | 219276918 | Hypo | blood |  | chr2 | 220080510 | 220081033 | Hypo | ovarian |  |
| chr2 | 221853201 | 221853352 | Hypo | hepatobiliary |  | chr2 | 222285828 | 222285858 | Hypo | hepatobiliary | EPHA4 |
| chr2 | 222310068 | 222310105 | Hypo | hepatobiliary | EPHA4 | chr2 | 223166270 | 223166408 | Hypo | cancer_general | CCDC140, DD413687, PAX3 |
| chr2 | 224661521 | 224661701 | Hypo | pancreas | AP1S3 | chr2 | 225464038 | 225464068 | Hypo | cancer_general |  |
| chr2 | 228411020 | 228411050 | Hypo | cancer_general | AGFG1 | chr2 | 228466625 | 228466777 | Hypo | cancer_general | C2orf83 |
| chr2 | 228638272 | 228638302 | Hypo | lung |  | chr2 | 228735680 | 228735736 | Hypo | cancer_general | DAW1 |
| chr2 | 230795535 | 230795565 | Hypo | lung | TRIP12, FBXO36 | chr2 | 231576609 | 231576643 | Hypo | cancer_general | CAB39 |
| chr2 | 232330451 | 232330481 | Hypo | cancer_general | SNORD82, SNORD20, SNORA75, NCL | chr2 | 232506220 | 232506294 | Hypo | cancer_general |  |
| chr2 | 232506605 | 232506635 | Hypo | cancer_general |  | chr2 | 232522844 | 232522874 | Hypo | cancer_general |  |
| chr2 | 232544500 | 232544530 | Hypo | cancer_general |  | chr2 | 232546736 | 232546842 | Hypo | cancer_general |  |
| chr2 | 232827168 | 232827349 | Hypo | cancer_general | DIS3L2 | chr2 | 233073078 | 233073223 | Hypo | ovarian |  |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 233220027 | 233220382 | Hypo | cancer_general | — | chr2 | 233750525 | 233750555 | Hypo | cancer_general | NGEF, C2orf82 |
| chr2 | 234776483 | 234776553 | Hypo | cancer_general | MSL3P1 | chr2 | 236444269 | 236444298 | Hypo | literature | AGAP1 |
| chr2 | 236877262 | 236877399 | Hypo | lung | AGAP1 | chr2 | 239031722 | 239031780 | Hypo | cancer_general | ESPNL |
| chr2 | 239051198 | 239051228 | Hypo | cancer_general | KLHL30, ESPNL | chr2 | 239265496 | 239265787 | Hypo | cancer_general | TRAF3IP1 |
| chr2 | 239482485 | 239482519 | Hypo | cancer_general | — | chr2 | 239705305 | 239705337 | Hypo | cancer_general | U4 |
| chr2 | 239957330 | 239957448 | Hypo | cancer_general | — | chr2 | 240167575 | 240167605 | Hypo | cancer_general | — |
| chr2 | 240168811 | 240169051 | Hypo | cancer_general | — | chr2 | 240319920 | 240320012 | Hypo | ovarian | — |
| chr2 | 240582379 | 240582524 | Hypo | cancer_general | — | chr2 | 240619459 | 240619604 | Hypo | cancer_general | — |
| chr2 | 240658227 | 240658421 | Hypo | cancer_general | — | chr2 | 240638667 | 240658697 | Hypo | cancer_general | — |
| chr2 | 240812243 | 240812374 | Hypo | cancer_general | — | chr2 | 241095604 | 241095772 | Hypo | cancer_general | — |
| chr2 | 241541932 | 241542357 | Hypo | cancer_general, colorectal | GPR35, CAPN10 | chr2 | 241545001 | 241545031 | Hypo | cancer_general | GPR35, CAPN10 |
| chr2 | 241865194 | 241865346 | Hypo | cancer_general | SNED1 | chr2 | 242009391 | 242009421 | Hypo | cancer_general | SNED1 |
| chr2 | 242021784 | 242021892 | Hypo | cancer_general | 5S_rRNA, THAP4 | chr2 | 242314494 | 242314524 | Hypo | cancer_general | FARP2 |
| chr2 | 242523907 | 242524147 | Hypo | lung, cancer_general | — | chr2 | 242554549 | 242554579 | Hypo | cancer_general | — |
| chr2 | 242636726 | 242636812 | Hypo | cancer_general | ING5 | chr2 | 242640015 | 242640045 | Hypo | cancer_general | ING5 |
| chr2 | 242716723 | 242716760 | Hypo | cancer_general | GAL3ST2, D2HGDH | chr2 | 242756144 | 242756297 | Hypo | cancer_general | NEU4, PABL |
| chr2 | 242832984 | 242833159 | Hypo | cancer_general | — | chr2 | 242833558 | 242833588 | Hypo | cancer_general | — |
| chr2 | 242833797 | 242833863 | Hypo | cancer_general | — | chr2 | 242836495 | 242836640 | Hypo | cancer_general | — |
| chr2 | 242925496 | 242925641 | Hypo | cancer_general | AK097934 | chrY | 3446305 | 3446441 | Hypo | hepatobiliary | TGIF2LY |
| chrY | 3838889 | 3838919 | Hypo | pancreas | — | chrY | 3968100 | 3968132 | Hypo | hepatobiliary | — |
| chrY | 13316007 | 13316132 | Hypo | esophageal | — | chrY | 21204734 | 21205113 | Hypo | head_neck | — |
| chrY | 22530026 | 22530073 | Hypo | head_neck | — | HHV5-CINCY-TOWNE | 1181 | 1210 | Hypo | virus | — |
| HHV5-CINCY-TOWNE | 1988 | 2017 | Hypo | virus | — | HHV5-CINCY-TOWNE | 2389 | 2418 | Hypo | virus | — |
| HHV5-CINCY-TOWNE | 3290 | 3319 | Hypo | virus | — | HHV5-CINCY-TOWNE | 3665 | 3694 | Hypo | virus | — |
| HHV5-CINCY-TOWNE | 4704 | 4733 | Hypo | virus | — | HHV5-CINCY-TOWNE | 5400 | 5429 | Hypo | virus | — |
| HHV5-CINCY-TOWNE | 7790 | 7819 | Hypo | virus | — | HHV5-CINCY-TOWNE | 9656 | 9685 | Hypo | virus | — |
| HHV5-CINCY-TOWNE | 10781 | 10810 | Hypo | virus | — | HHV5-CINCY-TOWNE | 11109 | 11138 | Hypo | virus | — |
| HHV5-CINCY-TOWNE | 12663 | 12692 | Hypo | virus | — | HHV5-CINCY-TOWNE | 13688 | 13717 | Hypo | virus | — |
| HHV5-CINCY-TOWNE | 14223 | 14252 | Hypo | virus | — | HHV5-CINCY-TOWNE | 14911 | 14940 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 15206 | 15235 | Hypo | virus | — | HHV5-CINCY-TOWNE | 15938 | 15967 | Hypo | virus | — |
| HHV5-CINCY-TOWNE | 16440 | 16469 | Hypo | virus | — | HHV5-CINCY-TOWNE | 16884 | 16913 | Hypo | virus | — |
| HHV5-CINCY-TOWNE | 17347 | 17376 | Hypo | virus | — | HHV5-CINCY-TOWNE | 17696 | 17725 | Hypo | virus | — |
| HHV5-CINCY-TOWNE | 17958 | 17987 | Hypo | virus | — | HHV5-CINCY-TOWNE | 18372 | 18401 | Hypo | virus | — |
| HHV5-CINCY-TOWNE | 19417 | 19446 | Hypo | virus | — | HHV5-CINCY-TOWNE | 19910 | 19939 | Hypo | virus | — |
| HHV5-CINCY-TOWNE | 20248 | 20277 | Hypo | virus | — | HHV5-CINCY-TOWNE | 20671 | 20700 | Hypo | virus | — |
| HHV5-CINCY-TOWNE | 21899 | 21928 | Hypo | virus | — | HHV5-CINCY-TOWNE | 22798 | 22827 | Hypo | virus | — |
| HHV5-CINCY-TOWNE | 23095 | 23124 | Hypo | virus | — | HHV5-CINCY-TOWNE | 26713 | 26742 | Hypo | virus | — |
| HHV5-CINCY-TOWNE | 27211 | 27240 | Hypo | virus | — | HHV5-CINCY-TOWNE | 29784 | 29813 | Hypo | virus | — |
| HHV5-CINCY-TOWNE | 31141 | 31170 | Hypo | virus | — | HHV5-CINCY-TOWNE | 32660 | 32689 | Hypo | virus | — |
| HHV5-CINCY-TOWNE | 35651 | 35680 | Hypo | virus | — | HHV5-CINCY-TOWNE | 36393 | 36422 | Hypo | virus | — |
| HHV5-CINCY-TOWNE | 37224 | 37253 | Hypo | virus | — | HHV5-CINCY-TOWNE | 37895 | 37924 | Hypo | virus | — |
| HHV5-CINCY-TOWNE | 39244 | 39273 | Hypo | virus | — | HHV5-CINCY-TOWNE | 43188 | 43217 | Hypo | virus | — |
| HHV5-CINCY-TOWNE | 44447 | 44476 | Hypo | virus | — | HHV5-CINCY-TOWNE | 44799 | 44828 | Hypo | virus | — |
| HHV5-CINCY-TOWNE | 45394 | 45423 | Hypo | virus | — | HHV5-CINCY-TOWNE | 46445 | 46474 | Hypo | virus | — |
| HHV5-CINCY-TOWNE | 46944 | 46973 | Hypo | virus | — | HHV5-CINCY-TOWNE | 47916 | 47945 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 48504 | 48533 | Hypo | virus | — | HHV5-CINCY-TOWNE | 49094 | 49123 | Hypo | virus | — |
| HHV5-CINCY-TOWNE | 49903 | 49932 | Hypo | virus | — | HHV5-CINCY-TOWNE | 50230 | 50259 | Hypo | virus | — |
| HHV5-CINCY-TOWNE | 51421 | 51450 | Hypo | virus | — | HHV5-CINCY-TOWNE | 53772 | 53801 | Hypo | virus | — |
| HHV5-CINCY-TOWNE | 55651 | 55680 | Hypo | virus | — | HHV5-CINCY-TOWNE | 56380 | 56409 | Hypo | virus | — |
| HHV5-CINCY-TOWNE | 57291 | 57320 | Hypo | virus | — | HHV5-CINCY-TOWNE | 58491 | 58520 | Hypo | virus | — |
| HHV5-CINCY-TOWNE | 59023 | 59052 | Hypo | virus | — | HHV5-CINCY-TOWNE | 59792 | 59821 | Hypo | virus | — |
| HHV5-CINCY-TOWNE | 60124 | 60153 | Hypo | virus | — | HHV5-CINCY-TOWNE | 60392 | 60421 | Hypo | virus | — |
| HHV5-CINCY-TOWNE | 60900 | 60929 | Hypo | virus | — | HHV5-CINCY-TOWNE | 63894 | 63923 | Hypo | virus | — |
| HHV5-CINCY-TOWNE | 65843 | 65872 | Hypo | virus | — | HHV5-CINCY-TOWNE | 68089 | 68118 | Hypo | virus | — |
| HHV5-CINCY-TOWNE | 72454 | 72483 | Hypo | virus | — | HHV5-CINCY-TOWNE | 81185 | 81214 | Hypo | virus | — |
| HHV5-CINCY-TOWNE | 84144 | 84173 | Hypo | virus | — | HHV5-CINCY-TOWNE | 85524 | 85553 | Hypo | virus | — |
| HHV5-CINCY-TOWNE | 85943 | 85972 | Hypo | virus | — | HHV5-CINCY-TOWNE | 86889 | 86918 | Hypo | virus | — |
| HHV5-CINCY-TOWNE | 87195 | 87224 | Hypo | virus | — | HHV5-CINCY-TOWNE | 87455 | 87484 | Hypo | virus | — |
| HHV5-CINCY-TOWNE | 87769 | 87798 | Hypo | virus | — | HHV5-CINCY-TOWNE | 88564 | 88593 | Hypo | virus | — |
| HHV5-CINCY-TOWNE | 93096 | 93125 | Hypo | virus | — | HHV5-CINCY-TOWNE | 93776 | 93805 | Hypo | virus | — |
| HHV5-CINCY-TOWNE | 97621 | 97650 | Hypo | virus | — | HHV5-CINCY-TOWNE | 98737 | 98766 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 99460 | 99489 | Hypo | virus | — | HHV5-CINCY-TOWNE | 107540 | 107569 | Hypo | virus | — |
| HHV5-CINCY-TOWNE | 108823 | 108852 | Hypo | virus | — | HHV5-CINCY-TOWNE | 109725 | 109754 | Hypo | virus | — |
| HHV5-CINCY-TOWNE | 112036 | 112065 | Hypo | virus | — | HHV5-CINCY-TOWNE | 112319 | 112348 | Hypo | virus | — |
| HHV5-CINCY-TOWNE | 112595 | 112624 | Hypo | virus | — | HHV5-CINCY-TOWNE | 112892 | 112921 | Hypo | virus | — |
| HHV5-CINCY-TOWNE | 113194 | 113223 | Hypo | virus | — | HHV5-CINCY-TOWNE | 113535 | 113564 | Hypo | virus | — |
| HHV5-CINCY-TOWNE | 113927 | 113956 | Hypo | virus | — | HHV5-CINCY-TOWNE | 114267 | 114296 | Hypo | virus | — |
| HHV5-CINCY-TOWNE | 114593 | 114622 | Hypo | virus | — | HHV5-CINCY-TOWNE | 114867 | 114896 | Hypo | virus | — |
| HHV5-CINCY-TOWNE | 115177 | 115206 | Hypo | virus | — | HHV5-CINCY-TOWNE | 115432 | 115461 | Hypo | virus | — |
| HHV5-CINCY-TOWNE | 115685 | 115714 | Hypo | virus | — | HHV5-CINCY-TOWNE | 115986 | 116015 | Hypo | virus | — |
| HHV5-CINCY-TOWNE | 116382 | 116411 | Hypo | virus | — | HHV5-CINCY-TOWNE | 116700 | 116729 | Hypo | virus | — |
| HHV5-CINCY-TOWNE | 118193 | 118222 | Hypo | virus | — | HHV5-CINCY-TOWNE | 118995 | 119024 | Hypo | virus | — |
| HHV5-CINCY-TOWNE | 120028 | 120057 | Hypo | virus | — | HHV5-CINCY-TOWNE | 121485 | 121514 | Hypo | virus | — |
| HHV5-CINCY-TOWNE | 122199 | 122228 | Hypo | virus | — | HHV5-CINCY-TOWNE | 122606 | 122635 | Hypo | virus | — |
| HHV5-CINCY-TOWNE | 124559 | 124588 | Hypo | virus | — | HHV5-CINCY-TOWNE | 125276 | 125305 | Hypo | virus | — |
| HHV5-CINCY-TOWNE | 132497 | 132526 | Hypo | virus | — | HHV5-CINCY-TOWNE | 135460 | 135489 | Hypo | virus | — |
| HHV5-CINCY-TOWNE | 135730 | 135759 | Hypo | virus | — | HHV5-CINCY-TOWNE | 137379 | 137408 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 139067 | 139096 | Hypo | virus | — | HHV5-CINCY-TOWNE | 139472 | 139501 | Hypo | virus | — |
| HHV5-CINCY-TOWNE | 140147 | 140176 | Hypo | virus | — | HHV5-CINCY-TOWNE | 140722 | 140751 | Hypo | virus | — |
| HHV5-CINCY-TOWNE | 142023 | 142052 | Hypo | virus | — | HHV5-CINCY-TOWNE | 143692 | 143721 | Hypo | virus | — |
| HHV5-CINCY-TOWNE | 144080 | 144109 | Hypo | virus | — | HHV5-CINCY-TOWNE | 147310 | 147339 | Hypo | virus | — |
| HHV5-CINCY-TOWNE | 149465 | 149494 | Hypo | virus | — | HHV5-CINCY-TOWNE | 150359 | 150388 | Hypo | virus | — |
| HHV5-CINCY-TOWNE | 151593 | 151622 | Hypo | virus | — | HHV5-CINCY-TOWNE | 152153 | 152182 | Hypo | virus | — |
| HHV5-CINCY-TOWNE | 154148 | 154177 | Hypo | virus | — | HHV5-CINCY-TOWNE | 154610 | 154639 | Hypo | virus | — |
| HHV5-CINCY-TOWNE | 157018 | 157047 | Hypo | virus | — | HHV5-CINCY-TOWNE | 157367 | 157396 | Hypo | virus | — |
| HHV5-CINCY-TOWNE | 169038 | 169067 | Hypo | virus | — | HHV5-CINCY-TOWNE | 171503 | 171532 | Hypo | virus | — |
| HHV5-CINCY-TOWNE | 175146 | 175175 | Hypo | virus | — | HHV5-CINCY-TOWNE | 177553 | 177582 | Hypo | virus | — |
| HHV5-CINCY-TOWNE | 182254 | 182283 | Hypo | virus | — | HHV5-CINCY-TOWNE | 183115 | 183144 | Hypo | virus | — |
| HHV5-CINCY-TOWNE | 184120 | 184149 | Hypo | virus | — | HHV5-CINCY-TOWNE | 185558 | 185587 | Hypo | virus | — |
| HHV5-CINCY-TOWNE | 186027 | 186056 | Hypo | virus | — | HHV5-CINCY-TOWNE | 186435 | 186464 | Hypo | virus | — |
| HHV5-CINCY-TOWNE | 186707 | 186736 | Hypo | virus | — | HHV5-CINCY-TOWNE | 187115 | 187144 | Hypo | virus | — |
| HHV5-CINCY-TOWNE | 187514 | 187543 | Hypo | virus | — | HHV5-CINCY-TOWNE | 187859 | 187888 | Hypo | virus | — |
| HHV5-CINCY-TOWNE | 188473 | 188502 | Hypo | virus | — | HHV5-CINCY-TOWNE | 188768 | 188797 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 189050 | 189079 | Hypo | virus | — | HHV5-CINCY-TOWNE | 189302 | 189331 | Hypo | virus | — |
| HHV5-CINCY-TOWNE | 189936 | 189965 | Hypo | virus | — | HHV5-CINCY-TOWNE | 190655 | 190684 | Hypo | virus | — |
| HHV5-CINCY-TOWNE | 190954 | 190983 | Hypo | virus | — | HHV5-CINCY-TOWNE | 191453 | 191482 | Hypo | virus | — |
| HHV5-CINCY-TOWNE | 191882 | 191911 | Hypo | virus | — | HHV5-CINCY-TOWNE | 192183 | 192212 | Hypo | virus | — |
| HHV5-CINCY-TOWNE | 192541 | 192570 | Hypo | virus | — | HHV5-CINCY-TOWNE | 193045 | 193074 | Hypo | virus | — |
| HHV5-CINCY-TOWNE | 193325 | 193354 | Hypo | virus | — | HHV5-CINCY-TOWNE | 193597 | 193626 | Hypo | virus | — |
| HHV5-CINCY-TOWNE | 194165 | 194194 | Hypo | virus | — | HHV5-CINCY-TOWNE | 194461 | 194490 | Hypo | virus | — |
| HHV5-CINCY-TOWNE | 194848 | 194877 | Hypo | virus | — | HHV5-CINCY-TOWNE | 195324 | 195353 | Hypo | virus | — |
| HHV5-CINCY-TOWNE | 195651 | 195680 | Hypo | virus | — | HHV5-CINCY-TOWNE | 196018 | 196047 | Hypo | virus | — |
| HHV5-CINCY-TOWNE | 196343 | 196372 | Hypo | virus | — | HHV5-CINCY-TOWNE | 196941 | 196970 | Hypo | virus | — |
| HHV5-CINCY-TOWNE | 197218 | 197247 | Hypo | virus | — | HHV5-CINCY-TOWNE | 198315 | 198344 | Hypo | virus | — |
| HHV5-CINCY-TOWNE | 198792 | 198821 | Hypo | virus | — | HHV5-CINCY-TOWNE | 199162 | 199191 | Hypo | virus | — |
| HHV5-CINCY-TOWNE | 200113 | 200142 | Hypo | virus | — | HHV5-CINCY-TOWNE | 200571 | 200600 | Hypo | virus | — |
| HHV5-CINCY-TOWNE | 201373 | 201402 | Hypo | virus | — | HHV5-CINCY-TOWNE | 201905 | 201934 | Hypo | virus | — |
| HHV5-CINCY-TOWNE | 202264 | 202293 | Hypo | virus | — | HHV5-CINCY-TOWNE | 202537 | 202566 | Hypo | virus | — |
| HHV5-CINCY-TOWNE | 203319 | 203348 | Hypo | virus | — | HHV5-CINCY-TOWNE | 203720 | 203749 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 204008 | 204037 | Hypo | virus | — | HHV5-CINCY-TOWNE | 206213 | 206242 | Hypo | virus | — |
| HHV5-CINCY-TOWNE | 206735 | 206764 | Hypo | virus | — | HHV5-CINCY-TOWNE | 211676 | 211705 | Hypo | virus | — |
| HHV5-CINCY-TOWNE | 212340 | 212369 | Hypo | virus | — | HHV5-CINCY-TOWNE | 212609 | 212638 | Hypo | virus | — |
| HHV5-CINCY-TOWNE | 213813 | 213842 | Hypo | virus | — | HHV5-CINCY-TOWNE | 214695 | 214724 | Hypo | virus | — |
| HHV5-CINCY-TOWNE | 214950 | 214979 | Hypo | virus | — | HHV5-CINCY-TOWNE | 215930 | 215959 | Hypo | virus | — |
| HHV5-CINCY-TOWNE | 216228 | 216257 | Hypo | virus | — | HHV5-CINCY-TOWNE | 222672 | 222701 | Hypo | virus | — |
| HHV5-CINCY-TOWNE | 223515 | 223544 | Hypo | virus | — | HHV5-CINCY-TOWNE | 225150 | 225179 | Hypo | virus | — |
| HHV5-CINCY-TOWNE | 226058 | 226087 | Hypo | virus | — | HHV5-CINCY-TOWNE | 226887 | 226916 | Hypo | virus | — |
| chr20 | 118577 | 118751 | Hypo | cancer_general | DEFB126 | chr20 | 304259 | 304408 | Hypo | cancer_general | SOX12 |
| chr20 | 400007 | 400087 | Hypo | cancer_general | RBCK1 | chr20 | 401153 | 401183 | Hypo | cancer_general | RBCK1 |
| chr20 | 401591 | 401756 | Hypo | cancer_general | RBCK1 | chr20 | 523146 | 523193 | Hypo | cancer_general | CSNK2A1 |
| chr20 | 799104 | 799247 | Hypo | cancer_general | | chr20 | 799458 | 799706 | Hypo | cancer_general | |
| chr20 | 1094560 | 1094682 | Hypo | ovarian | PSMF1 | chr20 | 1197670 | 1197711 | Hypo | cancer_general | RAD21L1, C20orf202 |
| chr20 | 1975357 | 1975386 | Hypo | literature | PDYN, AK090681 | chr20 | 2645540 | 2645795 | Hypo | cancer_general | IDH3B, SNORA51 |
| chr20 | 3027758 | 3027931 | Hypo | cancer_general | MRPS26, GNRH2, PTPRA | chr20 | 3154172 | 3154204 | Hypo | breast | LZTS3 |
| chr20 | 3204870 | 3204952 | Hypo | cancer_general | SLC4A11, ITPA | chr20 | 3762407 | 3762436 | Hypo | tcga | CENPB, CDC25B, SPEF1 |
| chr20 | 3858389 | 3858632 | Hypo | cancer_general | BC012193, MAVS | chr20 | 3996688 | 3996726 | Hypo | cancer_general | RNF24 |
| chr20 | 4040710 | 4040871 | Hypo | cancer_general | | chr20 | 4061323 | 4061452 | Hypo | hepatobiliary | |
| chr20 | 4085057 | 4085087 | Hypo | cancer_general | | chr20 | 4804703 | 4804732 | Hypo | tcga | RASSF2 |
| chr20 | 5025228 | 5025258 | Hypo | cancer_general | | chr20 | 5106720 | 5106750 | Hypo | cancer_general | CDS2, PCNA-AS1, PCNA |
| chr20 | 5433047 | 5433085 | Hypo | ovarian | LINC00658 LRRN4, | chr20 | 5610356 | 5610386 | Hypo | colorectal | CRLS1, |
| chr20 | 6022797 | 6023045 | Hypo | breast | CRLS1 | chr20 | 6023268 | 6023351 | Hypo | breast | LRRN4 |
| chr20 | 7980362 | 7980392 | Hypo | head_neck | TMX4 | chr20 | 9488780 | 9488848 | Hypo | cancer_general | LAMP5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 14447971 | 14448144 | Hypo | cancer_general | — | chr20 | 16554749 | 16555030 | Hypo | cancer_general | KIF16B |
| chr20 | 18073183 | 18073276 | Hypo | cancer_general | — | chr20 | 18448982 | 18449076 | Hypo | cancer_general | POLR3F, DZANK1, MIR3192 |
| chr20 | 18489463 | 18489658 | Hypo | cancer_general | SEC23B | chr20 | 19128288 | 19128473 | Hypo | cancer_general | NKX2-2 |
| chr20 | 19928306 | 19928461 | Hypo | cancer_general | RIN2 | chr20 | 21501381 | 21501417 | Hypo | literature | LOC284788 |
| chr20 | 21685385 | 21685526 | Hypo | cancer_general | PAX1 | chr20 | 22401392 | 22401421 | Hypo | cancer_general | — |
| chr20 | 23138383 | 23138444 | Hypo | cancer_general | — | chr20 | 23406698 | 23406830 | Hypo | cancer_general | — |
| chr20 | 24505190 | 24505252 | Hypo | cancer_general | SYNDIG1 | chr20 | 24726701 | 24726825 | Hypo | cancer_general | — |
| chr20 | 25086082 | 25086275 | Hypo | cancer_general | — | chr20 | 25223141 | 25223277 | Hypo | lung | PYGB |
| chr20 | 25230509 | 25230799 | Hypo | cancer_general | PYGB | chr20 | 25334513 | 25334650 | Hypo | cancer_general | ABHD12 |
| chr20 | 25344027 | 25344118 | Hypo | cancer_general | ABHD12 | chr20 | 29833090 | 29833090 | Hypo | cancer_general | — |
| chr20 | 29914002 | 29914139 | Hypo | cancer_general | — | chr20 | 29956013 | 29956042 | Hypo | literature | DEFB118, DEFB119 |
| chr20 | 29956570 | 29956599 | Hypo | literature | DEFB119, DEFB118 HM13-AS1 | chr20 | 30101523 | 30101743 | Hypo | cancer_general | HM13 |
| chr20 | 30162296 | 30162459 | Hypo | cancer_general | — | chr20 | 30174561 | 30174645 | Hypo | cancer_general | — |
| chr20 | 30186068 | 30186165 | Hypo | ovarian | MIR3193, ID1 | chr20 | 30201236 | 30201360 | Hypo | cancer_general | MIR3193, ID1 |
| chr20 | 30280423 | 30280509 | Hypo | blood | BCL2L1 | chr20 | 30297090 | 30297217 | Hypo | cancer_general | BCL2L1 |
| chr20 | 30468319 | 30468349 | Hypo | cancer_general | TTLL9 | chr20 | 31035471 | 31035518 | Hypo | breast | C20orf112, ASXL1 |
| chr20 | 31115683 | 31115799 | Hypo | cancer_general | C20orf112 | chr20 | 31151769 | 31151799 | Hypo | breast | C20orf112 |
| chr20 | 31207211 | 31207283 | Hypo | cancer_general | — | chr20 | 31282734 | 31282903 | Hypo | cancer_general | COMMD7 |
| chr20 | 32301797 | 32301953 | Hypo | breast | PXMP4 | chr20 | 32450248 | 32450427 | Hypo | cancer_general | CHMP4B |
| chr20 | 32701064 | 32701320 | Hypo | cancer_general | EIF2S2 | chr20 | 32716914 | 32716949 | Hypo | cancer_general | — |
| chr20 | 32768669 | 32768728 | Hypo | ovarian | — | chr20 | 32893006 | 32893125 | Hypo | ovarian | AHCY, GSS, MYH7B |
| chr20 | 33540284 | 33540550 | Hypo | cancer_general | MYH7B, GSS | chr20 | 33547485 | 33547585 | Hypo | colorectal | CEP250 |
| chr20 | 33574914 | 33574992 | Hypo | cancer_general | MIR499A, MIR499B, MYH7B | chr20 | 34041981 | 34042087 | Hypo | cancer_general | RBL1 |
| chr20 | 34148020 | 34148254 | Hypo | cancer_general | FER1L4, ERGIC3 | chr20 | 35640448 | 35640561 | Hypo | head_neck | GHRH |
| chr20 | 35742487 | 35742607 | Hypo | cancer_general | MROH8 | chr20 | 35892604 | 35892746 | Hypo | cancer_general | — |
| chr20 | 36183184 | 36183340 | Hypo | lung | — | chr20 | 40500546 | 40500638 | Hypo | cancer_general | PTPRT |
| chr20 | 40515378 | 40515504 | Hypo | cancer_general | — | chr20 | 40743859 | 40743888 | Hypo | literature | IFT52 |
| chr20 | 42218429 | 42218664 | Hypo | cancer_general | IFT52, SGK2 | chr20 | 42281425 | 42281455 | Hypo | cancer_general | SDC4, TRNA_Pseudo, RBPIL |
| chr20 | 42852751 | 42852915 | Hypo | colorectal, cancer_general | BC036500, OSER1-AS1 | chr20 | 43952174 | 43952302 | Hypo | cancer_general | ZNF335 |
| chr20 | 44003765 | 44003811 | Hypo | blood | SYS1, SYS1-DBNDD2, TP53TG5 | chr20 | 44601547 | 44601716 | Hypo | cancer_general | |
| chr20 | 44602074 | 44602364 | Hypo | cancer_general | ZNF335 | chr20 | 45280344 | 45280428 | Hypo | tcga | SLC13A3 |
| chr20 | 45337804 | 45337945 | Hypo | cancer_general | SLC2A10 | chr20 | 47247239 | 47247450 | Hypo | cancer_general | PREX1, AX746653 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 47274032 | 47274062 | Hypo | cancer_general | PREX1 | chr20 | 47296109 | 47296231 | Hypo | cancer_general | — |
| chr20 | 47450370 | 47450490 | Hypo | cancer_general | — | chr20 | 47815615 | 47815711 | Hypo | ovarian | — |
| chr20 | 47835328 | 47835358 | Hypo | cancer_general | DDX27 | chr20 | 47905426 | 47905603 | Hypo | cancer_general | ZFAS1, SNORD12, SNORD12B, SNORD12C |
| chr20 | 48695665 | 48696227 | Hypo | cancer_general | UBE2V1, TMEM189-UBE2V1 | chr20 | 48768118 | 48768148 | Hypo | cancer_general | — |
| chr20 | 48774527 | 48774569 | Hypo | cancer_general | — | chr20 | 49204179 | 49204449 | Hypo | cancer_general | FAM65C, MIR645, PTPN1 |
| chr20 | 49261803 | 49262104 | Hypo | cancer_general | FAM65C | chr20 | 49323924 | 49324125 | Hypo | cancer_general | — |
| chr20 | 49350910 | 49351041 | Hypo | cancer_general | PARD6B | chr20 | 49351564 | 49351649 | Hypo | cancer_general | PARD6B |
| chr20 | 49358137 | 49358396 | Hypo | cancer_general | PARD6B | chr20 | 49377755 | 49378043 | Hypo | cancer_general | PARD6B |
| chr20 | 49381140 | 49381240 | Hypo | cancer_general | — | chr20 | 49969348 | 49969515 | Hypo | colorectal | — |
| chr20 | 50160756 | 50160905 | Hypo | cancer_general | — | chr20 | 50083224 | 50083423 | Hypo | cancer_general | ATP9A |
| chr20 | 50602134 | 50602264 | Hypo | cancer_general | — | chr20 | 50693423 | 50693468 | Hypo | breast | ZFP64 |
| chr20 | 52311463 | 52311728 | Hypo | pancreas | — | chr20 | 52401713 | 52401775 | Hypo | cancer_general | — |
| chr20 | 54522432 | 54522631 | Hypo | cancer_general | — | chr20 | 55008041 | 55008194 | Hypo | cancer_general | CASS4 |
| chr20 | 55071563 | 55071717 | Hypo | ovarian | GCNT7, RTFDC1 | chr20 | 55499567 | 55499650 | Hypo | cancer_general | — |
| chr20 | 55693527 | 55693662 | Hypo | cancer_general | — | chr20 | 55959212 | 55959250 | Hypo | colorectal | RBM38 |
| chr20 | 56766160 | 56766190 | Hypo | cancer_general | — | chr20 | 56998280 | 56998337 | Hypo | lung | VAPB |
| chr20 | 57484406 | 57484445 | Hypo | literature | GNAS | chr20 | 59525138 | 59525300 | Hypo | cancer_general | — |
| chr20 | 59826192 | 59826221 | Hypo | literature | CDH4 | chr20 | 59880433 | 59880477 | Hypo | cancer_general | CDH4 |
| chr20 | 59910175 | 59910346 | Hypo | cancer_general | CDH4 | chr20 | 59973028 | 59973072 | Hypo | cancer_general | CDH4 |
| chr20 | 60202594 | 60202624 | Hypo | cancer_general | CDH4 | chr20 | 60235333 | 60235526 | Hypo | cancer_general | CDH4 |
| chr20 | 60238381 | 60238472 | Hypo | cancer_general | CDH4 | chr20 | 60238877 | 60238980 | Hypo | cancer_general | CDH4 |
| chr20 | 60243944 | 60244107 | Hypo | cancer_general | CDH4 | chr20 | 60329584 | 60329738 | Hypo | cancer_general | — |
| chr20 | 60333880 | 60333969 | Hypo | cancer_general | — | chr20 | 60359849 | 60359879 | Hypo | cancer_general | — |
| chr20 | 60375036 | 60375070 | Hypo | cancer_general | — | chr20 | 60396634 | 60439755 | Hypo | cancer_general | — |
| chr20 | 60453925 | 60454091 | Hypo | cancer_general | — | chr20 | 60477306 | 60477537 | Hypo | cancer_general | — |
| chr20 | 60485374 | 60485425 | Hypo | cancer_general | — | chr20 | 60503030 | 60503060 | Hypo | cancer_general | — |
| chr20 | 60545561 | 60545792 | Hypo | breast | TAF4 | chr20 | 60620122 | 60620557 | Hypo | breast | TAF4 |
| chr20 | 60772853 | 60773878 | Hypo | breast | MTG2 | chr20 | 60789965 | 60790124 | Hypo | cancer_general | HRH3 |
| chr20 | 60816241 | 60816671 | Hypo | head_neck | OSBPL2, AK126744 | chr20 | 60892164 | 60892222 | Hypo | cancer_general | LAMA5 |
| chr20 | 60926019 | 60926049 | Hypo | cancer_general | — | chr20 | 60970953 | 60970983 | Hypo | cancer_general | CABLES2, RPS21 |
| chr20 | 60983859 | 60984010 | Hypo | cancer_general | RBBP8NL, CABLES2 | chr20 | 60984341 | 60984465 | Hypo | cancer_general | RBBP8NL, CABLES2 |
| chr20 | 61288068 | 61288156 | Hypo | cancer_general | SLCO4A1, LOC100127888 | chr20 | 61288463 | 61288534 | Hypo | cancer_general | LOC100127888, SLCO4A1 |
| chr20 | 61294693 | 61294857 | Hypo | cancer_general | SLCO4A1, LOC100127888 | chr20 | 61412313 | 61412438 | Hypo | cancer_general | LINC00659, AX747649 |
| chr20 | 61505851 | 61506330 | Hypo | cancer_general | DIDO1 | chr20 | 61532546 | 61532605 | Hypo | cancer_general | DIDO1 |
| chr20 | 61714591 | 61714621 | Hypo | cancer_general | — | chr20 | 61763598 | 61763628 | Hypo | cancer_general | — |
| chr20 | 61765285 | 61765425 | Hypo | cancer_general | — | chr20 | 61823170 | 61823339 | Hypo | cancer_general | YTHDF1 |
| chr20 | 61974191 | 61974354 | Hypo | cancer_general | CHRNA4 | chr20 | 61980860 | 61980975 | Hypo | cancer_general | CHRNA4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 62031173 | 62031234 | Hypo | cancer_general | AK056267, KCNQ2 | chr20 | 62003058 | 62032095 | Hypo | cancer_general | KCNQ2, AK056267 |
| chr20 | 62037559 | 62037598 | Hypo | cancer_general | KCNQ2 | chr20 | 62046227 | 62046421 | Hypo | cancer_general | KCNQ2 |
| chr20 | 62090524 | 62090778 | Hypo | cancer_general | KCNQ2 | chr20 | 62097666 | 62097695 | Hypo | literature | KCNQ2 |
| chr20 | 62115047 | 62115266 | Hypo | cancer_general | EEF1A2 | chr20 | 62126118 | 62126429 | Hypo | cancer_general | EEF1A2 |
| chr20 | 62157151 | 62157307 | Hypo | cancer_general | PTK6, PPDPF | chr20 | 62165631 | 62165762 | Hypo | cancer_general | SRMS, PTK6 |
| chr20 | 62167554 | 62167584 | Hypo | cancer_general | SRMS, PTK6 | chr20 | 62170179 | 62170209 | Hypo | cancer_general | SRMS, PTK6 |
| chr20 | 62172945 | 62173055 | Hypo | cancer_general | SRMS, PTK6 | chr20 | 62260818 | 62260905 | Hypo | cancer_general | GMEB2 |
| chr20 | 62261532 | 62261562 | Hypo | cancer_general | STMN3, GMEB2 | chr20 | 62314848 | 62314955 | Hypo | breast | RTEL1-TNFRSF6B, RTEL1 |
| chr20 | 62321206 | 62321341 | Hypo | cancer_general | TNFRSF6B, ARFRP1, RTEL1-TNFRSF6B | chr20 | 62321638 | 62321881 | Hypo | pancreas, cancer_general | RTEL1-TNFRSF6B, TNFRSF6B, ARFRP1 |
| chr20 | 62340321 | 62340442 | Hypo | cancer_general | ZGPAT, ARFRP1 | chr20 | 62383218 | 62383289 | Hypo | cancer_general | ZBTB46, SLC2A4RG |
| chr20 | 62391938 | 62391968 | Hypo | colorectal | ZBTB46 | chr20 | 62488293 | 62488350 | Hypo | cancer_general | ABHD16B, TPD52L2 |
| chr20 | 62497836 | 62497920 | Hypo | cancer_general | TPD52L2, ABHD16B | chr20 | 62631351 | 62631593 | Hypo | ovarian | PRPF6 |
| chr20 | 62786577 | 62786726 | Hypo | cancer_general | MYT1 | chr20 | 62795643 | 62795672 | Hypo | literature | MYT1 |
| chr22 | 18009969 | 18010121 | Hypo | cancer_general | CECR2 | chr22 | 18110495 | 18110593 | Hypo | cancer_general | BCL2L13, ATP6V1E1 |
| chr22 | 18328127 | 18328268 | Hypo | cancer_general, lung | MICAL3, BC064400 | chr22 | 18340822 | 18340868 | Hypo | cancer_general | MICAL3 |
| chr22 | 18627328 | 18627537 | Hypo | ovarian | USP18 | chr22 | 19117564 | 19117594 | Hypo | cancer_general | DGCR14, TSSK2 |
| chr22 | 19136907 | 19136936 | Hypo | literature | GSC2 | chr22 | 19137859 | 19137888 | Hypo | literature | GSC2 |
| chr22 | 19138109 | 19138138 | Hypo | literature | GSC2 | chr22 | 20229079 | 20229239 | Hypo | pancreas | MIR1286, RTN4R |
| chr22 | 20864642 | 20864672 | Hypo | cancer_general | MED15 | chr22 | 20940868 | 20940898 | Hypo | head_neck | MED15 |
| chr22 | 21042829 | 21043014 | Hypo | cancer_general | DQ571461, POM121L4P | chr22 | 21153867 | 21154000 | Hypo | cancer_general | PI4KA |
| chr22 | 21270750 | 21270834 | Hypo | cancer_general | CRKL | chr22 | 21276140 | 21276261 | Hypo | cancer_general | CRKL |
| chr22 | 21299605 | 21299635 | Hypo | pancreas | BC033281, CRKL | chr22 | 21304771 | 21305007 | Hypo | cancer_general | BC033281, BC127858, CRKL |
| chr22 | 21977314 | 21977347 | Hypo | breast | YDJC, CCDC116, UBE2L3 | chr22 | 21982792 | 21982972 | Hypo | cancer_general | CCDC116, YDJC, UBE2L3 |
| chr22 | 22023273 | 22023451 | Hypo | cancer_general | PPIL2 | chr22 | 22058203 | 22058238 | Hypo | lung | YPEL1, PPIL2 |
| chr22 | 22201344 | 22201568 | Hypo | head_neck | MAPK1 | chr22 | 22901105 | 22901455 | Hypo | cancer_general | LOC648691, PRAME |
| chr22 | 23791402 | 23791432 | Hypo | cancer_general | — | chr22 | 23801459 | 23801610 | Hypo | breast | LOC388882 |
| chr22 | 23991201 | 23991272 | Hypo | pancreas | GUSBP11 | chr22 | 24145484 | 24145513 | Hypo | literature | SMARCB1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 24179940 | 24179982 | Hypo | blood | AK096976, DERL3 | chr22 | 24560375 | 24560526 | Hypo | breast | CABIN1 |
| chr22 | 28371649 | 28371679 | Hypo | cancer_general | TTC28 | chr22 | 29076592 | 29076622 | Hypo | lung | CHEK2 |
| chr22 | 29091824 | 29091853 | Hypo | literature | CHEK2 | chr22 | 29445752 | 29445923 | Hypo | lung | C22orf31 |
| chr22 | 29977614 | 29977863 | Hypo | cancer_general | NIPSNAP1 | chr22 | 30084358 | 30084388 | Hypo | cancer_general | NF2 |
| chr22 | 30090739 | 30090769 | Hypo | breast | NF2 | chr22 | 30158330 | 30158639 | Hypo | cancer_general | UQCR10, ZMAT5 |
| chr22 | 30784196 | 30784278 | Hypo | cancer_general | SEC14L2, RNF215 | chr22 | 32061344 | 32061374 | Hypo | cancer_general | — |
| chr22 | 32748936 | 32748966 | Hypo | cancer_general | RFPL3, RFPL3S, JB153905 | chr22 | 32868720 | 32868837 | Hypo | cancer_general | FBXO7, BPIFC |
| chr22 | 35079219 | 35079345 | Hypo | cancer_general | — | chr22 | 35768531 | 35768719 | Hypo | cancer_general | HMOX1 |
| chr22 | 35848358 | 35848670 | Hypo | cancer_general | — | chr22 | 35938746 | 35939000 | Hypo | esophageal | RASD2 |
| chr22 | 36567866 | 36567896 | Hypo | cancer_general | — | chr22 | 36855297 | 36855335 | Hypo | cancer_general | TXN2 |
| chr22 | 36855568 | 36855598 | Hypo | cancer_general | TXN2 | chr22 | 36880362 | 36880462 | Hypo | cancer_general | FOXRED2, TXN2 |
| chr22 | 36902291 | 36902381 | Hypo | head_neck | EIF3D, FOXRED2 | chr22 | 37302073 | 37302103 | Hypo | cancer_general | CSF2RB |
| chr22 | 38002684 | 38002733 | Hypo | cancer_general | GGA1 | chr22 | 38087310 | 38087367 | Hypo | head_neck | TRIOBP, NOL12 |
| chr22 | 38182815 | 38182981 | Hypo | head_neck | — | chr22 | 38199769 | 38199894 | Hypo | cancer_general | H1F0, GCAT |
| chr22 | 38507316 | 38507346 | Hypo | cancer_general | PLA2G6 | chr22 | 38593076 | 38593076 | Hypo | cancer_general | MAFF DDX17, KDELR3 |
| chr22 | 38639229 | 38639259 | Hypo | cancer_general | TMEM184B | chr22 | 38874215 | 38874362 | Hypo | head_neck | |
| chr22 | 39094890 | 39094964 | Hypo | cancer_general | GTPBP1, JOSD1 | chr22 | 39098022 | 39098064 | Hypo | cancer_general | GTPBP1, JOSD1 |
| chr22 | 39112502 | 39112584 | Hypo | head_neck | GTPBP1 | chr22 | 39830355 | 39830457 | Hypo | breast | LOC100506472, TAB1 |
| chr22 | 39932499 | 39932563 | Hypo | cancer_general | RPS19BP1 | chr22 | 40042627 | 40042743 | Hypo | cancer_general | CACNA1I |
| chr22 | 40075157 | 40075302 | Hypo | hepatobiliary | CACNA1I | chr22 | 40226345 | 40226389 | Hypo | cancer_general | ENTHD1 |
| chr22 | 40767753 | 40767936 | Hypo | cancer_general | ADSL, SGSM3 | chr22 | 40895978 | 40896029 | Hypo | cancer_general | MKL1 |
| chr22 | 41048488 | 41048518 | Hypo | cancer_general | ST13, MIR4766, SLC25A17 | chr22 | 41048732 | 41049109 | Hypo | cancer_general | — |
| chr22 | 41217105 | 41217405 | Hypo | lung, cancer_general | CHADL, RANGAP1 | chr22 | 41634393 | 41634542 | Hypo | pancreas, cancer_general | RANGAP1, CHADL |
| chr22 | 41637064 | 41637129 | Hypo | cancer_general | RANGAP1 | chr22 | 41648414 | 41648444 | Hypo | head_neck | RANGAP1 |
| chr22 | 41657233 | 41657350 | Hypo | breast | TOB2 | chr22 | 41690119 | 41690149 | Hypo | head_neck | ZC3H7B, RANGAP1 |
| chr22 | 41839432 | 41839498 | Hypo | cancer_general | TOB2 | chr22 | 42068010 | 42068172 | Hypo | cancer_general | NHP2L1, XRCC6 |
| chr22 | 42096002 | 42096190 | Hypo | head_neck | C22orf46, MEI1, FLJ23584 | chr22 | 42343416 | 42343676 | Hypo | cancer_general | LINC00634, CENPM |
| chr22 | 42667358 | 42667432 | Hypo | cancer_general | LOC388906 | chr22 | 42916449 | 42916479 | Hypo | cancer_general | RRP7A, SERHL |

TABLE 11-continued

| chr | Start | Stop | Hypo/hyper | classification | annotation |
|---|---|---|---|---|---|
| chr22 | 43012543 | 43012877 | Hypo | cancer_general | CYB5R3, DL490307, RNU12, POLDIP3 |
| chr22 | 43434441 | 43434477 | Hypo | cancer_general | TTLL1, BC039353 |
| chr22 | 44455707 | 44455740 | Hypo | cancer_general | PARVB |
| chr22 | 45088602 | 45088743 | Hypo | cancer_general | PRR5, PRR5-ARHGAP8 |
| chr22 | 45252427 | 45252463 | Hypo | hepatobiliary | ARHGAP8 |
| chr22 | 45313416 | 45313446 | Hypo | hepatobiliary | PHF21B |
| chr22 | 45604184 | 45604343 | Hypo | cancer_general | MIR1249, KIAA0930 |
| chr22 | 46455833 | 46455905 | Hypo | cancer_general | MIRLET7BHG, LOC150381, C22orf26, LOC554174 |
| chr22 | 46931260 | 46931332 | Hypo | ovarian | — |
| chr22 | 47023044 | 47023191 | Hypo | head_neck | GRAMD4 |
| chr22 | 47193335 | 47193371 | Hypo | cancer_general | TBC1D22A |
| chr22 | 47525846 | 47525885 | Hypo | cancer_general | — |
| chr22 | 48027626 | 48027655 | Hypo | literature | AK093107, BC039485, LINC00898 |
| chr22 | 49852617 | 49852647 | Hypo | cancer_general | BC033837 |
| chr22 | 50001699 | 50001882 | Hypo | cancer_general | BC033837 |
| chr22 | 50003204 | 50003234 | Hypo | cancer_general | BC033837 |
| chr22 | 50010461 | 50010585 | Hypo | cancer_general | C22orf34, BC033837 |
| chr22 | 50149431 | 50149470 | Hypo | cancer_general | — |
| chr22 | 50467005 | 50467035 | Hypo | cancer_general | — |
| chr22 | 50768840 | 50768876 | Hypo | cancer_general | DENND6B LMF2, NCAPH2 |
| chr22 | 50939073 | 50939111 | Hypo | cancer_general | DIP2C |
| chr10 | 524754 | 524784 | Hypo | head_neck | BC127786, LARP4B |
| chr10 | 978878 | 978933 | Hypo | cancer_general | WDR37 |
| chr10 | 1120778 | 1120937 | Hypo | lung | ADARB2-AS1 |
| chr10 | 1585111 | 1585239 | Hypo | cancer_general | BC039685, PITRM1-AS1, PITRM1 |
| chr10 | 3197004 | 3197113 | Hypo | ovarian | |
| chr22 | 43083130 | 43083166 | Hypo | cancer_general | A4GALT |
| chr22 | 43540672 | 43540702 | Hypo | breast | TSPO, MCAT |
| chr22 | 45087614 | 45087649 | Hypo | cancer_general | PRR5 |
| chr22 | 45135939 | 45135979 | Hypo | cancer_general | PRR5, PRR5-ARHGAP8 |
| chr22 | 45277292 | 45277322 | Hypo | cancer_general | PHF21B |
| chr22 | 45593643 | 45593715 | Hypo | cancer_general | KIAA0930, NUP50, MIR1249 |
| chr22 | 46438085 | 46438217 | Hypo | cancer_general | C22orf26, LINC00899 |
| chr22 | 46599623 | 46599725 | Hypo | colorectal | PPARA |
| chr22 | 47005080 | 47005154 | Hypo | cancer_general | — |
| chr22 | 47054686 | 47054716 | Hypo | head_neck | GRAMD4 |
| chr22 | 47395475 | 47395505 | Hypo | breast | — |
| chr22 | 47584867 | 47585024 | Hypo | cancer_general | LOC284933, FAM19A5 |
| chr22 | 48931881 | 48932027 | Hypo | cancer_general | BC033837 |
| chr22 | 49979646 | 49979757 | Hypo | cancer_general | BC033837 |
| chr22 | 50002787 | 50002819 | Hypo | cancer_general | C22orf34, BC033837 |
| chr22 | 50010113 | 50010258 | Hypo | cancer_general | C22orf34, BC033837 |
| chr22 | 50031691 | 50031721 | Hypo | cancer_general | ZBED4 |
| chr22 | 50251536 | 50251582 | Hypo | breast | SBF1 |
| chr22 | 50467876 | 50468105 | Hypo | cancer_general | SYCE3, KLHDC7B |
| chr22 | 50899293 | 50899672 | Hypo | literature | |
| chr22 | 50986016 | 50986045 | Hypo | cancer_general | IDI1, IDI2-AS1, IDI2 |
| chr10 | 833307 | 833386 | Hypo | breast | ADARB2-AS1 |
| chr10 | 1080377 | 1080513 | Hypo | hepatobiliary | — |
| chr10 | 1577394 | 1577424 | Hypo | cancer_general | — |
| chr10 | 1708327 | 1708478 | Hypo | cancer_general | |
| chr10 | 3285585 | 3285698 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 3330499 | 3330618 | Hypo | cancer_general | — | chr10 | 3641378 | 3641413 | Hypo | colorectal | BC037918 |
| chr10 | 3678597 | 3678637 | Hypo | lung | BC037918 | chr10 | 3895410 | 3895432 | Hypo | cancer_general | — |
| chr10 | 4599917 | 4599965 | Hypo | cancer_general | — | chr10 | 5530764 | 5530975 | Hypo | cancer_general | CALML5 |
| chr10 | 5765021 | 5765059 | Hypo | breast | FAM208B | chr10 | 5855154 | 5855194 | Hypo | pancreas | GDI2 |
| chr10 | 5875140 | 5875396 | Hypo | cancer_general | — | chr10 | 6003402 | 6003855 | Hypo | breast | IL15RA |
| chr10 | 6042309 | 6042571 | Hypo | cancer_general | — | chr10 | 6162159 | 6162225 | Hypo | cancer_general | RBM17 |
| chr10 | 6167619 | 6167742 | Hypo | ovarian | RBM17 | chr10 | 6206142 | 6206217 | Hypo | pancreas | — |
| chr10 | 6372343 | 6372373 | Hypo | ovarian | LOC399715 | chr10 | 6513976 | 6514006 | Hypo | hepatobiliary | PRKCQ |
| chr10 | 6577643 | 6577673 | Hypo | cancer_general | AX748236 | chr10 | 6586721 | 6586847 | Hypo | cancer_general | — |
| chr10 | 6963079 | 6963111 | Hypo | cancer_general | — | chr10 | 6984463 | 6984639 | Hypo | cancer_general | — |
| chr10 | 7205733 | 7205787 | Hypo | cancer_general | SFMBT2 | chr10 | 7212745 | 7213064 | Hypo | cancer_general | SFMBT2 |
| chr10 | 7213505 | 7213535 | Hypo | hepatobiliary | SFMBT2 | chr10 | 7216059 | 7216089 | Hypo | cancer_general | SFMBT2 |
| chr10 | 7236211 | 7236245 | Hypo | cancer_general | SFMBT2 | chr10 | 7255730 | 7255821 | Hypo | hepatobiliary | SFMBT2 |
| chr10 | 7323283 | 7323313 | Hypo | hepatobiliary | SFMBT2 | chr10 | 7334737 | 7334767 | Hypo | hepatobiliary | SFMBT2 |
| chr10 | 7363436 | 7363466 | Hypo | cancer_general | SFMBT2 | chr10 | 7371678 | 7371708 | Hypo | cancer_general | SFMBT2 |
| chr10 | 7414544 | 7414588 | Hypo | hepatobiliary | SFMBT2 | chr10 | 7424626 | 7424687 | Hypo | hepatobiliary | TAF3 |
| chr10 | 7436090 | 7436209 | Hypo | cancer_general | SFMBT2 | chr10 | 8055681 | 8055764 | Hypo | pancreas | CAMK1D |
| chr10 | 11700918 | 11701075 | Hypo | cancer_general | — | chr10 | 12554417 | 12554501 | Hypo | cancer_general | FRMD4A |
| chr10 | 13140861 | 13141020 | Hypo | cancer_general | OPTN, AK311458 | chr10 | 13715208 | 13715401 | Hypo | head_neck | DCLRE1C |
| chr10 | 14393819 | 14393893 | Hypo | colorectal | FRMD4A | chr10 | 14966129 | 14966212 | Hypo | cancer_general | RPP38, NMT2, C10orf111, ACBD7 |
| chr10 | 15002784 | 15003006 | Hypo | cancer_general | MEIG1 | chr10 | 15140484 | 15140526 | Hypo | cancer_general | |
| chr10 | 16175687 | 16175801 | Hypo | hepatobiliary | — | chr10 | 16564087 | 16564116 | Hypo | literature | C1QL3 |
| chr10 | 16564537 | 16564566 | Hypo | literature | C1QL3 | chr10 | 17269259 | 17269288 | Hypo | literature | VIM, BC078172 |
| chr10 | 17275584 | 17275613 | Hypo | literature | VIM, BC078172 | chr10 | 17277741 | 17277770 | Hypo | literature | VIM, BC078172 |
| chr10 | 17429165 | 17429622 | Hypo | cancer_general | ST8SIA6-AS1, ST8SIA6 | chr10 | 17503402 | 17503520 | Hypo | cancer_general | — |
| chr10 | 17509450 | 17509503 | Hypo | hepatobiliary | — | chr10 | 21101525 | 21101555 | Hypo | hepatobiliary | NEBL |
| chr10 | 21728064 | 21728124 | Hypo | cancer_general | — | chr10 | 22047336 | 22047635 | Hypo | breast | DNAJC1 |
| chr10 | 22567093 | 22567322 | Hypo | cancer_general | APBB1IP | chr10 | 24988589 | 24988619 | Hypo | cancer_general | ARHGAP21 |
| chr10 | 26747051 | 26747159 | Hypo | cancer_general | — | chr10 | 26803853 | 26803883 | Hypo | cancer_general | — |
| chr10 | 26816766 | 26816938 | Hypo | cancer_general | RAB18 | chr10 | 26931897 | 26931926 | Hypo | literature | LINC00202-2 |
| chr10 | 27794496 | 27794588 | Hypo | ovarian | BAMBI | chr10 | 27846637 | 27846816 | Hypo | cancer_general | — |
| chr10 | 28964745 | 28964800 | Hypo | cancer_general | — | chr10 | 30848200 | 30848230 | Hypo | cancer_general | — |
| chr10 | 31892922 | 31893079 | Hypo | cancer_general | EPC1 | chr10 | 32499044 | 32499176 | Hypo | cancer_general | ITGB1 |
| chr10 | 32672459 | 32672489 | Hypo | pancreas | — | chr10 | 33233313 | 33233361 | Hypo | cancer_general | ZNF33BP1, ZNF248 |
| chr10 | 37051865 | 37051895 | Hypo | cancer_general | — | chr10 | 38078948 | 38079105 | Hypo | cancer_general | — |
| chr10 | 43186151 | 43186181 | Hypo | cancer_general | AK123067 | chr10 | 43609055 | 43609117 | Hypo | literature | RET |
| chr10 | 43609922 | 43609963 | Hypo | literature | RET | chr10 | 43613890 | 43613919 | Hypo | literature | RET |
| chr10 | 43614982 | 43615011 | Hypo | literature | RET | chr10 | 43615554 | 43615607 | Hypo | literature | RET |
| chr10 | 43617401 | 43617430 | Hypo | literature | RET | chr10 | 43858343 | 43858470 | Hypo | cancer_general | FXYD4 |
| chr10 | 43905877 | 43906023 | Hypo | cancer_general | — | chr10 | 44434176 | 44434206 | Hypo | cancer_general | LINC00841 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 49652977 | 49653080 | Hypo | cancer_general | ARHGAP22, MAPK8 | chr10 | 50340119 | 50340149 | Hypo | cancer_general | FAM170B, FAM170B-AS1 |
| chr10 | 50507557 | 50507619 | Hypo | cancer_general | C10orf71 | chr10 | 50748131 | 50748350 | Hypo | cancer_general | — |
| chr10 | 53107427 | 53107563 | Hypo | cancer_general | — | chr10 | 63669223 | 63669344 | Hypo | ovarian | ARID5B |
| chr10 | 65262111 | 65262304 | Hypo | breast | — | chr10 | 69784459 | 69778588 | Hypo | cancer_general | DNAJC12 |
| chr10 | 69589153 | 69589407 | Hypo | cancer_general | DNAJC12 | chr10 | 70167678 | 70167708 | Hypo | cancer_general | DNA2, RUFY2 |
| chr10 | 70232345 | 70232485 | Hypo | cancer_general | SLC25A16, DNA2 | chr10 | 70275831 | 70275979 | Hypo | breast | SLC25A16 |
| chr10 | 70314814 | 70315148 | Hypo | cancer_general | TET1 | chr10 | 70565410 | 70565489 | Hypo | cancer_general | — |
| chr10 | 70586494 | 70586540 | Hypo | cancer_general | STOX1 | chr10 | 71084981 | 71085116 | Hypo | hepatobiliary | HK1 |
| chr10 | 73157867 | 73158027 | Hypo | pancreas | CDH23 | chr10 | 75384100 | 75384130 | Hypo | ovarian | MYOZ1 |
| chr10 | 75386789 | 75386893 | Hypo | cancer_general | MYOZ1 | chr10 | 75388129 | 75388173 | Hypo | cancer_general | MYOZ1 |
| chr10 | 75488953 | 75489125 | Hypo | cancer_general | GLUD1P3, BMS1P4, AGAP5 | chr10 | 81023884 | 81023914 | Hypo | cancer_general | ZMIZ1 |
| chr10 | 81860447 | 81860568 | Hypo | cancer_general | TMEM254 | chr10 | 81966737 | 81966828 | Hypo | cancer_general | LINC00857, ANXA11 |
| chr10 | 85792257 | 85792287 | Hypo | hepatobiliary | — | chr10 | 88304914 | 88304944 | Hypo | cancer_general | — |
| chr10 | 88684005 | 88684034 | Hypo | literature | BMPR1A | chr10 | 88698834 | 88698914 | Hypo | cancer_general | MMRN2 |
| chr10 | 89624255 | 89624311 | Hypo | literature | PTEN, KLLN | chr10 | 89653788 | 89653859 | Hypo | literature | PTEN |
| chr10 | 89685272 | 89685322 | Hypo | literature | PTEN | chr10 | 89690790 | 89690819 | Hypo | literature | PTEN |
| chr10 | 89692776 | 89693015 | Hypo | literature | PTEN | chr10 | 89711861 | 89711992 | Hypo | literature | AK130076, PTEN |
| chr10 | 89717610 | 89717744 | Hypo | literature | AK130076, PTEN | chr10 | 89720790 | 89720885 | Hypo | literature | — |
| chr10 | 89725030 | 89725071 | Hypo | literature | — | chr10 | 94062288 | 94062318 | Hypo | head_neck | 5-Mar |
| chr10 | 96304020 | 96304329 | Hypo | cancer_general | HELLS, TBC1D12 | chr10 | 98129822 | 98130033 | Hypo | cancer_general | TLL2 |
| chr10 | 98528023 | 98528107 | Hypo | cancer_general | ARHGAP19 | chr10 | 98558129 | 98558200 | Hypo | colorectal | — |
| chr10 | 99051122 | 99051253 | Hypo | cancer_general | MARVELD1 | chr10 | 99161398 | 99161560 | Hypo | cancer_general | — |
| chr10 | 99481747 | 99481905 | Hypo | colorectal | CUTC, COX15 | chr10 | 101363207 | 101363418 | Hypo | colorectal | SLC25A28 |
| chr10 | 101492942 | 101493074 | Hypo | cancer_general |  | chr10 | 101988223 | 101988404 | Hypo | cancer_general | CWF19L1, SNORA12, CHUK |
| chr10 | 103325743 | 103325773 | Hypo | cancer_general | DPCD, BTRC | chr10 | 103425950 | 103426174 | Hypo | ovarian | FBXW4 |
| chr10 | 103579635 | 103579713 | Hypo | cancer_general | KCNIP2, LOC100289509, MGEA5 | chr10 | 103814668 | 103814754 | Hypo | cancer_general | C10orf76 |
| chr10 | 103930034 | 103930161 | Hypo | cancer_general | NOLC1 | chr10 | 105126957 | 105127076 | Hypo | cancer_general | TAF5 |
| chr10 | 105155285 | 105155481 | Hypo | cancer_general | PDCD11, MIR1307, USMG5, TAF5 | chr10 | 105413627 | 105413784 | Hypo | cancer_general | SH3PXD2A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 105420861 | 105420891 | Hypo | breast | SH3PXD2A | chr10 | 105527028 | 105527057 | Hypo | literature | RBM20 |
| chr10 | 108469972 | 108470093 | Hypo | cancer_general | SORCS1 | chr10 | 122440378 | 122440408 | Hypo | cancer_general | — |
| chr10 | 115925505 | 115925552 | Hypo | cancer_general | MIR2110, C10orf118 | chr10 | 116331126 | 116331156 | Hypo | cancer_general | — |
| chr10 | 119807026 | 119807056 | Hypo | cancer_general | CASC2, RAB11FIP2 | chr10 | 120707028 | 120707111 | Hypo | cancer_general | — |
| chr10 | 120800789 | 120800835 | Hypo | ovarian | EIF3A, NANOS1 | chr10 | 120841558 | 120841590 | Hypo | cancer_general | — |
| chr10 | 120937014 | 120937139 | Hypo | breast | PRDX3 | chr10 | 121267480 | 121267626 | Hypo | hepatobiliary | RGS10 |
| chr10 | 121307542 | 121307572 | Hypo | cancer_general | — | chr10 | 123256044 | 123256232 | Hypo | literature | FGFR2 |
| chr10 | 123258020 | 123258091 | Hypo | literature | FGFR2 | chr10 | 123274758 | 123274787 | Hypo | literature | FGFR2 |
| chr10 | 123279697 | 123279697 | Hypo | literature | FGFR2 | chr10 | 123667184 | 123667222 | Hypo | breast | ATE1 |
| chr10 | 123688711 | 123688741 | Hypo | cancer_general | ATE1 | chr10 | 125527754 | 125527784 | Hypo | hepatobiliary | CPXM2 |
| chr10 | 126101966 | 126102095 | Hypo | head_neck | OAT | chr10 | 126198949 | 126199077 | Hypo | cancer_general | LHPP |
| chr10 | 126697789 | 126698107 | Hypo | cancer_general | CTBP2 | chr10 | 126782965 | 126783048 | Hypo | hepatobiliary | — |
| chr10 | 126828994 | 126829024 | Hypo | hepatobiliary | — | chr10 | 127406313 | 127406386 | Hypo | ovarian | C10orf137, FLJ37035, LOC283038 |
| chr10 | 127693923 | 127693959 | Hypo | hepatobiliary | ADAM12, FANK1 | chr10 | 129379338 | 129379367 | Hypo | literature | — |
| chr10 | 129888804 | 129888885 | Hypo | cancer_general | MKI67, PTPRE | chr10 | 130203435 | 130203480 | Hypo | cancer_general | — |
| chr10 | 130577764 | 130577794 | Hypo | cancer_general | — | chr10 | 131348513 | 131348793 | Hypo | pancreas | MGMT |
| chr10 | 131647903 | 131647933 | Hypo | cancer_general | MIR4297, EBF3 | chr10 | 131936451 | 131936626 | Hypo | cancer_general | GLRX3 |
| chr10 | 131937355 | 131937428 | Hypo | lung | GLRX3 | chr10 | 132000973 | 132001015 | Hypo | cancer_general | JAKMIP3 |
| chr10 | 132001252 | 132001556 | Hypo | cancer_general | — | chr10 | 133951602 | 133952025 | Hypo | cancer_general | STK32C, DPYSL4 |
| chr10 | 133979059 | 133979089 | Hypo | cancer_general | JAKMIP3 | chr10 | 134016203 | 134016388 | Hypo | cancer_general | STK32C |
| chr10 | 134022845 | 134022875 | Hypo | cancer_general | STK32C, DPYSL4 | chr10 | 134039087 | 134039117 | Hypo | hepatobiliary | — |
| chr10 | 134092153 | 134092202 | Hypo | cancer_general | STK32C | chr10 | 134095594 | 134095833 | Hypo | cancer_general | STK32C |
| chr10 | 134119401 | 134119447 | Hypo | hepatobiliary | STK32C | chr10 | 134273064 | 134273156 | Hypo | cancer_general | — |
| chr10 | 134301095 | 134301212 | Hypo | cancer_general | — | chr10 | 134481320 | 134481433 | Hypo | cancer_general | INPP5A |
| chr10 | 134491021 | 134491114 | Hypo | ovarian | INPP5A | chr10 | 134499773 | 134499803 | Hypo | pancreas | INPP5A |
| chr10 | 134593329 | 134593416 | Hypo | ovarian | NKX6-2, INPP5A | chr10 | 134607970 | 134608183 | Hypo | cancer_general | NKX6-2 |
| chr10 | 134665147 | 134665202 | Hypo | cancer_general | TTC40 | chr10 | 134679129 | 134679265 | Hypo | cancer_general | TTC40 |
| chr10 | 134690559 | 134690617 | Hypo | cancer_general | TTC40 | chr10 | 134693587 | 134693709 | Hypo | cancer_general | TTC40 |
| chr10 | 134699872 | 134699909 | Hypo | cancer_general | TTC40 | chr10 | 134733221 | 134733275 | Hypo | cancer_general | TTC40 |
| chr10 | 134733497 | 134733617 | Hypo | cancer_general | TTC40 | chr10 | 134738378 | 134738642 | Hypo | cancer_general | TTC40 |
| chr10 | 134788083 | 134788251 | Hypo | cancer_general | LOC399829 | chr10 | 134794271 | 134794342 | Hypo | cancer_general | LOC399829 |
| chr10 | 134796012 | 134796042 | Hypo | cancer_general | LOC399829 | chr10 | 134896060 | 134896092 | Hypo | hepatobiliary | GPR123 |
| chr10 | 134916714 | 134916774 | Hypo | cancer_general | GPR123 | chr10 | 134941145 | 134941178 | Hypo | cancer_general | GPR123 |
| chr10 | 134942840 | 134943114 | Hypo | cancer_general | GPR123 | chr10 | 134943445 | 134943542 | Hypo | cancer_general | GPR123 |
| chr10 | 134944742 | 134944772 | Hypo | cancer_general | GPR123 | chr10 | 134959217 | 134959391 | Hypo | cancer_general | CS330190 |
| chr10 | 135002063 | 135002156 | Hypo | cancer_general | KNDC1 | chr10 | 135014963 | 135015132 | Hypo | ovarian | KNDC1 |
| chr10 | 135017049 | 135017129 | Hypo | cancer_general | KNDC1 | chr10 | 135018032 | 135018070 | Hypo | cancer_general | KNDC1 |
| chr10 | 135018825 | 135018960 | Hypo | cancer_general | KNDC1 | chr10 | 135020801 | 135020893 | Hypo | cancer_general | KNDC1 |
| chr10 | 135023470 | 135023500 | Hypo | cancer_general | KNDC1 | chr10 | 135076368 | 135076503 | Hypo | cancer_general | ADAM8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 135122991 | 135123020 | Hypo | literature | PRAP1, ZNF511, TUBGCP2 | chr10 | 135153956 | 135154001 | Hypo | ovarian | PRAP1, CALY |
| chr4 | 21100748 | 21100778 | Hypo | head_neck | TRNA_Pro, OR6S1, TRNA_Thr, TRNA_Leu | chr4 | | | Hypo | esophageal | OXA1L, SLC7A7 |
| chr4 | 23400315 | 23400354 | Hypo | cancer_general | TRNA, TRNA_Arg, PRMT5 | chr14 | 23426755 | 23426785 | Hypo | cancer_general | MIR4707, HAUS4 |
| chr4 | 23701644 | 23701737 | Hypo | head_neck | — | chr14 | 23706727 | 23706765 | Hypo | cancer_general | — |
| chr4 | 24562744 | 24562774 | Hypo | cancer_general | PCK2 | chr14 | 25071566 | 25071612 | Hypo | cancer_general | GZMH |
| chr4 | 25155907 | 25155985 | Hypo | cancer_general | — | chr14 | 31027323 | 31027367 | Hypo | cancer_general | G2E3 |
| chr4 | 31925554 | 31925724 | Hypo | cancer_general | BC041327, DTD2 | chr14 | 32597620 | 32597657 | Hypo | pancreas | ARHGAP5 |
| chr4 | 34269897 | 34270004 | Hypo | head_neck | — | chr14 | 35023111 | 35023322 | Hypo | cancer_general | SNX6 |
| chr4 | 35024446 | 35024546 | Hypo | cancer_general | SNX6 | chr14 | 35389907 | 35389943 | Hypo | cancer_general | — |
| chr4 | 39579800 | 39579830 | Hypo | cancer_general | GEMIN2 | chr14 | 45602514 | 45602576 | Hypo | cancer_general | FANCM, FKBP3 |
| chr4 | 50233426 | 50233459 | Hypo | cancer_general | KLHDC2 Metazoa_SRP | chr14 | 50333754 | 50333994 | Hypo | cancer_general | Metazoa_SRP ARF6 |
| chr4 | 50334254 | 50334355 | Hypo | cancer_general | — | chr14 | 50355854 | 50355924 | Hypo | colorectal | ATP5S, L2HGDH |
| chr4 | 50681598 | 50681859 | Hypo | breast | — | chr14 | 50777663 | 50777714 | Hypo | cancer_general | FRMD6, FRMD6-AS2 |
| chr4 | 51829264 | 51829396 | Hypo | ovarian | LINC00640 | chr14 | 51955509 | 51955538 | Hypo | literature | — |
| chr4 | 52765920 | 52766075 | Hypo | cancer_general | — | chr14 | 55370202 | 55370235 | Hypo | cancer_general | FBXO34 |
| chr4 | 55668368 | 55668526 | Hypo | colorectal | DLGAP5 | chr14 | 55765285 | 55765714 | Hypo | lung, cancer_general | |
| chr4 | 55823079 | 55823218 | Hypo | breast | ATG14, FBXO34 | chr14 | 57045520 | 57045739 | Hypo | cancer_general | TMEM260 |
| chr4 | 57270936 | 57270987 | Hypo | cancer_general | OTX2, OTX2-AS1 | chr14 | 58857094 | 58857355 | Hypo | cancer_general | TOMM20L |
| chr4 | 58893052 | 58893183 | Hypo | cancer_general | KIAA0586, TIMM9 | chr14 | 59770326 | 59770452 | Hypo | breast | DAAM1 |
| chr4 | 62106193 | 62106242 | Hypo | colorectal | FLJ22447 | chr14 | 64107335 | 64107600 | Hypo | cancer_general | — |
| chr4 | 64222413 | 64222488 | Hypo | cancer_general | — | chr14 | 65005696 | 65005833 | Hypo | cancer_general | HSPA2 |
| chr4 | 65233339 | 65233464 | Hypo | cancer_general | SPTB | chr14 | 66498931 | 66498975 | Hypo | cancer_general | — |
| chr4 | 67585164 | 67585413 | Hypo | cancer_general | GPHN | chr14 | 67886678 | 67886606 | Hypo | cancer_general | PLEK2 |
| chr4 | 68334928 | 68335108 | Hypo | cancer_general | RAD51B | chr14 | 69014044 | 69014110 | Hypo | pancreas | — |
| chr4 | 69866541 | 69866706 | Hypo | cancer_general | SLC39A9, ERH | chr14 | 69867022 | 69867196 | Hypo | cancer_general | SLC39A9, ERH |
| chr4 | 73167750 | 73167899 | Hypo | cancer_general | DPF3 | chr14 | 73175026 | 73175148 | Hypo | cancer_general | DPF3 |
| chr4 | 73178807 | 73178865 | Hypo | cancer_general | DPF3 | chr14 | 73180208 | 73180314 | Hypo | cancer_general | DPF3 |
| chr4 | 73226952 | 73227005 | Hypo | cancer_general | DPF3 | chr14 | 73231266 | 73231414 | Hypo | lung, cancer_general | DPF3 |
| chr4 | 73236095 | 73236178 | Hypo | cancer_general | DPF3 | chr14 | 73318471 | 73318629 | Hypo | lung, cancer_general | DPF3 |
| chr4 | 73333249 | 73333396 | Hypo | cancer_general | DPF3 | chr14 | 73602250 | 73602389 | Hypo | cancer_general | PSEN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 73604570 | 73604718 | Hypo | cancer_general | PSEN1 | chr14 | 73855616 | 73855646 | Hypo | lung, cancer_general | NUMB |
| chr14 | 73956853 | 73956913 | Hypo | cancer_general | C14orf169, HEATR4 | chr14 | 74529109 | 74529139 | Hypo | cancer_general | ALDH6A1, CCDC176 |
| chr14 | 75760311 | 75760347 | Hypo | cancer_general | LOC731223 | chr14 | 76128674 | 76128842 | Hypo | cancer_general | C14orf1, TTLL5 |
| chr14 | 77737785 | 77737814 | Hypo | tcga | POMT2, MIR1260A, NGB | chr14 | 88457599 | 88457685 | Hypo | cancer_general | U6, GALC |
| chr14 | 90983328 | 90983360 | Hypo | cancer_general | — | chr14 | 91691163 | 91691306 | Hypo | lung | GPR68 |
| chr14 | 91691696 | 91691822 | Hypo | lung | GPR68 | chr14 | 91766154 | 91766450 | Hypo | lung | — |
| chr14 | 91780382 | 91780512 | Hypo | hepatobiliary | — | chr14 | 91801036 | 91801164 | Hypo | hepatobiliary | CCDC88C |
| chr14 | 92507578 | 92507792 | Hypo | pancreas, cancer_general | AX721199, BC039675, TRIP11 | chr14 | 93155061 | 93155315 | Hypo | cancer_general | — |
| chr14 | 93571193 | 93571326 | Hypo | breast | IFI27L2 | chr14 | 93706752 | 93706782 | Hypo | cancer_general | BTBD7 |
| chr14 | 94603542 | 94603670 | Hypo | lung | — | chr14 | 95233705 | 95233765 | Hypo | cancer_general | GSC |
| chr14 | 95240227 | 95240341 | Hypo | cancer_general | GSC | chr14 | 95557626 | 95557655 | Hypo | literature | DICER1 |
| chr14 | 95560448 | 95560477 | Hypo | literature | DICER1 | chr14 | 95740035 | 95740116 | Hypo | cancer_general | CLMN |
| chr14 | 96053974 | 96054020 | Hypo | cancer_general | BC038791 | chr14 | 97045354 | 97045431 | Hypo | cancer_general | — |
| chr14 | 100148073 | 100148230 | Hypo | cancer_general | HHIPL1, CYP46A1, MIR5698 | chr14 | 100643350 | 100643481 | Hypo | cancer_general | — |
| chr14 | 100843765 | 100843912 | Hypo | cancer_general | WDR25, WARS | chr14 | 101250109 | 101250272 | Hypo | cancer_general | — |
| chr14 | 101506231 | 101506260 | Hypo | literature | MIR539, JA715142, MIR376C, MIR543, MIR376A2, MIR1185-1, MIR381, MIR487B, MIR654, MIR1185-2, Mir_544, Mir_654, MIR1193, MIR300, MIR889, Mir_154, MIR495, MIR376B, MIR376A1, MIR655 | chr14 | 102418607 | 102418637 | Hypo | cancer_general | — |
| chr14 | 102521602 | 102521758 | Hypo | cancer_general | — | chr14 | 102529325 | 102529419 | Hypo | cancer_general | — |
| chr14 | 102530007 | 102530234 | Hypo | cancer_general | — | chr14 | 102530500 | 102530530 | Hypo | cancer_general | MOK, AK130824, WDR20 |
| chr14 | 102564464 | 102564605 | Hypo | breast | — | chr14 | 102682077 | 102682149 | Hypo | lung, cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 102772607 | 102772695 | Hypo | cancer_general | MOK | chr14 | 102973169 | 102973268 | Hypo | head_neck | ANKRD9, TECPR2 |
| chr14 | 103477643 | 103477794 | Hypo | cancer_general | — | chr14 | 104160060 | 104160134 | Hypo | cancer_general | AK097119, AX746968, XRCC3 |
| chr14 | 104202705 | 104202759 | Hypo | cancer_general | PPP1R13B, ZFYVE21 | chr14 | 104355204 | 104355273 | Hypo | cancer_general | — |
| chr14 | 104386476 | 104387067 | Hypo | cancer_general | C14orf2, TDRD9 | chr14 | 104547785 | 104547909 | Hypo | cancer_general | ASPG |
| chr14 | 104571985 | 104572116 | Hypo | cancer_general | ASPG | chr14 | 104620411 | 104620554 | Hypo | cancer_general | KIF26A |
| chr14 | 104627664 | 104627759 | Hypo | cancer_general | KIF26A | chr14 | 104645126 | 104645188 | Hypo | cancer_general | KIF26A |
| chr14 | 104646317 | 104646491 | Hypo | cancer_general | KIF26A | chr14 | 104647257 | 104647287 | Hypo | cancer_general | KIF26A |
| chr14 | 104682545 | 104682656 | Hypo | cancer_general | — | chr14 | 104862860 | 104863026 | Hypo | cancer_general | — |
| chr14 | 104897228 | 104897294 | Hypo | cancer_general | AKT1 | chr14 | 105157485 | 105157554 | Hypo | literature | INF2 |
| chr14 | 105239389 | 105239439 | Hypo | literature | AKT1 | chr14 | 105239793 | 105239825 | Hypo | literature | AKT1 |
| chr14 | 105246427 | 105246582 | Hypo | literature | AKT1 | chr14 | 105243032 | 105243064 | Hypo | literature | AKT1 |
| chr14 | 105714258 | 105714334 | Hypo | cancer_general | BTBD6, BRF1 | chr14 | 105658349 | 105658425 | Hypo | cancer_general | — |
| HCMV-AD169 | 17724 | 17753 | Hypo | virus | — | GL000231.1 | 12576 | 12717 | Hypo | cancer_general | — |
| HCMV-AD169 | 23851 | 23880 | Hypo | virus | — | HCMV-AD169 | 18691 | 18720 | Hypo | virus | — |
| HCMV-AD169 | 42909 | 42938 | Hypo | virus | — | HCMV-AD169 | 27296 | 27325 | Hypo | virus | — |
| HCMV-AD169 | 68427 | 68456 | Hypo | virus | — | HCMV-AD169 | 57909 | 57938 | Hypo | virus | — |
| HCMV-AD169 | 78956 | 78985 | Hypo | virus | — | HCMV-AD169 | 76862 | 76891 | Hypo | virus | — |
| HCMV-AD169 | 84448 | 84477 | Hypo | virus | — | HCMV-AD169 | 81188 | 81217 | Hypo | virus | — |
| HCMV-AD169 | 99889 | 99918 | Hypo | virus | — | HCMV-AD169 | 88920 | 88949 | Hypo | virus | — |
| HCMV-AD169 | 108021 | 108050 | Hypo | virus | — | HCMV-AD169 | 101238 | 101267 | Hypo | virus | — |
| HCMV-AD169 | 128011 | 128040 | Hypo | virus | — | HCMV-AD169 | 114824 | 114853 | Hypo | virus | — |
| HCMV-AD169 | 149187 | 149216 | Hypo | virus | — | HCMV-AD169 | 129567 | 129596 | Hypo | virus | — |
| HCMV-AD169 | 169250 | 169279 | Hypo | virus | — | HCMV-AD169 | 162299 | 162328 | Hypo | virus | — |
| HCMV-AD169 | 172561 | 172590 | Hypo | virus | — | HCMV-AD169 | 171221 | 171250 | Hypo | virus | — |
| HCMV-AD169 | 193060 | 193089 | Hypo | virus | — | HCMV-AD169 | 177053 | 177082 | Hypo | virus | — |
| HCMV-AD169 | 194176 | 194205 | Hypo | virus | — | HCMV-AD169 | 193858 | 193887 | Hypo | virus | — |
| HCMV-AD169 | 196060 | 196089 | Hypo | virus | — | HCMV-AD169 | 195222 | 195251 | Hypo | virus | — |
| HCMV-AD169 | | | | | | HCMV-AD169 | 196817 | 196846 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HCMV AD169 | 199152 | 199181 | Hypo | virus | — | HCMV-AD169 | 199906 | 199935 | Hypo | virus | — |
| HCMV AD169 | 201145 | 201174 | Hypo | virus | — | HCMV-AD169 | 204433 | 204462 | Hypo | virus | — |
| HCMV AD169 | 207682 | 207711 | Hypo | virus | — | HCMV-AD169 | 209510 | 209539 | Hypo | virus | — |
| HCMV AD169 | 210069 | 210098 | Hypo | virus | — | HCMV-AD169 | 212133 | 212162 | Hypo | virus | — |
| HCMV AD169 | 212591 | 212620 | Hypo | virus | — | HCMV-AD169 | 214453 | 214482 | Hypo | virus | — |
| HCMV AD169 | 220316 | 220345 | Hypo | virus | — | MCV-R17b | 111 | 140 | Hypo | virus | — |
| MCV-R17b | 368 | 397 | Hypo | virus | — | MCV-R17b | 625 | 654 | Hypo | virus | — |
| MCV-R17b | 882 | 911 | Hypo | virus | — | MCV-R17b | 1139 | 1168 | Hypo | virus | — |
| MCV-R17b | 1396 | 1425 | Hypo | virus | — | MCV-R17b | 1653 | 1682 | Hypo | virus | — |
| MCV-R17b | 1910 | 1939 | Hypo | virus | — | MCV-R17b | 2167 | 2196 | Hypo | virus | — |
| MCV-R17b | 2424 | 2453 | Hypo | virus | — | MCV-R17b | 2681 | 2710 | Hypo | virus | — |
| MCV-R17b | 2938 | 2967 | Hypo | virus | — | MCV-R17b | 3195 | 3224 | Hypo | virus | — |
| MCV-R17b | 3452 | 3481 | Hypo | virus | — | MCV-R17b | 3709 | 3738 | Hypo | virus | — |
| MCV-R17b | 3966 | 3995 | Hypo | virus | — | MCV-R17b | 4223 | 4252 | Hypo | virus | — |
| MCV-R17b | 4480 | 4509 | Hypo | virus | — | MCV-R17b | 4737 | 4766 | Hypo | virus | — |
| MCV-R17b | 4994 | 5023 | Hypo | virus | — | chr7 | 68930 | 68960 | Hypo | cancer_general | — |
| chr7 | 369494 | 369536 | Hypo | cancer_general | — | chr7 | 369844 | 369980 | Hypo | cancer_general | LOC442497 |
| chr7 | 389663 | 389693 | Hypo | cancer_general | LOC442497 | chr7 | 409826 | 409892 | Hypo | esophageal | LOC442497 |
| chr7 | 427454 | 427484 | Hypo | hepatobiliary | — | chr7 | 431386 | 431492 | Hypo | cancer_general | — |
| chr7 | 497782 | 497934 | Hypo | cancer_general | FLJ44511, PDGFA | chr7 | 503811 | 503936 | Hypo | cancer_general | — |
| chr7 | 551599 | 551697 | Hypo | cancer_general | PRKAR1B | chr7 | 564237 | 564271 | Hypo | breast | FLJ44511 |
| chr7 | 578922 | 579020 | Hypo | cancer_general | — | chr7 | 579827 | 579857 | Hypo | cancer_general | PRKAR1B SUN1, GET4 |
| chr7 | 842331 | 842414 | Hypo | cancer_general | GET4, SUN1 | chr7 | 907656 | 907709 | Hypo | breast | CYP2W1, COX19 |
| chr7 | 915058 | 915087 | Hypo | literature | CYP2W1, COX19 | chr7 | 1016343 | 1016373 | Hypo | colorectal | C7orf50, CYP2W1 |
| chr7 | 1022224 | 1022254 | Hypo | cancer_general | MIR339, C7orf50 | chr7 | 1030172 | 1030283 | Hypo | cancer_general | GPR146 |
| chr7 | 1054579 | 1054696 | Hypo | cancer_general | AK090593, AK123998, ZFAND2A | chr7 | 1086199 | 1086319 | Hypo | cancer_general | — |
| chr7 | 1195270 | 1195364 | Hypo | hepatobiliary | — | chr7 | 1308351 | 1308497 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 1325810 | 1325882 | Hypo | cancer_general | — | chr7 | 1416020 | 1416131 | Hypo | cancer_general | — |
| chr7 | 1423632 | 1423677 | Hypo | cancer_general | — | chr7 | 1459041 | 1459191 | Hypo | cancer_general | — |
| chr7 | 1503417 | 1503596 | Hypo | cancer_general | AK127339, INTS1 | chr7 | 1547311 | 1547394 | Hypo | cancer_general | INTS1 |
| chr7 | 1598639 | 1598697 | Hypo | cancer_general | TMEM184A, PSMG3 | chr7 | 1607386 | 1607465 | Hypo | cancer_general | PSMG3-AS1, PSMG3 |
| chr7 | 1607971 | 1608001 | Hypo | cancer_general | PSMG3-AS1, PSMG3 | chr7 | 1611443 | 1611522 | Hypo | cancer_general | PSMG3-AS1, PSMG3 |
| chr7 | 1615390 | 1615444 | Hypo | cancer_general | PSMG3, PSMG3-AS1 | chr7 | 1627404 | 1627434 | Hypo | cancer_general | KIAA1908, PSMG3-AS1 |
| chr7 | 1641774 | 1641923 | Hypo | cancer_general | — | chr7 | 1681189 | 1681239 | Hypo | cancer_general | — |
| chr7 | 1688977 | 1689146 | Hypo | cancer_general | — | chr7 | 1690745 | 1690851 | Hypo | cancer_general | — |
| chr7 | 1733166 | 1733378 | Hypo | cancer_general | LOC401296 | chr7 | 1735223 | 1735354 | Hypo | cancer_general | LOC401296 |
| chr7 | 1775831 | 1775861 | Hypo | cancer_general | ELFN1, JX046910 | chr7 | 1778875 | 1778914 | Hypo | cancer_general | ELFN1, JX046910 |
| chr7 | 1783551 | 1783623 | Hypo | cancer_general | ELFN1, JX046910, | chr7 | 1786514 | 1786899 | Hypo | cancer_general | ELFN1, JX046910 |
| chr7 | 1787166 | 1787324 | Hypo | cancer_general | ELFN1, JX046910 | chr7 | 1800882 | 1800912 | Hypo | cancer_general | — |
| chr7 | 1970842 | 1970872 | Hypo | pancreas | MAD1L1 | chr7 | 2109874 | 2109904 | Hypo | pancreas | MAD1L1 |
| chr7 | 2163332 | 2163467 | Hypo | cancer_general | MAD1L1 | chr7 | 2208670 | 2208808 | Hypo | cancer_general | MAD1L1 |
| chr7 | 2232963 | 2233056 | Hypo | cancer_general | MAD1L1 | chr7 | 2233292 | 2233414 | Hypo | cancer_general | MAD1L1 |
| chr7 | 2238118 | 2238235 | Hypo | lung | SNX8 | chr7 | 2300787 | 2300899 | Hypo | cancer_general | SNX8 |
| chr7 | 2361190 | 2361434 | Hypo | cancer_general | — | chr7 | 2473452 | 2473605 | Hypo | lung | BC034268, CHST12 |
| chr7 | 2565919 | 2566041 | Hypo | cancer_general | MIR4648, LFNG | chr7 | 2566600 | 2566630 | Hypo | cancer_general | MIR4648, LFNG |
| chr7 | 2595825 | 2595943 | Hypo | pancreas | IQCE, BRAT1 | chr7 | 2659340 | 2659370 | Hypo | cancer_general | — |
| chr7 | 2720013 | 2720140 | Hypo | cancer_general | AMZ1 | chr7 | 2979480 | 2979512 | Hypo | literature | CARD11 |
| chr7 | 2985518 | 2985547 | Hypo | literature | CARD11 | chr7 | 3033658 | 3033688 | Hypo | cancer_general | CARD11 |
| chr7 | 3283704 | 3283894 | Hypo | cancer_general | — | chr7 | 4215324 | 4215384 | Hypo | cancer_general | SDK1 |
| chr7 | 4657806 | 4657857 | Hypo | hepatobiliary | — | chr7 | 4856984 | 4857048 | Hypo | cancer_general | RADIL |
| chr7 | 5262433 | 5262562 | Hypo | lung | WIPI2 | chr7 | 5397777 | 5397938 | Hypo | breast | TNRC18 |
| chr7 | 5603717 | 5603947 | Hypo | cancer_general | — | chr7 | 5648107 | 5648393 | Hypo | literature, cancer_general | FSCN1 |
| chr7 | 6045612 | 6045641 | Hypo | literature | AIMP2, PMS2 | chr7 | 6059024 | 6059182 | Hypo | ovarian | EIF2AK1, AIMP2 |
| chr7 | 6060590 | 6060634 | Hypo | cancer_general | EIF2AK1, AIMP2 | chr7 | 6099217 | 6099334 | Hypo | cancer_general | — |
| chr7 | 6124585 | 6124714 | Hypo | cancer_general | — | chr7 | 6188610 | 6189061 | Hypo | breast | USP42 |
| chr7 | 6307943 | 6308066 | Hypo | cancer_general | CYTH3 | chr7 | 6414386 | 6414415 | Hypo | literature | RAC1 |
| chr7 | 6426878 | 6426907 | Hypo | literature | RAC1 | chr7 | 6443279 | 6443376 | Hypo | cancer_general | RAC1, DAGLB |
| chr7 | 6443826 | 6443856 | Hypo | cancer_general | DAGLB, RAC1 | chr7 | 6484445 | 6484545 | Hypo | lung | DAGLB |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 6524573 | 6524744 | Hypo | cancer_general | KDELR2 | chr7 | 6524977 | 6525012 | Hypo | cancer_general | KDELR2, Mir_633, GRID2IP |
| chr7 | 6525477 | 6525606 | Hypo | cancer_general | KDELR2 | chr7 | 6560235 | 6560345 | Hypo | cancer_general | |
| chr7 | 7015498 | 7015673 | Hypo | ovarian | | chr7 | 7605441 | 7605822 | Hypo | cancer_general | MIOS |
| chr7 | 8343630 | 8343724 | Hypo | cancer_general | | chr7 | 8391475 | 8391573 | Hypo | cancer_general | AX746880 |
| chr7 | 12751410 | 12751496 | Hypo | colorectal | | chr7 | 12776779 | 12776811 | Hypo | cancer_general | — |
| chr7 | 20089670 | 20089700 | Hypo | hepatobiliary | | chr7 | 20183238 | 20183283 | Hypo | hepatobiliary | MACC1-AS1, MACC1 |
| chr7 | 21403615 | 21403645 | Hypo | cancer_general | | chr7 | 22824965 | 22825009 | Hypo | colorectal, cancer_general | — |
| chr7 | 23253573 | 23253671 | Hypo | colorectal | AK057873 | chr7 | 23526549 | 23526698 | Hypo | cancer_general | RPS2P32 |
| chr7 | 23578703 | 23578857 | Hypo | cancer_general | TRA2A | chr7 | 24580644 | 24580806 | Hypo | cancer_general | — |
| chr7 | 25132558 | 25132726 | Hypo | cancer_general | | chr7 | 25133492 | 25133650 | Hypo | cancer_general | — |
| chr7 | 25165921 | 25166061 | Hypo | cancer_general | C7orf31, CYCS | chr7 | 26194906 | 26195024 | Hypo | cancer_general | NFE2L3 |
| chr7 | 26283775 | 26283954 | Hypo | cancer_general, breast | | chr7 | 27184015 | 27184190 | Hypo | literature | HOXA7, HOXA5, HOXA6, HOXA-AS3, DQ655986 |
| chr7 | 27245668 | 27245795 | Hypo | cancer_general | HOTTIP, HOXA13 | chr7 | 28110701 | 28110828 | Hypo | breast | JAZF1 |
| chr7 | 28238339 | 28238444 | Hypo | cancer_general | JAZF1-AS1 | chr7 | 28889065 | 28889159 | Hypo | cancer_general | TRIL, DQ601810 |
| chr7 | 30029923 | 30029952 | Hypo | tcga | SCRN1 FAM188B, NMT-FAM188B | chr7 | 30030307 | 30030337 | Hypo | cancer_general | SCRN1 |
| chr7 | 30857157 | 30857292 | Hypo | lung | | chr7 | 33167928 | 33168030 | Hypo | ovarian | BBS9 |
| chr7 | 33725803 | 33725938 | Hypo | lung | TBX20 | chr7 | 35298755 | 35298819 | Hypo | cancer_general | TBX20 |
| chr7 | 35301086 | 35301216 | Hypo | cancer_general | NME8 | chr7 | 37352957 | 37353062 | Hypo | cancer_general | — |
| chr7 | 37907440 | 37907470 | Hypo | cancer_general | | chr7 | 38588471 | 38588501 | Hypo | esophageal | — |
| chr7 | 42377468 | 42377497 | Hypo | literature | RASA4CP, DBNL, LINC00957 | chr7 | 43817999 | 43818119 | Hypo | cancer_general | BLVRA PGAM2, DBNL |
| chr7 | 44083283 | 44083416 | Hypo | cancer_general | | chr7 | 44097690 | 44097876 | Hypo | head_neck | |
| chr7 | 44151398 | 44151428 | Hypo | cancer_general | POLD2, AEBP1, MIR4649 | chr7 | 44151795 | 44151933 | Hypo | cancer_general | POLD2, AEBP1, MIR4649 |
| chr7 | 44740467 | 44740672 | Hypo | ovarian | OGDH | chr7 | 44835037 | 44835384 | Hypo | cancer_general | PPIA |
| chr7 | 44912004 | 44912034 | Hypo | head_neck | PURB | chr7 | 45026942 | 45027045 | Hypo | cancer_general | SNORA9, SNHG15, MYO1G |
| chr7 | 45038532 | 45038655 | Hypo | cancer_general | CCM2 | chr7 | 45046874 | 45046982 | Hypo | breast | CCM2 |
| chr7 | 45525402 | 45525432 | Hypo | cancer_general | | chr7 | 45614929 | 45615020 | Hypo | pancreas | ADCY1 |
| chr7 | 47515359 | 47515405 | Hypo | cancer_general | TNS3 | chr7 | 47704289 | 47704359 | Hypo | cancer_general | C7orf65 |
| chr7 | 49654508 | 49654538 | Hypo | cancer_general | | chr7 | 49819674 | 49819703 | Hypo | literature | VWC2 |
| chr7 | 50294451 | 50294481 | Hypo | cancer_general | | chr7 | 50365076 | 50365137 | Hypo | cancer_general | IKZF1 |
| chr7 | 50438618 | 50438648 | Hypo | cancer_general | IKZF1 | chr7 | 50441145 | 50441285 | Hypo | cancer_general | IKZF1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 50560588 | 50560637 | Hypo | cancer_general | DDC | chr7 | 55209976 | 55210005 | Hypo | literature | EGFR |
| chr7 | 55211065 | 55211094 | Hypo | literature | EGFR | chr7 | 55221729 | 55221836 | Hypo | literature | EGFR |
| chr7 | 55223589 | 55223636 | Hypo | literature | EGFR | chr7 | 55227993 | 55228022 | Hypo | literature | EGFR |
| chr7 | 55233028 | 55233123 | Hypo | literature | EGFR | chr7 | 55241663 | 55241737 | Hypo | literature | EGFR-AS1, EGFR |
| chr7 | 55242419 | 55242493 | Hypo | literature | EGFR-AS1, EGFR | chr7 | 55248975 | 55249085 | Hypo | literature | EGFR, EGFR-AS1 |
| chr7 | 55259404 | 55259547 | Hypo | literature | EGFR, EGFR-AS1 | chr7 | 55260469 | 55260498 | Hypo | literature | EGFR, EGFR-AS1 |
| chr7 | 55268867 | 55268896 | Hypo | literature | GU228584, EGFR | chr7 | 54410019 | 54410126 | Hypo | breast | |
| chr7 | 55506288 | 55506348 | Hypo | lung | LANCL2 | chr7 | 56018123 | 56018286 | Hypo | cancer_general | MRPS17, ZNF713 |
| chr7 | 56031716 | 56031869 | Hypo | cancer_general | GBAS, MRPS17 | chr7 | 63667431 | 63667460 | Hypo | literature | ZNF735 |
| chr7 | 64330411 | 64330470 | Hypo | hepatobiliary | AK097702 | chr7 | 64330734 | 64330833 | Hypo | cancer_general | AK097702 |
| chr7 | 64713317 | 64713449 | Hypo | cancer_general | | chr7 | 65510006 | 65510096 | Hypo | cancer_general | |
| chr7 | 65879649 | 65879883 | Hypo | cancer_general | | chr7 | 65880359 | 65880405 | Hypo | cancer_general | |
| chr7 | 66204493 | 66204617 | Hypo | cancer_general | RABGEF1 | chr7 | 66206923 | 66206953 | Hypo | cancer_general | RABGEF1 |
| chr7 | 66214923 | 66214961 | Hypo | cancer_general | RABGEF1 | chr7 | 67579765 | 67579911 | Hypo | cancer_general | |
| chr7 | 68204793 | 68204948 | Hypo | cancer_general | | chr7 | 69352121 | 69352272 | Hypo | cancer_general | AUTS2 |
| chr7 | 69897780 | 69897827 | Hypo | cancer_general | AUTS2 | chr7 | 70990312 | 70990342 | Hypo | cancer_general | |
| chr7 | 71438424 | 71438454 | Hypo | cancer_general | CALN1 | chr7 | 71603924 | 71604082 | Hypo | cancer_general | |
| chr7 | 71871203 | 71871245 | Hypo | cancer_general | | chr7 | 76033151 | 76033289 | Hypo | colorectal | ZP3 |
| chr7 | 77129743 | 77129907 | Hypo | lung | | chr7 | 77308664 | 77308899 | Hypo | cancer_general | RSBN1L-AS1 |
| chr7 | 77309437 | 77309511 | Hypo | cancer_general | RSBN1L-AS1 | chr7 | 77324362 | 77324593 | Hypo | cancer_general | RSBN1L, RSBN1L-AS1 |
| chr7 | 87105401 | 87105430 | Hypo | tcga | ABCB4 | chr7 | 87706818 | 87706877 | Hypo | cancer_general | ADAM22 |
| chr7 | 87825006 | 87825137 | Hypo | hepatobiliary | SRI | chr7 | 88388631 | 88388660 | Hypo | tcga | ZNF804B |
| chr7 | 90269263 | 90269563 | Hypo | literature, cancer_general | CDK14 | chr7 | 90797539 | 90797568 | Hypo | literature | CDK14 |
| chr7 | 92554253 | 92554452 | Hypo | cancer_general | | chr7 | 92689705 | 92689818 | Hypo | cancer_general | CASD1 |
| chr7 | 93220696 | 93220826 | Hypo | cancer_general | GNGT1 | chr7 | 94138158 | 94138315 | Hypo | cancer_general | DLX5 |
| chr7 | 96627013 | 96627064 | Hypo | cancer_general | DLX6, DLX6-AS1 | chr7 | 96651469 | 96651537 | Hypo | cancer_general | |
| chr7 | 97490474 | 97490508 | Hypo | hepatobiliary | ASNS | chr7 | 97580497 | 97580648 | Hypo | cancer_general | MGC72080 BHLHA15, TECPR1, LMTK2 |
| chr7 | 97600104 | 97600224 | Hypo | cancer_general | BC122864, MGC72080 | chr7 | 97839654 | 97839684 | Hypo | cancer_general | TECPR1 |
| chr7 | 97869290 | 97869391 | Hypo | cancer_general | TECPR1 | chr7 | 97869614 | 97869644 | Hypo | lung | ARPC1B, ARPC1A |
| chr7 | 98197206 | 98197242 | Hypo | cancer_general | | chr7 | 98966786 | 98966916 | Hypo | | ARPC1B, ARPC1A |
| chr7 | 98969875 | 98969928 | Hypo | cancer_general | ARPC1B, ARPC1A | chr7 | 98971509 | 98971549 | Hypo | | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 99035152 | 99035191 | Hypo | esophageal | CPSF4, ATP5J2-PTCD1, PTCD1 | chr7 | 99104258 | 99104388 | Hypo | cancer_general | ZKSCAN5, AJ297365, ZNF394 |
| chr7 | 995591579 | 99591762 | Hypo | cancer_general | AZGP1P1 | chr7 | 99642049 | 99642100 | Hypo | cancer_general | ZSCAN21, ZKSCAN1 |
| chr7 | 99751578 | 99751630 | Hypo | colorectal | C7orf43, MIR4658, GAL3ST4, LAMTOR4 | chr7 | 99934913 | 99934943 | Hypo | cancer_general | PMS2P1, PILRB |
| chr7 | 100088183 | 100088312 | Hypo | cancer_general | NYAP1 | chr7 | 100179889 | 100179927 | Hypo | cancer_general | FBXO24, PCOLCE-AS1, LRCH4, ZASP, SAP25 |
| chr7 | 100241592 | 100241697 | Hypo | cancer_general | ACTL6B, TFR2 | chr7 | 100295321 | 100295424 | Hypo | cancer_general | GIGYF1, POP7 |
| chr7 | 100320690 | 100320719 | Hypo | literature | EPO | chr7 | 101241993 | 101242023 | Hypo | cancer_general | CUX1 |
| chr7 | 101475790 | 101475858 | Hypo | cancer_general | CUX1 | chr7 | 101585887 | 101585917 | Hypo | cancer_general | CUX1 |
| chr7 | 101627741 | 101627787 | Hypo | cancer_general | CUX1 | chr7 | 101707502 | 101707532 | Hypo | cancer_general | — |
| chr7 | 102091406 | 102091534 | Hypo | blood | ALKBH4, ORAI2 | chr7 | 102801710 | 102801804 | Hypo | lung | — |
| chr7 | 105279467 | 105279671 | Hypo | cancer_general | ATXN7L1 | chr7 | 106622834 | 106622961 | Hypo | cancer_general | — |
| chr7 | 106797774 | 106797804 | Hypo | colorectal | PRKAR2B | chr7 | 107483694 | 107483918 | Hypo | colorectal | — |
| chr7 | 111202993 | 111203260 | Hypo | literature, cancer_general | — | chr7 | 116412008 | 116412058 | Hypo | literature | — |
| chr7 | 116415100 | 116415129 | Hypo | literature | — | chr7 | 116417443 | 116417496 | Hypo | literature | — |
| chr7 | 116422067 | 116422132 | Hypo | literature | — | chr7 | 116423399 | 116423488 | Hypo | literature | — |
| chr7 | 121956724 | 121956754 | Hypo | cancer_general | CADPS2, FEZF1-AS1 | chr7 | 123175689 | 123175899 | Hypo | cancer_general | NDUFA5, IQUB |
| chr7 | 125082621 | 125082698 | Hypo | cancer_general | SND1 | chr7 | 127371129 | 127371249 | Hypo | breast | SND1 |
| chr7 | 127615951 | 127615951 | Hypo | ovarian | FLNC | chr7 | 128097059 | 128097089 | Hypo | cancer_general | HILPDA |
| chr7 | 128486036 | 128486138 | Hypo | cancer_general | KCP | chr7 | 128528749 | 128528779 | Hypo | cancer_general | KCP |
| chr7 | 128529023 | 128529053 | Hypo | cancer_general | UBE2H, AL832212 | chr7 | 129229456 | 129229631 | Hypo | cancer_general | — |
| chr7 | 129483356 | 129483449 | Hypo | lung | TMEM209 | chr7 | 129794593 | 129794721 | Hypo | cancer_general | TMEM209 |
| chr7 | 129800243 | 129800434 | Hypo | breast | MKLN1 | chr7 | 129844226 | 129844493 | Hypo | cancer_general | SSMEM1, TMEM209 |
| chr7 | 1310041515 | 1310041596 | Hypo | breast | SNORD81, PTN | chr7 | 134918503 | 134918637 | Hypo | breast | STRA8 |
| chr7 | 136969053 | 136969083 | Hypo | cancer_general | LOC100134229, JHDM1D | chr7 | 138042221 | 138042288 | Hypo | ovarian | — |
| chr7 | 139878250 | 139878296 | Hypo | cancer_general | SLC37A3 | chr7 | 139939160 | 139939318 | Hypo | cancer_general | — |
| chr7 | 140027008 | 140027079 | Hypo | colorectal | AK131347, RAB19 | chr7 | 140096812 | 140096882 | Hypo | cancer_general | AK131347, RAB19 |
| chr7 | 140097126 | 140097196 | Hypo | cancer_general | DENND2A | chr7 | 140180094 | 140180444 | Hypo | ovarian | MKRN1 |
| chr7 | 140218123 | 140218352 | Hypo | tcga | BRAF | chr7 | 140219405 | 140219435 | Hypo | colorectal | DENND2A |
| chr7 | 140453121 | 140453167 | Hypo | literature | | chr7 | 140477779 | 140477868 | Hypo | literature | BRAF |

TABLE 11-continued

| chr | Start | Stop | Hypo/hyper | classification | annotation |
|---|---|---|---|---|---|
| chr7 | 140481381 | 140481431 | Hypo | literature | BRAF |
| chr7 | 144712934 | 144713064 | Hypo | cancer_general | — |
| chr7 | 148508712 | 148508741 | Hypo | literature | EZH2 |
| chr7 | 148846138 | 148846180 | Hypo | cancer_general | ZNF398 |
| chr7 | 148851143 | 148851234 | Hypo | breast | ZNF398 |
| chr7 | 149109648 | 149109785 | Hypo | cancer_general | TRNA_Cys |
| chr7 | 150069098 | 150069346 | Hypo | colorectal | ZNF775, RNU6-34P, REPIN1 |
| chr7 | 150070021 | 150070058 | Hypo | colorectal | ZNF775, REPIN1, RNU6-34P |
| chr7 | 150753942 | 150753981 | Hypo | cancer_general | SLC4A2, CDK5, ASIC3 |
| chr7 | 151001356 | 151001435 | Hypo | cancer_general | — |
| chr7 | 151298870 | 151299029 | Hypo | breast | PRKAG2 |
| chr7 | 151591667 | 151591705 | Hypo | cancer_general | — |
| chr7 | 153633796 | 153633942 | Hypo | cancer_general | DPP6 |
| chr7 | 154708275 | 154708338 | Hypo | cancer_general | — |
| chr7 | 155302881 | 155302917 | Hypo | cancer_general | CNPY1 |
| chr7 | 155580846 | 155580876 | Hypo | cancer_general | RBM33 |
| chr7 | 155581765 | 155581980 | Hypo | cancer_general | RBM33 |
| chr7 | 155877196 | 155877283 | Hypo | cancer_general | — |
| chr7 | 156707963 | 156708093 | Hypo | cancer_general | — |
| chr7 | 156779336 | 156779366 | Hypo | cancer_general | MNX1 |
| chr7 | 156832848 | 156833162 | Hypo | cancer_general | — |
| chr7 | 157085373 | 157085487 | Hypo | cancer_general | — |
| chr7 | 157262815 | 157263018 | Hypo | cancer_general | — |
| chr7 | 157335172 | 157335202 | Hypo | cancer_general | PTPRN2 |
| chr7 | 157588586 | 157588791 | Hypo | cancer_general | — |
| chr7 | 157690056 | 157690086 | Hypo | cancer_general | — |
| chr7 | 158065832 | 158065970 | Hypo | hepatobiliary | — |
| chr7 | 158298861 | 158299036 | Hypo | literature | LINC00689 |
| chr7 | 158799791 | — | Hypo | cancer_general | ARL8B |
| chr3 | 5165885 | 5165915 | Hypo | cancer_general | — |
| chr3 | 9941469 | 9941669 | Hypo | cancer_general, literature | IL17RE, JAGN1 |
| chr3 | 10182839 | 10183212 | Hypo | literature | VHL |
| chr3 | 10184304 | 10184333 | Hypo | literature | VHL |
| chr3 | 12586149 | 12586179 | Hypo | cancer_general | C3orf83 |
| chr3 | 12645678 | 12645713 | Hypo | literature | RAF1 |
| chr3 | 12870826 | 12870856 | Hypo | cancer_general | RPL32, CAND2 |
| chr7 | 142785612 | 142785728 | Hypo | cancer_general | — |
| chr7 | 148224541 | 148224686 | Hypo | cancer_general | — |
| chr7 | 148640171 | 148640250 | Hypo | cancer_general | — |
| chr7 | 148846434 | 148846644 | Hypo | cancer_general | ZNF398 |
| chr7 | 148883821 | 148883973 | Hypo | cancer_general | ZNF282, ZNF398 |
| chr7 | 150049604 | 150049718 | Hypo | cancer_general | — |
| chr7 | 150069679 | 150069820 | Hypo | colorectal | ZNF775, REPIN1, RNU6-34P |
| chr7 | 150081236 | 150081308 | Hypo | cancer_general | ZNF775 |
| chr7 | 150870816 | 150870889 | Hypo | cancer_general | ASB10, GBX1 |
| chr7 | 151188034 | 151188063 | Hypo | literature | RHEB |
| chr7 | 151423571 | 151423639 | Hypo | lung | PRKAG2 |
| chr7 | 152913656 | 152913826 | Hypo | cancer_general | — |
| chr7 | 154561150 | 154561189 | Hypo | cancer_general | DPP6 |
| chr7 | 154926351 | 154926397 | Hypo | cancer_general | — |
| chr7 | 155363304 | 155363417 | Hypo | cancer_general | RBM33 |
| chr7 | 155581330 | 155581553 | Hypo | cancer_general | RBM33 |
| chr7 | 155582277 | 155582340 | Hypo | cancer_general | — |
| chr7 | 156259192 | 156259221 | Hypo | literature | NOM1 |
| chr7 | 156744619 | 156744713 | Hypo | cancer_general | — |
| chr7 | 156832223 | 156832402 | Hypo | cancer_general | — |
| chr7 | 156880561 | 156880736 | Hypo | cancer_general | — |
| chr7 | 157085963 | 157086082 | Hypo | cancer_general | — |
| chr7 | 157263294 | 157263471 | Hypo | cancer_general | — |
| chr7 | 157584178 | 157584208 | Hypo | cancer_general | — |
| chr7 | 157606706 | 157606736 | Hypo | cancer_general | — |
| chr7 | 158059762 | 158059794 | Hypo | cancer_general | — |
| chr7 | 158198597 | 158198648 | Hypo | hepatobiliary | — |
| chr7 | 158741193 | 158741267 | Hypo | breast | WDR60 |
| chr3 | 3167720 | 3167750 | Hypo | cancer_general | TRNT1 |
| chr3 | 9924238 | 9924534 | Hypo | cancer_general | JAGN1, CIDEC |
| chr3 | 10027432 | 10027548 | Hypo | cancer_general | AX747493, AK125558, EMC3 |
| chr3 | 10183753 | 10183782 | Hypo | literature | VHL |
| chr3 | 10191477 | 10191620 | Hypo | literature | VHL |
| chr3 | 12632309 | 12632401 | Hypo | literature | RAF1, MKRN2 |
| chr3 | 12673006 | 12673036 | Hypo | lung | — |
| chr3 | 12926053 | 12926102 | Hypo | blood | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 12977067 | 12977144 | Hypo | breast | IQSEC1 | chr3 | 13171814 | 13171844 | Hypo | esophageal | ZFYVE20 |
| chr3 | 13679172 | 13679349 | Hypo | cancer_general | — | chr3 | 15123848 | 15123992 | Hypo | lung, cancer_general | — |
| chr3 | 15780510 | 15780638 | Hypo | esophageal | BC041363, ANKRD28 | chr3 | 17001303 | 17001333 | Hypo | cancer_general | — |
| chr3 | 17735273 | 17735340 | Hypo | cancer_general | TRNA_Pseudo RPL15, NKIRAS1 | chr3 | 20070714 | 20070903 | Hypo | ovarian | — |
| chr3 | 23964882 | 23965019 | Hypo | ovarian | — | chr3 | 31494108 | 31494138 | Hypo | colorectal | — |
| chr3 | 32708277 | 32708405 | Hypo | cancer_general | GOLGA4 | chr3 | 36984378 | 36984425 | Hypo | colorectal | TRANK1 VILL |
| chr3 | 37276385 | 37276490 | Hypo | cancer_general | VILL | chr3 | 38030618 | 38030782 | Hypo | pancreas | MYD88, ACAA1 |
| chr3 | 38032331 | 38032361 | Hypo | cancer_general | — | chr3 | 38182244 | 38182306 | Hypo | literature | — |
| chr3 | 38182626 | 38182655 | Hypo | literature | MYD88, ACAA1 | chr3 | 38208158 | 38208226 | Hypo | cancer_general | OXSR1 |
| chr3 | 40202174 | 40202255 | Hypo | cancer_general | MYRIP | chr3 | 41266086 | 41266151 | Hypo | literature | AK095242, AK311005, CTNNB1 |
| chr3 | 42222730 | 42222847 | Hypo | cancer_general | TRAK1 NKTR, SS18L2 | chr3 | 42329346 | 42329511 | Hypo | cancer_general | — |
| chr3 | 42640855 | 42640964 | Hypo | cancer_general | — | chr3 | 42852329 | 42852359 | Hypo | ovarian | CCBP2, HIGD1A |
| chr3 | 43735604 | 43735634 | Hypo | cancer_general | ABHD5 | chr3 | 47144864 | 47144893 | Hypo | literature | — |
| chr3 | 47352704 | 47352734 | Hypo | ovarian | KLHL18 | chr3 | 47521062 | 47521178 | Hypo | cancer_general | — |
| chr3 | 47555760 | 47555790 | Hypo | cancer_general | ELP6 | chr3 | 47830060 | 47830148 | Hypo | cancer_general | CDC25A |
| chr3 | 47831601 | 47831819 | Hypo | cancer_general | — | chr3 | 48227765 | 48227870 | Hypo | cancer_general | — |
| chr3 | 48236476 | 48236724 | Hypo | cancer_general | MIR4443, CDC25A ARIH2 | chr3 | 48698251 | 48698431 | Hypo | ovarian | — |
| chr3 | 48978413 | 48978479 | Hypo | cancer_general | — | chr3 | 49142883 | 49142913 | Hypo | cancer_general | QARS, USP19 RHOA |
| chr3 | 49196747 | 49196831 | Hypo | ovarian | CCDC71, LAMB2P1 RHOA | chr3 | 49405953 | 49405982 | Hypo | literature | — |
| chr3 | 49412883 | 49412987 | Hypo | literature | RBM6 | chr3 | 49939931 | 49940398 | Hypo | cancer_general | MON1A, MST1R |
| chr3 | 50072827 | 50072925 | Hypo | cancer_general | — | chr3 | 50395506 | 50395536 | Hypo | cancer_general | Mir_324, CACNA2D2, TMEM115, CYB56ID2, NPRL2 |
| chr3 | 50575616 | 50575658 | Hypo | cancer_general | DNAH1 | chr3 | 50968445 | 50968511 | Hypo | cancer_general | DOCK3 |
| chr3 | 52352194 | 52352326 | Hypo | cancer_general | — | chr3 | 52442062 | 52442091 | Hypo | literature | PHF7, BAP1, DNAH1 |
| chr3 | 52552556 | 52552661 | Hypo | cancer_general | STAB1, NT5DC2 | chr3 | 52553469 | 52553499 | Hypo | cancer_general | STAB1, NT5DC2 |
| chr3 | 53032733 | 53033524 | Hypo | cancer_general | DCP1A | chr3 | 53253306 | 53253599 | Hypo | cancer_general | TKT |
| chr3 | 53382392 | 53382565 | Hypo | cancer_general | — | chr3 | 53480628 | 53480683 | Hypo | cancer_general | — |
| chr3 | 54583435 | 54583465 | Hypo | hepatobiliary | BC041347 | chr3 | 55603443 | 55603632 | Hypo | cancer_general | ERC2 |
| chr3 | 57437452 | 57437482 | Hypo | cancer_general | — | chr3 | 57529094 | 57529218 | Hypo | breast | DNAH12 |
| chr3 | 58153446 | 58153608 | Hypo | ovarian | — | chr3 | 63719169 | 63719303 | Hypo | cancer_general | — |
| chr3 | 66053446 | 66053613 | Hypo | lung | — | chr3 | 69740944 | 69740990 | Hypo | cancer_general | — |
| chr3 | 69937703 | 69937848 | Hypo | cancer_general | MITF | chr3 | 70661011 | 70661079 | Hypo | hepatobiliary | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 73045340 | 73045583 | Hypo | cancer_general | PPP4R2 | chr3 | 88247941 | 88248049 | Hypo | cancer_general | CPOX |
| chr3 | 93698033 | 93698063 | Hypo | cancer_general | ARL13B | chr3 | 98313191 | 98313253 | Hypo | cancer_general | TMEM45A |
| chr3 | 98618182 | 98618376 | Hypo | colorectal | DCBLD2 | chr3 | 100228688 | 100228768 | Hypo | cancer_general | SENP7, FAM172BP |
| chr3 | 101094160 | 101094190 | Hypo | colorectal | SENP7 | chr3 | 101230678 | 101231070 | Hypo | cancer_general | |
| chr3 | 101331792 | 101331861 | Hypo | head_neck | | chr3 | 101354294 | 101354442 | Hypo | cancer_general | RPL24, ZBTB11-AS1 |
| chr3 | 101397240 | 101397358 | Hypo | cancer_general | ZBTB11, RPL24, ZBTB11-AS1 | chr3 | 101406823 | 101407190 | Hypo | cancer_general | |
| chr3 | 101411545 | 101411666 | Hypo | lung | RPL24 | chr3 | 101645019 | 101645181 | Hypo | cancer_general | |
| chr3 | 105015466 | 105015519 | Hypo | cancer_general | | chr3 | 105684885 | 105684987 | Hypo | breast | BTLA |
| chr3 | 106936157 | 106936336 | Hypo | cancer_general | LINC00882 | chr3 | 112185933 | 112185975 | Hypo | hepatobiliary | DRD3 |
| chr3 | 113557333 | 113557363 | Hypo | cancer_general | GRAMD1C | chr3 | 113847911 | 113847941 | Hypo | cancer_general | LSAMP |
| chr3 | 115502232 | 115502390 | Hypo | tcga | | chr3 | 115512319 | 115512448 | Hypo | pancreas | POLQ |
| chr3 | 120004468 | 120004497 | Hypo | cancer_general | | chr3 | 121215241 | 121215271 | Hypo | head_neck | ILDR1 |
| chr3 | 121657197 | 121657515 | Hypo | cancer_general | SLC15A2 | chr3 | 121741545 | 121741598 | Hypo | cancer_general | KPNA1 |
| chr3 | 122162036 | 122162117 | Hypo | cancer_general | KPNA1 | chr3 | 122162890 | 122163054 | Hypo | cancer_general | DIRC2 |
| chr3 | 122234242 | 122234538 | Hypo | cancer_general | SEMA5B | chr3 | 122573688 | 122573826 | Hypo | cancer_general | |
| chr3 | 122702288 | 122702451 | Hypo | cancer_general | TRNA_Glu | chr3 | 124410075 | 124410157 | Hypo | head_neck | UNQ2790, ZXDC, CCDC37 |
| chr3 | 125417341 | 125417424 | Hypo | cancer_general | | chr3 | 126157586 | 126157663 | Hypo | breast | MGLL |
| chr3 | 126261929 | 126262000 | Hypo | ovarian | C3orf22, CHST13 | chr3 | 127534814 | 127534897 | Hypo | cancer_general | |
| chr3 | 128056383 | 128056497 | Hypo | cancer_general | EEFSEC | chr3 | 128384991 | 128385132 | Hypo | cancer_general | GP9 |
| chr3 | 128599405 | 128599477 | Hypo | cancer_general | LOC653712, ACAD9 | chr3 | 128786496 | 128786526 | Hypo | colorectal | |
| chr3 | 129008841 | 129009004 | Hypo | head_neck | C3orf37 | chr3 | 129047978 | 129048008 | Hypo | cancer_general | H1FX-AS1 |
| chr3 | 129372419 | 129372546 | Hypo | hepatobiliary | TMCC1 | chr3 | 130502167 | 130502197 | Hypo | cancer_general | |
| chr3 | 130519901 | 130520077 | Hypo | cancer_general | | chr3 | 133217784 | 133217999 | Hypo | cancer_general | PCCB |
| chr3 | 133970381 | 133970474 | Hypo | cancer_general | RYK | chr3 | 136016868 | 136016942 | Hypo | head_neck | SOX14, BC038725 |
| chr3 | 136582883 | 136582951 | Hypo | cancer_general | NCK1, SLC35G2 | chr3 | 137490806 | 137490860 | Hypo | cancer_general | |
| chr3 | 137892691 | 137892721 | Hypo | cancer_general | DBR1 | chr3 | 137894374 | 137894415 | Hypo | cancer_general | DBR1 |
| chr3 | 138058859 | 138058897 | Hypo | cancer_general | MRAS | chr3 | 138318827 | 138318918 | Hypo | breast | FAIM, CEP70 |
| chr3 | 138374229 | 138374258 | Hypo | literature | PIK3CB | chr3 | 138635369 | 138635507 | Hypo | cancer_general | |
| chr3 | 138662266 | 138662296 | Hypo | cancer_general | FOXL2, C3orf72, AK304483, AK128202 | chr3 | 141174349 | 141174606 | Hypo | cancer_general | ZBTB38 |
| chr3 | 141363466 | 141363496 | Hypo | breast | | chr3 | 141481651 | 141482073 | Hypo | cancer_general | |
| chr3 | 141657032 | 141657079 | Hypo | cancer_general | TFDP2, AX748420 | chr3 | 141832939 | 141833015 | Hypo | head_neck | TFDP2 |
| chr3 | 141835935 | 141836077 | Hypo | cancer_general | TFDP2 | chr3 | 142159804 | 142159841 | Hypo | breast | XRN1, ATR |
| chr3 | 142537638 | 142537779 | Hypo | breast | PCOLCE2 | chr3 | 142718283 | 142718358 | Hypo | cancer_general | LOC100289361, U2SURP |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 142791151 | 142791255 | Hypo | colorectal | — | chr3 | 142896156 | 142896214 | Hypo | cancer_general | — |
| chr3 | 143280343 | 143280373 | Hypo | cancer_general | — | chr3 | 143614462 | 143614504 | Hypo | cancer_general | PLSCR2 |
| chr3 | 145735852 | 145735882 | Hypo | ovarian | — | chr3 | 146187946 | 146187978 | Hypo | cancer_general | HLTF-AS1, HLTF |
| chr3 | 148523213 | 148523297 | Hypo | cancer_general | — | chr3 | 148803120 | 148803276 | Hypo | cancer_general | — |
| chr3 | 150237792 | 150237822 | Hypo | cancer_general | — | chr3 | 152107022 | 152107052 | Hypo | pancreas | — |
| chr3 | 152707390 | 152707460 | Hypo | cancer_general | — | chr3 | 152877666 | 152877696 | Hypo | pancreas | RAP2B |
| chr3 | 155456372 | 155456630 | Hypo | pancreas, cancer_general | — | chr3 | 155461030 | 155461195 | Hypo | cancer_general | — |
| chr3 | 156007772 | 156007801 | Hypo | literature | KCNAB1 LRRIQ4, LRRC34 | chr3 | 158319235 | 158319359 | Hypo | hepatobiliary | MLF1 |
| chr3 | 169539898 | 169540679 | Hypo | cancer_general | — | chr3 | 169541070 | 169541102 | Hypo | cancer_general | LRRIQ4 |
| chr3 | 170602030 | 170602133 | Hypo | cancer_general | EIF5A2 | chr3 | 171193088 | 171193311 | Hypo | cancer_general | NCEH1 |
| chr3 | 171529811 | 171529958 | Hypo | cancer_general | — | chr3 | 172342101 | 172342147 | Hypo | cancer_general | NCEH1 |
| chr3 | 172355895 | 172356038 | Hypo | cancer_general | NCEH1 | chr3 | 172383550 | 172383600 | Hypo | cancer_general | ECT2 |
| chr3 | 172425382 | 172425717 | Hypo | cancer_general | U6, NCEH1 | chr3 | 172469925 | 172470036 | Hypo | cancer_general | — |
| chr3 | 173162817 | 173162847 | Hypo | cancer_general | NLGN1 | chr3 | 176710106 | 176710241 | Hypo | ovarian | — |
| chr3 | 176872357 | 176872443 | Hypo | cancer_general | TBL1XR1 | chr3 | 178861259 | 178861447 | Hypo | cancer_general | PIK3CA, BC032034 |
| chr3 | 178916711 | 178916959 | Hypo | literature | PIK3CA | chr3 | 178921537 | 178921568 | Hypo | literature | PIK3CA |
| chr3 | 178927966 | 178928094 | Hypo | literature | PIK3CA | chr3 | 178936059 | 178936111 | Hypo | literature | PIK3CA |
| chr3 | 178952004 | 178952105 | Hypo | literature | KCNMB3, PIK3CA | chr3 | 179367874 | 179367920 | Hypo | cancer_general | USP13 |
| chr3 | 181444108 | 181444236 | Hypo | cancer_general | — | chr3 | 182815811 | 182816027 | Hypo | cancer_general | MCCC1 |
| chr3 | 182895956 | 182896144 | Hypo | cancer_general | MCF2L2 | chr3 | 182911545 | 182911574 | Hypo | literature | MCF2L2 |
| chr3 | 183109854 | 183109883 | Hypo | literature | — | chr3 | 183183523 | 183183659 | Hypo | cancer_general | LINC00888 |
| chr3 | 183208370 | 183208469 | Hypo | cancer_general | KLHL6 | chr3 | 183217676 | 183217706 | Hypo | ovarian | KLHL6 |
| chr3 | 183647996 | 183648026 | Hypo | cancer_general | ABCC5 | chr3 | 183728793 | 183728952 | Hypo | breast | ABCC5-AS1, ABCC5 |
| chr3 | 183870824 | 183870858 | Hypo | cancer_general | DVL3 ECE2, ALG3, MIR1224, VWA5B2 | chr3 | 183872490 | 183872524 | Hypo | cancer_general | DVL3 |
| chr3 | 183965599 | 183965907 | Hypo | cancer_general | — | chr3 | 184018038 | 184018136 | Hypo | cancer_general | PSMD2, ECE2 |
| chr3 | 184031686 | 184031746 | Hypo | cancer_general | PSMD2, EIF4G1 | chr3 | 184057254 | 184057557 | Hypo | lung, cancer_general | FAM131A, CLCN2 |
| chr3 | 185001696 | 185001919 | Hypo | cancer_general | MAP3K13 | chr3 | 185271296 | 185271764 | Hypo | cancer_general | LIPH |
| chr3 | 185275856 | 185275886 | Hypo | cancer_general | LIPH | chr3 | 185303247 | 185303277 | Hypo | cancer_general | SENP2 |
| chr3 | 185363074 | 185363261 | Hypo | cancer_general | IGF2BP2 | chr3 | 185629516 | 185629546 | Hypo | cancer_general | TRA2B |
| chr3 | 185643324 | 185643405 | Hypo | cancer_general | TRA2B | chr3 | 185658513 | 185658543 | Hypo | cancer_general | TRA2B |
| chr3 | 185668237 | 185668311 | Hypo | cancer_general | LOC344887 | chr3 | 186287130 | 186287270 | Hypo | cancer_general | DNAJB11, TBCCD1 |
| chr3 | 186914705 | 186914734 | Hypo | literature | RTP1 | chr3 | 193312128 | 193312347 | Hypo | cancer_general | OPA1 |
| chr3 | 193419702 | 193419732 | Hypo | ovarian | — | chr3 | 193548637 | 193548835 | Hypo | cancer_general | — |
| chr3 | 194048751 | 194048919 | Hypo | cancer_general | — | chr3 | 194120812 | 194120841 | Hypo | literature | ATP13A3, GP5 |
| chr3 | 194981816 | 194981913 | Hypo | cancer_general | — | chr3 | 195095450 | 195095543 | Hypo | ovarian | ACAP2 |
| chr3 | 195184022 | 195184140 | Hypo | colorectal | — | chr3 | 195409773 | 195409813 | Hypo | ovarian | SDHAP2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 195536733 | 195536848 | Hypo | cancer_general | MUC4 | chr3 | 195538217 | 195538353 | Hypo | cancer_general | MUC4 |
| chr3 | 195587032 | 195587118 | Hypo | cancer_general | TNK2 | chr3 | 195601239 | 195601312 | Hypo | pancreas | TNK2 |
| chr3 | 195602330 | 195602576 | Hypo | pancreas | TNK2 | chr3 | 195639755 | 195639785 | Hypo | head_neck | AK127609, TNK2 |
| chr3 | 195648794 | 195649004 | Hypo | cancer_general | TM4SF19, TM4SF19-TCTEX1D2, AK124973, TCTEX1D2 | chr3 | 195834581 | 195834611 | Hypo | cancer_general | TM4SF19, TM4SF19-TCTEX1D2 |
| chr3 | 196046702 | 196046830 | Hypo | head_neck | TM4SF19, TM4SF19-TCTEX1D2 | chr3 | 196065342 | 196065583 | Hypo | literature | |
| chr3 | 196069743 | 196070340 | Hypo | cancer_general | TM4SF19, TM4SF19-TCTEX1D2 | chr3 | 196263303 | 196263471 | Hypo | cancer_general | |
| chr3 | 196344683 | 196344796 | Hypo | esophageal | LRRC33 | chr3 | 196387295 | 196387415 | Hypo | cancer_general | LRRC33 |
| chr3 | 196387628 | 196387665 | Hypo | cancer_general | PIGX, CEP19, U6 | chr3 | 196388383 | 196388581 | Hypo | cancer_general | LRRC33 |
| chr3 | 196433946 | 196434104 | Hypo | head_neck | | chr3 | 196440510 | 196440676 | Hypo | head_neck | PIGX, U6, CEP19 |
| chr3 | 196667872 | 196668080 | Hypo | cancer_general | NCBP2-AS2, PIGZ, NCBP2, SENP5 | chr3 | 196728418 | 196728448 | Hypo | head_neck | MFI2, MFI2-AS1 |
| chr3 | 196731155 | 196731313 | Hypo | cancer_general | MFI2-AS1, MFI2 | chr3 | 197209019 | 197209048 | Hypo | literature | |
| chr3 | 197247047 | 197247110 | Hypo | pancreas | BDH1 | chr3 | 197278926 | 197278988 | Hypo | pancreas | BDH1 |
| chr3 | 197313997 | 197314107 | Hypo | cancer_general | LOC220729 | chr3 | 197326860 | 197327042 | Hypo | cancer_general | LOC220729 |
| chr3 | 197330060 | 197330147 | Hypo | cancer_general | LOC220729 | chr3 | 197466364 | 197466540 | Hypo | cancer_general | FYTTD1, KIAA0226 |
| chr3 | 197616707 | 197616861 | Hypo | cancer_general | IQCG, LRCH3 | chr3 | 197685788 | 197686085 | Hypo | literature, cancer_general | LMLN, RPL35A, IQCG |
| chr3 | 197686495 | 197686524 | Hypo | literature | LMLN, RPL35A, IQCG | chr1 | 715373 | 715447 | Hypo | cancer_general | LOC100288069 |
| chr1 | 898654 | 898690 | Hypo | head_neck | PLEKHN1, KLHL17, NOC2L | chr1 | 913532 | 913955 | Hypo | cancer_general | PLEKHN1, C1orf170 |
| chr1 | 1047531 | 1047647 | Hypo | breast | C1orf159 | chr1 | 1080583 | 1080824 | Hypo | cancer_general | LOC254099 SDF4, TNFRSF4, TNFRSF18 |
| chr1 | 1095420 | 1095459 | Hypo | colorectal | MIR429, JA715143, MIR200B, MIR200A, JA715134 | chr1 | 1146734 | 1146818 | Hypo | cancer_general | |
| chr1 | 1218737 | 1218820 | Hypo | cancer_general | UBE2J2, ACAP3, SCNN1D | chr1 | 1223512 | 1223652 | Hypo | cancer_general | ACAP3, SCNN1D |
| chr1 | 1235813 | 1236078 | Hypo | cancer_general | PUSL1, ACAP3, SCNN1D | chr1 | 1253330 | 1253386 | Hypo | lung, cancer_general | CPSF3L, GLTPD1, PUSL1, ACAP3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 1267014 | 1267151 | Hypo | cancer_general | DVL1, TAS1R3, GLTPD1, CPSF3L | chr1 | 1267462 | 1267699 | Hypo | cancer_general | CPSF3L, DVL1, TAS1R3, GLTPD1 |
| chr1 | 1267906 | 1268158 | Hypo | cancer_general | CPSF3L, DVL1, TAS1R3, GLTPD1 | chr1 | 1281214 | 1281244 | Hypo | pancreas | MXRA8, DVL1 |
| chr1 | 1341668 | 1341743 | Hypo | cancer_general | MRPL20, LOC148413, CCNL2 | chr1 | 1436043 | 1436211 | Hypo | cancer_general | ATAD3B |
| chr1 | 1473125 | 1473207 | Hypo | head_neck | AX747755, ATAD3A, SSU72, TMEM240 | chr1 | 1483186 | 1483363 | Hypo | head_neck | TMEM240, SSU72 |
| chr1 | 1547129 | 1547348 | Hypo | lung | MIB2, AK094692 | chr1 | 1563193 | 1563223 | Hypo | cancer_general | CDK11B, MIB2, MMP23B |
| chr1 | 1805049 | 1805089 | Hypo | breast | GNB1 | chr1 | 1856436 | 1856466 | Hypo | head_neck | C1orf222, TMEM52, CALML6 |
| chr1 | 1857847 | 1857909 | Hypo | cancer_general | C1orf222, TMEM52, CALML6 | chr1 | 1874744 | 1874787 | Hypo | cancer_general | KIAA1751 |
| chr1 | 1910415 | 1910445 | Hypo | head_neck | KIAA1751 | chr1 | 1923457 | 1923521 | Hypo | cancer_general | KIAA1751 |
| chr1 | 1974848 | 1974925 | Hypo | cancer_general | PRKCZ | chr1 | 2066490 | 2066679 | Hypo | cancer_general | PRKCZ |
| chr1 | 2125216 | 2125483 | Hypo | cancer_general | C1orf86, BC018779 | chr1 | 2263169 | 2263263 | Hypo | cancer_general | MORN1 |
| chr1 | 2267552 | 2267690 | Hypo | cancer_general | MORN1 | chr1 | 2304327 | 2304389 | Hypo | cancer_general | MORN1 |
| chr1 | 2307925 | 2307955 | Hypo | cancer_general | MORN1 | chr1 | 2308376 | 2308636 | Hypo | cancer_general | MORN1 |
| chr1 | 2309868 | 2309953 | Hypo | cancer_general | MORN1 | chr1 | 2331363 | 2331437 | Hypo | ovarian | PEX10, RER1, MORN1 |
| chr1 | 2336397 | 2336427 | Hypo | breast | PEX10, RER1 | chr1 | 2397001 | 2397031 | Hypo | cancer_general | — |
| chr1 | 2428331 | 2428385 | Hypo | cancer_general | PLCH2 | chr1 | 2507063 | 2507183 | Hypo | cancer_general | MMEL1 |
| chr1 | 2514330 | 2514376 | Hypo | ovarian | FAM213B, MMEL1 | chr1 | 2521024 | 2521063 | Hypo | breast | FAM213B |
| chr1 | 2830155 | 2830185 | Hypo | cancer_general | — | chr1 | 2866038 | 2866068 | Hypo | cancer_general | — |
| chr1 | 3102653 | 3102779 | Hypo | cancer_general | — | chr1 | 3158823 | 3158962 | Hypo | cancer_general | — |
| chr1 | 3182883 | 3182917 | Hypo | ovarian | — | chr1 | 3183415 | 3183455 | Hypo | cancer_general | — |
| chr1 | 3322090 | 3322170 | Hypo | cancer_general | — | chr1 | 3601850 | 3601946 | Hypo | cancer_general | TP73 |
| chr1 | 3607081 | 3607236 | Hypo | literature, cancer_general | TP73 | chr1 | 3659550 | 3659716 | Hypo | colorectal | TP73-AS1, TP73, CCDC27 |
| chr1 | 3664461 | 3664741 | Hypo | cancer_general | CCDC27, TP73-AS1, LRRC47, SMIM1 | chr1 | 3683686 | 3683818 | Hypo | cancer_general | SMIM1, CCDC27 |
| chr1 | 3700384 | 3700414 | Hypo | ovarian | — | chr1 | 3733551 | 3733581 | Hypo | esophageal | CEP104 |
| chr1 | 4111061 | 4111231 | Hypo | cancer_general | — | chr1 | 4401433 | 4401463 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 5919973 | 5920071 | Hypo | hepatobiliary | MIR4689, NPHP4 | chr1 | 5920650 | 5920710 | Hypo | hepatobiliary | MIR4689, NPHP4 |
| chr1 | 5924296 | 5924431 | Hypo | hepatobiliary | NPHP4, MIR4689 | chr1 | 5924851 | 5924984 | Hypo | hepatobiliary | NPHP4, MIR4689 |
| chr1 | 5926596 | 5926645 | Hypo | hepatobiliary | NPHP4, MIR4689 | chr1 | 5933086 | 5933144 | Hypo | hepatobiliary | NPHP4 |
| chr1 | 5934925 | 5935061 | Hypo | hepatobiliary | NPHP4 | chr1 | 5940517 | 5940547 | Hypo | hepatobiliary | NPHP4 |
| chr1 | 5940945 | 5941132 | Hypo | hepatobiliary | NPHP4 | chr1 | 5944299 | 5944449 | Hypo | hepatobiliary | NPHP4 |
| chr1 | 5944962 | 5945001 | Hypo | hepatobiliary | NPHP4 | chr1 | 5945348 | 5945435 | Hypo | hepatobiliary | NPHP4 |
| chr1 | 5947258 | 5947288 | Hypo | hepatobiliary | NPHP4 | chr1 | 5949491 | 5949575 | Hypo | hepatobiliary | NPHP4 |
| chr1 | 5950965 | 5951039 | Hypo | hepatobiliary | NPHP4 | chr1 | 5957473 | 5957503 | Hypo | hepatobiliary | NPHP4 |
| chr1 | 5967237 | 5967267 | Hypo | hepatobiliary | NPHP4 | chr1 | 5969001 | 5969283 | Hypo | hepatobiliary | NPHP4 |
| chr1 | 5972104 | 5972134 | Hypo | hepatobiliary | NPHP4 | chr1 | 5972878 | 5972922 | Hypo | hepatobiliary | NPHP4 |
| chr1 | 6021621 | 6021651 | Hypo | hepatobiliary | — | chr1 | 6025872 | 6025950 | Hypo | hepatobiliary | — |
| chr1 | 6036766 | 6036796 | Hypo | hepatobiliary | KCNAB2 | chr1 | 6056157 | 6056201 | Hypo | hepatobiliary | KCNAB2 |
| chr1 | 6056606 | 6056651 | Hypo | hepatobiliary | CHD5, KCNAB2 | chr1 | 6059910 | 6059974 | Hypo | hepatobiliary | KCNAB2 |
| chr1 | 6166353 | 6166469 | Hypo | cancer_general | CHD5 | chr1 | 6171763 | 6171810 | Hypo | cancer_general | CHD5 |
| chr1 | 6186511 | 6186546 | Hypo | pancreas | ICMT, RNF207 | chr1 | 6280243 | 6280273 | Hypo | cancer_general | ICMT, RNF207 |
| chr1 | 6284828 | 6284858 | Hypo | pancreas | ACOT7 | chr1 | 6360593 | 6360634 | Hypo | cancer_general | ACOT7 |
| chr1 | 6410456 | 6410486 | Hypo | head_neck | ACOT7 PHF13, KLHL21 | chr1 | 6446131 | 6446308 | Hypo | cancer_general | ACOT7 |
| chr1 | 6672227 | 6672351 | Hypo | cancer_general | | chr1 | 6713914 | 6714041 | Hypo | ovarian | DNAJC11 |
| chr1 | 6714348 | 6714378 | Hypo | ovarian | DNAJC11 TNFRSF9 | chr1 | 6776304 | 6776388 | Hypo | cancer_general | RERE |
| chr1 | 7973843 | 7973948 | Hypo | cancer_general | | chr1 | 8549986 | 8550078 | Hypo | lung, cancer_general | |
| chr1 | 9402465 | 9402616 | Hypo | breast | SPSB1 C1orf200, PIK3CD | chr1 | 9601954 | 9601984 | Hypo | hepatobiliary | SLC25A33 CLSTN1, PIK3CD |
| chr1 | 9722138 | 9722215 | Hypo | esophageal | | chr1 | 9795995 | 9796196 | Hypo | ovarian | |
| chr1 | 9865110 | 9865140 | Hypo | cancer_general | CLSTN1 | chr1 | 9867157 | 9867316 | Hypo | lung | CLSTN1 |
| chr1 | 10091888 | 10092060 | Hypo | cancer_general | UBE4B | chr1 | 10095469 | 10095845 | Hypo | cancer_general | UBE4B |
| chr1 | 10123736 | 10123928 | Hypo | head_neck | UBE4B APTD1-CORT, APTD1 | chr1 | 10166521 | 10166551 | Hypo | head_neck | UBE4B |
| chr1 | 10491694 | 10491724 | Hypo | cancer_general | | chr1 | 11169346 | 11169375 | Hypo | literature | MTOR, EXOSC10 |
| chr1 | 11174404 | 11174433 | Hypo | literature | MTOR | chr1 | 11181358 | 11181432 | Hypo | literature | MTOR |
| chr1 | 11182142 | 11182171 | Hypo | literature | MTOR | chr1 | 11188149 | 11188178 | Hypo | literature | MTOR |
| chr1 | 11210182 | 11210211 | Hypo | literature | MTOR-AS1, MTOR | chr1 | 11217215 | 11217337 | Hypo | literature | MTOR-AS1, MTOR |
| chr1 | 11591719 | 11591826 | Hypo | cancer_general | PTCHD2 | chr1 | 11886250 | 11886280 | Hypo | head_neck | CLCN6 |
| chr1 | 11936748 | 11936778 | Hypo | cancer_general | — | chr1 | 12041374 | 12041525 | Hypo | cancer_general | MFN2, PLOD1 |
| chr1 | 12251443 | 12251958 | Hypo | lung, cancer_general | MIR4632, TNFRSF1B | chr1 | 12460299 | 12460356 | Hypo | ovarian | VPS13D |
| chr1 | 13984525 | 13984742 | Hypo | head_neck | PRDM2 | chr1 | 14032304 | 14032347 | Hypo | hepatobiliary | PRDM2 |
| chr1 | 14097878 | 14098015 | Hypo | esophageal | AK124197 | chr1 | 14128478 | 14128588 | Hypo | cancer_general | — |
| chr1 | 14149749 | 14149867 | Hypo | head_neck | | chr1 | 14730425 | 14730472 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 14746206 | 14746245 | Hypo | hepatobiliary | — | chr1 | 15128565 | 15128595 | Hypo | hepatobiliary | KAZN |
| chr1 | 16474413 | 16474576 | Hypo | pancreas | EPHA2 | chr1 | 16475031 | 16475207 | Hypo | pancreas | EPHA2 |
| chr1 | 17757538 | 17757570 | Hypo | colorectal | RCC2 | chr1 | 17787472 | 17787502 | Hypo | cancer_general | — |
| chr1 | 19980747 | 19980858 | Hypo | cancer_general | NBL1 | chr1 | 20127338 | 20127471 | Hypo | cancer_general | TMCO4 |
| chr1 | 20248109 | 20248141 | Hypo | cancer_general | PLA2G2E, OTUD3 | chr1 | 20492168 | 20492298 | Hypo | cancer_general | PLA2G2C |
| chr1 | 21026117 | 21026225 | Hypo | cancer_general | KIF17 | chr1 | 21042894 | 21042924 | Hypo | cancer_general | KIF17, SH2D5 |
| chr1 | 21050471 | 21050511 | Hypo | head_neck | SH2D5, KIF17 | chr1 | 21573283 | 21573362 | Hypo | breast | ECE1 |
| chr1 | 21573668 | 21574203 | Hypo | breast | ECE1 | chr1 | 21713716 | 21713792 | Hypo | head_neck | — |
| chr1 | 22141326 | 22141355 | Hypo | tcga | LDLRAD2, HSPG2 | chr1 | 22222711 | 22222793 | Hypo | breast | HSPG2 |
| chr1 | 22927410 | 22927482 | Hypo | cancer_general | EPHA8 | chr1 | 23347997 | 23348043 | Hypo | cancer_general | KDMIA, LOC729059 |
| chr1 | 23449766 | 23449859 | Hypo | head_neck | LUZP1 | chr1 | 24104000 | 24104062 | Hypo | cancer_general | LOC10506963, PITHD1 |
| chr1 | 24161782 | 24161882 | Hypo | colorectal | FUCA1 | chr1 | 24740603 | 24740829 | Hypo | cancer_general | NIPAL3 |
| chr1 | 25257490 | 25257529 | Hypo | literature | RUNX3 | chr1 | 25257916 | 25258250 | Hypo | literature | RUNX3 |
| chr1 | 25919307 | 25919337 | Hypo | ovarian | — | chr1 | 26183522 | 26183579 | Hypo | breast | PAQR7, AUNIP |
| chr1 | 26467523 | 26467630 | Hypo | cancer_general, lung | — | chr1 | 26917724 | 26917816 | Hypo | cancer_general | — |
| chr1 | 26963625 | 26963789 | Hypo | cancer_general | FAM46B | chr1 | 27190175 | 27190278 | Hypo | cancer_general | SFN |
| chr1 | 27332448 | 27332673 | Hypo | pancreas | WASF2, GPR3 | chr1 | 27340252 | 27340412 | Hypo | cancer_general | FAM46B |
| chr1 | 27724058 | 27724093 | Hypo | head_neck | — | chr1 | 27844518 | 27844548 | Hypo | cancer_general | — |
| chr1 | 28558539 | 28558571 | Hypo | cancer_general | ATPIF1, JA611241, DNAJC8 | chr1 | 28226724 | 28226812 | Hypo | ovarian | PHACTR4 |
| chr1 | 28727177 | 28727324 | Hypo | ovarian | PHACTR4 | chr1 | 28727894 | 28728020 | Hypo | ovarian | PHACTR4 |
| chr1 | 29047659 | 29048643 | Hypo | cancer_general | — | chr1 | 29060250 | 29060311 | Hypo | cancer_general | YTHDF2 |
| chr1 | 29065131 | 29065211 | Hypo | cancer_general | YTHDF2 | chr1 | 30351554 | 30351742 | Hypo | cancer_general | — |
| chr1 | 31863186 | 31863216 | Hypo | head_neck | — | chr1 | 32533211 | 32533653 | Hypo | cancer_general | TMEM39B, KHDRBS1 |
| chr1 | 32705488 | 32705550 | Hypo | cancer_general | FAM167B, MTMR9LP, EIF3I | chr1 | 32756498 | 32756581 | Hypo | cancer_general | HDAC1, LCK |
| chr1 | 32938720 | 32938750 | Hypo | cancer_general | ZBTB8A, ZBTB8B | chr1 | 33163605 | 33163786 | Hypo | head_neck | SYNC |
| chr1 | 35586911 | 35586962 | Hypo | cancer_general | ZMYM1 | chr1 | 35664625 | 35664746 | Hypo | cancer_general | SFPQ |
| chr1 | 36236269 | 36236299 | Hypo | cancer_general | CLSPN | chr1 | 36334925 | 36335053 | Hypo | cancer_general | AGO1 |
| chr1 | 36563479 | 36563522 | Hypo | cancer_general | COL8A2, ADPRHL2, TEKT2 | chr1 | 38060267 | 38060317 | Hypo | cancer_general | GNL2 |
| chr1 | 38398213 | 38398348 | Hypo | cancer_general | INPP5B | chr1 | 39416980 | 39417182 | Hypo | cancer_general | RHBDL2 |
| chr1 | 40072513 | 40072680 | Hypo | cancer_general | — | chr1 | 40349545 | 40349647 | Hypo | cancer_general | — |
| chr1 | 40625371 | 40625401 | Hypo | cancer_general | RLF | chr1 | 40708443 | 40708578 | Hypo | head_neck | TMCO2, RLF |
| chr1 | 41915253 | 41915283 | Hypo | breast | — | chr1 | 41967342 | 41967418 | Hypo | cancer_general | HIVEP3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 41991640 | 41991702 | Hypo | cancer_general | HIVEP3 | chr1 | 43188741 | 43188874 | Hypo | cancer_general | CLDN19 |
| chr1 | 43400336 | 43400386 | Hypo | head_neck | SLC2A1 | chr1 | 43478202 | 43478255 | Hypo | cancer_general | — |
| chr1 | 43814994 | 43815023 | Hypo | literature | CDC20, MPL | chr1 | 43834741 | 43834922 | Hypo | cancer_general | ELOVL1, CDC20 |
| chr1 | 43842664 | 43842779 | Hypo | lung | MED8, ELOVL1 | chr1 | 44068774 | 44068804 | Hypo | cancer_general | PTPRF |
| chr1 | 44109845 | 44109959 | Hypo | cancer_general | KDM4A | chr1 | 44310283 | 44310324 | Hypo | colorectal | ST3GAL3 |
| chr1 | 44494137 | 44494169 | Hypo | cancer_general | SLC6A9 | chr1 | 44726912 | 44727268 | Hypo | cancer_general | ERI3 |
| chr1 | 45240427 | 45240514 | Hypo | cancer_general | SNORD38B, BEST4, KIF2C, RPS8, SNORD55, SNORD46, SNORD38A | chr1 | 45308154 | 45308262 | Hypo | cancer_general | PTCH2, EIF2B3 |
| chr1 | 45645870 | 45645998 | Hypo | cancer_general | ZSWIM5 | chr1 | 45768429 | 45768504 | Hypo | cancer_general | LOC400752 |
| chr1 | 46077719 | 46077805 | Hypo | esophageal | CCDC17, NASP | chr1 | 46347598 | 46347689 | Hypo | cancer_general | MAST2 |
| chr1 | 46744657 | 46744733 | Hypo | breast | RAD54L, LRRC41 | chr1 | 47035373 | 47035403 | Hypo | ovarian | MKNK1 |
| chr1 | 47078736 | 47078782 | Hypo | head_neck | MOB3C, MKNK1 | chr1 | 47788247 | 47788348 | Hypo | colorectal | — |
| chr1 | 50881363 | 50881529 | Hypo | cancer_general | DMRTA2 | chr1 | 51424099 | 51424224 | Hypo | cancer_general | CDKN2C ORC1, CC2D1B |
| chr1 | 51763252 | 51763298 | Hypo | cancer_general | TTC39A | chr1 | 52832687 | 52832820 | Hypo | cancer_general | ZYG11B |
| chr1 | 53129154 | 53129244 | Hypo | cancer_general | FAM159A | chr1 | 53192045 | 53192075 | Hypo | breast | — |
| chr1 | 53705647 | 53705701 | Hypo | pancreas | LOC100507564, MAGOH, LRP8 | chr1 | 54586626 | 54586736 | Hypo | cancer_general | SSBP3 |
| chr1 | 54337089 | 54337119 | Hypo | esophageal | SSBP3 | chr1 | 54877027 | 54877451 | Hypo | ovarian | NFIA |
| chr1 | 55231115 | 55231177 | Hypo | cancer_general | PARS2 | chr1 | 61541602 | 61541718 | Hypo | cancer_general, lung | — |
| chr1 | 62189908 | 62189987 | Hypo | cancer_general | TM2D1 | chr1 | 62793237 | 62793267 | Hypo | pancreas | JAK1, RAVER2 |
| chr1 | 64734652 | 64734694 | Hypo | cancer_general | — | chr1 | 65303636 | 65303692 | Hypo | literature | JAK1, RAVER2 |
| chr1 | 65304227 | 65304256 | Hypo | literature | JAK1, RAVER2 | chr1 | 65305384 | 65305413 | Hypo | literature | JAK1, RAVER2 |
| chr1 | 65306926 | 65306955 | Hypo | literature | JAK1, RAVER2 | chr1 | 65309787 | 65309816 | Hypo | literature | JAK1 |
| chr1 | 65310487 | 65310531 | Hypo | literature | JAK1 | chr1 | 65311188 | 65311217 | Hypo | literature | JAK1 |
| chr1 | 65312331 | 65312432 | Hypo | literature | JAK1 | chr1 | 67669791 | 67669853 | Hypo | ovarian | IL23R, U6 |
| chr1 | 70599012 | 70599169 | Hypo | cancer_general | LRRC7 | chr1 | 70672778 | 70672878 | Hypo | cancer_general | SRSF11, LRRC40 |
| chr1 | 75600925 | 75601071 | Hypo | cancer_general | LHX8, AK055631 | chr1 | 76354624 | 76354754 | Hypo | cancer_general | MSH4 |
| chr1 | 78463647 | 78463677 | Hypo | cancer_general | DNAJB4 | chr1 | 84944491 | 84944568 | Hypo | cancer_general | RPF1 |
| chr1 | 85725639 | 85725668 | Hypo | tcga | BCL10, C1orf52 | chr1 | 86296345 | 86296375 | Hypo | cancer_general | COL24A1 |
| chr1 | 86860608 | 86860949 | Hypo | cancer_general | ODF2L | chr1 | 89394066 | 89394163 | Hypo | breast | CBL2 |
| chr1 | 91177989 | 91178149 | Hypo | cancer_general | BARHL2 | chr1 | 91182805 | 91182835 | Hypo | pancreas | BARHL2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 94147816 | 94147845 | Hypo | tcga | — | chr1 | 94343568 | 94343744 | Hypo | cancer_general | GCLM, DNTTIP2 |
| chr1 | 94911234 | 94911328 | Hypo | breast | ABCD3 | chr1 | 97185262 | 97185609 | Hypo | head_neck | PTBP2 |
| chr1 | 98515142 | 98515191 | Hypo | pancreas | MIR2682, MIR137HG, MIR137 | chr1 | 100239507 | 100239544 | Hypo | cancer_general | — |
| chr1 | 100310827 | 100310979 | Hypo | cancer_general | AGL | chr1 | 100437068 | 100437172 | Hypo | cancer_general | SLC35A3, BC112312 |
| chr1 | 108722798 | 108722828 | Hypo | hepatobiliary | SLC25A24 | chr1 | 109585463 | 109585632 | Hypo | cancer_general | WDR47 |
| chr1 | 109595405 | 109595534 | Hypo | ovarian | — | chr1 | 109631549 | 109631682 | Hypo | cancer_general | TMEM167B |
| chr1 | 109644226 | 109644336 | Hypo | cancer_general | C1orf94, SCARNA2, TMEM167B | chr1 | 110883542 | 110883965 | Hypo | cancer_general | RBM15, LOC440600, BC069739 |
| chr1 | 111440961 | 111440999 | Hypo | cancer_general | CD53 | chr1 | 112084954 | 112084984 | Hypo | cancer_general | RAP1A |
| chr1 | 113166315 | 113166394 | Hypo | head_neck | CAPZA1, ST7L | chr1 | 114428007 | 114428160 | Hypo | head_neck | BCL2L15, AP4B1-AS1, AP4B1 |
| chr1 | 114448943 | 114448990 | Hypo | cancer_general | DCLRE1B, AP4B1 | chr1 | 115055395 | 115055425 | Hypo | cancer_general | DENND2C |
| chr1 | 115256514 | 115256552 | Hypo | literature | CSDE1, NRAS | chr1 | 115258729 | 115258772 | Hypo | literature | CSDE1, NRAS |
| chr1 | 116214104 | 116214318 | Hypo | cancer_general | VANGL1 | chr1 | 117901133 | 117901264 | Hypo | cancer_general | MAN1A2 |
| chr1 | 146551186 | 146551215 | Hypo | literature | TRNA_Pseudo, TRNA_His | chr1 | 150603138 | 150603170 | Hypo | cancer_general | ENSA |
| chr1 | 150941425 | 150941847 | Hypo | breast | CERS2, SETDB1 | chr1 | 150994849 | 150995152 | Hypo | ovarian | U6, PRUNE |
| chr1 | 151042405 | 151042496 | Hypo | cancer_general | MLLT11, GABPB2 | chr1 | 151169248 | 151170206 | Hypo | cancer_general | PIP5K1A, VPS72 |
| chr1 | 151253146 | 151253427 | Hypo | cancer_general | ZNF687, BC021024 | chr1 | 151300888 | 151300918 | Hypo | cancer_general | — |
| chr1 | 151362640 | 151362779 | Hypo | colorectal | PSMB4 | chr1 | 153539476 | 153539637 | Hypo | cancer_general | S100A2 |
| chr1 | 153540096 | 153540154 | Hypo | cancer_general | S100A2 | chr1 | 153896746 | 153896800 | Hypo | cancer_general | DENND4B, GATAD2B |
| chr1 | 153937124 | 153937330 | Hypo | cancer_general | CREB3L4, JTB, SLC39A1, CRTC2 | chr1 | 153948791 | 153948823 | Hypo | cancer_general | RAB13, JTB, CREB3L4 |
| chr1 | 154156468 | 154156717 | Hypo | cancer_general | MIR190B, TPM3 | chr1 | 154491036 | 154491066 | Hypo | cancer_general | TDRD10 |
| chr1 | 154516810 | 154516845 | Hypo | cancer_general | UBE2Q1, TDRD10 | chr1 | 155161778 | 155162033 | Hypo | cancer_general | TRIM46, DM075093, MIR92B, THBS3, MUC1, AX746485 |
| chr1 | 155283218 | 155283248 | Hypo | breast | RUSC1-AS1, RUSC1, FDPS | chr1 | 155578375 | 155578921 | Hypo | cancer_general | MSTO1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 155617837 | 155611962 | Hypo | cancer_general | BC041646 | chr1 | 155653788 | 155653868 | Hypo | head_neck | YY1AP1, DAP3 |
| chr1 | 155826248 | 155826336 | Hypo | cancer_general | SYT11 | chr1 | 155874151 | 155874300 | Hypo | literature | KIAA0907, RIT1 |
| chr1 | 155874508 | 155874546 | Hypo | literature | KIAA0907, RIT1 | chr1 | 155954282 | 155954396 | Hypo | cancer_general | ARHGEF2 |
| chr1 | 156010377 | 156010548 | Hypo | lung, cancer_general | UBQLN4 | chr1 | 156017591 | 156017683 | Hypo | ovarian | LAMTOR2, UBQLN4 |
| chr1 | 156030286 | 156030621 | Hypo | cancer_general | RAB25, LAMTOR2, UBQLN4 | chr1 | 156432124 | 156432637 | Hypo | cancer_general | MEF2D |
| chr1 | 156838167 | 156838320 | Hypo | cancer_general | NTRK1 | chr1 | 157247347 | 157247388 | Hypo | cancer_general | — |
| chr1 | 157458909 | 157458961 | Hypo | cancer_general | — | chr1 | 157895413 | 157895443 | Hypo | cancer_general | AK057438 |
| chr1 | 158205040 | 158205070 | Hypo | cancer_general | — | chr1 | 158245556 | 158245586 | Hypo | cancer_general | — |
| chr1 | 158295829 | 158295935 | Hypo | cancer_general | CD1B | chr1 | 158318949 | 158318979 | Hypo | hepatobiliary | CD1E |
| chr1 | 158591699 | 158591947 | Hypo | cancer_general | SPTA1 | chr1 | 158669704 | 158669882 | Hypo | cancer_general | OR6K2 |
| chr1 | 158672628 | 158672678 | Hypo | cancer_general | OR6K2 | chr1 | 158687415 | 158687550 | Hypo | cancer_general | OR6K3 |
| chr1 | 158748648 | 158748771 | Hypo | cancer_general | OR6N2 | chr1 | 158760197 | 158760235 | Hypo | cancer_general | — |
| chr1 | 158778060 | 158778152 | Hypo | cancer_general | — | chr1 | 158815136 | 158815295 | Hypo | cancer_general | MNDA |
| chr1 | 158907635 | 158907665 | Hypo | cancer_general | PYHIN1 | chr1 | 159140357 | 159140386 | Hypo | literature | CADM3 |
| chr1 | 159187279 | 159187429 | Hypo | cancer_general | — | chr1 | 159258862 | 159258891 | Hypo | literature | FCER1A |
| chr1 | 159337419 | 159337615 | Hypo | cancer_general | BC038194 | chr1 | 159409192 | 159409221 | Hypo | literature | OR10J1, BC038194 |
| chr1 | 160451043 | 160451202 | Hypo | cancer_general | SLAMF6 | chr1 | 160693934 | 160694102 | Hypo | cancer_general | — |
| chr1 | 160880758 | 160880788 | Hypo | cancer_general | — | chr1 | 160986299 | 160986385 | Hypo | lung | F11R |
| chr1 | 160992336 | 160992587 | Hypo | cancer_general | F11R | chr1 | 161007587 | 161007746 | Hypo | cancer_general | USF1, ARHGAP30, TSTD1 |
| chr1 | 161013554 | 161013677 | Hypo | blood | USF1, TSTD1, ARHGAP30 | chr1 | 161086730 | 161086813 | Hypo | cancer_general | NIT1, DEDD, PFDN2 |
| chr1 | 161122645 | 161122778 | Hypo | cancer_general | UFC1, USP21 | chr1 | 161359069 | 161359099 | Hypo | cancer_general | — |
| chr1 | 161367577 | 161367701 | Hypo | lung, cancer_general | TRNA_Val | chr1 | 161368283 | 161368507 | Hypo | cancer_general | TRNA_Val |
| chr1 | 161442441 | 161442471 | Hypo | cancer_general | TRNA_Asp, TRNA_Glu, TRNA_Gly, TRNA_Leu | chr1 | 161466301 | 161466347 | Hypo | cancer_general | FCGR2A |
| chr1 | 161471657 | 161471779 | Hypo | lung | FCGR2A | chr1 | 162427088 | 162427153 | Hypo | lung | — |
| chr1 | 162724401 | 162724430 | Hypo | literature | DDR2 | chr1 | 162729615 | 162729686 | Hypo | literature | DDR2 |
| chr | 162748392 | 162748421 | Hypo | literature | AF268386, Metazoa_SRP, DDR2 | chr1 | 163393034 | 163393064 | Hypo | hepatobiliary | — |
| chr1 | 164428741 | 164428831 | Hypo | cancer_general | — | chr1 | 164518220 | 164518270 | Hypo | hepatobiliary | LMX1A |
| chr1 | 164730649 | 164730796 | Hypo | hepatobiliary | LOC100505795 | chr1 | 165324305 | 165324357 | Hypo | cancer_general | BLZF1, CCDC181 |
| chr1 | 167823339 | 167823461 | Hypo | cancer_general, breast | ADCY10 | chr1 | 169355697 | 169355727 | Hypo | pancreas | KIFAP3 |
| chr1 | 169838016 | 169838187 | Hypo | breast | Metazoa_SRP, SCYL3 | chr1 | 169930112 | 169930305 | Hypo | pancreas | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 170063947 | 170064218 | Hypo | cancer_general | — | chr1 | 170629999 | 170630029 | Hypo | cancer_general | PRRX1 |
| chr1 | 171625525 | 171625561 | Hypo | cancer_general | MYOC | chr1 | 171665240 | 171665330 | Hypo | cancer_general | VAMP4 |
| chr1 | 175346381 | 175346551 | Hypo | cancer_general | TNR | chr1 | 175388664 | 175388700 | Hypo | cancer_general | TNR |
| chr1 | 178063112 | 178063150 | Hypo | breast | RASAL2, RASAL2-AS1 | chr1 | 179046338 | 179046385 | Hypo | pancreas | FAM20B, TOR3A |
| chr1 | 179262226 | 179262256 | Hypo | cancer_general | SOAT1 | chr1 | 180235730 | 180235760 | Hypo | cancer_general | LHX4, LOC100527964 |
| chr1 | 180882640 | 180882669 | Hypo | tcga | KIAA1614 | chr1 | 180919682 | 180919718 | Hypo | breast | KIAA1614, AK056657 |
| chr1 | 180925271 | 180925402 | Hypo | cancer_general | AK056657, KIAA1614 | chr1 | 181014878 | 181014997 | Hypo | head_neck | MR1 |
| chr1 | 182807578 | 182807742 | Hypo | cancer_general | DHX9, NPL | chr1 | 182862133 | 182862328 | Hypo | cancer_general, colorectal | SHCBP1L, DHX9 |
| chr1 | 183129382 | 183129737 | Hypo | cancer_general | — | chr1 | 183462761 | 183463024 | Hypo | cancer_general | SMG7 |
| chr1 | 183627506 | 183627539 | Hypo | cancer_general | APOBEC4, RGL1 | chr1 | 184970783 | 184970847 | Hypo | cancer_general | — |
| chr1 | 185073818 | 185073966 | Hypo | breast | RNF2 | chr1 | 185076172 | 185076270 | Hypo | ovarian | RNF2 |
| chr1 | 185336061 | 185336095 | Hypo | cancer_general | — | chr1 | 186570930 | 186571030 | Hypo | hepatobiliary | — |
| chr1 | 195732322 | 195732539 | Hypo | cancer_general | — | chr1 | 197771547 | 197771893 | Hypo | cancer_general | — |
| chr1 | 197888831 | 197888945 | Hypo | cancer_general | LHX9 | chr1 | 198124799 | 198124932 | Hypo | cancer_general | NEK7 |
| chr1 | 200047843 | 200478932 | Hypo | cancer_general | — | chr1 | 200591054 | 200591225 | Hypo | cancer_general | KIF14 |
| chr1 | 201983113 | 201983200 | Hypo | cancer_general | ELF3, RNPEP | chr1 | 202081728 | 202081804 | Hypo | cancer_general | — |
| chr1 | 202311820 | 202311901 | Hypo | cancer_general | UBE2T, PPP1R12B | chr1 | 202531939 | 202532087 | Hypo | breast | PPP1R12B |
| chr1 | 202856858 | 202856937 | Hypo | cancer_general | RABIF, KLHL12 | chr1 | 203298307 | 203298710 | Hypo | cancer_general | — |
| chr1 | 203429564 | 203429594 | Hypo | cancer_general | — | chr1 | 203681332 | 203681362 | Hypo | blood | ATP2B4 |
| chr1 | 204333609 | 204333668 | Hypo | cancer_general | LINC00628 | chr1 | 204478284 | 204478427 | Hypo | cancer_general | MDM4, TRNA_Lys |
| chr1 | 204499813 | 204499842 | Hypo | literature | MDM4 | chr1 | 204524704 | 204524744 | Hypo | head_neck | MDM4 |
| chr1 | 204531203 | 204531757 | Hypo | breast | MDM4 | chr1 | 206950282 | 206950328 | Hypo | cancer_general | IL10 |
| chr1 | 207200870 | 207200962 | Hypo | cancer_general | PFKFB2, C1orf116 | chr1 | 207227318 | 207227556 | Hypo | cancer_general | PFKFB2, YOD1 |
| chr1 | 207794579 | 207794609 | Hypo | cancer_general | CR1 | chr1 | 207833206 | 207833370 | Hypo | cancer_general | CR1L |
| chr1 | 209164972 | 209165091 | Hypo | cancer_general | — | chr1 | 209604382 | 209604597 | Hypo | literature | MIR205, MIR205HG |
| chr1 | 209605386 | 209605415 | Hypo | literature | MIR205HG, MIR205 | chr1 | 211847706 | 211847787 | Hypo | cancer_general | NEK2 |
| chr1 | 212484610 | 212484816 | Hypo | ovarian | PPP2R5A | chr1 | 212963883 | 212964151 | Hypo | cancer_general | TATDN3, NSL1 |
| chr1 | 213189937 | 213190065 | Hypo | cancer_general | ANGEL2 | chr1 | 217307369 | 217307654 | Hypo | pancreas, cancer_general | — |
| chr1 | 217309764 | 217309816 | Hypo | cancer_general | — | chr1 | 217311463 | 217311516 | Hypo | cancer_general | EPRS |
| chr1 | 217805158 | 217805395 | Hypo | cancer_general | SPATA17, GPATCH2 | chr1 | 220132075 | 220132111 | Hypo | colorectal | — |
| chr1 | 220636466 | 220636510 | Hypo | cancer_general | C1orf140 | chr1 | 220896508 | 220896568 | Hypo | cancer_general | — |
| chr1 | 221510339 | 221510368 | Hypo | literature | CAPN2 | chr1 | 223894714 | 223894752 | Hypo | cancer_general | CAPN2 |
| chr1 | 223899470 | 223899500 | Hypo | cancer_general | — | chr1 | 224267615 | 224267662 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 224400490 | 224400524 | Hypo | cancer_general | — | chr1 | 224493975 | 224494083 | Hypo | lung | NVL |
| chr1 | 224804831 | 224804910 | Hypo | cancer_general | CNIH3 | chr1 | 224805564 | 224805620 | Hypo | cancer_general | CNIH3 |
| chr1 | 225118306 | 225118474 | Hypo | cancer_general | DNAH14 | chr1 | 225908076 | 225908184 | Hypo | cancer_general | AK124056 |
| chr1 | 226265194 | 226265257 | Hypo | cancer_general | BC032899, H3F3AP4, H3F3A | chr1 | 226384322 | 226384440 | Hypo | cancer_general | BC032899, H3F3AP4, ACBD3 |
| chr1 | 226997660 | 226997719 | Hypo | hepatobiliary | — | chr1 | 228201221 | 228201251 | Hypo | cancer_general | WNT3A |
| chr1 | 228461158 | 228461197 | Hypo | hepatobiliary | OBSCN | chr1 | 228528840 | 228529016 | Hypo | cancer_general | OBSCN |
| chr1 | 228558699 | 228559238 | Hypo | cancer_general | OBSCN | chr1 | 228693629 | 228693767 | Hypo | cancer_general | RNF187 |
| chr1 | 229476753 | 229476879 | Hypo | cancer_general | CCSAP | chr1 | 230404217 | 230404263 | Hypo | cancer_general | GALNT2 |
| chr1 | 231149928 | 231150098 | Hypo | cancer_general | FAM89A, MIR1182 | chr1 | 231475814 | 231476081 | Hypo | cancer_general | SPRTN, EXOC8 |
| chr1 | 233465473 | 233465503 | Hypo | cancer_general | KIAA1804 | chr1 | 234445373 | 234445403 | Hypo | cancer_general | MIR4671, SLC35F3 |
| chr1 | 234620866 | 234620979 | Hypo | ovarian | TARBP1 | chr1 | 234798171 | 234798201 | Hypo | cancer_general | BC032040 |
| chr1 | 234839889 | 234840058 | Hypo | ovarian | — | chr1 | 234844955 | 234845079 | Hypo | cancer_general | — |
| chr1 | 234845467 | 234845497 | Hypo | lung | — | chr1 | 235266920 | 235266950 | Hypo | cancer_general | TOMM20 |
| chr1 | 235665663 | 235665736 | Hypo | cancer_general | B3GALNT2 | chr1 | 235669296 | 235669398 | Hypo | cancer_general | B3GALNT2 |
| chr1 | 237970760 | 237970826 | Hypo | cancer_general | RYR2 | chr1 | 238024448 | 238024477 | Hypo | literature | LOC100130331 |
| chr1 | 240118848 | 240118973 | Hypo | cancer_general | — | chr1 | 240256663 | 240256780 | Hypo | pancreas | FMN2 |
| chr1 | 241052096 | 241052126 | Hypo | cancer_general | RGS7 | chr1 | 241052360 | 241052419 | Hypo | colorectal | RGS7 |
| chr1 | 241912749 | 241912778 | Hypo | literature | WDR64 | chr1 | 243859000 | 243859029 | Hypo | literature | — |
| chr1 | 243921295 | 243921330 | Hypo | cancer_general | HNRNPU | chr1 | 244115072 | 244115212 | Hypo | cancer_general | LOC339529 |
| chr1 | 245032517 | 245032603 | Hypo | lung | KIF26B | chr1 | 245135753 | 245136064 | Hypo | cancer_general | EFCAB2 |
| chr1 | 245494495 | 245494578 | Hypo | ovarian | SMYD3 | chr1 | 245849914 | 245849944 | Hypo | hepatobiliary | KIF26B |
| chr1 | 246198078 | 246198203 | Hypo | breast | SMYD3 | chr1 | 246330309 | 246330409 | Hypo | cancer_general | SMYD3 |
| chr1 | 246488175 | 246488336 | Hypo | head_neck | ZNF124, C1orf229 | chr1 | 246654652 | 246654851 | Hypo | breast | SMYD3 |
| chr1 | 247284422 | 247284452 | Hypo | cancer_general | GCSAML-AS1, OR2C3, AK130400, GCSAML | chr1 | 247608784 | 247608814 | Hypo | hepatobiliary | OR2B11, NLRP3 |
| chr1 | 247684856 | 247684929 | Hypo | cancer_general | | chr1 | 247910678 | 247910780 | Hypo | cancer_general | OR1C1 |
| chr1 | 248002278 | 248002437 | Hypo | cancer_general | OR11L1 | chr1 | 248028015 | 248028202 | Hypo | cancer_general | TRIM58 |
| chr1 | 248074729 | 248074927 | Hypo | cancer_general | OR2T8 | chr1 | 248099751 | 248099809 | Typo | cancer_general | OR2L13 |
| chr1 | 248198521 | 248198721 | Hypo | cancer_general | OR2L2 | chr1 | 248328701 | 248328841 | Hypo | cancer_general | — |
| chr1 | 248691575 | 248691616 | Hypo | cancer_general | OR2G6 | chr1 | 248860898 | 248861046 | Hypo | cancer_general | — |
| chr1 | 249121600 | 249121704 | Hypo | cancer_general | MIR3124, SH3BP5L | chr4 | 488816 | 488875 | Hypo | breast | PIGG, ZNF721 |
| chr4 | 512978 | 513008 | Hypo | head_neck | PIGG | chr4 | 513704 | 513734 | Hypo | head_neck | PIGG |
| chr4 | 628572 | 629061 | Hypo | cancer_general | PDE6B | chr4 | 651196 | 651261 | Hypo | cancer_general | BC020343, PDE6B |
| chr4 | 678471 | 678501 | Hypo | colorectal | MFSD7, MYL5 | chr4 | 718052 | 718112 | Hypo | colorectal | PCGF3 |
| chr4 | 718321 | 718456 | Hypo | colorectal | PCGF3 | chr4 | 829611 | 829641 | Hypo | cancer_general | CPLX1 |
| chr4 | 955367 | 955454 | Hypo | cancer_general | DGKQ, TMEM175 | chr4 | 955867 | 955919 | Hypo | cancer_general | DGKQ, TMEM175 |
| chr4 | 1008740 | 1008902 | Hypo | ovarian | FGFRL1 | chr4 | 1016127 | 1016252 | Hypo | cancer_general | FGFRL1 |
| chr4 | 1016586 | 1016747 | Hypo | cancer_general | FGFRL1 | chr4 | 1025928 | 1026074 | Hypo | cancer_general | FGFRL1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 1041763 | 1041926 | Hypo | cancer_general | AK124578 | chr4 | 1093536 | 1093675 | Hypo | pancreas | RNF212 |
| chr4 | 1189021 | 1189051 | Hypo | cancer_general | LOC100130872, AX747178 | chr4 | 1214894 | 1215162 | Hypo | ovarian | HV533487, HV533469, CTBP1 |
| chr4 | 1215415 | 1215451 | Hypo | ovarian | CTBP1, HV533487, HV533469 | | 1282515 | 1282545 | Hypo | ovarian | MAEA, C4orf42 |
| chr4 | 1331675 | 1331705 | Hypo | pancreas | UVSSA, MAEA | chr4 | 1336755 | 1336902 | Hypo | ovarian | UVSSA, MAEA |
| chr4 | 1338715 | 1338812 | Hypo | cancer_general | UVSSA, MAEA | chr4 | 1339099 | 1339221 | Hypo | cancer_general | UVSSA, MAEA |
| chr4 | 1512368 | 1512398 | Hypo | cancer_general | — | chr4 | 1556419 | 1556609 | Hypo | cancer_general | — |
| chr4 | 1576484 | 1576528 | Hypo | cancer_general | AX748388 | chr4 | 1616682 | 1617247 | Hypo | cancer_general | LETM1, FGFR3 |
| chr4 | 1687080 | 1687110 | Hypo | cancer_general | SLBP, FAM53A | chr4 | 1803550 | 1803582 | Hypo | literature | FGFR3, LETM1 |
| chr4 | 1806084 | 1806113 | Hypo | literature | LETM1, FGFR3 | chr4 | 1807355 | 1807384 | Hypo | literature | MIR943, NELFA |
| chr4 | 1962787 | 1962816 | Hypo | literature | WHSC1 | chr4 | 1993771 | 1994180 | Hypo | cancer_general | ZFYVE28 |
| chr4 | 2066114 | 2066265 | Hypo | cancer_general | POLN, NAT8L | chr4 | 2305672 | 2305827 | Hypo | cancer_general | |
| chr4 | 2527907 | 2527937 | Hypo | cancer_general | — | chr4 | 2532556 | 2532586 | Hypo | cancer_general | MFSD10 |
| chr4 | 2540073 | 2540297 | Hypo | cancer_general | — | chr4 | 2926366 | 2926396 | Hypo | cancer_general | GRK4 |
| chr4 | 2978968 | 2979145 | Hypo | cancer_general | GRK4 | chr4 | 3036118 | 3036148 | Hypo | esophageal | HGFAC |
| chr4 | 3217107 | 3217154 | Hypo | breast | — | chr4 | 3446991 | 3447021 | Hypo | lung | NSG1, STX18 |
| chr4 | 3447816 | 3448015 | Hypo | cancer_general | HGFAC | chr4 | 4417568 | 4417603 | Hypo | cancer_general | MAN2B2 |
| chr4 | 5519950 | 5520092 | Hypo | cancer_general | C4orf6 | chr4 | 6628453 | 6628500 | Hypo | ovarian | BLOC1S4, MRFAP1L1 |
| chr4 | 6670184 | 6670214 | Hypo | cancer_general | LOC93622 | chr4 | 6719599 | 6719637 | Hypo | cancer_general | KIAA0232 |
| chr4 | 6748346 | 6748557 | Hypo | cancer_general | AX747238, TBC1D14 | chr4 | 6839352 | 6839402 | Hypo | head_neck | — |
| chr4 | 6955114 | 6955144 | Hypo | cancer_general | — | chr4 | 6957481 | 6957620 | Hypo | cancer_general | — |
| chr4 | 7038560 | 7038688 | Hypo | breast | CCDC96, TADA2B, LOC100129931, TBC1D14 | chr4 | 7647770 | 7647945 | Hypo | cancer_general | — |
| chr4 | 7758476 | 7758561 | Hypo | pancreas | AFAP1, AFAP1-AS1 | chr4 | 8429086 | 8429178 | Hypo | cancer_general | ACOX3 |
| chr4 | 8607813 | 8607932 | Hypo | cancer_general | CPZ | chr4 | 8608556 | 8608600 | Hypo | cancer_general | CPZ |
| chr4 | 9423273 | 9423354 | Hypo | cancer_general | — | chr4 | 10782701 | 10782741 | Hypo | cancer_general | — |
| chr4 | 13524957 | 13525008 | Hypo | pancreas | LOC285547 | chr4 | 17430691 | 17430832 | Hypo | cancer_general | — |
| chr4 | 26256826 | 26256867 | Hypo | hepatobiliary | — | chr4 | 38566328 | 38566418 | Hypo | head_neck | — |
| chr4 | 38673115 | 38673144 | Hypo | literature | FLJ13197, KLF3 | chr4 | 39816807 | 39817064 | Hypo | cancer_general | PDS5A |
| chr4 | 40910303 | 40910465 | Hypo | cancer_general | TRNA_Gln, APBB2 | chr4 | 41938449 | 41938479 | Hypo | cancer_general | TMEM33 |
| chr4 | 41993676 | 41993815 | Hypo | cancer_general | SLC30A9, DCAF4L1 | chr4 | 42155293 | 42155322 | Hypo | literature | BEND4 |
| chr4 | 42348266 | 42348331 | Hypo | ovarian | — | chr4 | 44266683 | 44266780 | Hypo | cancer_general | KCTD8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 46067800 | 46067954 | Hypo | cancer_general | GABRG1 | chr4 | 46911535 | 46911564 | Hypo | literature | GABRA4 |
| chr4 | 47197142 | 47197270 | Hypo | cancer_general | GABRB1 | chr4 | 47914784 | 47914992 | Hypo | cancer_general | NFXL1, BC041434 |
| chr4 | 48848428 | 48848554 | Hypo | head_neck | OCIAD1 | chr4 | 55133613 | 55133642 | Hypo | literature | PDGFRA |
| chr4 | 55136787 | 55136816 | Hypo | literature | PDGFRA | chr4 | 55138657 | 55138686 | Hypo | literature | PDGFRA |
| chr4 | 55139691 | 55139720 | Hypo | literature | PDGFRA | chr4 | 55140731 | 55140784 | Hypo | literature | PDGFRA |
| chr4 | 55141015 | 55141050 | Hypo | literature | PDGFRA | chr4 | 55144105 | 55144134 | Hypo | literature | PDGFRA |
| chr4 | 55146554 | 55146583 | Hypo | literature | PDGFRA | chr4 | 55152075 | 55152140 | Hypo | literature | KIT, DL490879 |
| chr4 | 55589753 | 55589782 | Hypo | literature | DL490879, KIT | chr4 | 55592166 | 55592204 | Hypo | literature | KIT, DL490879 |
| chr4 | 55593417 | 55593675 | Hypo | literature | KIT, DL490879 | chr4 | 55594183 | 55594212 | Hypo | literature | KIT, DL490879 |
| chr4 | 55595504 | 55595614 | Hypo | literature | KIT, DL490879 | chr4 | 55599306 | 55599356 | Hypo | literature | KIT, DL490879 |
| chr4 | 55968165 | 55968194 | Hypo | literature | KDR | chr4 | 56594679 | 56594720 | Hypo | hepatobiliary | — |
| chr4 | 57017387 | 57017459 | Hypo | hepatobiliary | — | chr4 | 57777437 | 57777595 | Hypo | ovarian | REST |
| chr4 | 57803498 | 57803558 | Hypo | pancreas | REST | chr4 | 57813490 | 57813763 | Hypo | ovarian | REST |
| chr4 | 73459699 | 73459762 | Hypo | cancer_general | EREG | chr4 | 74142341 | 74142434 | Hypo | ovarian | — |
| chr4 | 75241080 | 75241435 | Hypo | cancer_general | — | chr4 | 76554873 | 76554935 | Hypo | lung | CDKL2 |
| chr4 | 76912698 | 76912733 | Hypo | cancer_general | CXCL9, SDAD1 | chr4 | 79611132 | 79611294 | Hypo | cancer_general | LOC100505702 |
| chr4 | 79689651 | 79689732 | Hypo | colorectal | BMP2K | chr4 | 79861530 | 79861560 | Hypo | cancer_general | PAQR3 |
| chr4 | 80273120 | 80273150 | Hypo | hepatobiliary | — | chr4 | 81188328 | 81188489 | Hypo | cancer_general | FGF5 |
| chr4 | 83323506 | 83323708 | Hypo | lung | — | chr4 | 83343366 | 83343396 | Hypo | cancer_general | HNRPDL, ENOPH1 |
| chr4 | 83809740 | 83809787 | Hypo | cancer_general | THAP9-AS1, AK128593, SEC31A | chr4 | 83955171 | 83955201 | Hypo | cancer_general | COPS4 |
| chr4 | 83988361 | 83988511 | Hypo | cancer_general | COPS4 | chr4 | 90043517 | 90043547 | Hypo | cancer_general | TIGD2 |
| chr4 | 91079842 | 91079899 | Hypo | cancer_general | CCSER1 | chr4 | 95127590 | 95127717 | Hypo | cancer_general | SMARCAD1 |
| chr4 | 95128038 | 95128068 | Hypo | cancer_general | SMARCAD1 | chr4 | 95762672 | 95762896 | Hypo | cancer_general | BMPR1B |
| chr4 | 102332467 | 102332611 | Hypo | cancer_general | BANK1 | chr4 | 103929647 | 103929796 | Hypo | cancer_general | SLC9B1 |
| chr4 | 103930065 | 103930095 | Hypo | cancer_general | SLC9B1 | chr4 | 106335495 | 106335617 | Hypo | cancer_general | PPA2 |
| chr4 | 110344202 | 110344294 | Hypo | cancer_general | SEC24B-AS1, AK058136 | chr4 | 110735672 | 110735702 | Hypo | breast | GAR1 |
| chr4 | 113154896 | 113155129 | Hypo | cancer_general | AP1AR | chr4 | 113431900 | 113431930 | Hypo | cancer_general | NEUROG2 |
| chr4 | 113559163 | 113559422 | Hypo | cancer_general | MIR302B, LARP7, C4orf21 | chr4 | 123664228 | 123664363 | Hypo | pancreas | BBS12 |
| chr4 | 128967250 | 128967329 | Hypo | colorectal | — | chr4 | 128968647 | 128968800 | Hypo | head_neck | — |
| chr4 | 128969310 | 128969382 | Hypo | head_neck | — | chr4 | 128984386 | 128984464 | Hypo | cancer_general | LARP1B |
| chr4 | 130018134 | 130018266 | Hypo | cancer_general | SCLT1, C4orf33 | chr4 | 134073862 | 134073919 | Hypo | cancer_general | PCDH10, BC040219 |
| chr4 | 144586035 | 144586088 | Hypo | cancer_general | FREM3 | chr4 | 146853951 | 146853981 | Hypo | head_neck | ZNF827 |
| chr4 | 151974287 | 151974510 | Hypo | pancreas | — | chr4 | 152148807 | 152148836 | Hypo | literature | SH3D19 |
| chr4 | 153247273 | 153247386 | Hypo | literature | FBXW7 | chr4 | 153249362 | 153249398 | Hypo | literature | FBXW7 |
| chr4 | 153251894 | 153251923 | Hypo | literature | FBXW7 | chr4 | 153702668 | 153702702 | Hypo | cancer_general | ARFIP1 |
| chr4 | 154216241 | 154216357 | Hypo | cancer_general | — | chr4 | 154374504 | 154374630 | Hypo | head_neck | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 155665445 | 155665475 | Hypo | esophageal | LRAT, DQ266889 | chr4 | 158101782 | 158102020 | Hypo | cancer_general | GLRB |
| chr4 | 159063301 | 159063331 | Hypo | hepatobiliary | FAM198B | chr4 | 159149784 | 159149824 | Hypo | head_neck | TMEM144 |
| chr4 | 164819191 | 164819221 | Hypo | hepatobiliary | — | chr4 | 170865234 | 170865287 | Hypo | cancer_general | LOC100506085 |
| chr4 | 171012375 | 171012409 | Hypo | cancer_general | AADAT | chr4 | 172132870 | 172133019 | Hypo | cancer_general | — |
| chr4 | 173953411 | 173953594 | Hypo | hepatobiliary | — | chr4 | 174083164 | 174083431 | Hypo | hepatobiliary | GALNT7, BC040577 |
| chr4 | 174124429 | 174124477 | Hypo | hepatobiliary | GALNT7 | chr4 | 174136704 | 174136734 | Hypo | hepatobiliary | GALNT7 |
| chr4 | 174224186 | 174224216 | Hypo | hepatobiliary | GALNT7 | chr4 | 178285756 | 178285879 | Hypo | head_neck | — |
| chr4 | 183064874 | 183064966 | Hypo | pancreas | TENM3, MGC45800 | chr4 | 184375546 | 184375726 | Hypo | cancer_general | CDKN2AIP |
| chr4 | 184491996 | 184492042 | Hypo | cancer_general | — | chr4 | 184921855 | 184922091 | Hypo | pancreas, cancer_general | STOX2 |
| chr19 | 403538 | 403809 | Hypo | cancer_general | C2CD4C | chr19 | 407189 | 407320 | Hypo | cancer_general | SHC2, C2CD4C |
| chr19 | 418225 | 418255 | Hypo | ovarian | SHC2, C2CD4C | chr19 | 468757 | 468787 | Hypo | cancer_general | ODF3L2, SHC2 |
| chr19 | 485165 | 485394 | Hypo | cancer_general | — | chr19 | 549361 | 549451 | Hypo | cancer_general | GZMM, CDC34 |
| chr19 | 555608 | 555768 | Hypo | cancer_general | GZMM | chr19 | 570156 | 570194 | Hypo | esophageal | BSG |
| chr19 | 592589 | 592632 | Hypo | cancer_general | HCN2, BSG | chr19 | 593290 | 593462 | Hypo | cancer_general | HCN2, BSG |
| chr19 | 599214 | 599333 | Hypo | cancer_general | HCN2 | chr19 | 607070 | 607110 | Hypo | head_neck | HCN2 |
| chr19 | 690888 | 690940 | Hypo | cancer_general | PRSS57, FSTL3 | chr19 | 752136 | 752462 | Hypo | cancer_general | MISP, PALM |
| chr19 | 869337 | 869394 | Hypo | pancreas | CFD, MED16 | chr19 | 883624 | 883791 | Hypo | cancer_general | MED16 |
| chr19 | 884018 | 884162 | Hypo | cancer_general | U6, MED16 | chr19 | 891516 | 891723 | Hypo | cancer_general | U6, R3HDM4, MED16 |
| chr19 | 955757 | 956237 | Hypo | cancer_general | ARID3A FLJ00277, TMEM259, GRIN3B, WDR18 | chr19 | 959128 | 959187 | Hypo | pancreas | ARID3A FLJ00277, TMEM259, GRIN3B, WDR18 |
| chr19 | 1003305 | 1003384 | Hypo | cancer_general | — | chr19 | 1003669 | 1003734 | Hypo | cancer_general | — |
| chr19 | 1004915 | 1005441 | Hypo | cancer_general | FLJ00277, TMEM259, GRIN3B | chr19 | 1030176 | 1030225 | Hypo | cancer_general | ABCA7, CNN2 |
| chr19 | 1047890 | 1047939 | Hypo | cancer_general | ABCA7 | chr19 | 1048348 | 1048465 | Hypo | ovarian | ABCA7 |
| chr19 | 1083314 | 1083437 | Hypo | cancer_general | POLR2E, HMHA1 | chr19 | 1156524 | 1156654 | Hypo | cancer_general | — |
| chr19 | 1170185 | 1170230 | Hypo | cancer_general | — | chr19 | 1171099 | 1171324 | Hypo | cancer_general | — |
| chr19 | 1220422 | 1220610 | Hypo | literature | C19orf26, STK11 | chr19 | 1221981 | 1222010 | Hypo | literature | STK11, C19orf26 |
| chr19 | 1236474 | 1236678 | Hypo | cancer_general | ATP5D, C19orf26, STK11 | chr19 | 1274778 | 1274826 | Hypo | cancer_general | CIRBP-AS1, C19orf24, DL492057, CIRBP |

TABLE 11-continued

| chr | Start | Stop | Hypo/hyper | classification | annotation |
|---|---|---|---|---|---|
| chr19 | 1325788 | 1325889 | Hypo | cancer_general | — |
| chr19 | 1496413 | 1496450 | Hypo | cancer_general | PCSK4, ADAMTSL5, REEP6 |
| chr19 | 1525605 | 1525960 | Hypo | cancer_general | PLK5 |
| chr19 | 1547233 | 1547263 | Hypo | cancer_general | MEX3D |
| chr19 | 1799466 | 1799516 | Hypo | cancer_general | ATP8B3 |
| chr19 | 1807970 | 1808413 | Hypo | cancer_general | MIR1909, ATP8B3, REXO1 |
| chr19 | 2274677 | 2274713 | Hypo | cancer_general | C19orf35, SPPL2B, OAZ1 |
| chr19 | 2331413 | 2331443 | Hypo | cancer_general | SPPL2B, LSM7 |
| chr19 | 2414257 | 2414337 | Hypo | cancer_general | TMPRSS9 |
| chr19 | 2642877 | 2642947 | Hypo | cancer_general | BC022568, GNG7 |
| chr19 | 3041417 | 3041447 | Hypo | cancer_general | — |
| chr19 | 3114998 | 3115027 | Hypo | literature | DKFZp434J194, GNA11 |
| chr19 | 3219512 | 3219565 | Hypo | cancer_general | CELF5, NCLN |
| chr19 | 3562128 | 3562797 | Hypo | cancer_general | MFSD12 |
| chr19 | 3578138 | 3578223 | Hypo | colorectal | GIPC3, HMG20B |
| chr19 | 3718052 | 3718082 | Hypo | cancer_general | TJP3 |
| chr19 | 3779277 | 3779435 | Hypo | cancer_general | JA611290, MATK, RAX2 |
| chr19 | 3834572 | 3834641 | Hypo | hepatobiliary | ZFR2 |
| chr19 | 3966086 | 3966755 | Hypo | cancer_general | EEF2, MIR637, DAPK3 |
| chr19 | 4054435 | 4054471 | Hypo | pancreas | ZBTB7A |
| chr19 | 4101087 | 4101116 | Hypo | literature | MAP2K2 |
| chr19 | 4117526 | 4117630 | Hypo | literature | MAP2K2 |
| chr19 | 4195767 | 4195853 | Hypo | cancer_general | ANKRD24 |
| chr19 | 4509338 | 4509440 | Hypo | cancer_general | PLIN4, HDGFRP2 |
| chr19 | 4549454 | 4549565 | Hypo | cancer_general | SEMA6B, LRG1, PLIN5 |
| chr19 | 1330064 | 1330214 | Hypo | cancer_general | — |
| chr19 | 1496654 | 1496694 | Hypo | cancer_general | ADAMTSL5, REEP6, PCSK4 |
| chr19 | 1527227 | 1527394 | Hypo | cancer_general | PLK5 |
| chr19 | 1689436 | 1689595 | Hypo | cancer_general | — |
| chr19 | 1800032 | 1800300 | Hypo | cancer_general | ATP8B3 |
| chr19 | 2155031 | 2155061 | Hypo | cancer_general | DOT1L |
| chr19 | 2330317 | 2330407 | Hypo | cancer_general | SPPL2B, LSM7 |
| chr19 | 2413125 | 2413155 | Hypo | cancer_general | TMPRSS9 |
| chr19 | 2513250 | 2513285 | Hypo | cancer_general | GNG7 |
| chr19 | 2683911 | 2684080 | Hypo | cancer_general | — |
| chr19 | 3093571 | 3093818 | Hypo | cancer_general | GNA11 |
| chr19 | 3118927 | 3118956 | Hypo | literature | DKFZp434J194, GNA11 |
| chr19 | 3296613 | 3296670 | Hypo | cancer_general | CELF5 |
| chr19 | 3570230 | 3570371 | Hypo | cancer_general | HMG20B |
| chr19 | 3716179 | 3716241 | Hypo | cancer_general | TJP3 |
| chr19 | 3778130 | 3778394 | Hypo | cancer_general | JA611290, MATK, RAX2 |
| chr19 | 3821044 | 3821217 | Hypo | cancer_general | ZFR2 |
| chr19 | 3855407 | 3855595 | Hypo | cancer_general | ZFR2 |
| chr19 | 3994540 | 3994595 | Hypo | colorectal | — |
| chr19 | 4095471 | 4095514 | Hypo | cancer_general | MAP2K2 |
| chr19 | 4110565 | 4110597 | Hypo | literature | MAP2K2 |
| chr19 | 4160800 | 4160898 | Hypo | cancer_general | CREB3L3 |
| chr19 | 4311273 | 4311430 | Hypo | cancer_general | TMIGD2, FSD1 |
| chr19 | 4548134 | 4548364 | Hypo | cancer_general | SEMA6B, LRG1, PLIN5 |
| chr19 | 4550246 | 4550330 | Hypo | cancer_general | SEMA6B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 4555896 | 4556112 | Hypo | cancer_general | SEMA6B | chr19 | 4557098 | 4557235 | Hypo | cancer_general | SEMA6B |
| chr19 | 4572332 | 4572459 | Hypo | cancer_general | — | chr19 | 4670765 | 4670949 | Hypo | cancer_general | DPP9, LOC100131094, C19orf10 |
| chr19 | 4789697 | 4789805 | Hypo | cancer_general | FEM1A, AK126532 | chr19 | 4790142 | 4790264 | Hypo | cancer_general | FEM1A, AK126532 |
| chr19 | 4835778 | 4835926 | Hypo | colorectal | PLIN3 | chr19 | 4910361 | 4910410 | Hypo | breast | ARRDC5, UHRF1, C19orf31 |
| chr19 | 5608519 | 5608569 | Hypo | cancer_general | SAFB2 | chr19 | 5676212 | 5676242 | Hypo | cancer_general | C19orf70, HSD11B1L |
| chr19 | 5759374 | 5759544 | Hypo | cancer_general | CATSPERD | chr19 | 5759744 | 5759774 | Hypo | cancer_general | CATSPERD |
| chr19 | 5767703 | 5767733 | Hypo | cancer_general | CATSPERD | chr19 | 5826179 | 5826209 | Hypo | cancer_general | FUT6, NRTN |
| chr19 | 5905517 | 5905547 | Hypo | cancer_general | CAPS, VMAC, NDUFA11 | chr19 | 5910356 | 5910492 | Hypo | cancer_general | CAPS, RANBP3, VMAC, NDUFA11 |
| chr19 | 5914761 | 5914791 | Hypo | cancer_general | RANBP3, CAPS, VMAC | chr19 | 5914992 | 5915060 | Hypo | cancer_general | RANBP3, CAPS, VMAC |
| chr19 | 6303268 | 6303298 | Hypo | cancer_general | ACER1 | chr19 | 6512913 | 6512943 | Hypo | cancer_general | — |
| chr19 | 6658279 | 6658422 | Hypo | cancer_general | TNFSF14 | chr19 | 6889423 | 6889574 | Hypo | cancer_general | EMR1 |
| chr19 | 7157547 | 7157628 | Hypo | lung | INSR | chr19 | 7554718 | 7554780 | Hypo | cancer_general | C19orf45, PEX11G |
| chr19 | 7635387 | 7635552 | Hypo | cancer_general | PNPLA6 | chr19 | 7747205 | 7747234 | Hypo | tcga | FCER2, TRAPPC5, C19orf59 |
| chr19 | 7870346 | 7870387 | Hypo | cancer_general | — | chr19 | 8391621 | 8391651 | Hypo | cancer_general | KANK3, RPS28, NDUFA7 |
| chr19 | 8554173 | 8554218 | Hypo | head_neck | PRAM1, DKFZp547H118, HNRNPM | chr19 | 8576914 | 8577000 | Hypo | lung | ZNF414, PRAM1, MYO1F |
| chr19 | 8579592 | 8579705 | Hypo | ovarian | MYO1F, ZNF414 | chr19 | 9239580 | 9239695 | Hypo | cancer_general | OR7G3 |
| chr19 | 9331918 | 9331955 | Hypo | hepatobiliary | OR7D4 | chr19 | 9937291 | 9937386 | Hypo | cancer_general | UBL5, PIN1, FBXL12 |
| chr19 | 10231077 | 10231242 | Hypo | cancer_general | P2RY11, EIF3G | chr19 | 10246506 | 10246566 | Hypo | lung | DNMT1 |
| chr19 | 10362045 | 10362182 | Hypo | cancer_general | MRPL4 | chr19 | 10600431 | 10600460 | Hypo | literature | KEAP1 |
| chr19 | 10602274 | 10602348 | Hypo | literature | KEAP1 | chr19 | 10602565 | 10602864 | Hypo | literature | KEAP1 |
| chr19 | 10610138 | 10610260 | Hypo | literature | KEAP1 | chr19 | 10621768 | 10621829 | Hypo | cancer_general | S1PR5, KEAP1 |
| chr19 | 10648372 | 10648546 | Hypo | cancer_general | ATG4D, DNM2, MIR638, QTRT1 | chr19 | 10729811 | 10729899 | Hypo | cancer_general | SLC44A2, DNM2, MIR638, QTRT1 |
| chr19 | 10823678 | 10823721 | Hypo | colorectal | — | chr19 | 10827675 | 10827705 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 10851287 | 10851362 | Hypo | colorectal | — | chr19 | 10955456 | 10955585 | Hypo | cancer_general | C19orf38, TMED1 |
| chr19 | 11063941 | 11063971 | Hypo | cancer_general | SMARCA4 | chr19 | 11134252 | 11134281 | Hypo | literature | SMARCA4 |
| chr19 | 11138507 | 11138536 | Hypo | literature | SMARCA4 | chr19 | 12147437 | 12147545 | Hypo | cancer_general | ZNF878, ZNF433, AX747405 |
| chr19 | 12205385 | 12205434 | Hypo | hepatobiliary | ZNF788 | chr19 | 12303495 | 12303551 | Hypo | breast | AX721123, AK023304, ZNF136 |
| chr19 | 12661175 | 12661221 | Hypo | cancer_general | ZNF564, ZNF709 | chr19 | 12846906 | 12847098 | Hypo | cancer_general | ASNA1, C19orf43 |
| chr19 | 12860307 | 12860433 | Hypo | cancer_general | BEST2, ASNA1 | chr19 | 12863412 | 12863520 | Hypo | cancer_general | ASNA1, BEST2 |
| chr19 | 13491305 | 13491340 | Hypo | esophageal | CACNA1A | chr19 | 13782965 | 13783028 | Hypo | hepatobiliary | — |
| chr19 | 13903520 | 13903603 | Hypo | cancer_general | ZSWIM4 | chr19 | 13965838 | 13965965 | Hypo | cancer_general | — |
| chr19 | 13988775 | 13988805 | Hypo | cancer_general | C19orf57, NANOS3, MIR181D, MIR181C | chr19 | 14085021 | 14085051 | Hypo | cancer_general | RFX1 |
| chr19 | 14181305 | 14181846 | Hypo | breast | LOC113230 | chr19 | 14324876 | 14324906 | Hypo | cancer_general | — |
| chr19 | 14327101 | 14327158 | Hypo | cancer_general | — | chr19 | 14334020 | 14334060 | Hypo | colorectal | — |
| chr19 | 14411056 | 14411086 | Hypo | cancer_general | — | chr19 | 14663925 | 14664183 | Hypo | breast | TECR |
| chr19 | 14664479 | 14664561 | Hypo | breast | TECR | chr19 | 14869496 | 14869526 | Hypo | cancer_general | EMR2 |
| chr19 | 15292384 | 15292499 | Hypo | cancer_general, literature | NOTCH3 | chr19 | 15519444 | 15519474 | Hypo | ovarian | AKAP8L |
| chr19 | 16766902 | 16766932 | Hypo | head_neck | TMEM38A, SMIM7 | chr19 | 17000570 | 17000599 | Hypo | literature | CPAMD8, F2RL3, SIN3B |
| chr19 | 17152333 | 17152363 | Hypo | cancer_general | HAUS8 | chr19 | 17335642 | 17335718 | Hypo | cancer_general | OCEL1, NR2F6, USE1 |
| chr19 | 17336042 | 17336111 | Hypo | cancer_general | OCEL1, NR2F6, USE1 | chr19 | 17359350 | 17359459 | Hypo | cancer_general | USHBP1, NR2F6 |
| chr19 | 17436061 | 17436203 | Hypo | head_neck | GTPBP3, ANO8, DDA1 | chr19 | 17446897 | 17447045 | Hypo | cancer_general | AK310794, GTPBP3, ANO8 |
| chr19 | 17759224 | 17759423 | Hypo | literature | UNC13A | chr19 | 17943423 | 17943452 | Hypo | literature | JAK3 |
| chr19 | 17945891 | 17945983 | Hypo | literature | JAK3 | chr19 | 17947991 | 17948023 | Hypo | literature | JAK3 |
| chr19 | 17949094 | 17949123 | Hypo | literature | JAK3 | chr19 | 18041069 | 18041203 | Hypo | cancer_general | CCDC124 |
| chr19 | 18057603 | 18057655 | Hypo | cancer_general | KCNN1, CCDC124 | chr19 | 18103711 | 18103741 | Hypo | cancer_general | ARRDC2, KCNN1 |
| chr19 | 18104472 | 18104606 | Hypo | cancer_general | ARRDC2, KCNN1 | chr19 | 18126412 | 18126442 | Hypo | ovarian | ARRDC2 |
| chr19 | 18271894 | 18271923 | Hypo | literature | PIK3R2, MAST3 | chr19 | 18278047 | 18278076 | Hypo | literature | IFI30, PIK3R2 |
| chr19 | 18300127 | 18300422 | Hypo | cancer_general | MPV17L2, RAB3A | chr19 | 18301007 | 18301037 | Hypo | cancer_general | RAB3A, MPV17L2 |
| chr19 | 18331031 | 18331136 | Hypo | cancer_general | PDE4C | chr19 | 18383211 | 18383351 | Hypo | cancer_general | JUND, MIR3188 |

TABLE 11-continued

| chr | Start | Stop | Hypo/hyper | classification | annotation |
|---|---|---|---|---|---|
| chr19 | 18488862 | 18488915 | Hypo | cancer_general | GDF15, MIR3189, PGPEP1 |
| chr19 | 18523115 | 18523145 | Hypo | cancer_general | SSBP4 |
| chr19 | 18681638 | 18681926 | Hypo | cancer_general | UBA52, DL491652, KXD1 |
| chr19 | 18872825 | 18872900 | Hypo | cancer_general | CRTC1 |
| chr19 | 18994887 | 18995206 | Hypo | cancer_general | GDF1, CERS1 |
| chr19 | 19261519 | 19261548 | Hypo | literature | MEF2B, MEF2BNB-MEF2B |
| chr19 | 19489251 | 19489297 | Hypo | cancer_general | GATAD2A |
| chr19 | 19645834 | 19645925 | Hypo | cancer_general | CILP2, YJEFN3, NDUFA13 |
| chr19 | 21237609 | 21237655 | Hypo | hepatobiliary | ZNF430 |
| chr19 | 21245066 | 21245152 | Hypo | hepatobiliary | ZNF430 |
| chr19 | 21289719 | 21289749 | Hypo | hepatobiliary | ZNF714 |
| chr19 | 21303863 | 21303993 | Hypo | hepatobiliary | AX746719, ZNF714 |
| chr19 | 21370382 | 21370479 | Hypo | hepatobiliary | ZNF431 |
| chr19 | 21665258 | 21665288 | Hypo | cancer_general | LINC00664 |
| chr19 | 30130889 | 30130919 | Hypo | cancer_general | — |
| chr19 | 30215753 | 30215782 | Hypo | tcga | C19orf12 |
| chr19 | 30555329 | 30555376 | Hypo | cancer_general | — |
| chr19 | 30582601 | 30582649 | Hypo | cancer_general | — |
| chr19 | 30703436 | 30703469 | Hypo | cancer_general | — |
| chr19 | 32364365 | 32364403 | Hypo | cancer_general | AK097493 |
| chr19 | 32516399 | 32516516 | Hypo | cancer_general | LOC400684, DPY19L3 |
| chr19 | 32898335 | 32898490 | Hypo | cancer_general | — |
| chr19 | 33571236 | 33571280 | Hypo | lung, cancer_general | GPATCH1 |
| chr19 | 35616341 | 35616397 | Hypo | cancer_general | LGI4, FXYD3 |
| chr19 | 35783136 | 35783231 | Hypo | cancer_general | MAG, HAMP |
| chr19 | 36194934 | 36194996 | Hypo | ovarian | ZBTB32 |
| chr19 | 36222432 | 36222534 | Hypo | cancer_general | IGFLR1, KMT2B |
| chr19 | 18496000 | 18496030 | Hypo | head_neck | GDF15, MIR3189, LRRC25 |
| chr19 | 18633926 | 18633980 | Hypo | cancer_general | FKBP8, ELL |
| chr19 | 18856379 | 18856409 | Hypo | ovarian | CRTC1 |
| chr19 | 18989821 | 18990281 | Hypo | cancer_general | CERS1, GDF1 |
| chr19 | 19260030 | 19260101 | Hypo | literature | MEF2B, MEF2BNB-MEF2B |
| chr19 | 19334831 | 19344915 | Hypo | cancer_general | NCAN |
| chr19 | 19636877 | 19636907 | Hypo | ovarian | NDUFA13, YJEFN3 |
| chr19 | 19775308 | 19775472 | Hypo | cancer_general | ZNF101, ATP13A1 |
| chr19 | 21239053 | 21239129 | Hypo | hepatobiliary | ZNF430 |
| chr19 | 21265890 | 21265920 | Hypo | cancer_general | ZNF714 |
| chr19 | 21290153 | 21290216 | Hypo | hepatobiliary | ZNF714 |
| chr19 | 21305707 | 21305737 | Hypo | hepatobiliary | AX746719, ZNF714 |
| chr19 | 21512594 | 21512660 | Hypo | cancer_general | ZNF708 |
| chr19 | 29505153 | 29505183 | Hypo | cancer_general | LOC100505835 |
| chr19 | 30186141 | 30186278 | Hypo | lung | C19orf12 |
| chr19 | 30252296 | 30252369 | Hypo | cancer_general | — |
| chr19 | 30362775 | 30363017 | Hypo | cancer_general | — |
| chr19 | 30637494 | 30637531 | Hypo | cancer_general | TSHZ3 |
| chr19 | 31804724 | 31804754 | Hypo | cancer_general | — |
| chr19 | 32380872 | 32380961 | Hypo | cancer_general | ZNF507 |
| chr19 | 32835279 | 32835309 | Hypo | cancer_general | RHPN2, C19orf40, CEP89 |
| chr19 | 33468018 | 33468055 | Hypo | breast | — |
| chr19 | 34896324 | 34896360 | Hypo | cancer_general | GPI, PDCD2L |
| chr19 | 35781374 | 35781459 | Hypo | cancer_general | MAG, HAMP |
| chr19 | 35797916 | 35797965 | Hypo | cancer_general | MAG |
| chr19 | 36200805 | 36200847 | Hypo | cancer_general | ZBTB32, KMT2B |
| chr19 | 36250029 | 36250134 | Hypo | cancer_general | HSPB6, LIN37, AL137752, C19orf55 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 36264697 | 36264773 | Hypo | cancer_general | ARHGAP33, C19orf55 | chr19 | 36265053 | 36265186 | Hypo | cancer_general | C19orf55, ARHGAP33 |
| chr19 | 36410956 | 36411042 | Hypo | esophageal | — | chr19 | 36413776 | 36413830 | Hypo | cancer_general | — |
| chr19 | 36531924 | 36531954 | Hypo | ovarian | BC071809, THAP8, CLIP3 | chr19 | 36707435 | 36707467 | Hypo | cancer_general | ZNF146, ZNF565 |
| chr19 | 37702003 | 37702169 | Hypo | cancer_general | ZNF383, ZNF585B | chr19 | 38441488 | 38441518 | Hypo | breast | SIPA1L3 |
| chr19 | 38481044 | 38481217 | Hypo | cancer_general | SIPA1L3 | chr19 | 38733924 | 38733954 | Hypo | cancer_general | PPP1R14A, SPINT2 |
| chr19 | 38736072 | 38736127 | Hypo | cancer_general | PPP1R14A | chr19 | 38747729 | 38747767 | Hypo | cancer_general | PPP1R14A, SPINT2 |
| chr19 | 38757128 | 38757308 | Hypo | cancer_general | PPP1R14A, SPINT2 | chr19 | 38782559 | 38782589 | Hypo | breast | SPINT2 |
| chr19 | 38789218 | 38789288 | Hypo | cancer_general | YIF1B, C19orf33, SPINT2 | chr19 | 38873935 | 38873965 | Hypo | cancer_general | GGN, SPRED3, PSMD8 |
| chr19 | 38905548 | 38905702 | Hypo | cancer_general | RASGRP4, FAM98C | chr19 | 38974232 | 38974262 | Hypo | cancer_general | RYR1 |
| chr19 | 39135294 | 39135454 | Hypo | cancer_general | ACTN4, EIF3K | chr19 | 39273027 | 39273062 | Hypo | ovarian | LGALS7B, LGALS7 |
| chr19 | 39290904 | 39290944 | Hypo | cancer_general | LGALS4, LGALS7B | chr19 | 39306433 | 39306545 | Hypo | colorectal | ECH1, HNRNPL, LGALS4 |
| chr19 | 39310469 | 39310584 | Hypo | colorectal | ECH1, LGALS4, HNRNPL | chr19 | 39650791 | 39650967 | Hypo | breast | PAK4 |
| chr19 | 39816936 | 39817085 | Hypo | cancer_general | BC110060, GMFG | chr19 | 39934694 | 39934784 | Hypo | cancer_general | SUPT5H, RPS16 |
| chr19 | 40210391 | 40210573 | Hypo | cancer_general | — | chr19 | 40762943 | 40762972 | Hypo | literature | AKT2 |
| chr19 | 40829079 | 40829211 | Hypo | breast | C19orf47 | chr19 | 40829793 | 40830032 | Hypo | cancer_general, breast | C19orf47 |
| chr19 | 40902425 | 40902812 | Hypo | cancer_general | PRX, HIPK4 | chr19 | 40951175 | 40951357 | Hypo | cancer_general | BLVRB, SERTAD3 |
| chr19 | 40951679 | 40951762 | Hypo | cancer_general | BLVRB, SERTAD3 | chr19 | 40991013 | 40991139 | Hypo | cancer_general | SPTBN4 |
| chr19 | 41473190 | 41473242 | Hypo | cancer_general | — | chr19 | 41694610 | 41694640 | Hypo | cancer_general | CYP2S1 |
| chr19 | 41846193 | 41846325 | Hypo | ovarian | TGFB1 | chr19 | 41881534 | 41881811 | Hypo | cancer_general | TMEM91, BCKDHA |
| chr19 | 41919917 | 41919971 | Hypo | pancreas | BCKDHA, ATP1A3, RABAC1 | chr19 | 42408300 | 42408330 | Hypo | cancer_general | ARHGEF1 |
| chr19 | 42460961 | 42461113 | Hypo | colorectal | — | chr19 | 42856453 | 42856483 | Hypo | lung | MEGF8 |
| chr19 | 42911568 | 42911598 | Hypo | esophageal | LIPE, LIPE-AS1 | chr19 | 44599783 | 44599883 | Hypo | cancer_general | LOC100379224, ZNF224, ZNF284 |
| chr19 | 45003211 | 45003323 | Hypo | cancer_general | CEACAM20, ZNF180 | chr19 | 45541556 | 45541679 | Hypo | cancer_general | CLASRP, RELB |
| chr19 | 45570401 | 45570450 | Hypo | breast | ZNF296, CLASRP | chr19 | 45574465 | 45574495 | Hypo | cancer_general | GEMIN7, CLASRP, ZNF296 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 45574773 | 45574888 | Hypo | breast | GEMIN7, ZNF296, CLASRP | chr19 | 45601380 | 45601410 | Hypo | cancer_general | PPP1R37, GEMIN7 |
| chr19 | 45678395 | 45678555 | Hypo | ovarian | BLOC1S3, TRAPPC6A | chr19 | 45810102 | 45810267 | Hypo | cancer_general | CKM |
| chr19 | 45835028 | 45835268 | Hypo | cancer_general | KLC3, CKM | chr19 | 45997528 | 45997584 | Hypo | cancer_general | PPM1N, RTN2 |
| chr19 | 46234803 | 46234887 | Hypo | cancer_general | LOC388553 | chr19 | 46404522 | 46404601 | Hypo | cancer_general | MYPOP |
| chr19 | 47200361 | 47200536 | Hypo | cancer_general | PRKD2 | chr19 | 47329748 | 47329867 | Hypo | cancer_general | SNAR-E |
| chr19 | 47358646 | 47358751 | Hypo | cancer_general | AP2S1 | chr19 | 47515017 | 47515047 | Hypo | cancer_general | NPAS1, ARHGAP35 |
| chr19 | 47618255 | 47618434 | Hypo | cancer_general | ZC3H4 | chr19 | 47976399 | 47976429 | Hypo | cancer_general | KPTN, SLC8A2 |
| chr19 | 48003607 | 48003714 | Hypo | cancer_general | NAPA, NAPA-AS1 | chr19 | 48082100 | 48082130 | Hypo | cancer_general | — |
| chr19 | 48108151 | 48108320 | Hypo | cancer_general | GLTSCR1 | chr19 | 48137171 | 48137307 | Hypo | cancer_general | GLTSCR1 |
| chr19 | 48151265 | 48151337 | Hypo | cancer_general | GLTSCR1 | chr19 | 48249451 | 48249602 | Hypo | cancer_general | GLTSCR2, SNORD23, EHD2 |
| chr19 | 48614843 | 48614873 | Hypo | cancer_general | LIG1, PLA2G4C | chr19 | 48771551 | 48771600 | Hypo | cancer_general | ZNF114 |
| chr19 | 48777059 | 48777121 | Hypo | cancer_general | ZNF114 | chr19 | 48800603 | 48800769 | Hypo | cancer_general | CCDC114, ZNF114 |
| chr19 | 48857725 | 48857831 | Hypo | cancer_general | Mir_324, SYNGR4, TMEM143 | chr19 | 48902848 | 48902878 | Hypo | cancer_general | GRIN2D, KDELR1 |
| chr19 | 49043242 | 49043272 | Hypo | cancer_general | — | chr19 | 49119229 | 49119259 | Hypo | cancer_general | SPACA4, FAM83E, RPL18, SPHK2 |
| chr19 | 49180462 | 49180558 | Hypo | cancer_general | NTN5 | chr19 | 49284546 | 49285593 | Hypo | cancer_general | — |
| chr19 | 49290711 | 49290844 | Hypo | cancer_general | BCAT2, Mir_324 | chr19 | 49375050 | 49375216 | Hypo | cancer_general | PPP1R15A, TULP2, PLEKHA4 |
| chr19 | 49402471 | 49402551 | Hypo | cancer_general | TULP2, NUCB1, Mir_324 | chr19 | 49498076 | 49498148 | Hypo | cancer_general | RUVBL2 |
| chr19 | 49590284 | 49590399 | Hypo | cancer_general | SNRNP70 | chr19 | 49628132 | 49628252 | Hypo | cancer_general | PPFIA3, C19orf73, Mir_324, LIN7B |
| chr19 | 49784869 | 49784935 | Hypo | cancer_general | SLC6A16 RPS11, SNORD34, SNORD32A, FLT3LG, SNORD35B, MIR150, SNORD35A, SNORD33, RPL13A | chr19 | 49890887 | 49890929 | Hypo | cancer_general | CCDC155 FLT3LG, SNORD35B, MIR150, SNORD34, RPL13A, RPS11, SNORD35A, SNORD33, SNORD32A |
| chr19 | 49997263 | 49997324 | Hypo | cancer_general |  | chr19 | 49998434 | 49998607 | Hypo | cancer_general |  |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 50028397 | 50028530 | Hypo | cancer_general | RCN3, TRNA_Lys, FCGRT | chr19 | 50049718 | 50049953 | Hypo | cancer_general | NOSIP |
| chr19 | 50203173 | 50203203 | Hypo | cancer_general | ADM5, CPT1C | chr19 | 50216042 | 50216072 | Hypo | cancer_general | CPT1C |
| chr19 | 50243339 | 50243379 | Hypo | head_neck | TSKS | chr19 | 50304736 | 50304766 | Hypo | pancreas | AP2A1, FUZ |
| chr19 | 50319874 | 50319916 | Hypo | cancer_general | MED25, FUZ, AP2A1 | chr19 | 50320233 | 50320277 | Hypo | cancer_general | MED25, FUZ, AP2A1 |
| chr19 | 50353394 | 50353574 | Hypo | cancer_general | PTOV1, MIR4749, PTOV1-AS1 | chr19 | 50589044 | 50589079 | Hypo | ovarian | SNAR-A3 |
| chr19 | 50874895 | 50874933 | Hypo | cancer_general | NR1H2, NAPSA | chr19 | 50898558 | 50898727 | Hypo | colorectal | POLD1 |
| chr19 | 50938547 | 50938691 | Hypo | cancer_general | MYBPC2, SPIB | chr19 | 51304554 | 51304602 | Hypo | cancer_general | SNORD88C, SNORD88A, SNORD88B, C19orf48, ACPT |
| chr19 | 51715329 | 51715359 | Hypo | cancer_general | — | chr19 | 52139210 | 52139326 | Hypo | cancer_general | SIGLEC14, SIGLEC5 |
| chr19 | 52391235 | 52391264 | Hypo | literature | ZNF649, ZNF577 | chr19 | 52715963 | 52715992 | Hypo | literature | PPP2R1A |
| chr19 | 53028928 | 53029035 | Hypo | cancer_general | ZNF808 | chr19 | 53204758 | 53204837 | Hypo | hepatobiliary | ZNF611 |
| chr19 | 53291021 | 53291081 | Hypo | cancer_general | ZNF28 | chr19 | 53398908 | 53399031 | Hypo | hepatobiliary | ZNF320 |
| chr19 | 53399814 | 53399848 | Hypo | cancer_general | ZNF320 | chr19 | 53436895 | 53437067 | Hypo | hepatobiliary | ZNF816-ZNF321P |
| chr19 | 53446951 | 53447130 | Hypo | cancer_general | ZNF816, ZNF816-ZNF321P, ZNF321P | chr19 | 53688015 | 53688059 | Hypo | hepatobiliary | ZNF665 |
| chr19 | 53860082 | 53860151 | Hypo | hepatobiliary | ZNF525, ZNF765, ZNF845 | chr19 | 53873182 | 53873212 | Hypo | hepatobiliary | ZNF765, ZNF525 |
| chr19 | 54271479 | 54271509 | Hypo | hepatobiliary | MIR519A2, MIR516A2, MIR1283-2 | chr19 | 54850630 | 54850659 | Hypo | literature | LILRA4 |
| chr19 | 55728901 | 55729104 | Hypo | cancer_general | PTPRH, TMEM86B | chr19 | 55849550 | 55849638 | Hypo | cancer_general | SUV420H2, TMEM150B |
| chr19 | 56201643 | 56201938 | Hypo | ovarian | EPN1 | chr19 | 56340995 | 56341033 | Hypo | cancer_general | NLRP4, NLRP11 |
| chr19 | 56588656 | 56588780 | Hypo | cancer_general | ZNF787 | chr19 | 56858084 | 56858227 | Hypo | cancer_general | ZNF552 |
| chr19 | 57323825 | 57323854 | Hypo | literature | PEG3-AS1, PEG3, ZIM2 | chr19 | 58316915 | 58317096 | Hypo | cancer_general | |
| chr19 | 58325075 | 58325282 | Hypo | cancer_general | ZNF587, ZNF587B, ZNF552 | chr19 | 58807869 | 58807931 | Hypo | ovarian | LOC113386, ZNF8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 58874735 | 58874987 | Hypo | cancer_general | BC023201, ZNF497, A1BG-AS1, A1BG, ZNF837 | chr19 | 58964180 | 58964266 | Hypo | cancer_general | ZNF324B |
| chr19 | 59054642 | 59054774 | Hypo | cancer_general | TRIM28, CHMP2A | AC160854.2_10710-13495 | 1027 | 1057 | Hypo | ovarian | — |
| HPV18 | 111 | 140 | Hypo | virus | — | HPV18 | 383 | 412 | Hypo | virus | — |
| HPV18 | 655 | 684 | Hypo | virus | — | HPV18 | 927 | 956 | Hypo | virus | — |
| HPV18 | 1199 | 1228 | Hypo | virus | — | HPV18 | 1471 | 1500 | Hypo | virus | — |
| HPV18 | 1743 | 1772 | Hypo | virus | — | HPV18 | 2015 | 2044 | Hypo | virus | — |
| HPV18 | 2287 | 2316 | Hypo | virus | — | HPV18 | 2559 | 2588 | Hypo | virus | — |
| HPV18 | 2831 | 2860 | Hypo | virus | — | HPV18 | 3103 | 3132 | Hypo | virus | — |
| HPV18 | 3375 | 3404 | Hypo | virus | — | HPV18 | 3647 | 3676 | Hypo | virus | — |
| HPV18 | 3919 | 3948 | Hypo | virus | — | HPV18 | 4191 | 4220 | Hypo | virus | — |
| HPV18 | 4463 | 4492 | Hypo | virus | — | HPV18 | 4735 | 4764 | Hypo | virus | — |
| HPV18 | 5007 | 5036 | Hypo | virus | — | HPV1 | 5279 | 5308 | Hypo | virus | — |
| HPV18 | 5551 | 5580 | Hypo | virus | — | HPV18 | 5823 | 5852 | Hypo | virus | — |
| HPV18 | 6095 | 6124 | Hypo | virus | — | HPV18 | 6367 | 6396 | Hypo | virus | — |
| HPV18 | 6639 | 6668 | Hypo | virus | — | HPV18 | 6911 | 6940 | Hypo | virus | — |
| HPV18 | 7183 | 7212 | Hypo | virus | — | HPV18 | 7455 | 7484 | Hypo | virus | — |
| chr17 | 415134 | 415163 | Hypo | literature | VPS53 | chr17 | 556252 | 556282 | Hypo | head_neck | VPS53 FAM57A |
| chr17 | 617001 | 617064 | Hypo | cancer_general | VPS53 | chr17 | 631704 | 631734 | Hypo | head_neck | SCARF1 WDR81, MIR22, AF070569, MIR22HG |
| chr17 | 1136593 | 1136653 | Hypo | cancer_general | — | chr17 | 1536116 | 1536146 | Hypo | head_neck | SRR, TSR1 |
| chr17 | 1545976 | 1546442 | Hypo | cancer_general | PRPF8, SCARF1, RILP | chr17 | 1623703 | 1623735 | Hypo | cancer_general | |
| chr17 | 2207718 | 2208063 | Hypo | cancer_general | SRR, SMG6 | chr17 | 2219952 | 2220319 | Hypo | cancer_general | SGSM2 |
| chr17 | 2220564 | 2221059 | Hypo | cancer_general | SRR, TSR1 SGSM2, MNT | chr17 | 2250051 | 2250081 | Hypo | cancer_general | PAFAH1B1, DD413682 |
| chr17 | 2278801 | 2278925 | Hypo | breast | | chr17 | 2496019 | 2496049 | Hypo | cancer_general | |
| chr17 | 2538269 | 2538337 | Hypo | hepatobiliary | PAFAH1B1 | chr17 | 2663898 | 2664032 | Hypo | cancer_general | RAP1GAP2 |
| chr17 | 2811362 | 2811392 | Hypo | cancer_general | RAP1GAP2 | chr17 | 2873476 | 2873551 | Hypo | hepatobiliary | |
| chr17 | 2950959 | 2951091 | Hypo | cancer_general | RAP1GAP2 | chr17 | 3657502 | 3657553 | Hypo | cancer_general | |
| chr17 | 3658849 | 3659011 | Hypo | cancer_general | — | chr17 | 4693354 | 4693388 | Hyp | breast | |
| chr17 | 4698990 | 4699252 | Hypo | cancer_general | PSMB6, GLTPD2, BC150535, VMO1 | chr17 | 5167638 | 5167681 | Hypo | breast | PSMB6, GLTPD2, BC150535, VMO1, TM4SF5 |
| chr17 | 5168597 | 5168732 | Hypo | breast | — | chr17 | 6470357 | 6470419 | Hypo | cancer_general | — |
| chr17 | 7043422 | 7043595 | Hypo | cancer_general | ZBTB4, CHRNB1 | chr17 | 7242844 | 7242899 | Hypo | cancer_general | ACAP1 |
| chr17 | 7368947 | 7369139 | Hypo | ovarian | | chr17 | 7471610 | 7471709 | Hypo | colorectal | SENP3-EIF4A1, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 7488151 | 7488249 | Hypo | cancer_general | SOX15, CD68, DD413682, SNORA67, SNORD10, SNORA48, MPDU1, FXR2, SENP3-EIF4A1 | | | | | | SNORA48, SNORD10, SNORA67, DD413682, SENP3, TNFSF13 |
| chr17 | 7573968 | 7574028 | Hypo | literature | HV941486, HV941440, HV941478, HV941429, HV941442, HV941444, HV941430, HV941433, HV941428, HV941434, HV941431 | chr17 | 7572957 | 7573018 | Hypo | literature | HV941442, HV941444, HV941430, HV941433, HV941428, HV941434, HV941429, HV941478, HV941431, TP53, HV941486, HV941440 |
| chr17 | 7577504 | 7577604 | Hypo | literature | TP53, HV941478, HV941442, HV941444, HV941430, HV941486, HV941428, HV941433, HV941429, HV941440, HV941434, HV941431 | chr17 | 7576847 | 7577167 | Hypo | literature | HV941486, HV941429, HV941430, HV941434, TP53, HV941440, HV941478, HV941442, HV941444, HV941431, HV941433, HV941428 |
| chr17 | 7579285 | 7579880 | Hypo | literature | TP53, HV941430, WRAP53, HV941478, HV941429, HV941428, HV941444, HV941440, | chr17 | 7578164 | 7578570 | Hypo | literature | HV941486, HV941434, HV941428, HV941440, HV941478, HV941442, HV941444, HV941429, HV941431, TP53, HV941430, HV941433 |
| | | | | | | chr17 | 7906832 | 7906861 | Hypo | tcga | GUCY2D |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 8104145 | 8104260 | Hypo | cancer_general | HV941486, HV941434, HV941433, HV941431, HV941442 AURKB | chr17 | 8774623 | 8774653 | Hypo | cancer_general | PIK3R5, PIK3R6 |
| chr17 | 9790805 | 9790835 | Hypo | cancer_general | GLP2R | chr17 | 10599510 | 10599546 | Hypo | cancer_general | SCO1, ADPRM |
| chr17 | 11984693 | 11984722 | Hypo | literature | MIR744, MAP2K4 | chr17 | 11998944 | 11998973 | Hypo | literature | — |
| chr17 | 12013726 | 12013755 | Hypo | literature | — | chr17 | 12016630 | 12016650 | Hypo | literature | — |
| chr17 | 12028618 | 12028647 | Hypo | literature | — | chr17 | 12659029 | 12659063 | Hypo | cancer_general | MYOCD |
| chr17 | 15926819 | 15926849 | Hypo | head_neck | TTC19, NCOR1 | chr17 | 16119860 | 16120047 | Hypo | cancer_general | PIGL, NCOR1 |
| chr17 | 16282251 | 16282300 | Hypo | cancer_general | UBB | chr17 | 16326144 | 16326216 | Hypo | head_neck | TRPV2 |
| chr17 | 16428708 | 16428738 | Hypo | head_neck | — | chr17 | 17062574 | 17062763 | Hypo | head_neck | MPRIP |
| chr17 | 17117365 | 17117395 | Hypo | breast | FLCN, PLD6 | chr17 | 17123963 | 17123993 | Hypo | head_neck | FLCN, PLD6 |
| chr17 | 17719242 | 17719355 | Hypo | breast | MIR33B, SREBP-1, SREBF1 | chr17 | 18162844 | 18163325 | Hypo | cancer_general | FLII, SMCR7, DQ596932 |
| chr17 | 18817198 | 18817284 | Hypo | esophageal | PRPSAP2 | chr17 | 19769739 | 19769821 | Hypo | cancer_general | TRNA_Gly |
| chr17 | 19886035 | 19886221 | Hypo | head_neck | AKAP10 | chr17 | 20039589 | 20039676 | Hypo | hepatobiliary | SPECC1 |
| chr17 | 20081131 | 20081161 | Hypo | hepatobiliary | SPECC1 | chr17 | 20205055 | 20205181 | Hypo | hepatobiliary | SPECC1 |
| chr17 | 20238152 | 20238198 | Hypo | hepatobiliary | CCDC144CP | chr17 | 20468021 | 20468090 | Hypo | cancer_general | DQ584223 |
| chr17 | 20817755 | 20817917 | Hypo | cancer_general | — | chr17 | 21003587 | 21003721 | Hypo | cancer_general | HP08942 |
| chr17 | 25620573 | 25620715 | Hypo | cancer_general | MIR4522, WSB1 | chr17 | 25676959 | 25676989 | Hypo | cancer_general | — |
| chr17 | 25680264 | 25680294 | Hypo | cancer_general | — | chr17 | 25907750 | 25907780 | Hypo | cancer_general | KSR1 |
| chr17 | 26263183 | 26263322 | Hypo | cancer_general | — | chr17 | 26927249 | 26927410 | Hypo | cancer_general | SGK494, SPAG5-AS1, SPAG5 |
| chr17 | 26961770 | 26961833 | Hypo | cancer_general, breast | KIAA0100 | chr17 | 27036492 | 27037023 | Hypo | cancer_general | RAB34, NARR, RPL23A, PROCA1 |
| chr17 | 27056577 | 27056857 | Hypo | cancer_general | SNORD42A, SNORD4A, SNORD42B, RPL23A, NEK8, TLCD1, SNORD4B | chr17 | 27081845 | 27081963 | Hypo | cancer_general | FAM222B, TRAF4 |
| chr17 | 27170162 | 27170460 | Hypo | cancer_general | FAM222B | chr17 | 27181180 | 27181371 | Hypo | lung | ERAL1, MIR451A, MIR451B, MIR144, MIR4732 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 27686651 | 27686783 | Hypo | colorectal | — | chr17 | 27716114 | 27716220 | Hypo | cancer_general | MIR4523, TAOK1 |
| chr17 | 27716436 | 27716642 | Hypo | cancer_general | MIR4523, TAOK1 | chr17 | 28112648 | 28112688 | Hypo | cancer_general | SSH2 |
| chr17 | 28112951 | 28113037 | Hypo | cancer_general | SSH2 | chr17 | 29232244 | 29232350 | Hypo | cancer_general | TEFM |
| chr17 | 29234283 | 29234313 | Hypo | cancer_general | TEFM | chr17 | 29508761 | 29508790 | Hypo | literature | NF1 |
| chr17 | 29541527 | 29541556 | Hypo | literature | NF1 | chr17 | 29562732 | 29562761 | Hypo | literature | NF1 |
| chr17 | 30243768 | 30243907 | Hypo | cancer_general | — | chr17 | 30250325 | 30250364 | Hypo | cancer_general | — |
| chr17 | 30258469 | 30258499 | Hypo | head_neck | SUZ12 | chr17 | 30568137 | 30568174 | Hypo | breast | — |
| chr17 | 30710818 | 30710888 | Hypo | cancer_general | ZNF207 | chr17 | 32386720 | 32386875 | Hypo | cancer_general | SLFN14 |
| chr17 | 33721211 | 33721349 | Hypo | cancer_general | — | chr17 | 33877286 | 33877439 | Hypo | cancer_general | SNORA21, C17orf98, RPL23 |
| chr17 | 33917210 | 33917268 | Hypo | cancer_general | AP2B1 | chr17 | 37001415 | 37001921 | Hypo | cancer_general | FBXO47 |
| chr17 | 37011176 | 37011236 | Hypo | cancer_general | RPL23, TRNA_Cys, SNORA21 | chr17 | 37131789 | 37132028 | Hypo | cancer_general | LRRC37A11P |
| chr17 | 37181771 | 37181865 | Hypo | cancer_general | LRRC37A11P ARL5C, TRNA_Cys, PLXDC1 | chr17 | 37192072 | 37192201 | Hypo | cancer_general | STAC2 |
| chr17 | 37312431 | 37312477 | Hypo | cancer_general | | chr17 | 37369180 | 37369210 | Hypo | cancer_general | RPL19 |
| chr17 | 37484062 | 37484128 | Hypo | cancer_general | FBXL20 | chr17 | 37868190 | 37868294 | Hypo | literature | ERBB2 |
| chr17 | 37879568 | 37879615 | Hypo | literature | MIR4728, MIEN1, ERBB2 | chr17 | 37880205 | 37880276 | Hypo | literature | MIR4728, MIEN1, ERBB2 |
| chr17 | 37880971 | 37881018 | Hypo | literature | MIEN1, ERBB2, MIR4728 | chr17 | 37881318 | 37881631 | Hypo | literature | MIR4728, MIEN1, ERBB2 |
| chr17 | 38179397 | 38179430 | Hypo | cancer_general | MED24, SNORD124, CSF3 | chr17 | 38335459 | 38335533 | Hypo | cancer_general | RAPGEFL1, CASC3 |
| chr17 | 38380553 | 38380598 | Hypo | cancer_general | WIPF2 | chr17 | 38473104 | 38473180 | Hypo | literature | RARA |
| chr17 | 38574991 | 38575021 | Hypo | cancer_general | TOP2A | chr17 | 39682352 | 39682711 | Hypo | cancer_general | AK090604, KRT15, JUP, KRT19 |
| chr17 | 39834201 | 39834287 | Hypo | cancer_general | — | chr17 | 40474467 | 40474496 | Hypo | literature | STAT3, AK024535, AK092965 |
| chr17 | 40897739 | 40897788 | Hypo | ovarian | RAMP2-AS1, BC047651, EZH1 | chr17 | 40975413 | 40975677 | Hypo | cancer_general | PSME3, BECN1 |
| chr17 | 41175146 | 41175331 | Hypo | cancer_general | RND2, VAT1, IFI35 | chr17 | 41197714 | 41197743 | Hypo | literature | BRCA1 |
| chr17 | 41201163 | 41201192 | Hypo | literature | BRCA1 | chr17 | 41203073 | 41203102 | Hypo | literature | BRCA1 |
| chr17 | 41209064 | 41209114 | Hypo | literature | NBR2, BRCA1 | chr17 | 41215890 | 41215961 | Hypo | literature | BRCA1 |
| chr17 | 41267731 | 41267775 | Hypo | literature | | chr17 | 41276031 | 41276075 | Hypo | literature | BRCA1, NBR2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 41278621 | 41278700 | Hypo | cancer_general | NBR2, BRCA1 | chr17 | 41651850 | 41651880 | Hypo | cancer_general | — |
| chr17 | 41745825 | 41745855 | Hypo | cancer_general | MEOX1 | chr17 | 41791665 | 41791694 | Hypo | tcga | LSM12, G6PC3, AX746969 |
| chr17 | 42110423 | 42110561 | Hypo | head_neck | LSM12 | chr17 | 42142661 | 42142808 | Hypo | cancer_general | SLC4A1 |
| chr17 | 42246452 | 42246521 | Hypo | cancer_general | ASB16, ASB16-AS1, C17orf65, C17orf53 | chr17 | 42321590 | 42321674 | Hypo | cancer_general | — |
| chr17 | 42331412 | 42331659 | Hypo | cancer_general | SLC4A1 | chr17 | 42580695 | 42580793 | Hypo | breast | — |
| chr17 | 42587249 | 42587355 | Hypo | cancer_general | — | chr17 | 42590091 | 42590224 | Hypo | cancer_general | DBF4B |
| chr17 | 42767947 | 42768198 | Hypo | cancer_general | CCDC43 | chr17 | 42787481 | 42787616 | Hypo | cancer_general | GFAP, |
| chr17 | 42975726 | 42975756 | Hypo | cancer_general | CCDC103, FAM187A, AK124465, GFAP, EFTUD2 | chr17 | 43001891 | 43001946 | Hypo | cancer_general | KIF18B |
| chr17 | 44897416 | 44897445 | Hypo | literature | WNT3 | chr17 | 45022106 | 45022140 | Hypo | cancer_general | GOSR2 |
| chr17 | 45187608 | 45187638 | Hypo | cancer_general | CDC27 | chr17 | 46567400 | 46567655 | Hypo | cancer_general | — |
| chr17 | 46827420 | 46827539 | Hypo | cancer_general | — | chr17 | 47657544 | 47657583 | Hypo | cancer_general | NXPH3 |
| chr17 | 48473056 | 48473236 | Hypo | cancer_general | — | chr17 | 48589801 | 48589831 | Hypo | colorectal | MYCBPAP |
| chr17 | 48612223 | 48612308 | Hypo | cancer_general | EPN3, SPATA20, MYCBPAP | chr17 | 48653128 | 48653158 | Hypo | cancer_general | CACNA1G |
| chr17 | 48799820 | 48799866 | Hypo | cancer_general | LUC7L3 | chr17 | 49229267 | 49229703 | Hypo | cancer_general | NME1-NME2, NME1 |
| chr17 | 53479184 | 53479316 | Hypo | colorectal | MMD | chr17 | 53814544 | 53814678 | Hypo | cancer_general | SRSF1 |
| chr17 | 55037326 | 55037626 | Hypo | cancer_general | COIL | chr17 | 56092600 | 56092736 | Hypo | cancer_general | TEX14 |
| chr17 | 56471121 | 56471167 | Hypo | colorectal | RNF43 | chr17 | 56743206 | 56743249 | Hypo | cancer_general | — |
| chr17 | 57296865 | 57297129 | Hypo | cancer_general | GDPD1, SMG8 | chr17 | 57386255 | 57386735 | Hypo | cancer_general | — |
| chr17 | 57787402 | 57787465 | Typo | cancer_general | VMP1, PTRH2 | chr17 | 57832475 | 57832607 | Hypo | cancer_general | VMP1 |
| chr17 | 59481657 | 59481694 | Hypo | esophageal | C17orf82, TBX2 | chr17 | 59924556 | 59924585 | Hypo | literature | — |
| chr17 | 59937192 | 59937236 | Hypo | literature | INTS2 | chr17 | 61673374 | 61677404 | Hypo | cancer_general | TACO1, BC024682, DQ577731, DCAF7 |
| chr17 | 61817576 | 61817955 | Hypo | cancer_general | STRADA, CCDC47 | chr17 | 62028596 | 62028790 | Hypo | cancer_general | SCN4A |
| chr17 | 64672366 | 64672544 | Hypo | cancer_general | — | chr17 | 65715296 | 65715493 | Hypo | cancer_general | NOL11 |
| chr17 | 66420718 | 66420837 | Hypo | lung | MIR635, WIPI1, ARSG | chr17 | 67410305 | 67410397 | Hypo | cancer_general | MAP2K6 |
| chr17 | 70586165 | 70586272 | Hypo | cancer_general | LINC00511, LINC00673 | chr17 | 71229815 | 71229918 | Hypo | cancer_general | C17orf80, FAM104A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 72236510 | 72236548 | Hypo | hepatobiliary | TTYH2 | chr17 | 72491378 | 72491531 | Hypo | ovarian | Metazoa_SRP, TRNA_Arg, JB153618, KCTD2, ATP5H |
| chr17 | 72862371 | 72862460 | Hypo | blood | FDXR, GRIN2C | chr17 | 73031637 | 73031935 | Hypo | cancer_general | ARMC7 HN1 |
| chr17 | 73115588 | 73115658 | Hypo | cancer_general | ARMC7 | chr17 | 73115884 | 73115914 | Hypo | cancer_general | |
| chr17 | 73128301 | 73128338 | Hypo | cancer_general | NT5C, ARMC7, HN1 | chr17 | 73147177 | 73147356 | Hypo | cancer_general | |
| chr17 | 73147774 | 73147992 | Hypo | cancer_general | HN1 | chr17 | 73215289 | 73215423 | Hypo | ovarian | NUP85 |
| chr17 | 73351981 | 73352086 | Hypo | breast | GRB2 | chr17 | 73545998 | 73546299 | Hypo | cancer_general | LLGL2 |
| chr17 | 73586015 | 73586418 | Hypo | cancer_general | MYO15B | chr17 | 73608306 | 73608336 | Hypo | cancer_general | MYO15B |
| chr17 | 73636144 | 73636337 | Hypo | cancer_general | RECQL5, SMIM5, SMIM6 | chr17 | 73692986 | 73693122 | Hypo | cancer_general | SAP30BP |
| chr17 | 73782870 | 73782947 | Hypo | cancer_general | UNK, MIR4738, H3F3B | chr17 | 73808631 | 73808671 | Hypo | head_neck | UNK |
| chr17 | 73827213 | 73827243 | Hypo | esophageal | UNC13D, UNK | chr17 | 73901630 | 73901893 | Hypo | cancer_general | MRPL38, TRIM65, FBF1 |
| chr17 | 73904093 | 73904127 | Hypo | lung | FBF1, MRPL38 | chr17 | 74028346 | 74028413 | Hypo | cancer_general | SRP68, EVPL |
| chr17 | 74047797 | 74048063 | Hypo | cancer_general | SRP68 | chr17 | 74087118 | 74087185 | Hypo | head_neck | EXOC7, ZACN |
| chr17 | 74299798 | 74299899 | Hypo | cancer_general | PRPSAP1, QRICH2 | chr17 | 74390363 | 74390393 | Hypo | cancer_general | UBE2O, SPHK1 |
| chr17 | 74663258 | 74663288 | Hypo | head_neck | MXRA7 | chr17 | 74732944 | 74732973 | Hypo | literature | MFSD11, MIR636, SRSF2, METTL23 |
| chr17 | 75207514 | 75207630 | Hypo | blood | SEC14L1 | chr17 | 75207839 | 75207987 | Hypo | blood | SEC14L1 |
| chr17 | 75276054 | 75276083 | Hypo | literature | 9-Sep | chr17 | 75276413 | 75276442 | Hypo | literature | 9-Sep |
| chr17 | 75277348 | 75277659 | Hypo | literature | 9-Sep | chr17 | 75278020 | 75278049 | Hypo | literature | 9-Sep |
| chr17 | 75279105 | 75279134 | Hypo | literature | 9-Sep | chr17 | 75282025 | 75282154 | Hypo | literature | 9-Sep |
| chr17 | 75316368 | 75316397 | Hypo | literature | 9-Sep | chr17 | 75317170 | 75317199 | Hypo | literature | 9-Sep |
| chr17 | 75347755 | 75347784 | Hypo | literature | 9-Sep | chr17 | 75373312 | 75373341 | Hypo | literature | 9-Sep |
| chr17 | 75405827 | 75405856 | Hypo | literature | | chr17 | 75523142 | 75523272 | Hypo | cancer_general | BC040189 |
| chr17 | 75733978 | 75734244 | Hypo | lung, cancer_general | | chr17 | 75797111 | 75797179 | Hypo | cancer_general | |
| chr17 | 76021047 | 76021077 | Hypo | cancer_general | TNRC6C | chr17 | 76130124 | 76130153 | Hypo | literature | TMC8, TMC6 |
| chr17 | 76135783 | 76136001 | Hypo | lung, cancer_general | C17orf99, TMC8 | chr17 | 76137951 | 76138190 | Hypo | cancer_general | C17orf99, TMC8 |
| chr17 | 76138498 | 76138622 | Hypo | cancer_general | TMC8, C17orf99 | chr17 | 76187407 | 76187544 | Hypo | ovarian | AFMID, TK1 |
| chr17 | 76207342 | 76207372 | Hypo | cancer_general | BIRC5, AFMID | chr17 | 76211302 | 76211506 | Hypo | cancer_general | EPR-1, BIRC5, AFMID |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 76404615 | 76404659 | Hypo | colorectal | PGS1 | chr17 | 76877177 | 76877212 | Hypo | hepatobiliary | LOC100653515, TIMP2 |
| chr17 | 76884417 | 76884447 | Hypo | hepatobiliary | LOC100653515, TIMP2 | chr17 | 76974447 | 76974499 | Hypo | cancer_general | LGALS3BP |
| chr17 | 76983518 | 76983669 | Hypo | cancer_general | CANT1, LGALS3BP | chr17 | 76984053 | 76984188 | Hypo | cancer_general | LGALS3BP, CANT1, DQ595190 |
| chr17 | 77070307 | 77070457 | Hypo | colorectal | ENGASE | chr17 | 77084518 | 77084727 | Hypo | ovarian | RBFOX3, ENGASE |
| chr17 | 77105055 | 77105198 | Hypo | cancer_general | RBFOX3 | chr17 | 77145129 | 77145242 | Hypo | cancer_general | RBFOX3 |
| chr17 | 77394706 | 77394850 | Hypo | ovarian | RBFOX3 | chr17 | 77825696 | 77825812 | Hypo | cancer_general | — |
| chr17 | 77827201 | 77827201 | Hypo | cancer_general | — | chr17 | 77919429 | 77919477 | Hypo | pancreas | TBC1D16 |
| chr17 | 77924259 | 77924351 | Hypo | pancreas | TBC1D16 | chr17 | 78122158 | 78122190 | Hypo | cancer_general | EIF4A3 |
| chr17 | 78194821 | 78194861 | Hypo | pancreas | SLC26A11, SGSH | chr17 | 78272278 | 78272313 | Hypo | breast | RNF213 |
| chr17 | 78447127 | 78447157 | Hypo | cancer_general | NPTX1, AX746631 | chr17 | 78518031 | 78518198 | Hypo | cancer_general | RPTOR |
| chr17 | 78599596 | 78599628 | Hypo | cancer_general | RPTOR | chr17 | 78667992 | 78668159 | Hypo | cancer_general | RPTOR, AF258550, CHMP6 |
| chr17 | 78874441 | 78874559 | Hypo | cancer_general | — | chr17 | 78975667 | 78975758 | Hypo | cancer_general | |
| chr17 | 78999625 | 78999654 | Hypo | literature | BAIAP2-AS1, BAIAP2 | chr17 | 79094182 | 79094245 | Hypo | cancer_general | MIR657, MIR3065, MIR338, AATK |
| chr17 | 79099770 | 79099799 | Hypo | literature | MIR1250, MIR338, MIR3065, MIR657, AATK | chr17 | 79626591 | 79626703 | Hypo | cancer_general | OXLD1, CCDC137, PDE6G |
| chr17 | 79626955 | 79626985 | Hypo | cancer_general | OXLD1, CCDC137, PDE6G | chr17 | 79769433 | 79769693 | Hypo | cancer_general | GCGR |
| chr17 | 79850445 | 79850537 | Hypo | cancer_general | ALYREF, ANAPC11, NPB | chr17 | 79896013 | 79896043 | Hypo | blood | MYADML2, PYCR1, MAFG-AS1 |
| chr17 | 79939605 | 79939835 | Hypo | cancer_general | ASPSCR1 | chr17 | 79945037 | 79945074 | Hypo | breast | ASPSCR1 |
| chr17 | 80254266 | 80254296 | Hypo | cancer_general | BC033560 | chr17 | 80289234 | 80289310 | Hypo | cancer_general | SECTM1 |
| chr17 | 80289858 | 80289892 | Hypo | cancer_general | SECTM1 | chr17 | 80294282 | 80294427 | Hypo | cancer_general | SECTM1 |
| chr17 | 80394063 | 80394185 | Hypo | breast | HEXDC, C17orf62 | chr17 | 80479311 | 80479559 | Hypo | cancer_general | FOXK2 |
| chr17 | 80491572 | 80491602 | Hypo | head_neck | FOXK2 | chr17 | 80535382 | 80535487 | Hypo | colorectal | FOXK2 |
| chr17 | 80571380 | 80571776 | Hypo | lung | WDR45B, FOXK2 | chr17 | 80593754 | 80594107 | Hypo | cancer_general | WDR45B |
| chr17 | 80654983 | 80655013 | Hypo | cancer_general | RAB40B | chr17 | 80749152 | 80749276 | Hypo | ovarian | TBCD |
| chr17 | 80751650 | 80751714 | Hypo | breast | TBCD | chr17 | 80794259 | 80794288 | Hypo | literature | TBCD, ZNF750 |
| chr17 | 80797692 | 80798345 | Hypo | cancer_general | ZNF750, TBCD | chr17 | 80832305 | 80832411 | Hypo | cancer_general | — |
| chr17 | 80832712 | 80832796 | Hypo | cancer_general | — | chr17 | 80859239 | 80859269 | Hypo | head_neck | TBCD |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 81008618 | 81008826 | Hypo | cancer_general | — | chr17 | 81033487 | 81033517 | Hypo | cancer_general | METRNL |
| chr17 | 81048993 | 81049023 | Hypo | cancer_general | METRNL | chr17 | 81049994 | 81050058 | Hypo | cancer_general | METRNL |
| chr20 | 291148 | 291373 | Hyper | cancer_general | — | chr20 | 590434 | 590502 | Hyper | cancer_general | TCF15 |
| chr20 | 590751 | 590868 | Hyper | liver_tcga, cancer_general | TCF15 | chr20 | 592405 | 592449 | Hyper | cancer_general | TCF15 |
| chr20 | 644182 | 644787 | Hyper | cancer_general | SCRT2 | chr20 | 982749 | 982989 | Hyper | cancer_general | RSPO4 |
| chr20 | 1206855 | 1207034 | Hyper | blood | RAD21L1 | chr20 | 1783761 | 1784365 | Hyper | tcga, liver_tcga, cancer_general | — |
| chr20 | 1874512 | 1874541 | Hyper | literature | SIRPA | chr20 | 1876110 | 1876176 | Hyper | esophageal | SIRPA |
| chr20 | 2539331 | 2539771 | Hyper | cancer_general | TMC2 | chr20 | 2668770 | 2668922 | Hyper | cancer_general | EBF4 |
| chr20 | 2780753 | 2781452 | Hyper | tcga, liver_tcga, cancer_general | CPXM1 | chr20 | 2781731 | 2781761 | Hyper | cancer_general | CPXM1 |
| chr20 | 2785659 | 2786060 | Hyper | cancer_general | TMEM239, C20orf141, CPXM1 | chr20 | 3052583 | 3052836 | Hyper | cancer_general | OXT |
| chr20 | 3073488 | 3073899 | Hyper | cancer_general | AVP | chr20 | 3220893 | 3220943 | Hyper | cancer_general | SLC4A11, C20orf194 |
| chr20 | 3229576 | 3229612 | Hyper | cancer_general | C20orf194, SLC4A11 | chr20 | 3389393 | 3389549 | Hyper | tcga | — |
| chr20 | 3641733 | 3641937 | Hyper | cancer_general | ADAM33, AX748440, GFRA4 | chr20 | 3663020 | 3663174 | Hyper | cancer_general | ADAM33, SIGLEC1 |
| chr20 | 3762152 | 3762181 | Hyper | tcga | CENPB, CDC25B, SPEF1 | chr20 | 4229402 | 4229432 | Hyper | cancer_general | ADRA1D |
| chr20 | 4229786 | 4230600 | Hyper | esophageal, cancer_general | ADRA1D | chr20 | 4803070 | 4803650 | Hyper | tcga, cancer_general | RASSF2 |
| chr20 | 4803921 | 4804008 | Hyper | colorectal | RASSF2 | chr20 | 4804566 | 4804724 | Hyper | tcga | RASSF2 |
| chr20 | 5296172 | 5296900 | Hyper | cancer_general | AX746654, PROKR2 | chr20 | 5297206 | 5297603 | Hyper | cancer_general | AX746654, PROKR2 |
| chr20 | 6748925 | 6749036 | Hyper | blood | BMP2 | chr20 | 8112378 | 8112408 | Hyper | cancer_general | PLCB1 |
| chr20 | 8112739 | 8113022 | Hyper | tcga, cancer_general | PLCB1 | chr20 | 8113557 | 8113605 | Hyper | cancer_general | PLCB1 |
| chr20 | 9487385 | 9487997 | Hyper | cancer_general | LAMP5 | chr20 | 9488376 | 9488795 | Hyper | cancer_general | LAMP5 |
| chr20 | 9489214 | 9489424 | Hyper | cancer_general | LAMP5 | chr20 | 9489424 | 9489708 | Hyper | cancer_general | LAMP5 |
| chr20 | 9495271 | 9495509 | Hyper | cancer_general | LAMP5 | chr20 | 9496330 | 9496833 | Hyper | cancer_general | SNAP25 |
| chr20 | 9497035 | 9497109 | Hyper | cancer_general | LAMP5 | chr20 | 10198289 | 10198600 | Hyper | cancer_general | ISM1, AY927515 |
| chr20 | 10198915 | 10198945 | Hyper | cancer_general | SNAP25 | chr20 | 13200599 | 13200634 | Hyper | cancer_general | PCSK2 |
| chr20 | 17206513 | 17206747 | Hyper | cancer_general | PCSK2 | chr20 | 17207874 | 17207930 | Hyper | cancer_general | PCSK2 |
| chr20 | 17208585 | 17208620 | Hyper | cancer_general | PCSK2 | chr20 | 18039823 | 18039897 | Hyper | blood | OVOL2 |
| chr20 | 18073312 | 18073461 | Hyper | pancreas | — | chr20 | 19739592 | 19739696 | Hyper | cancer_general | — |
| chr20 | 20344498 | 20344559 | Hyper | cancer_general | C20orf26, INSM1 | chr20 | 20345686 | 20346106 | Hyper | cancer_general | INSM1, C20orf26 |
| chr20 | 20347460 | 20348154 | Hyper | cancer_general | INSM1, C20orf26 | chr20 | 20348526 | 20348605 | Hyper | esophageal | — |
| chr20 | 20349153 | 20349255 | Hyper | tcga, liver_tcga | INSM1, C20orf26 | chr20 | 20349574 | 20349604 | Hyper | esophageal | INSM1, C20orf26 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 21080714 | 21082253 | Hyper | liver_tcga, cancer_general | — | chr20 | 21082532 | 21082917 | Hyper | cancer_general | — |
| chr20 | 21083421 | 21084361 | Hyper | cancer_general | — | chr20 | 21085831 | 21085864 | Hyper | cancer_general | — |
| chr20 | 21086176 | 21086451 | Hyper | cancer_general | — | chr20 | 21086866 | 21087188 | Hyper | cancer_general | — |
| chr20 | 21372174 | 21372725 | Hyper | cancer_general | NKX2-4, XRN2 | chr20 | 21376250 | 21378551 | Hyper | liver_tcga, cancer_general | NKX2-4, XRN2 |
| chr20 | 21486375 | 21486881 | Hyper | cancer_general | NKX2-2 | chr20 | 21487153 | 21487581 | Hyper | cancer_general | NKX2-2 |
| chr20 | 21488158 | 21488351 | Hyper | cancer_general | NKX2-2 | chr20 | 21489224 | 21489703 | Hyper | cancer_general | NKX2-2 |
| chr20 | 21490175 | 21491529 | Hyper | cancer_general | NKX2-2 | chr20 | 21492378 | 21492983 | Hyper | cancer_general | NKX2-2 |
| chr20 | 21493308 | 21494265 | Hyper | cancer_general | NKX2-2 | chr20 | 21494531 | 21494703 | Hyper | cancer_general | NKX2-2 |
| chr20 | 21495942 | 21495986 | Hyper | cancer_general | NKX2-2 | chr20 | 21496260 | 21496294 | Hyper | cancer_general | NKX2-2 |
| chr20 | 21496637 | 21497136 | Hyper | cancer_general | NKX2-2 | chr20 | 21497413 | 21498638 | Hyper | cancer_general | NKX2-2 |
| chr20 | 21499961 | 21500134 | Hyper | cancer_general | NKX2-2 | chr20 | 21501424 | 21501724 | Hyper | cancer_general | NKX2-2 |
| chr20 | 21502037 | 21502330 | Hyper | cancer_general | NKX2-2 | chr20 | 21502590 | 21503117 | Hyper | cancer_general | NKX2-2 |
| chr20 | 21503441 | 21503773 | Hyper | cancer_general, tcga | NKX2-2 | chr20 | 21682399 | 21682456 | Hyper | cancer_general | PAX1 |
| chr20 | 21683311 | 21683651 | Hyper | cancer_general | PAX1 | chr20 | 21686235 | 21686677 | Hyper | cancer_general | PAX1 |
| chr20 | 21687009 | 21687731 | Hyper | cancer_general | PAX1 | chr20 | 21689956 | 21690185 | Hyper | cancer_general | PAX1 |
| chr20 | 21694499 | 21694529 | Hyper | cancer_general | PAX1 | chr20 | 21695088 | 21695357 | Hyper | tcga, cancer_general | PAX1 |
| chr20 | 21748445 | 21748491 | Hyper | cancer_general | — | chr20 | 22557396 | 22557675 | Hyper | cancer_general | FOXA2, LINC00261 |
| chr20 | 22557979 | 22558114 | Hyper | cancer_general | FOXA2, LINC00261 | chr20 | 22558637 | 22558669 | Hyper | cancer_general | FOXA2, LINC00261 |
| chr20 | 22559645 | 22559690 | Hyper | cancer_general | FOXA2, LINC00261 | chr20 | 22562721 | 22562840 | Hyper | cancer_general | FOXA2, LINC00261 |
| chr20 | 22563563 | 22563602 | Hyper | literature | FOXA2, LINC00261 | chr20 | 22564235 | 22564265 | Hyper | blood | BC045663, SSTR4 |
| chr20 | 22566961 | 22566990 | Hyper | literature | — | chr20 | 23015917 | 23015946 | Hyper | literature | THBD, AX747264 |
| chr20 | 23029110 | 23029151 | Hyper | literature, cancer_general | THBD, AX747264 | chr20 | 23029387 | 23030357 | Hyper | literature, cancer_general | THBD, AX747264 |
| chr20 | 23031548 | 23031692 | Hyper | literature | THBD, AX747264 | chr20 | 24450231 | 24450513 | Hyper | tcga, cancer_general | SYNDIG1 |
| chr20 | 24450782 | 24451019 | Hyper | cancer_general | SYNDIG1 | chr20 | 24451450 | 24451592 | Hyper | cancer_general | SYNDIG1 |
| chr20 | 25058385 | 25058616 | Hyper | cancer_general | VSX1 | chr20 | 25061746 | 25062880 | Hyper | cancer_general | VSX1 |
| chr20 | 25063780 | 25064458 | Hyper | cancer_general | VSX1 | chr20 | 25065179 | 25065395 | Hyper | cancer_general | VSX1 |
| chr20 | 25129384 | 25129464 | Hyper | cancer_general | LOC284798 | chr20 | 26188812 | 26189011 | Hyper | liver_tcga, cancer_general, literature | MIR663A, LOC284801 |
| chr20 | 26190313 | 26190361 | Hyper | liver_tcga, literature | MIR663A, LOC284801 | chr20 | 30582750 | 30582978 | Hyper | cancer_general | XKR7 |
| chr20 | 30639141 | 30639319 | Hyper | cancer_general | HCK | chr20 | 30639632 | 30639847 | Hyper | cancer_general | HCK |
| chr20 | 30640106 | 30640270 | Hyper | tcga | HCK | chr20 | 30778024 | 30778313 | Hyper | tcga, liver_tcga, cancer_general | TSPY26P, PLAGL2 |
| chr20 | 34188617 | 34189391 | Hyper | cancer_general | FER1L4 | chr20 | 34189635 | 34189910 | Hyper | cancer_general | FER1L4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 36531799 | 36531910 | Hyper | colorectal | VSTM2L | chr20 | 36781324 | 36781354 | Hyper | cancer_general | TGM2, HV531029, HV530979, HV531015, HV531014, HV531011, HV531005 |
| chr20 | 37302697 | 37303343 | Hyper | cancer_general, tcga | — | chr20 | 37351793 | 37352626 | Hyper | cancer_general | SLC32A1 |
| chr20 | 37353193 | 37353236 | Hyper | cancer_general | SLC32A1 | chr20 | 37353455 | 37353779 | Hyper | cancer_general | SLC32A1 |
| chr20 | 37354145 | 37355202 | Hyper | cancer_general | SLC32A1 | chr20 | 37355847 | 37357353 | Hyper | cancer_general | SLC32A1 |
| chr20 | 37357825 | 37358190 | Hyper | colorectal | SLC32A1 | chr20 | 37434552 | 37434744 | Hyper | colorectal | PPP1R16B |
| chr20 | 37435104 | 37435218 | Hyper | tcga | PPP1R16B | chr20 | 37434461 | 37435860 | Hyper | cancer_general | PPP1R16B |
| chr20 | 39316203 | 39316322 | Hyper | tcga | MAFB | chr20 | 39316893 | 39317392 | Hyper | cancer_general, colorectal, esophageal | MAFB |
| chr20 | 39317750 | 39318166 | Hyper | esophageal | MAFB | chr20 | 39318383 | 39318415 | Hyper | cancer_general | MAFB |
| chr20 | 39319126 | 39319653 | Hyper | tcga, cancer_general | MAFB | chr20 | 39995146 | 39995813 | Hyper | cancer_general | EMILIN3, LPIN3 |
| chr20 | 40743859 | 40743888 | Hyper | literature | PTPRT | chr20 | 41817786 | 41818085 | Hyper | tcga, cancer_general | — |
| chr20 | 41818567 | 41818914 | Hyper | cancer_general | — | chr20 | 42136330 | 42136411 | Hyper | cancer_general | L3MBTL1 |
| chr20 | 42543754 | 42543853 | Hyper | cancer_general | TOX2 GDAP1L1 | chr20 | 42544091 | 42544984 | Hyper | cancer_general | TOX2 |
| chr20 | 42876525 | 42876675 | Hyper | cancer_general | RIMS4 | chr20 | 43438071 | 43438466 | Hyper | cancer_general | RIMS4 |
| chr20 | 43438982 | 43439022 | Hyper | lung, cancer_general | SNX21, TNNC2, UBE2C | chr20 | 43439291 | 43439510 | Hyper | cancer_general | RIMS4 |
| chr20 | 44452731 | 44453063 | Hyper | cancer_general | — | chr20 | 44519077 | 44519107 | Hyper | cancer_general | PLTP, NEURL2, SPATA25, ZSWIM1, CTSA |
| chr20 | 44639181 | 44639496 | Hyper | cancer_general | MMP9 | chr20 | 44640338 | 44640367 | Hyper | literature | SLC12A5, MMP9 |
| chr20 | 44660750 | 44660877 | Hyper | cancer_general | SLC12A5 | chr20 | 44686190 | 44686762 | Hyper | cancer_general | NCOA5, SLC12A5 |
| chr20 | 44746484 | 44746781 | Hyper | tcga | CD40 | chr20 | 44803174 | 44803675 | Hyper | cancer_general | CDH22 |
| chr20 | 44875240 | 44875411 | Hyper | cancer_general, tcga | — | chr20 | 44879801 | 44880076 | Hyper | cancer_general | — |
| chr20 | 44937202 | 44937643 | Hyper | cancer_general | — | chr20 | 44941518 | 44941661 | Hyper | cancer_general | — |
| chr20 | 45142000 | 45142272 | Hyper | tcga, cancer_general | ZNF334 | chr20 | 45279854 | 45280302 | Hyper | cancer_general, tcga | SLC13A3 |
| chr20 | 45524523 | 45524553 | Hyper | cancer_general | EYA2 | chr20 | 47443729 | 47444282 | Hyper | cancer_general | — |
| chr20 | 47934824 | 47935268 | Hyper | cancer_general | — | chr20 | 47935495 | 47935567 | Hyper | cancer_general | — |
| chr20 | 47935928 | 47936027 | Hyper | cancer_general | MOCS3, DPM1 | chr20 | 48184381 | 48184435 | Hyper | cancer_general | PTGIS |
| chr20 | 49575909 | 49575939 | Hyper | cancer_general | ATP9A | chr20 | 49639777 | 49640157 | Hyper | tcga, cancer_general | KCNG1 |
| chr20 | 50384767 | 50384896 | Hyper | blood | — | chr20 | 50720437 | 50722193 | Hyper | tcga, cancer_general, liver_tcga | — |
| chr20 | 50722598 | 50722821 | Hyper | cancer_general, liver_tcga | ZFP64 | chr20 | 51589766 | 51589908 | Hyper | cancer_general | ZFP64 |
| chr20 | 52226337 | 52226366 | Hyper | literature | — | chr20 | 52311483 | 52311602 | Hyper | pancreas | TSHZ2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 52789445 | 52789475 | Hyper | cancer_general | CYP24A1 | chr20 | 52789853 | 52790155 | Hyper | tcga, liver_tcga, cancer_general | CYP24A1 |
| chr20 | 53092192 | 53092376 | Hyper | cancer_general | DOK5 | chr20 | 53093085 | 53093115 | Hyper | cancer_general | DOK5 |
| chr20 | 54578507 | 54578725 | Hyper | cancer_general | CBLN4 | chr20 | 54579892 | 54580323 | Hyper | cancer_general | CBLN4 |
| chr20 | 54580574 | 54580691 | Hyper | literature, cancer_general | CBLN4 | chr20 | 55200035 | 55200706 | Hyper | cancer_general | TFAP2C |
| chr20 | 55200922 | 55201092 | Hyper | cancer_general | TFAP2C | chr20 | 55201486 | 55201549 | Hyper | cancer_general | TFAP2C |
| chr20 | 55201764 | 55202626 | Hyper | cancer_general | TFAP2C | chr20 | 55202826 | 55203107 | Hyper | cancer_general | TFAP2C |
| chr20 | 55204322 | 55204604 | Hyper | cancer_general | TFAP2C | chr20 | 55204966 | 55205000 | Hyper | cancer_general | TFAP2C |
| chr20 | 55206056 | 55206393 | Hyper | cancer_general | TFAP2C | chr20 | 55206739 | 55206774 | Hyper | cancer_general | TFAP2C |
| chr20 | 55499496 | 55499709 | Hyper | cancer_general | — | chr20 | 55500016 | 55500085 | Hyper | cancer_general | — |
| chr20 | 55500410 | 55500949 | Hyper | cancer_general | — | chr20 | 55841134 | 55841356 | Hyper | tcga | BC037891, BMP7 |
| chr20 | 55842096 | 55842189 | Hyper | cancer_general | BC037891, BMP7 | chr20 | 56803398 | 56803441 | Hyper | cancer_general | PPP4R1L |
| chr20 | 56803842 | 56803920 | Hyper | cancer_general | PPP4R1L | chr20 | 57089452 | 57089496 | Hyper | cancer_general | APCDD1L-AS1, APCDD1L |
| chr20 | 57089804 | 57090173 | Hyper | cancer_general | APCDD1L-AS1, APCDD1L | chr20 | 57224842 | 57225307 | Hyper | cancer_general | STX16 |
| chr20 | 57484406 | 57484445 | Hyper | literature | GNAS | chr20 | 58152637 | 58152714 | Hyper | cancer_general | PHACTR3 |
| chr20 | 58179809 | 58179854 | Hyper | cancer_general | PHACTR3 | chr20 | 58180099 | 58180414 | Hyper | cancer_general | PHACTR3 |
| chr20 | 58508887 | 58508943 | Hyper | liver_tcga | PPP1R3D, FAM217B | chr20 | 59804170 | 59804235 | Hyper | pancreas | — |
| chr20 | 59826962 | 59827226 | Hyper | literature, cancer_general | CDH4 | chr20 | 59827795 | 59828446 | Hyper | literature, cancer_general | CDH4 |
| chr20 | 61340581 | 61340689 | Hyper | cancer_general | NTSR1 | chr20 | 61560418 | 61560922 | Hyper | cancer_general | GID8 |
| chr20 | 61585771 | 61586004 | Hyper | cancer_general | SLC17A9, GID8 | chr20 | 61636858 | 61636890 | Hyper | cancer_general | BHLHE23, LOC63930 |
| chr20 | 61637468 | 61638631 | Hyper | cancer_general | LOC63930, BHLHE23 | chr20 | 61703709 | 61703875 | Hyper | cancer_general | — |
| chr20 | 61734420 | 61734481 | Hyper | cancer_general | HAR1A, HAR1B | chr20 | 61747894 | 61747934 | Hyper | cancer_general | — |
| chr20 | 61808181 | 61808270 | Hyper | cancer_general | MIR124-3 | chr20 | 61808485 | 61810089 | Hyper | tcga, cancer_general | MIR124-3 |
| chr20 | 61862380 | 61862452 | Hyper | cancer_general | BIRC7, MIR3196, NKAIN4 | chr20 | 61885247 | 61885462 | Hyper | tcga | FLJ16779, NKAIN4 |
| chr20 | 61885712 | 61885744 | Hyper | cancer_general | FLJ16779, NKAIN4 | chr20 | 61886068 | 61886258 | Hyper | cancer_general | FLJ16779, NKAIN4 |
| chr20 | 61886725 | 61886755 | Hyper | cancer_general | FLJ16779, NKAIN4 | chr20 | 62058700 | 62058786 | Hyper | cancer_general | NKAIN4, KCNQ2 |
| chr20 | 62119339 | 62120171 | Hyper | cancer_general | EEF1A2 | chr20 | 62185386 | 62185444 | Hyper | tcga, liver_tcga | C20orf195 HELZ2, SRMS |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 62284487 | 62284615 | Hyper | liver_tcga | RTEL1, RTEL1-TNFRSF6B, STMN3 | chr20 | 62461349 | 62461475 | Hyper | cancer_general | BC002534, ZBTB46 |
| chr20 | 62680657 | 62680739 | Hyper | esophageal | TCEA2, SOX18, LINC00176 | chr20 | 62715014 | 62715069 | Hyper | esophageal | OPRL1, C20orf201, RGS19 |
| chr16 | 215416 | 216224 | Hyper | cancer_general | HBM, HBA2 | chr16 | 216676 | 217036 | Hyper | cancer_general | HBA2, HBA1, HBM |
| chr16 | 230265 | 230610 | Hyper | tcga, liver_tcga, cancer_general | LUC7L, HBA1, HBA2, HBQ1 | chr16 | 565492 | 565623 | Hyper | liver_tcga | RAB11FIP3 |
| chr16 | 1030302 | 1030655 | Hyper | tcga, cancer_general | SOX8, LMF1 | chr16 | 1122858 | 1122951 | Hyper | tcga | BC084558, SSTR5, SSTR5-AS1 |
| chr16 | 1203970 | 1204034 | Hyper | cancer_general | CACNA1H IGFALS, NUBP2, SPSB3 | chr16 | 1382901 | 1382940 | Hyper | cancer_general | BALAP3 ZNF598, SYNGR3, GFER, NOXO1 |
| chr16 | 1842490 | 1842519 | Hyper | liver_tcga | | chr16 | 2040914 | 2042160 | Hyper | cancer_general | TSC2, NTHL1 |
| chr16 | 2086831 | 2086860 | Hyper | liver_tcga | NTHL1, SLC9A3R2 | chr16 | 2106703 | 2106732 | Hyper | literature | TSC2, NTHL1 |
| chr16 | 2111966 | 2111995 | Hyper | literature | TSC2 | chr16 | 2120515 | 2120544 | Hyper | literature | — |
| chr16 | 2122243 | 2122272 | Hyper | literature | — | chr16 | 2124205 | 2124348 | Hyper | literature | TSC2 |
| chr16 | 2126080 | 2126109 | Hyper | literature | TSC2 | chr16 | 2130361 | 2130390 | Hyper | literature | TSC2, PKD1, MIR1225 |
| chr16 | 2132244 | 2132315 | Hyper | liver_tcga | TSC2, PKD1, MIR1225 | chr16 | 2135301 | 2135330 | Hyper | literature | PKD1, MIR1225, TSC2 |
| chr16 | 2136228 | 2136257 | Hyper | literature | TSC2, PKD1, MIR1225 | chr16 | 2136727 | 2136855 | Hyper | literature | PKD1, MIR1225, TSC2 |
| chr16 | 2140403 | 2140438 | Hyper | liver_tcga | PKD1, MIR1225, TSC2 | chr16 | 2287295 | 2287370 | Hyper | cancer_general | MIR1225 |
| chr16 | 2892542 | 2892729 | Hyper | cancer_general | PRSS22, PRSS30P | chr16 | 3017052 | 3017628 | Hyper | cancer_general | ECI1, DNASE1L2, E4F1 |
| chr16 | 3068171 | 3068201 | Hyper | cancer_general | TNFRSF12A, HCFC1R1, THOC6, CCDC64B, CLDN6, CLDN9 | chr16 | 3220566 | 3222239 | Hyper | cancer_general, tcga | PAQR4, PKMYT1, KREMEN2 |
| chr16 | 3225471 | 3225607 | Hyper | cancer_general | TRNA_Lys, TRNA_Pro, TRNA_Pseudo | chr16 | 3232739 | 3234452 | Hyper | liver_tcga, cancer_general | TRNA_Pro, TRNA_Lys, TRNA_Pseudo |
| | | | | | | | | | | | TRNA_Pro, TRNA_Lys, TRNA_Arg |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 3237857 | 3238546 | Hyper | liver_tga, cancer_general | TRNA_Pro, TRNA_Lys, TRNA_Arg, TRNA_Pseudo | chr16 | 3238993 | 3239848 | Hyper | tcga, cancer_general | TRNA_Pro, TRNA_Lys, TRNA_Arg, TRNA_Pseudo |
| chr16 | 3241549 | 3241663 | Hyper | cancer_general | TRNA_Pseudo, TRNA_Lys, TRNA_Pro, TRNA_Arg | chr16 | 3241936 | 3241966 | Hyper | cancer_general | TRNA_Arg, TRNA_Pseudo, TRNA_Lys, TRNA_Pro |
| chr16 | 3355279 | 3355718 | Hyper | cancer_general | ZNF75A, TIGD7, ZNF263 | chr16 | 4431487 | 4431516 | Hyper | liver_tcga | VASN, CORO7-PAM16, CORO7 |
| chr16 | 4731638 | 4731718 | Hyper | liver_tga | — | chr16 | 4733166 | 4733195 | Hyper | liver_tcga | — |
| chr16 | 4738567 | 4738680 | Hyper | liver_tga | NUDT16L1, ANKS3 | chr16 | 4751554 | 4751583 | Hyper | liver_tcga | ANKS3, NUDT16L1 |
| chr16 | 5037900 | 5038004 | Hyper | cancer_general | SEC14L5 | chr16 | 6069925 | 6070019 | Hyper | cancer_general | RBFOX1 |
| chr16 | 7354634 | 7354664 | Hyper | cancer_general | RBFOX1 | chr16 | 9107184 | 9107213 | Hyper | liver_tcga, literature | — |
| chr16 | 10274399 | 10274429 | Hyper | cancer_general | GRIN2A | chr16 | 10275308 | 10275392 | Hyper | cancer_general | GRIN2A |
| chr16 | 10275752 | 10275948 | Hyper | tcga | GRIN2A | chr16 | 10276360 | 10277437 | Hyper | cancer_general, colorectal | GRIN2A |
| chr16 | 10479815 | 10479980 | Hyper | cancer_general | ATF7IP2 | chr16 | 12994459 | 12994737 | Hyper | cancer_general | SHISA9 |
| chr16 | 12995062 | 12995593 | Hyper | cancer_general, tcga | SHISA9 | chr16 | 12995803 | 12996328 | Hyper | tcga, cancer_general | SHISA9 |
| chr16 | 12996617 | 12996720 | Hyper | cancer_general | SHISA9 | chr16 | 12996948 | 12997011 | Hyper | pancreas | SHISA9 |
| chr16 | 12997386 | 12997703 | Hyper | cancer_general | SHISA9 | chr16 | 14021974 | 14022003 | Hyper | literature | ERCC4 |
| chr16 | 14041504 | 14041533 | Hyper | literature | ERCC4 | chr16 | 14041795 | 14041824 | Hyper | literature | ERCC4 |
| chr16 | 14042062 | 14042091 | Hyper | literature | ERCC4 | chr16 | 15489599 | 15489808 | Hyper | tcga | MPV17L |
| chr16 | 19567202 | 19567449 | Hyper | cancer_general | C16orf62, CCP110 | chr16 | 19895125 | 19895155 | Hyper | cancer_general | GPRC5B |
| chr16 | 21831621 | 21831957 | Hyper | tcga | RRN3P1 | chr16 | 22824701 | 22825094 | Hyper | cancer_general | HS3ST2 |
| chr16 | 22825327 | 22826081 | Hyper | cancer_general | HS3ST2 | chr16 | 23313464 | 23313522 | Hyper | esophageal | SCNN1B |
| chr16 | 23313749 | 23313836 | Hyper | esophageal | SCNN1B | chr16 | 23706317 | 23706520 | Hyper | cancer_general | ERN2, PLK1 |
| chr16 | 23766097 | 23766130 | Hyper | tcga | CHP2 | chr16 | 23847309 | 23847956 | Hyper | liver_tcga, cancer_general | PRKCB |
| chr16 | 24267115 | 24267208 | Hyper | cancer_general | CACNG3 | chr16 | 24267485 | 24267578 | Hyper | cancer_general | CACNG3 |
| chr16 | 25702955 | 25702992 | Hyper | cancer_general | HS3ST4 | chr16 | 25703642 | 25704628 | Hyper | cancer_general, tcga | HS3ST4 |
| chr16 | 28074176 | 28074684 | Hyper | tcga, cancer_general | — | chr16 | 28074959 | 28075197 | Hyper | tcga | — |
| chr16 | 28891040 | 28891072 | Hyper | esophageal | SH2B1, PAT2A1, LOC100289092 | chr16 | 29888136 | 29888227 | Hyper | cancer_general | SEZ6L2, CDIPT-AS1 |
| chr16 | 29888624 | 29888658 | Hyper | cancer_general | SEZ6L2, CDIPT-AS1 | chr16 | 31227914 | 31228313 | Hyper | tcga, cancer_general | PYDC1, TRIM72 |
| chr16 | 31580560 | 31581036 | Hyper | literature, cancer_general | YBX3P1 | chr16 | 47177525 | 47177606 | Hyper | hepatobiliary | — |
| chr16 | 48844792 | 48845125 | Hyper | cancer_general | — | chr16 | 49309170 | 49309262 | Hyper | cancer_general | CBLN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 49311523 | 49312299 | Hyper | cancer_general | CBLN1 | chr16 | 49313363 | 49313710 | Hyper | cancer_general | CBLN1 |
| chr16 | 49314022 | 49314118 | Hyper | cancer_general | CBLN1 | chr16 | 49314419 | 49314561 | Hyper | cancer_general | CBLN1 |
| chr16 | 49314784 | 49314837 | Hyper | cancer_general | CBLN1 | chr16 | 49315276 | 49315306 | Hyper | cancer_general | CBLN1 |
| chr16 | 49315919 | 49316580 | Hyper | cancer_general | SALL1 | chr16 | 51183900 | 51184406 | Hyper | tcga, cancer_general | SALL1 |
| chr16 | 51184807 | 51185360 | Hyper | literature, cancer_general | SALL1 | chr16 | 51185844 | 51186280 | Hyper | | SALL1 |
| chr16 | 51186592 | 51186939 | Hyper | cancer_general | SALL1 | chr16 | 51188682 | 51188711 | Hyper | literature | SALL1 |
| chr16 | 51189922 | 51190215 | Hyper | cancer_general | SALL1 | chr16 | 54318898 | 54318988 | Hyper | cancer_general | IRX3 |
| chr16 | 54319420 | 54319468 | Hyper | cancer_general | IRX3 | chr16 | 54321638 | 54321834 | Hyper | cancer_general | IRX3 |
| chr16 | 54324999 | 54325131 | Hyper | cancer_general | IRX3 | chr16 | 54628691 | 54628867 | Hyper | cancer_general | — |
| chr16 | 54964948 | 54965114 | Hyper | blood | IRX5, CRNDE | chr16 | 54960830 | 54967403 | Hyper | liver_tcga, cancer_general | IRX5, CRNDE |
| chr16 | 54971060 | 54971090 | Hyper | cancer_general | IRX5, CRNDE | chr16 | 54971400 | 54971430 | Hyper | cancer_general | IRX5, CRNDE |
| chr16 | 55090666 | 55090861 | Hyper | cancer_general | — | chr16 | 55357926 | 55358086 | Hyper | cancer_general | IRX6 |
| chr16 | 55358316 | 55358528 | Hyper | cancer_general | IRX6 | chr16 | 55358798 | 55359071 | Hyper | cancer_general | IRX6 |
| chr16 | 55363009 | 55363223 | Hyper | cancer_general | IRX6 | chr16 | 55364716 | 55364843 | Hyper | cancer_general | IRX6 |
| chr16 | 55365103 | 55365234 | Hyper | cancer_general | MMP2 | chr16 | 55404999 | 55405214 | Hyper | tcga | SLC6A2 |
| chr16 | 55512843 | 55512884 | Hyper | cancer_general | SLC6A2 | chr16 | 55689886 | 55689915 | Hyper | tcga | GNAO1, DKFZP434H168, LOC283856 |
| chr16 | 55690115 | 55690809 | Hyper | tcga, cancer_general | | chr16 | 56224557 | 56224879 | Hyper | cancer_general | |
| chr16 | 56228370 | 56228581 | Hyper | cancer_general, tcga | DKFZP434H168, GNAO1, LOC283856 | chr16 | 56651094 | 56651275 | Hyper | cancer_general | MT1L, MT1M, MT1E, MT1A, MT2A |
| chr16 | 56659175 | 56659673 | Hyper | cancer_general | MT1E, MT1M, MT1JP, MT1L, MT1A | chr16 | 56672158 | 56672654 | Hyper | tcga, cancer_general | MT1A, MT1DP, MT1JP, MT1M |
| chr16 | 56709837 | 56710030 | Hyper | cancer_general | MT1G, MT1E, MT1X, MT1JP, MT1H | chr16 | 57318379 | 57318412 | Hyper | blood | PLLP |
| chr16 | 58018634 | 58018845 | Hyper | cancer_general | ZNF319, TEPP | chr16 | 58019225 | 58019430 | Hyper | cancer_general | ZNF319, TEPP |
| chr16 | 58497221 | 58497409 | Hyper | literature | NDRG4 | chr16 | 58497752 | 58497829 | Hyper | literature | NDRG4 |
| chr16 | 58498175 | 58498204 | Hyper | literature | NDRG4 | chr16 | 58498570 | 58498724 | Hyper | literature | NDRG4 |
| chr16 | 58521708 | 58521737 | Hyper | literature | NDRG4 | chr16 | 58534666 | 58534695 | Hyper | literature | NDRG4 |
| chr16 | 62068463 | 62068517 | Hyper | cancer_general | — | chr16 | 62068952 | 62068982 | Hyper | cancer_general | — |
| chr16 | 62070743 | 62070773 | Hyper | cancer_general | — | chr16 | 65154933 | 65155091 | Hyper | cancer_general | BEAN1 |
| chr16 | 65156385 | 65156489 | Hyper | cancer_general | CMTM2, CMTM1 | chr16 | 66461786 | 66461840 | Hyper | cancer_general | HSF4, NOL3, FBXL8, TRADD |
| chr16 | 66612882 | 66613369 | Hyper | cancer_general, tcga | CMTM2, CMTM1 | chr16 | 67197698 | 67197769 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 67198009 | 67198039 | Hyper | cancer_general | HSF4, NOL3, FBXL8, TRADD | chr16 | 67198917 | 67198957 | Hyper | cancer_general | HSF4, FBXL8, TRADD, NOL3 |
| chr16 | 68481486 | 68481543 | Hyper | liver_tcga | SMPD3 | chr16 | 68482808 | 68482941 | Hyper | liver_tcga | SMPD3 |
| chr16 | 68544259 | 68544378 | Hyper | cancer_general | — | chr16 | 68676408 | 68676984 | Hyper | cancer_general | CDH3 |
| chr16 | 68770966 | 68771298 | Hyper | literature, blood | CDH1 | chr16 | 68844158 | 68844187 | Hyper | literature | CDH1 |
| chr16 | 68846033 | 68846062 | Hyper | literature | CDH1 | chr16 | 68856078 | 68856107 | Hyper | literature | CDH1 |
| chr16 | 71460027 | 71460351 | Hyper | cancer_general | TRNA_Met | chr16 | 73100460 | 73100524 | Hyper | cancer_general | — |
| chr16 | 77468261 | 77468775 | Hyper | cancer_general | ADAMTS18 | chr16 | 77822589 | 77822874 | Hyper | cancer_general | VAT1L |
| chr16 | 78079969 | 78080054 | Hyper | cancer_general | — | chr16 | 79623602 | 79623914 | Hyper | tcga, lung, cancer_general | MAF |
| chr16 | 80837962 | 80838143 | Hyper | esophageal | CDYL2 | chr16 | 80966399 | 80966431 | Hyper | blood | — |
| chr16 | 81946246 | 81946275 | Hyper | literature | PLCG2 | chr16 | 81962167 | 81962196 | Hyper | literature | PLCG2 |
| chr16 | 82660360 | 82660496 | Hyper | cancer_general, literature | CDH13 | chr16 | 82660712 | 82660741 | Hyper | literature | CDH13 |
| chr16 | 84402244 | 84402319 | Hyper | blood | ATP2C2 | chr16 | 84651793 | 84651822 | Hyper | liver_tcga | COTL1 |
| chr16 | 84853288 | 84853376 | Hyper | blood | CRISPLD2 | chr16 | 85932828 | 85932858 | Hyper | cancer_general | IRF8 |
| chr16 | 86320354 | 86320391 | Hyper | cancer_general | LOC146513 | chr16 | 86320755 | 86320800 | Hyper | cancer_general | LOC146513 |
| chr16 | 86321020 | 86321068 | Hyper | cancer_general, literature | LOC146513 | chr16 | 86530947 | 86531046 | Hyper | cancer_general | FENDRR |
| chr16 | 86531310 | 86531573 | Hyper | cancer_general | FENDRR | chr16 | 86541591 | 86541968 | Hyper | cancer_general | FOXF1, FENDRR |
| chr16 | 86542373 | 86542457 | Hyper | cancer_general | FOXF1, FENDRR | chr16 | 86544191 | 86544972 | Hyper | cancer_general | FENDRR, FOXF1 |
| chr16 | 86599477 | 86599844 | Hyper | cancer_general | FOXC2, FLJ30679 | chr16 | 86600483 | 86600686 | Hyper | cancer_general | FLJ30679, FOXC2 |
| chr16 | 86600958 | 86601015 | Hyper | cancer_general | FOXC2, FOXL1 | chr16 | 86601286 | 86601539 | Hyper | cancer_general | FOXC2 |
| chr16 | 86601945 | 86602514 | Hyper | cancer_general | FOXC2, FOXL1 | chr16 | 86613052 | 86613108 | Hyper | tcga | FOXL1 |
| chr16 | 87525622 | 87525701 | Hyper | blood | BC131758 | chr16 | 87635103 | 87635133 | Hyper | cancer_general | JPH3 |
| chr16 | 87636518 | 87636907 | Hyper | cancer_general, tcga | JPH3 | chr16 | 88543428 | 88543458 | Hyper | liver_tcga | MIR5189, ZFPM1 |
| chr16 | 89007520 | 89007558 | Hyper | pancreas | CBFA2T3 | chr16 | 89007880 | 89007995 | Hyper | esophageal | CBFA2T3 |
| chr16 | 89008562 | 89008592 | Hyper | pancreas | CBFA2T3 | chr16 | 89267334 | 89267364 | Hyper | cancer_general | CDH15, SLC22A31 |
| chr16 | 89267808 | 89267847 | Hyper | cancer_general | SLC22A31, CDH15 | JH636052.4 | 5118769 | 5118903 | Hyper | cancer_general | — |
| EBV-B95-8 | 967 | 996 | Hyper | virus | — | EBV-B95-8 | 3766 | 3795 | Hyper | virus | — |
| EBV-B95-8 | 4234 | 4263 | Hyper | virus | — | EBV-B95-8 | 5326 | 5355 | Hyper | virus | — |
| EBV-B95-8 | 6553 | 6582 | Hyper | virus | — | EBV-B95-8 | 8800 | 8829 | Hyper | virus | — |
| EBV-B95-8 | 13471 | 13500 | Hyper | virus | — | EBV-B95-8 | 46577 | 46606 | Hyper | virus | — |
| EBV-B95-8 | 48222 | 48251 | Hyper | virus | — | EBV-B95-8 | 52842 | 52871 | Hyper | virus | — |
| EBV-B95-8 | 53561 | 53590 | Hyper | virus | — | EBV-B95-8 | 54377 | 54406 | Hyper | virus | — |
| EBV-B95-8 | 54778 | 54807 | Hyper | virus | — | EBV-B95-8 | 55067 | 55096 | Hyper | virus | — |
| EBV-B95-8 | 55893 | 55922 | Hyper | virus | — | EBV-B95-8 | 56735 | 56764 | Hyper | virus | — |
| EBV-B95-8 | 58227 | 58256 | Hyper | virus | — | EBV-B95-8 | 58926 | 58955 | Hyper | virus | — |
| EBV-B95-8 | 59581 | 59610 | Hyper | virus | — | EBV-B95-8 | 60099 | 60128 | Hyper | virus | — |
| EBV-B95-8 | 60877 | 60906 | Hyper | virus | — | EBV-B95-8 | 61319 | 61348 | Hyper | virus | — |
| EBV-B95-8 | 62302 | 62331 | Hyper | virus | — | EBV-B95-8 | 62840 | 62869 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| EBV-B95-8 | 63178 | 63207 | Hyper | virus | — | EBV-B95-8 | 63601 | 63630 | Hyper | virus | — |
| EBV-B95-8 | 63935 | 63964 | Hyper | virus | — | EBV-B95-8 | 64590 | 64619 | Hyper | virus | — |
| EBV-B95-8 | 66726 | 66755 | Hyper | virus | — | EBV-B95-8 | 67486 | 67515 | Hyper | virus | — |
| EBV-B95-8 | 67857 | 67886 | Hyper | virus | — | EBV-B95-8 | 69228 | 69257 | Hyper | virus | — |
| EBV-B95-8 | 69798 | 69827 | Hyper | virus | — | EBV-B95-8 | 70439 | 70468 | Hyper | virus | — |
| EBV-B95-8 | 70839 | 70868 | Hyper | virus | — | EBV-B95-8 | 71938 | 71967 | Hyper | virus | — |
| EBV-B95-8 | 72204 | 72233 | Hyper | virus | — | EBV-B95-8 | 72535 | 72564 | Hyper | virus | — |
| EBV-B95-8 | 72983 | 73012 | Hyper | virus | — | EBV-B95-8 | 73950 | 73979 | Hyper | virus | — |
| EBV-B95-8 | 74304 | 74333 | Hyper | virus | — | EBV-B95-8 | 74689 | 74718 | Hyper | virus | — |
| EBV-B95-8 | 74978 | 75007 | Hyper | virus | — | EBV-B95-8 | 75256 | 75285 | Hyper | virus | — |
| EBV-B95-8 | 77784 | 77813 | Hyper | virus | — | EBV-B95-8 | 79618 | 79647 | Hyper | virus | — |
| EBV-B95-8 | 80289 | 80318 | Hyper | virus | — | EBV-B95-8 | 80704 | 80733 | Hyper | virus | — |
| EBV-B95-8 | 81198 | 81227 | Hyper | virus | — | EBV-B95-8 | 81629 | 81658 | Hyper | virus | — |
| EBV-B95-8 | 81888 | 81917 | Hyper | virus | — | EBV-B95-8 | 82225 | 82254 | Hyper | virus | — |
| EBV-B95-8 | 82703 | 82732 | Hyper | virus | — | EBV-B95-8 | 83438 | 83467 | Hyper | virus | — |
| EBV-B95-8 | 85345 | 85374 | Hyper | virus | — | EBV-B95-8 | 86299 | 86328 | Hyper | virus | — |
| EBV-B95-8 | 87104 | 87133 | Hyper | virus | — | EBV-B95-8 | 89959 | 89988 | Hyper | virus | — |
| EBV-B95-8 | 90915 | 90944 | Hyper | virus | — | EBV-B95-8 | 92531 | 92560 | Hyper | virus | — |
| EBV-B95-8 | 94071 | 94100 | Hyper | virus | — | EBV-B95-8 | 94731 | 94760 | Hyper | virus | — |
| EBV-B95-8 | 95084 | 95113 | Hyper | virus | — | EBV-B95-8 | 97482 | 97511 | Hyper | virus | — |
| EBV-B95-8 | 98245 | 98274 | Hyper | virus | — | EBV-B95-8 | 99224 | 99253 | Hyper | virus | — |
| EBV-B95-8 | 100235 | 100264 | Hyper | virus | — | EBV-B95-8 | 101009 | 101038 | Hyper | virus | — |
| EBV-B95-8 | 102716 | 102745 | Hyper | virus | — | EBV-B95-8 | 104004 | 104033 | Hyper | virus | — |
| EBV-B95-8 | 105019 | 105048 | Hyper | virus | — | EBV-B95-8 | 105284 | 105313 | Hyper | virus | — |
| EBV-B95-8 | 107231 | 107260 | Hyper | virus | — | EBV-B95-8 | 108023 | 108052 | Hyper | virus | — |
| EBV-B95-8 | 108370 | 108399 | Hyper | virus | — | EBV-B95-8 | 109086 | 109115 | Hyper | virus | — |
| EBV-B95-8 | 110250 | 110279 | Hyper | virus | — | EBV-B95-8 | 110626 | 110655 | Hyper | virus | — |
| EBV-B95-8 | 111690 | 111719 | Hyper | virus | — | EBV-B95-8 | 112112 | 112141 | Hyper | virus | — |
| EBV-B95-8 | 114429 | 114458 | Hyper | virus | — | EBV-B95-8 | 114749 | 114778 | Hyper | virus | — |
| EBV-B95-8 | 115006 | 115035 | Hyper | virus | — | EBV-B95-8 | 115597 | 115626 | Hyper | virus | — |
| EBV-B95-8 | 116382 | 116411 | Hyper | virus | — | EBV-B95-8 | 116649 | 116678 | Hyper | virus | — |
| EBV-B95-8 | 118647 | 118676 | Hyper | virus | — | EBV-B95-8 | 119542 | 119571 | Hyper | virus | — |
| EBV-B95-8 | 120350 | 120379 | Hyper | virus | — | EBV-B95-8 | 121382 | 121411 | Hyper | virus | — |
| EBV-B95-8 | 123037 | 123066 | Hyper | virus | — | EBV-B95-8 | 123570 | 123599 | Hyper | virus | — |
| EBV-B95-8 | 124913 | 124942 | Hyper | virus | — | EBV-B95-8 | 125376 | 125405 | Hyper | virus | — |
| EBV-B95-8 | 125805 | 125834 | Hyper | virus | — | EBV-B95-8 | 126337 | 126366 | Hyper | virus | — |
| EBV-B95-8 | 127493 | 127522 | Hyper | virus | — | EBV-B95-8 | 127905 | 127934 | Hyper | virus | — |
| EBV-B95-8 | 128805 | 128834 | Hyper | virus | — | EBV-B95-8 | 130244 | 130273 | Hyper | virus | — |
| EBV-B95-8 | 130690 | 130719 | Hyper | virus | — | EBV-B95-8 | 131603 | 131632 | Hyper | virus | — |
| EBV-B95-8 | 134325 | 134354 | Hyper | virus | — | EBV-B95-8 | 135032 | 135061 | Hyper | virus | — |
| EBV-B95-8 | 135599 | 135628 | Hyper | virus | — | EBV-B95-8 | 136148 | 136177 | Hyper | virus | — |
| EBV-B95-8 | 136680 | 136709 | Hyper | virus | — | EBV-B95-8 | 137805 | 137834 | Hyper | virus | — |
| EBV-B95-8 | 138375 | 138404 | Hyper | virus | — | EBV-B95-8 | 139745 | 139774 | Hyper | virus | — |
| EBV-B95-8 | 140610 | 140639 | Hyper | virus | — | EBV-B95-8 | 141137 | 141166 | Hyper | virus | — |
| EBV-B95-8 | 142290 | 142319 | Hyper | virus | — | EBV-B95-8 | 142763 | 142792 | Hyper | virus | — |
| EBV-B95-8 | 143078 | 143107 | Hyper | virus | — | EBV-B95-8 | 144318 | 144347 | Hyper | virus | — |
| EBV-B95-8 | 145216 | 145245 | Hyper | virus | — | EBV-B95-8 | 145638 | 145667 | Hyper | virus | — |
| EBV-B95-8 | 147044 | 147073 | Hyper | virus | — | EBV-B95-8 | 148404 | 148433 | Hyper | virus | — |
| EBV-B95-8 | 150099 | 150128 | Hyper | virus | — | EBV-B95-8 | 150443 | 150472 | Hyper | virus | — |
| EBV-B95-8 | 152230 | 152259 | Hyper | virus | — | EBV-B95-8 | 153127 | 153156 | Hyper | virus | — |

TABLE 11-continued

| chr | Start | Stop | Hypo/hyper | classification | annotation |
|---|---|---|---|---|---|
| EBV-B95-8 | 153468 | 153497 | Hyper | virus | — |
| EBV-B95-8 | 154204 | 154233 | Hyper | virus | — |
| EBV-B95-8 | 156773 | 156802 | Hyper | virus | — |
| EBV-B95-8 | 159211 | 159240 | Hyper | virus | — |
| EBV-B95-8 | 161193 | 161222 | Hyper | virus | — |
| EBV-B95-8 | 162343 | 162372 | Hyper | virus | — |
| EBV-B95-8 | 164471 | 164500 | Hyper | virus | — |
| EBV-B95-8 | 166280 | 166309 | Hyper | virus | — |
| EBV-B95-8 | 167600 | 167629 | Hyper | virus | — |
| EBV-B95-8 | 168551 | 168580 | Hyper | virus | — |
| HHV5-CINCY-TOWNE | 1181 | 1210 | Hyper | virus | — |
| HHV5-CINCY-TOWNE | 2389 | 2418 | Hyper | virus | — |
| HHV5-CINCY-TOWNE | 3665 | 3694 | Hyper | virus | — |
| HHV5-CINCY-TOWNE | 5400 | 5429 | Hyper | virus | — |
| HHV5-CINCY-TOWNE | 9656 | 9685 | Hyper | virus | — |
| HHV5-CINCY-TOWNE | 11109 | 11138 | Hyper | virus | — |
| HHV5-CINCY-TOWNE | 13688 | 13717 | Hyper | virus | — |
| HHV5-CINCY-TOWNE | 14911 | 14940 | Hyper | virus | — |
| HHV5-CINCY-TOWNE | 15938 | 15967 | Hyper | virus | — |
| HHV5-CINCY-TOWNE | 16884 | 16913 | Hyper | virus | — |
| HHV5-CINCY-TOWNE | 17696 | 17725 | Hyper | virus | — |
| HHV5-CINCY-TOWNE | 18372 | 18401 | Hyper | virus | — |
| HHV5-CINCY-TOWNE | 19910 | 19939 | Hyper | virus | — |
| EBV-B95-8 | 153800 | 153829 | Hyper | virus | — |
| EBV-B95-8 | 156501 | 156530 | Hyper | virus | — |
| EBV-B95-8 | 157345 | 157374 | Hyper | virus | — |
| EBV-B95-8 | 159561 | 159590 | Hyper | virus | — |
| EBV-B95-8 | 161698 | 161727 | Hyper | virus | — |
| EBV-B95-8 | 163798 | 163827 | Hyper | virus | — |
| EBV-B95-8 | 165234 | 165263 | Hyper | virus | — |
| EBV-B95-8 | 167347 | 167376 | Hyper | virus | — |
| EBV-B95-8 | 167942 | 167971 | Hyper | virus | — |
| EBV-B95-8 | 171304 | 171333 | Hyper | virus | — |
| HHV5-CINCY-TOWNE | 1988 | 2017 | Hyper | virus | — |
| HHV5-CINCY-TOWNE | 3290 | 3319 | Hyper | virus | — |
| HHV5-CINCY-TOWNE | 4704 | 4733 | Hyper | virus | — |
| HHV5-CINCY-TOWNE | 7790 | 7819 | Hyper | virus | — |
| HHV5-CINCY-TOWNE | 10781 | 10810 | Hyper | virus | — |
| HHV5-CINCY-TOWNE | 12663 | 12692 | Hyper | virus | — |
| HHV5-CINCY-TOWNE | 14223 | 14252 | Hyper | virus | — |
| HHV5-CINCY-TOWNE | 15206 | 15235 | Hyper | virus | — |
| HHV5-CINCY-TOWNE | 16440 | 16469 | Hyper | virus | — |
| HHV5-CINCY-TOWNE | 17347 | 17376 | Hyper | virus | — |
| HHV5-CINCY-TOWNE | 17958 | 17987 | Hyper | virus | — |
| HHV5-CINCY-TOWNE | 19417 | 19446 | Hyper | virus | — |
| HHV5-CINCY-TOWNE | 20248 | 20277 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 20671 | 20700 | Hyper | virus | — | HHV5-CINCY-TOWNE | 21899 | 21928 | Hyper | virus | — |
| HHV5-CINCY-TOWNE | 22798 | 22827 | Hyper | virus | — | HHV5-CINCY-TOWNE | 23095 | 23124 | Hyper | virus | — |
| HHV5-CINCY-TOWNE | 26713 | 26742 | Hyper | virus | — | HHV5-CINCY-TOWNE | 27211 | 27240 | Hyper | virus | — |
| HHV5-CINCY-TOWNE | 29784 | 29813 | Hyper | virus | — | HHV5-CINCY-TOWNE | 31141 | 31170 | Hyper | virus | — |
| HHV5-CINCY-TOWNE | 32660 | 32689 | Hyper | virus | — | HHV5-CINCY-TOWNE | 35651 | 35680 | Hyper | virus | — |
| HHV5-CINCY-TOWNE | 36393 | 36422 | Hyper | virus | — | HHV5-CINCY-TOWNE | 37224 | 37253 | Hyper | virus | — |
| HHV5-CINCY-TOWNE | 37895 | 37924 | Hyper | virus | — | HHV5-CINCY-TOWNE | 39244 | 39273 | Hyper | virus | — |
| HHV5-CINCY-TOWNE | 43188 | 43217 | Hyper | virus | — | HHV5-CINCY-TOWNE | 44447 | 44476 | Hyper | virus | — |
| HHV5-CINCY-TOWNE | 44799 | 44828 | Hyper | virus | — | HHV5-CINCY-TOWNE | 45394 | 45423 | Hyper | virus | — |
| HHV5-CINCY-TOWNE | 46445 | 46474 | Hyper | virus | — | HHV5-CINCY-TOWNE | 46944 | 46973 | Hyper | virus | — |
| HHV5-CINCY-TOWNE | 47916 | 47945 | Hyper | virus | — | HHV5-CINCY-TOWNE | 48504 | 48533 | Hyper | virus | — |
| HHV5-CINCY-TOWNE | 49094 | 49123 | Hyper | virus | — | HHV5-CINCY-TOWNE | 49903 | 49932 | Hyper | virus | — |
| HHV5-CINCY-TOWNE | 50230 | 50259 | Hyper | virus | — | HHV5-CINCY-TOWNE | 51421 | 51450 | Hyper | virus | — |
| HHV5-CINCY-TOWNE | 53772 | 53801 | Hyper | virus | — | HHV5-CINCY-TOWNE | 55651 | 55680 | Hyper | virus | — |
| HHV5-CINCY-TOWNE | 56380 | 56409 | Hyper | virus | — | HHV5-CINCY-TOWNE | 57291 | 57320 | Hyper | virus | — |
| HHV5-CINCY-TOWNE | 58491 | 58520 | Hyper | virus | — | HHV5-CINCY-TOWNE | 59023 | 59052 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 59792 | 59821 | Hyper | virus | — | HHV5-CINCY-TOWNE | 60124 | 60153 | Hyper | virus | — |
| HHV5-CINCY-TOWNE | 60392 | 60421 | Hyper | virus | — | HHV5-CINCY-TOWNE | 60900 | 60929 | Hyper | virus | — |
| HHV5-CINCY-TOWNE | 63894 | 63923 | Hyper | virus | — | HHV5-CINCY-TOWNE | 65843 | 65872 | Hyper | virus | — |
| HHV5-CINCY-TOWNE | 68089 | 68118 | Hyper | virus | — | HHV5-CINCY-TOWNE | 72454 | 72483 | Hyper | virus | — |
| HHV5-CINCY-TOWNE | 81185 | 81214 | Hyper | virus | — | HHV5-CINCY-TOWNE | 84144 | 84173 | Hyper | virus | — |
| HHV5-CINCY-TOWNE | 85524 | 85553 | Hyper | virus | — | HHV5-CINCY-TOWNE | 85943 | 85972 | Hyper | virus | — |
| HHV5-CINCY-TOWNE | 86889 | 86918 | Hyper | virus | — | HHV5-CINCY-TOWNE | 87195 | 87224 | Hyper | virus | — |
| HHV5-CINCY-TOWNE | 87455 | 87484 | Hyper | virus | — | HHV5-CINCY-TOWNE | 87769 | 87798 | Hyper | virus | — |
| HHV5-CINCY-TOWNE | 88564 | 88593 | Hyper | virus | — | HHV5-CINCY-TOWNE | 93096 | 93125 | Hyper | virus | — |
| HHV5-CINCY-TOWNE | 93776 | 93805 | Hyper | virus | — | HHV5-CINCY-TOWNE | 97621 | 97650 | Hyper | virus | — |
| HHV5-CINCY-TOWNE | 98737 | 98766 | Hyper | virus | — | HHV5-CINCY-TOWNE | 99460 | 99489 | Hyper | virus | — |
| HHV5-CINCY-TOWNE | 107540 | 107569 | Hyper | virus | — | HHV5-CINCY-TOWNE | 108823 | 108852 | Hyper | virus | — |
| HHV5-CINCY-TOWNE | 109725 | 109754 | Hyper | virus | — | HHV5-CINCY-TOWNE | 112036 | 112065 | Hyper | virus | — |
| HHV5-CINCY-TOWNE | 112319 | 112348 | Hyper | virus | — | HHV5-CINCY-TOWNE | 112595 | 112624 | Hyper | virus | — |
| HHV5-CINCY-TOWNE | 112892 | 112921 | Hyper | virus | — | HHV5-CINCY-TOWNE | 113194 | 113223 | Hyper | virus | — |
| HHV5-CINCY-TOWNE | 113535 | 113564 | Hyper | virus | — | HHV5-CINCY-TOWNE | 113927 | 113956 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 114267 | 114296 | Hyper | virus | — | HHV5-CINCY-TOWNE | 114593 | 114622 | Hyper | virus | — |
| HHV5-CINCY-TOWNE | 114867 | 114896 | Hyper | virus | — | HHV5-CINCY-TOWNE | 115177 | 115206 | Hyper | virus | — |
| HHV5-CINCY-TOWNE | 115432 | 115461 | Hyper | virus | — | HHV5-CINCY-TOWNE | 115685 | 115714 | Hyper | virus | — |
| HHV5-CINCY-TOWNE | 115986 | 116015 | Hyper | virus | — | HHV5-CINCY-TOWNE | 116382 | 116411 | Hyper | virus | — |
| HHV5-CINCY-TOWNE | 116700 | 116729 | Hyper | virus | — | HHV5-CINCY-TOWNE | 118193 | 118222 | Hyper | virus | — |
| HHV5-CINCY-TOWNE | 118995 | 119024 | Hyper | virus | — | HHV5-CINCY-TOWNE | 120028 | 120057 | Hyper | virus | — |
| HHV5-CINCY-TOWNE | 121485 | 121514 | Hyper | virus | — | HHV5-CINCY-TOWNE | 122199 | 122228 | Hyper | virus | — |
| HHV5-CINCY-TOWNE | 122606 | 122635 | Hyper | virus | — | HHV5-CINCY-TOWNE | 124559 | 124588 | Hyper | virus | — |
| HHV5-CINCY-TOWNE | 125276 | 125305 | Hyper | virus | — | HHV5-CINCY-TOWNE | 132497 | 132526 | Hyper | virus | — |
| HHV5-CINCY-TOWNE | 135460 | 135489 | Hyper | virus | — | HHV5-CINCY-TOWNE | 135730 | 135759 | Hyper | virus | — |
| HHV5-CINCY-TOWNE | 137379 | 137408 | Hyper | virus | — | HHV5-CINCY-TOWNE | 139067 | 139096 | Hyper | virus | — |
| HHV5-CINCY-TOWNE | 139472 | 139501 | Hyper | virus | — | HHV5-CINCY-TOWNE | 140147 | 140176 | Hyper | virus | — |
| HHV5-CINCY-TOWNE | 140722 | 140751 | Hyper | virus | — | HHV5-CINCY-TOWNE | 142023 | 142052 | Hyper | virus | — |
| HHV5-CINCY-TOWNE | 143692 | 143721 | Hyper | virus | — | HHV5-CINCY-TOWNE | 144080 | 144109 | Hyper | virus | — |
| HHV5-CINCY-TOWNE | 147310 | 147339 | Hyper | virus | — | HHV5-CINCY-TOWNE | 149465 | 149494 | Hyper | virus | — |
| HHV5-CINCY-TOWNE | 150359 | 150388 | Hyper | virus | — | HHV5-CINCY-TOWNE | 151593 | 151622 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 152153 | 152182 | Hyper | virus | — | HHV5-CINCY-TOWNE | 154148 | 154177 | Hyper | virus | — |
| HHV5-CINCY-TOWNE | 154610 | 154639 | Hyper | virus | — | HHV5-CINCY-TOWNE | 157018 | 157047 | Hyper | virus | — |
| HHV5-CINCY-TOWNE | 157367 | 157396 | Hyper | virus | — | HHV5-CINCY-TOWNE | 169038 | 169067 | Hyper | virus | — |
| HHV5-CINCY-TOWNE | 171503 | 171532 | Hyper | virus | — | HHV5-CINCY-TOWNE | 175146 | 175175 | Hyper | virus | — |
| HHV5-CINCY-TOWNE | 177553 | 177582 | Hyper | virus | — | HHV5-CINCY-TOWNE | 182254 | 182283 | Hyper | virus | — |
| HHV5-CINCY-TOWNE | 183115 | 183144 | Hyper | virus | — | HHV5-CINCY-TOWNE | 184120 | 184149 | Hyper | virus | — |
| HHV5-CINCY-TOWNE | 185558 | 185587 | Hyper | virus | — | HHV5-CINCY-TOWNE | 186027 | 186056 | Hyper | virus | — |
| HHV5-CINCY-TOWNE | 186435 | 186464 | Hyper | virus | — | HHV5-CINCY-TOWNE | 186707 | 186736 | Hyper | virus | — |
| HHV5-CINCY-TOWNE | 187115 | 187144 | Hyper | virus | — | HHV5-CINCY-TOWNE | 187514 | 187543 | Hyper | virus | — |
| HHV5-CINCY-TOWNE | 187859 | 187888 | Hyper | virus | — | HHV5-CINCY-TOWNE | 188473 | 188502 | Hyper | virus | — |
| HHV5-CINCY-TOWNE | 188768 | 188797 | Hyper | virus | — | HHV5-CINCY-TOWNE | 189050 | 189079 | Hyper | virus | — |
| HHV5-CINCY-TOWNE | 189302 | 189331 | Hyper | virus | — | HHV5-CINCY-TOWNE | 189936 | 189965 | Hyper | virus | — |
| HHV5-CINCY-TOWNE | 190655 | 190684 | Hyper | virus | — | HHV5-CINCY-TOWNE | 190954 | 190983 | Hyper | virus | — |
| HHV5-CINCY-TOWNE | 191453 | 191482 | Hyper | virus | — | HHV5-CINCY-TOWNE | 191882 | 191911 | Hyper | virus | — |
| HHV5-CINCY-TOWNE | 192183 | 192212 | Hyper | virus | — | HHV5-CINCY-TOWNE | 192541 | 192570 | Hyper | virus | — |
| HHV5-CINCY-TOWNE | 193045 | 193074 | Hyper | virus | — | HHV5-CINCY-TOWNE | 193325 | 193354 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 193597 | 193626 | Hyper | virus | — | HHV5-CINCY-TOWNE | 194165 | 194194 | Hyper | virus | — |
| HHV5-CINCY-TOWNE | 194461 | 194490 | Hyper | virus | — | HHV5-CINCY-TOWNE | 194848 | 194877 | Hyper | virus | — |
| HHV5-CINCY-TOWNE | 195324 | 195353 | Hyper | virus | — | HHV5-CINCY-TOWNE | 195651 | 195680 | Hyper | virus | — |
| HHV5-CINCY-TOWNE | 196018 | 196047 | Hyper | virus | — | HHV5-CINCY-TOWNE | 196343 | 196372 | Hyper | virus | — |
| HHV5-CINCY-TOWNE | 196941 | 196970 | Hyper | virus | — | HHV5-CINCY-TOWNE | 197218 | 197247 | Hyper | virus | — |
| HHV5-CINCY-TOWNE | 198315 | 198344 | Hyper | virus | — | HHV5-CINCY-TOWNE | 198792 | 198821 | Hyper | virus | — |
| HHV5-CINCY-TOWNE | 199162 | 199191 | Hyper | virus | — | HHV5-CINCY-TOWNE | 200113 | 200142 | Hyper | virus | — |
| HHV5-CINCY-TOWNE | 200571 | 200600 | Hyper | virus | — | HHV5-CINCY-TOWNE | 201373 | 201402 | Hyper | virus | — |
| HHV5-CINCY-TOWNE | 201905 | 201934 | Hyper | virus | — | HHV5-CINCY-TOWNE | 202264 | 202293 | Hyper | virus | — |
| HHV5-CINCY-TOWNE | 202537 | 202566 | Hyper | virus | — | HHV5-CINCY-TOWNE | 203319 | 203348 | Hyper | virus | — |
| HHV5-CINCY-TOWNE | 203720 | 203749 | Hyper | virus | — | HHV5-CINCY-TOWNE | 204008 | 204037 | Hyper | virus | — |
| HHV5-CINCY-TOWNE | 206213 | 206242 | Hyper | virus | — | HHV5-CINCY-TOWNE | 206735 | 206764 | Hyper | virus | — |
| HHV5-CINCY-TOWNE | 211676 | 211705 | Hyper | virus | — | HHV5-CINCY-TOWNE | 212340 | 212369 | Hyper | virus | — |
| HHV5-CINCY-TOWNE | 212609 | 212638 | Hyper | virus | — | HHV5-CINCY-TOWNE | 213813 | 213842 | Hyper | virus | — |
| HHV5-CINCY-TOWNE | 214695 | 214724 | Hyper | virus | — | HHV5-CINCY-TOWNE | 214950 | 214979 | Hyper | virus | — |
| HHV5-CINCY-TOWNE | 215930 | 215959 | Hyper | virus | — | HHV5-CINCY-TOWNE | 216228 | 216257 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 222672 | 222701 | Hyper | virus | — | HHV5-CINCY-TOWNE | 223515 | 223544 | Hyper | virus | — |
| HHV5-CINCY-TOWNE | 225150 | 225179 | Hyper | virus | — | HHV5-CINCY-TOWNE | 226058 | 226087 | Hyper | virus | — |
| HHV5-CINCY-TOWNE | 226887 | 226916 | Hyper | virus | — | chr11 | 406876 | 406939 | Hyper | cancer_general | SIGIRR, PKP3 |
| chr11 | 407427 | 407463 | Hyper | cancer_general | SIGIRR, PKP3 | chr11 | 533451 | 533567 | Hyper | literature | LRRC56, HRAS |
| chr11 | 533859 | 533888 | Hyper | literature | LRRC56, HRAS | chr11 | 534273 | 534302 | Hyper | literature | LRRC56, HRAS |
| chr11 | 611099 | 611128 | Hyper | liver_tcga | IRF7, CDHR5, PHRF1 | chr11 | 611691 | 611791 | Hyper | liver_tcga | IRF7, CDHR5, PHRF1 |
| chr11 | 627074 | 627189 | Hyper | literature, cancer_general | SCT, CDHR5 | chr11 | 636644 | 636673 | Hyper | literature | DRD4, DEAF1, SCT |
| chr11 | 636895 | 637441 | Hyper | tcga, cancer_general | DEAF1, SCT, DRD4 | chr11 | 679692 | 679722 | Hyper | liver_tcga | DEAF1 |
| chr11 | 726417 | 726466 | Hyper | cancer_general | EPS8L2 | chr11 | 829543 | 829708 | Hyper | cancer_general | CD151, EFCAB4A, PNPLA2, JB050151 |
| chr11 | 830174 | 830265 | Hyper | cancer_general | EFCAB4A, PNPLA2, JB050151, CD151, POLR2L | chr11 | 1318403 | 1318432 | Hyper | liver_tcga | TOLLIP |
| chr11 | 1358291 | 1358332 | Hyper | — | — | chr11 | 1411875 | 1411905 | Hyper | cancer_general | BRSK2 |
| chr11 | 1770051 | 1770248 | Hyper | cancer_general, tcga | CTSD, IFITM10 | chr11 | 2291259 | 2291768 | Hyper | tcga, cancer_general, liver_tcga | ASCL2 |
| chr11 | 2291984 | 2292636 | Hyper | liver_tcga, cancer_general | ASCL2 | chr11 | 2402376 | 2402405 | Hyper | liver_tcga | CD81, BC019904 |
| chr11 | 2465350 | 2465491 | Hyper | liver_tcga | KCNQ1 | chr11 | 2466597 | 2466788 | Hyper | liver_tcga | KCNQ1 |
| chr11 | 2884103 | 2884309 | Hyper | tcga | KCNQ1DN | chr11 | 3181913 | 3181942 | Hyper | tcga | — |
| chr11 | 4209105 | 4209134 | Hyper | tcga | LOC100506082, RRM1 | chr11 | 7273286 | 7273375 | Hyper | cancer_general | SYT9 |
| chr11 | 7274215 | 7274245 | Hyper | cancer_general | SYT9 | chr11 | 7695432 | 7695528 | Hyper | liver_tcga | CYB5R2 |
| chr11 | 8040536 | 8040770 | Hyper | tcga | TUB, BC027619 | chr11 | 8103002 | 8103115 | Hyper | tcga | TUB |
| chr11 | 8189987 | 8190766 | Hyper | cancer_general | RIC3 | chr11 | 8284535 | 8284760 | Hyper | tcga, cancer_general | LMO1 |
| chr11 | 8289517 | 8289745 | Hyper | cancer_general | LMO1 | chr11 | 8290195 | 8290423 | Hyper | tcga, cancer_general | LMO1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 8615674 | 8615704 | Hyper | liver_tcga | — | chr11 | 9025970 | 9026348 | Hyper | cancer_general | NRIP3 |
| chr11 | 9112446 | 9112741 | Hyper | cancer_general | KRT8P41, MIR5691, SCUBE2 | chr11 | 12029957 | 12030272 | Hyper | liver_tcga, cancer_general | DKK3 |
| chr11 | 12030823 | 12030852 | Hyper | liver_tcga | DKK3 | chr11 | 12132524 | 12132559 | Hyper | blood | MICAL2 |
| chr11 | 12399040 | 12399222 | Hyper | blood | PARVA | chr11 | 12399727 | 12399791 | Hyper | blood | PARVA |
| chr11 | 12695481 | 12695611 | Hyper | blood | TEAD1, DD413619 | chr11 | 12696611 | 12696746 | Hyper | blood | TEAD1, DD413619 |
| chr11 | 13030566 | 13030890 | Hyper | tcga, liver_tcga | RASSF10 | chr11 | 13690121 | 13690157 | Hyper | liver_tcga | FAR1 |
| chr11 | 14316375 | 14316404 | Hyper | literature | RRAS2 | chr11 | 15136085 | 15136394 | Hyper | tcga, cancer_general | INSC |
| chr11 | 16628819 | 16628933 | Hyper | blood | — | chr11 | 16632493 | 16632670 | Hyper | cancer_general | — |
| chr11 | 17497492 | 17497685 | Hyper | cancer_general | ABCC8 | chr11 | 17740493 | 17740570 | Hyper | cancer_general | MYOD1 |
| chr11 | 17741679 | 17742445 | Hyper | literature, cancer_general | MYOD1 | chr11 | 17743742 | 17743775 | Hyper | cancer_general | MYOD1 |
| chr11 | 18812614 | 18812653 | Hyper | cancer_general | PTPN5 | chr11 | 18813032 | 18813086 | Hyper | cancer_general | PTPN5 |
| chr11 | 18813451 | 18813558 | Hyper | tcga, cancer_general | PTPN5 | chr11 | 18813792 | 18813947 | Hyper | cancer_general | PTPN5 |
| chr11 | 19263848 | 19263878 | Hyper | cancer_general | E2F8 | chr11 | 19367102 | 19367330 | Hype | cancer_general | NAV2 |
| chr11 | 19735730 | 19735760 | Hyper | cancer_general | NAV2, LOC100126784 | chr11 | 20153718 | 20153764 | Hyper | cancer_general | — |
| chr11 | 20178066 | 20178305 | Hyper | cancer_general | DBX1 | chr11 | 20180279 | 20180793 | Hyper | cancer_general | DBX1 |
| chr11 | 20181213 | 20181254 | Hyper | cancer_general | DBX1 | chr11 | 20181701 | 20181993 | Hyper | literature, cancer_general | DBX1 |
| chr11 | 20182864 | 20182959 | Hyper | cancer_general | DBX1 | chr11 | 20183251 | 20183421 | Hyper | cancer_general | DBX1 |
| chr11 | 20183674 | 20183773 | Hyper | cancer_general | DBX1 | chr11 | 20184569 | 20185410 | Hyper | tcga, cancer_general | DBX1 |
| chr11 | 20229058 | 20229550 | Hyper | cancer_general | TRNA | chr11 | 20229863 | 20230091 | Hyper | literature, cancer_general | TRNA |
| chr11 | 20230398 | 20230464 | Hyper | cancer_general | TRNA | chr11 | 20618197 | 20619172 | Hyper | cancer_general, tcga, liver_tcga | SLC6A5 |
| chr11 | 20619717 | 20619974 | Hyper | cancer_general | SLC6A5 | chr11 | 20621341 | 20621644 | Hyper | cancer_general | SLC6A5 |
| chr11 | 20622705 | 20623359 | Hyper | cancer_general | SLC6A5 | chr11 | 20690653 | 20690935 | Hyper | cancer_general | NELL1 |
| chr11 | 20691219 | 20691452 | Hyper | cancer_general | NELL1 | chr11 | 20691685 | 20691914 | Hyper | cancer_general | NELL1 |
| chr11 | 20692453 | 20692529 | Hyper | cancer_general | NELL1 | chr11 | 22215123 | 22215287 | Hyper | cancer_general | ANO5 |
| chr11 | 22362934 | 22363189 | Hyper | cancer_general | SLC17A6 | chr11 | 22364821 | 22364975 | Hyper | cancer_general | SLC17A6 |
| chr11 | 22365407 | 22365477 | Hyper | cancer_general | SLC17A6 | chr11 | 27742185 | 27742215 | Hyper | cancer_general | — |
| chr11 | 27743115 | 27743173 | Hyper | cancer_general | — | chr11 | 27743436 | 27743608 | Hyper | cancer_general | — |
| chr11 | 27744147 | 27744504 | Hyper | cancer_general, pancreas | — | chr11 | 27744711 | 27744744 | Hyper | cancer_general | — |
| chr11 | 30037593 | 30037743 | Hyper | cancer_general | KCNA4 | chr11 | 30038689 | 30038739 | Hyper | cancer_general | KCNA4 |
| chr11 | 30605919 | 30606123 | Hyper | cancer_general | MPPED2 | chr11 | 30606763 | 30606864 | Hyper | cancer_general | MPPED2 |
| chr11 | 30607367 | 30607409 | Hyper | cancer_general | MPPED2 | chr11 | 31818458 | 31818652 | Hyper | cancer_general | PAX6 |
| chr11 | 31819302 | 31819833 | Hyper | cancer_general | PAX6 | chr11 | 31820045 | 31821025 | Hyper | cancer_general | PAX6 |
| chr11 | 31821297 | 31821778 | Hyper | cancer_general | PAX6 | chr11 | 31822325 | 31822393 | Hyper | cancer_general | PAX6 |
| chr11 | 31824300 | 31824355 | Hyper | cancer_general | PAX6 | chr11 | 31824564 | 31824680 | Hyper | cancer_general | PAX6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 31825017 | 31825280 | Hyper | cancer_general | PAX6 | chr11 | 31825696 | 31827204 | Hyper | cancer_general | PAX6 |
| chr11 | 31827438 | 31828123 | Hyper | cancer_general | DKFZp686K1684, RCN1, PAX6 | chr11 | 31833097 | 31833155 | Hyper | cancer_general | PAX6, DKFZp686K1684, RCN1 |
| chr11 | 31835707 | 31835797 | Hyper | cancer_general | DKFZp686K1684, RCN1, PAX6 | chr11 | 31836046 | 31836470 | Hyper | cancer_general | DKFZp686K1684, RCN1, PAX6 |
| chr11 | 31837019 | 31838392 | Hyper | cancer_general | DKFZp686K1684, RCN1, PAX6 | chr11 | 31838678 | 31839051 | Hyper | cancer_general | DKFZp686K1684 |
| chr11 | 31839307 | 31840080 | Hyper | cancer_general | RCN1, DKFZp686K1684 | chr11 | 31840587 | 31840922 | Hyper | cancer_general | RCN1, DKFZp686K1684 |
| chr11 | 31841376 | 31842276 | Hyper | cancer_general | RCN1, DKFZp686K1684 | chr11 | 31846022 | 31846230 | Hyper | cancer_general | RCN1, DKFZp686K1684 |
| chr11 | 31846434 | 31846985 | Hyper | literature, cancer_general | RCN1, DKFZp686K1684 | chr11 | 31847250 | 31847925 | Hyper | cancer_general | RCN1, DKFZp686K1684 |
| chr11 | 31848472 | 31849300 | Hyper | cancer_general | RCN1, DKFZp686K1684 | chr11 | 32009104 | 32009160 | Hyper | cancer_general | RCN1 |
| chr11 | 32354844 | 32355197 | Hyper | cancer_general | — | chr11 | 32448583 | 32448979 | Hyper | tcga, cancer_general | WT1-AS, WT1 |
| chr11 | 32455602 | 32455634 | Hyper | cancer_general | WT1-AS, WT1 | chr11 | 32455841 | 32456025 | Hyper | cancer_general | WT1-AS, WT1 |
| chr11 | 32456279 | 32457176 | Hyper | tcga, cancer_general | WT1-AS, WT1 | chr11 | 32457712 | 32458175 | Hyper | tcga, cancer_general | WT1-AS |
| chr11 | 32458389 | 32458823 | Hyper | cancer_general | WT1 | chr11 | 32459684 | 32460071 | Hyper | cancer_general | WT1, WT1-AS |
| chr11 | 32460468 | 32460515 | Hyper | cancer_general | WT1-AS, WT1 | chr11 | 32460796 | 32460864 | Hyper | cancer_general | WT1, WT1-AS |
| chr11 | 33037467 | 33037556 | Hyper | blood | DEPDC7 | chr11 | 33890297 | 33890334 | Hyper | cancer_general | LMO2 |
| chr11 | 35547499 | 35547562 | Hyper | tcga | PAMR1 | chr11 | 35641683 | 35641718 | Hyper | cancer_general | FJX1 |
| chr11 | 43596513 | 43596608 | Hyper | cancer_general | MIR 129-2, JA715139, BC031305 | chr11 | 43600453 | 43600557 | Hyper | cancer_general | BC031305, MIR129-2, JA715139 |
| chr11 | 43601094 | 43601467 | Hyper | cancer_general | MIR129-2, JA715139, BC031305 | chr11 | 43602468 | 43603228 | Hyper | liver_tcga, literature, cancer_general | MIR 129-2, JA715139 |
| chr11 | 43603628 | 43604177 | Hyper | cancer_general | JA715139, MIR129-2 | chr11 | 44325688 | 44325747 | Hyper | cancer_general | ALX4 |
| chr11 | 44326137 | 44326184 | Hyper | cancer_general | ALX4 | chr11 | 44326439 | 44326481 | Hyper | cancer_general | ALX4 |
| chr11 | 44327252 | 44327413 | Hyper | tcga | ALX4 | chr11 | 44330656 | 44331711 | Hyper | cancer_general | ALX4 |
| chr11 | 44333052 | 44333081 | Hyper | literature | ALX4 | chr11 | 44333371 | 44333480 | Hyper | cancer_general | ALX4 |
| chr11 | 44337690 | 44338077 | Hyper | cancer_general | ALX4 | chr11 | 44338335 | 44338367 | Hyper | cancer_general | ALX4 |
| chr11 | 44340823 | 44340858 | Hyper | cancer_general | ALX4 | chr11 | 44341966 | 44342034 | Hyper | cancer_general | |
| chr11 | 46316860 | 46317680 | Hyper | tcga, cancer_general | CREB3L1 | chr11 | 46313042 | 46413304 | Hyper | esophageal | AMBRA1, CHRM4, MDK |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 46940419 | 46940531 | Hyper | tcga | LRP4 | chr11 | 47209044 | 47209189 | Hyper | cancer_general | PACSIN3 |
| chr11 | 57194355 | 57194509 | Hyper | tcga | SLC43A3 | chr11 | 57414633 | 57414663 | Hyper | pancreas | YPEL4, MIR130A, AK096335 |
| chr11 | 58672746 | 58673064 | Hyper | cancer_general | AK294973 | chr11 | 59323596 | 59323729 | Hyper | cancer_general | TRNA_Val, TRNA_Lys, TRNA_Phe, U7, JB175310, TRNA_Leu, TRNA_Arg |
| chr11 | 59333405 | 59333541 | Hyper | cancer_general | TRNA_Phe, OSBP, JB175310, TRNA_Lys, U7 | chr11 | 60718668 | 60719163 | Hyper | cancer_general | SLC15A3 |
| chr11 | 61062822 | 61063138 | Hyper | tcga, cancer_general | DDB1, VWCE | chr11 | 61277002 | 61277220 | Hyper | liver_tcga, cancer_general | SYT7, LRRC10B, MIR4488 |
| chr11 | 61595086 | 61595262 | Hyper | cancer_general | FADS2 | chr11 | 61596420 | 61596640 | Hyper | cancer_general | FADS2 |
| chr11 | 61723067 | 61723159 | Hyper | cancer_general | FTH1, BEST1 | chr11 | 63767984 | 63768131 | Hyper | tcga, cancer_general | MACROD1, OTUB1 |
| chr11 | 63839478 | 63839528 | Hyper | liver_tcga | MACROD1 | chr11 | 64410723 | 64410759 | Hyper | esophageal | NRXN2 |
| chr11 | 64480429 | 64480593 | Hyper | cancer_general | — | chr11 | 64480824 | 64481042 | Hyper | liver_tcga, cancer_general | |
| chr11 | 64490435 | 64490561 | Hyper | esophageal | RASGRP2 | chr11 | 64490792 | 64491159 | Hyper | esophageal | RASGRP2 |
| chr11 | 64739468 | 64739508 | Hyper | cancer_general | — | chr11 | 65185548 | 65185728 | Hyper | cancer_general | NEAT1, FRMD8 |
| chr11 | 65405659 | 65405774 | Hyper | tcga | MIR4690, PCNXL3, SIPA1 | chr11 | 65409759 | 65409861 | Hyper | liver_tcga | MIR4489, SIPA1, MIR4690, PCNXL3 |
| chr11 | 65554041 | 65554410 | Hyper | liver_tcga | OVOL1, AP5B1 | chr11 | 65600810 | 65601640 | Hyper | liver_tcga, cancer_general | SNX32 |
| chr11 | 65779317 | 65779357 | Hyper | literature | EIF1AD, CST6, AX747517, CATSPER1, BANF1 | chr11 | 65816447 | 65816564 | Hyper | literature, cancer_general | GAL3ST3, SF3B2 |
| chr11 | 66188115 | 66188145 | Hyper | cancer_general | NPAS4 | chr11 | 66184473 | 66188974 | Hyper | cancer_general | NPAS4 |
| chr11 | 66725600 | 66725637 | Hyper | blood | — | chr11 | 66790621 | 66790655 | Hyper | blood | SYT12 |
| chr11 | 67139422 | 67139546 | Hyper | liver_tcga | CLCF1, 7SK | chr11 | 67350180 | 67350340 | Hyper | literature | GSTP1 |
| chr11 | 67350961 | 67350990 | Hyper | literature | GSTP1 | chr11 | 68096034 | 68096179 | Hyper | tcga | LRP5 |
| chr11 | 68118716 | 68118745 | Hyper | liver_tcga | LRP5 | chr11 | 68153950 | 68154098 | Hyper | liver_tcga | LRP5 |
| chr11 | 68181217 | 68181288 | Hyper | liver_tcga | LRP5 | chr11 | 69466004 | 69466042 | Hyper | literature | AK294004, ORAOV1, BC133018, CCND1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 69484356 | 69484454 | Hyper | head_neck | ORAOV1 | chr11 | 69516968 | 69517174 | Hyper | cancer_general | FGF19 |
| chr11 | 69518030 | 69518211 | Hyper | liver_tcga, cancer_general | FGF19 | chr11 | 69518530 | 69518718 | Hyper | tcga, liver_tcga | FGF19 |
| chr11 | 69588930 | 69589184 | Hyper | cancer_general | FGF4 | chr11 | 69589824 | 69589854 | Hyper | cancer_general | FGF4 |
| chr11 | 69590149 | 69590222 | Hyper | cancer_general | FGF4 | chr11 | 70211516 | 70211545 | Hyper | literature | PPF1A1, AK125463 |
| chr11 | 71318332 | 71318967 | Hyper | cancer_general | — | chr11 | 71951639 | 71951738 | Hyper | cancer_general | PHOX2A, INPPL1 |
| chr11 | 71952340 | 71952541 | Hyper | cancer_general | PHOX2A, INPPL1 | chr11 | 71954612 | 71954642 | Hyper | cancer_general | INPPL1 |
| chr11 | 71955344 | 71955377 | Hyper | cancer_general | PHOX2A, INPPL1 | chr11 | 71956007 | 71956340 | Hyper | cancer_general | PHOX2A, INPPL1 |
| chr11 | 72432837 | 72432916 | Hyper | cancer_general | — | chr11 | 72929747 | 72929883 | Hyper | blood | P2RY2 |
| chr11 | 73694609 | 73694659 | Hyper | hepatobiliary | UCP2 | chr11 | 74394491 | 74394600 | Hyper | cancer_general | — |
| chr11 | 74953265 | 74953422 | Hyper | cancer_general | TPBGL | chr11 | 75379252 | 75379895 | Hyper | cancer_general | MAP6 |
| chr11 | 78672917 | 78672964 | Hyper | cancer_general | ODZ4, TENM4 | chr11 | 79151173 | 79151216 | Hyper | tcga | — |
| chr11 | 82244376 | 82445101 | Hyper | cancer_general | FAM181B | chr11 | 86085742 | 86085968 | Hyper | literature, cancer_general | CCDC81 |
| chr11 | 86383167 | 86383710 | Hyper | literature, tcga | ME3 | chr11 | 88241705 | 88242618 | Hyper | tcga, cancer_general | GRM5, GRM5-AS1 |
| chr11 | 88799082 | 88799209 | Hyper | cancer_general | GRM5 | chr11 | 89867794 | 89867990 | Hyper | tcga, cancer_general | NAALAD2 |
| chr11 | 91957500 | 91957674 | Hyper | cancer_general | — | chr11 | 91957974 | 91958230 | Hyper | tcga, cancer_general | — |
| chr11 | 91958734 | 91959430 | Hyper | tcga, cancer_general | — | chr11 | 91959899 | 91960045 | Hyper | cancer_general | — |
| chr11 | 93063583 | 93063645 | Hyper | cancer_general | CCDC67 | chr11 | 93063870 | 93063948 | Hyper | liver_tcga, cancer_general | CCDC67 |
| chr11 | 94134086 | 94134853 | Hyper | tcga, cancer_general | GPR83 | chr11 | 94278456 | 94278603 | Hyper | liver_tcga | PIWIL4, FUT4 |
| chr11 | 94473600 | 94474139 | Hyper | tcga, colorectal, cancer_general | — | chr11 | 94474356 | 94474385 | Hyper | tcga | — |
| chr11 | 94502334 | 94502489 | Hyper | tcga, colorectal | AMOTL1 | chr11 | 94884130 | 94884160 | Hyper | head_neck | AK055250 |
| chr11 | 98891477 | 98891882 | Hyper | tcga, cancer_general | CNTN5 | chr11 | 100997649 | 100997981 | Hyper | cancer_general | LOC101054525, PGR |
| chr11 | 100998276 | 100998318 | Hyper | cancer_general | LOC101054525, PGR | chr11 | 100998667 | 100998747 | Hyper | cancer_general | LOC101054525, PGR |
| chr11 | 101453180 | 101453518 | Hyper | cancer_general | DCUN1D5 | chr11 | 101454190 | 101454490 | Hyper | cancer_general | DYNC2H1 |
| chr11 | 102962922 | 102963062 | Hyper | pancreas | — | chr11 | 102980027 | 102980056 | Hyper | literature | GRIA4 |
| chr11 | 104034521 | 104034996 | Hyper | tcga, cancer_general | — | chr11 | 105480755 | 105480806 | Hyper | cancer_general | — |
| chr11 | 105481216 | 105481571 | Hyper | tcga, cancer_general | GRIA4 | chr11 | 106888308 | 106888429 | Hyper | cancer_general | GUCY1A2 |
| chr11 | 106888641 | 106888801 | Hyper | tcga, cancer_general | GUCY1A2 | chr11 | 107461623 | 107461653 | Hyper | esophageal | ELMOD1, LOC643923 |
| chr11 | 107462415 | 107462459 | Hyper | tcga | LOC643923, ELMOD1 | chr11 | 108236072 | 108236101 | Hyper | literature | C11orf65 |
| chr11 | 109292906 | 109293052 | Hyper | cancer_general | C11orf87 | chr11 | 109293720 | 109293847 | Hyper | cancer_general | C11orf87 |
| chr11 | 110166519 | 110166935 | Hyper | esophageal | — | chr11 | 110582232 | 110582434 | Hyper | tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 110582895 | 110583050 | Hyper | tcga | — | chr11 | 110583574 | 110583730 | Hyper | cancer_general | LAYN, C11orf88 |
| chr11 | 111383183 | 111383682 | Hyper | cancer_general | MIR34B, MIR34C, C11orf88, BC021736, BTG4 | chr11 | 111411093 | 111412061 | Hyper | tcga, cancer_general | |
| chr11 | 114113022 | 114113052 | Hyper | esophageal | ZBTB16 | chr11 | 115375120 | 115375177 | Hyper | cancer_general | CADM1 |
| chr11 | 115530134 | 115530604 | Hyper | cancer_general, tcga | — | chr11 | 115630515 | 115630910 | Hyper | cancer_general | LINC00900 |
| chr11 | 115631307 | 115631364 | Hyper | cancer_general | LINC00900 | chr11 | 116147253 | 116147283 | Hyper | pancreas | DSCAML1 |
| chr11 | 116451023 | 116451190 | Hyper | tcga | — | chr11 | 117296921 | 117297109 | Hyper | tcga | CBL |
| chr11 | 119148865 | 119148945 | Hyper | literature | CBL | chr11 | 119149236 | 119149265 | Hyper | literature | THY1, LOC100499227 |
| chr11 | 119292779 | 119292809 | Hyper | cancer_general | THY1, LOC100499227 | chr11 | 119293370 | 119293615 | Hyper | tcga | |
| chr11 | 119612227 | 119612399 | Hyper | cancer_general | — | chr11 | 119612861 | 119613075 | Hyper | liver_tcga, cancer_general | — |
| chr11 | 120039833 | 120039865 | Hyper | blood | — | chr11 | 120435405 | 120435477 | Hyper | cancer_general | GRIK4 |
| chr11 | 120435800 | 120435830 | Hyper | cancer_general | GRIK4 | chr11 | 120894800 | 120895026 | Hyper | esophageal | TBCEL |
| chr11 | 122847265 | 122847696 | Hyper | cancer_general | BSX | chr11 | 122848079 | 122848591 | Hyper | cancer_general | BSX |
| chr11 | 122849301 | 122849331 | Hyper | cancer_general | BSX | chr11 | 122849642 | 122850163 | Hyper | cancer_general | BSX |
| chr11 | 122850424 | 122850536 | Hyper | cancer_general | BSX | chr11 | 122851177 | 122851209 | Hyper | tcga | BSX |
| chr11 | 122852438 | 122852475 | Hyper | cancer_general | BSX | chr11 | 122855008 | 122855043 | Hyper | tcga, cancer_general | — |
| chr11 | 123066433 | 123066463 | Hyper | cancer_general | CLMP | chr11 | 123229058 | 123229422 | | cancer_general | — |
| chr11 | 123300824 | 123302026 | Hyper | tcga, cancer_general | — | chr11 | 124735437 | 124735482 | Hyper | cancer_general | ROBO3 |
| chr11 | 124736196 | 124736252 | Hyper | cancer_general | ROBO3 | chr11 | 124738777 | 124739088 | Hyper | cancer_general | ROBO3 |
| chr11 | 125035763 | 125036208 | Hyper | cancer_general | PKNOX2 | chr11 | 125036598 | 125036645 | Hyper | cancer_general | PKNOX2 |
| chr11 | 125773675 | 125774096 | Hyper | cancer_general, liver_tcga | DDX25, HYLS1, PUS3 | chr11 | 126870182 | 126870212 | Hyper | cancer_general | KIRREL3-AS3 |
| chr11 | 126870453 | 126870543 | Hyper | cancer_general | KIRREL3-AS3 | chr11 | 126873390 | 126873515 | Hyper | cancer_general | KIRREL3-AS3 |
| chr11 | 128391893 | 128392116 | Hyper | tcga | BC043517, ETS1 | chr11 | 128562892 | 128563730 | Hyper | tcga, cancer_general | FLI1, FLI1-AS1, AX747861 |
| chr11 | 128563940 | 128564329 | Hyper | tcga, cancer_general | FLI1, FLI1-AS1, AX747861 | chr11 | 128564740 | 128565379 | Hyper | cancer_general | FLI1-AS1, AX747861, FLI1 |
| chr11 | 129242876 | 129243587 | Hyper | cancer_general | BARX2 | chr11 | 129243849 | 129244603 | Hyper | cancer_general | BARX2 |
| chr11 | 129244893 | 129244923 | Hyper | cancer_general | BARX2 | chr11 | 129245673 | 129245810 | Hyper | blood | BARX2 |
| chr11 | 129246070 | 129246129 | Hyper | blood | BARX2 | chr11 | 130318960 | 130318997 | Hyper | blood | ADAMTS15 |
| chr11 | 130319527 | 130319613 | Hyper | cancer_general | ADAMTS15 | chr11 | 131564970 | 131565073 | Hyper | pancreas | — |
| chr11 | 131780469 | 131781271 | Hyper | tcga, cancer_general | NTM | chr11 | 132813489 | 132813949 | Hyper | cancer_general | — |
| chr11 | 132864134 | 132864175 | Hyper | tcga, cancer_general | — | chr11 | 132934123 | 132934176 | Hyper | cancer_general | — |
| chr11 | 132952768 | 132953423 | Hyper | tcga, cancer_general | — | chr11 | 133402206 | 133402260 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 133825226 | 133825543 | Hyper | cancer_general | IGSF9B | chr11 | 133906783 | 133906918 | Hyper | cancer_general | LOC100128239 |
| chr11 | 133939002 | 133939177 | Hyper | cancer_general | JAM3 | chr11 | 134145703 | 134146393 | Hyper | liver_tcga, cancer_general, tcga | GLB1L3 |
| chr11 | 134146682 | 134146894 | Hyper | cancer_general | GLB1L3 | chr11 | 134201502 | 134201543 | Hyper | blood | GLB1L2 |
| chr11 | 134201841 | 134202084 | Hyper | blood, tcga, liver_tcga | GLB1L2 | chr11 | 134281365 | 134281509 | Hyper | cancer_general | LOC283177 |
| chrY | 2655316 | 2655346 | Hyper | cancer_general | SRY, RPS4Y1, XGPY2 | chrY | 14532822 | 14532852 | Hyper | head_neck | GYG2P1 |
| chrY | 14533556 | 14533613 | Hyper | head_neck | GYG2P1 | HPV18 | 111 | 140 | Hyper | virus | — |
| HPV18 | 383 | 412 | Hyper | virus | — | HPV18 | 655 | 684 | Hyper | virus | — |
| HPV18 | 927 | 956 | Hyper | virus | — | HPV18 | 1199 | 1228 | Hyper | virus | — |
| HPV18 | 1471 | 1500 | Hyper | virus | — | HPV18 | 1743 | 1772 | Hyper | virus | — |
| HPV18 | 2015 | 2044 | Hyper | virus | — | HPV18 | 2287 | 2316 | Hyper | virus | — |
| HPV18 | 2559 | 2588 | Hyper | virus | — | HPV18 | 2831 | 2860 | Hyper | virus | — |
| HPV18 | 3103 | 3132 | Hyper | virus | — | HPV18 | 3375 | 3404 | Hyper | virus | — |
| HPV18 | 3647 | 3676 | Hyper | virus | — | HPV18 | 3919 | 3948 | Hyper | virus | — |
| HPV18 | 4191 | 4220 | Hyper | virus | — | HPV18 | 4463 | 4492 | Hyper | virus | — |
| HPV18 | 4735 | 4764 | Hyper | virus | — | HPV18 | 5007 | 5036 | Hyper | virus | — |
| HPV18 | 5279 | 5308 | Hyper | virus | — | HPV18 | 5551 | 5580 | Hyper | virus | — |
| HPV18 | 5823 | 5852 | Hyper | virus | — | HPV18 | 6095 | 6124 | Hyper | virus | — |
| HPV18 | 6367 | 6396 | Hyper | virus | — | HPV18 | 6639 | 6668 | Hyper | virus | — |
| HPV18 | 6911 | 6940 | Hyper | virus | — | HPV18 | 7183 | 7212 | Hyper | virus | — |
| HPV18 | 7455 | 7484 | Hyper | virus | — | HBV | 111 | 140 | Hyper | virus | — |
| HBV | 381 | 410 | Hyper | virus | — | HBV | 651 | 680 | Hyper | virus | — |
| HBV | 921 | 950 | Hyper | virus | — | HBV | 1191 | 1220 | Hyper | virus | — |
| HBV | 1461 | 1490 | Hyper | virus | — | HBV | 1731 | 1760 | Hyper | virus | — |
| HBV | 2001 | 2030 | Hyper | virus | — | HBV | 2271 | 2300 | Hyper | virus | — |
| HBV | 2541 | 2570 | Hyper | virus | — | HBV | 2811 | 2840 | Hyper | virus | — |
| chr18 | 499367 | 499482 | Hyper | cancer_general | COLEC12 | chr18 | 500046 | 500738 | Hyper | cancer_general | COLEC12 |
| chr18 | 904462 | 904648 | Hyper | cancer_general | ADCYAP1 | chr18 | 905000 | 905030 | Hyper | cancer_general | ADCYAP1 |
| chr18 | 905434 | 905642 | Hyper | cancer_general | ADCYAP1 | chr18 | 906871 | 906907 | Hyper | cancer_general | ADCYAP1 |
| chr18 | 907472 | 907594 | Hyper | cancer_general | ADCYAP1 | chr18 | 907912 | 907977 | Hyper | cancer_general | ADCYAP1 |
| chr18 | 908454 | 908589 | Hyper | cancer_general | ADCYAP1 | chr18 | 909120 | 909150 | Hyper | cancer_general | ADCYAP1 |
| chr18 | 909487 | 909587 | Hyper | cancer_general | DLGAP1 | chr18 | 2906268 | 2906304 | Hyper | tcga | EMILIN2 |
| chr18 | 3499067 | 3499371 | Hyper | cancer_general | — | chr18 | 4453964 | 4454163 | Hyper | cancer_general | — |
| chr18 | 4455074 | 4455181 | Hyper | cancer_general | C18orf42 | chr18 | 5196516 | 5196959 | Hyper | cancer_general | C18orf42 LINC00667, LINC00526, LOC339290 |
| chr18 | 5197202 | 5197347 | Hyper | cancer_general | — | chr18 | 5237878 | 5238247 | Hyper | esophageal | — |
| chr18 | 5543231 | 5543331 | Hyper | cancer_general | EPB41L3 | chr18 | 5543640 | 5543853 | Hyper | cancer_general | EPB41L3 |
| chr18 | 5628167 | 5628515 | Hyper | cancer_general | — | chr18 | 5629774 | 5629984 | Hyper | cancer_general | — |
| chr18 | 5630312 | 5630362 | Hyper | cancer_general | TMEM200C | chr18 | 5890619 | 5891317 | Hyper | cancer_general | TMEM200C |
| chr18 | 5895023 | 5895205 | Hyper | cancer_general | TMEM200C | chr18 | 5895975 | 5896085 | Hyper | tcga | TMEM200C |
| chr18 | 6729952 | 6729993 | Hyper | cancer_general | LAMA1 | chr18 | 7116924 | 7116981 | Hyper | cancer_general | LAMA1 |
| chr18 | 7117665 | 7117804 | Hyper | tcga | LAMA1 | chr18 | 7567783 | 7568291 | Hyper | tcga, cancer_general | PTPRM |
| chr18 | 8608748 | 8608968 | Hyper | cancer_general | RAB12 | chr18 | 9771586 | 9771753 | Hyper | cancer_general | RAB31 |
| chr18 | 11148969 | 11149045 | Hyper | cancer_general | — | chr18 | 11149561 | 11149888 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 11689190 | 11689220 | Hyper | esophageal | GNAL | chr18 | 11751637 | 11751676 | Hyper | cancer_general | GNAL |
| chr18 | 11751966 | 11752379 | Hyper | cancer_general | GNAL | chr18 | 11752700 | 11752730 | Hyper | cancer_general | GNAL |
| chr18 | 12254226 | 12254578 | Hyper | cancer_general, tcga | CIDEA | chr18 | 12307247 | 12307751 | Hyper | tcga, cancer_general | TUBB6 |
| chr18 | 12911384 | 12911476 | Hyper | cancer_general | — | chr18 | 13824025 | 13824102 | Hyper | head_neck | MC5R |
| chr18 | 13868713 | 13868945 | Hyper | cancer_general | — | chr18 | 15198110 | 15198248 | Hyper | cancer_general | — |
| chr18 | 18822392 | 18823274 | Hyper | tcga, cancer_general | GREB1L | chr18 | 19750308 | 19750346 | Hyper | blood | GATA6, LOC100128893 |
| chr18 | 21269349 | 21269390 | Hyper | blood | LAMA3 | chr18 | 21269659 | 21269740 | Hyper | blood | LAMA3 |
| chr18 | 21719351 | 21719568 | Hyper | liver_tcga | CABYR, TTC39C | chr18 | 22929081 | 22930559 | Hyper | cancer_general, tcga | ZNF521 |
| chr18 | 22930790 | 22931178 | Hyper | cancer_general | ZNF521 | chr18 | 24127748 | 24128030 | Hyper | cancer_general | |
| chr18 | 24130809 | 24131187 | Hyper | cancer_general | — | chr18 | 24764951 | 24765168 | Hyper | tcga | CHST9 |
| chr18 | 25755593 | 25755655 | Hyper | tcga | — | chr18 | 25756010 | 25756040 | Hyper | cancer_general | |
| chr18 | 25756495 | 25756729 | Hyper | tcga, cancer_general | — | chr18 | 25757187 | 25757452 | Hyper | tcga | |
| chr18 | 25757787 | 25757824 | Hyper | cancer_general | — | chr18 | 25758084 | 25758141 | Hyper | cancer_general | |
| chr18 | 28620899 | 28621097 | Hyper | cancer_general | DSC3 | chr18 | 28621328 | 28621393 | Hyper | cancer_general | DSC3 |
| chr18 | 28621636 | 28621932 | Hyper | liver_tcga, cancer_general | DSC3 | chr18 | 28622419 | 28622488 | Hyper | cancer_general | DSC3 |
| chr18 | 30349740 | 30349781 | Hyper | cancer_general | KLHL14 | chr18 | 31020495 | 31020820 | Hyper | tcga, cancer_general | CCDC178 |
| chr18 | 31158093 | 31158158 | Hyper | cancer_general | ASXL3 | chr18 | 31739035 | 31739469 | Hyper | cancer_general | |
| chr18 | 31802132 | 31802167 | Hyper | cancer_general | — | chr18 | 31802938 | 31802968 | Hyper | cancer_general | |
| chr18 | 31803438 | 31803472 | Hyper | cancer_general | — | chr18 | 31902793 | 31902945 | Hyper | lung | |
| chr18 | 32073885 | 32074086 | Hyper | cancer_general | DTNA | chr18 | 32557832 | 32557864 | Hyper | head_neck | MAPRE2 |
| chr18 | 32847565 | 32847642 | Hyper | liver_tcga | ZSCAN30 | chr18 | 33877683 | 33877754 | Hyper | esophageal | FHOD3 |
| chr18 | 34833596 | 34833859 | Hyper | cancer_general | CELF4 | chr18 | 35065072 | 35065438 | Hyper | cancer_general | |
| chr18 | 35104666 | 35104882 | Hyper | cancer_general | — | chr18 | 35144845 | 35145465 | Hyper | cancer_general | |
| chr18 | 35145968 | 35146241 | Hyper | tcga | — | chr18 | 35147487 | 35147569 | Hyper | cancer_general | ST8SIA5 |
| chr18 | 43914211 | 43914278 | Hyper | tcga | C18orf23, RNF165 | chr18 | 44336034 | 44336697 | Hyper | cancer_general | ST8SIA5 |
| chr18 | 44336901 | 44336946 | Hyper | cancer_general | ST8SIA5 | chr18 | 44337174 | 44338074 | Hyper | cancer_general | ST8SIA5 |
| chr18 | 44733060 | 44733197 | Hyper | cancer_general | — | chr18 | 44773592 | 44774153 | Hyper | cancer_general | |
| chr18 | 44774406 | 44774890 | Hyper | cancer_general | — | chr18 | 44775380 | 44775554 | Hyper | cancer_general | |
| chr18 | 44776972 | 44777088 | Hyper | cancer_general | — | chr18 | 44777301 | 44777331 | Hyper | cancer_general | |
| chr18 | 44777596 | 44777750 | Hyper | cancer_general | — | chr18 | 44778049 | 44778326 | Hyper | cancer_general | |
| chr18 | 44781003 | 44781041 | Hyper | cancer_general | — | chr18 | 44787781 | 44787846 | Hyper | cancer_general | |
| chr18 | 44788251 | 44788281 | Hyper | cancer_general | — | chr18 | 44789474 | 44789514 | Hyper | cancer_general | |
| chr18 | 44789872 | 44789937 | Hyper | cancer_general | — | chr18 | 45058069 | 45058240 | Hyper | cancer_general | BC040860 |
| chr18 | 47720492 | 47720522 | Hyper | blood | — | chr18 | 48604773 | 48604802 | Hyper | literature | SMAD4 |
| chr18 | 49867303 | 49867399 | Hyper | cancer_general | DCC | chr18 | 49868634 | 49868664 | Hyper | cancer_general | DCC |
| chr18 | 52989009 | 52989220 | Hyper | cancer_general | TCF4 | chr18 | 52989741 | 52989882 | Hyper | cancer_general | TCF4 |
| chr18 | 53257137 | 53257204 | Hyper | cancer_general | TCF4 | chr18 | 53446970 | 53447816 | Hyper | tcga, liver_tcga, cancer_general | AK127787 |
| chr18 | 54789070 | 54789256 | Hyper | cancer_general | — | chr18 | 55019707 | 55019871 | Hyper | liver_tcga, cancer_general | ST8SIA3 |
| chr18 | 55020655 | 55020727 | Hyper | cancer_general | ST8SIA3 | chr18 | 55021078 | 55021242 | Hyper | cancer_general | ST8SIA3 |
| chr18 | 55103381 | 55103411 | Hyper | cancer_general | ONECUT2 | chr18 | 55103719 | 55103748 | Hyper | literature | ONECUT2 |
| chr18 | 55104808 | 55105140 | Hyper | cancer_general | ONECUT2 | chr18 | 55105728 | 55105830 | Hyper | cancer_general | ONECUT2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 55114480 | 55114644 | Hyper | cancer_general | ONECUT2 | chr18 | 56887076 | 56887424 | Hyper | cancer_general, tcga | GRP |
| chr18 | 56888554 | 56888623 | Hyper | cancer_general | GRP | chr18 | 56931541 | 56931583 | Hyper | cancer_general | RAX |
| chr18 | 56931967 | 56932107 | Hyper | cancer_general | RAX | chr18 | 56932352 | 56932637 | Hyper | cancer_general | RAX |
| chr18 | 56935010 | 56935319 | Hyper | cancer_general | RAX | chr18 | 56936004 | 56936074 | Hyper | cancer_general | RAX |
| chr18 | 56939113 | 56939174 | Hyper | cancer_general | RAX | chr18 | 56939423 | 56940722 | Hyper | cancer_general | RAX |
| chr18 | 56940955 | 56941788 | Hyper | cancer_general | RAX | chr18 | 57363706 | 57363743 | Hyper | cancer_general | CCBE1 |
| chr18 | 57364275 | 57364392 | Hyper | cancer_general | CCBE1 | chr18 | 57364658 | 57364691 | Hyper | pancreas | CCBE1 |
| chr18 | 59000988 | 59001022 | Hyper | cancer_general | CDH20 | chr18 | 59001301 | 59001740 | Hyper | cancer_general, tcga | CDH20 |
| chr18 | 60263547 | 60263895 | Hyper | cancer_general | DKFZp451A185 | chr18 | 60985498 | 60985732 | Hyper | liver_tcga, cancer_general | KDSR, BCL2 |
| chr18 | 67067558 | 67067907 | Hyper | tcga, cancer_general | DOK6 | chr18 | 67068152 | 67068203 | Hyper | cancer_general | DOK6 |
| chr18 | 67068442 | 67068471 | Hyper | tcga | DOK6 | chr18 | 67068715 | 67068811 | Hyper | tcga, cancer_general | DOK6 |
| chr18 | 67069216 | 67069246 | Hyper | cancer_general | DOK6 | chr18 | 70209148 | 70209205 | Hyper | cancer_general | CBLN2 |
| chr18 | 70209422 | 70209452 | Hyper | cancer_general | CBLN2 | chr18 | 70210418 | 70210508 | Hyper | tcga, cancer_general | CBLN2 |
| chr18 | 70211626 | 70211666 | Hyper | cancer_general | CBLN2 | chr18 | 70534282 | 70534969 | Hyper | cancer_general | NETO1 |
| chr18 | 70535373 | 70535582 | Hyper | cancer_general | NETO1 | chr18 | 70536010 | 70536604 | Hyper | cancer_general | NETO1 |
| chr18 | 70536833 | 70536871 | Hyper | cancer_general | NETO1 | chr18 | 70537188 | 70537218 | Hyper | cancer_general | NETO1 |
| chr18 | 73167585 | 73167832 | Hyper | cancer_general | — | chr18 | 73628019 | 73628068 | Hyper | cancer_general | — |
| chr18 | 74961326 | 74962147 | Hyper | cancer_general, literature | GALR1 | chr18 | 74962250 | 74962652 | Hyper | cancer_general | GALR1 |
| chr18 | 74962970 | 74963599 | Hyper | cancer_general | GALR1 | chr18 | 75362931 | 75362985 | Hyper | pancreas | SALL3 |
| chr18 | 75612225 | 75612286 | Hyper | cancer_general | — | chr18 | 76740079 | 76740285 | Hyper | liver_tcga | — |
| chr18 | 77548078 | 77548609 | Hyper | cancer_general | — | chr18 | 77558082 | 77558358 | Hyper | cancer_general | — |
| chr18 | 77558831 | 77558930 | Hyper | tcga | — | chr18 | 78004993 | 78005051 | Hyper | blood | PARD6G |
| chr9 | 113433 | 113556 | Hyper | cancer_general | FOXD4, CBWD1, FOXD4 | chr9 | 113850 | 113885 | Hyper | cancer_general | FOXD4, CBWD1 |
| chr9 | 117884 | 118090 | Hyper | cancer_general | DMRT1 | chr9 | 841691 | 842230 | Hyper | cancer_general | DMRT1 |
| chr9 | 842558 | 842673 | Hyper | cancer_general | DMRT3, DMRT1 | chr9 | 969556 | 969586 | Hyper | cancer_general | DMRT3, DMRT1 |
| chr9 | 969799 | 969846 | Hyper | cancer_general | DMRT3, DMRT1 | chr9 | 970096 | 970225 | Hyper | cancer_general | DMRT3, DMRT1 |
| chr9 | 970495 | 970525 | Hyper | cancer_general | DMRT3, DMRT1 | chr9 | 970897 | 971572 | Hyper | cancer_general | DMRT1, DMRT3 |
| chr9 | 972307 | 972759 | Hyper | tcga, cancer_general | DMRT3, DMRT1 | chr9 | 973143 | 973289 | Hyper | cancer_general | DMRT3, DMRT1 |
| chr9 | 974514 | 974547 | Hyper | cancer_general | DMRT1, DMRT3 | chr9 | 975117 | 975167 | Hyper | cancer_general | DMRT3, DMRT1 |
| chr9 | 975783 | 976321 | Hyper | cancer_general | DMRT3, DMRT1 | chr9 | 976618 | 976961 | Hyper | tcga, cancer_general | DMRT3, DMRT1 |
| chr9 | 981797 | 981830 | Hyper | cancer_general | DMRT3, DMRT1 | chr9 | 1042402 | 1042986 | Hyper | tcga, cancer_general | DMRT2 |
| chr9 | 1051848 | 1052166 | Hyper | cancer_general | DMRT2 | chr9 | 3181752 | 3181869 | Hyper | cancer_general | — |
| chr9 | 5070006 | 5070050 | Hyper | literature | JAK2 | chr9 | 5073756 | 5073788 | Hyper | literature | JAK2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 5078346 | 5078375 | Hyper | literature | JAK2 | chr9 | 5089711 | 5089740 | Hyper | literature | TRNA_Gln, JAK2 |
| chr9 | 6412571 | 6412809 | Hyper | cancer_general | UHRF2 | chr9 | 6644297 | 6644554 | Hyper | cancer_general | GLDC |
| chr9 | 6645017 | 6645333 | Hyper | cancer_general | GLDC | chr9 | 6645625 | 6645700 | Hyper | cancer_general | GLDC |
| chr9 | 13278818 | 13278864 | Hyper | blood | | chr9 | 14312994 | 14313096 | Hyper | blood | NFIB |
| chr9 | 14313319 | 14313785 | Hyper | cancer_general | NFIB | chr9 | 14347633 | 14347673 | Hyper | cancer_general | |
| chr9 | 14348314 | 14348452 | Hyper | cancer_general | | chr9 | 17906404 | 17906694 | Hyper | cancer_general | |
| chr9 | 17907004 | 17907061 | Hyper | cancer_general | | chr9 | 17907416 | 17907472 | Hyper | cancer_general | |
| chr9 | 19789107 | 19789301 | Hyper | cancer_general | SLC24A2 | chr9 | 21031734 | 21031836 | Hyper | cancer_general | PTPLAD2 |
| chr9 | 21402617 | 21403021 | Hyper | cancer_general | IFNA8 | chr9 | 21559294 | 21559381 | Hyper | blood | |
| chr9 | 21559665 | 21559702 | Hyper | blood | | chr9 | 21965057 | 21965757 | Hyper | lung, cancer_general | C9orf53, CDKN2A |
| chr9 | 21968218 | 21968475 | Hyper | literature, cancer_general | C9orf53, CDKN2A | chr9 | 21970959 | 21971220 | Hyper | literature, cancer_general | CDKN2A, C9orf53 |
| chr9 | 21973940 | 21974237 | Hyper | cancer_general | CDKN2A, C9orf53 | chr9 | 21974499 | 21974794 | Hyper | liver_tcga, literature, cancer_general | CDKN2A, C9orf53 |
| chr9 | 21994208 | 21994237 | Hyper | literature | CDKN2B-AS1, CDKN2B | chr9 | 21995297 | 21995326 | Hyper | literature | CDKN2B, CDKN2B-AS1 |
| chr9 | 21995720 | 21995749 | Hyper | literature | CDKN2B-AS1, CDKN2B | chr9 | 22006131 | 22006160 | Hyper | literature | CDKN2B, CDKN2B-AS1 |
| chr9 | 22008819 | 22008899 | Hyper | literature | CDKN2B, CDKN2B-AS1 | chr9 | 22447664 | 22447708 | Hyper | tcga | DMRTA1 |
| chr9 | 23822568 | 23822606 | Hyper | cancer_general | | chr9 | 23824561 | 23824591 | Hyper | cancer_general | |
| chr9 | 23831100 | 23831399 | Hyper | cancer_general | | chr9 | 29212170 | 29212294 | Hyper | cancer_general | |
| chr9 | 29213508 | 29213651 | Hyper | cancer_general | | chr9 | 29214030 | 29214144 | Hyper | cancer_general | |
| chr9 | 29214360 | 29214430 | Hyper | cancer_general | | chr9 | 29214681 | 29215086 | Hyper | cancer_general | |
| chr9 | 32782630 | 32783121 | Hyper | cancer_general | TMEM215 | chr9 | 32783346 | 32783657 | Hyper | cancer_general | TMEM215 |
| chr9 | 33524609 | 33524687 | Hyper | cancer_general | ANKRD18B | chr9 | 33676771 | 33676801 | Hyper | cancer_general | PTENP1 |
| chr9 | 33677360 | 33677415 | Hyper | cancer_general | PTENP1 | chr9 | 34589062 | 34589156 | Hyper | cancer_general | LOC415056, CNTFR |
| chr9 | 34809749 | 34809981 | Hyper | cancer_general | | chr9 | 35617291 | 35617337 | Hyper | tcga | CD72, MIR4667, TESK1 |
| chr9 | 35675539 | 35676180 | Hyper | tcga, cancer_general | HV781757, TPM2, CA9 | chr9 | 35844834 | 35844863 | Hyper | literature | TMEM8B |
| chr9 | 36037068 | 36037098 | Hyper | esophageal | RECK | chr9 | 36739755 | 36739980 | Hyper | cancer_general | |
| chr9 | 37002454 | 37003077 | Hyper | literature, cancer_general | PAX5 | chr9 | 37025564 | 37025783 | Hyper | literature, cancer_general | PAX5 |
| chr9 | 37026146 | 37026622 | Hyper | cancer_general | PAX5 | chr9 | 37026831 | 37027412 | Hyper | tcga, colorectal, cancer_general | PAX5 |
| chr9 | 37027800 | 37027829 | Hyper | literature | PAX5 | chr9 | 37028944 | 37029119 | Hyper | cancer_general | PAX5 |
| chr9 | 37029534 | 37030655 | Hyper | cancer_general, literature | PAX5 | chr9 | 37034197 | 37034247 | Hyper | cancer_general | PAX5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 37034616 | 37034731 | Hyper | cancer_general, literature | PAX5 | chr9 | 37035366 | 37035734 | Hyper | literature, cancer_general | PAX5 |
| chr9 | 37036425 | 37036647 | Hyper | cancer_general | PAX5 | chr9 | 37037671 | 37038354 | Hyper | cancer_general | — |
| chr9 | 38620530 | 38620725 | Hyper | blood | FAM201A, ANKRD18A | chr9 | 66455999 | 66456047 | Hyper | cancer_general | CR627148, AK308561 |
| chr9 | 71788952 | 71789757 | Hyper | cancer_general | TIP2, AK096834 | chr9 | 74061838 | 74062070 | Hyper | cancer_general | TRPM3 |
| chr9 | 74764547 | 74764648 | Hyper | cancer_general | GDA | chr9 | 77112993 | 77113825 | Hyper | pancreas, cancer_general | RORB |
| chr9 | 77114745 | 77114851 | Hyper | cancer_general | RORB | chr9 | 77115210 | 77115447 | Hyper | cancer_general | RORB |
| chr9 | 77115657 | 77115687 | Hyper | cancer_general | RORB | chr9 | 79628076 | 79627370 | Hyper | cancer_general | FOXB2 |
| chr9 | 79628289 | 79628329 | Hyper | cancer_general | FOXB2 | chr9 | 79629095 | 79629471 | Hyper | cancer_general | FOXB2 |
| chr9 | 79629879 | 79630420 | Hyper | cancer_general | FOXB2 | chr9 | 79631192 | 79631335 | Hyper | cancer_general | FOXB2 |
| chr9 | 79631555 | 79631591 | Hyper | cancer_general | FOXB2 | chr9 | 79631865 | 79632182 | Hyper | cancer_general | FOXB2 |
| chr9 | 79632860 | 79632890 | Hyper | tcga, cancer_general | FOXB2 | chr9 | 79633397 | 79633904 | Hyper | tcga, cancer_general | FOXB2 |
| chr9 | 79634170 | 79636043 | Hyper | cancer_general | FOXB2 | chr9 | 79636258 | 79637274 | Hyper | cancer_general | FOXB2 |
| chr9 | 79637555 | 79638150 | Hyper | cancer_general | FOXB2 | chr9 | 80409473 | 80409502 | Hyper | literature | GNAQ |
| chr9 | 85677905 | 85677992 | Hyper | blood | RASEF | chr9 | 86152387 | 86152417 | Hyper | cancer_general | — |
| chr9 | 86755532 | 86755952 | Hyper | cancer_general | — | chr9 | 86886706 | 86886736 | Hyper | cancer_general | SLC28A3 |
| chr9 | 87283008 | 87283038 | Hyper | cancer_general | NTRK2 | chr9 | 87283677 | 87283709 | Hyper | cancer_general | NTRK2 |
| chr9 | 87284706 | 87284798 | Hyper | tcga, cancer_general | NTRK2 | chr9 | 87285279 | 87285472 | Hyper | cancer_general | INTRK2 |
| chr9 | 88137524 | 88137998 | Hyper | cancer_general | — | chr9 | 89517699 | 89517835 | Hyper | cancer_general | — |
| chr9 | 89560760 | 89560827 | Hyper | cancer_general | LOC100506834, GAS1 | chr9 | 89561063 | 89561109 | Hyper | cancer_general | LOC100506834, GAS1 |
| chr9 | 91150222 | 91150335 | Hyper | cancer_general | NXNL2 | chr9 | 91606004 | 91606058 | Hyper | cancer_general | C9orf47, S1PR3 |
| chr9 | 91792357 | 91792387 | Hyper | cancer_general | SHC3 | chr9 | 91792776 | 91792907 | Hyper | cancer_general | SHC3 |
| chr9 | 91793177 | 91793526 | Hyper | cancer_general | SHC3 | chr9 | 94183870 | 94183954 | Hyper | cancer_general | — |
| chr9 | 94712163 | 94712236 | Hyper | cancer_general | ROR2 | chr9 | 95569759 | 95569822 | Hyper | cancer_general | ANKRD19P |
| chr9 | 95570247 | 95570434 | Hyper | cancer_general | ANKRD19P | chr9 | 95571617 | 95571760 | Hyper | cancer_general | ANKRD19P |
| chr9 | 95947130 | 95947296 | Hyper | cancer_general | WNK2 | chr9 | 96588804 | 96588885 | Hyper | cancer_general | MIR4291 |
| chr9 | 96710377 | 96710407 | Hyper | cancer_general | BARX1 | chr9 | 96710647 | 96710991 | Hyper | cancer_general | BARX1 |
| chr9 | 96711258 | 96711617 | Hyper | cancer_general | BARX1 | chr9 | 96711975 | 96712005 | Hyper | cancer_general | BARX1 |
| chr9 | 96713378 | 96713893 | Hyper | cancer_general | BARX1 | chr9 | 96715095 | 96715857 | Hyper | tcga, cancer_general | BARX1 |
| chr9 | 96716837 | 96717466 | Hyper | cancer_general | JB148981, BARX1 | chr9 | 96717979 | 96718149 | Hyper | cancer_general | JB148981, BARX1 |
| chr9 | 96720803 | 96721802 | Hyper | lung, cancer_general | JB148981, BARX1 | chr9 | 96722445 | 96722786 | Hyper | cancer_general, lung | JB148981, BARX1 |
| chr9 | 96723093 | 96723202 | Hyper | cancer_general | BARX1, JB148981 | chr9 | 98111365 | 98112395 | Hyper | cancer_general | — |
| chr9 | 98784772 | 98784802 | Hyper | cancer_general | LINC00092, C9orf102, ERCC6L2 | chr9 | 98789651 | 98790000 | Hyper | cancer_general | LINC00092, C9orf102 |
| chr9 | 99146020 | 99146153 | Hyper | blood | ZNF367, SLC35D2 | chr9 | 99449135 | 99449451 | Hyper | liver_tcga, cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 99639621 | 99639942 | Hyper | cancer_general | LOC100132781, ZNF782 | chr9 | 99983140 | 99983170 | Hyper | cancer_general | — |
| chr9 | 99983411 | 99983824 | Hyper | cancer_general | — | chr9 | 99984026 | 99984242 | Hyper | cancer_general | — |
| chr9 | 100503625 | 100503937 | Hyper | cancer_general | — | chr9 | 100609991 | 100610218 | Hyper | cancer_general | FOXE1 |
| chr9 | 100611640 | 100611640 | Hyper | cancer_general | FOXE1 | chr9 | 100613828 | 100614325 | Hyper | cancer_general | FOXE1 |
| chr9 | 100614541 | 100616902 | Hyper | cancer_general, liver_tcga, cancer_general | FOXE1 | chr9 | 100617293 | 100617365 | Hyper | cancer_general | FOXE1 |
| chr9 | 100617682 | 100618055 | Hyper | cancer_general | FOXE1 | chr9 | 100619722 | 100620069 | Hyper | cancer_general | FOXE1 |
| chr9 | 100620330 | 100620783 | Hyper | cancer_general | FOXE1 | chr9 | 101469269 | 101469307 | Hyper | cancer_general | GABBR2 |
| chr9 | 101469603 | 101469796 | Hyper | cancer_general | GABBR2 | chr9 | 101470116 | 101470250 | Hyper | cancer_general | GABBR2 |
| chr9 | 101470968 | 101471071 | Hyper | cancer_general | GABBR2 | chr9 | 101470572 | 101471621 | Hyper | cancer_general | GABBR2 |
| chr9 | 101471860 | 101472009 | Hyper | tcga, cancer_general | GABBR2 | chr9 | 101705996 | 101706695 | Hyper | cancer_general | COL15A1 |
| chr9 | 104248579 | 104248623 | Hyper | cancer_general | TMEM246 | chr9 | 104249475 | 104249562 | Hyper | tcga | — |
| chr9 | 104500625 | 104500774 | Hyper | liver_tcga | — | chr9 | 110228200 | 110228602 | Hyper | liver_tcga, cancer_general | — |
| chr9 | 110251388 | 110251418 | Hyper | blood | KLF4 PALM2, Mir_548 | chr9 | 110252363 | 110252515 | Hyper | blood | KLF4 |
| chr9 | 112403170 | 112403200 | Hyper | cancer_general | — | chr9 | 113341522 | 113341965 | Hyper | tcga, cancer_general | — |
| chr9 | 113342299 | 113342340 | Hyper | cancer_general | — | chr9 | 115652966 | 115653425 | Hyper | cancer_general | SLC46A2 |
| chr9 | 118917024 | 118917079 | Hyper | cancer_general | PAPPA | chr9 | 120175795 | 120175832 | Hyper | cancer_general | — |
| chr9 | 120176104 | 120176151 | Hyper | cancer_general | — | chr9 | 120176867 | 120176897 | Hyper | cancer_general | — |
| chr9 | 120507409 | 120507439 | Hyper | cancer_general | — | chr9 | 122131481 | 122131642 | Hyper | cancer_general | DBC1 |
| chr9 | 122131880 | 122132227 | Hyper | tcga, cancer_general | DBC1 | chr9 | 123004898 | 123004928 | Hyper | esophageal | MIR147A |
| chr9 | 124535347 | 124535611 | Hyper | liver_tcga | DAB2IP | chr9 | 126770257 | 126770298 | Hyper | cancer_general | LHX2, AK131516 |
| chr9 | 126771532 | 126771705 | Hyper | cancer_general | LHX2, AK131516 | chr9 | 126774517 | 126775144 | Hyper | cancer_general | LHX2, AK131516 |
| chr9 | 126775530 | 126775560 | Hyper | cancer_general | LHX2, AK131516 | chr9 | 126776044 | 126776119 | Hyper | cancer_general | AK131516, LHX2 |
| chr9 | 126777529 | 126777982 | Hyper | literature | LHX2, AK131516 | chr9 | 126778329 | 126778496 | Hyper | cancer_general | AK131516, LHX2 |
| chr9 | 126779485 | 126780315 | Hyper | cancer_general | LHX2, AK131516 | chr9 | 126780811 | 126780898 | Hyper | cancer_general | LHX2, AK131516 |
| chr9 | 126783295 | 126783499 | Hyper | cancer_general | LHX2 | chr9 | 127212851 | 127213006 | Hyper | cancer_general | GPR144 |
| chr9 | 127265688 | 127266025 | Hyper | cancer_general | NR5A1 | chr9 | 127266387 | 127266534 | Hyper | cancer_general | NR5A1 |
| chr9 | 127920543 | 127920572 | Hyper | literature | PPP6C | chr9 | 128652200 | 128652232 | Hyper | cancer_general | PBX3 |
| chr9 | 129276718 | 129276820 | Hyper | cancer_general | — | chr9 | 129372929 | 129373223 | Hyper | cancer_general | LMX1B |
| chr9 | 129376170 | 129376199 | Hyper | literature | LMX1B | chr9 | 129376889 | 129376918 | Hyper | literature | LMX1B |
| chr9 | 129377214 | 129377316 | Hyper | cancer_general | LMX1B | chr9 | 129377604 | 129378003 | Hyper | tcga, literature, cancer_general | LMX1B |
| chr9 | 129381111 | 129381180 | Hyper | cancer_general | LMX1B | chr9 | 129387434 | 129387464 | Hyper | cancer_general | LMX1B |
| chr9 | 129387800 | 129388200 | Hyper | cancer_general | LMX1B | chr9 | 129388996 | 129389192 | Hyper | cancer_general | LMX1B |
| chr9 | 129400986 | 129401195 | Hyper | cancer_general, breast | LMX1B | chr9 | 129445255 | 129445566 | Hyper | cancer_general | LMX1B |
| chr9 | 129445783 | 129445813 | Hyper | cancer_general | LMX1B | chr9 | 129485841 | 129485923 | Hyper | cancer_general | — |
| chr9 | 130461642 | 130461742 | Hyper | cancer_general | C9orf117, BC032117, | chr9 | 130689626 | 130689749 | Hyper | liver_tcga | DPM2, PIP5KL1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 132382383 | 132383109 | Hyper | tcga, literature, cancer_general | MIR3911, STXBP1, NTMT1, C9orf50 | chr9 | 132804405 | 132804455 | Hyper | esophageal | FNBP1 |
| chr9 | 132804796 | 132804974 | Hyper | esophageal | FNBP1 | chr9 | 132805318 | 132805445 | Hyper | esophageal | FNBP1 |
| chr9 | 132805737 | 132805893 | Hyper | esophageal | FNBP1 | chr9 | 133308893 | 133308941 | Hyper | cancer_general | AK074396 |
| chr9 | 133534683 | 133534713 | Hyper | cancer_general | PRDM12 | chr9 | 133535734 | 133535839 | Hyper | cancer_general | PRDM12 |
| chr9 | 133536097 | 133536344 | Hyper | cancer_general | PRDM12 | chr9 | 133536778 | 133536869 | Hyper | tcga | PRDM12 |
| chr9 | 133537182 | 133537549 | Hyper | cancer_general | PRDM12 | chr9 | 133538169 | 133538728 | Hyper | cancer_general | PRDM12 |
| chr9 | 133539606 | 133539709 | Hyper | cancer_general | PRDM12 | chr9 | 133541059 | 133541192 | Hyper | cancer_general | PRDM12 |
| chr9 | 133541689 | 133542337 | Hyper | cancer_general | PRDM12 | chr9 | 133738343 | 133738372 | Hyper | literature | ABL1, AX748265 |
| chr9 | 133747505 | 133747534 | Hyper | literature | AX748265, ABL1 | chr9 | 134421797 | 134421835 | Hyper | blood | — |
| chr9 | 135037119 | 135037357 | Hyper | tcga | NTNG2 | chr9 | 135455407 | 135455585 | Hyper | cancer_general | BARHL1, C9orf171 |
| chr9 | 135455996 | 135456065 | Hyper | cancer_general | BARHL1, C9orf171 | chr9 | 135456496 | 135456526 | Hyper | cancer_general | BARHL1, C9orf171 |
| chr9 | 135456897 | 135456932 | Hyper | cancer_general | BARHL1, C9orf171 | chr9 | 135458477 | 135458597 | Hyper | cancer_general | BARHL1, C9orf171 |
| chr9 | 135460001 | 135460176 | Hyper | cancer_general | BARHL1, DDX31 | chr9 | 135460869 | 135460899 | Hyper | cancer_general | DDX31, BARHL1 |
| chr9 | 135461511 | 135461773 | Hyper | cancer_general | DDX31, BARHL1 | chr9 | 135462048 | 135462967 | Hyper | cancer_general | DDX31, BARHL1 |
| chr9 | 135464798 | 135464918 | Hyper | cancer_general | DDX31, ABRHL1 | chr9 | 135465948 | 135466132 | Hyper | cancer_general | DDX31, BARHL1 |
| chr9 | 135466344 | 135466660 | Hyper | cancer_general | DDX31, BARHL1 | chr9 | 135796801 | 135796830 | Hyper | literature | TSC1 |
| chr9 | 136474490 | 136474607 | Hyper | cancer_general | — | chr9 | 137111397 | 137111426 | Hyper | liver_tcga | — |
| chr9 | 137229892 | 137229921 | Hyper | liver_tcga | RXRA | chr9 | 137299119 | 137299450 | Hyper | tcga, cancer_general | RXRA |
| chr9 | 137533974 | 137534238 | Hyper | cancer_general | COL5A1 | chr9 | 137702189 | 137702222 | Hyper | esophageal | LOC101448202, COL5A1 |
| chr9 | 137979893 | 137980011 | Hyper | cancer_general | OLFM1 | chr9 | 137980258 | 137980288 | Hyper | cancer_general | OLFM1 |
| chr9 | 137980880 | 137980910 | Hyper | cancer_general | OLFM1 | chr9 | 138606307 | 138606372 | Hyper | cancer_general | KCNT1 |
| chr9 | 138606796 | 138606923 | Hyper | tcga | KCNT1 | chr9 | 139024723 | 139024782 | Hyper | cancer_general | — |
| chr9 | 139085228 | 139085360 | Hyper | cancer_general | RBSG2, LHX3 | chr9 | 139085924 | 139085978 | Hyper | cancer_general | LHX3, RBSG2 |
| chr9 | 139090500 | 139090578 | Hyper | cancer_general | QSOX2, LHX3, RBSG2 | chr9 | 139090793 | 139091369 | Hyper | cancer_general | QSOX2, LHX3, RBSG2 |
| chr9 | 139093681 | 139093890 | Hyper | cancer_general | QSOX2, LHX3, RBSG2 | chr9 | 139094705 | 139094873 | Hyper | cancer_general | QSOX2, LHX3, RBSG2 |
| chr9 | 139095340 | 139095485 | Hyper | cancer_general | QSOX2, LHX3, RBSG2 | chr9 | 139096650 | 139097006 | Hyper | cancer_general | LHX3, QSOX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 139399407 | 139399436 | Hyper | literature | NOTCH1 | chr9 | 139739236 | 139739300 | Hyper | cancer_general | PHPT1, MAMDC4, C9orf172, RABL6 |
| chr9 | 140024842 | 140025023 | Hyper | colorectal, cancer_general | GRIN1 | chr9 | 140032891 | 140032951 | Hyper | cancer_general | GRIN1 |
| chr9 | 140033426 | 140033642 | Hyper | cancer_general | GRIN1 | chr9 | 140033909 | 140034079 | Hyper | cancer_general | GRIN1 |
| chr9 | 140050969 | 140051354 | Hyper | liver_tcga, cancer_general | GRIN1 | chr9 | 140197122 | 140197263 | Hyper | hepatobiliary | NRARP, EXD3 |
| chr9 | 140771975 | 140772347 | Hyper | literature, cancer_general | CACNA1B, AK128414 | chr9 | 140772586 | 140773301 | Hyper | cancer_general | CACNA1B, AK128414 |
| chr19 | 462181 | 462269 | Hyper | blood | ODF3L2, SHC2 | chr19 | 591365 | 591416 | Hyper | cancer_general | HCN2, BSG |
| chr19 | 1220422 | 1220610 | Hyper | literature | C19orf26, STK11 | chr19 | 1221981 | 1222010 | Hyper | literature | C19orf26, STK11 |
| chr19 | 1308047 | 1308081 | Hyper | head_neck | EFNA2 | chr19 | 1401752 | 1401795 | Hyper | tcga | NDUFS7, DAZAP1, GAMT, KA126693 |
| chr19 | 1450319 | 1450390 | Hyper | cancer_general | APC2, RPS15 | chr19 | 1467423 | 1468188 | Hyper | cancer_general | C19orf25, APC2 |
| chr19 | 1524368 | 1524447 | Hyper | cancer_general | PLK5 | chr19 | 1754172 | 1754254 | Hyper | cancer_general | ONECUT3 |
| chr19 | 1754739 | 1754804 | Hyper | cancer_general | ONECUT3 | chr19 | 1757416 | 1757615 | Hyper | cancer_general | ONECUT3 |
| chr19 | 1762474 | 1762575 | Hyper | cancer_general | ONECUT3 | chr19 | 1764293 | 1764339 | Hyper | pancreas | ONECUT3 |
| chr19 | 1775076 | 1775239 | Hyper | head_neck | ATP8B3, ONECUT3 | chr19 | 1776376 | 1776534 | Hyper | pancreas, cancer_general | ATP8B3, ONECUT3 |
| chr19 | 2135672 | 2135701 | Hyper | liver_tcga | — | chr19 | 2251152 | 2251715 | Hyper | cancer_general | JSRP1, MIR4321, AMH, SF3A2 |
| chr19 | 2252066 | 2252658 | Hyper | tcga, cancer_general | JSRP1, MIR4321, AMH, SF3A2 | chr19 | 2252984 | 2253775 | Hyper | tcga, cancer_general | JSRP1, MIR4321, AMH, SF3A2 |
| chr19 | 2290253 | 2291034 | Hyper | tcga, cancer_general | SPPL2B, AX747191, LINGO3, C19orf35 | chr19 | 2302793 | 2302951 | Hyper | cancer_general | — |
| chr19 | 3114998 | 3115027 | Hyper | literature | DKFZp434J194, GNA11 | chr19 | 3118927 | 3118956 | Hyper | literature | GNA11, DKFZp434J194 |
| chr19 | 3361139 | 3361388 | Hyper | tcga | NFIC | chr19 | 3659668 | 3659793 | Hyper | liver_tcga | PIP5K1C |
| chr19 | 3785649 | 3786260 | Hyper | tcga, liver_tcga, cancer_general | JA611290, MATK | chr19 | 3822111 | 3822203 | Hyper | tcga | ZFR2 |
| chr19 | 4101087 | 4101116 | Hyper | literature | MAP2K2 | chr19 | 4110565 | 4110597 | Hyper | literature | MAP2K2 |
| chr19 | 4117526 | 4117630 | Hyper | literature | MAP2K2 | chr19 | 4305057 | 4305086 | Hyper | literature | FSD1, TMIGD2 |
| chr19 | 4944145 | 4944174 | Hyper | liver_tcga | — | chr19 | 5292812 | 5292844 | Hyper | pancreas | PTPRS |
| chr19 | 5338914 | 5339143 | Hyper | tcga, cancer_general | — | chr19 | 6590325 | 6590478 | Hyper | cancer_general | CD70 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 7615996 | 7616025 | Hyper | liver_tcga | PNPLA6 | chr19 | 7746942 | 7747042 | Hyper | tcga | TRAPPC5, FCER2, C19orf59 |
| chr19 | 7795012 | 7795244 | Hyper | cancer_general | CD209, CLEC4G | chr19 | 7853028 | 7853157 | Hyper | cancer_general | CLEC4GP1 |
| chr19 | 7853361 | 7853460 | Hyper | cancer_general | CLEC4GP1 | chr19 | 8115235 | 8115276 | Hyper | cancer_general | CCL25 |
| chr19 | 9420142 | 9420240 | Hyper | esophageal | ZNF699 | chr19 | 9473564 | 9474056 | Hyper | liver_tcga, literature, cancer_general | ZNF177, ZNF559-ZNF177 |
| chr19 | 9517609 | 9517771 | Hyper | cancer_general | ZNF266 | chr19 | 9608895 | 9609036 | Hyper | cancer_general | ZNF560 |
| chr19 | 9609319 | 9609436 | Hyper | cancer_general, literature | ZNF560 | chr19 | 9903913 | 9904100 | Hyper | tcga, cancer_general | — |
| chr19 | 10398209 | 10398285 | Hyper | cancer_general | ICAM4, ICAM1, ICAM5 | chr19 | 10405972 | 10406349 | Hyper | cancer_general | ZGLP1, FDX1L, ICAM5, ICAM4, ICAM1 |
| chr19 | 10406806 | 10407135 | Hyper | lung, cancer_general | ICAM1, LZGP1, FDX1L, ICAM5, ICAM4 | chr19 | 10527165 | 10527243 | Hyper | esophageal | PDE4A |
| chr19 | 10531419 | 10531512 | Hyper | tcga | PDE4A | chr19 | 10531964 | 10531994 | Hyper | cancer_general | PDE4A |
| chr19 | 10600431 | 10600460 | Hyper | literature | KEAP1 | chr19 | 10602274 | 10602348 | Hyper | literature | KEAP1 |
| chr19 | 10602565 | 10602864 | Hyper | literature | KEAP1 | chr19 | 10610138 | 10610260 | Hyper | literature | KEAP1 |
| chr19 | 10624751 | 10625465 | Hyper | cancer_general | S1PR5 | chr19 | 11134252 | 11134281 | Hyper | literature | SMARCA4 |
| chr19 | 11138507 | 11138536 | Hyper | literature | SMARCA4 | chr19 | 11492252 | 11492528 | Hyper | lung | SMARCA4, RGL3, EPOR, SWSAP1 |
| chr19 | 11591031 | 11591185 | Hyper | cancer_general | ZNF653, ELAVL3 | chr19 | 11592710 | 11592750 | Hyper | cancer_general | ELAVL3, ZNF653 |
| chr19 | 11593022 | 11593159 | Hyper | cancer_general | ZNF653, ELAVL3 | chr19 | 11689460 | 11689564 | Hyper | cancer_general | ACP5, BC039523 |
| chr19 | 11959912 | 11960077 | Hyper | cancer_general | ZNF439 | chr19 | 12163448 | 12163672 | Hyper | esophageal | ZNF878 |
| chr19 | 12163893 | 12163923 | Hyper | esophageal | ZNF878 | chr19 | 12175445 | 12175504 | Hyper | esophageal | ZNF844 |
| chr19 | 12175814 | 12176005 | Hyper | cancer_general | ZNF844 | chr19 | 12203028 | 12203744 | Hyper | liver_tcga, cancer_general | ZNF788 |
| chr19 | 12267019 | 12267667 | Hyper | tcga, cancer_general | ZNF136, ZNF625 | chr19 | 12305839 | 12306263 | Hyper | liver_tcga, literature, cancer_general | AX721123, ZNF136, AK023304 |
| chr19 | 12476492 | 12476556 | Hyper | esophageal | ZNF442 | chr19 | 12595109 | 12595307 | Hyper | esophageal | ZNF709 |
| chr19 | 12595845 | 12595896 | Hyper | esophageal | ZNF709 | chr19 | 12606381 | 12606511 | Hyper | esophageal | ZNF709 |
| chr19 | 12750987 | 12751056 | Hyper | cancer_general | MAN2B1 | chr19 | 12952000 | 12952139 | Hyper | cancer_general | RTBDN, MAST1 |
| chr19 | 12996169 | 12996280 | Hyper | pancreas | DNASE2, GCDH, KLF1 | chr19 | 13113454 | 13113668 | Hyper | liver_tcga | NFIX |
| chr19 | 13210225 | 13210316 | Hyper | cancer_general | TRMT1, LYL1, NFIX | chr19 | 13616696 | 13617256 | Hyper | cancer_general | CACNA1A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 13618288 | 13618381 | Hyper | cancer_general | CACNA1A | chr19 | 14584240 | 14584775 | Hyper | cancer_general | GIPC1, PTGER1, PKN1 |
| chr19 | 15090172 | 15090499 | Hyper | cancer_general | SLC1A6 | chr19 | 15121685 | 15121894 | Hyper | cancer_general | CCDC105 |
| chr19 | 15122120 | 15122238 | Hyper | tcga | CCDC105 | chr19 | 15288433 | 15288856 | Hyper | cancer_general | NOTCH3 |
| chr19 | 15342734 | 15343373 | Hyper | cancer_general, liver_tcga | BRD4, EPHX3 | chr19 | 15344107 | 15344325 | Hyper | cancer_general | BRD4, EPHX3 |
| chr19 | 15580685 | 15580714 | Hyper | literature | PGLYRP2, RASAL3 | chr19 | 16999599 | 16999782 | Hyper | literature | SIN3B, F2RL3, CPAMD8 |
| chr19 | 17007086 | 17007662 | Hyper | cancer_general | CPAMD8, F2RL3 | chr19 | 17008523 | 17008799 | Hyper | cancer_general, liver_tcga | CPAMD8, F2RL3 |
| chr19 | 17392641 | 17392866 | Hyper | tcga | ANKLE1, BABAM1 | chr19 | 17717286 | 17717315 | Hyper | literature | UNC13A |
| chr19 | 17791182 | 17791211 | Hyper | literature | UNC13A | chr19 | 17943423 | 17943452 | Hyper | literature | JAK3 |
| chr19 | 17945891 | 17945983 | Hyper | literature | JAK3 | chr19 | 17947991 | 17948023 | Hyper | literature | JAK3 |
| chr19 | 17949094 | 17949123 | Hyper | literature | JAK3 | chr19 | 17958490 | 17958839 | Hyper | tcga | JAK3 |
| chr19 | 17983537 | 17983834 | Hyper | cancer_general | SLC5A5 | chr19 | 18271894 | 18271923 | Hyper | literature | PIK3R2, MAST3 |
| chr19 | 18278047 | 18278076 | Hyper | literature | PIK3R2, IFI30 | chr19 | 18343439 | 18343569 | Hyper | cancer_general | PDE4C |
| chr19 | 18343921 | 18343963 | Hyper | cancer_general | PDE4C | chr19 | 18714552 | 18714675 | Hyper | cancer_general | TMEM59L, CRLF1 |
| chr19 | 18811560 | 18811804 | Hyper | tcga | CRTC1 | chr19 | 18899432 | 18899652 | Hyper | cancer_general | COMP, CRTC1 |
| chr19 | 18901828 | 18902095 | Hyper | tcga, cancer_general | COMP, CRTC1 | chr19 | 18980760 | 18980897 | Hyper | cancer_general | UPF1, CERS1, GDF1 |
| chr19 | 19260030 | 19260101 | Hyper | literature | MEF2B, MEF2BNB-MEF2B | chr19 | 19261519 | 19261548 | Hyper | literature | MEF2B, MEF2BNB-MEF2B |
| chr19 | 19651961 | 19652066 | Hyper | liver_tcga | CILP2, YJEFN3 | chr19 | 19729251 | 19729395 | Hyper | liver_tcga | LPAR2, PBX4 |
| chr19 | 19739172 | 19739428 | Hyper | tcga, liver_tcga | GMIP, LPAR2, PBX4 | chr19 | 20011955 | 20012149 | Hyper | liver_tcga, cancer_general | ZNF93, ZNF253 |
| chr19 | 20188693 | 20188872 | Hyper | cancer_general | ZNF90 | chr19 | 20189322 | 20189438 | Hyper | cancer_general | ZNF90 |
| chr19 | 21646407 | 21646437 | Hyper | cancer_general | CR627135 | chr19 | 21688814 | 21688912 | Hyper | esophageal | ZNF429, LINC00664 |
| chr19 | 21769300 | 21769444 | Hyper | tcga | BC033373, AX748435 | chr19 | 22018523 | 22018805 | Hyper | tcga | ZNF43 |
| chr19 | 22034198 | 22034813 | Hyper | cancer_general | ZNF43 | chr19 | 22610635 | 22610747 | Hyper | cancer_general | MEF2B, MEF2BNB-MEF2B |
| chr19 | 22715140 | 22715443 | Hyper | cancer_general | — | chr19 | 23254189 | 23254219 | Hyper | cancer_general | ZNF429 |
| chr19 | 23257703 | 23258694 | Hyper | cancer_general | — | chr19 | 23299748 | 23300080 | Hyper | tcga, cancer_general | ZNF730 |
| chr19 | 23432562 | 23432723 | Hyper | esophageal | AK023040, ZNF724P | chr19 | 23433143 | 23433296 | Hyper | esophageal | ZNF98 |
| chr19 | 23456615 | 23456881 | Hyper | esophageal | AK023040 | chr19 | 23598274 | 23598326 | Hyper | cancer_general | AK023040, ZNF724P, BC043213, AK022793 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 24154592 | 24154621 | Hyper | liver_tcga | — | chr19 | 24216975 | 24217023 | Hyper | esophageal | ZNF254, AK092150, AK092080 |
| chr19 | 29284452 | 29284719 | Hyper | cancer_general | — | chr19 | 30015934 | 30016712 | Hyper | cancer_general | VSTM2B, LOC284395 |
| chr19 | 30016914 | 30018608 | Hyper | cancer_general | VSTM2B, LOC284395 | chr19 | 30019145 | 30019838 | Hyper | tcga, cancer_general | VSTM2B, LOC284395 |
| chr19 | 30020093 | 30020473 | Hyper | cancer_general | VSTM2B, LOC284395 | chr19 | 30021125 | 30021193 | Hyper | cancer_general | VSTM2B, LOC284395 |
| chr19 | 30215542 | 30215571 | Hyper | tcga | C19orf12 | chr19 | 30713480 | 30713706 | Hyper | cancer_general | — |
| chr19 | 30713909 | 30714047 | Hyper | cancer_general | — | chr19 | 30714403 | 30714433 | Hyper | cancer_general | — |
| chr19 | 30715402 | 30715766 | Hyper | cancer_general | — | chr19 | 30716313 | 30716576 | Hyper | cancer_general | — |
| chr19 | 30716812 | 30718149 | Hyper | tcga, cancer_general | — | chr19 | 30718847 | 30718913 | Hyper | cancer_general | — |
| chr19 | 30719449 | 30720067 | Hyper | tcga, cancer_general | — | chr19 | 30865713 | 30866436 | Hyper | cancer_general, tcga | ZNF536 |
| chr19 | 31839765 | 31839873 | Hyper | cancer_general | TSHZ3 | chr19 | 31841937 | 31842389 | Hyper | tcga, cancer_general | TSHZ3 |
| chr19 | 31842596 | 31842646 | Hyper | cancer_general | TSHZ3 RGS9BP, ANKRD27 | chr19 | 32715673 | 32715741 | Hyper | cancer_general | — |
| chr19 | 33167116 | 33167431 | Hyper | cancer_general | | chr19 | 33685544 | 33685581 | Hyper | esophageal | LRP3 |
| chr19 | 33792159 | 33792524 | Hyper | blood | CEBPA-AS1, CEBPA | chr19 | 33794675 | 33794760 | Hyper | tcga | CEBPA-AS1, CEBPA |
| chr19 | 34112288 | 34112320 | Hyper | cancer_general | CHST8 | chr19 | 34112524 | 34112973 | Hyper | cancer_general | CHST8 |
| chr19 | 34113349 | 34113587 | Hyper | cancer_general | CHST8 | chr19 | 34114006 | 34114113 | Hyper | cancer_general | CHST8 |
| chr19 | 34533139 | 34533169 | Hyper | head_neck | — | chr19 | 34972464 | 34972494 | Hyper | blood | WTIP |
| chr19 | 34973225 | 34973255 | Hyper | cancer_general | WTIP | chr19 | 34973656 | 34973697 | Hyper | cancer_general | WTIP |
| chr19 | 34973932 | 34973965 | Hyper | pancreas | WTIP | chr19 | 35264085 | 35264119 | Hyper | esophageal | ZNF599 |
| chr19 | 35396013 | 35396370 | Hyper | cancer_general | LINC00904, BC031235 | chr19 | 36048595 | 36048771 | Hyper | cancer_general, liver_tcga | ATP4A |
| chr19 | 36049327 | 36049462 | Hyper | tcga | ATP4A | chr19 | 36334979 | 36335147 | Hyper | cancer_general | NPHS1 |
| chr19 | 36347892 | 36348048 | Hyper | tcga | KIRREL2 | chr19 | 36450106 | 36450372 | Hyper | tcga, cancer_general | — |
| chr19 | 36523333 | 36523480 | Hyper | cancer_general | THAP8, CLIP3, BC071809 | chr19 | 36736027 | 36736057 | Hyper | cancer_general | ZNF146 |
| chr19 | 36736319 | 36736491 | Hyper | cancer_general | ZNF146 | chr19 | 36822324 | 36822892 | Hyper | cancer_general | ZFP14, LINC00665 |
| chr19 | 36909050 | 36909935 | Hyper | tcga, liver_tcga, cancer_general | LOC644189, ZFP82 | chr19 | 36912354 | 36912398 | Hyper | cancer_general | ZFP82, LOC644189 |
| chr19 | 37095665 | 37096575 | Hyper | tcga, literature, cancer_general | ZNF382, ZNF529 | chr19 | 37263532 | 37263584 | Hyper | esophageal | AX747375, BC024306, ZNF850 |
| chr19 | 37264222 | 37264421 | Hyper | cancer_general | BC024306, AX747375, ZNF850 | chr19 | 37288013 | 37288765 | Hyper | tcga, cancer_general | ZNF790-AS1 |
| chr19 | 37341761 | 37341962 | Hyper | esophageal | ZNF345, ZNF790 | chr19 | 37407127 | 37407443 | Hyper | cancer_general | ZNF568, ZNF829 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 37464048 | 37464696 | Hyper | tcga, cancer_general | ZNF568 | chr19 | 37569289 | 37569554 | Hyper | esophageal | ZNF420 |
| chr19 | 37808445 | 37808485 | Hyper | esophageal | HKR1 | chr19 | 37959858 | 37959963 | Hyper | cancer_general | ZNF570, ZNF569 |
| chr19 | 37997433 | 37998138 | Hyper | cancer_general, tcga | ZNF793 | chr19 | 38042365 | 38042693 | Hyper | cancer_general | ZNF571, ZNF540, ZNF571-AS1 |
| chr19 | 38085254 | 38086066 | Hyper | esophageal | ZNF540, ZNF571 ZFP30 | chr19 | 38146062 | 38146247 | Hyper | esophageal | ZFP30 |
| chr19 | 38146457 | 38146568 | Hyper | esophageal | ZFP30 | chr19 | 38182884 | 38183299 | Hyper | cancer_general, tcga, liver_tcga, literature | ZNF607 |
| chr19 | 38308080 | 38308466 | Hyper | cancer_general | LOC644554, LOC100631378 | chr19 | 38747159 | 38747582 | Hyper | tcga, cancer_general, liver_tcga | SPINT2, PPP1R14A |
| chr19 | 38755272 | 38755344 | Hyper | tcga, liver_tcga | SPINT2, PPP1R14A | chr19 | 39687663 | 39687844 | Hyper | cancer_general | SYCN, NCCRP1 |
| chr19 | 39754874 | 39755358 | Hyper | cancer_general | IFNL2 SELV, DLL3 | chr19 | 39993477 | 39993664 | Hyper | cancer_general | DLL3 |
| chr19 | 39997688 | 39997813 | Hyper | cancer_general | | chr19 | 40006177 | 40006306 | Hyper | tcga | DLL3, SELV |
| chr19 | 40006576 | 40006639 | Hyper | cancer_general | SELV, DLL3 | chr19 | 40724000 | 40724263 | Hyper | cancer_general | CNTD2, TTC9B, MAP3K10 |
| chr19 | 40762943 | 40762972 | Hyper | literature | AKT2 | chr19 | 41018510 | 41019031 | Hyper | cancer_general, pancreas, liver_tcga | SPTBN4 |
| chr19 | 41025539 | 41025683 | Hyper | cancer_general | SPTBN4 | chr19 | 41059909 | 41060306 | Hyper | cancer_general | |
| chr19 | 41073587 | 41073677 | Hyper | cancer_general | SPTBN4, SHKBP1 | chr19 | 41119177 | 41119633 | Hyper | cancer_general | LTBP4 |
| chr19 | 41354666 | 41354722 | Hyper | cancer_general | CYP2A6 | chr19 | 41641831 | 41641886 | Hyper | cancer_general | DQ590318, CYP2F1 |
| chr19 | 41698787 | 41698920 | Hyper | blood | CYP2S1 | chr19 | 42028502 | 42028549 | Hyper | pancreas | — |
| chr19 | 42827891 | 42828266 | Hyper | liver_tcga, literature, cancer_general | MEGF8, TMEM145 | chr19 | 44203830 | 44203877 | Hyper | cancer_general | — |
| chr19 | 44405908 | 44406087 | Hyper | cancer_general | LOC100505715 | chr19 | 44905499 | 44905529 | Hyper | cancer_general | ZNF285 |
| chr19 | 44952282 | 44952881 | Hyper | tcga, cancer_general | ZNF229 | chr19 | 45300144 | 45300197 | Hyper | cancer_general | CBLC |
| chr19 | 45655393 | 45656363 | Hyper | cancer_general | TRAPPC6A, NKPD1, PPP1R37 | chr19 | 45656682 | 45656913 | Hyper | cancer_general | TRAPPC6A, NKPD1, PPP1R37 |
| chr19 | 45657212 | 45657284 | Hyper | cancer_general | TRAPPC6A, NKPD1, PPP1R37 | chr19 | 45889946 | 45889397 | Hyper | cancer_general | PPP1R13L |
| chr19 | 46002048 | 46002320 | Hyper | cancer_general | PPM1N, VASP, RTN2 | chr19 | 46379914 | 46380148 | Hyper | tcga | FOXA3, IRF2BP1 |
| chr19 | 46916725 | 46917075 | Hyper | literature, cancer_general | CCDC8 | chr19 | 46930129 | 46930200 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 46974552 | 46974700 | Hyper | literature, cancer_general | PPP5D1, PNMAL1 | chr19 | 46992718 | 46992866 | Hyper | cancer_general | PNMAL2, BC132841, PPP5D1 |
| chr19 | 46993164 | 46993388 | Hyper | cancer_general | PNMAL2, BC132841, PPP5D1 | chr19 | 46996501 | 46996918 | Hyper | tcga, literature, cancer_general | BC132841, PNMAL2, PPP5D1 |
| chr19 | 47152617 | 47153011 | Hyper | cancer_general | DACT3 | chr19 | 47776713 | 47776742 | Hyper | liver_tcga | PRR24, CCDC9 |
| chr19 | 47910482 | 47910517 | Hyper | cancer_general | MEIS3 | chr19 | 47933311 | 47933732 | Hyper | cancer_general | SLC8A2 |
| chr19 | 47951288 | 47951318 | Hyper | liver_tcga | SLC8A2 | chr19 | 48076642 | 48076672 | Hyper | cancer_general | — |
| chr19 | 48918100 | 48918598 | Hyper | tcga, cancer_general | Mir_324, GRIN2D | chr19 | 49127373 | 49127674 | Hyper | tcga, cancer_general, liver_tcga | SPHK2, DBP, RPL18 |
| chr19 | 49256396 | 49256438 | Hyper | hepatobiliary | FGF21, FUT1, IZUMO1 | chr19 | 49399218 | 49399310 | Hyper | cancer_general | NUCB1, Mir_324, TULP2 |
| chr19 | 49575460 | 49575489 | Hyper | liver_tcga | KCNA7 | chr19 | 49646149 | 49646213 | Hyper | cancer_general | PPFIA3, HRC |
| chr19 | 49935736 | 49936174 | Hyper | cancer_general | LOC100507003, PTH2, SLC17A7 | chr19 | 49936864 | 49936894 | Hyper | cancer_general | SLC17A7, LOC100507003 |
| chr19 | 50316244 | 50316468 | Hyper | liver_tcga, colorectal | MED25, FUZ, AP2A1 | chr19 | 50553680 | 50553709 | Hyper | liver_tcga | FLJ26850, ZNF473 |
| chr19 | 50553997 | 50554510 | Hyper | liver_tcga, cancer_general | FLJ26850, ZNF473 | chr19 | 50816431 | 50816474 | Hyper | cancer_general | KCNC3, MYH14 |
| chr19 | 50833828 | 50833863 | Hyper | cancer_general | NAPSB, NR1H2, KCNC3 | chr19 | 51041149 | 51041189 | Hyper | head_neck | LRRC4B |
| chr19 | 51161225 | 51161255 | Hyper | cancer_general | SHANK1, C19orf81 | chr19 | 51162197 | 51162527 | Hyper | tcga, cancer_general | SHANK1, C19orf81 |
| chr19 | 51171219 | 51171278 | Hyper | cancer_general | SHANK1, C19orf81 | chr19 | 51171828 | 51171861 | Hyper | cancer_general | SHANK1, C19orf81 |
| chr19 | 51227719 | 51227785 | Hyper | cancer_general | CLEC11A, SHANK1 | chr19 | 51228049 | 51228079 | Hyper | pancreas | SHANK1, CLEC11A |
| chr19 | 51228308 | 51228507 | Hyper | cancer_general | CLEC11A, SHANK1 | chr19 | 51520423 | 51520453 | Hyper | cancer_general | KLK11, KLK10, KLK9 |
| chr19 | 51830845 | 51831128 | Hyper | cancer_general | VSIG10L, IGLON5 | chr19 | 51831360 | 51831390 | Hyper | cancer_general | VSIG10L, IGLON5 |
| chr19 | 51925127 | 51925272 | Hyper | liver_tcga | LOC100129083, SIGLEC10 | chr19 | 52097689 | 52097732 | Hyper | esophageal | FLJ30403, AX748312, ZNF175 |
| chr19 | 52207254 | 52207367 | Hyper | tcga, liver_tcga | LINC00085, HAS1 | chr19 | 52222523 | 52223131 | Hyper | cancer_general | HAS1 |
| chr19 | 52452316 | 52452447 | Hyper | liver_tcga | BC014606, ZNF613 | chr19 | 52552104 | 52552151 | Hyper | pancreas | ZNF432 |
| chr19 | 52715963 | 52715992 | Hyper | literature | PPP2R1A | chr19 | 52839588 | 52839938 | Hyper | tcga, cancer_general | ZNF610, AK097759 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 52872924 | 52873440 | Hyper | tcga, cancer_general | ZNF880, ZNF610 | chr19 | 52956805 | 52956848 | Hyper | cancer_general | ZNF578 |
| chr19 | 53031185 | 53031215 | Hyper | esophageal | ZNF808 | chr19 | 53073293 | 53073354 | Hyper | cancer_general | ZNF701 |
| chr19 | 53073563 | 53073987 | Hyper | cancer_general | ZNF701 | chr19 | 53141619 | 53141745 | Hyper | liver_tcga | — |
| chr19 | 53193858 | 53193893 | Hyper | esophageal | — | chr19 | 53194281 | 53194396 | Hyper | cancer_general | — |
| chr19 | 53496649 | 53496846 | Hyper | tcga, liver_tcga | ZNF702P | chr19 | 53561668 | 53561733 | Hyper | cancer_general | ZNF160, ERVV-2 |
| chr19 | 53635952 | 53636091 | Hyper | tcga | ZNF347, ZNF415 | chr19 | 53661647 | 53661902 | Hyper | tcga, cancer_general | ZNF665, ZNF347 |
| chr19 | 53662174 | 53662694 | Hyper | tcga, cancer_general | ZNF665, NZF347 | chr19 | 53696414 | 53696580 | Hyper | cancer_general | ZNF665 |
| chr19 | 53700596 | 53700729 | Hyper | cancer_general | ZNF665 | chr19 | 53757895 | 53758247 | Hyper | tcga, cancer_general | ZNF677, VN1R2 |
| chr19 | 53811858 | 53811988 | Hyper | cancer_general | — | chr19 | 53836936 | 53836975 | Hyper | esophageal | ZNF845 |
| chr19 | 53837377 | 53837432 | Hyper | esophageal | ZNF845 | chr19 | 53970501 | 53970725 | Hyper | tcga, cancer_general | ZNF813, ZNF761 |
| chr19 | 53970968 | 53971157 | Hyper | cancer_general | ZNF813, ZNF761 | chr19 | 54023887 | 54024196 | Hyper | tcga | ZNF331 |
| chr19 | 54024521 | 54024884 | Hyper | tcga, cancer_general | ZNF331 | chr19 | 54369555 | 54369681 | Hyper | liver_tcga | MYADM |
| chr19 | 54411125 | 54411168 | Hyper | cancer_general | CACNG7 | chr19 | 54411556 | 54411586 | Hyper | cancer_general | CACNG7 |
| chr19 | 54412873 | 54412985 | Hyper | cancer_general | CACNG7 | chr19 | 54445344 | 54445513 | Hyper | cancer_general | CACNG7 |
| chr19 | 54481771 | 54481968 | Hyper | cancer_general | MIR935, ACCNG8 | chr19 | 54483173 | 54483546 | Hyper | tcga, liver_tcga, cancer_general | MIR935, CACNG8 |
| chr19 | 54485403 | 54485823 | Hyper | liver_tcga, cancer_general | MIR935, CACNG6, CACNG8 | chr19 | 54976488 | 54976518 | Hyper | liver_tcga | CDC42EP5, LENG9, KIAA1932 |
| chr19 | 55598767 | 55598888 | Hyper | tcga | EPS8L1, PPP1R12C, Mir_324 | chr19 | 55629883 | 55630028 | Hyper | cancer_general | — |
| chr19 | 56159273 | 56159499 | Hyper | tcga | CCDC106, U2AF2, ZNF581, ZNF580 | chr19 | 56189937 | 56189966 | Hyper | liver_tcga | EPN1, U2AF2 |
| chr19 | 56728678 | 56728976 | Hyper | cancer_general | ZSCANSA | chr19 | 56879501 | 56880008 | Hyper | tcga, cancer_general | ZNF542 |
| chr19 | 56904740 | 56905203 | Hyper | cancer_general, tcga | ZNF582-AS1, ZNF582 | chr19 | 56915320 | 56915428 | Hyper | cancer_general | ZNF583, ZNF582-AS1 |
| chr19 | 56988557 | 56988716 | Hyper | cancer_general | ZNF667-AS1, ZNF667 | chr19 | 56989528 | 56989754 | Hyper | tcga, cancer_general | ZNF667-AS1, ZNF667 |
| chr19 | 57050463 | 57050493 | Hyper | cancer_general | BX647249, ZFP28 | chr19 | 57149579 | 57149619 | Hyper | cancer_general | SMIM17 |
| chr19 | 57154885 | 57155017 | Hyper | cancer_general | SMIM17 | chr19 | 57182994 | 57183356 | Hyper | tcga, cancer_general | ZNF835 |
| chr19 | 57276656 | 57276700 | Hyper | cancer_general | BC036412, ZIM2, FJ997633 | chr19 | 57610855 | 57610985 | Hyper | tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 57617522 | 57618121 | Hyper | cancer_general | — | chr19 | 57683148 | 57683295 | Hyper | cancer_general | DUXA |
| chr19 | 57862395 | 57862783 | Hyper | tcga, colorectal | ZNF304 | chr19 | 57863009 | 57863148 | Hyper | colorectal, cancer_general | ZNF304 |
| chr19 | 58011124 | 58011281 | Hyper | cancer_general | ZNF773, ZNF419 | chr19 | 58038805 | 58038969 | Hyper | cancer_general | ZNF549 |
| chr19 | 58095006 | 58095835 | Hyper | tcga, cancer_general | ZIK1, ZNF416 | chr19 | 58111632 | 58111783 | Hyper | tcga | AX721128, ZNF530, ZIK1 |
| chr19 | 58125544 | 58125881 | Hyper | tcga | ZNF134, ZNF211, AX721128, ZNF530 | chr19 | 58144494 | 58144701 | Hyper | head_neck | ZNF211 |
| chr19 | 58219839 | 58220832 | Hyper | liver_tcga, literature, cancer_general | ZNF154 | chr19 | 58238326 | 58239088 | Hyper | tcga, cancer_general | ZNF671 |
| chr19 | 58400079 | 58400175 | Hyper | cancer_general | ZNF814 | chr19 | 58400417 | 58400518 | Hyper | cancer_general | ZNF814 |
| chr19 | 58458754 | 58459201 | Hyper | tcga, cancer_general | ZNF256 | chr19 | 58514518 | 58514552 | Hyper | cancer_general | LOC100128398, ZNF606 |
| chr19 | 58520739 | 58520941 | Hyper | cancer_general | LOC100128398, ZNF606 | chr19 | 58545145 | 58545837 | Hyper | cancer_general, pancreas, literature, liver_tcga | ZSCAN1 |
| chr19 | 58570528 | 58570666 | Hyper | cancer_general | ZNF135, ZSCAN1 | chr19 | 58609254 | 58609854 | Hyper | tcga, cancer_general | ZSCAN18 |
| chr19 | 58629886 | 58629975 | Hyper | liver_tcga, literature | ZSCAN18, ZNF329 | chr19 | 58661894 | 58662094 | Hyper | cancer_general | — |
| chr19 | 58666171 | 58666313 | Hyper | cancer_general | RPS5, MIR4754, LOC646862 | chr19 | 58740086 | 58740118 | Hyper | esophageal | ZNF544 |
| chr19 | 58907689 | 58908195 | Hyper | cancer_general | — | chr19 | 58951271 | 58951916 | Hyper | cancer_general, tcga | ZNF132, DQ581862 |
| chr10 | 1651331 | 1651374 | Hyper | cancer_general, tcga | — | chr10 | 1774858 | 1774887 | Hyper | literature | PFKP |
| chr10 | 1779417 | 1779744 | Hyper | cancer_general | — | chr10 | 3109360 | 3109459 | Hyper | liver_tcga | |
| chr10 | 7449954 | 7451390 | Hyper | tcga, colorectal, cancer_general | SFMBT2 | chr10 | 7452227 | 7452777 | Hyper | tcga, cancer_general, colorectal | SFMBT2 |
| chr10 | 7453313 | 7453930 | Hyper | tcga, colorectal, cancer_general | SFMBT2 | chr10 | 7708274 | 7708304 | Hyper | cancer_general | ITIH5 |
| chr10 | 7708790 | 7709087 | Hyper | cancer_general, tcga | ITIH5 | chr10 | 7709723 | 7709752 | Hyper | literature | ITIH5 |
| chr10 | 8075930 | 8075971 | Hyper | cancer_general | — | chr10 | 8076338 | 8076487 | Hyper | cancer_general | — |
| chr10 | 8076804 | 8077374 | Hyper | cancer_general | — | chr10 | 8077874 | 8078218 | Hyper | cancer_general | — |
| chr10 | 8085039 | 8085721 | Hyper | cancer_general | GATA3-AS1, BC036297, GATA3 | chr10 | 8085978 | 8086010 | Hyper | cancer_general | GATA3-AS1, BC036297, GATA3 |
| chr10 | 8091895 | 8092278 | Hyper | tcga, cancer_general | GATA3-AS1, BC036297, GATA3 | chr10 | 8093738 | 8093985 | Hyper | cancer_general | GATA3-AS1, BC036297, GATA3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 8095603 | 8095845 | Hyper | tcga, cancer_general | GATA3, BC036297, GATA3-AS1 | chr10 | 8096160 | 8096190 | Hyper | cancer_general | GATA3, BC036297, GATA3-AS1 |
| chr10 | 8096975 | 8097197 | Hyper | tcga, cancer_general | GATA3, BC036297, GATA3-AS1 | chr10 | 8097474 | 8097537 | Hyper | cancer_general | GATA3, BC036297, GATA3-AS1 |
| chr10 | 11059715 | 11060062 | Hyper | pancreas, liver_tcga, cancer_general | CELF2 | chr10 | 11206206 | 11206235 | Hyper | literature | CELF2 |
| chr10 | 11207179 | 11207276 | Hyper | cancer_general | CELF2 | chr10 | 12390825 | 12390995 | Hyper | esophageal | CAMK1D |
| chr10 | 12391870 | 12392327 | Hyper | esophageal | CAMK1D | chr10 | 13043386 | 13043425 | Hyper | cancer_general | AK311458 |
| chr10 | 13933005 | 13933035 | Hyper | cancer_general | FRMD4A | chr10 | 13933436 | 13934183 | Hyper | tcga, cancer_general | FRMD4A |
| chr10 | 15761292 | 15761671 | Hyper | cancer_general | ITGA8 | chr10 | 15762124 | 15762154 | Hyper | cancer_general | ITGA8 |
| chr10 | 16562086 | 16563909 | Hyper | literature, cancer_general | C1QL3 | chr10 | 17269628 | 17269789 | Hyper | literature | VIM, BC078172 |
| chr10 | 17270072 | 17270445 | Hyper | literature | VIM, BC078172 | chr10 | 17270991 | 17271625 | Hyper | tcga, liver_tcga, cancer_general, literature | VIM, BC078172 |
| chr10 | 17271914 | 17272233 | Hyper | tcga, literature | VIM, BC078172 | chr10 | 17272601 | 17272630 | Hyper | literature | VIM, BC078172 |
| chr10 | 17273172 | 17273201 | Hyper | literature | VIM, BC078172 | chr10 | 17496214 | 17496734 | Hyper | cancer_general | — |
| chr10 | 18429245 | 18429287 | Hyper | cancer_general | CACNB2 | chr10 | 18429628 | 18429774 | Hyper | tcga | CACNB2 |
| chr10 | 21462533 | 21462607 | Hyper | blood | NEBL-AS1 | chr10 | 21462970 | 21463023 | Hyper | blood | NEBL-AS1 |
| chr10 | 21805217 | 21805277 | Hyper | cancer_general | AK303207, SKIDA1, AK055656 | chr10 | 22541638 | 22542265 | Hyper | tcga, liver_tcga, cancer_general | LOC100130992 |
| chr10 | 22624022 | 22625978 | Hyper | liver_tcga, cancer_general | COMMD3-BMI1, SPAG6, BMI1 | chr10 | 22633985 | 22634578 | Hyper | liver_tcga, cancer_general | SPAG6 |
| chr10 | 22764649 | 22765901 | Hyper | liver_tcga, cancer_general | — | chr10 | 23216865 | 23216945 | Hyper | cancer_general | ARMC3 |
| chr10 | 23460355 | 23460471 | Hyper | cancer_general | SNORA40 | chr10 | 23461222 | 23461754 | Hyper | cancer_general | SNORA40 |
| chr10 | 23462059 | 23462910 | Hyper | cancer_general | SNORA40 | chr10 | 23463150 | 23464077 | Hyper | cancer_general | SNORA40 |
| chr10 | 23479876 | 23481086 | Hyper | cancer_general | PTF1A | chr10 | 23481321 | 23481515 | Hyper | cancer_general | PTF1A |
| chr10 | 23481936 | 23482445 | Hyper | cancer_general | PTF1A | chr10 | 23483828 | 23484618 | Hyper | cancer_general | PTF1A |
| chr10 | 23486264 | 23486328 | Hyper | cancer_general | PTF1A | chr10 | 23487742 | 23487978 | Hyper | cancer_general | PTF1A |
| chr10 | 23488393 | 23489158 | Hyper | cancer_general | KIAA1217 | chr10 | 23489409 | 23489439 | Hyper | cancer_general | KIAA1217 |
| chr10 | 23982438 | 23982820 | Hyper | cancer_general | KIAA1217 | chr10 | 23983194 | 23983247 | Hyper | cancer_general | KIAA1217 |
| chr10 | 23983481 | 23983700 | Hyper | tcga, cancer_general | | chr10 | 23984087 | 23984226 | Hyper | cancer_general | |
| chr10 | 23984923 | 23984991 | Hyper | cancer_general | KIAA1217 | chr10 | 25464619 | 25464915 | Hyper | cancer_general | GPR158, GPR158-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 25465421 | 25465517 | Hyper | cancer_general | GPR158-AS1, GPR158 | chr10 | 26055811 | 26055841 | Hyper | cancer_general | — |
| chr10 | 26223001 | 26223424 | Hyper | cancer_general | MYO3A | chr10 | 26224031 | 26224061 | Hyper | cancer_general | MYO3A |
| chr10 | 26500619 | 26500915 | Hyper | cancer_general | GAD2, MYO3A | chr10 | 26501539 | 26501589 | Hyper | cancer_general | GAD2, MYO3A |
| chr10 | 26503693 | 26503731 | Hyper | cancer_general | GAD2, MYO3A | chr10 | 26504114 | 26504159 | Hyper | cancer_general | GAD2, MYO3A |
| chr10 | 26504491 | 26505227 | Hyper | cancer_general | GAD2, OMY3A | chr10 | 26505440 | 26505705 | Hyper | cancer_general | GAD2, MYO3A |
| chr10 | 26506057 | 26506163 | Hyper | cancer_general | GAD2, MYO3A | chr10 | 26506373 | 26507400 | Hyper | cancer_general | GAD2, MYO3A |
| chr10 | 26681099 | 26681129 | Hyper | cancer_general | — | chr10 | 26727098 | 26727368 | Hyper | cancer_general | APBB1IP |
| chr10 | 26727604 | 26727832 | Hyper | cancer_general | APBB1IP | chr10 | 27547946 | 27548484 | Hyper | cancer_general | AK125237, LRRC37A6P |
| chr10 | 28030892 | 28030925 | Hyper | cancer_general | MKX | chr10 | 28032966 | 28033020 | Hyper | cancer_general | MKX |
| chr10 | 28033410 | 28033481 | Hyper | cancer_general | MKX | chr10 | 28033770 | 28034341 | Hyper | tcga, cancer_general | MKX |
| chr10 | 28034575 | 28035300 | Hyper | tcga, cancer_general | MKX | chr10 | 28035615 | 28035782 | Hyper | cancer_general | MKX |
| chr10 | 28287373 | 28287557 | Hyper | tcga | — | chr10 | 28287777 | 28288070 | Hyper | cancer_general | — |
| chr10 | 28657255 | 28657343 | Hyper | literature | — | chr10 | 28958086 | 28958129 | Hyper | cancer_general | BAMBI |
| chr10 | 29011047 | 29011162 | Hyper | cancer_general | — | chr10 | 30025970 | 30026090 | Hyper | blood | — |
| chr10 | 31073368 | 31073481 | Hyper | tcga | — | chr10 | 33624166 | 33624230 | Hyper | blood | — |
| chr10 | 33624492 | 33624560 | Hyper | blood | — | chr10 | 35929150 | 35929528 | Hyper | cancer_general, liver_tcga, tcga | FZD8 |
| chr10 | 43250009 | 43250039 | Hyper | cancer_general | — | chr10 | 43250406 | 43250886 | Hyper | cancer_general | — |
| chr10 | 43428424 | 43428592 | Hyper | cancer_general | — | chr10 | 43429004 | 43429100 | Hyper | cancer_general | — |
| chr10 | 43429376 | 43429411 | Hyper | cancer_general | — | chr10 | 43572685 | 43572734 | Hyper | cancer_general | RET |
| chr10 | 43600561 | 43600720 | Hyper | cancer_general, liver_tcga | RET | chr10 | 43609055 | 43609117 | Hyper | literature | RET |
| chr10 | 43609922 | 43609963 | Hyper | literature | RET | chr10 | 43613890 | 43613919 | Hyper | literature | RET |
| chr10 | 43614982 | 43615011 | Hyper | literature | RET | chr10 | 43615554 | 43615607 | Hyper | literature | RET |
| chr10 | 43617401 | 43617430 | Hyper | literature | RET | chr10 | 43697887 | 43698155 | Hyper | cancer_general, tcga | RASGEF1A |
| chr10 | 44879944 | 44880228 | Hyper | cancer_general | CXCL12 | chr10 | 44880869 | 44880915 | Hyper | cancer_general, tcga | CXCL12 |
| chr10 | 49731548 | 49731749 | Hyper | tcga, colorectal, cancer_general | — | chr10 | 49732060 | 49732498 | Hyper | cancer_general | — |
| chr10 | 50323222 | 50323258 | Hyper | cancer_general | FAM170B-AS1, VSTM4 | chr10 | 50603967 | 50604159 | Hyper | cancer_general | DRGX |
| chr10 | 50604608 | 50604645 | Hyper | cancer_general | DRGX | chr10 | 50605057 | 50605654 | Hyper | cancer_general | DRGX |
| chr10 | 50606027 | 50606433 | Hyper | cancer_general | DRGX | chr10 | 50817015 | 50817132 | Hyper | cancer_general | CHAT, SLC18A3 |
| chr10 | 50817858 | 50817935 | Hyper | cancer_general | SLC18A3, CHAT | chr10 | 50818382 | 50818432 | Hyper | cancer_general | CHAT, SLC18A3 |
| chr10 | 50818823 | 50819102 | Hyper | cancer_general | CHAT, SLC18A3 | chr10 | 50821472 | 50821701 | Hyper | cancer_general | CHAT, SLC18A3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 50887655 | 50887816 | Hyper | cancer_general | C10orf53 | chr10 | 50976880 | 50977048 | Hyper | cancer_general | OGDHL |
| chr10 | 52177545 | 52177575 | Hyper | pancreas | SGMS1 | chr10 | 54068526 | 54068610 | Hyper | cancer_general | DKK1, PRKG1-AS1 |
| chr10 | 54072982 | 54073020 | Hyper | cancer_general | DKK1, PRKG1-AS1 | chr10 | 54073265 | 54073295 | Hyper | cancer_general | DKK1, PRKG1-AS1 |
| chr10 | 54074744 | 54074789 | Hyper | cancer_general | DKK1, PRKG1-AS1 | chr10 | 57387429 | 57387796 | Hyper | literature, cancer_general | — |
| chr10 | 57388325 | 57388510 | Hyper | cancer_general | — | chr10 | 57390290 | 57390637 | Hyper | cancer_general | BICC1 |
| chr10 | 57391166 | 57391215 | Hyper | cancer_general | — | chr10 | 60273130 | 60273294 | Hyper | cancer_general | PHYHIPL |
| chr10 | 60935887 | 60935996 | Hyper | cancer_general | PHYHIPL | chr10 | 60936524 | 60936732 | Hyper | cancer_general | BC041470, TMEM26 |
| chr10 | 60937073 | 60937103 | Hyper | cancer_general | PHYHIPL | chr10 | 63212324 | 63212701 | Hyper | cancer_general | EGR2, ADO |
| chr10 | 64575526 | 64575638 | Hyper | cancer_general | ADO, EGR2 | chr10 | 64578171 | 64578540 | Hyper | tcga, colorectal, cancer_general | NEUROG3 |
| chr10 | 71327725 | 71327764 | Hyper | lung, cancer_general | NEUROG3 | chr10 | 71328773 | 71328821 | Hyper | cancer_general | NEUROG3 |
| chr10 | 71329079 | 71329118 | Hyper | cancer_general | NEUROG3 | chr10 | 71329544 | 71329618 | Hyper | cancer_general | NPFFR1 |
| chr10 | 71332052 | 71333018 | Hyper | tcga, cancer_general | NEUROG3 | chr10 | 72015150 | 72015339 | Hyper | cancer_general | NODAL, UNC5B, UNC5B-AS1 |
| chr10 | 72043638 | 72043894 | Hyper | cancer_general | NPFFR1 | chr10 | 72200102 | 72200138 | Hyper | cancer_general | NODAL, UNC5B, UNC5B-AS1 |
| chr10 | 72200354 | 72201285 | Hyper | cancer_general | NODAL | chr10 | 72973130 | 72973180 | Hyper | blood | ASCC1, SPOCK2 |
| chr10 | 73156362 | 73156661 | Hyper | tcga | CDH23 | chr10 | 73847886 | 73848167 | Hyper | cancer_general, tcga | — |
| chr10 | 75407570 | 75407837 | Hyper | tcga, liver_tcga | SYNPO2L, MYOZ1 | chr10 | 77190039 | 77190068 | Hyper | literature | KCNMA1 |
| chr10 | 77191224 | 77191368 | Hyper | cancer_general | ZCCHC24 | chr10 | 79396921 | 79397089 | Hyper | cancer_general | LOC100288974 |
| chr10 | 81154141 | 81154192 | Hyper | liver_tcga | DYDC1, DYDC2 | chr10 | 81664867 | 81664899 | Hyper | cancer_general | NRG3 |
| chr10 | 82117074 | 82117271 | Hyper | tcga | NRG3 | chr10 | 83634261 | 83634499 | Hyper | tcga | — |
| chr10 | 83635515 | 83635545 | Hyper | cancer_general | — | chr10 | 85954425 | 85954457 | Hyper | pancreas | CDHR1, C10orf99 |
| chr10 | 88123438 | 88123467 | Hyper | tcga | — | chr10 | 88123672 | 88123701 | Hyper | tcga | — |
| chr10 | 88149363 | 88149601 | Hyper | cancer_general | — | chr10 | 89624255 | 89624311 | Hyper | literature | PTEN, KLLN |
| chr10 | 89653788 | 89653859 | Hyper | literature | PTEN | chr10 | 89685272 | 89685322 | Hyper | literature | PTEN |
| chr10 | 89690790 | 89690819 | Hyper | literature | PTEN | chr10 | 89692776 | 89693015 | Hyper | literature | PTEN |
| chr10 | 89711861 | 89711992 | Hyper | literature | AK130076, PTEN | chr10 | 89717610 | 89717744 | Hyper | literature | AK130076, PTEN |
| chr10 | 89720790 | 89720885 | Hyper | literature | — | chr10 | 89725030 | 89725071 | Hyper | literature | — |
| chr10 | 90966708 | 90966865 | Hyper | cancer_general | LIPA, CH25H | chr10 | 90967671 | 90968040 | Hyper | cancer_general | LIPA, CH25H |
| chr10 | 91295029 | 91295067 | Hyper | cancer_general | — | chr10 | 91295531 | 91295725 | Hyper | cancer_general | — |
| chr10 | 92617242 | 92617308 | Hyper | cancer_general | HTR7 | chr10 | 93647216 | 93647300 | Hyper | liver_tcga | — |
| chr10 | 93647562 | 93647648 | Hyper | liver_tcga | — | chr10 | 94450675 | 94450726 | Hyper | cancer_general | HHEX |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 94451448 | 94451653 | Hyper | cancer_general | HHEX | chr10 | 94826023 | 94826056 | Hyper | cancer_general | EXOC6, CYP26A1, CYP26C1 |
| chr10 | 94828163 | 94828498 | Hyper | cancer_general | CYP26A1, CYP26C1, EXOC6 | chr10 | 94828735 | 94828828 | Hyper | cancer_general | CYP26C1, EXOC6, CYP26A1 |
| chr10 | 94834413 | 94835047 | Hyper | tcga, liver_tcga, literature, cancer_general | CYP26A1, CYP26C1 | chr10 | 95360716 | 95360750 | Hyper | blood | RBP4 |
| chr10 | 99080262 | 99080447 | Hyper | cancer_general | FRAT1 | chr10 | 99080862 | 99080984 | Hyper | cancer_general tcga, cancer_general | FRAT1 |
| chr10 | 99474393 | 99474467 | Hyper | hepatobiliary | MARVELD1 | chr10 | 99531219 | 99531430 | Hyper | | SFRP5 |
| chr10 | 99789175 | 99789282 | Hyper | cancer_general | — | chr10 | 99790261 | 99790318 | Hyper | cancer_general | — |
| chr10 | 99790590 | 99790664 | Hyper | cancer_general tcga, cancer_general | — | chr10 | 99790947 | 99791161 | Hyper | cancer_general | — |
| chr10 | 100991907 | 100992443 | Hyper | cancer_general | HPSE2 | chr10 | 100992882 | 100992916 | Hyper | cancer_general | HPSE2 |
| chr10 | 100993537 | 100994016 | Hyper | cancer_general | HPSE2 | chr10 | 100996046 | 100996224 | Hyper | cancer_general | HPSE2 |
| chr10 | 101088995 | 101089439 | Hyper | colorectal, cancer_general | CNNM1 | chr10 | 101089908 | 101090203 | Hyper | cancer_general | CNNM1 |
| chr10 | 101280204 | 101280485 | Hyper | cancer_general | DQ372722, chromosome 10 open reading frame 139 | chr10 | 101283464 | 101283658 | Hyper | tcga | DQ372722, chromosome 10 open reading frame 139, NKX2-3 |
| chr10 | 101290117 | 101291191 | Hyper | cancer_general | NKX2-3, chromosome 10 open reading frame 139, DQ372722 | chr10 | 101292297 | 101292919 | Hyper | cancer_general | NKX2-3, chromosome 10 open reading frame 139, DQ372722 |
| chr10 | 101293156 | 101293343 | Hyper | cancer_general | NKX2-3, chromosome 10 open reading frame 139, DQ372722 | chr10 | 101294756 | 101295586 | Hyper | cancer_general | NKX2-3, chromosome 10 open reading frame 139, DQ372722 |
| chr10 | 101296768 | 101296800 | Hyper | cancer_general | NKX2-3, chromosome 10 open reading frame 139, DQ372722 | chr10 | 101874886 | 101875138 | Hyper | literature, liver_tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 102322230 | 102322260 | Hyper | cancer_general | HIF1AN | chr10 | 102419316 | 102419681 | Hyper | cancer_general | — |
| chr10 | 102430699 | 102430761 | Hyper | cancer_general | — | chr10 | 102473856 | 102473932 | Hyper | cancer_general | — |
| chr10 | 102483993 | 102484554 | Hyper | cancer_general | — | chr10 | 102495508 | 102495741 | Hyper | cancer_general | PAX2 |
| chr10 | 102497273 | 102497708 | Typer | tcga, cancer_general | PAX2 | chr10 | 102498280 | 102498433 | Hyper | cancer_general | PAX2 |
| chr10 | 102501359 | 102501389 | Hyper | cancer_general | PAX2 | chr10 | 102507509 | 102507605 | Hyper | cancer_general | — |
| chr10 | 102508996 | 102509285 | Hyper | cancer_general | PAX2 | chr10 | 102586505 | 102586822 | Hyper | cancer_general | — |
| chr10 | 102589425 | 102589493 | Hyper | cancer_general | — | chr10 | 102589786 | 102589915 | Hyper | cancer_general | — |
| chr10 | 102590152 | 102590415 | Hyper | cancer_general | — | chr10 | 102890941 | 102891582 | Hyper | tcga, cancer_general | TLX1, TLX1NB |
| chr10 | 102891823 | 102892025 | Hyper | cancer_general | TLX1, TLX1NB | chr10 | 102893624 | 102895289 | Hyper | liver_tcga, literature, cancer_general | TLX1, TLX1NB |
| chr10 | 102899173 | 102899601 | Hyper | cancer_general | TLX1, TLX1NB | chr10 | 102899807 | 102900575 | Hyper | liver_tcga, cancer_general | TLX1, TLX1NB |
| chr10 | 102906523 | 102906620 | Hyper | cancer_general | TLX1 | chr10 | 102975619 | 102975834 | Hyper | cancer_general | — |
| chr10 | 102976150 | 102976180 | Hyper | cancer_general | — | chr10 | 102977051 | 102977412 | Hyper | cancer_general | LBX1 |
| chr10 | 102983153 | 102983749 | Hyper | cancer_general | LBX1, FLJ41350 | chr10 | 102984407 | 102984516 | Hyper | cancer_general | LBX1, FLJ41350 |
| chr10 | 102985772 | 102985963 | Hyper | cancer_general | LBX1, FLJ41350 | chr10 | 102986534 | 102987558 | Hyper | lung, cancer_general | LBX1, FLJ41350 |
| chr10 | 102989629 | 102989659 | Hyper | cancer_general | LBX1, FLJ41350, LBX1 | chr10 | 102996116 | 102996638 | Hyper | cancer_general | FLJ41350, LBX1 |
| chr10 | 102997329 | 102997406 | Hyper | cancer_general | FLJ41350, LBX1 | chr10 | 102998576 | 102998828 | Hyper | cancer_general | FLJ41350, LBX1 |
| chr10 | 103043975 | 103044366 | Hyper | literature, cancer_general | — | chr10 | 103432412 | 103432441 | Hyper | cancer_general | FBXW4 |
| chr10 | 103535622 | 103535789 | Hyper | tcga | MGEA5, FGF8, NPM3 | chr10 | 103536227 | 103536416 | Hyper | liver_tcga, cancer_general | NPM3, MGEA5, FGF8 |
| chr10 | 104170096 | 104170732 | Hyper | tcga, cancer_general | PSD, FBXL15, NFKB2 | chr10 | 105036542 | 105036863 | Hyper | liver_tcga, cancer_general | INA |
| chr10 | 105037223 | 105037830 | Hyper | liver_tcga, cancer_general | INA | chr10 | 106398644 | 106398886 | Hyper | cancer_general | SORCS3 |
| chr10 | 106399581 | 106400387 | Hyper | cancer_general | SORCS3 | chr10 | 106400970 | 106402325 | Hyper | tcga, cancer_general | SORCS3 |
| chr10 | 106402712 | 106402825 | Hyper | cancer_general | SORCS3 | chr10 | 108924045 | 108924095 | Hyper | cancer_general | — |
| chr10 | 108924463 | 108924684 | Hyper | cancer_general | — | chr10 | 110226258 | 110226304 | Hyper | cancer_general | — |
| chr10 | 110671892 | 110672245 | Hyper | tcga, cancer_general | — | chr10 | 112216789 | 112216927 | Hyper | cancer_general | — |
| chr10 | 112403151 | 112403297 | Hyper | cancer_general | RBM20, Y_RNA | chr10 | 115804840 | 115805014 | Hyper | cancer_general | ADRB1 |
| chr10 | 116164248 | 116164341 | Hyper | blood | AFAP1L2 | chr10 | 116853875 | 116853908 | Hyper | esophageal | ATRNL1 |
| chr10 | 118030642 | 118030875 | Hyper | cancer_general | GFRA1 | chr10 | 118031302 | 118032547 | Hyper | tcga, cancer_general | GFRA1 |
| chr10 | 118032917 | 118033542 | Hyper | cancer_general | GFRA1, KIAA1598, ENO4 | chr10 | 118034138 | 118034168 | Hyper | cancer_general | GFRA1 |
| chr10 | 118609305 | 118609390 | Hyper | esophageal | | chr10 | 118890980 | 118891104 | Hyper | lung, cancer_general | GFRA1, KIAA1598, VAX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 118891517 | 118891774 | Hyper | cancer_general | VAX1, KIAA1598 | chr10 | 118892013 | 118893266 | Hyper | cancer_general | VAX1, KIAA1598 |
| chr10 | 118893582 | 118894283 | Hyper | tcga, cancer_general | VAX1, KIAA1598 | chr10 | 118896629 | 118896805 | Hyper | tcga, cancer_general | VAX1 |
| chr10 | 118897913 | 118897968 | Hyper | cancer_general | VAX1 | chr10 | 118899273 | 118899302 | Hyper | literature | VAX1 |
| chr10 | 118899511 | 118899957 | Hyper | cancer_general | VAX1 | chr10 | 118900166 | 118900498 | Hyper | cancer_general | VAX1 |
| chr10 | 118922143 | 118922208 | Hyper | cancer_general | MIR3663, BC039338 | chr10 | 118922721 | 118922901 | Hyper | cancer_general, tcga | MIR3663, BC039338 |
| chr10 | 118923138 | 118923259 | Hyper | cancer_general | MIR3663, BC039338 | chr10 | 118924604 | 118924896 | Hyper | cancer_general | MIR3663, BC039338 |
| chr10 | 118927086 | 118927296 | Hyper | cancer_general | MIR3663, BC039338 | chr10 | 118928548 | 118928727 | Hyper | cancer_general | MIR3663, BC039338 |
| chr10 | 119000662 | 119001304 | Hyper | cancer_general | SLC18A2 | chr10 | 119001534 | 119001564 | Hyper | cancer_general | SLC18A2 |
| chr10 | 119292277 | 119292320 | Hyper | cancer_general | EMX2, EMX2OS | chr10 | 119294352 | 119294461 | Hyper | cancer_general | EMX2, EMX2OS |
| chr10 | 119294847 | 119295245 | Hyper | cancer_general | EMX2, EMX2OS | chr10 | 119296706 | 119296788 | Hyper | cancer_general | EMX2, EMX2OS |
| chr10 | 119297384 | 119297529 | Hyper | cancer_general | EMX2 | chr10 | 119301365 | 119301669 | Hyper | cancer_general | EMX2OS, EMX2 |
| chr10 | 119302141 | 119302266 | Hyper | cancer_general | EMX2, EMX2OS | chr10 | 119302962 | 119303174 | Hyper | cancer_general | EMX2, EMX2OS |
| chr10 | 119304363 | 119304393 | Hyper | cancer_general | EMX2, EMX2OS | chr10 | 119304896 | 119305109 | Hyper | cancer_general | EMX2, EMX2OS |
| chr10 | 119307022 | 119307052 | Hyper | cancer_general | EMX2, EMX2OS | chr10 | 119311867 | 119311897 | Hyper | cancer_general | EMX2, EMX2OS |
| chr10 | 119312751 | 119313193 | Hyper | cancer_general | EMX2OS, EMX2 | chr10 | 119590435 | 119590464 | Hyper | literature | — |
| chr10 | 120354243 | 120354273 | Hyper | cancer_general | PRLHR | chr10 | 120355548 | 120355614 | Hyper | cancer_general | PRLHR |
| chr10 | 122216896 | 122217083 | Hyper | tcga | PPAPDC1A | chr10 | 122708495 | 122708691 | Hyper | cancer_general | — |
| chr10 | 122708992 | 122709022 | Hyper | cancer_general | — | chr10 | 123256044 | 123256232 | Hyper | literature | FGFR2 |
| chr10 | 123258020 | 123258091 | Hyper | literature | FGFR2 | chr10 | 123274758 | 123274787 | Hyper | literature | FGFR2 |
| chr10 | 123279548 | 123279697 | Hyper | literature | FGFR2 | chr10 | 123357206 | 123357242 | Hyper | blood | FGFR2 |
| chr10 | 123357766 | 123357893 | Hyper | blood | FGFR2 | chr10 | 123922645 | 123923464 | Hyper | cancer_general | TACC2 |
| chr10 | 124893178 | 124893350 | Hyper | cancer_general | HMX3 | chr10 | 124893635 | 124893765 | Hyper | cancer_general | HMX3 |
| chr10 | 124893965 | 124894479 | Hyper | cancer_general | HMX3 | chr10 | 124894889 | 124894922 | Hyper | cancer_general | HMX3 |
| chr10 | 124895426 | 124896456 | Hyper | tcga, cancer_general | HMX3 | chr10 | 124896861 | 124896913 | Hyper | cancer_general | HMX3 |
| chr10 | 124897220 | 124897973 | Hyper | cancer_general | HMX2, HMX3 | chr10 | 124899035 | 124899116 | Hyper | cancer_general | HMX2, HMX3 |
| chr10 | 124899754 | 124899786 | Hyper | cancer_general | HMX2, HMX3 | chr10 | 124901892 | 124903238 | Hyper | cancer_general | HMX2 |
| chr10 | 124904921 | 124905119 | Hyper | cancer_general | HMX2, HMX3 | chr10 | 124905481 | 124905511 | Hyper | cancer_general | BUB3, HMX3, HMX2 |
| chr10 | 124905911 | 124906174 | Hyper | cancer_general | HMX2, BUB3, HMX3 | chr10 | 124906436 | 124906544 | Hyper | cancer_general | HMX3, HMX2, BUB3 |
| chr10 | 124907312 | 124907534 | Hyper | cancer_general | HMX2, BUB3 | chr10 | 124908091 | 124908121 | Hyper | cancer_general | BUB3, HMX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 124909086 | 124909725 | Hyper | tcga, cancer_general | BUB3, HMX2 | chr10 | 124910363 | 124911048 | Hyper | cancer_general, lung | BUB3, HMX2 |
| chr10 | 125425515 | 125425547 | Hyper | cancer_general | GPR26 | chr10 | 125650866 | 125651348 | Hyper | cancer_general | CPXM2 |
| chr10 | 125851328 | 125851645 | Hyper | colorectal, cancer_general | CHST15 | chr10 | 125852299 | 125852524 | Hyper | colorectal | CHST15 |
| chr10 | 125852753 | 125853191 | Hyper | colorectal | CHST15 | chr10 | 126135927 | 126136065 | Hyper | cancer_general | NKX1-2 |
| chr10 | 126136506 | 126136723 | Hyper | tcga, cancer_general | NKX1-2 | chr10 | 126137181 | 126137405 | Hyper | cancer_general | NKX1-2 |
| chr10 | 128076561 | 128076630 | Hyper | cancer_general | ADAM12 | chr10 | 128077262 | 128077292 | Hyper | cancer_general | ADAM12 |
| chr10 | 128993904 | 128994446 | Hyper | cancer_general | FAM196A | chr10 | 128994727 | 128994903 | Hyper | cancer_general, pancreas, cancer_general | FAM196A |
| chr10 | 129534597 | 129535733 | Hyper | cancer_general | FOXI2, BC132944 | chr10 | 129536080 | 129536310 | Hyper | cancer_general | BC132944, FOXI2 |
| chr10 | 129948111 | 129948140 | Hyper | liver_tcga, pancreas, cancer_general | — | chr10 | 130085295 | 130085362 | Hyper | cancer_general | AK124226 |
| chr10 | 130338727 | 130338976 | Hyper | cancer_general | — | chr10 | 131757091 | 131757430 | Hyper | cancer_general | EBF3 |
| chr10 | 131757946 | 131758056 | Hyper | cancer_general | EBF3 | chr10 | 131761378 | 131761441 | Hyper | cancer_general | EBF3 |
| chr10 | 131761687 | 131761725 | Hyper | cancer_general | EBF3 | chr10 | 131762087 | 131762124 | Hyper | cancer_general | EBF3 |
| chr10 | 131762592 | 131762631 | Hyper | cancer_general | EBF3 | chr10 | 131762904 | 131762940 | Hyper | cancer_general | EBF3 |
| chr10 | 131763348 | 131763717 | Hyper | cancer_general | EBF3 | chr10 | 131767372 | 131767649 | Hyper | tcga, cancer_general | EBF3 |
| chr10 | 131768724 | 131769029 | Hyper | tcga, cancer_general | EBF3 | chr10 | 131769533 | 131770237 | Hyper | cancer_general | EBF3 |
| chr10 | 131770657 | 131770687 | Hyper | cancer_general | EBF3 | chr10 | 131770988 | 131771245 | Hyper | cancer_general | EBF3 |
| chr10 | 133109192 | 133109297 | Hyper | cancer_general | — | chr10 | 133109634 | 133109781 | Hyper | cancer_general | — |
| chr10 | 133110353 | 133110704 | Hyper | cancer_general | — | chr10 | 133794883 | 133795430 | Hyper | tcga, colorectal, cancer_general | BNIP3 |
| chr10 | 133795682 | 133796221 | Hyper | cancer_general | BNIP3 | chr10 | 133849598 | 133850008 | Hyper | cancer_general, pancreas, cancer_general | — |
| chr10 | 133850529 | 133850774 | Hyper | tcga, cancer_general | — | chr10 | 134000008 | 134000124 | Hyper | liver_tcga | — |
| chr10 | 134001097 | 134001260 | Hyper | tcga, cancer_general | DPYSL4, AL137551, JAKMIP3 | chr10 | 134121401 | 134121430 | Hyper | liver_tcga | DPYSL4, AL137551, JAKMIP3 STK32C |
| chr10 | 134598087 | 134598117 | Hyper | cancer_general | NKX6-2, INPP5A | chr10 | 134598336 | 134598530 | Hyper | liver_tcga, cancer_general | NKX6-2, INPP5A |
| chr10 | 134599062 | 134599482 | Hyper | liver_tcga, cancer_general | NKX6-2, INPP5A | chr10 | 134599808 | 134600998 | Hyper | liver_tcga, cancer_general | NKX6-2, INPP5A |
| chr10 | 134601556 | 134601798 | Hyper | cancer_general | NKX6-2, INPP5A | chr10 | 134602183 | 134602269 | Hyper | cancer_general | NKX6-2, INPP5A |
| chr10 | 134755757 | 134756183 | Hyper | tcga, esophageal, cancer_general | TTC40 | chr10 | 134901193 | 134901511 | Hyper | tcga | GPR123 |
| chr10 | 134902008 | 134902307 | Hyper | cancer_general | GPR123 | chr10 | 135043088 | 135043538 | Hyper | cancer_general | UTF1, VENTX |
| chr10 | 135043968 | 135044128 | Hyper | tcga, liver_tcga, cancer_general | VENTX, UTF1 | chr10 | 135044511 | 135044573 | Hyper | cancer_general | VENTX, UTF1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 135048782 | 135048939 | Hyper | cancer_general | VENTX, UTF1 | chr10 | 135050311 | 135050679 | Hyper | cancer_general, tcga | UTF1, VENTX |
| chr10 | 135121316 | 135121345 | Hyper | literature | ZNF511, PRAP1, TUBGCP2 | chr10 | 135121807 | 135122251 | Hyper | literature | ZNF511, PRAP1, TUBGCP2 |
| chr10 | 135122742 | 135122808 | Hyper | literature | PRAP1, ZNF511, TUBGCP2 | chr10 | 135139555 | 135139730 | Hyper | tcga | CALY, BC047942, PRAP1 |
| AC241851.2_88-34049 | 14729 | 14973 | Hyper | cancer_general | — | AC241851.2_88-34049 | 15261 | 15350 | Hyper | cancer_general | — |
| chr5 | 53849 | 53900 | Hyper | cancer_general | — | chr5 | 92163 | 92399 | Hyper | tcga | — |
| chr5 | 320840 | 320982 | Hyper | liver_tcga, literature, cancer_general | AHRR, PDCD6 | chr5 | 343912 | 343941 | Hyper | literature | AHRR |
| chr5 | 373872 | 374266 | Hyper | literature | AHRR | chr5 | 400186 | 400215 | Hyper | literature | AHRR |
| chr5 | 400502 | 400531 | Hyper | literature | AHRR | chr5 | 524337 | 524404 | Hyper | cancer_general | — |
| chr5 | 528565 | 528685 | Hyper | tcga, liver_tcga, cancer_general | MIR4456 | chr5 | 1093660 | 1093797 | Hyper | liver_tcga | — |
| chr5 | 1294630 | 1294767 | Hyper | cancer_general | TERT | chr5 | 1295031 | 1295662 | Hyper | cancer_general, literature | TERT |
| chr5 | 1445171 | 1445282 | Hyper | cancer_general | SLC6A3 | chr5 | 1445738 | 1445928 | Hyper | cancer_general | SLC6A3 |
| chr5 | 1446319 | 1446599 | Hyper | cancer_general | SLC6A3 | chr5 | 1874892 | 1875099 | Hyper | cancer_general | IRX4 |
| chr5 | 1875453 | 1875497 | Hyper | cancer_general | IRX4 | chr5 | 1875870 | 1876860 | Hyper | cancer_general | IRX4 |
| chr5 | 1877160 | 1877239 | Hyper | cancer_general | IRX4 | chr5 | 1878014 | 1878528 | Hyper | cancer_general | IRX4 |
| chr5 | 1878739 | 1879045 | Hyper | cancer_general | IRX4 | chr5 | 1879605 | 1879719 | Hyper | literature, cancer_general | IRX4 |
| chr5 | 1882294 | 1882605 | Hyper | cancer_general | IRX4 | chr5 | 1882844 | 1883089 | Hyper | cancer_general | IRX4 |
| chr5 | 1883515 | 1883820 | Hyper | cancer_general | IRX4 | chr5 | 1884178 | 1884237 | Hyper | cancer_general | IRX4 |
| chr5 | 1884557 | 1884698 | Hyper | cancer_general | IRX4 | chr5 | 1885158 | 1885458 | Hyper | cancer_general | IRX4 |
| chr5 | 1885985 | 1886192 | Hyper | cancer_general | IRX4 | chr5 | 1886542 | 1886581 | Hyper | cancer_general | IRX4 |
| chr5 | 1886812 | 1887737 | Hyper | cancer_general | IRX4 | chr5 | 1930786 | 1931754 | Hyper | pancreas, liver_tcga, cancer_general | — |
| chr5 | 1952624 | 1952654 | Hyper | cancer_general | — | chr5 | 2038705 | 2038850 | Hyper | cancer_general | IRX2 |
| chr5 | 2738848 | 2739422 | Hyper | cancer_general | IRX2 | chr5 | 2739877 | 2741061 | Hyper | tcga, cancer_general | — |
| chr5 | 2743617 | 2743713 | Hyper | cancer_general | C5orf38, IRX2 | chr5 | 2748374 | 2748459 | Hyper | cancer_general | C5orf38, IRX2 |
| chr5 | 2749213 | 2749425 | Hyper | cancer_general | C5orf38 | chr5 | 2749699 | 2749729 | Hyper | cancer_general | C5orf38, IRX2 |
| chr5 | 2750435 | 2751368 | Hyper | cancer_general | C5orf38, IRX2 | chr5 | 2751694 | 2751894 | Hyper | liver_tcga, cancer_general | IRX4 |
| chr5 | 2752991 | 2753040 | Hyper | cancer_general | C5orf38, IRX2 | chr5 | 2754738 | 2754767 | Hyper | literature | IRX2, C5orf38 |
| chr5 | 2755323 | 2756388 | Hyper | tcga, cancer_general | C5orf38, IRX2 | chr5 | 2756599 | 2757427 | Hyper | cancer_general | C5orf38, IRX2 |
| chr5 | 3590405 | 3590760 | Hyper | cancer_general | IRX1 | chr5 | 3591354 | 3591388 | Hyper | cancer_general | IRX1 |
| chr5 | 3591857 | 3592037 | Hyper | cancer_general | IRX1 | chr5 | 3592728 | 3592881 | Hyper | cancer_general | IRX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 3594250 | 3594717 | Hyper | cancer_general | IRX1 | chr5 | 3595090 | 3595178 | Hyper | cancer_general | IRX1 |
| chr5 | 3595448 | 3595991 | Hyper | cancer_general, tcga, pancreas | IRX1 | chr5 | 3596192 | 3596221 | Hyper | liver_tcga, tcga | IRX1 |
| chr5 | 3596540 | 3596880 | Hyper | cancer_general | IRX1 | chr5 | 3597411 | 3597461 | Hyper | cancer_general | IRX1 |
| chr5 | 3599833 | 3599863 | Hyper | cancer_general | IRX1 | chr5 | 3600150 | 3600180 | Hyper | cancer_general | IRX1 |
| chr5 | 3600868 | 3600898 | Hyper | cancer_general | IRX1 | chr5 | 3602804 | 3603320 | Hyper | cancer_general | IRX1 |
| chr5 | 3606633 | 3606668 | Hyper | cancer_general | IRX1 | chr5 | 5139673 | 5139900 | Hyper | cancer_general | ADAMTS16, AK094462 |
| chr5 | 5140170 | 5140225 | Hyper | cancer_general | AK094462, ADAMTS16 | chr5 | 5140630 | 5140901 | Hyper | cancer_general | ADAMTS16, AK094462 |
| chr5 | 6448930 | 6449582 | Hyper | cancer_general | UBE2QL1 | chr5 | 6383461 | 6583579 | Hyper | cancer_general | LOC255167 |
| chr5 | 6687277 | 6687431 | Hyper | lung, cancer_general | — | chr5 | 6755789 | 6755843 | Hyper | liver_tcga | PAPD7 |
| chr5 | 7395263 | 7395538 | Hyper | tcga, cancer_general | ADCY2 | chr5 | 7850069 | 7850203 | Hyper | liver_tcga | FASTKD3, C5orf49 |
| chr5 | 7851015 | 7851121 | Hyper | cancer_general | FASTKD3, C5orf49 | chr5 | 9546612 | 9546648 | Hyper | cancer_general | SNORD123, LOC100505806 |
| chr5 | 10333688 | 10334132 | Hyper | lung, cancer_general | — | chr5 | 10565021 | 10565607 | Hyper | cancer_general | ANKRD33B |
| chr5 | 11384906 | 11385363 | Hyper | cancer_general | CTNND2 | chr5 | 11903760 | 11904696 | Hyper | cancer_general | — |
| chr5 | 11904896 | 11904943 | Hyper | cancer_general | — | chr5 | 14872919 | 14873053 | Hyper | tcga | — |
| chr5 | 15500748 | 15500927 | Hyper | tcga, cancer_general | FBXL7 | chr5 | 16179049 | 16179141 | Hyper | cancer_general | MARCH11, BC043001 |
| chr5 | 16179516 | 16179713 | Hyper | cancer_general | BC043001, MARCH11 | chr5 | 16180047 | 16180260 | Hyper | liver_tcga, literature, cancer_general | BC043001, MARCH11 |
| chr5 | 16936354 | 16936514 | Hyper | tcga, liver_tcga | MYO10 | chr5 | 17217928 | 17217958 | Hyper | pancreas | BASP1, LOC285696 |
| chr5 | 17218195 | 17218225 | Hyper | pancreas | BASP1, LOC285696 | chr5 | 17218943 | 17219018 | Hyper | cancer_general | LOC285696, BASP1 |
| chr5 | 22853443 | 22853508 | Hyper | cancer_general | CDH6 | chr5 | 31193937 | 31193989 | Hyper | cancer_general | CDH6 |
| chr5 | 31194375 | 31194641 | Hyper | cancer_general | — | chr5 | 31639684 | 31639960 | Hyper | tcga, cancer_general | PDZD2 |
| chr5 | 31855073 | 31855199 | Hyper | tcga | PDZD2 | chr5 | 32710331 | 32710470 | Hyper | cancer_general | NPR3 |
| chr5 | 32710802 | 32711531 | Hyper | tcga, cancer_general | NPR3 | chr5 | 32711826 | 32711870 | Hyper | cancer_general | NPR3 |
| chr5 | 32712077 | 32712491 | Hyper | cancer_general | NPR3 | chr5 | 32712764 | 32713304 | Hyper | tcga, cancer_general | NPR3 |
| chr5 | 33892083 | 33892115 | Hyper | cancer_general | U6, ADAMTS12 RXFP3, SLC45A2 | chr5 | 33892413 | 33892443 | Hyper | cancer_general | U6, ADAMTS12 SLC45A2, RXFP3 |
| chr5 | 33936156 | 33936336 | Hyper | tcga, cancer_general | RAI14 | chr5 | 33936599 | 33936663 | Hyper | cancer_general | IL7R |
| chr5 | 34656932 | 34657034 | Hyper | blood | GDNF-AS1, GDNF | chr5 | 35874560 | 35874589 | Hyper | literature | GDNF, GDNF-AS1 |
| chr5 | 37834684 | 37834714 | Hyper | cancer_general | GDNF-AS1, GDNF | chr5 | 37834943 | 37835125 | Hyper | literature | |
| chr5 | 37836231 | 37836260 | Hyper | literature | | chr5 | 37836649 | 37837992 | Hyper | cancer_general | GDNF-AS1, GDNF |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 37838548 | 37838885 | Hyper | tcga, cancer_general | GDNF-AS1, GDNF | chr5 | 37839780 | 37840125 | Hyper | cancer_general | GDNF-AS1, GDNF |
| chr5 | 37840381 | 37840853 | Hyper | tcga, cancer_general | GDNF-AS1, GDNF | chr5 | 38257485 | 38257606 | Hyper | tcga, cancer_general | EGFLAM |
| chr5 | 38257842 | 38257959 | Hyper | cancer_general | EGFLAM | chr5 | 38557070 | 38557400 | Hyper | tcga | MIR3650, LIFR, BC045578 |
| chr5 | 38845675 | 38846431 | Hyper | tcga, colorectal, cancer_general | OSMR | chr5 | 40681122 | 40681367 | Hyper | liver_tcga, cancer_general | PTGER4 |
| chr5 | 40681676 | 40682004 | Hyper | cancer_general | PTGER4 | chr5 | 42424822 | 42425060 | Hyper | cancer_general | GHR |
| chr5 | 42950980 | 42952441 | Hyper | tcga, cancer_general | — | chr5 | 42991825 | 42992934 | Hyper | cancer_general | AK056817 |
| chr5 | 42993150 | 42994193 | Hyper | tcga, cancer_general | AK056817 | chr5 | 42994694 | 42994790 | Hyper | tcga, liver_tcga | AK056817 |
| chr5 | 42995115 | 42995153 | Hyper | tcga, cancer_general | AK056817 | chr5 | 43007936 | 43007966 | Hyper | breast | LOC648987 |
| chr5 | 43008202 | 43008562 | Hyper | tcga, cancer_general | LOC648987 | chr5 | 43017953 | 43018767 | Hyper | tcga, cancer_general | LOC648987 |
| chr5 | 43019238 | 43019347 | Hyper | cancer_general | LOC648987 | chr5 | 43019809 | 43019887 | Hyper | cancer_general | LOC648987 |
| chr5 | 43020146 | 43020294 | Hyper | tcga, breast | LOC648987 | chr5 | 43040544 | 43040635 | Hyper | tcga | LOC153684, DQ601842, ANXA2R |
| chr5 | 43040870 | 43040964 | Hyper | tcga, cancer_general | LOC153684, DQ601842, ANXA2R | chr5 | 43397002 | 43397246 | Hyper | cancer_general | CCL28 |
| chr5 | 44389766 | 44389852 | Hyper | cancer_general | FGF10 | chr5 | 45695186 | 45695533 | Hyper | cancer_general | HCN1 |
| chr5 | 45695906 | 45695947 | Hyper | cancer_general | HCN1 | chr5 | 45696336 | 45696439 | Hyper | cancer_general | HCN1 |
| chr5 | 49736592 | 49736685 | Hyper | cancer_general | — | chr5 | 50262893 | 50263014 | Hyper | cancer_general | — |
| chr5 | 50263568 | 50263641 | Hyper | cancer_general | — | chr5 | 50264307 | 50264603 | Hyper | cancer_general | — |
| chr5 | 50264820 | 50264850 | Hyper | lung | — | chr5 | 50265325 | 50265429 | Hyper | cancer_general | — |
| chr5 | 50265720 | 50265880 | Hyper | cancer_general | — | chr5 | 50674152 | 50674188 | Hyper | cancer_general | ISL1, LOC642366 |
| chr5 | 50674560 | 50674590 | Hyper | cancer_general | ISL1, LOC642366 | chr5 | 50675013 | 50675075 | Hyper | cancer_general | ISL1, LOC642366 |
| chr5 | 50678346 | 50678490 | Hyper | cancer_general | ISL1, LOC642366 | chr5 | 50695280 | 50695463 | Hyper | cancer_general | ISL1 |
| chr5 | 52084073 | 52084134 | Hyper | blood | PELO, ITGA1 | chr5 | 54179587 | 54179633 | Hyper | cancer_general | — |
| chr5 | 54180063 | 54180093 | Hyper | cancer_general | — | chr5 | 54516371 | 54517017 | Hyper | liver_tcga, cancer_general | — |
| chr5 | 54518651 | 54519321 | Hyper | cancer_general | CCNO, MCIDAS | chr5 | 54527304 | 54527343 | Hyper | cancer_general | CCNO, MCIDAS |
| chr5 | 56246546 | 56246575 | Hyper | literature | MIER3 | chr5 | 56247942 | 56247971 | Hyper | literature | MIER3 |
| chr5 | 56248218 | 56248257 | Hyper | literature | MIER3 | chr5 | 57878271 | 57878375 | Hyper | cancer_general | RAB3C |
| chr5 | 57878710 | 57878752 | Hyper | head_neck | RAB3C | chr5 | 59188291 | 59188327 | Hyper | cancer_general | — |
| chr5 | 59189055 | 59189206 | Hyper | liver_tcga, cancer_general | — | chr5 | 59189863 | 59189948 | Hyper | cancer_general | — |
| chr5 | 63254903 | 63255265 | Hyper | cancer_general | HTR1A | chr5 | 63256863 | 63256895 | Hyper | cancer_general | HTR1A |
| chr5 | 63257727 | 63257861 | Hyper | cancer_general | HTR1A | chr5 | 63802007 | 63802514 | Hyper | cancer_general | RGS7BP |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 63986488 | 63986807 | Hyper | cancer_general, tcga | FAM159B | chr5 | 67569803 | 67569832 | Hyper | literature | PIK3R1 |
| chr5 | 67588937 | 67589162 | Hyper | literature | PIK3R1 | chr5 | 67589598 | 67589627 | Hyper | literature | PIK3R1 |
| chr5 | 67590431 | 67590460 | Hyper | literature | PIK3R1 | chr5 | 67591068 | 67591157 | Hyper | literature | PIK3R1 |
| chr5 | 71014720 | 71014895 | Hyper | cancer_general | CARTPT | chr5 | 71015180 | 71015728 | Hyper | cancer_general | CARTPT |
| chr5 | 71403566 | 71403653 | Hyper | cancer_general | MAP1B | chr5 | 71403975 | 71404207 | Hyper | tcga | MAP1B |
| chr5 | 72416246 | 72416751 | Hyper | blood | TMEM171 | chr5 | 72526413 | 72526643 | Hyper | cancer_general | — |
| chr5 | 72529289 | 72530609 | Hyper | cancer_general | — | chr5 | 72594802 | 72595059 | Hyper | cancer_general | — |
| chr5 | 72595542 | 72595788 | Hyper | cancer_general | — | chr5 | 72599079 | 72599833 | Hyper | cancer_general | — |
| chr5 | 72677672 | 72678319 | Hyper | cancer_general | — | chr5 | 72715204 | 72715768 | Hyper | cancer_general | FOXD1 |
| chr5 | 72716102 | 72716180 | Hyper | cancer_general | — | chr5 | 72732801 | 72732884 | Hyper | lung, cancer_general | — |
| chr5 | 72733093 | 72733185 | Hyper | blood | FOXD1 | chr5 | 72740147 | 72740184 | Hyper | cancer_general | FOXD1 |
| chr5 | 72746680 | 72746710 | Hyper | cancer_general | FOXD1 | chr5 | 75377883 | 75378033 | Hyper | cancer_general | SV2C |
| chr5 | 75380163 | 75380193 | Hyper | cancer_general | SV2C | chr5 | 75380624 | 75380974 | Hyper | cancer_general | SV2C |
| chr5 | 76011285 | 76011337 | Hyper | cancer_general | F2R, NCRUPAR | chr5 | 76012576 | 76012605 | Hyper | liver_tcga | F2R, NCRUPAR |
| chr5 | 76249270 | 76250150 | Hyper | cancer_general | CRHBP | chr5 | 76250435 | 76250504 | Hyper | cancer_general | CRHBP |
| chr5 | 76506469 | 76506506 | Hyper | tcga | PDE8B | chr5 | 76507035 | 76507114 | Hyper | cancer_general | PDE8B |
| chr5 | 76923679 | 76924409 | Hyper | cancer_general | OTP | chr5 | 76924930 | 76924960 | Hyper | cancer_general | OTP |
| chr5 | 76925561 | 76925690 | Hyper | cancer_general | OTP | chr5 | 76928157 | 76928397 | Hyper | cancer_general | OTP |
| chr5 | 76928688 | 76928906 | Hyper | cancer_general | OTP | chr5 | 76932302 | 76932332 | Hyper | cancer_general | OTP |
| chr5 | 76932542 | 76933281 | Hyper | cancer_general | OTP | chr5 | 76934173 | 76934870 | Hyper | cancer_general | OTP |
| chr5 | 76936016 | 76936721 | Hyper | pancreas | OTP | chr5 | 76939420 | 76939774 | Hyper | cancer_general | OTP |
| chr5 | 76940340 | 76940374 | Hyper | cancer_general | — | chr5 | 76941201 | 76941326 | Hyper | cancer_general | — |
| chr5 | 77140527 | 77140711 | Hyper | cancer_general | — | chr5 | 77147563 | 77148195 | Hyper | cancer_general | — |
| chr5 | 77148498 | 77148712 | Hyper | cancer_general | — | chr5 | 77268367 | 77269309 | Hyper | tcga, cancer_general | — |
| chr5 | 77806057 | 77806128 | Hyper | cancer_general | LHFPL2 | chr5 | 78407651 | 78407840 | Hyper | cancer_general | BHMT |
| chr5 | 78408192 | 78408461 | Hyper | cancer_general | BHMT | chr5 | 79864898 | 79865078 | Hyper | cancer_general | ANKRD34B |
| chr5 | 79866062 | 79866414 | Hyper | cancer_general | — | chr5 | 80255816 | 80256166 | Hyper | cancer_general, liver_tcga | RASGRF2 |
| chr5 | 80689543 | 80689735 | Hyper | cancer_general | ACOT12 | chr5 | 80690118 | 80690239 | Hyper | tcga, cancer_general | ACOT12 |
| chr5 | 82767429 | 82767793 | Hyper | cancer_general | VCAN | chr5 | 82768892 | 82769061 | Hyper | tcga, colorectal | VCAN |
| chr5 | 83679195 | 83679225 | Hyper | cancer_general | — | chr5 | 83679681 | 83680340 | Hyper | tcga, cancer_general | — |
| chr5 | 83680615 | 83680708 | Hyper | cancer_general | — | chr5 | 87953460 | 87955797 | Hyper | cancer_general | — |
| chr5 | 87956199 | 87956964 | Hyper | cancer_general | LINC00461, MIR9-2 | chr5 | 87962966 | 87963002 | Hyper | cancer_general | LINC00461, MIR9-2 |
| chr5 | 87963390 | 87963511 | Hyper | cancer_general | MIR9-2, LINC00461 | chr5 | 87967773 | 87968077 | Hyper | cancer_general | MIR9-2, LINC00461 |
| chr5 | 87968486 | 87968858 | Hyper | cancer_general | MIR9-2, LINC00461 | chr5 | 87970193 | 87970872 | Hyper | cancer_general | MIR9-2, LINC00461 |
| chr5 | 87974104 | 87974307 | Hyper | cancer_general | — | chr5 | 87974868 | 87975023 | Hyper | cancer_general | — |
| chr5 | 87976028 | 87976308 | Hyper | head_neck | — | chr5 | 87976525 | 87976559 | Hyper | head_neck | — |
| chr5 | 87979756 | 87979912 | Hyper | cancer_general | — | chr5 | 87980142 | 87980250 | Hyper | cancer_general | — |
| chr5 | 87980954 | 87981325 | Hyper | cancer_general | — | chr5 | 87984332 | 87984657 | Hyper | cancer_general | — |
| chr5 | 87985922 | 87985954 | Hyper | cancer_general | — | chr5 | 87986210 | 87986281 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 87988516 | 87988584 | Hyper | cancer_general | | chr5 | 87990408 | 87990452 | Hyper | cancer_general | — |
| chr5 | 88185470 | 88186001 | Hyper | tcga, cancer_general | AL050132 | chr5 | 89854856 | 89854902 | Hyper | cancer_general | GPR98 |
| chr5 | 92939916 | 92940136 | Hyper | cancer_general | — | chr5 | 94955681 | 94955919 | Hyper | cancer_general | GPR150 |
| chr5 | 94956935 | 94957000 | Hyper | cancer_general | GPR150 | chr5 | 95767894 | 95768384 | Hyper | cancer_general | PCSK1 |
| chr5 | 95768920 | 95769093 | Hyper | cancer_general | PCSK1 | chr5 | 100236682 | 100236757 | Hyper | cancer_general | ST8SIA4 |
| chr5 | 100238882 | 100239151 | Hyper | tcga, cancer_general | ST8SIA4 | chr5 | 101631487 | 101631533 | Hyper | cancer_general | SLCO4C1 |
| chr5 | 101632295 | 101632573 | Hyper | tcga | SLCO4C1 | chr5 | 107005983 | 107006186 | Hyper | blood | EFNA5 |
| chr5 | 112042904 | 112043289 | Hyper | literature | APC | chr5 | 112073358 | 112073516 | Hyper | liver_tcga, literature | APC |
| chr5 | 112170808 | 112170837 | Hyper | literature | APC | chr5 | 112175198 | 112175227 | Hyper | literature | APC |
| chr5 | 112175640 | 112175669 | Hyper | literature | APC | chr5 | 112258359 | 112258388 | Hyper | tcga | — |
| chr5 | 112258634 | 112258663 | Hyper | tcga | — | chr5 | 112629427 | 112629674 | Hyper | cancer_general | MCC |
| chr5 | 113392018 | 113392018 | Hyper | tcga, cancer_general | — | chr5 | 113698567 | 113698783 | Hyper | cancer_general | KCNN2 |
| chr5 | 113699008 | 113699119 | Hyper | cancer_general | KCNN2 | chr5 | 114514960 | 114515671 | Hyper | cancer_general | TRIM36 |
| chr5 | 115151267 | 115152638 | Hyper | cancer_general, tcga | CDO1 | chr5 | 115297192 | 115297556 | Hyper | cancer_general | AQPEP, AX747550 |
| chr5 | 115297928 | 115298042 | Hyper | tcga | AQPEP, AX747550 | chr5 | 115298496 | 115298741 | Hyper | tcga, cancer_general | AX747550, AQPEP |
| chr5 | 115298985 | 115299041 | Hyper | cancer_general | — | chr5 | 119799931 | 119799986 | Hyper | cancer_general | PRR16 |
| chr5 | 119801445 | 119801445 | Hyper | cancer_general | PRR16 | chr5 | 121413537 | 121413590 | Hyper | blood | LOX |
| chr5 | 122422240 | 122422292 | Hyper | cancer_general | PRDM6 | chr5 | 122422616 | 122422651 | Hyper | cancer_general | PRDM6 |
| chr5 | 122423328 | 122423376 | Hyper | cancer_general | PRDM6 | chr5 | 122425128 | 122425168 | Hyper | cancer_general | PRDM6 |
| chr5 | 124431118 | 124431378 | Hyper | cancer_general | PRDM6 | chr5 | 126626283 | 126626738 | Hyper | cancer_general, tcga | MEGF10 |
| chr5 | 127872942 | 127872990 | Hyper | cancer_general | FBN2 | chr5 | 127873268 | 127873710 | Hyper | tcga, cancer_general | FBN2 |
| chr5 | 127874448 | 127874839 | Hyper | tcga, literature, cancer_general | FBN2 | chr5 | 128300680 | 128300794 | Hyper | cancer_general | SLC27A6 |
| chr5 | 128796081 | 128796244 | Hyper | cancer_general | ADAMTS19 | chr5 | 128796867 | 128796985 | Hyper | cancer_general | ADAMTS19 |
| chr5 | 128797344 | 128797386 | Hyper | cancer_general | ADAMTS19 | chr5 | 129240068 | 129240101 | Hyper | esophageal | CHSY3 |
| chr5 | 131992096 | 131992157 | Hyper | cancer_general | IL13, BC042122 | chr5 | 132947486 | 132947836 | Hyper | tcga, cancer_general | — |
| chr5 | 134363309 | 134363338 | Hyper | liver_tcga | PITX1, LOC100996485 | chr5 | 134363876 | 134363973 | Hyper | liver_tcga | LOC100996485, PITX1 |
| chr5 | 134364195 | 134364513 | Hyper | liver_tcga, cancer_general | LOC100996485, PITX1 | chr5 | 134366718 | 134366788 | Hyper | cancer_general | LOC100996485, PITX1 |
| chr5 | 134367108 | 134367203 | Hyper | cancer_general | LOC100996485, PITX1 | chr5 | 134374447 | 134375210 | Hyper | cancer_general | LOC100996485, PITX1 |
| chr5 | 134376222 | 134376375 | Hyper | cancer_general | PITX1, LOC100996485 | chr5 | 134376697 | 134376824 | Hyper | cancer_general | LOC100996485, PITX1 |
| chr5 | 134385952 | 134386383 | Hyper | cancer_general | LOC100996485 | chr5 | 134735622 | 134735651 | Hyper | literature | — |
| chr5 | 134825463 | 134825518 | Hyper | cancer_general | — | chr5 | 134825889 | 134826006 | Hyper | cancer_general | — |
| chr5 | 134870446 | 134870515 | Hyper | cancer_general | NEUROG1 | chr5 | 134870780 | 134871196 | Hyper | cancer_general | NEUROG1 |
| chr5 | 134871601 | 134872049 | Hyper | cancer_general | NEUROG1 | chr5 | 134879478 | 134880501 | Hyper | cancer_general | NEUROG1 |
| chr5 | 134914627 | 134914748 | Hyper | tcga | CXCL14 | chr5 | 135265737 | 135265767 | Hyper | cancer_general | FBXL21 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 135266114 | 135266672 | Hyper | cancer_general | FBXL21 | chr5 | 135528201 | 135528233 | Hyper | cancer_general | LOC389332, SMAD5 |
| chr5 | 136834050 | 136834506 | Hyper | tcga, cancer_general | SPOCK1 | chr5 | 136834720 | 136834826 | Hyper | cancer_general | SPOCK1 |
| chr5 | 137225092 | 137225297 | Hyper | liver_tcga, cancer_general | PKD2L2, MYOT | chr5 | 139045286 | 139045315 | Hyper | liver_tcga | CXXC5 |
| chr5 | 139047990 | 139048162 | Hyper | tcga, liver_tcga | CXXC5 | chr5 | 139056666 | 139056804 | Hyper | liver_tcga | CXXC5 |
| chr5 | 139227773 | 139227909 | Hyper | cancer_general | NRG2, PSD2 | chr5 | 139525728 | 139525758 | Hyper | cancer_general | — |
| chr5 | 140174798 | 140174901 | Hyper | cancer_general | PCDHA3, PCDHA2, PCDHA1 | chr5 | 140187094 | 140187146 | Hyper | cancer_general | PCDHA4, PCDHA3, PCDHA2 |
| chr5 | 140305978 | 140306050 | Hyper | cancer_general | PCDHAC1, PCDHA13 | chr5 | 140306321 | 140306733 | Hyper | cancer_general | PCDHAC1, PCDHA13 |
| chr5 | 140346595 | 140346671 | Hyper | cancer_general | PCDHAC2 | chr5 | 140514891 | 140514921 | Hyper | cancer_general | PCDHB5, PCDHB4 |
| chr5 | 140604459 | 140604501 | Hyper | cancer_general | PCDHB18, PCDHB14, PCDHB13 | chr5 | 140613926 | 140614014 | Hyper | cancer_general | PCDHB18, PCDHB19P, PCDHB14 |
| chr5 | 140614314 | 140614383 | Hyper | cancer_general | PCDHB14, PCDHB19P, PCDHB18 | chr5 | 140683631 | 140683772 | Hyper | liver_tcga | SLC25A2 |
| chr5 | 140777328 | 140777487 | Hyper | cancer_general | PCDHGB5, PCDHGA9, PCDHGA8, PCDHGB4, PCDHGA7 | chr5 | 140787608 | 140787637 | Hyper | literature | PCDHGA10, PCDHGB7, PCDHGA9, PCDHGB5, PCDHGA8, PCDHGB6 |
| chr5 | 140797076 | 140797342 | Hyper | liver_tcga, cancer_general | PCDHGB8P, PCDHGA10, PCDHGB6, PCDHGA9, PCDHGB7, PCDHGA11 | chr5 | 140800479 | 140801246 | Hyper | cancer_general, liver_tcga | PCDHGA11, PCDHGB8P, PCDHGA12, PCDHGB7, PCDHGA10, PCDHGB6 |
| chr5 | 140811087 | 140811116 | Hyper | liver_tcga | PCDHGB8P, PCDHGA11, PCDHGB7, PCDHGA12 | chr5 | 140855598 | 140856622 | Hyper | cancer_general | PCDHGC4, PCDHGC3 |
| chr5 | 141031121 | 141031150 | Hyper | liver_tcga | ARAP3, FCHSD1 | chr5 | 141263035 | 141263236 | Hyper | tcga, cancer_general | BC127870, PCDH1 |
| chr5 | 141931340 | 141931539 | Hyper | cancer_general | — | chr5 | 142784967 | 142785272 | Hyper | tcga | NR3C1 |
| chr5 | 145713645 | 145713896 | Hyper | cancer_general | POU4F3 | chr5 | 145717175 | 145717437 | Hyper | cancer_general | POU4F3 |
| chr5 | 145718802 | 145719925 | Hyper | cancer_general | POU4F3 | chr5 | 145720812 | 145720917 | Hyper | cancer_general | POU4F3 |
| chr5 | 145722116 | 145723027 | Hyper | cancer_general | POU4F3 | chr5 | 145724502 | 145724698 | Hyper | cancer_general | POU4F3 |
| chr5 | 145725212 | 145725844 | Hyper | cancer_general | POU4F3 | chr5 | 146257332 | 146257602 | Hyper | tcga, colorectal, cancer_general | PPP2R2B |
| chr5 | 146889220 | 146889575 | Hyper | tcga, cancer_general | DPYSL3 | chr5 | 149503827 | 149503856 | Hyper | literature | PDGFRB |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 149682074 | 149682166 | Hyper | cancer_general | ARSI | chr5 | 150051101 | 150051667 | Hyper | cancer_general | MYOZ3 |
| chr5 | 150326159 | 150326188 | Hyper | literature | ZNF300P1 | chr5 | 150400123 | 150400203 | Hyper | cancer_general | TNIP1, GPX3 |
| chr5 | 151066442 | 151066474 | Hyper | cancer_general | BC039364, SPARC | chr5 | 151304371 | 151304401 | Hyper | cancer_general | — |
| chr5 | 153852664 | 153852792 | Hyper | cancer_general | HAND1 | chr5 | 153853420 | 153853478 | Hyper | cancer_general | HAND1 |
| chr5 | 153854330 | 153854360 | Hyper | cancer_general | HAND1 | chr5 | 153855175 | 153855264 | Hyper | cancer_general | HAND1 |
| chr5 | 153855591 | 153855839 | Hyper | cancer_general | HAND1 | chr5 | 153856090 | 153856396 | Hyper | cancer_general | HAND1 |
| chr5 | 153856936 | 153856996 | Hyper | cancer_general | HAND1 | chr5 | 153857379 | 153857429 | Hyper | cancer_general | HAND1 |
| chr5 | 153858319 | 153858599 | Hyper | cancer_general | HAND1 | chr5 | 153859676 | 153859708 | Hyper | cancer_general | HAND1 |
| chr5 | 153862037 | 153862577 | Hyper | tcga, cancer_general | HAND1 | chr5 | 153863421 | 153863451 | Hyper | cancer_general | HAND1 |
| chr5 | 155107794 | 155107848 | Hyper | cancer_general | — | chr5 | 155108097 | 155108526 | Hyper | tcga, cancer_general | — |
| chr5 | 155108733 | 155108763 | Hyper | cancer_general | — | chr5 | 157001739 | 157001843 | Hyper | cancer_general | ADAM19 |
| chr5 | 157098362 | 157098619 | Hyper | liver_tcga, cancer_general | C5orf52 | chr5 | 158478483 | 158478764 | Hyper | cancer_general | EBF1 |
| chr5 | 158524692 | 158524748 | Hyper | cancer_general | AK123543, EBF1 | chr5 | 158527443 | 158528069 | Hyper | liver_tcga, cancer_general | AK123543, EBF1 |
| chr5 | 159399095 | 159399233 | Hyper | cancer_general | TRNA_Leu, ADRA1B | chr5 | 160975724 | 160975754 | Hyper | cancer_general | GABRB2 |
| chr5 | 161274310 | 161274554 | Hyper | literature, cancer_general | GABRA1 | chr5 | 167956177 | 167956595 | Hyper | tcga, cancer_general | FBLL1, RARS |
| chr5 | 168727924 | 168727988 | Hyper | cancer_general | — | chr5 | 169064327 | 169064805 | Hyper | tcga, liver_tcga, cancer_general | DOCK2 |
| chr5 | 170108287 | 170108372 | Hyper | cancer_general | KCNIP1 | chr5 | 170289444 | 170289498 | Hyper | pancreas | RANBP17 |
| chr5 | 170735154 | 170735206 | Hyper | cancer_general | TLX3, AX746723, RANBP17 | chr5 | 170735422 | 170735788 | Hyper | pancreas, cancer_general | TLX3, AX746723, RANBP17 |
| chr5 | 170736116 | 170737479 | Hyper | liver_tcga, cancer_general | TLX3, AX746723, RANBP17 | chr5 | 170737741 | 170739481 | Hyper | tcga, cancer_general | TLX3, AX746723 |
| chr5 | 170739823 | 170740027 | Hyper | cancer_general | TLX3, AX746723 | chr5 | 170740461 | 170741240 | Hyper | cancer_general | TLX3, AX746723 |
| chr5 | 170741465 | 170744128 | Hyper | cancer_general | TLX3, AX746723 | chr5 | 170744375 | 170744562 | Hyper | cancer_general | TLX3, AX746723 |
| chr5 | 170745389 | 170745480 | Hyper | cancer_general | TLX3, AX746723 | chr5 | 172655879 | 172656215 | Hyper | cancer_general | NKX2-5 |
| chr5 | 172659225 | 172659290 | Hyper | cancer_general | NKX2-5 | chr5 | 172659496 | 172659655 | Hyper | cancer_general | NKX2-5 |
| chr5 | 172659855 | 172660218 | Hyper | cancer_general | NKX2-5 | chr5 | 172660719 | 172661684 | Hyper | cancer_general | NKX2-5 |
| chr5 | 172664226 | 172664487 | Hyper | cancer_general | NKX2-5 | chr5 | 172665590 | 172665812 | Hyper | cancer_general | NKX2-5 |
| chr5 | 172670983 | 172671018 | Hyper | cancer_general | NKX2-5 | chr5 | 172671345 | 172671968 | Hyper | tcga, cancer_general | NKX2-5 |
| chr5 | 172754589 | 172754621 | Hyper | cancer_general | STC2 | chr5 | 172754832 | 172754931 | Hyper | cancer_general | STC2 |
| chr5 | 172755470 | 172755663 | Hyper | cancer_general | STC2 | chr5 | 172757048 | 172757111 | Hyper | cancer_general | STC2 |
| chr5 | 174115388 | 174115861 | Hyper | cancer_general | — | chr5 | 174147523 | 174147596 | Hyper | cancer_general | MSX2 |
| chr5 | 174150415 | 174150445 | Hyper | cancer_general | MSX2 | chr5 | 174158808 | 174159588 | Hyper | cancer_general | MSX2 |
| chr5 | 174162874 | 174162904 | Hyper | cancer_general | MSX2 | chr5 | 174220971 | 174221001 | Hyper | head_neck | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 174870738 | 174870786 | Hyper | cancer_general | DRD1 | chr5 | 174871174 | 174871497 | Hyper | cancer_general | DRD1 |
| chr5 | 175085147 | 175085209 | Hyper | cancer_general | HRH2 | chr5 | 175085476 | 175085719 | Hyper | cancer_general | HRH2 |
| chr5 | 175223671 | 175223709 | Hyper | cancer_general | CPLX2 | chr5 | 175224016 | 175224271 | Hyper | cancer_general | CPLX2 |
| chr5 | 175298549 | 175298883 | Hyper | tcga | CPLX2 | chr5 | 175299294 | 175299396 | Hyper | cancer_general | CPLX2 |
| chr5 | 175300351 | 175300381 | Hyper | cancer_general | Hfb1, CPLX2 | chr5 | 175621390 | 175621501 | Hyper | cancer_general | — |
| chr5 | 175792865 | 175793063 | Hyper | tcga, liver_tcga, cancer_general | KIAA1191, ARL10 | chr5 | 176023916 | 176024318 | Hyper | cancer_general | GPRIN1, CDHR2 |
| chr5 | 176046363 | 176046554 | Hyper | cancer_general | SNCB, MIR4281 | chr5 | 176107274 | 176107586 | Hyper | cancer_general | — |
| chr5 | 176236721 | 176236898 | Hyper | cancer_general | UNC5A | chr5 | 176264805 | 176264915 | Hyper | cancer_general | UNC5A |
| chr5 | 176520166 | 176520195 | Hyper | literature | FGFR4 | chr5 | 176522400 | 176522566 | Hyper | literature | FGFR4 |
| chr5 | 176827656 | 176827685 | Hyper | literature | F12, PFN3, SLC34A1 | chr5 | 177411638 | 177412141 | Hyper | cancer_general | PROP1 |
| chr5 | 178003708 | 178003848 | Hyper | cancer_general | — | chr5 | 178004325 | 178004374 | Hyper | cancer_general | — |
| chr5 | 178016575 | 178017867 | Hyper | tcga, cancer_general | — | chr5 | 178368074 | 178368383 | Hyper | cancer_general | ZNF454, ZFP2 |
| chr5 | 178421474 | 178421504 | Hyper | cancer_general | GRM6 | chr5 | 178421766 | 178422142 | Hyper | literature, cancer_general | GRM6 |
| chr5 | 178487107 | 178487398 | Hyper | tcga, cancer_general | ZNF354C | chr5 | 178771314 | 178771955 | Hyper | tcga, cancer_general | ADAMTS2 |
| chr5 | 178772205 | 178772272 | Hyper | cancer_general | ADAMTS2 | chr5 | 178772603 | 178772745 | Hyper | cancer_general | ADAMTS2 |
| chr5 | 178957637 | 178957944 | Hyper | tcga, cancer_general | AX747985 | chr5 | 179243984 | 179244277 | Hyper | cancer_general | SQSTM1 |
| chr5 | 179780104 | 179780144 | Hyper | cancer_general | GFPT2 | chr5 | 179780706 | 179780985 | Hyper | cancer_general | GFPT2 |
| chr5 | 179867486 | 179867548 | Hyper | cancer_general | — | chr5 | 180017118 | 180017198 | Hyper | cancer_general | SCGB3A1 |
| chr5 | 180017608 | 180017933 | Hyper | tcga, cancer_general | SCGB3A1 | chr5 | 180018311 | 180018498 | Hyper | cancer_general | SCGB3A1 |
| chr5 | 180075846 | 180076317 | Hyper | cancer_general | FLT4 | chr5 | 180076567 | 180076602 | Hyper | cancer_general | FLT4 |
| chr5 | 180076804 | 180076996 | Hyper | tcga, cancer_general | FLT4 | chr5 | 180100915 | 180101332 | Hyper | cancer_general | DQ589679 |
| chr5 | 180527546 | 180527766 | Hyper | liver_tcga, cancer_general | TRNA_Val, TRNA_Leu | chr5 | 180594851 | 180595002 | Hyper | head_neck | TRNA_Val, TRNA_Leu, TRNA_Pseudo |
| chr5 | 180600858 | 180601218 | Hyper | cancer_general | TRNA_Leu, TRNA_Val, TRNA_Pseudo | chr14 | 21093454 | 21093631 | Hyper | cancer_general | TRNA_Pro, TRNA_Leu, TRNA_Thr |
| chr14 | 21100801 | 21100831 | Hyper | head_neck | TRNA_Pro, OR6S1, TRNA_Thr, TRNA_Leu | chr14 | 22005029 | 22005073 | Hyper | cancer_general | — |
| chr14 | 23356044 | 23356384 | Hyper | tcga, liver_tcga | REM2, LRP10 | chr14 | 24045513 | 24045603 | Hyper | cancer_general | JPH4, AP1G2 |
| chr14 | 24640932 | 24641215 | Hyper | literature | REC8, IPO4, IRF9 | chr14 | 24803594 | 24804409 | Hyper | tcga, cancer_general, literature | ADCY4, RIPK3 |
| chr14 | 26674354 | 26674384 | Hyper | cancer_general | — | chr14 | 26674699 | 26674729 | Hyper | cancer_general | — |
| chr14 | 27066562 | 27066785 | Hyper | tcga | NOVA1 | chr14 | 27067161 | 27067386 | Hyper | cancer_general | NOVA1 |
| chr14 | 29225531 | 29225561 | Hyper | cancer_general | — | chr14 | 29226071 | 29226198 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 29228654 | 29228778 | Hyper | cancer_general | FOXG1 | chr14 | 29229107 | 29229386 | Hyper | cancer_general | FOXG1 |
| chr14 | 29231071 | 29231217 | Hyper | cancer_general | FOXG1 | chr14 | 29231425 | 29231590 | Hyper | cancer_general | FOXG1 |
| chr14 | 29235003 | 29235356 | Hyper | cancer_general | FOXG1, C14orf23 | chr14 | 29237063 | 29237107 | Hyper | cancer_general | C14orf23, FOXG1 |
| chr14 | 29242763 | 29242908 | Hyper | cancer_general | FOXG1, BC034423, C14orf23 | chr14 | 29243516 | 29243888 | Hyper | literature, cancer_general | BC034423, C14orf23, FOXG1 |
| chr14 | 29244224 | 29244308 | Hyper | cancer_general | BC034423, C14orf23, FOXG1 | chr14 | 29247689 | 29247740 | Hyper | cancer_general | BC034423, C14orf23, FOXG1 |
| chr14 | 29254575 | 29254713 | Hyper | cancer_general | BC034423, C14orf23 | chr14 | 31344346 | 31344549 | Hyper | cancer_general | COCH, LOC100506071 |
| chr14 | 33402462 | 33402762 | Hyper | cancer_general | NPAS3 | chr14 | 33403045 | 33403316 | Hyper | tcga, cancer_general | NPAS3 |
| chr14 | 33403866 | 33404418 | Hyper | cancer_general | NPAS3 | chr14 | 34420250 | 34420288 | Hyper | blood | EGLN3 |
| chr14 | 36003442 | 36003826 | Hyper | tcga, liver_tcga | RALGAPA1, INSM2 | chr14 | 36004063 | 36004493 | Hyper | cancer_general | RALGAPA1, INSM2 |
| chr14 | 36004711 | 36004983 | Hyper | cancer_general | INSM2, RALGAPA1 | chr14 | 36972803 | 36972912 | Hyper | cancer_general | SFTA3 |
| chr14 | 36973254 | 36973538 | Hyper | cancer_general | SFTA3 | chr14 | 36974294 | 36974982 | Hyper | tcga, cancer_general | SFTA3 |
| chr14 | 36975299 | 36975399 | Hyper | cancer_general | SFTA3 | chr14 | 36977645 | 36978009 | Hyper | cancer_general | NKX2-1, SFTA3 |
| chr14 | 36978548 | 36978578 | Hyper | cancer_general | NKX2-1, BX161496, SFTA3 | chr14 | 36979619 | 36979649 | Hyper | cancer_general | NKX2-1, BX161496, SFTA3 |
| chr14 | 36982927 | 36982969 | Hyper | cancer_general | NKX2-1, SFTA3, BX161496 | chr14 | 36983708 | 36984146 | Hyper | cancer_general | NKX2-1, BX161496, SFTA3 |
| chr14 | 36985841 | 36985871 | Hyper | cancer_general | BX161496, NKX2-1, SFTA3 | chr14 | 36986301 | 36986841 | Hyper | cancer_general | BX161496, NKX2-1, SFTA3 |
| chr14 | 36987168 | 36987685 | Hyper | cancer_general | BX161496, NKX2-1, SFTA3 | chr14 | 36987939 | 36988143 | Hyper | cancer_general | SFTA3, BX161496, NKX2-1 |
| chr14 | 36988428 | 36988460 | Hyper | tcga | NKX2-1, SFTA3, BX161496 | chr14 | 36990858 | 36991177 | Hyper | cancer_general | NKX2-1, BX161496, SFTA3 |
| chr14 | 36991532 | 36991613 | Hyper | cancer_general | BX161496, NKX2-1, SFTA3 | chr14 | 36991936 | 36992417 | Hyper | cancer_general | SFTA3, BX161496, NKX2-1 |
| chr14 | 36993473 | 36993956 | Hyper | cancer_general | BX161496, NKX2-1 | chr14 | 36994248 | 36994999 | Hyper | cancer_general | BX161496, NKX2-1 |
| chr14 | 37050752 | 37050794 | Hyper | cancer_general | NKX2-1 | chr14 | 37116105 | 37116381 | Hyper | cancer_general | NKX2-1 |
| chr14 | 37117611 | 37117697 | Hyper | cancer_general | NKX2-8 | chr14 | 37123438 | 37124077 | Hyper | lung, cancer_general | — |
| chr14 | 37124364 | 37124572 | Hyper | cancer_general | PAX9 | chr14 | 37124992 | 37125545 | Hyper | tcga, cancer_general | PAX9 |
| chr14 | 37126241 | 37126297 | Hyper | cancer_general | PAX9 | chr14 | 37126566 | 37126897 | Hyper | cancer_general | PAX9 |
| chr14 | 37127281 | 37127311 | Hyper | cancer_general | PAX9 | chr14 | 37127655 | 37128027 | Hyper | cancer_general | PAX9 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 37128553 | 37128723 | Hyper | literature, cancer_general | PAX9 | chr14 | 37130077 | 37130260 | Hyper | cancer_general | PAX9 |
| chr14 | 37132375 | 37132695 | Hyper | cancer_general | PAX9 | chr14 | 37133001 | 37133052 | Hyper | cancer_general | PAX9 |
| chr14 | 37135784 | 37136345 | Hyper | cancer_general | PAX9 | chr14 | 37136588 | 37136618 | Hyper | cancer_general | PAX9 |
| chr14 | 38060677 | 38060916 | Hyper | cancer_general | FOXA1 | chr14 | 38064401 | 38064549 | Hyper | blood | FOXA1 |
| chr14 | 38677519 | 38677548 | Hyper | cancer_general | SSTR1 | chr14 | 38677761 | 38677790 | Hyper | tcga | SSTR1 |
| chr14 | 38724294 | 38725258 | Hyper | literature, cancer_general | CLEC14A | chr14 | 38725521 | 38725764 | Hyper | tcga | CLEC14A |
| chr14 | 42074544 | 42074987 | Hyper | cancer_general | LRFN5 | chr14 | 42075588 | 42076212 | Hyper | tcga, cancer_general | LRFN5 |
| chr14 | 42076823 | 42076853 | Hyper | cancer_general | LRFN5 | chr14 | 42077230 | 42077268 | Hyper | cancer_general | LRFN5 |
| chr14 | 42077770 | 42077800 | Hyper | cancer_general | LRFN5 | chr14 | 42079289 | 42079328 | Hyper | cancer_general | LRFN5 |
| chr14 | 48143755 | 48144097 | Hyper | cancer_general | — | chr14 | 48144298 | 48144401 | Hyper | cancer_general | — |
| chr14 | 48144699 | 48145257 | Hyper | tcga, cancer_general | — | chr14 | 51338730 | 51338972 | Hyper | cancer_general | ABHD12B |
| chr14 | 51560304 | 51561428 | Hyper | cancer_general, tcga | TRIM9 | chr14 | 51561765 | 51562012 | Hyper | esophageal | TRIM9 |
| chr14 | 52534648 | 52534791 | Hyper | cancer_general | NID2 | chr14 | 52535012 | 52536404 | Hyper | tcga, cancer_general, literature | NID2 |
| chr14 | 52734509 | 52734557 | Hyper | cancer_general | PTGDR | chr14 | 52734777 | 52735255 | Hyper | cancer_general | PTGDR |
| chr14 | 52781525 | 52781916 | Hyper | cancer_general | PTGER2 | chr14 | 54422651 | 54422925 | Hyper | liver_tcga, cancer_general | BMP4, MIR5580 |
| chr14 | 55595938 | 55595968 | Hyper | liver_tcga | LGALS3 | chr14 | 57260946 | 57261821 | Hyper | cancer_general | OTX2 |
| chr14 | 57262072 | 57262179 | Hyper | cancer_general | OTX2 | chr14 | 57264079 | 57265240 | Hyper | cancer_general | OTX2 |
| chr14 | 57270995 | 57271266 | Hyper | cancer_general | OTX2-AS1, OTX2 | chr14 | 57272009 | 57272067 | Hyper | cancer_general | OTX2-AS1, OTX2 |
| chr14 | 57274486 | 57275305 | Hyper | cancer_general | OTX2-AS1, OTX2 | chr14 | 57275596 | 57276104 | Hyper | cancer_general | OTX2-AS1, OTX2 |
| chr14 | 57276440 | 57276666 | Hyper | cancer_general | OTX2-AS1, OTX2 | chr14 | 57277920 | 57279657 | Hyper | literature, cancer_general | OTX2-AS1, OTX2 |
| chr14 | 57283314 | 57284659 | Hyper | cancer_general | OTX2-AS1 | chr14 | 58332297 | 58332403 | Hyper | cancer_general | — |
| chr14 | 60097193 | 60097566 | Hyper | cancer_general | RTN1 | chr14 | 60386207 | 60386252 | Hyper | cancer_general | LRRC9 |
| chr14 | 60386638 | 60386701 | Hyper | cancer_general | LRRC9 | chr14 | 60794635 | 60794667 | Hyper | cancer_general | JB175233 |
| chr14 | 60952166 | 60952959 | Hyper | cancer_general | C14orf39 | chr14 | 60973151 | 60973324 | Hyper | cancer_general | SIX6 |
| chr14 | 60973697 | 60974077 | Hyper | literature, cancer_general | SIX6 | chr14 | 60974368 | 60974403 | Hyper | cancer_general | SIX6 |
| chr14 | 60975384 | 60976514 | Hyper | tcga, cancer_general | SIX6 | chr14 | 60976813 | 60976860 | Hyper | cancer_general | SIX6 |
| chr14 | 60977337 | 60978147 | Hyper | cancer_general | SIX6 | chr14 | 60981202 | 60981268 | Hyper | cancer_general | SIX6 |
| chr14 | 60981676 | 60981793 | Hyper | cancer_general | SIX6 | chr14 | 60982110 | 60982622 | Hyper | cancer_general | SIX6 |
| chr14 | 60982841 | 60982911 | Hyper | cancer_general | SIX6 | chr14 | 61104291 | 61104864 | Hyper | cancer_general | SIX1 |
| chr14 | 61108620 | 61108996 | Hyper | liver_tcga, cancer_general | SIX1 | chr14 | 61109206 | 61109470 | Hyper | liver_tcga, cancer_general | SIX1 |
| chr14 | 61109839 | 61110243 | Hyper | cancer_general, literature | SIX1 | chr14 | 61114137 | 61114456 | Hyper | cancer_general | SIX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 6115311 | 61115517 | Hyper | cancer_general | SIX1 | chr14 | 61118736 | 61118765 | Hyper | literature | SIX1 |
| chr14 | 61118965 | 61119136 | Hyper | cancer_general | SIX1 | chr14 | 61119536 | 61119639 | Hyper | cancer_general, tcga | SIX1 |
| chr14 | 61747300 | 61748033 | Hyper | blood | TMEM30B | chr14 | 62279578 | 62280006 | Hyper | cancer_general | — |
| chr14 | 62583809 | 62583909 | Hyper | cancer_general | LINC00643 | chr14 | 63512100 | 63512291 | Hyper | cancer_general | KCNH5 |
| chr14 | 63512573 | 63512816 | Hyper | tcga, cancer_general | KCNH5 | chr14 | 63513124 | 63513154 | Hyper | cancer_general | KCNH5 |
| chr14 | 65008994 | 65009193 | Hyper | cancer_general | PPP1R36, HSPA2 | chr14 | 70014723 | 70014974 | Hyper | cancer_general, liver_tcga | — |
| chr14 | 70038490 | 70038635 | Hyper | liver_tcga, cancer_general | CCDC177 | chr14 | 70038990 | 70039025 | Hyper | cancer_general | CCDC177 |
| chr14 | 70346136 | 70346491 | Hyper | tcga, cancer_general | SMOC1 | chr14 | 70654343 | 70654713 | Hyper | cancer_general | — |
| chr14 | 70655530 | 70656090 | Hyper | cancer_general, tcga | — | chr14 | 72398743 | 72399019 | Hyper | cancer_general | RGS6 |
| chr14 | 72399361 | 72399453 | Hyper | cancer_general | RGS6 | chr14 | 72399929 | 72400029 | Hyper | cancer_general | RGS6 |
| chr14 | 74706015 | 74706222 | Hyper | cancer_general | VSX2 | chr14 | 74706458 | 74707873 | Hyper | cancer_general | VSX2 |
| chr14 | 74708862 | 74708955 | Hyper | cancer_general | VSX2 | chr14 | 74892540 | 74892569 | Hyper | liver_tcga | SYNDIG1L |
| chr14 | 74893074 | 74893113 | Hyper | cancer_general | SYNDIG1L | chr14 | 75078170 | 75078507 | Hyper | cancer_general | LTBP2 |
| chr14 | 75988341 | 75988370 | Hyper | literature | BATF | chr14 | 75988732 | 75988761 | Hyper | literature | BATF |
| chr14 | 76604682 | 76604716 | Hyper | cancer_general | — | chr14 | 76605072 | 76605376 | Hyper | cancer_general | ESRRB |
| chr14 | 76843461 | 76843504 | Hyper | cancer_general | ESRRB | chr14 | 76843742 | 76843953 | Hyper | cancer_general | ZDHHC22 |
| chr14 | 77228121 | 77228159 | Hyper | liver_tcga | VASH1 | chr14 | 77606907 | 77607236 | Hyper | tcga, cancer_general | — |
| chr14 | 77737212 | 77737785 | Hyper | tcga, cancer_general | POMT2, MIR1260A, NGB | chr14 | 79745138 | 79745175 | Hyper | cancer_general | NRXN3 |
| chr14 | 85996479 | 85996608 | Hyper | cancer_general, tcga | FLRT2, BX248253 | chr14 | 85996851 | 85996906 | Hyper | cancer_general | FLRT2, BX248253 |
| chr14 | 85997821 | 85998006 | Hyper | cancer_general | BX248253, FLRT2 | chr14 | 85998288 | 85998683 | Hyper | tcga, cancer_general | FLRT2, BX248253 |
| chr14 | 85999569 | 85999613 | Hyper | cancer_general | BX248253, FLRT2 | chr14 | 86000270 | 86000511 | Hyper | cancer_general | — |
| chr14 | 86000918 | 86001114 | Hyper | cancer_general | FLRT2, BX248253 | chr14 | 89817889 | 89818034 | Hyper | cancer_general | — |
| chr14 | 90527714 | 90527758 | Hyper | cancer_general | KCNK13 | chr14 | 92789512 | 92789542 | Hyper | cancer_general | SLC24A4 |
| chr14 | 92789863 | 92790169 | Hyper | tcga, cancer_general | SLC24A4 | chr14 | 92790637 | 92790703 | Hyper | cancer_general | SLC24A4 |
| chr14 | 92979917 | 92979991 | Hyper | pancreas | RIN3 | chr14 | 93389542 | 93389776 | Hyper | liver_tcga, cancer_general | CHGA |
| chr14 | 94254389 | 94254513 | Hyper | cancer_general | PRIMA1 | chr14 | 94405734 | 94405785 | Hyper | cancer_general | ASB2 |
| chr14 | 94889856 | 94889886 | Hyper | head_neck | — | chr14 | 95234643 | 95235369 | Hyper | tcga, cancer_general, literature | GSC |
| chr14 | 95235989 | 95236111 | Hyper | cancer_general | GSC | chr14 | 95236524 | 95236553 | Hyper | literature | GSC |
| chr14 | 95236819 | 95236848 | Hyper | literature | GSC | chr14 | 95237622 | 95237651 | Hyper | literature | GSC |
| chr14 | 95239380 | 95239633 | Hyper | cancer_general | GSC | chr14 | 95240127 | 95240157 | Hyper | cancer_general | GSC |
| chr14 | 95240392 | 95240422 | Hyper | cancer_general | GSC | chr14 | 95557626 | 95557655 | Hyper | literature | DICER1 |
| chr14 | 95560448 | 95560477 | Hyper | literature | DICER1 | chr14 | 96342648 | 96342692 | Hyper | cancer_general | LINC00617 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 96342897 | 96343133 | Hyper | tcga, cancer_general | LINC00617 | chr14 | 96343404 | 96343433 | Hyper | tcga | LINC00617 |
| chr14 | 96343643 | 96343701 | Hyper | cancer_general | LINC00617 | chr14 | 97055856 | 97059083 | Hyper | cancer_general | BC035096 |
| chr14 | 97499277 | 97499315 | Hyper | cancer_general | — | chr14 | 97499706 | 97499944 | Hyper | cancer_general | — |
| chr14 | 97685044 | 97685288 | Hyper | cancer_general | — | chr14 | 97685707 | 97685959 | Hyper | cancer_general | — |
| chr14 | 99584575 | 99584664 | Hyper | cancer_general | BCL11B | chr14 | 99712321 | 99712394 | Hyper | tcga | BCL11B |
| chr14 | 99736151 | 99736183 | Hyper | cancer_general | EVL | chr14 | 99737398 | 99737462 | Hyper | blood | BCL11B |
| chr14 | 100437794 | 100437977 | Hyper | cancer_general | WARS, SLC25A47 | chr14 | 100438705 | 100438811 | Hyper | cancer_general | EVL |
| chr14 | 100793556 | 100793650 | Hyper | liver_tcga | BC148240, MEG9 | chr14 | 101193242 | 101193286 | Hyper | cancer_general | DLK1 |
| chr14 | 101543868 | 101544235 | Hyper | tcga, cancer_general | — | chr14 | 101923114 | 101923250 | Hyper | cancer_general | — |
| chr14 | 101923600 | 101923738 | Hyper | cancer_general | — | chr14 | 101923957 | 101924047 | Hyper | cancer_general | MIR1247, DIO3, DIO3AS, DIO3OS |
| chr14 | 101925049 | 101925901 | Hyper | tcga, cancer_general | — | chr14 | 102026360 | 102026484 | Hyper | cancer_general | MIR1247, DIO3, DIO3AS, DIO3OS |
| chr14 | 102026797 | 102026967 | Hyper | tcga | DIO3, MIR1247, DIO3AS, DIO3OS | chr14 | 102031231 | 102031271 | Hyper | cancer_general | MIR1247, DIO3AS, DIO3OS, DIO3 |
| chr14 | 102031512 | 102031580 | Hyper | cancer_general | DIO3OS, DIO3, MIR1247, DIO3AS | chr14 | 102247912 | 102248214 | Hyper | cancer_general | PPP2R5C |
| chr14 | 103021391 | 103022003 | Hyper | cancer_general | — | chr14 | 103394884 | 103395101 | Hyper | liver_tcga, cancer_general | CDC42BPB, AMN |
| chr14 | 103655226 | 103655601 | Hyper | cancer_general | LINC00605 | chr14 | 103674078 | 103674143 | Hyper | cancer_general | — |
| chr14 | 103687082 | 103687219 | Hyper | cancer_general | — | chr14 | 103739967 | 103740150 | Hyper | cancer_general | — |
| chr14 | 103740358 | 103740430 | Hyper | cancer_general | — | chr14 | 103745699 | 103745750 | Hyper | cancer_general | KIF26A |
| chr14 | 104601737 | 104601832 | Hyper | cancer_general | KIF26A | chr14 | 104602033 | 104602063 | Hyper | cancer_general | TMEM179 |
| chr14 | 104605032 | 104605114 | Hyper | cancer_general | KIF26A | chr14 | 105071298 | 105071396 | Hyper | tcga | AKT1 |
| chr14 | 105239389 | 105239439 | Hyper | literature | AKT1 | chr14 | 105239793 | 105239825 | Hyper | literature | AKT1 |
| chr14 | 105241309 | 105241428 | Hyper | literature | AKT1 | chr14 | 105243032 | 105243064 | Hyper | literature | GPR132 |
| chr14 | 105246427 | 105246582 | Hyper | literature | BTBD6, BRF1 | chr14 | 105512063 | 105512395 | Hyper | ovarian | PACS2 |
| chr14 | 105714415 | 105715529 | Hyper | pancreas | | chr14 | 105830630 | 105830859 | Hyper | liver_tcga | |
| chr14 | 105963655 | 105963772 | Hyper | liver_tcga | C14orf80, CRIP1 | AEKP01168736.1_1-4752 | 1754 | 2287 | Hyper | cancer_general | — |
| chr1 | 1475556 | 1476318 | Hyper | liver_tcga, cancer_general | SSU72, TMEM240, AX747755, ATAD3A | chr1 | 1688882 | 1689012 | Hyper | liver_tcga | NADK |
| chr1 | 1935274 | 1935459 | Hyper | tcga | AK054708, KIAA1751 | chr1 | 2165895 | 2165999 | Hyper | cancer_general | SKI |
| chr1 | 2375148 | 2375543 | Hyper | head_neck, cancer_general | — | chr1 | 2472174 | 2472301 | Hyper | pancreas | LOC115110 |
| chr1 | 2706197 | 2706469 | Hyper | cancer_general | TTC34 | chr1 | 2984719 | 2984749 | Hyper | cancer_general | PRDM16, FLJ42875 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 3567093 | 3568226 | Hyper | literature, cancer_general, liver_tcga | TP73, WRAP73 | chr1 | 3663532 | 3663562 | Hyper | colorectal | CCDC27, TP73-AS1 |
| chr1 | 3663874 | 3663921 | Hyper | esophageal | CCDC27, TP73-AS1 | chr1 | 4714018 | 4714345 | Hyper | literature, cancer_general | AJAP1 |
| chr1 | 4714741 | 4716701 | Hyper | cancer_general, tcga | AJAP1 | chr1 | 6304201 | 6304242 | Hyper | cancer_general | HES3, GPR153, C1orf211, ICMT |
| chr1 | 6480514 | 6480831 | Hyper | cancer_general | ESPN, MIR4252, HES2 | chr1 | 6501001 | 6501179 | Hyper | cancer_general | ESPN |
| chr1 | 6507678 | 6508126 | Hyper | tcga, breast | ESPN | chr1 | 7764641 | 7764737 | Hyper | liver_tcga, tcga | CAMTA1 |
| chr1 | 8085685 | 8085715 | Hyper | blood | ERRFI1 | chr1 | 8277374 | 8277760 | Hyper | cancer_general | — |
| chr1 | 9324231 | 9324274 | Hyper | liver_tcga | H6PD | chr1 | 9527172 | 9527208 | Hyper | liver_tcga | — |
| chr1 | 9712074 | 9712104 | Hyper | esophageal | C1orf200, PIK3CD | chr1 | 9712561 | 9713014 | Hyper | tcga, cancer_general | C1orf200, PIK3CD |
| chr1 | 10948552 | 10948582 | Hyper | cancer_general | — | chr1 | 11169346 | 11169375 | Hyper | literature | MTOR, EXOSC10 |
| chr1 | 11174404 | 11174433 | Hyper | literature | MTOR | chr1 | 11181358 | 11181432 | Hyper | literature | MTOR |
| chr1 | 11182142 | 11182171 | Hyper | literature | MTOR | chr1 | 11188149 | 11188178 | Hyper | literature | MTOR |
| chr1 | 11210182 | 11210211 | Hyper | literature | MTOR-AS1, MTOR | chr1 | 11217215 | 11217337 | Hyper | literature | MTOR-AS1, MTOR |
| chr1 | 11249032 | 11249061 | Hyper | liver_tcga | ANGPTL7 | chr1 | 11538705 | 11538821 | Hyper | esophageal | PTCHD2 |
| chr1 | 11539175 | 11539205 | Hyper | esophageal | PTCHD2 | chr1 | 11539410 | 11539440 | Hyper | esophageal | PTCHD2 |
| chr1 | 11540129 | 11540238 | Hyper | cancer_general | PTCHD2 | chr1 | 11752476 | 11752511 | Hyper | cancer_general | DRAXIN |
| chr1 | 11959093 | 11959196 | Hyper | cancer_general | — | chr1 | 12123243 | 12123640 | Hyper | tcga, cancer_general, colorectal | TNFRSF8 |
| chr1 | 12227685 | 12227941 | Hyper | tcga, cancer_general | TNFRSF1B | chr1 | 13839770 | 13839985 | Hyper | tcga, cancer_general | LRRC38 |
| chr1 | 13910436 | 13910714 | Hyper | tcga | PDPN | chr1 | 14026481 | 14026618 | Hyper | liver_tcga | PRDM2 |
| chr1 | 14925501 | 14926050 | Hyper | cancer_general | KAZN | chr1 | 15251120 | 15251211 | Hyper | blood | KAZN |
| chr1 | 15480593 | 15480892 | Hyper | literature, blood | TMEM51-AS1, TMEM51 | chr1 | 16085356 | 16085656 | Hyper | tcga | FBLIM1 |
| chr1 | 16861522 | 16861552 | Hyper | cancer_general | AX747988, BC036435, TRNA_Asn | chr1 | 17445857 | 17445943 | Hyper | pancreas | PADI2 |
| chr1 | 18434449 | 18434520 | Hyper | cancer_general | IGSF21 | chr1 | 18437457 | 18437526 | Hyper | cancer_general | IGSF21 |
| chr1 | 18956211 | 18956304 | Hyper | cancer_general | PAX7 | chr1 | 18956574 | 18956655 | Hyper | cancer_general | PAX7 |
| chr1 | 18956856 | 18957246 | Hyper | literature, cancer_general | PAX7 | chr1 | 18957507 | 18957587 | Hyper | cancer_general | PAX7 |
| chr1 | 18958033 | 18958381 | Hyper | tcga, cancer_general | PAX7 | chr1 | 18959440 | 18959550 | Hyper | cancer_general | PAX7 |
| chr1 | 18960897 | 18960990 | Hyper | cancer_general | PAX7 | chr1 | 18962727 | 18963135 | Hyper | cancer_general | PAX7 |
| chr1 | 18969625 | 18969819 | Hyper | cancer_general | PAX7 | chr1 | 18971852 | 18971929 | Hyper | cancer_general | PAX7 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 18972130 | 18972160 | Hyper | cancer_general | PAX7 | chr1 | 19043563 | 19043678 | Hyper | cancer_general | PAX7 |
| chr1 | 19992349 | 19992432 | Hyper | cancer_general | NBL1, HTR6 | chr1 | 20618329 | 20618369 | Hyper | cancer_general | VWA5B1 |
| chr1 | 20693317 | 20693420 | Hyper | blood | LOC339505 | chr1 | 20879035 | 20779289 | Hyper | cancer_general | FAM43B |
| chr1 | 20879562 | 20879640 | Hyper | cancer_general | FAM43B | chr1 | 20879845 | 20879957 | Hyper | cancer_general | FAM43B |
| chr1 | 20880182 | 20880605 | Hyper | tcga, cancer_general | FAM43B | chr1 | 21044125 | 21044161 | Hyper | cancer_general | KIF17, SH2D5 |
| chr1 | 21058635 | 21058776 | Hyper | esophageal | SH2D5 | chr1 | 21835943 | 21836007 | Hyper | cancer_general | ALPL, ASAP3, TCEA3 |
| chr1 | 22140753 | 22141184 | Hyper | tcga, cancer_general, liver_tcga | LDLRAD2, HSPG2 | chr1 | 23748982 | 23749070 | Hyper | cancer_general | |
| chr1 | 23885070 | 23885100 | Hyper | breast | ID3 | chr1 | 25255823 | 25255934 | Hyper | tcga | RUNX3 |
| chr1 | 25256354 | 25256383 | Hyper | literature | RUNX3 | chr1 | 25256924 | 25257205 | Hyper | literature, cancer_general | RUNX3 |
| chr1 | 25257532 | 25257561 | Hyper | literature | RUNX3 | chr1 | 26551695 | 26551796 | Hyper | tcga | BC030768, CEP85 |
| chr1 | 26552086 | 26552130 | Hyper | cancer_general | CEP85, BC030768 | chr1 | 26737583 | 26737613 | Hyper | cancer_general | LIN28A |
| chr1 | 26737946 | 26738182 | Hyper | cancer_general | LIN28A | chr1 | 29450491 | 29450543 | Hyper | esophageal | TMEM200B, EPB41 |
| chr1 | 29586072 | 29586674 | Hyper | tcga, lung, cancer_general | PTPRU | chr1 | 29804947 | 29805094 | Hyper | cancer_general | — |
| chr1 | 30815412 | 30815578 | Hyper | cancer_general | — | chr1 | 32180397 | 32180427 | Hyper | head_neck | — |
| chr1 | 32237584 | 32238507 | Hyper | tcga, cancer_general | — | chr1 | 32410276 | 32410306 | Hyper | cancer_general | PTP4A2 |
| chr1 | 32410519 | 32410614 | Hyper | liver_tcga | PTP4A2 | chr1 | 32930458 | 32930558 | Hyper | tcga | ZBTB8A, ZBTB8B |
| chr1 | 33219567 | 33219596 | Hyper | liver_tcga | KIAA1522 | chr1 | 34628948 | 34628978 | Hyper | cancer_general | C1orf94 |
| chr1 | 34629469 | 34629728 | Hyper | cancer_general | C1orf94 | chr1 | 34630548 | 34630635 | Hyper | cancer_general | C1orf94 |
| chr1 | 34630859 | 34630978 | Hyper | cancer_general | C1orf94 | chr1 | 34631580 | 34631662 | Hyper | cancer_general | C1orf94 |
| chr1 | 34631933 | 34631963 | Hyper | cancer_general | C1orf94 | chr1 | 34642380 | 34642573 | Hyper | cancer_general | C1orf94 |
| chr1 | 35258637 | 35258714 | Hyper | cancer_general | GJA4, GJB3 | chr1 | 35351078 | 35351659 | Hyper | cancer_general | DLGAP3 |
| chr1 | 35395526 | 35395851 | Hyper | tcga | — | chr1 | 36042679 | 36043489 | Hyper | tcga, cancer_general | TFAP2E, PSMB2 |
| chr1 | 36849009 | 36849038 | Hyper | liver_tcga | LSM10 | chr1 | 37498792 | 37499181 | Hyper | cancer_general | GRIK3 |
| chr1 | 37499460 | 37500153 | Hyper | cancer_general | GRIK3 | chr1 | 37500468 | 37500806 | Hyper | cancer_general | GRIK3 |
| chr1 | 37501072 | 37501102 | Hyper | cancer_general | GRIK3 | chr1 | 38100689 | 38100851 | Hyper | tcga, cancer_general | RSPO1 |
| chr1 | 38219712 | 38219795 | Hyper | cancer_general | EPHA10 | chr1 | 38230042 | 38230297 | Hyper | cancer_general | EPHA10 |
| chr1 | 38230779 | 38230859 | Hyper | literature, cancer_general | EPHA10 | chr1 | 38412504 | 38412832 | Hyper | tcga, cancer_general | SF3A3, INPP5B |
| chr1 | 38510178 | 38510217 | Hyper | tcga, cancer_general | POU3F1 | chr1 | 38510563 | 38510624 | Hyper | cancer_general | POU3F1 |
| chr1 | 38510854 | 38511119 | Hyper | esophageal | POU3F1 | chr1 | 38511337 | 38511824 | Hyper | cancer_general, colorectal, cancer_general | POU3F1 |
| chr1 | 38512385 | 38512415 | Hyper | tcga, cancer_general | POU3F1 | chr1 | 38513244 | 38513318 | Hyper | liver_tcga | POU3F1 |
| chr1 | 39269741 | 39270121 | Hyper | cancer_general | — | chr1 | 40137898 | 40137984 | Hyper | tcga | HPCAL4, NT5C1A |
| chr1 | 40237141 | 40237203 | Hyper | esophageal | OXCT2, BMP8B | chr1 | 40915590 | 40915620 | Hyper | esophageal | ZFP69B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 41283958 | 41284463 | Hyper | cancer_general | KCNQ4 | chr1 | 41847583 | 41847702 | Hyper | cancer_general | CDC20, MPL |
| chr1 | 41848810 | 41848840 | Hyper | cancer_general | — | chr1 | 43814994 | 43815023 | Hyper | literature | RNF220 |
| chr1 | 44872448 | 44873706 | Hyper | tcga, cancer_general | RNF220 | chr1 | 44883121 | 44884197 | Hyper | tcga, cancer_general | — |
| chr1 | 45308592 | 45308625 | Hyper | liver_tcga | EIF2B3, PTCH2 | chr1 | 46632876 | 46632923 | Hyper | cancer_general | TSPAN1 |
| chr1 | 46913837 | 46914283 | Hyper | tcga, cancer_general | LOC729041 | chr1 | 46914656 | 46914686 | Hyper | cancer_general | LOC729041 |
| chr1 | 46932765 | 46932905 | Hyper | tcga | — | chr1 | 46951207 | 46951739 | Hyper | liver_tcga, cancer_general | — |
| chr1 | 46956454 | 46956603 | Hyper | cancer_general | KNCN, MKNK1-AS1 | chr1 | 46956823 | 46957171 | Hyper | cancer_general | — |
| chr1 | 47009929 | 47010070 | Hyper | cancer_general | STIL, JA375062, TAL1 | chr1 | 47695122 | 47695422 | Hyper | cancer_general | STIL, JA375062, TAL1 |
| chr1 | 47696295 | 47696597 | Hyper | cancer_general | STIL, JA375062, TAL1 | chr1 | 47696821 | 47697110 | Hyper | cancer_general | STIL, JA375062, TAL1 |
| chr1 | 47697356 | 47697510 | Hyper | cancer_general, tcga | FOXE3 | chr1 | 47697732 | 47698210 | Hyper | liver_tcga, literature, cancer_general | FOXE3 |
| chr1 | 47882063 | 47882322 | Hyper | liver_tcga, cancer_general | FOXD2, FOXD2-AS1 | chr1 | 47882769 | 47882803 | Hyper | cancer_general | FOXD2 |
| chr1 | 47909718 | 47910160 | Hyper | cancer_general | FOXD2 | chr1 | 47910523 | 47910914 | Hyper | liver_tcga, cancer_general | — |
| chr1 | 47911335 | 47911508 | Hyper | liver_tcga | — | chr1 | 47999050 | 47999163 | Hyper | liver_tcga | BEND5, AGBL4 |
| chr1 | 48059078 | 48059243 | Hyper | cancer_general | ELAVL4 | chr1 | 49242344 | 49242533 | Hyper | tcga | — |
| chr1 | 50513629 | 50513745 | Hyper | cancer_general | DMRTA2 | chr1 | 50799278 | 50799400 | Hyper | cancer_general | DMRTA2 |
| chr1 | 50880911 | 50881302 | Hyper | liver_tcga, cancer_general | DMRTA2 | chr1 | 50881521 | 50882529 | Hyper | cancer_general | DMRTA2 |
| chr1 | 50882808 | 50883611 | Hyper | cancer_general | DMRTA2 | chr1 | 50883882 | 50884916 | Hyper | tcga, literature, cancer_general | DMRTA2 |
| chr1 | 50885336 | 50885366 | Hyper | cancer_general | DMRTA2 | chr1 | 50886188 | 50887284 | Hyper | literature, cancer_general | DMRTA2 |
| chr1 | 50888709 | 50888826 | Hyper | cancer_general, liver_tcga | DMRTA2 | chr1 | 50889104 | 50889510 | Hyper | liver_tcga, cancer_general | DMRTA2 |
| chr1 | 50889820 | 50890379 | Hyper | cancer_general, tcga | DMRTA2 | chr1 | 50890683 | 50891595 | Hyper | lung, cancer_general | DMRTA2 |
| chr1 | 50892153 | 50892351 | Hyper | cancer_general | DMRTA2 | chr1 | 50892607 | 50893877 | Hyper | cancer_general | DMRTA2 |
| chr1 | 53019468 | 53019568 | Hyper | esophageal | ZCCHC11 | chr1 | 53068166 | 53068546 | Hyper | tcga, esophageal, cancer_general | GPX7 |
| chr1 | 53098842 | 53099067 | Hyper | tcga | FAM159A | chr1 | 53308568 | 53309248 | Hyper | cancer_general | ZYG11A |
| chr1 | 53528374 | 53528439 | Hyper | cancer_general | PODN | chr1 | 54203516 | 54204399 | Hyper | cancer_general | GLIS1 |
| chr1 | 55462673 | 55462703 | Hyper | cancer_general | BSND, ETMM61 | chr1 | 57888367 | 57888397 | Hyper | cancer_general | DAB1 |
| chr1 | 57888987 | 57889087 | Hyper | cancer_general | DAB1 | chr1 | 57889402 | 57889654 | Hyper | tcga, cancer_general | DAB1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 57890431 | 57890650 | Hyper | tcga, cancer_general | DAB1 | chr1 | 58715153 | 58715194 | Hyper | cancer_general | — |
| chr1 | 58715475 | 58715993 | Hyper | tcga, cancer_general | — | chr1 | 61519360 | 61519394 | Hyper | cancer_general | — |
| chr1 | 62660740 | 62660861 | Hyper | liver_tcga | L1TD1 | chr1 | 63539509 | 63539887 | Hyper | tcga, cancer_general | — |
| chr1 | 63785333 | 63786329 | Hyper | liver_tcga, literature, cancer_general | FOXD3 | chr1 | 63787031 | 63787063 | Hyper | cancer_general | FOXD3 |
| chr1 | 63787302 | 63787568 | Hyper | cancer_general | FOXD3 | chr1 | 63788423 | 63788557 | Hyper | liver_tcga | FOXD3 |
| chr1 | 63788788 | 63790278 | Hyper | liver_tcga, cancer_general | U7, FOXD3 | chr1 | 63792561 | 63793072 | Hyper | cancer_general | U7, FOXD3 |
| chr1 | 63795263 | 63796277 | Hyper | cancer_general | U7, FOXD3 | chr1 | 63796498 | 63796575 | Hyper | cancer_general | U7, FOXD3 |
| chr1 | 64240026 | 64240118 | Hyper | blood | ROR1 | chr1 | 64240617 | 64240673 | Hyper | blood | ROR1 |
| chr1 | 64937330 | 64937542 | Hyper | tcga | CACHD1 | chr1 | 65303636 | 65303692 | Hyper | literature | JAK1, RAVER2 |
| chr1 | 65304227 | 65304256 | Hyper | literature | JAK1, RAVER2 | chr1 | 65305384 | 65305413 | Hyper | literature | JAK1, RAVER2 |
| chr1 | 65306926 | 65306955 | Hyper | literature | JAK1, RAVER2 | chr1 | 65309787 | 65309816 | Hyper | literature | JAK1 |
| chr1 | 65310487 | 65310531 | Hyper | literature | JAK1 | chr1 | 65311188 | 65311217 | Hyper | literature | JAK1 |
| chr1 | 65312331 | 65312432 | Hyper | literature | JAK1 | chr1 | 65731337 | 65731446 | Hyper | tcga, cancer_general | DNAJC6, AK123450 |
| chr1 | 65731649 | 65731752 | Hyper | tcga, cancer_general | DNAJC6, AK123450 | chr1 | 65990955 | 65991034 | Hyper | cancer_general | LEPR |
| chr1 | 65991446 | 65991779 | Hyper | tcga, cancer_general | LEPR | chr1 | 66258180 | 66258774 | Hyper | cancer_general, tcga | PDE4B |
| chr1 | 66259137 | 66259174 | Hyper | cancer_general | PDE4B | chr1 | 66998790 | 66999332 | Hyper | cancer_general | SGIP1 |
| chr1 | 66999636 | 66999673 | Hyper | cancer_general | SGIP1 | chr1 | 67218064 | 67218343 | Hyper | cancer_general | SGIP1, TCTEX1D1 |
| chr1 | 67390334 | 67390450 | Hyper | literature | MIER1, WDR78 | chr1 | 67391067 | 67391096 | Hyper | literature | MIER1, WDR78 |
| chr1 | 67773159 | 67773780 | Hyper | tcga, cancer_general, liver_tcga | IL12RB2 | chr1 | 70033609 | 70033916 | Hyper | tcga | LRRC7 |
| chr1 | 70034459 | 70034574 | Hyper | tcga, cancer_general | LRRC7 | chr1 | 70035088 | 70035537 | Hyper | cancer_general | LRRC7 |
| chr1 | 72749641 | 72749715 | Hyper | cancer_general | — | chr1 | 75595798 | 75596384 | Hyper | cancer_general | LHX8, AK055631 |
| chr1 | 75596687 | 75597584 | Hyper | cancer_general | LHX8, AK055631 | chr1 | 75597923 | 75598179 | Hyper | cancer_general | LHX8, AK055631 |
| chr1 | 75598384 | 75598414 | Hyper | cancer_general | LHX8, AK055631 | chr1 | 75599427 | 75599621 | Hyper | cancer_general | LHX8, AK055631 |
| chr1 | 75600225 | 75600848 | Hyper | cancer_general | LHX8, AK055631 | chr1 | 75601058 | 75601428 | Hyper | cancer_general | LHX8, AK055631 |
| chr1 | 75601983 | 75603052 | Hyper | tcga, cancer_general | LHX8, AK055631 | chr1 | 76080484 | 76080768 | Hyper | tcga, cancer_general | SLC44A5 |
| chr1 | 76082129 | 76082209 | Hyper | tcga, cancer_general | SLC44A5 | chr1 | 76440450 | 76440666 | Hyper | tcga, cancer_general | ST6GALNAC3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 77333058 | 77333088 | Hyper | cancer_general | ST6GALNAC5 | chr1 | 77333384 | 77333544 | Hyper | cancer_general | ST6GALNAC5 |
| chr1 | 77334030 | 77334762 | Hyper | tcga, cancer_general | ST6GALNAC5 | chr1 | 77747366 | 77747453 | Hyper | cancer_general | AK5 |
| chr1 | 77747939 | 77748235 | Hyper | tcga, cancer_general | AK5 | chr1 | 78511466 | 78512354 | Hyper | tcga, lung, cancer_general | GIPC2 |
| chr1 | 78957292 | 78957522 | Hyper | cancer_general | PTGFR | chr1 | 82267150 | 82267185 | Hyper | tcga | LPHN2 |
| chr1 | 82268573 | 82268815 | Hyper | tcga | LPHN2 | chr1 | 85358622 | 85358822 | Hyper | tcga | LPAR3 |
| chr1 | 85463349 | 85463378 | Hyper | liver_tcga | MCOLN2 | chr1 | 85725508 | 85725537 | Hyper | tcga | BCL10, C1orf52 |
| chr1 | 86621660 | 86622127 | Hyper | tcga, cancer_general | COL24A1 | chr1 | 86622526 | 86622751 | Hyper | cancer_general, tcga | COL24A1 |
| chr1 | 87617774 | 87617807 | Hyper | cancer_general | — | chr1 | 90099997 | 90100084 | Hyper | tcga | FLJ27354, LRRC8C |
| chr1 | 90309292 | 90309490 | Hyper | ovarian | LRRC8D | chr1 | 91172012 | 91172677 | Hyper | cancer_general | BARHL2 |
| chr1 | 91177941 | 91178207 | Hyper | cancer_general | BARHL2 | chr1 | 91180075 | 91180306 | Hyper | lung, cancer_general | BARHL2 |
| chr1 | 91181932 | 91182132 | Hyper | cancer_general | BARHL2 | chr1 | 91182338 | 91183711 | Hyper | cancer_general, tcga, liver_tcga, literature | BARHL2 |
| chr1 | 91183951 | 91183986 | Hyper | cancer_general | BARHL2 | chr1 | 91184423 | 91184672 | Hyper | cancer_general | BARHL2 |
| chr1 | 91185190 | 91185707 | Hyper | cancer_general | BARHL2 | chr1 | 91189983 | 91189383 | Hyper | cancer_general | BARHL2 |
| chr1 | 91189688 | 91190380 | Hyper | cancer_general | BARHL2 | chr1 | 91190869 | 91191310 | Hyper | cancer_general | BARHL2 |
| chr1 | 91192274 | 91192671 | Hyper | cancer_general | BARHL2 | chr1 | 91194414 | 91194569 | Hyper | cancer_general | BARHL2 |
| chr1 | 91195117 | 91195390 | Hyper | cancer_general | — | chr1 | 91195879 | 91196502 | Hyper | cancer_general | — |
| chr1 | 91316261 | 91316313 | Hyper | cancer_general | — | chr1 | 91316627 | 91316682 | Hyper | cancer_general | — |
| chr1 | 91869988 | 91870018 | Hyper | esophageal | HFM1 | chr1 | 92948324 | 92948597 | Hyper | cancer_general | GFI1 |
| chr1 | 92948841 | 92948976 | Hyper | cancer_general | GFI1 | chr1 | 92952145 | 92952655 | Hyper | tcga, cancer_general | GFI1 |
| chr1 | 94147641 | 94147670 | Hyper | tcga | — | chr1 | 95006795 | 95006902 | Hyper | blood | F3 |
| chr1 | 98510791 | 98511335 | Hyper | tcga, cancer_general | MIR2682, MIR137, MIR137HG | chr1 | 98511628 | 98511922 | Hyper | cancer_general | MIR2682, MIR137HG, MIR137 |
| chr1 | 98514225 | 98514255 | Hyper | cancer_general | MIR137HG, MIR137, MIR2682 | chr1 | 98515256 | 98515319 | Hyper | cancer_general | MIR137, MIR2682, MIR137HG |
| chr1 | 98519023 | 98519675 | Hyper | pancreas, tcga, cancer_general | MIR2682, MIR137HG, MIR137 | chr1 | 99469682 | 99469788 | Hyper | cancer_general | LOC100129620, LPPR5 |
| chr1 | 99470128 | 99470207 | Hyper | liver_tcga | LOC100129620, LPPR5 | chr1 | 99470785 | 99470847 | Hyper | cancer_general | LOC100129620, LPPR5 |
| chr1 | 101004456 | 101004737 | Hyper | cancer_general | GPR88 | chr1 | 101005071 | 101005144 | Hyper | tcga, cancer_general | GPR88 |
| chr1 | 101005360 | 101005675 | Hyper | cancer_general, tcga | GPR88 | chr1 | 101702504 | 101702616 | Hyper | tcga, cancer_general | S1PR1 |
| chr1 | 101703612 | 101703642 | Hyper | cancer_general, tcga | S1PR1 | chr1 | 103574508 | 103574537 | Hyper | literature | COL11A1 |
| chr1 | 107682735 | 107682977 | Hyper | tcga | NTNG1 | chr1 | 107683439 | 107683517 | Hyper | cancer_general | NTNG1 |
| chr1 | 107684240 | 107684439 | Hyper | tcga | NTNG1 | chr1 | 108507063 | 108507092 | Hyper | tcga | VAV3-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 108507320 | 108507497 | Hyper | tcga, cancer_general | VAV3-AS1 | chr1 | 108507717 | 108507810 | Hyper | cancer_general | VAV3-AS1 |
| chr1 | 108508052 | 108508640 | Hyper | cancer_general, tcga | VAV3-AS1 | chr1 | 109203609 | 109203672 | Hyper | liver_tcga | HENMT1 |
| chr1 | 110610586 | 110612058 | Hyper | liver_tcga, cancer_general, literature | DQ574855, ALX3 | chr1 | 110612846 | 110613152 | Hyper | cancer_general | DQ574855, ALX3 |
| chr1 | 110626684 | 110627578 | Hyper | cancer_general | — | chr1 | 110672889 | 110673233 | Hyper | cancer_general | — |
| chr1 | 110692973 | 110694117 | Hyper | tcga, cancer_general | SLC6A17 | chr1 | 110754003 | 110754101 | Hyper | liver_tcga | KCNC4 |
| chr1 | 110754309 | 110754830 | Hyper | cancer_general | KCNC4 | chr1 | 111097906 | 111097936 | Hyper | cancer_general | — |
| chr1 | 111098196 | 111098316 | Hyper | cancer_general | — | chr1 | 111216763 | 111217982 | Hyper | liver_tcga, tcga, cancer_general | KCNA3 |
| chr1 | 111506007 | 111506212 | Hyper | cancer_general | LRIF1 | chr1 | 111813546 | 111813587 | Hyper | cancer_general | CHLAP2 |
| chr1 | 114695439 | 114695943 | Hyper | tcga, cancer_general | — | chr1 | 114696210 | 114696712 | Hyper | cancer_general | — |
| chr1 | 115256514 | 115256552 | Hyper | literature | CSDE1, NRAS | chr1 | 115258729 | 115258772 | Hyper | literature | NRAS, CSDE1 |
| chr1 | 115631867 | 115631915 | Hyper | pancreas | TSPAN2 | chr1 | 115632469 | 115632555 | Hyper | cancer_general | TSPAN2 |
| chr1 | 115880184 | 115880395 | Hyper | pancreas, cancer_general | — | chr1 | 115880850 | 115881218 | Hyper | cancer_general | — |
| chr1 | 116371139 | 116371201 | Hyper | cancer_general | NHLH2 | chr1 | 116380651 | 116381287 | Hyper | cancer_general | NHLH2 |
| chr1 | 116382387 | 116382478 | Hyper | cancer_general | NHLH2 | chr1 | 119522074 | 119522530 | Hyper | cancer_general | TBX15 |
| chr1 | 119522839 | 119522940 | Hyper | cancer_general | TBX15 | chr1 | 119527072 | 119527391 | Hyper | liver_tcga, cancer_general | TBX15 |
| chr1 | 119527623 | 119527652 | Hyper | liver_tcga | TBX15 | chr1 | 119528653 | 119529118 | Hyper | liver_tcga, cancer_general | TBX15 |
| chr1 | 119529804 | 119529839 | Hyper | cancer_general | TBX15 | chr1 | 119530100 | 119530725 | Hyper | liver_tcga, cancer_general | TBX15 |
| chr1 | 119531029 | 119531157 | Hyper | cancer_general | TBX15 | chr1 | 119532043 | 119532320 | Hyper | liver_tcga | TBX15 |
| chr1 | 119535816 | 119536377 | Hyper | cancer_general, liver_tcga | TBX15 | chr1 | 119542322 | 119542352 | Hyper | cancer_general | — |
| chr1 | 119542997 | 119543230 | Hyper | cancer_general | — | chr1 | 119543532 | 119544182 | Hyper | cancer_general | — |
| chr1 | 119548823 | 119548853 | Hyper | liver_tcga | — | chr1 | 119549058 | 119549929 | Hyper | liver_tcga | — |
| chr1 | 119550155 | 119550278 | Hyper | cancer_general | — | chr1 | 119550533 | 119550633 | Hyper | cancer_general | — |
| chr1 | 119550904 | 119551269 | Hyper | cancer_general | — | chr1 | 145075523 | 145075552 | Hyper | liver_tcga | — |
| chr1 | 151693945 | 151694351 | Hyper | tcga, cancer_general | RIIAD1, CELF3 | chr1 | 151812413 | 151812442 | Hyper | liver_tcga | PDE4DIP THEM5, LOC100132111, C2CD4D, RORC |
| chr1 | 152009415 | 152009510 | Hyper | hepatobiliary | S100A11, AC2 | chr1 | 152085398 | 152085504 | Hyper | cancer_general | TCHH |
| chr1 | 152488150 | 152488197 | Hyper | cancer_general | CRCT1, LCE5A | chr1 | 153651965 | 153652379 | Hyper | tcga, liver_tcga, cancer_general | ILF2, NPR1, TRNA_Met |
| chr1 | 154127987 | 154128016 | Hyper | literature | TPM3, NUP210L | chr1 | 154298320 | 154298557 | Hyper | tcga | ATP8B2, AQP10 |
| chr1 | 154475153 | 154475531 | Hyper | cancer_general | TDRD10, SHE | chr1 | 155043331 | 155043657 | Hyper | breast | EFNA4, ADAM15, EFNA3 |

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 155164415 | 155164455 | Hyper | hepatobiliary | TRIM46, MIR92B, THBS3, DM075093, MUC1, AX746485 | chr1 | 155874151 | 155874300 | Hyper | literature | KIAA0907, RIT1 |
| chr1 | 155874508 | 155874546 | Hyper | literature | KIAA0907, RIT1 | | | | | | |
| chr1 | 156215607 | 156215805 | Hyper | cancer_general | SMG5, PAQR6, BGLAP | chr1 | 156215329 | 156215359 | Hyper | cancer_general | PAQR6, BGLAP, SMG5 |
| chr1 | 156390135 | 156390698 | Hyper | cancer_general | C1orf61 | chr1 | 156357993 | 156358508 | Hyper | cancer_general | RHBG |
| chr1 | 156594974 | 156595021 | Hyper | cancer_general | C1orf61, MIR9-1 | chr1 | 156405518 | 156406431 | Hyper | tcga, cancer_general | C1orf61 |
| chr1 | 156626589 | 156626658 | Hyper | cancer_general | HAPLN2 | chr1 | 156611889 | 156612119 | Hyper | cancer_general | BC005081, BCAN |
| chr1 | 156646278 | 156646307 | Hyper | literature | BCAN | chr1 | 156626891 | 156627034 | Hyper | cancer_general | BCAN |
| chr1 | 156814933 | 156815146 | Hyper | cancer_general | NES | chr1 | 156646593 | 156646647 | Hyper | cancer_general | NES |
| chr1 | 156830269 | 156830348 | Hyper | tcga | INSRR, NTRK1 | chr1 | 156815445 | 156815745 | Hyper | pancreas, cancer_general | INSRR, NTRK1 |
| chr1 | 156863662 | 156863724 | Hyper | cancer_general | NTRK1, INSRR | chr1 | 156863107 | 156863331 | Hyper | cancer_general | PEAR1 |
| chr1 | 161228659 | 161228891 | Hyper | tcga, cancer_general | PEAR1 | chr1 | 159158348 | 159158511 | Hyper | cancer_general | LOC100131825, CADM3 |
| chr1 | 161368993 | 161369405 | Hyper | head_neck | PCP4L1 | chr1 | 161275564 | 161276026 | Hyper | cancer_general | SDHC, MPZ |
| chr1 | 161591472 | 161591546 | Hyper | cancer_general | TRNA_Val FCGR3B, TRNA_Asn, TRNA_Glu, TRNA_Leu | chr1 | 161369859 | 161369945 | Hyper | head_neck | TRNA_Val |
| chr1 | 162729615 | 162729686 | Hyper | literature | DDR2 | chr1 | 162724401 | 162724430 | Hyper | literature | DDR2 |
| chr1 | 162792306 | 162792533 | Hyper | cancer_general | C1orf110, HSD17B7 | chr1 | 162748392 | 162748421 | Hyper | literature | AF268386, Metazoa_SRP, DDR2 |
| chr1 | 165086988 | 165087027 | Hyper | cancer_general | — | chr1 | 164290615 | 164290689 | Hyper | cancer_general | — |
| chr1 | 165321747 | 165321852 | Hyper | cancer_general | LMX1A | chr1 | 165205079 | 165205146 | Hyper | cancer_general | LMX1A |
| chr1 | 165324196 | 165324249 | Hyper | cancer_general | LMX1A | chr1 | 165323151 | 165323181 | Hyper | cancer_general | LMX1A |
| chr1 | 165325108 | 165325521 | Hyper | cancer_general | LMX1A | chr1 | 165324488 | 165324668 | Hyper | cancer_general | LMX1A |
| chr1 | 165326204 | 165326469 | Hyper | literature, cancer_general | LMX1A | chr1 | 165325896 | 165325950 | Hyper | cancer_general | LMX1A |
| chr1 | 166134247 | 166134306 | Hyper | cancer_general | — | chr1 | 165414191 | 165414272 | Hyper | cancer_general | RXRG |
| chr1 | 166135193 | 166135281 | Hyper | tcga | — | chr1 | 166134728 | 166134796 | Hyper | cancer_general | TADA1 |
| chr1 | 166890292 | 166890436 | Hyper | liver_tcga | ILDR2 | chr1 | 166853563 | 166853592 | Hyper | liver_tcga | ILDR2 |
| chr1 | 167090617 | 167090757 | Hyper | liver_tcga | DUSP27 | chr1 | 166916866 | 166917100 | Hyper | cancer_general | RCSD1 |
| chr1 | 167599616 | 167599844 | Hyper | tcga, cancer_general | RCSD1 | chr1 | 167599179 | 167599330 | Hyper | cancer_general | CCDC181 |
| | | | | | | chr1 | 169396376 | 169396923 | Hyper | cancer_general, literature | |
| chr1 | 170629540 | 170629569 | Hyper | literature | PRRX1 | chr1 | 170630055 | 170630084 | Hyper | liver_tcga, literature | PRRX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 170630456 | 170630810 | Hyper | literature, cancer_general, liver_tcga | PRRX1 | chr1 | 170631084 | 170631163 | Hyper | cancer_general | PRRX1 |
| chr1 | 170631477 | 170631559 | Hyper | cancer_general | PRRX1 | chr1 | 170633607 | 170633637 | Hyper | esophageal | PRRX1 |
| chr1 | 170637666 | 170637796 | Hyper | cancer_general | PRRX1 | chr1 | 170640517 | 170640691 | Hyper | cancer_general | PRRX1 |
| chr1 | 171810200 | 171810972 | Hyper | liver_tcga, cancer_general, literature | DNM3 | chr1 | 173638647 | 173639085 | Hyper | cancer_general | ANKRD45 |
| chr1 | 177133721 | 177133814 | Hyper | cancer_general | FAM5B | chr1 | 177140105 | 177140714 | Hyper | cancer_general | FAM5B |
| chr1 | 177150773 | 177150803 | Hyper | head_neck | FAM5B | chr1 | 179544967 | 179545098 | Hyper | cancer_general | — |
| chr1 | 179712164 | 179713399 | Hyper | tcga, cancer_general | FAM163A | chr1 | 180198061 | 180198209 | Hyper | cancer_general | LHX4 |
| chr1 | 180202424 | 180203016 | Hyper | cancer_general | LHX4 | chr1 | 180203413 | 180204924 | Hyper | tcga, lung, cancer_general | LHX4 |
| chr1 | 180882576 | 180882695 | Hyper | tcga | KIAA1614 | chr1 | 181287679 | 181287757 | Hyper | cancer_general | CACNA1E, Mir_544 |
| chr1 | 181288014 | 181288188 | Hyper | cancer_general | — | chr1 | 181451407 | 181452120 | Hyper | cancer_general | CACNA1E, Mir_544 |
| chr1 | 181452871 | 181452967 | Hyper | cancer_general | Mir_544, CACNA1E | chr1 | 181454873 | 181454912 | Hyper | cancer_general | CACNA1E |
| chr1 | 181455183 | 181455263 | Hyper | cancer_general | Mir_544, CACNA1E | chr1 | 182584048 | 182584613 | Hyper | pancreas | LOC284648 |
| chr1 | 182921839 | 182921868 | Hyper | liver_tcga | SHCBP1L | chr1 | 183386150 | 183386288 | Hyper | cancer_general | — |
| chr1 | 183386500 | 183386626 | Hyper | cancer_general | — | chr1 | 183386838 | 183386964 | Hyper | cancer_general | — |
| chr1 | 183387266 | 183387319 | Hyper | cancer_general | — | chr1 | 183774244 | 183774363 | Hyper | blood | RGL1 |
| chr1 | 184005701 | 184005814 | Hyper | cancer_general | COLGALT2 | chr1 | 190444855 | 190444885 | Hyper | cancer_general | CR936711, FAM5C |
| chr1 | 190445181 | 190445276 | Hyper | cancer_general | CR936711, FAM5C | chr1 | 190447373 | 190447519 | Hyper | cancer_general | CR936711, FAM5C |
| chr1 | 196577628 | 196577858 | Hyper | tcga, cancer_general | — | chr1 | 196578101 | 196578150 | Hyper | cancer_general | — |
| chr1 | 197879400 | 197880156 | Hyper | liver_tcga, cancer_general | LHX9, C1orf53 | chr1 | 197882140 | 197882201 | Hyper | cancer_general | LHX9, C1orf53 |
| chr1 | 197882453 | 197882611 | Hyper | cancer_general | LHX9, C1orf53 | chr1 | 197887052 | 197887741 | Hyper | cancer_general | LHX9 |
| chr1 | 197888052 | 197888319 | Hyper | cancer_general | LHX9 | chr1 | 197888643 | 197889286 | Hyper | cancer_general | LHX9 |
| chr1 | 200009357 | 200009450 | Hyper | cancer_general | NR5A2 | chr1 | 200009750 | 200010114 | Hyper | cancer_general | NR5A2 |
| chr1 | 200011323 | 200012227 | Hyper | tcga, cancer_general, lung | NR5A2 | chr1 | 201368582 | 201368727 | Hyper | blood | TNNI1, LAD1 |
| chr1 | 201476501 | 201476619 | Hyper | liver_tcga | CSRP1 | chr1 | 202081571 | 202081641 | Hyper | pancreas | — |
| chr1 | 202183371 | 202183401 | Hyper | blood | LGR6 | chr1 | 202679215 | 202679518 | Hyper | tcga, esophageal | SYT2 |
| chr1 | 204499813 | 204499842 | Hyper | literature | MDM4 | chr1 | 204653561 | 204653807 | Hyper | cancer_general | — |
| chr1 | 205312596 | 205312950 | Hyper | cancer_general | KLHDC8A | chr1 | 205424654 | 205424957 | Hyper | cancer_general | AK095633, MIR135B |
| chr1 | 205537663 | 205537772 | Hyper | cancer_general | MFSD4 | chr1 | 207669496 | 207670060 | Hyper | cancer_general | CR1 |
| chr1 | 207818394 | 207818493 | Hyper | liver_tcga | CR1L, CR1 | chr1 | 208084289 | 208084488 | Hyper | cancer_general | CD34 |
| chr1 | 209381132 | 209381165 | Hyper | esophageal | — | chr1 | 209849170 | 209849199 | Hyper | tcga | G0S2 |
| chr1 | 209849430 | 209849459 | Hyper | tcga | G0S2 | chr1 | 210111146 | 210111176 | Hyper | cancer_general | SYT14 |
| chr1 | 210111388 | 210112140 | Hyper | tcga, cancer_general | SYT14 | chr1 | 213123871 | 213123979 | Hyper | hepatobiliary, tcga | VASH2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 213124653 | 213124910 | Hyper | liver_tcga, cancer_general | VASH2 | chr1 | 214156419 | 214156928 | Hyper | cancer_general | PROX1 |
| chr1 | 214158838 | 214158966 | Hyper | cancer_general | PROX1 | chr1 | 214160107 | 214160184 | Hyper | cancer_general | PROX1 |
| chr1 | 214360675 | 214360968 | Hyper | tcga, cancer_general | — | chr1 | 214724531 | 214724561 | Hyper | blood | PTPN14 |
| chr1 | 215255094 | 215255799 | Hyper | cancer_general | KCNK2 | chr1 | 216897216 | 216897307 | Hyper | cancer_general | — |
| chr1 | 217307486 | 217308274 | Hyper | cancer_general | — | chr1 | 217309007 | 217309105 | Hyper | cancer_general | — |
| chr1 | 217311265 | 217311839 | Hyper | cancer_general | — | chr1 | 217313042 | 217313747 | Hyper | cancer_general | — |
| chr1 | 218520074 | 218520399 | Hyper | tcga, cancer_general | TGFB2, CLO728463, RRP15 | chr1 | 218520775 | 218520805 | Hyper | liver_tcga | TGFB2, LOC728463, RRP15 |
| chr1 | 219346992 | 219347035 | Hyper | ovarian | LYPLAL1, LOC643723 | chr1 | 219347394 | 219347472 | Hyper | ovarian | LYPLAL1, LOC643723 |
| chr1 | 220101145 | 220101385 | Hyper | tcga, cancer_general | SLC30A10, RNU5F-1 | chr1 | 220101683 | 220101712 | Hyper | tcga | SLC30A10, RNU5F-1 |
| chr1 | 220700814 | 220700897 | Hyper | cancer_general | MARK1 | chr1 | 221052038 | 221052492 | Hyper | cancer_general | HLX |
| chr1 | 221053610 | 221053862 | Hyper | cancer_general | HLX | chr1 | 221067506 | 221067688 | Hyper | cancer_general | HLX |
| chr1 | 221068156 | 221068185 | Hyper | liver_tcga | HLX | chr1 | 221068793 | 221069150 | Hyper | liver_tcga | — |
| chr1 | 221737191 | 221737220 | Hyper | liver_tcga | — | chr1 | 223302825 | 223302890 | Hyper | cancer_general | — |
| chr1 | 223538344 | 223538641 | Hyper | tcga | SUSD4 | chr1 | 223936633 | 223937057 | Hyper | lung, cancer_general | CAPN2 |
| chr1 | 224363560 | 224363589 | Hyper | literature | DEGS1 | chr1 | 224528814 | 224528844 | Hyper | cancer_general | — |
| chr1 | 224803717 | 224803751 | Hyper | cancer_general | CNIH3 | chr1 | 224804097 | 224804791 | Hyper | liver_tcga, cancer_general | CNIH3 |
| chr1 | 224805131 | 224805808 | Hyper | cancer_general | CNIH3 | chr1 | 226411243 | 226411273 | Hyper | liver_tcga | LIN9, MIXL1 |
| chr1 | 226411700 | 226411832 | Hyper | tcga, liver_tcga | LIN9, MIXL1 ITPKB | chr1 | 226814346 | 226814408 | Hyper | colorectal | ITPKB |
| chr1 | 226925067 | 226925195 | Hyper | tcga, cancer_general | ITPKB | chr1 | 227729780 | 227730075 | Hyper | cancer_general | — |
| chr1 | 227748700 | 227748733 | Hyper | liver_tcga, literature | ZNF678 | chr1 | 228194428 | 228194490 | Hyper | tcga | WNT3A |
| chr1 | 228195377 | 228196349 | Hyper | tcga, cancer_general | WNT3A | chr1 | 228247998 | 228248027 | Hyper | liver_tcga | WNT3A |
| chr1 | 228248302 | 228248332 | Hyper | cancer_general | WNT3A | chr1 | 228345999 | 228346195 | Hyper | liver_tcga | IBA57, GJC2, GUK1 |
| chr1 | 228463311 | 228463706 | Hyper | cancer_general | OBSCN | chr1 | 228566622 | 228566672 | Hyper | cancer_general | — |
| chr1 | 228604022 | 228604254 | Hyper | tcga, cancer_general | HIST3H3, HIST3H2A, TRIM17, TRIM11 | chr1 | 228633990 | 228634261 | Hyper | cancer_general | — |
| chr1 | 228645140 | 228645734 | Hyper | cancer_general, lung, tcga, liver_tcga | Histone3, HIST3H2A, HIST3H2BB, MIR4666A | chr1 | 228646032 | 228646238 | Hyper | tcga | MIR4666A, Histone3, HIST3H2BB, HIST3H2A |
| chr1 | 228651432 | 228651626 | Hyper | cancer_general | MIR4666A, HIST3H2BB, HIST3H2A, Histone3 | chr1 | 228651879 | 228652629 | Hyper | cancer_general | Histone3, MIR4666A, HIST3H2BB, HIST3H2A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 228871865 | 228872003 | Hyper | blood | RHOU | chr1 | 229542838 | 229543139 | Hyper | cancer_general | — |
| chr1 | 229543553 | 229543603 | Hyper | liver_tcga | — | chr1 | 229566753 | 229568204 | Hyper | cancer_general | ACTA1, NUP133 |
| chr1 | 229569810 | 229569852 | Hyper | cancer_general | NUP133, ACTA1 | chr1 | 230561779 | 230561824 | Hyper | esophageal | PGBD5 |
| chr1 | 231297103 | 231297221 | Hyper | cancer_general | TRIM67 | chr1 | 231298595 | 231298772 | Hyper | tcga, liver_tcga | TRIM67 |
| chr1 | 232765195 | 232765301 | Hyper | blood | — | chr1 | 233750082 | 233750302 | Hyper | blood | MIR4427, KCNK1 |
| chr1 | 234040247 | 234040319 | Hyper | cancer_general | SLC35F3 | chr1 | 234040750 | 234041064 | Hyper | tcga, cancer_general | SLC35F3 |
| chr1 | 234041400 | 234041624 | Hyper | cancer_general | SLC35F3 | chr1 | 234349988 | 234350100 | Hyper | tcga, cancer_general | SLC35F3, AK054726 |
| chr1 | 235813781 | 235814202 | Hyper | cancer_general, tcga, literature | — | chr1 | 235814447 | 235814476 | Hyper | literature | LYST |
| chr1 | 236227637 | 236228096 | Hyper | cancer_general | AX747246, NID1 | chr1 | 236228582 | 236228789 | Hyper | tcga, cancer_general | AX747246, NID1 |
| chr1 | 236559176 | 236559271 | Hyper | cancer_general | EDARADD | chr1 | 236849457 | 236850142 | Hyper | cancer_general | ACTN2 |
| chr1 | 237205159 | 237205188 | Hyper | literature | RYR2 | chr1 | 237205434 | 237205478 | Hyper | cancer_general | RYR2 |
| chr1 | 237205687 | 237206735 | Hyper | tcga, cancer_general | RYR2 | chr1 | 239550594 | 239551193 | Hyper | cancer_general | CHRM3 |
| chr1 | 240161098 | 240161493 | Hyper | cancer_general | RPS7P5 | chr1 | 240254944 | 240255011 | Hyper | cancer_general | FMN2 |
| chr1 | 240255361 | 240255500 | Hyper | cancer_general | FMN2 | chr1 | 240255819 | 240256197 | Hyper | cancer_general | FMN2 |
| chr1 | 240256663 | 240256721 | Hyper | cancer_general | FMN2 | chr1 | 240775425 | 240775455 | Hyper | cancer_general | — |
| chr1 | 241520296 | 241520345 | Hyper | tcga | — | chr1 | 241520583 | 241520612 | Hyper | tcga | — |
| chr1 | 241587034 | 241587113 | Hyper | cancer_general | — | chr1 | 241587587 | 241587797 | Hyper | tcga, cancer_general | — |
| chr1 | 242686734 | 242687688 | Hyper | tcga, cancer_general | PLD5 | chr1 | 242688184 | 242688259 | Hyper | cancer_general | PLD5 |
| chr1 | 242688477 | 242688695 | Hyper | cancer_general | PLD5 | chr1 | 243646610 | 243646673 | Hyper | cancer_general | AKT3 |
| chr1 | 243859000 | 243859029 | Hyper | literature | — | chr1 | 244014221 | 244014376 | Hyper | esophageal | — |
| chr1 | 244080672 | 244080702 | Hyper | cancer_general | LOC339529 | chr1 | 244080963 | 244081203 | Hyper | tcga | LOC339529 |
| chr1 | 244893214 | 244893315 | Hyper | cancer_general | — | chr1 | 246952347 | 246952376 | Hyper | literature | LOC149134 |
| chr1 | 247496038 | 247496108 | Hyper | tcga | ZNF496 | chr1 | 248020479 | 248021349 | Hyper | liver_tcga, cancer_general | TRIM58 |
| chrX | 6145331 | 6145688 | Hyper | tcga, cancer_general | NLGN4X | chrX | 8698863 | 8698897 | Hyper | cancer_general | KAL1 |
| chrX | 8699504 | 8699566 | Hyper | cancer_general | KAL1 | chrX | 20148710 | 20148739 | Hyper | literature | SCARNA9L, EIF1AX |
| chrX | 47039370 | 47039399 | Hyper | literature | RBM10 | chrX | 47426106 | 47426144 | Hyper | literature | SYN1, ARAF |
| chrX | 47426780 | 47426821 | Hyper | literature | SYN1, ARAF | chrX | 50557045 | 50557075 | Hyper | liver_tcga | — |
| chrX | 64626567 | 64626596 | Hyper | liver_tcga | AR | chrX | 66931448 | 66931477 | Hyper | literature | AR |
| chrX | 66937356 | 66937385 | Hyper | literature | MED12 | chrX | 66943529 | 66943567 | Hyper | literature | AR |
| chrX | 70339239 | 70339268 | Hyper | literature | IL2RG | chrX | 100740260 | 100740289 | Hyper | liver_tcga | ARMCX4 |
| chrX | 101906099 | 101906128 | Hyper | liver_tcga | GPRASP1 | chrX | 102000609 | 102000758 | Hyper | liver_tcga | BHLHB9 |
| chrX | 134156560 | 134156680 | Hyper | liver_tcga | FAM127A, FAM127C | chrX | 136656563 | 136656592 | Hyper | liver_tcga | ZIC3 |
| HCV | 111 | 140 | Hyper | virus | — | HCV | 374 | 403 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HCV | 637 | 666 | Hyper | virus | — | HCV | 900 | 929 | Hyper | virus | — |
| HCV | 1163 | 1192 | Hyper | virus | — | HCV | 1426 | 1455 | Hyper | virus | — |
| HCV | 1689 | 1718 | Hyper | virus | — | HCV | 1952 | 1981 | Hyper | virus | — |
| HCV | 2215 | 2244 | Hyper | virus | — | HCV | 2478 | 2507 | Hyper | virus | — |
| HCV | 2741 | 2770 | Hyper | virus | — | HCV | 3004 | 3033 | Hyper | virus | — |
| HCV | 3267 | 3296 | Hyper | virus | — | HCV | 3530 | 3559 | Hyper | virus | — |
| HCV | 3793 | 3822 | Hyper | virus | — | HCV | 4056 | 4085 | Hyper | virus | — |
| HCV | 4319 | 4348 | Hyper | virus | — | HCV | 4582 | 4611 | Hyper | virus | — |
| HCV | 4845 | 4874 | Hyper | virus | — | HCV | 5108 | 5137 | Hyper | virus | — |
| HCV | 5371 | 5400 | Hyper | virus | — | HCV | 5634 | 5663 | Hyper | virus | — |
| HCV | 5897 | 5926 | Hyper | virus | — | HCV | 6160 | 6189 | Hyper | virus | — |
| HCV | 6423 | 6452 | Hyper | virus | — | HCV | 6686 | 6715 | Hyper | virus | — |
| HCV | 6949 | 6978 | Hyper | virus | — | HCV | 7212 | 7241 | Hyper | virus | — |
| HCV | 7475 | 7504 | Hyper | virus | — | HCV | 7738 | 7767 | Hyper | virus | — |
| HCV | 8001 | 8030 | Hyper | virus | — | HCV | 8264 | 8293 | Hyper | virus | — |
| HCV | 8527 | 8556 | Hyper | virus | — | HCV | 8790 | 8819 | Hyper | virus | — |
| HCV | 9053 | 9082 | Hyper | virus | — | chr22 | 17081932 | 17082001 | Hyper | cancer_general | TPTEP1, CCT8L2 |
| chr22 | 17082566 | 17082595 | Hyper | liver_tcga | TPTEP1, CCT8L2 | chr22 | 17082943 | 17083003 | Hyper | cancer_general | TPTEP1, CCT8L2 |
| chr22 | 17083396 | 17083496 | Hyper | cancer_general, tcga | TPTEP1, CCT8L2 | chr22 | 17601086 | 17601368 | Hyper | cancer_general | BC021738, CECR6, IL17RA |
| chr22 | 17602511 | 17602624 | Hyper | cancer_general | IL17RA, BC021738, CECR6 | chr22 | 17850454 | 17850621 | Hyper | cancer_general | CECR2 |
| chr22 | 19017532 | 19017567 | Hyper | cancer_general | DGCR2, DGCR10, DGCR9 | chr22 | 19510799 | 19511567 | Hyper | liver_tcga, cancer_general | CLDN5, CDC45 |
| chr22 | 19511849 | 19512098 | Hyper | tcga, cancer_general | CLDN5, CDC45 | chr22 | 19702265 | 19702410 | Hyper | esophageal | SEPT5-GP1BB |
| chr22 | 19706171 | 19706677 | Hyper | cancer_general, tcga, lung | SEPT5-GP1BB | chr22 | 19742834 | 19742969 | Hyper | cancer_general | TBX1 |
| chr22 | 19748644 | 19748956 | Hyper | tcga, cancer_general | TBX1 | chr22 | 20792461 | 20792641 | Hyper | cancer_general, tcga | KLHL22, SCARF2 |
| chr22 | 21368587 | 21368617 | Hyper | esophageal | P2RX6, TUBA3FP, THAP7-AS1 | chr22 | 22005794 | 22006759 | Hyper | pancreas | MIR301B, MIR130B, SDF2L1 |
| chr22 | 22090595 | 22090742 | Hyper | cancer_general | YPEL1 | chr22 | 22862787 | 22863159 | Hyper | tcga, cancer_general | ZNF280A |
| chr22 | 24145484 | 24145513 | Hyper | literature | SMARCB1 | chr22 | 24180687 | 24180766 | Hyper | cancer_general | AK096976, DERL3 |
| chr22 | 24820330 | 24820396 | Hyper | esophageal | ADORA2A, ADORA2A-AS1, EU036692, SPECC1L | chr22 | 25678748 | 25679337 | Hyper | cancer_general | BC040576 |
| chr22 | 25817107 | 25817180 | Hyper | cancer_general | — | chr22 | 25817458 | 25817612 | Hyper | cancer_general | — |
| chr22 | 27053194 | 27053250 | Hyper | liver_tcga | MIAT | chr22 | 28198569 | 28198605 | Hyper | cancer_general | MN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 28838200 | 28838292 | Hyper | lung | — | chr22 | 28838509 | 28838551 | Hyper | cancer_general | CHEK2 |
| chr22 | 28839122 | 28839263 | Hyper | tcga | — | chr22 | 29091824 | 29091853 | Hyper | literature | — |
| chr22 | 29876191 | 29876220 | Hyper | liver_tcga | KIAA0845, NEFH | chr22 | 29877223 | 29877299 | Hyper | cancer_general | KIAA0845, NEFH |
| chr22 | 30116904 | 30117162 | Hyper | tcga | ZMAT5, CABP7 | chr22 | 30476191 | 30476220 | Hyper | literature | HORMAD2 |
| chr22 | 30881582 | 30881612 | Hyper | head_neck | SEC14L4, SDC4P | chr22 | 30938521 | 30938584 | Hyper | cancer_general | SEC14L6 |
| chr22 | 31198492 | 31198637 | Hyper | blood | OSBP2 | chr22 | 31218510 | 31218540 | Hyper | cancer_general | OSBP2 |
| chr22 | 31218794 | 31218829 | Hyper | cancer_general | OSBP2 | chr22 | 31481130 | 31481332 | Hyper | tcga | SMTN |
| chr22 | 33197603 | 33197652 | Hyper | literature | TIMP3 | chr22 | 33453877 | 33454366 | Hyper | cancer_general | — |
| chr22 | 35656581 | 35656610 | Hyper | liver_tcga | HMGXB4 | chr22 | 36681295 | 36681341 | Hyper | liver_tcga | MYH9 |
| chr22 | 37720961 | 37721163 | Hyper | tcga | CYTH4 | chr22 | 38220653 | 38221201 | Hyper | tcga, cancer_general | GCAT, ANKRD54, GALR3 |
| chr22 | 38477069 | 38477794 | Hyper | cancer_general | BAIAP2L2, SLC16A8, PICK1 | chr22 | 39784480 | 39784598 | Hyper | liver_tcga | — |
| chr22 | 39853521 | 39853592 | Hyper | colorectal | MGAT3 | chr22 | 39954413 | 39954516 | Hyper | cancer_general | — |
| chr22 | 40807034 | 40807063 | Hyper | liver_tcga | MKL1, SGSM3 | chr22 | 42310087 | 42310220 | Hyper | cancer_general | SHISA8 |
| chr22 | 42311521 | 42311587 | Hyper | cancer_general | TNFRSF13C, SHISA8 | chr22 | 42353611 | 42353892 | Hyper | cancer_general | LINC00634 |
| chr22 | 42679729 | 42679841 | Hyper | cancer_general | LOC38906 | chr22 | 43740084 | 43740128 | Hyper | cancer_general | — |
| chr22 | 43808280 | 43808428 | Hyper | cancer_general | MPPED1 | chr22 | 44208418 | 44208448 | Hyper | esophageal | — |
| chr22 | 44258366 | 44258506 | Hyper | cancer_general | SULT4A1 | chr22 | 44287650 | 44287696 | Hyper | cancer_general | PNPLA5 |
| chr22 | 45403086 | 45403133 | Hyper | cancer_general | PHF21B | chr22 | 45403478 | 45403714 | Hyper | tcga | PHF21B |
| chr22 | 45404197 | 45404433 | Hyper | tcga, cancer_general | PHF21B | chr22 | 45404994 | 45405061 | Hyper | cancer_general | PHF21B |
| chr22 | 45405318 | 45405418 | Hyper | tcga | PHF21B | chr22 | 45405620 | 45405768 | Hyper | liver_tcga | PHF21B |
| chr22 | 45406271 | 45406328 | Hyper | cancer_general | PHF21B | chr22 | 45719161 | 45719190 | Hyper | liver_tcga | DQ586951, FAM118A |
| chr22 | 46262452 | 46263809 | Hyper | tcga, cancer_general | — | chr22 | 46276749 | 46276820 | Hyper | cancer_general | — |
| chr22 | 46368029 | 46368059 | Hyper | cancer_general | WNT7B | chr22 | 46658791 | 46658846 | Hyper | cancer_general | TTC38, PKDREJ |
| chr22 | 46933089 | 46933237 | Hyper | liver_tcga | — | chr22 | 48885031 | 48885061 | Hyper | cancer_general | FAM19A5 |
| chr22 | 48885296 | 48885901 | Hyper | cancer_general | FAM19A5 | chr22 | 48886659 | 48886849 | Hyper | cancer_general | FAM19A5 |
| chr22 | 48971130 | 48971748 | Hyper | cancer_general | FAM19A5 | chr22 | 48972144 | 48972657 | Hyper | tcga, cancer_general | FAM19A5 |
| chr22 | 50064721 | 50064944 | Hyper | tcga | — | chr22 | 50496841 | 50496918 | Hyper | cancer_general | MLC1 |
| chr22 | 50497147 | 50497287 | Hyper | cancer_general | MLC1 | chr22 | 50623672 | 50623815 | Hyper | literature, cancer_general | TRABD, PANX2 |
| chr22 | 50943093 | 50943262 | Hyper | head_neck | NCAPH2, LMF2 | chr22 | 51042278 | 51042810 | Hyper | cancer_general | MAPK8IP2 |
| chr22 | 51112150 | 51112232 | Hyper | tcga | SHANK3 | chr6 | 391173 | 392000 | Hyper | tcga, liver_tcga, cancer_general | IRF4 |
| chr6 | 392307 | 393650 | Hyper | liver_tcga, tcga, cancer_general | IRF4 | chr6 | 711142 | 711293 | Hyper | pancreas | AX747750 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 1312000 | 1312096 | Hyper | blood | FOXQ1 | chr6 | 1312356 | 1312708 | Hyper | blood | FOXQ1 |
| chr6 | 1314088 | 1314118 | Hyper | blood | FOXQ1 | chr6 | 1378222 | 1379242 | Hyper | tcga, cancer_general | — |
| chr6 | 1379584 | 1379614 | Hyper | cancer_general | — | chr6 | 1379909 | 1379952 | Hyper | cancer_general | FOXF2 |
| chr6 | 1383677 | 1384644 | Hyper | cancer_general, tcga | FOXF2 | chr6 | 1385118 | 1385170 | Hyper | cancer_general | FOXF2 |
| chr6 | 1386071 | 1386112 | Hyper | cancer_general | FOXF2 | chr6 | 1389124 | 1389262 | Hyper | cancer_general | FOXF2 |
| chr6 | 1390241 | 1391035 | Hyper | tcga, cancer_general | FOXF2 | chr6 | 1391318 | 1391379 | Hyper | cancer_general | FOXF2 |
| chr6 | 1524199 | 1524283 | Hyper | cancer_general | GMDS, FOXC1 | chr6 | 1605387 | 1605454 | Hyper | cancer_general | FOXC1 |
| chr6 | 1614833 | 1615184 | Hyper | cancer_general | GMDS, FOXC1 | chr6 | 1620672 | 1620701 | Hyper | liver_tcga | FOXC1, GMDS |
| chr6 | 1624977 | 1625818 | Hyper | liver_tcga, cancer_general | GMDS | chr6 | 3229029 | 3229059 | Hyper | cancer_general | AK096219, TUBB2A, TUBB2B |
| chr6 | 3229423 | 3229510 | Hyper | cancer_general | AK096219, TUBB2A, TUBB2B | chr6 | 3232010 | 3232260 | Hyper | tcga | AK096219, TUBB2A, TUBB2B |
| chr6 | 4775062 | 4775222 | Hyper | liver_tcga | CDYL | chr6 | 5996952 | 5996989 | Hyper | cancer_general | NRN1 |
| chr6 | 5997802 | 5997832 | Hyper | cancer_general | NRN1 | chr6 | 6003287 | 6005417 | Hyper | tcga, cancer_general | NRN1 |
| chr6 | 6006374 | 6006419 | Hyper | cancer_general | NRN1 | chr6 | 6006674 | 6006883 | Hyper | cancer_general | NRN1 |
| chr6 | 6007593 | 6008277 | Hyper | cancer_general | NRN1 | chr6 | 7726334 | 7726363 | Hyper | literature | BMP6 |
| chr6 | 7726630 | 7726659 | Hyper | literature | BMP6 | chr6 | 7726952 | 7726981 | Hyper | literature | BMP6 |
| chr6 | 7727699 | 7728142 | Hyper | literature, cancer_general | BMP6 | chr6 | 7728849 | 7728941 | Hyper | literature | BMP6 |
| chr6 | 10381507 | 10382299 | Hyper | cancer_general | — | chr6 | 10382722 | 10383049 | Hyper | cancer_general | — |
| chr6 | 10383739 | 10383774 | Hyper | cancer_general | — | chr6 | 10384950 | 10385939 | Hyper | cancer_general | — |
| chr6 | 10386210 | 10386273 | Hyper | cancer_general | — | chr6 | 10390023 | 10391187 | Hyper | cancer_general | — |
| chr6 | 10410518 | 10410578 | Hyper | cancer_general | LOC100130275, TFAP2A | chr6 | 10411356 | 10411510 | Hyper | cancer_general | TFAP2A |
| chr6 | 10415113 | 10415215 | Hyper | cancer_general | LOC100130275, TFAP2A | chr6 | 10415559 | 10415713 | Hyper | cancer_general | LOC100130275, TFAP2A |
| chr6 | 10416118 | 10416351 | Hyper | lung, cancer_general | LOC100130275, TFAP2A | chr6 | 10417158 | 10417557 | Hyper | cancer_general | LOC100130275, TFAP2A |
| chr6 | 10419086 | 10419506 | Hyper | cancer_general | LINC00518, LOC100130275, TFAP2A | chr6 | 10419744 | 10419941 | Hyper | cancer_general | LINC00518, LOC100130275 |
| chr6 | 10421053 | 10422635 | Hyper | literature, cancer_general | LINC00518, LOC100130275, TFAP2A | chr6 | 10423613 | 10423704 | Hyper | cancer_general | TFAP2A, LINC00518, LOC100130275 |
| chr6 | 10425496 | 10426884 | Hyper | cancer_general | LINC00518, LOC100130275, TFAP2A | chr6 | 10881835 | 10882057 | Hyper | cancer_general | SYCP2L, GCM2 |
| chr6 | 10882321 | 10882350 | Hyper | literature | SYCP2L, GCM2 | chr6 | 10883008 | 10883038 | Hyper | cancer_general | SYCP2L, GCM2 |
| chr6 | 10883444 | 10883474 | Hyper | cancer_general | GCM2, SYCP2L | chr6 | 10887078 | 10887686 | Hyper | cancer_general | SYCP2L, GCM2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 11044062 | 11044572 | Hyper | tcga, cancer_general | ELOVL2, ELOVL2-AS1 | chr6 | 12749899 | 12749976 | Hyper | cancer_general | PHACTR1 |
| chr6 | 12750210 | 12750255 | Hyper | cancer_general | PHACTR1 | chr6 | 17281417 | 17281534 | Hyper | cancer_general | RBM24 |
| chr6 | 19691638 | 19691841 | Hyper | cancer_general | — | chr6 | 19692066 | 19692318 | Hyper | tcga, cancer_general | — |
| chr6 | 19837064 | 19837140 | Hyper | cancer_general | ID4 | chr6 | 21664719 | 21664749 | Hyper | cancer_general | LINC00340, KAAG1, DCDC2 |
| chr6 | 21665004 | 21665043 | Hyper | cancer_general | LINC00340 | chr6 | 24358291 | 24358320 | Hyper | liver_tcga | ALDH5A1, GPLD1 |
| chr6 | 24360074 | 24360170 | Hyper | hepatobiliary | DCDC2, KAAG1 | chr6 | 24494679 | 24494766 | Hyper | cancer_general | HIST1H4D, HIST1H2BE |
| chr6 | 26034268 | 26034311 | Hyper | cancer_general | HIST1H2BB, HIST1H2AB, HIST1H3B, HIST1H4B | chr6 | 26184095 | 26184391 | Hyper | cancer_general | HIST1H2BF, HIST1H4E, HIST1H2AD, HIST1H3F, HIST1H3D, HIST1H4D |
| chr6 | 26188696 | 26189393 | Hyper | cancer_general | HIST1H3F, HIST1H2AD, HIST1H2BE, HIST1H4D, HIST1H3D | chr6 | 26199137 | 26199167 | Hyper | pancreas | |
| chr6 | 26199686 | 26199716 | Hyper | pancreas | HIST1H2BF, HIST1H4E, HIST1H2AD, HIST1H3F, HIST1H3D | chr6 | 26235223 | 26235623 | Hyper | tcga, liver_tcga | HIST1H3E, HIST1H3F, HIST1H4F, HIST1H1D |
| chr6 | 26240504 | 26241118 | Hyper | liver_tcga, cancer_general | HIST1H4G, HIST1H3F, HIST1H1D, HIST1H4F | chr6 | 26250468 | 26250826 | Hyper | liver_tcga, cancer_general | HIST1H4F, HIST1H2BH, HIST1H3F, HIST1H4G |
| chr6 | 26251054 | 26251182 | Hyper | cancer_general | HIST1H2BH, HIST1H3F, HIST1H4G | chr6 | 26251816 | 26252151 | Hyper | liver_tcga, cancer_general | HIST1H2BH, HIST1H3F, HIST1H4G |
| chr6 | 26271406 | 26271762 | Hyper | cancer_general | BC079832, HIST1H2BI, HIST1H4H, HIST1H3G | chr6 | 26271971 | 26272001 | Hyper | cancer_general | BC079832, HIST1H2BI, HIST1H4H, HIST1H3G |
| chr6 | 26272512 | 26272617 | Hyper | cancer_general | HIST1H2BI, HIST1H4H, BC079832, HIST1H3G | chr6 | 26273400 | 26273480 | Hyper | cancer_general | HIST1H3G, HIST1H4H, HIST1H2BI, BC079832 |
| chr6 | 26284811 | 26284898 | Hyper | hepatobiliary | HIST1H4H, TRNA_Met | chr6 | 26327806 | 26327982 | Hyper | cancer_general | TRNA_Ser, TRNA_Arg, TRNA_Met, TRNA_Trp |
| chr6 | 26328294 | 26328457 | Hyper | cancer_general | TRNA_Arg, TRNA_Met, TRNA_Trp, TRNA_Ser | chr6 | 26332178 | 26332218 | Hyper | lung | TRNA_Trp, TRNA_Met, TRNA_Arg, TRNA_Ser |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 26501857 | 26502209 | Hyper | cancer_general | BTN1A1 | chr6 | 26550994 | 26551034 | Hyper | cancer_general | TRNA_Ile, TRNA_Pro, TRNA_Lys, HMGN4, TRNA_Ala |
| chr6 | 26577158 | 26577475 | Hyper | cancer_general | TRNA_Tyr, TRNA_Ala, BC033330 | chr6 | 26987967 | 26988166 | Hyper | blood | LOC100270746, LINC00240 |
| chr6 | 27059783 | 27059848 | Hyper | cancer_general | TRNA_Ser, TRNA_Pro | chr6 | 27064682 | 27065198 | Hyper | cancer_general | TRNA_Ser, TRNA_Pro |
| chr6 | 27173528 | 27174181 | Hyper | tcga, cancer_general | TRNA_Val, TRNA_Ser, TRNA_Arg | chr6 | 27182869 | 27182899 | Hyper | cancer_general | TRNA_Arg, TRNA_Ser, TRNA_Val |
| chr6 | 27203269 | 27203363 | Hyper | cancer_general | TRNA_Val, TRNA_Ile, TRNA_Leu | chr6 | 27205300 | 27205441 | Hyper | cancer_general | TRNA_Ile, TRNA_Val, TRNA_Leu |
| chr6 | 27205671 | 27206040 | Hyper | cancer_general | TRNA_Ile, TRNA_Val, TRNA_Leu, PRSS16 | chr6 | 27218951 | 27218980 | Hyper | liver_tcga | PRSS16 |
| chr6 | 27228180 | 27228395 | Hyper | cancer_general | PRSS16 | chr6 | 27235876 | 27235905 | Hyper | literature | TRNA_Ile |
| chr6 | 27247636 | 27247724 | Hyper | cancer_general | TRNA_Val, TRNA_Pseudo, TRNA_Ile | chr6 | 27256097 | 27256173 | Hyper | cancer_general | TRNA_Val, TRNA_Pseudo, TRNA_Gln, TRNA_Ser |
| chr6 | 27256383 | 27256420 | Hyper | cancer_general | TRNA_Val, TRNA_Pseudo, TRNA_Gln, TRNA_Ser | chr6 | 27264332 | 27264364 | Hyper | cancer_general | TRNA_Thr, TRNA_Gln, TRNA_Pseudo, TRNA_Val, TRNA_Ser |
| chr6 | 27279845 | 27280012 | Hyper | cancer_general | POM121L2, TRNA_Thr | chr6 | 27463029 | 27463687 | Hyper | liver_tcga, cancer_general | TRNA_Ser, TRNA_Asp |
| chr6 | 27512761 | 27513487 | Hyper | cancer_general | TRNA_Ser, TRNA_Gln | chr6 | 27533822 | 27534341 | Hyper | cancer_general | TRNA_Lys, TRNA_Arg |
| chr6 | 27559809 | 27560075 | Hyper | cancer_general | TRNA_Met, TRNA_Lys, TRNA_Asp | chr6 | 27573171 | 27573392 | Hyper | cancer_general | TRNA_Leu |
| chr6 | 27598738 | 27598860 | Hyper | cancer_general | TRNA_Ile | chr6 | 27599159 | 27599341 | Hyper | cancer_general | TRNA_Ile |
| chr6 | 27635265 | 27635434 | Hyper | cancer_general | TRNA_Ile, TRNA_Arg, TRNA_Ser, TRNA_Phe | chr6 | 27647712 | 27647896 | Hyper | liver_tcga, literature | TRNA_Thr, TRNA_Ile, TRNA_Ser, TRNA_Arg, TRNA_Val |
| chr6 | 27648912 | 27649134 | Hyper | cancer_general, literature | TRNA_Ser, TRNA_Val, TRNA_Thr, TRNA_Ile | chr6 | 27725187 | 27725308 | Hyper | liver_tcga | LOC100131289, TRNA_Val |
| chr6 | 27783039 | 27783068 | Hyper | liver_tcga | HIST1H2BL, HIST1H4I, HIST1H2BM, | chr6 | 27794464 | 27799581 | Hyper | pancreas | HIST1H2AK, HIST1H2BN, HIST1H4K, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| | | | | | HIST1H2AI, HIST1H3H | | | | | | BC016143, FKSG63, HIST1H4J |
| chr6 | 27834676 | 27834835 | Hyper | cancer_general | HIST1H3I, HIST1H4L, HIST1H1B, HIST1H2AL | chr6 | 27835047 | 27835417 | Hyper | cancer_general | HIST1H1B, HIST1H2AL, HIST1H3I, HIST1H4L |
| chr6 | 27839726 | 27840082 | Hyper | cancer_general | HIST1H4L, HIST1H3I, HIST1H1B, HIST1H2AL | chr6 | 27840543 | 27840617 | Hyper | cancer_general | HIST1H3I, HIST1H1B, HIST1H4L |
| chr6 | 27841104 | 27841136 | Hyper | cancer_general | HIST1H4L, HIST1H3I, HIST1H1B, HIST1H2AL | chr6 | 27858515 | 27858637 | Hyper | liver_tcga, cancer_general | HIST1H2AM, HIST1H2BO, HIST1H3J |
| chr6 | 28175189 | 28176212 | Hyper | tcga, cancer_general | TRNA_Ser, TOB2P1 | chr6 | 28227076 | 28227141 | Hyper | literature | ZSCAN26, NKAPL, ZKSCAN4 |
| chr6 | 28303562 | 28303607 | Hyper | lung | ZSCAN31 | chr6 | 28303815 | 28304263 | Hyper | tcga, lung | ZSCAN31 |
| chr6 | 28367109 | 28367774 | Hyper | tcga, cancer_general | ZSCAN12 | chr6 | 28410976 | 28411353 | Hyper | cancer_general | ZSCAN23 |
| chr6 | 28414977 | 28415034 | Hyper | cancer_general | — | chr6 | 28457608 | 28457638 | Hyper | cancer_general | TRNA_Thr |
| chr6 | 28457870 | 28458158 | Hyper | cancer_general | TRNA_Thr | chr6 | 28956323 | 28956719 | Hyper | liver_tcga | TRNA_Leu, ZNF311, TRNA_Glu, TRNA_Phe |
| chr6 | 30095418 | 30095570 | Hyper | liver_tcga | TRIM40, DQ580846 | chr6 | 30644680 | 30644798 | Hyper | liver_tcga | PPP1R18 |
| chr6 | 34113893 | 34113922 | Hyper | tcga | — | chr6 | 35182493 | 35182522 | Hyper | liver_tcga | SCUBE3, AY927475 |
| chr6 | 35479613 | 35479642 | Hyper | literature | TULP1 | chr6 | 35992428 | 35992458 | Hyper | cancer_general | MAPK14, SLC26A8 |
| chr6 | 36252984 | 36253171 | Hyper | cancer_general | PNPLA1 | chr6 | 36808323 | 36808441 | Hyper | cancer_general | AK096023, CPNE5 |
| chr6 | 37664140 | 37664187 | Hyper | cancer_general | DNAH8 | chr6 | 37673320 | 37673611 | Hyper | tcga | — |
| chr6 | 38683206 | 38683235 | Hyper | liver_tcga | DNAH8 | chr6 | 39281088 | 39281133 | Hyper | cancer_general | KCNK17, KCNK16 |
| chr6 | 39281824 | 39281875 | Hyper | cancer_general | KCNK16, KCNK17 | chr6 | 39329863 | 39329892 | Hyper | literature | KIF6 |
| chr6 | 39760401 | 39760661 | Hyper | tcga | DAAM2 | chr6 | 40554653 | 40554699 | Hyper | cancer_general | LRFN2 |
| chr6 | 41337072 | 41337128 | Hyper | cancer_general | — | chr6 | 41339263 | 41339838 | Hyper | cancer_general | — |
| chr6 | 41340902 | 41341182 | Hyper | tcga, cancer_general | — | chr6 | 41341501 | 41341549 | Hyper | cancer_general | — |
| chr6 | 41342243 | 41342275 | Hyper | tcga, cancer_general | MDFI | chr6 | 41342807 | 41342837 | Hyper | cancer_general | — |
| chr6 | 41605937 | 41606542 | Hyper | cancer_general | — | chr6 | 42738966 | 42739049 | Hyper | liver_tcga | — |
| chr6 | 42879554 | 42879718 | Hyper | cancer_general | PTCRA | chr6 | 42928321 | 42928454 | Hyper | blood | GNMT, BC040637, PEX6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 43211193 | 43211311 | Hyper | literature, liver_tcga | TTBK1 | chr6 | 43612825 | 43613067 | Hyper | cancer_general | RSPH9, MAD2L1BP |
| chr6 | 45388716 | 45388775 | Hyper | cancer_general | RUNX2 | chr6 | 46702982 | 46703123 | Hyper | liver_tcga | PLA2G7 |
| chr6 | 46703350 | 46703436 | Hyper | cancer_general | PLA2G7 | chr6 | 50674372 | 50674750 | Hyper | literature, cancer_general | TFAP2D |
| chr6 | 50681699 | 50681942 | Hyper | cancer_general | TFAP2D | chr6 | 50682319 | 50682386 | Hyper | cancer_general | TFAP2D |
| chr6 | 50682659 | 50683227 | Hyper | cancer_general | TFAP2D | chr6 | 50683834 | 50684969 | Hyper | cancer_general | TFAP2D |
| chr6 | 50689913 | 50690039 | Hyper | cancer_general | TFAP2D | chr6 | 50689681 | 50691095 | Hyper | lung | TFAP2D |
| chr6 | 50692083 | 50692481 | Hyper | cancer_general | TFAP2D | chr6 | 50787216 | 50788352 | Hyper | cancer_general | TFAP2B |
| chr6 | 50789374 | 50789404 | Hyper | cancer_general | TFAP2B | chr6 | 50791187 | 50791632 | Hyper | cancer_general, literature | TFAP2B |
| chr6 | 50793335 | 50793404 | Hyper | cancer_general | TFAP2B | chr6 | 50793728 | 50793882 | Hyper | cancer_general | TFAP2B |
| chr6 | 50794531 | 50794693 | Hyper | cancer_general | TFAP2B | chr6 | 50803834 | 50803867 | Hyper | cancer_general | TFAP2B |
| chr6 | 50804131 | 50804368 | Hyper | cancer_general | TFAP2B | chr6 | 50808681 | 50808854 | Hyper | cancer_general | TFAP2B |
| chr6 | 50810551 | 50810839 | Hyper | cancer_general | TFAP2B | chr6 | 50811062 | 50811488 | Hyper | cancer_general | TFAP2B |
| chr6 | 50813258 | 50813939 | Hyper | cancer_general | TFAP2B | chr6 | 50814569 | 50814599 | Hyper | cancer_general | TFAP2B |
| chr6 | 50817023 | 50817229 | Hyper | cancer_general | TFAP2B | chr6 | 50817905 | 50817935 | Hyper | cancer_general | TFAP2B |
| chr6 | 50818449 | 50818706 | Hyper | cancer_general | TFAP2B | chr6 | 50818920 | 50819000 | Hyper | cancer_general | TFAP2B |
| chr6 | 52227752 | 52227781 | Hyper | tcga | PAQR8 | chr6 | 52228008 | 52228037 | Hyper | tcga | PAQR8 |
| chr6 | 53212491 | 53213970 | Hyper | esophageal | — | chr6 | 54711448 | 54711626 | Hyper | blood | FAM83B |
| chr6 | 55443691 | 55443946 | Hyper | cancer_general | HMGCLL1 | chr6 | 56112262 | 56112386 | Hyper | cancer_general | COL21A1 |
| chr6 | 56716332 | 56716410 | Hyper | cancer_general | — | chr6 | 56818656 | 56818937 | Hyper | cancer_general | BEND6 |
| chr6 | 56819217 | 56819637 | Hyper | cancer_general, tcga, liver_tcga | BEND6 | chr6 | 56818897 | 56819926 | Hyper | liver_tcga | BEND6 |
| chr6 | 58147447 | 58147480 | Hyper | cancer_general | TRNA_Ile, TRNA_Ala | chr6 | 58147790 | 58147976 | Hyper | cancer_general | TRNA_Ala, TRNA_Ile |
| chr6 | 62995356 | 62996146 | Hyper | tcga, cancer_general | KHDRBS2 | chr6 | 62996443 | 62996489 | Hyper | cancer_general | KHDRBS2 |
| chr6 | 70992057 | 70992162 | Hyper | cancer_general | COL9A1 | chr6 | 70992415 | 70992560 | Hyper | cancer_general | COL9A1 |
| chr6 | 70992830 | 70993015 | Hyper | cancer_general | COL9A1 | chr6 | 71665638 | 71665723 | Hyper | esophageal | B3GAT2 |
| chr6 | 71666788 | 71666986 | Hyper | tcga, cancer_general | B3GAT2 | chr6 | 72129789 | 72129829 | Hyper | cancer_general | LINC00472 |
| chr6 | 72130107 | 72130464 | Hyper | tcga, cancer_general | LINC00472 | chr6 | 72596120 | 72596315 | Hyper | tcga, pancreas | RIMS1 |
| chr6 | 72596950 | 72596980 | Hyper | tcga, cancer_general | RIMS1 | chr6 | 73329784 | 73330126 | Hyper | cancer_general | KCNQ5 |
| chr6 | 73330834 | 73331304 | Hyper | tcga, cancer_general | KCNQ5 | chr6 | 73331515 | 73333122 | Hyper | cancer_general, colorectal, tcga | KCNQ5 |
| chr6 | 76059561 | 76059787 | Hyper | tcga | — | chr6 | 78172177 | 78172572 | Hyper | tcga, literature, cancer_general | HTR1B |
| chr6 | 78173212 | 78173264 | Hyper | literature | HTR1B | chr6 | 78173696 | 78173984 | Hyper | cancer_general | HTR1B |
| chr6 | 78176458 | 78176820 | Hyper | cancer_general, tcga | HTR1B | chr6 | 79620399 | 79620699 | Hyper | tcga, cancer_general | IRAK1BP1 |
| chr6 | 80656930 | 80657180 | Hyper | cancer_general | ELOVL4 | chr6 | 82463270 | 82463310 | Hyper | blood | FAM46A |
| chr6 | 84141298 | 84141412 | Hyper | pancreas | ME1 | chr6 | 84417436 | 84417778 | Hyper | cancer_general | SNAP91 |
| chr6 | 84418172 | 84418281 | Hyper | cancer_general | SNAP91 | chr6 | 84418644 | 84418803 | Hyper | cancer_general, tcga, liver_tcga | SNAP91 |
| chr6 | 84419157 | 84419415 | Hyper | cancer_general | SNAP91 | chr6 | 84562873 | 84563242 | Hyper | cancer_general, tcga | RIPPLY2, CYB5R4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 84563489 | 84563542 | Hyper | cancer_general | CYB5R4, RIPPLY2 | chr6 | 85472407 | 85473703 | Hyper | tcga, cancer_general | TBX18 |
| chr6 | 85473928 | 85474378 | Hyper | tcga, cancer_general | TBX18 | chr6 | 85474594 | 85474736 | Hyper | cancer_general | TBX18 |
| chr6 | 85476233 | 85476285 | Hyper | cancer_general | TBX18 | chr6 | 85476998 | 85477028 | Hyper | cancer_general | TBX18 |
| chr6 | 85478514 | 85478724 | Hyper | cancer_general | TBX18 | chr6 | 85482530 | 85482822 | Hyper | cancer_general | TBX18 |
| chr6 | 85483345 | 85483375 | Hyper | cancer_general | TBX18 | chr6 | 85483635 | 85484920 | Hyper | cancer_general, tcga | TBX18 |
| chr6 | 87647114 | 87647143 | Hyper | literature | HTR1E | chr6 | 87862092 | 87862172 | Hyper | cancer_general | ZNF292 |
| chr6 | 88876963 | 88877437 | Hyper | cancer_general | — | chr6 | 91320285 | 91320318 | Hyper | cancer_general | — |
| chr6 | 91320949 | 91321295 | Hyper | tcga | — | chr6 | 94126973 | 94127064 | Hyper | cancer_general | EPHA7 |
| chr6 | 94127455 | 94127544 | Hyper | cancer_general | EPHA7 | chr6 | 94128365 | 94128399 | Hyper | cancer_general | EPHA7 |
| chr6 | 94129219 | 94129257 | Hyper | tcga | EPHA7 | chr6 | 94129509 | 94129575 | Hyper | cancer_general | EPHA7 |
| chr6 | 96464100 | 96464204 | Hyper | cancer_general | FUT9 | chr6 | 99271926 | 99272810 | Hyper | cancer_general | POU3F2 |
| chr6 | 99273369 | 99273410 | Hyper | cancer_general | POU3F2 | chr6 | 99277180 | 99277330 | Hyper | cancer_general | POU3F2 |
| chr6 | 99279556 | 99279612 | Hyper | cancer_general | POU3F2 | chr6 | 99280557 | 99280744 | Hyper | cancer_general | POU3F2 |
| chr6 | 99281014 | 99281385 | Hyper | cancer_general | POU3F2 | chr6 | 99283512 | 99283582 | Hyper | cancer_general | POU3F2 |
| chr6 | 99290360 | 99290398 | Hyper | cancer_general | POU3F2 | chr6 | 99290657 | 99290693 | Hyper | cancer_general | POU3F2 |
| chr6 | 99291264 | 99291438 | Hyper | cancer_general | POU3F2 | chr6 | 99292252 | 99292417 | Hyper | cancer_general | POU3F2 |
| chr6 | 99295726 | 99296467 | Hyper | cancer_general | POU3F2 | chr6 | 99842067 | 99842258 | Hyper | tcga | PNISR, BC033061, COQ3 |
| chr6 | 100038682 | 100038964 | Hyper | cancer_general | — | chr6 | 100039259 | 100039289 | Hyper | cancer_general | — |
| chr6 | 100050754 | 100051971 | Hyper | cancer_general | PRDM13 | chr6 | 100053221 | 100053511 | Hyper | cancer_general | PRDM13 |
| chr6 | 100054866 | 100054917 | Hyper | cancer_general | PRDM13 | chr6 | 100061022 | 100061076 | Hyper | cancer_general | PRDM13 |
| chr6 | 100061311 | 100061419 | Hyper | cancer_general | PRDM13 | chr6 | 100061757 | 100061835 | Hyper | cancer_general | PRDM13 |
| chr6 | 100062178 | 100062586 | Hyper | cancer_general | MCHR2, LOC728012 | chr6 | 100062944 | 100063068 | Hyper | cancer_general | PRDM13 |
| chr6 | 100441364 | 100441966 | Hyper | cancer_general | SIM1 | chr6 | 100903384 | 100903631 | Hyper | cancer_general | SIM1 |
| chr6 | 100904214 | 100904275 | Hyper | cancer_general | SIM1 | chr6 | 100905969 | 100906016 | Hyper | cancer_general | SIM1 |
| chr6 | 100911686 | 100911723 | Hyper | literature | SIM1 | chr6 | 100912070 | 100912119 | Hyper | cancer_general | SIM1 |
| chr6 | 100912421 | 100912480 | Hyper | cancer_general | SIM1 | chr6 | 100912919 | 100913149 | Hyper | liver_tcga, literature, cancer_general | SIM1 |
| chr6 | 100915101 | 100915205 | Hyper | liver_tcga, cancer_general | SIM1 | chr6 | 101840708 | 101840820 | Hyper | cancer_general | GRIK2 |
| chr6 | 101846782 | 101846811 | Hyper | literature | GRIK2 | chr6 | 101847185 | 101847215 | Hyper | cancer_general | GRIK2 |
| chr6 | 101850147 | 101850275 | Hyper | cancer_general | GRIK2 | chr6 | 101850570 | 101850600 | Hyper | cancer_general | GRIK2 |
| chr6 | 105388679 | 105388708 | Hyper | literature, cancer_general | LINC00577 | chr6 | 105388913 | 105389710 | Hyper | cancer_general | LINC00577 |
| chr6 | 105400913 | 105401007 | Hyper | cancer_general | LIN28B | chr6 | 105401620 | 105401874 | Hyper | cancer_general | LIN28B |
| chr6 | 105404574 | 105404674 | Hyper | cancer_general | LIN28B | chr6 | 105405656 | 105405772 | Hyper | tcga, cancer_general, liver_tcga | LIN28B |
| chr6 | 105406098 | 105406128 | Hyper | cancer_general | LIN28B | chr6 | 105584264 | 105585554 | Hyper | literature | BVES-AS1, BVES |
| chr6 | 106429049 | 106429624 | Hyper | liver_tcga, cancer_general | — | chr6 | 106434339 | 106434368 | Hyper | cancer_general | — |
| chr6 | 106441869 | 106442979 | Hyper | cancer_general | SOBP | chr6 | 106960908 | 106961023 | Hyper | cancer_general | AIM1 |
| chr6 | 107955952 | 107955982 | Hyper | cancer_general | AF520419 | chr6 | 108435075 | 108435263 | Hyper | cancer_general | AF520419 |
| chr6 | 108436072 | 108436526 | Hyper | cancer_general | AF520419 | chr6 | 108438245 | 108438577 | Hyper | cancer_general | AF520419 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 108440091 | 108440961 | Hyper | cancer_general | AF520419 | chr6 | 108479290 | 108479665 | Hyper | cancer_general | NR2E1, AF520419 |
| chr6 | 108484909 | 108485406 | Hyper | cancer_general | NR2E1, AF520419 | chr6 | 108485665 | 108485905 | Hyper | cancer_general | NR2E1, AF520419 |
| chr6 | 108486158 | 108486394 | Hyper | liver_tcga, cancer_general | NR2E1, AF520419 | chr6 | 108487724 | 108488416 | Hyper | liver_tcga, cancer_general | NR2E1, AF520419 |
| chr6 | 108489385 | 108490633 | Hyper | liver_tcga, cancer_general | NR2E1 | chr6 | 108490978 | 108491423 | Hyper | cancer_general | NR2E1 |
| chr6 | 108492270 | 108492451 | Hyper | liver_tcga, cancer_general | NR2E1 | chr6 | 108495681 | 108495951 | Hyper | cancer_general | NR2E1 |
| chr6 | 108496208 | 108496649 | Hyper | cancer_general | NR2E1 | chr6 | 108497494 | 108497881 | Hyper | tcga, liver_tcga, cancer_general | NR2E1 |
| chr6 | 110679123 | 110679414 | Hyper | cancer_general | METTL24 | chr6 | 110797678 | 110797708 | Hyper | cancer_general | SLC22A16 |
| chr6 | 110799007 | 110799036 | Hyper | literature | SLC22A16 | chr6 | 116783448 | 116783493 | Hyper | cancer_general | FAM26F |
| chr6 | 117086249 | 117086864 | Hyper | tcga, cancer_general | FAM162B | chr6 | 117585967 | 117586004 | Hyper | cancer_general | VGLL2 |
| chr6 | 117586802 | 117587169 | Hyper | tcga, cancer_general | VGLL2 | chr6 | 117587480 | 117587577 | Hyper | cancer_general | VGLL2 |
| chr6 | 117591161 | 117591191 | Hyper | cancer_general | VGLL2 | chr6 | 117591411 | 117591743 | Hyper | cancer_general | VGLL2 |
| chr6 | 118228102 | 118228151 | Hyper | cancer_general | SLC35F1 | chr6 | 118228747 | 118228828 | Hyper | cancer_general | SLC35F1 |
| chr6 | 118229154 | 118229383 | Hyper | tcga, cancer_general | SLC35F1 | chr6 | 118229626 | 118229818 | Hyper | tcga, cancer_general | SLC35F1 |
| chr6 | 118241228 | 118241500 | Hyper | tcga, cancer_general | SLC35F1 | chr6 | 121758672 | 121758994 | Hyper | tcga, cancer_general | GJA1 |
| chr6 | 123317029 | 123317589 | Hyper | cancer_general | CLVS2 | chr6 | 123317797 | 123317833 | Hyper | cancer_general | CLVS2 |
| chr6 | 124124432 | 124124466 | Hyper | cancer_general | NKAIN2 | chr6 | 124124860 | 124125016 | Hyper | tcga | NKAIN2 |
| chr6 | 125284131 | 125284175 | Hyper | cancer_general | Metazoa_SRP, RNF217, STL | chr6 | 126068092 | 126068178 | Hyper | lung, cancer_general | HEY2, BC036196 |
| chr6 | 127439379 | 127439453 | Hyper | cancer_general | RSPO3 | chr6 | 127439985 | 127440127 | Hyper | cancer_general, tcga | RSPO3 |
| chr6 | 127440331 | 127441123 | Hyper | colorectal, cancer_general | RSPO3 | chr6 | 127441554 | 127441762 | Hyper | cancer_general | RSPO3 |
| chr6 | 127442021 | 127442104 | Hyper | cancer_general | RSPO3 | chr6 | 127840501 | 127840681 | Hyper | cancer_general | — |
| chr6 | 129204459 | 129204524 | Hyper | cancer_general | LAMA2 | chr6 | 130686534 | 130687057 | Hyper | tcga, cancer_general | TMEM200A |
| chr6 | 131602584 | 131602694 | Hyper | cancer_general | AKAP7 | chr6 | 132722078 | 132722196 | Hyper | cancer_general | MOXD1 |
| chr6 | 133561740 | 133562070 | Hyper | cancer_general | EYA4 | chr6 | 133562374 | 133563058 | Hyper | liver_tcga, cancer_general | EYA4 |
| chr6 | 133563327 | 133563918 | Hyper | tcga, cancer_general | EYA4 | chr6 | 134176549 | 134176579 | Hyper | cancer_general | MGC34034, BC041459 |
| chr6 | 134210528 | 134211367 | Hyper | cancer_general | AX747860, TCF21 | chr6 | 134213944 | 134214364 | Hyper | cancer_general | AX747860, TCF21 |
| chr6 | 134638950 | 134639003 | Hyper | cancer_general | SGK1 | chr6 | 137241928 | 137242205 | Hyper | cancer_general | SLC35D3, PEX7 |
| chr6 | 137243208 | 137243410 | Hyper | liver_tcga | PEX7, SLC35D3 | chr6 | 137244114 | 137244616 | Hyper | cancer_general | SLC35D3, PEX7 |
| chr6 | 137311158 | 137311380 | Hyper | cancer_general | IL20RA, NHEG1 | chr6 | 137809141 | 137811088 | Hyper | cancer_general | OLIG3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 137813787 | 137813895 | Hyper | cancer_general | OLIG3 | chr6 | 137814604 | 137814763 | Hyper | liver_tcga, cancer_general | OLIG3 |
| chr6 | 137815008 | 137815662 | Hyper | cancer_general | OLIG3 | chr6 | 137816472 | 137817351 | Hyper | cancer_general | OLIG3 |
| chr6 | 137818505 | 137819368 | Hyper | cancer_general | OLIG3 | chr6 | 146755567 | 146755649 | Hyper | cancer_general | — |
| chr6 | 150284552 | 150284581 | Hyper | literature | ULBP1 | chr6 | 150285056 | 150286639 | Hyper | liver_tcga, literature, cancer_general, tcga | ULBP1 |
| chr6 | 150358970 | 150359407 | Hyper | tcga, cancer_general | — | chr6 | 151561016 | 151561857 | Hyper | cancer_general, tcga | AKAP12 |
| chr6 | 151562066 | 151562563 | Hyper | cancer_general | AKAP12 | chr6 | 151815055 | 151815089 | Hyper | colorectal | CCDC170 |
| chr6 | 152419908 | 152419940 | Hyper | literature | ESR1 | chr6 | 152623015 | 152623493 | Hyper | lung, cancer_general | SYNE1 |
| chr6 | 152957895 | 152958076 | Hyper | cancer_general, tcga, colorectal | SYNE1 | chr6 | 153451236 | 153451500 | Hyper | cancer_general, tcga | RGS17 |
| chr6 | 153451890 | 153451968 | Hyper | cancer_general | RGS17 | chr6 | 153452232 | 153452320 | Hyper | liver_tcga | RGS17 |
| chr6 | 153452713 | 153452746 | Hyper | liver_tcga, literature | RGS17 | chr6 | 154360650 | 154360746 | Hyper | cancer_general | OPRM1 |
| chr6 | 155316235 | 155316265 | Hyper | cancer_general | — | chr6 | 157556764 | 157557912 | Hyper | cancer_general | — |
| chr6 | 159290823 | 159290852 | Hyper | liver_tcga | — | chr6 | 159590048 | 159590986 | Hyper | cancer_general | FNDC1 |
| chr6 | 159654923 | 159655003 | Hyper | cancer_general | FNDC1 | chr6 | 161100361 | 161100390 | Hyper | literature | — |
| chr6 | 161188513 | 161188543 | Hyper | cancer_general | — | chr6 | 161352101 | 161352135 | Hyper | cancer_general | — |
| chr6 | 163834314 | 163834637 | Hyper | colorectal | QKI, CAHM | chr6 | 163834857 | 163834938 | Hyper | tcga | QKI, CAHM |
| chr6 | 163836568 | 163836900 | Hyper | colorectal | QKI, CAHM | chr6 | 166074119 | 166074412 | Hyper | cancer_general | — |
| chr6 | 166076788 | 166077021 | Hyper | cancer_general | — | chr6 | 166077378 | 166077660 | Hyper | cancer_general | LINC00602, LINC00473, AK090688 |
| chr6 | 166267582 | 166268082 | Hyper | cancer_general | AK090688 | chr6 | 166401254 | 166401307 | Hyper | cancer_general | |
| chr6 | 166402240 | 166402546 | Hyper | cancer_general | LINC00473, AK090688, LINC00602 | chr6 | 166421911 | 166422185 | Hyper | cancer_general | — |
| chr6 | 166579723 | 166580144 | Hyper | cancer_general | T | chr6 | 166580344 | 166582797 | Hyper | tcga, cancer_general, literature | T |
| chr6 | 168842847 | 168842944 | Hyper | cancer_general | SMOC2 | chr6 | 169653638 | 169653668 | Hyper | cancer_general | THBS2 |
| chr4 | 107711 | 107759 | Hyper | cancer_general | — | chr4 | 206324 | 206353 | Hyper | literature | ZNF876P |
| chr4 | 330392 | 330708 | Hyper | tcga, cancer_general, liver_tcga | ZNF141 | chr4 | 331322 | 331352 | Hyper | esophageal | ZNF141 |
| chr4 | 568429 | 569914 | Hyper | cancer_general | — | chr4 | 570966 | 571013 | Hyper | cancer_general | — |
| chr4 | 571508 | 571689 | Hyper | cancer_general | — | chr4 | 657521 | 657552 | Hyper | tcga | — |
| chr4 | 682798 | 682919 | Hyper | cancer_general | MFSD7, MYL5 | chr4 | 995855 | 996357 | Hyper | cancer_general, tcga, liver_tcga | ATP5I, MYL5, PDE6B, BC020343 FGFRL1, SLC26A1, IDUA |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 996639 | 996708 | Hyper | cancer_general | IDUA, FGFRL1, SLC26A1 | chr4 | 1107494 | 1107585 | Hyper | liver_tcga | RNF212, TMED11P |
| chr4 | 1165379 | 1165470 | Hyper | cancer_general | SPON2 | | | | | | |
| chr4 | 1397396 | 1397495 | Hyper | cancer_general | CRIPAK | chr4 | 1396578 | 1396835 | Hyper | liver_tcga, cancer_general | CRIPAK |
| chr4 | 1399723 | 1399768 | Hyper | cancer_general | CRIPAK | chr4 | 1398303 | 1398378 | Hyper | cancer_general | CRIPAK |
| chr4 | 1401711 | 1401743 | Hyper | cancer_general | — | chr4 | 1400728 | 1400785 | Hyper | cancer_general | — |
| chr4 | 1803550 | 1803582 | Hyper | literature | LETM1, FGFR3 | chr4 | 1800153 | 1800191 | Hyper | liver_tcga | FGFR3 |
| chr4 | 1807355 | 1807384 | Hyper | literature | LETM1, FGFR3 | chr4 | 1806084 | 1806113 | Hyper | literature | LETM1, FGFR3 |
| chr4 | 2042106 | 2042556 | Hyper | cancer_general | C4orf48 | chr4 | 1962787 | 1962816 | Hyper | literature | WHSC1 |
| chr4 | 3371519 | 3371652 | Hyper | liver_3842731tcga | RGS12 | chr4 | 2765862 | 2765910 | Hyper | cancer_general | TNIP2 |
| chr4 | 3769542 | 3769574 | Hyper | cancer_general | ADRA2C | chr4 | 3768833 | 3769342 | Hyper | cancer_general | ADRA2C |
| chr4 | 4228185 | 4228241 | Hyper | cancer_general | TMEM128, OTOP1 | chr4 | 3873694 | 3873769 | Hyper | cancer_general | — |
| | | | | | | chr4 | 4229689 | 4229781 | Hyper | cancer_general | OTOP1, TMEM128 |
| chr4 | 4387533 | 4387627 | Hyper | cancer_general | NSG1 | chr4 | 4855102 | 4855171 | Hyper | cancer_general | MSX1 |
| chr4 | 4855371 | 4855433 | Hyper | cancer_general | MSX1 | chr4 | 4860046 | 4860075 | Hyper | literature | MSX1 |
| chr4 | 4862769 | 4863110 | Hyper | cancer_general | MSX1 | chr4 | 4867698 | 4867886 | Hyper | cancer_general | MSX1 |
| chr4 | 4868566 | 4869087 | Hyper | tcga, cancer_general | MSX1 | chr4 | 4872088 | 4872167 | Hyper | cancer_general | MSX1 |
| chr4 | 4872777 | 4872850 | Hyper | cancer_general | MSX1 | chr4 | 4873427 | 4873528 | Hyper | tcga | MSX1 |
| chr4 | 5021188 | 5021217 | Hyper | literature | CYTL1 | chr4 | 5053070 | 5053518 | Hyper | tcga, cancer_general | STK32B |
| chr4 | 5053747 | 5054093 | Hyper | cancer_general | STK32B | chr4 | 5709906 | 5710269 | Hyper | tcga, cancer_general | EVC, EVC2 |
| chr4 | 5712979 | 5713281 | Hyper | tcga | EVC, EVC2 | chr4 | 5889948 | 5890045 | Hyper | cancer_general | CRMP1, FLJ46481 |
| chr4 | 5890274 | 5890444 | Hyper | tcga | FLJ46481, CRMP1 | chr4 | 5891966 | 5892194 | Hyper | cancer_general, pancreas | FLJ46481, CRMP1 |
| chr4 | 5892750 | 5892780 | Hyper | cancer_general | CRMP1, FLJ46481 | chr4 | 5893981 | 5894347 | Hyper | cancer_general | FLJ46481, CRMP1 |
| chr4 | 5894676 | 5894787 | Hyper | liver_tcga, cancer_general | FLJ46481, CRMP1 | chr4 | 6200897 | 6201235 | Hyper | cancer_general | JAKMIP1, LOC285484 |
| chr4 | 6202103 | 6202276 | Hyper | cancer_general | LOC285484, JAKMIP1 | chr4 | 6247351 | 6247381 | Hyper | cancer_general | LOC285484 |
| chr4 | 6565004 | 6565042 | Hyper | cancer_general | — | chr4 | 8582549 | 8582579 | Hyper | cancer_general | CPZ, GPR78 |
| chr4 | 8858827 | 8859738 | Hyper | cancer_general | HMX1 | chr4 | 8859974 | 8860553 | Hyper | cancer_general | HMX1 |
| chr4 | 8861649 | 8862014 | Hyper | cancer_general | HMX1 | chr4 | 8862797 | 8862911 | Hyper | cancer_general | HMX1 |
| chr4 | 8863441 | 8863774 | Hyper | cancer_general | HMX1 | chr4 | 8864499 | 8864598 | Hyper | cancer_general | HMX1 |
| chr4 | 8864831 | 8865058 | Hyper | cancer_general | HMX1 | chr4 | 8868822 | 8869364 | Hyper | cancer_general | HMX1 |
| chr4 | 8869601 | 8869813 | Hyper | cancer_general | HMX1 | chr4 | 8873054 | 8873337 | Hyper | cancer_general | HMX1 |
| chr4 | 8873809 | 8873984 | Hyper | cancer_general | HMX1 | chr4 | 8874485 | 8874787 | Hyper | cancer_general | HMX1 |
| chr4 | 8875877 | 8875907 | Hyper | cancer_general | HMX1 | chr4 | 8893060 | 8893093 | Hyper | pancreas | — |
| chr4 | 8893501 | 8893531 | Hyper | cancer_general | — | chr4 | 8893794 | 8893931 | Hyper | cancer_general | — |
| chr4 | 8894641 | 8895350 | Hyper | cancer_general | — | chr4 | 8895554 | 8895584 | Hyper | cancer_general | — |
| chr4 | 8895915 | 8896052 | Hyper | cancer_general | — | chr4 | 9782992 | 9783412 | Hyper | literature, cancer_general | DRD5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 10458395 | 10459121 | Hyper | cancer_general | ZNF518B | chr4 | 10462833 | 10463604 | Hyper | tcga, cancer_general | ZNF518B |
| chr4 | 11429506 | 11429633 | Hyper | cancer_general | — | chr4 | 13524026 | 13524430 | Hyper | tcga, cancer_general | LOC285547 |
| chr4 | 13524665 | 13524775 | Hyper | cancer_general | LOC285547 | chr4 | 13537569 | 13537688 | Hyper | cancer_general | NKX3-2, LOC285547 |
| chr4 | 13540983 | 13541068 | Hyper | cancer_general | NKX3-2, LOC285548, LOC285547 | chr4 | 13541408 | 13541447 | Hyper | cancer_general | LOC285548, LOC285547, NKX3-2 |
| chr4 | 13543859 | 13544113 | Hyper | liver_tcga, cancer_general | LOC285548, NKX3-2 | chr4 | 13545563 | 13545760 | Hyper | liver_tcga, cancer_general | LOC285548, NKX3-2 |
| chr4 | 13546026 | 13546078 | Hyper | cancer_general | LOC285548, NKX3-2 | chr4 | 13548502 | 13548895 | Hyper | cancer_general | LOC285548, NKX3-2 |
| chr4 | 13549340 | 13549510 | Hyper | tcga | LOC285548, NKX3-2 | chr4 | 15780223 | 15780320 | Hyper | tcga, liver_tcga | CD38 |
| chr4 | 16084741 | 16085381 | Hyper | tcga, cancer_general | — | chr4 | 16085618 | 16085682 | Hyper | cancer_general | — |
| chr4 | 17783003 | 17783600 | Hyper | tcga, cancer_general, liver_tcga | FAM184B | chr4 | 20254693 | 20254723 | Hyper | cancer_general | SLIT2 |
| chr4 | 20255414 | 20255861 | Hyper | cancer_general | SLIT2 | chr4 | 20256152 | 20256340 | Hyper | cancer_general | SLIT2, CCDC149, SOD3 |
| chr4 | 21950248 | 21950341 | Hyper | cancer_general | — | chr4 | 24801809 | 24801985 | Hyper | cancer_general | CCDC149, SOD3 |
| chr4 | 24914638 | 24914668 | Hyper | blood | CCDC149 | chr4 | 25656815 | 25656879 | Hyper | tcga | SLC34A2 |
| chr4 | 25657437 | 25657477 | Hyper | cancer_general | SLC34A2 | chr4 | 27086432 | 27086462 | Hyper | cancer_general | — |
| chr4 | 30722243 | 30722273 | Hyper | cancer_general | PCDH7 | chr4 | 30723811 | 30723862 | Hyper | cancer_general | PCDH7 |
| chr4 | 30724249 | 30724372 | Hyper | cancer_general | PCDH7 | chr4 | 37245726 | 37245851 | Hyper | cancer_general | KIAA1239, MIR4801 |
| chr4 | 37246134 | 37246883 | Hyper | tcga, cancer_general | KIAA1239, MIR4801 | chr4 | 37247096 | 37247216 | Hyper | cancer_general | KIAA1239, MIR4801 |
| chr4 | 40632773 | 40632802 | Hyper | lung, cancer_general | — | chr4 | 41258716 | 41259176 | Hyper | liver_tcga, cancer_general | UCHL1, UCHL1-AS1 |
| chr4 | 41747009 | 41747133 | Hyper | cancer_general | PHOX2B | chr4 | 41747493 | 41747582 | Hyper | cancer_general | PHOX2B |
| chr4 | 41747958 | 41748296 | Hyper | cancer_general | PHOX2B | chr4 | 41748660 | 41748803 | Hyper | cancer_general | PHOX2B |
| chr4 | 41749033 | 41749063 | Hyper | cancer_general | PHOX2B | chr4 | 41749270 | 41749761 | Hyper | cancer_general | PHOX2B |
| chr4 | 41750223 | 41750504 | Hyper | lung, cancer_general | PHOX2B | chr4 | 41751870 | 41752006 | Hyper | cancer_general | PHOX2B |
| chr4 | 41752451 | 41752693 | Hyper | cancer_general | PHOX2B | chr4 | 41752968 | 41753398 | Hyper | cancer_general | PHOX2B |
| chr4 | 41753610 | 41754071 | Hyper | cancer_general | PHOX2B | chr4 | 41875430 | 41875902 | Hyper | cancer_general | BC025350 |
| chr4 | 41880331 | 41880412 | Hyper | cancer_general | BC025350 | chr4 | 41881385 | 41881425 | Hyper | cancer_general | BC025350 |
| chr4 | 41882549 | 41882627 | Hyper | literature, cancer_general | BC025350 | chr4 | 41883091 | 41883302 | Hyper | cancer_general | BC025350 |
| chr4 | 41883510 | 41883610 | Hyper | cancer_general | BC025350 | chr4 | 42152908 | 42154025 | Hyper | liver_tcga, cancer_general, tcga | BEND4 |
| chr4 | 42154280 | 42154359 | Hyper | cancer_general | BEND4 | chr4 | 42154662 | 42154997 | Hyper | pancreas, cancer_general, literature | BEND4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 42398842 | 42398872 | Hyper | lung | SHISA3 | chr4 | 42399137 | 42399191 | Hyper | cancer_general | SHISA3 |
| chr4 | 42399688 | 42399872 | Hyper | tcga, liver_tcga | SHISA3 | chr4 | 44449480 | 44449651 | Hyper | cancer_general | KCTD8 |
| chr4 | 44450263 | 44450375 | Hyper | cancer_general | KCTD8 | chr4 | 46691353 | 46691383 | Hyper | cancer_general | GABRA2 |
| chr4 | 46995161 | 46995835 | Hyper | tcga, cancer_general, liver_tcga | GABRA4 | chr4 | 47034908 | 47034938 | Hyper | cancer_general | GABRB1 |
| chr4 | 48485067 | 48486000 | Hyper | liver_tcga, cancer_general | SLC10A4, ZAR1 | chr4 | 48486356 | 48486389 | Hyper | cancer_general | ZAR1, SLC10A4 |
| chr4 | 48492181 | 48492433 | Hyper | tcga, liver_tcga, cancer_general | ZAR1, FRYL, SLC10A4 | chr4 | 48988109 | 48988335 | Hyper | tcga | CWH43 |
| chr4 | 53728495 | 53729056 | Hyper | tcga, cancer_general, liver_tcga | RASL11B | chr4 | 54966854 | 54967075 | Hyper | tcga, cancer_general | GSX2 |
| chr4 | 54967342 | 54967484 | Hyper | cancer_general | GSX2 | chr4 | 54969833 | 54970095 | Hyper | cancer_general | GSX2 |
| chr4 | 54970369 | 54970482 | Hyper | cancer_general | GSX2 | chr4 | 54975936 | 54976131 | Hyper | cancer_general | GSX2 |
| chr4 | 55093048 | 55093255 | Hyper | cancer_general | PDGFRA | chr4 | 55096239 | 55096344 | Hyper | cancer_general | PDGFRA |
| chr4 | 55097404 | 55097634 | Hyper | cancer_general | PDGFRA | chr4 | 55097973 | 55098373 | Hyper | tcga, cancer_general | PDGFRA |
| chr4 | 55098674 | 55098744 | Hyper | cancer_general | PDGFRA | chr4 | 55099016 | 55099062 | Hyper | cancer_general | PDGFRA |
| chr4 | 55133613 | 55133642 | Hyper | literature | PDGFRA | chr4 | 55136787 | 55136816 | Hyper | literature | PDGFRA |
| chr4 | 55138657 | 55138686 | Hyper | literature | PDGFRA | chr4 | 55139691 | 55139720 | Hyper | literature | PDGFRA |
| chr4 | 55140731 | 55140784 | Hyper | literature | PDGFRA | chr4 | 55141015 | 55141050 | Hyper | literature | PDGFRA |
| chr4 | 55144105 | 55144134 | Hyper | literature | PDGFRA | chr4 | 55146554 | 55146583 | Hyper | literature | PDGFRA |
| chr4 | 55152075 | 55152140 | Hyper | literature | PDGFRA | chr4 | 55524220 | 55524274 | Hyper | literature | KIT |
| chr4 | 55589753 | 55589782 | Hyper | literature | DL490879, KIT | chr4 | 55592166 | 55592204 | Hyper | literature | DL490879, KIT |
| chr4 | 55593417 | 55593675 | Hyper | literature | KIT, DL490879 | chr4 | 55594183 | 55594212 | Hyper | literature | DL490879, KIT |
| chr4 | 55595504 | 55595614 | Hyper | literature | KIT, DL490879 | chr4 | 55599306 | 55599356 | Hyper | literature | KIT, DL490879 |
| chr4 | 55968165 | 55968194 | Hyper | literature | KDR | chr4 | 55991107 | 55991228 | Hyper | cancer_general | KDR |
| chr4 | 55992129 | 55992169 | Hyper | cancer_general | KDR | chr4 | 56659692 | 56660021 | Hyper | cancer_general | U6 |
| chr4 | 57371718 | 57371963 | Hyper | liver_tcga, cancer_general | ARL9, SRP72 | chr4 | 57372336 | 57372504 | Hyper | cancer_general | ARL9, SRP72 |
| chr4 | 57396946 | 57397264 | Hyper | cancer_general | THEGL, ARL9 | chr4 | 57521403 | 57522815 | Hyper | tcga, cancer_general | HOPX |
| chr4 | 57687720 | 57687782 | Hyper | esophageal | SPINK2 | chr4 | 57976033 | 57976185 | Hyper | liver_tcga, tcga | LOC255130, IGFBP7 |
| chr4 | 57976416 | 57976573 | Hyper | tcga, liver_tcga | IGFBP7, LOC255130 | chr4 | 58030191 | 58030524 | Hyper | esophageal | LOC255130 |
| chr4 | 62066196 | 62066553 | Hyper | tcga | LPHN3 | chr4 | 62067511 | 62067624 | Hyper | cancer_general | LPHN3 |
| chr4 | 62068072 | 62068150 | Hyper | cancer_general | LPHN3 | chr4 | 66335130 | 66335443 | Hyper | tcga, cancer_general | LOC100144602, EPHA5 |
| chr4 | 66536171 | 66536323 | Hyper | tcga | LOC100144602, EPHA5 | chr4 | 74702479 | 74702516 | Hyper | cancer_general | CXCL6 |
| chr4 | 74735076 | 74735137 | Hyper | blood | CXCL1 | chr4 | 74809877 | 74809933 | Hyper | cancer_general | — |
| chr4 | 75858573 | 75858629 | Hyper | esophageal | PARM1 | chr4 | 76855532 | 76855856 | Hyper | cancer_general, tcga, liver_tcga | CDKL2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 81106351 | 81106871 | Hyper | tcga, cancer_general | PRDM8 | chr4 | 81122277 | 81124662 | Hyper | cancer_general | PRDM8 |
| chr4 | 81187046 | 81187076 | Hyper | cancer_general | FGF5 | chr4 | 81187559 | 81187589 | Hyper | cancer_general | FGF5 |
| chr4 | 81188491 | 81188556 | Hyper | cancer_general | FGF5 | chr4 | 81189419 | 81189911 | Hyper | cancer_general | FGF5 |
| chr4 | 81951431 | 81951460 | Hyper | literature | BMP3 | chr4 | 81951941 | 81951970 | Hyper | literature | BMP3 |
| chr4 | 81952170 | 81952344 | Hyper | literature, cancer_general | BMP3 | chr4 | 82135873 | 82136056 | Hyper | cancer_general | PRKG2 |
| chr4 | 82136495 | 82136548 | Hyper | cancer_general | PRKG2 | chr4 | 82136807 | 82136837 | Hyper | cancer_general | PRKG2 |
| chr4 | 83720611 | 83720643 | Hyper | tcga | — | chr4 | 84035907 | 84035936 | Hyper | literature | PLAC8 |
| chr4 | 85402377 | 85402511 | Hyper | cancer_general | — | chr4 | 85402776 | 85403423 | Hyper | cancer_general | — |
| chr4 | 85403913 | 85404693 | Hyper | cancer_general | NKX6-1 | chr4 | 85414045 | 85414142 | Hyper | cancer_general | NKX6-1 |
| chr4 | 85414373 | 85414405 | Hyper | cancer_general | NKX6-1 | chr4 | 85414725 | 85414846 | Hyper | cancer_general | NKX6-1 |
| chr4 | 85417336 | 85417564 | Hyper | cancer_general | NKX6-1 | chr4 | 85417953 | 85418079 | Hyper | cancer_general | NKX6-1 |
| chr4 | 85418393 | 85418963 | Hyper | cancer_general | NKX6-1 | chr4 | 85420591 | 85420621 | Hyper | cancer_general | NKX6-1 |
| chr4 | 85422188 | 85422432 | Hyper | cancer_general | NKX6-1 | chr4 | 85422953 | 85423316 | Hyper | cancer_general | NKX6-1 |
| chr4 | 85422401 | 85424483 | Hyper | cancer_general | NKX6-1 | chr4 | 87515337 | 87515367 | Hyper | esophageal | PTPN13 |
| chr4 | 89378464 | 89378497 | Hyper | cancer_general | HERC5 | chr4 | 89378744 | 89378888 | Hyper | cancer_general | HERC5 |
| chr4 | 90757517 | 90757828 | Hyper | cancer_general, tcga | LOC644248, SNCA | chr4 | 90758105 | 90758134 | Hyper | tcga | LOC644248, SNCA |
| chr4 | 90758776 | 90758883 | Hyper | liver_tcga, cancer_general | SNCA, LOC644248 | chr4 | 93224972 | 93225171 | Hyper | tcga | GRID2 |
| chr4 | 93226365 | 93227129 | Hyper | tcga, cancer_general | GRID2 | chr4 | 94749725 | 94749755 | Hyper | blood | ATOH1 |
| chr4 | 94750982 | 94751140 | Hyper | tcga, cancer_general | ATOH1 | chr4 | 94751419 | 94751502 | Hyper | cancer_general | ATOH1 |
| chr4 | 94753415 | 94753445 | Hyper | cancer_general | ATOH1 | chr4 | 94755963 | 94756109 | Hyper | cancer_general | ATOH1 |
| chr4 | 96470752 | 96470782 | Hyper | cancer_general | UNC5C | chr4 | 101111246 | 101111504 | Hyper | cancer_general, tcga | DDIT4L |
| chr4 | 101111857 | 101111970 | Hyper | tcga, cancer_general | DDIT4L | chr4 | 102711731 | 102711787 | Hyper | cancer_general | BANK1 |
| chr4 | 102711994 | 102712065 | Hyper | cancer_general | BANK1 | chr4 | 107955311 | 107955826 | Hyper | cancer_general | DKK2 |
| chr4 | 107956676 | 107957086 | Hyper | cancer_general | DKK2 | chr4 | 107957373 | 107957466 | Hyper | cancer_general | DKK2 |
| chr4 | 109093101 | 109093168 | Hyper | cancer_general | LEF1-AS1 | chr4 | 109093405 | 109093506 | Hyper | cancer_general | LEF1-AS1 |
| chr4 | 110223090 | 110223980 | Hyper | liver_tcga, cancer_general | COL25A1 | chr4 | 111532632 | 111532961 | Hyper | cancer_general | PITX2 |
| chr4 | 111536288 | 111536693 | Hyper | cancer_general | PITX2 | chr4 | 111536960 | 111537042 | Hyper | cancer_general | PITX2 |
| chr4 | 111537407 | 111537497 | Hyper | cancer_general | PITX2 | chr4 | 111540199 | 111540360 | Hyper | cancer_general | PITX2 |
| chr4 | 111542187 | 111542757 | Hyper | cancer_general | PITX2 | chr4 | 111543232 | 111543450 | Hyper | liver_tcga, literature, cancer_general | PITX2 |
| chr4 | 111543661 | 111543735 | Hyper | cancer_general | PITX2 | chr4 | 111544381 | 111544583 | Hyper | cancer_general | PITX2 |
| chr4 | 111549800 | 111549830 | Hyper | cancer_general | PITX2 | chr4 | 111550618 | 111550834 | Hyper | cancer_general | PITX2 |
| chr4 | 111552118 | 111552148 | Hyper | cancer_general | PITX2 | chr4 | 111553099 | 111553450 | Hyper | cancer_general | PITX2 |
| chr4 | 111553916 | 111553951 | Hyper | cancer_general | PITX2 | chr4 | 111554950 | 111555343 | Hyper | cancer_general | — |
| chr4 | 111557965 | 111558049 | Hyper | cancer_general | — | chr4 | 111558551 | 111559233 | Hyper | literature, cancer_general | — |
| chr4 | 111560249 | 111560636 | Hyper | cancer_general | — | chr4 | 111562576 | 111562648 | Hyper | cancer_general | NEUROG2 |
| chr4 | 113430640 | 113430672 | Hyper | cancer_general | NEUROG2 | chr4 | 113431834 | 113432573 | Hyper | cancer_general | NEUROG2 |
| chr4 | 113436216 | 113436287 | Hyper | cancer_general | NEUROG2 | chr4 | 113441592 | 113441733 | Hyper | cancer_general | NEUROG2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 113442098 | 113442525 | Hyper | cancer_general | NEUROG2 | chr4 | 113444020 | 113444448 | Hyper | cancer_general | NEUROG2 |
| chr4 | 117847399 | 117847458 | Hyper | cancer_general | — | chr4 | 121844063 | 121844206 | Hyper | cancer_general | PRDM5 |
| chr4 | 121992265 | 121992312 | Hyper | cancer_general | 7SK, NDNF | chr4 | 121993997 | 121994251 | Hyper | cancer_general | — |
| chr4 | 122301422 | 122301846 | Hyper | cancer_general | QRFPR | chr4 | 122302116 | 122302246 | Hyper | cancer_general | QRFPR |
| chr4 | 122685807 | 122685951 | Hyper | cancer_general | PP12613, TMEM155 | chr4 | 122686209 | 122686507 | Hyper | tcga, liver_tcga, cancer_general | PP12613, TMEM155 |
| chr4 | 122871294 | 122871334 | Hyper | cancer_general | — | chr4 | 122871573 | 122872000 | Hyper | cancer_general | — |
| chr4 | 126237310 | 126237611 | Hyper | tcga, cancer_general | FAT4 | chr4 | 126238024 | 126238436 | Hyper | cancer_general, tcga | FAT4 |
| chr4 | 128544048 | 128544161 | Hyper | tcga, cancer_general | INTU | chr4 | 128544646 | 128544789 | Hyper | cancer_general | INTU |
| chr4 | 134067881 | 134068004 | Hyper | literature | PCDH10, BC040219 | chr4 | 134068577 | 134068791 | Hyper | tcga, cancer_general | PCDH10, BC040219 |
| chr4 | 134069289 | 134069318 | Hyper | literature | BC040219, PCDH10 | chr4 | 134069578 | 134069896 | Hyper | literature, cancer_general | PCDH10, BC040219 |
| chr4 | 134070374 | 134070403 | Hyper | literature | PCDH10, BC040219 | chr4 | 134071648 | 134072967 | Hyper | literature, cancer_general | PCDH10, BC040219 |
| chr4 | 134073184 | 134073322 | Hyper | cancer_general | PCDH10, BC040219 | chr4 | 134073568 | 134073641 | Hyper | cancer_general | PCDH10, BC040219 |
| chr4 | 134074030 | 134074156 | Hyper | cancer_general | PCDH10, BC040219 | chr4 | 140200529 | 140201462 | Hyper | cancer_general | MGARP, NDUFC1 |
| chr4 | 140656643 | 140657089 | Hyper | tcga, cancer_general | MAML3 | chr4 | 141347942 | 141348151 | Hyper | cancer_general | CLGN |
| chr4 | 141418921 | 141419418 | Hyper | cancer_general | LOC152586 | chr4 | 141488870 | 141489128 | Hyper | cancer_general | UCP1 |
| chr4 | 142053130 | 142053160 | Hyper | cancer_general | RNF150 | chr4 | 142053520 | 142053734 | Hyper | tcga, cancer_general | RNF150 |
| chr4 | 142054239 | 142054460 | Hyper | tcga | RNF150 | chr4 | 143766796 | 143766930 | Hyper | cancer_general | — |
| chr4 | 144621336 | 144622058 | Hyper | cancer_general, tcga | FREM3 | chr4 | 145568052 | 145568147 | Hyper | cancer_general | HHIP, HHIP-AS1 |
| chr4 | 145568459 | 145568741 | Hyper | cancer_general | HHIP, HHIP-AS1 | chr4 | 147558272 | 147558504 | Hyper | cancer_general | POU4F2 |
| chr4 | 147559321 | 147560617 | Hyper | tcga, cancer_general | POU4F2 | chr4 | 147560933 | 147562055 | Hyper | cancer_general | POU4F2 |
| chr4 | 147568636 | 147569060 | Hyper | cancer_general | POU4F2 | chr4 | 147569620 | 147569650 | Hyper | cancer_general | POU4F2 |
| chr4 | 147576177 | 147576639 | Hyper | cancer_general | — | chr4 | 152246132 | 152246314 | Hyper | blood | — |
| chr4 | 153247273 | 153247386 | Hyper | literature | FBXW7 | chr4 | 153249362 | 153249398 | Hyper | literature | FBXW7 |
| chr4 | 153251894 | 153251923 | Hyper | literature | FBXW7 | chr4 | 154709524 | 154710914 | Hyper | tcga, literature, cancer_general | SFRP2 |
| chr4 | 154712172 | 154712594 | Hyper | tcga, cancer_general | SFRP2 | chr4 | 154713500 | 154713530 | Hyper | cancer_general | SFRP2 |
| chr4 | 154713949 | 154714010 | Hyper | cancer_general | SFRP2 | chr4 | 155254166 | 155254196 | Hyper | cancer_general | DCHS2 |
| chr4 | 155411501 | 155412279 | Hyper | cancer_general | DCHS2 | chr4 | 155663209 | 155663647 | Hyper | cancer_general, tcga | LRAT, DQ266889 |
| chr4 | 156129153 | 156129183 | Hyper | cancer_general | NPY2R | chr4 | 156129451 | 156129495 | Hyper | cancer_general | NPY2R |
| chr4 | 156129746 | 156129797 | Hyper | cancer_general | NPY2R | chr4 | 156130047 | 156130297 | Hyper | cancer_general | NPY2R |
| chr4 | 156297416 | 156297556 | Hyper | colorectal, cancer_general | MAP9 | chr4 | 156297839 | 156298073 | Hyper | tcga, colorectal | MAP9 |
| chr4 | 156588311 | 156588401 | Hyper | tcga | GUCY1A3 | chr4 | 156589273 | 156589323 | Hyper | cancer_general | GUCY1A3 |
| chr4 | 156680257 | 156680532 | Hyper | tcga, cancer_general | GUCY1B3 | chr4 | 156681370 | 156681489 | Hyper | tcga | GUCY1B3 |
| chr4 | 158141576 | 158141606 | Hyper | cancer_general | GRIA2 | chr4 | 158142847 | 158142999 | Hyper | cancer_general | GRIA2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 158143443 | 158143564 | Hyper | cancer_general | GRIA2 | chr4 | 164252991 | 164253447 | Hyper | tcga, cancer_general | NPY1R, NPYY1 |
| chr4 | 165304515 | 165304578 | Hyper | cancer_general, lung | — | chr4 | 165305030 | 165305163 | Hyper | cancer_general | — |
| chr4 | 166414834 | 166414921 | Hyper | cancer_general | — | chr4 | 166794771 | 166794909 | Hyper | tcga | TLL1 |
| chr4 | 166796011 | 166796212 | Hyper | cancer_general | TLL1 | chr4 | 168155109 | 168155269 | Hyper | tcga, cancer_general | — |
| chr4 | 170947287 | 170947325 | Hyper | blood | BC031941 | chr4 | 172734168 | 172734203 | Hyper | cancer_general | GALNTL6 |
| chr4 | 172734550 | 172734790 | Hyper | cancer_general | GALNTL6 | chr4 | 174429658 | 174429688 | Hyper | cancer_general | — |
| chr4 | 174430310 | 174431072 | Hyper | cancer_general | — | chr4 | 174438567 | 174438744 | Hyper | cancer_general | HAND2 |
| chr4 | 174439822 | 174440257 | Hyper | literature, cancer_general | HAND2 | chr4 | 174440635 | 174440713 | Hyper | cancer_general | HAND2 |
| chr4 | 174443212 | 174443242 | Hyper | cancer_general | HAND2, NBLA00301 | chr4 | 174443563 | 174443934 | Hyper | tcga, cancer_general | HAND2, NBLA00301 |
| chr4 | 174444151 | 174444180 | Hyper | tcga | HAND2, NBLA00301 | chr4 | 174446486 | 174446525 | Hyper | cancer_general | HAND2, NBLA00301 |
| chr4 | 174446952 | 174447005 | Hyper | cancer_general | HAND2, NBLA00301 | chr4 | 174449950 | 174451482 | Hyper | tcga, cancer_general, literature | HAND2, NBLA00301 |
| chr4 | 174451855 | 174452098 | Hyper | cancer_general | NBLA00301, HAND2 | chr4 | 174459185 | 174459840 | Hyper | cancer_general | HAND2, NBLA00301 |
| chr4 | 174460186 | 174460221 | Hyper | cancer_general | NBLA00301, HAND2 | chr4 | 175132735 | 175132765 | Hyper | cancer_general | AK125257 |
| chr4 | 175133085 | 175133201 | Hyper | cancer_general | AK125257 | chr4 | 175134897 | 175135672 | Hyper | cancer_general | AK125257 |
| chr4 | 175135921 | 175136011 | Hyper | cancer_general | AK125257 | chr4 | 175138411 | 175138546 | Hyper | cancer_general | AK125257 |
| chr4 | 175138964 | 175139254 | Hyper | cancer_general | AK125257 | chr4 | 175139559 | 175139685 | Hyper | cancer_general | AK125257 |
| chr4 | 175750456 | 175750738 | Hyper | cancer_general | AK093264, BC034301, GLRA3 | chr4 | 176923424 | 176923558 | Hyper | tcga, cancer_general | — |
| chr4 | 176987324 | 176987373 | Hyper | cancer_general | WDR17 | chr4 | 177713228 | 177713437 | Hyper | tcga, cancer_general | VEGFC |
| chr4 | 180979270 | 180979300 | Hyper | cancer_general | — | chr4 | 180980297 | 180980356 | Hyper | cancer_general | — |
| chr4 | 183063666 | 183063950 | Hyper | cancer_general | TENM3, MGC45800 | chr4 | 183064617 | 183064655 | Hyper | cancer_general | TENM3, MGC45800 |
| chr4 | 184019249 | 184019316 | Hyper | cancer_general | WWC2, WWC2-AS2 | chr4 | 184019692 | 184019736 | Hyper | blood | WWC2-AS2, WWC2 |
| chr4 | 184020106 | 184020179 | Hyper | blood | WWC2, WWC2-AS2 | chr4 | 184644053 | 184644249 | Hyper | hepatobiliary | — |
| chr4 | 184718260 | 184718352 | Hyper | cancer_general | — | chr4 | 184826238 | 184826493 | Hyper | cancer_general, tcga | STOX2 |
| chr4 | 184826938 | 184827237 | Hyper | tcga, cancer_general | STOX2 | chr4 | 185089696 | 185089797 | Hyper | head_neck | ENPP6 |
| chr4 | 185937333 | 185937889 | Hyper | cancer_general | HELT | chr4 | 185938497 | 185938564 | Hyper | cancer_general | HELT |
| chr4 | 185940338 | 185940460 | Hyper | cancer_general | HELT | chr4 | 185941585 | 185942760 | Hyper | cancer_general | HELT |
| chr4 | 187647073 | 187647457 | Hyper | blood | FAT1 | chr3 | 238536 | 239094 | Hyper | cancer_general | CHL1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 239622 | 240223 | Hyper | cancer_general | CHL1 | chr3 | 2140277 | 2140398 | Hyper | cancer_general | CNTN4 |
| chr3 | 3840498 | 3840758 | Hyper | liver_tcga, cancer_general | LRRN1, BC141932, SUMF1 | chr3 | 3841046 | 3841144 | Hyper | tcga, liver_tcga | LRRN1, BC141932, SUMF1 |
| chr3 | 3842679 | 3842731 | Hyper | tcga | SUMF1, BC141932, LRRN1 | chr3 | 5137960 | 5138019 | Hyper | pancreas | |
| chr3 | 6902288 | 6902353 | Hyper | cancer_general | GRM7 | chr3 | 6903425 | 6903463 | Hyper | cancer_general | GRM7 |
| chr3 | 8725296 | 8725348 | Hyper | esophageal | | chr3 | 8810136 | 8810220 | Hyper | cancer_general | Mir_548, OXTR |
| chr3 | 9178165 | 9178263 | Hyper | literature, tcga | SRGAP3 | chr3 | 9393979 | 9594015 | Hyper | cancer_general | LHFPL4 |
| chr3 | 9594263 | 9594382 | Hyper | liver_tcga | LHFPL4 | chr3 | 9595292 | 9595584 | Hyper | cancer_general | LHFPL4 |
| chr3 | 9904233 | 9904554 | Hyper | cancer_general | CIDEC | chr3 | 9957064 | 9957142 | Hyper | cancer_general | IL17RC, IL17RE |
| chr3 | 9957451 | 9957677 | Hyper | cancer_general | IL17RE, IL17RC | chr3 | 10183321 | 10183350 | Hyper | literature | VHL |
| chr3 | 10183706 | 10183782 | Hyper | literature | VHL | chr3 | 10191477 | 10191620 | Hyper | literature | VHL |
| chr3 | 10857987 | 10858019 | Hyper | cancer_general | SLC6A11 | chr3 | 11034264 | 11034359 | Hyper | tcga | SLC6A1 |
| chr3 | 11035070 | 11035330 | Hyper | cancer_general | SLC6A1 | chr3 | 12046405 | 12046632 | Hyper | tcga | SYN2 |
| chr3 | 12632309 | 12632401 | Hyper | literature | MKRN2, RAF1 | chr3 | 12645678 | 12645713 | Hyper | literature | RAF1 |
| chr3 | 12729424 | 12729454 | Hyper | esophageal | | chr3 | 12917606 | 12917655 | Hyper | cancer_general | DQ581328 |
| chr3 | 13323494 | 13323973 | Hyper | cancer_general | | chr3 | 13324358 | 13324433 | Hyper | cancer_general | |
| chr3 | 13324847 | 13324938 | Hyper | cancer_general | | chr3 | 13590416 | 13590863 | Hyper | cancer_general | FBLN2 |
| chr3 | 13679284 | 13679319 | Hyper | pancreas | FGD5 | chr3 | 13921407 | 13921463 | Hyper | cancer_general | WNT7A |
| chr3 | 14851850 | 14851897 | Hyper | cancer_general | | chr3 | 14852325 | 14852919 | Hyper | tcga, cancer_general | FGD5 |
| chr3 | 16554052 | 16554111 | Hyper | cancer_general | | chr3 | 16554347 | 16554633 | Hyper | cancer_general | |
| chr3 | 19189441 | 19189470 | Hyper | tcga | KCNH8 | chr3 | 19189694 | 19189765 | Hyper | tcga | KCNH8 |
| chr3 | 19190143 | 19190216 | Hyper | tcga | KCNH8 | chr3 | 22413665 | 22413694 | Hyper | tcga | ZNF385D |
| chr3 | 22413945 | 22413974 | Hyper | tcga | ZNF385D | chr3 | 24871002 | 24871245 | Hyper | tcga | |
| chr3 | 25469110 | 25469139 | Hyper | literature | RARB, LOC100130354 | chr3 | 25469377 | 25469406 | Hyper | literature | RARB, LOC100130354 |
| chr3 | 25469679 | 25469708 | Hyper | literature | LOC100130354, RARB | chr3 | 26664045 | 26664119 | Hyper | cancer_general | LRRC3B |
| chr3 | 26664389 | 26664755 | Hyper | tcga | LRRC3B | chr3 | 27754478 | 27754508 | Hyper | cancer_general | EOMES |
| chr3 | 27762336 | 27762650 | Hyper | cancer_general | EOMES | chr3 | 27762857 | 27762887 | Hyper | cancer_general | EOMES |
| chr3 | 27763566 | 27763595 | Hyper | liver_tcga | EOMES | chr3 | 27764457 | 27764503 | Hyper | cancer_general | EOMES |
| chr3 | 27765181 | 27765347 | Hyper | cancer_general | EOMES | chr3 | 27771497 | 27772004 | Hyper | cancer_general | EOMES |
| chr3 | 27772790 | 27772819 | Hyper | literature | EOMES | chr3 | 28616832 | 28617675 | Hyper | tcga, cancer_general | LINC00693, AX746710 |
| chr3 | 32858353 | 32859693 | Hyper | tcga, cancer_general | TRIM71 | chr3 | 32860068 | 32860273 | Hyper | cancer_general | TRIM71 |
| chr3 | 33259904 | 33260776 | Hyper | tcga, cancer_general | SUSD5 | chr3 | 35680842 | 35680872 | Hyper | cancer_general | ARPP21 |
| chr3 | 36805815 | 36805863 | Hyper | cancer_general | | chr3 | 36806151 | 36806193 | Hyper | cancer_general | CTDSPL, BC040563 |
| chr3 | 37493519 | 37493621 | Hyper | esophageal | ITGA9 | chr3 | 37901923 | 37901953 | Hyper | blood | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 38035767 | 38035989 | Hyper | cancer_general | VILL | chr3 | 38080685 | 38080925 | Hyper | cancer_general, liver_tcga | DLEC1, PLCD1 |
| chr3 | 38081148 | 38081271 | Hyper | cancer_general | DLEC1, PLCD1 | chr3 | 38182244 | 38182306 | Hyper | literature | MYD88, ACAA1 |
| chr3 | 38182626 | 38182655 | Hyper | literature | MYD88, ACAA1 | chr3 | 38690624 | 38690668 | Hyper | cancer_general | SCN5A |
| chr3 | 38691348 | 38691466 | Hyper | esophageal | SCN5A | chr3 | 39851772 | 39851814 | Hyper | cancer_general | MYRIP |
| chr3 | 40428507 | 40428713 | Hyper | liver_tcga | ENTPD3, ENTPD3-AS1 | chr3 | 41266086 | 41266151 | Hyper | literature | AK095242, AK311005, CTNNB1 |
| chr3 | 42814569 | 42814603 | Hyper | cancer_general | HIGD1A, CCDC13 | chr3 | 42947411 | 42947552 | Hyper | cancer_general | ZNF662 |
| chr3 | 44036260 | 44036330 | Hyper | tcga, cancer_general | — | chr3 | 44036570 | 44036600 | Hyper | cancer_general | — |
| chr3 | 44036820 | 44037203 | Hyper | cancer_general | — | chr3 | 44037625 | 44037662 | Hyper | cancer_general | — |
| chr3 | 44037874 | 44038646 | Hyper | cancer_general, tcga | — | chr3 | 44039348 | 44040006 | Hyper | cancer_general | — |
| chr3 | 44040511 | 44040553 | Hyper | tcga | — | chr3 | 44040796 | 44041039 | Hyper | tcga, cancer_general | — |
| chr3 | 44063434 | 44063872 | Hyper | cancer_general | ZKSCAN7 | chr3 | 44596479 | 44596509 | Hyper | cancer_general | ZKSCAN7 |
| chr3 | 44596716 | 44596809 | Hyper | cancer_general | ZKSCAN7 | chr3 | 44626438 | 44626711 | Hyper | tcga, cancer_general | ZNF660, ZKSCAN7 |
| chr3 | 44726875 | 44727193 | Hyper | cancer_general | — | chr3 | 45187296 | 45187582 | Hyper | blood | CDCP1 |
| chr3 | 46924934 | 46924964 | Hyper | esophageal | PTH1R | chr3 | 47144864 | 47144893 | Hyper | literature | — |
| chr3 | 48693304 | 48694170 | Hyper | tcga, liver_tcga, cancer_general | — | chr3 | 48698810 | 48699767 | Hyper | cancer_general, tcga | — |
| chr3 | 49236845 | 49236874 | Hyper | literature | CCDC36, LOC646498 | chr3 | 49405953 | 49405982 | Hyper | literature | RHOA |
| chr3 | 49412883 | 49412987 | Hyper | literature | RHOA | chr3 | 49591832 | 49592076 | Hyper | esophageal | BSN, BSN-AS2 |
| chr3 | 49907093 | 49907130 | Hyper | esophageal | CAMKV | chr3 | 50243383 | 50243480 | Hyper | cancer_general | SLC38A3, GNAT1 |
| chr3 | 50374655 | 50374684 | Hyper | literature | RASSF1, TUSC2, AB209621, ZMYND10 | chr3 | 50374917 | 50374946 | Hyper | literature | AB209621, ZMYND10, NPRL2, RASSF1, TUSC2 |
| chr3 | 50375179 | 50375559 | Hyper | literature | TUSC2, AB209621, ZMYND10, NPRL2, RASSF1 | chr3 | 50377973 | 50378002 | Hyper | literature | AB209621, ZMYND10, NPRL2, RASSF1 |
| chr3 | 50378277 | 50378306 | Hyper | literature | AB209621, ZMYND10, NPRL2, CYB561D2, RASSF1 | chr3 | 50378512 | 50378541 | | | ZMYND10, NPRL2, CYB561D2, AB209621, RASSF1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 50402170 | 50402944 | Hyper | lung, cancer_general | Mir_324, TMEM115, CACNA2D2 | chr3 | 52442062 | 52442091 | Hyper | literature | PHF7, BAP1, DNAH1 |
| chr3 | 54155611 | 54155677 | Hyper | tcga | CACNA2D3 | chr3 | 54157381 | 54157450 | Hyper | cancer_general | CACNA2D3 |
| chr3 | 54157878 | 54157919 | Hyper | cancer_general | CACNA2D3 | chr3 | 55519219 | 55519253 | Hyper | esophageal | WNT5A |
| chr3 | 55523106 | 55523290 | Hyper | cancer_general | WNT5A | chr3 | 62304560 | 62304669 | Hyper | cancer_general | PTPRG-AS1, C3orf14 |
| chr3 | 62353371 | 62354049 | Hyper | cancer_general | FEZF2 | chr3 | 62354283 | 62354328 | Hyper | cancer_general | FEZF2 |
| chr3 | 62354625 | 62354914 | Hyper | cancer_general | FEZF2 | chr3 | 62355424 | 62355478 | Hyper | cancer_general | FEZF2 |
| chr3 | 62355774 | 62357347 | Hyper | cancer_general | FEZF2 | chr3 | 62357624 | 62357667 | Hyper | cancer_general | FEZF2 |
| chr3 | 62358161 | 62358194 | Hyper | cancer_general | FEZF2 | chr3 | 62358530 | 62358595 | Hyper | cancer_general | FEZF2 |
| chr3 | 62358858 | 62359011 | Hyper | cancer_general | FEZF2 | chr3 | 62359376 | 62359893 | Hyper | cancer_general | FEZF2 |
| chr3 | 62360302 | 62360560 | Hyper | cancer_general | FEZF2 | chr3 | 62362902 | 62363200 | Hyper | cancer_general | FEZF2 |
| chr3 | 62363626 | 62363693 | Hyper | cancer_general | FEZF2 | chr3 | 62363906 | 62364329 | Hyper | cancer_general | FEZF2 |
| chr3 | 62364702 | 62365154 | Hyper | cancer_general | FEZF2 | chr3 | 62861118 | 62861148 | Hyper | cancer_general | FAM19A1, AX747367 |
| chr3 | 63264139 | 63264169 | Hyper | cancer_general | SYNPR | chr3 | 68056904 | 68057145 | Hyper | liver_tcga, cancer_general | — |
| chr3 | 68980931 | 68981113 | Hyper | cancer_general | — | chr3 | 68981552 | 68981624 | Hyper | cancer_general | — |
| chr3 | 69590939 | 69590969 | Hyper | cancer_general | — | chr3 | 69591363 | 69592063 | Hyper | tcga, cancer_general | — |
| chr3 | 71802518 | 71802622 | Hyper | tcga | GPR27, EIF4E3 | chr3 | 71803126 | 71803372 | Hyper | tcga, cancer_general | GPR27, EIF4E3 |
| chr3 | 71803643 | 71803821 | Hyper | cancer_general | GPR27, EIF4E3 | chr3 | 75956011 | 75956375 | Hyper | cancer_general | — |
| chr3 | 79815522 | 79815557 | Hyper | cancer_general | — | chr3 | 79816778 | 79817015 | Hyper | cancer_general | CADM2 |
| chr3 | 79817288 | 79817318 | Hyper | cancer_general | — | chr3 | 85008553 | 85008708 | Hyper | tcga, cancer_general | — |
| chr3 | 96532817 | 96532873 | Hyper | tcga | EPHA6 | chr3 | 96533383 | 96533458 | Hyper | cancer_general | EPHA6 |
| chr3 | 96534035 | 96534096 | Hyper | cancer_general | EPHA6 | chr3 | 98620891 | 98620980 | Hyper | esophageal | DCBLD2 |
| chr3 | 99594925 | 99595105 | Hyper | cancer_general | FILIP1L | chr3 | 101497841 | 101497996 | Hyper | liver_tcga, hepatobiliary | NXPE3 |
| chr3 | 112052203 | 112052419 | Hyper | tcga | CD200, BC041484 | chr3 | 117715549 | 117716473 | Hyper | cancer_general, tcga | — |
| chr3 | 120004040 | 120004405 | Hyper | tcga, liver_tcga, cancer_general | — | chr3 | 120169104 | 120169149 | Hyper | esophageal | FSTL1 |
| chr3 | 120169768 | 120169835 | Hyper | tcga | FSTL1 | chr3 | 120627317 | 120627453 | Hyper | cancer_general | STXBP5L |
| chr3 | 121902975 | 121903619 | Hyper | cancer_general | CASR | chr3 | 123167073 | 123167529 | Hyper | liver_tcga, cancer_general | — |
| chr3 | 123167769 | 123167827 | Hyper | cancer_general | — | chr3 | 124860671 | 124860700 | Hyper | literature | SLC12A8, MIR5092 |
| chr3 | 125898597 | 125899207 | Hyper | cancer_general | ALDH1L1-AS2, ALDH1L1 | chr3 | 125899525 | 125899962 | Hyper | cancer_general | ALDH1L1-AS2 |
| chr3 | 125932252 | 125932500 | Hyper | cancer_general | ALDH1L1-AS2 | chr3 | 126373520 | 126373704 | Hyper | blood | ALDH1L1 NUP210P1, TXNRD3 |
| chr3 | 126854699 | 126854796 | Hyper | cancer_general | — | chr3 | 127634186 | 127634216 | Hyper | cancer_general | KBTBD12 |
| chr3 | 127794546 | 127794860 | Hyper | cancer_general | RUVBL1, SEC61A1 | chr3 | 127795325 | 127795408 | Hyper | tcga | RUVBL1, SEC61A1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 128202447 | 128202477 | Hyper | cancer_general | GATA2 | chr3 | 128208903 | 128209232 | Hyper | cancer_general | GATA2 |
| chr3 | 128273993 | 128274611 | Hyper | tcga, pancreas, cancer_general | — | chr3 | 128417201 | 128417231 | Hyper | cancer_general | — |
| chr3 | 128720061 | 128720611 | Hyper | tcga, cancer_general | EFCC1, KIAA1257 | chr3 | 128720869 | 128721229 | Hyper | liver_tcga, cancer_general | EFCC1, KIAA1257 |
| chr3 | 128764489 | 128764632 | Hyper | cancer_general | EFCC1 | chr3 | 129693108 | 129694299 | Hyper | liver_tcga, tcga, cancer_general | TRH |
| chr3 | 129694504 | 129694534 | Hyper | cancer_general | TRH | chr3 | 130064451 | 130064484 | Hyper | cancer_general | COL6A5 |
| chr3 | 130064818 | 130064848 | Hyper | cancer_general | COL6A5 | chr3 | 130236049 | 130236273 | Hyper | cancer_general | — |
| chr3 | 131754031 | 131754061 | Hyper | cancer_general | — | chr3 | 132757065 | 132757104 | Hyper | cancer_general | TMEM108 |
| chr3 | 133748140 | 133748245 | Hyper | blood | SLCO2A1 | chr3 | 133748481 | 133748576 | Hyper | blood | SLCO2A1 |
| chr3 | 134369646 | 134369855 | Hyper | tcga, cancer_general | KY | chr3 | 134514866 | 134514895 | Hyper | tcga | EPHB1 |
| chr3 | 134515128 | 134515369 | Hyper | tcga, cancer_general | EPHB1 | chr3 | 134515676 | 134516222 | Hyper | cancer_general | EPHB1 |
| chr3 | 136537642 | 136537730 | Hyper | cancer_general | SLC35G2 | chr3 | 136538585 | 136538815 | Hyper | tcga, cancer_general | SLC35G2 |
| chr3 | 136751641 | 136751809 | Hyper | tcga | SOX14 | chr3 | 137479233 | 137479302 | Hyper | cancer_general | SOX14 |
| chr3 | 137479601 | 137479687 | Hyper | cancer_general | SOX14 | chr3 | 137479980 | 137480764 | Hyper | cancer_general | SOX14 |
| chr3 | 137481170 | 137481315 | Hyper | cancer_general | SOX14 | chr3 | 137481858 | 137482183 | Hyper | cancer_general | SOX14 |
| chr3 | 137483313 | 137483589 | Hyper | tcga, cancer_general | BC038725, SOX14 | chr3 | 137483848 | 137484002 | Hyper | cancer_general | BC038725, SOX14 |
| chr3 | 137484405 | 137484531 | Hyper | cancer_general | BC038725, SOX14, | chr3 | 137486029 | 137486310 | Hyper | cancer_general | BC038725 SOX14, |
| chr3 | 137486516 | 137486550 | Hyper | cancer_general | SOX14, BC038725 | chr3 | 137487964 | 137488021 | Hyper | cancer_general | BC038725, SOX14 |
| chr3 | 137488950 | 137491040 | Hyper | tcga, cancer_general | SOX14 | chr3 | 138067717 | 138067747 | Hyper | blood | MRAS |
| chr3 | 138153963 | 138153993 | Hyper | cancer_general | ESYT3 | chr3 | 138154340 | 138154377 | Hyper | cancer_general | ESYT3 |
| chr3 | 138374229 | 138374258 | Hyper | literature | PIK3CB | chr3 | 138655934 | 138656138 | Hyper | cancer_general | FOXL2, C3orf72, AK128202 |
| chr3 | 138656834 | 138656889 | Hyper | cancer_general | C3orf72, AK304483, AK128202, OFXL2 | chr3 | 138657414 | 138659099 | Hyper | tcga, cancer_general | AK128202, FOXL2, C3orf72, AK304483 |
| chr3 | 138662134 | 138662164 | Hyper | cancer_general | FOXL2, C3orf72, AK304483, AK128202 | chr3 | 138662382 | 138662448 | Hyper | cancer_general | FOXL2, C3orf72, AK304483, AK128202 |
| chr3 | 138662799 | 138662842 | Hyper | cancer_general | FOXL2, C3orf72, AK304483, AK128202 | chr3 | 138663613 | 138664165 | Hyper | cancer_general | C3orf72, AK304483, FOXL2, AK128202 |
| chr3 | 138664408 | 138664489 | Hyper | cancer_general | AK304483, FOXL2, AK128202, C3orf72 | chr3 | 138664928 | 138665323 | Hyper | cancer_general | C3orf72, AK304483, FOXL2, AK128202 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 138665562 | 138666294 | Hyper | cancer_general, liver_tcga, tcga | AK128202, C3orf72, AK304483, FOXL2 | chr3 | 138668742 | 138669387 | Hyper | cancer_general | AK128202, AK304483, C3orf72, FOXL2 |
| chr3 | 138679462 | 138679526 | Hyper | cancer_general | AK304483, C3orf72 | chr3 | 139258267 | 139258316 | Hyper | cancer_general | RBP1 |
| chr3 | 139653491 | 139653693 | Hyper | cancer_general | CLSTN2 | chr3 | 140769513 | 140769705 | Hyper | cancer_general | SPSB4 |
| chr3 | 140769908 | 140770829 | Hyper | tcga, pancreas, cancer_general | SPSB4 | chr3 | 140771305 | 140771335 | Hyper | cancer_general | SPSB4 |
| chr3 | 140771816 | 140771854 | Hyper | cancer_general | SPSB4 | chr3 | 141516389 | 141516719 | Hyper | cancer_general | GRK7 |
| chr3 | 142682273 | 142682392 | Hyper | tcga | PAQR9, KA093381 | chr3 | 142837980 | 142838370 | Hyper | tcga, cancer_general | CHST2 |
| chr3 | 142838621 | 142839036 | Hyper | tcga, cancer_general | CHST2 | chr3 | 142839539 | 142840236 | Hyper | tcga, colorectal, liver_tcga, cancer_general | CHST2 |
| chr3 | 145878665 | 145878695 | Hyper | blood | — | chr3 | 147074457 | 147074487 | Hyper | cancer_general | — |
| chr3 | 147074974 | 147075006 | Hyper | cancer_general | — | chr3 | 147077289 | 147077671 | Hyper | liver_tcga, cancer_general | — |
| chr3 | 147078959 | 147079188 | Hyper | cancer_general | — | chr3 | 147087562 | 147087799 | Hyper | cancer_general | — |
| chr3 | 147088440 | 147088523 | Hyper | cancer_general | — | chr3 | 147088939 | 147089099 | Hyper | cancer_general | — |
| chr3 | 147098431 | 147098470 | Hyper | cancer_general | ZIC4 | chr3 | 147105898 | 147106010 | Hyper | liver_tcga | ZIC4 |
| chr3 | 147108841 | 147110932 | Hyper | cancer_general | ZIC4 | chr3 | 147110145 | 147110683 | Hyper | cancer_general | ZIC4 |
| chr3 | 147110927 | 147111089 | Hyper | cancer_general | ZIC4 | chr3 | 147111545 | 147111674 | Hyper | literature, cancer_general | ZIC4 |
| chr3 | 147125697 | 147125726 | Hyper | literature | ZIC1, ZIC4 | chr3 | 147127037 | 147127067 | Hyper | cancer_general | ZIC1, ZIC4 |
| chr3 | 147127681 | 147127902 | Hyper | cancer_general | ZIC1, ZIC4 | chr3 | 147128287 | 147128326 | Hyper | cancer_general | ZIC1, ZIC4 |
| chr3 | 147136931 | 147137164 | Hyper | cancer_general | ZIC1 | chr3 | 147138768 | 147138856 | Hyper | cancer_general | ZIC1 |
| chr3 | 147139126 | 147139156 | Hyper | cancer_general | ZIC1 | chr3 | 147139374 | 147139528 | Hyper | cancer_general | ZIC1 |
| chr3 | 147142225 | 147142265 | Hyper | cancer_general | AGTR1 | chr3 | 148415427 | 148415644 | Hyper | cancer_general | AGTR1 |
| chr3 | 149374947 | 149375023 | Hyper | cancer_general | WWTR1-AS1, AK309441 | chr3 | 150802981 | 150803080 | Hyper | cancer_general | MED12L, CLRN1-AS1 |
| chr3 | 150804043 | 150804077 | Hyper | tcga | MED12L, CLRN1-AS1 | chr3 | 150804967 | 150805030 | Hyper | cancer_general | MED12L, CLRN1-AS1 |
| chr3 | 152553343 | 152553384 | Hyper | cancer_general | P2RY1 | chr3 | 152553658 | 152553725 | Hyper | tcga, blood, cancer_general | P2RY1 |
| chr3 | 153838818 | 153838870 | Hyper | blood | ARHGEF26-AS1, ARHGEF26 | chr3 | 153839518 | 153840057 | Hyper | cancer_general | ARHGEF26, ARHGEF26-AS1 |
| chr3 | 154146133 | 154146412 | Hyper | cancer_general | GPR149 | chr3 | 154146654 | 154146908 | Hyper | cancer_general | GPR149 |
| chr3 | 154797334 | 154797703 | Hyper | cancer_general, tcga, head_neck | MME | chr3 | 155463041 | 155463071 | Hyper | hepatobiliary | — |
| chr3 | 156008976 | 156009425 | Hyper | cancer_general | KCNAB1 | chr3 | 156534302 | 156534332 | Hyper | cancer_general | AK094480, LEKR1, AP2G4P4, LINC00886 |
| chr3 | 157155252 | 157155490 | Hyper | tcga, cancer_general | PTX3, VEPH1, Mir_584 | chr3 | 157155982 | 157156194 | Hyper | cancer_general, tcga | VEPH1, Mir_584, PTX3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 157812196 | 157812645 | Hyper | cancer_general | SHOX2 | chr3 | 157812912 | 157813070 | Hyper | cancer_general | SHOX2 |
| chr3 | 157813608 | 157813824 | Hyper | literature, cancer_general | SHOX2 | chr3 | 157814311 | 157814340 | Hyper | literature | SHOX2 |
| chr3 | 157815657 | 157815822 | Hyper | literature | SHOX2 | chr3 | 157820576 | 157820605 | Hyper | literature | RSRC1, SHOX2 |
| chr3 | 157821085 | 157821662 | Hyper | literature, cancer_general | RSRC1, SHOX2 | chr3 | 157821904 | 157822008 | Hyper | literature | RSRC1, SHOX2 |
| chr3 | 157823073 | 157823143 | Hyper | cancer_general | RSRC1, SHOX2 | chr3 | 157823464 | 157823493 | Hyper | literature | RSRC1, SHOX2 |
| chr3 | 157824133 | 157824231 | Hyper | literature | RSRC1, SHOX2 | chr3 | 157824495 | 157824871 | Hyper | literature, cancer_general | RSRC1, SHOX2 |
| chr3 | 157825176 | 157825408 | Hyper | cancer_general | RSRC1, SHOX2 | chr3 | 158288836 | 158288872 | Hyper | liver_tcga | MLF1, AK097794 |
| chr3 | 159756687 | 159756856 | Hyper | cancer_general | — | chr3 | 159944486 | 159944546 | Hyper | cancer_general | IFT80, C3orf80 |
| chr3 | 160168003 | 160168033 | Hyper | cancer_general | — | chr3 | 164912376 | 164912568 | Hyper | cancer_general | SLITRK3 |
| chr3 | 164912907 | 164913872 | Hyper | cancer_general | SLITRK3 | chr3 | 164914980 | 164915129 | Hyper | cancer_general | SLITRK3 |
| chr3 | 169376183 | 169376215 | Hyper | cancer_general | — | chr3 | 169376680 | 169376780 | Hyper | cancer_general | CLDN11 |
| chr3 | 169378825 | 169379024 | Hyper | cancer_general | — | chr3 | 170136627 | 170136751 | Hyper | cancer_general | BC039437, SLC7A14 |
| chr3 | 170137667 | 170137772 | Hyper | cancer_general | CLDN11 | chr3 | 170302617 | 170302677 | Hyper | cancer_general | BC039437, SLC7A14 |
| chr3 | 170303087 | 170303129 | Hyper | cancer_general | BC039437, SLC7A14 | chr3 | 170303331 | 170303423 | Hyper | cancer_general | BC039437, SLC7A14 |
| chr3 | 170303639 | 170303844 | Hyper | liver_tcga, cancer_general | BC039437, SLC7A14 | chr3 | 171527930 | 171527971 | Hyper | blood | — |
| chr3 | 172165443 | 172166627 | Hyper | cancer_general | GHSR, GU289929 | chr3 | 172166879 | 172167044 | Hyper | cancer_general | GHSR, GU289929 |
| chr3 | 172167297 | 172167327 | Hyper | cancer_general | GHSR, GU289929 | chr3 | 172167660 | 172167917 | Hyper | cancer_general | GU289929, GHSR |
| chr3 | 173115237 | 173115550 | Hyper | tcga | NLGN1 | chr3 | 173302542 | 173302684 | Hyper | cancer_general | NLGN1 |
| chr3 | 173302992 | 173303225 | Hyper | cancer_general | NLGN1 | chr3 | 178916711 | 178916959 | Hyper | literature | PIK3CA |
| chr3 | 178921537 | 178921568 | Hyper | literature | PIK3CA | chr3 | 178927966 | 178928094 | Hyper | literature | PIK3CA |
| chr3 | 178936059 | 178936111 | Hyper | literature | PIK3CA | chr3 | 178952004 | 178952105 | Hyper | literature | KCNMB3, PIK3CA |
| chr3 | 179168661 | 179169266 | Hyper | liver_tcga, colorectal, cancer_general | GNB4 | chr3 | 179754178 | 179755372 | Hyper | cancer_general | — |
| chr3 | 180320256 | 180320294 | Hyper | esophageal | TTC14 | chr3 | 181413084 | 181413355 | Hyper | cancer_general | JA611300, SOX2-OT |
| chr3 | 181413742 | 181414330 | Hyper | tcga, cancer_general | JA611300, SOX2-OT | chr3 | 181420065 | 181420116 | Hyper | cancer_general | SOX2, JA611300, SOX2-OT |
| chr3 | 181420316 | 181420374 | Hyper | cancer_general | SOX2, JA611300, SOX2-OT | chr3 | 181421411 | 181422282 | Hyper | tcga, cancer_general | JA611300, SOX2-OT |
| chr3 | 181422541 | 181422985 | Hyper | cancer_general | SOX2, JA611300, SOX2-OT | chr3 | 181428388 | 181428772 | Hyper | cancer_general | SOX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 181430695 | 181430771 | Hyper | cancer_general | SOX2 | chr3 | 181437129 | 181437349 | Hyper | cancer_general | SOX2 |
| chr3 | 181438194 | 181438353 | Hyper | cancer_general | SOX2 | chr3 | 181440892 | 181441927 | Hyper | literature, cancer_general | SOX2 |
| chr3 | 181442145 | 181442410 | Hyper | lung, cancer_general | SOX2 | chr3 | 181443014 | 181443557 | Hyper | cancer_general | |
| chr3 | 181443760 | 181443861 | Hyper | cancer_general | | chr3 | 181444434 | 181445013 | Hyper | cancer_general | |
| chr3 | 181445369 | 181445464 | Hyper | cancer_general | | chr3 | 181445735 | 181445861 | Hyper | cancer_general | |
| chr3 | 183145412 | 183145618 | Hyper | literature, cancer_general | | chr3 | 183145931 | 183146025 | Hyper | literature | |
| chr3 | 183146397 | 183146435 | Hyper | literature | | chr3 | 183146648 | 183146677 | Hyper | literature | EPHB3 |
| chr3 | 184099417 | 184099446 | Hyper | literature | CHRD, THPO | chr3 | 184301734 | 184301772 | Hyper | cancer_general | |
| chr3 | 184319424 | 184319612 | Hyper | pancreas | | chr3 | 184319828 | 184319891 | Hyper | pancreas | |
| chr3 | 186078766 | 186078898 | Hyper | cancer_general | | chr3 | 186079204 | 186079331 | Hyper | cancer_general | |
| chr3 | 186080188 | 186080218 | Hyper | cancer_general | | chr3 | 186857152 | 186857607 | Hyper | tcga, cancer_general | |
| chr3 | 187387850 | 187388239 | Hyper | cancer_general | SST | chr3 | 192125828 | 192125858 | Hyper | cancer_general | FGF12 |
| chr3 | 192126146 | 192126863 | Hyper | cancer_general, tcga | FGF12 | chr3 | 192127354 | 192128074 | Hyper | cancer_general | FGF12 |
| chr3 | 192232097 | 192232175 | Hyper | cancer_general | FGF12 | chr3 | 192232452 | 192232570 | Hyper | cancer_general | FGF12 |
| chr3 | 192232834 | 192233150 | Hyper | cancer_general | FGF12 | chr3 | 192958725 | 192958968 | Hyper | liver_tcga | HRASLS, MGC2889 |
| chr3 | 193776089 | 193776119 | Hyper | cancer_general | BC038368 | chr3 | 194120008 | 194120164 | Hyper | literature | ATP13A3, GP5 |
| chr3 | 194120934 | 194120963 | Hyper | literature | ATP13A3, GP5 | chr3 | 194208286 | 194208562 | Hyper | cancer_general | AX746839, LINC00884 |
| chr3 | 194407998 | 194408028 | Hyper | pancreas | FAM43A | chr3 | 194408375 | 194409021 | Hyper | liver_tcga, cancer_general, tcga | FAM43A |
| chr3 | 196255617 | 196255646 | Hyper | liver_tcga hepatobiliary | | chr3 | 196755958 | 196755987 | Hyper | liver_tcga | MFI2 |
| chr3 | 197236945 | 197237111 | Hyper | literature | BDH1 | chr3 | 197677029 | 197677058 | Hyper | literature | IQCG, RPL35A |
| chr3 | 197686941 | 197687223 | Hyper | literature | LMLN, RPL35A | chr3 | 197687694 | 197687723 | Hyper | literature | LMLN, RPL35A |
| chr2 | 46214 | 46450 | Hyper | blood | FAM110C | chr2 | 264163 | 264204 | Hyper | liver_tcga | ACP1, SH3YL1 |
| chr2 | 287580 | 287641 | Hyper | cancer_general | FAM150B | chr2 | 288404 | 288470 | Hyper | cancer_general | FAM150B |
| chr2 | 468045 | 468078 | Hyper | cancer_general | | chr2 | 468299 | 468672 | Hyper | tcga, cancer_general | |
| chr2 | 945913 | 946000 | Hyper | cancer_general | SNTG2 | chr2 | 946208 | 946263 | Hyper | cancer_general | SNTG2 |
| chr2 | 946526 | 946610 | Hyper | cancer_general | SNTG2 | chr2 | 946896 | 947159 | Hyper | cancer_general | SNTG2 |
| chr2 | 1746614 | 1747210 | Hyper | cancer_general | PXDN | chr2 | 1747670 | 1748890 | Hyper | tcga, cancer_general | PXDN |
| chr2 | 3750947 | 3750977 | Hyper | liver_tcga | ALLC | chr2 | 3751335 | 3751439 | Hyper | cancer_general | ALLC |
| chr2 | 5831178 | 5831324 | Hyper | cancer_general | SOX11 | chr2 | 5831789 | 5831819 | Hyper | cancer_general | SOX11 |
| chr2 | 5832069 | 5832222 | Hyper | cancer_general | SOX11 | chr2 | 5832890 | 5834028 | Hyper | cancer_general, pancreas | SOX11 |
| chr2 | 5836085 | 5836253 | Hyper | cancer_general | SOX11 | chr2 | 5836548 | 5837071 | Hyper | tcga, cancer_general | SOX11 |
| chr2 | 5837278 | 5837414 | Hyper | cancer_general | SOX11 | chr2 | 5866098 | 5866211 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 7571510 | 7571747 | Hyper | pancreas, cancer_general | LOC100506274 | chr2 | 10182827 | 10182904 | Hyper | cancer_general | KLF11 |
| chr2 | 10688874 | 10688904 | Hyper | cancer_general | — | chr2 | 11052217 | 11052559 | Hyper | cancer_general | KCNF1 |
| chr2 | 11809957 | 11810117 | Hyper | cancer_general | LPIN1, NTSR2 | chr2 | 12858452 | 12858618 | Hyper | tcga, colorectal | TRIB2 |
| chr2 | 14772761 | 14772823 | Hyper | blood | FAM84A, AX747684 | chr2 | 14774281 | 14774567 | Hyper | blood | AX747684, FAM84A |
| chr2 | 17719688 | 17719812 | Hyper | cancer_general | VSNL1 | chr2 | 18059035 | 18059085 | Hyper | cancer_general | KCNS3 |
| chr2 | 18059781 | 18059841 | Hyper | pancreas | KCNS3 | chr2 | 19550214 | 19550244 | Hyper | cancer_general | OSR1, MIR4757 |
| chr2 | 19551322 | 19551366 | Hyper | cancer_general | OSR1, MIR4757 | chr2 | 19556318 | 19556672 | Hyper | cancer_general | OSR1, MIR4757 |
| chr2 | 19557068 | 19557098 | Hyper | cancer_general | OSR1, MIR4757 | chr2 | 19557685 | 19557727 | Hyper | blood | OSR1, MIR4757 |
| chr2 | 19558832 | 19558893 | Hyper | cancer_general | OSR1 | chr2 | 19561131 | 19561316 | Hyper | cancer_general | OSR1 |
| chr2 | 19561517 | 19561685 | Hyper | cancer_general | OSR1 | chr2 | 19563358 | 19563433 | Hyper | cancer_general | OSR1 |
| chr2 | 20068798 | 20068885 | Hyper | cancer_general | LINC00954 | chr2 | 20865636 | 20865927 | Hyper | tcga, cancer_general | GDF7 |
| chr2 | 25390994 | 25391212 | Hyper | cancer_general | POMC, EFR3B | chr2 | 25391684 | 25391725 | Hyper | cancer_general | POMC, EFR3B |
| chr2 | 25438821 | 25439465 | Hyper | tcga, liver_tcga, cancer_general | — | chr2 | 26395447 | 26395556 | Hyper | liver_tcga | GAREML |
| chr2 | 26402030 | 26402060 | Hyper | cancer_general | GAREML | chr2 | 26407492 | 26408181 | Hyper | tcga, cancer_general | HADHA, GAREML |
| chr2 | 26521972 | 26522221 | Hyper | cancer_general | HADHB, GPR113 | chr2 | 26915763 | 26916259 | Hyper | cancer_general | KCNK3 |
| chr2 | 27070324 | 27070414 | Hyper | cancer_general | DPYSL5 | chr2 | 27071240 | 27071346 | Hyper | tcga | DPYSL5 |
| chr2 | 27072492 | 27072534 | Hyper | cancer_general | DPYSL5 | chr2 | 27072822 | 27072989 | Hyper | cancer_general | DPYSL5 |
| chr2 | 27665125 | 27665154 | Hyper | liver_tcga | KRTCAP3, IFT172, NRBP1 | chr2 | 27665506 | 27665711 | Hyper | liver_tcga | IFT172, KRTCAP3, NRBP1 |
| chr2 | 29033336 | 29033924 | Hyper | cancer_general | SPDYA, PPP1CB | chr2 | 29338084 | 29338969 | Hyper | colorectal, cancer_general | CLIP4 |
| chr2 | 29420483 | 29420512 | Hyper | literature | ALK | chr2 | 29432640 | 29432696 | Hyper | literature | ALK |
| chr2 | 29436844 | 29436888 | Hyper | literature | ALK | chr2 | 29443573 | 29443710 | Hyper | literature | ALK |
| chr2 | 29445198 | 29445482 | Hyper | literature | ALK | chr2 | 29446361 | 29446396 | Hyper | literature | ALK |
| chr2 | 30143304 | 30143492 | Hyper | cancer_general | — | chr2 | 30144041 | 30144411 | Hyper | tcga, cancer_general | — |
| chr2 | 30453714 | 30453941 | Hyper | cancer_general | LBH | chr2 | 31360306 | 31360831 | Hyper | colorectal | GALNT14 |
| chr2 | 31361089 | 31361118 | Hyper | tcga | GALNT14 | chr2 | 31361356 | 31361385 | Hyper | tcga | GALNT14 |
| chr2 | 31456682 | 31457039 | Hyper | tcga, esophageal, colorectal | EHD3, 5S_rRNA, CAPN14 | chr2 | 38302253 | 38302876 | Hyper | cancer_general | CYP1B1 |
| chr2 | 39187218 | 39187722 | Hyper | liver_tcga, cancer_general | LOC375196, ARHGEF33 | chr2 | 39893090 | 39893501 | Hyper | cancer_general | TMEM178A |
| chr2 | 39893972 | 39894059 | Hyper | cancer_general | TMEM178A | chr2 | 40678603 | 40679620 | Hyper | tcga, cancer_general | SLC8A1 |
| chr2 | 42274595 | 42274633 | Hyper | tcga | PKDCC | chr2 | 42329431 | 42329666 | Hyper | tcga | — |
| chr2 | 42720262 | 42720546 | Hyper | cancer_general | KCNG3, MTA3 | chr2 | 43019599 | 43019868 | Hyper | tcga | HAAO |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 43451909 | 43452327 | Hyper | lung | LOC100129726, THADA, ZFP36L2 | chr2 | 45028988 | 45029371 | Hyper | cancer_general | — |
| chr2 | 45029682 | 45029712 | Hyper | cancer_general | — | chr2 | 45155125 | 45157711 | Hyper | cancer_general | SIX3 |
| chr2 | 45159956 | 45160267 | Hyper | cancer_general | SIX3 | chr2 | 45160596 | 45160634 | Hyper | cancer_general | SIX3 |
| chr2 | 45161663 | 45162112 | Hyper | cancer_general | SIX3 | chr2 | 45162394 | 45162481 | Hyper | cancer_general | SIX3 |
| chr2 | 45162751 | 45162913 | Hyper | cancer_general | SIX3 | chr2 | 45164663 | 45164693 | Hyper | cancer_general | SIX3 |
| chr2 | 45165564 | 45165594 | Hyper | cancer_general | SIX3 | chr2 | 45168803 | 45168833 | Hyper | cancer_general | SIX3 |
| chr2 | 45169446 | 45170029 | Hyper | liver_tcga, cancer_general | SIX3 | chr2 | 45171385 | 45171862 | Hyper | liver_tcga, cancer_general | SIX3 |
| chr2 | 45176601 | 45176768 | Hyper | cancer_general | SIX3 | chr2 | 45179620 | 45179650 | Hyper | cancer_general | SIX3 |
| chr2 | 45179939 | 45180203 | Hyper | cancer_general | SIX3 | chr2 | 45181520 | 45181672 | Hyper | cancer_general | SIX3 |
| chr2 | 45181887 | 45182001 | Hyper | cancer_general | SIX3 | chr2 | 45228618 | 45228730 | Hyper | tcga | SIX2 |
| chr2 | 45231320 | 45231396 | Hyper | cancer_general | SIX2 | chr2 | 45231805 | 45232131 | Hyper | cancer_general | SIX2 |
| chr2 | 45233385 | 45233586 | Hyper | cancer_general | SIX2 | chr2 | 45233594 | 45233926 | Hyper | cancer_general | SIX2 |
| chr2 | 45237673 | 45237795 | Hyper | tcga, cancer_general | SIX2 | chr2 | 45240548 | 45240784 | Hyper | liver_tcga, cancer_general | SIX2 |
| chr2 | 45241136 | 45241184 | Hyper | cancer_general | SIX2 | chr2 | 45395854 | 45395920 | Hyper | cancer_general | UNQ6975 |
| chr2 | 45396315 | 45396451 | Hyper | cancer_general | UNQ6975 | chr2 | 45396688 | 45396995 | Hyper | cancer_general | UNQ6975 |
| chr2 | 46526302 | 46526448 | Hyper | blood | EPAS1 | chr2 | 47748140 | 47748494 | Hyper | cancer_general | KCNK12 |
| chr2 | 47797043 | 47797818 | Hyper | tcga, cancer_general | KCNK12 | chr2 | 47798180 | 47798663 | Hyper | cancer_general | KCNK12 |
| chr2 | 47798954 | 47799109 | Hyper | cancer_general | KCNK12 | chr2 | 48982582 | 48982866 | Hyper | cancer_general | LHCGR |
| chr2 | 50573595 | 50573803 | Hyper | cancer_general | NRXN1 | chr2 | 50574121 | 50574859 | Hyper | tcga, cancer_general | NRXN1 |
| chr2 | 56149836 | 56149866 | Hyper | cancer_general | EFEMP1 | chr2 | 56150729 | 56151193 | Hyper | tcga, cancer_general | EFEMP1 |
| chr2 | 56410817 | 56410996 | Hyper | esophageal | CCDC85A, AK311113, AK295617 | chr2 | 56411691 | 56411733 | Hyper | esophageal | AK295617, CCDC85A, AK311113 |
| chr2 | 58656049 | 58656125 | Hyper | tcga, cancer_general | — | chr2 | 60796587 | 60796646 | Hyper | cancer_general | — |
| chr2 | 60797137 | 60797281 | Hyper | cancer_general | OTX1, LOC100132215 | chr2 | 62798343 | 62798386 | Hyper | cancer_general | OTX1, LOC100132215 |
| chr2 | 63275563 | 63275855 | Hyper | cancer_general | OTX1, LOC100132215 | chr2 | 63278962 | 63278992 | Hyper | cancer_general | OTX1, LOC100132215 |
| chr2 | 63280952 | 63281651 | Hyper | liver_tcga, cancer_general, tcga | OTX1, LOC100132215 | chr2 | 63282716 | 63282786 | Hyper | cancer_general | OTX1, LOC100132215 |
| chr2 | 63282998 | 63283027 | Hyper | literature | OTX1, LOC100132215 | chr2 | 63283952 | 63284146 | Hyper | liver_tcga, literature | OTX1, LOC100132215 |
| chr2 | 63284777 | 63284811 | Hyper | cancer_general | OTX1, LOC100132215 | chr2 | 63285081 | 63287368 | Hyper | liver_tcga, literature, cancer_general | OTX1 |
| chr2 | 66652863 | 66652963 | Hyper | tcga | MEIS1, MEIS1-AS3 | chr2 | 66653238 | 66653496 | Hyper | cancer_general | MEIS1, EMIS1-AS3 |
| chr2 | 66653764 | 66653914 | Hyper | cancer_general | MEIS1, MEIS1-AS3 | chr2 | 66660650 | 66660888 | Hyper | tcga | MEIS1, MEIS1-AS3, MEIS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 66662749 | 66662824 | Hyper | tcga | MEIS1, MEIS1-AS3 | chr2 | 66808525 | 66809361 | Hyper | tcga, cancer_general | MEIS1 |
| chr2 | 68546324 | 68546892 | Hyper | tcga, cancer_general | CNRIP1 | chr2 | 71503790 | 71503823 | Hyper | cancer_general | ZNF638 |
| chr2 | 71504103 | 71504148 | Hyper | cancer_general | ZNF638 | chr2 | 71680833 | 71680863 | Hyper | cancer_general | DYSF |
| chr2 | 71693374 | 71693593 | Hyper | tcga | DYSF | chr2 | 72374375 | 72374432 | Hyper | cancer_general | CYP26B1 |
| chr2 | 72374694 | 72374765 | Hyper | cancer_general | CYP26B1 | chr2 | 73145640 | 73145694 | Hyper | cancer_general | EMX1 |
| chr2 | 73145924 | 73146021 | Hyper | cancer_general | EMX1 | chr2 | 73147324 | 73148243 | Hyper | tcga, cancer_general | EMX1 |
| chr2 | 73150924 | 73150954 | Hyper | cancer_general | EMX1 | chr2 | 73151187 | 73151831 | Hyper | liver_tcga, cancer_general | EMX1 |
| chr2 | 73152683 | 73152754 | Hyper | cancer_general | EMX1 | chr2 | 73429523 | 73429614 | Hyper | cancer_general | NOTO |
| chr2 | 73429952 | 73430069 | Hyper | cancer_general | NOTO | chr2 | 73430322 | 73430743 | Hyper | cancer_general | NOTO |
| chr2 | 73518448 | 73518919 | Hyper | cancer_general | EGR4, U6, AK125051 | chr2 | 73519579 | 73519841 | Hyper | cancer_general | U6, EGR4, AK125051 |
| chr2 | 74426185 | 74426214 | Hyper | liver_tcga | MTHFD2 | chr2 | 74726744 | 74726774 | Hyper | cancer_general | LBX2-AS1, PCGF1, LBX2, TTC31 |
| chr2 | 74740852 | 74741387 | Hyper | liver_tcga, cancer_general | LBX2-AS1, TLX2, DQX1, PCGF1 | chr2 | 74741835 | 74741955 | Hyper | tcga, cancer_general | DQX1, TLX2, PCGF1, LBX2-AS1 |
| chr2 | 74742176 | 74743732 | Hyper | liver_tcga, cancer_general | DQX1, TLX2, PCGF1, LBX2-AS1 | chr2 | 74782081 | 74782271 | Hyper | liver_tcga, cancer_general | DOK1, MLAP, LOXL3 |
| chr2 | 75427040 | 75427114 | Hyper | cancer_general | — | chr2 | 75427369 | 75427399 | Hyper | blood | — |
| chr2 | 75427930 | 75428177 | Hyper | cancer_general, tcga | — | chr2 | 75720510 | 75720541 | Hyper | liver_tcga | EVA1A |
| chr2 | 80529378 | 80529443 | Hyper | cancer_general | CTNNA2, LRRTM1 | chr2 | 80529662 | 80530022 | Hyper | cancer_general | CTNNA2, LRRTM1 |
| chr2 | 80530505 | 80530558 | Hyper | cancer_general | CTNNA2, LRRTM1 | chr2 | 80531725 | 80531755 | Hyper | cancer_general | CTNNA2, LRRTM1 |
| chr2 | 80549585 | 80549745 | Hyper | cancer_general | CTNNA2 | chr2 | 85107454 | 85107538 | Hyper | cancer_general | TRABD2A |
| chr2 | 85361317 | 85361609 | Hyper | cancer_general | TCF7L1 | chr2 | 86263223 | 86263270 | Hyper | liver_tcga | POLR1A |
| chr2 | 87016579 | 87016636 | Hyper | cancer_general | CD8A, RMND5A | chr2 | 87017796 | 87018396 | Hyper | tcga, cancer_general | RMND5A, CD8A |
| chr2 | 87036611 | 87036640 | Hyper | literature | CD8B | chr2 | 88751281 | 88751800 | Hyper | tcga, cancer_general | FOXI3 |
| chr2 | 88752055 | 88752285 | Hyper | liver_tcga, cancer_general | FOXI3 | chr2 | 88752603 | 88752785 | Hyper | cancer_general | FOXI3 |
| chr2 | 89064610 | 89065278 | Hyper | literature, cancer_general | ANKRD36BP2 | chr2 | 95663969 | 95664014 | Hyper | cancer_general | — |
| chr2 | 95690747 | 95690793 | Hyper | cancer_general | MAL | chr2 | 95691036 | 95691269 | Hyper | tcga, cancer_general, literature | MAL |
| chr2 | 95691530 | 95691769 | Hyper | literature, cancer_general | MAL | chr2 | 95691994 | 95692480 | Hyper | tcga, cancer_general, literature | MAL |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 96990898 | 96991316 | Hyper | literature, cancer_general | ITPRIPL1 | chr2 | 97193097 | 97193626 | Hyper | cancer_general | ARIDSA |
| chr2 | 98703323 | 98703475 | Hyper | liver_tcga | VWA3B | chr2 | 98703675 | 98703736 | Hyper | hepatobiliary | VWA3B |
| chr2 | 98962898 | 98962940 | Hyper | cancer_general | CNGA3 | chr2 | 98963329 | 98963599 | Hyper | cancer_general | CNGA3 |
| chr2 | 98963838 | 98964200 | Hyper | cancer_general | CNGA3 | chr2 | 98964596 | 98964645 | Hyper | cancer_general | CNGA3 |
| chr2 | 99439138 | 99439507 | Hyper | pancreas, cancer_general | KIAA1211L | chr2 | 99553391 | 99553656 | Hyper | tcga | KIAA1211L |
| chr2 | 100937836 | 100939155 | Hyper | tcga, colorectal, cancer_general | LONRF2 | chr2 | 101034242 | 101034293 | Hyper | tcga | CHST10 |
| chr2 | 101436632 | 101436708 | Hyper | blood | NPAS2 | chr2 | 101666893 | 101667004 | Hyper | liver_tcga | TBC1D8 |
| chr2 | 102091180 | 102091335 | Hyper | tcga | RFX8 | chr2 | 103236165 | 103236292 | Hyper | blood | SLC9A2 |
| chr2 | 105459081 | 105459518 | Hyper | cancer_general | LOC100506421 | chr2 | 105459908 | 105460599 | Hyper | cancer_general | LOC100506421 |
| chr2 | 105460921 | 105460951 | Hyper | cancer_general | LOC100506421 | chr2 | 105461187 | 105461243 | Hyper | cancer_general | LOC100506421 |
| chr2 | 105461564 | 105461896 | Hyper | cancer_general | LOC100506421 | chr2 | 105462165 | 105462222 | Hyper | cancer_general | POU3F3, LOC100506421 |
| chr2 | 105468791 | 105468908 | Hyper | cancer_general | LOC100506421, POU3F3 | chr2 | 105469645 | 105470091 | Hyper | cancer_general | POU3F3, LOC100506421 |
| chr2 | 105470350 | 105470840 | Hyper | tcga, literature, cancer_general, liver_tcga | POU3F3, LOC100506421 | chr2 | 105472231 | 105472845 | Hyper | cancer_general | AK095498, POU3F3, LOC100506421 |
| chr2 | 105473248 | 105473553 | Hyper | cancer_general | AK095498, POU3F3, LOC100506421 | chr2 | 105478762 | 105479089 | Hyper | cancer_general | AK095498, POU3F3 |
| chr2 | 105480530 | 105480595 | Hyper | cancer_general | AK095498, POU3F3 | chr2 | 105483655 | 105483719 | Hyper | cancer_general | AK095498 |
| chr2 | 105484450 | 105484522 | Hyper | cancer_general | AK095498 | chr2 | 105760981 | 105761037 | Hyper | cancer_general | |
| chr2 | 106681733 | 106681767 | Hyper | cancer_general | C2orf40 | chr2 | 106682012 | 106682098 | Hyper | cancer_general | C2orf40 |
| chr2 | 107103865 | 107103928 | Hyper | cancer_general | — | chr2 | 107502600 | 107502815 | Hyper | tcga, cancer_general | ST6GAL2 |
| chr2 | 107503218 | 107503328 | Hyper | tcga, cancer_general | ST6GAL2 | chr2 | 107503532 | 107503561 | Hyper | tcga | ST6GAL2 |
| chr2 | 107503884 | 107504018 | Hyper | cancer_general | ST6GAL2 | chr2 | 109648080 | 109648222 | Hyper | tcga | — |
| chr2 | 109745989 | 109746079 | Hyper | cancer_general | SH3RF3, SH3RF3-AS1 | chr2 | 109746289 | 109746477 | Hyper | cancer_general | SH3RF3, SH3RF3-AS1 |
| chr2 | 110370941 | 110371219 | Hyper | blood | SOWAHC | chr2 | 110873016 | 110873045 | Hyper | literature | NPHP1 |
| chr2 | 111875191 | 111875611 | Hyper | lung, cancer_general | AK125994, BCL2L11 | chr2 | 111876698 | 111876870 | Hyper | cancer_general | BCL2L11, AK125994 |
| chr2 | 112657033 | 112657092 | Hyper | cancer_general | MERTK | chr2 | 113594639 | 113594668 | Hyper | literature | IL1B |
| chr2 | 113931503 | 113931532 | Hyper | literature | PSD4 | chr2 | 114034892 | 114035180 | Hyper | cancer_general | PAX8 |
| chr2 | 114256978 | 114257137 | Hyper | cancer_general | FOXD4L1, CBWD2 | chr2 | 114261300 | 114261458 | Hyper | cancer_general | FOXD4L1, CBWD2 |
| chr2 | 115918661 | 115920534 | Hyper | tcga, cancer_general | LOC389023, DPP10 | chr2 | 118981151 | 118982497 | Hyper | cancer_general, tcga, lung | — |
| chr2 | 119067636 | 119068049 | Hyper | liver_tcga, cancer_general | — | chr2 | 119532161 | 119532255 | Hyper | cancer_general | — |
| chr2 | 119566239 | 119566272 | Hyper | tcga, cancer_general | EN1 | chr2 | 119591351 | 119591465 | Hyper | cancer_general | EN1 |
| chr2 | 119592588 | 119592777 | Hyper | tcga, cancer_general | EN1 | chr2 | 119592997 | 119593567 | Hyper | tcga, cancer_general | EN1 |
| chr2 | 119599926 | 119600031 | Hyper | cancer_general | EN1 | chr2 | 119600332 | 119600555 | Hyper | cancer_general | EN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 119600949 | 119601061 | Hyper | cancer_general | EN1 | chr2 | 119602601 | 119603086 | Hyper | cancer_general | EN1 |
| chr2 | 119604032 | 119604158 | Hyper | cancer_general | EN1 | chr2 | 119604809 | 119604851 | Hyper | cancer_general | EN1 |
| chr2 | 119606135 | 119606558 | Hyper | cancer_general | EN1 | chr2 | 119606783 | 119606839 | Hyper | cancer_general | EN1 |
| chr2 | 119607176 | 119607411 | Hyper | cancer_general | EN1 | chr2 | 119607783 | 119607842 | Hyper | cancer_general | EN1 |
| chr2 | 119610844 | 119610969 | Hyper | cancer_general | EN1 | chr2 | 119611745 | 119611799 | Hyper | cancer_general | EN1 |
| chr2 | 119612324 | 119612354 | Hyper | cancer_general | EN1 | chr2 | 119614130 | 119614171 | Hyper | cancer_general | EN1 |
| chr2 | 119614780 | 119614852 | Hyper | cancer_general | EN1 | chr2 | 119615055 | 119615627 | Hyper | cancer_general | EN1 |
| chr2 | 119616155 | 119616582 | Hyper | cancer_general | — | chr2 | 119616809 | 119616870 | Hyper | cancer_general | — |
| chr2 | 119914720 | 119914752 | Hyper | cancer_general | C1QL2 | chr2 | 119916049 | 119916082 | Hyper | cancer_general | C1QL2 |
| chr2 | 119916299 | 119916595 | Hyper | tcga, cancer_general | C1QL2 | chr2 | 120281646 | 120281693 | Hyper | cancer_general | SCTR |
| chr2 | 120281923 | 120281953 | Hyper | cancer_general | SCTR | chr2 | 121200390 | 121200433 | Hyper | cancer_general | — |
| chr2 | 121345081 | 121345111 | Hyper | cancer_general | — | chr2 | 121411888 | 121412153 | Hyper | liver_tcga, literature | — |
| chr2 | 122176232 | 122176293 | Hyper | liver_tcga | CLASP1 | chr2 | 124782333 | 124782458 | Hyper | cancer_general | CNTNAP5 |
| chr2 | 124782692 | 124783097 | Hyper | tcga, cancer_general | CNTNAP5 | chr2 | 127413918 | 127414036 | Hyper | cancer_general | GYPC |
| chr2 | 127783043 | 127783257 | Hyper | liver_tcga, cancer_general | — | chr2 | 127863601 | 127863725 | Hyper | breast | BIN1 |
| chr2 | 127976467 | 127976672 | Hyper | cancer_general | CYP27C1 | chr2 | 128421866 | 128421947 | Hyper | cancer_general | — |
| chr2 | 129494389 | 129494421 | Hyper | head_neck | — | chr2 | 130763584 | 130763623 | Hyper | cancer_general | — |
| chr2 | 130971149 | 130971321 | Hyper | liver_tcga, literature, cancer_general | — | chr2 | 131594989 | 131595019 | Hyper | pancreas | AK127124, AX746725 |
| chr2 | 131673756 | 131673785 | Hyper | literature | ARHGEF4, AK127124 | chr2 | 131720852 | 131721253 | Hyper | cancer_general | ARHGEF4 |
| chr2 | 131721461 | 131721949 | Hyper | cancer_general | ARHGEF4 | chr2 | 131792260 | 131793131 | Hyper | cancer_general, tcga | ARHGEF4 |
| chr2 | 132088770 | 132088828 | Hyper | cancer_general | — | chr2 | 132121661 | 132121829 | Hyper | tcga | TRNA, WTH3DI |
| chr2 | 132152361 | 132152495 | Hyper | cancer_general | LOC389043, TRNA_Pseudo | chr2 | 132182790 | 132183089 | Hyper | cancer_general | — |
| chr2 | 132767457 | 132767707 | Hyper | cancer_general | — | chr2 | 132795240 | 132795419 | Hyper | cancer_general | — |
| chr2 | 132795670 | 132795728 | Hyper | cancer_general | — | chr2 | 133014598 | 133014638 | Hyper | cancer_general | ANKRD30BL, JA668105, MIR663B |
| chr2 | 133015275 | 133015323 | Hyper | cancer_general | JA668105, MIR663B, ANKRD30BL | chr2 | 133062326 | 133062389 | Hyper | cancer_general | AK094599 |
| chr2 | 133426249 | 133426279 | Hyper | cancer_general | NCKAP5, LYPD1 | chr2 | 133426637 | 133426674 | Hyper | cancer_general | LYPD1, NCKAP5 |
| chr2 | 137522445 | 137522475 | Hyper | cancer_general | THSD7B | chr2 | 137523825 | 137523855 | Hyper | cancer_general | THSD7B |
| chr2 | 139536937 | 139537145 | Hyper | cancer_general | NXPH2 | chr2 | 139537443 | 139537865 | Hyper | tcga, cancer_general | NXPH2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 142887871 | 142888066 | Hyper | tcga | — | chr2 | 142888348 | 142888418 | Hyper | cancer_general | — |
| chr2 | 144694367 | 144695135 | Hyper | tcga, colorectal cancer_general | GTDC1 | chr2 | 145273404 | 145273751 | Hyper | cancer_general | ZEB2_AS1_1, ZEB2-AS1, ZEB2_AS1_3, ZEB2_AS1_4, AK124806, ZEB2 |
| chr2 | 145274186 | 145274455 | Hyper | tcga, cancer_general | AK124806, ZEB2, ZEB 2_AS1_1, ZEB2-AS1, ZEB2_AS1_3, ZEB2_AS1_4 | chr2 | 145274814 | 145275213 | Hyper | tcga, cancer_general | ZEB2-AS1, ZEB2_AS1_3, ZEB2_AS1_4, AK124806, ZEB2 |
| chr2 | 145282119 | 145282149 | Hyper | pancreas | ZEB2_AS1_4, ZEB2_AS1_3, ZEB2-AS1, ZEB2_AS1_1 | chr2 | 149633097 | 149633399 | Hyper | tcga, cancer_general | ZEB2_AS1_1 |
| chr2 | 149633744 | 149633965 | Hyper | cancer_general | JB137817, KIF5C | chr2 | 149645496 | 149645894 | Hyper | cancer_general | JB137817, KIF5C |
| chr2 | 151342903 | 151343277 | Hyper | blood | RND3 | chr2 | 154333535 | 154333567 | Hyper | cancer_general | RPRM |
| chr2 | 154334272 | 154334665 | Hyper | cancer_general | RPRM | chr2 | 154335139 | 154335271 | Hyper | cancer_general | RPRM |
| chr2 | 154728042 | 154728482 | Hyper | cancer_general, liver_tcga, tcga | GALNT13 | chr2 | 154729044 | 154729240 | Hyper | tcga, cancer_general | GALNT13 |
| chr2 | 154729559 | 154729589 | Hyper | cancer_general | GALNT13 | chr2 | 155555038 | 155555361 | Hyper | tcga | KCNJ3 |
| chr2 | 157176592 | 157176717 | Hyper | cancer_general | NR4A2 | chr2 | 157177003 | 157178310 | Hyper | cancer_general | NR4A2 |
| chr2 | 157178646 | 157178731 | Hyper | liver_tcga | NR4A2 | chr2 | 160761070 | 160761556 | Hyper | tcga, liver_tcga | LY75 |
| chr2 | 162272989 | 162274338 | Hyper | lung, literature, cancer_general | TBR1 | chr2 | 162274717 | 162274866 | Hyper | cancer_general | TBR1 |
| chr2 | 162275146 | 162275802 | Hyper | tcga, cancer_general | TBR1 | chr2 | 162280003 | 162280956 | Hyper | liver_tcga, cancer_general | TBR1 |
| chr2 | 162283365 | 162284055 | Hyper | liver_tcga, cancer_general | TBR1 | chr2 | 164593096 | 164593137 | Hyper | cancer_general | FIGN |
| chr2 | 168150069 | 168150245 | Hyper | cancer_general | — | chr2 | 168150751 | 168150945 | Hyper | cancer_general | AK023515, LOC440925, SP5 |
| chr2 | 171570082 | 171570428 | Hyper | cancer_general | LOC440925, SP5, AK023515 | chr2 | 171570684 | 171570733 | Hyper | cancer_general | AK023515, LOC440925, SP5 |
| chr2 | 171571264 | 171571315 | Hyper | blood | AK023515, SP5, LOC440925 | chr2 | 171571889 | 171572068 | Hyper | blood | AK023515, SP5, LOC440925 |
| chr2 | 171670349 | 171670467 | Hyper | cancer_general | GAD1 | chr2 | 171671487 | 171671881 | Hyper | cancer_general | GAD1 |
| chr2 | 171673873 | 171673939 | Hyper | blood | GAD1 | chr2 | 171674739 | 171675066 | Hyper | liver_tcga, cancer_general | GAD1 |
| chr2 | 171675361 | 171675592 | Hyper | cancer_general | GAD1 | chr2 | 171676684 | 171676785 | Hyper | cancer_general | GAD1 |
| chr2 | 172945124 | 172945167 | Hyper | cancer_general | DLX1, METAP1D | chr2 | 172945896 | 172946211 | Hyper | cancer_general | DLX1, METAP1D |
| chr2 | 172947717 | 172948314 | Hyper | cancer_general | METAP1D, DLX1 | chr2 | 172948709 | 172948751 | Hyper | cancer_general | DLX1, METAP1D |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 172949186 | 172949711 | Hyper | cancer_general | DLX1, METAP1D | chr2 | 172951596 | 172951689 | Hyper | cancer_general | DLX1, METAP1D |
| chr2 | 172952521 | 172953046 | Hyper | cancer_general | DLX1, METAP1D | chr2 | 172955444 | 172955545 | Hyper | cancer_general | DLX2, DLX1, METAP1D |
| chr2 | 172957907 | 172958066 | Hyper | cancer_general | DLX2, DLX1 | chr2 | 172961398 | 172961598 | Hyper | cancer_general | DLX2, DLX1 |
| chr2 | 172964821 | 172965802 | Hyper | cancer_general | DLX2 | chr2 | 172966264 | 172966442 | Hyper | cancer_general | DLX2 |
| chr2 | 172972735 | 172973218 | Hyper | cancer_general | DLX2 | chr2 | 173099784 | 173099814 | Hyper | cancer_general | — |
| chr2 | 173100262 | 173100430 | Hyper | cancer_general | — | chr2 | 175190871 | 175192468 | Hyper | lung, cancer_general | SP9, LOC285084 |
| chr2 | 175193268 | 175193823 | Hyper | lung, cancer_general | SP9, LOC285084 | chr2 | 175195831 | 175195861 | Hyper | cancer_general | SP9, LOC285084 |
| chr2 | 175196432 | 175196575 | Hyper | cancer_general | SP9, LOC285084 | chr2 | 175197089 | 175197119 | Hyper | cancer_general | SP9, LOC285084 |
| chr2 | 175198752 | 175198966 | Hyper | literature, cancer_general | SP9, LOC285084 | chr2 | 175199527 | 175199935 | Hyper | literature, cancer_general | SP9, LOC285084 |
| chr2 | 175200140 | 175202652 | Hyper | lung, cancer_general | SP9, LOC285084 | chr2 | 175204174 | 175204204 | Hyper | cancer_general | SP9, LOC285084, CIR1 |
| chr2 | 175204786 | 175205799 | Hyper | cancer_general | LOC285084, CIR1, SP9 | chr2 | 175206833 | 175207028 | Hyper | cancer_general | CIR1, SP9 |
| chr2 | 175207228 | 175207258 | Hyper | cancer_general | CIR1, SP9 | chr2 | 175207536 | 175207653 | Hyper | cancer_general | CIR1, SP9 |
| chr2 | 175208311 | 175209135 | Hyper | cancer_general | CIR1, SP9 | chr2 | 175547041 | 175547140 | Hyper | tcga | WIPF1 |
| chr2 | 175547384 | 175547413 | Hyper | tcga | WIPF1 | chr2 | 176940167 | 176940315 | Hyper | cancer_general | EVX2 |
| chr2 | 176943269 | 176943568 | Hyper | cancer_general | EVX2 | chr2 | 176943861 | 176943902 | Hyper | cancer_general | EVX2 |
| chr2 | 176944426 | 176945784 | Hyper | cancer_general | EVX2 | chr2 | 176946578 | 176947389 | Hyper | cancer_general | EVX2 |
| chr2 | 176947748 | 176947903 | Hyper | cancer_general | EVX2 | chr2 | 176948599 | 176948742 | Hyper | literature, cancer_general | HOXD13, EVX2 |
| chr2 | 176949045 | 176949075 | Hyper | cancer_general | HOXD13, EVX2 | chr2 | 176949695 | 176949869 | Hyper | cancer_general | HOXD13, EVX2 |
| chr2 | 176950142 | 176950258 | Hyper | literature, cancer_general | HOXD13, EVX2 | chr2 | 176956558 | 176956640 | Hyper | literature, cancer_general | HOXD13, HOXD12, EVX2 |
| chr2 | 176956921 | 176957199 | Hyper | cancer_general | HOXD13, HOXD12, EVX2 | chr2 | 176957497 | 176957919 | Hyper | cancer_general | HOXD13, HOXD12, EVX2 |
| chr2 | 176958138 | 176958489 | Hyper | cancer_general | HOXD12, HOXD13 | chr2 | 176959289 | 176959511 | Hyper | cancer_general | HOXD12, HOXD11, HOXD13 |
| chr2 | 176963448 | 176963522 | Hyper | cancer_general | HOXD12, HOXD11, HOXD13 | chr2 | 176964085 | 176964151 | Hyper | literature, cancer_general | HOXD11, HOXD13, HOXD12 |
| chr2 | 176964369 | 176965492 | Hyper | literature, cancer_general | HOXD12, HOXD11, HOXD13 | chr2 | 176969463 | 176969908 | Hyper | cancer_general | HOXD13, HOXD12, HOXD11 |
| chr2 | 176971628 | 176971712 | Hyper | pancreas | HOXD11, HOXD10, HOXD12 | chr2 | 176972557 | 176972586 | Hyper | liver_tcga | HOXD11, HOXD12, HOXD10 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 176976029 | 176976188 | Hyper | tcga, cancer_general | HOXD10, HOXD11 | chr2 | 176980750 | 176981506 | Hyper | cancer_general, literature | HOXD9, HOXD11, HOXD10 |
| chr2 | 176982584 | 176982627 | Hyper | cancer_general | HOXD10, HOXD11, HOXD9, AX747372 | chr2 | 176986715 | 176986848 | Hyper | cancer_general | AX747372, HOXD8, HOXD10, HOXD9 |
| chr2 | 176987057 | 176988304 | Hyper | cancer_general, literature | HOXD10, HOXD9, AX747372, HOXD8 | chr2 | 176993074 | 176993103 | Hyper | literature | BC047605, HOXD9, HOXD10, AX747372, HOXD8, HOXD-AS2 |
| chr2 | 176993547 | 176993855 | Hyper | tcga, literature, cancer_general | AX747372, HOXD9, HOXD10, HOXD8, HOXD-AS2, BC047605 | chr2 | 176994124 | 176994764 | Hyper | liver_tcga, cancer_general | AX747372, HOXD9, HOXD10, HOXD8, HOXD-AS2 |
| chr2 | 176995072 | 176995668 | Hyper | cancer_general | HOXD8, AX747372, HOXD9, HOXD-AS2, BC047605 | chr2 | 177001102 | 177001976 | Hyper | tcga, lung, cancer_general | BC047605, HOXD-AS2, HOXD8, AX747372 |
| chr2 | 177004566 | 177004658 | Hyper | cancer_general | BC047605, HOXD-AS2, HOXD8 | chr2 | 177014981 | 177015010 | Hyper | literature | MIR10B, HOXD4, BC047605 |
| chr2 | 177027425 | 177027454 | Hyper | literature | HOXD3, HOXD4 | chr2 | 177030149 | 177030228 | Hyper | liver_tcga | HOXD3, HOXD-AS1 |
| chr2 | 177042984 | 177043515 | Hyper | tcga, cancer_general | HOXD1, HOXD-AS1, HOXD3 | chr2 | 177053276 | 177053816 | Hyper | cancer_general | HOXD1, HOXD-AS1 |
| chr2 | 177054113 | 177054351 | Hyper | cancer_general | HOXD1, HOXD-AS1 | chr2 | 177503048 | 177503077 | Hyper | literature | LOC375295 |
| chr2 | 177503581 | 177503610 | Hyper | literature | LOC375295 | chr2 | 178098791 | 178098967 | Hyper | literature | NFE2L2 |
| chr2 | 182321397 | 182321637 | Hyper | cancer_general | ITGA4 | chr2 | 182321839 | 182322170 | Hyper | cancer_general | ITGA4 |
| chr2 | 182322379 | 182323042 | Hyper | cancer_general | ITGA4 | chr2 | 182451522 | 182451551 | Hyper | literature | CERKL |
| chr2 | 182542903 | 182542933 | Hyper | cancer_general | NEUROD1 | chr2 | 182543321 | 182543418 | Hyper | cancer_general | NEUROD1 |
| chr2 | 182543764 | 182543925 | Hyper | cancer_general | NEUROD1 | chr2 | 182545211 | 182545275 | Hyper | cancer_general | NEUROD1 |
| chr2 | 182545539 | 182545694 | Hyper | cancer_general | NEUROD1 | chr2 | 182545986 | 182546085 | Hyper | cancer_general | NEUROD1 |
| chr2 | 182546435 | 182546465 | Hyper | cancer_general | NEUROD1 | chr2 | 182547385 | 182547613 | Hyper | cancer_general | NEUROD1 |
| chr2 | 182547937 | 182548161 | Hyper | cancer_general | NEUROD1 | chr2 | 182549088 | 182549134 | Hyper | cancer_general | NEUROD1 |
| chr2 | 182549337 | 182549454 | Hyper | cancer_general | NEUROD1 | chr2 | 182550094 | 182550124 | Hyper | cancer_general | NEUROD1 |
| chr2 | 182819048 | 182819216 | Hyper | cancer_general | — | chr2 | 183731294 | 183731524 | Hyper | cancer_general | FRZB |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 183731809 | 183732076 | Hyper | tcga, cancer_general, literature | FRZB | chr2 | 185462869 | 185462980 | Hyper | cancer_general | ZNF804A |
| chr2 | 185463193 | 185463817 | Hyper | tcga, cancer_general | ZNF804A | chr2 | 186603488 | 186603518 | Hyper | cancer_general | FSIP2, BC039382 |
| chr2 | 188419047 | 188419204 | Hyper | cancer_general | TFPI | chr2 | 189157427 | 189157688 | Hyper | cancer_general, blood | MIR561, GULP1 |
| chr2 | 190708790 | 190708819 | Hyper | literature | PMS1 | chr2 | 193059025 | 193060067 | Hyper | cancer_general, tcga | TMEFF2 |
| chr2 | 193060385 | 193060441 | Hyper | cancer_general | TMEFF2 | chr2 | 193060683 | 193060891 | Hyper | tcga, cancer_general | TMEFF2 |
| chr2 | 193061388 | 193061480 | Hyper | cancer_general | TMEFF2 | chr2 | 198267345 | 198267374 | Hyper | literature | SnR39B, SF3B1 |
| chr2 | 198650984 | 198651076 | Hyper | liver_tcga | BOLL | chr2 | 200326590 | 200326735 | Hyper | liver_tcga, literature | SATB2-AS1, AK056625, AK125157 |
| chr2 | 200327287 | 200327565 | Hyper | liver_tcga, cancer_general | AK125157, SATB2-AS1, AK056625 | chr2 | 200328747 | 200329668 | Hyper | cancer_general | SATB2-AS1, AK056625, AK125157 |
| chr2 | 200333775 | 200333834 | Hyper | cancer_general | AK056625, SATB2-AS1, AK125157 | chr2 | 200334976 | 200335952 | Hyper | cancer_general, liver_tcga | AK056625, SATB2-AS1 |
| chr2 | 201172444 | 201172480 | Hyper | blood | SPATS2L | chr2 | 201450556 | 201450707 | Hyper | cancer_general | AOX1, SGOL2 |
| chr2 | 201450947 | 201451040 | Hyper | tcga | SGOL2, AOX1 | chr2 | 202097078 | 202097143 | Hyper | literature | CASP8 |
| chr2 | 202098936 | 202098965 | Hyper | literature | CASP8 | chr2 | 202101190 | 202101219 | Hyper | literature | CASP8 |
| chr2 | 202122459 | 202122683 | Hyper | literature | CASP8 | chr2 | 202899862 | 202899891 | Hyper | liver_tcga | FZD7 |
| chr2 | 206551056 | 206551378 | Hyper | tcga, cancer_general | NRP2 | chr2 | 207139072 | 207139102 | Hyper | cancer_general | ZDBF2, BC028329 |
| chr2 | 207139347 | 207139605 | Hyper | liver_tcga, cancer_general | ZDBF2, BC028329 | chr2 | 207307528 | 207307562 | Hyper | cancer_general | ADAM23 |
| chr2 | 207308802 | 207308857 | Hyper | cancer_general | ADAM23 | chr2 | 207506691 | 207507181 | Hyper | cancer_general | DYTN, LOC200726 |
| chr2 | 208635534 | 208635774 | Hyper | tcga, cancer_general | FZD5 | chr2 | 208989208 | 208989382 | Hyper | liver_tcga, literature | CRYGD, LOC100507443, CRYGC |
| chr2 | 209113097 | 209113126 | Hyper | literature | IDH1-AS1, IDH1 | chr2 | 209271322 | 209271551 | Hyper | cancer_general | PTH2R |
| chr2 | 210636335 | 210636892 | Hyper | cancer_general, tcga | UNC80 | chr2 | 212248428 | 212248457 | Hyper | literature | ERBB4 |
| chr2 | 212288927 | 212288956 | Hyper | literature | ERBB4 | chr2 | 212295683 | 212295820 | Hyper | literature | ERBB4 |
| chr2 | 212530120 | 212530149 | Hyper | literature | ERBB4 | chr2 | 212537902 | 212537994 | Hyper | literature | ERBB4 |
| chr2 | 212566811 | 212566840 | Hyper | literature | ERBB4 | chr2 | 212578292 | 212578321 | Hyper | literature | ERBB4 |
| chr2 | 212587132 | 212587161 | Hyper | literature | — | chr2 | 213401235 | 213401339 | Hyper | cancer_general | — |
| chr2 | 213401613 | 213401947 | Hyper | cancer_general | — | chr2 | 213403110 | 213403337 | Hyper | tcga, cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 215275823 | 215275852 | Hyper | literature | VWC2L | chr2 | 217559296 | 217559326 | Hyper | cancer_general | IGFBP5 |
| chr2 | 217559966 | 217559999 | Hyper | cancer_general | IGFBP5 | chr2 | 218770207 | 218770270 | Hyper | liver_tcga, tcga, cancer_general | TNS1 |
| chr2 | 218806147 | 218806302 | Hyper | cancer_general | TNS1 | chr2 | 219736151 | 219736691 | Hyper | cancer_general | WNT10A, WNT6 |
| chr2 | 219828049 | 219828117 | Hyper | cancer_general | CDK5R2 | chr2 | 219847462 | 219847555 | Hyper | cancer_general | CRYBA2, FEV, LINC00608 |
| chr2 | 219848809 | 219849001 | Hyper | cancer_general | CRYBA2, FEV, LINC00608 | chr2 | 219857723 | 219857756 | Hyper | cancer_general | CRYBA2, FEV, MIR375, LOC100129175, CCDC108 |
| chr2 | 220173989 | 220174296 | Hyper | literature, cancer_general | — | chr2 | 220196354 | 220196567 | Hyper | cancer_general | RESP18 |
| chr2 | 220223098 | 220223128 | Hyper | cancer_general | — | chr2 | 220223648 | 220223703 | Hyper | cancer_general | — |
| chr2 | 220283338 | 220283519 | Hyper | cancer_general | DES | chr2 | 220299588 | 220300059 | Hyper | cancer_general | SPEG, DES |
| chr2 | 220313621 | 220313692 | Hyper | cancer_general | SPEG | chr2 | 220349029 | 220349706 | Hyper | cancer_general | — |
| chr2 | 220361447 | 220361531 | Hyper | cancer_general | GMPPA | chr2 | 220416379 | 220416513 | Hyper | cancer_general | CHPF, OBSL1, MIR3132, TMEM198 |
| chr2 | 220416848 | 220417649 | Hyper | liver_tcga, cancer_general | CHPF, OBSL1, MIR3132, TMEM198 | chr2 | 222435773 | 222435863 | Hyper | cancer_general | AX747413, EPHA4 |
| chr2 | 223155722 | 223156188 | Hyper | cancer_general | CCDC140, DD413687, PAX3 | chr2 | 223158730 | 223159453 | Hyper | cancer_general, lung | CCDC140, DD413687, PAX3 |
| chr2 | 223159823 | 223160065 | Hyper | tcga, cancer_general | CCDC140, DD413687, PAX3 | chr2 | 223160342 | 223160379 | Hyper | cancer_general | CCDC140, DD413687, PAX3 |
| chr2 | 223161247 | 223162063 | Hyper | tcga, cancer_general | CCDC140, DD413687, PAX3 | chr2 | 223162779 | 223163535 | Hyper | cancer_general | CCDC140, DD413687, PAX3 |
| chr2 | 223163768 | 223163954 | Hyper | cancer_general | CCDC140, DD413687, PAX3 | chr2 | 223164534 | 223164883 | Hyper | cancer_general, literature | CCDC140, DD413687, PAX3 |
| chr2 | 223165434 | 223165832 | Hyper | cancer_general, lung | DD413687, PAX3, CCDC140 | chr2 | 223166449 | 223166721 | Hyper | cancer_general | CCDC140, DD413687, PAX3 |
| chr2 | 223167389 | 223167573 | Hyper | cancer_general | PAX3, CCDC140, DD413687 | chr2 | 223168437 | 223168852 | Hyper | cancer_general | CCDC140, DD413687, PAX3 |
| chr2 | 223169640 | 223169864 | Hyper | lung, cancer_general | CCDC140, DD413687, PAX3 | chr2 | 223170375 | 223170434 | Hyper | cancer_general | CCDC140, DD413687, PAX3 |
| chr2 | 223171109 | 223171180 | Hyper | cancer_general | CCDC140, DD413687, PAX3 | chr2 | 223172337 | 223172367 | Hyper | lung | CCDC140, DD413687, PAX3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 223172924 | 223173173 | Hyper | cancer_general | CCDC140, DD413687, PAX3 | chr2 | 223175663 | 223176181 | Hyper | cancer_general, lung | LOC440934, CCDC140 |
| chr2 | 223176456 | 223176983 | Hyper | cancer_general | LOC440934, CCDC140 | chr2 | 223177315 | 223177610 | Hyper | cancer_general | LOC440934, CCDC140 |
| chr2 | 224903260 | 224903440 | Hyper | esophageal | SERPINE2 | chr2 | 224903690 | 224903755 | Hyper | esophageal | SERPINE2 |
| chr2 | 224904108 | 224904237 | Hyper | esophageal | SERPINE2 | chr2 | 228029418 | 228029531 | Hyper | tcga, esophageal | COL4A3 |
| chr2 | 228736215 | 228736473 | Hyper | liver_tcga, cancer_general, tcga | DAW1 | chr2 | 229046107 | 229046503 | Hyper | cancer_general | SPHKAP |
| chr2 | 231693216 | 231693268 | Hyper | cancer_general | CAB39 | chr2 | 232394970 | 232395061 | Hyper | liver_tcga | NMUR1 |
| chr2 | 232479822 | 232479938 | Hyper | tcga | | chr2 | 232791704 | 232792012 | Hyper | tcga, cancer_general | NPPC |
| chr2 | 233350208 | 233351394 | Hyper | cancer_general, tcga, cancer_general | ECEL1 EFHD1 | chr2 | 233352025 | 233352853 | Hyper | cancer_general | ECEL1 |
| chr2 | 233498710 | 233499297 | Hyper | | | chr2 | 235404545 | 235404575 | Hyper | cancer_general | ARL4C |
| chr2 | 235860746 | 235860808 | Hyper | blood | SH3BP4 | chr2 | 235861389 | 235861533 | Hyper | blood | SH3BP4 |
| chr2 | 236402771 | 236403013 | Hyper | blood | AGAP1 | chr2 | 236403270 | 236403736 | Hyper | blood | AGAP1 |
| chr2 | 236578362 | 236578677 | Hyper | blood | AGAP1 | chr2 | 237072413 | 237073030 | Hyper | tcga, cancer_general | GBX2 |
| chr2 | 237073354 | 237073414 | Hyper | cancer_general | GBX2 | chr2 | 237076725 | 237076815 | Hyper | liver_tcga | GBX2 |
| chr2 | 237077562 | 237077608 | Hyper | cancer_general | GBX2 | chr2 | 237077846 | 237078348 | Hyper | cancer_general | GBX2 |
| chr2 | 237080264 | 237080294 | Hyper | cancer_general | GBX2 | chr2 | 237081341 | 237081826 | Hyper | cancer_general | GBX2 |
| chr2 | 237082117 | 237082720 | Hyper | cancer_general | GBX2 | chr2 | 237086349 | 237086468 | Hyper | cancer_general | GBX2 |
| chr2 | 237145422 | 237145601 | Hyper | tcga, cancer_general | ASB18 | chr2 | 237416216 | 237416429 | Hyper | cancer_general | IQCA1 |
| chr2 | 238395291 | 238395356 | Hyper | cancer_general | MLPH | chr2 | 238395906 | 238395961 | Hyper | blood | MLPH |
| chr2 | 238535895 | 238536114 | Hyper | tcga | LRRFIP1 | chr2 | 238864644 | 238864913 | Hyper | cancer_general | — |
| chr2 | 239072648 | 239072692 | Hyper | pancreas | FAM132B, ILKAP | chr2 | 239140025 | 239140249 | Hyper | cancer_general | LOC643387, HES6, LOC151174 |
| chr2 | 239149844 | 239149951 | Hyper | tcga | PER2, HES6, LOC643387, LOC151174 | chr2 | 239755164 | 239755194 | Hyper | cancer_general | TWIST2 |
| chr2 | 239755736 | 239755778 | Hyper | cancer_general | TWIST2 | chr2 | 239756373 | 239756648 | Hyper | cancer_general | TWIST2 |
| chr2 | 239757636 | 239757824 | Hyper | cancer_general | TWIST2 | chr2 | 239758078 | 239758144 | Hyper | cancer_general | TWIST2 |
| chr2 | 239758345 | 239758394 | Hyper | cancer_general | TWIST2 | chr2 | 241393200 | 241393469 | Hyper | cancer_general | MIR149, PP14571, GPC1 |
| chr2 | 241497411 | 241497554 | Hyper | liver_tcga | DUSP28, ANKMY1 | chr2 | 241758377 | 241758819 | Hyper | literature, cancer_general | KIF1A |
| chr2 | 241759597 | 241759694 | Hyper | cancer_general | KIF1A | chr2 | 241760149 | 241760178 | Hyper | literature | KIF1A |
| chr2 | 241760494 | 241760523 | Hyper | literature | KIF1A | chr2 | 241771165 | 241771257 | Hyper | cancer_general | — |
| chr2 | 242549849 | 242549957 | Hyper | tcga | — | HPV16 | 111 | 140 | Hyper | virus | — |
| HPV16 | 367 | 396 | Hyper | virus | — | HPV16 | 623 | 652 | Hyper | virus | — |
| HPV16 | 879 | 908 | Hyper | virus | — | HPV16 | 1135 | 1164 | Hyper | virus | — |
| HPV16 | 1391 | 1420 | Hyper | virus | — | HPV16 | 1647 | 1676 | Hyper | virus | — |
| HPV16 | 1903 | 1932 | Hyper | virus | — | HPV16 | 2159 | 2188 | Hyper | virus | — |
| HPV16 | 2415 | 2444 | Hyper | virus | — | HPV16 | 2671 | 2700 | Hyper | virus | — |

TABLE 11-continued

| chr | Start | Stop | Hypo/hyper | classification | annotation |
|---|---|---|---|---|---|
| HPV16 | 2927 | 2956 | Hyper | virus | — |
| HPV16 | 3183 | 3212 | Hyper | virus | — |
| HPV16 | 3439 | 3468 | Hyper | virus | — |
| HPV16 | 3695 | 3724 | Hyper | virus | — |
| HPV16 | 3951 | 3980 | Hyper | virus | — |
| HPV16 | 4207 | 4236 | Hyper | virus | — |
| HPV16 | 4463 | 4492 | Hyper | virus | — |
| HPV16 | 4719 | 4748 | Hyper | virus | — |
| HPV16 | 4975 | 5004 | Hyper | virus | — |
| HPV16 | 5231 | 5260 | Hyper | virus | — |
| HPV16 | 5487 | 5516 | Hyper | virus | — |
| HPV16 | 5743 | 5772 | Hyper | virus | — |
| HPV16 | 5999 | 6028 | Hyper | virus | — |
| HPV16 | 6255 | 6284 | Hyper | virus | — |
| HPV16 | 6511 | 6540 | Hyper | virus | — |
| HPV16 | 6767 | 6796 | Hyper | virus | — |
| HPV16 | 7023 | 7052 | Hyper | virus | — |
| HPV16 | 7279 | 7308 | Hyper | virus | — |
| HPV16 | 7535 | 7564 | Hyper | virus | — |
| chr17 | 1082884 | 1083002 | Hyper | liver_tcga | SLC43A2 |
| chr17 | 1173996 | 1174413 | Hyper | cancer_general | TUSC5, BHLHA9 |
| chr17 | 1494550 | 1494613 | Hyper | pancreas | CLUH |
| chr17 | 1959468 | 1959520 | Hyper | cancer_general | MIR132, HIC1, SMG6, AX747853, MIR212 |
| chr17 | 2607905 | 2607986 | Hyper | liver_tcga | — |
| chr17 | 3438914 | 3438959 | Hyper | cancer_general | TRPV3 |
| chr17 | 3658490 | 3658519 | Hyper | liver_tcga | — |
| chr17 | 4544607 | 4544710 | Hyper | cancer_general | ALOX15 |
| chr17 | 4891276 | 4891305 | Hyper | tcga | KIF1C, CAMTA2, INCA1, ZNF232, ZFP3 |
| chr17 | 4891527 | 4891556 | Hyper | tcga | KIF1C, INCA1, CAMTA2, ZNF232, ZFP3 |
| chr17 | 5000428 | 5000790 | Hyper | cancer_general | — |
| chr17 | 5001032 | 5001061 | Hyper | liver_tcga | SLC13A5 |
| chr17 | 5019637 | 5019761 | Hyper | liver_tcga | ZNF232, USP6 |
| chr17 | 6616637 | 6616686 | Hyper | cancer_general | FBXO39, XAF1 |
| chr17 | 6616911 | 6617192 | Hyper | liver_tcga, cancer_general | SLC13A5 |
| chr17 | 6679190 | 6679296 | Hyper | cancer_general | CHRNB1, FGF11, TMEM102 |
| chr17 | 6946107 | 6946141 | Hyper | cancer_general | SLC16A11, SLC16A13 |
| chr17 | 7348885 | 7348997 | Hyper | head_neck | HV941478, HV941442, HV941433, HV941434, HV941486, HV941440, HV941444, HV941430, HV941431, HV941428, TP53, HV941429 |
| chr17 | 7555117 | 7555425 | Hyper | tcga | TP53, ATP1B2 |
| chr17 | 7572957 | 7573018 | Hyper | literature | HV941430, HV941431, HV941428, TP53, HV941429, |
| chr17 | 7573968 | 7574028 | Hyper | literature | HV941428, HV941434, TP53, HV941478, HV941442, HV941444, HV941433, HV941486, HV941429, HV941440, HV941430, HV941431 |
| chr17 | 7576847 | 7577167 | Hyper | literature | HV941430, HV941431, HV941428, TP53, HV941429, |
| chr17 | 7577504 | 7577604 | Hyper | literature | HV941429, HV941440, HV941478, HV941442, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| | | | | | HV941440, HV941478, HV941442, HV941433, HV941434, HV941486, HV941444 | | | | | | HV941430, HV941428, HV941433, HV941431, HV941444, HV941486, HV941434 |
| chr17 | 7578164 | 7578570 | Hyper | literature | HV941478, HV941444, TP53, HV941429, HV941434, HV941440, HV941442, HV941430, HV941486, HV941428, HV941433, HV941431 | chr17 | 7579285 | 7579880 | Hyper | literature | WRAP53, HV941442, HV941440, HV941429, HV941428, TP53, HV941430, HV941486, HV941434, HV941433, HV941431, HV941444 |
| chr17 | 7906254 | 7906535 | Hyper | tcga, cancer_general | GUCY2D | chr17 | 8230335 | 8230694 | Hyper | cancer_general, tcga | ARHGEF15 |
| chr17 | 8534493 | 8534582 | Hyper | esophageal | — | chr17 | 8868620 | 8869385 | Hyper | cancer_general | PIK3R5 |
| chr17 | 8906266 | 8906518 | Hyper | cancer_general | — | chr17 | 8906993 | 8907575 | Hyper | tcga, cancer_general | — |
| chr17 | 8926060 | 8926263 | Hyper | tcga, cancer_general | NTN1 | chr17 | 10101084 | 10101984 | Hyper | cancer_general | — |
| chr17 | 10102415 | 10102665 | Hyper | tcga, cancer_general | — | chr17 | 11144167 | 11144320 | Hyper | cancer_general | SHISA6 |
| chr17 | 11144926 | 11144989 | Hyper | cancer_general | SHISA6 | chr17 | 11984693 | 11984722 | Hyper | literature | MIR744, MAP2K4 |
| chr17 | 11998944 | 11998973 | Hyper | literature | — | chr17 | 12013726 | 12013755 | Hyper | literature | — |
| chr17 | 12016550 | 12016630 | Hyper | literature | — | chr17 | 12028618 | 12028647 | Hyper | literature | — |
| chr17 | 13503972 | 13504195 | Hyper | cancer_general | HS3ST3A1 | chr17 | 13504557 | 13504681 | Hyper | cancer_general | HS3ST3A1 |
| chr17 | 13504975 | 13505188 | Hyper | tcga, cancer_general | HS3ST3A1 | chr17 | 13505418 | 13505572 | Hyper | cancer_general | HS3ST3A1 |
| chr17 | 14201041 | 14201181 | Hyper | cancer_general | HS3ST3B1, MGC12916, HS3ST3B1 | chr17 | 14204212 | 14204242 | Hyper | cancer_general esophageal | MGC12916, HS3ST3B1 |
| chr17 | 14204527 | 14204620 | Hyper | esophageal | MGC12916, HS3ST3B1 | chr17 | 15245050 | 15245139 | Hyper | cancer_general | TEKT3 |
| chr17 | 16284630 | 16285065 | Hyper | ovarian | UBB | chr17 | 16570699 | 16570794 | Hyper | cancer_general | — |
| chr17 | 17398404 | 17398440 | Hyper | pancreas | MED9, RASD1 | chr17 | 18538154 | 18538275 | Hyper | cancer_general | TBC1D28, CCDC144B |
| chr17 | 26554634 | 26554705 | Hyper | cancer_general | PYY2 | chr17 | 27038649 | 27038900 | Hyper | cancer_general, tcga | RAB34, NARR, RPL23A, SNORD42B, PROCA1 |
| chr17 | 27044770 | 27044800 | Hyper | colorectal | SNORD42A, SNORD4B, NARR, | chr17 | 27332453 | 27332660 | Hyper | cancer_general | SEZ6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 27940359 | 27940911 | Hyper | cancer_general | RAB34, PROCA1, RPL23A, SNORD42B, SNORD4A, TLCD1 | chr17 | 28562701 | 28562765 | Hyper | cancer_general | SLC6A4 |
| chr17 | 29249717 | 29249930 | Hyper | cancer_general | CORO6, ANKRD13B ADAP2 | chr17 | 29298080 | 29298581 | Hyper | tcga, liver_tcga, hepatobiliary | DPRXP4, RNF135 |
| chr17 | 29508761 | 29508790 | Hyper | literature | NF1 | chr17 | 29541527 | 29541556 | Hyper | literature | NF1 |
| chr17 | 29562732 | 29562761 | Hyper | literature | NF1 | chr17 | 29718215 | 29718269 | Hyper | cancer_general | RAB11FIP4 |
| chr17 | 29719187 | 29719242 | Hyper | cancer_general | RAB11FIP4 | chr17 | 31618425 | 31619319 | Hyper | cancer_general | ASIC2 |
| chr17 | 31619951 | 31620026 | Hyper | cancer_general | ASIC2 | chr17 | 32484020 | 32484049 | Hyper | literature | — |
| chr17 | 32906379 | 32906636 | Hyper | tcga | TMEM132E, C17orf102 | chr17 | 32906987 | 32907146 | Hyper | tcga | TMEM132E, C17orf102 |
| chr17 | 32907652 | 32907753 | Hyper | cancer_general | TMEM132E, C17orf102 | chr17 | 32908132 | 32908374 | Hyper | colorectal, cancer_general | TMEM132E, C17orf102 |
| chr17 | 32908647 | 32908931 | Hyper | cancer_general | TMEM132E | chr17 | 33288229 | 33288351 | Hyper | esophageal | ZNF830, CCT6B |
| chr17 | 33288890 | 33288988 | Hyper | esophageal | CCT6B, ZNF830 | chr17 | 33672916 | 33672986 | Hyper | cancer_general | SLFN11 |
| chr17 | 35165645 | 35165691 | Hyper | cancer_general | — | chr17 | 35165986 | 35166016 | Hyper | cancer_general | — |
| chr17 | 35285542 | 35285666 | Hyper | cancer_general | BC084573, LHX1 | chr17 | 35290388 | 35290655 | Hyper | cancer_general | BC084573, LHX1 |
| chr17 | 35291320 | 35291354 | Hyper | cancer_general | LHX1, BC084573 | chr17 | 35291829 | 35292626 | Hyper | cancer_general | BC084573, LHX1 |
| chr17 | 35293704 | 35294154 | Hyper | tcga, cancer_general | LHX1, BC084573 | chr17 | 35294461 | 35294505 | Hyper | literature | LHX1, BC084573 |
| chr17 | 35295047 | 35295160 | Hyper | cancer_general | LHX1, BC084573 | chr17 | 35296143 | 35296292 | Hyper | cancer_general | AATF, LHX1, BC084573 |
| chr17 | 35296728 | 35296888 | Hyper | cancer_general | AATF, LHX1, BC084573 | chr17 | 35297619 | 35298153 | Hyper | cancer_general | BC084573, AATF, LHX1 |
| chr17 | 35299251 | 35300854 | Hyper | cancer_general, literature | LHX1, BC084573, AATF | chr17 | 35303340 | 35303535 | Hyper | cancer_general | AATF, LHX1, BC084573 |
| chr17 | 35872722 | 35872861 | Hyper | liver_tcga | SYNRG, DUSP14 | chr17 | 36103021 | 36103326 | Hyper | tcga, cancer_general | HNF1B |
| chr17 | 36103571 | 36103601 | Hyper | cancer_general | HNF1B | chr17 | 36104120 | 36104779 | Hyper | cancer_general | — |
| chr17 | 36105223 | 36105596 | Hyper | cancer_general | — | chr17 | 36715772 | 36715967 | Hyper | tcga | SRCIN1 |
| chr17 | 37321186 | 37321972 | Hyper | tcga, cancer_general | CACNB1, ARL5C | chr17 | 37366337 | 37366552 | Hyper | cancer_general | STAC2, RPL19 |
| chr17 | 37381011 | 37381850 | Hyper | tcga, literature, cancer_general | STAC2 | chr17 | 37382146 | 37382248 | Hyper | literature | STAC2 |
| chr17 | 37757153 | 37757217 | Hyper | lung | NEUROD2 | chr17 | 37760488 | 37760561 | Hyper | cancer_general | NEUROD2 |
| chr17 | 37761997 | 37762334 | Hyper | cancer_general | NEUROD2 | chr17 | 37868190 | 37868294 | Hyper | literature | ERBB2 |
| chr17 | 37879568 | 37879615 | Hyper | literature | MIR4728, MIEN1, | chr17 | 37880205 | 37880276 | Hyper | literature | MIR4728, MIEN1, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 37880971 | 37881018 | Hyper | literature | ERBB2, MIR4728, MIEN1, ERBB2 | chr17 | 37881318 | 37881631 | Hyper | literature | ERBB2, MIR4728, MIEN1, ERBB2 |
| chr17 | 38347560 | 38347624 | Hyper | cancer_general | RAPGEFL1 | chr17 | 38474363 | 38474502 | Hyper | literature | RARA |
| chr17 | 38497616 | 38497645 | Hyper | literature | RARA | chr17 | 38498083 | 38498112 | Hyper | literature | RARA, GJD3, RARA |
| chr17 | 38504087 | 38504116 | Hyper | literature | RARA | chr17 | 38510555 | 38510584 | Hyper | liver_tcga | STAT5B |
| chr17 | 40332943 | 40333226 | Hyper | tcga, esophageal | HCRT, GHDC, KCNH4 | chr17 | 40400867 | 40401031 | Hyper | cancer_general | AK024535, STAT3, AK092965, STAT5A |
| chr17 | 40464278 | 40464317 | Hyper | cancer_general | AK024535, STAT3, AK092965, STAT5A | chr17 | 40464517 | 40464607 | Hyper | cancer_general | CNTNAP1, PLEKHH3, TUBG2, CCR10 |
| chr17 | 40474467 | 40474496 | Hyper | literature | AK092965, STAT3, AK024535 | chr17 | 40826197 | 40826226 | Hyper | liver_tcga | CCR10, PLEKHH3, CNTNAP1 |
| chr17 | 40837022 | 40837051 | Hyper | liver_tcga | PLEKHH3, CNTNAP1, CCR10 | chr17 | 40837287 | 40837383 | Hyper | liver_tcga | RND2, VAT1 |
| chr17 | 40838982 | 40839022 | Hyper | liver_tcga | CNTNAP1, CCR10, PLEKHH3 | chr17 | 41177394 | 41177459 | Hyper | tcga | |
| chr17 | 41197714 | 41197743 | Hyper | literature | BRCA1 | chr17 | 41201163 | 41201192 | Hyper | literature | BRCA1 |
| chr17 | 41203073 | 41203102 | Hyper | literature | BRCA1 | chr17 | 41209064 | 41209114 | Hyper | literature | BRCA1 |
| chr17 | 41215890 | 41215961 | Hyper | literature | BRCA1 | chr17 | 41267731 | 41267775 | Hyper | literature | NBR2, BRCA1 |
| chr17 | 41276031 | 41276075 | Hyper | literature | BRCA1, NBR2 | chr17 | 41277259 | 41277721 | Hyper | literature | NBR2, BRCA1 |
| chr17 | 41791460 | 41791489 | Hyper | tcga | — | chr17 | 42030329 | 42030756 | Hyper | liver_tcga, cancer_general | PYY |
| chr17 | 42061336 | 42061381 | Hyper | blood | — | chr17 | 42082522 | 42082557 | Hyper | cancer_general | NAGS, TMEM101 |
| chr17 | 42084361 | 42084626 | Hyper | tcga | TMEM101, NAGS | chr17 | 42092190 | 42092220 | Hyper | breast | TMEM101, NAGS |
| chr17 | 42393842 | 42394024 | Hyper | cancer_general | SLC25A39, RUNDC3A, AK055254 | chr17 | 42402884 | 42402917 | Hyper | hepatobiliary | SLC25A39, RUNDC3A |
| chr17 | 42635295 | 42635760 | Hyper | tcga, cancer_general, esophageal | FZD2 | chr17 | 42733711 | 42733884 | Hyper | cancer_general, liver_tcga | C17orf104 |
| chr17 | 42907564 | 42907951 | Hyper | cancer_general | — | chr17 | 43037399 | 43037429 | Hyper | cancer_general | C1QL1 |
| chr17 | 43044658 | 43044688 | Hyper | cancer_general | C1QL1 | chr17 | 43044999 | 43045116 | Hyper | liver_tcga, cancer_general | C1QL1 |
| chr17 | 43046260 | 43046385 | Hyper | tcga | C1QL1 | chr17 | 43047436 | 43047751 | Hyper | liver_tcga, cancer_general | C1QL1 |
| chr17 | 43339109 | 43339333 | Hyper | cancer_general | MAP3K14-AS1, | chr17 | 43339609 | 43339899 | Hyper | cancer_general | MAP3K14, MAP3K14- |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 43974256 | 43974358 | Hyper | cancer_general | MAP3K14, SPATA32 | chr17 | 45331014 | 45331313 | Hyper | esophageal | AS1, SPATA32 |
| chr17 | 45810850 | 45811341 | Hyper | tcga, cancer_general | MAPT-IT1, MAPT TBX21 | chr17 | 45867315 | 45867460 | Hyper | tcga | ITGB3 |
| chr17 | 46124991 | 46125061 | Hyper | colorectal | NFE2L1 | chr17 | 46619298 | 46619327 | Hyper | tcga | — |
| chr17 | 46619540 | 46619569 | Hyper | tcga | HOXB2, HOXB-AS1, HOXB3 | chr17 | 46620494 | 46621094 | Hyper | cancer_general | HOXB3, HOXB2, HOXB-AS1, HOXB3, HOXB2 |
| chr17 | 46621353 | 46621458 | Hyper | cancer_general | HOXB-AS1, HOXB3, HOXB2 | chr17 | 46621856 | 46621909 | Hyper | cancer_general | HOXB3, HOXB-AS1, HOXB2 |
| chr17 | 46655148 | 46655178 | Hyper | lung | MIR10A, HOXB4, HOXB3 | chr17 | 46654435 | 46656704 | Hyper | tcga, cancer_general, literature | MIR10A, HOXB4, HOXB3 |
| chr17 | 46659429 | 46659859 | Hyper | cancer_general | HOXB-AS3, HOXB5, MIR10A, HOXB4, HOXB3 | chr17 | 46663743 | 46663887 | Hyper | tcga, cancer_general | HOXB5, HOXB6, MIR10A, HOXB4, HOXB-AS3 |
| chr17 | 46674873 | 46674970 | Hyper | cancer_general | HOXB7, HOXB-AS3, HOXB6, HOXB5 | chr17 | 46675170 | 46675600 | Hyper | lung, cancer_general | HOXB7, HOXB-AS3, HOXB6, HOXB5 |
| chr17 | 46690467 | 46690664 | Hyper | cancer_general | HOXB9, HOXB8, HOXB7 | chr17 | 46691505 | 46691592 | Hyper | cancer_general | HOXB9, HOXB8, HOXB7 |
| chr17 | 46691805 | 46692110 | Hyper | tcga, lung, cancer_general | HOXB9, HOXB8, HOXB7 | chr17 | 46692439 | 46692606 | Hyper | tcga | HOXB9, HOXB8, HOXB7 |
| chr17 | 46710946 | 46711065 | Hyper | literature, cancer_general, tcga | MIR196A1, HOXB9 | chr17 | 46711281 | 46711375 | Hyper | tcga, literature, cancer_general | MIR196A1, HOXB9 |
| chr17 | 46713959 | 46714072 | Hyper | cancer_general | MIR196A1 | chr17 | 46795641 | 46797582 | Hyper | cancer_general | PRAC, HOXB-AS5, MIR3185, HOXB13 |
| chr17 | 46799625 | 46799896 | Hyper | literature, cancer_general | HOXB-AS5, MIR3185, HOXB13, PRAC | chr17 | 46800601 | 46800668 | Hyper | cancer_general | MIR3185, HOXB13, HOXB-AS5, PRAC |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 46800961 | 46801416 | Hyper | lung, cancer_general | HOXB-AS5, PRAC, MIR3185, HOXB13 | chr17 | 46802459 | 46803286 | Hyper | cancer_general | HOXB13, MIR3185, HOXB-AS5, PRAC |
| chr17 | 46804107 | 46804428 | Hyper | cancer_general | HOXB13, MIR3185, HOXB-AS5, PRAC | chr17 | 46810416 | 46810958 | Hyper | cancer_general | HOXB13, MIR3185 |
| chr17 | 46811354 | 46811541 | Hyper | cancer_general | HOXB13, MIR3185, HOXB-AS5 | chr17 | 46816282 | 46816877 | Hyper | cancer_general | — |
| chr17 | 46824224 | 46825054 | Hyper | cancer_general | — | chr17 | 46825284 | 46825514 | Hyper | cancer_general | — |
| chr17 | 46826930 | 46827127 | Hyper | cancer_general | — | chr17 | 46827330 | 46827756 | Hyper | cancer_general | — |
| chr17 | 46829498 | 46829579 | Hyper | cancer_general | — | chr17 | 46829979 | 46830110 | Hyper | cancer_general | TTLL6 |
| chr17 | 46831779 | 46832639 | Hyper | cancer_general | TTLL6 | chr17 | 47072805 | 47073465 | Hyper | cancer_general | IGF2BP1 |
| chr17 | 47073988 | 47074228 | Hyper | cancer_general | IGF2BP1 | chr17 | 47074561 | 47074895 | Hyper | cancer_general, tcga | IGF2BP1 |
| chr17 | 47075160 | 47075364 | Hyper | tcga, cancer_general | IGF2BP1 | chr17 | 47075715 | 47076055 | Hyper | tcga, cancer_general | IGF2BP1 |
| chr17 | 47574090 | 47574149 | Hyper | colorectal | NGFR | chr17 | 47865514 | 47865555 | Hyper | cancer_general | KAT7, FAM117A |
| chr17 | 47987525 | 47987619 | Hyper | cancer_general | — | chr17 | 47987930 | 47988114 | Hyper | cancer_general | — |
| chr17 | 48041152 | 48041320 | Hyper | cancer_general | DLX4 | chr17 | 48041672 | 48041721 | Hyper | cancer_general | DLX4 |
| chr17 | 48042039 | 48042069 | Hyper | cancer_general | DLX4 | chr17 | 48042435 | 48042956 | Hyper | cancer_general | DLX4 |
| chr17 | 48048952 | 48049059 | Hyper | cancer_general | DLX3 | chr17 | 48049307 | 48050526 | Hyper | cancer_general | DLX3 |
| chr17 | 48071020 | 48071050 | Hyper | esophageal | ACSF2, CHAD | chr17 | 48071791 | 48071894 | Hyper | cancer_general | DLX3 |
| chr17 | 48545804 | 48545950 | Hyper | liver_tcga | | chr17 | 48636581 | 48637136 | Hyper | liver_tcga, cancer_general | CACNA1G, CACNA1G-AS1, SPATA20 |
| chr17 | 49027838 | 49027876 | Hyper | head_neck | | chr17 | 50235216 | 50235274 | Hyper | cancer_general | CA10 |
| chr17 | 50235631 | 50235952 | Hyper | cancer_general | CA10 | chr17 | 51901004 | 51901034 | Hyper | esophageal tcga, cancer_general | KIF2B |
| chr17 | 53341252 | 53341536 | Hyper | cancer_general | HLF | chr17 | 53342876 | 53343089 | Hyper | cancer_general | HLF |
| chr17 | 53922649 | 53922790 | Hyper | cancer_general | — | chr17 | 54674986 | 54675272 | Hyper | tcga, cancer_general | NOG |
| chr17 | 54755969 | 54756014 | Hyper | cancer_general | — | chr17 | 55122813 | 55122842 | Hyper | literature | RNF126P1 |
| chr17 | 55213641 | 55213670 | Hyper | literature | — | chr17 | 55962573 | 55962841 | Hyper | liver_tcga | CUEDC1 |
| chr17 | 56234405 | 56234743 | Hyper | cancer_general | MSX2P1, OR4D1 | chr17 | 56326949 | 56326994 | Hyper | cancer_general | LPO |
| chr17 | 56327271 | 56327301 | Hyper | esophageal | LPO | chr17 | 56833127 | 56833221 | Hyper | cancer_general | PPM1E |
| chr17 | 56833707 | 56834075 | Hyper | esophageal tcga, esophageal | PPM1E | chr17 | 56834306 | 56834375 | Hyper | tcga | PPM1E |
| chr17 | 58216613 | 58217551 | Hyper | cancer_general | CA4 | chr17 | 58218765 | 58218993 | Hyper | cancer_general tcga | CA4 |
| chr17 | 58227374 | 58227426 | Hyper | cancer_general | CA4 | chr17 | 58498697 | 58499314 | Hyper | cancer_general tcga, cancer_general | CA4 C17orf64 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 59474157 | 59474620 | Hyper | cancer_general | TBX2, BCAS3 | chr17 | 59474833 | 59475100 | Hyper | cancer_general | TBX2, BCAS3 |
| chr17 | 59475678 | 59476127 | Hyper | cancer_general | BCAS3, TBX2 | chr17 | 59476410 | 59476635 | Hyper | cancer_general | TBX2, BCAS3 |
| chr17 | 59478147 | 59478602 | Hyper | cancer_general | TBX2, BCAS3 | chr17 | 59488101 | 59488457 | Hyper | tcga | C17orf82, TBX2 |
| chr17 | 59528876 | 59530352 | Hyper | tcga, cancer_general | TBX4 | chr17 | 59531667 | 59532139 | Hyper | cancer_general | TBX4 |
| chr17 | 59533828 | 59534491 | Hyper | cancer_general | TBX4 | chr17 | 59534751 | 59534781 | Hyper | cancer_general | TBX4 |
| chr17 | 59535137 | 59535219 | Hyper | cancer_general | TBX4 | chr17 | 59539236 | 59539601 | Hyper | tcga, cancer_general, lung | TBX4 |
| chr17 | 59924556 | 59924585 | Hyper | literature | — | chr17 | 59937192 | 59937236 | Hyper | literature | INTS2 |
| chr17 | 61778085 | 61778300 | Hyper | cancer_general | STRADA, LOC729683, LIMD2, MAP3K3 | chr17 | 61926172 | 61926603 | Hyper | cancer_general | TCAM1P |
| chr17 | 62777335 | 62777450 | Hyper | hepatobiliary | PLEKHM1P, LOC146880 | chr17 | 62777746 | 62777791 | Hyper | tcga | PLEKHM1P, LOC146880 |
| chr17 | 66596471 | 66596525 | Hyper | cancer_general | FAM20A | chr17 | 66596984 | 66597021 | Hyper | tcga | FAM20A |
| chr17 | 68164733 | 68164928 | Hyper | tcga, cancer_general | KCNJ2, KCNJ2-AS1 | chr17 | 70026543 | 70026667 | Hyper | cancer_general, breast | D43770 |
| chr17 | 70112916 | 70114517 | Hyper | cancer_general | AK094963, SOX9, AL833139 | chr17 | 70215683 | 70216585 | Hyper | cancer_general | — |
| chr17 | 71641544 | 71641683 | Hyper | cancer_general | — | chr17 | 71948439 | 71948863 | Hyper | cancer_general | KIF19 |
| chr17 | 72270286 | 72270415 | Hyper | cancer_general | DNAI2 | chr17 | 72321933 | 72321975 | Hyper | cancer_general | BTBD17, KIF19 |
| chr17 | 72322363 | 72322604 | Hyper | cancer_general | KIF19 | chr17 | 72353213 | 72353550 | Hyper | cancer_general, tcga | KIF19 |
| chr17 | 72427853 | 72427999 | Hyper | blood | GPRC5C | chr17 | 72428344 | 72428381 | Hyper | blood | GPRC5C |
| chr17 | 72667337 | 72667565 | Hyper | cancer_general | RAB37 | chr17 | 72849010 | 72849079 | Hyper | cancer_general | FDXR, GRIN2C |
| chr17 | 72857038 | 72857368 | Hyper | cancer_general, tcga | FDXR, GRIN2C | chr17 | 72920796 | 72921032 | Hyper | cancer_general | USH1G, OTOP2 |
| chr17 | 73073684 | 73073954 | Hyper | tcga, cancer_general | SLC16A5 | chr17 | 73584821 | 73584883 | Hyper | cancer_general | MYO15B |
| chr17 | 73709838 | 73709955 | Hyper | cancer_general | ITGB4, SAP30BP | chr17 | 74070281 | 74070582 | Hyper | cancer_general | SRP68, GALR2, ZACN, EXOC7 |
| chr17 | 74071445 | 74071481 | Hyper | cancer_general | ZACN, EXOC7, GALR2, SRP68 | chr17 | 74071689 | 74071729 | Hyper | cancer_general | ZACN, EXOC7, GALR2, SRP68 |
| chr17 | 74072941 | 74073036 | Hyper | cancer_general | ZACN, EXOC7, GALR2, SRP68 | chr17 | 74073269 | 74073433 | Hyper | cancer_general | SRP68, GALR2, ZACN, EXOC7 |
| chr17 | 74533844 | 74534310 | Hyper | tcga, liver_tcga, cancer_general | PRCD, CYGB | chr17 | 74581182 | 74581221 | Hyper | cancer_general | ST6GALNAC2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 74732944 | 74732973 | Hyper | literature | MFSD11, MIR636, SRSF2, METTL23 | chr17 | 74865053 | 74865192 | Hyper | tcga | MGAT5B, BC038218 |
| chr17 | 74865698 | 74866243 | Hyper | cancer_general | MGAT5B, BC038218 | chr17 | 75137660 | 75137887 | Hyper | tcga | SEC14L1 |
| chr17 | 75315512 | 75315681 | Hyper | literature | 9-Sep | chr17 | 75368735 | 75369238 | Hyper | literature, tcga, liver_tcga, cancer_general | 9-Sep |
| chr17 | 75369440 | 75369860 | Hyper | liver_tcga, literature, cancer_general | 9-Sep | chr17 | 75370269 | 75370316 | Hyper | literature, cancer_general | 9-Sep |
| chr17 | 75370596 | 75370625 | Hyper | liver_tcga, literature | 9-Sep | chr17 | 75385071 | 75385446 | Hyper | literature | MIR4316, SEPT9 |
| chr17 | 75417150 | 75417179 | Hyper | literature | 9-Sep | chr17 | 75524636 | 75525194 | Hyper | tcga, cancer_general | BC040189 |
| chr17 | 76125196 | 76125225 | Hyper | literature | TMC8, TMC6 | chr17 | 76126434 | 76126463 | Hyper | literature | TMC8, TMC6 |
| chr17 | 76128466 | 76128690 | Hyper | literature | TMC8, TMC6 | chr17 | 76130481 | 76130510 | Hyper | literature | TMC8, TMC6 |
| chr17 | 76227849 | 76228357 | Hyper | tcga, cancer_general | TMEM235, EPR-1, BIRC5 | chr17 | 76921830 | 76921859 | Hyper | literature | — |
| chr17 | 77179113 | 77179278 | Hyper | cancer_general | RBFOX3 | chr17 | 77179630 | 77179792 | Hyper | tcga, cancer_general | RBFOX3 |
| chr17 | 77776827 | 77777056 | Hyper | cancer_general | CBX8 | chr17 | 77777585 | 77777961 | Hyper | tcga, cancer_general | CBX8 |
| chr17 | 77778943 | 77779179 | Hyper | cancer_general | CBX8 | chr17 | 77788841 | 77788969 | Hyper | cancer_general | — |
| chr17 | 77789296 | 77789500 | Hyper | cancer_general | — | chr17 | 77899664 | 77899693 | Hyper | liver_tcga | TBC1D16, BC044939 |
| chr17 | 78451931 | 78452051 | Hyper | cancer_general | NPTX1 | chr17 | 78452296 | 78452340 | Hyper | cancer_general | NPTX1 |
| chr17 | 78452681 | 78452833 | Hyper | cancer_general | NPTX1 | chr17 | 79058302 | 79058333 | Hyper | liver_tcga | BALAP2 |
| chr17 | 79615176 | 79615356 | Hyper | cancer_general | PDE6G, TSPAN10 | chr17 | 79813409 | 79813507 | Hyper | liver_tcga | P4HB |
| chr17 | 80186260 | 80186289 | Hyper | literature | SLC16A3 | chr17 | 80197756 | 80197898 | Hyper | liver_tcga | CSNK1D, SLC16A3 |
| chr17 | 80329709 | 80330085 | Hyper | liver_tcga, cancer_general | UTS2R, AF075112, TEX19 | chr17 | 80394573 | 80394602 | Hyper | liver_tcga | C17orf62, HEXDC |
| chr17 | 80693317 | 80693554 | Hyper | blood | FN3K, FN3KRP | chr12 | 570090 | 570171 | Hyper | cancer_general | B4GALNT3 |
| chr12 | 1639135 | 1639222 | Hyper | cancer_general | — | chr12 | 2162554 | 2162817 | Hyper | cancer_general | CACNA1C |
| chr12 | 2163164 | 2163276 | Hyper | cancer_general | CACNA1C | chr12 | 2862068 | 2862225 | Hyper | cancer_general | LOC283440 |
| chr12 | 3371882 | 3371911 | Hyper | liver_tcga | TSPAN9 | chr12 | 3373533 | 3373666 | Hyper | liver_tcga | TSPAN9 |
| chr12 | 3600315 | 3600345 | Hyper | cancer_general | AK125333, DQ579489, DQ583138, DQ596092, PRMT8 | chr12 | 3602270 | 3602879 | Hyper | cancer_general | PRMT8, AK125333, DQ579489 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 3603100 | 3603156 | Hyper | cancer_general | PRMT8, AK125333 | chr12 | 3862254 | 3862298 | Hyper | pancreas | EFCAB4B |
| chr12 | 4274054 | 4274188 | Hyper | cancer_general | — | chr12 | 4378252 | 4378330 | Hyper | tcga | CCND2 |
| chr12 | 4381433 | 4382386 | Hyper | literature, pancreas | CCND2 | chr12 | 4382965 | 4382999 | Hyper | literature | CCND2 |
| chr12 | 4383492 | 4383784 | Hyper | literature | CCND2 | chr12 | 4384389 | 4384418 | Hyper | literature | CCND2 |
| chr12 | 4384736 | 4384902 | Hyper | literature | CCND2 | chr12 | 4918986 | 4919244 | Hyper | tcga | KCNA6 |
| chr12 | 5018073 | 5018692 | Hyper | tcga, cancer_general | KCNA1 | chr12 | 5019050 | 5020416 | Hyper | tcga, cancer_general | KCNA1 |
| chr12 | 5153039 | 5153520 | Hyper | tcga, cancer_general | KCNA5 | chr12 | 5541100 | 5541177 | Hyper | pancreas | NTF3 |
| chr12 | 5542325 | 5542439 | Hyper | cancer_general | NTF3 | chr12 | 5542759 | 5542911 | Hyper | literature, tcga, cancer_general | NTF3 |
| chr12 | 6308743 | 6308772 | Hyper | literature | CD9 | chr12 | 6664508 | 6665384 | Hyper | cancer_general | NOP2, IFFO1 |
| chr12 | 8025631 | 8025660 | Hyper | literature | NANOGP1 | chr12 | 8171360 | 8171745 | Hyper | tcga, cancer_general | — |
| chr12 | 8549178 | 8549208 | Hyper | esophageal | LINC00937 | chr12 | 8850658 | 8850744 | Hyper | esophageal | RIMKLB |
| chr12 | 11653449 | 11653479 | Hyper | cancer_general | — | chr12 | 14133152 | 14133263 | Hyper | cancer_general | — |
| chr12 | 14133619 | 14133881 | Hyper | cancer_general | — | chr12 | 14135111 | 14135339 | Hyper | cancer_general | — |
| chr12 | 15374258 | 15374291 | Hyper | cancer_general | RERG | chr12 | 16500576 | 16500621 | Hyper | blood | MGST1 |
| chr12 | 19282333 | 19282363 | Hyper | blood | PLEKHA5 | chr12 | 20521704 | 20521841 | Hyper | cancer_general | PDE3A |
| chr12 | 20522457 | 20522487 | Hyper | cancer_general | PDE3A | chr12 | 20522769 | 20522891 | Hyper | cancer_general | PDE3A |
| chr12 | 21680394 | 21680683 | Hyper | tcga, cancer_general | C12orf39, GYS2, GOLT1B | chr12 | 21810264 | 21810868 | Hyper | tcga, liver_tcga | LDHB |
| chr12 | 22093825 | 22094810 | Hyper | literature, cancer_general | ABCC9 | chr12 | 22095095 | 22095136 | Hyper | cancer_general | ABCC9 |
| chr12 | 22486799 | 22487473 | Hyper | cancer_general, tcga, liver_tcga | ST8SIA1 | chr12 | 24714909 | 24714938 | Hyper | tcga | LINC00477 |
| chr12 | 24715235 | 24715264 | Hyper | tcga | LINC00477 | chr12 | 24716033 | 24716218 | Hyper | tcga | LINC00477 |
| chr12 | 25055952 | 25056436 | Hyper | liver_tcga, literature, cancer_general | BCAT1 | chr12 | 25101592 | 25101660 | Hyper | cancer_general | — |
| chr12 | 25101919 | 25102086 | Hyper | cancer_general | — | chr12 | 25362824 | 25362853 | Hyper | literature | KRAS, LYRM5 |
| chr12 | 25368463 | 25368492 | Hyper | literature | KRAS | chr12 | 25378543 | 25378662 | Hyper | literature | KRAS |
| chr12 | 25380231 | 25380299 | Hyper | literature | KRAS | chr12 | 25398203 | 25398319 | Hyper | literature | DD157417, KRAS |
| chr12 | 28123996 | 28124247 | Hyper | tcga | PTHLH | chr12 | 28127767 | 28128302 | Hyper | tcga, cancer_general, lung | PTHLH |
| chr12 | 28128547 | 28129084 | Hyper | lung, cancer_general | PTHLH | chr12 | 29936016 | 29936048 | Hyper | cancer_general | TMTC1 |
| chr12 | 29936602 | 29936864 | Hyper | tcga, cancer_general | TMTC1 | chr12 | 29937331 | 29937374 | Hyper | cancer_general | TMTC1 |
| chr12 | 30322774 | 30323517 | Hyper | cancer_general | — | chr12 | 30975572 | 30976030 | Hyper | tcga, cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 31079268 | 31079499 | Hyper | cancer_general | TSPAN11 | chr12 | 33591774 | 33591804 | Hyper | cancer_general | SYT10 |
| chr12 | 33592613 | 33592889 | Hyper | cancer_general | SYT10 | chr12 | 39299117 | 39299560 | Hyper | tcga, cancer_general | CPNE8 |
| chr12 | 39539353 | 39539436 | Hyper | cancer_general | — | chr12 | 40618404 | 40618470 | Hyper | cancer_general | LRRK2 |
| chr12 | 41086183 | 41086379 | Hyper | tcga | CNTN1 | chr12 | 41086784 | 41087106 | Hyper | cancer_general | CNTN1 |
| chr12 | 41582513 | 41582988 | Hyper | cancer_general | PDZRN4 | chr12 | 41583374 | 41583419 | Hyper | cancer_general | PDZRN4 |
| chr12 | 43944893 | 43945124 | Hyper | cancer_general | — | chr12 | 43945356 | 43945526 | Hyper | cancer_general | — |
| chr12 | 43945844 | 43946298 | Hyper | literature, cancer_general | — | chr12 | 45269504 | 45269624 | Hyper | tcga | NELL2 |
| chr12 | 45444118 | 45445258 | Hyper | cancer_general | DBX2 | chr12 | 46767650 | 46767697 | Hyper | tcga | SLC38A2 |
| chr12 | 47225381 | 47225579 | Hyper | cancer_general | SLC38A4 | chr12 | 48397195 | 48398070 | Hyper | cancer_general | COL2A1 |
| chr12 | 48398641 | 48398671 | Hyper | cancer_general | COL2A1 | chr12 | 48690674 | 48690929 | Hyper | tcga | — |
| chr12 | 49297802 | 49297915 | Hyper | cancer_general | CCDC65 | chr12 | 49366374 | 49366423 | Hyper | cancer_general | WNT1, WNT10B |
| chr12 | 49374914 | 49375119 | Hyper | cancer_general | WNT1, WNT10B | chr12 | 49375325 | 49375529 | Hyper | cancer_general, tcga | WNT1, WNT10B |
| chr12 | 49390873 | 49391877 | Hyper | cancer_general | PRKAG1, DDN | chr12 | 49691049 | 49691078 | Hyper | liver_tcga | PRPH |
| chr12 | 49727049 | 49727127 | Hyper | cancer_general | TROAP, C1QL4 | chr12 | 49729728 | 49730090 | Hyper | cancer_general | C1QL4, TROAP |
| chr12 | 49759530 | 49759559 | Hyper | literature | SPATS2 | chr12 | 50297497 | 50298055 | Hyper | cancer_general, literature, liver_tcga | FAIM2, LOC283332, BC034605 |
| chr12 | 50355275 | 50355469 | Hyper | cancer_general | AQP6, AQP2, AQP5 | chr12 | 50426748 | 50426799 | Hyper | cancer_general | RACGAP1 |
| chr12 | 52262983 | 52263106 | Hyper | cancer_general | — | chr12 | 52301280 | 52301367 | Hyper | cancer_general | ACVRL1 |
| chr12 | 52400831 | 52401537 | Hyper | tcga, liver_tcga, cancer_general | GRASP, ACVR1B | chr12 | 52408905 | 52409033 | Hyper | liver_tcga | NR4A1, GRASP |
| chr12 | 52627184 | 52627438 | Hyper | liver_tcga, cancer_general | KRT7, LINC00592 | chr12 | 52652153 | 52652613 | Hyper | cancer_general | KRT121P, KRT86, KRT7 |
| chr12 | 53108089 | 53108218 | Hyper | cancer_general | — | chr12 | 53359345 | 53359563 | Hyper | cancer_general | — |
| chr12 | 54089093 | 54089511 | Hyper | liver_tcga, cancer_general, tcga | — | chr12 | 54132252 | 54132329 | Hyper | cancer_general | — |
| chr12 | 54145843 | 54145895 | Hyper | cancer_general | — | chr12 | 54321250 | 54321628 | Hyper | literature, cancer_general | HOXC-AS5 |
| chr12 | 54322201 | 54322252 | Hyper | cancer_general | HOXC-AS5 | chr12 | 54324799 | 54324937 | Hyper | cancer_general | HOXC-AS5, HOXC13 |
| chr12 | 54329358 | 54329947 | Hyper | cancer_general | HOXC13, HOXC-AS5 | chr12 | 54331062 | 54331135 | Hyper | cancer_general | HOXC13, HOXC-AS5 |
| chr12 | 54332868 | 54333337 | Hyper | cancer_general | HOXC13, HOXC-AS5 | chr12 | 54338666 | 54339681 | Hyper | cancer_general | HOXC13, HOXC-AS5, HOXC12 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 54343812 | 54343861 | Hyper | cancer_general | HOXC12, HOXC13 | chr12 | 54345611 | 54346032 | Hyper | cancer_general | HOXC12, HOXC13 |
| chr12 | 54348844 | 54349336 | Hyper | cancer_general | HOTAIR, HOXC12, HOXC13 | chr12 | 54354514 | 54354621 | Hyper | cancer_general | HOTAIR, HOTAIR_4, HOTAIR_5, HOXC12 |
| chr12 | 54354905 | 54355542 | Hyper | tcga, literature, cancer_general | HOTAIR, HOTAIR_4, HOTAIR_5, HOXC12 | chr12 | 54359960 | 54360084 | Hyper | cancer_general | HOTAIR, HOTAIR_4, HOTAIR_5, HOXC11, HOXC12 |
| chr12 | 54360608 | 54360649 | Hyper | cancer_general | HOTAIR_4, HOTAIR_5, HOXC11, HOTAIR | chr12 | 54377912 | 54378115 | Hyper | cancer_general | HOXC10, MIR196A2, HOXC11 |
| chr12 | 54379174 | 54379623 | Hyper | cancer_general | MIR196A2, HOXC10, HOXC11 | chr12 | 54379888 | 54380459 | Hyper | cancer_general | MIR196A2, HOXC10, HOXC11 |
| chr12 | 54387842 | 54387959 | Hyper | cancer_general | HOXC9, MIR196A2, HOXC10 | chr12 | 54388215 | 54388245 | Hyper | cancer_general | HOXC9, MIR196A2, HOXC10 |
| chr12 | 54391369 | 54391403 | Hyper | cancer_general | HOXC9, MIR196A2, HOXC10 | chr12 | 54393479 | 54393684 | Hyper | cancer_general | HOXC8, MIR196A2, HOXC10 |
| chr12 | 54393950 | 54394162 | Hyper | cancer_general | HOXC8, HOXC9, MIR196A2, HOXC10 | chr12 | 54394410 | 54394442 | Hyper | cancer_general | HOXC8, HOXC9, MIR196A2 |
| chr12 | 54398793 | 54398959 | Hyper | cancer_general | HOXC8, HOXC9 | chr12 | 54399616 | 54399646 | Hyper | head_neck | HOXC8, HOXC9 |
| chr12 | 54402690 | 54402796 | Hyper | cancer_general | HOXC8, HOXC6, HOXC4, HOXC5, HOXC9 | chr12 | 54403067 | 54403360 | Hyper | cancer_general | HOXC8, HOXC9 |
| chr12 | 54408411 | 54408726 | Hyper | cancer_general | HOXC6, HOXC4, HOXC5, HOXC8 | chr12 | 54409476 | 54409505 | Hyper | literature | HOXC6, HOXC4, HOXC5, HOXC8 |
| chr12 | 54423565 | 54423697 | Hyper | cancer_general | HOXC5, MIR615, HOXC6, HOXC4 | chr12 | 54424746 | 54424788 | Hyper | cancer_general | HOXC5, MIR615, HOXC6, HOXC4 |
| chr12 | 54425003 | 54425119 | Hyper | cancer_general | HOXC5, MIR615, HOXC6, HOXC4 | chr12 | 54447351 | 54447581 | Hyper | cancer_general | HOXC4, FLJ12825 |
| chr12 | 54447883 | 54447977 | Hyper | cancer_general | HOXC4, FLJ12825 | chr12 | 54520745 | 54520868 | Hyper | cancer_general | LOC400043 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 54812238 | 54812359 | Hyper | cancer_general | ITGA5 | chr12 | 54942994 | 54943116 | Hyper | tcga | PDE1B, NCKAP1L |
| chr12 | 56478840 | 56478869 | Hyper | literature | ERBB3 | chr12 | 56481645 | 56481937 | Hyper | literature | ERBB3 |
| chr12 | 56486572 | 56486601 | Hyper | literature | ERBB3 | chr12 | 56490965 | 56490994 | Hyper | literature | ERBB3, PA2G4 |
| chr12 | 56491630 | 56491659 | Hyper | literature | PA2G4, ERBB3 | chr12 | 56492618 | 56492647 | Hyper | literature | PA2G4, ERBB3 |
| chr12 | 56873601 | 56873630 | Hyper | liver_tcga | BC059370, GLS2, SPRYD4 | chr12 | 56882240 | 56882380 | Hyper | blood | BC059370, GLS2 |
| chr12 | 57387303 | 57387332 | Hyper | liver_tcga | GPR182, ZBTB39 | chr12 | 57618574 | 57618979 | Hyper | tcga, cancer_general | SHMT2, NDUFA4L2, NXPH4 |
| chr12 | 57944081 | 57944117 | Hyper | cancer_general | KIF5A, DCTN2 | chr12 | 58021320 | 58021713 | Hyper | cancer_general, liver_tcga | BC073932, B4GALNT1, SLC26A10 |
| chr12 | 58021916 | 58022029 | Hyper | liver_tcga | B4GALNT1, SLC26A10 | chr12 | 58025646 | 58025873 | Hyper | cancer_general | JA611266, B4GALNT1, SLC26A10 |
| chr12 | 58145415 | 58145450 | Hyper | literature | DM110804, MARCH9, CDK4, TSPAN31 | chr12 | 59314159 | 59314189 | Hyper | blood | LRIG3 |
| chr12 | 62584838 | 62586017 | Hyper | tcga, cancer_general | FAM19A2 | chr12 | 62586252 | 62586281 | Hyper | tcga | FAM19A2 |
| chr12 | 63025574 | 63026160 | Hyper | tcga, cancer_general |  | chr12 | 63543848 | 63544727 | Hyper | cancer_general | AVPR1A |
| chr12 | 63545313 | 63545343 | Hyper | cancer_general | AVPR1A | chr12 | 64061821 | 64062159 | Hyper | cancer_general | DPY19L2 |
| chr12 | 64062369 | 64062578 | Hyper | tcga, liver_tcga | DPY19L2 | chr12 | 64062921 | 64063096 | Hyper | cancer_general | DPY19L2 |
| chr12 | 64784092 | 64784252 | Hyper | liver_tcga, cancer_general |  | chr12 | 64784534 | 64784564 | Hyper | cancer_general | — |
| chr12 | 65218102 | 65219156 | Hyper | tcga, cancer_general | TBC1D30 | chr12 | 65219376 | 65219784 | Hyper | cancer_general | TBC1D30 |
| chr12 | 65220205 | 65220350 | Hyper | cancer_general | TBC1D30 | chr12 | 65514863 | 65515596 | Hyper | cancer_general | WIF1 |
| chr12 | 66122800 | 66123519 | Hyper | cancer_general | — | chr12 | 66135984 | 66136014 | Hyper | cancer_general | — |
| chr12 | 66582827 | 66583137 | Hyper | liver_tcga, cancer_general | IRAK3 | chr12 | 69327259 | 69327463 | Hyper | cancer_general | CPM |
| chr12 | 72332641 | 72332696 | Hyper | lung | TPH2 | chr12 | 72665186 | 72665788 | Hyper | cancer_general | TRHDE-AS1, BC093903, TRHDE |
| chr12 | 72666115 | 72666211 | Hyper | cancer_general | BC093903, TRHDE-AS1, TRHDE | chr12 | 72666713 | 72667425 | Hyper | tcga, cancer_general | TRHDE-AS1, TRHDE, BC093903 |
| chr12 | 72667652 | 72667682 | Hyper | cancer_general | TRHDE, BC093903, TRHDE-AS1 | chr12 | 75601264 | 75601910 | Hyper | cancer_general | KCNC2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 75602976 | 75603231 | Hyper | cancer_general | KCNC2 | chr12 | 75728336 | 75728485 | Hyper | tcga, cancer_general | GLIPR1L1, CAPS2 |
| chr12 | 75728737 | 75728766 | Hyper | tcga | GLIPR1L1, CAPS2 | chr12 | 77719311 | 77719422 | Hyper | tcga | |
| chr12 | 79257222 | 79257351 | Hyper | pancreas | SYT1 | chr12 | 79258924 | 79258954 | Hyper | cancer_general | SYT1 |
| chr12 | 81102185 | 81102562 | Hyper | cancer_general, liver_tcga | MYF5, MYF6 | chr12 | 81107989 | 81108034 | Hyper | liver_tcga | MYF5, MYF6 |
| chr12 | 81471517 | 81472111 | Hyper | cancer_general | ACSS3 | chr12 | 85306519 | 85306578 | Hyper | cancer_general | SLC6A15 |
| chr12 | 85667272 | 85667731 | Hyper | cancer_general | ALX1 | chr12 | 85673206 | 85673235 | Hyper | literature | ALX1 |
| chr12 | 85673460 | 85674807 | Hyper | cancer_general | ALX1 | chr12 | 88973544 | 88973582 | Hyper | blood | U1 |
| chr12 | 88974159 | 88974253 | Hyper | blood | U1 | chr12 | 93966429 | 93966603 | Hyper | cancer_general | SOCS2, SOCS2-AS1 |
| chr12 | 93966998 | 93967239 | Hyper | cancer_general | SOCS2, SOCS2-AS1 | chr12 | 94543409 | 94543445 | Hyper | cancer_general | PLXNC1 |
| chr12 | 94543899 | 94543961 | Hyper | cancer_general | PLXNC1 | chr12 | 95267524 | 95267554 | Hyper | esophageal | |
| chr12 | 95267865 | 95267976 | Hyper | cancer_general | | chr12 | 95941868 | 95942978 | Hyper | cancer_general, liver_tcga, literature | USP44 |
| chr12 | 99288312 | 99289309 | Hyper | cancer_general, tcga | ANKS1B | chr12 | 101111029 | 101111061 | Hyper | cancer_general | ANO4 |
| chr12 | 101111373 | 101111479 | Hyper | cancer_general | ANO4 | chr12 | 103218495 | 103218595 | Hyper | cancer_general | LINC00485 |
| chr12 | 103350324 | 103350354 | Hyper | cancer_general | ASCL1 | chr12 | 103351564 | 103352681 | Hyper | cancer_general, tcga, cancer_general | ASCL1 |
| chr12 | 103358865 | 103358899 | Hyper | cancer_general | ASCL1 | chr12 | 103359556 | 103359586 | Hyper | cancer_general | ASCL1 |
| chr12 | 103889160 | 103889211 | Hyper | pancreas | C12orf42 | chr12 | 103889746 | 103889812 | Hyper | cancer_general | C12orf42 |
| chr12 | 104609417 | 104610100 | Hyper | tcga, cancer_general | TXNRD1 | chr12 | 104850505 | 104850592 | Hyper | colorectal | CHST11 |
| chr12 | 104851077 | 104851186 | Hyper | colorectal | CHST11 | chr12 | 104852032 | 104852508 | Hyper | cancer_general, tcga | CHST11 |
| chr12 | 105478323 | 105478419 | Hyper | liver_tcga, hepatobiliary | ALDH1L2 | chr12 | 106533852 | 106533881 | Hyper | literature | NUAK1 |
| chr12 | 106974353 | 106974383 | Hyper | cancer_general | LOC100287944, RFX4 | chr12 | 106976725 | 106976795 | Hyper | cancer_general | RFX4, LOC100287944 |
| chr12 | 106977321 | 106977497 | Hyper | cancer_general | RFX4, LOC100287944 | chr12 | 106979161 | 106979534 | Hyper | cancer_general | LOC100287944, RFX4 |
| chr12 | 106979799 | 106979995 | Hyper | cancer_general | RFX4, LOC100287944 | chr12 | 106980223 | 106980333 | Hyper | cancer_general | RFX4, LOC100287944 |
| chr12 | 106980854 | 106981406 | Hyper | cancer_general | RFX4, LOC100287944 | chr12 | 107486550 | 107486672 | Hyper | blood | CRY1 |
| chr12 | 107487194 | 107487855 | Hyper | blood | CRY1 | chr12 | 107712273 | 107712303 | Hyper | blood | BTBD11 |
| chr12 | 107713205 | 107713235 | Hyper | cancer_general | BTBD11 | chr12 | 107714866 | 107715153 | Hyper | cancer_general | BTBD11 |
| chr12 | 108168971 | 108169573 | Hyper | literature, cancer_general, liver_tcga | ASCL4 | chr12 | 108237466 | 108237586 | Hyper | cancer_general | |
| chr12 | 108238102 | 108238616 | Hyper | cancer_general, tcga | | chr12 | 108297411 | 108297466 | Hyper | cancer_general | LOC728739 |
| chr12 | 109639281 | 109639475 | Hyper | liver_tcga | ACACB | chr12 | 111127124 | 111127455 | Hyper | tcga, cancer_general | HVCN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 111471177 | 111471559 | Hyper | tcga, literature, cancer_general | CUX2 | chr12 | 111471948 | 111472752 | Hyper | cancer_general, tcga | CUX2 |
| chr12 | 112888151 | 112888315 | Hyper | literature | PTPN11 | chr12 | 112910821 | 112910850 | Hyper | literature | PTPN11 |
| chr12 | 112915509 | 112915538 | Hyper | literature | PTPN11 | chr12 | 112926255 | 112926284 | Hyper | literature | PTPN11 |
| chr12 | 112926876 | 112926914 | Hyper | literature | PTPN11 | chr12 | 113012954 | 113013157 | Hyper | cancer_general | RPH3A |
| chr12 | 113541667 | 113542099 | Hyper | cancer_general | RASAL1, DTX1 | chr12 | 113592238 | 113592359 | Hyper | cancer_general | DDX54, CCDC42B |
| chr12 | 113900704 | 113900765 | Hyper | tcga | LHX5 | chr12 | 113901074 | 113901591 | Hyper | tcga, cancer_general | LHX5 |
| chr12 | 113902026 | 113902353 | Hyper | cancer_general | LHX5 | chr12 | 113903468 | 113903498 | Hyper | cancer_general | LHX5 |
| chr12 | 113904779 | 113905016 | Hyper | cancer_general | LHX5 | chr12 | 113908990 | 113909455 | Hyper | cancer_general | LHX5 |
| chr12 | 113909667 | 113909708 | Hyper | cancer_general | LHX5 | chr12 | 113914050 | 113914050 | Hyper | cancer_general | LHX5 |
| chr12 | 113916222 | 113916316 | Hyper | cancer_general | LHX5 | chr12 | 113916649 | 113916678 | Hyper | literature | LHX5 |
| chr12 | 113916972 | 113917012 | Hyper | cancer_general | LHX5 | chr12 | 113917232 | 113917310 | Hyper | cancer_general | LHX5 |
| chr12 | 113917775 | 113917890 | Hyper | cancer_general | LHX5 | chr12 | 114029408 | 114029660 | Hyper | tcga | LHX5 |
| chr12 | 114076029 | 114076093 | Hyper | cancer_general | — | chr12 | 114833985 | 114834102 | Hyper | cancer_general | TBX5 |
| chr12 | 114838325 | 114838726 | Hyper | cancer_general | TBX5-AS1, TBX5 | chr12 | 114839104 | 114839147 | Hyper | cancer_general | TBX5-AS1, TBX5 |
| chr12 | 114841046 | 114841084 | Hyper | cancer_general | TBX5-AS1, TBX5 | chr12 | 114841425 | 114841493 | Hyper | cancer_general | TBX5-AS1, TBX5 |
| chr12 | 114843112 | 114843278 | Hyper | cancer_general | TBX5-AS1, TBX5 | chr12 | 114843545 | 114843660 | Hyper | cancer_general | TBX5-AS1, TBX5 |
| chr12 | 114844201 | 114844300 | Hyper | cancer_general | TBX5-AS1, TBX5 | chr12 | 114846715 | 114846768 | Hyper | cancer_general | TBX5-AS1, TBX5 |
| chr12 | 114846979 | 114847691 | Hyper | cancer_general | TBX5-AS1, TBX5 | chr12 | 114852040 | 114852082 | Hyper | cancer_general | TBX5-AS1, TBX5 |
| chr12 | 114852293 | 114852373 | Hyper | tcga | TBX5-AS1 | chr12 | 114877171 | 114877262 | Hyper | cancer_general | — |
| chr12 | 114878550 | 114878584 | Hyper | cancer_general | — | chr12 | 114878813 | 114879012 | Hyper | cancer_general | — |
| chr12 | 114881634 | 114881764 | Hyper | cancer_general | — | chr12 | 114882555 | 114882646 | Hyper | cancer_general | — |
| chr12 | 114883473 | 114883535 | Hyper | cancer_general | — | chr12 | 114885222 | 114885284 | Hyper | cancer_general | — |
| chr12 | 114918594 | 114918717 | Hyper | cancer_general | — | chr12 | 115136159 | 115136363 | Hyper | cancer_general | — |
| chr12 | 116946086 | 116946548 | Hyper | tcga, cancer_general | NOS1 | chr12 | 117798065 | 117798095 | Hyper | cancer_general | NOS1 |
| chr12 | 117798690 | 117798965 | Hyper | cancer_general | — | chr12 | 117799413 | 117799529 | Hyper | cancer_general | NOS1 |
| chr12 | 119212216 | 119212381 | Hyper | cancer_general | SRRM4 | chr12 | 119418594 | 119418847 | Hyper | cancer_general | SRRM4 |
| chr12 | 119419436 | 119419466 | Hyper | cancer_general | TMEM233, AF086288 | chr12 | 119419720 | 119419899 | Hyper | cancer_general | RAB35, CCDC64 |
| chr12 | 120032862 | 120033169 | Hyper | cancer_general | RAB35, CCDC64 | chr12 | 120535158 | 120535187 | Hyper | literature | — |
| chr12 | 120536625 | 120536654 | Hyper | literature | DNAH10, ATP6V0A2 | chr12 | 124246908 | 124246937 | Hyper | liver_tcga | DNAH10, ATP6V0A2 |
| chr12 | 124247208 | 124247237 | Hyper | liver_tcga | — | chr12 | 124865115 | 124865144 | Hyper | literature | NCOR2 |
| chr12 | 125533949 | 125534407 | Hyper | liver_tcga, cancer_general | — | chr12 | 125670117 | 125670289 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 126168554 | 126168620 | Hyper | cancer_general | — | chr12 | 127210965 | 127211378 | Hyper | cancer_general | LINC00944 |
| chr12 | 127765158 | 127765432 | Hyper | cancer_general | — | chr12 | 127940086 | 127940247 | Hyper | pancreas | — |
| chr12 | 128751384 | 128751443 | Hyper | cancer_general | TMEM132C | chr12 | 128751821 | 128752240 | Hyper | cancer_general | TMEM132C |
| chr12 | 128752499 | 128752944 | Hyper | cancer_general | TMEM132C | chr12 | 128753210 | 128753240 | Hyper | cancer_general | TMEM132C |
| chr12 | 128850534 | 128850644 | Hyper | cancer_general | — | chr12 | 129338003 | 129338816 | Hyper | cancer_general | GLT1D1 |
| chr12 | 129427424 | 129427557 | Hyper | pancreas, cancer_general | GLT1D1 | chr12 | 130387776 | 130387811 | Hyper | cancer_general | — |
| chr12 | 130388410 | 130389152 | Hyper | cancer_general | — | chr12 | 130589202 | 130589266 | Hyper | cancer_general | — |
| chr12 | 130645233 | 130645627 | Hyper | cancer_general | FZD10, FZD10-AS1 | chr12 | 130646686 | 130648472 | Hyper | tcga, cancer_general | FZD10-AS1, FZD10 |
| chr12 | 131200379 | 131200645 | Hyper | tcga | RIMBP2 | chr12 | 131400816 | 131400919 | Hyper | cancer_general | CHFR |
| chr12 | 133195093 | 133195196 | Hyper | liver_tcga | LRCOL1, P2RX2, POLE | chr12 | 133463736 | 133463876 | Hyper | esophageal | — |
| chr12 | 133464108 | 133464166 | Hyper | esophageal | CHFR | chr12 | 133464840 | 133465027 | Hyper | tcga | CHFR |
| chr12 | 133481389 | 133481655 | Hyper | liver_tcga, cancer_general | AK055957 | chr12 | 133484742 | 133485355 | Hyper | liver_tcga, cancer_general | AK055957 |
| chr12 | 133485557 | 133485847 | Hyper | tcga, cancer_general | AK055957 | chr12 | 133758048 | 133758107 | Hyper | esophageal | ZNF268 |
| chr8 | 686870 | 687316 | Hyper | cancer_general | ERICH1-AS1 | chr8 | 687745 | 688032 | Hyper | tcga, cancer_general | ERICH1-AS1 |
| chr8 | 688360 | 688390 | Hyper | cancer_general | ERICH1-AS1 | chr8 | 688985 | 689043 | Hyper | cancer_general | — |
| chr8 | 1950097 | 1950134 | Hyper | tcga | KBTBD11 | chr8 | 4849141 | 4849177 | Hyper | cancer_general | — |
| chr8 | 4849466 | 4849500 | Hyper | cancer_general | — | chr8 | 4850247 | 4850516 | Hyper | cancer_general | — |
| chr8 | 4851736 | 4851765 | Hyper | tcga | — | chr8 | 4852021 | 4852118 | Hyper | tcga, cancer_general | — |
| chr8 | 9756051 | 9756476 | Hype | cancer_general | LINC00599, AK091593, MIR124-1 | chr8 | 9760735 | 9761155 | Hyper | tcga, cancer_general | MIR124-1, AK091593, LINC00599 |
| chr8 | 9762586 | 9762864 | Hyper | cancer_general | MIR124-1, AK091593, LINC00599 | chr8 | 9763143 | 9763275 | Hyper | cancer_general | MIR124-1, AK091593, LINC00599 |
| chr8 | 9763895 | 9764214 | Hyper | cancer_general | MIR124-1, AK091593, LINC00599 | chr8 | 9764434 | 9764551 | Hyper | cancer_general | MIR124-1, AK091593, LINC00599 |
| chr8 | 10587589 | 10587783 | Hyper | tcga | BC043573, SOX7 | chr8 | 10588383 | 10588456 | Hyper | cancer_general | BC043573, SOX7 |
| chr8 | 11204479 | 11204509 | Hyper | cancer_general | BC038546, TDH | chr8 | 11204810 | 11204905 | Hyper | cancer_general | TDH, BC038546 |
| chr8 | 11536827 | 11536857 | Hyper | cancer_general | GATA4 | chr8 | 11537225 | 11537259 | Hyper | cancer_general | GATA4 |
| chr8 | 11554885 | 11554915 | Hyper | cancer_general | GATA4 | chr8 | 11555152 | 11555521 | Hyper | cancer_general | GATA4 |
| chr8 | 11559759 | 11560375 | Hyper | cancer_general | GATA4 | chr8 | 11560711 | 11560793 | Hyper | cancer_general | GATA4 |
| chr8 | 11561442 | 11562169 | Hyper | tcga, cancer_general | GATA4 | chr8 | 11562422 | 11562485 | Hyper | cancer_general | GATA4 |
| chr8 | 11562701 | 11562917 | Hyper | cancer_general | GATA4 | chr8 | 12990386 | 12990431 | Hyper | cancer_general | DLC1 |
| chr8 | 12990664 | 12990784 | Hyper | cancer_general | DLC1 | chr8 | 15094505 | 15094582 | Hyper | cancer_general | — |
| chr8 | 15397735 | 15397845 | Hyper | cancer_general | TUSC3 | chr8 | 16884182 | 16884239 | Hyper | tcga | MICU3 |
| chr8 | 16885205 | 16885241 | Hyper | cancer_general | MICU3 | chr8 | 17271066 | 17271119 | Hyper | liver_tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 19779433 | 19797463 | Hyper | cancer_general | LPL | chr8 | 19779939 | 19798019 | Hyper | cancer_general | LPL |
| chr8 | 20160762 | 20160894 | Hyper | cancer_general | — | chr8 | 22089409 | 22089560 | Hyper | cancer_general | PHYHIP |
| chr8 | 22562345 | 22562483 | Hyper | cancer_general | PEBP4 | chr8 | 22960648 | 22960723 | Hyper | cancer_general | TNFRSF10C, LOC254896 |
| chr8 | 23020951 | 23021107 | Hyper | tcga | TNFRSF10D | chr8 | 23260683 | 23260870 | Hyper | cancer_general | ENTPD4 |
| chr8 | 23559385 | 23560525 | Hyper | cancer_general | NKX2-6 | chr8 | 23563791 | 23564388 | Hyper | cancer_general | NKX2-6 |
| chr8 | 23564652 | 23565024 | Hyper | cancer_general | NKX2-6 | chr8 | 23566803 | 23567492 | Hyper | cancer_general | NKX2-6 |
| chr8 | 23571681 | 23571973 | Hyper | cancer_general | NKX2-6 | chr8 | 23572377 | 23572554 | Hyper | cancer_general | NKX2-6 |
| chr8 | 23584078 | 23584760 | Hyper | tcga, cancer_general | — | chr8 | 24770314 | 24770581 | Hyper | cancer_general | AK308605, NEFM |
| chr8 | 24771168 | 24771213 | Hyper | cancer_general | NEFM, AK308605 | chr8 | 24771431 | 24771562 | Hyper | literature, cancer_general | NEFM, AK308605 |
| chr8 | 24813188 | 24813287 | Hyper | cancer_general | NEFL | chr8 | 24813750 | 24814407 | Hyper | tcga, cancer_general | NEFL |
| chr8 | 24857776 | 24857808 | Hyper | cancer_general | — | chr8 | 24858336 | 24858440 | Hyper | cancer_general | — |
| chr8 | 24858856 | 24859161 | Hyper | tcga, cancer_general | — | chr8 | 24859496 | 24859526 | Hyper | cancer_general | — |
| chr8 | 25041746 | 25041864 | Hyper | blood | DOCK5 | chr8 | 25042534 | 25042567 | Hyper | blood | DOCK5 |
| chr8 | 25900408 | 25901317 | Hyper | cancer_general | EBF2 | chr8 | 25901540 | 25901765 | Hyper | cancer_general | EBF2 |
| chr8 | 25902146 | 25902176 | Hyper | cancer_general | EBF2 | chr8 | 25902619 | 25902649 | Hyper | cancer_general | EBF2 |
| chr8 | 25903662 | 25903854 | Hyper | cancer_general | EBF2 | chr8 | 25904157 | 25904191 | Hyper | cancer_general | EBF2 |
| chr8 | 25905096 | 25905126 | Hyper | cancer_general | EBF2 | chr8 | 25905762 | 25905811 | Hyper | cancer_general | EBF2 |
| chr8 | 25909197 | 25909597 | Hyper | cancer_general | — | chr8 | 26372863 | 26372893 | Hyper | cancer_general | DPYSL2, PNMA2 |
| chr8 | 26723985 | 26724080 | Hyper | cancer_general | AK311558, ADRA1A | chr8 | 30243388 | 30243423 | Hyper | cancer_general | RBPMS, LOC100128750 |
| chr8 | 30769249 | 30769411 | Hyper | cancer_general | — | chr8 | 30770106 | 30770188 | Hyper | tcga | — |
| chr8 | 31496481 | 31496757 | Hyper | cancer_general | NRG1 | chr8 | 31497024 | 31497152 | Hyper | cancer_general | NRG1 |
| chr8 | 31497499 | 31497639 | Hyper | cancer_general | NRG1 | chr8 | 31498117 | 31498150 | Hyper | cancer_general | NRG1 |
| chr8 | 32406598 | 32406914 | Hyper | tcga, cancer_general | NRG1 | chr8 | 33372069 | 33372125 | Hyper | cancer_general | TTI2 |
| chr8 | 33457142 | 33457379 | Hyper | cancer_general | DUSP26 | chr8 | 35092985 | 35093054 | Hyper | cancer_general | UNC5D |
| chr8 | 35093951 | 35093981 | Hyper | cancer_general | UNC5D | chr8 | 37655454 | 37655517 | Hyper | cancer_general | GPR124 |
| chr8 | 37655810 | 37656081 | Hyper | cancer_general | GPR124 | chr8 | 37822796 | 37823423 | Hyper | tcga, cancer_general | ADRB3 |
| chr8 | 37823678 | 37823726 | Hyper | cancer_general | ADRB3 | chr8 | 38008234 | 38008557 | Hyper | cancer_general | STAR |
| chr8 | 38274835 | 38274864 | Hyper | literature | FGFR1, LETM2 | chr8 | 38323911 | 38323941 | Hyper | cancer_general | FGFR1 |
| chr8 | 38965121 | 38965386 | Hyper | liver_tcga | ADAM32 | chr8 | 41165865 | 41166723 | Hyper | cancer_general | SFRP1 |
| chr8 | 41166974 | 41167035 | Hyper | cancer_general | SFRP1 | chr8 | 41424760 | 41424842 | Hyper | cancer_general | — |
| chr8 | 41624826 | 41624855 | Hyper | tcga | — | chr8 | 41625112 | 41625141 | Hyper | tcga | — |
| chr8 | 41733505 | 41733640 | Hyper | cancer_general | — | chr8 | 41753593 | 41753761 | Hyper | cancer_general | — |
| chr8 | 41754152 | 41754885 | Hyper | liver_tcga, cancer_general | — | chr8 | 41755178 | 41755208 | Hyper | cancer_general | — |
| chr8 | 48100155 | 48100443 | Hyper | tcga | LOC100287846 | chr8 | 49293364 | 49293614 | Hyper | tcga, cancer_general | — |
| chr8 | 49468669 | 49469127 | Hyper | tcga, liver_tcga, cancer_general | — | chr8 | 49783041 | 49783283 | Hyper | tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 50822179 | 50822308 | Hyper | cancer_general | SNTG1 | chr8 | 50822686 | 50822734 | Hyper | cancer_general | SNTG1 |
| chr8 | 50823452 | 50823562 | Hyper | cancer_general | SNTG1 | chr8 | 53477408 | 53477780 | Hyper | cancer_general | FAM150A |
| chr8 | 53478008 | 53478275 | Hyper | cancer_general, tcga | FAM150A | chr8 | 53478480 | 53478720 | Hyper | cancer_general, tcga | FAM150A |
| chr8 | 53851141 | 53851170 | Hyper | literature | NPBWR1 | chr8 | 53853811 | 53854509 | Hyper | tcga, colorectal, cancer_general | NPBWR1 |
| chr8 | 54163316 | 54164175 | Hyper | tcga, cancer_general | OPRK1 | chr8 | 54789278 | 54789310 | Hyper | cancer_general | RGS20 |
| chr8 | 54789632 | 54790077 | Hyper | cancer_general | RGS20 | chr8 | 54790291 | 54790855 | Hyper | cancer_general | RGS20 |
| chr8 | 54791809 | 54792237 | Hyper | cancer_general | RGS20 | chr8 | 54792634 | 54792760 | Hyper | cancer_general | RGS20 |
| chr8 | 54794217 | 54794327 | Hyper | cancer_general | RGS20 | chr8 | 54794713 | 54795196 | Hyper | cancer_general | RGS20 |
| chr8 | 55366188 | 55367641 | Hyper | tcga, cancer_general | SOX17 | chr8 | 55370113 | 55370858 | Hyper | literature, cancer_general | SOX17 |
| chr8 | 55371178 | 55372538 | Hyper | cancer_general | SOX17 | chr8 | 55379280 | 55379962 | Hyper | cancer_general | SOX17 |
| chr8 | 55382766 | 55383237 | Hyper | cancer_general | SOX17 | chr8 | 56013641 | 56013927 | Hyper | cancer_general | XKR4 |
| chr8 | 56014157 | 56014317 | Hyper | cancer_general | XKR4 | chr8 | 56014623 | 56014783 | Hyper | cancer_general | XKR4 |
| chr8 | 56015038 | 56015357 | Hyper | cancer_general | XKR4 | chr8 | 56015560 | 56015619 | Hyper | cancer_general | XKR4 |
| chr8 | 56015908 | 56015938 | Hyper | pancreas | XKR4 | chr8 | 57025692 | 57025943 | Hyper | cancer_general | MOS, SNORA3, MOS |
| chr8 | 57026168 | 57026213 | Hyper | cancer_general | SNORA3, MOS | chr8 | 57026503 | 57026547 | Hyper | cancer_general | SNORA3, MOS |
| chr8 | 57069553 | 57070157 | Hyper | tcga, cancer_general, liver_tcga | PLAG1 | chr8 | 57358147 | 57359636 | Hyper | literature, cancer_general | AX747062, PENK |
| chr8 | 57359893 | 57359922 | Hyper | literature | PENK, AX747062 | chr8 | 57360570 | 57360791 | Hyper | literature, cancer_general | AX747062, PENK |
| chr8 | 58907698 | 58907835 | Hyper | cancer_general | FAM110B | chr8 | 60032680 | 60032738 | Hyper | cancer_general | TOX |
| chr8 | 62200502 | 62200776 | Hyper | cancer_general | CLVS1 | chr8 | 63161658 | 63161800 | Hyper | cancer_general | NKAIN3 |
| chr8 | 65281616 | 65281760 | Hyper | cancer_general | BX537900, MIR124-2, LOC100130155 | chr8 | 65281984 | 65283341 | Hyper | cancer_general | LOC100130155, BX537900, RMI124-2 |
| chr8 | 65283799 | 65284094 | Hyper | cancer_general | LOC100130155, BX537900, MIR124-2 | chr8 | 65286056 | 65286366 | Hyper | cancer_general | BX537900, MIR124-2, LOC100130155 |
| chr8 | 65286682 | 65286753 | Hyper | cancer_general | LOC100130155, BX537900, MIR124-2 | chr8 | 65286963 | 65287251 | Hyper | cancer_general | BX537900, MIR124-2, LOC100130155 |
| chr8 | 65289123 | 65289241 | Hyper | cancer_general | BX537900, MIR124-2, LOC100130155 | chr8 | 65289614 | 65290798 | Hyper | literature, cancer_general | BX537900, MIR 124-2, LOC100130155 |
| chr8 | 65291034 | 65291284 | Hyper | cancer_general | MIR124-2, BX537900, LOC100130155 | chr8 | 65292185 | 65292727 | Hyper | cancer_general | BX537900, LOC100130155, MIR124-2 |
| chr8 | 65488271 | 65488322 | Hyper | cancer_general | BHLHE22, LOC401463 | chr8 | 65488661 | 65488697 | Hyper | cancer_general | BHLHE22, LOC401463 |
| chr8 | 65489099 | 65489129 | Hyper | cancer_general | BHLHE22, LOC401463 | chr8 | 65492712 | 65492979 | Hyper | tcga, cancer_general | BHLHE22, LOC401463 |
| chr8 | 65493195 | 65493433 | Hyper | cancer_general | BHLHE22, LOC401463 | chr8 | 65493658 | 65493751 | Hyper | cancer_general | BHLHE22, LOC401463 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 65493961 | 65494193 | Hyper | cancer_general | BHLHE22, LOC401463 | chr8 | 65498566 | 65498841 | Hyper | cancer_general | CYP7B1, BHLHE22, LOC401463 |
| chr8 | 65499757 | 65500015 | Hyper | cancer_general | CYP7B1, BHLHE22, LOC401463 | chr8 | 65710938 | 65711046 | Hyper | cancer_general | CYP7B1 |
| chr8 | 67025063 | 67025640 | Hyper | head_neck | TRNA_Ala, TRNA_Tyr | chr8 | 67025920 | 67026578 | Hyper | head_neck | |
| chr8 | 67026812 | 67026990 | Hyper | head_neck | TRNA_Ala, TRNA_Tyr | chr8 | 67344538 | 67344771 | Hyper | tcga, cancer_general | TRNA_Tyr, TRNA_Ala, ADHFE1, RRS1, LOC100505676 |
| chr8 | 67873327 | 67875682 | Hyper | tcga, liver_tcga, cancer_general | TCF24 | chr8 | 67940624 | 67940875 | Hyper | cancer_general | |
| chr8 | 68864578 | 68864765 | Hyper | cancer_general | BC036055, PREX2 | chr8 | 69242905 | 69242988 | Hyper | tcga, cancer_general | C8orf34, LOC286189 |
| chr8 | 69243269 | 69243994 | Hyper | tcga, cancer_general | LOC286189, C8orf34 | chr8 | 69244370 | 69244500 | Hyper | cancer_general | C8orf34, LOC286189 |
| chr8 | 70744860 | 70744925 | Hyper | cancer_general | SLCOSA1 | chr8 | 70946760 | 70947658 | Hyper | cancer_general | |
| chr8 | 70981944 | 70983226 | Hyper | cancer_general, literature | PRDM14 | chr8 | 70983504 | 70984978 | Hyper | liver_tcga, cancer_general | PRDM14 |
| chr8 | 72273998 | 72274033 | Hyper | cancer_general | EYA1 | chr8 | 72460007 | 72460269 | Hyper | cancer_general | |
| chr8 | 72468569 | 72469574 | Hyper | tcga, cancer_general | | chr8 | 72471053 | 72471083 | Hyper | cancer_general | |
| chr8 | 72754394 | 72754609 | Hyper | cancer_general | LOC100132891, MSC | chr8 | 72754821 | 72755176 | Hyper | tcga, cancer_general | LOC100132891, MSC |
| chr8 | 72755666 | 72756896 | Hyper | cancer_general | MSC, LOC100132891 | chr8 | 72917335 | 72917446 | Hyper | tcga | LOC100132891 |
| chr8 | 72987600 | 72988036 | Hyper | cancer_general | TRPA1 | chr8 | 73163777 | 73164180 | Hyper | cancer_general | LOC392232 |
| chr8 | 73450064 | 73450100 | Hyper | cancer_general | KCNB2 | chr8 | 73450515 | 73450559 | Hyper | cancer_general | KCNB2 |
| chr8 | 75896574 | 75897337 | Hyper | tcga, cancer_general | CRISPLD1 | chr8 | 75885219 | 77585698 | Hyper | cancer_general | ZFHX4, ZFHX4-AS1 |
| chr8 | 77586175 | 77586278 | Hyper | cancer_general | ZFHX4, ZFHX4-AS1 | chr8 | 77586563 | 77586617 | Hyper | cancer_general | ZFHX4, ZFHX4-AS1 |
| chr8 | 77590239 | 77590466 | Hyper | cancer_general | ZFHX4, ZFHX4-AS1 | chr8 | 77593110 | 77593376 | Hyper | cancer_general | ZFHX4, ZFHX4-AS1 |
| chr8 | 77593889 | 77594124 | Hyper | cancer_general | ZFHX4, ZFHX4-AS1 | chr8 | 77594648 | 77594993 | Hyper | tcga, cancer_general | ZFHX4, ZFHX4-AS1 |
| chr8 | 77595339 | 77595494 | Hyper | cancer_general | ZFHX4, ZFHX4-AS1, ZFHX4 | chr8 | 79428297 | 79428401 | Hyper | cancer_general | PKIA |
| chr8 | 80523983 | 80524029 | Hyper | cancer_general | STMN2 | chr8 | 80524253 | 80524318 | Hyper | cancer_general | STMN2 |
| chr8 | 80524946 | 80525020 | Hyper | cancer_general | STMN2 | chr8 | 80525604 | 80525733 | Hyper | colorectal, cancer_general | STMN2 |
| chr8 | 80695902 | 80695932 | Hyper | cancer_general | AK055332 | chr8 | 80803673 | 80803872 | Hyper | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 81398018 | 81398155 | Hyper | esophageal | ZBTB10, DJ031142 | chr8 | 81398428 | 81399496 | Hyper | esophageal | ZBTB10, DJ031142 |
| chr8 | 81478185 | 81478350 | Hyper | cancer_general | — | chr8 | 85095482 | 85095668 | Hyper | cancer_general | RALYL |
| chr8 | 85096583 | 85096805 | Hyper | cancer_general | RALYL | chr8 | 85097015 | 85097220 | Hyper | cancer_general | RALYL |
| chr8 | 86350553 | 86350595 | Hyper | literature | CA3 | chr8 | 89339389 | 89339745 | Hyper | tcga, cancer_general | MMP16 |
| chr8 | 89340270 | 89340345 | Hyper | cancer_general | MMP16 | chr8 | 91094221 | 91094251 | Hyper | cancer_general | Metazoa_SRP, CALB1 |
| chr8 | 91803676 | 91803718 | Hyper | cancer_general | NECAB1 | chr8 | 91803991 | 91804253 | Hyper | cancer_general | NECAB1 |
| chr8 | 91997046 | 91997947 | Hyper | tcga, cancer_general | TMEM55A, LOC100127983 | chr8 | 93114135 | 93114528 | Hyper | cancer_general, tcga | — |
| chr8 | 95651098 | 95651218 | Hyper | liver_tcga | ESRP1, LOC100288748 | chr8 | 95651538 | 95651655 | Hyper | blood | ESRP1, LOC100288748 |
| chr8 | 97157085 | 97158066 | Hyper | tcga, cancer_general | GDF6 | chr8 | 97165644 | 97165676 | Hyper | cancer_general | GDF6 |
| chr8 | 97166425 | 97166455 | Hyper | cancer_general | GDF6 | chr8 | 97167178 | 97167223 | Hyper | cancer_general, tcga | GDF6 |
| chr8 | 97167811 | 97167855 | Hyper | pancreas | GDF6 | chr8 | 97169838 | 97170334 | Hyper | cancer_general | GDF6 |
| chr8 | 97170867 | 97170897 | Hyper | cancer_general | GDF6 | chr8 | 97171129 | 97172200 | Hyper | cancer_general | GDF6 |
| chr8 | 97172433 | 97173458 | Hyper | tcga, cancer_general | GDF6 | chr8 | 97173822 | 97173935 | Hyper | cancer_general | GDF6 |
| chr8 | 97506034 | 97506524 | Hyper | colorectal, cancer_general | SDC2 | chr8 | 97507115 | 97507284 | Hyper | colorectal, cancer_general | SDC2 |
| chr8 | 97507546 | 97507680 | Hyper | tcga | SDC2 | chr8 | 98289825 | 98290260 | Hyper | liver_tcga, cancer_general | TSPYL5 |
| chr8 | 99439104 | 99439133 | Hyper | liver_tcga | KCNS2 | chr8 | 99439382 | 99440354 | Hyper | literature, liver_tcga, cancer_general, tcga | KCNS2 |
| chr8 | 99951404 | 99951434 | Hyper | liver_tcga, cancer_general | OSR2 | chr8 | 99951836 | 99952815 | Hyper | cancer_general | OSR2 |
| chr8 | 99954490 | 99954727 | Hyper | cancer_general | OSR2 | chr8 | 99955180 | 99955327 | Hyper | cancer_general, tcga | OSR2 |
| chr8 | 99959429 | 99959549 | Hyper | liver_tcga | OSR2 | chr8 | 99960329 | 99960971 | Hyper | cancer_general | OSR2 |
| chr8 | 99961187 | 99961272 | Hyper | cancer_general | OSR2 | chr8 | 99961792 | 99961822 | Hyper | literature, liver_tcga, cancer_general | OSR2 |
| chr8 | 99985866 | 99987014 | Hyper | cancer_general | — | chr8 | 101118241 | 101118577 | Hyper | cancer_general | — |
| chr8 | 101661920 | 101661991 | Hyper | liver_tcga | SNX31 | chr8 | 101821973 | 101822047 | Hyper | cancer_general | GRHL2 |
| chr8 | 101920382 | 101920468 | Hyper | head_neck | — | chr8 | 102504464 | 102504506 | Hyper | liver_tcga, literature | GRHL2 |
| chr8 | 102505512 | 102505556 | Hyper | liver_tcga | GRHL2 | chr8 | 102505797 | 102506000 | Hyper | liver tcga, blood | GRHL2 |
| chr8 | 104153202 | 104153246 | Hyper | cancer_general | BAALC, C8orf56, AK001351 | chr8 | 104153449 | 104153641 | Hyper | cancer_general | BAALC, C8orf56, AK001351 |
| chr8 | 104383700 | 104383985 | Hyper | liver_tcga, tcga | CTHRC1 | chr8 | 104512123 | 104513186 | Hyper | tcga, liver_tcga, cancer_general | RIMS2 |
| chr8 | 104513462 | 104513926 | Hyper | tcga, cancer_general | RIMS2 | chr8 | 105235369 | 105236054 | Hyper | tcga, cancer_general | — |
| chr8 | 105478725 | 105479176 | Hyper | cancer_general | — | chr8 | 105479404 | 105479464 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 106331160 | 106331237 | Hyper | cancer_general | ZFPM2 | chr8 | 106332104 | 106332202 | Hyper | tcga | ZFPM2 |
| chr8 | 107282163 | 107282195 | Hyper | esophageal | OXR1 | chr8 | 107284038 | 107284075 | Hyper | cancer_general | OXR1 |
| chr8 | 108509543 | 108509697 | Hyper | lung, cancer_general | — | chr8 | 109093679 | 109094180 | Hyper | cancer_general | RSPO2 |
| chr8 | 109094485 | 109094595 | Hyper | cancer_general | RSPO2 | chr8 | 109094840 | 109095932 | Hyper | cancer_general | RSPO2 |
| chr8 | 109799588 | 109799770 | Hyper | tcga | TMEM74 | chr8 | 110986443 | 110986682 | Hyper | cancer_general | KCNV1 |
| chr8 | 114444580 | 114445192 | Hyper | tcga, cancer_general | CSMD3 | chr8 | 114445763 | 114446068 | Hyper | cancer_general | CSMD3 |
| chr8 | 114446405 | 114446435 | Hyper | cancer_general | CSMD3 | chr8 | 114446931 | 114447368 | Hyper | cancer_general | CSMD3 |
| chr8 | 114449039 | 114449257 | Hyper | cancer_general | CSMD3 | chr8 | 114449550 | 114449602 | Hyper | cancer_general | CSMD3 |
| chr8 | 116660527 | 116660760 | Hyper | cancer_general | TRPS1 | chr8 | 117950438 | 117950468 | Hyper | cancer_general | AARD, AL832163 |
| chr8 | 117950783 | 117950914 | Hyper | cancer_general | AARD, AL832163 | chr8 | 120220116 | 120220145 | Hyper | literature | MAL2 |
| chr8 | 120220428 | 120220592 | Hyper | blood | MAL2 | chr8 | 120650979 | 120651008 | Hyper | literature | — |
| chr8 | 120651221 | 120651412 | Hyper | literature | — | chr8 | 121136879 | 121137748 | Hyper | tcga, cancer_general | COL14A1 |
| chr8 | 121823901 | 121823930 | Hyper | literature | — | chr8 | 121824203 | 121824481 | Hyper | literature | — |
| chr8 | 122651872 | 122651905 | Hyper | cancer_general | HAS2, HAS2-AS1 | chr8 | 124173246 | 124173501 | Hyper | cancer_general | TRNA_Met, WDR67 |
| chr8 | 127569621 | 127569676 | Hyper | blood | FAM84B | chr8 | 132052147 | 132053164 | Hyper | cancer_general | ADCY8 |
| chr8 | 132053715 | 132054749 | Hyper | cancer_general | ADCY8 | chr8 | 139508757 | 139509295 | Hyper | cancer_general | — |
| chr8 | 139509741 | 139509928 | Hyper | cancer_general | — | chr8 | 140714570 | 140714877 | Hyper | cancer_general | KCNK9 |
| chr8 | 140715090 | 140715120 | Hyper | cancer_general | KCNK9 | chr8 | 140715469 | 140715646 | Hyper | liver_tcga, cancer_general | KCNK9 |
| chr8 | 140715965 | 140716382 | Hyper | cancer_general | KCNK9 | chr8 | 142318155 | 142318184 | Hyper | liver_tcga | — |
| chr8 | 142528400 | 142529004 | Hyper | cancer_general, tcga | — | chr8 | 143532122 | 143532846 | Hyper | tcga, cancer_general | — |
| chr8 | 143533611 | 143533906 | Hyper | cancer_general | — | chr8 | 143592657 | 143592687 | Hyper | cancer_general | BAI1 |
| chr8 | 143858522 | 143858699 | Hyper | cancer_general, colorectal | LYNX1, LY6D | chr8 | 143859322 | 143859361 | Hyper | cancer_general | LY6D, LYNX1 |
| chr8 | 144203653 | 144203708 | Hyper | ovarian | LY6H | chr8 | 144241250 | 144241287 | Hyper | tcga, cancer_general | LY6H |
| chr8 | 144241543 | 144241582 | Hyper | cancer_general | LY6H | chr8 | 144241871 | 144242356 | Hyper | cancer_general | LY6H |
| chr8 | 144328321 | 144328565 | Hyper | cancer_general | ZFP41 | chr8 | 144509325 | 144510529 | Hyper | cancer_general | MAFA, ZC3H3 |
| chr8 | 144511225 | 144511424 | Hyper | cancer_general | ZC3H3, MAFA | chr8 | 144512041 | 144512192 | Hyper | liver_tcga, cancer_general | ZC3H3, MAFA |
| chr8 | 144512473 | 144512503 | Hyper | blood | ZC3H3, MAFA | chr8 | 144601799 | 144601851 | Hyper | liver_tcga | ZC3H3 |
| chr8 | 144650594 | 144650730 | Hyper | liver_tcga | GSDMD, MROH6, NAPRT1 | chr8 | 145033304 | 145033333 | Hyper | liver_tcga | — |
| chr8 | 145698347 | 145698379 | Hyper | cancer_general | CYHR1, FOXH1, KIFC2 | chr8 | 145806258 | 145806287 | Hyper | liver_tcga | ARHGAP39 |
| chr8 | 145925461 | 145925491 | Hyper | cancer_general | DQ588968 | chr8 | 145925947 | 145926089 | Hyper | liver_tcga | DQ588968 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 20175911 | 20175941 | Hypo | hepatobiliary | — | chr13 | 20733804 | 20736089 | Hyper | tcga | IL17D, AK05408, N6AMT2 |
| chr13 | 20875763 | 20875919 | Hyper | cancer_general | — | chr13 | 21295926 | 21295955 | Hyper | liver_tcga | FGF9 |
| chr13 | 21649636 | 21649775 | Hyper | cancer_general | — | chr13 | 22243273 | 22243469 | Hyper | tcga, cancer_general | — |
| chr13 | 23489851 | 23489914 | Hyper | cancer_general | — | chr13 | 23733447 | 23734020 | Hyper | cancer_general | ANKRD20A19P, C1QTNF9B |
| chr13 | 23734284 | 23734678 | Hyper | tcga, cancer_general | — | chr13 | 24477643 | 24477906 | Hyper | cancer_general | — |
| chr13 | 25115713 | 25115771 | Hyper | cancer_general | — | chr13 | 25319856 | 25321350 | Hyper | cancer_general, tcga | — |
| chr13 | 25321699 | 25321942 | Hyper | cancer_general | — | chr13 | 25593042 | 25593242 | Hyper | tcga | BC022569, AMER2 |
| chr13 | 25621045 | 25621394 | Hyper | cancer_general | — | chr13 | 25744716 | 25746000 | Hyper | tcga, cancer_general | ATP8A2 |
| chr13 | 25946205 | 25946411 | Hyper | tcga, cancer_general | ATP8A2 | chr13 | 25946620 | 25946796 | Hyper | cancer_general | ATP8A2 |
| chr13 | 26042678 | 26043499 | Hyper | cancer_general | ATP8A2 | chr13 | 26625301 | 26625727 | Hyper | cancer_general, colorectal | SHISA2 |
| chr13 | 26626077 | 26626148 | Hyper | tcga | SHISA2 | chr13 | 27132407 | 27132445 | Hyper | tcga | WASF3 |
| chr13 | 27334211 | 27334563 | Hyper | cancer_general | GPR12 | chr13 | 27334772 | 27334894 | Hyper | cancer_general | GPR12 |
| chr13 | 28365705 | 28366122 | Hyper | cancer_general | GSX1 | chr13 | 28366482 | 28366577 | Hyper | cancer_general | GSX1 |
| chr13 | 28367024 | 28367059 | Hyper | cancer_general | GSX1 | chr13 | 28367794 | 28368168 | Hyper | cancer_general | GSX1 |
| chr13 | 28368451 | 28368593 | Hyper | cancer_general | GSX1 | chr13 | 28368952 | 28369990 | Hyper | cancer_general | GSX1 |
| chr13 | 28370947 | 28371061 | Hyper | cancer_general | GSX1 | chr13 | 28394766 | 28394866 | Hyper | cancer_general | — |
| chr13 | 28395501 | 28395553 | Hyper | cancer_general | — | chr13 | 28395998 | 28396073 | Hyper | cancer_general | PDX1 |
| chr13 | 28491793 | 28491946 | Hyper | cancer_general | PDX1 | chr13 | 28492244 | 28492553 | Hyper | cancer_general | PDX1 |
| chr13 | 28503042 | 28503074 | Hyper | cancer_general | PDX1 | chr13 | 28528534 | 28528748 | Hyper | cancer_general | CDX2, ATP5EP2 |
| chr13 | 28540745 | 28540927 | Hyper | cancer_general | CDX2 | chr13 | 28543212 | 28543242 | Hyper | cancer_general | PRHOXNB, CDX2 |
| chr13 | 28544397 | 28544903 | Hyper | cancer_general | PRHOXNB, CDX2 | chr13 | 28549497 | 28550552 | Hyper | cancer_general | PRHOXNB, CDX2 |
| chr13 | 28551417 | 28551461 | Hyper | cancer_general | PRHOXNB | chr13 | 28551950 | 28552167 | Hyper | cancer_general | PRHOXNB, CDX2 |
| chr13 | 28552555 | 28552585 | Hyper | cancer_general | PRHOXNB, CDX2 | chr13 | 28552794 | 28552824 | Hyper | cancer_general | PRHOXNB, CDX2 |
| chr13 | 28553030 | 28553138 | Hyper | cancer_general | PRHOXNB, CDX2 | chr13 | 28589765 | 28589794 | Hyper | literature | FLT3 |
| chr13 | 28592605 | 28592658 | Hyper | literature | FLT3 | chr13 | 28601345 | 28601374 | Hyper | literature | FLT3 |
| chr13 | 28602326 | 28602355 | Hyper | literature | FLT3 | chr13 | 28608233 | 28608355 | Hyper | literature | FLT3 |
| chr13 | 28610123 | 28610152 | Hyper | literature | FLT3 | chr13 | 28674018 | 28674734 | Hyper | tcga, cancer_general | FLT3 |
| chr13 | 29067773 | 29068416 | Hyper | cancer_general | BC048278, FLT1 | chr13 | 29068926 | 29069065 | Hyper | cancer_general | BC048278, FLT1 |
| chr13 | 29106308 | 29107309 | Hyper | tcga, cancer_general | — | chr13 | 32605034 | 32605966 | Hyper | pancreas | BC035084, FRY |
| chr13 | 33590822 | 33590949 | Hyper | cancer_general | KL | chr13 | 33591300 | 33591419 | Hyper | cancer_general | KL |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 33924666 | 33924790 | Hyper | cancer_general | — | chr13 | 35517395 | 35517648 | Hyper | tcga | NBEA |
| chr13 | 36044829 | 36044930 | Hyper | cancer_general | NBEA, MIR548F5 | chr13 | 36045267 | 36045297 | Hyper | cancer_general | NBEA, MIR548F5 |
| chr13 | 36049995 | 36050025 | Hyper | pancreas | NBEA, MIR548F5 | chr13 | 36704939 | 36705055 | Hyper | cancer_general, tcga | — |
| chr13 | 36705451 | 36705489 | Hyper | cancer_general | — | chr13 | 36729093 | 36729125 | Hyper | cancer_general | — |
| chr13 | 36920317 | 36920413 | Hyper | liver_tcga, colorectal, cancer_general | SPG20OS, SPG20 | chr13 | 36920628 | 36920785 | Hyper | tcga, cancer_general, colorectal | SPG20OS, SPG20 |
| chr13 | 37004771 | 37005129 | Hyper | cancer_general | CCNA1 | chr13 | 37006577 | 37006762 | Hyper | cancer_general | CCNA1 |
| chr13 | 37248063 | 37248319 | Hyper | tcga | SERTM1 | chr13 | 37248979 | 37249030 | Hyper | cancer_general | SERTM1 |
| chr13 | 37633989 | 37634018 | Hyper | literature | SUPT20H | chr13 | 38443618 | 38443827 | Hyper | cancer_general | Mir_720, TRPC4 |
| chr13 | 39261410 | 39261446 | Hyper | tcga | FREM2 | chr13 | 43148421 | 43148450 | Hyper | tcga | TNFSF11 |
| chr13 | 43148669 | 43148698 | Hyper | tcga | TNFSF11 | chr13 | 43566247 | 43566647 | Hyper | tcga, cancer_general | EPSTI1 |
| chr13 | 44947746 | 44948197 | Hyper | cancer_general | SERP2 | chr13 | 45150013 | 45150276 | Hyper | tcga, liver_tcga | TSC22D1-AS1, TSC22D1 |
| chr13 | 45885876 | 45885905 | Hyper | liver_tcga | — | chr13 | 46425548 | 46425584 | Hyper | cancer_general | SLAH3 |
| chr13 | 46961494 | 46961533 | Hyper | esophageal | KIAA0226L | chr13 | 46961952 | 46961982 | Hyper | esophageal | KIAA0226L |
| chr13 | 47468139 | 47468168 | Hyper | literature | HTR2A | chr13 | 49794117 | 49795168 | Hyper | esophageal, cancer_general | MLNR |
| chr13 | 53312991 | 53313920 | Hyper | cancer_general | LECT1 | chr13 | 53419734 | 53419775 | Hyper | liver_tcga | PCDH8 |
| chr13 | 53420020 | 53420080 | Hyper | cancer_general | PCDH8 | chr13 | 53420385 | 53420720 | Hyper | cancer_general | PCDH8 |
| chr13 | 53421253 | 53421787 | Hyper | cancer_general | PCDH8 | chr13 | 53422315 | 53422362 | Hyper | cancer_general | PCDH8 |
| chr13 | 53423838 | 53423978 | Hyper | cancer_general | PCDH8 | chr13 | 58203602 | 58203644 | Hyper | cancer_general | PCDH17 |
| chr13 | 58203851 | 58204103 | Hyper | cancer_general | PCDH17 | chr13 | 58204350 | 58204393 | Hyper | tcga | PCDH17 |
| chr13 | 58206042 | 58206983 | Hyper | cancer_general | PCDH17 | chr13 | 58207462 | 58208020 | Hyper | cancer_general | PCDH17 |
| chr13 | 58208495 | 58208926 | Hyper | cancer_general | PCDH17 | chr13 | 67803735 | 67804074 | Hyper | tcga, cancer_general | PCDH9 |
| chr13 | 67804494 | 67804523 | Hyper | literature | PCDH9 | chr13 | 67805191 | 67805247 | Hyper | cancer_general | PCDH9 |
| chr13 | 70681626 | 70682071 | Hyper | cancer_general | ATXN8OS, KLHL1 | chr13 | 72439142 | 72439250 | Hyper | cancer_general | DACH1 |
| chr13 | 73336049 | 73336078 | Hyper | literature | DIS3, BORA | chr13 | 78492684 | 78492840 | Hyper | esophageal | RNF219-AS1, EDNRB |
| chr13 | 78493166 | 78493196 | Hyper | cancer_general | RNF219-AS1, EDNRB | chr13 | 78493455 | 78493809 | Hyper | cancer_general | RNF219-AS1, EDNRB |
| chr13 | 79168067 | 79168102 | Hyper | pancreas | POU4F1, RNF219-AS1 | chr13 | 79169818 | 79170884 | Hyper | literature, cancer_general | IRNF219-AS1, POU4F1 |
| chr13 | 79171118 | 79171196 | Hyper | cancer_general | POU4F1, RNF219-AS1 | chr13 | 79175770 | 79176783 | Hyper | liver_tcga, cancer_general | RNF219-AS1, POU4F1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 79176993 | 79177998 | Hyper | tcga, liver_tcga, cancer_general | POU4F1, RNF219-AS1 | chr13 | 79183406 | 79183485 | Hyper | cancer_general | RNF219, POU4F1, RNF219-AS1 |
| chr13 | 81229343 | 81229372 | Hyper | literature | | chr13 | 84455236 | 84455292 | Hyper | cancer_general | SLITRK1 |
| chr13 | 84455581 | 84455715 | Hyper | cancer_general | SLITRK1 | chr13 | 84457491 | 84457521 | Hyper | cancer_general | SLITRK1 |
| chr13 | 88323579 | 88324207 | Hyper | tcga, cancer_general | SLITRK5 | chr13 | 88324516 | 88324611 | Hyper | cancer_general, colorectal, | SLITRK5 |
| chr13 | 88325300 | 88325460 | Hyper | cancer_general | SLITRK5 | chr13 | 88325819 | 88326061 | Hyper | cancer_general | SLITRK5 |
| chr13 | 88326538 | 88327014 | Hyper | cancer_general, tcga | SLITRK5 | chr13 | 92050760 | 92050814 | Hyper | esophageal | GPC5 |
| chr13 | 92051139 | 92051168 | Hyper | tcga | GPC5 | chr13 | 92051374 | 92051529 | Hyper | tcga, cancer_general | GPC5 |
| chr13 | 93879288 | 93879375 | Hyper | tcga | GPC6 | chr13 | 93879670 | 93879700 | Hyper | cancer_general | GPC6 |
| chr13 | 93880089 | 93880856 | Hyper | tcga, colorectal, cancer_general | GPC6 | chr13 | 93357311 | 93357341 | Hyper | cancer_general | SOX21, AK055459 |
| chr13 | 95357574 | 95357775 | Hyper | cancer_general | SOX21, AK055459 | chr13 | 95358041 | 95358165 | Hyper | cancer_general | SOX21, AK055459 |
| chr13 | 95359747 | 95359803 | Hyper | cancer_general | SOX21, AK055459 | chr13 | 95360322 | 95360371 | Hyper | cancer_general | SOX21, AK055459 |
| chr13 | 95363210 | 95363429 | Hyper | cancer_general | SOX21, AK055459 | chr13 | 95363796 | 95364196 | Hyper | tcga, cancer_general | AK055459, SOX21 |
| chr13 | 95364495 | 95364800 | Hyper | tcga, cancer_general, colorectal | SOX21, AK055459, SOX21 | chr13 | 95620021 | 95620078 | Hyper | cancer_general, colorectal, cancer_general | |
| chr13 | 95620647 | 95621011 | Hyper | cancer_general, tcga | | chr13 | 96204853 | 96205363 | Hyper | liver_tcga, cancer_general | CLDN10 |
| chr13 | 96296225 | 96296473 | Hyper | cancer_general | | chr13 | 96296693 | 96297137 | Hyper | tcga, cancer_general | |
| chr13 | 96743788 | 96744175 | Hyper | tcga, cancer_general | HS6ST3 | chr13 | 100547713 | 100547982 | Hyper | tcga, cancer_general | |
| chr13 | 100608257 | 100609055 | Hyper | cancer_general | ZIC5 | chr13 | 100621941 | 100622015 | Hyper | cancer_general | ZIC5 |
| chr13 | 100624316 | 100624348 | Hyper | cancer_general | ZIC2, ZIC5 | chr13 | 100624587 | 100624729 | Hyper | cancer_general | ZIC2, ZIC5 |
| chr13 | 100626929 | 100627009 | Hyper | cancer_general | ZIC2, ZIC5 | chr13 | 100627295 | 100627348 | Hyper | cancer_general | ZIC2, ZIC5 |
| chr13 | 100627688 | 100627717 | Hyper | liver_tcga | ZIC2, ZIC5 | chr13 | 100630169 | 100630430 | Hyper | liver_tcga | ZIC2, ZIC5 |
| chr13 | 100630630 | 100630997 | Hyper | cancer_general | ZIC5, ZIC2 | chr13 | 100633089 | 100633184 | Hyper | blood | ZIC2 |
| chr13 | 100634314 | 100634617 | Hyper | blood | ZIC2 | chr13 | 100635406 | 100635451 | Hyper | cancer_general | ZIC2 |
| chr13 | 100636167 | 100636238 | Hyper | cancer_general | ZIC2 | chr13 | 100637390 | 100637485 | Hyper | cancer_general | ZIC2 |
| chr13 | 100641282 | 100642201 | Hyper | cancer_general | ZIC2 | chr13 | 100643296 | 100643435 | Hyper | cancer_general | ZIC2 |
| chr13 | 100644055 | 100644212 | Hyper | cancer_general | ZIC2 | chr13 | 100649325 | 100649931 | Hyper | cancer_general | |
| chr13 | 102568454 | 102568484 | Hyper | cancer_general | FGF14 | chr13 | 102568856 | 102568994 | Hyper | cancer_general | FGF14 |
| chr13 | 102569203 | 102569542 | Hyper | cancer_general | FGF14 | chr13 | 103046721 | 103046995 | Hyper | tcga, cancer_general | FGF14-AS2 |
| chr13 | 103052347 | 103052574 | Hyper | tcga | FGF14-AS2 | chr13 | 103052892 | 103052940 | Hyper | cancer_general | FGF14-AS2 |
| chr13 | 103053394 | 103053496 | Hyper | tcga | FGF14-AS2 | chr13 | 105791875 | 105791904 | Hyper | literature | |
| chr13 | 107186855 | 107186884 | Hyper | liver_tcga | ARGLU1, EFNB2 | chr13 | 107187162 | 107187426 | Hyper | liver_tcga, tcga | ARGLU1, EFNB2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 107187666 | 107187695 | Hyper | liver_tcga | ARGLU1, EFNB2 | chr13 | 107188241 | 107188430 | Hyper | tcga, liver_tcga | ARGLU1, EFNB2 |
| chr13 | 108518355 | 108518392 | Hyper | cancer_general | — | chr13 | 108518813 | 108518933 | Hyper | cancer_general | — |
| chr13 | 108519254 | 108519367 | Hyper | cancer_general | — | chr13 | 108519737 | 108519894 | Hyper | tcga | — |
| chr13 | 108520376 | 108520580 | Hyper | tcga, cancer_general | — | chr13 | 108520979 | 108521076 | Hyper | cancer_general | — |
| chr13 | 109147685 | 109148351 | Hyper | cancer_general | — | chr13 | 109148783 | 109149185 | Hyper | tcga, cancer_general | — |
| chr13 | 110958816 | 110958981 | Hyper | cancer_general | COL4A1, COL4A2 | chr13 | 110959220 | 110959255 | Hyper | cancer_general | COL4A2, COL4A1 |
| chr13 | 110959705 | 110959970 | Hyper | colorectal, cancer_general | COL4A2, COL4A1 | chr13 | 110960250 | 110960282 | Hyper | cancer_general | COL4A2, COL4A1 |
| chr13 | 110960541 | 110960603 | Hyper | cancer_general | COL4A2, COL4A1 | chr13 | 112707694 | 112707869 | Hyper | cancer_general | — |
| chr13 | 112708088 | 112708513 | Hyper | cancer_general | — | chr13 | 112709388 | 112709617 | Hyper | cancer_general | — |
| chr13 | 112709883 | 112709928 | Hyper | cancer_general | — | chr13 | 112710344 | 112710508 | Hyper | cancer_general | — |
| chr13 | 112710759 | 112711776 | Hyper | cancer_general | — | chr13 | 112712017 | 112713029 | Hyper | cancer_general | SOX1 |
| chr13 | 112715370 | 112715642 | Hyper | cancer_general | SOX1 | chr13 | 112715985 | 112716313 | Hyper | cancer_general | SOX1 |
| chr13 | 112716677 | 112716721 | Hyper | cancer_general | SOX1 | chr13 | 112717026 | 112717536 | Hyper | cancer_general | SOX1 |
| chr13 | 112717835 | 112717949 | Hyper | cancer_general | SOX1 | chr13 | 112720033 | 112720505 | Hyper | cancer_general | SOX1 |
| chr13 | 112720723 | 112720767 | Hyper | cancer_general | SOX1 | chr13 | 112721012 | 112721042 | Hyper | cancer_general | SOX1 |
| chr13 | 112721261 | 112722312 | Hyper | liver_tcga, literature, cancer_general | SOX1 | chr13 | 112724505 | 112724535 | Hyper | cancer_general | SOX1 |
| chr13 | 112726337 | 112726560 | Hyper | cancer_general | SOX1 | chr13 | 112727984 | 112728270 | Hyper | cancer_general | SOX1 |
| chr13 | 112758107 | 112758257 | Hyper | cancer_general | AK055145 | chr13 | 112758463 | 112758613 | Hyper | cancer_general | AK055145 |
| chr13 | 112758849 | 112759248 | Hyper | cancer_general | AK055145 | chr13 | 112759612 | 112759642 | Hyper | cancer_general | AK055145 |
| chr13 | 112759959 | 112760327 | Hyper | cancer_general | AK055145 | chr13 | 112760795 | 112761214 | Hyper | cancer_general | — |
| chr13 | 113244509 | 113244595 | Hyper | pancreas | TUBGCP3 | chr13 | 114897194 | 114897240 | Hyper | hepatobiliary | — |
| AC211950.2_11234-25326 | 129 | 257 | Hyper | cancer_general | — | AC211950.2_11234-25326 | 13335 | 13445 | Hyper | cancer_general | — |
| chr15 | 13743 | 13889 | Hyper | cancer_general | — | chr15 | 23158397 | 23158489 | Hyper | cancer_general | — |
| chr15 | 26107640 | 26107860 | Hyper | cancer_general | — | chr15 | 26108096 | 26108701 | Hyper | tcga, cancer_general | — |
| chr15 | 27018363 | 27018436 | Hyper | cancer_general | — | chr15 | 27212887 | 27213172 | Hyper | cancer_general | GABRG3 |
| chr15 | 27216396 | 27216429 | Hyper | cancer_general | GABRG3 | chr15 | 27604062 | 27604139 | Hyper | cancer_general | GABRG3 |
| chr15 | 28341699 | 28342429 | Hyper | tcga, cancer_general | OCA2 | chr15 | 28344173 | 28344287 | Hyper | cancer_general | OCA2 |
| chr15 | 28352240 | 28352850 | Hyper | cancer_general, tcga | HERC2, OCA2 | chr15 | 29077284 | 29077383 | Hyper | cancer_general | LOC646278 |
| chr15 | 29130807 | 29131875 | Hyper | cancer_general | APBA2 | chr15 | 29396330 | 29396360 | Hyper | pancreas | APBA2 |
| chr15 | 29407777 | 29408001 | Hyper | tcga | FAM189A1 | chr15 | 29862502 | 29862582 | Hyper | tcga | — |
| chr15 | 30115185 | 30115228 | Hyper | blood | TJP1 | chr15 | 31775596 | 31776121 | Hyper | cancer_general | OTUD7A |
| chr15 | 32933918 | 32934018 | Hyper | liver_tcga, literature | SCG5, ARHGAP11A | chr15 | 33009747 | 33011348 | Hyper | tcga, liver_tcga, cancer_general | GREM1, AX747968 |
| chr15 | 33011601 | 33011633 | Hyper | cancer_general | GREM1, AX747968 | chr15 | 33487057 | 33487120 | Hyper | liver_tcga | FMN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 33602801 | 33602886 | Hyper | cancer_general | RYR3 | chr15 | 33603194 | 33603624 | Hyper | cancer_general | RYR3 |
| chr15 | 34517058 | 34517334 | Hyper | esophageal | EMC4, SLC12A6 | chr15 | 34630420 | 34630449 | Hyper | tcga | NOP10, NUTM1, SLC12A6 |
| chr15 | 34729478 | 34729582 | Hyper | cancer_general | — | chr15 | 34786504 | 34787304 | Hyper | cancer_general | — |
| chr15 | 35046607 | 35046637 | Hyper | cancer_general | AK092087, GJD2 | chr15 | 35047034 | 35047133 | Hyper | cancer_general | AK092087, GJD2 |
| chr15 | 35087666 | 35087698 | Hyper | cancer_general | AK092087, ACTC1 | chr15 | 37180309 | 37180743 | Hyper | cancer_general | MEIS2, LOC145845 |
| chr15 | 37402974 | 37403238 | Hyper | lung, cancer_general | MEIS2 | chr15 | 40211819 | 40212190 | Hyper | cancer_general | GPR176 |
| chr15 | 40575630 | 40575744 | Hyper | tcga, cancer_general | PLCB2, ANKRD63, PAK6 | chr15 | 40675092 | 40675121 | Hyper | literature | KNSTRN |
| chr15 | 40763811 | 40763862 | Hyper | hepatobiliary | CHST14, BAHD1 | chr15 | 41787804 | 41787852 | Hyper | cancer_general | LTK, ITPKA |
| chr15 | 41804878 | 41805772 | Hyper | cancer_general | RPAP1, LTK, ITPKA | chr15 | 41913750 | 41913807 | Hyper | cancer_general | MGA |
| chr15 | 41952572 | 41952711 | Hyper | cancer_general | MGA | chr15 | 43810405 | 43810435 | Hyper | pancreas | MAP1A |
| chr15 | 45403636 | 45404130 | Hyper | cancer_general | DUOXA2, DUOXA1, DUOX2 | chr15 | 45404881 | 45405117 | Hyper | tcga | DUOXA2, DUOXA1, DUOX2 |
| chr15 | 45421385 | 45421435 | Hyper | cancer_general | DUOX1, DUOXA1 | chr15 | 45421950 | 45422095 | Hyper | liver_tcga | DUOX1, DUOXA1 |
| chr15 | 45427354 | 45427410 | Hyper | cancer_general | DUOXA1, DUOX1 | chr15 | 45427611 | 45427786 | Hyper | cancer_general | DUOX1, DUOXA1 |
| chr15 | 45479460 | 45479697 | Hyper | cancer_general | SHF | chr15 | 45493209 | 45493371 | Hyper | ovarian | TRNA, TRNA_His |
| chr15 | 45670462 | 45670879 | Hyper | colorectal | BC039389, GATM, GATM-AS1 | chr15 | 47476118 | 47476450 | Hyper | tcga | SEMA6D |
| chr15 | 47476868 | 47477018 | Hyper | tcga | SEMA6D | chr15 | 48483956 | 48483986 | Hyper | cancer_general | CTXN2, SLC12A1 |
| chr15 | 48936726 | 48937987 | Hyper | colorectal, cancer_general, tcga | FBN1 | chr15 | 48938212 | 48938510 | Hyper | cancer_general | FBN1 |
| chr15 | 51385913 | 51386181 | Hyper | cancer_general | TNFAIP8L3 | chr15 | 51634075 | 51634135 | Hyper | cancer_general | GLDN |
| chr15 | 51973646 | 51973934 | Hyper | tcga | SCG3 | chr15 | 53075809 | 53077361 | Hyper | cancer_general | ONECUT1 |
| chr15 | 53077655 | 53077731 | Hyper | cancer_general | ONECUT1 | chr15 | 53078064 | 53078236 | Hyper | cancer_general | ONECUT1 |
| chr15 | 53079340 | 53080082 | Hyper | cancer_general | ONECUT1 | chr15 | 53080337 | 53080606 | Hyper | cancer_general | ONECUT1 |
| chr15 | 53080935 | 53081025 | Hyper | cancer_general | ONECUT1 | chr15 | 53081306 | 53081677 | Hyper | cancer_general | ONECUT1 |
| chr15 | 53082443 | 53082491 | Hyper | esophageal | — | chr15 | 53096816 | 53096891 | Hyper | cancer_general | — |
| chr15 | 53097231 | 53097261 | Hyper | cancer_general | — | chr15 | 53097634 | 53097974 | Hyper | tcga, cancer_general | — |
| chr15 | 53098316 | 53098658 | Hyper | cancer_general | — | chr15 | 54270498 | 54270707 | Hyper | cancer_general | — |
| chr15 | 54270932 | 54270961 | Hyper | tcga | — | chr15 | 55880879 | 55881011 | Hyper | tcga | PYGO1 |
| chr15 | 58357318 | 58357451 | Hyper | cancer_general | ALDH1A2 | chr15 | 58357733 | 58358200 | Hyper | cancer_general, liver_tcga | ALDH1A2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 59158809 | 59158901 | Hyper | pancreas | unknown, FAM63B | chr15 | 60287038 | 60287733 | Hyper | cancer_general | FOXB1 |
| chr15 | 60288786 | 60288844 | Hyper | cancer_general | FOXB1 | chr15 | 60289310 | 60289546 | Hyper | tcga, cancer_general | FOXB1 |
| chr15 | 60296122 | 60296209 | Hyper | cancer_general | FOXB1 | chr15 | 60296598 | 60297409 | Hyper | tcga, liver_tcga, cancer_general | FOXB1 |
| chr15 | 60297637 | 60298108 | Hyper | cancer_general | FOXB1 | chr15 | 61520916 | 61521014 | Hyper | tcga | — |
| chr15 | 61521659 | 61521937 | Hyper | tcga | — | chr15 | 62456922 | 62456952 | Hyper | blood | C2CD4B |
| chr15 | 65669859 | 65669899 | Hyper | esophageal | IGDCC4 | chr15 | 66727409 | 66727498 | Hyper | literature | MAP2K1 |
| chr15 | 66729148 | 66729177 | Hyper | literature | MAP2K1 | chr15 | 66774117 | 66774203 | Hyper | literature | SNAPC5, MAP2K1 |
| chr15 | 68112611 | 68112641 | Hyper | cancer_general | SKOR1 | chr15 | 68113868 | 68113898 | Hyper | cancer_general | SKOR1 |
| chr15 | 68114139 | 68114195 | Hyper | cancer_general | SKOR1 | chr15 | 68116369 | 68116621 | Hyper | cancer_general | SKOR1 |
| chr15 | 68117830 | 68118633 | Hyper | cancer_general | SKOR1 | chr15 | 68118886 | 68119218 | Hyper | cancer_general | SKOR1 |
| chr15 | 68119548 | 68120576 | Hyper | cancer_general | SKOR1 | chr15 | 68120827 | 68120857 | Hyper | cancer_general | SKOR1 |
| chr15 | 68121058 | 68122076 | Hyper | lung, cancer_general | SKOR1 | chr15 | 68122643 | 68122673 | Hyper | cancer_general | SKOR1 |
| chr15 | 68125261 | 68125664 | Hyper | cancer_general | SKOR1 | chr15 | 68127801 | 68128350 | Hyper | cancer_general | SKOR1 |
| chr15 | 68128594 | 68128688 | Hyper | pancreas | SKOR1 | chr15 | 68260519 | 68260709 | Hyper | liver_tcga | — |
| chr15 | 71055636 | 71055815 | Hyper | blood | — | chr15 | 72612540 | 72612906 | Hyper | liver_tcga, hepatobiliary | CELF6 |
| chr15 | 73660004 | 73660067 | Hyper | cancer_general | HCN4 | chr15 | 73661469 | 73661666 | Hyper | cancer_general, tcga | HCN4 |
| chr15 | 74045060 | 74045097 | Hyper | tcga | C15orf59 | chr15 | 74422006 | 74422146 | Hyper | cancer_general | ISLR2, LOC283731 |
| chr15 | 74422869 | 74423002 | Hyper | cancer_general | ISLR2, LOC283731 | chr15 | 74658151 | 74658587 | Hyper | cancer_general | BC013681, CYP11A1, LOC729739 |
| chr15 | 75251346 | 75251382 | Hyper | cancer_general | RPP25 | chr15 | 75251672 | 75251786 | Hyper | cancer_general | RPP25 |
| chr15 | 75471116 | 75471193 | Hyper | cancer_general | — | chr15 | 76627508 | 76627826 | Hyper | liver_tcga, cancer_general | ISL2 |
| chr15 | 76629056 | 76629220 | Hyper | cancer_general | ISL2 | chr15 | 76629494 | 76629531 | Hyper | lung | ISL2 |
| chr15 | 76629814 | 76630847 | Hyper | cancer_general | SCAPER, ISL2 | chr15 | 76632257 | 76632423 | Hyper | cancer_general | SCAPER, ISL2 |
| chr15 | 76635120 | 76635197 | Hyper | cancer_general | SCAPER, ISL2 | chr15 | 76635530 | 76635560 | Hyper | cancer_general | SCAPER, ISL2 |
| chr15 | 76638472 | 76638719 | Hyper | cancer_general | SCAPER, ISL2 | chr15 | 78111154 | 78111210 | Hyper | cancer_general | — |
| chr15 | 78556819 | 78557108 | Hyper | tcga, liver_tcga | DNAJA4 | chr15 | 78632727 | 78632823 | Hyper | cancer_general | CRABP1 |
| chr15 | 78912281 | 78912401 | Hyper | cancer_general | CHRNB4, AX748237, CHRNA3 | chr15 | 78912623 | 78912653 | Hyper | cancer_general | CHRNB4, AX748237, CHRNA3 |
| chr15 | 78912912 | 78913170 | Hyper | tcga, cancer_general | CHRNB4, AX748237, CHRNA3 | chr15 | 78913535 | 78913651 | Hyper | cancer_general | CHRNB4, AX748237, CHRNA3 |
| chr15 | 79104217 | 79104246 | Hyper | tcga | ADAMTS7 | chr15 | 79104466 | 79104495 | Hyper | tcga | ADAMTS7 |
| chr15 | 79381705 | 79382571 | Hyper | cancer_general | — | chr15 | 79382786 | 79383257 | Hyper | cancer_general | MIR184, LOC729911 |
| chr15 | 79383947 | 79383977 | Hyper | colorectal | — | chr15 | 79502211 | 79502360 | Hyper | cancer_general | — |
| chr15 | 79575278 | 79575474 | Hyper | cancer_general | ANKRD34C | chr15 | 79576145 | 79576277 | Hyper | cancer_general | ANKRD34C |

TABLE 11-continued

| chr | Start | Stop | Hypo/hyper | classification | annotation |
|---|---|---|---|---|---|
| chr15 | 79724126 | 79724240 | Hyper | cancer_general | KIAA1024 |
| chr15 | 79725422 | 79725539 | Hyper | cancer_general | KIAA1024 |
| chr15 | 82336879 | 82336972 | Hyper | cancer_general | MEX3B |
| chr15 | 83315336 | 83315393 | Hyper | cancer_general | LOC283692 |
| chr15 | 83349234 | 83349686 | Hyper | cancer_general | AP3B2 |
| chr15 | 83776255 | 83776785 | Hyper | liver_tcga, colorectal, cancer_general | TM6SF1 |
| chr15 | 83877055 | 83877149 | Hyper | tcga | HDGFRP3 |
| chr15 | 83953102 | 83953903 | Hyper | tcga, cancer_general | BNC1 |
| chr15 | 84115747 | 84115966 | Hyper | cancer_general | SH3GL3 |
| chr15 | 84322851 | 84323037 | Hyper | cancer_general | ADAMTSL3 |
| chr15 | 88798688 | 88798791 | Hyper | cancer_general | NTRK3, NTRK3-AS1 |
| chr15 | 88800541 | 88801103 | Hyper | cancer_general | NTRK3-AS1, NTRK3 |
| chr15 | 89248753 | 89248907 | Hyper | tcga, cancer_general | — |
| chr15 | 89346670 | 89346943 | Hyper | cancer_general | ACAN |
| chr15 | 89910521 | 89910748 | Hyper | cancer_general | MIR9-3, LINC00925 |
| chr15 | 89913750 | 89913780 | Hyper | cancer_general | MIR9-3, LINC00925, MIR9-3 |
| chr15 | 89915240 | 89915369 | Hyper | cancer_general | LINC00925 |
| chr15 | 89921956 | 89922006 | Hyper | cancer_general | LINC00925, AK054710, LINC00925 |
| chr15 | 89942755 | 89942945 | Hyper | cancer_general | AK054710, LINC00925 |
| chr15 | 89949410 | 89949942 | Hyper | cancer_general | AK054710, LINC00925 |
| chr15 | 89951400 | 89951801 | Hyper | cancer_general | — |
| chr15 | 89954197 | 89954335 | Hyper | cancer_general | LINC00928, RHCG |
| chr15 | 90039563 | 90039711 | Hyper | cancer_general | SV2B |
| chr15 | 91643360 | 91643586 | Hyper | esophageal | ST8SIA2 |
| chr15 | 92937153 | 92937374 | Hyper | cancer_general, tcga | — |
| chr15 | 93631739 | 93632014 | Hyper | tcga, cancer_general | — |

| Chr | Start | Stop | Hypo/hyper | Classification | annotation |
|---|---|---|---|---|---|
| chr15 | 79724502 | 79725140 | Hyper | tcga, cancer_general | KIAA1024 |
| chr15 | 81071827 | 81071867 | Hyper | blood | KIAA1199 |
| chr15 | 82340070 | 82340157 | Hyper | cancer_general | MEX3B |
| chr15 | 83316251 | 83317087 | Hyper | cancer_general | LOC283692 |
| chr15 | 83378212 | 83378370 | Hyper | esophageal | LOC338963, AP3B2 |
| chr15 | 83875648 | 83875901 | Hyper | liver_tcga, cancer_general | HDGFRP3 |
| chr15 | 83952198 | 83952736 | Hyper | tcga, cancer_general | BNC1 |
| chr15 | 83954380 | 83954409 | Hyper | literature | BNC1 |
| chr15 | 84116905 | 84116949 | Hyper | tcga | SH3GL3 |
| chr15 | 84748578 | 84749260 | Hyper | cancer_general | EFTUD1P1 |
| chr15 | 88799537 | 88800317 | Hyper | cancer_general, tcga | NTRK3-AS1, NTRK3 |
| chr15 | 89149169 | 89149448 | Hyper | cancer_general | MIR1179, MIR7-2, MIR3529, AK054749 |
| chr15 | 89346050 | 89346393 | Hyper | cancer_general | ACAN |
| chr15 | 89903484 | 89903814 | Hyper | cancer_general | MIR9-3, LINC00925 |
| chr15 | 89911087 | 89911186 | Hyper | cancer_general | MIR9-3, LINC00925 |
| chr15 | 89914231 | 89914895 | Hyper | cancer_general | LINC00925, MIR9-3 |
| chr15 | 89920809 | 89920901 | Hyper | literature | MIR9-3 |
| chr15 | 89922211 | 89922546 | Hyper | cancer_general | LINC00925, AK054710, LINC00925 |
| chr15 | 89943410 | 89943706 | Hyper | pancreas, liver_tcga, tcga | |
| chr15 | 89950236 | 89951113 | Hyper | cancer_general | AK054710, LINC00925 |
| chr15 | 89952153 | 89953055 | Hyper | literature, cancer_general | |
| chr15 | 89956364 | 89956450 | Hyper | cancer_general | LINC00925 |
| chr15 | 90631823 | 90631948 | Hyper | literature | IDH2 |
| chr15 | 92936290 | 92936322 | Hyper | cancer_general | ST8SIA2 |
| chr15 | 92937927 | 92938309 | Hyper | cancer_general, tcga | ST8SIA2 |
| chr15 | 93632660 | 93633233 | Hyper | cancer_general, tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 95388568 | 95388616 | Hyper | cancer_general | LOC440311 | chr15 | 96874362 | 96874514 | Hyper | blood | NR2F2, MIR1469, NR2F2-AS1 |
| chr15 | 96889154 | 96889183 | Hyper | tcga | NR2F2 | chr15 | 96889401 | 96889430 | Hyper | tcga | NR2F2 |
| chr15 | 96897934 | 96898010 | Hyper | cancer_general | — | chr15 | 96911559 | 96911710 | Hyper | cancer_general | — |
| chr15 | 96952696 | 96953209 | Hyper | tcga, cancer_general | — | chr15 | 96959730 | 96959976 | Hyper | cancer_general | — |
| chr15 | 96960376 | 96960409 | Hyper | cancer_general | — | chr15 | 96960732 | 96960826 | Hyper | cancer_general | — |
| chr15 | 98504114 | 98504144 | Hyper | blood | ARRDC4 | chr15 | 98836178 | 98836393 | Hyper | tcga, cancer_general | |
| chr15 | 98964786 | 98965138 | Hyper | esophageal | — | chr15 | 99193206 | 99193480 | Hyper | blood, tcga, liver_tcga | IGF1R |
| chr15 | 99193914 | 99194186 | Hyper | tcga, liver_tcga | IGF1R | chr15 | 100913423 | 100913880 | Hyper | cancer_general | — |
| chr15 | 101389973 | 101390023 | Hyper | liver_tcga | LOC145757 | chr15 | 101420521 | 101420610 | Hyper | cancer_general | ALDH1A3 |
| chr15 | 101420945 | 101420989 | Hyper | cancer_general | ALDH1A3 | chr15 | 101513607 | 101513754 | Hyper | tcga | LRRK1 |
| chr15 | 102286533 | 102286563 | Hyper | cancer_general | DQ588428, DQ593627, DQ588362, DQ578285, DQ597461, DQ582666, DQ593630, DQ582294, DQ588439, BC101079, DQ596486, DQ597703, DQ585237, DQ588452, DQ586526, DQ576888, DQ582460, DQ586138, DQ578289, DQ593624, DQ593353, DQ571896, DQ584425, DQ597539, DQ585740, DQ595661 | chr21 | 22370332 | 22370458 | Hyper | cancer_general | NCAM2 |
| chr21 | 22370688 | 22370718 | Hyper | cancer_general | NCAM2 | chr21 | 26934368 | 26934786 | Hyper | tcga, liver_tcga, cancer_general | MIR155HG |
| chr21 | 27011773 | 27011807 | Hyper | tcga | JAM2 | chr21 | 27012373 | 27012431 | Hyper | colorectal | JAM2 |
| chr21 | 27944995 | 27945081 | Hyper | cancer_general | CYYR1 | chr21 | 27945398 | 27945427 | Hyper | tcga | CYYR1 |
| chr21 | 27945693 | 27945722 | Hyper | tcga | CYYR1 | chr21 | 28216585 | 28217690 | Hyper | cancer_general | ADAMTS1 |
| chr21 | 28218774 | 28219045 | Hyper | cancer_general, tcga | ADAMTS1 | chr21 | 28338836 | 28338887 | Hyper | cancer_general | — |

TABLE 11-continued

| chr | Start | Stop | Hypo/hyper | classification | annotation |
|---|---|---|---|---|---|
| chr21 | 28339247 | 28339501 | Hyper | tcga, cancer_general | — |
| chr21 | 31311404 | 31311553 | Hyper | cancer_general | — |
| chr21 | 31312313 | 31312445 | Hyper | tcga, cancer_general | — |
| chr21 | 33245683 | 33245718 | Hyper | esophageal | HUNK |
| chr21 | 33785288 | 33785325 | Hyper | blood | EVA1C |
| chr21 | 34395302 | 34396269 | Hyper | tcga, cancer_general | OLIG2 |
| chr21 | 34398070 | 34398634 | Hyper | tcga | OLIG2 |
| chr21 | 34401185 | 34401392 | Hyper | cancer_general | OLIG2 |
| chr21 | 34443103 | 34443262 | Hyper | cancer_general | OLIG1 |
| chr21 | 34443893 | 34443956 | Hyper | cancer_general | OLIG1 |
| chr21 | 36041468 | 36041697 | Hyper | cancer_general | CLIC6 |
| chr21 | 36042658 | 36042861 | Hyper | cancer_general | CLIC6 |
| chr21 | 38064966 | 38065737 | Hyper | cancer_general | SIM2 |
| chr21 | 38067203 | 38067233 | Hyper | cancer_general | SIM2 |
| chr21 | 38068565 | 38068783 | Hyper | cancer_general | SIM2 |
| chr21 | 38069459 | 38069496 | Hyper | cancer_general | SIM2 |
| chr21 | 38070705 | 38070765 | Hyper | blood | SIM2 |
| chr21 | 38073007 | 38073070 | Hyper | cancer_general | SIM2 |
| chr21 | 38076854 | 38077152 | Hyper | tcga, cancer_general | SIM2 |
| chr21 | 38079988 | 38080684 | Hyper | cancer_general | SIM2 |
| chr21 | 38081445 | 38081835 | Hyper | cancer_general | SIM2 |
| chr21 | 38082315 | 38082345 | Hyper | cancer_general | SIM2 |
| chr21 | 38119904 | 38120312 | Hyper | cancer_general | HLCS |
| chr21 | 39870612 | 39870641 | Hyper | literature | ERG |
| chr21 | 40033877 | 40033906 | Hyper | literature | ERG |
| chr21 | 43186698 | 43186889 | Hyper | blood | RIPK4 |
| chr21 | 44514762 | 44514791 | Hyper | literature | U2AF1 |
| chr21 | 44847591 | 44847622 | Hyper | tcga | SIK1 |
| chr21 | 45717477 | 45717548 | Hyper | head_neck | PFKL, AIRE |
| chr21 | 46127039 | 46127094 | Hyper | cancer_general | KRTAP10-12 |
| chr21 | 46128902 | 46128938 | Hyper | cancer_general | — |
| chr21 | 46825825 | 46826067 | Hyper | tcga | COL18A1-AS2, COL18A1 |
| chr21 | 47062544 | 47062825 | Hyper | cancer_general | PCBP3 |
| chr21 | 47064250 | 47064377 | Hyper | cancer_general | PCBP3 |
| chr21 | 28339892 | 28340318 | Hyper | tcga, cancer_general | — |
| chr21 | 31311944 | 31312105 | Hyper | tcga, cancer_general | — |
| chr21 | 33244921 | 33245040 | Hyper | esophageal | HUNK |
| chr21 | 33246009 | 33246190 | Hyper | esophageal | HUNK |
| chr21 | 34392171 | 34392566 | Hyper | cancer_general, tcga | OLIG2 |
| chr21 | 34396795 | 34397037 | Hyper | cancer_general | OLIG2 |
| chr21 | 34398933 | 34400258 | Hyper | cancer_general | OLIG2 |
| chr21 | 34442547 | 34442665 | Hyper | cancer_general | OLIG1 |
| chr21 | 34443509 | 34443686 | Hyper | cancer_general | OLIG1 |
| chr21 | 34444163 | 34444598 | Hyper | tcga, cancer_general | OLIG1 |
| chr21 | 36041985 | 36042238 | Hyper | cancer_general | CLIC6 |
| chr21 | 36042457 | 36042683 | Hyper | cancer_general | SIM2 |
| chr21 | 38065955 | 38066112 | Hyper | cancer_general | SIM2 |
| chr21 | 38068178 | 38068289 | Hyper | cancer_general | SIM2 |
| chr21 | 38069093 | 38069203 | Hyper | cancer_general | SIM2 |
| chr21 | 38069825 | 38070162 | Hyper | cancer_general, tcga | SIM2 |
| chr21 | 38071791 | 38071905 | Hyper | blood | SIM2 |
| chr21 | 38073300 | 38073860 | Hyper | cancer_general | SIM2 |
| chr21 | 38078415 | 38078487 | Hyper | cancer_general | SIM2 |
| chr21 | 38081085 | 38081207 | Hyper | tcga | SIM2 |
| chr21 | 38082042 | 38082072 | Hyper | cancer_general | SIM2 |
| chr21 | 38082930 | 38083196 | Hyper | cancer_general | SIM2 |
| chr21 | 39047776 | 39047838 | Hyper | head_neck | KCNJ6 |
| chr21 | 40033619 | 40033648 | Hyper | literature | ERG |
| chr21 | 40984685 | 40984900 | Hyper | tcga | B3GALT5, C21orf88 |
| chr21 | 44494891 | 44495155 | Hyper | tcga, cancer_general | CBS |
| chr21 | 44524441 | 44524470 | Hyper | literature | U2AF1 |
| chr21 | 45148615 | 45148758 | Hyper | cancer_general | PDXK |
| chr21 | 46125933 | 46126721 | Hyper | cancer_general | KRTAP10-12 |
| chr21 | 46127542 | 46127692 | Hyper | cancer_general | KRTAP10-12 |
| chr21 | 46129444 | 46129485 | Hyper | cancer_general | — |
| chr21 | 47010243 | 47010451 | Hyper | cancer_general | — |
| chr21 | 47063538 | 47063962 | Hyper | cancer_general | PCBP3 |
| chr21 | 47518776 | 47518814 | Hyper | cancer_general | COL6A2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr21 | 47717560 | 47717589 | Hyper | liver_tcga | C21orf58, YBEY | chr7 | 329805 | 329838 | Hyper | cancer_general | LOC100288524 |
| chr7 | 556928 | 556983 | Hyper | blood | FLJ44511, PDGFA | chr7 | 751816 | 751874 | Hyper | liver_tcga, cancer_general | — |
| chr7 | 752120 | 752221 | Hyper | liver_tcga, cancer_general | — | chr7 | 922050 | 922235 | Hyper | liver_tcga | GET4, SUN1 |
| chr7 | 927933 | 927986 | Hyper | liver_tcga | ADAP1, GET4 | chr7 | 1263761 | 1263960 | Hyper | cancer_general | UNCX |
| chr7 | 1268318 | 1268366 | Hyper | cancer_general | UNCX | chr7 | 1269305 | 1269808 | Hyper | cancer_general | UNCX |
| chr7 | 1270406 | 1270440 | Hyper | cancer_general | UNCX | chr7 | 1273167 | 1273330 | Hyper | cancer_general | UNCX |
| chr7 | 1274641 | 1274677 | Hyper | cancer_general | UNCX | chr7 | 1275008 | 1275038 | Hyper | cancer_general | UNCX |
| chr7 | 1275579 | 1275680 | Hyper | cancer_general | UNCX | chr7 | 1277817 | 1277865 | Hyper | cancer_general | UNCX |
| chr7 | 1279099 | 1279129 | Hyper | cancer_general | UNCX | chr7 | 1279965 | 1279995 | Hyper | cancer_general | UNCX |
| chr7 | 1281131 | 1281232 | Hyper | cancer_general | UNCX | chr7 | 1281493 | 1281555 | Hyper | cancer_general | UNCX |
| chr7 | 1282042 | 1282150 | Hyper | cancer_general | UNCX | chr7 | 1282506 | 1282644 | Hyper | cancer_general | UNCX |
| chr7 | 1286244 | 1286338 | Hyper | cancer_general | UNCX | chr7 | 1286810 | 1286858 | Hyper | cancer_general | UNCX |
| chr7 | 1288582 | 1288753 | Hyper | cancer_general | — | chr7 | 1709138 | 1709235 | Hyper | cancer_general | — |
| chr7 | 1709474 | 1709594 | Hyper | tcga | AMZ1 | chr7 | 1748514 | 1748766 | Hyper | liver_tcga | ELFN1 |
| chr7 | 2728068 | 2728165 | Hyper | cancer_general, colorectal | — | chr7 | 2979480 | 2979512 | Hyper | literature | CARD11 |
| chr7 | 2985518 | 2985547 | Hyper | literature | CARD11 | chr7 | 3083318 | 3083352 | Hyper | tcga | CARD11 |
| chr7 | 3340444 | 3340473 | Hyper | liver tcga | SDK1 | chr7 | 3340964 | 3340993 | Hyper | liver_tcga | SDK1 |
| chr7 | 3341489 | 3341597 | Hyper | liver_tcga, cancer_general | SDK1 | chr7 | 4922550 | 4922722 | Hyper | tcga | MMD2 |
| chr7 | 4923072 | 4923397 | Hyper | liver_tcga, cancer_general, tcga | MMD2 | chr7 | 4998201 | 4998388 | Hyper | cancer_general | MMD2 |
| chr7 | 4998698 | 4998736 | Hyper | cancer_general | MMD2 | chr7 | 5111528 | 5111669 | Hyper | liver_tcga | RBAKDN, RBAK, RBAK-RBAKDN |
| chr7 | 5632939 | 5633100 | Hyper | tcga | FSCN1 | chr7 | 6045612 | 6045641 | Hyper | literature | AIMP2, PMS2 |
| chr7 | 6414386 | 6414415 | Hyper | literature | RAC1 | chr7 | 6426878 | 6426907 | Hyper | literature | RAC1 |
| chr7 | 6643150 | 6643216 | Hyper | hepatobiliary | GRID2IP | chr7 | 6566413 | 6566663 | Hyper | tcga | — |
| chr7 | 6570959 | 6571130 | Hyper | tcga | SDK1 | chr7 | 6576137 | 6576367 | Hyper | tcga | — |
| chr7 | 6703555 | 6703959 | Hyper | liver_tcga, cancer_general | AK123300 | chr7 | 8473070 | 8473674 | Hyper | cancer_general | NXPH1 |
| chr7 | 8473956 | 8474562 | Hyper | cancer_general | NXPH1 | chr7 | 8474814 | 8475057 | Hyper | cancer_general | NXPH1 |
| chr7 | 8480640 | 8481159 | Hyper | literature, cancer_general | NXPH1 | chr7 | 8481642 | 8481833 | Hyper | cancer_general | NXPH1 |
| chr7 | 8482056 | 8482921 | Hyper | literature, cancer_general | NXPH1 | chr7 | 8483147 | 8483950 | Hyper | cancer_general | NXPH1 |
| chr7 | 12151440 | 12151678 | Hyper | cancer_general | — | chr7 | 12443317 | 12443403 | Hyper | cancer_general | VWDE |
| chr7 | 12443841 | 12443871 | Hyper | cancer_general | VWDE | chr7 | 12610339 | 12610476 | Hyper | blood | SCIN, BC075797 |
| chr7 | 15725983 | 15726081 | Hyper | cancer_general | BX538274, MEOX2 | chr7 | 15726634 | 15727077 | Hyper | tcga, cancer_general | BX538274, MEOX2 |
| chr7 | 15727290 | 15727320 | Hyper | cancer_general | BX538274, MEOX2 | chr7 | 19145808 | 19146249 | Hyper | cancer_general | TWIST1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 19146502 | 19146558 | Hyper | cancer_general | TWIST1 | chr7 | 19147122 | 19147798 | Hyper | tcga, cancer_general | TWIST1 |
| chr7 | 19152002 | 19152349 | Hyper | tcga, cancer_general | TWIST1 | chr7 | 19155791 | 19155820 | Hyper | literature | TWIST1 |
| chr7 | 19156070 | 19156916 | Hyper | tcga, literature, cancer_general | TWIST1 | chr7 | 19157144 | 19158015 | Hyper | tcga, literature, cancer_general | TWIST1 |
| chr7 | 19158632 | 19158735 | Hyper | literature | TWIST1 | chr7 | 19184058 | 19184255 | Hyper | cancer_general | BC043576, FERD3L |
| chr7 | 19813284 | 19813313 | Hyper | literature | TMEM196 | chr7 | 20816252 | 20816447 | Hyper | cancer_general | SP8 |
| chr7 | 20817380 | 20817410 | Hyper | cancer_general | SP8 | chr7 | 20818130 | 20818362 | Hyper | cancer_general | SP8 |
| chr7 | 20823292 | 20823432 | Hyper | cancer_general | SP8 | chr7 | 20823904 | 20824946 | Hyper | cancer_general, literature, tcga | SP8 |
| chr7 | 20825379 | 20825559 | Hyper | literature | SP8 | chr7 | 20826113 | 20826202 | Hyper | literature | SP8 |
| chr7 | 20826884 | 20827199 | Hyper | pancreas, literature | SP8 | chr7 | 20830670 | 20830700 | Hyper | cancer_general | SP8 |
| chr7 | 20833167 | 20833322 | Hyper | cancer_general | SP8 | chr7 | 21582593 | 21582868 | Hyper | cancer_general | DNAH11 |
| chr7 | 21583263 | 21583326 | Hyper | cancer_general | DNAH11 | chr7 | 22539833 | 22539909 | Hyper | cancer_general | STEAP1B |
| chr7 | 22589356 | 22589870 | Hyper | cancer_general | — | chr7 | 23287253 | 23287624 | Hyper | cancer_general, tcga | GPNMB |
| chr7 | 24323763 | 24323939 | Hyper | liver_tcga | NPY | chr7 | 24796478 | 24796567 | Hyper | cancer_general, tcga | DFNA5 |
| chr7 | 25892510 | 25892588 | Hyper | cancer_general | — | chr7 | 25896521 | 25896864 | Hyper | cancer_general | — |
| chr7 | 25897133 | 25897246 | Hyper | tcga, pancreas | — | chr7 | 27127863 | 27127898 | Hyper | cancer_general | HOTAIRM1 |
| chr7 | 27135327 | 27135794 | Hyper | tcga, cancer_general | HOTAIRM1, HOXA2, AK291164, HOXA1 | chr7 | 27136013 | 27136790 | Hyper | tcga, lung, cancer_general | HOXA2, AK291164, HOXA3, HOTAIRM1, HOXA1 |
| chr7 | 27138381 | 27138410 | Hyper | literature | HOXA2, AK291164, HOXA3, HOTAIRM1, HOXA1 | chr7 | 27187535 | 27187570 | Hyper | cancer_general | HOXA7, DQ655986, HOXA-AS3, HOXA6, HOXA5 |
| chr7 | 27190591 | 27191226 | Hyper | tcga, liver_tcga, cancer_general | HOXA5, HOXA7, DQ655986, HOXA-AS3, HOXA6 | chr7 | 27192061 | 27192098 | Hyper | cancer_general | HOXA7, HOXA9, HOXA10-HOXA9, DQ655986, HOXA-AS3, HOXA6, HOXA5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 27195462 | 27196839 | Hyper | tcga, cancer_general, lung | DQ655986, HOXA-AS3, HOXA6, HOXA9, HOXA10-HOXA9, HOXA7 | chr7 | 27204487 | 27205395 | Hyper | literature, cancer_general, liver_tcga, tcga | HOXA10-HOXA9, MIR196B, HOXA7, HOXA-AS4, MIR196B, HOXA10 |
| chr7 | 27205678 | 27206058 | Hyper | cancer_general | HOXA10, HOXA10-HOXA9, OHXA9, HOXA7, HOXA-AS4, MIR196B | chr7 | 27208187 | 27208285 | Hyper | liver_tcga | HOXA-AS4, MIR196B, HOXA10-HOXA10, HOXA9, HOXA9 |
| chr7 | 27209462 | 27209582 | Hyper | liver_tcga | HOXA-AS4, HOXA10-HOXA9, HOXA10, MIR196B | chr7 | 27209789 | 27209828 | Hyper | liver_tcga | HOXA10, MIR196B, HOXA-AS4, HOXA10-HOXA9 |
| chr7 | 27212499 | 27212899 | Hyper | cancer_general | HOXA11, HOXA10, MIR196B, HOXA-AS4, HOXA10-HOXA9 | chr7 | 27213172 | 27214310 | Hyper | tcga, literature, cancer_general | HOXA11, HOXA10, MIR 196B, HOXA-AS4, HOXA10-HOXA9 |
| chr7 | 27217042 | 27217071 | Hyper | liver_tcga | HOXA11, HOXA11-AS, HOXA10, MIR196B, HOXA-AS4, HOXA10-HOXA9 | chr7 | 27223114 | 27223151 | Hyper | cancer_general | HOXA11-AS, LOC402470, HOXA11, HOXA10 |
| chr7 | 27223601 | 27223696 | Hyper | cancer_general | HOXA10, HOXA11-AS, LOC402470, HOXA11 | chr7 | 27224069 | 27224609 | Hyper | cancer_general | HOXA11, HOXA10, HOXA11-AS, LOC402470 |
| chr7 | 27225035 | 27225092 | Hyper | cancer_general | LOC402470, HOXA11-AS, HOXA11, HOXA10 | chr7 | 27225447 | 27225543 | Hyper | liver_tcga, literature | HOXA11, HOXA10, HOXA11-AS, LOC402470, HOXA11, HOXA10 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 27227874 | 27227953 | Hyper | cancer_general | LOC402470, HOXA11-AS, HOXA11, HOXA10, HOXA13 | chr7 | 27231476 | 27231505 | Hyper | liver_tcga | HOXA11-AS, HOXA11, HOXA13, HOTTIP, LOC402470 |
| chr7 | 27231818 | 27231894 | Hyper | liver_tcga | LOC402470, HOXA11-AS, HOXA11, HOXA13, HOTTIP | chr7 | 27232289 | 27232962 | Hyper | liver_tcga, cancer_general | HOXA13, HOTTIP, LOC402470, HOXA11-AS, HOXA11 |
| chr7 | 27233410 | 27233454 | Hyper | liver_tcga | HOXA13, HOTTIP, LOC402470, HOXA11-AS, HOXA11 | chr7 | 27238887 | 27238917 | Hyper | cancer_general | HOXA13, HOTTIP, LOC402470, HOXA11-AS |
| chr7 | 27239177 | 27239234 | Hyper | cancer_general | HOTTIP, HOXA13 | chr7 | 27240230 | 27240381 | Hyper | cancer_general | HOTTIP, HOXA13 |
| chr7 | 27244515 | 27245310 | Hyper | cancer_general | HOTTIP, HOXA13 | chr7 | 27252380 | 27252410 | Hyper | cancer_general | HOTTIP |
| chr7 | 27260092 | 27260122 | Hyper | liver_tcga | — | chr7 | 27264875 | 27265325 | Hyper | cancer_general | EVX1 |
| chr7 | 27265538 | 27265584 | Hyper | cancer_general | — | chr7 | 27275513 | 27275543 | Hyper | blood | EVX1 |
| chr7 | 27279915 | 27279453 | Hyper | cancer_general | EVX1 | chr7 | 27281329 | 27281360 | Hyper | literature | EVX1 |
| chr7 | 27282089 | 27283013 | Hyper | cancer_general | EVX1 | chr7 | 27283351 | 27283627 | Hyper | cancer_general | EVX1 |
| chr7 | 27285522 | 27286248 | Hyper | cancer_general | EVX1 | chr7 | 27288946 | 27289449 | Hyper | cancer_general | EVX1 |
| chr7 | 27291143 | 27291851 | Hyper | literature, cancer_general | EVX1 | chr7 | 28449276 | 28450015 | Hyper | tcga, colorectal, cancer_general | CREB5, BC087859 |
| chr7 | 28995657 | 28995978 | Hyper | blood | DQ601810, TRIL | chr7 | 28996457 | 28996495 | Hyper | cancer_general, blood | DQ601810, TRIL |
| chr7 | 28996840 | 28996916 | Hyper | liver_tcga, cancer_general | DQ601810, TRIL | chr7 | 28997136 | 28997625 | Hyper | cancer_general, liver_tcga | DQ601810, TRIL |
| chr7 | 28998053 | 28998119 | Hyper | cancer_general | DQ601810, TRIL | chr7 | 30029702 | 30029822 | Hyper | tcga | SCRN1 |
| chr7 | 30721280 | 30721902 | Hyper | tcga, cancer_general | CRHR2 | chr7 | 30722290 | 30722375 | Hyper | liver_tcga, cancer_general | CRHR2 |
| chr7 | 31093003 | 31093133 | Hyper | cancer_general | ADCYAP1R1 | chr7 | 31232909 | 31232939 | Hyper | blood | — |
| chr7 | 31375965 | 31376135 | Hyper | cancer_general | NEUROD6 | chr7 | 32110698 | 32110772 | Hyper | cancer_general | — |
| chr7 | 32337807 | 32337837 | Hyper | cancer_general | — | chr7 | 32338088 | 32338410 | Hyper | tcga, cancer_general | — |
| chr7 | 32338900 | 32338930 | Hyper | cancer_general | — | chr7 | 32467461 | 32468062 | Hyper | cancer_general | BMPER |
| chr7 | 32997124 | 32997454 | Hyper | blood | FKBP9 | chr7 | 33943459 | 33943759 | Hyper | cancer_general | — |
| chr7 | 35225809 | 35225876 | Hyper | cancer_general | — | chr7 | 35226193 | 35226765 | Hyper | tcga, cancer_general | — |
| chr7 | 35292970 | 35293293 | Hyper | cancer_general | TBX20 | chr7 | 35293654 | 35294141 | Hyper | cancer_general, literature, liver_tcga | TBX20 |
| chr7 | 35294502 | 35294536 | Hyper | cancer_general | TBX20 | chr7 | 35295104 | 35295134 | Hyper | cancer_general | TBX20 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 35295908 | 35295944 | Hyper | cancer_general | TBX20 | chr7 | 35296935 | 35298032 | Hyper | cancer_general | TBX20 |
| chr7 | 35300951 | 35301948 | Hyper | cancer_general, literature | TBX20 | chr7 | 35494353 | 35494440 | Hyper | cancer_general | — |
| chr7 | 37487164 | 37487826 | Hyper | tcga, cancer_general | — | chr7 | 37488257 | 37488578 | Hyper | cancer_general | — |
| chr7 | 37488920 | 37488992 | Hyper | cancer_general | — | chr7 | 37955878 | 37955979 | Hyper | cancer_general | EPDR1, SFRP4 |
| chr7 | 37956271 | 37956439 | Hyper | cancer_general | EPDR1, SFRP4 | chr7 | 37960301 | 37960335 | Hyper | cancer_general | EPDR1, SFRP4 |
| chr7 | 38670357 | 38671015 | Hyper | tcga, cancer_general | — | chr7 | 39015542 | 39015981 | Hyper | tcga | POU6F2, AK023033 |
| chr7 | 39649223 | 39649457 | Hyper | liver_tcga, literature | LOC646999 | chr7 | 39872836 | 39873015 | Hyper | tcga | — |
| chr7 | 41739663 | 41739879 | Hyper | pancreas, tcga | INHBA-AS1, INHBA | chr7 | 41982690 | 41982874 | Hyper | esophageal | — |
| chr7 | 42267647 | 42267677 | Hyper | cancer_general | GLI3 | chr7 | 42276346 | 42276634 | Hyper | cancer_general | GLI3 |
| chr7 | 42533118 | 42533296 | Hyper | tcga | — | chr7 | 43152109 | 43152700 | Hyper | cancer_general | HECW1, AX748020 |
| chr7 | 43152957 | 43153237 | Hyper | cancer_general, tcga | AX748020, HECW1 | chr7 | 44143980 | 44144010 | Hyper | liver_tcga | AEBP1, MIR4649 |
| chr7 | 44163926 | 44163989 | Hyper | tcga | POLD2, AEBP1 | chr7 | 44364838 | 44364903 | Hyper | colorectal | CAMK2B |
| chr7 | 45613785 | 45613898 | Hyper | cancer_general | ADCY1 | chr7 | 45614341 | 45614474 | Hyper | cancer_general | ADCY1 |
| chr7 | 45614738 | 45614809 | Hyper | cancer_general | ADCY1 | chr7 | 45615440 | 45615495 | Hyper | cancer_general | ADCY1 |
| chr7 | 45960743 | 45960794 | Hyper | cancer_general | IGFBP3 | chr7 | 45961146 | 45961176 | Hyper | cancer_general | IGFBP3 |
| chr7 | 45961508 | 45961576 | Hyper | cancer_general | IGFBP3 | chr7 | 45961833 | 45961888 | Hyper | cancer_general | IGFBP3 |
| chr7 | 49812820 | 49813994 | Hyper | liver_tcga, literature, cancer_general | VWC2 | chr7 | 49814531 | 49814795 | Hyper | tcga, cancer_general | VWC2 |
| chr7 | 49815101 | 49815765 | Hyper | tcga, literature, cancer_general | VWC2 | chr7 | 50343263 | 50343401 | Hyper | cancer_general | IKZF1 |
| chr7 | 50343698 | 50343994 | Hyper | cancer_general | IKZF1 | chr7 | 50344226 | 50344491 | Hyper | cancer_general | IKZF1 |
| chr7 | 50860226 | 50861121 | Hyper | blood | — | chr7 | 51383754 | 51383790 | Hyper | blood | COBL |
| chr7 | 51384327 | 51384440 | Hyper | blood | COBL | chr7 | 51384915 | 51384951 | Hyper | blood | COBL |
| chr7 | 52156231 | 52156261 | Hyper | cancer_general | — | chr7 | 54609852 | 54610153 | Hyper | esophageal, cancer_general | VSTM2A |
| chr7 | 54612418 | 54612730 | Hyper | cancer_general | VSTM2A | chr7 | 55086473 | 55086601 | Hyper | blood | EGFR |
| chr7 | 55086983 | 55087533 | Hyper | blood | EGFR | chr7 | 55209976 | 55210005 | Hyper | literature | EGFR |
| chr7 | 55211065 | 55211094 | Hyper | literature | EGFR | chr7 | 55221729 | 55221836 | Hyper | literature | EGFR |
| chr7 | 55223589 | 55223636 | Hyper | literature | EGFR | chr7 | 55227993 | 55228022 | Hyper | literature | EGFR |
| chr7 | 55233028 | 55233123 | Hyper | literature | EGFR | chr7 | 55241663 | 55241737 | Hyper | literature | EGFR-AS1, EGFR |
| chr7 | 55242419 | 55242493 | Hyper | literature | EGFR-AS1, EGFR | chr7 | 55248975 | 55249085 | Hyper | literature | EGFR-AS1, EGFR |
| chr7 | 55259404 | 55259547 | Hyper | literature | EGFR, EGFR-AS1 | chr7 | 55260469 | 55260498 | Hyper | literature | EGFR, EGFR-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 55268867 | 55268896 | Hyper | literature | GU228584, EGFR | chr7 | 64349026 | 64349056 | Hyper | cancer_general | ZNF273, AK097702 |
| chr7 | 64349331 | 64349470 | Hyper | cancer_general | AK097702, ZNF273 | chr7 | 64700283 | 64700329 | Hyper | cancer_general | — |
| chr7 | 64712364 | 64712510 | Hyper | cancer_general, tcga | — | chr7 | 64974382 | 64974422 | Hyper | cancer_general | — |
| chr7 | 65037609 | 65037734 | Hyper | cancer_general | — | chr7 | 65508995 | 65509043 | Hyper | cancer_general | — |
| chr7 | 65878743 | 65878793 | Hyper | cancer_general | AUTS2 | chr7 | 69062519 | 69062635 | Hyper | tcga | AUTS2 |
| chr7 | 69064590 | 69065045 | Hyper | tcga, colorectal | WBSCR17 | chr7 | 70596436 | 70596688 | Hyper | cancer_general | WBSCR17 |
| chr7 | 70596942 | 70597105 | Hyper | tcga, cancer_general | WBSCR17 | chr7 | 70597406 | 70597451 | Hyper | cancer_general | WBSCR17 |
| chr7 | 70597835 | 70598387 | Hyper | cancer_general | — | chr7 | 71217108 | 71217332 | Hyper | cancer_general | MAGI2-AS3 |
| chr7 | 71800676 | 71801899 | Hyper | cancer_general | — | chr7 | 71802410 | 71802637 | Hyper | cancer_general | MAGI2-AS3 |
| chr7 | 75511201 | 75511298 | Hyper | liver_tcga | RHBDD2 | chr7 | 79081792 | 79081821 | Hyper | tcga | MAGI2-AS3 |
| chr7 | 79082023 | 79082218 | Hyper | tcga, cancer_general | MAGI2-AS3 | chr7 | 79083093 | 79083177 | Hyper | cancer_general | MAGI2-AS3 |
| chr7 | 79083392 | 79083834 | Hyper | cancer_general | MAGI2-AS3 | chr7 | 80548257 | 80548403 | Hyper | blood | SEMA3C |
| chr7 | 82072350 | 82072503 | Hyper | cancer_general | — | chr7 | 82073495 | 82073533 | Hyper | blood | — |
| chr7 | 84815141 | 84815375 | Hyper | tcga | SEMA3D | chr7 | 84815744 | 84815954 | Hyper | cancer_general, tcga | SEMA3D |
| chr7 | 86273208 | 86273541 | Hyper | cancer_general | GRM3 | chr7 | 86274117 | 86274457 | Hyper | cancer_general | GRM3 |
| chr7 | 87104816 | 87105412 | Hyper | tcga, esophageal | ABCB4 | chr7 | 87229537 | 87230433 | Hyper | tcga, cancer_general | ABCB1 |
| chr7 | 87257012 | 87257047 | Hyper | cancer_general | RUNDC3B, ABCB1 | chr7 | 87257931 | 87258054 | Hyper | esophageal | RUNDC3B, ABCB1 |
| chr7 | 87563370 | 87563614 | Hyper | esophageal | ADAM22 | chr7 | 87563829 | 87563890 | Hyper | esophageal | ADAM22 |
| chr7 | 88387982 | 88388183 | Hyper | cancer_general | ZNF804B | chr7 | 88388540 | 88388636 | Hyper | tcga | ZNF804B |
| chr7 | 88388879 | 88389356 | Hyper | tcga, cancer_general | ZNF804B | chr7 | 89747996 | 89748340 | Hyper | cancer_general | DPY19L2P4 |
| chr7 | 89950183 | 89950810 | Hyper | cancer_general, tcga | C7orf63 | chr7 | 90226269 | 90226464 | Hyper | tcga, colorectal | CDK14 |
| chr7 | 90895012 | 90895097 | Hyper | tcga | FZD1 | chr7 | 92466152 | 92466400 | Hyper | tcga | CDK6 |
| chr7 | 93203708 | 93203756 | Hyper | cancer_general | — | chr7 | 93204332 | 93204492 | Hyper | tcga | — |
| chr7 | 93519351 | 93520137 | Hyper | liver_tcga, cancer_general | TFPI2 | chr7 | 93551323 | 93551425 | Hyper | cancer_general | GNG11 |
| chr7 | 94284302 | 94284873 | Hyper | cancer_general | PEG10, SGCE | chr7 | 96619560 | 96619603 | Hyper | cancer_general | DLX6-AS1 |
| chr7 | 96621715 | 96621811 | Hyper | cancer_general | DLX6-AS1 | chr7 | 96622107 | 96622349 | Hyper | cancer_general | DLX6-AS1 |
| chr7 | 96622694 | 96622723 | Hyper | literature | DLX6-AS1 | chr7 | 96625537 | 96625720 | Hyper | cancer_general | DLX6, DLX6-AS1 |
| chr7 | 96625998 | 96626051 | Hyper | cancer_general | DLX6, DLX6-AS1 | chr7 | 96631579 | 96631680 | Hyper | liver_tcga | DLX6, DLX6-AS1 |
| chr7 | 96634645 | 96634928 | Hyper | tcga | DLX6, DLX6-AS1 | chr7 | 96635345 | 96635473 | Hyper | cancer_general | DLX6-AS1, DLX6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 96635733 | 96636645 | Hyper | tcga, cancer_general | DLX6, DLX6-AS1 | chr7 | 96639318 | 96639348 | Hyper | cancer_general | DLX6-AS1, DLX6 |
| chr7 | 96646662 | 96647131 | Hyper | cancer_general | DLX5, DLX6, DLX6-AS1 | chr7 | 96647809 | 96648219 | Hyper | cancer_general | DLX6-AS1, DLX5, DLX6 |
| chr7 | 96649955 | 96650192 | Hyper | liver_tcga, cancer_general | DLX5, DLX6, DLX6-AS1 | chr7 | 96650884 | 96651151 | Hyper | cancer_general | DLX5 |
| chr7 | 96651472 | 96651502 | Hyper | cancer_general | DLX5 | chr7 | 96652144 | 96652174 | Hyper | cancer_general | DLX5 |
| chr7 | 96653507 | 96653993 | Hyper | cancer_general | DLX5 | chr7 | 97361098 | 97361781 | Hyper | cancer_general, literature | TAC1 |
| chr7 | 97362292 | 97362607 | Hyper | cancer_general | TAC1 | chr7 | 98245885 | 98246868 | Hyper | literature, cancer_general | NPTX2 |
| chr7 | 98247126 | 98247656 | Hyper | cancer_general | NPTX2 | chr7 | 99177742 | 99177870 | Hyper | cancer_general | ZNF655 |
| chr7 | 99595194 | 99595337 | Hyper | cancer_general | — | chr7 | 99775192 | 99775558 | Hype | tcga, liver_tcga | STAG3, GPC2, GAL3ST4 |
| chr7 | 100091210 | 100091378 | Hyper | cancer_general, literature | NYAP1 | chr7 | 100318505 | 100318575 | Hyper | cancer_general | EPO |
| chr7 | 100320690 | 100320719 | Hyper | literature | EPO | chr7 | 100547037 | 100547073 | Hyper | cancer_general | MUC3A, MUC3B |
| chr7 | 100609750 | 100609780 | Hyper | pancreas | MUC12, MUC3B, AK096803, AK057259, MUC3A | chr7 | 100808466 | 100808502 | Hyper | pancreas | AP1S1, NAT16, VGF, MIR4653 |
| chr7 | 100809436 | 100809521 | Hyper | tcga | MIR4653, AP1S1, NAT16, VGF | chr7 | 100823436 | 100823497 | Hyper | cancer_general | NAT16 |
| chr7 | 101005968 | 101005998 | Hyper | cancer_general | COL26A1 | chr7 | 101558399 | 101558698 | Hyper | liver_tcga | CUX1 |
| chr7 | 103085876 | 103086474 | Hyper | liver_tcga, cancer_general | — | chr7 | 103629059 | 103630125 | Hyper | tcga, cancer_general | — |
| chr7 | 103630475 | 103630824 | Hyper | tcga, cancer_general | — | chr7 | 103969217 | 103969341 | Hyper | cancer_general | JB175200, LHFPL3 |
| chr7 | 103969694 | 103969794 | Hyper | cancer_general | JB175200, LHFPL3 | chr7 | 106685282 | 106685345 | Hyper | esophageal | PRKAR2B |
| chr7 | 107301494 | 107301640 | Hyper | cancer_general | SLC26A4, SLC26A4-AS1 | chr7 | 108095329 | 108095362 | Hyper | cancer_general | NRCAM |
| chr7 | 108095686 | 108096055 | Hyper | tcga, colorectal | NRCAM | chr7 | 108097172 | 108097491 | Hyper | tcga, cancer_general | NRCAM |
| chr7 | 112726558 | 112726614 | Hyper | cancer_general | GPR85 | chr7 | 113722810 | 113723439 | Hyper | lung, cancer_general | FOXP2 |
| chr7 | 113724956 | 113725081 | Hyper | cancer_general | FOXP2 | chr7 | 113726509 | 113726539 | Hyper | esophageal | FOXP2 |
| chr7 | 113727442 | 113727486 | Hyper | cancer_general | FOXP2 | chr7 | 113727722 | 113727781 | Hyper | cancer_general | FOXP2 |
| chr7 | 115117552 | 115117647 | Hyper | cancer_general | — | chr7 | 116140252 | 116140356 | Hyper | tcga | CAV2 |
| chr7 | 116412008 | 116412058 | Hyper | literature | — | chr7 | 116415100 | 116415129 | Hyper | literature | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 116417443 | 116417496 | Hyper | literature | — | chr7 | 116422067 | 116422132 | Hyper | literature | — |
| chr7 | 116423399 | 116423488 | Hyper | literature | — | chr7 | 116962893 | 116963476 | Hyper | liver_tcga, cancer_general, tcga | WNT2 |
| chr7 | 117119381 | 117120271 | Hyper | liver_tcga, literature, cancer_general | CFTR | chr7 | 117513675 | 117513849 | Hyper | blood | CTTNBP2 |
| chr7 | 119913561 | 119913785 | Hyper | tcga | KCND2 | chr7 | 120969672 | 120969800 | Hyper | cancer_general | WNT16 |
| chr7 | 121513523 | 121513709 | Hyper | tcga | PTPRZ1 | chr7 | 121939677 | 121940448 | Hyper | liver_tcga, literature, cancer_general | FEZF1, FEZF1-AS1 |
| chr7 | 121940935 | 121941052 | Hyper | cancer_general | FEZF1, FEZF1-AS1 | chr7 | 121941881 | 121942170 | Hyper | cancer_general | FEZF1-AS1, FEZF1 |
| chr7 | 121944001 | 121944166 | Hyper | cancer_general | FEZF1-AS1, FEZF1 | chr7 | 121945822 | 121945920 | Hyper | blood | FEZF1-AS1, FEZF1 |
| chr7 | 121946478 | 121947406 | Hyper | cancer_general | FEZF1-AS1, FEZF1 | chr7 | 121950137 | 121951069 | Hyper | cancer_general | CADPS2, FEZF1-AS1, FEZF1 |
| chr7 | 121951877 | 121952169 | Hyper | cancer_general | CADPS2, FEZF1-AS1, FEZF1 | chr7 | 121956486 | 121956567 | Hyper | cancer_general | CADPS2, FEZF1-AS1, FEZF1 |
| chr7 | 121956830 | 121957331 | Hyper | cancer_general | CADPS2, FEZF1-AS1, FEZF1 | chr7 | 122526833 | 122526873 | Hyper | blood | — |
| chr7 | 123173150 | 123173244 | Hyper | cancer_general | IQUB, NDUFA5 | chr7 | 123672048 | 123672086 | Hyper | cancer_general | EU233817, TMEM229A, L13779, BC041947 |
| chr7 | 124404415 | 124404522 | Hyper | cancer_general | GPR37 | chr7 | 126891220 | 126891250 | Hyper | cancer_general | — |
| chr7 | 126891504 | 126891593 | Hyper | cancer_general | — | chr7 | 126894076 | 126894197 | Hyper | esophageal | — |
| chr7 | 127744122 | 127744631 | Hyper | cancer_general | — | chr7 | 127806634 | 127806664 | Hyper | cancer_general | — |
| chr7 | 127807817 | 127807846 | Hyper | tcga | — | chr7 | 127808047 | 127808792 | Hyper | tcga, cancer_general | — |
| chr7 | 127841505 | 127841704 | Hyper | cancer_general | MIR129-1, PRRT4, RBM28 | chr7 | 127881254 | 127881283 | Hyper | literature | LEP |
| chr7 | 127991826 | 127992135 | Hyper | cancer_general | — | chr7 | 128337467 | 128337921 | Hyper | cancer_general | — |
| chr7 | 128470897 | 128471032 | Hyper | cancer_general | FLNC, CCDC136 | chr7 | 128828195 | 128828272 | Hyper | cancer_general | SMO |
| chr7 | 129418057 | 129418428 | Hyper | pancreas, cancer_general | MIR183, MIR96, MIR182 | chr7 | 129422160 | 129423418 | Hyper | cancer_general | MIR183, MIR96 |
| chr7 | 129423834 | 129424034 | Hyper | lung, cancer_general | MIR183, MIR96 | chr7 | 129424655 | 129425887 | Hyper | cancer_general | MIR183 |
| chr7 | 129426195 | 129426236 | Hyper | cancer_general | — | chr7 | 131242738 | 131242824 | Hyper | cancer_general | PODXL |
| chr7 | 131514824 | 131514854 | Hyper | cancer_general | — | chr7 | 132261272 | 132261432 | Hyper | tcga | PLXNA4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 134143164 | 134143475 | Hyper | cancer_general | AKR1B1 | chr7 | 134143807 | 134144132 | Hyper | tcga, liver_tcga, colorectal, cancer_general | AKR1B1 |
| chr7 | 136553311 | 136554366 | Hyper | cancer_general | CHRM2 | chr7 | 136554638 | 136554966 | Hyper | cancer_general | CHRM2 |
| chr7 | 136555235 | 136555412 | Hyper | cancer_general | CHRM2 | chr7 | 136555681 | 136556091 | Hyper | tcga, cancer_general | CHRM2 |
| chr7 | 137028481 | 137028524 | Hyper | cancer_general |  | chr7 | 137531158 | 137532337 | Hyper | tcga, cancer_general | DGKI |
| chr7 | 138720785 | 138720909 | Hyper | liver_tcga | ZC3HAV1L, ZC3HAV1 | chr7 | 139167617 | 139167744 | Hyper | cancer_general | KLRG2 |
| chr7 | 139168042 | 139168379 | Hyper | cancer_general | KLRG2 | chr7 | 139208772 | 139208979 | Hyper | liver_tcga, cancer_general | CLEC2L |
| chr7 | 139930051 | 139930270 | Hyper | tcga, liver_tcga |  | chr7 | 140218053 | 140218082 | Hyper | tcga | DENND2A |
| chr7 | 140339934 | 140339982 | Hyper | cancer_general | DENND2A | chr7 | 140453121 | 140453167 | Hyper | literature | BRAF |
| chr7 | 140477779 | 140477868 | Hyper | literature | BRAF | chr7 | 140481381 | 140481431 | Hyper | literature | BRAF |
| chr7 | 140772795 | 140773228 | Hyper | tcga, cancer_general | TMEM178B | chr7 | 140773563 | 140773750 | Hyper | tcga | TMEM178B |
| chr7 | 143042634 | 143042798 | Hyper | liver_tcga | FAM131B | chr7 | 143579739 | 143580069 | Hyper | cancer_general | FAM115A |
| chr7 | 145812992 | 145813082 | Hyper | cancer_general | CNTNAP2 | chr7 | 145813412 | 145813494 | Hyper | liver_tcga | CNTNAP2 |
| chr7 | 145813891 | 145814166 | Hyper | tcga, cancer_general | CNTNAP2 | chr7 | 148508712 | 148508741 | Hyper | literature | EZH2 |
| chr7 | 149112058 | 149112416 | Hyper | literature, cancer_general | TRNA_Cys | chr7 | 149119948 | 149120073 | Hyper | cancer_general | ZNF777, TRNA_Cys |
| chr7 | 149411541 | 149412304 | Hyper | colorectal | TRNA_Cys, KRBA1 | chr7 | 149570368 | 149570406 | Hyper | esophageal | ATP6V0E2-AS1, ZNF862, DQ590227, ATP6V0E2 |
| chr7 | 149744505 | 149744560 | Hyper | cancer_general | AL162052 | chr7 | 149917248 | 149917336 | Hyper | liver_tcga, cancer_general |  |
| chr7 | 149918119 | 149918149 | Hyper | cancer_general |  | chr7 | 150038883 | 150038912 | Hyper | literature | RARRES2, LRRC61, ZBED6CL |
| chr7 | 150716169 | 150716305 | Hyper | cancer_general | ABCB8, ATG9B | chr7 | 150748192 | 150748406 | Hyper | cancer_general | CDK5, SLC4A2, ASIC3, ABCB8 |
| chr7 | 151106451 | 151107004 | Hyper | cancer_general | WDR86-AS1, WDR86 | chr7 | 151107486 | 151107651 | Hyper | cancer_general | WDR86-AS1, WDR86 |
| chr7 | 151188034 | 151188063 | Hyper | literature | RHEB | chr7 | 152133406 | 152133436 | Hyper | liver_tcga | FABP5P3, KMT2C |
| chr7 | 152622621 | 152622697 | Hyper | cancer_general |  | chr7 | 152623016 | 152623057 | Hyper | cancer_general |  |
| chr7 | 153583595 | 153584069 | Hyper | cancer_general | DPP6 | chr7 | 153584389 | 153584623 | Hyper | literature, cancer_general | DPP6 |
| chr7 | 153584848 | 153585206 | Hyper | cancer_general | DPP6 | chr7 | 153585418 | 153585606 | Hyper | cancer_general | DPP6 |
| chr7 | 153749720 | 153750115 | Hyper | cancer_general | DPP6, AK127966 | chr7 | 154862046 | 154862266 | Hyper | cancer_general | LOC100128264, HTR5A |
| chr7 | 155164454 | 155165562 | Hyper | tcga, cancer_general | BC150495 | chr7 | 155165875 | 155166784 | Hyper | cancer_general | BC150495 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 155167034 | 155167909 | Hyper | tcga, cancer_general | BC150495 | chr7 | 155174656 | 155174788 | Hyper | cancer_general | BC150495 |
| chr7 | 155241318 | 155242049 | Hyper | cancer_general | EN2 | chr7 | 155242729 | 155243102 | Hyper | cancer_general | EN2 |
| chr7 | 155243346 | 155243561 | Hyper | cancer_general | EN2 | chr7 | 155243825 | 155243895 | Hyper | cancer_general | EN2 |
| chr7 | 155244180 | 155244361 | Hyper | cancer_general | EN2 | chr7 | 155246886 | 155247584 | Hyper | cancer_general | EN2 |
| chr7 | 155248913 | 155248943 | Hyper | cancer_general | EN2 | chr7 | 155249512 | 155249565 | Hyper | cancer_general | EN2 |
| chr7 | 155249925 | 155250011 | Hyper | cancer_general | EN2 | chr7 | 155250283 | 155250355 | Hyper | cancer_general | EN2 |
| chr7 | 155250787 | 155250996 | Hyper | cancer_general | EN2 | chr7 | 155251701 | 155251939 | Hyper | tcga | EN2 |
| chr7 | 155252247 | 155252490 | Hyper | cancer_general | EN2 | chr7 | 155252862 | 155253041 | Hyper | cancer_general | EN2 |
| chr7 | 155254848 | 155255324 | Hyper | cancer_general | EN2 | chr7 | 155256237 | 155256312 | Hyper | cancer_general | EN2 |
| chr7 | 155257040 | 155257189 | Hyper | cancer_general | EN2 | chr7 | 155258193 | 155258487 | Hyper | cancer_general | EN2 |
| chr7 | 155258949 | 155260137 | Hyper | tcga, cancer_general | EN2 | chr7 | 155260880 | 155261210 | Hyper | cancer_general, tcga | EN2 |
| chr7 | 155301838 | 155301931 | Hyper | cancer_general | CNPY1 | chr7 | 155302328 | 155303335 | Hyper | tcga, cancer_general | CNPY1 |
| chr7 | 155325796 | 155325872 | Hyper | cancer_general | CNPY1 | chr7 | 155326169 | 155326527 | Hyper | cancer_general | CNPY1 |
| chr7 | 155580165 | 155580211 | Hyper | cancer_general | RBM33 | chr7 | 155600629 | 155600723 | Hyper | cancer_general | SHH |
| chr7 | 155602751 | 155602805 | Hyper | blood | SHH | chr7 | 156409144 | 156409347 | Hyper | cancer_general | — |
| chr7 | 156409665 | 156409802 | Hyper | cancer_general | — | chr7 | 156701846 | 156701908 | Hyper | cancer_general | MNX1, LOC645249 |
| chr7 | 156794153 | 156794235 | Hyper | cancer_general | MNX1, LOC645249 | chr7 | 156794443 | 156794485 | Hyper | cancer_general | MNX1, LOC645249 |
| chr7 | 156794998 | 156795914 | Hyper | cancer_general | MNX1, LOC645249 | chr7 | 156796534 | 156799467 | Hyper | cancer_general, tcga | MNX1, LOC645249 |
| chr7 | 156800999 | 156801029 | Hyper | cancer_general | LOC645249, MNX1 | chr7 | 156801403 | 156801601 | Hyper | lung, cancer_general | LOC64524 |
| chr7 | 156808858 | 156809199 | Hyper | cancer_general | LOC645249, MNX1 | chr7 | 156809983 | 156811436 | Hyper | cancer_general | MNX19, LOC645249, MNX1 |
| chr7 | 156812852 | 156815092 | Hyper | tcga, cancer_general | LOC645249, MNX1 | chr7 | 156871168 | 156871297 | Hyper | cancer_general | — |
| chr7 | 157361605 | 157361635 | Hyper | cancer_general | MIR153-2, PTPRN2 | chr7 | 157476879 | 157477272 | Hyper | cancer_general | — |
| chr7 | 157477473 | 157477914 | Hyper | cancer_general | — | chr7 | 157481130 | 157481160 | Hyper | pancreas | — |
| chr7 | 157481364 | 157481756 | Hyper | cancer_general | — | chr7 | 157481969 | 157482168 | Hyper | cancer_general | — |
| chr7 | 157482492 | 157482667 | Hyper | cancer_general | — | chr7 | 157483320 | 157483538 | Hyper | tcga, cancer_general | — |
| chr7 | 157484877 | 157485277 | Hyper | cancer_general | — | chr7 | 157485527 | 157485705 | Hyper | liver_tcga | WDR60 |
| chr7 | 157485976 | 157486503 | Hyper | cancer_general | — | chr7 | 158673836 | 158673942 | Hyper | liver_tcga | VIPR2 |
| chr7 | 158936492 | 158936880 | Hyper | cancer_general, liver_tcga | VIPR2 | chr7 | 158937158 | 158937624 | Hyper | cancer_general, tcga | — |
| chr7 | 158938210 | 158938399 | Hyper | cancer_general | VIPR2 | HCMV-AD169 | 17724 | 17753 | Hyper | virus | — |
| HCMV-AD169 | 18691 | 18720 | Hyper | virus | — | HCMV-AD169 | 23851 | 23880 | Hyper | virus | — |
| HCMV-AD169 | 27296 | 27325 | Hyper | virus | — | HCMV-AD169 | 42909 | 42938 | Hyper | virus | — |
| HCMV-AD169 | 57909 | 57938 | Hyper | virus | — | HCMV-AD169 | 68427 | 68456 | Hyper | virus | — |
| HCMV-AD169 | 76862 | 76891 | Hyper | virus | — | HCMV-AD169 | 78956 | 78985 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HCMV-AD169 | 81188 | 81217 | Hyper | virus | — | HCMV-AD169 | 84448 | 84477 | Hyper | virus | — |
| HCMV-AD169 | 88920 | 88949 | Hyper | virus | — | HCMV-AD169 | 99889 | 99918 | Hyper | virus | — |
| HCMV-AD169 | 101238 | 101267 | Hyper | virus | — | HCMV-AD169 | 108021 | 108050 | Hyper | virus | — |
| HCMV-AD169 | 114824 | 114853 | Hyper | virus | — | HCMV-AD169 | 128011 | 128040 | Hyper | virus | — |
| HCMV-AD169 | 129567 | 129596 | Hyper | virus | — | HCMV-AD169 | 149187 | 149216 | Hyper | virus | — |
| HCMV-AD169 | 162299 | 162328 | Hyper | virus | — | HCMV-AD169 | 169250 | 169279 | Hyper | virus | — |
| HCMV-AD169 | 171221 | 171250 | Hyper | virus | — | HCMV-AD169 | 172561 | 172590 | Hyper | virus | — |
| HCMV-AD169 | 177053 | 177082 | Hyper | virus | — | HCMV-AD169 | 193060 | 193089 | Hyper | virus | — |
| HCMV-AD169 | 193858 | 193887 | Hyper | virus | — | HCMV-AD169 | 194176 | 194205 | Hyper | virus | — |
| HCMV-AD169 | 195222 | 195251 | Hyper | virus | — | HCMV-AD169 | 196060 | 196089 | Hyper | virus | — |
| HCMV-AD169 | 196817 | 196846 | Hyper | virus | — | HCMV-AD169 | 199152 | 199181 | Hyper | virus | — |
| HCMV-AD169 | 199906 | 199935 | Hyper | virus | — | HCMV-AD169 | 201145 | 201174 | Hyper | virus | — |
| HCMV-AD169 | 204433 | 204462 | Hyper | virus | — | HCMV-AD169 | 207682 | 207711 | Hyper | virus | — |
| HCMV-AD169 | 209510 | 209539 | Hyper | virus | — | HCMV-AD169 | 210069 | 210098 | Hyper | virus | — |
| HCMV-AD169 | 212133 | 212162 | Hyper | virus | — | HCMV-AD169 | 212591 | 212620 | Hyper | virus | — |
| HCMV-AD169 | 214453 | 214482 | Hyper | virus | — | HCMV-AD169 | 220316 | 220345 | Hyper | virus | — |
| GL000225.1 | 37720 | 37842 | Hyper | esophageal | — | MCV-R17b | 111 | 140 | Hyper | virus | — |
| MCV-R17b | 368 | 397 | Hyper | virus | — | MCV-R17b | 625 | 654 | Hyper | virus | — |
| MCV-R17b | 882 | 911 | Hyper | virus | — | MCV-R17b | 1139 | 1168 | Hyper | virus | — |
| MCV-R17b | 1396 | 1425 | Hyper | virus | — | MCV-R17b | 1653 | 1682 | Hyper | virus | — |
| MCV-R17b | 1910 | 1939 | Hyper | virus | — | MCV-R17b | 2167 | 2196 | Hyper | virus | — |
| MCV-R17b | 2424 | 2453 | Hyper | virus | — | MCV-R17b | 2681 | 2710 | Hyper | virus | — |
| MCV-R17b | 2938 | 2967 | Hyper | virus | — | MCV-R17b | 3195 | 3224 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| MCV-R17b | 3452 | 3481 | Hyper | virus | — | MCV-R17b | 3709 | 3738 | Hyper | virus | — |
| MCV-R17b | 3966 | 3995 | Hyper | virus | — | MCV-R17b | 4223 | 4252 | Hyper | virus | — |
| MCV-R17b | 4480 | 4509 | Hyper | virus | — | MCV-R17b | 4737 | 4766 | Hyper | virus | — |
| MCV-R17b | 4994 | 5023 | Hyper | virus | — | | | | | | |

TABLE 12

| chr | start | end | chr | start | end | chr | start | end |
|---|---|---|---|---|---|---|---|---|
| chr1 | 715373 | 715447 | chr1 | 898654 | 898690 | chr1 | 913532 | 913955 |
| chr1 | 1047531 | 1047647 | chr1 | 1080583 | 1080824 | chr1 | 1095420 | 1095459 |
| chr1 | 1146734 | 1146818 | chr1 | 1218737 | 1218820 | chr1 | 1223512 | 1223652 |
| chr1 | 1235813 | 1236078 | chr1 | 1253330 | 1253386 | chr1 | 1267014 | 1267151 |
| chr1 | 1267462 | 1267699 | chr1 | 1267906 | 1268158 | chr1 | 1281214 | 1281244 |
| chr1 | 1341668 | 1341743 | chr1 | 1436043 | 1436211 | chr1 | 1473125 | 1473207 |
| chr1 | 1475556 | 1475643 | chr1 | 1476255 | 1476318 | chr1 | 1483186 | 1483363 |
| chr1 | 1547129 | 1547348 | chr1 | 1563193 | 1563223 | chr1 | 1688882 | 1689012 |
| chr1 | 1805049 | 1805089 | chr1 | 1856436 | 1856466 | chr1 | 1857847 | 1857909 |
| chr1 | 1874744 | 1874787 | chr1 | 1910415 | 1910445 | chr1 | 1923457 | 1923521 |
| chr1 | 1935274 | 1935459 | chr1 | 1974848 | 1974925 | chr1 | 2066490 | 2066679 |
| chr1 | 2125216 | 2126483 | chr1 | 2165895 | 2165999 | chr1 | 2263169 | 2263263 |
| chr1 | 2267552 | 2267690 | chr1 | 2304327 | 2304389 | chr1 | 2307925 | 2307955 |
| chr1 | 2308376 | 2308636 | chr1 | 2309868 | 2309953 | chr1 | 2331363 | 2331437 |
| chr1 | 2336397 | 2336427 | chr1 | 2375148 | 2375543 | chr1 | 2397001 | 2397031 |
| chr1 | 2428331 | 2428385 | chr1 | 2472174 | 2472301 | chr1 | 2507063 | 2507183 |
| chr1 | 2514330 | 2514376 | chr1 | 2521024 | 2521063 | chr1 | 2706308 | 2706334 |
| chr1 | 2830155 | 2830185 | chr1 | 2866038 | 2866068 | chr1 | 2984719 | 2984749 |
| chr1 | 3102653 | 3102779 | chr1 | 3158823 | 3158962 | chr1 | 3182883 | 3182917 |
| chr1 | 3183415 | 3183455 | chr1 | 3322090 | 3322170 | chr1 | 3567093 | 3567344 |
| chr1 | 3567738 | 3567850 | chr1 | 3567883 | 3568226 | chr1 | 3601850 | 3601946 |
| chr1 | 3607081 | 3607236 | chr1 | 3659550 | 3659642 | chr1 | 3659672 | 3659716 |
| chr1 | 3663532 | 3663562 | chr1 | 3663874 | 3653921 | chr1 | 3664461 | 3664741 |
| chr1 | 3683686 | 3683818 | chr1 | 3700384 | 3700414 | chr1 | 3733551 | 3733581 |
| chr1 | 4111061 | 4111231 | chr1 | 4401433 | 4401463 | chr1 | 4214018 | 4714074 |
| chr1 | 4714164 | 4714345 | chr1 | 4715428 | 4715539 | chr1 | 4715575 | 4716701 |
| chr1 | 5919973 | 5920071 | chr1 | 5920650 | 5920710 | chr1 | 5924296 | 5924431 |
| chr1 | 5924851 | 5924984 | chr1 | 5926596 | 5926645 | chr1 | 5933086 | 5933144 |
| chr1 | 5934925 | 5935061 | chr1 | 5940517 | 5940542 | chr1 | 5940945 | 5941132 |
| chr1 | 5944299 | 5944449 | chr1 | 5944962 | 5945001 | chr1 | 5945348 | 5945435 |
| chr1 | 5947258 | 5947288 | chr1 | 5949491 | 5949575 | chr1 | 5950965 | 5951039 |
| chr1 | 5957473 | 5967503 | chr1 | 5967237 | 5967267 | chr1 | 5969001 | 5969283 |
| chr1 | 5972104 | 5972134 | chr1 | 5972878 | 5972922 | chr1 | 6021621 | 6021651 |
| chr1 | 6025872 | 6025950 | chr1 | 6036766 | 6036796 | chr1 | 6056157 | 6056201 |
| chr1 | 6056506 | 6056651 | chr1 | 6059910 | 6059974 | chr1 | 6166353 | 6166469 |
| chr1 | 6171763 | 6171810 | chr1 | 6186511 | 6186546 | chr1 | 6280243 | 6280273 |
| chr1 | 6284828 | 6284858 | chr1 | 6304201 | 6304242 | chr1 | 6360593 | 6360634 |
| chr1 | 6410456 | 6410486 | chr1 | 6446131 | 6446308 | chr1 | 6480514 | 6480831 |
| chr1 | 6501055 | 6501179 | chr1 | 6507678 | 6508126 | chr1 | 6672227 | 6672351 |
| chr1 | 6713914 | 6714041 | chr1 | 6714348 | 6714378 | chr1 | 6776304 | 6776388 |
| chr1 | 7764641 | 7764737 | chr1 | 7973843 | 7973948 | chr1 | 8085685 | 8085715 |
| chr1 | 8549986 | 8550078 | chr1 | 9324231 | 9324274 | chr1 | 9402465 | 9402616 |
| chr1 | 9527172 | 9527208 | chr1 | 9601954 | 9601984 | chr1 | 9712074 | 9712104 |
| chr1 | 9712561 | 9713014 | chr1 | 9722138 | 9722215 | chr1 | 9795995 | 9796196 |
| chr1 | 9865110 | 9865140 | chr1 | 9867157 | 9867316 | chr1 | 10091888 | 10092060 |
| chr1 | 10095469 | 10095845 | chr1 | 10123736 | 10123928 | chr1 | 10166521 | 10166551 |
| chr1 | 10491694 | 10491724 | chr1 | 10948552 | 10948582 | chr1 | 11169346 | 11169375 |
| chr1 | 11174404 | 11174433 | chr1 | 11181358 | 11181432 | chr1 | 11182142 | 11182171 |
| chr1 | 11188149 | 11188178 | chr1 | 11210182 | 11210211 | chr1 | 11217215 | 11217337 |
| chr1 | 11249032 | 11249061 | chr1 | 11538705 | 11538821 | chr1 | 11539175 | 11539205 |
| chr1 | 11539410 | 11639440 | chr1 | 11540129 | 11640178 | chr1 | 11591719 | 11591826 |
| chr1 | 11752476 | 11752511 | chr1 | 11886250 | 11886280 | chr1 | 11936748 | 11936778 |
| chr1 | 11959093 | 11959196 | chr1 | 12041374 | 12041525 | chr1 | 12123243 | 12123553 |
| chr1 | 12227685 | 12227941 | chr1 | 12251443 | 12251958 | chr1 | 12460299 | 12460356 |
| chr1 | 13910436 | 13910714 | chr1 | 13984525 | 13984742 | chr1 | 14026481 | 14026618 |
| chr1 | 14032304 | 14032347 | chr1 | 14097878 | 14098015 | chr1 | 14128478 | 14128588 |
| chr1 | 14149749 | 14149867 | chr1 | 14730425 | 14730472 | chr1 | 14746206 | 14746245 |
| chr1 | 14925501 | 14926050 | chr1 | 15128565 | 15128595 | chr1 | 15251120 | 15251211 |
| chr1 | 15480593 | 15480892 | chr1 | 16474413 | 16474576 | chr1 | 16475031 | 16475207 |
| chr1 | 16861522 | 16861552 | chr1 | 17445857 | 17445943 | chr1 | 17757538 | 17757570 |
| chr1 | 17787472 | 17787502 | chr1 | 18437457 | 18437526 | chr1 | 18956211 | 18956304 |
| chr1 | 18956574 | 18956610 | chr1 | 18956856 | 18957246 | chr1 | 18957507 | 18957587 |
| chr1 | 18958033 | 18958228 | chr1 | 18958359 | 18958381 | chr1 | 18959456 | 18959550 |
| chr1 | 18960897 | 18960990 | chr1 | 18962727 | 18963135 | chr1 | 18969625 | 18969819 |
| chr1 | 18971852 | 18971929 | chr1 | 18972130 | 18972160 | chr1 | 19043563 | 19043678 |
| chr1 | 19980747 | 19980858 | chr1 | 19992418 | 19992432 | chr1 | 20127338 | 20127421 |
| chr1 | 20248109 | 20248141 | chr1 | 20492168 | 20492298 | chr1 | 20618329 | 20618369 |
| chr1 | 20693317 | 20693420 | chr1 | 20879035 | 20879228 | chr1 | 20879256 | 20879289 |
| chr1 | 20879562 | 20879640 | chr1 | 20879845 | 20879957 | chr1 | 20880182 | 20880605 |
| chr1 | 21026117 | 21026225 | chr1 | 21042894 | 21042924 | chr1 | 21044125 | 21044161 |
| chr1 | 21050471 | 21050511 | chr1 | 21058635 | 21058776 | chr1 | 21573283 | 21573362 |
| chr1 | 21573668 | 21574203 | chr1 | 21713716 | 21713792 | chr1 | 21835943 | 21836007 |
| chr1 | 22140753 | 22141184 | chr1 | 22141326 | 22141355 | chr1 | 22222711 | 22222793 |
| chr1 | 22927410 | 22927482 | chr1 | 23347997 | 23348043 | chr1 | 23449766 | 23449859 |
| chr1 | 23748982 | 23749070 | chr1 | 23885070 | 23885100 | chr1 | 24104000 | 24104062 |
| chr1 | 24161782 | 24161882 | chr1 | 24740603 | 24740829 | chr1 | 26255921 | 25255934 |
| chr1 | 25256354 | 25256383 | chr1 | 25257157 | 25257205 | chr1 | 25257490 | 25257529 |
| chr1 | 25257532 | 25267561 | chr1 | 25257916 | 25258250 | chr1 | 25919307 | 25919337 |

TABLE 12-continued

| chr | start | end | chr | start | end | chr | start | end |
|---|---|---|---|---|---|---|---|---|
| chr1 | 26183522 | 26183579 | chr1 | 26467523 | 26467630 | chr1 | 26651729 | 26551796 |
| chr1 | 26552086 | 26552130 | chr1 | 26737583 | 26737613 | chr1 | 26737946 | 26738182 |
| chr1 | 26917724 | 26917816 | chr1 | 26963625 | 26963789 | chr1 | 27190175 | 27190278 |
| chr1 | 27332448 | 27332673 | chr1 | 27340252 | 27340412 | chr1 | 27724058 | 27724093 |
| chr1 | 27844518 | 27844548 | chr1 | 28558539 | 28558571 | chr1 | 28726724 | 28726812 |
| chr1 | 28727177 | 28727324 | chr1 | 28727894 | 28728020 | chr1 | 29047659 | 29048643 |
| chr1 | 29060250 | 29060311 | chr1 | 29065131 | 29065211 | chr1 | 29450491 | 29450543 |
| chr1 | 29586072 | 29586674 | chr1 | 29804947 | 29805094 | chr1 | 30351554 | 30351742 |
| chr1 | 30815412 | 30815416 | chr1 | 30815455 | 30815578 | chr1 | 31863186 | 31863216 |
| chr1 | 32180397 | 32180427 | chr1 | 32237639 | 32238507 | chr1 | 32410276 | 32410306 |
| chr1 | 32410519 | 32410614 | chr1 | 32533211 | 32533653 | chr1 | 32705488 | 32705550 |
| chr1 | 32756498 | 32756581 | chr1 | 32930458 | 32930558 | chr1 | 32938720 | 32938750 |
| chr1 | 33163605 | 33163786 | chr1 | 33219567 | 33219596 | chr1 | 34628948 | 34628978 |
| chr1 | 34629469 | 34629728 | chr1 | 34630548 | 34630635 | chr1 | 34630859 | 34630978 |
| chr1 | 34631580 | 34631662 | chr1 | 34631933 | 34631963 | chr1 | 34642380 | 34642489 |
| chr1 | 35258637 | 35258714 | chr1 | 35351078 | 35351659 | chr1 | 35395526 | 35395851 |
| chr1 | 35586911 | 35586962 | chr1 | 35664625 | 35664746 | chr1 | 36042679 | 36043489 |
| chr1 | 36236269 | 36236299 | chr1 | 36334925 | 36335053 | chr1 | 36563479 | 36563522 |
| chr1 | 36849009 | 36849038 | chr1 | 37498792 | 37498844 | chr1 | 37498889 | 37499181 |
| chr1 | 37499460 | 37499682 | chr1 | 37500014 | 37500153 | chr1 | 37500468 | 37500574 |
| chr1 | 37500603 | 37500806 | chr1 | 37501072 | 37501102 | chr1 | 38060267 | 38060317 |
| chr1 | 38100689 | 38100851 | chr1 | 38219712 | 38219795 | chr1 | 38230042 | 38230242 |
| chr1 | 38230283 | 38230297 | chr1 | 38230779 | 38230859 | chr1 | 38398213 | 38398348 |
| chr1 | 38412504 | 38412832 | chr1 | 38510178 | 38510217 | chr1 | 38510563 | 38510624 |
| chr1 | 38510854 | 38511119 | chr1 | 38511337 | 38511799 | chr1 | 38511822 | 38511824 |
| chr1 | 38512385 | 38512415 | chr1 | 38513244 | 38513318 | chr1 | 39269741 | 39270121 |
| chr1 | 39416980 | 39417182 | chr1 | 40072513 | 40072680 | chr1 | 40137898 | 40137984 |
| chr1 | 40237141 | 40237203 | chr1 | 40349545 | 40349647 | chr1 | 40625371 | 40625401 |
| chr1 | 40708443 | 40708578 | chr1 | 40915590 | 40915620 | chr1 | 41283958 | 41284453 |
| chr1 | 41847583 | 41847702 | chr1 | 41848810 | 41848840 | chr1 | 41915253 | 41915283 |
| chr1 | 41967342 | 41967418 | chr1 | 41991640 | 41991702 | chr1 | 43188741 | 43188874 |
| chr1 | 43400336 | 43400386 | chr1 | 43478202 | 43478255 | chr1 | 43814994 | 43815023 |
| chr1 | 43834741 | 43834922 | chr1 | 43842664 | 43842779 | chr1 | 44068774 | 44068804 |
| chr1 | 44109845 | 44109959 | chr1 | 44310283 | 44310324 | chr1 | 44494137 | 44494169 |
| chr1 | 44726912 | 44727268 | chr1 | 44872448 | 44872722 | chr1 | 44872924 | 44873172 |
| chr1 | 44873510 | 44873706 | chr1 | 44883121 | 44883214 | chr1 | 44883752 | 44884122 |
| chr1 | 45240427 | 45240514 | chr1 | 45308154 | 45308262 | chr1 | 45308592 | 45308625 |
| chr1 | 45645870 | 45645998 | chr1 | 45768429 | 45768504 | chr1 | 46077719 | 46077805 |
| chr1 | 46347598 | 46347689 | chr1 | 46632876 | 46632923 | chr1 | 46744657 | 46744733 |
| chr1 | 46913837 | 46913876 | chr1 | 46913887 | 46914245 | chr1 | 46914656 | 46914686 |
| chr1 | 46932765 | 46932905 | chr1 | 46951207 | 46951317 | chr1 | 46951645 | 46951739 |
| chr1 | 46956454 | 46956603 | chr1 | 46956823 | 46957171 | chr1 | 47009929 | 47010035 |
| chr1 | 47035373 | 47035403 | chr1 | 47078736 | 47078782 | chr1 | 47695122 | 47695422 |
| chr1 | 47696295 | 47696520 | chr1 | 47696821 | 47696964 | chr1 | 47696987 | 47697110 |
| chr1 | 47697356 | 47697510 | chr1 | 47697732 | 47697946 | chr1 | 47698007 | 47698210 |
| chr1 | 47788247 | 47788348 | chr1 | 47882063 | 47882322 | chr1 | 47882769 | 47882803 |
| chr1 | 47909718 | 47910160 | chr1 | 47910523 | 47910624 | chr1 | 47910749 | 47910914 |
| chr1 | 47911424 | 47911508 | chr1 | 47999050 | 47999163 | chr1 | 48059078 | 48059243 |
| chr1 | 49242344 | 49242533 | chr1 | 50513629 | 50513745 | chr1 | 50799278 | 50799316 |
| chr1 | 50799394 | 50799400 | chr1 | 50880932 | 50881302 | chr1 | 50881427 | 50881956 |
| chr1 | 50882144 | 50882529 | chr1 | 50882808 | 50883611 | chr1 | 50883882 | 50883976 |
| chr1 | 50884021 | 50884352 | chr1 | 50884691 | 50884887 | chr1 | 50885336 | 50885366 |
| chr1 | 50886188 | 50887084 | chr1 | 50887176 | 50887284 | chr1 | 50885709 | 50888795 |
| chr1 | 50889124 | 50889510 | chr1 | 50889820 | 50890379 | chr1 | 50890796 | 50891595 |
| chr1 | 50892153 | 50892283 | chr1 | 50892337 | 50892351 | chr1 | 50892607 | 50893422 |
| chr1 | 50893519 | 50893877 | chr1 | 51424099 | 51424224 | chr1 | 51763252 | 51763298 |
| chr1 | 52832687 | 52832820 | chr1 | 53019468 | 53019568 | chr1 | 53068166 | 53068546 |
| chr1 | 53098842 | 53099067 | chr1 | 53129154 | 53129244 | chr1 | 53192045 | 53192075 |
| chr1 | 53308568 | 53308607 | chr1 | 53308908 | 53309248 | chr1 | 53528374 | 53528439 |
| chr1 | 53705647 | 53705701 | chr1 | 54203829 | 54204399 | chr1 | 54586626 | 54586736 |
| chr1 | 54837089 | 54837119 | chr1 | 54877027 | 54877451 | chr1 | 55231115 | 55231177 |
| chr1 | 55462673 | 55462703 | chr1 | 57888367 | 57888397 | chr1 | 57888987 | 57889087 |
| chr1 | 57889402 | 57889654 | chr1 | 57890431 | 57890650 | chr1 | 58715153 | 58715194 |
| chr1 | 58715475 | 58715854 | chr1 | 58715979 | 58715993 | chr1 | 61519360 | 61519394 |
| chr1 | 61541602 | 61641718 | chr1 | 62189908 | 62189987 | chr1 | 62660740 | 62660768 |
| chr1 | 62660786 | 62660861 | chr1 | 62793237 | 62793267 | chr1 | 63539509 | 63539887 |
| chr1 | 63785619 | 63785766 | chr1 | 63786079 | 63786329 | chr1 | 63787031 | 63787063 |
| chr1 | 63787302 | 63787568 | chr1 | 63788423 | 63788557 | chr1 | 63788920 | 63789496 |
| chr1 | 63789729 | 63789791 | chr1 | 63789850 | 63789912 | chr1 | 63790253 | 63790278 |
| chr1 | 63792561 | 63792648 | chr1 | 63792798 | 63793072 | chr1 | 63795263 | 63796277 |
| chr1 | 63796498 | 63796575 | chr1 | 64240026 | 64240118 | chr1 | 64240617 | 64240673 |
| chr1 | 64734652 | 64734694 | chr1 | 64937330 | 64937542 | chr1 | 65303636 | 65303692 |
| chr1 | 65304227 | 65304256 | chr1 | 65305384 | 65305413 | chr1 | 65306926 | 65306955 |
| chr1 | 65309787 | 65309816 | chr1 | 65310487 | 65310531 | chr1 | 65311188 | 65311217 |
| chr1 | 65312331 | 65312432 | chr1 | 55731337 | 65731446 | chr1 | 65990955 | 65991018 |
| chr1 | 65991446 | 65991560 | chr1 | 65991606 | 65991757 | chr1 | 66258180 | 66258650 |
| chr1 | 66258672 | 66258774 | chr1 | 66259137 | 66259174 | chr1 | 66998790 | 66999332 |
| chr1 | 66999636 | 66999673 | chr1 | 67218064 | 67218343 | chr1 | 67390334 | 67390450 |

TABLE 12-continued

| chr | start | end | chr | start | end | chr | start | end |
|---|---|---|---|---|---|---|---|---|
| chr1 | 67391067 | 67391096 | chr1 | 67669791 | 67669853 | chr1 | 67773159 | 67773780 |
| chr1 | 70033609 | 70033916 | chr1 | 70034459 | 70034574 | chr1 | 70035088 | 70035537 |
| chr1 | 70599012 | 70599169 | chr1 | 70672778 | 70672878 | chr1 | 72749641 | 72749699 |
| chr1 | 75595819 | 75595990 | chr1 | 75596136 | 75596384 | chr1 | 75596687 | 75596858 |
| chr1 | 75596930 | 75597584 | chr1 | 75597923 | 75598179 | chr1 | 75598384 | 75598414 |
| chr1 | 75599427 | 75599621 | chr1 | 75600225 | 75600848 | chr1 | 75600925 | 75601118 |
| chr1 | 75601188 | 75601428 | chr1 | 75601983 | 75603052 | chr1 | 76080484 | 76080768 |
| chr1 | 76082129 | 76082209 | chr1 | 76354624 | 76354754 | chr1 | 76540450 | 76540666 |
| chr1 | 77333058 | 77333088 | chr1 | 77333384 | 77333433 | chr1 | 77334169 | 77334385 |
| chr1 | 77334409 | 77334756 | chr1 | 77747366 | 77747453 | chr1 | 77747939 | 77748235 |
| chr1 | 78463647 | 78463677 | chr1 | 78511466 | 78512354 | chr1 | 78957292 | 78957522 |
| chr1 | 82267150 | 82267185 | chr1 | 82268573 | 82268815 | chr1 | 84944491 | 84944568 |
| chr1 | 85358752 | 85358822 | chr1 | 85463349 | 85463378 | chr1 | 85725508 | 85725537 |
| chr1 | 85725639 | 85725668 | chr1 | 86296345 | 86296375 | chr1 | 86621660 | 86622127 |
| chr1 | 86622526 | 86622551 | chr1 | 86860608 | 86860949 | chr1 | 87617774 | 87617807 |
| chr1 | 89394066 | 89394163 | chr1 | 90099997 | 90100084 | chr1 | 90309292 | 90309490 |
| chr1 | 91172012 | 91172677 | chr1 | 91177941 | 91178207 | chr1 | 91180075 | 91180306 |
| chr1 | 91181932 | 91182132 | chr1 | 91182338 | 91183195 | chr1 | 91183251 | 91183610 |
| chr1 | 91183951 | 91183986 | chr1 | 91184423 | 91184672 | chr1 | 91185190 | 91185308 |
| chr1 | 91185348 | 91185707 | chr1 | 91188983 | 91189383 | chr1 | 91189688 | 91190380 |
| chr1 | 91190869 | 91190948 | chr1 | 91190985 | 91191234 | chr1 | 91191290 | 91191310 |
| chr1 | 91192274 | 91192576 | chr1 | 91194414 | 91194569 | chr1 | 91195117 | 91195390 |
| chr1 | 91195879 | 91196194 | chr1 | 91196226 | 91196502 | chr1 | 91316261 | 91316313 |
| chr1 | 91316627 | 91316682 | chr1 | 91869988 | 91870018 | chr1 | 92948324 | 92948597 |
| chr1 | 92948841 | 92948975 | chr1 | 92952145 | 92952655 | chr1 | 94147641 | 94147670 |
| chr1 | 94147816 | 94147845 | chr1 | 94343568 | 94343744 | chr1 | 94911234 | 94911328 |
| chr1 | 95006795 | 95006902 | chr1 | 97185262 | 97185609 | chr1 | 98510791 | 98511335 |
| chr1 | 98511628 | 98511922 | chr1 | 98514225 | 98514255 | chr1 | 98515142 | 98515191 |
| chr1 | 98515256 | 98515319 | chr1 | 98519023 | 98519675 | chr1 | 99469682 | 99469696 |
| chr1 | 99469760 | 99469788 | chr1 | 99470785 | 99470847 | chr1 | 100239507 | 100239544 |
| chr1 | 100310827 | 100310979 | chr1 | 100437068 | 100437172 | chr1 | 101004456 | 101004737 |
| chr1 | 101005071 | 101005144 | chr1 | 101005360 | 101005675 | chr1 | 101702504 | 101702616 |
| chr1 | 101703612 | 101703642 | chr1 | 103574508 | 103574537 | chr1 | 107682735 | 107682977 |
| chr1 | 107683439 | 107683517 | chr1 | 107684240 | 107684439 | chr1 | 108507063 | 108507076 |
| chr1 | 108507320 | 108507375 | chr1 | 108507495 | 108507497 | chr1 | 108507717 | 108507810 |
| chr1 | 108508052 | 108508640 | chr1 | 108722798 | 108722828 | chr1 | 109203609 | 109203672 |
| chr1 | 109585463 | 109585632 | chr1 | 109595405 | 109595534 | chr1 | 109631549 | 109631682 |
| chr1 | 109644226 | 109644336 | chr1 | 110610586 | 110610897 | chr1 | 110611046 | 110611276 |
| chr1 | 110611435 | 110611513 | chr1 | 110611654 | 110611965 | chr1 | 110626684 | 110627578 |
| chr1 | 110672889 | 110673233 | chr1 | 110692973 | 110693496 | chr1 | 110693737 | 110694117 |
| chr1 | 110754003 | 110754101 | chr1 | 110754309 | 110754356 | chr1 | 110883542 | 110883965 |
| chr1 | 111097906 | 111097936 | chr1 | 111098196 | 111098316 | chr1 | 111216763 | 111216972 |
| chr1 | 111217195 | 111217891 | chr1 | 111217924 | 111217982 | chr1 | 111440961 | 111440999 |
| chr1 | 111506007 | 111506212 | chr1 | 111813546 | 111813587 | chr1 | 112084954 | 112084984 |
| chr1 | 113166315 | 113166394 | chr1 | 114428007 | 114428160 | chr1 | 114448943 | 114448990 |
| chr1 | 114695439 | 114695736 | chr1 | 114695800 | 114695943 | chr1 | 114696350 | 114696463 |
| chr1 | 114696541 | 114696712 | chr1 | 115055395 | 115055425 | chr1 | 115256514 | 115256552 |
| chr1 | 115258729 | 115258772 | chr1 | 115631867 | 115631915 | chr1 | 115632469 | 115632555 |
| chr1 | 115880184 | 115880395 | chr1 | 115880873 | 115881042 | chr1 | 116214104 | 116214318 |
| chr1 | 116371139 | 116371201 | chr1 | 116380651 | 116381287 | chr1 | 116382387 | 116382478 |
| chr1 | 117901133 | 117901264 | chr1 | 119522074 | 119522434 | chr1 | 119522839 | 119522853 |
| chr1 | 119522926 | 119522940 | chr1 | 119527237 | 119527391 | chr1 | 119527623 | 119527662 |
| chr1 | 119528653 | 119629118 | chr1 | 119529804 | 119529839 | chr1 | 119530100 | 119530148 |
| chr1 | 119530202 | 119530507 | chr1 | 119530554 | 119530725 | chr1 | 119531029 | 119531157 |
| chr1 | 119532318 | 119532320 | chr1 | 119535908 | 119536377 | chr1 | 119542322 | 119542352 |
| chr1 | 119543070 | 119543214 | chr1 | 119543532 | 119544182 | chr1 | 119548823 | 119548853 |
| chr1 | 119549058 | 119549734 | chr1 | 119549915 | 119549929 | chr1 | 119550155 | 119550278 |
| chr1 | 119550533 | 119550633 | chr1 | 119551014 | 119551269 | chr1 | 146551186 | 146551215 |
| chr1 | 150603138 | 150603170 | chr1 | 150941425 | 150941847 | chr1 | 150994849 | 150995152 |
| chr1 | 151042405 | 151042496 | chr1 | 151169248 | 151170206 | chr1 | 151253146 | 151253427 |
| chr1 | 151300888 | 151300918 | chr1 | 151362640 | 151362779 | chr1 | 151693945 | 151694351 |
| chr1 | 151812413 | 151812442 | chr1 | 152009415 | 152009510 | chr1 | 152085398 | 152085504 |
| chr1 | 152488150 | 152488197 | chr1 | 153539476 | 153539637 | chr1 | 153540096 | 153540154 |
| chr1 | 153651965 | 153652379 | chr1 | 153896746 | 153896800 | chr1 | 153937124 | 153937330 |
| chr1 | 153948791 | 153948823 | chr1 | 154127987 | 154128016 | chr1 | 154156468 | 154156717 |
| chr1 | 154298320 | 154298557 | chr1 | 154475372 | 154475531 | chr1 | 154491036 | 154491066 |
| chr1 | 154516810 | 154516845 | chr1 | 155043331 | 155043657 | chr1 | 155161778 | 155162033 |
| chr1 | 155164415 | 155164455 | chr1 | 155283218 | 155283248 | chr1 | 155578375 | 155578921 |
| chr1 | 155617837 | 155617962 | chr1 | 155653788 | 155653868 | chr1 | 155826248 | 155826336 |
| chr1 | 155874151 | 155874300 | chr1 | 155874508 | 155874546 | chr1 | 155954282 | 155954396 |
| chr1 | 156010377 | 156010548 | chr1 | 156017591 | 156017683 | chr1 | 156030286 | 156030621 |
| chr1 | 156215329 | 156215359 | chr1 | 156215607 | 156215805 | chr1 | 156357993 | 156358508 |
| chr1 | 156390135 | 156390698 | chr1 | 156405635 | 156406070 | chr1 | 156406105 | 156406431 |
| chr1 | 156432124 | 156432637 | chr1 | 156594974 | 156595021 | chr1 | 156611889 | 156611943 |
| chr1 | 156611994 | 156612119 | chr1 | 156626589 | 156626658 | chr1 | 156626891 | 156627018 |
| chr1 | 156646278 | 156646307 | chr1 | 156646593 | 156646596 | chr1 | 156646635 | 156646647 |
| chr1 | 156814933 | 156814952 | chr1 | 156815031 | 156815146 | chr1 | 156815445 | 156815745 |
| chr1 | 156830269 | 156830348 | chr1 | 156838167 | 156838320 | chr1 | 156863107 | 156863331 |

TABLE 12-continued

| chr | start | end | chr | start | end | chr | start | end |
|---|---|---|---|---|---|---|---|---|
| chr1 | 156863662 | 156863724 | chr1 | 157247347 | 157247388 | chr1 | 157458909 | 157458961 |
| chr1 | 157895413 | 157895443 | chr1 | 158205040 | 158205070 | chr1 | 158245556 | 158245586 |
| chr1 | 158295829 | 158295935 | chr1 | 158318949 | 158318979 | chr1 | 158591699 | 158591947 |
| chr1 | 158669704 | 158669882 | chr1 | 158672648 | 158672678 | chr1 | 158687415 | 158687550 |
| chr1 | 158748648 | 158748771 | chr1 | 158760197 | 158760235 | chr1 | 158778060 | 158778152 |
| chr1 | 158815136 | 158815295 | chr1 | 158907635 | 158907665 | chr1 | 159140357 | 159140386 |
| chr1 | 159158348 | 159158368 | chr1 | 159158472 | 159158511 | chr1 | 159187279 | 159187429 |
| chr1 | 159258862 | 159258891 | chr1 | 159337419 | 159337615 | chr1 | 159409192 | 159409221 |
| chr1 | 160451043 | 160451202 | chr1 | 160693934 | 160694102 | chr1 | 160880758 | 160880788 |
| chr1 | 160986299 | 160986385 | chr1 | 160992336 | 160992587 | chr1 | 161007587 | 161007746 |
| chr1 | 161013554 | 161013677 | chr1 | 161086730 | 161086813 | chr1 | 161122645 | 161122778 |
| chr1 | 161228659 | 161228891 | chr1 | 161275564 | 161275578 | chr1 | 161275640 | 161276026 |
| chr1 | 161359069 | 161359099 | chr1 | 161367577 | 161367701 | chr1 | 161368283 | 161368507 |
| chr1 | 161368993 | 161369405 | chr1 | 161369859 | 161369945 | chr1 | 161442441 | 161442471 |
| chr1 | 161466301 | 161466347 | chr1 | 161471652 | 161471779 | chr1 | 161591472 | 161591546 |
| chr1 | 162427088 | 162427153 | chr1 | 162724401 | 162724430 | chr1 | 162729615 | 162729686 |
| chr1 | 162748392 | 162748421 | chr1 | 162792306 | 162792533 | chr1 | 163393034 | 163393064 |
| chr1 | 164290615 | 164290671 | chr1 | 164428741 | 164428831 | chr1 | 164518220 | 164518270 |
| chr1 | 164730649 | 164730796 | chr1 | 165086988 | 165087027 | chr1 | 165205079 | 165205146 |
| chr1 | 165321747 | 165321786 | chr1 | 165323151 | 165323181 | chr1 | 165324196 | 165324249 |
| chr1 | 165324305 | 165324357 | chr1 | 165324428 | 165324668 | chr1 | 165325108 | 165325356 |
| chr1 | 165325395 | 165325521 | chr1 | 165325896 | 165325950 | chr1 | 165326204 | 165326204 |
| chr1 | 165326297 | 165326469 | chr1 | 165414191 | 165414272 | chr1 | 166134247 | 166134306 |
| chr1 | 166134728 | 166134796 | chr1 | 166135193 | 166135281 | chr1 | 166853563 | 166853592 |
| chr1 | 166890292 | 166890436 | chr1 | 166916866 | 166916920 | chr1 | 166916937 | 166916949 |
| chr1 | 167090617 | 167090757 | chr1 | 167599179 | 167599330 | chr1 | 167599616 | 167599844 |
| chr1 | 167823339 | 167823461 | chr1 | 169355697 | 169355727 | chr1 | 169396376 | 169396688 |
| chr1 | 169396731 | 169396923 | chr1 | 169838016 | 169838187 | chr1 | 169930112 | 169930305 |
| chr1 | 170063947 | 170064218 | chr1 | 170629540 | 170629569 | chr1 | 170629999 | 170630029 |
| chr1 | 170630456 | 170630810 | chr1 | 170631084 | 170631163 | chr1 | 170631477 | 170631559 |
| chr1 | 170633607 | 170633637 | chr1 | 170637666 | 170637796 | chr1 | 170640517 | 170640624 |
| chr1 | 170640665 | 170640691 | chr1 | 171625525 | 171625561 | chr1 | 171665240 | 171665330 |
| chr1 | 171810200 | 171810972 | chr1 | 173638647 | 173639085 | chr1 | 175346381 | 175346551 |
| chr1 | 175388664 | 175388700 | chr1 | 177133721 | 177133814 | chr1 | 177140105 | 177140173 |
| chr1 | 177140305 | 177140714 | chr1 | 177150773 | 177150803 | chr1 | 178063112 | 178063150 |
| chr1 | 179046338 | 179046385 | chr1 | 179262226 | 179262256 | chr1 | 179544967 | 179545098 |
| chr1 | 179712164 | 179712338 | chr1 | 179712411 | 179712553 | chr1 | 179712568 | 179712733 |
| chr1 | 179712831 | 179713174 | chr1 | 180198061 | 180198209 | chr1 | 180202649 | 180203016 |
| chr1 | 180203413 | 180203607 | chr1 | 180203634 | 180204619 | chr1 | 180204898 | 180204924 |
| chr1 | 180235730 | 180235760 | chr1 | 180882576 | 180882695 | chr1 | 180919682 | 180919718 |
| chr1 | 180925271 | 180925402 | chr1 | 181014878 | 181014997 | chr1 | 181287679 | 181287757 |
| chr1 | 181288014 | 181288188 | chr1 | 181451407 | 181452120 | chr1 | 181452871 | 181452967 |
| chr1 | 181454873 | 181454912 | chr1 | 181455183 | 181455263 | chr1 | 182584048 | 182584339 |
| chr1 | 182584404 | 182584613 | chr1 | 182807578 | 182807742 | chr1 | 182862133 | 182862328 |
| chr1 | 182921839 | 182921868 | chr1 | 183129382 | 183129737 | chr1 | 183386150 | 183386288 |
| chr1 | 183386599 | 183386626 | chr1 | 183386947 | 183386964 | chr1 | 183387266 | 183387319 |
| chr1 | 183462761 | 183463024 | chr1 | 183627506 | 183627539 | chr1 | 183774244 | 183774363 |
| chr1 | 184005701 | 184005814 | chr1 | 184970783 | 184970847 | chr1 | 185073818 | 185073966 |
| chr1 | 185076172 | 185076270 | chr1 | 185336061 | 185336095 | chr1 | 186570930 | 186571030 |
| chr1 | 190444855 | 190444885 | chr1 | 190445181 | 190445276 | chr1 | 190447389 | 190447519 |
| chr1 | 195732322 | 195732539 | chr1 | 196577628 | 196577858 | chr1 | 196578101 | 196578150 |
| chr1 | 197771547 | 197771893 | chr1 | 197879400 | 197879660 | chr1 | 197879717 | 197880156 |
| chr1 | 197882140 | 197882201 | chr1 | 197882453 | 197882611 | chr1 | 197887052 | 197887066 |
| chr1 | 197887147 | 197887456 | chr1 | 197887707 | 197887741 | chr1 | 197888052 | 197888121 |
| chr1 | 197888181 | 197888319 | chr1 | 197888643 | 197889286 | chr1 | 198124799 | 198124932 |
| chr1 | 200009357 | 200009450 | chr1 | 200009750 | 200010114 | chr1 | 200011323 | 200012227 |
| chr1 | 200478843 | 200478932 | chr1 | 200591054 | 200591225 | chr1 | 201368582 | 201368727 |
| chr1 | 201476501 | 201476619 | chr1 | 201983113 | 201983200 | chr1 | 202081571 | 202081641 |
| chr1 | 202081728 | 202081804 | chr1 | 202183371 | 202183401 | chr1 | 202311820 | 202311901 |
| chr1 | 202531939 | 202532087 | chr1 | 202679215 | 202679518 | chr1 | 202856858 | 202856937 |
| chr1 | 203298307 | 203298710 | chr1 | 203429564 | 203429594 | chr1 | 203681332 | 203681362 |
| chr1 | 204333609 | 204333668 | chr1 | 204478284 | 204478427 | chr1 | 204499813 | 204499842 |
| chr1 | 204524704 | 204524744 | chr1 | 204531203 | 204531757 | chr1 | 204653561 | 204653595 |
| chr1 | 204653793 | 204653807 | chr1 | 205312596 | 205312911 | chr1 | 205424654 | 205424957 |
| chr1 | 205537663 | 205537772 | chr1 | 206950282 | 206950328 | chr1 | 207200870 | 207200962 |
| chr1 | 207227318 | 207227556 | chr1 | 207669496 | 207669787 | chr1 | 207669829 | 207670060 |
| chr1 | 207794579 | 207794609 | chr1 | 207818394 | 207818396 | chr1 | 207818434 | 207818493 |
| chr1 | 207833206 | 207833370 | chr1 | 208084289 | 208084488 | chr1 | 209164972 | 209165091 |
| chr1 | 209381132 | 209381165 | chr1 | 209604382 | 209604597 | chr1 | 209605386 | 209605415 |
| chr1 | 209849170 | 209849199 | chr1 | 209849430 | 209849459 | chr1 | 210111146 | 210111176 |
| chr1 | 210111388 | 210111421 | chr1 | 210111797 | 210111922 | chr1 | 210112037 | 210112140 |
| chr1 | 211847706 | 211847787 | chr1 | 212484610 | 212484816 | chr1 | 212963883 | 212964151 |
| chr1 | 213123871 | 213123979 | chr1 | 213124669 | 213124706 | chr1 | 213189937 | 213190065 |
| chr1 | 214156419 | 214156928 | chr1 | 214158838 | 214158910 | chr1 | 214160107 | 214160184 |
| chr1 | 214360675 | 214360858 | chr1 | 214360927 | 214360968 | chr1 | 214724531 | 214724561 |
| chr1 | 215255094 | 215255799 | chr1 | 216897216 | 216897307 | chr1 | 217307385 | 217308274 |
| chr1 | 217309007 | 217309105 | chr1 | 217309764 | 217309816 | chr1 | 217311265 | 217311839 |
| chr1 | 217313042 | 217313042 | chr1 | 217313069 | 217313747 | chr1 | 217805158 | 217805395 |

TABLE 12-continued

| chr | start | end | chr | start | end | chr | start | end |
|---|---|---|---|---|---|---|---|---|
| chr1 | 218520096 | 218520291 | chr1 | 218520310 | 218520399 | chr1 | 218520775 | 218520805 |
| chr1 | 219346992 | 219347035 | chr1 | 219347394 | 219347425 | chr1 | 220101145 | 220101210 |
| chr1 | 220101371 | 220101385 | chr1 | 220101683 | 220101712 | chr1 | 220132075 | 220132111 |
| chr1 | 220636466 | 220636510 | chr1 | 220700814 | 220700897 | chr1 | 220896508 | 220896568 |
| chr1 | 221052038 | 221052492 | chr1 | 221053610 | 221053862 | chr1 | 221067506 | 221067688 |
| chr1 | 221068156 | 221068185 | chr1 | 221068793 | 221069150 | chr1 | 221510339 | 221510368 |
| chr1 | 221737191 | 221737220 | chr1 | 223302825 | 223302890 | chr1 | 223538344 | 223538641 |
| chr1 | 223894714 | 223894752 | chr1 | 223899470 | 223899500 | chr1 | 223936633 | 223936752 |
| chr1 | 223936996 | 223937057 | chr1 | 224267615 | 224267662 | chr1 | 224363560 | 224363589 |
| chr1 | 224400490 | 224400524 | chr1 | 224493975 | 224494083 | chr1 | 224528814 | 224528844 |
| chr1 | 224803717 | 224803751 | chr1 | 224804097 | 224804295 | chr1 | 224804396 | 224804686 |
| chr1 | 224804847 | 224804910 | chr1 | 224805198 | 224805751 | chr1 | 225118306 | 225118474 |
| chr1 | 225908076 | 225908184 | chr1 | 226265194 | 226265257 | chr1 | 226384322 | 226384440 |
| chr1 | 226411247 | 226411273 | chr1 | 226411700 | 226411832 | chr1 | 226814346 | 226814408 |
| chr1 | 226925067 | 226925195 | chr1 | 226997660 | 226997719 | chr1 | 227729830 | 227730075 |
| chr1 | 227748700 | 227748733 | chr1 | 228195377 | 228196349 | chr1 | 228201221 | 228201251 |
| chr1 | 228247998 | 228248027 | chr1 | 228248302 | 228248332 | chr1 | 228345999 | 228346195 |
| chr1 | 228461158 | 228461197 | chr1 | 228463311 | 228463706 | chr1 | 228528840 | 228529016 |
| chr1 | 228558699 | 228559238 | chr1 | 228566622 | 228566753 | chr1 | 228604124 | 228604254 |
| chr1 | 228633990 | 228634261 | chr1 | 228645140 | 228645243 | chr1 | 228645306 | 228645734 |
| chr1 | 228646032 | 228646238 | chr1 | 228651432 | 228651626 | chr1 | 228651879 | 228651901 |
| chr1 | 228652207 | 228652452 | chr1 | 228652509 | 228652629 | chr1 | 228693629 | 228693767 |
| chr1 | 228871865 | 228872003 | chr1 | 229476753 | 229476879 | chr1 | 229542838 | 229542952 |
| chr1 | 229543553 | 229543603 | chr1 | 229566753 | 229567276 | chr1 | 229567370 | 229567992 |
| chr1 | 229568158 | 229568204 | chr1 | 229569810 | 229569852 | chr1 | 230404217 | 230404263 |
| chr1 | 230661779 | 230561824 | chr1 | 231149928 | 231150098 | chr1 | 231297103 | 231297221 |
| chr1 | 231298595 | 231298707 | chr1 | 231475814 | 231476081 | chr1 | 232765195 | 232765301 |
| chr1 | 233465473 | 233465503 | chr1 | 233750082 | 233750302 | chr1 | 234040247 | 234040319 |
| chr1 | 234040886 | 234040973 | chr1 | 234041416 | 234041624 | chr1 | 234349988 | 234350100 |
| chr1 | 234445373 | 234445403 | chr1 | 234620866 | 234620979 | chr1 | 234798171 | 234798201 |
| chr1 | 234839889 | 234840058 | chr1 | 234844955 | 234845079 | chr1 | 234845467 | 234845497 |
| chr1 | 235266920 | 235266950 | chr1 | 235665663 | 235665736 | chr1 | 235669296 | 235669398 |
| chr1 | 235813781 | 235813796 | chr1 | 235814010 | 235814202 | chr1 | 235814447 | 235814476 |
| chr1 | 236227637 | 236227743 | chr1 | 236227770 | 236227920 | chr1 | 236228022 | 236228096 |
| chr1 | 236228582 | 236228623 | chr1 | 236228706 | 236228789 | chr1 | 236559176 | 236559206 |
| chr1 | 236559257 | 236559271 | chr1 | 236849457 | 236849505 | chr1 | 237205159 | 237205188 |
| chr1 | 237206102 | 237206265 | chr1 | 237206512 | 237206735 | chr1 | 237970760 | 237970826 |
| chr1 | 238024448 | 238024477 | chr1 | 239550594 | 239551193 | chr1 | 240118848 | 240118973 |
| chr1 | 240161123 | 240161380 | chr1 | 240254944 | 240255011 | chr1 | 240255361 | 240255500 |
| chr1 | 240255819 | 240256158 | chr1 | 240256663 | 240256780 | chr1 | 240775425 | 240775455 |
| chr1 | 241052096 | 241052126 | chr1 | 241052360 | 241052419 | chr1 | 241520296 | 241520345 |
| chr1 | 241520583 | 241520612 | chr1 | 241587034 | 241587113 | chr1 | 241587587 | 241587797 |
| chr1 | 241912749 | 241912778 | chr1 | 242686734 | 242687688 | chr1 | 242688184 | 242688243 |
| chr1 | 242688477 | 242688695 | chr1 | 243646610 | 243646673 | chr1 | 243859000 | 243859029 |
| chr1 | 243921295 | 243921330 | chr1 | 244014221 | 244014376 | chr1 | 244080572 | 244080702 |
| chr1 | 244080963 | 244081061 | chr1 | 244081078 | 244081203 | chr1 | 244115072 | 244115212 |
| chr1 | 244893214 | 244893315 | chr1 | 245032517 | 245032603 | chr1 | 245135753 | 245136064 |
| chr1 | 245494495 | 245494578 | chr1 | 245849914 | 245849944 | chr1 | 246198078 | 246198203 |
| chr1 | 246330309 | 246330409 | chr1 | 246488175 | 246488336 | chr1 | 246654652 | 246654851 |
| chr1 | 247284422 | 247284452 | chr1 | 247496038 | 247496057 | chr1 | 247608784 | 247608814 |
| chr1 | 247684856 | 247684929 | chr1 | 247910678 | 247910780 | chr1 | 248002278 | 248002437 |
| chr1 | 248020516 | 248020630 | chr1 | 248020957 | 248021349 | chr1 | 248028015 | 248028202 |
| chr1 | 248074729 | 248074927 | chr1 | 248099751 | 248099809 | chr1 | 248198552 | 248198721 |
| chr1 | 248328701 | 248328841 | chr1 | 248691575 | 248691616 | chr1 | 248860898 | 248861046 |
| chr1 | 249121600 | 249121704 | chr2 | 46214 | 46450 | chr2 | 142427 | 142468 |
| chr2 | 264163 | 264204 | chr2 | 287580 | 287641 | chr2 | 288404 | 288470 |
| chr2 | 468424 | 468672 | chr2 | 496228 | 496380 | chr2 | 602657 | 602687 |
| chr2 | 720836 | 720894 | chr2 | 875961 | 875991 | chr2 | 945913 | 946000 |
| chr2 | 946208 | 946217 | chr2 | 946526 | 946566 | chr2 | 946917 | 947043 |
| chr2 | 947127 | 947159 | chr2 | 1652837 | 1653230 | chr2 | 1670168 | 1670216 |
| chr2 | 1746614 | 1747032 | chr2 | 1747670 | 1748007 | chr2 | 1748397 | 1748890 |
| chr2 | 2321773 | 2321802 | chr2 | 2336413 | 2336442 | chr2 | 2646900 | 2646930 |
| chr2 | 2672620 | 2672732 | chr2 | 2844720 | 2844750 | chr2 | 2893165 | 2893195 |
| chr2 | 3259989 | 3260103 | chr2 | 4019911 | 4020036 | chr2 | 4050752 | 4050781 |
| chr2 | 5831178 | 5831204 | chr2 | 5831238 | 5831324 | chr2 | 5831789 | 5831819 |
| chr2 | 5833283 | 5833432 | chr2 | 5833500 | 5833639 | chr2 | 5833735 | 5834028 |
| chr2 | 5836085 | 5836253 | chr2 | 5836548 | 5836574 | chr2 | 5836622 | 5836744 |
| chr2 | 5836828 | 5836991 | chr2 | 5837353 | 5837414 | chr2 | 5866098 | 5866211 |
| chr2 | 7062891 | 7062959 | chr2 | 7164467 | 7164788 | chr2 | 7236859 | 7236974 |
| chr2 | 7571577 | 7571747 | chr2 | 8735932 | 8736064 | chr2 | 8835493 | 8835523 |
| chr2 | 9090685 | 9090760 | chr2 | 9134404 | 9134493 | chr2 | 9192356 | 9192402 |
| chr2 | 9289969 | 9290114 | chr2 | 9960734 | 9960764 | chr2 | 10115730 | 10115772 |
| chr2 | 10152798 | 10153325 | chr2 | 10154266 | 10154564 | chr2 | 10154930 | 10155298 |
| chr2 | 10156116 | 10156389 | chr2 | 10182827 | 10182904 | chr2 | 10369155 | 10369242 |
| chr2 | 10408398 | 10408459 | chr2 | 10688874 | 10688904 | chr2 | 11052517 | 11052559 |
| chr2 | 11142174 | 11142315 | chr2 | 11356651 | 11356762 | chr2 | 11672746 | 11672775 |
| chr2 | 11809957 | 11810115 | chr2 | 11903450 | 11903480 | chr2 | 12246114 | 12246217 |
| chr2 | 12297534 | 12297564 | chr2 | 12858452 | 12858618 | chr2 | 13557899 | 13558057 |

TABLE 12-continued

| chr | start | end | chr | start | end | chr | start | end |
|---|---|---|---|---|---|---|---|---|
| chr2 | 14772761 | 14772823 | chr2 | 14774281 | 14774567 | chr2 | 15579989 | 15580019 |
| chr2 | 17719688 | 17719812 | chr2 | 18059035 | 18059085 | chr2 | 18059781 | 18059841 |
| chr2 | 19550214 | 19550244 | chr2 | 19551322 | 19551366 | chr2 | 19556318 | 19556672 |
| chr2 | 19557068 | 19557098 | chr2 | 19557685 | 19557727 | chr2 | 19558832 | 19558893 |
| chr2 | 19561131 | 19561316 | chr2 | 19561524 | 19561685 | chr2 | 19563358 | 19563433 |
| chr2 | 20068798 | 20068885 | chr2 | 20442433 | 20442498 | chr2 | 20641988 | 20642081 |
| chr2 | 20642541 | 20642648 | chr2 | 20710145 | 20710324 | chr2 | 20865636 | 20865927 |
| chr2 | 22404181 | 22404227 | chr2 | 24318290 | 24318357 | chr2 | 25029252 | 25029300 |
| chr2 | 25374762 | 25374804 | chr2 | 25390994 | 25391212 | chr2 | 25391684 | 25391725 |
| chr2 | 25438821 | 25438871 | chr2 | 25439139 | 25439465 | chr2 | 25439727 | 25439915 |
| chr2 | 25600736 | 25600804 | chr2 | 26928094 | 25928166 | chr2 | 26372967 | 26372997 |
| chr2 | 26395447 | 26395556 | chr2 | 26402030 | 26402060 | chr2 | 26407744 | 26407921 |
| chr2 | 26521972 | 26522221 | chr2 | 26915763 | 26916066 | chr2 | 26916089 | 26916259 |
| chr2 | 27070324 | 27070414 | chr2 | 27071240 | 27071346 | chr2 | 27072492 | 27072534 |
| chr2 | 27072822 | 27072989 | chr2 | 27271699 | 27272218 | chr2 | 27356168 | 27356198 |
| chr2 | 27433532 | 27433601 | chr2 | 27543012 | 27543074 | chr2 | 27578243 | 27578396 |
| chr2 | 27648172 | 27648294 | chr2 | 27665125 | 27665154 | chr2 | 27665506 | 27665711 |
| chr2 | 27764046 | 27764168 | chr2 | 27887525 | 27887555 | chr2 | 29033336 | 29033697 |
| chr2 | 29091592 | 29091838 | chr2 | 29338159 | 29338747 | chr2 | 29338810 | 29338969 |
| chr2 | 29420483 | 29420512 | chr2 | 29432640 | 29432696 | chr2 | 29436844 | 29436888 |
| chr2 | 29443573 | 29443710 | chr2 | 29445198 | 29445482 | chr2 | 29446361 | 29446396 |
| chr2 | 30143304 | 30143322 | chr2 | 30143383 | 30143492 | chr2 | 30144041 | 30144150 |
| chr2 | 30144175 | 30144411 | chr2 | 30368444 | 30368586 | chr2 | 30453785 | 30453941 |
| chr2 | 30514753 | 30514783 | chr2 | 31360306 | 31360589 | chr2 | 31360631 | 31360755 |
| chr2 | 31360804 | 31360831 | chr2 | 31361089 | 31361118 | chr2 | 31361356 | 31361385 |
| chr2 | 31456682 | 31457039 | chr2 | 32275196 | 32275303 | chr2 | 32504169 | 32504378 |
| chr2 | 32580386 | 32580476 | chr2 | 38302370 | 38302876 | chr2 | 38365525 | 38365748 |
| chr2 | 38551124 | 38551390 | chr2 | 38594819 | 38594874 | chr2 | 38727561 | 38727707 |
| chr2 | 38762382 | 38762412 | chr2 | 38953573 | 38953603 | chr2 | 38983213 | 38983333 |
| chr2 | 39187218 | 39187237 | chr2 | 39187544 | 39187722 | chr2 | 39893090 | 39893501 |
| chr2 | 39893972 | 39894059 | chr2 | 40678603 | 40679604 | chr2 | 41789816 | 41789853 |
| chr2 | 42274595 | 42274633 | chr2 | 42329431 | 42329444 | chr2 | 42329494 | 42329666 |
| chr2 | 42720262 | 42720446 | chr2 | 43019599 | 43019868 | chr2 | 43388330 | 43388529 |
| chr2 | 43451909 | 43452327 | chr2 | 43824133 | 43824353 | chr2 | 44226958 | 44226988 |
| chr2 | 44227193 | 44227223 | chr2 | 44497708 | 44497875 | chr2 | 44809187 | 44809217 |
| chr2 | 45028988 | 45029058 | chr2 | 45029184 | 45029371 | chr2 | 45029682 | 45029712 |
| chr2 | 45155125 | 45155210 | chr2 | 45155356 | 45156811 | chr2 | 45156833 | 45157711 |
| chr2 | 45159956 | 45160267 | chr2 | 45160596 | 45160634 | chr2 | 45161663 | 45162112 |
| chr2 | 45162394 | 45162481 | chr2 | 45162751 | 45162913 | chr2 | 45164663 | 45164693 |
| chr2 | 45165564 | 45165594 | chr2 | 45168803 | 45168833 | chr2 | 45169446 | 45170029 |
| chr2 | 45171385 | 45171563 | chr2 | 45171837 | 45171862 | chr2 | 45176601 | 45176768 |
| chr2 | 45179620 | 45179650 | chr2 | 45179939 | 45180203 | chr2 | 45181520 | 45181672 |
| chr2 | 45181887 | 45182001 | chr2 | 45228627 | 45228730 | chr2 | 45231320 | 45231396 |
| chr2 | 45231805 | 45232131 | chr2 | 45233385 | 45233586 | chr2 | 45235594 | 45235926 |
| chr2 | 45237673 | 45237795 | chr2 | 45240548 | 45240630 | chr2 | 45240764 | 45240784 |
| chr2 | 45241136 | 45241168 | chr2 | 45395854 | 45395920 | chr2 | 45396315 | 45396451 |
| chr2 | 45396688 | 45396995 | chr2 | 46526302 | 46526448 | chr2 | 47193930 | 47194136 |
| chr2 | 47200591 | 47200621 | chr2 | 47249725 | 47249848 | chr2 | 47597455 | 47598620 |
| chr2 | 47599589 | 47599753 | chr2 | 47748140 | 47748494 | chr2 | 47797043 | 47797818 |
| chr2 | 47798180 | 47798663 | chr2 | 47798954 | 47799032 | chr2 | 42629615 | 48629685 |
| chr2 | 48636504 | 48636669 | chr2 | 48648878 | 48648940 | chr2 | 48982582 | 48982700 |
| chr2 | 48982754 | 48982865 | chr2 | 50573595 | 50573638 | chr2 | 50573692 | 50573722 |
| chr2 | 50574121 | 50574355 | chr2 | 50574402 | 50574684 | chr2 | 50574739 | 50574859 |
| chr2 | 54322431 | 54322576 | chr2 | 55289011 | 55289296 | chr2 | 55612770 | 55612800 |
| chr2 | 55669261 | 55669454 | chr2 | 56149836 | 56149866 | chr2 | 56150729 | 56151193 |
| chr2 | 56410817 | 56410996 | chr2 | 56411691 | 56411733 | chr2 | 58552519 | 58552689 |
| chr2 | 58656049 | 58656125 | chr2 | 59400384 | 59400424 | chr2 | 60416280 | 60416494 |
| chr2 | 60706759 | 60706804 | chr2 | 60796587 | 60796646 | chr2 | 60797137 | 60797281 |
| chr2 | 61135032 | 61135137 | chr2 | 61232163 | 61232232 | chr2 | 61242732 | 61242802 |
| chr2 | 61395039 | 61395069 | chr2 | 61556203 | 61556239 | chr2 | 61656393 | 61656423 |
| chr2 | 61992076 | 61992289 | chr2 | 52798343 | 62798386 | chr2 | 53278962 | 63278992 |
| chr2 | 63280952 | 63281651 | chr2 | 63282716 | 63282786 | chr2 | 63283014 | 63283027 |
| chr2 | 63283952 | 63284146 | chr2 | 63284777 | 63284811 | chr2 | 63285081 | 63286047 |
| chr2 | 63286359 | 63286584 | chr2 | 63286694 | 63286747 | chr2 | 63287083 | 63287368 |
| chr2 | 65251310 | 65251340 | chr2 | 65779892 | 65779983 | chr2 | 66652863 | 66652963 |
| chr2 | 66653238 | 66653496 | chr2 | 66653764 | 66653914 | chr2 | 66660650 | 66660888 |
| chr2 | 66662749 | 66662824 | chr2 | 66808525 | 66808633 | chr2 | 66808727 | 66809361 |
| chr2 | 67625453 | 67625770 | chr2 | 57626102 | 67626257 | chr2 | 68287707 | 68287799 |
| chr2 | 68546324 | 68546516 | chr2 | 68546553 | 68546892 | chr2 | 68559261 | 68559365 |
| chr2 | 68672853 | 68672938 | chr2 | 69027024 | 69027053 | chr2 | 69975443 | 69975523 |
| chr2 | 70058262 | 70058292 | chr2 | 70367670 | 70367710 | chr2 | 70418528 | 70418627 |
| chr2 | 70427556 | 70427646 | chr2 | 70430997 | 70431160 | chr2 | 71355019 | 71355117 |
| chr2 | 71355768 | 71355961 | chr2 | 71503790 | 71503826 | chr2 | 71504103 | 71504148 |
| chr2 | 71680833 | 71680863 | chr2 | 71693374 | 71693593 | chr2 | 72374375 | 72374432 |
| chr2 | 72374714 | 72374765 | chr2 | 73145640 | 73145694 | chr2 | 73145924 | 73146021 |
| chr2 | 73147324 | 73147527 | chr2 | 73147967 | 73148066 | chr2 | 73148175 | 73148243 |
| chr2 | 73150924 | 73150954 | chr2 | 73151187 | 73161831 | chr2 | 73152740 | 73152754 |
| chr2 | 73416356 | 73416535 | chr2 | 73429523 | 73429614 | chr2 | 73429977 | 73430069 |

TABLE 12-continued

| chr | start | end | chr | start | end | chr | start | end |
|---|---|---|---|---|---|---|---|---|
| chr2 | 73430322 | 73430372 | chr2 | 73430443 | 73430743 | chr2 | 73440205 | 73440293 |
| chr2 | 73518448 | 73519919 | chr2 | 73519579 | 73519841 | chr2 | 74010528 | 74010773 |
| chr2 | 74153198 | 74153227 | chr2 | 74350410 | 74350497 | chr2 | 74426185 | 74426214 |
| chr2 | 74454074 | 74454261 | chr2 | 74647864 | 74648007 | chr2 | 74679047 | 74679123 |
| chr2 | 74726744 | 74726774 | chr2 | 74740852 | 74741387 | chr2 | 74741835 | 74741844 |
| chr2 | 74741873 | 74741955 | chr2 | 74742325 | 74742647 | chr2 | 74742694 | 74743144 |
| chr2 | 74782081 | 74782087 | chr2 | 74782219 | 74782271 | chr2 | 74874865 | 74874903 |
| chr2 | 75427040 | 75427114 | chr2 | 75427369 | 75427399 | chr2 | 75427930 | 75428177 |
| chr2 | 75720510 | 75720541 | chr2 | 79347459 | 79347546 | chr2 | 80529378 | 80529443 |
| chr2 | 80529662 | 80529908 | chr2 | 80529986 | 80530022 | chr2 | 80530505 | 80530558 |
| chr2 | 80531725 | 80531755 | chr2 | 80549585 | 80549745 | chr2 | 85107454 | 85107538 |
| chr2 | 85361467 | 85361528 | chr2 | 85838101 | 85838299 | chr2 | 86191145 | 86191309 |
| chr2 | 86263223 | 86263270 | chr2 | 86423330 | 86423592 | chr2 | 86783725 | 86783755 |
| chr2 | 86791221 | 86791251 | chr2 | 87016579 | 87016636 | chr2 | 87017796 | 87018396 |
| chr2 | 87036611 | 87036640 | chr2 | 88469312 | 88469483 | chr2 | 88751281 | 88751419 |
| chr2 | 88751461 | 88751800 | chr2 | 88752055 | 88752285 | chr2 | 88752603 | 88752785 |
| chr2 | 88990189 | 88990264 | chr2 | 89064806 | 89064975 | chr2 | 89065129 | 89065278 |
| chr2 | 89262535 | 89252679 | chr2 | 95663969 | 95664014 | chr2 | 95690747 | 95690793 |
| chr2 | 95691036 | 95691269 | chr2 | 95691530 | 95691769 | chr2 | 95691994 | 95692480 |
| chr2 | 95941678 | 95941812 | chr2 | 96070057 | 96070165 | chr2 | 96974485 | 96974516 |
| chr2 | 96990898 | 96991316 | chr2 | 97126702 | 97126832 | chr2 | 97193252 | 97193626 |
| chr2 | 97427515 | 97428093 | chr2 | 98581819 | 98581849 | chr2 | 98703323 | 98703475 |
| chr2 | 98703675 | 98703736 | chr2 | 98962898 | 98962900 | chr2 | 98963329 | 98963595 |
| chr2 | 98963869 | 98964200 | chr2 | 98964596 | 98964645 | chr2 | 99439369 | 99439507 |
| chr2 | 99553391 | 99553656 | chr2 | 99796259 | 99796330 | chr2 | 99798646 | 99799153 |
| chr2 | 100618451 | 100618480 | chr2 | 100937836 | 100938209 | chr2 | 100938330 | 100938544 |
| chr2 | 100938575 | 100938809 | chr2 | 100938985 | 100939155 | chr2 | 101009832 | 101009927 |
| chr2 | 101034242 | 101034293 | chr2 | 101186368 | 101186458 | chr2 | 101436632 | 101436708 |
| chr2 | 101666893 | 101667004 | chr2 | 101834977 | 101835057 | chr2 | 102091180 | 102091335 |
| chr2 | 103236165 | 103236292 | chr2 | 105459081 | 105459151 | chr2 | 105459908 | 105460599 |
| chr2 | 105460921 | 105460951 | chr2 | 105461187 | 105461243 | chr2 | 105461564 | 105461667 |
| chr2 | 105461700 | 105461896 | chr2 | 105462165 | 105462222 | chr2 | 105468791 | 105468908 |
| chr2 | 105469645 | 105469856 | chr2 | 105469881 | 105470091 | chr2 | 105470350 | 105470840 |
| chr2 | 105472231 | 105472425 | chr2 | 105472213 | 105472845 | chr2 | 105473248 | 105473553 |
| chr2 | 105478762 | 105479089 | chr2 | 105483655 | 105483719 | chr2 | 105484450 | 105484522 |
| chr2 | 105488437 | 105488496 | chr2 | 105760981 | 105761037 | chr2 | 105937344 | 105937498 |
| chr2 | 106060615 | 106060792 | chr2 | 106681733 | 106681767 | chr2 | 106682012 | 106682098 |
| chr2 | 106730223 | 106730256 | chr2 | 106959368 | 106959568 | chr2 | 106959916 | 106959988 |
| chr2 | 107103865 | 107103928 | chr2 | 107502600 | 107502729 | chr2 | 107503532 | 107503561 |
| chr2 | 107503884 | 107504018 | chr2 | 108364897 | 108364940 | chr2 | 109335133 | 109335166 |
| chr2 | 109648080 | 109648222 | chr2 | 109745989 | 109746079 | chr2 | 109746289 | 109746387 |
| chr2 | 109746463 | 109746477 | chr2 | 110015080 | 110015110 | chr2 | 110370941 | 110371219 |
| chr2 | 110873016 | 110873045 | chr2 | 111544817 | 111544997 | chr2 | 111875191 | 111875611 |
| chr2 | 112657033 | 112657092 | chr2 | 112817735 | 112817765 | chr2 | 113227024 | 113227225 |
| chr2 | 113594639 | 113594668 | chr2 | 113803960 | 113803990 | chr2 | 113931503 | 113931532 |
| chr2 | 114256978 | 114257137 | chr2 | 114261300 | 114261458 | chr2 | 114461746 | 114461879 |
| chr2 | 114470022 | 114470201 | chr2 | 114515528 | 114515618 | chr2 | 114634867 | 114634988 |
| chr2 | 115918661 | 115918892 | chr2 | 115919338 | 115919424 | chr2 | 115919831 | 115920534 |
| chr2 | 118380865 | 118380904 | chr2 | 118981151 | 118981856 | chr2 | 118981946 | 118982147 |
| chr2 | 118982254 | 118982497 | chr2 | 119067636 | 119068049 | chr2 | 119532161 | 119532255 |
| chr2 | 119566239 | 119566272 | chr2 | 119591351 | 119591465 | chr2 | 119592588 | 119592777 |
| chr2 | 119592997 | 119593567 | chr2 | 119599926 | 119600031 | chr2 | 119600332 | 119600555 |
| chr2 | 119600570 | 119600747 | chr2 | 119600949 | 119600952 | chr2 | 119600996 | 119601061 |
| chr2 | 119602601 | 119602629 | chr2 | 119602829 | 119603086 | chr2 | 119604032 | 119604158 |
| chr2 | 119604809 | 119604851 | chr2 | 119606135 | 119606499 | chr2 | 119606783 | 119606839 |
| chr2 | 119607176 | 119607411 | chr2 | 119610844 | 119610939 | chr2 | 119611745 | 119611799 |
| chr2 | 119612324 | 119612354 | chr2 | 119614130 | 119614171 | chr2 | 119614780 | 119614852 |
| chr2 | 119615055 | 119615627 | chr2 | 119616155 | 119616551 | chr2 | 119616809 | 119616870 |
| chr2 | 119914720 | 119914752 | chr2 | 119916525 | 119916595 | chr2 | 120281646 | 120281693 |
| chr2 | 120281939 | 120281953 | chr2 | 120769511 | 120769746 | chr2 | 120825608 | 120825769 |
| chr2 | 120980068 | 120980098 | chr2 | 120980353 | 120980395 | chr2 | 121200390 | 121200433 |
| chr2 | 121345081 | 121345111 | chr2 | 121411888 | 121412153 | chr2 | 122176232 | 122176293 |
| chr2 | 122495267 | 122495413 | chr2 | 122809705 | 122809801 | chr2 | 124782333 | 124782458 |
| chr2 | 124782692 | 124783097 | chr2 | 127412291 | 127412386 | chr2 | 127413970 | 127413995 |
| chr2 | 127423220 | 127423350 | chr2 | 127429010 | 127429044 | chr2 | 127438633 | 127438663 |
| chr2 | 127783043 | 127783257 | chr2 | 127863601 | 127863725 | chr2 | 127976467 | 127976672 |
| chr2 | 128421891 | 128421947 | chr2 | 128616617 | 128616838 | chr2 | 128680057 | 128680087 |
| chr2 | 128847677 | 128847723 | chr2 | 129174888 | 129174918 | chr2 | 129494389 | 129494421 |
| chr2 | 130763584 | 130763623 | chr2 | 130937868 | 130937898 | chr2 | 130971149 | 130971321 |
| chr2 | 131084953 | 131085013 | chr2 | 131477785 | 131477936 | chr2 | 131594989 | 131595019 |
| chr2 | 131673756 | 131673785 | chr2 | 131720852 | 131721098 | chr2 | 131721461 | 131721584 |
| chr2 | 131721867 | 131721949 | chr2 | 131792260 | 131792519 | chr2 | 131792532 | 131792746 |
| chr2 | 131792921 | 131793131 | chr2 | 132088786 | 132088828 | chr2 | 132121661 | 132121829 |
| chr2 | 132152361 | 132152495 | chr2 | 132182790 | 132183089 | chr2 | 132208115 | 132208278 |
| chr2 | 132767457 | 132767707 | chr2 | 132795261 | 132795403 | chr2 | 132795670 | 132795728 |
| chr2 | 133014598 | 133014638 | chr2 | 133015275 | 133015323 | chr2 | 133062362 | 133062389 |
| chr2 | 133426249 | 133426279 | chr2 | 133426637 | 133426674 | chr2 | 136287358 | 136287390 |
| chr2 | 137522445 | 137522475 | chr2 | 137523825 | 137523855 | chr2 | 139536937 | 139537145 |

TABLE 12-continued

| chr | start | end | chr | start | end | chr | start | end |
|---|---|---|---|---|---|---|---|---|
| chr2 | 139537443 | 139537822 | chr2 | 139537851 | 139537865 | chr2 | 142887871 | 142888066 |
| chr2 | 142888348 | 142888418 | chr2 | 143569561 | 143569634 | chr2 | 144129765 | 144129795 |
| chr2 | 144299758 | 144299788 | chr2 | 144694367 | 144694514 | chr2 | 144694554 | 144695135 |
| chr2 | 145273404 | 145273751 | chr2 | 145274186 | 145274455 | chr2 | 145274814 | 145275213 |
| chr2 | 145282119 | 146282149 | chr2 | 148776809 | 148777035 | chr2 | 149633097 | 149633399 |
| chr2 | 149633744 | 149633965 | chr2 | 149645496 | 149645864 | chr2 | 151342903 | 151343277 |
| chr2 | 152248835 | 152248983 | chr2 | 154333535 | 154333567 | chr2 | 154334272 | 154334665 |
| chr2 | 154335185 | 154335271 | chr2 | 154728245 | 154728440 | chr2 | 154729083 | 154729240 |
| chr2 | 154729559 | 154729589 | chr2 | 155555038 | 155555361 | chr2 | 157176592 | 157176717 |
| chr2 | 157177003 | 157178310 | chr2 | 157178646 | 157178731 | chr2 | 160761070 | 160761556 |
| chr2 | 161253293 | 161253455 | chr2 | 162166600 | 162166632 | chr2 | 162272989 | 162273314 |
| chr2 | 162273383 | 162274338 | chr2 | 162274717 | 162274866 | chr2 | 162275146 | 162275226 |
| chr2 | 162275311 | 162275437 | chr2 | 162275473 | 162275802 | chr2 | 162280153 | 162280415 |
| chr2 | 162280741 | 162280956 | chr2 | 162283365 | 162283602 | chr2 | 162283783 | 162284055 |
| chr2 | 164593096 | 164593137 | chr2 | 166929478 | 166929613 | chr2 | 168150069 | 168150245 |
| chr2 | 168150751 | 168150945 | chr2 | 170255970 | 170256139 | chr2 | 170282981 | 170283080 |
| chr2 | 170373281 | 170373413 | chr2 | 170551730 | 170551942 | chr2 | 170681880 | 170682422 |
| chr2 | 171570182 | 171570189 | chr2 | 171570684 | 171570733 | chr2 | 171571264 | 171571315 |
| chr2 | 171571889 | 171572068 | chr2 | 171670349 | 171670446 | chr2 | 171671487 | 171671789 |
| chr2 | 171671800 | 171671881 | chr2 | 171673873 | 171673939 | chr2 | 171674739 | 171675066 |
| chr2 | 171675361 | 171675382 | chr2 | 171675523 | 171675592 | chr2 | 171676684 | 171676785 |
| chr2 | 171822428 | 171822480 | chr2 | 171839017 | 171839047 | chr2 | 172367021 | 172367125 |
| chr2 | 172411136 | 172411166 | chr2 | 172945124 | 172945167 | chr2 | 172945896 | 172946211 |
| chr2 | 172947717 | 172947913 | chr2 | 172948184 | 172948314 | chr2 | 172948709 | 172948751 |
| chr2 | 172949186 | 172949282 | chr2 | 172949349 | 172949711 | chr2 | 172952521 | 172952881 |
| chr2 | 172952993 | 172953046 | chr2 | 172955472 | 172955545 | chr2 | 172957907 | 172958066 |
| chr2 | 172961398 | 172961598 | chr2 | 172964821 | 172964888 | chr2 | 172965296 | 172965298 |
| chr2 | 172965648 | 172965762 | chr2 | 172966264 | 172966442 | chr2 | 172972735 | 122972890 |
| chr2 | 172972931 | 172973218 | chr2 | 173099784 | 173099814 | chr2 | 173100262 | 173100430 |
| chr2 | 173422685 | 173422734 | chr2 | 174148058 | 174148157 | chr2 | 175111870 | 175112092 |
| chr2 | 175190871 | 175191972 | chr2 | 175192085 | 175192468 | chr2 | 175193268 | 175193644 |
| chr2 | 175193809 | 175193823 | chr2 | 175195831 | 175195858 | chr2 | 175196432 | 175196575 |
| chr2 | 175197089 | 175197119 | chr2 | 175198752 | 175198766 | chr2 | 175198846 | 175198966 |
| chr2 | 175199527 | 175199554 | chr2 | 175199922 | 175199935 | chr2 | 175200140 | 175200440 |
| chr2 | 175200710 | 175200852 | chr2 | 175200917 | 175201182 | chr2 | 175201360 | 175201541 |
| chr2 | 175201776 | 175201828 | chr2 | 175202127 | 175202245 | chr2 | 175202569 | 175202600 |
| chr2 | 175202634 | 175202652 | chr2 | 175204174 | 175204204 | chr2 | 175204786 | 175204946 |
| chr2 | 175205588 | 175205799 | chr2 | 175206833 | 175206905 | chr2 | 175206961 | 175207028 |
| chr2 | 175207228 | 175207258 | chr2 | 175207536 | 175207653 | chr2 | 175208311 | 175208868 |
| chr2 | 175208997 | 175209135 | chr2 | 175261402 | 175261432 | chr2 | 175383935 | 175383965 |
| chr2 | 175547041 | 175547140 | chr2 | 175547384 | 175547413 | chr2 | 176940167 | 176940315 |
| chr2 | 176943269 | 176943568 | chr2 | 176943861 | 176943902 | chr2 | 176944457 | 176944846 |
| chr2 | 176945138 | 176945268 | chr2 | 176945582 | 176945784 | chr2 | 176946578 | 176946867 |
| chr2 | 176947285 | 176947389 | chr2 | 176947764 | 176947903 | chr2 | 176948599 | 176948742 |
| chr2 | 176949045 | 176949075 | chr2 | 176949695 | 176949869 | chr2 | 176950142 | 176950258 |
| chr2 | 176956558 | 176956599 | chr2 | 176956921 | 176957199 | chr2 | 176957577 | 176957628 |
| chr2 | 176957915 | 176957919 | chr2 | 176958138 | 176958489 | chr2 | 176959289 | 176959511 |
| chr2 | 176963448 | 176963522 | chr2 | 176964085 | 176964149 | chr2 | 176964390 | 176964767 |
| chr2 | 176965265 | 176965492 | chr2 | 176969463 | 176969613 | chr2 | 176969677 | 176969908 |
| chr2 | 176971628 | 176971651 | chr2 | 176976029 | 176976188 | chr2 | 176980750 | 176980937 |
| chr2 | 176981377 | 176981505 | chr2 | 176982584 | 176982627 | chr2 | 176986715 | 176986848 |
| chr2 | 176987057 | 176987224 | chr2 | 176987971 | 176988103 | chr2 | 176988155 | 176988304 |
| chr2 | 176993074 | 176993103 | chr2 | 176993547 | 176993855 | chr2 | 176994031 | 176994379 |
| chr2 | 176994498 | 176994621 | chr2 | 176995072 | 176995269 | chr2 | 176995332 | 176995668 |
| chr2 | 177001102 | 177001695 | chr2 | 177001782 | 177001976 | chr2 | 177004566 | 177004658 |
| chr2 | 177014981 | 177015010 | chr2 | 177027425 | 177027438 | chr2 | 177030149 | 177030226 |
| chr2 | 177042984 | 177042998 | chr2 | 177043267 | 177043515 | chr2 | 177053276 | 177053434 |
| chr2 | 177053619 | 177053702 | chr2 | 177054113 | 177054351 | chr2 | 177503048 | 177503077 |
| chr2 | 177503581 | 177503610 | chr2 | 177872600 | 177872629 | chr2 | 178098791 | 178098967 |
| chr2 | 178973003 | 178973042 | chr2 | 179303534 | 179303727 | chr2 | 179316860 | 179317057 |
| chr2 | 182202233 | 182202291 | chr2 | 182321397 | 182321637 | chr2 | 182322039 | 182322170 |
| chr2 | 182322400 | 182323042 | chr2 | 182451522 | 182451551 | chr2 | 182542903 | 182542933 |
| chr2 | 182543321 | 182543418 | chr2 | 182543764 | 182543925 | chr2 | 182545211 | 182545275 |
| chr2 | 182545539 | 182545694 | chr2 | 182546002 | 182546085 | chr2 | 182546435 | 182546465 |
| chr2 | 182547385 | 182547387 | chr2 | 182547438 | 182547613 | chr2 | 182548062 | 182548161 |
| chr2 | 182549088 | 182549134 | chr2 | 182549337 | 182549454 | chr2 | 182550094 | 182550124 |
| chr2 | 182819048 | 182819216 | chr2 | 183251240 | 183251303 | chr2 | 183731294 | 183731331 |
| chr2 | 183731467 | 183731524 | chr2 | 183731809 | 183732076 | chr2 | 185462869 | 185462980 |
| chr2 | 185463193 | 185463817 | chr2 | 186603488 | 186603518 | chr2 | 188419047 | 188419204 |
| chr2 | 189157427 | 189157688 | chr2 | 190708790 | 190708819 | chr2 | 193059025 | 193059317 |
| chr2 | 193059345 | 193059548 | chr2 | 193059662 | 193060067 | chr2 | 193060385 | 193060441 |
| chr2 | 193060683 | 193060891 | chr2 | 193061388 | 193061480 | chr2 | 197793125 | 197793267 |
| chr2 | 198238409 | 198238439 | chr2 | 198267345 | 198267374 | chr2 | 198456480 | 198456719 |
| chr2 | 198651002 | 198651076 | chr2 | 200326590 | 200326735 | chr2 | 200327424 | 200327451 |
| chr2 | 200329030 | 200329393 | chr2 | 200329433 | 200329668 | chr2 | 200333801 | 200333834 |
| chr2 | 200334976 | 200335451 | chr2 | 200335592 | 200335952 | chr2 | 200818892 | 200819130 |
| chr2 | 201156690 | 201156804 | chr2 | 201172444 | 201172480 | chr2 | 201450556 | 201450707 |
| chr2 | 201451014 | 201451040 | chr2 | 201693680 | 201693718 | chr2 | 202097078 | 202097143 |

TABLE 12-continued

| chr | start | end | chr | start | end | chr | start | end |
|---|---|---|---|---|---|---|---|---|
| chr2 | 202098936 | 202098965 | chr2 | 202101190 | 202101219 | chr2 | 202122459 | 202122683 |
| chr2 | 202477462 | 202477621 | chr2 | 202899862 | 202899876 | chr2 | 203484608 | 203484646 |
| chr2 | 203498452 | 203498489 | chr2 | 203880390 | 203880492 | chr2 | 204194588 | 204194725 |
| chr2 | 206551072 | 206551362 | chr2 | 207022702 | 207022802 | chr2 | 207139072 | 207139102 |
| chr2 | 207139347 | 207139605 | chr2 | 207307548 | 207307562 | chr2 | 207308802 | 207308857 |
| chr2 | 207506691 | 207507181 | chr2 | 208574821 | 208574917 | chr2 | 208588311 | 208588341 |
| chr2 | 208635534 | 208635774 | chr2 | 208662170 | 208662376 | chr2 | 208662672 | 208662710 |
| chr2 | 208989294 | 208989382 | chr2 | 209094739 | 209094845 | chr2 | 209113097 | 209113126 |
| chr2 | 209225237 | 209225275 | chr2 | 209271322 | 209271336 | chr2 | 210636335 | 210636381 |
| chr2 | 210636430 | 210636689 | chr2 | 210636738 | 210636876 | chr2 | 212248428 | 212248457 |
| chr2 | 212288927 | 212288956 | chr2 | 212295683 | 212295820 | chr2 | 212530120 | 212530149 |
| chr2 | 212537902 | 212537994 | chr2 | 212566811 | 212566840 | chr2 | 212578292 | 212578321 |
| chr2 | 212587132 | 212587151 | chr2 | 213401235 | 213401339 | chr2 | 213401613 | 213401947 |
| chr2 | 213403110 | 213403337 | chr2 | 215275823 | 215275852 | chr2 | 215276310 | 215276339 |
| chr2 | 217396039 | 217396069 | chr2 | 217448294 | 217448441 | chr2 | 217559296 | 217559326 |
| chr2 | 217559966 | 217559999 | chr2 | 218770207 | 218770270 | chr2 | 218806147 | 218806302 |
| chr2 | 219276888 | 219276918 | chr2 | 219736151 | 219736691 | chr2 | 219828049 | 219828117 |
| chr2 | 219847462 | 219847555 | chr2 | 219848809 | 219848891 | chr2 | 219848936 | 219849001 |
| chr2 | 219857723 | 219857737 | chr2 | 220080510 | 220081033 | chr2 | 220173989 | 220174036 |
| chr2 | 220174060 | 220174296 | chr2 | 220196354 | 220196567 | chr2 | 220223098 | 220223128 |
| chr2 | 220223648 | 220223699 | chr2 | 220283363 | 220283519 | chr2 | 220299588 | 220299634 |
| chr2 | 220299886 | 220300059 | chr2 | 220349055 | 220349706 | chr2 | 220361447 | 220361466 |
| chr2 | 220416379 | 220416513 | chr2 | 220417649 | 220417649 | chr2 | 221853201 | 221853352 |
| chr2 | 222285828 | 222285858 | chr2 | 222310068 | 222310105 | chr2 | 222435773 | 222435863 |
| chr2 | 223155722 | 223156188 | chr2 | 223158730 | 223159453 | chr2 | 223159869 | 223160065 |
| chr2 | 223160342 | 223160379 | chr2 | 223161247 | 223161684 | chr2 | 223161807 | 223162063 |
| chr2 | 223162779 | 223162890 | chr2 | 223162929 | 223163224 | chr2 | 223163473 | 223163535 |
| chr2 | 223163768 | 223163954 | chr2 | 223164534 | 223164883 | chr2 | 223165434 | 223165832 |
| chr2 | 223166294 | 223166408 | chr2 | 223166449 | 223166721 | chr2 | 223167389 | 223167573 |
| chr2 | 223168437 | 223168831 | chr2 | 223169640 | 223169864 | chr2 | 223170375 | 223170434 |
| chr2 | 223171109 | 223171180 | chr2 | 223172337 | 223172367 | chr2 | 223172924 | 223173173 |
| chr2 | 223175663 | 223175694 | chr2 | 223175746 | 223176181 | chr2 | 223176456 | 223176511 |
| chr2 | 223176720 | 223176983 | chr2 | 223177315 | 223177610 | chr2 | 224661521 | 224661701 |
| chr2 | 224903260 | 224903440 | chr2 | 224903690 | 224903755 | chr2 | 224904108 | 224904237 |
| chr2 | 225464038 | 225464068 | chr2 | 228029418 | 228029531 | chr2 | 228411020 | 228411050 |
| chr2 | 228466625 | 228466777 | chr2 | 228638272 | 228638302 | chr2 | 228735680 | 228735736 |
| chr2 | 228736215 | 228736295 | chr2 | 228736336 | 228736473 | chr2 | 229046107 | 229046503 |
| chr2 | 230795535 | 230795555 | chr2 | 231576609 | 231576643 | chr2 | 232330451 | 232330481 |
| chr2 | 232394970 | 232395021 | chr2 | 232395055 | 232395061 | chr2 | 232479822 | 232479938 |
| chr2 | 232506220 | 232506294 | chr2 | 232506505 | 232606635 | chr2 | 232522844 | 232522874 |
| chr2 | 232544500 | 232544530 | chr2 | 232546736 | 232546842 | chr2 | 232791704 | 232792012 |
| chr2 | 232827168 | 232827349 | chr2 | 233073078 | 233073223 | chr2 | 233220227 | 233220382 |
| chr2 | 233350208 | 233350539 | chr2 | 233350844 | 233351278 | chr2 | 233352102 | 233352451 |
| chr2 | 233352507 | 233352762 | chr2 | 233352776 | 233352853 | chr2 | 233498710 | 233498873 |
| chr2 | 233498896 | 233499297 | chr2 | 233750525 | 233750555 | chr2 | 234776483 | 234776553 |
| chr2 | 235404551 | 235404575 | chr2 | 235860746 | 235860808 | chr2 | 235861389 | 235861533 |
| chr2 | 236402771 | 236403013 | chr2 | 236403270 | 236403736 | chr2 | 236444269 | 236444298 |
| chr2 | 236578362 | 236578677 | chr2 | 236877262 | 236877399 | chr2 | 237072642 | 237073014 |
| chr2 | 237073354 | 237073414 | chr2 | 237076725 | 237076815 | chr2 | 237077562 | 237077608 |
| chr2 | 237077846 | 237078348 | chr2 | 237080264 | 237080294 | chr2 | 237081341 | 237081426 |
| chr2 | 237081537 | 237081553 | chr2 | 237082344 | 237082720 | chr2 | 237086349 | 237086468 |
| chr2 | 237145422 | 237145601 | chr2 | 237416216 | 237416429 | chr2 | 238395291 | 238395356 |
| chr2 | 238395906 | 238395961 | chr2 | 238535895 | 238535984 | chr2 | 238536005 | 238536114 |
| chr2 | 238864727 | 238864913 | chr2 | 239031722 | 239031780 | chr2 | 239051198 | 239051228 |
| chr2 | 239140139 | 239140249 | chr2 | 239149844 | 239149951 | chr2 | 239265496 | 239265787 |
| chr2 | 239482485 | 239482519 | chr2 | 239705305 | 239705357 | chr2 | 239755164 | 239755194 |
| chr2 | 239756373 | 239756462 | chr2 | 239756488 | 239756607 | chr2 | 239756634 | 239756648 |
| chr2 | 239757636 | 239757730 | chr2 | 239758126 | 239758144 | chr2 | 239758345 | 239758394 |
| chr2 | 239957330 | 239957448 | chr2 | 240167575 | 240167605 | chr2 | 240168811 | 240169061 |
| chr2 | 240319920 | 240320012 | chr2 | 240582379 | 240582524 | chr2 | 240619459 | 240619604 |
| chr2 | 240658227 | 240658421 | chr2 | 240658667 | 240658721 | chr2 | 240812243 | 240812374 |
| chr2 | 241095604 | 241095772 | chr2 | 241393200 | 241393469 | chr2 | 241497411 | 241497554 |
| chr2 | 241541932 | 241542357 | chr2 | 241545001 | 241545031 | chr2 | 241758377 | 241758819 |
| chr2 | 241759597 | 241759694 | chr2 | 241760149 | 241760178 | chr2 | 241760494 | 241760523 |
| chr2 | 241771165 | 241771257 | chr2 | 241865194 | 241865346 | chr2 | 242009391 | 242009421 |
| chr2 | 242021784 | 242021892 | chr2 | 242314494 | 242314524 | chr2 | 242523907 | 242524147 |
| chr2 | 242549849 | 242549957 | chr2 | 242554549 | 242554579 | chr2 | 242636726 | 242636812 |
| chr2 | 242640015 | 242640045 | chr2 | 242716723 | 242716760 | chr2 | 242756144 | 242756297 |
| chr2 | 242832984 | 242833159 | chr2 | 242833558 | 242833588 | chr2 | 242833797 | 242833863 |
| chr2 | 242836495 | 242836640 | chr2 | 242925496 | 242925641 | chr3 | 238536 | 238715 |
| chr3 | 239007 | 239094 | chr3 | 239622 | 239868 | chr3 | 240110 | 240223 |
| chr3 | 2140277 | 2140398 | chr3 | 3167720 | 3167750 | chr3 | 3840498 | 3840758 |
| chr3 | 3841046 | 3841144 | chr3 | 3842679 | 3842731 | chr3 | 5137960 | 5138019 |
| chr3 | 5165885 | 5165915 | chr3 | 6902288 | 6902353 | chr3 | 6903425 | 6903463 |
| chr3 | 8725296 | 8725348 | chr3 | 8810152 | 8810220 | chr3 | 9593979 | 9594015 |
| chr3 | 9594263 | 9594382 | chr3 | 9595396 | 9595502 | chr3 | 9904233 | 9904554 |
| chr3 | 9924238 | 9924534 | chr3 | 9941469 | 9941669 | chr3 | 9957064 | 9957142 |
| chr3 | 9957451 | 9957677 | chr3 | 10027432 | 10027548 | chr3 | 10182839 | 10183212 |

TABLE 12-continued

| chr | start | end | chr | start | end | chr | start | end |
|---|---|---|---|---|---|---|---|---|
| chr3 | 10183321 | 10183350 | chr3 | 10183706 | 10183782 | chr3 | 10184304 | 10184333 |
| chr3 | 10191477 | 10191620 | chr3 | 11034264 | 11034359 | chr3 | 11035070 | 11035330 |
| chr3 | 12046405 | 12046632 | chr3 | 12586149 | 12586179 | chr3 | 12632309 | 12632401 |
| chr3 | 12645678 | 12645713 | chr3 | 12673006 | 12673036 | chr3 | 12729424 | 12729454 |
| chr3 | 12870826 | 12870856 | chr3 | 12917606 | 12917655 | chr3 | 12926053 | 12926102 |
| chr3 | 12977067 | 12977144 | chr3 | 13171814 | 13171844 | chr3 | 13323494 | 13323973 |
| chr3 | 13324420 | 13324433 | chr3 | 13324847 | 13324938 | chr3 | 13590448 | 13590640 |
| chr3 | 13679172 | 13679349 | chr3 | 13921407 | 13921463 | chr3 | 14851850 | 14851897 |
| chr3 | 14852325 | 14852919 | chr3 | 15123848 | 15123992 | chr3 | 15780510 | 16780638 |
| chr3 | 16554052 | 16554111 | chr3 | 16554347 | 16554633 | chr3 | 17001303 | 17001333 |
| chr3 | 17735273 | 17735340 | chr3 | 19189441 | 19189470 | chr3 | 19189694 | 19189765 |
| chr3 | 19190143 | 19190216 | chr3 | 20070714 | 20070903 | chr3 | 22413665 | 22413694 |
| chr3 | 22413960 | 22413974 | chr3 | 23964882 | 23965019 | chr3 | 24871002 | 24871176 |
| chr3 | 25469110 | 25469139 | chr3 | 25469377 | 25469406 | chr3 | 25469679 | 25469708 |
| chr3 | 26664045 | 26664119 | chr3 | 26664389 | 26664755 | chr3 | 27754478 | 27754508 |
| chr3 | 27762336 | 27762650 | chr3 | 27762857 | 27762887 | chr3 | 27763566 | 27763595 |
| chr3 | 27764457 | 27764471 | chr3 | 27765181 | 27765347 | chr3 | 27771497 | 27772004 |
| chr3 | 27772790 | 27772819 | chr3 | 28616832 | 28617675 | chr3 | 31494108 | 31494138 |
| chr3 | 32708277 | 32708405 | chr3 | 32858353 | 32858958 | chr3 | 32859256 | 32859284 |
| chr3 | 32859418 | 32859693 | chr3 | 32860068 | 32860273 | chr3 | 33259904 | 33260776 |
| chr3 | 35680842 | 35680872 | chr3 | 36805815 | 36805863 | chr3 | 36806179 | 36806193 |
| chr3 | 36984378 | 36984425 | chr3 | 37276385 | 37276490 | chr3 | 37493519 | 37493621 |
| chr3 | 37901923 | 37901953 | chr3 | 38030618 | 38030782 | chr3 | 38032331 | 38032361 |
| chr3 | 38035774 | 38035989 | chr3 | 38080685 | 38080925 | chr3 | 38081154 | 38081271 |
| chr3 | 38182244 | 38182305 | chr3 | 38182626 | 38182655 | chr3 | 38208158 | 38208226 |
| chr3 | 38690624 | 38690668 | chr3 | 39851772 | 39851814 | chr3 | 40202174 | 40202255 |
| chr3 | 40428507 | 40428713 | chr3 | 41266086 | 41266151 | chr3 | 42222730 | 42222847 |
| chr3 | 42329346 | 42329511 | chr3 | 42640855 | 42640964 | chr3 | 42814569 | 42814603 |
| chr3 | 42852329 | 42852359 | chr3 | 42947411 | 42947552 | chr3 | 43735604 | 43735634 |
| chr3 | 44036260 | 44036330 | chr3 | 44036570 | 44036600 | chr3 | 44036820 | 44037203 |
| chr3 | 44037625 | 44037662 | chr3 | 44037874 | 44038646 | chr3 | 44039348 | 44040006 |
| chr3 | 44040511 | 44040553 | chr3 | 44040796 | 44041039 | chr3 | 44063434 | 44063872 |
| chr3 | 44596479 | 44596509 | chr3 | 44596716 | 44596809 | chr3 | 44626438 | 44626211 |
| chr3 | 44726875 | 44727193 | chr3 | 45187296 | 45187327 | chr3 | 46924934 | 46924964 |
| chr3 | 47144864 | 47144893 | chr3 | 47352704 | 47352734 | chr3 | 47521062 | 47521178 |
| chr3 | 47555760 | 47555790 | chr3 | 47830060 | 47830148 | chr3 | 47831601 | 47831819 |
| chr3 | 48227765 | 48227870 | chr3 | 48236476 | 48236724 | chr3 | 48693304 | 48693700 |
| chr3 | 48693852 | 48694154 | chr3 | 48698251 | 48698431 | chr3 | 48698810 | 48699010 |
| chr3 | 48699377 | 48699767 | chr3 | 48978413 | 48978479 | chr3 | 49142883 | 49142913 |
| chr3 | 49196747 | 49196831 | chr3 | 49236845 | 49236874 | chr3 | 49405953 | 49405982 |
| chr3 | 49412883 | 49412987 | chr3 | 49591832 | 49592076 | chr3 | 49907093 | 49907130 |
| chr3 | 49939931 | 49940398 | chr3 | 50072827 | 50072925 | chr3 | 50243383 | 50243480 |
| chr3 | 50374655 | 50374684 | chr3 | 50374917 | 50374946 | chr3 | 50375179 | 50375559 |
| chr3 | 50377973 | 50378002 | chr3 | 50378277 | 50378306 | chr3 | 50378512 | 50378541 |
| chr3 | 50395506 | 50395536 | chr3 | 50402170 | 50402944 | chr3 | 50575616 | 50575658 |
| chr3 | 50968445 | 50968511 | chr3 | 52352194 | 52352326 | chr3 | 52442052 | 52442091 |
| chr3 | 52552556 | 52552661 | chr3 | 52553469 | 52553499 | chr3 | 53032733 | 53033524 |
| chr3 | 53253306 | 53253599 | chr3 | 53382392 | 53382565 | chr3 | 53480528 | 53480683 |
| chr3 | 54155611 | 54155677 | chr3 | 54157381 | 54157450 | chr3 | 54157878 | 54157919 |
| chr3 | 54583435 | 54583465 | chr3 | 55519219 | 55519253 | chr3 | 55523106 | 55523290 |
| chr3 | 55603443 | 55603632 | chr3 | 57437452 | 57437482 | chr3 | 57529094 | 57529218 |
| chr3 | 58153446 | 58153608 | chr3 | 62304567 | 62304669 | chr3 | 62353371 | 62354049 |
| chr3 | 62354283 | 62354328 | chr3 | 62354625 | 62354792 | chr3 | 62354900 | 62354914 |
| chr3 | 62355424 | 62355478 | chr3 | 62355774 | 62356219 | chr3 | 62356367 | 62356644 |
| chr3 | 62356793 | 62357192 | chr3 | 62357279 | 62357347 | chr3 | 62357624 | 62357667 |
| chr3 | 62358530 | 62358595 | chr3 | 52358858 | 62359011 | chr3 | 62359376 | 62359893 |
| chr3 | 62360302 | 62360560 | chr3 | 62362902 | 62362916 | chr3 | 62363099 | 62363200 |
| chr3 | 62363626 | 62363693 | chr3 | 62363906 | 62364176 | chr3 | 62364280 | 62364329 |
| chr3 | 62364702 | 62365154 | chr3 | 62861118 | 62861148 | chr3 | 63264139 | 63264169 |
| chr3 | 63719169 | 63719303 | chr3 | 66053446 | 66053613 | chr3 | 68056904 | 68057145 |
| chr3 | 68980931 | 68981113 | chr3 | 68981552 | 68981624 | chr3 | 69590939 | 69590969 |
| chr3 | 69591363 | 69591414 | chr3 | 69591780 | 69591977 | chr3 | 69740944 | 69740990 |
| chr3 | 69937703 | 69937848 | chr3 | 70661011 | 70661079 | chr3 | 71802518 | 71802622 |
| chr3 | 71803126 | 71803372 | chr3 | 71803643 | 71803783 | chr3 | 73045340 | 73045583 |
| chr3 | 75956027 | 75956375 | chr3 | 79815522 | 79815557 | chr3 | 79816778 | 79817015 |
| chr3 | 79817288 | 79817318 | chr3 | 85008553 | 85008708 | chr3 | 88247941 | 88248049 |
| chr3 | 93698033 | 93698063 | chr3 | 96532817 | 96532873 | chr3 | 96533383 | 96533458 |
| chr3 | 96534035 | 96534096 | chr3 | 98313191 | 98313253 | chr3 | 98618182 | 98618376 |
| chr3 | 98620891 | 98620980 | chr3 | 99594925 | 99595105 | chr3 | 100228688 | 100228768 |
| chr3 | 101094160 | 101094190 | chr3 | 101230678 | 101231070 | chr3 | 101331792 | 101331861 |
| chr3 | 101354294 | 101354442 | chr3 | 101397240 | 101397358 | chr3 | 101406823 | 101407190 |
| chr3 | 101411545 | 101411666 | chr3 | 101497841 | 101497996 | chr3 | 101645019 | 101645181 |
| chr3 | 105015466 | 105015519 | chr3 | 105684885 | 105684987 | chr3 | 106936157 | 106936336 |
| chr3 | 112052252 | 112052419 | chr3 | 112185933 | 112185975 | chr3 | 113557333 | 113557363 |
| chr3 | 113847911 | 113847941 | chr3 | 115502232 | 115502390 | chr3 | 115512319 | 115512448 |
| chr3 | 117715549 | 117716123 | chr3 | 117716214 | 117716473 | chr3 | 120004080 | 120004405 |
| chr3 | 120004468 | 120004497 | chr3 | 120169104 | 120169149 | chr3 | 120169768 | 120169835 |
| chr3 | 120627317 | 120627453 | chr3 | 121215241 | 121215271 | chr3 | 121657197 | 121657515 |

TABLE 12-continued

| chr | start | end | chr | start | end | chr | start | end |
|---|---|---|---|---|---|---|---|---|
| chr3 | 121741545 | 121741598 | chr3 | 121902991 | 121903218 | chr3 | 121903324 | 121903619 |
| chr3 | 122162036 | 122162117 | chr3 | 122162890 | 122163054 | chr3 | 122234242 | 122234538 |
| chr3 | 122573688 | 122573826 | chr3 | 122702288 | 122702451 | chr3 | 123167301 | 123167529 |
| chr3 | 123167769 | 123167827 | chr3 | 124410075 | 124410157 | chr3 | 125417341 | 125417424 |
| chr3 | 125898597 | 125899207 | chr3 | 125899525 | 125899962 | chr3 | 125932252 | 125932500 |
| chr3 | 126157586 | 126157663 | chr3 | 126261929 | 126262000 | chr3 | 126373520 | 126373704 |
| chr3 | 126854699 | 126854796 | chr3 | 127534814 | 127534897 | chr3 | 127634186 | 127634216 |
| chr3 | 127794546 | 127794860 | chr3 | 127795325 | 127795408 | chr3 | 128056383 | 128056497 |
| chr3 | 128202447 | 128202477 | chr3 | 128208903 | 128209232 | chr3 | 128273993 | 128274051 |
| chr3 | 128274309 | 128274611 | chr3 | 128384991 | 128385132 | chr3 | 128417201 | 128417231 |
| chr3 | 128599405 | 128599477 | chr3 | 128720061 | 128720142 | chr3 | 128720164 | 128720346 |
| chr3 | 128720419 | 128720533 | chr3 | 128720567 | 128720611 | chr3 | 128720869 | 128721229 |
| chr3 | 128764489 | 128764605 | chr3 | 128786496 | 128786525 | chr3 | 129008841 | 129009004 |
| chr3 | 129047978 | 129048008 | chr3 | 129372419 | 129372546 | chr3 | 129693108 | 129693199 |
| chr3 | 129693305 | 129693498 | chr3 | 129693955 | 129694299 | chr3 | 130064451 | 130064484 |
| chr3 | 130064818 | 130064848 | chr3 | 130236049 | 130236063 | chr3 | 130236174 | 130236273 |
| chr3 | 130502167 | 130502197 | chr3 | 130519901 | 130520077 | chr3 | 131754031 | 131754061 |
| chr3 | 132757065 | 132757104 | chr3 | 133217784 | 133217999 | chr3 | 133748140 | 133748245 |
| chr3 | 133748481 | 133748576 | chr3 | 133970381 | 133970743 | chr3 | 134369646 | 134369855 |
| chr3 | 134514866 | 134514895 | chr3 | 134515128 | 134515369 | chr3 | 134515676 | 134516222 |
| chr3 | 136016868 | 136016942 | chr3 | 136537642 | 136537730 | chr3 | 136538585 | 136538815 |
| chr3 | 136582883 | 136582951 | chr3 | 136751641 | 136751809 | chr3 | 137479233 | 137479302 |
| chr3 | 137479601 | 137479687 | chr3 | 137479980 | 137480764 | chr3 | 137481170 | 137481315 |
| chr3 | 137481858 | 137481872 | chr3 | 137481936 | 137482183 | chr3 | 137483313 | 137483437 |
| chr3 | 137483514 | 137483589 | chr3 | 137483848 | 137484002 | chr3 | 137484405 | 137484531 |
| chr3 | 137486029 | 137486310 | chr3 | 137486516 | 137486550 | chr3 | 137487964 | 137488003 |
| chr3 | 137488950 | 137489698 | chr3 | 137489876 | 137491040 | chr3 | 137892691 | 137892721 |
| chr3 | 137894374 | 137894415 | chr3 | 138058859 | 138058897 | chr3 | 138067717 | 138067747 |
| chr3 | 138153963 | 138153993 | chr3 | 138318827 | 138318918 | chr3 | 138374229 | 138374258 |
| chr3 | 138635369 | 138635507 | chr3 | 138655934 | 138656138 | chr3 | 138656834 | 138656889 |
| chr3 | 138667414 | 138657494 | chr3 | 138657618 | 138658296 | chr3 | 138658704 | 138658863 |
| chr3 | 138659081 | 138659099 | chr3 | 138662134 | 138662164 | chr3 | 138662282 | 138662296 |
| chr3 | 138662382 | 138662448 | chr3 | 138662799 | 138662842 | chr3 | 138663613 | 138663727 |
| chr3 | 138664142 | 138664165 | chr3 | 138664928 | 138665323 | chr3 | 138665562 | 138666294 |
| chr3 | 138668758 | 138669108 | chr3 | 138669141 | 138669387 | chr3 | 139258267 | 139258316 |
| chr3 | 139653491 | 139653693 | chr3 | 140769513 | 140769705 | chr3 | 140769908 | 140770301 |
| chr3 | 140770408 | 140770589 | chr3 | 140770644 | 140770829 | chr3 | 140771305 | 140771335 |
| chr3 | 140771816 | 140771854 | chr3 | 141174349 | 141174606 | chr3 | 141363466 | 141363496 |
| chr3 | 141481651 | 141482073 | chr3 | 141516389 | 141516719 | chr3 | 141657032 | 141657079 |
| chr3 | 141832939 | 141833015 | chr3 | 141835935 | 141836470 | chr3 | 142159804 | 142159841 |
| chr3 | 142537638 | 142537779 | chr3 | 142682273 | 142682392 | chr3 | 142718283 | 142718358 |
| chr3 | 142791151 | 142791255 | chr3 | 142837980 | 142838318 | chr3 | 142838621 | 142838646 |
| chr3 | 142838877 | 142839036 | chr3 | 142839563 | 142839688 | chr3 | 142839784 | 142839901 |
| chr3 | 142839945 | 142840127 | chr3 | 142840222 | 142840236 | chr3 | 142896156 | 142896214 |
| chr3 | 143280343 | 143280373 | chr3 | 143614462 | 143614504 | chr3 | 145735852 | 145735882 |
| chr3 | 145878665 | 145878695 | chr3 | 146187946 | 146187978 | chr3 | 147074457 | 147074487 |
| chr3 | 147074974 | 147075006 | chr3 | 147077289 | 147077671 | chr3 | 147078959 | 147079188 |
| chr3 | 147087562 | 147087799 | chr3 | 147088440 | 147088523 | chr3 | 147088939 | 147089099 |
| chr3 | 147098431 | 147098470 | chr3 | 147105898 | 147106010 | chr3 | 147108841 | 147109765 |
| chr3 | 147110229 | 147110683 | chr3 | 147110927 | 147111089 | chr3 | 147125697 | 147125726 |
| chr3 | 147127037 | 147127057 | chr3 | 147127681 | 147127902 | chr3 | 147136931 | 147137000 |
| chr3 | 147137076 | 147137164 | chr3 | 147138768 | 147138856 | chr3 | 147139374 | 147139528 |
| chr3 | 148415427 | 148415644 | chr3 | 148523213 | 148523297 | chr3 | 148803120 | 148803276 |
| chr3 | 149374947 | 149375023 | chr3 | 150237792 | 150237822 | chr3 | 150802981 | 150802999 |
| chr3 | 150803026 | 150803080 | chr3 | 150804043 | 150804077 | chr3 | 150804967 | 150805030 |
| chr3 | 152107022 | 152107052 | chr3 | 152553343 | 152553384 | chr3 | 152553658 | 152553725 |
| chr3 | 152707390 | 152707460 | chr3 | 152877666 | 152877696 | chr3 | 153838818 | 153838870 |
| chr3 | 153839518 | 153839952 | chr3 | 154146133 | 154146394 | chr3 | 154146654 | 154146908 |
| chr3 | 154797334 | 154797703 | chr3 | 155456372 | 155456630 | chr3 | 155461030 | 155461195 |
| chr3 | 155463041 | 155463071 | chr3 | 156007772 | 156007801 | chr3 | 156008976 | 156009299 |
| chr3 | 156009319 | 156009425 | chr3 | 157155252 | 157155490 | chr3 | 157155982 | 157156194 |
| chr3 | 157812196 | 157812257 | chr3 | 157812437 | 157812645 | chr3 | 157812912 | 157813070 |
| chr3 | 157813670 | 157813824 | chr3 | 157814311 | 157814340 | chr3 | 157815657 | 157815822 |
| chr3 | 157820576 | 157820605 | chr3 | 157821537 | 157821662 | chr3 | 157821904 | 157822008 |
| chr3 | 157823073 | 157823119 | chr3 | 157823139 | 157823143 | chr3 | 157823464 | 157823493 |
| chr3 | 157824133 | 157824146 | chr3 | 157824212 | 157824231 | chr3 | 157824495 | 157824871 |
| chr3 | 157825176 | 157825408 | chr3 | 158319235 | 158319359 | chr3 | 159756687 | 159756856 |
| chr3 | 159944486 | 159944546 | chr3 | 164912376 | 164912568 | chr3 | 164912907 | 164913872 |
| chr3 | 164914980 | 164915129 | chr3 | 169376183 | 169376215 | chr3 | 169376680 | 169376700 |
| chr3 | 169378825 | 169379024 | chr3 | 169539898 | 169540679 | chr3 | 169541070 | 169541102 |
| chr3 | 170136627 | 170136751 | chr3 | 170302617 | 170302677 | chr3 | 170303087 | 170303129 |
| chr3 | 170303380 | 170303423 | chr3 | 170303639 | 170303844 | chr3 | 170602030 | 170602133 |
| chr3 | 171193088 | 171193311 | chr3 | 171527930 | 171527971 | chr3 | 171529811 | 171529958 |
| chr3 | 172165443 | 172165784 | chr3 | 172165867 | 172166512 | chr3 | 172166879 | 172166893 |
| chr3 | 172167000 | 172167044 | chr3 | 172167297 | 172167327 | chr3 | 172167660 | 172167917 |
| chr3 | 172342101 | 172342147 | chr3 | 172355895 | 172356038 | chr3 | 172383550 | 172383600 |
| chr3 | 172425382 | 172425717 | chr3 | 172469925 | 172470036 | chr3 | 173115237 | 173115550 |
| chr3 | 173162817 | 173162847 | chr3 | 173302542 | 173302668 | chr3 | 173302992 | 173303225 |

TABLE 12-continued

| chr | start | end | chr | start | end | chr | start | end |
|---|---|---|---|---|---|---|---|---|
| chr3 | 176710106 | 176710241 | chr3 | 176872357 | 176872443 | chr3 | 178861259 | 178861447 |
| chr3 | 178916711 | 178916959 | chr3 | 178921532 | 178921568 | chr3 | 178927966 | 178928094 |
| chr3 | 178936059 | 178936111 | chr3 | 178952004 | 178952105 | chr3 | 179168661 | 179169266 |
| chr3 | 179367874 | 179367920 | chr3 | 179754178 | 179754192 | chr3 | 179754239 | 179754759 |
| chr3 | 179754804 | 179754872 | chr3 | 179755087 | 179755372 | chr3 | 180320256 | 180320294 |
| chr3 | 181413742 | 181414330 | chr3 | 181420065 | 181420116 | chr3 | 181420316 | 181420374 |
| chr3 | 181421411 | 181422282 | chr3 | 181422541 | 181422985 | chr3 | 181428388 | 181428772 |
| chr3 | 181430695 | 181430771 | chr3 | 181437129 | 181437349 | chr3 | 181438194 | 181438353 |
| chr3 | 181440892 | 181441927 | chr3 | 181442145 | 181442410 | chr3 | 181443014 | 181443557 |
| chr3 | 181443760 | 181443861 | chr3 | 181444108 | 181444236 | chr3 | 181444434 | 181444524 |
| chr3 | 181444613 | 181444948 | chr3 | 181444989 | 181445013 | chr3 | 181445369 | 181445464 |
| chr3 | 181445800 | 181445861 | chr3 | 182815811 | 182816027 | chr3 | 182895956 | 182896144 |
| chr3 | 182911545 | 182911574 | chr3 | 183109854 | 183109883 | chr3 | 183145412 | 183145618 |
| chr3 | 183145931 | 183146025 | chr3 | 183146397 | 183146435 | chr3 | 183146648 | 183146677 |
| chr3 | 183183523 | 183183659 | chr3 | 183208370 | 183208469 | chr3 | 183217676 | 183217706 |
| chr3 | 183647996 | 183648026 | chr3 | 183728793 | 183728952 | chr3 | 183870824 | 183870858 |
| chr3 | 183872490 | 183872524 | chr3 | 183965599 | 183965907 | chr3 | 184018038 | 184018136 |
| chr3 | 184031686 | 184031745 | chr3 | 184057254 | 184057557 | chr3 | 184099417 | 184099446 |
| chr3 | 184319470 | 184319612 | chr3 | 184319828 | 184319842 | chr3 | 184319874 | 184319891 |
| chr3 | 185001696 | 185001919 | chr3 | 185271296 | 185271764 | chr3 | 185275856 | 185275886 |
| chr3 | 185303247 | 185303277 | chr3 | 185363074 | 185363261 | chr3 | 185629516 | 185629546 |
| chr3 | 185643324 | 185643405 | chr3 | 185658513 | 185658543 | chr3 | 185668237 | 185668311 |
| chr3 | 186078766 | 186078898 | chr3 | 186079204 | 186079331 | chr3 | 186080188 | 186080218 |
| chr3 | 186287130 | 186287270 | chr3 | 186857152 | 186857607 | chr3 | 186914705 | 186914734 |
| chr3 | 187387850 | 187387920 | chr3 | 187388007 | 187388239 | chr3 | 192125828 | 192125828 |
| chr3 | 192126146 | 192126710 | chr3 | 192126787 | 192126863 | chr3 | 192127354 | 192127372 |
| chr3 | 192127557 | 192127730 | chr3 | 192127937 | 192128074 | chr3 | 192232097 | 192232175 |
| chr3 | 192232452 | 192232570 | chr3 | 192232860 | 192232951 | chr3 | 192233095 | 192233150 |
| chr3 | 192958725 | 192958968 | chr3 | 193312128 | 193312347 | chr3 | 193419702 | 193419732 |
| chr3 | 193548637 | 193548835 | chr3 | 193776089 | 193776119 | chr3 | 194048751 | 194048919 |
| chr3 | 194120008 | 194120164 | chr3 | 194120812 | 194120841 | chr3 | 194120934 | 194120963 |
| chr3 | 194208468 | 194208562 | chr3 | 194407998 | 194408028 | chr3 | 194408375 | 194408768 |
| chr3 | 194408839 | 194409021 | chr3 | 194981816 | 194981913 | chr3 | 195095450 | 195095543 |
| chr3 | 195184022 | 195184140 | chr3 | 195409773 | 195409813 | chr3 | 195536733 | 195536848 |
| chr3 | 195538217 | 195538353 | chr3 | 195587032 | 195587118 | chr3 | 195601239 | 195601312 |
| chr3 | 195602330 | 195602576 | chr3 | 195639755 | 195639785 | chr3 | 195648794 | 195649004 |
| chr3 | 195834581 | 195834611 | chr3 | 196046702 | 196046830 | chr3 | 196065342 | 196065583 |
| chr3 | 196069743 | 196070340 | chr3 | 196255617 | 196255631 | chr3 | 196263303 | 196263471 |
| chr3 | 196344683 | 196344795 | chr3 | 196387295 | 196387415 | chr3 | 196387628 | 196387665 |
| chr3 | 196388383 | 196388581 | chr3 | 196433946 | 196434104 | chr3 | 196440510 | 196440676 |
| chr3 | 196667872 | 196668080 | chr3 | 196728418 | 196728448 | chr3 | 196731155 | 196731313 |
| chr3 | 196755958 | 196755987 | chr3 | 197209019 | 197209048 | chr3 | 197236945 | 197237111 |
| chr3 | 197247047 | 197247110 | chr3 | 197278926 | 197278988 | chr3 | 197313997 | 197314107 |
| chr3 | 197326860 | 197327042 | chr3 | 197330060 | 197330147 | chr3 | 197466364 | 197466540 |
| chr3 | 197616707 | 197616861 | chr3 | 197677029 | 197677058 | chr3 | 197685788 | 197686085 |
| chr3 | 197686495 | 197686524 | chr3 | 197686941 | 197687223 | chr3 | 197687694 | 197687723 |
| chr4 | 206324 | 206353 | chr4 | 331322 | 331352 | chr4 | 488816 | 488875 |
| chr4 | 512978 | 513008 | chr4 | 513704 | 513734 | chr4 | 568429 | 568652 |
| chr4 | 569048 | 569115 | chr4 | 569275 | 569435 | chr4 | 569461 | 569732 |
| chr4 | 570966 | 571013 | chr4 | 571508 | 571689 | chr4 | 628572 | 629061 |
| chr4 | 651196 | 651261 | chr4 | 657521 | 657552 | chr4 | 678471 | 678501 |
| chr4 | 718052 | 718112 | chr4 | 718321 | 718456 | chr4 | 829611 | 829641 |
| chr4 | 955367 | 955454 | chr4 | 955867 | 955919 | chr4 | 995876 | 995993 |
| chr4 | 996101 | 996174 | chr4 | 1008740 | 1008902 | chr4 | 1016127 | 1016252 |
| chr4 | 1016586 | 1016747 | chr4 | 1025928 | 1026074 | chr4 | 1041763 | 1041926 |
| chr4 | 1093536 | 1093675 | chr4 | 1107494 | 1107585 | chr4 | 1165450 | 1165470 |
| chr4 | 1189021 | 1189051 | chr4 | 1214894 | 1215162 | chr4 | 1215415 | 1215451 |
| chr4 | 1282515 | 1282545 | chr4 | 1331675 | 1331705 | chr4 | 1336755 | 1336902 |
| chr4 | 1338715 | 1338812 | chr4 | 1339099 | 1339221 | chr4 | 1396578 | 1396696 |
| chr4 | 1397396 | 1397495 | chr4 | 1398303 | 1398378 | chr4 | 1399723 | 1399768 |
| chr4 | 1401711 | 1401743 | chr4 | 1512368 | 1512398 | chr4 | 1556419 | 1556609 |
| chr4 | 1576484 | 1576528 | chr4 | 1616682 | 1617247 | chr4 | 1687080 | 1687110 |
| chr4 | 1800153 | 1800191 | chr4 | 1803550 | 1803582 | chr4 | 1206084 | 1806113 |
| chr4 | 1807355 | 1807384 | chr4 | 1962787 | 1962816 | chr4 | 1993771 | 1994180 |
| chr4 | 2042106 | 2042122 | chr4 | 2042169 | 2042258 | chr4 | 2066114 | 2066265 |
| chr4 | 2305672 | 2305827 | chr4 | 2627907 | 2527937 | chr4 | 2532556 | 2532586 |
| chr4 | 2540073 | 2540297 | chr4 | 2765862 | 2765910 | chr4 | 2926366 | 2926396 |
| chr4 | 2978968 | 2979145 | chr4 | 3036118 | 3036148 | chr4 | 3217107 | 3217154 |
| chr4 | 3371519 | 3371652 | chr4 | 3446991 | 3447021 | chr4 | 3447816 | 3448015 |
| chr4 | 3768833 | 3768949 | chr4 | 3768995 | 3769189 | chr4 | 3769560 | 3769574 |
| chr4 | 3873694 | 3873769 | chr4 | 4228189 | 4228241 | chr4 | 4229689 | 4229781 |
| chr4 | 4387533 | 4387627 | chr4 | 4417568 | 4417603 | chr4 | 4855102 | 4855171 |
| chr4 | 4855371 | 4855433 | chr4 | 4860046 | 4860075 | chr4 | 4862769 | 4863110 |
| chr4 | 4867698 | 4867886 | chr4 | 4868566 | 4868792 | chr4 | 4868829 | 4868999 |
| chr4 | 4872088 | 4872167 | chr4 | 4872777 | 4872850 | chr4 | 4873427 | 4873528 |
| chr4 | 5021188 | 5021217 | chr4 | 5053070 | 5053518 | chr4 | 5053747 | 5054093 |
| chr4 | 5519950 | 5520092 | chr4 | 5709906 | 5709984 | chr4 | 5712979 | 5713231 |
| chr4 | 5889948 | 5890045 | chr4 | 5890274 | 5890444 | chr4 | 5891966 | 5892081 |

TABLE 12-continued

| chr | start | end | chr | start | end | chr | start | end |
|---|---|---|---|---|---|---|---|---|
| chr4 | 5892110 | 5892194 | chr4 | 5892750 | 5892780 | chr4 | 5893981 | 5894082 |
| chr4 | 6200897 | 6201235 | chr4 | 6202103 | 6202276 | chr4 | 6247351 | 6247381 |
| chr4 | 6565004 | 6565042 | chr4 | 6628453 | 6628500 | chr4 | 6670184 | 6670214 |
| chr4 | 6719599 | 6719637 | chr4 | 6748346 | 6748557 | chr4 | 6839352 | 6839402 |
| chr4 | 6955114 | 6955144 | chr4 | 6957481 | 6957620 | chr4 | 7038560 | 7038688 |
| chr4 | 7647770 | 7647945 | chr4 | 7758476 | 7758561 | chr4 | 8429086 | 8429178 |
| chr4 | 8582549 | 8582579 | chr4 | 8607813 | 8607932 | chr4 | 8608556 | 8608600 |
| chr4 | 8858827 | 8859047 | chr4 | 8859382 | 8859738 | chr4 | 8860398 | 8860553 |
| chr4 | 8861649 | 8861752 | chr4 | 8861919 | 8862014 | chr4 | 8862797 | 8862811 |
| chr4 | 8863441 | 8863526 | chr4 | 8864499 | 8864598 | chr4 | 8864831 | 8865058 |
| chr4 | 8868822 | 8868845 | chr4 | 8868932 | 8869270 | chr4 | 8869601 | 8869813 |
| chr4 | 8873054 | 8873072 | chr4 | 8873809 | 8873984 | chr4 | 8874485 | 8874534 |
| chr4 | 8874773 | 8874787 | chr4 | 8875877 | 8875907 | chr4 | 8893060 | 8893093 |
| chr4 | 8893501 | 8893531 | chr4 | 8893816 | 8893931 | chr4 | 8894641 | 8894957 |
| chr4 | 8895232 | 8895350 | chr4 | 8895554 | 8895584 | chr4 | 8895965 | 8896052 |
| chr4 | 9423273 | 9423354 | chr4 | 9782992 | 9783095 | chr4 | 9783126 | 9783412 |
| chr4 | 10458395 | 10459121 | chr4 | 10462833 | 10463047 | chr4 | 10463073 | 10463604 |
| chr4 | 10782701 | 10782741 | chr4 | 11429506 | 11429633 | chr4 | 13524026 | 13524251 |
| chr4 | 13524665 | 13524775 | chr4 | 13524957 | 13524971 | chr4 | 13537569 | 13537688 |
| chr4 | 13540983 | 13541068 | chr4 | 13546026 | 13546078 | chr4 | 13548502 | 13548589 |
| chr4 | 13548635 | 13548895 | chr4 | 13549340 | 13549510 | chr4 | 15780223 | 15780320 |
| chr4 | 16084741 | 16084818 | chr4 | 16085167 | 16085301 | chr4 | 16085352 | 16085381 |
| chr4 | 16085675 | 16085682 | chr4 | 17430691 | 17430832 | chr4 | 17783003 | 17783480 |
| chr4 | 20254693 | 20254723 | chr4 | 20255525 | 20255861 | chr4 | 20256152 | 20256285 |
| chr4 | 21950248 | 21950295 | chr4 | 24801868 | 24801985 | chr4 | 24914638 | 24914668 |
| chr4 | 25656815 | 25656879 | chr4 | 25657437 | 25657477 | chr4 | 26256826 | 26256867 |
| chr4 | 27086432 | 27086462 | chr4 | 30722243 | 30722273 | chr4 | 30723856 | 30723862 |
| chr4 | 30724249 | 30724372 | chr4 | 37245837 | 37245851 | chr4 | 37246134 | 37246360 |
| chr4 | 37246490 | 37246699 | chr4 | 37247096 | 37247216 | chr4 | 38566328 | 38566418 |
| chr4 | 38673115 | 38673144 | chr4 | 39816807 | 39817064 | chr4 | 40632773 | 40632802 |
| chr4 | 40910303 | 40910465 | chr4 | 41258716 | 41258788 | chr4 | 41259086 | 41259176 |
| chr4 | 41747009 | 41747133 | chr4 | 41747493 | 41747582 | chr4 | 41747958 | 41748011 |
| chr4 | 41748144 | 41748296 | chr4 | 41748660 | 41748766 | chr4 | 41749033 | 41749063 |
| chr4 | 41749270 | 41749761 | chr4 | 41750223 | 41750504 | chr4 | 41751870 | 41752006 |
| chr4 | 41752451 | 41752693 | chr4 | 41752968 | 41753398 | chr4 | 41753610 | 41753916 |
| chr4 | 41754031 | 41754071 | chr4 | 41875430 | 41875902 | chr4 | 41880331 | 41880412 |
| chr4 | 41881385 | 41881425 | chr4 | 41883091 | 41883302 | chr4 | 41883510 | 41883610 |
| chr4 | 41938449 | 41938479 | chr4 | 41993676 | 41993815 | chr4 | 42152962 | 42153411 |
| chr4 | 42153533 | 42153632 | chr4 | 42153882 | 42154025 | chr4 | 42154280 | 42154359 |
| chr4 | 42154662 | 42154997 | chr4 | 42155293 | 42155322 | chr4 | 42348266 | 42348331 |
| chr4 | 42398842 | 42398872 | chr4 | 42399137 | 42399191 | chr4 | 42399688 | 42399872 |
| chr4 | 44266683 | 44266780 | chr4 | 44449480 | 44449569 | chr4 | 46067800 | 46067954 |
| chr4 | 46391353 | 46391383 | chr4 | 46911535 | 46911564 | chr4 | 46995161 | 46995835 |
| chr4 | 47034908 | 47034938 | chr4 | 47197142 | 47197270 | chr4 | 47914784 | 47914992 |
| chr4 | 48485067 | 48485288 | chr4 | 48485590 | 48486000 | chr4 | 48486356 | 48486389 |
| chr4 | 48492181 | 48492433 | chr4 | 48848428 | 48848554 | chr4 | 48988109 | 48988335 |
| chr4 | 53728495 | 53729056 | chr4 | 54966854 | 54967075 | chr4 | 54967342 | 54967484 |
| chr4 | 54969833 | 54970095 | chr4 | 54970369 | 54970482 | chr4 | 54975991 | 54976115 |
| chr4 | 55093048 | 55093255 | chr4 | 55096239 | 55096344 | chr4 | 55097404 | 55097634 |
| chr4 | 55097973 | 55098092 | chr4 | 55098198 | 55098373 | chr4 | 55098674 | 55098744 |
| chr4 | 55099016 | 55099062 | chr4 | 56133613 | 55133642 | chr4 | 55136787 | 55136816 |
| chr4 | 55138657 | 55138686 | chr4 | 55139691 | 55139720 | chr4 | 55140731 | 55140784 |
| chr4 | 55141015 | 55141050 | chr4 | 55144105 | 55144134 | chr4 | 55146554 | 55146583 |
| chr4 | 55152075 | 55152140 | chr4 | 55524220 | 55524274 | chr4 | 55589753 | 55589782 |
| chr4 | 55592166 | 55592204 | chr4 | 55593417 | 55593675 | chr4 | 55594183 | 55594212 |
| chr4 | 55595504 | 55595614 | chr4 | 55599306 | 55599356 | chr4 | 55968165 | 55968194 |
| chr4 | 55991107 | 55991228 | chr4 | 55992153 | 55992169 | chr4 | 56594679 | 56594720 |
| chr4 | 56659692 | 56659866 | chr4 | 56659935 | 56660021 | chr4 | 57017387 | 57017459 |
| chr4 | 57371718 | 57371963 | chr4 | 57372336 | 57372504 | chr4 | 57396946 | 57397264 |
| chr4 | 57521506 | 57521663 | chr4 | 57522301 | 57522382 | chr4 | 57522420 | 57522815 |
| chr4 | 57687720 | 57687782 | chr4 | 57777437 | 57777595 | chr4 | 57803498 | 57803558 |
| chr4 | 57813490 | 57813763 | chr4 | 57976033 | 57976185 | chr4 | 57976416 | 57976573 |
| chr4 | 58030191 | 58030524 | chr4 | 62066196 | 62066553 | chr4 | 62067511 | 62067624 |
| chr4 | 62068072 | 62068150 | chr4 | 66535130 | 66535314 | chr4 | 66535351 | 66535443 |
| chr4 | 66536171 | 66536323 | chr4 | 73459699 | 73459762 | chr4 | 74142341 | 74142434 |
| chr4 | 74702479 | 74702516 | chr4 | 74735076 | 74735137 | chr4 | 74809877 | 74809933 |
| chr4 | 75241080 | 75241435 | chr4 | 75858573 | 75858629 | chr4 | 76554873 | 76554935 |
| chr4 | 76555532 | 76555856 | chr4 | 76912698 | 76912733 | chr4 | 79611132 | 79611294 |
| chr4 | 79689651 | 79689732 | chr4 | 79861530 | 79861560 | chr4 | 80273120 | 80273150 |
| chr4 | 81106351 | 81106871 | chr4 | 81124277 | 81124662 | chr4 | 81187046 | 81187076 |
| chr4 | 81187559 | 81187589 | chr4 | 81188385 | 81188489 | chr4 | 81188491 | 81188556 |
| chr4 | 81189419 | 81189660 | chr4 | 81189714 | 81189911 | chr4 | 81951431 | 81951460 |
| chr4 | 81951941 | 81951970 | chr4 | 81952170 | 81952311 | chr4 | 82135873 | 82135887 |
| chr4 | 82135920 | 82136056 | chr4 | 82136495 | 82136548 | chr4 | 82136807 | 82136837 |
| chr4 | 83323506 | 83323708 | chr4 | 83343366 | 83343396 | chr4 | 83720611 | 83720643 |
| chr4 | 83809740 | 83809787 | chr4 | 83955171 | 83955201 | chr4 | 83988361 | 83988511 |
| chr4 | 84035907 | 84035936 | chr4 | 85402377 | 85402511 | chr4 | 85402776 | 85403423 |
| chr4 | 85403913 | 85403927 | chr4 | 85404112 | 85404140 | chr4 | 85404225 | 85404475 |

TABLE 12-continued

| chr | start | end | chr | start | end | chr | start | end |
|---|---|---|---|---|---|---|---|---|
| chr4 | 85404650 | 85404693 | chr4 | 85414045 | 85414113 | chr4 | 85414725 | 85414846 |
| chr4 | 85417336 | 85417564 | chr4 | 85418079 | 85418079 | chr4 | 85418522 | 85418582 |
| chr4 | 85420591 | 85420621 | chr4 | 85422188 | 85422432 | chr4 | 85422973 | 85423316 |
| chr4 | 85424401 | 85424483 | chr4 | 87515337 | 87515367 | chr4 | 89378464 | 89378497 |
| chr4 | 89378744 | 89378766 | chr4 | 89378832 | 89378888 | chr4 | 90043517 | 90043547 |
| chr4 | 90757517 | 90757828 | chr4 | 90758105 | 90758134 | chr4 | 90758776 | 90758883 |
| chr4 | 91079842 | 91079899 | chr4 | 93224972 | 93225171 | chr4 | 93226365 | 93226703 |
| chr4 | 93226729 | 93227129 | chr4 | 94749725 | 94749755 | chr4 | 94750982 | 94751140 |
| chr4 | 94751419 | 94751502 | chr4 | 94753415 | 94753445 | chr4 | 94756002 | 94756109 |
| chr4 | 95127590 | 95122717 | chr4 | 95128038 | 95128068 | chr4 | 95762672 | 95762896 |
| chr4 | 96470752 | 96470782 | chr4 | 101111246 | 101111504 | chr4 | 101111857 | 101111970 |
| chr4 | 102332467 | 102332611 | chr4 | 102711731 | 102711787 | chr4 | 103929647 | 103929796 |
| chr4 | 103930065 | 103930095 | chr4 | 106335495 | 106335617 | chr4 | 107955311 | 107955826 |
| chr4 | 107956676 | 107957086 | chr4 | 107957373 | 107957466 | chr4 | 109093101 | 109093168 |
| chr4 | 109093405 | 109093506 | chr4 | 110223090 | 110223427 | chr4 | 110223579 | 110223980 |
| chr4 | 110344202 | 110344294 | chr4 | 110735672 | 110735702 | chr4 | 111532705 | 111532961 |
| chr4 | 111536288 | 111536505 | chr4 | 111536562 | 111536693 | chr4 | 111536960 | 111536974 |
| chr4 | 111537407 | 111537497 | chr4 | 111540199 | 111540360 | chr4 | 111542474 | 111542757 |
| chr4 | 111543232 | 111543345 | chr4 | 111543404 | 111543450 | chr4 | 111543661 | 111543695 |
| chr4 | 111543721 | 111543735 | chr4 | 111544381 | 111544583 | chr4 | 111549800 | 111549830 |
| chr4 | 111550618 | 111550834 | chr4 | 111552118 | 111552148 | chr4 | 111553099 | 111553450 |
| chr4 | 111553916 | 111553951 | chr4 | 111554950 | 111554964 | chr4 | 111555194 | 111555343 |
| chr4 | 111557965 | 111558049 | chr4 | 111558551 | 111559233 | chr4 | 111560249 | 111560636 |
| chr4 | 111562576 | 111562648 | chr4 | 113154896 | 113155129 | chr4 | 113430640 | 113430672 |
| chr4 | 113431834 | 113431854 | chr4 | 113431916 | 113432154 | chr4 | 113432227 | 113432503 |
| chr4 | 113432519 | 113432573 | chr4 | 113436216 | 113436287 | chr4 | 113441592 | 113441733 |
| chr4 | 113442098 | 113442185 | chr4 | 113442247 | 113442525 | chr4 | 113444020 | 113444448 |
| chr4 | 113559163 | 113559422 | chr4 | 117847399 | 117847458 | chr4 | 121844063 | 121844206 |
| chr4 | 121992265 | 121992312 | chr4 | 121993997 | 121994251 | chr4 | 122301422 | 122301712 |
| chr4 | 122302116 | 122302246 | chr4 | 122685807 | 122685890 | chr4 | 122686209 | 122686507 |
| chr4 | 122871294 | 122871334 | chr4 | 122871573 | 122872000 | chr4 | 123664228 | 123664363 |
| chr4 | 126237310 | 126237611 | chr4 | 126238024 | 126238436 | chr4 | 128544048 | 128544161 |
| chr4 | 128544646 | 128544789 | chr4 | 128967250 | 128967329 | chr4 | 128968647 | 128968800 |
| chr4 | 128969310 | 128969382 | chr4 | 128984386 | 128984464 | chr4 | 130018134 | 130018266 |
| chr4 | 134067881 | 134068004 | chr4 | 134068577 | 134068791 | chr4 | 134069289 | 134069318 |
| chr4 | 134069578 | 134069896 | chr4 | 134070374 | 134070403 | chr4 | 134071648 | 134072610 |
| chr4 | 134072677 | 134072967 | chr4 | 134073184 | 134073322 | chr4 | 134073568 | 134073641 |
| chr4 | 134073862 | 134073919 | chr4 | 134074030 | 134074156 | chr4 | 140200529 | 140201166 |
| chr4 | 140201193 | 140201462 | chr4 | 140656643 | 140656666 | chr4 | 140656858 | 140657089 |
| chr4 | 141347942 | 141348151 | chr4 | 141418921 | 141419420 | chr4 | 141488870 | 141489128 |
| chr4 | 142053130 | 142053160 | chr4 | 142053520 | 142053734 | chr4 | 142054239 | 142054460 |
| chr4 | 143766796 | 143766930 | chr4 | 144586035 | 144586088 | chr4 | 144621336 | 144621439 |
| chr4 | 144621515 | 144621896 | chr4 | 144621982 | 144622058 | chr4 | 145568052 | 145568147 |
| chr4 | 145568459 | 145568741 | chr4 | 146853951 | 146853981 | chr4 | 147558272 | 147558381 |
| chr4 | 147558477 | 147558504 | chr4 | 147559321 | 147560078 | chr4 | 147560134 | 147560418 |
| chr4 | 147560460 | 147560617 | chr4 | 147560933 | 147561145 | chr4 | 147561360 | 147561949 |
| chr4 | 147562000 | 147562055 | chr4 | 147568636 | 147569060 | chr4 | 147569620 | 147569650 |
| chr4 | 147576177 | 147576201 | chr4 | 147576330 | 147576639 | chr4 | 151974287 | 151974510 |
| chr4 | 152148807 | 152148836 | chr4 | 152246132 | 152246314 | chr4 | 153247273 | 153247386 |
| chr4 | 153249362 | 153249398 | chr4 | 153251894 | 153251923 | chr4 | 153702668 | 153702702 |
| chr4 | 154216241 | 154216357 | chr4 | 154374504 | 154374630 | chr4 | 154709524 | 154709610 |
| chr4 | 154709759 | 154710617 | chr4 | 154710729 | 154710914 | chr4 | 154712172 | 154712594 |
| chr4 | 154713500 | 154713530 | chr4 | 154713949 | 154714010 | chr4 | 155254166 | 155254196 |
| chr4 | 155411851 | 155412279 | chr4 | 155663209 | 155663647 | chr4 | 155665445 | 155665475 |
| chr4 | 156129153 | 156129183 | chr4 | 156129451 | 156129495 | chr4 | 156129746 | 156129797 |
| chr4 | 156130047 | 156130297 | chr4 | 156297416 | 156297556 | chr4 | 156297942 | 156298073 |
| chr4 | 156588311 | 156588401 | chr4 | 156589273 | 156589323 | chr4 | 156680257 | 156680532 |
| chr4 | 156681370 | 156681489 | chr4 | 158101782 | 158102020 | chr4 | 158141576 | 158141606 |
| chr4 | 158142847 | 158142999 | chr4 | 168143443 | 158143465 | chr4 | 169063301 | 159063331 |
| chr4 | 159149784 | 159149824 | chr4 | 164252991 | 164253447 | chr4 | 164819191 | 164819221 |
| chr4 | 165304515 | 165304578 | chr4 | 165305060 | 165305163 | chr4 | 166414834 | 166414921 |
| chr4 | 166794771 | 166794909 | chr4 | 166796118 | 166796212 | chr4 | 168155109 | 168155269 |
| chr4 | 170865234 | 170865287 | chr4 | 170947287 | 170947325 | chr4 | 171012375 | 171012409 |
| chr4 | 172132870 | 172133019 | chr4 | 172734189 | 172734203 | chr4 | 172734592 | 172734790 |
| chr4 | 173953411 | 173953594 | chr4 | 174083164 | 174083431 | chr4 | 174124429 | 174124477 |
| chr4 | 174136704 | 174136734 | chr4 | 174224186 | 174224216 | chr4 | 174429658 | 174429688 |
| chr4 | 174430310 | 174430553 | chr4 | 174430794 | 174431072 | chr4 | 174438567 | 174438744 |
| chr4 | 174439822 | 174440257 | chr4 | 174440636 | 174440713 | chr4 | 174443212 | 174443242 |
| chr4 | 174443563 | 174443934 | chr4 | 174446508 | 174446525 | chr4 | 174446952 | 174447005 |
| chr4 | 174449950 | 174450726 | chr4 | 174450752 | 174451482 | chr4 | 174451855 | 174452098 |
| chr4 | 174459185 | 174459374 | chr4 | 174459528 | 174459840 | chr4 | 174460186 | 174460221 |
| chr4 | 175132735 | 175132765 | chr4 | 175133085 | 175133201 | chr4 | 175134897 | 175135672 |
| chr4 | 175135921 | 175136011 | chr4 | 175138411 | 175138546 | chr4 | 175138964 | 175139254 |
| chr4 | 175139559 | 175139685 | chr4 | 175750456 | 175750738 | chr4 | 176923424 | 176923558 |
| chr4 | 176987324 | 176987373 | chr4 | 177713228 | 177713437 | chr4 | 178285756 | 178285879 |
| chr4 | 180979270 | 180979300 | chr4 | 180980297 | 180980356 | chr4 | 183063666 | 183063950 |
| chr4 | 183064617 | 183064655 | chr4 | 183064874 | 183064965 | chr4 | 184019249 | 184019316 |
| chr4 | 184019692 | 184019736 | chr4 | 184020106 | 184020179 | chr4 | 184375546 | 184375726 |

TABLE 12-continued

| chr | start | end | chr | start | end | chr | start | end |
|---|---|---|---|---|---|---|---|---|
| chr4 | 184491996 | 184492042 | chr4 | 184644053 | 184644249 | chr4 | 184718260 | 184718352 |
| chr4 | 184826238 | 184826493 | chr4 | 184826938 | 184827237 | chr4 | 184921855 | 184922091 |
| chr4 | 185089696 | 185089797 | chr4 | 185937333 | 185937889 | chr4 | 185938497 | 185938564 |
| chr4 | 185940338 | 185940460 | chr4 | 185941585 | 185942472 | chr4 | 185942492 | 185942760 |
| chr4 | 187647073 | 187647457 | chr5 | 53849 | 53898 | chr5 | 92163 | 92399 |
| chr5 | 230673 | 230709 | chr5 | 303272 | 303301 | chr5 | 320840 | 320982 |
| chr5 | 343916 | 343941 | chr5 | 373363 | 373392 | chr5 | 373872 | 374266 |
| chr5 | 400186 | 400215 | chr5 | 400502 | 400531 | chr5 | 415870 | 415899 |
| chr5 | 481012 | 481121 | chr5 | 491335 | 491536 | chr5 | 524337 | 524404 |
| chr5 | 538758 | 538806 | chr5 | 554299 | 554538 | chr5 | 554871 | 564900 |
| chr5 | 555158 | 555285 | chr5 | 555965 | 555995 | chr5 | 677889 | 678006 |
| chr5 | 909204 | 909304 | chr5 | 912806 | 912835 | chr5 | 1034600 | 1034653 |
| chr5 | 1059523 | 1059556 | chr5 | 1093660 | 1093797 | chr5 | 1117778 | 1118270 |
| chr5 | 1131217 | 1131378 | chr5 | 1136590 | 1136845 | chr5 | 1193381 | 1193521 |
| chr5 | 1193880 | 1193944 | chr5 | 1221197 | 1221307 | chr5 | 1259524 | 1259558 |
| chr5 | 1271339 | 1271396 | chr5 | 1294630 | 1294767 | chr5 | 1295031 | 1295442 |
| chr5 | 1295605 | 1295662 | chr5 | 1445171 | 1445255 | chr5 | 1445738 | 1445759 |
| chr5 | 1445841 | 1445928 | chr5 | 1446319 | 1446369 | chr5 | 1446443 | 1446599 |
| chr5 | 1747022 | 1747098 | chr5 | 1779526 | 1779556 | chr5 | 1787378 | 1787418 |
| chr5 | 1874892 | 1875099 | chr5 | 1875453 | 1875497 | chr5 | 1875870 | 1876306 |
| chr5 | 1876638 | 1876860 | chr5 | 1877195 | 1877239 | chr5 | 1878014 | 1878028 |
| chr5 | 1878224 | 1878528 | chr5 | 1878831 | 1879045 | chr5 | 1879605 | 1879661 |
| chr5 | 1879690 | 1879719 | chr5 | 1882420 | 1882605 | chr5 | 1882844 | 1882921 |
| chr5 | 1883515 | 1883616 | chr5 | 1884178 | 1884237 | chr5 | 1884557 | 1884698 |
| chr5 | 1885158 | 1885458 | chr5 | 1885985 | 1886076 | chr5 | 1886542 | 1886581 |
| chr5 | 1886812 | 1886841 | chr5 | 1886998 | 1887145 | chr5 | 1887547 | 1887581 |
| chr5 | 1887656 | 1887737 | chr5 | 1930786 | 1931004 | chr5 | 1931065 | 1931286 |
| chr5 | 1931445 | 1931576 | chr5 | 1931618 | 1931754 | chr5 | 1950794 | 1950960 |
| chr5 | 1952624 | 1952638 | chr5 | 2038705 | 2038850 | chr5 | 2225439 | 2225469 |
| chr5 | 2324383 | 2324413 | chr5 | 2367718 | 2367892 | chr5 | 2541487 | 2541611 |
| chr5 | 2738848 | 2739129 | chr5 | 2739211 | 2739354 | chr5 | 2739877 | 2740300 |
| chr5 | 2740431 | 2740664 | chr5 | 2743617 | 2743659 | chr5 | 2743699 | 2743713 |
| chr5 | 2748374 | 2748459 | chr5 | 2749213 | 2749406 | chr5 | 2749699 | 2749729 |
| chr5 | 2750435 | 2750516 | chr5 | 2750655 | 2250769 | chr5 | 2751855 | 2751894 |
| chr5 | 2752991 | 2753040 | chr5 | 2753048 | 2753078 | chr5 | 2754738 | 2754767 |
| chr5 | 2755323 | 2756388 | chr5 | 2756599 | 2756602 | chr5 | 2756674 | 2757427 |
| chr5 | 3031879 | 3032018 | chr5 | 3152146 | 3152176 | chr5 | 3325042 | 3325272 |
| chr5 | 3590405 | 3590657 | chr5 | 3591354 | 3591388 | chr5 | 3591857 | 3592037 |
| chr5 | 3592728 | 3592881 | chr5 | 3594250 | 3594519 | chr5 | 3595090 | 3595178 |
| chr5 | 3595850 | 3595991 | chr5 | 3596556 | 3596724 | chr5 | 3596825 | 3596880 |
| chr5 | 3597411 | 3597461 | chr5 | 3600150 | 3600180 | chr5 | 3602804 | 3603320 |
| chr5 | 3674053 | 3674224 | chr5 | 4144367 | 4144516 | chr5 | 5139754 | 5139900 |
| chr5 | 5140170 | 5140225 | chr5 | 5140630 | 5140757 | chr5 | 5140850 | 5140901 |
| chr5 | 6228617 | 6228790 | chr5 | 6448930 | 6449582 | chr5 | 6482458 | 6482620 |
| chr5 | 6583461 | 6583579 | chr5 | 6687277 | 6687431 | chr5 | 6755789 | 6755843 |
| chr5 | 7395263 | 7395393 | chr5 | 7395434 | 7395638 | chr5 | 7851015 | 7851121 |
| chr5 | 9546612 | 9546648 | chr5 | 10249098 | 10249127 | chr5 | 10333688 | 10334132 |
| chr5 | 10565021 | 10565227 | chr5 | 10565263 | 10565607 | chr5 | 10616516 | 10616550 |
| chr5 | 11384965 | 11385363 | chr5 | 11903822 | 11904173 | chr5 | 11904196 | 11904379 |
| chr5 | 11904456 | 11904696 | chr5 | 11904896 | 11904943 | chr5 | 14872919 | 14873053 |
| chr5 | 15500748 | 15500927 | chr5 | 16179049 | 16179141 | chr5 | 16179555 | 16179713 |
| chr5 | 16180183 | 16180260 | chr5 | 16466784 | 16467120 | chr5 | 16793851 | 16794008 |
| chr5 | 16845452 | 16845619 | chr5 | 16936354 | 16936514 | chr5 | 16968118 | 16968148 |
| chr5 | 17095895 | 17095927 | chr5 | 17203012 | 17203177 | chr5 | 17218195 | 17218225 |
| chr5 | 17218986 | 17219018 | chr5 | 17311046 | 17311076 | chr5 | 17512114 | 17512144 |
| chr5 | 18034335 | 18034365 | chr5 | 22853443 | 22853508 | chr5 | 23011928 | 23011958 |
| chr5 | 31193937 | 31193989 | chr5 | 31194375 | 31194641 | chr5 | 31572285 | 31572344 |
| chr5 | 31639684 | 31639960 | chr5 | 31691477 | 31691652 | chr5 | 31855073 | 31855199 |
| chr5 | 31879243 | 31879282 | chr5 | 32042283 | 32042419 | chr5 | 32314345 | 32314379 |
| chr5 | 32333032 | 32333111 | chr5 | 32446143 | 32446274 | chr5 | 32710331 | 32710470 |
| chr5 | 32710802 | 32711531 | chr5 | 32711826 | 32711870 | chr5 | 32712077 | 32712101 |
| chr5 | 32712290 | 32712491 | chr5 | 32712764 | 32713304 | chr5 | 33234280 | 33234411 |
| chr5 | 33298005 | 33298076 | chr5 | 33509607 | 33509776 | chr5 | 33892083 | 33892115 |
| chr5 | 33892413 | 33892443 | chr5 | 33936156 | 33936336 | chr5 | 33936486 | 33936516 |
| chr5 | 33936599 | 33936663 | chr5 | 34656932 | 34657034 | chr5 | 35874560 | 35874589 |
| chr5 | 35939832 | 35939861 | chr5 | 37376644 | 37376674 | chr5 | 37834684 | 37834714 |
| chr5 | 37835015 | 37835125 | chr5 | 37836231 | 37836260 | chr5 | 37836649 | 37837992 |
| chr5 | 37838548 | 37838885 | chr5 | 37839808 | 37840125 | chr5 | 37840530 | 37840853 |
| chr5 | 38257485 | 38257606 | chr5 | 38257842 | 38257908 | chr5 | 38257945 | 38257959 |
| chr5 | 38557070 | 38557400 | chr5 | 38845675 | 38846164 | chr5 | 39281800 | 39281943 |
| chr5 | 39343181 | 39343348 | chr5 | 40681122 | 40681227 | chr5 | 40681262 | 40681367 |
| chr5 | 40681676 | 40681839 | chr5 | 40775147 | 40775313 | chr5 | 42260050 | 42260453 |
| chr5 | 42424822 | 42425060 | chr5 | 42931966 | 42931996 | chr5 | 42950980 | 42951311 |
| chr5 | 42951420 | 42952111 | chr5 | 42991825 | 42992241 | chr5 | 42992376 | 42992597 |
| chr5 | 42992783 | 42992934 | chr5 | 42993150 | 42994193 | chr5 | 42994694 | 42994790 |
| chr5 | 42995115 | 42995153 | chr5 | 43007936 | 43007966 | chr5 | 43008202 | 43008562 |
| chr5 | 43017953 | 43018176 | chr5 | 43018327 | 43018767 | chr5 | 43019238 | 43019347 |
| chr5 | 43019809 | 43019887 | chr5 | 43020146 | 43020294 | chr5 | 43040544 | 43040635 |

TABLE 12-continued

| chr | start | end | chr | start | end | chr | start | end |
|---|---|---|---|---|---|---|---|---|
| chr5 | 43040870 | 43040964 | chr5 | 43215538 | 43215738 | chr5 | 43397002 | 43397229 |
| chr5 | 43402678 | 43403084 | chr5 | 43558065 | 43558099 | chr5 | 44389782 | 44389852 |
| chr5 | 45695186 | 45695239 | chr5 | 45695314 | 45695533 | chr5 | 45695906 | 45695947 |
| chr5 | 45696336 | 45696439 | chr5 | 49736592 | 49736685 | chr5 | 50262893 | 50263014 |
| chr5 | 50263568 | 50263641 | chr5 | 50264307 | 50264603 | chr5 | 50264820 | 50264850 |
| chr5 | 50265325 | 50265429 | chr5 | 50265721 | 50265880 | chr5 | 50674152 | 50674188 |
| chr5 | 50674560 | 50674590 | chr5 | 50675013 | 50675075 | chr5 | 50678346 | 50678490 |
| chr5 | 50695351 | 50695463 | chr5 | 52084073 | 52084134 | chr5 | 52887899 | 52888047 |
| chr5 | 54179610 | 54179633 | chr5 | 54180063 | 54180093 | chr5 | 54516371 | 54516680 |
| chr5 | 54516832 | 54517017 | chr5 | 54518651 | 54519288 | chr5 | 54527323 | 54527343 |
| chr5 | 56077938 | 56078065 | chr5 | 56246546 | 56246575 | chr5 | 56247942 | 56247971 |
| chr5 | 56248218 | 56248257 | chr5 | 56467399 | 66467666 | chr5 | 57878271 | 57878375 |
| chr5 | 57878710 | 57878752 | chr5 | 59188291 | 59188327 | chr5 | 59189055 | 59189057 |
| chr5 | 59189189 | 59189206 | chr5 | 59189863 | 59189948 | chr5 | 63254903 | 63255242 |
| chr5 | 63256863 | 63256895 | chr5 | 63257727 | 63257861 | chr5 | 63802007 | 63802304 |
| chr5 | 63802340 | 63802514 | chr5 | 63986488 | 63986527 | chr5 | 63986570 | 63986807 |
| chr5 | 65181732 | 65181778 | chr5 | 67569803 | 67569832 | chr5 | 67588937 | 67589162 |
| chr5 | 67589598 | 67589627 | chr5 | 67590431 | 67590460 | chr5 | 67591068 | 67591157 |
| chr5 | 68391042 | 68391336 | chr5 | 71014720 | 71014895 | chr5 | 71015180 | 71015728 |
| chr5 | 71106820 | 71107027 | chr5 | 71403566 | 71403653 | chr5 | 71403975 | 71404207 |
| chr5 | 72416246 | 72416751 | chr5 | 72526413 | 72526414 | chr5 | 72526492 | 72526643 |
| chr5 | 72528434 | 72528464 | chr5 | 72529289 | 72529825 | chr5 | 72529890 | 72530609 |
| chr5 | 72594802 | 72594836 | chr5 | 72594868 | 72595016 | chr5 | 72595047 | 72595059 |
| chr5 | 72595542 | 72595721 | chr5 | 72595774 | 72595788 | chr5 | 72599079 | 72599441 |
| chr5 | 72599463 | 72599833 | chr5 | 72677775 | 72677825 | chr5 | 72677998 | 72678028 |
| chr5 | 72715204 | 72715347 | chr5 | 72715591 | 72715695 | chr5 | 72715731 | 72715768 |
| chr5 | 72716102 | 72716180 | chr5 | 72732870 | 72732884 | chr5 | 72733093 | 72733185 |
| chr5 | 72740147 | 72740184 | chr5 | 72746680 | 72746683 | chr5 | 74061571 | 74061786 |
| chr5 | 74991793 | 74991908 | chr5 | 75377883 | 75378033 | chr5 | 75380163 | 75380193 |
| chr5 | 75380624 | 75380974 | chr5 | 76011285 | 76011337 | chr5 | 76012576 | 76012605 |
| chr5 | 76249270 | 76249670 | chr5 | 76249696 | 76249906 | chr5 | 76249945 | 76250150 |
| chr5 | 76250435 | 76250504 | chr5 | 76327468 | 76327697 | chr5 | 76506469 | 76506506 |
| chr5 | 76507035 | 76507114 | chr5 | 76923679 | 76924023 | chr5 | 76924087 | 76924299 |
| chr5 | 76924930 | 76924960 | chr5 | 76925561 | 76925690 | chr5 | 76928157 | 76928397 |
| chr5 | 76928688 | 76928906 | chr5 | 76932302 | 76932332 | chr5 | 76932542 | 76933265 |
| chr5 | 76934173 | 76934653 | chr5 | 76934677 | 76934870 | chr5 | 76936016 | 76936721 |
| chr5 | 76939436 | 76939774 | chr5 | 76940340 | 76940374 | chr5 | 76941201 | 76941326 |
| chr5 | 77140527 | 77140711 | chr5 | 77147563 | 77147649 | chr5 | 77147873 | 77148195 |
| chr5 | 77148498 | 77148712 | chr5 | 77268367 | 77269237 | chr5 | 77269264 | 77269309 |
| chr5 | 77655342 | 77655388 | chr5 | 78005726 | 78005913 | chr5 | 78039632 | 78039673 |
| chr5 | 78407651 | 78407840 | chr5 | 78408192 | 78408274 | chr5 | 78408298 | 78408461 |
| chr5 | 78910189 | 78910332 | chr5 | 79554097 | 79554169 | chr5 | 79563425 | 79563643 |
| chr5 | 79598681 | 79598836 | chr5 | 79783240 | 79783421 | chr5 | 79864898 | 79865078 |
| chr5 | 79866100 | 79866414 | chr5 | 79947584 | 79947707 | chr5 | 80255816 | 80256074 |
| chr5 | 80689543 | 80689735 | chr5 | 80690118 | 80690239 | chr5 | 82168369 | 82168480 |
| chr5 | 82767429 | 82767793 | chr5 | 82768892 | 82769061 | chr5 | 83679195 | 83679225 |
| chr5 | 83679681 | 83680340 | chr5 | 83680615 | 83680664 | chr5 | 83680694 | 83680708 |
| chr5 | 86414242 | 86414297 | chr5 | 87955460 | 87955664 | chr5 | 87956199 | 87956662 |
| chr5 | 87956680 | 87956964 | chr5 | 87962966 | 87963002 | chr5 | 87963390 | 87963511 |
| chr5 | 87967773 | 87968077 | chr5 | 87968486 | 87968685 | chr5 | 87968773 | 87968858 |
| chr5 | 87970193 | 87970872 | chr5 | 87974104 | 87974307 | chr5 | 87974868 | 87975023 |
| chr5 | 87976028 | 87976308 | chr5 | 87976525 | 87976559 | chr5 | 87979756 | 87979912 |
| chr5 | 87980142 | 87980250 | chr5 | 87980954 | 87981325 | chr5 | 87984532 | 87984657 |
| chr5 | 87985922 | 87985954 | chr5 | 87986210 | 87986281 | chr5 | 87986547 | 87986581 |
| chr5 | 87988516 | 87988584 | chr5 | 87990408 | 87990452 | chr5 | 88185470 | 88186001 |
| chr5 | 89854856 | 89854902 | chr5 | 94889396 | 94889434 | chr5 | 94955681 | 94955919 |
| chr5 | 94956935 | 94957000 | chr5 | 94982042 | 94982225 | chr5 | 95767894 | 95768384 |
| chr5 | 95768920 | 95769093 | chr5 | 96114587 | 96114632 | chr5 | 100236682 | 100236757 |
| chr5 | 100238882 | 100239119 | chr5 | 100239135 | 100239151 | chr5 | 101631487 | 101631533 |
| chr5 | 101632295 | 101632573 | chr5 | 107005983 | 107006186 | chr5 | 111987744 | 111987818 |
| chr5 | 112042844 | 112042873 | chr5 | 112042904 | 112043289 | chr5 | 112073358 | 112073516 |
| chr5 | 112170808 | 112170837 | chr5 | 112175198 | 112175227 | chr5 | 112175640 | 112175669 |
| chr5 | 112258359 | 112258388 | chr5 | 112258634 | 112258663 | chr5 | 112340666 | 112340704 |
| chr5 | 112629427 | 112629674 | chr5 | 113391265 | 113392018 | chr5 | 113698567 | 113698583 |
| chr5 | 113698670 | 113698783 | chr5 | 113699008 | 113699119 | chr5 | 114515010 | 114515579 |
| chr5 | 114515611 | 114515671 | chr5 | 115151267 | 115151357 | chr5 | 115151650 | 115152384 |
| chr5 | 115152617 | 115152638 | chr5 | 115154758 | 115154825 | chr5 | 115176039 | 115176228 |
| chr5 | 115297192 | 115297292 | chr5 | 115297377 | 115297556 | chr5 | 115297928 | 115297985 |
| chr5 | 115298496 | 115298581 | chr5 | 115298985 | 115299041 | chr5 | 116143271 | 116143325 |
| chr5 | 119799931 | 119799986 | chr5 | 119801299 | 119801445 | chr5 | 120399966 | 120400129 |
| chr5 | 121413537 | 121413590 | chr5 | 122422240 | 122422292 | chr5 | 122422616 | 122422651 |
| chr5 | 122423328 | 122423376 | chr5 | 122425128 | 122425168 | chr5 | 122431118 | 122431378 |
| chr5 | 124128410 | 124128497 | chr5 | 126231644 | 126231674 | chr5 | 126245097 | 126245133 |
| chr5 | 126626283 | 126626738 | chr5 | 127088743 | 127088773 | chr5 | 127872942 | 127872990 |
| chr5 | 127873553 | 127873710 | chr5 | 127874448 | 127874477 | chr5 | 127874706 | 127874839 |
| chr5 | 128300680 | 128300694 | chr5 | 128300713 | 128300794 | chr5 | 128796081 | 128796244 |
| chr5 | 128796867 | 128796985 | chr5 | 128797344 | 128797386 | chr5 | 129240068 | 129240101 |
| chr5 | 130153448 | 130153623 | chr5 | 131134159 | 131134203 | chr5 | 131992096 | 131992167 |

TABLE 12-continued

| chr | start | end | chr | start | end | chr | start | end |
|---|---|---|---|---|---|---|---|---|
| chr5 | 132947486 | 132947836 | chr5 | 133820008 | 133820040 | chr5 | 133968996 | 133969192 |
| chr5 | 134364195 | 134364289 | chr5 | 134366718 | 134366788 | chr5 | 134367108 | 134367203 |
| chr5 | 134374447 | 134374505 | chr5 | 134374792 | 134375210 | chr5 | 134376222 | 134376375 |
| chr5 | 134376732 | 134376824 | chr5 | 134385952 | 134386167 | chr5 | 134386185 | 134386383 |
| chr5 | 134582864 | 134582894 | chr5 | 134735622 | 134735651 | chr5 | 134825463 | 134825518 |
| chr5 | 134825913 | 134826006 | chr5 | 134870446 | 134870515 | chr5 | 134870780 | 134870926 |
| chr5 | 134871601 | 134872049 | chr5 | 134879478 | 134880022 | chr5 | 134880049 | 134880501 |
| chr5 | 134914627 | 134914748 | chr5 | 135265737 | 135265767 | chr5 | 135266114 | 135266128 |
| chr5 | 135266578 | 135266672 | chr5 | 135528201 | 135528233 | chr5 | 136834050 | 136834050 |
| chr5 | 136834290 | 136834506 | chr5 | 136834720 | 136834826 | chr5 | 137225092 | 137225297 |
| chr5 | 137404150 | 137404180 | chr5 | 137912037 | 137912148 | chr5 | 138196197 | 138196408 |
| chr5 | 138273817 | 138273854 | chr5 | 139045286 | 139045315 | chr5 | 139047990 | 139048162 |
| chr5 | 139056666 | 139056804 | chr5 | 139227773 | 139227909 | chr5 | 139454108 | 139454202 |
| chr5 | 139525728 | 139525758 | chr5 | 139779555 | 139779871 | chr5 | 140174798 | 140174839 |
| chr5 | 140187094 | 140187146 | chr5 | 140305978 | 140306050 | chr5 | 140306445 | 140306619 |
| chr5 | 140306675 | 140306733 | chr5 | 140346595 | 140346671 | chr5 | 140514891 | 140514921 |
| chr5 | 140604459 | 140604501 | chr5 | 140613926 | 140614014 | chr5 | 140614314 | 140614328 |
| chr5 | 140683631 | 140683772 | chr5 | 140777328 | 140777487 | chr5 | 140787623 | 140787637 |
| chr5 | 140797076 | 140797278 | chr5 | 140797328 | 140797342 | chr5 | 140800479 | 140800964 |
| chr5 | 140801035 | 140801246 | chr5 | 140855598 | 140856458 | chr5 | 140856547 | 140856622 |
| chr5 | 141031121 | 141031150 | chr5 | 141263035 | 141263142 | chr5 | 141931340 | 141931354 |
| chr5 | 141931425 | 141931539 | chr5 | 142784967 | 142785272 | chr5 | 145713645 | 145713896 |
| chr5 | 145717175 | 145717196 | chr5 | 145717249 | 145717437 | chr5 | 145718802 | 145719753 |
| chr5 | 145719835 | 145719925 | chr5 | 145720812 | 145720917 | chr5 | 145722116 | 145722466 |
| chr5 | 145722561 | 145723027 | chr5 | 145724502 | 145724698 | chr5 | 145725694 | 145725844 |
| chr5 | 146257332 | 146257602 | chr5 | 146889332 | 146889575 | chr5 | 147003444 | 147003536 |
| chr5 | 147326357 | 147326510 | chr5 | 149503827 | 149503856 | chr5 | 149682074 | 149682166 |
| chr5 | 150029147 | 150029245 | chr5 | 150051101 | 150051667 | chr5 | 150326159 | 150326188 |
| chr5 | 150400123 | 150400203 | chr5 | 151066442 | 151066474 | chr5 | 151304371 | 151304401 |
| chr5 | 153852664 | 153852792 | chr5 | 153853420 | 153853478 | chr5 | 153854330 | 153854360 |
| chr5 | 153855175 | 153855264 | chr5 | 153855658 | 153855839 | chr5 | 153856149 | 153856396 |
| chr5 | 153856936 | 153856996 | chr5 | 153857379 | 153857429 | chr5 | 153858319 | 153858599 |
| chr5 | 153859676 | 153859708 | chr5 | 153862037 | 153862179 | chr5 | 153862219 | 153862577 |
| chr5 | 153863421 | 153863451 | chr5 | 154030048 | 154030160 | chr5 | 154061801 | 154061894 |
| chr5 | 154209926 | 154209987 | chr5 | 154318148 | 154318329 | chr5 | 155107794 | 155107848 |
| chr5 | 155108161 | 155108267 | chr5 | 155108356 | 155108526 | chr5 | 155108733 | 155108763 |
| chr5 | 156485385 | 156485415 | chr5 | 156558444 | 156558689 | chr5 | 156655170 | 156655200 |
| chr5 | 156874257 | 156874308 | chr5 | 157001739 | 157001843 | chr5 | 157078419 | 157078449 |
| chr5 | 157098362 | 157098619 | chr5 | 167673799 | 157673964 | chr5 | 158478513 | 158478764 |
| chr5 | 158524692 | 158524748 | chr5 | 158524865 | 158524925 | chr5 | 158527443 | 158528069 |
| chr5 | 158612981 | 158613074 | chr5 | 159399095 | 159399099 | chr5 | 159437197 | 159437235 |
| chr5 | 160975724 | 160975754 | chr5 | 161274310 | 161274554 | chr5 | 166865449 | 166865616 |
| chr5 | 167956177 | 167956266 | chr5 | 167956414 | 167956595 | chr5 | 168233396 | 168233482 |
| chr5 | 168727924 | 168727927 | chr5 | 169064327 | 169064805 | chr5 | 169366082 | 169366201 |
| chr5 | 169532927 | 169533012 | chr5 | 170108287 | 170108372 | chr5 | 170735154 | 170735206 |
| chr5 | 170735731 | 170735788 | chr5 | 170736116 | 170736163 | chr5 | 170736716 | 170736830 |
| chr5 | 170737282 | 170737479 | chr5 | 170737741 | 170737863 | chr5 | 170737936 | 170738689 |
| chr5 | 170738824 | 170739481 | chr5 | 170739823 | 170740027 | chr5 | 170740461 | 170740477 |
| chr5 | 170740575 | 170741240 | chr5 | 170741465 | 170742275 | chr5 | 170742387 | 170742599 |
| chr5 | 170742673 | 170743479 | chr5 | 170743647 | 170744128 | chr5 | 170744375 | 170744562 |
| chr5 | 170745389 | 170745480 | chr5 | 171352123 | 171352153 | chr5 | 172354043 | 172354118 |
| chr5 | 172485539 | 172485586 | chr5 | 172655879 | 172656216 | chr5 | 172659225 | 172659290 |
| chr5 | 172659496 | 172659655 | chr5 | 172659855 | 172660025 | chr5 | 172660142 | 172660218 |
| chr5 | 172660719 | 172661000 | chr5 | 172661127 | 172661684 | chr5 | 172664226 | 172664487 |
| chr5 | 172665590 | 172665812 | chr5 | 172670983 | 172671018 | chr5 | 172671345 | 172671481 |
| chr5 | 172671640 | 172671968 | chr5 | 172672477 | 172672663 | chr5 | 172754589 | 172754621 |
| chr5 | 172754832 | 172754931 | chr5 | 172755470 | 172755562 | chr5 | 172755595 | 172755663 |
| chr5 | 172757048 | 172757111 | chr5 | 174115388 | 174115861 | chr5 | 174147523 | 174147596 |
| chr5 | 174150415 | 174150445 | chr5 | 174159300 | 174159588 | chr5 | 174162874 | 174162904 |
| chr5 | 174220971 | 174221001 | chr5 | 174870738 | 174870786 | chr5 | 174871174 | 174871497 |
| chr5 | 174921456 | 174921629 | chr5 | 175085147 | 175085209 | chr5 | 175085525 | 175085719 |
| chr5 | 175223671 | 175223709 | chr5 | 175298549 | 175298883 | chr5 | 175299294 | 175299396 |
| chr5 | 175300351 | 175300381 | chr5 | 175621390 | 175621501 | chr5 | 175790961 | 175790991 |
| chr5 | 175792865 | 175792931 | chr5 | 175792998 | 175793063 | chr5 | 175831257 | 175831326 |
| chr5 | 175876388 | 175876504 | chr5 | 175971447 | 175971615 | chr5 | 175978889 | 175978976 |
| chr5 | 176024006 | 176024318 | chr5 | 176046363 | 176046554 | chr5 | 176107274 | 176107484 |
| chr5 | 176107518 | 176107586 | chr5 | 176236721 | 176236898 | chr5 | 176264805 | 176264915 |
| chr5 | 176295786 | 176295892 | chr5 | 176520166 | 176520195 | chr5 | 176522400 | 176522566 |
| chr5 | 176764100 | 176764169 | chr5 | 176827656 | 176827685 | chr5 | 177020093 | 177020153 |
| chr5 | 177031167 | 177031197 | chr5 | 177408292 | 177408443 | chr5 | 177411638 | 177412141 |
| chr5 | 177512244 | 177512377 | chr5 | 177556807 | 177557022 | chr5 | 177579824 | 177580065 |
| chr5 | 177644565 | 177644601 | chr5 | 177713376 | 177713468 | chr5 | 178004325 | 178004374 |
| chr5 | 178016682 | 178016983 | chr5 | 178017520 | 178017867 | chr5 | 178151333 | 178151363 |
| chr5 | 178368074 | 178368121 | chr5 | 178487107 | 178487303 | chr5 | 178487342 | 178487398 |
| chr5 | 178576356 | 178576499 | chr5 | 178655753 | 178655871 | chr5 | 178771314 | 178771630 |
| chr5 | 178771724 | 178771859 | chr5 | 178772205 | 178772272 | chr5 | 178772603 | 178772729 |
| chr5 | 178781548 | 178781577 | chr5 | 178955527 | 178955656 | chr5 | 178957637 | 178957944 |
| chr5 | 178969722 | 178969752 | chr5 | 178978946 | 178978976 | chr5 | 179060235 | 179060655 |

TABLE 12-continued

| chr | start | end | chr | start | end | chr | start | end |
|---|---|---|---|---|---|---|---|---|
| chr5 | 179098595 | 179098633 | chr5 | 179214113 | 179214196 | chr5 | 179217327 | 179217447 |
| chr5 | 179270584 | 179270748 | chr5 | 179553207 | 179553237 | chr5 | 179780104 | 179780144 |
| chr5 | 179780706 | 179780985 | chr5 | 179867486 | 179867548 | chr5 | 120012118 | 180017198 |
| chr5 | 180017608 | 180017933 | chr5 | 180018485 | 180018498 | chr5 | 180030654 | 180030700 |
| chr5 | 180047440 | 180047605 | chr5 | 180075846 | 180075857 | chr5 | 180076054 | 180076317 |
| chr5 | 180076567 | 180076602 | chr5 | 180076804 | 180076996 | chr5 | 180101016 | 180101167 |
| chr5 | 180101252 | 180101332 | chr5 | 180326126 | 180326156 | chr5 | 180454232 | 180454334 |
| chr5 | 180527546 | 180527698 | chr5 | 180594851 | 180595002 | chr5 | 180600858 | 180601218 |
| chr5 | 180612346 | 180612376 | chr5 | 180629320 | 180629350 | chr5 | 180636016 | 180636205 |
| chr6 | 373148 | 373290 | chr6 | 391173 | 391899 | chr6 | 392410 | 392433 |
| chr6 | 392588 | 392958 | chr6 | 393125 | 393472 | chr6 | 711142 | 711293 |
| chr6 | 1312000 | 1312096 | chr6 | 1312595 | 1312708 | chr6 | 1314088 | 1314100 |
| chr6 | 1378222 | 1378475 | chr6 | 1379584 | 1379614 | chr6 | 1379909 | 1379952 |
| chr6 | 1383677 | 1383708 | chr6 | 1383860 | 1384179 | chr6 | 1384626 | 1384644 |
| chr6 | 1385118 | 1385170 | chr6 | 1386071 | 1386112 | chr6 | 1389124 | 1389262 |
| chr6 | 1390241 | 1390405 | chr6 | 1390424 | 1390758 | chr6 | 1390956 | 1391035 |
| chr6 | 1391318 | 1391379 | chr6 | 1524199 | 1524283 | chr6 | 1605387 | 1605454 |
| chr6 | 1620672 | 1620701 | chr6 | 1624977 | 1625818 | chr6 | 2986688 | 2986718 |
| chr6 | 3053299 | 3053386 | chr6 | 3229029 | 3229062 | chr6 | 3229423 | 3229510 |
| chr6 | 3232010 | 3232260 | chr6 | 3247675 | 3247704 | chr6 | 3285222 | 3285513 |
| chr6 | 3405645 | 3405713 | chr6 | 4775062 | 4775222 | chr6 | 4836002 | 4836458 |
| chr6 | 4951247 | 4951390 | chr6 | 5359500 | 5359539 | chr6 | 5783325 | 5783496 |
| chr6 | 5996952 | 5996989 | chr6 | 5997802 | 5997832 | chr6 | 6003287 | 6003528 |
| chr6 | 6004350 | 6004743 | chr6 | 6004837 | 6005417 | chr6 | 6006374 | 6006419 |
| chr6 | 6006674 | 6006883 | chr6 | 6007593 | 6008277 | chr6 | 6367086 | 6367271 |
| chr6 | 6753803 | 6753839 | chr6 | 7726334 | 7726363 | chr6 | 7726630 | 7726659 |
| chr6 | 7726952 | 7726981 | chr6 | 7727699 | 7727768 | chr6 | 7728087 | 7728142 |
| chr6 | 7728849 | 7728941 | chr6 | 7731054 | 7731083 | chr6 | 7892314 | 7892412 |
| chr6 | 8014600 | 8014772 | chr6 | 10381507 | 10381592 | chr6 | 10381695 | 10381968 |
| chr6 | 10382722 | 10383049 | chr6 | 10383739 | 10383774 | chr6 | 10384950 | 10384974 |
| chr6 | 10385280 | 10385939 | chr6 | 10386210 | 10386273 | chr6 | 10390023 | 10391187 |
| chr6 | 10410518 | 10410578 | chr6 | 10411356 | 10411510 | chr6 | 10415113 | 10415215 |
| chr6 | 10415559 | 10415713 | chr6 | 10416118 | 10416351 | chr6 | 10417158 | 10417529 |
| chr6 | 10419086 | 10419439 | chr6 | 10419477 | 10419506 | chr6 | 10419744 | 10419941 |
| chr6 | 10421053 | 10421451 | chr6 | 10421549 | 10422635 | chr6 | 10423613 | 10423704 |
| chr6 | 10425630 | 10425789 | chr6 | 10425839 | 10426884 | chr6 | 10542836 | 10542977 |
| chr6 | 10734917 | 10735045 | chr6 | 10881835 | 10882057 | chr6 | 10882321 | 10882350 |
| chr6 | 10883008 | 10883022 | chr6 | 10883444 | 10883474 | chr6 | 10887078 | 10887686 |
| chr6 | 11044062 | 11044572 | chr6 | 12288517 | 12288681 | chr6 | 12749899 | 12749940 |
| chr6 | 13797690 | 13797736 | chr6 | 14687918 | 14688084 | chr6 | 14986483 | 14986522 |
| chr6 | 15513780 | 15513981 | chr6 | 16197030 | 16197112 | chr6 | 16729595 | 16729624 |
| chr6 | 17281417 | 17281534 | chr6 | 17666654 | 17666707 | chr6 | 17750276 | 17750306 |
| chr6 | 18035867 | 18036015 | chr6 | 19691638 | 19691841 | chr6 | 19692143 | 19692318 |
| chr6 | 19837064 | 19837140 | chr6 | 19892448 | 19892627 | chr6 | 21664719 | 21664749 |
| chr6 | 21665004 | 21665043 | chr6 | 22172209 | 22172305 | chr6 | 22172536 | 22172566 |
| chr6 | 24358291 | 24358320 | chr6 | 24360074 | 24360170 | chr6 | 24494679 | 24494766 |
| chr6 | 24647342 | 24647599 | chr6 | 24662439 | 24662469 | chr6 | 26034268 | 26034311 |
| chr6 | 26184095 | 26184391 | chr6 | 26188696 | 26189393 | chr6 | 26189859 | 26189991 |
| chr6 | 26199137 | 26199167 | chr6 | 26199686 | 26199716 | chr6 | 26214514 | 26214648 |
| chr6 | 26235223 | 26235623 | chr6 | 26240504 | 26241118 | chr6 | 26250468 | 26250826 |
| chr6 | 26251054 | 26251182 | chr6 | 26251816 | 26252098 | chr6 | 26252141 | 26252151 |
| chr6 | 26254617 | 26254647 | chr6 | 26260956 | 26260986 | chr6 | 26271406 | 26271762 |
| chr6 | 26271971 | 26272001 | chr6 | 26272512 | 26272617 | chr6 | 26273400 | 26273418 |
| chr6 | 26284811 | 26284898 | chr6 | 26327806 | 26327982 | chr6 | 26328294 | 26328457 |
| chr6 | 26332178 | 26332218 | chr6 | 26501950 | 26502209 | chr6 | 26550994 | 26551034 |
| chr6 | 26577158 | 26577475 | chr6 | 26987967 | 26988166 | chr6 | 27059783 | 27059848 |
| chr6 | 27064682 | 27065198 | chr6 | 27173528 | 27173546 | chr6 | 27173633 | 27174181 |
| chr6 | 27182869 | 27182899 | chr6 | 27203269 | 27203336 | chr6 | 27205300 | 27205441 |
| chr6 | 22205671 | 27205836 | chr6 | 27205914 | 27206040 | chr6 | 27218951 | 27218980 |
| chr6 | 27228180 | 27228186 | chr6 | 27228290 | 27228395 | chr6 | 27235876 | 27235905 |
| chr6 | 27247636 | 27247724 | chr6 | 27256097 | 27256173 | chr6 | 27256383 | 27256420 |
| chr6 | 27264332 | 27264364 | chr6 | 27279845 | 27280012 | chr6 | 27441812 | 27441842 |
| chr6 | 27463029 | 27463687 | chr6 | 27512761 | 27512883 | chr6 | 27512995 | 27513487 |
| chr6 | 27533822 | 27534341 | chr6 | 27559809 | 27560075 | chr6 | 27573171 | 27573392 |
| chr6 | 27598738 | 27598860 | chr6 | 27599159 | 27599341 | chr6 | 27635265 | 27635434 |
| chr6 | 27647712 | 27647735 | chr6 | 27647891 | 27647896 | chr6 | 27648912 | 27649134 |
| chr6 | 27783039 | 27783052 | chr6 | 27799464 | 27799581 | chr6 | 27834676 | 27834835 |
| chr6 | 27835047 | 27835096 | chr6 | 27835378 | 27835417 | chr6 | 27839726 | 27840082 |
| chr6 | 27840543 | 27840617 | chr6 | 27841104 | 27841136 | chr6 | 27858515 | 27858637 |
| chr6 | 28175189 | 28176212 | chr6 | 28227076 | 28227141 | chr6 | 28303562 | 28303607 |
| chr6 | 28303815 | 28304263 | chr6 | 28367109 | 28367346 | chr6 | 28367491 | 28367774 |
| chr6 | 28410976 | 28411087 | chr6 | 28411152 | 28411353 | chr6 | 28414977 | 28414991 |
| chr6 | 28457608 | 28457638 | chr6 | 28457870 | 28458158 | chr6 | 28956323 | 28956511 |
| chr6 | 28956660 | 28956719 | chr6 | 30095233 | 30095262 | chr6 | 30095418 | 30095570 |
| chr6 | 30130804 | 30130895 | chr6 | 30644680 | 30644798 | chr6 | 32374147 | 32374176 |
| chr6 | 32374739 | 32374768 | chr6 | 32376051 | 32376080 | chr6 | 33161275 | 33161342 |
| chr6 | 33632930 | 33633000 | chr6 | 33636388 | 33636418 | chr6 | 33955505 | 33955731 |
| chr6 | 34113872 | 34113957 | chr6 | 34170970 | 34171061 | chr6 | 34219930 | 34219972 |

TABLE 12-continued

| chr | start | end | chr | start | end | chr | start | end |
|---|---|---|---|---|---|---|---|---|
| chr6 | 34396431 | 34396542 | chr6 | 34535802 | 34535832 | chr6 | 34714803 | 34714896 |
| chr6 | 34724047 | 34724228 | chr6 | 35150041 | 35150080 | chr6 | 35182493 | 35182522 |
| chr6 | 35470285 | 35470399 | chr6 | 35479613 | 35479642 | chr6 | 35992428 | 35992458 |
| chr6 | 36165662 | 36165692 | chr6 | 36178031 | 36178301 | chr6 | 36252984 | 36253171 |
| chr6 | 36313883 | 36313913 | chr6 | 36392273 | 36392323 | chr6 | 36406316 | 36406370 |
| chr6 | 36808323 | 36808441 | chr6 | 37024559 | 37024589 | chr6 | 37392127 | 37392189 |
| chr6 | 37545401 | 37545495 | chr6 | 37664140 | 37664187 | chr6 | 37673320 | 37673611 |
| chr6 | 37776410 | 37276440 | chr6 | 37776703 | 37776735 | chr6 | 38683212 | 38683235 |
| chr6 | 39281088 | 39281133 | chr6 | 39281824 | 39281875 | chr6 | 39329863 | 39329892 |
| chr6 | 39508464 | 39508493 | chr6 | 39760401 | 39760661 | chr6 | 40554653 | 40554699 |
| chr6 | 41273881 | 41273942 | chr6 | 41337072 | 41337128 | chr6 | 41339263 | 41339558 |
| chr6 | 41339602 | 41339838 | chr6 | 41340902 | 41341182 | chr6 | 41341501 | 41341549 |
| chr6 | 41342243 | 41342275 | chr6 | 41342807 | 41342837 | chr6 | 41605937 | 41605951 |
| chr6 | 41606038 | 41606356 | chr6 | 41606528 | 41606542 | chr6 | 41773520 | 41773903 |
| chr6 | 41774459 | 41774576 | chr6 | 42062143 | 42062346 | chr6 | 42090977 | 42091027 |
| chr6 | 42111015 | 42111051 | chr6 | 42711893 | 42711923 | chr6 | 42738966 | 42739049 |
| chr6 | 42773440 | 42773622 | chr6 | 42846662 | 42846705 | chr6 | 42879554 | 42879568 |
| chr6 | 42879622 | 42879718 | chr6 | 42928321 | 42928454 | chr6 | 42990166 | 42990485 |
| chr6 | 43119019 | 43119580 | chr6 | 43211193 | 43211311 | chr6 | 43424297 | 43424470 |
| chr6 | 43425152 | 43425207 | chr6 | 43425479 | 43425509 | chr6 | 43478676 | 43478745 |
| chr6 | 43612825 | 43612898 | chr6 | 43613053 | 43613067 | chr6 | 43639548 | 43639710 |
| chr6 | 43748463 | 43748616 | chr6 | 44240914 | 44241108 | chr6 | 44695763 | 44695795 |
| chr6 | 45388716 | 45388775 | chr6 | 46702982 | 46703123 | chr6 | 46703350 | 46703436 |
| chr6 | 47473194 | 47473287 | chr6 | 47590439 | 47590604 | chr6 | 49590555 | 49590786 |
| chr6 | 49765146 | 49765202 | chr6 | 50674372 | 50674750 | chr6 | 50681699 | 50681942 |
| chr6 | 50682319 | 50682338 | chr6 | 50682659 | 50682683 | chr6 | 50682712 | 50682940 |
| chr6 | 50682992 | 50683227 | chr6 | 50684969 | 50684969 | chr6 | 50689913 | 50690039 |
| chr6 | 50691065 | 50691095 | chr6 | 50692083 | 50692212 | chr6 | 50692300 | 50692481 |
| chr6 | 50787216 | 50787876 | chr6 | 50787950 | 50788352 | chr6 | 50789374 | 50789404 |
| chr6 | 50791187 | 50791494 | chr6 | 50791551 | 50791632 | chr6 | 50793335 | 50793404 |
| chr6 | 50793728 | 50793882 | chr6 | 50794531 | 50794693 | chr6 | 50803834 | 50803867 |
| chr6 | 50804131 | 50804368 | chr6 | 50808681 | 50808854 | chr6 | 50810551 | 50810713 |
| chr6 | 50811062 | 50811488 | chr6 | 50813258 | 50813939 | chr6 | 50814569 | 50814599 |
| chr6 | 50817023 | 50817229 | chr6 | 50817905 | 50817935 | chr6 | 50818449 | 50818706 |
| chr6 | 50818920 | 50819000 | chr6 | 52227752 | 52227781 | chr6 | 52228008 | 52228037 |
| chr6 | 52344375 | 52344405 | chr6 | 52763812 | 52763982 | chr6 | 52928742 | 52928776 |
| chr6 | 52929051 | 52929233 | chr6 | 53052723 | 53052859 | chr6 | 53212491 | 53213970 |
| chr6 | 55443691 | 55443946 | chr6 | 56112262 | 56112386 | chr6 | 56716390 | 56716410 |
| chr6 | 56818656 | 56818937 | chr6 | 56819217 | 56819637 | chr6 | 56819897 | 56819926 |
| chr6 | 57694587 | 57694617 | chr6 | 58147447 | 58147480 | chr6 | 58147790 | 58147976 |
| chr6 | 62995356 | 62995874 | chr6 | 62996078 | 62996146 | chr6 | 62996443 | 62996489 |
| chr6 | 70992137 | 70992162 | chr6 | 70992415 | 70992560 | chr6 | 70992830 | 70993015 |
| chr6 | 71090933 | 71090963 | chr6 | 71665638 | 71665723 | chr6 | 71666788 | 71666986 |
| chr6 | 72129789 | 72129829 | chr6 | 72130191 | 72130464 | chr6 | 72596120 | 72596315 |
| chr6 | 72596950 | 72596980 | chr6 | 73329784 | 73330126 | chr6 | 73330834 | 73331304 |
| chr6 | 73331515 | 73331850 | chr6 | 73331876 | 73333122 | chr6 | 73980676 | 73980722 |
| chr6 | 73982025 | 73982058 | chr6 | 74097722 | 74097763 | chr6 | 75995789 | 75995819 |
| chr6 | 76059561 | 76059787 | chr6 | 78172177 | 78172275 | chr6 | 78172323 | 78172572 |
| chr6 | 78173212 | 78173264 | chr6 | 78173696 | 78173725 | chr6 | 78173772 | 78173984 |
| chr6 | 78176458 | 78176820 | chr6 | 79620475 | 79620699 | chr6 | 80656930 | 80657180 |
| chr6 | 82463270 | 82463310 | chrf | 82958615 | 82958917 | chr6 | 83546464 | 83546498 |
| chr6 | 84141298 | 84141412 | chr6 | 84417436 | 84417700 | chr6 | 84418261 | 84418281 |
| chr6 | 84418644 | 84418788 | chr6 | 84419157 | 84419415 | chr6 | 84562873 | 84563242 |
| chr6 | 84563489 | 84563542 | chr6 | 85050415 | 85050504 | chr6 | 85472407 | 85473703 |
| chr6 | 85473928 | 85474378 | chr6 | 85474594 | 85474736 | chr6 | 85476233 | 85476285 |
| chr6 | 85476998 | 85477028 | chr6 | 85478514 | 85478724 | chr6 | 85482530 | 85482822 |
| chr6 | 85483345 | 85483375 | chr6 | 85483760 | 85483931 | chr6 | 85484558 | 85484625 |
| chr6 | 85484717 | 85484920 | chr6 | 86302413 | 86302614 | chr6 | 87647114 | 87647143 |
| chr6 | 87862092 | 87862172 | chr6 | 88518712 | 88518742 | chr6 | 88876963 | 88877421 |
| chr6 | 89672213 | 89672376 | chr6 | 91320285 | 91320318 | chr6 | 91320949 | 91321295 |
| chr6 | 94126973 | 94127064 | chr6 | 94127455 | 94127544 | chr6 | 94128365 | 94128399 |
| chr6 | 94129219 | 94129257 | chr6 | 94129509 | 94129575 | chr6 | 96464100 | 96464204 |
| chr6 | 97412429 | 97412529 | chr6 | 97930083 | 97930113 | chr6 | 99271926 | 99272810 |
| chr6 | 99273369 | 99273410 | chr6 | 99277180 | 99277330 | chr6 | 99279556 | 99279612 |
| chr6 | 99280557 | 99280744 | chr6 | 99281014 | 99281036 | chr6 | 99281068 | 99281385 |
| chr6 | 99283512 | 99283582 | chr6 | 99290360 | 99290398 | chr6 | 99291264 | 99291341 |
| chr6 | 99292252 | 99292417 | chr6 | 99295726 | 99295863 | chr6 | 99296062 | 99296364 |
| chr6 | 99296408 | 99296467 | chr6 | 99396456 | 99396609 | chr6 | 99842067 | 99842258 |
| chr6 | 99842336 | 99842382 | chr6 | 100038682 | 100038706 | chr6 | 100038786 | 100038964 |
| chr6 | 100039275 | 100039289 | chr6 | 100050754 | 100050810 | chr6 | 100050859 | 100051108 |
| chr6 | 100051360 | 100051507 | chr6 | 100051772 | 100051971 | chr6 | 100053221 | 100053511 |
| chr6 | 100054866 | 100054917 | chr6 | 100061022 | 100061076 | chr6 | 100061311 | 100061419 |
| chr6 | 100062178 | 100062586 | chr6 | 100062944 | 100063068 | chr6 | 100135425 | 100135583 |
| chr6 | 100441498 | 100441737 | chr6 | 100441762 | 100441966 | chr6 | 100903384 | 100903404 |
| chr6 | 100903561 | 100903631 | chr6 | 100904214 | 100904225 | chr6 | 100905969 | 100906016 |
| chr6 | 100911686 | 100911723 | chr6 | 100912070 | 100912119 | chr6 | 100912421 | 100912445 |
| chr6 | 100912466 | 100912480 | chr6 | 100912919 | 100913050 | chr6 | 100915101 | 100915205 |
| chr6 | 101840708 | 101840820 | chr6 | 101846782 | 101846789 | chr6 | 101847185 | 101847215 |

TABLE 12-continued

| chr | start | end | chr | start | end | chr | start | end |
|---|---|---|---|---|---|---|---|---|
| chr6 | 101850147 | 101850275 | chr6 | 105388679 | 105388708 | chr6 | 105389510 | 105389710 |
| chr6 | 105400913 | 105401007 | chr6 | 105401620 | 105401874 | chr6 | 105404574 | 105404674 |
| chr6 | 105405656 | 105405772 | chr6 | 105406098 | 105406128 | chr6 | 105584264 | 105584319 |
| chr6 | 105584367 | 105585554 | chr6 | 105821423 | 105821453 | chr6 | 106429049 | 106429475 |
| chr6 | 106429590 | 106429624 | chr6 | 106434339 | 106434368 | chr6 | 106441869 | 106442979 |
| chr6 | 106731509 | 106731597 | chr6 | 106960908 | 106961020 | chr6 | 107075651 | 107075704 |
| chr6 | 107562769 | 107562859 | chr6 | 108181556 | 108181721 | chr6 | 108280292 | 108280352 |
| chr6 | 108435075 | 108435263 | chr6 | 108436072 | 108436526 | chr6 | 108438261 | 108438577 |
| chr6 | 108440091 | 108440644 | chr6 | 108440745 | 108440961 | chr6 | 108479290 | 108479665 |
| chr6 | 108484909 | 108485406 | chr6 | 108485665 | 108485905 | chr6 | 108486158 | 108486394 |
| chr6 | 108487724 | 108488416 | chr6 | 108489662 | 108489808 | chr6 | 108490067 | 108490245 |
| chr6 | 108490297 | 108490514 | chr6 | 108490538 | 108490633 | chr6 | 108490978 | 108491000 |
| chr6 | 108491108 | 108491423 | chr6 | 108492270 | 108492451 | chr6 | 108495681 | 108495817 |
| chr6 | 108495916 | 108495951 | chr6 | 108496208 | 108496649 | chr6 | 108497494 | 108497796 |
| chr6 | 108497827 | 108497881 | chr6 | 109057882 | 109057928 | chr6 | 109058799 | 109058861 |
| chr6 | 110437721 | 110437751 | chr6 | 110679123 | 110679414 | chr6 | 110797678 | 110797708 |
| chr6 | 110798007 | 110798036 | chr6 | 110848558 | 110848682 | chr6 | 113852508 | 113852634 |
| chr6 | 116783448 | 116783493 | chr6 | 117000853 | 117001032 | chr6 | 117086249 | 117086639 |
| chr6 | 117585967 | 117586004 | chr6 | 117586847 | 117587169 | chr6 | 117587480 | 117587527 |
| chr6 | 117591161 | 117591191 | chr6 | 117591411 | 117591596 | chr6 | 117591684 | 117591743 |
| chr6 | 118228102 | 118228151 | chr6 | 118228747 | 118228828 | chr6 | 118229154 | 118229383 |
| chr6 | 118229626 | 118229818 | chr6 | 118241228 | 118241308 | chr6 | 118241395 | 118241500 |
| chr6 | 119254629 | 119254678 | chr6 | 119483052 | 119483082 | chr6 | 121758672 | 121758994 |
| chr6 | 121797231 | 121797265 | chr6 | 123317073 | 123317589 | chr6 | 123317797 | 123317833 |
| chr6 | 124124432 | 124124465 | chr6 | 124124860 | 124125016 | chr6 | 126284131 | 125284175 |
| chr6 | 126068092 | 126068178 | chr6 | 127439379 | 127439453 | chr6 | 127439985 | 127440127 |
| chr6 | 127440331 | 127440962 | chr6 | 127441031 | 127441123 | chr6 | 127441554 | 127441762 |
| chr6 | 127442021 | 127442070 | chr6 | 127442090 | 127442104 | chr6 | 127840501 | 127840681 |
| chr6 | 129204459 | 129204524 | chr6 | 130686534 | 130687057 | chr6 | 131602584 | 131602694 |
| chr6 | 132722078 | 132722141 | chr6 | 132722158 | 132722196 | chr6 | 133561740 | 133562070 |
| chr6 | 133562374 | 133562436 | chr6 | 133562675 | 133562755 | chr6 | 133563327 | 133563918 |
| chr6 | 134067194 | 134067471 | chr6 | 134176232 | 134176299 | chr6 | 134176549 | 134176579 |
| chr6 | 134210528 | 134211018 | chr6 | 134211112 | 134211367 | chr6 | 134213944 | 134213987 |
| chr6 | 134214077 | 134214364 | chr6 | 134589500 | 134589767 | chr6 | 134638950 | 134639003 |
| chr6 | 137241928 | 137242205 | chr6 | 137243208 | 137243410 | chr6 | 137244114 | 137244148 |
| chr6 | 137244236 | 137244465 | chr6 | 137311168 | 137311380 | chr6 | 137366354 | 137366383 |
| chr6 | 137809141 | 137809365 | chr6 | 137809446 | 137809916 | chr6 | 137810033 | 137811088 |
| chr6 | 137813787 | 137813895 | chr6 | 137814604 | 137814618 | chr6 | 137814654 | 137814763 |
| chr6 | 137815008 | 137815170 | chr6 | 137815225 | 137815662 | chr6 | 137816472 | 137817351 |
| chr6 | 137818505 | 137818598 | chr6 | 137818619 | 137819368 | chr6 | 146755567 | 146755649 |
| chr6 | 149868348 | 149868387 | chr6 | 150183760 | 150183874 | chr6 | 150284552 | 150284581 |
| chr6 | 150285056 | 150285368 | chr6 | 150285545 | 150285885 | chr6 | 150286100 | 150286639 |
| chr6 | 150358970 | 150359192 | chr6 | 151561016 | 151561340 | chr6 | 151561369 | 151561857 |
| chr6 | 151562066 | 151562563 | chr6 | 151650396 | 151650453 | chr6 | 161815055 | 151815069 |
| chr6 | 152419908 | 152419940 | chr6 | 162623015 | 152623493 | chr6 | 152957895 | 152958076 |
| chr6 | 153461236 | 153451500 | chr6 | 163451890 | 153461968 | chr6 | 163452232 | 153452320 |
| chr6 | 153452713 | 153452746 | chr6 | 154360650 | 154360746 | chr6 | 154970558 | 154970676 |
| chr6 | 155316257 | 155316265 | chr6 | 155569208 | 155569305 | chr6 | 157037549 | 157037677 |
| chr6 | 157266063 | 157266109 | chr6 | 157502438 | 157502561 | chr6 | 157506082 | 157506112 |
| chr6 | 157556764 | 157557296 | chr6 | 157637455 | 157637500 | chr6 | 159211558 | 159211701 |
| chr6 | 159228187 | 159228217 | chr6 | 159290823 | 159290852 | chr6 | 159419589 | 159419717 |
| chr6 | 159590048 | 159590086 | chr6 | 159590155 | 159590761 | chr6 | 159590972 | 159590986 |
| chr6 | 159654923 | 159655003 | chr6 | 161100361 | 161100390 | chr6 | 161188513 | 161188543 |
| chr6 | 161352101 | 161352135 | chr6 | 161645992 | 161646255 | chr6 | 161780056 | 161780139 |
| chr6 | 163602842 | 163602872 | chr6 | 163834314 | 163834382 | chr6 | 163834406 | 163834532 |
| chr6 | 163834857 | 163834901 | chr6 | 163836568 | 163836900 | chr6 | 164114396 | 164114524 |
| chr6 | 164179636 | 164179668 | chr6 | 164183602 | 164183632 | chr6 | 164196971 | 164197003 |
| chr6 | 164215532 | 164215633 | chr6 | 164228294 | 164228363 | chr6 | 164246015 | 164246143 |
| chr6 | 164283254 | 164283377 | chr6 | 164314289 | 164314443 | chr6 | 164322666 | 164322775 |
| chr6 | 166074119 | 166074412 | chr6 | 166076788 | 166077021 | chr6 | 166077378 | 166077632 |
| chr6 | 166267582 | 166267891 | chr6 | 166401254 | 166401307 | chr6 | 166402240 | 166402546 |
| chr6 | 166421911 | 166422185 | chr6 | 166579723 | 166580144 | chr6 | 166580344 | 166582797 |
| chr6 | 166944367 | 166944403 | chr6 | 167202601 | 167202801 | chr6 | 167835129 | 167835171 |
| chr6 | 168719983 | 168720019 | chr6 | 168842847 | 168842944 | chr6 | 168858122 | 168858296 |
| chr6 | 168972472 | 168972502 | chr6 | 169002054 | 169002084 | chr6 | 169653638 | 169653668 |
| chr6 | 170047467 | 170047499 | chr6 | 170240639 | 170240714 | chr6 | 170264728 | 170264761 |
| chr6 | 170475105 | 170475267 | chr6 | 170494286 | 170494315 | chr6 | 170894820 | 170894912 |
| chr7 | 68930 | 68960 | chr7 | 329805 | 329838 | chr7 | 369494 | 369536 |
| chr7 | 369844 | 369980 | chr7 | 389663 | 389693 | chr7 | 409826 | 409892 |
| chr7 | 427454 | 427484 | chr7 | 431386 | 431492 | chr7 | 497782 | 497934 |
| chr7 | 503811 | 503936 | chr7 | 551599 | 551697 | chr7 | 556928 | 556983 |
| chr7 | 564237 | 564271 | chr7 | 578922 | 579020 | chr7 | 579827 | 579857 |
| chr7 | 752120 | 752221 | chr7 | 842331 | 842414 | chr7 | 907656 | 902709 |
| chr7 | 915058 | 915087 | chr7 | 922050 | 922235 | chr7 | 927933 | 927986 |
| chr7 | 1016343 | 1016373 | chr7 | 1022224 | 1022254 | chr7 | 1030172 | 1030283 |
| chr7 | 1054579 | 1054696 | chr7 | 1086199 | 1086319 | chr7 | 1195270 | 1195364 |
| chr7 | 1263761 | 1263960 | chr7 | 1268318 | 1268366 | chr7 | 1269305 | 1269463 |
| chr7 | 1269553 | 1269808 | chr7 | 1270406 | 1270440 | chr7 | 1273167 | 1273330 |

TABLE 12-continued

| chr | start | end | chr | start | end | chr | start | end |
|---|---|---|---|---|---|---|---|---|
| chr7 | 1274641 | 1274677 | chr7 | 1275579 | 1275680 | chr7 | 1277817 | 1277865 |
| chr7 | 1279099 | 1279129 | chr7 | 1279965 | 1279995 | chr7 | 1281131 | 1281232 |
| chr7 | 1281493 | 1281555 | chr7 | 1282042 | 1282150 | chr7 | 1282506 | 1282644 |
| chr7 | 1288582 | 1288753 | chr7 | 1308351 | 1308497 | chr7 | 1325810 | 1325882 |
| chr7 | 1416020 | 1416131 | chr7 | 1423632 | 1423677 | chr7 | 1459041 | 1459191 |
| chr7 | 1503417 | 1503596 | chr7 | 1547311 | 1547394 | chr7 | 1598639 | 1598697 |
| chr7 | 1607386 | 1607465 | chr7 | 1607971 | 1608001 | chr7 | 1611443 | 1611522 |
| chr7 | 1615390 | 1615444 | chr7 | 1627404 | 1627434 | chr7 | 1641774 | 1641923 |
| chr7 | 1681189 | 1681239 | chr7 | 1688977 | 1689146 | chr7 | 1690745 | 1690851 |
| chr7 | 1709138 | 1709235 | chr7 | 1709474 | 1709561 | chr7 | 1733166 | 1733378 |
| chr7 | 1735223 | 1735354 | chr7 | 1748514 | 1748766 | chr7 | 1775831 | 1775861 |
| chr7 | 1778875 | 1778914 | chr7 | 1783551 | 1783623 | chr7 | 1786514 | 1786899 |
| chr7 | 1787166 | 1787324 | chr7 | 1800882 | 1800912 | chr7 | 1970842 | 1970872 |
| chr7 | 2109874 | 2109904 | chr7 | 2163332 | 2163467 | chr7 | 2208670 | 2208808 |
| chr7 | 2232963 | 2233056 | chr7 | 2233292 | 2233414 | chr7 | 2238118 | 2238235 |
| chr7 | 2300787 | 2300899 | chr7 | 2361190 | 2361434 | chr7 | 2473452 | 2473605 |
| chr7 | 2565919 | 2566041 | chr7 | 2566600 | 2566630 | chr7 | 2595825 | 2595943 |
| chr7 | 2659340 | 2659370 | chr7 | 2720013 | 2720140 | chr7 | 2728068 | 2728165 |
| chr7 | 2979480 | 2979512 | chr7 | 2985518 | 2985547 | chr7 | 3033658 | 3033688 |
| chr7 | 3083331 | 3083352 | chr7 | 3283704 | 3283894 | chr7 | 3340444 | 3340473 |
| chr7 | 3341570 | 3341597 | chr7 | 4215324 | 4215384 | chr7 | 4657806 | 4657857 |
| chr7 | 4856984 | 4857048 | chr7 | 4922550 | 4922706 | chr7 | 4923328 | 4923397 |
| chr7 | 4998201 | 4998388 | chr7 | 5111528 | 5111669 | chr7 | 5262433 | 5262562 |
| chr7 | 5397777 | 5397938 | chr7 | 5603717 | 5603947 | chr7 | 5632939 | 5633100 |
| chr7 | 5648107 | 5648393 | chr7 | 6045612 | 6045641 | chr7 | 6059024 | 6059182 |
| chr7 | 6060590 | 6060634 | chr7 | 6099217 | 6099334 | chr7 | 6124585 | 6124714 |
| chr7 | 6188610 | 6189061 | chr7 | 6307943 | 6308066 | chr7 | 6414386 | 6414415 |
| chr7 | 6426878 | 6426907 | chr7 | 6443279 | 6443376 | chr7 | 6443826 | 6443856 |
| chr7 | 6484445 | 6484545 | chr7 | 6524573 | 6524744 | chr7 | 6524977 | 6525012 |
| chr7 | 6525477 | 6525606 | chr7 | 6543150 | 6543216 | chr7 | 6560235 | 6560345 |
| chr7 | 6566413 | 6566663 | chr7 | 6570959 | 6571130 | chr7 | 6576137 | 6576367 |
| chr7 | 6703555 | 6703869 | chr7 | 6703916 | 6703959 | chr7 | 701498 | 7015673 |
| chr7 | 7605441 | 7605822 | chr7 | 8343630 | 8343724 | chr7 | 8391475 | 8391573 |
| chr7 | 8473070 | 8473455 | chr7 | 8473480 | 8473674 | chr7 | 8473956 | 8474241 |
| chr7 | 8474516 | 8474562 | chr7 | 8474814 | 8475057 | chr7 | 8480640 | 8481159 |
| chr7 | 8481642 | 8481833 | chr7 | 8482056 | 8482297 | chr7 | 8482670 | 8482824 |
| chr7 | 8482885 | 8482921 | chr7 | 8483147 | 8483950 | chr7 | 12151440 | 12151472 |
| chr7 | 12151524 | 12151678 | chr7 | 12443317 | 12443403 | chr7 | 12443841 | 12443871 |
| chr7 | 12610339 | 12610476 | chr7 | 12751410 | 12751496 | chr7 | 12776779 | 12776811 |
| chr7 | 15725983 | 15726081 | chr7 | 15726634 | 15727077 | chr7 | 15727290 | 15727320 |
| chr7 | 19145808 | 19145893 | chr7 | 19146032 | 19146184 | chr7 | 19146238 | 19146249 |
| chr7 | 19146502 | 19146558 | chr7 | 19147122 | 19147798 | chr7 | 19152224 | 19152349 |
| chr7 | 19155791 | 19155820 | chr7 | 19156126 | 19156132 | chr7 | 19156304 | 19156745 |
| chr7 | 19157144 | 19157566 | chr7 | 19157634 | 19158015 | chr7 | 19158632 | 19158735 |
| chr7 | 19184058 | 19184255 | chr7 | 19813284 | 19813313 | chr7 | 20089670 | 20089700 |
| chr7 | 20183238 | 20183283 | chr7 | 20816252 | 20816447 | chr7 | 20817380 | 20817410 |
| chr7 | 20818130 | 20818362 | chr7 | 20823292 | 20823330 | chr7 | 20823383 | 20823432 |
| chr7 | 20823920 | 20824143 | chr7 | 20824476 | 20824819 | chr7 | 20824836 | 20824946 |
| chr7 | 20825379 | 20825559 | chr7 | 20826113 | 20826202 | chr7 | 20826884 | 20827199 |
| chr7 | 20830670 | 20830700 | chr7 | 20833167 | 20833322 | chr7 | 21403615 | 21403645 |
| chr7 | 21582593 | 21682640 | chr7 | 21582792 | 21582868 | chr7 | 21583263 | 21583277 |
| chr7 | 21583304 | 21583326 | chr7 | 22539833 | 22539909 | chr7 | 22589355 | 22589870 |
| chr7 | 22824965 | 22825009 | chr7 | 23253573 | 23253671 | chr7 | 23287253 | 23287350 |
| chr7 | 23287533 | 23287624 | chr7 | 23526549 | 23526698 | chr7 | 23578703 | 23578857 |
| chr7 | 24323763 | 24323939 | chr7 | 24580644 | 24580806 | chr7 | 24796478 | 24796567 |
| chr7 | 25132558 | 25132726 | chr7 | 25133492 | 25133650 | chr7 | 25165921 | 25166061 |
| chr7 | 25896521 | 25896864 | chr7 | 25897133 | 25897246 | chr7 | 26194906 | 26195024 |
| chr7 | 26283775 | 26283954 | chr7 | 27127863 | 27127898 | chr7 | 27135327 | 27135770 |
| chr7 | 27136013 | 27136790 | chr7 | 27138381 | 27138410 | chr7 | 27184015 | 27184190 |
| chr7 | 22190591 | 27191226 | chr7 | 27192061 | 27192098 | chr7 | 27195462 | 27195601 |
| chr7 | 27195867 | 27195892 | chr7 | 27196153 | 27196839 | chr7 | 27204487 | 27204769 |
| chr7 | 27205266 | 27205395 | chr7 | 27205678 | 27205789 | chr7 | 27208187 | 27208285 |
| chr7 | 27209462 | 27209582 | chr7 | 27212499 | 27212899 | chr7 | 22213189 | 27214261 |
| chr7 | 27217042 | 27217071 | chr7 | 27223114 | 27223151 | chr7 | 27223601 | 27223696 |
| chr7 | 27224069 | 27224609 | chr7 | 27225035 | 27225057 | chr7 | 27225447 | 27225483 |
| chr7 | 27227874 | 27227953 | chr7 | 27231476 | 27231505 | chr7 | 27231818 | 27231894 |
| chr7 | 27232289 | 27232962 | chr7 | 27233410 | 27233454 | chr7 | 27238887 | 27238917 |
| chr7 | 27239226 | 27239234 | chr7 | 27240230 | 27240381 | chr7 | 27244515 | 27244610 |
| chr7 | 27244798 | 27245310 | chr7 | 27245668 | 27245795 | chr7 | 27252380 | 27252410 |
| chr7 | 27260092 | 27260100 | chr7 | 27264875 | 27265325 | chr7 | 27265538 | 27265584 |
| chr7 | 27275513 | 27275543 | chr7 | 27279238 | 27279368 | chr7 | 27281329 | 27281360 |
| chr7 | 27282089 | 27283013 | chr7 | 27283351 | 27283627 | chr7 | 27285621 | 27285913 |
| chr7 | 27285980 | 27286098 | chr7 | 27286171 | 27286248 | chr7 | 27288946 | 27289100 |
| chr7 | 27289170 | 27289449 | chr7 | 27291315 | 27291851 | chr7 | 28110701 | 28110828 |
| chr7 | 28238339 | 28238444 | chr7 | 28449276 | 28449290 | chr7 | 28449659 | 28449781 |
| chr7 | 28449858 | 28450015 | chr7 | 28989065 | 28989159 | chr7 | 28995657 | 28995978 |
| chr7 | 28996457 | 28996495 | chr7 | 28996840 | 28996916 | chr7 | 28997135 | 28997625 |
| chr7 | 28998053 | 28998119 | chr7 | 30029702 | 30029822 | chr7 | 30029923 | 30029952 |

TABLE 12-continued

| chr | start | end | chr | start | end | chr | start | end |
|---|---|---|---|---|---|---|---|---|
| chr7 | 30030307 | 30030337 | chr7 | 30721280 | 30721902 | chr7 | 30722290 | 30722375 |
| chr7 | 30857157 | 30857292 | chr7 | 31093003 | 31093133 | chr7 | 31232909 | 31232939 |
| chr7 | 31375965 | 31376135 | chr7 | 32110704 | 32110772 | chr7 | 32337807 | 32337837 |
| chr7 | 32338088 | 32338217 | chr7 | 32338284 | 32338410 | chr7 | 32338900 | 32338930 |
| chr7 | 32467461 | 32467655 | chr7 | 32467947 | 32468062 | chr7 | 32997124 | 32997454 |
| chr7 | 33167928 | 33168030 | chr7 | 33725803 | 33725938 | chr7 | 33943459 | 33943759 |
| chr7 | 35225809 | 35225833 | chr7 | 35226193 | 35226522 | chr7 | 35226557 | 35226765 |
| chr7 | 35292970 | 35293086 | chr7 | 35293183 | 35293293 | chr7 | 35294032 | 35294141 |
| chr7 | 35294502 | 35294536 | chr7 | 35295104 | 35295105 | chr7 | 35295908 | 35295944 |
| chr7 | 35296935 | 35297004 | chr7 | 35297138 | 35297353 | chr7 | 35297471 | 35298016 |
| chr7 | 35300951 | 35301008 | chr7 | 35301102 | 35301948 | chr7 | 32352957 | 37353062 |
| chr7 | 37487164 | 37487453 | chr7 | 37487756 | 37487826 | chr7 | 37488257 | 37488578 |
| chr7 | 37488920 | 37488992 | chr7 | 37907440 | 37907470 | chr7 | 37955878 | 37955979 |
| chr7 | 37956271 | 37956439 | chr7 | 37960301 | 37960335 | chr7 | 38588471 | 38588501 |
| chr7 | 38670357 | 38670663 | chr7 | 38670957 | 38671015 | chr7 | 39015542 | 39015981 |
| chr7 | 39649223 | 39649253 | chr7 | 39649444 | 39649457 | chr7 | 39872836 | 39873015 |
| chr7 | 41739663 | 41739879 | chr7 | 41982690 | 41982874 | chr7 | 42267647 | 42267677 |
| chr7 | 42276346 | 42276634 | chr7 | 42377468 | 42377497 | chr7 | 42533257 | 42533296 |
| chr7 | 43152109 | 43152207 | chr7 | 43152414 | 43152700 | chr7 | 43152957 | 43153199 |
| chr7 | 43153230 | 43163237 | chr7 | 43817999 | 43818119 | chr7 | 44083283 | 44083416 |
| chr7 | 44097690 | 44097876 | chr7 | 44151398 | 44151428 | chr7 | 44151795 | 44151933 |
| chr7 | 44163926 | 44163989 | chr7 | 44364838 | 44364903 | chr7 | 44740467 | 44740672 |
| chr7 | 44835037 | 44835384 | chr7 | 44912004 | 44912034 | chr7 | 45026942 | 45027045 |
| chr7 | 45038532 | 45038655 | chr7 | 45046874 | 45046982 | chr7 | 45525402 | 45525432 |
| chr7 | 45613785 | 45613813 | chr7 | 45613858 | 45613898 | chr7 | 45614341 | 45614474 |
| chr7 | 45614738 | 45614809 | chr7 | 45614929 | 45615020 | chr7 | 45615440 | 45615495 |
| chr7 | 45960743 | 45960794 | chr7 | 45961146 | 45961176 | chr7 | 45961508 | 45961576 |
| chr7 | 45961833 | 45961888 | chr7 | 47515359 | 47515405 | chr7 | 47704289 | 47704359 |
| chr7 | 49654508 | 49654538 | chr7 | 49812820 | 49813017 | chr7 | 49813810 | 49813994 |
| chr7 | 49814531 | 49814750 | chr7 | 49815117 | 49815249 | chr7 | 49815657 | 49815765 |
| chr7 | 49819674 | 49819703 | chr7 | 50294451 | 50294481 | chr7 | 50343263 | 50343401 |
| chr7 | 50343975 | 50343994 | chr7 | 50344226 | 50344491 | chr7 | 50365076 | 50365137 |
| chr7 | 50438618 | 50438648 | chr7 | 50441145 | 50441285 | chr7 | 50560588 | 50560637 |
| chr7 | 50860226 | 50861102 | chr7 | 51383754 | 51383790 | chr7 | 51384327 | 51384440 |
| chr7 | 51384915 | 51384951 | chr7 | 52156231 | 52156261 | chr7 | 54609852 | 54609951 |
| chr7 | 54609992 | 54610153 | chr7 | 54612418 | 54612730 | chr7 | 55086473 | 55086601 |
| chr7 | 55086983 | 55087533 | chr7 | 55209976 | 55210005 | chr7 | 55211065 | 55211094 |
| chr7 | 55221729 | 55221836 | chr7 | 55223589 | 55223636 | chr7 | 55227993 | 55228022 |
| chr7 | 55233028 | 55233123 | chr7 | 55241663 | 55241737 | chr7 | 56242419 | 55242493 |
| chr7 | 55248975 | 55249085 | chr7 | 55259404 | 55259547 | chr7 | 55260469 | 55260498 |
| chr7 | 55268867 | 55268896 | chr7 | 55410019 | 55410126 | chr7 | 55506288 | 55506348 |
| chr7 | 56018123 | 56018286 | chr7 | 56031716 | 56031869 | chr7 | 63667431 | 63667460 |
| chr7 | 64330411 | 64330470 | chr7 | 64330734 | 64330833 | chr7 | 64349042 | 64349056 |
| chr7 | 64349331 | 64349470 | chr7 | 64700283 | 64700329 | chr7 | 64712364 | 64712510 |
| chr7 | 64713317 | 64713449 | chr7 | 64974382 | 64974422 | chr7 | 65037609 | 65037734 |
| chr7 | 65508995 | 65509043 | chr7 | 65510006 | 65510096 | chr7 | 65878743 | 65878793 |
| chr7 | 65879649 | 65879883 | chr7 | 65880359 | 65880405 | chr7 | 66204493 | 66204617 |
| chr7 | 66206923 | 65206953 | chr7 | 66214923 | 66214961 | chr7 | 67579765 | 67579911 |
| chr7 | 68204793 | 68204948 | chr7 | 69062519 | 69062635 | chr7 | 69064590 | 69064771 |
| chr7 | 69064834 | 69065045 | chr7 | 69352121 | 69352272 | chr7 | 69897780 | 69897827 |
| chr7 | 70596454 | 70596688 | chr7 | 70597406 | 70597451 | chr7 | 70597835 | 70597871 |
| chr7 | 70597991 | 70598123 | chr7 | 70598170 | 70598387 | chr7 | 70990312 | 70990342 |
| chr7 | 71217108 | 71217332 | chr7 | 71438424 | 71438454 | chr7 | 71603924 | 71604082 |
| chr7 | 71800676 | 71800756 | chr7 | 71800934 | 71801104 | chr7 | 71802410 | 71802522 |
| chr7 | 71802578 | 71802637 | chr7 | 71871203 | 71871245 | chr7 | 75511201 | 75511298 |
| chr7 | 76033151 | 76033289 | chr7 | 77129743 | 77129907 | chr7 | 77308664 | 77308899 |
| chr7 | 77309437 | 77309511 | chr7 | 77324362 | 77324593 | chr7 | 79081792 | 79081821 |
| chr7 | 79082023 | 79082218 | chr7 | 79083392 | 79083834 | chr7 | 80548257 | 80548403 |
| chr7 | 82072350 | 82072503 | chr7 | 82073495 | 82073533 | chr7 | 84815141 | 84815226 |
| chr7 | 84815744 | 84815954 | chr7 | 86273208 | 86273541 | chr7 | 86274258 | 86274457 |
| chr7 | 87104816 | 87105430 | chr7 | 87229537 | 87230433 | chr7 | 87257012 | 87257047 |
| chr7 | 87257931 | 87258054 | chr7 | 87563370 | 87563614 | chr7 | 87563829 | 87563890 |
| chr7 | 87706818 | 87706877 | chr7 | 87825006 | 87825137 | chr7 | 88387982 | 88388167 |
| chr7 | 88388540 | 88388660 | chr7 | 88388879 | 88388901 | chr7 | 88389047 | 88389356 |
| chr7 | 89747996 | 89748340 | chr7 | 89950183 | 89950810 | chr7 | 90226259 | 90226464 |
| chr7 | 90269263 | 90269563 | chr7 | 90797539 | 90797568 | chr7 | 90895012 | 90895097 |
| chr7 | 92466152 | 92466400 | chr7 | 92554253 | 92554452 | chr7 | 92689705 | 92689818 |
| chr7 | 93203708 | 93203756 | chr7 | 93204332 | 93204492 | chr7 | 93220696 | 93220826 |
| chr7 | 93519351 | 93519765 | chr7 | 93519899 | 93520137 | chr7 | 93551323 | 93551425 |
| chr7 | 94138158 | 94138315 | chr7 | 94284302 | 94284873 | chr7 | 96619560 | 96619603 |
| chr7 | 96621715 | 96621811 | chr7 | 96622107 | 96622349 | chr7 | 96622694 | 96622723 |
| chr7 | 96625537 | 96625720 | chr7 | 96625998 | 96626051 | chr7 | 96627013 | 96627048 |
| chr7 | 96631579 | 96631680 | chr7 | 96634645 | 96634928 | chr7 | 96635345 | 96635451 |
| chr7 | 96535733 | 96635971 | chr7 | 96636034 | 96636645 | chr7 | 96639318 | 96639348 |
| chr7 | 96646662 | 96647131 | chr7 | 96647809 | 96648219 | chr7 | 96649955 | 96650094 |
| chr7 | 96650884 | 96651076 | chr7 | 96651137 | 96651151 | chr7 | 96651469 | 96651537 |
| chr7 | 96652144 | 96652174 | chr7 | 96653507 | 96653819 | chr7 | 96653863 | 96653993 |
| chr7 | 97361098 | 97361422 | chr7 | 97361521 | 97361781 | chr7 | 97362292 | 97362607 |

TABLE 12-continued

| chr | start | end | chr | start | end | chr | start | end |
|---|---|---|---|---|---|---|---|---|
| chr7 | 97490474 | 97490508 | chr7 | 97580497 | 97580648 | chr7 | 97600104 | 97600224 |
| chr7 | 97839654 | 97839684 | chr7 | 97869290 | 97869391 | chr7 | 97869614 | 97869644 |
| chr7 | 98197206 | 98197242 | chr7 | 98245885 | 98246078 | chr7 | 98246305 | 98246507 |
| chr7 | 98246534 | 98246868 | chr7 | 98247126 | 98247656 | chr7 | 98966786 | 98966916 |
| chr7 | 98969875 | 98969928 | chr7 | 98971509 | 98971549 | chr7 | 99035152 | 99035191 |
| chr7 | 99104258 | 99104388 | chr7 | 99177742 | 99177870 | chr7 | 99591579 | 99591762 |
| chr7 | 99596194 | 99595335 | chr7 | 99642049 | 99642100 | chr7 | 99751578 | 99751630 |
| chr7 | 99775192 | 99775558 | chr7 | 99934913 | 99934943 | chr7 | 100088183 | 100088312 |
| chr7 | 100179889 | 100179927 | chr7 | 100241592 | 100241697 | chr7 | 100295321 | 100295424 |
| chr7 | 100318505 | 100318575 | chr7 | 100320690 | 100320719 | chr7 | 100547037 | 100547073 |
| chr7 | 100609750 | 100609780 | chr7 | 100808466 | 100808502 | chr7 | 100809436 | 100809521 |
| chr7 | 100823436 | 100823497 | chr7 | 101005968 | 101005998 | chr7 | 101241993 | 101242023 |
| chr7 | 101475790 | 101475858 | chr7 | 101558399 | 101558698 | chr7 | 101585887 | 101585917 |
| chr7 | 101627741 | 101627787 | chr7 | 101707502 | 101707532 | chr7 | 102091406 | 102091534 |
| chr7 | 102801710 | 102801804 | chr7 | 103085876 | 103086074 | chr7 | 103629059 | 103629794 |
| chr7 | 103630054 | 103630082 | chr7 | 103630475 | 103630824 | chr7 | 103969217 | 103969341 |
| chr7 | 103969694 | 103969794 | chr7 | 105279467 | 105279671 | chr7 | 106622834 | 106622961 |
| chr7 | 106685282 | 106685345 | chr7 | 106797774 | 106797804 | chr7 | 107301494 | 107301640 |
| chr7 | 107483694 | 107483918 | chr7 | 108095329 | 108095362 | chr7 | 108095781 | 108096055 |
| chr7 | 108097172 | 108097491 | chr7 | 111202993 | 111203260 | chr7 | 112726558 | 112726614 |
| chr7 | 113722810 | 113723283 | chr7 | 113723339 | 113723439 | chr7 | 113724956 | 113725081 |
| chr7 | 113726509 | 113726539 | chr7 | 113727442 | 113727486 | chr7 | 113727754 | 113727781 |
| chr7 | 115117552 | 115117647 | chr7 | 116140252 | 116140356 | chr7 | 116412008 | 116412058 |
| chr7 | 116415100 | 116415129 | chr7 | 116417443 | 116417496 | chr7 | 116422067 | 116422132 |
| chr7 | 116423399 | 116423488 | chr7 | 116962893 | 116963146 | chr7 | 116963331 | 116963476 |
| chr7 | 117119381 | 117120271 | chr7 | 117513675 | 117513849 | chr7 | 119913561 | 119913785 |
| chr7 | 120969672 | 120969800 | chr7 | 121513523 | 121513709 | chr7 | 121939672 | 121940244 |
| chr7 | 121940434 | 121940448 | chr7 | 121940935 | 121941052 | chr7 | 121941881 | 121942170 |
| chr7 | 121945822 | 121945920 | chr7 | 121946478 | 121946982 | chr7 | 121947098 | 121947406 |
| chr7 | 121950132 | 121950264 | chr7 | 121950429 | 121950552 | chr7 | 121950995 | 121951069 |
| chr7 | 121951877 | 121952010 | chr7 | 121952044 | 121952169 | chr7 | 121956486 | 121956567 |
| chr7 | 121956955 | 121957076 | chr7 | 121957254 | 121957331 | chr7 | 122526833 | 122526873 |
| chr7 | 123173150 | 123173244 | chr7 | 123175689 | 123175899 | chr7 | 123672048 | 123672086 |
| chr7 | 124404415 | 124404497 | chr7 | 125082621 | 125082698 | chr7 | 126891220 | 126891250 |
| chr7 | 126891504 | 126891593 | chr7 | 126894076 | 126894197 | chr7 | 127371129 | 127371249 |
| chr7 | 127615921 | 127615951 | chr7 | 127744122 | 127744631 | chr7 | 127806634 | 127806664 |
| chr7 | 127807817 | 127807846 | chr7 | 127808047 | 127808792 | chr7 | 127841626 | 127841704 |
| chr7 | 127991826 | 127991922 | chr7 | 127992045 | 127992135 | chr7 | 128097059 | 128097089 |
| chr7 | 128337467 | 128337594 | chr7 | 128337788 | 128337921 | chr7 | 128470897 | 128471032 |
| chr7 | 128486036 | 128486138 | chr7 | 128528749 | 128528779 | chr7 | 128529023 | 128529053 |
| chr7 | 128828195 | 128828272 | chr7 | 129229456 | 129229631 | chr7 | 129418057 | 129418428 |
| chr7 | 129422160 | 129422968 | chr7 | 129423126 | 129423418 | chr7 | 129423834 | 129424034 |
| chr7 | 129424655 | 129425887 | chr7 | 129426195 | 129426236 | chr7 | 129483356 | 129483449 |
| chr7 | 129794593 | 129794721 | chr7 | 129800243 | 129800404 | chr7 | 129844226 | 129844493 |
| chr7 | 131041515 | 131041596 | chr7 | 131242738 | 131242824 | chr7 | 131514824 | 131514854 |
| chr7 | 132261272 | 132261432 | chr7 | 134143164 | 134143475 | chr7 | 134143807 | 134144132 |
| chr7 | 134918503 | 134918637 | chr7 | 136553311 | 136554025 | chr7 | 136554104 | 136554366 |
| chr7 | 136554638 | 136554966 | chr7 | 136555235 | 136555412 | chr7 | 136555681 | 136555841 |
| chr7 | 136556013 | 136556091 | chr7 | 136969053 | 136969083 | chr7 | 137028481 | 137028524 |
| chr7 | 137531158 | 137531211 | chr7 | 137531263 | 137531888 | chr7 | 137531909 | 137532187 |
| chr7 | 138042221 | 138042288 | chr7 | 138720785 | 138720909 | chr7 | 139167617 | 139167744 |
| chr7 | 139168115 | 139168379 | chr7 | 139208772 | 139208929 | chr7 | 139878250 | 139878296 |
| chr7 | 139930051 | 139930270 | chr7 | 139939160 | 139939318 | chr7 | 140027008 | 140027079 |
| chr7 | 140096812 | 140096882 | chr7 | 140097126 | 140097196 | chr7 | 140180094 | 140180444 |
| chr7 | 140218053 | 140218082 | chr7 | 140218123 | 140218352 | chr7 | 140219405 | 140219435 |
| chr7 | 140339952 | 140339982 | chr7 | 140453121 | 140453167 | chr7 | 140477779 | 140477868 |
| chr7 | 140481381 | 140481431 | chr7 | 140772795 | 140773228 | chr7 | 140773563 | 140773750 |
| chr7 | 142785612 | 142785728 | chr7 | 143042634 | 143042798 | chr7 | 143579739 | 143580069 |
| chr7 | 144712934 | 144713064 | chr7 | 145812992 | 145813082 | chr7 | 145813412 | 145813494 |
| chr7 | 145813946 | 145814166 | chr7 | 148224541 | 148224686 | chr7 | 148508712 | 148508741 |
| chr7 | 148640171 | 148640250 | chr7 | 148846138 | 148846250 | chr7 | 148846434 | 148846644 |
| chr7 | 148851143 | 148851234 | chr7 | 148883821 | 148883973 | chr7 | 149109648 | 149109785 |
| chr7 | 149112058 | 149112248 | chr7 | 149119948 | 149120073 | chr7 | 149411541 | 149411727 |
| chr7 | 149411835 | 149412304 | chr7 | 149570368 | 149570406 | chr7 | 149744505 | 149744560 |
| chr7 | 149917322 | 149917336 | chr7 | 149918119 | 149918149 | chr7 | 150038883 | 150038912 |
| chr7 | 150049604 | 150049718 | chr7 | 150069098 | 150069346 | chr7 | 150069679 | 150069820 |
| chr7 | 150070021 | 150070058 | chr7 | 150081236 | 150081308 | chr7 | 150716169 | 150716305 |
| chr7 | 150748192 | 150748406 | chr7 | 150753942 | 150753981 | chr7 | 150870816 | 150870889 |
| chr7 | 151001356 | 151001435 | chr7 | 151106451 | 151106565 | chr7 | 151106590 | 151106988 |
| chr7 | 151107485 | 151107651 | chr7 | 151188034 | 151188063 | chr7 | 151298870 | 151299029 |
| chr7 | 151423571 | 151423639 | chr7 | 151591667 | 151691705 | chr7 | 162133406 | 152133436 |
| chr7 | 152622621 | 152622697 | chr7 | 152913656 | 152913826 | chr7 | 153583632 | 153584069 |
| chr7 | 153584389 | 153584623 | chr7 | 153584848 | 153585206 | chr7 | 153585602 | 153585606 |
| chr7 | 153633796 | 153633942 | chr7 | 153749720 | 153750042 | chr7 | 154561150 | 154561189 |
| chr7 | 154708275 | 154708338 | chr7 | 154862046 | 154862266 | chr7 | 154926351 | 154926397 |
| chr7 | 155164454 | 155165562 | chr7 | 155165875 | 155166784 | chr7 | 155167034 | 155167089 |
| chr7 | 155167175 | 155167660 | chr7 | 155167834 | 155167909 | chr7 | 155174656 | 155174788 |
| chr7 | 155241318 | 155242049 | chr7 | 155242729 | 155243102 | chr7 | 155243346 | 155243533 |

TABLE 12-continued

| chr | start | end | chr | start | end | chr | start | end |
|---|---|---|---|---|---|---|---|---|
| chr7 | 155243825 | 155243895 | chr7 | 155244180 | 155244361 | chr7 | 155246886 | 155247479 |
| chr7 | 155248913 | 155248943 | chr7 | 155249512 | 155249565 | chr7 | 155249925 | 155250011 |
| chr7 | 155250283 | 155250303 | chr7 | 155250324 | 155250355 | chr7 | 155250787 | 155250996 |
| chr7 | 155251701 | 155251854 | chr7 | 155251891 | 155251939 | chr7 | 155252247 | 155252261 |
| chr7 | 155252317 | 155252490 | chr7 | 155252862 | 155253041 | chr7 | 155254848 | 155255324 |
| chr7 | 155256269 | 155256312 | chr7 | 155257040 | 155257189 | chr7 | 155258193 | 155258487 |
| chr7 | 155258949 | 155259077 | chr7 | 155259120 | 155259622 | chr7 | 155259834 | 155259957 |
| chr7 | 155260039 | 155260137 | chr7 | 155260880 | 155260890 | chr7 | 155261071 | 155261210 |
| chr7 | 155301838 | 155301931 | chr7 | 155302328 | 155302895 | chr7 | 155302964 | 155303335 |
| chr7 | 155325796 | 155325872 | chr7 | 155326169 | 155326527 | chr7 | 155363304 | 155363417 |
| chr7 | 155580182 | 155580211 | chr7 | 155580846 | 155580876 | chr7 | 155581330 | 155581553 |
| chr7 | 155581765 | 155581980 | chr7 | 155582277 | 155582340 | chr7 | 155600629 | 155600723 |
| chr7 | 155602751 | 155602805 | chr7 | 155877196 | 155877283 | chr7 | 156259192 | 156259221 |
| chr7 | 156409144 | 156409347 | chr7 | 156409728 | 156409802 | chr7 | 156701846 | 156701908 |
| chr7 | 156707963 | 156708093 | chr7 | 156744619 | 156744713 | chr7 | 156779336 | 156779366 |
| chr7 | 156794153 | 156794235 | chr7 | 156794443 | 156794485 | chr7 | 156794998 | 156795354 |
| chr7 | 156795402 | 156795635 | chr7 | 156795900 | 156795914 | chr7 | 156796534 | 156796739 |
| chr7 | 156797006 | 156798434 | chr7 | 156798527 | 156799146 | chr7 | 156799291 | 156799467 |
| chr7 | 156800999 | 156801029 | chr7 | 156801403 | 156801601 | chr7 | 156808858 | 156809199 |
| chr7 | 156809983 | 156810521 | chr7 | 156810598 | 156810800 | chr7 | 156811303 | 156811436 |
| chr7 | 156812852 | 156813825 | chr7 | 156813987 | 156814707 | chr7 | 156814784 | 156815092 |
| chr7 | 156832223 | 156832402 | chr7 | 156832848 | 156833162 | chr7 | 156871283 | 156871297 |
| chr7 | 156880531 | 156880561 | chr7 | 157085373 | 157085487 | chr7 | 157085963 | 157086082 |
| chr7 | 157262815 | 157263018 | chr7 | 157263294 | 157263471 | chr7 | 157335172 | 157335202 |
| chr7 | 157361605 | 157361635 | chr7 | 157476879 | 157476973 | chr7 | 157476995 | 157477272 |
| chr7 | 157477473 | 157477488 | chr7 | 1574777 | 157477819 | chr7 | 157481130 | 157481160 |
| chr7 | 157481534 | 157481549 | chr7 | 157481969 | 157482073 | chr7 | 157482492 | 157482667 |
| chr7 | 157483320 | 157483538 | chr7 | 157484877 | 157485277 | chr7 | 157485527 | 157485501 |
| chr7 | 157485650 | 157485705 | chr7 | 157485976 | 157486081 | chr7 | 157486205 | 157486414 |
| chr7 | 157486476 | 157486503 | chr7 | 157584178 | 157584208 | chr7 | 157588586 | 157588791 |
| chr7 | 157606706 | 157606736 | chr7 | 157690056 | 157690086 | chr7 | 158059762 | 158059794 |
| chr7 | 158065832 | 158065970 | chr7 | 158198597 | 158198648 | chr7 | 158298861 | 158299036 |
| chr7 | 158673836 | 158673942 | chr7 | 158741193 | 158741267 | chr7 | 158799762 | 158799791 |
| chr7 | 158936492 | 158936880 | chr7 | 158937203 | 158937374 | chr7 | 158937577 | 158937624 |
| chr7 | 158938210 | 158938399 | chr8 | 686870 | 686884 | chr8 | 687163 | 687217 |
| chr8 | 687838 | 687975 | chr8 | 1085573 | 1085603 | chr8 | 1325465 | 1325606 |
| chr8 | 1444165 | 1444205 | chr8 | 1950097 | 1950134 | chr8 | 4849141 | 4849177 |
| chr8 | 4849466 | 4849500 | chr8 | 4850247 | 4850322 | chr8 | 4850419 | 4850516 |
| chr8 | 4851736 | 4851749 | chr8 | 4852021 | 4852118 | chr8 | 8640024 | 8640100 |
| chr8 | 8681258 | 8681353 | chr8 | 8748422 | 8748713 | chr8 | 8748919 | 8748956 |
| chr8 | 9722850 | 9722896 | chr8 | 9756051 | 9756283 | chr8 | 9760735 | 9761155 |
| chr8 | 9762586 | 9762689 | chr8 | 9762752 | 9762864 | chr8 | 9763143 | 9763275 |
| chr8 | 9763895 | 9764049 | chr8 | 9764196 | 9764214 | chr8 | 9764434 | 9764551 |
| chr8 | 10587589 | 10587602 | chr8 | 10652917 | 10653017 | chr8 | 10980452 | 10980589 |
| chr8 | 11204479 | 11204509 | chr8 | 11204810 | 11204905 | chr8 | 11536827 | 11536857 |
| chr8 | 11537225 | 11537259 | chr8 | 11554885 | 11554915 | chr8 | 11555152 | 11555166 |
| chr8 | 11555474 | 11555521 | chr8 | 11559759 | 11559794 | chr8 | 11560068 | 11560375 |
| chr8 | 11560711 | 11560793 | chr8 | 11561442 | 11562169 | chr8 | 11562422 | 11562485 |
| chr8 | 11562701 | 11562917 | chr8 | 11700190 | 11700284 | chr8 | 11705960 | 11706136 |
| chr8 | 11706580 | 11706613 | chr8 | 11726469 | 11726975 | chr8 | 11790579 | 11790653 |
| chr8 | 12990386 | 12990431 | chr8 | 12990664 | 12990784 | chr8 | 13319931 | 13319961 |
| chr8 | 15094505 | 15094566 | chr8 | 16884182 | 16884239 | chr8 | 16885205 | 16885241 |
| chr8 | 17271091 | 17271119 | chr8 | 19797433 | 19797463 | chr8 | 19797939 | 19798019 |
| chr8 | 20375563 | 20375592 | chr8 | 21876649 | 21876819 | chr8 | 22089409 | 22089560 |
| chr8 | 22101641 | 22101699 | chr8 | 22458657 | 22458687 | chr8 | 22562345 | 22562483 |
| chr8 | 22960648 | 22960723 | chr8 | 23020951 | 23021107 | chr8 | 23260683 | 23260870 |
| chr8 | 23423923 | 23423974 | chr8 | 23559385 | 23559601 | chr8 | 23559666 | 23560525 |
| chr8 | 23563791 | 23564023 | chr8 | 23564193 | 23564388 | chr8 | 23564652 | 23564668 |
| chr8 | 23564703 | 23565024 | chr8 | 23566803 | 23566854 | chr8 | 23566901 | 23567213 |
| chr8 | 23567312 | 23567492 | chr8 | 23571681 | 23571973 | chr8 | 23572377 | 23572554 |
| chr8 | 23584094 | 23584400 | chr8 | 23584582 | 23584760 | chr8 | 24770314 | 24770361 |
| chr8 | 24770414 | 24770581 | chr8 | 24771431 | 24771562 | chr8 | 24813188 | 24813287 |
| chr8 | 24813750 | 24813893 | chr8 | 24814011 | 24814407 | chr8 | 24857776 | 24857808 |
| chr8 | 24858336 | 24858440 | chr8 | 24858856 | 24859161 | chr8 | 24859496 | 24859526 |
| chr8 | 25041746 | 25041864 | chr8 | 25042534 | 25042567 | chr8 | 25900408 | 25900692 |
| chr8 | 25900781 | 25901317 | chr8 | 25901540 | 25901765 | chr8 | 25902146 | 25902176 |
| chr8 | 25902619 | 25902649 | chr8 | 25903662 | 25903854 | chr8 | 25904157 | 25904191 |
| chr8 | 25905096 | 25905126 | chr8 | 25905762 | 25905811 | chr8 | 25909197 | 25909597 |
| chr8 | 26372863 | 26372893 | chr8 | 26723985 | 26724080 | chr8 | 28266438 | 28266484 |
| chr8 | 28737884 | 28738023 | chr8 | 30243388 | 30243423 | chr8 | 30475450 | 30475480 |
| chr8 | 30769249 | 30769411 | chr8 | 30770106 | 30770109 | chr8 | 30770158 | 30770188 |
| chr8 | 31044103 | 31044133 | chr8 | 31496481 | 31496757 | chr8 | 31497024 | 31497152 |
| chr8 | 31497499 | 31497639 | chr8 | 32406598 | 32406914 | chr8 | 33372069 | 33372125 |
| chr8 | 33457142 | 33457379 | chr8 | 35093037 | 35093054 | chr8 | 35093951 | 35093973 |
| chr8 | 37655476 | 37655512 | chr8 | 37655810 | 37655990 | chr8 | 37656050 | 37656081 |
| chr8 | 37755922 | 37755952 | chr8 | 37822796 | 37823423 | chr8 | 37906396 | 37906513 |
| chr8 | 37961793 | 37961902 | chr8 | 38008234 | 38008557 | chr8 | 38020213 | 38020272 |
| chr8 | 38032345 | 38032827 | chr8 | 38256378 | 38256412 | chr8 | 38262472 | 38262502 |

TABLE 12-continued

| chr | start | end | chr | start | end | chr | start | end |
|---|---|---|---|---|---|---|---|---|
| chr8 | 38274835 | 38274864 | chr8 | 38323911 | 38323941 | chr8 | 38965322 | 38965386 |
| chr8 | 39172082 | 39172134 | chr8 | 41165865 | 41165918 | chr8 | 41166001 | 41166151 |
| chr8 | 41166267 | 41166679 | chr8 | 41166974 | 41166988 | chr8 | 41167026 | 41167035 |
| chr8 | 41424760 | 41424842 | chr8 | 41624826 | 41624855 | chr8 | 41625112 | 41625141 |
| chr8 | 41700639 | 41700751 | chr8 | 41711325 | 41711447 | chr8 | 41733505 | 41733640 |
| chr8 | 41753593 | 41753752 | chr8 | 41754152 | 41754885 | chr8 | 41755178 | 41755208 |
| chr8 | 41910270 | 41910339 | chr8 | 42082721 | 42082874 | chr8 | 42147392 | 42147521 |
| chr8 | 42293604 | 42293722 | chr8 | 42350324 | 42350492 | chr8 | 42749816 | 42750012 |
| chr8 | 47093246 | 47093276 | chr8 | 47334619 | 47334678 | chr8 | 48044710 | 48044753 |
| chr8 | 48100155 | 48100443 | chr8 | 49293364 | 49293524 | chr8 | 49293581 | 49293614 |
| chr8 | 49468669 | 49469127 | chr8 | 49572029 | 49572058 | chr8 | 49783041 | 49783283 |
| chr8 | 49836145 | 49836174 | chr8 | 49959230 | 49959260 | chr8 | 50822179 | 50822308 |
| chr8 | 50822686 | 50822734 | chr8 | 50823452 | 50823562 | chr8 | 52230518 | 52230548 |
| chr8 | 53322495 | 53322524 | chr8 | 53477408 | 53477736 | chr8 | 53478008 | 53478275 |
| chr8 | 53478480 | 53478720 | chr8 | 53851141 | 53851170 | chr8 | 53853811 | 53854509 |
| chr8 | 54163316 | 54163349 | chr8 | 54163674 | 54164126 | chr8 | 54698973 | 54699103 |
| chr8 | 54789278 | 54789310 | chr8 | 54789632 | 54789805 | chr8 | 54790023 | 54790077 |
| chr8 | 54790291 | 54790855 | chr8 | 54791898 | 54791945 | chr8 | 54792185 | 54792237 |
| chr8 | 54792634 | 54792670 | chr8 | 54792702 | 54792760 | chr8 | 54794217 | 54794322 |
| chr8 | 54794713 | 54794780 | chr8 | 54794827 | 54794949 | chr8 | 54795140 | 54795196 |
| chr8 | 55366188 | 55366367 | chr8 | 55366952 | 55367641 | chr8 | 55370113 | 55370432 |
| chr8 | 55370568 | 55370713 | chr8 | 55370836 | 55370858 | chr8 | 55371178 | 55371375 |
| chr8 | 55371440 | 55371724 | chr8 | 55371994 | 55372067 | chr8 | 55372417 | 55372538 |
| chr8 | 55379296 | 55379456 | chr8 | 55383183 | 55383237 | chr8 | 55826087 | 55826117 |
| chr8 | 56013641 | 56013892 | chr8 | 56014157 | 6014184 | chr8 | 56014623 | 56014743 |
| chr8 | 56015038 | 56015052 | chr8 | 56015186 | 56015357 | chr8 | 56015560 | 56015619 |
| chr8 | 56015908 | 56015938 | chr8 | 56542925 | 56543064 | chr8 | 57025776 | 57025943 |
| chr8 | 57026168 | 57026213 | chr8 | 57026503 | 57026547 | chr8 | 57069553 | 57069737 |
| chr8 | 57069851 | 57070157 | chr8 | 57358465 | 57358661 | chr8 | 57358807 | 57359091 |
| chr8 | 57359260 | 57359636 | chr8 | 57359893 | 57359922 | chr8 | 57360211 | 57360240 |
| chr8 | 57360570 | 57360625 | chr8 | 57360770 | 57360791 | chr8 | 58105946 | 58106115 |
| chr8 | 58117004 | 58117079 | chr8 | 58130364 | 58130574 | chr8 | 58907698 | 58907835 |
| chr8 | 59058941 | 59059343 | chr8 | 59747186 | 59747318 | chr8 | 60032680 | 60032738 |
| chr8 | 61777575 | 61777699 | chr8 | 61789974 | 61790004 | chr8 | 62033879 | 62034059 |
| chr8 | 62200502 | 62200776 | chr8 | 62763403 | 62763433 | chr8 | 63161658 | 63161800 |
| chr8 | 65281616 | 65281760 | chr8 | 65281984 | 65282004 | chr8 | 65282333 | 65282440 |
| chr8 | 65282713 | 65282944 | chr8 | 65283042 | 65283341 | chr8 | 65283799 | 65284094 |
| chr8 | 65286056 | 65286066 | chr8 | 65286682 | 65286753 | chr8 | 65286963 | 65287251 |
| chr8 | 65289123 | 65289241 | chr8 | 65289614 | 65290681 | chr8 | 65291034 | 65291284 |
| chr8 | 65292185 | 65292727 | chr8 | 65488271 | 65488322 | chr8 | 65488661 | 65488697 |
| chr8 | 65489099 | 65489129 | chr8 | 65492712 | 65492979 | chr8 | 65493195 | 65493433 |
| chr8 | 65494077 | 65494193 | chr8 | 65498566 | 65498841 | chr8 | 65499757 | 65500015 |
| chr8 | 65710938 | 65711046 | chr8 | 66548717 | 66548800 | chr8 | 66560323 | 66560545 |
| chr8 | 67025063 | 67025640 | chr8 | 67025920 | 67026578 | chr8 | 67026812 | 67026990 |
| chr8 | 67344538 | 67344701 | chr8 | 67580735 | 67580829 | chr8 | 67873327 | 67873421 |
| chr8 | 67873799 | 67874050 | chr8 | 67874165 | 67874672 | chr8 | 67874755 | 67875682 |
| chr8 | 67940624 | 67940875 | chr8 | 68864578 | 68864765 | chr8 | 69242905 | 69242988 |
| chr8 | 69243285 | 69243902 | chr8 | 69243964 | 69243994 | chr8 | 69244370 | 69244500 |
| chr8 | 70744860 | 70744925 | chr8 | 70946760 | 70946914 | chr8 | 70947091 | 70947658 |
| chr8 | 70982263 | 70982566 | chr8 | 70982851 | 70983226 | chr8 | 70983504 | 70983869 |
| chr8 | 70984017 | 70984292 | chr8 | 70984344 | 70984661 | chr8 | 70984745 | 70984978 |
| chr8 | 71017156 | 71017195 | chr8 | 71308096 | 71308126 | chr8 | 71447529 | 71447559 |
| chr8 | 72273998 | 72274033 | chr8 | 72468569 | 72469574 | chr8 | 72470399 | 72470441 |
| chr8 | 72471053 | 72471083 | chr8 | 72754491 | 72754609 | chr8 | 72754821 | 72755176 |
| chr8 | 72755666 | 72755814 | chr8 | 72756656 | 72756896 | chr8 | 72917335 | 72917428 |
| chr8 | 72987600 | 72988036 | chr8 | 73163860 | 73164180 | chr8 | 73450064 | 73450100 |
| chr8 | 73450515 | 73450559 | chr8 | 74759306 | 74759463 | chr8 | 74759819 | 74759966 |
| chr8 | 74889486 | 74889592 | chr8 | 75896574 | 75897337 | chr8 | 76316329 | 76316452 |
| chr8 | 77585219 | 77585698 | chr8 | 77586175 | 77586278 | chr8 | 77586563 | 77586617 |
| chr8 | 77590239 | 77590466 | chr8 | 77593110 | 77593376 | chr8 | 77593889 | 77594124 |
| chr8 | 77594648 | 77594674 | chr8 | 77594758 | 77594993 | chr8 | 77595339 | 77595494 |
| chr8 | 79428297 | 79428401 | chr8 | 80523983 | 80524029 | chr8 | 80524253 | 80524318 |
| chr8 | 80524946 | 80525020 | chr8 | 80525604 | 80525733 | chr8 | 80695902 | 80695932 |
| chr8 | 80803673 | 80803872 | chr8 | 80894529 | 80894594 | chr8 | 80998525 | 80998601 |
| chr8 | 81128658 | 81128782 | chr8 | 81398018 | 81398155 | chr8 | 81398428 | 81399496 |
| chr8 | 81414643 | 81414831 | chr8 | 81478185 | 81478350 | chr8 | 82243813 | 82243843 |
| chr8 | 82902963 | 82902993 | chr8 | 84932902 | 84932942 | chr8 | 85095482 | 85095668 |
| chr8 | 85096583 | 85096772 | chr8 | 85097063 | 85097220 | chr8 | 86131760 | 86131850 |
| chr8 | 86350553 | 86350566 | chr8 | 86405788 | 86405818 | chr8 | 86406716 | 86406849 |
| chr8 | 86436621 | 86436651 | chr8 | 86495193 | 86495287 | chr8 | 86544756 | 86544959 |
| chr8 | 89339389 | 89339745 | chr8 | 89340274 | 89340345 | chr8 | 90702972 | 90703034 |
| chr8 | 90913079 | 90913653 | chr8 | 91094221 | 91094251 | chr8 | 91411537 | 91411567 |
| chr8 | 91803676 | 91803718 | chr8 | 91804065 | 91804253 | chr8 | 91997046 | 91997508 |
| chr8 | 91997528 | 91997947 | chr8 | 92083523 | 92083751 | chr8 | 93114135 | 93114241 |
| chr8 | 93114307 | 93114528 | chr8 | 94684190 | 94684560 | chr8 | 95485999 | 95486029 |
| chr8 | 95651098 | 95651218 | chr8 | 95651538 | 95651655 | chr8 | 96038540 | 96038580 |
| chr8 | 96219863 | 96219901 | chr8 | 96285420 | 96285553 | chr8 | 97157085 | 97157209 |
| chr8 | 97157667 | 97157897 | chr8 | 97158022 | 97158066 | chr8 | 97165644 | 97165676 |

TABLE 12-continued

| chr | start | end | chr | start | end | chr | start | end |
|---|---|---|---|---|---|---|---|---|
| chr8 | 97166425 | 97166455 | chr8 | 97167178 | 97167223 | chr8 | 97167811 | 97167855 |
| chr8 | 97169838 | 97169955 | chr8 | 97170054 | 97170334 | chr8 | 97170867 | 97170897 |
| chr8 | 97171129 | 97171264 | chr8 | 97171318 | 97171958 | chr8 | 97172019 | 97172200 |
| chr8 | 97172433 | 97172739 | chr8 | 97172822 | 97173458 | chr8 | 97173822 | 97173863 |
| chr8 | 97173921 | 97173935 | chr8 | 97339846 | 97340195 | chr8 | 97506034 | 97506048 |
| chr8 | 97506178 | 97506407 | chr8 | 97506448 | 97506524 | chr8 | 97507115 | 97507284 |
| chr8 | 97507546 | 97507680 | chr8 | 98289825 | 98289867 | chr8 | 98289923 | 98290260 |
| chr8 | 98744202 | 98744325 | chr8 | 98786343 | 98786387 | chr8 | 98786918 | 98786972 |
| chr8 | 99234962 | 99235037 | chr8 | 99439104 | 99439133 | chr8 | 99439382 | 99440354 |
| chr8 | 99951404 | 99951434 | chr8 | 99951836 | 99952143 | chr8 | 99952199 | 99952303 |
| chr8 | 99952533 | 99952815 | chr8 | 99954490 | 99954562 | chr8 | 99954679 | 99954727 |
| chr8 | 99955180 | 99955327 | chr8 | 99959429 | 99959549 | chr8 | 99960329 | 99960497 |
| chr8 | 99960922 | 99960971 | chr8 | 99961792 | 99961822 | chr8 | 99985856 | 99986043 |
| chr8 | 99986226 | 99986525 | chr8 | 99986792 | 99987014 | chr8 | 100117651 | 100117765 |
| chr8 | 101118241 | 101118490 | chr8 | 101169625 | 101169659 | chr8 | 101661920 | 101661991 |
| chr8 | 101726865 | 101726945 | chr8 | 101736027 | 101736202 | chr8 | 101821973 | 101822047 |
| chr8 | 101920382 | 101920468 | chr8 | 102504464 | 102504506 | chr8 | 102505512 | 102505556 |
| chr8 | 102505797 | 102505985 | chr8 | 103575128 | 103575296 | chr8 | 103629590 | 103629882 |
| chr8 | 104153202 | 104153246 | chr8 | 104153449 | 104153561 | chr8 | 104383700 | 104383985 |
| chr8 | 104512123 | 104513186 | chr8 | 104513462 | 104513926 | chr8 | 105235369 | 105235501 |
| chr8 | 105235644 | 105235803 | chr8 | 105235864 | 105236054 | chr8 | 105478725 | 105478779 |
| chr8 | 105479404 | 105479464 | chr8 | 106301844 | 106301978 | chr8 | 106331160 | 106331237 |
| chr8 | 106332104 | 106332202 | chr8 | 106434115 | 106434145 | chr8 | 107282163 | 107282195 |
| chr8 | 107284038 | 107284075 | chr8 | 108509543 | 108509697 | chr8 | 109093679 | 109094180 |
| chr8 | 109094485 | 109094595 | chr8 | 109094840 | 109095436 | chr8 | 109095506 | 109095932 |
| chr8 | 109500408 | 109500507 | chr8 | 109799588 | 109799739 | chr8 | 110275006 | 110275040 |
| chr8 | 110406028 | 110406243 | chr8 | 110592198 | 110592228 | chr8 | 110704001 | 110704144 |
| chr8 | 110986443 | 110986682 | chr8 | 111133092 | 111133257 | chr8 | 114444580 | 114445192 |
| chr8 | 114445763 | 114446068 | chr8 | 114446405 | 114446435 | chr8 | 114446931 | 114447368 |
| chr8 | 114449039 | 114449257 | chr8 | 114449550 | 114449602 | chr8 | 115516296 | 115516440 |
| chr8 | 116660527 | 116660571 | chr8 | 116660616 | 116660760 | chr8 | 117950438 | 117950468 |
| chr8 | 117950783 | 117950914 | chr8 | 118532128 | 118532292 | chr8 | 119043568 | 119043732 |
| chr8 | 120219912 | 120219941 | chr8 | 120220116 | 120220145 | chr8 | 120220428 | 120220592 |
| chr8 | 120650979 | 120651008 | chr8 | 120651221 | 120651412 | chr8 | 120844095 | 120844285 |
| chr8 | 120845586 | 120845807 | chr8 | 121136879 | 121137748 | chr8 | 121823901 | 121823930 |
| chr8 | 121824203 | 121824481 | chr8 | 121825455 | 121825484 | chr8 | 122068889 | 122068919 |
| chr8 | 122346689 | 122346719 | chr8 | 122346940 | 122347052 | chr8 | 122651872 | 122651905 |
| chr8 | 123695532 | 123695660 | chr8 | 124014063 | 124014111 | chr8 | 124055236 | 124055336 |
| chr8 | 124173246 | 124173501 | chr8 | 124332846 | 124332875 | chr8 | 124427887 | 124428082 |
| chr8 | 125411827 | 125411857 | chr8 | 125452366 | 125452484 | chr8 | 126007690 | 126008051 |
| chr8 | 126044442 | 126044563 | chr8 | 127354106 | 127354261 | chr8 | 127569621 | 127569676 |
| chr8 | 128403354 | 128403383 | chr8 | 128745542 | 128745633 | chr8 | 128808002 | 128808077 |
| chr8 | 128872385 | 128872415 | chr8 | 128889324 | 128889422 | chr8 | 128893019 | 128893049 |
| chr8 | 128931133 | 128931261 | chr8 | 128964114 | 128964309 | chr8 | 129356009 | 129356039 |
| chr8 | 130369244 | 130369364 | chr8 | 132052147 | 132052299 | chr8 | 132052399 | 132052515 |
| chr8 | 132052590 | 132053164 | chr8 | 132053715 | 132054583 | chr8 | 132054594 | 132054785 |
| chr8 | 133360080 | 133360194 | chr8 | 133686745 | 133687107 | chr8 | 135301097 | 135301142 |
| chr8 | 139508757 | 139508946 | chr8 | 139509741 | 139509928 | chr8 | 140714570 | 140714877 |
| chr8 | 140715090 | 140715094 | chr8 | 140715469 | 140715587 | chr8 | 140715965 | 140716021 |
| chr8 | 140716340 | 140716382 | chr8 | 140755383 | 140755550 | chr8 | 140834237 | 140834321 |
| chr8 | 140963292 | 140963362 | chr8 | 141054845 | 141054875 | chr8 | 141159919 | 141159949 |
| chr8 | 141588056 | 141588132 | chr8 | 141596886 | 141597022 | chr8 | 141614252 | 141614287 |
| chr8 | 142210914 | 142211043 | chr8 | 142265206 | 142265339 | chr8 | 142282078 | 142282202 |
| chr8 | 142292552 | 142292774 | chr8 | 142318155 | 142318184 | chr8 | 142361233 | 142361487 |
| chr8 | 142367368 | 142367790 | chr8 | 142444600 | 142444752 | chr8 | 142528400 | 142528402 |
| chr8 | 142528455 | 142528606 | chr8 | 142528671 | 142528781 | chr8 | 142528835 | 142528961 |
| chr8 | 142535343 | 142535496 | chr8 | 142568598 | 142568652 | chr8 | 142632436 | 142632465 |
| chr8 | 142694847 | 142694953 | chr8 | 142984512 | 142984666 | chr8 | 143082777 | 143082810 |
| chr8 | 143089030 | 143089100 | chr8 | 143105244 | 143105377 | chr8 | 143368318 | 143368469 |
| chr8 | 143509457 | 143509594 | chr8 | 143532122 | 143532509 | chr8 | 143532542 | 143532846 |
| chr8 | 143533611 | 143533640 | chr8 | 143533709 | 143533906 | chr8 | 143557980 | 143558080 |
| chr8 | 143558472 | 143558604 | chr8 | 143587331 | 143587382 | chr8 | 143592664 | 143592687 |
| chr8 | 143611232 | 143611262 | chr8 | 143621980 | 143622096 | chr8 | 143702052 | 143702101 |
| chr8 | 143819384 | 143819428 | chr8 | 143858522 | 143858699 | chr8 | 143859338 | 143859361 |
| chr8 | 143876928 | 143876958 | chr8 | 143993974 | 143994165 | chr8 | 144069546 | 144069651 |
| chr8 | 144190378 | 144190432 | chr8 | 144203653 | 144203708 | chr8 | 144203977 | 144204021 |
| chr8 | 144226174 | 144226204 | chr8 | 144238822 | 144238901 | chr8 | 144241250 | 144241287 |
| chr8 | 144241871 | 144242356 | chr8 | 144303562 | 144303592 | chr8 | 144328321 | 144328565 |
| chr8 | 144330193 | 144330380 | chr8 | 144344293 | 144344442 | chr8 | 144347397 | 144347740 |
| chr8 | 144359977 | 144360076 | chr8 | 144360394 | 144360453 | chr8 | 144361758 | 144361823 |
| chr8 | 144372323 | 144372503 | chr8 | 144382679 | 144382775 | chr8 | 144421487 | 144421517 |
| chr8 | 144509325 | 144510529 | chr8 | 144511225 | 144511424 | chr8 | 144512041 | 144512192 |
| chr8 | 144512473 | 144512503 | chr8 | 144557003 | 144557088 | chr8 | 144601799 | 144601851 |
| chr8 | 144617065 | 144617347 | chr8 | 144650594 | 144650730 | chr8 | 144668566 | 144668667 |
| chr8 | 144668909 | 144668972 | chr8 | 145033304 | 145033333 | chr8 | 145218226 | 145218301 |
| chr8 | 145223902 | 145224061 | chr8 | 145753517 | 145753547 | chr8 | 145758572 | 145758692 |
| chr8 | 145806258 | 145806271 | chr8 | 145918683 | 145918835 | chr8 | 145925451 | 145925491 |
| chr8 | 145925947 | 145926058 | chr8 | 146013617 | 146013647 | chr8 | 146079215 | 146079379 |

TABLE 12-continued

| chr | start | end | chr | start | end | chr | start | end |
|---|---|---|---|---|---|---|---|---|
| chr8 | 146175120 | 146175269 | chr8 | 146176756 | 146176795 | chr9 | 113433 | 113512 |
| chr9 | 113550 | 113556 | chr9 | 113850 | 113885 | chr9 | 117884 | 117959 |
| chr9 | 841691 | 842031 | chr9 | 842208 | 842230 | chr9 | 842611 | 842673 |
| chr9 | 969556 | 969586 | chr9 | 969788 | 969846 | chr9 | 970096 | 970104 |
| chr9 | 970186 | 970225 | chr9 | 970495 | 970525 | chr9 | 970897 | 970911 |
| chr9 | 970993 | 971338 | chr9 | 972307 | 972759 | chr9 | 973184 | 973289 |
| chr9 | 974514 | 974547 | chr9 | 975117 | 975167 | chr9 | 975783 | 976321 |
| chr9 | 976618 | 976689 | chr9 | 976912 | 976961 | chr9 | 981797 | 981830 |
| chr9 | 1042402 | 1042500 | chr9 | 1042616 | 1042986 | chr9 | 1051905 | 1052166 |
| chr9 | 2115824 | 2115981 | chr9 | 3181752 | 3181869 | chr9 | 5070006 | 5070050 |
| chr9 | 5073756 | 5073788 | chr9 | 5078346 | 5078375 | chr9 | 5089711 | 5089740 |
| chr9 | 5153325 | 5153380 | chr9 | 6182901 | 6182931 | chr9 | 6412571 | 6412809 |
| chr9 | 6644297 | 6644367 | chr9 | 6644540 | 6644554 | chr9 | 6645017 | 6645333 |
| chr9 | 6645625 | 6645700 | chr9 | 6756353 | 6756623 | chr9 | 13278818 | 13278864 |
| chr9 | 14312994 | 14313096 | chr9 | 14313319 | 14313785 | chr9 | 14347633 | 14347673 |
| chr9 | 14348314 | 14348452 | chr9 | 14884008 | 14884061 | chr9 | 17906404 | 17906432 |
| chr9 | 17906461 | 17906694 | chr9 | 17907004 | 17907061 | chr9 | 17907451 | 17907472 |
| chr9 | 19789107 | 19789301 | chr9 | 20199955 | 20199985 | chr9 | 21031734 | 21031836 |
| chr9 | 21402617 | 21403021 | chr9 | 21559294 | 21559381 | chr9 | 21559665 | 21559702 |
| chr9 | 21965057 | 21965424 | chr9 | 21965570 | 21965757 | chr9 | 21968218 | 21968433 |
| chr9 | 21968457 | 21968475 | chr9 | 21970959 | 21971154 | chr9 | 21971185 | 21971220 |
| chr9 | 21973940 | 21974076 | chr9 | 21974182 | 21974237 | chr9 | 21974499 | 21974794 |
| chr9 | 21994208 | 21994237 | chr9 | 21995297 | 21995326 | chr9 | 21995720 | 21995749 |
| chr9 | 22006131 | 22006152 | chr9 | 22008819 | 22008899 | chr9 | 22447664 | 22447708 |
| chr9 | 23822568 | 23822606 | chr9 | 23824561 | 23824591 | chr9 | 23831100 | 23831370 |
| chr9 | 29212170 | 29212170 | chr9 | 29212211 | 29212294 | chr9 | 29213508 | 29213651 |
| chr9 | 29214030 | 29214144 | chr9 | 29214360 | 29214430 | chr9 | 29214681 | 29215086 |
| chr9 | 32782630 | 32782935 | chr9 | 32783084 | 32783121 | chr9 | 32783346 | 32783419 |
| chr9 | 32783591 | 32783657 | chr9 | 33000470 | 33000512 | chr9 | 33524609 | 33524687 |
| chr9 | 33676771 | 33676801 | chr9 | 33677360 | 33677415 | chr9 | 34136792 | 34136903 |
| chr9 | 34224348 | 34224474 | chr9 | 34372805 | 34372983 | chr9 | 34589062 | 34589156 |
| chr9 | 35617291 | 35617337 | chr9 | 35675539 | 35675647 | chr9 | 35675838 | 35676180 |
| chr9 | 35844834 | 35844863 | chr9 | 36036323 | 36036353 | chr9 | 36037068 | 36037098 |
| chr9 | 36167272 | 36167544 | chr9 | 36196920 | 36197005 | chr9 | 36318375 | 36318410 |
| chr9 | 36433491 | 36433629 | chr9 | 36739812 | 36739980 | chr9 | 36832204 | 36832343 |
| chr9 | 37002454 | 37002517 | chr9 | 37002819 | 37003077 | chr9 | 37025564 | 37025783 |
| chr9 | 37026146 | 37026351 | chr9 | 37026434 | 37026622 | chr9 | 37026831 | 37027271 |
| chr9 | 37027325 | 37027412 | chr9 | 37027800 | 37027829 | chr9 | 37028944 | 37029119 |
| chr9 | 37029534 | 37030655 | chr9 | 37034197 | 37034247 | chr9 | 37034616 | 37034731 |
| chr9 | 37035366 | 37035734 | chr9 | 37036425 | 37036647 | chr9 | 37037671 | 37038354 |
| chr9 | 37119301 | 37119331 | chr9 | 37467610 | 37467898 | chr9 | 37593684 | 37593795 |
| chr9 | 37697404 | 37697438 | chr9 | 38620530 | 38620725 | chr9 | 38646763 | 38646839 |
| chr9 | 66455999 | 66456047 | chr9 | 71200632 | 71200662 | chr9 | 71500847 | 71500886 |
| chr9 | 71584152 | 71584254 | chr9 | 71734816 | 71735024 | chr9 | 71788952 | 71789260 |
| chr9 | 71789453 | 71789757 | chr9 | 72435189 | 72435317 | chr9 | 73032801 | 73032831 |
| chr9 | 74061838 | 74062070 | chr9 | 74210499 | 74210654 | chr9 | 74764547 | 74764648 |
| chr9 | 77112993 | 77113340 | chr9 | 77113559 | 77113708 | chr9 | 77113806 | 77113825 |
| chr9 | 77114745 | 77114851 | chr9 | 77115210 | 77115447 | chr9 | 77115657 | 77115687 |
| chr9 | 77823177 | 77823315 | chr9 | 79197119 | 79197149 | chr9 | 79231003 | 79231033 |
| chr9 | 79626876 | 79627370 | chr9 | 79628289 | 79628329 | chr9 | 79629208 | 79629471 |
| chr9 | 79629879 | 79630420 | chr9 | 79631192 | 79631335 | chr9 | 79631555 | 79631591 |
| chr9 | 79631865 | 79632182 | chr9 | 79632860 | 79632890 | chr9 | 79633397 | 79633904 |
| chr9 | 79634170 | 79635448 | chr9 | 79635746 | 79636043 | chr9 | 79636258 | 79637274 |
| chr9 | 79637555 | 79637888 | chr9 | 79638137 | 79638244 | chr9 | 80303132 | 80303171 |
| chr9 | 80409473 | 80409502 | chr9 | 80833933 | 80834011 | chr9 | 85372494 | 85372596 |
| chr9 | 85677905 | 85677992 | chr9 | 86152387 | 86152417 | chr9 | 86578079 | 86578366 |
| chr9 | 86755532 | 86755952 | chr9 | 86886706 | 86886736 | chr9 | 87283008 | 87283038 |
| chr9 | 87283677 | 87283709 | chr9 | 87284706 | 87284798 | chr9 | 87285279 | 87285472 |
| chr9 | 88137524 | 88137725 | chr9 | 88137875 | 88137998 | chr9 | 88694345 | 88694438 |
| chr9 | 89560760 | 89560827 | chr9 | 89561063 | 89561109 | chr9 | 90907408 | 90907438 |
| chr9 | 90937357 | 90937387 | chr9 | 91150222 | 91150335 | chr9 | 91606004 | 91606058 |
| chr9 | 91792357 | 91792387 | chr9 | 91792776 | 91792907 | chr9 | 91793177 | 91793526 |
| chr9 | 91914276 | 91914306 | chr9 | 92053911 | 92053949 | chr9 | 93698029 | 93698133 |
| chr9 | 94183870 | 94183954 | chr9 | 94572641 | 94572743 | chr9 | 94686919 | 94686957 |
| chr9 | 95417551 | 95417651 | chr9 | 95560810 | 95560840 | chr9 | 95569759 | 95569822 |
| chr9 | 95570247 | 95570434 | chr9 | 95571617 | 95571760 | chr9 | 95761687 | 95761828 |
| chr9 | 95947130 | 95947296 | chr9 | 96230296 | 96230334 | chr9 | 96573748 | 96573869 |
| chr9 | 96588858 | 96588885 | chr9 | 96710377 | 96710407 | chr9 | 96710647 | 96710991 |
| chr9 | 96711258 | 96711446 | chr9 | 96711535 | 96711617 | chr9 | 96711975 | 96712005 |
| chr9 | 96713378 | 96713893 | chr9 | 96715095 | 96715372 | chr9 | 96715688 | 96715857 |
| chr9 | 96716905 | 96717427 | chr9 | 96717450 | 96717466 | chr9 | 96717979 | 96718149 |
| chr9 | 96720803 | 96720885 | chr9 | 96721103 | 96721467 | chr9 | 96721689 | 96721802 |
| chr9 | 96722445 | 96722547 | chr9 | 96723093 | 96723159 | chr9 | 96723171 | 96723202 |
| chr9 | 96856991 | 96857144 | chr9 | 97020978 | 97021126 | chr9 | 97845915 | 97845947 |
| chr9 | 98076746 | 98076776 | chr9 | 98111365 | 98111560 | chr9 | 98111895 | 98112157 |
| chr9 | 98112344 | 98112395 | chr9 | 98784772 | 98784802 | chr9 | 98789651 | 98790000 |
| chr9 | 99146020 | 99146153 | chr9 | 99259362 | 99259405 | chr9 | 99449135 | 99449451 |
| chr9 | 99450020 | 99450142 | chr9 | 99639621 | 99639942 | chr9 | 99983140 | 99983170 |

TABLE 12-continued

| chr | start | end | chr | start | end | chr | start | end |
|---|---|---|---|---|---|---|---|---|
| chr9 | 99983411 | 99983824 | chr9 | 99984026 | 99984057 | chr9 | 99984108 | 99984242 |
| chr9 | 100397821 | 100398016 | chr9 | 100503625 | 100503937 | chr9 | 100609991 | 100610134 |
| chr9 | 100610201 | 100610218 | chr9 | 100610681 | 100610816 | chr9 | 100611125 | 100611640 |
| chr9 | 100613828 | 100613999 | chr9 | 100614193 | 100614325 | chr9 | 100614541 | 100616035 |
| chr9 | 100616271 | 100616468 | chr9 | 100617293 | 100617365 | chr9 | 100617682 | 100618055 |
| chr9 | 100619722 | 100620069 | chr9 | 100620330 | 100620783 | chr9 | 100818295 | 100818437 |
| chr9 | 100835828 | 100835870 | chr9 | 101469269 | 101469307 | chr9 | 101469603 | 101469796 |
| chr9 | 101470116 | 101470250 | chr9 | 101470968 | 101471071 | chr9 | 101471570 | 101471621 |
| chr9 | 101471860 | 101472009 | chr9 | 101705996 | 101706195 | chr9 | 101706313 | 101706695 |
| chr9 | 103174620 | 103174730 | chr9 | 104248579 | 104248623 | chr9 | 104249475 | 104249562 |
| chr9 | 104500625 | 104500774 | chr9 | 106998039 | 106998134 | chr9 | 110126074 | 110126247 |
| chr9 | 110228200 | 110228602 | chr9 | 110251388 | 110251418 | chr9 | 110252363 | 110252515 |
| chr9 | 111894386 | 111894520 | chr9 | 112403170 | 112403200 | chr9 | 112403364 | 112403394 |
| chr9 | 113341522 | 113341621 | chr9 | 113341680 | 113341847 | chr9 | 113341927 | 113341965 |
| chr9 | 113342299 | 113342340 | chr9 | 114247454 | 114247578 | chr9 | 115067932 | 115068106 |
| chr9 | 115087567 | 115087597 | chr9 | 115478932 | 115479250 | chr9 | 115566363 | 115566583 |
| chr9 | 115652966 | 115653425 | chr9 | 116633883 | 116633987 | chr9 | 117050981 | 117051030 |
| chr9 | 118917024 | 118917079 | chr9 | 119603412 | 119603535 | chr9 | 120175795 | 120175832 |
| chr9 | 120176104 | 120176151 | chr9 | 120176867 | 120176910 | chr9 | 122131497 | 122131642 |
| chr9 | 122131880 | 122132025 | chr9 | 122132052 | 122132227 | chr9 | 123004898 | 123004928 |
| chr9 | 123295355 | 123295463 | chr9 | 124535347 | 124535611 | chr9 | 124749865 | 124749953 |
| chr9 | 124751485 | 124751515 | chr9 | 125676633 | 125676753 | chr9 | 125704789 | 125704835 |
| chr9 | 126133778 | 126133856 | chr9 | 126154304 | 126154575 | chr9 | 126349038 | 126349104 |
| chr9 | 126770257 | 126770298 | chr9 | 126771532 | 126771705 | chr9 | 126774517 | 126774619 |
| chr9 | 126775530 | 126775560 | chr9 | 126776044 | 126776098 | chr9 | 126777529 | 126777746 |
| chr9 | 126777974 | 126777982 | chr9 | 126778359 | 126778496 | chr9 | 126779485 | 126780043 |
| chr9 | 126780285 | 126780315 | chr9 | 126780811 | 126780898 | chr9 | 126783295 | 126783499 |
| chr9 | 127212851 | 127213006 | chr9 | 127265876 | 127266025 | chr9 | 127266387 | 127266534 |
| chr9 | 127605297 | 127605327 | chr9 | 127630125 | 127630205 | chr9 | 127853274 | 127853304 |
| chr9 | 127920543 | 127920572 | chr9 | 128136065 | 128136095 | chr9 | 128635180 | 128635210 |
| chr9 | 128652200 | 128652232 | chr9 | 128759852 | 128759954 | chr9 | 129276718 | 129276820 |
| chr9 | 129372929 | 129373037 | chr9 | 129376170 | 129376199 | chr9 | 129376889 | 129376918 |
| chr9 | 129377214 | 129377316 | chr9 | 129377604 | 129377635 | chr9 | 129377773 | 129377959 |
| chr9 | 129387434 | 129387464 | chr9 | 129387848 | 129388200 | chr9 | 129388719 | 129388753 |
| chr9 | 129388996 | 129389192 | chr9 | 129400986 | 129401195 | chr9 | 129445255 | 129445566 |
| chr9 | 129445783 | 129445813 | chr9 | 129517783 | 129517821 | chr9 | 130248419 | 130248449 |
| chr9 | 130325967 | 130325997 | chr9 | 130461687 | 130461742 | chr9 | 130675509 | 130675615 |
| chr9 | 130689631 | 130689667 | chr9 | 130689742 | 130689749 | chr9 | 130694413 | 130694468 |
| chr9 | 130694809 | 130694948 | chr9 | 131177975 | 131178094 | chr9 | 131417698 | 131417940 |
| chr9 | 131542193 | 131542267 | chr9 | 131580038 | 131580257 | chr9 | 131607517 | 131607547 |
| chr9 | 131607770 | 131607800 | chr9 | 131854231 | 131854328 | chr9 | 131854564 | 131854732 |
| chr9 | 132373058 | 132373091 | chr9 | 132382635 | 132383109 | chr9 | 132383347 | 132383376 |
| chr9 | 132402840 | 132402883 | chr9 | 132403149 | 132403216 | chr9 | 132559377 | 132559456 |
| chr9 | 132804405 | 132804455 | chr9 | 132804796 | 132804974 | chr9 | 132805318 | 132805445 |
| chr9 | 132805737 | 132805893 | chr9 | 132815175 | 132815205 | chr9 | 132881814 | 132881844 |
| chr9 | 133308893 | 133308941 | chr9 | 133534683 | 133534713 | chr9 | 133535734 | 133535839 |
| chr9 | 133536097 | 133536119 | chr9 | 133536150 | 133536344 | chr9 | 133536778 | 133536869 |
| chr9 | 133537182 | 133537549 | chr9 | 133538169 | 133538728 | chr9 | 133539606 | 133539709 |
| chr9 | 133541059 | 133541192 | chr9 | 133541689 | 133542337 | chr9 | 133605601 | 133605631 |
| chr9 | 133738343 | 133738372 | chr9 | 133747505 | 133747534 | chr9 | 133773766 | 133773923 |
| chr9 | 133927347 | 133927481 | chr9 | 133928236 | 133928265 | chr9 | 134126670 | 134126741 |
| chr9 | 134191085 | 134191218 | chr9 | 134207916 | 134208048 | chr9 | 134421797 | 134421835 |
| chr9 | 134717313 | 134717367 | chr9 | 135037119 | 135037287 | chr9 | 135037334 | 135037357 |
| chr9 | 135073463 | 135073506 | chr9 | 135135114 | 135135247 | chr9 | 135231073 | 135231158 |
| chr9 | 135455407 | 135455585 | chr9 | 135455996 | 135456023 | chr9 | 135456476 | 135456544 |
| chr9 | 135456897 | 135456932 | chr9 | 135458477 | 135458597 | chr9 | 135460001 | 135460176 |
| chr9 | 135460869 | 135460899 | chr9 | 135461511 | 135461773 | chr9 | 135462048 | 135462077 |
| chr9 | 135462648 | 135462967 | chr9 | 135464798 | 135464918 | chr9 | 135465948 | 135466064 |
| chr9 | 135466118 | 135466132 | chr9 | 135466344 | 135466660 | chr9 | 135548238 | 135548313 |
| chr9 | 135590218 | 135590334 | chr9 | 135796801 | 135796830 | chr9 | 135865090 | 135865161 |
| chr9 | 135898911 | 135899124 | chr9 | 136474490 | 136474591 | chr9 | 137002646 | 137002692 |
| chr9 | 137111397 | 137111426 | chr9 | 137229892 | 137229921 | chr9 | 137299119 | 137299450 |
| chr9 | 137299670 | 137299699 | chr9 | 137534066 | 137534238 | chr9 | 137575915 | 137575945 |
| chr9 | 137656958 | 137657128 | chr9 | 137667327 | 137667357 | chr9 | 137702189 | 137702222 |
| chr9 | 137718901 | 137719001 | chr9 | 137722087 | 137722209 | chr9 | 137979893 | 137980011 |
| chr9 | 137980258 | 137980288 | chr9 | 137980880 | 137980910 | chr9 | 138265123 | 138265251 |
| chr9 | 138474557 | 138474590 | chr9 | 138563059 | 138563280 | chr9 | 138606821 | 138606923 |
| chr9 | 138627636 | 138627893 | chr9 | 138634047 | 138634159 | chr9 | 138659800 | 138659905 |
| chr9 | 138660943 | 138661012 | chr9 | 138661648 | 138661870 | chr9 | 138666455 | 138666558 |
| chr9 | 138826382 | 138826412 | chr9 | 138880711 | 138880875 | chr9 | 138991798 | 138991828 |
| chr9 | 139000565 | 139000642 | chr9 | 139012272 | 139012411 | chr9 | 139024750 | 139024782 |
| chr9 | 139045653 | 139045683 | chr9 | 139047532 | 139047633 | chr9 | 139085228 | 139085350 |
| chr9 | 139090500 | 139090551 | chr9 | 139091072 | 139091369 | chr9 | 139093773 | 139093890 |
| chr9 | 139094705 | 139094732 | chr9 | 139095340 | 139095485 | chr9 | 139096650 | 139097006 |
| chr9 | 139111268 | 139111298 | chr9 | 139269039 | 139269121 | chr9 | 139399407 | 139399436 |
| chr9 | 139421955 | 139421985 | chr9 | 139477862 | 139478020 | chr9 | 139698921 | 139699051 |
| chr9 | 139704008 | 139704279 | chr9 | 139859041 | 139859268 | chr9 | 139888945 | 139888980 |
| chr9 | 140015209 | 140015241 | chr9 | 140024842 | 140024918 | chr9 | 140024957 | 140025023 |

TABLE 12-continued

| chr | start | end | chr | start | end | chr | start | end |
|---|---|---|---|---|---|---|---|---|
| chr9 | 140030498 | 140030528 | chr9 | 140031944 | 140032082 | chr9 | 140032891 | 140032951 |
| chr9 | 140033001 | 140033092 | chr9 | 140033426 | 140033490 | chr9 | 140033619 | 140033626 |
| chr9 | 140033909 | 140034079 | chr9 | 140050969 | 140051096 | chr9 | 140051220 | 140051354 |
| chr9 | 140127883 | 140128080 | chr9 | 140137310 | 140137488 | chr9 | 140197122 | 140197263 |
| chr9 | 140205394 | 140205519 | chr9 | 140245877 | 140245998 | chr9 | 140332708 | 140333018 |
| chr9 | 140382557 | 140382596 | chr9 | 140392454 | 140392484 | chr9 | 140397029 | 140397097 |
| chr9 | 140498318 | 140498394 | chr9 | 140507256 | 140507419 | chr9 | 140704046 | 140704131 |
| chr9 | 140709046 | 140709174 | chr9 | 140727471 | 140727511 | chr9 | 140727845 | 140727930 |
| chr9 | 140769943 | 140769973 | chr9 | 140771975 | 140772347 | chr9 | 140772586 | 140772593 |
| chr9 | 140772757 | 140773301 | chr10 | 524754 | 524784 | chr10 | 833307 | 833386 |
| chr10 | 978878 | 978933 | chr10 | 1080377 | 1080513 | chr10 | 1120778 | 1120937 |
| chr10 | 1577394 | 1577424 | chr10 | 1585111 | 1585239 | chr10 | 1651360 | 1651374 |
| chr10 | 1708327 | 1708478 | chr10 | 1774858 | 1774887 | chr10 | 1779417 | 1779744 |
| chr10 | 3109360 | 3109459 | chr10 | 3197004 | 3197113 | chr10 | 3285585 | 3285698 |
| chr10 | 3330499 | 3330618 | chr10 | 3641378 | 3641413 | chr10 | 3678597 | 3678637 |
| chr10 | 3895410 | 3895452 | chr10 | 4599917 | 4599965 | chr10 | 5530764 | 5530975 |
| chr10 | 5765021 | 5765059 | chr10 | 5855154 | 5855184 | chr10 | 5875140 | 5875396 |
| chr10 | 6003402 | 6003855 | chr10 | 6042309 | 6042571 | chr10 | 6162159 | 6162225 |
| chr10 | 6167619 | 6167742 | chr10 | 6206142 | 6206170 | chr10 | 6372343 | 6372373 |
| chr10 | 6513976 | 6514006 | chr10 | 6577643 | 6577673 | chr10 | 6586721 | 6586847 |
| chr10 | 6963079 | 6963111 | chr10 | 6984463 | 6984639 | chr10 | 7205733 | 7205787 |
| chr10 | 7212745 | 7213064 | chr10 | 7213505 | 7213535 | chr10 | 7216059 | 7216089 |
| chr10 | 7236211 | 7236245 | chr10 | 7255730 | 7255821 | chr10 | 7323283 | 7323313 |
| chr10 | 7334737 | 7334767 | chr10 | 7363436 | 7363466 | chr10 | 7371678 | 7371708 |
| chr10 | 7414544 | 7414588 | chr10 | 7424626 | 7424687 | chr10 | 7436090 | 7436209 |
| chr10 | 7449954 | 7450189 | chr10 | 7450491 | 7451390 | chr10 | 7452227 | 7452777 |
| chr10 | 7453313 | 7453656 | chr10 | 7453903 | 7453930 | chr10 | 7708274 | 7708304 |
| chr10 | 7708790 | 7708856 | chr10 | 7708955 | 7709087 | chr10 | 7709723 | 7709752 |
| chr10 | 8055681 | 8055764 | chr10 | 8075930 | 8075944 | chr10 | 8076341 | 8076487 |
| chr10 | 8076804 | 8077374 | chr10 | 8077874 | 8078218 | chr10 | 8085039 | 8085721 |
| chr10 | 8085978 | 8086010 | chr10 | 8091895 | 8092278 | chr10 | 8093738 | 8093824 |
| chr10 | 8093860 | 8093963 | chr10 | 8095603 | 8095845 | chr10 | 8096160 | 8096190 |
| chr10 | 8096975 | 8097197 | chr10 | 8097474 | 8097537 | chr10 | 11059933 | 11060062 |
| chr10 | 11206206 | 11206235 | chr10 | 11207179 | 11207276 | chr10 | 11700918 | 11701075 |
| chr10 | 12390825 | 12390995 | chr10 | 12391870 | 12392327 | chr10 | 12554417 | 12554501 |
| chr10 | 13043386 | 13043425 | chr10 | 13140861 | 13141020 | chr10 | 13715208 | 13715401 |
| chr10 | 13933005 | 13933035 | chr10 | 13933436 | 13933538 | chr10 | 13933597 | 13933934 |
| chr10 | 13933983 | 13934125 | chr10 | 13934169 | 13934183 | chr10 | 14393819 | 14393893 |
| chr10 | 14966129 | 14966212 | chr10 | 15002784 | 15003006 | chr10 | 15140484 | 15140526 |
| chr10 | 15761292 | 15761671 | chr10 | 15762124 | 15762154 | chr10 | 16175687 | 16175801 |
| chr10 | 16562369 | 16562672 | chr10 | 16562710 | 16563664 | chr10 | 16563691 | 16563909 |
| chr10 | 16564087 | 16564116 | chr10 | 16564537 | 16564566 | chr10 | 17269259 | 17269288 |
| chr10 | 17269628 | 17269789 | chr10 | 17270072 | 17270445 | chr10 | 17270991 | 17271254 |
| chr10 | 17271444 | 17271625 | chr10 | 17271914 | 17272233 | chr10 | 17272601 | 17272630 |
| chr10 | 17273172 | 17273201 | chr10 | 17275584 | 17275613 | chr10 | 17277741 | 17227770 |
| chr10 | 17429165 | 17429622 | chr10 | 17496545 | 17496734 | chr10 | 17503402 | 17503520 |
| chr10 | 17509450 | 17509503 | chr10 | 18429628 | 18429774 | chr10 | 21101525 | 21101555 |
| chr10 | 21462533 | 21462607 | chr10 | 21462970 | 21463023 | chr10 | 21728064 | 21728124 |
| chr10 | 21805217 | 21805277 | chr10 | 22047336 | 22047635 | chr10 | 22541638 | 22541850 |
| chr10 | 22542025 | 22542249 | chr10 | 22567093 | 22567322 | chr10 | 22624022 | 22624305 |
| chr10 | 22624562 | 22625120 | chr10 | 22625383 | 22625782 | chr10 | 22625812 | 22625978 |
| chr10 | 22633985 | 22634174 | chr10 | 22634325 | 22634578 | chr10 | 22764649 | 22765791 |
| chr10 | 22765821 | 22765901 | chr10 | 23216865 | 23216945 | chr10 | 23460355 | 23460471 |
| chr10 | 23461222 | 23461754 | chr10 | 23462059 | 23462462 | chr10 | 23462486 | 23462614 |
| chr10 | 23462635 | 23462910 | chr10 | 23463267 | 23463853 | chr10 | 23463888 | 23464077 |
| chr10 | 23479876 | 23480696 | chr10 | 23480904 | 23481049 | chr10 | 23481321 | 23481515 |
| chr10 | 23481936 | 23482232 | chr10 | 23482289 | 23482445 | chr10 | 23483828 | 23484618 |
| chr10 | 23486264 | 23486328 | chr10 | 23487742 | 23487978 | chr10 | 23488393 | 23489158 |
| chr10 | 23489409 | 23489439 | chr10 | 23982438 | 23982820 | chr10 | 23983194 | 23983247 |
| chr10 | 23983618 | 23983700 | chr10 | 23984082 | 23984226 | chr10 | 23984923 | 23984991 |
| chr10 | 24988589 | 24988619 | chr10 | 25464619 | 25464915 | chr10 | 25465421 | 25465517 |
| chr10 | 26055811 | 26055841 | chr10 | 26223001 | 26223205 | chr10 | 26224031 | 26224061 |
| chr10 | 26500619 | 26500870 | chr10 | 26501539 | 26501589 | chr10 | 26503693 | 26503731 |
| chr10 | 26504114 | 26504143 | chr10 | 26504491 | 26504883 | chr10 | 26505009 | 26505227 |
| chr10 | 26505442 | 26505617 | chr10 | 26506057 | 26506163 | chr10 | 26506373 | 26506618 |
| chr10 | 26506903 | 26507400 | chr10 | 26681099 | 26681129 | chr10 | 26727098 | 26727368 |
| chr10 | 26727604 | 26727816 | chr10 | 26747051 | 26747159 | chr10 | 26803853 | 26803883 |
| chr10 | 26816766 | 26816938 | chr10 | 26931897 | 26931926 | chr10 | 27547946 | 27548331 |
| chr10 | 27548401 | 27548484 | chr10 | 27794496 | 27794588 | chr10 | 27846637 | 27846816 |
| chr10 | 28030892 | 28030925 | chr10 | 28032966 | 28033020 | chr10 | 28033410 | 28033481 |
| chr10 | 28033770 | 28034186 | chr10 | 28034327 | 28034341 | chr10 | 28034874 | 28035300 |
| chr10 | 28035615 | 28035782 | chr10 | 28287373 | 28287557 | chr10 | 28287777 | 28288070 |
| chr10 | 28657255 | 28657343 | chr10 | 28958086 | 28958129 | chr10 | 28964745 | 28964800 |
| chr10 | 29011047 | 29011162 | chr10 | 30026077 | 30026090 | chr10 | 30848200 | 30848230 |
| chr10 | 31073368 | 31073481 | chr10 | 31892922 | 31893079 | chr10 | 32499044 | 32499176 |
| chr10 | 32672459 | 32672489 | chr10 | 33233313 | 33233361 | chr10 | 33624166 | 33624230 |
| chr10 | 33624492 | 33624560 | chr10 | 35929334 | 35929528 | chr10 | 37051865 | 37051895 |
| chr10 | 38078948 | 38079105 | chr10 | 43186151 | 43186181 | chr10 | 43250009 | 43250039 |

TABLE 12-continued

| chr | start | end | chr | start | end | chr | start | end |
|---|---|---|---|---|---|---|---|---|
| chr10 | 43250406 | 43250779 | chr10 | 43250855 | 43250886 | chr10 | 43428424 | 43428576 |
| chr10 | 43429067 | 43429100 | chr10 | 43429376 | 43429411 | chr10 | 43572685 | 43572734 |
| chr10 | 43600561 | 43600720 | chr10 | 43609055 | 43609117 | chr10 | 43609922 | 43609963 |
| chr10 | 43613890 | 43613919 | chr10 | 43614982 | 43615011 | chr10 | 43615554 | 43615607 |
| chr10 | 43617401 | 43617430 | chr10 | 43697887 | 43698086 | chr10 | 43698115 | 43698155 |
| chr10 | 43858343 | 43858470 | chr10 | 43905877 | 43906023 | chr10 | 44434176 | 44434206 |
| chr10 | 44879944 | 44880228 | chr10 | 44880869 | 44880915 | chr10 | 49652977 | 49653080 |
| chr10 | 49731548 | 49731749 | chr10 | 49732060 | 49732087 | chr10 | 49732156 | 49732498 |
| chr10 | 50323222 | 50323258 | chr10 | 50340119 | 50340149 | chr10 | 50507557 | 50507619 |
| chr10 | 50603967 | 50604159 | chr10 | 50604608 | 50604645 | chr10 | 50605057 | 50605654 |
| chr10 | 50606027 | 50606433 | chr10 | 50748131 | 50748350 | chr10 | 50817015 | 50817132 |
| chr10 | 50817858 | 50817872 | chr10 | 50818382 | 50818432 | chr10 | 50818987 | 50819102 |
| chr10 | 50821472 | 50821701 | chr10 | 50887655 | 50887753 | chr10 | 50887790 | 50887816 |
| chr10 | 50977034 | 50977048 | chr10 | 52177545 | 52177575 | chr10 | 53107427 | 53107563 |
| chr10 | 54068526 | 54068610 | chr10 | 54072982 | 54073020 | chr10 | 54073265 | 54073295 |
| chr10 | 54074744 | 54074789 | chr10 | 57387429 | 57387796 | chr10 | 57388325 | 57388510 |
| chr10 | 57390290 | 57390637 | chr10 | 57391166 | 57391215 | chr10 | 60273130 | 60273278 |
| chr10 | 60935887 | 60935996 | chr10 | 60936524 | 60936729 | chr10 | 60937073 | 60937103 |
| chr10 | 63212324 | 63212701 | chr10 | 63669223 | 63669344 | chr10 | 64575526 | 64575638 |
| chr10 | 64578171 | 64578540 | chr10 | 65262111 | 65262304 | chr10 | 69578459 | 69578588 |
| chr10 | 69589153 | 69589407 | chr10 | 70167678 | 70167708 | chr10 | 70232345 | 70232485 |
| chr10 | 70275831 | 70275979 | chr10 | 70314814 | 70315148 | chr10 | 70565410 | 70565489 |
| chr10 | 70586494 | 70586540 | chr10 | 71084981 | 71085116 | chr10 | 71327725 | 71327764 |
| chr10 | 71328773 | 71328821 | chr10 | 71329079 | 71329118 | chr10 | 71329544 | 71329618 |
| chr10 | 71332052 | 71333018 | chr10 | 72015150 | 72015339 | chr10 | 72043779 | 72043894 |
| chr10 | 72200118 | 72200138 | chr10 | 72200354 | 72200771 | chr10 | 72200825 | 72201285 |
| chr10 | 72973130 | 72973180 | chr10 | 73156362 | 73166661 | chr10 | 73157867 | 73158027 |
| chr10 | 75384100 | 75384130 | chr10 | 75386789 | 75386893 | chr10 | 75388129 | 75388173 |
| chr10 | 75407570 | 75407837 | chr10 | 75488953 | 75489125 | chr10 | 77190039 | 77190068 |
| chr10 | 77191224 | 77191368 | chr10 | 79396921 | 79397089 | chr10 | 81023884 | 81023914 |
| chr10 | 81154141 | 81154192 | chr10 | 81664867 | 81664899 | chr10 | 81860447 | 81860568 |
| chr10 | 81966737 | 81966828 | chr10 | 82117074 | 82117271 | chr10 | 83634261 | 83634361 |
| chr10 | 83634467 | 83634499 | chr10 | 83635531 | 83635545 | chr10 | 85792257 | 85792287 |
| chr10 | 85954425 | 85954457 | chr10 | 88123672 | 88123701 | chr10 | 88149363 | 88149601 |
| chr10 | 88304914 | 88304944 | chr10 | 88684005 | 88684034 | chr10 | 88698834 | 88698914 |
| chr10 | 89624255 | 89624311 | chr10 | 89653788 | 89653859 | chr10 | 89685272 | 89685322 |
| chr10 | 89690790 | 89690819 | chr10 | 89692776 | 89693015 | chr10 | 89711861 | 89711992 |
| chr10 | 89717610 | 89717744 | chr10 | 89720790 | 89720885 | chr10 | 89725030 | 89725071 |
| chr10 | 90966708 | 90966865 | chr10 | 90967671 | 90968040 | chr10 | 91295029 | 91295067 |
| chr10 | 91295585 | 91295725 | chr10 | 92617242 | 92617308 | chr10 | 93647216 | 93647300 |
| chr10 | 93647562 | 93647648 | chr10 | 94062288 | 94062318 | chr10 | 94450675 | 94450726 |
| chr10 | 94451448 | 94451602 | chr10 | 94826023 | 94826056 | chr10 | 94828194 | 94828498 |
| chr10 | 94828735 | 94828828 | chr10 | 94834413 | 94835047 | chr10 | 95360216 | 95360750 |
| chr10 | 96304020 | 96304329 | chr10 | 98129822 | 98130033 | chr10 | 98528023 | 98528107 |
| chr10 | 98558129 | 98558200 | chr10 | 99081122 | 99061253 | chr10 | 99080252 | 99080447 |
| chr10 | 99080862 | 99080930 | chr10 | 99161398 | 99161560 | chr10 | 99474393 | 99474467 |
| chr10 | 99481747 | 99481905 | chr10 | 99531219 | 99531430 | chr10 | 99789175 | 99789282 |
| chr10 | 99790261 | 99790318 | chr10 | 99790590 | 99790664 | chr10 | 99790947 | 99791161 |
| chr10 | 100991907 | 100992190 | chr10 | 100992222 | 100992443 | chr10 | 100992882 | 100992916 |
| chr10 | 100993537 | 100994016 | chr10 | 100996046 | 100996224 | chr10 | 101088995 | 101089439 |
| chr10 | 101089908 | 101090203 | chr10 | 101280204 | 101280485 | chr10 | 101283464 | 101283658 |
| chr10 | 101290117 | 101290160 | chr10 | 101290180 | 101291142 | chr10 | 101292297 | 101292919 |
| chr10 | 101293156 | 101293343 | chr10 | 101294756 | 101295586 | chr10 | 101296768 | 101296800 |
| chr10 | 101363207 | 101363418 | chr10 | 101492942 | 101493074 | chr10 | 101874886 | 101875138 |
| chr10 | 101988223 | 101988404 | chr10 | 102322230 | 102322260 | chr10 | 102419400 | 102419681 |
| chr10 | 102430699 | 102430761 | chr10 | 102473856 | 102473932 | chr10 | 102483993 | 102484245 |
| chr10 | 102484270 | 102484554 | chr10 | 102495508 | 102495741 | chr10 | 102497273 | 102497708 |
| chr10 | 102498280 | 102498433 | chr10 | 102501359 | 102501389 | chr10 | 102507509 | 102507535 |
| chr10 | 102508996 | 102509285 | chr10 | 102589425 | 102589493 | chr10 | 102589786 | 102589915 |
| chr10 | 102590152 | 102590415 | chr10 | 102890941 | 102891582 | chr10 | 102891823 | 102891955 |
| chr10 | 102893624 | 102893951 | chr10 | 102894091 | 102895289 | chr10 | 102899173 | 102899601 |
| chr10 | 102899807 | 102899855 | chr10 | 102900263 | 102900575 | chr10 | 102906525 | 102906620 |
| chr10 | 102975619 | 102975834 | chr10 | 102976150 | 102976180 | chr10 | 102977051 | 102977412 |
| chr10 | 102983153 | 102983379 | chr10 | 102983435 | 102983749 | chr10 | 102984513 | 102984516 |
| chr10 | 102985772 | 102985963 | chr10 | 102986534 | 102986952 | chr10 | 102987207 | 102987558 |
| chr10 | 102989629 | 102989659 | chr10 | 102996116 | 102996480 | chr10 | 102996597 | 102996638 |
| chr10 | 102997329 | 102997406 | chr10 | 102998576 | 102998828 | chr10 | 103043975 | 103044227 |
| chr10 | 103044301 | 103044366 | chr10 | 103325743 | 103325773 | chr10 | 103425950 | 103426174 |
| chr10 | 103432412 | 103432441 | chr10 | 103535622 | 103535770 | chr10 | 103536227 | 103536256 |
| chr10 | 103536300 | 103536416 | chr10 | 103579635 | 103579713 | chr10 | 103814668 | 103814754 |
| chr10 | 103930034 | 103930161 | chr10 | 104170096 | 104170262 | chr10 | 104170408 | 104170732 |
| chr10 | 105036542 | 105036658 | chr10 | 105036701 | 105036863 | chr10 | 105037223 | 105037830 |
| chr10 | 105126957 | 105127076 | chr10 | 105155285 | 105155481 | chr10 | 105413627 | 105413784 |
| chr10 | 105420861 | 105420891 | chr10 | 105527028 | 105527057 | chr10 | 106398644 | 106398687 |
| chr10 | 106398826 | 106398886 | chr10 | 106399581 | 106400387 | chr10 | 106401323 | 106401432 |
| chr10 | 106401511 | 106402190 | chr10 | 106402272 | 106402325 | chr10 | 106402712 | 106402825 |
| chr10 | 108469972 | 108470093 | chr10 | 108924045 | 108924059 | chr10 | 110671930 | 110672245 |
| chr10 | 111216789 | 111216803 | chr10 | 112403151 | 112403297 | chr10 | 112440378 | 112440408 |

TABLE 12-continued

| chr | start | end | chr | start | end | chr | start | end |
|---|---|---|---|---|---|---|---|---|
| chr10 | 115804840 | 115805014 | chr10 | 115925505 | 115925552 | chr10 | 116164248 | 116164341 |
| chr10 | 116331126 | 116331156 | chr10 | 116853875 | 116853908 | chr10 | 118030642 | 118030705 |
| chr10 | 118031302 | 118031548 | chr10 | 118031625 | 118032229 | chr10 | 118032413 | 118032547 |
| chr10 | 118032917 | 118033542 | chr10 | 118034143 | 118034168 | chr10 | 118609305 | 118609390 |
| chr10 | 118890980 | 118891104 | chr10 | 118891517 | 118891661 | chr10 | 118891716 | 118891774 |
| chr10 | 118892013 | 118892456 | chr10 | 118892518 | 118893266 | chr10 | 118893680 | 118893825 |
| chr10 | 118894035 | 118894071 | chr10 | 118896629 | 118896805 | chr10 | 118897913 | 118897968 |
| chr10 | 118899273 | 118899302 | chr10 | 118899583 | 118899602 | chr10 | 118899893 | 118899957 |
| chr10 | 118900166 | 118900244 | chr10 | 118900324 | 118900498 | chr10 | 118922143 | 118922208 |
| chr10 | 118922721 | 118922901 | chr10 | 118923138 | 118923259 | chr10 | 118924604 | 118924896 |
| chr10 | 118927086 | 118927296 | chr10 | 118928548 | 118928727 | chr10 | 119000690 | 119001154 |
| chr10 | 119001534 | 119001564 | chr10 | 119294352 | 119294461 | chr10 | 119294847 | 119294897 |
| chr10 | 119294909 | 119295245 | chr10 | 119296756 | 119296788 | chr10 | 119297384 | 119297529 |
| chr10 | 119301365 | 119301427 | chr10 | 119302141 | 119302155 | chr10 | 119302222 | 119302266 |
| chr10 | 119302962 | 119303174 | chr10 | 119304363 | 119304393 | chr10 | 119304896 | 119304985 |
| chr10 | 119305062 | 119305109 | chr10 | 119307022 | 119307052 | chr10 | 119311867 | 119311897 |
| chr10 | 119312751 | 119313193 | chr10 | 119590435 | 119590464 | chr10 | 119807026 | 119807056 |
| chr10 | 120354243 | 120354273 | chr10 | 120355548 | 120355614 | chr10 | 120707028 | 120707111 |
| chr10 | 120800789 | 120800835 | chr10 | 120841558 | 120841590 | chr10 | 120937014 | 120937139 |
| chr10 | 121267480 | 121267626 | chr10 | 121307542 | 121307572 | chr10 | 122216896 | 122217083 |
| chr10 | 122708495 | 122708691 | chr10 | 122708992 | 122709022 | chr10 | 123256044 | 123256232 |
| chr10 | 123258020 | 123258091 | chr10 | 123274758 | 123274787 | chr10 | 123279548 | 123279697 |
| chr10 | 123357206 | 123357242 | chr10 | 123357766 | 123357893 | chr10 | 123667184 | 123667222 |
| chr10 | 123688711 | 123688741 | chr10 | 123922645 | 123922682 | chr10 | 124893178 | 124893192 |
| chr10 | 124893238 | 124893350 | chr10 | 124893635 | 124893765 | chr10 | 124893965 | 124894479 |
| chr10 | 124894889 | 124894922 | chr10 | 124895426 | 124895695 | chr10 | 124895833 | 124896456 |
| chr10 | 124897220 | 124897973 | chr10 | 124899035 | 124899116 | chr10 | 124899754 | 124899786 |
| chr10 | 124901892 | 124902046 | chr10 | 124902139 | 124902568 | chr10 | 124902608 | 124903238 |
| chr10 | 124904921 | 124905119 | chr10 | 124905481 | 124905511 | chr10 | 124905920 | 124906174 |
| chr10 | 124906436 | 124906544 | chr10 | 124907312 | 124907534 | chr10 | 124908091 | 124908121 |
| chr10 | 124909085 | 124909114 | chr10 | 124909253 | 124909537 | chr10 | 124909674 | 124909726 |
| chr10 | 124910363 | 124910454 | chr10 | 124910709 | 124911048 | chr10 | 125425515 | 125425547 |
| chr10 | 125527754 | 125627784 | chr10 | 125650866 | 125651162 | chr10 | 125851328 | 125851645 |
| chr10 | 125852299 | 125852497 | chr10 | 125852753 | 125853191 | chr10 | 126101966 | 126102095 |
| chr10 | 126135927 | 126136065 | chr10 | 126136506 | 126136723 | chr10 | 126137181 | 126137405 |
| chr10 | 126198949 | 126199077 | chr10 | 126697789 | 126698107 | chr10 | 126782965 | 126783048 |
| chr10 | 126828994 | 126829024 | chr10 | 127406313 | 127406386 | chr10 | 127693923 | 127693959 |
| chr10 | 128076561 | 128076630 | chr10 | 128993904 | 128994446 | chr10 | 128994727 | 128994903 |
| chr10 | 129379338 | 129379367 | chr10 | 129534993 | 129535446 | chr10 | 129535696 | 129535733 |
| chr10 | 129536080 | 129536223 | chr10 | 129536259 | 129536310 | chr10 | 129888804 | 129888885 |
| chr10 | 129948111 | 129948140 | chr10 | 130085356 | 130085362 | chr10 | 130203435 | 130203480 |
| chr10 | 130338727 | 130338768 | chr10 | 130338804 | 130338976 | chr10 | 130577764 | 130577794 |
| chr10 | 131348513 | 131348793 | chr10 | 131647903 | 131647933 | chr10 | 131761378 | 131761441 |
| chr10 | 131761687 | 131761725 | chr10 | 131762087 | 131762124 | chr10 | 131762592 | 131762631 |
| chr10 | 131762904 | 131762940 | chr10 | 131763633 | 131763717 | chr10 | 131767372 | 131767503 |
| chr10 | 131767543 | 131767649 | chr10 | 131768724 | 131769029 | chr10 | 131769533 | 131770237 |
| chr10 | 131770657 | 131770687 | chr10 | 131770988 | 131771093 | chr10 | 131936451 | 131936626 |
| chr10 | 131937355 | 131937428 | chr10 | 132000973 | 132001015 | chr10 | 132001252 | 132001556 |
| chr10 | 133109192 | 133109260 | chr10 | 133110554 | 133110704 | chr10 | 133794883 | 133795241 |
| chr10 | 133795313 | 133795430 | chr10 | 133795682 | 133795883 | chr10 | 133795976 | 133796058 |
| chr10 | 133849598 | 133850008 | chr10 | 133850529 | 133860774 | chr10 | 133951602 | 133952025 |
| chr10 | 133979059 | 133979089 | chr10 | 134000008 | 134000028 | chr10 | 134000109 | 134000124 |
| chr10 | 134001140 | 134001260 | chr10 | 134016203 | 134016388 | chr10 | 134022845 | 134022875 |
| chr10 | 134039087 | 134039117 | chr10 | 134092153 | 134092202 | chr10 | 134095594 | 134095833 |
| chr10 | 134119401 | 134119447 | chr10 | 134121401 | 134121430 | chr10 | 134273064 | 134273156 |
| chr10 | 134301095 | 134301212 | chr10 | 134481320 | 134481433 | chr10 | 134491021 | 134491114 |
| chr10 | 134499773 | 134499803 | chr10 | 134593329 | 134593416 | chr10 | 134598087 | 134598090 |
| chr10 | 134598368 | 134598530 | chr10 | 134599432 | 134599482 | chr10 | 134599808 | 134600016 |
| chr10 | 134600038 | 134600998 | chr10 | 134601556 | 134601715 | chr10 | 134602183 | 134602269 |
| chr10 | 134607970 | 134608183 | chr10 | 134665147 | 134665202 | chr10 | 134679129 | 134679265 |
| chr10 | 134690559 | 134690617 | chr10 | 134693587 | 134693709 | chr10 | 134699872 | 134699909 |
| chr10 | 134733221 | 134733275 | chr10 | 134733497 | 134733617 | chr10 | 134738378 | 134738642 |
| chr10 | 134755773 | 134756183 | chr10 | 134788083 | 134788251 | chr10 | 134794271 | 134794342 |
| chr10 | 134796012 | 134796042 | chr10 | 134896060 | 134896092 | chr10 | 134901193 | 134901511 |
| chr10 | 134902008 | 134902124 | chr10 | 134902188 | 134902307 | chr10 | 134916714 | 134916774 |
| chr10 | 134941145 | 134941178 | chr10 | 134942840 | 134943114 | chr10 | 134943445 | 134943542 |
| chr10 | 134944742 | 134944772 | chr10 | 134959217 | 134959391 | chr10 | 135002063 | 135002156 |
| chr10 | 135014963 | 135015132 | chr10 | 135017049 | 135017129 | chr10 | 135018032 | 135018070 |
| chr10 | 135018825 | 135018960 | chr10 | 135020801 | 135020893 | chr10 | 135023470 | 135023500 |
| chr10 | 135043088 | 135043538 | chr10 | 135043968 | 135044128 | chr10 | 135044555 | 135044573 |
| chr10 | 135048782 | 135048939 | chr10 | 135050311 | 135050679 | chr10 | 135076368 | 135076503 |
| chr10 | 135121316 | 135121345 | chr10 | 135121807 | 135122251 | chr10 | 135122742 | 135122808 |
| chr10 | 135122991 | 135123020 | chr10 | 135139555 | 135139730 | chr10 | 135153956 | 135154001 |
| chr11 | 232863 | 233062 | chr11 | 392576 | 392720 | chr11 | 394815 | 394968 |
| chr11 | 406876 | 406939 | chr11 | 407427 | 407463 | chr11 | 505732 | 505869 |
| chr11 | 518400 | 518430 | chr11 | 526389 | 526419 | chr11 | 533451 | 533567 |
| chr11 | 533869 | 533888 | chr11 | 534273 | 534302 | chr11 | 548731 | 548800 |
| chr11 | 611099 | 611128 | chr11 | 611691 | 611791 | chr11 | 636644 | 636673 |

TABLE 12-continued

| chr | start | end | chr | start | end | chr | start | end |
|---|---|---|---|---|---|---|---|---|
| chr11 | 636895 | 636906 | chr11 | 637162 | 637263 | chr11 | 637350 | 637441 |
| chr11 | 679692 | 679722 | chr11 | 726417 | 726466 | chr11 | 763323 | 763686 |
| chr11 | 775261 | 775291 | chr11 | 829543 | 829708 | chr11 | 830174 | 830243 |
| chr11 | 850555 | 850823 | chr11 | 861612 | 861657 | chr11 | 863062 | 863092 |
| chr11 | 1006077 | 1006107 | chr11 | 1027540 | 1027574 | chr11 | 1029238 | 1029403 |
| chr11 | 1030215 | 1030296 | chr11 | 1080391 | 1080454 | chr11 | 1081667 | 1081715 |
| chr11 | 1214665 | 1214917 | chr11 | 1215899 | 1215999 | chr11 | 1229945 | 1229975 |
| chr11 | 1244381 | 1244465 | chr11 | 1250889 | 1250924 | chr11 | 1251183 | 1251351 |
| chr11 | 1263602 | 1263644 | chr11 | 1274085 | 1274189 | chr11 | 1318403 | 1318432 |
| chr11 | 1358291 | 1358332 | chr11 | 1374959 | 1375003 | chr11 | 1411875 | 1411905 |
| chr11 | 1430714 | 1430794 | chr11 | 1464280 | 1464428 | chr11 | 1469228 | 1469379 |
| chr11 | 1471920 | 1472058 | chr11 | 1868081 | 1868237 | chr11 | 1946130 | 1946160 |
| chr11 | 1957391 | 1957530 | chr11 | 1959077 | 1959187 | chr11 | 2040107 | 2040148 |
| chr11 | 2209907 | 2210278 | chr11 | 2226048 | 2226078 | chr11 | 2278708 | 2278839 |
| chr11 | 2291259 | 2291493 | chr11 | 2291984 | 2292057 | chr11 | 2292106 | 2292359 |
| chr11 | 2292392 | 2292636 | chr11 | 2402376 | 2402405 | chr11 | 2437991 | 2438144 |
| chr11 | 2465350 | 2465447 | chr11 | 2465462 | 2465491 | chr11 | 2466597 | 2466788 |
| chr11 | 2884103 | 2884143 | chr11 | 2884159 | 2884309 | chr11 | 3027425 | 3027562 |
| chr11 | 3169665 | 3169835 | chr11 | 3181913 | 3181942 | chr11 | 3182104 | 3182133 |
| chr11 | 3511446 | 3511501 | chr11 | 3767205 | 3767284 | chr11 | 4038082 | 4038176 |
| chr11 | 4095819 | 4095864 | chr11 | 4209105 | 4209134 | chr11 | 4209382 | 4209411 |
| chr11 | 5641077 | 5641140 | chr11 | 5993897 | 5994029 | chr11 | 6497192 | 6497222 |
| chr11 | 7274215 | 7274245 | chr11 | 7695432 | 7695528 | chr11 | 8040536 | 8040563 |
| chr11 | 8040582 | 8040770 | chr11 | 8103002 | 8103115 | chr11 | 8189987 | 8190766 |
| chr11 | 8284535 | 8284760 | chr11 | 8289517 | 8289745 | chr11 | 8290195 | 8290423 |
| chr11 | 8615674 | 8615704 | chr11 | 9025970 | 9026348 | chr11 | 9112446 | 9112585 |
| chr11 | 9112640 | 9112741 | chr11 | 9405392 | 9405752 | chr11 | 10509678 | 10509807 |
| chr11 | 10811151 | 10811224 | chr11 | 10815867 | 10815998 | chr11 | 12029957 | 12030272 |
| chr11 | 12030823 | 12030852 | chr11 | 12132524 | 12132559 | chr11 | 12399040 | 12399222 |
| chr11 | 12399727 | 12399791 | chr11 | 12695481 | 12695495 | chr11 | 12695573 | 12695611 |
| chr11 | 12696611 | 12696746 | chr11 | 13030566 | 13030596 | chr11 | 13690121 | 13690157 |
| chr11 | 13711492 | 13711529 | chr11 | 14316375 | 14316404 | chr11 | 14543250 | 14543304 |
| chr11 | 14866247 | 14866285 | chr11 | 15136085 | 15136394 | chr11 | 16628819 | 16628933 |
| chr11 | 16632514 | 16632670 | chr11 | 17497492 | 17497520 | chr11 | 17497546 | 17497685 |
| chr11 | 17740493 | 17740570 | chr11 | 17741679 | 17741889 | chr11 | 17741953 | 17742445 |
| chr11 | 17743742 | 17743775 | chr11 | 18100096 | 18100259 | chr11 | 18812614 | 18812653 |
| chr11 | 18813032 | 18813086 | chr11 | 18813451 | 18813542 | chr11 | 18813792 | 18813947 |
| chr11 | 19263848 | 19263878 | chr11 | 19367102 | 19367134 | chr11 | 19367268 | 19367330 |
| chr11 | 19736730 | 19735760 | chr11 | 20153718 | 20163764 | chr11 | 20178094 | 20178305 |
| chr11 | 20180279 | 20180793 | chr11 | 20181213 | 20181254 | chr11 | 20181725 | 20181993 |
| chr11 | 20182864 | 20182959 | chr11 | 20183251 | 20183421 | chr11 | 20183674 | 20183773 |
| chr11 | 20184569 | 20185410 | chr11 | 20229058 | 20229550 | chr11 | 20229863 | 20230091 |
| chr11 | 20230398 | 20230464 | chr11 | 20408219 | 20408341 | chr11 | 20618197 | 20618392 |
| chr11 | 20618423 | 20618924 | chr11 | 20619717 | 20619974 | chr11 | 20621341 | 20621644 |
| chr11 | 20622705 | 20622792 | chr11 | 20623259 | 20623359 | chr11 | 20690653 | 20690877 |
| chr11 | 20691219 | 20691379 | chr11 | 20691432 | 20691452 | chr11 | 20691748 | 20691914 |
| chr11 | 20692453 | 20692529 | chr11 | 22215123 | 22215287 | chr11 | 22362934 | 22363189 |
| chr11 | 22364821 | 22364975 | chr11 | 22365407 | 22365477 | chr11 | 22742185 | 22742215 |
| chr11 | 27743115 | 27743173 | chr11 | 27743436 | 27743608 | chr11 | 27744147 | 27744504 |
| chr11 | 27744711 | 27744744 | chr11 | 30037593 | 30037743 | chr11 | 30038689 | 30038739 |
| chr11 | 30605919 | 30606123 | chr11 | 30606796 | 30606864 | chr11 | 30607367 | 30607409 |
| chr11 | 31760124 | 31760235 | chr11 | 31818458 | 31818512 | chr11 | 31818571 | 31818652 |
| chr11 | 31819302 | 31819833 | chr11 | 31820045 | 31820360 | chr11 | 31820461 | 31821025 |
| chr11 | 31821297 | 31821778 | chr11 | 31822325 | 31822393 | chr11 | 31824300 | 31824355 |
| chr11 | 31824564 | 31824680 | chr11 | 31825017 | 31825280 | chr11 | 31825696 | 31825754 |
| chr11 | 31825833 | 31826070 | chr11 | 31826107 | 31826303 | chr11 | 31826409 | 31826732 |
| chr11 | 31827114 | 31827204 | chr11 | 31827438 | 31827519 | chr11 | 31827598 | 31828123 |
| chr11 | 31833097 | 31833155 | chr11 | 31835707 | 31835797 | chr11 | 31836046 | 31836470 |
| chr11 | 31837019 | 31837512 | chr11 | 31837542 | 31838392 | chr11 | 31838678 | 31839051 |
| chr11 | 31839307 | 31839945 | chr11 | 31840042 | 31840080 | chr11 | 31840603 | 31840710 |
| chr11 | 31840769 | 31840922 | chr11 | 31841376 | 31842088 | chr11 | 31842175 | 31842276 |
| chr11 | 31846022 | 31846230 | chr11 | 31846434 | 31846985 | chr11 | 31847250 | 31847301 |
| chr11 | 31847371 | 31847712 | chr11 | 31847770 | 31847822 | chr11 | 31847896 | 31847925 |
| chr11 | 31848472 | 31848602 | chr11 | 31848723 | 31849300 | chr11 | 32009104 | 32009126 |
| chr11 | 32354844 | 32354959 | chr11 | 32355000 | 32355197 | chr11 | 32448583 | 32448893 |
| chr11 | 32455602 | 32455634 | chr11 | 32455841 | 32456025 | chr11 | 32456279 | 32456446 |
| chr11 | 32456759 | 32457176 | chr11 | 32457712 | 32458175 | chr11 | 32458389 | 32458823 |
| chr11 | 32459684 | 32460071 | chr11 | 32460468 | 32460515 | chr11 | 32460796 | 32460864 |
| chr11 | 33037467 | 33037556 | chr11 | 33264773 | 33264935 | chr11 | 33277455 | 33277485 |
| chr11 | 33318780 | 33318945 | chr11 | 33858324 | 33858463 | chr11 | 33890297 | 33890334 |
| chr11 | 33993984 | 33994014 | chr11 | 34535093 | 34535123 | chr11 | 35547499 | 35547562 |
| chr11 | 35641683 | 35641718 | chr11 | 35684958 | 35685131 | chr11 | 43596513 | 43596608 |
| chr11 | 43600453 | 43600557 | chr11 | 43601094 | 43601467 | chr11 | 43602468 | 43603036 |
| chr11 | 43603077 | 43603228 | chr11 | 43603628 | 43604145 | chr11 | 44325688 | 44325747 |
| chr11 | 44326137 | 44326184 | chr11 | 44327252 | 44327413 | chr11 | 44330878 | 44331439 |
| chr11 | 44331483 | 44331711 | chr11 | 44333052 | 44333081 | chr11 | 44333371 | 44333461 |
| chr11 | 44333477 | 44333480 | chr11 | 44337533 | 44337571 | chr11 | 44337727 | 44337861 |
| chr11 | 44337883 | 44338057 | chr11 | 44338335 | 44338367 | chr11 | 44340823 | 44340858 |

TABLE 12-continued

| chr | start | end | chr | start | end | chr | start | end |
|---|---|---|---|---|---|---|---|---|
| chr11 | 44341966 | 44342034 | chr11 | 46227561 | 46227654 | chr11 | 46316896 | 46317355 |
| chr11 | 46317408 | 46317680 | chr11 | 46413042 | 46413304 | chr11 | 46866293 | 46866510 |
| chr11 | 46940419 | 46940531 | chr11 | 46959190 | 46959251 | chr11 | 47209044 | 47209189 |
| chr11 | 47260168 | 47260258 | chr11 | 47358926 | 47359237 | chr11 | 47363557 | 47363625 |
| chr11 | 47372828 | 47373002 | chr11 | 47478438 | 47478500 | chr11 | 47485995 | 47486141 |
| chr11 | 57194355 | 57194509 | chr11 | 57235406 | 57235436 | chr11 | 57414663 | 57414673 |
| chr11 | 57437157 | 57437234 | chr11 | 57500982 | 57501068 | chr11 | 58672746 | 58673064 |
| chr11 | 59323596 | 59323729 | chr11 | 59329086 | 59329240 | chr11 | 59333405 | 59333541 |
| chr11 | 59841403 | 59841533 | chr11 | 60718668 | 60718853 | chr11 | 60718977 | 60719163 |
| chr11 | 60927079 | 60927319 | chr11 | 61049694 | 61049736 | chr11 | 61058283 | 61058341 |
| chr11 | 61062822 | 61063023 | chr11 | 61063062 | 61063138 | chr11 | 61148730 | 61148768 |
| chr11 | 61154806 | 61154836 | chr11 | 61277002 | 61277119 | chr11 | 61536985 | 61537014 |
| chr11 | 61595086 | 61595262 | chr11 | 61596420 | 61596640 | chr11 | 61664655 | 61664770 |
| chr11 | 61666106 | 61666136 | chr11 | 61811996 | 61812151 | chr11 | 61880361 | 61880398 |
| chr11 | 62370720 | 62370750 | chr11 | 62440509 | 62440588 | chr11 | 62484517 | 62484547 |
| chr11 | 62497600 | 62497630 | chr11 | 62555752 | 62555782 | chr11 | 63202941 | 63203091 |
| chr11 | 63431856 | 63431918 | chr11 | 63432139 | 63432218 | chr11 | 63609824 | 63610013 |
| chr11 | 63641072 | 63641256 | chr11 | 63839478 | 63839528 | chr11 | 63849394 | 63849426 |
| chr11 | 63934498 | 63934619 | chr11 | 64105954 | 64106108 | chr11 | 64120879 | 64120909 |
| chr11 | 64140397 | 64140427 | chr11 | 64410723 | 64410759 | chr11 | 64480429 | 64480593 |
| chr11 | 64480824 | 64481042 | chr11 | 64490435 | 64490561 | chr11 | 64490792 | 64490806 |
| chr11 | 64490826 | 64491159 | chr11 | 64578577 | 64578743 | chr11 | 64739468 | 64739508 |
| chr11 | 64796439 | 64796571 | chr11 | 64809584 | 64809906 | chr11 | 64903331 | 64903361 |
| chr11 | 64950292 | 64950374 | chr11 | 65091272 | 65091369 | chr11 | 65185548 | 65185728 |
| chr11 | 65364470 | 65364557 | chr11 | 65405659 | 65405774 | chr11 | 65409759 | 65409861 |
| chr11 | 65448943 | 65449022 | chr11 | 65478376 | 65478611 | chr11 | 65510941 | 65511172 |
| chr11 | 65511392 | 65511522 | chr11 | 65554043 | 65554410 | chr11 | 65600810 | 65601640 |
| chr11 | 65778952 | 65778981 | chr11 | 65779317 | 65779357 | chr11 | 65816447 | 65816519 |
| chr11 | 65816561 | 65816564 | chr11 | 65891131 | 65891227 | chr11 | 66114279 | 66114331 |
| chr11 | 66138094 | 66138260 | chr11 | 66188115 | 66188145 | chr11 | 66188473 | 66188484 |
| chr11 | 66188571 | 66188783 | chr11 | 56188853 | 66188974 | chr11 | 66324254 | 66324447 |
| chr11 | 66454424 | 66454454 | chr11 | 66511223 | 66511431 | chr11 | 66513217 | 66513646 |
| chr11 | 66557543 | 66557710 | chr11 | 66625207 | 66625240 | chr11 | 66649028 | 66649058 |
| chr11 | 66658224 | 66658290 | chr11 | 66725600 | 66725637 | chr11 | 66790621 | 66790655 |
| chr11 | 67072239 | 67072396 | chr11 | 67139422 | 67139460 | chr11 | 67139535 | 67139546 |
| chr11 | 67210017 | 67210057 | chr11 | 67248321 | 67248458 | chr11 | 57350180 | 67350340 |
| chr11 | 67350961 | 67350990 | chr11 | 67462643 | 67462833 | chr11 | 62764187 | 67764254 |
| chr11 | 67781196 | 67781564 | chr11 | 67797202 | 67797420 | chr11 | 67918044 | 67918145 |
| chr11 | 67999703 | 67999866 | chr11 | 68096034 | 68096179 | chr11 | 68118716 | 68118745 |
| chr11 | 68153950 | 68154098 | chr11 | 68181217 | 68181288 | chr11 | 68221758 | 68222056 |
| chr11 | 68409558 | 68409588 | chr11 | 58804728 | 68804776 | chr11 | 69192566 | 69192784 |
| chr11 | 69280561 | 69280633 | chr11 | 69466004 | 69466042 | chr11 | 69484356 | 69484454 |
| chr11 | 69516968 | 69517174 | chr11 | 69518030 | 69518211 | chr11 | 69518530 | 69518718 |
| chr11 | 69588930 | 69589184 | chr11 | 69589824 | 69589854 | chr11 | 69590149 | 69590222 |
| chr11 | 70211516 | 70211545 | chr11 | 71192746 | 71192889 | chr11 | 71318332 | 71318809 |
| chr11 | 71318953 | 71318967 | chr11 | 71647544 | 71647574 | chr11 | 71792437 | 71792496 |
| chr11 | 71863650 | 71863785 | chr11 | 71951639 | 71951738 | chr11 | 71952340 | 71952416 |
| chr11 | 71952459 | 71952541 | chr11 | 71954612 | 71954642 | chr11 | 71955344 | 71955377 |
| chr11 | 71956007 | 71956340 | chr11 | 72413980 | 72414010 | chr11 | 72432837 | 72432916 |
| chr11 | 72475677 | 72475711 | chr11 | 72532348 | 72532378 | chr11 | 72929747 | 72929883 |
| chr11 | 73072907 | 73072953 | chr11 | 73310367 | 73310441 | chr11 | 73481055 | 73481085 |
| chr11 | 73561763 | 73561798 | chr11 | 73685698 | 73685845 | chr11 | 73694609 | 73694659 |
| chr11 | 74246487 | 74246521 | chr11 | 74394491 | 74394600 | chr11 | 74953265 | 74953336 |
| chr11 | 75379283 | 75379895 | chr11 | 75459486 | 75459775 | chr11 | 75858210 | 75858240 |
| chr11 | 75859012 | 75859053 | chr11 | 76293588 | 76293618 | chr11 | 76371738 | 76372077 |
| chr11 | 76594692 | 76594722 | chr11 | 77533964 | 77534145 | chr11 | 78672917 | 78672964 |
| chr11 | 79151173 | 79151216 | chr11 | 82444376 | 82445101 | chr11 | 82998001 | 82998121 |
| chr11 | 85709169 | 85709254 | chr11 | 86085742 | 86085861 | chr11 | 86085932 | 86085968 |
| chr11 | 86383167 | 86383710 | chr11 | 88241705 | 88241975 | chr11 | 88242131 | 88242274 |
| chr11 | 88242359 | 88242618 | chr11 | 88799082 | 88799209 | chr11 | 89052235 | 89052282 |
| chr11 | 89867794 | 89867990 | chr11 | 91957500 | 91957674 | chr11 | 91957974 | 91958230 |
| chr11 | 91958734 | 91959326 | chr11 | 91959355 | 91959430 | chr11 | 91959899 | 91960045 |
| chr11 | 93063583 | 93063645 | chr11 | 93063870 | 93063948 | chr11 | 93911651 | 93911800 |
| chr11 | 94134086 | 94134463 | chr11 | 94134683 | 94134853 | chr11 | 94275794 | 94275951 |
| chr11 | 94278456 | 94278603 | chr11 | 94473600 | 94473768 | chr11 | 94473803 | 94474139 |
| chr11 | 94474356 | 94474385 | chr11 | 94502334 | 94502489 | chr11 | 94884130 | 94884160 |
| chr11 | 96517902 | 96517932 | chr11 | 98891477 | 98891882 | chr11 | 100997649 | 100997981 |
| chr11 | 100998276 | 100998318 | chr11 | 100998667 | 100998744 | chr11 | 101453180 | 101453518 |
| chr11 | 101723359 | 101723455 | chr11 | 102158378 | 102158427 | chr11 | 102961347 | 102961649 |
| chr11 | 102962922 | 102963052 | chr11 | 102980027 | 102980055 | chr11 | 104034521 | 104034996 |
| chr11 | 105480755 | 105480785 | chr11 | 105481216 | 105481571 | chr11 | 106888308 | 106888429 |
| chr11 | 106888641 | 106888801 | chr11 | 107461623 | 107461653 | chr11 | 107462415 | 107462459 |
| chr11 | 108236072 | 108236101 | chr11 | 108603233 | 108603263 | chr11 | 109292906 | 109293052 |
| chr11 | 109293720 | 109293763 | chr11 | 110166519 | 110166935 | chr11 | 110582232 | 110582434 |
| chr11 | 110582895 | 110583028 | chr11 | 110583044 | 110583050 | chr11 | 110583574 | 110583730 |
| chr11 | 111383183 | 111383531 | chr11 | 111383558 | 111383682 | chr11 | 111411093 | 111411581 |
| chr11 | 111411822 | 111412061 | chr11 | 111783548 | 111783577 | chr11 | 111976911 | 111976941 |
| chr11 | 114113022 | 114113052 | chr11 | 115375120 | 115375177 | chr11 | 115530222 | 115530604 |

TABLE 12-continued

| chr | start | end | chr | start | end | chr | start | end |
|---|---|---|---|---|---|---|---|---|
| chr11 | 115630531 | 115630910 | chr11 | 115631307 | 115631364 | chr11 | 116147253 | 116147283 |
| chr11 | 116451023 | 116451190 | chr11 | 116976126 | 116976156 | chr11 | 116984568 | 116984565 |
| chr11 | 117017686 | 117017773 | chr11 | 117055950 | 117056073 | chr11 | 117296921 | 117297109 |
| chr11 | 118724458 | 118724605 | chr11 | 118991033 | 118991079 | chr11 | 119148865 | 119148945 |
| chr11 | 119149236 | 119149265 | chr11 | 119292779 | 119292809 | chr11 | 119293370 | 119293615 |
| chr11 | 119612227 | 119612267 | chr11 | 119612324 | 119612399 | chr11 | 119612861 | 119613075 |
| chr11 | 120008105 | 120008504 | chr11 | 120039833 | 120039865 | chr11 | 120367948 | 120368008 |
| chr11 | 120435405 | 120435477 | chr11 | 120435800 | 120435830 | chr11 | 120894800 | 120895026 |
| chr11 | 120998701 | 120998825 | chr11 | 121152057 | 121152203 | chr11 | 122847265 | 122847696 |
| chr11 | 122848079 | 122848312 | chr11 | 122848369 | 122848591 | chr11 | 122849301 | 122849331 |
| chr11 | 122849642 | 122850123 | chr11 | 122850149 | 122850163 | chr11 | 122850424 | 122850536 |
| chr11 | 122851177 | 122851209 | chr11 | 122852438 | 122862475 | chr11 | 122855008 | 122855043 |
| chr11 | 122895443 | 122895485 | chr11 | 122961054 | 122961219 | chr11 | 123066433 | 123066463 |
| chr11 | 123229058 | 123229406 | chr11 | 123300824 | 123301028 | chr11 | 123301083 | 123302026 |
| chr11 | 123963874 | 123963994 | chr11 | 124735437 | 124735482 | chr11 | 124736196 | 124736252 |
| chr11 | 124738777 | 124739088 | chr11 | 125035763 | 125036208 | chr11 | 125220500 | 125220643 |
| chr11 | 125755612 | 125755710 | chr11 | 125758604 | 125758660 | chr11 | 125773675 | 125774060 |
| chr11 | 126870182 | 126870212 | chr11 | 126870453 | 126870500 | chr11 | 126870525 | 126870543 |
| chr11 | 126873390 | 126873515 | chr11 | 128391893 | 128392116 | chr11 | 128562892 | 128563185 |
| chr11 | 128563337 | 128563730 | chr11 | 128563940 | 128564329 | chr11 | 128564740 | 128564876 |
| chr11 | 128564992 | 128565379 | chr11 | 128657892 | 128657970 | chr11 | 129242876 | 129243241 |
| chr11 | 129243305 | 129243587 | chr11 | 129243849 | 129244300 | chr11 | 129244441 | 129244603 |
| chr11 | 129244893 | 129244923 | chr11 | 129245673 | 129245810 | chr11 | 129246070 | 129246129 |
| chr11 | 129907552 | 129907714 | chr11 | 129931742 | 129931851 | chr11 | 130318960 | 130318997 |
| chr11 | 130319527 | 130319613 | chr11 | 130343061 | 130343100 | chr11 | 130359769 | 130359915 |
| chr11 | 130781550 | 130781781 | chr11 | 130785487 | 130785622 | chr11 | 130854324 | 130854490 |
| chr11 | 131522763 | 131522947 | chr11 | 131564970 | 131565073 | chr11 | 131766715 | 131766960 |
| chr11 | 131780877 | 131781078 | chr11 | 132484215 | 132484404 | chr11 | 132813489 | 132813757 |
| chr11 | 132813908 | 132813949 | chr11 | 132864134 | 132864175 | chr11 | 132934123 | 132934176 |
| chr11 | 132952768 | 132953050 | chr11 | 132953233 | 132953423 | chr11 | 133231739 | 133231832 |
| chr11 | 133402206 | 133402260 | chr11 | 133792055 | 133792214 | chr11 | 133825226 | 133825543 |
| chr11 | 133906783 | 133906918 | chr11 | 133939002 | 133939177 | chr11 | 134145703 | 134146393 |
| chr11 | 134146682 | 134146894 | chr11 | 134201502 | 134201543 | chr11 | 134201841 | 134202084 |
| chr11 | 134281365 | 134281509 | chr12 | 570090 | 570171 | chr12 | 1639135 | 1639222 |
| chr12 | 1650475 | 1650577 | chr12 | 2046104 | 2046134 | chr12 | 2162554 | 2162817 |
| chr12 | 2163164 | 2163276 | chr12 | 2403658 | 2403714 | chr12 | 2566053 | 2566247 |
| chr12 | 2595199 | 2595339 | chr12 | 2862068 | 2862142 | chr12 | 2964465 | 2964577 |
| chr12 | 3371882 | 3371911 | chr12 | 3373533 | 3373666 | chr12 | 3600315 | 3600345 |
| chr12 | 3602270 | 3602716 | chr12 | 3602865 | 3602879 | chr12 | 3603100 | 3603156 |
| chr12 | 3862254 | 3862298 | chr12 | 4213973 | 4214157 | chr12 | 4231674 | 4231767 |
| chr12 | 4274054 | 4274188 | chr12 | 4274271 | 4274409 | chr12 | 4323835 | 4323912 |
| chr12 | 4362436 | 4362471 | chr12 | 4378252 | 4378330 | chr12 | 4379357 | 4379491 |
| chr12 | 4381433 | 4382386 | chr12 | 4382965 | 4382999 | chr12 | 4383492 | 4383784 |
| chr12 | 4384389 | 4384418 | chr12 | 4384736 | 4384902 | chr12 | 4392883 | 4392922 |
| chr12 | 4405589 | 4405619 | chr12 | 4431271 | 4431301 | chr12 | 4554801 | 4554831 |
| chr12 | 4919145 | 4919213 | chr12 | 4919239 | 4919244 | chr12 | 5018073 | 5018692 |
| chr12 | 5019085 | 5019742 | chr12 | 5019794 | 5020313 | chr12 | 5153039 | 5153286 |
| chr12 | 5153358 | 5153460 | chr12 | 5541100 | 5541177 | chr12 | 5542325 | 5542439 |
| chr12 | 5542759 | 5542911 | chr12 | 5840200 | 5840363 | chr12 | 6308743 | 6308772 |
| chr12 | 6473721 | 6473762 | chr12 | 6483615 | 6483756 | chr12 | 6664508 | 6664522 |
| chr12 | 6678158 | 6678203 | chr12 | 7403914 | 7404060 | chr12 | 7559160 | 7559307 |
| chr12 | 8025635 | 8025660 | chr12 | 8036526 | 8036634 | chr12 | 8122523 | 8122628 |
| chr12 | 8127036 | 8127140 | chr12 | 8127565 | 8127595 | chr12 | 8139203 | 8139233 |
| chr12 | 8163573 | 8163603 | chr12 | 8171360 | 8171745 | chr12 | 8180999 | 8181065 |
| chr12 | 8549178 | 8549208 | chr12 | 8808599 | 8808709 | chr12 | 8850658 | 8850744 |
| chr12 | 8975182 | 8975361 | chr12 | 9916313 | 9916343 | chr12 | 10085916 | 10085948 |
| chr12 | 10363278 | 10363607 | chr12 | 10772771 | 10772896 | chr12 | 11653449 | 11653463 |
| chr12 | 12456859 | 12456889 | chr12 | 12504616 | 12504850 | chr12 | 12848390 | 12848556 |
| chr12 | 13036048 | 13036078 | chr12 | 13055966 | 13055996 | chr12 | 14133152 | 14133263 |
| chr12 | 14133619 | 14133881 | chr12 | 14135111 | 14135339 | chr12 | 14719937 | 14719967 |
| chr12 | 14818824 | 14818867 | chr12 | 15374258 | 15374291 | chr12 | 16500576 | 16500621 |
| chr12 | 19282333 | 19282363 | chr12 | 20521704 | 20521841 | chr12 | 20522457 | 20522487 |
| chr12 | 20522769 | 20522891 | chr12 | 21680394 | 21680683 | chr12 | 21810264 | 21810868 |
| chr12 | 21833068 | 21833265 | chr12 | 22093825 | 22094268 | chr12 | 22094578 | 22094810 |
| chr12 | 22486799 | 22486881 | chr12 | 22487134 | 22487473 | chr12 | 22698063 | 22698110 |
| chr12 | 23229390 | 23229420 | chr12 | 24714909 | 24714938 | chr12 | 24715235 | 24715264 |
| chr12 | 24716033 | 24716218 | chr12 | 25056243 | 25056436 | chr12 | 25101592 | 25101660 |
| chr12 | 25101919 | 25101997 | chr12 | 25102010 | 25102086 | chr12 | 25362824 | 25362853 |
| chr12 | 25368463 | 25368492 | chr12 | 25378543 | 25378662 | chr12 | 25380231 | 26380299 |
| chr12 | 25398203 | 25398319 | chr12 | 26178334 | 26178376 | chr12 | 27114515 | 27114639 |
| chr12 | 27176441 | 27176539 | chr12 | 27494550 | 27494580 | chr12 | 28123996 | 28124247 |
| chr12 | 28127767 | 28128302 | chr12 | 28128547 | 28129084 | chr12 | 29936016 | 29936048 |
| chr12 | 29936602 | 29936642 | chr12 | 29936662 | 29936831 | chr12 | 29937331 | 29937374 |
| chr12 | 30322774 | 30322924 | chr12 | 30323015 | 30323439 | chr12 | 30323503 | 30323517 |
| chr12 | 30975572 | 30975959 | chr12 | 31079268 | 31079367 | chr12 | 31079418 | 31079499 |
| chr12 | 31316012 | 31316362 | chr12 | 31366306 | 31366336 | chr12 | 32086716 | 32086982 |
| chr12 | 32340317 | 32340534 | chr12 | 32831622 | 32831652 | chr12 | 33691774 | 33591804 |
| chr12 | 33592613 | 33592847 | chr12 | 34494888 | 34494918 | chr12 | 34502733 | 34502803 |

TABLE 12-continued

| chr | start | end | chr | start | end | chr | start | end |
|---|---|---|---|---|---|---|---|---|
| chr12 | 39299117 | 39299560 | chr12 | 39539353 | 39539436 | chr12 | 40618404 | 40618470 |
| chr12 | 41086183 | 41086379 | chr12 | 41086784 | 41087106 | chr12 | 41582513 | 41582988 |
| chr12 | 41583374 | 41583419 | chr12 | 43945110 | 43945124 | chr12 | 43945356 | 43945379 |
| chr12 | 43945417 | 43945526 | chr12 | 43946203 | 43946298 | chr12 | 45269504 | 45269624 |
| chr12 | 45444118 | 45444681 | chr12 | 45444715 | 45445258 | chr12 | 46767650 | 46767697 |
| chr12 | 47225381 | 47225476 | chr12 | 47225551 | 47225579 | chr12 | 47629349 | 47629379 |
| chr12 | 48397195 | 48398070 | chr12 | 48398641 | 48398671 | chr12 | 48690674 | 48690880 |
| chr12 | 49035233 | 49035414 | chr12 | 49074601 | 49074843 | chr12 | 49297802 | 49297915 |
| chr12 | 49366374 | 49366423 | chr12 | 49374914 | 49375026 | chr12 | 49375116 | 49375119 |
| chr12 | 49375325 | 49375529 | chr12 | 49390873 | 49391104 | chr12 | 49391147 | 49391877 |
| chr12 | 49515852 | 49515920 | chr12 | 49657705 | 49657901 | chr12 | 49691049 | 49691078 |
| chr12 | 49727092 | 49727127 | chr12 | 49729728 | 49730090 | chr12 | 49759530 | 49759559 |
| chr12 | 49989786 | 49989816 | chr12 | 50297497 | 50297554 | chr12 | 50297974 | 50298055 |
| chr12 | 50426748 | 50426799 | chr12 | 50507349 | 50507522 | chr12 | 50673944 | 50674096 |
| chr12 | 50897763 | 50898273 | chr12 | 51400044 | 51400091 | chr12 | 51420874 | 51421271 |
| chr12 | 51421556 | 51421586 | chr12 | 51441284 | 51441368 | chr12 | 51565269 | 51565548 |
| chr12 | 51625514 | 51625587 | chr12 | 51930708 | 51930862 | chr12 | 52262983 | 52263106 |
| chr12 | 52301280 | 52301305 | chr12 | 52400831 | 52401537 | chr12 | 52408905 | 52409033 |
| chr12 | 52627273 | 52627438 | chr12 | 52652153 | 52652219 | chr12 | 52652600 | 52652613 |
| chr12 | 53108089 | 53108218 | chr12 | 53359386 | 53359563 | chr12 | 53763427 | 53763885 |
| chr12 | 53766833 | 53766964 | chr12 | 53834392 | 53834475 | chr12 | 53885346 | 53885651 |
| chr12 | 54089093 | 54089511 | chr12 | 54132252 | 54132329 | chr12 | 54145843 | 54145857 |
| chr12 | 54145881 | 54145895 | chr12 | 54321250 | 54321628 | chr12 | 54322201 | 54322252 |
| chr12 | 54324799 | 54324937 | chr12 | 54329358 | 54329478 | chr12 | 54329605 | 54329947 |
| chr12 | 54331062 | 54331135 | chr12 | 54332868 | 54333337 | chr12 | 54338666 | 54338817 |
| chr12 | 54338979 | 54339681 | chr12 | 54343812 | 54343829 | chr12 | 54345611 | 54345658 |
| chr12 | 54345966 | 54346032 | chr12 | 54348844 | 64349079 | chr12 | 54349256 | 54349336 |
| chr12 | 54354514 | 54354621 | chr12 | 54354905 | 54355086 | chr12 | 54359960 | 54360084 |
| chr12 | 54360608 | 54360649 | chr12 | 54377912 | 54377946 | chr12 | 54377978 | 54378115 |
| chr12 | 54379174 | 54379623 | chr12 | 54379888 | 54379930 | chr12 | 54379959 | 54380459 |
| chr12 | 54387842 | 54387959 | chr12 | 54388215 | 54388245 | chr12 | 54391400 | 54391403 |
| chr12 | 54393479 | 54393684 | chr12 | 54393950 | 54394162 | chr12 | 54394410 | 54394418 |
| chr12 | 54398889 | 54398959 | chr12 | 54399616 | 54399646 | chr12 | 54402690 | 54402796 |
| chr12 | 54403067 | 54403360 | chr12 | 54408411 | 54408726 | chr12 | 54409476 | 54409505 |
| chr12 | 54423616 | 54423697 | chr12 | 54424746 | 54424748 | chr12 | 54425032 | 54425119 |
| chr12 | 54447351 | 54447581 | chr12 | 54447899 | 54447977 | chr12 | 54520745 | 54520868 |
| chr12 | 54613463 | 54613615 | chr12 | 54719808 | 54720232 | chr12 | 54812238 | 54812359 |
| chr12 | 54894048 | 54894173 | chr12 | 54922624 | 54922803 | chr12 | 54942994 | 54943116 |
| chr12 | 55480923 | 55481067 | chr12 | 55561202 | 55561354 | chr12 | 56231108 | 56231148 |
| chr12 | 56400463 | 56400591 | chr12 | 56478840 | 56478869 | chr12 | 56481645 | 56481937 |
| chr12 | 56486572 | 56486601 | chr12 | 56490965 | 56490994 | chr12 | 56491630 | 56491659 |
| chr12 | 56492618 | 56492642 | chr12 | 56558381 | 56558519 | chr12 | 56653281 | 56653369 |
| chr12 | 56873601 | 56873630 | chr12 | 56882240 | 56882380 | chr12 | 57174355 | 57174452 |
| chr12 | 57359920 | 57359950 | chr12 | 57387303 | 57387332 | chr12 | 57559869 | 57559925 |
| chr12 | 57618574 | 57618710 | chr12 | 57881127 | 57881383 | chr12 | 57944081 | 57944117 |
| chr12 | 57983314 | 57983348 | chr12 | 58021320 | 58021458 | chr12 | 58021916 | 58022029 |
| chr12 | 58025646 | 58025733 | chr12 | 58025870 | 58025873 | chr12 | 58145415 | 58145450 |
| chr12 | 59314159 | 59314189 | chr12 | 62584838 | 62585012 | chr12 | 62585031 | 62586017 |
| chr12 | 62586252 | 62586281 | chr12 | 62603907 | 62603937 | chr12 | 62858444 | 62858575 |
| chr12 | 63025574 | 63026160 | chr12 | 63326618 | 63326648 | chr12 | 63543848 | 63544401 |
| chr12 | 63544499 | 63544599 | chr12 | 63545313 | 63545343 | chr12 | 64028352 | 64028382 |
| chr12 | 64061821 | 64062159 | chr12 | 64062369 | 64062578 | chr12 | 64062921 | 64063096 |
| chr12 | 64783185 | 64783308 | chr12 | 64784108 | 64784252 | chr12 | 64784534 | 64784564 |
| chr12 | 65218102 | 65218550 | chr12 | 65218901 | 65219156 | chr12 | 65219376 | 65219527 |
| chr12 | 65219606 | 65219784 | chr12 | 65220206 | 65220350 | chr12 | 65514863 | 65515596 |
| chr12 | 65516360 | 65516455 | chr12 | 53557212 | 65557376 | chr12 | 55561778 | 65562086 |
| chr12 | 66122800 | 66122995 | chr12 | 66123381 | 66123519 | chr12 | 66135984 | 66136014 |
| chr12 | 66582827 | 66583137 | chr12 | 68433260 | 68433321 | chr12 | 68964473 | 68964503 |
| chr12 | 68978322 | 68978576 | chr12 | 69327259 | 69327463 | chr12 | 69754451 | 69754729 |
| chr12 | 69964176 | 69964264 | chr12 | 70087493 | 70087568 | chr12 | 70698883 | 70699050 |
| chr12 | 72332641 | 72332696 | chr12 | 72665186 | 72665788 | chr12 | 72666713 | 72666807 |
| chr12 | 72666998 | 72667425 | chr12 | 72667652 | 72667682 | chr12 | 75601379 | 75601499 |
| chr12 | 75601696 | 75601910 | chr12 | 75602976 | 75603231 | chr12 | 75728336 | 75728485 |
| chr12 | 75728737 | 75728766 | chr12 | 77719311 | 77719422 | chr12 | 79257222 | 79257351 |
| chr12 | 81102185 | 81102455 | chr12 | 81102513 | 81102562 | chr12 | 81107997 | 81108034 |
| chr12 | 81471517 | 81471614 | chr12 | 81471754 | 81472111 | chr12 | 85306519 | 85306572 |
| chr12 | 85667272 | 85667731 | chr12 | 85673206 | 85673235 | chr12 | 85673460 | 85674807 |
| chr12 | 88973544 | 88973582 | chr12 | 88974159 | 88974253 | chr12 | 89915009 | 89915043 |
| chr12 | 93476304 | 93476342 | chr12 | 93966429 | 93966603 | chr12 | 93966998 | 93967215 |
| chr12 | 94543409 | 94543445 | chr12 | 94543899 | 94543961 | chr12 | 94544022 | 94544052 |
| chr12 | 94852412 | 94852506 | chr12 | 95216830 | 95216960 | chr12 | 95267524 | 95267554 |
| chr12 | 95267865 | 95267976 | chr12 | 95822981 | 95823011 | chr12 | 95866563 | 95866609 |
| chr12 | 95942965 | 95942978 | chr12 | 96880822 | 96881029 | chr12 | 98948200 | 98948295 |
| chr12 | 98949938 | 98949972 | chr12 | 98961066 | 98961241 | chr12 | 98986343 | 98986491 |
| chr12 | 99288312 | 99288407 | chr12 | 99288622 | 99288936 | chr12 | 99289162 | 99289309 |
| chr12 | 100595495 | 100595558 | chr12 | 101025380 | 101025410 | chr12 | 101111029 | 101111061 |
| chr12 | 101111373 | 101111479 | chr12 | 102457208 | 102457238 | chr12 | 103218495 | 103218595 |
| chr12 | 103351564 | 103351985 | chr12 | 103352052 | 103352154 | chr12 | 103352171 | 103352282 |

TABLE 12-continued

| chr | start | end | chr | start | end | chr | start | end |
|---|---|---|---|---|---|---|---|---|
| chr12 | 103352314 | 103352681 | chr12 | 103358865 | 103358899 | chr12 | 103359556 | 103359586 |
| chr12 | 103889160 | 103889211 | chr12 | 103889789 | 103889812 | chr12 | 104506691 | 104506783 |
| chr12 | 104609417 | 104609796 | chr12 | 104671030 | 104671064 | chr12 | 104671699 | 104671761 |
| chr12 | 104684181 | 104684258 | chr12 | 104696376 | 104696502 | chr12 | 104850505 | 104850536 |
| chr12 | 104850578 | 104850592 | chr12 | 104851077 | 104851186 | chr12 | 104852032 | 104852508 |
| chr12 | 105017109 | 105017228 | chr12 | 105478323 | 105478419 | chr12 | 106533852 | 106533881 |
| chr12 | 106974353 | 106974383 | chr12 | 106976725 | 106976779 | chr12 | 106977321 | 106977497 |
| chr12 | 106979161 | 106979534 | chr12 | 106979799 | 106979995 | chr12 | 106980223 | 106980333 |
| chr12 | 106980912 | 106981406 | chr12 | 107486550 | 107486672 | chr12 | 107487194 | 107487855 |
| chr12 | 107712273 | 107712303 | chr12 | 107713205 | 107713235 | chr12 | 107714866 | 107715153 |
| chr12 | 108080498 | 108080553 | chr12 | 108168971 | 108168413 | chr12 | 108169550 | 108169573 |
| chr12 | 108237466 | 108237524 | chr12 | 108238102 | 108238513 | chr12 | 108297411 | 108297466 |
| chr12 | 109488519 | 109488685 | chr12 | 109639281 | 109639475 | chr12 | 110353414 | 110353451 |
| chr12 | 110507084 | 110507207 | chr12 | 110717541 | 110717710 | chr12 | 110840344 | 110840404 |
| chr12 | 110854243 | 110854288 | chr12 | 110887179 | 110887209 | chr12 | 110983706 | 110983736 |
| chr12 | 111127124 | 111127455 | chr12 | 111143726 | 111143756 | chr12 | 111471177 | 111471559 |
| chr12 | 111471948 | 111471959 | chr12 | 111472059 | 111472195 | chr12 | 111472357 | 111472671 |
| chr12 | 111763122 | 111763152 | chr12 | 112547662 | 112547692 | chr12 | 112574734 | 112574995 |
| chr12 | 112792829 | 112792944 | chr12 | 112825760 | 112825896 | chr12 | 112888151 | 112888315 |
| chr12 | 112910821 | 112910850 | chr12 | 112915509 | 112915538 | chr12 | 112926255 | 112926284 |
| chr12 | 112926876 | 112926914 | chr12 | 113012954 | 113013157 | chr12 | 113541667 | 113542099 |
| chr12 | 113592238 | 113592359 | chr12 | 113795506 | 113795657 | chr12 | 113900753 | 113900765 |
| chr12 | 113901074 | 113901158 | chr12 | 113901408 | 113901591 | chr12 | 113902042 | 113902353 |
| chr12 | 113903468 | 113903498 | chr12 | 113904779 | 113905016 | chr12 | 113908990 | 113909314 |
| chr12 | 113909329 | 113909455 | chr12 | 113913267 | 113913681 | chr12 | 113913884 | 113914050 |
| chr12 | 113916222 | 113916316 | chr12 | 113916649 | 113916678 | chr12 | 113916972 | 113917012 |
| chr12 | 113917232 | 113917310 | chr12 | 113917775 | 113917890 | chr12 | 114029408 | 114029660 |
| chr12 | 114076029 | 114076093 | chr12 | 114337763 | 114337793 | chr12 | 114833985 | 114834102 |
| chr12 | 114838369 | 114838726 | chr12 | 114839104 | 114839147 | chr12 | 114841046 | 114841084 |
| chr12 | 114841425 | 114841493 | chr12 | 114843112 | 114843186 | chr12 | 114843261 | 114843278 |
| chr12 | 114843545 | 114843660 | chr12 | 114844201 | 114844300 | chr12 | 114846715 | 114846768 |
| chr12 | 114847043 | 114847435 | chr12 | 114847578 | 114847691 | chr12 | 114852040 | 114852082 |
| chr12 | 114852293 | 114852373 | chr12 | 114877171 | 114877262 | chr12 | 114878550 | 114878584 |
| chr12 | 114878813 | 114879012 | chr12 | 114881634 | 114881764 | chr12 | 114882555 | 114882646 |
| chr12 | 114883473 | 114883535 | chr12 | 114918594 | 114918717 | chr12 | 115136159 | 115136363 |
| chr12 | 116946086 | 116946199 | chr12 | 116946251 | 116946548 | chr12 | 117474065 | 117474198 |
| chr12 | 117526330 | 117526368 | chr12 | 117798065 | 117798095 | chr12 | 117799413 | 117799529 |
| chr12 | 118860397 | 118860654 | chr12 | 118920764 | 118920804 | chr12 | 119212319 | 119212381 |
| chr12 | 119418594 | 119418847 | chr12 | 119419436 | 119419466 | chr12 | 119419720 | 119419899 |
| chr12 | 120032862 | 120033169 | chr12 | 120148142 | 120148248 | chr12 | 120148923 | 120148962 |
| chr12 | 120535158 | 120535187 | chr12 | 120536625 | 120536654 | chr12 | 120885215 | 120885245 |
| chr12 | 120971686 | 120971716 | chr12 | 121622546 | 121622576 | chr12 | 122108464 | 122108601 |
| chr12 | 122192723 | 122192843 | chr12 | 122278388 | 122278580 | chr12 | 122285067 | 122285108 |
| chr12 | 122473581 | 122473611 | chr12 | 122940449 | 122940479 | chr12 | 123129129 | 123129550 |
| chr12 | 123211316 | 123211390 | chr12 | 123233646 | 123233846 | chr12 | 123410210 | 123410240 |
| chr12 | 123942025 | 123942189 | chr12 | 124117199 | 124117289 | chr12 | 124246908 | 124246937 |
| chr12 | 124247208 | 124247237 | chr12 | 124393560 | 124393604 | chr12 | 124397464 | 124397618 |
| chr12 | 124865115 | 124865144 | chr12 | 125009276 | 125009306 | chr12 | 125533949 | 125534407 |
| chr12 | 125589840 | 125589872 | chr12 | 125670117 | 125670260 | chr12 | 126168554 | 126168620 |
| chr12 | 127211317 | 127211378 | chr12 | 127765158 | 127765432 | chr12 | 127940086 | 127940247 |
| chr12 | 128751384 | 128751443 | chr12 | 128751821 | 128751877 | chr12 | 128752115 | 128752240 |
| chr12 | 128752499 | 128752944 | chr12 | 128753210 | 128753240 | chr12 | 128850534 | 128850644 |
| chr12 | 129338588 | 129338816 | chr12 | 129427424 | 129427557 | chr12 | 129447299 | 129447450 |
| chr12 | 130037653 | 130037778 | chr12 | 130387797 | 130387811 | chr12 | 130388410 | 130388434 |
| chr12 | 130389013 | 130389152 | chr12 | 130589202 | 130589266 | chr12 | 130645233 | 130645627 |
| chr12 | 130646946 | 130647115 | chr12 | 130647574 | 130647908 | chr12 | 130647951 | 130648069 |
| chr12 | 130821371 | 130821621 | chr12 | 130968621 | 130968654 | chr12 | 131200379 | 131200645 |
| chr12 | 131400816 | 131400919 | chr12 | 131403032 | 131403125 | chr12 | 131513345 | 131513403 |
| chr12 | 132102173 | 132102202 | chr12 | 132169288 | 132169442 | chr12 | 132221689 | 132222076 |
| chr12 | 132332910 | 132332940 | chr12 | 132333434 | 132333597 | chr12 | 132348651 | 132348684 |
| chr12 | 132423516 | 132423854 | chr12 | 132643233 | 132643279 | chr12 | 132986495 | 132986581 |
| chr12 | 133002792 | 133003231 | chr12 | 133172907 | 133173021 | chr12 | 133195093 | 133195196 |
| chr12 | 133199738 | 133199784 | chr12 | 133262698 | 133262926 | chr12 | 133280578 | 133280682 |
| chr12 | 133463736 | 133463876 | chr12 | 133464108 | 133464166 | chr12 | 133464840 | 133465027 |
| chr12 | 133481490 | 133481655 | chr12 | 133484742 | 133484823 | chr12 | 133485162 | 133485347 |
| chr12 | 133485557 | 133485689 | chr12 | 133485816 | 133485847 | chr12 | 133758048 | 133758107 |
| chr13 | 20175911 | 20175941 | chr13 | 20451144 | 20451360 | chr13 | 20735804 | 20736089 |
| chr13 | 21649636 | 21649775 | chr13 | 21713233 | 21713513 | chr13 | 22243273 | 22243469 |
| chr13 | 23489851 | 23489914 | chr13 | 23653781 | 23653813 | chr13 | 23733447 | 23734020 |
| chr13 | 23734284 | 23734297 | chr13 | 24099683 | 24099713 | chr13 | 24477643 | 24477906 |
| chr13 | 25115713 | 25115771 | chr13 | 25319856 | 25319904 | chr13 | 25320388 | 25320539 |
| chr13 | 25320614 | 25321028 | chr13 | 25321113 | 25321350 | chr13 | 25321699 | 25321942 |
| chr13 | 25593062 | 25593242 | chr13 | 25621045 | 25621205 | chr13 | 25621264 | 25621394 |
| chr13 | 25668799 | 25668829 | chr13 | 25744716 | 25744734 | chr13 | 25745301 | 25745594 |
| chr13 | 25745722 | 25746000 | chr13 | 25946301 | 25946411 | chr13 | 25946620 | 25946673 |
| chr13 | 26042678 | 26042707 | chr13 | 26042769 | 26043170 | chr13 | 26043341 | 26043499 |
| chr13 | 26340608 | 26340755 | chr13 | 26625301 | 26625656 | chr13 | 27334211 | 27334563 |
| chr13 | 27334772 | 27334894 | chr13 | 27699893 | 77699981 | chr13 | 28239909 | 28240164 |

TABLE 12-continued

| chr | start | end | chr | start | end | chr | start | end |
|---|---|---|---|---|---|---|---|---|
| chr13 | 28365705 | 28366122 | chr13 | 28366482 | 28366577 | chr13 | 28367024 | 28367038 |
| chr13 | 28367794 | 28367945 | chr13 | 28368154 | 28368168 | chr13 | 28368451 | 28368593 |
| chr13 | 28368952 | 28369070 | chr13 | 28369162 | 28369990 | chr13 | 28370947 | 28371061 |
| chr13 | 28394766 | 28394866 | chr13 | 28395501 | 28395553 | chr13 | 28395998 | 28396073 |
| chr13 | 28491793 | 28491946 | chr13 | 28492244 | 28492553 | chr13 | 28503042 | 28503074 |
| chr13 | 28528534 | 28528748 | chr13 | 28540745 | 28540927 | chr13 | 28543212 | 28543242 |
| chr13 | 28544397 | 28544584 | chr13 | 28544666 | 28544903 | chr13 | 28549497 | 28549891 |
| chr13 | 28550240 | 28550552 | chr13 | 28551417 | 28551461 | chr13 | 28551950 | 28552167 |
| chr13 | 28552794 | 28552824 | chr13 | 28553030 | 28553138 | chr13 | 28589765 | 28589794 |
| chr13 | 28592605 | 28592658 | chr13 | 28601345 | 28601374 | chr13 | 28602326 | 28602355 |
| chr13 | 28608233 | 28608355 | chr13 | 28610123 | 28610152 | chr13 | 28674018 | 28674226 |
| chr13 | 28674721 | 28674734 | chr13 | 28706016 | 28706140 | chr13 | 29067773 | 29068416 |
| chr13 | 29068926 | 29068985 | chr13 | 29068994 | 29069065 | chr13 | 29106308 | 29106814 |
| chr13 | 29106899 | 29107063 | chr13 | 29107253 | 29107309 | chr13 | 29112395 | 29112444 |
| chr13 | 30141688 | 30141718 | chr13 | 30707569 | 30707599 | chr13 | 31185432 | 31185548 |
| chr13 | 31742953 | 31743177 | chr13 | 32605034 | 32605324 | chr13 | 32605443 | 32605623 |
| chr13 | 32605675 | 32605966 | chr13 | 33591300 | 33591419 | chr13 | 33924666 | 33924790 |
| chr13 | 35517410 | 35517648 | chr13 | 36044829 | 36044930 | chr13 | 36049995 | 36050025 |
| chr13 | 36269480 | 36269509 | chr13 | 36541300 | 36541329 | chr13 | 36553399 | 36553428 |
| chr13 | 36588100 | 36588129 | chr13 | 36704939 | 36705055 | chr13 | 36705451 | 36705489 |
| chr13 | 36909206 | 36909236 | chr13 | 36920317 | 36920386 | chr13 | 36920628 | 36920785 |
| chr13 | 37004771 | 37005129 | chr13 | 37005900 | 37006062 | chr13 | 37006434 | 37006657 |
| chr13 | 37006704 | 37006762 | chr13 | 37248063 | 37248148 | chr13 | 37248295 | 37248319 |
| chr13 | 37248979 | 37248993 | chr13 | 37633989 | 37634018 | chr13 | 37643942 | 37644005 |
| chr13 | 38402239 | 38402268 | chr13 | 38443618 | 38443715 | chr13 | 39261410 | 39261446 |
| chr13 | 40000498 | 40000528 | chr13 | 41346048 | 41346088 | chr13 | 41496324 | 41496478 |
| chr13 | 41884500 | 41884688 | chr13 | 43148669 | 43148698 | chr13 | 43566247 | 43566647 |
| chr13 | 43620862 | 43621006 | chr13 | 44947746 | 44948197 | chr13 | 45150013 | 45150276 |
| chr13 | 45885876 | 45885905 | chr13 | 45905088 | 45905264 | chr13 | 46425548 | 46425554 |
| chr13 | 46425576 | 46425584 | chr13 | 46649031 | 46649141 | chr13 | 46660839 | 46660869 |
| chr13 | 46961494 | 46961533 | chr13 | 46961952 | 46961982 | chr13 | 47407767 | 47407796 |
| chr13 | 47468139 | 47468168 | chr13 | 47472315 | 47472344 | chr13 | 47526030 | 47526182 |
| chr13 | 48478576 | 48478605 | chr13 | 48667877 | 48667907 | chr13 | 49794117 | 49794925 |
| chr13 | 50266473 | 50266573 | chr13 | 50367946 | 50368123 | chr13 | 50421504 | 50421696 |
| chr13 | 50639705 | 50639799 | chr13 | 52270145 | 52270175 | chr13 | 52565068 | 52565194 |
| chr13 | 52580318 | 52580369 | chr13 | 53312991 | 53313313 | chr13 | 53313513 | 53313612 |
| chr13 | 53313678 | 53313920 | chr13 | 53419734 | 53419775 | chr13 | 53420020 | 53420020 |
| chr13 | 53423838 | 53423978 | chr13 | 55146522 | 55146551 | chr13 | 55373897 | 55373926 |
| chr13 | 55628658 | 55628687 | chr13 | 56762456 | 56762485 | chr13 | 57714539 | 57714568 |
| chr13 | 58203602 | 58203644 | chr13 | 58203851 | 58204103 | chr13 | 58204350 | 58204393 |
| chr13 | 58206042 | 58206231 | chr13 | 58206453 | 58206771 | chr13 | 58206862 | 58206983 |
| chr13 | 58207568 | 58207813 | chr13 | 58207892 | 58208020 | chr13 | 58208495 | 58208926 |
| chr13 | 58892774 | 58892803 | chr13 | 59531686 | 59531715 | chr13 | 62132346 | 62132375 |
| chr13 | 64650200 | 64650229 | chr13 | 65532258 | 65532287 | chr13 | 66697959 | 66698124 |
| chr13 | 67196371 | 67196400 | chr13 | 67197158 | 67197187 | chr13 | 67803735 | 67804074 |
| chr13 | 67804494 | 67804523 | chr13 | 67805191 | 67805247 | chr13 | 68488923 | 68488952 |
| chr13 | 68682015 | 68682044 | chr13 | 68745282 | 68745311 | chr13 | 69796842 | 69796871 |
| chr13 | 70681626 | 70681777 | chr13 | 70681867 | 70682071 | chr13 | 71498386 | 71498415 |
| chr13 | 72439142 | 72439250 | chr13 | 73184723 | 73184752 | chr13 | 73336049 | 73336078 |
| chr13 | 73619660 | 73619784 | chr13 | 76440730 | 76440760 | chr13 | 76869421 | 76869450 |
| chr13 | 77553779 | 77553809 | chr13 | 78492684 | 78492840 | chr13 | 78493166 | 78493196 |
| chr13 | 78493455 | 78493809 | chr13 | 79168067 | 79168102 | chr13 | 79169850 | 79170113 |
| chr13 | 79170348 | 79170383 | chr13 | 79170468 | 79170884 | chr13 | 79171118 | 79171196 |
| chr13 | 79175770 | 79175943 | chr13 | 79176078 | 79176125 | chr13 | 79176277 | 79176420 |
| chr13 | 79176609 | 79176783 | chr13 | 79176993 | 79177184 | chr13 | 79177306 | 79177622 |
| chr13 | 79177886 | 79177998 | chr13 | 79183406 | 79183423 | chr13 | 79693095 | 79693124 |
| chr13 | 79993101 | 79993142 | chr13 | 81229343 | 81229372 | chr13 | 84455236 | 84455292 |
| chr13 | 84455581 | 84455715 | chr13 | 84457491 | 84457521 | chr13 | 82731371 | 87731400 |
| chr13 | 88323579 | 88323830 | chr13 | 88323868 | 88324207 | chr13 | 88324516 | 88324518 |
| chr13 | 88325300 | 88325460 | chr13 | 88325819 | 88326061 | chr13 | 88326538 | 88326707 |
| chr13 | 88326937 | 88327014 | chr13 | 88629123 | 88629152 | chr13 | 88788883 | 88788912 |
| chr13 | 88997906 | 88997935 | chr13 | 89815436 | 89815465 | chr13 | 90015503 | 90015532 |
| chr13 | 90015897 | 90015926 | chr13 | 91755723 | 91755837 | chr13 | 91948489 | 91948519 |
| chr13 | 92050760 | 92060814 | chr13 | 92051139 | 92051168 | chr13 | 92051374 | 92051513 |
| chr13 | 93859304 | 93859333 | chr13 | 93879288 | 93879375 | chr13 | 93879670 | 93879700 |
| chr13 | 93880089 | 93880216 | chr13 | 93880534 | 93880737 | chr13 | 93880794 | 93880856 |
| chr13 | 94107209 | 94107238 | chr13 | 95086143 | 95086172 | chr13 | 95357311 | 95357341 |
| chr13 | 95357574 | 95357775 | chr13 | 95358041 | 95358165 | chr13 | 95359747 | 95359803 |
| chr13 | 95360322 | 95360371 | chr13 | 95363210 | 95363429 | chr13 | 95363796 | 95363959 |
| chr13 | 95364065 | 95364196 | chr13 | 95364495 | 95364800 | chr13 | 95620021 | 95620078 |
| chr13 | 95620647 | 95620781 | chr13 | 95620854 | 95621011 | chr13 | 96031705 | 96031815 |
| chr13 | 96177285 | 96177315 | chr13 | 96204923 | 96205363 | chr13 | 96296225 | 96296345 |
| chr13 | 96296373 | 96296473 | chr13 | 96296841 | 96296949 | chr13 | 96296992 | 96297137 |
| chr13 | 96743788 | 96744175 | chr13 | 97761876 | 97761925 | chr13 | 99851676 | 99851706 |
| chr13 | 100547713 | 100547893 | chr13 | 100608462 | 100608804 | chr13 | 100608839 | 100609055 |
| chr13 | 100621941 | 100622015 | chr13 | 100624324 | 100624348 | chr13 | 100624587 | 100624729 |
| chr13 | 100626929 | 100627009 | chr13 | 100627295 | 100627348 | chr13 | 100627688 | 100627712 |
| chr13 | 100630169 | 100630298 | chr13 | 100630329 | 100630430 | chr13 | 100630630 | 100630997 |

TABLE 12-continued

| chr | start | end | chr | start | end | chr | start | end |
|---|---|---|---|---|---|---|---|---|
| chr13 | 100633089 | 100633184 | chr13 | 100634314 | 100634617 | chr13 | 100635406 | 100635451 |
| chr13 | 100636167 | 100636238 | chr13 | 100637390 | 100637485 | chr13 | 100641282 | 100641408 |
| chr13 | 100642120 | 100642201 | chr13 | 100643296 | 100643435 | chr13 | 100644055 | 100644179 |
| chr13 | 100649325 | 100649575 | chr13 | 100649800 | 100649884 | chr13 | 102197373 | 102197408 |
| chr13 | 102568454 | 102568484 | chr13 | 102569313 | 102569542 | chr13 | 103046721 | 103046995 |
| chr13 | 103062347 | 103052574 | chr13 | 103052892 | 103062940 | chr13 | 103053394 | 103053496 |
| chr13 | 103821419 | 103821448 | chr13 | 105484285 | 105484314 | chr13 | 105791875 | 105791904 |
| chr13 | 107186855 | 107186884 | chr13 | 107187162 | 107187426 | chr13 | 107187666 | 107187695 |
| chr13 | 107188241 | 107188430 | chr13 | 107827301 | 107827331 | chr13 | 108518813 | 108518933 |
| chr13 | 108519254 | 108519367 | chr13 | 108519737 | 108519745 | chr13 | 108520376 | 108520534 |
| chr13 | 108520979 | 108521076 | chr13 | 108816328 | 108816378 | chr13 | 108869613 | 108869830 |
| chr13 | 109147685 | 109147862 | chr13 | 109148155 | 109148278 | chr13 | 109148783 | 109149185 |
| chr13 | 110434451 | 110434593 | chr13 | 110958816 | 110958981 | chr13 | 110959753 | 110959970 |
| chr13 | 110960541 | 110960603 | chr13 | 111278255 | 111278426 | chr13 | 111363787 | 111363972 |
| chr13 | 112272991 | 112273088 | chr13 | 112707694 | 112707869 | chr13 | 112708308 | 112708513 |
| chr13 | 112709388 | 112709617 | chr13 | 112709883 | 112709928 | chr13 | 112710360 | 112710475 |
| chr13 | 112710759 | 112711293 | chr13 | 112711376 | 112711776 | chr13 | 112712017 | 112713029 |
| chr13 | 112715370 | 112715642 | chr13 | 112715985 | 112716313 | chr13 | 112716677 | 112716721 |
| chr13 | 112717026 | 112717242 | chr13 | 112717323 | 112717536 | chr13 | 112717835 | 112717949 |
| chr13 | 112720033 | 112720505 | chr13 | 112720723 | 112720767 | chr13 | 112721012 | 112721026 |
| chr13 | 112722129 | 112722220 | chr13 | 112722275 | 112722312 | chr13 | 112724505 | 112724535 |
| chr13 | 112726436 | 112726560 | chr13 | 112727984 | 112728200 | chr13 | 112758107 | 112758257 |
| chr13 | 112758274 | 112758372 | chr13 | 112758496 | 112758613 | chr13 | 112759112 | 112759248 |
| chr13 | 112759612 | 112759642 | chr13 | 112760007 | 112760327 | chr13 | 112760795 | 112761214 |
| chr13 | 113244509 | 113244595 | chr13 | 113598618 | 113598851 | chr13 | 113938542 | 113938603 |
| chr13 | 113985679 | 113986053 | chr13 | 114055983 | 114056137 | chr13 | 114060064 | 114060333 |
| chr13 | 114074768 | 114074853 | chr13 | 114082984 | 114083046 | chr13 | 114123168 | 114123291 |
| chr13 | 114189737 | 114189809 | chr13 | 114221622 | 114221652 | chr13 | 114304565 | 114304927 |
| chr13 | 114479404 | 114479434 | chr13 | 114498017 | 114498260 | chr13 | 114568046 | 114568076 |
| chr13 | 114748342 | 114748638 | chr13 | 114766270 | 114766300 | chr13 | 114780561 | 114781061 |
| chr13 | 114807617 | 114807815 | chr13 | 114855635 | 114855669 | chr13 | 114862308 | 114862368 |
| chr13 | 114897194 | 114897240 | chr13 | 114961823 | 114961933 | chr14 | 21093454 | 21093631 |
| chr14 | 21100748 | 21100778 | chr14 | 21100801 | 21100831 | chr14 | 22005029 | 22005073 |
| chr14 | 23234956 | 23235032 | chr14 | 23356044 | 23356384 | chr14 | 23400315 | 23400354 |
| chr14 | 23426755 | 23426785 | chr14 | 23701644 | 23701737 | chr14 | 23706727 | 23706765 |
| chr14 | 24562744 | 24562774 | chr14 | 24641010 | 24641215 | chr14 | 24803594 | 24804122 |
| chr14 | 25071566 | 25071612 | chr14 | 25155907 | 25155985 | chr14 | 26674354 | 26674384 |
| chr14 | 26674699 | 26674729 | chr14 | 27066562 | 27066785 | chr14 | 27067373 | 27067386 |
| chr14 | 29225531 | 29225561 | chr14 | 29226071 | 29226198 | chr14 | 29228654 | 29228778 |
| chr14 | 29229107 | 29229386 | chr14 | 29231071 | 29231185 | chr14 | 29231425 | 29231590 |
| chr14 | 29235003 | 29235308 | chr14 | 29235342 | 29235356 | chr14 | 29237063 | 29237066 |
| chr14 | 29242763 | 29242908 | chr14 | 29243516 | 29243669 | chr14 | 29243731 | 29243888 |
| chr14 | 29244224 | 29244308 | chr14 | 29247689 | 29247740 | chr14 | 29254612 | 29254713 |
| chr14 | 31027323 | 31027367 | chr14 | 31344346 | 31344549 | chr14 | 31925554 | 31925724 |
| chr14 | 32597620 | 32597657 | chr14 | 33402462 | 33402762 | chr14 | 33403045 | 33403316 |
| chr14 | 33403866 | 33404418 | chr14 | 34269897 | 34270004 | chr14 | 34420250 | 34420288 |
| chr14 | 35023111 | 35023322 | chr14 | 35024446 | 35024546 | chr14 | 35389907 | 35389943 |
| chr14 | 36003442 | 36003826 | chr14 | 36004081 | 36004493 | chr14 | 36004711 | 36004734 |
| chr14 | 36004822 | 36004921 | chr14 | 36972803 | 36972912 | chr14 | 36973455 | 36973538 |
| chr14 | 36974294 | 36974927 | chr14 | 36974968 | 36974982 | chr14 | 36975299 | 36975399 |
| chr14 | 36977645 | 36977929 | chr14 | 36977975 | 36978009 | chr14 | 36978548 | 36978578 |
| chr14 | 36979619 | 36979649 | chr14 | 36982927 | 36982969 | chr14 | 36983708 | 36984146 |
| chr14 | 36985841 | 36985871 | chr14 | 36986301 | 36986471 | chr14 | 36987302 | 36987685 |
| chr14 | 36987939 | 36988143 | chr14 | 36988428 | 36988460 | chr14 | 36990858 | 36991032 |
| chr14 | 36991095 | 36991177 | chr14 | 36991532 | 36991613 | chr14 | 36991989 | 36992163 |
| chr14 | 36992222 | 36992417 | chr14 | 36993473 | 36993487 | chr14 | 36993694 | 36993956 |
| chr14 | 36994248 | 36994999 | chr14 | 37050752 | 37050794 | chr14 | 37116105 | 37116294 |
| chr14 | 37117611 | 37117697 | chr14 | 37123438 | 37124077 | chr14 | 37124482 | 37124572 |
| chr14 | 37124992 | 37125545 | chr14 | 37126241 | 37126297 | chr14 | 37126566 | 37126213 |
| chr14 | 37127281 | 37127311 | chr14 | 37127655 | 37127779 | chr14 | 37128553 | 37128723 |
| chr14 | 37130077 | 37130260 | chr14 | 37132375 | 37132553 | chr14 | 37132603 | 37132695 |
| chr14 | 37133001 | 37133052 | chr14 | 37135784 | 37136017 | chr14 | 37136295 | 37136345 |
| chr14 | 37136588 | 37136618 | chr14 | 38060677 | 38060916 | chr14 | 38064401 | 38064549 |
| chr14 | 38627519 | 38677548 | chr14 | 38677761 | 38627790 | chr14 | 38724294 | 38724525 |
| chr14 | 38724979 | 38725258 | chr14 | 38725521 | 38725764 | chr14 | 39579800 | 39579830 |
| chr14 | 42074544 | 42074586 | chr14 | 42074669 | 42074987 | chr14 | 42075588 | 42076043 |
| chr14 | 42076106 | 42076212 | chr14 | 42076823 | 42076853 | chr14 | 42077230 | 42077268 |
| chr14 | 42077770 | 42077800 | chr14 | 42079289 | 42079328 | chr14 | 45602514 | 45602576 |
| chr14 | 48143798 | 48143957 | chr14 | 48144359 | 48144401 | chr14 | 48144699 | 48144763 |
| chr14 | 48145237 | 48145257 | chr14 | 50233426 | 50233459 | chr14 | 50333754 | 50333994 |
| chr14 | 50334254 | 50334355 | chr14 | 50355854 | 50355924 | chr14 | 50681598 | 50681859 |
| chr14 | 50777663 | 50777714 | chr14 | 51338730 | 51338731 | chr14 | 51560304 | 51560713 |
| chr14 | 51560773 | 51561428 | chr14 | 51561765 | 51562012 | chr14 | 51829264 | 51829396 |
| chr14 | 51955509 | 51955538 | chr14 | 52534648 | 52534791 | chr14 | 52535012 | 52535026 |
| chr14 | 52535056 | 52535263 | chr14 | 52535335 | 52536104 | chr14 | 52536343 | 52536404 |
| chr14 | 52734509 | 52734557 | chr14 | 52734777 | 52735001 | chr14 | 52735045 | 52735255 |
| chr14 | 52765920 | 52766075 | chr14 | 52781525 | 52781916 | chr14 | 54422651 | 54422925 |
| chr14 | 55370202 | 55370235 | chr14 | 55595938 | 55595968 | chr14 | 55668368 | 55668526 |

TABLE 12-continued

| chr | start | end | chr | start | end | chr | start | end |
|---|---|---|---|---|---|---|---|---|
| chr14 | 55765285 | 55765714 | chr14 | 55823079 | 55823218 | chr14 | 57045520 | 57045739 |
| chr14 | 57260946 | 57261094 | chr14 | 57261175 | 57261407 | chr14 | 57261466 | 57261821 |
| chr14 | 57262072 | 57262179 | chr14 | 57264079 | 57264645 | chr14 | 57264765 | 57264806 |
| chr14 | 57265148 | 57265240 | chr14 | 57270936 | 57270971 | chr14 | 57271154 | 57271266 |
| chr14 | 57272009 | 57272067 | chr14 | 57274486 | 57275049 | chr14 | 57275211 | 57275305 |
| chr14 | 57275596 | 57275685 | chr14 | 57276074 | 57276104 | chr14 | 57276440 | 57276666 |
| chr14 | 57277920 | 57278762 | chr14 | 57278838 | 57279564 | chr14 | 57279643 | 57279657 |
| chr14 | 57283314 | 57283408 | chr14 | 57283446 | 57284036 | chr14 | 57284071 | 57284659 |
| chr14 | 58332297 | 58332403 | chr14 | 58857094 | 58857355 | chr14 | 58893052 | 58893183 |
| chr14 | 59770326 | 59770452 | chr14 | 60097193 | 60097246 | chr14 | 60097407 | 60097566 |
| chr14 | 60386202 | 60386252 | chr14 | 60386638 | 60386701 | chr14 | 60794635 | 60794667 |
| chr14 | 60952196 | 60952419 | chr14 | 60952517 | 60952632 | chr14 | 60952730 | 60952959 |
| chr14 | 60973151 | 60973324 | chr14 | 60973697 | 60974007 | chr14 | 60974368 | 60974403 |
| chr14 | 60975384 | 60975888 | chr14 | 60976075 | 60976514 | chr14 | 60976813 | 60976860 |
| chr14 | 60977337 | 60977712 | chr14 | 60977880 | 60978147 | chr14 | 60981202 | 60981268 |
| chr14 | 60981676 | 60981793 | chr14 | 60982110 | 60982367 | chr14 | 60982574 | 60982622 |
| chr14 | 60982841 | 60982911 | chr14 | 61104291 | 61104556 | chr14 | 61104624 | 61104864 |
| chr14 | 61108620 | 61108996 | chr14 | 61109206 | 61109470 | chr14 | 61109839 | 61110243 |
| chr14 | 61114137 | 61114456 | chr14 | 61115311 | 61115517 | chr14 | 61118743 | 61118765 |
| chr14 | 61118965 | 61119136 | chr14 | 61119536 | 61119639 | chr14 | 61747389 | 61747527 |
| chr14 | 61747583 | 61748033 | chr14 | 62106193 | 62106242 | chr14 | 62279578 | 62279852 |
| chr14 | 62279899 | 62280006 | chr14 | 52583809 | 62583869 | chr14 | 63512100 | 63512291 |
| chr14 | 63512573 | 63512708 | chr14 | 63512741 | 63512816 | chr14 | 63513124 | 63513154 |
| chr14 | 64107335 | 64107600 | chr14 | 64222413 | 64222488 | chr14 | 65005696 | 65005833 |
| chr14 | 65008998 | 65009193 | chr14 | 65233339 | 65233464 | chr14 | 66498931 | 66498975 |
| chr14 | 67585164 | 67585413 | chr14 | 67886378 | 67886606 | chr14 | 68334928 | 68335108 |
| chr14 | 69014044 | 69014110 | chr14 | 69866541 | 69866706 | chr14 | 69867024 | 69867196 |
| chr14 | 70014723 | 70014974 | chr14 | 70038990 | 70039025 | chr14 | 70346136 | 70346491 |
| chr14 | 70654343 | 70654713 | chr14 | 70655530 | 70655889 | chr14 | 70655920 | 70656090 |
| chr14 | 72398743 | 72399019 | chr14 | 72399452 | 72399453 | chr14 | 72399929 | 72400029 |
| chr14 | 73167750 | 73167899 | chr14 | 73175026 | 73175148 | chr14 | 73178807 | 73178865 |
| chr14 | 73180208 | 73180314 | chr14 | 73226952 | 73227005 | chr14 | 73231266 | 73231414 |
| chr14 | 73236095 | 73236178 | chr14 | 73318471 | 73318629 | chr14 | 73333249 | 73333396 |
| chr14 | 73602250 | 73602389 | chr14 | 73604570 | 73604718 | chr14 | 73855616 | 73855646 |
| chr14 | 73956853 | 73956913 | chr14 | 74529109 | 74529139 | chr14 | 74706015 | 74706222 |
| chr14 | 74706941 | 74707544 | chr14 | 74707573 | 74707742 | chr14 | 74707792 | 74707873 |
| chr14 | 74708862 | 74708955 | chr14 | 74892540 | 74892569 | chr14 | 74893074 | 74893113 |
| chr14 | 75078170 | 75078242 | chr14 | 75760311 | 75760347 | chr14 | 75988341 | 75988370 |
| chr14 | 75988732 | 75988761 | chr14 | 76128674 | 76128842 | chr14 | 76604682 | 76604716 |
| chr14 | 76605072 | 76605376 | chr14 | 76843742 | 76843953 | chr14 | 77228121 | 77228159 |
| chr14 | 77606922 | 77607236 | chr14 | 77737212 | 77737814 | chr14 | 79745138 | 79745175 |
| chr14 | 85996479 | 85996608 | chr14 | 85996892 | 85996906 | chr14 | 85997821 | 85997925 |
| chr14 | 85998288 | 85998574 | chr14 | 85998630 | 85998683 | chr14 | 85999597 | 85999613 |
| chr14 | 86000270 | 86000511 | chr14 | 86000918 | 86001114 | chr14 | 88437599 | 88457685 |
| chr14 | 89817889 | 89818034 | chr14 | 90527714 | 90527758 | chr14 | 90983328 | 90983360 |
| chr14 | 91691163 | 91691306 | chr14 | 91691696 | 91691822 | chr14 | 91766154 | 91766450 |
| chr14 | 91780382 | 91780512 | chr14 | 91801036 | 91801164 | chr14 | 92507578 | 92507792 |
| chr14 | 92789512 | 92789542 | chr14 | 92789960 | 92790098 | chr14 | 92790637 | 92790703 |
| chr14 | 92979917 | 92979991 | chr14 | 93155061 | 93155315 | chr14 | 93389557 | 93389693 |
| chr14 | 93389713 | 93389776 | chr14 | 93571193 | 93571326 | chr14 | 93706752 | 93706782 |
| chr14 | 94254389 | 94254458 | chr14 | 94254499 | 94254513 | chr14 | 94405734 | 94405785 |
| chr14 | 94603542 | 94603670 | chr14 | 94889856 | 94889870 | chr14 | 95233705 | 95233765 |
| chr14 | 95234643 | 95234710 | chr14 | 95235026 | 95235369 | chr14 | 95235989 | 95236111 |
| chr14 | 95236524 | 95236553 | chr14 | 95236819 | 95236848 | chr14 | 95237622 | 95237642 |
| chr14 | 95239422 | 95239633 | chr14 | 95240127 | 95240157 | chr14 | 95240227 | 95240341 |
| chr14 | 95240392 | 95240422 | chr14 | 95557626 | 95557655 | chr14 | 95560448 | 95560477 |
| chr14 | 95740035 | 95740115 | chr14 | 96053974 | 96054020 | chr14 | 96342897 | 96343133 |
| chr14 | 96343404 | 96343433 | chr14 | 96343668 | 96343701 | chr14 | 97045354 | 97045431 |
| chr14 | 97058944 | 97059083 | chr14 | 97499277 | 97499315 | chr14 | 97499847 | 97499849 |
| chr14 | 97685044 | 97685288 | chr14 | 97685707 | 97685959 | chr14 | 99584575 | 99584664 |
| chr14 | 99712321 | 99712394 | chr14 | 99736151 | 99736183 | chr14 | 99737398 | 99737462 |
| chr14 | 100148073 | 100148230 | chr14 | 100437794 | 100437949 | chr14 | 100438705 | 100438811 |
| chr14 | 100643350 | 100643481 | chr14 | 100793556 | 100793650 | chr14 | 100843765 | 100843912 |
| chr14 | 101250109 | 101250272 | chr14 | 101506231 | 101506260 | chr14 | 101543868 | 101544235 |
| chr14 | 101923114 | 101923250 | chr14 | 101923600 | 101923686 | chr14 | 101924031 | 101924047 |
| chr14 | 101925049 | 101925071 | chr14 | 101925656 | 101925901 | chr14 | 102026360 | 102026484 |
| chr14 | 102026797 | 102026967 | chr14 | 102031236 | 102031271 | chr14 | 102031512 | 102031580 |
| chr14 | 102247912 | 102248214 | chr14 | 102418607 | 102418637 | chr14 | 102521602 | 102521758 |
| chr14 | 102529325 | 102529419 | chr14 | 102530007 | 102530234 | chr14 | 102530500 | 102530530 |
| chr14 | 102564464 | 102564605 | chr14 | 102682077 | 102682149 | chr14 | 102772607 | 102772695 |
| chr14 | 102973169 | 102973268 | chr14 | 103021391 | 103022003 | chr14 | 103394884 | 103395101 |
| chr14 | 103477643 | 103477794 | chr14 | 103655226 | 103655601 | chr14 | 103674078 | 103674079 |
| chr14 | 103687082 | 103687219 | chr14 | 103739967 | 103740150 | chr14 | 103740358 | 103740430 |
| chr14 | 103745699 | 103745750 | chr14 | 104160060 | 104160134 | chr14 | 104202705 | 104202759 |
| chr14 | 104355204 | 104355273 | chr14 | 104386476 | 104387067 | chr14 | 104547785 | 104547909 |
| chr14 | 104571985 | 104572116 | chr14 | 104601737 | 104601832 | chr14 | 104602033 | 104602063 |
| chr14 | 104605032 | 104605114 | chr14 | 104620411 | 104620554 | chr14 | 104627654 | 104627759 |
| chr14 | 104645126 | 104645188 | chr14 | 104646317 | 104646491 | chr14 | 104647257 | 104647287 |

TABLE 12-continued

| chr | start | end | chr | start | end | chr | start | end |
|---|---|---|---|---|---|---|---|---|
| chr14 | 104682545 | 104682656 | chr14 | 104862860 | 104863026 | chr14 | 104897228 | 104897294 |
| chr14 | 105071298 | 105071396 | chr14 | 105157485 | 105157554 | chr14 | 105239389 | 105239439 |
| chr14 | 105239793 | 105239825 | chr14 | 105241309 | 105241428 | chr14 | 105243032 | 105243064 |
| chr14 | 105246427 | 105246582 | chr14 | 105512063 | 105512395 | chr14 | 105658349 | 105658425 |
| chr14 | 105714258 | 105714334 | chr14 | 105714415 | 105714441 | chr14 | 105715248 | 105715392 |
| chr14 | 105830630 | 105830859 | chr14 | 105963655 | 105963772 | chr15 | 22822348 | 22822488 |
| chr15 | 23035709 | 23035781 | chr15 | 23158397 | 23158489 | chr15 | 23162337 | 23162372 |
| chr15 | 23273146 | 23273330 | chr15 | 23692316 | 23692453 | chr15 | 26107640 | 26107743 |
| chr15 | 26107846 | 26107860 | chr15 | 26108096 | 26108326 | chr15 | 26108549 | 26108701 |
| chr15 | 27212887 | 27213172 | chr15 | 27604062 | 27604123 | chr15 | 28341699 | 28342019 |
| chr15 | 28344173 | 28344187 | chr15 | 28344224 | 28344287 | chr15 | 28352240 | 28352421 |
| chr15 | 29077284 | 29077383 | chr15 | 29130807 | 29131047 | chr15 | 29131533 | 29131630 |
| chr15 | 29131756 | 29131875 | chr15 | 29396330 | 29396360 | chr15 | 29407777 | 29407813 |
| chr15 | 29407867 | 29408001 | chr15 | 29452432 | 29452462 | chr15 | 29862502 | 29862582 |
| chr15 | 30115185 | 30115228 | chr15 | 31455370 | 31455485 | chr15 | 31775596 | 31775637 |
| chr15 | 31775679 | 31775782 | chr15 | 32933918 | 32934018 | chr15 | 33009747 | 33009761 |
| chr15 | 33009822 | 33010675 | chr15 | 33010721 | 33011348 | chr15 | 33011601 | 33011633 |
| chr15 | 33487057 | 33487120 | chr15 | 33602801 | 33602886 | chr15 | 33603194 | 33603608 |
| chr15 | 33879242 | 33879272 | chr15 | 34517058 | 34517334 | chr15 | 34630439 | 34630449 |
| chr15 | 34630515 | 34630544 | chr15 | 34630818 | 34630865 | chr15 | 34729478 | 34729582 |
| chr15 | 34786504 | 34786943 | chr15 | 34787233 | 34787304 | chr15 | 34879708 | 34879866 |
| chr15 | 35046607 | 35046608 | chr15 | 35047034 | 35047133 | chr15 | 35087666 | 35087698 |
| chr15 | 35310631 | 35310868 | chr15 | 37180309 | 37180743 | chr15 | 37402974 | 37403086 |
| chr15 | 37403116 | 37403238 | chr15 | 40211819 | 40212190 | chr15 | 40575630 | 40575744 |
| chr15 | 40671495 | 40671620 | chr15 | 40675092 | 40675121 | chr15 | 40763811 | 40763862 |
| chr15 | 40782219 | 40782249 | chr15 | 40856224 | 40856254 | chr15 | 40877650 | 40877714 |
| chr15 | 41165245 | 41165700 | chr15 | 41541844 | 41541874 | chr15 | 41693679 | 41693794 |
| chr15 | 41708225 | 41708305 | chr15 | 41732398 | 41732471 | chr15 | 41804878 | 41805772 |
| chr15 | 41835548 | 41835720 | chr15 | 41913750 | 41913807 | chr15 | 41952572 | 41952711 |
| chr15 | 42749733 | 42749899 | chr15 | 42866975 | 42867049 | chr15 | 43551059 | 43551196 |
| chr15 | 43810405 | 43810435 | chr15 | 44037568 | 44037699 | chr15 | 45403636 | 45403680 |
| chr15 | 45403799 | 45403999 | chr15 | 45404103 | 45404130 | chr15 | 45404898 | 45405117 |
| chr15 | 45421385 | 45421435 | chr15 | 45421998 | 45422095 | chr15 | 45427370 | 45427410 |
| chr15 | 45427611 | 45427719 | chr15 | 45427772 | 45427786 | chr15 | 45444061 | 45444141 |
| chr15 | 45479460 | 45479516 | chr15 | 45493209 | 45493371 | chr15 | 45670462 | 45670838 |
| chr15 | 46021437 | 46021467 | chr15 | 47476118 | 47476239 | chr15 | 47476291 | 47476419 |
| chr15 | 47476877 | 47476980 | chr15 | 47477013 | 47477018 | chr15 | 48483956 | 48483986 |
| chr15 | 48936726 | 48937645 | chr15 | 48937710 | 48937987 | chr15 | 48938212 | 48938510 |
| chr15 | 50450454 | 50450574 | chr15 | 50464583 | 50464622 | chr15 | 51146606 | 51146636 |
| chr15 | 51385913 | 51386181 | chr15 | 51634075 | 51634135 | chr15 | 51973646 | 51973694 |
| chr15 | 51973764 | 51973934 | chr15 | 52000818 | 52000937 | chr15 | 53075809 | 53075864 |
| chr15 | 53075986 | 53077000 | chr15 | 53077066 | 53077361 | chr15 | 53077655 | 53077731 |
| chr15 | 53078064 | 53078236 | chr15 | 53079340 | 53079677 | chr15 | 53079718 | 53079891 |
| chr15 | 53079971 | 53080082 | chr15 | 53080337 | 53080606 | chr15 | 53080935 | 53080990 |
| chr15 | 53081399 | 53081677 | chr15 | 53082443 | 53082491 | chr15 | 53096816 | 53096891 |
| chr15 | 53097231 | 53097261 | chr15 | 53097778 | 53097906 | chr15 | 53098382 | 53098658 |
| chr15 | 54270498 | 54270707 | chr15 | 54270932 | 54270961 | chr15 | 54642236 | 54642352 |
| chr15 | 55452761 | 55452993 | chr15 | 55610440 | 55610698 | chr15 | 55699089 | 55699164 |
| chr15 | 55806758 | 55806900 | chr15 | 55880891 | 55881011 | chr15 | 56832508 | 56832546 |
| chr15 | 58357800 | 58357819 | chr15 | 59158488 | 59158537 | chr15 | 59158781 | 59158901 |
| chr15 | 59950198 | 59950363 | chr15 | 60084984 | 60085014 | chr15 | 60287038 | 60287585 |
| chr15 | 60287644 | 60287733 | chr15 | 60288786 | 60288844 | chr15 | 60289310 | 60289546 |
| chr15 | 60296122 | 60296209 | chr15 | 60296598 | 60296617 | chr15 | 60296861 | 60296923 |
| chr15 | 60297152 | 60297409 | chr15 | 60297637 | 60297826 | chr15 | 60297942 | 60298108 |
| chr15 | 60705106 | 60705204 | chr15 | 61520916 | 61521014 | chr15 | 61521659 | 61521937 |
| chr15 | 62456922 | 62456952 | chr15 | 64109724 | 64109788 | chr15 | 64618655 | 64618813 |
| chr15 | 64649481 | 64649553 | chr15 | 65118954 | 65118984 | chr15 | 65119265 | 65119295 |
| chr15 | 65119499 | 65119632 | chr15 | 65436137 | 65436213 | chr15 | 65669859 | 65669899 |
| chr15 | 65685591 | 65685708 | chr15 | 65823926 | 65824103 | chr15 | 65826189 | 65826359 |
| chr15 | 65862004 | 65862121 | chr15 | 66113240 | 66113270 | chr15 | 66649915 | 66649945 |
| chr15 | 66727409 | 66727498 | chr15 | 66729148 | 66729177 | chr15 | 66774117 | 66774203 |
| chr15 | 66789220 | 66789321 | chr15 | 66963816 | 66963871 | chr15 | 67146145 | 67146431 |
| chr15 | 67545536 | 67545566 | chr15 | 68112611 | 68112641 | chr15 | 68113868 | 68113898 |
| chr15 | 68114139 | 68114195 | chr15 | 68116369 | 68116621 | chr15 | 68117830 | 68118633 |
| chr15 | 68118930 | 68119174 | chr15 | 68119579 | 68120352 | chr15 | 68120827 | 68120857 |
| chr15 | 68121150 | 68121957 | chr15 | 68122643 | 68122673 | chr15 | 68125261 | 68125664 |
| chr15 | 68127801 | 68128350 | chr15 | 68128594 | 68128688 | chr15 | 68260519 | 68260709 |
| chr15 | 71055636 | 71055815 | chr15 | 72411929 | 72412176 | chr15 | 72612540 | 72612906 |
| chr15 | 72743741 | 72743796 | chr15 | 72979757 | 72979873 | chr15 | 73660004 | 73660067 |
| chr15 | 73661469 | 73661666 | chr15 | 74045075 | 74045097 | chr15 | 74422006 | 74422146 |
| chr15 | 74422869 | 74423002 | chr15 | 74658151 | 74658396 | chr15 | 74658502 | 74658587 |
| chr15 | 74686021 | 74686051 | chr15 | 74818772 | 74818806 | chr15 | 74903896 | 74903926 |
| chr15 | 74906463 | 74906493 | chr15 | 75205413 | 75205481 | chr15 | 75251346 | 75251382 |
| chr15 | 75251672 | 75251786 | chr15 | 75412459 | 75412714 | chr15 | 76627508 | 76627536 |
| chr15 | 76627576 | 76627826 | chr15 | 76629163 | 76629220 | chr15 | 76629494 | 76629531 |
| chr15 | 76629814 | 76630124 | chr15 | 76630520 | 76630847 | chr15 | 76638472 | 76638496 |
| chr15 | 77448873 | 77449001 | chr15 | 78111196 | 78111210 | chr15 | 78501806 | 78501942 |
| chr15 | 78556819 | 78557108 | chr15 | 78595791 | 78596218 | chr15 | 78632727 | 78632823 |

TABLE 12-continued

| chr | start | end | chr | start | end | chr | start | end |
|---|---|---|---|---|---|---|---|---|
| chr15 | 78859435 | 78859603 | chr15 | 78912281 | 78912371 | chr15 | 78912623 | 78912653 |
| chr15 | 78912912 | 78913027 | chr15 | 78913095 | 78913170 | chr15 | 78913535 | 78913651 |
| chr15 | 79104217 | 79104246 | chr15 | 79104466 | 79104495 | chr15 | 79151898 | 79152007 |
| chr15 | 79381705 | 79381745 | chr15 | 79382099 | 79382571 | chr15 | 79382786 | 79383257 |
| chr15 | 79383947 | 79383977 | chr15 | 79502211 | 79502360 | chr15 | 79575278 | 79575474 |
| chr15 | 79576145 | 79576277 | chr15 | 79724502 | 79724560 | chr15 | 79724607 | 79724792 |
| chr15 | 79724864 | 79725140 | chr15 | 79725422 | 79725539 | chr15 | 80216803 | 80216884 |
| chr15 | 81071827 | 81071867 | chr15 | 82336879 | 82336972 | chr15 | 82340070 | 82340157 |
| chr15 | 83314048 | 83314106 | chr15 | 83315336 | 83315393 | chr15 | 83316251 | 83317087 |
| chr15 | 83349234 | 83349611 | chr15 | 83349672 | 83349686 | chr15 | 83378212 | 83378370 |
| chr15 | 83622512 | 83622565 | chr15 | 83655843 | 83655934 | chr15 | 83776255 | 83776306 |
| chr15 | 83776333 | 83776716 | chr15 | 83776769 | 83776785 | chr15 | 83866523 | 83866559 |
| chr15 | 83875648 | 83875665 | chr15 | 83875706 | 83875901 | chr15 | 83877055 | 83877149 |
| chr15 | 83953884 | 83953903 | chr15 | 83954380 | 83964409 | chr15 | 84115747 | 84115853 |
| chr15 | 84115932 | 84115966 | chr15 | 84116905 | 84116949 | chr15 | 84322994 | 84323037 |
| chr15 | 84711204 | 84711367 | chr15 | 84748578 | 84748619 | chr15 | 84748679 | 84749260 |
| chr15 | 85142994 | 85143054 | chr15 | 85886518 | 85886604 | chr15 | 86002524 | 86002690 |
| chr15 | 88798725 | 88798791 | chr15 | 88799537 | 88800301 | chr15 | 88800541 | 88801008 |
| chr15 | 88801089 | 88801103 | chr15 | 89149169 | 89149448 | chr15 | 89248753 | 89248907 |
| chr15 | 89346050 | 89346326 | chr15 | 89346347 | 89346393 | chr15 | 89346670 | 89346793 |
| chr15 | 89346882 | 89346943 | chr15 | 89903484 | 89903814 | chr15 | 89910521 | 89910748 |
| chr15 | 89911087 | 89911186 | chr15 | 89913750 | 89913780 | chr15 | 89914231 | 89914449 |
| chr15 | 89914867 | 89914895 | chr15 | 89915240 | 89915369 | chr15 | 89921956 | 89922006 |
| chr15 | 89922500 | 89922546 | chr15 | 89942755 | 89942945 | chr15 | 89943410 | 89943706 |
| chr15 | 89949617 | 89949942 | chr15 | 89950236 | 89950736 | chr15 | 89951082 | 89951113 |
| chr15 | 89951466 | 89951801 | chr15 | 89952153 | 89952452 | chr15 | 89952700 | 89953055 |
| chr15 | 89954197 | 89954335 | chr15 | 89956423 | 89956450 | chr15 | 90039563 | 90039711 |
| chr15 | 90631823 | 90631948 | chr15 | 90667461 | 90667586 | chr15 | 90703262 | 90703345 |
| chr15 | 90755916 | 90756079 | chr15 | 91643360 | 91643586 | chr15 | 92936290 | 92936322 |
| chr15 | 92937153 | 92937374 | chr15 | 92937927 | 92938060 | chr15 | 92938123 | 92938293 |
| chr15 | 93158592 | 93158739 | chr15 | 93350668 | 93350698 | chr15 | 93364552 | 93364624 |
| chr15 | 93631739 | 93632014 | chr15 | 93632660 | 93633233 | chr15 | 94347602 | 94347632 |
| chr15 | 96874362 | 96874514 | chr15 | 96889154 | 96889183 | chr15 | 96889401 | 96889430 |
| chr15 | 96897934 | 96898010 | chr15 | 96911559 | 96911691 | chr15 | 96952696 | 96953098 |
| chr15 | 96953132 | 96953209 | chr15 | 96959730 | 96959960 | chr15 | 96960376 | 96960409 |
| chr15 | 96960732 | 96960826 | chr15 | 97006372 | 97006533 | chr15 | 98504114 | 98504144 |
| chr15 | 98634851 | 98634949 | chr15 | 98776762 | 98776792 | chr15 | 98836178 | 98836393 |
| chr15 | 98964786 | 98965138 | chr15 | 99193206 | 99193480 | chr15 | 99193914 | 99194186 |
| chr15 | 99254040 | 99254208 | chr15 | 99295692 | 99295749 | chr15 | 99346861 | 99347040 |
| chr15 | 99354999 | 99355041 | chr15 | 99453230 | 99453440 | chr15 | 99456299 | 99456329 |
| chr15 | 99497059 | 99497132 | chr15 | 100274325 | 100274385 | chr15 | 100339980 | 100340010 |
| chr15 | 100913423 | 100913595 | chr15 | 101420521 | 101420610 | chr15 | 101420972 | 101420989 |
| chr15 | 101818327 | 101818357 | chr15 | 102115873 | 102115905 | chr15 | 102193587 | 102193713 |
| chr15 | 102286533 | 102286563 | chr16 | 93831 | 93932 | chr16 | 142649 | 142783 |
| chr16 | 189744 | 189933 | chr16 | 199886 | 199943 | chr16 | 215416 | 215872 |
| chr16 | 215913 | 216224 | chr16 | 216676 | 217036 | chr16 | 230265 | 230315 |
| chr16 | 230497 | 230610 | chr16 | 232136 | 232166 | chr16 | 280323 | 280395 |
| chr16 | 318104 | 318227 | chr16 | 318498 | 318763 | chr16 | 337599 | 337659 |
| chr16 | 410377 | 410402 | chr16 | 565492 | 565623 | chr16 | 571714 | 571959 |
| chr16 | 611385 | 611520 | chr16 | 611969 | 612260 | chr16 | 612869 | 613037 |
| chr16 | 667141 | 667297 | chr16 | 667547 | 667622 | chr16 | 667876 | 668074 |
| chr16 | 672730 | 672806 | chr16 | 677972 | 678084 | chr16 | 700299 | 700329 |
| chr16 | 726626 | 726990 | chr16 | 731488 | 731610 | chr16 | 735205 | 735594 |
| chr16 | 740791 | 740914 | chr16 | 741376 | 741601 | chr16 | 762523 | 762694 |
| chr16 | 837361 | 837460 | chr16 | 845955 | 845985 | chr16 | 882484 | 882588 |
| chr16 | 895093 | 895166 | chr16 | 943481 | 943553 | chr16 | 1018120 | 1018150 |
| chr16 | 1019640 | 1019685 | chr16 | 1030444 | 1030655 | chr16 | 1052587 | 1052627 |
| chr16 | 1102927 | 1102957 | chr16 | 1116661 | 1116691 | chr16 | 1122858 | 1122946 |
| chr16 | 1129011 | 1129140 | chr16 | 1155162 | 1155212 | chr16 | 1186809 | 1186850 |
| chr16 | 1204003 | 1204034 | chr16 | 1217307 | 1217503 | chr16 | 1218034 | 1218090 |
| chr16 | 1228804 | 1228916 | chr16 | 1229970 | 1230142 | chr16 | 1248604 | 1248675 |
| chr16 | 1267925 | 1268120 | chr16 | 1271546 | 1271646 | chr16 | 1312526 | 1312611 |
| chr16 | 1323976 | 1324061 | chr16 | 1382901 | 1382940 | chr16 | 1394502 | 1394596 |
| chr16 | 1397454 | 1397484 | chr16 | 1407370 | 1407846 | chr16 | 1408210 | 1408240 |
| chr16 | 1428508 | 1428873 | chr16 | 1466425 | 1466455 | chr16 | 1469334 | 1469527 |
| chr16 | 1491567 | 1491613 | chr16 | 1523925 | 1523971 | chr16 | 1704656 | 1704800 |
| chr16 | 1729868 | 1730022 | chr16 | 1730306 | 1730597 | chr16 | 1741853 | 1742079 |
| chr16 | 1750769 | 1750907 | chr16 | 1842490 | 1842519 | chr16 | 1993818 | 1993848 |
| chr16 | 2029072 | 2029137 | chr16 | 2040914 | 2040960 | chr16 | 2040981 | 2041512 |
| chr16 | 2041582 | 2042160 | chr16 | 2042875 | 2042905 | chr16 | 2086831 | 2086860 |
| chr16 | 2106703 | 2106732 | chr16 | 2111966 | 2111995 | chr16 | 2120515 | 2120544 |
| chr16 | 2122243 | 2122272 | chr16 | 2124205 | 2124348 | chr16 | 2126080 | 2126109 |
| chr16 | 2128527 | 2129581 | chr16 | 2130361 | 2130390 | chr16 | 2132244 | 2132315 |
| chr16 | 2135301 | 2135330 | chr16 | 2136228 | 2136257 | chr16 | 2136727 | 2136855 |
| chr16 | 2140403 | 2140438 | chr16 | 2141909 | 2141972 | chr16 | 2142546 | 2142628 |
| chr16 | 2213313 | 2213343 | chr16 | 2232745 | 2233003 | chr16 | 2234726 | 2235020 |
| chr16 | 2275129 | 2275182 | chr16 | 2281249 | 2281314 | chr16 | 2287295 | 2287370 |
| chr16 | 2466225 | 2466307 | chr16 | 2485858 | 2485917 | chr16 | 2508414 | 2508453 |

TABLE 12-continued

| chr | start | end | chr | start | end | chr | start | end |
|---|---|---|---|---|---|---|---|---|
| chr16 | 2531069 | 2531177 | chr16 | 2731530 | 2731660 | chr16 | 2764377 | 2764470 |
| chr16 | 2770122 | 2770602 | chr16 | 2818101 | 2818156 | chr16 | 2892542 | 2892602 |
| chr16 | 2892627 | 2892729 | chr16 | 2956451 | 2956670 | chr16 | 2974601 | 2974650 |
| chr16 | 3017157 | 3017430 | chr16 | 3068171 | 3068201 | chr16 | 3151127 | 3151186 |
| chr16 | 3211708 | 3212019 | chr16 | 3220591 | 3220892 | chr16 | 3221142 | 3221700 |
| chr16 | 3221787 | 3222239 | chr16 | 3225471 | 3225607 | chr16 | 3232739 | 3233016 |
| chr16 | 3233199 | 3233330 | chr16 | 3233435 | 3234103 | chr16 | 3234165 | 3234452 |
| chr16 | 3237857 | 3238546 | chr16 | 3238993 | 3239848 | chr16 | 3241549 | 3241663 |
| chr16 | 3241936 | 3241966 | chr16 | 3269249 | 3269350 | chr16 | 3284117 | 3284147 |
| chr16 | 3355279 | 3355718 | chr16 | 3492583 | 3492675 | chr16 | 3598920 | 3598953 |
| chr16 | 3696694 | 3696724 | chr16 | 3802981 | 3803074 | chr16 | 3950127 | 3950279 |
| chr16 | 4264529 | 4264694 | chr16 | 4303144 | 4303174 | chr16 | 4310735 | 4310847 |
| chr16 | 4431126 | 4431189 | chr16 | 4431487 | 4431516 | chr16 | 4731638 | 4731718 |
| chr16 | 4733166 | 4733195 | chr16 | 4738567 | 4738680 | chr16 | 4751554 | 4751583 |
| chr16 | 4783226 | 4783375 | chr16 | 4846136 | 4846514 | chr16 | 4887144 | 4887244 |
| chr16 | 5037900 | 5038004 | chr16 | 5541116 | 5541158 | chr16 | 6035056 | 6035208 |
| chr16 | 6069941 | 6070019 | chr16 | 7354634 | 7354657 | chr16 | 7382499 | 7382534 |
| chr16 | 7525361 | 7525531 | chr16 | 8781032 | 8781177 | chr16 | 8870353 | 8870383 |
| chr16 | 9009860 | 9009989 | chr16 | 10274399 | 10274429 | chr16 | 10275308 | 10275392 |
| chr16 | 10275752 | 10275948 | chr16 | 10276360 | 10277050 | chr16 | 10277072 | 10277437 |
| chr16 | 10479815 | 10479980 | chr16 | 11242000 | 11242138 | chr16 | 11427659 | 11427732 |
| chr16 | 11490632 | 11490662 | chr16 | 11923005 | 11923035 | chr16 | 12011258 | 12011325 |
| chr16 | 12011940 | 12012073 | chr16 | 12066767 | 12066806 | chr16 | 12210772 | 12210896 |
| chr16 | 12211279 | 12211416 | chr16 | 12530169 | 12530199 | chr16 | 12971776 | 12971934 |
| chr16 | 12994459 | 12994737 | chr16 | 12995062 | 12995593 | chr16 | 12995803 | 12995803 |
| chr16 | 12996074 | 12996328 | chr16 | 12996617 | 12996720 | chr16 | 12996948 | 12997011 |
| chr16 | 12997386 | 12997703 | chr16 | 14021974 | 14022003 | chr16 | 14041504 | 14041533 |
| chr16 | 14041795 | 14041824 | chr16 | 14042062 | 14042091 | chr16 | 14189948 | 14190059 |
| chr16 | 14724632 | 14724736 | chr16 | 14725842 | 14726005 | chr16 | 15489599 | 15489808 |
| chr16 | 15708247 | 15708309 | chr16 | 15738905 | 15739042 | chr16 | 15820825 | 15820865 |
| chr16 | 16868746 | 16868905 | chr16 | 18163245 | 18163352 | chr16 | 18802250 | 18802680 |
| chr16 | 18950928 | 18951018 | chr16 | 19430908 | 19430949 | chr16 | 19531564 | 19531697 |
| chr16 | 19567202 | 19567449 | chr16 | 19895125 | 19895155 | chr16 | 21541606 | 21541636 |
| chr16 | 21665540 | 21665570 | chr16 | 21666641 | 21666771 | chr16 | 21674664 | 21674777 |
| chr16 | 21831621 | 21831957 | chr16 | 21839328 | 21839470 | chr16 | 22300599 | 22300637 |
| chr16 | 22326397 | 22326427 | chr16 | 22824701 | 22825076 | chr16 | 22825327 | 22825469 |
| chr16 | 22825886 | 22826081 | chr16 | 23313464 | 23313522 | chr16 | 23313780 | 23313836 |
| chr16 | 23706412 | 23706520 | chr16 | 23766097 | 23766130 | chr16 | 23847311 | 23847511 |
| chr16 | 23847789 | 23847874 | chr16 | 23847934 | 23847956 | chr16 | 24127251 | 24127338 |
| chr16 | 24172241 | 24172271 | chr16 | 24180710 | 24180760 | chr16 | 24267115 | 24267144 |
| chr16 | 24267485 | 24267578 | chr16 | 24415106 | 24415176 | chr16 | 25266537 | 25266573 |
| chr16 | 25542301 | 25542452 | chr16 | 25551107 | 25551264 | chr16 | 25702955 | 25702992 |
| chr16 | 25703642 | 25704122 | chr16 | 25704390 | 25704628 | chr16 | 25921574 | 25921604 |
| chr16 | 26302585 | 26302619 | chr16 | 26664739 | 26664775 | chr16 | 27207774 | 27207852 |
| chr16 | 27459938 | 27460074 | chr16 | 27749857 | 27750033 | chr16 | 27961122 | 27961254 |
| chr16 | 28074176 | 28074254 | chr16 | 28074418 | 28074684 | chr16 | 28074959 | 28075197 |
| chr16 | 28093825 | 28093866 | chr16 | 28224516 | 28224546 | chr16 | 28491774 | 28491924 |
| chr16 | 28560309 | 28560381 | chr16 | 28823157 | 28823459 | chr16 | 28850998 | 28851028 |
| chr16 | 28877839 | 28877883 | chr16 | 28891040 | 28891072 | chr16 | 29119008 | 29119058 |
| chr16 | 29153284 | 29153356 | chr16 | 29244900 | 29244997 | chr16 | 29830871 | 29831078 |
| chr16 | 29888624 | 29888658 | chr16 | 29936211 | 29936272 | chr16 | 30017330 | 30017447 |
| chr16 | 30065485 | 30065525 | chr16 | 30085867 | 30085995 | chr16 | 30116285 | 30116315 |
| chr16 | 30124691 | 30124861 | chr16 | 30169925 | 30170103 | chr16 | 30388542 | 30388574 |
| chr16 | 30402082 | 30402112 | chr16 | 30609373 | 30609408 | chr16 | 30639693 | 30639735 |
| chr16 | 30804321 | 30804472 | chr16 | 30826334 | 30826509 | chr16 | 30907010 | 30907148 |
| chr16 | 31227914 | 31228313 | chr16 | 31384593 | 31384623 | chr16 | 31446830 | 31447096 |
| chr16 | 31498008 | 31498165 | chr16 | 31500544 | 31500673 | chr16 | 31580560 | 31581036 |
| chr16 | 46569239 | 46569474 | chr16 | 46721567 | 46721707 | chr16 | 46803280 | 46803355 |
| chr16 | 47177525 | 47177606 | chr16 | 48450544 | 48450574 | chr16 | 48641663 | 48641693 |
| chr16 | 48642149 | 48642179 | chr16 | 48845120 | 48845125 | chr16 | 49309170 | 49309262 |
| chr16 | 49311523 | 49311989 | chr16 | 49312033 | 49312299 | chr16 | 49313363 | 49313710 |
| chr16 | 49314022 | 49314118 | chr16 | 49314419 | 49314561 | chr16 | 49314784 | 49314821 |
| chr16 | 49315276 | 49315306 | chr16 | 49315919 | 49316315 | chr16 | 49316509 | 49316580 |
| chr16 | 49638060 | 49638090 | chr16 | 50335767 | 50336797 | chr16 | 51183964 | 51184406 |
| chr16 | 51184807 | 51184957 | chr16 | 51185055 | 51185291 | chr16 | 51185844 | 51185964 |
| chr16 | 51186026 | 51186280 | chr16 | 51186596 | 51186939 | chr16 | 51188697 | 51188711 |
| chr16 | 51189922 | 51190037 | chr16 | 51190122 | 51190215 | chr16 | 53447826 | 53448002 |
| chr16 | 53467271 | 53467395 | chr16 | 53563622 | 53563654 | chr16 | 54128645 | 54128713 |
| chr16 | 54318898 | 54318988 | chr16 | 54319420 | 54319468 | chr16 | 54321638 | 54321818 |
| chr16 | 54324999 | 54325131 | chr16 | 54628691 | 54628867 | chr16 | 54964948 | 54965114 |
| chr16 | 54966830 | 54967264 | chr16 | 54971400 | 54971430 | chr16 | 55090666 | 55090861 |
| chr16 | 55357926 | 55357940 | chr16 | 55357992 | 55358086 | chr16 | 55358316 | 55358350 |
| chr16 | 55358798 | 55359071 | chr16 | 55363009 | 55363223 | chr16 | 55364716 | 55364843 |
| chr16 | 55365103 | 55365218 | chr16 | 55404999 | 55405214 | chr16 | 55689886 | 55689915 |
| chr16 | 55690115 | 55690379 | chr16 | 55690454 | 55690576 | chr16 | 55690762 | 56690809 |
| chr16 | 56224557 | 56224832 | chr16 | 56228370 | 56228416 | chr16 | 56228578 | 56228581 |
| chr16 | 56651094 | 56651123 | chr16 | 56651239 | 56651275 | chr16 | 56659175 | 56659673 |
| chr16 | 56672158 | 56672172 | chr16 | 56672222 | 56672385 | chr16 | 56672514 | 56672654 |

TABLE 12-continued

| chr | start | end | chr | start | end | chr | start | end |
|---|---|---|---|---|---|---|---|---|
| chr16 | 56672656 | 56672685 | chr16 | 56709837 | 56709892 | chr16 | 56709950 | 56710030 |
| chr16 | 57222663 | 57222709 | chr16 | 57318379 | 57318412 | chr16 | 57326422 | 57326613 |
| chr16 | 57935454 | 57935605 | chr16 | 58018634 | 58018845 | chr16 | 58019225 | 58019430 |
| chr16 | 58120795 | 58120961 | chr16 | 58427501 | 58427542 | chr16 | 58497221 | 58497335 |
| chr16 | 58497752 | 58497829 | chr16 | 58498175 | 58498204 | chr16 | 58498570 | 58498724 |
| chr16 | 58521708 | 58621737 | chr16 | 58534666 | 58534695 | chr16 | 58545487 | 58545516 |
| chr16 | 58550489 | 58550519 | chr16 | 58969757 | 58969792 | chr16 | 62068463 | 62068517 |
| chr16 | 62068952 | 62068982 | chr16 | 62070743 | 62070773 | chr16 | 65154933 | 65155091 |
| chr16 | 65156385 | 65156489 | chr16 | 66461786 | 66461840 | chr16 | 66612882 | 66613095 |
| chr16 | 66613335 | 66613369 | chr16 | 66863917 | 66863959 | chr16 | 67197698 | 67197769 |
| chr16 | 67198009 | 67198039 | chr16 | 67198917 | 67198957 | chr16 | 67241204 | 67241234 |
| chr16 | 67313865 | 67313895 | chr16 | 67850955 | 67850985 | chr16 | 67871102 | 67871134 |
| chr16 | 68481486 | 68481543 | chr16 | 68482808 | 68482941 | chr16 | 68544259 | 68544378 |
| chr16 | 68676408 | 68676604 | chr16 | 68676842 | 68676984 | chr16 | 68770755 | 68771298 |
| chr16 | 68844158 | 68844187 | chr16 | 68846033 | 68846062 | chr16 | 68856078 | 68856107 |
| chr16 | 68876782 | 68876996 | chr16 | 59026784 | 69026814 | chr16 | 69564118 | 69564200 |
| chr16 | 69969260 | 69969290 | chr16 | 70489585 | 70489681 | chr16 | 70595535 | 70595700 |
| chr16 | 70794492 | 70794633 | chr16 | 71460027 | 71460088 | chr16 | 71460271 | 71460351 |
| chr16 | 71507759 | 71507791 | chr16 | 71677557 | 71677661 | chr16 | 71715779 | 71715809 |
| chr16 | 71918889 | 71919024 | chr16 | 72957763 | 72957795 | chr16 | 74886148 | 74886268 |
| chr16 | 74901594 | 74901659 | chr16 | 75019751 | 75019781 | chr16 | 75549798 | 75549836 |
| chr16 | 76008985 | 76009154 | chr16 | 77247440 | 77247470 | chr16 | 77468261 | 77468457 |
| chr16 | 77822589 | 77822874 | chr16 | 78079969 | 78080054 | chr16 | 79623602 | 79623616 |
| chr16 | 79623798 | 79623914 | chr16 | 80837962 | 80838143 | chr16 | 80966399 | 80966431 |
| chr16 | 81564199 | 81564229 | chr16 | 81929362 | 81929392 | chr16 | 81946246 | 81946275 |
| chr16 | 81962167 | 81962196 | chr16 | 82660360 | 82660496 | chr16 | 82660712 | 82660741 |
| chr16 | 84074836 | 84074871 | chr16 | 84153364 | 84153394 | chr16 | 84402244 | 84402319 |
| chr16 | 84519974 | 84520010 | chr16 | 84651793 | 84651822 | chr16 | 84823626 | 84823656 |
| chr16 | 84853288 | 84853376 | chr16 | 85075434 | 85075553 | chr16 | 85317850 | 85317882 |
| chr16 | 85485747 | 85485855 | chr16 | 85497445 | 85497475 | chr16 | 85517345 | 85517521 |
| chr16 | 85651520 | 85651550 | chr16 | 85678639 | 85678761 | chr16 | 85684308 | 85684457 |
| chr16 | 85699689 | 85699921 | chr16 | 85834460 | 85834495 | chr16 | 85932828 | 85932858 |
| chr16 | 86320354 | 86320391 | chr16 | 86320755 | 86320800 | chr16 | 86321020 | 86321068 |
| chr16 | 86530947 | 86530992 | chr16 | 86531017 | 86531046 | chr16 | 86531375 | 86531480 |
| chr16 | 86531528 | 86531573 | chr16 | 86541591 | 86541968 | chr16 | 86542373 | 86542457 |
| chr16 | 86544191 | 85544557 | chr16 | 86571984 | 86572014 | chr16 | 86599481 | 86599844 |
| chr16 | 86600483 | 86600686 | chr16 | 86600958 | 86601015 | chr16 | 86601286 | 86601539 |
| chr16 | 86602038 | 86602514 | chr16 | 86878150 | 86878180 | chr16 | 87092439 | 87092553 |
| chr16 | 87525622 | 87525701 | chr16 | 87635103 | 87635133 | chr16 | 87636627 | 87636907 |
| chr16 | 87714272 | 87714381 | chr16 | 87723735 | 87724098 | chr16 | 88007072 | 88007108 |
| chr16 | 88106322 | 88106398 | chr16 | 88164401 | 88164468 | chr16 | 88498241 | 88498760 |
| chr16 | 88504058 | 88504315 | chr16 | 88506346 | 88506526 | chr16 | 88512427 | 88512529 |
| chr16 | 88543428 | 88543458 | chr16 | 88550263 | 88550483 | chr16 | 88603696 | 88603760 |
| chr16 | 88623960 | 88624167 | chr16 | 88711337 | 88711507 | chr16 | 88757466 | 88757496 |
| chr16 | 88879949 | 88880124 | chr16 | 88883238 | 88883377 | chr16 | 88941058 | 88941141 |
| chr16 | 88942119 | 88942160 | chr16 | 88943559 | 88944024 | chr16 | 88945815 | 88945995 |
| chr16 | 88955249 | 88955368 | chr16 | 88956230 | 88956399 | chr16 | 88957350 | 88957857 |
| chr16 | 88958397 | 88958431 | chr16 | 88963277 | 88963763 | chr16 | 88966303 | 88966588 |
| chr16 | 88968709 | 88968789 | chr16 | 88978024 | 88978072 | chr16 | 88993078 | 88993230 |
| chr16 | 88999617 | 88999647 | chr16 | 89000168 | 89000204 | chr16 | 89001094 | 89001124 |
| chr16 | 89007520 | 89007558 | chr16 | 89007880 | 89007995 | chr16 | 89008552 | 89008592 |
| chr16 | 89047717 | 89047747 | chr16 | 89072503 | 89072774 | chr16 | 89086109 | 89086197 |
| chr16 | 89107675 | 89107732 | chr16 | 89109385 | 89109415 | chr16 | 89120038 | 89120319 |
| chr16 | 89120708 | 89120864 | chr16 | 89138016 | 89138060 | chr16 | 89220327 | 89220398 |
| chr16 | 89220655 | 89220922 | chr16 | 89240843 | 89240873 | chr16 | 89254653 | 89254830 |
| chr16 | 89267334 | 89267364 | chr16 | 89267808 | 89267824 | chr16 | 89558610 | 89558703 |
| chr16 | 89575728 | 89575861 | chr16 | 89584136 | 89584417 | chr16 | 89676025 | 89676197 |
| chr16 | 89883972 | 89884185 | chr16 | 89884966 | 89885142 | chr16 | 89900124 | 89900180 |
| chr16 | 89900455 | 89900526 | chr16 | 90115428 | 90115458 | chr17 | 415134 | 415163 |
| chr17 | 556252 | 556282 | chr17 | 617001 | 617064 | chr17 | 631704 | 631734 |
| chr17 | 1082884 | 1083002 | chr17 | 1136593 | 1136653 | chr17 | 1174274 | 1174361 |
| chr17 | 1174385 | 1174413 | chr17 | 1494550 | 1494613 | chr17 | 1536116 | 1636146 |
| chr17 | 1545976 | 1546442 | chr17 | 1623703 | 1623735 | chr17 | 1959468 | 1959520 |
| chr17 | 2207718 | 2208063 | chr17 | 2219952 | 2220319 | chr17 | 2220564 | 2221059 |
| chr17 | 2250051 | 2250081 | chr17 | 2278801 | 2278925 | chr17 | 2496019 | 2496049 |
| chr17 | 2538269 | 2538337 | chr17 | 2607905 | 2607986 | chr17 | 2663898 | 2664032 |
| chr17 | 2811362 | 2811392 | chr17 | 2873476 | 2873551 | chr17 | 2950959 | 2951091 |
| chr17 | 3438914 | 3438932 | chr17 | 3657502 | 3657553 | chr17 | 3658490 | 3658519 |
| chr17 | 3658849 | 3659011 | chr17 | 4544607 | 4544710 | chr17 | 4693354 | 4693388 |
| chr17 | 4698990 | 4699252 | chr17 | 4891275 | 4891305 | chr17 | 4891527 | 4891556 |
| chr17 | 5000428 | 5000790 | chr17 | 5019637 | 5019662 | chr17 | 5019738 | 5019761 |
| chr17 | 5167638 | 5167681 | chr17 | 5168597 | 5168732 | chr17 | 6470357 | 6470419 |
| chr17 | 6616637 | 6616686 | chr17 | 6616911 | 6617173 | chr17 | 6679190 | 6679296 |
| chr17 | 6946107 | 6946141 | chr17 | 7043422 | 7043595 | chr17 | 7242844 | 7242899 |
| chr17 | 7348885 | 7348997 | chr17 | 7368947 | 7369139 | chr17 | 7471610 | 7471709 |
| chr17 | 7488151 | 7488249 | chr17 | 7555117 | 7555425 | chr17 | 7572957 | 7573018 |
| chr17 | 7573968 | 7574028 | chr17 | 7576847 | 7577167 | chr17 | 7577504 | 7577604 |
| chr17 | 7578164 | 7578570 | chr17 | 7579285 | 7579880 | chr17 | 7906254 | 7906535 |

TABLE 12-continued

| chr | start | end | chr | start | end | chr | start | end |
|---|---|---|---|---|---|---|---|---|
| chr17 | 7906832 | 7906861 | chr17 | 8104145 | 8104260 | chr17 | 8230335 | 8230694 |
| chr17 | 8534493 | 8534582 | chr17 | 8774623 | 8774653 | chr17 | 8868620 | 8868667 |
| chr17 | 8868815 | 8869385 | chr17 | 8906266 | 8906518 | chr17 | 8906993 | 8907575 |
| chr17 | 8926060 | 8926263 | chr17 | 9790805 | 9790835 | chr17 | 10101084 | 10101109 |
| chr17 | 10101132 | 10101447 | chr17 | 10102415 | 10102665 | chr17 | 10599510 | 10599546 |
| chr17 | 11144926 | 11144989 | chr17 | 11984693 | 11984722 | chr17 | 11998944 | 11998973 |
| chr17 | 12013726 | 12013755 | chr17 | 12016550 | 12016630 | chr17 | 12028618 | 12028647 |
| chr17 | 12659029 | 12659063 | chr17 | 13504195 | 13504195 | chr17 | 13504557 | 13504681 |
| chr17 | 13505002 | 13505188 | chr17 | 13505418 | 13505572 | chr17 | 14201041 | 14201181 |
| chr17 | 14204212 | 14204242 | chr17 | 14204527 | 14204620 | chr17 | 15245050 | 15245139 |
| chr17 | 15926819 | 15926849 | chr17 | 16119860 | 16120047 | chr17 | 16282251 | 16282300 |
| chr17 | 16284630 | 16285065 | chr17 | 16326144 | 16326216 | chr17 | 16428708 | 16428738 |
| chr17 | 16570699 | 16570794 | chr17 | 17062574 | 17062763 | chr17 | 17117365 | 17117395 |
| chr17 | 17123963 | 17123993 | chr17 | 17398404 | 17398440 | chr17 | 17719242 | 17719355 |
| chr17 | 18162844 | 18163325 | chr17 | 18538154 | 18538275 | chr17 | 18817198 | 18817284 |
| chr17 | 19769739 | 19769821 | chr17 | 19886035 | 19886221 | chr17 | 20039589 | 20039676 |
| chr17 | 20081131 | 20081161 | chr17 | 20205055 | 20205181 | chr17 | 20238152 | 20238198 |
| chr17 | 20468021 | 20468090 | chr17 | 20817755 | 20817917 | chr17 | 21003587 | 21003721 |
| chr17 | 25620573 | 25620715 | chr17 | 25676959 | 25676989 | chr17 | 25680264 | 25680294 |
| chr17 | 25907750 | 25907780 | chr17 | 26263183 | 26263322 | chr17 | 26554634 | 26554705 |
| chr17 | 26927249 | 26927410 | chr17 | 26961770 | 26961833 | chr17 | 27036492 | 27037023 |
| chr17 | 27038649 | 27038685 | chr17 | 27056577 | 27056857 | chr17 | 27081845 | 27081963 |
| chr17 | 27170162 | 27170460 | chr17 | 27181180 | 27181371 | chr17 | 27332453 | 27332660 |
| chr17 | 27686651 | 27686783 | chr17 | 27716114 | 27716220 | chr17 | 27716436 | 27716642 |
| chr17 | 27940591 | 27940911 | chr17 | 28112648 | 28112688 | chr17 | 28112951 | 28113032 |
| chr17 | 28562701 | 28562765 | chr17 | 29232244 | 29232350 | chr17 | 29234283 | 29234313 |
| chr17 | 29249717 | 29249930 | chr17 | 29298080 | 29298581 | chr17 | 29508761 | 29508790 |
| chr17 | 29541527 | 29541556 | chr17 | 29562732 | 29562761 | chr17 | 29718215 | 29718269 |
| chr17 | 29719187 | 29719242 | chr17 | 30243768 | 30243907 | chr17 | 30250325 | 30250364 |
| chr17 | 30258469 | 30258499 | chr17 | 30568137 | 30568174 | chr17 | 30710818 | 30710888 |
| chr17 | 31618425 | 31619319 | chr17 | 31620026 | 31620155 | chr17 | 32386720 | 32386875 |
| chr17 | 32484020 | 32484049 | chr17 | 32906379 | 32906555 | chr17 | 32906599 | 32906636 |
| chr17 | 32906987 | 32907146 | chr17 | 32907652 | 32907753 | chr17 | 32908132 | 32908146 |
| chr17 | 32908171 | 32908374 | chr17 | 32908647 | 32908931 | chr17 | 33288229 | 33288351 |
| chr17 | 33288890 | 33288988 | chr17 | 33672916 | 33672986 | chr17 | 33721211 | 33721349 |
| chr17 | 33877286 | 33877439 | chr17 | 33917210 | 33917268 | chr17 | 35165645 | 35165691 |
| chr17 | 35165986 | 35166016 | chr17 | 35285542 | 35285666 | chr17 | 35290388 | 35290655 |
| chr17 | 35291320 | 35291354 | chr17 | 35291829 | 35291898 | chr17 | 35291921 | 35292626 |
| chr17 | 35293704 | 35294154 | chr17 | 35294461 | 35294505 | chr17 | 35295047 | 35295160 |
| chr17 | 35296143 | 35296292 | chr17 | 35296728 | 35296888 | chr17 | 35297619 | 35298153 |
| chr17 | 35299251 | 35299443 | chr17 | 35299601 | 35299965 | chr17 | 35300261 | 35300712 |
| chr17 | 35300813 | 35300854 | chr17 | 35303340 | 35303535 | chr17 | 35872722 | 35872861 |
| chr17 | 36103021 | 36103326 | chr17 | 36103571 | 36103601 | chr17 | 36104218 | 36104550 |
| chr17 | 36104644 | 36104779 | chr17 | 36105223 | 36105349 | chr17 | 36105459 | 36105596 |
| chr17 | 36715772 | 36715967 | chr17 | 37001415 | 37001921 | chr17 | 37011176 | 37011236 |
| chr17 | 37131789 | 37132028 | chr17 | 37181771 | 37181865 | chr17 | 37192072 | 37192201 |
| chr17 | 37312431 | 37312477 | chr17 | 37321186 | 37321624 | chr17 | 37321788 | 37321972 |
| chr17 | 37366337 | 37366552 | chr17 | 37369180 | 37369210 | chr17 | 37381011 | 37381429 |
| chr17 | 37381571 | 37381726 | chr17 | 37381826 | 37381850 | chr17 | 37382146 | 37382248 |
| chr17 | 37484062 | 37484128 | chr17 | 32757153 | 37752217 | chr17 | 32760488 | 37760561 |
| chr17 | 37761997 | 37762334 | chr17 | 37868190 | 37868294 | chr17 | 37879568 | 37879615 |
| chr17 | 37880205 | 37880276 | chr17 | 37880971 | 37881018 | chr17 | 37881318 | 37881631 |
| chr17 | 38179397 | 38179430 | chr17 | 38335459 | 38335533 | chr17 | 38347560 | 38347615 |
| chr17 | 38380553 | 38380598 | chr17 | 38474363 | 38474502 | chr17 | 38497616 | 38497645 |
| chr17 | 38498083 | 38498112 | chr17 | 38504087 | 38504116 | chr17 | 38510555 | 38510584 |
| chr17 | 38574991 | 38575021 | chr17 | 39682352 | 39682711 | chr17 | 39834201 | 39834287 |
| chr17 | 40332943 | 40333226 | chr17 | 40400857 | 40401031 | chr17 | 40464278 | 40464317 |
| chr17 | 40464517 | 40464607 | chr17 | 40474467 | 40474496 | chr17 | 40826197 | 40826226 |
| chr17 | 40837022 | 40837051 | chr17 | 40837287 | 40837383 | chr17 | 40838982 | 40839022 |
| chr17 | 40897739 | 40897788 | chr17 | 40975413 | 40975677 | chr17 | 41175146 | 41175331 |
| chr17 | 41177394 | 41177459 | chr17 | 41197714 | 41197743 | chr17 | 41201163 | 41201192 |
| chr17 | 41203073 | 41203102 | chr17 | 41209064 | 41209114 | chr17 | 41215890 | 41215961 |
| chr17 | 41267731 | 41267775 | chr17 | 41276031 | 41276075 | chr17 | 41277259 | 41277721 |
| chr17 | 41278621 | 41278700 | chr17 | 41651850 | 41651880 | chr17 | 41745825 | 41745855 |
| chr17 | 41791460 | 41791489 | chr17 | 41791665 | 41791694 | chr17 | 42030329 | 42030750 |
| chr17 | 42061336 | 42061381 | chr17 | 42082522 | 42082557 | chr17 | 42084361 | 42084626 |
| chr17 | 42092190 | 42092220 | chr17 | 42110423 | 42110561 | chr17 | 42142661 | 42142808 |
| chr17 | 42246452 | 42246521 | chr17 | 42321590 | 42321674 | chr17 | 42331412 | 42331659 |
| chr17 | 42393842 | 42394024 | chr17 | 42402884 | 42402917 | chr17 | 42580695 | 42580793 |
| chr17 | 42587249 | 42587355 | chr17 | 42590091 | 42590224 | chr17 | 42635295 | 42635760 |
| chr17 | 42733711 | 42733884 | chr17 | 42767947 | 42768198 | chr17 | 42787481 | 42787616 |
| chr17 | 42907564 | 42907630 | chr17 | 42907655 | 42907951 | chr17 | 42975726 | 42975756 |
| chr17 | 43001891 | 43001946 | chr17 | 43044658 | 43044688 | chr17 | 43045039 | 43045116 |
| chr17 | 43046260 | 43046385 | chr17 | 43339109 | 43339333 | chr17 | 43339609 | 43339899 |
| chr17 | 43974256 | 43974358 | chr17 | 44897416 | 44897445 | chr17 | 45022106 | 45022140 |
| chr17 | 45187608 | 45187638 | chr17 | 45331014 | 45331313 | chr17 | 45810850 | 45811341 |
| chr17 | 45867315 | 45867460 | chr17 | 46125007 | 46125061 | chr17 | 46567400 | 46567655 |
| chr17 | 46619540 | 46619569 | chr17 | 46620494 | 46621094 | chr17 | 46621353 | 46621458 |

TABLE 12-continued

| chr | start | end | chr | start | end | chr | start | end |
|---|---|---|---|---|---|---|---|---|
| chr17 | 46621856 | 46621909 | chr17 | 46655148 | 46655178 | chr17 | 46655451 | 46655998 |
| chr17 | 46656058 | 46656704 | chr17 | 46659429 | 46659859 | chr17 | 46663743 | 46663824 |
| chr17 | 46663856 | 46663887 | chr17 | 46674873 | 46674970 | chr17 | 46675170 | 46675600 |
| chr17 | 46690467 | 46690664 | chr17 | 46691505 | 46691592 | chr17 | 46691805 | 46691818 |
| chr17 | 46691988 | 46692110 | chr17 | 46692439 | 46692606 | chr17 | 46710946 | 46710989 |
| chr17 | 46713959 | 46714072 | chr17 | 46795641 | 46796373 | chr17 | 46796499 | 46796637 |
| chr17 | 46796850 | 46797213 | chr17 | 46797275 | 46797582 | chr17 | 46799625 | 46799896 |
| chr17 | 46800601 | 46800668 | chr17 | 46800961 | 46801047 | chr17 | 46801109 | 46801416 |
| chr17 | 46802459 | 46802911 | chr17 | 46802994 | 46803286 | chr17 | 46804107 | 46804428 |
| chr17 | 46810416 | 46810958 | chr17 | 46811354 | 46811499 | chr17 | 46816282 | 46816877 |
| chr17 | 46824224 | 46824275 | chr17 | 46824359 | 46825054 | chr17 | 46825284 | 46825514 |
| chr17 | 46826930 | 46827127 | chr17 | 46827330 | 46827501 | chr17 | 46827626 | 46827756 |
| chr17 | 46829498 | 46829579 | chr17 | 46829979 | 46830110 | chr17 | 46831779 | 46832325 |
| chr17 | 46832490 | 46832639 | chr17 | 47072805 | 47073028 | chr17 | 47073104 | 47073327 |
| chr17 | 47073389 | 47073465 | chr17 | 47073988 | 47074228 | chr17 | 47074561 | 47074895 |
| chr17 | 47075160 | 47075364 | chr17 | 47075715 | 47075734 | chr17 | 47075880 | 47076055 |
| chr17 | 47574090 | 47574149 | chr17 | 47657544 | 47657583 | chr17 | 47865514 | 47865555 |
| chr17 | 47987525 | 47987619 | chr17 | 47987930 | 47988114 | chr17 | 48041152 | 48041320 |
| chr17 | 48041672 | 48041721 | chr17 | 48042039 | 48042069 | chr17 | 48042435 | 48042647 |
| chr17 | 48042751 | 48042956 | chr17 | 48048952 | 48049059 | chr17 | 48049307 | 48050526 |
| chr17 | 48071020 | 48071050 | chr17 | 48071807 | 48071894 | chr17 | 48473056 | 48473236 |
| chr17 | 48545804 | 48545950 | chr17 | 48589801 | 48589831 | chr17 | 48612223 | 48612308 |
| chr17 | 48636581 | 48637136 | chr17 | 48653128 | 48653158 | chr17 | 48799820 | 48799866 |
| chr17 | 49027838 | 49027876 | chr17 | 49229267 | 49229703 | chr17 | 50235216 | 50235258 |
| chr17 | 50235631 | 50235952 | chr17 | 51901004 | 51901034 | chr17 | 53341252 | 53341536 |
| chr17 | 53342876 | 53343089 | chr17 | 53479184 | 53479316 | chr17 | 53814544 | 53814678 |
| chr17 | 53922649 | 53922790 | chr17 | 54674986 | 54675272 | chr17 | 54755969 | 54755990 |
| chr17 | 55037326 | 55037626 | chr17 | 55122813 | 55122842 | chr17 | 55213641 | 55213670 |
| chr17 | 55962573 | 55962841 | chr17 | 56092600 | 46092736 | chr17 | 56234405 | 56234743 |
| chr17 | 56326949 | 56326994 | chr17 | 56327271 | 56327301 | chr17 | 56471121 | 56471167 |
| chr17 | 56743206 | 56743249 | chr17 | 56833127 | 56833221 | chr17 | 56833707 | 56834000 |
| chr17 | 56834020 | 56834075 | chr17 | 56834306 | 56834375 | chr17 | 57296865 | 57297129 |
| chr17 | 57386255 | 57386735 | chr17 | 57787402 | 57787465 | chr17 | 57832475 | 57832607 |
| chr17 | 58216613 | 58216836 | chr17 | 58216866 | 58217298 | chr17 | 58217357 | 58217551 |
| chr17 | 58218765 | 58218993 | chr17 | 58227374 | 58227397 | chr17 | 58498697 | 58499314 |
| chr17 | 59474157 | 59474246 | chr17 | 59474833 | 59475100 | chr17 | 59475678 | 59476127 |
| chr17 | 59476410 | 59476635 | chr17 | 59478147 | 59478602 | chr17 | 59481657 | 59481678 |
| chr17 | 59488101 | 59488423 | chr17 | 59528876 | 59529150 | chr17 | 59529254 | 59529264 |
| chr17 | 59529844 | 59530352 | chr17 | 59531667 | 59532017 | chr17 | 59533875 | 59534405 |
| chr17 | 59534751 | 59534781 | chr17 | 59535137 | 59535219 | chr17 | 59539236 | 59539601 |
| chr17 | 59924556 | 59924585 | chr17 | 59937192 | 59937236 | chr17 | 61677374 | 61677404 |
| chr17 | 61778235 | 61778248 | chr17 | 61817576 | 61817955 | chr17 | 61926172 | 61926324 |
| chr17 | 61926508 | 61926603 | chr17 | 62028596 | 62028790 | chr17 | 62777335 | 62777450 |
| chr17 | 62777746 | 62777791 | chr17 | 64672366 | 64672544 | chr17 | 65715296 | 65715493 |
| chr17 | 66420718 | 66420837 | chr17 | 66596471 | 66596525 | chr17 | 66596984 | 66597021 |
| chr17 | 67410305 | 67410397 | chr17 | 68164733 | 68164928 | chr17 | 70026543 | 70026667 |
| chr17 | 70112916 | 70113566 | chr17 | 70113648 | 70114018 | chr17 | 70114153 | 70114517 |
| chr17 | 70215683 | 70216306 | chr17 | 70216393 | 70216595 | chr17 | 70586165 | 70586272 |
| chr17 | 71229815 | 71229918 | chr17 | 71641544 | 71641683 | chr17 | 71948439 | 71948863 |
| chr17 | 72236510 | 72236548 | chr17 | 72270286 | 72270415 | chr17 | 72321933 | 72321975 |
| chr17 | 72322363 | 72322557 | chr17 | 72353213 | 72353259 | chr17 | 72353417 | 72353550 |
| chr17 | 72427853 | 72427999 | chr17 | 72428344 | 72428381 | chr17 | 72491378 | 72491531 |
| chr17 | 72667337 | 72667481 | chr17 | 72849010 | 72849079 | chr17 | 72857038 | 72857368 |
| chr17 | 72862371 | 72862460 | chr17 | 72920796 | 72921032 | chr17 | 73031637 | 73031935 |
| chr17 | 73115588 | 73115658 | chr17 | 73115884 | 73115914 | chr17 | 73128301 | 73128338 |
| chr17 | 73147177 | 73147356 | chr17 | 73147774 | 73147992 | chr17 | 73215289 | 73215423 |
| chr17 | 73351981 | 73352086 | chr17 | 73545998 | 73546299 | chr17 | 73586015 | 73586418 |
| chr17 | 73608306 | 73608336 | chr17 | 73636144 | 73636337 | chr17 | 73692986 | 73693122 |
| chr17 | 73709838 | 73709955 | chr17 | 73782870 | 73782947 | chr17 | 73808631 | 73808671 |
| chr17 | 73827213 | 73827243 | chr17 | 73901630 | 73901893 | chr17 | 73904093 | 73904127 |
| chr17 | 74028346 | 74028413 | chr17 | 74047797 | 74048063 | chr17 | 74070281 | 74070479 |
| chr17 | 74071445 | 74071481 | chr17 | 74071689 | 74071729 | chr17 | 74072999 | 74073036 |
| chr17 | 74073269 | 74073433 | chr17 | 74087118 | 74087185 | chr17 | 74299798 | 74299899 |
| chr17 | 74390363 | 74390393 | chr17 | 74533844 | 74534310 | chr17 | 74581182 | 74581221 |
| chr17 | 74663258 | 74663288 | chr17 | 74732944 | 74732973 | chr17 | 74865053 | 74865192 |
| chr17 | 74865698 | 74866243 | chr17 | 75137660 | 75137887 | chr17 | 75207514 | 75207630 |
| chr17 | 75207839 | 75207987 | chr17 | 75276054 | 75276083 | chr17 | 75276413 | 75276442 |
| chr17 | 75277348 | 75277659 | chr17 | 75278020 | 75278049 | chr17 | 75279105 | 75279134 |
| chr17 | 75282025 | 75282154 | chr17 | 75315512 | 75315681 | chr17 | 75316368 | 75316397 |
| chr17 | 75317170 | 75317199 | chr17 | 75347755 | 75347784 | chr17 | 75368735 | 75369238 |
| chr17 | 75369440 | 75369457 | chr17 | 75369493 | 75369860 | chr17 | 75370269 | 75370316 |
| chr17 | 75370596 | 75370625 | chr17 | 75373312 | 75373341 | chr17 | 75385071 | 75385446 |
| chr17 | 75405827 | 75405856 | chr17 | 75417150 | 75417179 | chr17 | 75523142 | 75523272 |
| chr17 | 75524636 | 75525194 | chr17 | 75733978 | 75734244 | chr17 | 75797111 | 75797179 |
| chr17 | 76021047 | 76021077 | chr17 | 76125196 | 76125225 | chr17 | 76126434 | 76126463 |
| chr17 | 76128466 | 76128663 | chr17 | 76130124 | 76130153 | chr17 | 76130481 | 76130510 |
| chr17 | 76135783 | 76136001 | chr17 | 76137951 | 76138190 | chr17 | 76138498 | 76138622 |
| chr17 | 76187407 | 76187544 | chr17 | 76207342 | 76207372 | chr17 | 76211302 | 76211506 |

TABLE 12-continued

| chr | start | end | chr | start | end | chr | start | end |
|---|---|---|---|---|---|---|---|---|
| chr17 | 76227849 | 76228161 | chr17 | 76228214 | 76228357 | chr17 | 76404615 | 76404659 |
| chr17 | 76877177 | 76877212 | chr17 | 76884417 | 76884447 | chr17 | 76974447 | 76974499 |
| chr17 | 76983518 | 76983669 | chr17 | 76984053 | 76984188 | chr17 | 77070307 | 77070457 |
| chr17 | 77084518 | 77084727 | chr17 | 77105055 | 77105198 | chr17 | 77145129 | 77145242 |
| chr17 | 77179113 | 77179278 | chr17 | 77179630 | 77179776 | chr17 | 77394706 | 77394850 |
| chr17 | 77776827 | 77776995 | chr17 | 77777053 | 77777056 | chr17 | 77777585 | 77777903 |
| chr17 | 77777944 | 77777961 | chr17 | 77778943 | 77779179 | chr17 | 77789474 | 77789500 |
| chr17 | 77825696 | 77825812 | chr17 | 77827114 | 77827201 | chr17 | 77899664 | 77899693 |
| chr17 | 77919429 | 77919477 | chr17 | 77924259 | 77924351 | chr17 | 78122158 | 78122190 |
| chr17 | 78194821 | 78194861 | chr17 | 78272278 | 78272313 | chr17 | 78447127 | 78447157 |
| chr17 | 78451931 | 78451953 | chr17 | 78452296 | 78452340 | chr17 | 78452681 | 78452833 |
| chr17 | 78518031 | 78518198 | chr17 | 78599596 | 78599628 | chr17 | 78667992 | 78668159 |
| chr17 | 78874441 | 78874559 | chr17 | 78975667 | 78975758 | chr17 | 78999625 | 78999654 |
| chr17 | 79058302 | 79058333 | chr17 | 79094182 | 79094245 | chr17 | 79099770 | 79099799 |
| chr17 | 79626591 | 79626703 | chr17 | 79626955 | 79626985 | chr17 | 79769433 | 79769503 |
| chr17 | 79813409 | 79813507 | chr17 | 79850445 | 79850537 | chr17 | 79896013 | 79896043 |
| chr17 | 79939605 | 79939835 | chr17 | 79945037 | 79945074 | chr17 | 80186260 | 80186289 |
| chr17 | 80197756 | 80197898 | chr17 | 80254266 | 80254296 | chr17 | 80289234 | 80289310 |
| chr17 | 80289858 | 80289892 | chr17 | 80294282 | 80294427 | chr17 | 80329709 | 80330000 |
| chr17 | 80394063 | 80394185 | chr17 | 80394573 | 80394602 | chr17 | 80479311 | 80479559 |
| chr17 | 80491572 | 80491602 | chr17 | 80535382 | 80535487 | chr17 | 80571380 | 80571776 |
| chr17 | 80593754 | 80594107 | chr17 | 80654983 | 80555013 | chr17 | 80693317 | 80693554 |
| chr17 | 80749152 | 80749276 | chr17 | 80751650 | 80751714 | chr17 | 80794259 | 80794288 |
| chr17 | 80797692 | 80798345 | chr17 | 80832305 | 80832411 | chr17 | 80832712 | 80832796 |
| chr17 | 80859239 | 80859269 | chr17 | 81008618 | 81008826 | chr17 | 81033487 | 81033517 |
| chr17 | 81048993 | 81049023 | chr17 | 81049994 | 81050058 | chr18 | 147543 | 147613 |
| chr18 | 499367 | 499482 | chr18 | 500046 | 500738 | chr18 | 597548 | 597578 |
| chr18 | 697854 | 697901 | chr18 | 904462 | 904648 | chr18 | 905000 | 905030 |
| chr18 | 905434 | 905615 | chr18 | 906871 | 906907 | chr18 | 907472 | 907594 |
| chr18 | 907912 | 907977 | chr18 | 908454 | 908589 | chr18 | 909487 | 909587 |
| chr18 | 2755770 | 2755878 | chr18 | 2906268 | 2906304 | chr18 | 3214441 | 3214825 |
| chr18 | 3215042 | 3215256 | chr18 | 3499067 | 3499371 | chr18 | 4453964 | 4454163 |
| chr18 | 5133207 | 5133343 | chr18 | 5196576 | 5196959 | chr18 | 5197202 | 5197271 |
| chr18 | 5197330 | 5197347 | chr18 | 5237878 | 5238247 | chr18 | 5628167 | 5628515 |
| chr18 | 5629774 | 5629825 | chr18 | 5630312 | 5630362 | chr18 | 5895023 | 5895205 |
| chr18 | 5895975 | 5896085 | chr18 | 6729952 | 6729993 | chr18 | 6908056 | 6908243 |
| chr18 | 7117665 | 7117804 | chr18 | 7567783 | 7568291 | chr18 | 8608748 | 8608837 |
| chr18 | 8608902 | 8608968 | chr18 | 8612252 | 8612282 | chr18 | 9771586 | 9771753 |
| chr18 | 9868137 | 9868174 | chr18 | 9912767 | 9912797 | chr18 | 10251324 | 10251432 |
| chr18 | 10589096 | 10589348 | chr18 | 10733492 | 10733605 | chr18 | 11148969 | 11149045 |
| chr18 | 11149561 | 11149759 | chr18 | 11149780 | 11149888 | chr18 | 11401654 | 11401817 |
| chr18 | 11689190 | 11689220 | chr18 | 11752128 | 11752379 | chr18 | 11752700 | 11752730 |
| chr18 | 11942728 | 11942838 | chr18 | 11979677 | 11979860 | chr18 | 12254305 | 12254578 |
| chr18 | 12277243 | 12277273 | chr18 | 12307247 | 12307505 | chr18 | 12307603 | 12307751 |
| chr18 | 12375483 | 12375597 | chr18 | 12375923 | 12376129 | chr18 | 12890152 | 12890278 |
| chr18 | 12948993 | 12949023 | chr18 | 13132080 | 13132246 | chr18 | 13824025 | 13824102 |
| chr18 | 13826393 | 13826536 | chr18 | 13868713 | 13868919 | chr18 | 15198110 | 15198248 |
| chr18 | 18822392 | 18823274 | chr18 | 19191525 | 19191585 | chr18 | 19750308 | 19750346 |
| chr18 | 20911541 | 20911571 | chr18 | 21035222 | 21035252 | chr18 | 21269349 | 21269390 |
| chr18 | 21269659 | 21269740 | chr18 | 21719351 | 21719568 | chr18 | 21719938 | 21720064 |
| chr18 | 22929081 | 22929095 | chr18 | 22929187 | 22929718 | chr18 | 22929927 | 22930559 |
| chr18 | 22930790 | 22931178 | chr18 | 23686462 | 23686618 | chr18 | 24127748 | 24128030 |
| chr18 | 24130809 | 24130946 | chr18 | 24131099 | 24131187 | chr18 | 24764951 | 24765168 |
| chr18 | 25755593 | 25755655 | chr18 | 25756010 | 25756040 | chr18 | 25756495 | 25756729 |
| chr18 | 25757187 | 25757452 | chr18 | 25757787 | 25757824 | chr18 | 25758129 | 25758141 |
| chr18 | 28620899 | 28620955 | chr18 | 28621034 | 28621097 | chr18 | 28621328 | 28621393 |
| chr18 | 28621636 | 28621932 | chr18 | 28622419 | 28622488 | chr18 | 29413805 | 29413839 |
| chr18 | 29719775 | 29720012 | chr18 | 30349740 | 30349781 | chr18 | 31020495 | 31020510 |
| chr18 | 31158093 | 31158158 | chr18 | 31739035 | 31739469 | chr18 | 31802132 | 31802167 |
| chr18 | 31802938 | 31802968 | chr18 | 31803438 | 31803472 | chr18 | 31902793 | 31902945 |
| chr18 | 32073908 | 32074086 | chr18 | 32557832 | 32557864 | chr18 | 32847598 | 32847642 |
| chr18 | 32957803 | 32957839 | chr18 | 33078363 | 33078662 | chr18 | 33877683 | 33877754 |
| chr18 | 35065072 | 35065145 | chr18 | 35144845 | 35144936 | chr18 | 35144969 | 35145465 |
| chr18 | 35145968 | 35146036 | chr18 | 35146062 | 35146241 | chr18 | 35147487 | 35147569 |
| chr18 | 43546048 | 43546134 | chr18 | 43914211 | 43914278 | chr18 | 44259903 | 44259990 |
| chr18 | 44336034 | 44336449 | chr18 | 44337174 | 44337617 | chr18 | 44337650 | 44337841 |
| chr18 | 44773060 | 44773116 | chr18 | 44773592 | 44773966 | chr18 | 44774406 | 44774890 |
| chr18 | 44775380 | 44775554 | chr18 | 44776972 | 44777088 | chr18 | 44777301 | 44777331 |
| chr18 | 44777596 | 44777750 | chr18 | 44778049 | 44778326 | chr18 | 44781003 | 44781041 |
| chr18 | 44787781 | 44787846 | chr18 | 44788251 | 44788281 | chr18 | 44789474 | 44789514 |
| chr18 | 44789872 | 44789937 | chr18 | 45058069 | 45058240 | chr18 | 46142662 | 46142809 |
| chr18 | 47720492 | 47720522 | chr18 | 48604773 | 48604802 | chr18 | 48636211 | 48636320 |
| chr18 | 49867303 | 49867399 | chr18 | 49868634 | 49868664 | chr18 | 51771058 | 51771128 |
| chr18 | 52989009 | 52989220 | chr18 | 52989741 | 52989882 | chr18 | 53257137 | 53257204 |
| chr18 | 53446970 | 53447474 | chr18 | 53447799 | 53447816 | chr18 | 53989796 | 53989877 |
| chr18 | 54789070 | 54789256 | chr18 | 55019707 | 55019775 | chr18 | 55020655 | 55020698 |
| chr18 | 55021078 | 55021242 | chr18 | 55103381 | 55103411 | chr18 | 55104808 | 55105140 |
| chr18 | 55105728 | 55105830 | chr18 | 55114480 | 55114644 | chr18 | 55426948 | 55426978 |

TABLE 12-continued

| chr | start | end | chr | start | end | chr | start | end |
|---|---|---|---|---|---|---|---|---|
| chr18 | 55850845 | 55850987 | chr18 | 56483918 | 56483958 | chr18 | 56815734 | 56816107 |
| chr18 | 56887076 | 56887424 | chr18 | 56888554 | 56888623 | chr18 | 56931541 | 56931583 |
| chr18 | 56931967 | 56932107 | chr18 | 56932352 | 56932637 | chr18 | 56935010 | 56935319 |
| chr18 | 56936004 | 56936074 | chr18 | 56939113 | 56939174 | chr18 | 56939423 | 56939651 |
| chr18 | 56939764 | 56940170 | chr18 | 56940566 | 56940722 | chr18 | 56940955 | 56941244 |
| chr18 | 56941558 | 56941788 | chr18 | 57363706 | 57363743 | chr18 | 57364658 | 57364691 |
| chr18 | 59000988 | 59001022 | chr18 | 59001301 | 59001343 | chr18 | 59001498 | 59001740 |
| chr18 | 60263661 | 60263895 | chr18 | 60557729 | 60557759 | chr18 | 60985498 | 60985532 |
| chr18 | 60985593 | 60985732 | chr18 | 61143911 | 61143975 | chr18 | 67067558 | 67067907 |
| chr18 | 67068715 | 67068811 | chr18 | 67069216 | 67069246 | chr18 | 70209148 | 70209205 |
| chr18 | 70210418 | 70210508 | chr18 | 70211626 | 70211666 | chr18 | 70534282 | 70534315 |
| chr18 | 70534428 | 70534731 | chr18 | 70535373 | 70535554 | chr18 | 70535576 | 70535582 |
| chr18 | 70536010 | 70536083 | chr18 | 70536188 | 70536604 | chr18 | 70536833 | 70536871 |
| chr18 | 70537188 | 70537218 | chr18 | 72845833 | 72845863 | chr18 | 73167585 | 73167832 |
| chr18 | 73628019 | 73628068 | chr18 | 74501144 | 74501183 | chr18 | 74755508 | 74755590 |
| chr18 | 74961326 | 74961955 | chr18 | 74962019 | 74962147 | chr18 | 74962970 | 74963545 |
| chr18 | 75335093 | 75335123 | chr18 | 75339231 | 75339340 | chr18 | 75362931 | 75362985 |
| chr18 | 75551271 | 75551301 | chr18 | 75612225 | 75612286 | chr18 | 75999404 | 75999434 |
| chr18 | 76239541 | 76239615 | chr18 | 76501479 | 76501509 | chr18 | 76653631 | 76653661 |
| chr18 | 76686249 | 76686279 | chr18 | 76689735 | 76689765 | chr18 | 76740102 | 76740223 |
| chr18 | 77050480 | 77050678 | chr18 | 77143346 | 77143376 | chr18 | 77167824 | 77167854 |
| chr18 | 77181355 | 77181409 | chr18 | 77194936 | 77194978 | chr18 | 77205532 | 77205638 |
| chr18 | 77285897 | 77286028 | chr18 | 77300326 | 77300483 | chr18 | 77309533 | 77309563 |
| chr18 | 77312866 | 77312927 | chr18 | 77329727 | 77330017 | chr18 | 27371430 | 77371547 |
| chr18 | 77459762 | 77459877 | chr18 | 77512225 | 77512255 | chr18 | 27543249 | 77543481 |
| chr18 | 77543700 | 77543824 | chr18 | 77548352 | 77548609 | chr18 | 77550206 | 77550367 |
| chr18 | 77558082 | 77558358 | chr18 | 77558831 | 77558930 | chr18 | 77576934 | 77577043 |
| chr18 | 77636591 | 77636621 | chr18 | 77698881 | 77698919 | chr18 | 78004993 | 78005051 |
| chr19 | 403538 | 403809 | chr19 | 407189 | 407320 | chr19 | 418225 | 418255 |
| chr19 | 462181 | 462269 | chr19 | 468757 | 468787 | chr19 | 485165 | 485394 |
| chr19 | 549361 | 549451 | chr19 | 555608 | 555768 | chr19 | 570156 | 570194 |
| chr19 | 591365 | 591416 | chr19 | 592589 | 592632 | chr19 | 593290 | 593462 |
| chr19 | 599214 | 599333 | chr19 | 607070 | 607110 | chr19 | 690888 | 690940 |
| chr19 | 752136 | 752462 | chr19 | 869337 | 869394 | chr19 | 883624 | 883791 |
| chr19 | 884018 | 884162 | chr19 | 891516 | 891723 | chr19 | 955757 | 956237 |
| chr19 | 959128 | 959187 | chr19 | 1003305 | 1003384 | chr19 | 1003669 | 1003734 |
| chr19 | 1004915 | 1005441 | chr19 | 1030176 | 1030225 | chr19 | 1047890 | 1047939 |
| chr19 | 1048348 | 1048465 | chr19 | 1083314 | 1083437 | chr19 | 1156524 | 1156554 |
| chr19 | 1170185 | 1170230 | chr19 | 1171099 | 1171324 | chr19 | 1220422 | 1220610 |
| chr19 | 1221981 | 1222010 | chr19 | 1236474 | 1236678 | chr19 | 1274778 | 1274826 |
| chr19 | 1308047 | 1308081 | chr19 | 1325788 | 1325889 | chr19 | 1330064 | 1330214 |
| chr19 | 1401752 | 1401795 | chr19 | 1450319 | 1450390 | chr19 | 1496413 | 1496450 |
| chr19 | 1496654 | 1496694 | chr19 | 1524443 | 1524447 | chr19 | 1525605 | 1525960 |
| chr19 | 1527227 | 1527394 | chr19 | 1547233 | 1547263 | chr19 | 1689436 | 1689595 |
| chr19 | 1754172 | 1754193 | chr19 | 1754225 | 1754254 | chr19 | 1754739 | 1754804 |
| chr19 | 1757416 | 1757615 | chr19 | 1762474 | 1762505 | chr19 | 1764293 | 1764339 |
| chr19 | 1775076 | 1775239 | chr19 | 1776376 | 1776534 | chr19 | 1799466 | 1799516 |
| chr19 | 1800032 | 1800300 | chr19 | 1807970 | 1808413 | chr19 | 2135672 | 2135701 |
| chr19 | 2155031 | 2155061 | chr19 | 2251152 | 2251234 | chr19 | 2251611 | 2251715 |
| chr19 | 2252589 | 2252658 | chr19 | 2252984 | 2253735 | chr19 | 2274677 | 2274713 |
| chr19 | 2290253 | 2290271 | chr19 | 2290631 | 2290867 | chr19 | 2302793 | 2302951 |
| chr19 | 2330317 | 2330407 | chr19 | 2331413 | 2331443 | chr19 | 2413125 | 2413155 |
| chr19 | 2414257 | 2414337 | chr19 | 2513250 | 2513285 | chr19 | 2642877 | 2642947 |
| chr19 | 2683911 | 2684080 | chr19 | 3041417 | 3041447 | chr19 | 3093571 | 3093818 |
| chr19 | 3114998 | 3115027 | chr19 | 3118927 | 3118956 | chr19 | 3219512 | 3219565 |
| chr19 | 3296613 | 3296670 | chr19 | 3361139 | 3361388 | chr19 | 3562128 | 3562797 |
| chr19 | 3570230 | 3570371 | chr19 | 3578138 | 3578223 | chr19 | 3659668 | 3659793 |
| chr19 | 3716179 | 3716241 | chr19 | 3718052 | 3718082 | chr19 | 3278130 | 3778394 |
| chr19 | 3779277 | 3779435 | chr19 | 3785649 | 3785835 | chr19 | 3785865 | 3786220 |
| chr19 | 3821044 | 3821217 | chr19 | 3822135 | 3822203 | chr19 | 3834572 | 3834641 |
| chr19 | 3855407 | 3855595 | chr19 | 3966686 | 3966755 | chr19 | 3994540 | 3994595 |
| chr19 | 4054435 | 4054471 | chr19 | 4095471 | 4095514 | chr19 | 4101087 | 4101116 |
| chr19 | 4110565 | 4110597 | chr19 | 4117526 | 4117630 | chr19 | 4160800 | 4160898 |
| chr19 | 4195767 | 4195853 | chr19 | 4305057 | 4305086 | chr19 | 4311273 | 4311430 |
| chr19 | 4509338 | 4509440 | chr19 | 4548134 | 4548364 | chr19 | 4549454 | 4549565 |
| chr19 | 4550246 | 4550330 | chr19 | 4555895 | 4556112 | chr19 | 4567098 | 4557235 |
| chr19 | 4572332 | 4572459 | chr19 | 4670765 | 4670949 | chr19 | 4789697 | 4789805 |
| chr19 | 4790142 | 4790264 | chr19 | 4835778 | 4835926 | chr19 | 4910361 | 4910410 |
| chr19 | 4944145 | 4944174 | chr19 | 5292812 | 5292844 | chr19 | 5338914 | 5339143 |
| chr19 | 5608519 | 5608569 | chr19 | 5676212 | 5676242 | chr19 | 5759374 | 5759544 |
| chr19 | 5759744 | 5759774 | chr19 | 5767703 | 5767733 | chr19 | 5826179 | 5826209 |
| chr19 | 5905517 | 5905547 | chr19 | 5910356 | 5910492 | chr19 | 5914761 | 5914791 |
| chr19 | 5914992 | 5915060 | chr19 | 6303268 | 6303298 | chr19 | 6512913 | 6512943 |
| chr19 | 6590325 | 6590478 | chr19 | 6658279 | 6658422 | chr19 | 6889423 | 6889574 |
| chr19 | 7157547 | 7157628 | chr19 | 7554718 | 7554780 | chr19 | 7615996 | 7616025 |
| chr19 | 7635387 | 7635552 | chr19 | 7746942 | 7747042 | chr19 | 7747205 | 7747234 |
| chr19 | 7795012 | 7795244 | chr19 | 7853028 | 7853157 | chr19 | 7853361 | 7853460 |
| chr19 | 7870346 | 7870387 | chr19 | 8115235 | 8115276 | chr19 | 8391621 | 8391651 |

TABLE 12-continued

| chr | start | end | chr | start | end | chr | start | end |
| --- | --- | --- | --- | --- | --- | --- | --- | --- |
| chr19 | 8554173 | 8554218 | chr19 | 8576914 | 8577000 | chr19 | 8579592 | 8579705 |
| chr19 | 9239580 | 9239695 | chr19 | 9331918 | 9331955 | chr19 | 9420142 | 9420240 |
| chr19 | 9473564 | 9473597 | chr19 | 9473869 | 9474056 | chr19 | 9517609 | 9517771 |
| chr19 | 9608895 | 9609036 | chr19 | 9609319 | 9609436 | chr19 | 9903913 | 9904100 |
| chr19 | 9937291 | 9937386 | chr19 | 10231077 | 10231242 | chr19 | 10246505 | 10246566 |
| chr19 | 10362045 | 10362182 | chr19 | 10398209 | 10398285 | chr19 | 10405972 | 10406159 |
| chr19 | 10406279 | 10406349 | chr19 | 10406806 | 10407029 | chr19 | 10407045 | 10407135 |
| chr19 | 10527165 | 10527243 | chr19 | 10531419 | 10531512 | chr19 | 10531964 | 10531994 |
| chr19 | 10600431 | 10600460 | chr19 | 10602274 | 10602348 | chr19 | 10602565 | 10602864 |
| chr19 | 10610138 | 10610260 | chr19 | 10621768 | 10621829 | chr19 | 10624751 | 10624852 |
| chr19 | 10624966 | 10625465 | chr19 | 10648372 | 10648546 | chr19 | 10729811 | 10729899 |
| chr19 | 10823678 | 10823721 | chr19 | 10827675 | 10827705 | chr19 | 10851287 | 10851362 |
| chr19 | 10955456 | 10955585 | chr19 | 11063941 | 11063971 | chr19 | 11134252 | 11134281 |
| chr19 | 11138507 | 11138536 | chr19 | 11492252 | 11492528 | chr19 | 11591031 | 11591185 |
| chr19 | 11592710 | 11592750 | chr19 | 11593022 | 11593159 | chr19 | 11689460 | 11689564 |
| chr19 | 11959912 | 11960077 | chr19 | 12147437 | 12147545 | chr19 | 12163448 | 12163672 |
| chr19 | 12163893 | 12163923 | chr19 | 12175445 | 12175504 | chr19 | 12175814 | 12176005 |
| chr19 | 12203028 | 12203744 | chr19 | 12205385 | 12205434 | chr19 | 12267019 | 12267662 |
| chr19 | 12303495 | 12303551 | chr19 | 12305839 | 12306193 | chr19 | 12306230 | 12306263 |
| chr19 | 12476492 | 12476556 | chr19 | 12595109 | 12595307 | chr19 | 12595845 | 12595896 |
| chr19 | 12606381 | 12606511 | chr19 | 12661175 | 12661221 | chr19 | 12750987 | 12751056 |
| chr19 | 12846906 | 12847098 | chr19 | 12860307 | 12860433 | chr19 | 12863412 | 12863520 |
| chr19 | 12952000 | 12952139 | chr19 | 12996169 | 12996280 | chr19 | 13113454 | 13113668 |
| chr19 | 13491305 | 13491340 | chr19 | 13616696 | 13616956 | chr19 | 13617159 | 13617256 |
| chr19 | 13618288 | 13618381 | chr19 | 13782965 | 13783028 | chr19 | 13903520 | 13903603 |
| chr19 | 13965838 | 13965965 | chr19 | 13988775 | 13988805 | chr19 | 14085021 | 14085051 |
| chr19 | 14181305 | 14181846 | chr19 | 14324876 | 14324906 | chr19 | 14327101 | 14327158 |
| chr19 | 14334020 | 14334060 | chr19 | 14411056 | 14411086 | chr19 | 14584240 | 14584412 |
| chr19 | 14584537 | 14584775 | chr19 | 14663925 | 14664183 | chr19 | 14664479 | 14664561 |
| chr19 | 14869496 | 14869526 | chr19 | 15090172 | 15090499 | chr19 | 15121685 | 15121894 |
| chr19 | 15122120 | 15122238 | chr19 | 15288433 | 15288856 | chr19 | 15292384 | 15292499 |
| chr19 | 15342734 | 15343373 | chr19 | 15344107 | 15344130 | chr19 | 15519444 | 15519474 |
| chr19 | 16766902 | 16766932 | chr19 | 16999599 | 16999782 | chr19 | 17000570 | 17000599 |
| chr19 | 17007086 | 17007388 | chr19 | 17007447 | 17007662 | chr19 | 17008586 | 17008698 |
| chr19 | 17152333 | 17152363 | chr19 | 17335642 | 17335718 | chr19 | 17336042 | 17336111 |
| chr19 | 17359350 | 17359459 | chr19 | 17392641 | 17392866 | chr19 | 17436061 | 17436203 |
| chr19 | 17446897 | 17447045 | chr19 | 17717286 | 17717315 | chr19 | 17759224 | 17759423 |
| chr19 | 17791182 | 17791211 | chr19 | 17943423 | 17943452 | chr19 | 17945891 | 17945983 |
| chr19 | 17947991 | 17948023 | chr19 | 17949094 | 17949123 | chr19 | 17958490 | 17958839 |
| chr19 | 17983537 | 17983665 | chr19 | 18041069 | 18041203 | chr19 | 18057603 | 18057655 |
| chr19 | 18103711 | 18103741 | chr19 | 18104472 | 18104606 | chr19 | 18126412 | 18126442 |
| chr19 | 18271894 | 18271923 | chr19 | 18278047 | 18278076 | chr19 | 18300127 | 18300422 |
| chr19 | 18301007 | 18301037 | chr19 | 18331031 | 18331136 | chr19 | 18343439 | 18343569 |
| chr19 | 18343921 | 18343963 | chr19 | 18383211 | 18383351 | chr19 | 18488862 | 18488915 |
| chr19 | 18496000 | 18496030 | chr19 | 18523115 | 18523145 | chr19 | 18633926 | 18633980 |
| chr19 | 18681638 | 18681926 | chr19 | 18714552 | 18714580 | chr19 | 18811560 | 18811804 |
| chr19 | 18856379 | 18856409 | chr19 | 18872825 | 18872900 | chr19 | 18899432 | 18899652 |
| chr19 | 18901828 | 18902095 | chr19 | 18989821 | 18990281 | chr19 | 18994887 | 18995206 |
| chr19 | 19260030 | 19260101 | chr19 | 19261519 | 19261548 | chr19 | 19334831 | 19334915 |
| chr19 | 19489251 | 19489297 | chr19 | 19636877 | 19636907 | chr19 | 19645834 | 19645925 |
| chr19 | 19651991 | 19652065 | chr19 | 19729251 | 19729395 | chr19 | 19739172 | 19739428 |
| chr19 | 19776308 | 19775472 | chr19 | 20011955 | 20012149 | chr19 | 20188693 | 20188872 |
| chr19 | 20189322 | 20189438 | chr19 | 21237609 | 21237655 | chr19 | 21239053 | 21239129 |
| chr19 | 21245066 | 21245152 | chr19 | 21265890 | 21265920 | chr19 | 21289719 | 21289749 |
| chr19 | 21290153 | 21290216 | chr19 | 21303863 | 21303993 | chr19 | 21305707 | 21305737 |
| chr19 | 21370382 | 21370479 | chr19 | 21512594 | 21512660 | chr19 | 21646407 | 21646437 |
| chr19 | 21665258 | 21665288 | chr19 | 21688814 | 21688912 | chr19 | 21769300 | 21769374 |
| chr19 | 22018523 | 22018805 | chr19 | 22034198 | 22034421 | chr19 | 22034447 | 22034813 |
| chr19 | 22610635 | 22610700 | chr19 | 22715140 | 22715443 | chr19 | 23254189 | 23254219 |
| chr19 | 23257703 | 23258007 | chr19 | 23258306 | 23258694 | chr19 | 23299748 | 23300080 |
| chr19 | 23432562 | 23432723 | chr19 | 23433143 | 23433296 | chr19 | 23456615 | 23456881 |
| chr19 | 23598274 | 23598326 | chr19 | 24154592 | 24154621 | chr19 | 24216975 | 24217023 |
| chr19 | 29284452 | 29284575 | chr19 | 29505153 | 29505183 | chr19 | 30015934 | 30015962 |
| chr19 | 30016025 | 30016712 | chr19 | 30016914 | 30016928 | chr19 | 30017452 | 30017509 |
| chr19 | 30017578 | 30017721 | chr19 | 30017766 | 30018608 | chr19 | 30019145 | 30019610 |
| chr19 | 30019661 | 30019838 | chr19 | 30020093 | 30020473 | chr19 | 30130889 | 30130919 |
| chr19 | 30186141 | 30186278 | chr19 | 30215542 | 30215571 | chr19 | 30215753 | 30215782 |
| chr19 | 30252296 | 30252369 | chr19 | 30555329 | 30555376 | chr19 | 30562775 | 30563017 |
| chr19 | 30582601 | 30582649 | chr19 | 30637494 | 30637531 | chr19 | 30703436 | 30703469 |
| chr19 | 30713480 | 30713592 | chr19 | 30713686 | 30713706 | chr19 | 30713909 | 30714047 |
| chr19 | 30714403 | 30714433 | chr19 | 30715402 | 30715766 | chr19 | 30716313 | 30716576 |
| chr19 | 30716953 | 30718149 | chr19 | 30718847 | 30718913 | chr19 | 30719449 | 30720067 |
| chr19 | 30865713 | 30866024 | chr19 | 31804724 | 31804754 | chr19 | 31839838 | 31839873 |
| chr19 | 31841937 | 31842389 | chr19 | 32364365 | 32364403 | chr19 | 32380872 | 32380961 |
| chr19 | 32516399 | 32516516 | chr19 | 32715673 | 32715741 | chr19 | 32835279 | 32835309 |
| chr19 | 32898335 | 32898490 | chr19 | 33167116 | 33167431 | chr19 | 33468018 | 33468055 |
| chr19 | 33571236 | 33571280 | chr19 | 33685544 | 33685581 | chr19 | 33792159 | 33792524 |
| chr19 | 33794675 | 33794744 | chr19 | 34112524 | 34112729 | chr19 | 34113367 | 34113587 |

TABLE 12-continued

| chr | start | end | chr | start | end | chr | start | end |
|---|---|---|---|---|---|---|---|---|
| chr19 | 34114006 | 34114049 | chr19 | 34533139 | 34533169 | chr19 | 34896324 | 34896360 |
| chr19 | 34973243 | 34973255 | chr19 | 34973656 | 34973697 | chr19 | 34973932 | 34973965 |
| chr19 | 35264085 | 35264119 | chr19 | 35396251 | 35396370 | chr19 | 35616341 | 35616397 |
| chr19 | 35781374 | 35781459 | chr19 | 35783136 | 35783231 | chr19 | 35797916 | 35797965 |
| chr19 | 36048595 | 36048771 | chr19 | 36049327 | 36049367 | chr19 | 36049397 | 36049462 |
| chr19 | 36194934 | 36194996 | chr19 | 36200805 | 36200847 | chr19 | 36222432 | 36222534 |
| chr19 | 36250029 | 36250134 | chr19 | 36264697 | 36264773 | chr19 | 36265053 | 36265186 |
| chr19 | 36334979 | 36335147 | chr19 | 36347892 | 36348048 | chr19 | 36410956 | 36411042 |
| chr19 | 36413776 | 36413830 | chr19 | 36450106 | 36450295 | chr19 | 36523333 | 36523480 |
| chr19 | 36531924 | 36531954 | chr19 | 36707435 | 36707467 | chr19 | 36736027 | 36736057 |
| chr19 | 36736319 | 36736491 | chr19 | 36822324 | 36822466 | chr19 | 36822558 | 36822892 |
| chr19 | 36909050 | 36909348 | chr19 | 36909624 | 36909935 | chr19 | 37095665 | 37095812 |
| chr19 | 37096488 | 37096575 | chr19 | 37263532 | 37263584 | chr19 | 37264222 | 37264421 |
| chr19 | 37288013 | 37288424 | chr19 | 37288607 | 37288765 | chr19 | 37341761 | 37341962 |
| chr19 | 37407127 | 37407443 | chr19 | 37464048 | 37464267 | chr19 | 37464667 | 37464696 |
| chr19 | 37569289 | 37569554 | chr19 | 37702003 | 37702169 | chr19 | 37808445 | 37808485 |
| chr19 | 37959874 | 37959963 | chr19 | 37997433 | 37998138 | chr19 | 38042365 | 38042693 |
| chr19 | 38085254 | 38086066 | chr19 | 38146062 | 38146247 | chr19 | 38146457 | 38146568 |
| chr19 | 38182884 | 38182959 | chr19 | 38183112 | 38183299 | chr19 | 38308080 | 38308336 |
| chr19 | 38308395 | 38308466 | chr19 | 38441488 | 38441518 | chr19 | 38481044 | 38481217 |
| chr19 | 38733924 | 38733954 | chr19 | 38736072 | 38736127 | chr19 | 38747159 | 38747582 |
| chr19 | 38747729 | 38747767 | chr19 | 38755272 | 38755344 | chr19 | 38757128 | 38757308 |
| chr19 | 38782559 | 38782589 | chr19 | 38789218 | 38789288 | chr19 | 38873935 | 38873965 |
| chr19 | 38905548 | 38905702 | chr19 | 38974232 | 38974262 | chr19 | 39135294 | 39135454 |
| chr19 | 39273027 | 39273062 | chr19 | 39290904 | 39290944 | chr19 | 39306433 | 39306545 |
| chr19 | 39310469 | 39310584 | chr19 | 39650791 | 39650967 | chr19 | 39687756 | 39687844 |
| chr19 | 39754874 | 39755232 | chr19 | 39755265 | 39755358 | chr19 | 39816936 | 39817085 |
| chr19 | 39934694 | 39934784 | chr19 | 39993477 | 39993656 | chr19 | 39997688 | 39997732 |
| chr19 | 39997749 | 39997813 | chr19 | 40006187 | 40006306 | chr19 | 40006576 | 40006639 |
| chr19 | 40210391 | 40210573 | chr19 | 40724000 | 40724263 | chr19 | 40762943 | 40762972 |
| chr19 | 40829079 | 40829211 | chr19 | 40830032 | 40830059 | chr19 | 40902425 | 40902812 |
| chr19 | 40951175 | 40951357 | chr19 | 40951679 | 40951762 | chr19 | 40991013 | 40991139 |
| chr19 | 41018510 | 41019031 | chr19 | 41025539 | 41025683 | chr19 | 41059909 | 41060306 |
| chr19 | 41073587 | 41073677 | chr19 | 41119177 | 41119276 | chr19 | 41119371 | 41119408 |
| chr19 | 41354666 | 41354722 | chr19 | 41473190 | 41473242 | chr19 | 41641831 | 41641886 |
| chr19 | 41694610 | 41694640 | chr19 | 41698787 | 41698920 | chr19 | 41846193 | 41846325 |
| chr19 | 41881534 | 41881811 | chr19 | 41919917 | 41919971 | chr19 | 42028502 | 42028549 |
| chr19 | 42408300 | 42408330 | chr19 | 42460961 | 42461113 | chr19 | 42827982 | 42828084 |
| chr19 | 42856453 | 42856483 | chr19 | 42911568 | 42911598 | chr19 | 44203830 | 44203877 |
| chr19 | 44405908 | 44406087 | chr19 | 44599783 | 44599883 | chr19 | 44905499 | 44905529 |
| chr19 | 44952282 | 44952881 | chr19 | 45003211 | 45003323 | chr19 | 45300144 | 45300197 |
| chr19 | 45541556 | 45541679 | chr19 | 45570401 | 45570450 | chr19 | 45574465 | 45574495 |
| chr19 | 45574773 | 45574888 | chr19 | 45601380 | 45601410 | chr19 | 45655400 | 45655556 |
| chr19 | 45655648 | 45656363 | chr19 | 45656682 | 45656742 | chr19 | 45656791 | 45656913 |
| chr19 | 45657212 | 45657284 | chr19 | 45678395 | 45678555 | chr19 | 45810102 | 45810267 |
| chr19 | 45835028 | 45835268 | chr19 | 45888946 | 45889224 | chr19 | 45889316 | 45889397 |
| chr19 | 45997528 | 45997584 | chr19 | 46002048 | 46002320 | chr19 | 46234803 | 46234887 |
| chr19 | 46379914 | 46380148 | chr19 | 46404522 | 46404601 | chr19 | 46916725 | 46916987 |
| chr19 | 46917061 | 46917075 | chr19 | 46930129 | 46930200 | chr19 | 46974552 | 46974608 |
| chr19 | 46992718 | 46992866 | chr19 | 46993164 | 46993260 | chr19 | 46993282 | 46993388 |
| chr19 | 46996501 | 46996514 | chr19 | 46996578 | 46996838 | chr19 | 47152978 | 47152990 |
| chr19 | 47200361 | 47200536 | chr19 | 47329748 | 47329867 | chr19 | 47358646 | 47358751 |
| chr19 | 47515017 | 47515047 | chr19 | 47618255 | 47618434 | chr19 | 47776713 | 47776742 |
| chr19 | 47933311 | 47933732 | chr19 | 47951288 | 47951318 | chr19 | 47976399 | 47976429 |
| chr19 | 48003607 | 48003714 | chr19 | 48076642 | 48076672 | chr19 | 48082100 | 48082130 |
| chr19 | 48108151 | 48108320 | chr19 | 48137171 | 48137307 | chr19 | 48151265 | 48151337 |
| chr19 | 48249451 | 48249602 | chr19 | 48614843 | 48614873 | chr19 | 48771551 | 48771600 |
| chr19 | 48777059 | 48777121 | chr19 | 48800603 | 48800769 | chr19 | 48857725 | 48857831 |
| chr19 | 48902848 | 48902878 | chr19 | 48918100 | 48918598 | chr19 | 49043242 | 49043272 |
| chr19 | 49119229 | 49119259 | chr19 | 49127373 | 49127674 | chr19 | 49180462 | 49180558 |
| chr19 | 49256396 | 49256438 | chr19 | 49285456 | 49285593 | chr19 | 49290711 | 49290844 |
| chr19 | 49375050 | 49375216 | chr19 | 49399218 | 49399310 | chr19 | 49402471 | 49402551 |
| chr19 | 49498076 | 49498148 | chr19 | 49575460 | 49575474 | chr19 | 49590284 | 49590399 |
| chr19 | 49628132 | 49628252 | chr19 | 49784869 | 49784935 | chr19 | 49890887 | 49890929 |
| chr19 | 49935736 | 49936174 | chr19 | 49936864 | 49936894 | chr19 | 49997263 | 49997324 |
| chr19 | 49998434 | 49998607 | chr19 | 50028397 | 50028530 | chr19 | 50049718 | 50049953 |
| chr19 | 50203173 | 50203203 | chr19 | 50216042 | 50216072 | chr19 | 50243339 | 50243379 |
| chr19 | 50304736 | 50304766 | chr19 | 50316244 | 50316468 | chr19 | 50319874 | 50319916 |
| chr19 | 50320233 | 50320277 | chr19 | 50353394 | 50353574 | chr19 | 50553680 | 50553709 |
| chr19 | 50553997 | 50554510 | chr19 | 50589044 | 50589079 | chr19 | 50816431 | 50816474 |
| chr19 | 50833828 | 50833863 | chr19 | 50874895 | 50874933 | chr19 | 50898558 | 50898727 |
| chr19 | 50938547 | 50938691 | chr19 | 51041149 | 51041189 | chr19 | 51161225 | 51161255 |
| chr19 | 51162197 | 51162253 | chr19 | 51162428 | 51162527 | chr19 | 51171219 | 51171275 |
| chr19 | 51171828 | 51171860 | chr19 | 51227719 | 51227785 | chr19 | 51228049 | 51228079 |
| chr19 | 51228369 | 51228507 | chr19 | 51304554 | 51304602 | chr19 | 51520423 | 51520453 |
| chr19 | 51715329 | 51715359 | chr19 | 51830845 | 51831002 | chr19 | 51831121 | 51831128 |
| chr19 | 51831360 | 51831390 | chr19 | 51925127 | 51925272 | chr19 | 52097689 | 52097732 |
| chr19 | 52139210 | 52139326 | chr19 | 52207254 | 52207367 | chr19 | 52222523 | 52222923 |

TABLE 12-continued

| chr | start | end | chr | start | end | chr | start | end |
|---|---|---|---|---|---|---|---|---|
| chr19 | 52391235 | 52391264 | chr19 | 52452316 | 52452335 | chr19 | 52552104 | 52552119 |
| chr19 | 52715963 | 52715992 | chr19 | 52839588 | 52839717 | chr19 | 52839742 | 52839938 |
| chr19 | 52872924 | 52873440 | chr19 | 52956805 | 52956848 | chr19 | 53028928 | 53029035 |
| chr19 | 53031185 | 53031215 | chr19 | 53073314 | 53073354 | chr19 | 53073563 | 53073772 |
| chr19 | 53073820 | 53073987 | chr19 | 53141648 | 53141745 | chr19 | 53193858 | 53193893 |
| chr19 | 53194281 | 53194396 | chr19 | 53204758 | 53204837 | chr19 | 53291021 | 53291081 |
| chr19 | 53398908 | 53399031 | chr19 | 53399814 | 53399848 | chr19 | 53436895 | 53437067 |
| chr19 | 53446951 | 53447130 | chr19 | 53496649 | 53496786 | chr19 | 53496814 | 53496846 |
| chr19 | 53561668 | 53561733 | chr19 | 53635952 | 53636091 | chr19 | 53661647 | 53661902 |
| chr19 | 53662174 | 53662694 | chr19 | 53688015 | 53688059 | chr19 | 53696414 | 53696580 |
| chr19 | 53700596 | 53700729 | chr19 | 53757895 | 53758247 | chr19 | 53811858 | 53811988 |
| chr19 | 53836954 | 53836975 | chr19 | 53837377 | 53837432 | chr19 | 53860082 | 53860151 |
| chr19 | 53873182 | 53873212 | chr19 | 53970501 | 53970725 | chr19 | 53970968 | 53971039 |
| chr19 | 53971110 | 53971157 | chr19 | 54023887 | 54024196 | chr19 | 54024521 | 54024884 |
| chr19 | 54271479 | 54271509 | chr19 | 54369555 | 54369681 | chr19 | 54411125 | 54411168 |
| chr19 | 54411556 | 54411586 | chr19 | 54412873 | 54412985 | chr19 | 54481771 | 54481968 |
| chr19 | 54483173 | 54483305 | chr19 | 54483365 | 54483546 | chr19 | 54485403 | 54485646 |
| chr19 | 54485673 | 54485823 | chr19 | 54850630 | 54850659 | chr19 | 55598811 | 55598888 |
| chr19 | 55629883 | 55630028 | chr19 | 55728901 | 55729104 | chr19 | 55849550 | 55849638 |
| chr19 | 56159273 | 56159499 | chr19 | 56189937 | 56189966 | chr19 | 56201643 | 56201938 |
| chr19 | 56340995 | 56341033 | chr19 | 56588656 | 56588780 | chr19 | 56728678 | 56728788 |
| chr19 | 56858084 | 56858227 | chr19 | 56879501 | 56880008 | chr19 | 56904740 | 56905203 |
| chr19 | 56915320 | 56915428 | chr19 | 56988557 | 56988663 | chr19 | 56989528 | 56989625 |
| chr19 | 56989697 | 56989754 | chr19 | 57050463 | 57050493 | chr19 | 57149579 | 57149619 |
| chr19 | 57154885 | 57155017 | chr19 | 57182994 | 57183126 | chr19 | 57276656 | 57276700 |
| chr19 | 57323825 | 57323854 | chr19 | 57610896 | 57610985 | chr19 | 57617522 | 57617715 |
| chr19 | 57617832 | 57618121 | chr19 | 57683148 | 57683162 | chr19 | 57683240 | 57683295 |
| chr19 | 57862395 | 57862783 | chr19 | 58011124 | 58011281 | chr19 | 58038924 | 58038969 |
| chr19 | 58095006 | 58095835 | chr19 | 58111632 | 58111783 | chr19 | 58125544 | 58125881 |
| chr19 | 58144494 | 58144701 | chr19 | 58219839 | 58220392 | chr19 | 58220516 | 58220832 |
| chr19 | 58238326 | 58238738 | chr19 | 58238988 | 58239088 | chr19 | 58316915 | 58317096 |
| chr19 | 58325075 | 58325282 | chr19 | 58400079 | 58400175 | chr19 | 58400417 | 58400518 |
| chr19 | 58458754 | 58458890 | chr19 | 58458979 | 58459201 | chr19 | 58514518 | 58514552 |
| chr19 | 58520739 | 58520941 | chr19 | 58545145 | 58545387 | chr19 | 58545578 | 58545589 |
| chr19 | 58545652 | 58545837 | chr19 | 58609254 | 58609359 | chr19 | 58609473 | 58609525 |
| chr19 | 58509713 | 58609854 | chr19 | 58629975 | 58529975 | chr19 | 58661894 | 58662094 |
| chr19 | 58666171 | 58666313 | chr19 | 58740086 | 58740118 | chr19 | 58807869 | 58807931 |
| chr19 | 58874735 | 58874987 | chr19 | 58951271 | 58951400 | chr19 | 58951526 | 58951916 |
| chr19 | 58964180 | 58964266 | chr19 | 59054642 | 59054774 | chr20 | 118577 | 118751 |
| chr20 | 291148 | 291162 | chr20 | 291221 | 291373 | chr20 | 304259 | 304408 |
| chr20 | 400007 | 400087 | chr20 | 401153 | 401183 | chr20 | 401591 | 401756 |
| chr20 | 523146 | 523193 | chr20 | 590434 | 590502 | chr20 | 592405 | 592449 |
| chr20 | 644182 | 644351 | chr20 | 644407 | 644787 | chr20 | 799104 | 799247 |
| chr20 | 799458 | 799706 | chr20 | 982749 | 982798 | chr20 | 982892 | 982989 |
| chr20 | 1094560 | 1094682 | chr20 | 1197670 | 1197711 | chr20 | 1206855 | 1207034 |
| chr20 | 1783761 | 1784305 | chr20 | 1876110 | 1876176 | chr20 | 1975357 | 1975386 |
| chr20 | 2539331 | 2539771 | chr20 | 2645540 | 2645795 | chr20 | 2668770 | 2668922 |
| chr20 | 2780753 | 2781452 | chr20 | 2781731 | 2781761 | chr20 | 2785659 | 2785866 |
| chr20 | 2785956 | 2786060 | chr20 | 3027758 | 3027931 | chr20 | 3052583 | 3052836 |
| chr20 | 3073561 | 3073899 | chr20 | 3154172 | 3154204 | chr20 | 3204870 | 3204952 |
| chr20 | 3220893 | 3220943 | chr20 | 3229576 | 3229612 | chr20 | 3641774 | 3641937 |
| chr20 | 3663020 | 3663174 | chr20 | 3762152 | 3762181 | chr20 | 3762407 | 3762433 |
| chr20 | 3858389 | 3858632 | chr20 | 3996688 | 3996726 | chr20 | 4040710 | 4040871 |
| chr20 | 4051323 | 4061452 | chr20 | 4085057 | 4085087 | chr20 | 4229402 | 4229432 |
| chr20 | 4229786 | 4230600 | chr20 | 4803070 | 4803650 | chr20 | 4803921 | 4804008 |
| chr20 | 4804566 | 4804732 | chr20 | 5025228 | 5025258 | chr20 | 5106720 | 5106750 |
| chr20 | 5296172 | 5296900 | chr20 | 5297226 | 5297418 | chr20 | 5433047 | 5433085 |
| chr20 | 5610356 | 5610386 | chr20 | 6022797 | 6023045 | chr20 | 6023268 | 6023351 |
| chr20 | 6748925 | 6749036 | chr20 | 7980362 | 7980392 | chr20 | 8112378 | 8112408 |
| chr20 | 8112739 | 8113022 | chr20 | 8113557 | 8113605 | chr20 | 9487385 | 9487719 |
| chr20 | 9487789 | 9487997 | chr20 | 9488349 | 9488848 | chr20 | 9489070 | 9489214 |
| chr20 | 9489424 | 9489708 | chr20 | 9495271 | 9495509 | chr20 | 9496330 | 9496530 |
| chr20 | 9496581 | 9496833 | chr20 | 9497035 | 9497109 | chr20 | 10198289 | 10198600 |
| chr20 | 10198941 | 10198945 | chr20 | 13200599 | 13200634 | chr20 | 14447971 | 14448144 |
| chr20 | 16564749 | 16555030 | chr20 | 17206513 | 17206747 | chr20 | 17207874 | 17207930 |
| chr20 | 17208585 | 17208620 | chr20 | 18039823 | 18039897 | chr20 | 18073183 | 18073276 |
| chr20 | 18073312 | 18073461 | chr20 | 18448982 | 18449076 | chr20 | 18489463 | 18489658 |
| chr20 | 19128288 | 19128473 | chr20 | 19739613 | 19739696 | chr20 | 19928306 | 19928461 |
| chr20 | 20344498 | 20344559 | chr20 | 20347460 | 20347709 | chr20 | 20347737 | 20348154 |
| chr20 | 20348526 | 20348605 | chr20 | 20349153 | 20349255 | chr20 | 20349574 | 20349604 |
| chr20 | 21080714 | 21080956 | chr20 | 21081029 | 21081844 | chr20 | 21082095 | 21082123 |
| chr20 | 21082216 | 21082253 | chr20 | 21082532 | 21082917 | chr20 | 21083421 | 21084361 |
| chr20 | 21085831 | 21085864 | chr20 | 21086195 | 21086451 | chr20 | 21086866 | 21087188 |
| chr20 | 21372174 | 21372192 | chr20 | 21372295 | 21372725 | chr20 | 21376250 | 21376336 |
| chr20 | 21376703 | 21376733 | chr20 | 21376877 | 21377128 | chr20 | 21377474 | 21377640 |
| chr20 | 21327738 | 21378551 | chr20 | 21486375 | 21486659 | chr20 | 21486786 | 21486881 |
| chr20 | 21487153 | 21487581 | chr20 | 21488158 | 21488351 | chr20 | 21489240 | 21489446 |
| chr20 | 21489622 | 21489703 | chr20 | 21490175 | 21490762 | chr20 | 21490815 | 21491345 |

TABLE 12-continued

| chr | start | end | chr | start | end | chr | start | end |
|---|---|---|---|---|---|---|---|---|
| chr20 | 21492378 | 21492409 | chr20 | 21492508 | 21492825 | chr20 | 21493308 | 21493993 |
| chr20 | 21494531 | 21494703 | chr20 | 21495942 | 21495986 | chr20 | 21496260 | 21496294 |
| chr20 | 21496684 | 21497136 | chr20 | 21497413 | 21498638 | chr20 | 21499961 | 21500134 |
| chr20 | 21501445 | 21501724 | chr20 | 21502037 | 21502144 | chr20 | 21502590 | 21502699 |
| chr20 | 21502838 | 21503117 | chr20 | 21503455 | 21503773 | chr20 | 21682399 | 21682456 |
| chr20 | 21683311 | 21683651 | chr20 | 21685385 | 21685526 | chr20 | 21686235 | 21686677 |
| chr20 | 21687009 | 21687382 | chr20 | 21689956 | 21690185 | chr20 | 21694499 | 21694529 |
| chr20 | 21695088 | 21695273 | chr20 | 21695306 | 21695357 | chr20 | 21748445 | 21748491 |
| chr20 | 22401392 | 22401421 | chr20 | 22557396 | 22557675 | chr20 | 22557979 | 22558114 |
| chr20 | 22558637 | 22558669 | chr20 | 22559645 | 22559690 | chr20 | 22562721 | 22562840 |
| chr20 | 22563563 | 22563602 | chr20 | 22564235 | 22564265 | chr20 | 22566961 | 22566990 |
| chr20 | 23015917 | 23015946 | chr20 | 23029110 | 23029151 | chr20 | 23029589 | 23030085 |
| chr20 | 23030292 | 23030357 | chr20 | 23031548 | 23031692 | chr20 | 23138383 | 23138444 |
| chr20 | 23406698 | 23406830 | chr20 | 24450231 | 24450513 | chr20 | 24450820 | 24451019 |
| chr20 | 24451450 | 24451592 | chr20 | 24505190 | 24505252 | chr20 | 24726701 | 24726825 |
| chr20 | 25058385 | 25058616 | chr20 | 25061746 | 25061788 | chr20 | 25061979 | 25062311 |
| chr20 | 25062511 | 25062645 | chr20 | 25062708 | 25062817 | chr20 | 25062871 | 25062880 |
| chr20 | 25063780 | 25063906 | chr20 | 25063994 | 25064458 | chr20 | 25065179 | 25065395 |
| chr20 | 25086082 | 25086275 | chr20 | 25223141 | 25223277 | chr20 | 25230509 | 25230799 |
| chr20 | 25334513 | 25334650 | chr20 | 25344027 | 25344118 | chr20 | 26188812 | 26188961 |
| chr20 | 26190313 | 26190361 | chr20 | 29832911 | 29833090 | chr20 | 29914002 | 29914139 |
| chr20 | 29956013 | 29956042 | chr20 | 29956570 | 29956599 | chr20 | 30101523 | 30101743 |
| chr20 | 30162296 | 30162459 | chr20 | 30174561 | 30174645 | chr20 | 30186068 | 30186165 |
| chr20 | 30201236 | 30201360 | chr20 | 30280423 | 30280509 | chr20 | 30297090 | 30297217 |
| chr20 | 30468319 | 30468349 | chr20 | 30582750 | 30582978 | chr20 | 30639141 | 30639319 |
| chr20 | 30639632 | 30639847 | chr20 | 30640106 | 30640270 | chr20 | 30778024 | 30778313 |
| chr20 | 31035471 | 31035518 | chr20 | 31115683 | 31115799 | chr20 | 31151769 | 31151799 |
| chr20 | 31207211 | 31207283 | chr20 | 31282734 | 31282903 | chr20 | 32301797 | 32301953 |
| chr20 | 32450248 | 32450427 | chr20 | 32701064 | 32701320 | chr20 | 32716914 | 32716949 |
| chr20 | 32768669 | 32768728 | chr20 | 32893006 | 32893125 | chr20 | 33540284 | 33540550 |
| chr20 | 33547485 | 33547585 | chr20 | 33574914 | 33574992 | chr20 | 34041981 | 34042087 |
| chr20 | 34148020 | 34148254 | chr20 | 34188617 | 34188631 | chr20 | 34188748 | 34189088 |
| chr20 | 34189167 | 34189391 | chr20 | 34189680 | 34189910 | chr20 | 35640448 | 35640561 |
| chr20 | 35742487 | 35742607 | chr20 | 35892604 | 35892746 | chr20 | 36183184 | 36183340 |
| chr20 | 36531799 | 36531910 | chr20 | 36781324 | 36781354 | chr20 | 37302697 | 37303343 |
| chr20 | 37351793 | 37352515 | chr20 | 37352607 | 37352626 | chr20 | 37353193 | 37353236 |
| chr20 | 37353455 | 37353718 | chr20 | 37354145 | 37354831 | chr20 | 37354994 | 37355202 |
| chr20 | 37355847 | 37356042 | chr20 | 37356169 | 37356827 | chr20 | 37357216 | 37357353 |
| chr20 | 37357825 | 37358190 | chr20 | 37434552 | 37434721 | chr20 | 37434737 | 37434744 |
| chr20 | 37435104 | 37435218 | chr20 | 37435488 | 37435860 | chr20 | 39316203 | 39316322 |
| chr20 | 39316984 | 39317392 | chr20 | 39317750 | 39318166 | chr20 | 39318383 | 39318415 |
| chr20 | 39319126 | 39319203 | chr20 | 39319515 | 39319653 | chr20 | 39995146 | 39995813 |
| chr20 | 40500546 | 40500638 | chr20 | 40515378 | 40515504 | chr20 | 40743859 | 40743888 |
| chr20 | 41817786 | 41817915 | chr20 | 41818008 | 41818085 | chr20 | 41818567 | 41818748 |
| chr20 | 41818805 | 41818914 | chr20 | 42136330 | 42136411 | chr20 | 42218429 | 42218664 |
| chr20 | 42281425 | 42281455 | chr20 | 42543754 | 42543853 | chr20 | 42544091 | 42544533 |
| chr20 | 42544728 | 42544984 | chr20 | 42852751 | 42852915 | chr20 | 42876525 | 42876575 |
| chr20 | 43438071 | 43438085 | chr20 | 43438335 | 43438466 | chr20 | 43438982 | 43439022 |
| chr20 | 43439291 | 43439510 | chr20 | 43952174 | 43952302 | chr20 | 44003765 | 44003811 |
| chr20 | 44452731 | 44453063 | chr20 | 44519077 | 44519107 | chr20 | 44601547 | 44601716 |
| chr20 | 44602074 | 44602364 | chr20 | 44639181 | 44639496 | chr20 | 44640338 | 44640367 |
| chr20 | 44660750 | 44660877 | chr20 | 44686423 | 44686614 | chr20 | 44686628 | 44686762 |
| chr20 | 44746484 | 44746781 | chr20 | 44803174 | 44803675 | chr20 | 44875240 | 44875411 |
| chr20 | 44880041 | 44880076 | chr20 | 44937202 | 44937411 | chr20 | 44937426 | 44937643 |
| chr20 | 44941518 | 44941661 | chr20 | 45142000 | 45142038 | chr20 | 45142152 | 45142272 |
| chr20 | 45279854 | 45279981 | chr20 | 45280040 | 45280302 | chr20 | 45280344 | 45280428 |
| chr20 | 45337804 | 45337945 | chr20 | 45524523 | 45524553 | chr20 | 47247239 | 47247450 |
| chr20 | 47274032 | 47274062 | chr20 | 47296109 | 47296231 | chr20 | 47443729 | 47443936 |
| chr20 | 47443945 | 47444282 | chr20 | 47450370 | 47450490 | chr20 | 47815615 | 47815711 |
| chr20 | 47835328 | 47835358 | chr20 | 47905426 | 47905603 | chr20 | 47934824 | 47935268 |
| chr20 | 47935475 | 47935567 | chr20 | 47935928 | 47936027 | chr20 | 48184381 | 48184435 |
| chr20 | 48695665 | 48696227 | chr20 | 48768118 | 48768148 | chr20 | 48774527 | 48774569 |
| chr20 | 49204179 | 49204449 | chr20 | 49261803 | 49262104 | chr20 | 49323924 | 49324125 |
| chr20 | 49350910 | 49351041 | chr20 | 49351564 | 49351649 | chr20 | 49358137 | 49358396 |
| chr20 | 49377755 | 49378043 | chr20 | 49381140 | 49381240 | chr20 | 49575909 | 49575939 |
| chr20 | 49639777 | 49639856 | chr20 | 49639883 | 49639996 | chr20 | 49640095 | 49640157 |
| chr20 | 49969348 | 49969515 | chr20 | 50160756 | 50160905 | chr20 | 50383224 | 50383423 |
| chr20 | 50384767 | 50384896 | chr20 | 50602134 | 50602264 | chr20 | 50693423 | 50693468 |
| chr20 | 50720437 | 50721200 | chr20 | 50721235 | 50721670 | chr20 | 50721989 | 50722193 |
| chr20 | 50722598 | 50722821 | chr20 | 51589766 | 51589908 | chr20 | 52226337 | 52226366 |
| chr20 | 52311463 | 52311728 | chr20 | 52401713 | 52401775 | chr20 | 52789445 | 52789475 |
| chr20 | 52789853 | 52789948 | chr20 | 52790082 | 52790155 | chr20 | 53092192 | 53092376 |
| chr20 | 53093085 | 53093115 | chr20 | 54522432 | 54522631 | chr20 | 54578507 | 54578725 |
| chr20 | 54579892 | 54579958 | chr20 | 54580070 | 54580323 | chr20 | 54580622 | 54580691 |
| chr20 | 55008041 | 55008194 | chr20 | 55071563 | 55071712 | chr20 | 55200035 | 55200310 |
| chr20 | 55200616 | 55200706 | chr20 | 55200922 | 55201092 | chr20 | 55201764 | 55202068 |
| chr20 | 55202359 | 55202625 | chr20 | 55202826 | 55203107 | chr20 | 55204322 | 55204604 |
| chr20 | 55204966 | 55205000 | chr20 | 56206294 | 55206393 | chr20 | 55206739 | 55206774 |

TABLE 12-continued

| chr | start | end | chr | start | end | chr | start | end |
|---|---|---|---|---|---|---|---|---|
| chr20 | 55499496 | 55499709 | chr20 | 55500016 | 55500085 | chr20 | 55600441 | 55500720 |
| chr20 | 55693527 | 55693662 | chr20 | 55841134 | 55841356 | chr20 | 55842096 | 55842189 |
| chr20 | 55959212 | 55959250 | chr20 | 56766160 | 56766190 | chr20 | 56803398 | 56803441 |
| chr20 | 56803842 | 56803920 | chr20 | 56998280 | 56998337 | chr20 | 57089452 | 57089459 |
| chr20 | 57090104 | 57090173 | chr20 | 57224842 | 57225079 | chr20 | 57225219 | 57225307 |
| chr20 | 57484406 | 57484445 | chr20 | 58179809 | 58179854 | chr20 | 58180214 | 58180402 |
| chr20 | 58508887 | 58508943 | chr20 | 59525138 | 59525300 | chr20 | 59804170 | 59804235 |
| chr20 | 59826192 | 59826221 | chr20 | 59826962 | 59826977 | chr20 | 59828341 | 59828407 |
| chr20 | 59880433 | 59880477 | chr20 | 59910175 | 59910346 | chr20 | 59973028 | 59973072 |
| chr20 | 60202594 | 60202624 | chr20 | 50235333 | 60235526 | chr20 | 50238381 | 60238472 |
| chr20 | 60238877 | 60238980 | chr20 | 60243944 | 60244107 | chr20 | 60329584 | 60329738 |
| chr20 | 60333880 | 60333969 | chr20 | 60359849 | 60359879 | chr20 | 60375036 | 60375070 |
| chr20 | 60439634 | 60439755 | chr20 | 60453925 | 60454091 | chr20 | 60477306 | 60477537 |
| chr20 | 60485374 | 60485425 | chr20 | 60503030 | 60503060 | chr20 | 60545561 | 60545792 |
| chr20 | 60620122 | 60620557 | chr20 | 60772853 | 60773878 | chr20 | 60789965 | 60790124 |
| chr20 | 60816241 | 60816221 | chr20 | 60892164 | 60892222 | chr20 | 60926019 | 60926049 |
| chr20 | 60970953 | 60970983 | chr20 | 60983859 | 60984010 | chr20 | 60984341 | 60984465 |
| chr20 | 61288068 | 61288155 | chr20 | 61288453 | 61288534 | chr20 | 61294693 | 61294857 |
| chr20 | 61340581 | 61340689 | chr20 | 61412313 | 61412438 | chr20 | 61605851 | 61506330 |
| chr20 | 61532546 | 61532605 | chr20 | 61560418 | 61560460 | chr20 | 61560529 | 61560922 |
| chr20 | 61585771 | 61585922 | chr20 | 61585990 | 61586004 | chr20 | 61636876 | 61636890 |
| chr20 | 61637468 | 61637648 | chr20 | 61637736 | 61637956 | chr20 | 61638221 | 61638469 |
| chr20 | 61638535 | 61638631 | chr20 | 61703710 | 61703761 | chr20 | 61703846 | 61703875 |
| chr20 | 61714591 | 61714621 | chr20 | 61734420 | 61734481 | chr20 | 61747894 | 61747934 |
| chr20 | 61763598 | 61763628 | chr20 | 61765285 | 61765425 | chr20 | 61808181 | 61808270 |
| chr20 | 61808667 | 61809005 | chr20 | 61809219 | 61809631 | chr20 | 61809841 | 61810089 |
| chr20 | 61823170 | 61823339 | chr20 | 61862380 | 61862452 | chr20 | 61885247 | 61885462 |
| chr20 | 61886068 | 61886203 | chr20 | 61886257 | 61886258 | chr20 | 61886725 | 61886755 |
| chr20 | 61974191 | 61974354 | chr20 | 51980860 | 61980975 | chr20 | 62031173 | 62031234 |
| chr20 | 62032058 | 62032095 | chr20 | 62037559 | 62037598 | chr20 | 62046227 | 62046421 |
| chr20 | 62058700 | 62058786 | chr20 | 62090524 | 62090776 | chr20 | 62097666 | 62097695 |
| chr20 | 62115047 | 62115266 | chr20 | 62119339 | 62119618 | chr20 | 62119923 | 62120171 |
| chr20 | 62126118 | 62126429 | chr20 | 62157151 | 62157307 | chr20 | 62165631 | 62165762 |
| chr20 | 62167554 | 62167584 | chr20 | 62170179 | 62170209 | chr20 | 62172945 | 62173055 |
| chr20 | 62185386 | 62185444 | chr20 | 62260818 | 62260905 | chr20 | 62261532 | 62261562 |
| chr20 | 62284487 | 62284615 | chr20 | 62314848 | 62314955 | chr20 | 62321206 | 62321341 |
| chr20 | 62321638 | 62321881 | chr20 | 62340321 | 62340442 | chr20 | 62383218 | 62383289 |
| chr20 | 62391938 | 62391968 | chr20 | 62461349 | 62461475 | chr20 | 62488293 | 62488350 |
| chr20 | 62497836 | 62497920 | chr20 | 62631351 | 62631593 | chr20 | 62680657 | 62680739 |
| chr20 | 62715014 | 62715069 | chr20 | 62786572 | 62786726 | chr20 | 62795643 | 62795762 |
| chr21 | 19274828 | 19274858 | chr21 | 22370332 | 22370458 | chr21 | 22370688 | 22370718 |
| chr21 | 26934368 | 26934786 | chr21 | 27011773 | 27011807 | chr21 | 27012373 | 27012431 |
| chr21 | 27944995 | 27945081 | chr21 | 27945693 | 27945722 | chr21 | 28216634 | 28217690 |
| chr21 | 28218774 | 28219045 | chr21 | 28338836 | 28338887 | chr21 | 28339247 | 28339501 |
| chr21 | 28339892 | 28340048 | chr21 | 28340063 | 28340318 | chr21 | 31015201 | 31015231 |
| chr21 | 31056850 | 31056927 | chr21 | 31311404 | 31311553 | chr21 | 31312080 | 31312105 |
| chr21 | 31312313 | 31312445 | chr21 | 32253745 | 32253774 | chr21 | 33043985 | 33044051 |
| chr21 | 33244921 | 33245040 | chr21 | 33245683 | 33245718 | chr21 | 33246009 | 33246190 |
| chr21 | 33627549 | 33627649 | chr21 | 33721756 | 33721824 | chr21 | 33785288 | 33785325 |
| chr21 | 33983236 | 33983488 | chr21 | 34392206 | 34392403 | chr21 | 34392437 | 34392566 |
| chr21 | 34395302 | 34396269 | chr21 | 34396795 | 34397091 | chr21 | 34398070 | 34398634 |
| chr21 | 34398933 | 34399258 | chr21 | 34399442 | 34400104 | chr21 | 34400232 | 34400258 |
| chr21 | 34401185 | 34401392 | chr21 | 34442595 | 34442665 | chr21 | 34443103 | 34443262 |
| chr21 | 34443509 | 34443686 | chr21 | 34443893 | 34443956 | chr21 | 34444163 | 34444362 |
| chr21 | 34444445 | 34444598 | chr21 | 34469746 | 34469844 | chr21 | 35051159 | 35051231 |
| chr21 | 36041985 | 36042028 | chr21 | 36042092 | 36042238 | chr21 | 36042658 | 36042861 |
| chr21 | 37527928 | 37527958 | chr21 | 37758570 | 37758652 | chr21 | 32775034 | 37775141 |
| chr21 | 38064457 | 38064683 | chr21 | 38064966 | 38065522 | chr21 | 38065955 | 38066112 |
| chr21 | 38067203 | 38067233 | chr21 | 38068178 | 38068229 | chr21 | 38068647 | 38068783 |
| chr21 | 38069093 | 38069203 | chr21 | 38069459 | 38069496 | chr21 | 38069854 | 38070162 |
| chr21 | 38070705 | 38070765 | chr21 | 38071791 | 38071905 | chr21 | 38073007 | 38073070 |
| chr21 | 38073300 | 38073525 | chr21 | 38073616 | 38073860 | chr21 | 38078415 | 38078487 |
| chr21 | 38079988 | 38080062 | chr21 | 38080175 | 38080386 | chr21 | 38080551 | 38080684 |
| chr21 | 38081085 | 38081192 | chr21 | 38081666 | 38081835 | chr21 | 38082042 | 38082072 |
| chr21 | 38082315 | 38082345 | chr21 | 38082930 | 38083196 | chr21 | 38092179 | 38092221 |
| chr21 | 38119904 | 38120312 | chr21 | 38638422 | 38638526 | chr21 | 38935478 | 38935549 |
| chr21 | 39047776 | 39047838 | chr21 | 39870612 | 39870641 | chr21 | 40033619 | 40033648 |
| chr21 | 40033877 | 40033906 | chr21 | 40034756 | 40034785 | chr21 | 40984685 | 40984900 |
| chr21 | 42596911 | 42597043 | chr21 | 42617963 | 42617995 | chr21 | 42649172 | 42649202 |
| chr21 | 43186698 | 43186889 | chr21 | 43240082 | 43240112 | chr21 | 43256565 | 43256603 |
| chr21 | 43376373 | 43376403 | chr21 | 43393528 | 43393713 | chr21 | 43485279 | 43485348 |
| chr21 | 43786683 | 43786713 | chr21 | 43991463 | 43991493 | chr21 | 44250815 | 44250855 |
| chr21 | 44283581 | 44283774 | chr21 | 44494941 | 44495155 | chr21 | 44514762 | 44514791 |
| chr21 | 44524441 | 44524470 | chr21 | 44837088 | 44837213 | chr21 | 44847591 | 44847622 |
| chr21 | 44866603 | 44866711 | chr21 | 44886709 | 44886870 | chr21 | 45118492 | 45118644 |
| chr21 | 45131875 | 45131905 | chr21 | 45148615 | 45148758 | chr21 | 45195149 | 45195319 |
| chr21 | 45271643 | 45271688 | chr21 | 45273717 | 45273913 | chr21 | 45277332 | 45277513 |
| chr21 | 45290014 | 45290044 | chr21 | 45508617 | 45508647 | chr21 | 45521343 | 45521438 |

TABLE 12-continued

| chr | start | end | chr | start | end | chr | start | end |
|---|---|---|---|---|---|---|---|---|
| chr21 | 45621533 | 45621573 | chr21 | 45717477 | 45717548 | chr21 | 45791079 | 45791109 |
| chr21 | 45847832 | 45847973 | chr21 | 46036642 | 46036767 | chr21 | 46125933 | 46126427 |
| chr21 | 46126562 | 46126721 | chr21 | 46127039 | 46127094 | chr21 | 46127542 | 46127692 |
| chr21 | 46128902 | 46128938 | chr21 | 46129444 | 46129485 | chr21 | 46193414 | 46193542 |
| chr21 | 46257116 | 46257273 | chr21 | 46310428 | 46310491 | chr21 | 46318285 | 46318343 |
| chr21 | 46319156 | 46319459 | chr21 | 46359187 | 46359248 | chr21 | 46452374 | 46452539 |
| chr21 | 46677734 | 46677796 | chr21 | 46825825 | 46826067 | chr21 | 46847654 | 46847684 |
| chr21 | 46863658 | 46863708 | chr21 | 46925780 | 46925925 | chr21 | 46926459 | 46926565 |
| chr21 | 46935739 | 46935936 | chr21 | 47010409 | 47010451 | chr21 | 47062753 | 47062825 |
| chr21 | 47063538 | 47063962 | chr21 | 47064250 | 47064377 | chr21 | 47404174 | 47404325 |
| chr21 | 47504861 | 47504895 | chr21 | 47518776 | 47518814 | chr21 | 47717560 | 47717589 |
| chr21 | 47746270 | 47746393 | chr22 | 17081932 | 17081935 | chr22 | 17082989 | 17083003 |
| chr22 | 17083396 | 17083410 | chr22 | 17601086 | 17601133 | chr22 | 17601260 | 17601368 |
| chr22 | 17602511 | 17602624 | chr22 | 17850454 | 17850621 | chr22 | 18009969 | 18010121 |
| chr22 | 18110495 | 18110593 | chr22 | 18328127 | 18328268 | chr22 | 18340822 | 18340868 |
| chr22 | 18627328 | 18627537 | chr22 | 19017532 | 19017567 | chr22 | 19117564 | 19117594 |
| chr22 | 19136907 | 19136936 | chr22 | 19137859 | 19137888 | chr22 | 19138109 | 19138138 |
| chr22 | 19510799 | 19510946 | chr22 | 19511142 | 19511455 | chr22 | 19511542 | 19511567 |
| chr22 | 19511849 | 19511875 | chr22 | 19702265 | 19702410 | chr22 | 19706171 | 19706677 |
| chr22 | 19742834 | 19742969 | chr22 | 19748644 | 19748908 | chr22 | 20229079 | 20229239 |
| chr22 | 20792482 | 20792641 | chr22 | 20864642 | 20864672 | chr22 | 20940868 | 20940898 |
| chr22 | 21042829 | 21043014 | chr22 | 21153867 | 21154000 | chr22 | 21270750 | 21270834 |
| chr22 | 21276140 | 21276261 | chr22 | 21299605 | 21299635 | chr22 | 21304771 | 21305007 |
| chr22 | 21368587 | 21368617 | chr22 | 21977314 | 21977347 | chr22 | 21982792 | 21982972 |
| chr22 | 22005794 | 22006759 | chr22 | 22023273 | 22023451 | chr22 | 22058203 | 22058238 |
| chr22 | 22201344 | 22201568 | chr22 | 22862787 | 22862862 | chr22 | 22901105 | 22901455 |
| chr22 | 23791402 | 23791432 | chr22 | 23801459 | 23801610 | chr22 | 23991201 | 23991272 |
| chr22 | 24145484 | 24145513 | chr22 | 24179940 | 24179982 | chr22 | 24180687 | 24180766 |
| chr22 | 24560375 | 24560526 | chr22 | 24820330 | 24820396 | chr22 | 25678748 | 25678868 |
| chr22 | 25679043 | 25679249 | chr22 | 25679268 | 25679337 | chr22 | 25817107 | 25817180 |
| chr22 | 25817458 | 25817612 | chr22 | 27053194 | 27053250 | chr22 | 28198569 | 28198605 |
| chr22 | 28371649 | 28371679 | chr22 | 28838200 | 28838292 | chr22 | 28838509 | 28838551 |
| chr22 | 28839122 | 28839263 | chr22 | 29076592 | 29076622 | chr22 | 29091824 | 29091853 |
| chr22 | 29445752 | 29445923 | chr22 | 29876191 | 29876220 | chr22 | 29877223 | 29877299 |
| chr22 | 29977614 | 29977863 | chr22 | 30084358 | 30084388 | chr22 | 30090739 | 30090769 |
| chr22 | 30116904 | 30117146 | chr22 | 30158330 | 30158639 | chr22 | 30476197 | 30476220 |
| chr22 | 30784196 | 30784278 | chr22 | 30881582 | 30881612 | chr22 | 30938543 | 30938584 |
| chr22 | 31198492 | 31198637 | chr22 | 31218510 | 31218540 | chr22 | 31218794 | 31218829 |
| chr22 | 31481130 | 31481332 | chr22 | 32061344 | 32061374 | chr22 | 32748936 | 32748966 |
| chr22 | 32868720 | 32868837 | chr22 | 33197603 | 33197652 | chr22 | 33453877 | 33454074 |
| chr22 | 33454194 | 33454258 | chr22 | 33454346 | 33454366 | chr22 | 35079219 | 35079345 |
| chr22 | 35656581 | 35656610 | chr22 | 35768531 | 35768719 | chr22 | 35848358 | 35848670 |
| chr22 | 35938746 | 35939000 | chr22 | 36567866 | 36567896 | chr22 | 36681295 | 36681341 |
| chr22 | 36855297 | 36855335 | chr22 | 36855568 | 36855598 | chr22 | 36880362 | 36880462 |
| chr22 | 36902291 | 36902381 | chr22 | 37302073 | 37302103 | chr22 | 37720961 | 37721163 |
| chr22 | 38002684 | 38002733 | chr22 | 38087310 | 38087367 | chr22 | 38182815 | 38182981 |
| chr22 | 38199769 | 38199894 | chr22 | 38220653 | 38221201 | chr22 | 38477069 | 38477131 |
| chr22 | 38477297 | 38477794 | chr22 | 38507316 | 38507346 | chr22 | 38592856 | 38593076 |
| chr22 | 38639229 | 38639259 | chr22 | 38874215 | 38874362 | chr22 | 39094890 | 39094964 |
| chr22 | 39098022 | 39098064 | chr22 | 39112502 | 39112584 | chr22 | 39784480 | 39784598 |
| chr22 | 39830355 | 39830457 | chr22 | 39853521 | 39853592 | chr22 | 39932499 | 39932563 |
| chr22 | 39954429 | 39954516 | chr22 | 40042627 | 40042743 | chr22 | 40075157 | 40075302 |
| chr22 | 40226345 | 40226389 | chr22 | 40767753 | 40767936 | chr22 | 40807034 | 40807063 |
| chr22 | 40895978 | 40896029 | chr22 | 41048732 | 41049109 | chr22 | 41217105 | 41217405 |
| chr22 | 41634393 | 41634542 | chr22 | 41637064 | 41637129 | chr22 | 41648414 | 41648444 |
| chr22 | 41657233 | 41657350 | chr22 | 41690119 | 41690149 | chr22 | 41839432 | 41839498 |
| chr22 | 42068010 | 42068172 | chr22 | 42096002 | 42096190 | chr22 | 42310087 | 42310220 |
| chr22 | 42311521 | 42311587 | chr22 | 42343416 | 42343676 | chr22 | 42353611 | 42353892 |
| chr22 | 42667358 | 42667432 | chr22 | 42916449 | 42916479 | chr22 | 43012543 | 43012877 |
| chr22 | 43083130 | 43083166 | chr22 | 43434441 | 43434477 | chr22 | 43540672 | 43540702 |
| chr22 | 43740084 | 43740128 | chr22 | 43808280 | 43808428 | chr22 | 44208418 | 44208448 |
| chr22 | 44258366 | 44258506 | chr22 | 44287650 | 44287696 | chr22 | 44455707 | 44455740 |
| chr22 | 45087614 | 45087649 | chr22 | 45088602 | 45088743 | chr22 | 45135939 | 45135979 |
| chr22 | 45252427 | 45252463 | chr22 | 45277292 | 45277322 | chr22 | 45313416 | 45313446 |
| chr22 | 45403086 | 45403133 | chr22 | 45403478 | 45403714 | chr22 | 45404197 | 45404433 |
| chr22 | 45404994 | 45405010 | chr22 | 45405047 | 45405061 | chr22 | 45405318 | 45405418 |
| chr22 | 45405620 | 45405768 | chr22 | 45406271 | 45406328 | chr22 | 45593643 | 45593715 |
| chr22 | 45604184 | 45604343 | chr22 | 45719161 | 45719190 | chr22 | 46262452 | 46263051 |
| chr22 | 46263512 | 46263623 | chr22 | 46263744 | 46263809 | chr22 | 46276749 | 46276820 |
| chr22 | 46438085 | 46438217 | chr22 | 46455833 | 46455905 | chr22 | 46599623 | 46599725 |
| chr22 | 46931260 | 46931332 | chr22 | 46933089 | 46933237 | chr22 | 47005080 | 47005154 |
| chr22 | 47023044 | 47023191 | chr22 | 47054686 | 47064716 | chr22 | 47193335 | 47193371 |
| chr22 | 47395475 | 47395505 | chr22 | 47525846 | 47525885 | chr22 | 47584867 | 47585024 |
| chr22 | 48027626 | 48027655 | chr22 | 48885530 | 48885837 | chr22 | 48886659 | 48886849 |
| chr22 | 48931881 | 48932027 | chr22 | 48971533 | 48971679 | chr22 | 48972220 | 48972465 |
| chr22 | 49852617 | 49852647 | chr22 | 49979646 | 49979757 | chr22 | 50001699 | 50001882 |
| chr22 | 50002787 | 50002819 | chr22 | 50003204 | 50003234 | chr22 | 50010113 | 50010258 |
| chr22 | 50010461 | 50010585 | chr22 | 50031691 | 50031721 | chr22 | 50064760 | 50064944 |

TABLE 12-continued

| chr | start | end | chr | start | end | chr | start | end |
|---|---|---|---|---|---|---|---|---|
| chr22 | 50149431 | 50149470 | chr22 | 50251536 | 50251582 | chr22 | 50467005 | 50467035 |
| chr22 | 50467876 | 50468105 | chr22 | 50497147 | 50497182 | chr22 | 50497214 | 50497287 |
| chr22 | 50623672 | 50623714 | chr22 | 50623742 | 50623815 | chr22 | 50768840 | 50768876 |
| chr22 | 50899293 | 50899672 | chr22 | 50939073 | 50939111 | chr22 | 50943093 | 50943262 |
| chr22 | 50986016 | 50986045 | chr22 | 51042278 | 51042404 | chr22 | 51042458 | 51042565 |
| chr22 | 51112150 | 51112232 | chrX | 3631506 | 3631633 | chrX | 3746612 | 3746642 |
| chrX | 6145331 | 6145688 | chrX | 8698863 | 8698897 | chrX | 8699504 | 8699566 |
| chrX | 15807465 | 15807693 | chrX | 20148710 | 20148739 | chrX | 20160594 | 20160914 |
| chrX | 44730179 | 44730271 | chrX | 47039370 | 47039399 | chrX | 47426106 | 47426144 |
| chrX | 47426780 | 47426821 | chrX | 50557075 | 50557075 | chrX | 66931448 | 66931477 |
| chrX | 66937356 | 66937385 | chrX | 66943529 | 66943567 | chrX | 70339239 | 70339268 |
| chrX | 100228394 | 100228431 | chrX | 100740260 | 100740289 | chrX | 101906099 | 101906120 |
| chrX | 102000609 | 102000758 | chrX | 134156560 | 134156680 | chrX | 136656553 | 136656592 |
| chrY | 2655316 | 2655346 | chrY | 3446305 | 3446441 | chrY | 3838889 | 3838919 |
| chrY | 3968100 | 3968132 | chrY | 13316007 | 13316132 | chrY | 14532822 | 14532852 |
| chrY | 14533556 | 14533613 | chrY | 21204734 | 21205113 | chrY | 22530026 | 22530073 |
| MCV-R17b | 111 | 140 | MCV-R17b | 368 | 397 | MCV-R17b | 625 | 654 |
| MCV-R17b | 882 | 911 | MCV-R17b | 1139 | 1168 | MCV-R17b | 1396 | 1425 |
| MCV-R17b | 1653 | 1682 | MCV-R17b | 1910 | 1939 | MCV-R17b | 2167 | 2196 |
| MCV-R17b | 2424 | 2453 | MCV-R17b | 2681 | 2710 | MCV-R17b | 2938 | 2967 |
| MCV-R17b | 3195 | 3224 | MCV-R17b | 3452 | 3481 | MCV-R17b | 3709 | 3738 |
| MCV-R17b | 3966 | 3995 | MCV-R17b | 4223 | 4252 | MCV-R17b | 4480 | 4509 |
| MCV-R17b | 4737 | 4766 | MCV-R17b | 4994 | 5023 | AC160854.2_10710-13495 | 1027 | 1057 |
| AC211950.2_11234-25326 | 129 | 257 | AC211950.2_11234-25326 | 13335 | 13445 | AC211950.2_11234-25326 | 13743 | 13889 |
| AC241851.2_88-34049 | 14729 | 14973 | AC241851.2_88-34049 | 15261 | 15350 | AEKP01168736.1_1-4752 | 1754 | 2287 |
| EBV-B95-8 | 967 | 996 | EBV-B95-8 | 3766 | 3795 | EBV-B95-8 | 4234 | 4263 |
| EBV-B95-8 | 5326 | 5355 | EBV-B95-8 | 6553 | 6582 | EBV-B95-8 | 8800 | 8829 |
| EBV-B95-8 | 13471 | 13500 | EBV-B95-8 | 46577 | 46606 | EBV-B95-8 | 48222 | 48251 |
| EBV-B95-8 | 52842 | 52871 | EBV-B95-8 | 53561 | 53590 | EBV-B95-8 | 54377 | 54406 |
| EBV-B95-8 | 54778 | 54802 | EBV-B95-8 | 55062 | 55096 | EBV-B95-8 | 55893 | 55922 |
| EBV-B95-8 | 56735 | 56764 | EBV-B95-8 | 58222 | 58256 | EBV-B95-8 | 58926 | 58955 |
| EBV-B95-8 | 59581 | 59610 | EBV-B95-8 | 60099 | 60128 | EBV-B95-8 | 60877 | 60906 |
| EBV-B95-8 | 61319 | 61348 | EBV-B95-8 | 62302 | 62331 | EBV-B95-8 | 62840 | 62869 |
| EBV-B95-8 | 63178 | 63207 | EBV-B95-8 | 63601 | 63630 | EBV-B95-8 | 63935 | 63964 |
| EBV-B95-8 | 64590 | 64619 | EBV-B95-8 | 66726 | 66755 | EBV-B95-8 | 67486 | 67515 |
| EBV-B95-8 | 67857 | 67886 | EBV-B95-8 | 69228 | 69257 | EBV-B95-8 | 69798 | 69827 |
| EBV-B95-8 | 70439 | 70468 | EBV-B95-8 | 70839 | 70868 | EBV-B95-8 | 71938 | 71967 |
| EBV-B95-8 | 72204 | 72233 | EBV-B95-8 | 72535 | 72564 | EBV-B95-8 | 72983 | 73012 |
| EBV-B95-8 | 73950 | 73979 | EBV-B95-8 | 74304 | 74333 | EBV-B95-8 | 74689 | 74718 |
| EBV-B95-8 | 74978 | 75007 | EBV-B95-8 | 75256 | 75285 | EBV-B95-8 | 77784 | 77813 |
| EBV-B95-8 | 79618 | 79647 | EBV-B95-8 | 80289 | 80318 | EBV-B95-8 | 80704 | 80733 |
| EBV-B95-8 | 81198 | 81227 | EBV-B95-8 | 81629 | 81658 | EBV-B95-8 | 81888 | 81917 |
| EBV-B95-8 | 82225 | 82254 | EBV-B95-8 | 82703 | 82732 | EBV-B95-8 | 83438 | 83467 |
| EBV-B95-8 | 85345 | 85374 | EBV-B95-8 | 86299 | 86328 | EBV-B95-8 | 87104 | 87133 |
| EBV-B95-8 | 89959 | 89988 | EBV-B95-8 | 90915 | 90944 | EBV-B95-8 | 92531 | 92560 |
| EBV-B95-8 | 94071 | 94100 | EBV-B95-8 | 94731 | 94760 | EBV-B95-8 | 95084 | 95113 |
| EBV-B95-8 | 97482 | 97511 | EBV-B95-8 | 98245 | 98274 | EBV-B95-8 | 99224 | 99253 |
| EBV-B95-8 | 100235 | 100264 | EBV-B95-8 | 101009 | 101038 | EBV-B95-8 | 102716 | 102745 |
| EBV-B95-8 | 104004 | 104033 | EBV-B95-8 | 105019 | 105048 | EBV-B95-8 | 105284 | 105313 |
| EBV-B95-8 | 107231 | 107260 | EBV-B95-8 | 108023 | 108052 | EBV-B95-8 | 108370 | 108399 |
| EBV-B95-8 | 109086 | 109115 | EBV-B95-8 | 110250 | 110279 | EBV-B95-8 | 110626 | 110655 |
| EBV-B95-8 | 111690 | 111719 | EBV-B95-8 | 112112 | 112141 | EBV-B95-8 | 114429 | 114458 |
| EBV-B95-8 | 114749 | 114778 | EBV-B95-8 | 115006 | 115035 | EBV-B95-8 | 115597 | 115626 |
| EBV-B95-8 | 116382 | 116411 | EBV-B95-8 | 116649 | 116678 | EBV-B95-8 | 118647 | 118676 |
| EBV-B95-8 | 119542 | 119571 | EBV-B95-8 | 120350 | 120379 | EBV-B95-8 | 121382 | 121411 |
| EBV-B95-8 | 123037 | 123066 | EBV-B95-8 | 123570 | 123599 | EBV-B95-8 | 124913 | 124942 |
| EBV-B95-8 | 125376 | 125405 | EBV-B95-8 | 125805 | 125834 | EBV-B95-8 | 126337 | 126366 |
| EBV-B95-8 | 127493 | 127522 | EBV-B95-8 | 127905 | 127934 | EBV-B95-8 | 128805 | 128834 |
| EBV-B95-8 | 130244 | 130273 | EBV-B95-8 | 130690 | 130719 | EBV-B95-8 | 131603 | 131632 |
| EBV-B95-8 | 134325 | 134354 | EBV-B95-8 | 135032 | 135061 | EBV-B95-8 | 135599 | 135628 |
| EBV-B95-8 | 136148 | 136177 | EBV-B95-8 | 136680 | 136709 | EBV-B95-8 | 137805 | 137834 |
| EBV-B95-8 | 138375 | 138404 | EBV-B95-8 | 139745 | 139774 | EBV-B95-8 | 140610 | 140639 |
| EBV-B95-8 | 141137 | 141166 | EBV-B95-8 | 142290 | 142319 | EBV-B95-8 | 142763 | 142792 |
| EBV-B95-8 | 143078 | 143107 | EBV-B95-8 | 144318 | 144347 | EBV-B95-8 | 145216 | 145245 |
| EBV-B95-8 | 145638 | 145667 | EBV-B95-8 | 147044 | 147073 | EBV-B95-8 | 148404 | 148433 |
| EBV-B95-8 | 150099 | 150128 | EBV-B95-8 | 150443 | 150472 | EBV-B95-8 | 152230 | 152259 |
| EBV-B95-8 | 153127 | 153156 | EBV-B95-8 | 153468 | 153497 | EBV-B95-8 | 153800 | 153829 |
| EBV-B95-8 | 154204 | 154233 | EBV-B95-8 | 156501 | 156530 | EBV-B95-8 | 156773 | 156802 |
| EBV-B95-8 | 157345 | 157374 | EBV-B95-8 | 159211 | 159240 | EBV-B95-8 | 159561 | 159590 |
| EBV-B95-8 | 161193 | 161222 | EBV-B95-8 | 161698 | 161722 | EBV-B95-8 | 162343 | 162372 |
| EBV-B95-8 | 163798 | 163827 | EBV-B95-8 | 164471 | 164500 | EBV-B95-8 | 166234 | 165263 |
| EBV-B95-8 | 166280 | 166309 | EBV-B95-8 | 167347 | 167376 | EBV-B95-8 | 167600 | 167629 |
| EBV-B95-8 | 167942 | 167971 | EBV-B95-8 | 168551 | 168580 | EBV-B95-8 | 171304 | 171333 |
| GL000225.1 | 37720 | 37842 | GL000231.1 | 12576 | 12717 | HBV | 111 | 140 |
| HBV | 381 | 410 | HBV | 651 | 680 | HBV | 921 | 950 |

TABLE 12-continued

| chr | start | end | chr | start | end | chr | start | end |
|---|---|---|---|---|---|---|---|---|
| HBV | 1191 | 1220 | HBV | 1461 | 1490 | HBV | 1731 | 1760 |
| HBV | 2001 | 2030 | HBV | 2271 | 2300 | HBV | 2541 | 2570 |
| HBV | 2811 | 2840 | HCMV-AD169 | 17724 | 17753 | HCMV-AD169 | 18691 | 18720 |
| HCMV-AD169 | 23851 | 23880 | HCMV-AD169 | 27296 | 27325 | HCMV-AD169 | 42909 | 42938 |
| HCMV-AD169 | 57909 | 57938 | HCMV-AD169 | 68427 | 68456 | HCMV-AD169 | 76862 | 76891 |
| HCMV-AD169 | 78956 | 78985 | HCMV-AD169 | 81188 | 81217 | HCMV-AD169 | 84448 | 84477 |
| HCMV-AD169 | 88920 | 88949 | HCMV-AD169 | 99889 | 99918 | HCMV-AD169 | 101238 | 101267 |
| HCMV-AD169 | 108021 | 108050 | HCMV-AD169 | 114824 | 114853 | HCMV-AD169 | 128011 | 128040 |
| HCMV-AD169 | 129567 | 129596 | HCMV-AD169 | 149187 | 149216 | HCMV-AD169 | 162299 | 162328 |
| HCMV-AD169 | 169250 | 169279 | HCMV-AD169 | 171221 | 171250 | HCMV-AD169 | 172561 | 172590 |
| HCMV-AD169 | 177053 | 177082 | HCMV-AD169 | 193060 | 193089 | HCMV-AD169 | 193858 | 193887 |
| HCMV-AD169 | 194176 | 194205 | HCMV-AD169 | 195222 | 195251 | HCMV-AD169 | 196060 | 196089 |
| HCMV-AD169 | 196817 | 196846 | HCMV-AD169 | 199152 | 199181 | HCMV-AD169 | 199906 | 199935 |
| HCMV-AD169 | 201145 | 201174 | HCMV-AD169 | 204433 | 204462 | HCMV-AD169 | 207682 | 207711 |
| HCMV-AD169 | 209510 | 209539 | HCMV-AD169 | 210069 | 210098 | HCMV-AD169 | 212133 | 212162 |
| HCMV-AD169 | 212591 | 212620 | HCMV-AD169 | 214453 | 214482 | HCMV-AD169 | 220316 | 220345 |
| HCV | 111 | 140 | HCV | 374 | 403 | HCV | 637 | 666 |
| HCV | 900 | 929 | HCV | 1163 | 1192 | HCV | 1426 | 1455 |
| HCV | 1689 | 1718 | HCV | 1952 | 1981 | HCV | 2215 | 2244 |
| HCV | 2478 | 2507 | HCV | 2741 | 2770 | HCV | 3004 | 3033 |
| HCV | 3267 | 3296 | HCV | 3530 | 3559 | HCV | 3793 | 3822 |
| HCV | 4056 | 4085 | HCV | 4319 | 4348 | HCV | 4582 | 4611 |
| HCV | 4845 | 4874 | HCV | 5108 | 5137 | HCV | 5371 | 5400 |
| HCV | 5634 | 5663 | HCV | 5897 | 5926 | HCV | 6160 | 6189 |
| HCV | 6423 | 6452 | HCV | 6686 | 6715 | HCV | 6949 | 6978 |
| HCV | 7212 | 7241 | HCV | 7475 | 7504 | HCV | 7738 | 7767 |
| HCV | 8001 | 8030 | HCV | 8264 | 8293 | HCV | 8527 | 8556 |
| HCV | 8790 | 8819 | HCV | 9053 | 9082 | HHV5-CINCY-TOWNE | 1181 | 1210 |
| HHV5-CINCY-TOWNE | 1988 | 2017 | HHV5-CINCY-TOWNE | 2389 | 2418 | HHV5-CINCY-TOWNE | 3290 | 3319 |
| HHV5-CINCY-TOWNE | 3665 | 3694 | HHV5-CINCY-TOWNE | 4704 | 4733 | HHV5-CINCY-TOWNE | 5400 | 5429 |
| HHV5-CINCY-TOWNE | 7790 | 7819 | HHV5-CINCY-TOWNE | 9656 | 9685 | HHV5-CINCY-TOWNE | 10781 | 10810 |
| HHV5-CINCY-TOWNE | 11109 | 11138 | HHV5-CINCY-TOWNE | 12663 | 12692 | HHV5-CINCY-TOWNE | 13688 | 13717 |
| HHV5-CINCY-TOWNE | 14223 | 14252 | HHV5-CINCY-TOWNE | 14911 | 14940 | HHV5-CINCY-TOWNE | 15206 | 15235 |
| HHV5-CINCY-TOWNE | 15938 | 15967 | HHV5-CINCY-TOWNE | 16440 | 16469 | HHV5-CINCY-TOWNE | 16884 | 16913 |
| HHV5-CINCY-TOWNE | 17347 | 17376 | HHV5-CINCY-TOWNE | 17696 | 17725 | HHV5-CINCY-TOWNE | 17958 | 17987 |
| HHV5-CINCY-TOWNE | 18372 | 18401 | HHV5-CINCY-TOWNE | 19417 | 19446 | HHV5-CINCY-TOWNE | 19910 | 19939 |
| HHV5-CINCY-TOWNE | 20248 | 20277 | HHV5-CINCY-TOWNE | 20671 | 20700 | HHV5-CINCY-TOWNE | 21899 | 21928 |
| HHV5-CINCY-TOWNE | 22798 | 22827 | HHV5-CINCY-TOWNE | 23095 | 23124 | HHV5-CINCY-TOWNE | 26713 | 26742 |
| HHV5-CINCY-TOWNE | 27211 | 27240 | HHV5-CINCY-TOWNE | 29784 | 29813 | HHV5-CINCY-TOWNE | 31141 | 31170 |

TABLE 12-continued

| chr | start | end | chr | start | end | chr | start | end |
|---|---|---|---|---|---|---|---|---|
| HHV5-CINCY-TOWNE | 32660 | 32689 | HHV5-CINCY-TOWNE | 35651 | 35680 | HHV5-CINCY-TOWNE | 36393 | 36422 |
| HHV5-CINCY-TOWNE | 37224 | 37253 | HHV5-CINCY-TOWNE | 37895 | 37924 | HHV5-CINCY-TOWNE | 39244 | 39273 |
| HHV5-CINCY-TOWNE | 43188 | 43217 | HHV5-CINCY-TOWNE | 44447 | 44476 | HHV5-CINCY-TOWNE | 44799 | 44828 |
| HHV5-CINCY-TOWNE | 45394 | 45423 | HHV5-CINCY-TOWNE | 46445 | 46474 | HHV5-CINCY-TOWNE | 46944 | 46973 |
| HHV5-CINCY-TOWNE | 47916 | 47945 | HHV5-CINCY-TOWNE | 48504 | 48533 | HHV5-CINCY-TOWNE | 49094 | 49123 |
| HHV5-CINCY-TOWNE | 49903 | 49932 | HHV5-CINCY-TOWNE | 50230 | 50259 | HHV5-CINCY-TOWNE | 51421 | 51450 |
| HHV5-CINCY-TOWNE | 53772 | 53801 | HHV5-CINCY-TOWNE | 55651 | 55680 | HHV5-CINCY-TOWNE | 56380 | 56409 |
| HHV5-CINCY-TOWNE | 57291 | 57320 | HHV5-CINCY-TOWNE | 58491 | 58520 | HHV5-CINCY-TOWNE | 59023 | 59052 |
| HHV5-CINCY-TOWNE | 59792 | 59821 | HHV5-CINCY-TOWNE | 60124 | 60153 | HHV5-CINCY-TOWNE | 60392 | 60421 |
| HHV5-CINCY-TOWNE | 60900 | 60929 | HHV5-CINCY-TOWNE | 63894 | 63923 | HHV5-CINCY-TOWNE | 65843 | 65872 |
| HHV5-CINCY-TOWNE | 68089 | 68118 | HHV5-CINCY-TOWNE | 72454 | 72483 | HHV5-CINCY-TOWNE | 81185 | 81214 |
| HHV5-CINCY-TOWNE | 84144 | 84173 | HHV5-CINCY-TOWNE | 85524 | 85553 | HHV5-CINCY-TOWNE | 85943 | 85972 |
| HHV5-CINCY-TOWNE | 86889 | 86918 | HHV5-CINCY-TOWNE | 87195 | 87224 | HHV5-CINCY-TOWNE | 87455 | 87484 |
| HHV5-CINCY-TOWNE | 87769 | 87798 | HHV5-CINCY-TOWNE | 88564 | 88593 | HHV5-CINCY-TOWNE | 93096 | 93125 |
| HHV5-CINCY-TOWNE | 93776 | 93805 | HHV5-CINCY-TOWNE | 97621 | 97650 | HHV5-CINCY-TOWNE | 98732 | 98766 |
| HHV5-CINCY-TOWNE | 99460 | 99489 | HHV5-CINCY-TOWNE | 107540 | 107569 | HHV5-CINCY-TOWNE | 108823 | 108852 |
| HHV5-CINCY-TOWNE | 109725 | 109754 | HHV5-CINCY-TOWNE | 112036 | 112065 | HHV5-CINCY-TOWNE | 112319 | 112348 |
| HHV5-CINCY-TOWNE | 112595 | 112624 | HHV5-CINCY-TOWNE | 112892 | 112921 | HHV5-CINCY-TOWNE | 113194 | 113223 |
| HHV5-CINCY-TOWNE | 113535 | 113564 | HHV5-CINCY-TOWNE | 113927 | 113956 | HHV5-CINCY-TOWNE | 114267 | 114296 |
| HHV5-CINCY-TOWNE | 114593 | 114622 | HHV5-CINCY-TOWNE | 114867 | 114896 | HHV5-CINCY-TOWNE | 115177 | 115206 |
| HHV5-CINCY-TOWNE | 115432 | 115461 | HHV5-CINCY-TOWNE | 115685 | 115714 | HHV5-CINCY-TOWNE | 115986 | 116015 |
| HHV5-CINCY-TOWNE | 116382 | 116411 | HHV5-CINCY-TOWNE | 116700 | 116729 | HHV5-CINCY-TOWNE | 118193 | 118222 |
| HHV5-CINCY-TOWNE | 118995 | 119024 | HHV5-CINCY-TOWNE | 120028 | 120067 | HHV5-CINCY-TOWNE | 121485 | 121514 |
| HHV5-CINCY-TOWNE | 122199 | 122228 | HHV5-CINCY-TOWNE | 122606 | 122635 | HHV5-CINCY-TOWNE | 124559 | 124588 |
| HHV5-CINCY-TOWNE | 125276 | 125305 | HHV5-CINCY-TOWNE | 132497 | 132526 | HHV5-CINCY-TOWNE | 135460 | 135489 |
| HHV5-CINCY-TOWNE | 135730 | 135759 | HHV5-CINCY-TOWNE | 137379 | 137408 | HHV5-CINCY-TOWNE | 139067 | 139096 |

TABLE 12-continued

| chr | start | end | chr | start | end | chr | start | end |
|---|---|---|---|---|---|---|---|---|
| HHV5-CINCY-TOWNE | 139472 | 139501 | HHV5-CINCY-TOWNE | 140147 | 140176 | HHV5-CINCY-TOWNE | 140722 | 140751 |
| HHV5-CINCY-TOWNE | 142023 | 142052 | HHV5-CINCY-TOWNE | 143692 | 143721 | HHV5-CINCY-TOWNE | 144080 | 144109 |
| HHV5-CINCY-TOWNE | 147310 | 147339 | HHV5-CINCY-TOWNE | 149465 | 149494 | HHV5-CINCY-TOWNE | 150359 | 150388 |
| HHV5-CINCY-TOWNE | 151593 | 151622 | HHV5-CINCY-TOWNE | 152153 | 152182 | HHV5-CINCY-TOWNE | 154148 | 164177 |
| HHV5-CINCY-TOWNE | 154610 | 154639 | HHV5-CINCY-TOWNE | 157018 | 157047 | HHV5-CINCY-TOWNE | 157367 | 157396 |
| HHV5-CINCY-TOWNE | 169038 | 169067 | HHV5-CINCY-TOWNE | 171503 | 171532 | HHV5-CINCY-TOWNE | 175146 | 175175 |
| HHV5-CINCY-TOWNE | 177553 | 177582 | HHV5-CINCY-TOWNE | 182254 | 182283 | HHV5-CINCY-TOWNE | 183115 | 183144 |
| HHV5-CINCY-TOWNE | 184120 | 184149 | HHV5-CINCY-TOWNE | 185558 | 185587 | HHV5-CINCY-TOWNE | 186027 | 186056 |
| HHV5-CINCY-TOWNE | 186435 | 186464 | HHV5-CINCY-TOWNE | 186707 | 186736 | HHV5-CINCY-TOWNE | 187115 | 187144 |
| HHV5-CINCY-TOWNE | 187514 | 187543 | HHV5-CINCY-TOWNE | 187859 | 187888 | HHV5-CINCY-TOWNE | 188473 | 188502 |
| HHV5-CINCY-TOWNE | 188768 | 188797 | HHV5-CINCY-TOWNE | 189050 | 189079 | HHV5-CINCY-TOWNE | 189302 | 189331 |
| HHV5-CINCY-TOWNE | 189936 | 189965 | HHV5-CINCY-TOWNE | 190655 | 190684 | HHV5-CINCY-TOWNE | 190954 | 190983 |
| HHV5-CINCY-TOWNE | 191453 | 191482 | HHV5-CINCY-TOWNE | 191882 | 191911 | HHV5-CINCY-TOWNE | 192183 | 192212 |
| HHV5-CINCY-TOWNE | 192541 | 192570 | HHV5-CINCY-TOWNE | 193045 | 193074 | HHV5-CINCY-TOWNE | 193325 | 193354 |
| HHV5-CINCY-TOWNE | 193597 | 193626 | HHV5-CINCY-TOWNE | 194165 | 194194 | HHV5-CINCY-TOWNE | 194461 | 194490 |
| HHV5-CINCY-TOWNE | 194848 | 194877 | HHV5-CINCY-TOWNE | 195324 | 195353 | HHV5-CINCY-TOWNE | 195651 | 195680 |
| HHV5-CINCY-TOWNE | 196018 | 196047 | HHV5-CINCY-TOWNE | 196343 | 196372 | HHV5-CINCY-TOWNE | 196941 | 196970 |
| HHV5-CINCY-TOWNE | 197218 | 197247 | HHV5-CINCY-TOWNE | 198315 | 198344 | HHV5-CINCY-TOWNE | 198792 | 198821 |
| HHV5-CINCY-TOWNE | 199162 | 199191 | HHV5-CINCY-TOWNE | 200113 | 200142 | HHV5-CINCY-TOWNE | 200571 | 200600 |
| HHV5-CINCY-TOWNE | 201373 | 201402 | HHV5-CINCY-TOWNE | 201905 | 201934 | HHV5-CINCY-TOWNE | 202264 | 202293 |
| HHV5-CINCY-TOWNE | 202537 | 202566 | HHV5-CINCY-TOWNE | 203319 | 203348 | HHV5-CINCY-TOWNE | 203720 | 203749 |
| HHV5-CINCY-TOWNE | 204008 | 204037 | HHV5-CINCY-TOWNE | 206213 | 206242 | HHV5-CINCY-TOWNE | 206735 | 206764 |
| HHV5-CINCY-TOWNE | 211676 | 211705 | HHV5-CINCY-TOWNE | 212340 | 212369 | HHV5-CINCY-TOWNE | 212609 | 212638 |
| HHV5-CINCY-TOWNE | 213813 | 213842 | HHV5-CINCY-TOWNE | 214695 | 214724 | HHV5-CINCY-TOWNE | 214950 | 214979 |
| HHV5-CINCY-TOWNE | 215930 | 215959 | HHV5-CINCY-TOWNE | 216228 | 216257 | HHV5-CINCY-TOWNE | 222672 | 222701 |
| HHV5-CINCY-TOWNE | 223515 | 223544 | HHV5-CINCY-TOWNE | 225150 | 225179 | HHV5-CINCY-TOWNE | 226058 | 226087 |

TABLE 12-continued

| chr | start | end | chr | start | end | chr | start | end |
|---|---|---|---|---|---|---|---|---|
| HHV5-CINCY-TOWNE | 226887 | 226916 | HPV16 | 111 | 140 | HPV16 | 367 | 396 |
| HPV16 | 623 | 652 | HPV16 | 879 | 908 | HPV16 | 1135 | 1164 |
| HPV16 | 1391 | 1420 | HPV16 | 1647 | 1676 | HPV16 | 1903 | 1932 |
| HPV16 | 2159 | 2188 | HPV16 | 2415 | 2444 | HPV16 | 2671 | 2700 |
| HPV16 | 2927 | 2956 | HPV16 | 3183 | 3212 | HPV16 | 3439 | 3468 |
| HPV16 | 3695 | 3724 | HPV16 | 3951 | 3980 | HPV16 | 4207 | 4236 |
| HPV16 | 4463 | 4492 | HPV16 | 4719 | 4748 | HPV16 | 4975 | 5004 |
| HPV16 | 5231 | 5260 | HPV16 | 5487 | 5516 | HPV16 | 5743 | 5772 |
| HPV16 | 5999 | 6028 | HPV16 | 6255 | 6284 | HPV16 | 6511 | 6540 |
| HPV16 | 6767 | 6796 | HPV16 | 7023 | 7052 | HPV16 | 7279 | 7308 |
| HPV16 | 7535 | 7564 | HPV18 | 111 | 140 | HPV18 | 383 | 412 |
| HPV18 | 655 | 684 | HPV18 | 927 | 956 | HPV18 | 1199 | 1228 |
| HPV18 | 1471 | 1500 | HPV18 | 1743 | 1772 | HPV18 | 2015 | 2044 |
| HPV18 | 2287 | 2316 | HPV18 | 2559 | 2588 | HPV18 | 2831 | 2860 |
| HPV18 | 3103 | 3132 | HPV18 | 3375 | 3404 | HPV18 | 3647 | 3676 |
| HPV18 | 3919 | 3948 | HPV18 | 4191 | 4220 | HPV18 | 4463 | 4492 |
| HPV18 | 4735 | 4764 | HPV18 | 5007 | 5036 | HPV18 | 5279 | 5308 |
| HPV18 | 5551 | 5580 | HPV18 | 5823 | 5852 | HPV18 | 6095 | 6124 |
| HPV18 | 6367 | 6396 | HPV18 | 6639 | 6668 | HPV18 | 6911 | 6940 |
| HPV18 | 7183 | 7212 | HPV18 | 7455 | 7484 | — | — | — |

TABLE 13

| chr | start | end | chr | start | end | chr | start | end |
|---|---|---|---|---|---|---|---|---|
| chr1 | 898654 | 898690 | chr1 | 913532 | 913955 | chr1 | 1047531 | 1047619 |
| chr1 | 1080583 | 1080824 | chr1 | 1146734 | 1146818 | chr1 | 1218737 | 1218779 |
| chr1 | 1223512 | 1223612 | chr1 | 1235813 | 1236078 | chr1 | 1267014 | 1267151 |
| chr1 | 1267462 | 1267699 | chr1 | 1267906 | 1268158 | chr1 | 1281214 | 1281244 |
| chr1 | 1341706 | 1341743 | chr1 | 1473125 | 1473207 | chr1 | 1475556 | 1475643 |
| chr1 | 1476255 | 1476318 | chr1 | 1483186 | 1483363 | chr1 | 1563193 | 1563223 |
| chr1 | 1688882 | 1689012 | chr1 | 1805049 | 1805069 | chr1 | 1856436 | 1856466 |
| chr1 | 1857847 | 1857909 | chr1 | 1874744 | 1874787 | chr1 | 1910415 | 1910445 |
| chr1 | 1923489 | 1923521 | chr1 | 1935274 | 1935459 | chr1 | 1974848 | 1974925 |
| chr1 | 2066490 | 2066679 | chr1 | 2125216 | 2125483 | chr1 | 2165895 | 2165999 |
| chr1 | 2263169 | 2263263 | chr1 | 2267552 | 2267690 | chr1 | 2304327 | 2304389 |
| chr1 | 2307925 | 2307955 | chr1 | 2308376 | 2308636 | chr1 | 2309868 | 2309953 |
| chr1 | 2331363 | 2331437 | chr1 | 2336397 | 2336427 | chr1 | 2375148 | 2375543 |
| chr1 | 2397001 | 2397031 | chr1 | 2428331 | 2428385 | chr1 | 2472174 | 2472301 |
| chr1 | 2507063 | 2507183 | chr1 | 2514330 | 2514353 | chr1 | 2521024 | 2521063 |
| chr1 | 2706308 | 2706334 | chr1 | 2830155 | 2830185 | chr1 | 2866038 | 2866068 |
| chr1 | 2984719 | 2984749 | chr1 | 3102653 | 3102779 | chr1 | 3158823 | 3158962 |
| chr1 | 3182883 | 3182917 | chr1 | 3322090 | 3322170 | chr1 | 3567093 | 3567344 |
| chr1 | 3567738 | 3567850 | chr1 | 3567883 | 3568226 | chr1 | 3601850 | 3601946 |
| chr1 | 3607081 | 3607236 | chr1 | 3659550 | 3659642 | chr1 | 3659672 | 3659716 |
| chr1 | 3663532 | 3663562 | chr1 | 3663874 | 3663921 | chr1 | 3664481 | 3664741 |
| chr1 | 3683722 | 3683818 | chr1 | 3700384 | 3700414 | chr1 | 3733551 | 3733581 |
| chr1 | 4111086 | 4111231 | chr1 | 4401433 | 4401463 | chr1 | 4714074 | |
| chr1 | 4714164 | 4714345 | chr1 | 4715428 | 4715539 | chr1 | 4715575 | 4716701 |
| chr1 | 5919973 | 5920071 | chr1 | 5920650 | 5920710 | chr1 | 5924296 | 5924431 |
| chr1 | 5924851 | 5924984 | chr1 | 5926596 | 5926645 | chr1 | 5933086 | 5933144 |
| chr1 | 5934925 | 5935061 | chr1 | 5940517 | 5940547 | chr1 | 5941099 | 5941132 |
| chr1 | 5944299 | 5944449 | chr1 | 5945348 | 5945435 | chr1 | 5947258 | 5947288 |
| chr1 | 5949491 | 5949575 | chr1 | 5950965 | 5951039 | chr1 | 5957473 | 5957503 |
| chr1 | 5967237 | 5967267 | chr1 | 5969001 | 5969283 | chr1 | 5972104 | 5972134 |
| chr1 | 5972878 | 5972922 | chr1 | 6021621 | 6021651 | chr1 | 6025872 | 6025950 |
| chr1 | 6036766 | 6036796 | chr1 | 6056157 | 6056201 | chr1 | 6056506 | 6056651 |
| chr1 | 6059910 | 6059974 | chr1 | 6166353 | 6166469 | chr1 | 5171763 | 6171810 |
| chr1 | 6186511 | 6186546 | chr1 | 6280243 | 6280273 | chr1 | 6284828 | 6284858 |
| chr1 | 6304201 | 6304242 | chr1 | 6360593 | 6360634 | chr1 | 6410456 | 6410486 |
| chr1 | 6446131 | 6446308 | chr1 | 6480514 | 6480831 | chr1 | 6501055 | 6501179 |
| chr1 | 6507678 | 6508126 | chr1 | 6713914 | 6714041 | chr1 | 6714348 | 6714378 |
| chr1 | 7764641 | 7764737 | chr1 | 8085685 | 8085715 | chr1 | 9324231 | 9324274 |
| chr1 | 9402465 | 9402616 | chr1 | 9527172 | 9527208 | chr1 | 9712074 | 9712104 |
| chr1 | 9712561 | 9713014 | chr1 | 9795995 | 9796196 | chr1 | 9867157 | 9867316 |
| chr1 | 10091888 | 10091914 | chr1 | 10166521 | 10166551 | chr1 | 10948552 | 10948582 |
| chr1 | 11169346 | 11169375 | chr1 | 11174404 | 11174433 | chr1 | 11181358 | 11181432 |
| chr1 | 11182142 | 11182171 | chr1 | 11188149 | 11188178 | chr1 | 11210182 | 11210211 |
| chr1 | 11217215 | 11217337 | chr1 | 11249032 | 11249061 | chr1 | 11538705 | 11538821 |
| chr1 | 11539175 | 11539205 | chr1 | 11539410 | 11539440 | chr1 | 11540129 | 11540178 |
| chr1 | 11591719 | 11591826 | chr1 | 11752476 | 11752511 | chr1 | 11886250 | 11886280 |
| chr1 | 11936748 | 11936778 | chr1 | 11959093 | 11959196 | chr1 | 12041510 | 12041525 |
| chr1 | 12123243 | 12123553 | chr1 | 12227685 | 12227941 | chr1 | 12251443 | 12251958 |

TABLE 13-continued

| chr | start | end | chr | start | end | chr | start | end |
|---|---|---|---|---|---|---|---|---|
| chr1 | 12460299 | 12460356 | chr1 | 13910436 | 13910714 | chr1 | 14026481 | 14026618 |
| chr1 | 14097878 | 14097977 | chr1 | 14128478 | 14128588 | chr1 | 14149749 | 14149867 |
| chr1 | 14730425 | 14730472 | chr1 | 14925501 | 14926050 | chr1 | 15128565 | 15128595 |
| chr1 | 15251120 | 15251211 | chr1 | 15480593 | 15480892 | chr1 | 16475031 | 16475207 |
| chr1 | 16861522 | 16861552 | chr1 | 17445857 | 17445943 | chr1 | 18437457 | 18437526 |
| chr1 | 18956211 | 18956304 | chr1 | 18956574 | 18956610 | chr1 | 18956956 | 18957246 |
| chr1 | 18957507 | 18957587 | chr1 | 18958033 | 18958228 | chr1 | 18958359 | 18958381 |
| chr1 | 18959456 | 18959550 | chr1 | 18960897 | 18960990 | chr1 | 18962727 | 18963135 |
| chr1 | 18969625 | 18969819 | chr1 | 18971852 | 18971929 | chr1 | 18972130 | 18972160 |
| chr1 | 19043563 | 19043678 | chr1 | 19992418 | 19992432 | chr1 | 20127435 | 20127471 |
| chr1 | 20248109 | 20248141 | chr1 | 20618329 | 20618369 | chr1 | 20693317 | 20693420 |
| chr1 | 20879035 | 20879228 | chr1 | 20879256 | 20879289 | chr1 | 20879562 | 20879640 |
| chr 1 | 20879845 | 20879957 | chr1 | 20880182 | 20880605 | chr1 | 21026117 | 21026225 |
| chr1 | 21042894 | 21042924 | chr1 | 21044125 | 21044161 | chr1 | 21050471 | 21050511 |
| chr1 | 21058635 | 21058776 | chr1 | 21573668 | 21574203 | chr1 | 21835943 | 21836007 |
| chr1 | 22140753 | 22141184 | chr1 | 22141326 | 22141355 | chr1 | 22222711 | 22222793 |
| chr1 | 22927410 | 22927482 | chr1 | 23748982 | 23749070 | chr1 | 23885070 | 23885100 |
| chr1 | 25255921 | 25255934 | chr1 | 25256354 | 25256383 | chr1 | 25257157 | 25257205 |
| chr1 | 25257490 | 25257529 | chr1 | 25257532 | 25257561 | chr1 | 25257916 | 25258250 |
| chr1 | 25919307 | 25919337 | chr1 | 26467523 | 26467547 | chr1 | 26551729 | 26551796 |
| chr1 | 26552086 | 26552130 | chr1 | 26737583 | 26737613 | chr1 | 26737946 | 26738182 |
| chr1 | 26917724 | 26917740 | chr1 | 27190175 | 27190278 | chr1 | 27332448 | 27332673 |
| chr1 | 27844518 | 27844548 | chr1 | 29048601 | 29048643 | chr1 | 29450491 | 29450543 |
| chr1 | 29586072 | 29586674 | chr1 | 29804947 | 29805094 | chr1 | 30351554 | 30351742 |
| chr1 | 30815412 | 30815416 | chr1 | 30815455 | 30815578 | chr1 | 31863186 | 31863216 |
| chr1 | 32180397 | 32180427 | chr1 | 32237639 | 32238507 | chr1 | 32410276 | 32410306 |
| chr1 | 32410519 | 32410614 | chr1 | 32705488 | 32705550 | chr1 | 32756498 | 32756540 |
| chr1 | 32930458 | 32930558 | chr1 | 32938720 | 32938750 | chr1 | 33219567 | 33219596 |
| chr1 | 34628948 | 34628978 | chr1 | 34629469 | 34629728 | chr1 | 34630548 | 34630635 |
| chr1 | 34630859 | 34630978 | chr1 | 34631580 | 34631662 | chr1 | 34631933 | 34631963 |
| chr1 | 34642380 | 34642489 | chr1 | 35258637 | 35258714 | chr1 | 35351078 | 35351659 |
| chr1 | 35395526 | 35395851 | chr1 | 35664716 | 35664746 | chr1 | 36042679 | 36043489 |
| chr1 | 36563479 | 36563522 | chr1 | 36849009 | 36849038 | chr1 | 37498792 | 37498844 |
| chr] | 37498889 | 37499181 | chr1 | 37499460 | 37499682 | chr1 | 37500014 | 37500153 |
| chr1 | 37500468 | 37500574 | chr1 | 37500603 | 37500806 | chr1 | 37501072 | 37501102 |
| chr1 | 38100689 | 38100851 | chr1 | 38219712 | 38219795 | chr1 | 38230042 | 38230242 |
| chr1 | 38230283 | 38230297 | chr1 | 38230779 | 38230859 | chr1 | 38398311 | 38398348 |
| chr1 | 38412504 | 38412832 | chr1 | 38510178 | 38510217 | chr1 | 38510563 | 38510624 |
| chr1 | 38510854 | 38511119 | chr1 | 38511337 | 38611799 | chr1 | 38511822 | 38511824 |
| chr1 | 38512385 | 38512415 | chr1 | 38513244 | 38613318 | chr1 | 39269741 | 39270121 |
| chr1 | 40137898 | 40137984 | chr1 | 40237141 | 40237203 | chr1 | 40349626 | 40349647 |
| chr1 | 40708443 | 40708481 | chr1 | 40915590 | 40915620 | chr1 | 41283958 | 41284463 |
| chr1 | 41847583 | 41847702 | chr1 | 41848810 | 41848840 | chr1 | 41915253 | 41915283 |
| chr1 | 41967342 | 41967418 | chr1 | 41991640 | 41991702 | chr1 | 43400336 | 43400386 |
| chr1 | 43814994 | 43815023 | chr1 | 43834741 | 43834832 | chr1 | 43842664 | 43842779 |
| chr1 | 44068774 | 44068804 | chr1 | 44494137 | 44494153 | chr1 | 44726912 | 44727268 |
| chr1 | 44872448 | 44872722 | chr1 | 44872924 | 44873172 | chr1 | 44873510 | 44873706 |
| chr1 | 44883121 | 44883214 | chr1 | 44883752 | 44884122 | chr1 | 45308238 | 45308262 |
| chr1 | 45308592 | 45308625 | chr1 | 46632876 | 46632923 | chr1 | 46744657 | 46744733 |
| chr1 | 46913837 | 46913876 | chr1 | 46913887 | 46914245 | chr1 | 46914656 | 46914686 |
| chr1 | 46932765 | 46932905 | chr1 | 46951207 | 46951317 | chr1 | 46951645 | 46951739 |
| chr1 | 46956454 | 46956603 | chr1 | 46956823 | 46957171 | chr1 | 47009929 | 47010035 |
| chr1 | 47035373 | 47035403 | chr1 | 47078736 | 47078782 | chr1 | 47695122 | 47695422 |
| chr1 | 47696295 | 47696520 | chr1 | 47696821 | 47696964 | chr1 | 47696987 | 47697110 |
| chr1 | 47697356 | 47697510 | chr1 | 47697732 | 47697946 | chr1 | 47698007 | 47698210 |
| chr1 | 47788328 | 47788348 | chr1 | 47882063 | 47882322 | chr1 | 47882769 | 47882803 |
| chr1 | 47909718 | 47910160 | chr1 | 47910523 | 47910624 | chr1 | 47910749 | 47910914 |
| chr1 | 47911424 | 47911608 | chr1 | 47999050 | 47999163 | chr1 | 48059078 | 48059243 |
| chr1 | 49242344 | 49242533 | chr1 | 50513629 | 50513745 | chr1 | 50799278 | 50799316 |
| chr 1 | 50799394 | 50799400 | chr1 | 50880932 | 50881302 | chr1 | 50881427 | 50881956 |
| chr1 | 50882144 | 50882529 | chr1 | 50882808 | 50883611 | chr1 | 50883882 | 50883976 |
| chr1 | 50884021 | 50884352 | chr1 | 50884691 | 50884887 | chr1 | 50885336 | 50885366 |
| chr1 | 50886188 | 50887084 | chr1 | 50887176 | 50887284 | chr1 | 50888709 | 50888795 |
| chr1 | 50889124 | 50889510 | chr1 | 50889820 | 50890379 | chr1 | 50890796 | 50891595 |
| chr1 | 50892153 | 50892283 | chr1 | 50892337 | 50892351 | chr1 | 50893242 | 50893422 |
| chr1 | 50893519 | 50893877 | chr1 | 51763252 | 51763298 | chr1 | 52832687 | 52832724 |
| chr1 | 53019468 | 53019568 | chr1 | 53068166 | 53068546 | chr1 | 53098842 | 53099067 |
| chr1 | 53192045 | 53192075 | chr1 | 53308568 | 53308607 | chr1 | 53308908 | 53309248 |
| chr1 | 53528374 | 53528439 | chr1 | 53705674 | 53705701 | chr1 | 54203849 | 54204399 |
| chr1 | 54586626 | 54585736 | chr1 | 54837089 | 54837119 | chr1 | 55462673 | 55462703 |
| chr1 | 57888367 | 57888397 | chr1 | 57888987 | 57889087 | chr1 | 57889402 | 57889654 |
| chr1 | 57890431 | 57890650 | chr1 | 58715153 | 58715194 | chr1 | 58715475 | 58715854 |
| chr1 | 58715979 | 58715993 | chr1 | 61519360 | 61519394 | chr1 | 62660740 | 62660768 |
| chr1 | 62660786 | 62660861 | chr1 | 62793237 | 62793267 | chr1 | 63539509 | 63539887 |
| chr1 | 63785619 | 63785766 | chr1 | 63786079 | 63786329 | chr3 | 63787031 | 63787063 |
| chr1 | 63787302 | 63787568 | chr1 | 63788423 | 63788557 | chr1 | 63788920 | 63789496 |
| chr1 | 63789729 | 63789791 | chr1 | 63789850 | 63789912 | chr1 | 63790253 | 63790278 |
| chr1 | 63792561 | 63792648 | chr1 | 63792798 | 63793072 | chr1 | 63795263 | 63796277 |

TABLE 13-continued

| chr | start | end | chr | start | end | chr | start | end |
|---|---|---|---|---|---|---|---|---|
| chr1 | 63796498 | 63796575 | chr1 | 64240026 | 64240118 | chr1 | 64240517 | 64240673 |
| chr1 | 64734652 | 64734673 | chr1 | 64937330 | 64937542 | chr1 | 65303636 | 65303692 |
| chr1 | 65304227 | 65304256 | chr1 | 65305384 | 65305413 | chr1 | 65306926 | 65306955 |
| chr1 | 65309787 | 65309816 | chr1 | 65310487 | 65310531 | chr1 | 65311188 | 65311217 |
| chr1 | 65312331 | 65312432 | chr1 | 65731337 | 65731446 | chr1 | 65990955 | 65991018 |
| chr1 | 65991446 | 65991560 | chr1 | 65991606 | 65991757 | chr1 | 66258180 | 66258650 |
| chr1 | 66258672 | 66258774 | chr1 | 66259137 | 66259174 | chr1 | 66998790 | 66999332 |
| chr1 | 66999636 | 66999673 | chr1 | 67218064 | 67218343 | chr1 | 67390334 | 67390450 |
| chr1 | 67391067 | 67391096 | chr1 | 67773159 | 67773780 | chr1 | 70033609 | 70033916 |
| chr1 | 70034459 | 70034574 | chr1 | 70035088 | 70035537 | chr1 | 70599151 | 70599169 |
| chr1 | 70672858 | 70672878 | chr1 | 72749641 | 72749699 | chr1 | 75595819 | 75595990 |
| chr1 | 75596136 | 75596384 | chr1 | 75596687 | 75596858 | chr1 | 75596930 | 75597584 |
| chr1 | 75597923 | 75598179 | chr1 | 75598384 | 75598414 | chr1 | 75599427 | 75599621 |
| chr1 | 75600225 | 75600848 | chr1 | 75600925 | 75601118 | chr1 | 75601188 | 75601428 |
| chr1 | 75601983 | 75603052 | chr1 | 76080484 | 76080768 | chr1 | 76082129 | 76082209 |
| chr1 | 76354719 | 76354754 | chr1 | 76540450 | 76540666 | chr1 | 77333058 | 77333088 |
| chr1 | 77333384 | 77333433 | chr1 | 77334169 | 77334385 | chr1 | 77334409 | 77334756 |
| chr1 | 77747366 | 77747453 | chr1 | 77747939 | 77748235 | chr1 | 78511466 | 78512354 |
| chr1 | 78957292 | 78957522 | chr1 | 82267150 | 82267185 | chr1 | 82268573 | 82268815 |
| chr1 | 84944530 | 84944568 | chr1 | 85358752 | 85358822 | chr1 | 85463349 | 85463378 |
| chr1 | 85725508 | 85725537 | chr1 | 85725639 | 85725668 | chr1 | 86621660 | 86622127 |
| chr1 | 86622526 | 86622551 | chr1 | 86860809 | 86860949 | chr1 | 87617774 | 87617807 |
| chr1 | 90099997 | 90100084 | chr1 | 90309292 | 90309490 | chr1 | 91172012 | 91172677 |
| chr1 | 91177941 | 91178207 | chr1 | 91180075 | 91180306 | chr1 | 91181932 | 91182132 |
| chr1 | 91182338 | 91183195 | chr1 | 91183251 | 91183610 | chr1 | 91183951 | 91183986 |
| chr1 | 91184423 | 91184672 | chr1 | 91186190 | 91185308 | chr1 | 91185348 | 91185707 |
| chr1 | 91188983 | 91189383 | chr1 | 91189688 | 91190380 | chr1 | 91190896 | 91190948 |
| chr1 | 91190985 | 91191234 | chr1 | 91191290 | 91191310 | chr1 | 91192274 | 91192576 |
| chr1 | 91194414 | 91194569 | chr1 | 91195117 | 91195390 | chr1 | 91195879 | 91196194 |
| chr1 | 91196226 | 91196502 | chr1 | 91316261 | 91316313 | chr1 | 91316627 | 91316682 |
| chr1 | 91869988 | 91870018 | chr1 | 92948324 | 92948597 | chr1 | 92948841 | 92948976 |
| chr1 | 92952145 | 92952655 | chr1 | 94147641 | 94147670 | chr1 | 94147816 | 94147845 |
| chr1 | 94343568 | 94343596 | chr1 | 95006795 | 95006902 | chr1 | 97185262 | 97185406 |
| chr1 | 98510791 | 98511335 | chr1 | 98511628 | 98511922 | chr1 | 98514225 | 98514255 |
| chr1 | 98515142 | 98515191 | chr1 | 98515256 | 98515319 | chr1 | 98519023 | 98519675 |
| chr1 | 99469682 | 99469696 | chr1 | 99469760 | 99469788 | chr1 | 99470785 | 99470847 |
| chr1 | 100437150 | 100437172 | chr1 | 101004456 | 101004737 | chr1 | 101005071 | 101005144 |
| chr1 | 101005360 | 101005675 | chr1 | 101702504 | 101702616 | chr1 | 101703612 | 101703642 |
| chr1 | 103574508 | 103574537 | chr1 | 107682735 | 107682977 | chr1 | 107683439 | 107683517 |
| chr1 | 107684240 | 107684439 | chr1 | 108507063 | 108507076 | chr1 | 108507320 | 108507375 |
| chr1 | 108507495 | 108507497 | chr1 | 108507717 | 108507810 | chr1 | 108508052 | 108508640 |
| chr1 | 109203609 | 109203672 | chr1 | 109585463 | 109585488 | chr1 | 109631646 | 109631682 |
| chr1 | 109644251 | 109644336 | chr1 | 110610586 | 110610897 | chr1 | 110611046 | 110611276 |
| chr1 | 110611435 | 110611513 | chr1 | 110611654 | 110611965 | chr1 | 110626684 | 110627578 |
| chr1 | 110672889 | 110673233 | chr1 | 110692973 | 110693496 | chr1 | 110693737 | 110694117 |
| chr1 | 110754003 | 110754101 | chr1 | 110754309 | 110754356 | chr1 | 110883542 | 110883965 |
| chr1 | 111097906 | 111097936 | chr1 | 111098195 | 111098316 | chr1 | 111216763 | 111216972 |
| chr1 | 111217195 | 111217891 | chr1 | 111217924 | 111217982 | chr1 | 111506090 | 111506212 |
| chr1 | 111813546 | 111813587 | chr1 | 112084954 | 112084984 | chr1 | 114428007 | 114428084 |
| chr1 | 114448967 | 114448990 | chr1 | 114695439 | 114695736 | chr1 | 114695800 | 114695943 |
| chr1 | 114696350 | 114696463 | chr1 | 114696541 | 114696712 | chr1 | 115256514 | 115256552 |
| chr1 | 115258729 | 115258772 | chr1 | 115631867 | 115631915 | chr1 | 115632469 | 115632555 |
| chr1 | 115880184 | 115880395 | chr1 | 115880873 | 115881042 | chr1 | 116214104 | 116214318 |
| chr1 | 116371139 | 116371201 | chr1 | 116380651 | 116381287 | chr1 | 116382387 | 116382478 |
| chr1 | 119522074 | 119522434 | chr1 | 119522839 | 119522853 | chr1 | 119522926 | 119522940 |
| chr1 | 119527237 | 119527391 | chr1 | 119527623 | 119527652 | chr1 | 119528653 | 119529118 |
| chr1 | 119529804 | 119529839 | chr1 | 119530100 | 119530148 | chr1 | 119530202 | 119530507 |
| chr1 | 119530554 | 119530725 | chr1 | 119531029 | 119531157 | chr1 | 119532318 | 119532320 |
| chr1 | 119535908 | 119536377 | chr1 | 119542322 | 119542352 | chr1 | 119543070 | 119543214 |
| chr1 | 119543532 | 119544182 | chr1 | 119548823 | 119548853 | chr1 | 119549758 | 119549734 |
| chr1 | 119549915 | 119549929 | chr1 | 119550155 | 119550278 | chr1 | 119550533 | 119550633 |
| chr1 | 119551014 | 119551269 | chr1 | 150603138 | 150603154 | chr1 | 150941425 | 150941756 |
| chr1 | 151169637 | 151169757 | chr1 | 151170057 | 151170206 | chr1 | 151300888 | 151300918 |
| chr1 | 151362740 | 151362779 | chr1 | 151693945 | 151694351 | chr1 | 151812413 | 151812442 |
| chr1 | 152009415 | 152009510 | chr1 | 152085398 | 152085504 | chr1 | 152488129 | 152488197 |
| chr1 | 153539476 | 153539637 | chr1 | 153540095 | 153540154 | chr1 | 153651965 | 153652379 |
| chr1 | 153937124 | 153937167 | chr1 | 154127987 | 154128016 | chr1 | 154298320 | 154298557 |
| chr1 | 154475372 | 154475531 | chr1 | 154516810 | 154516845 | chr1 | 155043331 | 155043657 |
| chr1 | 155161778 | 155162033 | chr1 | 155164415 | 155164455 | chr1 | 155283218 | 155283248 |
| chr1 | 155578888 | 155578921 | chr1 | 155826292 | 155826336 | chr1 | 155874151 | 155874300 |
| chr1 | 155874508 | 155874546 | chr1 | 155954282 | 155954396 | chr1 | 156010523 | 156010548 |
| chr1 | 156215329 | 156215359 | chr1 | 156215607 | 156215805 | chr1 | 156357993 | 156358508 |
| chr1 | 156390135 | 156390698 | chr1 | 156405635 | 156406070 | chr1 | 156406105 | 156406431 |
| chr1 | 156432124 | 156432321 | chr1 | 156594974 | 156595021 | chr1 | 156611889 | 156611943 |
| chr1 | 156611994 | 156612119 | chr1 | 156626589 | 156626658 | chr1 | 156626891 | 166627018 |
| chr1 | 156546278 | 156546307 | chr1 | 156646593 | 156646596 | chr1 | 156646635 | 156646547 |
| chr1 | 156814933 | 156814952 | chr1 | 156815031 | 156815146 | chr1 | 156815445 | 156815745 |
| chr1 | 156830269 | 156830348 | chr1 | 156838167 | 156838320 | chr1 | 156863107 | 156863331 |

TABLE 13-continued

| chr | start | end | chr | start | end | chr | start | end |
|---|---|---|---|---|---|---|---|---|
| chr1 | 156863662 | 156863724 | chr1 | 157247368 | 157247388 | chr1 | 157458909 | 157458935 |
| chr1 | 157895413 | 157895443 | chr1 | 158669704 | 158669882 | chr1 | 158687415 | 158687550 |
| chr1 | 159140357 | 159140386 | chr1 | 159158348 | 159158368 | chr1 | 159158472 | 159158511 |
| chr1 | 159187279 | 159187429 | chr1 | 159258862 | 159258891 | chr1 | 159337517 | 159337615 |
| chr1 | 159409192 | 159409221 | chr1 | 160693934 | 160693958 | chr1 | 160992336 | 160992372 |
| chr1 | 161007587 | 161007746 | chr1 | 161086730 | 161086772 | chr1 | 161228659 | 161228891 |
| chr1 | 161275564 | 161275578 | chr1 | 161275640 | 161276026 | chr1 | 161368993 | 161369405 |
| chr1 | 161369859 | 161369945 | chr1 | 161442441 | 161442471 | chr1 | 161466301 | 161466324 |
| chr1 | 161471748 | 161471779 | chr1 | 161591472 | 161591546 | chr1 | 162724401 | 162724430 |
| chr1 | 162729615 | 162729686 | chr1 | 162748392 | 162748421 | chr1 | 162792306 | 162792533 |
| chr1 | 163393034 | 163393064 | chr1 | 164290615 | 164290671 | chr1 | 164730649 | 164730693 |
| chr1 | 165086988 | 165087027 | chr1 | 165205079 | 165205146 | chr1 | 165321747 | 165321786 |
| chr1 | 165323151 | 165323181 | chr1 | 165324196 | 165324249 | chr1 | 165324305 | 165324357 |
| chr1 | 165324488 | 165324668 | chr1 | 165325108 | 165325355 | chr1 | 165325395 | 165325521 |
| chr1 | 165325896 | 165325950 | chr1 | 165326204 | 165326204 | chr1 | 165326297 | 165326469 |
| chr1 | 165414191 | 165414272 | chr1 | 166134247 | 166134306 | chr1 | 166134728 | 166134796 |
| chr1 | 166135193 | 166135281 | chr1 | 166853563 | 166853592 | chr1 | 166890292 | 166890436 |
| chr1 | 166916866 | 166916920 | chr1 | 166916937 | 166916949 | chr1 | 167090617 | 167090757 |
| chr1 | 167599179 | 167599330 | chr1 | 167599616 | 167599844 | chr1 | 167823370 | 167823461 |
| chr1 | 169396376 | 169396688 | chr1 | 169396731 | 169396923 | chr1 | 169838016 | 169838187 |
| chr1 | 169930112 | 169930305 | chr1 | 170629540 | 170629569 | chr1 | 170629999 | 170630029 |
| chr1 | 170630456 | 170630810 | chr1 | 170631084 | 170631163 | chr1 | 170631477 | 170631559 |
| chr1 | 170633607 | 170633637 | chr1 | 170637666 | 170637796 | chr1 | 170640517 | 170640624 |
| chr1 | 170640665 | 170640691 | chr1 | 171625525 | 171625543 | chr1 | 171810200 | 171810972 |
| chr1 | 173638647 | 173639085 | chr1 | 175346381 | 175346551 | chr1 | 175388664 | 175388682 |
| chr1 | 177133721 | 177133814 | chr1 | 177140105 | 177140173 | chr1 | 177140305 | 177140714 |
| chr1 | 177150773 | 177150803 | chr1 | 178063112 | 178063150 | chr1 | 179544967 | 179545098 |
| chr1 | 179712164 | 179712338 | chr1 | 179712411 | 179712553 | chr1 | 179712568 | 179712733 |
| chr1 | 179712831 | 179713174 | chr1 | 180198061 | 180198209 | chr1 | 180202649 | 180203016 |
| chr1 | 180203413 | 180203607 | chr1 | 180203634 | 180204619 | chr1 | 180204898 | 180204924 |
| chr1 | 180235730 | 180235760 | chr1 | 180882576 | 180882695 | chr1 | 180919686 | 180919718 |
| chr1 | 180925271 | 180925402 | chr1 | 181287679 | 181287757 | chr1 | 181288014 | 181288188 |
| chr1 | 181451407 | 181452120 | chr1 | 181452871 | 181452967 | chr1 | 181454873 | 181454912 |
| chr1 | 181455183 | 181455263 | chr1 | 182584048 | 182584339 | chr1 | 182584404 | 182584613 |
| chr1 | 182807578 | 182807660 | chr1 | 182921839 | 182921868 | chr1 | 183129382 | 183129530 |
| chr1 | 183386150 | 183386288 | chr1 | 183386599 | 183386626 | chr1 | 183386947 | 183386964 |
| chr1 | 183387266 | 183387319 | chr1 | 183462983 | 183463024 | chr1 | 183774244 | 183774363 |
| chr1 | 184005701 | 184005814 | chr1 | 185073818 | 185073966 | chr1 | 186570930 | 186570950 |
| chr1 | 190444855 | 190444885 | chr1 | 190445181 | 190445276 | chr1 | 190447389 | 190447519 |
| chr1 | 195732322 | 195732521 | chr1 | 196577628 | 196577858 | chr1 | 196578101 | 196578150 |
| chr1 | 197879400 | 197879660 | chr1 | 197879717 | 197880156 | chr1 | 197882140 | 197882201 |
| chr1 | 197882453 | 197882611 | chr1 | 197887052 | 197887066 | chr1 | 197887147 | 197887456 |
| chr1 | 197887707 | 197887741 | chr1 | 197888052 | 197888121 | chr1 | 197888181 | 197888319 |
| chr1 | 197888643 | 197889286 | chr1 | 200009357 | 200009450 | chr1 | 200009750 | 200010114 |
| chr1 | 200011323 | 200012227 | chr1 | 200591054 | 200591080 | chr1 | 201368582 | 201368727 |
| chr1 | 201476501 | 201476619 | chr1 | 201983113 | 201983200 | chr1 | 202081766 | 202081804 |
| chr1 | 202183371 | 202183401 | chr1 | 202531939 | 202532087 | chr1 | 202679215 | 202679518 |
| chr1 | 203298307 | 203298449 | chr1 | 203429564 | 203429594 | chr1 | 203681253 | 203681362 |
| chr1 | 204333609 | 204333668 | chr1 | 204478326 | 204478427 | chr1 | 204499813 | 204499842 |
| chr1 | 204524704 | 204524724 | chr1 | 204531203 | 204531540 | chr1 | 204531600 | 204531757 |
| chr1 | 204653561 | 204653595 | chr1 | 204653793 | 204653807 | chr1 | 205312596 | 205312911 |
| chr1 | 205424654 | 205424957 | chr1 | 205537663 | 205537772 | chr1 | 207200870 | 207200962 |
| chr1 | 207227527 | 207227556 | chr1 | 207669496 | 207669787 | chr1 | 207669829 | 207670060 |
| chr1 | 207818394 | 207818396 | chr1 | 207818434 | 207818493 | chr1 | 208084289 | 208084488 |
| chr1 | 209381132 | 209381165 | chr1 | 209604382 | 209604597 | chr1 | 209605386 | 209605415 |
| chr1 | 209849170 | 209849199 | chr1 | 209849430 | 209849459 | chr1 | 210111146 | 210111176 |
| chr1 | 210111388 | 210111421 | chr1 | 210111797 | 210111922 | chr1 | 210112037 | 210112140 |
| chr1 | 211847706 | 211847787 | chr1 | 212963883 | 212963987 | chr1 | 213123871 | 213123979 |
| chr1 | 213124669 | 213124910 | chr1 | 214156419 | 214156928 | chr1 | 214158838 | 214158910 |
| chr1 | 214160107 | 214160184 | chr1 | 214360675 | 214360858 | chr1 | 214360927 | 214360968 |
| chr1 | 214724531 | 214724561 | chr1 | 215255094 | 215255799 | chr1 | 216897216 | 216897307 |
| chr1 | 217307385 | 217308274 | chr1 | 217309007 | 217309105 | chr1 | 217309764 | 217309816 |
| chr1 | 217311265 | 217311839 | chr1 | 217313042 | 217313042 | chr1 | 217313069 | 217313747 |
| chr1 | 217805158 | 217805247 | chr1 | 218520096 | 218520291 | chr1 | 218520310 | 218520399 |
| chr1 | 218520775 | 218520805 | chr1 | 219346992 | 219347035 | chr1 | 219347429 | 219347472 |
| chr1 | 220101145 | 220101210 | chr1 | 220101371 | 220101385 | chr1 | 220101683 | 220101712 |
| chr1 | 220132075 | 220132111 | chr1 | 220636466 | 220636510 | chr1 | 220700814 | 220700897 |
| chr1 | 221052038 | 221052492 | chr1 | 221053610 | 221053862 | chr1 | 221067506 | 221067688 |
| chr1 | 221068156 | 221068185 | chr1 | 221068793 | 221069150 | chr1 | 221510339 | 221510368 |
| chr1 | 221737191 | 221737220 | chr1 | 223302825 | 223302890 | chr1 | 223538344 | 223538641 |
| chr1 | 223936633 | 223936752 | chr1 | 223936996 | 223937057 | chr1 | 224363560 | 224363589 |
| chr1 | 224400490 | 224400524 | chr1 | 224493975 | 224493999 | chr1 | 224528814 | 224528844 |
| chr1 | 224803717 | 224803751 | chr1 | 224804097 | 224804295 | chr1 | 224804396 | 224804686 |
| chr1 | 224804847 | 224804910 | chr1 | 224805198 | 224805751 | chr1 | 226411247 | 226411273 |
| chr1 | 226411700 | 226411832 | chr1 | 226814346 | 226814408 | chr1 | 226925067 | 226925195 |
| chr1 | 226997660 | 226997719 | chr1 | 227729830 | 227730075 | chr1 | 227748700 | 227748733 |
| chr1 | 228195377 | 228196349 | chr1 | 228201221 | 228201251 | chr1 | 228247998 | 228248027 |
| chr1 | 228248302 | 228248332 | chr1 | 228345999 | 228346195 | chr1 | 228461158 | 228461197 |

TABLE 13-continued

| chr | start | end | chr | start | end | chr | start | end |
|---|---|---|---|---|---|---|---|---|
| chr1 | 228463311 | 228463706 | chr1 | 228528840 | 228529016 | chr1 | 228558699 | 228559238 |
| chr1 | 228566622 | 228566672 | chr1 | 228604124 | 228604254 | chr1 | 228633990 | 228634261 |
| chr1 | 228645140 | 228645243 | chr1 | 228645306 | 228645734 | chr1 | 228646195 | 228646238 |
| chr1 | 228651432 | 228651626 | chr1 | 228651879 | 228651901 | chr1 | 228652224 | 228652452 |
| chr1 | 228652509 | 228652629 | chr1 | 228871865 | 228872003 | chr1 | 229542838 | 229542952 |
| chr1 | 229543553 | 229543603 | chr1 | 229566753 | 229567276 | chr1 | 229567770 | 229567992 |
| chr1 | 229568158 | 229568204 | chr1 | 229569810 | 229569852 | chr1 | 230404217 | 230404263 |
| chr1 | 230561779 | 230561824 | chr1 | 231297103 | 231297221 | chr1 | 231298595 | 231298707 |
| chr1 | 232765195 | 232765301 | chr1 | 233465473 | 233465503 | chr1 | 233750082 | 233750302 |
| chr1 | 234040247 | 234040319 | chr1 | 234040886 | 234040973 | chr1 | 234041416 | 234041624 |
| chr1 | 234349988 | 234350100 | chr1 | 234445373 | 234445403 | chr1 | 234620866 | 234620979 |
| chr1 | 234798171 | 234798201 | chr1 | 234839889 | 234840058 | chr1 | 234844955 | 234845079 |
| chr1 | 234845467 | 234845497 | chr1 | 235665700 | 235665736 | chr1 | 235813781 | 235813796 |
| chr1 | 235814010 | 235814202 | chr1 | 235814447 | 235814476 | chr1 | 236227637 | 236227743 |
| chr1 | 236227770 | 236227920 | chr1 | 236228022 | 236228096 | chr1 | 236228585 | 236228623 |
| chr1 | 236228706 | 236228789 | chr1 | 236559176 | 236559206 | chr1 | 236559257 | 236559271 |
| chr1 | 236849457 | 236849505 | chr1 | 237205159 | 237205188 | chr1 | 237206102 | 237206265 |
| chr1 | 237206512 | 237206735 | chr1 | 238024448 | 238024477 | chr1 | 239550594 | 239551193 |
| chr1 | 240118848 | 240118973 | chr1 | 240161123 | 240161380 | chr1 | 240254944 | 240255011 |
| chr1 | 240255361 | 240255500 | chr1 | 240255819 | 240256158 | chr1 | 240256663 | 240256721 |
| chr1 | 240775425 | 240775455 | chr1 | 241052096 | 241052126 | chr1 | 241520296 | 241520345 |
| chr1 | 241520583 | 241520612 | chr1 | 241587034 | 241587113 | chr1 | 241587587 | 241587797 |
| chr1 | 241912749 | 241912778 | chr1 | 242686734 | 242687688 | chr1 | 242688184 | 242688243 |
| chr1 | 242688477 | 242688695 | chr1 | 243646610 | 243646673 | chr1 | 243859000 | 243859029 |
| chr1 | 244014221 | 244014376 | chr1 | 244080672 | 244080702 | chr1 | 244080963 | 244081061 |
| chr1 | 244081078 | 244081203 | chr1 | 244893214 | 244893295 | chr1 | 245032517 | 245032603 |
| chr1 | 245135753 | 245135849 | chr1 | 245494495 | 245494578 | chr1 | 245849914 | 245849944 |
| chr1 | 246198078 | 246198203 | chr1 | 246330309 | 246330409 | chr1 | 246488175 | 246488316 |
| chr1 | 247496038 | 247496057 | chr1 | 247608784 | 247608814 | chr1 | 248002278 | 248002358 |
| chr1 | 248020516 | 248020630 | chr1 | 248020957 | 248021349 | chr1 | 248028015 | 248028202 |
| chr1 | 248074729 | 248074768 | chr1 | 248074828 | 248074927 | chr1 | 248099751 | 248099809 |
| chr1 | 248328701 | 248328841 | chr1 | 249121622 | 249121704 | chr2 | 46214 | 46450 |
| chr2 | 264163 | 264204 | chr2 | 287580 | 287641 | chr2 | 288404 | 288470 |
| chr2 | 468424 | 468672 | chr2 | 496228 | 496380 | chr2 | 602657 | 602687 |
| chr2 | 720836 | 720894 | chr2 | 875961 | 875991 | chr2 | 945913 | 946000 |
| chr2 | 946208 | 946217 | chr2 | 946526 | 946566 | chr2 | 946917 | 947043 |
| chr2 | 947127 | 947159 | chr2 | 1652837 | 1653230 | chr2 | 1670168 | 1670216 |
| chr2 | 1746614 | 1747032 | chr2 | 1747670 | 1748007 | chr2 | 1748397 | 1748890 |
| chr2 | 2321773 | 2321802 | chr2 | 2336413 | 2336442 | chr2 | 2646900 | 2646930 |
| chr2 | 2672620 | 2672732 | chr2 | 2844720 | 2844750 | chr2 | 2893165 | 2893195 |
| chr2 | 3259989 | 3260103 | chr2 | 4019911 | 4020036 | chr2 | 4050752 | 4050781 |
| chr2 | 5831178 | 5831204 | chr2 | 5831238 | 5831324 | chr2 | 5831789 | 5831819 |
| chr2 | 5833283 | 5833432 | chr2 | 5833500 | 5833639 | chr2 | 5833735 | 5834028 |
| chr2 | 5836085 | 5836253 | chr2 | 5836548 | 5836574 | chr2 | 5836622 | 5836744 |
| chr2 | 5836828 | 5836991 | chr2 | 5837353 | 5837414 | chr2 | 5866098 | 5866211 |
| chr2 | 2164467 | 7164788 | chr2 | 7571577 | 7571747 | chr2 | 8735932 | 8736064 |
| chr2 | 9134404 | 9134493 | chr2 | 9192356 | 9192379 | chr2 | 9289969 | 9290114 |
| chr2 | 9960734 | 9960764 | chr2 | 10115730 | 10115751 | chr2 | 10153062 | 10153325 |
| chr2 | 10154930 | 10155024 | chr2 | 10155264 | 10155298 | chr2 | 10156313 | 10156389 |
| chr2 | 10182827 | 10182904 | chr2 | 10369155 | 10369242 | chr2 | 10408398 | 10408459 |
| chr2 | 10688874 | 10688904 | chr2 | 11052517 | 11052559 | chr2 | 11142275 | 11142315 |
| chr2 | 11672746 | 11672775 | chr2 | 11809957 | 11810115 | chr2 | 11903450 | 11903486 |
| chr2 | 12246114 | 12246196 | chr2 | 12858452 | 12858618 | chr2 | 14772761 | 14772823 |
| chr2 | 14774281 | 14774567 | chr2 | 17719688 | 17719812 | chr2 | 18059035 | 18059085 |
| chr2 | 18059781 | 18059841 | chr2 | 19550214 | 19550244 | chr2 | 19551322 | 19551366 |
| chr2 | 19556318 | 19556672 | chr2 | 19557068 | 19557098 | chr2 | 19557685 | 19557727 |
| chr2 | 19558832 | 19558893 | chr2 | 19561131 | 19561316 | chr2 | 19561524 | 19561685 |
| chr2 | 19563358 | 19563433 | chr2 | 20068798 | 20068885 | chr2 | 20442466 | 20442498 |
| chr2 | 20642625 | 20642648 | chr2 | 20865636 | 20865927 | chr2 | 25374762 | 25374804 |
| chr2 | 25391013 | 25391212 | chr2 | 25391684 | 25391725 | chr2 | 25438821 | 25438871 |
| chr2 | 25439139 | 25439383 | chr2 | 25600736 | 25600804 | chr2 | 26372967 | 26372997 |
| chr2 | 26395447 | 26395556 | chr2 | 26402030 | 26402060 | chr2 | 26407744 | 26407921 |
| chr2 | 26521972 | 26522127 | chr2 | 26915763 | 26916066 | chr2 | 26916089 | 26916259 |
| chr2 | 27070324 | 27070414 | chr2 | 27071240 | 27071346 | chr2 | 27072492 | 27072534 |
| chr2 | 27072822 | 27072989 | chr2 | 27356168 | 27356198 | chr2 | 27578242 | 27578396 |
| chr2 | 27665125 | 27665154 | chr2 | 27665506 | 27665711 | chr2 | 27887525 | 27887555 |
| chr2 | 29033336 | 29033697 | chr2 | 29091592 | 29091625 | chr2 | 29338159 | 29338747 |
| chr2 | 29338810 | 29338969 | chr2 | 29420483 | 29420512 | chr2 | 29432640 | 29432696 |
| chr2 | 29436844 | 29436888 | chr2 | 29443573 | 29443710 | chr2 | 29445198 | 29445482 |
| chr2 | 29446361 | 29446396 | chr2 | 30143304 | 30143322 | chr2 | 30143383 | 30143492 |
| chr2 | 30144041 | 30144150 | chr2 | 30144175 | 30144411 | chr2 | 30453785 | 30453941 |
| chr2 | 31360306 | 31360589 | chr2 | 31360631 | 31360755 | chr2 | 31360804 | 31360831 |
| chr2 | 31361089 | 31361118 | chr2 | 31361356 | 31361385 | chr2 | 31456682 | 31457039 |
| chr2 | 32504334 | 32504378 | chr2 | 32580386 | 32580431 | chr2 | 38302370 | 38302876 |
| chr2 | 38365727 | 38365748 | chr2 | 38551124 | 38551167 | chr2 | 38727561 | 38727707 |
| chr2 | 38762382 | 38762412 | chr2 | 39187218 | 39187237 | chr2 | 39187544 | 39187722 |
| chr2 | 39893090 | 39893501 | chr2 | 39893972 | 39894059 | chr2 | 40678603 | 40678872 |
| chr2 | 40678932 | 40679604 | chr2 | 42274595 | 42274633 | chr2 | 42329431 | 42329444 |

TABLE 13-continued

| chr | start | end | chr | start | end | chr | start | end |
|---|---|---|---|---|---|---|---|---|
| chr2 | 42329494 | 42329666 | chr2 | 42720262 | 42720446 | chr2 | 43019599 | 43019868 |
| chr2 | 43451909 | 43452327 | chr2 | 43824133 | 43824153 | chr2 | 44497708 | 44497875 |
| chr2 | 44809187 | 44809217 | chr2 | 45028988 | 45029058 | chr2 | 45029184 | 45029371 |
| chr2 | 45029682 | 45029712 | chr2 | 45155125 | 45155210 | chr2 | 45155356 | 45156811 |
| chr2 | 45156833 | 45157711 | chr2 | 45159956 | 45160267 | chr2 | 45160596 | 45160634 |
| chr2 | 45161663 | 45162112 | chr2 | 45162394 | 45162481 | chr2 | 45162751 | 45162913 |
| chr2 | 45164663 | 45164693 | chr2 | 45165564 | 45165594 | chr2 | 45168803 | 45168833 |
| chr2 | 45169446 | 45170029 | chr2 | 45171385 | 45171563 | chr2 | 45171837 | 45171862 |
| chr2 | 45176601 | 45176768 | chr2 | 45179620 | 45179650 | chr2 | 45179939 | 45180203 |
| chr2 | 45181520 | 45181672 | chr2 | 45181887 | 45182001 | chr2 | 45228625 | 45228730 |
| chr2 | 45231320 | 45231396 | chr2 | 45231805 | 45232131 | chr2 | 45233385 | 45233586 |
| chr2 | 45235594 | 45235926 | chr2 | 45237673 | 45237795 | chr2 | 45240548 | 45240630 |
| chr2 | 45240764 | 45240784 | chr2 | 45241136 | 45241168 | chr2 | 45395854 | 45395920 |
| chr2 | 45396315 | 45396451 | chr2 | 45396688 | 45396995 | chr2 | 46526302 | 46526448 |
| chr2 | 42193930 | 42194093 | chr2 | 47200591 | 47200621 | chr2 | 47249725 | 47249848 |
| chr2 | 47598278 | 47598518 | chr2 | 47598578 | 47598620 | chr2 | 47748140 | 47748494 |
| chr2 | 47797043 | 47797818 | chr2 | 47798180 | 47798663 | chr2 | 47798954 | 47799032 |
| chr2 | 48636504 | 48636647 | chr2 | 48982582 | 48982700 | chr2 | 48982754 | 48982866 |
| chr2 | 50573595 | 50573638 | chr2 | 50573692 | 50573865 | chr2 | 50574121 | 50574355 |
| chr2 | 50574402 | 50574684 | chr2 | 50574739 | 50574859 | chr2 | 55289094 | 55289274 |
| chr2 | 56149836 | 56149866 | chr2 | 56150729 | 56151193 | chr2 | 56410817 | 56410996 |
| chr2 | 56411691 | 56411733 | chr2 | 58656049 | 58656125 | chr2 | 60706759 | 60706804 |
| chr2 | 60796587 | 60796617 | chr2 | 60797137 | 60797281 | chr2 | 61135115 | 61135137 |
| chr2 | 62798343 | 62798386 | chr2 | 63278962 | 63278992 | chr2 | 63280952 | 63281651 |
| chr2 | 63282716 | 63282786 | chr2 | 63283014 | 63283027 | chr2 | 63283952 | 63284146 |
| chr2 | 63284777 | 63284811 | chr2 | 63285081 | 63286047 | chr2 | 63286359 | 63286584 |
| chr2 | 63286694 | 63286747 | chr2 | 63287083 | 63287368 | chr2 | 65251310 | 65251340 |
| chr2 | 66652863 | 66652963 | chr2 | 66653238 | 66653496 | chr2 | 66653764 | 66653914 |
| chr2 | 66660650 | 66660888 | chr2 | 66662749 | 66662824 | chr2 | 66808525 | 66808633 |
| chr2 | 66808727 | 66809361 | chr2 | 67625453 | 67625492 | chr2 | 67625732 | 67625770 |
| chr2 | 67626102 | 67626257 | chr2 | 68287783 | 68287799 | chr2 | 68546324 | 68546516 |
| chr2 | 68546553 | 68546892 | chr2 | 68559343 | 68559365 | chr2 | 68672853 | 68672938 |
| chr2 | 69027024 | 69027053 | chr2 | 70418608 | 70418627 | chr2 | 71355038 | 71355117 |
| chr2 | 71503790 | 71503823 | chr2 | 71504103 | 71504148 | chr2 | 71680833 | 71680863 |
| chr2 | 71693374 | 71693593 | chr2 | 72374375 | 72374432 | chr2 | 72374714 | 72374765 |
| chr2 | 73145640 | 73145694 | chr2 | 73145924 | 73146021 | chr2 | 73147473 | 73147527 |
| chr2 | 73147967 | 73148066 | chr2 | 73148175 | 73148243 | chr2 | 73150924 | 73150954 |
| chr2 | 73151187 | 73151831 | chr2 | 73152740 | 73152754 | chr2 | 73416356 | 73416386 |
| chr2 | 73429523 | 73429614 | chr2 | 73429977 | 73430069 | chr2 | 73430322 | 73430372 |
| chr2 | 73430443 | 73430743 | chr2 | 73440250 | 73440293 | chr2 | 73518448 | 73518919 |
| chr2 | 73519579 | 73519841 | chr2 | 74010528 | 74010621 | chr2 | 74153198 | 74153227 |
| chr2 | 74426185 | 74426214 | chr2 | 74454074 | 74454261 | chr2 | 74647864 | 74647906 |
| chr2 | 74726744 | 74726774 | chr2 | 74740852 | 74741387 | chr2 | 74741835 | 74741844 |
| chr2 | 74741873 | 74741955 | chr2 | 74742325 | 74742647 | chr2 | 74742694 | 74743144 |
| chr2 | 74782081 | 74782087 | chr2 | 74782219 | 74782271 | chr2 | 75427040 | 75427114 |
| chr2 | 75427369 | 75427399 | chr2 | 75427930 | 75428177 | chr2 | 75720510 | 75720541 |
| chr2 | 79347459 | 79347546 | chr2 | 80529378 | 80529443 | chr2 | 80529662 | 80529908 |
| chr2 | 80529986 | 80530022 | chr2 | 80530505 | 80530558 | chr2 | 80531725 | 80531755 |
| chr2 | 80549585 | 80549745 | chr2 | 85107454 | 85107538 | chr2 | 85361467 | 85361528 |
| chr2 | 86263223 | 86263270 | chr2 | 86791221 | 86791251 | chr2 | 87016579 | 87016636 |
| chr2 | 87017796 | 87018396 | chr2 | 87036611 | 87036640 | chr2 | 88469312 | 88469398 |
| chr2 | 88751281 | 88751419 | chr2 | 88751461 | 88751800 | chr2 | 88752055 | 88752285 |
| chr2 | 88752603 | 88752785 | chr2 | 88990189 | 88990264 | chr2 | 89064806 | 89064975 |
| chr2 | 89065129 | 89065278 | chr2 | 95663969 | 95664014 | chr2 | 95690747 | 95690793 |
| chr2 | 95691036 | 95691269 | chr2 | 95691530 | 95691769 | chr2 | 95691994 | 95692480 |
| chr2 | 95941678 | 95941812 | chr2 | 96070057 | 96070081 | chr2 | 96990898 | 96991316 |
| chr2 | 97193252 | 97193626 | chr2 | 97427515 | 97428093 | chr2 | 98703323 | 98703475 |
| chr2 | 98703675 | 98703736 | chr2 | 98962898 | 98962900 | chr2 | 98963329 | 98963599 |
| chr2 | 98963869 | 98964200 | chr2 | 98964596 | 98964645 | chr2 | 99439369 | 99439507 |
| chr2 | 99553391 | 99553656 | chr2 | 99796295 | 99796330 | chr2 | 99798646 | 99798750 |
| chr2 | 99799050 | 99799153 | chr2 | 100618451 | 100618480 | chr2 | 100937836 | 100938209 |
| chr2 | 100938330 | 100938544 | chr2 | 100938575 | 100938809 | chr2 | 100938985 | 100939155 |
| chr2 | 101009832 | 101009927 | chr2 | 101034242 | 101034293 | chr2 | 101436632 | 101436708 |
| chr2 | 101666893 | 101667004 | chr2 | 102091180 | 102091335 | chr2 | 103236165 | 103236292 |
| chr2 | 105459081 | 105459151 | chr2 | 105459908 | 105460599 | chr2 | 105460701 | 105460951 |
| chr2 | 105461187 | 105461243 | chr2 | 105461564 | 105461667 | chr2 | 105461700 | 105461896 |
| chr2 | 105462165 | 105462222 | chr2 | 105468791 | 105468908 | chr2 | 105469645 | 105469856 |
| chr2 | 105469881 | 105470091 | chr2 | 105470350 | 105470840 | chr2 | 105472231 | 105472425 |
| chr2 | 105472713 | 105472845 | chr2 | 105473248 | 105473521 | chr2 | 105478762 | 105479089 |
| chr2 | 105483655 | 105483719 | chr2 | 105484450 | 105484522 | chr2 | 105488437 | 105488496 |
| chr2 | 105760981 | 105761009 | chr2 | 105937344 | 105937498 | chr2 | 106060615 | 106060792 |
| chr2 | 106681733 | 106681767 | chr2 | 106682012 | 106682098 | chr2 | 106730223 | 106730256 |
| chr2 | 106959368 | 106959568 | chr2 | 106969916 | 106959988 | chr2 | 107103865 | 107103928 |
| chr2 | 107502600 | 107502729 | chr2 | 107503532 | 107503561 | chr2 | 107503884 | 107504018 |
| chr2 | 109335133 | 109335166 | chr2 | 109648080 | 109648222 | chr2 | 109745989 | 109746079 |
| chr2 | 109746289 | 109746387 | chr2 | 109746463 | 109746477 | chr2 | 110015080 | 110015110 |
| chr2 | 110370941 | 110371219 | chr2 | 110873016 | 110873045 | chr2 | 111544817 | 111544847 |
| chr2 | 111875191 | 111875611 | chr2 | 112657033 | 112657092 | chr2 | 113227125 | 113227225 |

TABLE 13-continued

| chr | start | end | chr | start | end | chr | start | end |
|---|---|---|---|---|---|---|---|---|
| chr2 | 113594639 | 113594668 | chr2 | 113931503 | 113931532 | chr2 | 114256978 | 114257137 |
| chr2 | 114261300 | 114261458 | chr2 | 114470172 | 114470201 | chr2 | 115918661 | 115918892 |
| chr2 | 115919338 | 115919424 | chr2 | 115919831 | 115920534 | chr2 | 118981161 | 118981856 |
| chr2 | 118981946 | 118982147 | chr2 | 118982254 | 118982497 | chr2 | 119067636 | 119068049 |
| chr2 | 119532161 | 119532255 | chr2 | 119566239 | 119566272 | chr2 | 119591351 | 119591465 |
| chr2 | 119592588 | 119592777 | chr2 | 119592997 | 119593567 | chr2 | 119599926 | 119600031 |
| chr2 | 119600332 | 119600555 | chr2 | 119600570 | 119600747 | chr2 | 119600949 | 119600952 |
| chr2 | 119600996 | 119601061 | chr2 | 119602601 | 119602629 | chr2 | 119602829 | 119603086 |
| chr2 | 119604032 | 119604158 | chr2 | 119604809 | 119604851 | chr2 | 119606135 | 119606499 |
| chr2 | 119606783 | 119606839 | chr2 | 119607176 | 119607411 | chr2 | 119610844 | 119610939 |
| chr2 | 119611745 | 119611799 | chr2 | 119612324 | 119612354 | chr2 | 119614130 | 119614171 |
| chr2 | 119614780 | 19614852 | chr2 | 119615055 | 119615627 | chr2 | 119616155 | 119616551 |
| chr2 | 119616809 | 119616870 | chr2 | 119914720 | 119914752 | chr2 | 119916525 | 119916595 |
| chr2 | 120281646 | 120281693 | chr2 | 120281939 | 120281953 | chr2 | 120980068 | 120980098 |
| chr2 | 120980353 | 120980395 | chr2 | 121200390 | 121200433 | chr2 | 121345081 | 121345111 |
| chr2 | 121411888 | 121412153 | chr2 | 122176232 | 122176293 | chr2 | 122495310 | 122495413 |
| chr2 | 122809783 | 122809801 | chr2 | 124782333 | 124782458 | chr2 | 124782692 | 124783097 |
| chr2 | 127413970 | 127413995 | chr2 | 127423220 | 127423350 | chr2 | 127429010 | 127429044 |
| chr2 | 127438633 | 127438663 | chr2 | 127783043 | 127783257 | chr2 | 127863617 | 127863725 |
| chr2 | 127976467 | 127976672 | chr2 | 128421891 | 128421947 | chr2 | 128616617 | 128616638 |
| chr2 | 128847700 | 128847723 | chr2 | 129494389 | 129494421 | chr2 | 130763584 | 130763623 |
| chr2 | 130971149 | 130971321 | chr2 | 131477785 | 131477936 | chr2 | 131594989 | 131595019 |
| chr2 | 131673756 | 131673785 | chr2 | 131720852 | 131721098 | chr2 | 131721461 | 131721584 |
| chr2 | 131721867 | 131721949 | chr2 | 131792260 | 131792519 | chr2 | 131792532 | 131792746 |
| chr2 | 131792921 | 131793131 | chr2 | 132088786 | 132088828 | chr2 | 132121661 | 132121829 |
| chr2 | 132152361 | 132152495 | chr2 | 132182790 | 132183089 | chr2 | 132208257 | 132208278 |
| chr2 | 132767457 | 132767492 | chr2 | 133014598 | 133014638 | chr2 | 133015299 | 133015323 |
| chr2 | 133062362 | 133062389 | chr2 | 133426249 | 133426279 | chr2 | 133426637 | 133426674 |
| chr2 | 136287374 | 136287390 | chr2 | 137522445 | 137522475 | chr2 | 137523825 | 137523855 |
| chr2 | 139536937 | 139537145 | chr2 | 139537443 | 139537822 | chr2 | 139537851 | 139537865 |
| chr2 | 142887871 | 142888066 | chr2 | 142888348 | 142888418 | chr2 | 144694503 | 144694514 |
| chr2 | 144694554 | 144695135 | chr2 | 145273404 | 145273751 | chr2 | 145274186 | 145274455 |
| chr2 | 145274814 | 145275213 | chr2 | 145282119 | 145282149 | chr2 | 148776809 | 148776892 |
| chr2 | 149633097 | 149633399 | chr2 | 149633744 | 149633965 | chr2 | 149645496 | 149645894 |
| chr2 | 151342903 | 151343277 | chr2 | 154333535 | 154333567 | chr2 | 154334272 | 154334665 |
| chr2 | 154335185 | 154335271 | chr2 | 154728245 | 154728440 | chr2 | 154729083 | 154729240 |
| chr2 | 154729559 | 154729589 | chr2 | 155555038 | 155555361 | chr2 | 157176592 | 157176717 |
| chr2 | 157177003 | 157178310 | chr2 | 157178646 | 157178731 | chr2 | 160761070 | 160761556 |
| chr2 | 161253374 | 161253455 | chr2 | 162272989 | 162273314 | chr2 | 162273383 | 162274338 |
| chr2 | 162274717 | 162274866 | chr2 | 162275146 | 162275226 | chr2 | 162275382 | 162275437 |
| chr2 | 162275473 | 162275802 | chr2 | 162280153 | 162280415 | chr2 | 162280741 | 162280956 |
| chr2 | 162283365 | 162283602 | chr2 | 162283783 | 162284055 | chr2 | 164593096 | 164593137 |
| chr2 | 168150069 | 168150245 | chr2 | 168150751 | 168150945 | chr2 | 170282981 | 170283080 |
| chr2 | 170551730 | 170551866 | chr2 | 170681880 | 170681911 | chr2 | 170682536 | 170682751 |
| chr2 | 171570182 | 171570189 | chr2 | 171570684 | 171570733 | chr2 | 171571264 | 171571315 |
| chr2 | 171571889 | 171572068 | chr2 | 171670349 | 171670446 | chr2 | 171671487 | 171671789 |
| chr2 | 171671800 | 171671881 | chr2 | 171673873 | 171673939 | chr2 | 171674739 | 171675066 |
| chr2 | 17167536] | 171675382 | chr2 | 171675523 | 171675592 | chr2 | 171676684 | 171676785 |
| chr2 | 171822428 | 171822480 | chr2 | 172367021 | 172367125 | chr2 | 172411136 | 172411166 |
| chr2 | 172945124 | 172945167 | chr2 | 172945896 | 172946211 | chr2 | 172947717 | 172947913 |
| chr2 | 172948184 | 172948314 | chr2 | 172948709 | 172948751 | chr2 | 172949186 | 172949282 |
| chr2 | 172949349 | 172949711 | chr2 | 172952521 | 172952881 | chr2 | 172952999 | 172953046 |
| chr2 | 172955472 | 172955545 | chr2 | 172957907 | 172958066 | chr2 | 172961398 | 172961598 |
| chr2 | 172964821 | 172964888 | chr2 | 172965296 | 172965298 | chr2 | 172965648 | 172965762 |
| chr2 | 172966264 | 172966442 | chr2 | 172972735 | 172972890 | chr2 | 172972931 | 172973218 |
| chr2 | 173099784 | 173099814 | chr2 | 173100262 | 173100430 | chr2 | 173422685 | 173422734 |
| chr2 | 174148138 | 174148157 | chr2 | 175190871 | 175191972 | chr2 | 175192085 | 175192468 |
| chr2 | 175193268 | 175193644 | chr2 | 175193809 | 175193823 | chr2 | 175195831 | 175195858 |
| chr2 | 175196432 | 175196575 | chr2 | 175197089 | 175197119 | chr2 | 175198752 | 175198766 |
| chr2 | 175198846 | 175198966 | chr2 | 175199527 | 175199554 | chr2 | 175199922 | 175199935 |
| chr2 | 175200140 | 175200440 | chr2 | 175200710 | 175200852 | chr2 | 175200917 | 175201182 |
| chr2 | 175201360 | 175201541 | chr2 | 175201776 | 175201828 | chr2 | 175202127 | 175202245 |
| chr2 | 175202569 | 175202600 | chr2 | 175202634 | 175202652 | chr2 | 175204174 | 175204204 |
| chr2 | 175204786 | 175204946 | chr2 | 175205588 | 175205799 | chr2 | 175206833 | 175206905 |
| chr2 | 175206961 | 175207028 | chr2 | 175207228 | 175207258 | chr2 | 175207536 | 175207653 |
| chr2 | 175208311 | 175208868 | chr2 | 175208997 | 175209135 | chr2 | 175547041 | 175547140 |
| chr2 | 175547384 | 175547413 | chr2 | 176940167 | 176940315 | chr2 | 176943269 | 176943568 |
| chr2 | 176943861 | 176943902 | chr2 | 176944457 | 176944846 | chr2 | 176945138 | 176945268 |
| chr2 | 176945582 | 176945784 | chr2 | 176946578 | 176946867 | chr2 | 176947285 | 176947389 |
| chr2 | 176947764 | 176947903 | chr2 | 176948599 | 176948742 | chr2 | 176949045 | 176949075 |
| chr2 | 176949695 | 176949869 | chr2 | 176950142 | 176950258 | chr2 | 176956558 | 176956599 |
| chr2 | 176956921 | 176957199 | chr2 | 176957577 | 176957628 | chr2 | 176957915 | 176957919 |
| chr2 | 176958138 | 176958489 | chr2 | 176959289 | 176959511 | chr2 | 176963448 | 176963522 |
| chr2 | 176964085 | 176964149 | chr2 | 176964390 | 176964767 | chr2 | 176965265 | 176965492 |
| chr2 | 176969463 | 176969613 | chr2 | 176969677 | 176969908 | chr2 | 176971628 | 176971651 |
| chr2 | 176976029 | 176976188 | chr2 | 176980750 | 176980937 | chr2 | 176981377 | 176981506 |
| chr2 | 176982584 | 176982627 | chr2 | 176986715 | 176986848 | chr2 | 176987057 | 176987224 |
| chr2 | 176987971 | 176988103 | chr2 | 176988155 | 176988304 | chr2 | 176993074 | 176993103 |

TABLE 13-continued

| chr | start | end | chr | start | end | chr | start | end |
|---|---|---|---|---|---|---|---|---|
| chr2 | 176993547 | 176993855 | chr2 | 176994031 | 176994379 | chr2 | 176994498 | 176994621 |
| chr2 | 176995072 | 176995269 | chr2 | 176995332 | 176995668 | chr2 | 177001102 | 177001695 |
| chr2 | 177001782 | 177001976 | chr2 | 177004566 | 177004658 | chr2 | 177014981 | 177015010 |
| chr2 | 177027425 | 177027438 | chr2 | 177030149 | 177030226 | chr2 | 177042984 | 177042998 |
| chr2 | 177043267 | 177043515 | chr2 | 177053276 | 177053434 | chr2 | 177053619 | 177053702 |
| chr2 | 177054113 | 177054351 | chr2 | 177503048 | 177503077 | chr2 | 177503581 | 177503610 |
| chr2 | 178098791 | 178098967 | chr2 | 178973003 | 178973042 | chr2 | 179303691 | 179303727 |
| chr2 | 179317019 | 179317057 | chr2 | 182321397 | 182321637 | chr2 | 182322039 | 182322170 |
| chr2 | 182322400 | 182323042 | chr2 | 182451522 | 182451551 | chr2 | 182542903 | 182542933 |
| chr2 | 182543321 | 182543418 | chr2 | 182543764 | 182543925 | chr2 | 182545211 | 182545275 |
| chr2 | 182545539 | 182545694 | chr2 | 182546002 | 182546085 | chr2 | 182546435 | 182546465 |
| chr2 | 182547385 | 182547387 | chr2 | 182547438 | 182547613 | chr2 | 182548062 | 182548161 |
| chr2 | 182549088 | 182549134 | chr2 | 182549337 | 182549454 | chr2 | 182550094 | 182550124 |
| chr2 | 182819048 | 182819216 | chr2 | 183731294 | 183731331 | chr2 | 183731467 | 183731524 |
| chr2 | 183731809 | 183732076 | chr2 | 185462869 | 185462980 | chr2 | 185463193 | 185463817 |
| chr2 | 186603488 | 186603518 | chr2 | 188419047 | 188419204 | chr2 | 189157427 | 189157688 |
| chr2 | 190708790 | 190708819 | chr2 | 193059025 | 193059317 | chr2 | 193059345 | 193059548 |
| chr2 | 193059662 | 193060067 | chr2 | 193060385 | 193060441 | chr2 | 193060683 | 193060891 |
| chr2 | 193061388 | 193061480 | chr2 | 198267345 | 198267374 | chr2 | 198456570 | 198456690 |
| chr2 | 198651002 | 198651076 | chr2 | 200326590 | 200326735 | chr2 | 200327424 | 200327451 |
| chr2 | 200329030 | 200329393 | chr2 | 200329433 | 200329668 | chr2 | 200333801 | 200333834 |
| chr2 | 200334976 | 200335451 | chr2 | 200335592 | 200335952 | chr2 | 201172444 | 201172480 |
| chr2 | 201450556 | 201450707 | chr2 | 201451014 | 201451040 | chr2 | 202097078 | 202097143 |
| chr2 | 202098936 | 202098965 | chr2 | 202101190 | 202101219 | chr2 | 202122459 | 202122683 |
| chr2 | 202899862 | 202899891 | chr2 | 203484608 | 203484627 | chr2 | 203880471 | 203880492 |
| chr2 | 206551072 | 206551362 | chr2 | 207139072 | 207139102 | chr2 | 207139347 | 207139605 |
| chr2 | 207307548 | 207307562 | chr2 | 207308802 | 207308857 | chr2 | 207506691 | 207507181 |
| chr2 | 208588311 | 208588341 | chr2 | 208635534 | 208635774 | chr2 | 208662170 | 208662213 |
| chr2 | 208989294 | 208989382 | chr2 | 209113097 | 209113126 | chr2 | 209225237 | 209225275 |
| chr2 | 209271322 | 209271336 | chr2 | 210636335 | 210636381 | chr2 | 210636430 | 210636689 |
| chr2 | 210636738 | 210636876 | chr2 | 212248428 | 212248457 | chr2 | 212288927 | 212288956 |
| chr2 | 212295683 | 212295820 | chr2 | 212530120 | 212530149 | chr2 | 212537902 | 212537994 |
| chr2 | 212566811 | 212566840 | chr2 | 212578292 | 212578321 | chr2 | 212587132 | 212587161 |
| chr2 | 213401235 | 213401339 | chr2 | 213401613 | 213401947 | chr2 | 213403110 | 213403337 |
| chr2 | 215275823 | 215275852 | chr2 | 215276310 | 215276339 | chr2 | 217448294 | 217448441 |
| chr2 | 217559296 | 217559326 | chr2 | 217559966 | 217559999 | chr2 | 218770207 | 218770270 |
| chr2 | 218806147 | 218806302 | chr2 | 219736151 | 219736691 | chr2 | 219828049 | 219828117 |
| chr2 | 219847462 | 219847555 | chr2 | 219848809 | 219848891 | chr2 | 219848936 | 219849001 |
| chr2 | 219857723 | 219852737 | chr2 | 220080510 | 220081033 | chr2 | 220173989 | 220174036 |
| chr2 | 220174060 | 220174296 | chr2 | 220196354 | 220196567 | chr2 | 220223098 | 220223128 |
| chr2 | 220223648 | 220223699 | chr2 | 220283363 | 220283519 | chr2 | 220299588 | 220299634 |
| chr2 | 220299886 | 220300059 | chr2 | 220349055 | 220349706 | chr2 | 220361447 | 220361466 |
| chr2 | 220416379 | 220416513 | chr2 | 220416848 | 220417649 | chr2 | 222435773 | 222435863 |
| chr2 | 223155722 | 223156188 | chr2 | 223158730 | 223159453 | chr2 | 223159869 | 223160065 |
| chr2 | 223160342 | 223160379 | chr2 | 223161247 | 223161684 | chr2 | 223161807 | 223162063 |
| chr2 | 223162779 | 223162890 | chr2 | 223162929 | 223163224 | chr2 | 223163473 | 223163535 |
| chr2 | 223163768 | 223163954 | chr2 | 223164534 | 223164883 | chr2 | 223165434 | 223165832 |
| chr2 | 223166294 | 223166408 | chr2 | 223166449 | 223166721 | chr2 | 223167389 | 223167573 |
| chr2 | 223168437 | 223168831 | chr2 | 223169640 | 223169864 | chr2 | 223170375 | 223170434 |
| chr2 | 223171109 | 223171180 | chr2 | 223172337 | 223172367 | chr2 | 223172924 | 223173173 |
| chr2 | 223175922 | 223176181 | chr2 | 223176456 | 223176511 | chr2 | 223176720 | 223176983 |
| chr2 | 223177315 | 223177610 | chr2 | 224661671 | 224661701 | chr2 | 224903406 | 224903440 |
| chr2 | 224903690 | 224903755 | chr2 | 224904108 | 224904237 | chr2 | 228029418 | 228029531 |
| chr2 | 228466761 | 228466777 | chr2 | 228735680 | 228735736 | chr2 | 228736215 | 228736295 |
| chr2 | 228736336 | 228736473 | chr2 | 229046107 | 229046503 | chr2 | 230795535 | 230795565 |
| chr2 | 232394970 | 232395021 | chr2 | 232395055 | 232395061 | chr2 | 232479822 | 232479938 |
| chr2 | 232522844 | 232522874 | chr2 | 232791704 | 232792012 | chr2 | 233350208 | 233350539 |
| chr2 | 233350844 | 233351278 | chr2 | 233352102 | 233352451 | chr2 | 233352507 | 233352762 |
| chr2 | 233352776 | 233352853 | chr2 | 233498710 | 233498873 | chr2 | 233498896 | 233499297 |
| chr2 | 233750525 | 233750555 | chr2 | 235404551 | 235404575 | chr2 | 235860746 | 235860808 |
| chr2 | 235861389 | 235861533 | chr2 | 236402771 | 236403013 | chr2 | 236403270 | 236403736 |
| chr2 | 236444269 | 236444298 | chr2 | 236578362 | 236578677 | chr2 | 236877262 | 236877399 |
| chr2 | 237072642 | 237073014 | chr2 | 237073354 | 237073414 | chr2 | 237076725 | 237076815 |
| chr2 | 237077562 | 237077608 | chr2 | 237077846 | 237078348 | chr2 | 237080264 | 237080294 |
| chr2 | 237081341 | 237081426 | chr2 | 237081537 | 237081553 | chr2 | 237082344 | 237082720 |
| chr2 | 237086349 | 237086468 | chr2 | 237145422 | 237145601 | chr2 | 237416216 | 237416429 |
| chr2 | 238395291 | 238395356 | chr2 | 238395906 | 238395961 | chr2 | 238535895 | 238535984 |
| chr2 | 238536005 | 238536114 | chr2 | 238864727 | 238864913 | chr2 | 239031722 | 239031780 |
| chr2 | 239051198 | 239051228 | chr2 | 239140139 | 239140249 | chr2 | 239149844 | 239149951 |
| chr2 | 239265702 | 239265787 | chr2 | 239482485 | 239482519 | chr2 | 239705305 | 239705337 |
| chr2 | 239755164 | 239755194 | chr2 | 239756373 | 239756462 | chr2 | 239756488 | 239756607 |
| chr2 | 239756634 | 239756648 | chr2 | 239757636 | 239757730 | chr2 | 239758126 | 239758144 |
| chr2 | 239758345 | 239758394 | chr2 | 239957330 | 239957448 | chr2 | 240167575 | 240167605 |
| chr2 | 240168811 | 240169051 | chr2 | 240319920 | 240320012 | chr2 | 240582379 | 240582524 |
| chr2 | 240619459 | 240619604 | chr2 | 240658227 | 240658421 | chr2 | 240658667 | 240658697 |
| chr2 | 241095604 | 241095772 | chr2 | 241393200 | 241393469 | chr2 | 241497411 | 241497554 |
| chr2 | 241541932 | 241542357 | chr2 | 241545001 | 241545031 | chr2 | 241758377 | 241758819 |
| chr2 | 241759597 | 241759694 | chr2 | 241760149 | 241760178 | chr2 | 241760494 | 241760523 |

TABLE 13-continued

| chr | start | end | chr | start | end | chr | start | end |
| --- | --- | --- | --- | --- | --- | --- | --- | --- |
| chr2 | 241771165 | 241771257 | chr2 | 241865194 | 241865346 | chr2 | 242009391 | 242009421 |
| chr2 | 242021784 | 242021892 | chr2 | 242523907 | 242524147 | chr2 | 242549849 | 242549957 |
| chr2 | 242554549 | 242554579 | chr2 | 242716723 | 242716760 | chr2 | 242756144 | 242756297 |
| chr2 | 242832984 | 242833159 | chr2 | 242833558 | 242833588 | chr2 | 242833797 | 242833863 |
| chr2 | 242836495 | 242836640 | chr2 | 242925496 | 242925641 | chr3 | 238536 | 238715 |
| chr3 | 239007 | 239094 | chr3 | 239622 | 239868 | chr3 | 240110 | 240223 |
| chr3 | 2140277 | 2140398 | chr3 | 3840498 | 3840758 | chr3 | 3841046 | 3841144 |
| chr3 | 3842679 | 3842731 | chr3 | 5137960 | 5138019 | chr3 | 6902288 | 6902353 |
| chr3 | 6903425 | 6903463 | chr3 | 8810152 | 8810220 | chr3 | 9593979 | 9594015 |
| chr3 | 9594263 | 9594382 | chr3 | 9595396 | 9595502 | chr3 | 9904233 | 9904554 |
| chr3 | 9941469 | 9941509 | chr3 | 9957064 | 9957142 | chr3 | 9957451 | 9957677 |
| chr3 | 10182839 | 10182996 | chr3 | 10183321 | 10183350 | chr3 | 10183706 | 10183782 |
| chr3 | 10184304 | 10184333 | chr3 | 10191477 | 10191620 | chr3 | 11034264 | 11034359 |
| chr3 | 11035070 | 11035330 | chr3 | 12046405 | 12046632 | chr3 | 12632309 | 12632401 |
| chr3 | 12645678 | 12645713 | chr3 | 12729424 | 12729454 | chr3 | 12917606 | 12917655 |
| chr3 | 12926053 | 12926102 | chr3 | 12977067 | 12977144 | chr3 | 13323494 | 13323973 |
| chr3 | 13324420 | 13324433 | chr3 | 13324847 | 13324938 | chr3 | 13590448 | 13590640 |
| chr3 | 13679172 | 13679349 | chr3 | 13921407 | 13921463 | chr3 | 14851850 | 14851897 |
| chr3 | 14852325 | 14852919 | chr3 | 15123848 | 15123992 | chr3 | 16554052 | 16554111 |
| chr3 | 16554347 | 16554633 | chr3 | 17001303 | 17001333 | chr3 | 19189441 | 19189470 |
| chr3 | 19189694 | 19189765 | chr3 | 19190143 | 19190216 | chr3 | 20070714 | 20070869 |
| chr3 | 22413665 | 22413694 | chr3 | 22413960 | 22413974 | chr3 | 23964981 | 23965019 |
| chr3 | 24871002 | 24871176 | chr3 | 25469110 | 25469139 | chr3 | 25469377 | 25469406 |
| chr3 | 25469679 | 25469708 | chr3 | 26664045 | 26664119 | chr3 | 26664389 | 26664755 |
| chr3 | 27754478 | 27754508 | chr3 | 27762336 | 27762650 | chr3 | 27762857 | 27762887 |
| chr3 | 27763566 | 27763595 | chr3 | 27764457 | 27764471 | chr3 | 27765181 | 27765347 |
| chr3 | 27771497 | 27772004 | chr3 | 27772790 | 27772819 | chr3 | 28616832 | 28617675 |
| chr3 | 31494108 | 31494138 | chr3 | 32858353 | 32858958 | chr3 | 32859256 | 32859284 |
| chr3 | 32859418 | 32859693 | chr3 | 32860068 | 32860273 | chr3 | 33259904 | 33260776 |
| chr3 | 35680842 | 35680872 | chr3 | 36805815 | 36805863 | chr3 | 36806179 | 36806193 |
| chr3 | 36984378 | 36984402 | chr3 | 37493519 | 37493621 | chr3 | 37901923 | 37901953 |
| chr3 | 38030618 | 38030782 | chr3 | 38032331 | 38032361 | chr3 | 38035774 | 38035989 |
| chr3 | 38080685 | 38080925 | chr3 | 38081154 | 38081271 | chr3 | 38182244 | 38182306 |
| chr3 | 38182626 | 38182655 | chr3 | 38690624 | 38690668 | chr3 | 39851772 | 39851814 |
| chr3 | 40428507 | 40428713 | chr3 | 41266086 | 41266151 | chr3 | 42222730 | 42222759 |
| chr3 | 42640855 | 42640880 | chr3 | 42814569 | 42814603 | chr3 | 42947411 | 42947455 |
| chr3 | 44036260 | 44036330 | chr3 | 44036570 | 44036600 | chr3 | 44036820 | 44037203 |
| chr3 | 44037625 | 44037662 | chr3 | 44037874 | 44038646 | chr3 | 44039348 | 44040006 |
| chr3 | 44040511 | 44040553 | chr3 | 44040796 | 44041039 | chr3 | 44063434 | 44063872 |
| chr3 | 44596479 | 44596509 | chr3 | 44596716 | 44596809 | chr3 | 44626438 | 44626711 |
| chr3 | 44726875 | 44727193 | chr3 | 45187296 | 45187327 | chr3 | 46924934 | 46924964 |
| chr3 | 47144864 | 47144893 | chr3 | 48227765 | 48227788 | chr3 | 48236476 | 48236570 |
| chr3 | 48693304 | 48693700 | chr3 | 48693852 | 48694154 | chr3 | 48698251 | 48698431 |
| chr3 | 48698810 | 48699010 | chr3 | 48699377 | 48699767 | chr3 | 49236845 | 49236874 |
| chr3 | 49405953 | 49405982 | chr3 | 49412883 | 49412987 | chr3 | 49591832 | 49592076 |
| chr3 | 49907093 | 49907130 | chr3 | 49939931 | 49940398 | chr3 | 50072827 | 50072846 |
| chr3 | 50243383 | 50243480 | chr3 | 50374655 | 50374684 | chr3 | 50374917 | 50374946 |
| chr3 | 50375179 | 50375559 | chr3 | 50377973 | 50378002 | chr3 | 50378277 | 50378306 |
| chr3 | 50378512 | 50378541 | chr3 | 50395506 | 50395536 | chr3 | 50402170 | 50402944 |
| chr3 | 50575616 | 50575637 | chr3 | 50968445 | 50968511 | chr3 | 52442062 | 52442091 |
| chr3 | 52552556 | 52552661 | chr3 | 52553469 | 52553499 | chr3 | 53032733 | 53033524 |
| chr3 | 54155611 | 54155677 | chr3 | 54157381 | 54157450 | chr3 | 54157878 | 54157919 |
| chr3 | 55519219 | 55519253 | chr3 | 55523106 | 55523290 | chr3 | 56603443 | 55603632 |
| chr3 | 58153446 | 58153608 | chr3 | 62304567 | 62304669 | chr3 | 62353371 | 62354049 |
| chr3 | 62354283 | 62354328 | chr3 | 62354625 | 62354792 | chr3 | 62354900 | 62354914 |
| chr3 | 62355424 | 62355478 | chr3 | 62355774 | 62356219 | chr3 | 62356367 | 62356644 |
| chr3 | 62356793 | 62357192 | chr3 | 62357279 | 62357347 | chr3 | 62357624 | 62357667 |
| chr3 | 62358530 | 62358595 | chr3 | 62358858 | 62359011 | chr3 | 62359376 | 62359893 |
| chr3 | 62360302 | 62360560 | chr3 | 62362902 | 62362916 | chr3 | 62363099 | 62363200 |
| chr3 | 62363626 | 62363693 | chr3 | 62363906 | 62364176 | chr3 | 62364280 | 62364329 |
| chr3 | 62364702 | 62365154 | chr3 | 62861118 | 62861148 | chr3 | 63264139 | 63264169 |
| chr3 | 66053446 | 66053470 | chr3 | 68056904 | 68057145 | chr3 | 68980931 | 68981113 |
| chr3 | 68981552 | 68981624 | chr3 | 69590939 | 69590969 | chr3 | 69591363 | 69591414 |
| chr3 | 69591780 | 69591977 | chr3 | 69740967 | 69740990 | chr3 | 69937703 | 69937848 |
| chr3 | 71802518 | 71802622 | chr3 | 71803126 | 71803372 | chr3 | 71803643 | 71803845 |
| chr3 | 73045492 | 73045583 | chr3 | 75956027 | 75956375 | chr3 | 79815522 | 79815557 |
| chr3 | 79816778 | 79817015 | chr3 | 79817288 | 79817318 | chr3 | 85008553 | 85008708 |
| chr3 | 88248025 | 88248049 | chr3 | 96532817 | 96532873 | chr3 | 96533383 | 96533458 |
| chr3 | 96534035 | 96534096 | chr3 | 98620891 | 98620980 | chr3 | 99594925 | 99595105 |
| chr3 | 101230678 | 101230694 | chr3 | 101230934 | 101231070 | chr3 | 101397240 | 101397329 |
| chr3 | 101497841 | 101497996 | chr3 | 106936157 | 106936336 | chr3 | 112052252 | 112052419 |
| chr3 | 115512319 | 115512354 | chr3 | 117715549 | 117715651 | chr3 | 117715771 | 117716123 |
| chr3 | 117716214 | 117716473 | chr3 | 120004080 | 120004405 | chr3 | 120004468 | 120004497 |
| chr3 | 120169104 | 120169149 | chr3 | 120169768 | 120169835 | chr3 | 120627317 | 120627453 |
| chr3 | 121902991 | 121903218 | chr3 | 121903324 | 121903619 | chr3 | 122234242 | 122234270 |
| chr3 | 122702288 | 122702430 | chr3 | 123167301 | 123167529 | chr3 | 123167769 | 123167827 |
| chr3 | 125898597 | 125899207 | chr3 | 125899525 | 125899962 | chr3 | 125932252 | 125932500 |
| chr3 | 126157586 | 126157663 | chr3 | 126261929 | 126262000 | chr3 | 126373520 | 126373704 |

TABLE 13-continued

| chr | start | end | chr | start | end | chr | start | end |
|---|---|---|---|---|---|---|---|---|
| chr3 | 126854699 | 126854796 | chr3 | 127534814 | 127534897 | chr3 | 127634186 | 127634216 |
| chr3 | 127794546 | 127794860 | chr3 | 127795325 | 127795408 | chr3 | 128056383 | 128056497 |
| chr3 | 128202447 | 128202477 | chr3 | 128208903 | 128209232 | chr3 | 128273993 | 128274051 |
| chr3 | 128274309 | 128274611 | chr3 | 128417201 | 128417231 | chr3 | 128720061 | 128720142 |
| chr3 | 128720164 | 128720346 | chr3 | 128720419 | 128720533 | chr3 | 128720567 | 128720611 |
| chr3 | 128720869 | 128721229 | chr3 | 128764489 | 128764606 | chr3 | 129693108 | 129693199 |
| chr3 | 129693305 | 129693498 | chr3 | 129693955 | 129694299 | chr3 | 130064451 | 130064484 |
| chr3 | 130064818 | 130064848 | chr3 | 130236049 | 130236063 | chr3 | 130236174 | 130236273 |
| chr3 | 130519901 | 130519929 | chr3 | 131754031 | 131754061 | chr3 | 132757065 | 132757104 |
| chr3 | 133217922 | 133217999 | chr3 | 133748140 | 133748245 | chr3 | 133748481 | 133748576 |
| chr3 | 134369646 | 134369855 | chr3 | 134514866 | 134514895 | chr3 | 134515128 | 134515369 |
| chr3 | 134515676 | 134516222 | chr3 | 136016868 | 136016942 | chr3 | 136537642 | 136537730 |
| chr3 | 136538585 | 136538815 | chr3 | 136582917 | 136582951 | chr3 | 136751641 | 136751809 |
| chr3 | 137479233 | 137479302 | chr3 | 137479601 | 137479687 | chr3 | 137479980 | 137480764 |
| chr3 | 137481170 | 137481315 | chr3 | 137481858 | 137481872 | chr3 | 137481936 | 137482183 |
| chr3 | 137483313 | 137483437 | chr3 | 137483514 | 137483589 | chr3 | 137483848 | 137484002 |
| chr3 | 137484405 | 137484531 | chr3 | 137486029 | 137486310 | chr3 | 137486516 | 137486550 |
| chr3 | 137487964 | 137488003 | chr3 | 137488950 | 137489698 | chr3 | 137489876 | 137491040 |
| chr3 | 138067717 | 138067747 | chr3 | 138153963 | 138153993 | chr3 | 138374229 | 138374258 |
| chr3 | 138655934 | 138656138 | chr3 | 138666834 | 138656889 | chr3 | 138657414 | 138657494 |
| chr3 | 138657618 | 138658296 | chr3 | 138658704 | 138658863 | chr3 | 138659081 | 138659099 |
| chr3 | 138662134 | 138662164 | chr3 | 138662282 | 138662296 | chr3 | 138662382 | 138662448 |
| chr3 | 138662799 | 138662842 | chr3 | 138663613 | 138663727 | chr3 | 138664142 | 138664165 |
| chr3 | 138664928 | 138665323 | chr3 | 138665562 | 138665718 | chr3 | 138665778 | 138666294 |
| chr3 | 138668758 | 138669108 | chr3 | 138669141 | 138669387 | chr3 | 139258267 | 139258316 |
| chr3 | 139653491 | 139653693 | chr3 | 140769513 | 140769705 | chr3 | 140769908 | 140770301 |
| chr3 | 140770408 | 140770589 | chr3 | 140770644 | 140770829 | chr3 | 140771305 | 140771335 |
| chr3 | 140771816 | 140771854 | chr3 | 141174349 | 141174606 | chr3 | 141481982 | 141482073 |
| chr3 | 141516389 | 141516719 | chr3 | 141657032 | 141657079 | chr3 | 141836036 | 141836077 |
| chr3 | 142537638 | 142537779 | chr3 | 142682273 | 142682392 | chr3 | 142791151 | 142791173 |
| chr3 | 142837980 | 142838318 | chr3 | 142838621 | 142838646 | chr3 | 142838877 | 142839036 |
| chr3 | 142839563 | 142839688 | chr3 | 142839784 | 142839901 | chr3 | 142839945 | 142840127 |
| chr3 | 142840222 | 142840236 | chr3 | 142896156 | 142896214 | chr3 | 143280343 | 143280373 |
| chr3 | 145878665 | 145878695 | chr3 | 146187946 | 146187978 | chr3 | 147074457 | 147074487 |
| chr3 | 147074974 | 147075006 | chr3 | 147077289 | 147077671 | chr3 | 147078959 | 147079188 |
| chr3 | 147087562 | 147087799 | chr3 | 147088440 | 147088523 | chr3 | 147088939 | 147089099 |
| chr3 | 147098431 | 147098470 | chr3 | 147105898 | 147106010 | chr3 | 147108841 | 147109765 |
| chr3 | 147110229 | 147110683 | chr3 | 147110927 | 147111089 | chr3 | 147125697 | 147125726 |
| chr3 | 147127037 | 147127067 | chr3 | 147127681 | 147127902 | chr3 | 147136931 | 147137000 |
| chr3 | 147137076 | 147137164 | chr3 | 147138768 | 147138855 | chr3 | 147139374 | 147139528 |
| chr3 | 148415427 | 148415644 | chr3 | 148523213 | 148523255 | chr3 | 148803258 | 148803276 |
| chr3 | 149374947 | 149375023 | chr3 | 150802981 | 150802999 | chr3 | 150803026 | 150803080 |
| chr3 | 150804043 | 150804077 | chr3 | 150804967 | 150805030 | chr3 | 152553343 | 152553384 |
| chr3 | 152553658 | 152553725 | chr3 | 152877666 | 152877696 | chr3 | 153838818 | 153838870 |
| chr3 | 153839518 | 153839952 | chr3 | 154146133 | 154146394 | chr3 | 154146654 | 154146908 |
| chr3 | 154797334 | 154797703 | chr3 | 155461030 | 155461053 | chr3 | 155463041 | 155463071 |
| chr3 | 156007772 | 156007801 | chr3 | 156008976 | 156009299 | chr3 | 156009319 | 156009425 |
| chr3 | 157155252 | 157155490 | chr3 | 157155982 | 157156194 | chr3 | 157812196 | 157812257 |
| chr3 | 157812437 | 157812645 | chr3 | 157812912 | 157813070 | chr3 | 157813670 | 157813824 |
| chr3 | 157814311 | 157814340 | chr3 | 157815657 | 157815822 | chr3 | 157820576 | 157820605 |
| chr3 | 157821537 | 157821662 | chr3 | 157821904 | 157822008 | chr3 | 157823073 | 157823119 |
| chr3 | 157823139 | 157823143 | chr3 | 157823464 | 157823493 | chr3 | 157824133 | 157824146 |
| chr3 | 157824212 | 157824231 | chr3 | 157824495 | 157824871 | chr3 | 157825176 | 157825408 |
| chr3 | 159756687 | 159756856 | chr3 | 159944486 | 159944546 | chr3 | 164912376 | 164912568 |
| chr3 | 164912907 | 164913872 | chr3 | 164914980 | 164915129 | chr3 | 169376183 | 169376215 |
| chr3 | 169376680 | 169376780 | chr3 | 169378825 | 169379024 | chr3 | 169539894 | 169540679 |
| chr3 | 169541070 | 169541102 | chr3 | 170136627 | 170136751 | chr3 | 170302617 | 170302677 |
| chr3 | 170303087 | 170303129 | chr3 | 170303380 | 170303423 | chr3 | 170303639 | 170303844 |
| chr3 | 171527930 | 171527971 | chr3 | 172165443 | 172165784 | chr3 | 172165867 | 172166512 |
| chr3 | 172166879 | 172166893 | chr3 | 172167000 | 172167044 | chr3 | 172167297 | 172167327 |
| chr3 | 172167660 | 172167917 | chr3 | 172355895 | 172355997 | chr3 | 172425382 | 172425400 |
| chr3 | 172425700 | 172425717 | chr3 | 172469925 | 172469951 | chr3 | 173115237 | 173115550 |
| chr3 | 173302542 | 173302668 | chr3 | 173302992 | 173303225 | chr3 | 176710106 | 176710144 |
| chr3 | 178861413 | 178861447 | chr3 | 178916711 | 178916959 | chr3 | 178921537 | 178921568 |
| chr3 | 178927966 | 178928094 | chr3 | 178936059 | 178936111 | chr3 | 178952059 | 178952105 |
| chr3 | 179168661 | 179169266 | chr3 | 179367897 | 179367920 | chr3 | 179754178 | 179754192 |
| chr3 | 179754239 | 179754759 | chr3 | 179754804 | 179754872 | chr3 | 179755087 | 179755372 |
| chr3 | 180320256 | 180320294 | chr3 | 181413742 | 181414330 | chr3 | 181420065 | 181420116 |
| chr3 | 181420316 | 181420374 | chr3 | 181421411 | 181422282 | chr3 | 181422541 | 181422985 |
| chr3 | 181428388 | 181428772 | chr3 | 181430695 | 181430771 | chr3 | 181437129 | 181437349 |
| chr3 | 181438194 | 181438353 | chr3 | 181440892 | 181441927 | chr3 | 181442145 | 181442410 |
| chr3 | 181443014 | 181443557 | chr3 | 181443760 | 181443861 | chr3 | 181444108 | 181444236 |
| chr3 | 181444434 | 181444524 | chr3 | 181444613 | 181444754 | chr3 | 181444844 | 181444948 |
| chr3 | 181444989 | 181445013 | chr3 | 181445369 | 181445464 | chr3 | 181445800 | 181445861 |
| chr3 | 182816009 | 182816027 | chr3 | 182895956 | 182895990 | chr3 | 182911545 | 182911574 |
| chr3 | 183109854 | 183109883 | chr3 | 183145412 | 183145618 | chr3 | 183145931 | 183146025 |
| chr3 | 183146397 | 183146435 | chr3 | 183146648 | 183146677 | chr3 | 183217676 | 183217706 |
| chr3 | 183647996 | 183648026 | chr3 | 183728813 | 183728952 | chr3 | 183965599 | 183965633 |

TABLE 13-continued

| chr | start | end | chr | start | end | chr | start | end |
|---|---|---|---|---|---|---|---|---|
| chr3 | 184018038 | 184018136 | chr3 | 184031686 | 184031746 | chr3 | 184057526 | 184057557 |
| chr3 | 184099417 | 184099446 | chr3 | 184319470 | 184319612 | chr3 | 184319828 | 184319842 |
| chr3 | 184319874 | 184319891 | chr3 | 185001898 | 185001919 | chr3 | 185271296 | 185271380 |
| chr3 | 185303242 | 185303277 | chr3 | 185363074 | 185363261 | chr3 | 185643324 | 185643405 |
| chr3 | 186078766 | 186078898 | chr3 | 186079204 | 186079331 | chr3 | 186080188 | 186080218 |
| chr3 | 186857152 | 186857607 | chr3 | 186914705 | 186914734 | chr3 | 187387850 | 187387920 |
| chr3 | 187388007 | 187388239 | chr3 | 192125828 | 192125828 | chr3 | 192126146 | 192126710 |
| chr3 | 192126787 | 192126863 | chr3 | 192127354 | 192127372 | chr3 | 192127557 | 192127730 |
| chr3 | 192127937 | 192128074 | chr3 | 192232097 | 192232175 | chr3 | 192232452 | 192232570 |
| chr3 | 192232850 | 192232951 | chr3 | 192233095 | 192233150 | chr3 | 192958725 | 192958968 |
| chr3 | 193312128 | 193312208 | chr3 | 193419702 | 193419732 | chr3 | 193548637 | 193548835 |
| chr3 | 193776089 | 193776119 | chr3 | 194048751 | 194048919 | chr3 | 194120008 | 194120164 |
| chr3 | 194120812 | 194120841 | chr3 | 194120934 | 194120963 | chr3 | 194208468 | 194208562 |
| chr3 | 194407998 | 194408028 | chr3 | 194408375 | 194408768 | chr3 | 194408839 | 194409021 |
| chr3 | 194981816 | 194981895 | chr3 | 195095450 | 195095467 | chr3 | 195095527 | 195095543 |
| chr3 | 195536733 | 195536848 | chr3 | 195538315 | 195538353 | chr3 | 195587032 | 195587118 |
| chr3 | 195601239 | 195601312 | chr3 | 195602363 | 195602576 | chr3 | 195648794 | 195648899 |
| chr3 | 196046702 | 196046736 | chr3 | 196065342 | 196065583 | chr3 | 196069892 | 196070192 |
| chr3 | 196255617 | 196255631 | chr3 | 196344683 | 196344710 | chr3 | 196387395 | 196387415 |
| chr3 | 196387628 | 196387665 | chr3 | 196388383 | 196388581 | chr3 | 196440510 | 196440593 |
| chr3 | 196728418 | 196728448 | chr3 | 196731155 | 196731313 | chr3 | 196755958 | 196755987 |
| chr3 | 197209019 | 197209048 | chr3 | 197236945 | 197237111 | chr3 | 197247047 | 197247110 |
| chr3 | 197278926 | 197278988 | chr3 | 197327011 | 197327042 | chr3 | 197330104 | 197330147 |
| chr3 | 197616707 | 197616861 | chr3 | 197677029 | 197677058 | chr3 | 197685788 | 197685817 |
| chr3 | 197686057 | 197686085 | chr3 | 197686495 | 197686524 | chr3 | 197686941 | 197687223 |
| chr3 | 197687694 | 197687723 | chr4 | 206324 | 206353 | chr4 | 331322 | 331352 |
| chr4 | 512978 | 513008 | chr4 | 513704 | 513734 | chr4 | 568429 | 568652 |
| chr4 | 569048 | 569115 | chr4 | 569275 | 569435 | chr4 | 569461 | 569732 |
| chr4 | 570966 | 571013 | chr4 | 571508 | 571689 | chr4 | 628572 | 628787 |
| chr4 | 651196 | 651261 | chr4 | 657521 | 657552 | chr4 | 678471 | 678501 |
| chr4 | 718052 | 718112 | chr4 | 718321 | 718359 | chr4 | 829611 | 829641 |
| chr4 | 955367 | 955454 | chr4 | 955867 | 955919 | chr4 | 995876 | 995993 |
| chr4 | 996101 | 996174 | chr4 | 1008740 | 1008902 | chr4 | 1016127 | 1016252 |
| chr4 | 1016586 | 1016747 | chr4 | 1025928 | 1026074 | chr4 | 1041763 | 1041926 |
| chr4 | 1093536 | 1093675 | chr4 | 1107494 | 1107585 | chr4 | 1165450 | 1165470 |
| chr4 | 1189021 | 1189051 | chr4 | 1214894 | 1215162 | chr4 | 1215415 | 1215451 |
| chr4 | 1282515 | 1282545 | chr4 | 1331675 | 1331705 | chr4 | 1336755 | 1336902 |
| chr4 | 1338715 | 1338812 | chr4 | 1339099 | 1339130 | chr4 | 1396578 | 1396696 |
| chr4 | 1397396 | 1397495 | chr4 | 1398303 | 1398378 | chr4 | 1399723 | 1399768 |
| chr4 | 1401711 | 1401743 | chr4 | 1512368 | 1512398 | chr4 | 1556419 | 1556609 |
| chr4 | 1576484 | 1576528 | chr4 | 1616682 | 1617247 | chr4 | 1687080 | 1687110 |
| chr4 | 1800153 | 1800191 | chr4 | 1803550 | 1803582 | chr4 | 1806084 | 1806113 |
| chr4 | 1807355 | 1807384 | chr4 | 1962787 | 1962816 | chr4 | 1993771 | 1994180 |
| chr4 | 2042106 | 2042122 | chr4 | 2042169 | 2042258 | chr4 | 2066114 | 2066265 |
| chr4 | 2305672 | 2305827 | chr4 | 2527907 | 2527937 | chr4 | 2540215 | 2540297 |
| chr4 | 2765862 | 2765910 | chr4 | 2926366 | 2926396 | chr4 | 2978968 | 2979145 |
| chr4 | 3036118 | 3036148 | chr4 | 3217107 | 3217154 | chr4 | 3371519 | 3371652 |
| chr4 | 3446991 | 3447021 | chr4 | 3447816 | 3448015 | chr4 | 3768833 | 3768949 |
| chr4 | 3768995 | 3769189 | chr4 | 3769560 | 3769574 | chr4 | 3873694 | 3873769 |
| chr4 | 4228189 | 4228241 | chr4 | 4229689 | 4229781 | chr4 | 4387533 | 4387627 |
| chr4 | 4417568 | 4417603 | chr4 | 4855102 | 4855171 | chr4 | 4855371 | 4855433 |
| chr4 | 4860046 | 4860075 | chr4 | 4862769 | 4863110 | chr4 | 4867698 | 4867886 |
| chr4 | 4868566 | 4868792 | chr4 | 4868829 | 4868999 | chr4 | 4872088 | 4872167 |
| chr4 | 4872777 | 4872850 | chr4 | 4873427 | 4873528 | chr4 | 5021188 | 5021217 |
| chr4 | 5053070 | 5053518 | chr4 | 5053747 | 5054093 | chr4 | 5709906 | 5709984 |
| chr4 | 5712979 | 5713231 | chr4 | 5889948 | 5890045 | chr4 | 5890274 | 5890444 |
| chr4 | 5891966 | 5892081 | chr4 | 5892110 | 5892194 | chr4 | 5892750 | 5892780 |
| chr4 | 5893981 | 5894082 | chr4 | 6200897 | 6201235 | chr4 | 6202103 | 6202276 |
| chr4 | 6247351 | 6247381 | chr4 | 6565004 | 6565042 | chr4 | 6670184 | 6670214 |
| chr4 | 6748346 | 6748557 | chr4 | 6957481 | 6957620 | chr4 | 7647770 | 7647945 |
| chr4 | 2758476 | 2758561 | chr4 | 8582549 | 8582579 | chr4 | 8607813 | 8607932 |
| chr4 | 8608556 | 8608600 | chr4 | 8858827 | 8859047 | chr4 | 8859382 | 8859738 |
| chr4 | 8860398 | 8860553 | chr4 | 8861649 | 8861752 | chr4 | 8861919 | 8862014 |
| chr4 | 8862797 | 8862811 | chr4 | 8863441 | 8863526 | chr4 | 8864499 | 8864598 |
| chr4 | 8864831 | 8865058 | chr4 | 8868822 | 8868845 | chr4 | 8868932 | 8869270 |
| chr4 | 8869601 | 8869813 | chr4 | 8873054 | 8873072 | chr4 | 8873809 | 8873984 |
| chr4 | 8874485 | 8874534 | chr4 | 8874773 | 8874787 | chr4 | 8875877 | 8875907 |
| chr4 | 8893060 | 8893093 | chr4 | 8893501 | 8893531 | chr4 | 8893816 | 8893931 |
| chr4 | 8894641 | 8894957 | chr4 | 8895232 | 8895350 | chr4 | 8895554 | 8895584 |
| chr4 | 8895965 | 8896052 | chr4 | 9423273 | 9423314 | chr4 | 9782992 | 9783095 |
| chr4 | 9783126 | 9783412 | chr4 | 10458395 | 10459121 | chr4 | 10462833 | 10463047 |
| chr4 | 10463073 | 10463604 | chr4 | 11429506 | 11429633 | chr4 | 13524026 | 13524251 |
| chr4 | 13524665 | 13524775 | chr4 | 13524957 | 13524971 | chr4 | 13537569 | 13537688 |
| chr4 | 13540983 | 13541068 | chr4 | 13546026 | 13546078 | chr4 | 13548502 | 13548589 |
| chr4 | 13548635 | 13548895 | chr4 | 13549340 | 13549510 | chr4 | 15780223 | 15780320 |
| chr4 | 16084741 | 16084818 | chr4 | 16085167 | 16085301 | chr4 | 16085352 | 16085381 |
| chr4 | 16085675 | 16085682 | chr4 | 17783003 | 17783480 | chr4 | 20254693 | 20254723 |
| chr4 | 20255525 | 20255861 | chr4 | 20256152 | 20256285 | chr4 | 21950248 | 21950295 |

TABLE 13-continued

| chr | start | end | chr | start | end | chr | start | end |
|---|---|---|---|---|---|---|---|---|
| chr4 | 24801868 | 24801985 | chr4 | 24914638 | 24914668 | chr4 | 25656815 | 25656879 |
| chr4 | 25657437 | 25657477 | chr4 | 27086432 | 27086462 | chr4 | 30722243 | 30722273 |
| chr4 | 30723856 | 30723862 | chr4 | 30724249 | 30724372 | chr4 | 37245837 | 37245851 |
| chr4 | 37246134 | 37246360 | chr4 | 37246490 | 37246699 | chr4 | 37247096 | 37247216 |
| chr4 | 38565373 | 38566418 | chr4 | 38673115 | 38673144 | chr4 | 40632773 | 40632802 |
| chr4 | 40910303 | 40910465 | chr4 | 41258716 | 41258788 | chr4 | 41259076 | 41259176 |
| chr4 | 41747009 | 41747133 | chr4 | 41747493 | 41747582 | chr4 | 41747958 | 41747977 |
| chr4 | 41748144 | 41748296 | chr4 | 41748660 | 41748766 | chr4 | 41749033 | 41749063 |
| chr4 | 41749270 | 41749761 | chr4 | 41750223 | 41750504 | chr4 | 41751870 | 41752006 |
| chr4 | 41752451 | 41752693 | chr4 | 41752968 | 41753398 | chr4 | 41753610 | 41753916 |
| chr4 | 41754031 | 41754071 | chr4 | 41875430 | 41875902 | chr4 | 41880331 | 41880412 |
| chr4 | 41881385 | 41881425 | chr4 | 41883091 | 41883302 | chr4 | 41883510 | 41883610 |
| chr4 | 41993716 | 41993815 | chr4 | 42152962 | 42163411 | chr4 | 42153533 | 42153632 |
| chr4 | 42153882 | 42154025 | chr4 | 42154280 | 42154359 | chr4 | 42154652 | 42154997 |
| chr4 | 42155293 | 42155322 | chr4 | 42348266 | 42348331 | chr4 | 42398842 | 42398872 |
| chr4 | 42399137 | 42399191 | chr4 | 42399688 | 42399872 | chr4 | 44449480 | 44449569 |
| chr4 | 46391353 | 46391383 | chr4 | 46911535 | 46911564 | chr4 | 46995161 | 46995835 |
| chr4 | 47034908 | 47034938 | chr4 | 48485067 | 48485288 | chr4 | 48485590 | 48486000 |
| chr4 | 48486356 | 48486389 | chr4 | 48492181 | 48492433 | chr4 | 48848428 | 48848461 |
| chr4 | 48988109 | 48988335 | chr4 | 53728495 | 53729056 | chr4 | 54966854 | 54967075 |
| chr4 | 54967342 | 54967484 | chr4 | 54969833 | 54970095 | chr4 | 54970369 | 54970482 |
| chr4 | 54975991 | 54976115 | chr4 | 55093048 | 55093255 | chr4 | 55096239 | 55096344 |
| chr4 | 55097404 | 55097634 | chr4 | 55097973 | 55098092 | chr4 | 55098198 | 55098373 |
| chr4 | 55098674 | 55098744 | chr4 | 55099039 | 55099062 | chr4 | 55133613 | 55133642 |
| chr4 | 55136787 | 55136816 | chr4 | 55138657 | 55138686 | chr4 | 55139691 | 55139720 |
| chr4 | 55140731 | 55140784 | chr4 | 55141015 | 55141050 | chr4 | 55144105 | 55144134 |
| chr4 | 55146554 | 55146583 | chr4 | 55152075 | 55152140 | chr4 | 55524220 | 55524274 |
| chr4 | 55589753 | 55589782 | chr4 | 55592166 | 55592204 | chr4 | 55593417 | 55593675 |
| chr4 | 55594183 | 55594212 | chr4 | 55595504 | 55595614 | chr4 | 55599306 | 55599356 |
| chr4 | 55968165 | 55968194 | chr4 | 55991107 | 55991228 | chr4 | 55992153 | 55992169 |
| chr4 | 56659692 | 56659866 | chr4 | 56660021 | 56660021 | chr4 | 57017423 | 57017459 |
| chr4 | 57371718 | 57371963 | chr4 | 57372336 | 57372504 | chr4 | 57396946 | 57397264 |
| chr4 | 57521506 | 57521663 | chr4 | 57521701 | 57522382 | chr4 | 57522420 | 57522815 |
| chr4 | 57687720 | 57687782 | chr4 | 57777437 | 57777595 | chr4 | 57803528 | 57803558 |
| chr4 | 57976033 | 57976185 | chr4 | 57976416 | 57976573 | chr4 | 58030191 | 58030524 |
| chr4 | 62066196 | 62066553 | chr4 | 62067511 | 62067624 | chr4 | 62068072 | 62068150 |
| chr4 | 66535130 | 66535314 | chr4 | 66535351 | 66535443 | chr4 | 66536171 | 66536323 |
| chr4 | 74702479 | 74702516 | chr4 | 74735076 | 74735137 | chr4 | 74809877 | 74809933 |
| chr4 | 75241348 | 75241435 | chr4 | 75858573 | 75858629 | chr4 | 76555532 | 76555856 |
| chr4 | 76912716 | 76912733 | chr4 | 79611273 | 79611294 | chr4 | 79689651 | 79689732 |
| chr4 | 81106351 | 81106871 | chr4 | 81124277 | 81124662 | chr4 | 81187046 | 81187076 |
| chr4 | 81187559 | 81187589 | chr4 | 81188385 | 81188489 | chr4 | 81188491 | 81188556 |
| chr4 | 81189419 | 81189660 | chr4 | 81189714 | 81189911 | chr4 | 81951431 | 81951460 |
| chr4 | 81951941 | 81951970 | chr4 | 81952170 | 81952311 | chir4 | 82135873 | 82135887 |
| chr4 | 82135920 | 82136056 | chr4 | 82136495 | 82136548 | chr4 | 82136807 | 82136837 |
| chr4 | 83323506 | 83323708 | chr4 | 83720611 | 83720643 | chr4 | 84035907 | 84035936 |
| chr4 | 85402377 | 85402511 | chr4 | 85402776 | 85403423 | chr4 | 85403913 | 85403927 |
| chr4 | 85404112 | 85404140 | chr4 | 85404225 | 85404475 | chr4 | 85404650 | 85404693 |
| chr4 | 85414045 | 85414113 | chr4 | 85414725 | 85414846 | chr4 | 85417336 | 85417564 |
| chr4 | 85417953 | 85418079 | chr4 | 85418522 | 85418582 | chr4 | 85420591 | 85420621 |
| chr4 | 85422188 | 85422432 | chr4 | 85422973 | 85423316 | chr4 | 85424401 | 85424483 |
| chr4 | 87515337 | 87515367 | chr4 | 89378464 | 89378497 | chr4 | 89378744 | 89378766 |
| chr4 | 89378832 | 89378888 | chr4 | 90757517 | 90757828 | chr4 | 90758105 | 90758134 |
| chr4 | 90758776 | 90758883 | chr4 | 93224972 | 93225171 | chr4 | 93226365 | 93226703 |
| chr4 | 93226729 | 93227129 | chr4 | 94749725 | 94749755 | chr4 | 94750982 | 94751140 |
| chr4 | 94751419 | 94751502 | chr4 | 94753415 | 94753445 | chr4 | 94756002 | 94756109 |
| chr4 | 95127590 | 95127684 | chr4 | 96470752 | 96470782 | chr4 | 101111246 | 101111504 |
| chr4 | 101111857 | 101111970 | chr4 | 102711731 | 102711787 | chr4 | 106335495 | 106335526 |
| chr4 | 107956311 | 107955826 | chr4 | 107956676 | 107957085 | chr4 | 107957373 | 107957466 |
| chr4 | 109093101 | 109093168 | chr4 | 109093405 | 109093506 | chr4 | 110223200 | 110223427 |
| chr4 | 110223579 | 110223980 | chr4 | 110344278 | 110344294 | chr4 | 111532705 | 111532961 |
| chr4 | 111536288 | 111536505 | chr4 | 111536562 | 111536693 | chr4 | 111536960 | 111536974 |
| chr4 | 111537407 | 111537497 | chr4 | 111540199 | 111540360 | chr4 | 111542474 | 111542757 |
| chr4 | 111543232 | 111543345 | chr4 | 111543404 | 111543450 | chr4 | 111543661 | 111543695 |
| chr4 | 111543721 | 111543735 | chr4 | 111544381 | 111544583 | chr4 | 111549800 | 111549830 |
| chr4 | 111550618 | 111550834 | chr4 | 111552118 | 111552148 | chr4 | 111553099 | 111553450 |
| chr4 | 111553916 | 111553951 | chr4 | 111554950 | 111554964 | chr4 | 111555194 | 111555343 |
| chr4 | 111557965 | 111558049 | chr4 | 111558551 | 111559233 | chr4 | 111560249 | 111560636 |
| chr4 | 111562576 | 111562648 | chr4 | 113154896 | 113155043 | chr4 | 113430640 | 113430672 |
| chr4 | 113431834 | 113431854 | chr4 | 113431916 | 113432154 | chr4 | 113432227 | 113432503 |
| chr4 | 113432519 | 113432573 | chr4 | 113436216 | 113436287 | chr4 | 113441592 | 113441733 |
| chr4 | 113442098 | 113442185 | chr4 | 113442247 | 113442525 | chr4 | 113444020 | 113444448 |
| chr4 | 117847399 | 117847458 | chr4 | 121844063 | 121844206 | chr4 | 121992265 | 121992312 |
| chr4 | 121993997 | 121994251 | chr4 | 122301422 | 122301712 | chr4 | 122302116 | 122302246 |
| chr4 | 122685807 | 122685890 | chr4 | 122686209 | 122686507 | chr4 | 122871294 | 122871334 |
| chr4 | 122871573 | 122872000 | chr4 | 123664228 | 123664363 | chr4 | 126237310 | 126237611 |
| chr4 | 126238024 | 126238436 | chr4 | 128544048 | 128544161 | chr4 | 128544646 | 128544789 |
| chr4 | 128967290 | 128967329 | chr4 | 134067881 | 134068004 | chr4 | 134068577 | 134068791 |

TABLE 13-continued

| chr | start | end | chr | start | end | chr | start | end |
|---|---|---|---|---|---|---|---|---|
| chr4 | 134069289 | 134069318 | chr4 | 134069578 | 134069896 | chr4 | 134070374 | 134070403 |
| chr4 | 134071648 | 134072610 | chr4 | 134072677 | 134072967 | chr4 | 134073184 | 134073322 |
| chr4 | 134073568 | 134073641 | chr4 | 134073862 | 134073919 | chr4 | 134074030 | 134074156 |
| chr4 | 140200529 | 140201156 | chr4 | 140201193 | 140201462 | chr4 | 140656643 | 140656666 |
| chr4 | 140656858 | 140657089 | chr4 | 141347942 | 141348151 | chr4 | 141418921 | 141419418 |
| chr4 | 141488870 | 141489128 | chr4 | 142053130 | 142053160 | chr4 | 142053520 | 142053734 |
| chr4 | 142054239 | 142054460 | chr4 | 143766796 | 143766930 | chr4 | 144621336 | 144621439 |
| chr4 | 144621515 | 144621896 | chr4 | 144621982 | 144622058 | chr4 | 145568052 | 145568147 |
| chr4 | 145568459 | 145568741 | chr4 | 146853951 | 146853981 | chr4 | 147558272 | 147558381 |
| chr4 | 147558477 | 147558504 | chr4 | 147559321 | 147560078 | chr4 | 147560134 | 147560418 |
| chr4 | 147560460 | 147560617 | chr4 | 147560933 | 147561145 | chr4 | 147561360 | 147561949 |
| chr4 | 147562000 | 147562055 | chr4 | 147568636 | 147569060 | chr4 | 147569620 | 147569650 |
| chr4 | 147576177 | 147576201 | chr4 | 147576330 | 147576639 | chr4 | 151974287 | 151974489 |
| chr4 | 152148807 | 152148836 | chr4 | 152246132 | 152246314 | chr4 | 153247273 | 153247386 |
| chr4 | 153249362 | 153249398 | chr4 | 153251894 | 153251923 | chr4 | 153702685 | 153702702 |
| chr4 | 154216241 | 154216357 | chr4 | 154709524 | 154709610 | chr4 | 154709759 | 154710617 |
| chr4 | 154710729 | 154710914 | chr4 | 154712172 | 154712594 | chr4 | 154713500 | 154713530 |
| chr4 | 154713949 | 154714010 | chr4 | 155254166 | 155254196 | chr4 | 155411851 | 155412279 |
| chr4 | 155663209 | 155663647 | chr4 | 155665445 | 155665475 | chr4 | 156129129 | 156129183 |
| chr4 | 156129451 | 156129495 | chr4 | 156129746 | 156129797 | chr4 | 156130047 | 156130297 |
| chr4 | 156297416 | 156297556 | chr4 | 156297942 | 156298073 | chr4 | 156588311 | 156588401 |
| chr4 | 156589273 | 156589323 | chr4 | 156680257 | 156680532 | chr4 | 156681370 | 156681489 |
| chr4 | 158141576 | 158141606 | chr4 | 158142847 | 158142999 | chr4 | 158143443 | 158143465 |
| chr4 | 164252991 | 164253447 | chr4 | 165304515 | 165304578 | chr4 | 165305060 | 165305163 |
| chr4 | 166414834 | 166414921 | chr4 | 166794771 | 166794909 | chr4 | 166796118 | 166796212 |
| chr4 | 168155109 | 168156269 | chr4 | 170865261 | 170865287 | chr4 | 170947287 | 170947325 |
| chr4 | 172734189 | 172734203 | chr4 | 172734592 | 172734790 | chr4 | 174083164 | 174083208 |
| chr4 | 174136704 | 174136734 | chr4 | 174429658 | 174429688 | chr4 | 174430310 | 174430553 |
| chr4 | 174430794 | 174431072 | chr4 | 174438567 | 174438744 | chr4 | 174439822 | 174440257 |
| chr4 | 174440635 | 174440713 | chr4 | 174443212 | 174443242 | chr4 | 174443563 | 174443934 |
| chr4 | 174446508 | 174446525 | chr4 | 174446952 | 174447005 | chr4 | 174449950 | 174450726 |
| chr4 | 174450752 | 174451482 | chr4 | 174451855 | 174452098 | chr4 | 174459185 | 174459374 |
| chr4 | 174459528 | 174459840 | chr4 | 174460186 | 174460221 | chr4 | 175132735 | 175132765 |
| chr4 | 175133085 | 175133201 | chr4 | 175134897 | 175135672 | chr4 | 175135921 | 175136011 |
| chr4 | 175138411 | 175138546 | chr4 | 175138964 | 175139254 | chr4 | 175139593 | 175139685 |
| chr4 | 175750456 | 175750738 | chr4 | 176923424 | 176923558 | chr4 | 176987324 | 176987373 |
| chr4 | 177713228 | 177713437 | chr4 | 178285756 | 178285788 | chr4 | 180979270 | 180979300 |
| chr4 | 180980297 | 180980356 | chr4 | 183063666 | 183063950 | chr4 | 183064617 | 183064655 |
| chr4 | 183064874 | 183064966 | chr4 | 184019249 | 184019316 | chr4 | 184019692 | 184019736 |
| chr4 | 184020106 | 184020179 | chr4 | 184375696 | 184375726 | chr4 | 184644053 | 184644249 |
| chr4 | 184718260 | 184718352 | chr4 | 184826238 | 184826493 | chr4 | 184826938 | 184827237 |
| chr4 | 184921855 | 184922091 | chr4 | 185089696 | 185089797 | chr4 | 185937333 | 185937889 |
| chr4 | 185938497 | 185938564 | chr4 | 185940338 | 185940460 | chr4 | 185941585 | 185942472 |
| chr4 | 185942492 | 185942760 | chr4 | 187647073 | 187647457 | chr5 | 53849 | 53898 |
| chr5 | 92163 | 92399 | chr5 | 303272 | 303301 | chr5 | 320840 | 320982 |
| chr5 | 343916 | 343941 | chr5 | 373363 | 373392 | chr5 | 373872 | 374266 |
| chr5 | 400186 | 400215 | chr5 | 400502 | 400631 | chr5 | 415870 | 415899 |
| chr5 | 481012 | 481037 | chr5 | 491335 | 491536 | chr5 | 524337 | 524404 |
| chr5 | 538758 | 538806 | chr5 | 554299 | 554538 | chr5 | 554871 | 554900 |
| chr5 | 555192 | 555285 | chr5 | 555965 | 555995 | chr5 | 677889 | 678006 |
| chr5 | 909204 | 909304 | chr5 | 912806 | 912835 | chr5 | 1034600 | 1034653 |
| chr5 | 1059523 | 1059556 | chr5 | 1093660 | 1093797 | chr5 | 1131217 | 1131378 |
| chr5 | 1193381 | 1193521 | chr5 | 1193880 | 1193944 | chr5 | 1221197 | 1221307 |
| chr5 | 1271339 | 1271396 | chr5 | 1294630 | 1294767 | chr5 | 1295031 | 1295442 |
| chr5 | 1295605 | 1295662 | chr5 | 1445171 | 1445255 | chr5 | 1445738 | 1445759 |
| chr5 | 1445841 | 1445928 | chr5 | 1446319 | 1446369 | chr5 | 1446443 | 1446599 |
| chr5 | 1747022 | 1747098 | chr5 | 1779526 | 1779556 | chr5 | 1787378 | 1787418 |
| chr5 | 1874892 | 1875099 | chr5 | 1875453 | 1875497 | chr5 | 1875870 | 1876306 |
| chr5 | 1876638 | 1876860 | chr5 | 1877195 | 1877239 | chr5 | 1878014 | 1878028 |
| chr5 | 1878224 | 1878528 | chr5 | 1878831 | 1879045 | chr5 | 1879605 | 1879661 |
| chr5 | 1879690 | 1879719 | chr5 | 1882420 | 1882605 | chr5 | 1882844 | 1882921 |
| chr5 | 1883515 | 1883616 | chr5 | 1884178 | 1884237 | chr5 | 1884557 | 1884698 |
| chr5 | 1885158 | 1885458 | chr5 | 1885985 | 1886076 | chr5 | 1886542 | 1886581 |
| chr5 | 1886812 | 1886841 | chr5 | 1886998 | 1887145 | chr5 | 1887547 | 1887581 |
| chr5 | 1887656 | 1887737 | chr5 | 1930786 | 1931004 | chr5 | 1931055 | 1931286 |
| chr5 | 1931445 | 1931576 | chr5 | 1931618 | 1931754 | chr5 | 1950794 | 1950960 |
| chr5 | 1952624 | 1952638 | chr5 | 2038705 | 2038850 | chr5 | 2225439 | 2225469 |
| chr5 | 2324383 | 2324413 | chr5 | 2541487 | 2541611 | chr5 | 2738848 | 2739129 |
| chr5 | 2739211 | 2739354 | chr5 | 2739877 | 2740300 | chr5 | 2740431 | 2740664 |
| chr5 | 2743617 | 2743659 | chr5 | 2743699 | 2743713 | chr5 | 2748374 | 2748459 |
| chr5 | 2749213 | 2749406 | chr5 | 2749699 | 2749729 | chr5 | 2750435 | 2750516 |
| chr5 | 2750655 | 2750769 | chr5 | 2751855 | 2751894 | chr5 | 2752991 | 2753040 |
| chr5 | 2753048 | 2753078 | chr5 | 2754738 | 2754767 | chr5 | 2755323 | 2756388 |
| chr5 | 2756599 | 2756602 | chr5 | 2756674 | 2757427 | chr5 | 3031879 | 3032018 |
| chr5 | 3152146 | 3152176 | chr5 | 3325042 | 3325272 | chr5 | 3590405 | 3590657 |
| chr5 | 3591354 | 3591388 | chr5 | 3591857 | 3592037 | chr5 | 3592728 | 3592881 |
| chr5 | 3594250 | 3594519 | chr5 | 3595090 | 3595178 | chr5 | 3595850 | 3595991 |
| chr5 | 3596556 | 3596724 | chr5 | 3596825 | 3596880 | chr5 | 3597411 | 3597461 |

TABLE 13-continued

| chr | start | end | chr | start | end | chr | start | end |
|---|---|---|---|---|---|---|---|---|
| chr5 | 3600150 | 3600180 | chr5 | 3602804 | 3603320 | chr5 | 3674053 | 3674224 |
| chr5 | 4144367 | 4144516 | chr5 | 5139754 | 5139900 | chr5 | 5140170 | 5140225 |
| chr5 | 5140630 | 5140757 | chr5 | 5140850 | 5140901 | chr5 | 6228617 | 6228790 |
| chr5 | 6448930 | 6449582 | chr5 | 6482458 | 6482620 | chr5 | 5583461 | 6583579 |
| chr5 | 6687277 | 6687431 | chr5 | 6755789 | 6755843 | chr5 | 7395263 | 7395393 |
| chr5 | 7395434 | 7395538 | chr5 | 7851015 | 7851121 | chr5 | 9546612 | 9546648 |
| chr5 | 10249098 | 10249127 | chr5 | 10333688 | 10334132 | chr5 | 10565021 | 10565227 |
| chr5 | 10565263 | 10565607 | chr5 | 11384965 | 11385363 | chr5 | 11903822 | 11904173 |
| chr5 | 11904196 | 11904379 | chr5 | 11904456 | 11904696 | chr5 | 11904896 | 11904943 |
| chr5 | 14872919 | 14873053 | chr5 | 15500748 | 15500927 | chr5 | 16179049 | 16179141 |
| chr5 | 16179555 | 16179713 | chr5 | 16180183 | 16180260 | chr5 | 16466784 | 16466802 |
| chr5 | 16467042 | 16467120 | chr5 | 16845452 | 16845476 | chr5 | 16845536 | 16845619 |
| chr5 | 16936354 | 16936514 | chr5 | 17203035 | 17203177 | chr5 | 17218195 | 17218225 |
| chr5 | 17218986 | 17219018 | chr5 | 17512114 | 17512144 | chr5 | 22853443 | 22853508 |
| chr5 | 31193937 | 31193989 | chr5 | 31194375 | 31194641 | chr5 | 31639684 | 31639960 |
| chr5 | 31691565 | 31691652 | chr5 | 31855073 | 31855199 | chr5 | 32710331 | 32710470 |
| chr5 | 32710802 | 32710957 | chr5 | 32711017 | 32711531 | chr5 | 32711826 | 32711870 |
| chr5 | 32712077 | 32712101 | chr5 | 32712290 | 32712491 | chr5 | 32712764 | 32713304 |
| chr5 | 33298005 | 33298076 | chr5 | 33892083 | 33892115 | chr5 | 33892413 | 33892443 |
| chr5 | 33936156 | 33936336 | chr5 | 33936486 | 33936516 | chr5 | 33936599 | 33936663 |
| chr5 | 34656932 | 34657034 | chr5 | 35874560 | 35874589 | chr5 | 35939832 | 35939861 |
| chr5 | 37834684 | 37834714 | chr5 | 37835015 | 37835125 | chr5 | 37836231 | 37836260 |
| chr5 | 37836649 | 37837992 | chr5 | 37838548 | 37838885 | chr5 | 37839808 | 37840125 |
| chr5 | 37840530 | 37840853 | chr5 | 38257485 | 38257606 | chr5 | 38257842 | 38257908 |
| chr5 | 38257945 | 38257959 | chr5 | 38557070 | 38557400 | chr5 | 38845675 | 38846164 |
| chr5 | 39343181 | 39343205 | chr5 | 40681122 | 40681227 | chr5 | 40681262 | 40681367 |
| chr5 | 40681676 | 40681839 | chr5 | 40775147 | 40775313 | chr5 | 42424822 | 42425060 |
| chr5 | 42950980 | 42951311 | chr5 | 42951420 | 42952111 | chr5 | 42991825 | 42992241 |
| chr5 | 42992376 | 42992597 | chr5 | 42992783 | 42992934 | chr5 | 42993312 | 42993552 |
| chr5 | 42993852 | 42994193 | chr5 | 42994694 | 42994790 | chr5 | 42995115 | 42995153 |
| chr5 | 43007936 | 43007966 | chr5 | 43008202 | 43008472 | chr5 | 43017953 | 43018176 |
| chr5 | 43018327 | 43018690 | chr5 | 43019238 | 43019347 | chr5 | 43019809 | 43019887 |
| chr5 | 43020146 | 43020294 | chr5 | 43040544 | 43040635 | chr5 | 43040870 | 43040964 |
| chr5 | 43215538 | 43215578 | chr5 | 43397002 | 43397229 | chr5 | 44389782 | 44389852 |
| chr5 | 45695186 | 45695239 | chr5 | 45695314 | 45695533 | chr5 | 45695906 | 45695947 |
| chr5 | 45696336 | 45696439 | chr5 | 49736592 | 49736685 | chr5 | 50262893 | 50263014 |
| chr5 | 50263568 | 50263641 | chr5 | 50264307 | 50264603 | chr5 | 50264820 | 50264850 |
| chr5 | 50265325 | 50265429 | chr5 | 50265721 | 50265880 | chr5 | 50674152 | 50674188 |
| chr5 | 50674560 | 50674590 | chr5 | 50675013 | 50675075 | chr5 | 50678346 | 50678490 |
| chr5 | 50695351 | 50695463 | chr5 | 52084073 | 52084134 | chr5 | 54179610 | 54179633 |
| chr5 | 54180063 | 54180093 | chr5 | 54516371 | 54516680 | chr5 | 54516832 | 54517017 |
| chr5 | 54518651 | 54519288 | chr5 | 54527323 | 54527343 | chr5 | 56246546 | 56246575 |
| chr5 | 56247942 | 56247971 | chr5 | 56248218 | 56248257 | chr5 | 57878271 | 57878375 |
| chr5 | 57878710 | 57878752 | chr5 | 59188291 | 59188327 | chr5 | 59189055 | 59189067 |
| chr5 | 59189189 | 59189206 | chr5 | 59189863 | 59189948 | chr5 | 63254903 | 63255242 |
| chr5 | 63256863 | 63256895 | chr5 | 63257727 | 63257861 | chr5 | 63802007 | 63802304 |
| chr5 | 63802340 | 63802514 | chr5 | 63986488 | 63986527 | chr5 | 63986570 | 63986807 |
| chr5 | 67569803 | 67569832 | chr5 | 67588937 | 67589162 | chr5 | 67589598 | 67589627 |
| chr5 | 67590431 | 67590460 | chr5 | 67591068 | 67591157 | chr5 | 68391309 | 68391336 |
| chr5 | 71014720 | 71014895 | chr5 | 71015180 | 71015728 | chr5 | 71106820 | 71106984 |
| chr5 | 71403566 | 71403653 | chr5 | 71403975 | 71404207 | chr5 | 72416246 | 72416751 |
| chr5 | 72526413 | 72526414 | chr5 | 72526492 | 72526643 | chr5 | 72528434 | 72528464 |
| chr5 | 72529289 | 72529825 | chr5 | 72529890 | 72530609 | chr5 | 72594802 | 72594836 |
| chr5 | 72594868 | 72595016 | chr5 | 72595047 | 72595059 | chr5 | 72595542 | 72595721 |
| chr5 | 72595774 | 72595788 | chr5 | 72599079 | 72599441 | chr5 | 72599463 | 72599833 |
| chr5 | 72677775 | 72677825 | chr5 | 72677998 | 72678028 | chr5 | 72715204 | 72715347 |
| chr5 | 72715591 | 72715695 | chr5 | 72715731 | 72715768 | chr5 | 72716102 | 72716180 |
| chr5 | 72732870 | 72732884 | chr5 | 72733093 | 72733185 | chr5 | 72740147 | 72740184 |
| chr5 | 72746680 | 72746683 | chr5 | 75377883 | 75378033 | chr5 | 75380163 | 75380193 |
| chr5 | 75380624 | 75380974 | chr5 | 76011285 | 76011337 | chr5 | 76012576 | 76012605 |
| chr5 | 76249270 | 76249670 | chr5 | 76249696 | 76249906 | chr5 | 76249945 | 76250150 |
| chr5 | 76250435 | 76250504 | chr5 | 76506469 | 76506506 | chr5 | 76507036 | 76507114 |
| chr5 | 76923679 | 76924023 | chr5 | 76924087 | 76924299 | chr5 | 76924930 | 76924960 |
| chr5 | 76925561 | 76925690 | chr5 | 76928157 | 76928397 | chr5 | 76928688 | 76928906 |
| chr5 | 76932302 | 76932332 | chr5 | 76932542 | 76933265 | chr5 | 76934371 | 76934653 |
| chr5 | 76934677 | 76934870 | chr5 | 76936016 | 76936039 | chr5 | 76936099 | 76936721 |
| chr5 | 76939436 | 76939774 | chr5 | 76940340 | 76940374 | chr5 | 76941201 | 76941326 |
| chr5 | 77140527 | 77140711 | chr5 | 77147563 | 77147649 | chr5 | 77147873 | 77148195 |
| chr5 | 77148498 | 77148695 | chr5 | 77268367 | 77269237 | chr5 | 77269270 | 77269309 |
| chr5 | 78407651 | 78407840 | chr5 | 78408192 | 78408274 | chr5 | 78408298 | 78408461 |
| chr5 | 78910231 | 78910332 | chr5 | 79598681 | 79598759 | chr5 | 79783240 | 79783271 |
| chr5 | 79864898 | 79865078 | chr5 | 79866100 | 79866414 | chr5 | 79947584 | 79947707 |
| chr5 | 80255816 | 80256074 | chr5 | 80689543 | 80689735 | chr5 | 80690118 | 80690239 |
| chr5 | 82767429 | 82767793 | chr5 | 82768892 | 82769061 | chr5 | 83679195 | 83679225 |
| chr5 | 83679681 | 83680340 | chr5 | 83680615 | 83680664 | chr5 | 83680694 | 83680708 |
| chr5 | 87955460 | 87955664 | chr5 | 87956199 | 87956662 | chr5 | 87956680 | 87956964 |
| chr5 | 87962966 | 87963002 | chr5 | 87963390 | 87963511 | chr5 | 87967773 | 87968077 |
| chr5 | 87968486 | 87968685 | chr5 | 87968773 | 87968858 | chr5 | 87970193 | 87970872 |

TABLE 13-continued

| chr | start | end | chr | start | end | chr | start | end |
|---|---|---|---|---|---|---|---|---|
| chr5 | 87974104 | 87974307 | chr5 | 87974868 | 87975023 | chr5 | 87976028 | 87976308 |
| chr5 | 87976525 | 87976559 | chr5 | 87979756 | 87979834 | chr5 | 87979894 | 87979912 |
| chr5 | 87980142 | 87980250 | chr5 | 87980954 | 87981325 | chr5 | 87984532 | 87984657 |
| chr5 | 87985922 | 87985954 | chr5 | 87986210 | 87986281 | chr5 | 87986547 | 87986581 |
| chr5 | 87988516 | 87988584 | chr5 | 87990408 | 87990452 | chr5 | 88185470 | 88186001 |
| chr5 | 89854856 | 89854902 | chr5 | 94955681 | 94955919 | chr5 | 94956935 | 94957000 |
| chr5 | 94982134 | 94982225 | chr5 | 95767894 | 95768384 | chr5 | 95768920 | 95769093 |
| chr5 | 96114587 | 96114632 | chr5 | 100236682 | 100236757 | chr5 | 100238882 | 100239119 |
| chr5 | 100239135 | 100239151 | chr5 | 101631487 | 101631533 | chr5 | 101632295 | 101632573 |
| chr5 | 107005983 | 107006186 | chr5 | 111987781 | 111987818 | chr5 | 112042844 | 112042873 |
| chr5 | 112042904 | 112043289 | chr5 | 112073358 | 112073516 | chr5 | 112170808 | 112170837 |
| chr5 | 112175198 | 112175227 | chr5 | 112175640 | 112175669 | chr5 | 112258359 | 112258388 |
| chr5 | 112258634 | 112258663 | chr5 | 112629427 | 112629674 | chr5 | 113391265 | 113392018 |
| chr5 | 113698567 | 113698583 | chr5 | 113698670 | 113698783 | chr5 | 113699008 | 113699119 |
| chr5 | 114515010 | 114515579 | chr5 | 114515611 | 114515671 | chr5 | 115151267 | 115151357 |
| chr5 | 115151650 | 115152384 | chr5 | 115152617 | 115152638 | chr5 | 115297192 | 115297292 |
| chr5 | 115297327 | 115297556 | chr5 | 115297928 | 115297985 | chr5 | 115298496 | 115298581 |
| chr5 | 115298985 | 115299041 | chr5 | 119799931 | 119799986 | chr5 | 119801299 | 119801445 |
| chr5 | 121413537 | 121413590 | chr5 | 122422240 | 122422292 | chr5 | 122422616 | 122422661 |
| chr5 | 122423328 | 122423376 | chr5 | 122425128 | 122425168 | chr5 | 122431118 | 122431378 |
| chr5 | 124128454 | 124128497 | chr5 | 126626283 | 126626738 | chr5 | 127872942 | 127872990 |
| chr5 | 127873553 | 127873710 | chr5 | 127874448 | 127874477 | chr5 | 127874706 | 127874839 |
| chr5 | 128300680 | 128300694 | chr5 | 128300713 | 128300794 | chr5 | 128796081 | 128796244 |
| chr5 | 128796867 | 128796985 | chr5 | 128797344 | 128797386 | chr5 | 129240068 | 129240101 |
| chr5 | 131992096 | 131992157 | chr5 | 132947486 | 132947836 | chr5 | 133820024 | 133820040 |
| chr5 | 134364195 | 134364234 | chr5 | 134366718 | 134366788 | chr5 | 134367108 | 134367203 |
| chr5 | 134374447 | 134374505 | chr5 | 134374792 | 134375210 | chr5 | 134376222 | 134376375 |
| chr5 | 134376732 | 134376824 | chr5 | 134385952 | 134386167 | chr5 | 134386185 | 134386383 |
| chr5 | 134582864 | 134582894 | chr5 | 134735622 | 134735651 | chr5 | 134825463 | 134825518 |
| chr5 | 134825913 | 134826006 | chr5 | 134870446 | 134870515 | chr5 | 134870780 | 134870926 |
| chr5 | 134871601 | 134872049 | chr5 | 134879478 | 134879990 | chr5 | 134880110 | 134880501 |
| chr5 | 134914627 | 134914748 | chr5 | 135265737 | 135265767 | chr5 | 135266114 | 135266128 |
| chr5 | 135266578 | 135266672 | chr5 | 135528201 | 135528233 | chr5 | 136834050 | 136834050 |
| chr5 | 136834290 | 136834506 | chr5 | 136834720 | 136834826 | chr5 | 137225092 | 137225297 |
| chr5 | 137912123 | 137912148 | chr5 | 138196197 | 138196213 | chr5 | 138196393 | 138196408 |
| chr5 | 138273817 | 138273854 | chr5 | 139045286 | 139045315 | chr5 | 139047990 | 139048162 |
| chr5 | 139056666 | 139056804 | chr5 | 139227773 | 139227909 | chr5 | 139525728 | 139525758 |
| chr5 | 139779833 | 139779871 | chr5 | 140174798 | 140174839 | chr5 | 140187094 | 140187146 |
| chr5 | 140305978 | 140306050 | chr5 | 140306445 | 140306619 | chr5 | 140306575 | 140306733 |
| chr5 | 140346595 | 140346671 | chr5 | 140514891 | 140614921 | chr5 | 140604459 | 140604501 |
| chr5 | 140613926 | 140614014 | chr5 | 140614314 | 140614328 | chr5 | 140683631 | 140683772 |
| chr5 | 140777328 | 140777487 | chr5 | 140787623 | 140787637 | chr5 | 140797076 | 140797278 |
| chr5 | 140797328 | 140797342 | chr5 | 140800479 | 140800964 | chr5 | 140801035 | 140801246 |
| chr5 | 140855598 | 140856458 | chr5 | 140856547 | 140856622 | chr5 | 141031121 | 141031150 |
| chr5 | 141263035 | 141263142 | chr5 | 141931340 | 141931354 | chr5 | 141931425 | 141931539 |
| chr5 | 142784967 | 142785272 | chr5 | 145713645 | 145713896 | chr5 | 145717175 | 145717196 |
| chr5 | 145717249 | 145717437 | chr5 | 145718802 | 145719753 | chr5 | 145719835 | 145719925 |
| chr5 | 145720812 | 145720917 | chr5 | 145722116 | 145722466 | chr5 | 145722561 | 145723027 |
| chr5 | 145724502 | 145724698 | chr5 | 145725694 | 145725844 | chr5 | 146257332 | 146257602 |
| chr5 | 146889332 | 146889575 | chr5 | 149503827 | 149503856 | chr5 | 149682074 | 149682166 |
| chr5 | 150029147 | 150029245 | chr5 | 150051101 | 150051667 | chr5 | 150326159 | 150326188 |
| chr5 | 150400123 | 150400203 | chr5 | 151066442 | 151066474 | chr5 | 151304301 | 151304401 |
| chr5 | 153852664 | 153852792 | chr5 | 153853420 | 153853478 | chr5 | 153854330 | 153854360 |
| chr5 | 153855175 | 153855264 | chr5 | 153855658 | 153855839 | chr5 | 153856149 | 153856396 |
| chr5 | 153856936 | 153856996 | chr5 | 153857379 | 153857429 | chr5 | 153858319 | 163858599 |
| chr5 | 153859676 | 153859708 | chr5 | 153862037 | 153862179 | chr5 | 153862219 | 153862577 |
| chr5 | 153863421 | 153863451 | chr5 | 154030048 | 154030074 | chr5 | 154209926 | 154209987 |
| chr5 | 154318148 | 154318179 | chr5 | 155107794 | 155107848 | chr5 | 155108161 | 155108267 |
| chr5 | 155108356 | 155108526 | chr5 | 155108733 | 155108763 | chr5 | 156558444 | 156558477 |
| chr5 | 156655170 | 156655200 | chr5 | 156874257 | 156874308 | chr5 | 157001739 | 157001843 |
| chr5 | 157078419 | 157078449 | chr5 | 157098362 | 157098619 | chr5 | 157673769 | 157673964 |
| chr5 | 158478513 | 158478764 | chr5 | 158524692 | 158524748 | chr5 | 158524865 | 158524925 |
| chr5 | 158527443 | 158528069 | chr5 | 159399095 | 159399099 | chr5 | 160975724 | 160975754 |
| chr5 | 161274310 | 161274554 | chr5 | 166865449 | 166865473 | chr5 | 167956177 | 167956266 |
| chr5 | 167956414 | 167956595 | chr5 | 168233396 | 168233482 | chr5 | 168727924 | 168727927 |
| chr5 | 169064327 | 169064805 | chr5 | 169532927 | 169533012 | chr5 | 170108287 | 170108372 |
| chr5 | 170735154 | 170735206 | chr5 | 170735731 | 170735788 | chr5 | 170736116 | 170736163 |
| chr5 | 170736716 | 170736830 | chr5 | 170737282 | 170737479 | chr5 | 170737771 | 170737863 |
| chr5 | 170737936 | 170738689 | chr5 | 170738824 | 170739481 | chr5 | 170739823 | 170740027 |
| chr5 | 170740461 | 170740477 | chr5 | 170740575 | 170741031 | chr5 | 170741507 | 170742275 |
| chr5 | 170742387 | 170742599 | chr5 | 170742673 | 170742827 | chr5 | 170743127 | 170743479 |
| chr5 | 170743647 | 170744128 | chr5 | 170744375 | 170744562 | chr5 | 170745389 | 170745480 |
| chr5 | 171352123 | 171352153 | chr5 | 172354043 | 172354118 | chr5 | 172655879 | 172656215 |
| chr5 | 172659225 | 172659290 | chr5 | 172659496 | 172659655 | chr5 | 172659855 | 172660025 |
| chr5 | 172660142 | 172660218 | chr5 | 172660719 | 172661000 | chr5 | 172661127 | 172661684 |
| chr5 | 172664226 | 172654487 | chr5 | 172665590 | 172665812 | chr5 | 172670983 | 172671018 |
| chr5 | 172671345 | 172671481 | chr5 | 172671640 | 172671968 | chr5 | 172672477 | 172672663 |
| chr5 | 172754589 | 172754621 | chr5 | 172754832 | 172754931 | chr5 | 172755470 | 172755562 |

TABLE 13-continued

| chr | start | end | chr | start | end | chr | start | end |
|---|---|---|---|---|---|---|---|---|
| chr5 | 172755595 | 172755663 | chr5 | 172757048 | 172757111 | chr5 | 174115388 | 174115861 |
| chr5 | 174147523 | 174147596 | chr5 | 174150415 | 174150445 | chr5 | 174159300 | 174159588 |
| chr5 | 174162874 | 174162904 | chr5 | 174220971 | 174221001 | chr5 | 174870738 | 174870786 |
| chr5 | 174871174 | 174871497 | chr5 | 174921456 | 174921483 | chr5 | 175085147 | 175085209 |
| chr5 | 175085525 | 175085719 | chr5 | 175223671 | 175223709 | chr5 | 175298549 | 175298883 |
| chr5 | 175299294 | 175299396 | chr5 | 175300351 | 175300381 | chr5 | 175621390 | 175621501 |
| chr5 | 175792865 | 175792931 | chr5 | 175792998 | 175793063 | chr5 | 175831257 | 175831326 |
| chr5 | 175971447 | 175971471 | chr5 | 176024005 | 176024318 | chr5 | 176046363 | 176046554 |
| chr5 | 176107274 | 176107484 | chr5 | 176107518 | 176107586 | chr5 | 176236721 | 176236898 |
| chr5 | 176264805 | 176264915 | chr5 | 176295786 | 176295892 | chr5 | 176520166 | 176520195 |
| chr5 | 176522400 | 176522566 | chr5 | 176764100 | 176764169 | chr5 | 176827656 | 176827685 |
| chr5 | 177031167 | 177031197 | chr5 | 177408292 | 177408443 | chr5 | 177411638 | 177412141 |
| chr5 | 177713376 | 177713468 | chr5 | 178004325 | 178004374 | chr5 | 178016682 | 178016983 |
| chr5 | 178017520 | 178017867 | chr5 | 178368074 | 178368121 | chr5 | 178487107 | 178487303 |
| chr5 | 178487342 | 178487398 | chr5 | 178576356 | 178576499 | chr5 | 178655753 | 178655871 |
| chr5 | 178771314 | 178771630 | chr5 | 178771724 | 178771859 | chr5 | 178772205 | 178772272 |
| chr5 | 178772603 | 178772729 | chr5 | 178781548 | 178781577 | chr5 | 178957637 | 178957944 |
| chr5 | 179214113 | 179214196 | chr5 | 179270726 | 179270748 | chr5 | 179780104 | 179780144 |
| chr5 | 179780706 | 179780985 | chr5 | 179867486 | 179867548 | chr5 | 180017118 | 180017198 |
| chr5 | 180017608 | 180017933 | chr5 | 180018485 | 180018498 | chr5 | 180047440 | 180047606 |
| chr5 | 180075846 | 180075857 | chr5 | 180076054 | 180076317 | chr5 | 180076567 | 180076602 |
| chr5 | 180076804 | 180076996 | chr5 | 180101016 | 180101167 | chr5 | 180101252 | 180101332 |
| chr5 | 180326126 | 180326156 | chr5 | 180527546 | 180527698 | chr5 | 180594851 | 180594927 |
| chr5 | 180594987 | 180595002 | chr5 | 180600858 | 180601068 | chr5 | 180601128 | 180601218 |
| chr6 | 373148 | 373290 | chr6 | 391173 | 391899 | chr6 | 392410 | 392433 |
| chr6 | 392588 | 392958 | chr6 | 393125 | 393472 | chr6 | 711142 | 711293 |
| chr6 | 1312000 | 1312096 | chr6 | 1312595 | 1312708 | chr6 | 1314088 | 1314100 |
| chr6 | 1378222 | 1378475 | chr6 | 1379584 | 1379614 | chr6 | 1379909 | 1379952 |
| chr6 | 1383677 | 1383708 | chr6 | 1383860 | 1384179 | chr6 | 1384626 | 1384644 |
| chr6 | 1385118 | 1385170 | chr6 | 1386071 | 1386112 | chr6 | 1389124 | 1389262 |
| chr6 | 1390241 | 1390405 | chr6 | 1390424 | 1390758 | chr6 | 1390956 | 1391035 |
| chr6 | 1391318 | 1391379 | chr6 | 1524199 | 1524283 | chr6 | 1605387 | 1605454 |
| chr6 | 1620672 | 1620701 | chr6 | 1624977 | 1625068 | chr6 | 1625128 | 1625818 |
| chr6 | 3053299 | 3053386 | chr6 | 3229029 | 3229059 | chr6 | 3229423 | 3229510 |
| chr6 | 3232010 | 3232260 | chr6 | 3247675 | 3247704 | chr6 | 3285222 | 3285513 |
| chr6 | 3405645 | 3405713 | chr6 | 4775062 | 4775222 | chr6 | 4836440 | 4836458 |
| chr6 | 4951247 | 4951390 | chr6 | 5783325 | 5783496 | chr6 | 5996952 | 5996989 |
| chr6 | 5997802 | 5997832 | chr6 | 6003287 | 6003528 | chr6 | 6004350 | 6004743 |
| chr6 | 6004837 | 6005417 | chr6 | 6006374 | 6006419 | chr6 | 6006674 | 6006883 |
| chr6 | 6007593 | 6008227 | chr6 | 6367086 | 6367271 | chr6 | 6753803 | 6753839 |
| chr6 | 7226334 | 2226363 | chr6 | 7726630 | 7726659 | chr6 | 7726952 | 7726981 |
| chr6 | 7727699 | 7727768 | chr6 | 7728087 | 7728142 | chr6 | 7728849 | 7728941 |
| chr6 | 7731054 | 7731083 | chr6 | 7892314 | 7892412 | chr6 | 10381507 | 10381592 |
| chr6 | 10381695 | 10381968 | chr6 | 10382722 | 10383049 | chr6 | 10383739 | 10383774 |
| chr6 | 10384950 | 10384974 | chr6 | 10385280 | 10385939 | chr6 | 10386210 | 10386273 |
| chr6 | 10390023 | 10391187 | chr6 | 10410518 | 10410578 | chr6 | 10411356 | 10411510 |
| chr6 | 10415113 | 10415215 | chr6 | 10415559 | 10415713 | chr6 | 10416118 | 10416351 |
| chr6 | 10417158 | 10417529 | chr6 | 10419086 | 10419439 | chr6 | 10419477 | 10419506 |
| chr6 | 10419744 | 10419941 | chr6 | 10421053 | 10421451 | chr6 | 10421549 | 10422635 |
| chr6 | 10423613 | 10423704 | chr6 | 10425630 | 10425789 | chr6 | 10425839 | 10426884 |
| chr6 | 10542836 | 10542977 | chr6 | 10881856 | 10882057 | chr6 | 10882321 | 10882350 |
| chr6 | 10883008 | 10883022 | chr6 | 10887078 | 10887685 | chr6 | 11044052 | 11044572 |
| chr6 | 12288517 | 12288681 | chr6 | 12749899 | 12749940 | chr6 | 15513780 | 15513981 |
| chr6 | 16197030 | 16197112 | chr6 | 16729595 | 16729624 | chr6 | 17281417 | 17281534 |
| chr6 | 18035867 | 18036015 | chr6 | 19691638 | 19691841 | chr6 | 19692143 | 19692318 |
| chr6 | 19837064 | 19837140 | chr6 | 19892478 | 19892627 | chr6 | 21664729 | 21664749 |
| chr6 | 21665004 | 21665043 | chr6 | 24358291 | 24358320 | chr6 | 24360074 | 24360170 |
| chr6 | 24494679 | 24494766 | chr6 | 24647342 | 24647381 | chr6 | 26184363 | 26184391 |
| chr6 | 26188715 | 26189393 | chr6 | 26189955 | 26189991 | chr6 | 26199137 | 26199167 |
| chr6 | 26199686 | 26199716 | chr6 | 26214611 | 26214648 | chr6 | 26235223 | 26235623 |
| chr6 | 26240504 | 26241118 | chr6 | 26250468 | 26250826 | chr6 | 26251054 | 26251182 |
| chr6 | 26251816 | 26251954 | chr6 | 26252074 | 26252098 | chr6 | 26252141 | 26252151 |
| chr6 | 26271406 | 26271762 | chr6 | 26271971 | 26272001 | chr6 | 26272512 | 26272617 |
| chr6 | 26273400 | 26273418 | chr6 | 26284811 | 26284898 | chr6 | 26327806 | 26327982 |
| chr6 | 26328294 | 26328457 | chr6 | 26332178 | 26332218 | chr6 | 26501790 | 26502209 |
| chr6 | 26550994 | 26551034 | chr6 | 26577158 | 26577475 | chr6 | 26987967 | 26988166 |
| chr6 | 27059783 | 27059848 | chr6 | 27064682 | 27065198 | chr6 | 27173528 | 27173546 |
| chr6 | 27173633 | 27173855 | chr6 | 27173915 | 27174181 | chr6 | 27182869 | 27182899 |
| chr6 | 27203269 | 27203286 | chr6 | 27205300 | 27205441 | chr6 | 27205671 | 27205836 |
| chr6 | 27205914 | 27206040 | chr6 | 27218951 | 27218980 | chr6 | 27228180 | 27228186 |
| chr6 | 27228290 | 27228395 | chr6 | 27235876 | 27235905 | chr6 | 27247636 | 27247724 |
| chr6 | 27256097 | 27256173 | chr6 | 27256383 | 27256420 | chr6 | 27264332 | 27264364 |
| chr6 | 27279845 | 27280012 | chr6 | 27463029 | 27463687 | chr6 | 27512761 | 27512883 |
| chr6 | 27512995 | 27513487 | chr6 | 27533822 | 27534341 | chr6 | 27559809 | 27560075 |
| chr6 | 27573171 | 27573392 | chr6 | 27598738 | 27598860 | chr6 | 27599159 | 27599341 |
| chr6 | 27635265 | 27635434 | chr6 | 27647712 | 27647735 | chr6 | 27647891 | 27647896 |
| chr6 | 27648933 | 27649134 | chr6 | 27783039 | 27783052 | chr6 | 27799464 | 27799581 |
| chr6 | 27834676 | 27834835 | chr6 | 27835047 | 27835096 | chr6 | 27835378 | 27835417 |

TABLE 13-continued

| chr | start | end | chr | start | end | chr | start | end |
|---|---|---|---|---|---|---|---|---|
| chr6 | 27839726 | 27840082 | chr6 | 27840543 | 27840617 | chr6 | 27841104 | 27841136 |
| chr6 | 27858515 | 27858637 | chr6 | 28175189 | 28176212 | chr6 | 28227076 | 28227141 |
| chr6 | 28303562 | 28303607 | chr6 | 28303815 | 28304263 | chr6 | 28367109 | 28367346 |
| chr6 | 28367491 | 28367774 | chr6 | 28410976 | 28411087 | chr6 | 28411152 | 28411353 |
| chr6 | 28414977 | 28414991 | chr6 | 28457608 | 28457638 | chr6 | 28457870 | 28458158 |
| chr6 | 28956323 | 28956511 | chr6 | 28956660 | 28956719 | chr6 | 30095233 | 30095262 |
| chr6 | 30095418 | 30095570 | chr6 | 30130804 | 30130895 | chr6 | 30644680 | 30644798 |
| chr6 | 32374147 | 32374176 | chr6 | 32374739 | 32374768 | chr6 | 32376051 | 32376080 |
| chr6 | 33161275 | 33161342 | chr6 | 33632930 | 33633000 | chr6 | 33636388 | 33636418 |
| chr6 | 33955505 | 33955731 | chr6 | 34113872 | 34113957 | chr6 | 34170970 | 34170986 |
| chr6 | 34171046 | 34171061 | chr6 | 34219930 | 34219951 | chr6 | 34396517 | 34396542 |
| chr6 | 34714803 | 34714820 | chr6 | 34724198 | 34724228 | chr6 | 35150041 | 35150080 |
| chr6 | 35182493 | 35182522 | chr6 | 35479613 | 35479642 | chr6 | 35992428 | 35992458 |
| chr6 | 36165662 | 36165692 | chr6 | 36178031 | 36178301 | chr6 | 36252984 | 36253171 |
| chr6 | 36313883 | 36313913 | chr6 | 36808323 | 36808441 | chr6 | 37024559 | 37024589 |
| chr6 | 37664140 | 37664187 | chr6 | 37673320 | 37673611 | chr6 | 37776410 | 32776440 |
| chr6 | 37776719 | 37776735 | chr6 | 38683212 | 38683235 | chr6 | 39281088 | 39281133 |
| chr6 | 39281824 | 39281875 | chr6 | 39329863 | 39329892 | chr6 | 39508464 | 39508493 |
| chr6 | 39760401 | 39760661 | chr6 | 40554653 | 40554699 | chr6 | 41337072 | 41337128 |
| chr6 | 41339263 | 41339558 | chr6 | 41339602 | 41339838 | chr6 | 41340902 | 41341182 |
| chr6 | 41341501 | 41341549 | chr6 | 41342243 | 41342275 | chr6 | 41342807 | 41342837 |
| chr6 | 41605937 | 41605951 | chr6 | 41606038 | 41606356 | chr6 | 41606528 | 41606542 |
| chr6 | 41773520 | 41773903 | chr6 | 41774459 | 41774576 | chr6 | 42738966 | 42739049 |
| chr6 | 42773440 | 42773471 | chr6 | 42846662 | 42846705 | chr6 | 42879554 | 42879568 |
| chr6 | 42879622 | 42879718 | chr6 | 42928321 | 42928454 | chr6 | 43211193 | 43211311 |
| chr6 | 43424444 | 43424470 | chr6 | 43425479 | 43425509 | chr6 | 43478676 | 43478745 |
| chr6 | 43612825 | 43612898 | chr6 | 43613053 | 43613067 | chr6 | 43639548 | 43639710 |
| chr6 | 43748463 | 43748616 | chr6 | 44240914 | 44241108 | chr6 | 44695763 | 44695795 |
| chr6 | 45388716 | 45388775 | chr6 | 46702982 | 46703123 | chr6 | 46703350 | 46703436 |
| chr6 | 47590582 | 47590604 | chr6 | 50674372 | 50674750 | chr6 | 50681699 | 50681851 |
| chr6 | 50681911 | 50681942 | chr6 | 50682319 | 50682338 | chr6 | 50682659 | 50682683 |
| chr6 | 50682712 | 50682940 | chr6 | 50682992 | 50683227 | chr6 | 50684939 | 50684969 |
| chr6 | 50689913 | 50690039 | chr6 | 50691065 | 50691095 | chr6 | 50692083 | 50692212 |
| chr6 | 50692300 | 50692481 | chr6 | 50787216 | 50787876 | chr6 | 50787950 | 50788352 |
| chr6 | 50789374 | 50789404 | chr6 | 50791187 | 50791494 | chr6 | 50791551 | 50791632 |
| chr6 | 50793335 | 50793404 | chr6 | 50793728 | 50793882 | chr6 | 50794531 | 50794693 |
| chr6 | 50803834 | 50803867 | chr6 | 50804131 | 50804368 | chr6 | 50808681 | 50808854 |
| chr6 | 50810551 | 50810713 | chr6 | 50811062 | 50811488 | chr6 | 50813258 | 50813939 |
| chr6 | 50814569 | 50814599 | chr6 | 50817023 | 50817229 | chr6 | 50817905 | 50817935 |
| chr6 | 50818449 | 50818706 | chr6 | 50818920 | 50819000 | chr6 | 52227752 | 52227781 |
| chr6 | 52228008 | 52228037 | chr6 | 52344375 | 52344405 | chr6 | 63212491 | 53213970 |
| chr6 | 55443691 | 55443946 | chr6 | 56112262 | 56112386 | chr6 | 56716390 | 56716410 |
| chr6 | 56818656 | 56818937 | chr6 | 56819217 | 56819637 | chr6 | 56819897 | 56819926 |
| chr6 | 58147447 | 58147480 | chr6 | 58147790 | 58147976 | chr6 | 62995356 | 62995874 |
| chr6 | 62996078 | 62996146 | chr6 | 62996443 | 62996489 | chr6 | 70992137 | 70992162 |
| chr6 | 70992415 | 70992560 | chr6 | 70992830 | 70993015 | chr6 | 71665638 | 71665723 |
| chr6 | 71666788 | 21666986 | chr6 | 22129789 | 72129829 | chr6 | 72130191 | 72130464 |
| chr6 | 72596120 | 72596315 | chr6 | 72596950 | 72596980 | chr6 | 73329784 | 73330126 |
| chr6 | 73330834 | 73331304 | chr6 | 73331515 | 73331850 | chr6 | 73331876 | 73333099 |
| chr6 | 73980699 | 73980722 | chr6 | 76059561 | 76059787 | chr6 | 78172177 | 78172275 |
| chr6 | 78172323 | 78172572 | chr6 | 78173212 | 78173264 | chr6 | 78173696 | 78173725 |
| chr6 | 78173772 | 78173984 | chr6 | 78176458 | 78176820 | chr6 | 79620475 | 79620699 |
| chr6 | 80656930 | 80657180 | chr6 | 82463270 | 82463310 | chr6 | 82958615 | 82958646 |
| chr6 | 84141298 | 84141412 | chr6 | 84417436 | 84417700 | chr6 | 84418261 | 84418281 |
| chr6 | 84418644 | 84418788 | chr6 | 84419157 | 84419415 | chr6 | 84562873 | 84563242 |
| chr6 | 84563489 | 84563542 | chr6 | 85050460 | 85050504 | chr6 | 85472407 | 85473703 |
| chr6 | 85473928 | 85474378 | chr6 | 85474594 | 85474736 | chr6 | 85476233 | 85476285 |
| chr6 | 85476998 | 85477028 | chr6 | 85478514 | 85478724 | chr6 | 85482530 | 85482796 |
| chr6 | 85483345 | 85483375 | chr6 | 85483760 | 85483931 | chr6 | 85484558 | 85484625 |
| chr6 | 85484717 | 85484920 | chr6 | 86302413 | 86302454 | chr6 | 87647114 | 87647143 |
| chr6 | 87862092 | 87862172 | chr6 | 88876963 | 88877421 | chr6 | 91320285 | 91320318 |
| chr6 | 91320949 | 91321295 | chr6 | 94126973 | 94127064 | chr6 | 94127455 | 94127544 |
| chr6 | 94128365 | 94128399 | chr6 | 94129219 | 94129252 | chr6 | 94129509 | 94129575 |
| chr6 | 96464100 | 96464204 | chr6 | 99271926 | 99272810 | chr6 | 99273369 | 99273410 |
| chr6 | 99277180 | 99277330 | chr6 | 99279556 | 99279612 | chr6 | 99280594 | 99280744 |
| chr6 | 99281014 | 99281036 | chr6 | 99281068 | 99281385 | chr6 | 99283512 | 99283582 |
| chr6 | 99290360 | 99290398 | chr6 | 99291264 | 99291341 | chr6 | 99292252 | 99292417 |
| chr6 | 99295726 | 99295863 | chr6 | 99296062 | 99296364 | chr6 | 99296408 | 99296467 |
| chr6 | 99396456 | 99396473 | chr6 | 99842067 | 99842163 | chr6 | 99842358 | 99842382 |
| chr6 | 100038682 | 100038706 | chr6 | 100038786 | 100038964 | chr6 | 100039275 | 100039289 |
| chr6 | 100050754 | 100050810 | chr6 | 100050859 | 100051108 | chr6 | 100051360 | 100051507 |
| chr6 | 100051772 | 100051971 | chr6 | 100053221 | 100053511 | chr6 | 100054866 | 100054917 |
| chr6 | 100061022 | 100061076 | chr6 | 100061311 | 100061419 | chr6 | 100062178 | 100062586 |
| chr6 | 100062944 | 100063068 | chr6 | 100441498 | 100441737 | chr6 | 100441762 | 100441966 |
| chr6 | 100903384 | 100903404 | chr6 | 100903561 | 100903631 | chr6 | 100904214 | 100904275 |
| chr6 | 100905969 | 100906016 | chr6 | 100911686 | 100911723 | chr6 | 100912070 | 100912119 |
| chr6 | 100912421 | 100912445 | chr6 | 100912466 | 100912480 | chr6 | 100912919 | 100913050 |
| chr6 | 100916101 | 100915205 | chr6 | 101840708 | 101840820 | chr6 | 101846782 | 101846789 |

TABLE 13-continued

| chr | start | end | chr | start | end | chr | start | end |
|---|---|---|---|---|---|---|---|---|
| chr6 | 101847185 | 101847215 | chr6 | 101850147 | 101850275 | chr6 | 105388679 | 105388708 |
| chr6 | 105389510 | 105389710 | chr6 | 105400913 | 105401007 | chr6 | 105401620 | 105401874 |
| chr6 | 105404574 | 105404674 | chr6 | 105405656 | 105405772 | chr6 | 105406098 | 105406128 |
| chr6 | 105584264 | 105584319 | chr6 | 105584367 | 105585554 | chr6 | 105821423 | 105821453 |
| chr6 | 106429049 | 106429475 | chr6 | 106429590 | 106429624 | chr6 | 106434339 | 106434368 |
| chr6 | 106441869 | 106442979 | chr6 | 106731553 | 106731597 | chr6 | 106960908 | 106961023 |
| chr6 | 107562814 | 107562859 | chr6 | 108280322 | 108280352 | chr6 | 108435075 | 108435263 |
| chr6 | 108436072 | 108436526 | chr6 | 108438261 | 108438577 | chr6 | 108440091 | 108440644 |
| chr6 | 108440745 | 108440961 | chr6 | 108479290 | 108479665 | chr6 | 108484909 | 108485406 |
| chr6 | 108485665 | 108485905 | chr6 | 108486158 | 108486394 | chr6 | 108487724 | 108488416 |
| chr6 | 108489662 | 108489808 | chr6 | 108490067 | 108490245 | chr6 | 108490297 | 108490514 |
| chr6 | 108490538 | 108490633 | chr6 | 108490978 | 108491000 | chr6 | 108491108 | 108491423 |
| chr6 | 108492270 | 108492451 | chr6 | 108495681 | 108495817 | chr6 | 108495916 | 108495951 |
| chr6 | 108496208 | 108496649 | chr6 | 108497494 | 108497796 | chr6 | 108497827 | 108497881 |
| chr6 | 110437721 | 110437751 | chr6 | 110679123 | 110679414 | chr6 | 110797678 | 110797708 |
| chr6 | 110798007 | 110798036 | chr6 | 116783448 | 116783493 | chr6 | 117086249 | 117086639 |
| chr6 | 117585967 | 117586004 | chr6 | 117586847 | 117587169 | chr6 | 117587480 | 117587577 |
| chr6 | 117591161 | 117591191 | chr6 | 117591411 | 117591596 | chr6 | 117591684 | 117591743 |
| chr6 | 118228102 | 118228151 | chr6 | 118228747 | 118228828 | chr6 | 118229305 | 118229383 |
| chr6 | 118229626 | 118229818 | chr6 | 118241228 | 118241308 | chr6 | 118241395 | 118241500 |
| chr6 | 119254654 | 119254678 | chr6 | 121758672 | 121758994 | chr6 | 123317073 | 123317589 |
| chr6 | 123317797 | 123317833 | chr6 | 124124432 | 124124466 | chr6 | 124124860 | 124125016 |
| chr6 | 125284131 | 125284175 | chr6 | 126068092 | 126068178 | chr6 | 127439379 | 127439453 |
| chr6 | 127439985 | 127440127 | chr6 | 127440331 | 127440962 | chr6 | 127441031 | 127441123 |
| chr6 | 127441554 | 127441762 | chr6 | 127442021 | 127442070 | chr6 | 127442090 | 127442104 |
| chr6 | 127840501 | 127840681 | chr6 | 129204459 | 129204524 | chr6 | 130686534 | 130687057 |
| chr6 | 131602584 | 131602694 | chr6 | 132722078 | 132722141 | chr6 | 132722158 | 132722196 |
| chr6 | 133561740 | 133562070 | chr6 | 133562374 | 133562435 | chr6 | 133562675 | 133563058 |
| chr6 | 133563327 | 133563918 | chr6 | 134067453 | 134067471 | chr6 | 134176232 | 134176299 |
| chr6 | 134176549 | 134176579 | chr6 | 134210528 | 134211018 | chr6 | 134211112 | 134211367 |
| chr6 | 134213944 | 134213987 | chr6 | 134214077 | 134214364 | chr6 | 134589500 | 134589604 |
| chr6 | 134638950 | 134639003 | chr6 | 137241928 | 137242205 | chr6 | 137243208 | 137243410 |
| chr6 | 137244114 | 137244148 | chr6 | 137244236 | 137244465 | chr6 | 137311158 | 137311380 |
| chr6 | 137366354 | 137366383 | chr6 | 137809141 | 137809365 | chr6 | 137809446 | 137809916 |
| chr6 | 137810033 | 137811088 | chr6 | 137813787 | 137813895 | chr6 | 137814604 | 137814618 |
| chr6 | 137814654 | 137814763 | chr6 | 137815008 | 137815170 | chr6 | 137815225 | 137815662 |
| chr6 | 137816472 | 137817351 | chr6 | 137818505 | 137818598 | chr6 | 137818619 | 137819368 |
| chr6 | 146755567 | 146755649 | chr6 | 149868368 | 149868387 | chr6 | 150284552 | 150284581 |
| chr6 | 150285056 | 150285368 | chr6 | 150285545 | 150285885 | chr6 | 150286100 | 150286639 |
| chr6 | 150358970 | 150359192 | chr6 | 151561016 | 151561340 | chr6 | 151561369 | 151561857 |
| chr6 | 151562066 | 151562563 | chr6 | 151815055 | 151815089 | chr6 | 152419908 | 152419940 |
| chr6 | 152623015 | 152623493 | chr6 | 152957895 | 152958076 | chr6 | 153451236 | 153451500 |
| chr6 | 153451890 | 153451968 | chr6 | 153452232 | 153452320 | chr6 | 153452713 | 153452746 |
| chr6 | 154360650 | 154360746 | chr6 | 154970558 | 154970587 | chr6 | 155316257 | 155316265 |
| chr6 | 155569208 | 155569305 | chr6 | 157502438 | 157502561 | chr6 | 157506082 | 157506112 |
| chr6 | 157556764 | 157557296 | chr6 | 159290823 | 159290852 | chr6 | 159590048 | 159590086 |
| chr6 | 159590155 | 159590761 | chr6 | 159590972 | 159590985 | chr6 | 159654923 | 159655003 |
| chr6 | 161100361 | 161100390 | chr6 | 161188513 | 161188543 | chr6 | 161352101 | 161352135 |
| chr6 | 161780098 | 161780139 | chr6 | 163602842 | 163602872 | chr6 | 163834314 | 163834382 |
| chr6 | 163834406 | 163834532 | chr6 | 163834857 | 163834901 | chr6 | 163836568 | 163836900 |
| chr6 | 164179652 | 164179668 | chr6 | 164196987 | 164197003 | chr6 | 164228294 | 164228363 |
| chr6 | 164246109 | 164246143 | chr6 | 164283254 | 164283377 | chr6 | 164314290 | 164314443 |
| chr6 | 164322666 | 164322775 | chr6 | 166074119 | 166074412 | chr6 | 166076788 | 166077021 |
| chr6 | 166077378 | 166077632 | chr6 | 166267582 | 166267891 | chr6 | 166401254 | 166401307 |
| chr6 | 166402240 | 166402546 | chr6 | 166421911 | 166422185 | chr6 | 166579723 | 166580144 |
| chr6 | 166580344 | 166582797 | chr6 | 166944367 | 166944403 | chr6 | 167835129 | 167835171 |
| chr6 | 168719983 | 168720019 | chr6 | 168842847 | 168842944 | chr6 | 168858122 | 168858296 |
| chr6 | 168972472 | 168972502 | chr6 | 169002054 | 169002084 | chr6 | 169653638 | 169653668 |
| chr6 | 170047467 | 170047499 | chr6 | 170240639 | 170240714 | chr6 | 170264728 | 170264761 |
| chr6 | 170475105 | 170475267 | chr6 | 170494286 | 170494315 | chr6 | 170894820 | 170894836 |
| chr6 | 68930 | 68960 | chr7 | 329805 | 329838 | chr7 | 369844 | 369980 |
| chr7 | 389663 | 389693 | chr7 | 409826 | 409892 | chr7 | 427454 | 427484 |
| chr7 | 431386 | 431492 | chr7 | 497782 | 497934 | chr7 | 503811 | 503936 |
| chr7 | 551599 | 551697 | chr7 | 556928 | 556983 | chr7 | 564237 | 564271 |
| chr7 | 578922 | 579020 | chr7 | 579827 | 579857 | chr7 | 752120 | 752221 |
| chr7 | 907656 | 907709 | chr7 | 915058 | 915087 | chr7 | 922050 | 922235 |
| chr7 | 927933 | 927986 | chr7 | 1022224 | 1022254 | chr7 | 1030172 | 1030283 |
| chr7 | 1054579 | 1054696 | chr7 | 1086199 | 1086319 | chr7 | 1195270 | 1195364 |
| chr7 | 1263761 | 1263960 | chr7 | 1268318 | 1268366 | chr7 | 1269305 | 1269463 |
| chr7 | 1269553 | 1269808 | chr7 | 1270406 | 1270440 | chr7 | 1273167 | 1273330 |
| chr7 | 1274641 | 1274677 | chr7 | 1275579 | 1275680 | chr7 | 1277817 | 1277865 |
| chr7 | 1279099 | 1279129 | chr7 | 1279965 | 1279995 | chr7 | 1281131 | 1281232 |
| chr7 | 1281493 | 1281555 | chr7 | 1282042 | 1282150 | chr7 | 1282506 | 1282644 |
| chr7 | 1288582 | 1288753 | chr7 | 1308351 | 1308497 | chr7 | 1325810 | 1325882 |
| chr7 | 1416020 | 1416131 | chr7 | 1423632 | 1423677 | chr7 | 1459041 | 1459191 |
| chr7 | 1503417 | 1503596 | chr7 | 1547311 | 1547394 | chr7 | 1598639 | 1598697 |
| chr7 | 1607386 | 1607465 | chr7 | 1607971 | 1608001 | chr7 | 1615390 | 1615444 |
| chr7 | 1627404 | 1627434 | chr7 | 1641774 | 1641923 | chr7 | 1681189 | 1681239 |

TABLE 13-continued

| chr | start | end | chr | start | end | chr | start | end |
|---|---|---|---|---|---|---|---|---|
| chr7 | 1688977 | 1689122 | chr7 | 1690745 | 1690851 | chr7 | 1709138 | 1709235 |
| chr7 | 1709474 | 1709561 | chr7 | 1733166 | 1733378 | chr7 | 1748514 | 1748766 |
| chr7 | 1775831 | 1775861 | chr7 | 1778875 | 1778914 | chr7 | 1783551 | 1783623 |
| chr7 | 1786514 | 1786899 | chr7 | 1787166 | 1787324 | chr7 | 1800882 | 1800912 |
| chr7 | 1970842 | 1970872 | chr7 | 2109874 | 2109904 | chr7 | 2163332 | 2163467 |
| chr7 | 2208670 | 2208808 | chr7 | 2232963 | 2233056 | chr7 | 2233292 | 2233414 |
| chr7 | 2238118 | 2238235 | chr7 | 2300787 | 2300813 | chr7 | 2473452 | 2473605 |
| chr7 | 2565919 | 2566041 | chr7 | 2566600 | 2566630 | chr7 | 2720013 | 2720140 |
| chr7 | 2728068 | 2728165 | chr7 | 2979480 | 2979512 | chr7 | 2985518 | 2985547 |
| chr7 | 3033658 | 3033688 | chr7 | 3083331 | 3083352 | chr7 | 3283704 | 3283894 |
| chr7 | 3340444 | 3340473 | chr7 | 3341570 | 3341597 | chr7 | 4215324 | 4215384 |
| chr7 | 4856984 | 4857048 | chr7 | 4922550 | 4922706 | chr7 | 4923328 | 4923397 |
| chr7 | 4998201 | 4998388 | chr7 | 5111528 | 5111669 | chr7 | 5262433 | 5262562 |
| chr7 | 5397777 | 5397938 | chr7 | 5632939 | 5633100 | chr7 | 5648107 | 5648393 |
| chr7 | 6059103 | 6059182 | chr7 | 6060690 | 6060612 | chr7 | 6099217 | 6099246 |
| chr7 | 6124620 | 6124714 | chr7 | 6188610 | 6189061 | chr7 | 6414386 | 6414415 |
| chr7 | 6426878 | 6426907 | chr7 | 6443279 | 6443376 | chr7 | 6443826 | 6443856 |
| chr7 | 6524573 | 6524599 | chr7 | 6524977 | 6525012 | chr7 | 5525477 | 6525512 |
| chr7 | 6543150 | 6543216 | chr7 | 6560235 | 6560345 | chr7 | 6566413 | 6566663 |
| chr7 | 6570959 | 6571130 | chr7 | 6576137 | 6576367 | chr7 | 5703555 | 6703869 |
| chr7 | 6703916 | 6703959 | chr7 | 7605662 | 7605822 | chr7 | 8473070 | 8473455 |
| chr7 | 8473480 | 8473674 | chr7 | 8473956 | 8474241 | chr7 | 8474516 | 8474562 |
| chr7 | 8474814 | 8475057 | chr7 | 8480640 | 8481159 | chr7 | 8481642 | 8481833 |
| chr7 | 8482056 | 8482297 | chr7 | 8482670 | 8482824 | chr7 | 8482885 | 8482921 |
| chr7 | 8483147 | 8483950 | chr7 | 12151440 | 12151472 | chr7 | 12151524 | 12151678 |
| chr7 | 12443317 | 12443403 | chr7 | 12443841 | 12443871 | chr7 | 12610339 | 12610476 |
| chr7 | 15725983 | 15726081 | chr7 | 15726634 | 15727077 | chr7 | 15727290 | 15727320 |
| chr7 | 19145808 | 19145893 | chr7 | 19146032 | 19146184 | chr7 | 19146238 | 19146249 |
| chr7 | 19146502 | 19146558 | chr7 | 19147122 | 19147798 | chr7 | 19152224 | 19152349 |
| chr7 | 19155791 | 19155820 | chr7 | 19156126 | 19156132 | chr7 | 19156304 | 19156643 |
| chr7 | 19156703 | 19156745 | chr7 | 19157144 | 19157566 | chr7 | 19157634 | 19158015 |
| chr7 | 19158632 | 19158735 | chr7 | 19184058 | 19184255 | chr7 | 19813284 | 19813313 |
| chr7 | 20816252 | 20816447 | chr7 | 20817380 | 20817410 | chr7 | 20818130 | 20818276 |
| chr7 | 20823292 | 20823330 | chr7 | 20823383 | 20823432 | chr7 | 20823920 | 20824143 |
| chr7 | 20824476 | 20824819 | chr7 | 20824836 | 20824946 | chr7 | 20825379 | 20825559 |
| chr7 | 20826113 | 20826202 | chr7 | 20826884 | 20827199 | chr7 | 20830670 | 20830700 |
| chr7 | 20833167 | 20833322 | chr7 | 21582593 | 21582640 | chr7 | 21582792 | 21582868 |
| chr7 | 21583263 | 21583277 | chr7 | 21583304 | 21583326 | chr7 | 22539833 | 22539909 |
| chr7 | 22589356 | 22589870 | chr7 | 23287253 | 23287350 | chr7 | 23287533 | 23287624 |
| chr7 | 23578780 | 23578857 | chr7 | 24323763 | 24323939 | chr7 | 24580785 | 24580806 |
| chr7 | 24796478 | 24796567 | chr7 | 25132702 | 25132726 | chr7 | 25896521 | 25896603 |
| chr7 | 25896663 | 25896864 | chr7 | 25897133 | 25897246 | chr7 | 27127863 | 27127898 |
| chr7 | 27135327 | 27135770 | chr7 | 27136013 | 27136790 | chr7 | 27138381 | 27138410 |
| chr7 | 27184015 | 27184190 | chr7 | 27190591 | 27191226 | chr7 | 27192061 | 27192098 |
| chr7 | 27195462 | 27195601 | chr7 | 27195867 | 27195892 | chr7 | 27196153 | 27196839 |
| chr7 | 27204487 | 27204769 | chr7 | 27205266 | 27205395 | chr7 | 27205678 | 27205789 |
| chr7 | 27208187 | 27208285 | chr7 | 27209462 | 27209582 | chr7 | 27212499 | 27212899 |
| chr7 | 27213189 | 27214261 | chr7 | 27217042 | 27217071 | chr7 | 2223114 | 27223151 |
| chr7 | 27223601 | 27223696 | chr7 | 27224069 | 27224609 | chr7 | 27225035 | 27225057 |
| chr7 | 27225442 | 27225483 | chr7 | 27227874 | 27227953 | chr7 | 27231476 | 27231505 |
| chr7 | 27231818 | 27231894 | chr7 | 27232289 | 27232962 | chr7 | 27233410 | 27233454 |
| chr7 | 27238887 | 27238917 | chr7 | 27239226 | 27239234 | chr7 | 27240229 | 27240381 |
| chr7 | 27244515 | 27244610 | chr7 | 27244798 | 27245310 | chr7 | 27245668 | 27245795 |
| chr7 | 27252380 | 27252410 | chr7 | 27260092 | 27260100 | chr7 | 27264875 | 27265325 |
| chr7 | 27265538 | 27265584 | chr7 | 27275513 | 27275543 | chr7 | 27279238 | 27279368 |
| chr7 | 27281329 | 27281360 | chr7 | 27282089 | 27283013 | chr7 | 27283351 | 27283627 |
| chr7 | 27285621 | 27285913 | chr7 | 27285980 | 27286098 | chr7 | 27286171 | 27286248 |
| chr7 | 27288946 | 27289100 | chr7 | 27289170 | 27289449 | chr7 | 27291315 | 27291851 |
| chr7 | 28110701 | 28110828 | chr7 | 28449276 | 28449290 | chr7 | 28449659 | 28449781 |
| chr7 | 28449858 | 28450015 | chr7 | 28995657 | 28995978 | chr7 | 28996457 | 28996495 |
| chr7 | 28996840 | 28996916 | chr7 | 28997136 | 28997625 | chr7 | 28998053 | 28998119 |
| chr7 | 30029702 | 30029822 | chr7 | 30029923 | 30029952 | chr7 | 30721280 | 30721902 |
| chr7 | 30722290 | 30722375 | chr7 | 30857157 | 30857292 | chr7 | 31093003 | 31093133 |
| chr7 | 31232909 | 31232939 | chr7 | 31375965 | 31376135 | chr7 | 32110704 | 32110772 |
| chr7 | 32337807 | 32337837 | chr7 | 32338088 | 32338217 | chr7 | 32338284 | 32338370 |
| chr7 | 32338900 | 32338930 | chr7 | 32467461 | 32467655 | chr7 | 32467947 | 32468062 |
| chr7 | 32997124 | 32997454 | chr7 | 33167928 | 33167949 | chr7 | 33725803 | 33725938 |
| chr7 | 33943459 | 33943759 | chr7 | 35225809 | 35225833 | chr7 | 35226193 | 35226522 |
| chr7 | 35226557 | 35226765 | chr7 | 35292970 | 35293086 | chr7 | 35293183 | 35293293 |
| chr7 | 35294032 | 35294141 | chr7 | 35294502 | 35294536 | chr7 | 35295104 | 36295105 |
| chr7 | 35295908 | 35295944 | chr7 | 35296935 | 35297004 | chr7 | 35297138 | 35297353 |
| chr7 | 35297471 | 35298016 | chr7 | 35300951 | 35301008 | chr7 | 35301102 | 35301948 |
| chr7 | 37487164 | 37487255 | chr7 | 37487375 | 37487453 | chr7 | 37487756 | 37487826 |
| chr7 | 37488257 | 37488578 | chr7 | 37488920 | 37488992 | chr7 | 37907440 | 37907470 |
| chr7 | 37955878 | 37955979 | chr7 | 37956271 | 37956439 | chr7 | 37960301 | 37960335 |
| chr7 | 38588471 | 38588501 | chr7 | 38670357 | 38670663 | chr7 | 38670957 | 38671015 |
| chr7 | 39015542 | 39015981 | chr7 | 39649223 | 39649253 | chr7 | 39649444 | 39649457 |
| chr7 | 39872836 | 39873015 | chr7 | 41739663 | 41739879 | chr7 | 41982690 | 41982874 |

TABLE 13-continued

| chr | start | end | chr | start | end | chr | start | end |
|---|---|---|---|---|---|---|---|---|
| chr7 | 42267647 | 42267677 | chr7 | 42276346 | 42276634 | chr7 | 42377468 | 42377497 |
| chr7 | 42533257 | 42533296 | chr7 | 43162109 | 43152207 | chr7 | 43152414 | 43152700 |
| chr7 | 43152957 | 43153199 | chr7 | 43153230 | 43153237 | chr7 | 44097690 | 44097876 |
| chr7 | 44151398 | 44151428 | chr7 | 44151795 | 44151933 | chr7 | 44163926 | 44163989 |
| chr7 | 44364838 | 44364903 | chr7 | 44740630 | 44740672 | chr7 | 44835121 | 44835384 |
| chr7 | 45038532 | 45038564 | chr7 | 45046874 | 45046982 | chr7 | 45613785 | 45613813 |
| chr7 | 45613858 | 45613898 | chr7 | 45614341 | 45614474 | chr7 | 45614738 | 45614809 |
| chr7 | 45614929 | 45615020 | chr7 | 45615440 | 45615495 | chr7 | 45960743 | 45960794 |
| chr7 | 45961146 | 45961176 | chr7 | 45961508 | 45961576 | chr7 | 45961833 | 45961888 |
| chr7 | 47515359 | 47515405 | chr7 | 47704324 | 47704359 | chr7 | 49812820 | 49813017 |
| chr7 | 49813810 | 49813994 | chr7 | 49814531 | 49814750 | chr7 | 49815117 | 49815249 |
| chr7 | 49815657 | 49815765 | chr7 | 49819674 | 49819703 | chr7 | 50294451 | 50294481 |
| chr7 | 50343263 | 50343401 | chr7 | 50343975 | 50343994 | chr7 | 50344226 | 50344491 |
| chr7 | 50365076 | 50365107 | chr7 | 50438618 | 50438648 | chr7 | 50441145 | 50441285 |
| chr7 | 50560588 | 50560637 | chr7 | 50860226 | 50861102 | chr7 | 51383754 | 51383790 |
| chr7 | 51384327 | 51384440 | chr7 | 51384915 | 51384951 | chr7 | 52156231 | 52156261 |
| chr7 | 54609852 | 54609951 | chr7 | 54609992 | 54610153 | chr7 | 54612418 | 54612730 |
| chr7 | 55086473 | 55086601 | chr7 | 55086983 | 55087533 | chr7 | 55209976 | 55210005 |
| chr7 | 55211065 | 55211094 | chr7 | 55221729 | 55221836 | chr7 | 55223589 | 55223636 |
| chr7 | 55227993 | 55228022 | chr7 | 55233028 | 55233123 | chr7 | 55241653 | 55241737 |
| chr7 | 55242419 | 55242493 | chr7 | 55248975 | 55249085 | chr7 | 56259404 | 55259547 |
| chr7 | 55260469 | 55260498 | chr7 | 55268867 | 55268896 | chr7 | 55410019 | 55410126 |
| chr7 | 55506288 | 55506348 | chr7 | 56018123 | 56018205 | chr7 | 56031793 | 56031869 |
| chr7 | 63667431 | 63667460 | chr7 | 64330411 | 64330470 | chr7 | 64330734 | 64330833 |
| chr7 | 64349042 | 64349056 | chr7 | 64349331 | 64349470 | chr7 | 64700283 | 64700329 |
| chr7 | 64712364 | 64712510 | chr7 | 64974382 | 64974402 | chr7 | 65037609 | 65037702 |
| chr7 | 65508995 | 65509043 | chr7 | 65878743 | 65878793 | chr7 | 66214942 | 66214961 |
| chr7 | 68204793 | 68204931 | chr7 | 69062519 | 69062635 | chr7 | 69064590 | 69064771 |
| chr7 | 69064834 | 69065045 | chr7 | 69897780 | 69897827 | chr7 | 70596454 | 70596688 |
| chr7 | 70597406 | 70597451 | chr7 | 70597835 | 70597871 | chr7 | 70597991 | 70598123 |
| chr7 | 70598170 | 70598387 | chr7 | 71217108 | 71217332 | chr7 | 71603924 | 71604032 |
| chr7 | 71800676 | 71800756 | chr7 | 71800934 | 71801104 | chr7 | 71802410 | 71802522 |
| chr7 | 71802578 | 71802637 | chr7 | 71871203 | 71871245 | chr7 | 75511201 | 75511298 |
| chr7 | 76033250 | 76033289 | chr7 | 77129885 | 77129907 | chr7 | 77324362 | 77324448 |
| chr7 | 79081792 | 79081821 | chr7 | 79082023 | 79082218 | chr7 | 79083392 | 79083834 |
| chr7 | 80548257 | 80548403 | chr7 | 82072350 | 82072503 | chr7 | 82073495 | 82073533 |
| chr7 | 84815141 | 84815226 | chr7 | 84815744 | 84815954 | chr7 | 86273208 | 86273541 |
| chr7 | 86274258 | 86274457 | chr7 | 87104816 | 87105430 | chr7 | 87229537 | 87230433 |
| chr7 | 87257012 | 87257047 | chr7 | 87257963 | 87258054 | chr7 | 87563370 | 87563614 |
| chr7 | 87563829 | 87563890 | chr7 | 87825102 | 87825137 | chr7 | 88387982 | 88388167 |
| chr7 | 88388540 | 88388660 | chr7 | 88388879 | 88388901 | chr7 | 88389047 | 88389356 |
| chr7 | 89747996 | 89748340 | chr7 | 89950183 | 89950810 | chr7 | 90226269 | 90226464 |
| chr7 | 90895012 | 90895097 | chr7 | 92466152 | 92466400 | chr7 | 92689705 | 92689792 |
| chr7 | 93203708 | 93203756 | chr7 | 93204332 | 93204492 | chr7 | 93519351 | 93519765 |
| chr7 | 93519855 | 93520137 | chr7 | 93551323 | 93551425 | chr7 | 94284302 | 94284873 |
| chr7 | 96619560 | 96619603 | chr7 | 96621715 | 96621811 | chr7 | 96622107 | 96622349 |
| chr7 | 96622694 | 96622723 | chr7 | 96625537 | 96625720 | chr7 | 96625998 | 96626051 |
| chr7 | 96627013 | 96627048 | chr7 | 96631579 | 96631680 | chr7 | 96634645 | 96634928 |
| chr7 | 96635345 | 96635379 | chr7 | 96635439 | 96635451 | chr7 | 96635733 | 96635971 |
| chr7 | 96636034 | 96636645 | chr7 | 96639318 | 96639348 | chr7 | 96646662 | 96647131 |
| chr7 | 96647809 | 96648219 | chr7 | 96649955 | 96650094 | chr7 | 96650884 | 96651076 |
| chr7 | 96651137 | 96651151 | chr7 | 96651469 | 96651537 | chr7 | 96652144 | 96652174 |
| chr7 | 96653507 | 96653819 | chr7 | 96653863 | 96653993 | chr7 | 97361098 | 97361422 |
| chr7 | 97361521 | 97361781 | chr7 | 97362292 | 97362607 | chr7 | 97600104 | 97600194 |
| chr7 | 97869614 | 97869644 | chr7 | 98197224 | 98197242 | chr7 | 98245885 | 98246078 |
| chr7 | 98246305 | 98246507 | chr7 | 98246534 | 98246868 | chr7 | 98247126 | 98247656 |
| chr7 | 98965786 | 98966881 | chr7 | 98971529 | 98971549 | chr7 | 99104258 | 99104293 |
| chr7 | 99177742 | 99177870 | chr7 | 99591731 | 99591762 | chr7 | 99595194 | 99595335 |
| chr7 | 99751578 | 99751630 | chr7 | 99775192 | 99275558 | chr7 | 100088183 | 100088312 |
| chr7 | 100179889 | 100179927 | chr7 | 100295403 | 100295424 | chr7 | 100318505 | 100318575 |
| chr7 | 100320690 | 100320719 | chr7 | 100547037 | 100547073 | chr7 | 100609780 | 100609780 |
| chr7 | 100808466 | 100808502 | chr7 | 100809436 | 100809521 | chr7 | 100823436 | 100823497 |
| chr7 | 101005968 | 101005998 | chr7 | 101241993 | 101242023 | chr7 | 101475790 | 101475858 |
| chr7 | 101558399 | 101558698 | chr7 | 101627741 | 101627787 | chr7 | 101707502 | 101707532 |
| chr7 | 103085876 | 103086474 | chr7 | 103629059 | 103629794 | chr7 | 103630054 | 103630082 |
| chr7 | 103630475 | 103630824 | chr7 | 103969217 | 103969341 | chr7 | 103969694 | 103969794 |
| chr7 | 105279467 | 105279671 | chr7 | 106622834 | 106622961 | chr7 | 106685282 | 106685345 |
| chr7 | 106797774 | 106797804 | chr7 | 107301494 | 107301640 | chr7 | 107483694 | 107483918 |
| chr7 | 108095329 | 108095362 | chr7 | 108095781 | 108096055 | chr7 | 108097172 | 108097491 |
| chr7 | 111202993 | 111203097 | chr7 | 112726558 | 112726614 | chr7 | 113722810 | 113723283 |
| chr7 | 113723339 | 113723439 | chr7 | 113724956 | 113725081 | chr7 | 113726509 | 113726539 |
| chr7 | 113727442 | 113727486 | chr7 | 113727754 | 113727781 | chr7 | 115117552 | 115117647 |
| chr7 | 116140252 | 116140356 | chr7 | 116412008 | 116412058 | chr7 | 116415100 | 116415129 |
| chr7 | 116417443 | 116417496 | chr7 | 116422067 | 116422132 | chr7 | 116423399 | 116423488 |
| chr7 | 116962893 | 116963146 | chr7 | 116963331 | 116963476 | chr7 | 117119381 | 117120271 |
| chr7 | 117513675 | 117513849 | chr7 | 119913561 | 119913785 | chr7 | 120969672 | 120969800 |
| chr7 | 121513523 | 121513709 | chr7 | 121939677 | 121940244 | chr7 | 121940434 | 121940448 |
| chr7 | 121940935 | 121941052 | chr7 | 121941881 | 121942170 | chr7 | 121945822 | 121945920 |

TABLE 13-continued

| chr | start | end | chr | start | end | chr | start | end |
|---|---|---|---|---|---|---|---|---|
| chr7 | 121946478 | 121946982 | chr7 | 121947098 | 121947406 | chr7 | 121950137 | 121950264 |
| chr7 | 121950429 | 121950552 | chr7 | 121950995 | 121951069 | chr7 | 121951877 | 121952010 |
| chr7 | 121952044 | 121952169 | chr7 | 121956486 | 121956567 | chr7 | 121956955 | 121957076 |
| chr7 | 121957254 | 121957331 | chr7 | 122526833 | 122526873 | chr7 | 123173150 | 123173244 |
| chr7 | 123672048 | 123672086 | chr7 | 124404415 | 124404497 | chr7 | 126891220 | 126891250 |
| chr7 | 126891504 | 126891593 | chr7 | 126894076 | 126894197 | chr7 | 127371129 | 127371249 |
| chr7 | 127615921 | 127615951 | chr7 | 127744122 | 127744631 | chr7 | 127806534 | 127806664 |
| chr7 | 127807817 | 127807846 | chr7 | 127808047 | 127808792 | chr7 | 127841626 | 127841704 |
| chr7 | 127991826 | 127991922 | chr7 | 127992045 | 127992135 | chr7 | 128097059 | 128097089 |
| chr7 | 128337467 | 128337544 | chr7 | 128337788 | 128337921 | chr7 | 128470897 | 128471032 |
| chr7 | 128486036 | 128486138 | chr7 | 128528749 | 128528779 | chr7 | 128529023 | 128529053 |
| chr7 | 128828195 | 128828272 | chr7 | 129229604 | 129229631 | chr7 | 129418057 | 129418428 |
| chr7 | 129422160 | 129422968 | chr7 | 129423126 | 129423418 | chr7 | 129424655 | 129425887 |
| chr7 | 129426195 | 129426236 | chr7 | 129483356 | 129483449 | chr7 | 129794593 | 129794721 |
| chr7 | 129800243 | 129800434 | chr7 | 129844450 | 129844493 | chr7 | 131041515 | 131041596 |
| chr7 | 131242738 | 131242824 | chr7 | 131514824 | 131514854 | chr7 | 132261272 | 132261432 |
| chr7 | 134143164 | 134143475 | chr7 | 134143807 | 134144132 | chr7 | 134918503 | 134918637 |
| chr7 | 136553311 | 136554025 | chr7 | 136554104 | 136554366 | chr7 | 136554638 | 136554966 |
| chr7 | 136555235 | 136555412 | chr7 | 136555681 | 136555841 | chr7 | 136556013 | 136556091 |
| chr7 | 136969053 | 136969083 | chr7 | 137028481 | 137028524 | chr7 | 137531158 | 137531211 |
| chr7 | 137531263 | 137531888 | chr7 | 137531909 | 137532187 | chr7 | 138042221 | 138042288 |
| chr7 | 138720785 | 138720909 | chr7 | 139167617 | 139167744 | chr7 | 139168115 | 139168379 |
| chr7 | 139208772 | 139208979 | chr7 | 139930051 | 139930270 | chr7 | 139939160 | 139939318 |
| chr7 | 140027008 | 140027079 | chr7 | 140180179 | 140180299 | chr7 | 140218053 | 140218082 |
| chr7 | 140218123 | 140218352 | chr7 | 140219405 | 140219435 | chr7 | 140339952 | 140339982 |
| chr7 | 140453121 | 140453167 | chr7 | 140477779 | 140477868 | chr7 | 140481381 | 140481431 |
| chr7 | 140772795 | 140773228 | chr7 | 140773563 | 140773750 | chr7 | 143042634 | 143042798 |
| chr7 | 143579739 | 143580069 | chr7 | 145812992 | 145813082 | chr7 | 145813412 | 145813494 |
| chr7 | 145813946 | 145814166 | chr7 | 148224584 | 148224686 | chr7 | 148508712 | 148508741 |
| chr7 | 148640211 | 148640250 | chr7 | 148846138 | 148846180 | chr7 | 148851143 | 148851234 |
| chr7 | 149112058 | 149112248 | chr7 | 149119948 | 149120073 | chr7 | 149411521 | 149411727 |
| chr7 | 149411835 | 149412304 | chr7 | 149570368 | 149570406 | chr7 | 149744505 | 149744560 |
| chr7 | 149917322 | 149917336 | chr7 | 149918119 | 149918149 | chr7 | 150038883 | 150038912 |
| chr7 | 150049604 | 150049631 | chr7 | 150069098 | 150069346 | chr7 | 150069679 | 150069820 |
| chr7 | 150070021 | 150070058 | chr7 | 150081236 | 150081308 | chr7 | 150716169 | 150716305 |
| chr7 | 150748192 | 150748406 | chr7 | 150753942 | 150753981 | chr7 | 150870816 | 150870889 |
| chr7 | 151106451 | 151106565 | chr7 | 151106590 | 151106988 | chr7 | 151107486 | 151107651 |
| chr7 | 151188034 | 151188063 | chr7 | 151298870 | 151299029 | chr7 | 151423571 | 151423639 |
| chr7 | 151591667 | 151591705 | chr7 | 152133406 | 152133436 | chr7 | 152622621 | 152622697 |
| chr7 | 152913656 | 152913801 | chr7 | 153583632 | 153584069 | chr7 | 153584389 | 153584623 |
| chr7 | 153584848 | 153585206 | chr7 | 153585602 | 153585606 | chr7 | 153633899 | 153633942 |
| chr7 | 153749720 | 153750042 | chr7 | 154561150 | 154561189 | chr7 | 154708275 | 154708338 |
| chr7 | 154852046 | 154852266 | chr7 | 155164454 | 155165562 | chr7 | 155165875 | 155166784 |
| chr7 | 155167034 | 155167089 | chr7 | 155167175 | 155167660 | chr7 | 155167834 | 165167909 |
| chr7 | 155174656 | 155174788 | chr7 | 155241318 | 155242049 | chr7 | 155242729 | 155243102 |
| chr7 | 155243346 | 155243533 | chr7 | 155243825 | 155243895 | chr7 | 155244180 | 155244361 |
| chr7 | 155246886 | 155247479 | chr7 | 155248913 | 155248943 | chr7 | 155249512 | 155249565 |
| chr7 | 155249925 | 155250011 | chr7 | 155250283 | 155250303 | chr7 | 155250324 | 155250355 |
| chr7 | 155250787 | 155250996 | chr7 | 155251701 | 155251854 | chr7 | 155251891 | 155251939 |
| chr7 | 155252247 | 155252261 | chr7 | 155252317 | 155252490 | chr7 | 155252862 | 155253041 |
| chr7 | 155254848 | 155255324 | chr7 | 155256269 | 155256312 | chr7 | 155257040 | 155257189 |
| chr7 | 155258193 | 155258487 | chr7 | 155258949 | 156259077 | chr7 | 155259120 | 155259622 |
| chr7 | 155259834 | 155259957 | chr7 | 155260039 | 155260137 | chr7 | 155260880 | 155260890 |
| chr7 | 155261071 | 155261210 | chr7 | 155301838 | 155301931 | chr7 | 155302328 | 155302895 |
| chr7 | 155302964 | 155303335 | chr7 | 155325796 | 155325872 | chr7 | 155326169 | 155326527 |
| chr7 | 155363304 | 155363417 | chr7 | 155580182 | 155580211 | chr7 | 155580846 | 155580876 |
| chr7 | 155581330 | 155581553 | chr7 | 155581765 | 155581980 | chr7 | 155582277 | 155582340 |
| chr7 | 155600629 | 155600723 | chr7 | 155602751 | 155602805 | chr7 | 156259192 | 156259221 |
| chr7 | 156409144 | 156409347 | chr7 | 156409728 | 156409802 | chr7 | 156701846 | 156701908 |
| chr7 | 156744696 | 156744713 | chr7 | 156794464 | 156794485 | chr7 | 156794989 | 156795354 |
| chr7 | 156795402 | 156795635 | chr7 | 156795900 | 156795914 | chr7 | 156796534 | 156796739 |
| chr7 | 156797006 | 156798434 | chr7 | 156798527 | 156799146 | chr7 | 156799291 | 166799467 |
| chr7 | 156800999 | 156801029 | chr7 | 156801403 | 156801601 | chr7 | 156808858 | 156809199 |
| chr7 | 156809983 | 156810521 | chr7 | 156810598 | 156810800 | chr7 | 156811303 | 156811436 |
| chr7 | 156812852 | 156813825 | chr7 | 156813987 | 156814707 | chr7 | 156814784 | 156815092 |
| chr7 | 156832223 | 156832402 | chr7 | 156832848 | 156833162 | chr7 | 156871283 | 156871297 |
| chr7 | 156880531 | 156880561 | chr7 | 157085373 | 157085487 | chr7 | 157085963 | 157086082 |
| chr7 | 157262815 | 157263018 | chr7 | 157263294 | 157263471 | chr7 | 157335172 | 157335202 |
| chr7 | 157361605 | 157361635 | chr7 | 157476879 | 157476973 | chr7 | 157476995 | 157477272 |
| chr7 | 157477473 | 157477488 | chr7 | 157477711 | 157477819 | chr7 | 157481130 | 157481160 |
| chr7 | 157481534 | 157481549 | chr7 | 157481969 | 157482073 | chr7 | 157482492 | 157482667 |
| chr7 | 157483320 | 157483538 | chr7 | 157484877 | 157485277 | chr7 | 157485527 | 157485601 |
| chr7 | 157485650 | 157485705 | chr7 | 157485976 | 157486081 | chr7 | 157486205 | 157486414 |
| chr7 | 157486476 | 157486503 | chr7 | 157584178 | 157584208 | chr7 | 157588586 | 157588791 |
| chr7 | 157606706 | 157606736 | chr7 | 157690056 | 157690086 | chr7 | 158059762 | 158059794 |
| chr7 | 158065832 | 158065970 | chr7 | 158298861 | 158299036 | chr7 | 158673836 | 158673942 |
| chr7 | 158741193 | 158741267 | chr7 | 158799762 | 158799791 | chr7 | 158936492 | 158936880 |
| chr7 | 158937203 | 158937374 | chr7 | 158937577 | 158937624 | chr7 | 158938210 | 158938399 |

TABLE 13-continued

| chr | start | end | chr | start | end | chr | start | end |
|---|---|---|---|---|---|---|---|---|
| chr8 | 686870 | 686884 | chr8 | 687163 | 687217 | chr8 | 687838 | 687975 |
| chr8 | 1085573 | 1085603 | chr8 | 1444165 | 1444205 | chr8 | 1950097 | 1950134 |
| chr8 | 4849141 | 4849177 | chr8 | 4849466 | 4849500 | chr8 | 4850247 | 4850322 |
| chr8 | 4850419 | 1850516 | chr8 | 4851736 | 4851749 | chr8 | 4852021 | 4852118 |
| chr8 | 8681258 | 8681353 | chr8 | 8748422 | 8748713 | chr8 | 8748919 | 8748956 |
| chr8 | 9722850 | 9722896 | chr8 | 9756051 | 9756283 | chr8 | 9760735 | 9761155 |
| chr8 | 9762586 | 9762689 | chr8 | 9762752 | 9762864 | chr8 | 9763143 | 9763275 |
| chr8 | 9763895 | 9764049 | chr8 | 9764196 | 9764214 | chr8 | 9764434 | 9764551 |
| chr8 | 10587589 | 10587602 | chr8 | 10652917 | 10652937 | chr8 | 10980452 | 10980491 |
| chr8 | 11204479 | 11204509 | chr8 | 11204810 | 11204905 | chr8 | 11536827 | 11536857 |
| chr8 | 11537225 | 11537259 | chr8 | 11554885 | 11554915 | chr8 | 11555152 | 11555166 |
| chr8 | 11555474 | 11555521 | chr8 | 11559759 | 11559794 | chr8 | 11560068 | 11560375 |
| chr8 | 11560711 | 11560793 | chr8 | 11561442 | 11562169 | chr8 | 11562422 | 11562485 |
| chr8 | 11562701 | 11562917 | chr8 | 11706960 | 11706136 | chr8 | 11706580 | 11706613 |
| chr8 | 11726469 | 11726512 | chr8 | 12990386 | 12990431 | chr8 | 12990664 | 12990784 |
| chr8 | 13319931 | 13319961 | chr8 | 15094505 | 15094566 | chr8 | 16884182 | 16884239 |
| chr8 | 16885205 | 16885241 | chr8 | 17271091 | 17271119 | chr8 | 19797433 | 19797463 |
| chr8 | 19797939 | 19798019 | chr8 | 20375563 | 20375592 | chr8 | 22089409 | 22089560 |
| chr8 | 22458657 | 22458687 | chr8 | 22562345 | 22562483 | chr8 | 22960648 | 22960723 |
| chr8 | 23020951 | 23021107 | chr8 | 23260683 | 23260870 | chr8 | 23423923 | 23423974 |
| chr8 | 23559385 | 23559601 | chr8 | 23559666 | 23560525 | chr8 | 23563791 | 23564023 |
| chr8 | 23564193 | 23564388 | chr8 | 23564652 | 23564668 | chr8 | 23564703 | 23565024 |
| chr8 | 23566803 | 23566854 | chr8 | 23566901 | 23567213 | chr8 | 23567312 | 23567492 |
| chr8 | 23571681 | 23571973 | chr8 | 23572377 | 23572554 | chr8 | 23584094 | 23584400 |
| chr8 | 23584582 | 23584760 | chr8 | 24770314 | 24270361 | chr8 | 24770414 | 24770581 |
| chr8 | 24771431 | 24771562 | chr8 | 24813188 | 24813287 | chr8 | 24813750 | 24813893 |
| chr8 | 24814011 | 24814407 | chr8 | 24857776 | 24857808 | chr8 | 24858336 | 24858440 |
| chr8 | 24858856 | 24859161 | chr8 | 24859496 | 24859526 | chr8 | 25041746 | 25041864 |
| chr8 | 25042534 | 25042567 | chr8 | 25900408 | 25900692 | chr8 | 25900781 | 26901317 |
| chr8 | 25901540 | 25901765 | chr8 | 25902146 | 25902176 | chr8 | 25902619 | 26902649 |
| chr8 | 25903662 | 25903854 | chr8 | 25904157 | 25904191 | chr8 | 25905096 | 25905126 |
| chr8 | 25905762 | 25905811 | chr8 | 25909197 | 25909597 | chr8 | 26372863 | 26372893 |
| chr8 | 26723985 | 26724080 | chr8 | 30243388 | 30243423 | chr8 | 30475450 | 30475480 |
| chr8 | 30769249 | 30769411 | chr8 | 30770106 | 30770109 | chr8 | 30770158 | 30770188 |
| chr8 | 31496481 | 31496757 | chr8 | 31497024 | 31497152 | chr8 | 31497499 | 31497639 |
| chr8 | 32406598 | 32406914 | chr8 | 33372069 | 33372125 | chr8 | 33457142 | 33457379 |
| chr8 | 35093037 | 35093054 | chr8 | 35093951 | 35093973 | chr8 | 37655476 | 37655517 |
| chr8 | 37655810 | 37655990 | chr8 | 37656050 | 37656081 | chr8 | 37822796 | 37823423 |
| chr8 | 37961878 | 37961902 | chr8 | 38008234 | 38008557 | chr8 | 38020213 | 38020272 |
| chr8 | 38274835 | 38274864 | chr8 | 38323911 | 38323941 | chr8 | 38965322 | 38965386 |
| chr8 | 39172082 | 39172134 | chr8 | 41165865 | 41165918 | chr8 | 41166001 | 41166151 |
| chr8 | 41166267 | 41166679 | chr8 | 41166974 | 41166988 | chr8 | 41167026 | 41167035 |
| chr8 | 41424760 | 41424842 | chr8 | 41624826 | 41624855 | chr8 | 41625112 | 41625141 |
| chr8 | 41700665 | 41700751 | chr8 | 41711416 | 41711447 | chr8 | 41733505 | 41733640 |
| chr8 | 41753593 | 41753752 | chr8 | 41754152 | 41754885 | chr8 | 41755178 | 41755208 |
| chr8 | 41910270 | 41910339 | chr8 | 42082721 | 42082798 | chr8 | 42147392 | 42147521 |
| chr8 | 42293633 | 42293722 | chr8 | 42350468 | 42350492 | chr8 | 42749974 | 42750012 |
| chr8 | 47093246 | 47093276 | chr8 | 47334619 | 47334678 | chr8 | 48044710 | 48044753 |
| chr8 | 48100155 | 48100443 | chr8 | 49293364 | 49293524 | chr8 | 49293581 | 49293614 |
| chr8 | 49468669 | 49469127 | chr8 | 49572029 | 49572058 | chr8 | 49783041 | 49783283 |
| chr8 | 49836145 | 49836174 | chr8 | 49959230 | 49959260 | chr8 | 50822179 | 50822308 |
| chr8 | 50822686 | 50822734 | chr8 | 50823452 | 50823562 | chr8 | 53322495 | 53322524 |
| chr8 | 53477408 | 53477736 | chr8 | 53478008 | 53478275 | chr8 | 53478480 | 53478720 |
| chr8 | 53851141 | 53851170 | chr8 | 53853811 | 53854509 | chr8 | 54163316 | 54163349 |
| chr8 | 54163674 | 54164126 | chr8 | 54789278 | 54789310 | chr8 | 54789632 | 54789805 |
| chr8 | 54790023 | 54790077 | chr8 | 54790291 | 54790855 | chr8 | 54791898 | 54791945 |
| chr8 | 54792185 | 54792237 | chr8 | 54792634 | 54792670 | chr8 | 54792702 | 54792760 |
| chr8 | 54794217 | 54794327 | chr8 | 54794713 | 54794780 | chr8 | 54794827 | 54794949 |
| chr8 | 54795140 | 54795165 | chr8 | 55366188 | 55366367 | chr8 | 55366952 | 55367641 |
| chr8 | 55370113 | 55370432 | chr8 | 55370568 | 55370713 | chr8 | 55370798 | 55370858 |
| chr8 | 55371178 | 55371375 | chr8 | 55371440 | 55371724 | chr8 | 55371994 | 55372067 |
| chr8 | 55372417 | 55372538 | chr8 | 55379296 | 55379456 | chr8 | 55383183 | 55383237 |
| chr8 | 56013641 | 56013892 | chr8 | 56014157 | 56014184 | chr8 | 56014623 | 56014743 |
| chr8 | 56015038 | 56015052 | chr8 | 56015186 | 56015357 | chr8 | 56015560 | 56015619 |
| chr8 | 56015908 | 56015938 | chr8 | 57025776 | 57025943 | chr8 | 57026168 | 57026213 |
| chr8 | 57026503 | 57026547 | chr8 | 57069553 | 57069737 | chr8 | 57069851 | 57070157 |
| chr8 | 57358465 | 57358661 | chr8 | 57358807 | 57359091 | chr8 | 57359260 | 57359636 |
| chr8 | 57359893 | 57359922 | chr8 | 57360211 | 57360240 | chr8 | 57360570 | 57360625 |
| chr8 | 57360770 | 57360791 | chr8 | 58105946 | 58106115 | chr8 | 58117004 | 58117079 |
| chr8 | 58130364 | 58130574 | chr8 | 58907698 | 58907835 | chr8 | 59058941 | 59059343 |
| chr8 | 59747186 | 59747318 | chr8 | 60032680 | 60032738 | chr8 | 61777575 | 61777699 |
| chr8 | 61789974 | 61790004 | chr8 | 62034029 | 62034059 | chr8 | 62200502 | 62200776 |
| chr8 | 63161658 | 63161800 | chr8 | 65281616 | 65281760 | chr8 | 65282004 | 65282004 |
| chr8 | 65282333 | 65282440 | chr8 | 65282713 | 65282944 | chr8 | 65283042 | 65283341 |
| chr8 | 65283799 | 65284094 | chr8 | 65286056 | 65286066 | chr8 | 65286682 | 65286753 |
| chr8 | 65286963 | 65287251 | chr8 | 65289123 | 65289241 | chr8 | 65289614 | 65290681 |
| chr8 | 65291034 | 65291284 | chr8 | 65292185 | 65292727 | chr8 | 65488271 | 65488322 |
| chr8 | 65488661 | 65488697 | chr8 | 65489099 | 65489129 | chr8 | 65492712 | 65492979 |

TABLE 13-continued

| chr | start | end | chr | start | end | chr | start | end |
|---|---|---|---|---|---|---|---|---|
| chr8 | 65493195 | 65493433 | chr8 | 65494077 | 65494193 | chr8 | 65498566 | 65498584 |
| chr8 | 65498644 | 65498841 | chr8 | 65499757 | 65500015 | chr8 | 65710938 | 65711046 |
| chr8 | 66548717 | 66548759 | chr8 | 66560524 | 66560545 | chr8 | 67025063 | 67025640 |
| chr8 | 67025920 | 67026429 | chr8 | 67026489 | 67026578 | chr8 | 67026812 | 67026990 |
| chr8 | 67344538 | 67344701 | chr8 | 67873327 | 67873421 | chr8 | 67873799 | 67874050 |
| chr8 | 67874165 | 67874672 | chr8 | 67874756 | 67875682 | chr8 | 67940674 | 67940875 |
| chr8 | 68864578 | 68864765 | chr8 | 69242905 | 69242988 | chr8 | 69243285 | 69243902 |
| chr8 | 69243964 | 69243994 | chr8 | 69244370 | 69244500 | chr8 | 70744860 | 70744925 |
| chr8 | 70946760 | 70946914 | chr8 | 70947091 | 70947658 | chr8 | 70982263 | 70982566 |
| chr8 | 70982851 | 70983226 | chr8 | 70983504 | 70983869 | chr8 | 70984202 | 70984292 |
| chr8 | 70984344 | 70984661 | chr8 | 70984745 | 70984978 | chr8 | 71308096 | 71308126 |
| chr8 | 71447529 | 71447559 | chr8 | 72273998 | 72274033 | chr8 | 72468569 | 72469574 |
| chr8 | 72470399 | 72470441 | chr8 | 72471053 | 72471083 | chr8 | 72754491 | 72754609 |
| chr8 | 72754821 | 72755176 | chr8 | 72755666 | 72755814 | chr8 | 72756656 | 72756896 |
| chr8 | 72917335 | 72917428 | chr8 | 72987600 | 72988036 | chr8 | 73163860 | 73164180 |
| chr8 | 73450064 | 73450100 | chr8 | 73450515 | 73450559 | chr8 | 74759385 | 74759463 |
| chr8 | 74759819 | 74759863 | chr8 | 75896574 | 75897337 | chr8 | 76316329 | 76316452 |
| chr8 | 77585219 | 77585698 | chr8 | 77586175 | 77586278 | chr8 | 77586563 | 77586617 |
| chr8 | 77590239 | 77590466 | chr8 | 77593110 | 77593376 | chr8 | 77593889 | 77594124 |
| chr8 | 77594648 | 77594674 | chr8 | 77594758 | 77594993 | chr8 | 77595339 | 77595494 |
| chr8 | 79428297 | 79428401 | chr8 | 80523983 | 80524029 | chr8 | 80524253 | 80524318 |
| chr8 | 80524946 | 80525020 | chr8 | 80525604 | 80525733 | chr8 | 80695902 | 80695932 |
| chr8 | 80803673 | 80803872 | chr8 | 81398018 | 81398155 | chr8 | 81398428 | 81399496 |
| chr8 | 81414737 | 81414831 | chr8 | 81478185 | 81478350 | chr8 | 85095482 | 85095668 |
| chr8 | 85096583 | 85096724 | chr8 | 85097063 | 85097220 | chr8 | 86350553 | 86350566 |
| chr8 | 86406813 | 86406849 | chr8 | 86436621 | 86436651 | chr8 | 86544756 | 86544798 |
| chr8 | 89339389 | 89339745 | chr8 | 89340274 | 89340345 | chr8 | 90913516 | 90913653 |
| chr8 | 91094221 | 91094251 | chr8 | 91803676 | 91803718 | chr8 | 91804055 | 91804253 |
| chr8 | 91997046 | 91997508 | chr8 | 91997528 | 91997947 | chr8 | 92083523 | 92083667 |
| chr8 | 93114135 | 93114241 | chr8 | 93114307 | 93114528 | chr8 | 95485999 | 95486029 |
| chr8 | 95651098 | 95651218 | chr8 | 95651538 | 95651655 | chr8 | 96219882 | 96219901 |
| chr8 | 96285420 | 96285457 | chr8 | 97157085 | 97157209 | chr8 | 97157667 | 97157897 |
| chr8 | 97158022 | 97158066 | chr8 | 97165644 | 97165676 | chr8 | 97166425 | 97166455 |
| chr8 | 97167178 | 97167223 | chr8 | 97167811 | 97167855 | chr8 | 97169838 | 97169955 |
| chr8 | 97170054 | 97170334 | chr8 | 97170867 | 97170897 | chr8 | 97171129 | 97171264 |
| chr8 | 97171318 | 97171958 | chr8 | 97172019 | 97172200 | chr8 | 97172433 | 97172739 |
| chr8 | 97172822 | 97173458 | chr8 | 97173822 | 97173863 | chr8 | 97173921 | 97173935 |
| chr8 | 97339846 | 97340195 | chr8 | 97506034 | 97506048 | chr8 | 97506178 | 97506407 |
| chr8 | 97506448 | 97506524 | chr8 | 97507115 | 97507284 | chr8 | 97507546 | 97507680 |
| chr8 | 98289825 | 98289867 | chr8 | 98290923 | 98290260 | chr8 | 98744202 | 98744234 |
| chr8 | 99234962 | 99235037 | chr8 | 99439104 | 99439133 | chr8 | 99439382 | 99440354 |
| chr8 | 99951404 | 99951434 | chr8 | 99951836 | 99952143 | chr8 | 99952199 | 99952303 |
| chr8 | 99952533 | 99952815 | chr8 | 99954490 | 99954562 | chr8 | 99954679 | 99954727 |
| chr8 | 99955180 | 99955327 | chr8 | 99959429 | 99959549 | chr8 | 99960329 | 99960407 |
| chr8 | 99960922 | 99960971 | chr8 | 99961792 | 99961822 | chr8 | 99985866 | 99986043 |
| chr8 | 99986226 | 99986526 | chr8 | 99986792 | 99987014 | chr8 | 101118241 | 101118490 |
| chr8 | 101661920 | 101661991 | chr8 | 101821973 | 101822047 | chr8 | 101920382 | 101920468 |
| chr8 | 102504464 | 102504506 | chr8 | 102505512 | 102505556 | chr8 | 102505797 | 102505985 |
| chr8 | 103629856 | 103629882 | chr8 | 104153202 | 104153246 | chr8 | 104153449 | 104153561 |
| chr8 | 104383700 | 104383985 | chr8 | 104512123 | 104513186 | chr8 | 104513462 | 104513926 |
| chr8 | 105235369 | 105235501 | chr8 | 105235644 | 105235803 | chr8 | 105235864 | 105236054 |
| chr8 | 105478725 | 105478779 | chr8 | 105479404 | 105479464 | chr8 | 106331160 | 106331237 |
| chr8 | 106332104 | 106332202 | chr8 | 107282163 | 107282195 | chr8 | 107284038 | 107284075 |
| chr8 | 108509543 | 108509697 | chr8 | 109093679 | 109094180 | chr8 | 109094485 | 109094595 |
| chr8 | 109094840 | 109095436 | chr8 | 109095506 | 109095932 | chr8 | 109799588 | 109799739 |
| chr8 | 110275006 | 110275023 | chr8 | 110406028 | 110406106 | chr8 | 110592198 | 110592228 |
| chr8 | 110704001 | 110704144 | chr8 | 110986443 | 110986682 | chr8 | 114444580 | 114445192 |
| chr8 | 114445763 | 114446068 | chr8 | 114446405 | 114446435 | chr8 | 114446931 | 114447368 |
| chr8 | 114449039 | 114449257 | chr8 | 114449550 | 114449602 | chr8 | 116660527 | 116660571 |
| chr8 | 116660616 | 116660760 | chr8 | 117950438 | 117950468 | chr8 | 117950783 | 117950914 |
| chr8 | 118532128 | 118532150 | chr8 | 120219912 | 120219941 | chr8 | 120220116 | 120220145 |
| chr8 | 120220428 | 120220592 | chr8 | 120650979 | 120651008 | chr8 | 120651221 | 120651412 |
| chr8 | 120844095 | 120844130 | chr8 | 121136879 | 121137748 | chr8 | 121823901 | 121823930 |
| chr8 | 121824203 | 121824481 | chr8 | 121825455 | 121825484 | chr8 | 122347026 | 122347052 |
| chr8 | 122651872 | 122651905 | chr8 | 123695532 | 123695660 | chr8 | 124055256 | 124055256 |
| chr8 | 124173246 | 124173501 | chr8 | 124332846 | 124332875 | chr8 | 125411827 | 125411857 |
| chr8 | 125452366 | 125452394 | chr8 | 126007961 | 126008051 | chr8 | 126044442 | 126044563 |
| chr8 | 127569621 | 127569676 | chr8 | 128403354 | 128403383 | chr8 | 128745542 | 128745618 |
| chr8 | 128808002 | 128808077 | chr8 | 128872385 | 128872415 | chr8 | 128889324 | 128889422 |
| chr8 | 128931133 | 128931261 | chr8 | 130369274 | 130369364 | chr8 | 132052147 | 132052299 |
| chr8 | 132052399 | 132052515 | chr8 | 132052590 | 132053164 | chr8 | 132053715 | 132054583 |
| chr8 | 132054594 | 132054785 | chr8 | 133686745 | 133686836 | chr8 | 139508757 | 139508946 |
| chr8 | 139509741 | 139509928 | chr8 | 140714570 | 140714877 | chr8 | 140715090 | 140715094 |
| chr8 | 140715469 | 140715587 | chr8 | 140715965 | 140716021 | chr8 | 140716340 | 140716354 |
| chr8 | 140755383 | 140755550 | chr8 | 140834237 | 140834321 | chr8 | 140963292 | 140963362 |
| chr8 | 141054845 | 141054875 | chr8 | 141159919 | 141159949 | chr8 | 141588056 | 141588132 |
| chr8 | 141596886 | 141597022 | chr8 | 141614252 | 141614287 | chr8 | 142265206 | 142265243 |
| chr8 | 142282078 | 142282202 | chr8 | 142292552 | 142292774 | chr8 | 142318155 | 142318184 |

TABLE 13-continued

| chr | start | end | chr | start | end | chr | start | end |
|---|---|---|---|---|---|---|---|---|
| chr8 | 142361233 | 142361487 | chr8 | 142367368 | 142367790 | chr8 | 142444600 | 142444752 |
| chr8 | 142528400 | 142528402 | chr8 | 142528455 | 142528606 | chr8 | 142528671 | 142528781 |
| chr8 | 142528835 | 142528961 | chr8 | 142535343 | 142535496 | chr8 | 142568598 | 142568652 |
| chr8 | 142632436 | 142632465 | chr8 | 142694847 | 142694953 | chr8 | 142984512 | 142984666 |
| chr8 | 143082777 | 143082810 | chr8 | 143089030 | 143089100 | chr8 | 143105244 | 143105377 |
| chr8 | 143368318 | 143368469 | chr8 | 143509457 | 143509594 | chr8 | 143532122 | 143532509 |
| chr8 | 143532542 | 143532846 | chr8 | 143533611 | 143533640 | chr8 | 143533709 | 143533906 |
| chr8 | 143557980 | 143558080 | chr8 | 143558472 | 143558604 | chr8 | 143587331 | 143587382 |
| chr8 | 143592664 | 143592687 | chr8 | 143611232 | 143611262 | chr8 | 143621980 | 143622096 |
| chr8 | 143702052 | 143702101 | chr8 | 143819384 | 143819406 | chr8 | 143858522 | 143858699 |
| chr8 | 143859338 | 143859361 | chr8 | 143876928 | 143876958 | chr8 | 143993974 | 143994165 |
| chr8 | 144069546 | 144069651 | chr8 | 144190378 | 144190432 | chr8 | 144203653 | 144203708 |
| chr8 | 144203977 | 144204021 | chr8 | 144226174 | 144226204 | chr8 | 144238822 | 144238901 |
| chr8 | 144241250 | 144241287 | chr8 | 144241871 | 144242356 | chr8 | 144303562 | 144303592 |
| chr8 | 144328321 | 144328565 | chr8 | 144330287 | 144330380 | chr8 | 144344293 | 144344442 |
| chr8 | 144347719 | 144347740 | chr8 | 144359977 | 144360076 | chr8 | 144360394 | 144360453 |
| chr8 | 144361758 | 144361823 | chr8 | 144372473 | 144372503 | chr8 | 144382679 | 144382697 |
| chr8 | 144421487 | 144421517 | chr8 | 144509325 | 144510529 | chr8 | 144511225 | 144511424 |
| chr8 | 144512041 | 144512192 | chr8 | 144512473 | 144512503 | chr8 | 144557046 | 144557088 |
| chr8 | 144601799 | 144601851 | chr8 | 144617065 | 144617206 | chr8 | 144650594 | 144650730 |
| chr8 | 144668566 | 144668667 | chr8 | 144668909 | 144668972 | chr8 | 145033304 | 145033333 |
| chr8 | 145218226 | 145218301 | chr8 | 145223902 | 145224061 | chr8 | 145753517 | 145753547 |
| chr8 | 145758572 | 145758692 | chr8 | 145806258 | 145806271 | chr8 | 145925461 | 145925491 |
| chr8 | 145925947 | 145926068 | chr8 | 146013617 | 146013647 | chr8 | 146079215 | 146079297 |
| chr9 | 113433 | 113512 | chr9 | 113550 | 113556 | chr9 | 113850 | 113885 |
| chr9 | 117884 | 117959 | chr9 | 841691 | 842031 | chr9 | 842208 | 842230 |
| chr9 | 842611 | 842673 | chr9 | 969556 | 969586 | chr9 | 969788 | 969846 |
| chr9 | 970096 | 970104 | chr9 | 970186 | 970225 | chr9 | 970495 | 970525 |
| chr9 | 970897 | 970911 | chr9 | 970993 | 971175 | chr9 | 972307 | 972759 |
| chr9 | 973184 | 973289 | chr9 | 974514 | 974547 | chr9 | 975117 | 975167 |
| chr9 | 975783 | 976321 | chr9 | 976618 | 976689 | chr9 | 976912 | 976961 |
| chr9 | 981797 | 981830 | chr9 | 1042402 | 1042500 | chr9 | 1042616 | 1042986 |
| chr9 | 1051905 | 1052166 | chr9 | 2115824 | 2115981 | chr9 | 3181752 | 3181869 |
| chr9 | 5070006 | 5070050 | chr9 | 5073756 | 5073788 | chr9 | 5078346 | 5078375 |
| chr9 | 5089711 | 5089740 | chr9 | 6412571 | 6412809 | chr9 | 6644297 | 6644367 |
| chr9 | 6644540 | 6644554 | chr9 | 6645017 | 6645333 | chr9 | 6645625 | 6645700 |
| chr9 | 6756353 | 6756458 | chr9 | 13278818 | 13278864 | chr9 | 14312994 | 14313096 |
| chr9 | 14313319 | 14313785 | chr9 | 14347633 | 14347673 | chr9 | 14348314 | 14348452 |
| chr9 | 17906404 | 17906432 | chr9 | 17906461 | 17906694 | chr9 | 17907004 | 17907061 |
| chr9 | 17907451 | 17907472 | chr9 | 19789107 | 19789301 | chr9 | 21031734 | 21031836 |
| chr9 | 21402617 | 21403021 | chr9 | 21559294 | 21559381 | chr9 | 21559665 | 21559702 |
| chr9 | 21965057 | 21965424 | chr9 | 21965570 | 21965757 | chr9 | 21968218 | 21968433 |
| chr9 | 21968457 | 21968475 | chr9 | 21970959 | 21971154 | chr9 | 21971185 | 21971220 |
| chr9 | 21974182 | 21974237 | chr9 | 21974499 | 21974794 | chr9 | 21994208 | 21994237 |
| chr9 | 21995297 | 21995326 | chr9 | 21995720 | 21995749 | chr9 | 22006131 | 22006152 |
| chr9 | 22008819 | 22008899 | chr9 | 22447664 | 22447708 | chr9 | 23822568 | 23822606 |
| chr9 | 23824561 | 23824591 | chr9 | 23831100 | 23831370 | chr9 | 29212170 | 29212170 |
| chr9 | 29212211 | 29212294 | chr9 | 29213508 | 29213651 | chr9 | 29214030 | 29214144 |
| chr9 | 29214360 | 29214430 | chr9 | 29214681 | 29215086 | chr9 | 32782630 | 32782935 |
| chr9 | 32783084 | 32783121 | chr9 | 32783346 | 32783419 | chr9 | 32783591 | 32783657 |
| chr9 | 33524609 | 33524687 | chr9 | 33676771 | 33676801 | chr9 | 33677360 | 33677415 |
| chr9 | 34224348 | 34224474 | chr9 | 34372805 | 34372983 | chr9 | 34589062 | 34589156 |
| chr9 | 35617291 | 35617337 | chr9 | 35675539 | 35675647 | chr9 | 35675838 | 35676180 |
| chr9 | 35844834 | 35844863 | chr9 | 36037068 | 36037098 | chr9 | 36318375 | 36318393 |
| chr9 | 36739812 | 36739980 | chr9 | 36832204 | 36832343 | chr9 | 37002454 | 37002517 |
| chr9 | 37002819 | 37003077 | chr9 | 37025564 | 37025783 | chr9 | 37026146 | 37026351 |
| chr9 | 37026434 | 37026622 | chr9 | 37026831 | 37027271 | chr9 | 37027325 | 37027412 |
| chr9 | 37027800 | 37027829 | chr9 | 37028944 | 37029119 | chr9 | 37029534 | 37030655 |
| chr9 | 37034197 | 37034247 | chr9 | 37034616 | 37034731 | chr9 | 37035366 | 37035734 |
| chr9 | 37036425 | 37036647 | chr9 | 37037671 | 37038354 | chr9 | 37467610 | 37467634 |
| chr9 | 38620530 | 38620725 | chr9 | 66456023 | 66456047 | chr9 | 71200632 | 71200662 |
| chr9 | 71734816 | 71734920 | chr9 | 71788952 | 71789260 | chr9 | 71789453 | 71789757 |
| chr9 | 73032801 | 73032831 | chr9 | 74061838 | 74062070 | chr9 | 74210499 | 74210517 |
| chr9 | 74764547 | 74764648 | chr9 | 77112993 | 77113340 | chr9 | 77113559 | 77113708 |
| chr9 | 77113806 | 77113825 | chr9 | 77114745 | 77114851 | chr9 | 77115210 | 77115447 |
| chr9 | 77115657 | 77115687 | chr9 | 79231003 | 79231033 | chr9 | 79626876 | 79627370 |
| chr9 | 79628289 | 79628329 | chr9 | 79629208 | 79629471 | chr9 | 79629879 | 79630420 |
| chr9 | 79631192 | 79631335 | chr9 | 79631555 | 79631591 | chr9 | 79631865 | 79632182 |
| chr9 | 79632860 | 79632890 | chr9 | 79533397 | 79633904 | chr9 | 79634170 | 79634987 |
| chr9 | 79635047 | 79635448 | chr9 | 79635746 | 79636043 | chr9 | 79636258 | 79637274 |
| chr9 | 79637643 | 79637888 | chr9 | 79638137 | 79638244 | chr9 | 80409473 | 80409502 |
| chr9 | 80833933 | 80834011 | chr9 | 85677905 | 85677992 | chr9 | 86152387 | 86152417 |
| chr9 | 86578079 | 86578103 | chr9 | 86755532 | 86755952 | chr9 | 86886706 | 86886836 |
| chr9 | 87283008 | 87283038 | chr9 | 87283677 | 87283709 | chr9 | 87284706 | 87284798 |
| chr9 | 87285279 | 87285472 | chr9 | 88137524 | 88137725 | chr9 | 88137875 | 88137998 |
| chr9 | 88694345 | 88694438 | chr9 | 89560760 | 89560827 | chr9 | 89561063 | 89561109 |
| chr9 | 91150222 | 91150335 | chr9 | 91606004 | 91606058 | chr9 | 91792357 | 91792387 |
| chr9 | 91792776 | 91792907 | chr9 | 91793177 | 91793526 | chr9 | 93698029 | 93698051 |

TABLE 13-continued

| chr | start | end | chr | start | end | chr | start | end |
|---|---|---|---|---|---|---|---|---|
| chr9 | 94183870 | 94183954 | chr9 | 94572641 | 94572743 | chr9 | 95417551 | 95417651 |
| chr9 | 95560810 | 95560840 | chr9 | 95569759 | 95569822 | chr9 | 95570247 | 95570434 |
| chr9 | 95571617 | 95571659 | chr9 | 95571719 | 95571760 | chr9 | 95947130 | 95947296 |
| chr9 | 96588858 | 96588885 | chr9 | 96710377 | 96710407 | chr9 | 96710647 | 96710991 |
| chr9 | 96711258 | 96711446 | chr9 | 96711535 | 96711617 | chr9 | 96711975 | 96712005 |
| chr9 | 96713378 | 96713893 | chr9 | 96715095 | 96715372 | chr9 | 96715688 | 96715857 |
| chr9 | 96716905 | 96717427 | chr9 | 96717450 | 96717466 | chr9 | 96717979 | 96718149 |
| chr9 | 96720803 | 96720885 | chr9 | 96721103 | 96721467 | chr9 | 96721689 | 96721802 |
| chr9 | 96722445 | 96722547 | chr9 | 96723093 | 96723159 | chr9 | 96723171 | 96723202 |
| chr9 | 97845915 | 97845947 | chr9 | 98111365 | 98111560 | chr9 | 98111895 | 98112157 |
| chr9 | 98112344 | 98112395 | chr9 | 98784772 | 98784802 | chr9 | 98789651 | 98790000 |
| chr9 | 99146020 | 99146153 | chr9 | 99259362 | 99259405 | chr9 | 99449135 | 99449451 |
| chr9 | 99639621 | 99639942 | chr9 | 99983140 | 99983170 | chr9 | 99983411 | 99983738 |
| chr9 | 09983798 | 99983824 | chr9 | 99984026 | 99984044 | chr9 | 100397979 | 100398016 |
| chr9 | 100503625 | 100503937 | chr9 | 100609991 | 100610134 | chr9 | 100610201 | 100610218 |
| chr9 | 100610681 | 100610816 | chr9 | 100611125 | 100611640 | chr9 | 100613828 | 100613999 |
| chr9 | 100614193 | 100614325 | chr9 | 100614541 | 100616035 | chr9 | 100616271 | 100616468 |
| chr9 | 100617293 | 100617365 | chr9 | 100617682 | 100618055 | chr9 | 100619722 | 100620069 |
| chr9 | 100620330 | 100620783 | chr9 | 100818336 | 100818437 | chr9 | 100835849 | 100835870 |
| chr9 | 101469269 | 101469307 | chr9 | 101469603 | 101469796 | chr9 | 101470116 | 101470260 |
| chr9 | 101470990 | 101471071 | chr9 | 101471570 | 101471621 | chr9 | 101471860 | 101472009 |
| chr9 | 101705996 | 101706195 | chr9 | 101706313 | 101706695 | chr9 | 103174705 | 103174730 |
| chr9 | 104248579 | 104248623 | chr9 | 104249475 | 104249562 | chr9 | 104500625 | 104500774 |
| chr9 | 110126074 | 110126247 | chr9 | 110228200 | 110228602 | chr9 | 110251388 | 110251418 |
| chr9 | 110252363 | 110252515 | chr9 | 112403170 | 112403200 | chr9 | 112403364 | 112403394 |
| chr9 | 113341522 | 113341621 | chr9 | 113341680 | 113341847 | chr9 | 113341927 | 113341965 |
| chr9 | 113342299 | 113342340 | chr9 | 115067932 | 115067959 | chr9 | 115478932 | 115478971 |
| chr9 | 115652966 | 115653425 | chr9 | 116633883 | 116633905 | chr9 | 117050981 | 117051030 |
| chr9 | 118917024 | 118917079 | chr9 | 120175795 | 120175832 | chr9 | 120176104 | 120176151 |
| chr9 | 120176867 | 120176897 | chr9 | 122131497 | 122131642 | chr9 | 122131880 | 122132025 |
| chr9 | 122132052 | 122132227 | chr9 | 123004898 | 123004928 | chr9 | 123295355 | 123295463 |
| chr9 | 124535347 | 124535611 | chr9 | 124749865 | 124749953 | chr9 | 124751485 | 124751515 |
| chr9 | 125676723 | 125676753 | chr9 | 126133778 | 126133856 | chr9 | 126154304 | 126154575 |
| chr9 | 126349038 | 126349104 | chr9 | 126770257 | 126770298 | chr9 | 126771532 | 126771705 |
| chr9 | 126774517 | 126774619 | chr9 | 126775530 | 126775560 | chr9 | 126776044 | 126776098 |
| chr9 | 126777529 | 126777746 | chr9 | 126777974 | 126777982 | chr9 | 126778359 | 126778496 |
| chr9 | 126779485 | 126780043 | chr9 | 126780285 | 126780315 | chr9 | 126780811 | 126780898 |
| chr9 | 126783295 | 126783499 | chr9 | 127212851 | 127213006 | chr9 | 127265876 | 127266025 |
| chr9 | 127266387 | 127266534 | chr9 | 127920543 | 127920572 | chr9 | 128635180 | 128635210 |
| chr9 | 128652200 | 128652232 | chr9 | 128759852 | 128759954 | chr9 | 129276718 | 129276820 |
| chr9 | 129372929 | 129373037 | chr9 | 129376170 | 129376199 | chr9 | 129376889 | 129376918 |
| chr9 | 129377214 | 129377316 | chr9 | 129377604 | 129377635 | chr9 | 129377773 | 129377959 |
| chr9 | 129387434 | 129387464 | chr9 | 129387848 | 129388200 | chr9 | 129388719 | 129388753 |
| chr9 | 129388996 | 129389192 | chr9 | 129400986 | 129401195 | chr9 | 129445255 | 129445566 |
| chr9 | 129445783 | 129445813 | chr9 | 129517783 | 129517821 | chr9 | 130248419 | 130248449 |
| chr9 | 130461687 | 130461742 | chr9 | 130675509 | 130675592 | chr9 | 130689631 | 130689667 |
| chr9 | 130689742 | 130689749 | chr9 | 131580038 | 131580118 | chr9 | 131607517 | 131607547 |
| chr9 | 131607770 | 131607800 | chr9 | 131854231 | 131854328 | chr9 | 131854708 | 131854732 |
| chr9 | 132373058 | 132373091 | chr9 | 132382635 | 132383109 | chr9 | 132383347 | 132383376 |
| chr9 | 132402840 | 132402883 | chr9 | 132403149 | 132403216 | chr9 | 132559377 | 132559417 |
| chr9 | 132804405 | 132804455 | chr9 | 132804796 | 132804974 | chr9 | 132805318 | 132805445 |
| chr9 | 132805737 | 132805893 | chr9 | 132881814 | 132881844 | chr9 | 133308893 | 133308941 |
| chr9 | 133534683 | 133534713 | chr9 | 133535734 | 133535839 | chr9 | 133536097 | 133536119 |
| chr9 | 133536150 | 133536344 | chr9 | 133536778 | 133536869 | chr9 | 133537182 | 133537549 |
| chr9 | 133538169 | 133538728 | chr9 | 133539606 | 133539709 | chr9 | 133541059 | 13341192 |
| chr9 | 133541689 | 133542337 | chr9 | 133738343 | 133738372 | chr9 | 133747505 | 133747534 |
| chr9 | 133773766 | 133773923 | chr9 | 133927347 | 133927481 | chr9 | 133928236 | 133928266 |
| chr9 | 134126670 | 134126741 | chr9 | 134191085 | 134191218 | chr9 | 134207916 | 134208012 |
| chr9 | 134421797 | 134421835 | chr9 | 134717313 | 134717367 | chr9 | 135037119 | 135037287 |
| chr9 | 135037334 | 135037357 | chr9 | 135073463 | 135073506 | chr9 | 135455407 | 135455585 |
| chr9 | 135455996 | 135456023 | chr9 | 135456476 | 135456544 | chr9 | 135456897 | 135456915 |
| chr9 | 135458477 | 135458597 | chr9 | 135460001 | 135460176 | chr9 | 135460869 | 135460899 |
| chr9 | 135461511 | 135461773 | chr9 | 135462048 | 135462077 | chr9 | 135462648 | 135462967 |
| chr9 | 135464798 | 135464918 | chr9 | 135465948 | 135466064 | chr9 | 135466118 | 135466132 |
| chr9 | 135466344 | 135466660 | chr9 | 135648238 | 135648275 | chr9 | 135796830 | 135796830 |
| chr9 | 135865090 | 135865161 | chr9 | 135898911 | 135899124 | chr9 | 136474490 | 136474591 |
| chr9 | 137111397 | 137111426 | chr9 | 137229892 | 137229921 | chr9 | 137299119 | 137299450 |
| chr9 | 137299670 | 137299699 | chr9 | 137534066 | 137534238 | chr9 | 137575915 | 137575945 |
| chr9 | 137656958 | 137657128 | chr9 | 137667327 | 137667357 | chr9 | 137702189 | 137702222 |
| chr9 | 137718901 | 137719001 | chr9 | 137722087 | 137722209 | chr9 | 137979893 | 137980011 |
| chr9 | 137980258 | 137980288 | chr9 | 137980880 | 137980910 | chr9 | 138265123 | 138265251 |
| chr9 | 138563059 | 138563280 | chr9 | 138606821 | 138606923 | chr9 | 138627636 | 138627893 |
| chr9 | 138634047 | 138634159 | chr9 | 138659800 | 138659905 | chr9 | 138660943 | 138661012 |
| chr9 | 138661648 | 138661870 | chr9 | 138666455 | 138666558 | chr9 | 138880711 | 138880875 |
| chr9 | 138991798 | 138991828 | chr9 | 139000566 | 139000642 | chr9 | 139012272 | 139012411 |
| chr9 | 139024750 | 139024782 | chr9 | 139045653 | 139045683 | chr9 | 139047532 | 139047633 |
| chr9 | 139085228 | 139085350 | chr9 | 139090500 | 139090551 | chr9 | 139091072 | 139091369 |
| chr9 | 139093773 | 139093890 | chr9 | 139094705 | 139094732 | chr9 | 139095340 | 139095485 |

TABLE 13-continued

| chr | start | end | chr | start | end | chr | start | end |
|---|---|---|---|---|---|---|---|---|
| chr9 | 139096650 | 139097006 | chr9 | 139111268 | 139111298 | chr9 | 139269039 | 139269121 |
| chr9 | 139399407 | 139399436 | chr9 | 139421955 | 139421985 | chr9 | 139477862 | 139478020 |
| chr9 | 139698925 | 139699051 | chr9 | 139704084 | 139704279 | chr9 | 139859041 | 139859268 |
| chr9 | 139888945 | 139888980 | chr9 | 140024842 | 140024918 | chr9 | 140024957 | 140025023 |
| chr9 | 140030498 | 140030528 | chr9 | 140031944 | 140031983 | chr9 | 140032891 | 140032951 |
| chr9 | 140033001 | 140033092 | chr9 | 140033426 | 140033490 | chr9 | 140033619 | 140033626 |
| chr9 | 140033909 | 140034079 | chr9 | 140050969 | 140051096 | chr9 | 140051220 | 140051354 |
| chr9 | 140127883 | 140128080 | chr9 | 140137310 | 140137339 | chr9 | 140197122 | 140197263 |
| chr9 | 140205394 | 140205519 | chr9 | 140245877 | 140245998 | chr9 | 140332708 | 140333018 |
| chr9 | 140382557 | 140382596 | chr9 | 140392454 | 140392484 | chr9 | 140397029 | 140397097 |
| chr9 | 140507256 | 140507419 | chr9 | 140704046 | 140704131 | chr9 | 140709046 | 140709174 |
| chr9 | 140727471 | 140727511 | chr9 | 140727845 | 140727930 | chr9 | 140769943 | 140769973 |
| chr9 | 140771975 | 140772347 | chr9 | 140772586 | 140772593 | chr9 | 140772757 | 140773301 |
| chr10 | 524754 | 524784 | chr10 | 833307 | 833386 | chr10 | 978878 | 978933 |
| chr10 | 1080415 | 1080513 | chr10 | 1120778 | 1120937 | chr10 | 1577394 | 1577424 |
| chr10 | 1585145 | 1585239 | chr10 | 1651360 | 1651374 | chr10 | 1708327 | 1708478 |
| chr10 | 1774858 | 1774887 | chr10 | 1779417 | 1779744 | chr10 | 3109360 | 3109459 |
| chr10 | 3197004 | 3197113 | chr10 | 3285672 | 3285698 | chr10 | 3330499 | 3330618 |
| chr10 | 3641378 | 3641396 | chr10 | 3678617 | 3678637 | chr10 | 3895410 | 3895452 |
| chr10 | 4599917 | 4599965 | chr10 | 5530764 | 5530975 | chr10 | 5855154 | 5855184 |
| chr10 | 5875140 | 5875358 | chr10 | 6003402 | 6003855 | chr10 | 6042309 | 6042571 |
| chr10 | 6162159 | 6162225 | chr10 | 6206142 | 6206217 | chr10 | 6372343 | 6372373 |
| chr10 | 6513976 | 6514006 | chr10 | 6577643 | 6577673 | chr10 | 6984463 | 6984639 |
| chr10 | 7205733 | 7205787 | chr10 | 7212745 | 7213064 | chr10 | 7213505 | 7213535 |
| chr10 | 7216059 | 7216089 | chr10 | 7236211 | 7236245 | chr10 | 7255730 | 7255821 |
| chr10 | 7323283 | 7323313 | chr10 | 7371678 | 7371708 | chr10 | 7414544 | 7414588 |
| chr10 | 7424626 | 7424687 | chr10 | 7436180 | 7436209 | chr10 | 7449954 | 7450189 |
| chr10 | 7450491 | 7451390 | chr10 | 7452227 | 7452777 | chr10 | 7453313 | 7453656 |
| chr10 | 7453903 | 7453930 | chr10 | 7708274 | 7708304 | chr10 | 7708790 | 7708856 |
| chr10 | 7708955 | 7709087 | chr10 | 7709723 | 7709752 | chr10 | 8055681 | 8055764 |
| chr10 | 8075930 | 8075944 | chr10 | 8076341 | 8076487 | chr10 | 8076804 | 8077374 |
| chr10 | 8077874 | 8078218 | chr10 | 8085039 | 8085721 | chr10 | 8085978 | 8086010 |
| chr10 | 8091895 | 8092278 | chr10 | 8093738 | 8093824 | chr10 | 8093860 | 8093963 |
| chr10 | 8095603 | 8095845 | chr10 | 8096160 | 8096190 | chr10 | 8096975 | 8097197 |
| chr10 | 8097474 | 8097537 | chr10 | 11059933 | 11060062 | chr10 | 11206206 | 11206235 |
| chr10 | 11207179 | 11207276 | chr10 | 11700918 | 11701075 | chr10 | 12390825 | 12390995 |
| chr10 | 12391870 | 12392327 | chr10 | 13043386 | 13043425 | chr10 | 13141001 | 13141020 |
| chr10 | 13715208 | 13715401 | chr10 | 13933005 | 13933035 | chr10 | 13933436 | 13933538 |
| chr10 | 13933597 | 13933934 | chr10 | 13933983 | 13934125 | chr10 | 13934169 | 13934183 |
| chr10 | 14393819 | 14393893 | chr10 | 14966129 | 14966212 | chr10 | 15140505 | 15140526 |
| chr10 | 15761292 | 15761671 | chr10 | 15762124 | 15762154 | chr10 | 16562369 | 16562672 |
| chr10 | 16562710 | 16563664 | chr10 | 16563691 | 16563909 | chr10 | 16564087 | 16564116 |
| chr10 | 16564537 | 16564566 | chr10 | 17269259 | 17269288 | chr10 | 17269628 | 17269789 |
| chr10 | 17270072 | 17270445 | chr10 | 17270991 | 17271254 | chr10 | 17271444 | 17271625 |
| chr10 | 17271914 | 17272233 | chr10 | 17272601 | 17272630 | chr10 | 17273172 | 17273201 |
| chr10 | 17275584 | 17275613 | chr10 | 17277741 | 17277770 | chr10 | 17429165 | 17429244 |
| chr10 | 17429544 | 17429622 | chr10 | 17496545 | 17496734 | chr10 | 18429628 | 18429774 |
| chr10 | 21101525 | 21101555 | chr10 | 21462533 | 21462607 | chr10 | 21462970 | 21463023 |
| chr10 | 21805217 | 21805277 | chr10 | 22047336 | 22047635 | chr10 | 22541638 | 22541850 |
| chr10 | 22542025 | 22542249 | chr10 | 22624022 | 22624305 | chr10 | 22624562 | 22625120 |
| chr10 | 22625383 | 22625782 | chr10 | 22625812 | 22625978 | chr10 | 22633985 | 22634174 |
| chr10 | 22634325 | 22634578 | chr10 | 22764649 | 22765791 | chr10 | 22765901 | 22765901 |
| chr10 | 23216865 | 23216945 | chr10 | 23460355 | 23460471 | chr10 | 23461222 | 23461754 |
| chr10 | 23462059 | 23462462 | chr10 | 23462486 | 23462614 | chr10 | 23462635 | 23462910 |
| chr10 | 23463267 | 23463853 | chr10 | 23463888 | 23464077 | chr10 | 23479876 | 23480696 |
| chr10 | 23480904 | 23481049 | chr10 | 23481321 | 23481515 | chr10 | 23481936 | 23482232 |
| chr10 | 23482289 | 23482445 | chr10 | 23483828 | 23484618 | chr10 | 23486264 | 23486328 |
| chr10 | 23487742 | 23487978 | chr10 | 23488393 | 23489158 | chr10 | 23489409 | 23489439 |
| chr10 | 23982438 | 23982820 | chr10 | 23983194 | 23983247 | chr10 | 23983618 | 23983700 |
| chr10 | 23984087 | 23984226 | chr10 | 23984923 | 23984991 | chr10 | 24988589 | 24988619 |
| chr10 | 25464619 | 25464915 | chr10 | 25465421 | 25465517 | chr10 | 26055755 | 26055841 |
| chr10 | 26223001 | 26223205 | chr10 | 26224031 | 26224061 | chr10 | 26500619 | 26500870 |
| chr10 | 26501539 | 26501589 | chr10 | 26503693 | 26503731 | chr10 | 26504114 | 26504143 |
| chr10 | 26504491 | 26504883 | chr10 | 26505009 | 26505227 | chr10 | 26505442 | 26505617 |
| chr10 | 26506057 | 26506163 | chr10 | 26506373 | 26506618 | chr10 | 26506950 | 26507400 |
| chr10 | 26681099 | 26681129 | chr10 | 26727098 | 26727368 | chr10 | 26727604 | 26727816 |
| chr10 | 26747051 | 26747075 | chr10 | 26816912 | 26816938 | chr10 | 26931897 | 26931926 |
| chr10 | 27547946 | 27548331 | chr10 | 27548401 | 27548484 | chr10 | 27794496 | 27794512 |
| chr10 | 27846637 | 27846727 | chr10 | 28030892 | 28030925 | chr10 | 28032966 | 28033020 |
| chr10 | 28033410 | 28033481 | chr10 | 28033770 | 28034186 | chr10 | 28034327 | 28034341 |
| chr10 | 28034874 | 28035300 | chr10 | 28035615 | 28035782 | chr10 | 28287373 | 28287557 |
| chr10 | 28287777 | 28288070 | chr10 | 28657255 | 28657343 | chr10 | 28958086 | 28958129 |
| chr10 | 29011047 | 29011162 | chr10 | 30026077 | 30026090 | chr10 | 30848200 | 30848230 |
| chr10 | 31073368 | 31073481 | chr10 | 31892922 | 31893079 | chr10 | 32499044 | 32499176 |
| chr10 | 33233313 | 33233361 | chr10 | 33624166 | 33624230 | chr10 | 33624492 | 33624560 |
| chr10 | 35929334 | 35929528 | chr10 | 43186151 | 43186181 | chr10 | 43250009 | 43250039 |
| chr10 | 43250406 | 43250779 | chr10 | 43250855 | 43250886 | chr10 | 43428424 | 43428576 |
| chr10 | 43429067 | 43429100 | chr10 | 43429376 | 43429411 | chr10 | 43572685 | 43572734 |

TABLE 13-continued

| chr | start | end | chr | start | end | chr | start | end |
|---|---|---|---|---|---|---|---|---|
| chr10 | 43600561 | 43600720 | chr10 | 43609055 | 43609117 | chr10 | 43609922 | 43609963 |
| chr10 | 43613890 | 43613919 | chr10 | 43614982 | 43615011 | chr10 | 43615554 | 43615607 |
| chr10 | 43617401 | 43617430 | chr10 | 43697887 | 43698086 | chr10 | 43698115 | 43698155 |
| chr10 | 43858343 | 43858437 | chr10 | 44879944 | 44880228 | chr10 | 44880869 | 44880915 |
| chr10 | 49652977 | 49653080 | chr10 | 49731548 | 49731749 | chr10 | 49732060 | 49732087 |
| chr10 | 49732156 | 49732498 | chr10 | 50323222 | 50323258 | chr10 | 50340119 | 50340149 |
| chr10 | 50507557 | 50507619 | chr10 | 50603967 | 50604159 | chr10 | 50604608 | 50604645 |
| chr10 | 50605057 | 50605654 | chr10 | 50606027 | 50606433 | chr10 | 50817015 | 50817132 |
| chr10 | 50817858 | 50817872 | chr10 | 50818382 | 50818432 | chr10 | 50818987 | 50819102 |
| chr10 | 50821472 | 50821701 | chr10 | 50887655 | 50887753 | chr10 | 50887790 | 50887816 |
| chr10 | 50977034 | 50977048 | chr10 | 52177545 | 52177575 | chr10 | 53107427 | 53107525 |
| chr10 | 54068526 | 54068610 | chr10 | 54072982 | 54073020 | chr10 | 54073265 | 54073295 |
| chr10 | 54074744 | 54074789 | chr10 | 57387429 | 57387796 | chr10 | 57388325 | 57388510 |
| chr10 | 57390290 | 57390637 | chr10 | 57391166 | 57391215 | chr10 | 60273130 | 60273278 |
| chr10 | 60935887 | 60935996 | chr10 | 60936524 | 60936729 | chr10 | 60937073 | 60937103 |
| chr10 | 63212324 | 63212701 | chr10 | 64575526 | 64575638 | chr10 | 64578171 | 64578540 |
| chr10 | 65262111 | 65262148 | chr10 | 70232445 | 70232485 | chr10 | 70275831 | 70275875 |
| chr10 | 70315131 | 70315148 | chr10 | 70586517 | 70586540 | chr10 | 71327725 | 71327764 |
| chr10 | 71328773 | 71328821 | chr10 | 71329079 | 71329118 | chr10 | 71329544 | 71329618 |
| chr10 | 71332052 | 21333018 | chr10 | 22015150 | 72015339 | chr10 | 72043779 | 72043894 |
| chr10 | 22200118 | 72200138 | chr10 | 72200354 | 72200771 | chr10 | 72200825 | 72201285 |
| chr10 | 72973130 | 72973180 | chr10 | 73156362 | 73156661 | chr10 | 73157867 | 73158027 |
| chr10 | 75407570 | 75407837 | chr10 | 75488953 | 75488979 | chr10 | 77190039 | 77190068 |
| chr10 | 77191224 | 77191368 | chr10 | 79396921 | 79397089 | chr10 | 81023884 | 81023914 |
| chr10 | 81154141 | 81154192 | chr10 | 81664867 | 81664899 | chr10 | 82117074 | 82117271 |
| chr10 | 83634261 | 83634361 | chr10 | 83634467 | 83634499 | chr10 | 83635531 | 83635545 |
| chr10 | 85954425 | 85954457 | chr10 | 88123672 | 88123701 | chr10 | 88149363 | 88149601 |
| chr10 | 88304914 | 88304944 | chr10 | 88684005 | 88684034 | chr10 | 89624255 | 89624311 |
| chr10 | 89653788 | 89653859 | chr10 | 89685272 | 89685322 | chr10 | 89690790 | 89690819 |
| chr10 | 89692776 | 89693015 | chr10 | 89711861 | 89711992 | chr10 | 89717610 | 89717744 |
| chr10 | 89720790 | 89720885 | chr10 | 89725030 | 89725071 | chr10 | 90966708 | 90966865 |
| chr10 | 90967671 | 90968040 | chr10 | 91295029 | 91295067 | chr10 | 91295585 | 91295725 |
| chr10 | 92617242 | 92617308 | chr10 | 93647216 | 93647300 | chr10 | 93647562 | 93647648 |
| chr10 | 94450675 | 94450726 | chr10 | 94451448 | 94451602 | chr10 | 94826023 | 94826056 |
| chr10 | 94828194 | 94828498 | chr10 | 94828735 | 94828828 | chr10 | 94834413 | 94835047 |
| chr10 | 95360716 | 95360750 | chr10 | 96304115 | 96304235 | chr10 | 98129822 | 98130033 |
| chr10 | 99080262 | 99080447 | chr10 | 99080862 | 99080930 | chr10 | 99474393 | 99474467 |
| chr10 | 99481826 | 99481905 | chr10 | 99531219 | 99531430 | chr10 | 99789175 | 99789282 |
| chr10 | 99790261 | 99790318 | chr10 | 99790590 | 99790664 | chr10 | 99790947 | 99791161 |
| chr10 | 100991907 | 100991935 | chr10 | 100992055 | 100992190 | chr10 | 100992222 | 100992443 |
| chr10 | 100992882 | 100992916 | chr10 | 100993537 | 100994016 | chr10 | 100996046 | 100996224 |
| chr10 | 101088995 | 101089439 | chr10 | 101089908 | 101090203 | chr10 | 101280204 | 101280485 |
| chr10 | 101283464 | 101283658 | chr10 | 101290117 | 101290160 | chr10 | 101290180 | 101291142 |
| chr10 | 101292297 | 101292919 | chr10 | 101293156 | 101293343 | chr10 | 101294750 | 101295586 |
| chr10 | 101296768 | 101296800 | chr10 | 101874886 | 101875138 | chr10 | 102322230 | 102322260 |
| chr10 | 102419400 | 102419681 | chr10 | 102430699 | 102430761 | chr10 | 102473856 | 102473932 |
| chr10 | 102483993 | 102484245 | chr10 | 102484270 | 102484554 | chr10 | 102495508 | 102495741 |
| chr10 | 102497273 | 102497708 | chr10 | 102498280 | 102498433 | chr10 | 102501359 | 102501389 |
| chr10 | 102507509 | 102507535 | chr10 | 102508996 | 102509285 | chr10 | 102589425 | 102589493 |
| chr10 | 102589786 | 102589915 | chr10 | 102590152 | 102590415 | chr10 | 102890941 | 102891582 |
| chr10 | 102891823 | 102891955 | chr10 | 102893624 | 102893951 | chr10 | 102894091 | 102895289 |
| chr10 | 102899173 | 102899601 | chr10 | 102899807 | 102899855 | chr10 | 102900263 | 102900575 |
| chr10 | 102906525 | 102906620 | chr10 | 102975619 | 102975834 | chr10 | 102976150 | 102976180 |
| chr10 | 102977051 | 102977412 | chr10 | 102983153 | 102983379 | chr10 | 102983435 | 102983749 |
| chr10 | 102984513 | 102984516 | chr10 | 102985772 | 102985963 | chr10 | 102986534 | 102986952 |
| chr10 | 102987207 | 102987558 | chr10 | 102989629 | 102989659 | chr10 | 102996116 | 102996480 |
| chr10 | 102996597 | 102996638 | chr10 | 102997329 | 102997406 | chr10 | 102998576 | 102998828 |
| chr10 | 103043975 | 103044227 | chr10 | 103044301 | 103044365 | chr10 | 103425950 | 103426174 |
| chr10 | 103432412 | 103432441 | chr10 | 103535622 | 103635770 | chr10 | 103536227 | 103536266 |
| chr10 | 103536300 | 103536416 | chr10 | 103579674 | 103579713 | chr10 | 103930126 | 103930161 |
| chr10 | 104170096 | 104170262 | chr10 | 104170408 | 104170732 | chr10 | 105036542 | 105036658 |
| chr10 | 105036701 | 105036863 | chr10 | 105037223 | 105037830 | chr10 | 105127047 | 105127076 |
| chr10 | 105155323 | 105155481 | chr10 | 105413627 | 105413784 | chr10 | 105420861 | 105420891 |
| chr10 | 105527028 | 105527057 | chr10 | 106398644 | 106398687 | chr10 | 106398826 | 106398886 |
| chr10 | 106399581 | 106400387 | chr10 | 106401323 | 106401432 | chr10 | 106401511 | 106402190 |
| chr10 | 106402272 | 106402325 | chr10 | 106402712 | 106402825 | chr10 | 108924045 | 108924059 |
| chr10 | 110671930 | 110672245 | chr10 | 111216789 | 111216803 | chr10 | 112403151 | 112403297 |
| chr10 | 112440378 | 112440408 | chr10 | 115804840 | 115805014 | chr10 | 116164248 | 116164341 |
| chr10 | 116331126 | 116331156 | chr10 | 116853875 | 116853908 | chr10 | 118030642 | 118030705 |
| chr10 | 118031302 | 118031548 | chr10 | 118031625 | 118032229 | chr10 | 118032413 | 118032547 |
| chr10 | 118032917 | 118033140 | chr10 | 118033260 | 118033542 | chr10 | 118034143 | 118034168 |
| chr10 | 118609305 | 118609390 | chr10 | 118890980 | 118891104 | chr10 | 118891517 | 118891661 |
| chr10 | 118891716 | 118891774 | chr10 | 118892013 | 118892456 | chr10 | 118892518 | 118893266 |
| chr10 | 118893680 | 118893825 | chr10 | 118894035 | 118894071 | chr10 | 118896629 | 118896805 |
| chr10 | 118897913 | 118897968 | chr10 | 118899273 | 118899302 | chr10 | 118899583 | 118899602 |
| chr10 | 118899893 | 118899957 | chr10 | 118900166 | 118900244 | chr10 | 118900324 | 118900498 |
| chr10 | 118922143 | 118922208 | chr10 | 118922721 | 118922901 | chr10 | 118923138 | 118923259 |
| chr10 | 118924604 | 118924896 | chr10 | 118927085 | 118927296 | chr10 | 118928548 | 118928727 |

TABLE 13-continued

| chr | start | end | chr | start | end | chr | start | end |
|---|---|---|---|---|---|---|---|---|
| chr10 | 119000690 | 119001154 | chr10 | 119001534 | 119001564 | chr10 | 119294352 | 119294461 |
| chr10 | 119294847 | 119294897 | chr10 | 119294909 | 119295245 | chr10 | 119296756 | 119296788 |
| chr10 | 119297384 | 119297529 | chr10 | 119301365 | 119301427 | chr10 | 119302141 | 119302155 |
| chr10 | 119302222 | 119302266 | chr10 | 119302962 | 119303174 | chr10 | 119304363 | 119304393 |
| chr10 | 119304896 | 119304985 | chr10 | 119305062 | 119305109 | chr10 | 119307022 | 119307052 |
| chr10 | 119311867 | 119311897 | chr10 | 119312751 | 119313193 | chr10 | 119590435 | 119590464 |
| chr10 | 119807026 | 119807056 | chr10 | 120354243 | 120354273 | chr10 | 120355548 | 120355614 |
| chr10 | 120800789 | 120800835 | chr10 | 120841558 | 120841574 | chr10 | 121267480 | 121267523 |
| chr10 | 122216896 | 122217083 | chr10 | 122708495 | 122708691 | chr10 | 122708992 | 122709022 |
| chr10 | 123256044 | 123256232 | chr10 | 123258020 | 123258091 | chr10 | 123274758 | 123274787 |
| chr10 | 123279548 | 123279697 | chr10 | 123357206 | 123357242 | chr10 | 123357766 | 123357893 |
| chr10 | 123922645 | 123922682 | chr10 | 124893178 | 124893192 | chr10 | 124893238 | 124893350 |
| chr10 | 124893635 | 124893765 | chr10 | 124893965 | 124894479 | chr10 | 124894889 | 124894922 |
| chr10 | 124895426 | 124895695 | chr10 | 124895833 | 124896456 | chr10 | 124897220 | 124897657 |
| chr10 | 124897957 | 124897973 | chr10 | 124899035 | 124899116 | chr10 | 124899754 | 124899786 |
| chr10 | 124901892 | 124902046 | chr10 | 124902139 | 124902568 | chr10 | 124902608 | 124903238 |
| chr10 | 124904921 | 124905119 | chr10 | 124905481 | 124905511 | chr10 | 124905920 | 124906174 |
| chr10 | 124906436 | 124906544 | chr10 | 124907312 | 124907534 | chr10 | 124908091 | 124908121 |
| chr10 | 124909086 | 124909114 | chr10 | 124909253 | 124909537 | chr10 | 124909674 | 124909725 |
| chr10 | 124910363 | 124910454 | chr10 | 124910709 | 124911048 | chr10 | 125425515 | 125425547 |
| chr10 | 125650866 | 125651162 | chr10 | 125851328 | 125851645 | chr10 | 125852299 | 125852497 |
| chr10 | 125852753 | 125853191 | chr10 | 126101966 | 126102001 | chr10 | 126135927 | 126136065 |
| chr10 | 126136506 | 126136723 | chr10 | 126137181 | 126137405 | chr10 | 126198949 | 126199077 |
| chr10 | 126697828 | 126698107 | chr10 | 126782965 | 126783048 | chr10 | 126828994 | 126829024 |
| chr10 | 128076561 | 128076630 | chr10 | 128993904 | 128994446 | chr10 | 128994727 | 128994903 |
| chr10 | 129379338 | 129379367 | chr10 | 129634993 | 129535445 | chr10 | 129535696 | 129535733 |
| chr10 | 129536080 | 129536223 | chr10 | 129536259 | 129536310 | chr10 | 129888804 | 129888885 |
| chr10 | 129948111 | 129948140 | chr10 | 130085356 | 130085362 | chr10 | 130203435 | 130203480 |
| chr10 | 130338727 | 130338768 | chr10 | 130338804 | 130338976 | chr10 | 130577764 | 130577794 |
| chr10 | 131348513 | 131348713 | chr10 | 131647903 | 131647933 | chr10 | 131761378 | 131761441 |
| chr10 | 131761687 | 131761725 | chr10 | 131762087 | 131762124 | chr10 | 131762592 | 131762631 |
| chr10 | 131762904 | 131762940 | chr10 | 131763633 | 131763717 | chr10 | 131767372 | 131767503 |
| chr10 | 131767543 | 131767649 | chr10 | 131768724 | 131769029 | chr10 | 131769533 | 131770237 |
| chr10 | 131770657 | 131770687 | chr10 | 131770988 | 131771093 | chr10 | 131936599 | 131936626 |
| chr10 | 131937392 | 131937428 | chr10 | 132001252 | 132001556 | chr10 | 133109192 | 133109260 |
| chr10 | 133110554 | 133110704 | chr10 | 133794883 | 133795241 | chr10 | 133795313 | 133795430 |
| chr10 | 133795682 | 133795883 | chr10 | 133795976 | 133796058 | chr10 | 133849598 | 133850008 |
| chr10 | 133850529 | 133850774 | chr10 | 133951602 | 133952025 | chr10 | 133979059 | 133979089 |
| chr10 | 134000008 | 134000052 | chr10 | 134000109 | 134000124 | chr10 | 134001140 | 134001260 |
| chr10 | 134016203 | 134016388 | chr10 | 134022845 | 134022875 | chr10 | 134039087 | 134039117 |
| chr10 | 134095594 | 134095833 | chr10 | 134119401 | 134119447 | chr10 | 134121401 | 134121430 |
| chr10 | 134273064 | 134273156 | chr10 | 134301095 | 134301212 | chr10 | 134481320 | 134481433 |
| chr10 | 134491021 | 134491114 | chr10 | 134499773 | 134499803 | chr10 | 134593329 | 134593416 |
| chr10 | 134598087 | 134598090 | chr10 | 134598368 | 134598530 | chr10 | 134599432 | 134599482 |
| chr10 | 134599808 | 134600016 | chr10 | 134600038 | 134600998 | chr10 | 134601556 | 134601715 |
| chr10 | 134602183 | 134602269 | chr10 | 134607970 | 134608183 | chr10 | 134665147 | 134665202 |
| chr10 | 134679129 | 134679265 | chr10 | 134690559 | 134690617 | chr10 | 134693587 | 134693709 |
| chr10 | 134699872 | 134699909 | chr10 | 134733221 | 134733275 | chr10 | 134733497 | 134733617 |
| chr10 | 134738378 | 134738642 | chr10 | 134755773 | 134756183 | chr10 | 134788083 | 134788251 |
| chr10 | 134796012 | 134796042 | chr10 | 134896060 | 134896092 | chr10 | 134901193 | 134901511 |
| chr10 | 134902008 | 134902124 | chr10 | 134902188 | 134902307 | chr10 | 134916714 | 134916774 |
| chr10 | 134941145 | 134941178 | chr10 | 134942840 | 134943114 | chr10 | 134943445 | 134943542 |
| chr10 | 134944742 | 134944772 | chr10 | 135002063 | 135002156 | chr10 | 135014963 | 135015132 |
| chr10 | 135017049 | 135017129 | chr10 | 135018032 | 135018070 | chr10 | 135018825 | 135018960 |
| chr10 | 135020801 | 135020893 | chr10 | 135023470 | 135023500 | chr10 | 135043088 | 135043538 |
| chr10 | 135043968 | 135044128 | chr10 | 135044555 | 135044573 | chr10 | 135048782 | 135048939 |
| chr10 | 135050311 | 135050679 | chr10 | 135076368 | 135076503 | chr10 | 135121316 | 135121345 |
| chr10 | 135121807 | 135122251 | chr10 | 135122742 | 135122808 | chr10 | 135122991 | 135123020 |
| chr10 | 135139555 | 135139730 | chr10 | 135153956 | 135154001 | chr11 | 232863 | 233062 |
| chr11 | 392576 | 392720 | chr11 | 394815 | 394968 | chr11 | 406876 | 406939 |
| chr11 | 407427 | 407463 | chr11 | 526389 | 526419 | chr11 | 533451 | 533567 |
| chr11 | 533859 | 533888 | chr11 | 534273 | 534302 | chr11 | 548766 | 548800 |
| chr11 | 611099 | 611128 | chr11 | 611691 | 611791 | chr11 | 636644 | 636673 |
| chr11 | 636895 | 636906 | chr11 | 637162 | 637263 | chr11 | 637350 | 637441 |
| chr11 | 679692 | 679722 | chr11 | 726417 | 726466 | chr11 | 763323 | 763686 |
| chr11 | 775261 | 775291 | chr11 | 829543 | 829708 | chr11 | 830174 | 830243 |
| chr11 | 850555 | 850823 | chr11 | 863062 | 863092 | chr11 | 1006077 | 1006107 |
| chr11 | 1027540 | 1027574 | chr11 | 1029238 | 1029403 | chr11 | 1030215 | 1030296 |
| chr11 | 1080391 | 1080454 | chr11 | 1081667 | 1081715 | chr11 | 1214665 | 1214917 |
| chr11 | 1215899 | 1215999 | chr11 | 1229945 | 1229975 | chr11 | 1244381 | 1244465 |
| chr11 | 1250889 | 1250924 | chr11 | 1251183 | 1251351 | chr11 | 1263602 | 1263644 |
| chr11 | 1274085 | 1274189 | chr11 | 1318403 | 1318432 | chr11 | 1358291 | 1358332 |
| chr11 | 1374959 | 1375003 | chr11 | 1411875 | 1411905 | chr11 | 1430714 | 1430794 |
| chr11 | 1464280 | 1464428 | chr11 | 1469228 | 1469379 | chr11 | 1471920 | 1472058 |
| chr11 | 1868081 | 1868237 | chr11 | 1946130 | 1946160 | chr11 | 1957391 | 1957530 |
| chr11 | 1959077 | 1959187 | chr11 | 2040107 | 2040148 | chr11 | 2209907 | 2210278 |
| chr11 | 2226048 | 2226078 | chr11 | 2278708 | 2278839 | chr11 | 2291259 | 2291493 |
| chr11 | 2291984 | 2292057 | chr11 | 2292106 | 2292359 | chr11 | 2292392 | 2292636 |

TABLE 13-continued

| chr | start | end | chr | start | end | chr | start | end |
|---|---|---|---|---|---|---|---|---|
| chr11 | 2402376 | 2402405 | chr11 | 2437991 | 2438144 | chr11 | 2465350 | 2465447 |
| chr11 | 2465462 | 2465491 | chr11 | 2466597 | 2466788 | chr11 | 2884103 | 2884143 |
| chr11 | 2884159 | 2884309 | chr11 | 3169665 | 3169835 | chr11 | 3181913 | 3181942 |
| chr11 | 3182104 | 3182133 | chr11 | 3767205 | 3767245 | chr11 | 4095819 | 4095864 |
| chr11 | 4209105 | 4209134 | chr11 | 4209382 | 4209411 | chr11 | 5993897 | 5993933 |
| chr11 | 7274215 | 7274245 | chr11 | 7695432 | 7695528 | chr11 | 8040536 | 8040563 |
| chr11 | 8040582 | 8040770 | chr11 | 8103002 | 8103115 | chr11 | 8189987 | 8190766 |
| chr11 | 8284535 | 8284760 | chr11 | 8289517 | 8289745 | chr11 | 8290195 | 8290423 |
| chr11 | 8615674 | 8615704 | chr11 | 9025970 | 9026348 | chr11 | 9112446 | 9112585 |
| chr11 | 9112640 | 9112741 | chr11 | 9405392 | 9405542 | chr11 | 10509678 | 10509807 |
| chr11 | 10811151 | 10811188 | chr11 | 10815867 | 10815903 | chr11 | 12029957 | 12030272 |
| chr11 | 12030823 | 12030852 | chr11 | 12132524 | 12132559 | chr11 | 12399040 | 12399222 |
| chr11 | 12399727 | 12399791 | chr11 | 12695481 | 12695495 | chr11 | 12695573 | 12695611 |
| chr11 | 12696611 | 12696746 | chr11 | 13030566 | 13030890 | chr11 | 13690121 | 13690157 |
| chr11 | 14316375 | 14316404 | chr11 | 15136085 | 15136394 | chr11 | 16628819 | 16628933 |
| chr11 | 16632514 | 16632670 | chr11 | 17497492 | 17497520 | chr11 | 17497546 | 17497685 |
| chr11 | 17740493 | 17740570 | chr11 | 17741679 | 17741889 | chr11 | 17741953 | 17742445 |
| chr11 | 17743742 | 17743775 | chr11 | 18100096 | 18100118 | chr11 | 18812614 | 18812653 |
| chr11 | 18813032 | 18813086 | chr11 | 18813451 | 18813542 | chr11 | 18813792 | 18813947 |
| chr11 | 19263848 | 19263878 | chr11 | 19367102 | 19367134 | chr11 | 19367268 | 19367330 |
| chr11 | 19735730 | 19735760 | chr11 | 20153718 | 20153764 | chr11 | 20178094 | 20178305 |
| chr11 | 20180279 | 20180793 | chr11 | 20181213 | 20181254 | chr11 | 20181725 | 20181993 |
| chr11 | 20182864 | 20182959 | chr11 | 20183251 | 20183421 | chr11 | 20183674 | 20183773 |
| chr11 | 20184569 | 20185410 | chr11 | 20229274 | 20229550 | chr11 | 20229863 | 20230091 |
| chr11 | 20230398 | 20230464 | chr11 | 20618197 | 20618392 | chr11 | 20618423 | 20618924 |
| chr11 | 20619717 | 20619974 | chr11 | 20621341 | 20621644 | chr11 | 20622705 | 20622792 |
| chr11 | 20623259 | 20623359 | chr11 | 20690653 | 20690877 | chr11 | 20691219 | 20691379 |
| chr11 | 20691432 | 20691452 | chr11 | 20691748 | 20691914 | chr11 | 20692453 | 20692529 |
| chr11 | 22215123 | 22215287 | chr11 | 22362934 | 22363189 | chr11 | 22364821 | 22364975 |
| chr11 | 22365407 | 22365477 | chr11 | 27742185 | 27742215 | chr11 | 27743115 | 27743173 |
| chr11 | 27743436 | 27743608 | chr11 | 27744147 | 27744504 | chr11 | 27744711 | 27744744 |
| chr11 | 30037593 | 30037743 | chr11 | 30038689 | 30038739 | chr11 | 30605919 | 30606123 |
| chr11 | 30606796 | 30606864 | chr11 | 30607367 | 30607409 | chr11 | 31818458 | 31818512 |
| chr11 | 31818671 | 31818652 | chr11 | 31819302 | 31819508 | chr11 | 31819568 | 31819833 |
| chr11 | 31820045 | 31820360 | chr11 | 31820461 | 31821025 | chr11 | 31821297 | 31821778 |
| chr11 | 31822325 | 31822393 | chr11 | 31824300 | 31824355 | chr11 | 31824564 | 31824680 |
| chr11 | 31825017 | 31825280 | chr11 | 31825696 | 31825754 | chr11 | 31825833 | 31826070 |
| chr11 | 31826107 | 31826303 | chr11 | 31826409 | 31826732 | chr11 | 31827114 | 31827204 |
| chr11 | 31827438 | 31827519 | chr11 | 31827598 | 31828123 | chr11 | 31833097 | 31833155 |
| chr11 | 31835707 | 31835797 | chr11 | 31836046 | 31836470 | chr11 | 31837019 | 31837512 |
| chr11 | 31837542 | 31838392 | chr11 | 31838678 | 31839051 | chr11 | 31839307 | 31839945 |
| chr11 | 31840042 | 31840080 | chr11 | 31840603 | 31840710 | chr11 | 31840769 | 31840922 |
| chr11 | 31841376 | 31842088 | chr11 | 31842175 | 31842276 | chr11 | 31846022 | 31846230 |
| chr11 | 31846434 | 31846985 | chr11 | 31847250 | 31847301 | chr11 | 31847371 | 31847712 |
| chr11 | 31847770 | 31847872 | chr11 | 31847896 | 31847925 | chr11 | 31848472 | 31848602 |
| chr11 | 31848723 | 31849300 | chr11 | 32009104 | 32009126 | chr11 | 32354844 | 32354959 |
| chr11 | 32355000 | 32355197 | chr11 | 32448583 | 32448893 | chr11 | 32455602 | 32455634 |
| chr11 | 32455841 | 32456025 | chr11 | 32456279 | 32456445 | chr11 | 32456759 | 32457176 |
| chr11 | 32457712 | 32458175 | chr11 | 32458389 | 32458823 | chr11 | 32459684 | 32460071 |
| chr11 | 32460468 | 32460515 | chr11 | 32460796 | 32460864 | chr11 | 33037467 | 33037556 |
| chr11 | 33858424 | 33858463 | chr11 | 33890297 | 33890334 | chr11 | 33993984 | 33994014 |
| chr11 | 34535093 | 34535123 | chr11 | 35547499 | 35547562 | chr11 | 35641683 | 35641718 |
| chr11 | 35684958 | 35685131 | chr11 | 43596513 | 43596608 | chr11 | 43600453 | 43600557 |
| chr11 | 43601094 | 43601467 | chr11 | 43602468 | 43603036 | chr11 | 43603077 | 43603228 |
| chr11 | 43603628 | 43604145 | chr11 | 44325688 | 44325747 | chr11 | 44326137 | 44326184 |
| chr11 | 44327252 | 44327413 | chr11 | 44330878 | 44331439 | chr11 | 44331483 | 44331711 |
| chr11 | 44333052 | 44333081 | chr11 | 44333371 | 44333461 | chr11 | 44333477 | 44333480 |
| chr11 | 44337533 | 44337571 | chr11 | 44337727 | 44337861 | chr11 | 44337883 | 44338057 |
| chr11 | 44338335 | 44338367 | chr11 | 44340823 | 44340858 | chr11 | 44341966 | 44342034 |
| chr11 | 46316896 | 46317355 | chr11 | 46317408 | 46317680 | chr11 | 46413042 | 46413304 |
| chr11 | 46866492 | 46866510 | chr11 | 46940419 | 46940531 | chr11 | 47209044 | 47209189 |
| chr11 | 47358926 | 47359237 | chr11 | 47363557 | 47363625 | chr11 | 47372828 | 47373002 |
| chr11 | 47485995 | 47485141 | chr11 | 57194355 | 57194509 | chr11 | 57235406 | 57235436 |
| chr11 | 57414663 | 57414663 | chr11 | 57437196 | 57437234 | chr11 | 57501025 | 57501068 |
| chr11 | 58672746 | 58673064 | chr11 | 59323596 | 59323729 | chr11 | 59329223 | 59329240 |
| chr11 | 59333405 | 59333541 | chr11 | 60718668 | 60718853 | chr11 | 60718977 | 60719163 |
| chr11 | 61049694 | 61049736 | chr11 | 61058283 | 61058341 | chr11 | 61062822 | 61063023 |
| chr11 | 61063062 | 61063138 | chr11 | 61148730 | 61148749 | chr11 | 61277002 | 61277119 |
| chr11 | 61536985 | 61537014 | chr11 | 61595086 | 61595262 | chr11 | 61596420 | 61596640 |
| chr11 | 61654655 | 61654770 | chr11 | 61666106 | 61666136 | chr11 | 52370720 | 62370750 |
| chr11 | 62440549 | 62440588 | chr11 | 62484517 | 62484547 | chr11 | 63609979 | 63610013 |
| chr11 | 63641072 | 63641104 | chr11 | 63839478 | 63839528 | chr11 | 63849394 | 63849426 |
| chr11 | 63934589 | 63934619 | chr11 | 64105954 | 64106031 | chr11 | 64120879 | 64120909 |
| chr11 | 64140397 | 64140427 | chr11 | 64410723 | 64410759 | chr11 | 64480429 | 64480593 |
| chr11 | 64480824 | 64481042 | chr11 | 64490435 | 64490561 | chr11 | 64490792 | 64490806 |
| chr11 | 64490826 | 64491159 | chr11 | 64578577 | 64578600 | chr11 | 64739468 | 64739508 |
| chr11 | 64809865 | 64809906 | chr11 | 64950292 | 64950374 | chr11 | 65091291 | 65091369 |
| chr11 | 65185548 | 65185728 | chr11 | 65405659 | 65405774 | chr11 | 65409759 | 65409861 |

TABLE 13-continued

| chr | start | end | chr | start | end | chr | start | end |
|---|---|---|---|---|---|---|---|---|
| chr11 | 65478524 | 65478611 | chr11 | 65511027 | 65611172 | chr11 | 65511392 | 55511522 |
| chr11 | 65554043 | 65554410 | chr11 | 65600810 | 65601640 | chr11 | 65778952 | 55778981 |
| chr11 | 65779317 | 65779357 | chr11 | 65816447 | 65816519 | chr11 | 65816561 | 65816564 |
| chr11 | 66114279 | 66114331 | chr11 | 66188115 | 66188145 | chr11 | 66188473 | 66188484 |
| chr11 | 66188571 | 66188783 | chr11 | 66188853 | 66188974 | chr11 | 66454424 | 66454454 |
| chr11 | 66511223 | 66511327 | chr11 | 66513217 | 66513252 | chr11 | 66513552 | 66513646 |
| chr11 | 66625207 | 66625240 | chr11 | 66649028 | 66649058 | chr11 | 66658257 | 66658290 |
| chr11 | 66725600 | 66725637 | chr11 | 66790621 | 66790655 | chr11 | 67072239 | 67072396 |
| chr11 | 67139422 | 67139460 | chr11 | 67139535 | 67139546 | chr11 | 67210017 | 67210057 |
| chr11 | 67248420 | 67248458 | chr11 | 67350961 | 67350990 | chr11 | 57462643 | 67462833 |
| chr11 | 67764187 | 67764254 | chr11 | 67781196 | 67781564 | chr11 | 67797202 | 67797281 |
| chr11 | 68096034 | 68096179 | chr11 | 68118716 | 68118745 | chr11 | 68153950 | 68154098 |
| chr11 | 68181217 | 68181288 | chr11 | 68409558 | 68409588 | chr11 | 68804728 | 68804776 |
| chr11 | 69192566 | 69192784 | chr11 | 69280561 | 69280633 | chr11 | 69466004 | 69466042 |
| chr11 | 69484356 | 69484454 | chr11 | 69516968 | 69517174 | chr11 | 69518030 | 69518211 |
| chr11 | 69518530 | 69518718 | chr11 | 69588930 | 69589184 | chr11 | 69589824 | 69589854 |
| chr11 | 69590149 | 69590222 | chr11 | 70211516 | 70211545 | chr11 | 71192746 | 71192889 |
| chr11 | 71318332 | 71318809 | chr11 | 71318953 | 71318967 | chr11 | 71951639 | 71951738 |
| chr11 | 71952340 | 71952416 | chr11 | 71952459 | 71952541 | chr11 | 71954492 | 71954642 |
| chr11 | 71955344 | 71955377 | chr11 | 71956007 | 71966340 | chr11 | 72413980 | 72414010 |
| chr11 | 72432837 | 72432916 | chr11 | 72475677 | 72475711 | chr11 | 72532348 | 72532378 |
| chr11 | 72929747 | 72929883 | chr11 | 73072907 | 73072953 | chr11 | 73310367 | 73310441 |
| chr11 | 73685698 | 73685845 | chr11 | 73694609 | 73694659 | chr11 | 74394491 | 74394600 |
| chr11 | 74953265 | 74953336 | chr11 | 75379283 | 75379895 | chr11 | 75459486 | 75459571 |
| chr11 | 75858210 | 75858240 | chr11 | 76371738 | 76372077 | chr11 | 78672917 | 78672964 |
| chr11 | 79151173 | 79151216 | chr11 | 82444376 | 82445101 | chr11 | 82998001 | 82998031 |
| chr11 | 86085742 | 86085861 | chr11 | 86085932 | 86085968 | chr11 | 86383167 | 86383710 |
| chr11 | 88241705 | 88241975 | chr11 | 88242131 | 88242274 | chr11 | 88242359 | 88242618 |
| chr11 | 88799082 | 88799209 | chr11 | 89867794 | 89867990 | chr11 | 91957500 | 91957674 |
| chr11 | 91957974 | 91958230 | chr11 | 91958734 | 91959326 | chr11 | 91959355 | 91959430 |
| chr11 | 91959899 | 91960045 | chr11 | 93063583 | 93063645 | chr11 | 93063870 | 93063948 |
| chr11 | 93911651 | 93911800 | chr11 | 94134086 | 94134463 | chr11 | 94134683 | 94134853 |
| chr11 | 94275794 | 94275813 | chr11 | 94278456 | 94278603 | chr11 | 94473600 | 94473768 |
| chr11 | 94473803 | 94474139 | chr11 | 94474356 | 94474385 | chr11 | 94502334 | 94502489 |
| chr11 | 94884130 | 94884160 | chr11 | 98891477 | 98891882 | chr11 | 100997649 | 100997981 |
| chr11 | 100998276 | 100998318 | chr11 | 100998667 | 100998744 | chr11 | 101453180 | 101453518 |
| chr11 | 102961347 | 102961378 | chr11 | 102962922 | 102963062 | chr11 | 102980027 | 102980056 |
| chr11 | 104034521 | 104034996 | chr11 | 105480755 | 105480786 | chr11 | 105481216 | 105481571 |
| chr11 | 106888308 | 106888429 | chr11 | 106888641 | 106888801 | chr11 | 107461623 | 107461653 |
| chr11 | 107462415 | 107462459 | chr11 | 108236072 | 108236101 | chr11 | 108603233 | 108603263 |
| chr11 | 109292906 | 109293052 | chr11 | 109293720 | 109293763 | chr11 | 110166519 | 110166935 |
| chr11 | 110582232 | 110582434 | chr11 | 110582895 | 110583028 | chr11 | 110583044 | 110583050 |
| chr11 | 110583574 | 110583730 | chr11 | 111383183 | 111383531 | chr11 | 111383558 | 111383682 |
| chr11 | 111411093 | 111411581 | chr11 | 111411822 | 111412061 | chr11 | 111783506 | 111783577 |
| chr11 | 114113022 | 114113052 | chr11 | 115375120 | 115375177 | chr11 | 115530222 | 115530604 |
| chr11 | 115630531 | 115630910 | chr11 | 115631307 | 115631364 | chr11 | 116147253 | 116147283 |
| chr11 | 116451023 | 116451190 | chr11 | 117056042 | 117056073 | chr11 | 117296921 | 117297109 |
| chr11 | 118991056 | 118991079 | chr11 | 119148865 | 119148945 | chr11 | 119149236 | 119149265 |
| chr11 | 119292779 | 119292809 | chr11 | 119293370 | 119293615 | chr11 | 119612227 | 119612267 |
| chr11 | 119612324 | 119612399 | chr11 | 119612998 | 119613075 | chr11 | 120008105 | 120008504 |
| chr11 | 120039833 | 120039865 | chr11 | 120435405 | 120435477 | chr11 | 120435800 | 120435830 |
| chr11 | 120894800 | 120895026 | chr11 | 120998701 | 120998825 | chr11 | 122847265 | 122847696 |
| chr11 | 122848079 | 122848312 | chr11 | 122848369 | 122848591 | chr11 | 122849301 | 122849331 |
| chr11 | 122849783 | 122850123 | chr11 | 122850149 | 122850163 | chr11 | 122850424 | 122850536 |
| chr11 | 122851177 | 122851209 | chr11 | 122852438 | 122852475 | chr11 | 122855008 | 122855043 |
| chr11 | 122961137 | 122961219 | chr11 | 123066433 | 123066463 | chr11 | 123229058 | 123229406 |
| chr11 | 123300824 | 123301028 | chr11 | 123301083 | 123302026 | chr11 | 124735437 | 124735482 |
| chr11 | 124736196 | 124736252 | chr11 | 124738777 | 124739088 | chr11 | 125035763 | 125036208 |
| chr11 | 125220500 | 125220643 | chr11 | 125755612 | 125755710 | chr11 | 125773675 | 125774060 |
| chr11 | 126870182 | 126870212 | chr11 | 126870453 | 126870500 | chr11 | 126870525 | 126870543 |
| chr11 | 126873390 | 126873515 | chr11 | 128391893 | 128392116 | chr11 | 128562892 | 128563185 |
| chr11 | 128563337 | 128563730 | chr11 | 128563940 | 128564329 | chr11 | 128564740 | 128564876 |
| chr11 | 128564992 | 128565379 | chr11 | 128657931 | 128657970 | chr11 | 129242876 | 129243241 |
| chr11 | 129243305 | 129243582 | chr11 | 129243926 | 129244300 | chr11 | 129244441 | 129244603 |
| chr11 | 129245673 | 129245810 | chr11 | 129246070 | 129246129 | chr11 | 130318609 | 130318997 |
| chr11 | 130319527 | 130319613 | chr11 | 130343061 | 130343100 | chr11 | 130359769 | 130359812 |
| chr11 | 130359872 | 130359915 | chr11 | 130781550 | 130781781 | chr11 | 130785487 | 130785622 |
| chr11 | 131522763 | 131522947 | chr11 | 131564970 | 131565073 | chr11 | 131766868 | 131766960 |
| chr11 | 131780877 | 131781078 | chr11 | 132484215 | 132484404 | chr11 | 132813489 | 132813757 |
| chr11 | 132813908 | 132813949 | chr11 | 132864134 | 132864175 | chr11 | 132934123 | 132934176 |
| chr11 | 132952768 | 132953050 | chr11 | 132953233 | 132953423 | chr11 | 133231739 | 133231832 |
| chr11 | 133402206 | 133402260 | chr11 | 133792055 | 133792214 | chr11 | 133825226 | 133825543 |
| chr11 | 133906783 | 133906918 | chr11 | 133939002 | 133939177 | chr11 | 134145703 | 134146393 |
| chr11 | 134146682 | 134146894 | chr11 | 134201502 | 134201543 | chr11 | 134201841 | 134202084 |
| chr11 | 134281365 | 134281509 | chr12 | 570090 | 570171 | chr12 | 1639135 | 1639222 |
| chr12 | 2046104 | 2046134 | chr12 | 2162554 | 2162817 | chr12 | 2163164 | 2163276 |
| chr12 | 2403658 | 2403714 | chr12 | 2566053 | 2566247 | chr12 | 2595199 | 2595339 |
| chr12 | 2862068 | 2862142 | chr12 | 2964465 | 2964577 | chr12 | 3371882 | 3371911 |

TABLE 13-continued

| chr | start | end | chr | start | end | chr | start | end |
|---|---|---|---|---|---|---|---|---|
| chr12 | 3373533 | 3373666 | chr12 | 3600315 | 3600345 | chr12 | 3602270 | 3602716 |
| chr12 | 3602865 | 3602879 | chr12 | 3603100 | 3603156 | chr12 | 3862254 | 3862298 |
| chr12 | 4214005 | 4214157 | chr12 | 4274054 | 4274188 | chr12 | 4274271 | 4274409 |
| chr12 | 4362436 | 4362471 | chr12 | 4378252 | 4378330 | chr12 | 4379357 | 4379491 |
| chr12 | 4381433 | 4382386 | chr12 | 4382965 | 4382999 | chr12 | 4383492 | 4383784 |
| chr12 | 4384389 | 4384418 | chr12 | 4384736 | 4384902 | chr12 | 4392883 | 4392922 |
| chr12 | 4405589 | 4405619 | chr12 | 4554801 | 4554831 | chr12 | 4919145 | 4919213 |
| chr12 | 4919239 | 4919244 | chr12 | 5018073 | 5018692 | chr12 | 5019085 | 5019742 |
| chr12 | 5019794 | 5020313 | chr12 | 5153039 | 5153286 | chr12 | 5153358 | 5153460 |
| chr12 | 5541100 | 5541177 | chr12 | 5542325 | 5542439 | chr12 | 5542759 | 5542911 |
| chr12 | 5840200 | 5840363 | chr12 | 6308743 | 6308772 | chr12 | 6483615 | 6483756 |
| chr12 | 6664508 | 6664522 | chr12 | 7559160 | 7559307 | chr12 | 8025635 | 8025660 |
| chr12 | 8127118 | 8127140 | chr12 | 8171360 | 8171745 | chr12 | 8808599 | 8808684 |
| chr12 | 8850658 | 8850744 | chr12 | 8975182 | 8975361 | chr12 | 10085916 | 10085932 |
| chr12 | 10363278 | 10363323 | chr12 | 10772771 | 10772896 | chr12 | 11653449 | 11653463 |
| chr12 | 12504823 | 12504850 | chr12 | 12848390 | 12848556 | chr12 | 14133152 | 14133263 |
| chr12 | 14133619 | 14133881 | chr12 | 14135111 | 14135339 | chr12 | 14818824 | 14818857 |
| chr12 | 15374258 | 15374291 | chr12 | 16500576 | 16500621 | chr12 | 19282333 | 19282363 |
| chr12 | 20521704 | 20521841 | chr12 | 20522457 | 20522487 | chr12 | 20522769 | 20522891 |
| chr12 | 21680394 | 21680683 | chr12 | 21810264 | 21810868 | chr12 | 21833068 | 21833107 |
| chr12 | 22093825 | 22094268 | chr12 | 22094578 | 22094810 | chr12 | 22486799 | 22486881 |
| chr12 | 22487134 | 22487473 | chr12 | 22698087 | 22698110 | chr12 | 24714909 | 24714938 |
| chr12 | 24715235 | 24715264 | chr12 | 24716033 | 24716218 | chr12 | 25056243 | 25056436 |
| chr12 | 25101592 | 25101660 | chr12 | 25101919 | 25101997 | chr12 | 25102010 | 25102086 |
| chr12 | 25362824 | 25362853 | chr12 | 25368463 | 25368492 | chr12 | 25378543 | 25378662 |
| chr12 | 25380231 | 25380299 | chr12 | 25398203 | 25398319 | chr12 | 27176520 | 27176539 |
| chr12 | 27494550 | 27494580 | chr12 | 28123996 | 28124247 | chr12 | 28127757 | 28128302 |
| chr12 | 28128547 | 28129084 | chr12 | 29936016 | 29936048 | chr12 | 29936602 | 29936642 |
| chr12 | 29936662 | 29936831 | chr12 | 29937331 | 29937374 | chr12 | 30322774 | 30322924 |
| chr12 | 30323015 | 30323439 | chr12 | 30323503 | 30323517 | chr12 | 30975572 | 30975959 |
| chr12 | 31079268 | 31079367 | chr12 | 31079418 | 31079499 | chr12 | 31316012 | 31316037 |
| chr12 | 32340317 | 32340336 | chr12 | 33591774 | 33591804 | chr12 | 33592613 | 33592847 |
| chr12 | 34494888 | 34494918 | chr12 | 34502733 | 34502803 | chr12 | 39299117 | 39299560 |
| chr12 | 39539353 | 39539436 | chr12 | 40618404 | 40618470 | chr12 | 41086183 | 41086379 |
| chr12 | 41086784 | 41087106 | chr12 | 41582513 | 41582988 | chr12 | 41583374 | 41583419 |
| chr12 | 43945110 | 43945124 | chr12 | 43945356 | 43945379 | chr12 | 43945417 | 43945526 |
| chr12 | 43946203 | 43946298 | chr12 | 45269504 | 45269624 | chr12 | 45444118 | 45444681 |
| chr12 | 45444715 | 45445258 | chr12 | 46767650 | 46767697 | chr12 | 47225381 | 47225476 |
| chr12 | 47225551 | 47225579 | chr12 | 47629349 | 47629379 | chr12 | 48397195 | 48398070 |
| chr12 | 48398641 | 48398671 | chr12 | 48690674 | 48690880 | chr12 | 49297802 | 49297915 |
| chr12 | 49366374 | 49366423 | chr12 | 49374914 | 49375026 | chr12 | 49375116 | 49375119 |
| chr12 | 49375325 | 49375529 | chr12 | 49390873 | 49391104 | chr12 | 49391147 | 49391877 |
| chr12 | 49657705 | 49657743 | chr12 | 49691049 | 49691078 | chr12 | 49727092 | 49727127 |
| chr12 | 49729728 | 49730090 | chr12 | 49759530 | 49759559 | chr12 | 49989786 | 49989816 |
| chr12 | 50297497 | 50297554 | chr12 | 50297974 | 50298055 | chr12 | 50426748 | 50426799 |
| chr12 | 51421133 | 51421271 | chr12 | 51421556 | 51421586 | chr12 | 51565469 | 51565548 |
| chr12 | 51930708 | 51930785 | chr12 | 52262983 | 52263106 | chr12 | 52301280 | 52301305 |
| chr12 | 52400831 | 52401537 | chr12 | 52408905 | 52409033 | chr12 | 52627273 | 52627438 |
| chr12 | 52652153 | 52652219 | chr12 | 52652600 | 52652613 | chr12 | 53108089 | 53108218 |
| chr12 | 53359386 | 53359563 | chr12 | 54089093 | 54089511 | chr12 | 54132252 | 54132329 |
| chr12 | 54145843 | 54145857 | chr12 | 54145881 | 54145895 | chr12 | 54321250 | 54321628 |
| chr12 | 54322201 | 54322252 | chr12 | 54324799 | 54324937 | chr12 | 54329358 | 54329478 |
| chr12 | 54329605 | 54329947 | chr12 | 54331062 | 54331135 | chr12 | 54332868 | 54333337 |
| chr12 | 54338666 | 54338817 | chr12 | 54338979 | 54339681 | chr12 | 54343812 | 54343829 |
| chr12 | 54345611 | 54345658 | chr12 | 54345966 | 54346032 | chr12 | 54348844 | 54349079 |
| chr12 | 54349256 | 54349336 | chr12 | 54354514 | 54354621 | chr12 | 54354905 | 54355086 |
| chr12 | 54359960 | 54360084 | chr12 | 54360608 | 54360649 | chr12 | 54377912 | 54377946 |
| chr12 | 54377978 | 54378115 | chr12 | 54379174 | 54379623 | chr12 | 54379888 | 54379930 |
| chr12 | 54379959 | 54380459 | chr12 | 54387842 | 54387959 | chr12 | 54388215 | 54388245 |
| chr12 | 54391400 | 54391403 | chr12 | 54393479 | 54393684 | chr12 | 54393950 | 54394162 |
| chr12 | 54394410 | 54394418 | chr12 | 54398889 | 54398959 | chr12 | 54399616 | 54399646 |
| chr12 | 54402690 | 54402796 | chr12 | 54403067 | 54403360 | chr12 | 54408411 | 54408726 |
| chr12 | 54409476 | 54409505 | chr12 | 54423616 | 54423697 | chr12 | 54424746 | 54424748 |
| chr12 | 54425032 | 54425119 | chr12 | 54447351 | 54447581 | chr12 | 54447899 | 54447977 |
| chr12 | 54520745 | 54520868 | chr12 | 54720200 | 54720232 | chr12 | 54812238 | 54812359 |
| chr12 | 54922714 | 54922803 | chr12 | 54942994 | 54943116 | chr12 | 56231108 | 56231148 |
| chr12 | 56478840 | 56478869 | chr12 | 56481645 | 56481937 | chr12 | 56486572 | 56486601 |
| chr12 | 56490965 | 56490994 | chr12 | 56491630 | 56491659 | chr12 | 56492618 | 56492647 |
| chr12 | 56558381 | 56558519 | chr12 | 56873601 | 56873630 | chr12 | 56882240 | 56882380 |
| chr12 | 57387303 | 57387332 | chr12 | 57559869 | 57559925 | chr12 | 57618574 | 57618710 |
| chr12 | 57881127 | 57881345 | chr12 | 57944081 | 57944117 | chr12 | 58021320 | 58021458 |
| chr12 | 58021916 | 58022029 | chr12 | 58025646 | 58025733 | chr12 | 58025870 | 58025873 |
| chr12 | 58145415 | 58145450 | chr12 | 59314159 | 59314189 | chr12 | 52584838 | 52585012 |
| chr12 | 62585031 | 62586017 | chr12 | 62586252 | 62586281 | chr12 | 62858540 | 62858575 |
| chr12 | 63025574 | 63026160 | chr12 | 63543848 | 63544401 | chr12 | 63544499 | 63544599 |
| chr12 | 63545313 | 63545343 | chr12 | 64061821 | 64062159 | chr12 | 64062369 | 64062578 |
| chr12 | 64062921 | 64063096 | chr12 | 64783185 | 64783308 | chr12 | 54784108 | 64784252 |
| chr12 | 64784534 | 64784564 | chr12 | 65218102 | 65218550 | chr12 | 65218901 | 65219156 |

TABLE 13-continued

| chr | start | end | chr | start | end | chr | start | end |
|---|---|---|---|---|---|---|---|---|
| chr12 | 65219376 | 65219527 | chr12 | 65219606 | 65219784 | chr12 | 65220205 | 65220350 |
| chr12 | 65514863 | 65515596 | chr12 | 65516378 | 65516455 | chr12 | 65557212 | 65557234 |
| chr12 | 65562052 | 65562086 | chr12 | 66122800 | 66122995 | chr12 | 66123381 | 66123519 |
| chr12 | 66135984 | 66136014 | chr12 | 66582827 | 66583137 | chr12 | 69327259 | 69327463 |
| chr12 | 69754451 | 69754470 | chr12 | 69754590 | 69754710 | chr12 | 69964176 | 69964264 |
| chr12 | 70087493 | 70087568 | chr12 | 72332641 | 72332696 | chr12 | 72665786 | 72665788 |
| chr12 | 72666713 | 72666807 | chr12 | 72666998 | 72667425 | chr12 | 72667652 | 72667682 |
| chr12 | 75601379 | 75601499 | chr12 | 75601696 | 75601910 | chr12 | 75602976 | 75603231 |
| chr12 | 75728336 | 75728485 | chr12 | 75728737 | 75728766 | chr12 | 77719311 | 77719422 |
| chr12 | 79257222 | 79257351 | chr12 | 81102185 | 81102455 | chr12 | 81102513 | 81102562 |
| chr12 | 81107997 | 81108034 | chr12 | 81471517 | 81471614 | chr12 | 81471754 | 81472111 |
| chr12 | 85306519 | 85306549 | chr12 | 85667272 | 85667731 | chr12 | 85673206 | 85673235 |
| chr12 | 85673460 | 85674807 | chr12 | 88973544 | 88973582 | chr12 | 88974159 | 88974253 |
| chr12 | 93966429 | 93966603 | chr12 | 93966998 | 93967215 | chr12 | 94543409 | 94543445 |
| chr12 | 94543899 | 94543961 | chr12 | 94544022 | 94544052 | chr12 | 94852489 | 94852506 |
| chr12 | 95267524 | 95267554 | chr12 | 95267865 | 95267976 | chr12 | 95942965 | 95942978 |
| chr12 | 99288312 | 99288407 | chr12 | 99288622 | 99288936 | chr12 | 99289162 | 99289309 |
| chr12 | 101025380 | 101025410 | chr12 | 101111029 | 101111061 | chr12 | 101111373 | 101111479 |
| chr12 | 103218495 | 103218595 | chr12 | 103351564 | 103351985 | chr12 | 103352052 | 103352154 |
| chr12 | 103352171 | 103352282 | chr12 | 103352314 | 103352681 | chr12 | 103358865 | 103358899 |
| chr12 | 103359556 | 103359586 | chr12 | 103889160 | 103889211 | chr12 | 103889789 | 103889812 |
| chr12 | 104609417 | 104609796 | chr12 | 104684181 | 104684220 | chr12 | 104850505 | 104850536 |
| chr12 | 104850578 | 104850592 | chr12 | 104851077 | 104851186 | chr12 | 104852032 | 104852508 |
| chr12 | 105017109 | 105017199 | chr12 | 105478323 | 105478419 | chr12 | 106533852 | 106533881 |
| chr12 | 106974353 | 106974383 | chr12 | 106976725 | 106976779 | chr12 | 106977321 | 106977492 |
| chr12 | 106979161 | 106979534 | chr12 | 106979799 | 106979995 | chr12 | 106980223 | 106980333 |
| chr12 | 106980912 | 106981406 | chr12 | 107486550 | 107486672 | chr12 | 107487194 | 107487855 |
| chr12 | 107712273 | 107712303 | chr12 | 107713205 | 107713235 | chr12 | 107714866 | 107715153 |
| chr12 | 108168971 | 108169413 | chr12 | 108169550 | 108169573 | chr12 | 108237466 | 108237524 |
| chr12 | 108238102 | 108238513 | chr12 | 108297411 | 108297466 | chr12 | 109488519 | 109488543 |
| chr12 | 109639281 | 109639475 | chr12 | 110353414 | 110353451 | chr12 | 110717564 | 110717710 |
| chr12 | 110983706 | 110983736 | chr12 | 111127124 | 111127455 | chr12 | 111471177 | 111471559 |
| chr12 | 111471948 | 111471959 | chr12 | 111472059 | 111472195 | chr12 | 111472357 | 111472621 |
| chr12 | 111763122 | 111763152 | chr12 | 112574734 | 112574775 | chr12 | 112888151 | 112888315 |
| chr12 | 112910821 | 112910850 | chr12 | 112915509 | 112915538 | chr12 | 112926255 | 112926284 |
| chr12 | 112926876 | 112926914 | chr12 | 113012954 | 113013157 | chr12 | 113541667 | 113542099 |
| chr12 | 113592238 | 113592359 | chr12 | 113900753 | 113900765 | chr12 | 113901074 | 113901158 |
| chr12 | 113901408 | 113901591 | chr12 | 113902042 | 113902353 | chr12 | 113903468 | 113903498 |
| chr12 | 113904779 | 113905016 | chr12 | 113908990 | 113909314 | chr12 | 113909329 | 113909455 |
| chr12 | 113913267 | 113913681 | chr12 | 113913884 | 113914050 | chr12 | 113916222 | 113916316 |
| chr12 | 113916649 | 113916678 | chr12 | 113916972 | 113917012 | chr12 | 113917232 | 113917310 |
| chr12 | 113917775 | 113917890 | chr12 | 114029408 | 114029660 | chr12 | 114076029 | 114076093 |
| chr12 | 114337763 | 114337793 | chr12 | 114833985 | 114834102 | chr12 | 114838369 | 114838726 |
| chr12 | 114839104 | 114839147 | chr12 | 114841046 | 114841084 | chr12 | 114841425 | 114841493 |
| chr12 | 114843112 | 114843186 | chr12 | 114843261 | 114843278 | chr12 | 114843545 | 114843660 |
| chr12 | 114844201 | 114844300 | chr12 | 114846715 | 114846768 | chr12 | 114847043 | 114847436 |
| chr12 | 114847578 | 114847691 | chr12 | 114852040 | 114852082 | chr12 | 114852293 | 114852373 |
| chr12 | 114877171 | 114877262 | chr12 | 114878550 | 114878584 | chr12 | 114878813 | 114879012 |
| chr12 | 114881634 | 114881764 | chr12 | 114882555 | 114882646 | chr12 | 114883473 | 114883535 |
| chr12 | 114918594 | 114918717 | chr12 | 115136159 | 115136363 | chr12 | 116946086 | 116946199 |
| chr12 | 116946251 | 116946548 | chr12 | 117474065 | 117474198 | chr12 | 117798065 | 117798095 |
| chr12 | 117799413 | 117799529 | chr12 | 118860397 | 118860436 | chr12 | 119212319 | 119212381 |
| chr12 | 119418594 | 119418847 | chr12 | 119419436 | 119419466 | chr12 | 119419720 | 119419899 |
| chr12 | 120032862 | 120033169 | chr12 | 120148142 | 120148248 | chr12 | 120148923 | 120148962 |
| chr12 | 120535158 | 120535187 | chr12 | 120536625 | 120536654 | chr12 | 120885215 | 120885245 |
| chr12 | 121622546 | 121622576 | chr12 | 122192223 | 122192843 | chr12 | 122278484 | 122278580 |
| chr12 | 122285067 | 122285108 | chr12 | 122473581 | 122473611 | chr12 | 123129129 | 123129160 |
| chr12 | 123233806 | 123233846 | chr12 | 124246908 | 124246937 | chr12 | 124247208 | 124247237 |
| chr12 | 124393560 | 124393604 | chr12 | 124397464 | 124397618 | chr12 | 124865115 | 124865144 |
| chr12 | 125009276 | 125009306 | chr12 | 125533949 | 125534407 | chr12 | 125589840 | 125589872 |
| chr12 | 125670117 | 125670260 | chr12 | 126168554 | 126168620 | chr12 | 127211317 | 127211378 |
| chr12 | 127765158 | 127765432 | chr12 | 127940086 | 127940247 | chr12 | 128751384 | 128751443 |
| chr12 | 128751821 | 128751877 | chr12 | 128752115 | 128752240 | chr12 | 128752499 | 128752944 |
| chr12 | 128753210 | 128753240 | chr12 | 128850534 | 128850644 | chr12 | 129338588 | 129338816 |
| chr12 | 130037653 | 130037778 | chr12 | 130387797 | 130387811 | chr12 | 130388410 | 130388434 |
| chr12 | 130389013 | 130389152 | chr12 | 130589202 | 130589266 | chr12 | 130645233 | 130645627 |
| chr12 | 130646946 | 130647115 | chr12 | 130647574 | 130647908 | chr12 | 130647951 | 130648069 |
| chr12 | 130821371 | 130821621 | chr12 | 130968621 | 130968654 | chr12 | 131200379 | 131200645 |
| chr12 | 131400816 | 131400919 | chr12 | 131403032 | 131403125 | chr12 | 131513345 | 131513403 |
| chr12 | 132102173 | 132102202 | chr12 | 132169288 | 132169365 | chr12 | 132221689 | 132222076 |
| chr12 | 132333434 | 132333456 | chr12 | 132333516 | 132333597 | chr12 | 132348651 | 132348684 |
| chr12 | 132423595 | 132423854 | chr12 | 132643233 | 132643279 | chr12 | 132986495 | 132986581 |
| chr12 | 133002792 | 133003231 | chr12 | 133172907 | 133173021 | chr12 | 133195093 | 133195196 |
| chr12 | 133199738 | 133199784 | chr12 | 133280578 | 133280682 | chr12 | 133463736 | 133463876 |
| chr12 | 133464108 | 133464166 | chr12 | 133464840 | 133464934 | chr12 | 133464994 | 133465027 |
| chr12 | 133481490 | 133481655 | chr12 | 133484742 | 133484852 | chr12 | 133485162 | 133485347 |
| chr12 | 133485557 | 133485689 | chr12 | 133485816 | 133485847 | chr12 | 133758048 | 133758107 |
| chr13 | 20175911 | 20175941 | chr13 | 20735804 | 20736089 | chr13 | 21649636 | 21649775 |

TABLE 13-continued

| chr | start | end | chr | start | end | chr | start | end |
|---|---|---|---|---|---|---|---|---|
| chr13 | 22243273 | 22243469 | chr13 | 23489851 | 23489914 | chr13 | 23653797 | 23653813 |
| chr13 | 23733447 | 23734020 | chr13 | 23734284 | 23734297 | chr13 | 24477643 | 24477906 |
| chr13 | 25115713 | 25115771 | chr13 | 25319856 | 25319904 | chr13 | 25320388 | 25320539 |
| chr13 | 25320614 | 25321028 | chr13 | 25321113 | 25321350 | chr13 | 25321699 | 25321942 |
| chr13 | 25593062 | 25593242 | chr13 | 25621045 | 25621205 | chr13 | 25621264 | 25621394 |
| chr13 | 25744716 | 25744734 | chr13 | 25745301 | 25745594 | chr13 | 25745727 | 25746000 |
| chr13 | 25946301 | 25946411 | chr13 | 25946620 | 25946673 | chr13 | 26042678 | 26042707 |
| chr13 | 26042769 | 26043170 | chr13 | 26043341 | 26043499 | chr13 | 26340608 | 26340755 |
| chr13 | 26625301 | 26625656 | chr13 | 27334211 | 27334563 | chr13 | 27334772 | 27334894 |
| chr13 | 28239909 | 28240164 | chr13 | 28365705 | 28366122 | chr13 | 28366482 | 28366577 |
| chr13 | 28367024 | 28367038 | chr13 | 28367794 | 28367945 | chr13 | 28368154 | 28368168 |
| chr13 | 28368451 | 28368593 | chr13 | 28368952 | 28369070 | chr13 | 28369162 | 28369891 |
| chr13 | 28369951 | 28369990 | chr13 | 28370947 | 28371061 | chr13 | 28394766 | 28394866 |
| chr13 | 28395501 | 28395553 | chr13 | 28395998 | 28396073 | chr13 | 28491793 | 28491946 |
| chr13 | 28492244 | 28492553 | chr13 | 28503042 | 28503074 | chr13 | 28528534 | 28528748 |
| chr13 | 28540745 | 28540927 | chr13 | 28543212 | 28543242 | chr13 | 28544397 | 28544584 |
| chr13 | 28544666 | 28544903 | chr13 | 28549497 | 28549891 | chr13 | 28550240 | 28550552 |
| chr13 | 28551417 | 28551461 | chr13 | 28551950 | 28552167 | chr13 | 28552794 | 28552824 |
| chr13 | 28553030 | 28553138 | chr13 | 28589765 | 28589794 | chr13 | 28592605 | 28592658 |
| chr13 | 28601345 | 28601374 | chr13 | 28602326 | 28602355 | chr13 | 28608233 | 28608355 |
| chr13 | 28610123 | 28610152 | chr13 | 28674018 | 28674226 | chr13 | 28674721 | 28674734 |
| chr13 | 29067773 | 29068416 | chr13 | 29068926 | 29068985 | chr13 | 29068994 | 29069065 |
| chr13 | 29106308 | 29106814 | chr13 | 29106899 | 29107063 | chr13 | 29107253 | 29107309 |
| chr13 | 29112420 | 29112444 | chr13 | 30141688 | 30141718 | chr13 | 30707569 | 30707599 |
| chr13 | 31742953 | 31743177 | chr13 | 32605034 | 32605324 | chr13 | 32605443 | 32605623 |
| chr13 | 32605675 | 32605966 | chr13 | 33591300 | 33591419 | chr13 | 33924666 | 33924790 |
| chr13 | 35517410 | 35517648 | chr13 | 36044829 | 36044930 | chr13 | 36049995 | 36050025 |
| chr13 | 36269480 | 36269509 | chr13 | 36553399 | 36553428 | chr13 | 36704939 | 36705055 |
| chr13 | 36705451 | 36705489 | chr13 | 36909206 | 36909236 | chr13 | 36920317 | 36920386 |
| chr13 | 36920628 | 36920785 | chr13 | 37004771 | 37005129 | chr13 | 37005900 | 37006062 |
| chr13 | 37006434 | 37006657 | chr13 | 37006734 | 37006762 | chr13 | 37248063 | 37248148 |
| chr13 | 37248295 | 37248319 | chr13 | 37248979 | 37248993 | chr13 | 37633989 | 37634018 |
| chr13 | 37643942 | 37644005 | chr13 | 38443618 | 38443715 | chr13 | 39261410 | 39261446 |
| chr13 | 41884500 | 41884534 | chr13 | 43148669 | 43148698 | chr13 | 43566247 | 43566647 |
| chr13 | 44947746 | 44948197 | chr13 | 45150013 | 45150276 | chr13 | 45885876 | 45885905 |
| chr13 | 45905236 | 45905264 | chr13 | 46425548 | 46425554 | chr13 | 46425576 | 46425584 |
| chr13 | 46660839 | 46660869 | chr13 | 46961494 | 46961533 | chr13 | 46961952 | 46961982 |
| chr13 | 47468139 | 47468168 | chr13 | 47472315 | 47472344 | chr13 | 47526166 | 47526182 |
| chr13 | 48478576 | 48478605 | chr13 | 48667877 | 48667907 | chr13 | 49794117 | 49794925 |
| chr13 | 50421504 | 50421696 | chr13 | 50639782 | 50639799 | chr13 | 52580344 | 52580369 |
| chr13 | 53312991 | 53313313 | chr13 | 53313513 | 53313612 | chr13 | 53313678 | 53313920 |
| chr13 | 53419734 | 53419775 | chr13 | 53420020 | 53420020 | chr13 | 53423838 | 53423978 |
| chr13 | 57714539 | 57714568 | chr13 | 58203602 | 58203644 | chr13 | 58203851 | 58204103 |
| chr13 | 58204350 | 58204393 | chr13 | 58206042 | 58206231 | chr13 | 58206453 | 58206771 |
| chr13 | 58206862 | 58206983 | chr13 | 58207568 | 58207813 | chr13 | 58207892 | 58208020 |
| chr13 | 58208495 | 58208926 | chr13 | 62132346 | 62132375 | chr13 | 64650200 | 54650229 |
| chr13 | 65532258 | 65532287 | chr13 | 67803735 | 67804074 | chr13 | 67804494 | 67804523 |
| chr13 | 67805191 | 67805247 | chr13 | 70681626 | 70681777 | chr13 | 70681867 | 70682071 |
| chr13 | 71498386 | 71498415 | chr13 | 72439142 | 72439250 | chr13 | 73336049 | 73336078 |
| chr13 | 73619660 | 73619752 | chr13 | 78492684 | 78492840 | chr13 | 78493166 | 78493196 |
| chr13 | 78493455 | 78493809 | chr13 | 79168067 | 79168102 | chr13 | 79169850 | 79170113 |
| chr13 | 79170348 | 79170383 | chr13 | 79170468 | 79170884 | chr13 | 79171118 | 79171196 |
| chr13 | 79175770 | 79175943 | chr13 | 79176078 | 79176125 | chr13 | 79176277 | 79176420 |
| chr13 | 79176609 | 79176783 | chr13 | 79176993 | 79177184 | chr13 | 79177306 | 79177622 |
| chr13 | 79177886 | 79177998 | chr13 | 79183406 | 79183423 | chr13 | 81229343 | 81229372 |
| chr13 | 84455236 | 84455292 | chr13 | 84455581 | 84455715 | chr13 | 84457491 | 84457521 |
| chr13 | 87731371 | 87731400 | chr13 | 88323579 | 88323830 | chr13 | 88323868 | 88324207 |
| chr13 | 88324516 | 88324518 | chr13 | 88325300 | 88325460 | chr13 | 88325819 | 88326061 |
| chr13 | 88326538 | 88326707 | chr13 | 88326937 | 88327014 | chr13 | 88788883 | 88788912 |
| chr13 | 88997906 | 88997935 | chr13 | 89815436 | 89815465 | chr13 | 90015503 | 90015532 |
| chr13 | 91755723 | 91755750 | chr13 | 91948489 | 91948519 | chr13 | 92050760 | 92050814 |
| chr13 | 92051139 | 92051168 | chr13 | 92051374 | 92051513 | chr13 | 93879288 | 93879375 |
| chr13 | 93879670 | 93879700 | chr13 | 93880089 | 93880216 | chr13 | 93880534 | 93880737 |
| chr13 | 93880794 | 93880856 | chr13 | 95086143 | 95086172 | chr13 | 95357311 | 95357341 |
| chr13 | 95357574 | 95357775 | chr13 | 95358041 | 95358165 | chr13 | 95359747 | 95359803 |
| chr13 | 95360322 | 95360371 | chr13 | 95363210 | 95363429 | chr13 | 96363796 | 95363959 |
| chr13 | 95364065 | 95364196 | chr13 | 95364495 | 95364800 | chr13 | 95620021 | 95620078 |
| chr13 | 95620647 | 95620781 | chr13 | 95620854 | 95621011 | chr13 | 96031705 | 96031730 |
| chr13 | 96204923 | 96205363 | chr13 | 96296225 | 96296345 | chr13 | 96296373 | 96296473 |
| chr13 | 96296841 | 96296949 | chr13 | 96296992 | 96297137 | chr13 | 96743788 | 96744175 |
| chr13 | 97761876 | 97761925 | chr13 | 99851676 | 99851706 | chr13 | 100547713 | 100547893 |
| chr13 | 100608462 | 100608536 | chr13 | 100608596 | 100608804 | chr13 | 100608839 | 100609055 |
| chr13 | 100621941 | 100622015 | chr13 | 100624324 | 100624348 | chr13 | 100624587 | 100624729 |
| chr13 | 100626929 | 100627009 | chr13 | 100627295 | 100627348 | chr13 | 100627688 | 100627717 |
| chr13 | 100630169 | 100630298 | chr13 | 100630329 | 100630430 | chr13 | 100630630 | 100630997 |
| chr13 | 100633089 | 100633184 | chr13 | 100634314 | 100634617 | chr13 | 100635406 | 100635451 |
| chr13 | 100636167 | 100636238 | chr13 | 100637390 | 100637485 | chr13 | 100641282 | 100641408 |
| chr13 | 100642120 | 100642201 | chr13 | 100643296 | 100643435 | chr13 | 100644055 | 100644179 |

TABLE 13-continued

| chr | start | end | chr | start | end | chr | start | end |
|---|---|---|---|---|---|---|---|---|
| chr13 | 100649325 | 100649575 | chr13 | 100649800 | 100649884 | chr13 | 102568454 | 102568484 |
| chr13 | 102569313 | 102569542 | chr13 | 103046721 | 103046995 | chr13 | 103052342 | 103052574 |
| chr13 | 103052892 | 103052940 | chr13 | 103053394 | 103053496 | chr13 | 105484285 | 105484314 |
| chr13 | 105791875 | 105791904 | chr13 | 107186855 | 107186884 | chr13 | 107187162 | 107187426 |
| chr13 | 107187666 | 107187695 | chr13 | 107188241 | 107188430 | chr13 | 108518813 | 108518933 |
| chr13 | 108519254 | 108519367 | chr13 | 108519737 | 108519745 | chr13 | 108520376 | 108520534 |
| chr13 | 108520979 | 108521076 | chr13 | 109147685 | 109147862 | chr13 | 109148155 | 109148278 |
| chr13 | 109148783 | 109149185 | chr13 | 110434451 | 110434593 | chr13 | 110958816 | 110958981 |
| chr13 | 110959753 | 110959970 | chr13 | 110960541 | 110960603 | chr13 | 111278255 | 111278426 |
| chr13 | 111363880 | 111363972 | chr13 | 112272991 | 112273088 | chr13 | 112707694 | 112707869 |
| chr13 | 112708308 | 112708513 | chr13 | 112709388 | 112709612 | chr13 | 112709883 | 112709928 |
| chr13 | 112710360 | 112710475 | chr13 | 112710759 | 112711293 | chr13 | 112711376 | 112711776 |
| chr13 | 112712017 | 112713029 | chr13 | 112715370 | 112715642 | chr13 | 112715985 | 112716313 |
| chr13 | 112716677 | 112716721 | chr13 | 112717026 | 112717242 | chr13 | 112717323 | 112717536 |
| chr13 | 112717835 | 112717949 | chr13 | 112720033 | 112720505 | chr13 | 112720723 | 112720767 |
| chr13 | 112721012 | 112721026 | chr13 | 112722129 | 112722220 | chr13 | 112722275 | 112722312 |
| chr13 | 112724505 | 112724535 | chr13 | 112726436 | 112726560 | chr13 | 112727984 | 112728200 |
| chr13 | A12758107 | 112758257 | chr13 | 112758274 | 112758372 | chr13 | 112758496 | 112758613 |
| chr13 | 112759112 | 112759248 | chr13 | 112759612 | 112759642 | chr13 | 112760007 | 112760327 |
| chr13 | 112760795 | 112761214 | chr13 | 113598618 | 113598851 | chr13 | 113985679 | 113985956 |
| chr13 | 114055983 | 114056137 | chr13 | 114060064 | 114060333 | chr13 | 114074768 | 114074853 |
| chr13 | 114082984 | 114083014 | chr13 | 114123168 | 114123291 | chr13 | 114189737 | 114189809 |
| chr13 | 114221622 | 114221652 | chr13 | 114304565 | 114304927 | chr13 | 114479404 | 114479434 |
| chr13 | 114498017 | 114498260 | chr13 | 114748342 | 114748638 | chr13 | 114766270 | 114766300 |
| chr13 | 114780561 | 114781061 | chr13 | 114807617 | 114807815 | chr13 | 114855635 | 114855669 |
| chr13 | 114862308 | 114862368 | chr13 | 114897194 | 114897217 | chr13 | 114961823 | 114961933 |
| chr14 | 21093454 | 21093543 | chr14 | 21093603 | 21093631 | chr14 | 21100748 | 21100778 |
| chr14 | 21100801 | 21100831 | chr14 | 22005029 | 22005073 | chr14 | 23234956 | 23234994 |
| chr14 | 23356044 | 23356384 | chr14 | 23706727 | 23706765 | chr14 | 24641010 | 24641215 |
| chr14 | 24803594 | 24804122 | chr14 | 26674354 | 26674384 | chr14 | 26674699 | 26674729 |
| chr14 | 27066562 | 27066704 | chr14 | 27066764 | 27066785 | chr14 | 27067373 | 27067386 |
| chr14 | 29225631 | 29225561 | chr14 | 29226071 | 29226198 | chr14 | 29228654 | 29228778 |
| chr14 | 29229107 | 29229386 | chr14 | 29231071 | 29231185 | chr14 | 29231425 | 29231590 |
| chr14 | 29235003 | 29235308 | chr14 | 29236342 | 29235356 | chr14 | 29237063 | 29237066 |
| chr14 | 29242763 | 29242908 | chr14 | 29243516 | 29243669 | chr14 | 29243731 | 29243888 |
| chr14 | 29244224 | 29244308 | chr14 | 29247689 | 29247740 | chr14 | 29254612 | 29254713 |
| chr14 | 31344346 | 31344549 | chr14 | 31925639 | 31925724 | chr14 | 32597620 | 32597657 |
| chr14 | 33402462 | 33402762 | chr14 | 33403045 | 33403316 | chr14 | 33403866 | 33404418 |
| chr14 | 34269897 | 34270004 | chr14 | 34420250 | 34420288 | chr14 | 35023187 | 35023322 |
| chr14 | 35024446 | 35024466 | chr14 | 35389907 | 35389943 | chr14 | 36003442 | 36003826 |
| chr14 | 36004081 | 36004493 | chr14 | 36004711 | 36004734 | chr14 | 36004822 | 36004921 |
| chr14 | 36972803 | 36972912 | chr14 | 36973455 | 36973538 | chr14 | 36974294 | 36974927 |
| chr14 | 36974968 | 36974982 | chr14 | 36975299 | 36975399 | chr14 | 36977645 | 36977929 |
| chr14 | 36977975 | 36978009 | chr14 | 36978548 | 36978578 | chr14 | 36979619 | 36979649 |
| chr14 | 36982927 | 36982969 | chr14 | 36983708 | 36984146 | chr14 | 36985841 | 36985871 |
| chr14 | 36986301 | 36986471 | chr14 | 36987302 | 36987685 | chr14 | 36987939 | 36988143 |
| chr14 | 36988428 | 36988460 | chr14 | 36990858 | 36991032 | chr14 | 36991095 | 36991177 |
| chr14 | 36991532 | 36991613 | chr14 | 36991989 | 36992163 | chr14 | 36992222 | 36992417 |
| chr14 | 36993473 | 36993487 | chr14 | 36993694 | 36993956 | chr14 | 36994248 | 36994999 |
| chr14 | 37050752 | 37050794 | chr14 | 37116105 | 37116294 | chr14 | 37117611 | 37117697 |
| chr14 | 37123438 | 37124077 | chr14 | 37124482 | 37124572 | chr14 | 37124992 | 37125545 |
| chr14 | 37126241 | 37126297 | chr14 | 37126566 | 37126713 | chr14 | 37127281 | 37127311 |
| chr14 | 37127655 | 37127779 | chr14 | 37128553 | 37128723 | chr14 | 37130077 | 37130260 |
| chr14 | 37132375 | 37132553 | chr14 | 37132603 | 37132695 | chr14 | 37133001 | 37133052 |
| chr14 | 37135784 | 37136017 | chr14 | 37136295 | 37136345 | chr14 | 37136588 | 37136618 |
| chr14 | 38060677 | 38060916 | chr14 | 38064401 | 38064549 | chr14 | 38677519 | 38677548 |
| chr14 | 38677761 | 38677790 | chr14 | 38724294 | 38724525 | chr14 | 38724979 | 38725258 |
| chr14 | 38725521 | 38725764 | chr14 | 39579800 | 39579830 | chr14 | 42074544 | 42074586 |
| chr14 | 42074669 | 42074987 | chr14 | 42075588 | 42076043 | chr14 | 42076106 | 42076212 |
| chr14 | 42076823 | 42076853 | chr14 | 42077230 | 42077268 | chr14 | 42077770 | 42077800 |
| chr14 | 42079289 | 42079328 | chr14 | 48143798 | 48143957 | chr14 | 48144359 | 48144401 |
| chr14 | 48144699 | 48144763 | chr14 | 48145237 | 48145257 | chr14 | 50333964 | 50333994 |
| chr14 | 50334335 | 50334355 | chr14 | 51338730 | 51338731 | chr14 | 51560304 | 51560713 |
| chr14 | 51560771 | 51561428 | chr14 | 51561765 | 51562012 | chr14 | 51955509 | 51955538 |
| chr14 | 52534648 | 52534791 | chr14 | 52535012 | 52535026 | chr14 | 52535056 | 52535263 |
| chr14 | 52535335 | 52536104 | chr14 | 52536343 | 52536404 | chr14 | 52734509 | 52734557 |
| chr14 | 52734777 | 52735001 | chr14 | 52735045 | 52735255 | chr14 | 52781525 | 52781916 |
| chr14 | 54422651 | 54422925 | chr14 | 55370202 | 55370219 | chr14 | 55595938 | 55595968 |
| chr14 | 55765285 | 55765714 | chr14 | 55823079 | 55823179 | chr14 | 57045520 | 57045739 |
| chr14 | 57260946 | 57261094 | chr14 | 57261175 | 57261407 | chr14 | 57261466 | 57261821 |
| chr14 | 57262072 | 57262179 | chr14 | 57264079 | 57264645 | chr14 | 57264765 | 57264806 |
| chr14 | 57265148 | 57265240 | chr14 | 57270936 | 57270971 | chr14 | 57271154 | 57271266 |
| chr14 | 57272009 | 57272067 | chr14 | 57274486 | 57275049 | chr14 | 57275211 | 57275305 |
| chr14 | 57275596 | 57275685 | chr14 | 57276074 | 57276104 | chr14 | 57276440 | 57276666 |
| chr14 | 57277920 | 57278762 | chr14 | 57278838 | 57279564 | chr14 | 57279643 | 57279657 |
| chr14 | 57283314 | 57283408 | chr14 | 57283446 | 57284036 | chr14 | 57284071 | 57284659 |
| chr14 | 58332297 | 58332403 | chr14 | 59770326 | 59770359 | chr14 | 60097193 | 60097246 |
| chr14 | 60097407 | 60097566 | chr14 | 60386207 | 60386252 | chr14 | 60386638 | 60386701 |

TABLE 13-continued

| chr | start | end | chr | start | end | chr | start | end |
|---|---|---|---|---|---|---|---|---|
| chr14 | 60794635 | 60794667 | chr14 | 60952196 | 60952419 | chr14 | 60952517 | 60952632 |
| chr14 | 60952730 | 60952959 | chr14 | 60973151 | 60973324 | chr14 | 60973697 | 60974007 |
| chr14 | 60974368 | 60974403 | chr14 | 60975384 | 60975888 | chr14 | 60976075 | 60976514 |
| chr14 | 60976813 | 60976860 | chr14 | 60977337 | 60977712 | chr14 | 60977880 | 60978147 |
| chr14 | 60981202 | 60981268 | chr14 | 60981676 | 60981793 | chr14 | 60982110 | 60982367 |
| chr14 | 60982574 | 60982622 | chr14 | 60982841 | 60982911 | chr14 | 61104291 | 61104556 |
| chr14 | 61104624 | 61104864 | chr14 | 61108620 | 61108996 | chr14 | 61109206 | 61109470 |
| chr14 | 61109839 | 61110243 | chr14 | 61114137 | 61114456 | chr14 | 61115311 | 61115517 |
| chr14 | 61118743 | 61118765 | chr14 | 61118965 | 61119136 | chr14 | 61119536 | 61119639 |
| chr14 | 61747389 | 61747527 | chr14 | 61747583 | 61748033 | chr14 | 62279578 | 62279852 |
| chr14 | 62279899 | 62280006 | chr14 | 62583809 | 62583869 | chr14 | 63512100 | 63512291 |
| chr14 | 63512573 | 63512708 | chr14 | 63512741 | 63512816 | chr14 | 63513124 | 63513154 |
| chr14 | 64222413 | 64222451 | chr14 | 65005795 | 65005833 | chr14 | 65008998 | 65009193 |
| chr14 | 65233339 | 65233464 | chr14 | 67585164 | 67585199 | chr14 | 67886582 | 67886606 |
| chr14 | 69014044 | 69014110 | chr14 | 69866541 | 69866564 | chr14 | 69867022 | 69867196 |
| chr14 | 70014723 | 70014974 | chr14 | 70038990 | 70039025 | chr14 | 70346136 | 70346491 |
| chr14 | 70654378 | 70654713 | chr14 | 70655530 | 70655889 | chr14 | 70655920 | 70656090 |
| chr14 | 72398743 | 72399019 | chr14 | 72399452 | 72399453 | chr14 | 72399929 | 72400029 |
| chr14 | 73167750 | 73167899 | chr14 | 73175026 | 73175148 | chr14 | 73178807 | 73178865 |
| chr14 | 73180208 | 73180314 | chr14 | 73236095 | 73236137 | chr14 | 73318471 | 73318629 |
| chr14 | 73333249 | 73333293 | chr14 | 73602350 | 73602389 | chr14 | 74706015 | 74706222 |
| chr14 | 74706941 | 74707544 | chr14 | 74707573 | 74707747 | chr14 | 74707792 | 74707873 |
| chr14 | 74708862 | 74708955 | chr14 | 74892540 | 74892569 | chr14 | 74893074 | 74893113 |
| chr14 | 75078170 | 75078242 | chr14 | 75760311 | 75760329 | chr14 | 75988341 | 25988370 |
| chr14 | 75988732 | 75988761 | chr14 | 76128674 | 76128698 | chr14 | 76604682 | 76604716 |
| chr14 | 76605072 | 76605376 | chr14 | 76843742 | 76843953 | chr14 | 77228121 | 77228159 |
| chr14 | 27606922 | 27607236 | chr14 | 77737212 | 77737814 | chr14 | 79745138 | 79745175 |
| chr14 | 85996479 | 85996608 | chr14 | 85996892 | 85996906 | chr14 | 85997821 | 85997925 |
| chr14 | 85998288 | 85998574 | chr14 | 85998630 | 85998683 | chr14 | 85999597 | 85999613 |
| chr14 | 86000270 | 86000511 | chr14 | 86000918 | 86001114 | chr14 | 89817889 | 89818034 |
| chr14 | 90527714 | 90527758 | chr14 | 90983328 | 90983360 | chr14 | 91691163 | 91691306 |
| chr14 | 91691789 | 91691822 | chr14 | 91766154 | 91766450 | chr14 | 91780382 | 91780512 |
| chr14 | 91801036 | 91801164 | chr14 | 92507655 | 92507792 | chr14 | 92789512 | 92789542 |
| chr14 | 92789960 | 92790098 | chr14 | 92790637 | 92790703 | chr14 | 92979917 | 92979991 |
| chr14 | 93155061 | 93155315 | chr14 | 93389557 | 93389693 | chr14 | 93389713 | 93389776 |
| chr14 | 93571193 | 93571326 | chr14 | 93706752 | 93706782 | chr14 | 94254389 | 94254458 |
| chr14 | 94254499 | 94254513 | chr14 | 94405734 | 94405785 | chr14 | 94603542 | 94603670 |
| chr14 | 94889856 | 94889870 | chr14 | 95233705 | 95233765 | chr14 | 95234643 | 95234710 |
| chr14 | 95235026 | 95235369 | chr14 | 95235989 | 95236111 | chr14 | 95236524 | 95236553 |
| chr14 | 95236819 | 95236848 | chr14 | 95237622 | 95237642 | chr14 | 96239422 | 95239633 |
| chr14 | 95240127 | 95240157 | chr14 | 95240227 | 95240341 | chr14 | 95240392 | 95240422 |
| chr14 | 95557626 | 95557655 | chr14 | 95560448 | 95560477 | chr14 | 95740035 | 95740116 |
| chr14 | 96342897 | 96343133 | chr14 | 96343404 | 96343433 | chr14 | 96343668 | 96343701 |
| chr14 | 97045354 | 97045431 | chr14 | 97058944 | 97059083 | chr14 | 97499277 | 97499315 |
| chr14 | 97499847 | 97499849 | chr14 | 97685044 | 97685288 | chr14 | 97685707 | 97685959 |
| chr14 | 99584575 | 99584664 | chr14 | 99712321 | 99712394 | chr14 | 99736151 | 99736183 |
| chr14 | 99737398 | 99737462 | chr14 | 100437794 | 100437949 | chr14 | 100438705 | 100438811 |
| chr14 | 100643350 | 100643481 | chr14 | 100793556 | 100793650 | chr14 | 101250109 | 101250272 |
| chr14 | 101506231 | 101506260 | chr14 | 101543868 | 101544235 | chr14 | 101923114 | 101923250 |
| chr14 | 101923600 | 101923686 | chr14 | 101924031 | 101924047 | chr14 | 101925049 | 101925071 |
| chr14 | 101925656 | 101925901 | chr14 | 102026360 | 102026484 | chr14 | 102026797 | 102026967 |
| chr14 | 102031236 | 102031271 | chr14 | 102031512 | 102031580 | chr14 | 102247912 | 102248214 |
| chr14 | 102418607 | 102418637 | chr14 | 102521602 | 102521758 | chr14 | 102530007 | 102530234 |
| chr14 | 102530500 | 102530530 | chr14 | 102564464 | 102564505 | chr14 | 102682077 | 102682149 |
| chr14 | 102973169 | 102973268 | chr14 | 103021391 | 103022003 | chr14 | 103394884 | 103395101 |
| chr14 | 103477643 | 103477779 | chr14 | 103655226 | 103655601 | chr14 | 103674078 | 103674079 |
| chr14 | 103687082 | 103687219 | chr14 | 103739967 | 103740150 | chr14 | 103740358 | 103740430 |
| chr14 | 103745699 | 103745750 | chr14 | 104160060 | 104160134 | chr14 | 104202705 | 104202759 |
| chr14 | 104547785 | 104547909 | chr14 | 104571985 | 104572116 | chr14 | 104601737 | 104601832 |
| chr14 | 104602033 | 104602063 | chr14 | 104605032 | 104605114 | chr14 | 104620411 | 104620554 |
| chr14 | 104627664 | 104627759 | chr14 | 104645126 | 104645188 | chr14 | 104646317 | 104646491 |
| chr14 | 104647257 | 104647287 | chr14 | 104682545 | 104682656 | chr14 | 104862860 | 104863026 |
| chr14 | 105071298 | 105071396 | chr14 | 105157485 | 105157554 | chr14 | 105239389 | 105239439 |
| chr14 | 105239793 | 105239825 | chr14 | 105241309 | 105241428 | chr14 | 105243032 | 105243064 |
| chr14 | 105246427 | 105246582 | chr14 | 105512063 | 105512395 | chr14 | 105658456 | 105658425 |
| chr14 | 105714258 | 105714334 | chr14 | 105714415 | 106714441 | chr14 | 105715248 | 105715392 |
| chr14 | 105830630 | 105830859 | chr14 | 105963655 | 105963772 | chr15 | 22822348 | 22822388 |
| chr15 | 23158397 | 23158489 | chr15 | 23692316 | 23692415 | chr15 | 26107640 | 26107743 |
| chr15 | 26107846 | 26107860 | chr15 | 26108096 | 26108326 | chr15 | 26108549 | 26108701 |
| chr15 | 27212887 | 27213172 | chr15 | 27604062 | 27604123 | chr15 | 28341699 | 28342019 |
| chr15 | 28344173 | 28344187 | chr15 | 28344224 | 28344287 | chr15 | 28352240 | 28352421 |
| chr15 | 29077284 | 29077383 | chr15 | 29130807 | 29131047 | chr15 | 29131533 | 29131630 |
| chr15 | 29131756 | 29131875 | chr15 | 29396330 | 29396360 | chr15 | 29407777 | 29407813 |
| chr15 | 29407867 | 29408001 | chr15 | 29862502 | 29862582 | chr15 | 30115185 | 30115228 |
| chr15 | 31455370 | 31455485 | chr15 | 31775596 | 31775637 | chr15 | 31775679 | 31775782 |
| chr15 | 32933918 | 32934018 | chr15 | 33009747 | 33009761 | chr15 | 33009822 | 33010675 |
| chr15 | 33010721 | 33011348 | chr15 | 33011601 | 33011633 | chr15 | 33487057 | 33487120 |
| chr15 | 33602801 | 33602886 | chr15 | 33603194 | 33603608 | chr15 | 33879242 | 33879272 |

TABLE 13-continued

| chr | start | end | chr | start | end | chr | start | end |
|---|---|---|---|---|---|---|---|---|
| chr15 | 34517058 | 34517334 | chr15 | 34630439 | 34630449 | chr15 | 34630515 | 34630544 |
| chr15 | 34729478 | 34729582 | chr15 | 34786504 | 34786943 | chr15 | 34787233 | 34787304 |
| chr15 | 35046607 | 35046608 | chr15 | 35047034 | 35047133 | chr15 | 35087666 | 35087698 |
| chr15 | 37180309 | 37180743 | chr15 | 37402974 | 37403086 | chr15 | 37403116 | 37403238 |
| chr15 | 40211819 | 40212190 | chr15 | 40575630 | 40575744 | chr15 | 40671588 | 40671620 |
| chr15 | 40675092 | 40675121 | chr15 | 40763811 | 40763862 | chr15 | 40782219 | 40782249 |
| chr15 | 41165245 | 41165700 | chr15 | 41804878 | 41805772 | chr15 | 41835694 | 41835720 |
| chr15 | 41913750 | 41913807 | chr15 | 41952572 | 41952711 | chr15 | 42749733 | 42749899 |
| chr15 | 43551059 | 43551196 | chr15 | 43810405 | 43810435 | chr15 | 44037568 | 44037604 |
| chr15 | 45403636 | 45403680 | chr15 | 45403799 | 45403999 | chr15 | 45404103 | 45404130 |
| chr15 | 45404898 | 45405117 | chr15 | 45421385 | 45421435 | chr15 | 45421998 | 45422095 |
| chr15 | 45427370 | 45427410 | chr15 | 45427611 | 45427719 | chr15 | 45427772 | 45427786 |
| chr15 | 45444061 | 45444141 | chr15 | 45479460 | 45479516 | chr15 | 45493209 | 45493371 |
| chr15 | 45670462 | 45670838 | chr15 | 46021437 | 46021467 | chr15 | 47476118 | 47476239 |
| chr15 | 47476291 | 47476419 | chr15 | 47476877 | 47476980 | chr15 | 47477013 | 47477018 |
| chr15 | 48483956 | 48483986 | chr15 | 48936726 | 48937645 | chr15 | 48937710 | 48937987 |
| chr15 | 48938212 | 48938510 | chr15 | 51385913 | 51386181 | chr15 | 51634075 | 51634135 |
| chr15 | 51973646 | 51973694 | chr15 | 51973764 | 51973934 | chr15 | 53075809 | 53075864 |
| chr15 | 53075986 | 53077000 | chr15 | 53077066 | 53077361 | chr15 | 53077655 | 53077731 |
| chr15 | 53078064 | 53078236 | chr15 | 53079340 | 53079677 | chr15 | 53079718 | 53079891 |
| chr15 | 53079971 | 53080082 | chr15 | 53080337 | 53080606 | chr15 | 53080935 | 53080990 |
| chr15 | 53081399 | 53081677 | chr15 | 53082443 | 53082491 | chr15 | 53096816 | 53096891 |
| chr15 | 53097231 | 53097261 | chr15 | 53097778 | 53097906 | chr15 | 53098382 | 53098658 |
| chr15 | 54270498 | 54270707 | chr15 | 54270932 | 54270961 | chr15 | 55452967 | 55452993 |
| chr15 | 55699089 | 55699127 | chr15 | 55806758 | 55806859 | chr15 | 55880891 | 55881011 |
| chr15 | 58357800 | 58357819 | chr15 | 59158488 | 59158537 | chr15 | 59950341 | 59950363 |
| chr15 | 60287038 | 60287585 | chr15 | 60287644 | 60287733 | chr15 | 60288786 | 50288844 |
| chr15 | 60289310 | 60289546 | chr15 | 60296122 | 60296209 | chr15 | 60296598 | 60296617 |
| chr15 | 60296861 | 60296923 | chr15 | 60297152 | 60297409 | chr15 | 60297637 | 60297826 |
| chr15 | 60297942 | 60298108 | chr15 | 61520916 | 61521014 | chr15 | 61521659 | 61521937 |
| chr15 | 62456922 | 62456952 | chr15 | 65669859 | 65669899 | chr15 | 65685595 | 65685708 |
| chr15 | 65862033 | 65862121 | chr15 | 66727409 | 66727498 | chr15 | 66729148 | 66729177 |
| chr15 | 66774117 | 66274203 | chr15 | 66963816 | 66963871 | chr15 | 68112611 | 68112641 |
| chr15 | 68113868 | 68113898 | chr15 | 68114139 | 68114195 | chr15 | 68116369 | 68116621 |
| chr15 | 68117830 | 68118633 | chr15 | 68118930 | 68119174 | chr15 | 68119579 | 68120352 |
| chr15 | 68120827 | 68120857 | chr15 | 68121150 | 68121957 | chr15 | 58122643 | 68122673 |
| chr15 | 68125261 | 68125664 | chr15 | 68127801 | 68128350 | chr15 | 68128594 | 68128688 |
| chr15 | 68260519 | 68260709 | chr15 | 71055636 | 71055815 | chr15 | 72412083 | 72412176 |
| chr15 | 72612540 | 72612906 | chr15 | 72743741 | 72743796 | chr15 | 73660004 | 73660067 |
| chr15 | 73661469 | 73661666 | chr15 | 74045075 | 74045097 | chr15 | 74422006 | 74422146 |
| chr15 | 74422869 | 74423002 | chr15 | 74658151 | 74658396 | chr15 | 74658502 | 74658587 |
| chr15 | 74686021 | 74685051 | chr15 | 74818772 | 74818789 | chr15 | 74903896 | 74903926 |
| chr15 | 75251346 | 75251382 | chr15 | 75251672 | 75251786 | chr15 | 76627508 | 76627536 |
| chr15 | 76627576 | 76627826 | chr15 | 76629163 | 76629220 | chr15 | 76629494 | 76629531 |
| chr15 | 76629814 | 76630124 | chr15 | 76630520 | 76630847 | chr15 | 76638472 | 76638496 |
| chr15 | 77448967 | 77449001 | chr15 | 78111196 | 78111210 | chr15 | 78501806 | 78501942 |
| chr15 | 78556819 | 78557108 | chr15 | 78596065 | 78596218 | chr15 | 78632727 | 78632823 |
| chr15 | 78912281 | 78912371 | chr15 | 78912623 | 78912653 | chr15 | 78912912 | 78913027 |
| chr15 | 78913095 | 78913170 | chr15 | 78913535 | 78913651 | chr15 | 79104217 | 79104246 |
| chr15 | 79104466 | 79104495 | chr15 | 79381705 | 79381745 | chr15 | 79382099 | 79382571 |
| chr15 | 79382786 | 79383252 | chr15 | 79383947 | 79383977 | chr15 | 79502211 | 79502360 |
| chr15 | 79575278 | 79575474 | chr15 | 79576145 | 79576277 | chr15 | 79724502 | 79724560 |
| chr15 | 79724607 | 79724792 | chr15 | 79724864 | 79725140 | chr15 | 79725422 | 79725539 |
| chr15 | 81071827 | 81071867 | chr15 | 82336879 | 82336972 | chr15 | 82340070 | 82340157 |
| chr15 | 83315336 | 83315393 | chr15 | 83316251 | 83317087 | chr15 | 83349234 | 83349611 |
| chr15 | 83349672 | 83349686 | chr15 | 83378212 | 83378370 | chr15 | 83776255 | 83776306 |
| chr15 | 83776333 | 83776716 | chr15 | 83776769 | 83776785 | chr15 | 83866523 | 83866541 |
| chr15 | 83875648 | 83875665 | chr15 | 83875706 | 83875901 | chr15 | 83877055 | 83877149 |
| chr15 | 83953884 | 83953903 | chr15 | 83954380 | 83954409 | chr15 | 84115747 | 84115853 |
| chr15 | 84115932 | 84115966 | chr15 | 84116905 | 84116949 | chr15 | 84322994 | 84323037 |
| chr15 | 84748578 | 84748619 | chr15 | 84748679 | 84749260 | chr15 | 85143024 | 85143054 |
| chr15 | 88798725 | 88798791 | chr15 | 88799537 | 88800301 | chr15 | 88800541 | 88801008 |
| chr15 | 88801089 | 88801103 | chr15 | 89149169 | 89149448 | chr15 | 89248753 | 89248907 |
| chr15 | 89346050 | 89346326 | chr15 | 89346347 | 89346393 | chr15 | 89346670 | 89346793 |
| chr15 | 89346882 | 89346943 | chr15 | 89903484 | 89903814 | chr15 | 89910521 | 89910748 |
| chr15 | 89911087 | 89911186 | chr15 | 89913750 | 89913780 | chr15 | 89914231 | 89914449 |
| chr15 | 89914867 | 89914895 | chr15 | 89915240 | 89915369 | chr15 | 89921956 | 89922006 |
| chr15 | 89922500 | 89922546 | chr15 | 89942755 | 89942945 | chr15 | 89943410 | 89943706 |
| chr15 | 89949617 | 89949942 | chr15 | 89950236 | 89950736 | chr15 | 89951082 | 89951113 |
| chr15 | 89951466 | 89951801 | chr15 | 89952153 | 89952452 | chr15 | 89952700 | 89953055 |
| chr15 | 89954197 | 89954335 | chr15 | 89956423 | 89956450 | chr15 | 90039563 | 90039711 |
| chr15 | 90631823 | 90631948 | chr15 | 90755916 | 90756079 | chr15 | 91643360 | 91643586 |
| chr15 | 92936290 | 92936322 | chr15 | 92937153 | 92937374 | chr15 | 92937927 | 92938060 |
| chr15 | 92938123 | 92938293 | chr15 | 93158592 | 93158739 | chr15 | 93631739 | 93632014 |
| chr15 | 93632660 | 93633233 | chr15 | 94347602 | 94347632 | chr15 | 96874362 | 96874514 |
| chr15 | 96889154 | 96889183 | chr15 | 96889401 | 96889430 | chr15 | 96897934 | 96898010 |
| chr15 | 96911559 | 96911691 | chr15 | 96952696 | 96953098 | chr15 | 96953132 | 96953209 |
| chr15 | 96959730 | 96959960 | chr15 | 96960376 | 96960409 | chr15 | 96960732 | 96960826 |

TABLE 13-continued

| chr | start | end | chr | start | end | chr | start | end |
|---|---|---|---|---|---|---|---|---|
| chr15 | 97006372 | 97006533 | chr15 | 98504114 | 98504144 | chr15 | 98836178 | 98836393 |
| chr15 | 98964786 | 98965138 | chr15 | 99193206 | 99193480 | chr15 | 99193914 | 99194186 |
| chr15 | 99453230 | 99453440 | chr15 | 99456299 | 99456329 | chr15 | 99497059 | 99497132 |
| chr15 | 100913423 | 100913595 | chr15 | 101420521 | 101420610 | chr15 | 101420972 | 101420989 |
| chr15 | 101818327 | 101818357 | chr16 | 93831 | 93932 | chr16 | 142649 | 142783 |
| chr16 | 215416 | 215872 | chr16 | 215913 | 216224 | chr16 | 216676 | 217036 |
| chr16 | 230265 | 230315 | chr16 | 230497 | 230610 | chr16 | 318104 | 318227 |
| chr16 | 318498 | 318763 | chr16 | 337599 | 337659 | chr16 | 410377 | 410407 |
| chr16 | 565492 | 565623 | chr16 | 571714 | 571959 | chr16 | 611385 | 611520 |
| chr16 | 611969 | 612260 | chr16 | 612869 | 613037 | chr16 | 667141 | 667297 |
| chr16 | 667547 | 667585 | chr16 | 667876 | 668074 | chr16 | 672768 | 672806 |
| chr16 | 677972 | 678084 | chr16 | 700299 | 700329 | chr16 | 726626 | 726990 |
| chr16 | 731488 | 731610 | chr16 | 735205 | 735594 | chr16 | 740883 | 740914 |
| chr16 | 741376 | 741519 | chr16 | 762669 | 762694 | chr16 | 837361 | 837460 |
| chr16 | 845955 | 845985 | chr16 | 882566 | 882588 | chr16 | 895093 | 895166 |
| chr16 | 943481 | 943553 | chr16 | 1018120 | 1018150 | chr16 | 1019640 | 1019685 |
| chr16 | 1030444 | 1030655 | chr16 | 1052587 | 1052627 | chr16 | 1102927 | 1102957 |
| chr16 | 1116661 | 1116691 | chr16 | 1122858 | 1122946 | chr16 | 1129011 | 1129140 |
| chr16 | 1155162 | 1155212 | chr16 | 1204003 | 1204034 | chr16 | 1217307 | 1217503 |
| chr16 | 1218034 | 1218090 | chr16 | 1228804 | 1228916 | chr16 | 1230056 | 1230142 |
| chr16 | 1248604 | 1248675 | chr16 | 1267925 | 1268120 | chr16 | 1271546 | 1271646 |
| chr16 | 1312526 | 1312611 | chr16 | 1323976 | 1324061 | chr16 | 1382901 | 1382940 |
| chr16 | 1394502 | 1394596 | chr16 | 1397454 | 1397484 | chr16 | 1407370 | 1407518 |
| chr16 | 1407818 | 1407846 | chr16 | 1408210 | 1408240 | chr16 | 1428508 | 1428873 |
| chr16 | 1491567 | 1491613 | chr16 | 1704656 | 1704800 | chr16 | 1730306 | 1730597 |
| chr16 | 1741853 | 1742079 | chr16 | 1750769 | 1750907 | chr16 | 1842490 | 1842519 |
| chr16 | 2029072 | 2029137 | chr16 | 2040914 | 2040960 | chr16 | 2040981 | 2041512 |
| chr16 | 2041582 | 2042160 | chr16 | 2042875 | 2042905 | chr16 | 2086831 | 2086860 |
| chr16 | 2106703 | 2106732 | chr16 | 2111966 | 2111995 | chr16 | 2120515 | 2120544 |
| chr16 | 2122243 | 2122272 | chr16 | 2124205 | 2124348 | chr16 | 2126080 | 2126109 |
| chr16 | 2128577 | 2129581 | chr16 | 2130361 | 2130390 | chr16 | 2132244 | 2132315 |
| chr16 | 2135301 | 2135330 | chr16 | 2136228 | 2136257 | chr16 | 2136727 | 2136855 |
| chr16 | 2140403 | 2140438 | chr16 | 2141909 | 2141972 | chr16 | 2142546 | 2142628 |
| chr16 | 2213313 | 2213343 | chr16 | 2232745 | 2232784 | chr16 | 2234726 | 2235020 |
| chr16 | 2281249 | 2281314 | chr16 | 2287295 | 2287370 | chr16 | 2485858 | 2485917 |
| chr16 | 2531069 | 2531177 | chr16 | 2764377 | 2764470 | chr16 | 2770122 | 2770512 |
| chr16 | 2818101 | 2818156 | chr16 | 2892542 | 2892602 | chr16 | 2892627 | 2892729 |
| chr16 | 2974601 | 2974650 | chr16 | 3017157 | 3017430 | chr16 | 3068171 | 3068201 |
| chr16 | 3151127 | 3151186 | chr16 | 3211708 | 3211744 | chr16 | 3211804 | 3211984 |
| chr16 | 3220591 | 3220892 | chr16 | 3221142 | 3221700 | chr16 | 3221787 | 3222239 |
| chr16 | 3225471 | 3225607 | chr16 | 3232739 | 3233016 | chr16 | 3233199 | 3233330 |
| chr16 | 3233435 | 3234103 | chr16 | 3234196 | 3234452 | chr16 | 3237857 | 3238022 |
| chr16 | 3238142 | 3238546 | chr16 | 3238993 | 3239631 | chr16 | 3239691 | 3239848 |
| chr16 | 3241549 | 3241663 | chr16 | 3241936 | 3241966 | chr16 | 3355279 | 3355718 |
| chr16 | 3598920 | 3598953 | chr16 | 3696694 | 3696724 | chr16 | 3802981 | 3803074 |
| chr16 | 3950263 | 3950279 | chr16 | 4264529 | 4264694 | chr16 | 4310735 | 4310847 |
| chr16 | 4431126 | 4431189 | chr16 | 4431487 | 4431516 | chr16 | 4731638 | 4731718 |
| chr16 | 4733166 | 4733195 | chr16 | 4738567 | 4738680 | chr16 | 4751554 | 4751583 |
| chr16 | 4846136 | 4846415 | chr16 | 4887144 | 4887164 | chr16 | 5037900 | 5038004 |
| chr16 | 5541116 | 5541158 | chr16 | 6069941 | 6070019 | chr16 | 7354634 | 7354657 |
| chr16 | 7382499 | 7382534 | chr16 | 8781032 | 8781135 | chr16 | 8870353 | 8870383 |
| chr16 | 9009860 | 9009989 | chr16 | 10274399 | 10274429 | chr16 | 10275370 | 10275392 |
| chr16 | 10275752 | 10275948 | chr16 | 10276360 | 10277050 | chr16 | 10277072 | 10277409 |
| chr16 | 10479815 | 10479980 | chr16 | 11242000 | 11242138 | chr16 | 11427659 | 11427732 |
| chr16 | 11490632 | 11490662 | chr16 | 12210772 | 12210896 | chr16 | 12211279 | 12211416 |
| chr16 | 12530169 | 12530199 | chr16 | 12971776 | 12971934 | chr16 | 12994459 | 12994737 |
| chr16 | 12995062 | 12995593 | chr16 | 12995803 | 12995803 | chr16 | 12996074 | 12996328 |
| chr16 | 12996617 | 12996720 | chr16 | 12996948 | 12997011 | chr16 | 12997386 | 12997703 |
| chr16 | 14021974 | 14022003 | chr16 | 14041504 | 14041533 | chr16 | 14041795 | 14041824 |
| chr16 | 14042062 | 14042091 | chr16 | 14726842 | 14725864 | chr16 | 15489599 | 15489808 |
| chr16 | 15739004 | 15739042 | chr16 | 15820825 | 15820865 | chr16 | 18802465 | 18802680 |
| chr16 | 18950973 | 18951018 | chr16 | 19531564 | 19531601 | chr16 | 19567202 | 19567449 |
| chr16 | 19895125 | 19895155 | chr16 | 21666641 | 21666771 | chr16 | 21831621 | 21831957 |
| chr16 | 21839328 | 21839369 | chr16 | 22326397 | 22326427 | chr16 | 22824701 | 22825076 |
| chr16 | 22825327 | 22825469 | chr16 | 22825886 | 22826081 | chr16 | 23313464 | 23313522 |
| chr16 | 23313780 | 23313836 | chr16 | 23706412 | 23706520 | chr16 | 23766097 | 23766130 |
| chr16 | 23847311 | 23847511 | chr16 | 23847789 | 23847874 | chr16 | 23847934 | 23847956 |
| chr16 | 24127295 | 24127338 | chr16 | 24172241 | 24172271 | chr16 | 24180710 | 24180760 |
| chr16 | 24267115 | 24267144 | chr16 | 24267485 | 24267578 | chr16 | 25266537 | 25266573 |
| chr16 | 25542437 | 25542452 | chr16 | 25702955 | 25702992 | chr16 | 25703685 | 26704122 |
| chr16 | 25704390 | 25704628 | chr16 | 25921574 | 25921604 | chr16 | 26664757 | 26664775 |
| chr16 | 27459938 | 27460074 | chr16 | 27749857 | 27750033 | chr16 | 28074176 | 28074254 |
| chr16 | 28074418 | 28074684 | chr16 | 28024959 | 28025197 | chr16 | 28877839 | 28877883 |
| chr16 | 28891040 | 28891072 | chr16 | 29119008 | 29119058 | chr16 | 29153284 | 29153320 |
| chr16 | 29244900 | 29244997 | chr16 | 29830871 | 29831078 | chr16 | 29888624 | 29888658 |
| chr16 | 30017330 | 30017447 | chr16 | 30116285 | 30116315 | chr16 | 30124691 | 30124861 |
| chr16 | 30804457 | 30804472 | chr16 | 30826362 | 30826509 | chr16 | 30907010 | 30907049 |
| chr16 | 30907109 | 30907148 | chr16 | 31227914 | 31228313 | chr16 | 31384593 | 31384623 |

TABLE 13-continued

| chr | start | end | chr | start | end | chr | start | end |
|---|---|---|---|---|---|---|---|---|
| chr16 | 31446873 | 31447096 | chr1e | 31498008 | 31498087 | chr16 | 31500544 | 31500673 |
| chr16 | 31580560 | 31581036 | chr16 | 46721567 | 46721707 | chr16 | 47177525 | 42177606 |
| chr16 | 48641663 | 48641693 | chr16 | 48845120 | 48845125 | chr16 | 49309170 | 49309262 |
| chr16 | 49311523 | 49311989 | chr16 | 49312033 | 49312299 | chr16 | 49313363 | 49313710 |
| chr16 | 49314022 | 49314118 | chr16 | 49314419 | 49314561 | chr16 | 49314784 | 49314821 |
| chr16 | 49315276 | 49315306 | chr16 | 49315919 | 49316315 | chr16 | 49316509 | 49316580 |
| chr16 | 49638060 | 49638090 | chr16 | 50335767 | 50335797 | chr16 | 51183964 | 51184406 |
| chr16 | 51184807 | 51184957 | chr16 | 51185055 | 51185291 | chr16 | 51185844 | 51185964 |
| chr16 | 51186026 | 51186280 | chr16 | 51186596 | 51186939 | chr16 | 51188697 | 51188711 |
| chr16 | 51189922 | 51190037 | chr16 | 51190122 | 51190215 | chr16 | 53467363 | 53467395 |
| chr16 | 53563622 | 53563654 | chr16 | 54128645 | 54128713 | chr16 | 54318898 | 54318988 |
| chr16 | 54319420 | 54319468 | chr16 | 54321638 | 54321818 | chr16 | 54324999 | 54325131 |
| chr16 | 54628691 | 54628867 | chr16 | 54964948 | 54965114 | chr16 | 54966830 | 54967264 |
| chr16 | 54971400 | 54971430 | chr16 | 55090666 | 55090861 | chr16 | 55357926 | 55357940 |
| chr16 | 55357992 | 55358086 | chr16 | 55358316 | 55358350 | chr16 | 55358798 | 55359071 |
| chr16 | 55363009 | 55363223 | chr16 | 55364716 | 55364843 | chr16 | 55365103 | 55365218 |
| chr15 | 55404999 | 55405214 | chr16 | 55689886 | 55689915 | chr16 | 55690115 | 55690379 |
| chr16 | 55690454 | 55690576 | chr16 | 55690762 | 55690809 | chr16 | 56224557 | 56224832 |
| chr16 | 56228370 | 56228416 | chr16 | 56228578 | 56228581 | chr16 | 56651094 | 56651123 |
| chr16 | 56651239 | 56651275 | chr16 | 56659175 | 56659673 | chr16 | 56672158 | 56672172 |
| chr16 | 56672222 | 56672385 | chr16 | 56672514 | 56672654 | chr16 | 56672656 | 56672685 |
| chr16 | 56709837 | 56709892 | chr16 | 56709950 | 56710030 | chr16 | 57222686 | 57222709 |
| chr16 | 57318379 | 57318412 | chr16 | 57935454 | 57935605 | chr16 | 58018634 | 58018845 |
| chr16 | 58019225 | 58019430 | chr16 | 58120795 | 58120961 | chr16 | 58497221 | 58497335 |
| chr16 | 58497752 | 58497829 | chr16 | 58498175 | 58498204 | chr16 | 58498570 | 58498724 |
| chr16 | 58521708 | 58521737 | chr16 | 58534666 | 58534695 | chr16 | 58545487 | 58545516 |
| chr16 | 58550489 | 58550519 | chr16 | 58969757 | 58969792 | chr16 | 62068463 | 62068517 |
| chr16 | 62068952 | 62068982 | chr16 | 62070743 | 62070773 | chr16 | 65154933 | 65155091 |
| chr16 | 65156385 | 65156489 | chr16 | 66461786 | 66461840 | chr16 | 66612882 | 66613095 |
| chr16 | 66613335 | 66613369 | chr16 | 67197698 | 67197769 | chr16 | 67198009 | 67198039 |
| chr16 | 67198917 | 67198957 | chr16 | 67241204 | 67241234 | chr16 | 67313865 | 67313895 |
| chr16 | 68481486 | 68481543 | chr16 | 68482808 | 68482941 | chr16 | 68544259 | 68544378 |
| chr16 | 68676408 | 68676604 | chr16 | 68676842 | 68676984 | chr16 | 68770835 | 68771298 |
| chr16 | 68844158 | 68844187 | chr16 | 68846033 | 68846062 | chr16 | 68856078 | 68856107 |
| chr16 | 68876782 | 68876859 | chr16 | 69969260 | 69969290 | chr16 | 70595535 | 70595700 |
| chr16 | 70794492 | 70794633 | chr16 | 71460027 | 71460088 | chr16 | 71460271 | 71460351 |
| chr16 | 71507775 | 71507791 | chr16 | 71715779 | 71715809 | chr16 | 72957763 | 72957795 |
| chr16 | 75019751 | 75019781 | chr16 | 77247440 | 77247470 | chr16 | 77468261 | 77468457 |
| chr16 | 77822589 | 77822874 | chr16 | 78079969 | 78080054 | chr16 | 79623602 | 79623616 |
| chr16 | 79623798 | 79623914 | chr16 | 80837962 | 80838143 | chr16 | 80966399 | 80966431 |
| chr16 | 81564199 | 81564229 | chr16 | 81929362 | 81929392 | chr16 | 81946246 | 81946275 |
| chr16 | 81962167 | 81962196 | chr16 | 82660360 | 82660496 | chr16 | 82660712 | 82660741 |
| chr16 | 84074836 | 84074871 | chr16 | 84153364 | 84153394 | chr16 | 84402244 | 84402319 |
| chr16 | 84519974 | 84520010 | chr16 | 84651793 | 84651822 | chr16 | 84823626 | 84823656 |
| chr16 | 84853288 | 84853376 | chr16 | 85075434 | 85075553 | chr16 | 85317850 | 85317882 |
| chr16 | 85485747 | 85485855 | chr16 | 85497445 | 85497475 | chr16 | 85517345 | 85517521 |
| chr16 | 85651520 | 85651550 | chr16 | 85678639 | 85678761 | chr16 | 85684308 | 85684457 |
| chr16 | 85699689 | 85699921 | chr16 | 85932828 | 85932858 | chr16 | 86320354 | 86320391 |
| chr16 | 86320755 | 86320800 | chr16 | 86321020 | 86321068 | chr16 | 86530947 | 86530992 |
| chr16 | 86531017 | 86531046 | chr16 | 86531375 | 86531480 | chr16 | 86531528 | 86531573 |
| chr16 | 86541591 | 86541968 | chr16 | 86542373 | 86542457 | chr16 | 86544191 | 86544557 |
| chr16 | 86571984 | 86572014 | chr16 | 86599481 | 86599844 | chr16 | 86600483 | 86600686 |
| chr16 | 86600958 | 86601015 | chr16 | 86601286 | 86601539 | chr16 | 86602038 | 86602514 |
| chr16 | 87092439 | 87092553 | chr16 | 87525622 | 87525701 | chr16 | 87635103 | 87635133 |
| chr16 | 87636627 | 87636907 | chr16 | 87714272 | 87714381 | chr16 | 87723735 | 87724098 |
| chr16 | 88007072 | 88007090 | chr16 | 88106322 | 88106398 | chr16 | 88164401 | 88164468 |
| chr16 | 88498241 | 88498760 | chr16 | 88504058 | 88504315 | chr16 | 88506346 | 88506526 |
| chr16 | 88512427 | 88512529 | chr16 | 88543428 | 88543458 | chr16 | 88550263 | 88550483 |
| chr16 | 88603696 | 88603760 | chr16 | 88623960 | 88624167 | chr16 | 88711337 | 88711507 |
| chr16 | 88757466 | 88757496 | chr16 | 88879949 | 88880097 | chr16 | 88883238 | 88883372 |
| chr16 | 88941058 | 88941141 | chr16 | 88942119 | 88942160 | chr16 | 88943559 | 88944024 |
| chr16 | 88945815 | 88945995 | chr16 | 88955249 | 88955368 | chr16 | 88956230 | 88956399 |
| chr16 | 88957350 | 88957857 | chr16 | 88958397 | 88958431 | chr16 | 88963277 | 88963763 |
| chr16 | 88966303 | 88966588 | chr16 | 88968709 | 88968789 | chr16 | 88978024 | 88978072 |
| chr16 | 88993078 | 88993230 | chr16 | 88999617 | 88999647 | chr16 | 89000168 | 89000204 |
| chr16 | 89001094 | 89001124 | chr16 | 89007520 | 89007558 | chr16 | 89007880 | 89007995 |
| chr16 | 89008562 | 89008592 | chr16 | 89047717 | 89047747 | chr16 | 89072503 | 89072774 |
| chr16 | 89086109 | 89086197 | chr16 | 89107675 | 89107732 | chr16 | 89109385 | 89109415 |
| chr16 | 89120038 | 89120319 | chr16 | 89120708 | 89120864 | chr16 | 89138016 | 89138060 |
| chr16 | 89220327 | 89220398 | chr16 | 89220655 | 89220922 | chr16 | 89240843 | 89240873 |
| chr16 | 89254653 | 89254742 | chr16 | 89267334 | 89267364 | chr16 | 89267808 | 89267824 |
| chr16 | 89558610 | 89558703 | chr16 | 89584337 | 89584417 | chr16 | 89883972 | 89884185 |
| chr16 | 89884966 | 89884994 | chr16 | 89885114 | 89885142 | chr16 | 89900124 | 89900180 |
| chr16 | 89900455 | 89900526 | chr17 | 415134 | 415163 | chr17 | 556252 | 556282 |
| chr17 | 617001 | 617033 | chr17 | 1082884 | 1083002 | chr17 | 1174274 | 1174361 |
| chr17 | 1174385 | 1174413 | chr17 | 1494550 | 1494613 | chr17 | 1536116 | 1636146 |
| chr17 | 1545976 | 1545999 | chr17 | 1546299 | 1546442 | chr17 | 1623703 | 1623735 |
| chr17 | 1959468 | 1959520 | chr17 | 2207801 | 2207981 | chr17 | 2208041 | 2208063 |

TABLE 13-continued

| chr | start | end | chr | start | end | chr | start | end |
|---|---|---|---|---|---|---|---|---|
| chr17 | 2220962 | 2221059 | chr17 | 2250051 | 2250081 | chr17 | 2278801 | 2278925 |
| chr17 | 2607905 | 2607986 | chr17 | 2663935 | 2664032 | chr17 | 3438914 | 3438932 |
| chr17 | 3657502 | 3657553 | chr17 | 3658490 | 3658519 | chr17 | 3658849 | 3658930 |
| chr17 | 3658990 | 3659011 | chr17 | 4544607 | 4544710 | chr17 | 4693354 | 4693388 |
| chr17 | 4699211 | 4699252 | chr17 | 4891276 | 4891305 | chr17 | 4891527 | 4891555 |
| chr17 | 5000428 | 5000790 | chr17 | 5019637 | 5019662 | chr17 | 5019738 | 5019761 |
| chr17 | 6616637 | 6616686 | chr17 | 6616911 | 6617173 | chr17 | 6679190 | 6679296 |
| chr17 | 6946107 | 6946141 | chr17 | 7348885 | 7348997 | chr17 | 7368947 | 7369139 |
| chr17 | 7471610 | 7471630 | chr17 | 7555117 | 7555425 | chr17 | 7572957 | 7573018 |
| chr17 | 7573968 | 7574028 | chr17 | 7576847 | 7577167 | chr17 | 7577504 | 7577604 |
| chr17 | 7578164 | 7578570 | chr17 | 7579285 | 7579880 | chr17 | 7906254 | 7906535 |
| chr17 | 7906832 | 7906861 | chr17 | 8104145 | 8104173 | chr17 | 8230335 | 8230694 |
| chr17 | 8534493 | 8534582 | chr17 | 8774623 | 8774653 | chr17 | 8868620 | 8868667 |
| chr17 | 8868815 | 8869385 | chr17 | 8906266 | 8906518 | chr17 | 8906993 | 8907575 |
| chr17 | 8926060 | 8926263 | chr17 | 10101084 | 10101109 | chr17 | 10101132 | 10101447 |
| chr17 | 10102415 | 10102665 | chr17 | 11144926 | 11144989 | chr17 | 11984693 | 11984722 |
| chr17 | 11998944 | 11998973 | chr17 | 12013726 | 12013755 | chr17 | 12016550 | 12016630 |
| chr17 | 12028618 | 12028647 | chr17 | 13504195 | 13504195 | chr17 | 13504557 | 13504681 |
| chr17 | 13505002 | 13505188 | chr17 | 13505418 | 13505572 | chr17 | 14201041 | 14201181 |
| chr17 | 14204212 | 14204242 | chr17 | 14204527 | 14204620 | chr17 | 15245050 | 15245139 |
| chr17 | 16282251 | 16282300 | chr17 | 16284630 | 16285065 | chr17 | 16326144 | 16326216 |
| chr17 | 16570699 | 16570794 | chr17 | 17062574 | 17062763 | chr17 | 17117365 | 17117395 |
| chr17 | 17123963 | 17123993 | chr17 | 17398404 | 17398440 | chr17 | 17719242 | 17719355 |
| chr17 | 18163055 | 18163325 | chr17 | 18538185 | 18538275 | chr17 | 18817198 | 18817241 |
| chr17 | 20238152 | 20238175 | chr17 | 20468021 | 20468090 | chr17 | 20817896 | 20817917 |
| chr17 | 25620573 | 25620715 | chr17 | 25676959 | 25676989 | chr17 | 25680264 | 25680294 |
| chr17 | 25907750 | 25907780 | chr17 | 26263183 | 26263223 | chr17 | 26554634 | 26554705 |
| chr17 | 26961770 | 26961833 | chr17 | 27036998 | 27037023 | chr17 | 27038649 | 27038685 |
| chr17 | 27056837 | 27056857 | chr17 | 27170162 | 27170191 | chr17 | 27181276 | 27181371 |
| chr17 | 27332453 | 27332660 | chr17 | 27716114 | 27716137 | chr17 | 27716197 | 27716220 |
| chr17 | 27940591 | 27940911 | chr17 | 28562701 | 28562765 | chr17 | 29232244 | 29232267 |
| chr17 | 29249717 | 29249930 | chr17 | 29298080 | 29298581 | chr17 | 29508761 | 29508790 |
| chr17 | 29541627 | 29541556 | chr17 | 29562732 | 29562761 | chr17 | 29718215 | 29718269 |
| chr17 | 29719187 | 29719242 | chr17 | 30243768 | 30243907 | chr17 | 30250325 | 30250345 |
| chr17 | 30568137 | 30568174 | chr17 | 31618425 | 31619319 | chr17 | 31619951 | 31620026 |
| chr17 | 32484020 | 32484049 | chr17 | 32906379 | 32906555 | chr17 | 32906599 | 32906636 |
| chr17 | 32906987 | 32907146 | chr17 | 32907652 | 32907753 | chr17 | 32908132 | 32908146 |
| chr17 | 32908171 | 32908374 | chr17 | 32908647 | 32908931 | chr17 | 33288229 | 33288351 |
| chr17 | 33288890 | 33288988 | chr17 | 33672916 | 33672986 | chr17 | 33877286 | 33877303 |
| chr17 | 33917239 | 33917268 | chr17 | 35165645 | 35165691 | chr17 | 35165986 | 35166011 |
| chr17 | 35285542 | 35285666 | chr17 | 35290388 | 35290655 | chr17 | 35291320 | 35291354 |
| chr17 | 35291829 | 35291898 | chr17 | 35291921 | 35292626 | chr17 | 35293704 | 35294154 |
| chr17 | 35294461 | 35294505 | chr17 | 35295047 | 35295160 | chr17 | 35296143 | 35296292 |
| chr17 | 35296728 | 35296888 | chr17 | 35297619 | 35298153 | chr17 | 35299251 | 35299443 |
| chr17 | 35299601 | 35299965 | chr17 | 35300261 | 35300712 | chr17 | 35300813 | 35300854 |
| chr17 | 35303340 | 35303535 | chr17 | 35872722 | 35872861 | chr17 | 36103021 | 36103326 |
| chr17 | 36103571 | 36103601 | chr17 | 36104218 | 36104550 | chr17 | 36104644 | 36104779 |
| chr17 | 36105223 | 36105349 | chr17 | 36105459 | 36105596 | chr17 | 36715772 | 36715967 |
| chr17 | 37192162 | 37192201 | chr17 | 37321186 | 37321624 | chr17 | 37321788 | 37321972 |
| chr17 | 37366337 | 37366552 | chr17 | 37369180 | 37369210 | chr17 | 37381011 | 37381429 |
| chr17 | 37381571 | 37381726 | chr17 | 37381826 | 37381850 | chr17 | 37382146 | 37382248 |
| chr17 | 37484095 | 37484128 | chr17 | 37757153 | 37767217 | chr17 | 37760484 | 37760561 |
| chr17 | 37761997 | 37762334 | chr17 | 37868190 | 37868294 | chr17 | 37879568 | 37879616 |
| chr17 | 37880205 | 37880276 | chr17 | 37880971 | 37881018 | chr17 | 37881318 | 37881631 |
| chr17 | 38179397 | 38179430 | chr17 | 38347560 | 38347615 | chr17 | 38474363 | 38474502 |
| chr17 | 38497616 | 38497645 | chr17 | 38498083 | 38498112 | chr17 | 38504087 | 38504116 |
| chr17 | 38510555 | 38510584 | chr17 | 39682502 | 39682711 | chr17 | 40332943 | 40333226 |
| chr17 | 40400867 | 40401031 | chr17 | 40464278 | 40464317 | chr17 | 40464517 | 40464607 |
| chr17 | 40474467 | 40474496 | chr17 | 40826197 | 40826226 | chr17 | 40837022 | 40837051 |
| chr17 | 40837287 | 40837383 | chr17 | 40838982 | 40839022 | chr17 | 40975575 | 40975677 |
| chr17 | 41177394 | 41177459 | chr17 | 41197714 | 41197743 | chr17 | 41201163 | 41201192 |
| chr17 | 41203073 | 41203102 | chr17 | 41209064 | 41209114 | chr17 | 41215890 | 41215951 |
| chr17 | 41267731 | 41267775 | chr17 | 41276031 | 41276075 | chr17 | 41277259 | 41277721 |
| chr17 | 41278621 | 41278700 | chr17 | 41651850 | 41651880 | chr17 | 41791460 | 41791489 |
| chr17 | 41791665 | 41791694 | chr17 | 42030329 | 42030750 | chr17 | 42061304 | 42061381 |
| chr17 | 42082522 | 42082557 | chr17 | 42084361 | 42084626 | chr17 | 42092190 | 42092220 |
| chr17 | 42331626 | 42331659 | chr17 | 42393842 | 42394024 | chr17 | 42402884 | 42402917 |
| chr17 | 42580695 | 42580793 | chr17 | 42587332 | 42587355 | chr17 | 42635295 | 42635760 |
| chr17 | 42733711 | 42733884 | chr17 | 42787579 | 42787616 | chr17 | 42907564 | 42907630 |
| chr17 | 42907655 | 42907951 | chr17 | 43001891 | 43001946 | chr17 | 43044658 | 43044688 |
| chr17 | 43045039 | 43045116 | chr17 | 43046260 | 43046385 | chr17 | 43339109 | 43339333 |
| chr17 | 43339609 | 43339899 | chr17 | 43974256 | 43974358 | chr17 | 44897416 | 44897445 |
| chr17 | 45331014 | 45331313 | chr17 | 45810850 | 45811341 | chr17 | 45867315 | 45867460 |
| chr17 | 46125007 | 46125061 | chr17 | 46567618 | 46567655 | chr17 | 46619540 | 46619569 |
| chr17 | 46620494 | 46621094 | chr17 | 46621353 | 46621458 | chr17 | 46621856 | 46621909 |
| chr17 | 46655148 | 46655178 | chr17 | 46655451 | 46655998 | chr17 | 46656058 | 46656704 |
| chr17 | 46659429 | 46659859 | chr17 | 46663743 | 46663824 | chr17 | 46663856 | 46663887 |
| chr17 | 46674873 | 46674970 | chr17 | 46675170 | 46675600 | chr17 | 46690467 | 46690664 |

TABLE 13-continued

| chr | start | end | chr | start | end | chr | start | end |
|---|---|---|---|---|---|---|---|---|
| chr17 | 46691505 | 46691592 | chr17 | 46691805 | 46691818 | chr17 | 46691988 | 46692110 |
| chr17 | 46692439 | 46692606 | chr17 | 46710946 | 46710989 | chr17 | 46713959 | 46714072 |
| chr17 | 46795641 | 46796373 | chr17 | 46796499 | 46796637 | chr17 | 46796850 | 46797213 |
| chr17 | 46797275 | 46797582 | chr17 | 46799625 | 46799896 | chr17 | 46800601 | 46800668 |
| chr17 | 46800961 | 46801047 | chr17 | 46801109 | 46801416 | chr17 | 46802459 | 46802911 |
| chr17 | 46802994 | 46803286 | chr17 | 46804107 | 46804428 | chr17 | 46810416 | 46810958 |
| chr17 | 46811354 | 46811499 | chr17 | 46816282 | 46816730 | chr17 | 46824224 | 46824275 |
| chr17 | 46824359 | 46825054 | chr17 | 46825284 | 46825514 | chr17 | 46826930 | 46827127 |
| chr17 | 46827330 | 46827501 | chr17 | 46827626 | 46827756 | chr17 | 46829498 | 46829579 |
| chr17 | 46829979 | 46830110 | chr17 | 46831779 | 46832325 | chr17 | 46832490 | 46832639 |
| chr17 | 47072805 | 47073028 | chr17 | 47073104 | 47073327 | chr17 | 47073389 | 47073465 |
| chr17 | 47073988 | 47074228 | chr17 | 47074561 | 47074895 | chr17 | 47075160 | 47075364 |
| chr17 | 47075715 | 47075734 | chr17 | 47075880 | 47076055 | chr17 | 47574090 | 47574149 |
| chr17 | 47657544 | 47657583 | chr17 | 47865514 | 47865555 | chr17 | 47987525 | 47987619 |
| chr17 | 47987930 | 47988114 | chr17 | 48041152 | 48041320 | chr17 | 48041672 | 48041721 |
| chr17 | 48042039 | 48042069 | chr17 | 48042435 | 48042647 | chr17 | 48042751 | 48042956 |
| chr17 | 48048952 | 48049059 | chr17 | 48049307 | 48050526 | chr17 | 48071020 | 48071050 |
| chr17 | 48071807 | 48071894 | chr17 | 48473206 | 48473236 | chr17 | 48545804 | 48545950 |
| chr17 | 48589801 | 48589831 | chr17 | 48612223 | 48612308 | chr17 | 48636361 | 48637136 |
| chr17 | 48653128 | 48653158 | chr17 | 48799843 | 48799866 | chr17 | 49027838 | 49027876 |
| chr17 | 49229485 | 49229605 | chr17 | 50235216 | 50235258 | chr17 | 50235631 | 50235952 |
| chr17 | 51901004 | 51901034 | chr17 | 53341252 | 53341536 | chr17 | 53342876 | 53343089 |
| chr17 | 53922649 | 53922790 | chr17 | 54674986 | 54675272 | chr17 | 54755969 | 54755990 |
| chr17 | 55122813 | 55122842 | chr17 | 55213641 | 55213670 | chr17 | 55962573 | 55962841 |
| chr17 | 56092600 | 56092638 | chr17 | 56234405 | 56234743 | chr17 | 56326949 | 56326994 |
| chr17 | 56327271 | 56327301 | chr17 | 56471121 | 56471144 | chr17 | 56833127 | 56833221 |
| chr17 | 56833707 | 56834000 | chr17 | 56834020 | 56834075 | chr17 | 56834306 | 56834375 |
| chr17 | 57297027 | 57297129 | chr17 | 58216613 | 58216836 | chr17 | 58216866 | 58212298 |
| chr17 | 58217357 | 58217551 | chr17 | 58218765 | 58218993 | chr17 | 58227374 | 58227397 |
| chr17 | 58498697 | 58499314 | chr17 | 59474157 | 59474246 | chr17 | 59474833 | 59475100 |
| chr17 | 59475678 | 59476023 | chr17 | 59476083 | 59476127 | chr17 | 59476410 | 59476635 |
| chr17 | 59478147 | 59478602 | chr17 | 59481657 | 59481678 | chr17 | 59488101 | 59488423 |
| chr17 | 59528876 | 59529150 | chr17 | 59529254 | 59529264 | chr17 | 59529844 | 59530352 |
| chr17 | 59531667 | 59532017 | chr17 | 59533875 | 59534405 | chr17 | 59534751 | 59534781 |
| chr17 | 59535137 | 59535219 | chr17 | 59539236 | 59539601 | chr17 | 59924556 | 59924585 |
| chr17 | 59937192 | 59937236 | chr17 | 61778235 | 61778248 | chr17 | 61817856 | 61817955 |
| chr17 | 61926172 | 61926324 | chr17 | 61926508 | 61926603 | chr17 | 62028596 | 62028790 |
| chr17 | 62777335 | 62777450 | chr17 | 62777746 | 62777791 | chr17 | 64672366 | 64672544 |
| chr17 | 66420718 | 66420748 | chr17 | 66596471 | 66596525 | chr17 | 66596984 | 66597021 |
| chr17 | 67410381 | 67410397 | chr17 | 68164733 | 68164928 | chr17 | 70026543 | 70026667 |
| chr17 | 70112916 | 70113566 | chr17 | 70113648 | 70114018 | chr17 | 70114153 | 70114517 |
| chr17 | 70215683 | 70216306 | chr17 | 70216393 | 70216585 | chr17 | 71641544 | 71641683 |
| chr17 | 71948439 | 71948863 | chr17 | 72270286 | 72270415 | chr17 | 72321933 | 72321975 |
| chr17 | 72322363 | 12322557 | chr17 | 72353213 | 72353259 | chr17 | 72353417 | 72353550 |
| chr17 | 72427853 | 72427999 | chr17 | 72428344 | 72428381 | chr17 | 72491378 | 72491395 |
| chr17 | 72667337 | 72667481 | chr17 | 72849010 | 72849079 | chr17 | 72857038 | 72857368 |
| chr17 | 72862371 | 72862460 | chr17 | 72920796 | 72921032 | chr17 | 73031637 | 73031666 |
| chr17 | 73115884 | 73115914 | chr17 | 73215289 | 73215386 | chr17 | 73545998 | 73546299 |
| chr17 | 73586015 | 73586418 | chr17 | 73608306 | 73608336 | chr17 | 73636144 | 73636337 |
| chr17 | 73808631 | 73808671 | chr17 | 73827213 | 73827243 | chr17 | 74028346 | 74028413 |
| chr17 | 74047797 | 74048020 | chr17 | 74070372 | 74070479 | chr17 | 74071445 | 74071481 |
| chr17 | 74071689 | 74071729 | chr17 | 74072999 | 74073036 | chr17 | 74073269 | 74073433 |
| chr17 | 74087118 | 74087185 | chr17 | 74390363 | 74390393 | chr17 | 74533844 | 74534310 |
| chr17 | 74581182 | 74581221 | chr17 | 74732944 | 74732973 | chr17 | 74865053 | 74865192 |
| chr17 | 74855698 | 74866243 | chr17 | 75137660 | 75137887 | chr17 | 75207514 | 76207630 |
| chr17 | 75207839 | 75207987 | chr17 | 75276054 | 75276083 | chr17 | 75276413 | 75276442 |
| chr17 | 75277348 | 75277659 | chr17 | 75278020 | 75278049 | chr17 | 75279105 | 75279134 |
| chr17 | 75282025 | 75282154 | chr17 | 75315512 | 75315681 | chr17 | 75316368 | 75316397 |
| chr17 | 75317170 | 75317199 | chr17 | 75347755 | 75347784 | chr17 | 75368735 | 75369238 |
| chr17 | 75369440 | 75369457 | chr17 | 75369493 | 75369860 | chr17 | 75370269 | 75370316 |
| chr17 | 75370596 | 75370625 | chr17 | 75373312 | 75373341 | chr17 | 75385071 | 75385446 |
| chr17 | 75405827 | 75405856 | chr17 | 75417150 | 75417179 | chr17 | 75523142 | 75523272 |
| chr17 | 75524636 | 75525194 | chr17 | 75733978 | 75734244 | chr17 | 75797111 | 75797179 |
| chr17 | 76125196 | 76125225 | chr17 | 76126434 | 76126463 | chr17 | 76128466 | 76128663 |
| chr17 | 76130124 | 76130153 | chr17 | 76130481 | 76130510 | chr17 | 76137951 | 76138190 |
| chr17 | 76138498 | 76138622 | chr17 | 76187407 | 76187505 | chr17 | 76207342 | 76207372 |
| chr17 | 76227849 | 76228161 | chr17 | 76228214 | 76228357 | chr17 | 76404615 | 76404659 |
| chr17 | 76877177 | 76877212 | chr17 | 76974447 | 76974499 | chr17 | 77084518 | 77084727 |
| chr17 | 77105055 | 77105198 | chr17 | 77145129 | 77145242 | chr17 | 77179113 | 77179278 |
| chr17 | 77179630 | 77179776 | chr17 | 77394706 | 77394850 | chr17 | 77776827 | 77776995 |
| chr17 | 77777053 | 77777056 | chr17 | 77777585 | 77777903 | chr17 | 77777944 | 77777961 |
| chr17 | 77778943 | 77779179 | chr17 | 77789474 | 77789500 | chr17 | 77825696 | 77825812 |
| chr17 | 27899664 | 77899693 | chr17 | 77919429 | 77919477 | chr17 | 77924259 | 77924351 |
| chr17 | 78122174 | 78122190 | chr17 | 78194821 | 78194861 | chr17 | 78272278 | 78272313 |
| chr17 | 78447127 | 78447157 | chr17 | 78451931 | 78451953 | chr17 | 78452296 | 78452340 |
| chr17 | 78452681 | 78452833 | chr17 | 78518175 | 78518198 | chr17 | 78599596 | 78599628 |
| chr17 | 78667992 | 78668159 | chr17 | 78874441 | 78874559 | chr17 | 78999625 | 78999654 |
| chr17 | 79058302 | 79058333 | chr17 | 79094182 | 79094245 | chr17 | 79099770 | 79099799 |

TABLE 13-continued

| chr | start | end | chr | start | end | chr | start | end |
|---|---|---|---|---|---|---|---|---|
| chr17 | 79626617 | 79626703 | chr17 | 79769433 | 79769693 | chr17 | 79813409 | 79813507 |
| chr17 | 79896013 | 79896043 | chr17 | 79945037 | 79945074 | chr17 | 80186260 | 80186289 |
| chr17 | 80197756 | 80197898 | chr17 | 80254266 | 80254296 | chr17 | 80289234 | 80289310 |
| chr17 | 80329709 | 80330000 | chr17 | 80394063 | 80394185 | chr17 | 80394573 | 80394602 |
| chr17 | 80479345 | 80479525 | chr17 | 80491572 | 80491602 | chr17 | 80535382 | 80535487 |
| chr17 | 80571380 | 80571776 | chr17 | 80654983 | 80655013 | chr17 | 80693017 | 80693554 |
| chr17 | 80749244 | 80749276 | chr17 | 80751650 | 80751714 | chr17 | 80794259 | 80794288 |
| chr17 | 80797692 | 80798345 | chr17 | 80832305 | 80832411 | chr17 | 80832712 | 80832796 |
| chr17 | 80859239 | 80859269 | chr17 | 81008618 | 81008826 | chr17 | 81033487 | 81033517 |
| chr17 | 81048993 | 81049023 | chr17 | 81049994 | 81050058 | chr18 | 499367 | 499482 |
| chr18 | 500046 | 500738 | chr18 | 904462 | 904648 | chr18 | 905000 | 905030 |
| chr18 | 905434 | 905615 | chr18 | 906871 | 906907 | chr18 | 907472 | 907594 |
| chr18 | 907912 | 907977 | chr18 | 908454 | 908589 | chr18 | 909487 | 909587 |
| chr18 | 2755854 | 2755878 | chr18 | 2906268 | 2906304 | chr18 | 3214441 | 3214543 |
| chr18 | 3215042 | 3215256 | chr18 | 3499067 | 3499371 | chr18 | 4453964 | 4454163 |
| chr18 | 5133207 | 5133343 | chr18 | 5196576 | 5196959 | chr18 | 5197202 | 5197271 |
| chr18 | 5197330 | 5197347 | chr18 | 5237878 | 5238247 | chr18 | 5628167 | 5628515 |
| chr18 | 5629774 | 5629825 | chr18 | 5630312 | 5630362 | chr18 | 5895023 | 5895205 |
| chr18 | 5895975 | 5896085 | chr18 | 6729952 | 6729993 | chr18 | 6908056 | 6908090 |
| chr18 | 7117665 | 7117804 | chr18 | 7567783 | 7568291 | chr18 | 8608748 | 8608837 |
| chr18 | 8608902 | 8608968 | chr18 | 8612252 | 8612282 | chr18 | 9771586 | 9771753 |
| chr18 | 9912767 | 9912797 | chr18 | 10251324 | 10251348 | chr18 | 10589096 | 10589348 |
| chr18 | 11148969 | 11149045 | chr18 | 11149561 | 11149759 | chr18 | 11149780 | 11149888 |
| chr18 | 11401654 | 11401817 | chr18 | 11689190 | 11689220 | chr18 | 11752128 | 11752379 |
| chr18 | 11752700 | 11752730 | chr18 | 11942728 | 11942753 | chr18 | 12254305 | 12254578 |
| chr18 | 12277243 | 12277273 | chr18 | 12307247 | 12307505 | chr18 | 12307603 | 12307751 |
| chr18 | 12376086 | 12376129 | chr18 | 13132080 | 13132223 | chr18 | 13824025 | 13824102 |
| chr18 | 13826393 | 13826536 | chr18 | 13868713 | 13868919 | chr18 | 15198149 | 15198248 |
| chr18 | 18822392 | 18823274 | chr18 | 19750308 | 19750346 | chr18 | 20911541 | 20911571 |
| chr18 | 21269349 | 21269390 | chr18 | 21269659 | 21269740 | chr18 | 21719351 | 21719568 |
| chr18 | 22929081 | 22929095 | chr18 | 22929187 | 22929718 | chr18 | 22929729 | 22930559 |
| chr18 | 22930790 | 22931178 | chr18 | 23686462 | 23686540 | chr18 | 24127748 | 24128030 |
| chr18 | 24130809 | 24130946 | chr18 | 24131099 | 24131187 | chr18 | 24764951 | 24765168 |
| chr18 | 25755593 | 25755655 | chr18 | 25756010 | 25756040 | chr18 | 25756495 | 25756729 |
| chr18 | 25757187 | 25757452 | chr18 | 25757787 | 25757824 | chr18 | 25758129 | 25758141 |
| chr18 | 28620899 | 28620955 | chr18 | 28621034 | 28621097 | chr18 | 28621328 | 28621393 |
| chr18 | 28621636 | 28621932 | chr18 | 28622419 | 28622488 | chr18 | 30349740 | 30349781 |
| chr18 | 31020495 | 31020510 | chr18 | 31158093 | 31158158 | chr18 | 31739035 | 31739469 |
| chr18 | 31802132 | 31802167 | chr18 | 31802938 | 31802968 | chr18 | 31803438 | 31803472 |
| chr18 | 31902793 | 31902945 | chr18 | 32073908 | 32074086 | chr18 | 32557832 | 32557864 |
| chr18 | 32847598 | 32847642 | chr18 | 32957803 | 32957821 | chr18 | 33078363 | 33078393 |
| chr18 | 33078633 | 33078662 | chr18 | 33877683 | 33877754 | chr18 | 35065072 | 35065145 |
| chr18 | 35144845 | 35144936 | chr18 | 35144969 | 35145465 | chr18 | 35145985 | 35146036 |
| chr18 | 35146062 | 35146241 | chr18 | 35147487 | 35147569 | chr18 | 43914211 | 43914278 |
| chr18 | 44259903 | 44259990 | chr18 | 44336034 | 44336449 | chr18 | 44337444 | 44337617 |
| chr18 | 44337650 | 44337841 | chr18 | 44773060 | 44773116 | chr18 | 44773592 | 44773966 |
| chr18 | 44774406 | 44774890 | chr18 | 44775380 | 44775554 | chr18 | 44776972 | 44777088 |
| chr18 | 44777301 | 44777331 | chr18 | 44777596 | 44777750 | chr18 | 44778049 | 44778326 |
| chr18 | 44781003 | 44781041 | chr18 | 44787781 | 44787846 | chr18 | 44788251 | 44788281 |
| chr18 | 44789474 | 44789514 | chr18 | 44789872 | 44789937 | chr18 | 45058069 | 45058240 |
| chr18 | 46142662 | 46142809 | chr18 | 47720492 | 47720522 | chr18 | 48604773 | 48604802 |
| chr18 | 48636211 | 48636320 | chr18 | 49867303 | 49867399 | chr18 | 52989009 | 52989220 |
| chr18 | 52989741 | 52989882 | chr18 | 53267137 | 53257204 | chr18 | 53446970 | 53447474 |
| chr18 | 53447799 | 53447816 | chr18 | 53989796 | 53989877 | chr18 | 54789070 | 54789256 |
| chr18 | 55019707 | 55019775 | chr18 | 55020655 | 55020698 | chr18 | 55021078 | 55021242 |
| chr18 | 55103381 | 55103411 | chr18 | 55104808 | 55105140 | chr18 | 55105728 | 55105830 |
| chr18 | 55114480 | 55114644 | chr18 | 55850845 | 55850987 | chr18 | 56483918 | 56483938 |
| chr18 | 56815734 | 56815891 | chr18 | 56887076 | 56887424 | chr18 | 56888554 | 56888623 |
| chr18 | 56931541 | 56931583 | chr18 | 56931967 | 56932107 | chr18 | 56932352 | 56932375 |
| chr18 | 56935010 | 56935319 | chr18 | 56936004 | 56936074 | chr18 | 56939113 | 56939174 |
| chr18 | 56939423 | 56939651 | chr18 | 56939764 | 56940170 | chr18 | 56940566 | 56940722 |
| chr18 | 56940955 | 56941244 | chr18 | 56941558 | 56941788 | chr18 | 57363706 | 57363743 |
| chr18 | 57364658 | 57364691 | chr18 | 59000988 | 59001022 | chr18 | 59001301 | 59001343 |
| chr18 | 59001498 | 59001740 | chr18 | 60263661 | 60263895 | chr18 | 60985498 | 60985532 |
| chr18 | 60985593 | 60985732 | chr18 | 61143911 | 61143975 | chr18 | 67067558 | 67067907 |
| chr18 | 67068715 | 67068811 | chr18 | 67069216 | 67069246 | chr18 | 70209148 | 70209205 |
| chr18 | 70210418 | 70210508 | chr18 | 70211626 | 70211666 | chr18 | 70534282 | 70534315 |
| chr18 | 70534428 | 70534731 | chr18 | 70535373 | 70535554 | chr18 | 70535576 | 70535582 |
| chr18 | 70536010 | 70536083 | chr18 | 70536188 | 70536604 | chr18 | 70536833 | 70536871 |
| chr18 | 70537188 | 70537218 | chr18 | 72845833 | 72845863 | chr18 | 73167585 | 73167832 |
| chr18 | 73628019 | 73628068 | chr18 | 74501144 | 74501183 | chr18 | 74755508 | 74755590 |
| chr18 | 74961326 | 74961955 | chr18 | 74962019 | 74962147 | chr18 | 74962970 | 74963545 |
| chr18 | 75335093 | 75335123 | chr18 | 75339231 | 75339340 | chr18 | 75362793 | 75362985 |
| chr18 | 75551271 | 75551301 | chr18 | 75612225 | 75612286 | chr18 | 75999404 | 75999434 |
| chr18 | 76239541 | 76239616 | chr18 | 76501479 | 76501509 | chr18 | 76653631 | 76653661 |
| chr18 | 76686249 | 76686279 | chr18 | 76740102 | 76740223 | chr18 | 77143346 | 77143376 |
| chr18 | 77167824 | 77167854 | chr18 | 77181355 | 77181409 | chr18 | 77194936 | 77194978 |
| chr18 | 77205532 | 77205638 | chr18 | 77285897 | 77286028 | chr18 | 77300326 | 77300483 |

TABLE 13-continued

| chr | start | end | chr | start | end | chr | start | end |
|---|---|---|---|---|---|---|---|---|
| chr18 | 27309533 | 77309563 | chr18 | 77312866 | 77312927 | chr18 | 77329727 | 77330017 |
| chr18 | 77371430 | 77371547 | chr18 | 77459762 | 77459877 | chr18 | 77543249 | 77543335 |
| chr18 | 77543700 | 77543824 | chr18 | 77548352 | 77548609 | chr18 | 77550206 | 77550367 |
| chr18 | 77558082 | 77558358 | chr18 | 77558831 | 77558930 | chr18 | 77576934 | 77577043 |
| chr18 | 77636591 | 77636621 | chr18 | 78004993 | 78005051 | chr19 | 403538 | 403809 |
| chr19 | 407189 | 407320 | chr19 | 418225 | 418255 | chr19 | 462181 | 462269 |
| chr19 | 468757 | 468787 | chr19 | 485165 | 485394 | chr19 | 549361 | 549451 |
| chr19 | 555608 | 555628 | chr19 | 570156 | 570175 | chr19 | 591365 | 591416 |
| chr19 | 592589 | 592632 | chr19 | 593290 | 593376 | chr19 | 599214 | 599333 |
| chr19 | 752136 | 752359 | chr19 | 869337 | 869394 | chr19 | 883624 | 883791 |
| chr19 | 884018 | 884162 | chr19 | 891516 | 891620 | chr19 | 955757 | 956237 |
| chr19 | 959128 | 959158 | chr19 | 1003305 | 1003384 | chr19 | 1003669 | 1003734 |
| chr19 | 1004915 | 1005441 | chr19 | 1030176 | 1030225 | chr19 | 1047890 | 1047915 |
| chr19 | 1083314 | 1083437 | chr19 | 1156624 | 1156554 | chr19 | 1170185 | 1170230 |
| chr19 | 1171099 | 1171324 | chr19 | 1220422 | 1220610 | chr19 | 1221981 | 1222010 |
| chr19 | 1236474 | 1236678 | chr19 | 1274778 | 1274826 | chr19 | 1308047 | 1308081 |
| chr19 | 1325788 | 1325889 | chr19 | 1401752 | 1401795 | chr19 | 1450319 | 1450390 |
| chr19 | 1496413 | 1496450 | chr19 | 1496654 | 1496674 | chr19 | 1524443 | 1524447 |
| chr19 | 1525605 | 1525960 | chr19 | 1527227 | 1527311 | chr19 | 1754172 | 1754193 |
| chr19 | 1754225 | 1754254 | chr19 | 1754739 | 1754804 | chr19 | 1757416 | 1757615 |
| chr19 | 1762474 | 1762505 | chr19 | 1764293 | 1764339 | chr19 | 1775076 | 1775239 |
| chr19 | 1776376 | 1776534 | chr19 | 1800032 | 1800300 | chr19 | 1807970 | 1808413 |
| chr19 | 2135672 | 2135701 | chr19 | 2251152 | 2251234 | chr19 | 2251611 | 2251715 |
| chr19 | 2252589 | 2252658 | chr19 | 2252984 | 2253735 | chr19 | 2274677 | 2274695 |
| chr19 | 2290253 | 2290271 | chr19 | 2290631 | 2290867 | chr19 | 2302793 | 2302951 |
| chr19 | 2331413 | 2331443 | chr19 | 2513250 | 2513285 | chr19 | 2642877 | 2642947 |
| chr19 | 2683911 | 2684056 | chr19 | 3041417 | 3041447 | chr19 | 3114998 | 3115027 |
| chr19 | 3118927 | 3118956 | chr19 | 3219539 | 3219565 | chr19 | 3296613 | 3296670 |
| chr19 | 3361139 | 3361388 | chr19 | 3562223 | 3562583 | chr19 | 3578138 | 3678223 |
| chr19 | 3659668 | 3659793 | chr19 | 3778130 | 3778394 | chr19 | 3779277 | 3779435 |
| chr19 | 3785649 | 3785835 | chr19 | 3785865 | 3786220 | chr19 | 3821044 | 3821217 |
| chr19 | 3822135 | 3822203 | chr19 | 3834572 | 3834641 | chr19 | 3855407 | 3855595 |
| chr19 | 3966686 | 3966755 | chr19 | 3994540 | 3994568 | chr19 | 4054435 | 4054471 |
| chr19 | 4095471 | 4095514 | chr19 | 4101087 | 4101116 | chr19 | 4110565 | 4110597 |
| chr19 | 4117526 | 4117630 | chr19 | 4305057 | 4305086 | chr19 | 4311273 | 4311412 |
| chr19 | 4548134 | 4548364 | chr19 | 4550246 | 4550330 | chr19 | 4555896 | 4556112 |
| chr19 | 4557098 | 4557235 | chr19 | 4670765 | 4670857 | chr19 | 4789697 | 4789721 |
| chr19 | 4910361 | 4910410 | chr19 | 4944145 | 4944174 | chr19 | 5292812 | 5292844 |
| chr19 | 5338914 | 5339143 | chr19 | 5608619 | 5608569 | chr19 | 5676212 | 5676242 |
| chr19 | 5759744 | 5759774 | chr19 | 5826179 | 5826209 | chr19 | 5910356 | 5910454 |
| chr19 | 5914761 | 5914791 | chr19 | 5914992 | 5915060 | chr19 | 6590325 | 6590478 |
| chr19 | 6658279 | 6658422 | chr19 | 6889423 | 6889439 | chr19 | 7157588 | 7157628 |
| chr19 | 7554718 | 7554749 | chr19 | 7615996 | 7616025 | chr19 | 7635530 | 7635552 |
| chr19 | 7746942 | 7747042 | chr19 | 7747205 | 7747234 | chr19 | 7795012 | 7795244 |
| chr19 | 7853028 | 7853157 | chr19 | 7853361 | 7853460 | chr19 | 8115235 | 8115276 |
| chr19 | 8554173 | 8554218 | chr19 | 8576914 | 8577000 | chr19 | 9420142 | 9420240 |
| chr19 | 9473564 | 9473597 | chr19 | 9473869 | 9474056 | chr19 | 9517609 | 9517771 |
| chr19 | 9608895 | 9609036 | chr19 | 9609319 | 9609436 | chr19 | 9903913 | 9904067 |
| chr19 | 9937369 | 9937386 | chr19 | 10231220 | 10231242 | chr19 | 10246506 | 10246566 |
| chr19 | 10362045 | 10362084 | chr19 | 10398209 | 10398285 | chr19 | 10405972 | 10406159 |
| chr19 | 10406279 | 10406349 | chr19 | 10406806 | 10407029 | chr19 | 10407045 | 10407135 |
| chr19 | 10527165 | 10527243 | chr19 | 10531419 | 10531512 | chr19 | 10531964 | 10531994 |
| chr19 | 10600431 | 10600460 | chr19 | 10602274 | 10602348 | chr19 | 10602565 | 10602864 |
| chr19 | 10610138 | 10610260 | chr19 | 10624751 | 10624852 | chr19 | 10624966 | 10625465 |
| chr19 | 10823678 | 10823721 | chr19 | 11134252 | 11134281 | chr19 | 11138507 | 11138536 |
| chr19 | 11492252 | 11492528 | chr19 | 11591031 | 11591185 | chr19 | 11592710 | 11592750 |
| chr19 | 11593022 | 11593159 | chr19 | 11689460 | 11689564 | chr19 | 11959912 | 11960077 |
| chr19 | 12147437 | 12147461 | chr19 | 12163448 | 12163672 | chr19 | 12163893 | 12163923 |
| chr19 | 12175445 | 12175604 | chr19 | 12175814 | 12176005 | chr19 | 12203028 | 12203656 |
| chr19 | 12267019 | 12267667 | chr19 | 12305839 | 12306193 | chr19 | 12306220 | 12306263 |
| chr19 | 12476492 | 12476556 | chr19 | 12595109 | 12595307 | chr19 | 12595845 | 12595896 |
| chr19 | 12606381 | 12606511 | chr19 | 12750987 | 12751056 | chr19 | 12863412 | 12863520 |
| chr19 | 12952000 | 12952139 | chr19 | 12996169 | 12996280 | chr19 | 13113454 | 13113668 |
| chr19 | 13616696 | 13616956 | chr19 | 13617159 | 13617256 | chr19 | 13618288 | 13618381 |
| chr19 | 13965932 | 13965965 | chr19 | 14085021 | 14085051 | chr19 | 14181305 | 14181846 |
| chr19 | 14584240 | 14584412 | chr19 | 14584537 | 14584775 | chr19 | 14663925 | 14664183 |
| chr19 | 14664479 | 14664561 | chr19 | 15090172 | 15090499 | chr19 | 15121685 | 15121894 |
| chr19 | 15122120 | 15122238 | chr19 | 15288433 | 15288856 | chr19 | 15292384 | 15292499 |
| chr19 | 15342734 | 15343373 | chr19 | 15344107 | 15344130 | chr19 | 16766902 | 16766932 |
| chr19 | 16999599 | 16999782 | chr19 | 17000570 | 17000599 | chr19 | 17007086 | 17007388 |
| chr19 | 17007447 | 17007662 | chr19 | 17008586 | 17008698 | chr19 | 17359350 | 17359459 |
| chr19 | 17392641 | 17392866 | chr19 | 17436061 | 17436203 | chr19 | 12717286 | 17717315 |
| chr19 | 17759224 | 17759423 | chr19 | 17791182 | 17791211 | chr19 | 17943423 | 17943452 |
| chr19 | 17945891 | 17945983 | chr19 | 17947991 | 17948023 | chr19 | 17949094 | 17949123 |
| chr19 | 17958490 | 17958839 | chr19 | 17983537 | 17983665 | chr19 | 18041166 | 18041203 |
| chr19 | 18103711 | 18103741 | chr19 | 18104472 | 18104509 | chr19 | 18271894 | 18271923 |
| chr19 | 18278047 | 18278076 | chr19 | 18331031 | 18331136 | chr19 | 18343439 | 18343569 |
| chr19 | 18343921 | 18343963 | chr19 | 18383251 | 18383351 | chr19 | 18714552 | 18714580 |

TABLE 13-continued

| chr | start | end | chr | start | end | chr | start | end |
|---|---|---|---|---|---|---|---|---|
| chr19 | 18811560 | 18811804 | chr19 | 18856379 | 18856409 | chr19 | 18872825 | 18872900 |
| chr19 | 18899432 | 18899652 | chr19 | 18901828 | 18902095 | chr19 | 18989821 | 18990281 |
| chr19 | 18994887 | 18995206 | chr19 | 19260030 | 19260101 | chr19 | 19261519 | 19261548 |
| chr19 | 19334831 | 19334915 | chr19 | 19636877 | 19636907 | chr19 | 19645834 | 19645925 |
| chr19 | 19651991 | 19652066 | chr19 | 19729251 | 19729395 | chr19 | 19739172 | 19739428 |
| chr19 | 20011955 | 20011992 | chr19 | 20012052 | 20012149 | chr19 | 20188723 | 20188872 |
| chr19 | 20189410 | 20189438 | chr19 | 21646407 | 21646437 | chr19 | 21688814 | 21688893 |
| chr19 | 21769300 | 21769374 | chr19 | 22018523 | 22018724 | chr19 | 22034356 | 22034421 |
| chr19 | 22034447 | 22034813 | chr19 | 22610635 | 22610700 | chr19 | 22715140 | 22715443 |
| chr19 | 23254189 | 23254219 | chr19 | 23257779 | 23258007 | chr19 | 23258306 | 23258559 |
| chr19 | 23258679 | 23258694 | chr19 | 23299748 | 23299824 | chr19 | 23433143 | 23433296 |
| chr19 | 23456615 | 23456881 | chr19 | 23598300 | 23598326 | chr19 | 24154592 | 24154621 |
| chr19 | 24216975 | 24217023 | chr19 | 29284452 | 29284575 | chr19 | 29505153 | 29505183 |
| chr19 | 30015934 | 30015962 | chr19 | 30016025 | 30016712 | chr19 | 30016914 | 30016928 |
| chr19 | 30017452 | 30017509 | chr19 | 30017578 | 30017721 | chr19 | 30017766 | 30018608 |
| chr19 | 30019145 | 30019610 | chr19 | 30019661 | 30019838 | chr19 | 30020093 | 30020473 |
| chr19 | 30185141 | 30186240 | chr19 | 30215542 | 30215571 | chr19 | 30215753 | 30215782 |
| chr19 | 30252296 | 30252333 | chr19 | 30555329 | 30555376 | chr19 | 30562775 | 30563017 |
| chr19 | 30582601 | 30582649 | chr19 | 30637494 | 30637531 | chr19 | 30703436 | 30703469 |
| chr19 | 30713480 | 30713592 | chr19 | 30713686 | 30713706 | chr19 | 30713909 | 30714047 |
| chr19 | 30714403 | 30714433 | chr19 | 30715402 | 30715766 | chr19 | 30716313 | 30716576 |
| chr19 | 30716953 | 30718149 | chr19 | 30718847 | 30718913 | chr19 | 30719449 | 30720067 |
| chr19 | 30865713 | 30866024 | chr19 | 31804724 | 31804754 | chr19 | 31839838 | 31839873 |
| chr19 | 31841937 | 31842389 | chr19 | 32364365 | 32364403 | chr19 | 32380872 | 32380961 |
| chr19 | 32516399 | 32516516 | chr19 | 32715673 | 32715741 | chr19 | 32898335 | 32898490 |
| chr19 | 33167116 | 33167431 | chr19 | 33468018 | 33468055 | chr19 | 33685544 | 33685581 |
| chr19 | 33792159 | 33792524 | chr19 | 33794675 | 33794744 | chr19 | 34112524 | 34112729 |
| chr19 | 34113367 | 34113587 | chr19 | 34114006 | 34114049 | chr19 | 34533139 | 34533169 |
| chr19 | 34973243 | 34973255 | chr19 | 34973656 | 34973697 | chr19 | 35264085 | 35264119 |
| chr19 | 35396251 | 35396370 | chr19 | 35616341 | 35616397 | chr19 | 35781374 | 35781459 |
| chr19 | 35783136 | 35783231 | chr19 | 35797916 | 35797965 | chr19 | 36048575 | 36048771 |
| chr19 | 36049327 | 36049367 | chr19 | 36049397 | 36049462 | chr19 | 36222432 | 36222534 |
| chr19 | 36250029 | 36250134 | chr19 | 36334979 | 36335147 | chr19 | 36347892 | 36348048 |
| chr19 | 36450106 | 36450295 | chr19 | 36523333 | 36523480 | chr19 | 36736027 | 36736057 |
| chr19 | 36736319 | 36736491 | chr19 | 36822324 | 36822466 | chr19 | 36822558 | 36822892 |
| chr19 | 36909073 | 36909348 | chr19 | 36909624 | 36909935 | chr19 | 37095665 | 37095812 |
| chr19 | 37096488 | 37096575 | chr19 | 37263532 | 37263584 | chr19 | 37264222 | 37264421 |
| chr19 | 37288209 | 37288424 | chr19 | 37288607 | 37288765 | chr19 | 37341761 | 37341962 |
| chr19 | 37407127 | 37407443 | chr19 | 37464048 | 37464567 | chr19 | 37464667 | 37464696 |
| chr19 | 37569289 | 37569554 | chr19 | 37702086 | 37702169 | chr19 | 37808445 | 37808485 |
| chr19 | 37959874 | 37959963 | chr19 | 37997433 | 37998138 | chr19 | 38042365 | 38042693 |
| chr19 | 38085254 | 38086066 | chr19 | 38146062 | 38146247 | chr19 | 38146457 | 38146568 |
| chr19 | 38182884 | 38182959 | chr19 | 38183112 | 38183299 | chr19 | 38308080 | 38308336 |
| chr19 | 38308395 | 38308466 | chr19 | 38441488 | 38441518 | chr19 | 38481044 | 38481217 |
| chr19 | 38747159 | 38747491 | chr19 | 38747748 | 38747767 | chr19 | 38755272 | 38755344 |
| chr19 | 38782559 | 38782589 | chr19 | 38789218 | 38789288 | chr19 | 38873935 | 38873965 |
| chr19 | 38905548 | 38905702 | chr19 | 38974232 | 38974262 | chr19 | 39135434 | 39135454 |
| chr19 | 39306433 | 39306545 | chr19 | 39650791 | 39650967 | chr19 | 39687756 | 39687844 |
| chr19 | 39754874 | 39755232 | chr19 | 39755265 | 39755358 | chr19 | 39816936 | 39817085 |
| chr19 | 39993477 | 39993656 | chr19 | 39997688 | 39997732 | chr19 | 39997749 | 39997813 |
| chr19 | 40006187 | 40006306 | chr19 | 40006576 | 40006639 | chr19 | 40724000 | 40724263 |
| chr19 | 40762943 | 40762972 | chr19 | 40829079 | 40829211 | chr19 | 40829793 | 40830032 |
| chr19 | 40902425 | 40902812 | chr19 | 40951175 | 40951206 | chr19 | 40951679 | 40951762 |
| chr19 | 41018510 | 41019031 | chr19 | 41025539 | 41025683 | chr19 | 41059909 | 41060306 |
| chr19 | 41073587 | 41073677 | chr19 | 41119177 | 41119276 | chr19 | 41119371 | 41119408 |
| chr19 | 41354666 | 41354722 | chr19 | 41641831 | 41641886 | chr19 | 41698787 | 41698920 |
| chr19 | 41919917 | 41919971 | chr19 | 42028502 | 42028549 | chr19 | 42408300 | 42408330 |
| chr19 | 42460961 | 42461113 | chr19 | 42827982 | 42828084 | chr19 | 42856453 | 42856483 |
| chr19 | 42911568 | 42911598 | chr19 | 44203830 | 44203877 | chr19 | 44405908 | 44406087 |
| chr19 | 44599783 | 44599803 | chr19 | 44905499 | 44905529 | chr19 | 44952282 | 44952881 |
| chr19 | 45003211 | 45003323 | chr19 | 45300144 | 45300197 | chr19 | 45570401 | 45570450 |
| chr19 | 45574465 | 45574495 | chr19 | 45574773 | 45574888 | chr19 | 45601380 | 45601410 |
| chr19 | 45655400 | 45655556 | chr19 | 45655648 | 45656363 | chr19 | 45656682 | 45656742 |
| chr19 | 45656791 | 45656913 | chr19 | 45657212 | 45657284 | chr19 | 45810102 | 45810267 |
| chr19 | 45835238 | 45835268 | chr19 | 45888946 | 45889224 | chr19 | 45889316 | 45889397 |
| chr19 | 45997528 | 45997584 | chr19 | 46002048 | 46002320 | chr19 | 46234845 | 46234887 |
| chr19 | 46379914 | 46380148 | chr19 | 46404522 | 46404601 | chr19 | 46916725 | 46916987 |
| chr19 | 46917061 | 46917075 | chr19 | 46930129 | 46930200 | chr19 | 46974552 | 46974608 |
| chr19 | 46992718 | 46992866 | chr19 | 46993164 | 46993260 | chr19 | 46993282 | 46993388 |
| chr19 | 46996501 | 46996514 | chr19 | 46996578 | 46996838 | chr19 | 47152978 | 47152990 |
| chr19 | 47200361 | 47200536 | chr19 | 47776713 | 47776742 | chr19 | 47933311 | 47933732 |
| chr19 | 47951288 | 47951318 | chr19 | 48003607 | 48003714 | chr19 | 48076642 | 48076672 |
| chr19 | 48137171 | 48137307 | chr19 | 48151265 | 48151337 | chr19 | 48614843 | 48614873 |
| chr19 | 48771551 | 48771600 | chr19 | 48800603 | 48800769 | chr19 | 48857808 | 48857831 |
| chr19 | 48902848 | 48902878 | chr19 | 48918100 | 48918379 | chr19 | 49119229 | 49119259 |
| chr19 | 49127373 | 49127674 | chr19 | 49180462 | 49180558 | chr19 | 49256396 | 49256438 |
| chr19 | 49399218 | 49399310 | chr19 | 49402471 | 49402551 | chr19 | 49575460 | 49575474 |
| chr19 | 49890887 | 49890908 | chr19 | 49935736 | 49936174 | chr19 | 49936864 | 49936894 |

TABLE 13-continued

| chr | start | end | chr | start | end | chr | start | end |
|---|---|---|---|---|---|---|---|---|
| chr19 | 50028397 | 50028530 | chr19 | 50049718 | 50049746 | chr19 | 50216042 | 50216072 |
| chr19 | 50243339 | 50243379 | chr19 | 50304736 | 50304766 | chr19 | 50316244 | 50316468 |
| chr19 | 50353394 | 50353574 | chr19 | 50553680 | 50553709 | chr19 | 50553997 | 50554510 |
| chr19 | 50816431 | 50816474 | chr19 | 50833828 | 50833863 | chr19 | 50898558 | 50898583 |
| chr19 | 50938547 | 50938691 | chr19 | 51041149 | 51041189 | chr19 | 51161225 | 51161255 |
| chr19 | 51162197 | 51162253 | chr19 | 51162428 | 51162527 | chr19 | 51171219 | 51171275 |
| chr19 | 51171828 | 51171860 | chr19 | 51227719 | 51227785 | chr19 | 51228049 | 51228079 |
| chr19 | 51228369 | 51228507 | chr19 | 51304554 | 51304602 | chr19 | 51520423 | 51520453 |
| chr19 | 51715329 | 51715359 | chr19 | 51830845 | 51831002 | chr19 | 51831121 | 51831128 |
| chr19 | 51831360 | 51831390 | chr19 | 51925127 | 51925272 | chr19 | 52097689 | 52097732 |
| chr19 | 52207254 | 52207362 | chr19 | 52222523 | 52222923 | chr19 | 52391235 | 52391264 |
| chr19 | 52452316 | 52452335 | chr19 | 52552104 | 52552119 | chr19 | 52715963 | 52715992 |
| chr19 | 52839588 | 52839717 | chr19 | 52839742 | 52839938 | chr19 | 52872942 | 52873440 |
| chr19 | 52956805 | 52956848 | chr19 | 53028928 | 53028952 | chr19 | 53031185 | 53031215 |
| chr19 | 53073563 | 53073772 | chr19 | 53073820 | 53073987 | chr19 | 53141648 | 53141745 |
| chr19 | 53193858 | 53193893 | chr19 | 53194281 | 53194396 | chr19 | 53204758 | 53204798 |
| chr19 | 53496649 | 53496786 | chr19 | 53496814 | 53496846 | chr19 | 53561668 | 53561733 |
| chr19 | 53635952 | 53636091 | chr19 | 53661647 | 53661865 | chr19 | 53662194 | 53662694 |
| chr19 | 53696414 | 53696580 | chr19 | 53700596 | 53700693 | chr19 | 53757895 | 53758247 |
| chr19 | 53811858 | 53811988 | chr19 | 53836954 | 53836975 | chr19 | 53837377 | 53837432 |
| chr19 | 53970501 | 53970643 | chr19 | 53970968 | 53971039 | chr19 | 53971110 | 53971157 |
| chr19 | 54023887 | 54024196 | chr19 | 54024521 | 54024553 | chr19 | 54024613 | 54024884 |
| chr19 | 54369555 | 54369681 | chr19 | 54411125 | 54411168 | chr19 | 54411556 | 54411586 |
| chr19 | 54412873 | 54412985 | chr19 | 54481771 | 54481968 | chr19 | 54483173 | 54483305 |
| chr19 | 54483365 | 54483546 | chr19 | 54485403 | 54485646 | chr19 | 54485673 | 54485823 |
| chr19 | 54850630 | 54850659 | chr19 | 55598811 | 55598888 | chr19 | 55629883 | 55630028 |
| chr19 | 56159273 | 56159499 | chr19 | 56189937 | 56189966 | chr19 | 56201643 | 56201938 |
| chr19 | 56588656 | 56588780 | chr19 | 56728678 | 56728788 | chr19 | 56879501 | 56880008 |
| chr19 | 56904740 | 56905203 | chr19 | 56915320 | 56915428 | chr19 | 56988557 | 56988663 |
| chr19 | 56989528 | 56989625 | chr19 | 56989697 | 56989754 | chr19 | 57050463 | 57050493 |
| chr19 | 57149579 | 57149619 | chr19 | 57154885 | 57155017 | chr19 | 57182990 | 57183126 |
| chr19 | 57276656 | 57276700 | chr19 | 57323825 | 57323854 | chr19 | 57610896 | 57610985 |
| chr19 | 57617522 | 57617715 | chr19 | 57617832 | 57618121 | chr19 | 57683148 | 57683162 |
| chr19 | 57683240 | 57683295 | chr19 | 57862395 | 57862783 | chr19 | 58011124 | 58011281 |
| chr19 | 58038924 | 58038969 | chr19 | 58095006 | 58095835 | chr19 | 58111632 | 58111783 |
| chr19 | 58125544 | 58125881 | chr19 | 58144494 | 58144701 | chr19 | 58219916 | 58220392 |
| chr19 | 58220516 | 58220832 | chr19 | 58238326 | 58238738 | chr19 | 58238988 | 58239088 |
| chr19 | 58400079 | 58400175 | chr19 | 58400417 | 58400518 | chr19 | 58458754 | 58458890 |
| chr19 | 58458979 | 58459201 | chr19 | 58514518 | 58514552 | chr19 | 58520739 | 58520941 |
| chr19 | 58545145 | 58545387 | chr19 | 58545578 | 58545589 | chr19 | 58545652 | 58545837 |
| chr19 | 58609254 | 58609359 | chr19 | 58609473 | 58609525 | chr19 | 58609713 | 58609854 |
| chr19 | 58629975 | 58629975 | chr19 | 58661894 | 58662094 | chr19 | 58666171 | 58666313 |
| chr19 | 58740086 | 58740118 | chr19 | 58874831 | 58874951 | chr19 | 58951271 | 58951400 |
| chr19 | 58951526 | 58951916 | chr19 | 58964180 | 58964266 | chr20 | 118577 | 118751 |
| chr20 | 291148 | 291162 | chr20 | 291221 | 291373 | chr20 | 400007 | 400087 |
| chr20 | 401153 | 401183 | chr20 | 401591 | 401756 | chr20 | 590434 | 590502 |
| chr20 | 592405 | 592449 | chr20 | 644182 | 644351 | chr20 | 644407 | 644787 |
| chr20 | 799104 | 799146 | chr20 | 982749 | 982798 | chr20 | 982892 | 982989 |
| chr20 | 1094651 | 1094682 | chr20 | 1206855 | 1207034 | chr20 | 1783761 | 1784305 |
| chr20 | 1876110 | 1876176 | chr20 | 1975357 | 1975386 | chr20 | 2539331 | 2539771 |
| chr20 | 2668770 | 2668922 | chr20 | 2780753 | 2780273 | chr20 | 2780893 | 2781452 |
| chr20 | 2781731 | 2781761 | chr20 | 2785659 | 2785866 | chr20 | 2785955 | 2786060 |
| chr20 | 3027758 | 3027785 | chr20 | 3052583 | 3052836 | chr20 | 3073561 | 3073899 |
| chr20 | 3154172 | 3154204 | chr20 | 3204870 | 3204952 | chr20 | 3220893 | 3220943 |
| chr20 | 3229576 | 3229612 | chr20 | 3641774 | 3641937 | chr20 | 3663020 | 3663174 |
| chr20 | 3762152 | 3762181 | chr20 | 3762407 | 3762436 | chr20 | 4040731 | 4040871 |
| chr20 | 4085057 | 4085087 | chr20 | 4229402 | 4229432 | chr20 | 4229786 | 4230600 |
| chr20 | 4803070 | 4803650 | chr20 | 4803921 | 4804008 | chr20 | 4804566 | 4804732 |
| chr20 | 5296172 | 5296900 | chr20 | 5297226 | 5297418 | chr20 | 5610356 | 5610386 |
| chr20 | 6022797 | 6023045 | chr20 | 6023268 | 6023310 | chr20 | 6748925 | 6749036 |
| chr20 | 7980362 | 7980392 | chr20 | 8112378 | 8112408 | chr20 | 8112739 | 8113022 |
| chr20 | 8113557 | 8113605 | chr20 | 9487385 | 9487719 | chr20 | 9487789 | 9487997 |
| chr20 | 9488376 | 9488848 | chr20 | 9489070 | 9489214 | chr20 | 9489424 | 9489708 |
| chr20 | 9495271 | 9495509 | chr20 | 9496330 | 9496530 | chr20 | 9496581 | 9496833 |
| chr20 | 9497035 | 9497109 | chr20 | 10198289 | 10198600 | chr20 | 10198941 | 10198945 |
| chr20 | 13200599 | 13200634 | chr20 | 16555010 | 16555030 | chr20 | 17206513 | 17206747 |
| chr20 | 17207874 | 17207930 | chr20 | 17208585 | 17208620 | chr20 | 18039823 | 18039897 |
| chr20 | 18073417 | 18073461 | chr20 | 18448999 | 18449076 | chr20 | 19739613 | 19739696 |
| chr20 | 19928306 | 19928461 | chr20 | 20344498 | 20344559 | chr20 | 20347460 | 20347709 |
| chr20 | 20347737 | 20348154 | chr20 | 20348526 | 20348605 | chr20 | 20349153 | 20349255 |
| chr20 | 20349574 | 20349604 | chr20 | 21080714 | 21080956 | chr20 | 21081029 | 21081844 |
| chr20 | 21082095 | 21082123 | chr20 | 21082216 | 21082253 | chr20 | 21082532 | 21082917 |
| chr20 | 21083421 | 21084361 | chr20 | 21085831 | 21085864 | chr20 | 21086195 | 21086451 |
| chr20 | 21086866 | 21087188 | chr20 | 21372174 | 21372192 | chr20 | 21372295 | 21372725 |
| chr20 | 21376250 | 21376336 | chr20 | 21376703 | 21376733 | chr20 | 21376877 | 21377128 |
| chr20 | 21377474 | 21377640 | chr20 | 21377738 | 21378551 | chr20 | 21486375 | 21486659 |
| chr20 | 21486786 | 21486881 | chr20 | 21487153 | 21487302 | chr20 | 21487367 | 21487581 |
| chr20 | 21488158 | 21488351 | chr20 | 21489240 | 21489446 | chr20 | 21489622 | 21489703 |

TABLE 13-continued

| chr | start | end | chr | start | end | chr | start | end |
|---|---|---|---|---|---|---|---|---|
| chr20 | 21490175 | 21490762 | chr20 | 21490815 | 21491345 | chr20 | 21492378 | 21492409 |
| chr20 | 21492508 | 21492825 | chr20 | 21493308 | 21493993 | chr20 | 21494531 | 21494703 |
| chr20 | 21495942 | 21495986 | chr20 | 21496260 | 21496294 | chr20 | 21496684 | 21497136 |
| chr20 | 21497413 | 21498638 | chr20 | 21499961 | 21500134 | chr20 | 21501445 | 21501724 |
| chr20 | 21502037 | 21502144 | chr20 | 21502590 | 21502699 | chr20 | 21502838 | 21503117 |
| chr20 | 21503455 | 21503773 | chr20 | 21682399 | 21682456 | chr20 | 21683311 | 21683651 |
| chr20 | 21685385 | 21685526 | chr20 | 21686235 | 21686677 | chr20 | 21687009 | 21687382 |
| chr20 | 21689956 | 21690185 | chr20 | 21694499 | 21694529 | chr20 | 21695088 | 21695273 |
| chr20 | 21695306 | 21695357 | chr20 | 21748445 | 21748491 | chr20 | 22401392 | 22401421 |
| chr20 | 22557396 | 22557675 | chr20 | 22557979 | 22558114 | chr20 | 22558637 | 22558669 |
| chr20 | 22559645 | 22559690 | chr20 | 22562721 | 22562840 | chr20 | 22563563 | 22563602 |
| chr20 | 22564235 | 22564265 | chr20 | 22566961 | 22566990 | chr20 | 23015917 | 23015946 |
| chr20 | 23029110 | 23029151 | chr20 | 23029589 | 23030085 | chr20 | 23030292 | 23030352 |
| chr20 | 23031548 | 23031692 | chr20 | 24450231 | 24450513 | chr20 | 24450820 | 24451019 |
| chr20 | 24451450 | 24451592 | chr20 | 24726701 | 24726825 | chr20 | 25058385 | 25058616 |
| chr20 | 25061746 | 25061788 | chr20 | 25061979 | 25062311 | chr20 | 25062511 | 25062645 |
| chr20 | 25062708 | 25062817 | chr20 | 25062871 | 25062880 | chr20 | 25063780 | 25063906 |
| chr20 | 25063994 | 25064458 | chr20 | 25065179 | 25065395 | chr20 | 25223141 | 2522327Z |
| chr20 | 25230509 | 25230534 | chr20 | 25230774 | 25230799 | chr20 | 25334513 | 25334650 |
| chr20 | 26188812 | 26188961 | chr20 | 26190313 | 26190361 | chr20 | 29956013 | 29956042 |
| chr20 | 29956570 | 29956599 | chr20 | 30101723 | 30101743 | chr20 | 30297090 | 30297184 |
| chr20 | 30582750 | 30582978 | chr20 | 30639141 | 30639319 | chr20 | 30639632 | 30639847 |
| chr20 | 30640106 | 30640270 | chr20 | 30778024 | 30778313 | chr20 | 31035471 | 31035518 |
| chr20 | 31115683 | 31115799 | chr20 | 31151769 | 31151799 | chr20 | 31207211 | 31207283 |
| chr20 | 31282879 | 31282903 | chr20 | 32301797 | 32301953 | chr20 | 32450398 | 32450427 |
| chr20 | 33547565 | 33547585 | chr20 | 33574914 | 33574992 | chr20 | 34041981 | 34042004 |
| chr20 | 34148020 | 34148254 | chr20 | 34188617 | 34188631 | chr20 | 34188748 | 34189088 |
| chr20 | 34189167 | 34189391 | chr20 | 34189680 | 34189910 | chr20 | 35742487 | 35742607 |
| chr20 | 36531799 | 36531910 | chr20 | 36781324 | 36781354 | chr20 | 37302697 | 37303343 |
| chr20 | 37351793 | 37352515 | chr20 | 37352607 | 37352626 | chr20 | 37353193 | 37353236 |
| chr20 | 37353455 | 37353718 | chr20 | 37354145 | 37354831 | chr20 | 37354994 | 37355202 |
| chr20 | 37355847 | 37356042 | chr20 | 37356169 | 37356827 | chr20 | 37357216 | 37357353 |
| chr20 | 37357825 | 37358190 | chr20 | 37434552 | 37434721 | chr20 | 37434737 | 37434744 |
| chr20 | 37435104 | 37435218 | chr20 | 37435488 | 37435860 | chr20 | 39316203 | 39316322 |
| chr20 | 39316984 | 39317392 | chr20 | 39317750 | 39318166 | chr20 | 39318383 | 39318415 |
| chr20 | 39319126 | 39319203 | chr20 | 39319515 | 39319653 | chr20 | 39995146 | 39995813 |
| chr20 | 40743859 | 40743888 | chr20 | 41817786 | 41817915 | chr20 | 41818008 | 41818085 |
| chr20 | 41818567 | 41818748 | chr20 | 41818805 | 41818914 | chr20 | 42136330 | 42136411 |
| chr20 | 42218577 | 42218664 | chr20 | 42543754 | 42543853 | chr20 | 42544091 | 42544533 |
| chr20 | 42544728 | 42544984 | chr20 | 42852751 | 42852773 | chr20 | 42876525 | 42876575 |
| chr20 | 43438071 | 43438085 | chr20 | 43438335 | 43438466 | chr20 | 43438982 | 43439022 |
| chr20 | 43439291 | 43439510 | chr20 | 44003765 | 44003811 | chr20 | 44452731 | 44453063 |
| chr20 | 44519077 | 44519107 | chr20 | 44602074 | 44602099 | chr20 | 44602339 | 44602364 |
| chr20 | 44639181 | 44639496 | chr20 | 44640338 | 44640367 | chr20 | 44660750 | 44660877 |
| chr20 | 44686423 | 44686614 | chr20 | 44686628 | 44686762 | chr20 | 44746484 | 44746781 |
| chr20 | 44803174 | 44803675 | chr20 | 44875240 | 44875411 | chr20 | 44880041 | 44880076 |
| chr20 | 44937202 | 44937411 | chr20 | 44937426 | 44937643 | chr20 | 44941518 | 44941661 |
| chr20 | 45142000 | 45142038 | chr20 | 45142152 | 45142272 | chr20 | 45279854 | 45279981 |
| chr20 | 45280040 | 45280302 | chr20 | 45280344 | 45280428 | chr20 | 45337804 | 45337945 |
| chr20 | 45524523 | 45524553 | chr20 | 47247239 | 47247450 | chr20 | 47274032 | 47274062 |
| chr20 | 47296109 | 47296231 | chr20 | 47443729 | 47443936 | chr20 | 47443945 | 47444282 |
| chr20 | 47905426 | 47905603 | chr20 | 47934824 | 47935268 | chr20 | 47935495 | 47935567 |
| chr20 | 47935928 | 47936027 | chr20 | 48184381 | 48184435 | chr20 | 49204179 | 49204449 |
| chr20 | 49261803 | 49262104 | chr20 | 49358357 | 49358396 | chr20 | 49377899 | 49378043 |
| chr20 | 49381160 | 49381240 | chr20 | 49575909 | 49575939 | chr20 | 49639777 | 49639856 |
| chr20 | 49639883 | 49639996 | chr20 | 49640095 | 49640157 | chr20 | 49969348 | 49969515 |
| chr20 | 50160801 | 50160905 | chr20 | 50383384 | 50383423 | chr20 | 50384767 | 50384896 |
| chr20 | 50720437 | 50721200 | chr20 | 50721235 | 50721670 | chr20 | 50721989 | 50722035 |
| chr20 | 50722095 | 50722193 | chr20 | 50722598 | 50722821 | chr20 | 51589766 | 51589908 |
| chr20 | 52226337 | 52226366 | chr20 | 52311463 | 52311513 | chr20 | 52789445 | 52789475 |
| chr20 | 52789853 | 52789948 | chr20 | 52790082 | 52790155 | chr20 | 53092192 | 53092376 |
| chr20 | 53093085 | 53093115 | chr20 | 54578507 | 54578725 | chr20 | 54579892 | 54579958 |
| chr20 | 54580070 | 54580323 | chr20 | 54580622 | 54580691 | chr20 | 55008041 | 55008194 |
| chr20 | 55071640 | 55071717 | chr20 | 55200035 | 55200310 | chr20 | 55200616 | 55200706 |
| chr20 | 55200922 | 55201092 | chr20 | 55201764 | 55202068 | chr20 | 55202359 | 55202626 |
| chr20 | 55202826 | 55203107 | chr20 | 55204322 | 55204604 | chr20 | 55204966 | 55205000 |
| chr20 | 55206294 | 55206393 | chr20 | 55206739 | 55206774 | chr20 | 56499496 | 55499709 |
| chr20 | 55500016 | 55500085 | chr20 | 55500441 | 55500720 | chr20 | 55693527 | 55693625 |
| chr20 | 55841134 | 55841356 | chr20 | 55842096 | 55842189 | chr20 | 56766160 | 56766190 |
| chr20 | 56803398 | 56803441 | chr20 | 56803842 | 56803920 | chr20 | 57089452 | 57089459 |
| chr20 | 57090104 | 57090173 | chr20 | 57224842 | 57225079 | chr20 | 57225219 | 57225307 |
| chr20 | 57484406 | 57484445 | chr20 | 58179809 | 58179854 | chr20 | 58180214 | 58180402 |
| chr20 | 58508887 | 58508943 | chr20 | 59804170 | 59804235 | chr20 | 59826192 | 59826221 |
| chr20 | 59826962 | 59826977 | chr20 | 59828341 | 59828407 | chr20 | 59880433 | 59880477 |
| chr20 | 59910175 | 59910346 | chr20 | 59973028 | 59973072 | chr20 | 50202594 | 60202624 |
| chr20 | 60235333 | 60235526 | chr20 | 60238381 | 60238472 | chr20 | 50238877 | 60238980 |
| chr20 | 60243944 | 60244107 | chr20 | 60329584 | 60329661 | chr20 | 60333880 | 60333969 |
| chr20 | 60359849 | 60359879 | chr20 | 60375036 | 60375070 | chr20 | 60439634 | 60439755 |

TABLE 13-continued

| chr | start | end | chr | start | end | chr | start | end |
|---|---|---|---|---|---|---|---|---|
| chr20 | 60453925 | 60454091 | chr20 | 60477306 | 60477537 | chr20 | 60485374 | 60485425 |
| chr20 | 60503030 | 60503060 | chr20 | 60545561 | 60545792 | chr20 | 60620122 | 60620557 |
| chr20 | 60772853 | 60773878 | chr20 | 60789965 | 60790124 | chr20 | 60892164 | 60892222 |
| chr20 | 60926019 | 60926049 | chr20 | 60970953 | 60970983 | chr20 | 60983859 | 60984010 |
| chr20 | 60984341 | 60984465 | chr20 | 61288068 | 61288156 | chr20 | 61288463 | 61288534 |
| chr20 | 61294693 | 61294857 | chr20 | 61340581 | 61340689 | chr20 | 61412313 | 51412438 |
| chr20 | 61505881 | 61506330 | chr20 | 61532546 | 61532605 | chr20 | 61560418 | 61560460 |
| chr20 | 61560529 | 61560922 | chr20 | 61586771 | 61585922 | chr20 | 61585990 | 61586004 |
| chr20 | 61636876 | 61636890 | chr20 | 61637468 | 61637648 | chr20 | 61637736 | 61637956 |
| chr20 | 61638221 | 61638469 | chr20 | 61638535 | 61638631 | chr20 | 61703710 | 61703761 |
| chr20 | 61703846 | 61703875 | chr20 | 61714591 | 61714621 | chr20 | 61734420 | 61734481 |
| chr20 | 61747894 | 61747934 | chr20 | 61763598 | 61763628 | chr20 | 61765285 | 61765425 |
| chr20 | 61808181 | 61808270 | chr20 | 61808667 | 61809005 | chr20 | 61809219 | 61809631 |
| chr20 | 61809841 | 61810089 | chr20 | 61823170 | 61823195 | chr20 | 61862380 | 61862452 |
| chr20 | 61885247 | 61885462 | chr20 | 61886068 | 61886203 | chr20 | 61886257 | 61886258 |
| chr20 | 61885725 | 61885755 | chr20 | 61974191 | 61974354 | chr20 | 51980860 | 61980975 |
| chr20 | 62031173 | 62031234 | chr20 | 62032058 | 62032095 | chr20 | 62037559 | 62037598 |
| chr20 | 62046227 | 62046421 | chr20 | 62058700 | 62058786 | chr20 | 62090524 | 62090621 |
| chr20 | 62097666 | 62097695 | chr20 | 62115187 | 62115266 | chr20 | 62119339 | 62119618 |
| chr20 | 62119923 | 62120171 | chr20 | 62126118 | 62126429 | chr20 | 62157229 | 62157307 |
| chr20 | 62165631 | 62165762 | chr20 | 62167554 | 62167584 | chr20 | 62170179 | 62170209 |
| chr20 | 62172945 | 62173055 | chr20 | 62185386 | 62185444 | chr20 | 62260862 | 62260905 |
| chr20 | 62284487 | 62284615 | chr20 | 62314848 | 62314955 | chr20 | 62321206 | 62321341 |
| chr20 | 62321638 | 62321881 | chr20 | 62340321 | 62340442 | chr20 | 62383218 | 62383289 |
| chr20 | 62461349 | 62461475 | chr20 | 62488293 | 62488350 | chr20 | 62631442 | 62631562 |
| chr20 | 62680657 | 62680739 | chr20 | 62716014 | 62715069 | chr20 | 62786577 | 62786726 |
| chr20 | 62795643 | 62795672 | chr21 | 22370332 | 22370458 | chr21 | 22370688 | 22370718 |
| chr21 | 26934368 | 26934786 | chr21 | 27011773 | 27011807 | chr21 | 27012373 | 27012431 |
| chr21 | 27944995 | 27945081 | chr21 | 27945693 | 27945722 | chr21 | 28216634 | 28217690 |
| chr21 | 28218774 | 28219045 | chr21 | 28338836 | 28338887 | chr21 | 28339247 | 28339501 |
| chr21 | 28339892 | 28340048 | chr21 | 28340063 | 28340318 | chr21 | 31015201 | 31015231 |
| chr21 | 31311404 | 31311553 | chr21 | 31312080 | 31312105 | chr21 | 31312313 | 31312409 |
| chr21 | 32253745 | 32253774 | chr21 | 33043985 | 33044051 | chr21 | 33244921 | 33245040 |
| chr21 | 33245683 | 33245718 | chr21 | 33246009 | 33246190 | chr21 | 33627549 | 33627569 |
| chr21 | 33721756 | 33721824 | chr21 | 33785288 | 33785325 | chr21 | 33983236 | 33983332 |
| chr21 | 34392206 | 34392403 | chr21 | 34392437 | 34392566 | chr21 | 34395302 | 34396269 |
| chr21 | 34396795 | 34397091 | chr21 | 34398070 | 34398634 | chr21 | 34398933 | 34399258 |
| chr21 | 34399442 | 34400104 | chr21 | 34400232 | 34400258 | chr21 | 34401185 | 34401392 |
| chr21 | 34442595 | 34442665 | chr21 | 34443103 | 34443262 | chr21 | 34443509 | 34443686 |
| chr21 | 34444893 | 34443956 | chr21 | 34444163 | 34444362 | chr21 | 34444445 | 34444598 |
| chr21 | 35051195 | 35051231 | chr21 | 36041985 | 36042028 | chr21 | 36042092 | 36042238 |
| chr21 | 36042658 | 36042861 | chr21 | 37527928 | 37527958 | chr21 | 37758570 | 37758611 |
| chr21 | 37775034 | 37775141 | chr21 | 38064457 | 38064683 | chr21 | 38064966 | 38065522 |
| chr21 | 38065955 | 38066112 | chr21 | 38067203 | 38067233 | chr21 | 38068178 | 38068229 |
| chr21 | 38068647 | 38068783 | chr21 | 38069093 | 38069203 | chr21 | 38069459 | 38069496 |
| chr21 | 38069854 | 38070162 | chr21 | 38070705 | 38070765 | chr21 | 38071791 | 38071905 |
| chr21 | 38073007 | 38073070 | chr21 | 38073300 | 38073525 | chr21 | 38073616 | 38073860 |
| chr21 | 38078415 | 38078487 | chr21 | 38079988 | 38080062 | chr21 | 38080175 | 38080386 |
| chr21 | 38080551 | 38080684 | chr21 | 38081085 | 38081192 | chr21 | 38081666 | 38081835 |
| chr21 | 38082042 | 38082072 | chr21 | 38082930 | 38083196 | chr21 | 38092179 | 38092221 |
| chr21 | 38119904 | 38120312 | chr21 | 38638504 | 38638526 | chr21 | 38935478 | 38935549 |
| chr21 | 39047776 | 39047838 | chr21 | 39870612 | 39870641 | chr21 | 40033619 | 40033648 |
| chr21 | 40033877 | 40033906 | chr21 | 40034756 | 40034785 | chr21 | 40984685 | 40984900 |
| chr21 | 42617963 | 42617995 | chr21 | 42649172 | 42649202 | chr21 | 43186698 | 43186889 |
| chr21 | 43240082 | 43240112 | chr21 | 43256565 | 43256603 | chr21 | 43376373 | 43376403 |
| chr21 | 43393528 | 43393713 | chr21 | 43485279 | 43485348 | chr21 | 43786683 | 43786713 |
| chr21 | 43991463 | 43991493 | chr21 | 44283581 | 44283774 | chr21 | 44494941 | 44495155 |
| chr21 | 44514762 | 44514791 | chr21 | 44524441 | 44524470 | chr21 | 44837088 | 44837213 |
| chr21 | 44847591 | 44847622 | chr21 | 44866603 | 44866711 | chr21 | 44886709 | 44886870 |
| chr21 | 45148615 | 45148758 | chr21 | 45195149 | 45195319 | chr21 | 45271643 | 45271688 |
| chr21 | 45273717 | 45273913 | chr21 | 45290014 | 45290044 | chr21 | 45508617 | 45508647 |
| chr21 | 45521343 | 45521438 | chr21 | 45717477 | 45717548 | chr21 | 45791079 | 45791109 |
| chr21 | 45847832 | 45847973 | chr21 | 46036642 | 46036767 | chr21 | 46125967 | 46126267 |
| chr21 | 46126387 | 46126427 | chr21 | 46126567 | 46126721 | chr21 | 46127039 | 46127094 |
| chr21 | 46127542 | 46127692 | chr21 | 46126902 | 46128938 | chr21 | 46129444 | 46129485 |
| chr21 | 46193414 | 46193542 | chr21 | 46257116 | 46257273 | chr21 | 46310428 | 46310491 |
| chr21 | 46318286 | 46318343 | chr21 | 46319156 | 46319459 | chr21 | 46359187 | 46359248 |
| chr21 | 46452374 | 46452539 | chr21 | 46677734 | 46677796 | chr21 | 46825825 | 46826067 |
| chr21 | 46847654 | 46847684 | chr21 | 46863658 | 46863708 | chr21 | 46925790 | 46925925 |
| chr21 | 46926459 | 46926565 | chr21 | 46935739 | 46935936 | chr21 | 47010409 | 47010451 |
| chr21 | 47062753 | 47062825 | chr21 | 47063538 | 47063962 | chr21 | 47064250 | 47064377 |
| chr21 | 47404174 | 47404325 | chr21 | 47504861 | 47504895 | chr21 | 47518776 | 47518814 |
| chr21 | 47717560 | 47717589 | chr21 | 47746270 | 47746393 | chr21 | 47081932 | 47081935 |
| chr22 | 17082989 | 17083003 | chr22 | 17083396 | 17083410 | chr22 | 17601086 | 17601133 |
| chr22 | 17601260 | 17601368 | chr22 | 17602511 | 17602624 | chr22 | 17850454 | 17850621 |
| chr22 | 18009985 | 18010105 | chr22 | 18328127 | 18328268 | chr22 | 18340822 | 18340868 |
| chr22 | 18627328 | 18627433 | chr22 | 19017532 | 19017567 | chr22 | 19117564 | 19117594 |
| chr22 | 19136907 | 19136936 | chr22 | 19137859 | 19137888 | chr22 | 19138109 | 19138138 |

TABLE 13-continued

| chr | start | end | chr | start | end | chr | start | end |
|---|---|---|---|---|---|---|---|---|
| chr22 | 19510799 | 19510946 | chr22 | 19511142 | 19511455 | chr22 | 19511542 | 19511567 |
| chr22 | 19511849 | 19511875 | chr22 | 19702265 | 19702410 | chr22 | 19706171 | 19706677 |
| chr22 | 19742834 | 19742969 | chr22 | 19748644 | 19748908 | chr22 | 20229079 | 20229239 |
| chr22 | 20792482 | 20792641 | chr22 | 20940868 | 20940898 | chr22 | 21153867 | 21154000 |
| chr22 | 21299605 | 21299635 | chr22 | 21304979 | 21305007 | chr22 | 21368587 | 21368617 |
| chr22 | 21977314 | 21977347 | chr22 | 21982792 | 21982972 | chr22 | 22005794 | 22006759 |
| chr22 | 22058203 | 22058238 | chr22 | 22862787 | 22862862 | chr22 | 22901105 | 22901455 |
| chr22 | 23791402 | 23791432 | chr22 | 23801459 | 23801610 | chr22 | 23991237 | 23991272 |
| chr22 | 24145484 | 24145513 | chr22 | 24179940 | 24179982 | chr22 | 24180687 | 24180766 |
| chr22 | 24560375 | 24560526 | chr22 | 24820330 | 24820396 | chr22 | 25678748 | 25678868 |
| chr22 | 25679043 | 25679249 | chr22 | 25679268 | 25679337 | chr22 | 25817107 | 25817180 |
| chr22 | 25817458 | 25817612 | chr22 | 27053194 | 27053250 | chr22 | 28198569 | 28198605 |
| chr22 | 28371649 | 28371679 | chr22 | 28838200 | 28838292 | chr22 | 28838509 | 28838551 |
| chr22 | 28839122 | 28839263 | chr22 | 29091824 | 29091853 | chr22 | 29445752 | 29445923 |
| chr22 | 29876191 | 29876220 | chr22 | 29877223 | 29877299 | chr22 | 29977649 | 29977769 |
| chr22 | 30084358 | 30084388 | chr22 | 30090739 | 30090769 | chr22 | 30116904 | 30117146 |
| chr22 | 30158330 | 30158365 | chr22 | 30476197 | 30476220 | chr22 | 30881582 | 30881612 |
| chr22 | 30938543 | 30938584 | chr22 | 31198492 | 31198637 | chr22 | 31218510 | 31218540 |
| chr22 | 31218794 | 31218829 | chr22 | 31481130 | 31481332 | chr22 | 32748908 | 32748966 |
| chr22 | 33197603 | 33197652 | chr22 | 33453877 | 33454074 | chr22 | 33454194 | 33454258 |
| chr22 | 33454346 | 33454366 | chr22 | 35656581 | 35656610 | chr22 | 35848358 | 35848670 |
| chr22 | 35938746 | 35939000 | chr22 | 36681295 | 36681341 | chr22 | 36855568 | 36855598 |
| chr22 | 36902291 | 36902381 | chr22 | 37720961 | 37721163 | chr22 | 38087310 | 38087367 |
| chr22 | 38199769 | 38199894 | chr22 | 38220653 | 38221201 | chr22 | 38477069 | 38477131 |
| chr22 | 38477297 | 38477794 | chr22 | 38507316 | 38507346 | chr22 | 38592936 | 38593076 |
| chr22 | 38639229 | 38639259 | chr22 | 38874215 | 38874259 | chr22 | 39112502 | 39112584 |
| chr22 | 39784480 | 39784598 | chr22 | 39830355 | 39830457 | chr22 | 39853521 | 39853592 |
| chr22 | 39932499 | 39932563 | chr22 | 39954429 | 39954516 | chr22 | 40042627 | 40042743 |
| chr22 | 40075157 | 40075302 | chr22 | 40226367 | 40226389 | chr22 | 40807034 | 40807063 |
| chr22 | 41048732 | 41048951 | chr22 | 41534393 | 41634542 | chr22 | 41637064 | 41637129 |
| chr22 | 41648414 | 41648444 | chr22 | 41657233 | 41657350 | chr22 | 42096002 | 42096190 |
| chr22 | 42310087 | 42310220 | chr22 | 42311521 | 42311587 | chr22 | 42353611 | 42353892 |
| chr22 | 42667358 | 42667432 | chr22 | 43012543 | 43012560 | chr22 | 43012860 | 43012877 |
| chr22 | 43083130 | 43083148 | chr22 | 43434441 | 43434477 | chr22 | 43740084 | 43740128 |
| chr22 | 43808280 | 43808428 | chr22 | 44208418 | 44208448 | chr22 | 44258366 | 44258506 |
| chr22 | 44287650 | 44287696 | chr22 | 44455707 | 44455740 | chr22 | 45087632 | 45087649 |
| chr22 | 45088602 | 45088743 | chr22 | 45135939 | 45135979 | chr22 | 45252445 | 45252463 |
| chr22 | 45277292 | 45277322 | chr22 | 45313416 | 45313446 | chr22 | 45403086 | 45403133 |
| chr22 | 45403478 | 45403714 | chr22 | 45404197 | 45404433 | chr22 | 45404994 | 45405010 |
| chr22 | 45405047 | 45405061 | chr22 | 45406318 | 45405418 | chr22 | 45405620 | 45405768 |
| chr22 | 45406271 | 45406328 | chr22 | 45593643 | 45593715 | chr22 | 45604184 | 45604343 |
| chr22 | 45719161 | 45719190 | chr22 | 46262452 | 46263051 | chr22 | 46263512 | 46263623 |
| chr22 | 46263744 | 46263809 | chr22 | 46276749 | 46276820 | chr22 | 46438085 | 46438121 |
| chr22 | 46599623 | 46599725 | chr22 | 46931260 | 46931332 | chr22 | 46933089 | 46933237 |
| chr22 | 47005080 | 47005154 | chr22 | 47023044 | 47023191 | chr22 | 47054686 | 47054716 |
| chr22 | 47193335 | 47193371 | chr22 | 47395475 | 47395505 | chr22 | 47525846 | 47525885 |
| chr22 | 47584867 | 47585024 | chr22 | 48027626 | 48027655 | chr22 | 48885530 | 48885837 |
| chr22 | 48886659 | 48886849 | chr22 | 48931881 | 48932027 | chr22 | 48971533 | 48971679 |
| chr22 | 48972220 | 48972465 | chr22 | 49852617 | 49852647 | chr22 | 49979646 | 49979757 |
| chr22 | 50001699 | 50001882 | chr22 | 50002787 | 50002819 | chr22 | 50003204 | 50003234 |
| chr22 | 50010113 | 50010258 | chr22 | 50010461 | 50010585 | chr22 | 50031691 | 50031721 |
| chr22 | 50064760 | 50064944 | chr22 | 50149431 | 50149470 | chr22 | 50467005 | 50467035 |
| chr22 | 50497147 | 50497182 | chr22 | 50497214 | 50497287 | chr22 | 50623672 | 50623714 |
| chr22 | 50623742 | 50623815 | chr22 | 50899293 | 50899672 | chr22 | 50939073 | 50939111 |
| chr22 | 50943093 | 50943262 | chr22 | 50986016 | 50986045 | chr22 | 51042278 | 51042404 |
| chr22 | 51042458 | 51042565 | chr22 | 51112150 | 51112232 | chrX | 3631506 | 3631633 |
| chrX | 3746612 | 3746642 | chrX | 6145331 | 6145688 | chrX | 8698863 | 8698897 |
| chrX | 8699504 | 8699566 | chrX | 20148710 | 20148739 | chrX | 47039370 | 47039399 |
| chX | 47426106 | 47426144 | chrX | 47426780 | 47426821 | chrX | 50557075 | 50557075 |
| chrX | 66931448 | 66931477 | chrX | 66937356 | 66937385 | chrX | 66943529 | 56943567 |
| chrX | 70339239 | 70339268 | chrX | 100740260 | 100740289 | chrX | 101906099 | 101906120 |
| chrX | 102000609 | 102000758 | chrX | 134156560 | 134156680 | chrX | 136656563 | 136656592 |
| chrY | 2655316 | 2655346 | chrY | 3446305 | 3446343 | chrY | 13316007 | 13316132 |
| chrY | 14532822 | 14532852 | chrY | 14533556 | 14533613 | chrY | 21204734 | 21205113 |

TABLE 14

| chr | start | end | chr | start | end | chr | start | end |
|---|---|---|---|---|---|---|---|---|
| chr1 | 898633 | 898792 | chr1 | 913445 | 914044 | chr1 | 1080495 | 1080914 |
| chr1 | 1146657 | 1146896 | chr1 | 1218688 | 1218779 | chr1 | 1223433 | 1223595 |
| chr1 | 1235811 | 1236156 | chr1 | 1266957 | 1267233 | chr1 | 1267372 | 1267791 |
| chr1 | 1267823 | 1268242 | chr1 | 1341738 | 1341826 | chr1 | 1475458 | 1476417 |
| chr1 | 1483096 | 1483139 | chr1 | 1563119 | 1563298 | chr1 | 1856362 | 1856471 |
| chr1 | 1857759 | 1857811 | chr1 | 1874647 | 1874877 | chr1 | 1910341 | 1910465 |

TABLE 14-continued

| chr | start | end | chr | start | end | chr | start | end |
|---|---|---|---|---|---|---|---|---|
| chr1 | 1935188 | 1935547 | chr1 | 1974768 | 1974802 | chr1 | 2066406 | 2066756 |
| chr1 | 2125141 | 2125560 | chr1 | 2263067 | 2263366 | chr1 | 2267472 | 2267771 |
| chr] | 2304239 | 2304478 | chr1 | 2307851 | 2307970 | chr1 | 2308023 | 2308030 |
| chr1 | 2308297 | 2308716 | chr1 | 2309792 | 2309994 | chr1 | 2331281 | 2331500 |
| chr1 | 2336323 | 2336440 | chr1 | 2375047 | 2375646 | chr1 | 2396927 | 2397106 |
| chr1 | 2428239 | 2428478 | chr1 | 2472089 | 2472388 | chr1 | 2506974 | 2507150 |
| chr1 | 2520925 | 2521062 | chr1 | 2706094 | 2706552 | chr1 | 2830081 | 2830147 |
| che1 | 2865964 | 2866143 | chr1 | 2984645 | 2984824 | chr1 | 3102567 | 3102866 |
| che1 | 3182781 | 3182874 | che1 | 3182942 | 3183020 | chr1 | 3322011 | 3322250 |
| chr1 | 3567062 | 3568320 | chr1 | 3601749 | 3602030 | chr1 | 3606995 | 3607339 |
| chr1 | 3659530 | 3659769 | chr1 | 3663458 | 3663637 | chr1 | 3663779 | 3664018 |
| chr1 | 3664606 | 3664781 | chr1 | 3683723 | 3683902 | chr1 | 4111087 | 4111323 |
| chr1 | 4713943 | 4714422 | chr1 | 4714642 | 4716744 | chr1 | 6166262 | 6166561 |
| chr1 | 6171668 | 6171907 | chr1 | 6186410 | 6186649 | chr1 | 6280169 | 6280348 |
| chr1 | 6304103 | 6304342 | chr1 | 6360495 | 6360728 | chr1 | 6446041 | 6446400 |
| chr1 | 6480434 | 6480913 | chr1 | 6500911 | 6501262 | chr1 | 6507603 | 6508202 |
| chr1 | 7764540 | 7764775 | chr1 | 8277298 | 8277837 | chr1 | 9712017 | 9712179 |
| chr1 | 9712459 | 9713096 | chr1 | 10166481 | 10166626 | chr1 | 10948478 | 10948657 |
| chr1 | 11538796 | 11538913 | chr1 | 11539101 | 11539280 | chr1 | 11539336 | 11539515 |
| chr1 | 11540035 | 11540334 | chr1 | 11591712 | 11591863 | chr1 | 11752375 | 11752614 |
| chr1 | 11936674 | 11936779 | chr1 | 11958996 | 11959295 | chr1 | 12041511 | 12041630 |
| chr1 | 12123143 | 12123742 | chr1 | 12227604 | 12227805 | chr1 | 12251342 | 12252059 |
| chr1 | 13839669 | 13910088 | chr1 | 13910336 | 13910815 | chr1 | 14026401 | 14026700 |
| chr1 | 14730390 | 14730502 | chr1 | 14925417 | 14926136 | chr1 | 15251113 | 15251316 |
| chr1 | 15480854 | 15480983 | chr1 | 16085267 | 16085746 | chr1 | 16474984 | 16475299 |
| chr1 | 16861448 | 16861627 | chr1 | 17445781 | 17446011 | chr1 | 18434366 | 18434605 |
| chr1 | 18437373 | 18437612 | chr1 | 18956114 | 18956353 | chr1 | 18956383 | 18956408 |
| chr1 | 18956496 | 18956735 | chr1 | 18956782 | 18967321 | chr1 | 18957428 | 18957667 |
| chr1 | 18957938 | 18958477 | chr1 | 18959346 | 18959645 | chr1 | 18960795 | 18961094 |
| chr1 | 18962648 | 18963231 | chr1 | 18969543 | 18969902 | chr1 | 18971772 | 18972011 |
| chr1 | 18972056 | 18972170 | chr1 | 19043472 | 19043771 | chr1 | 19992272 | 19992511 |
| chr1 | 20127444 | 20127555 | chr1 | 20618230 | 20618469 | chr1 | 20878953 | 20829372 |
| chr1 | 20879482 | 20879721 | chr1 | 20879752 | 20880051 | chr1 | 20880095 | 20880694 |
| chr1 | 21026082 | 21026253 | chr1 | 21042820 | 21042999 | chr1 | 21044024 | 21044263 |
| chr1 | 21573736 | 21574215 | chr1 | 21835856 | 21836095 | chr1 | 22140674 | 22141393 |
| chr1 | 22927327 | 22927566 | chr1 | 23748907 | 23749146 | chr1 | 23884996 | 23885088 |
| chr1 | 25255845 | 25256029 | chr1 | 25256280 | 25256459 | chr1 | 25256826 | 25257305 |
| chr1 | 25257391 | 25257464 | chr1 | 26551597 | 26551896 | chr1 | 26551989 | 26552228 |
| chr1 | 26737509 | 26737688 | chr1 | 26737855 | 26738274 | chr1 | 27190078 | 27190377 |
| chr1 | 27844444 | 27844623 | chr1 | 29450398 | 29450637 | chr1 | 29585984 | 29586763 |
| chr1 | 29804872 | 29805171 | chr1 | 30351469 | 30351828 | chr1 | 30815328 | 30815675 |
| chr1 | 31863112 | 31863130 | chr1 | 32180323 | 32180502 | chr1 | 32237507 | 32238586 |
| chr1 | 32410202 | 32410381 | chr1 | 32410418 | 32410717 | chr1 | 32705425 | 32705639 |
| chr1 | 32756421 | 32756519 | chr1 | 32930524 | 32930658 | chr1 | 34628874 | 34629053 |
| chr1 | 34629390 | 34629809 | chr1 | 34630473 | 34630712 | chr1 | 34630770 | 34631069 |
| chr1 | 34631502 | 34631741 | chr1 | 34631859 | 34631892 | chr1 | 34632023 | 34632038 |
| chr1 | 34642298 | 34642657 | chr1 | 35258557 | 35258796 | chr1 | 35350980 | 35351759 |
| chr1 | 35395450 | 35395929 | chr1 | 35664721 | 35664836 | chr1 | 36042605 | 36043564 |
| chr1 | 36563382 | 36563621 | chr1 | 37498718 | 37499257 | chr1 | 37499358 | 37500257 |
| chr1 | 37500368 | 37500907 | chr1 | 37500998 | 37501107 | chr1 | 38100591 | 38100787 |
| chr1 | 38219635 | 38219874 | chr1 | 38229961 | 38230380 | chr1 | 38230700 | 38230937 |
| chr1 | 38398356 | 38398431 | chr1 | 38510079 | 38510258 | chr1 | 38510475 | 38510714 |
| chr1 | 38510778 | 38511197 | chr1 | 38511252 | 38511911 | chr1 | 38512311 | 38512490 |
| chr1 | 38513162 | 38513229 | chr1 | 39269662 | 39270201 | chr1 | 40137822 | 40138061 |
| chr1 | 40237053 | 40237281 | chr1 | 40349627 | 40349746 | chr1 | 41284058 | 41284541 |
| chr1 | 41847494 | 41847793 | chr1 | 41848778 | 41848915 | chr1 | 41967261 | 41967360 |
| chr1 | 41991552 | 41991791 | chr1 | 43834653 | 43834807 | chr1 | 44068700 | 44068879 |
| chr1 | 44726821 | 44727360 | chr1 | 44872358 | 44873797 | chr1 | 44883030 | 44884289 |
| chr1 | 45308239 | 45308358 | chr1 | 45308655 | 45308729 | chr1 | 46632781 | 46633020 |
| chr1 | 46913761 | 46914360 | chr1 | 46914582 | 46914641 | chr1 | 46932686 | 46932842 |
| chr1 | 46951114 | 46951833 | chr1 | 46956380 | 46956679 | chr1 | 46956728 | 46957246 |
| chr1 | 47009851 | 47010150 | chr1 | 47695033 | 47695512 | chr1 | 47696207 | 47696686 |
| chr1 | 47696727 | 47697206 | chr1 | 47697254 | 47697613 | chr1 | 47697642 | 47698301 |
| chr1 | 47881984 | 47882403 | chr1 | 47882667 | 47882906 | chr1 | 47909640 | 47910239 |
| chr1 | 47910420 | 47911019 | chr1 | 47911243 | 47911365 | chr1 | 48058982 | 48059341 |
| chr1 | 49242260 | 49242619 | chr1 | 50513541 | 50513837 | chr1 | 50799190 | 50799489 |
| chr1 | 50880808 | 50882625 | chr1 | 50882731 | 50883690 | chr1 | 50883800 | 50884999 |
| chr1 | 50885262 | 50885441 | chr1 | 50886107 | 50887366 | chr1 | 50888619 | 50888918 |
| chr1 | 50889008 | 50889607 | chr1 | 50889741 | 50890460 | chr1 | 50890600 | 50891565 |
| chr1 | 50892073 | 50892432 | chr1 | 50892523 | 50893962 | chr1 | 51763181 | 51763395 |
| chr1 | 52832605 | 52832712 | chr1 | 53068087 | 53068626 | chr1 | 53098746 | 53099165 |
| chr1 | 53308489 | 53309328 | chr1 | 53528288 | 53528527 | chr1 | 53705675 | 53705794 |
| chr1 | 54203419 | 54204498 | chr1 | 54586432 | 54586831 | chr1 | 55462599 | 55462778 |
| chr1 | 57888293 | 57888472 | chr1 | 57888888 | 57889187 | chr1 | 57889319 | 57889738 |
| chr1 | 57890332 | 57890671 | chr1 | 58715055 | 58715294 | chr1 | 58715375 | 58716094 |
| chr1 | 61519265 | 61619497 | chr1 | 62793169 | 62793342 | chr1 | 53539429 | 63539968 |
| chr1 | 63785232 | 63786431 | chr1 | 63786928 | 63787167 | chr1 | 63787226 | 63787645 |
| chr1 | 63788341 | 63788640 | chr1 | 63788694 | 63790373 | chr1 | 63792458 | 63793171 |

TABLE 14-continued

| chr | start | end | chr | start | end | chr | start | end |
|---|---|---|---|---|---|---|---|---|
| chr1 | 63795265 | 63796370 | chr1 | 63796418 | 63796584 | chr1 | 64240031 | 64240222 |
| chr1 | 64240526 | 64240765 | chr1 | 64734554 | 64734669 | chr1 | 64937227 | 64937401 |
| chr1 | 65731243 | 65731542 | chr1 | 65731552 | 65731851 | chr1 | 65990876 | 65991115 |
| chr1 | 65991344 | 65991883 | chr1 | 66258088 | 66258867 | chr1 | 66259037 | 66259276 |
| chr1 | 66998702 | 66999412 | chr1 | 66999536 | 66999772 | chr1 | 67217965 | 67218424 |
| chr1 | 67390243 | 67390542 | chr1 | 67390993 | 67391172 | chr1 | 57773081 | 67773860 |
| chr1 | 70033524 | 70033709 | chr1 | 70033829 | 70034003 | chr1 | 70034368 | 70034667 |
| chr1 | 70035014 | 70035526 | chr1 | 70599152 | 70599260 | chr1 | 70672859 | 70672978 |
| chr1 | 72749635 | 72749798 | chr1 | 75595702 | 75596479 | chr1 | 75596597 | 75597668 |
| chr1 | 75597842 | 75598261 | chr1 | 75598310 | 75598489 | chr1 | 75599345 | 75599704 |
| chr1 | 75600148 | 75601513 | chr1 | 75601889 | 75603148 | chr1 | 76080387 | 76080866 |
| chr1 | 76082050 | 76082289 | chr1 | 76354731 | 76354839 | chr1 | 76540398 | 76540757 |
| chr1 | 77332984 | 77333163 | chr1 | 77333285 | 77333625 | chr1 | 77333947 | 77334846 |
| chr1 | 77747291 | 77747530 | chr1 | 77747848 | 77748327 | chr1 | 78611371 | 78512450 |
| chr1 | 78957198 | 78957617 | chr1 | 82268586 | 82268904 | chr1 | 84944531 | 84944650 |
| chr1 | 85358543 | 85358902 | chr1 | 85463275 | 85463454 | chr1 | 86621565 | 86522024 |
| chr1 | 86622112 | 86622224 | chr1 | 86622430 | 86622831 | chr1 | 86860815 | 86861049 |
| chr1 | 87617672 | 87617911 | chr1 | 90309344 | 90309571 | chr1 | 91171926 | 91172765 |
| chr1 | 91177865 | 91178284 | chr1 | 91179982 | 91180401 | chr1 | 91181853 | 91182212 |
| chr1 | 91182246 | 91182969 | chr1 | 91183001 | 91183805 | chr1 | 91183850 | 91184080 |
| chr1 | 91184339 | 91184758 | chr1 | 91185126 | 91185809 | chr1 | 91188891 | 91189483 |
| chr1 | 91189585 | 91190484 | chr1 | 91190791 | 91191390 | chr1 | 91192174 | 91192773 |
| chr1 | 91194446 | 91194672 | chr1 | 91195015 | 91195494 | chr1 | 91195802 | 91196581 |
| chr1 | 91316168 | 91316407 | chr1 | 91316536 | 91316775 | chr1 | 91869914 | 91870093 |
| chr1 | 92948236 | 92948701 | chr1 | 92948760 | 92949059 | chr1 | 92952071 | 92952632 |
| chr1 | 94343486 | 94343596 | chr1 | 97185167 | 97185357 | chr1 | 98510704 | 98511423 |
| chr1 | 98511536 | 98512015 | chr1 | 98514151 | 98514330 | chr1 | 98515048 | 98515408 |
| chr1 | 98518930 | 98519769 | chr1 | 99469586 | 99469885 | chr1 | 99470049 | 99470288 |
| chr1 | 99470697 | 99470924 | chr1 | 100437184 | 100437270 | chr1 | 101004358 | 101004837 |
| chr1 | 101004989 | 101005228 | chr1 | 101005279 | 101005758 | chr1 | 101702411 | 101702710 |
| chr1 | 101703538 | 101703717 | chr1 | 107682647 | 107683066 | chr1 | 107683359 | 107683598 |
| chr1 | 107684161 | 107684520 | chr1 | 108506989 | 108507168 | chr1 | 108507230 | 108507589 |
| chr1 | 108507615 | 108507914 | chr1 | 108507957 | 108508671 | chr1 | 109203582 | 109203761 |
| chr1 | 109585369 | 109585472 | chr1 | 109631647 | 109631766 | chr1 | 109644252 | 109644413 |
| chr1 | 110610483 | 110612162 | chr1 | 110612760 | 110613239 | chr1 | 110626592 | 110627671 |
| chr1 | 110672792 | 110673331 | chr1 | 110692886 | 110694205 | chr1 | 110754040 | 110754202 |
| chr1 | 110754211 | 110754930 | chr1 | 110883455 | 110884054 | chr1 | 111097832 | 111098011 |
| chr1 | 111098107 | 111098406 | chr1 | 111216684 | 111218063 | chr1 | 111505931 | 111506290 |
| chr1 | 111813448 | 111813687 | chr1 | 112084880 | 112085059 | chr1 | 114448981 | 114449087 |
| chr1 | 114695362 | 114696021 | chr1 | 114696132 | 114696299 | chr1 | 114696335 | 114696791 |
| chr1 | 115256441 | 115256620 | chr1 | 115258659 | 115258838 | chr1 | 115631842 | 115632011 |
| chr1 | 115632393 | 115632632 | chr1 | 115880081 | 115880500 | chr1 | 115880765 | 115881304 |
| chr1 | 116214002 | 116214132 | chr1 | 116214207 | 116214421 | chr1 | 116371051 | 116371290 |
| chr1 | 116380550 | 116381389 | chr1 | 116382294 | 116382583 | chr1 | 119521973 | 119522121 |
| chr1 | 119522200 | 119522632 | chr1 | 119522741 | 119523039 | chr1 | 119526993 | 119527472 |
| chr1 | 119527549 | 119527728 | chr1 | 119528557 | 119529216 | chr1 | 119529703 | 119529942 |
| chr1 | 119530024 | 119530743 | chr1 | 119530944 | 119531243 | chr1 | 119531943 | 119532177 |
| chr1 | 119535738 | 119535857 | chr1 | 119536058 | 119536457 | chr1 | 119542248 | 119542427 |
| chr1 | 119542905 | 119543324 | chr1 | 119543438 | 119544277 | chr1 | 119548749 | 119548928 |
| chr1 | 119548955 | 119549017 | chr1 | 119549032 | 119550034 | chr1 | 119550068 | 119550367 |
| chr1 | 119550434 | 119550733 | chr1 | 119550818 | 119551357 | chr1 | 150603035 | 150603141 |
| chr1 | 151169649 | 151169757 | chr1 | 151170069 | 151170297 | chr1 | 151300814 | 151300933 |
| chr1 | 151693849 | 151694448 | chr1 | 162085302 | 152085601 | chr1 | 152488055 | 152488294 |
| chr1 | 153539382 | 153539681 | chr1 | 153540006 | 153540245 | chr1 | 153651873 | 153652472 |
| chr1 | 153937048 | 153937167 | chr1 | 154298230 | 154298562 | chr1 | 154475073 | 154475612 |
| chr1 | 154516709 | 154516926 | chr1 | 155043313 | 155043734 | chr1 | 155161767 | 155161886 |
| chr1 | 155578918 | 155579008 | chr1 | 155826303 | 155826412 | chr1 | 155954190 | 155954391 |
| chr1 | 156010529 | 156010643 | chr1 | 156215255 | 156215434 | chr1 | 156215527 | 156215886 |
| chr1 | 156357892 | 156358611 | chr1 | 156390058 | 156390777 | chr1 | 156405436 | 156406515 |
| chr1 | 156432076 | 156432315 | chr1 | 156594879 | 156595118 | chr1 | 156611795 | 156612214 |
| chr1 | 156626505 | 156626744 | chr1 | 156626814 | 156627113 | chr1 | 156646516 | 156646740 |
| chr1 | 156814831 | 156815250 | chr1 | 156815356 | 156815835 | chr1 | 156830190 | 156830429 |
| chr1 | 156838078 | 156838424 | chr1 | 156863010 | 156863429 | chr1 | 156863574 | 156863808 |
| chr1 | 157247369 | 157247487 | chr1 | 157458816 | 157458935 | chr1 | 157895339 | 157896518 |
| chr1 | 158669614 | 158669973 | chr1 | 158687334 | 158687633 | chr1 | 159158251 | 159158588 |
| chr1 | 159187205 | 159187390 | chr1 | 160693839 | 160693957 | chr1 | 160992253 | 160992363 |
| chr1 | 161007615 | 161007847 | chr1 | 161228566 | 161228971 | chr1 | 161275466 | 161276125 |
| chr1 | 161442367 | 161442546 | chr1 | 161471751 | 161471868 | chr1 | 161591390 | 161591444 |
| chr1 | 161591549 | 161591629 | chr1 | 162792211 | 162792630 | chr1 | 164290533 | 164290772 |
| chr1 | 165086889 | 165087114 | chr1 | 165204994 | 165205233 | chr1 | 165321651 | 165321950 |
| chr1 | 165324104 | 165324758 | chr1 | 165325016 | 165325615 | chr1 | 165325804 | 165326043 |
| chr1 | 165326128 | 165326547 | chr1 | 165414124 | 165414352 | chr1 | 166134158 | 166134397 |
| chr1 | 166134643 | 166134882 | chr1 | 166135118 | 166135357 | chr1 | 166853551 | 166853668 |
| chr1 | 166916774 | 166917193 | chr1 | 167599076 | 167599435 | chr1 | 167599521 | 167599940 |
| chr1 | 167823371 | 167823524 | chr1 | 169396291 | 169397010 | chr1 | 170629466 | 170629513 |
| chr1 | 170629925 | 170630151 | chr1 | 170630364 | 170630903 | chr1 | 170631005 | 170631244 |
| chr1 | 170631399 | 170631638 | chr1 | 170633533 | 170633712 | chr1 | 170637582 | 170637881 |
| chr1 | 170640425 | 170640784 | chr1 | 171625443 | 171625543 | chr1 | 171810113 | 171811066 |

TABLE 14-continued

| chr | start | end | chr | start | end | chr | start | end |
|---|---|---|---|---|---|---|---|---|
| chr1 | 173638567 | 173639153 | chr1 | 175346411 | 175346646 | chr1 | 175388553 | 175388682 |
| chr1 | 177133619 | 177133918 | chr1 | 177140021 | 177140790 | chr1 | 177150699 | 177150878 |
| chr1 | 179644884 | 179545183 | chr1 | 179712063 | 179713502 | chr1 | 180197986 | 180198285 |
| chr1 | 180202331 | 180203110 | chr1 | 180203355 | 180205009 | chr1 | 180235656 | 180235835 |
| chr1 | 180882487 | 180882518 | chr1 | 180925188 | 180925289 | chr1 | 180925330 | 180925487 |
| chr1 | 181287599 | 181287838 | chr1 | 181287922 | 181288281 | chr1 | 181451315 | 181452214 |
| chr1 | 181452770 | 181453069 | chr1 | 181454774 | 181455013 | chr1 | 181455104 | 181455343 |
| chr1 | 182584084 | 182584623 | chr1 | 182807488 | 182807607 | chr1 | 183129301 | 183129530 |
| chr1 | 183386070 | 183386369 | chr1 | 183386414 | 183386713 | chr1 | 183386752 | 183387051 |
| chr1 | 183387174 | 183387413 | chr1 | 183462984 | 183463103 | chr1 | 183774155 | 183774454 |
| chr1 | 184005609 | 184005908 | chr1 | 185073803 | 185074028 | chr1 | 190444781 | 190444892 |
| chr1 | 190445080 | 190445379 | chr1 | 190447297 | 190447596 | chr1 | 195732240 | 195732521 |
| chr1 | 196577628 | 196577953 | chr1 | 196578007 | 196578246 | chr1 | 197879307 | 197879546 |
| chr1 | 197879607 | 197880258 | chr1 | 197882052 | 197882291 | chr1 | 197882353 | 197882581 |
| chr1 | 197886978 | 197887817 | chr1 | 197887977 | 197888396 | chr1 | 197888546 | 197889385 |
| chr1 | 200009312 | 200009551 | chr1 | 200009665 | 200010202 | chr1 | 200011236 | 200012191 |
| chr1 | 201368752 | 201368805 | chr1 | 201983038 | 201983277 | chr1 | 202081790 | 202081886 |
| chr1 | 202183343 | 202183476 | chr1 | 202679128 | 202679607 | chr1 | 203298210 | 203298441 |
| chr1 | 203429530 | 203429649 | chr1 | 204333520 | 204333660 | chr1 | 204653475 | 204653894 |
| chr1 | 205312504 | 205313043 | chr1 | 20424577 | 205425046 | chr1 | 205537569 | 205537868 |
| chr1 | 207200767 | 207201066 | chr1 | 207669419 | 207670138 | chr1 | 207818295 | 207818424 |
| chr1 | 208084210 | 208084569 | chr1 | 209381030 | 209381269 | chr1 | 210111072 | 210111251 |
| chr1 | 210111285 | 210112244 | chr1 | 211847683 | 211847862 | chr1 | 212963808 | 212963979 |
| chr1 | 213123776 | 213124075 | chr1 | 213124573 | 213124992 | chr1 | 214156345 | 214157004 |
| chr1 | 214158753 | 214159052 | chr1 | 214160028 | 214160266 | chr1 | 214360583 | 214361062 |
| chr1 | 214724457 | 214724588 | chr1 | 215254998 | 215255897 | chr1 | 216897142 | 216897321 |
| chr1 | 217307273 | 217307311 | chr1 | 217307368 | 217308360 | chr1 | 217308907 | 217309206 |
| chr1 | 217309671 | 217309910 | chr1 | 217311163 | 217311942 | chr1 | 217312946 | 217313822 |
| chr1 | 217805068 | 217805236 | chr1 | 218520021 | 218520477 | chr1 | 218520701 | 218520740 |
| chr1 | 219347112 | 219347134 | chr1 | 219347314 | 219347553 | chr1 | 220101056 | 220101475 |
| chr1 | 220101692 | 220101788 | chr1 | 220132115 | 220132213 | chr1 | 220636429 | 220636548 |
| chr1 | 220700737 | 220700976 | chr1 | 221051936 | 221052595 | chr1 | 221053527 | 221053946 |
| chr1 | 221067418 | 221067777 | chr1 | 223302739 | 223302978 | chr1 | 223538254 | 223538670 |
| chr1 | 223936546 | 223937145 | chr1 | 224400388 | 224400627 | chr1 | 224528740 | 224528919 |
| chr1 | 224803668 | 224803854 | chr1 | 224803995 | 224804991 | chr1 | 224805051 | 224805890 |
| chr1 | 226411169 | 226411348 | chr1 | 226411617 | 226411916 | chr1 | 226924982 | 226925281 |
| chr1 | 227729689 | 227730168 | chr1 | 228194340 | 228194579 | chr1 | 228195294 | 228196433 |
| chr1 | 228201147 | 228201326 | chr1 | 228247924 | 228247961 | chr1 | 428248228 | 228248407 |
| chr1 | 228463210 | 228463809 | chr1 | 228528749 | 228529108 | chr1 | 228558623 | 228559329 |
| chr1 | 228566528 | 228566618 | chr1 | 228566537 | 228566767 | chr1 | 228603929 | 228604348 |
| chr1 | 228633887 | 228634354 | chr1 | 228645048 | 228645827 | chr1 | 228646196 | 228646315 |
| chr1 | 228651350 | 228651709 | chr1 | 228651805 | 228651924 | chr1 | 228652243 | 228652704 |
| chr1 | 229542750 | 229543229 | chr1 | 229543459 | 229543612 | chr1 | 229566670 | 229566942 |
| chr1 | 229567012 | 229568289 | chr1 | 229569712 | 229569951 | chr1 | 230404150 | 230404360 |
| chr1 | 230561683 | 230561922 | chr1 | 231297013 | 231297312 | chr1 | 231298505 | 231298864 |
| chr1 | 232765226 | 232765398 | chr1 | 233750126 | 233750402 | chr1 | 234040224 | 234040403 |
| chr1 | 234040668 | 234041147 | chr1 | 234041303 | 234041716 | chr1 | 234349895 | 234350194 |
| chr1 | 234445299 | 234445478 | chr1 | 234620965 | 234621073 | chr1 | 234844947 | 234845167 |
| chr1 | 235813693 | 235814292 | chr1 | 236227538 | 236228197 | chr1 | 236228507 | 236228866 |
| chr1 | 236559075 | 236559374 | chr1 | 236849381 | 236850220 | chr1 | 237205085 | 237206098 |
| chr1 | 237205157 | 237205264 | chr1 | 237205337 | 237205576 | chr1 | 237205612 | 237206811 |
| chr1 | 239550505 | 239551284 | chr1 | 240118762 | 240119061 | chr1 | 240160997 | 240161571 |
| chr1 | 240254859 | 240255098 | chr1 | 240255282 | 240255581 | chr1 | 240255739 | 240256278 |
| chr1 | 240256573 | 240256872 | chr1 | 240775351 | 240775530 | chr1 | 241052047 | 241052201 |
| chr1 | 241520202 | 241520441 | chr1 | 241520509 | 241520632 | chr1 | 241520685 | 241520688 |
| chr1 | 241587013 | 241587194 | chr1 | 241587513 | 241587872 | chr1 | 242686642 | 242687781 |
| chr1 | 242688103 | 242688342 | chr1 | 242688377 | 242688773 | chr1 | 243646523 | 243646762 |
| chr1 | 244014160 | 244014479 | chr1 | 244080598 | 244080777 | chr1 | 244080874 | 244080883 |
| chr1 | 244893136 | 244893255 | chr1 | 245135670 | 245135849 | chr1 | 245494418 | 245494631 |
| chr1 | 246330402 | 246330509 | chr1 | 246488077 | 246488316 | chr1 | 248002191 | 248002310 |
| chr1 | 248020405 | 248021424 | chr1 | 248027930 | 248028289 | chr1 | 248074658 | 248074768 |
| chr1 | 248074838 | 248075008 | chr1 | 248099661 | 248099900 | chr1 | 248328674 | 248328921 |
| chr1 | 249121623 | 249121738 | chr2 | 287492 | 287731 | chr2 | 288318 | 288557 |
| chr2 | 467943 | 468182 | chr2 | 468212 | 468756 | chr2 | 496125 | 496465 |
| chr2 | 720748 | 720985 | chr2 | 875887 | 876066 | chr2 | 945838 | 946077 |
| chr2 | 946117 | 946356 | chr2 | 946449 | 946688 | chr2 | 946819 | 947238 |
| chr2 | 1653023 | 1653262 | chr2 | 1746523 | 1747302 | chr2 | 1747591 | 1748906 |
| chr2 | 2844646 | 2844676 | chr2 | 2844802 | 2844825 | chr2 | 3750873 | 3751052 |
| chr2 | 3751238 | 3751537 | chr2 | 5831102 | 5831401 | chr2 | 5831715 | 5831894 |
| chr2 | 5831967 | 5832326 | chr2 | 5832800 | 5834119 | chr2 | 5835990 | 5836349 |
| chr2 | 5836451 | 5837170 | chr2 | 5837197 | 5837496 | chr2 | 5866006 | 3866305 |
| chr2 | 7164389 | 7164704 | chr2 | 7571420 | 7571828 | chr2 | 9134330 | 9134569 |
| chr2 | 9960660 | 9960839 | chr2 | 10115632 | 10115739 | chr2 | 10153063 | 10153168 |
| chr2 | 10153229 | 10153422 | chr2 | 10154909 | 10155024 | chr2 | 10155269 | 10155384 |
| chr2 | 10156334 | 10156493 | chr2 | 10182747 | 10182986 | chr2 | 10408310 | 10408347 |
| chr2 | 10688800 | 10688979 | chr2 | 11052419 | 11052658 | chr2 | 11809858 | 11810217 |
| chr2 | 12246027 | 12246196 | chr2 | 12858356 | 12858715 | chr2 | 14772673 | 14772888 |
| chr2 | 14774475 | 14774664 | chr2 | 12719601 | 17719900 | chr2 | 18058941 | 18059180 |

TABLE 14-continued

| chr | start | end | chr | start | end | chr | start | end |
|---|---|---|---|---|---|---|---|---|
| chr2 | 18059692 | 18059931 | chr2 | 19550140 | 19550319 | chr2 | 19551225 | 19551464 |
| chr2 | 19556226 | 19556765 | chr2 | 19556994 | 19557173 | chr2 | 19558744 | 19558983 |
| chr2 | 19561045 | 19561404 | chr2 | 19561422 | 19561781 | chr2 | 19563277 | 19563516 |
| chr2 | 20068723 | 20068962 | chr2 | 20442485 | 20442586 | chr2 | 20642626 | 20642745 |
| chr2 | 20865560 | 20866022 | chr2 | 25391060 | 25391313 | chr2 | 25391586 | 25391825 |
| chr2 | 25438724 | 25439356 | chr2 | 26372893 | 26373072 | chr2 | 26395353 | 26395652 |
| chr2 | 26401956 | 26402135 | chr2 | 26407418 | 26408085 | chr2 | 26521960 | 26522079 |
| chr2 | 26915682 | 26916341 | chr2 | 27070250 | 27070489 | chr2 | 27071144 | 27071443 |
| chr2 | 27072394 | 27072633 | chr2 | 27072727 | 27073086 | chr2 | 27578410 | 27578500 |
| chr2 | 27887451 | 27887630 | chr2 | 29033261 | 29034020 | chr2 | 29337988 | 29339067 |
| chr2 | 30143219 | 30143578 | chr2 | 30143957 | 30144496 | chr2 | 30453619 | 30454298 |
| chr2 | 31360210 | 31360929 | chr2 | 31361015 | 31361118 | chr2 | 31361194 | 31361194 |
| chr2 | 31361282 | 31361461 | chr2 | 31456606 | 31457131 | chr2 | 32504335 | 32504449 |
| chr2 | 38302176 | 38302955 | chr2 | 38365728 | 38365847 | chr2 | 39187141 | 39187800 |
| chr2 | 39892997 | 39893596 | chr2 | 39893897 | 39894136 | chr2 | 40678513 | 40678872 |
| chr2 | 40678945 | 40679712 | chr2 | 42274495 | 42274734 | chr2 | 42329340 | 42329759 |
| chr2 | 42720185 | 42720644 | chr2 | 43019525 | 43019944 | chr2 | 43451819 | 43452418 |
| chr2 | 43824034 | 43824132 | chr2 | 44497613 | 44497842 | chr2 | 45028911 | 45029450 |
| chr2 | 45029637 | 45029787 | chr2 | 45155039 | 45157783 | chr2 | 45159873 | 45160352 |
| chr2 | 45160496 | 45160735 | chr2 | 45161589 | 45162188 | chr2 | 45162319 | 45162558 |
| chr2 | 45162653 | 45163012 | chr2 | 45164589 | 45164768 | chr2 | 45165490 | 45165669 |
| chr2 | 45168857 | 45168908 | chr2 | 45169349 | 45170128 | chr2 | 45171295 | 45171954 |
| chr2 | 45176506 | 45176865 | chr2 | 45179546 | 45179725 | chr2 | 45179862 | 45180156 |
| chr2 | 45181412 | 45181776 | chr2 | 45181795 | 45182094 | chr2 | 45231239 | 45231478 |
| chr2 | 45231754 | 45232208 | chr2 | 45233307 | 45233666 | chr2 | 45235491 | 45236030 |
| chr2 | 45237585 | 45237884 | chr2 | 45240457 | 45240876 | chr2 | 45241041 | 45241280 |
| chr2 | 45395768 | 45396007 | chr2 | 45396234 | 45396533 | chr2 | 45396603 | 45397082 |
| chr2 | 46526226 | 46526331 | chr2 | 47193958 | 47194077 | chr2 | 47200517 | 47200696 |
| chr2 | 47249735 | 47249914 | chr2 | 47598298 | 47598477 | chr2 | 47598579 | 47598698 |
| chr2 | 47748048 | 47748587 | chr2 | 47796952 | 47797911 | chr2 | 47798093 | 47798752 |
| chr2 | 47798853 | 47799212 | chr2 | 48982485 | 48982964 | chr2 | 50573520 | 50573924 |
| chr2 | 50574041 | 50574940 | chr2 | 55289095 | 55289274 | chr2 | 56149762 | 56149941 |
| chr2 | 56150632 | 56151256 | chr2 | 56410918 | 56411087 | chr2 | 56411593 | 56411832 |
| chr2 | 58655968 | 58656207 | chr2 | 60706663 | 60706902 | chr2 | 60796498 | 60796617 |
| chr2 | 60797060 | 60797359 | chr2 | 61135116 | 61135235 | chr2 | 62798248 | 62798485 |
| chr2 | 63275470 | 63275949 | chr2 | 63278888 | 63279067 | chr2 | 63280853 | 63281752 |
| chr2 | 63282632 | 63282871 | chr2 | 53282924 | 63283053 | chr2 | 63283870 | 63284229 |
| chr2 | 63284675 | 63284914 | chr2 | 63284996 | 63287412 | chr2 | 56652937 | 66653063 |
| chr2 | 66653158 | 66653577 | chr2 | 66653690 | 66653989 | chr2 | 66660560 | 66660791 |
| chr2 | 66808447 | 66809453 | chr2 | 67625373 | 67625492 | chr2 | 67625733 | 67625852 |
| chr2 | 67626153 | 67626332 | chr2 | 68546249 | 68546968 | chr2 | 68559344 | 68559463 |
| chr2 | 68672777 | 68672956 | chr2 | 70418609 | 70418722 | chr2 | 71355039 | 71355218 |
| chr2 | 71503688 | 71503927 | chr2 | 71504007 | 71504246 | chr2 | 71680759 | 71680938 |
| chr2 | 71693423 | 71693694 | chr2 | 72374295 | 72374524 | chr2 | 72374611 | 72374850 |
| chr2 | 73145548 | 73145787 | chr2 | 73145824 | 73146123 | chr2 | 73147245 | 73148313 |
| chr2 | 73150850 | 73151029 | chr2 | 73151098 | 73151929 | chr2 | 73152600 | 73152839 |
| chr2 | 73429420 | 73429719 | chr2 | 73429862 | 73430161 | chr2 | 73430234 | 73430818 |
| chr2 | 73440271 | 73440370 | chr2 | 73518355 | 73519204 | chr2 | 73519501 | 73519920 |
| chr2 | 74010442 | 74010621 | chr2 | 74453989 | 74454348 | chr2 | 74726670 | 74726849 |
| chr2 | 74740761 | 74741480 | chr2 | 74741746 | 74742045 | chr2 | 74742085 | 74743824 |
| chr2 | 74781997 | 74782356 | chr2 | 75426958 | 75426980 | chr2 | 75427295 | 75427474 |
| chr2 | 75427845 | 75428264 | chr2 | 80529292 | 80529573 | chr2 | 80529573 | 80530112 |
| chr2 | 80530413 | 80530652 | chr2 | 80531651 | 80531830 | chr2 | 80549485 | 80549845 |
| chr2 | 85107377 | 85107616 | chr2 | 85361224 | 85361703 | chr2 | 87016489 | 87016728 |
| chr2 | 87017707 | 87018313 | chr2 | 88469219 | 88469398 | chr2 | 88751182 | 88751901 |
| chr2 | 88751961 | 88752380 | chr2 | 88752515 | 88752874 | chr2 | 88990108 | 88990347 |
| chr2 | 89064525 | 89065364 | chr2 | 95663873 | 95664112 | chr2 | 95690654 | 95690890 |
| chr2 | 95690944 | 95691363 | chr2 | 95691441 | 95691860 | chr2 | 95691908 | 95692567 |
| chr2 | 95941596 | 95941895 | chr2 | 96990808 | 96991399 | chr2 | 97193003 | 97193722 |
| chr2 | 97427415 | 97428194 | chr2 | 98703220 | 98703491 | chr2 | 98962800 | 98963039 |
| chr2 | 98963255 | 98963674 | chr2 | 98963750 | 98964289 | chr2 | 98964502 | 98964741 |
| chr2 | 99439054 | 99439593 | chr2 | 99553333 | 99553632 | chr2 | 99553723 | 99553734 |
| chr2 | 99796327 | 99796415 | chr2 | 99798571 | 99798746 | chr2 | 99799229 | 99799230 |
| chr2 | 100937747 | 100939246 | chr2 | 101009731 | 101010030 | chr2 | 101034149 | 101034388 |
| chr2 | 101436638 | 101436790 | chr2 | 102091079 | 102091335 | chr2 | 103236080 | 103236277 |
| chr2 | 105459001 | 105459600 | chr2 | 105459805 | 105460604 | chr2 | 105460847 | 105461026 |
| chr2 | 105461096 | 105461335 | chr2 | 105461461 | 105462000 | chr2 | 105462075 | 105462314 |
| chr2 | 105468701 | 105469000 | chr2 | 105469569 | 105470168 | chr2 | 105470266 | 105470925 |
| chr2 | 105472149 | 105472928 | chr2 | 105473162 | 105473521 | chr2 | 105478687 | 105479166 |
| chr2 | 105480444 | 105480683 | chr2 | 105483568 | 105483807 | chr2 | 105484367 | 105484480 |
| chr2 | 105488348 | 105488527 | chr2 | 105760890 | 105761004 | chr2 | 106060525 | 106060884 |
| chr2 | 106681644 | 106681870 | chr2 | 106681936 | 106682175 | chr2 | 106730137 | 106730316 |
| chr2 | 106959289 | 106959648 | chr2 | 106959833 | 106960072 | chr2 | 107103778 | 107104017 |
| chr2 | 107502499 | 107502918 | chr2 | 107503124 | 107503423 | chr2 | 107503458 | 107503637 |
| chr2 | 107503802 | 107504101 | chr2 | 109335091 | 109335264 | chr2 | 109648002 | 109648301 |
| chr2 | 109745915 | 109746154 | chr2 | 109746204 | 109746563 | chr2 | 111875279 | 111875518 |
| chr2 | 111876621 | 111876964 | chr2 | 112656944 | 112657123 | chr2 | 114034797 | 114035276 |
| chr2 | 114256879 | 114257238 | chr2 | 114261200 | 114261559 | chr2 | 115918579 | 115920618 |

TABLE 14-continued

| chr | start | end | chr | start | end | chr | start | end |
|---|---|---|---|---|---|---|---|---|
| chr2 | 118981075 | 118982574 | chr2 | 119067545 | 119068143 | chr2 | 119532059 | 119532358 |
| chr2 | 119566137 | 119566376 | chr2 | 119591259 | 119591558 | chr2 | 119592666 | 119592863 |
| chr2 | 119592923 | 119593642 | chr2 | 119599830 | 119600129 | chr2 | 119600235 | 119600839 |
| chr2 | 119600856 | 119600957 | chr2 | 119602515 | 119603174 | chr2 | 119603946 | 119604093 |
| chr2 | 119604154 | 119604245 | chr2 | 119604711 | 119604933 | chr2 | 119606048 | 119606283 |
| chr2 | 119606625 | 119606647 | chr2 | 119606692 | 119606931 | chr2 | 119607085 | 119607504 |
| chr2 | 119607694 | 119607933 | chr2 | 119610758 | 119611057 | chr2 | 119611653 | 119611892 |
| chr2 | 119612250 | 119612429 | chr2 | 119614047 | 119614271 | chr2 | 119614697 | 119614936 |
| chr2 | 119614952 | 119615719 | chr2 | 119616070 | 119616669 | chr2 | 119616721 | 119616960 |
| chr2 | 119914617 | 119914856 | chr2 | 119915947 | 119916186 | chr2 | 119916208 | 119916687 |
| chr2 | 120281556 | 120281790 | chr2 | 120281849 | 120282028 | chr2 | 120979994 | 120980173 |
| chr2 | 120980255 | 120980494 | chr2 | 121200303 | 121200532 | chr2 | 121345007 | 121345169 |
| chr2 | 121411987 | 121412231 | chr2 | 122495323 | 122495490 | chr2 | 124782247 | 124782546 |
| chr2 | 124782595 | 124783195 | chr2 | 127413828 | 127413908 | chr2 | 127423136 | 127423434 |
| chr2 | 127428910 | 127429147 | chr2 | 127438559 | 127438738 | chr2 | 127782953 | 127783360 |
| chr2 | 127863514 | 127863813 | chr2 | 127976391 | 127976750 | chr2 | 128421788 | 128422027 |
| chr2 | 128616519 | 128616628 | chr2 | 128847701 | 128847799 | chr2 | 130763485 | 130763724 |
| chr2 | 130971056 | 130971355 | chr2 | 131477742 | 131478023 | chr2 | 131594915 | 131595094 |
| chr2 | 131720754 | 131721353 | chr2 | 131721376 | 131722035 | chr2 | 131792157 | 131793236 |
| chr2 | 132088680 | 132088919 | chr2 | 132121566 | 132121823 | chr2 | 132152279 | 132152578 |
| chr2 | 132182701 | 132183180 | chr2 | 132767373 | 132767492 | chr2 | 133014571 | 133014678 |
| chr2 | 133015300 | 133015419 | chr2 | 133062239 | 133062478 | chr2 | 133426175 | 133426354 |
| chr2 | 133426561 | 133426776 | chr2 | 137522371 | 137522550 | chr2 | 137523751 | 137523759 |
| chr2 | 139536863 | 139537221 | chr2 | 139537355 | 139537954 | chr2 | 142887816 | 142888149 |
| chr2 | 142888264 | 142888503 | chr2 | 144694272 | 144695231 | chr2 | 145273369 | 145273848 |
| chr2 | 145274112 | 145274531 | chr2 | 145274715 | 145275314 | chr2 | 145282045 | 145282224 |
| chr2 | 148776713 | 148776876 | chr2 | 149633009 | 149633488 | chr2 | 149633646 | 149634065 |
| chr2 | 149645413 | 149645995 | chr2 | 151342979 | 151343218 | chr2 | 154333432 | 154333671 |
| chr2 | 154334170 | 154334769 | chr2 | 154335056 | 154335355 | chr2 | 154727963 | 154728442 |
| chr2 | 154728963 | 154729322 | chr2 | 154729485 | 154729664 | chr2 | 155555064 | 155555440 |
| chr2 | 157176591 | 157176805 | chr2 | 157178198 | 157178407 | chr2 | 157178637 | 157178809 |
| chr2 | 160760984 | 160761454 | chr2 | 161253375 | 161253554 | chr2 | 162272983 | 162274182 |
| chr2 | 162274220 | 162274414 | chr2 | 162274748 | 162274942 | chr2 | 162275055 | 162275887 |
| chr2 | 162279911 | 162281050 | chr2 | 162283291 | 162284130 | chr2 | 164592998 | 164593237 |
| chr2 | 168149978 | 168150337 | chr2 | 168150669 | 168151028 | chr2 | 170282882 | 170283178 |
| chr2 | 170551654 | 170551866 | chr2 | 170681792 | 170681909 | chr2 | 170682152 | 170682329 |
| chr2 | 171569986 | 171570525 | chr2 | 171570590 | 171570829 | chr2 | 171571171 | 171571342 |
| chr2 | 171571379 | 171571410 | chr2 | 171571800 | 171571997 | chr2 | 171670259 | 171670558 |
| chr2 | 171671385 | 171671984 | chr2 | 171674001 | 171674026 | chr2 | 171674664 | 171675143 |
| chr2 | 171675268 | 171675687 | chr2 | 171676590 | 171676885 | chr2 | 171822419 | 171822574 |
| chr2 | 172366939 | 172367178 | chr2 | 172411062 | 172411241 | chr2 | 172945027 | 172945266 |
| chr2 | 172945821 | 172946294 | chr2 | 172947684 | 172948405 | chr2 | 172948813 | 172948850 |
| chr2 | 172949090 | 172949809 | chr2 | 172951494 | 172951754 | chr2 | 172952425 | 172952640 |
| chr2 | 172952685 | 172953144 | chr2 | 172955346 | 172955645 | chr2 | 172957808 | 172958157 |
| chr2 | 172961319 | 172961678 | chr2 | 172964743 | 172965882 | chr2 | 172966174 | 172966533 |
| chr2 | 172972648 | 172973307 | chr2 | 173099710 | 173099889 | chr2 | 173100167 | 173100506 |
| chr2 | 173422651 | 173422270 | chr2 | 175190771 | 175192550 | chr2 | 175193187 | 175193906 |
| chr2 | 175195785 | 175195936 | chr2 | 175196355 | 175196371 | chr2 | 175196426 | 175196654 |
| chr2 | 175197015 | 175197194 | chr2 | 175198650 | 175198987 | chr2 | 175199432 | 175200012 |
| chr2 | 175200093 | 175202746 | chr2 | 175204100 | 175204279 | chr2 | 175204694 | 175205893 |
| chr2 | 175206752 | 175207111 | chr2 | 175207154 | 175207333 | chr2 | 175207446 | 175207745 |
| chr2 | 175208214 | 175209218 | chr2 | 175546942 | 175547241 | chr2 | 175547310 | 175547489 |
| chr2 | 176940092 | 176940391 | chr2 | 176943180 | 176943659 | chr2 | 176943763 | 176943863 |
| chr2 | 176943995 | 176944002 | chr2 | 176944326 | 176945885 | chr2 | 176946475 | 176947494 |
| chr2 | 176947647 | 176948006 | chr2 | 176948522 | 176948821 | chr2 | 176948971 | 176949150 |
| chr2 | 176949603 | 176949962 | chr2 | 176950051 | 176950350 | chr2 | 176956480 | 176956719 |
| chr2 | 176956821 | 176957300 | chr2 | 176957409 | 176957768 | chr2 | 176957829 | 176958008 |
| chr2 | 176958045 | 176958584 | chr2 | 176959191 | 176959589 | chr2 | 176963366 | 176963605 |
| chr2 | 176963999 | 176964238 | chr2 | 176964272 | 176965591 | chr2 | 176969387 | 176969984 |
| chr2 | 176972611 | 176972662 | chr2 | 176975946 | 176976289 | chr2 | 176980649 | 176981592 |
| chr2 | 176982487 | 176982726 | chr2 | 176986633 | 176986932 | chr2 | 176986952 | 176988401 |
| chr2 | 176993000 | 176993082 | chr2 | 176993462 | 176994741 | chr2 | 176994813 | 176994864 |
| chr2 | 176994981 | 176995712 | chr2 | 177001000 | 177001058 | chr2 | 177001118 | 177002079 |
| chr2 | 177004463 | 177004762 | chr2 | 177042891 | 177043610 | chr2 | 177053187 | 177053906 |
| chr2 | 177054023 | 177054442 | chr2 | 177502981 | 177503153 | chr2 | 178972904 | 178973143 |
| chr2 | 179317039 | 179317139 | chr2 | 182321308 | 182321727 | chr2 | 182321736 | 182322275 |
| chr2 | 182322292 | 182323131 | chr2 | 182542829 | 182543008 | chr2 | 182543221 | 182543413 |
| chr2 | 182543666 | 182544025 | chr2 | 182545124 | 182545363 | chr2 | 182545438 | 182545797 |
| chr2 | 182545887 | 182546179 | chr2 | 182546361 | 182546540 | chr2 | 182547290 | 182547709 |
| chr2 | 182547840 | 182548259 | chr2 | 182548992 | 182549231 | chr2 | 182549247 | 182549546 |
| chr2 | 182550020 | 182550199 | chr2 | 182819031 | 182819312 | chr2 | 183731200 | 183731619 |
| chr2 | 183731734 | 183732153 | chr2 | 185462776 | 185463075 | chr2 | 185463116 | 185463895 |
| chr2 | 186603414 | 186603593 | chr2 | 188418947 | 188419178 | chr2 | 189157513 | 189157692 |
| chr2 | 193058947 | 193060146 | chr2 | 193060294 | 193060533 | chr2 | 193060608 | 193060967 |
| chr2 | 193061341 | 193061580 | chr2 | 198456572 | 198456690 | chr2 | 200326551 | 200326730 |
| chr2 | 200326765 | 200326813 | chr2 | 200327187 | 200327666 | chr2 | 200328669 | 200329748 |
| chr2 | 200333686 | 200333925 | chr2 | 200334895 | 200335308 | chr2 | 200335363 | 200336034 |
| chr2 | 201450453 | 201450812 | chr2 | 201450845 | 201451144 | chr2 | 202096992 | 202097231 |

TABLE 14-continued

| chr | start | end | chr | start | end | chr | start | end |
|---|---|---|---|---|---|---|---|---|
| chr2 | 202899788 | 202899967 | chr2 | 206550978 | 206551457 | chr2 | 207138998 | 207139177 |
| chr2 | 207139267 | 207139686 | chr2 | 207307426 | 207307665 | chr2 | 207308711 | 207308950 |
| chr2 | 207506612 | 207507266 | chr2 | 208635519 | 208635864 | chr2 | 209113024 | 209113202 |
| chr2 | 209225137 | 209225376 | chr2 | 209271228 | 209271647 | chr2 | 210636255 | 210636974 |
| chr2 | 213401138 | 213401437 | chr2 | 213401511 | 213402050 | chr2 | 213403015 | 213403434 |
| chr2 | 217559222 | 217559401 | chr2 | 218806046 | 218806405 | chr2 | 219736062 | 219736705 |
| chr2 | 219827964 | 219827975 | chr2 | 219847360 | 219847659 | chr2 | 219848726 | 219849085 |
| chr2 | 219857648 | 219857860 | chr2 | 220080582 | 220080941 | chr2 | 220173904 | 220174383 |
| chr2 | 220196266 | 220196671 | chr2 | 220223024 | 220223203 | chr2 | 220223557 | 220223796 |
| chr2 | 220283250 | 220283609 | chr2 | 220299495 | 220300154 | chr2 | 220313696 | 220313777 |
| chr2 | 220348949 | 220349788 | chr2 | 220361370 | 220361609 | chr2 | 220416297 | 220416596 |
| chr2 | 220416770 | 220417729 | chr2 | 222435699 | 222435857 | chr2 | 223155678 | 223156277 |
| chr2 | 223158648 | 223159542 | chr2 | 223159735 | 223160154 | chr2 | 223160242 | 223160481 |
| chr2 | 223161173 | 223161352 | chr2 | 223161452 | 223162165 | chr2 | 223162678 | 223163637 |
| chr2 | 223163682 | 223164034 | chr2 | 223164440 | 223164979 | chr2 | 223165334 | 223165933 |
| chr2 | 223166190 | 223166825 | chr2 | 223167302 | 223167661 | chr2 | 223168346 | 223168945 |
| chr2 | 223169543 | 223169962 | chr2 | 223170286 | 223170525 | chr2 | 223171026 | 223171265 |
| chr2 | 223172263 | 223172356 | chr2 | 223172969 | 223173259 | chr2 | 223176018 | 223176282 |
| chr2 | 223176361 | 223177080 | chr2 | 223177224 | 223177703 | chr2 | 228029326 | 228029625 |
| chr2 | 228466762 | 228466881 | chr2 | 228735702 | 228735828 | chr2 | 228736135 | 228736554 |
| chr2 | 229046024 | 229046605 | chr2 | 230795461 | 230795640 | chr2 | 231693123 | 231693362 |
| chr2 | 232394867 | 232395166 | chr2 | 232791619 | 232792098 | chr2 | 233350112 | 233351491 |
| chr2 | 233351930 | 233352949 | chr2 | 233498615 | 233499394 | chr2 | 233750451 | 233750630 |
| chr2 | 235404471 | 235404590 | chr2 | 235860803 | 235860897 | chr2 | 236402683 | 236402901 |
| chr2 | 236403060 | 236403102 | chr2 | 236403174 | 236403419 | chr2 | 236403779 | 236403833 |
| chr2 | 236877188 | 236877367 | chr2 | 237072333 | 237073112 | chr2 | 237073265 | 237073504 |
| chr2 | 237076651 | 237076833 | chr2 | 237077466 | 237077685 | chr2 | 237077815 | 237078054 |
| chr2 | 237078097 | 237078427 | chr2 | 237080190 | 237080369 | chr2 | 237081255 | 237081914 |
| chr2 | 237082030 | 237082809 | chr2 | 237086291 | 237086559 | chr2 | 237145333 | 237145692 |
| chr2 | 237416114 | 237416504 | chr2 | 238395205 | 238395444 | chr2 | 238395815 | 238395988 |
| chr2 | 238535790 | 238536215 | chr2 | 238864570 | 238864989 | chr2 | 239051124 | 239051303 |
| chr2 | 239072551 | 239072790 | chr2 | 239139928 | 239140347 | chr2 | 239265703 | 239265881 |
| chr2 | 239482400 | 239482622 | chr2 | 239705202 | 239705364 | chr2 | 239755090 | 239755269 |
| chr2 | 239755638 | 239755877 | chr2 | 239756347 | 239756586 | chr2 | 239757551 | 239757910 |
| chr2 | 239757992 | 239758231 | chr2 | 239758251 | 239758490 | chr2 | 239957240 | 239957539 |
| chr2 | 240168722 | 240169141 | chr2 | 240319908 | 240320087 | chr2 | 240582303 | 240582448 |
| chr2 | 240619443 | 240619682 | chr2 | 240658145 | 240658504 | chr2 | 240658593 | 240658772 |
| chr2 | 241095576 | 241095868 | chr2 | 241393126 | 241393545 | chr2 | 241542045 | 241542344 |
| chr2 | 241544927 | 241545106 | chr2 | 241758299 | 241758898 | chr2 | 241759497 | 241759796 |
| chr2 | 241760075 | 241760254 | chr2 | 241760420 | 241760599 | chr2 | 241771062 | 241771361 |
| chr2 | 241865091 | 241865450 | chr2 | 242009317 | 242009496 | chr2 | 242021689 | 242021916 |
| chr2 | 242523873 | 242524172 | chr2 | 242549754 | 242549772 | chr2 | 242549918 | 242550053 |
| chr2 | 242554475 | 242554654 | chr2 | 242756042 | 242756401 | chr2 | 242832893 | 242833252 |
| chr2 | 242833484 | 242833663 | chr2 | 242833711 | 242833930 | chr2 | 242836419 | 242836718 |
| chr2 | 242925420 | 242925719 | chr3 | 238456 | 239175 | chr3 | 239534 | 240313 |
| chr3 | 2140189 | 2140488 | chr3 | 3840419 | 3840838 | chr3 | 3840946 | 3841245 |
| chr3 | 3842586 | 3842689 | chr3 | 5137871 | 5138109 | chr3 | 6902228 | 6902441 |
| chr3 | 6903600 | 6903564 | chr3 | 8810059 | 8810298 | chr3 | 9178065 | 9178281 |
| chr3 | 9593878 | 9594117 | chr3 | 9594286 | 9594473 | chr3 | 9595199 | 9595678 |
| chr3 | 9904155 | 9904634 | chr3 | 9941391 | 9941509 | chr3 | 9956984 | 9957223 |
| chr3 | 9957355 | 9957774 | chr3 | 10182757 | 10182917 | chr3 | 10183247 | 10183426 |
| chr3 | 10183632 | 10183811 | chr3 | 10857884 | 10858123 | chr3 | 11034163 | 11034462 |
| chr3 | 11034991 | 11035410 | chr3 | 12046310 | 12046727 | chr3 | 12917512 | 12917751 |
| chr3 | 12976987 | 12977150 | chr3 | 13323405 | 13324064 | chr3 | 13324277 | 13324516 |
| chr3 | 13324744 | 13325023 | chr3 | 13590341 | 13590940 | chr3 | 13679082 | 13679441 |
| chr3 | 13921316 | 13921555 | chr3 | 14851755 | 14851994 | chr3 | 14852233 | 14853012 |
| chr3 | 16553963 | 16554202 | chr3 | 16554251 | 15554730 | chr3 | 17001229 | 17001341 |
| chr3 | 19189367 | 19189545 | chr3 | 19189611 | 19189850 | chr3 | 19190061 | 19190253 |
| chr3 | 22413591 | 22413770 | chr3 | 22413871 | 22414050 | chr3 | 24870915 | 24870925 |
| chr3 | 24870982 | 24871281 | chr3 | 25469303 | 25469602 | chr3 | 25469605 | 25469784 |
| chr3 | 26663963 | 26664202 | chr3 | 26664303 | 26664842 | chr3 | 27754404 | 27754583 |
| chr3 | 27762260 | 27762733 | chr3 | 27762783 | 27762962 | chr3 | 27763492 | 27763671 |
| chr3 | 27764421 | 27764600 | chr3 | 27765085 | 27765444 | chr3 | 27771422 | 27772081 |
| chr3 | 28616745 | 28617764 | chr3 | 32858274 | 32859773 | chr3 | 32859992 | 32860351 |
| chr3 | 33259801 | 33260876 | chr3 | 35680768 | 35680947 | chr3 | 36805720 | 36805959 |
| chr3 | 36806053 | 36806292 | chr3 | 37493429 | 37493720 | chr3 | 37901952 | 37902028 |
| chr3 | 38030610 | 38030789 | chr3 | 38032257 | 38032436 | chr3 | 38035669 | 38036088 |
| chr3 | 38080596 | 38081015 | chr3 | 38081061 | 38081360 | chr3 | 38690527 | 38690766 |
| chr3 | 38691316 | 38691557 | chr3 | 39851674 | 39851913 | chr3 | 41266012 | 41266239 |
| chr3 | 42222640 | 42222737 | chr3 | 42640761 | 42640874 | chr3 | 42814467 | 42814706 |
| chr3 | 42947333 | 42947632 | chr3 | 44036176 | 44036415 | chr3 | 44036496 | 44036675 |
| chr3 | 44036743 | 44037282 | chr3 | 44037525 | 44037764 | chr3 | 44037781 | 44038740 |
| chr3 | 44039265 | 44040097 | chr3 | 44040413 | 44040652 | chr3 | 44040709 | 44041128 |
| chr3 | 44063354 | 44063953 | chr3 | 44596405 | 44596584 | chr3 | 44596614 | 44596913 |
| chr3 | 44626336 | 44626815 | chr3 | 44726855 | 44727274 | chr3 | 45187222 | 45187461 |
| chr3 | 46924905 | 46925039 | chr3 | 48227686 | 48227788 | chr3 | 48236391 | 48236553 |
| chr3 | 48693228 | 48694247 | chr3 | 48698723 | 48699859 | chr3 | 49906993 | 49907232 |
| chr3 | 49939836 | 49940495 | chr3 | 50243283 | 50243582 | chr3 | 50374581 | 50374760 |

TABLE 14-continued

| chr | start | end | chr | start | end | chr | start | end |
|---|---|---|---|---|---|---|---|---|
| chr3 | 50374843 | 50375022 | chr3 | 50375104 | 50375639 | chr3 | 50395432 | 50395611 |
| chr3 | 50402078 | 50403037 | chr3 | 50575518 | 50575635 | chr3 | 52552500 | 52552739 |
| chr3 | 52553395 | 52553537 | chr3 | 53032708 | 53033609 | chr3 | 54155525 | 54155764 |
| chr3 | 54157297 | 54157536 | chr3 | 54157780 | 54158006 | chr3 | 55519117 | 55519228 |
| chr3 | 55523019 | 55523318 | chr3 | 62353291 | 62354130 | chr3 | 62354187 | 62354426 |
| chr3 | 62354531 | 62355010 | chr3 | 62355332 | 62355571 | chr3 | 62355692 | 62357431 |
| chr3 | 62357527 | 62357766 | chr3 | 62358059 | 62358178 | chr3 | 62358444 | 62358683 |
| chr3 | 62358758 | 62359115 | chr3 | 62359276 | 62359995 | chr3 | 62360222 | 62360641 |
| chr3 | 62362812 | 62363206 | chr3 | 62363541 | 62363780 | chr3 | 62363819 | 62364418 |
| chr3 | 62364659 | 62365205 | chr3 | 62861044 | 62861223 | chr3 | 63264065 | 63264135 |
| chr3 | 63264158 | 63264244 | chr3 | 68056816 | 68057235 | chr3 | 68980843 | 68981202 |
| chr3 | 68981469 | 68981708 | chr3 | 69590865 | 69591044 | chr3 | 69591264 | 69592163 |
| chr3 | 69741004 | 69741087 | chr3 | 69937792 | 69937926 | chr3 | 71802489 | 71802720 |
| chr3 | 71803040 | 71803459 | chr3 | 71803553 | 71803912 | chr3 | 73045525 | 73045672 |
| chr3 | 75956924 | 75956463 | chr3 | 79815421 | 79815660 | chr3 | 79816688 | 79817099 |
| chr3 | 79817214 | 79817393 | chr3 | 85008452 | 85008811 | chr3 | 88248026 | 88248142 |
| chr3 | 96532726 | 96532965 | chr3 | 96533302 | 96533541 | chr3 | 96533947 | 96534186 |
| chr3 | 98620817 | 98621056 | chr3 | 99594836 | 99595195 | chr3 | 101230575 | 101230641 |
| chr3 | 101230942 | 101231174 | chr3 | 101397150 | 101397302 | chr3 | 106936068 | 106936294 |
| chr3 | 112052411 | 112052521 | chr3 | 117715472 | 117715643 | chr3 | 117715772 | 117716551 |
| chr3 | 120003954 | 120004438 | chr3 | 120169683 | 120169922 | chr3 | 120627319 | 120627535 |
| chr3 | 121902878 | 121903717 | chr3 | 122234151 | 122234246 | chr3 | 122702194 | 122702430 |
| chr3 | 123166972 | 123167631 | chr3 | 123167679 | 123167918 | chr3 | 125898567 | 125899292 |
| chr3 | 125899445 | 125899706 | chr3 | 125899740 | 125899979 | chr3 | 125932169 | 125932586 |
| chr3 | 126373433 | 126373619 | chr3 | 126373669 | 126373792 | chr3 | 126854599 | 126854898 |
| chr3 | 127534879 | 127534976 | chr3 | 127634112 | 127634291 | chr3 | 127794464 | 127794943 |
| chr3 | 127795248 | 127795253 | chr3 | 128202373 | 128202552 | chr3 | 128208829 | 128209308 |
| chr3 | 128273913 | 128274692 | chr3 | 128417127 | 128417306 | chr3 | 128719977 | 128720696 |
| chr3 | 128720780 | 128721319 | chr3 | 128764472 | 128764711 | chr3 | 129693075 | 129694391 |
| chr3 | 129694430 | 129694609 | chr3 | 130064351 | 130064588 | chr3 | 130064744 | 130064923 |
| chr3 | 130235952 | 130236298 | chr3 | 130519821 | 130519929 | chr3 | 131753957 | 131754136 |
| chr3 | 132756966 | 132757205 | chr3 | 133217923 | 133218102 | chr3 | 133748044 | 133748206 |
| chr3 | 133748552 | 133748679 | chr3 | 134369572 | 134369931 | chr3 | 134514792 | 134514879 |
| chr3 | 134514960 | 134514971 | chr3 | 134515040 | 134515459 | chr3 | 134515590 | 134516309 |
| chr3 | 136537567 | 136537806 | chr3 | 136538520 | 136538910 | chr3 | 136582941 | 136583037 |
| chr3 | 136751546 | 136751833 | chr3 | 137479149 | 137479388 | chr3 | 137479525 | 137479764 |
| chr3 | 137479893 | 137480847 | chr3 | 137481094 | 137481393 | chr3 | 137481782 | 137482261 |
| chr3 | 137483212 | 137483319 | chr3 | 137483570 | 137483691 | chr3 | 137483746 | 137484105 |
| chr3 | 137484319 | 137484618 | chr3 | 137485931 | 137486390 | chr3 | 137486429 | 137486653 |
| chr3 | 137487874 | 137488113 | chr3 | 137488856 | 137491135 | chr3 | 138153889 | 138154068 |
| chr3 | 138154240 | 138154479 | chr3 | 138655857 | 138656216 | chr3 | 138656743 | 138656982 |
| chr3 | 138657347 | 138659187 | chr3 | 138662060 | 138662535 | chr3 | 138662705 | 138662941 |
| chr3 | 138663611 | 138664249 | chr3 | 138664330 | 138664569 | chr3 | 138664827 | 138665426 |
| chr3 | 138665479 | 138665718 | chr3 | 138665779 | 138666378 | chr3 | 138668646 | 138669485 |
| chr3 | 138679375 | 138679614 | chr3 | 139258173 | 139258412 | chr3 | 139653413 | 139653772 |
| chr3 | 140769430 | 140769789 | chr3 | 140769830 | 140770909 | chr3 | 140771231 | 140771410 |
| chr3 | 140271716 | 140771955 | chr3 | 141174269 | 141174688 | chr3 | 141481983 | 141482162 |
| chr3 | 141516315 | 141516794 | chr3 | 142682184 | 142682483 | chr3 | 142791076 | 142791173 |
| chr3 | 142837906 | 142838445 | chr3 | 142838530 | 142839129 | chr3 | 142839439 | 142840338 |
| chr3 | 142896066 | 142896305 | chr3 | 145878591 | 145878641 | chr3 | 146187843 | 146188069 |
| chr3 | 147074871 | 147075110 | chr3 | 147027211 | 147077640 | chr3 | 147078865 | 147079284 |
| chr3 | 147087874 | 147087891 | chr3 | 147088363 | 147088542 | chr3 | 147088840 | 147089136 |
| chr3 | 147098332 | 147098571 | chr3 | 147105805 | 147106104 | chr3 | 147108758 | 147110017 |
| chr3 | 147110055 | 147110774 | chr3 | 147110835 | 147111188 | chr3 | 147111461 | 147111734 |
| chr3 | 147126963 | 147127142 | chr3 | 147127583 | 147128002 | chr3 | 147128188 | 147128420 |
| chr3 | 147136876 | 147137258 | chr3 | 147138694 | 147138932 | chr3 | 147139052 | 147139231 |
| chr3 | 147139272 | 147139631 | chr3 | 147142126 | 147142365 | chr3 | 148415327 | 148415746 |
| chr3 | 148803259 | 148803370 | chr3 | 149374866 | 149375105 | chr3 | 150802882 | 150803181 |
| chr3 | 150803941 | 150804180 | chr3 | 150804880 | 150805119 | chr3 | 152553245 | 152553484 |
| chr3 | 152553573 | 152553807 | chr3 | 152877592 | 152877703 | chr3 | 153838725 | 153838964 |
| chr3 | 153839429 | 153839559 | chr3 | 153839641 | 153840148 | chr3 | 154146034 | 154146513 |
| chr3 | 154146572 | 154146991 | chr3 | 154797250 | 154797289 | chr3 | 154797377 | 154797789 |
| chr3 | 156008943 | 156009501 | chr3 | 156534228 | 156534407 | chr3 | 157155164 | 157156523 |
| chr3 | 157155922 | 157156298 | chr3 | 157812122 | 157812721 | chr3 | 157812812 | 157813171 |
| chr3 | 157813507 | 157813926 | chr3 | 157815787 | 157815920 | chr3 | 157820502 | 157820681 |
| chr3 | 157820985 | 157821764 | chr3 | 157821939 | 157822106 | chr3 | 157822989 | 157823228 |
| chr3 | 157823390 | 157823569 | chr3 | 157824052 | 157824332 | chr3 | 157824414 | 157824953 |
| chr3 | 157825083 | 157825491 | chr3 | 158288801 | 158288974 | chr3 | 159756593 | 159756952 |
| chr3 | 159944397 | 159944636 | chr3 | 160167929 | 160168108 | chr3 | 164912329 | 164912568 |
| chr3 | 164912827 | 164913960 | chr3 | 164914906 | 164915205 | chr3 | 169376080 | 169376319 |
| chr3 | 169376581 | 169376878 | chr3 | 169378746 | 169379105 | chr3 | 169539810 | 169540704 |
| chr3 | 169540967 | 169541134 | chr3 | 170136540 | 170136839 | chr3 | 170137571 | 170137585 |
| chr3 | 170137624 | 170137803 | chr3 | 170302528 | 170302767 | chr3 | 170302989 | 170303257 |
| chr3 | 170303563 | 170303922 | chr3 | 171527953 | 171528071 | chr3 | 172165356 | 172166725 |
| chr3 | 172166783 | 172167142 | chr3 | 172167223 | 172167402 | chr3 | 172167580 | 172167995 |
| chr3 | 172355818 | 172355888 | chr3 | 172355903 | 172355997 | chr3 | 172425281 | 172425382 |
| chr3 | 172425701 | 172425802 | chr3 | 172469837 | 172469951 | chr3 | 173115155 | 173115634 |
| chr3 | 173302464 | 173302763 | chr3 | 173302900 | 173303319 | chr3 | 178861414 | 178861533 |

TABLE 14-continued

| chr | start | end | chr | start | end | chr | start | end |
|---|---|---|---|---|---|---|---|---|
| chr3 | 178916788 | 178916967 | chr3 | 178921465 | 178921644 | chr3 | 178935968 | 178936205 |
| chr3 | 178961997 | 178952176 | chr3 | 179168582 | 179169354 | chr3 | 179754086 | 179755465 |
| chr3 | 181413068 | 181413460 | chr3 | 181413647 | 181414425 | chr3 | 181419972 | 181420211 |
| chr3 | 181420226 | 181420465 | chr3 | 181421308 | 181422387 | chr3 | 181422464 | 181423063 |
| chr3 | 181428311 | 181428850 | chr3 | 181430614 | 181430853 | chr3 | 181437030 | 181437449 |
| chr3 | 181438095 | 181438454 | chr3 | 181440811 | 181442010 | chr3 | 181442069 | 181442488 |
| chr3 | 181442927 | 181443646 | chr3 | 181443662 | 181443961 | chr3 | 181444023 | 181444322 |
| chr3 | 181444335 | 181444754 | chr3 | 181444828 | 181445114 | chr3 | 181445268 | 181445567 |
| chr3 | 181445649 | 181445948 | chr3 | 182816010 | 182816129 | chr3 | 182895871 | 182895990 |
| chr3 | 183145336 | 183145695 | chr3 | 183145829 | 183146128 | chr3 | 183146297 | 183146536 |
| chr3 | 183146574 | 183146753 | chr3 | 183648036 | 183648101 | chr3 | 183728814 | 183728926 |
| chr3 | 183965514 | 183965625 | chr3 | 184017964 | 184018237 | chr3 | 184031616 | 184031734 |
| chr3 | 184057527 | 184057636 | chr3 | 184301634 | 184301873 | chr3 | 184319741 | 184319980 |
| chr3 | 185001908 | 185002018 | chr3 | 185271201 | 185271380 | chr3 | 185303173 | 185303352 |
| chr3 | 185362989 | 185363348 | chr3 | 185643246 | 185643485 | chr3 | 186078683 | 186078982 |
| chr3 | 186079119 | 186079412 | chr3 | 186080114 | 186080293 | chr3 | 186857051 | 186857710 |
| chr3 | 187387776 | 187388315 | chr3 | 192125754 | 192125933 | chr3 | 192126056 | 192126955 |
| chr3 | 192127265 | 192128164 | chr3 | 192232017 | 192232256 | chr3 | 192232362 | 192232437 |
| chr3 | 192232478 | 192232661 | chr3 | 192232753 | 192233232 | chr3 | 192958830 | 192959057 |
| chr3 | 193312046 | 193312165 | chr3 | 193419628 | 193419745 | chr3 | 193548557 | 193548797 |
| chr3 | 193548842 | 193548916 | chr3 | 193776015 | 193776194 | chr3 | 194048731 | 194049015 |
| chr3 | 194208185 | 194208664 | chr3 | 194407924 | 194407936 | chr3 | 194408055 | 194408103 |
| chr3 | 194408279 | 194409118 | chr3 | 195536642 | 195536828 | chr3 | 195538330 | 195538435 |
| chr3 | 195586956 | 195587195 | chr3 | 195601157 | 195601363 | chr3 | 195602364 | 195602435 |
| chr3 | 195648720 | 195648899 | chr3 | 196069893 | 196070192 | chr3 | 196255543 | 196255722 |
| chr3 | 196387206 | 196387505 | chr3 | 196387528 | 196387767 | chr3 | 196388303 | 196388662 |
| chr3 | 196731055 | 196731133 | chr3 | 196731197 | 196731414 | chr3 | 196755893 | 196756063 |
| chr3 | 197327025 | 197327131 | chr3 | 197616633 | 197616812 | chr3 | 197676955 | 197677134 |
| chr3 | 197685698 | 197685817 | chr3 | 197686060 | 197686177 | chr3 | 197686891 | 197687310 |
| chr4 | 107616 | 107855 | chr4 | 330311 | 330790 | chr4 | 331308 | 331416 |
| chr4 | 568333 | 570012 | chr4 | 570931 | 571110 | chr4 | 571420 | 571779 |
| chr4 | 628488 | 628770 | chr4 | 651110 | 651348 | chr4 | 657570 | 657657 |
| chr4 | 678397 | 678576 | chr4 | 682710 | 683009 | chr4 | 718082 | 718202 |
| chr4 | 718240 | 718321 | chr4 | 829537 | 829716 | chr4 | 955292 | 955531 |
| chr4 | 955774 | 956013 | chr4 | 995777 | 996436 | chr4 | 996555 | 996794 |
| chr4 | 1008642 | 1008806 | chr4 | 1016041 | 1016340 | chr4 | 1016533 | 1016787 |
| chr4 | 1025852 | 1026151 | chr4 | 1093457 | 1093558 | chr4 | 1165276 | 1165575 |
| chr4 | 1188947 | 1189126 | chr4 | 1282441 | 1282620 | chr4 | 1331636 | 1331780 |
| chr4 | 1338615 | 1338891 | chr4 | 1339023 | 1339130 | chr4 | 1396498 | 1396917 |
| chr4 | 1397297 | 1397596 | chr4 | 1398222 | 1398461 | chr4 | 1399627 | 1399652 |
| chr4 | 1400638 | 1400877 | chr4 | 1401608 | 1401847 | chr4 | 1612294 | 1512473 |
| chr4 | 1556335 | 1556603 | chr4 | 1576387 | 1576626 | chr4 | 1616606 | 1617173 |
| chr4 | 1687006 | 1687185 | chr4 | 1803447 | 1803686 | chr4 | 1806010 | 1806089 |
| chr4 | 1807281 | 1807460 | chr4 | 1993677 | 1994276 | chr4 | 2042117 | 2042626 |
| chr4 | 2066011 | 2066370 | chr4 | 2305571 | 2305930 | chr4 | 2527903 | 2528012 |
| chr4 | 2540247 | 2540395 | chr4 | 2765767 | 2766006 | chr4 | 2926292 | 2926471 |
| chr4 | 2978878 | 2979094 | chr4 | 3446917 | 3447096 | chr4 | 3447737 | 3448096 |
| chr4 | 3768759 | 3769418 | chr4 | 3769439 | 3769678 | chr4 | 3873613 | 3873852 |
| chr4 | 4228094 | 4228333 | chr4 | 4229586 | 4229885 | chr4 | 4387431 | 4387730 |
| chr4 | 4417467 | 4417706 | chr4 | 4855018 | 4855257 | chr4 | 4855283 | 4855522 |
| chr4 | 4862671 | 4863210 | chr4 | 4867613 | 4867864 | chr4 | 4867924 | 4867972 |
| chr4 | 4868468 | 4869187 | chr4 | 4872009 | 4872248 | chr4 | 4872695 | 4872934 |
| chr4 | 4873329 | 4873580 | chr4 | 5052995 | 5053594 | chr4 | 5053651 | 5054190 |
| chr4 | 5709819 | 5710358 | chr4 | 5712891 | 5713370 | chr4 | 5889848 | 5890147 |
| chr4 | 5890180 | 5890539 | chr4 | 5891871 | 5892290 | chr4 | 5892676 | 5892791 |
| chr4 | 5893898 | 5894434 | chr4 | 5894583 | 5894882 | chr4 | 6200797 | 6201336 |
| chr4 | 6202011 | 6202370 | chr4 | 6247277 | 6247456 | chr4 | 6564904 | 6565143 |
| chr4 | 6670110 | 6670289 | chr4 | 6748251 | 6748662 | chr4 | 6957489 | 6957701 |
| chr4 | 7647679 | 7648038 | chr4 | 7758402 | 7758581 | chr4 | 8582475 | 8582654 |
| chr4 | 8607724 | 8608023 | chr4 | 8608459 | 8608698 | chr4 | 8858804 | 8859823 |
| chr4 | 8859875 | 8860654 | chr4 | 8861563 | 8862102 | chr4 | 8862705 | 8863004 |
| chr4 | 8863339 | 8863878 | chr4 | 8864434 | 8864699 | chr4 | 8864736 | 8865155 |
| chr4 | 2868734 | 8869453 | chr4 | 8869498 | 8869917 | chr4 | 8872957 | 8873436 |
| chr4 | 8873718 | 8874077 | chr4 | 8874397 | 8874812 | chr4 | 8875803 | 8875982 |
| chr4 | 8893427 | 8893606 | chr4 | 8893714 | 8894013 | chr4 | 8894547 | 8895446 |
| chr4 | 8895480 | 8895659 | chr4 | 8895835 | 8896134 | chr4 | 9423195 | 9423281 |
| chr4 | 9782942 | 9783502 | chr4 | 10458309 | 10459208 | chr4 | 10462740 | 10463636 |
| chr4 | 11429482 | 11429720 | chr4 | 13523929 | 13524528 | chr4 | 13524571 | 13524872 |
| chr4 | 13537492 | 13537779 | chr4 | 13540907 | 13541146 | chr4 | 13541309 | 13541548 |
| chr4 | 13543777 | 13544196 | chr4 | 13545483 | 13545842 | chr4 | 13545933 | 13546172 |
| chr4 | 13548404 | 13548999 | chr4 | 13549246 | 13549605 | chr4 | 15780123 | 15780422 |
| chr4 | 16084642 | 16085481 | chr4 | 16085531 | 16085770 | chr4 | 17782913 | 17783692 |
| chr4 | 20254619 | 20254798 | chr4 | 20255339 | 20255938 | chr4 | 20256067 | 20256426 |
| chr4 | 21950146 | 21950445 | chr4 | 24801718 | 24802077 | chr4 | 24914564 | 24914743 |
| chr4 | 25656728 | 25656893 | chr4 | 25657338 | 25657577 | chr4 | 27086358 | 27086537 |
| chr4 | 30724162 | 30724461 | chr4 | 37245640 | 37245939 | chr4 | 37246060 | 37246959 |
| chr4 | 37247007 | 37247306 | chr4 | 40910206 | 40910563 | chr4 | 41258624 | 41259276 |
| chr4 | 41746922 | 41747221 | chr4 | 41747419 | 41747658 | chr4 | 41747858 | 41747977 |

TABLE 14-continued

| chr | start | end | chr | start | end | chr | start | end |
|---|---|---|---|---|---|---|---|---|
| chr4 | 41748038 | 41748397 | chr4 | 41748583 | 41748882 | chr4 | 41748976 | 41749138 |
| chr4 | 41749187 | 41749846 | chr4 | 41750125 | 41750604 | chr4 | 41751789 | 41751990 |
| chr4 | 41752363 | 41752782 | chr4 | 41752884 | 41753483 | chr4 | 41753512 | 41754171 |
| chr4 | 41875337 | 41875891 | chr4 | 41881286 | 41881517 | chr4 | 41882469 | 41882682 |
| chr4 | 41882988 | 41883407 | chr4 | 41883411 | 41883710 | chr4 | 41993731 | 41993896 |
| chr4 | 42152808 | 42154127 | chr4 | 42154201 | 42154440 | chr4 | 42154561 | 42155100 |
| chr4 | 42398768 | 42398947 | chr4 | 42399045 | 42399284 | chr4 | 42399601 | 42399960 |
| chr4 | 44449387 | 44449746 | chr4 | 44450170 | 44450469 | chr4 | 46995079 | 46995918 |
| chr4 | 47034834 | 47035013 | chr4 | 48485152 | 48486104 | chr4 | 48486254 | 48486493 |
| chr4 | 48492100 | 48492517 | chr4 | 48988013 | 48988229 | chr4 | 48988380 | 48988432 |
| chr4 | 53728417 | 53729087 | chr4 | 54966756 | 54967175 | chr4 | 54967264 | 54967563 |
| chr4 | 54969832 | 54970174 | chr4 | 54970277 | 54970576 | chr4 | 54975855 | 54976214 |
| chr4 | 55092973 | 55093332 | chr4 | 55096143 | 55096363 | chr4 | 55096441 | 55096442 |
| chr4 | 55097315 | 55097554 | chr4 | 55097709 | 55097729 | chr4 | 55097874 | 55098473 |
| chr4 | 55098590 | 55098769 | chr4 | 55099040 | 55099159 | chr4 | 55524138 | 55524367 |
| chr4 | 55991019 | 55991270 | chr4 | 55992030 | 55992269 | chr4 | 56659618 | 56660097 |
| chr4 | 57371632 | 57372051 | chr4 | 57372241 | 57372600 | chr4 | 57396866 | 57397345 |
| chr4 | 57521300 | 57522908 | chr4 | 57687632 | 57687871 | chr4 | 57777338 | 57777577 |
| chr4 | 57803529 | 57803613 | chr4 | 57975930 | 57976289 | chr4 | 57976316 | 57976675 |
| chr4 | 62066106 | 62066645 | chr4 | 62067419 | 62067718 | chr4 | 62067992 | 62068231 |
| chr4 | 66535048 | 66535527 | chr4 | 66536068 | 66536427 | chr4 | 74702379 | 74702608 |
| chr4 | 74809786 | 74810025 | chr4 | 75241349 | 75241528 | chr4 | 75858482 | 75858611 |
| chr4 | 76555455 | 76555934 | chr4 | 76912717 | 76912836 | chr4 | 79689573 | 79689812 |
| chr4 | 81106252 | 81106669 | chr4 | 81124201 | 81124740 | chr4 | 81186972 | 81187151 |
| chr4 | 81187485 | 81187664 | chr4 | 81188230 | 81188644 | chr4 | 81189336 | 81189995 |
| chr4 | 81951357 | 81951536 | chr4 | 81951938 | 81952046 | chr4 | 81952078 | 81952437 |
| chr4 | 82136786 | 82136145 | chr4 | 82136403 | 82136642 | chr4 | 82136733 | 82136912 |
| chr4 | 83323428 | 83323677 | chr4 | 85402681 | 85403425 | chr4 | 85403824 | 85404783 |
| chr4 | 85413977 | 85414244 | chr4 | 85414270 | 85414509 | chr4 | 85414637 | 85414936 |
| chr4 | 85417241 | 85417474 | chr4 | 85417517 | 85417660 | chr4 | 85417873 | 85418166 |
| chr4 | 85418319 | 85419038 | chr4 | 85422101 | 85422520 | chr4 | 85422866 | 85423405 |
| chr4 | 85424323 | 85424562 | chr4 | 87515263 | 87515442 | chr4 | 89378362 | 89378601 |
| chr4 | 89378667 | 89378966 | chr4 | 90757439 | 90757913 | chr4 | 90758031 | 90758210 |
| chr4 | 90758681 | 90758980 | chr4 | 93225163 | 93225252 | chr4 | 93226367 | 93226606 |
| chr4 | 93226719 | 93226958 | chr4 | 94750882 | 94751241 | chr4 | 94751342 | 94751581 |
| chr4 | 94753341 | 94753520 | chr4 | 94755887 | 94756186 | chr4 | 95127560 | 95127679 |
| chr4 | 96470678 | 96470857 | chr4 | 101111166 | 101111585 | chr4 | 101111765 | 101112058 |
| chr4 | 107955210 | 107955929 | chr4 | 107956582 | 107957181 | chr4 | 107957271 | 107957570 |
| chr4 | 109093016 | 109093255 | chr4 | 109093307 | 109093606 | chr4 | 110222996 | 110224075 |
| chr4 | 111532558 | 111533032 | chr4 | 111536192 | 111536791 | chr4 | 111536882 | 111537121 |
| chr4 | 111537356 | 111537572 | chr4 | 111540101 | 111540460 | chr4 | 111542113 | 111542570 |
| chr4 | 111542728 | 111542832 | chr4 | 111543132 | 111543551 | chr4 | 111543579 | 111543807 |
| chr4 | 111544303 | 111544662 | chr4 | 111549726 | 111549905 | chr4 | 111550517 | 111550930 |
| chr4 | 111552044 | 111552223 | chr4 | 111553006 | 111553545 | chr4 | 111553815 | 111564054 |
| chr4 | 111554864 | 111555447 | chr4 | 111557888 | 111558127 | chr4 | 111558473 | 111569312 |
| chr4 | 111560174 | 111560713 | chr4 | 111562493 | 111562732 | chr4 | 113154804 | 113155043 |
| chr4 | 113430537 | 113430776 | chr4 | 113431755 | 113432654 | chr4 | 113436133 | 113436372 |
| chr4 | 113441514 | 113441813 | chr4 | 113442013 | 113442612 | chr4 | 113444003 | 113444534 |
| chr4 | 117847310 | 117847549 | chr4 | 121843986 | 121844285 | chr4 | 121992170 | 121992409 |
| chr4 | 121993915 | 121994334 | chr4 | 122301405 | 122301934 | chr4 | 122302032 | 122302331 |
| chr4 | 122685744 | 122686029 | chr4 | 122686119 | 122686598 | chr4 | 122871195 | 122871434 |
| chr4 | 122871488 | 122872087 | chr4 | 123664147 | 123664249 | chr4 | 126237252 | 126237491 |
| chr4 | 126237552 | 126237701 | chr4 | 126237931 | 126238511 | chr4 | 128543956 | 128544255 |
| chr4 | 128544569 | 128544868 | chr4 | 134067794 | 134068093 | chr4 | 134068475 | 134068894 |
| chr4 | 134069215 | 134069394 | chr4 | 134069498 | 134069977 | chr4 | 134070300 | 134070479 |
| chr4 | 134071559 | 134073058 | chr4 | 134073104 | 134073403 | chr4 | 134073486 | 134073725 |
| chr4 | 134073772 | 134073789 | chr4 | 134073944 | 134074243 | chr4 | 140200427 | 140201566 |
| chr4 | 140656567 | 140657166 | chr4 | 141347925 | 141348227 | chr4 | 141418841 | 141419500 |
| chr4 | 141488790 | 141489159 | chr4 | 142053155 | 142053235 | chr4 | 142053418 | 142053837 |
| chr4 | 142054141 | 142054560 | chr4 | 143766714 | 143767013 | chr4 | 144621248 | 144622147 |
| chr4 | 145567951 | 145568250 | chr4 | 145568361 | 145568745 | chr4 | 146853937 | 146854056 |
| chr4 | 147558179 | 147558598 | chr4 | 147559220 | 147560659 | chr4 | 147560835 | 147562154 |
| chr4 | 147568549 | 147569148 | chr4 | 147569546 | 147569685 | chr4 | 147569697 | 147569725 |
| chr4 | 147576079 | 147576738 | chr4 | 152246058 | 152246237 | chr4 | 152246398 | 152246403 |
| chr4 | 153249297 | 153249476 | chr4 | 153702690 | 153702805 | chr4 | 154216277 | 154216449 |
| chr4 | 154709440 | 154710639 | chr4 | 154710701 | 154710999 | chr4 | 154712084 | 154712683 |
| chr4 | 154713426 | 154713605 | chr4 | 154713861 | 154714085 | chr4 | 155254092 | 155254271 |
| chr4 | 155411411 | 155411786 | chr4 | 155411930 | 155412370 | chr4 | 155663129 | 155663728 |
| chr4 | 155665371 | 155665550 | chr4 | 156129079 | 156129258 | chr4 | 156129354 | 156129593 |
| chr4 | 156129653 | 156129892 | chr4 | 156129963 | 156130382 | chr4 | 156297337 | 156297636 |
| chr4 | 156297747 | 156298130 | chr4 | 156588237 | 156588245 | chr4 | 156588364 | 156588476 |
| chr4 | 156589179 | 156589203 | chr4 | 156589259 | 156589418 | chr4 | 156680156 | 156680485 |
| chr4 | 156680596 | 156680635 | chr4 | 156681281 | 156681465 | chr4 | 158141502 | 158141681 |
| chr4 | 158142744 | 158143101 | chr4 | 158143355 | 158143654 | chr4 | 164252890 | 164253549 |
| chr4 | 165304428 | 165304667 | chr4 | 165304948 | 165305247 | chr4 | 166414817 | 166414996 |
| chr4 | 166794691 | 166794990 | chr4 | 166795933 | 166796292 | chr4 | 168155010 | 168155369 |
| chr4 | 170865262 | 170865381 | chr4 | 170947187 | 170947426 | chr4 | 172734067 | 172734306 |
| chr4 | 172734461 | 172734880 | chr4 | 174429584 | 174429763 | chr4 | 174430212 | 174431171 |

TABLE 14-continued

| chr | start | end | chr | start | end | chr | start | end |
|---|---|---|---|---|---|---|---|---|
| chr4 | 174438477 | 174438627 | chr4 | 174439741 | 174440340 | chr4 | 174440555 | 174440794 |
| chr4 | 174443138 | 174443317 | chr4 | 174443480 | 174444019 | chr4 | 174444077 | 174444256 |
| chr4 | 174446387 | 174446595 | chr4 | 174449847 | 174451586 | chr4 | 174451768 | 174452187 |
| chr4 | 174459094 | 174459747 | chr4 | 174459770 | 174459933 | chr4 | 174460085 | 174460309 |
| chr4 | 175132661 | 175132840 | chr4 | 175132994 | 175133293 | chr4 | 175134806 | 175135765 |
| chr4 | 175135847 | 175136086 | chr4 | 175138419 | 175138629 | chr4 | 175138870 | 175139349 |
| chr4 | 175139473 | 175139772 | chr4 | 175750358 | 175750805 | chr4 | 176923342 | 176923641 |
| chr4 | 176987230 | 176987448 | chr4 | 177713154 | 177713513 | chr4 | 180979196 | 180979375 |
| chr4 | 180980208 | 180980447 | chr4 | 183063573 | 183064048 | chr4 | 183064517 | 183064756 |
| chr4 | 183064771 | 183065070 | chr4 | 184019164 | 184019403 | chr4 | 184019595 | 184019834 |
| chr4 | 184020043 | 184020263 | chr4 | 184375709 | 184375816 | chr4 | 184718157 | 184718456 |
| chr4 | 184826157 | 184826576 | chr4 | 184826976 | 184827328 | chr4 | 184921806 | 184922165 |
| chr4 | 185089598 | 185089897 | chr4 | 185937252 | 185937971 | chr4 | 185938412 | 185938651 |
| chr4 | 185940250 | 185940549 | chr4 | 185941484 | 185942863 | chr5 | 53756 | 53995 |
| chr5 | 92072 | 92210 | chr5 | 320762 | 321061 | chr5 | 343957 | 344017 |
| chr5 | 373976 | 374369 | chr5 | 400112 | 400291 | chr5 | 480918 | 481037 |
| chr5 | 491257 | 491616 | chr5 | 524252 | 524491 | chr5 | 528502 | 528775 |
| chr5 | 538663 | 538902 | chr5 | 554212 | 554569 | chr5 | 554812 | 554916 |
| chr5 | 555193 | 555372 | chr5 | 555891 | 556070 | chr5 | 677799 | 678098 |
| chr5 | 1034508 | 1034747 | chr5 | 1131130 | 1131478 | chr5 | 1193302 | 1193465 |
| chr5 | 1193793 | 1194032 | chr5 | 1221103 | 1221402 | chr5 | 1294550 | 1294849 |
| chr5 | 1294928 | 1295767 | chr5 | 1445078 | 1445369 | chr5 | 1445654 | 1446013 |
| chr5 | 1446220 | 1446699 | chr5 | 1746941 | 1747180 | chr5 | 1874877 | 1875176 |
| chr5 | 1875356 | 1875595 | chr5 | 1875796 | 1876935 | chr5 | 1877081 | 1877320 |
| chr5 | 1877912 | 1878631 | chr5 | 1878653 | 1879090 | chr5 | 1879513 | 1879812 |
| chr5 | 1882211 | 1882690 | chr5 | 1882758 | 1883177 | chr5 | 1883429 | 1883908 |
| chr5 | 1884089 | 1884328 | chr5 | 1884479 | 1884778 | chr5 | 1885069 | 1885548 |
| chr5 | 1885910 | 1886269 | chr5 | 1886443 | 1886682 | chr5 | 1886736 | 1887815 |
| chr5 | 1930701 | 1931840 | chr5 | 1950698 | 1951057 | chr5 | 1952550 | 1952729 |
| chr5 | 2038629 | 2038928 | chr5 | 2324309 | 2324488 | chr5 | 2541400 | 2541699 |
| chr5 | 2738746 | 2739525 | chr5 | 2739780 | 2741139 | chr5 | 2743516 | 2743815 |
| chr5 | 2748298 | 2748537 | chr5 | 2749110 | 2749529 | chr5 | 2749625 | 2749804 |
| chr5 | 2750617 | 2751456 | chr5 | 2751615 | 2751974 | chr5 | 2752897 | 2753153 |
| chr5 | 2754664 | 2754703 | chr5 | 2754804 | 2754843 | chr5 | 2755227 | 2756486 |
| chr5 | 2756504 | 2757523 | chr5 | 3031800 | 3032099 | chr5 | 3324948 | 3325367 |
| chr5 | 3590314 | 3590853 | chr5 | 3591252 | 3591491 | chr5 | 3591768 | 3592127 |
| chr5 | 3592626 | 3592961 | chr5 | 3594155 | 3594814 | chr5 | 3595015 | 3595254 |
| chr5 | 3595361 | 3596080 | chr5 | 3596118 | 3596297 | chr5 | 3596441 | 3596980 |
| chr5 | 3597317 | 3597556 | chr5 | 3599759 | 3599938 | chr5 | 3600076 | 3600255 |
| chr5 | 3600794 | 3600973 | chr5 | 3602712 | 3603422 | chr5 | 3606532 | 3606771 |
| chr5 | 3673960 | 3674256 | chr5 | 4144300 | 4144592 | chr5 | 5139578 | 5139997 |
| chr5 | 5140079 | 5140318 | chr5 | 5140527 | 5141006 | chr5 | 6228525 | 6228650 |
| chr5 | 6448837 | 6449676 | chr5 | 6583371 | 6583670 | chr5 | 6687175 | 6687528 |
| chr5 | 7395162 | 7395641 | chr5 | 7850181 | 7850286 | chr5 | 7850919 | 7851218 |
| chr5 | 9546511 | 9546750 | chr5 | 10333611 | 10334210 | chr5 | 10564925 | 10565704 |
| chr5 | 11384806 | 11385465 | chr5 | 11903659 | 11904798 | chr5 | 11904801 | 11905040 |
| chr5 | 15500659 | 15501018 | chr5 | 16178946 | 16179245 | chr5 | 16179436 | 16179795 |
| chr5 | 16179945 | 16180364 | chr5 | 16466683 | 16466796 | chr5 | 16467097 | 16467216 |
| chr5 | 16936255 | 16936402 | chr5 | 16936500 | 16936614 | chr5 | 17203036 | 17203266 |
| chr5 | 17217854 | 17218033 | chr5 | 17218121 | 17218300 | chr5 | 17218862 | 17219101 |
| chr5 | 17512040 | 17512192 | chr5 | 22853425 | 22853596 | chr5 | 31193844 | 31194083 |
| chr5 | 31194299 | 31194511 | chr5 | 31639583 | 31640008 | chr5 | 31691580 | 31691745 |
| chr5 | 31854987 | 31855286 | chr5 | 32710252 | 32710551 | chr5 | 32710718 | 32710957 |
| chr5 | 32711024 | 32711617 | chr5 | 32711729 | 32711968 | chr5 | 32711985 | 32712584 |
| chr5 | 32712675 | 32712943 | chr5 | 33298097 | 33298101 | chr5 | 33891980 | 33892219 |
| chr5 | 33892339 | 33892518 | chr5 | 33936067 | 33936761 | chr5 | 34656834 | 34657042 |
| chr5 | 37834610 | 37834789 | chr5 | 37834855 | 37834900 | chr5 | 37836572 | 37838071 |
| chr5 | 37838448 | 37838987 | chr5 | 37839684 | 37840223 | chr5 | 37840288 | 37840843 |
| chr5 | 38257397 | 38257696 | chr5 | 38257752 | 38258051 | chr5 | 38656996 | 38557076 |
| chr5 | 38567188 | 38557427 | chr5 | 38845574 | 38845955 | chr5 | 38846219 | 38846533 |
| chr5 | 39343086 | 39343201 | chr5 | 40681036 | 40681455 | chr5 | 40681601 | 40682080 |
| chr5 | 42424732 | 42425151 | chr5 | 42950902 | 42952445 | chr5 | 42991751 | 42993010 |
| chr5 | 42993313 | 42993547 | chr5 | 42993853 | 42994272 | chr5 | 42994593 | 42994892 |
| chr5 | 42995015 | 42995254 | chr5 | 43007862 | 43008041 | chr5 | 43008113 | 43008472 |
| chr5 | 43017851 | 43018690 | chr5 | 43019144 | 43019424 | chr5 | 43019729 | 43019968 |
| chr5 | 43040768 | 43041067 | chr5 | 43215459 | 43215562 | chr5 | 43396915 | 43397334 |
| chr5 | 44389705 | 44389929 | chr5 | 45695091 | 45695630 | chr5 | 45695823 | 45696047 |
| chr5 | 45696239 | 45696538 | chr5 | 49736497 | 49736789 | chr5 | 50262842 | 50263104 |
| chr5 | 50263486 | 50263725 | chr5 | 50264216 | 50264695 | chr5 | 50264746 | 50264925 |
| chr5 | 50265228 | 50265527 | chr5 | 50265621 | 50265960 | chr5 | 50674051 | 50674290 |
| chr5 | 50674486 | 50674557 | chr5 | 50674638 | 50674665 | chr5 | 50674925 | 50675164 |
| chr5 | 50678269 | 50678273 | chr5 | 50678373 | 50678552 | chr5 | 50695193 | 50695540 |
| chr5 | 54179491 | 54179730 | chr5 | 54179989 | 54180168 | chr5 | 54516275 | 54517114 |
| chr5 | 54518577 | 54519406 | chr5 | 54527226 | 54527444 | chr5 | 56248119 | 56248358 |
| chr5 | 57878174 | 57878473 | chr5 | 57878612 | 57878775 | chr5 | 57878811 | 57878851 |
| chr5 | 59188293 | 59188429 | chr5 | 59188952 | 59189311 | chr5 | 59189787 | 59190026 |
| chr5 | 63254815 | 63255354 | chr5 | 63257645 | 63257944 | chr5 | 63801932 | 63802591 |
| chr5 | 63986409 | 63986888 | chr5 | 67591197 | 67591233 | chr5 | 68391320 | 68391429 |

TABLE 14-continued

| chr | start | end | chr | start | end | chr | start | end |
|---|---|---|---|---|---|---|---|---|
| chr5 | 71014629 | 71014988 | chr5 | 71015095 | 71015814 | chr5 | 71403491 | 71403730 |
| chr5 | 71403882 | 71404158 | chr5 | 72416170 | 72416262 | chr5 | 72526319 | 72526738 |
| chr5 | 72528360 | 72528539 | chr5 | 72529200 | 72530699 | chr5 | 72594722 | 72595141 |
| chr5 | 72595456 | 72595875 | chr5 | 72598977 | 72599936 | chr5 | 72677577 | 72678416 |
| chr5 | 72715160 | 72715846 | chr5 | 72716022 | 72716239 | chr5 | 72732724 | 72732963 |
| chr5 | 72732990 | 72733268 | chr5 | 72740047 | 72740286 | chr5 | 72746606 | 72746785 |
| chr5 | 75377809 | 75378108 | chr5 | 75380089 | 75380268 | chr5 | 75380530 | 75381006 |
| chr5 | 76011192 | 76011431 | chr5 | 76012504 | 76012681 | chr5 | 76249176 | 76250250 |
| chr5 | 76250351 | 76250590 | chr5 | 76506369 | 76506608 | chr5 | 76506956 | 76507195 |
| chr5 | 76923601 | 76924494 | chr5 | 76924856 | 76925018 | chr5 | 76925477 | 76925776 |
| chr5 | 76928070 | 76928487 | chr5 | 76928588 | 76929007 | chr5 | 76932228 | 76932407 |
| chr5 | 76932463 | 76933362 | chr5 | 76934073 | 76934972 | chr5 | 76935937 | 76936039 |
| chr5 | 76936100 | 76936819 | chr5 | 76939328 | 76939867 | chr5 | 76940241 | 76940477 |
| chr5 | 76941115 | 76941414 | chr5 | 77140440 | 77140799 | chr5 | 77147520 | 77148214 |
| chr5 | 77148396 | 77148669 | chr5 | 27268278 | 77269408 | chr5 | 77806123 | 77806213 |
| chr5 | 78407567 | 78407926 | chr5 | 78408118 | 78408537 | chr5 | 79783152 | 79783256 |
| chr5 | 79864809 | 79865168 | chr5 | 79865969 | 79866508 | chr5 | 79947497 | 79947796 |
| chr5 | 80255722 | 80256261 | chr5 | 80689499 | 80689819 | chr5 | 80690030 | 80690278 |
| chr5 | 82767342 | 82767881 | chr5 | 82768798 | 82769157 | chr5 | 83679121 | 83679300 |
| chr5 | 83679592 | 83680431 | chr5 | 83680592 | 83680812 | chr5 | 87955360 | 87955455 |
| chr5 | 87955502 | 87955899 | chr5 | 87956103 | 87957062 | chr5 | 87962865 | 87963006 |
| chr5 | 87963365 | 87963601 | chr5 | 87967686 | 87968165 | chr5 | 87968411 | 87968942 |
| chr5 | 87970114 | 87970953 | chr5 | 87974027 | 87974386 | chr5 | 87974767 | 87975126 |
| chr5 | 87976104 | 87976408 | chr5 | 87976423 | 87976662 | chr5 | 87979655 | 87979779 |
| chr5 | 87979900 | 87980014 | chr5 | 87980047 | 87980079 | chr5 | 87980322 | 87980346 |
| chr5 | 87980871 | 87981341 | chr5 | 87985819 | 87986058 | chr5 | 87986127 | 87986154 |
| chr5 | 87986233 | 87986366 | chr5 | 87986445 | 87986472 | chr5 | 87988431 | 87988670 |
| chr5 | 87990311 | 87990530 | chr5 | 88185377 | 88186087 | chr5 | 89854760 | 89854999 |
| chr5 | 92939817 | 92940236 | chr5 | 94955591 | 94966010 | chr5 | 94956849 | 94957088 |
| chr5 | 94982143 | 94982314 | chr5 | 95767856 | 95768035 | chr5 | 95768068 | 95768427 |
| chr5 | 95768828 | 95769173 | chr5 | 100236601 | 100236840 | chr5 | 100238808 | 100239167 |
| chr5 | 101631391 | 101631630 | chr5 | 107005906 | 107006265 | chr5 | 111987788 | 111987901 |
| chr5 | 112043011 | 112043367 | chr5 | 112073328 | 112073567 | chr5 | 112175566 | 112175730 |
| chr5 | 112629342 | 112629359 | chr5 | 112629394 | 112629761 | chr5 | 113391163 | 113391218 |
| chr5 | 113391284 | 113392122 | chr5 | 113698466 | 113698885 | chr5 | 113698915 | 113699203 |
| chr5 | 114514867 | 114515754 | chr5 | 115151174 | 115152733 | chr5 | 115297105 | 115297644 |
| chr5 | 115297836 | 115298135 | chr5 | 115298410 | 115298829 | chr5 | 115298894 | 115299133 |
| chr5 | 119799840 | 119800079 | chr5 | 119801223 | 119801522 | chr5 | 121413445 | 121413684 |
| chr5 | 122422161 | 122422386 | chr5 | 122422516 | 122422754 | chr5 | 122423233 | 122423452 |
| chr5 | 122425029 | 122425268 | chr5 | 122431039 | 122431458 | chr5 | 124128503 | 124128574 |
| chr5 | 126626256 | 126626795 | chr5 | 127872847 | 127873086 | chr5 | 127873190 | 127873789 |
| chr5 | 127874345 | 127874944 | chr5 | 128300588 | 128300887 | chr5 | 128795984 | 128796343 |
| chr5 | 128796777 | 128797076 | chr5 | 128797246 | 128797485 | chr5 | 129239966 | 129240205 |
| chr5 | 131992008 | 131992247 | chr5 | 132947392 | 132947931 | chr5 | 133820025 | 133820136 |
| chr5 | 134363235 | 134363320 | chr5 | 134364026 | 134364075 | chr5 | 134364115 | 134364205 |
| chr5 | 134364295 | 134364594 | chr5 | 134366634 | 134366873 | chr5 | 134367007 | 134367306 |
| chr5 | 134374370 | 134375309 | chr5 | 134376120 | 134376474 | chr5 | 134376612 | 134376911 |
| chr5 | 134385869 | 134386466 | chr5 | 134582953 | 134582969 | chr5 | 134825372 | 134825611 |
| chr5 | 134825799 | 134826098 | chr5 | 134870362 | 134870601 | chr5 | 134870689 | 134871288 |
| chr5 | 134871526 | 134872125 | chr5 | 134879391 | 134879973 | chr5 | 134880154 | 134880590 |
| chr5 | 134914539 | 134914838 | chr5 | 135265664 | 135265842 | chr5 | 135266034 | 135266753 |
| chr5 | 135528098 | 135528337 | chr5 | 136834009 | 136834608 | chr5 | 136834624 | 136834923 |
| chr5 | 137225016 | 137225268 | chr5 | 138273717 | 138273845 | chr5 | 139047897 | 139048256 |
| chr5 | 139227692 | 139227991 | chr5 | 139525654 | 139525833 | chr5 | 139779840 | 139779953 |
| chr5 | 140174701 | 140174994 | chr5 | 140187003 | 140187240 | chr5 | 140305895 | 140306134 |
| chr5 | 140306228 | 140306827 | chr5 | 140346514 | 140346753 | chr5 | 140514817 | 140514996 |
| chr5 | 140604361 | 140604596 | chr5 | 140613851 | 140614089 | chr5 | 140614230 | 140614469 |
| chr5 | 140777354 | 140777588 | chr5 | 140797000 | 140797419 | chr5 | 140800384 | 140801343 |
| chr5 | 140811013 | 140811138 | chr5 | 140855515 | 140856710 | chr5 | 141031047 | 141031205 |
| chr5 | 141262957 | 141263316 | chr5 | 141931261 | 141931585 | chr5 | 142784881 | 142785305 |
| chr5 | 145713562 | 145713981 | chr5 | 145717097 | 145717516 | chr5 | 145718714 | 145720024 |
| chr5 | 145720763 | 145720942 | chr5 | 145722033 | 145723112 | chr5 | 145724421 | 145724780 |
| chr5 | 145725109 | 145725948 | chr5 | 146257258 | 146257677 | chr5 | 146889129 | 146889668 |
| chr5 | 149681971 | 149682270 | chr5 | 150051025 | 150051744 | chr5 | 150400044 | 150400283 |
| chr5 | 151066339 | 151066578 | chr5 | 151304297 | 151304476 | chr5 | 153852579 | 153852878 |
| chr5 | 153853330 | 153853569 | chr5 | 153855101 | 153855340 | chr5 | 153855506 | 153855925 |
| chr5 | 153856004 | 153856483 | chr5 | 153856847 | 153857085 | chr5 | 153857285 | 153857524 |
| chr5 | 153858220 | 153858699 | chr5 | 153859573 | 153859812 | chr5 | 153861948 | 153862667 |
| chr5 | 153863347 | 153863526 | chr5 | 154209838 | 154210070 | chr5 | 154318060 | 154318178 |
| chr5 | 155107702 | 155107941 | chr5 | 155108042 | 155108612 | chr5 | 155108659 | 155108838 |
| chr5 | 156874164 | 156874403 | chr5 | 157001643 | 157001941 | chr5 | 157078345 | 157078524 |
| chr5 | 157098282 | 157098701 | chr5 | 158478385 | 158478864 | chr5 | 158524601 | 158524837 |
| chr5 | 158527367 | 158528146 | chr5 | 159399075 | 159399314 | chr5 | 160975650 | 160975829 |
| chr5 | 161274223 | 161274358 | chr5 | 161274506 | 161274642 | chr5 | 166865354 | 166865462 |
| chr5 | 167956087 | 167956560 | chr5 | 167956601 | 167956686 | chr5 | 168233320 | 168233559 |
| chr5 | 168727837 | 168728076 | chr5 | 169064237 | 169064887 | chr5 | 169532851 | 169533090 |
| chr5 | 170108211 | 170108450 | chr5 | 170289352 | 170289395 | chr5 | 170735061 | 170735300 |
| chr5 | 170735336 | 170735875 | chr5 | 170736019 | 170737578 | chr5 | 170737729 | 170739571 |

TABLE 14-continued

| chr | start | end | chr | start | end | chr | start | end |
|---|---|---|---|---|---|---|---|---|
| chr5 | 170739746 | 170740058 | chr5 | 170740091 | 170740105 | chr5 | 170740391 | 170741031 |
| chr5 | 170741508 | 170742827 | chr5 | 170743151 | 170744207 | chr5 | 170744290 | 170744649 |
| chr5 | 170745286 | 170745560 | chr5 | 172655778 | 172656317 | chr5 | 172659314 | 172659378 |
| chr5 | 172659397 | 172659756 | chr5 | 172659768 | 172660307 | chr5 | 172660633 | 172661228 |
| chr5 | 172661368 | 172661772 | chr5 | 172664148 | 172664567 | chr5 | 172665492 | 172665911 |
| chr5 | 172670882 | 172671121 | chr5 | 172671268 | 172671926 | chr5 | 172672391 | 172672406 |
| chr5 | 172672593 | 172672750 | chr5 | 172754486 | 172754725 | chr5 | 172754733 | 172755032 |
| chr5 | 172755388 | 172755745 | chr5 | 172756961 | 172757200 | chr5 | 174115296 | 174115690 |
| chr5 | 174115864 | 174115955 | chr5 | 174147441 | 174147680 | chr5 | 174150341 | 174150520 |
| chr5 | 174158719 | 174159669 | chr5 | 174162800 | 174162945 | chr5 | 174220897 | 174221036 |
| chr5 | 174870643 | 174870882 | chr5 | 174871097 | 174871576 | chr5 | 174921381 | 174921483 |
| chr5 | 175085059 | 175085298 | chr5 | 175085389 | 175085808 | chr5 | 175223571 | 175223810 |
| chr5 | 175223935 | 175224354 | chr5 | 175298507 | 175298986 | chr5 | 175299196 | 175299495 |
| chr5 | 175300277 | 175300456 | chr5 | 175621297 | 175621596 | chr5 | 175792785 | 175793144 |
| chr5 | 176023818 | 176024350 | chr5 | 176046280 | 176046639 | chr5 | 176107191 | 176107670 |
| chr5 | 176236631 | 176236990 | chr5 | 176264711 | 176264998 | chr5 | 176764020 | 176764255 |
| chr5 | 177031093 | 177031272 | chr5 | 177408416 | 177408548 | chr5 | 177411561 | 177412210 |
| chr5 | 77713273 | 177713572 | chr5 | 178003629 | 178003928 | chr5 | 178004231 | 178004470 |
| chr5 | 178016513 | 178017971 | chr5 | 178367990 | 178368462 | chr5 | 178421400 | 178421579 |
| chr5 | 178421685 | 178422099 | chr5 | 178422167 | 178422224 | chr5 | 178487023 | 178487493 |
| chr5 | 178576382 | 178576578 | chr5 | 178655663 | 178655962 | chr5 | 178771216 | 178772055 |
| chr5 | 178772120 | 178772359 | chr5 | 178772525 | 178772824 | chr5 | 178957552 | 178958023 |
| chr5 | 179214036 | 179214275 | chr5 | 179243892 | 179244371 | chr5 | 179780005 | 179780244 |
| chr5 | 179780607 | 179781086 | chr5 | 179867405 | 179867637 | chr5 | 180017039 | 180017278 |
| chr5 | 180017532 | 180018011 | chr5 | 180018226 | 180018585 | chr5 | 180047646 | 180047703 |
| chr5 | 180075753 | 180076412 | chr5 | 180076466 | 180076705 | chr5 | 180076721 | 180077080 |
| chr5 | 180100825 | 180101410 | chr5 | 180326052 | 180326231 | chr5 | 180527447 | 180527866 |
| chr5 | 180600769 | 180601030 | chr5 | 180601129 | 180601308 | chr6 | 391089 | 392097 |
| chr6 | 392230 | 393729 | chr6 | 711039 | 711392 | chr6 | 1311899 | 1312095 |
| chr6 | 1312680 | 1312802 | chr6 | 1314014 | 1314150 | chr6 | 1378133 | 1379332 |
| chr6 | 1379510 | 1379689 | chr6 | 1379812 | 1380051 | chr6 | 1383598 | 1384731 |
| chr6 | 1385025 | 1385264 | chr6 | 1386020 | 1386212 | chr6 | 1389044 | 1389343 |
| chr6 | 1390159 | 1391118 | chr6 | 1391230 | 1391469 | chr6 | 1524122 | 1524361 |
| chr6 | 1606302 | 1605541 | chr6 | 1614740 | 1615279 | chr6 | 1624940 | 1625059 |
| chr6 | 1626129 | 1625779 | chr6 | 3053237 | 3053463 | chr6 | 3228955 | 3229134 |
| chr6 | 3229348 | 3229587 | chr6 | 3231926 | 3232029 | chr6 | 3285129 | 3285608 |
| chr6 | 3405599 | 3405778 | chr6 | 4775080 | 4775322 | chr6 | 4836441 | 4836545 |
| chr6 | 4951178 | 4951469 | chr6 | 5783232 | 5783457 | chr6 | 5996852 | 5997091 |
| chr6 | 5997728 | 5997907 | chr6 | 6003213 | 6005450 | chr6 | 6006278 | 6006498 |
| chr6 | 6006600 | 6006959 | chr6 | 6007516 | 6007772 | chr6 | 6007833 | 6008355 |
| chr6 | 6367000 | 6367218 | chr6 | 7726260 | 7726439 | chr6 | 7726556 | 7726735 |
| chr6 | 7726878 | 7727052 | chr6 | 7727622 | 7728221 | chr6 | 7728746 | 7729045 |
| chr6 | 10381428 | 10382383 | chr6 | 10382648 | 10383126 | chr6 | 10383638 | 10383877 |
| chr6 | 10384876 | 10386015 | chr6 | 10386123 | 10386357 | chr6 | 10389946 | 10391265 |
| chr6 | 10410429 | 10410668 | chr6 | 10411254 | 10411613 | chr6 | 10415015 | 10416314 |
| chr6 | 10415457 | 10415816 | chr6 | 10416039 | 10416445 | chr6 | 10417059 | 10417658 |
| chr6 | 10418997 | 10419596 | chr6 | 10419664 | 10420023 | chr6 | 10420975 | 10421171 |
| chr6 | 10421253 | 10422714 | chr6 | 10425411 | 10426970 | chr6 | 10881857 | 10882156 |
| chr6 | 10882247 | 10882426 | chr6 | 10882934 | 10883113 | chr6 | 10886993 | 10887772 |
| chr6 | 11043988 | 11044647 | chr6 | 12288420 | 12288779 | chr6 | 12749819 | 12750058 |
| chr6 | 12750114 | 12750353 | chr6 | 16196952 | 16197191 | chr6 | 17281327 | 17281351 |
| chr6 | 18035792 | 18036091 | chr6 | 19691621 | 19691920 | chr6 | 19691983 | 19692280 |
| chr6 | 19836983 | 19837222 | chr6 | 21664905 | 21665144 | chr6 | 24494604 | 24494843 |
| chr6 | 24647262 | 24647371 | chr6 | 26184364 | 26184476 | chr6 | 26188754 | 26189495 |
| chr6 | 26189956 | 26190075 | chr6 | 26199099 | 26199242 | chr6 | 26199612 | 26199791 |
| chr6 | 26214613 | 26214731 | chr6 | 26235124 | 26235437 | chr6 | 26240532 | 26241201 |
| chr6 | 26250378 | 26250917 | chr6 | 26250969 | 26251261 | chr6 | 26251715 | 26251940 |
| chr6 | 26252075 | 26252180 | chr6 | 26271315 | 26271854 | chr6 | 26271897 | 26272076 |
| chr6 | 26272416 | 26272715 | chr6 | 26273381 | 26273560 | chr6 | 26284786 | 26284975 |
| chr6 | 26327725 | 26328074 | chr6 | 26328206 | 26328505 | chr6 | 26332079 | 26332318 |
| chr6 | 26501764 | 26502296 | chr6 | 26550895 | 26551134 | chr6 | 26577078 | 26577557 |
| chr6 | 26987930 | 26988169 | chr6 | 27059697 | 27059936 | chr6 | 27064581 | 27065300 |
| chr6 | 27173436 | 27173855 | chr6 | 27173925 | 27174275 | chr6 | 27182856 | 27182974 |
| chr6 | 27203167 | 27203286 | chr6 | 27205240 | 27205359 | chr6 | 27205420 | 27205521 |
| chr6 | 27205587 | 27206126 | chr6 | 27228079 | 27228498 | chr6 | 27247561 | 27247800 |
| chr6 | 27256016 | 27256255 | chr6 | 27256283 | 27256522 | chr6 | 27264344 | 27264468 |
| chr6 | 27279750 | 27280109 | chr6 | 27462939 | 27463778 | chr6 | 27512675 | 27513574 |
| chr6 | 27533723 | 27534442 | chr6 | 27559775 | 27560074 | chr6 | 27573073 | 27573492 |
| chr6 | 27598650 | 27598949 | chr6 | 27599071 | 27599427 | chr6 | 27635171 | 27635530 |
| chr6 | 27647625 | 27647984 | chr6 | 27648934 | 27649153 | chr6 | 27834577 | 27834936 |
| chr6 | 27834963 | 27835502 | chr6 | 27839635 | 27840174 | chr6 | 27840461 | 27840668 |
| chr6 | 27841002 | 27841240 | chr6 | 27858427 | 27858726 | chr6 | 28175105 | 28176301 |
| chr6 | 28303466 | 28303571 | chr6 | 28303847 | 28304339 | chr6 | 28367023 | 28367862 |
| chr6 | 28410896 | 28411435 | chr6 | 28414887 | 28415126 | chr6 | 28457534 | 28457713 |
| chr6 | 28457775 | 28458254 | chr6 | 33955409 | 33955828 | chr6 | 34170869 | 34170986 |
| chr6 | 34171049 | 34171166 | chr6 | 34396518 | 34396631 | chr6 | 34724210 | 34724318 |
| chr6 | 35149942 | 35150181 | chr6 | 35479539 | 35479718 | chr6 | 35992354 | 35992533 |
| chr6 | 36165588 | 36165767 | chr6 | 36252899 | 36253258 | chr6 | 36313887 | 36313988 |

TABLE 14-continued

| chr | start | end | chr | start | end | chr | start | end |
|---|---|---|---|---|---|---|---|---|
| chr6 | 36808233 | 36808532 | chr6 | 37024485 | 37024664 | chr6 | 37664045 | 37664284 |
| chr6 | 37673227 | 37673573 | chr6 | 37776336 | 37776455 | chr6 | 37776737 | 37776839 |
| chr6 | 39281005 | 39281231 | chr6 | 39281731 | 39281970 | chr6 | 39329789 | 39329968 |
| chr6 | 39760322 | 39760663 | chr6 | 40554557 | 40554796 | chr6 | 41336981 | 41337220 |
| chr6 | 41339162 | 41339941 | chr6 | 41340803 | 41341282 | chr6 | 41341406 | 41341645 |
| chr6 | 41342140 | 41342370 | chr6 | 41342733 | 41342912 | chr6 | 41605851 | 41606630 |
| chr6 | 41773485 | 41773844 | chr6 | 42773364 | 42773471 | chr6 | 42846625 | 42846729 |
| chr6 | 42879457 | 42879756 | chr6 | 42928239 | 42928460 | chr6 | 43211113 | 43211402 |
| chr6 | 43424445 | 43424564 | chr6 | 43425407 | 43425524 | chr6 | 43478592 | 43478821 |
| chr6 | 43612737 | 43613156 | chr6 | 43639525 | 43639809 | chr6 | 43748380 | 43748619 |
| chr6 | 44240961 | 44241191 | chr6 | 44695775 | 44695899 | chr6 | 45388701 | 45388866 |
| chr6 | 46702904 | 46703203 | chr6 | 46703274 | 46703513 | chr6 | 50674292 | 50674831 |
| chr6 | 50681612 | 50681851 | chr6 | 50681912 | 50682031 | chr6 | 50682234 | 50682473 |
| chr6 | 50682584 | 50683303 | chr6 | 50684865 | 50685044 | chr6 | 50689827 | 50690126 |
| chr6 | 50690991 | 50691170 | chr6 | 50691983 | 50692582 | chr6 | 50787125 | 50788444 |
| chr6 | 50789300 | 50789479 | chr6 | 50791111 | 50791708 | chr6 | 50793251 | 50793490 |
| chr6 | 50793626 | 50793850 | chr6 | 50794525 | 50794792 | chr6 | 50803732 | 50803971 |
| chr6 | 50804041 | 50804446 | chr6 | 50808589 | 50808845 | chr6 | 50810456 | 50810935 |
| chr6 | 50810976 | 50811575 | chr6 | 50813200 | 50814019 | chr6 | 50814495 | 50814674 |
| chr6 | 50816947 | 50817306 | chr6 | 50817831 | 50817841 | chr6 | 50818369 | 50818788 |
| chr6 | 50818841 | 50819080 | chr6 | 52227678 | 52227857 | chr6 | 52227934 | 52227964 |
| chr6 | 52344301 | 52344480 | chr6 | 53212553 | 53213932 | chr6 | 55443610 | 55444029 |
| chr6 | 56112175 | 56112474 | chr6 | 56716252 | 56716491 | chr6 | 56818618 | 56819037 |
| chr6 | 56819128 | 56819727 | chr6 | 56819823 | 56820002 | chr6 | 58147345 | 58147619 |
| chr6 | 58147764 | 58148058 | chr6 | 62995272 | 62996231 | chr6 | 62996347 | 62996586 |
| chr6 | 70991961 | 70992260 | chr6 | 70992339 | 70992638 | chr6 | 70992744 | 70993103 |
| chr6 | 71665562 | 71665801 | chr6 | 71666708 | 71667066 | chr6 | 72129690 | 72129929 |
| chr6 | 72130017 | 72130556 | chr6 | 72596039 | 72596398 | chr6 | 72596876 | 72597055 |
| chr6 | 73329686 | 73330225 | chr6 | 73330740 | 73331399 | chr6 | 73331420 | 73333099 |
| chr6 | 78172096 | 78172675 | chr6 | 78173119 | 78173295 | chr6 | 78173610 | 78174080 |
| chr6 | 78176370 | 78176607 | chr6 | 78176693 | 78176909 | chr6 | 79620310 | 79620789 |
| chr6 | 80656846 | 80657265 | chr6 | 82958527 | 82958646 | chr6 | 84417343 | 84417877 |
| chr6 | 84418078 | 84418377 | chr6 | 84418545 | 84418904 | chr6 | 84419077 | 84419496 |
| chr6 | 84562789 | 84563328 | chr6 | 84563397 | 84563636 | chr6 | 85472306 | 85473805 |
| chr6 | 85473854 | 85474453 | chr6 | 85474516 | 85474767 | chr6 | 85474795 | 85474815 |
| chr6 | 85476140 | 85476379 | chr6 | 85476924 | 85477103 | chr6 | 85478440 | 85478557 |
| chr6 | 85478615 | 85478799 | chr6 | 85482437 | 85482796 | chr6 | 85483271 | 85483450 |
| chr6 | 85483559 | 85484998 | chr6 | 86302335 | 86302422 | chr6 | 87647130 | 87647219 |
| chr6 | 87862013 | 87862252 | chr6 | 88876871 | 88877530 | chr6 | 91320191 | 91320422 |
| chr6 | 91320853 | 91321390 | chr6 | 94126870 | 94127169 | chr6 | 94127381 | 94127620 |
| chr6 | 94128340 | 94128502 | chr6 | 94129119 | 94129358 | chr6 | 94129423 | 94129662 |
| chr6 | 96464003 | 96464293 | chr6 | 99271829 | 99272908 | chr6 | 99273271 | 99273510 |
| chr6 | 99277106 | 99277201 | chr6 | 99277262 | 99277405 | chr6 | 99279465 | 99279704 |
| chr6 | 99280472 | 99280831 | chr6 | 99281470 | 99281470 | chr6 | 99283428 | 99283667 |
| chr6 | 99290260 | 99290499 | chr6 | 99290556 | 99290738 | chr6 | 99291191 | 99291531 |
| chr6 | 99292156 | 99292515 | chr6 | 99295648 | 99296547 | chr6 | 99396354 | 99396473 |
| chr6 | 100038584 | 100039063 | chr6 | 100039185 | 100039364 | chr6 | 100050674 | 100052053 |
| chr6 | 100053191 | 100053606 | chr6 | 100054773 | 100055012 | chr6 | 100060930 | 100061169 |
| chr6 | 100061216 | 100061515 | chr6 | 100061677 | 100061916 | chr6 | 100062083 | 100062682 |
| chr6 | 100062857 | 100063156 | chr6 | 100441276 | 100442055 | chr6 | 100903299 | 100903718 |
| chr6 | 100904126 | 100904365 | chr6 | 100905936 | 100906113 | chr6 | 100911976 | 100912215 |
| chr6 | 100912332 | 100912571 | chr6 | 100912825 | 100913244 | chr6 | 100915004 | 100915303 |
| chr6 | 101840615 | 101840914 | chr6 | 101847215 | 101847290 | chr6 | 101850062 | 101850314 |
| chr6 | 101850496 | 101850675 | chr6 | 105388605 | 105388784 | chr6 | 105388833 | 105389792 |
| chr6 | 105400811 | 105401110 | chr6 | 105401538 | 105401908 | chr6 | 105404475 | 105404774 |
| chr6 | 105405565 | 105405864 | chr6 | 105406024 | 105406203 | chr6 | 105584190 | 105585629 |
| chr6 | 106428948 | 106429704 | chr6 | 106434265 | 106434371 | chr6 | 106441795 | 106443054 |
| chr6 | 106960817 | 106961116 | chr6 | 107955878 | 107956057 | chr6 | 108280341 | 108280442 |
| chr6 | 108434990 | 108435327 | chr6 | 108435970 | 108436629 | chr6 | 108438142 | 108438612 |
| chr6 | 108440017 | 108441036 | chr6 | 108479209 | 108479748 | chr6 | 108484829 | 108485274 |
| chr6 | 108485419 | 108485488 | chr6 | 108485576 | 108485995 | chr6 | 108486067 | 108486486 |
| chr6 | 108487701 | 108488520 | chr6 | 108489290 | 108490729 | chr6 | 108490902 | 108491501 |
| chr6 | 108492182 | 108492541 | chr6 | 108495607 | 108496026 | chr6 | 108496130 | 108496729 |
| chr6 | 108497419 | 108497958 | chr6 | 110679030 | 110679509 | chr6 | 110797604 | 110797783 |
| chr6 | 110797933 | 110798047 | chr6 | 116783418 | 116783591 | chr6 | 117086168 | 117086947 |
| chr6 | 117585867 | 117586106 | chr6 | 117586717 | 117586781 | chr6 | 117587028 | 117587256 |
| chr6 | 117587380 | 117587387 | chr6 | 117587449 | 117587679 | chr6 | 117591087 | 117591266 |
| chr6 | 117591308 | 117591847 | chr6 | 118228008 | 118228247 | chr6 | 118228669 | 118228908 |
| chr6 | 118229060 | 118229479 | chr6 | 118229543 | 118229902 | chr6 | 118241125 | 118241604 |
| chr6 | 119254661 | 119254774 | chr6 | 121758594 | 121759048 | chr6 | 123316950 | 123317669 |
| chr6 | 123317696 | 123317935 | chr6 | 124124330 | 124124569 | chr6 | 124124759 | 124125118 |
| chr6 | 125284034 | 125284273 | chr6 | 126068016 | 126068255 | chr6 | 127439297 | 127439536 |
| chr6 | 127439907 | 127440206 | chr6 | 127440248 | 127441207 | chr6 | 127441479 | 127441838 |
| chr6 | 127441944 | 127442183 | chr6 | 127840412 | 127840771 | chr6 | 129204373 | 129204612 |
| chr6 | 130686437 | 130687156 | chr6 | 131602689 | 131602789 | chr6 | 132721988 | 1327222 |
| chr6 | 133561666 | 133562145 | chr6 | 133562297 | 133563136 | chr6 | 133563234 | 133564013 |
| chr6 | 134067456 | 134067573 | chr6 | 134176147 | 134176149 | chr6 | 134210439 | 134211458 |
| chr6 | 134213855 | 134214454 | chr6 | 134589425 | 134589586 | chr6 | 134638858 | 134639095 |

TABLE 14-continued

| chr | start | end | chr | start | end | chr | start | end |
|---|---|---|---|---|---|---|---|---|
| chr6 | 137241828 | 137242302 | chr6 | 137243130 | 137243342 | chr6 | 132243367 | 137243489 |
| chr6 | 137244036 | 137244695 | chr6 | 137311060 | 137311479 | chr6 | 137366280 | 137366459 |
| chr6 | 137809066 | 137811165 | chr6 | 137813692 | 137813991 | chr6 | 137814505 | 137814864 |
| chr6 | 137814916 | 137815755 | chr6 | 137816373 | 137817377 | chr6 | 137818428 | 137819447 |
| chr6 | 146755489 | 146755728 | chr6 | 149868369 | 149868478 | chr6 | 150284574 | 150284657 |
| chr6 | 150284759 | 150286718 | chr6 | 150358890 | 150359489 | chr6 | 151560928 | 151561947 |
| chr6 | 151561986 | 151562645 | chr6 | 151814953 | 151815192 | chr6 | 152622925 | 152623584 |
| chr6 | 152957807 | 152958166 | chr6 | 163451159 | 153451578 | chr6 | 163451810 | 153452049 |
| chr6 | 153452157 | 153452396 | chr6 | 153452611 | 153452850 | chr6 | 154360549 | 154360848 |
| chr6 | 154970468 | 154970587 | chr6 | 155316161 | 155316340 | chr6 | 155569193 | 155569407 |
| chr6 | 157502364 | 157502543 | chr6 | 157506008 | 157506187 | chr6 | 157556755 | 157557954 |
| chr6 | 159589948 | 159591087 | chr6 | 159654844 | 159655083 | chr6 | 161100422 | 161100466 |
| chr6 | 161188439 | 161188618 | chr6 | 161351999 | 161352238 | chr6 | 161780141 | 161780218 |
| chr6 | 163834237 | 163834716 | chr6 | 163834779 | 163834907 | chr6 | 163834988 | 163835018 |
| chr6 | 163836465 | 163837004 | chr6 | 164179653 | 164179772 | chr6 | 164196997 | 164197107 |
| chr6 | 164228212 | 164228449 | chr6 | 164246123 | 164246229 | chr6 | 164283167 | 164283370 |
| chr6 | 164314286 | 164314525 | chr6 | 164322572 | 164322871 | chr6 | 166074027 | 166074506 |
| chr6 | 166076696 | 166077115 | chr6 | 166077280 | 166077759 | chr6 | 166267503 | 166268162 |
| chr6 | 166401162 | 166401401 | chr6 | 166402154 | 166402633 | chr6 | 166421871 | 166422288 |
| chr6 | 166579636 | 166580234 | chr6 | 166580252 | 166582891 | chr6 | 166944266 | 166944505 |
| chr6 | 167835031 | 167835270 | chr6 | 168719882 | 168720121 | chr6 | 168842760 | 168843046 |
| chr6 | 168858030 | 168858389 | chr6 | 169653564 | 169653743 | chr6 | 170240691 | 170240797 |
| chr6 | 170264630 | 170264865 | chr6 | 170475007 | 170475366 | chr7 | 329703 | 329942 |
| chr7 | 369763 | 370062 | chr7 | 389589 | 389768 | chr7 | 409740 | 409872 |
| chr7 | 409882 | 409979 | chr7 | 431290 | 431589 | chr7 | 497679 | 498006 |
| chr7 | 503725 | 504024 | chr7 | 551499 | 551778 | chr7 | 557008 | 557076 |
| chr7 | 578836 | 579121 | chr7 | 751726 | 751965 | chr7 | 752022 | 752321 |
| chr7 | 907582 | 907761 | chr7 | 914984 | 915163 | chr7 | 1022150 | 1022329 |
| chr7 | 1030079 | 1030378 | chr7 | 1054489 | 1054780 | chr7 | 1086110 | 1086409 |
| chr7 | 1263682 | 1264041 | chr7 | 1269228 | 1269887 | chr7 | 1270304 | 1270543 |
| chr7 | 1273170 | 1273429 | chr7 | 1274540 | 1274779 | chr7 | 1274934 | 1275113 |
| chr7 | 1275481 | 1275780 | chr7 | 1277722 | 1277961 | chr7 | 1279136 | 1279204 |
| chr7 | 1279891 | 1280070 | chr7 | 1281033 | 1281332 | chr7 | 1281405 | 1281644 |
| chr7 | 1281947 | 1282246 | chr7 | 1282426 | 1282725 | chr7 | 1286142 | 1286441 |
| chr7 | 1286715 | 1286954 | chr7 | 1288489 | 1288848 | chr7 | 1308275 | 1308574 |
| chr7 | 1325727 | 1325966 | chr7 | 1415941 | 1416226 | chr7 | 1423536 | 1423740 |
| chr7 | 1458967 | 1459183 | chr7 | 1503328 | 1503687 | chr7 | 1547234 | 1547413 |
| chr7 | 1598549 | 1598788 | chr7 | 1607307 | 1607546 | chr7 | 1607897 | 1608076 |
| chr7 | 1641700 | 1641999 | chr7 | 1681095 | 1681334 | chr7 | 1688883 | 1689101 |
| chr7 | 1690696 | 1690801 | chr7 | 1690903 | 1690948 | chr7 | 1709038 | 1709337 |
| chr7 | 1709385 | 1709684 | chr7 | 1733066 | 1733482 | chr7 | 1775757 | 1775936 |
| chr7 | 1783468 | 1783470 | chr7 | 1786438 | 1786916 | chr7 | 1787066 | 1787425 |
| chr7 | 1800808 | 1800987 | chr7 | 1970776 | 1970947 | chr7 | 2163251 | 2163496 |
| chr7 | 2208635 | 2208889 | chr7 | 2232861 | 2233154 | chr7 | 2233204 | 2233503 |
| chr7 | 2238051 | 2238327 | chr7 | 2300694 | 2300803 | chr7 | 2473350 | 2473614 |
| chr7 | 2473624 | 2473709 | chr7 | 2565961 | 2566130 | chr7 | 2566526 | 2566705 |
| chr7 | 2719928 | 2720227 | chr7 | 2727968 | 2728267 | chr7 | 3033584 | 3033763 |
| chr7 | 3083216 | 3083455 | chr7 | 3283620 | 3283978 | chr7 | 3340370 | 3340549 |
| chr7 | 3340890 | 3341069 | chr7 | 3341394 | 3341693 | chr7 | 4215235 | 4215469 |
| chr7 | 4856897 | 4857136 | chr7 | 4922460 | 4922816 | chr7 | 4922996 | 4923475 |
| chr7 | 4998116 | 4998475 | chr7 | 4998598 | 4998837 | chr7 | 5262472 | 5262648 |
| chr7 | 5632841 | 5633200 | chr7 | 5648011 | 5648490 | chr7 | 6060493 | 6060556 |
| chr7 | 6099127 | 6099234 | chr7 | 6124621 | 6124740 | chr7 | 6188652 | 6188831 |
| chr7 | 6188926 | 6189165 | chr7 | 6443198 | 6443478 | chr7 | 6443752 | 6443794 |
| chr7 | 6443871 | 6443931 | chr7 | 6524492 | 6524599 | chr7 | 6524936 | 6525055 |
| chr7 | 6543060 | 6543303 | chr7 | 6560141 | 6560440 | chr7 | 6566329 | 6566748 |
| chr7 | 6570866 | 6571225 | chr7 | 6576043 | 6576185 | chr7 | 6703458 | 6704057 |
| chr7 | 7605665 | 7605902 | chr7 | 8472995 | 8473762 | chr7 | 8473870 | 8474649 |
| chr7 | 8474727 | 8475146 | chr7 | 8480647 | 8481126 | chr7 | 8481228 | 5481260 |
| chr7 | 8481559 | 8481918 | chr7 | 8481980 | 8482999 | chr7 | 8483070 | 8484029 |
| chr7 | 12151350 | 12151769 | chr7 | 12443241 | 12443480 | chr7 | 12443767 | 12443806 |
| chr7 | 12610259 | 12610317 | chr7 | 12610539 | 12610558 | chr7 | 15725883 | 15726182 |
| chr7 | 15726557 | 15727156 | chr7 | 15727216 | 15727395 | chr7 | 19145730 | 19146329 |
| chr7 | 19146411 | 19146650 | chr7 | 19147041 | 19147880 | chr7 | 19152069 | 19152368 |
| chr7 | 19155865 | 19155896 | chr7 | 19155984 | 19156643 | chr7 | 19156705 | 19157003 |
| chr7 | 19157041 | 19158120 | chr7 | 19183978 | 19184337 | chr7 | 19813210 | 19813350 |
| chr7 | 20816175 | 20816530 | chr7 | 20817306 | 20817332 | chr7 | 20817452 | 20817485 |
| chr7 | 20818037 | 20818276 | chr7 | 20823213 | 20823512 | chr7 | 20823826 | 20825025 |
| chr7 | 20825290 | 20825363 | chr7 | 20826803 | 20826939 | chr7 | 20827224 | 20827282 |
| chr7 | 20830596 | 20830775 | chr7 | 20833066 | 20833425 | chr7 | 21582492 | 21582971 |
| chr7 | 21583176 | 21583415 | chr7 | 22539752 | 22539991 | chr7 | 22589254 | 22589973 |
| chr7 | 23287170 | 23287709 | chr7 | 23578824 | 23578943 | chr7 | 24324002 | 24324031 |
| chr7 | 24580786 | 24580905 | chr7 | 24796404 | 24796643 | chr7 | 25892430 | 25892669 |
| chr7 | 25896424 | 25896603 | chr7 | 25896675 | 25896963 | chr7 | 27127919 | 27128001 |
| chr7 | 27135232 | 27135891 | chr7 | 27135923 | 27136868 | chr7 | 27190490 | 27191329 |
| chr7 | 27195483 | 27196742 | chr7 | 27204402 | 27205481 | chr7 | 27205599 | 27206138 |
| chr7 | 27209413 | 27209672 | chr7 | 27209690 | 27209772 | chr7 | 27212400 | 27212999 |
| chr7 | 27213082 | 27214401 | chr7 | 27223031 | 27223253 | chr7 | 27223500 | 27223799 |

TABLE 14-continued

| chr | start | end | chr | start | end | chr | start | end |
|---|---|---|---|---|---|---|---|---|
| chr7 | 27223980 | 27224699 | chr7 | 27224945 | 27225184 | chr7 | 27227795 | 27228034 |
| chr7 | 27232207 | 27233046 | chr7 | 27238813 | 27238992 | chr7 | 27239087 | 27239326 |
| chr7 | 27240127 | 27240423 | chr7 | 27244446 | 27245393 | chr7 | 27245583 | 27245733 |
| chr7 | 27252306 | 27252485 | chr7 | 27264801 | 27265400 | chr7 | 27265442 | 27265678 |
| chr7 | 27275439 | 27275532 | chr7 | 27279015 | 27279554 | chr7 | 27282012 | 27283091 |
| chr7 | 27283250 | 27283662 | chr7 | 27285436 | 27286249 | chr7 | 27288869 | 27289528 |
| chr7 | 27291048 | 27291947 | chr7 | 28449197 | 28450096 | chr7 | 28995579 | 28996058 |
| chr7 | 28996357 | 28996596 | chr7 | 28996759 | 28996998 | chr7 | 28997052 | 28997711 |
| chr7 | 28997967 | 28998206 | chr7 | 30721202 | 30721981 | chr7 | 30722214 | 30722453 |
| chr7 | 31092919 | 31093218 | chr7 | 31375899 | 31376230 | chr7 | 32110616 | 32110855 |
| chr7 | 32337733 | 32337912 | chr7 | 32338010 | 32338489 | chr7 | 32338826 | 32339005 |
| chr7 | 32467373 | 32468151 | chr7 | 32997050 | 32997463 | chr7 | 33943370 | 33943849 |
| chr7 | 35225724 | 35225963 | chr7 | 35226090 | 35226811 | chr7 | 35292893 | 35293372 |
| chr7 | 35293569 | 35294228 | chr7 | 35294400 | 35294639 | chr7 | 35295030 | 35295182 |
| chr7 | 35295807 | 35296000 | chr7 | 35296855 | 35298114 | chr7 | 35300851 | 35302050 |
| chr7 | 35494278 | 35494517 | chr7 | 37487076 | 37487251 | chr7 | 37487376 | 37487915 |
| chr7 | 37488179 | 37488658 | chr7 | 37488837 | 37489076 | chr7 | 37907366 | 37907545 |
| chr7 | 37955780 | 37956079 | chr7 | 37956176 | 37956535 | chr7 | 37960199 | 37960438 |
| chr7 | 38670267 | 38671106 | chr7 | 39015463 | 39016062 | chr7 | 42267573 | 42267752 |
| chr7 | 42276251 | 42276730 | chr7 | 42533028 | 42533387 | chr7 | 43152016 | 43152795 |
| chr7 | 43152858 | 43153337 | chr7 | 44097656 | 44097895 | chr7 | 44143906 | 44144085 |
| chr7 | 44151324 | 44151503 | chr7 | 44151715 | 44151857 | chr7 | 44164017 | 44164078 |
| chr7 | 44364752 | 44364991 | chr7 | 44835122 | 44835467 | chr7 | 45038447 | 45038564 |
| chr7 | 45613693 | 45613992 | chr7 | 45614259 | 45614558 | chr7 | 45614655 | 45615061 |
| chr7 | 45615536 | 45615588 | chr7 | 45960650 | 45960889 | chr7 | 45961072 | 45961251 |
| chr7 | 45961423 | 45961630 | chr7 | 45961656 | 45961662 | chr7 | 45961742 | 45961981 |
| chr7 | 49812718 | 49814097 | chr7 | 49814454 | 49814873 | chr7 | 49815014 | 49815848 |
| chr7 | 50294460 | 50294556 | chr7 | 50343183 | 50343482 | chr7 | 50343607 | 50344086 |
| chr7 | 50344150 | 50344569 | chr7 | 50364988 | 50365069 | chr7 | 50438544 | 50438723 |
| chr7 | 50560494 | 50560733 | chr7 | 50860135 | 50860393 | chr7 | 50860980 | 50861214 |
| chr7 | 51384235 | 51384534 | chr7 | 51384814 | 51385006 | chr7 | 54609764 | 54610243 |
| chr7 | 54612335 | 54612814 | chr7 | 55086481 | 55086687 | chr7 | 55086899 | 55087618 |
| chr7 | 55409933 | 55410223 | chr7 | 56018026 | 56018205 | chr7 | 56031847 | 56031966 |
| chr7 | 64330322 | 64330561 | chr7 | 64330635 | 64330645 | chr7 | 64348952 | 64349131 |
| chr7 | 64349318 | 64349551 | chr7 | 64700198 | 64700426 | chr7 | 64712288 | 64712587 |
| chr7 | 64974283 | 64974402 | chr7 | 65037592 | 65037702 | chr7 | 65508900 | 65509124 |
| chr7 | 66214974 | 66215062 | chr7 | 68204692 | 68204931 | chr7 | 69062428 | 69062727 |
| chr7 | 69064489 | 69065148 | chr7 | 69897685 | 69897924 | chr7 | 70596353 | 70596772 |
| chr7 | 70596845 | 70597204 | chr7 | 70597310 | 70597368 | chr7 | 70597395 | 70597549 |
| chr7 | 70597752 | 70597754 | chr7 | 7097780 | 70598471 | chr7 | 71217011 | 71217366 |
| chr7 | 71800599 | 71801978 | chr7 | 71802315 | 71802396 | chr7 | 71802457 | 71802734 |
| chr7 | 71871105 | 71871157 | chr7 | 76033251 | 76033364 | chr7 | 77324278 | 77324397 |
| chr7 | 79081718 | 79081897 | chr7 | 79081942 | 79081969 | chr7 | 79082070 | 79082301 |
| chr7 | 79083016 | 79083255 | chr7 | 79083314 | 79083913 | chr7 | 82072248 | 82072607 |
| chr7 | 84815049 | 84815135 | chr7 | 84815252 | 84815468 | chr7 | 84815670 | 84816029 |
| chr7 | 86273108 | 86273645 | chr7 | 86274018 | 86274547 | chr7 | 87104725 | 87105445 |
| chr7 | 87229446 | 87230525 | chr7 | 87256911 | 87257150 | chr7 | 87257964 | 87258143 |
| chr7 | 88388904 | 88388130 | chr7 | 88388190 | 88388263 | chr7 | 88388439 | 88388738 |
| chr7 | 88388789 | 88389389 | chr7 | 89747928 | 89748438 | chr7 | 89950108 | 89950813 |
| chr7 | 90226188 | 90226547 | chr7 | 90894936 | 90895175 | chr7 | 92466078 | 92466486 |
| chr7 | 92689613 | 92689774 | chr7 | 93203613 | 93203852 | chr7 | 93204233 | 93204592 |
| chr7 | 93519265 | 93520224 | chr7 | 93551225 | 93551524 | chr7 | 94284277 | 94284978 |
| chr7 | 96619499 | 96619678 | chr7 | 96621614 | 96621913 | chr7 | 96622019 | 96622438 |
| chr7 | 96625472 | 96625809 | chr7 | 96625906 | 96626145 | chr7 | 96631614 | 96631780 |
| chr7 | 96634577 | 96634996 | chr7 | 96635260 | 96635379 | chr7 | 96635440 | 96635559 |
| chr7 | 96635650 | 96636729 | chr7 | 96646568 | 96647227 | chr7 | 96647715 | 96648314 |
| chr7 | 96649965 | 96650284 | chr7 | 96650809 | 96651228 | chr7 | 96651384 | 96651584 |
| chr7 | 96652070 | 96652249 | chr7 | 96653421 | 96654080 | chr7 | 97361021 | 97361860 |
| chr7 | 97362211 | 97362690 | chr7 | 97600015 | 97600194 | chr7 | 97869540 | 97869719 |
| chr7 | 98245808 | 98246947 | chr7 | 98247032 | 98247751 | chr7 | 98971530 | 98971649 |
| chr7 | 99104174 | 99104293 | chr7 | 99177657 | 99177956 | chr7 | 99591732 | 99591851 |
| chr7 | 99595184 | 99595416 | chr7 | 99751485 | 99751553 | chr7 | 99775118 | 99775297 |
| chr7 | 100088099 | 100088398 | chr7 | 100091115 | 100091474 | chr7 | 100179789 | 100180017 |
| chr7 | 100318421 | 100318660 | chr7 | 100808365 | 100808596 | chr7 | 100809360 | 100809599 |
| chr7 | 100823348 | 100823587 | chr7 | 101005901 | 101006073 | chr7 | 101241919 | 101242098 |
| chr7 | 101475705 | 101475944 | chr7 | 101627683 | 101627884 | chr7 | 101707428 | 101707535 |
| chr7 | 103085786 | 103086565 | chr7 | 103628963 | 103630222 | chr7 | 103630381 | 103630920 |
| chr7 | 103969130 | 103969429 | chr7 | 103969595 | 103969894 | chr7 | 105279390 | 105279749 |
| chr7 | 106685195 | 106685434 | chr7 | 106797700 | 105797856 | chr7 | 107301418 | 107301717 |
| chr7 | 107483597 | 107484016 | chr7 | 108095227 | 108095466 | chr7 | 108095602 | 108096141 |
| chr7 | 108097093 | 108097572 | chr7 | 112726529 | 112726706 | chr7 | 113722736 | 113723515 |
| chr7 | 113724870 | 113725169 | chr7 | 113726435 | 113726614 | chr7 | 113727345 | 113727584 |
| chr7 | 113727633 | 113727872 | chr7 | 115117451 | 115117750 | chr7 | 116140155 | 116140268 |
| chr7 | 116962796 | 116963575 | chr7 | 117119347 | 117120366 | chr7 | 119913464 | 119913837 |
| chr7 | 120969587 | 120969886 | chr7 | 121513457 | 121513796 | chr7 | 121939584 | 121940543 |
| chr7 | 121940845 | 121941144 | chr7 | 121941807 | 121942266 | chr7 | 121943905 | 121944264 |
| chr7 | 121945722 | 121946021 | chr7 | 121946403 | 121947482 | chr7 | 121950034 | 121951029 |
| chr7 | 121951784 | 121952256 | chr7 | 121956408 | 121956647 | chr7 | 121956650 | 121957411 |

TABLE 14-continued

| chr | start | end | chr | start | end | chr | start | end |
|---|---|---|---|---|---|---|---|---|
| chr7 | 123173048 | 123173327 | chr7 | 123671948 | 123672187 | chr7 | 124404320 | 124404619 |
| chr7 | 126891146 | 126891325 | chr7 | 126891430 | 126891669 | chr7 | 127371055 | 127371234 |
| chr7 | 127615847 | 127616026 | chr7 | 127744048 | 127744707 | chr7 | 127806560 | 127806739 |
| chr7 | 127807743 | 127807922 | chr7 | 127807971 | 127808822 | chr7 | 127841426 | 127841785 |
| chr7 | 127991742 | 127992221 | chr7 | 128096988 | 128097164 | chr7 | 128337365 | 128337543 |
| chr7 | 128337605 | 128338023 | chr7 | 128470816 | 128471115 | chr7 | 128486020 | 128486237 |
| chr7 | 128528729 | 128528854 | chr7 | 128528949 | 128529128 | chr7 | 128828115 | 128828354 |
| chr7 | 129229605 | 129229724 | chr7 | 129418168 | 129418513 | chr7 | 129422070 | 129423509 |
| chr7 | 129424552 | 129425991 | chr7 | 129426215 | 129426336 | chr7 | 129794508 | 129794807 |
| chr7 | 129800223 | 129800462 | chr7 | 131041437 | 131041676 | chr7 | 131242662 | 131242901 |
| chr7 | 131514750 | 131514929 | chr7 | 132261173 | 132261532 | chr7 | 134143081 | 134143560 |
| chr7 | 134143731 | 134144209 | chr7 | 134918421 | 134918720 | chr7 | 136553316 | 136553495 |
| chr7 | 136553556 | 136554469 | chr7 | 136554563 | 136555042 | chr7 | 136555145 | 136555504 |
| chr7 | 136555587 | 136556186 | chr7 | 137028402 | 137028623 | chr7 | 137531153 | 137532438 |
| chr7 | 138042136 | 138042315 | chr7 | 139167532 | 139167831 | chr7 | 139167942 | 139168481 |
| chr7 | 139208697 | 139208888 | chr7 | 139930070 | 139930371 | chr7 | 139939060 | 139939314 |
| chr7 | 140026925 | 140027043 | chr7 | 140180180 | 140180298 | chr7 | 140339839 | 140339905 |
| chr7 | 140339966 | 140340078 | chr7 | 140453048 | 140453227 | chr7 | 140772713 | 140773312 |
| chr7 | 140773478 | 140773837 | chr7 | 143042579 | 143042896 | chr7 | 143579665 | 143580144 |
| chr7 | 145812918 | 145813157 | chr7 | 145813334 | 145813573 | chr7 | 145813790 | 145814269 |
| chr7 | 148224592 | 148224711 | chr7 | 148640242 | 148640331 | chr7 | 148846061 | 148846279 |
| chr7 | 149111968 | 149112226 | chr7 | 149112287 | 149112507 | chr7 | 149119862 | 149120161 |
| chr7 | 149411444 | 149412403 | chr7 | 149744414 | 149744653 | chr7 | 149917173 | 149917412 |
| chr7 | 149918045 | 149918224 | chr7 | 150049512 | 150049626 | chr7 | 150069013 | 150069432 |
| chr7 | 150069601 | 150069662 | chr7 | 150069837 | 150069900 | chr7 | 150069921 | 150070160 |
| chr7 | 150081153 | 150081354 | chr7 | 150716088 | 150716387 | chr7 | 150748090 | 150748509 |
| chr7 | 150753843 | 150754082 | chr7 | 150870734 | 150870973 | chr7 | 151106369 | 151107088 |
| chr7 | 151107390 | 151107749 | chr7 | 151591567 | 151691805 | chr7 | 152622540 | 152622779 |
| chr7 | 152622918 | 152623157 | chr7 | 153583503 | 153584162 | chr7 | 153584297 | 153584546 |
| chr7 | 153584694 | 153584716 | chr7 | 153584758 | 153585233 | chr7 | 153585333 | 153585692 |
| chr7 | 153749619 | 153750218 | chr7 | 154561051 | 154561290 | chr7 | 154708188 | 154708355 |
| chr7 | 154861947 | 154862366 | chr7 | 155164379 | 155165638 | chr7 | 155165791 | 155166870 |
| chr7 | 155166933 | 155167992 | chr7 | 155174573 | 155174872 | chr7 | 155241235 | 155242134 |
| chr7 | 155242647 | 155243186 | chr7 | 155243245 | 155243664 | chr7 | 155243741 | 155243980 |
| chr7 | 155244092 | 155244451 | chr7 | 155246786 | 155247685 | chr7 | 155248839 | 155249018 |
| chr7 | 155249420 | 155249659 | chr7 | 155249849 | 155250088 | chr7 | 155250200 | 155250439 |
| chr7 | 155250713 | 155251072 | chr7 | 155251611 | 155252030 | chr7 | 155252160 | 155252579 |
| chr7 | 155252773 | 155253132 | chr7 | 155254765 | 155255416 | chr7 | 155256216 | 155256395 |
| chr7 | 155256986 | 155257265 | chr7 | 155258101 | 155258580 | chr7 | 155258854 | 155260233 |
| chr7 | 155260806 | 155261285 | chr7 | 155301736 | 155302035 | chr7 | 155302267 | 155303432 |
| chr7 | 155325720 | 155325954 | chr7 | 155326079 | 155326618 | chr7 | 155363212 | 155363511 |
| chr7 | 155580069 | 155580308 | chr7 | 155580772 | 155580882 | chr7 | 155581243 | 155581652 |
| chr7 | 155581664 | 155581962 | chr7 | 155582190 | 155582369 | chr7 | 155600527 | 155600825 |
| chr7 | 155602726 | 155602898 | chr7 | 156409214 | 156409426 | chr7 | 156409585 | 156409884 |
| chr7 | 156701758 | 156701997 | chr7 | 156744697 | 156744816 | chr7 | 156794465 | 156794579 |
| chr7 | 156794922 | 156795996 | chr7 | 156796442 | 156799561 | chr7 | 156800925 | 156801104 |
| chr7 | 156801323 | 156801682 | chr7 | 156808760 | 156809299 | chr7 | 156809953 | 156811520 |
| chr7 | 156812773 | 156815170 | chr7 | 156832194 | 156832493 | chr7 | 166832766 | 156833245 |
| chr7 | 156871084 | 156871383 | chr7 | 156880457 | 156880636 | chr7 | 157085281 | 157085580 |
| chr7 | 157085874 | 157086173 | chr7 | 157262738 | 157263097 | chr7 | 157263204 | 157263563 |
| chr7 | 157361531 | 157361710 | chr7 | 157476790 | 157477376 | chr7 | 157477395 | 157477994 |
| chr7 | 157481289 | 157481860 | chr7 | 157481890 | 157482249 | chr7 | 157482401 | 157482760 |
| chr7 | 157483220 | 157483639 | chr7 | 157484778 | 157485377 | chr7 | 157485437 | 157485796 |
| chr7 | 157485881 | 157486600 | chr7 | 157584104 | 157584283 | chr7 | 157588510 | 157588869 |
| chr7 | 157606632 | 157606811 | chr7 | 157690145 | 157690161 | chr7 | 158059659 | 158059898 |
| chr7 | 158936420 | 158936956 | chr7 | 158937062 | 158937721 | chr7 | 158938126 | 158938485 |
| chr8 | 686794 | 687393 | chr8 | 687650 | 688129 | chr8 | 688286 | 688465 |
| chr8 | 688895 | 689134 | chr8 | 1085559 | 1085678 | chr8 | 4849040 | 4849279 |
| chr8 | 4849364 | 4849603 | chr8 | 4850173 | 4850592 | chr8 | 4851662 | 4851686 |
| chr8 | 4851722 | 4851841 | chr8 | 4851921 | 4852220 | chr8 | 8748329 | 8748808 |
| chr8 | 8748819 | 8749058 | chr8 | 97227 | 9722993 | chr8 | 9755965 | 9756564 |
| chr8 | 9760646 | 9761245 | chr8 | 9762487 | 9762965 | chr8 | 9763060 | 9763359 |
| chr8 | 9763816 | 9764295 | chr8 | 9764344 | 9764643 | chr8 | 10587507 | 10587866 |
| chr8 | 10588301 | 10588540 | chr8 | 11204405 | 11204584 | chr8 | 11204709 | 11205008 |
| chr8 | 11536753 | 11536932 | chr8 | 11537123 | 11537362 | chr8 | 11554886 | 11554990 |
| chr8 | 11555068 | 11555605 | chr8 | 11559678 | 11559792 | chr8 | 1159920 | 11560457 |
| chr8 | 11560633 | 11560872 | chr8 | 11561352 | 11562256 | chr8 | 11562335 | 11562574 |
| chr8 | 11562600 | 11563019 | chr8 | 11705869 | 11706228 | chr8 | 11726393 | 11726505 |
| chr8 | 12990409 | 12990529 | chr8 | 12990575 | 12990874 | chr8 | 13319857 | 13319930 |
| chr8 | 15094425 | 15094664 | chr8 | 15397641 | 15397940 | chr8 | 16884239 | 16884331 |
| chr8 | 16885104 | 16885343 | chr8 | 17270974 | 17271213 | chr8 | 19797396 | 19797538 |
| chr8 | 19797860 | 19798099 | chr8 | 20160679 | 20160978 | chr8 | 22089428 | 22089665 |
| chr8 | 22562265 | 22562564 | chr8 | 22960567 | 22960806 | chr8 | 23021083 | 23021209 |
| chr8 | 23260598 | 23260957 | chr8 | 23423830 | 23424009 | chr8 | 23559296 | 23560615 |
| chr8 | 23563712 | 23564480 | chr8 | 23564697 | 23565108 | chr8 | 23566729 | 23567568 |
| chr8 | 23571588 | 23572067 | chr8 | 23572334 | 23572646 | chr8 | 23584000 | 23584839 |
| chr8 | 24770239 | 24770658 | chr8 | 24771072 | 24771311 | chr8 | 24771348 | 24771647 |
| chr8 | 24813089 | 24813388 | chr8 | 24813660 | 24814499 | chr8 | 24857673 | 24857912 |

TABLE 14-continued

| chr | start | end | chr | start | end | chr | start | end |
|---|---|---|---|---|---|---|---|---|
| chr8 | 24858239 | 24858538 | chr8 | 24858770 | 24859249 | chr8 | 24859422 | 24859601 |
| chr8 | 25041656 | 25041955 | chr8 | 25042636 | 25042671 | chr8 | 25900324 | 25901403 |
| chr8 | 25901444 | 25901863 | chr8 | 25902072 | 25902251 | chr8 | 25902545 | 25902640 |
| chr8 | 25903579 | 25903938 | chr8 | 25904055 | 25904294 | chr8 | 25905022 | 25905201 |
| chr8 | 25905668 | 25905907 | chr8 | 25909098 | 25909697 | chr8 | 26372789 | 26372968 |
| chr8 | 26723884 | 26724183 | chr8 | 30243289 | 30243526 | chr8 | 30769151 | 30769510 |
| chr8 | 30770028 | 30770267 | chr8 | 31496380 | 31496859 | chr8 | 31496939 | 31497176 |
| chr8 | 31497420 | 31497719 | chr8 | 31498015 | 31498254 | chr8 | 32406517 | 32406996 |
| chr8 | 33371978 | 33372217 | chr8 | 33457052 | 33457471 | chr8 | 35092906 | 35093140 |
| chr8 | 35093877 | 35094056 | chr8 | 37655367 | 37655606 | chr8 | 37655707 | 37656186 |
| chr8 | 37822721 | 37823500 | chr8 | 37823583 | 37823805 | chr8 | 37961879 | 37961998 |
| chr8 | 38008157 | 38008636 | chr8 | 38323837 | 38324016 | chr8 | 38965450 | 38965464 |
| chr8 | 41165785 | 41166804 | chr8 | 41166886 | 41167125 | chr8 | 41424682 | 41424921 |
| chr8 | 41624752 | 41624931 | chr8 | 41625038 | 41626217 | chr8 | 41733424 | 41733723 |
| chr8 | 41753498 | 41753857 | chr8 | 41754070 | 41754969 | chr8 | 41755104 | 41755283 |
| chr8 | 41910186 | 41910425 | chr8 | 42147417 | 42147596 | chr8 | 42749996 | 42750094 |
| chr8 | 47093172 | 47093351 | chr8 | 47334530 | 47334694 | chr8 | 48100075 | 48100539 |
| chr8 | 49293280 | 49293699 | chr8 | 49468571 | 49469228 | chr8 | 49571955 | 49572134 |
| chr8 | 49782953 | 49783235 | chr8 | 49959156 | 49959335 | chr8 | 50822095 | 50822394 |
| chr8 | 50822591 | 50822830 | chr8 | 50823358 | 50823657 | chr8 | 53477325 | 53477864 |
| chr8 | 53477933 | 53478352 | chr8 | 53478391 | 53478744 | chr8 | 53853711 | 53854552 |
| chr8 | 54163240 | 54164256 | chr8 | 54789175 | 54789414 | chr8 | 54789556 | 54790155 |
| chr8 | 54790214 | 54790883 | chr8 | 54791724 | 54792323 | chr8 | 54792548 | 54792847 |
| chr8 | 54794123 | 54794422 | chr8 | 54794626 | 54795165 | chr8 | 55366106 | 55367725 |
| chr8 | 55370037 | 55370936 | chr8 | 55371079 | 55372638 | chr8 | 55379202 | 55380041 |
| chr8 | 55382673 | 55383332 | chr8 | 56013545 | 56014024 | chr8 | 56014058 | 56014417 |
| chr8 | 56014524 | 56014883 | chr8 | 56014959 | 56015438 | chr8 | 56015471 | 56015710 |
| chr8 | 56015834 | 56015893 | chr8 | 57025609 | 57026028 | chr8 | 57026072 | 57026311 |
| chr8 | 57026406 | 57026644 | chr8 | 57069473 | 57070245 | chr8 | 57358053 | 57359732 |
| chr8 | 57360472 | 57360891 | chr8 | 58105852 | 58106211 | chr8 | 58116923 | 58117162 |
| chr8 | 58130290 | 58130649 | chr8 | 58907618 | 58907917 | chr8 | 59058934 | 59059233 |
| chr8 | 59747274 | 59747402 | chr8 | 60032590 | 60032829 | chr8 | 61777488 | 61777622 |
| chr8 | 61789900 | 61790076 | chr8 | 62200414 | 62200879 | chr8 | 63161580 | 63161879 |
| chr8 | 65281539 | 65281778 | chr8 | 65281884 | 65283443 | chr8 | 65283708 | 65284187 |
| chr8 | 65285972 | 65286451 | chr8 | 65286599 | 65286838 | chr8 | 65286868 | 65287229 |
| chr8 | 65289033 | 65289332 | chr8 | 65289517 | 65290450 | chr8 | 65290570 | 65290896 |
| chr8 | 65290950 | 65291369 | chr8 | 65292097 | 65292102 | chr8 | 65292180 | 65292816 |
| chr8 | 65488178 | 65488417 | chr8 | 65488618 | 65488799 | chr8 | 65489025 | 65489204 |
| chr8 | 65492637 | 65493056 | chr8 | 65493105 | 65493524 | chr8 | 65493556 | 65493855 |
| chr8 | 65493868 | 65493969 | chr8 | 65494048 | 65494287 | chr8 | 65498465 | 65498550 |
| chr8 | 65498645 | 65498910 | chr8 | 65498926 | 65498944 | chr8 | 65499677 | 65500096 |
| chr8 | 65710868 | 65711142 | chr8 | 66548640 | 66548749 | chr8 | 67024963 | 67025365 |
| chr8 | 67344446 | 67344865 | chr8 | 67873246 | 67875697 | chr8 | 67940548 | 67940960 |
| chr8 | 68864493 | 68864852 | chr8 | 59242828 | 69243007 | chr8 | 69243183 | 69243971 |
| chr8 | 69244286 | 69244585 | chr8 | 70744774 | 70745013 | chr8 | 70946670 | 70947742 |
| chr8 | 70981866 | 70983305 | chr8 | 70983402 | 70985081 | chr8 | 72273897 | 72274136 |
| chr8 | 72459929 | 72460348 | chr8 | 72468473 | 72469664 | chr8 | 72470301 | 72470540 |
| chr8 | 72471037 | 72471158 | chr8 | 72754293 | 72754712 | chr8 | 72754730 | 72755240 |
| chr8 | 72755592 | 72756971 | chr8 | 72917268 | 72917541 | chr8 | 72987519 | 72988118 |
| chr8 | 73163680 | 73164261 | chr8 | 73449963 | 73450202 | chr8 | 73450418 | 73450657 |
| chr8 | 74759411 | 74759565 | chr8 | 74759744 | 74759863 | chr8 | 75896477 | 75897436 |
| chr8 | 76316242 | 76316541 | chr8 | 77585130 | 77585789 | chr8 | 77586079 | 77586377 |
| chr8 | 77586471 | 77586710 | chr8 | 77590144 | 77590563 | chr8 | 77593075 | 77593453 |
| chr8 | 77593798 | 77594217 | chr8 | 77594552 | 77595091 | chr8 | 77595238 | 77595594 |
| chr8 | 79428200 | 79428499 | chr8 | 80523887 | 80524126 | chr8 | 80524167 | 80524406 |
| chr8 | 80524864 | 80525103 | chr8 | 80525520 | 80525819 | chr8 | 80695842 | 80696007 |
| chr8 | 80803594 | 80803953 | chr8 | 81478089 | 81478448 | chr8 | 85095396 | 85095755 |
| chr8 | 85096485 | 85096721 | chr8 | 85096785 | 85096904 | chr8 | 85096939 | 85097298 |
| chr8 | 86350455 | 86350633 | chr8 | 86406814 | 86406933 | chr8 | 86436547 | 86436726 |
| chr8 | 86544681 | 86544798 | chr8 | 89339298 | 89339837 | chr8 | 89340189 | 89340428 |
| chr8 | 90913517 | 90913756 | chr8 | 91094161 | 91094326 | chr8 | 91803578 | 91803872 |
| chr8 | 91803913 | 91804332 | chr8 | 91996958 | 91998037 | chr8 | 92083443 | 92083622 |
| chr8 | 93114033 | 93114632 | chr8 | 95651240 | 95651308 | chr8 | 95651448 | 95651599 |
| chr8 | 95651637 | 95651747 | chr8 | 96219911 | 96220002 | chr8 | 97157007 | 97158146 |
| chr8 | 97165541 | 97165780 | chr8 | 97166351 | 97166590 | chr8 | 97167082 | 97167321 |
| chr8 | 97169757 | 97170416 | chr8 | 97170793 | 97170972 | chr8 | 97171036 | 97172295 |
| chr8 | 97172347 | 97173546 | chr8 | 97173730 | 97173991 | chr8 | 97339752 | 97340291 |
| chr8 | 97505950 | 97506609 | chr8 | 97507021 | 97507380 | chr8 | 97507464 | 97507763 |
| chr8 | 98289744 | 98290343 | chr8 | 99439030 | 99439209 | chr8 | 99439299 | 99440438 |
| chr8 | 99951330 | 99951509 | chr8 | 99951757 | 99952896 | chr8 | 99954400 | 99954819 |
| chr8 | 99955105 | 99955394 | chr8 | 99960231 | 99961070 | chr8 | 99961111 | 99961350 |
| chr8 | 99961718 | 99961897 | chr8 | 99985781 | 99987020 | chr8 | 101118140 | 101118679 |
| chr8 | 101661837 | 101662000 | chr8 | 101821891 | 101822130 | chr8 | 102505458 | 102505654 |
| chr8 | 102505720 | 102506079 | chr8 | 103629857 | 103629961 | chr8 | 104153105 | 104153344 |
| chr8 | 104153366 | 104153725 | chr8 | 104512026 | 104513285 | chr8 | 104513365 | 104514005 |
| chr8 | 105235293 | 105236132 | chr8 | 105478632 | 105479281 | chr8 | 105479315 | 105479531 |
| chr8 | 106331080 | 106331319 | chr8 | 106332004 | 106332286 | chr8 | 107282060 | 107282299 |
| chr8 | 107283938 | 107284177 | chr8 | 108509441 | 108509734 | chr8 | 109093601 | 109094260 |

TABLE 14-continued

| chr | start | end | chr | start | end | chr | start | end |
|---|---|---|---|---|---|---|---|---|
| chr8 | 109094391 | 109094690 | chr8 | 109094757 | 109096016 | chr8 | 109799500 | 109799859 |
| chr8 | 110274904 | 110275021 | chr8 | 110405946 | 110406105 | chr8 | 110592245 | 110592303 |
| chr8 | 110703924 | 110704029 | chr8 | 110704098 | 110704223 | chr8 | 110986354 | 110986773 |
| chr8 | 114444497 | 114444640 | chr8 | 114444709 | 114445276 | chr8 | 114445677 | 114446101 |
| chr8 | 114446851 | 114447450 | chr8 | 114448939 | 114449358 | chr8 | 114449457 | 114449688 |
| chr8 | 116660435 | 116660854 | chr8 | 117950364 | 117950543 | chr8 | 117950700 | 117950999 |
| chr8 | 120220390 | 120220629 | chr8 | 120844011 | 120844126 | chr8 | 121136805 | 121137824 |
| chr8 | 121823827 | 121824006 | chr8 | 121824103 | 121824582 | chr8 | 121825512 | 121825560 |
| chr8 | 122651770 | 122652009 | chr8 | 123695447 | 123695746 | chr8 | 124055137 | 124055235 |
| chr8 | 124173165 | 124173544 | chr8 | 125452275 | 125452394 | chr8 | 126044494 | 126044653 |
| chr8 | 128745443 | 128745618 | chr8 | 128872311 | 128872490 | chr8 | 128889224 | 128889483 |
| chr8 | 128931157 | 128931336 | chr8 | 130369290 | 130369454 | chr8 | 132052057 | 132053256 |
| chr8 | 132053633 | 132054876 | chr8 | 133686658 | 133686836 | chr8 | 139508668 | 139509386 |
| chr8 | 139509656 | 139510015 | chr8 | 140714485 | 140714964 | chr8 | 140715016 | 140715195 |
| chr8 | 140715379 | 140715738 | chr8 | 140715875 | 140716348 | chr8 | 140834160 | 140834399 |
| chr8 | 140963208 | 140963447 | chr8 | 141159845 | 141160024 | chr8 | 141587975 | 141588214 |
| chr8 | 141596805 | 141597104 | chr8 | 142292454 | 142292808 | chr8 | 142361151 | 142361430 |
| chr8 | 142367673 | 142367879 | chr8 | 142444648 | 142444827 | chr8 | 142528313 | 142529092 |
| chr8 | 142535241 | 142535587 | chr8 | 142568506 | 142568745 | chr8 | 142694751 | 142695030 |
| chr8 | 142984437 | 142984736 | chr8 | 143088946 | 143089153 | chr8 | 143105162 | 143105461 |
| chr8 | 143509377 | 143509676 | chr8 | 143532035 | 143532934 | chr8 | 143533520 | 143533999 |
| chr8 | 143557881 | 143558172 | chr8 | 143558389 | 143558688 | chr8 | 143587238 | 143587477 |
| chr8 | 143592583 | 143592762 | chr8 | 143621889 | 143622188 | chr8 | 143701978 | 143702157 |
| chr8 | 143819303 | 143819406 | chr8 | 143858435 | 143858791 | chr8 | 143859223 | 143859454 |
| chr8 | 143876854 | 143877033 | chr8 | 143993891 | 143994250 | chr8 | 144069457 | 144069749 |
| chr8 | 144190286 | 144190525 | chr8 | 144203601 | 144203801 | chr8 | 144203880 | 144204020 |
| chr8 | 144226100 | 144226279 | chr8 | 144238743 | 144238982 | chr8 | 144241150 | 144241389 |
| chr8 | 144241444 | 144241683 | chr8 | 144241785 | 144242381 | chr8 | 144303488 | 144303662 |
| chr8 | 144328234 | 144328653 | chr8 | 144330288 | 144330467 | chr8 | 144344219 | 144344518 |
| chr8 | 144359928 | 144360177 | chr8 | 144360305 | 144360544 | chr8 | 144361672 | 144361911 |
| chr8 | 144372474 | 144372583 | chr8 | 144509238 | 144510617 | chr8 | 144511146 | 144511505 |
| chr8 | 144511938 | 144512297 | chr8 | 144512399 | 144512466 | chr8 | 144650791 | 144650812 |
| chr8 | 144668532 | 144668767 | chr8 | 144668822 | 144669061 | chr8 | 145698244 | 145698483 |
| chr8 | 145753443 | 145753622 | chr8 | 145758483 | 145758782 | chr8 | 145806184 | 145806350 |
| chr8 | 145925387 | 145925566 | chr8 | 145925869 | 145926080 | chr8 | 146013543 | 146013722 |
| chr8 | 146079134 | 146079297 | chr9 | 113346 | 113645 | chr9 | 113749 | 113988 |
| chr9 | 117808 | 118167 | chr9 | 841602 | 842244 | chr9 | 842545 | 842766 |
| chr9 | 969482 | 969661 | chr9 | 969685 | 969943 | chr9 | 970012 | 970311 |
| chr9 | 970421 | 970600 | chr9 | 970816 | 971175 | chr9 | 971435 | 971655 |
| chr9 | 972204 | 972863 | chr9 | 973067 | 973366 | chr9 | 975248 | 975262 |
| chr9 | 975693 | 976412 | chr9 | 976521 | 977047 | chr9 | 981695 | 981934 |
| chr9 | 1042305 | 1043076 | chr9 | 1051768 | 1052247 | chr9 | 3181662 | 3181961 |
| chr9 | 6412497 | 6412900 | chr9 | 6644217 | 6644636 | chr9 | 6644936 | 6645415 |
| chr9 | 6645544 | 6645783 | chr9 | 6756279 | 6756429 | chr9 | 13278722 | 13278961 |
| chr9 | 14312943 | 14313182 | chr9 | 14347534 | 14347759 | chr9 | 14348234 | 14348533 |
| chr9 | 17906310 | 17906789 | chr9 | 17906914 | 17907153 | chr9 | 17907325 | 17907564 |
| chr9 | 19789025 | 19789381 | chr9 | 21031636 | 21031924 | chr9 | 21402520 | 21403119 |
| chr9 | 21559219 | 21559446 | chr9 | 21559678 | 21559904 | chr9 | 21964958 | 21965852 |
| chr9 | 21968138 | 21968557 | chr9 | 21970881 | 21971282 | chr9 | 21974164 | 21974329 |
| chr9 | 21974408 | 21974887 | chr9 | 21994134 | 21994313 | chr9 | 21995223 | 21996402 |
| chr9 | 21995646 | 21995825 | chr9 | 22006057 | 22006236 | chr9 | 22447567 | 22447772 |
| chr9 | 23824468 | 23822707 | chr9 | 23824487 | 23824666 | chr9 | 23831023 | 23831490 |
| chr9 | 29212083 | 29212382 | chr9 | 29213431 | 29213730 | chr9 | 29213938 | 29214237 |
| chr9 | 29214276 | 29214515 | chr9 | 29214585 | 29215184 | chr9 | 32782547 | 32783206 |
| chr9 | 32783263 | 32783742 | chr9 | 33524529 | 33524768 | chr9 | 33676697 | 33676876 |
| chr9 | 33677269 | 33677508 | chr9 | 34224262 | 34224497 | chr9 | 34372761 | 34373000 |
| chr9 | 34588960 | 34589259 | chr9 | 34809656 | 34810075 | chr9 | 35617195 | 35617434 |
| chr9 | 35675441 | 35676233 | chr9 | 36036994 | 36037173 | chr9 | 36318274 | 36318389 |
| chr9 | 36739659 | 36740078 | chr9 | 37002394 | 37003113 | chr9 | 37025465 | 37025884 |
| chr9 | 37026055 | 37026714 | chr9 | 37026733 | 37027512 | chr9 | 37027726 | 37027905 |
| chr9 | 37028870 | 37029049 | chr9 | 37029436 | 37030755 | chr9 | 37034163 | 37034342 |
| chr9 | 37034525 | 37034824 | chr9 | 37035427 | 37035820 | chr9 | 37036327 | 37036746 |
| chr9 | 37037594 | 37038433 | chr9 | 37467521 | 37467634 | chr9 | 38620642 | 38620808 |
| chr9 | 66456024 | 66456117 | chr9 | 71200618 | 71200720 | chr9 | 71734803 | 21734920 |
| chr9 | 71788876 | 71789512 | chr9 | 71789608 | 71789835 | chr9 | 73032727 | 73032835 |
| chr9 | 74061745 | 74062164 | chr9 | 74764449 | 74764748 | chr9 | 77112900 | 77113919 |
| chr9 | 77114649 | 77114948 | chr9 | 77115120 | 77115539 | chr9 | 77115583 | 77115587 |
| chr9 | 79626794 | 79627453 | chr9 | 79628190 | 79628429 | chr9 | 79629014 | 79629499 |
| chr9 | 79629533 | 79629553 | chr9 | 79629791 | 79630510 | chr9 | 79631115 | 79631414 |
| chr9 | 79631454 | 79631693 | chr9 | 79631785 | 79632264 | chr9 | 79632786 | 79632965 |
| chr9 | 79633322 | 79633981 | chr9 | 79634088 | 79634987 | chr9 | 79635048 | 79636066 |
| chr9 | 79636103 | 79636127 | chr9 | 79636167 | 79636642 | chr9 | 79636717 | 79637366 |
| chr9 | 79637644 | 79638336 | chr9 | 86152313 | 86152492 | chr9 | 86755443 | 86756042 |
| chr9 | 86886632 | 86886811 | chr9 | 87282934 | 87283113 | chr9 | 87283574 | 87283813 |
| chr9 | 87284603 | 87284902 | chr9 | 87285203 | 87285556 | chr9 | 88137487 | 88138091 |
| chr9 | 89517623 | 89517917 | chr9 | 89560675 | 89560914 | chr9 | 89560967 | 89561206 |
| chr9 | 91150130 | 91150429 | chr9 | 91605912 | 91606151 | chr9 | 91792283 | 91792462 |
| chr9 | 91792693 | 91792992 | chr9 | 91793083 | 91793622 | chr9 | 93697942 | 93698051 |

TABLE 14-continued

| chr | start | end | chr | start | end | chr | start | end |
|---|---|---|---|---|---|---|---|---|
| chr9 | 94183793 | 94184032 | chr9 | 94572543 | 94572703 | chr9 | 94712081 | 94712320 |
| chr9 | 95417452 | 95417747 | chr9 | 95560736 | 95560915 | chr9 | 95569672 | 95569911 |
| chr9 | 95570162 | 95570521 | chr9 | 95571540 | 95571659 | chr9 | 95571753 | 95571839 |
| chr9 | 95947121 | 95947360 | chr9 | 96588726 | 96588965 | chr9 | 96710303 | 96710482 |
| chr9 | 96710582 | 96711089 | chr9 | 96711169 | 96711708 | chr9 | 96711901 | 96712080 |
| chr9 | 96713277 | 96713996 | chr9 | 96714997 | 96715068 | chr9 | 96715135 | 96715794 |
| chr9 | 96716763 | 96717542 | chr9 | 96717885 | 96718244 | chr9 | 96720752 | 96721903 |
| chr9 | 96722477 | 96722886 | chr9 | 96722999 | 96723298 | chr9 | 98111281 | 98112472 |
| chr9 | 98784698 | 98784877 | chr9 | 98789557 | 98790096 | chr9 | 99449054 | 99449487 |
| chr9 | 99639543 | 99640022 | chr9 | 99983066 | 99983245 | chr9 | 99983319 | 99983704 |
| chr9 | 99983799 | 99983918 | chr9 | 99983925 | 99984004 | chr9 | 100503542 | 100504021 |
| chr9 | 100609970 | 100610315 | chr9 | 100610603 | 100611731 | chr9 | 100613748 | 100614407 |
| chr9 | 100614463 | 100616682 | chr9 | 100616743 | 100616982 | chr9 | 100617210 | 100617449 |
| chr9 | 100617600 | 100618139 | chr9 | 100619627 | 100620166 | chr9 | 100620228 | 100620862 |
| chr9 | 100818337 | 100818516 | chr9 | 100835850 | 100835969 | chr9 | 101469169 | 101469408 |
| chr9 | 101469521 | 101469880 | chr9 | 101470034 | 101470333 | chr9 | 101470991 | 101471170 |
| chr9 | 101471477 | 101471716 | chr9 | 101471786 | 101472030 | chr9 | 101705897 | 101706796 |
| chr9 | 103174718 | 103174825 | chr9 | 104248482 | 104248721 | chr9 | 104249400 | 104249632 |
| chr9 | 104500551 | 104500850 | chr9 | 110126159 | 110126338 | chr9 | 110228102 | 110228701 |
| chr9 | 110251381 | 110251493 | chr9 | 110252260 | 110252455 | chr9 | 110252548 | 110252619 |
| chr9 | 112403096 | 112403275 | chr9 | 112403290 | 112403469 | chr9 | 113341445 | 113342044 |
| chr9 | 113342201 | 113342428 | chr9 | 115067840 | 115067945 | chr9 | 115478852 | 115478971 |
| chr9 | 115652867 | 115653526 | chr9 | 116633786 | 116633905 | chr9 | 117050887 | 117051126 |
| chr9 | 118916933 | 118917172 | chr9 | 120175695 | 120175934 | chr9 | 120176009 | 120176248 |
| chr9 | 120176793 | 120176972 | chr9 | 120507335 | 120507514 | chr9 | 122131383 | 122131742 |
| chr9 | 122131785 | 122132320 | chr9 | 123295404 | 123295559 | chr9 | 124751411 | 124751590 |
| chr9 | 125676724 | 125676798 | chr9 | 126133698 | 126133937 | chr9 | 126154201 | 126154651 |
| chr9 | 126349070 | 126349191 | chr9 | 126770159 | 126770398 | chr9 | 126771440 | 126771799 |
| chr9 | 126774442 | 126775221 | chr9 | 126775456 | 126775620 | chr9 | 126775963 | 126776202 |
| chr9 | 126777488 | 126778086 | chr9 | 126778301 | 126778593 | chr9 | 126779391 | 126780406 |
| chr9 | 126780736 | 126780975 | chr9 | 126783321 | 126783577 | chr9 | 127212750 | 127213109 |
| chr9 | 127265588 | 127266127 | chr9 | 127266372 | 127266611 | chr9 | 128652097 | 128652336 |
| chr9 | 128759764 | 128760053 | chr9 | 129276620 | 129276919 | chr9 | 129372837 | 129373316 |
| chr9 | 129376096 | 129376275 | chr9 | 129376815 | 129376892 | chr9 | 129376932 | 129376994 |
| chr9 | 129377116 | 129377415 | chr9 | 129377505 | 129378104 | chr9 | 129381027 | 129381266 |
| chr9 | 129387421 | 129387539 | chr9 | 129387701 | 129388300 | chr9 | 129388639 | 129388878 |
| chr9 | 129388915 | 129389274 | chr9 | 129400912 | 129401271 | chr9 | 129445232 | 129445651 |
| chr9 | 129445709 | 129445888 | chr9 | 129485763 | 129486002 | chr9 | 130248345 | 130248524 |
| chr9 | 130461543 | 130461842 | chr9 | 130689539 | 130689742 | chr9 | 131579939 | 131580104 |
| chr9 | 131607443 | 131607622 | chr9 | 131607696 | 131607875 | chr9 | 131854131 | 131854430 |
| chr9 | 132382297 | 132383116 | chr9 | 132402743 | 132402982 | chr9 | 132403064 | 132403303 |
| chr9 | 132559298 | 132559413 | chr9 | 132805270 | 132805449 | chr9 | 132805750 | 132805989 |
| chr9 | 133308798 | 133309037 | chr9 | 133534609 | 133534788 | chr9 | 133535638 | 133535937 |
| chr9 | 133536012 | 133536431 | chr9 | 133536675 | 133536974 | chr9 | 133537097 | 133537636 |
| chr9 | 133538090 | 133538809 | chr9 | 133539509 | 133539808 | chr9 | 133540977 | 133541276 |
| chr9 | 133541594 | 133542433 | chr9 | 133773666 | 133274025 | chr9 | 133927265 | 133927564 |
| chr9 | 133928162 | 133928341 | chr9 | 134191003 | 134191302 | chr9 | 134207833 | 134207997 |
| chr9 | 134421818 | 134421936 | chr9 | 134717221 | 134717434 | chr9 | 135037029 | 135037448 |
| chr9 | 135455317 | 135455676 | chr9 | 135455912 | 135456151 | chr9 | 135456391 | 35456630 |
| chr9 | 135456796 | 135456915 | chr9 | 135458388 | 135458687 | chr9 | 135459920 | 135460269 |
| chr9 | 135460795 | 135460819 | chr9 | 135461455 | 135461852 | chr9 | 135461969 | 135463048 |
| chr9 | 135464709 | 135465008 | chr9 | 135465861 | 135466220 | chr9 | 135466263 | 135466742 |
| chr9 | 135548157 | 135548265 | chr9 | 135865007 | 135865245 | chr9 | 135898809 | 135899211 |
| chr9 | 136474400 | 136474699 | chr9 | 137299018 | 137299555 | chr9 | 137299596 | 137299677 |
| chr9 | 137533897 | 137534316 | chr9 | 137656864 | 137657223 | chr9 | 137667253 | 137667432 |
| chr9 | 137718802 | 132719101 | chr9 | 137721999 | 137722197 | chr9 | 137979803 | 137980102 |
| chr9 | 137980184 | 137980363 | chr9 | 137980806 | 137980985 | chr9 | 138265038 | 138265337 |
| chr9 | 138562961 | 138563377 | chr9 | 138606221 | 138606460 | chr9 | 138606711 | 138606850 |
| chr9 | 138606927 | 138607010 | chr9 | 138627556 | 138627925 | chr9 | 138633954 | 138634253 |
| chr9 | 138659704 | 138660003 | chr9 | 138660859 | 138661098 | chr9 | 138661550 | 138661969 |
| chr9 | 138666358 | 138666657 | chr9 | 138880882 | 138880973 | chr9 | 138991833 | 138991903 |
| chr9 | 139000485 | 139000724 | chr9 | 139012193 | 139012492 | chr9 | 139024634 | 139024873 |
| chr9 | 139045579 | 139045758 | chr9 | 139047494 | 139047733 | chr9 | 139085145 | 139085444 |
| chr9 | 139085832 | 139086071 | chr9 | 139090420 | 139090659 | chr9 | 139090692 | 139091471 |
| chr9 | 139093067 | 139093966 | chr9 | 139094610 | 139094969 | chr9 | 139095264 | 139095563 |
| chr9 | 139096559 | 139097098 | chr9 | 139111194 | 139111373 | chr9 | 139268961 | 139268987 |
| chr9 | 139421881 | 139422060 | chr9 | 139698839 | 139699138 | chr9 | 139704085 | 139704384 |
| chr9 | 139739149 | 139739388 | chr9 | 139858946 | 139859365 | chr9 | 139888844 | 139889083 |
| chr9 | 140024754 | 140025113 | chr9 | 140030424 | 140030603 | chr9 | 140032802 | 140033050 |
| chr9 | 140033192 | 140033197 | chr9 | 140033325 | 140033744 | chr9 | 140033815 | 140034174 |
| chr9 | 140050893 | 140051432 | chr9 | 140127803 | 140128162 | chr9 | 140137220 | 140137334 |
| chr9 | 140205346 | 140205607 | chr9 | 140245789 | 140246084 | chr9 | 140332524 | 140333103 |
| chr9 | 140382472 | 140382697 | chr9 | 140392380 | 140392559 | chr9 | 140396944 | 140397183 |
| chr9 | 140507207 | 140507506 | chr9 | 140708961 | 140709260 | chr9 | 140727429 | 140727611 |
| chr9 | 140727769 | 140728008 | chr9 | 140769913 | 140770048 | chr9 | 140771969 | 140772431 |
| chr9 | 140772495 | 140773394 | chr10 | 524680 | 524770 | chr10 | 833228 | 833419 |
| chr10 | 978787 | 979026 | chr10 | 1585208 | 1585325 | chr10 | 1708551 | 1708583 |
| chr10 | 1779342 | 1779821 | chr10 | 3285686 | 3285792 | chr10 | 3330410 | 3330696 |

TABLE 14-continued

| chr | start | end | chr | start | end | chr | start | end |
|---|---|---|---|---|---|---|---|---|
| chr10 | 3641277 | 3641396 | chr10 | 3678618 | 3678737 | chr10 | 3895312 | 3895551 |
| chr10 | 4599822 | 4600061 | chr10 | 5530673 | 5531080 | chr10 | 5875059 | 5875345 |
| chr10 | 6003386 | 6003625 | chr10 | 6042233 | 6042592 | chr10 | 6162073 | 6162302 |
| chr10 | 6577569 | 6577748 | chr10 | 6984626 | 6984731 | chr10 | 7205641 | 7205880 |
| chr10 | 7212666 | 7213145 | chr10 | 7213532 | 7213610 | chr10 | 7215985 | 7216164 |
| chr10 | 7236109 | 7236348 | chr10 | 7255627 | 7255659 | chr10 | 7414447 | 7414686 |
| chr10 | 7424552 | 7424731 | chr10 | 7449863 | 7451482 | chr10 | 7452143 | 7452862 |
| chr10 | 7453233 | 7454012 | chr10 | 7708311 | 7708379 | chr10 | 7708700 | 7709090 |
| chr10 | 7709649 | 7709807 | chr10 | 8075843 | 8076071 | chr10 | 8076264 | 8076563 |
| chr10 | 8076730 | 8077449 | chr10 | 8077790 | 8078316 | chr10 | 8084961 | 8085800 |
| chr10 | 8085875 | 8086114 | chr10 | 8091818 | 8092099 | chr10 | 8093653 | 8094072 |
| chr10 | 8095515 | 8095774 | chr10 | 8095842 | 8095934 | chr10 | 8096086 | 8096265 |
| chr10 | 8096877 | 8097296 | chr10 | 8097387 | 8097626 | chr10 | 11059620 | 11060159 |
| chr10 | 11207079 | 11207378 | chr10 | 11700861 | 11701100 | chr10 | 13043287 | 13043526 |
| chr10 | 13141002 | 13141106 | chr10 | 13715452 | 13715485 | chr10 | 13933361 | 13934260 |
| chr10 | 14966052 | 14966291 | chr10 | 15140509 | 15140625 | chr10 | 15761213 | 15761752 |
| chr10 | 15762050 | 15762211 | chr10 | 16562009 | 16563988 | chr10 | 16564013 | 16564127 |
| chr10 | 17270131 | 17270529 | chr10 | 17270889 | 17271728 | chr10 | 17271835 | 17272313 |
| chr10 | 17272527 | 17272706 | chr10 | 17429082 | 17429244 | chr10 | 17429562 | 17429724 |
| chr10 | 17496115 | 17496834 | chr10 | 18429147 | 18429386 | chr10 | 18429552 | 18429851 |
| chr10 | 21462526 | 21462690 | chr10 | 21805128 | 21805367 | chr10 | 22047362 | 22047601 |
| chr10 | 22541563 | 22542342 | chr10 | 22623924 | 22626080 | chr10 | 22633902 | 22634672 |
| chr10 | 22764556 | 22765991 | chr10 | 23216786 | 23217025 | chr10 | 23460264 | 23460552 |
| chr10 | 23461129 | 23461848 | chr10 | 23461976 | 23462995 | chr10 | 23463075 | 23464154 |
| chr10 | 23479793 | 23481171 | chr10 | 23481239 | 23481598 | chr10 | 23481862 | 23482621 |
| chr10 | 23483744 | 23484703 | chr10 | 23486177 | 23486416 | chr10 | 23487651 | 23488070 |
| chr10 | 23488297 | 23489256 | chr10 | 23489335 | 23489514 | chr10 | 23982360 | 23982899 |
| chr10 | 23983102 | 23983341 | chr10 | 23983382 | 23983801 | chr10 | 23984008 | 23984307 |
| chr10 | 23984838 | 23985066 | chr10 | 24988575 | 24988641 | chr10 | 25464528 | 25464910 |
| chr10 | 25465320 | 25465619 | chr10 | 26055737 | 26055916 | chr10 | 26222916 | 26223513 |
| chr10 | 26223957 | 26224136 | chr10 | 26500528 | 26501007 | chr10 | 26501445 | 26501668 |
| chr10 | 26503593 | 26503832 | chr10 | 26504018 | 26504257 | chr10 | 26504410 | 26505309 |
| chr10 | 26505364 | 26505783 | chr10 | 26505961 | 26506260 | chr10 | 26506288 | 26507427 |
| chr10 | 26681025 | 26681204 | chr10 | 26727024 | 26727443 | chr10 | 26727509 | 26727928 |
| chr10 | 26746956 | 26747074 | chr10 | 26816913 | 26817032 | chr10 | 27547856 | 27548575 |
| chr10 | 27794394 | 27794512 | chr10 | 27846608 | 27846719 | chr10 | 28030790 | 28031029 |
| chr10 | 28032874 | 28033113 | chr10 | 28033327 | 28033566 | chr10 | 28033667 | 28034446 |
| chr10 | 28034489 | 28035388 | chr10 | 28035520 | 28035879 | chr10 | 28287286 | 28287481 |
| chr10 | 28287693 | 28288164 | chr10 | 28957989 | 28958226 | chr10 | 29010956 | 29011239 |
| chr10 | 30025881 | 30026180 | chr10 | 31073276 | 31073545 | chr10 | 31892822 | 31893181 |
| chr10 | 32499021 | 32499260 | chr10 | 33233249 | 33233457 | chr10 | 33624079 | 33624318 |
| chr10 | 33624407 | 33624550 | chr10 | 33624621 | 33624646 | chr10 | 36929070 | 35929609 |
| chr10 | 43249935 | 43250114 | chr10 | 43250317 | 43250976 | chr10 | 43428329 | 43428688 |
| chr10 | 43428903 | 43429202 | chr10 | 43429275 | 43429514 | chr10 | 43572591 | 43572830 |
| chr10 | 43600462 | 43600733 | chr10 | 43615462 | 43615639 | chr10 | 43697812 | 43698092 |
| chr10 | 43698199 | 43698231 | chr10 | 43858258 | 43858437 | chr10 | 44879847 | 44880326 |
| chr10 | 44880773 | 44881012 | chr10 | 49652880 | 49653179 | chr10 | 49731470 | 49731829 |
| chr10 | 49731980 | 49732579 | chr10 | 50323162 | 50323360 | chr10 | 50340179 | 50340224 |
| chr10 | 50507469 | 50507708 | chr10 | 50603884 | 50604243 | chr10 | 50604508 | 50604747 |
| chr10 | 50604967 | 50604979 | chr10 | 50605053 | 50505746 | chr10 | 50605931 | 50606530 |
| chr10 | 50816972 | 50817224 | chr10 | 50817778 | 50818017 | chr10 | 50818288 | 50818527 |
| chr10 | 50818724 | 50819203 | chr10 | 50821378 | 50821797 | chr10 | 50887557 | 50887916 |
| chr10 | 50976785 | 50977144 | chr10 | 54068449 | 54068688 | chr10 | 54072882 | 54073121 |
| chr10 | 54073191 | 54073370 | chr10 | 54074648 | 54074887 | chr10 | 57387344 | 57387883 |
| chr10 | 57388239 | 57388598 | chr10 | 57390195 | 57390734 | chr10 | 57391072 | 57391311 |
| chr10 | 60273033 | 60273392 | chr10 | 60935793 | 60936091 | chr10 | 60936449 | 60936808 |
| chr10 | 60936999 | 60937178 | chr10 | 63212244 | 63212783 | chr10 | 64575433 | 64575732 |
| chr10 | 64578189 | 64578626 | chr10 | 71327627 | 71327865 | chr10 | 71328678 | 21328917 |
| chr10 | 71328980 | 71329219 | chr10 | 71329462 | 71329633 | chr10 | 71331965 | 71332650 |
| chr10 | 71332686 | 71333105 | chr10 | 72015070 | 72015425 | chr10 | 72043557 | 72043976 |
| chr10 | 72200001 | 72200240 | chr10 | 72200251 | 72201390 | chr10 | 72973124 | 72973275 |
| chr10 | 73156273 | 73156465 | chr10 | 73156550 | 73156752 | chr10 | 73157768 | 73158049 |
| chr10 | 73847788 | 73848267 | chr10 | 75407495 | 75407782 | chr10 | 75488860 | 75488975 |
| chr10 | 77191147 | 77191446 | chr10 | 79396826 | 79397185 | chr10 | 81023964 | 81023989 |
| chr10 | 81664764 | 81665003 | chr10 | 82116994 | 82117283 | chr10 | 83634171 | 83634234 |
| chr10 | 83635441 | 83635620 | chr10 | 85954322 | 85954561 | chr10 | 88149273 | 88149692 |
| chr10 | 89692817 | 89692996 | chr10 | 89717584 | 89717763 | chr10 | 90966608 | 90966967 |
| chr10 | 90967587 | 90968126 | chr10 | 91294929 | 91295168 | chr10 | 91295449 | 91295808 |
| chr10 | 92617156 | 92617395 | chr10 | 93647139 | 93647378 | chr10 | 93647486 | 93647725 |
| chr10 | 94450582 | 94450805 | chr10 | 94451372 | 94451587 | chr10 | 94825999 | 94826160 |
| chr10 | 94828062 | 94828601 | chr10 | 94828633 | 94828932 | chr10 | 94834311 | 94835088 |
| chr10 | 96304116 | 96304200 | chr10 | 98129719 | 98130138 | chr10 | 99080176 | 99080535 |
| chr10 | 99080774 | 99081061 | chr10 | 99531116 | 99531535 | chr10 | 99789080 | 99789379 |
| chr10 | 99790171 | 99790410 | chr10 | 99790508 | 99790747 | chr10 | 99790845 | 99791258 |
| chr10 | 100991863 | 100991935 | chr10 | 100992056 | 100992535 | chr10 | 100992780 | 100992822 |
| chr10 | 100993448 | 100994107 | chr10 | 100995956 | 100996315 | chr10 | 101088918 | 101089517 |
| chr10 | 101089817 | 101090296 | chr10 | 101280106 | 101280569 | chr10 | 101283382 | 101283577 |
| chr10 | 101290028 | 101291284 | chr10 | 101292254 | 101292998 | chr10 | 101293071 | 101293430 |

TABLE 14-continued

| chr | start | end | chr | start | end | chr | start | end |
|---|---|---|---|---|---|---|---|---|
| chr10 | 101294662 | 101295681 | chr10 | 101295665 | 101296892 | chr10 | 101874886 | 101875222 |
| chr10 | 102322155 | 102322335 | chr10 | 102419230 | 102419769 | chr10 | 102430611 | 102430850 |
| chr10 | 102473775 | 102474014 | chr10 | 102483915 | 102484632 | chr10 | 102495416 | 102495717 |
| chr10 | 102497192 | 102497791 | chr10 | 102498178 | 102498537 | chr10 | 102501285 | 102501464 |
| chr10 | 102507408 | 102507707 | chr10 | 102508902 | 102509381 | chr10 | 102586425 | 102586904 |
| chr10 | 102589340 | 102589579 | chr10 | 102589702 | 102590001 | chr10 | 102590075 | 102590494 |
| chr10 | 102890843 | 102891682 | chr10 | 102891745 | 102892104 | chr10 | 102893528 | 102895366 |
| chr10 | 102899088 | 102899687 | chr10 | 102899712 | 102900671 | chr10 | 102906423 | 102906662 |
| chr10 | 102975518 | 102975937 | chr10 | 102976963 | 102977502 | chr10 | 102983062 | 102983841 |
| chr10 | 102984313 | 102984612 | chr10 | 102985689 | 102986048 | chr10 | 102986447 | 102987646 |
| chr10 | 102989555 | 102989734 | chr10 | 102996018 | 102996737 | chr10 | 102997249 | 102997488 |
| chr10 | 102998493 | 102998912 | chr10 | 103043872 | 103044471 | chr10 | 103535527 | 103535586 |
| chr10 | 103535634 | 103535886 | chr10 | 103536143 | 103536502 | chr10 | 103579718 | 103579794 |
| chr10 | 103930133 | 103930248 | chr10 | 104169995 | 104170834 | chr10 | 105036464 | 105036943 |
| chr10 | 105037138 | 105037917 | chr10 | 105127048 | 105127156 | chr10 | 105155378 | 105155563 |
| chr10 | 105413527 | 105413886 | chr10 | 106398556 | 106398975 | chr10 | 106399505 | 106400464 |
| chr10 | 106400869 | 106402428 | chr10 | 106402620 | 106402919 | chr10 | 108923951 | 108924190 |
| chr10 | 108924365 | 108924784 | chr10 | 110226162 | 110226401 | chr10 | 110671800 | 110672339 |
| chr10 | 111216709 | 111217008 | chr10 | 112403075 | 112403374 | chr10 | 112440312 | 1124404.83 |
| chr10 | 115804748 | 115805107 | chr10 | 116164146 | 116164445 | chr10 | 116331052 | 116331231 |
| chr10 | 116853773 | 116854012 | chr10 | 118030550 | 118030969 | chr10 | 118031206 | 118032645 |
| chr10 | 118032841 | 118033140 | chr10 | 118033261 | 118033620 | chr10 | 118034064 | 118034243 |
| chr10 | 118890893 | 118891192 | chr10 | 118891437 | 118891854 | chr10 | 118891938 | 118893360 |
| chr10 | 118893484 | 118894383 | chr10 | 118896538 | 118896897 | chr10 | 118897822 | 118898061 |
| chr10 | 118899199 | 118899378 | chr10 | 118899435 | 118900034 | chr10 | 118900063 | 118900602 |
| chr10 | 118922061 | 118922296 | chr10 | 118922632 | 118922900 | chr10 | 118922944 | 118922991 |
| chr10 | 118923050 | 118923349 | chr10 | 118924511 | 118924990 | chr10 | 118927012 | 118927371 |
| chr10 | 118928459 | 118928614 | chr10 | 119000564 | 119001403 | chr10 | 119001460 | 119001639 |
| chr10 | 119292187 | 119292419 | chr10 | 119294258 | 119294557 | chr10 | 119294747 | 119295346 |
| chr10 | 119296628 | 119296867 | chr10 | 119297308 | 119297607 | chr10 | 119301278 | 119301757 |
| chr10 | 119302055 | 119302080 | chr10 | 119302859 | 119303278 | chr10 | 119304289 | 119304468 |
| chr10 | 119304794 | 119305213 | chr10 | 119306948 | 119307127 | chr10 | 119311793 | 119311830 |
| chr10 | 119311905 | 119311972 | chr10 | 119312673 | 119313272 | chr10 | 119806952 | 119807131 |
| chr10 | 120354169 | 120354348 | chr10 | 120355462 | 120355701 | chr10 | 120841455 | 120841563 |
| chr10 | 122216811 | 122217170 | chr10 | 122708479 | 122708773 | chr10 | 123357681 | 123357757 |
| chr10 | 123922546 | 123923565 | chr10 | 124893085 | 124893444 | chr10 | 124893551 | 124893850 |
| chr10 | 124893863 | 124894582 | chr10 | 124894787 | 124895026 | chr10 | 124895342 | 124896541 |
| chr10 | 124896768 | 124897007 | chr10 | 124897118 | 124897657 | chr10 | 124897958 | 124898056 |
| chr10 | 124898957 | 124899196 | chr10 | 124899651 | 124899890 | chr10 | 124901816 | 124903315 |
| chr10 | 124904841 | 124905200 | chr10 | 124905407 | 124905586 | chr10 | 124905834 | 124906186 |
| chr10 | 124907214 | 124907633 | chr10 | 124908017 | 124908196 | chr10 | 124908987 | 124909769 |
| chr10 | 124910287 | 124911126 | chr10 | 125425412 | 125425651 | chr10 | 125650778 | 125651437 |
| chr10 | 125851248 | 125851727 | chr10 | 125852203 | 125852622 | chr10 | 125852673 | 125853272 |
| chr10 | 126135847 | 126136146 | chr10 | 126136406 | 126136810 | chr10 | 126137145 | 126137503 |
| chr10 | 126198864 | 126199163 | chr10 | 126697829 | 126698125 | chr10 | 128076477 | 128076716 |
| chr10 | 128077188 | 128077367 | chr10 | 128993816 | 128994535 | chr10 | 128994636 | 128994995 |
| chr10 | 129534562 | 129535825 | chr10 | 129535986 | 129536405 | chr10 | 129888774 | 129888965 |
| chr10 | 129948037 | 129948216 | chr10 | 130085210 | 130085449 | chr10 | 130203339 | 130203578 |
| chr10 | 130338713 | 130339062 | chr10 | 130577690 | 130577869 | chr10 | 131647829 | 131648008 |
| chr10 | 131756992 | 131757531 | chr10 | 131757852 | 131758151 | chr10 | 131761291 | 131761530 |
| chr10 | 131761587 | 131761826 | chr10 | 131761987 | 131762226 | chr10 | 131762493 | 131762732 |
| chr10 | 131762803 | 131763042 | chr10 | 131763264 | 131763803 | chr10 | 131767343 | 131767522 |
| chr10 | 131768638 | 131769117 | chr10 | 131769436 | 131770335 | chr10 | 131770583 | 131770762 |
| chr10 | 131770908 | 131771327 | chr10 | 131936600 | 131936719 | chr10 | 131937393 | 131937512 |
| chr10 | 132001196 | 132001615 | chr10 | 133109096 | 133109395 | chr10 | 133109559 | 133109858 |
| chr10 | 133110260 | 133110799 | chr10 | 133794798 | 133795517 | chr10 | 133795593 | 133796312 |
| chr10 | 133849561 | 133850103 | chr10 | 133850443 | 133850862 | chr10 | 133951516 | 133962107 |
| chr10 | 133979076 | 133979164 | chr10 | 133999917 | 134000216 | chr10 | 134001000 | 134001359 |
| chr10 | 134016117 | 134016476 | chr10 | 134022771 | 134022950 | chr10 | 134095505 | 134095924 |
| chr10 | 134272961 | 134272970 | chr10 | 134301005 | 134301304 | chr10 | 134481228 | 134481527 |
| chr10 | 134598013 | 134598192 | chr10 | 134598254 | 134598613 | chr10 | 134598973 | 134599572 |
| chr10 | 134599714 | 134601053 | chr10 | 134601468 | 134601887 | chr10 | 134602107 | 134602346 |
| chr10 | 134607868 | 134608284 | chr10 | 134665056 | 134665295 | chr10 | 134679326 | 134679347 |
| chr10 | 134690469 | 134690636 | chr10 | 134693499 | 134693798 | chr10 | 134699772 | 134700011 |
| chr10 | 134733129 | 134733368 | chr10 | 134733707 | 134733946 | chr10 | 134738301 | 134738720 |
| chr10 | 134755743 | 134756270 | chr10 | 134787988 | 134788194 | chr10 | 134795938 | 134796117 |
| chr10 | 134901113 | 134901592 | chr10 | 134901919 | 134902352 | chr10 | 134916625 | 134916864 |
| chr10 | 134941043 | 134941282 | chr10 | 134942738 | 134943216 | chr10 | 134943461 | 134943644 |
| chr10 | 134944668 | 134944847 | chr10 | 135001961 | 135002260 | chr10 | 135014869 | 135015228 |
| chr10 | 135016972 | 135017209 | chr10 | 135017932 | 135018148 | chr10 | 135018744 | 135019043 |
| chr10 | 135020698 | 135020988 | chr10 | 135023396 | 135023575 | chr10 | 135043080 | 135043613 |
| chr10 | 135043869 | 135044228 | chr10 | 135044423 | 135044662 | chr10 | 135048742 | 135049041 |
| chr10 | 135050226 | 135050765 | chr10 | 135076308 | 135076586 | chr10 | 135121730 | 135122131 |
| chr10 | 135139464 | 135139805 | chr11 | 232816 | 233115 | chr11 | 392560 | 392739 |
| chr11 | 394713 | 395072 | chr11 | 406789 | 407028 | chr11 | 407326 | 407565 |
| chr11 | 626983 | 627282 | chr11 | 536821 | 637000 | chr11 | 637100 | 637528 |
| chr11 | 726323 | 726562 | chr11 | 763236 | 763775 | chr11 | 829453 | 829806 |
| chr11 | 830021 | 830370 | chr11 | 850480 | 850899 | chr11 | 862988 | 863167 |

TABLE 14-continued

| chr | start | end | chr | start | end | chr | start | end |
|---|---|---|---|---|---|---|---|---|
| chr11 | 1027438 | 1027676 | chr11 | 1029142 | 1029501 | chr11 | 1030137 | 1030376 |
| chr11 | 1080304 | 1080416 | chr11 | 1081572 | 1081811 | chr11 | 1214582 | 1215001 |
| chr11 | 1215800 | 1216099 | chr11 | 1229871 | 1230050 | chr11 | 1244304 | 1244543 |
| chr11 | 1250788 | 1251027 | chr11 | 1251088 | 1251447 | chr11 | 1263504 | 1263743 |
| chr11 | 1273988 | 1274287 | chr11 | 1358284 | 1358432 | chr11 | 1374862 | 1375101 |
| chr11 | 1411801 | 1411980 | chr11 | 1430635 | 1430874 | chr11 | 1464205 | 1464504 |
| chr11 | 1469125 | 1469484 | chr11 | 1471840 | 1472139 | chr11 | 1769971 | 1770330 |
| chr11 | 1867980 | 1868339 | chr11 | 1946056 | 1.946235 | chr11 | 1957312 | 1957611 |
| chr11 | 1958983 | 1959282 | chr11 | 2040009 | 2040248 | chr11 | 2209824 | 2210363 |
| chr11 | 2225974 | 2226153 | chr11 | 2278625 | 2278924 | chr11 | 2291185 | 2291844 |
| chr11 | 2291891 | 2292730 | chr11 | 2437889 | 2438246 | chr11 | 2465323 | 2465571 |
| chr11 | 2466514 | 2466873 | chr11 | 2884027 | 2884121 | chr11 | 2884158 | 2884386 |
| chr11 | 3169689 | 3169930 | chr11 | 4209031 | 4209210 | chr11 | 7273212 | 7273451 |
| chr11 | 7274141 | 7274320 | chr11 | 8040444 | 8040863 | chr11 | 8102910 | 8103209 |
| chr11 | 8189898 | 8190857 | chr11 | 8284465 | 8284858 | chr11 | 8289436 | 8289841 |
| chr11 | 8290100 | 8290515 | chr11 | 8615600 | 8615779 | chr11 | 9025890 | 9026429 |
| chr11 | 9112372 | 9112834 | chr11 | 9405310 | 9405542 | chr11 | 10509594 | 10509893 |
| chr11 | 10811069 | 10811188 | chr11 | 10815784 | 10815896 | chr11 | 12029876 | 12030355 |
| chr11 | 12030749 | 12030928 | chr11 | 12132423 | 12132662 | chr11 | 12398952 | 12399145 |
| chr11 | 12399181 | 12399311 | chr11 | 12695397 | 12695696 | chr11 | 12696530 | 12696764 |
| chr11 | 13030489 | 13030792 | chr11 | 13030862 | 13030968 | chr11 | 15136001 | 15136480 |
| chr11 | 16628727 | 16628998 | chr11 | 16632403 | 16632752 | chr11 | 17497410 | 17497769 |
| chr11 | 17740413 | 17740652 | chr11 | 17741583 | 17741685 | chr11 | 17741718 | 17742542 |
| chr11 | 17743640 | 17743874 | chr11 | 18812515 | 18812754 | chr11 | 18812940 | 18813179 |
| chr11 | 18813356 | 18813655 | chr11 | 18813691 | 18814050 | chr11 | 19263774 | 19263953 |
| chr11 | 19367007 | 19367426 | chr11 | 19735656 | 19735835 | chr11 | 20153622 | 20153861 |
| chr11 | 20177977 | 20178396 | chr11 | 20180244 | 20180896 | chr11 | 20181115 | 20181354 |
| chr11 | 20181608 | 20182087 | chr11 | 20182763 | 20183062 | chr11 | 20183157 | 20183211 |
| chr11 | 20183313 | 20183516 | chr11 | 20183575 | 20183852 | chr11 | 20184481 | 20185500 |
| chr11 | 20229275 | 20229634 | chr11 | 20229811 | 20230110 | chr11 | 20230312 | 20230551 |
| chr11 | 20618116 | 20619255 | chr11 | 20619637 | 20620056 | chr11 | 20621460 | 20621733 |
| chr11 | 20622613 | 20623452 | chr11 | 20690555 | 20691034 | chr11 | 20691127 | 20691546 |
| chr11 | 20691591 | 20692010 | chr11 | 20692372 | 20692611 | chr11 | 22215025 | 22215385 |
| chr11 | 22362853 | 22363272 | chr11 | 22364719 | 12365078 | chr11 | 22365323 | 22365562 |
| chr11 | 27742111 | 27742290 | chr11 | 27743025 | 27743264 | chr11 | 27743343 | 27743702 |
| chr11 | 27744057 | 27744596 | chr11 | 27744609 | 27744832 | chr11 | 30037596 | 30037818 |
| chr11 | 30038595 | 30038834 | chr11 | 30605946 | 30606201 | chr11 | 30606665 | 30606964 |
| chr11 | 30607269 | 30607508 | chr11 | 31818376 | 31818674 | chr11 | 31819221 | 31819508 |
| chr11 | 31819569 | 31819928 | chr11 | 31819966 | 31821105 | chr11 | 31821209 | 31821860 |
| chr11 | 31822240 | 31822479 | chr11 | 31824209 | 31824448 | chr11 | 31824473 | 31824772 |
| chr11 | 31824940 | 31825359 | chr11 | 31825611 | 31827290 | chr11 | 31827362 | 31828142 |
| chr11 | 31833007 | 31833232 | chr11 | 31835633 | 31835872 | chr11 | 31835959 | 31836517 |
| chr11 | 31836927 | 31838485 | chr11 | 31838596 | 31839135 | chr11 | 31839215 | 31840174 |
| chr11 | 31840486 | 31841025 | chr11 | 31841287 | 31842366 | chr11 | 31845947 | 31845991 |
| chr11 | 31846078 | 31846306 | chr11 | 31846351 | 31847070 | chr11 | 31847169 | 31848008 |
| chr11 | 31848377 | 31849177 | chr11 | 32009013 | 32009252 | chr11 | 32354816 | 32355291 |
| chr11 | 32448482 | 32449081 | chr11 | 32455499 | 32455738 | chr11 | 32455754 | 32456113 |
| chr11 | 32456189 | 32457268 | chr11 | 32457615 | 32458274 | chr11 | 32458307 | 32458860 |
| chr11 | 32459609 | 32459971 | chr11 | 32460118 | 32460148 | chr11 | 32460373 | 32460612 |
| chr11 | 32460711 | 32460950 | chr11 | 33037393 | 33037632 | chr11 | 33858439 | 33858544 |
| chr11 | 33890197 | 33890436 | chr11 | 33993910 | 33993979 | chr11 | 34535019 | 34535198 |
| chr11 | 35547412 | 35547651 | chr11 | 35641582 | 35641718 | chr11 | 35684866 | 35685225 |
| chr11 | 43596412 | 43596693 | chr11 | 43600416 | 43600655 | chr11 | 43601012 | 43601551 |
| chr11 | 43602369 | 43603328 | chr11 | 43603544 | 43604263 | chr11 | 44325599 | 44325838 |
| chr11 | 44326042 | 44326281 | chr11 | 44326341 | 44326580 | chr11 | 44330555 | 44331814 |
| chr11 | 44332978 | 44333157 | chr11 | 44333466 | 44333576 | chr11 | 44337564 | 44338154 |
| chr11 | 44338232 | 44338471 | chr11 | 44340722 | 44340808 | chr11 | 44341881 | 44342120 |
| chr11 | 46316761 | 46317780 | chr11 | 47208968 | 47209267 | chr11 | 47358895 | 47359314 |
| chr11 | 57194253 | 57194612 | chr11 | 57235332 | 57235511 | chr11 | 57437215 | 57437316 |
| chr11 | 57501032 | 57501145 | chr11 | 58672666 | 58673145 | chr11 | 59323514 | 59323551 |
| chr11 | 59323780 | 59323813 | chr11 | 59329224 | 59329343 | chr11 | 59333344 | 59333623 |
| chr11 | 60718587 | 60719246 | chr11 | 61049596 | 61049756 | chr11 | 61058193 | 61058432 |
| chr11 | 61062741 | 61063220 | chr11 | 61276902 | 61277321 | chr11 | 61594995 | 61595354 |
| chr11 | 61596321 | 61596740 | chr11 | 61664564 | 61664863 | chr11 | 61666032 | 61666211 |
| chr11 | 61722964 | 61723262 | chr11 | 62370646 | 62370825 | chr11 | 62440550 | 62440669 |
| chr11 | 63609981 | 63610099 | chr11 | 63641023 | 63641104 | chr11 | 63767909 | 63768208 |
| chr11 | 63849298 | 63849530 | chr11 | 63934600 | 63934709 | chr11 | 64105852 | 64106031 |
| chr11 | 64120805 | 64120984 | chr11 | 64140323 | 64140502 | chr11 | 64410622 | 64410861 |
| chr11 | 64480332 | 64480691 | chr11 | 64480724 | 64481143 | chr11 | 64578481 | 64578600 |
| chr11 | 64739369 | 64739608 | chr11 | 64809866 | 64809965 | chr11 | 54950214 | 64950438 |
| chr11 | 65091311 | 65091471 | chr11 | 65185459 | 65185818 | chr11 | 55405568 | 65405597 |
| chr11 | 65478529 | 65478644 | chr11 | 65511077 | 65511256 | chr11 | 65511332 | 65511571 |
| chr11 | 65553957 | 65554195 | chr11 | 65600716 | 65601735 | chr11 | 65779218 | 65779457 |
| chr11 | 65816357 | 65816656 | chr11 | 66188041 | 66188220 | chr11 | 66188395 | 66189054 |
| chr11 | 66454350 | 66454529 | chr11 | 66511148 | 66511327 | chr11 | 66513133 | 66513252 |
| chr11 | 66513554 | 66513732 | chr11 | 66625105 | 66625344 | chr11 | 66648954 | 66649133 |
| chr11 | 66658258 | 66658365 | chr11 | 66790519 | 66790758 | chr11 | 67072139 | 67072489 |
| chr11 | 67209918 | 67210157 | chr11 | 67350887 | 67351066 | chr11 | 67462559 | 67462918 |

TABLE 14-continued

| chr | start | end | chr | start | end | chr | start | end |
|---|---|---|---|---|---|---|---|---|
| chr11 | 67764102 | 67764341 | chr11 | 67781387 | 67781650 | chr11 | 67797102 | 67797281 |
| chr11 | 68096026 | 68096257 | chr11 | 68409507 | 68409663 | chr11 | 68804647 | 68804872 |
| chr11 | 69192466 | 69192885 | chr11 | 69280478 | 69280717 | chr11 | 69465962 | 69466143 |
| chr11 | 69516896 | 69517251 | chr11 | 69517942 | 69518301 | chr11 | 69518445 | 69518708 |
| chr11 | 69588848 | 69589267 | chr11 | 69589750 | 69589929 | chr11 | 69590067 | 69590306 |
| chr11 | 71192669 | 71192921 | chr11 | 71318231 | 71319070 | chr11 | 71951540 | 71951815 |
| chr11 | 71952262 | 71952621 | chr11 | 71954538 | 71954717 | chr11 | 71955242 | 71955481 |
| chr11 | 71955905 | 71956444 | chr11 | 72432759 | 72432997 | chr11 | 72475581 | 72475814 |
| chr11 | 72532274 | 72532453 | chr11 | 72929666 | 72929731 | chr11 | 73072871 | 73073050 |
| chr11 | 73310285 | 73310445 | chr11 | 74394397 | 74394696 | chr11 | 74953165 | 74953524 |
| chr11 | 75379155 | 75379994 | chr11 | 75459452 | 75459564 | chr11 | 76371639 | 76372178 |
| chr11 | 78672822 | 78673061 | chr11 | 79151076 | 79151315 | chr11 | 82444290 | 82445189 |
| chr11 | 86085657 | 86086065 | chr11 | 86383080 | 86383186 | chr11 | 88241623 | 88242702 |
| chr11 | 88798997 | 88799296 | chr11 | 91957408 | 91957767 | chr11 | 91957893 | 91958312 |
| chr11 | 91958633 | 91959532 | chr11 | 91959901 | 91960122 | chr11 | 93063495 | 93063734 |
| chr11 | 93063790 | 93064029 | chr11 | 94133991 | 94134950 | chr11 | 94275701 | 94275813 |
| chr11 | 94473511 | 94473997 | chr11 | 94474399 | 94474401 | chr11 | 94502273 | 94502592 |
| chr11 | 94884070 | 94884235 | chr11 | 98891381 | 98891980 | chr11 | 100997579 | 100998085 |
| chr11 | 100998178 | 100998417 | chr11 | 100998588 | 100998827 | chr11 | 101453080 | 101453619 |
| chr11 | 101454101 | 101454580 | chr11 | 102961259 | 102961378 | chr11 | 102979953 | 102980132 |
| chr11 | 104034430 | 104035089 | chr11 | 105480562 | 105480901 | chr11 | 106481125 | 106481604 |
| chr11 | 106888220 | 106888519 | chr11 | 106888542 | 106888901 | chr11 | 107461549 | 107461728 |
| chr11 | 107462318 | 107462557 | chr11 | 108603286 | 108603338 | chr11 | 109292830 | 109293129 |
| chr11 | 109293635 | 109293934 | chr11 | 110582154 | 110582513 | chr11 | 110582794 | 110583153 |
| chr11 | 110583473 | 110583832 | chr11 | 111383104 | 111383763 | chr11 | 111411019 | 111412147 |
| chr11 | 114112948 | 114113127 | chr11 | 115375030 | 115375269 | chr11 | 115530040 | 115530662 |
| chr11 | 115630414 | 115631013 | chr11 | 115631217 | 115631456 | chr11 | 116451226 | 116451287 |
| chr11 | 119292705 | 119292884 | chr11 | 119293284 | 119293703 | chr11 | 119612134 | 119612493 |
| chr11 | 119612999 | 119613178 | chr11 | 120008006 | 120008605 | chr11 | 120039730 | 120039969 |
| chr11 | 120435322 | 120435561 | chr11 | 120435726 | 120435905 | chr11 | 120998614 | 120998913 |
| chr11 | 122847182 | 122847781 | chr11 | 122847976 | 122848695 | chr11 | 122849808 | 122860263 |
| chr11 | 122850331 | 122850630 | chr11 | 122851074 | 122851313 | chr11 | 122852338 | 122852577 |
| chr11 | 122854907 | 122855136 | chr11 | 123066359 | 123066538 | chr11 | 123228971 | 123229510 |
| chr11 | 123300736 | 123300955 | chr11 | 123301016 | 123302115 | chr11 | 124735341 | 124735580 |
| chr11 | 124736105 | 124736344 | chr11 | 124738694 | 124739125 | chr11 | 124739149 | 124739173 |
| chr11 | 125035687 | 125036286 | chr11 | 125036503 | 125036742 | chr11 | 125220423 | 125220722 |
| chr11 | 125755512 | 125755727 | chr11 | 125773587 | 125774186 | chr11 | 126870108 | 126870287 |
| chr11 | 126870379 | 126870618 | chr11 | 126873304 | 126873603 | chr11 | 128562802 | 128563818 |
| chr11 | 128563879 | 128564405 | chr11 | 128564641 | 128565480 | chr11 | 128657933 | 128658051 |
| chr11 | 129242783 | 129243643 | chr11 | 129243944 | 129244645 | chr11 | 129245747 | 129245892 |
| chr11 | 129245981 | 129246046 | chr11 | 130318860 | 130319099 | chr11 | 130319451 | 130319690 |
| chr11 | 130785406 | 130785705 | chr11 | 131522676 | 131522960 | chr11 | 131564873 | 131565101 |
| chr11 | 131766899 | 131767048 | chr11 | 131780391 | 131781350 | chr11 | 132484279 | 132484490 |
| chr11 | 132813545 | 132814049 | chr11 | 132864036 | 132864275 | chr11 | 132934031 | 132934270 |
| chr11 | 132952677 | 132953003 | chr11 | 132953064 | 132953423 | chr11 | 133231637 | 133231930 |
| chr11 | 133402114 | 133402353 | chr11 | 133825146 | 133825625 | chr11 | 133906702 | 133907001 |
| chr11 | 133938911 | 133939270 | chr11 | 134145629 | 134146468 | chr11 | 134146579 | 134146998 |
| chr11 | 134201404 | 134201640 | chr11 | 134201754 | 134202170 | chr11 | 134281288 | 134281543 |
| chr12 | 570012 | 570251 | chr12 | 1639060 | 1639299 | chr12 | 2162477 | 2162896 |
| chr12 | 2163071 | 2163370 | chr12 | 2403649 | 2403806 | chr12 | 2565971 | 2566330 |
| chr12 | 2861968 | 2862327 | chr12 | 2964372 | 2964671 | chr12 | 3600241 | 3600420 |
| chr12 | 3602186 | 3602965 | chr12 | 3603009 | 3603061 | chr12 | 4214010 | 4214245 |
| chr12 | 4273972 | 4274490 | chr12 | 4362362 | 4362541 | chr12 | 4378172 | 4378411 |
| chr12 | 4379275 | 4379574 | chr12 | 4381341 | 4382480 | chr12 | 4382863 | 4383102 |
| chr12 | 4383399 | 4383878 | chr12 | 4384315 | 4384494 | chr12 | 4392801 | 4393023 |
| chr12 | 4405515 | 4405694 | chr12 | 4554727 | 4554906 | chr12 | 5017994 | 5018773 |
| chr12 | 5018954 | 5020513 | chr12 | 5152951 | 5153610 | chr12 | 5541020 | 5541259 |
| chr12 | 5542233 | 5542532 | chr12 | 5542656 | 5543015 | chr12 | 5840126 | 5840305 |
| chr12 | 6483537 | 6483836 | chr12 | 6664407 | 6665486 | chr12 | 7559085 | 7559384 |
| chr12 | 8127119 | 8127238 | chr12 | 8171284 | 8171823 | chr12 | 8808505 | 8808640 |
| chr12 | 8850582 | 8850818 | chr12 | 8975096 | 8975452 | chr12 | 10085826 | 10085932 |
| chr12 | 10363204 | 10363319 | chr12 | 11653375 | 11653554 | chr12 | 12848294 | 12848653 |
| chr12 | 14133059 | 14133358 | chr12 | 14133541 | 14133960 | chr12 | 14135016 | 14135354 |
| chr12 | 15374156 | 15374395 | chr12 | 16500480 | 16500685 | chr12 | 20521624 | 20521923 |
| chr12 | 20522383 | 20522562 | chr12 | 20522681 | 20522860 | chr12 | 20522976 | 20522980 |
| chr12 | 21680300 | 21680779 | chr12 | 21810395 | 21810956 | chr12 | 21832988 | 21833095 |
| chr12 | 22093749 | 22094888 | chr12 | 22094997 | 22096236 | chr12 | 22486717 | 22487556 |
| chr12 | 22698102 | 22698207 | chr12 | 24714835 | 24715014 | chr12 | 24715161 | 24715340 |
| chr12 | 24715947 | 24716306 | chr12 | 25055865 | 25056524 | chr12 | 25101507 | 25101746 |
| chr12 | 25101824 | 25102183 | chr12 | 25380187 | 25380366 | chr12 | 25398165 | 25398404 |
| chr12 | 28127676 | 28128395 | chr12 | 28128457 | 28129176 | chr12 | 29935913 | 29936152 |
| chr12 | 29936524 | 29936777 | chr12 | 29936792 | 29936943 | chr12 | 29937234 | 29937473 |
| chr12 | 30322697 | 30323596 | chr12 | 30975472 | 30976015 | chr12 | 31079179 | 31079594 |
| chr12 | 32340225 | 32340336 | chr12 | 33591700 | 33591879 | chr12 | 33592512 | 33592991 |
| chr12 | 34494814 | 34494993 | chr12 | 34502649 | 34502888 | chr12 | 39299040 | 39299185 |
| chr12 | 39299269 | 39299639 | chr12 | 39539276 | 39539515 | chr12 | 40618318 | 40618557 |
| chr12 | 41086102 | 41086461 | chr12 | 41086706 | 41087185 | chr12 | 41582422 | 41583081 |
| chr12 | 41583278 | 41583471 | chr12 | 43944800 | 43945219 | chr12 | 43945262 | 43945621 |

TABLE 14-continued

| chr | start | end | chr | start | end | chr | start | end |
|---|---|---|---|---|---|---|---|---|
| chr12 | 43945742 | 43946401 | chr12 | 45269415 | 45269714 | chr12 | 45444029 | 45444920 |
| chr12 | 45445062 | 45445348 | chr12 | 46767555 | 46767558 | chr12 | 47225301 | 47225660 |
| chr12 | 47629275 | 47629307 | chr12 | 47629398 | 47629454 | chr12 | 48397154 | 48398173 |
| chr12 | 48398567 | 48398746 | chr12 | 49297770 | 49298009 | chr12 | 49366280 | 49366519 |
| chr12 | 49374838 | 49375197 | chr12 | 49375248 | 49375607 | chr12 | 49390776 | 49391975 |
| chr12 | 49657624 | 49657722 | chr12 | 49690975 | 49691154 | chr12 | 49726969 | 49727208 |
| chr12 | 49729640 | 49730179 | chr12 | 50297417 | 50298136 | chr12 | 50355193 | 50355552 |
| chr12 | 50426672 | 50426894 | chr12 | 51421134 | 51421373 | chr12 | 51421482 | 51421661 |
| chr12 | 51565470 | 51565562 | chr12 | 51930515 | 51930785 | chr12 | 52262895 | 52263195 |
| chr12 | 52301205 | 52301444 | chr12 | 52400735 | 52401616 | chr12 | 52627102 | 52627381 |
| chr12 | 52652054 | 52652713 | chr12 | 53108005 | 53108304 | chr12 | 53359245 | 53359664 |
| chr12 | 54089004 | 54089602 | chr12 | 54132172 | 54132411 | chr12 | 54145750 | 54145989 |
| chr12 | 54321170 | 54321709 | chr12 | 54322108 | 54322302 | chr12 | 54324719 | 54325018 |
| chr12 | 54329264 | 54330007 | chr12 | 54330980 | 54331219 | chr12 | 54332774 | 54333433 |
| chr12 | 54338589 | 54339668 | chr12 | 54343718 | 54343955 | chr12 | 54345523 | 54346122 |
| chr12 | 54348761 | 54349420 | chr12 | 54354419 | 54354718 | chr12 | 54354805 | 54355575 |
| chr12 | 54359873 | 54360172 | chr12 | 54360510 | 54360729 | chr12 | 54377835 | 54378194 |
| chr12 | 54379100 | 54379699 | chr12 | 54379785 | 54380486 | chr12 | 54387752 | 54388051 |
| chr12 | 54388141 | 54388320 | chr12 | 54391267 | 54391506 | chr12 | 54393403 | 54393762 |
| chr12 | 54393847 | 54394266 | chr12 | 54394307 | 54394546 | chr12 | 54398697 | 54399056 |
| chr12 | 54399542 | 54399721 | chr12 | 54402654 | 54402812 | chr12 | 54402975 | 54403454 |
| chr12 | 54408330 | 54408809 | chr12 | 54424670 | 54424887 | chr12 | 54424912 | 54425211 |
| chr12 | 54447460 | 54447519 | chr12 | 54447781 | 54448080 | chr12 | 54520658 | 54520957 |
| chr12 | 54720221 | 54720320 | chr12 | 54812150 | 54812449 | chr12 | 54942906 | 54943191 |
| chr12 | 56882365 | 56882460 | chr12 | 57559778 | 57559914 | chr12 | 57618478 | 57619077 |
| chr12 | 57881046 | 57881345 | chr12 | 57943980 | 57944219 | chr12 | 58021218 | 58021817 |
| chr12 | 58021824 | 58022093 | chr12 | 58025551 | 58025970 | chr12 | 62584739 | 62586118 |
| chr12 | 62586178 | 62586357 | chr12 | 63025515 | 63026257 | chr12 | 63543749 | 63544828 |
| chr12 | 63545239 | 63545418 | chr12 | 64061721 | 64062260 | chr12 | 64062295 | 64062654 |
| chr12 | 64062830 | 64063189 | chr12 | 64783098 | 64783322 | chr12 | 64784007 | 64784352 |
| chr12 | 64784460 | 64784639 | chr12 | 65218000 | 65219259 | chr12 | 65219281 | 65219880 |
| chr12 | 65220129 | 65220428 | chr12 | 65514781 | 65515620 | chr12 | 65516379 | 65516558 |
| chr12 | 65557115 | 65557234 | chr12 | 65562064 | 65562172 | chr12 | 66122711 | 66123610 |
| chr12 | 66135910 | 66136089 | chr12 | 66582743 | 66583222 | chr12 | 69327182 | 69327541 |
| chr12 | 69754351 | 69754470 | chr12 | 69754600 | 69754710 | chr12 | 69964101 | 69964340 |
| chr12 | 70087412 | 70087651 | chr12 | 72332550 | 72332789 | chr12 | 72665167 | 72665526 |
| chr12 | 72665566 | 72665877 | chr12 | 72666014 | 72666313 | chr12 | 72666620 | 72667519 |
| chr12 | 72667578 | 72667757 | chr12 | 75601168 | 75602007 | chr12 | 75602895 | 75603314 |
| chr12 | 75728262 | 75728561 | chr12 | 77719218 | 77719517 | chr12 | 79257138 | 79257437 |
| chr12 | 79258850 | 79259029 | chr12 | 81102105 | 81102603 | chr12 | 81107921 | 81108100 |
| chr12 | 81471425 | 81472204 | chr12 | 85306430 | 85306549 | chr12 | 85667173 | 85667832 |
| chr12 | 85673132 | 85673311 | chr12 | 85673385 | 85674884 | chr12 | 88974346 | 88974356 |
| chr12 | 93966337 | 93966696 | chr12 | 93966910 | 93967329 | chr12 | 94543308 | 94543547 |
| chr12 | 94543811 | 94544080 | chr12 | 95267450 | 95267772 | chr12 | 95267977 | 95268000 |
| chr12 | 95941794 | 95943053 | chr12 | 99288212 | 99289411 | chr12 | 101025306 | 101025485 |
| chr12 | 101110926 | 101111165 | chr12 | 101111277 | 101111576 | chr12 | 103218396 | 103218655 |
| chr12 | 103350250 | 103350429 | chr12 | 103351464 | 103352783 | chr12 | 103358763 | 103359002 |
| chr12 | 103359482 | 103359661 | chr12 | 103889086 | 103889306 | chr12 | 103889660 | 103889899 |
| chr12 | 104609340 | 104610179 | chr12 | 104850430 | 104850669 | chr12 | 104850983 | 104851282 |
| chr12 | 104851941 | 104852600 | chr12 | 105478222 | 105478457 | chr12 | 106974279 | 106974458 |
| chr12 | 106976641 | 106976880 | chr12 | 106977394 | 106977589 | chr12 | 106979079 | 106979618 |
| chr12 | 106979718 | 106980077 | chr12 | 106980129 | 106980428 | chr12 | 106980771 | 106981490 |
| chr12 | 107486462 | 107486673 | chr12 | 107487114 | 107487945 | chr12 | 107712199 | 107712378 |
| chr12 | 107713131 | 107713310 | chr12 | 107714771 | 107715250 | chr12 | 108168883 | 108169662 |
| chr12 | 108237377 | 108237676 | chr12 | 108238034 | 108238719 | chr12 | 108297320 | 108297559 |
| chr12 | 110353315 | 110353553 | chr12 | 110717447 | 110717806 | chr12 | 111127079 | 111127438 |
| chr12 | 111471099 | 111471638 | chr12 | 111471871 | 111472511 | chr12 | 111472572 | 111472830 |
| chr12 | 111763136 | 111763227 | chr12 | 113012877 | 113013236 | chr12 | 113541644 | 113542183 |
| chr12 | 113592150 | 113592449 | chr12 | 113900616 | 113900855 | chr12 | 113900974 | 113901693 |
| chr12 | 113901951 | 113902429 | chr12 | 113903394 | 113903573 | chr12 | 113904689 | 113905108 |
| chr12 | 113908894 | 113909553 | chr12 | 113909569 | 113909808 | chr12 | 113913180 | 113914139 |
| chr12 | 113916147 | 113916266 | chr12 | 113916322 | 113916419 | chr12 | 113916575 | 113916754 |
| chr12 | 113916873 | 113917112 | chr12 | 113917212 | 113917391 | chr12 | 113917684 | 113917983 |
| chr12 | 114029325 | 114029509 | chr12 | 114029546 | 114029744 | chr12 | 114075942 | 114076177 |
| chr12 | 114337849 | 114337868 | chr12 | 114833895 | 114834194 | chr12 | 114838227 | 114838826 |
| chr12 | 114840946 | 114841185 | chr12 | 114843016 | 114843375 | chr12 | 114843454 | 114843753 |
| chr12 | 114844102 | 114844401 | chr12 | 114846623 | 114846862 | chr12 | 114846886 | 114847741 |
| chr12 | 114851969 | 114852181 | chr12 | 114852214 | 114852268 | chr12 | 114877068 | 114877367 |
| chr12 | 114878448 | 114878687 | chr12 | 114878734 | 114879093 | chr12 | 114881550 | 114881849 |
| chr12 | 114882488 | 114882727 | chr12 | 114883385 | 114883554 | chr12 | 114885134 | 114885373 |
| chr12 | 114918513 | 114918806 | chr12 | 115136153 | 115136441 | chr12 | 116945988 | 116946647 |
| chr12 | 117473983 | 117474282 | chr12 | 117797999 | 117798170 | chr12 | 117798589 | 117799068 |
| chr12 | 117799322 | 117799621 | chr12 | 118860317 | 118860436 | chr12 | 119212120 | 119212479 |
| chr12 | 119418512 | 119418931 | chr12 | 119419362 | 119419541 | chr12 | 119419631 | 119419920 |
| chr12 | 120032777 | 120033256 | chr12 | 120148125 | 120148345 | chr12 | 120148824 | 120149063 |
| chr12 | 120885155 | 120885274 | chr12 | 121622472 | 121622591 | chr12 | 122192885 | 122192933 |
| chr12 | 122284969 | 122285189 | chr12 | 123129041 | 123129139 | chr12 | 123233818 | 123233926 |
| chr12 | 124393463 | 124393702 | chr12 | 124397514 | 124397693 | chr12 | 125009254 | 125009381 |

TABLE 14-continued

| chr | start | end | chr | start | end | chr | start | end |
|---|---|---|---|---|---|---|---|---|
| chr12 | 125533851 | 125534508 | chr12 | 125670024 | 125670383 | chr12 | 126168468 | 126168707 |
| chr12 | 127210933 | 127211472 | chr12 | 127765066 | 127765535 | chr12 | 127939988 | 127940189 |
| chr12 | 127940271 | 127940347 | chr12 | 128751295 | 128751534 | chr12 | 128751732 | 128752331 |
| chr12 | 128752423 | 128753022 | chr12 | 128753136 | 128753315 | chr12 | 128850442 | 128850739 |
| chr12 | 129337901 | 129338919 | chr12 | 130037571 | 130037866 | chr12 | 130387716 | 130387914 |
| chr12 | 130388332 | 130389231 | chr12 | 130589116 | 130589354 | chr12 | 130645131 | 130645730 |
| chr12 | 130646590 | 130647179 | chr12 | 130647263 | 130648569 | chr12 | 130821287 | 130821706 |
| chr12 | 130968586 | 130968758 | chr12 | 131200303 | 131200649 | chr12 | 131400719 | 131401018 |
| chr12 | 131402943 | 131403229 | chr12 | 131513255 | 131513494 | chr12 | 132169246 | 132169357 |
| chr12 | 132221614 | 132222153 | chr12 | 132333337 | 132333418 | chr12 | 132333517 | 132333696 |
| chr12 | 132348549 | 132348788 | chr12 | 132423596 | 132423829 | chr12 | 132643371 | 132643376 |
| chr12 | 132986419 | 132986658 | chr12 | 133002713 | 133003312 | chr12 | 133194996 | 133195295 |
| chr12 | 133199642 | 133199797 | chr12 | 133463657 | 133463956 | chr12 | 133464018 | 133464074 |
| chr12 | 133464755 | 133464920 | chr12 | 133481333 | 133481732 | chr12 | 133484650 | 133485439 |
| chr12 | 133485463 | 133485942 | chr12 | 133757959 | 133758198 | chr13 | 20735708 | 20736187 |
| chr13 | 20875662 | 20876021 | chr13 | 21649557 | 21649856 | chr13 | 22243192 | 22243551 |
| chr13 | 23489764 | 23490003 | chr13 | 23733355 | 23734124 | chr13 | 23734182 | 23734781 |
| chr13 | 24477566 | 24477985 | chr13 | 25115623 | 25115852 | chr13 | 25319764 | 25321443 |
| chr13 | 25321612 | 25322031 | chr13 | 25592963 | 25593201 | chr13 | 25620951 | 25621490 |
| chr13 | 25744639 | 25746054 | chr13 | 25946129 | 25946488 | chr13 | 25946529 | 25946888 |
| chr13 | 26042580 | 26043590 | chr13 | 26625215 | 26625814 | chr13 | 26625994 | 26626233 |
| chr13 | 22132307 | 27132546 | chr13 | 27334118 | 27334657 | chr13 | 27334684 | 27334983 |
| chr13 | 28239896 | 28240195 | chr13 | 28365615 | 28366181 | chr13 | 28366381 | 28366680 |
| chr13 | 28366923 | 28367162 | chr13 | 28367712 | 28368251 | chr13 | 28368373 | 28368672 |
| chr13 | 28368872 | 28369891 | chr13 | 28369952 | 28370071 | chr13 | 28370855 | 28371154 |
| chr13 | 28394667 | 28394966 | chr13 | 28395408 | 28395647 | chr13 | 28395917 | 28396156 |
| chr13 | 28491694 | 28492050 | chr13 | 28492160 | 28492639 | chr13 | 28528432 | 28528851 |
| chr13 | 28540657 | 28541016 | chr13 | 28543138 | 28543317 | chr13 | 28544321 | 28544980 |
| chr13 | 28549396 | 28550655 | chr13 | 28551320 | 28551559 | chr13 | 28551850 | 28552269 |
| chr13 | 28552481 | 28552660 | chr13 | 28552720 | 28552899 | chr13 | 28552935 | 28553234 |
| chr13 | 28673927 | 28674826 | chr13 | 29068675 | 29068515 | chr13 | 29068847 | 29069146 |
| chr13 | 29106217 | 29107409 | chr13 | 30707495 | 30707674 | chr13 | 31742856 | 31743242 |
| chr13 | 32605033 | 32605212 | chr13 | 32605357 | 32605596 | chr13 | 32605642 | 32606001 |
| chr13 | 33590737 | 33591036 | chr13 | 33591211 | 33591510 | chr13 | 33924579 | 33924812 |
| chr13 | 36045193 | 36045372 | chr13 | 36704848 | 36705147 | chr13 | 36705351 | 36705590 |
| chr13 | 36729006 | 36729229 | chr13 | 36920216 | 36920515 | chr13 | 36920528 | 36920887 |
| chr13 | 37004681 | 37004992 | chr13 | 37005581 | 37006840 | chr13 | 37247982 | 37248316 |
| chr13 | 37248886 | 37249125 | chr13 | 37633915 | 37634094 | chr13 | 37643855 | 37644094 |
| chr13 | 38443544 | 38443796 | chr13 | 39261309 | 39261472 | chr13 | 43566148 | 43566678 |
| chr13 | 44947643 | 44948302 | chr13 | 45885802 | 45885981 | chr13 | 45905243 | 45905356 |
| chr13 | 46425447 | 46425686 | chr13 | 46660850 | 46660944 | chr13 | 46961395 | 46961634 |
| chr13 | 47468065 | 47468244 | chr13 | 47526167 | 47526286 | chr13 | 48667803 | 48557982 |
| chr13 | 49794034 | 49795273 | chr13 | 53312917 | 53313996 | chr13 | 53419636 | 53419875 |
| chr13 | 53419931 | 53420170 | chr13 | 53420284 | 53420823 | chr13 | 53421161 | 53421164 |
| chr13 | 53421288 | 53421880 | chr13 | 53422220 | 53422459 | chr13 | 53423759 | 53424058 |
| chr13 | 58203504 | 58203743 | chr13 | 58203768 | 58204187 | chr13 | 58204253 | 58204492 |
| chr13 | 58205944 | 58207083 | chr13 | 58207382 | 58208101 | chr13 | 58208412 | 58209011 |
| chr13 | 67804144 | 67804175 | chr13 | 67804420 | 67804599 | chr13 | 67805100 | 67805339 |
| chr13 | 70681550 | 70682149 | chr13 | 72439047 | 72439109 | chr13 | 73619573 | 73619698 |
| chr13 | 78492724 | 78492942 | chr13 | 78493092 | 78493271 | chr13 | 78493363 | 78493902 |
| chr13 | 79169722 | 79170981 | chr13 | 79171038 | 79171277 | chr13 | 79175678 | 79176877 |
| chr13 | 79176897 | 79178096 | chr13 | 79183327 | 79183566 | chr13 | 84455499 | 84455798 |
| chr13 | 88323504 | 88324283 | chr13 | 88324415 | 88324714 | chr13 | 88325201 | 88325560 |
| chr13 | 88325731 | 88326140 | chr13 | 88326447 | 88327106 | chr13 | 88997832 | 88997951 |
| chr13 | 91948415 | 91948594 | chr13 | 92050668 | 92050843 | chr13 | 92051065 | 92051244 |
| chr13 | 92051273 | 92051632 | chr13 | 93879519 | 93879452 | chr13 | 93879596 | 93879775 |
| chr13 | 93879994 | 93880953 | chr13 | 95352237 | 95357416 | chr13 | 95357496 | 95357855 |
| chr13 | 95357954 | 95358253 | chr13 | 95359656 | 95359895 | chr13 | 95360228 | 95360467 |
| chr13 | 95363111 | 95363530 | chr13 | 95363697 | 95364296 | chr13 | 95364409 | 95364888 |
| chr13 | 95619931 | 95620170 | chr13 | 95620560 | 95621099 | chr13 | 96031611 | 96031725 |
| chr13 | 96204779 | 96205438 | chr13 | 96296297 | 96296559 | chr13 | 96296616 | 96297215 |
| chr13 | 96743713 | 96744212 | chr13 | 99851662 | 99851748 | chr13 | 100547770 | 100548009 |
| chr13 | 100608177 | 100608536 | chr13 | 100608597 | 100609136 | chr13 | 100621859 | 100622098 |
| chr13 | 100624213 | 100624452 | chr13 | 100624509 | 100624766 | chr13 | 100624801 | 100624808 |
| chr13 | 100626905 | 100627084 | chr13 | 100627203 | 100627442 | chr13 | 100630545 | 100631084 |
| chr13 | 100634227 | 100634382 | chr13 | 100635310 | 100635549 | chr13 | 100636084 | 100636323 |
| chr13 | 100637289 | 100637588 | chr13 | 100641203 | 100642282 | chr13 | 100643217 | 100643516 |
| chr13 | 100643955 | 100644314 | chr13 | 100649334 | 100650018 | chr13 | 102568380 | 102568559 |
| chr13 | 102568776 | 102569075 | chr13 | 102569104 | 102569643 | chr13 | 103046619 | 103047098 |
| chr13 | 103052252 | 103052671 | chr13 | 103052797 | 103053036 | chr13 | 103053296 | 103053509 |
| chr13 | 107186781 | 107186950 | chr13 | 107187085 | 107187242 | chr13 | 108518298 | 108518494 |
| chr13 | 108518724 | 108519017 | chr13 | 108519162 | 108519461 | chr13 | 108519637 | 108519996 |
| chr13 | 108520370 | 108520658 | chr13 | 108520879 | 108520969 | chr13 | 109147599 | 109148438 |
| chr13 | 109148685 | 109149115 | chr13 | 109149164 | 109149284 | chr13 | 110434373 | 110434672 |
| chr13 | 110958720 | 110959079 | chr13 | 110959119 | 110959358 | chr13 | 110959629 | 110960048 |
| chr13 | 110960147 | 110960386 | chr13 | 110960453 | 110960692 | chr13 | 111278225 | 111278521 |
| chr13 | 111363885 | 111364060 | chr13 | 112272891 | 112273102 | chr13 | 112707603 | 112707962 |
| chr13 | 112708002 | 112708601 | chr13 | 112709408 | 112709647 | chr13 | 112709713 | 112709713 |

TABLE 14-continued

| chr | start | end | chr | start | end | chr | start | end |
|---|---|---|---|---|---|---|---|---|
| chr13 | 112709787 | 112710026 | chr13 | 112710247 | 112710606 | chr13 | 112710669 | 112711868 |
| chr13 | 112711924 | 112715267 | chr13 | 112715267 | 112715745 | chr13 | 112715910 | 112716389 |
| chr13 | 112716695 | 112716814 | chr13 | 112716982 | 112717611 | chr13 | 112717743 | 112718042 |
| chr13 | 112719940 | 112720599 | chr13 | 112720626 | 112720865 | chr13 | 112720938 | 112721117 |
| chr13 | 112721158 | 112722417 | chr13 | 112724431 | 112724610 | chr13 | 112726240 | 112726659 |
| chr13 | 112727888 | 112728367 | chr13 | 112758033 | 112758688 | chr13 | 112758750 | 112759349 |
| chr13 | 112759538 | 112759717 | chr13 | 112759874 | 112760413 | chr13 | 112760755 | 112761305 |
| chr13 | 113598526 | 113598877 | chr13 | 113985597 | 113985956 | chr13 | 114055881 | 114056240 |
| chr13 | 114059990 | 114060409 | chr13 | 114074692 | 114074931 | chr13 | 114123081 | 114123358 |
| chr13 | 114189654 | 114189732 | chr13 | 114221548 | 114221655 | chr13 | 114304637 | 114305016 |
| chr13 | 114479330 | 114479509 | chr13 | 114497930 | 114498349 | chr13 | 114748251 | 114748730 |
| chr13 | 114780482 | 114781141 | chr13 | 114807537 | 114807896 | chr13 | 114855533 | 114855772 |
| chr13 | 114862381 | 114862458 | chr13 | 114961729 | 114962028 | chr14 | 21093364 | 21093531 |
| chr14 | 21093604 | 21093723 | chr14 | 21100674 | 21100906 | chr14 | 22004932 | 22005171 |
| chr14 | 23356162 | 23356341 | chr14 | 23706666 | 23706905 | chr14 | 24045439 | 24045678 |
| chr14 | 24803493 | 24804512 | chr14 | 26674280 | 26674459 | chr14 | 26674625 | 26674703 |
| chr14 | 27066520 | 27066699 | chr14 | 27067065 | 27067427 | chr14 | 29225457 | 29225636 |
| chr14 | 29225986 | 29226285 | chr14 | 29228567 | 29228866 | chr14 | 29229008 | 29229487 |
| chr14 | 29230995 | 29231229 | chr14 | 29231329 | 29231688 | chr14 | 29234911 | 29235450 |
| chr14 | 29236966 | 29237205 | chr14 | 29242687 | 29242707 | chr14 | 29243433 | 29243972 |
| chr14 | 29244147 | 29244383 | chr14 | 29247596 | 29247835 | chr14 | 29254495 | 29254794 |
| chr14 | 31344269 | 31344628 | chr14 | 31925640 | 31925804 | chr14 | 32597619 | 32597759 |
| chr14 | 33402373 | 33402852 | chr14 | 33403019 | 33403421 | chr14 | 33403125 | 33403421 |
| chr14 | 33403783 | 33404502 | chr14 | 34420150 | 34420389 | chr14 | 35023188 | 35023427 |
| chr14 | 35024347 | 35024454 | chr14 | 36003471 | 36003904 | chr14 | 36003979 | 36004578 |
| chr14 | 36004608 | 36005087 | chr14 | 36972709 | 36973008 | chr14 | 36973157 | 36973636 |
| chr14 | 36974421 | 36975058 | chr14 | 36975200 | 36975499 | chr14 | 36977558 | 36978097 |
| chr14 | 36978474 | 36978653 | chr14 | 36979657 | 36979724 | chr14 | 36982829 | 36983068 |
| chr14 | 36983628 | 36984227 | chr14 | 36985757 | 36985946 | chr14 | 36986212 | 36986931 |
| chr14 | 36987068 | 36987787 | chr14 | 36987862 | 36988221 | chr14 | 36988449 | 36988564 |
| chr14 | 36990799 | 36991258 | chr14 | 36991501 | 36991693 | chr14 | 36991848 | 36992507 |
| chr14 | 36993386 | 36994045 | chr14 | 36994145 | 36995104 | chr14 | 37116026 | 37116483 |
| chr14 | 37117535 | 37117745 | chr14 | 37123339 | 37124178 | chr14 | 37124289 | 37124648 |
| chr14 | 37124910 | 37125629 | chr14 | 37126150 | 37126389 | chr14 | 37126463 | 37127002 |
| chr14 | 37127207 | 37127386 | chr14 | 37127572 | 37128111 | chr14 | 37128459 | 37128818 |
| chr14 | 37129990 | 37130349 | chr14 | 37132296 | 37132775 | chr14 | 37132908 | 37133147 |
| chr14 | 37135706 | 37135868 | chr14 | 37135922 | 37136425 | chr14 | 37136514 | 37136693 |
| chr14 | 38060588 | 38061007 | chr14 | 38677445 | 38677581 | chr14 | 38724207 | 38725346 |
| chr14 | 38725434 | 38725560 | chr14 | 42074467 | 42074944 | chr14 | 42075023 | 42075066 |
| chr14 | 42075511 | 42076290 | chr14 | 42076749 | 42076928 | chr14 | 42077130 | 42077369 |
| chr14 | 42077696 | 42077804 | chr14 | 42079190 | 42079429 | chr14 | 48143657 | 48144196 |
| chr14 | 48144201 | 48144500 | chr14 | 48144619 | 48145158 | chr14 | 48145219 | 48145338 |
| chr14 | 50333976 | 50334084 | chr14 | 50334336 | 50334455 | chr14 | 51338642 | 51339061 |
| chr14 | 51561285 | 51561526 | chr14 | 51561680 | 51562090 | chr14 | 52534571 | 52534870 |
| chr14 | 52534929 | 52536488 | chr14 | 52734414 | 52734653 | chr14 | 52734687 | 52735346 |
| chr14 | 52781422 | 52782021 | chr14 | 54422549 | 54423028 | chr14 | 55370100 | 55370219 |
| chr14 | 55596008 | 55596043 | chr14 | 56765207 | 55765686 | chr14 | 57045445 | 57045840 |
| chr14 | 57260845 | 57261924 | chr14 | 57261977 | 57262276 | chr14 | 57264001 | 57265320 |
| chr14 | 57270854 | 57271333 | chr14 | 57271919 | 57272158 | chr14 | 57274387 | 57275406 |
| chr14 | 57275521 | 57276180 | chr14 | 57276344 | 57276763 | chr14 | 57277830 | 57279712 |
| chr14 | 57283238 | 57284737 | chr14 | 58332201 | 58332494 | chr14 | 60097111 | 60097650 |
| chr14 | 60386111 | 60386350 | chr14 | 60386551 | 60386790 | chr14 | 60794532 | 60794771 |
| chr14 | 60952084 | 60953039 | chr14 | 60973157 | 60973418 | chr14 | 60973618 | 60974157 |
| chr14 | 60974273 | 60974506 | chr14 | 60975290 | 60976609 | chr14 | 60976718 | 60976957 |
| chr14 | 60977263 | 60978222 | chr14 | 60981116 | 60981355 | chr14 | 60981586 | 60981885 |
| chr14 | 60982007 | 60982725 | chr14 | 60982996 | 60982996 | chr14 | 61104189 | 61104952 |
| chr14 | 61108539 | 61108904 | chr14 | 61109031 | 61109078 | chr14 | 61109129 | 61109548 |
| chr14 | 61109742 | 61110341 | chr14 | 61114058 | 61114537 | chr14 | 61115235 | 61115694 |
| chr14 | 61118688 | 61118841 | chr14 | 61118872 | 61119227 | chr14 | 61747277 | 61747816 |
| chr14 | 61748002 | 61748117 | chr14 | 62279493 | 62280092 | chr14 | 62583710 | 62584009 |
| chr14 | 63512017 | 63512376 | chr14 | 63512486 | 63512905 | chr14 | 63513050 | 63513229 |
| chr14 | 64222332 | 64222450 | chr14 | 65005803 | 65005915 | chr14 | 65008915 | 65009274 |
| chr14 | 65233253 | 65233552 | chr14 | 67886583 | 67886702 | chr14 | 69013958 | 69014195 |
| chr14 | 69866930 | 69867289 | chr14 | 70014640 | 70015059 | chr14 | 70038414 | 70038713 |
| chr14 | 70038889 | 70039101 | chr14 | 70346045 | 70346584 | chr14 | 70654379 | 70654798 |
| chr14 | 70655451 | 70656170 | chr14 | 72398642 | 73399121 | chr14 | 72399258 | 72399557 |
| chr14 | 72399830 | 72400129 | chr14 | 73167676 | 73167975 | chr14 | 73174938 | 73175237 |
| chr14 | 73178717 | 73178956 | chr14 | 73180112 | 73180336 | chr14 | 73318371 | 73318730 |
| chr14 | 73333174 | 73333256 | chr14 | 73602351 | 73602470 | chr14 | 74705940 | 74706299 |
| chr14 | 74706357 | 74707976 | chr14 | 74708760 | 74709059 | chr14 | 74892472 | 74892645 |
| chr14 | 74892975 | 74893191 | chr14 | 75078070 | 75078609 | chr14 | 75760210 | 75760329 |
| chr14 | 76604580 | 76604819 | chr14 | 76604985 | 76605464 | chr14 | 76843364 | 76843603 |
| chr14 | 76843639 | 76844058 | chr14 | 77228021 | 77228107 | chr14 | 77606833 | 77607312 |
| chr14 | 77737110 | 77737685 | chr14 | 79745088 | 79745277 | chr14 | 85996395 | 85996694 |
| chr14 | 85996760 | 85996999 | chr14 | 85997735 | 85998094 | chr14 | 85998468 | 85998786 |
| chr14 | 85999472 | 85999711 | chr14 | 86000182 | 85000574 | chr14 | 86000886 | 86001196 |
| chr14 | 89817813 | 89818112 | chr14 | 90527617 | 90527856 | chr14 | 90983225 | 90983385 |
| chr14 | 91691167 | 91691385 | chr14 | 91766189 | 91766542 | chr14 | 92789438 | 92789617 |

TABLE 14-continued

| chr | start | end | chr | start | end | chr | start | end |
|---|---|---|---|---|---|---|---|---|
| chr14 | 92789777 | 92790256 | chr14 | 92790551 | 92790790 | chr14 | 92979835 | 92980074 |
| chr14 | 93154979 | 93155385 | chr14 | 93389450 | 93389869 | chr14 | 93706678 | 93706857 |
| chr14 | 94254302 | 94254601 | chr14 | 94405641 | 94405880 | chr14 | 95233616 | 95233646 |
| chr14 | 95234557 | 95235456 | chr14 | 95235939 | 95236200 | chr14 | 95236450 | 95236598 |
| chr14 | 95239298 | 95239717 | chr14 | 95240053 | 95240268 | chr14 | 95240410 | 95240497 |
| chr14 | 96342551 | 96342790 | chr14 | 96342806 | 96343205 | chr14 | 96343330 | 96343509 |
| chr14 | 96343553 | 96343792 | chr14 | 97045327 | 97045506 | chr14 | 97058761 | 97059180 |
| chr14 | 97499257 | 97499416 | chr14 | 97499616 | 97500035 | chr14 | 97684957 | 97685376 |
| chr14 | 97685624 | 97686038 | chr14 | 99584501 | 99584740 | chr14 | 99736048 | 99736213 |
| chr14 | 100437707 | 100438066 | chr14 | 100438609 | 100438908 | chr14 | 100643267 | 100643566 |
| chr14 | 101193145 | 101193384 | chr14 | 101250012 | 101250371 | chr14 | 101543783 | 101544270 |
| chr14 | 101923033 | 101923332 | chr14 | 101923520 | 101923819 | chr14 | 101923883 | 101924122 |
| chr14 | 101924966 | 101925985 | chr14 | 102026273 | 102026572 | chr14 | 102026703 | 102027062 |
| chr14 | 102031132 | 102031371 | chr14 | 102031434 | 102031665 | chr14 | 102247824 | 102248303 |
| chr14 | 102418533 | 102418652 | chr14 | 102521501 | 102521860 | chr14 | 102529912 | 102530178 |
| chr14 | 102630426 | 102530605 | chr14 | 102564386 | 102564502 | chr14 | 102681994 | 102682233 |
| chr14 | 103021308 | 103022087 | chr14 | 103394784 | 103395203 | chr14 | 103477540 | 103477771 |
| chr14 | 103655154 | 103655684 | chr14 | 103673992 | 103673994 | chr14 | 103674069 | 103674231 |
| chr14 | 103687002 | 103687301 | chr14 | 103739880 | 103740239 | chr14 | 103740275 | 103740514 |
| chr14 | 103745606 | 103745845 | chr14 | 104159978 | 104160160 | chr14 | 104202624 | 104202852 |
| chr14 | 104547814 | 104547993 | chr14 | 104571902 | 104572201 | chr14 | 104601657 | 104601935 |
| chr14 | 104601959 | 104602138 | chr14 | 104604954 | 104605193 | chr14 | 104620334 | 104620633 |
| chr14 | 104627564 | 104627862 | chr14 | 104645048 | 104645277 | chr14 | 104646225 | 104646584 |
| chr14 | 104647183 | 104647362 | chr14 | 104682452 | 104682751 | chr14 | 104862764 | 104863123 |
| chr14 | 105071198 | 106071340 | chr14 | 105157401 | 105157640 | chr14 | 105241220 | 105241267 |
| chr14 | 105246463 | 105246642 | chr14 | 105511960 | 105512463 | chr14 | 105658268 | 105658507 |
| chr14 | 105714177 | 105714690 | chr14 | 105714906 | 105715565 | chr15 | 22822269 | 22822384 |
| chr15 | 23158294 | 23158593 | chr15 | 26107541 | 26107960 | chr15 | 26108010 | 26108789 |
| chr15 | 27018281 | 27018520 | chr15 | 27212791 | 27213270 | chr15 | 27216294 | 27216533 |
| chr15 | 27603982 | 27604057 | chr15 | 28341615 | 28342514 | chr15 | 28344081 | 28344380 |
| chr15 | 28352935 | 28352935 | chr15 | 29077185 | 29077484 | chr15 | 29130712 | 29131971 |
| chr15 | 29407680 | 29408099 | chr15 | 29862423 | 29862537 | chr15 | 31455297 | 31455578 |
| chr15 | 31775500 | 31776216 | chr15 | 33009649 | 33011448 | chr15 | 33011498 | 33011737 |
| chr15 | 33486970 | 33487209 | chr15 | 33602725 | 33602964 | chr15 | 33603110 | 33603709 |
| chr15 | 33879168 | 33879347 | chr15 | 34630346 | 34630525 | chr15 | 34729381 | 34729680 |
| chr15 | 34786425 | 34787384 | chr15 | 35046935 | 35047234 | chr15 | 35087563 | 35087802 |
| chr15 | 37180227 | 37180241 | chr15 | 37180414 | 37180826 | chr15 | 37402898 | 37403316 |
| chr15 | 40211736 | 40212275 | chr15 | 40575538 | 40575837 | chr15 | 41165152 | 41165751 |
| chr15 | 41787709 | 41787948 | chr15 | 41804786 | 41805865 | chr15 | 41835732 | 41835814 |
| chr15 | 41913660 | 41913899 | chr15 | 41952493 | 41952792 | chr15 | 43810472 | 43810510 |
| chr15 | 44037485 | 44037604 | chr15 | 45403554 | 45404213 | chr15 | 45404833 | 45405209 |
| chr15 | 45421291 | 45421530 | chr15 | 45421874 | 45421947 | chr15 | 45427263 | 45427502 |
| chr15 | 45427520 | 45427879 | chr15 | 45479371 | 45479789 | chr15 | 45670503 | 45670971 |
| chr15 | 47476794 | 47477093 | chr15 | 48483882 | 48483963 | chr15 | 48936639 | 48938077 |
| chr15 | 48938122 | 48938601 | chr15 | 51385838 | 51386257 | chr15 | 51633986 | 51634225 |
| chr15 | 51973695 | 51974030 | chr15 | 53075716 | 53077455 | chr15 | 53077574 | 53077813 |
| chr15 | 53077971 | 53078320 | chr15 | 53079262 | 53080161 | chr15 | 53080263 | 53080682 |
| chr15 | 53080861 | 53081100 | chr15 | 53081223 | 53081702 | chr15 | 53082348 | 53082587 |
| chr15 | 53096735 | 53096974 | chr15 | 53097157 | 53097336 | chr15 | 53097535 | 53098074 |
| chr15 | 53098218 | 53098757 | chr15 | 54270424 | 54270783 | chr15 | 54270858 | 54271025 |
| chr15 | 55452972 | 55453087 | chr15 | 55699008 | 55699122 | chr15 | 55880796 | 55881095 |
| chr15 | 58357236 | 58357535 | chr15 | 58357638 | 58358297 | chr15 | 59158454 | 59158616 |
| chr15 | 59950343 | 59950461 | chr15 | 60286937 | 60287780 | chr15 | 60288703 | 60288935 |
| chr15 | 60289229 | 60289638 | chr15 | 60296047 | 60296286 | chr15 | 60296495 | 60297514 |
| chr15 | 60297544 | 60298203 | chr15 | 61520816 | 61521115 | chr15 | 61521559 | 61521676 |
| chr15 | 61521713 | 61522038 | chr15 | 62456848 | 62457019 | chr15 | 65669760 | 65669999 |
| chr15 | 65862054 | 65862213 | chr15 | 66963725 | 66963823 | chr15 | 66963928 | 66963964 |
| chr15 | 68112537 | 68112716 | chr15 | 68113794 | 68113973 | chr15 | 68114048 | 68114287 |
| chr15 | 68116286 | 68116682 | chr15 | 68117753 | 68118712 | chr15 | 68118783 | 68118784 |
| chr15 | 68118799 | 68119322 | chr15 | 68119463 | 68120662 | chr15 | 68120753 | 68120932 |
| chr15 | 68120968 | 68122167 | chr15 | 68122569 | 68122748 | chr15 | 68125164 | 68125763 |
| chr15 | 68127717 | 68128436 | chr15 | 68128492 | 68128597 | chr15 | 68260435 | 68260735 |
| chr15 | 71055770 | 71055905 | chr15 | 72412113 | 72412263 | chr15 | 72743650 | 72743859 |
| chr15 | 73659917 | 73660156 | chr15 | 73661476 | 73661748 | chr15 | 74044960 | 74045199 |
| chr15 | 74421927 | 74422226 | chr15 | 74422787 | 74423012 | chr15 | 74658070 | 74658595 |
| chr15 | 74686082 | 74686126 | chr15 | 74818670 | 74818789 | chr15 | 74903822 | 74904001 |
| chr15 | 75251245 | 75251484 | chr15 | 75251580 | 75251879 | chr15 | 75471036 | 75471275 |
| chr15 | 76627515 | 76627907 | chr15 | 76628959 | 76629314 | chr15 | 76629588 | 76629633 |
| chr15 | 76629732 | 76630931 | chr15 | 76632161 | 76632520 | chr15 | 76635040 | 76635279 |
| chr15 | 76635456 | 76635635 | chr15 | 76638387 | 76638806 | chr15 | 77448976 | 77449087 |
| chr15 | 78501725 | 78502024 | chr15 | 78556795 | 78557034 | chr15 | 78557110 | 78557204 |
| chr15 | 78596066 | 78596245 | chr15 | 78632626 | 78632925 | chr15 | 78912192 | 78912491 |
| chr15 | 78912549 | 78912728 | chr15 | 78912832 | 78913251 | chr15 | 78913444 | 78913683 |
| chr15 | 79104143 | 79104159 | chr15 | 79381709 | 79382648 | chr15 | 79382693 | 79383268 |
| chr15 | 79383873 | 79384052 | chr15 | 79502137 | 79502381 | chr15 | 79575197 | 79575556 |
| chr15 | 79576062 | 79576361 | chr15 | 79724034 | 79724333 | chr15 | 79724402 | 79725241 |
| chr15 | 79725332 | 79725584 | chr15 | 82336777 | 82337076 | chr15 | 82339995 | 82340234 |
| chr15 | 83315246 | 83315474 | chr15 | 83316160 | 83317162 | chr15 | 83349131 | 83349790 |

TABLE 14-continued

| chr | start | end | chr | start | end | chr | start | end |
|---|---|---|---|---|---|---|---|---|
| chr15 | 83378112 | 83378164 | chr15 | 83378186 | 83378471 | chr15 | 83776161 | 83776880 |
| chr15 | 83875571 | 83875985 | chr15 | 83876953 | 83877252 | chr15 | 83952108 | 83952827 |
| chr15 | 83953024 | 83953983 | chr15 | 84115648 | 84116067 | chr15 | 84116808 | 84116995 |
| chr15 | 84322765 | 84323124 | chr15 | 84748500 | 84749339 | chr15 | 85143052 | 85143144 |
| chr15 | 88798591 | 88798890 | chr15 | 88799448 | 88800407 | chr15 | 88800463 | 88801182 |
| chr15 | 89149070 | 89149489 | chr15 | 89248651 | 89249150 | chr15 | 89345953 | 89346492 |
| chr15 | 89346568 | 89347047 | chr15 | 89903410 | 89903889 | chr15 | 89910426 | 89910845 |
| chr15 | 89910988 | 89911287 | chr15 | 89913676 | 89913855 | chr15 | 89914144 | 89914983 |
| chr15 | 89915156 | 89915455 | chr15 | 89921862 | 89922101 | chr15 | 89922110 | 89922649 |
| chr15 | 89942671 | 89943030 | chr15 | 89943319 | 89943798 | chr15 | 89949317 | 89950036 |
| chr15 | 89950154 | 89951215 | chr15 | 89951302 | 89951901 | chr15 | 89952065 | 89953144 |
| chr15 | 89954122 | 89954415 | chr15 | 89956288 | 89956527 | chr15 | 90039488 | 90039787 |
| chr15 | 90755819 | 90756144 | chr15 | 91643264 | 91643683 | chr15 | 92936281 | 92936426 |
| chr15 | 92937115 | 92937474 | chr15 | 92937849 | 92938388 | chr15 | 93631638 | 93632117 |
| chr15 | 93632558 | 93633337 | chr15 | 94347588 | 94347707 | chr15 | 95388473 | 95388712 |
| chr15 | 96874259 | 96874416 | chr15 | 96889374 | 96889506 | chr15 | 96897853 | 96898092 |
| chr15 | 96911456 | 96911815 | chr15 | 96952594 | 96953313 | chr15 | 96959644 | 96960063 |
| chr15 | 96960428 | 96960513 | chr15 | 96960630 | 96960907 | chr15 | 97006274 | 97006623 |
| chr15 | 98504040 | 98504219 | chr15 | 98836077 | 98836479 | chr15 | 98965179 | 98965232 |
| chr15 | 99193106 | 99193345 | chr15 | 99193350 | 99193583 | chr15 | 99193873 | 99194172 |
| chr15 | 99456272 | 99456404 | chr15 | 100913332 | 100913982 | chr15 | 101420447 | 101420686 |
| chr15 | 101420848 | 101421087 | chr15 | 101513532 | 101513831 | chr16 | 142567 | 142775 |
| chr16 | 215341 | 216300 | chr16 | 216587 | 217070 | chr16 | 230229 | 230708 |
| chr16 | 318040 | 318316 | chr16 | 318422 | 318841 | chr16 | 337510 | 337749 |
| chr16 | 410303 | 410482 | chr16 | 611304 | 611603 | chr16 | 611876 | 612355 |
| chr16 | 612774 | 613133 | chr16 | 667040 | 667349 | chr16 | 667382 | 667399 |
| chr16 | 667466 | 667561 | chr16 | 677879 | 677993 | chr16 | 700225 | 700404 |
| chr16 | 726539 | 727078 | chr16 | 731400 | 731699 | chr16 | 735131 | 735670 |
| chr16 | 740888 | 741003 | chr16 | 741280 | 741507 | chr16 | 837262 | 837561 |
| chr16 | 845881 | 846060 | chr16 | 882567 | 882686 | chr16 | 895011 | 895250 |
| chr16 | 943398 | 943637 | chr16 | 1018046 | 1018225 | chr16 | 1030210 | 1030749 |
| chr16 | 1052488 | 1052727 | chr16 | 1103032 | 1103032 | chr16 | 1116721 | 1116766 |
| chr16 | 1128927 | 1129226 | chr16 | 1155068 | 1155307 | chr16 | 1203883 | 1204122 |
| chr16 | 1217226 | 1217583 | chr16 | 1217943 | 1218182 | chr16 | 1228711 | 1229010 |
| chr16 | 1230057 | 1230236 | chr16 | 1248521 | 1248760 | chr16 | 1267844 | 1268203 |
| chr16 | 1271447 | 1271746 | chr16 | 1312450 | 1312689 | chr16 | 1323900 | 1324139 |
| chr16 | 1382862 | 1383041 | chr16 | 1394400 | 1394579 | chr16 | 1397380 | 1397559 |
| chr16 | 1407366 | 1407485 | chr16 | 1407819 | 1407938 | chr16 | 1428422 | 1428961 |
| chr16 | 1491471 | 1491694 | chr16 | 1730213 | 1730692 | chr16 | 1741757 | 1742176 |
| chr16 | 2028986 | 2029225 | chr16 | 2040818 | 2042257 | chr16 | 2106629 | 2106741 |
| chr16 | 2128503 | 2128682 | chr16 | 2129033 | 2129332 | chr16 | 2141835 | 2142014 |
| chr16 | 2142468 | 2142707 | chr16 | 2213239 | 2213396 | chr16 | 2232665 | 2232784 |
| chr16 | 2234634 | 2235113 | chr16 | 2281163 | 2281402 | chr16 | 2287214 | 2287453 |
| chr16 | 2531136 | 2531255 | chr16 | 2764275 | 2764574 | chr16 | 2770033 | 2770512 |
| chr16 | 2818018 | 2818249 | chr16 | 2892457 | 2892816 | chr16 | 3016951 | 3017730 |
| chr16 | 3068097 | 3068276 | chr16 | 3151038 | 3151264 | chr16 | 3211625 | 3211742 |
| chr16 | 3211805 | 3211982 | chr16 | 3220474 | 3222325 | chr16 | 3225390 | 3225689 |
| chr16 | 3232697 | 3234121 | chr16 | 3234197 | 3234541 | chr16 | 3237783 | 3238022 |
| chr16 | 3238164 | 3238622 | chr16 | 3238912 | 3239631 | chr16 | 3239692 | 3239931 |
| chr16 | 3241517 | 3241756 | chr16 | 3241862 | 3241981 | chr16 | 3355200 | 3355799 |
| chr16 | 3598818 | 3599057 | chr16 | 3696620 | 3696799 | chr16 | 3802932 | 3803171 |
| chr16 | 4264433 | 4264792 | chr16 | 4431039 | 4431213 | chr16 | 4846061 | 4846415 |
| chr16 | 5037803 | 5038102 | chr16 | 5541026 | 5541257 | chr16 | 6069989 | 6070122 |
| chr16 | 7354560 | 7354739 | chr16 | 8780956 | 8781135 | chr16 | 8870279 | 8870458 |
| chr16 | 9009781 | 9010075 | chr16 | 10274325 | 10274504 | chr16 | 10275231 | 10275470 |
| chr16 | 10275671 | 10276030 | chr16 | 10276270 | 10277409 | chr16 | 10479719 | 10480078 |
| chr16 | 12530095 | 12630274 | chr16 | 12971812 | 12972035 | chr16 | 12994359 | 12994838 |
| chr16 | 12994969 | 12995688 | chr16 | 12995707 | 12996426 | chr16 | 12996520 | 12996819 |
| chr16 | 12996861 | 12997100 | chr16 | 12997306 | 12997785 | chr16 | 14725745 | 14725864 |
| chr16 | 15489851 | 15489884 | chr16 | 15820726 | 15820965 | chr16 | 18802486 | 18802725 |
| chr16 | 18950987 | 18951093 | chr16 | 19567117 | 19567536 | chr16 | 19895051 | 19895230 |
| chr16 | 21831520 | 21832052 | chr16 | 21839250 | 21839348 | chr16 | 22824599 | 22825198 |
| chr16 | 22825225 | 22826184 | chr16 | 23313374 | 23313613 | chr16 | 23313674 | 23313913 |
| chr16 | 23706240 | 23706599 | chr16 | 23765995 | 23766098 | chr16 | 23766133 | 23766234 |
| chr16 | 23847214 | 23848053 | chr16 | 24267101 | 24267312 | chr16 | 24267383 | 24267594 |
| chr16 | 25266436 | 25266675 | chr16 | 25702855 | 25703094 | chr16 | 25703685 | 25704705 |
| chr16 | 26664758 | 26664853 | chr16 | 27460002 | 27460156 | chr16 | 28074101 | 28074760 |
| chr16 | 28074869 | 28075288 | chr16 | 29118954 | 29119133 | chr16 | 29153201 | 29153254 |
| chr16 | 29244800 | 29245099 | chr16 | 29830796 | 29831155 | chr16 | 29888045 | 29888332 |
| chr16 | 29888549 | 29888761 | chr16 | 30017240 | 30017539 | chr16 | 30116211 | 30116390 |
| chr16 | 30124597 | 30124949 | chr16 | 30804458 | 30804575 | chr16 | 30826363 | 30826570 |
| chr16 | 30906930 | 30907049 | chr16 | 30907123 | 30907229 | chr16 | 31227815 | 31228402 |
| chr16 | 31446904 | 31447173 | chr16 | 31497971 | 31498087 | chr16 | 31500460 | 31500759 |
| chr16 | 31580469 | 31581058 | chr16 | 46721556 | 46721787 | chr16 | 47177447 | 47177686 |
| chr16 | 48844690 | 48845229 | chr16 | 49309067 | 49309366 | chr16 | 49311432 | 49312391 |
| chr16 | 49313268 | 49313807 | chr16 | 49313921 | 49314220 | chr16 | 49314341 | 49314640 |
| chr16 | 49314692 | 49314931 | chr16 | 49315202 | 49315381 | chr16 | 49315831 | 49316670 |
| chr16 | 49637986 | 49638165 | chr16 | 50335693 | 50335872 | chr16 | 51183824 | 51184483 |

TABLE 14-continued

| chr | start | end | chr | start | end | chr | start | end |
|---|---|---|---|---|---|---|---|---|
| chr16 | 51184725 | 51185444 | chr16 | 51185763 | 51186362 | chr16 | 51186497 | 51187036 |
| chr16 | 51189848 | 51190309 | chr16 | 53563519 | 53563734 | chr16 | 54318824 | 54318838 |
| chr16 | 54318855 | 54319063 | chr16 | 54319325 | 54319564 | chr16 | 54321557 | 54321916 |
| chr16 | 54324960 | 54325199 | chr16 | 54628600 | 54628959 | chr16 | 54964875 | 54965211 |
| chr16 | 54966728 | 54967388 | chr16 | 54970986 | 54971165 | chr16 | 54971326 | 54971505 |
| chr16 | 55090585 | 55090944 | chr16 | 55357827 | 55358213 | chr16 | 55358213 | 55358632 |
| chr16 | 55358696 | 55359175 | chr16 | 55362907 | 55363326 | chr16 | 55364631 | 55364930 |
| chr16 | 55365020 | 55365319 | chr16 | 55404898 | 55405317 | chr16 | 55512745 | 55512984 |
| chr16 | 55689812 | 55689991 | chr16 | 55690013 | 55690912 | chr16 | 56224479 | 56224958 |
| chr16 | 56228271 | 56228686 | chr16 | 56651006 | 56651365 | chr16 | 56659095 | 56659754 |
| chr16 | 56672077 | 56672761 | chr16 | 56709755 | 56710114 | chr16 | 57222710 | 57222806 |
| chr16 | 57935476 | 57935655 | chr16 | 58018531 | 58018950 | chr16 | 58019149 | 58019508 |
| chr16 | 58120875 | 58121058 | chr16 | 58497136 | 58497495 | chr16 | 58497672 | 58497911 |
| chr16 | 58498101 | 58498280 | chr16 | 58498468 | 58498809 | chr16 | 58521634 | 58521813 |
| chr16 | 58550415 | 58550587 | chr16 | 58969669 | 58969895 | chr16 | 62068387 | 62068610 |
| chr16 | 62068923 | 62069057 | chr16 | 62070669 | 62070848 | chr16 | 65154833 | 65155192 |
| chr16 | 65156288 | 65156587 | chr16 | 66461694 | 66461933 | chr16 | 66612797 | 66613359 |
| chr16 | 67197615 | 67197854 | chr16 | 67197935 | 67198114 | chr16 | 67198818 | 67199057 |
| chr16 | 67241130 | 67241309 | chr16 | 67313791 | 67314170 | chr16 | 68544170 | 68544409 |
| chr16 | 68676307 | 68677086 | chr16 | 68770847 | 68771086 | chr16 | 68771167 | 68771402 |
| chr16 | 68876728 | 68876847 | chr16 | 70595543 | 70595782 | chr16 | 71459950 | 71460429 |
| chr16 | 71715705 | 71715884 | chr16 | 72957660 | 72957899 | chr16 | 73100373 | 73100612 |
| chr16 | 75019677 | 75019856 | chr16 | 77247366 | 77247545 | chr16 | 77468182 | 77468878 |
| chr16 | 77822493 | 77822972 | chr16 | 78079893 | 78080132 | chr16 | 79623729 | 79623968 |
| chr16 | 80838052 | 80838173 | chr16 | 80966296 | 80966535 | chr16 | 81929288 | 81929467 |
| chr16 | 82660279 | 82660578 | chr16 | 82660638 | 82660817 | chr16 | 84074767 | 84074946 |
| chr16 | 84153290 | 84153469 | chr16 | 84402163 | 84402402 | chr16 | 84853274 | 84853452 |
| chr16 | 85076418 | 85075644 | chr16 | 85317747 | 85317879 | chr16 | 85485652 | 85485951 |
| chr16 | 85517254 | 85517613 | chr16 | 85678551 | 85678850 | chr16 | 85684234 | 85684533 |
| chr16 | 85699596 | 85699925 | chr16 | 85932754 | 85932933 | chr16 | 86320254 | 86320493 |
| chr16 | 86320659 | 86320898 | chr16 | 86320925 | 86321147 | chr16 | 86530848 | 86531147 |
| chr16 | 86531233 | 86531652 | chr16 | 86541537 | 86541956 | chr16 | 86542296 | 86542535 |
| chr16 | 86544103 | 86545062 | chr16 | 86599392 | 86599931 | chr16 | 86600406 | 86600765 |
| chr16 | 86600868 | 86601107 | chr16 | 86601204 | 86601623 | chr16 | 86601871 | 86602590 |
| chr16 | 86612961 | 86613017 | chr16 | 87092347 | 87092646 | chr16 | 87635029 | 87635208 |
| chr16 | 87636444 | 87636983 | chr16 | 87714178 | 87714477 | chr16 | 87723648 | 87724187 |
| chr16 | 88164316 | 88164555 | chr16 | 88498142 | 88498861 | chr16 | 88503978 | 88504397 |
| chr16 | 88506265 | 88506615 | chr16 | 88512329 | 88512628 | chr16 | 88603617 | 88603848 |
| chr16 | 88623885 | 88624165 | chr16 | 88757428 | 88757571 | chr16 | 88879858 | 88880097 |
| chr16 | 88883159 | 88883458 | chr16 | 88940981 | 88941220 | chr16 | 88942021 | 88942239 |
| chr16 | 88943463 | 88944122 | chr16 | 88945726 | 88946085 | chr16 | 88955160 | 88955459 |
| chr16 | 88956136 | 88956495 | chr16 | 88957374 | 88957934 | chr16 | 88958295 | 88958534 |
| chr16 | 88963191 | 88963850 | chr16 | 88966207 | 88966686 | chr16 | 88968630 | 88968869 |
| chr16 | 88977929 | 88978168 | chr16 | 88992975 | 88993334 | chr16 | 88999543 | 88999557 |
| chr16 | 88999574 | 88999693 | chr16 | 89000127 | 89000306 | chr16 | 89001020 | 89001139 |
| chr16 | 89007420 | 89007659 | chr16 | 89007789 | 89007879 | chr16 | 89008488 | 89008667 |
| chr16 | 89047643 | 89047822 | chr16 | 89072400 | 89022879 | chr16 | 89086034 | 89086273 |
| chr16 | 89107585 | 89107824 | chr16 | 89109345 | 89109493 | chr16 | 89119940 | 89120419 |
| chr16 | 89120607 | 89120963 | chr16 | 89137919 | 89138158 | chr16 | 89220244 | 89220483 |
| chr16 | 89220580 | 89220999 | chr16 | 89254563 | 89254742 | chr16 | 89267260 | 89267439 |
| chr16 | 89267709 | 89267948 | chr16 | 89558549 | 89558807 | chr16 | 89883930 | 89884289 |
| chr16 | 89884875 | 89884989 | chr16 | 89885115 | 89885229 | chr16 | 89900033 | 89900272 |
| chr16 | 89900372 | 89900611 | chr17 | 616914 | 617026 | chr17 | 1082923 | 1083093 |
| chr17 | 1173906 | 1174505 | chr17 | 1536129 | 1536221 | chr17 | 1646312 | 1546539 |
| chr17 | 1623600 | 1623779 | chr17 | 1959375 | 1959614 | chr17 | 2207848 | 2207967 |
| chr17 | 2208042 | 2208147 | chr17 | 2220974 | 2221142 | chr17 | 2249977 | 2250096 |
| chr17 | 3438818 | 3439057 | chr17 | 3658751 | 3658930 | chr17 | 3658991 | 3659110 |
| chr17 | 4544510 | 4544809 | chr17 | 4699212 | 4699331 | chr17 | 4891237 | 4891381 |
| chr17 | 5000340 | 5000879 | chr17 | 5000958 | 5001137 | chr17 | 6616543 | 6616782 |
| chr17 | 6616813 | 6617191 | chr17 | 6679220 | 6679393 | chr17 | 6946113 | 6946244 |
| chr17 | 7348792 | 7349070 | chr17 | 7368864 | 7369223 | chr17 | 7555099 | 7555338 |
| chr17 | 7573915 | 7574094 | chr17 | 7576923 | 7577222 | chr17 | 7577423 | 7577662 |
| chr17 | 7578078 | 7578557 | chr17 | 7906156 | 7906514 | chr17 | 8104071 | 8104173 |
| chr17 | 8230246 | 8230785 | chr17 | 8774685 | 8774728 | chr17 | 8868524 | 8869483 |
| chr17 | 8906183 | 8906602 | chr17 | 8906895 | 8907674 | chr17 | 8925983 | 8926201 |
| chr17 | 10100995 | 10102074 | chr17 | 10102331 | 10102750 | chr17 | 11144218 | 11144424 |
| chr17 | 11144839 | 11145078 | chr17 | 13503875 | 13504294 | chr17 | 13504470 | 13504769 |
| chr17 | 13504873 | 13505292 | chr17 | 13505316 | 13505675 | chr17 | 14200962 | 14201261 |
| chr17 | 14204178 | 14204317 | chr17 | 14204425 | 14204724 | chr17 | 15244976 | 15245215 |
| chr17 | 16282157 | 16282396 | chr17 | 16570674 | 16570897 | chr17 | 17062513 | 17062752 |
| chr17 | 17123889 | 17124068 | chr17 | 17398520 | 17398542 | chr17 | 18163094 | 18163415 |
| chr17 | 18538207 | 18538365 | chr17 | 20817897 | 20817998 | chr17 | 25620495 | 25620794 |
| chr17 | 25676885 | 25677004 | chr17 | 25680190 | 25680276 | chr17 | 25907676 | 25907855 |
| chr17 | 26263104 | 26263214 | chr17 | 26554551 | 26554790 | chr17 | 26961721 | 26961922 |
| chr17 | 27038568 | 27038985 | chr17 | 27044696 | 27044875 | chr17 | 27056846 | 27056957 |
| chr17 | 27170072 | 27170182 | chr17 | 27181284 | 27181456 | chr17 | 27332378 | 27332737 |
| chr17 | 27716018 | 27716134 | chr17 | 27716198 | 27716314 | chr17 | 27940276 | 27940995 |
| chr17 | 28562614 | 28562853 | chr17 | 29232148 | 29232267 | chr17 | 29249615 | 29250034 |

TABLE 14-continued

| chr | start | end | chr | start | end | chr | start | end |
|---|---|---|---|---|---|---|---|---|
| chr17 | 29298002 | 29298463 | chr17 | 29718123 | 29718362 | chr17 | 29719096 | 29719335 |
| chr17 | 30243689 | 30243988 | chr17 | 30250242 | 30250345 | chr17 | 31618333 | 31619412 |
| chr17 | 31619870 | 31620109 | chr17 | 32483946 | 32484125 | chr17 | 32906299 | 32906718 |
| chr17 | 32906888 | 32907112 | chr17 | 32907136 | 32907247 | chr17 | 32907554 | 32907853 |
| chr17 | 32908044 | 32908463 | chr17 | 32908550 | 32909029 | chr17 | 33672832 | 33673071 |
| chr17 | 33877184 | 33877303 | chr17 | 33917240 | 33917523 | chr17 | 35165549 | 35165788 |
| chr17 | 35165912 | 35166091 | chr17 | 35285455 | 35285754 | chr17 | 35290313 | 35290732 |
| chr17 | 35291242 | 35291457 | chr17 | 35291749 | 35292708 | chr17 | 35293630 | 35294229 |
| chr17 | 35294364 | 35294603 | chr17 | 35294955 | 35295254 | chr17 | 35296069 | 35296368 |
| chr17 | 35296629 | 35296988 | chr17 | 35297527 | 35298246 | chr17 | 35299154 | 35300953 |
| chr17 | 35303259 | 35303618 | chr17 | 36102935 | 36102414 | chr17 | 36103497 | 36103676 |
| chr17 | 36104031 | 36104870 | chr17 | 36105141 | 36105680 | chr17 | 37192168 | 37192281 |
| chr17 | 37321100 | 37322010 | chr17 | 37366236 | 37366655 | chr17 | 37369106 | 37369285 |
| chr17 | 37380922 | 37381941 | chr17 | 37382048 | 37382347 | chr17 | 37757066 | 37757305 |
| chr17 | 37760406 | 37760645 | chr17 | 37761897 | 37762436 | chr17 | 37879697 | 37879712 |
| chr17 | 38179295 | 38179348 | chr17 | 38179492 | 38179534 | chr17 | 38347473 | 38342212 |
| chr17 | 38497542 | 38497721 | chr17 | 38498009 | 38498188 | chr17 | 39682550 | 39682729 |
| chr17 | 40332846 | 40333268 | chr17 | 40400770 | 40401109 | chr17 | 40464179 | 40464418 |
| chr17 | 40464443 | 40464627 | chr17 | 40975576 | 40975754 | chr17 | 41278542 | 41278693 |
| chr17 | 41651776 | 41651887 | chr17 | 41791386 | 41791565 | chr17 | 41791591 | 41791599 |
| chr17 | 42030244 | 42030843 | chr17 | 42061240 | 42061479 | chr17 | 42082421 | 42082660 |
| chr17 | 42092116 | 42092295 | chr17 | 42331637 | 42331746 | chr17 | 42393780 | 42394113 |
| chr17 | 42402782 | 42402984 | chr17 | 42587336 | 42587452 | chr17 | 42635199 | 42635844 |
| chr17 | 42733619 | 42733978 | chr17 | 42787580 | 42787699 | chr17 | 42907489 | 42908028 |
| chr17 | 43001800 | 43002029 | chr17 | 43037408 | 43037504 | chr17 | 43044584 | 43044763 |
| chr17 | 43044909 | 43045208 | chr17 | 43047355 | 43047834 | chr17 | 43339012 | 43339431 |
| chr17 | 43339546 | 43339994 | chr17 | 43974158 | 43974457 | chr17 | 45331345 | 45331404 |
| chr17 | 45810767 | 45811426 | chr17 | 45867239 | 45867538 | chr17 | 46124907 | 46125146 |
| chr17 | 46619224 | 46619224 | chr17 | 46620405 | 46621184 | chr17 | 46621257 | 46621535 |
| chr17 | 46621764 | 46622003 | chr17 | 46655074 | 46655253 | chr17 | 46655351 | 46656531 |
| chr17 | 46659345 | 46659944 | chr17 | 46663666 | 46663928 | chr17 | 46674831 | 46675072 |
| chr17 | 46675086 | 46675685 | chr17 | 46690387 | 46690746 | chr17 | 46691430 | 46691669 |
| chr17 | 46691719 | 46692198 | chr17 | 46692344 | 46692509 | chr17 | 46710857 | 46711156 |
| chr17 | 46711179 | 46711213 | chr17 | 46711240 | 46711478 | chr17 | 46713934 | 46714166 |
| chr17 | 46795563 | 46796545 | chr17 | 46796606 | 46797662 | chr17 | 46799522 | 46800001 |
| chr17 | 46800516 | 46800755 | chr17 | 46800860 | 46801418 | chr17 | 46802364 | 46803286 |
| chr17 | 46804029 | 46804508 | chr17 | 46810328 | 46811047 | chr17 | 46811269 | 46811628 |
| chr17 | 46816191 | 46816730 | chr17 | 46824218 | 46825149 | chr17 | 46825190 | 46825609 |
| chr17 | 46826897 | 46827196 | chr17 | 46827244 | 46827843 | chr17 | 46829420 | 46829659 |
| chr17 | 46829898 | 46830195 | chr17 | 46831700 | 46832719 | chr17 | 47072716 | 47073555 |
| chr17 | 47073899 | 47074318 | chr17 | 47074459 | 47074489 | chr17 | 47074597 | 47074998 |
| chr17 | 47075083 | 47075442 | chr17 | 47075616 | 47076155 | chr17 | 47574001 | 47574240 |
| chr17 | 47657445 | 47657684 | chr17 | 47865416 | 47865655 | chr17 | 47987423 | 47987722 |
| chr17 | 47987843 | 47988202 | chr17 | 48041057 | 48041416 | chr17 | 48041578 | 48041817 |
| chr17 | 48041965 | 48042144 | chr17 | 48042337 | 48043056 | chr17 | 48048857 | 48049156 |
| chr17 | 48049228 | 48050607 | chr17 | 48070946 | 48071125 | chr17 | 48071694 | 48071957 |
| chr17 | 48612147 | 48612386 | chr17 | 48636500 | 48637219 | chr17 | 48653054 | 48653233 |
| chr17 | 48799847 | 48799963 | chr17 | 49229486 | 49229601 | chr17 | 50235126 | 50235365 |
| chr17 | 50235625 | 50236032 | chr17 | 51900930 | 51901109 | chr17 | 53341155 | 53341557 |
| chr17 | 53342774 | 53343193 | chr17 | 53922571 | 53922870 | chr17 | 54674890 | 54675369 |
| chr17 | 54755873 | 54756112 | chr17 | 56092519 | 56092620 | chr17 | 56234305 | 56234844 |
| chr17 | 56326853 | 56327092 | chr17 | 56327197 | 56327376 | chr17 | 56833025 | 56833324 |
| chr17 | 56833622 | 56834161 | chr17 | 56834222 | 56834461 | chr17 | 57297028 | 57297207 |
| chr17 | 58216513 | 58217652 | chr17 | 58218670 | 58219089 | chr17 | 58227281 | 58227520 |
| chr17 | 58498657 | 58499396 | chr17 | 59474060 | 59474719 | chr17 | 59474758 | 59475177 |
| chr17 | 59475504 | 59476023 | chr17 | 59476084 | 59476203 | chr17 | 59476314 | 59476733 |
| chr17 | 59478046 | 59478705 | chr17 | 59488010 | 59488549 | chr17 | 59528775 | 59530454 |
| chr17 | 59531574 | 59532233 | chr17 | 59533741 | 59534580 | chr17 | 59534677 | 59534856 |
| chr17 | 59535059 | 59535298 | chr17 | 59539150 | 59539689 | chr17 | 61777984 | 61778403 |
| chr17 | 61817858 | 61818036 | chr17 | 61926149 | 61926688 | chr17 | 62777244 | 62777543 |
| chr17 | 62777650 | 62777889 | chr17 | 64672276 | 64672635 | chr17 | 66596379 | 66596618 |
| chr17 | 66596884 | 66597123 | chr17 | 67410389 | 67410501 | chr17 | 68164667 | 68164906 |
| chr17 | 70026473 | 70026755 | chr17 | 70112818 | 70114617 | chr17 | 70215595 | 70216674 |
| chr17 | 71641465 | 71641761 | chr17 | 71948352 | 71948951 | chr17 | 72270202 | 72270501 |
| chr17 | 72321844 | 72322074 | chr17 | 72322269 | 72322694 | chr17 | 72353113 | 72353531 |
| chr17 | 72427777 | 72427963 | chr17 | 72428244 | 72428483 | chr17 | 72667242 | 72667661 |
| chr17 | 72848926 | 72849165 | chr17 | 72856964 | 72857443 | chr17 | 72920705 | 72921124 |
| chr17 | 73031547 | 73031619 | chr17 | 73073610 | 73073876 | chr17 | 73545910 | 73546120 |
| chr17 | 73584733 | 73584972 | chr17 | 73585918 | 73586517 | chr17 | 73608232 | 73608411 |
| chr17 | 73636062 | 73636421 | chr17 | 74028261 | 74028461 | chr17 | 74047755 | 74047994 |
| chr17 | 74070386 | 74070672 | chr17 | 74071344 | 74071583 | chr17 | 74071590 | 74071825 |
| chr17 | 74072840 | 74073139 | chr17 | 74073172 | 74073531 | chr17 | 74390289 | 74390468 |
| chr17 | 74533808 | 74534407 | chr17 | 74581083 | 74581322 | chr17 | 74864974 | 74865273 |
| chr17 | 74865612 | 74866331 | chr17 | 75207765 | 75207944 | chr17 | 75368658 | 75369317 |
| chr17 | 75369351 | 75369950 | chr17 | 75370174 | 75370413 | chr17 | 75370522 | 75370701 |
| chr17 | 75385122 | 75385301 | chr17 | 75523058 | 75523354 | chr17 | 75524556 | 75525275 |
| chr17 | 75733902 | 75734108 | chr17 | 75797121 | 75797265 | chr17 | 76125122 | 76125301 |
| chr17 | 76137862 | 76138281 | chr17 | 76138525 | 76138710 | chr17 | 76227774 | 76228433 |

TABLE 14-continued

| chr | start | end | chr | start | end | chr | start | end |
|---|---|---|---|---|---|---|---|---|
| chr17 | 76404662 | 76404757 | chr17 | 76921756 | 76921934 | chr17 | 76974354 | 76974582 |
| chr17 | 77084488 | 77084667 | chr17 | 77104978 | 77105277 | chr17 | 77145037 | 77145336 |
| chr17 | 77179017 | 77179376 | chr17 | 77179532 | 77179891 | chr17 | 77776733 | 77777152 |
| chr17 | 77777504 | 77778043 | chr17 | 77778852 | 77779136 | chr17 | 77788756 | 77789055 |
| chr17 | 77789219 | 77789578 | chr17 | 77825605 | 77825858 | chr17 | 77899590 | 77899634 |
| chr17 | 78122175 | 78122294 | chr17 | 78447053 | 78447213 | chr17 | 78451842 | 78452141 |
| chr17 | 78452199 | 78452438 | chr17 | 78452578 | 78452937 | chr17 | 78518204 | 78518295 |
| chr17 | 78599493 | 78599732 | chr17 | 78667897 | 78668256 | chr17 | 78874418 | 78874650 |
| chr17 | 79094095 | 79094334 | chr17 | 79099696 | 79099875 | chr17 | 79615087 | 79615446 |
| chr17 | 79626656 | 79626797 | chr17 | 79769354 | 79769773 | chr17 | 80254258 | 80254371 |
| chr17 | 80289153 | 80289392 | chr17 | 80329628 | 80330167 | chr17 | 80394659 | 80394678 |
| chr17 | 80479366 | 80479525 | chr17 | 80535286 | 80535469 | chr17 | 80654909 | 80655088 |
| chr17 | 80693343 | 80693582 | chr17 | 80797600 | 80798439 | chr17 | 80832209 | 80832508 |
| chr17 | 80832635 | 80832874 | chr17 | 81008543 | 81008902 | chr17 | 81033413 | 81033592 |
| chr17 | 81048919 | 81049098 | chr17 | 81049943 | 81050146 | chr18 | 499454 | 499575 |
| chr18 | 499947 | 500842 | chr18 | 904376 | 904735 | chr18 | 904926 | 905105 |
| chr18 | 905359 | 905718 | chr18 | 906770 | 907009 | chr18 | 907384 | 907683 |
| chr18 | 907826 | 908065 | chr18 | 908373 | 908607 | chr18 | 909046 | 909225 |
| chr18 | 909388 | 909687 | chr18 | 2755855 | 2755974 | chr18 | 2906167 | 2906406 |
| chr18 | 3215032 | 3215271 | chr18 | 3498980 | 3499447 | chr18 | 4453885 | 4454244 |
| chr18 | 4454979 | 4455278 | chr18 | 5133126 | 5133405 | chr18 | 5196439 | 5197038 |
| chr18 | 5197126 | 5197425 | chr18 | 5543132 | 5543431 | chr18 | 5543606 | 5543957 |
| chr18 | 5628072 | 5628611 | chr18 | 5629700 | 5630059 | chr18 | 5630218 | 5630457 |
| chr18 | 5890519 | 5891418 | chr18 | 5894935 | 5895294 | chr18 | 5895881 | 5896180 |
| chr18 | 6729881 | 6730093 | chr18 | 7116858 | 7117073 | chr18 | 7117586 | 2117885 |
| chr18 | 7567708 | 7568367 | chr18 | 8608649 | 8609062 | chr18 | 8612178 | 8612357 |
| chr18 | 9771621 | 9771850 | chr18 | 9912693 | 9912872 | chr18 | 10589013 | 10589432 |
| chr18 | 11148888 | 11149127 | chr18 | 11149486 | 11149965 | chr18 | 11401557 | 11401846 |
| chr18 | 11751538 | 11751777 | chr18 | 11751874 | 11752473 | chr18 | 11752625 | 11752805 |
| chr18 | 11942634 | 11942746 | chr18 | 12254133 | 12254672 | chr18 | 12307170 | 12307829 |
| chr18 | 12376133 | 12376206 | chr18 | 12911281 | 12911408 | chr18 | 13824125 | 13824184 |
| chr18 | 13826316 | 13826615 | chr18 | 13868620 | 13869039 | chr18 | 15198162 | 15198269 |
| chr18 | 18822294 | 18823060 | chr18 | 18823101 | 18823373 | chr18 | 19750286 | 19750447 |
| chr18 | 20911467 | 20911646 | chr18 | 21269344 | 21269490 | chr18 | 21269581 | 21269763 |
| chr18 | 22928981 | 22930660 | chr18 | 22930715 | 22931254 | chr18 | 23686388 | 23686502 |
| chr18 | 24127650 | 24128129 | chr18 | 24130729 | 24131267 | chr18 | 24764851 | 24765252 |
| chr18 | 25755505 | 25755744 | chr18 | 25755936 | 25756115 | chr18 | 25756542 | 25756822 |
| chr18 | 25757151 | 25757530 | chr18 | 25757687 | 25757926 | chr18 | 25757994 | 25758233 |
| chr18 | 28620819 | 28621178 | chr18 | 28621242 | 28621274 | chr18 | 28621383 | 28621481 |
| chr18 | 28621545 | 28622024 | chr18 | 28622335 | 28622575 | chr18 | 30349642 | 30349872 |
| chr18 | 31020419 | 31020898 | chr18 | 31158007 | 31158049 | chr18 | 31738953 | 31739552 |
| chr18 | 31802031 | 31802270 | chr18 | 31802864 | 31803043 | chr18 | 31803336 | 31803575 |
| chr18 | 31902690 | 31902944 | chr18 | 32073807 | 32074166 | chr18 | 32557847 | 32557968 |
| chr18 | 32957702 | 32957813 | chr18 | 33078274 | 33078393 | chr18 | 33078634 | 33078753 |
| chr18 | 33877784 | 33877839 | chr18 | 34833519 | 34833938 | chr18 | 35064986 | 35065525 |
| chr18 | 35104565 | 35104984 | chr18 | 35144766 | 35145545 | chr18 | 35146023 | 35146322 |
| chr18 | 35147409 | 35147648 | chr18 | 43914126 | 43914365 | chr18 | 44259911 | 44260067 |
| chr18 | 44335999 | 44336786 | chr18 | 44336805 | 44337044 | chr18 | 44337445 | 44338164 |
| chr18 | 44772980 | 44773279 | chr18 | 44773574 | 44774233 | chr18 | 44774319 | 44774804 |
| chr18 | 44775309 | 44775647 | chr18 | 44776881 | 44777180 | chr18 | 44777227 | 44777406 |
| chr18 | 44777512 | 44777853 | chr18 | 44777949 | 44778411 | chr18 | 44780903 | 44781142 |
| chr18 | 44787695 | 44787934 | chr18 | 44788177 | 44788356 | chr18 | 44789375 | 44789614 |
| chr18 | 44789786 | 44790025 | chr18 | 45057993 | 45058335 | chr18 | 46142587 | 46142715 |
| chr18 | 49867202 | 49867483 | chr18 | 52988906 | 52989316 | chr18 | 52989723 | 52989962 |
| chr18 | 53257052 | 53257291 | chr18 | 53446884 | 53447903 | chr18 | 53989718 | 53989828 |
| chr18 | 53989876 | 53989957 | chr18 | 54788984 | 54789343 | chr18 | 55019610 | 55019918 |
| chr18 | 55020572 | 55020811 | chr18 | 55020981 | 55021340 | chr18 | 55103307 | 55103486 |
| chr18 | 55103645 | 55103824 | chr18 | 55104744 | 55105244 | chr18 | 55105630 | 55105929 |
| chr18 | 55114441 | 55114740 | chr18 | 55850767 | 55851066 | chr18 | 56483824 | 56483938 |
| chr18 | 56815757 | 56815876 | chr18 | 56886981 | 56887517 | chr18 | 56888470 | 56888709 |
| chr18 | 56931460 | 56931682 | chr18 | 56931888 | 56932187 | chr18 | 56932256 | 56932375 |
| chr18 | 56934926 | 56935405 | chr18 | 56935920 | 56936159 | chr18 | 56939025 | 56939264 |
| chr18 | 56939324 | 56940823 | chr18 | 56940863 | 56941882 | chr18 | 57363606 | 57363845 |
| chr18 | 57364185 | 57364484 | chr18 | 57364556 | 57364795 | chr18 | 59000886 | 59001125 |
| chr18 | 59001222 | 59001821 | chr18 | 60263452 | 60263991 | chr18 | 60985417 | 60985825 |
| chr18 | 67067464 | 67068003 | chr18 | 67068059 | 67068298 | chr18 | 67068368 | 67068547 |
| chr18 | 67068614 | 67068913 | chr18 | 67069142 | 67069321 | chr18 | 70209058 | 70209297 |
| chr18 | 70209348 | 70209527 | chr18 | 70210483 | 70210583 | chr18 | 70211527 | 70211766 |
| chr18 | 70534207 | 70534686 | chr18 | 70535046 | 70535225 | chr18 | 70535299 | 70535658 |
| chr18 | 70535918 | 70536697 | chr18 | 70536733 | 70536972 | chr18 | 70537230 | 70537293 |
| chr18 | 73167500 | 73167919 | chr18 | 73627925 | 73628153 | chr18 | 74501045 | 74501267 |
| chr18 | 74755430 | 74755577 | chr18 | 74961264 | 74962247 | chr18 | 74962452 | 74962751 |
| chr18 | 74962896 | 74963675 | chr18 | 75339137 | 75339406 | chr18 | 75362839 | 75363078 |
| chr18 | 75551197 | 75551376 | chr18 | 75612137 | 75612376 | chr18 | 75999330 | 75999509 |
| chr18 | 76239460 | 76239699 | chr18 | 76501405 | 76501584 | chr18 | 76653557 | 76653736 |
| chr18 | 76686175 | 76686354 | chr18 | 77143365 | 77143451 | chr18 | 77167752 | 77167929 |
| chr18 | 77181263 | 77181502 | chr18 | 77194838 | 77195077 | chr18 | 77205436 | 77205735 |
| chr18 | 77285814 | 77286113 | chr18 | 77309459 | 77309638 | chr18 | 77312784 | 77313017 |

TABLE 14-continued

| chr | start | end | chr | start | end | chr | start | end |
|---|---|---|---|---|---|---|---|---|
| chr18 | 77329633 | 77330101 | chr18 | 77371350 | 77371589 | chr18 | 77543156 | 77543335 |
| chr18 | 77543673 | 77543912 | chr18 | 77547985 | 77548700 | chr18 | 77550108 | 77550467 |
| chr18 | 77557981 | 77558460 | chr18 | 77558732 | 77559031 | chr18 | 77576853 | 77577139 |
| chr18 | 77636517 | 77636696 | chr18 | 78005004 | 78005142 | chr19 | 403435 | 403888 |
| chr19 | 407106 | 407405 | chr19 | 462106 | 462235 | chr19 | 468683 | 468862 |
| chr19 | 485071 | 485490 | chr19 | 549287 | 549526 | chr19 | 555509 | 555625 |
| chr19 | 591272 | 591511 | chr19 | 592492 | 592654 | chr19 | 593197 | 593325 |
| chr19 | 599125 | 599424 | chr19 | 752060 | 752359 | chr19 | 869247 | 869363 |
| chr19 | 883529 | 883888 | chr19 | 883941 | 884240 | chr19 | 891441 | 891616 |
| chr19 | 955668 | 956327 | chr19 | 1003226 | 1003465 | chr19 | 1003583 | 1003822 |
| chr19 | 1004819 | 1005528 | chr19 | 1030082 | 1030309 | chr19 | 1047796 | 1047915 |
| chr19 | 1083392 | 1083526 | chr19 | 1156450 | 1156629 | chr19 | 1170089 | 1170328 |
| chr19 | 1171003 | 1171422 | chr19 | 1220349 | 1220696 | chr19 | 1236397 | 1236631 |
| chr19 | 1274683 | 1274922 | chr19 | 1308065 | 1308184 | chr19 | 1325714 | 1325989 |
| chr19 | 1401655 | 1401894 | chr19 | 1450236 | 1450475 | chr19 | 1467327 | 1468286 |
| chr19 | 1496313 | 1496552 | chr19 | 1496555 | 1496672 | chr19 | 1524289 | 1524528 |
| chr19 | 1525530 | 1526053 | chr19 | 1527132 | 1527307 | chr19 | 1754094 | 1754333 |
| chr19 | 1754653 | 1754892 | chr19 | 1757337 | 1757696 | chr19 | 1762376 | 1762675 |
| chr19 | 1764197 | 1764374 | chr19 | 1775037 | 1775338 | chr19 | 1776276 | 1776635 |
| chr19 | 1799957 | 1800376 | chr19 | 1807893 | 1808492 | chr19 | 2251075 | 2251794 |
| chr19 | 2251973 | 2252752 | chr19 | 2252901 | 2253860 | chr19 | 2274576 | 2274692 |
| chr19 | 2290165 | 2291124 | chr19 | 2302693 | 2303052 | chr19 | 2331339 | 2331518 |
| chr19 | 2513149 | 2513388 | chr19 | 2683817 | 2684046 | chr19 | 3041486 | 3041522 |
| chr19 | 3219555 | 3219659 | chr19 | 3296523 | 3296762 | chr19 | 3361055 | 3361474 |
| chr19 | 3562249 | 3562583 | chr19 | 3578062 | 3578301 | chr19 | 3778053 | 3778472 |
| chr19 | 3779177 | 3779536 | chr19 | 3785566 | 3786345 | chr19 | 3820952 | 3821311 |
| chr19 | 3822008 | 3822307 | chr19 | 3855322 | 3855630 | chr19 | 4054334 | 4054463 |
| chr19 | 4054540 | 4054573 | chr19 | 4311173 | 4311350 | chr19 | 4548040 | 4548459 |
| chr19 | 4550169 | 4550408 | chr19 | 4555813 | 4556214 | chr19 | 4557018 | 4557317 |
| chr19 | 4670678 | 4670857 | chr19 | 5292709 | 5292948 | chr19 | 5338820 | 5339239 |
| chr19 | 5759670 | 5759789 | chr19 | 5826175 | 5826284 | chr19 | 5910275 | 5910429 |
| chr19 | 5914687 | 5914866 | chr19 | 5914907 | 5915146 | chr19 | 6590244 | 6590582 |
| chr19 | 7794919 | 7795338 | chr19 | 7852944 | 7853243 | chr19 | 7853262 | 7853561 |
| chr19 | 8116149 | 8115376 | chr19 | 8576838 | 8577077 | chr19 | 9473555 | 9474140 |
| chr19 | 9517115 | 9517870 | chr19 | 9608817 | 9609116 | chr19 | 9609229 | 9609528 |
| chr19 | 9903828 | 9904054 | chr19 | 9937370 | 9937489 | chr19 | 10231221 | 10231331 |
| chr19 | 10361965 | 10362076 | chr19 | 10398128 | 10398367 | chr19 | 10405892 | 10406431 |
| chr19 | 10406798 | 10407211 | chr19 | 10527085 | 10527282 | chr19 | 10531317 | 10531616 |
| chr19 | 10531890 | 10532069 | chr19 | 10624659 | 10625558 | chr19 | 10823581 | 10823708 |
| chr19 | 11590929 | 11591288 | chr19 | 11592611 | 11592850 | chr19 | 11592942 | 11593241 |
| chr19 | 11689363 | 11689662 | chr19 | 11959816 | 11960175 | chr19 | 12163452 | 12163770 |
| chr19 | 12163819 | 12163998 | chr19 | 12175356 | 12175595 | chr19 | 12175731 | 12176090 |
| chr19 | 12202937 | 12203638 | chr19 | 12266924 | 12267763 | chr19 | 12305754 | 12306351 |
| chr19 | 12476465 | 12476465 | chr19 | 12476501 | 12476644 | chr19 | 12606297 | 12606556 |
| chr19 | 12750903 | 12751142 | chr19 | 12863329 | 12863616 | chr19 | 12951921 | 12952220 |
| chr19 | 12996076 | 12996375 | chr19 | 13210122 | 13210421 | chr19 | 13616617 | 13617336 |
| chr19 | 13618186 | 13618485 | chr19 | 13965933 | 13966022 | chr19 | 14181217 | 14181682 |
| chr19 | 14584149 | 14584868 | chr19 | 15090097 | 15090576 | chr19 | 15121611 | 15121970 |
| chr19 | 15122030 | 15122314 | chr19 | 15288346 | 15288945 | chr19 | 15292293 | 15292592 |
| chr19 | 15342635 | 15343411 | chr19 | 15344007 | 15344426 | chr19 | 17006991 | 17007764 |
| chr19 | 17008422 | 17008884 | chr19 | 17392545 | 17392964 | chr19 | 17717212 | 17717391 |
| chr19 | 17759145 | 17759504 | chr19 | 17791108 | 17791287 | chr19 | 17958396 | 17958935 |
| chr19 | 17983447 | 17983910 | chr19 | 18041167 | 18041286 | chr19 | 18103637 | 18103816 |
| chr19 | 18104390 | 18104493 | chr19 | 18271871 | 18271999 | chr19 | 18330935 | 18331234 |
| chr19 | 18343355 | 18343654 | chr19 | 18343823 | 18344062 | chr19 | 18383252 | 18383431 |
| chr19 | 18714465 | 18714764 | chr19 | 18811473 | 18811791 | chr19 | 18899333 | 18899718 |
| chr19 | 18901753 | 18902172 | chr19 | 18980680 | 18980979 | chr19 | 18989722 | 18990360 |
| chr19 | 18994808 | 18995227 | chr19 | 19334769 | 19334993 | chr19 | 19645776 | 19646015 |
| chr19 | 19651865 | 19652164 | chr19 | 20011908 | 20011992 | chr19 | 20012053 | 20012172 |
| chr19 | 20188746 | 20188865 | chr19 | 20189411 | 20189530 | chr19 | 21646333 | 21646512 |
| chr19 | 21769223 | 21769522 | chr19 | 22018429 | 22018724 | chr19 | 22034402 | 22034896 |
| chr19 | 22610542 | 22610827 | chr19 | 22715053 | 22715532 | chr19 | 23254115 | 23254294 |
| chr19 | 23257780 | 23258559 | chr19 | 23258680 | 23258799 | chr19 | 23299705 | 23299784 |
| chr19 | 23433104 | 23433223 | chr19 | 23598358 | 23598420 | chr19 | 24154518 | 24154697 |
| chr19 | 24216940 | 24217119 | chr19 | 29284377 | 29284796 | chr19 | 29505081 | 29505258 |
| chr19 | 30015844 | 30016803 | chr19 | 30016832 | 30018691 | chr19 | 30019043 | 30019942 |
| chr19 | 30020014 | 30020553 | chr19 | 30021040 | 30021279 | chr19 | 30215468 | 30215572 |
| chr19 | 30252214 | 30252330 | chr19 | 30555254 | 30555473 | chr19 | 30562687 | 30562831 |
| chr19 | 30637413 | 30637633 | chr19 | 30713384 | 30713803 | chr19 | 30713829 | 30714128 |
| chr19 | 30714425 | 30714508 | chr19 | 30715315 | 30715854 | chr19 | 30716236 | 30716655 |
| chr19 | 30716732 | 30718231 | chr19 | 30718761 | 30718934 | chr19 | 30719369 | 30720134 |
| chr19 | 30865626 | 30866525 | chr19 | 31804650 | 31804829 | chr19 | 31839670 | 31839969 |
| chr19 | 31841834 | 31842072 | chr19 | 31842116 | 31842493 | chr19 | 31842502 | 31842741 |
| chr19 | 32364265 | 32364504 | chr19 | 32516309 | 32516495 | chr19 | 32715588 | 32715827 |
| chr19 | 32898350 | 32898589 | chr19 | 33167035 | 33167514 | chr19 | 33467984 | 33468157 |
| chr19 | 33685493 | 33685683 | chr19 | 33792412 | 33792612 | chr19 | 33794599 | 33794838 |
| chr19 | 34112185 | 34112424 | chr19 | 34112450 | 34113049 | chr19 | 34113259 | 34113678 |
| chr19 | 34113911 | 34114210 | chr19 | 34972390 | 34972569 | chr19 | 34973151 | 34973330 |

TABLE 14-continued

| chr | start | end | chr | start | end | chr | start | end |
|---|---|---|---|---|---|---|---|---|
| chr19 | 34973558 | 34973797 | chr19 | 35263983 | 35264092 | chr19 | 35395923 | 35396462 |
| chr19 | 35616250 | 35616489 | chr19 | 35781298 | 35781537 | chr19 | 35797822 | 35798061 |
| chr19 | 36048504 | 36048863 | chr19 | 36049246 | 36049497 | chr19 | 36222334 | 36222567 |
| chr19 | 36249933 | 36250232 | chr19 | 36334884 | 36335243 | chr19 | 36347791 | 36348147 |
| chr19 | 36450030 | 36450449 | chr19 | 36523258 | 36523557 | chr19 | 36735953 | 36736132 |
| chr19 | 36736226 | 36736585 | chr19 | 36822249 | 36822968 | chr19 | 36909074 | 36910028 |
| chr19 | 36912257 | 36912496 | chr19 | 37095591 | 37096660 | chr19 | 37263439 | 37263678 |
| chr19 | 37264143 | 37264487 | chr19 | 37288237 | 37288869 | chr19 | 37341683 | 37342042 |
| chr19 | 37407046 | 37407525 | chr19 | 37463953 | 37464792 | chr19 | 37569394 | 37569573 |
| chr19 | 37702087 | 37702265 | chr19 | 37959762 | 37960061 | chr19 | 37997337 | 37998206 |
| chr19 | 38042290 | 38042769 | chr19 | 38085160 | 38085759 | chr19 | 38085958 | 38086110 |
| chr19 | 38145976 | 38146335 | chr19 | 38146364 | 38146663 | chr19 | 38182793 | 38183392 |
| chr19 | 38308031 | 38308543 | chr19 | 38480952 | 38481190 | chr19 | 38747072 | 38747448 |
| chr19 | 38755189 | 38755422 | chr19 | 38782485 | 38782664 | chr19 | 38789223 | 38789373 |
| chr19 | 38873861 | 38874040 | chr19 | 38905446 | 38905624 | chr19 | 38974158 | 38974337 |
| chr19 | 39135435 | 39135554 | chr19 | 39687575 | 39687934 | chr19 | 39754787 | 39755446 |
| chr19 | 39816862 | 39817161 | chr19 | 39993392 | 39993751 | chr19 | 39997602 | 39997901 |
| chr19 | 40006093 | 40006392 | chr19 | 40006489 | 40006728 | chr19 | 40723923 | 40724342 |
| chr19 | 40829768 | 40830123 | chr19 | 40902350 | 40902279 | chr19 | 40951087 | 40951197 |
| chr19 | 40951602 | 40951841 | chr19 | 41018456 | 41019131 | chr19 | 41025462 | 41025761 |
| chr19 | 41069832 | 41060408 | chr19 | 41073513 | 41073752 | chr19 | 41119097 | 41119735 |
| chr19 | 41354575 | 41354814 | chr19 | 41641740 | 41641979 | chr19 | 42028407 | 42028646 |
| chr19 | 42408226 | 42408405 | chr19 | 42827810 | 42828349 | chr19 | 42856486 | 42856558 |
| chr19 | 44203735 | 44203962 | chr19 | 44405819 | 44406178 | chr19 | 44599691 | 44599803 |
| chr19 | 44905425 | 44905604 | chr19 | 44952193 | 44952909 | chr19 | 45003142 | 45003417 |
| chr19 | 45300052 | 45300291 | chr19 | 45570307 | 45570546 | chr19 | 45574391 | 45574570 |
| chr19 | 45574682 | 45574782 | chr19 | 45574837 | 45574974 | chr19 | 45655309 | 45656448 |
| chr19 | 45656589 | 45657008 | chr19 | 45657129 | 45657368 | chr19 | 45810006 | 45810345 |
| chr19 | 45835239 | 45835353 | chr19 | 45888843 | 45889484 | chr19 | 45997437 | 45997676 |
| chr19 | 46001945 | 46002424 | chr19 | 46234853 | 46234965 | chr19 | 46379822 | 46380241 |
| chr19 | 46404448 | 46404682 | chr19 | 46916631 | 46917170 | chr19 | 46930046 | 46930278 |
| chr19 | 46974477 | 46974776 | chr19 | 46992643 | 46992942 | chr19 | 46993067 | 46993486 |
| chr19 | 46996509 | 46996748 | chr19 | 46996775 | 46997010 | chr19 | 47152515 | 47153114 |
| chr19 | 47200270 | 47200629 | chr19 | 47910405 | 47910620 | chr19 | 47933223 | 47933822 |
| chr19 | 48003512 | 48003747 | chr19 | 48076568 | 48076747 | chr19 | 48137090 | 48137187 |
| chr19 | 48137247 | 48137389 | chr19 | 48151189 | 48151421 | chr19 | 48614769 | 48614851 |
| chr19 | 48771496 | 48771636 | chr19 | 48800507 | 48800866 | chr19 | 48857809 | 48857917 |
| chr19 | 48902834 | 48902953 | chr19 | 48918040 | 48918339 | chr19 | 49119155 | 49119334 |
| chr19 | 49127285 | 49127764 | chr19 | 49180431 | 49180610 | chr19 | 49399126 | 49399414 |
| chr19 | 49575365 | 49575565 | chr19 | 49646062 | 49646294 | chr19 | 49890810 | 49890908 |
| chr19 | 49935656 | 49936255 | chr19 | 49936790 | 49936969 | chr19 | 50028455 | 50028614 |
| chr19 | 50049635 | 50049746 | chr19 | 50215991 | 50216147 | chr19 | 50316147 | 50316566 |
| chr19 | 50353305 | 50353664 | chr19 | 50553917 | 50554516 | chr19 | 50816339 | 50816573 |
| chr19 | 50833750 | 50833966 | chr19 | 50938470 | 50938706 | chr19 | 51161151 | 51161330 |
| chr19 | 51162123 | 51162602 | chr19 | 51171130 | 51171369 | chr19 | 51227633 | 51227872 |
| chr19 | 51227975 | 51228154 | chr19 | 51228229 | 51228588 | chr19 | 51304487 | 51304666 |
| chr19 | 51520349 | 51520528 | chr19 | 51830748 | 51831227 | chr19 | 51831286 | 51831465 |
| chr19 | 52097592 | 52097831 | chr19 | 52207162 | 52207461 | chr19 | 52222438 | 52223192 |
| chr19 | 52552089 | 52552248 | chr19 | 52839494 | 52839634 | chr19 | 52839700 | 52840033 |
| chr19 | 52872943 | 52873542 | chr19 | 52956708 | 52956947 | chr19 | 53028835 | 53028952 |
| chr19 | 53031202 | 53031290 | chr19 | 53073476 | 53074075 | chr19 | 53141533 | 53141832 |
| chr19 | 53193757 | 53193996 | chr19 | 53194190 | 53194366 | chr19 | 53496630 | 53496928 |
| chr19 | 53561582 | 53561821 | chr19 | 53635873 | 53636168 | chr19 | 53661566 | 53661865 |
| chr19 | 53757802 | 53758341 | chr19 | 53811774 | 53811986 | chr19 | 53836837 | 53836952 |
| chr19 | 53970464 | 53970636 | chr19 | 53970884 | 53971243 | chr19 | 54023803 | 54024282 |
| chr19 | 54024434 | 54024553 | chr19 | 54024619 | 54024978 | chr19 | 54411032 | 54411267 |
| chr19 | 54411482 | 54411661 | chr19 | 54412780 | 54413079 | chr19 | 54445250 | 54445609 |
| chr19 | 54481691 | 54482050 | chr19 | 54483091 | 54483630 | chr19 | 54485442 | 54485913 |
| chr19 | 56159350 | 56159596 | chr19 | 56201573 | 56201812 | chr19 | 56588806 | 56588868 |
| chr19 | 56728588 | 56729067 | chr19 | 56879426 | 56880075 | chr19 | 56904643 | 56905302 |
| chr19 | 56915225 | 56915524 | chr19 | 56988458 | 56988817 | chr19 | 56989432 | 56989851 |
| chr19 | 57050389 | 57050568 | chr19 | 57149480 | 57149719 | chr19 | 57154802 | 57155101 |
| chr19 | 57182906 | 57183423 | chr19 | 57276559 | 57276798 | chr19 | 57610771 | 57611067 |
| chr19 | 57617433 | 57618212 | chr19 | 57683078 | 57683372 | chr19 | 57862330 | 57862859 |
| chr19 | 57862930 | 57863229 | chr19 | 58011040 | 58011383 | chr19 | 58038708 | 58039067 |
| chr19 | 58094912 | 58095931 | chr19 | 58111529 | 58111888 | chr19 | 58125444 | 58125983 |
| chr19 | 58144419 | 58144778 | chr19 | 58219924 | 58220883 | chr19 | 58238234 | 58239187 |
| chr19 | 58399978 | 58400277 | chr19 | 58400319 | 58400618 | chr19 | 58458679 | 58459278 |
| chr19 | 58514196 | 58514655 | chr19 | 58520661 | 58521020 | chr19 | 58545042 | 58545843 |
| chr19 | 58570448 | 58570747 | chr19 | 58609299 | 58609944 | chr19 | 58629812 | 58630026 |
| chr19 | 58661815 | 58662174 | chr19 | 58666093 | 58666392 | chr19 | 58739983 | 58740222 |
| chr19 | 58874834 | 58874951 | chr19 | 58907613 | 58908272 | chr19 | 58951175 | 58952014 |
| chr19 | 58964105 | 58964283 | chr20 | 291052 | 291453 | chr20 | 399928 | 400167 |
| chr20 | 401079 | 401258 | chr20 | 401495 | 401854 | chr20 | 590349 | 590588 |
| chr20 | 590661 | 590960 | chr20 | 592323 | 592547 | chr20 | 644096 | 644875 |
| chr20 | 799030 | 799146 | chr20 | 982660 | 983079 | chr20 | 1206766 | 1207125 |
| chr20 | 1783674 | 1784453 | chr20 | 2539252 | 2539851 | chr20 | 2668670 | 2669026 |
| chr20 | 2780654 | 2780747 | chr20 | 2780894 | 2781553 | chr20 | 2781657 | 2781836 |

TABLE 14-continued

| chr | start | end | chr | start | end | chr | start | end |
|---|---|---|---|---|---|---|---|---|
| chr20 | 2785561 | 2786160 | chr20 | 3027666 | 3027780 | chr20 | 3052501 | 3052920 |
| chr20 | 3073395 | 3073994 | chr20 | 3204792 | 3205031 | chr20 | 3220799 | 3221038 |
| chr20 | 3229475 | 3229714 | chr20 | 3641656 | 3642015 | chr20 | 3662918 | 3663277 |
| chr20 | 4084983 | 4085146 | chr20 | 4229328 | 4229507 | chr20 | 4229684 | 4230684 |
| chr20 | 4802971 | 4803750 | chr20 | 4803846 | 4804053 | chr20 | 5296095 | 5296986 |
| chr20 | 5297106 | 5297705 | chr20 | 6022813 | 6023052 | chr20 | 6748832 | 6749131 |
| chr20 | 8112304 | 8112483 | chr20 | 8112642 | 8113121 | chr20 | 8113462 | 8113701 |
| chr20 | 9487302 | 9488032 | chr20 | 9488287 | 9488613 | chr20 | 9488650 | 9488934 |
| chr20 | 9488993 | 9489249 | chr20 | 9489377 | 9489796 | chr20 | 9495181 | 9495600 |
| chr20 | 9496253 | 9496912 | chr20 | 9496953 | 9497074 | chr20 | 10198206 | 10198685 |
| chr20 | 10198841 | 10199020 | chr20 | 13200498 | 13200737 | chr20 | 16555037 | 16555130 |
| chr20 | 17206434 | 17206840 | chr20 | 17207783 | 17208022 | chr20 | 17208484 | 17208723 |
| chr20 | 18039741 | 18039980 | chr20 | 19739495 | 19739794 | chr20 | 19928211 | 19928450 |
| chr20 | 20344410 | 20344649 | chr20 | 20345597 | 20346196 | chr20 | 20347358 | 20348257 |
| chr20 | 20348447 | 20348686 | chr20 | 20349055 | 20349354 | chr20 | 20349500 | 20349679 |
| chr20 | 21080615 | 21082354 | chr20 | 21082456 | 21082995 | chr20 | 21083322 | 21084461 |
| chr20 | 21085729 | 21085968 | chr20 | 21086075 | 21086554 | chr20 | 21086808 | 21087267 |
| chr20 | 21372091 | 21372810 | chr20 | 21376172 | 21378631 | chr20 | 21486299 | 21486958 |
| chr20 | 21487068 | 21487276 | chr20 | 21487368 | 21487667 | chr20 | 21488076 | 21488435 |
| chr20 | 21489135 | 21489794 | chr20 | 21490099 | 21491632 | chr20 | 21492292 | 21493071 |
| chr20 | 21493218 | 21494357 | chr20 | 21494438 | 21494797 | chr20 | 21495845 | 21496084 |
| chr20 | 21496158 | 21496397 | chr20 | 21496558 | 21497217 | chr20 | 21497337 | 21498716 |
| chr20 | 21500019 | 21500228 | chr20 | 21501294 | 21501814 | chr20 | 21501945 | 21502424 |
| chr20 | 21502495 | 21503214 | chr20 | 21503490 | 21503877 | chr20 | 21682309 | 21682548 |
| chr20 | 21683213 | 21683751 | chr20 | 21685592 | 21685606 | chr20 | 21686157 | 21686756 |
| chr20 | 21686921 | 21687820 | chr20 | 21689852 | 21690137 | chr20 | 21694425 | 21694604 |
| chr20 | 21695014 | 21695391 | chr20 | 21748349 | 21748588 | chr20 | 22657301 | 22557776 |
| chr20 | 22557898 | 22558197 | chr20 | 22558534 | 22558773 | chr20 | 22559549 | 22559788 |
| chr20 | 22562632 | 22562931 | chr20 | 22563690 | 22563703 | chr20 | 22564161 | 22564291 |
| chr20 | 23015843 | 23015942 | chr20 | 23029012 | 23029251 | chr20 | 23029303 | 23030442 |
| chr20 | 23031471 | 23031729 | chr20 | 24450133 | 24450612 | chr20 | 24450692 | 24451111 |
| chr20 | 24451372 | 24451671 | chr20 | 25058292 | 25058711 | chr20 | 25061654 | 25062973 |
| chr20 | 25063700 | 25064539 | chr20 | 25065078 | 25065497 | chr20 | 25129345 | 25129544 |
| chr20 | 25230415 | 25230513 | chr20 | 25230775 | 25230894 | chr20 | 26188813 | 26189092 |
| chr20 | 26190218 | 26190432 | chr20 | 30101724 | 30101833 | chr20 | 30582655 | 30583074 |
| chr20 | 30539051 | 30539410 | chr20 | 30639531 | 30539570 | chr20 | 30639603 | 30639950 |
| chr20 | 30640009 | 30640368 | chr20 | 30777930 | 30778339 | chr20 | 31115592 | 31115891 |
| chr20 | 31151695 | 31151874 | chr20 | 32301800 | 32302039 | chr20 | 32450399 | 32450518 |
| chr20 | 33547579 | 33547685 | chr20 | 33574834 | 33574981 | chr20 | 34041903 | 34042004 |
| chr20 | 34187928 | 34148347 | chr20 | 34188525 | 34189498 | chr20 | 34189534 | 34190013 |
| chr20 | 36531706 | 36532005 | chr20 | 36781250 | 36781429 | chr20 | 37302601 | 37303440 |
| chr20 | 37351701 | 37352720 | chr20 | 37353096 | 37353335 | chr20 | 37353378 | 37353857 |
| chr20 | 37354045 | 37355304 | chr20 | 37355761 | 37357440 | chr20 | 37357739 | 37358278 |
| chr20 | 37434469 | 37434828 | chr20 | 37435012 | 37435311 | chr20 | 37435362 | 37435961 |
| chr20 | 39316114 | 39316413 | chr20 | 39316814 | 39317473 | chr20 | 39317659 | 39318138 |
| chr20 | 39319031 | 39319750 | chr20 | 39995061 | 39995900 | chr20 | 41817697 | 41818176 |
| chr20 | 41818472 | 418:9011 | chr20 | 42136252 | 42136491 | chr20 | 42218593 | 42218757 |
| chr20 | 42543655 | 42543954 | chr20 | 42543999 | 42545078 | chr20 | 42876457 | 42876670 |
| chr20 | 43437970 | 43438569 | chr20 | 43438883 | 43439122 | chr20 | 43439192 | 43439611 |
| chr20 | 44452628 | 44453152 | chr20 | 44519003 | 44519182 | chr20 | 44601980 | 44602069 |
| chr20 | 44639100 | 44639579 | chr20 | 44640264 | 44640443 | chr20 | 44660665 | 44660964 |
| chr20 | 44686087 | 44686866 | chr20 | 44803096 | 44803755 | chr20 | 44875147 | 44875506 |
| chr20 | 44879700 | 44880179 | chr20 | 44937124 | 44937369 | chr20 | 44937444 | 44937723 |
| chr20 | 44941441 | 44941740 | chr20 | 45141897 | 45142331 | chr20 | 45279779 | 45280491 |
| chr20 | 45337726 | 45338025 | chr20 | 45524449 | 45524628 | chr20 | 47247136 | 47247407 |
| chr20 | 47274032 | 47274137 | chr20 | 47296320 | 47296920 | chr20 | 47443647 | 47444366 |
| chr20 | 47905336 | 47905687 | chr20 | 47934747 | 47935346 | chr20 | 47935412 | 47935651 |
| chr20 | 47935829 | 47936128 | chr20 | 48184289 | 48184528 | chr20 | 49204105 | 49204524 |
| chr20 | 49261715 | 49262194 | chr20 | 49358363 | 49358477 | chr20 | 49377912 | 49378139 |
| chr20 | 49381177 | 49381340 | chr20 | 49575835 | 49575938 | chr20 | 49575988 | 49576014 |
| chr20 | 49639698 | 49640237 | chr20 | 50383399 | 50383504 | chr20 | 50384683 | 50384982 |
| chr20 | 50720356 | 50722021 | chr20 | 50722096 | 50722201 | chr20 | 50722609 | 50722908 |
| chr20 | 51589688 | 51589987 | chr20 | 52311387 | 52311505 | chr20 | 52789371 | 52789550 |
| chr20 | 52789765 | 52790244 | chr20 | 53092165 | 53092464 | chr20 | 53093011 | 53093190 |
| chr20 | 54578407 | 54578826 | chr20 | 54579809 | 54580408 | chr20 | 54580484 | 54580783 |
| chr20 | 55199952 | 55200791 | chr20 | 55200828 | 55201187 | chr20 | 55201399 | 55201638 |
| chr20 | 55201686 | 55202705 | chr20 | 55202728 | 55203207 | chr20 | 55204224 | 55204703 |
| chr20 | 55204864 | 55205103 | chr20 | 55205956 | 55206495 | chr20 | 55499394 | 55499813 |
| chr20 | 55499932 | 55500171 | chr20 | 55500321 | 55501040 | chr20 | 55693446 | 55693610 |
| chr20 | 55841036 | 55841455 | chr20 | 55841994 | 55842293 | chr20 | 56766086 | 56766203 |
| chr20 | 56803301 | 56803540 | chr20 | 56803762 | 56804001 | chr20 | 57089355 | 57089594 |
| chr20 | 57089720 | 57090259 | chr20 | 57224746 | 57225405 | chr20 | 58152557 | 58152796 |
| chr20 | 58179713 | 58179952 | chr20 | 58180018 | 58180497 | chr20 | 58508796 | 58509005 |
| chr20 | 59804233 | 59804323 | chr20 | 59826885 | 59827304 | chr20 | 59827702 | 59828541 |
| chr20 | 59880480 | 59880575 | chr20 | 59910084 | 59910441 | chr20 | 59972951 | 59973170 |
| chr20 | 60202541 | 60202699 | chr20 | 50235251 | 60235610 | chr20 | 60238278 | 60238574 |
| chr20 | 60238780 | 60239079 | chr20 | 60243860 | 60244206 | chr20 | 60329482 | 60329661 |
| chr20 | 60359835 | 60359954 | chr20 | 60374934 | 60375173 | chr20 | 60439546 | 60439845 |

TABLE 14-continued

| chr | start | end | chr | start | end | chr | start | end |
|---|---|---|---|---|---|---|---|---|
| chr20 | 60453829 | 60454186 | chr20 | 60477213 | 60477632 | chr20 | 60485281 | 60485480 |
| chr20 | 60502956 | 60503135 | chr20 | 60620233 | 60620412 | chr20 | 60772886 | 60773905 |
| chr20 | 60789866 | 60790225 | chr20 | 60925945 | 60926124 | chr20 | 60970879 | 60971058 |
| chr20 | 60983756 | 60984115 | chr20 | 60984356 | 60984553 | chr20 | 61287993 | 61288232 |
| chr20 | 61288380 | 61288619 | chr20 | 61294596 | 61294955 | chr20 | 61340486 | 61340785 |
| chr20 | 61412227 | 61412451 | chr20 | 61505882 | 61506421 | chr20 | 61532457 | 61532696 |
| chr20 | 61560341 | 61561000 | chr20 | 61585679 | 61585823 | chr20 | 61585900 | 61586079 |
| chr20 | 61636755 | 61636994 | chr20 | 61637391 | 61638710 | chr20 | 61703613 | 61703972 |
| chr20 | 61714683 | 61714696 | chr20 | 61734332 | 61734571 | chr20 | 61747795 | 61748034 |
| chr20 | 61763524 | 61763703 | chr20 | 61765251 | 61765490 | chr20 | 61808107 | 61808346 |
| chr20 | 61808388 | 61810187 | chr20 | 61823076 | 61823195 | chr20 | 61862297 | 61862460 |
| chr20 | 61885146 | 61885565 | chr20 | 61885609 | 61885848 | chr20 | 61885984 | 61886343 |
| chr20 | 61886651 | 61886830 | chr20 | 61974094 | 61974453 | chr20 | 61980769 | 61981068 |
| chr20 | 62031085 | 62031324 | chr20 | 62031958 | 62032197 | chr20 | 62037460 | 62037699 |
| chr20 | 62046145 | 62046504 | chr20 | 62058624 | 62058859 | chr20 | 62090442 | 62090621 |
| chr20 | 62097763 | 62097771 | chr20 | 62115188 | 62115367 | chr20 | 62119246 | 62120252 |
| chr20 | 62126035 | 62126514 | chr20 | 62157232 | 62157349 | chr20 | 62165548 | 62165847 |
| chr20 | 62167480 | 62167659 | chr20 | 62170105 | 62170284 | chr20 | 62172851 | 62173150 |
| chr20 | 62185296 | 62185535 | chr20 | 62321125 | 62321424 | chr20 | 62321551 | 62321970 |
| chr20 | 62340233 | 62340423 | chr20 | 62383135 | 62383374 | chr20 | 62461263 | 62461562 |
| chr20 | 62488263 | 62488442 | chr20 | 62680682 | 62680818 | chr20 | 62714923 | 62714946 |
| chr20 | 62715097 | 62715162 | chr21 | 22370246 | 22370545 | chr21 | 22370614 | 22370793 |
| chr21 | 26934278 | 26934877 | chr21 | 27011671 | 27011910 | chr21 | 27012283 | 27012622 |
| chr21 | 27944919 | 27945158 | chr21 | 27945324 | 27945503 | chr21 | 27945619 | 27945798 |
| chr21 | 28216509 | 28217768 | chr21 | 28218671 | 28218815 | chr21 | 28218877 | 28219150 |
| chr21 | 28338743 | 28338848 | chr21 | 28339165 | 28339584 | chr21 | 28339806 | 28340405 |
| chr21 | 31015127 | 31015306 | chr21 | 31311330 | 31311769 | chr21 | 31311846 | 31312205 |
| chr21 | 31312230 | 31312259 | chr21 | 31312305 | 31312409 | chr21 | 33244901 | 33245131 |
| chr21 | 33245582 | 33245593 | chr21 | 33245716 | 33245821 | chr21 | 33245921 | 33245955 |
| chr21 | 33246038 | 33246280 | chr21 | 33627450 | 33627569 | chr21 | 33721671 | 33721910 |
| chr21 | 33983153 | 33983320 | chr21 | 34392070 | 34392669 | chr21 | 34395217 | 34396356 |
| chr21 | 34396707 | 34396870 | chr21 | 34396903 | 34397178 | chr21 | 34397993 | 34398712 |
| chr21 | 34398847 | 34400346 | chr21 | 34401110 | 34401469 | chr21 | 34442457 | 34442696 |
| chr21 | 34443004 | 34443363 | chr21 | 34443419 | 34443778 | chr21 | 34443806 | 34444045 |
| chr21 | 34444082 | 34444681 | chr21 | 36041374 | 36041793 | chr21 | 36041903 | 36042322 |
| chr21 | 36042581 | 36042940 | chr21 | 37527854 | 37528033 | chr21 | 37758492 | 37758611 |
| chr21 | 37774963 | 37775238 | chr21 | 38064415 | 38064714 | chr21 | 38064917 | 38065832 |
| chr21 | 38065855 | 38066214 | chr21 | 38067247 | 38067308 | chr21 | 38068092 | 38068384 |
| chr21 | 38068465 | 38068871 | chr21 | 38069125 | 38069298 | chr21 | 38069359 | 38069598 |
| chr21 | 38069725 | 38070144 | chr21 | 38070616 | 38070855 | chr21 | 38071699 | 38071781 |
| chr21 | 38071933 | 38071998 | chr21 | 38072920 | 38073159 | chr21 | 38073221 | 38073940 |
| chr21 | 38076764 | 38077243 | chr21 | 38078332 | 38078571 | chr21 | 38079887 | 38080786 |
| chr21 | 38081112 | 38081296 | chr21 | 38081371 | 38081910 | chr21 | 38081968 | 38082011 |
| chr21 | 38082854 | 38083258 | chr21 | 38092081 | 38092320 | chr21 | 38119809 | 38120408 |
| chr21 | 38638505 | 38638624 | chr21 | 38935395 | 38935601 | chr21 | 39047688 | 39047889 |
| chr21 | 40984719 | 40984898 | chr21 | 43376299 | 43376478 | chr21 | 43786609 | 43786788 |
| chr21 | 43991389 | 43991568 | chr21 | 44283611 | 44283850 | chr21 | 44494814 | 44495233 |
| chr21 | 44837002 | 44837245 | chr21 | 44837296 | 44837301 | chr21 | 44847488 | 44847722 |
| chr21 | 44866508 | 44866807 | chr21 | 45148538 | 45148837 | chr21 | 45195115 | 45196414 |
| chr21 | 45273636 | 45273995 | chr21 | 45508543 | 45508662 | chr21 | 45791006 | 45791184 |
| chr21 | 46036556 | 46036855 | chr21 | 46126009 | 46126267 | chr21 | 46126388 | 46126807 |
| chr21 | 46126948 | 46127187 | chr21 | 46127468 | 46127726 | chr21 | 46128801 | 46129040 |
| chr21 | 46129346 | 46129585 | chr21 | 46257016 | 46257375 | chr21 | 46310341 | 46310580 |
| chr21 | 46318196 | 46318435 | chr21 | 46319069 | 46319548 | chr21 | 46359099 | 46359338 |
| chr21 | 46452278 | 46452637 | chr21 | 46677646 | 46677885 | chr21 | 46825737 | 46825823 |
| chr21 | 46863675 | 46863803 | chr21 | 46925704 | 46925999 | chr21 | 46926363 | 46926662 |
| chr21 | 46935727 | 46936018 | chr21 | 47010168 | 47010522 | chr21 | 47062446 | 47062925 |
| chr21 | 47063451 | 47064050 | chr21 | 47064165 | 47064464 | chr21 | 47404071 | 47404429 |
| chr21 | 47504759 | 47504994 | chr21 | 47518676 | 47518915 | chr21 | 47717485 | 47717541 |
| chr21 | 47717623 | 47717665 | chr21 | 47744183 | 47746482 | chr22 | 17081848 | 17082087 |
| chr22 | 17082492 | 17082671 | chr22 | 17082854 | 17083093 | chr22 | 17083297 | 17083596 |
| chr22 | 17600988 | 17601467 | chr22 | 17602419 | 17602718 | chr22 | 17850359 | 17850718 |
| chr22 | 18009986 | 18010085 | chr22 | 18328049 | 18328348 | chr22 | 19017431 | 19017670 |
| chr22 | 19117490 | 19117669 | chr22 | 19510704 | 19511663 | chr22 | 19511765 | 19512184 |
| chr22 | 19706119 | 19706754 | chr22 | 19742753 | 19743052 | chr22 | 19748561 | 19749040 |
| chr22 | 20792372 | 20792689 | chr22 | 21153919 | 21154084 | chr22 | 21304980 | 21305098 |
| chr22 | 21368513 | 21368692 | chr22 | 21977249 | 21977451 | chr22 | 21982708 | 21983062 |
| chr22 | 22006004 | 22006243 | chr22 | 22058102 | 22058341 | chr22 | 22090520 | 22090819 |
| chr22 | 22862704 | 22863243 | chr22 | 22901011 | 22901550 | chr22 | 23791328 | 23791507 |
| chr22 | 23801388 | 23801567 | chr22 | 24180608 | 24180847 | chr22 | 24560283 | 24560522 |
| chr22 | 24820244 | 24820483 | chr22 | 25678654 | 25679433 | chr22 | 25817025 | 25817264 |
| chr22 | 25817356 | 25817715 | chr22 | 28198468 | 28198601 | chr22 | 28371575 | 28371754 |
| chr22 | 28838105 | 28838396 | chr22 | 28838411 | 28838524 | chr22 | 29091752 | 29091929 |
| chr22 | 29445659 | 29446018 | chr22 | 29876117 | 29876189 | chr22 | 29877142 | 29877381 |
| chr22 | 29977650 | 29977755 | chr22 | 30116824 | 30117240 | chr22 | 30158246 | 30158365 |
| chr22 | 30938434 | 30938673 | chr22 | 31198416 | 31198715 | chr22 | 31218436 | 31218615 |
| chr22 | 31218693 | 31218932 | chr22 | 31481052 | 31481411 | chr22 | 32748862 | 32749041 |
| chr22 | 33197509 | 33197748 | chr22 | 33453802 | 33454452 | chr22 | 35848275 | 35848476 |

TABLE 14-continued

| chr | start | end | chr | start | end | chr | start | end |
|---|---|---|---|---|---|---|---|---|
| chr22 | 36902217 | 36902456 | chr22 | 38199683 | 38199982 | chr22 | 38220568 | 38221287 |
| chr22 | 38476983 | 38477882 | chr22 | 38592953 | 38593132 | chr22 | 38639155 | 38639308 |
| chr22 | 39784390 | 39784599 | chr22 | 39830257 | 39830492 | chr22 | 39853438 | 39853677 |
| chr22 | 39932459 | 39932638 | chr22 | 39954323 | 39954615 | chr22 | 40042536 | 40042835 |
| chr22 | 40075089 | 40075328 | chr22 | 40226368 | 40226487 | chr22 | 41048414 | 41048593 |
| chr22 | 41048654 | 41048951 | chr22 | 41634334 | 41634618 | chr22 | 41636999 | 41637217 |
| chr22 | 41657217 | 41657442 | chr22 | 42095992 | 42096276 | chr22 | 42310005 | 42310304 |
| chr22 | 42311435 | 42311674 | chr22 | 42353530 | 42353992 | chr22 | 42667276 | 42667501 |
| chr22 | 42679636 | 42679935 | chr22 | 43012441 | 43012560 | chr22 | 43012883 | 43012980 |
| chr22 | 43083029 | 43083145 | chr22 | 43434340 | 43434579 | chr22 | 43739987 | 43740226 |
| chr22 | 43808205 | 43808502 | chr22 | 44208422 | 44208523 | chr22 | 44258287 | 44258516 |
| chr22 | 44287554 | 44287793 | chr22 | 44455605 | 44455844 | chr22 | 45088524 | 45088823 |
| chr22 | 45135840 | 45136079 | chr22 | 45277218 | 45277397 | chr22 | 45402991 | 45403230 |
| chr22 | 45404106 | 45404525 | chr22 | 45404909 | 45405148 | chr22 | 45405219 | 45405518 |
| chr22 | 45405545 | 45405803 | chr22 | 45406181 | 45406420 | chr22 | 45593572 | 45593799 |
| chr22 | 45604107 | 45604444 | chr22 | 46262352 | 46263911 | chr22 | 46367955 | 46368134 |
| chr22 | 46438002 | 46438112 | chr22 | 46658700 | 46658939 | chr22 | 46931177 | 46931336 |
| chr22 | 46933014 | 46933104 | chr22 | 47004998 | 47005237 | chr22 | 47023028 | 47023267 |
| chr22 | 47054612 | 47054700 | chr22 | 47193234 | 47193473 | chr22 | 47525747 | 47525986 |
| chr22 | 48027582 | 48027731 | chr22 | 48884957 | 48885136 | chr22 | 48885210 | 48885989 |
| chr22 | 48886575 | 48886934 | chr22 | 48931805 | 48932104 | chr22 | 48971050 | 48971829 |
| chr22 | 48972042 | 48972761 | chr22 | 49852543 | 49852722 | chr22 | 49979553 | 49979835 |
| chr22 | 50001612 | 50001912 | chr22 | 50002684 | 50002911 | chr22 | 50003130 | 50003309 |
| chr22 | 50010037 | 50010336 | chr22 | 50010374 | 50010673 | chr22 | 50031617 | 50031796 |
| chr22 | 50149332 | 50149548 | chr22 | 50466931 | 50467045 | chr22 | 50496761 | 50497000 |
| chr22 | 50497068 | 50497367 | chr22 | 50623595 | 50623894 | chr22 | 50899214 | 50899753 |
| chr22 | 50943082 | 50943358 | chr22 | 51042185 | 51042881 | chr22 | 51112072 | 51112311 |
| chrX | 3746638 | 3746717 | chrX | 6145241 | 6145780 | chrX | 8698761 | 8699000 |
| chrX | 8699416 | 8699655 | chrX | 136656489 | 136656534 | AC211950.2_11234-25326 | 181 | 343 |
| AC211950.2_11234-25326 | 13241 | 13420 | AC211950.2_11234-25326 | 13667 | 13966 | AC241851.2_88-34049 | 15187 | 15426 |
| AEKP01168736.1_1-4752 | 1662 | 1781 | AEKP01168736.1_1-4752 | 1874 | 2381 | JH636052.4 | 5118687 | 5118986 |
| NW_001838016.1_818233-828058 | 6095 | 6142 | — | — | — | — | — | — |

TABLE 15

| chr | start | end | chr | start | end | chr | start | end |
|---|---|---|---|---|---|---|---|---|
| chr1 | 898633 | 898792 | chr1 | 913445 | 914044 | chr1 | 1080495 | 1080914 |
| chr1 | 1146657 | 1146896 | chr1 | 1218688 | 1218779 | chr1 | 1223433 | 1223595 |
| chr1 | 1235811 | 1236156 | chr1 | 1266957 | 1267233 | chr1 | 1267372 | 1267791 |
| chr1 | 1267823 | 1268242 | chr1 | 1341738 | 1341826 | chr1 | 1475458 | 1475644 |
| chr1 | 1476255 | 1476417 | chr1 | 1483096 | 1483139 | chr1 | 1563119 | 1563298 |
| chr1 | 1856362 | 1856471 | chr1 | 1857759 | 1857811 | chr1 | 1874647 | 1874877 |
| chr1 | 1910341 | 1910465 | chr1 | 1935188 | 1935207 | chr1 | 1935232 | 1935289 |
| chr1 | 1935291 | 1935547 | chr1 | 1974768 | 1974802 | chr1 | 2066406 | 2066756 |
| chr1 | 2125141 | 2125560 | chr1 | 2263067 | 2263366 | chr1 | 2267472 | 2267771 |
| chr1 | 2304239 | 2304478 | chr1 | 2307851 | 2307970 | chr1 | 2308023 | 2308030 |
| chr1 | 2308297 | 2308716 | chr1 | 2309792 | 2309994 | chr1 | 2331281 | 2331500 |
| chr1 | 2336323 | 2336440 | chr1 | 2375047 | 2375646 | chr1 | 2396927 | 2397106 |
| chr1 | 2428239 | 2428478 | chr1 | 2472089 | 2472388 | chr1 | 2506974 | 2507150 |
| chr1 | 2520925 | 2521062 | chr1 | 2706308 | 2706335 | chr1 | 2830081 | 2830147 |
| chr1 | 2865964 | 2866143 | chr1 | 2984645 | 2984824 | chr1 | 3102567 | 3102856 |
| chr1 | 3182781 | 3182874 | chr1 | 3182942 | 3183020 | chr1 | 3322011 | 3322250 |
| chr1 | 3567062 | 3567345 | chr1 | 3567738 | 3567851 | chr1 | 3567883 | 3568320 |
| chr1 | 3601749 | 3602030 | chr1 | 3659530 | 3659643 | chr1 | 3659672 | 3659769 |
| chr1 | 3663458 | 3663637 | chr1 | 3663779 | 3664018 | chr1 | 3664606 | 3664781 |
| chr1 | 3683723 | 3683902 | chr1 | 4111087 | 4111323 | chr1 | 4713943 | 4714075 |
| chr1 | 4714164 | 4714362 | chr1 | 4715428 | 4715540 | chr1 | 4715575 | 4716537 |
| chr1 | 4716539 | 4716744 | chr1 | 6166262 | 6166561 | chr1 | 6171668 | 6171907 |
| chr1 | 6186410 | 6186649 | chr1 | 6280169 | 6280348 | chr1 | 6304103 | 6304342 |
| chr1 | 6446041 | 6446400 | chr1 | 6480434 | 6480913 | chr1 | 6500911 | 6500988 |
| chr1 | 6501055 | 6501262 | chr1 | 6507603 | 6508202 | chr1 | 7764540 | 7764775 |
| chr1 | 8277776 | 8277837 | chr1 | 9712017 | 9712179 | chr1 | 9712459 | 9713096 |
| chr1 | 10166481 | 10166626 | chr1 | 10948478 | 10948657 | chr1 | 11538796 | 11538913 |
| chr1 | 11539101 | 11539280 | chr1 | 11539336 | 11539515 | chr1 | 11540040 | 11540179 |
| chr1 | 11591712 | 11591863 | chr1 | 11752375 | 11752614 | chr1 | 11936674 | 11936779 |
| chr1 | 11958996 | 11959295 | chr1 | 12041511 | 12041630 | chr1 | 12123143 | 12123554 |
| chr1 | 12227604 | 12227805 | chr1 | 12251342 | 12252059 | chr1 | 13839669 | 13839769 |
| chr1 | 13910336 | 13910698 | chr1 | 13910700 | 13910757 | chr1 | 13910794 | 13910815 |
| chr1 | 14026401 | 14026700 | chr1 | 14730390 | 14730502 | chr1 | 14925417 | 14926136 |
| chr1 | 15251113 | 15251316 | chr1 | 15480854 | 15480983 | chr1 | 16085267 | 16085288 |

TABLE 15-continued

| chr | start | end | chr | start | end | chr | start | end |
|---|---|---|---|---|---|---|---|---|
| chr1 | 16474984 | 16475299 | chr1 | 16861448 | 16861627 | chr1 | 17445781 | 17446011 |
| chr1 | 18437373 | 18437431 | chr1 | 18437433 | 18437612 | chr1 | 18956114 | 18956353 |
| chr1 | 18956383 | 18956408 | chr1 | 18956496 | 18956611 | chr1 | 18956782 | 18957321 |
| chr1 | 18957428 | 18957667 | chr1 | 18957938 | 18958229 | chr1 | 18958359 | 18958477 |
| chr1 | 18959346 | 18959390 | chr1 | 18959456 | 18959645 | chr1 | 18960795 | 18961094 |
| chr1 | 18962648 | 18963231 | chr1 | 18969543 | 18969902 | chr1 | 18971772 | 18972011 |
| chr1 | 18972056 | 18972170 | chr1 | 19043472 | 19043743 | chr1 | 19043757 | 19043771 |
| chr1 | 19992272 | 19992313 | chr1 | 19992433 | 19992511 | chr1 | 20127444 | 20127555 |
| chr1 | 20618230 | 20618469 | chr1 | 20878953 | 20879029 | chr1 | 20879031 | 20879229 |
| chr1 | 20879256 | 20879372 | chr1 | 20879482 | 20879721 | chr1 | 20879752 | 20880051 |
| chr1 | 20880095 | 20880694 | chr1 | 21026082 | 21026253 | chr1 | 21042820 | 21042999 |
| chr1 | 21044024 | 21044263 | chr1 | 21573736 | 21574215 | chr1 | 21835856 | 21836095 |
| chr1 | 22140674 | 22141014 | chr1 | 22141016 | 22141393 | chr1 | 22927327 | 22927556 |
| chr1 | 23748907 | 23749146 | chr1 | 23884996 | 23885088 | chr1 | 26255921 | 26256029 |
| chr1 | 25256280 | 25256459 | chr1 | 25257157 | 25257305 | chr1 | 25257391 | 25257464 |
| chr1 | 26551597 | 26551625 | chr1 | 26551729 | 26551896 | chr1 | 26551989 | 26552228 |
| chr1 | 26737509 | 26737688 | chr1 | 26737855 | 26737883 | chr1 | 26737908 | 26738274 |
| chr1 | 27190078 | 27190377 | chr1 | 27844444 | 27844623 | chr1 | 29450398 | 29450637 |
| chr1 | 29585984 | 29586763 | chr1 | 29804872 | 29805171 | chr1 | 30351469 | 30351828 |
| chr1 | 30815328 | 30815417 | chr1 | 30815455 | 30815675 | chr1 | 31863112 | 31863130 |
| chr1 | 32180323 | 32180502 | chr1 | 32237507 | 32237546 | chr1 | 32237639 | 32238586 |
| chr1 | 32410202 | 32410364 | chr1 | 32705425 | 32705639 | chr1 | 32756421 | 32756519 |
| chr1 | 32930524 | 32930658 | chr1 | 34628874 | 34629053 | chr1 | 34629390 | 34629809 |
| chr1 | 34630473 | 34630712 | chr1 | 34630770 | 34631069 | chr1 | 34631502 | 34631741 |
| chr1 | 34631872 | 34631892 | chr1 | 34632023 | 34632038 | chr1 | 34642298 | 34642490 |
| chr1 | 35258557 | 35258796 | chr1 | 35350980 | 35351759 | chr1 | 35395450 | 35395541 |
| chr1 | 35395543 | 35395929 | chr1 | 35664721 | 35664836 | chr1 | 36042605 | 36043564 |
| chr1 | 36563382 | 36563621 | chr1 | 37498718 | 37498845 | chr1 | 37498889 | 37499257 |
| chr1 | 37499358 | 37499683 | chr1 | 37500014 | 37500257 | chr1 | 37500368 | 37500441 |
| chr1 | 37500443 | 37500575 | chr1 | 37500603 | 37500907 | chr1 | 37500998 | 37501107 |
| chr1 | 38100591 | 38100787 | chr1 | 38219635 | 38219874 | chr1 | 38229961 | 38230243 |
| chr1 | 38230283 | 38230380 | chr1 | 38230700 | 38230937 | chr1 | 38398356 | 38398431 |
| chr1 | 38510079 | 38510258 | chr1 | 38510475 | 38510714 | chr1 | 38510778 | 38510933 |
| chr1 | 38510935 | 38511197 | chr1 | 38511252 | 38511800 | chr1 | 38511822 | 38511911 |
| chr1 | 38512311 | 38512490 | chr1 | 38513162 | 38513273 | chr1 | 39269662 | 39270201 |
| chr1 | 40137822 | 40138061 | chr1 | 40237053 | 40237281 | chr1 | 40349627 | 40349746 |
| chr1 | 41284058 | 41284541 | chr1 | 41847494 | 41847793 | chr1 | 41848778 | 41848889 |
| chr1 | 41967261 | 41967360 | chr1 | 41991552 | 41991791 | chr1 | 43834653 | 43834807 |
| chr1 | 44068700 | 44068879 | chr1 | 44726821 | 44727360 | chr1 | 44872358 | 44872723 |
| chr1 | 44872924 | 44873064 | chr1 | 44873066 | 44873173 | chr1 | 44873510 | 44873797 |
| chr1 | 44883030 | 44883215 | chr1 | 44883752 | 44884123 | chr1 | 44884204 | 44884289 |
| chr1 | 45308239 | 45308358 | chr1 | 45308655 | 45308729 | chr1 | 46632781 | 46633020 |
| chr1 | 46913761 | 46913877 | chr1 | 46913887 | 46914246 | chr1 | 46914286 | 46914360 |
| chr1 | 46914582 | 46914641 | chr1 | 46932686 | 46932842 | chr1 | 46951114 | 46951318 |
| chr1 | 46951645 | 46951833 | chr1 | 46956380 | 46956616 | chr1 | 46956728 | 46956839 |
| chr1 | 46956841 | 46957246 | chr1 | 47009851 | 47009886 | chr1 | 47009911 | 47010036 |
| chr1 | 47010105 | 47010150 | chr1 | 47695033 | 47695512 | chr1 | 47696207 | 47696521 |
| chr1 | 47696621 | 47696686 | chr1 | 47696727 | 47696965 | chr1 | 47696987 | 47697206 |
| chr1 | 47697254 | 47697255 | chr1 | 47697280 | 47697613 | chr1 | 47697642 | 47697947 |
| chr1 | 47692007 | 47698301 | chr1 | 47881984 | 47882265 | chr1 | 47882267 | 47882403 |
| chr1 | 47882697 | 47882906 | chr1 | 47909640 | 47910239 | chr1 | 47910420 | 47910625 |
| chr1 | 47910749 | 47911019 | chr1 | 47911243 | 47911335 | chr1 | 48058982 | 48059341 |
| chr1 | 49242260 | 49242359 | chr1 | 49242361 | 49242513 | chr1 | 49242515 | 49242619 |
| chr1 | 50513541 | 50513837 | chr1 | 50799190 | 50799317 | chr1 | 50799394 | 50799489 |
| chr1 | 50880932 | 50881317 | chr1 | 50881427 | 50881957 | chr1 | 50882144 | 50882625 |
| chr1 | 50882731 | 50883690 | chr1 | 50883800 | 50883977 | chr1 | 50884021 | 50884353 |
| chr1 | 50884691 | 50884888 | chr1 | 50885262 | 50885441 | chr1 | 50886107 | 50887085 |
| chr1 | 50887176 | 50887366 | chr1 | 50888619 | 50888796 | chr1 | 50889124 | 50889607 |
| chr1 | 50889741 | 50890460 | chr1 | 50890600 | 50890649 | chr1 | 50890796 | 50891565 |
| chr1 | 50892073 | 50892284 | chr1 | 50892337 | 50892432 | chr1 | 50892523 | 50893149 |
| chr1 | 50893151 | 50893423 | chr1 | 50893519 | 50893962 | chr1 | 51763181 | 51763395 |
| chr1 | 52832605 | 52832712 | chr1 | 53068087 | 53068181 | chr1 | 53068183 | 53068626 |
| chr1 | 53098746 | 53099053 | chr1 | 53099055 | 53099165 | chr1 | 53308489 | 53308608 |
| chr1 | 53308908 | 53309328 | chr1 | 53528288 | 53528527 | chr1 | 53705675 | 53705794 |
| chr1 | 54203419 | 54203422 | chr1 | 54203829 | 54204498 | chr1 | 54586532 | 54586831 |
| chr1 | 55462599 | 55462778 | chr1 | 57888293 | 57888472 | chr1 | 57888888 | 57889035 |
| chr1 | 57889037 | 57889187 | chr1 | 57889319 | 57889604 | chr1 | 57889606 | 57889738 |
| chr1 | 57890332 | 57890671 | chr1 | 58715055 | 58715294 | chr1 | 58715375 | 58715532 |
| chr1 | 58715534 | 58715855 | chr1 | 58715979 | 58716094 | chr1 | 61519265 | 61519405 |
| chr1 | 61519473 | 61519497 | chr1 | 62793169 | 62793342 | chr1 | 63539429 | 63539968 |
| chr1 | 63785232 | 63785293 | chr1 | 63785619 | 63785767 | chr1 | 63786079 | 63786431 |
| chr1 | 63786928 | 63787167 | chr1 | 63787226 | 63787249 | chr1 | 63787283 | 63787645 |
| chr1 | 63788341 | 63788640 | chr1 | 63788694 | 63788767 | chr1 | 63788920 | 63789497 |
| chr1 | 63789729 | 63789792 | chr1 | 63789850 | 63789913 | chr1 | 63790253 | 63790373 |
| chr1 | 63792458 | 63792649 | chr1 | 63792798 | 63793171 | chr1 | 63795265 | 63795934 |
| chr1 | 63795936 | 63796370 | chr1 | 63796418 | 63796584 | chr1 | 64240031 | 64240222 |
| chr1 | 64240533 | 64240765 | chr1 | 64734554 | 64734669 | chr1 | 64937227 | 64937401 |
| chr1 | 65731243 | 65731505 | chr1 | 65731782 | 65731851 | chr1 | 65990876 | 65991019 |

TABLE 15-continued

| chr | start | end | chr | start | end | chr | start | end |
|---|---|---|---|---|---|---|---|---|
| chr1 | 65991344 | 65991561 | chr1 | 65991606 | 65991758 | chr1 | 65991784 | 65991883 |
| chr1 | 66258088 | 66258651 | chr1 | 66258672 | 66258760 | chr1 | 66258762 | 66258867 |
| chr1 | 66259037 | 66259276 | chr1 | 66998702 | 66999412 | chr1 | 66999536 | 66999772 |
| chr1 | 67217965 | 67218424 | chr1 | 67390243 | 67390542 | chr1 | 67390993 | 67391172 |
| chr1 | 67773081 | 67773860 | chr1 | 70033524 | 70033709 | chr1 | 70033829 | 70034003 |
| chr1 | 70034368 | 70034491 | chr1 | 70034493 | 70034667 | chr1 | 70035014 | 70035208 |
| chr1 | 70035210 | 70035526 | chr1 | 70599152 | 70599260 | chr1 | 70672859 | 70672978 |
| chr1 | 72749635 | 72749700 | chr1 | 72749732 | 72749798 | chr1 | 75595702 | 75595759 |
| chr1 | 75595819 | 75595991 | chr1 | 75596136 | 75596479 | chr1 | 75596597 | 75596859 |
| chr1 | 75596930 | 75597668 | chr1 | 75597842 | 75598261 | chr1 | 75598310 | 75598489 |
| chr1 | 75599345 | 75599704 | chr1 | 75600148 | 75600685 | chr1 | 75600687 | 75601119 |
| chr1 | 75601188 | 75601276 | chr1 | 75601278 | 75601513 | chr1 | 75601889 | 75603148 |
| chr1 | 76080387 | 76080727 | chr1 | 76080729 | 76080866 | chr1 | 76082050 | 76082289 |
| chr1 | 76354731 | 76354839 | chr1 | 76540398 | 76540574 | chr1 | 76540576 | 76540757 |
| chr1 | 77332984 | 77333159 | chr1 | 77333161 | 77333163 | chr1 | 77333285 | 77333434 |
| chr1 | 77333580 | 77333625 | chr1 | 77334169 | 77334386 | chr1 | 27334409 | 77334757 |
| chr1 | 77334796 | 77334846 | chr1 | 77747291 | 77747382 | chr1 | 77747384 | 77747530 |
| chr1 | 77747848 | 77748327 | chr1 | 78511371 | 78511856 | chr1 | 78511858 | 78512450 |
| chr1 | 78967198 | 78957617 | chr1 | 82268586 | 82268904 | chr1 | 84944531 | 84944650 |
| chr1 | 85358543 | 85358593 | chr1 | 85358752 | 85358902 | chr1 | 85463275 | 85463454 |
| chr1 | 86621565 | 86622024 | chr1 | 86622112 | 86622113 | chr1 | 86622115 | 86622224 |
| chr1 | 86622430 | 86622552 | chr1 | 86622813 | 86622831 | chr1 | 86860815 | 86861049 |
| chr1 | 87617672 | 876:7911 | chr1 | 90309344 | 90309571 | chr1 | 91171926 | 91172765 |
| chr1 | 91177865 | 91178284 | chr1 | 91179982 | 91180401 | chr1 | 91181853 | 91182212 |
| chr1 | 91182246 | 91182969 | chr1 | 91183001 | 91183196 | chr1 | 91183251 | 91183519 |
| chr1 | 91183521 | 91183611 | chr1 | 91183776 | 91183805 | chr1 | 91183850 | 91184080 |
| chr1 | 91184339 | 91184413 | chr1 | 91184415 | 91184758 | chr1 | 91185126 | 91185309 |
| chr1 | 91185348 | 91185809 | chr1 | 91188891 | 91189483 | chr1 | 91189585 | 91190484 |
| chr1 | 91190791 | 91190949 | chr1 | 91190985 | 91191001 | chr1 | 91191003 | 91191235 |
| chr1 | 91191290 | 91191390 | chr1 | 91192174 | 91192577 | chr1 | 91192682 | 91192773 |
| chr1 | 91194446 | 91194672 | chr1 | 91195015 | 91195494 | chr1 | 91195802 | 91196195 |
| chr1 | 91196226 | 91196581 | chr1 | 91316168 | 91316407 | chr1 | 91316536 | 91316775 |
| chr1 | 91869914 | 91870093 | chr1 | 92948236 | 92948701 | chr1 | 92948760 | 92949059 |
| chr1 | 92952071 | 92952632 | chr1 | 94343486 | 94343596 | chr1 | 97185167 | 97185357 |
| chr1 | 98510704 | 98511031 | chr1 | 98511033 | 98511423 | chr1 | 98511536 | 98512015 |
| chr1 | 98514151 | 98514330 | chr1 | 98515048 | 98515087 | chr1 | 98515089 | 98515408 |
| chr1 | 98518930 | 98519661 | chr1 | 98519663 | 98519769 | chr1 | 99469586 | 99469697 |
| chr1 | 99469760 | 99469885 | chr1 | 99470049 | 99470062 | chr1 | 99470212 | 99470288 |
| chr1 | 99470697 | 99470924 | chr1 | 100437184 | 100437270 | chr1 | 101004358 | 101004817 |
| chr1 | 101004989 | 101005228 | chr1 | 101005279 | 101005758 | chr1 | 101702411 | 101702602 |
| chr1 | 101702604 | 101702710 | chr1 | 101703538 | 101703717 | chr1 | 107682647 | 107683066 |
| chr1 | 107683359 | 107683598 | chr1 | 107684161 | 107684520 | chr1 | 108506989 | 108507077 |
| chr1 | 108507149 | 108507168 | chr1 | 108507230 | 108507376 | chr1 | 108507495 | 108507589 |
| chr1 | 108507658 | 108507914 | chr1 | 108507957 | 108508207 | chr1 | 108508209 | 108508548 |
| chr1 | 108508550 | 108508671 | chr1 | 109203582 | 109203761 | chr1 | 109585369 | 109585472 |
| chr1 | 109631647 | 109631766 | chr1 | 109644252 | 109644413 | chr1 | 110610483 | 110610898 |
| chr1 | 110611046 | 110611277 | chr1 | 110611435 | 110611514 | chr1 | 110611654 | 110611794 |
| chr1 | 110626791 | 110627671 | chr1 | 110672792 | 110673082 | chr1 | 110673084 | 110673331 |
| chr1 | 110692886 | 110693497 | chr1 | 110693737 | 110694205 | chr1 | 110754040 | 110754202 |
| chr1 | 110754211 | 110754357 | chr1 | 110754872 | 110754930 | chr1 | 110883455 | 110884054 |
| chr1 | 111097832 | 111098011 | chr1 | 111098107 | 111098406 | chr1 | 111216684 | 111216973 |
| chr1 | 111217195 | 111217575 | chr1 | 111217577 | 111217712 | chr1 | 111217714 | 111217892 |
| chr1 | 111217924 | 111218063 | chr1 | 111505931 | 111506290 | chr1 | 111813448 | 111813687 |
| chr1 | 112084880 | 112085059 | chr1 | 114448981 | 114449087 | chr1 | 114695362 | 114695695 |
| chr1 | 114695697 | 114695737 | chr1 | 114695800 | 114696021 | chr1 | 114696132 | 114696183 |
| chr1 | 114696350 | 114696464 | chr1 | 114696541 | 114696791 | chr1 | 115256441 | 115256620 |
| chr1 | 115258659 | 115258838 | chr1 | 115631842 | 115632011 | chr1 | 115632393 | 115632632 |
| chr1 | 115880081 | 115880207 | chr1 | 115880209 | 115880500 | chr1 | 115880765 | 115880795 |
| chr1 | 115880873 | 115881043 | chr1 | 115881249 | 115881304 | chr1 | 116214002 | 116214132 |
| chr1 | 116214207 | 116214421 | chr1 | 116371051 | 116371187 | chr1 | 116371189 | 116371290 |
| chr1 | 116380550 | 116381389 | chr1 | 116382294 | 116382583 | chr1 | 119521979 | 119522121 |
| chr1 | 119522200 | 119522435 | chr1 | 119522566 | 119522632 | chr1 | 119522741 | 119522854 |
| chr1 | 119522926 | 119523039 | chr1 | 119527237 | 119527472 | chr1 | 119527549 | 119527728 |
| chr1 | 119528557 | 119529216 | chr1 | 119529703 | 119529912 | chr1 | 119530024 | 119530149 |
| chr1 | 119530202 | 119530508 | chr1 | 119530554 | 119630600 | chr1 | 119530602 | 119530743 |
| chr1 | 119630944 | 119531243 | chr1 | 119531943 | 119531997 | chr1 | 119536058 | 119536457 |
| chr1 | 119542905 | 119542994 | chr1 | 119543070 | 119543215 | chr1 | 119543274 | 119543324 |
| chr1 | 119543438 | 119544277 | chr1 | 119548749 | 119548928 | chr1 | 119548955 | 119549017 |
| chr1 | 119549032 | 119549735 | chr1 | 119549915 | 119550034 | chr1 | 119550068 | 119550367 |
| chr1 | 119550434 | 119550721 | chr1 | 119551014 | 119551357 | chr1 | 150603035 | 150603141 |
| chr1 | 151169649 | 151169757 | chr1 | 151170069 | 151170297 | chr1 | 151300814 | 151300933 |
| chr1 | 151693849 | 151694448 | chr1 | 152085302 | 152085601 | chr1 | 152488055 | 152488294 |
| chr1 | 153539382 | 153539681 | chr1 | 153540006 | 153540245 | chr1 | 153651873 | 153652472 |
| chr1 | 153937048 | 153937167 | chr1 | 154298254 | 154298562 | chr1 | 154475372 | 154475612 |
| chr1 | 154516709 | 154516926 | chr1 | 155043313 | 155043734 | chr1 | 155578918 | 155579008 |
| chr1 | 155826303 | 155826412 | chr1 | 155954190 | 155954391 | chr1 | 156010529 | 156010643 |
| chr1 | 156215255 | 156215434 | chr1 | 156215527 | 156215886 | chr1 | 156357892 | 156358611 |
| chr1 | 156390058 | 156390777 | chr1 | 156405635 | 156406071 | chr1 | 156406105 | 156406515 |

TABLE 15-continued

| chr | start | end | chr | start | end | chr | start | end |
|---|---|---|---|---|---|---|---|---|
| chr1 | 156432076 | 156432315 | chr1 | 156594879 | 156595053 | chr1 | 156595081 | 156595118 |
| chr1 | 156611795 | 156611944 | chr1 | 156611994 | 156612214 | chr1 | 156626505 | 156626744 |
| chr1 | 156626814 | 156627019 | chr1 | 156627084 | 156627113 | chr1 | 156646516 | 156646597 |
| chr1 | 156646635 | 156646740 | chr1 | 156814831 | 156814953 | chr1 | 156815031 | 156815240 |
| chr1 | 156815356 | 156815835 | chr1 | 156830190 | 156830192 | chr1 | 156830266 | 156830429 |
| chr1 | 156838078 | 156838424 | chr1 | 156863062 | 156863429 | chr1 | 156863641 | 156863808 |
| chr1 | 157247369 | 157247487 | chr1 | 157458816 | 157458935 | chr1 | 167895339 | 157895518 |
| chr1 | 158669614 | 158669973 | chr1 | 158687334 | 158687633 | chr1 | 159158251 | 159158369 |
| chr1 | 159158472 | 159158588 | chr1 | 159187205 | 159187390 | chr1 | 160693839 | 160693957 |
| chr1 | 160992253 | 160992363 | chr1 | 161007615 | 161007847 | chr1 | 161228566 | 161228971 |
| chr1 | 161275466 | 161275579 | chr1 | 161275640 | 161276125 | chr1 | 161442367 | 161442546 |
| chr1 | 161471751 | 161471868 | chr1 | 161591390 | 161591444 | chr1 | 161591549 | 161591629 |
| chr1 | 162792211 | 162792630 | chr1 | 164290533 | 164290672 | chr1 | 164290724 | 164290772 |
| chr1 | 165086889 | 165087114 | chr1 | 165204994 | 165205233 | chr1 | 165321651 | 165321782 |
| chr1 | 165321943 | 165321950 | chr1 | 165324104 | 165324758 | chr1 | 165325016 | 165325357 |
| chr1 | 165325395 | 165325615 | chr1 | 165325804 | 165326043 | chr1 | 165326128 | 165326205 |
| chr1 | 165326297 | 165326547 | chr1 | 165414124 | 165414352 | chr1 | 166134158 | 166134282 |
| chr1 | 166134284 | 166134397 | chr1 | 166134643 | 166134882 | chr1 | 166135118 | 166135357 |
| chr1 | 166853551 | 166853578 | chr1 | 166853580 | 166853636 | chr1 | 166916774 | 166916921 |
| chr1 | 166916937 | 166916950 | chr1 | 166917125 | 166917193 | chr1 | 167599076 | 167599435 |
| chr1 | 167599521 | 167599940 | chr1 | 167823371 | 167823524 | chr1 | 169396291 | 169396635 |
| chr1 | 169396637 | 169396689 | chr1 | 169396731 | 169397010 | chr1 | 170629466 | 170629513 |
| chr1 | 170630364 | 170630602 | chr1 | 170630604 | 170630903 | chr1 | 170631005 | 170631244 |
| chr1 | 170631399 | 170631638 | chr1 | 170633533 | 170633712 | chr1 | 170637582 | 170637881 |
| chr1 | 170640425 | 170640625 | chr1 | 170640665 | 170640784 | chr1 | 171625443 | 171625543 |
| chr1 | 171810113 | 171811066 | chr1 | 173638567 | 173639153 | chr1 | 175346411 | 175346646 |
| chr1 | 175388563 | 175388682 | chr1 | 177133690 | 177133918 | chr1 | 177140021 | 177140145 |
| chr1 | 177140147 | 177140174 | chr1 | 177140305 | 177140790 | chr1 | 177150699 | 177150878 |
| chr1 | 179544884 | 179545091 | chr1 | 179545093 | 179545183 | chr1 | 179712063 | 179712339 |
| chr1 | 179712411 | 179712554 | chr1 | 179712568 | 179712591 | chr1 | 179712593 | 179712734 |
| chr1 | 179712831 | 179713175 | chr1 | 180197986 | 180198285 | chr1 | 180202331 | 180202395 |
| chr1 | 180202649 | 180203110 | chr1 | 180203355 | 180203608 | chr1 | 180203634 | 180204221 |
| chr1 | 180204223 | 180204620 | chr1 | 180204898 | 180205009 | chr1 | 180235656 | 180235835 |
| chr1 | 180882487 | 180882518 | chr1 | 180925188 | 180925289 | chr1 | 180925330 | 180925487 |
| chr1 | 181287599 | 181287838 | chr1 | 181287922 | 181288281 | chr1 | 181451315 | 181452214 |
| chr1 | 181452770 | 181452986 | chr1 | 181453051 | 181453069 | chr1 | 181454774 | 181455013 |
| chr1 | 181455104 | 181455343 | chr1 | 182584084 | 182584340 | chr1 | 182584404 | 182584623 |
| chr1 | 182807488 | 182807607 | chr1 | 183129301 | 183129530 | chr1 | 183386070 | 183386319 |
| chr1 | 183386599 | 183386713 | chr1 | 183386752 | 183386827 | chr1 | 183386947 | 183387051 |
| chr1 | 183387174 | 183387413 | chr1 | 183462984 | 183463103 | chr1 | 183774155 | 183774454 |
| chr1 | 184005609 | 184005908 | chr1 | 185073803 | 185074028 | chr1 | 190444781 | 190444892 |
| chr1 | 190445080 | 190445197 | chr1 | 190445199 | 190445379 | chr1 | 190447297 | 190447300 |
| chr1 | 190447389 | 190447596 | chr1 | 195732240 | 195732521 | chr1 | 196577628 | 196577953 |
| chr1 | 196578007 | 196578246 | chr1 | 197879307 | 197879546 | chr1 | 197879607 | 197879661 |
| chr1 | 197879717 | 197880258 | chr1 | 197882052 | 197882291 | chr1 | 197882353 | 197882581 |
| chr1 | 197886978 | 197887067 | chr1 | 197887147 | 197887457 | chr1 | 197887707 | 197887817 |
| chr1 | 197887977 | 197888122 | chr1 | 197888181 | 197888396 | chr1 | 197888546 | 197889385 |
| chr1 | 200009312 | 200009551 | chr1 | 200009665 | 200010202 | chr1 | 200011236 | 200011684 |
| chr1 | 200011686 | 200012191 | chr1 | 201368752 | 201368805 | chr1 | 201983038 | 201983277 |
| chr1 | 202081790 | 202081886 | chr1 | 202183343 | 202183476 | chr1 | 202679128 | 202679607 |
| chr1 | 203298210 | 203298441 | chr1 | 203429530 | 203429649 | chr1 | 204333520 | 204333660 |
| chr1 | 204653475 | 204653596 | chr1 | 204653793 | 204653894 | chr1 | 206312504 | 205312912 |
| chr1 | 205312962 | 205313043 | chr1 | 205424577 | 205425045 | chr1 | 205537569 | 205537587 |
| chr1 | 207200767 | 207201066 | chr1 | 207669419 | 207669788 | chr1 | 207669829 | 207670138 |
| chr1 | 207818295 | 207818397 | chr1 | 208084210 | 208084569 | chr1 | 209381030 | 209381269 |
| chr1 | 210111072 | 210111211 | chr1 | 210111285 | 210111422 | chr1 | 210111797 | 210111923 |
| chr1 | 210112037 | 210112244 | chr1 | 211847683 | 211847862 | chr1 | 212963808 | 212963979 |
| chr1 | 213123776 | 213124075 | chr1 | 213124573 | 213124623 | chr1 | 213124669 | 213124992 |
| chr1 | 214156395 | 214157004 | chr1 | 214158753 | 214158911 | chr1 | 214159037 | 214159052 |
| chr1 | 214160028 | 214160262 | chr1 | 214360583 | 214360753 | chr1 | 214360755 | 214360859 |
| chr1 | 214360927 | 214361062 | chr1 | 214724457 | 214724588 | chr1 | 215254998 | 215255897 |
| chr1 | 216897142 | 216897321 | chr1 | 217307385 | 217308360 | chr1 | 217308907 | 217309206 |
| chr1 | 217309671 | 217309910 | chr1 | 217311163 | 217311942 | chr1 | 217312946 | 217313043 |
| chr1 | 217313069 | 217313827 | chr1 | 217805068 | 217805236 | chr1 | 218520021 | 218520063 |
| chr1 | 218520096 | 218520292 | chr1 | 218520310 | 218520477 | chr1 | 218520701 | 218520740 |
| chr1 | 219347112 | 219347134 | chr1 | 219347314 | 219347553 | chr1 | 220101056 | 220101211 |
| chr1 | 220101371 | 220101475 | chr1 | 220101609 | 220101613 | chr1 | 220101675 | 220101788 |
| chr1 | 220636429 | 220636548 | chr1 | 220700737 | 220700976 | chr1 | 221051936 | 221052595 |
| chr1 | 221053527 | 221053946 | chr1 | 221067418 | 221067777 | chr1 | 223302739 | 223302935 |
| chr1 | 223538254 | 223538670 | chr1 | 223936546 | 223936753 | chr1 | 223936996 | 223937145 |
| chr1 | 224400388 | 224400627 | chr1 | 224528740 | 224628919 | chr1 | 224803668 | 224803854 |
| chr1 | 224803995 | 224804296 | chr1 | 224804396 | 224804687 | chr1 | 224804847 | 224804991 |
| chr1 | 224805051 | 224805116 | chr1 | 224805198 | 224805752 | chr1 | 224805849 | 224805890 |
| chr1 | 226411169 | 226411224 | chr1 | 226411247 | 226411348 | chr1 | 226411617 | 226411916 |
| chr1 | 226924982 | 226925281 | chr1 | 227729830 | 227730168 | chr1 | 228194340 | 228194411 |
| chr1 | 228194571 | 228194579 | chr1 | 228195294 | 228196433 | chr1 | 228201147 | 228201326 |
| chr1 | 228247924 | 228247961 | chr1 | 228248228 | 228248407 | chr1 | 228463210 | 228463809 |
| chr1 | 228528749 | 228529108 | chr1 | 228558623 | 228559329 | chr1 | 228566548 | 228566618 |

TABLE 15-continued

| chr | start | end | chr | start | end | chr | start | end |
|---|---|---|---|---|---|---|---|---|
| chr1 | 228566637 | 228566767 | chr1 | 228604124 | 228604348 | chr1 | 228633887 | 228633920 |
| chr1 | 228633922 | 228633950 | chr1 | 228633984 | 228634354 | chr1 | 228645048 | 228645244 |
| chr1 | 228645306 | 228645827 | chr1 | 228646196 | 228646315 | chr1 | 228651350 | 228651709 |
| chr1 | 228651805 | 228651902 | chr1 | 228652243 | 228652453 | chr1 | 228652509 | 228652704 |
| chr1 | 229542750 | 229542953 | chr1 | 229543221 | 229543229 | chr1 | 229543459 | 229543612 |
| chr1 | 229566670 | 229566942 | chr1 | 229567012 | 229567277 | chr1 | 229567370 | 229567993 |
| chr1 | 229568158 | 229568289 | chr1 | 229569712 | 229569951 | chr1 | 230404150 | 230404360 |
| chr1 | 230561683 | 230561922 | chr1 | 231297013 | 231297103 | chr1 | 231297105 | 231297312 |
| chr1 | 231298505 | 231298651 | chr1 | 231298653 | 231298708 | chr1 | 232765226 | 232765398 |
| chr1 | 233750126 | 233750402 | chr1 | 234040224 | 234040403 | chr1 | 234040886 | 234040974 |
| chr1 | 234041303 | 234041361 | chr1 | 234041416 | 234041659 | chr1 | 234349895 | 234350051 |
| chr1 | 234350053 | 234350194 | chr1 | 234445299 | 234445478 | chr1 | 234620955 | 234621073 |
| chr1 | 234844947 | 234845167 | chr1 | 235813693 | 235813797 | chr1 | 235814010 | 235814292 |
| chr1 | 236227538 | 236227744 | chr1 | 236227770 | 236227921 | chr1 | 236228022 | 236228197 |
| chr1 | 236228507 | 236228624 | chr1 | 236228706 | 236228866 | chr1 | 236559075 | 236559207 |
| chr1 | 236559257 | 236559374 | chr1 | 236849381 | 236849506 | chr1 | 236850198 | 236850220 |
| chr1 | 237205085 | 237205098 | chr1 | 237205157 | 237205174 | chr1 | 237205176 | 237205224 |
| chr1 | 237206102 | 237206266 | chr1 | 237206512 | 237206811 | chr1 | 239550505 | 239551284 |
| chr1 | 240118762 | 240119061 | chr1 | 240160997 | 240161086 | chr1 | 240161123 | 240161381 |
| chr1 | 240161547 | 240161571 | chr1 | 240254859 | 240255098 | chr1 | 240255282 | 240255486 |
| chr1 | 240255488 | 240255581 | chr1 | 240255739 | 240256159 | chr1 | 240256625 | 240256872 |
| chr1 | 240775379 | 240775530 | chr1 | 241052047 | 241052201 | chr1 | 241520202 | 241520441 |
| chr1 | 241520509 | 241520632 | chr1 | 241520685 | 241520688 | chr1 | 241587013 | 241587194 |
| chr1 | 241587513 | 241587609 | chr1 | 241587611 | 241587872 | chr1 | 242686642 | 242687781 |
| chr1 | 242688103 | 242688244 | chr1 | 242688278 | 242688342 | chr1 | 242688377 | 242688773 |
| chr1 | 243646523 | 243646762 | chr1 | 244014160 | 244014479 | chr1 | 244080598 | 244080777 |
| chr1 | 244080670 | 244080883 | chr1 | 244893136 | 244893255 | chr1 | 245135670 | 245135849 |
| chr1 | 245494418 | 245494631 | chr1 | 246330402 | 246330509 | chr1 | 246488077 | 246488316 |
| chr1 | 248002191 | 248002310 | chr1 | 248020405 | 248020449 | chr1 | 248020516 | 248020631 |
| chr1 | 248020957 | 248021424 | chr1 | 248027930 | 248028289 | chr1 | 248074658 | 248074768 |
| chr1 | 248074838 | 248075008 | chr1 | 248099661 | 248099900 | chr1 | 248328674 | 248328921 |
| chr1 | 249121623 | 249121738 | chr2 | 287492 | 287731 | chr2 | 288318 | 288557 |
| chr2 | 468116 | 468182 | chr2 | 468217 | 468234 | chr2 | 468424 | 468756 |
| chr2 | 496125 | 496465 | chr2 | 720748 | 720985 | chr2 | 875887 | 876066 |
| chr2 | 945838 | 946010 | chr2 | 946012 | 946077 | chr2 | 946117 | 946218 |
| chr2 | 946290 | 946356 | chr2 | 946449 | 946567 | chr2 | 946917 | 947044 |
| chr2 | 947127 | 947238 | chr2 | 1653023 | 1653262 | chr2 | 1746523 | 1747033 |
| chr2 | 1747591 | 1748008 | chr2 | 1748397 | 1748906 | chr2 | 2844645 | 2844676 |
| chr2 | 2844802 | 2844825 | chr2 | 5831102 | 5831205 | chr2 | 5831238 | 5831401 |
| chr2 | 5831715 | 5831894 | chr2 | 5831967 | 5832048 | chr2 | 5832284 | 5832326 |
| chr2 | 5832800 | 5832847 | chr2 | 5833283 | 5833433 | chr2 | 5833500 | 5833640 |
| chr2 | 5833735 | 5834119 | chr2 | 5835990 | 5836349 | chr2 | 5836451 | 5836575 |
| chr2 | 5836622 | 5836745 | chr2 | 5836828 | 5836992 | chr2 | 5837353 | 5837468 |
| chr2 | 5866006 | 5866305 | chr2 | 7164389 | 7164704 | chr2 | 7571420 | 7571477 |
| chr2 | 7571577 | 7571828 | chr2 | 9134330 | 9134569 | chr2 | 9960660 | 9960839 |
| chr2 | 10115632 | 10115739 | chr2 | 10153063 | 10153168 | chr2 | 10153229 | 10153422 |
| chr2 | 10154909 | 10155024 | chr2 | 10155269 | 10155384 | chr2 | 10156334 | 10156493 |
| chr2 | 10182747 | 10182986 | chr2 | 10408310 | 10408347 | chr2 | 10688800 | 10688931 |
| chr2 | 11052419 | 11052658 | chr2 | 11809858 | 11810116 | chr2 | 11810147 | 11810217 |
| chr2 | 12246027 | 12246196 | chr2 | 12858356 | 12858715 | chr2 | 14772673 | 14772888 |
| chr2 | 14774475 | 14774664 | chr2 | 17719601 | 17719900 | chr2 | 18058941 | 18059180 |
| chr2 | 18059692 | 18059931 | chr2 | 19550140 | 19550319 | chr2 | 19551225 | 19551449 |
| chr2 | 19556245 | 19556765 | chr2 | 19556994 | 19557173 | chr2 | 19558744 | 19558983 |
| chr2 | 19561045 | 19561404 | chr2 | 19561422 | 19561473 | chr2 | 19561524 | 19561781 |
| chr2 | 19563227 | 19563516 | chr2 | 20068723 | 20068962 | chr2 | 20442485 | 20442586 |
| chr2 | 20642626 | 20642745 | chr2 | 20865560 | 20865847 | chr2 | 20865849 | 20866022 |
| chr2 | 25391060 | 25391313 | chr2 | 25391586 | 25391825 | chr2 | 25438724 | 25438872 |
| chr2 | 25439139 | 25439356 | chr2 | 26372893 | 26373072 | chr2 | 26395353 | 26395458 |
| chr2 | 26396460 | 26395652 | chr2 | 26401956 | 26402135 | chr2 | 26407744 | 26407922 |
| chr2 | 26521960 | 26522079 | chr2 | 26915682 | 26916067 | chr2 | 26916089 | 26916341 |
| chr2 | 27070250 | 27070489 | chr2 | 27071144 | 27071443 | chr2 | 27072394 | 27072633 |
| chr2 | 27072727 | 27073086 | chr2 | 27578410 | 27578500 | chr2 | 27887451 | 27887630 |
| chr2 | 29033261 | 29033698 | chr2 | 29337988 | 29338052 | chr2 | 29338159 | 29338748 |
| chr2 | 29338810 | 29339067 | chr2 | 30143219 | 30143323 | chr2 | 30143383 | 30143578 |
| chr2 | 30143957 | 30144151 | chr2 | 30144175 | 30144496 | chr2 | 30453619 | 30453654 |
| chr2 | 30453785 | 30454038 | chr2 | 31360210 | 31360590 | chr2 | 31360631 | 31360693 |
| chr2 | 31360695 | 31360756 | chr2 | 31360804 | 31360929 | chr2 | 31361015 | 31361118 |
| chr2 | 31361194 | 31361194 | chr2 | 31361282 | 31361461 | chr2 | 31456606 | 31457131 |
| chr2 | 32504335 | 32504449 | chr2 | 38302176 | 38302188 | chr2 | 38302370 | 38302901 |
| chr2 | 38302949 | 38302955 | chr2 | 38365728 | 38365847 | chr2 | 39187141 | 39187238 |
| chr2 | 39187545 | 39187800 | chr2 | 39892997 | 39893596 | chr2 | 39893897 | 39894136 |
| chr2 | 40678513 | 40678872 | chr2 | 40678945 | 40679086 | chr2 | 40679088 | 40679519 |
| chr2 | 40679521 | 40679605 | chr2 | 40679689 | 40679712 | chr2 | 42274495 | 42274734 |
| chr2 | 42329340 | 42329445 | chr2 | 42329494 | 42329759 | chr2 | 42720185 | 42720447 |
| chr2 | 43019525 | 43019944 | chr2 | 43451819 | 43451846 | chr2 | 43451892 | 43452418 |
| chr2 | 43824034 | 43824132 | chr2 | 44497613 | 44497842 | chr2 | 45028911 | 45029059 |
| chr2 | 45029184 | 45029450 | chr2 | 45029537 | 45029779 | chr2 | 45155039 | 45155211 |
| chr2 | 45155356 | 45155991 | chr2 | 45155993 | 45156812 | chr2 | 45156833 | 45157783 |

TABLE 15-continued

| chr | start | end | chr | start | end | chr | start | end |
|---|---|---|---|---|---|---|---|---|
| chr2 | 45159873 | 45160352 | chr2 | 45160496 | 45160735 | chr2 | 45161598 | 45162036 |
| chr2 | 45162038 | 45162188 | chr2 | 45162319 | 45162558 | chr2 | 45162653 | 45163012 |
| chr2 | 45164589 | 45164608 | chr2 | 45164657 | 45164768 | chr2 | 45165490 | 45165669 |
| chr2 | 45168857 | 45168908 | chr2 | 45169349 | 45169548 | chr2 | 45169550 | 45170123 |
| chr2 | 45171295 | 45171564 | chr2 | 45171837 | 45171954 | chr2 | 45176506 | 45176865 |
| chr2 | 45179546 | 45179725 | chr2 | 45179862 | 45180156 | chr2 | 45181417 | 45181776 |
| chr2 | 45181795 | 45182094 | chr2 | 45231245 | 45231478 | chr2 | 45231754 | 45232208 |
| chr2 | 45233307 | 45233666 | chr2 | 45235491 | 45236030 | chr2 | 45237585 | 45237689 |
| chr2 | 45237691 | 45237884 | chr2 | 45240491 | 45240631 | chr2 | 45240764 | 45240876 |
| chr2 | 45241041 | 45241169 | chr2 | 45241233 | 45241280 | chr2 | 45395768 | 45396007 |
| chr2 | 45396234 | 45396533 | chr2 | 45396603 | 45397082 | chr2 | 46526226 | 46526331 |
| chr2 | 47193958 | 47194077 | chr2 | 47200517 | 47200696 | chr2 | 47249735 | 47249914 |
| chr2 | 47598298 | 47598477 | chr2 | 47598579 | 47598698 | chr2 | 47748048 | 47748587 |
| chr2 | 47796952 | 47797488 | chr2 | 47797490 | 47797911 | chr2 | 47798093 | 47798752 |
| chr2 | 47798853 | 47799033 | chr2 | 47799124 | 47799212 | chr2 | 48982485 | 48982701 |
| chr2 | 48982754 | 48982964 | chr2 | 50573520 | 50573639 | chr2 | 50573692 | 50573924 |
| chr2 | 50574041 | 50574356 | chr2 | 50574402 | 50574685 | chr2 | 50574739 | 50574940 |
| chr2 | 55289095 | 55289274 | chr2 | 56149762 | 56149941 | chr2 | 56150682 | 56151256 |
| chr2 | 56410918 | 56411087 | chr2 | 56411593 | 56411832 | chr2 | 58655968 | 58656207 |
| chr2 | 60706663 | 60706902 | chr2 | 60796498 | 60796617 | chr2 | 60797060 | 60797359 |
| chr2 | 61135116 | 61135235 | chr2 | 62798248 | 62798447 | chr2 | 63275470 | 63275509 |
| chr2 | 63275878 | 63275949 | chr2 | 63278888 | 63279022 | chr2 | 63280853 | 63281752 |
| chr2 | 63282632 | 63282867 | chr2 | 63283014 | 63283053 | chr2 | 63283870 | 63284229 |
| chr2 | 63284675 | 63284914 | chr2 | 63284996 | 63285799 | chr2 | 63286359 | 63286585 |
| chr2 | 63286694 | 63286748 | chr2 | 63287083 | 63287412 | chr2 | 66652937 | 66653053 |
| chr2 | 66653158 | 66653254 | chr2 | 66653256 | 66663577 | chr2 | 66653690 | 66653934 |
| chr2 | 66660560 | 66660791 | chr2 | 66808447 | 66808634 | chr2 | 66808727 | 66809453 |
| chr2 | 67625373 | 67625492 | chr2 | 67625733 | 67625852 | chr2 | 67626153 | 67626332 |
| chr2 | 68546250 | 68546517 | chr2 | 68546553 | 68546968 | chr2 | 68559344 | 68559463 |
| chr2 | 68672777 | 68672956 | chr2 | 70418609 | 70418722 | chr2 | 71355039 | 71355218 |
| chr2 | 71503688 | 71503927 | chr2 | 71504007 | 71504246 | chr2 | 71680759 | 71680938 |
| chr2 | 71693423 | 71693694 | chr2 | 72374295 | 72374524 | chr2 | 72374611 | 72374690 |
| chr2 | 72374714 | 72374850 | chr2 | 73145548 | 73145787 | chr2 | 73145824 | 73146123 |
| chr2 | 73147245 | 73147528 | chr2 | 73147967 | 73148067 | chr2 | 73148175 | 73148313 |
| chr2 | 73150850 | 73151029 | chr2 | 73151098 | 73151884 | chr2 | 73152600 | 73152679 |
| chr2 | 73152740 | 73152839 | chr2 | 73429420 | 73429719 | chr2 | 73429862 | 73429923 |
| chr2 | 73429977 | 73430161 | chr2 | 73430234 | 73430373 | chr2 | 73430443 | 73430818 |
| chr2 | 73440271 | 73440370 | chr2 | 73518355 | 73519014 | chr2 | 73519501 | 73519920 |
| chr2 | 74010442 | 74010621 | chr2 | 74453989 | 74454348 | chr2 | 74726670 | 74726849 |
| chr2 | 74740761 | 74741136 | chr2 | 74741138 | 74741480 | chr2 | 74741746 | 74741845 |
| chr2 | 74741873 | 74742045 | chr2 | 74742085 | 74742151 | chr2 | 74742325 | 74742648 |
| chr2 | 74742694 | 74743145 | chr2 | 74743767 | 74743824 | chr2 | 74781997 | 74782088 |
| chr2 | 74782219 | 74782356 | chr2 | 75426958 | 75426980 | chr2 | 75427295 | 75427474 |
| chr2 | 75427845 | 75428264 | chr2 | 80529292 | 80529520 | chr2 | 80529573 | 80529909 |
| chr2 | 80529986 | 80530112 | chr2 | 80530413 | 80530587 | chr2 | 80630623 | 80530552 |
| chr2 | 80531651 | 80531830 | chr2 | 80549486 | 80549845 | chr2 | 85107377 | 85107616 |
| chr2 | 85361224 | 85361310 | chr2 | 85361462 | 85361529 | chr2 | 85361629 | 85361703 |
| chr2 | 87016489 | 87016509 | chr2 | 87016576 | 87016728 | chr2 | 87017707 | 87018313 |
| chr2 | 88469219 | 88469398 | chr2 | 88751182 | 88751420 | chr2 | 88751461 | 88751816 |
| chr2 | 88751961 | 88752380 | chr2 | 88752515 | 88752874 | chr2 | 88990108 | 88990342 |
| chr2 | 89064806 | 89064976 | chr2 | 89065129 | 89065364 | chr2 | 95663873 | 95664112 |
| chr2 | 95690654 | 95690890 | chr2 | 95690944 | 95691363 | chr2 | 95691441 | 95691500 |
| chr2 | 95691502 | 95691860 | chr2 | 95691908 | 95692567 | chr2 | 95941596 | 95941895 |
| chr2 | 96990808 | 96991399 | chr2 | 97193003 | 97193064 | chr2 | 97193252 | 97193722 |
| chr2 | 97427415 | 97428194 | chr2 | 98703220 | 98703491 | chr2 | 98962800 | 98962900 |
| chr2 | 98962974 | 98963039 | chr2 | 98963255 | 98963408 | chr2 | 98963410 | 98963674 |
| chr2 | 98963750 | 98963826 | chr2 | 98963869 | 98964289 | chr2 | 98964502 | 98964741 |
| chr2 | 99439369 | 99439593 | chr2 | 99553333 | 99553632 | chr2 | 99796327 | 99796415 |
| chr2 | 99798571 | 99798746 | chr2 | 99799229 | 99799230 | chr2 | 100937747 | 100938210 |
| chr2 | 100938330 | 100938545 | chr2 | 100938575 | 100938799 | chr2 | 100938801 | 100938810 |
| chr2 | 100938985 | 100939246 | chr2 | 101009731 | 101010030 | chr2 | 101034149 | 101034388 |
| chr2 | 101436638 | 101436790 | chr2 | 102091079 | 102091335 | chr2 | 103236080 | 103236277 |
| chr2 | 105459001 | 105459152 | chr2 | 105459903 | 105460263 | chr2 | 105460265 | 105460604 |
| chr2 | 105460847 | 105461026 | chr2 | 105461164 | 105461335 | chr2 | 105461556 | 105461668 |
| chr2 | 105461700 | 105462000 | chr2 | 105462075 | 105462314 | chr2 | 106468701 | 105469000 |
| chr2 | 105469569 | 105469857 | chr2 | 105469881 | 105470168 | chr2 | 105470266 | 105470561 |
| chr2 | 105470563 | 105470925 | chr2 | 105472149 | 105472426 | chr2 | 105472713 | 105472928 |
| chr2 | 105473162 | 105473521 | chr2 | 105478687 | 105479054 | chr2 | 105479056 | 105479166 |
| chr2 | 105480630 | 105480683 | chr2 | 105483568 | 105483807 | chr2 | 105484367 | 105484480 |
| chr2 | 105488348 | 105488527 | chr2 | 105760890 | 105761004 | chr2 | 106060525 | 106060884 |
| chr2 | 106681644 | 106681870 | chr2 | 106681936 | 106681983 | chr2 | 106681985 | 106682175 |
| chr2 | 106730137 | 106730316 | chr2 | 106959289 | 106959648 | chr2 | 106959833 | 106960072 |
| chr2 | 107103778 | 107104017 | chr2 | 107502519 | 107502730 | chr2 | 107502866 | 107502908 |
| chr2 | 107503422 | 107503423 | chr2 | 107503458 | 107503637 | chr2 | 107503802 | 107504101 |
| chr2 | 109335091 | 109335264 | chr2 | 109648002 | 109648301 | chr2 | 109745915 | 109746164 |
| chr2 | 109746204 | 109746388 | chr2 | 109746463 | 109746563 | chr2 | 111875279 | 111875518 |
| chr2 | 112656944 | 112657123 | chr2 | 114256879 | 114257238 | chr2 | 114261200 | 114261559 |
| chr2 | 115918579 | 115918893 | chr2 | 115919338 | 115919425 | chr2 | 115919831 | 115920612 |

TABLE 15-continued

| chr | start | end | chr | start | end | chr | start | end |
|---|---|---|---|---|---|---|---|---|
| chr2 | 115920614 | 115920618 | chr2 | 118981075 | 118981857 | chr2 | 118981946 | 118982148 |
| chr2 | 118982254 | 118982574 | chr2 | 119067562 | 119068143 | chr2 | 119532059 | 119532358 |
| chr2 | 119566137 | 119566376 | chr2 | 119591259 | 119591558 | chr2 | 119592666 | 119592863 |
| chr2 | 119592923 | 119593464 | chr2 | 119593466 | 119593642 | chr2 | 119599830 | 119600129 |
| chr2 | 119600235 | 119600839 | chr2 | 119600856 | 119600953 | chr2 | 119602515 | 119602630 |
| chr2 | 119602829 | 119603174 | chr2 | 119603946 | 119604093 | chr2 | 119604154 | 119604245 |
| chr2 | 119604711 | 119604933 | chr2 | 119606048 | 119606283 | chr2 | 119606631 | 119606647 |
| chr2 | 119606692 | 119606931 | chr2 | 119607443 | 119607504 | chr2 | 119607848 | 119607933 |
| chr2 | 119610758 | 119610940 | chr2 | 119610999 | 119611057 | chr2 | 119611653 | 119611892 |
| chr2 | 119612250 | 119612429 | chr2 | 119614047 | 119614221 | chr2 | 119614697 | 119614936 |
| chr2 | 119614952 | 119615719 | chr2 | 119616070 | 119616552 | chr2 | 119616782 | 119616960 |
| chr2 | 119914617 | 119914856 | chr2 | 119916525 | 119916687 | chr2 | 120281556 | 120281790 |
| chr2 | 120281849 | 120281901 | chr2 | 120281939 | 120282028 | chr2 | 120979994 | 120980173 |
| chr2 | 120980255 | 120980494 | chr2 | 121200303 | 121200532 | chr2 | 121345007 | 121345169 |
| chr2 | 121411987 | 121412231 | chr2 | 122495323 | 122495490 | chr2 | 124782289 | 124782546 |
| chr2 | 124782596 | 124783195 | chr2 | 127423136 | 127423434 | chr2 | 127428910 | 127429147 |
| chr2 | 127438559 | 127438738 | chr2 | 127782953 | 127783168 | chr2 | 127783170 | 127783360 |
| chr2 | 127863514 | 127863813 | chr2 | 127976391 | 127976750 | chr2 | 128421788 | 128421850 |
| chr2 | 128421891 | 128422027 | chr2 | 128616519 | 128616628 | chr2 | 128847701 | 128847799 |
| chr2 | 130763485 | 130763677 | chr2 | 130971063 | 130971355 | chr2 | 131477742 | 131478023 |
| chr2 | 131594915 | 131594922 | chr2 | 131594948 | 131595094 | chr2 | 131720787 | 131721099 |
| chr2 | 131721438 | 131721585 | chr2 | 131721867 | 131722035 | chr2 | 131792157 | 131792520 |
| chr2 | 131792532 | 131792747 | chr2 | 131792921 | 131793154 | chr2 | 131793188 | 131793236 |
| chr2 | 132088786 | 132088919 | chr2 | 132121566 | 132121618 | chr2 | 132121652 | 132121676 |
| chr2 | 132121678 | 132121823 | chr2 | 132152279 | 132152578 | chr2 | 132182701 | 132183180 |
| chr2 | 132767373 | 132767492 | chr2 | 133014571 | 133014662 | chr2 | 133015300 | 133015419 |
| chr2 | 133062239 | 133062299 | chr2 | 133062362 | 133062478 | chr2 | 133426175 | 133426354 |
| chr2 | 133426561 | 133426776 | chr2 | 137522371 | 137522550 | chr2 | 137523751 | 137523759 |
| chr2 | 139536863 | 139537221 | chr2 | 139537355 | 139537823 | chr2 | 139537851 | 139537954 |
| chr2 | 142887816 | 142887886 | chr2 | 142887888 | 142888149 | chr2 | 142888264 | 142888503 |
| chr2 | 144694272 | 144694515 | chr2 | 144694554 | 144695231 | chr2 | 145273369 | 145273848 |
| chr2 | 145274112 | 145274511 | chr2 | 145274715 | 145274975 | chr2 | 145274977 | 145275314 |
| chr2 | 145282045 | 145282224 | chr2 | 148776713 | 148776876 | chr2 | 149633009 | 149633488 |
| chr2 | 149633646 | 149634065 | chr2 | 149645413 | 149645559 | chr2 | 149645561 | 149645995 |
| chr2 | 151342979 | 151343218 | chr2 | 154333432 | 154333671 | chr2 | 154334170 | 154334450 |
| chr2 | 154334452 | 154334769. | chr2 | 154335185 | 154335355 | chr2 | 154727963 | 154727992 |
| chr2 | 154728245 | 154728441 | chr2 | 154729083 | 154729316 | chr2 | 154729485 | 154729664 |
| chr2 | 155555064 | 155555440 | chr2 | 157176506 | 157176805 | chr2 | 157176908 | 157178165 |
| chr2 | 157178167 | 157178407 | chr2 | 157178637 | 157178809 | chr2 | 160760984 | 160761454 |
| chr2 | 161253375 | 161253554 | chr2 | 162272983 | 162273315 | chr2 | 162273383 | 162274182 |
| chr2 | 162274220 | 162274414 | chr2 | 162274748 | 162274942 | chr2 | 162275055 | 162275227 |
| chr2 | 162275311 | 162275438 | chr2 | 162275473 | 162275887 | chr2 | 162280153 | 162280416 |
| chr2 | 162280741 | 162281050 | chr2 | 162283291 | 162283603 | chr2 | 162283783 | 162284130 |
| chr2 | 164592998 | 164593221 | chr2 | 164593223 | 164593237 | chr2 | 168149978 | 168149991 |
| chr2 | 168149993 | 168150337 | chr2 | 168150669 | 168151028 | chr2 | 170282882 | 170283178 |
| chr2 | 170551654 | 170551866 | chr2 | 170681792 | 170681909 | chr2 | 170682152 | 170682329 |
| chr2 | 171569986 | 171570062 | chr2 | 171570182 | 171570190 | chr2 | 171570471 | 171570525 |
| chr2 | 171570590 | 171570829 | chr2 | 171571171 | 171571342 | chr2 | 171571379 | 171571410 |
| chr2 | 171571800 | 171571997 | chr2 | 171670259 | 171670447 | chr2 | 171670472 | 171670558 |
| chr2 | 171671385 | 171671790 | chr2 | 171671800 | 171671984 | chr2 | 171674001 | 171674026 |
| chr2 | 171674664 | 171675143 | chr2 | 171675268 | 171675383 | chr2 | 171675523 | 171675687 |
| chr2 | 171676590 | 171676787 | chr2 | 171676858 | 171676885 | chr2 | 171822419 | 171822574 |
| chr2 | 172366939 | 172367178 | chr2 | 172411062 | 172411241 | chr2 | 172945027 | 172945266 |
| chr2 | 172945821 | 172946294 | chr2 | 172947684 | 172947914 | chr2 | 172948184 | 172948406 |
| chr2 | 172948813 | 172948850 | chr2 | 172949090 | 172949283 | chr2 | 172949349 | 172949809 |
| chr2 | 172951494 | 172951543 | chr2 | 172952425 | 172952640 | chr2 | 172952685 | 172952882 |
| chr2 | 172952993 | 172953096 | chr2 | 172953125 | 172953144 | chr2 | 172955346 | 172955403 |
| chr2 | 172955472 | 172955645 | chr2 | 172957808 | 172958157 | chr2 | 172961319 | 172961678 |
| chr2 | 172964743 | 172964889 | chr2 | 172965296 | 172965299 | chr2 | 172965648 | 172965763 |
| chr2 | 172966174 | 172966533 | chr2 | 172972648 | 172972891 | chr2 | 172972931 | 172973307 |
| chr2 | 173099710 | 173099889 | chr2 | 173100167 | 173100506 | chr2 | 173422651 | 173422770 |
| chr2 | 175190771 | 175191973 | chr2 | 175192085 | 175192550 | chr2 | 175193187 | 175193377 |
| chr2 | 175193379 | 175193645 | chr2 | 175193809 | 175193906 | chr2 | 175195785 | 175195859 |
| chr2 | 175196355 | 175196371 | chr2 | 175196426 | 175196654 | chr2 | 175197015 | 175197194 |
| chr2 | 175199432 | 175199555 | chr2 | 175199922 | 175200012 | chr2 | 175200093 | 175200441 |
| chr2 | 175200710 | 175200853 | chr2 | 175200917 | 175201183 | chr2 | 175201360 | 175201542 |
| chr2 | 175201776 | 175201829 | chr2 | 175202127 | 175202246 | chr2 | 175202569 | 175202601 |
| chr2 | 175202634 | 175202746 | chr2 | 175204100 | 175204279 | chr2 | 175204694 | 175204947 |
| chr2 | 175206752 | 175206906 | chr2 | 175206961 | 175207111 | chr2 | 175207154 | 175207333 |
| chr2 | 175207446 | 175207745 | chr2 | 175208214 | 175208869 | chr2 | 175208997 | 175209218 |
| chr2 | 175546942 | 175547241 | chr2 | 175547310 | 175547489 | chr2 | 176940092 | 176940391 |
| chr2 | 176943180 | 176943659 | chr2 | 176943763 | 176943863 | chr2 | 176943995 | 176944002 |
| chr2 | 176944326 | 176944405 | chr2 | 176944457 | 176944847 | chr2 | 176945138 | 176945269 |
| chr2 | 176945582 | 176945885 | chr2 | 176946475 | 176946868 | chr2 | 176947285 | 176947494 |
| chr2 | 176947647 | 176947654 | chr2 | 176947764 | 176947940 | chr2 | 176947942 | 176948006 |
| chr2 | 176948522 | 176948821 | chr2 | 176948971 | 176949150 | chr2 | 176949603 | 176949962 |
| chr2 | 176950075 | 176950350 | chr2 | 176956929 | 176957300 | chr2 | 176957409 | 176957415 |
| chr2 | 176957577 | 176957629 | chr2 | 176957915 | 176958008 | chr2 | 176958045 | 176958584 |

TABLE 15-continued

| chr | start | end | chr | start | end | chr | start | end |
|---|---|---|---|---|---|---|---|---|
| chr2 | 176959191 | 176959589 | chr2 | 176963366 | 176963605 | chr2 | 176963999 | 176964150 |
| chr2 | 176964180 | 176964238 | chr2 | 176964222 | 176964334 | chr2 | 176964390 | 176964768 |
| chr2 | 176965265 | 176965591 | chr2 | 176969387 | 176969614 | chr2 | 176969677 | 176969984 |
| chr2 | 176975946 | 176976289 | chr2 | 176980649 | 176980938 | chr2 | 176981377 | 176981592 |
| chr2 | 176982518 | 176982726 | chr2 | 176986712 | 176986932 | chr2 | 176986962 | 176987215 |
| chr2 | 176993462 | 176994380 | chr2 | 176994498 | 176994622 | chr2 | 176995071 | 176995270 |
| chr2 | 176995332 | 176995712 | chr2 | 177001000 | 177001058 | chr2 | 177001118 | 177001263 |
| chr2 | 177001265 | 177001696 | chr2 | 177001782 | 177002079 | chr2 | 177004463 | 177004498 |
| chr2 | 177004556 | 177004762 | chr2 | 177042914 | 177042999 | chr2 | 177043267 | 177043610 |
| chr2 | 177053187 | 177053435 | chr2 | 177053619 | 177053703 | chr2 | 177054023 | 177054442 |
| chr2 | 177502981 | 177503153 | chr2 | 178972904 | 178973143 | chr2 | 179317039 | 179317139 |
| chr2 | 182321308 | 182321727 | chr2 | 182321736 | 182321838 | chr2 | 182322039 | 182322192 |
| chr2 | 182322400 | 182323131 | chr2 | 182542829 | 182542864 | chr2 | 182542866 | 182543008 |
| chr2 | 182543221 | 182543413 | chr2 | 182543666 | 182544025 | chr2 | 182545124 | 182545363 |
| chr2 | 182545438 | 182545797 | chr2 | 182545887 | 182545948 | chr2 | 182546002 | 182546179 |
| chr2 | 182546361 | 182546535 | chr2 | 182547290 | 182547388 | chr2 | 182547438 | 182547709 |
| chr2 | 182547840 | 182547932 | chr2 | 182548062 | 182548259 | chr2 | 182548992 | 182549026 |
| chr2 | 182549038 | 182549231 | chr2 | 182549247 | 182549546 | chr2 | 182550054 | 182550199 |
| chr2 | 182819031 | 182819312 | chr2 | 183731200 | 183731332 | chr2 | 183731467 | 183731619 |
| chr2 | 183731734 | 183732153 | chr2 | 185462776 | 185463075 | chr2 | 185463116 | 185463895 |
| chr2 | 186603414 | 186603593 | chr2 | 188418947 | 188419178 | chr2 | 189157513 | 189157692 |
| chr2 | 193058947 | 193059318 | chr2 | 193059345 | 193059549 | chr2 | 193059662 | 193059717 |
| chr2 | 193059719 | 193060146 | chr2 | 193060294 | 193060533 | chr2 | 193060608 | 193060967 |
| chr2 | 193061341 | 193061580 | chr2 | 198456572 | 198456690 | chr2 | 200326551 | 200326730 |
| chr2 | 200326765 | 200326813 | chr2 | 200327187 | 200327254 | chr2 | 200327424 | 200327452 |
| chr2 | 200327576 | 200327666 | chr2 | 200328669 | 200328685 | chr2 | 200329030 | 200329394 |
| chr2 | 200329433 | 200329748 | chr2 | 200333686 | 200333759 | chr2 | 200333801 | 200333925 |
| chr2 | 200334895 | 200335308 | chr2 | 200335363 | 200335452 | chr2 | 200335592 | 200336034 |
| chr2 | 201450453 | 201450743 | chr2 | 201450745 | 201450812 | chr2 | 201450845 | 201450922 |
| chr2 | 201451014 | 201451144 | chr2 | 202096992 | 202097231 | chr2 | 202899788 | 202899967 |
| chr2 | 206550978 | 206551015 | chr2 | 206551072 | 206551363 | chr2 | 206551451 | 206551457 |
| chr2 | 207138998 | 207139155 | chr2 | 207139267 | 207139686 | chr2 | 207307426 | 207307478 |
| chr2 | 207307548 | 207307665 | chr2 | 207308711 | 207308950 | chr2 | 207506612 | 207507266 |
| chr2 | 208635519 | 208635864 | chr2 | 209113024 | 209113202 | chr2 | 209225137 | 209225376 |
| chr2 | 209271228 | 209271337 | chr2 | 210636255 | 210636284 | chr2 | 210636430 | 210636690 |
| chr2 | 210636738 | 210636877 | chr2 | 210636934 | 210636974 | chr2 | 213401138 | 213401437 |
| chr2 | 213401511 | 213401565 | chr2 | 213401567 | 213402050 | chr2 | 213403015 | 213403434 |
| chr2 | 217559222 | 217559401 | chr2 | 218806046 | 218806405 | chr2 | 219736052 | 219736705 |
| chr2 | 219827964 | 219827975 | chr2 | 219847360 | 219847659 | chr2 | 219848726 | 219848892 |
| chr2 | 219848936 | 219849085 | chr2 | 219857648 | 219857738 | chr2 | 219857781 | 219857860 |
| chr2 | 220080582 | 220080941 | chr2 | 220173904 | 220174037 | chr2 | 220174060 | 220174383 |
| chr2 | 220196266 | 220196671 | chr2 | 220223024 | 220223203 | chr2 | 220223557 | 220223700 |
| chr2 | 220223795 | 220223796 | chr2 | 220283250 | 220283290 | chr2 | 220283363 | 220283609 |
| chr2 | 220299495 | 220299635 | chr2 | 220299886 | 220300154 | chr2 | 220348949 | 220348984 |
| chr2 | 220349055 | 220349788 | chr2 | 220361370 | 220361467 | chr2 | 220416297 | 220416596 |
| chr2 | 220416770 | 220417729 | chr2 | 222435699 | 222435857 | chr2 | 223155678 | 223156277 |
| chr2 | 223158648 | 223159542 | chr2 | 223159735 | 223159806 | chr2 | 223159869 | 223160154 |
| chr2 | 223160251 | 223160481 | chr2 | 223161173 | 223161352 | chr2 | 223161452 | 223161685 |
| chr2 | 223161807 | 223162165 | chr2 | 223162678 | 223162891 | chr2 | 223162929 | 223163225 |
| chr2 | 223163473 | 223163637 | chr2 | 223163682 | 223163809 | chr2 | 223163811 | 223164034 |
| chr2 | 223164440 | 223164617 | chr2 | 223165334 | 223165503 | chr2 | 223166190 | 223166226 |
| chr2 | 223166294 | 223166825 | chr2 | 223167302 | 223167661 | chr2 | 223168346 | 223168832 |
| chr2 | 223168917 | 223168945 | chr2 | 223169543 | 223169962 | chr2 | 223170286 | 223170525 |
| chr2 | 223171026 | 223171265 | chr2 | 223172969 | 223173259 | chr2 | 223176018 | 223176282 |
| chr2 | 223176361 | 223176512 | chr2 | 223176720 | 223177080 | chr2 | 223177245 | 223177703 |
| chr2 | 228029326 | 228029351 | chr2 | 228029373 | 228029625 | chr2 | 228466762 | 228466881 |
| chr2 | 228735702 | 228735828 | chr2 | 228736135 | 228736296 | chr2 | 228736336 | 228736554 |
| chr2 | 229046024 | 229046605 | chr2 | 230795461 | 230795640 | chr2 | 232394867 | 232395022 |
| chr2 | 232395055 | 232395166 | chr2 | 232791619 | 232792098 | chr2 | 233350112 | 233350540 |
| chr2 | 233350844 | 233351270 | chr2 | 233351416 | 233351491 | chr2 | 233351930 | 233352007 |
| chr2 | 233352102 | 233352452 | chr2 | 233352507 | 233352763 | chr2 | 233352776 | 233352949 |
| chr2 | 233498615 | 233498874 | chr2 | 233498896 | 233499345 | chr2 | 233499386 | 233499394 |
| chr2 | 233750451 | 233750630 | chr2 | 235404471 | 235404533 | chr2 | 235404551 | 235404590 |
| chr2 | 235860803 | 235860897 | chr2 | 236402683 | 236402901 | chr2 | 236403060 | 236403102 |
| chr2 | 236403174 | 236403419 | chr2 | 236403779 | 236403833 | chr2 | 236877188 | 236877367 |
| chr2 | 237072642 | 237072998 | chr2 | 237073000 | 237073015 | chr2 | 237073057 | 237073112 |
| chr2 | 237073265 | 237073496 | chr2 | 237076657 | 237076833 | chr2 | 237077466 | 237077685 |
| chr2 | 237077815 | 237078054 | chr2 | 237078097 | 237078427 | chr2 | 237080190 | 237080369 |
| chr2 | 237081255 | 237081427 | chr2 | 237081537 | 237081554 | chr2 | 237082344 | 237082809 |
| chr2 | 237086291 | 237086398 | chr2 | 237086400 | 237086559 | chr2 | 237145333 | 237145437 |
| chr2 | 237145439 | 237145692 | chr2 | 237416114 | 237416504 | chr2 | 238395205 | 238395444 |
| chr2 | 238395815 | 238395988 | chr2 | 238535876 | 238535985 | chr2 | 238536005 | 238536215 |
| chr2 | 238864570 | 238864631 | chr2 | 238864727 | 238864989 | chr2 | 239051124 | 239051303 |
| chr2 | 239140139 | 239140347 | chr2 | 239265703 | 239265881 | chr2 | 239482400 | 239482622 |
| chr2 | 239705202 | 239705364 | chr2 | 239755090 | 239755198 | chr2 | 239755638 | 239755664 |
| chr2 | 239756347 | 239756463 | chr2 | 239756488 | 239756586 | chr2 | 239757551 | 239757731 |
| chr2 | 239757899 | 239757910 | chr2 | 239757992 | 239758061 | chr2 | 239758126 | 239758231 |
| chr2 | 239758251 | 239758490 | chr2 | 239957240 | 239957539 | chr2 | 240168722 | 240169141 |

TABLE 15-continued

| chr | start | end | chr | start | end | chr | start | end |
|---|---|---|---|---|---|---|---|---|
| chr2 | 240319908 | 240320087 | chr2 | 240582303 | 240582448 | chr2 | 240619443 | 240619682 |
| chr2 | 240658145 | 240658504 | chr2 | 240658593 | 240658772 | chr2 | 241095576 | 241095868 |
| chr2 | 241393126 | 241393167 | chr2 | 241393199 | 241393545 | chr2 | 241542045 | 241542344 |
| chr2 | 241544927 | 241545106 | chr2 | 241758299 | 241758898 | chr2 | 241759497 | 241759796 |
| chr2 | 241760075 | 241760254 | chr2 | 241760420 | 241760599 | chr2 | 241771052 | 241771361 |
| chr2 | 241865091 | 241865450 | chr2 | 242009317 | 242009466 | chr2 | 242021689 | 242021916 |
| chr2 | 242523873 | 242524172 | chr2 | 242549754 | 242649772 | chr2 | 242549918 | 242550053 |
| chr2 | 242554475 | 242554654 | chr2 | 242756042 | 242756401 | chr2 | 242832893 | 242833252 |
| chr2 | 242833484 | 242833663 | chr2 | 242833711 | 242833930 | chr2 | 242836419 | 242836718 |
| chr2 | 242925420 | 242925719 | chr3 | 238456 | 238716 | chr3 | 239007 | 239126 |
| chr3 | 239159 | 239175 | chr3 | 239534 | 239869 | chr3 | 240110 | 240313 |
| chr3 | 2140189 | 2140435 | chr3 | 3840419 | 3840838 | chr3 | 3840946 | 3841245 |
| chr3 | 3842586 | 3842689 | chr3 | 5137871 | 5138109 | chr3 | 6902228 | 6902441 |
| chr3 | 6903500 | 6903564 | chr3 | 88:0152 | 8810298 | chr3 | 9178065 | 9178130 |
| chr3 | 9593878 | 9594117 | chr3 | 9594286 | 9594473 | chr3 | 9595199 | 9595199 |
| chr3 | 9595396 | 9595503 | chr3 | 9595599 | 9595678 | chr3 | 9904155 | 9904634 |
| chr3 | 9941391 | 9941509 | chr3 | 9956984 | 9957223 | chr3 | 9957355 | 9957774 |
| chr3 | 10182757 | 10182917 | chr3 | 10183247 | 10183396 | chr3 | 10183632 | 10183811 |
| chr3 | 10858055 | 10858123 | chr3 | 11034163 | 11034462 | chr3 | 11034991 | 11035353 |
| chr3 | 11035383 | 11035410 | chr3 | 12046310 | 12046353 | chr3 | 12046378 | 12046727 |
| chr3 | 12917512 | 12917751 | chr3 | 12976987 | 12977150 | chr3 | 13323405 | 13324029 |
| chr3 | 13324277 | 13324348 | chr3 | 13324420 | 13324516 | chr3 | 13324744 | 13325023 |
| chr3 | 13590341 | 13590414 | chr3 | 13590448 | 13590641 | chr3 | 13679082 | 13679441 |
| chr3 | 13921316 | 13921555 | chr3 | 14851755 | 14851994 | chr3 | 14852233 | 14852659 |
| chr3 | 14852661 | 14853012 | chr3 | 16553963 | 16564202 | chr3 | 16554251 | 16554466 |
| chr3 | 16554468 | 16554730 | chr3 | 17001229 | 17001341 | chr3 | 19189367 | 19189546 |
| chr3 | 19189611 | 19189850 | chr3 | 19190061 | 19190253 | chr3 | 22413591 | 22413770 |
| chr3 | 22413871 | 22413911 | chr3 | 22413960 | 22414050 | chr3 | 24870915 | 24870925 |
| chr3 | 24870982 | 24871177 | chr3 | 24871246 | 24871281 | chr3 | 25469303 | 25469402 |
| chr3 | 25469404 | 25469482 | chr3 | 25469605 | 25469784 | chr3 | 26663963 | 26664202 |
| chr3 | 26664303 | 26664842 | chr3 | 27754404 | 27754583 | chr3 | 27762260 | 27762733 |
| chr3 | 27762783 | 27762962 | chr3 | 27763492 | 27763671 | chr3 | 27764421 | 27764472 |
| chr3 | 27764596 | 27764600 | chr3 | 27765085 | 27765362 | chr3 | 27765401 | 27765444 |
| chr3 | 22771422 | 27772081 | chr3 | 28616745 | 28617764 | chr3 | 32858274 | 32858959 |
| chr3 | 32859256 | 32859285 | chr3 | 32859418 | 32859773 | chr3 | 32859992 | 32860306 |
| chr3 | 33259801 | 33260876 | chr3 | 35680815 | 35680947 | chr3 | 36805720 | 36805959 |
| chr3 | 36806053 | 36806130 | chr3 | 36806179 | 36806292 | chr3 | 37493429 | 37493720 |
| chr3 | 37901952 | 37902028 | chr3 | 38030610 | 38030789 | chr3 | 38032257 | 38032436 |
| chr3 | 38035774 | 38036088 | chr3 | 38080596 | 38081009 | chr3 | 38081154 | 38081286 |
| chr3 | 38081339 | 38081360 | chr3 | 38690527 | 38690766 | chr3 | 38691469 | 38691557 |
| chr3 | 39851674 | 39851913 | chr3 | 41266012 | 41266239 | chr3 | 42222640 | 42222737 |
| chr3 | 42640761 | 42640874 | chr3 | 42814467 | 42814706 | chr3 | 42947333 | 42947632 |
| chr3 | 44036176 | 44036415 | chr3 | 44036496 | 44036675 | chr3 | 44036743 | 44037128 |
| chr3 | 44037130 | 44037282 | chr3 | 44037525 | 44037764 | chr3 | 44037781 | 44038740 |
| chr3 | 44039265 | 44040026 | chr3 | 44040057 | 44040097 | chr3 | 44040413 | 44040652 |
| chr3 | 44040709 | 44041128 | chr3 | 44063354 | 44063953 | chr3 | 44596405 | 44596584 |
| chr3 | 44596614 | 44596913 | chr3 | 44626336 | 44626538 | chr3 | 44626540 | 44626815 |
| chr3 | 44726855 | 44727069 | chr3 | 44727071 | 44727274 | chr3 | 45187222 | 45187328 |
| chr3 | 46924905 | 46925039 | chr3 | 48227686 | 48227788 | chr3 | 48236391 | 48236553 |
| chr3 | 48693228 | 48693701 | chr3 | 48693852 | 48693882 | chr3 | 48693884 | 48694155 |
| chr3 | 48694227 | 48694247 | chr3 | 48698723 | 48699011 | chr3 | 48699377 | 48699859 |
| chr3 | 49906993 | 49907232 | chr3 | 49939836 | 49940495 | chr3 | 50243283 | 50243582 |
| chr3 | 50374581 | 50374760 | chr3 | 50374843 | 50375022 | chr3 | 50375104 | 50375639 |
| chr3 | 50395432 | 50395611 | chr3 | 50402078 | 50403037 | chr3 | 50575518 | 50575635 |
| chr3 | 52552500 | $2552739 | chr3 | 52553395 | 52553537 | chr3 | 53032708 | 53033609 |
| chr3 | 54155525 | 54155764 | chr3 | 54157297 | 54157536 | chr3 | 54157780 | 54158006 |
| chr3 | 55519117 | 55519228 | chr3 | 55523019 | 55523318 | chr3 | 62353291 | 62354130 |
| chr3 | 62354187 | 62354385 | chr3 | 62354531 | 62354793 | chr3 | 62354900 | 62355010 |
| chr3 | 62355332 | 62355571 | chr3 | 62355692 | 62356220 | chr3 | 62356367 | 62356645 |
| chr3 | 62356793 | 62357193 | chr3 | 62357279 | 62357431 | chr3 | 62357527 | 62357671 |
| chr3 | 62357736 | 62357766 | chr3 | 62358059 | 62358117 | chr3 | 62358444 | 62358683 |
| chr3 | 62358758 | 62359115 | chr3 | 62359276 | 62359392 | chr3 | 62359394 | 62359995 |
| chr3 | 62360222 | 62360641 | chr3 | 62362817 | 62362917 | chr3 | 62363099 | 62363206 |
| chr3 | 62363541 | 62363780 | chr3 | 62363819 | 62364177 | chr3 | 62364280 | 62364418 |
| chr3 | 62364659 | 62365205 | chr3 | 62861044 | 62861142 | chr3 | 62861144 | 62861223 |
| chr3 | 63264065 | 63264135 | chr3 | 63264158 | 63264244 | chr3 | 68056816 | 68057235 |
| chr3 | 68980843 | 68980947 | chr3 | 68980949 | 68981202 | chr3 | 68981469 | 68981708 |
| chr3 | 69590865 | 69591044 | chr3 | 69591311 | 69591415 | chr3 | 69591780 | 69591978 |
| chr3 | 69592069 | 69592163 | chr3 | 69741004 | 69741087 | chr3 | 69937792 | 69937926 |
| chr3 | 718024.89 | 71802594 | chr3 | 71802596 | 71802720 | chr3 | 71803040 | 71803459 |
| chr3 | 71803553 | 71803558 | chr3 | 71803560 | 71803784 | chr3 | 71803827 | 71803912 |
| chr3 | 73045525 | 73045672 | chr3 | 75955924 | 75955997 | chr3 | 75956027 | 75956453 |
| chr3 | 79815421 | 79815660 | chr3 | 79816688 | 79817099 | chr3 | 79817214 | 79817393 |
| chr3 | 85008452 | 85008726 | chr3 | 85008803 | 85008811 | chr3 | 88248026 | 88248142 |
| chr3 | 96532726 | 96532965 | chr3 | 96533302 | 96533541 | chr3 | 96533947 | 96534186 |
| chr3 | 98620817 | 98621056 | chr3 | 99594836 | 99595195 | chr3 | 101230575 | 101230641 |
| chr3 | 101230942 | 101231174 | chr3 | 101397150 | 101397302 | chr3 | 106936068 | 106936294 |
| chr3 | 112052411 | 112052521 | chr3 | 117715472 | 117715643 | chr3 | 117715772 | 117716124 |

TABLE 15-continued

| chr | start | end | chr | start | end | chr | start | end |
|---|---|---|---|---|---|---|---|---|
| chr3 | 117716214 | 117716312 | chr3 | 117716314 | 117716551 | chr3 | 120003954 | 120004036 |
| chr3 | 120004080 | 120004438 | chr3 | 120169683 | 120169922 | chr3 | 120627319 | 120627535 |
| chr3 | 121902878 | 121902950 | chr3 | 121902991 | 121903219 | chr3 | 121903324 | 121903717 |
| chr3 | 122234151 | 122234246 | chr3 | 122702194 | 122702430 | chr3 | 123166972 | 123167006 |
| chr3 | 123167301 | 123167631 | chr3 | 123167679 | 123167918 | chr3 | 125898567 | 125899292 |
| chr3 | 125899445 | 125899706 | chr3 | 125899740 | 125899873 | chr3 | 125899927 | 125899979 |
| chr3 | 125932169 | 125932586 | chr3 | 126373433 | 126373619 | chr3 | 126373669 | 126373792 |
| chr3 | 126854599 | 126854898 | chr3 | 127534879 | 127534976 | chr3 | 127634112 | 12763429] |
| chr3 | 127794464 | 127794943 | chr3 | 127795248 | 127795253 | chr3 | 128202373 | 128202552 |
| chr3 | 128208829 | 128209308 | chr3 | 128273913 | 128274052 | chr3 | 128274309 | 128274655 |
| chr3 | 128417127 | 128417306 | chr3 | 128719977 | 128720143 | chr3 | 128720164 | 128720347 |
| chr3 | 128720419 | 128720534 | chr3 | 128720567 | 128720696 | chr3 | 128720780 | 128720884 |
| chr3 | 128720885 | 128721319 | chr3 | 128764472 | 128764607 | chr3 | 129693075 | 129693200 |
| chr3 | 129693305 | 129693499 | chr3 | 129693955 | 129694347 | chr3 | 130064351 | 130064588 |
| chr3 | 130064781 | 130064923 | chr3 | 130235952 | 130236064 | chr3 | 130236174 | 130236298 |
| chr3 | 130519821 | 130519929 | chr3 | 131753957 | 131754136 | chr3 | 132756966 | 132757205 |
| chr3 | 133217923 | 133218102 | chr3 | 133748044 | 133748206 | chr3 | 133748552 | 133748679 |
| chr3 | 134369572 | 134369919 | chr3 | 134369921 | 134369931 | chr3 | 134514792 | 134514879 |
| chr3 | 134514960 | 134514971 | chr3 | 134515040 | 134515459 | chr3 | 134515590 | 134516309 |
| chr3 | 136537567 | 136537806 | chr3 | 136538520 | 136538910 | chr3 | 136582941 | 136583037 |
| chr3 | 136751546 | 136751833 | chr3 | 137479149 | 137479388 | chr3 | 137479525 | 137479764 |
| chr3 | 137479893 | 137480847 | chr3 | 137481094 | 137481393 | chr3 | 137481782 | 137481873 |
| chr3 | 137481936 | 137482261 | chr3 | 137483212 | 137483319 | chr3 | 137483570 | 137483691 |
| chr3 | 137483746 | 137484026 | chr3 | 137484085 | 137484105 | chr3 | 137484319 | 137484618 |
| chr3 | 137485931 | 137486390 | chr3 | 137486429 | 137486653 | chr3 | 137487874 | 137488004 |
| chr3 | 137488091 | 137488113 | chr3 | 137488856 | 137489699 | chr3 | 137489876 | 137491135 |
| chr3 | 138153889 | 138154068 | chr3 | 138154240 | 138154277 | chr3 | 138655857 | 138656216 |
| chr3 | 138656743 | 138656982 | chr3 | 138657347 | 138657495 | chr3 | 138657618 | 138658297 |
| chr3 | 138658704 | 138658864 | chr3 | 138659081 | 138659187 | chr3 | 138662060 | 138662180 |
| chr3 | 138662282 | 138662535 | chr3 | 138662705 | 138662941 | chr3 | 138663611 | 138663728 |
| chr3 | 138664142 | 138664249 | chr3 | 138664330 | 138664383 | chr3 | 138664827 | 138665336 |
| chr3 | 138665397 | 138665426 | chr3 | 138665479 | 138665528 | chr3 | 138665540 | 138665718 |
| chr3 | 138665779 | 138666378 | chr3 | 138668646 | 138668685 | chr3 | 138668758 | 138669109 |
| chr3 | 138669141 | 138669485 | chr3 | 138679566 | 138679614 | chr3 | 139258173 | 139258412 |
| chr3 | 139653413 | 139653573 | chr3 | 139653575 | 139653772 | chr3 | 140769430 | 140769789 |
| chr3 | 140769830 | 140770302 | chr3 | 140770408 | 140770590 | chr3 | 140770644 | 140770683 |
| chr3 | 140770685 | 140770909 | chr3 | 140771231 | 140771410 | chr3 | 140771716 | 140771955 |
| chr3 | 141174269 | 141174688 | chr3 | 141481983 | 141482162 | chr3 | 141516315 | 141516794 |
| chr3 | 142682184 | 142682483 | chr3 | 142791076 | 142791173 | chr3 | 142837906 | 142838319 |
| chr3 | 142838530 | 142838647 | chr3 | 142838877 | 142839073 | chr3 | 142839439 | 142839526 |
| chr3 | 142839563 | 142839578 | chr3 | 142839580 | 142839689 | chr3 | 142839784 | 142839902 |
| chr3 | 142839945 | 142839991 | chr3 | 142839993 | 142840128 | chr3 | 142840222 | 142840338 |
| chr3 | 142896066 | 142896305 | chr3 | 145878591 | 145878641 | chr3 | 146187843 | 146188069 |
| chr3 | 147074871 | 147075110 | chr3 | 147077211 | 147077366 | chr3 | 147078865 | 147079284 |
| chr3 | 147087472 | 147087891 | chr3 | 147088363 | 147088542 | chr3 | 147088840 | 147089136 |
| chr3 | 147098332 | 147098571 | chr3 | 147105805 | 147106104 | chr3 | 147108758 | 147109766 |
| chr3 | 147110011 | 147110017 | chr3 | 147110055 | 147110115 | chr3 | 147110229 | 147110774 |
| chr3 | 147110835 | 147111188 | chr3 | 147111703 | 147111734 | chr3 | 147126963 | 147127142 |
| chr3 | 147127677 | 147127913 | chr3 | 147136839 | 147137001 | chr3 | 147137076 | 147137268 |
| chr3 | 147138694 | 147138932 | chr3 | 147139272 | 147139631 | chr3 | 147142126 | 147142152 |
| chr3 | 148415327 | 148415746 | chr3 | 148803259 | 148803370 | chr3 | 149374866 | 149375105 |
| chr3 | 150802882 | 150803000 | chr3 | 150803026 | 150803181 | chr3 | 150803941 | 150804180 |
| chr3 | 150804880 | 150804896 | chr3 | 150804937 | 150805119 | chr3 | 152553245 | 152553484 |
| chr3 | 152553573 | 152553807 | chr3 | 152877592 | 152877703 | chr3 | 153838725 | 153838964 |
| chr3 | 153839429 | 153839559 | chr3 | 153839641 | 153839953 | chr3 | 154146034 | 154146395 |
| chr3 | 154146489 | 154146513 | chr3 | 154146572 | 154146991 | chr3 | 154797250 | 154797289 |
| chr3 | 154797377 | 154797778 | chr3 | 156008943 | 156009300 | chr3 | 156009319 | 156009501 |
| chr3 | 156534393 | 156534407 | chr3 | 157155164 | 157155523 | chr3 | 157155922 | 157156298 |
| chr3 | 157812122 | 157812258 | chr3 | 157812437 | 157812721 | chr3 | 157812812 | 167813171 |
| chr3 | 157813507 | 157813605 | chr3 | 157813670 | 157813926 | chr3 | 157815787 | 157815920 |
| chr3 | 157820502 | 157820681 | chr3 | 157821537 | 157821764 | chr3 | 157821939 | 157822106 |
| chr3 | 157823012 | 157823120 | chr3 | 157823139 | 157823228 | chr3 | 157823390 | 157823569 |
| chr3 | 157824052 | 157824147 | chr3 | 157824212 | 157824332 | chr3 | 157824414 | 157824909 |
| chr3 | 157825083 | 157825491 | chr3 | 158288801 | 158288819 | chr3 | 158288887 | 158288974 |
| chr3 | 159756593 | 159756952 | chr3 | 159944397 | 159944636 | chr3 | 160167929 | 160167989 |
| chr3 | 160168071 | 160168108 | chr3 | 164912329 | 164912568 | chr3 | 164912827 | 164913960 |
| chr3 | 164914906 | 164915205 | chr3 | 169376080 | 169376319 | chr3 | 169376581 | 169376878 |
| chr3 | 169539810 | 169540704 | chr3 | 169540967 | 169541134 | chr3 | 170136540 | 170136839 |
| chr3 | 170302528 | 170302767 | chr3 | 170302989 | 170303143 | chr3 | 170303380 | 170303495 |
| chr3 | 170303563 | 170303922 | chr3 | 171527953 | 171528071 | chr3 | 172165356 | 172165785 |
| chr3 | 172165867 | 172166234 | chr3 | 172166236 | 172166513 | chr3 | 172166673 | 172166725 |
| chr3 | 172166783 | 172166894 | chr3 | 172167000 | 172167142 | chr3 | 172167223 | 172167402 |
| chr3 | 172167596 | 172167995 | chr3 | 172355818 | 172355888 | chr3 | 172355903 | 172355997 |
| chr3 | 172425281 | 172425382 | chr3 | 172425701 | 172425802 | chr3 | 172469837 | 172469951 |
| chr3 | 173115155 | 173115634 | chr3 | 173302464 | 173302669 | chr3 | 173302735 | 173302763 |
| chr3 | 173302900 | 173303319 | chr3 | 178861414 | 178861533 | chr3 | 178916788 | 178916967 |
| chr3 | 178921465 | 178921644 | chr3 | 178935968 | 178936205 | chr3 | 178951997 | 178952176 |
| chr3 | 179168582 | 179169354 | chr3 | 179754086 | 179764193 | chr3 | 179754239 | 179754483 |

TABLE 15-continued

| chr | start | end | chr | start | end | chr | start | end |
|---|---|---|---|---|---|---|---|---|
| chr3 | 179754485 | 179754760 | chr3 | 179754804 | 179754873 | chr3 | 179755087 | 179755465 |
| chr3 | 181413068 | 181413069 | chr3 | 181413422 | 181413460 | chr3 | 181413642 | 181414426 |
| chr3 | 181419972 | 181420211 | chr3 | 181420226 | 181420465 | chr3 | 181421308 | 181422387 |
| chr3 | 181422464 | 181423063 | chr3 | 18:428311 | 181428850 | chr3 | 181430614 | 181430853 |
| chr3 | 181437030 | 181437299 | chr3 | 181437301 | 181437449 | chr3 | 181438095 | 181438454 |
| chr3 | 181440811 | 181442010 | chr3 | 18:442069 | 181442426 | chr3 | 181442964 | 181443550 |
| chr3 | 181444051 | 181444322 | chr3 | 181444335 | 181444525 | chr3 | 181444613 | 181444754 |
| chr3 | 181444828 | 181444949 | chr3 | 18:444989 | 181444989 | chr3 | 181444991 | 18:445114 |
| chr3 | 181445268 | 181445567 | chr3 | 181445649 | 181445725 | chr3 | 181445800 | 181445948 |
| chr3 | 182816010 | 182816129 | chr3 | 182895871 | 182895990 | chr3 | 183145336 | 183145695 |
| chr3 | 183145829 | 183146128 | chr3 | 183146297 | 183146536 | chr3 | 183146574 | 183146753 |
| chr3 | 183648036 | 183648101 | chr3 | 183728814 | 183728926 | chr3 | 183965514 | 183965625 |
| chr3 | 184017964 | 184018237 | chr3 | 184031615 | 184031734 | chr3 | 184057527 | 184057636 |
| chr3 | 184301634 | 184301671 | chr3 | 184319741 | 184319843 | chr3 | 184319874 | 184319980 |
| chr3 | 185001908 | 185002018 | chr3 | 185271201 | 185271380 | chr3 | 185303173 | 185303352 |
| chr3 | 185362989 | 185363348 | chr3 | 185643246 | 185643485 | chr3 | 186078683 | 186078982 |
| chr3 | 186079119 | 186079412 | chr3 | 186080114 | 186080245 | chr3 | 186080247 | 186080293 |
| chr3 | 186857051 | 186857710 | chr3 | 187387776 | 187387921 | chr3 | 187388007 | 187388315 |
| chr3 | 192125754 | 192125829 | chr3 | 192126116 | 192126131 | chr3 | 192126787 | 192126849 |
| chr3 | 192126851 | 192126955 | chr3 | 192127265 | 192127373 | chr3 | 192127557 | 192127731 |
| chr3 | 192127937 | 192128164 | chr3 | 192232017 | 192232077 | chr3 | 192232079 | 192232256 |
| chr3 | 192232362 | 192232432 | chr3 | 192232478 | 192232661 | chr3 | 192232753 | 192232819 |
| chr3 | 192232850 | 192232952 | chr3 | 192233095 | 192233232 | chr3 | 192958830 | 192959057 |
| chr3 | 193312046 | 193312165 | chr3 | 193419628 | 193419745 | chr3 | 193548557 | 193548797 |
| chr3 | 193548842 | 193548916 | chr3 | 193776015 | 193776194 | chr3 | 194048731 | 194049015 |
| chr3 | 194208185 | 194208258 | chr3 | 194208468 | 194208664 | chr3 | 194407924 | 194407936 |
| chr3 | 194408055 | 194408103 | chr3 | 194408279 | 194408769 | chr3 | 194408839 | 194409118 |
| chr3 | 195536642 | 195536828 | chr3 | 195538330 | 195538435 | chr3 | 195586956 | 195587195 |
| chr3 | 195601157 | 195601363 | chr3 | 195602364 | 195602435 | chr3 | 195648720 | 195648899 |
| chr3 | 196069893 | 196070192 | chr3 | 196255543 | 196255632 | chr3 | 196387206 | 196387505 |
| chr3 | 196387528 | 196387767 | chr3 | 196388303 | 196388662 | chr3 | 196731055 | 196731133 |
| chr3 | 196731197 | 196731414 | chr3 | 196755893 | 196756063 | chr3 | 197327025 | 197327131 |
| chr3 | 197616633 | 197616812 | chr3 | 197676955 | 197677134 | chr3 | 197685698 | 197685817 |
| chr3 | 197686060 | 197686177 | chr3 | 197686891 | 197687310 | chr4 | 330716 | 330790 |
| chr4 | 331308 | 331416 | chr4 | 568333 | 568653 | chr4 | 569048 | 569116 |
| chr4 | 569275 | 569436 | chr4 | 569461 | 569733 | chr4 | 570931 | 571110 |
| chr4 | 571420 | 571779 | chr4 | 628488 | 628770 | chr4 | 651110 | 651348 |
| chr4 | 657570 | 657657 | chr4 | 678397 | 678576 | chr4 | 718082 | 718202 |
| chr4 | 718240 | 718321 | chr4 | 829537 | 829716 | chr4 | 955292 | 955531 |
| chr4 | 955774 | 956013 | chr4 | 995876 | 995994 | chr4 | 996101 | 996175 |
| chr4 | 1008642 | 1008806 | chr4 | 1016332 | 1016340 | chr4 | 1016533 | 1016787 |
| chr4 | 1025852 | 1026151 | chr4 | 1093452 | 1093558 | chr4 | 1165276 | 1165287 |
| chr4 | 1165450 | 1165575 | chr4 | 1188947 | 1189126 | chr4 | 1282441 | 1282620 |
| chr4 | 1331636 | 1331780 | chr4 | 1338615 | 1338891 | chr4 | 1339023 | 1339130 |
| chr4 | 1396498 | 1396593 | chr4 | 1396595 | 1396697 | chr4 | 1397297 | 1397595 |
| chr4 | 1398222 | 1398247 | chr4 | 1398264 | 1398461 | chr4 | 1399627 | 1399633 |
| chr4 | 1401643 | 1401847 | chr4 | 1512294 | 1512473 | chr4 | 1556335 | 1556603 |
| chr4 | 1576387 | 1576626 | chr4 | 1616606 | 1617173 | chr4 | 1687006 | 1687185 |
| chr4 | 1803447 | 1803686 | chr4 | 1806010 | 1806089 | chr4 | 1807281 | 1807460 |
| chr4 | 1993677 | 1994276 | chr4 | 2042117 | 2042123 | chr4 | 2042169 | 2042259 |
| chr4 | 2066011 | 2066370 | chr4 | 2305571 | 2305930 | chr4 | 2527903 | 2528012 |
| chr4 | 2540247 | 2540395 | chr4 | 2765767 | 2766006 | chr4 | 2926292 | 2926471 |
| chr4 | 2978878 | 2979094 | chr4 | 3446917 | 3447096 | chr4 | 3447737 | 3448096 |
| chr4 | 3768759 | 3768950 | chr4 | 3768995 | 3769190 | chr4 | 3769560 | 3769665 |
| chr4 | 3873613 | 3873852 | chr4 | 4228094 | 4228168 | chr4 | 4228189 | 4228333 |
| chr4 | 4229586 | 4229885 | chr4 | 4387431 | 4387734 | chr4 | 4417467 | 4417706 |
| chr4 | 4855018 | 4855192 | chr4 | 4855231 | 4855257 | chr4 | 4855283 | 4855522 |
| chr4 | 4862671 | 4863210 | chr4 | 4867613 | 4867864 | chr4 | 4867924 | 4867972 |
| chr4 | 4868468 | 4868793 | chr4 | 4868829 | 4869000 | chr4 | 4869132 | 4869187 |
| chr4 | 4872009 | 4872032 | chr4 | 4872060 | 4872248 | chr4 | 4872695 | 4872934 |
| chr4 | 4873329 | 4873580 | chr4 | 5052995 | 5053594 | chr4 | 5053651 | 5054190 |
| chr4 | 5709819 | 5709985 | chr4 | 5712891 | 5713232 | chr4 | 5713327 | 5713370 |
| chr4 | 5889848 | 5890147 | chr4 | 5890180 | 5890539 | chr4 | 5891871 | 5892082 |
| chr4 | 5892110 | 5892251 | chr4 | 5892675 | 5892791 | chr4 | 5893898 | 5894083 |
| chr4 | 5894600 | 5894633 | chr4 | 5894813 | 5894882 | chr4 | 6200797 | 6201293 |
| chr4 | 6202011 | 6202370 | chr4 | 6247277 | 6247456 | chr4 | 6564904 | 6565143 |
| chr4 | 6670110 | 6670289 | chr4 | 6748251 | 6748662 | chr4 | 6957489 | 6957701 |
| chr4 | 7647679 | 7648038 | chr4 | 7758402 | 7758581 | chr4 | 8582475 | 8582619 |
| chr4 | 8607724 | 8608023 | chr4 | 8608459 | 8608698 | chr4 | 8858804 | 8859048 |
| chr4 | 8859382 | 8859823 | chr4 | 8859875 | 8859938 | chr4 | 8860398 | 8860654 |
| chr4 | 8861606 | 8861753 | chr4 | 8861919 | 8862102 | chr4 | 8862705 | 8862812 |
| chr4 | 8863339 | 8863527 | chr4 | 8863857 | 8863878 | chr4 | 8864434 | 8864683 |
| chr4 | 8864764 | 8865155 | chr4 | 8868734 | 8868846 | chr4 | 8868932 | 8869271 |
| chr4 | 8869369 | 8869453 | chr4 | 8869498 | 8869917 | chr4 | 8872957 | 8873073 |
| chr4 | 8873774 | 8874077 | chr4 | 8874397 | 8874535 | chr4 | 8874773 | 8874812 |
| chr4 | 8875803 | 8875982 | chr4 | 8893427 | 8893606 | chr4 | 8893714 | 8893726 |
| chr4 | 8893816 | 8894013 | chr4 | 8894547 | 8894958 | chr4 | 8895232 | 8895446 |
| chr4 | 8895480 | 8895659 | chr4 | 8895965 | 8896098 | chr4 | 8896118 | 8896134 |

TABLE 15-continued

| chr | start | end | chr | start | end | chr | start | end |
|---|---|---|---|---|---|---|---|---|
| chr4 | 9423195 | 9423281 | chr4 | 9782942 | 9783096 | chr4 | 9783126 | 9783424 |
| chr4 | 9783501 | 9783502 | chr4 | 10458309 | 10459208 | chr4 | 10462740 | 10463048 |
| chr4 | 10463073 | 10463256 | chr4 | 10463258 | 10463636 | chr4 | 11429482 | 11429720 |
| chr4 | 13523929 | 13524252 | chr4 | 13524571 | 13524872 | chr4 | 13537492 | 13537779 |
| chr4 | 13540946 | 13541146 | chr4 | 13541309 | 13541348 | chr4 | 13545941 | 13546172 |
| chr4 | 13548404 | 13548590 | chr4 | 13548635 | 13548999 | chr4 | 13549246 | 13549605 |
| chr4 | 15780123 | 15780422 | chr4 | 16084642 | 16084819 | chr4 | 16085167 | 16085180 |
| chr4 | 16085182 | 16085302 | chr4 | 16085352 | 16085481 | chr4 | 16085531 | 16085602 |
| chr4 | 16085675 | 16085770 | chr4 | 17782913 | 17783294 | chr4 | 17783296 | 17783322 |
| chr4 | 17783324 | 17783481 | chr4 | 17783610 | 17783692 | chr4 | 20254619 | 20254774 |
| chr4 | 20255339 | 20255368 | chr4 | 20255525 | 20255938 | chr4 | 20256067 | 20256286 |
| chr4 | 20256383 | 20256426 | chr4 | 21950146 | 21950155 | chr4 | 21950157 | 21950296 |
| chr4 | 24801868 | 24802053 | chr4 | 24914564 | 24914743 | chr4 | 25656728 | 25656893 |
| chr4 | 25657338 | 25657365 | chr4 | 25657357 | 25657414 | chr4 | 25657416 | 25657577 |
| chr4 | 27086358 | 27086537 | chr4 | 30724162 | 30724461 | chr4 | 37245837 | 37245939 |
| chr4 | 37246060 | 37246361 | chr4 | 37246490 | 37246700 | chr4 | 37247016 | 37247238 |
| chr4 | 37247294 | 37247306 | chr4 | 40910205 | 40910563 | chr4 | 41258624 | 41258789 |
| chr4 | 41259086 | 41259276 | chr4 | 41746922 | 41747221 | chr4 | 41747419 | 41747658 |
| chr4 | 41747889 | 41747977 | chr4 | 41748144 | 41748397 | chr4 | 41748583 | 41748767 |
| chr4 | 41748857 | 41748882 | chr4 | 41748976 | 41749138 | chr4 | 41749187 | 41749846 |
| chr4 | 41750125 | 41750604 | chr4 | 41751789 | 41751990 | chr4 | 41752363 | 41752782 |
| chr4 | 41752884 | 41753483 | chr4 | 41753512 | 41753712 | chr4 | 41753714 | 41753803 |
| chr4 | 41753805 | 41753917 | chr4 | 41754031 | 41754171 | chr4 | 41875337 | 41875891 |
| chr4 | 41881286 | 41881517 | chr4 | 41882469 | 41882533 | chr4 | 41882652 | 41882682 |
| chr4 | 41882988 | 41883407 | chr4 | 41883411 | 41883710 | chr4 | 41993731 | 41993896 |
| chr4 | 42152962 | 42153412 | chr4 | 42153533 | 42153633 | chr4 | 42153882 | 42154127 |
| chr4 | 42154201 | 42154385 | chr4 | 42154387 | 42154440 | chr4 | 42154561 | 42155100 |
| chr4 | 42398768 | 42398947 | chr4 | 42399045 | 42399284 | chr4 | 42399601 | 42399960 |
| chr4 | 44449387 | 44449570 | chr4 | 44449653 | 44449743 | chr4 | 44450170 | 44450177 |
| chr4 | 46995079 | 46995821 | chr4 | 46995823 | 46995918 | chr4 | 47034834 | 47035013 |
| chr4 | 48485152 | 48485289 | chr4 | 48485590 | 48486104 | chr4 | 48486254 | 48486493 |
| chr4 | 48492100 | 48492517 | chr4 | 48988013 | 48988229 | chr4 | 48988380 | 48988432 |
| chr4 | 53728417 | 53729087 | chr4 | 54966756 | 54967175 | chr4 | 54967264 | 54967563 |
| chr4 | 54969832 | 54970174 | chr4 | 54970277 | $4970576 | chr4 | 54975855 | 54975932 |
| chr4 | 54975991 | $4976116 | chr4 | 54976171 | 54976214 | chr4 | 55092973 | 55093332 |
| chr4 | 55096143 | 55096363 | chr4 | 55096441 | 55096442 | chr4 | 55097315 | 55097554 |
| chr4 | 55097709 | 55097729 | chr4 | 55097874 | 55098093 | chr4 | 55098198 | 55098473 |
| chr4 | 55098590 | 55098769 | chr4 | 55099040 | 55099:59 | chr4 | 55524138 | 55524367 |
| chr4 | 55991019 | 55991270 | chr4 | 55992030 | 55992090 | chr4 | 55992153 | 55992269 |
| chr4 | 56659618 | 56659867 | chr4 | 56659935 | 56660097 | chr4 | 57371632 | 57371868 |
| chr4 | 57371870 | 57372051 | chr4 | 57372241 | 57372600 | chr4 | 57396866 | 57397345 |
| chr4 | 57521300 | 57521396 | chr4 | 57521506 | 57521664 | chr4 | 57521701 | 57522383 |
| chr4 | 57522420 | 57522908 | chr4 | 57687632 | 57687871 | chr4 | 57777338 | 57777577 |
| chr4 | 57803529 | 57803613 | chr4 | 57975930 | 57976289 | chr4 | 57976316 | 57976675 |
| chr4 | 62066134 | 62066645 | chr4 | 62067419 | 62067718 | chr4 | 62067992 | 62068202 |
| chr4 | 66535048 | 66535315 | chr4 | 66535351 | 66535483 | chr4 | 66536068 | 66536427 |
| chr4 | 74702379 | 74702448 | chr4 | 74702450 | 74702608 | chr4 | 74809786 | 74810025 |
| chr4 | 75241349 | 75241528 | chr4 | 75858482 | 75858611 | chr4 | 76555455 | 76555547 |
| chr4 | 76555549 | 76555934 | chr4 | 76912717 | 76912836 | chr4 | 79689573 | 79689812 |
| chr4 | 81106252 | 81106663 | chr4 | 81106665 | 81106669 | chr4 | 81124201 | 81124740 |
| chr4 | 81186972 | 81187151 | chr4 | 81187485 | 81187664 | chr4 | 81188230 | 81188316 |
| chr4 | 81188385 | 81188644 | chr4 | 81189336 | 81189661 | chr4 | 81189714 | 81189995 |
| chr4 | 81951357 | 81951536 | chr4 | 81951938 | 81952046 | chr4 | 81952078 | 81952312 |
| chr4 | 81952364 | 81952437 | chr4 | 82135786 | 82135888 | chr4 | 82135920 | 82136145 |
| chr4 | 82136403 | 82136642 | chr4 | 82136733 | 82136912 | chr4 | 83323428 | 83323677 |
| chr4 | 85402748 | 85403425 | chr4 | 85403824 | 85403928 | chr4 | 85404112 | 85404141 |
| chr4 | 85404225 | 85404476 | chr4 | 85404650 | 85404783 | chr4 | 85413977 | 85414114 |
| chr4 | 85414149 | 85414244 | chr4 | 85414270 | 85414337 | chr4 | 85414458 | 85414509 |
| chr4 | 85414637 | 85414936 | chr4 | 85417241 | 85417474 | chr4 | 85417517 | 85417660 |
| chr4 | 85417873 | 85418166 | chr4 | 85418319 | 85418370 | chr4 | 85418522 | 85418583 |
| chr4 | 85422101 | 85422520 | chr4 | 85422866 | 85422929 | chr4 | 85422973 | 85423052 |
| chr4 | 85424323 | 85424562 | chr4 | 87515263 | 87515442 | chr4 | 89378362 | 89378601 |
| chr4 | 89378667 | 89378767 | chr4 | 89378832 | 89378966 | chr4 | 90257439 | 90757913 |
| chr4 | 90758031 | 90758210 | chr4 | 90758681 | 90758980 | chr4 | 93225163 | 93225252 |
| chr4 | 93226367 | 93226380 | chr4 | 93226382 | 93226606 | chr4 | 93226729 | 93226958 |
| chr4 | 94750882 | 94751241 | chr4 | 94751342 | 94751581 | chr4 | 94753341 | 94753520 |
| chr4 | 94756002 | 94756186 | chr4 | 95127560 | 95127679 | chr4 | 96470678 | 96470857 |
| chr4 | 101111166 | 101111585 | chr4 | 101111765 | 101111872 | chr4 | 101111874 | 101112058 |
| chr4 | 107955210 | 107955929 | chr4 | 107956582 | 107957181 | chr4 | 107957271 | 107957362 |
| chr4 | 107957364 | 107957570 | chr4 | 109093016 | 109093255 | chr4 | 109093307 | 109093606 |
| chr4 | 110222996 | 110223428 | chr4 | 110223579 | 110223598 | chr4 | 110223600 | 110223967 |
| chr4 | 110223969 | 110224075 | chr4 | 111532705 | 111533037 | chr4 | 111536192 | 111536506 |
| chr4 | 111536562 | 111536791 | chr4 | 111536882 | 111536975 | chr4 | 111537067 | 111537156 |
| chr4 | 111537356 | 111537572 | chr4 | 111540187 | 111540460 | chr4 | 111542474 | 111542570 |
| chr4 | 111542728 | 111542832 | chr4 | 111543132 | 111543346 | chr4 | 111543404 | 111543551 |
| chr4 | 111543579 | 111543696 | chr4 | 111543721 | 111543807 | chr4 | 111544303 | 111544662 |
| chr4 | 111549726 | 111549905 | chr4 | 111550517 | 111550930 | chr4 | 111552044 | 111552223 |
| chr4 | 111553005 | 111553545 | chr4 | 111553815 | 111564054 | chr4 | 111554854 | 111554965 |

TABLE 15-continued

| chr | start | end | chr | start | end | chr | start | end |
|---|---|---|---|---|---|---|---|---|
| chr4 | 111555194 | 111555447 | chr4 | 111557888 | 111558127 | chr4 | 111558499 | 111559312 |
| chr4 | 111560174 | 111560713 | chr4 | 111562493 | 111562732 | chr4 | 113154804 | 113155043 |
| chr4 | 113430537 | 113430776 | chr4 | 113431755 | 113431855 | chr4 | 113431916 | 113432155 |
| chr4 | 113432227 | 113432504 | chr4 | 113432519 | 113432654 | chr4 | 113436133 | 113436372 |
| chr4 | 113441514 | 113441813 | chr4 | 113442013 | 113442186 | chr4 | 113442247 | 113442612 |
| chr4 | 113444003 | 113444295 | chr4 | 113444297 | 113444534 | chr4 | 117847310 | 117847459 |
| chr4 | 117847470 | 117847549 | chr4 | 121843986 | 121844285 | chr4 | 121992170 | 121992409 |
| chr4 | 121993915 | 121994334 | chr4 | 122301405 | 122301713 | chr4 | 122302032 | 122302331 |
| chr4 | 122685744 | 122685891 | chr4 | 122686119 | 122686453 | chr4 | 122686455 | 122686598 |
| chr4 | 122871195 | 122871434 | chr4 | 122871488 | 122872087 | chr4 | 123664147 | 123664249 |
| chr4 | 126237252 | 126237491 | chr4 | 126237552 | 126237701 | chr4 | 126237931 | 126238511 |
| chr4 | 128543956 | 128544255 | chr4 | 128544569 | 128544868 | chr4 | 134067794 | 134068093 |
| chr4 | 134068475 | 134068777 | chr4 | 134068779 | 134068894 | chr4 | 134069215 | 134069394 |
| chr4 | 134069498 | 134069977 | chr4 | 134070300 | 134070369 | chr4 | 134070371 | 134070479 |
| chr4 | 134071559 | 134072611 | chr4 | 134072677 | 134073058 | chr4 | 134073128 | 134073403 |
| chr4 | 134073486 | 134073725 | chr4 | 134073772 | 134073789 | chr4 | 134073944 | 134074243 |
| chr4 | 140200422 | 140201157 | chr4 | 140201193 | 140201566 | chr4 | 140657000 | 140657166 |
| chr4 | 141347925 | 141348227 | chr4 | 141418841 | 141419500 | chr4 | 141488790 | 141489159 |
| chr4 | 142053155 | 142053235 | chr4 | 142053418 | 142063837 | chr4 | 142054141 | 142054254 |
| chr4 | 142064256 | 142054550 | chr4 | 143766714 | 143767013 | chr4 | 144621248 | 144621440 |
| chr4 | 144621515 | 144621897 | chr4 | 144621982 | 144622147 | chr4 | 145567951 | 145568250 |
| chr4 | 145568361 | 145568745 | chr4 | 146853937 | 146854056 | chr4 | 147558179 | 147558382 |
| chr4 | 147558477 | 147558598 | chr4 | 147559220 | 147560079 | chr4 | 147560134 | 147560419 |
| chr4 | 147560460 | 147560659 | chr4 | 147560835 | 147561146 | chr4 | 147561360 | 147561950 |
| chr4 | 147562000 | 147562154 | chr4 | 147568549 | 147569148 | chr4 | 147569546 | 147569685 |
| chr4 | 147569697 | 147569725 | chr4 | 147576079 | 147576202 | chr4 | 147576330 | 147576738 |
| chr4 | 152246058 | 152246237 | chr4 | 152246398 | 152246403 | chr4 | 153249297 | 153249476 |
| chr4 | 153702690 | 153702805 | chr4 | 154216277 | 154216449 | chr4 | 154709440 | 154709611 |
| chr4 | 154709759 | 154709828 | chr4 | 154709830 | 154710598 | chr4 | 154710600 | 154710618 |
| chr4 | 154710729 | 154710999 | chr4 | 154712084 | 154712683 | chr4 | 154713426 | 154713605 |
| chr4 | 154713861 | 154714085 | chr4 | 155254092 | 155254271 | chr4 | 155411411 | 155411494 |
| chr4 | 155411930 | 155412370 | chr4 | 155663476 | 155663728 | chr4 | 155665371 | 155665550 |
| chr4 | 156129079 | 156129258 | chr4 | 156129354 | 156129387 | chr4 | 156129444 | 156129593 |
| chr4 | 156129653 | 156129892 | chr4 | 156129963 | 156130382 | chr4 | 156297337 | 156297636 |
| chr4 | 156297942 | 156298130 | chr4 | 156588237 | 156588245 | chr4 | 156588364 | 156588476 |
| chr4 | 156589179 | 156589203 | chr4 | 156589259 | 156589418 | chr4 | 156680156 | 156680485 |
| chr4 | 156680596 | 156680635 | chr4 | 156681281 | 156681465 | chr4 | 158141502 | 158141657 |
| chr4 | 158142744 | 158143101 | chr4 | 168143355 | 158143466 | chr4 | 158143610 | 158143654 |
| chr4 | 164252890 | 164253207 | chr4 | 164253209 | 164253549 | chr4 | 165304428 | 165304667 |
| chr4 | 165304948 | 165305024 | chr4 | 165305060 | 165305247 | chr4 | 166414897 | 166414996 |
| chr4 | 166794691 | 166794990 | chr4 | 166795933 | 166795993 | chr4 | 166796118 | 166796292 |
| chr4 | 168155010 | 168155124 | chr4 | 168155126 | 168155369 | chr4 | 170865262 | 170865381 |
| chr4 | 170947187 | 170947426 | chr4 | 172734067 | 172734148 | chr4 | 172734189 | 172734276 |
| chr4 | 172734278 | 172734306 | chr4 | 172734592 | 172734860 | chr4 | 174429584 | 174429763 |
| chr4 | 174430212 | 174430554 | chr4 | 174430794 | 174431171 | chr4 | 174438477 | 174438622 |
| chr4 | 174439741 | 174440340 | chr4 | 174440555 | 174440794 | chr4 | 174443138 | 174443317 |
| chr4 | 174443480 | 174444019 | chr4 | 174444199 | 174444256 | chr4 | 174446508 | 174446595 |
| chr4 | 174449847 | 174450408 | chr4 | 174450410 | 174450727 | chr4 | 174450752 | 174451586 |
| chr4 | 174451768 | 174452187 | chr4 | 174459094 | 174459375 | chr4 | 174459528 | 174459747 |
| chr4 | 174459770 | 174459933 | chr4 | 174460085 | 174460309 | chr4 | 175132661 | 175132840 |
| chr4 | 175132994 | 175133293 | chr4 | 175134806 | 175135765 | chr4 | 175135847 | 175136086 |
| chr4 | 175138419 | 175138629 | chr4 | 175138870 | 175139349 | chr4 | 175139473 | 175139772 |
| chr4 | 175750358 | 175750805 | chr4 | 176923342 | 176923641 | chr4 | 176987230 | 176987313 |
| chr4 | 176987315 | 176987448 | chr4 | 177713154 | 177713513 | chr4 | 180979196 | 180979375 |
| chr4 | 180980208 | 180980447 | chr4 | 183063573 | 183063973 | chr4 | 183063995 | 183064048 |
| chr4 | 183064517 | 183064756 | chr4 | 183064771 | 183065070 | chr4 | 184019164 | 184019403 |
| chr4 | 184019595 | 184019834 | chr4 | 184020043 | 184020263 | chr4 | 184375709 | 184375816 |
| chr4 | 184718157 | 184718456 | chr4 | 184826157 | 184826576 | chr4 | 184826976 | 184827328 |
| chr4 | 184921806 | 184922165 | chr4 | 185089598 | 185089897 | chr4 | 185937252 | 185937971 |
| chr4 | 185938412 | 185938651 | chr4 | 185940250 | 185940549 | chr4 | 185941484 | 185942473 |
| chr4 | 185942492 | 185942863 | chr5 | 53756 | 53899 | chr5 | 92072 | 92210 |
| chr5 | 320762 | 321061 | chr5 | 343957 | 344017 | chr5 | 373976 | 374369 |
| chr5 | 400112 | 400291 | chr5 | 480918 | 481032 | chr5 | 491257 | 491616 |
| chr5 | 524252 | 524491 | chr5 | 538663 | 538902 | chr5 | 554212 | 554569 |
| chr5 | 554812 | 554916 | chr5 | 555193 | 555372 | chr5 | 556891 | 556070 |
| chr5 | 677799 | 678098 | chr5 | 1034508 | 1034747 | chr5 | 1131130 | 1131478 |
| chr5 | 1193302 | 1193465 | chr5 | 1193793 | 1194032 | chr5 | 1221103 | 1221402 |
| chr5 | 1294550 | 1294849 | chr5 | 1294928 | 1295443 | chr5 | 1295605 | 1295724 |
| chr5 | 1295759 | 1295767 | chr5 | 1445078 | 1445256 | chr5 | 1445654 | 1445760 |
| chr5 | 1445841 | 1446013 | chr5 | 1446237 | 1446370 | chr5 | 1446443 | 1446699 |
| chr5 | 1746941 | 1747180 | chr5 | 1874877 | 1875176 | chr5 | 1875356 | 1875595 |
| chr5 | 1875796 | 1876307 | chr5 | 1876638 | 1876921 | chr5 | 1877090 | 1877103 |
| chr5 | 1877195 | 1877320 | chr5 | 1877912 | 1878029 | chr5 | 1878224 | 1878577 |
| chr5 | 1878831 | 1879090 | chr5 | 1879513 | 1879662 | chr5 | 1879690 | 1879812 |
| chr5 | 1882420 | 1882690 | chr5 | 1882758 | 1882922 | chr5 | 1883132 | 1883177 |
| chr5 | 1883429 | 1883617 | chr5 | 1883880 | 1883908 | chr5 | 1884089 | 1884328 |
| chr5 | 1884479 | 1884778 | chr5 | 1885069 | 1885548 | chr5 | 1885910 | 1886077 |
| chr5 | 1886443 | 1886682 | chr5 | 1886736 | 1886842 | chr5 | 1886998 | 1887146 |

TABLE 15-continued

| chr | start | end | chr | start | end | chr | start | end |
|---|---|---|---|---|---|---|---|---|
| chr5 | 1887547 | 1887582 | chr5 | 1887656 | 1887815 | chr5 | 1930701 | 1931005 |
| chr5 | 1931065 | 1931287 | chr5 | 1931445 | 1931577 | chr5 | 1931618 | 1931840 |
| chr5 | 1950698 | 1951057 | chr5 | 1952550 | 1952639 | chr5 | 1952724 | 1952729 |
| chr5 | 2038629 | 2038863 | chr5 | 2324309 | 2324488 | chr5 | 2541400 | 2541699 |
| chr5 | 2738746 | 2739130 | chr5 | 2739211 | 2739355 | chr5 | 2739780 | 2739803 |
| chr5 | 2739861 | 2740301 | chr5 | 2740431 | 2740665 | chr5 | 2741123 | 2741139 |
| chr5 | 2743616 | 2743660 | chr5 | 2743699 | 2743815 | chr5 | 2748298 | 274.8490 |
| chr5 | 2749110 | 2749407 | chr5 | 2749625 | 2749777 | chr5 | 2750655 | 2750770 |
| chr5 | 2751855 | 2751974 | chr5 | 2752897 | 2753153 | chr5 | 2754664 | 2754703 |
| chr5 | 2754804 | 2754807 | chr5 | 2755227 | 2756486 | chr5 | 2756504 | 2756603 |
| chr5 | 2756674 | 2757523 | chr5 | 3031800 | 3032099 | chr5 | 3324948 | 3325367 |
| chr5 | 3590314 | 3590658 | chr5 | 3590804 | 3590853 | chr5 | 3591252 | 3591491 |
| chr5 | 3591768 | 3592127 | chr5 | 3592643 | 3592961 | chr5 | 3594155 | 3594520 |
| chr5 | 3594778 | 3594814 | chr5 | 3595056 | 3595254 | chr5 | 3595361 | 3595369 |
| chr5 | 3595850 | 3596080 | chr5 | 3596556 | 3596725 | chr5 | 3596825 | 3596980 |
| chr5 | 3597317 | 3597556 | chr5 | 3600076 | 3600255 | chr5 | 3602717 | 3603422 |
| chr5 | 3606712 | 3606771 | chr5 | 3673960 | 3674256 | chr5 | 4144300 | 4144592 |
| chr5 | 5139578 | 5139621 | chr5 | 5139754 | 5139997 | chr5 | 5140079 | 5140318 |
| chr5 | 5140528 | 5140758 | chr5 | 5140850 | 5141006 | chr5 | 6228525 | 6228650 |
| chr5 | 6448837 | 6449676 | chr5 | 6583371 | 6583670 | chr5 | 6687175 | 6687528 |
| chr5 | 7395162 | 7395394 | chr5 | 7395434 | 7395641 | chr5 | 7850251 | 7850286 |
| chr5 | 7850919 | 7851218 | chr5 | 9546511 | 9546750 | chr5 | 10333611 | 10334210 |
| chr5 | 10564925 | 10565228 | chr5 | 10565263 | 10565463 | chr5 | 10565265 | 10565704 |
| chr5 | 11384965 | 11385067 | chr5 | 11385069 | 11385465 | chr5 | 11903659 | 11903725 |
| chr5 | 11903822 | 11904114 | chr5 | 11904116 | 11904174 | chr5 | 11904195 | 11904380 |
| chr5 | 11904456 | 11904798 | chr5 | 11904801 | 11906040 | chr5 | 15500659 | 15500689 |
| chr5 | 15500736 | 15500833 | chr5 | 15500835 | 15501018 | chr5 | 16178946 | 16179153 |
| chr5 | 16179555 | 16179795 | chr5 | 16180183 | 16180321 | chr5 | 16466683 | 16466796 |
| chr5 | 16467097 | 16467216 | chr5 | 16936255 | 16936402 | chr5 | 16936500 | 16936614 |
| chr5 | 17203036 | 17203266 | chr5 | 17217854 | 17217865 | chr5 | 17217992 | 17218033 |
| chr5 | 17218121 | 17218300 | chr5 | 17218862 | 17218934 | chr5 | 17218986 | 17219101 |
| chr5 | 17512040 | 17512192 | chr5 | 22853425 | 22853596 | chr5 | 31193844 | 31194083 |
| chr5 | 31194312 | 31194511 | chr5 | 31639583 | 31640008 | chr5 | 31691580 | 31691745 |
| chr5 | 31854987 | 31855286 | chr5 | 32710252 | 32710551 | chr5 | 32710718 | 32710957 |
| chr5 | 32711024 | 32711429 | chr5 | 32711431 | 32711617 | chr5 | 32711729 | 32711968 |
| chr5 | 32711985 | 32712102 | chr5 | 32712290 | 32712584 | chr5 | 32712675 | 32712943 |
| chr5 | 33298097 | 33298101 | chr5 | 33891980 | 33892219 | chr5 | 33892339 | 33892518 |
| chr5 | 33936067 | 33936232 | chr5 | 33936234 | 33936362 | chr5 | 33936364 | 33936751 |
| chr5 | 34656834 | 34657042 | chr5 | 37834610 | 37834737 | chr5 | 37836572 | 37838071 |
| chr5 | 37838448 | 37838987 | chr5 | 37839684 | 37839736 | chr5 | 37839808 | 37840075 |
| chr5 | 37840077 | 37840220 | chr5 | 37840288 | 37840363 | chr5 | 37840530 | 37840843 |
| chr5 | 38257397 | 38257541 | chr5 | 38257543 | 38257696 | chr5 | 38257752 | 38257909 |
| chr5 | 38257945 | 38258051 | chr5 | 38556996 | 38557076 | chr5 | 38557188 | 38557427 |
| chr5 | 38845574 | 38845955 | chr5 | 38846469 | 38846533 | chr5 | 39343086 | 39343201 |
| chr5 | 40681036 | 40681228 | chr5 | 40681262 | 40681455 | chr5 | 40681601 | 40681840 |
| chr5 | 40682070 | 40682080 | chr5 | 42424732 | 42425151 | chr5 | 42950902 | 42951312 |
| chr5 | 42951420 | 42952112 | chr5 | 42991751 | 42992242 | chr5 | 42992376 | 42992555 |
| chr5 | 42992557 | 42992598 | chr5 | 42992783 | 42993010 | chr5 | 42993313 | 42993547 |
| chr5 | 42993853 | 42994272 | chr5 | 42994593 | 42994892 | chr5 | 42995073 | 42995254 |
| chr5 | 43007862 | 43008041 | chr5 | 43008113 | 43008472 | chr5 | 43017851 | 43018177 |
| chr5 | 43018327 | 43018690 | chr5 | 43019144 | 43019424 | chr5 | 43019729 | 43019968 |
| chr5 | 43040768 | 43041067 | chr5 | 43215459 | 43215562 | chr5 | 43396915 | 43397230 |
| chr5 | 43397306 | 43397334 | chr5 | 44389782 | 44389929 | chr5 | 45695091 | 45695240 |
| chr5 | 45695314 | 45695608 | chr5 | 45695823 | 45695964 | chr5 | 45696239 | 45696455 |
| chr5 | 45696457 | 45696465 | chr5 | 45696467 | 45696538 | chr5 | 49736497 | 49736789 |
| chr5 | 50262842 | 50263104 | chr5 | 50263486 | 50263725 | chr5 | 50264216 | 50264695 |
| chr5 | 50264746 | 50264925 | chr5 | 50265228 | 50265527 | chr5 | 50265621 | 50265672 |
| chr5 | 50265721 | 50265960 | chr5 | 50674051 | 50674290 | chr5 | 50674486 | 50674557 |
| chr5 | 50674638 | 50674665 | chr5 | 50674925 | 50675164 | chr5 | 50678269 | 50678273 |
| chr5 | 50678373 | 50678552 | chr5 | 50695193 | 50695241 | chr5 | 50695351 | 50695540 |
| chr5 | 54179491 | 54179537 | chr5 | 54179539 | 54179558 | chr5 | 54179610 | 54179730 |
| chr5 | 54179989 | 54180168 | chr5 | 54516275 | 54516681 | chr5 | 54516832 | 54517114 |
| chr5 | 54518577 | 54518633 | chr5 | 54519134 | 54519289 | chr5 | 54519383 | 54519406 |
| chr5 | 54527323 | 54527444 | chr5 | 56248119 | 56248358 | chr5 | 57878174 | 57878473 |
| chr5 | 57878612 | 57878775 | chr5 | 57878811 | 57878851 | chr5 | 59188293 | 59188429 |
| chr5 | 59188952 | 59189058 | chr5 | 59189189 | 59189311 | chr5 | 59189787 | 59190026 |
| chr5 | 63254815 | 63255243 | chr5 | 63255316 | 63255354 | chr5 | 63257645 | 63257944 |
| chr5 | 63801932 | 63802272 | chr5 | 63802274 | 63802305 | chr5 | 63802340 | 63802591 |
| chr5 | 63986409 | 63986528 | chr5 | 63986570 | 63986888 | chr5 | 67591197 | 67591233 |
| chr5 | 68391320 | 68391429 | chr5 | 71014629 | 71014979 | chr5 | 71015095 | 71015814 |
| chr5 | 71403491 | 71403730 | chr5 | 71403882 | 71404158 | chr5 | 72416170 | 72416262 |
| chr5 | 72526319 | 72526415 | chr5 | 72526492 | 72526738 | chr5 | 72528360 | 72528539 |
| chr5 | 72529200 | 72529826 | chr5 | 72529890 | 72530699 | chr5 | 72594722 | 72594837 |
| chr5 | 72594868 | 72595017 | chr5 | 72595047 | 72595141 | chr5 | 72595456 | 72595722 |
| chr5 | 72595774 | 72595875 | chr5 | 72598977 | 72598983 | chr5 | 72599060 | 72599442 |
| chr5 | 72599463 | 72599936 | chr5 | 72677775 | 72677826 | chr5 | 72677998 | 72678029 |
| chr5 | 72678366 | 72678416 | chr5 | 72715160 | 72715348 | chr5 | 72715591 | 72715696 |
| chr5 | 72715731 | 72715846 | chr5 | 72716022 | 72716239 | chr5 | 72732870 | 72732910 |

TABLE 15-continued

| chr | start | end | chr | start | end | chr | start | end |
|---|---|---|---|---|---|---|---|---|
| chr5 | 72733013 | 72733268 | chr5 | 72740047 | 72740286 | chr5 | 72746606 | 72746684 |
| chr5 | 72746730 | 72746785 | chr5 | 75377860 | 75378108 | chr5 | 75380089 | 75380268 |
| chr5 | 75380530 | 75381006 | chr5 | 76011192 | 76011431 | chr5 | 76012504 | 76012681 |
| chr5 | 76249176 | 76249671 | chr5 | 76249696 | 76249907 | chr5 | 76249945 | 76250250 |
| chr5 | 76250351 | 76250590 | chr5 | 76506369 | 76506608 | chr5 | 76506956 | 76507195 |
| chr5 | 76923601 | 76924024 | chr5 | 76924087 | 76924300 | chr5 | 76924417 | 76924494 |
| chr5 | 76924856 | 76925018 | chr5 | 76925477 | 76925776 | chr5 | 76928070 | 76928487 |
| chr5 | 76928588 | 76929007 | chr5 | 76932228 | 76932407 | chr5 | 76932463 | 76933266 |
| chr5 | 76934073 | 76934654 | chr5 | 76934677 | 76934972 | chr5 | 76935937 | 76936039 |
| chr5 | 76936100 | 76936819 | chr5 | 76939436 | 76939867 | chr5 | 76940241 | 76940477 |
| chr5 | 76941115 | 76941414 | chr5 | 77140440 | 77140799 | chr5 | 77147520 | 77147650 |
| chr5 | 77147873 | 77148214 | chr5 | 77148396 | 77148669 | chr5 | 77268278 | 77268734 |
| chr5 | 77268736 | 77269238 | chr5 | 77269264 | 77269408 | chr5 | 78407567 | 78407926 |
| chr5 | 78408118 | 78408275 | chr5 | 78408298 | 78408537 | chr5 | 79783152 | 79783256 |
| chr5 | 79864809 | 79865168 | chr5 | 79866100 | 79866508 | chr5 | 79947497 | 79947796 |
| chr5 | 80255722 | 80256075 | chr5 | 80689499 | 80689795 | chr5 | 80690030 | 80690278 |
| chr5 | 82767342 | 82767881 | chr5 | 82768798 | 82769157 | chr5 | 83679121 | 83679300 |
| chr5 | 83679592 | 83679643 | chr5 | 83679645 | 83680431 | chr5 | 83680592 | 83680665 |
| chr5 | 83680694 | 83680812 | chr5 | 87955360 | 87955455 | chr5 | 87955502 | 87955665 |
| chr5 | 87955840 | 87955899 | chr5 | 87956103 | 87956663 | chr5 | 87956680 | 87957062 |
| chr5 | 87962865 | 87963006 | chr5 | 87963365 | 87963601 | chr5 | 87967686 | 87968165 |
| chr5 | 87968411 | 87968686 | chr5 | 87968773 | 87968942 | chr5 | 87970114 | 87970114 |
| chr5 | 87970116 | 87970953 | chr5 | 87974027 | 87974386 | chr5 | 87974767 | 87975126 |
| chr5 | 87976104 | 87976408 | chr5 | 87976423 | 87976662 | chr5 | 87979655 | 87979779 |
| chr5 | 87979900 | 87980014 | chr5 | 87980047 | 87980079 | chr5 | 87980322 | 87980346 |
| chr5 | 87980871 | 87981341 | chr5 | 87985819 | 87986058 | chr5 | 87986127 | 87986154 |
| chr5 | 87986233 | 87986366 | chr5 | 87986445 | 87986472 | chr5 | 87988431 | 87988670 |
| chr5 | 87990311 | 87990530 | chr5 | 88185377 | 88185387 | chr5 | 88185389 | 88186087 |
| chr5 | 89854760 | 89854999 | chr5 | 92939817 | 92939837 | chr5 | 92940178 | 92940236 |
| chr5 | 94955591 | 94956010 | chr5 | 94956849 | 94957088 | chr5 | 94982143 | 94982314 |
| chr5 | 95767856 | 95768035 | chr5 | 95768068 | 95768427 | chr5 | 95768828 | 95769173 |
| chr5 | 100236601 | 100236840 | chr5 | 100238808 | 100238977 | chr5 | 100238979 | 100239022 |
| chr5 | 100239024 | 100239120 | chr5 | 100239135 | 100239167 | chr5 | 101631391 | 101631630 |
| chr5 | 107005906 | 107006265 | chr5 | 111987788 | 111987901 | chr5 | 112043011 | 112043367 |
| chr5 | 112073328 | 112073567 | chr5 | 112175566 | 112175730 | chr5 | 112629342 | 112629359 |
| chr5 | 112629394 | 112629761 | chr5 | 113391163 | 113391218 | chr5 | 113391284 | 113391774 |
| chr5 | 113391776 | 113392122 | chr5 | 113698466 | 113698584 | chr5 | 113698670 | 113698844 |
| chr5 | 113698952 | 113699203 | chr5 | 114515010 | 114515580 | chr5 | 114515611 | 114515728 |
| chr5 | 115161174 | 115151358 | chr5 | 115151650 | 115162385 | chr5 | 115152617 | 115152733 |
| chr5 | 115297105 | 115297293 | chr5 | 115297377 | 115297644 | chr5 | 115297836 | 115297986 |
| chr5 | 115298410 | 115298582 | chr5 | 115298782 | 115298829 | chr5 | 115298894 | 115299133 |
| chr5 | 119799840 | 119800079 | chr5 | 119801223 | 119801522 | chr5 | 121413445 | 121413684 |
| chr5 | 122422161 | 122422315 | chr5 | 122422516 | 122422754 | chr5 | 122423233 | 122423432 |
| chr5 | 122425029 | 122425268 | chr5 | 122431039 | 122431458 | chr5 | 124128503 | 124128574 |
| chr5 | 126626256 | 126626298 | chr5 | 126626300 | 126626795 | chr5 | 127872847 | 127873086 |
| chr5 | 127873553 | 127873789 | chr5 | 127874345 | 127874478 | chr5 | 127874706 | 127874944 |
| chr5 | 128300588 | 128300695 | chr5 | 128300713 | 128300874 | chr5 | 128795984 | 128796097 |
| chr5 | 128796099 | 128796343 | chr5 | 128796777 | 128797076 | chr5 | 128797246 | 128797485 |
| chr5 | 129239966 | 129240205 | chr5 | 131992008 | 131992247 | chr5 | 132947392 | 132947931 |
| chr5 | 133820025 | 133820136 | chr5 | 134366634 | 134366873 | chr5 | 134367007 | 134367266 |
| chr5 | 134367285 | 134367306 | chr5 | 134374370 | 134374506 | chr5 | 134374792 | 134375309 |
| chr5 | 134376120 | 134376474 | chr5 | 134376732 | 134376911 | chr5 | 134385869 | 134386168 |
| chr5 | 134386185 | 134386466 | chr5 | 134582953 | 134582969 | chr5 | 134825372 | 134825611 |
| chr5 | 134825913 | 134826098 | chr5 | 134870362 | 134870601 | chr5 | 134870689 | 134870927 |
| chr5 | 134871526 | 134872125 | chr5 | 134879391 | 134879973 | chr5 | 134914539 | 134914838 |
| chr5 | 135265664 | 135265842 | chr5 | 135266034 | 135266129 | chr5 | 135266578 | 135266753 |
| chr5 | 135528098 | 135528337 | chr5 | 136834009 | 136834051 | chr5 | 136834290 | 136834492 |
| chr5 | 136834494 | 136834608 | chr5 | 136834624 | 136834664 | chr5 | 136834707 | 136834881 |
| chr5 | 136834913 | 136834923 | chr5 | 137225092 | 137225268 | chr5 | 138273717 | 138273845 |
| chr5 | 139047897 | 139048256 | chr5 | 139227705 | 139227991 | chr5 | 139525654 | 139525833 |
| chr5 | 139779840 | 139779953 | chr5 | 140174701 | 140174840 | chr5 | 140174938 | 140174994 |
| chr5 | 140187003 | 140187240 | chr5 | 140305895 | 140306134 | chr5 | 140306445 | 140306620 |
| chr5 | 140306675 | 140306787 | chr5 | 140346514 | 140346753 | chr5 | 140514817 | 140514996 |
| chr5 | 140604361 | 140604596 | chr5 | 140613851 | 140614089 | chr5 | 140614230 | 140614329 |
| chr5 | 140614384 | 140614469 | chr5 | 140777354 | 140777588 | chr5 | 140797000 | 140797279 |
| chr5 | 140797328 | 140797419 | chr5 | 140800384 | 140800965 | chr5 | 140801035 | 140801343 |
| chr5 | 140811136 | 140811138 | chr5 | 140855515 | 140856459 | chr5 | 140856547 | 140856710 |
| chr5 | 141031047 | 141031205 | chr5 | 141262957 | 141263143 | chr5 | 141263261 | 141263316 |
| chr5 | 141931261 | 141931355 | chr5 | 141931425 | 141931585 | chr5 | 142784881 | 142785305 |
| chr5 | 145713562 | 145713981 | chr5 | 145717097 | 145717197 | chr5 | 145717249 | 145717516 |
| chr5 | 145718714 | 145719754 | chr5 | 145719835 | 145719937 | chr5 | 145720019 | 145720024 |
| chr5 | 145720763 | 145720942 | chr5 | 145722033 | 145722467 | chr5 | 145722561 | 145723112 |
| chr5 | 145724421 | 145724780 | chr5 | 145725109 | 145725188 | chr5 | 145725694 | 145725948 |
| chr5 | 146257258 | 146257484 | chr5 | 146257486 | 146257677 | chr5 | 146889129 | 146889183 |
| chr5 | 146889332 | 146889538 | chr5 | 146889540 | 146889668 | chr5 | 149681971 | 149682270 |
| chr5 | 150051025 | 150051744 | chr5 | 150400044 | 150400283 | chr5 | 151066339 | 151066578 |
| chr5 | 151304297 | 151304476 | chr5 | 153852579 | 153862878 | chr5 | 153853387 | 153853569 |
| chr5 | 153855101 | 153855340 | chr5 | 153855558 | 153855925 | chr5 | 153856149 | 153856483 |

TABLE 15-continued

| chr | start | end | chr | start | end | chr | start | end |
|---|---|---|---|---|---|---|---|---|
| chr5 | 153856847 | 153857086 | chr5 | 153857285 | 153857524 | chr5 | 153858220 | 153858699 |
| chr5 | 153859573 | 153859812 | chr5 | 153861948 | 153862180 | chr5 | 153862219 | 153862667 |
| chr5 | 153863347 | 153863417 | chr5 | 153863419 | 153863526 | chr5 | 154209838 | 154210070 |
| chr5 | 154318060 | 154318178 | chr5 | 155107702 | 155107941 | chr5 | 155108042 | 155108084 |
| chr5 | 155108161 | 155108268 | chr5 | 155108356 | 155108612 | chr5 | 155108659 | 155108838 |
| chr5 | 156874164 | 156874403 | chr5 | 157001643 | 157001941 | chr5 | 157078345 | 157078524 |
| chr5 | 157098282 | 157098701 | chr5 | 158478385 | 158478466 | chr5 | 158478513 | 158478864 |
| chr5 | 158524641 | 158524837 | chr5 | 158527367 | 158527817 | chr5 | 158527819 | 158528146 |
| chr5 | 159399015 | 159399100 | chr5 | 160975650 | 160975829 | chr5 | 161274223 | 161274358 |
| chr5 | 161274506 | 161274642 | chr5 | 166865354 | 166865462 | chr5 | 167956087 | 167956267 |
| chr5 | 167956414 | 167956560 | chr5 | 167956601 | 167956686 | chr5 | 168233320 | 168233559 |
| chr5 | 168727837 | 168727928 | chr5 | 168727995 | 168728076 | chr5 | 169064237 | 169064530 |
| chr5 | 169064532 | 169064887 | chr5 | 169532851 | 169533090 | chr5 | 170108211 | 170108450 |
| chr5 | 170735061 | 170735300 | chr5 | 170735731 | 170735875 | chr5 | 170736019 | 170736164 |
| chr5 | 170736716 | 170736831 | chr5 | 170737282 | 170737578 | chr5 | 170737779 | 170737864 |
| chr5 | 170737936 | 170738690 | chr5 | 170738824 | 170739571 | chr5 | 170739746 | 170740058 |
| chr5 | 170740091 | 170740105 | chr5 | 170740391 | 170740478 | chr5 | 170740575 | 170740673 |
| chr5 | 170740675 | 170741031 | chr5 | 170741508 | 170742276 | chr5 | 170742387 | 170742600 |
| chr5 | 170742673 | 170742827 | chr5 | 170743151 | 170743480 | chr5 | 170743647 | 170744207 |
| chr5 | 170744290 | 170744649 | chr5 | 170745286 | 170745560 | chr5 | 172655778 | 172656317 |
| chr5 | 172659314 | 172659378 | chr5 | 172659397 | 172659756 | chr5 | 172659768 | 172660026 |
| chr5 | 172660142 | 172660307 | chr5 | 172660633 | 172661001 | chr5 | 172661127 | 172661228 |
| chr5 | 172661368 | 172661772 | chr5 | 172664148 | 172664567 | chr5 | 172665492 | 172665911 |
| chr5 | 172670882 | 172671121 | chr5 | 172671268 | 172671482 | chr5 | 172671640 | 172671926 |
| chr5 | 172672391 | 172672406 | chr5 | 172672593 | 172672750 | chr5 | 172754486 | 172754725 |
| chr5 | 172754733 | 172754963 | chr5 | 172754986 | 172755032 | chr5 | 172755421 | 172755563 |
| chr5 | 172755595 | 172755745 | chr5 | 172756961 | 172757200 | chr5 | 174115296 | 174115690 |
| chr5 | 174115864 | 174115955 | chr5 | 174147441 | 174147680 | chr5 | 174150341 | 174150520 |
| chr5 | 174159300 | 174159669 | chr5 | 174162800 | 174162945 | chr5 | 174220897 | 174221036 |
| chr5 | 174870643 | 174870882 | chr5 | 174871097 | 174871576 | chr5 | 174921381 | 174921483 |
| chr5 | 175085059 | 175085298 | chr5 | 175085525 | 175085808 | chr5 | 175223571 | 175223748 |
| chr5 | 175223935 | 175223950 | chr5 | 175298507 | 175298986 | chr5 | 175299196 | 175299495 |
| chr5 | 175300277 | 175300456 | chr5 | 175621297 | 175621596 | chr5 | 175792785 | 175792932 |
| chr5 | 175792998 | 175793144 | chr5 | 176023818 | 176023882 | chr5 | 176024006 | 176024350 |
| chr5 | 176046280 | 176046639 | chr5 | 176107191 | 176107485 | chr5 | 176107518 | 176107670 |
| chr5 | 175236631 | 176236990 | chr5 | 176264711 | 176264998 | chr5 | 176764020 | 176764255 |
| chr5 | 177031093 | 177031272 | chr5 | 177408416 | 177408548 | chr5 | 177411561 | 177412210 |
| chr5 | 177713273 | 177713572 | chr5 | 178003629 | 178003662 | chr5 | 178004286 | 178004398 |
| chr5 | 178016513 | 178016571 | chr5 | 178016682 | 178016984 | chr5 | 178017520 | 178017571 |
| chr5 | 178017573 | 178017971 | chr5 | 178367990 | 178368122 | chr5 | 178368415 | 178368462 |
| chr5 | 178421400 | 178421423 | chr5 | 178422167 | 178422224 | chr5 | 178487023 | 178487304 |
| chr5 | 178487342 | 178487493 | chr5 | 178576382 | 178576578 | chr5 | 178655663 | 178655962 |
| chr5 | 178771216 | 178771631 | chr5 | 178771724 | 178771781 | chr5 | 178221783 | 178771860 |
| chr5 | 178771968 | 178772055 | chr5 | 178772120 | 178772359 | chr5 | 178772525 | 178772730 |
| chr5 | 178772779 | 178772824 | chr5 | 178957598 | 178958023 | chr5 | 179214036 | 179214275 |
| chr5 | 179244321 | 179244371 | chr5 | 179780005 | 179780013 | chr5 | 179780036 | 179780244 |
| chr5 | 179780607 | 179781086 | chr5 | 179867405 | 179867637 | chr5 | 180017039 | 180017278 |
| chr5 | 180017532 | 180017689 | chr5 | 180017691 | 180018011 | chr5 | 180018485 | 180018585 |
| chr5 | 180047646 | 180047703 | chr5 | 180075753 | 180075858 | chr5 | 180076054 | 180076412 |
| chr5 | 180076533 | 180076705 | chr5 | 180076721 | 180077080 | chr5 | 180100825 | 180100874 |
| chr5 | 180101016 | 180101168 | chr5 | 180101252 | 180101410 | chr5 | 180326052 | 180326231 |
| chr5 | 180527447 | 180527699 | chr5 | 180527794 | 180527866 | chr5 | 180600769 | 180601030 |
| chr5 | 180601129 | 180601308 | chr6 | 391089 | 391743 | chr6 | 391745 | 391764 |
| chr6 | 391766 | 391900 | chr6 | 392410 | 392434 | chr6 | 392588 | 392959 |
| chr6 | 393125 | 393239 | chr6 | 393241 | 393473 | chr6 | 711039 | 711392 |
| chr6 | 1311899 | 1312095 | chr6 | 1312680 | 1312802 | chr6 | 1314014 | 1314101 |
| chr6 | 1378133 | 1378476 | chr6 | 1379268 | 1379332 | chr6 | 1379510 | 1379689 |
| chr6 | 1379812 | 1380051 | chr6 | 1383598 | 1383709 | chr6 | 1383860 | 1383982 |
| chr6 | 1383984 | 1384180 | chr6 | 1384626 | 1384731 | chr6 | 1385025 | 1385264 |
| chr6 | 1386020 | 1386212 | chr6 | 1389044 | 1389275 | chr6 | 1390159 | 1390361 |
| chr6 | 1390363 | 1390406 | chr6 | 1390424 | 1390759 | chr6 | 1390956 | 1391118 |
| chr6 | 1391230 | 1391469 | chr6 | 1524122 | 1524361 | chr6 | 1605302 | 1605541 |
| chr6 | 1615243 | 1615279 | chr6 | 1624940 | 1625059 | chr6 | 1625129 | 1625779 |
| chr6 | 3053237 | 3063463 | chr6 | 3228955 | 3229134 | chr6 | 3229348 | 3229587 |
| chr6 | 3231926 | 3232029 | chr6 | 3285129 | 3285608 | chr6 | 3405599 | 3405778 |
| chr6 | 4775080 | 4775322 | chr6 | 4836441 | 4836545 | chr6 | 4951178 | 4951469 |
| chr6 | 5783232 | 5783457 | chr6 | 5996852 | 5997091 | chr6 | 5997728 | 5997907 |
| chr6 | 6003213 | 6003529 | chr6 | 6004350 | 6004744 | chr6 | 6004837 | 6005450 |
| chr6 | 6006278 | 6006498 | chr6 | 6006600 | 6006959 | chr6 | 6007516 | 6007670 |
| chr6 | 6007672 | 6007772 | chr6 | 6007833 | 6008355 | chr6 | 6367000 | 6367218 |
| chr6 | 7726260 | 7726439 | chr6 | 7726556 | 7726735 | chr6 | 7726878 | 7727057 |
| chr6 | 7727622 | 7727769 | chr6 | 7728087 | 7728221 | chr6 | 7728746 | 7729045 |
| chr6 | 10381428 | 10381593 | chr6 | 10381695 | 10381969 | chr6 | 10382322 | 10382383 |
| chr6 | 10382648 | 10383126 | chr6 | 10383638 | 10383877 | chr6 | 10384876 | 10384975 |
| chr6 | 10385280 | 10386015 | chr6 | 10386123 | 10386357 | chr6 | 10389946 | 10391216 |
| chr6 | 10410429 | 10410668 | chr6 | 10411254 | 10411613 | chr6 | 10415015 | 10415314 |
| chr6 | 10415457 | 10415816 | chr6 | 10416039 | 10416399 | chr6 | 10417059 | 10417530 |
| chr6 | 10418997 | 10419440 | chr6 | 10419477 | 10419596 | chr6 | 10419664 | 10420002 |

TABLE 15-continued

| chr | start | end | chr | start | end | chr | start | end |
|---|---|---|---|---|---|---|---|---|
| chr6 | 10420975 | 10421171 | chr6 | 10421253 | 10421452 | chr6 | 10421549 | 10422714 |
| chr6 | 10425411 | 10425478 | chr6 | 10425630 | 10425790 | chr6 | 10425839 | 10426970 |
| chr6 | 10881857 | 10882156 | chr6 | 10882247 | 10882426 | chr6 | 10882934 | 10883023 |
| chr6 | 10886993 | 10887185 | chr6 | 10887187 | 10887772 | chr6 | 11043988 | 11044106 |
| chr6 | 11044108 | 11044541 | chr6 | 11044543 | 11044647 | chr6 | 12288420 | 12288779 |
| chr6 | 12749819 | 12749941 | chr6 | 16196952 | 16197191 | chr6 | 17281327 | 17281327 |
| chr6 | 17281329 | 17281351 | chr6 | 18035792 | 18036091 | chr6 | 19691621 | 19691920 |
| chr6 | 19691983 | 19691997 | chr6 | 19692143 | 19692280 | chr6 | 19836983 | 19837064 |
| chr6 | 19837141 | 19837205 | chr6 | 21664905 | 21665144 | chr6 | 2.4494604 | 24494843 |
| chr6 | 24647262 | 24647371 | chr6 | 26184364 | 26184476 | chr6 | 26188754 | 26189234 |
| chr6 | 26189236 | 26189495 | chr6 | 26199099 | 26199242 | chr6 | 26199612 | 26199791 |
| chr6 | 26214613 | 26214731 | chr6 | 26235124 | 26235437 | chr6 | 26240532 | 26241201 |
| chr6 | 26250378 | 26250685 | chr6 | 26250687 | 26250917 | chr6 | 26250969 | 26251261 |
| chr6 | 26251715 | 26251940 | chr6 | 26252075 | 26252099 | chr6 | 26252141 | 26252180 |
| chr6 | 26271315 | 26271816 | chr6 | 26271818 | 26271854 | chr6 | 26271897 | 26272076 |
| chr6 | 26272416 | 26272715 | chr6 | 26273381 | 26273419 | chr6 | 26273515 | 26273560 |
| chr6 | 26284786 | 26284975 | chr6 | 26327725 | 26328074 | chr6 | 26328206 | 26328505 |
| chr6 | 26332079 | 26332318 | chr6 | 26501764 | 26501841 | chr6 | 26501950 | 26502296 |
| chr6 | 26550895 | 26551059 | chr6 | 26551084 | 26551134 | chr6 | 26577078 | 26577557 |
| chr6 | 26987930 | 26988169 | chr6 | 27059697 | 27059936 | chr6 | 27064581 | 27064769 |
| chr6 | 27064771 | 27065003 | chr6 | 27065005 | 27065300 | chr6 | 27173436 | 27173547 |
| chr6 | 27173633 | 27173855 | chr6 | 27173925 | 27174275 | chr6 | 27182856 | 27182974 |
| chr6 | 27203167 | 27203286 | chr6 | 27205240 | 27205359 | chr6 | 27205420 | 27205521 |
| chr6 | 27205587 | 27205837 | chr6 | 27205914 | 27206126 | chr6 | 27228079 | 27228187 |
| chr6 | 27228290 | 27228498 | chr6 | 27247561 | 27247800 | chr6 | 27256016 | 27256255 |
| chr6 | 27256283 | 27256522 | chr6 | 27264344 | 27264468 | chr6 | 27279750 | 27280109 |
| chr6 | 27462939 | 27463778 | chr6 | 27512675 | 27512884 | chr6 | 27512995 | 27513574 |
| chr6 | 27533723 | 27534442 | chr6 | 27559775 | 27560074 | chr6 | 27573073 | 27573492 |
| chr6 | 27598650 | 27598949 | chr6 | 27599071 | 27599422 | chr6 | 27635171 | 27635530 |
| chr6 | 27647625 | 27647736 | chr6 | 27647891 | 27647984 | chr6 | 27648934 | 27649153 |
| chr6 | 27834577 | 27834863 | chr6 | 27834905 | 27834936 | chr6 | 27834963 | 27835097 |
| chr6 | 27835378 | 27835502 | chr6 | 27839635 | 27840174 | chr6 | 27840461 | 27840668 |
| chr6 | 27841002 | 27841240 | chr6 | 27858427 | 27858726 | chr6 | 28175105 | 28176301 |
| chr6 | 28303466 | 28303571 | chr6 | 28303847 | 28304339 | chr6 | 28367023 | 28367279 |
| chr6 | 28367281 | 28367347 | chr6 | 28367491 | 28367571 | chr6 | 28367573 | 28367862 |
| chr6 | 28410896 | 28411030 | chr6 | 28411032 | 28411088 | chr6 | 28411152 | 28411435 |
| chr6 | 28414887 | 28414992 | chr6 | 28415092 | 28415126 | chr6 | 28457534 | 28457713 |
| chr6 | 28457775 | 28458254 | chr6 | 33955409 | 33955828 | chr6 | 34170869 | 34170986 |
| chr6 | 34171049 | 34171166 | chr6 | 34396518 | 34396631 | chr6 | 34724210 | 34724318 |
| chr6 | 35149942 | 35150181 | chr6 | 35992410 | 35992533 | chr6 | 36165588 | 36165767 |
| chr6 | 36252899 | 36253258 | chr6 | 36313887 | 36313988 | chr6 | 36808233 | 36808532 |
| chr6 | 37024485 | 37024664 | chr6 | 37664045 | 37664284 | chr6 | 37673227 | 37673573 |
| chr6 | 37776336 | 37776455 | chr6 | 37776737 | 37776839 | chr6 | 39281005 | 39281231 |
| chr6 | 39281731 | 39281970 | chr6 | 39329789 | 39329968 | chr6 | 39760322 | 39760663 |
| chr6 | 40554557 | 40554796 | chr6 | 41336981 | 41337220 | chr6 | 41339162 | 41339559 |
| chr6 | 41339602 | 41339941 | chr6 | 41340803 | 41341282 | chr6 | 41341406 | 41341604 |
| chr6 | 41342140 | 41342370 | chr6 | 41342733 | 41342912 | chr6 | 41605851 | 41605952 |
| chr6 | 41606038 | 41606357 | chr6 | 41606528 | 41606630 | chr6 | 41773485 | 41773844 |
| chr6 | 42773364 | 42773471 | chr6 | 42846625 | 42846729 | chr6 | 42879457 | 42879569 |
| chr6 | 42879622 | 42879756 | chr6 | 42928239 | 42928460 | chr6 | 43211113 | 43211402 |
| chr6 | 43424445 | 43424564 | chr6 | 43425407 | 43425524 | chr6 | 43478592 | 43478821 |
| chr6 | 43612737 | 43612899 | chr6 | 43613053 | 43613156 | chr6 | 43639525 | 43639809 |
| chr6 | 43748380 | 43748619 | chr6 | 44240961 | 44241191 | chr6 | 44695775 | 44695899 |
| chr6 | 45388701 | 45388866 | chr6 | 46702904 | 46703203 | chr6 | 46703274 | 46703513 |
| chr6 | 50674292 | 50674.831 | chr6 | 50681612 | 50681851 | chr6 | 50681912 | 50682031 |
| chr6 | 50682234 | 50682339 | chr6 | 50682449 | 50682473 | chr6 | 50682584 | 50682684 |
| chr6 | 50682712 | 50682941 | chr6 | 50682992 | 50683303 | chr6 | 50684865 | 50685044 |
| chr6 | 50689827 | 50690126 | chr6 | 50690991 | 50691170 | chr6 | 50691983 | 50692213 |
| chr6 | 50692300 | 50692582 | chr6 | 50787125 | 50787877 | chr6 | 50787950 | 50788444 |
| chr6 | 50789300 | 50789479 | chr6 | 50791111 | 50791495 | chr6 | 50791551 | 50791708 |
| chr6 | 50793251 | 50793490 | chr6 | 50793626 | 50793850 | chr6 | 50794525 | 50794792 |
| chr6 | 50803732 | 50803971 | chr6 | 50804041 | 50804446 | chr6 | 50808589 | 50808845 |
| chr6 | 50810456 | 50810714 | chr6 | 50810976 | 50811575 | chr6 | 50813200 | 50814019 |
| chr6 | 50814495 | 50814674 | chr6 | 50816947 | 50817306 | chr6 | 50817831 | 50817841 |
| chr6 | 50818369 | 50818788 | chr6 | 50818841 | 50819080 | chr6 | 52227678 | 52227857 |
| chr6 | 52227934 | 52227964 | chr6 | 52344301 | 52344480 | chr6 | 53212553 | 53213932 |
| chr6 | 55443610 | 55444029 | chr6 | 56112175 | 56112474 | chr6 | 56716262 | 56716300 |
| chr6 | 56716390 | 56716491 | chr6 | 56818618 | 56819037 | chr6 | 56819128 | 56819727 |
| chr6 | 56819823 | 56820002 | chr6 | 58147345 | 58147511 | chr6 | 58147764 | 58148058 |
| chr6 | 6299527) | 62995875 | chr6 | 62996078 | 62996130 | chr6 | 62996132 | 62996214 |
| chr6 | 62996216 | 62996231 | chr6 | 62996347 | 62996586 | chr6 | 70991961 | 70992049 |
| chr6 | 70992137 | 70992260 | chr6 | 70992339 | 70992638 | chr6 | 70992744 | 70993103 |
| chr6 | 71665562 | 71665801 | chr6 | 71666708 | 71667066 | chr6 | 72129690 | 72129869 |
| chr6 | 72129922 | 72129929 | chr6 | 72130017 | 72130045 | chr6 | 72130191 | 72130499 |
| chr6 | 72596039 | 72596135 | chr6 | 72596137 | 72596398 | chr6 | 72596876 | 72597055 |
| chr6 | 73329686 | 73330225 | chr6 | 73330740 | 73331114 | chr6 | 73331116 | 73331238 |
| chr6 | 73331240 | 73331399 | chr6 | 73331420 | 73331851 | chr6 | 73331876 | 73333099 |
| chr6 | 78172096 | 78172276 | chr6 | 78172323 | 78172675 | chr6 | 78173119 | 78173227 |

TABLE 15-continued

| chr | start | end | chr | start | end | chr | start | end |
|---|---|---|---|---|---|---|---|---|
| chr6 | 78173229 | 78173295 | chr6 | 78173610 | 78173726 | chr6 | 78173772 | 78174080 |
| chr6 | 78176370 | 78176607 | chr6 | 78176693 | 78176909 | chr6 | 79620310 | 79620342 |
| chr6 | 79620475 | 79620685 | chr6 | 79620687 | 79620789 | chr6 | 80656846 | 80657265 |
| chr6 | 82958527 | 82958646 | chr6 | 84417343 | 84417701 | chr6 | 84418261 | 84418377 |
| chr6 | 84418545 | 84418724 | chr6 | 84418726 | 84418789 | chr6 | 84419077 | 84419202 |
| chr6 | 84419204 | 84419329 | chr6 | 84419331 | 84419496 | chr6 | 84562789 | 84562929 |
| chr6 | 84562932 | 84563285 | chr6 | 84563417 | 84563636 | chr6 | 85472306 | 85473805 |
| chr6 | 85473854 | 85474453 | chr6 | 85474516 | 85474767 | chr6 | 85474795 | 85474815 |
| chr6 | 85476140 | 85476379 | chr6 | 85476924 | 85477103 | chr6 | 85478440 | 85478557 |
| chr6 | 85478615 | 85478799 | chr6 | 85482437 | 85482796 | chr6 | 85483271 | 85483450 |
| chr6 | 85483760 | 85483932 | chr6 | 85484558 | 85484626 | chr6 | 85484717 | 85484998 |
| chr6 | 86302335 | 86302422 | chr6 | 87647130 | 87647219 | chr6 | 87862013 | 87862252 |
| chr6 | 88876871 | 88877064 | chr6 | 88877066 | 88827422 | chr6 | 88877475 | 88877530 |
| chr6 | 91320191 | 91320422 | chr6 | 91320853 | 91321390 | chr6 | 94126870 | 94127066 |
| chr6 | 94127086 | 94127169 | chr6 | 94127381 | 94127620 | chr6 | 94128340 | 94128502 |
| chr6 | 94129119 | 94129358 | chr6 | 94129423 | 94129627 | chr6 | 94129629 | 94129662 |
| chr6 | 96464003 | 96464293 | chr6 | 99271829 | 99272908 | chr6 | 99273271 | 99223510 |
| chr6 | 99277106 | 99277201 | chr6 | 99277262 | 99277405 | chr6 | 99279465 | 99279704 |
| chr6 | 99280472 | 99280831 | chr6 | 99280931 | 99281037 | chr6 | 99281068 | 99281470 |
| chr6 | 99283428 | 99283667 | chr6 | 99290260 | 99290473 | chr6 | 99290710 | 99290738 |
| chr6 | 99291191 | 99291342 | chr6 | 99292156 | 99292515 | chr6 | 99295648 | 99295864 |
| chr6 | 99296062 | 99296365 | chr6 | 99296408 | 99296547 | chr6 | 99396354 | 99396473 |
| chr6 | 100038584 | 100038707 | chr6 | 100038786 | 100039063 | chr6 | 100039275 | 100039364 |
| chr6 | 100050674 | 100050811 | chr6 | 100050859 | 100051109 | chr6 | 100051360 | 100051508 |
| chr6 | 100051772 | 100052053 | chr6 | 100053191 | 100053606 | chr6 | 100054773 | 100055012 |
| chr6 | 100060930 | 100061169 | chr6 | 100061216 | 100061515 | chr6 | 100061677 | 100061697 |
| chr6 | 100062083 | 100062682 | chr6 | 100062857 | 100063156 | chr6 | 100441276 | 100441308 |
| chr6 | 100441498 | 100441738 | chr6 | 100441762 | 100442055 | chr6 | 100903299 | 100903405 |
| chr6 | 100903561 | 100903718 | chr6 | 100904126 | 100904365 | chr6 | 100905936 | 100906113 |
| chr6 | 100911976 | 100912215 | chr6 | 100912332 | 100912446 | chr6 | 100912466 | 100912571 |
| chr6 | 100912825 | 100913051 | chr6 | 101840615 | 101840914 | chr6 | 101850062 | 101850314 |
| chr6 | 101850496 | 101850539 | chr6 | 105388605 | 105388717 | chr6 | 105389510 | 105389792 |
| chr6 | 105400811 | 105401110 | chr6 | 105401538 | 105401908 | chr6 | 105404475 | 105404774 |
| chr6 | 105405565 | 105405864 | chr6 | 105406024 | 105406203 | chr6 | 105584190 | 105584216 |
| chr6 | 105584218 | 105584320 | chr6 | 105584367 | 105584551 | chr6 | 105584553 | 105585629 |
| chr6 | 106428948 | 106429476 | chr6 | 106429590 | 106429704 | chr6 | 106434265 | 106434371 |
| chr6 | 106441795 | 106443054 | chr6 | 106960817 | 106961116 | chr6 | 108280341 | 108280442 |
| chr6 | 108434990 | 108435327 | chr6 | 108435970 | 108436629 | chr6 | 108438142 | 108438157 |
| chr6 | 108438261 | 108438612 | chr6 | 108440017 | 108440645 | chr6 | 108440745 | 108441036 |
| chr6 | 108479209 | 108479748 | chr6 | 108484829 | 108485274 | chr6 | 108485419 | 108485488 |
| chr6 | 108485576 | 108485995 | chr6 | 108486067 | 108486486 | chr6 | 108487701 | 108488520 |
| chr6 | 108489662 | 108489809 | chr6 | 108490067 | 108490246 | chr6 | 108490297 | 108490515 |
| chr6 | 108490538 | 108490729 | chr6 | 108490902 | 108491001 | chr6 | 108491108 | 108491501 |
| chr6 | 108492182 | 108492541 | chr6 | 108495607 | 108495818 | chr6 | 108495916 | 108496026 |
| chr6 | 108496130 | 108496466 | chr6 | 108497419 | 108497467 | chr6 | 110679030 | 110679400 |
| chr6 | 110679402 | 110679509 | chr6 | 110797604 | 110797783 | chr6 | 110797977 | 110798042 |
| chr6 | 116783418 | 116783591 | chr6 | 117086168 | 117086479 | chr6 | 117086481 | 117086640 |
| chr6 | 117086903 | 117086947 | chr6 | 117585867 | 117586106 | chr6 | 117587028 | 117587256 |
| chr6 | 117587380 | 117587387 | chr6 | 117587449 | 117587679 | chr6 | 117591087 | 117591266 |
| chr6 | 117591308 | 117591597 | chr6 | 117591684 | 117591847 | chr6 | 118228008 | 118228232 |
| chr6 | 118228669 | 118228869 | chr6 | 118228871 | 118228908 | chr6 | 118229060 | 118229390 |
| chr6 | 118229417 | 118229479 | chr6 | 118229543 | 118229573 | chr6 | 118229617 | 118229732 |
| chr6 | 118229734 | 118229902 | chr6 | 118241125 | 11824:309 | chr6 | 118241395 | 118241604 |
| chr6 | 119254661 | 119254774 | chr6 | 121758594 | 121758980 | chr6 | 121758982 | 121759048 |
| chr6 | 123316950 | 123317007 | chr6 | 123317073 | 123317669 | chr6 | 123317696 | 123317714 |
| chr6 | 123317716 | 123317935 | chr6 | 124124330 | 124124569 | chr6 | 124124759 | 124125118 |
| chr6 | 125284034 | 125284273 | chr6 | 126068016 | 126068022 | chr6 | 126068069 | 126068255 |
| chr6 | 127439322 | 127439536 | chr6 | 127439907 | 127440206 | chr6 | 127440248 | 127440510 |
| chr6 | 127440512 | 127440963 | chr6 | 127441031 | 127441207 | chr6 | 127441479 | 127441838 |
| chr6 | 127441944 | 127442071 | chr6 | 127442090 | 127442183 | chr6 | 127840412 | 127840771 |
| chr6 | 129204373 | 129204612 | chr6 | 130686437 | 130687156 | chr6 | 131602689 | 131602789 |
| chr6 | 132721988 | 132722142 | chr6 | 132722158 | 132722287 | chr6 | 133561967 | 133562145 |
| chr6 | 133562349 | 133562437 | chr6 | 133562675 | 133563095 | chr6 | 133563234 | 133564013 |
| chr6 | 134067456 | 134067573 | chr6 | 134176147 | 134176149 | chr6 | 134210558 | 134211019 |
| chr6 | 134211112 | 134211458 | chr6 | 134213855 | 134213988 | chr6 | 134214077 | 134214454 |
| chr6 | 134589425 | 134589586 | chr6 | 134638858 | 134639095 | chr6 | 137241828 | 137242062 |
| chr6 | 137242064 | 137242307 | chr6 | 137243130 | 137243342 | chr6 | 137243367 | 137243489 |
| chr6 | 137244036 | 137244149 | chr6 | 137244236 | 137244466 | chr6 | 137311060 | 137311479 |
| chr6 | 137366280 | 137366459 | chr6 | 137809066 | 137809366 | chr6 | 137809446 | 137809917 |
| chr6 | 137810033 | 137811165 | chr6 | 137813692 | 137813991 | chr6 | 137814505 | 137814619 |
| chr6 | 137814654 | 137814864 | chr6 | 137814916 | 137815171 | chr6 | 137815225 | 137815755 |
| chr6 | 137816373 | 137817377 | chr6 | 137818428 | 137818599 | chr6 | 137818619 | 137819262 |
| chr6 | 137819269 | 137819447 | chr6 | 146755489 | 146755914 | chr6 | 149868369 | 149868478 |
| chr6 | 150284574 | 150284657 | chr6 | 150284979 | 150285369 | chr6 | 150285545 | 150285886 |
| chr6 | 150286100 | 150286718 | chr6 | 150358890 | 150358985 | chr6 | 150358987 | 150359193 |
| chr6 | 150359439 | 150359489 | chr6 | 151560928 | 151561341 | chr6 | 151561369 | 151561947 |
| chr6 | 151561986 | 151561992 | chr6 | 151562057 | 151562645 | chr6 | 151814953 | 151815192 |
| chr6 | 152622925 | 152623584 | chr6 | 152957816 | 152957999 | chr6 | 152958001 | 152958166 |

TABLE 15-continued

| chr | start | end | chr | start | end | chr | start | end |
|---|---|---|---|---|---|---|---|---|
| chr6 | 153451159 | 153451578 | chr6 | 153451810 | 153452049 | chr6 | 153452157 | 153452396 |
| chr6 | 153452611 | 153452755 | chr6 | 153452789 | 153452850 | chr6 | 154360549 | 154360848 |
| chr6 | 154970468 | 154970587 | chr6 | 155316161 | 155316221 | chr6 | 155316257 | 155316340 |
| chr6 | 155569193 | 155569407 | chr6 | 157502364 | 157502543 | chr6 | 157506008 | 157506187 |
| chr6 | 157556755 | 157557297 | chr6 | 159589948 | 159590087 | chr6 | 159590155 | 159590762 |
| chr6 | 159590972 | 159591087 | chr6 | 159654844 | 159655083 | chr6 | 161188439 | 161188618 |
| chr6 | 161361999 | 161352146 | chr6 | 161352199 | 161352238 | chr6 | 161780141 | 161780218 |
| chr6 | 163834237 | 163834383 | chr6 | 163834406 | 163834533 | chr6 | 163834711 | 163834716 |
| chr6 | 163834779 | 163834902 | chr6 | 163834988 | 163835018 | chr6 | 163836465 | 163837004 |
| chr6 | 164179653 | 164179772 | chr6 | 164196997 | 164197107 | chr6 | 164228212 | 164228449 |
| chr6 | 164246123 | 164246229 | chr6 | 164283167 | 164283370 | chr6 | 164314286 | 164314525 |
| chr6 | 164322572 | 164322871 | chr6 | 166074027 | 166074506 | chr6 | 166076696 | 166077115 |
| chr6 | 166077280 | 166077633 | chr6 | 166077669 | 166077759 | chr6 | 166267503 | 166267892 |
| chr6 | 166401162 | 166401401 | chr6 | 166402154 | 166402633 | chr6 | 166421831 | 166421992 |
| chr6 | 166421994 | 166422288 | chr6 | 166579636 | 166580234 | chr6 | 166580252 | 166582393 |
| chr6 | 166582395 | 166582827 | chr6 | 166944266 | 166944505 | chr6 | 167835031 | 167835270 |
| chr6 | 168719890 | 168720121 | chr6 | 168842760 | 168843046 | chr6 | 168858030 | 168858389 |
| chr6 | 169653564 | 169653743 | chr6 | 170240691 | 170240797 | chr6 | 170264630 | 170264865 |
| chr6 | 170475007 | 170475366 | chr7 | 329765 | 329942 | chr7 | 369763 | 370062 |
| chr7 | 389589 | 389768 | chr7 | 409740 | 409872 | chr7 | 409887 | 409979 |
| chr7 | 431290 | 431589 | chr7 | 497679 | 498006 | chr7 | 503725 | 504024 |
| chr7 | 551499 | 551778 | chr7 | 557008 | 557076 | chr7 | 578836 | 579121 |
| chr7 | 751726 | 751765 | chr7 | 752022 | 752149 | chr7 | 752151 | 752306 |
| chr7 | 907582 | 907761 | chr7 | 1022150 | 1022329 | chr7 | 1030079 | 1030378 |
| chr7 | 1054489 | 1054780 | chr7 | 1086110 | 1086409 | chr7 | 1263682 | 1264041 |
| chr7 | 1269228 | 1269464 | chr7 | 1269553 | 1269887 | chr7 | 1270304 | 1270543 |
| chr7 | 1273070 | 1273388 | chr7 | 1274540 | 1274779 | chr7 | 1275046 | 1275113 |
| chr7 | 1275481 | 1275682 | chr7 | 1275734 | 1275780 | chr7 | 1277722 | 1277961 |
| chr7 | 1279136 | 1279204 | chr7 | 1279891 | 1280070 | chr7 | 1281033 | 1281332 |
| chr7 | 1281405 | 1281644 | chr7 | 1281947 | 1282246 | chr7 | 1282426 | 1282725 |
| chr7 | 1286715 | 1286754 | chr7 | 1286887 | 1286954 | chr7 | 1288489 | 1288848 |
| chr7 | 1308275 | 1308574 | chr7 | 1325727 | 1325966 | chr7 | 1415941 | 1416226 |
| chr7 | 1423536 | 1423740 | chr7 | 1458967 | 1459183 | chr7 | 1503328 | 1503687 |
| chr7 | 1547234 | 1547413 | chr7 | 1598549 | 1598788 | chr7 | 1607307 | 1607546 |
| chr7 | 1607897 | 1608076 | chr7 | 1641700 | 1641999 | chr7 | 1681095 | 1681334 |
| chr7 | 1688883 | 1689101 | chr7 | 1690649 | 1690801 | chr7 | 1690903 | 1690948 |
| chr7 | 1709038 | 1709337 | chr7 | 1709385 | 1709562 | chr7 | 1709618 | 1709684 |
| chr7 | 1733066 | 1733482 | chr7 | 1775757 | 1775936 | chr7 | 1783468 | 1783470 |
| chr7 | 1786438 | 1786916 | chr7 | 1787066 | 1787425 | chr7 | 1800808 | 1800987 |
| chr7 | 1970776 | 1970947 | chr7 | 2163251 | 2163496 | chr7 | 2208635 | 2208889 |
| chr7 | 2232861 | 2233154 | chr7 | 2233204 | 2233503 | chr7 | 2238051 | 2238327 |
| chr7 | 2300694 | 2300803 | chr7 | 2565961 | 2566130 | chr7 | 2566526 | 2566705 |
| chr7 | 2719928 | 2720227 | chr7 | 2727968 | 2728267 | chr7 | 3033584 | 3033763 |
| chr7 | 3083216 | 3083288 | chr7 | 3083331 | 3083333 | chr7 | 3083335 | 3083338 |
| chr7 | 3083340 | 3083455 | chr7 | 3283620 | 3283978 | chr7 | 3340370 | 3340549 |
| chr7 | 3341394 | 3341409 | chr7 | 3341570 | 3341693 | chr7 | 4215235 | 4215469 |
| chr7 | 4856897 | 4857136 | chr7 | 4922460 | 4922707 | chr7 | 4923328 | 4923475 |
| chr7 | 4998116 | 4998475 | chr7 | 4998771 | 4998837 | chr7 | 5262472 | 5262648 |
| chr7 | 5632841 | 5633200 | chr7 | 5648011 | 5648490 | chr7 | 6060493 | 6060556 |
| chr7 | 6099127 | 6099234 | chr7 | 6124621 | 6124740 | chr7 | 6188652 | 6188831 |
| chr7 | 6188926 | 6189165 | chr7 | 6443198 | 6443478 | chr7 | 6443752 | 6443794 |
| chr7 | 6443871 | 6443931 | chr7 | 6524492 | 6524599 | chr7 | 6524936 | 6525055 |
| chr7 | 6543064 | 6543303 | chr7 | 6560141 | 6560440 | chr7 | 6566329 | 6566748 |
| chr7 | 6570901 | 6571225 | chr7 | 6576043 | 6576185 | chr7 | 6703458 | 6703708 |
| chr7 | 6703710 | 6703803 | chr7 | 6703805 | 6703870 | chr7 | 6703916 | 6704057 |
| chr7 | 7605665 | 7605902 | chr7 | 8472995 | 8473456 | chr7 | 8473480 | 8473762 |
| chr7 | 8473870 | 8474242 | chr7 | 8474516 | 8474649 | chr7 | 8474727 | 8475146 |
| chr7 | 8480647 | 8481126 | chr7 | 8481228 | 8481260 | chr7 | 8481559 | 8481918 |
| chr7 | 8481980 | 8482298 | chr7 | 8482670 | 8482825 | chr7 | 8482885 | 8482999 |
| chr7 | 8483070 | 8484029 | chr7 | 12151350 | 12151473 | chr7 | 12151524 | 12151769 |
| chr7 | 12443241 | 12443480 | chr7 | 12443767 | 12443806 | chr7 | 12610259 | 12610317 |
| chr7 | 12610539 | 12610558 | chr7 | 15725883 | 15726182 | chr7 | 15726557 | 15727156 |
| chr7 | 15727216 | 15727395 | chr7 | 19145730 | 19145894 | chr7 | 19146032 | 19146185 |
| chr7 | 19146238 | 19146329 | chr7 | 19146411 | 19146650 | chr7 | 19147041 | 19147880 |
| chr7 | 19152224 | 19152368 | chr7 | 19155865 | 19155896 | chr7 | 19155984 | 19156062 |
| chr7 | 19156126 | 19156133 | chr7 | 19156304 | 19156643 | chr7 | 19156705 | 19156746 |
| chr7 | 19157056 | 19157193 | chr7 | 19157195 | 19157263 | chr7 | 19157265 | 19157567 |
| chr7 | 19157634 | 19158099 | chr7 | 19183978 | 19184337 | chr7 | 19813210 | 19813350 |
| chr7 | 20816175 | 20816530 | chr7 | 20817306 | 20817332 | chr7 | 20817452 | 20817485 |
| chr7 | 20818037 | 20818276 | chr7 | 20823213 | 20823331 | chr7 | 20823383 | 20823512 |
| chr7 | 20823826 | 20823879 | chr7 | 20823920 | 20824144 | chr7 | 20824476 | 20824820 |
| chr7 | 20824836 | 20825025 | chr7 | 20825290 | 20825363 | chr7 | 20826803 | 20826939 |
| chr7 | 20827224 | 20827282 | chr7 | 20830596 | 20830775 | chr7 | 20833066 | 20833425 |
| chr7 | 21582492 | 21582641 | chr7 | 21582792 | 21582971 | chr7 | 21583176 | 21583278 |
| chr7 | 21583304 | 21583415 | chr7 | 22539752 | 22539991 | chr7 | 22589254 | 22589973 |
| chr7 | 23287170 | 23287351 | chr7 | 23287533 | 23287709 | chr7 | 23578824 | 23578943 |
| chr7 | 24324002 | 24324028 | chr7 | 24580786 | 24580905 | chr7 | 24796404 | 24796643 |
| chr7 | 25892430 | 25892431 | chr7 | 25892609 | 25892669 | chr7 | 25896424 | 25896603 |

TABLE 15-continued

| chr | start | end | chr | start | end | chr | start | end |
| --- | --- | --- | --- | --- | --- | --- | --- | --- |
| chr7 | 25896675 | 25896963 | chr7 | 27127919 | 27128001 | chr7 | 27135232 | 27135771 |
| chr7 | 27135980 | 27136424 | chr7 | 27136426 | 27136868 | chr7 | 27190490 | 27191329 |
| chr7 | 27195483 | 27195602 | chr7 | 27195867 | 27195893 | chr7 | 27196153 | 27196153 |
| chr7 | 27196155 | 27196286 | chr7 | 27196288 | 27196742 | chr7 | 27204402 | 27204770 |
| chr7 | 27205266 | 27205381 | chr7 | 27205383 | 27205481 | chr7 | 27205599 | 27205790 |
| chr7 | 27206083 | 27206138 | chr7 | 27209413 | 27209672 | chr7 | 27209690 | 27209772 |
| chr7 | 27212400 | 27212984 | chr7 | 27213189 | 27213984 | chr7 | 27213986 | 27214262 |
| chr7 | 27214330 | 27214401 | chr7 | 27223031 | 22223193 | chr7 | 27223222 | 27223253 |
| chr7 | 27223500 | 27223799 | chr7 | 27223980 | 27224699 | chr7 | 27224945 | 27225058 |
| chr7 | 27227795 | 27228034 | chr7 | 27232207 | 27233046 | chr7 | 27238813 | 27238992 |
| chr7 | 27239087 | 27239173 | chr7 | 27239226 | 27239326 | chr7 | 27240127 | 27240423 |
| chr7 | 27244446 | 27244611 | chr7 | 27244798 | 27245393 | chr7 | 27245583 | 27245733 |
| chr7 | 27252306 | 27252485 | chr7 | 27264801 | 27266400 | chr7 | 27265442 | 27265678 |
| chr7 | 27275467 | 27275532 | chr7 | 27279238 | 27279369 | chr7 | 27279454 | 27279554 |
| chr7 | 27282012 | 27283091 | chr7 | 27283250 | 27283295 | chr7 | 27285436 | 27285519 |
| chr7 | 27285621 | 27285825 | chr7 | 27288869 | 27288945 | chr7 | 27289446 | 27289528 |
| chr7 | 27291048 | 27291119 | chr7 | 27291315 | 27291947 | chr7 | 28449197 | 28449291 |
| chr7 | 28449659 | 28449782 | chr7 | 28449858 | 28450096 | chr7 | 28995579 | 28996058 |
| chr7 | 28996357 | 28996596 | chr7 | 28996759 | 28996998 | chr7 | 28997052 | 28997485 |
| chr7 | 28997487 | 28997646 | chr7 | 28997677 | 28997711 | chr7 | 28997967 | 28998206 |
| chr7 | 30721202 | 30721943 | chr7 | 30722214 | 30722453 | chr7 | 31092919 | 31093218 |
| chr7 | 31375899 | 31376230 | chr7 | 32110616 | 32110650 | chr7 | 32110652 | 32110692 |
| chr7 | 32110704 | 32110855 | chr7 | 32337733 | 32337912 | chr7 | 32338044 | 32338218 |
| chr7 | 32338284 | 32338489 | chr7 | 32338826 | 32339005 | chr7 | 32467373 | 32467656 |
| chr7 | 32467947 | 32468151 | chr7 | 32997050 | 32997463 | chr7 | 33943370 | 33943849 |
| chr7 | 35225724 | 35225834 | chr7 | 35226090 | 35226523 | chr7 | 35226557 | 35226610 |
| chr7 | 35226612 | 35226811 | chr7 | 35292893 | 35293067 | chr7 | 35293183 | 35293372 |
| chr7 | 35294032 | 35294228 | chr7 | 35294400 | 35294639 | chr7 | 35295030 | 35295106 |
| chr7 | 35295807 | 35296000 | chr7 | 35296855 | 35297005 | chr7 | 35297138 | 35297354 |
| chr7 | 35297471 | 35298017 | chr7 | 35300851 | 35301009 | chr7 | 35301102 | 35302050 |
| chr7 | 35494278 | 35494333 | chr7 | 35494470 | 35494517 | chr7 | 37487076 | 37487251 |
| chr7 | 37487376 | 37487454 | chr7 | 37487756 | 37487915 | chr7 | 37488179 | 37488658 |
| chr7 | 37488837 | 37489076 | chr7 | 37907366 | 37907545 | chr7 | 37955780 | 37956079 |
| chr7 | 37956176 | 37956535 | chr7 | 37960199 | 37960438 | chr7 | 38670267 | 38670664 |
| chr7 | 38670957 | 38670985 | chr7 | 38670987 | 38671106 | chr7 | 39015463 | 39016062 |
| chr7 | 42267573 | 42267712 | chr7 | 42276251 | 42276730 | chr7 | 42533028 | 42533081 |
| chr7 | 42533257 | 42533387 | chr7 | 43152016 | 43152208 | chr7 | 43152414 | 43152795 |
| chr7 | 43152858 | 43153200 | chr7 | 43153230 | 43153337 | chr7 | 44097655 | 44097895 |
| chr7 | 44143906 | 44143942 | chr7 | 44144030 | 44144085 | chr7 | 44151324 | 44151503 |
| chr7 | 44151715 | 44151857 | chr7 | 44164017 | 44164078 | chr7 | 44364752 | 44364991 |
| chr7 | 44835122 | 44835467 | chr7 | 45038447 | 45038564 | chr7 | 45613693 | 45613814 |
| chr7 | 45613858 | 45613992 | chr7 | 45614259 | 45614558 | chr7 | 45614655 | 45615061 |
| chr7 | 45615536 | 45615588 | chr7 | 45960650 | 45960889 | chr7 | 45961072 | 45961251 |
| chr7 | 45961423 | 45961630 | chr7 | 45961656 | 45961662 | chr7 | 45961742 | 45961981 |
| chr7 | 49812718 | 49813018 | chr7 | 49813810 | 49814093 | chr7 | 49814454 | 49814751 |
| chr7 | 49815117 | 49815250 | chr7 | 49815657 | 49815848 | chr7 | 50294460 | 50294556 |
| chr7 | 50343183 | 50343482 | chr7 | 50343975 | 50344086 | chr7 | 50344150 | 50344294 |
| chr7 | 50344296 | 50344331 | chr7 | 50344333 | 50344569 | chr7 | 50364988 | 50365069 |
| chr7 | 50438544 | 50438723 | chr7 | 50560494 | 50560733 | chr7 | 50860135 | 50860393 |
| chr7 | 50860980 | 50861103 | chr7 | 50861128 | 50861214 | chr7 | 51384235 | 51384534 |
| chr7 | 51384814 | 51385006 | chr7 | 54609764 | 54609952 | chr7 | 54609992 | 54610022 |
| chr7 | 54610024 | 54610243 | chr7 | 54612335 | 54612814 | chr7 | 55086481 | 55086687 |
| chr7 | 55086899 | 55087618 | chr7 | 55409933 | 55410223 | chr7 | 56018026 | 56018205 |
| chr7 | 56031847 | 56031966 | chr7 | 64330322 | 64330561 | chr7 | 64330635 | 64330645 |
| chr7 | 64348952 | 64348968 | chr7 | 64349042 | 64349131 | chr7 | 64349318 | 64349551 |
| chr7 | 64700198 | 64700426 | chr7 | 64712288 | 64712587 | chr7 | 64974283 | 64974402 |
| chr7 | 65037592 | 65037702 | chr7 | 65508900 | 65509124 | chr7 | 66214974 | 66215052 |
| chr7 | 68204692 | 68204931 | chr7 | 69062428 | 69062727 | chr7 | 69064489 | 69064772 |
| chr7 | 69064834 | 69065148 | chr7 | 69897585 | 69897924 | chr7 | 70596353 | 70596416 |
| chr7 | 70596454 | 70596711 | chr7 | 70597368 | 70597368 | chr7 | 70597395 | 70597549 |
| chr7 | 70597752 | 70597754 | chr7 | 70597780 | 70597872 | chr7 | 70597991 | 70598124 |
| chr7 | 70598170 | 70598471 | chr7 | 71217011 | 71217320 | chr7 | 71217322 | 71217366 |
| chr7 | 71800599 | 71800757 | chr7 | 71800934 | 71801105 | chr7 | 71802315 | 71802347 |
| chr7 | 71802390 | 71802396 | chr7 | 71802457 | 71802523 | chr7 | 71802578 | 71802734 |
| chr7 | 71871105 | 71871157 | chr7 | 76033251 | 76033364 | chr7 | 77324278 | 77324397 |
| chr7 | 79081718 | 79081897 | chr7 | 79081942 | 79081969 | chr7 | 79082070 | 79082301 |
| chr7 | 79083016 | 79083035 | chr7 | 79083191 | 79083255 | chr7 | 79083314 | 79083913 |
| chr7 | 82072248 | 82072562 | chr7 | 84815049 | 84815135 | chr7 | 84815397 | 84815468 |
| chr7 | 84815670 | 84816029 | chr7 | 86273108 | 86273645 | chr7 | 86274018 | 86274117 |
| chr7 | 86274258 | 86274547 | chr7 | 87104725 | 87105445 | chr7 | 87229446 | 87230189 |
| chr7 | 87230191 | 87230344 | chr7 | 87230346 | 87230525 | chr7 | 87256911 | 87257074 |
| chr7 | 87257076 | 87257150 | chr7 | 87257964 | 87258143 | chr7 | 88387904 | 88388130 |
| chr7 | 88388247 | 88388263 | chr7 | 88388439 | 88388646 | chr7 | 88388648 | 88388738 |
| chr7 | 88388789 | 88388902 | chr7 | 88389047 | 88389389 | chr7 | 89747928 | 89748294 |
| chr7 | 89748296 | 89748438 | chr7 | 89950108 | 89950813 | chr7 | 90226188 | 90226284 |
| chr7 | 90226286 | 90226547 | chr7 | 90894936 | 90895027 | chr7 | 90895029 | 90895175 |
| chr7 | 92466078 | 92466485 | chr7 | 92689613 | 92689774 | chr7 | 93203613 | 93203852 |
| chr7 | 93204299 | 93204592 | chr7 | 93519265 | 93519766 | chr7 | 93519855 | 93520024 |

TABLE 15-continued

| chr | start | end | chr | start | end | chr | start | end |
|---|---|---|---|---|---|---|---|---|
| chr7 | 93520026 | 93520224 | chr7 | 93551225 | 93551524 | chr7 | 94284277 | 94284978 |
| chr7 | 96619499 | 96619678 | chr7 | 96621614 | 96621913 | chr7 | 96622019 | 96622438 |
| chr7 | 96625472 | 96625809 | chr7 | 96625906 | 96626145 | chr7 | 96631614 | 96631780 |
| chr7 | 96634577 | 96634996 | chr7 | 96635260 | 96635379 | chr7 | 96635440 | 96635452 |
| chr7 | 96635487 | 96635559 | chr7 | 96635650 | 96635972 | chr7 | 96636034 | 96636729 |
| chr7 | 96646568 | 96647227 | chr7 | 96647715 | 96648314 | chr7 | 96650809 | 96651077 |
| chr7 | 96651137 | 96651228 | chr7 | 96651384 | 96651584 | chr7 | 96652070 | 96652249 |
| chr7 | 96653421 | 96653820 | chr7 | 96653863 | 96654080 | chr7 | 97361021 | 97361423 |
| chr7 | 97361521 | 97361860 | chr7 | 97362211 | 97362690 | chr7 | 97600015 | 97600194 |
| chr7 | 97869540 | 97869719 | chr7 | 98245857 | 98246079 | chr7 | 98246305 | 98246508 |
| chr7 | 98246534 | 98246947 | chr7 | 98247032 | 98242751 | chr7 | 98971530 | 98971649 |
| chr7 | 99104174 | 99104293 | chr7 | 99177657 | 99177663 | chr7 | 99177695 | 99177956 |
| chr7 | 99591732 | 99591851 | chr7 | 99595184 | 99595336 | chr7 | 99751485 | 99751553 |
| chr7 | 99775118 | 99775297 | chr7 | 100088099 | 100088398 | chr7 | 100091115 | 100091181 |
| chr7 | 100179789 | 100180017 | chr7 | 100318467 | 100318660 | chr7 | 100808365 | 100808596 |
| chr7 | 100809360 | 100809599 | chr7 | 100823348 | 100823351 | chr7 | 100823381 | 100823587 |
| chr7 | 101005901 | 101006073 | chr7 | 101241919 | 101242098 | chr7 | 101475705 | 101475944 |
| chr7 | 101627683 | 101627884 | chr7 | 101707428 | 101707535 | chr7 | 103085786 | 103086565 |
| chr7 | 103628963 | 103629795 | chr7 | 103630054 | 103630083 | chr7 | 103630381 | 103630549 |
| chr7 | 103630551 | 103630920 | chr7 | 103969130 | 103969166 | chr7 | 103969168 | 103969429 |
| chr7 | 103969595 | 103969679 | chr7 | 103969694 | 103969894 | chr7 | 105279390 | 105279749 |
| chr7 | 106685195 | 106685434 | chr7 | 106797700 | 106797856 | chr7 | 107301418 | 107301717 |
| chr7 | 107483597 | 107484016 | chr7 | 108095227 | 108095466 | chr7 | 108095781 | 108096141 |
| chr7 | 108097093 | 108097572 | chr7 | 112726529 | 112726538 | chr7 | 112726540 | 112726706 |
| chr7 | 113722736 | 113723284 | chr7 | 113723339 | 113723515 | chr7 | 113724870 | 113725169 |
| chr7 | 113726435 | 113726614 | chr7 | 113727345 | 113727584 | chr7 | 113727755 | 113727872 |
| chr7 | 115117451 | 116117750 | chr7 | 116140155 | 116140268 | chr7 | 116962796 | 116963147 |
| chr7 | 116963331 | 116963575 | chr7 | 117119347 | 117120366 | chr7 | 119913464 | 119913837 |
| chr7 | 120969587 | 120969886 | chr7 | 121513457 | 121513796 | chr7 | 121939584 | 121940245 |
| chr7 | 121940434 | 121940543 | chr7 | 121940845 | 121941144 | chr7 | 121941807 | 121942266 |
| chr7 | 121943905 | 121943989 | chr7 | 121944177 | 121944264 | chr7 | 121945722 | 121946021 |
| chr7 | 121946403 | 121946983 | chr7 | 121947098 | 121947482 | chr7 | 121950034 | 121950265 |
| chr7 | 121950429 | 121950553 | chr7 | 121950995 | 121951029 | chr7 | 121951784 | 121952011 |
| chr7 | 121952044 | 121952256 | chr7 | 121956408 | 121956582 | chr7 | 121956955 | 121957072 |
| chr7 | 121957254 | 121957254 | chr7 | 121957256 | 121957411 | chr7 | 123173048 | 123173327 |
| chr7 | 123671948 | 123672187 | chr7 | 124404320 | 124404498 | chr7 | 124404544 | 124404619 |
| chr7 | 126891146 | 126891325 | chr7 | 126891430 | 126891669 | chr7 | 127371055 | 127371234 |
| chr7 | 127615847 | 127616026 | chr7 | 127744048 | 127744210 | chr7 | 127744212 | 127744707 |
| chr7 | 127806560 | 127806739 | chr7 | 127807743 | 127807922 | chr7 | 127807971 | 127808822 |
| chr7 | 127841426 | 127841497 | chr7 | 127841626 | 127841785 | chr7 | 127991742 | 127991743 |
| chr7 | 127991788 | 127991923 | chr7 | 127992045 | 127992221 | chr7 | 128096988 | 128097164 |
| chr7 | 128337365 | 128337543 | chr7 | 128337788 | 128338023 | chr7 | 128470816 | 128471057 |
| chr7 | 128486020 | 128486237 | chr7 | 128528729 | 128528854 | chr7 | 128528949 | 128529128 |
| chr7 | 128828115 | 128828354 | chr7 | 129229605 | 129229724 | chr7 | 129418168 | 129418513 |
| chr7 | 129422115 | 129422969 | chr7 | 129423126 | 129423509 | chr7 | 129424552 | 129425991 |
| chr7 | 129426215 | 129426336 | chr7 | 129794508 | 129794807 | chr7 | 129800223 | 129800462 |
| chr7 | 131041437 | 131041676 | chr7 | 131242662 | 131242901 | chr7 | 131514750 | 131514929 |
| chr7 | 132261173 | 132261208 | chr7 | 132261257 | 132261505 | chr7 | 134143081 | 134143560 |
| chr7 | 134143731 | 134143971 | chr7 | 134143973 | 134144055 | chr7 | 134144057 | 134144209 |
| chr7 | 134918421 | 134918720 | chr7 | 136553316 | 136553495 | chr7 | 136553556 | 136554026 |
| chr7 | 136554104 | 136554469 | chr7 | 136554563 | 136554581 | chr7 | 136554626 | 136555001 |
| chr7 | 136555145 | 136555504 | chr7 | 136555587 | 136555842 | chr7 | 136556013 | 136556186 |
| chr7 | 137028402 | 137028623 | chr7 | 137531153 | 137531212 | chr7 | 137531263 | 137531889 |
| chr7 | 137531909 | 137532188 | chr7 | 137532374 | 137532438 | chr7 | 138042136 | 138042315 |
| chr7 | 139167532 | 139167827 | chr7 | 139168115 | 139168481 | chr7 | 139208697 | 139208888 |
| chr7 | 139930070 | 139930371 | chr7 | 139939060 | 139939314 | chr7 | 140026925 | 140027043 |
| chr7 | 140180180 | 140180298 | chr7 | 140339839 | 140339868 | chr7 | 140339966 | 140340078 |
| chr7 | 140453048 | 140453227 | chr7 | 140772717 | 140773312 | chr7 | 140773478 | 140773837 |
| chr7 | 143042537 | 143042896 | chr7 | 143579665 | 143579665 | chr7 | 143579667 | 143579951 |
| chr7 | 143579953 | 143580144 | chr7 | 145812918 | 145813008 | chr7 | 145813010 | 145813157 |
| chr7 | 145813334 | 145813391 | chr7 | 145813404 | 145813573 | chr7 | 145813946 | 145814269 |
| chr7 | 148224592 | 148224711 | chr7 | 148640242 | 148640331 | chr7 | 148846061 | 148846279 |
| chr7 | 149111968 | 149112226 | chr7 | 149112421 | 149112507 | chr7 | 149119862 | 149120124 |
| chr7 | 149411444 | 149411728 | chr7 | 149411835 | 149412403 | chr7 | 149744462 | 149744553 |
| chr7 | 149917322 | 149917412 | chr7 | 149918045 | 149918191 | chr7 | 150049512 | 150049626 |
| chr7 | 150069013 | 150069432 | chr7 | 150069601 | 150069662 | chr7 | 150069837 | 150069900 |
| chr7 | 150069921 | 150070160 | chr7 | 150081153 | 150081354 | chr7 | 150716088 | 150716387 |
| chr7 | 150748090 | 150748509 | chr7 | 150753843 | 150754082 | chr7 | 150870734 | 150870973 |
| chr7 | 151106369 | 151106566 | chr7 | 151106590 | 151106989 | chr7 | 151107396 | 151107637 |
| chr7 | 151107639 | 151107749 | chr7 | 151591567 | 151591806 | chr7 | 152622546 | 152622779 |
| chr7 | 153583503 | 153583530 | chr7 | 153583632 | 153584162 | chr7 | 153584297 | 153584546 |
| chr7 | 153584694 | 153584716 | chr7 | 153584758 | 153585233 | chr7 | 153585333 | 153585396 |
| chr7 | 153585602 | 153585692 | chr7 | 153749619 | 153750043 | chr7 | 154561051 | 154561290 |
| chr7 | 154708188 | 154708355 | chr7 | 154861947 | 154862030 | chr7 | 154862032 | 154862366 |
| chr7 | 155164379 | 155165638 | chr7 | 155165791 | 155166870 | chr7 | 155166933 | 155167038 |
| chr7 | 155167040 | 155167090 | chr7 | 155167175 | 155167661 | chr7 | 155167834 | 155167844 |
| chr7 | 155167846 | 155167992 | chr7 | 155174573 | 155174872 | chr7 | 155241235 | 155241490 |
| chr7 | 155241492 | 155242134 | chr7 | 155242700 | 155243186 | chr7 | 155243245 | 155243534 |

TABLE 15-continued

| chr | start | end | chr | start | end | chr | start | end |
|---|---|---|---|---|---|---|---|---|
| chr7 | 155243756 | 155243980 | chr7 | 155244092 | 155244451 | chr7 | 155246859 | 155247480 |
| chr7 | 155247651 | 155247685 | chr7 | 155248839 | 155249018 | chr7 | 155249420 | 155249659 |
| chr7 | 155249849 | 155250088 | chr7 | 155250200 | 155250304 | chr7 | 155250324 | 155250439 |
| chr7 | 155250713 | 155251072 | chr7 | 155251662 | 155251855 | chr7 | 155251891 | 155252030 |
| chr7 | 155252160 | 155252262 | chr7 | 155252317 | 155252579 | chr7 | 155252773 | 155253132 |
| chr7 | 155254765 | 155255416 | chr7 | 155256216 | 155256233 | chr7 | 155256269 | 155256395 |
| chr7 | 155256986 | 155257265 | chr7 | 155258101 | 155258580 | chr7 | 155258854 | 155258864 |
| chr7 | 155258915 | 155259078 | chr7 | 155259120 | 155259623 | chr7 | 155259834 | 155259845 |
| chr7 | 155259847 | 155259958 | chr7 | 155260039 | 155260233 | chr7 | 155260806 | 155260891 |
| chr7 | 155261071 | 155261285 | chr7 | 155301736 | 155302035 | chr7 | 155302267 | 155302896 |
| chr7 | 155302964 | 155303432 | chr7 | 155325720 | 155325954 | chr7 | 155326079 | 155326618 |
| chr7 | 155363212 | 155363511 | chr7 | 155580182 | 155580308 | chr7 | 155580772 | 155580882 |
| chr7 | 155581243 | 155581652 | chr7 | 155581664 | 155581962 | chr7 | 155582190 | 155582369 |
| chr7 | 155600527 | 155600825 | chr7 | 155602726 | 155602898 | chr7 | 156409214 | 156409426 |
| chr7 | 156409728 | 156409884 | chr7 | 156701794 | 156701997 | chr7 | 156744697 | 156744816 |
| chr7 | 156794465 | 156794579 | chr7 | 156794922 | 156795355 | chr7 | 156795402 | 156795636 |
| chr7 | 156795900 | 156795996 | chr7 | 156796442 | 156796740 | chr7 | 156797006 | 156798435 |
| chr7 | 156798527 | 156799147 | chr7 | 156799291 | 156799561 | chr7 | 156800925 | 156801104 |
| chr7 | 156801323 | 156801682 | chr7 | 156808760 | 156809299 | chr7 | 156809953 | 156810522 |
| chr7 | 156810598 | 156810801 | chr7 | 156811303 | 156811520 | chr7 | 156812773 | 156813826 |
| chr7 | 156813987 | 156814230 | chr7 | 156815096 | 156815170 | chr7 | 156832194 | 156832493 |
| chr7 | 156832766 | 156833245 | chr7 | 156871084 | 156871153 | chr7 | 156871283 | 156871383 |
| chr7 | 156880457 | 156880636 | chr7 | 157085281 | 157085580 | chr7 | 157085874 | 157086173 |
| chr7 | 157262738 | 157263097 | chr7 | 157263204 | 157263563 | chr7 | 157361531 | 157361653 |
| chr7 | 157476790 | 157476974 | chr7 | 157476995 | 157477376 | chr7 | 157477395 | 157477489 |
| chr7 | 157477711 | 157477820 | chr7 | 157481534 | 157481550 | chr7 | 157481760 | 157481860 |
| chr7 | 157481890 | 157482074 | chr7 | 157482201 | 157482249 | chr7 | 157482401 | 157482508 |
| chr7 | 157482510 | 157482760 | chr7 | 157483220 | 157483639 | chr7 | 157484778 | 157485377 |
| chr7 | 157485437 | 157485602 | chr7 | 157485650 | 157485796 | chr7 | 157485881 | 157486082 |
| chr7 | 157486205 | 157486415 | chr7 | 157486476 | 157486600 | chr7 | 157584104 | 157584283 |
| chr7 | 157588510 | 157588869 | chr7 | 157606632 | 157606811 | chr7 | 157690145 | 157690161 |
| chr7 | 158059659 | 158059898 | chr7 | 158936420 | 158936956 | chr7 | 158937062 | 158937091 |
| chr7 | 158937203 | 158937375 | chr7 | 158937577 | 158937610 | chr7 | 168937612 | 158937721 |
| chr7 | 158938132 | 158938485 | chr8 | 686794 | 686885 | chr8 | 687163 | 687218 |
| chr8 | 687838 | 687976 | chr8 | 1085559 | 1085678 | chr8 | 4849040 | 4849263 |
| chr8 | 4849364 | 4849603 | chr8 | 4850173 | 4850323 | chr8 | 4850419 | 4850592 |
| chr8 | 4851662 | 4851686 | chr8 | 4851722 | 4851750 | chr8 | 4851781 | 4851841 |
| chr8 | 4851921 | 4852220 | chr8 | 8748329 | 8748808 | chr8 | 8748819 | 8749058 |
| chr8 | 9722754 | 9722993 | chr8 | 9755973 | 9756284 | chr8 | 9756487 | 9756564 |
| chr8 | 9760646 | 9761245 | chr8 | 9762487 | 9762690 | chr8 | 9762752 | 9762965 |
| chr8 | 9763060 | 9763359 | chr8 | 9763816 | 9764050 | chr8 | 9764196 | 9764295 |
| chr8 | 9764344 | 9764643 | chr8 | 10587507 | 10587603 | chr8 | 11204405 | 11204584 |
| chr8 | 11204709 | 11205008 | chr8 | 11536753 | 11536932 | chr8 | 11537157 | 11537362 |
| chr8 | 11554886 | 11554990 | chr8 | 11555068 | 11555167 | chr8 | 11555474 | 11555605 |
| chr8 | 11559707 | 11559792 | chr8 | 11560068 | 11560457 | chr8 | 11560633 | 11560872 |
| chr8 | 11561357 | 11561724 | chr8 | 11561726 | 11562196 | chr8 | 11562236 | 11562256 |
| chr8 | 11562335 | 11562574 | chr8 | 11562600 | 11563019 | chr8 | 11705869 | 11706228 |
| chr8 | 11726393 | 11726505 | chr8 | 12990409 | 12990529 | chr8 | 12990575 | 12990874 |
| chr8 | 13319857 | 13319937 | chr8 | 15094425 | 15094567 | chr8 | 15094646 | 15094664 |
| chr8 | 15397641 | 15397660 | chr8 | 16884239 | 16884331 | chr8 | 16885104 | 16885343 |
| chr8 | 17271091 | 17271213 | chr8 | 19797396 | 19797538 | chr8 | 19797860 | 19798099 |
| chr8 | 20160679 | 20160710 | chr8 | 22089428 | 22089665 | chr8 | 22562487 | 22562564 |
| chr8 | 22960567 | 22960806 | chr8 | 23021083 | 23021131 | chr8 | 23021193 | 23021209 |
| chr8 | 23260598 | 23260957 | chr8 | 23423830 | 23424009 | chr8 | 23559296 | 23559602 |
| chr8 | 23559666 | 23560615 | chr8 | 23563712 | 23564024 | chr8 | 23564193 | 23564480 |
| chr8 | 23564703 | 23565108 | chr8 | 23566729 | 23566855 | chr8 | 23566901 | 23567214 |
| chr8 | 23567312 | 23567568 | chr8 | 23571588 | 23572029 | chr8 | 23572031 | 23572067 |
| chr8 | 23572334 | 23572646 | chr8 | 23584000 | 23584017 | chr8 | 23584094 | 23584401 |
| chr8 | 23584582 | 23584839 | chr8 | 24770239 | 24770362 | chr8 | 24770414 | 24770658 |
| chr8 | 24771072 | 24771125 | chr8 | 24771350 | 24771575 | chr8 | 24771633 | 24771647 |
| chr8 | 24813089 | 24813388 | chr8 | 24813660 | 24813894 | chr8 | 24814011 | 24814499 |
| chr8 | 24857673 | 24857912 | chr8 | 24858239 | 24858538 | chr8 | 24858770 | 24859249 |
| chr8 | 24859422 | 24859601 | chr8 | 25041656 | 25041955 | chr8 | 25042636 | 25042671 |
| chr8 | 25900324 | 25900693 | chr8 | 25900781 | 25901017 | chr8 | 25901019 | 25901403 |
| chr8 | 25901444 | 25901863 | chr8 | 25902072 | 25902251 | chr8 | 25902545 | 25902640 |
| chr8 | 25903579 | 25903938 | chr8 | 25904055 | 25904294 | chr8 | 25905022 | 25905201 |
| chr8 | 25905696 | 25905907 | chr8 | 25909098 | 25909599 | chr8 | 25909601 | 25909697 |
| chr8 | 26372789 | 26372968 | chr8 | 26723884 | 26724183 | chr8 | 30243289 | 30243526 |
| chr8 | 30769151 | 30769510 | chr8 | 30770028 | 30770110 | chr8 | 30770158 | 30770267 |
| chr8 | 31496380 | 31496859 | chr8 | 31496939 | 31497042 | chr8 | 31497044 | 31497176 |
| chr8 | 31497420 | 31497719 | chr8 | 32406517 | 32406928 | chr8 | 32406930 | 32406996 |
| chr8 | 33371978 | 33372217 | chr8 | 33457052 | 33457471 | chr8 | 35093037 | 35093140 |
| chr8 | 35093877 | 35093974 | chr8 | 35094036 | 35094056 | chr8 | 35093367 | 37655376 |
| chr8 | 37655476 | 37655606 | chr8 | 37655707 | 37655991 | chr8 | 37656050 | 37656186 |
| chr8 | 37822721 | 37823409 | chr8 | 37823411 | 37823475 | chr8 | 37823477 | 37823500 |
| chr8 | 37823790 | 37823805 | chr8 | 37961879 | 37961998 | chr8 | 38008157 | 38008636 |
| chr8 | 38323837 | 38324016 | chr8 | 38965450 | 38965464 | chr8 | 41165785 | 41165919 |
| chr8 | 41166001 | 41166152 | chr8 | 41166267 | 41166680 | chr8 | 41166746 | 41166804 |

TABLE 15-continued

| chr | start | end | chr | start | end | chr | start | end |
|---|---|---|---|---|---|---|---|---|
| chr8 | 41166886 | 41166989 | chr8 | 41167026 | 41167125 | chr8 | 41424682 | 41424921 |
| chr8 | 41624752 | 41624931 | chr8 | 41625038 | 41625217 | chr8 | 41733424 | 41733654 |
| chr8 | 41733685 | 41733723 | chr8 | 41753498 | 41753753 | chr8 | 41753771 | 41753857 |
| chr8 | 41754070 | 41754181 | chr8 | 41754183 | 41754969 | chr8 | 41755104 | 41755283 |
| chr8 | 41910186 | 41910425 | chr8 | 42147417 | 42147596 | chr8 | 42749996 | 42750094 |
| chr8 | 47093172 | 47093351 | chr8 | 47334530 | 47334694 | chr8 | 48100075 | 48100539 |
| chr8 | 49293280 | 49293525 | chr8 | 49293581 | 49293699 | chr8 | 49468571 | 49468828 |
| chr8 | 49468830 | 49469228 | chr8 | 49571955 | 49572134 | chr8 | 49782953 | 49783235 |
| chr8 | 49959156 | 49959335 | chr8 | 50822095 | 50822358 | chr8 | 50822591 | 50822830 |
| chr8 | 50823358 | 50823657 | chr8 | 53477325 | 53477737 | chr8 | 53477945 | 53478352 |
| chr8 | 53478391 | 53478454 | chr8 | 53478456 | 53478744 | chr8 | 53853711 | 53854552 |
| chr8 | 54163240 | 54163350 | chr8 | 54163674 | 54164127 | chr8 | 54789175 | 54789414 |
| chr8 | 54789556 | 54789806 | chr8 | 54790023 | 54790155 | chr8 | 54790214 | 54790883 |
| chr8 | 54791724 | 54791782 | chr8 | 54791898 | 54791946 | chr8 | 54792185 | 54792323 |
| chr8 | 54792548 | 54792671 | chr8 | 54792702 | 54792847 | chr8 | 54794123 | 54794422 |
| chr8 | 54794626 | 54794781 | chr8 | 54794827 | 54794950 | chr8 | 54795140 | 54795165 |
| chr8 | 55366106 | 55366368 | chr8 | 55366952 | 55367725 | chr8 | 55370037 | 55370336 |
| chr8 | 55370338 | 55370423 | chr8 | 55370425 | 55370433 | chr8 | 55370558 | 55370714 |
| chr8 | 55370836 | 55370936 | chr8 | 55371173 | 55371376 | chr8 | 56371440 | 55371725 |
| chr8 | 55371994 | 55372068 | chr8 | 55372417 | 55372638 | chr8 | 55379202 | 55379231 |
| chr8 | 55379296 | 55379457 | chr8 | 55380037 | 55380041 | chr8 | 55382673 | 55382673 |
| chr8 | 55383183 | $5383332 | chr8 | 56013545 | 56013893 | chr8 | 56014012 | 56014024 |
| chr8 | 56014058 | 56014185 | chr8 | 56014377 | 56014417 | chr8 | 56014524 | 56014744 |
| chr8 | 56015035 | 56015053 | chr8 | 56015186 | 56015438 | chr8 | 56015471 | 56015662 |
| chr8 | 56015834 | 56015893 | chr8 | 57025609 | 57025620 | chr8 | 57025776 | 57026028 |
| chr8 | 57026072 | 57026311 | chr8 | 57026502 | 57026644 | chr8 | 57069473 | 57069738 |
| chr8 | 57069851 | 57070013 | chr8 | 57070015 | 57070245 | chr8 | 57358053 | 57358147 |
| chr8 | 57358465 | 57358662 | chr8 | 57358807 | 57359092 | chr8 | 57359260 | 57359732 |
| chr8 | 57360472 | 57360626 | chr8 | 57360770 | 57360891 | chr8 | 58105852 | 58106211 |
| chr8 | 58116923 | 58117162 | chr8 | 58130290 | 58130649 | chr8 | 58907618 | 58907821 |
| chr8 | 58907823 | 58907917 | chr8 | 59058934 | 59059233 | chr8 | 59747274 | 59747402 |
| chr8 | 60032590 | 60032829 | chr8 | 61777488 | 61777622 | chr8 | 61789900 | 61790076 |
| chr8 | 62200414 | 62200879 | chr8 | 63161580 | 63161879 | chr8 | 65281539 | 65281778 |
| chr8 | 65281884 | 65282005 | chr8 | 65282333 | 65282441 | chr8 | 65283708 | 65284187 |
| chr8 | 65285972 | 65286067 | chr8 | 65286371 | 65286451 | chr8 | 65286599 | 65286838 |
| chr8 | 65286868 | 65287229 | chr8 | 65289033 | 65289332 | chr8 | 65289517 | 65290450 |
| chr8 | 65290570 | 65290682 | chr8 | 65290950 | 65291369 | chr8 | 65292572 | 65292816 |
| chr8 | 65488178 | 65488417 | chr8 | 65488618 | 65488799 | chr8 | 65489025 | 654-89065 |
| chr8 | 65489067 | 65489204 | chr8 | 65492637 | 65493056 | chr8 | 65493105 | 65493524 |
| chr8 | 65493556 | 65493579 | chr8 | 65493807 | 65493855 | chr8 | 65493868 | 65493955 |
| chr8 | 65494077 | 65494101 | chr8 | 65494103 | 65494287 | chr8 | 65498465 | 65498550 |
| chr8 | 65498645 | 65498910 | chr8 | 65498926 | 65498944 | chr8 | 65499677 | 65500096 |
| chr8 | 65710868 | 65711084 | chr8 | 66548640 | 66548749 | chr8 | 67024963 | 67025365 |
| chr8 | 67344446 | 67344665 | chr8 | 67344667 | 67344702 | chr8 | 67344810 | 67344865 |
| chr8 | 67873246 | 67873422 | chr8 | 67873799 | 67873799 | chr8 | 67873801 | 67874051 |
| chr8 | 67874165 | 67874673 | chr8 | 67874756 | 67874858 | chr8 | 67874860 | 67875261 |
| chr8 | 67875263 | 67875441 | chr8 | 67875443 | 67875697 | chr8 | 67940548 | 67940960 |
| chr8 | 68864546 | 68864852 | chr8 | 69242828 | 69243007 | chr8 | 69243285 | 69243486 |
| chr8 | 69243488 | 69243903 | chr8 | 69243964 | 69243971 | chr8 | 69244286 | 69244510 |
| chr8 | 69244512 | 69244585 | chr8 | 70744774 | 70745013 | chr8 | 70946670 | 70946915 |
| chr8 | 70947091 | 70947742 | chr8 | 70981866 | 70981880 | chr8 | 70982263 | 70982285 |
| chr8 | 70982287 | 70982567 | chr8 | 70982851 | 70983305 | chr8 | 70983402 | 70983870 |
| chr8 | 70984017 | 70984293 | chr8 | 70984344 | 70984662 | chr8 | 70984745 | 70985081 |
| chr8 | 72273897 | 72274136 | chr8 | 72468473 | 72469664 | chr8 | 72470301 | 72470540 |
| chr8 | 72471037 | 72471158 | chr8 | 72754293 | 72754361 | chr8 | 72754491 | 72754712 |
| chr8 | 72754730 | 72755240 | chr8 | 72755592 | 72755815 | chr8 | 72756656 | 72756812 |
| chr8 | 72756814 | 72756971 | chr8 | 72917268 | 72917429 | chr8 | 72917516 | 72917541 |
| chr8 | 72987519 | 72987916 | chr8 | 72987918 | 72988118 | chr8 | 73163860 | 73164261 |
| chr8 | 73450027 | 73450202 | chr8 | 73450418 | 73450657 | chr8 | 74759411 | 74759565 |
| chr8 | 74759744 | 74759863 | chr8 | 75896477 | 75896836 | chr8 | 75896838 | 75897297 |
| chr8 | 75897299 | 75897436 | chr8 | 76316242 | 76316541 | chr8 | 77585130 | 77585789 |
| chr8 | 77586078 | 77586377 | chr8 | 77586471 | 77586710 | chr8 | 77590144 | 77590563 |
| chr8 | 77593075 | 77593233 | chr8 | 77593235 | 77593453 | chr8 | 77593798 | 77594217 |
| chr8 | 77594552 | 77694595 | chr8 | 77594597 | 77594675 | chr8 | 77594758 | 77595091 |
| chr8 | 77595238 | 77595594 | chr8 | 79428200 | 79428499 | chr8 | 80623887 | 80524126 |
| chr8 | 80524167 | 8024406 | chr8 | 80524854 | 80526103 | chr8 | 80525520 | 80525819 |
| chr8 | 80695842 | 80696007 | chr8 | 80803594 | 80803953 | chr8 | 81478089 | 81478448 |
| chr8 | 85095396 | 85095498 | chr8 | 85095500 | 85095755 | chr8 | 85096485 | 85096721 |
| chr8 | 85096853 | 85096904 | chr8 | 85096939 | 85097003 | chr8 | 85097063 | 85097298 |
| chr8 | 86350455 | 86350567 | chr8 | 86406814 | 86406933 | chr8 | 86436547 | 86436726 |
| chr8 | 86544681 | 86544798 | chr8 | 89339298 | 89339837 | chr8 | 89340189 | 89340237 |
| chr8 | 89340274 | 89340428 | chr8 | 90913517 | 90913756 | chr8 | 91094161 | 91094326 |
| chr8 | 91803578 | 91803720 | chr8 | 91804065 | 91804332 | chr8 | 91996958 | 91997509 |
| chr8 | 91997528 | 91998037 | chr8 | 92083443 | 92083622 | chr8 | 93114033 | 93114150 |
| chr8 | 93114152 | 93114242 | chr8 | 93114307 | 93114632 | chr8 | 95651240 | 95651269 |
| chr8 | 95651448 | 95651599 | chr8 | 95651637 | 95651747 | chr8 | 96219911 | 96220002 |
| chr8 | 97157007 | 97157210 | chr8 | 97157667 | 97157898 | chr8 | 97158022 | 97158146 |
| chr8 | 97165541 | 97165780 | chr8 | 97166351 | 97166530 | chr8 | 97167082 | 97167321 |

TABLE 15-continued

| chr | start | end | chr | start | end | chr | start | end |
|---|---|---|---|---|---|---|---|---|
| chr8 | 97169757 | 97169920 | chr8 | 97169922 | 97169956 | chr8 | 97170054 | 97170338 |
| chr8 | 97170378 | 97170416 | chr8 | 97170793 | 97170972 | chr8 | 97171036 | 97171265 |
| chr8 | 97171318 | 97171959 | chr8 | 97172019 | 97172295 | chr8 | 97172347 | 97172740 |
| chr8 | 97172822 | 97172961 | chr8 | 97172963 | 97173526 | chr8 | 97173528 | 97173546 |
| chr8 | 97173730 | 97173864 | chr8 | 97173921 | 97173991 | chr8 | 97339752 | 97340291 |
| chr8 | 97505950 | 97506049 | chr8 | 97506178 | 97506408 | chr8 | 97506448 | 97506609 |
| chr8 | 97507021 | 97507380 | chr8 | 97507464 | 97507763 | chr8 | 98289744 | 98289868 |
| chr8 | 98289923 | 98290343 | chr8 | 99439030 | 99439209 | chr8 | 99439299 | 99440438 |
| chr8 | 99951330 | 99951509 | chr8 | 99951757 | 99952144 | chr8 | 99952199 | 99952304 |
| chr8 | 99952533 | 99952896 | chr8 | 99954400 | 99954563 | chr8 | 99954679 | 99954819 |
| chr8 | 99955105 | 99955394 | chr8 | 99960231 | 99960498 | chr8 | 99960922 | 99961070 |
| chr8 | 99961111 | 99961174 | chr8 | 19961718 | 99961897 | chr8 | 99985781 | 99986044 |
| chr8 | 99986226 | 99986527 | chr8 | 99986792 | 99987020 | chr8 | 101118140 | 101118491 |
| chr8 | 101118659 | 101118679 | chr8 | 101661837 | 101662000 | chr8 | 101821891 | 101822130 |
| chr8 | 102505458 | 102505654 | chr8 | 102505720 | 102505986 | chr8 | 103629857 | 103629961 |
| chr8 | 104153105 | 104153344 | chr8 | 104153366 | 104153562 | chr8 | 104153682 | 104153725 |
| chr8 | 104512026 | 104513285 | chr8 | 104513365 | 104513909 | chr8 | 104513911 | 104514005 |
| chr8 | 105235293 | 105235502 | chr8 | 105235644 | 105235804 | chr8 | 105235864 | 105236132 |
| chr8 | 105478632 | 105478780 | chr8 | 105479248 | 105479281 | chr8 | 105479315 | 105479531 |
| chr8 | 106331084 | 106331257 | chr8 | 106332004 | 106332286 | chr8 | 107282060 | 107282299 |
| chr8 | 107283938 | 107284054 | chr8 | 107284056 | 107284177 | chr8 | 108509441 | 108509734 |
| chr8 | 109093601 | 109094260 | chr8 | 109094391 | 109094690 | chr8 | 109094757 | 109095437 |
| chr8 | 109095506 | 109095568 | chr8 | 109095570 | 109095974 | chr8 | 109799500 | 109799740 |
| chr8 | 110274904 | 110275021 | chr8 | 110405946 | 110406106 | chr8 | 110592245 | 110592303 |
| chr8 | 110703924 | 110704029 | chr8 | 110704098 | 110704223 | chr8 | 110986354 | 110986773 |
| chr8 | 114444497 | 114444640 | chr8 | 114444709 | 114445275 | chr8 | 114445677 | 114446101 |
| chr8 | 114446851 | 114447346 | chr8 | 114447348 | 114447450 | chr8 | 114448939 | 114449358 |
| chr8 | 114449457 | 114449688 | chr8 | 116660435 | 116660572 | chr8 | 116660616 | 116660854 |
| chr8 | 117950364 | 117950543 | chr8 | 117950700 | 117950999 | chr8 | 120220390 | 120220606 |
| chr8 | 120844011 | 120844126 | chr8 | 121136805 | 121137824 | chr8 | 121823827 | 121824006 |
| chr8 | 121824103 | 121824582 | chr8 | 121825512 | 121825560 | chr8 | 122651770 | 122652009 |
| chr8 | 123695447 | 123695746 | chr8 | 124055137 | 124055235 | chr8 | 124173165 | 124173544 |
| chr8 | 125452275 | 125452394 | chr8 | 126044494 | 126044653 | chr8 | 128745443 | 128745618 |
| chr8 | 128872311 | 128872490 | chr8 | 128889224 | 128889483 | chr8 | 128931157 | 128931336 |
| chr8 | 130369290 | 130369454 | chr8 | 132052057 | 132052300 | chr8 | 132052399 | 132052516 |
| chr8 | 132052590 | 132053256 | chr8 | 132053633 | 132054584 | chr8 | 132054594 | 132054876 |
| chr8 | 133686658 | 133686836 | chr8 | 139508668 | 139508947 | chr8 | 139509656 | 139509671 |
| chr8 | 139509694 | 139510015 | chr8 | 140714485 | 140714964 | chr8 | 140715016 | 140715095 |
| chr8 | 140715379 | 140715588 | chr8 | 140715700 | 140715738 | chr8 | 140715875 | 140716022 |
| chr8 | 140716340 | 140716348 | chr8 | 140834160 | 140834399 | chr8 | 140963208 | 140963447 |
| chr8 | 141159845 | 141160024 | chr8 | 141587975 | 141588214 | chr8 | 141596805 | 141597104 |
| chr8 | 142292454 | 142292808 | chr8 | 142361151 | 142361430 | chr8 | 142367673 | 142367879 |
| chr8 | 142444648 | 142444827 | chr8 | 142528313 | 142528403 | chr8 | 142528455 | 142528607 |
| chr8 | 142528671 | 142528782 | chr8 | 142528835 | 142528962 | chr8 | 142529028 | 142529092 |
| chr8 | 142535241 | 142535587 | chr8 | 142568506 | 142568745 | chr8 | 142694751 | 142695030 |
| chr8 | 142984437 | 142984736 | chr8 | 143088946 | 143089153 | chr8 | 143105162 | 143105461 |
| chr8 | 143509377 | 143509607 | chr8 | 143509629 | 1.43509676 | chr8 | 143532035 | 143532510 |
| chr8 | 143532542 | 143532934 | chr8 | 143533520 | 143533641 | chr8 | 143533709 | 143533999 |
| chr8 | 143557881 | 143558172 | chr8 | 143558389 | 143558688 | chr8 | 143587238 | 143587477 |
| chr8 | 143592664 | 143592762 | chr8 | 143621889 | 143622188 | chr8 | 143701978 | 143702157 |
| chr8 | 143819303 | 143819406 | chr8 | 143858435 | 143858791 | chr8 | 143859223 | 143859281 |
| chr8 | 143859338 | 143859454 | chr8 | 143876854 | 143877033 | chr8 | 143993891 | 143994250 |
| chr8 | 144069457 | 144069749 | chr8 | 144190286 | 144190525 | chr8 | 144203601 | 144203801 |
| chr8 | 144203880 | 144204020 | chr8 | 144226100 | 144226279 | chr8 | 144238743 | 144238982 |
| chr8 | 144241150 | 144241389 | chr8 | 144241444 | 144241522 | chr8 | 144241584 | 144241683 |
| chr8 | 144241785 | 144242381 | chr8 | 144303488 | 144303667 | chr8 | 144328234 | 144328653 |
| chr8 | 144330288 | 144330467 | chr8 | 144344219 | 144344518 | chr8 | 144359928 | 144360177 |
| chr8 | 144360305 | 144360544 | chr8 | 144361672 | 144361911 | chr8 | 144372474 | 144372583 |
| chr8 | 144509238 | 144510617 | chr8 | 144511146 | 144511505 | chr8 | 144511938 | 144512297 |
| chr8 | 144512399 | 144512466 | chr8 | 144650791 | 144650812 | chr8 | 144668532 | 144668767 |
| chr8 | 144668822 | 144669061 | chr8 | 145753443 | 145753622 | chr8 | 145758483 | 145758782 |
| chr8 | 145806184 | 145806272 | chr8 | 145925387 | 145925429 | chr8 | 145925459 | 145925566 |
| chr8 | 145925869 | 145926069 | chr8 | 146013543 | 146013722 | chr8 | 146079134 | 146079297 |
| chr9 | 113346 | 113513 | chr9 | 113550 | 113645 | chr9 | 113749 | 113988 |
| chr9 | 117808 | 117960 | chr9 | 118140 | 118167 | chr9 | 841602 | 841850 |
| chr9 | 841852 | 842032 | chr9 | 842208 | 842244 | chr9 | 842611 | 842748 |
| chr9 | 969482 | 969615 | chr9 | 969685 | 969943 | chr9 | 970012 | 970105 |
| chr9 | 970186 | 970311 | chr9 | 970421 | 970600 | chr9 | 970816 | 970912 |
| chr9 | 970993 | 971175 | chr9 | 971639 | 971655 | chr9 | 972204 | 972863 |
| chr9 | 973184 | 973366 | chr9 | 975248 | 975262 | chr9 | 975693 | 976412 |
| chr9 | 976521 | 976690 | chr9 | 976912 | 977047 | chr9 | 981695 | 981934 |
| chr9 | 1042305 | 1042501 | chr9 | 1042616 | 1043076 | chr9 | 1051905 | 1052247 |
| chr9 | 3181662 | 3181961 | chr9 | 6412497 | 6412900 | chr9 | 6644217 | 6644368 |
| chr9 | 6644540 | 6644636 | chr9 | 6644936 | 6645415 | chr9 | 6645544 | 6645783 |
| chr9 | 6756279 | 6756429 | chr9 | 13278722 | 13278961 | chr9 | 14312943 | 14313182 |
| chr9 | 14347534 | 14347759 | chr9 | 14348234 | 14348533 | chr9 | 17906310 | 17906433 |
| chr9 | 17906461 | 17906789 | chr9 | 17906914 | 17907153 | chr9 | 17907325 | 17907371 |
| chr9 | 17907451 | 17907564 | chr9 | 19789025 | 19789381 | chr9 | 21031636 | 21031924 |

TABLE 15-continued

| chr | start | end | chr | start | end | chr | start | end |
|---|---|---|---|---|---|---|---|---|
| chr9 | 21402520 | 21403119 | chr9 | 21559219 | 21559446 | chr9 | 21559678 | 21559804 |
| chr9 | 21964958 | 21965425 | chr9 | 21965570 | 21965857 | chr9 | 21968138 | 21968434 |
| chr9 | 21968457 | 21968557 | chr9 | 21970881 | 21971155 | chr9 | 21971185 | 21971282 |
| chr9 | 21974182 | 21974329 | chr9 | 21974408 | 21974887 | chr9 | 21994134 | 21994313 |
| chr9 | 21995223 | 21995402 | chr9 | 21995646 | 21995825 | chr9 | 22006057 | 22006153 |
| chr9 | 22006228 | 22006236 | chr9 | 22447567 | 22447772 | chr9 | 23822468 | 23822707 |
| chr9 | 23824487 | 23824666 | chr9 | 23831023 | 23831371 | chr9 | 23831451 | 23831490 |
| chr9 | 29212083 | 29212171 | chr9 | 29212211 | 29212382 | chr9 | 29213431 | 29213730 |
| chr9 | 29213938 | 29214237 | chr9 | 29214276 | 29214515 | chr9 | 29214585 | 29215184 |
| chr9 | 32782547 | 32782936 | chr9 | 32783084 | 32783206 | chr9 | 32783263 | 32783420 |
| chr9 | 32783591 | 32783742 | chr9 | 33524529 | 33524768 | chr9 | 33676697 | 33676876 |
| chr9 | 33677269 | 33677508 | chr9 | 34224262 | 34224497 | chr9 | 34372761 | 34373000 |
| chr9 | 34588960 | 34589259 | chr9 | 35617195 | 35617434 | chr9 | 35675441 | 35675648 |
| chr9 | 35675838 | 35676233 | chr9 | 36036994 | 36037173 | chr9 | 36318274 | 36318389 |
| chr9 | 36739812 | 36740078 | chr9 | 37002394 | 37002518 | chr9 | 37002819 | 37003113 |
| chr9 | 37025465 | 37025884 | chr9 | 37026055 | 37026352 | chr9 | 37026434 | 37026714 |
| chr9 | 37026733 | 37027272 | chr9 | 37027325 | 37027384 | chr9 | 37027386 | 37027512 |
| chr9 | 37027726 | 37027905 | chr9 | 37028870 | 37029049 | chr9 | 37029436 | 37030755 |
| chr9 | 37034163 | 37034342 | chr9 | 37034525 | 37034824 | chr9 | 37035427 | 37035820 |
| chr9 | 37036327 | 37036746 | chr9 | 37037594 | 37038433 | chr9 | 37467521 | 37467634 |
| chr9 | 38620642 | 38620808 | chr9 | 66456024 | 66456117 | chr9 | 71200618 | 71200720 |
| chr9 | 71734803 | 71734920 | chr9 | 71788876 | 71789261 | chr9 | 71789453 | 71789512 |
| chr9 | 71789608 | 71789835 | chr9 | 73032727 | 73032835 | chr9 | 74061745 | 74061759 |
| chr9 | 74061788 | 74062164 | chr9 | 74764449 | 74764748 | chr9 | 77112900 | 77113341 |
| chr9 | 77113559 | 77113709 | chr9 | 77113806 | 77113919 | chr9 | 77114649 | 77114948 |
| chr9 | 77115120 | 77115539 | chr9 | 77115583 | 77115587 | chr9 | 79626794 | 79627453 |
| chr9 | 79628190 | 79628429 | chr9 | 79629208 | 79629499 | chr9 | 79629533 | 79629553 |
| chr9 | 79629791 | 79630491 | chr9 | 79631115 | 79631414 | chr9 | 79631454 | 79631693 |
| chr9 | 79631785 | 79632264 | chr9 | 79632786 | 79632965 | chr9 | 79633322 | 79633737 |
| chr9 | 79633739 | 79633981 | chr9 | 79634088 | 79634987 | chr9 | 79635048 | 79635449 |
| chr9 | 79635746 | 79636066 | chr9 | 79636103 | 79636127 | chr9 | 79636167 | 79636642 |
| chr9 | 79636717 | 79637366 | chr9 | 79637644 | 79637889 | chr9 | 79638137 | 79638336 |
| chr9 | 86152313 | 86152372 | chr9 | 86152382 | 86152492 | chr9 | 86755443 | 86756042 |
| chr9 | 86886632 | 86886811 | chr9 | 87282934 | 87283113 | chr9 | 87283574 | 87283813 |
| chr9 | 87284603 | 87284902 | chr9 | 87285273 | 87285533 | chr9 | 87285555 | 87285556 |
| chr9 | 88137487 | 88137726 | chr9 | 88137875 | 88138091 | chr9 | 89517623 | 89517655 |
| chr9 | 89517861 | 89517917 | chr9 | 89560675 | 89560914 | chr9 | 89560967 | 89561206 |
| chr9 | 91160130 | 91150429 | chr9 | 91605912 | 91606151 | chr9 | 91792283 | 91792452 |
| chr9 | 91792693 | 91792992 | chr9 | 91793083 | 91793622 | chr9 | 93697942 | 93698051 |
| chr9 | 94183793 | 94184032 | chr9 | 94572543 | 94572703 | chr9 | 94712295 | 94712320 |
| chr9 | 95417452 | 95417747 | chr9 | 95560736 | 95560915 | chr9 | 95569672 | 95569911 |
| chr9 | 95570162 | 95570521 | chr9 | 95571540 | 95571659 | chr9 | 95571753 | 95571839 |
| chr9 | 95947121 | 95947360 | chr9 | 96588726 | 96588740 | chr9 | 96588858 | 96588965 |
| chr9 | 96710303 | 96710482 | chr9 | 96710582 | 96711089 | chr9 | 96711169 | 96711447 |
| chr9 | 96711535 | 96711708 | chr9 | 96711901 | 96712080 | chr9 | 96713277 | 96713996 |
| chr9 | 96714997 | 96715068 | chr9 | 96715135 | 96715373 | chr9 | 96715688 | 96715794 |
| chr9 | 96716763 | 96716824 | chr9 | 96716905 | 96717428 | chr9 | 96717450 | 96717542 |
| chr9 | 96717885 | 96718244 | chr9 | 96720752 | 96720886 | chr9 | 96721103 | 96721468 |
| chr9 | 96721689 | 96721903 | chr9 | 96722477 | 96722548 | chr9 | 96722863 | 96722886 |
| chr9 | 96722999 | 96723160 | chr9 | 96723171 | 96723298 | chr9 | 98111281 | 98111561 |
| chr9 | 98111895 | 98112158 | chr9 | 98112344 | 98112472 | chr9 | 98784698 | 98784877 |
| chr9 | 98789557 | 98790013 | chr9 | 98790084 | 98790096 | chr9 | 99449054 | 99449487 |
| chr9 | 99639543 | 99640022 | chr9 | 99983066 | 99983245 | chr9 | 99983319 | 99983704 |
| chr9 | 99983799 | 99983918 | chr9 | 99983925 | 99984004 | chr9 | 100503542 | 100504021 |
| chr9 | 100609970 | 100610135 | chr9 | 100610201 | 100610315 | chr9 | 100610603 | 100610817 |
| chr9 | 100611125 | 100611731 | chr9 | 100613748 | 100614000 | chr9 | 100614193 | 100614407 |
| chr9 | 100614463 | 100615201 | chr9 | 100615203 | 100616036 | chr9 | 100616271 | 100616407 |
| chr9 | 100617285 | 100617449 | chr9 | 100617600 | 100618139 | chr9 | 100619627 | 100620166 |
| chr9 | 100620228 | 100620862 | chr9 | 100818337 | 100818516 | chr9 | 100835850 | 100835969 |
| chr9 | 101469169 | 101469408 | chr9 | 101469521 | 101469880 | chr9 | 101470034 | 101470333 |
| chr9 | 101470991 | 101471170 | chr9 | 101471477 | 101471553 | chr9 | 101471555 | 101471716 |
| chr9 | 101471786 | 101472030 | chr9 | 101705897 | 101706041 | chr9 | 101706043 | 101706196 |
| chr9 | 101706313 | 101706796 | chr9 | 103174718 | 103174825 | chr9 | 104248482 | 104248650 |
| chr9 | 104248698 | 104248721 | chr9 | 104249400 | 104249632 | chr9 | 104500551 | 104500850 |
| chr9 | 110126159 | 110126338 | chr9 | 110228102 | 110228701 | chr9 | 110251381 | 110251493 |
| chr9 | 110252260 | 110252455 | chr9 | 110252548 | 110252619 | chr9 | 112403096 | 112403275 |
| chr9 | 112403290 | 112403301 | chr9 | 112403303 | 112403469 | chr9 | 113341445 | 113341622 |
| chr9 | 113341680 | 113341848 | chr9 | 113341927 | 113342044 | chr9 | 113342201 | 113342428 |
| chr9 | 115067840 | 115067945 | chr9 | 115478852 | 115478971 | chr9 | 115652867 | 115653526 |
| chr9 | 116633786 | 116633905 | chr9 | 117050887 | 117051126 | chr9 | 118916933 | 118917172 |
| chr9 | 120175695 | 120175934 | chr9 | 120176009 | 120176248 | chr9 | 120176793 | 120176972 |
| chr9 | 120507467 | 120507514 | chr9 | 122131383 | 122131439 | chr9 | 122131497 | 122131742 |
| chr9 | 122131785 | 122132026 | chr9 | 122132052 | 122132320 | chr9 | 123295404 | 123295559 |
| chr9 | 124751411 | 124751590 | chr9 | 125676724 | 125676798 | chr9 | 126133698 | 126133937 |
| chr9 | 126154201 | 126154651 | chr9 | 126349070 | 126349191 | chr9 | 126770159 | 126770398 |
| chr9 | 126771440 | 126771799 | chr9 | 126774460 | 126774620 | chr9 | 126775456 | 126775620 |
| chr9 | 126775963 | 126776099 | chr9 | 126777488 | 126777747 | chr9 | 126777974 | 126778086 |
| chr9 | 126778359 | 126778593 | chr9 | 126779391 | 126780044 | chr9 | 126780285 | 126780406 |

TABLE 15-continued

| chr | start | end | chr | start | end | chr | start | end |
|---|---|---|---|---|---|---|---|---|
| chr9 | 126780736 | 126780975 | chr9 | 126783321 | 126783577 | chr9 | 127212750 | 127213109 |
| chr9 | 127265588 | 127265610 | chr9 | 127265876 | 127266127 | chr9 | 127266372 | 127266588 |
| chr9 | 128652097 | 128652336 | chr9 | 128759764 | 128760053 | chr9 | 129276620 | 129276919 |
| chr9 | 129372837 | 129373038 | chr9 | 129373251 | 129373316 | chr9 | 129376096 | 129376275 |
| chr9 | 129376815 | 129376892 | chr9 | 129376932 | 129376994 | chr9 | 129377116 | 129377352 |
| chr9 | 129377593 | 129377636 | chr9 | 129377773 | 129377960 | chr9 | 129378025 | 129378104 |
| chr9 | 129381027 | 129381084 | chr9 | 129387421 | 129387539 | chr9 | 129387701 | 129387749 |
| chr9 | 129387848 | 129388300 | chr9 | 129388639 | 129388754 | chr9 | 129388817 | 129388878 |
| chr9 | 129388915 | 129389274 | chr9 | 129400912 | 129401271 | chr9 | 129445232 | 129445651 |
| chr9 | 129445709 | 129445888 | chr9 | 129485763 | 129485772 | chr9 | 130248345 | 130248524 |
| chr9 | 130461543 | 130461571 | chr9 | 130461687 | 130461842 | chr9 | 130689631 | 130689668 |
| chr9 | 130689742 | 130689742 | chr9 | 131579939 | 131580104 | chr9 | 131607443 | 131607622 |
| chr9 | 131607696 | 131607875 | chr9 | 131854131 | 131854430 | chr9 | 132382297 | 132382355 |
| chr9 | 132382635 | 132383116 | chr9 | 132402743 | 132402982 | chr9 | 132403064 | 132403303 |
| chr9 | 132559298 | 132559413 | chr9 | 132805270 | 132805449 | chr9 | 132805750 | 132805989 |
| chr9 | 133308798 | 133309037 | chr9 | 133534609 | 133534788 | chr9 | 133535707 | 133535934 |
| chr9 | 133536012 | 133536120 | chr9 | 133536150 | 133536345 | chr9 | 133536347 | 133536431 |
| chr9 | 133536675 | 133536974 | chr9 | 133537097 | 133537636 | chr9 | 133538090 | 133538809 |
| chr9 | 133539511 | 133539808 | chr9 | 133540977 | 133541276 | chr9 | 133541594 | 133542433 |
| chr9 | 133773666 | 133774025 | chr9 | 133927265 | 133927564 | chr9 | 133928162 | 133928341 |
| chr9 | 134191003 | 134191302 | chr9 | 134207833 | 134207997 | chr9 | 134421818 | 134421936 |
| chr9 | 134717221 | 134717434 | chr9 | 135037029 | 135037288 | chr9 | 135037334 | 135037448 |
| chr9 | 135455317 | 135455676 | chr9 | 135455912 | 135456024 | chr9 | 135456080 | 135456151 |
| chr9 | 135456391 | 135456630 | chr9 | 135456796 | 135456915 | chr9 | 135458388 | 135458440 |
| chr9 | 135458457 | 135458687 | chr9 | 135459920 | 135460269 | chr9 | 135460795 | 135460819 |
| chr9 | 135461455 | 135461852 | chr9 | 135461969 | 135462078 | chr9 | 13462648 | 135463048 |
| chr9 | 135464709 | 135465008 | chr9 | 135465861 | 135466065 | chr9 | 135466118 | 135466220 |
| chr9 | 135466263 | 135466742. | chr9 | 135548157 | 135548265 | chr9 | 135865007 | 135865246 |
| chr9 | 135898809 | 135899211 | chr9 | 136474432 | 136474592 | chr9 | 137299018 | 137299555 |
| chr9 | 137299596 | 137299677 | chr9 | 137533897 | 137533967 | chr9 | 137534066 | 137534316 |
| chr9 | 137656864 | 137657223 | chr9 | 137667253 | 137667432 | chr9 | 137718802 | 137719101 |
| chr9 | 137721999 | 137722197 | chr9 | 137979803 | 137980102 | chr9 | 137980217 | 137980363 |
| chr9 | 137980806 | 137980985 | chr9 | 138265038 | 138265337 | chr9 | 138562961 | 138563377 |
| chr9 | 138606221 | 138606249 | chr9 | 138606711 | 138606774 | chr9 | 138606821 | 138606850 |
| chr9 | 138606927 | 138607010 | chr9 | 138627556 | 138627925 | chr9 | 138633954 | 138634253 |
| chr9 | 138659704 | 138660003 | chr9 | 138660859 | 138661098 | chr9 | 138661550 | 138661969 |
| chr9 | 138666358 | 138666657 | chr9 | 138880882 | 138880973 | chr9 | 138991833 | 138991903 |
| chr9 | 139000485 | 139000724 | chr9 | 139012193 | 139012492 | chr9 | 139024750 | 139024873 |
| chr9 | 139045579 | 139045758 | chr9 | 139047494 | 139047733 | chr9 | 139085145 | 139085351 |
| chr9 | 139085373 | 139085444 | chr9 | 139085986 | 139086071 | chr9 | 139090420 | 139090552 |
| chr9 | 139090587 | 139090659 | chr9 | 139090692 | 139090742 | chr9 | 139091072 | 139091471 |
| chr9 | 139093273 | 139093923 | chr9 | 139094610 | 139094733 | chr9 | 139095264 | 139095563 |
| chr9 | 139096559 | 139097098 | chr9 | 139111194 | 139111373 | chr9 | 139268961 | 139268987 |
| chr9 | 139421881 | 139422060 | chr9 | 139698839 | 139699138 | chr9 | 139704085 | 139704384 |
| chr9 | 139858945 | 139859365 | chr9 | 139888844 | 139889083 | chr9 | 140024754 | 140024771 |
| chr9 | 140024787 | 140024919 | chr9 | 140024957 | 140025113 | chr9 | 140030424 | 140030603 |
| chr9 | 140032802 | 140033050 | chr9 | 140033192 | 140033197 | chr9 | 140033325 | 140033491 |
| chr9 | 140033619 | 140033627 | chr9 | 140033815 | 140034174 | chr9 | 140050893 | 140051097 |
| chr9 | 140051220 | 140051432 | chr9 | 140127803 | 140128162 | chr9 | 140137220 | 140137334 |
| chr9 | 140205346 | 140205607 | chr9 | 140245789 | 140246084 | chr9 | 140332624 | 140333103 |
| chr9 | 140382472 | 140382697 | chr9 | 140392380 | 140392559 | chr9 | 140396944 | 140397183 |
| chr9 | 140507207 | 140507506 | chr9 | 140708961 | 140709260 | chr9 | 140727429 | 140727611 |
| chr9 | 140727769 | 140728008 | chr9 | 140769913 | 140770048 | chr9 | 140771969 | 140772431 |
| chr9 | 140772495 | 140772594 | chr9 | 140772757 | 140773394 | chr10 | 524680 | 524770 |
| chr10 | 833228 | 833419 | chr10 | 978787 | 979026 | chr10 | 1585208 | 1585325 |
| chr10 | 1708551 | 1708583 | chr10 | 1779342 | 1779821 | chr10 | 3285686 | 3285792 |
| chr10 | 3330410 | 3330696 | chr10 | 3641277 | 3641396 | chr10 | 3678618 | 3678737 |
| chr10 | 3895312 | 3895551 | chr10 | 4599822 | 4600061 | chr10 | 5530673 | 5531080 |
| chr10 | 5875059 | 5875345 | chr10 | 6003386 | 6003625 | chr10 | 6042233 | 6042592 |
| chr10 | 6162073 | 6162302 | chr10 | 6577569 | 6577748 | chr10 | 6984626 | 6984731 |
| chr10 | 7205641 | 7205880 | chr10 | 7212666 | 7213145 | chr10 | 7213532 | 7213610 |
| chr10 | 7215985 | 7216164 | chr10 | 7236109 | 7236348 | chr10 | 7255627 | 7255659 |
| chr10 | 7414447 | 7414686 | chr10 | 7424552 | 7424731 | chr10 | 7449863 | 7450190 |
| chr10 | 7450491 | 7451482 | chr10 | 7452143 | 7452862 | chr10 | 7453233 | 7453657 |
| chr10 | 7453903 | 7454012 | chr10 | 7708311 | 7708379 | chr10 | 7708700 | 7708857 |
| chr10 | 7708955 | 7709090 | chr10 | 7709649 | 7709807 | chr10 | 8075843 | 8075945 |
| chr10 | 8076054 | 8076071 | chr10 | 8076341 | 8076563 | chr10 | 8076730 | 8077449 |
| chr10 | 8077790 | 8078316 | chr10 | 8085600 | 8085800 | chr10 | 8085875 | 8086114 |
| chr10 | 8091818 | 8092099 | chr10 | 8093653 | 8093825 | chr10 | 8093860 | 8093964 |
| chr10 | 8095515 | 8095774 | chr10 | 8095842 | 8095934 | chr10 | 8096086 | 8096265 |
| chr10 | 8096877 | 8097296 | chr10 | 8097387 | 8097588 | chr10 | 11059620 | 11059664 |
| chr10 | 11059933 | 11060158 | chr10 | 11207079 | 11207378 | chr10 | 11700861 | 11701100 |
| chr10 | 13043287 | 13043526 | chr10 | 13141002 | 13141106 | chr10 | 13715462 | 13715485 |
| chr10 | 13933361 | 13933539 | chr10 | 13933597 | 13933935 | chr10 | 13933983 | 13933996 |
| chr10 | 13933998 | 13934126 | chr10 | 13934169 | 13934260 | chr10 | 14966052 | 14966291 |
| chr10 | 15140509 | 15140625 | chr10 | 15761213 | 15761752 | chr10 | 15762050 | 15762211 |
| chr10 | 16562009 | 16562043 | chr10 | 16562369 | 16562626 | chr10 | 16562628 | 16562673 |
| chr10 | 16562710 | 16563665 | chr10 | 16563691 | 16563988 | chr10 | 16564013 | 16564127 |

TABLE 15-continued

| chr | start | end | chr | start | end | chr | start | end |
|---|---|---|---|---|---|---|---|---|
| chr10 | 12270131 | 17270529 | chr10 | 17270889 | 17271255 | chr10 | 17271444 | 17271519 |
| chr10 | 17271521 | 17271728 | chr10 | 17271835 | 17272313 | chr10 | 17272527 | 17272706 |
| chr10 | 17429082 | 17429244 | chr10 | 17429562 | 17429724 | chr10 | 17496545 | 17496834 |
| chr10 | 18429147 | 18429149 | chr10 | 18429552 | 18429749 | chr10 | 18429751 | 18429851 |
| chr10 | 21462526 | 21462690 | chr10 | 21805128 | 21805367 | chr10 | 22047362 | 22047601 |
| chr10 | 22541563 | 22541851 | chr10 | 22542025 | 22542250 | chr10 | 22623924 | 22624306 |
| chr10 | 22624562 | 22625121 | chr10 | 22625383 | 22625783 | chr10 | 22625812 | 22626080 |
| chr10 | 22633902 | 22634175 | chr10 | 22634325 | 22634432 | chr10 | 22634434 | 22634439 |
| chr10 | 22634441 | 22634655 | chr10 | 22764556 | 22765590 | chr10 | 23216786 | 23216843 |
| chr10 | 23216845 | 23217025 | chr10 | 23460264 | 23460552 | chr10 | 23461129 | 23461848 |
| chr10 | 23461976 | 23462463 | chr10 | 23462486 | 23462615 | chr10 | 23462635 | 23462995 |
| chr10 | 23463267 | 23463854 | chr10 | 23463888 | 23464154 | chr10 | 23479793 | 23480597 |
| chr10 | 23480904 | 23481050 | chr10 | 23481304 | 23481385 | chr10 | 23481387 | 23481598 |
| chr10 | 23481862 | 23482233 | chr10 | 23482289 | 23482521 | chr10 | 23483744 | 23484703 |
| chr10 | 23486177 | 23486416 | chr10 | 23487651 | 23488070 | chr10 | 23488343 | 23489256 |
| chr10 | 23489335 | 23489514 | chr10 | 23982360 | 23982899 | chr10 | 23983102 | 23983341 |
| chr10 | 23983618 | 23983801 | chr10 | 23984008 | 23984307 | chr10 | 23984842 | 23985066 |
| chr10 | 24988575 | 24988641 | chr10 | 25464528 | 25464910 | chr10 | 25465320 | 25465350 |
| chr10 | 25465352 | 25465619 | chr10 | 26055737 | 26055916 | chr10 | 26222916 | 26223100 |
| chr10 | 26223102 | 26223206 | chr10 | 26223426 | 26223513 | chr10 | 26223957 | 26224136 |
| chr10 | 26500528 | 26500871 | chr10 | 26501445 | 26501668 | chr10 | 26503593 | 26503832 |
| chr10 | 26504018 | 26504144 | chr10 | 26504191 | 26504257 | chr10 | 26504410 | 26504884 |
| chr10 | 26505009 | 26505236 | chr10 | 26505442 | 26505503 | chr10 | 26505505 | 26505618 |
| chr10 | 26505714 | 26505783 | chr10 | 26505961 | 26506260 | chr10 | 26506288 | 26506353 |
| chr10 | 26506355 | 26506619 | chr10 | 26506903 | 26507427 | chr10 | 26681025 | 26681204 |
| chr10 | 26727024 | 26727443 | chr10 | 26727509 | 26727817 | chr10 | 26727868 | 26727928 |
| chr10 | 26746956 | 26747074 | chr10 | 26816913 | 26817032 | chr10 | 27547856 | 27548332 |
| chr10 | 27548401 | 27548575 | chr10 | 27794394 | 27794512 | chr10 | 27846608 | 27846719 |
| chr10 | 28030790 | 28031029 | chr10 | 28032874 | 28033113 | chr10 | 28033327 | 28033566 |
| chr10 | 28033667 | 28034091 | chr10 | 28034093 | 28034187 | chr10 | 28034327 | 28034446 |
| chr10 | 28034489 | 28034555 | chr10 | 28034874 | 28035388 | chr10 | 28035520 | 28035879 |
| chr10 | 28287286 | 28287318 | chr10 | 28287366 | 28287481 | chr10 | 28287693 | 28288154 |
| chr10 | 28957989 | 28957995 | chr10 | 28958044 | 28958226 | chr10 | 29010956 | 29011239 |
| chr10 | 30026077 | 30026180 | chr10 | 31073276 | 31073541 | chr10 | 31892822 | 31893181 |
| chr10 | 32499021 | 32499260 | chr10 | 33233249 | 33233457 | chr10 | 33624079 | 33624318 |
| chr10 | 33624407 | 33624550 | chr10 | 33624621 | 33624646 | chr10 | 35929334 | 35929609 |
| chr10 | 43249935 | 43250114 | chr10 | 43250317 | 43250780 | chr10 | 43250855 | 43250976 |
| chr10 | 43428329 | 43428577 | chr10 | 43428637 | 43428688 | chr10 | 43428903 | 43428977 |
| chr10 | 43429067 | 43429197 | chr10 | 43429275 | 43429514 | chr10 | 43572591 | 43572830 |
| chr10 | 43600551 | 43600733 | chr10 | 43615462 | 43615639 | chr10 | 43697812 | 43698087 |
| chr10 | 43698199 | 43698231 | chr10 | 43858258 | 43858437 | chr10 | 44879847 | 44880326 |
| chr10 | 44880773 | 44881012 | chr10 | 49652880 | 49653179 | chr10 | 49731470 | 49731829 |
| chr10 | 49731980 | 49732088 | chr10 | 49732156 | 49732315 | chr10 | 49732317 | 49732579 |
| chr10 | 50323162 | 50323360 | chr10 | 50340179 | 50340224 | chr10 | 50507469 | 50507708 |
| chr10 | 50603884 | 50604243 | chr10 | 50604508 | 50604747 | chr10 | 50604967 | 50604979 |
| chr10 | 50605053 | 50605746 | chr10 | 50605931 | 50606530 | chr10 | 50816972 | 50817224 |
| chr10 | 50817778 | 50817810 | chr10 | 50817812 | 50817873 | chr10 | 50818288 | 50818527 |
| chr10 | 50818987 | 50819203 | chr10 | 50821378 | 50821797 | chr10 | 50887557 | 50887616 |
| chr10 | 50887618 | 50887754 | chr10 | 50887790 | 50887916 | chr10 | 50927034 | 50927144 |
| chr10 | 54068449 | 54068688 | chr10 | 54072882 | 54073121 | chr10 | 54073191 | 54073370 |
| chr10 | 54074648 | 54074887 | chr10 | 57387344 | 57387883 | chr10 | 57388239 | 57388598 |
| chr10 | 57390195 | 57390734 | chr10 | 57391072 | 57391311 | chr10 | 60273033 | 60273279 |
| chr10 | 60273347 | 60273392 | chr10 | 60935793 | 60936091 | chr10 | 60936449 | 60936730 |
| chr10 | 60937042 | 60937178 | chr10 | 63212244 | 63212783 | chr10 | 64575433 | 64575732 |
| chr10 | 64578189 | 64578626 | chr10 | 71327627 | 71327865 | chr10 | 71328678 | 71328917 |
| chr10 | 71328980 | 71329002 | chr10 | 71329077 | 71329219 | chr10 | 71329462 | 71329633 |
| chr10 | 71331966 | 71332650 | chr10 | 71332686 | 71333105 | chr10 | 72015070 | 72015425 |
| chr10 | 72043779 | 72043976 | chr10 | 72200001 | 72200065 | chr10 | 72200118 | 72200240 |
| chr10 | 72200251 | 72200772 | chr10 | 72200825 | 72201390 | chr10 | 72973124 | 72973275 |
| chr10 | 73156347 | 73156465 | chr10 | 73156550 | 73156752 | chr10 | 73157768 | 73158049 |
| chr10 | 73847788 | 73847792 | chr10 | 73848209 | 73848267 | chr10 | 75407495 | 75407782 |
| chr10 | 75488860 | 75488975 | chr10 | 77191147 | 77191446 | chr10 | 79396826 | 79397185 |
| chr10 | 81023964 | 81023989 | chr10 | 81664764 | 81665003 | chr10 | 82116994 | 82117283 |
| chr10 | 83634171 | 83634234 | chr10 | 83635441 | 83635499 | chr10 | 83635531 | 83635620 |
| chr10 | 85954322 | 85954561 | chr10 | 88149273 | 88149692 | chr10 | 89692817 | 89692996 |
| chr10 | 89717584 | 89717763 | chr10 | 90966608 | 90966967 | chr10 | 90967587 | 90968126 |
| chr10 | 91294929 | 91295168 | chr10 | 91295449 | 91295492 | chr10 | 91295585 | 91295808 |
| chr10 | 92617156 | 92617395 | chr10 | 93647139 | 93647378 | chr10 | 93647486 | 93647648 |
| chr10 | 93647650 | 93647725 | chr10 | 94450582 | 94450806 | chr10 | 94451372 | 94451587 |
| chr10 | 94825999 | 94826160 | chr10 | 94828062 | 94828125 | chr10 | 94828194 | 94828601 |
| chr10 | 94828633 | 94828932 | chr10 | 94834311 | 94835088 | chr10 | 96304116 | 96304200 |
| chr10 | 98129719 | 98130138 | chr10 | 99080176 | 99080535 | chr10 | 99080774 | 99080931 |
| chr10 | 99080990 | 99081061 | chr10 | 99531116 | 99531535 | chr10 | 99789080 | 99789379 |
| chr10 | 99790171 | 99790340 | chr10 | 99790508 | 99790747 | chr10 | 99790918 | 99791258 |
| chr10 | 100991863 | 100991935 | chr10 | 100992056 | 100992191 | chr10 | 100992222 | 100992535 |
| chr10 | 100992780 | 100992822 | chr10 | 100993448 | 100993938 | chr10 | 100993940 | 100994107 |
| chr10 | 100995956 | 100996315 | chr10 | 101088918 | 101089517 | chr10 | 101089817 | 101090296 |
| chr10 | 101280106 | 101280569 | chr10 | 101283382 | 101283577 | chr10 | 101290028 | 101290161 |

TABLE 15-continued

| chr | start | end | chr | start | end | chr | start | end |
|---|---|---|---|---|---|---|---|---|
| chr10 | 101290180 | 101290699 | chr10 | 101290701 | 101291143 | chr10 | 101291231 | 101291284 |
| chr10 | 101292254 | 101292998 | chr10 | 101293071 | 101293430 | chr10 | 101294662 | 101295400 |
| chr10 | 101295402 | 101295681 | chr10 | 101296665 | 101296717 | chr10 | 101296738 | 101296892 |
| chr10 | 101874886 | 101875222 | chr10 | 102322156 | 102322335 | chr10 | 102419230 | 102419267 |
| chr10 | 102419400 | 102419769 | chr10 | 102430611 | 102430850 | chr10 | 102473775 | 102474014 |
| chr10 | 102483915 | 102484232 | chr10 | 102484234 | 102484246 | chr10 | 102484270 | 102484632 |
| chr10 | 102495416 | 102495717 | chr10 | 102497253 | 102497298 | chr10 | 102497300 | 102497791 |
| chr10 | 102498178 | 102498537 | chr10 | 102501285 | 102501464 | chr10 | 102507408 | 102507536 |
| chr10 | 102508902 | 102509381 | chr10 | 102589340 | 102589579 | chr10 | 102589702 | 102590001 |
| chr10 | 102590075 | 102590494 | chr10 | 102890843 | 102891019 | chr10 | 102891021 | 102891682 |
| chr10 | 102891745 | 102891956 | chr10 | 102892091 | 102892104 | chr10 | 102893528 | 102893952 |
| chr10 | 102894091 | 102895366 | chr10 | 102899088 | 102899687 | chr10 | 102899712 | 102899856 |
| chr10 | 102900263 | 102900671 | chr10 | 102906423 | 102906470 | chr10 | 102906525 | 102906667 |
| chr10 | 102975518 | 102975937 | chr10 | 102976963 | 102977502 | chr10 | 102983088 | 102983380 |
| chr10 | 102983435 | 102983841 | chr10 | 102984313 | 102984375 | chr10 | 102984513 | 102984612 |
| chr10 | 102985689 | 102986048 | chr10 | 102986447 | 102986953 | chr10 | 102987207 | 102987646 |
| chr10 | 102989555 | 102989734 | chr10 | 102996018 | 102996481 | chr10 | 102996597 | 102996737 |
| chr10 | 102997282 | 102997488 | chr10 | 102998493 | 102998912 | chr10 | 103043925 | 103044228 |
| chr10 | 103044301 | 103044471 | chr10 | 103535527 | 103535586 | chr10 | 103535634 | 103535771 |
| chr10 | 103535842 | 103535886 | chr10 | 103536143 | 103536257 | chr10 | 103536300 | 103536502 |
| chr10 | 103579718 | 103579794 | chr10 | 103930133 | 103930248 | chr10 | 104169995 | 104170263 |
| chr10 | 104170408 | 104170513 | chr10 | 104170515 | 104170801 | chr10 | 105036464 | 105036659 |
| chr10 | 105036701 | 105036863 | chr10 | 105036865 | 105036883 | chr10 | 105036894 | 105036943 |
| chr10 | 105037138 | 105037892 | chr10 | 105127048 | 105127156 | chr10 | 105155378 | 105155563 |
| chr10 | 105413527 | 105413886 | chr10 | 106398556 | 106398688 | chr10 | 106398826 | 106398975 |
| chr10 | 106399505 | 106400464 | chr10 | 106400869 | 106400918 | chr10 | 106401323 | 106401433 |
| chr10 | 106401511 | 106402191 | chr10 | 106402272 | 106402428 | chr10 | 106402620 | 106402919 |
| chr10 | 108923951 | 108924060 | chr10 | 108924365 | 108924366 | chr10 | 108924368 | 108924401 |
| chr10 | 108924770 | 108924784 | chr10 | 110226162 | 110226169 | chr10 | 110671800 | 110671884 |
| chr10 | 110671930 | 110672339 | chr10 | 111216709 | 111216804 | chr10 | 112403075 | 112403374 |
| chr10 | 112440312 | 112440483 | chr10 | 115804748 | 115805107 | chr10 | 116164146 | 116164445 |
| chr10 | 116331052 | 116331231 | chr10 | 116853773 | 116854012 | chr10 | 118030550 | 118030706 |
| chr10 | 118031206 | 118031549 | chr10 | 118031625 | 118031864 | chr10 | 118031866 | 118032230 |
| chr10 | 118032413 | 118032645 | chr10 | 118032841 | 118033140 | chr10 | 118033261 | 118033620 |
| chr10 | 118034143 | 118034243 | chr10 | 118890893 | 118891134 | chr10 | 118891180 | 118891192 |
| chr10 | 118891432 | 118891662 | chr10 | 118891716 | 118891854 | chr10 | 118891938 | 118892457 |
| chr10 | 118892518 | 118893360 | chr10 | 118893484 | 118893581 | chr10 | 118893680 | 118893826 |
| chr10 | 118894035 | 118894072 | chr10 | 118896538 | 118896897 | chr10 | 118897822 | 118897847 |
| chr10 | 118897849 | 118898051 | chr10 | 118899199 | 118899378 | chr10 | 118899583 | 118899603 |
| chr10 | 118899893 | 118900034 | chr10 | 118900063 | 118900245 | chr10 | 118900324 | 118900602 |
| chr10 | 118922061 | 118922296 | chr10 | 118922632 | 118922900 | chr10 | 118922944 | 118922991 |
| chr10 | 118923050 | 118923349 | chr10 | 118924511 | 118924990 | chr10 | 118927012 | 118927321 |
| chr10 | 118928459 | 118928614 | chr10 | 119000564 | 119000592 | chr10 | 119000690 | 119001155 |
| chr10 | 119001329 | 119001403 | chr10 | 119001460 | 119001639 | chr10 | 119292324 | 119292419 |
| chr10 | 119294258 | 119294557 | chr10 | 119294747 | 119294898 | chr10 | 119294909 | 119295346 |
| chr10 | 119296628 | 119296644 | chr10 | 119296756 | 119296867 | chr10 | 119297308 | 119297602 |
| chr10 | 119301278 | 119301428 | chr10 | 119302055 | 119302080 | chr10 | 119302859 | 119303278 |
| chr10 | 119304289 | 119304468 | chr10 | 119304794 | 119304829 | chr10 | 119304851 | 119304986 |
| chr10 | 119305062 | 119305213 | chr10 | 119306948 | 119307127 | chr10 | 119311793 | 119311830 |
| chr10 | 119311905 | 119311972 | chr10 | 119312673 | 119313272 | chr10 | 119806952 | 119807131 |
| chr10 | 120354169 | 120354330 | chr10 | 120355462 | 120355701 | chr10 | 120841455 | 120841563 |
| chr10 | 122216811 | 122217170 | chr10 | 122708479 | 122708773 | chr10 | 123357681 | 123357757 |
| chr10 | 123922546 | 123922683 | chr10 | 123923518 | 123923565 | chr10 | 124893085 | 124893193 |
| chr10 | 124893238 | 124893444 | chr10 | 124893551 | 124893850 | chr10 | 124893863 | 124894582 |
| chr10 | 124894871 | 124895026 | chr10 | 124895342 | 124895696 | chr10 | 124895833 | 124896533 |
| chr10 | 124896938 | 124897007 | chr10 | 124897118 | 124897657 | chr10 | 124897958 | 124898056 |
| chr10 | 124898957 | 124899196 | chr10 | 124899651 | 124899890 | chr10 | 124901816 | 124902047 |
| chr10 | 124902139 | 124902569 | chr10 | 124902608 | 124903315 | chr10 | 124904841 | 124905200 |
| chr10 | 124905407 | 124905586 | chr10 | 124905834 | 124905880 | chr10 | 124905920 | 124906186 |
| chr10 | 124907214 | 124907633 | chr10 | 124908017 | 124908196 | chr10 | 124908987 | 124909115 |
| chr10 | 124909253 | 124909538 | chr10 | 124909674 | 124909769 | chr10 | 124910287 | 124910455 |
| chr10 | 124910709 | 124911126 | chr10 | 125425412 | 125425612 | chr10 | 125650778 | 125651163 |
| chr10 | 125651373 | 125651437 | chr10 | 125851248 | 125851727 | chr10 | 125852203 | 125852498 |
| chr10 | 125852541 | 125852622 | chr10 | 125852673 | 125853272 | chr10 | 126135878 | 126136146 |
| chr10 | 126136405 | 126136810 | chr10 | 126137145 | 126137503 | chr10 | 126198864 | 126199162 |
| chr10 | 126697829 | 126698125 | chr10 | 128076477 | 128076716 | chr10 | 128077188 | 128077241 |
| chr10 | 128993816 | 128994529 | chr10 | 128994636 | 128994995 | chr10 | 129534562 | 129534586 |
| chr10 | 129534993 | 129535447 | chr10 | 129535696 | 129535825 | chr10 | 129535986 | 129536224 |
| chr10 | 129536259 | 129536405 | chr10 | 129888774 | 129888965 | chr10 | 129948037 | 129948216 |
| chr10 | 130085210 | 130085276 | chr10 | 130085356 | 130085449 | chr10 | 130203339 | 130203578 |
| chr10 | 130338713 | 130338769 | chr10 | 130338804 | 130339062 | chr10 | 130577690 | 130577869 |
| chr10 | 131647829 | 131648008 | chr10 | 131756992 | 131757051 | chr10 | 131757852 | 131757853 |
| chr10 | 131761291 | 131761530 | chr10 | 131761582 | 131761826 | chr10 | 131761987 | 131762226 |
| chr10 | 131762493 | 131762732 | chr10 | 131762803 | 131763042 | chr10 | 131763264 | 131763337 |
| chr10 | 131763633 | 131763803 | chr10 | 131767343 | 131767504 | chr10 | 131768638 | 131768928 |
| chr10 | 131768930 | 131769117 | chr10 | 131769436 | 131770335 | chr10 | 131770583 | 131770762 |
| chr10 | 131770908 | 131771094 | chr10 | 131771282 | 131771302 | chr10 | 131936600 | 131936719 |
| chr10 | 131937393 | 131937512 | chr10 | 132001196 | 132001615 | chr10 | 133109096 | 133109261 |

TABLE 15-continued

| chr | start | end | chr | start | end | chr | start | end |
|---|---|---|---|---|---|---|---|---|
| chr10 | 133110554 | 133110799 | chr10 | 133794798 | 133795242 | chr10 | 133795313 | 133795517 |
| chr10 | 133795593 | 133795884 | chr10 | 133795976 | 133796059 | chr10 | 133796302 | 133796312 |
| chr10 | 133849561 | 133850103 | chr10 | 133850443 | 133850862 | chr10 | 133951515 | 133952107 |
| chr10 | 133979076 | 133979164 | chr10 | 133999917 | 134000053 | chr10 | 134000109 | 134000124 |
| chr10 | 134000126 | 134000216 | chr10 | 134001140 | 134001359 | chr10 | 134016117 | 134016476 |
| chr10 | 134022771 | 134022950 | chr10 | 134095505 | 134095924 | chr10 | 134272961 | 134272970 |
| chr10 | 134301005 | 134301304 | chr10 | 134481228 | 134481527 | chr10 | 134598013 | 134598091 |
| chr10 | 134598368 | 134598534 | chr10 | 134598973 | 134599022 | chr10 | 134599432 | 134599546 |
| chr10 | 134599714 | 134600017 | chr10 | 134600038 | 134601053 | chr10 | 134601468 | 134601716 |
| chr10 | 134602128 | 134602346 | chr10 | 134607868 | 134608284 | chr10 | 134665056 | 134665295 |
| chr10 | 134679326 | 134679347 | chr10 | 134690469 | 134690636 | chr10 | 134693499 | 134693798 |
| chr10 | 134699772 | 134700011 | chr10 | 134733129 | 134733368 | chr10 | 134733408 | 134733707 |
| chr10 | 134738301 | 134738720 | chr10 | 134755773 | 134756270 | chr10 | 134787988 | 134788194 |
| chr10 | 134795938 | 134796117 | chr10 | 134901113 | 134901294 | chr10 | 134901296 | 134901592 |
| chr10 | 134901919 | 134902125 | chr10 | 134902188 | 134902352 | chr10 | 134916625 | 134916864 |
| chr10 | 134941043 | 134941282 | chr10 | 134942738 | 134943216 | chr10 | 134943461 | 134943644 |
| chr10 | 134944668 | 134944847 | chr10 | 135001961 | 135002260 | chr10 | 135014869 | 135015228 |
| chr10 | 135016972 | 135017209 | chr10 | 135017932 | 135018148 | chr10 | 135018744 | 135019043 |
| chr10 | 135020698 | 135020988 | chr10 | 135023396 | 135023575 | chr10 | 135043080 | 135043613 |
| chr10 | 135043869 | 135044228 | chr10 | 135044555 | 135044662 | chr10 | 135048742 | 135049041 |
| chr10 | 135050226 | 135050355 | chr10 | 135050357 | 135050765 | chr10 | 135076308 | 135076586 |
| chr10 | 135121730 | 135122131 | chr10 | 135139464 | 135139805 | chr11 | 232816 | 233115 |
| chr11 | 392560 | 392739 | chr11 | 394713 | 395072 | chr11 | 406789 | 407028 |
| chr11 | 407326 | 407565 | chr11 | 636821 | 636907 | chr11 | 637162 | 637264 |
| chr11 | 637350 | 637528 | chr11 | 726323 | 726662 | chr11 | 763236 | 763775 |
| chr11 | 829453 | 829533 | chr11 | 850480 | 850899 | chr11 | 862988 | 863167 |
| chr11 | 1027438 | 1027676 | chr11 | 1029142 | 1029501 | chr11 | 1030137 | 1030376 |
| chr11 | 1080304 | 1080416 | chr11 | 1081572 | 1081811 | chr11 | 1214582 | 1215001 |
| chr11 | 1215800 | 1216099 | chr11 | 1229871 | 1230050 | chr11 | 1244304 | 1244543 |
| chr11 | 1250788 | 1251027 | chr11 | 1251088 | 1251447 | chr11 | 1263504 | 1263743 |
| chr11 | 1273988 | 1274287 | chr11 | 1358284 | 1358387 | chr11 | 1374862 | 1375101 |
| chr11 | 1411842 | 1411980 | chr11 | 1430635 | 1430874 | chr11 | 1464205 | 1464504 |
| chr11 | 1469125 | 1469484 | chr11 | 1471840 | 1472139 | chr11 | 1770263 | 1770330 |
| chr11 | 1867980 | 1868339 | chr11 | 1946056 | 1946235 | chr11 | 1957312 | 1957611 |
| chr11 | 1958983 | 1959282 | chr11 | 2040009 | 2040248 | chr11 | 2209824 | 2210363 |
| chr11 | 2225974 | 2226153 | chr11 | 2278625 | 2278924 | chr11 | 2291185 | 2291494 |
| chr11 | 2291801 | 2291844 | chr11 | 2291891 | 2291925 | chr11 | 2291945 | 2292058 |
| chr11 | 2292106 | 2292360 | chr11 | 2292392 | 2292730 | chr11 | 2437889 | 2438246 |
| chr11 | 2465323 | 2465448 | chr11 | 2465462 | 2465571 | chr11 | 2466514 | 2466873 |
| chr11 | 2884027 | 2884121 | chr11 | 2884159 | 2884386 | chr11 | 3169689 | 3169930 |
| chr11 | 4209031 | 4209210 | chr11 | 7273212 | 7273260 | chr11 | 7274141 | 7274320 |
| chr11 | 8040444 | 8040551 | chr11 | 8040553 | 8040564 | chr11 | 8040582 | 8040776 |
| chr11 | 8102910 | 8103209 | chr11 | 8189898 | 8190857 | chr11 | 8284466 | 8284858 |
| chr11 | 8289436 | 8289841 | chr11 | 8290100 | 8290515 | chr11 | 8615600 | 8615779 |
| chr11 | 9025890 | 9026429 | chr11 | 9112372 | 9112586 | chr11 | 9112640 | 9112834 |
| chr11 | 9405310 | 9405542 | chr11 | 10509594 | 10509893 | chr11 | 10811069 | 10811188 |
| chr11 | 10815784 | 10815896 | chr11 | 12029876 | 12030272 | chr11 | 12030274 | 12030355 |
| chr11 | 12030749 | 12030928 | chr11 | 12132423 | 12132662 | chr11 | 12398952 | 12399145 |
| chr11 | 12399181 | 12399311 | chr11 | 12695397 | 12695496 | chr11 | 12695573 | 12695696 |
| chr11 | 12696530 | 12696764 | chr11 | 13030489 | 13030792 | chr11 | 13030862 | 13030919 |
| chr11 | 15136001 | 15136455 | chr11 | 15136458 | 15136480 | chr11 | 16628727 | 16628998 |
| chr11 | 16632403 | 16632428 | chr11 | 16632514 | 16632752 | chr11 | 17497410 | 17497521 |
| chr11 | 17497546 | 17497769 | chr11 | 17740413 | 17740652 | chr11 | 17741583 | 17741585 |
| chr11 | 17741718 | 17741890 | chr11 | 17741953 | 17742484 | chr11 | 17742519 | 17742542 |
| chr11 | 17743640 | 17743874 | chr11 | 18812515 | 18812754 | chr11 | 18812940 | 18813179 |
| chr11 | 18813356 | 18813543 | chr11 | 18813610 | 18813655 | chr11 | 18813691 | 18814050 |
| chr11 | 19263774 | 19263953 | chr11 | 19367007 | 19367135 | chr11 | 19367268 | 19367426 |
| chr11 | 19735656 | 19735835 | chr11 | 20153622 | 20153861 | chr11 | 20178094 | 20178396 |
| chr11 | 20180244 | 20180896 | chr11 | 20181115 | 20181354 | chr11 | 20181608 | 20181644 |
| chr11 | 20181725 | 20182087 | chr11 | 20182763 | 20183062 | chr11 | 20183157 | 20183211 |
| chr11 | 20183313 | 20183516 | chr11 | 20183575 | 20183852 | chr11 | 20184481 | 20185500 |
| chr11 | 20229275 | 20229634 | chr11 | 20229811 | 20230110 | chr11 | 20230312 | 20230551 |
| chr11 | 20618116 | 20618393 | chr11 | 20618423 | 20618925 | chr11 | 20619220 | 20619255 |
| chr11 | 20619637 | 20620056 | chr11 | 20621460 | 20621733 | chr11 | 20622613 | 20622793 |
| chr11 | 20623259 | 20623452 | chr11 | 20690555 | 20690878 | chr11 | 20690983 | 20691034 |
| chr11 | 20691127 | 20691161 | chr11 | 20691163 | 20691380 | chr11 | 20691432 | 20691546 |
| chr11 | 20691591 | 20691616 | chr11 | 20691748 | 20692010 | chr11 | 20692372 | 20692611 |
| chr11 | 22215026 | 22215385 | chr11 | 22362853 | 22363222 | chr11 | 22364719 | 22365078 |
| chr11 | 22365323 | 22365562 | chr11 | 27742111 | 27742290 | chr11 | 27743025 | 27743261 |
| chr11 | 27743343 | 27743702 | chr11 | 27744057 | 27744557 | chr11 | 27744559 | 27744596 |
| chr11 | 27744609 | 27744832 | chr11 | 30037596 | 30037752 | chr11 | 30038595 | 30038834 |
| chr11 | 30605946 | 30606026 | chr11 | 30606028 | 30606161 | chr11 | 30606665 | 30606755 |
| chr11 | 30606796 | 30606964 | chr11 | 30607269 | 30607508 | chr11 | 31818376 | 31818513 |
| chr11 | 31818571 | 31818674 | chr11 | 31819221 | 31819508 | chr11 | 31819569 | 31819928 |
| chr11 | 31819966 | 31820361 | chr11 | 31820461 | 31821105 | chr11 | 31821209 | 31821388 |
| chr11 | 31821390 | 31821860 | chr11 | 31822240 | 31822479 | chr11 | 31824209 | 31824448 |
| chr11 | 31824473 | 31824772 | chr11 | 31824940 | 31824964 | chr11 | 31826043 | 31826071 |
| chr11 | 31826107 | 31826304 | chr11 | 31826409 | 31826733 | chr11 | 31827114 | 31827290 |

TABLE 15-continued

| chr | start | end | chr | start | end | chr | start | end |
|---|---|---|---|---|---|---|---|---|
| chr11 | 31827362 | 31827520 | chr11 | 31827598 | 31828142 | chr11 | 31833007 | 31833232 |
| chr11 | 31835633 | 31835872 | chr11 | 31835959 | 31836517 | chr11 | 31837355 | 31837513 |
| chr11 | 31837542 | 31838486 | chr11 | 31838596 | 31839135 | chr11 | 31839215 | 31839946 |
| chr11 | 31840042 | 31840174 | chr11 | 31840879 | 31841025 | chr11 | 31841775 | 31842089 |
| chr11 | 31842175 | 31842366 | chr11 | 31845947 | 31845991 | chr11 | 31846078 | 31846306 |
| chr11 | 31846351 | 31847070 | chr11 | 31847169 | 31847302 | chr11 | 31847371 | 31847713 |
| chr11 | 31847770 | 31847873 | chr11 | 31847896 | 31848008 | chr11 | 31848377 | 31848603 |
| chr11 | 31848723 | 31849177 | chr11 | 32009013 | 32009127 | chr11 | 32354816 | 32354960 |
| chr11 | 32355000 | 32355291 | chr11 | 32448482 | 32448894 | chr11 | 32455499 | 32455738 |
| chr11 | 32455754 | 32456113 | chr11 | 32456189 | 32456446 | chr11 | 32456759 | 32456912 |
| chr11 | 32456914 | 32457199 | chr11 | 32457220 | 32457268 | chr11 | 32457615 | 32458274 |
| chr11 | 32458307 | 32458860 | chr11 | 32459609 | 32459971 | chr11 | 32460118 | 32460148 |
| chr11 | 32460465 | 32460585 | chr11 | 32460711 | 32460908 | chr11 | 33037393 | 33037632 |
| chr11 | 33858439 | 33858544 | chr11 | 33890197 | 33890436 | chr11 | 33993910 | 33993979 |
| chr11 | 34535019 | 34535198 | chr11 | 35547412 | 35547651 | chr11 | 35641582 | 35641718 |
| chr11 | 35684866 | 35685225 | chr11 | 43596412 | 43596693 | chr11 | 43600416 | 43600655 |
| chr11 | 43601012 | 43601551 | chr11 | 43602369 | 43602847 | chr11 | 43602849 | 43603037 |
| chr11 | 43603077 | 43603328 | chr11 | 43603544 | 43604146 | chr11 | 43604241 | 43604263 |
| chr11 | 44325599 | 44325770 | chr11 | 44326042 | 44326281 | chr11 | 44326341 | 44326350 |
| chr11 | 44326516 | 44326580 | chr11 | 44330555 | 44330609 | chr11 | 44330878 | 44330958 |
| chr11 | 44330960 | 44331440 | chr11 | 44331483 | 44331814 | chr11 | 44332978 | 44333157 |
| chr11 | 44333477 | 44333576 | chr11 | 44337564 | 44337629 | chr11 | 44337727 | 44337862 |
| chr11 | 44337883 | 44338058 | chr11 | 44338087 | 44338154 | chr11 | 44338232 | 44338471 |
| chr11 | 44340722 | 44340808 | chr11 | 44341881 | 44342120 | chr11 | 46316761 | 46316833 |
| chr11 | 46316896 | 46317356 | chr11 | 46317408 | 46317780 | chr11 | 47208968 | 47209267 |
| chr11 | 47358895 | 47359314 | chr11 | 57194253 | 57194612 | chr11 | 57235332 | 57235511 |
| chr11 | 57437215 | 57437316 | chr11 | 57501032 | 57501145 | chr11 | 58672666 | 58673145 |
| chr11 | 59323514 | 59323551 | chr11 | 59323780 | 59323813 | chr11 | 59329224 | 59329343 |
| chr11 | 59333344 | 59333623 | chr11 | 50718587 | 60718854 | chr11 | 60718977 | 50719246 |
| chr11 | 61049596 | 61049756 | chr11 | 61058193 | 61058432 | chr11 | 61062741 | 61063024 |
| chr11 | 61063062 | 61063220 | chr11 | 61276902 | 61277120 | chr11 | 61594995 | 61595354 |
| chr11 | 61596321 | 61596740 | chr11 | 61664564 | 61664863 | chr11 | 61666032 | 61666211 |
| chr11 | 61722964 | 61722987 | chr11 | 62370646 | 62370825 | chr11 | 62440550 | 62440669 |
| chr11 | 63609981 | 63610099 | chr11 | 63641023 | 63641104 | chr11 | 63849298 | 63849530 |
| chr11 | 63934600 | 63934709 | chr11 | 64105852 | 64106031 | chr11 | 64120805 | 64120984 |
| chr11 | 64140323 | 64140502 | chr11 | 64410622 | 64410861 | chr11 | 64480380 | 64480691 |
| chr11 | 64480724 | 64481143 | chr11 | 64578481 | 64578600 | chr11 | 64739369 | 64739608 |
| chr11 | 64809866 | 64809965 | chr11 | 64950214 | 64950438 | chr11 | 65091311 | 65091471 |
| chr11 | 65185459 | 65185818 | chr11 | 65405568 | 65405597 | chr11 | 65478529 | 65478544 |
| chr11 | 65511077 | 65611256 | chr11 | 65511332 | 65511571 | chr11 | 65554043 | 65554195 |
| chr11 | 65600716 | 65600846 | chr11 | 65600848 | 65601735 | chr11 | 65779218 | 65779452 |
| chr11 | 65816357 | 65816520 | chr11 | 65816561 | 65816656 | chr11 | 66188041 | 66188220 |
| chr11 | 66188395 | 66188485 | chr11 | 66188571 | 66188784 | chr11 | 66188853 | 66189054 |
| chr11 | 66454350 | 66454529 | chr11 | 66511148 | 66511327 | chr11 | 66513133 | 66513252 |
| chr11 | 66513554 | 66513732 | chr11 | 66625105 | 66625344 | chr11 | 66648954 | 66649133 |
| chr11 | 66658258 | 66658365 | chr11 | 66790519 | 66790758 | chr11 | 67072139 | 67072489 |
| chr11 | 67209918 | 67210157 | chr11 | 67350887 | 67350961 | chr11 | 67350991 | 67351066 |
| chr11 | 67462559 | 67462918 | chr11 | 67764102 | 67764341 | chr11 | 67781387 | 67781650 |
| chr11 | 67797102 | 67797281 | chr11 | 68096026 | 68096257 | chr11 | 68409507 | 68409663 |
| chr11 | 68804647 | 68804872 | chr11 | 69192466 | 69192885 | chr11 | 69280478 | 69280717 |
| chr11 | 69465962 | 69466143 | chr11 | 69516896 | 69517251 | chr11 | 69517942 | 69518197 |
| chr11 | 69518199 | 69518301 | chr11 | 69518445 | 69518708 | chr11 | 69588848 | 69589267 |
| chr11 | 69589750 | 69589929 | chr11 | 69590067 | 69590113 | chr11 | 69590115 | 69590306 |
| chr11 | 71192669 | 71192921 | chr11 | 71318231 | 71318810 | chr11 | 71318953 | 71319070 |
| chr11 | 71951540 | 71951815 | chr11 | 71952262 | 71952412 | chr11 | 71952459 | 71952621 |
| chr11 | 71954538 | 71954717 | chr11 | 71955242 | 71955481 | chr11 | 71955905 | 71956444 |
| chr11 | 72432759 | 72432997 | chr11 | 72475581 | 72475814 | chr11 | 72532274 | 72532453 |
| chr11 | 72929666 | 72929731 | chr11 | 73072871 | 73073050 | chr11 | 73310285 | 73310445 |
| chr11 | 74394397 | 74394696 | chr11 | 74953165 | 74953337 | chr11 | 74953490 | 74953524 |
| chr11 | 75379155 | 75379249 | chr11 | 75379283 | 75379994 | chr11 | 75459452 | 75459564 |
| chr11 | 76371639 | 76372178 | chr11 | 78672822 | 78673061 | chr11 | 79151076 | 79151315 |
| chr11 | 82444290 | 82445189 | chr11 | 86085657 | 86085862 | chr11 | 86085932 | 86086065 |
| chr11 | 86383080 | 86383186 | chr11 | 88241623 | 88241976 | chr11 | 88242131 | 88242275 |
| chr11 | 88242359 | 88242624 | chr11 | 88798997 | 88799296 | chr11 | 91957408 | 91957767 |
| chr11 | 91957893 | 91957989 | chr11 | 91957991 | 91958312 | chr11 | 91958633 | 91959327 |
| chr11 | 91959355 | 91959532 | chr11 | 91959901 | 91960122 | chr11 | 93063495 | 93063734 |
| chr11 | 93063790 | 93064029 | chr11 | 94133991 | 94134464 | chr11 | 94134683 | 94134950 |
| chr11 | 94275701 | 94275813 | chr11 | 94473511 | 94473671 | chr11 | 94473673 | 94473769 |
| chr11 | 94473803 | 94473997 | chr11 | 94474399 | 94474401 | chr11 | 94502273 | 94502552 |
| chr11 | 94884070 | 94884235 | chr11 | 98891381 | 98891980 | chr11 | 100997579 | 100998085 |
| chr11 | 100998178 | 100998417 | chr11 | 100998588 | 100998745 | chr11 | 101453080 | 101453538 |
| chr11 | 101454511 | 101454580 | chr11 | 102961259 | 102961378 | chr11 | 102979953 | 102980132 |
| chr11 | 104034430 | 104034754 | chr11 | 104034756 | 104035089 | chr11 | 105480662 | 105480787 |
| chr11 | 105480859 | 105480901 | chr11 | 105481125 | 105481317 | chr11 | 105481319 | 105481319 |
| chr11 | 105481321 | 105481322 | chr11 | 105481324 | 105481604 | chr11 | 106888220 | 106888519 |
| chr11 | 106888542 | 106888901 | chr11 | 107461549 | 107461728 | chr11 | 107462318 | 107462557 |
| chr11 | 108603286 | 108603338 | chr11 | 109292830 | 109292830 | chr11 | 109292892 | 109293129 |
| chr11 | 109293635 | 109293764 | chr11 | 109293874 | 109293934 | chr11 | 110582154 | 110582420 |

TABLE 15-continued

| chr | start | end | chr | start | end | chr | start | end |
|---|---|---|---|---|---|---|---|---|
| chr11 | 110582422 | 110582513 | chr11 | 110582794 | 110583029 | chr11 | 110583044 | 110583153 |
| chr11 | 110583473 | 110583832 | chr11 | 111383104 | 111383515 | chr11 | 111383517 | 111383532 |
| chr11 | 111383558 | 111383763 | chr11 | 111411019 | 111411199 | chr11 | 111411201 | 111411582 |
| chr11 | 111411822 | 111412147 | chr11 | 114112948 | 114113127 | chr11 | 115375030 | 115375269 |
| chr11 | 115530040 | 115530096 | chr11 | 115530222 | 115530590 | chr11 | 115530592 | 115530662 |
| chr11 | 115630414 | 115630474 | chr11 | 115630531 | 115630629 | chr11 | 115630631 | 115630889 |
| chr11 | 115630891 | 115631013 | chr11 | 115631217 | 115631456 | chr11 | 116451226 | 116451287 |
| chr11 | 119292705 | 119292884 | chr11 | 119293284 | 119293320 | chr11 | 119293353 | 119293385 |
| chr11 | 119293387 | 119293703 | chr11 | 119612134 | 119612268 | chr11 | 119612324 | 119612493 |
| chr11 | 119612999 | 119613178 | chr11 | 120008006 | 120008605 | chr11 | 120039730 | 120039969 |
| chr11 | 120435322 | 120435561 | chr11 | 120435726 | 120435905 | chr11 | 120998614 | 120998913 |
| chr11 | 122847182 | 122847781 | chr11 | 122847976 | 122848313 | chr11 | 122848369 | 122848695 |
| chr11 | 122849808 | 122850124 | chr11 | 122850149 | 122850263 | chr11 | 122850331 | 122850630 |
| chr11 | 122851074 | 122851313 | chr11 | 122852338 | 122852577 | chr11 | 122854907 | 122855029 |
| chr11 | 122855031 | 122855136 | chr11 | 123066359 | 123066538 | chr11 | 123228971 | 123229180 |
| chr11 | 123229182 | 123229407 | chr11 | 123229462 | 123229510 | chr11 | 123300736 | 123300955 |
| chr11 | 123301016 | 123301029 | chr11 | 123301083 | 123302115 | chr11 | 124735341 | 124735352 |
| chr11 | 124735375 | 124735580 | chr11 | 124736105 | 124736344 | chr11 | 124738694 | 124739125 |
| chr11 | 124739149 | 124739173 | chr11 | 125035687 | 125036286 | chr11 | 125036721 | 125036742 |
| chr11 | 125220423 | 125220722 | chr11 | 125755512 | 125755727 | chr11 | 125773587 | 125774061 |
| chr11 | 125774123 | 125774186 | chr11 | 126870108 | 126870287 | chr11 | 126870379 | 126870429 |
| chr11 | 126870431 | 126870501 | chr11 | 126870525 | 126870618 | chr11 | 126873304 | 126873603 |
| chr11 | 128562802 | 128563186 | chr11 | 128563337 | 128563818 | chr11 | 128563879 | 128564405 |
| chr11 | 128564641 | 128564874 | chr11 | 128564876 | 128564877 | chr11 | 128564992 | 128565480 |
| chr11 | 128657933 | 128658051 | chr11 | 129242783 | 129243242 | chr11 | 129243305 | 129243643 |
| chr11 | 129243944 | 129244301 | chr11 | 129244441 | 129244646 | chr11 | 129245747 | 129245892 |
| chr11 | 129245981 | 129246046 | chr11 | 130318860 | 130319099 | chr11 | 130319451 | 130319690 |
| chr11 | 130785406 | 130785705 | chr11 | 131522676 | 131522960 | chr11 | 131564873 | 131565101 |
| chr11 | 131766899 | 131767048 | chr11 | 131780877 | 131781079 | chr11 | 131781294 | 131781350 |
| chr11 | 132484279 | 132484490 | chr11 | 132813545 | 132813758 | chr11 | 132813908 | 132814049 |
| chr11 | 132864036 | 132864275 | chr11 | 132934031 | 132934139 | chr11 | 132934141 | 132934276 |
| chr11 | 132952677 | 132953003 | chr11 | 132953233 | 132953423 | chr11 | 133231637 | 133231930 |
| chr11 | 133402114 | 133402353 | chr11 | 133825146 | 133825519 | chr11 | 133825521 | 133825625 |
| chr11 | 133906702 | 133907001 | chr11 | 133938911 | 133939064 | chr11 | 133939066 | 133939270 |
| chr11 | 134145629 | 134146427 | chr11 | 134146445 | 134146468 | chr11 | 134146579 | 134146676 |
| chr11 | 134146678 | 134146998 | chr11 | 134201404 | 134201640 | chr11 | 134201754 | 134202173 |
| chr11 | 134281288 | 134281543 | chr12 | 570012 | 570251 | chr12 | 1639060 | 1639299 |
| chr12 | 2162477 | 2162896 | chr12 | 2163071 | 2163370 | chr12 | 2403649 | 2403806 |
| chr12 | 2565971 | 2566330 | chr12 | 2861968 | 2862143 | chr12 | 2862268 | 2862327 |
| chr12 | 2964372 | 2964671 | chr12 | 3600241 | 3600420 | chr12 | 3602186 | 3602717 |
| chr12 | 3602865 | 3602965 | chr12 | 3603009 | 3603061 | chr12 | 4214010 | 4214245 |
| chr12 | 4274002 | 4274420 | chr12 | 4274475 | 4274490 | chr12 | 4362362 | 4362541 |
| chr12 | 4378172 | 4378411 | chr12 | 4379275 | 4379574 | chr12 | 4381341 | 4382480 |
| chr12 | 4382863 | 4383102 | chr12 | 4383399 | 4383878 | chr12 | 4384315 | 4384494 |
| chr12 | 4392801 | 4393023 | chr12 | 4405515 | 4406694 | chr12 | 4554727 | 4554905 |
| chr12 | 5017994 | 5018773 | chr12 | 5018954 | 5019035 | chr12 | 5019085 | 5019743 |
| chr12 | 5019794 | 5020314 | chr12 | 5020441 | 5020513 | chr12 | 5152951 | 5153287 |
| chr12 | 5153358 | 5153461 | chr12 | 5541020 | 5541259 | chr12 | 5542233 | 5542532 |
| chr12 | 5542656 | 5543015 | chr12 | 5840126 | 5840305 | chr12 | 6483537 | 6483836 |
| chr12 | 6664407 | 6664523 | chr12 | 7559085 | 7559384 | chr12 | 8127:19 | 8127238 |
| chr12 | 8171284 | 8171823 | chr12 | 8808505 | 8808640 | chr12 | 8850582 | 8850818 |
| chr12 | 8975096 | 8975452 | chr12 | 10085826 | 10085932 | chr12 | 10363204 | 10363319 |
| chr12 | 11653375 | 11653464 | chr12 | 11653510 | 11653554 | chr12 | 12848294 | 12848653 |
| chr12 | 14133059 | 14133358 | chr12 | 14133541 | 14133960 | chr12 | 14135016 | 14135354 |
| chr12 | 15374156 | 15374395 | chr12 | 16500480 | 16500685 | chr12 | 20521624 | 20521923 |
| chr12 | 20522383 | 20522562 | chr12 | 20522681 | 20522860 | chr12 | 20522976 | 20522980 |
| chr12 | 21680300 | 21680779 | chr12 | 21810395 | 21810956 | chr12 | 21832988 | 21833095 |
| chr12 | 22093749 | 22093960 | chr12 | 22093962 | 22094269 | chr12 | 22094578 | 22094888 |
| chr12 | 22094997 | 22095048 | chr12 | 22095182 | 22095236 | chr12 | 22486717 | 22486882 |
| chr12 | 22487134 | 22487459 | chr12 | 22487461 | 22487556 | chr12 | 22698102 | 22698207 |
| chr12 | 24714835 | 24715014 | chr12 | 24715161 | 24715340 | chr12 | 24715947 | 24716204 |
| chr12 | 24716206 | 24716306 | chr12 | 25056243 | 25056524 | chr12 | 25101507 | 25101746 |
| chr12 | 25101824 | 25101998 | chr12 | 25102010 | 25102183 | chr12 | 25380187 | 25380366 |
| chr12 | 25398165 | 25398404 | chr12 | 28127576 | 28128395 | chr12 | 28128457 | 28129176 |
| chr12 | 29935913 | 29936152 | chr12 | 29936543 | 29936643 | chr12 | 29936652 | 29936777 |
| chr12 | 29936792 | 29936832 | chr12 | 29937234 | 29937343 | chr12 | 29937345 | 29937402 |
| chr12 | 30322697 | 30322925 | chr12 | 30323015 | 30323440 | chr12 | 30323503 | 30323596 |
| chr12 | 30975472 | 30975960 | chr12 | 31079179 | 31079368 | chr12 | 31079418 | 31079594 |
| chr12 | 32340225 | 32340336 | chr12 | 33591700 | 33591879 | chr12 | 33592512 | 33592642 |
| chr12 | 33592644 | 33592848 | chr12 | 33592933 | 33592991 | chr12 | 34494814 | 34494993 |
| chr12 | 34502649 | 34502888 | chr12 | 39299040 | 39299185 | chr12 | 39299269 | 39299639 |
| chr12 | 39539284 | 39539515 | chr12 | 40618318 | 40618557 | chr12 | 41086102 | 41086227 |
| chr12 | 41086229 | 41086461 | chr12 | 41086706 | 41087185 | chr12 | 41582422 | 41583081 |
| chr12 | 41583278 | 41583471 | chr12 | 43944800 | 43944881 | chr12 | 43945110 | 43945219 |
| chr12 | 43945262 | 43945380 | chr12 | 43945417 | 43945621 | chr12 | 43945742 | 43945781 |
| chr12 | 43946203 | 43946401 | chr12 | 45269417 | 45269714 | chr12 | 45444029 | 45444682 |
| chr12 | 45444715 | 45444895 | chr12 | 45444897 | 45444920 | chr12 | 45445062 | 45445348 |
| chr12 | 47225301 | 47225303 | chr12 | 47225320 | 47225477 | chr12 | 47225551 | 47225660 |

TABLE 15-continued

| chr | start | end | chr | start | end | chr | start | end |
|---|---|---|---|---|---|---|---|---|
| chr12 | 47629275 | 47629307 | chr12 | 47629398 | 47629454 | chr12 | 48397154 | 48398173 |
| chr12 | 48398567 | 48398746 | chr12 | 49297770 | 49298009 | chr12 | 49366280 | 49366519 |
| chr12 | 49374838 | 49375027 | chr12 | 49375116 | 49375197 | chr12 | 49375248 | 49375607 |
| chr12 | 49390824 | 49391105 | chr12 | 49391147 | 49391975 | chr12 | 49657624 | 49657722 |
| chr12 | 49690975 | 49691154 | chr12 | 49727092 | 49727208 | chr12 | 49729640 | 49730179 |
| chr12 | 50297417 | 50297555 | chr12 | 50297974 | 50298136 | chr12 | 50426672 | 50426894 |
| chr12 | 51421134 | 51421373 | chr12 | 51421482 | 51421661 | chr12 | 51565470 | 51565562 |
| chr12 | 51930615 | 51930785 | chr12 | 52262896 | 52263195 | chr12 | 52301205 | 52301306 |
| chr12 | 52400735 | 52400907 | chr12 | 52400909 | 52401539 | chr12 | 52401606 | 52401616 |
| chr12 | 52627273 | 52627381 | chr12 | 52652054 | 52652220 | chr12 | 52652600 | 52652713 |
| chr12 | 53108005 | 53108304 | chr12 | 53359245 | 53359316 | chr12 | 53359386 | 53359664 |
| chr12 | 54089004 | 54089602 | chr12 | 54132172 | 54132411 | chr12 | 54145750 | 64145858 |
| chr12 | 54145881 | 54145989 | chr12 | 54321170 | 54321709 | chr12 | 54322108 | 54322302 |
| chr12 | 54324719 | 54325018 | chr12 | 54329264 | 54329479 | chr12 | 54329605 | 54330007 |
| chr12 | $4330980 | 54331219 | chr12 | 54332774. | 54333433 | chr12 | 54338589 | 54338818 |
| chr12 | 54338979 | 54339668 | chr12 | 54343718 | 54343830 | chr12 | 54345523 | 54345659 |
| chr12 | 54345966 | 54346122 | chr12 | 54348761 | 54349080 | chr12 | 54349256 | 54349420 |
| chr12 | 54354419 | 54354694 | chr12 | 54354815 | 54355087 | chr12 | 54355571 | 54355575 |
| chr12 | 54359873 | 54360172 | chr12 | 54360510 | 54360729 | chr12 | 54377835 | 54377947 |
| chr12 | 54377978 | 54378194 | chr12 | 54379100 | 54379699 | chr12 | 54379785 | 54379931 |
| chr12 | 54379959 | 54380486 | chr12 | 54387752 | 54388051 | chr12 | 54388141 | 54388320 |
| chr12 | 54391267 | 54391324 | chr12 | 54391400 | 54391506 | chr12 | 54393403 | 54393460 |
| chr12 | 54393462 | 54393724 | chr12 | 54393847 | 54394266 | chr12 | 54394307 | 54394419 |
| chr12 | 54394467 | 54394546 | chr12 | 54398697 | 54398786 | chr12 | 54398889 | 54399056 |
| chr12 | 54399542 | 54399721 | chr12 | 54402654 | 54402812 | chr12 | 54402975 | 54403454 |
| chr12 | 54408330 | 54408809 | chr12 | 54424670 | 54424749 | chr12 | 54425032 | 54425141 |
| chr12 | 54447781 | 54447833 | chr12 | 54447899 | 54448080 | chr12 | 54520658 | 54520957 |
| chr12 | 54720221 | 54720320 | chr12 | 54812150 | 54812449 | chr12 | 54942906 | 54943191 |
| chr12 | 56882365 | 56882460 | chr12 | 57559778 | 57559914 | chr12 | 57618478 | 57618711 |
| chr12 | 57881046 | 57881345 | chr12 | 57943980 | 57944219 | chr12 | 58021218 | 52021459 |
| chr12 | 58021714 | 58021817 | chr12 | 58021824 | 58022093 | chr12 | 58025551 | 58025734 |
| chr12 | 58025870 | 58025970 | chr12 | 62584739 | 62585013 | chr12 | 62585031 | 62586118 |
| chr12 | 62586178 | 62586357 | chr12 | 63025615 | 63026257 | chr12 | 63543754 | 63544402 |
| chr12 | 63544499 | 63544600 | chr12 | 63544729 | 63544828 | chr12 | 63545239 | 63545418 |
| chr12 | 64061721 | 64062260 | chr12 | 64062295 | 64062498 | chr12 | 64062500 | 64062526 |
| chr12 | 64062528 | 64062654 | chr12 | 64062830 | 64063189 | chr12 | 64783098 | 64783322 |
| chr12 | 64784007 | 64784081 | chr12 | 64784108 | 64784352 | chr12 | 64784460 | 64784639 |
| chr12 | 65218320 | 65218551 | chr12 | 65218901 | 65219259 | chr12 | 65219281 | 65219528 |
| chr12 | 65219606 | 65219880 | chr12 | 65220129 | 65220428 | chr12 | 65514781 | 65515620 |
| chr12 | 65516379 | 65516558 | chr12 | 65557115 | 65557234 | chr12 | 65562064 | 65562172 |
| chr12 | 66122711 | 66122996 | chr12 | 66123381 | 66123610 | chr12 | 66135910 | 66136089 |
| chr12 | 66582743 | 66583048 | chr12 | 56583060 | 66583222 | chr12 | 69327182 | 69327541 |
| chr12 | 69754351 | 69754470 | chr12 | 69754600 | 69754710 | chr12 | 69964101 | 69964340 |
| chr12 | 70087412 | 70087651 | chr12 | 72332550 | 72332789 | chr12 | 72665167 | 72665526 |
| chr12 | 72665566 | 72665771 | chr12 | 72665773 | 72665877 | chr12 | 72666014 | 72666032 |
| chr12 | 72666620 | 72666808 | chr12 | 72666998 | 72667386 | chr12 | 72667388 | 72667519 |
| chr12 | 72667578 | 72667757 | chr12 | 75601168 | 75601231 | chr12 | 75601379 | 75601500 |
| chr12 | 75601696 | 75602007 | chr12 | 75602895 | 75603314 | chr12 | 75728262 | 75728561 |
| chr12 | 77719218 | 77719517 | chr12 | 79257138 | 79257437 | chr12 | 79258850 | 79258879 |
| chr12 | 79258966 | 79259029 | chr12 | 81102136 | 81102456 | chr12 | 81102513 | 81102603 |
| chr12 | 81107921 | 81107932 | chr12 | 81107997 | 81108100 | chr12 | 81471425 | 81471615 |
| chr12 | 81471754 | 81472204 | chr12 | 85306430 | 85306549 | chr12 | 85667173 | 85667832 |
| chr12 | 85673132 | 85673311 | chr12 | 85673385 | 85673915 | chr12 | 85673917 | 85674884 |
| chr12 | 88974346 | 88974356 | chr12 | 93966337 | 93966696 | chr12 | 93966910 | 93967216 |
| chr12 | 93967275 | 93967329 | chr12 | 94543308 | 94543547 | chr12 | 94543811 | 94543947 |
| chr12 | 94543949 | 94544080 | chr12 | 95267450 | 95267629 | chr12 | 95267772 | 95268000 |
| chr12 | 95941794 | 95941795 | chr12 | 95942965 | 95943053 | chr12 | 99288212 | 99288408 |
| chr12 | 99288622 | 99288937 | chr12 | 99288962 | 99288962 | chr12 | 99289162 | 99289411 |
| chr12 | 101025306 | 101025485 | chr12 | 101110926 | 101111165 | chr12 | 101111277 | 101111576 |
| chr12 | 103218396 | 103218655 | chr12 | 103350250 | 103350304 | chr12 | 103350384 | 103350429 |
| chr12 | 103351464 | 103351986 | chr12 | 103352062 | 103352155 | chr12 | 103352171 | 103352267 |
| chr12 | 103352269 | 103352283 | chr12 | 103352314 | 103352783 | chr12 | 103358763 | 103359002 |
| chr12 | 103359482 | 103359572 | chr12 | 103359574 | 103359661 | chr12 | 103889086 | 103889306 |
| chr12 | 103889660 | 103889714 | chr12 | 103889789 | 103889899 | chr12 | 104609340 | 104609526 |
| chr12 | 104609528 | 104609797 | chr12 | 104610163 | 104610179 | chr12 | 104850430 | 104850537 |
| chr12 | 104850578 | 104850669 | chr12 | 104850983 | 104851282 | chr12 | 104851941 | 104852151 |
| chr12 | 104852153 | 104852439 | chr12 | 104852441 | 104852446 | chr12 | 104852448 | 104852600 |
| chr12 | 105478222 | 105478457 | chr12 | 106974279 | 106974458 | chr12 | 106976641 | 106976780 |
| chr12 | 106976843 | 106976880 | chr12 | 106977394 | 106977589 | chr12 | 106979079 | 106979590 |
| chr12 | 106979718 | 106979874 | chr12 | 106979876 | 106980077 | chr12 | 106980129 | 106980428 |
| chr12 | 106980912 | 1.06981490 | chr12 | 107486462 | 107486673 | chr12 | 107487114 | 107487945 |
| chr12 | 107712199 | 107712378 | chr12 | 107713137 | 107713310 | chr12 | 107714771 | 107715250 |
| chr12 | 108168883 | 108169414 | chr12 | 108169550 | 108169602 | chr12 | 108237377 | 108237525 |
| chr12 | 108237661 | 108237676 | chr12 | 108238034 | 108238514 | chr12 | 108238684 | 108238719 |
| chr12 | 108297320 | 108297559 | chr12 | 110353315 | 110353553 | chr12 | 110717447 | 110717806 |
| chr12 | 111127079 | 111127438 | chr12 | 111471099 | 111471309 | chr12 | 111471311 | 111471638 |
| chr12 | 111471871 | 111471960 | chr12 | 111472059 | 111472196 | chr12 | 111472357 | 111472511 |
| chr12 | 111472572 | 111472672 | chr12 | 111763136 | 111763227 | chr12 | 113012877 | 113013236 |

TABLE 15-continued

| chr | start | end | chr | start | end | chr | start | end |
|---|---|---|---|---|---|---|---|---|
| chr12 | 113541644 | 113542183 | chr12 | 113592150 | 113592449 | chr12 | 113900616 | 113900678 |
| chr12 | 113900753 | 113900855 | chr12 | 113900974 | 113901159 | chr12 | 113901408 | 113901693 |
| chr12 | 113901951 | 113902018 | chr12 | 113902042 | 113902429 | chr12 | 113903394 | 113903573 |
| chr12 | 113904689 | 113905108 | chr12 | 113908894 | 113909315 | chr12 | 113909329 | 113909503 |
| chr12 | 113909535 | 113909553 | chr12 | 113909569 | 113909657 | chr12 | 113909718 | 113909808 |
| chr12 | 113913180 | 113913682 | chr12 | 113913884 | 113913887 | chr12 | 1139:3889 | 113914139 |
| chr12 | 113916147 | 113916266 | chr12 | 113916327 | 113916419 | chr12 | 113916575 | 113916754 |
| chr12 | 113916873 | 113917112 | chr12 | 113917212 | 113917391 | chr12 | 113917684 | 113917701 |
| chr12 | 113917731 | 113917983 | chr12 | 114029325 | 114029509 | chr12 | 114029546 | 114029744 |
| chr12 | 114075942 | 114076177 | chr12 | 114337849 | 114337868 | chr12 | 114833895 | 114834173 |
| chr12 | 114838227 | 114838312 | chr12 | 114838369 | 114838826 | chr12 | 114840946 | 114841185 |
| chr12 | 114843016 | 114843187 | chr12 | 114843261 | 114843375 | chr12 | 114843454 | 114843753 |
| chr12 | 114844102 | 114844401 | chr12 | 114846623 | 114846862 | chr12 | 114846886 | 114846947 |
| chr12 | 114847043 | 114847164 | chr12 | 114847166 | 114847437 | chr12 | 114847578 | 114847741 |
| chr12 | 114851969 | 114852181 | chr12 | 114852214 | 114852268 | chr12 | 114877068 | 114877367 |
| chr12 | 114878448 | 114878594 | chr12 | 114878809 | 114879093 | chr12 | 114881550 | 114881849 |
| chr12 | 114882488 | 114882727 | chr12 | 114883385 | 114883554 | chr12 | 114885134 | 114885184 |
| chr12 | 114885372 | 114885373 | chr12 | 114918513 | 114918806 | chr12 | 115136153 | 115136441 |
| chr12 | 116945988 | 116946200 | chr12 | 116946251 | 116946647 | chr12 | 117473983 | 117474282 |
| chr12 | 117797999 | 117798170 | chr12 | 117799331 | 117799621 | chr12 | 118860317 | 118860436 |
| chr12 | 119212120 | 119212200 | chr12 | 119212319 | 119212479 | chr12 | 119418512 | 119418931 |
| chr12 | 119419369 | 119419541 | chr12 | 119419631 | 119419920 | chr12 | 120032777 | 120033256 |
| chr12 | 120148125 | 120148345 | chr12 | 120148824 | 120149063 | chr12 | 120885155 | 120885274 |
| chr12 | 121622472 | 121622591 | chr12 | 122192885 | 122192933 | chr12 | 122284969 | 122285189 |
| chr12 | 123129041 | 123129139 | chr12 | 123233818 | 123233926 | chr12 | 124393463 | 124393702 |
| chr12 | 124397514 | 124397693 | chr12 | 125009254 | 125009381 | chr12 | 125533851 | 125534508 |
| chr12 | 125670024 | 125670261 | chr12 | 125670335 | 125670383 | chr12 | 126168468 | 126168702 |
| chr12 | 127210933 | 127210935 | chr12 | 127211317 | 127211472 | chr12 | 127765066 | 127765535 |
| chr12 | 127939988 | 127940189 | chr12 | 127940271 | 127940347 | chr12 | 128751295 | 128751534 |
| chr12 | 128751732 | 128751878 | chr12 | 128752115 | 128752331 | chr12 | 128752423 | 128753022 |
| chr12 | 128753136 | 128753315 | chr12 | 128850442 | 128850630 | chr12 | 128850632 | 128850739 |
| chr12 | 129337901 | 129337910 | chr12 | 129338588 | 129338826 | chr12 | 129338852 | 129338919 |
| chr12 | 130037571 | 130037866 | chr12 | 130387797 | 130387914 | chr12 | 130388332 | 130388435 |
| chr12 | 130389013 | 130389231 | chr12 | 130589116 | 130589354 | chr12 | 130645131 | 130645730 |
| chr12 | 130646590 | 130646654 | chr12 | 130646946 | 130647116 | chr12 | 130647574 | 130647909 |
| chr12 | 130647951 | 130648070 | chr12 | 130821287 | 130821706 | chr12 | 130968586 | 130968758 |
| chr12 | 131200303 | 131200649 | chr12 | 131400719 | 131401018 | chr12 | 131402943 | 131403229 |
| chr12 | 131613255 | 131513494 | chr12 | 132169246 | 132169357 | chr12 | 132221614 | 132222153 |
| chr12 | 132333337 | 132333418 | chr12 | 132333517 | 132333696 | chr12 | 132348549 | 132348788 |
| chr12 | 132423596 | 132423829 | chr12 | 132643321 | 132643474 | chr12 | 132986419 | 132986658 |
| chr12 | 133002713 | 133003312 | chr12 | 133194996 | 133195061 | chr12 | 133195063 | 133195229 |
| chr12 | 133199642 | 133199797 | chr12 | 133463657 | 133463956 | chr12 | 133464018 | 133464074 |
| chr12 | 133464755 | 133464920 | chr12 | 133481333 | 133481383 | chr12 | 133481490 | 133481520 |
| chr12 | 133481522 | 133481732 | chr12 | 133484660 | 133484853 | chr12 | 133485162 | 133485348 |
| chr12 | 133485463 | 133485690 | chr12 | 133485816 | 133485942 | chr12 | 133757959 | 133758198 |
| chr13 | 20735708 | 20736187 | chr13 | 21649557 | 21649856 | chr13 | 22243192 | 22243551 |
| chr13 | 23489764 | 23490003 | chr13 | 23733355 | 23734124 | chr13 | 23734182 | 23734298 |
| chr13 | 24477566 | 24477985 | chr13 | 25115623 | 25115648 | chr13 | 25115694 | 25115852 |
| chr13 | 25319764 | 25319905 | chr13 | 25320109 | 25320109 | chr13 | 25320388 | 25320540 |
| chr13 | 25320614 | 25321029 | chr13 | 25321113 | 25321443 | chr13 | 25321612 | 25322031 |
| chr13 | 25592963 | 25593040 | chr13 | 25593062 | 25593201 | chr13 | 25620951 | 25620954 |
| chr13 | 25620956 | 25621206 | chr13 | 25621264 | 25621490 | chr13 | 25744639 | 25744735 |
| chr13 | 25745301 | 25745595 | chr13 | 25745727 | 25746054 | chr13 | 25946301 | 25946488 |
| chr13 | 25946529 | 25946674 | chr13 | 25946802 | 25946888 | chr13 | 26042580 | 26042708 |
| chr13 | 26042769 | 26043171 | chr13 | 26043341 | 26043590 | chr13 | 26625267 | 26625657 |
| chr13 | 27132307 | 27132310 | chr13 | 27334118 | 27334657 | chr13 | 27334684 | 27334723 |
| chr13 | 27334725 | 27334983 | chr13 | 28239896 | 28240195 | chr13 | 28365615 | 28366181 |
| chr13 | 28366381 | 28366602 | chr13 | 28366665 | 28366680 | chr13 | 28366923 | 28367039 |
| chr13 | 28367712 | 28367946 | chr13 | 28368154 | 28368251 | chr13 | 28368373 | 28368672 |
| chr13 | 28368872 | 28369071 | chr13 | 28369162 | 28369891 | chr13 | 28369952 | 28370071 |
| chr13 | 28370855 | 28371154 | chr13 | 28394667 | 28394966 | chr13 | 28395408 | 28395647 |
| chr13 | 28395917 | 28396156 | chr13 | 28491694 | 28492050 | chr13 | 28492160 | 28492425 |
| chr13 | 28492422 | 28492639 | chr13 | 28528432 | 28528851 | chr13 | 28540657 | 28541016 |
| chr13 | 28543138 | 28543317 | chr13 | 28544321 | 28544585 | chr13 | 28544665 | 28544980 |
| chr13 | 28549396 | 28549892 | chr13 | 28550240 | 28550655 | chr13 | 28551320 | 28551549 |
| chr13 | 28551850 | 28552269 | chr13 | 28552660 | 28552660 | chr13 | 28652720 | 28552899 |
| chr13 | 28552935 | 28553234 | chr13 | 28673927 | 28674227 | chr13 | 28674721 | 28674826 |
| chr13 | 29067676 | 29068515 | chr13 | 29068847 | 29068986 | chr13 | 29068994 | 29069146 |
| chr13 | 29106217 | 29106422 | chr13 | 29106624 | 29106815 | chr13 | 29106899 | 29107064 |
| chr13 | 29107253 | 29107409 | chr13 | 30707495 | 30707674 | chr13 | 31742856 | 31743242 |
| chr13 | 32605033 | 32605212 | chr13 | 32605443 | 32605596 | chr13 | 32605675 | 32606001 |
| chr13 | 33591211 | 33591510 | chr13 | 33924579 | 33924812 | chr13 | 36704848 | 36705147 |
| chr13 | 36705351 | 36705446 | chr13 | 36705448 | 36705566 | chr13 | 36920216 | 36920224 |
| chr13 | 36920267 | 36920332 | chr13 | 36920334 | 36920387 | chr13 | 36920465 | 36920515 |
| chr13 | 36920528 | 36920887 | chr13 | 37004681 | 37004992 | chr13 | 37005581 | 37005581 |
| chr13 | 37005900 | 37006063 | chr13 | 37006434 | 37006658 | chr13 | 37006734 | 37006840 |
| chr13 | 37247982 | 37248149 | chr13 | 32248295 | 37248305 | chr13 | 37248307 | 37248316 |
| chr13 | 37248886 | 37248994 | chr13 | 37249040 | 37249125 | chr13 | 37633915 | 37634094 |

TABLE 15-continued

| chr | start | end | chr | start | end | chr | start | end |
|---|---|---|---|---|---|---|---|---|
| chr13 | 37643855 | 37644094 | chr13 | 38443544 | 38443634 | chr13 | 38443636 | 38443716 |
| chr13 | 39261309 | 39261472 | chr13 | 43566148 | 43566652 | chr13 | 44947643 | 44947700 |
| chr13 | 44947726 | 44948302 | chr13 | 45885802 | 45885981 | chr13 | 45905243 | 45905356 |
| chr13 | 46425447 | 46425555 | chr13 | 46425576 | 46425654 | chr13 | 46660850 | 46660944 |
| chr13 | 46961395 | 46961634 | chr13 | 47468065 | 47468244 | chr13 | 47526167 | 47526286 |
| chr13 | 48667803 | 48667982 | chr13 | 49794034 | 49794926 | chr13 | 53312917 | 53313314 |
| chr13 | 53313513 | 53313529 | chr13 | 53313531 | 53313613 | chr13 | 53313678 | 53313950 |
| chr13 | 53419636 | 53419729 | chr13 | 53419731 | 53419875 | chr13 | 53419931 | 53420021 |
| chr13 | 53421822 | 53421880 | chr13 | 53422220 | 53422252 | chr13 | 53422433. | 53422459 |
| chr13 | 53423759 | 53424058 | chr13 | 58203504 | 58203743 | chr13 | 58203768 | 58204187 |
| chr13 | 58204253 | 58204492 | chr13 | 58205944 | 58206232 | chr13 | 58206453 | 58206772 |
| chr13 | 58206862 | 58207083 | chr13 | 58207382 | 58207401 | chr13 | 58207568 | 58207814 |
| chr13 | 58207892 | 58208101 | chr13 | 58208412 | 58209011 | chr13 | 67804144 | 67804175 |
| chr13 | 67804420 | 67804531 | chr13 | 67805100 | 67805286 | chr13 | 70681550 | 70681778 |
| chr13 | 70681867 | 70682149 | chr13 | 72439047 | 72439109 | chr13 | 73619573 | 73619698 |
| chr13 | 78492724 | 78492942 | chr13 | 78493092 | 78493271 | chr13 | 78493363 | 78493902 |
| chr13 | 79169850 | 79170114 | chr13 | 79170348 | 79170384 | chr13 | 79170468 | 79170981 |
| chr13 | 79171038 | 79171277 | chr13 | 79175678 | 79175944 | chr13 | 79176078 | 79176126 |
| chr13 | 79176277 | 79176421 | chr13 | 79176609 | 79176873 | chr13 | 79176897 | 79177185 |
| chr13 | 79177306 | 79177623 | chr13 | 79177886 | 79178096 | chr13 | 79183327 | 79183424 |
| chr13 | 84455499 | 84455798 | chr13 | 88323504 | 88323831 | chr13 | 88323868 | 88324169 |
| chr13 | 88324171 | 88324283 | chr13 | 88324415 | 88324519 | chr13 | 88325201 | 88325560 |
| chr13 | 88325731 | 88326140 | chr13 | 88326447 | 88326708 | chr13 | 88326937 | 88322106 |
| chr13 | 88997832 | 88997951 | chr13 | 91948415 | 91948594 | chr13 | 92050668 | 92050843 |
| chr13 | 92051065 | 92051244 | chr13 | 92051273 | 92061400 | chr13 | 92051402 | 92051514 |
| chr13 | 93879213 | 93879303 | chr13 | 93879305 | 93879452 | chr13 | 93879595 | 93879775 |
| chr13 | 93879994 | 93880217 | chr13 | 93880534 | 93880738 | chr13 | 93880794 | 93880842 |
| chr13 | 93880844 | 93880953 | chr13 | 95357237 | 95357416 | chr13 | 95357496 | 95357855 |
| chr13 | 95357954 | 95358253 | chr13 | 95359656 | 95359895 | chr13 | 95360228 | 95360467 |
| chr13 | 95363111 | 95363452 | chr13 | 95363494 | 95363530 | chr13 | 95363697 | 95363960 |
| chr13 | 95364065 | 95364291 | chr13 | 95364409 | 95364675 | chr13 | 95364677 | 95364888 |
| chr13 | 95619931 | 95620170 | chr13 | 95620560 | 95620782 | chr13 | 95620854 | 95621099 |
| chr13 | 96031611 | 96031725 | chr13 | 96204923 | 96205438 | chr13 | 96296297 | 96296346 |
| chr13 | 96296373 | 96296556 | chr13 | 96296841 | 96296950 | chr13 | 96296992 | 96297215 |
| chr13 | 96743713 | 96743895 | chr13 | 96743897 | 96744212 | chr13 | 99851662 | 99851748 |
| chr13 | 100547770 | 100547894 | chr13 | 100608462 | 100608536 | chr13 | 100608597 | 100608805 |
| chr13 | 100608839 | 100609136 | chr13 | 100621859 | 100622031 | chr13 | 100624213 | 100624233 |
| chr13 | 100624324 | 100624452 | chr13 | 100624509 | 100624715 | chr13 | 100626905 | 100626925 |
| chr13 | 100630545 | 100631084 | chr13 | 100634227 | 100634382 | chr13 | 100635310 | 100635330 |
| chr13 | 100635399 | 100635518 | chr13 | 100636084 | 100636111 | chr13 | 100636131 | 100636323 |
| chr13 | 100637289 | 100637588 | chr13 | 100642161 | 100642282 | chr13 | 100643955 | 100644170 |
| chr13 | 100649334 | 100649576 | chr13 | 100649800 | 100649885 | chr13 | 100649945 | 100650018 |
| chr13 | 102568380 | 102568559 | chr13 | 102569313 | 102569643 | chr13 | 103046619 | 103047053 |
| chr13 | 103047055 | 103047098 | chr13 | 103052252 | 103052468 | chr13 | 103052470 | 103052671 |
| chr13 | 103052797 | 103052828 | chr13 | 103052830 | 103053036 | chr13 | 103053296 | 103053509 |
| chr13 | 107186781 | 107186960 | chr13 | 107187085 | 107187242 | chr13 | 108518298 | 108518354 |
| chr13 | 108518445 | 108518494 | chr13 | 108518724 | 108519017 | chr13 | 108519162 | 108519461 |
| chr13 | 108519637 | 108519746 | chr13 | 108519902 | 108519996 | chr13 | 108520370 | 108520535 |
| chr13 | 108520916 | 108520945 | chr13 | 108520947 | 108520969 | chr13 | 109147599 | 109147863 |
| chr13 | 109148155 | 109:48279 | chr13 | 109148377 | 109148438 | chr13 | 109148685 | 109149115 |
| chr13 | 109149164 | 109149284 | chr13 | 110434373 | 110434672 | chr13 | 110958720 | 110958977 |
| chr13 | 110958979 | 110959054 | chr13 | 110959629 | 110959649 | chr13 | 110959753 | 110960048 |
| chr13 | 110960345 | 110960386 | chr13 | 110960453 | 110960692 | chr13 | 111278225 | 111278521 |
| chr13 | 111363885 | 111364060 | chr13 | 112272891 | 112273102 | chr13 | 112707603 | 112707962 |
| chr13 | 112708002 | 112708005 | chr13 | 112708308 | 112708601 | chr13 | 112709408 | 112709647 |
| chr13 | 112709713 | 112709713 | chr13 | 112709787 | 112710026 | chr13 | 112710247 | 112710253 |
| chr13 | 112710360 | 112710476 | chr13 | 112710669 | 112710823 | chr13 | 112710825 | 112711294 |
| chr13 | 112711376 | 112711868 | chr13 | 112711924 | 112713123 | chr13 | 112715267 | 112715719 |
| chr13 | 112715910 | 112716389 | chr13 | 112716695 | 112716814 | chr13 | 112716982 | 112717243 |
| chr13 | 112717323 | 112717611 | chr13 | 112717743 | 112718042 | chr13 | 112719940 | 112720599 |
| chr13 | 112720626 | 112720865 | chr13 | 112720938 | 112721027 | chr13 | 112722129 | 112722221 |
| chr13 | 112722275 | 112722403 | chr13 | 112724431 | 112724610 | chr13 | 112726240 | 112726293 |
| chr13 | 112726436 | 112726659 | chr13 | 112727962 | 112728201 | chr13 | 112728336 | 112728367 |
| chr13 | 112758033 | 112758373 | chr13 | 112758496 | 112758688 | chr13 | 112759112 | 112759349 |
| chr13 | 112759538 | 112759717 | chr13 | 112760007 | 112760413 | chr13 | 112760755 | 112761305 |
| chr13 | 113598526 | 113598877 | chr13 | 113985597 | 113985956 | chr13 | 114055881 | 114056240 |
| chr13 | 114059990 | 114060409 | chr13 | 114074692 | 114074931 | chr13 | 114123081 | 114123358 |
| chr13 | 114189654 | 114189732 | chr13 | 114221548 | 114221655 | chr13 | 114304637 | 114305016 |
| chr13 | 114479330 | 114479509 | chr13 | 114497930 | 114498349 | chr13 | 114748251 | 114748730 |
| chr13 | 114780482 | 114781141 | chr13 | 114807537 | 114807896 | chr13 | 114855533 | 114855772 |
| chr13 | 114862381 | 114862458 | chr13 | 114961729 | 114962028 | chr14 | 21093364 | 21093531 |
| chr14 | 21093604 | 21093723 | chr14 | 21100674 | 21100906 | chr14 | 22004932 | 22004993 |
| chr14 | 22004995 | 22005171 | chr14 | 23356162 | 23356341 | chr14 | 23706666 | 23706805 |
| chr14 | 24803493 | 24803917 | chr14 | 24803919 | 24804123 | chr14 | 24804425 | 24804512 |
| chr14 | 26674280 | 26674459 | chr14 | 26674625 | 26674703 | chr14 | 27066520 | 27066699 |
| chr14 | 27067065 | 27067157 | chr14 | 27067373 | 27067427 | chr14 | 29225457 | 29225636 |
| chr14 | 29225986 | 29226285 | chr14 | 29228567 | 29228866 | chr14 | 29229008 | 29229249 |
| chr14 | 29229251 | 29229487 | chr14 | 29230995 | 29231186 | chr14 | 29231329 | 29231688 |

TABLE 15-continued

| chr | start | end | chr | start | end | chr | start | end |
|---|---|---|---|---|---|---|---|---|
| chr14 | 29234911 | 29235309 | chr14 | 29235342 | 29235450 | chr14 | 29236966 | 29237067 |
| chr14 | 29237140 | 29237205 | chr14 | 29242687 | 29242707 | chr14 | 29243433 | 29243670 |
| chr14 | 29243731 | 29243972 | chr14 | 29244147 | 29244383 | chr14 | 29247596 | 29247835 |
| chr14 | 29254612 | 29254794 | chr14 | 31344269 | 31344628 | chr14 | 31925640 | 31925804 |
| chr14 | 32597619 | 32597759 | chr14 | 33402373 | 33402512 | chr14 | 33402514 | 33402852 |
| chr14 | 33402942 | 33403019 | chr14 | 33403125 | 33403421 | chr14 | 33403783 | 33403502 |
| chr14 | 34420150 | 34420389 | chr14 | 35023188 | 35023427 | chr14 | 35024347 | 35024454 |
| chr14 | 36003471 | 36003904 | chr14 | 36004081 | 36004578 | chr14 | 36004608 | 36004735 |
| chr14 | 36004822 | 36004922 | chr14 | 36005012 | 36005087 | chr14 | 36972709 | 36973008 |
| chr14 | 36973157 | 36973222 | chr14 | 36973455 | 36973636 | chr14 | 36974421 | 36974800 |
| chr14 | 36974802 | 36974928 | chr14 | 36974968 | 36975058 | chr14 | 36975200 | 36975229 |
| chr14 | 36975281 | 36975499 | chr14 | 36977558 | 36977930 | chr14 | 36977975 | 36978097 |
| chr14 | 36978474 | 36978653 | chr14 | 36979657 | 36979724 | chr14 | 36982870 | 36983068 |
| chr14 | 36983674 | 36984227 | chr14 | 36985767 | 36985946 | chr14 | 36986212 | 36986472 |
| chr14 | 36987302 | 36987787 | chr14 | 36987862 | 36988221 | chr14 | 36988449 | 36988564 |
| chr14 | 36990779 | 36991033 | chr14 | 36991095 | 36991258 | chr14 | 36991501 | 36991693 |
| chr14 | 36991989 | 36992164 | chr14 | 36992222 | 36992507 | chr14 | 36993386 | 36993488 |
| chr14 | 36993694 | 36994045 | chr14 | 36994145 | 36995009 | chr14 | 36995011 | 36995104 |
| chr14 | 37116026 | 37116295 | chr14 | 37117535 | 37117697 | chr14 | 37123339 | 37124178 |
| chr14 | 37124482 | 37124648 | chr14 | 37124910 | 37125629 | chr14 | 37126150 | 37126389 |
| chr14 | 37126463 | 37126714 | chr14 | 37126965 | 37127002 | chr14 | 37127207 | 37127386 |
| chr14 | 37127572 | 37127780 | chr14 | 37129990 | 37130349 | chr14 | 37132296 | 37132554 |
| chr14 | 37132603 | 37132775 | chr14 | 37132908 | 37133147 | chr14 | 37135740 | 37135868 |
| chr14 | 37135922 | 37136018 | chr14 | 37136295 | 37136425 | chr14 | 37136514 | 37136693 |
| chr14 | 38060588 | 38060917 | chr14 | 38677445 | 38677581 | chr14 | 38724207 | 38724526 |
| chr14 | 38724979 | 38725346 | chr14 | 38725455 | 38725560 | chr14 | 42074467 | 42074587 |
| chr14 | 42074669 | 42074944 | chr14 | 42075023 | 42075066 | chr14 | 42075511 | 42075810 |
| chr14 | 42075812 | 42076044 | chr14 | 42076106 | 42076290 | chr14 | 42076749 | 42076928 |
| chr14 | 42077130 | 42077368 | chr14 | 42077696 | 42077804 | chr14 | 42079190 | 42079429 |
| chr14 | 48143657 | 48143719 | chr14 | 48143798 | 48143958 | chr14 | 48144359 | 48144500 |
| chr14 | 48144619 | 48144764 | chr14 | 48145237 | 48145338 | chr14 | 50333976 | 50334084 |
| chr14 | 50334336 | 50334455 | chr14 | 51338642 | 51338732 | chr14 | 51339048 | 51339061 |
| chr14 | 51560207 | 51560714 | chr14 | 51560771 | 51561293 | chr14 | 51561295 | 51561526 |
| chr14 | 51561680 | 51562099 | chr14 | 52534571 | 52534870 | chr14 | 52534929 | 52535027 |
| chr14 | 52535056 | 52535264 | chr14 | 52535335 | 52535425 | chr14 | 52535427 | 52535758 |
| chr14 | 52535760 | 52635973 | chr14 | 52535975 | 52536066 | chr14 | 52536068 | 52536105 |
| chr14 | 52536343 | 52536488 | chr14 | 52734414 | 52734525 | chr14 | 52734527 | 52734653 |
| chr14 | 52734687 | 52735002 | chr14 | 52735045 | 52735346 | chr14 | 52781422 | 52782021 |
| chr14 | 54422549 | 44422925 | chr14 | 54422927 | 54423028 | chr14 | 55370100 | 56370219 |
| chr14 | 55596008 | 55596043 | chr14 | 55765207 | 55765686 | chr14 | 57045445 | 57045840 |
| chr14 | 57260845 | 57261095 | chr14 | 57261175 | 57261408 | chr14 | 57261466 | 57261880 |
| chr14 | 57261977 | 57262276 | chr14 | 57264001 | 57264646 | chr14 | 57264765 | 57264807 |
| chr14 | 57265148 | 57265320 | chr14 | 57270854 | 57270972 | chr14 | 57271154 | 57271333 |
| chr14 | 57271919 | 57272114 | chr14 | 57274387 | 57274739 | chr14 | 57274741 | 57275050 |
| chr14 | 57275211 | 57275406 | chr14 | 57275521 | 57275686 | chr14 | 57276074 | 57276180 |
| chr14 | 57276344 | 57276763 | chr14 | 57277830 | 57278763 | chr14 | 57278838 | 57279565 |
| chr14 | 57279643 | 57279712 | chr14 | 57283238 | 57283409 | chr14 | 57283446 | 57284037 |
| chr14 | 57284071 | 57284737 | chr14 | 58332201 | 58332494 | chr14 | 60097111 | 60097247 |
| chr14 | 60097407 | 60097650 | chr14 | 60386111 | 60386350 | chr14 | 60386551 | 60386743 |
| chr14 | 60794532 | 60794771 | chr14 | 60952196 | 60952420 | chr14 | 60952517 | 60952633 |
| chr14 | 60952730 | 60953039 | chr14 | 60973157 | 60973418 | chr14 | 60973618 | 60974008 |
| chr14 | 60974078 | 60974157 | chr14 | 60974273 | 60974506 | chr14 | 60975290 | 60975889 |
| chr14 | 60976075 | 60976609 | chr14 | 60976803 | 60976957 | chr14 | 60977263 | 60977713 |
| chr14 | 60977880 | 60978222 | chr14 | 60981116 | 60981355 | chr14 | 60981586 | 60981813 |
| chr14 | 60982007 | 60982368 | chr14 | 60982574 | 60982726 | chr14 | 60982757 | 60982996 |
| chr14 | 61104242 | 61104557 | chr14 | 61104624 | 61104952 | chr14 | 61108539 | 61108904 |
| chr14 | 61109031 | 61109078 | chr14 | 61109129 | 61109548 | chr14 | 61109742 | 61110341 |
| chr14 | 61114058 | 61114537 | chr14 | 61115235 | 61115594 | chr14 | 61118743 | 61118841 |
| chr14 | 61118872 | 61119227 | chr14 | 61747389 | 61747528 | chr14 | 61747583 | 61747816 |
| chr14 | 61748002 | 61748117 | chr14 | 62279520 | 62279623 | chr14 | 62279625 | 62279853 |
| chr14 | 62279899 | 62280092 | chr14 | 62583710 | 62583870 | chr14 | 62583919 | 62584009 |
| chr14 | 63512064 | 63512376 | chr14 | 63512486 | 63512709 | chr14 | 63512741 | 63512905 |
| chr14 | 63513050 | 63513229 | chr14 | 64222332 | 64222450 | chr14 | 65005803 | 65005915 |
| chr14 | 65008915 | 65008975 | chr14 | 65008998 | 65009274 | chr14 | 65233253 | 65233552 |
| chr14 | 67886583 | 67886702 | chr14 | 69013958 | 69014195 | chr14 | 69866930 | 69867289 |
| chr14 | 70014640 | 70015059 | chr14 | 70346045 | 70346584 | chr14 | 70654379 | 70654597 |
| chr14 | 70654599 | 70654639 | chr14 | 70654641 | 70654798 | chr14 | 70655451 | 70655890 |
| chr14 | 70655920 | 70656170 | chr14 | 72398642 | 72399121 | chr14 | 72399452 | 72399557 |
| chr14 | 72399830 | 72400129 | chr14 | 73167676 | 73167975 | chr14 | 73174938 | 73175237 |
| chr14 | 73178717 | 73178956 | chr14 | 73180112 | 73180336 | chr14 | 73318371 | 73318730 |
| chr14 | 73333174 | 73333256 | chr14 | 73602351 | 73602470 | chr14 | 74705940 | 74706299 |
| chr14 | 74706357 | 74706397 | chr14 | 74706941 | 74707545 | chr14 | 74707523 | 74707748 |
| chr14 | 74707792 | 74707911 | chr14 | 74707913 | 74707976 | chr14 | 74708760 | 74709059 |
| chr14 | 74892472 | 74892645 | chr14 | 74892975 | 74893191 | chr14 | 75078070 | 75078243 |
| chr14 | 75760210 | 75760329 | chr14 | 76604580 | 76604819 | chr14 | 76604985 | 76605464 |
| chr14 | 76843364 | 76843386 | chr14 | 76843733 | 76844058 | chr14 | 77228021 | 77228107 |
| chr14 | 77606833 | 77606856 | chr14 | 77606922 | 77607312 | chr14 | 77737110 | 77737146 |
| chr14 | 77737148 | 77737685 | chr14 | 79745088 | 79746277 | chr14 | 85996395 | 85996694 |

TABLE 15-continued

| chr | start | end | chr | start | end | chr | start | end |
|---|---|---|---|---|---|---|---|---|
| chr14 | 85996760 | 85996796 | chr14 | 85996892 | 85996999 | chr14 | 85997735 | 85997926 |
| chr14 | 85998468 | 85998575 | chr14 | 85998630 | 85998786 | chr14 | 85999472 | 85999532 |
| chr14 | 85999597 | 85999711 | chr14 | 86000182 | 86000574 | chr14 | 86000886 | 86001196 |
| chr14 | 89817813 | 89818112 | chr14 | 90527617 | 90527856 | chr14 | 90983225 | 90983385 |
| chr14 | 91691167 | 91691385 | chr14 | 91766189 | 91766542 | chr14 | 92789438 | 92789617 |
| chr14 | 92789777 | 92789822 | chr14 | 92789960 | 92790099 | chr14 | 92790551 | 92790790 |
| chr14 | 92979835 | 92980074 | chr14 | 93154979 | 93155385 | chr14 | 93389450 | 93389458 |
| chr14 | 93389557 | 93389694 | chr14 | 93389713 | 93389869 | chr14 | 93706678 | 93706857 |
| chr14 | 94254302 | 94254459 | chr14 | 94254499 | 94254601 | chr14 | 94405641 | 94405880 |
| chr14 | 95233616 | 95233646 | chr14 | 95234557 | 95234711 | chr14 | 95235026 | 95235383 |
| chr14 | 95235939 | 95236200 | chr14 | 95236450 | 95236598 | chr14 | 95239298 | 95239349 |
| chr14 | 95239422 | 95239717 | chr14 | 95240053 | 95240268 | chr14 | 95240410 | 95240497 |
| chr14 | 96342551 | 96342631 | chr14 | 96342880 | 96343225 | chr14 | 96343330 | 96343435 |
| chr14 | 96343668 | 96343792 | chr14 | 97045327 | 97045506 | chr14 | 97058761 | 97058818 |
| chr14 | 97058944 | 97059180 | chr14 | 97499257 | 97499416 | chr14 | 97499616 | 97499627 |
| chr14 | 97499847 | 97499850 | chr14 | 97499971 | 97500035 | chr14 | 97684957 | 97685297 |
| chr14 | 97685624 | 97686038 | chr14 | 99584501 | 99584740 | chr14 | 99736048 | 99736213 |
| chr14 | 100437707 | 100437950 | chr14 | 100438018 | 100438066 | chr14 | 100438609 | 100438908 |
| chr14 | 100643267 | 100643566 | chr14 | 101193145 | 101193147 | chr14 | 101250012 | 101250371 |
| chr14 | 101543783 | 101544270 | chr14 | 101923033 | 101923332 | chr14 | 101923520 | 101923687 |
| chr14 | 101924031 | 101924122 | chr14 | 101924966 | 101925072 | chr14 | 101925656 | 101925705 |
| chr14 | 101925707 | 101925985 | chr14 | 102026273 | 102026572 | chr14 | 102026703 | 102027062 |
| chr14 | 102031132 | 102031194 | chr14 | 102031236 | 102031371 | chr14 | 102031434 | 102031450 |
| chr14 | 102031508 | 102031666 | chr14 | 102247824 | 102248303 | chr14 | 102418533 | 102418652 |
| chr14 | 102521501 | 102521860 | chr14 | 102529912 | 102530178 | chr14 | 102530426 | 102530605 |
| chr14 | 102564386 | 102564502 | chr14 | 102681994 | 102682233 | chr14 | 103021308 | 103022087 |
| chr14 | 103394784 | 103395203 | chr14 | 103477540 | 103477771 | chr14 | 103655154 | 103655568 |
| chr14 | 103655570 | 103655684 | chr14 | 103673992 | 103673994 | chr14 | 103674069 | 103674080 |
| chr14 | 103674216 | 103674231 | chr14 | 103687002 | 103687301 | chr14 | 103739885 | 103740239 |
| chr14 | 103740275 | 103740437 | chr14 | 103745606 | 103745845 | chr14 | 104159978 | 104160160 |
| chr14 | 104202624 | 104202852 | chr14 | 104547814 | 104547993 | chr14 | 104571902 | 104572201 |
| chr14 | 104601657 | 104601873 | chr14 | 104601964 | 104602138 | chr14 | 104604954 | 104605193 |
| chr14 | 104620334 | 104620633 | chr14 | 104627564 | 104627862 | chr14 | 104645048 | 104645277 |
| chr14 | 104646225 | 104646584 | chr14 | 104647183 | 104647362 | chr14 | 104682452 | 104682751 |
| chr14 | 104862764 | 104863123 | chr14 | 105071198 | 105071340 | chr14 | 105157401 | 105157640 |
| chr14 | 105241220 | 105241267 | chr14 | 105246463 | 105246642 | chr14 | 105511960 | 105512463 |
| chr14 | 105658268 | 105658507 | chr14 | 105714177 | 105714442 | chr14 | 105715248 | 105715393 |
| chr14 | 105715539 | 105715565 | chr15 | 22822269 | 22822384 | chr15 | 23158294 | 23158593 |
| chr15 | 26107541 | 26107744 | chr15 | 26107846 | 26107960 | chr15 | 26108010 | 26108327 |
| chr15 | 26108549 | 26108789 | chr15 | 27018281 | 27018329 | chr15 | 27212791 | 27213270 |
| chr15 | 27603982 | 27604057 | chr15 | 28341615 | 28341980 | chr15 | 28341982 | 28342020 |
| chr15 | 28344081 | 28344188 | chr15 | 28344224 | 28344350 | chr15 | 28352156 | 28352422 |
| chr15 | 29077185 | 29077394 | chr15 | 29077429 | 29077484 | chr15 | 29130712 | 29131048 |
| chr15 | 29131533 | 29131631 | chr15 | 29131756 | 29131971 | chr15 | 29407680 | 29407814 |
| chr15 | 29407867 | 29408099 | chr15 | 29862423 | 29862537 | chr15 | 31455297 | 31455578 |
| chr15 | 31775500 | 31775638 | chr15 | 31775679 | 31775783 | chr15 | 31776145 | 31776190 |
| chr15 | 33009649 | 33009762 | chr15 | 33009822 | 33010399 | chr15 | 33010401 | 33010676 |
| chr15 | 33010721 | 33011166 | chr15 | 33011168 | 33011448 | chr15 | 33011498 | 33011737 |
| chr15 | 33486970 | 33487209 | chr15 | 33602725 | 33602964 | chr15 | 33603110 | 33603609 |
| chr15 | 33603648 | 33603709 | chr15 | 33879168 | 33879347 | chr15 | 34630346 | 34630389 |
| chr15 | 34630439 | 34630525 | chr15 | 34729381 | 34729680 | chr15 | 34786425 | 34786944 |
| chr15 | 34787233 | 34787384 | chr15 | 35046935 | 35047149 | chr15 | 35087563 | 35087802 |
| chr15 | 37180227 | 37180241 | chr15 | 37180414 | 37180826 | chr15 | 37402898 | 37403087 |
| chr15 | 37403116 | 37403316 | chr15 | 40211736 | 40212275 | chr15 | 40575538 | 40575837 |
| chr15 | 41165152 | 41165751 | chr15 | 41804786 | 41805865 | chr15 | 41835732 | 41835814 |
| chr15 | 41913660 | 41913899 | chr15 | 41952493 | 41952792 | chr15 | 43810472 | 43810510 |
| chr15 | 44037485 | 44037604 | chr15 | 45403554 | 45403681 | chr15 | 45403799 | 45404000 |
| chr15 | 45404103 | 45404213 | chr15 | 45404833 | 45404833 | chr15 | 45404898 | 45405209 |
| chr15 | 45421291 | 45421530 | chr15 | 45421874 | 45421947 | chr15 | 45427263 | 45427341 |
| chr15 | 45427370 | 45427502 | chr15 | 45427520 | 45427720 | chr15 | 45427772 | 45427879 |
| chr15 | 45479371 | 45479517 | chr15 | 45479775 | 45479789 | chr15 | 45670503 | 45670839 |
| chr15 | 45670933 | 45670971 | chr15 | 47476794 | 47476806 | chr15 | 47476877 | 47476981 |
| chr15 | 47477013 | 47477093 | chr15 | 48483907 | 48483963 | chr15 | 48936639 | 48937213 |
| chr15 | 48937215 | 48937646 | chr15 | 48937710 | 48938077 | chr15 | 48938122 | 48938347 |
| chr15 | 48938349 | 48938601 | chr15 | 51385838 | 51386257 | chr15 | 51633986 | 51634151 |
| chr15 | 51634175 | 51634225 | chr15 | 51973695 | 51973695 | chr15 | 51973764 | 51974030 |
| chr15 | 53075740 | 53075865 | chr15 | 53075986 | $3077001 | chr15 | 53077066 | 53077455 |
| chr15 | 53077574 | 53077813 | chr15 | 53077971 | 53078320 | chr15 | 53079262 | 53079678 |
| chr15 | 53079718 | 53079892 | chr15 | 53079971 | 53080161 | chr15 | 53080263 | 53080620 |
| chr15 | 53080861 | 53080991 | chr15 | 53081055 | 53081100 | chr15 | 53081223 | 53081297 |
| chr15 | 53081399 | 53081702 | chr15 | 53082348 | 53082587 | chr15 | 53096735 | 53096974 |
| chr15 | 53097157 | 53097336 | chr15 | 53097535 | 53097569 | chr15 | 53097778 | 53097907 |
| chr15 | 53098382 | 53098757 | chr15 | 54270424 | 54270783 | chr15 | 54270858 | 54271025 |
| chr15 | 55452972 | 55453087 | chr15 | 55699008 | 55699127 | chr15 | 55880891 | 55881044 |
| chr15 | 55881046 | 55881095 | chr15 | 58357800 | 58357820 | chr15 | 59158454 | 59158616 |
| chr15 | 59950343 | 59950461 | chr15 | 60286937 | 60287586 | chr15 | 60287644 | 60287780 |
| chr15 | 60288703 | 60288935 | chr15 | 60289229 | 60289638 | chr15 | 60296047 | 60296286 |
| chr15 | 60296495 | 60296618 | chr15 | 60296861 | 60296924 | chr15 | 60297152 | 60297514 |

TABLE 15-continued

| chr | start | end | chr | start | end | chr | start | end |
| --- | --- | --- | --- | --- | --- | --- | --- | --- |
| chr15 | 60297544 | 60297827 | chr15 | 60297942 | 60298203 | chr15 | 61520816 | 61521115 |
| chr15 | 61521559 | 61521621 | chr15 | 61521657 | 61521676 | chr15 | 61521713 | 51522038 |
| chr15 | 62456848 | 62456966 | chr15 | 62457009 | 62457019 | chr15 | 65669760 | 65669999 |
| chr15 | 65862054 | 65862213 | chr15 | 66963726 | 66963823 | chr15 | 66963928 | 66963964 |
| chr15 | 68112537 | 68112716 | chr15 | 68113794 | 68113973 | chr15 | 68114048 | 68114287 |
| chr15 | 68116286 | 68116682 | chr15 | 68117753 | 68118712 | chr15 | 68118783 | 68118784 |
| chr15 | 68118799 | 68118876 | chr15 | 68118930 | 68119175 | chr15 | 68119579 | 68120353 |
| chr15 | 68120631 | 68120662 | chr15 | 68120753 | 68120932 | chr15 | 68121150 | 68121958 |
| chr15 | 68122569 | 68122748 | chr15 | 68125164 | 68125763 | chr15 | 68127717 | 68128436 |
| chr15 | 68128492 | 68128597 | chr15 | 68260435 | 68260735 | chr15 | 71055770 | 71055906 |
| chr15 | 72412113 | 72412263 | chr15 | 72743650 | 72743859 | chr15 | 73659917 | 73660156 |
| chr15 | 73661476 | 73661748 | chr15 | 74044960 | 74045023 | chr15 | 74045075 | 74045199 |
| chr15 | 74421927 | 74421954 | chr15 | 74421980 | 74422226 | chr15 | 74422787 | 74423012 |
| chr15 | 74658070 | 74658397 | chr15 | 74658502 | 74658553 | chr15 | 74658555 | 74658595 |
| chr15 | 74686082 | 74686126 | chr15 | 74818670 | 74818789 | chr15 | 74903822 | 74904001 |
| chr15 | 75251245 | 75251414 | chr15 | 75251479 | 75251484 | chr15 | 75251580 | 75251879 |
| chr15 | 75471218 | 75471275 | chr15 | 76627515 | 76627537 | chr15 | 76627576 | 76627907 |
| chr15 | 76628959 | 76629026 | chr15 | 76629163 | 76629314 | chr15 | 76629588 | 76629633 |
| chr15 | 76629732 | 76630095 | chr15 | 76630097 | 76630125 | chr15 | 76630520 | 76630931 |
| chr15 | 76632518 | 76632520 | chr15 | 76635040 | 76635110 | chr15 | 76635576 | 76635635 |
| chr15 | 76638387 | 76638497 | chr15 | 77448976 | 77449087 | chr15 | 78501725 | 78502024 |
| chr15 | 78556795 | 78557034 | chr15 | 78557110 | 78557204 | chr15 | 78596066 | 78596245 |
| chr15 | 78632626 | 78632669 | chr15 | 78632684 | 78532925 | chr15 | 78912192 | 78912372 |
| chr15 | 78912442 | 78912491 | chr15 | 78912549 | 78912728 | chr15 | 78912832 | 78913028 |
| chr15 | 78913095 | 78913251 | chr15 | 78913444 | 78913470 | chr15 | 78913481 | 78913683 |
| chr15 | 79104143 | 79104159 | chr15 | 79381709 | 79381746 | chr15 | 79382099 | 79382648 |
| chr15 | 79382693 | 79382998 | chr15 | 79383000 | 79383268 | chr15 | 79383873 | 79384052 |
| chr15 | 79502137 | 79502381 | chr15 | 79575197 | 79575556 | chr15 | 79576062 | 79576361 |
| chr15 | 79724034 | 79724120 | chr15 | 79724402 | 79724561 | chr15 | 79724607 | 79724793 |
| chr15 | 79724864 | 79725241 | chr15 | 79725332 | 79725584 | chr15 | 82336777 | 82337076 |
| chr15 | 82339995 | 82340234 | chr15 | 83315246 | 83315474 | chr15 | 83316232 | 83316640 |
| chr15 | 83316642 | 83317162 | chr15 | 83349131 | 83349612 | chr15 | 83349672 | 83349790 |
| chr15 | 83378112 | 83378164 | chr15 | 83378186 | 83378471 | chr15 | 83776161 | 83776269 |
| chr15 | 83776271 | 83776307 | chr15 | 83776333 | 83776717 | chr15 | 83776769 | 83776880 |
| chr15 | 83875571 | 83875666 | chr15 | 83875706 | 83875985 | chr15 | 83876953 | 83877252 |
| chr15 | 83952108 | 83952113 | chr15 | 83952769 | 83952827 | chr15 | 83953024 | 83953049 |
| chr15 | 84115648 | 84115811 | chr15 | 84115813 | 84115854 | chr15 | 84115932 | 84116067 |
| chr15 | 84116829 | 84116995 | chr15 | 84322994 | 84323124 | chr15 | 84748500 | 84748620 |
| chr15 | 84748679 | 84749339 | chr15 | 85143052 | 85143144 | chr15 | 88798591 | 88798654 |
| chr15 | 88798725 | 88798890 | chr15 | 88799448 | 88799999 | chr15 | 88800001 | 88800302 |
| chr15 | 88800463 | 88801004 | chr15 | 88801006 | 88801009 | chr15 | 88801089 | 88801182 |
| chr15 | 89149070 | 89149489 | chr15 | 89248651 | 89249010 | chr15 | 89345953 | 89346327 |
| chr15 | 89346347 | 89346492 | chr15 | 89346568 | 89346794 | chr15 | 89346882 | 89347047 |
| chr15 | 89903410 | 89903889 | chr15 | 89910426 | 89910845 | chr15 | 89910988 | 89911287 |
| chr15 | 89913676 | 89913855 | chr15 | 89914144 | 89914450 | chr15 | 89914867 | 89914983 |
| chr15 | 89915156 | 89915455 | chr15 | 89921862 | 89922038 | chr15 | 89922500 | 89922649 |
| chr15 | 89942671 | 89943030 | chr15 | 89943319 | 89943775 | chr15 | 89949317 | 89949410 |
| chr15 | 89949617 | 89950036 | chr15 | 89950154 | 89950737 | chr15 | 89951082 | 89951215 |
| chr15 | 89951302 | 89951377 | chr15 | 89951466 | 89951901 | chr15 | 89952065 | 89952453 |
| chr15 | 89952700 | 89953144 | chr15 | 89954122 | 89954416 | chr15 | 89956288 | 89956354 |
| chr15 | 89956423 | 89956527 | chr15 | 90039488 | 90039787 | chr15 | 90755819 | 90756144 |
| chr15 | 91643264 | 91643683 | chr15 | 92936281 | 92936426 | chr15 | 92937115 | 92937474 |
| chr15 | 92937849 | 92938061 | chr15 | 92938123 | 92938294 | chr15 | 92938316 | 92938388 |
| chr15 | 93631638 | 93632117 | chr15 | 93632558 | 93632730 | chr15 | 93632732 | 93633332 |
| chr15 | 94347588 | 94347707 | chr15 | 95388666 | 95388712 | chr15 | 96874259 | 96874416 |
| chr15 | 96889374 | 96889506 | chr15 | 96897853 | 96898092 | chr15 | 96911456 | 96911692 |
| chr15 | 96911764 | 96911815 | chr15 | 96952594 | 96953099 | chr15 | 96953132 | 96953313 |
| chr15 | 96959720 | 96959961 | chr15 | 96960428 | 96960513 | chr15 | 96960630 | 96960907 |
| chr15 | 97006274 | 97006623 | chr15 | 98504040 | 98504219 | chr15 | 98836077 | 98836477 |
| chr15 | 98965179 | 98965232 | chr15 | 99193106 | 99193345 | chr15 | 99193350 | 99193583 |
| chr15 | 99193873 | 99194172 | chr15 | 99456272 | 99456404 | chr15 | 100913332 | 100913596 |
| chr15 | 101420447 | 101420665 | chr15 | 101420848 | 101420860 | chr15 | 101420972 | 101421087 |
| chr15 | 101513806 | 101513831 | chr16 | 142567 | 142775 | chr16 | 215341 | 215873 |
| chr16 | 215913 | 215960 | chr16 | 215962 | 216300 | chr16 | 216587 | 217070 |
| chr16 | 230229 | 230316 | chr16 | 230497 | 230708 | chr16 | 318040 | 318316 |
| chr16 | 318422 | 318444 | chr16 | 337510 | 337749 | chr16 | 410303 | 410482 |
| chr16 | 611304 | 611603 | chr16 | 611876 | 612355 | chr16 | 612774 | 613133 |
| chr16 | 667466 | 667561 | chr16 | 677879 | 677993 | chr16 | 700225 | 700404 |
| chr16 | 726539 | 727078 | chr16 | 731400 | 731699 | chr16 | 735131 | 735670 |
| chr16 | 740888 | 741003 | chr16 | 741280 | 741507 | chr16 | 837262 | 837561 |
| chr16 | 845881 | 846060 | chr16 | 882567 | 882686 | chr16 | 895011 | 895250 |
| chr16 | 943398 | 943637 | chr16 | 1018046 | 1018225 | chr16 | 1030210 | 1030271 |
| chr16 | 1030444 | 1030749 | chr16 | 1052488 | 1052727 | chr16 | 1103032 | 1103263 |
| chr16 | 1116721 | 1116766 | chr16 | 1128927 | 1129226 | chr16 | 1155068 | 1155307 |
| chr16 | 1203883 | 1203963 | chr16 | 1204003 | 1204111 | chr16 | 1217226 | 1217583 |
| chr16 | 1217943 | 1218182 | chr16 | 1228711 | 1229010 | chr16 | 1230057 | 1230236 |
| chr16 | 1248621 | 1248760 | chr16 | 1267844 | 1268203 | chr16 | 1271447 | 1271746 |
| chr16 | 1312450 | 1312689 | chr16 | 1323900 | 1324139 | chr16 | 1382862 | 1383041 |

TABLE 15-continued

| chr | start | end | chr | start | end | chr | start | end |
|---|---|---|---|---|---|---|---|---|
| chr16 | 1394400 | 1394579 | chr16 | 1397380 | 1397559 | chr16 | 1407366 | 1407485 |
| chr16 | 1407819 | 1407938 | chr16 | 1428422 | 1428961 | chr16 | 1491471 | 1491694 |
| chr16 | 1730213 | 1730692 | chr16 | 1741757 | 1742176 | chr16 | 2028986 | 2029225 |
| chr16 | 2040818 | 2040961 | chr16 | 2040981 | 2040981 | chr16 | 2040983 | 2041513 |
| chr16 | 2041582 | 2042257 | chr16 | 2106629 | 2106741 | chr16 | 2128503 | 2128682 |
| chr16 | 2129033 | 2129332 | chr16 | 2141835 | 2142014 | chr16 | 2142468 | 2142707 |
| chr16 | 2213239 | 2213396 | chr16 | 2232665 | 2232784 | chr16 | 2234634 | 2235113 |
| chr16 | 2281163 | 2281402 | chr16 | 2287231 | 2287453 | chr16 | 2531136 | 2531255 |
| chr16 | 2764275 | 2764574 | chr16 | 2770033 | 2770512 | chr16 | 2818018 | 2818249 |
| chr16 | 2892457 | 2892603 | chr16 | 2892627 | 2892797 | chr16 | 3017157 | 3017431 |
| chr16 | 3068097 | 3068276 | chr16 | 3151038 | 3151264 | chr16 | 3211625 | 3211742 |
| chr16 | 3211805 | 3211982 | chr16 | 3220474 | 3220557 | chr16 | 3220591 | 3220893 |
| chr16 | 3221142 | 3221701 | chr16 | 3221787 | 3222325 | chr16 | 3225390 | 3225689 |
| chr16 | 3232697 | 3233017 | chr16 | 3233199 | 3233331 | chr16 | 3233435 | 3234104 |
| chr16 | 3234197 | 3234541 | chr16 | 3237783 | 3238022 | chr16 | 3238164 | 3238622 |
| chr16 | 3238912 | 3239631 | chr16 | 3239692 | 3239931 | chr16 | 3241517 | 3241756 |
| chr16 | 3241862 | 3241981 | chr16 | 3355200 | 3355234 | chr16 | 3355251 | 3355799 |
| chr16 | 3598818 | 3599057 | chr16 | 3696620 | 3696799 | chr16 | 3802932 | 3803171 |
| chr16 | 4264433 | 4264792 | chr16 | 4431039 | 4431213 | chr16 | 4846061 | 4846415 |
| chr16 | 5037803 | 5038102 | chr16 | 5641026 | 5541257 | chr16 | 6069989 | 6070122 |
| chr16 | 7354560 | 7354658 | chr16 | 7354700 | 7354739 | chr16 | 8780956 | 8781135 |
| chr16 | 8870279 | 8870458 | chr16 | 9009781 | 9010075 | chr16 | 10274325 | 10274504 |
| chr16 | 10275231 | 10275470 | chr16 | 10275671 | 10276030 | chr16 | 10276270 | 10276799 |
| chr16 | 10276801 | 10277051 | chr16 | 10277072 | 10277409 | chr16 | 10479719 | 10479966 |
| chr16 | 10479968 | 10480078 | chr16 | 12971812 | 12972035 | chr16 | 12994359 | 12994838 |
| chr16 | 12994969 | 12995688 | chr16 | 12995707 | 12995804 | chr16 | 12996074 | 12996426 |
| chr16 | 12996520 | 12996819 | chr16 | 12996861 | 12997100 | chr16 | 12997306 | 12997785 |
| chr16 | 14725745 | 14725864 | chr16 | 15489851 | 15489884 | chr16 | 15820726 | 15820965 |
| chr16 | 18802486 | 18802725 | chr16 | 18950987 | 18951093 | chr16 | 19567117 | 19567536 |
| chr16 | 19895051 | 19895125 | chr16 | 19895156 | 19895230 | chr16 | 21831520 | 21832052 |
| chr16 | 21839250 | 21839348 | chr16 | 22824599 | 22825077 | chr16 | 22825158 | 22825198 |
| chr16 | 22825225 | 22825470 | chr16 | 22825886 | 22826184 | chr16 | 23313374 | 23313613 |
| chr16 | 23313674 | 23313739 | chr16 | 23313780 | 23313913 | chr16 | 23706240 | 23706287 |
| chr16 | 23706412 | 23706599 | chr16 | 23765995 | 23766098 | chr16 | 23766133 | 23766234 |
| chr16 | 23847311 | 23847325 | chr16 | 23847327 | 23847512 | chr16 | 23847789 | 23847816 |
| chr16 | 23847818 | 23847875 | chr16 | 23847934 | 23848003 | chr16 | 23848005 | 23848053 |
| chr16 | 24267013 | 24267145 | chr16 | 24267221 | 24267312 | chr16 | 24267383 | 24267594 |
| chr16 | 25266436 | 25266675 | chr16 | 26702855 | 25703094 | chr16 | 25703685 | 25704123 |
| chr16 | 25704390 | 25704705 | chr16 | 26664758 | 26664853 | chr16 | 27460002 | 27460156 |
| chr16 | 28074101 | 28074255 | chr16 | 28074418 | 28074760 | chr16 | 28074869 | 28074937 |
| chr16 | 28074956 | 28075288 | chr16 | 29118954 | 29119133 | chr16 | 29153201 | 29153254 |
| chr16 | 29244800 | 29245099 | chr16 | 29830796 | 29831155 | chr16 | 29888549 | 19888761 |
| chr16 | 30017240 | 30017539 | chr16 | 30116211 | 30116390 | chr16 | 30124597 | 30124949 |
| chr16 | 30804458 | 30804575 | chr16 | 30826363 | 30826570 | chr16 | 30906930 | 30907049 |
| chr16 | 30907123 | 30907229 | chr16 | 31228310 | 31228402 | chr16 | 31446904 | 31447173 |
| chr16 | 31497971 | 31498087 | chr16 | 31500460 | 31500759 | chr16 | 31580469 | 31580739 |
| chr16 | 46721556 | 46721787 | chr16 | 47177447 | 47177686 | chr16 | 48845120 | 48845229 |
| chr16 | 49309067 | 49309366 | chr16 | 49311432 | 49311691 | chr16 | 49312033 | 49312391 |
| chr16 | 49313268 | 49313807 | chr16 | 49313921 | 49314220 | chr16 | 49314341 | 49314640 |
| chr16 | 49314692 | 49314822 | chr16 | 49315202 | 49315381 | chr16 | 49315831 | 49316316 |
| chr16 | 49316509 | 49316670 | chr16 | 49637986 | 49638165 | chr16 | 50335693 | 50335872 |
| chr16 | 51183964 | 51184431 | chr16 | 51184725 | 51184958 | chr16 | 51185055 | 51185292 |
| chr16 | 51185763 | 51185965 | chr16 | 51186026 | 51186329 | chr16 | 51186596 | 51187036 |
| chr16 | 51189848 | 51190038 | chr16 | 51190122 | 51190309 | chr16 | 53563519 | 53563734 |
| chr16 | 54318855 | 54319063 | chr16 | 54319325 | 54319564 | chr16 | 54321557 | 54321819 |
| chr16 | 54321908 | 54321916 | chr16 | 54324960 | 54325199 | chr16 | 54628600 | 54628959 |
| chr16 | 54964875 | 54965211 | chr16 | 54966728 | 54967265 | chr16 | 54970986 | 54971007 |
| chr16 | 54971326 | 54971505 | chr16 | 55090585 | 55090944 | chr16 | 55357827 | 55357941 |
| chr16 | 55357992 | 55358186 | chr16 | 55358213 | 55358351 | chr16 | 55358567 | 55358632 |
| chr16 | 55358785 | 55359175 | chr16 | 55362963 | 55363326 | chr16 | 55364631 | 55364930 |
| chr16 | 55365020 | 55365219 | chr16 | 55404898 | 55405202 | chr16 | 55405202 | 55405317 |
| chr16 | 55512745 | 55512763 | chr16 | 55512936 | 55512984 | chr16 | 55689853 | 55689901 |
| chr16 | 55689903 | 55689991 | chr16 | 55690013 | 55690380 | chr16 | 55690454 | 55690577 |
| chr16 | 55690762 | 55690912 | chr16 | 56224479 | 56224782 | chr16 | 56224784 | 56224793 |
| chr16 | 56224795 | 56224833 | chr16 | 56224881 | 56224958 | chr16 | 56228271 | 56228417 |
| chr16 | 56228578 | 56228685 | chr16 | 56651006 | 56651124 | chr16 | 56651239 | 56651365 |
| chr16 | 56659095 | 56659754 | chr16 | 56672077 | 56672173 | chr16 | 56672222 | 56672386 |
| chr16 | 56672514 | 56672761 | chr16 | 56709755 | 56709893 | chr16 | 56709950 | 56710114 |
| chr16 | 57222710 | 57222806 | chr16 | 57935476 | 57935655 | chr16 | 58018531 | 58018950 |
| chr16 | 58019149 | 58019508 | chr16 | 58120875 | 58121058 | chr16 | 58497136 | 58497336 |
| chr16 | 58497470 | 58497495 | chr16 | 58497672 | 58497911 | chr16 | 58498101 | 58498280 |
| chr16 | 58498468 | 58498585 | chr16 | 58498587 | 58498809 | chr16 | 58521634 | 58521813 |
| chr16 | 58550415 | 58550587 | chr16 | 58969669 | 58969895 | chr16 | 62068387 | 62068610 |
| chr16 | 62068923 | 62069057 | chr16 | 62070669 | 62070848 | chr16 | 65154833 | 65155192 |
| chr16 | 65156288 | 65156587 | chr16 | 66461694 | 66461933 | chr16 | 66612797 | 66613096 |
| chr16 | 66613335 | 66613359 | chr16 | 67197615 | 67197854 | chr16 | 67197935 | 67198114 |
| chr16 | 67198818 | 67199057 | chr16 | 67241130 | 67241309 | chr16 | 67313791 | 67313970 |
| chr16 | 68544170 | 68544409 | chr16 | 68676307 | 68676605 | chr16 | 68676842 | 68677086 |

TABLE 15-continued

| chr | start | end | chr | start | end | chr | start | end |
|---|---|---|---|---|---|---|---|---|
| chr16 | 68770847 | 68771086 | chr16 | 68771167 | 68771402 | chr16 | 68876728 | 68876847 |
| chr16 | 70595543 | 70595782 | chr16 | 71459957 | 71460029 | chr16 | 71460271 | 71460429 |
| chr16 | 71715705 | 71715884 | chr16 | 72957660 | 72957899 | chr16 | 73100576 | 73100612 |
| chr16 | 75019677 | 75019856 | chr16 | 77247366 | 77247545 | chr16 | 77468182 | 77468458 |
| chr16 | 77822493 | 77822589 | chr16 | 77822875 | 77822972 | chr16 | 78079893 | 78080132 |
| chr16 | 79623798 | 79623968 | chr16 | 80838052 | 80838173 | chr16 | 80966296 | 80966535 |
| chr16 | 82660279 | 82660578 | chr16 | 82660638 | 82660727 | chr16 | 82660729 | 82660817 |
| chr16 | 84074767 | 84074946 | chr16 | 84153290 | 84153469 | chr16 | 84402163 | 84402402 |
| chr16 | 84853274 | 84853452 | chr16 | 85075418 | 85075644 | chr16 | 85317747 | 85317879 |
| chr16 | 85485652 | 85485951 | chr16 | 85517254 | 85517613 | chr16 | 85678551 | 85678850 |
| chr16 | 85684234 | 85684533 | chr16 | 85699596 | 85699925 | chr16 | 85932754 | 85932933 |
| chr16 | 86320254 | 86320489 | chr16 | 86320491 | 86320493 | chr16 | 86320659 | 86320898 |
| chr16 | 86320925 | 86321147 | chr16 | 86530848 | 86530993 | chr16 | 86531017 | 86531147 |
| chr16 | 86531233 | 86531289 | chr16 | 86531375 | 86531481 | chr16 | 86531528 | 86531652 |
| chr16 | 86541537 | 86541956 | chr16 | 86542296 | 85542535 | chr16 | 86544103 | 86544558 |
| chr16 | 86545060 | 86545062 | chr16 | 86599481 | 86599931 | chr16 | 86600406 | 86600765 |
| chr16 | 86600868 | 86601107 | chr16 | 86601204 | 86601623 | chr16 | 86602038 | 86602590 |
| chr16 | 87092347 | 87092646 | chr16 | 87635029 | 87635208 | chr16 | 87636444 | 87636491 |
| chr16 | 87636627 | 87636782 | chr16 | 87636784 | 87636983 | chr16 | 87714178 | 87714477 |
| chr16 | 87723648 | 87724187 | chr16 | 88164316 | 88164555 | chr16 | 88498142 | 88498861 |
| chr16 | 88503978 | 88504397 | chr16 | 88506265 | 88506616 | chr16 | 88512329 | 88512628 |
| chr16 | 88603617 | 88603848 | chr16 | 88623885 | 88624165 | chr16 | 88757428 | 88757571 |
| chr16 | 88879858 | 88880097 | chr16 | 88883159 | 88883458 | chr16 | 88940981 | 88941220 |
| chr16 | 88942021 | 88942239 | chr16 | 88943463 | 88944122 | chr16 | 88945726 | 88946085 |
| chr16 | 88955160 | 88955459 | chr16 | 88956136 | 88956495 | chr16 | 88957374 | 88957934 |
| chr16 | 88958295 | 88958534 | chr16 | 88963191 | R8963850 | chr16 | 88966207 | 88966586 |
| chr16 | 88968630 | 88968869 | chr16 | 88977929 | 88978126 | chr16 | 88992975 | 88993334 |
| chr16 | 88999543 | 88999557 | chr16 | 88999574 | 88999693 | chr16 | 89000127 | 89000306 |
| chr16 | 89001020 | 89001139 | chr16 | 89007420 | 89007659 | chr16 | 89007789 | 89007879 |
| chr16 | 89008488 | 89008667 | chr16 | 89047643 | 89047822 | chr16 | 89072400 | 89072879 |
| chr16 | 89086034 | 89086273 | chr16 | 89107585 | 89107824 | chr16 | 89109345 | 89109490 |
| chr16 | 89119940 | 89120419 | chr16 | 89120607 | 89120963 | chr16 | 89137919 | 89138158 |
| chr16 | 89220244 | 89220483 | chr16 | 89220580 | 89220999 | chr16 | 89254563 | 89254742 |
| chr16 | 89267260 | 89267439 | chr16 | 89267709 | 89267825 | chr16 | 89558549 | 89558807 |
| chr16 | 89883930 | 89884289 | chr16 | 89884875 | 89884989 | chr16 | 89885115 | 89885229 |
| chr16 | 89900033 | 89900272 | chr16 | 89900372 | 89900611 | chr17 | 616914 | 517026 |
| chr17 | 1082923 | 1083093 | chr17 | 1174274 | 1174362 | chr17 | 1174385 | 1174505 |
| chr17 | 1536129 | 1536221 | chr17 | 1546312 | 1546539 | chr17 | 1623600 | 1623779 |
| chr17 | 1959437 | 1959614 | chr17 | 2207848 | 2207967 | chr17 | 2208042 | 2208147 |
| chr17 | 2220974 | 2221142 | chr17 | 2249977 | 2250096 | chr17 | 3438818 | 3438938 |
| chr17 | 3439030 | 3439057 | chr17 | 3658751 | 3658930 | chr17 | 3658991 | 3659110 |
| chr17 | 4544510 | 4544809 | chr17 | 4699212 | 4699331 | chr17 | 4891237 | 4891381 |
| chr17 | 5000340 | 5000879 | chr17 | 6616543 | 6516782 | chr17 | 6616813 | 6616883 |
| chr17 | 6616885 | 6617174 | chr17 | 6679220 | 6679393 | chr17 | 6946113 | 6946153 |
| chr17 | 6946176 | 6946244 | chr17 | 7348792 | 7349070 | chr17 | 7368864 | 7369223 |
| chr17 | 7555099 | 7555338 | chr17 | 7573915 | 7574094 | chr17 | 7576923 | 7577222 |
| chr17 | 7577423 | 7577662 | chr17 | 7578078 | 7578557 | chr17 | 7906156 | 7906514 |
| chr17 | 8104071 | 8104173 | chr17 | 8230246 | 8230350 | chr17 | 8230352 | 8230785 |
| chr17 | 8774685 | 8774728 | chr17 | 8868524 | 8868668 | chr17 | 8868815 | 8869213 |
| chr17 | 8869215 | 8869483 | chr17 | 8906183 | 8906602 | chr17 | 8906895 | 8907213 |
| chr17 | 8907215 | 8907674 | chr17 | 8925983 | 8926201 | chr17 | 10100995 | 10101110 |
| chr17 | 10101132 | 10101448 | chr17 | 10102331 | 10102750 | chr17 | 11144839 | 11144852 |
| chr17 | 11144923 | 11145078 | chr17 | 13503875 | 13503945 | chr17 | 13504195 | 13504294 |
| chr17 | 13504470 | 13504769 | chr17 | 13505002 | 13505292 | chr17 | 13505316 | 13505675 |
| chr17 | 14200962 | 14201261 | chr17 | 14204138 | 14204317 | chr17 | 14204425 | 14204724 |
| chr17 | 15244988 | 15245215 | chr17 | 16282157 | 16282396 | chr17 | 16570674 | 16570897 |
| chr17 | 17062513 | 17062752 | chr17 | 17123889 | 17124068 | chr17 | 17398520 | 17398542 |
| chr17 | 18163094 | 18163415 | chr17 | 18538207 | 18538360 | chr17 | 20817897 | 20817998 |
| chr17 | 25620495 | 25620794 | chr17 | 25676885 | 25677004 | chr17 | 25680190 | 25680276 |
| chr17 | 25907676 | 25907855 | chr17 | 26263104 | 26263214 | chr17 | 26554551 | 26554753 |
| chr17 | 26961721 | 26961922 | chr17 | 27038568 | 27038686 | chr17 | 27038907 | 27038985 |
| chr17 | 27044696 | 27044744 | chr17 | 27056846 | 27056957 | chr17 | 27170072 | 27170182 |
| chr17 | 27181284 | 27181456 | chr17 | 27332378 | 27332737 | chr17 | 27716018 | 27716134 |
| chr17 | 27716198 | 27716314 | chr17 | 27940276 | 27940338 | chr17 | 27940591 | 27940995 |
| chr17 | 28562614 | 28562853 | chr17 | 29232148 | 29232267 | chr17 | 29249615 | 29249961 |
| chr17 | 29250020 | 29250034 | chr17 | 29298002 | 29298184 | chr17 | 29298186 | 29298463 |
| chr17 | 29718123 | 29718362 | chr17 | 29719096 | 29719247 | chr17 | 29719290 | 29719335 |
| chr17 | 30243689 | 30243988 | chr17 | 30250242 | 30250345 | chr17 | 31618333 | 31618409 |
| chr17 | 31618411 | 31619412 | chr17 | 31619870 | 31620109 | chr17 | 32483946 | 32484125 |
| chr17 | 32906299 | 32906555 | chr17 | 32906599 | 32906718 | chr17 | 32906888 | 32907112 |
| chr17 | 32907136 | 32907247 | chr17 | 32907554 | 32907705 | chr17 | 32907707 | 32907805 |
| chr17 | 32908044 | 32908147 | chr17 | 32908171 | 32908463 | chr17 | 32908550 | 32909029 |
| chr17 | 33672832 | 33673071 | chr17 | 33877184 | 33877303 | chr17 | 33917240 | 33917350 |
| chr17 | 35165549 | 35165788 | chr17 | 35165912 | 35166091 | chr17 | 35285455 | 35285754 |
| chr17 | 35290313 | 35290732 | chr17 | 35291242 | 35291457 | chr17 | 35291749 | 35291899 |
| chr17 | 35291921 | 35292708 | chr17 | 35293630 | 35294229 | chr17 | 35294364 | 35294481 |
| chr17 | 35294483 | 35294491 | chr17 | 35294493 | 35294603 | chr17 | 35294955 | 35295254 |
| chr17 | 35296069 | 35296368 | chr17 | 35296629 | 35296988 | chr17 | 35297527 | 35298246 |

TABLE 15-continued

| chr | start | end | chr | start | end | chr | start | end |
|---|---|---|---|---|---|---|---|---|
| chr17 | 35299154 | 35299444 | chr17 | 35299601 | 35299966 | chr17 | 35300261 | 35300713 |
| chr17 | 35300813 | 35300953 | chr17 | 35303259 | 35303618 | chr17 | 36102935 | 36103289 |
| chr17 | 36103291 | 36103414 | chr17 | 36103497 | 36103676 | chr17 | 36104031 | 36104035 |
| chr17 | 36104218 | 36104551 | chr17 | 36104644 | 36104870 | chr17 | 36105141 | 36105350 |
| chr17 | 36105459 | 36105680 | chr17 | 32192168 | 37192281 | chr17 | 37321100 | 37321625 |
| chr17 | 37321788 | 37322010 | chr17 | 37366236 | 37366655 | chr17 | 32369106 | 37369285 |
| chr17 | 37380922 | 37381430 | chr17 | 37381571 | 37381727 | chr17 | 37381826 | 37381941 |
| chr17 | 37382048 | 37382347 | chr17 | 37757066 | 37757305 | chr17 | 37760406 | 32760645 |
| chr17 | 37761897 | 37762436 | chr17 | 37879697 | 37879712 | chr17 | 38179295 | 38179348 |
| chr17 | 38179492 | 38179534 | chr17 | 38347473 | 38347616 | chr17 | 38497542 | 38497721 |
| chr17 | 38498009 | 38498188 | chr17 | 39682550 | 39682729 | chr17 | 40332846 | 40333268 |
| chr17 | 40400770 | 40401109 | chr17 | 40464179 | 40464418 | chr17 | 40464443 | 40464627 |
| chr17 | 40975576 | 40975754 | chr17 | 41278542 | 41278693 | chr17 | 41651776 | 41651887 |
| chr17 | 41791413 | 41791565 | chr17 | 41791591 | 41791599 | chr17 | 42030244 | 42030751 |
| chr17 | 42030780 | 42030843 | chr17 | 42061240 | 42061479 | chr17 | 42082421 | 42082660 |
| chr17 | 42092116 | 42092187 | chr17 | 42092189 | 42092295 | chr17 | 42331637 | 42331746 |
| chr17 | 42393780 | 42394113 | chr17 | 42402782 | 42402984 | chr17 | 42587336 | 42587452 |
| chr17 | 42635199 | 42635844 | chr17 | 42733619 | 42733978 | chr17 | 42787580 | 42787699 |
| chr17 | 42907489 | 42907631 | chr17 | 42907655 | 42908028 | chr17 | 43001800 | 43002029 |
| chr17 | 43044584 | 43044763 | chr17 | 43045039 | 43045208 | chr17 | 43047355 | 43047404 |
| chr17 | 43047753 | 43047834 | chr17 | 43339012 | 43339408 | chr17 | 43339546 | 43339994 |
| chr17 | 43974158 | 43974400 | chr17 | 45331345 | 45331404 | chr17 | 45810767 | 45811426 |
| chr17 | 45867239 | 45867538 | chr17 | 46124907 | 46124970 | chr17 | 46125007 | 46125146 |
| chr17 | 46619224 | 46619224 | chr17 | 46620405 | 46621184 | chr17 | 46621257 | 46621535 |
| chr17 | 46621764 | 46622003 | chr17 | 46655074 | 46655253 | chr17 | 46655351 | 46655394 |
| chr17 | 46655396 | 46655419 | chr17 | 46655451 | 46655561 | chr17 | 46655563 | 46655999 |
| chr17 | 46656058 | 46656531 | chr17 | 46659385 | 46659926 | chr17 | 46663666 | 46663825 |
| chr17 | 46663856 | 46663928 | chr17 | 46674831 | 46675072 | chr17 | 46675086 | 46675685 |
| chr17 | 46690430 | 46690705 | chr17 | 46691430 | 46691669 | chr17 | 46691719 | 46691819 |
| chr17 | 46691988 | 46692198 | chr17 | 46692344 | 46692509 | chr17 | 46710857 | 46710990 |
| chr17 | 46713934 | 46714130 | chr17 | 46714132 | 46714166 | chr17 | 46795563 | 46796374 |
| chr17 | 46796499 | 46796545 | chr17 | 46796606 | 46796638 | chr17 | 46796850 | 46797214 |
| chr17 | 46797275 | 46797662 | chr17 | 46799522 | 46800001 | chr17 | 46800516 | 46800755 |
| chr17 | 46800860 | 46801048 | chr17 | 46801109 | 46801418 | chr17 | 46802364 | 46802912 |
| chr17 | 46802994 | 46803286 | chr17 | 46804029 | 46804508 | chr17 | 46810328 | 46811047 |
| chr17 | 46811269 | 46811500 | chr17 | 46811595 | 46811628 | chr17 | 46816191 | 46816730 |
| chr17 | 46824218 | 46824276 | chr17 | 46824359 | 46824915 | chr17 | 46824917 | 46825149 |
| chr17 | 46825190 | 46825609 | chr17 | 46826897 | 46827196 | chr17 | 46827244 | 46827502 |
| chr17 | 46827626 | 46827843 | chr17 | 46829420 | 46829659 | chr17 | 46829898 | 46830136 |
| chr17 | 46830190 | 46830195 | chr17 | 46831700 | 46832326 | chr17 | 46832490 | 46832719 |
| chr17 | 47072716 | 47073029 | chr17 | 47073104 | 47073328 | chr17 | 47073389 | 47073555 |
| chr17 | 47073899 | 47074318 | chr17 | 47074459 | 47074489 | chr17 | 47074597 | 47074998 |
| chr17 | 47075083 | 47075442 | chr17 | 47075616 | 47075735 | chr17 | 47075880 | 47076155 |
| chr17 | 47574001 | 47574240 | chr17 | 47657445 | 47657684 | chr17 | 47865416 | 47865655 |
| chr17 | 47987423 | 47987722 | chr17 | 47987843 | 47988202 | chr17 | 48041057 | 48041416 |
| chr17 | 48041578 | 48041817 | chr17 | 48041965 | 48042141 | chr17 | 48042337 | 48042648 |
| chr17 | 48042751 | 48043056 | chr17 | 48048857 | 48049156 | chr17 | 48049228 | 48050607 |
| chr17 | 48070946 | 48071125 | chr17 | 48071694 | 48071705 | chr17 | 48071807 | 48071957 |
| chr17 | 48612147 | 48612386 | chr17 | 48636500 | 48637219 | chr17 | 48653054 | 48653233 |
| chr17 | 48799847 | 48799963 | chr17 | 49229486 | 49229601 | chr17 | 50235126 | 50235259 |
| chr17 | 50235625 | 50236032 | chr17 | 51900930 | 51901109 | chr17 | 53341155 | 53341557 |
| chr17 | 53342774 | 53343029 | chr17 | 53343031 | 53343193 | chr17 | 53922571 | 53922870 |
| chr17 | 54674890 | 54675137 | chr17 | 54675139 | 54675369 | chr17 | 54755873 | 54755991 |
| chr17 | 56092519 | 56092620 | chr17 | 56234305 | 56234844 | chr17 | 56326853 | 56327092 |
| chr17 | 56327197 | 56327376 | chr17 | 56833025 | 56833324 | chr17 | 56833622 | 56834001 |
| chr17 | 56834020 | 56834161 | chr17 | 56834222 | 56834461 | chr17 | 57297028 | 57297207 |
| chr17 | 58216566 | 58216837 | chr17 | 58216866 | 58217299 | chr17 | 58217357 | 58217652 |
| chr17 | 58218670 | 58219089 | chr17 | 58227281 | 58227398 | chr17 | 58498657 | 58498977 |
| chr17 | 58498979 | 58499396 | chr17 | 59474050 | 59474247 | chr17 | 59474758 | 59475177 |
| chr17 | 59475604 | 59476023 | chr17 | 59476084 | 59476203 | chr17 | 59476314 | 59476733 |
| chr17 | 59478046 | 59478705 | chr17 | 59488010 | 59488424 | chr17 | 59528775 | 59529151 |
| chr17 | 59529254 | 59529265 | chr17 | 59529844 | 59530454 | chr17 | 59531574 | 59532018 |
| chr17 | $9533741 | 59533768 | chr17 | 59533875 | 59534406 | chr17 | 59534557 | 59534580 |
| chr17 | 59534677 | 59534856 | chr17 | 59535059 | $9535298 | chr17 | 59539150 | 59539689 |
| chr17 | 61777984 | 61778074 | chr17 | 61778235 | 61778249 | chr17 | 61817858 | 61818036 |
| chr17 | 61926149 | 61926325 | chr17 | 61926508 | 61926625 | chr17 | 62777244 | 62777543 |
| chr17 | 62777650 | 62777889 | chr17 | 54672276 | 64672635 | chr17 | 66596379 | 66596618 |
| chr17 | 66596884 | 66597123 | chr17 | 67410389 | 67410501 | chr17 | 68164667 | 68164906 |
| chr17 | 70026473 | 70026755 | chr17 | 70112818 | 70113567 | chr17 | 70113648 | 70114019 |
| chr17 | 70114153 | 70114617 | chr17 | 70215595 | 70216307 | chr17 | 70216393 | 70216674 |
| chr17 | 71641465 | 71641761 | chr17 | 71948352 | 71948951 | chr17 | 72270202 | 72270501 |
| chr17 | 72321844 | 72322074 | chr17 | 72322275 | 72322558 | chr17 | 72322612 | 72322694 |
| chr17 | 72353148 | 72353260 | chr17 | 72353417 | 72353531 | chr17 | 72427777 | 72427963 |
| chr17 | 72428244 | 72428483 | chr17 | 72667242 | 72667482 | chr17 | 72848926 | 72849165 |
| chr17 | 72856964 | 72857443 | chr17 | 72920705 | 72921124 | chr17 | 73031547 | 73031619 |
| chr17 | 73073610 | 73023684 | chr17 | 73545910 | 73546120 | chr17 | 73584938 | 73584972 |
| chr17 | 73585918 | 73586517 | chr17 | 73608232 | 73608411 | chr17 | 73636052 | 73636421 |
| chr17 | 74028261 | 74028461 | chr17 | 74047755 | 74047994 | chr17 | 74070386 | 74070480 |

TABLE 15-continued

| chr | start | end | chr | start | end | chr | start | end |
|---|---|---|---|---|---|---|---|---|
| chr17 | 74071344 | 74071583 | chr17 | 74071590 | 74071825 | chr17 | 74072999 | 74073139 |
| chr17 | 74073172 | 74073531 | chr17 | 74390289 | 74390468 | chr17 | 74533808 | 74534363 |
| chr17 | 74534388 | 74534407 | chr17 | 74581083 | 74581322 | chr17 | 74864974 | 74865068 |
| chr17 | 74865070 | 74865273 | chr17 | 74865612 | 74866331 | chr17 | 75207765 | 75207944 |
| chr17 | 75368658 | 75368902 | chr17 | 75368904 | 75369091 | chr17 | 75369093 | 75369317 |
| chr17 | 75369351 | 75369458 | chr17 | 75369493 | 75369950 | chr17 | 75370186 | 75370413 |
| chr17 | 75370522 | 75370701 | chr17 | 75385122 | 75385301 | chr17 | 75523058 | 75523354 |
| chr17 | 75524556 | 75525004 | chr17 | 75525006 | 75525275 | chr17 | 75733902 | 75734108 |
| chr17 | 75797121 | 75797265 | chr17 | 76125122 | 76125301 | chr17 | 76137862 | 76138281 |
| chr17 | 76138525 | 76138710 | chr17 | 76227774 | 76228162 | chr17 | 76228214 | 76228433 |
| chr17 | 76404662 | 76404757 | chr17 | 76921756 | 76921806 | chr17 | 76921860 | 76921934 |
| chr17 | 76974354 | 76974582 | chr17 | 77084488 | 77084667 | chr17 | 77104978 | 77105277 |
| chr17 | 77145037 | 77145336 | chr17 | 77179017 | 77179064 | chr17 | 77179082 | 77179330 |
| chr17 | 77179618 | 77179709 | chr17 | 77179711 | 77179777 | chr17 | 77179800 | 77179891 |
| chr17 | 77776733 | 77776996 | chr17 | 77777053 | 77777152 | chr17 | 77777504 | 77777649 |
| chr17 | 77777651 | 77777904 | chr17 | 77777944 | 77778043 | chr17 | 77778852 | 77779136 |
| chr17 | 77789474 | 77789528 | chr17 | 77825605 | 77825858 | chr17 | 77899590 | 77899634 |
| chr17 | 78122175 | 78122294 | chr17 | 78447053 | 78447213 | chr17 | 78451842 | 78451954 |
| chr17 | 78452109 | 78452141 | chr17 | 78452199 | 78452438 | chr17 | 78452578 | 78452937 |
| chr17 | 78518204 | 78518295 | chr17 | 78599493 | 78599732 | chr17 | 78667897 | 78668256 |
| chr17 | 78874418 | 78874650 | chr17 | 79094095 | 79094334 | chr17 | 79099696 | 79099875 |
| chr17 | 79615087 | 79615136 | chr17 | 79615435 | 79615446 | chr17 | 79626656 | 79626797 |
| chr17 | 79769354 | 79769773 | chr17 | 80254258 | 80254371 | chr17 | 80289153 | 80289392 |
| chr17 | 80329628 | 80330001 | chr17 | 80330165 | 80330167 | chr17 | 80394659 | 80394678 |
| chr17 | 80479366 | 80479525 | chr17 | 80535286 | 80536469 | chr17 | 80654909 | 80655088 |
| chr17 | 80693343 | 80693582 | chr17 | 80797600 | 80798439 | chr17 | 80832209 | 80832508 |
| chr17 | 80832635 | 80832874 | chr17 | 81008543 | 81008902 | chr17 | 81033413 | 81033592 |
| chr17 | 81048919 | 81049098 | chr17 | 81049943 | 81050146 | chr18 | 199454 | 499575 |
| chr18 | 499947 | 500842 | chr18 | 904376 | 904735 | chr18 | 904926 | 905105 |
| chr18 | 905359 | 905616 | chr18 | 905693 | 905718 | chr18 | 906770 | 907009 |
| chr18 | 907384 | 907683 | chr18 | 907826 | 908065 | chr18 | 908373 | 908607 |
| chr18 | 909046 | 909085 | chr18 | 909184 | 909225 | chr18 | 909388 | 909687 |
| chr18 | 2755855 | 2755974 | chr18 | 2906167 | 2906406 | chr18 | 3215032 | 3215271 |
| chr18 | 3498980 | 3499447 | chr18 | 4453885 | 4454244 | chr18 | 4454979 | 4455031 |
| chr18 | 4455259 | 4455272 | chr18 | 5133126 | 5133405 | chr18 | 5196576 | 5197038 |
| chr18 | 5197126 | 5197272 | chr18 | 5197330 | 5197425 | chr18 | 5543132 | 5543158 |
| chr18 | 5543431 | 5543431 | chr18 | 5543900 | 5543957 | chr18 | 5628072 | 5628611 |
| chr18 | 5629700 | 5629826 | chr18 | 5630218 | 5630457 | chr18 | 5891337 | 5891418 |
| chr18 | 5894935 | 5894946 | chr18 | 5895018 | 5895294 | chr18 | 5895881 | 5896180 |
| chr18 | 6729881 | 6730093 | chr18 | 7116858 | 7116883 | chr18 | 7117060 | 7112023 |
| chr18 | 7117616 | 7117885 | chr18 | 7567708 | 7568367 | chr18 | 8608649 | 8608838 |
| chr18 | 8608902 | 8609062 | chr18 | 8612178 | 8612357 | chr18 | 9771621 | 9771850 |
| chr18 | 9912693 | 9912872 | chr18 | 10589013 | 10589432 | chr18 | 11148888 | 11149094 |
| chr18 | 11149116 | 11149127 | chr18 | 11149486 | 11149760 | chr18 | 11149780 | 11149955 |
| chr18 | 11401557 | 11401845 | chr18 | 11751538 | 11751632 | chr18 | 11752128 | 11752473 |
| chr18 | 11752641 | 11752805 | chr18 | 11942634 | 11942746 | chr18 | 12254133 | 12254147 |
| chr18 | 12254305 | 12254672 | chr18 | 12307603 | 12307829 | chr18 | 12376133 | 12376206 |
| chr18 | 13824125 | 13824184 | chr18 | 13826316 | 13826615 | chr18 | 13868620 | 13868920 |
| chr18 | 13868947 | 13869039 | chr18 | 15198162 | 15198269 | chr18 | 18822294 | 18823060 |
| chr18 | 18823101 | 18823373 | chr18 | 19750286 | 19750447 | chr18 | 20911467 | 20911646 |
| chr18 | 21269344 | 21269490 | chr18 | 21269581 | 21269763 | chr18 | 22928981 | 22929096 |
| chr18 | 22929187 | 22929719 | chr18 | 22929927 | 22930283 | chr18 | 22930285 | 22930660 |
| chr18 | 22930715 | 22931254 | chr18 | 23686388 | 23686507 | chr18 | 24127650 | 24128129 |
| chr18 | 24130729 | 24130947 | chr18 | 24131099 | 24131267 | chr18 | 24764851 | 24765188 |
| chr18 | 24765231 | 24765252 | chr18 | 25755556 | 25755744 | chr18 | 25755936 | 25756115 |
| chr18 | 25756542 | 25756822 | chr18 | 25757151 | 25757438 | chr18 | 25757440 | 25757530 |
| chr18 | 25757687 | 25757926 | chr18 | 25758129 | 25758233 | chr18 | 28620819 | 28620956 |
| chr18 | 28621034 | 28621178 | chr18 | 28621242 | 28621274 | chr18 | 28621383 | 28621481 |
| chr18 | 28621545 | 28622024 | chr18 | 28622335 | 28622574 | chr18 | 30349642 | 30349872 |
| chr18 | 31020419 | 31020511 | chr18 | 31158007 | 31158049 | chr18 | 31738953 | 31739552 |
| chr18 | 31802031 | 31802270 | chr18 | 31802864 | 31803043 | chr18 | 31803336 | 31803575 |
| chr18 | 31902690 | 31902944 | chr18 | 32073807 | 32073831 | chr18 | 32073908 | 32074166 |
| chr18 | 32557847 | 32557882 | chr18 | 32557884 | 32557968 | chr18 | 32957702 | 32957813 |
| chr18 | 33078274 | 33078393 | chr18 | 33078634 | 33078753 | chr18 | 33877784 | 33877839 |
| chr18 | 34833519 | 34833554 | chr18 | 35064986 | 35065146 | chr18 | 35065517 | 35065525 |
| chr18 | 35104935 | 35104984 | chr18 | 35144766 | 35144937 | chr18 | 35144969 | 35145545 |
| chr18 | 35146023 | 35146037 | chr18 | 35146062 | 35146322 | chr18 | 35147409 | 35147648 |
| chr18 | 43914156 | 43914226 | chr18 | 43914228 | 43914365 | chr18 | 44259911 | 44260067 |
| chr18 | 44335999 | 44336450 | chr18 | 44337013 | 44337044 | chr18 | 44337445 | 44337618 |
| chr18 | 44337650 | 44337842 | chr18 | 44338099 | 44338164 | chr18 | 44772980 | 44773117 |
| chr18 | 44773574 | 44773967 | chr18 | 44774202 | 44774233 | chr18 | 44774319 | 44774804 |
| chr18 | 44775309 | 44775647 | chr18 | 44776881 | 44777180 | chr18 | 44777227 | 44777406 |
| chr18 | 44777512 | 44777792 | chr18 | 44777949 | 44778411 | chr18 | 44780903 | 44781142 |
| chr18 | 44787695 | 44787934 | chr18 | 44788177 | 44788356 | chr18 | 44789375 | 44789614 |
| chr18 | 44789786 | 44790025 | chr18 | 45057993 | 45058293 | chr18 | 45058308 | 45058335 |
| chr18 | 46142587 | 46142715 | chr18 | 49867202 | 49867483 | chr18 | 52988906 | 52989155 |
| chr18 | 52989157 | 52989316 | chr18 | 52989723 | 52989962 | chr18 | 53257052 | 53257291 |
| chr18 | 53446884 | 53447475 | chr18 | 53447799 | 53447903 | chr18 | 53989718 | 53989828 |

TABLE 15-continued

| chr | start | end | chr | start | end | chr | start | end |
|---|---|---|---|---|---|---|---|---|
| chr18 | 53989876 | 53989957 | chr18 | 54788984 | 54789343 | chr18 | 55019610 | 55019776 |
| chr18 | 55020572 | 55020699 | chr18 | 55020805 | 55020811 | chr18 | 55020981 | 55021340 |
| chr18 | 55103307 | 55103414 | chr18 | 55103762 | 55103824 | chr18 | 55104744 | 55105244 |
| chr18 | 55105630 | 55105929 | chr18 | 55114441 | 55114740 | chr18 | 55850767 | 55851066 |
| chr18 | 56483824 | 56483938 | chr18 | 56815757 | 56815876 | chr18 | 56886981 | 56887469 |
| chr18 | 56887503 | 56887517 | chr18 | 56888470 | 56888656 | chr18 | 56888687 | 56888709 |
| chr18 | 56931460 | 56931682 | chr18 | 56931888 | 56932187 | chr18 | 56932256 | 56932375 |
| chr18 | 56934926 | 56935405 | chr18 | 56935920 | 56936159 | chr18 | 56939025 | 56939264 |
| chr18 | 56939324 | 56939652 | chr18 | 56939764 | 56940171 | chr18 | 56940566 | 56940823 |
| chr18 | 56940863 | 56941245 | chr18 | 56941558 | 56941882 | chr18 | 57363606 | 57363845 |
| chr18 | 57364449 | 57364484 | chr18 | 57364556 | 57364795 | chr18 | 59000886 | 59001125 |
| chr18 | 59001222 | 59001344 | chr18 | 59001498 | 59001821 | chr18 | 60263452 | 60263544 |
| chr18 | 60263661 | 60263991 | chr18 | 60985417 | 60985533 | chr18 | 60985593 | 60985732 |
| chr18 | 60985734 | 60985825 | chr18 | 67067464 | 67067893 | chr18 | 67067895 | 67067971 |
| chr18 | 67067996 | 67068003 | chr18 | 67068059 | 67068114 | chr18 | 67068614 | 67068913 |
| chr18 | 67069142 | 67069321 | chr18 | 70209102 | 70209297 | chr18 | 70209348 | 70209386 |
| chr18 | 70209494 | 70209527 | chr18 | 70210483 | 70210583 | chr18 | 70211527 | 70211766 |
| chr18 | 70534207 | 70534316 | chr18 | 70534428 | 70534686 | chr18 | 70535299 | 70535555 |
| chr18 | 70535576 | 70535658 | chr18 | 70535918 | 70536084 | chr18 | 70536188 | 70536697 |
| chr18 | 70536733 | 70536972 | chr18 | 70537230 | 70537293 | chr18 | 73167500 | 73167919 |
| chr18 | 73627925 | 73628153 | chr18 | 74501045 | 74501267 | chr18 | 74755430 | 74755577 |
| chr18 | 74961264 | 74961737 | chr18 | 74961739 | 74961956 | chr18 | 74962019 | 74962171 |
| chr18 | 74962210 | 74962247 | chr18 | 74962693 | 74962751 | chr18 | 74962896 | 74963546 |
| chr18 | 75339137 | 75339436 | chr18 | 75362839 | 75363078 | chr18 | 75551197 | 75551376 |
| chr18 | 75612137 | 75612376 | chr18 | 75999330 | 75999509 | chr18 | 76239460 | 76239699 |
| chr18 | 76501405 | 76501584 | chr18 | 76653557 | 76653736 | chr18 | 76686175 | 76686354 |
| chr18 | 77143365 | 77143451 | chr18 | 77167752 | 77167929 | chr18 | 77181263 | 77181502 |
| chr18 | 77194838 | 77195077 | chr18 | 77205436 | 77205735 | chr18 | 77285814 | 77286113 |
| chr18 | 77309459 | 77309638 | chr18 | 77312784 | 77313012 | chr18 | 77329633 | 77330101 |
| chr18 | 77371350 | 77371589 | chr18 | 77543156 | 77543335 | chr18 | 77543673 | 77543912 |
| chr18 | 77547985 | 77548048 | chr18 | 77548352 | 77548700 | chr18 | 77550108 | 77550457 |
| chr18 | 77557981 | 77558397 | chr18 | 77558417 | 77558460 | chr18 | 77558732 | 77559031 |
| chr18 | 77576853 | 77577139 | chr18 | 77636517 | 77636696 | chr18 | 78005004 | 78005142 |
| chr19 | 403435 | 403888 | chr19 | 407106 | 407405 | chr19 | 462106 | 462235 |
| chr19 | 468683 | 468862 | chr19 | 485071 | 485490 | chr19 | 549287 | 549526 |
| chr19 | 555509 | 555625 | chr19 | 591272 | 591511 | chr19 | 592492 | 592654 |
| chr19 | 593197 | 593325 | chr19 | 599125 | 599424 | chr19 | 752060 | 752359 |
| chr19 | 869247 | 869363 | chr19 | 883529 | 883888 | chr19 | 883941 | 884240 |
| chr19 | 891441 | 891616 | chr19 | 955668 | 956327 | chr19 | 1003226 | 1003465 |
| chr19 | 1003583 | 1003822 | chr19 | 1004819 | 1005528 | chr19 | 1030082 | 1030309 |
| chr19 | 1047796 | 1047915 | chr19 | 1083392 | 1083526 | chr19 | 1156450 | 1156629 |
| chr19 | 1170089 | 1170328 | chr19 | 1171003 | 1171422 | chr19 | 1220349 | 1220696 |
| chr19 | 1236397 | 1236631 | chr19 | 1274683 | 1274922 | chr19 | 1308066 | 1308184 |
| chr19 | 1325714 | 1325989 | chr19 | 1401655 | 1401894 | chr19 | 1450236 | 1450475 |
| chr19 | 1496313 | 1496552 | chr19 | 1496555 | 1496672 | chr19 | 1524443 | 1524528 |
| chr19 | 1525530 | 1526053 | chr19 | 1527132 | 1527307 | chr19 | 1754094 | 1754194 |
| chr19 | 1754225 | 1754333 | chr19 | 1754653 | 1754892 | chr19 | 1757337 | 1757696 |
| chr19 | 1762376 | 1762506 | chr19 | 1762628 | 1762675 | chr19 | 1764197 | 1764374 |
| chr19 | 1775037 | 1775338 | chr19 | 1776276 | 1776635 | chr19 | 1807893 | 1808492 |
| chr19 | 2251075 | 2251235 | chr19 | 2251611 | 2251794 | chr19 | 2252589 | 2252752 |
| chr19 | 2252901 | 2263736 | chr19 | 2253781 | 2253860 | chr19 | 2274576 | 2274692 |
| chr19 | 2290165 | 2290272 | chr19 | 2290631 | 2290868 | chr19 | 2302693 | 2303052 |
| chr19 | 2331339 | 2331518 | chr19 | 2513149 | 2513388 | chr19 | 2683817 | 2684046 |
| chr19 | 3041486 | 3041522 | chr19 | 3219555 | 3219659 | chr19 | 3296523 | 3296762 |
| chr19 | 3361055 | 3361374 | chr19 | 3361376 | 3361474 | chr19 | 3562249 | 3562583 |
| chr19 | 3578062 | 3578301 | chr19 | 3778053 | 3778472 | chr19 | 3779177 | 3779536 |
| chr19 | 3785566 | 3785836 | chr19 | 3785865 | 3786221 | chr19 | 3820952 | 3821311 |
| chr19 | 3822008 | 3822110 | chr19 | 3822135 | 3822307 | chr19 | 3855322 | 3855681 |
| chr19 | 4054334 | 4054463 | chr19 | 4054540 | 4054573 | chr19 | 4311173 | 4311350 |
| chr19 | 4548040 | 4548459 | chr19 | 4550169 | 4550408 | chr19 | 4555813 | 4556214 |
| chr19 | 4557018 | 4557317 | chr19 | 4670678 | 4670857 | chr19 | 5292709 | 5292948 |
| chr19 | 5338820 | 5338851 | chr19 | 5338901 | 5339239 | chr19 | 5759670 | 5759789 |
| chr19 | 5826175 | 5826284 | chr19 | 5910275 | 5910429 | chr19 | 5914687 | 5914866 |
| chr19 | 5914907 | 5915146 | chr19 | 6590244 | 6590582 | chr19 | 7794919 | 7795338 |
| chr19 | 7852944 | 7853243 | chr19 | 7853262 | 7853471 | chr19 | 7853544 | 7853561 |
| chr19 | 8115149 | 8115376 | chr19 | 8576838 | 8577077 | chr19 | 9473939 | 9474140 |
| chr19 | 9517511 | 9517791 | chr19 | 9608817 | 9609116 | chr19 | 9609229 | 9609528 |
| chr19 | 9903828 | 9904054 | chr19 | 9937370 | 9937489 | chr19 | 10231221 | 10231331 |
| chr19 | 10361965 | 10362076 | chr19 | 10398128 | 10398367 | chr19 | 10405892 | 10406160 |
| chr19 | 10406279 | 10406431 | chr19 | 10406798 | 10407030 | chr19 | 10407045 | 10407211 |
| chr19 | 10527085 | 10527282 | chr19 | 10531317 | 10531616 | chr19 | 10531890 | 10532069 |
| chr19 | 10624740 | 10624853 | chr19 | 10624966 | 10625558 | chr19 | 10823581 | 10823708 |
| chr19 | 11590929 | 11591288 | chr19 | 11592611 | 11592850 | chr19 | 11592942 | 11593241 |
| chr19 | 11689363 | 11689662 | chr19 | 11959816 | 11960175 | chr19 | 12163452 | 12163770 |
| chr19 | 12163819 | 12163998 | chr19 | 12175356 | 12175595 | chr19 | 12175731 | 12176090 |
| chr19 | 12202937 | 12203349 | chr19 | 12203351 | 12203638 | chr19 | 12266924 | 12267308 |
| chr19 | 12267310 | 12267763 | chr19 | 12305754 | 12306194 | chr19 | 12306230 | 12306303 |
| chr19 | 12306305 | 12306351 | chr19 | 12476405 | 12476465 | chr19 | 12476501 | 12476644 |

TABLE 15-continued

| chr | start | end | chr | start | end | chr | start | end |
|---|---|---|---|---|---|---|---|---|
| chr19 | 12606297 | 12606555 | chr19 | 12750903 | 12751142 | chr19 | 12863329 | 12863616 |
| chr19 | 12951921 | 12952129 | chr19 | 12952131 | 12952220 | chr19 | 12996076 | 12996375 |
| chr19 | 13616617 | 13616957 | chr19 | 13617159 | 13617336 | chr19 | 13618186 | 13618485 |
| chr19 | 13965933 | 13966022 | chr19 | 14181217 | 14181682 | chr19 | 14584168 | 14584413 |
| chr19 | 14584537 | 14584868 | chr19 | 15090097 | 15090576 | chr19 | 15121611 | 15121970 |
| chr19 | 15122030 | 15122314 | chr19 | 15288346 | 15288945 | chr19 | 15292293 | 15292592 |
| chr19 | 15342635 | 15343411 | chr19 | 15344007 | 15344131 | chr19 | 15344418 | 15344426 |
| chr19 | 17006991 | 17007389 | chr19 | 17007447 | 17007764 | chr19 | 17008422 | 17008519 |
| chr19 | 17008586 | 17008699 | chr19 | 17008821 | 17008884 | chr19 | 17392545 | 17392964 |
| chr19 | 17717212 | 17717391 | chr19 | 17759145 | 17759504 | chr19 | 17791108 | 17791287 |
| chr19 | 17958396 | 17958935 | chr19 | 17983447 | 17983666 | chr19 | 17983840 | 17983910 |
| chr19 | 18041167 | 18041286 | chr19 | 18103637 | 18103816 | chr19 | 18104390 | 18104493 |
| chr19 | 18271871 | 18271999 | chr19 | 18330935 | 18331234 | chr19 | 18343355 | 18343654 |
| chr19 | 18343880 | 18344062 | chr19 | 18383252 | 18383431 | chr19 | 18714465 | 18714581 |
| chr19 | 18811473 | 18811771 | chr19 | 18899333 | 18899718 | chr19 | 18901753 | 18902172 |
| chr19 | 18980680 | 18980718 | chr19 | 18980912 | 18980979 | chr19 | 18989722 | 18990360 |
| chr19 | 18994808 | 18995227 | chr19 | 19334769 | 19334993 | chr19 | 19645776 | 19646015 |
| chr19 | 19651991 | 19652164 | chr19 | 20011908 | 20011992 | chr19 | 20012053 | 20012172 |
| chr19 | 20188746 | 20188865 | chr19 | 20189411 | 20189530 | chr19 | 21646333 | 21646512 |
| chr19 | 21769223 | 21769375 | chr19 | 22018429 | 22018724 | chr19 | 22034402 | 22034418 |
| chr19 | 22034420 | 22034422 | chr19 | 22034447 | 22034896 | chr19 | 22610542 | 22610701 |
| chr19 | 22715053 | 22715532 | chr19 | 23254115 | 23254294 | chr19 | 23257780 | 23258008 |
| chr19 | 23258306 | 23258559 | chr19 | 23258680 | 23258799 | chr19 | 23299705 | 23299784 |
| chr19 | 23433104 | 23433223 | chr19 | 23598358 | 23598420 | chr19 | 24154518 | 24154697 |
| chr19 | 24216940 | 24217119 | chr19 | 29284377 | 29284576 | chr19 | 29505081 | 29505258 |
| chr19 | 30015844 | 30015963 | chr19 | 30016025 | 30016803 | chr19 | 30016832 | 30016929 |
| chr19 | 30017452 | 30017510 | chr19 | 30017578 | 30017722 | chr19 | 30017766 | 30018691 |
| chr19 | 30019043 | 30019529 | chr19 | 30019531 | 30019611 | chr19 | 30019661 | 30019931 |
| chr19 | 30020014 | 30020553 | chr19 | 30021263 | 30021279 | chr19 | 30215468 | 30215572 |
| chr19 | 30252214 | 30252330 | chr19 | 30555254 | 30555473 | chr19 | 30562687 | 30562831 |
| chr19 | 30637413 | 30637633 | chr19 | 30713384 | 30713593 | chr19 | 30713686 | 30713803 |
| chr19 | 30713829 | 30714128 | chr19 | 30714425 | 30714508 | chr19 | 30715315 | 30715854 |
| chr19 | 30716236 | 30716655 | chr19 | 30716732 | 30716770 | chr19 | 30716953 | 30718231 |
| chr19 | 30718761 | 30718934 | chr19 | 30719369 | 30720134 | chr19 | 30865626 | 30866025 |
| chr19 | 30866453 | 30866525 | chr19 | 31804650 | 31804829 | chr19 | 31839838 | 31839928 |
| chr19 | 31839942 | 31839969 | chr19 | 31841834 | 31842072 | chr19 | 31842116 | 31842481 |
| chr19 | 32364265 | 32364504 | chr19 | 32516309 | 32516495 | chr19 | 32715588 | 32715827 |
| chr19 | 32898350 | 32898589 | chr19 | 33167035 | 331674.88 | chr19 | 33167497 | 33167514 |
| chr19 | 33467984 | 33468157 | chr19 | 33685493 | 33686683 | chr19 | 33792412 | 33792612 |
| chr19 | 33794599 | 33794745 | chr19 | 33794780 | 33794838 | chr19 | 34112185 | 34112287 |
| chr19 | 34112327 | 34112424 | chr19 | 34112450 | 34112730 | chr19 | 34113259 | 34113303 |
| chr19 | 34113367 | 34113398 | chr19 | 34113400 | 34113678 | chr19 | 34113911 | 34114050 |
| chr19 | 34972523 | 34972569 | chr19 | 34973243 | 34973330 | chr19 | 34973558 | 34973644 |
| chr19 | 34973646 | 34973797 | chr19 | 35263983 | 35264092 | chr19 | 35395923 | 35395949 |
| chr19 | 35396251 | 35396462 | chr19 | 35616250 | 35616489 | chr19 | 35781298 | 35781537 |
| chr19 | 35797822 | 35798061 | chr19 | 36048504 | 36048863 | chr19 | 36049246 | 36049368 |
| chr19 | 36049397 | 36049497 | chr19 | 36222334 | 36222567 | chr19 | 36249933 | 36250232 |
| chr19 | 36334884 | 36335243 | chr19 | 36347791 | 36348147 | chr19 | 36450030 | 36450296 |
| chr19 | 36523258 | 36523557 | chr19 | 36735953 | 36736132 | chr19 | 36736226 | 36736296 |
| chr19 | 36736315 | 36736585 | chr19 | 36822249 | 36822467 | chr19 | 36822558 | 36822968 |
| chr19 | 36909074. | 36909349 | chr19 | 36909624 | 36910028 | chr19 | 36912257 | 36912350 |
| chr19 | 36912481 | 36912496 | chr19 | 37095591 | 37095813 | chr19 | 37096488 | 37096660 |
| chr19 | 37263439 | 37263678 | chr19 | 37264143 | 37264487 | chr19 | 37288237 | 37288425 |
| chr19 | 37288607 | 37288705 | chr19 | 37288707 | 37288869 | chr19 | 37341683 | 37342042 |
| chr19 | 37407046 | 37407152 | chr19 | 37407154 | 37407374 | chr19 | 37407376 | 37407525 |
| chr19 | 37463953 | 37464568 | chr19 | 37464667 | 37464792 | chr19 | 37569394 | 37569573 |
| chr19 | 37702087 | 37702265 | chr19 | 37959762 | 37959801 | chr19 | 37959874 | 37960061 |
| chr19 | 37997337 | 37997991 | chr19 | 37997993 | 37998206 | chr19 | 38042357 | 38042769 |
| chr19 | 38085160 | 38085759 | chr19 | 38085958 | 38086110 | chr19 | 38145976 | 38146335 |
| chr19 | 38146364 | 38146663 | chr19 | 38182793 | 38182960 | chr19 | 38183112 | 38183259 |
| chr19 | 38183261 | 38183262 | chr19 | 38183264 | 38183392 | chr19 | 38308031 | 38308337 |
| chr19 | 38308395 | 38308543 | chr19 | 38480952 | 38481190 | chr19 | 38747072 | 38747078 |
| chr19 | 38747107 | 38747201 | chr19 | 38747203 | 38747448 | chr19 | 38755189 | 38755422 |
| chr19 | 38782485 | 38782664 | chr19 | 38789223 | 38789373 | chr19 | 38873861 | 38874040 |
| chr19 | 38906446 | 38905805 | chr19 | 38974158 | 38974337 | chr19 | 39135435 | 39135554 |
| chr19 | 39687575 | 39687647 | chr19 | 39687756 | 39687934 | chr19 | 39754787 | 39755233 |
| chr19 | 39755265 | 39755446 | chr19 | 39816862 | 39817161 | chr19 | 39993392 | 39993652 |
| chr19 | 39993712 | 39993751 | chr19 | 39997602 | 39997733 | chr19 | 39997749 | 39997901 |
| chr19 | 40006093 | 40006161 | chr19 | 40006187 | 40006392 | chr19 | 40006499 | 40006728 |
| chr19 | 40723923 | 40724342 | chr19 | 40829768 | 40830123 | chr19 | 40902350 | 40902779 |
| chr19 | 40951087 | 40951197 | chr19 | 40951602 | 40951841 | chr19 | 41018456 | 41019063 |
| chr19 | 41019076 | 41019131 | chr19 | 41025462 | 41025761 | chr19 | 41059832 | 41060385 |
| chr19 | 41073513 | 41073752 | chr19 | 41119097 | 41119277 | chr19 | 41119371 | 41119409 |
| chr19 | 41119670 | 41119735 | chr19 | 41354576 | 41354814 | chr19 | 41641740 | 41641979 |
| chr19 | 42028407 | 42028646 | chr19 | 42408226 | 42408405 | chr19 | 42827810 | 42827820 |
| chr19 | 42827982 | 42828085 | chr19 | 42828317 | 42828349 | chr19 | 42856486 | 42856558 |
| chr19 | 44203735 | 44203962 | chr19 | 44405819 | 44405924 | chr19 | 44405926 | 44406178 |
| chr19 | 44599691 | 44599803 | chr19 | 44905425 | 44905604 | chr19 | 44952193 | 44952618 |

TABLE 15-continued

| chr | start | end | chr | start | end | chr | start | end |
|---|---|---|---|---|---|---|---|---|
| chr19 | 44952620 | 44952665 | chr19 | 44952667 | 44952909 | chr19 | 45003142 | 45003417 |
| chr19 | 45300052 | 45300291 | chr19 | 45570307 | 45570546 | chr19 | 45574391 | 45574570 |
| chr19 | 45574682 | 45574782 | chr19 | 45574837 | 45574981 | chr19 | 45655309 | 45655349 |
| chr19 | 45655400 | 45655557 | chr19 | 45655648 | 45656448 | chr19 | 45656589 | 45656743 |
| chr19 | 45656791 | 45657008 | chr19 | 45657129 | 45657368 | chr19 | 45810005 | 45810345 |
| chr19 | 45835239 | 45835353 | chr19 | 45888843 | 45889225 | chr19 | 45889316 | 45889484 |
| chr19 | 45997437 | 45997676 | chr19 | 46001945 | 46002353 | chr19 | 46234853 | 46234965 |
| chr19 | 46379822 | 46379858 | chr19 | 46379894 | 46380241 | chr19 | 46404448 | 46404682 |
| chr19 | 46916631 | 46916988 | chr19 | 46917061 | 46917170 | chr19 | 46930046 | 46930278 |
| chr19 | 46974477 | 46974567 | chr19 | 46974569 | 46974609 | chr19 | 46992643 | 46992942 |
| chr19 | 46993067 | 46993261 | chr19 | 46993282 | 46993486 | chr19 | 46996509 | 46996515 |
| chr19 | 46996578 | 46996748 | chr19 | 46996775 | 46996839 | chr19 | 47152978 | 47152991 |
| chr19 | 42200270 | 47200629 | chr19 | 47910559 | 47910584 | chr19 | 47933223 | 47933822 |
| chr19 | 48003512 | 48003747 | chr19 | 48076568 | 48076747 | chr19 | 48137090 | 48137187 |
| chr19 | 48137247 | 48137389 | chr19 | 48151189 | 48151421 | chr19 | 48614769 | 48614851 |
| chr19 | 48771496 | 48771636 | chr19 | 48800507 | 48800866 | chr19 | 48857809 | 48857917 |
| chr19 | 48902834 | 48902953 | chr19 | 48918040 | 48918339 | chr19 | 49119155 | 49119334 |
| chr19 | 49127285 | 49127764 | chr19 | 49180431 | 49180610 | chr19 | 49399126 | 49399414 |
| chr19 | 49575386 | 49575475 | chr19 | 49646062 | 49646116 | chr19 | 49646246 | 49646294 |
| chr19 | 49890810 | 49890908 | chr19 | 49935656 | 49936255 | chr19 | 49936828 | 49936969 |
| chr19 | 50028531 | 50028614 | chr19 | 50049635 | 50049746 | chr19 | 50215991 | 50216147 |
| chr19 | 50316147 | 50316566 | chr19 | 50353305 | 50353664 | chr19 | 50553917 | 50554516 |
| chr19 | 50816339 | 50816573 | chr19 | 50833750 | 50833966 | chr19 | 50938470 | 50938769 |
| chr19 | 51161151 | 51161330 | chr19 | 51162123 | 51162254 | chr19 | 51162428 | 51162602 |
| chr19 | 51171130 | 51171275 | chr19 | 51227633 | 51227872 | chr19 | 51227975 | 51228154 |
| chr19 | 51228229 | 51228269 | chr19 | 51228369 | 51228588 | chr19 | 51304487 | 51304666 |
| chr19 | 51520349 | 51520528 | chr19 | 51830748 | 51831003 | chr19 | 51831121 | 51831227 |
| chr19 | 51831286 | 51831465 | chr19 | 52097592 | $2097831 | chr19 | 52207162 | 52207461 |
| chr19 | 52222438 | 52222924 | chr19 | 52223143 | $2223192 | chr19 | 52552089 | 52552120 |
| chr19 | 52552234 | 52552248 | chr19 | 52839494 | 52839634 | chr19 | 52839700 | 52839718 |
| chr19 | $2839742 | 52839924 | chr19 | 52839926 | 52840033 | chr19 | 52872943 | 52873106 |
| chr19 | 52873108 | 52873534 | chr19 | 52956708 | 52956947 | chr19 | 53028835 | 53028952 |
| chr19 | 53031202 | 53031290 | chr19 | 53073476 | 53073773 | chr19 | 53073820 | 53073865 |
| chr19 | 53073867 | 53074075 | chr19 | 53141533 | 53141619 | chr19 | 53141648 | 53141832 |
| chr19 | 53193757 | 53193996 | chr19 | 53194190 | 53194366 | chr19 | 53496630 | 53496787 |
| chr19 | 53496814 | 53496928 | chr19 | 53561582 | 53561821 | chr19 | 53635873 | 53636108 |
| chr19 | 53636110 | 53636168 | chr19 | 53661566 | 53661865 | chr19 | 53662195 | 53662722 |
| chr19 | 53696318 | 53696649 | chr19 | 53696651 | 53696677 | chr19 | 53700514 | 53700693 |
| chr19 | 53757802 | 53758341 | chr19 | 53811774 | 53811986 | chr19 | 53836837 | 53836912 |
| chr19 | 53970464 | 53970636 | chr19 | 53970884 | 53971040 | chr19 | 53971110 | 53971243 |
| chr19 | 54023803 | 54023999 | chr19 | 54024001 | 54024282 | chr19 | 54024434 | 54024553 |
| chr19 | 54024619 | 54024973 | chr19 | 54411032 | 54411267 | chr19 | 54411482 | 54411661 |
| chr19 | 54412809 | 54412992 | chr19 | 54413009 | 54413079 | chr19 | 54445250 | 54445297 |
| chr19 | 54445559 | 54445609 | chr19 | 54481691 | 54482050 | chr19 | 54483091 | 54483188 |
| chr19 | 54483190 | 54483306 | chr19 | 54483365 | 54483532 | chr19 | 54483534 | 54483630 |
| chr19 | 54485442 | 54485647 | chr19 | 54485673 | 54485913 | chr19 | 56159350 | 56159596 |
| chr19 | 56201573 | 56201812 | chr19 | 56588806 | 56588868 | chr19 | 56728588 | 56728603 |
| chr19 | 56728659 | 56728789 | chr19 | 56879475 | 56879554 | chr19 | 56879556 | 56879645 |
| chr19 | 56879647 | 56879994 | chr19 | 56879996 | 56880075 | chr19 | 56904643 | 56904704 |
| chr19 | 56904724 | 56904997 | chr19 | 56904999 | 56905302 | chr19 | 56915225 | 56915524 |
| chr19 | 56988458 | 56988664 | chr19 | 56989502 | 56989626 | chr19 | 56989697 | 56989851 |
| chr19 | 57060429 | 57050568 | chr19 | 57149480 | 57149719 | chr19 | 57154802 | 57155101 |
| chr19 | 57182906 | 57183127 | chr19 | 57183374 | 57183423 | chr19 | 57276559 | 57276798 |
| chr19 | 57610771 | 57610828 | chr19 | 57610896 | 57611067 | chr19 | 57617433 | 57617716 |
| chr19 | 57617832 | 57618170 | chr19 | 57683078 | 57683163 | chr19 | 57683240 | 57683372 |
| chr19 | 57862330 | 57862638 | chr19 | 57862640 | 57862859 | chr19 | 57862930 | 57862958 |
| chr19 | 57863222 | 57863229 | chr19 | 58011040 | 58011345 | chr19 | 58011347 | 58011383 |
| chr19 | 58038924 | 58039067 | chr19 | 58094925 | 58095468 | chr19 | 58095470 | 58095931 |
| chr19 | 58111529 | 58111888 | chr19 | 58125444 | 58125983 | chr19 | 58144419 | 58:44778 |
| chr19 | 58219924 | 58220393 | chr19 | 58220516 | 58220883 | chr19 | 58238234 | 58238739 |
| chr19 | 58238988 | 58239012 | chr19 | 58239014 | 58239187 | chr19 | 58399978 | 58400277 |
| chr19 | 58400319 | 58400618 | chr19 | 58458679 | 58458891 | chr19 | 58458979 | 58459278 |
| chr19 | 58514416 | 58514655 | chr19 | 58520661 | 58521020 | chr19 | 58545042 | 58545388 |
| chr19 | 58545578 | 58545590 | chr19 | 58545652 | 58545843 | chr19 | 58609299 | 58609360 |
| chr19 | 58609473 | 58609526 | chr19 | 58609713 | 58609744 | chr19 | 58609746 | 58609944 |
| chr19 | 58629812 | 58629864 | chr19 | 58629975 | 58630026 | chr19 | 58661815 | 58662174 |
| chr19 | 58666093 | 58666392 | chr19 | 58739983 | 58740222 | chr19 | 58874834 | 58874951 |
| chr19 | 58907613 | 58907637 | chr19 | 58951175 | 58951401 | chr19 | 58951526 | 58951599 |
| chr19 | 58951601 | 58951778 | chr19 | 58951780 | 58952014 | chr19 | 58964105 | 58964283 |
| chr20 | 291052 | 291163 | chr20 | 291221 | 291453 | chr20 | 399928 | 400167 |
| chr20 | 401079 | 401258 | chr20 | 401495 | 401854 | chr20 | 590349 | 590588 |
| chr20 | 592323 | 592547 | chr20 | 644553 | 644826 | chr20 | 799030 | 799146 |
| chr20 | 982660 | 982799 | chr20 | 982892 | 983079 | chr20 | 1206766 | 1207125 |
| chr20 | 1783674 | 1784306 | chr20 | 2539252 | 2539552 | chr20 | 2539554 | 2539851 |
| chr20 | 2668670 | 2669026 | chr20 | 2780654 | 2780747 | chr20 | 2780894 | 2781122 |
| chr20 | 2781124 | 2781553 | chr20 | 2781657 | 2781836 | chr20 | 2785561 | 2785867 |
| chr20 | 2785956 | 2786160 | chr20 | 3027666 | 3027780 | chr20 | 3052501 | 3052692 |
| chr20 | 3052694 | 3052920 | chr20 | 3073561 | 3073994 | chr20 | 3204792 | 3205031 |

TABLE 15-continued

| chr | start | end | chr | start | end | chr | start | end |
|---|---|---|---|---|---|---|---|---|
| chr20 | 3220799 | 3221038 | chr20 | 3229475 | 3229480 | chr20 | 3229527 | 3229714 |
| chr20 | 3641774 | 3642015 | chr20 | 3662918 | 3663277 | chr20 | 4084983 | 4085146 |
| chr20 | 4229328 | 4229507 | chr20 | 4229684 | 4230684 | chr20 | 4802971 | 4803750 |
| chr20 | 4803846 | 4804053 | chr20 | 5296095 | 5296986 | chr20 | 5297226 | 5297419 |
| chr20 | 5297673 | 5297705 | chr20 | 6022813 | 6023052 | chr20 | 6748832 | 6749131 |
| chr20 | 8112304 | 8112483 | chr20 | 8112642 | 8113121 | chr20 | 8113462 | 8113701 |
| chr20 | 9487302 | 9487720 | chr20 | 9487789 | 9488032 | chr20 | 9488329 | 9488613 |
| chr20 | 9488650 | 9488934 | chr20 | 9488993 | 9489249 | chr20 | 9489377 | 9489796 |
| chr20 | 9495181 | 9495572 | chr20 | 9495574 | 9495600 | chr20 | 9496253 | 9496531 |
| chr20 | 9496581 | 9496912 | chr20 | 9496953 | 9497074 | chr20 | 10198206 | 10198685 |
| chr20 | 10198941 | 10199020 | chr20 | 13200498 | 13200737 | chr20 | 16555037 | 16555130 |
| chr20 | 17206434 | 17206840 | chr20 | 17207783 | 17208022 | chr20 | 17208484 | 17208657 |
| chr20 | 18039741 | 18039980 | chr20 | 19739495 | 19739566 | chr20 | 19739613 | 19739794 |
| chr20 | 19928211 | 19928450 | chr20 | 20344410 | 20344649 | chr20 | 20345597 | 20345631 |
| chr20 | 20346167 | 20346176 | chr20 | 20347358 | 20347710 | chr20 | 20347737 | 20348222 |
| chr20 | 20348447 | 20348686 | chr20 | 20349055 | 20349354 | chr20 | 20349500 | 20349679 |
| chr20 | 21080615 | 21080957 | chr20 | 21081029 | 21081845 | chr20 | 21082095 | 21082124 |
| chr20 | 21082216 | 21082354 | chr20 | 21082456 | 21082995 | chr20 | 21083322 | 21084461 |
| chr20 | 21085768 | 21085968 | chr20 | 21086075 | 21086152 | chr20 | 21086195 | 21086554 |
| chr20 | 21086808 | 21087267 | chr20 | 21372091 | 21372193 | chr20 | 21372295 | 21372810 |
| chr20 | 21376172 | 21376337 | chr20 | 21376703 | 21376734 | chr20 | 21376877 | 21377129 |
| chr20 | 21377474 | 21377641 | chr20 | 21377738 | 21378631 | chr20 | 21486299 | 21486660 |
| chr20 | 21486786 | 21486917 | chr20 | 21486955 | 21486958 | chr20 | 21487068 | 21487276 |
| chr20 | 21487368 | 21487667 | chr20 | 21488076 | 21488435 | chr20 | 21489135 | 21489159 |
| chr20 | 21489240 | 21489447 | chr20 | 21489622 | 21489794 | chr20 | 21490099 | 21490763 |
| chr20 | 21490815 | 21491346 | chr20 | 21491617 | 21491632 | chr20 | 21492309 | 21492410 |
| chr20 | 21492508 | 21492826 | chr20 | 21492991 | 21493071 | chr20 | 21493218 | 21493994 |
| chr20 | 21494438 | 21494797 | chr20 | 21495845 | 21496084 | chr20 | 21496158 | 21496397 |
| chr20 | 21496684 | 21497217 | chr20 | 21497337 | 21498716 | chr20 | 21500019 | 21500228 |
| chr20 | 21501294 | 21501360 | chr20 | 21501445 | 21501814 | chr20 | 21501945 | 21502145 |
| chr20 | 21502495 | 21502700 | chr20 | 21502838 | 21503174 | chr20 | 21503490 | 21503877 |
| chr20 | 21682309 | 21682329 | chr20 | 21682362 | 21682548 | chr20 | 21683213 | 21683751 |
| chr20 | 21685592 | 21685606 | chr20 | 21686157 | 21686293 | chr20 | 21686295 | 21686756 |
| chr20 | 21686921 | 21687383 | chr20 | 21687756 | 21687820 | chr20 | 21689862 | 21690137 |
| chr20 | 21694425 | 21694604 | chr20 | 21695014 | 21695274 | chr20 | 21695306 | 21695391 |
| chr20 | 21748349 | 21748588 | chr20 | 22557301 | 22557776 | chr20 | 22557898 | 22558197 |
| chr20 | 22558534 | 22658773 | chr20 | 22559549 | 22559676 | chr20 | 22559678 | 22559788 |
| chr20 | 22562632 | 22562885 | chr20 | 22563690 | 22563703 | chr20 | 22564161 | 22564291 |
| chr20 | 23015843 | 23015942 | chr20 | 23029012 | 23029232 | chr20 | 23029589 | 23030086 |
| chr20 | 23030292 | 23030442 | chr20 | 23031471 | 23031729 | chr20 | 24450133 | 24450612 |
| chr20 | 24450692 | 24450704 | chr20 | 24450820 | 24451084 | chr20 | 24451086 | 24451111 |
| chr20 | 24451372 | 24451671 | chr20 | 25058292 | 25058711 | chr20 | 25061654 | 25061789 |
| chr20 | 25061979 | 25062312 | chr20 | 25062511 | 25062646 | chr20 | 25062708 | 25062818 |
| chr20 | 25062871 | 25062973 | chr20 | 25063700 | 25063907 | chr20 | 25063994 | 25064539 |
| chr20 | 25065078 | 25065207 | chr20 | 25065209 | 25065497 | chr20 | 25129465 | 25129520 |
| chr20 | 25129522 | 25129544 | chr20 | 25230415 | 25230513 | chr20 | 25230775 | 25230894 |
| chr20 | 26188813 | 26188962 | chr20 | 26190218 | 26190432 | chr20 | 30101724 | 30101833 |
| chr20 | 30582655 | 30583074 | chr20 | 30639051 | 30539410 | chr20 | 30639531 | 30639570 |
| chr20 | 30639603 | 30639950 | chr20 | 30640009 | 30640256 | chr20 | 30640258 | 30640368 |
| chr20 | 30777930 | 30278339 | chr20 | 31115592 | 31115891 | chr20 | 31151695 | 31151874 |
| chr20 | 32301800 | 32302039 | chr20 | 32450399 | 32450518 | chr20 | 33547579 | 33547685 |
| chr20 | 33574834 | 33574981 | chr20 | 34041903 | 34042004 | chr20 | 34147928 | 34148347 |
| chr20 | 34188525 | 34188632 | chr20 | 34188748 | 34189089 | chr20 | 34189167 | 34189484 |
| chr20 | 34189680 | 34190013 | chr20 | 36531706 | 36532005 | chr20 | 36781250 | 36781429 |
| chr20 | 37302601 | 37303440 | chr20 | 37351701 | 37352516 | chr20 | 37352607 | 37352720 |
| chr20 | 37353096 | 37353335 | chr20 | 37353378 | 37353719 | chr20 | 37353807 | 37353857 |
| chr20 | 37354045 | 37354832 | chr20 | 37354994 | 37355304 | chr20 | 37355761 | 37356043 |
| chr20 | 37356169 | 37356828 | chr20 | 37357216 | 37357440 | chr20 | 37357739 | 37358278 |
| chr20 | 37434489 | 37434722 | chr20 | 37434737 | 37434828 | chr20 | 37435012 | 37435311 |
| chr20 | 37435362 | 37435370 | chr20 | 37435488 | 37435716 | chr20 | 37435718 | 37435961 |
| chr20 | 39316114 | 39316413 | chr20 | 39316814 | 39316853 | chr20 | 39316984 | 39317034 |
| chr20 | 39317036 | 39317473 | chr20 | 39317659 | 39318138 | chr20 | 39319031 | 39319204 |
| chr20 | 39319515 | 39319750 | chr20 | 39995061 | 39995546 | chr20 | 39995548 | 39995900 |
| chr20 | 41817697 | 41817916 | chr20 | 41818008 | 41818176 | chr20 | 41818472 | 41818749 |
| chr20 | 41818805 | 41819011 | chr20 | 42136252 | 42136491 | chr20 | 42218593 | 42218757 |
| chr20 | 42543655 | 42543954 | chr20 | 42543999 | 42544534 | chr20 | 42544728 | 42545078 |
| chr20 | 42876457 | 42876670 | chr20 | 43437970 | 43438086 | chr20 | 43438335 | 43438569 |
| chr20 | 43438883 | 43439122 | chr20 | 43439192 | 43439219 | chr20 | 43439248 | 43439611 |
| chr20 | 44452666 | 44453152 | chr20 | 44519003 | 44519182 | chr20 | 44601980 | 44602069 |
| chr20 | 44639100 | 44639579 | chr20 | 44640264 | 44640288 | chr20 | 44640313 | 44640443 |
| chr20 | 44660665 | 44660964 | chr20 | 44686423 | 44686615 | chr20 | 44686628 | 44686866 |
| chr20 | 44803096 | 44803126 | chr20 | 44803173 | 44803755 | chr20 | 44879700 | 44879791 |
| chr20 | 44880041 | 44880167 | chr20 | 44937124 | 44937369 | chr20 | 44937444 | 44937723 |
| chr20 | 44941441 | 44941740 | chr20 | 45141897 | 45142039 | chr20 | 45142152 | 45142244 |
| chr20 | 45142246 | 45142331 | chr20 | 45279779 | 45279982 | chr20 | 45280040 | 45280491 |
| chr20 | 45337726 | 45338025 | chr20 | 45524449 | 45524628 | chr20 | 47247136 | 47247407 |
| chr20 | 47274032 | 47274137 | chr20 | 47296021 | 47296320 | chr20 | 47443647 | 47443937 |
| chr20 | 47443945 | 47444241 | chr20 | 47444243 | 47444366 | chr20 | 47905336 | 47905687 |

TABLE 15-continued

| chr | start | end | chr | start | end | chr | start | end |
|---|---|---|---|---|---|---|---|---|
| chr20 | 47934747 | 47934987 | chr20 | 47934989 | 47935346 | chr20 | 47935412 | 47935651 |
| chr20 | 47935829 | 47936128 | chr20 | 48184289 | 48184292 | chr20 | 48184329 | 48184528 |
| chr20 | 49204105 | 49204524 | chr20 | 49261715 | 49262194 | chr20 | 49358363 | 49358477 |
| chr20 | 49377912 | 49378139 | chr20 | 49381177 | 49381340 | chr20 | 49575835 | 49575938 |
| chr20 | 49575988 | 49576014 | chr20 | 49639698 | 49639857 | chr20 | 49639883 | 49639997 |
| chr20 | 49640095 | 49640237 | chr20 | 50383399 | 50383504 | chr20 | 50384683 | 50384982 |
| chr20 | 50720356 | 50721201 | chr20 | 50721235 | 50721671 | chr20 | 50721989 | 50722021 |
| chr20 | 50722096 | 50722201 | chr20 | 50722609 | 50722908 | chr20 | 51589688 | 51589987 |
| chr20 | 52311387 | 52311505 | chr20 | 52789371 | 52789550 | chr20 | 52789765 | 52789949 |
| chr20 | 52790082 | 52790244 | chr20 | 53092165 | 53092233 | chr20 | 53092235 | 53092334 |
| chr20 | 53092336 | 53092464 | chr20 | 53093011 | 53093190 | chr20 | 54578407 | 54578826 |
| chr20 | 54579809 | 54579959 | chr20 | 54580070 | 54580408 | chr20 | 54580484 | 54580522 |
| chr20 | 54580622 | 54580783 | chr20 | 55199952 | 55200311 | chr20 | 55200616 | 55200791 |
| chr20 | 55200828 | 55201187 | chr20 | 55201451 | 55201452 | chr20 | 55201581 | 55201638 |
| chr20 | 55201686 | 55202069 | chr20 | 55202359 | 55202705 | chr20 | 55202728 | 55203207 |
| chr20 | 55204224 | 55204703 | chr20 | 55204864 | 55205103 | chr20 | 55206294 | 55206430 |
| chr20 | 55206464 | 55206495 | chr20 | 55499394 | 55499813 | chr20 | 55499932 | 55500171 |
| chr20 | 55500441 | 55500670 | chr20 | 55500672 | 55500721 | chr20 | 55693446 | 55693610 |
| chr20 | 55841036 | 55841455 | chr20 | 55842056 | 55842293 | chr20 | 56766086 | 56766203 |
| chr20 | 56803301 | 56803540 | chr20 | 56803762 | 56804001 | chr20 | 57089355 | 57089460 |
| chr20 | 57090104 | 57090259 | chr20 | 57224799 | 57225080 | chr20 | 57225219 | 57225405 |
| chr20 | 58152557 | 58152559 | chr20 | 58152776 | 58152796 | chr20 | 58179713 | 58179952 |
| chr20 | 58180214 | 58180403 | chr20 | 58180471 | 58180497 | chr20 | 58508796 | 58509005 |
| chr20 | 59804233 | 59804323 | chr20 | 59826885 | 59826978 | chr20 | 59828341 | 59828408 |
| chr20 | 598804.80 | 59880575 | chr20 | 59910084 | 59910441 | chr20 | 59972951 | 59973170 |
| chr20 | 60202541 | 60202699 | chr20 | 60235251 | 60236610 | chr20 | 60238278 | 60238574 |
| chr20 | 60238780 | 60239079 | chr20 | 60243850 | 60244206 | chr20 | 60329482 | 60329661 |
| chr20 | 60359835 | 60359954 | chr20 | 60374934 | 60375173 | chr20 | 60439546 | 60439845 |
| chr20 | 60453829 | 60454186 | chr20 | 60477213 | 60477632 | chr20 | 60485281 | 60485480 |
| chr20 | 60502956 | 60503135 | chr20 | 60620233 | 60620412 | chr20 | 60772886 | 60773905 |
| chr20 | 60789866 | 60790225 | chr20 | 60925945 | 60926124 | chr20 | 60970879 | 60971058 |
| chr20 | 60983756 | 60984115 | chr20 | 60984356 | 60984553 | chr20 | 61287993 | 61288232 |
| chr20 | 61288380 | 61288619 | chr20 | 61294596 | 61294955 | chr20 | 61340486 | 61340785 |
| chr20 | 61412227 | 61412451 | chr20 | 61505882 | 61506421 | chr20 | 61532457 | 61532696 |
| chr20 | 61560341 | 61560461 | chr20 | 61560529 | 61561000 | chr20 | 61636755 | 61636779 |
| chr20 | 61636876 | 61636994 | chr20 | 61637391 | 61637649 | chr20 | 61637736 | 61637957 |
| chr20 | 61638221 | 61638470 | chr20 | 61638535 | 61638710 | chr20 | 61703710 | 61703762 |
| chr20 | 61703846 | 61703972 | chr20 | 61714683 | 61714696 | chr20 | 61734332 | 61734571 |
| chr20 | 61747795 | 61748034 | chr20 | 61763524 | 61763703 | chr20 | 61765251 | 61765490 |
| chr20 | 61808107 | 61808346 | chr20 | 61808667 | 61808888 | chr20 | 61808890 | 61809006 |
| chr20 | 61809219 | 61809557 | chr20 | 61809559 | 61809632 | chr20 | 61809841 | 61810135 |
| chr20 | 61810160 | 61810187 | chr20 | 61823076 | 61823195 | chr20 | 61862297 | 61862460 |
| chr20 | 61885196 | 61885291 | chr20 | 61885293 | 61885551 | chr20 | 61885778 | 61885848 |
| chr20 | 61885984 | 61886204 | chr20 | 61886257 | 61886343 | chr20 | 61886651 | 61886830 |
| chr20 | 61974094 | 61974453 | chr20 | 61980769 | 61981068 | chr20 | 62031085 | 62031324 |
| chr20 | 62031958 | 62032197 | chr20 | 62037460 | 62037699 | chr20 | 62046145 | 62046504 |
| chr20 | 62058624 | 62058859 | chr20 | 62090442 | 62090621 | chr20 | 62097763 | 62097771 |
| chr20 | 62115188 | 62115367 | chr20 | 62119246 | 62119619 | chr20 | 62119923 | 62120252 |
| chr20 | 62126035 | 62126514 | chr20 | 62157232 | 62157349 | chr20 | 62165548 | 62165847 |
| chr20 | 62167480 | 62167659 | chr20 | 62170105 | 62170284 | chr20 | 62172851 | 62173150 |
| chr20 | 62185296 | 62185535 | chr20 | 62321125 | 62321424 | chr20 | 62321551 | 62321970 |
| chr20 | 62340233 | 62340423 | chr20 | 62383135 | 62383374 | chr20 | 62461263 | 62461562 |
| chr20 | 62488263 | 62488442 | chr20 | 62680682 | 62680818 | chr20 | 62714923 | 62714946 |
| chr20 | 62715097 | 62715162 | chr21 | 22370246 | 22370347 | chr21 | 22370349 | 22370476 |
| chr21 | 22370614 | 22370733 | chr21 | 22370735 | 22370793 | chr21 | 26934278 | 26934877 |
| chr21 | 27011671 | 27011910 | chr21 | 27012283 | 27012522 | chr21 | 27944919 | 27945148 |
| chr21 | 27945619 | 27945798 | chr21 | 28216509 | 28216583 | chr21 | 28216634 | 28217768 |
| chr21 | 28218671 | 28218815 | chr21 | 28218877 | 28219150 | chr21 | 28338743 | 28338848 |
| chr21 | 28339165 | 28339584 | chr21 | 28339806 | 28339907 | chr21 | 28339909 | 28340049 |
| chr21 | 28340063 | 28340405 | chr21 | 31015127 | 31015306 | chr21 | 31311387 | 31311629 |
| chr21 | 31311846 | 31311920 | chr21 | 31312080 | 31312205 | chr21 | 31312230 | 31312259 |
| chr21 | 31312305 | 31312409 | chr21 | 33244901 | 33245131 | chr21 | 33245582 | 33245593 |
| chr21 | 33245716 | 33245821 | chr21 | 33245921 | 33245955 | chr21 | 33246038 | 33246280 |
| chr21 | 33627450 | 33627569 | chr21 | 33721671 | 33721910 | chr21 | 33983153 | 33983320 |
| chr21 | 34392070 | 34392168 | chr21 | 34392206 | 34392404 | chr21 | 34392437 | 34392669 |
| chr21 | 34395217 | 34396356 | chr21 | 34396702 | 34396870 | chr21 | 34396903 | 34397178 |
| chr21 | 34397993 | 34398131 | chr21 | 34398133 | 34398199 | chr21 | 34398201 | 34398222 |
| chr21 | 34398224 | 34398712 | chr21 | 34398847 | 34399259 | chr21 | 34399442 | 34400105 |
| chr21 | 34400232 | 34400346 | chr21 | 34401110 | 34401469 | chr21 | 34442595 | 34442696 |
| chr21 | 34443004 | 34443363 | chr21 | 34443419 | 34443778 | chr21 | 34443806 | 34444045 |
| chr21 | 34444082 | 34444363 | chr21 | 34444445 | 34444681 | chr21 | 36041934 | 36042029 |
| chr21 | 36042092 | 36042170 | chr21 | 36042172 | 36042322 | chr21 | 36042581 | 36042940 |
| chr21 | 37527854 | 37528033 | chr21 | 37758492 | 37758611 | chr21 | 37774963 | 37775238 |
| chr21 | 38064415 | 38064714 | chr21 | 38064917 | 38065523 | chr21 | 38065800 | 38065832 |
| chr21 | 38065855 | 38066214 | chr21 | 38067247 | 38067308 | chr21 | 38068092 | 38068230 |
| chr21 | 38068647 | 38068871 | chr21 | 38069125 | 38069298 | chr21 | 38069359 | 38069598 |
| chr21 | 38069725 | 38069806 | chr21 | 38069854 | 38070144 | chr21 | 38070616 | 38070855 |
| chr21 | 38071699 | 38071781 | chr21 | 38071933 | 38071998 | chr21 | 38072920 | 38073159 |

TABLE 15-continued

| chr | start | end | chr | start | end | chr | start | end |
|---|---|---|---|---|---|---|---|---|
| chr21 | 38073240 | 38073526 | chr21 | 38073616 | 38073940 | chr21 | 38077207 | 38077243 |
| chr21 | 38078332 | 38078571 | chr21 | 38079887 | 38080063 | chr21 | 38080175 | 38080387 |
| chr21 | 38080551 | 38080786 | chr21 | 38081112 | 38081193 | chr21 | 38081666 | 38081910 |
| chr21 | 38081968 | 38082011 | chr21 | 38082854 | 38083258 | chr21 | 38092081 | 38092320 |
| chr21 | 38119809 | 38120408 | chr21 | 38638505 | 38638624 | chr21 | 38935395 | 38935601 |
| chr21 | 39047688 | 39047889 | chr21 | 40984719 | 40984898 | chr21 | 43376299 | 43376478 |
| chr21 | 43786609 | 43786788 | chr21 | 43991389 | 43991568 | chr21 | 44283611 | 44283850 |
| chr21 | 44494941 | 44494997 | chr21 | 44494999 | 44495233 | chr21 | 44837002 | 44837245 |
| chr21 | 44837296 | 44837301 | chr21 | 44847488 | 44847606 | chr21 | 44847608 | 44847727 |
| chr21 | 44866508 | 44866807 | chr21 | 45148538 | 45148837 | chr21 | 45195115 | 45195414 |
| chr21 | 45273636 | 45273995 | chr21 | 45508543 | 45508662 | chr21 | 45791005 | 45791184 |
| chr21 | 46036556 | 46036855 | chr21 | 46126388 | 46126428 | chr21 | 46126567 | 46126807 |
| chr21 | 46126948 | 46127187 | chr21 | 46127468 | 46127628 | chr21 | 46128801 | 46129040 |
| chr21 | 46129346 | 46129585 | chr21 | 46257016 | 46257375 | chr21 | 46310341 | 46310580 |
| chr21 | 46318196 | 46318435 | chr21 | 46319069 | 46319548 | chr21 | 46359099 | 46359338 |
| chr21 | 46452278 | 46452637 | chr21 | 46677646 | 46677885 | chr21 | 46825737 | 46825823 |
| chr21 | 46863675 | 46863803 | chr21 | 46925704 | 46925999 | chr21 | 46926363 | 46926662 |
| chr21 | 46935727 | 46936018 | chr21 | 47010409 | 47010527 | chr21 | 47062753 | 47062925 |
| chr21 | 47063451 | 47064050 | chr21 | 47064165 | 47064464 | chr21 | 47404071 | 47404429 |
| chr21 | 47504759 | 47504994 | chr21 | 47518676 | 47518866 | chr21 | 47518888 | 47518915 |
| chr21 | 47717486 | 47717541 | chr21 | 47717623 | 47717665 | chr21 | 47746183 | 47746482 |
| chr22 | 17081848 | 17081936 | chr22 | 17082069 | 17082087 | chr22 | 17082492 | 17082524 |
| chr22 | 17082854 | 17082894 | chr22 | 17082989 | 17083062 | chr22 | 17083297 | 17083411 |
| chr22 | 17083525 | 17083596 | chr22 | 17600988 | 17601134 | chr22 | 17601260 | 17601467 |
| chr22 | 17602419 | 17602718 | chr22 | 17850359 | 17850718 | chr22 | 18009986 | 18010085 |
| chr22 | 18328049 | 18328348 | chr22 | 19017431 | 19017670 | chr22 | 19117490 | 19117669 |
| chr22 | 19510704 | 19510947 | chr22 | 19511142 | 19511456 | chr22 | 19511542 | 19511663 |
| chr22 | 19511765 | 19511876 | chr22 | 19706119 | 19706365 | chr22 | 19706367 | 19706754 |
| chr22 | 19742753 | 19742758 | chr22 | 19742789 | 19743052 | chr22 | 19748561 | 19748909 |
| chr22 | 19748961 | 19749040 | chr22 | 20792482 | 20792689 | chr22 | 21153919 | 21154084 |
| chr22 | 21304980 | 21305098 | chr22 | 21368513 | 21368692 | chr22 | 21977249 | 21977451 |
| chr22 | 21982708 | 21983062 | chr22 | 22006004 | 12006243 | chr22 | 22058102 | 22058341 |
| chr22 | 22090520 | 22090528 | chr22 | 22862704 | 22862863 | chr22 | 22863220 | 22863243 |
| chr22 | 22901011 | 22901550 | chr22 | 23791328 | 23791507 | chr22 | 23801388 | 23801567 |
| chr22 | 24180608 | 24180847 | chr22 | 24560283 | 24560522 | chr22 | 24820244 | 24820483 |
| chr22 | 25678654 | 25678869 | chr22 | 25679043 | 25679250 | chr22 | 25679268 | 25679433 |
| chr22 | 25817025 | 25817264 | chr22 | 25817356 | 25817715 | chr22 | 28198468 | 28198601 |
| chr22 | 28371575 | 28371754 | chr22 | 28838105 | 28838396 | chr22 | 28838411 | 28838524 |
| chr22 | 29091752 | 29091929 | chr22 | 29445659 | 29446018 | chr22 | 29876117 | 29876189 |
| chr22 | 29877142 | 29877381 | chr22 | 29977650 | 29977755 | chr22 | 30116824 | 30117147 |
| chr22 | 30158246 | 30158365 | chr22 | 30938434 | 30938507 | chr22 | 30938543 | 30938673 |
| chr22 | 31198416 | 31198715 | chr22 | 31218436 | 31218615 | chr22 | 31218693 | 31218932 |
| chr22 | 31481052 | 31481411 | chr22 | 32748862 | 32749041 | chr22 | 33197509 | 33197748 |
| chr22 | 33453802 | 33454075 | chr22 | 33454194 | 33454259 | chr22 | 33454346 | 33454452 |
| chr22 | 35848275 | 35848476 | chr22 | 36902217 | 36902456 | chr22 | 38199683 | 38199982 |
| chr22 | 38220568 | 38221287 | chr22 | 38476983 | 38477132 | chr22 | 38477297 | 38477882 |
| chr22 | 38592953 | 38593132 | chr22 | 38639155 | 38639308 | chr22 | 39784390 | 39784599 |
| chr22 | 39830257 | 39830492 | chr22 | 39853438 | 39853590 | chr22 | 39853592 | 39853657 |
| chr22 | 39932459 | 39932638 | chr22 | 39954323 | 39954400 | chr22 | 39954429 | 39954615 |
| chr22 | 40042536 | 40042835 | chr22 | 40075089 | 40075328 | chr22 | 40226368 | 40226487 |
| chr22 | 41048654 | 41048951 | chr22 | 41634334 | 41634618 | chr22 | 41636999 | 41637217 |
| chr22 | 41657217 | 41657442 | chr22 | 42095992 | 42096276 | chr22 | 42310005 | 42310304 |
| chr22 | 42311435 | 42311674 | chr22 | 42353530 | 42353992 | chr22 | 42667276 | 42667501 |
| chr22 | 42679917 | 42679935 | chr22 | 43012441 | 43012560 | chr22 | 43012883 | 43012980 |
| chr22 | 43083029 | 43083145 | chr22 | 43434340 | 43434579 | chr22 | 43739987 | 43740226 |
| chr22 | 43808205 | 43808502 | chr22 | 44208422 | 44208523 | chr22 | 44258287 | 44258586 |
| chr22 | 44287554 | 44287793 | chr22 | 44455605 | 44455844 | chr22 | 45088524 | 45088823 |
| chr22 | 45135854 | 45136079 | chr22 | 45277218 | 45277397 | chr22 | 45402991 | 45403230 |
| chr22 | 45404106 | 45404525 | chr22 | 45404909 | 45405011 | chr22 | 45405047 | 45405148 |
| chr22 | 45405219 | 45405432 | chr22 | 45405477 | 45405518 | chr22 | 45405545 | 45405627 |
| chr22 | 45405629 | 45405803 | chr22 | 45406181 | 45406420 | chr22 | 45593572 | 45593799 |
| chr22 | 45604107 | 45604444 | chr22 | 46262368 | 46263052 | chr22 | 46263512 | 46263624 |
| chr22 | 46263744 | 46263911 | chr22 | 46367955 | 46367987 | chr22 | 46368103 | 46368124 |
| chr22 | 46438002 | 46438112 | chr22 | 46658700 | 46658743 | chr22 | 46931177 | 46931336 |
| chr22 | 46933014 | 46933104 | chr22 | 47004998 | 47005237 | chr22 | 47023028 | 47023267 |
| chr22 | 47054612 | 47054700 | chr22 | 47193234 | 47193473 | chr22 | 47525747 | 47525986 |
| chr22 | 48027582 | 48027731 | chr22 | 48884960 | 48884960 | chr22 | 48885530 | 48885838 |
| chr22 | 48885908 | 48885989 | chr22 | 48886575 | 48886934 | chr22 | 48931805 | 48932104 |
| chr22 | 48971533 | 48971680 | chr22 | 48971759 | 48971829 | chr22 | 48972042 | 48972136 |
| chr22 | 48972220 | 48972466 | chr22 | 49852543 | 49852722 | chr22 | 49979553 | 49979835 |
| chr22 | 50001612 | 50001912 | chr22 | 50002684 | 50002911 | chr22 | 50003130 | 50003309 |
| chr22 | 50010037 | 50010336 | chr22 | 50010374 | 50010673 | chr22 | 50031617 | 50031796 |
| chr22 | 50149332 | 50149548 | chr22 | 50466931 | 50467045 | chr22 | 50496972 | 50497000 |
| chr22 | 50497068 | 50497183 | chr22 | 50497214 | 50497367 | chr22 | 50623613 | 50623715 |

TABLE 15-continued

| chr | start | end | chr | start | end | chr | start | end |
|---|---|---|---|---|---|---|---|---|
| chr22 | 50623742 | 50623894 | chr22 | 50899214 | 50899753 | chr22 | 50943082 | 50943358 |
| chr22 | 51042185 | 51042405 | chr22 | 51042458 | 51042566 | chr22 | 51112072 | 51112311 |
| chrX | 3746538 | 3746717 | chrX | 6145241 | 6145720 | chrX | 8698761 | 8699000 |
| chrX | 8699416 | 8699655 | chrX | 136656523 | 136656534 | AC211950.2_11234-25326 | 181 | 343 |
| AC211950.2_11234-25326 | 13241 | 13420 | AC211950.2_11234-25326 | 13667 | 13966 | AC241851.2_88-34049 | 15187 | 15426 |
| AEKP01168736.1_1-4752 | 1662 | 1781 | APKP01168736.1_1-4752 | 1874 | 2381 | JH636052.4 | 5118687 | 5118986 |
| NW_001838016.1_818233-828058 | 6095 | 6142 | — | — | — | — | — | — |

15

7. The method of claim 5, wherein at least 50 of the at least 500 target genomic regions are selected from one or more of Tables 16-24 as follows:

TABLE 16

| chr | start | end | chr | start | end | chr | start | end |
|---|---|---|---|---|---|---|---|---|
| chr1 | 15251121 | 15251211 | chr1 | 15480854 | 15480892 | chr1 | 64240031 | 64240118 |
| chr1 | 64240618 | 64240673 | chr1 | 183774245 | 183774363 | chr1 | 202183372 | 202183401 |
| chr1 | 214724532 | 214724561 | chr1 | 232765226 | 232765301 | chr1 | 233750126 | 233750302 |
| chr2 | 14772762 | 14772823 | chr2 | 14774475 | 14774567 | chr2 | 46526303 | 46526331 |
| chr2 | 75427370 | 75427399 | chr2 | 101436638 | 101436708 | chr2 | 103236166 | 103236277 |
| chr2 | 151342979 | 151343218 | chr2 | 171571265 | 171571315 | chr2 | 171571890 | 171571997 |
| chr2 | 189157513 | 189157617 | chr2 | 235860803 | 235860808 | chr2 | 236402772 | 236402901 |
| chr2 | 236403271 | 236403419 | chr2 | 238395907 | 238395961 | chr3 | 37901952 | 37901953 |
| chr3 | 45187297 | 45187328 | chr3 | 126373521 | 126373619 | chr3 | 126373669 | 126373704 |
| chr3 | 133748141 | 133748206 | chr3 | 133748552 | 133748576 | chr3 | 153838819 | 153838870 |
| chr3 | 153839519 | 153839559 | chr3 | 153839641 | 153839775 | chr3 | 171527953 | 171527971 |
| chr4 | 24914639 | 24914668 | chr4 | 152246133 | 152246237 | chr4 | 170947288 | 170947325 |
| chr4 | 84019693 | 184019736 | chr4 | 184020107 | 184020179 | chr5 | 34656933 | 34657034 |
| chr5 | 72416247 | 72416262 | chr5 | 72733094 | 72733185 | chr5 | 107005984 | 107006186 |
| chr5 | 121413538 | 121413590 | chr6 | 1312001 | 1312095 | chr6 | 1312680 | 1312708 |
| chr6 | 1314089 | 1314101 | chr6 | 26987968 | 26988166 | chr6 | 42928322 | 42928454 |
| chr7 | 27275514 | 27275532 | chr7 | 28995658 | 28995978 | chr7 | 28996458 | 28996495 |
| chr7 | 32997125 | 32997454 | chr7 | 50860227 | 50860393 | chr7 | 50860980 | 50861103 |
| chr7 | 51384328 | 51384440 | chr7 | 51384916 | 51384951 | chr7 | 55086481 | 55086601 |
| chr7 | 55086984 | 55087533 | chr7 | 121945823 | 121945920 | chr7 | 155602752 | 155602805 |
| chr8 | 25041747 | 25041864 | chr8 | 95651539 | 95651599 | chr8 | 95651637 | 95651655 |
| chr8 | 102505798 | 102505934 | chr8 | 120220429 | 120220592 | chr9 | 14312995 | 14313096 |
| chr9 | 21559295 | 21559381 | chr9 | 21559678 | 21559702 | chr9 | 38620642 | 38620725 |
| chr9 | 110251389 | 110251418 | chr9 | 110252364 | 110252455 | chr9 | 134421818 | 134421835 |
| chr10 | 21462534 | 21462607 | chr10 | 30026077 | 30026090 | chr10 | 33624167 | 33624230 |
| chr10 | 33624493 | 33624550 | chr10 | 72973131 | 72973180 | chr10 | 116164249 | 116164341 |
| chr11 | 12132525 | 12132659 | chr11 | 12399041 | 12399145 | chr11 | 12399181 | 12399222 |
| chr11 | 12695482 | 12695496 | chr11 | 12695573 | 12695611 | chr11 | 12696612 | 12696746 |
| chr11 | 16628820 | 16628933 | chr11 | 33037468 | 33037556 | chr11 | 66790622 | 66790655 |
| chr11 | 120039834 | 120039865 | chr11 | 129245747 | 129245810 | chr11 | 130318961 | 130318997 |
| chr11 | 134201503 | 134201543 | chr11 | 134201842 | 134202084 | chr11 | 16500577 | 16500621 |
| chr12 | 56882365 | 56882380 | chr12 | 107486551 | 107486672 | chr12 | 107487195 | 107487855 |
| chr12 | 107712274 | 107712303 | chr13 | 100634315 | 100634382 | chr14 | 34420251 | 34420288 |
| chr14 | 61747389 | 61747528 | chr14 | 61747583 | 61747816 | chr14 | 61748002 | 61748033 |
| chr15 | 62456923 | 62456952 | chr15 | 71055770 | 71055815 | chr15 | 96874363 | 96874416 |
| chr15 | 98504115 | 98504144 | chr15 | 99193297 | 99193345 | chr15 | 99193350 | 99193465 |
| chr16 | 54964949 | 54965114 | chr16 | 68771167 | 68771298 | chr16 | 80966400 | 80966431 |
| chr16 | 84402245 | 84402319 | chr16 | 84853289 | 84853376 | chr17 | 42061337 | 42061381 |
| chr17 | 72427854 | 72427963 | chr17 | 72428345 | 72428381 | chr17 | 75207840 | 75207944 |
| chr17 | 80693343 | 80693554 | chr18 | 19750309 | 19750346 | chr18 | 21269350 | 21269390 |
| chr18 | 21269660 | 21269740 | chr18 | 78005004 | 78005051 | chr19 | 462182 | 462235 |
| chr19 | 33792412 | 33792524 | chr20 | 1206856 | 1207034 | chr20 | 6748926 | 6749036 |
| chr20 | 18039824 | 18039897 | chr20 | 22564236 | 22564265 | chr20 | 50384768 | 50384896 |
| chr21 | 38070706 | 38070765 | chr22 | 31198493 | 31198637 | — | — | — |

TABLE 17

| chr | start | end | chr | start | end | chr | start | end |
|---|---|---|---|---|---|---|---|---|
| chr1 | 2336398 | 2336427 | chr1 | 2521025 | 2521062 | chr1 | 6507954 | 6508126 |
| chr1 | 21573736 | 21574203 | chr1 | 23885071 | 23885088 | chr1 | 155043332 | 155043657 |
| chr1 | 167823371 | 167823461 | chr1 | 185073819 | 185073966 | chr2 | 44497709. | 44497842 |

TABLE 17-continued

| chr | start | end | chr | start | end | chr | start | end |
|---|---|---|---|---|---|---|---|---|
| chr2 | 61135116 | 61135137 | chr2 | 127863602 | 127863725 | chr3 | 12977068 | 12977144 |
| chr3 | 183728814 | 183728926 | chr5 | 43007937 | 43007966 | chr5 | 176764101 | 176764169 |
| chr6 | 41773521 | 41773844 | chr6 | 43748464 | 43748616 | chr7 | 907657 | 907709 |
| chr7 | 6188652 | 6188831 | chr7 | 6188926 | 6189061 | chr7 | 55410020 | 55410126 |
| chr7 | 127371130 | 127371234 | chr7 | 129800244 | 129800434 | chr7 | 131041516 | 131041596 |
| chr7 | 134918504 | 134918637 | chr8 | 61777576 | 61777622 | chr8 | 142367673 | 142367790 |
| chr8 | 144668567 | 144668667 | chr8 | 144668910 | 144668972 | chr9 | 34224349 | 34224474 |
| chr9 | 34372806 | 34372983 | chr9 | 129401098 | 129401195 | chr9 | 139888946 | 139888980 |
| chr10 | 6003403 | 6003625 | chr10 | 22047362 | 22047601 | chr11 | 232864 | 233062 |
| chr11 | 63641073 | 63641104 | chr12 | 110353415 | 110353451 | chr13 | 28239910 | 28240164 |
| chr14 | 102564465 | 102564502 | chr16 | 380298 | 3803074 | chr16 | 85699690 | 85699921 |
| chr17 | 26961771 | 26961833 | chr17 | 42092191 | 42092220 | chr17 | 70026544 | 70026667 |
| chr18 | 74755509 | 74755577 | chr19 | 14181306 | 14181682 | chr19 | 33468019 | 33468055 |
| chr19 | 38782560 | 38782589 | chr19 | 40829794 | 40830032 | chr19 | 45570402 | 45570450 |
| chr19 | 45574774 | 45574782 | chr19 | 45574832 | 45574888 | chr20 | 6022813 | 6023045 |
| chr20 | 32301200 | 32301953 | chr20 | 60620233 | 60620412 | chr20 | 60772886 | 60773878 |
| chr21 | 37775035 | 37775141 | chr21 | 46935740 | 46935936 | chr22 | 21977315 | 21977347 |
| chr22 | 23801460 | 23801567 | chr22 | 24560376 | 24560522 | chr22 | 39830356 | 39830457 |
| chr22 | 41657234 | 41657350 | — | — | — | — | — | — |

TABLE 18

| chr | start | end | chr | start | end | chr | start | end |
|---|---|---|---|---|---|---|---|---|
| chr1 | 3659551 | 3659643 | chr1 | 3659672 | 3659716 | chr1 | 3663533 | 3663562 |
| chr1 | 12123244 | 12123276 | chr1 | 38511662 | 38511757 | chr2 | 12858453 | 12858499 |
| chr2 | 29338159 | 29338748 | chr2 | 29338810 | 29338969 | chr2 | 31360307 | 31360590 |
| chr2 | 31360631 | 31360693 | chr2 | 31360695 | 31360756 | chr2 | 31360804 | 31360831 |
| chr2 | 31456893 | 31457039 | chr2 | 100937837 | 100938164 | chr2 | 100938481 | 100938545 |
| chr2 | 100938575 | 100938799 | chr2 | 100938801 | 100938810 | chr2 | 100938985 | 100939155 |
| chr2 | 144694753 | 144695135 | chr2 | 172367022 | 172367125 | chr2 | 241542045 | 241542344 |
| chr3 | 142791152 | 142791173 | chr3 | 142839563 | 142839578 | chr3 | 142839580 | 142839607 |
| chr3 | 179168977 | 179169016 | chr4 | 718082 | 718112 | chr4 | 79689652 | 79689732 |
| chr4 | 156297417 | 156297556 | chr4 | 156297980 | 156298073 | chr5 | 38845676 | 38845705 |
| chr5 | 82769015 | 82769061 | chr5 | 111987788 | 111987818 | chr5 | 146257500 | 146257602 |
| chr6 | 73331516 | 73331851 | chr6 | 73331876 | 73332169 | chr6 | 73332392 | 73332674 |
| chr6 | 73332987 | 73333099 | chr6 | 127440332 | 127440510 | chr6 | 127440512 | 127440524 |
| chr6 | 151815056 | 151815089 | chr6 | 152957954 | 152957995 | chr6 | 163834315 | 163834383 |
| chr6 | 163834406 | 163834533 | chr6 | 163836569 | 163836900 | chr7 | 2728069 | 2728108 |
| chr7 | 28449277 | 28449291 | chr7 | 44364839 | 44364903 | chr7 | 69064591 | 69064772 |
| chr7 | 69064834 | 69064858 | chr7 | 76033251 | 76033289 | chr7 | 90226290 | 90226363 |
| chr7 | 106797775 | 106797804 | chr7 | 107483695 | 107483918 | chr7 | 134143808 | 134143908 |
| chr7 | 140027009 | 140027043 | chr7 | 149411542 | 149411728 | chr7 | 149411835 | 149412304 |
| chr7 | 150069099 | 150069346 | chr7 | 150070022 | 150070058 | chr8 | 53853998 | 53854207 |
| chr8 | 80803674 | 80803831 | chr8 | 97507150 | 97507246 | chr8 | 143533745 | 143533774 |
| chr9 | 37026964 | 37026993 | chr9 | 93698030 | 93698051 | chr9 | 140024843 | 140024919 |
| chr9 | 140024957 | 140025023 | chr10 | 3641379 | 3641396 | chr10 | 7450525 | 7450567 |
| chr10 | 7452350 | 7452550 | chr10 | 7453492 | 7453521 | chr10 | 49731643 | 49731749 |
| chr10 | 64578319 | 64578355 | chr10 | 101089410 | 101089439 | chr10 | 125851518 | 125851645 |
| chr10 | 125852300 | 125852498 | chr10 | 125852754 | 125853191 | chr10 | 133795401 | 133795430 |
| chr11 | 2040108 | 2040148 | chr11 | 3169689 | 3169835 | chr11 | 94275795 | 94275813 |
| chr11 | 94473683 | 94473769 | chr11 | 94473803 | 94473984 | chr11 | 94502453 | 94502489 |
| chr12 | 104850506 | 104850537 | chr12 | 104850578 | 104850592 | chr12 | 104851078 | 104851186 |
| chr13 | 26625302 | 26625502 | chr13 | 28366066 | 28366122 | chr13 | 36920350 | 36920379 |
| chr13 | 36920629 | 36920769 | chr13 | 73619661 | 73619698 | chr13 | 95364499 | 95364528 |
| chr13 | 95364771 | 95364800 | chr13 | 95620022 | 95620057 | chr13 | 110959797 | 110959860 |
| chr15 | 45670503 | 45670839 | chr15 | 48937059 | 48937095 | chr15 | 48937428 | 48937646 |
| chr15 | 48937710 | 48937987 | chr15 | 79383948 | 79383977 | chr15 | 83776497 | 83776596 |
| chr16 | 10276758 | 10276799 | chr16 | 10276801 | 10276841 | chr16 | 71715780 | 71715809 |
| chr17 | 32908287 | 32908371 | chr17 | 46125007 | 46125061 | chr17 | 47574091 | 47574149 |
| chr17 | 80535383 | 80535469 | chr19 | 3578139 | 3578223 | chr19 | 10823679 | 10823708 |
| chr19 | 50316245 | 50316330 | chr19 | 57862640 | 57862783 | chr20 | 4803922 | 4804008 |
| chr20 | 33547579 | 33547585 | chr20 | 36531800 | 36531910 | chr20 | 37434553 | 37434722 |
| chr20 | 37434737 | 37434744 | chr20 | 39317088 | 39317196 | chr21 | 27012374 | 27012431 |
| chr21 | 45508618 | 45508647 | chr22 | 39853522 | 39853590 | chr22 | 39853592 | 39853592 |

TABLE 19

| chr | start | end | chr | start | end | chr | start | end |
|---|---|---|---|---|---|---|---|---|
| chr1 | 3663875 | 3663921 | chr1 | 9712075 | 9712104 | chr1 | 11538796 | 11538821 |
| chr1 | 11539176 | 11539205 | chr1 | 11539411 | 11539440 | chr1 | 29450492 | 29450543 |
| chr1 | 38512386 | 38512415 | chr1 | 53068387 | 53068425 | chr1 | 91869989 | 91870018 |
| chr1 | 170633608 | 170633637 | chr1 | 202679216 | 202679327 | chr1 | 209381133 | 209381165 |
| chr1 | 230561780 | 230561824 | chr1 | 244014222 | 244014376 | chr2 | 31456683 | 31456712 |
| chr2 | 56410918 | 56410996 | chr2 | 56411692 | 56411733 | chr2 | 228029471 | 228029500 |
| chr3 | 37493520 | 37493621 | chr3 | 46924935 | 46924964 | chr3 | 49907094 | 49907130 |
| chr3 | 55519220 | 55519228 | chr3 | 98620892 | 98620980 | chr4 | 331323 | 331352 |
| chr4 | 5768772 | 57687782 | chr4 | 75858574 | 75858611 | chr4 | 87515338 | 87515367 |
| chr4 | 155665446 | 155665475 | chr5 | 129240069 | 129240101 | chr6 | 53212553 | 53213932 |
| chr6 | 71665639 | 71665723 | chr6 | 168719984 | 168720019 | chr7 | 409827 | 409872 |
| chr7 | 409887 | 409892 | chr7 | 54609992 | 54610006 | chr7 | 87104817 | 87105101 |
| che7 | 87257964 | 87258054 | chr7 | 106685283 | 106685345 | chr7 | 113726510 | 113726539 |
| chr8 | 107282164 | 107282195 | chr8 | 110704002 | 110704029 | chr8 | 110704098 | 110704144 |
| chr9 | 21974208 | 21974237 | chr9 | 36037069 | 36037098 | chr9 | 112403365 | 112403394 |
| chr9 | 132805319 | 132805445 | chr9 | 132805750 | 132805893 | chr10 | 116853876 | 116853908 |
| chr10 | 134755905 | 134755934 | chr11 | 20618293 | 20618322 | chr11 | 20618527 | 20618556 |
| chr11 | 64410724 | 64410759 | chr11 | 107461624 | 107461653 | chr11 | 114113023 | 114113052 |
| chr12 | 8850659 | 8850744 | chr12 | 95267525 | 95267554 | chr12 | 133463737 | 133463876 |
| chr12 | 133758049 | 133758107 | chr13 | 46961495 | 46961533 | chr13 | 49794118 | 49794179 |
| chr13 | 78492724 | 78492748 | chr13 | 92050761 | 92050814 | chr14 | 51561766 | 51562012 |
| chr15 | 53082444 | 53082491 | chr15 | 65669860 | 65669899 | chr15 | 83378213 | 83378370 |
| chr15 | 91643361 | 91643586 | chr16 | 23313465 | 23313522 | chr16 | 23313780 | 23313836 |
| chr16 | 80838052 | 80838143 | chr17 | 14204213 | 14204242 | chr17 | 14204528 | 14204620 |
| chr17 | 40333045 | 40333226 | chr17 | 42907565 | 42907630 | chr17 | 48071021 | 48071050 |
| chr17 | 51901005 | 51901034 | cbr17 | 56327272 | 56327301 | chr17 | 56833708 | 56833953 |
| chr19 | 10527166 | 10527243 | chr19 | 12163452 | 12163672 | chr19 | 12163894 | 12163923 |
| chr19 | 12175446 | 12175504 | chr19 | 12476501 | 12476556 | chr19 | 12606382 | 12606511 |
| chr19 | 23433144 | 23433223 | chr19 | 24216976 | 24217023 | chr19 | 33685545 | 33685581 |
| chr19 | 35264086 | 35264092 | chr19 | 37263533 | 37263584 | chr19 | 37341762 | 37341962 |
| chr19 | 37569394 | 37569554 | chr19 | 38085255 | 38085759 | chr19 | 38085958 | 38086066 |
| chr19 | 38146063 | 38146247 | chr19 | 38146458 | 38146568 | chr19 | 52097690 | 52097732 |
| chr19 | 53031202 | 53031215 | chr19 | 53193859 | 53193893 | chr19 | 58740087 | 58740118 |
| chr20 | 4230571 | 4230600 | chr20 | 20348527 | 20348605 | chr20 | 20349575 | 20349604 |
| chr20 | 39317751 | 39318138 | chr20 | 62680682 | 62680739 | chr21 | 33244922 | 33245040 |
| chr21 | 33245716 | 13245718 | chr21 | 33246038 | 33246190 | chr22 | 21368588 | 21368617 |
| chr22 | 24820331 | 24820396 | chr22 | 44208422 | 44208448 | — | — | — |

TABLE 20

| chr | start | end | chr | start | end | chr | start | end |
|---|---|---|---|---|---|---|---|---|
| chr1 | 898655 | 898690 | chr1 | 1856437 | 1856466 | chr1 | 1910416 | 1910445 |
| chr1 | 2375149 | 2375355 | chr1 | 10166522 | 10166551 | chr1 | 32180398 | 32180427 |
| chr1 | 97185263 | 97185357 | chr1 | 177150774 | 177150803 | chr1 | 246488176 | 246488316 |
| chr3 | 154797384 | 154797416 | chr4 | 146853952 | 146853981 | chr4 | 185089697 | 185089797 |
| chr5 | 57878711 | 57878752 | chr5 | 87976104 | 87976308 | chr5 | 87976526 | 87976559 |
| chr5 | 174220972 | 174221001 | chr7 | 44097691 | 44097876 | chr8 | 67025054 | 67025365 |
| chr9 | 140709047 | 140709174 | chr9 | 140727472 | 140727511 | chr9 | 140727846 | 140727930 |
| chr10 | 524755 | 524770 | chr11 | 392577 | 392720 | chr11 | 1027541 | 1027574 |
| chr11 | 66454425 | 66454454 | chr11 | 94884131 | 94884160 | chr12 | 54399617 | 54399646 |
| chr13 | 114807745 | 114807815 | chr14 | 21100749 | 21100778 | chr14 | 21100802 | 21100831 |
| chr16 | 1397455 | 1397484 | chr16 | 2128578 | 2128682 | chr16 | 2129143 | 2129332 |
| chr16 | 88757467 | 88757496 | chr17 | 1536129 | 1536146 | chr17 | 7348886 | 7348997 |
| chr17 | 17062575 | 7062752 | chr17 | 17123964 | 17123993 | chr18 | 32557847 | 32557864 |
| chr18 | 74501145 | 74501183 | chr19 | 1308066 | 1308081 | chr19 | 1775077 | 1775239 |
| chr19 | 58144295 | 58144701 | chr21 | 39047777 | 39047838 | chr21 | 44283611 | 44283774 |
| chr22 | 36902292 | 36902381 | chr22 | 42096003 | 42096190 | chr22 | 47023045 | 47023191 |
| chr22 | 47054687 | 47054700 | chr22 | 50943094 | 50943262 | chrX | 3746613 | 3746642 |

TABLE 21

| chr | start | end | ch | start | end | chr | start | end |
|---|---|---|---|---|---|---|---|---|
| chr1 | 213123890 | 213123919 | chr2 | 1653023 | 1653230 | chr5 | 17512115 | 17512144 |
| chr6 | 26284812 | 26284898 | chr7 | 6543151 | 6543216 | chr7 | 64330412 | 64330470 |
| chr10 | 7213532 | 7213535 | chr10 | 7424627 | 7424687 | chr11 | 68409559 | 68409588 |
| chr12 | 105478324 | 105478359 | chr15 | 99456300 | 99456329 | chr16 | 47177526 | 42177606 |
| chr16 | 88942120 | 88942160 | chr17 | 29298081 | 29298184 | chr17 | 29298186 | 29298463 |

TABLE 21-continued

| chr | start | end | ch | start | end | chr | start | end |
|---|---|---|---|---|---|---|---|---|
| chr17 | 42402885 | 42402917 | chr17 | 62777336 | 62777450 | chr18 | 77309534 | 77309563 |
| chr22 | 40075158 | 40075302 | — | — | — | — | — | — |

TABLE 22

| chr | start | end | chr | start | end | chr | start | end |
|---|---|---|---|---|---|---|---|---|
| chr1 | 12251874 | 12251958 | chr1 | 23586244 | 29586563 | chr1 | 50891347 | 50891376 |
| chr1 | 78511638 | 78511718 | chr1 | 91180277 | 91180306 | chr1 | 156010529 | 156010548 |
| chr1 | 161471751 | 161471779 | chr1 | 180204063 | 180204092 | chr1 | 200012190 | 200012191 |
| chr1 | 223936996 | 223937014 | chr1 | 228645141 | 228645244 | chr1 | 228645305 | 228645536 |
| chr2 | 43451910 | 43452327 | chr2 | 55289095 | 55289274 | chr2 | 106060616 | 106060792 |
| chr2 | 111875279 | 111875518 | chr2 | 118981668 | 118981738 | chr2 | 162272990 | 162273057 |
| chr2 | 175192104 | 175192136 | chr2 | 175193269 | 175193324 | chr2 | 175200141 | 175200170 |
| chr2 | 177001532 | 177001561 | chr2 | 223158970 | 223158999 | chr2 | 223165435 | 223165503 |
| chr2 | 223169835 | 223169864 | chr2 | 223176152 | 223176181 | chr2 | 230795536 | 230795555 |
| chr2 | 236877263 | 236877367 | chr2 | 242523908 | 242523985 | chr3 | 50402318 | 50402944 |
| chr3 | 181442377 | 181442410 | chr3 | 184057527 | 184057557 | chr4 | 3446992 | 3447021 |
| chr4 | 41750224 | 41750262 | chr4 | 42398843 | 42398872 | chr4 | 83323507 | 83323677 |
| chr4 | 166414897 | 166414921 | chr5 | 6687381 | 6687431 | chr5 | 10333726 | 10333762 |
| chr5 | 43215539 | 43215562 | chr5 | 50264821 | 50264850 | chr6 | 10416119 | 10416148 |
| chr6 | 18035868 | 18036015 | chr6 | 26332179 | 26332218 | chr6 | 28303563 | 28303571 |
| chr6 | 28303847 | 28304263 | chr6 | 50691066 | 50691095 | chr6 | 126068093 | 126068158 |
| chr6 | 152623016 | 152623493 | chr6 | 154970559 | 154970587 | chr7 | 2238119 | 2238235 |
| chr7 | 5262472 | 5262562 | chr7 | 27136761 | 27136790 | chr7 | 27195483 | 27195492 |
| chr7 | 113722940 | 113722969 | chr7 | 156801417 | 156801446 | chr8 | 108509544 | 108509650 |
| chr8 | 128931157 | 128931261 | chr8 | 142292553 | 142292774 | chr9 | 21965102 | 21965372 |
| chr9 | 21965686 | 21965757 | chr9 | 96721121 | 96721275 | chr9 | 96722477 | 96722546 |
| chr9 | 126349070 | 126349104 | chr10 | 3678618 | 3678537 | chr10 | 71327726 | 71327755 |
| chr10 | 102986586 | 102986758 | chr10 | 118890981 | 118891010 | chr10 | 124910364 | 124910439 |
| chr10 | 131937393 | 131937428 | chr11 | 67781387 | 67781564 | chr12 | 28127931 | 28127997 |
| chr12 | 28128620 | 28129054 | chr12 | 64783186 | 64783308 | chr12 | 72332642 | 72332696 |
| chr12 | 117474066 | 117474125 | chr14 | 37124038 | 37124067 | chr14 | 55765286 | 55765686 |
| chr14 | 73318472 | 73318629 | chr14 | 91691167 | 91691306 | chr14 | 91766189 | 91766450 |
| chr14 | 102682120 | 102682149 | chr15 | 37402975 | 37403087 | chr15 | 37403116 | 37403127 |
| chr15 | 65862054 | 65862121 | chr15 | 68125459 | 68125496 | chr16 | 142650 | 142775 |
| chr16 | 667548 | 667561 | chr16 | 677973 | 677993 | chr16 | 1407819 | 1407846 |
| chr16 | 2281250 | 2281314 | chr16 | 30907011 | 30907049 | chr16 | 30907123 | 30907148 |
| chr16 | 79623805 | 79623854 | chr16 | 85517346 | 85517388 | chr17 | 27181284 | 27181371 |
| chr17 | 37757154 | 37757217 | chr17 | 46655149 | 46655178 | chr17 | 46675420 | 46675449 |
| chr17 | 46691988 | 46692022 | chr17 | 46801219 | 46801277 | chr17 | 59539492 | 59539601 |
| chr17 | 75733979 | 75734108 | chr18 | 31902794 | 31902944 | chr18 | 55850846 | 55850987 |
| chr18 | 77550281 | 77550367 | chr19 | 8576915 | 8577000 | chr19 | 10407091 | 10407120 |
| chr20 | 44452732 | 44453063 | chr22 | 18328128 | 18328268 | chr22 | 19706634 | 19706677 |
| chr22 | 22058204 | 22058238 | chr22 | 28838201 | 28838292 | chr22 | 29445753 | 29445923 |

TABLE 23

| chr | start | end | chr | start | end | chr | start | end |
|---|---|---|---|---|---|---|---|---|
| chr1 | 2331364 | 2331437 | chr1 | 90309344 | 90309490 | chr1 | 219347395 | 219347472 |
| chr1 | 234620965 | 234620979 | chr1 | 245494496 | 245494578 | chr2 | 47200592 | 47200621 |
| chr2 | 47249735 | 47249848 | chr2 | 178973004 | 178973042 | chr2 | 209225238 | 209225275 |
| chr2 | 220080582 | 220080941 | chr2 | 240319921 | 240320012 | chr3 | 193419703 | 193419732 |
| chr4 | 1008741 | 1008806 | chr4 | 1282516 | 1282545 | chr4 | 57777438 | 57777577 |
| chr6 | 43639549 | 43639710 | chr7 | 127615922 | 127615951 | chr7 | 138042222 | 138042288 |
| chr7 | 140180180 | 140180298 | chr8 | 59058942 | 59059233 | chr8 | 141596887 | 141597022 |
| chr8 | 143558473 | 143558604 | chr8 | 144203654 | 144203708 | chr8 | 144303563 | 144303592 |
| chr10 | 135018033 | 135018070 | chr11 | 66658258 | 66658290 | chr11 | 120998702 | 120938825 |
| chr14 | 105512064 | 105512395 | chr16 | 4431127 | 4431189 | chr17 | 7368948 | 7369139 |
| chr17 | 77084519 | 77084667 | chr19 | 56201644 | 56201812 | chr22 | 46931261 | 46931332 |

TABLE 24

| chr | start | end | chr | start | end | Chr | start | end |
|---|---|---|---|---|---|---|---|---|
| chr1 | 2472175 | 2472301 | chr1 | 6186512 | 6186546 | chr1 | 16475032 | 16475207 |
| chr1 | 17445858 | 17445943 | chr1 | 53705675 | 53705701 | chr1 | 62793238 | 62793267 |
| chr1 | 91182806 | 91182835 | chr1 | 98515143 | 98515191 | chr1 | 98519024 | 98519056 |
| chr1 | 115631868 | 115631915 | chr1 | 115880364 | 115880395 | chr1 | 156815693 | 156815745 |
| chr1 | 182584084 | 182584340 | chr1 | 182584404 | 182584613 | chr1 | 217307385 | 217307437 |
| chr1 | 240256664 | 240256780 | chr2 | 5833900 | 5833932 | chr2 | 7164468 | 7164704 |
| chr2 | 7571718 | 7571747 | chr2 | 18059782 | 18059841 | chr2 | 47193958 | 47193960 |
| chr2 | 99439478 | 99439507 | chr2 | 131594990 | 131595019 | chr2 | 145282120 | 145282149 |
| chr2 | 171822429 | 171822480 | chr3 | 5137961 | 5138019 | chr3 | 13679285 | 13679319 |
| chr3 | 38030619 | 38030782 | chr3 | 140770070 | 140770099 | chr3 | 152877667 | 152877696 |
| chr3 | 184319829 | 184319843 | chr3 | 184319874 | 184319891 | chr3 | 195601240 | 195601312 |
| chr3 | 195602364 | 195602435 | chr4 | 1093537 | 1093558 | chr4 | 1331676 | 1331705 |
| chr4 | 5892136 | 5892194 | chr4 | 7758477 | 7758561 | chr4 | 42154663 | 42154697 |
| chr4 | 57803529 | 57803558 | chr4 | 113431916 | 113431930 | chr4 | 183064875 | 183064966 |
| chr4 | 184921856 | 184921885 | chr5 | 1930991 | 1931005 | chr5 | 2753049 | 2753078 |
| chr5 | 3595850 | 3595876 | chr5 | 17218196 | 17218225 | chr5 | 76940341 | 76940374 |
| chr5 | 138273818 | 138273845 | chr6 | 711143 | 711293 | chr6 | 26199138 | 26199167 |
| chr6 | 26199687 | 26199716 | chr6 | 52344376 | S2344405 | chr6 | 72596273 | 72596315 |
| chr7 | 1970843 | 1970872 | chr7 | 20826885 | 20826939 | chr7 | 45614930 | 45615020 |
| chr7 | 100808467 | 100808502 | chr8 | 41166306 | 41166374 | chr9 | 77113806 | 77113825 |
| chr9 | 135456477 | 135456544 | chr9 | 140033002 | 140033050 | chr10 | 73157868 | 73158027 |
| chr10 | 85954426 | 85954457 | chr10 | 128994871 | 128994903 | chr10 | 130338728 | 130338761 |
| chr10 | 133849599 | 133849628 | chr11 | 27744451 | 27744480 | chr11 | 131564971 | 131565073 |
| chr12 | 4274272 | 4274409 | chr12 | 4379358 | 4379491 | chr12 | 4382007 | 4382162 |
| chr12 | 5541101 | 5541177 | chr12 | 79257223 | 79257351 | chr12 | 94544023 | 94544052 |
| chr12 | 101025381 | 101025410 | chr12 | 103889161 | 103889211 | chr12 | 127940087 | 127940189 |
| chr13 | 32605035 | 32605212 | chr13 | 32605443 | 32605596 | chr13 | 32605675 | 32605966 |
| chr14 | 32597621 | 32597657 | chr14 | 69014045 | 69014110 | chr14 | 92979918 | 92979991 |
| chr14 | 105714416 | 105714442 | chr14 | 105715248 | 105715393 | chr15 | 68128595 | 68128597 |
| chr15 | 74818773 | 74818789 | chr15 | 89943411 | 89943440 | chr16 | 12996949 | 12997011 |
| chr16 | 89007521 | 89007558 | chr16 | 89008563 | 89008592 | chr18 | 3215043 | 3215256 |
| chr18 | 57364659 | 57364691 | chr18 | 75362932 | 75362985 | chr19 | 869338 | 869363 |
| chr19 | 1764294 | 1764339 | chr19 | 1776505 | 1776534 | chr19 | 4054436 | 4054463 |
| chr19 | 5292813 | 5292844 | chr19 | 12996170 | 12996280 | chr19 | 41018717 | 41018746 |
| chr19 | 42028503 | 42028549 | chr19 | 51228050 | 51228079 | chr19 | 52552105 | 52552120 |
| chr20 | 52311464 | 52311505 | chr20 | 59804233 | 59804235 | chr20 | 62321824 | 62321881 |
| chr22 | 22006004 | 22006243 | chr22 | 41634394 | 41634423 | — | — | —. |

8. The method of claim 1, further comprising:
c) sequencing a subset of the isolated converted DNA molecules that hybridized to the at least 1,000 different oligonucleotide probes,
thereby obtaining a first set of sequence reads.

9. The method of claim 8, further comprising
d) applying the first set of sequence reads to a model trained on:
a second set of sequence reads from a second set of DNA molecules processed to comprise uracils at positions of unmethylated cytosines,
wherein the second set of DNA molecules is isolated from samples obtained from individuals with cancer, and
a third set of sequence reads from a third set of DNA molecules processed to comprise uracils at positions of unmethylated cytosines,
wherein the third set of DNA molecules is isolated from samples obtained from individuals without cancer.

10. The method of claim 9, wherein the model comprises a kernel logistic regression classifier, a random forest classifier, a mixture model, a convolutional neural network, or an autoencoder model.

11. The method of claim 9, wherein the second set of DNA molecules and the third set of DNA molecules comprise target genomic regions comprising at least 5 CpG dinucleotides, and at least 80% of the at least 5 CpG dinucleotides of the target genomic regions of the second set of DNA molecules and the third set of DNA molecules are unmethylated, or
at least 80% of the at least 5 CpG dinucleotides of the target genomic regions of the second set of DNA molecules and the third set of DNA molecules are methylated.

12. The method of claim 9, wherein
the model is configured to determine a cancer classification, and
the cancer classification is a presence or absence of cancer, a type of cancer, and/or a stage of cancer.

13. The method of claim 9, wherein the cancer comprises at least 3 different types of cancer.

14. The method of claim 13, wherein the at least 3 different types of cancer are selected from the group consisting of blood cancer, breast cancer, colorectal cancer, esophageal cancer, head and neck cancer, hepatobiliary cancer, lung cancer, ovarian cancer, and pancreatic cancer.

15. The method of claim 9, wherein the bait set comprises pairs of oligonucleotide probes for at least 500 target genomic regions.

16. The method of claim 15, wherein the at least 500 target genomic regions are selected from Table 11, Table 12, Table 13, Table 14 or Table 15 as follows:

TABLE 11

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 147543 | 147613 | Hypo | cancer_general | — | chr18 | 597548 | 597578 | Hypo | cancer_general | CLUL1 |
| chr18 | 697854 | 697901 | Hypo | cancer_general | ENOSF1 | chr18 | 2755770 | 2755878 | Hypo | cancer_general | SMCHD1 |
| chr18 | 3214441 | 3214825 | Hypo | pancreas | MYOM1 | chr18 | 3215042 | 3215256 | Hypo | pancreas | MYOM1 |
| chr18 | 5133207 | 5133343 | Hypo | cancer_general | — | chr18 | 6908056 | 6908243 | Hypo | esophageal | ARHGAP28 |
| chr18 | 8612252 | 8612282 | Hypo | cancer_general | RAB12 | chr18 | 9868137 | 9868174 | Hypo | cancer_general | — |
| chr18 | 9912767 | 9912797 | Hypo | cancer_general | VAPA | chr18 | 10251324 | 10251432 | Hypo | cancer_general | AX747048 |
| chr18 | 10589096 | 10589348 | Hypo | cancer_general | — | chr18 | 10733492 | 10733605 | Hypo | cancer_general | PIEZO2 |
| chr18 | 11401654 | 11401817 | Hypo | cancer_general | — | chr18 | 11942728 | 11942838 | Hypo | cancer_general | — |
| chr18 | 11979677 | 11979860 | Hypo | cancer_general | IMPA2 | chr18 | 12277243 | 12277273 | Hypo | hepatobiliary | CIDEA |
| chr18 | 12375483 | 12375597 | Hypo | cancer_general | AFG3L2 | chr18 | 12375923 | 12376129 | Hypo | cancer_general | AFG3L2 |
| chr18 | 12890152 | 12890278 | Hypo | cancer_general | PTPN2 | chr18 | 12948993 | 12949023 | Hypo | cancer_general | SEH1L |
| chr18 | 13132080 | 13132246 | Hypo | ovarian | CEP192 | chr18 | 13826393 | 13826536 | Hypo | cancer_general | MC5R |
| chr18 | 19191525 | 19191585 | Hypo | cancer_general | SNRPD1 | chr18 | 20911541 | 20911571 | Hypo | cancer_general | TMEM241 |
| chr18 | 21035222 | 21035252 | Hypo | cancer_general | RIOK3 | chr18 | 21719938 | 21720064 | Hypo | cancer_general | CABYR, TTC39C |
| chr18 | 23686462 | 23686618 | Hypo | cancer_general | — | chr18 | 29413805 | 29413839 | Hypo | breast | TRAPPC8 |
| chr18 | 29719775 | 29720012 | Hypo | cancer_general | RNF138 | chr18 | 32957803 | 32957839 | Hypo | cancer_general | ZNF396 |
| chr18 | 33078363 | 33078662 | Hypo | cancer_general | INO80C | chr18 | 43546048 | 43546134 | Hypo | cancer_general | EPG5 |
| chr18 | 44259903 | 44259990 | Hypo | cancer_general | STSSIA5, AK095045 | chr18 | 46142662 | 46142809 | Hypo | cancer_general | CTIF |
| chr18 | 48604773 | 48604802 | Hypo | literature | SMAD4 | chr18 | 48636211 | 48636320 | Hypo | cancer_general | — |
| chr18 | 51771058 | 51771128 | Hypo | cancer_general | — | chr18 | 53989796 | 53989877 | Hypo | cancer_general | — |
| chr18 | 55426948 | 55426978 | Hypo | cancer_general | — | chr18 | 55850845 | 55850987 | Hypo | lung, cancer_general | NEDD4L |
| chr18 | 56483918 | 56483958 | Hypo | cancer_general | — | chr18 | 56815734 | 56816107 | Hypo | cancer_general | SEC11C, AK311213 |
| chr18 | 60557729 | 60557759 | Hypo | cancer_general | PHLPP1 | chr18 | 61143911 | 61143975 | Hypo | literature | SERPINB5 |
| chr18 | 72845833 | 72845863 | Hypo | cancer_general | — | chr18 | 74501144 | 74501183 | Hypo | head_neck | LOC100131655 |
| chr18 | 74755508 | 74755590 | Hypo | breast | MBP | chr18 | 75335093 | 75335123 | Hypo | cancer_general | — |
| chr18 | 75339231 | 75339340 | Hypo | cancer_general | — | chr18 | 75551271 | 75551301 | Hypo | cancer_general | — |
| chr18 | 75999404 | 75999434 | Hypo | cancer_general | — | chr18 | 76239541 | 76239616 | Hypo | cancer_general | — |
| chr18 | 76501479 | 76501509 | Hypo | cancer_general | — | chr18 | 76653631 | 76653661 | Hypo | cancer_general | — |
| chr18 | 76886249 | 76886279 | Hypo | cancer_general | — | chr18 | 76689735 | 76689765 | Hypo | cancer_general | — |
| chr18 | 77050480 | 77050678 | Hypo | cancer_general | ATP9B | chr18 | 77143346 | 77143376 | Hypo | cancer_general | ATP9B |
| chr18 | 77167824 | 77167854 | Hypo | cancer_general | NFATC1 | chr18 | 77181355 | 77181409 | Hypo | cancer_general | NFATC1 |
| chr18 | 77194936 | 77194978 | Hypo | cancer_general | NFATC1 | chr18 | 77205525 | 77205638 | Hypo | cancer_general | NFATC1 |
| chr18 | 77285897 | 77286028 | Hypo | cancer_general | — | chr18 | 77300326 | 77300483 | Hypo | cancer_general | — |
| chr18 | 77309533 | 77309563 | Hypo | hepatobiliary | — | chr18 | 77312866 | 77312927 | Hypo | cancer_general | — |
| chr18 | 77329727 | 77330017 | Hypo | colorectal | CTDP1 | chr18 | 77371430 | 77371547 | Hypo | cancer_general | CTDP1 |
| chr18 | 77459762 | 77459877 | Hypo | cancer_general | — | chr18 | 77512225 | 77512255 | Hypo | cancer_general | — |
| chr18 | 77543249 | 77543481 | Hypo | cancer_general | — | chr18 | 77543700 | 77543824 | Hypo | cancer_general | — |
| chr18 | 77550206 | 77550367 | Hypo | lung, cancer_general | — | chr18 | 77576934 | 77577043 | Hypo | cancer_general | — |
| chr18 | 77636591 | 77636621 | Hypo | cancer_general | KCNG2 | chr18 | 77698881 | 77698919 | Hypo | breast | — |
| HCV | 111 | 140 | Hypo | virus | — | HCV | 374 | 403 | Hypo | virus | — |
| HCV | 637 | 666 | Hypo | virus | — | HCV | 900 | 929 | Hypo | virus | — |
| HCV | 1163 | 1192 | Hypo | virus | — | HCV | 1426 | 1455 | Hypo | virus | — |
| HCV | 1689 | 1718 | Hypo | virus | — | HCV | 1952 | 1981 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HCV | 2215 | 2244 | Hypo | virus | — | HCV | 2478 | 2507 | Hypo | virus | — |
| HCV | 2741 | 2770 | Hypo | virus | — | HCV | 3004 | 3033 | Hypo | virus | — |
| HCV | 3267 | 3296 | Hypo | virus | — | HCV | 3530 | 3559 | Hypo | virus | — |
| HCV | 3793 | 3822 | Hypo | virus | — | HCV | 4056 | 4085 | Hypo | virus | — |
| HCV | 4319 | 4348 | Hypo | virus | — | HCV | 4582 | 4611 | Hypo | virus | — |
| HCV | 4845 | 4874 | Hypo | virus | — | HCV | 5108 | 5137 | Hypo | virus | — |
| HCV | 5371 | 5400 | Hypo | virus | — | HCV | 5634 | 5663 | Hypo | virus | — |
| HCV | 5897 | 5926 | Hypo | virus | — | HCV | 6160 | 6189 | Hypo | virus | — |
| HCV | 6423 | 6452 | Hypo | virus | — | HCV | 6686 | 6715 | Hypo | virus | — |
| HCV | 6949 | 6978 | Hypo | virus | — | HCV | 7212 | 7241 | Hypo | virus | — |
| HCV | 7475 | 7504 | Hypo | virus | — | HCV | 7738 | 7767 | Hypo | virus | — |
| HCV | 8001 | 8030 | Hypo | virus | — | HCV | 8264 | 8293 | Hypo | virus | — |
| HCV | 8527 | 8556 | Hypo | virus | — | HCV | 8790 | 8819 | Hypo | virus | — |
| HCV | 9053 | 9082 | Hypo | virus | — | chr8 | 1085573 | 1085603 | Hypo | cancer_general | — |
| chr8 | 1325465 | 1325606 | Hypo | cancer_general | — | chr8 | 1444052 | 1444205 | Hypo | cancer_general | DLGAP2 |
| chr8 | 8640024 | 8640100 | Hypo | cancer_general | MFHAS1 | chr8 | 8681258 | 8681353 | Hypo | blood | MFHAS1 |
| chr8 | 8748422 | 8748713 | Hypo | cancer_general | MFHAS1 | chr8 | 8748919 | 8748956 | Hypo | cancer_general | MFHAS1 |
| chr8 | 9722850 | 9722896 | Hypo | cancer_general | — | chr8 | 10652917 | 10653017 | Hypo | ovarian | CTSB, FDFT1 |
| chr8 | 10980452 | 10980589 | Hypo | cancer_general | C8orf15 | chr8 | 11700190 | 11700284 | Hypo | head_neck | CTSB, FDFT1 |
| chr8 | 11705960 | 11706136 | Hypo | cancer_general | FDFT1, CTSB | chr8 | 11706580 | 11706613 | Hypo | cancer_general | TRNA_Pseudo |
| chr8 | 11726469 | 11726975 | Hypo | cancer_general | — | chr8 | 11790579 | 11790653 | Hypo | cancer_general | — |
| chr8 | 13319931 | 13319961 | Hypo | cancer_general | — | chr8 | 20375563 | 20375592 | Hypo | literature | MIR320A, POLR3D |
| chr8 | 21876649 | 21876819 | Hypo | cancer_general | NPM2 | chr8 | 22101641 | 22101699 | Hypo | cancer_general | SLC25A37, AF116693, FP15737 |
| chr8 | 22458657 | 22458687 | Hypo | head_neck | KIAA1967, C8orf58, PDLIM2 | chr8 | 23423923 | 23423974 | Hypo | cancer_general | HMBOX1, INTS9 |
| chr8 | 28266438 | 28266484 | Hypo | breast | — | chr8 | 28737884 | 28738023 | Hypo | head_neck | |
| chr8 | 30475450 | 30475480 | Hypo | breast | GTF2E2 | chr8 | 31044103 | 31044133 | Hypo | ovarian | EIF4EBP1 |
| chr8 | 37755922 | 37755952 | Hypo | cancer_general | — | chr8 | 37906396 | 37906513 | Hypo | head_neck | LSM1 |
| chr8 | 37961793 | 37961902 | Hypo | cancer_general | ASH2L BAG4, LSM1 | chr8 | 38020213 | 38020272 | Hypo | head_neck | LETM2 |
| chr8 | 38032345 | 38032827 | Hypo | cancer_general | — | chr8 | 38256378 | 38256412 | Hypo | cancer_general | |
| chr8 | 38262472 | 38262502 | Hypo | pancreas | FGFR1, LETM2 | chr8 | 38274835 | 38274864 | Hypo | literature | FGFR1, LETM2 |
| chr8 | 39172082 | 39172134 | Hypo | literature | ADAM5 | chr8 | 41166305 | 41166374 | Hypo | pancreas | SFRP1 |
| chr8 | 41700639 | 41700751 | Hypo | cancer_general | — | chr8 | 41711325 | 41711447 | Hypo | cancer_general | — |
| chr8 | 41910270 | 41910339 | Hypo | cancer_general | KAT6A | chr8 | 42082721 | 42082874 | Hypo | pancreas | SLC20A2 MIR4469, HOOK3, RNF170 |
| chr8 | 42147392 | 42147521 | Hypo | cancer_general | IKBKB | chr8 | 42293604 | 42293722 | Hypo | breast | |
| chr8 | 42350324 | 42350492 | Hypo | cancer_general | SLC20A2 | chr8 | 42749816 | 42750012 | Hypo | cancer_general | |
| chr8 | 47093246 | 47093276 | Hypo | cancer_general | — | chr8 | 47334619 | 47334678 | Hypo | cancer_general | |
| chr8 | 48044710 | 48044753 | Hypo | ovarian | — | chr8 | 49572029 | 49572058 | Hypo | literature | C8orf22 |
| chr8 | 49836145 | 49836174 | Hypo | literature | — | chr8 | 49959230 | 49959260 | Hypo | cancer_general | ST18 |
| chr8 | 52230518 | 52230548 | Hypo | cancer_general | SNAI2 | chr8 | 53322495 | 53322524 | Hypo | literature | — |
| chr8 | 54698973 | 54699103 | Hypo | breast | PXDNL ATP6V1H | chr8 | 55826087 | 55826117 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 56542925 | 56543064 | Hypo | cancer_general | — | chr8 | 57360211 | 57360240 | Hypo | literature | AX747062, PENK |
| chr8 | 58105946 | 58106115 | Hypo | cancer_general | — | chr8 | 58117004 | 58117079 | Hypo | cancer_general | — |
| chr8 | 58130364 | 58130574 | Hypo | cancer_general | LOC100507651 | chr8 | 59058941 | 59059343 | Hypo | ovarian | FAM110B |
| chr8 | 59747186 | 59747318 | Hypo | cancer_general | TOX | chr8 | 61777575 | 61777699 | Hypo | breast | — |
| chr8 | 61789974 | 61790004 | Hypo | cancer_general | — | chr8 | 62033879 | 62034059 | Hypo | cancer_general | — |
| chr8 | 62763403 | 62763433 | Hypo | cancer_general | — | chr8 | 66548717 | 66548800 | Hypo | cancer_general | MTFR1, ARMC1 |
| chr8 | 66560323 | 66560545 | Hypo | cancer_general | MTFR1 | chr8 | 67580735 | 67580829 | Hypo | cancer_general | C8orf44-SGK3, VCPIP1, C8orf44 |
| chr8 | 71017156 | 71017195 | Hypo | cancer_general | NCOA2 | chr8 | 71308096 | 71308126 | Hypo | cancer_general | — |
| chr8 | 71447529 | 71447559 | Hypo | cancer_general | — | chr8 | 72470399 | 72470441 | Hypo | cancer_general | — |
| chr8 | 74759306 | 74759463 | Hypo | cancer_general | UBE2W, TCEB1, TMEM70 | chr8 | 74759819 | 74759966 | Hypo | cancer_general | UBE2W |
| chr8 | 74889486 | 74889592 | Hypo | cancer_general | — | chr8 | 76316329 | 76316452 | Hypo | cancer_general | HNF4G |
| chr8 | 80894529 | 80894594 | Hypo | cancer_general | TPD52, MRPS28 | chr8 | 80998526 | 80998601 | Hypo | lung | TPD52 |
| chr8 | 81128658 | 81128782 | Hypo | breast | — | chr8 | 81414643 | 81414831 | Hypo | colorectal | ZBTB10 |
| chr8 | 82243813 | 82243843 | Hypo | cancer_general | — | chr8 | 82902963 | 82902993 | Hypo | cancer_general | — |
| chr8 | 84932902 | 84932942 | Hypo | cancer_general | — | chr8 | 86131760 | 86131850 | Hypo | cancer_general | E2F5, CA13, AB209185, C8orf59 |
| chr8 | 86405788 | 86405818 | Hypo | lung | — | chr8 | 86406716 | 86406849 | Hypo | cancer_general | — |
| chr8 | 86436621 | 86436651 | Hypo | cancer_general | — | chr8 | 86495193 | 86495287 | Hypo | cancer_general | — |
| chr8 | 86544756 | 86544959 | Hypo | cancer_general | — | chr8 | 90702972 | 90703034 | Hypo | cancer_general | — |
| chr8 | 90913079 | 90913653 | Hypo | cancer_general | OSGIN2 | chr8 | 91411537 | 91411567 | Hypo | cancer_general | — |
| chr8 | 92083523 | 92083751 | Hypo | cancer_general | OTUD6B, BC067244 | chr8 | 94684190 | 94684560 | Hypo | cancer_general | LINC00535 |
| chr8 | 95485999 | 95486029 | Hypo | cancer_general | RAD54B C8orf69 | chr8 | 96038540 | 96038580 | Hypo | cancer_general | NDUFAF6 C8orf37, TRNA_Ser, LOC100616530 |
| chr8 | 96219863 | 96219901 | Hypo | cancer_general | — | chr8 | 96285420 | 96285553 | Hypo | ovarian | |
| chr8 | 97339846 | 97340195 | Hypo | cancer_general | PTDSS1 | chr8 | 98744202 | 98744325 | Hypo | cancer_general | MTDH |
| chr8 | 98786343 | 98786387 | Hypo | ovarian | LAPTM4B | chr8 | 98786918 | 98786972 | Hypo | ovarian | LAPTM4B |
| chr8 | 99235037 | 99235037 | Hypo | breast | NIPAL2 | chr8 | 99951897 | 99951939 | Hypo | cancer_general | OSR2 |
| chr8 | 100117651 | 100117765 | Hypo | breast | VPS13B | chr8 | 101169625 | 101169659 | Hypo | cancer_general | SPAG1, POLR2K |
| chr8 | 101226865 | 101226945 | Hypo | lung | PABPC1 | chr8 | 101736027 | 101736202 | Hypo | cancer_general | PABPC1 |
| chr8 | 103575128 | 103575296 | Hypo | pancreas | ODF1 | chr8 | 103629590 | 103629882 | Hypo | cancer_general | — |
| chr8 | 106301844 | 106301978 | Hypo | cancer_general | — | chr8 | 106434115 | 106434145 | Hypo | cancer_general | ZFPM2 |
| chr8 | 109500408 | 109500507 | Hypo | lung | EMC2 | chr8 | 110275006 | 110275040 | Hypo | cancer_general | NUDCD1 |
| chr8 | 110406028 | 110406243 | Hypo | cancer_general | PKHD1L1 | chr8 | 110592198 | 110592228 | Hypo | cancer_general | SYBU |
| chr8 | 110704001 | 110704144 | Hypo | esophageal | — | chr8 | 111133092 | 111133257 | Hypo | cancer_general | — |
| chr8 | 115516296 | 115516440 | Hypo | cancer_general | EXT1 | chr8 | 118532128 | 118532292 | Hypo | cancer_general | MED30 |
| chr8 | 119043568 | 119043732 | Hypo | cancer_general | — | chr8 | 120219912 | 120219941 | Hypo | literature | MAL2 |
| chr8 | 120844095 | 120844285 | Hypo | cancer_general | DSCC1, TAF2 | chr8 | 120845586 | 120845807 | Hypo | cancer_general | DSCC1, TAF2 |
| chr8 | 121825455 | 121825484 | Hypo | literature | — | chr8 | 122068889 | 122068919 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 122346689 | 122346719 | Hypo | cancer_general | — | chr8 | 122346940 | 122347052 | Hypo | cancer_general | — |
| chr8 | 123695532 | 123695660 | Hypo | cancer_general | — | chr8 | 124014063 | 124014111 | Hypo | lung | ATAD2 |
| chr8 | 124055236 | 124055336 | Hypo | cancer_general | DERL1 | chr8 | 124332846 | 124332875 | Hypo | literature | — |
| chr8 | 124427887 | 124428082 | Hypo | cancer_general | WDYHV1 | chr8 | 125411827 | 125411857 | Hypo | head_neck | — |
| chr8 | 125452366 | 125452541 | Hypo | cancer_general | — | chr8 | 126007690 | 126008051 | Hypo | ovarian | SQLE |
| chr8 | 126044442 | 126044563 | Hypo | cancer_general | KIAA0196, SQLE | chr8 | 127354106 | 127354261 | Hypo | cancer_general | — |
| chr8 | 128403354 | 128403383 | Hypo | literature | DQ515899, DQ515898, LOC727677 | chr8 | 128745542 | 128745633 | Hypo | cancer_general | MYC, HV975509, BC042052 |
| chr8 | 128808002 | 128808077 | Hypo | literature | MIR1204, PVT1, MYC | chr8 | 128872385 | 128872415 | Hypo | cancer_general | PVT1 |
| chr8 | 128889324 | 128889422 | Hypo | cancer_general | — | chr8 | 128893019 | 128893049 | Hypo | ovarian | MIR1205, TMEM75, PVT1 |
| chr8 | 128931133 | 128931261 | Hypo | lung | PVT1 | chr8 | 128964114 | 128964309 | Hypo | breast | — |
| chr8 | 129356009 | 129356039 | Hypo | cancer_general | — | chr8 | 130369244 | 130369364 | Hypo | cancer_general | CCDC26 |
| chr8 | 132054727 | 132054785 | Hypo | cancer_general | ADCY8 | chr8 | 133360080 | 133360194 | Hypo | cancer_general | KCNQ3 |
| chr8 | 133686745 | 133687107 | Hypo | cancer_general | LRRC6 | chr8 | 135301097 | 135301142 | Hypo | cancer_general | — |
| chr8 | 140755383 | 140755550 | Hypo | breast | TRAPPC9 | chr8 | 140834237 | 140834321 | Hypo | cancer_general | TRAPPC9 |
| chr8 | 140963292 | 140963362 | Hypo | cancer_general | TRAPPC9 | chr8 | 141054845 | 141054875 | Hypo | cancer_general | TRAPPC9 |
| chr8 | 141159919 | 141159949 | Hypo | cancer_general | — | chr8 | 141588056 | 141588132 | Hypo | cancer_general | AGO2 |
| chr8 | 141596886 | 141597022 | Hypo | ovarian | AGO2 | chr8 | 141614252 | 141614287 | Hypo | breast | AGO2 |
| chr8 | 142210914 | 142211043 | Hypo | lung | DENND3, SLC45A4 | chr8 | 142265206 | 142265339 | Hypo | ovarian | — |
| chr8 | 142282078 | 142282202 | Hypo | hepatobiliary | — | chr8 | 142292552 | 142292774 | Hypo | cancer_general, lung | — |
| chr8 | 142361233 | 142361487 | Hypo | cancer_general | GPR20, LOC731779 | chr8 | 142367368 | 142367790 | Hypo | breast | GPR20 |
| chr8 | 142444600 | 142444752 | Hypo | cancer_general | MROH5, PTP4A3 | chr8 | 142535343 | 142535496 | Hypo | cancer_general | — |
| chr8 | 142568598 | 142568652 | Hypo | cancer_general | — | chr8 | 142632436 | 142632465 | Hypo | literature | — |
| chr8 | 142694847 | 142694953 | Hypo | cancer_general | — | chr8 | 142984512 | 142984666 | Hypo | cancer_general | TSNARE1 |
| chr8 | 143082777 | 143082810 | Hypo | cancer_general | — | chr8 | 143089030 | 143089100 | Hypo | cancer_general | BAI1 |
| chr8 | 143105244 | 143105377 | Hypo | cancer_general | — | chr8 | 143368318 | 143368469 | Hypo | pancreas | BAI1 |
| chr8 | 143509457 | 143509594 | Hypo | ovarian | BAI1 | chr8 | 143557980 | 143558080 | Hypo | cancer_general | BAI1 |
| chr8 | 143558604 | 143558666 | Hypo | hepatobiliary | BAI1 | chr8 | 143587331 | 143587382 | Hypo | cancer_general | SLURP1, THEM6 |
| chr8 | 143611232 | 143611262 | Hypo | cancer_general | ARC | chr8 | 143621980 | 143622096 | Hypo | cancer_general | — |
| chr8 | 143702052 | 143702101 | Hypo | cancer_general | LY6D | chr8 | 143819384 | 143819428 | Hypo | cancer_general | — |
| chr8 | 143876928 | 143876958 | Hypo | cancer_general | CDC42P3, LOC100133669 | chr8 | 143993974 | 143994165 | Hypo | cancer_general | CYP11B2 |
| chr8 | 144069546 | 144069651 | Hypo | cancer_general | — | chr8 | 144190378 | 144190432 | Hypo | cancer_general | — |
| chr8 | 144203977 | 144204021 | Hypo | cancer_general | LY6H | chr8 | 144226174 | 144226204 | Hypo | cancer_general | GPIHBP1 |
| chr8 | 144238822 | 144238901 | Hypo | cancer_general | ZFP41 | chr8 | 144303562 | 144303592 | Hypo | ovarian | GLI4 |
| chr8 | 144330193 | 144330380 | Hypo | cancer_general | GLI4 | chr8 | 144344293 | 144344442 | Hypo | cancer_general | GLI4 |
| chr8 | 144347397 | 144347740 | Hypo | cancer_general | GLI4 | chr8 | 144359977 | 144360076 | Hypo | cancer_general | GLI4 |
| chr8 | 144360394 | 144360453 | Hypo | cancer_general | ZNF696 | chr8 | 144361758 | 144361823 | Hypo | cancer_general | — |
| chr8 | 144372323 | 144372503 | Hypo | cancer_general | — | chr8 | 144382679 | 144382775 | Hypo | cancer_general | TOP1MT, ZNF696 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 144421487 | 144421517 | Hypo | blood | TOP1MT | chr8 | 144557003 | 144557088 | Hypo | head_neck | ZC3H3 |
| chr8 | 144617065 | 144617347 | Hypo | ovarian | ZC3H3 | chr8 | 144668566 | 144668667 | Hypo | breast | BC034020, EEF1D, NAPRT1 |
| chr8 | 144668909 | 144668972 | Hypo | breast | BC034020, EEF1D, NAPRT1 | chr8 | 145218226 | 145218301 | Hypo | blood | MROH1 |
| chr8 | 145223902 | 145224061 | Hypo | ovarian | MROH1 | chr8 | 145753517 | 145753547 | Hypo | cancer_general | DQ579335, LRRC14, ARHGAP39, C8orf82, LRRC24 |
| chr8 | 145758572 | 145758692 | Hypo | cancer_general | ARHGAP39, C8orf82, LRRC24 | chr8 | 145918683 | 145918835 | Hypo | cancer_general | ARHGAP39 |
| chr8 | 146013617 | 146013647 | Hypo | cancer_general | RPL8, DL491750, ZNF34 | chr8 | 146079215 | 146079379 | Hypo | cancer_general | COMMD5 |
| chr8 | 146175120 | 146175269 | Hypo | cancer_general | ZNF16 | chr8 | 146176756 | 146176795 | Hypo | cancer_general | ZNF16 |
| chr21 | 19274828 | 19274858 | Hypo | cancer_general | CHODL | chr21 | 31015201 | 31015231 | Hypo | cancer_general | GRIK1 |
| chr21 | 31056850 | 31056927 | Hypo | hepatobiliary | GRIK1 | chr21 | 32253745 | 32253774 | Hypo | literature | KRTAP11-1 |
| chr21 | 33043985 | 33044051 | Hypo | breast | SOD1, SCAF4 | chr21 | 33627549 | 33627649 | Hypo | cancer_general | — |
| chr21 | 33721756 | 33721824 | Hypo | cancer_general | URB1 | chr21 | 33983236 | 33983488 | Hypo | cancer_general | C21orf59 |
| chr21 | 34397024 | 34397091 | Hypo | cancer_general | OLIG2 | chr21 | 34469746 | 34469844 | Hypo | cancer_general | — |
| chr21 | 35051159 | 35051231 | Hypo | cancer_general | ITSN1 | chr21 | 37527928 | 37527958 | Hypo | cancer_general | DOPEY2, CBR3-AS1, CBR3 |
| chr21 | 37758570 | 37758652 | Hypo | cancer_general | CHAF1B | chr21 | 37775034 | 37775141 | Hypo | cancer_general, breast | CHAF1B |
| chr21 | 38092179 | 38092221 | Hypo | cancer_general | SIM2 | chr21 | 38638422 | 38638526 | Hypo | cancer_general | DSCR3 |
| chr21 | 38935478 | 38935549 | Hypo | cancer_general | — | chr21 | 40034756 | 40034785 | Hypo | literature | ERG |
| chr21 | 42596911 | 42597043 | Hypo | hepatobiliary | — | chr21 | 42617963 | 42617995 | Hypo | hepatobiliary | BACE2 |
| chr21 | 42649172 | 42649202 | Hypo | hepatobiliary | BACE2 | chr21 | 43240082 | 43240112 | Hypo | ovarian | PRDM15 |
| chr21 | 43256565 | 43256603 | Hypo | blood | PRDM15 | chr21 | 43376373 | 43376403 | Hypo | cancer_general | AX748362, UMODL1 |
| chr21 | 43393528 | 43393713 | Hypo | pancreas | — | chr21 | 43485279 | 43485348 | Hypo | head_neck | SLC37A1 |
| chr21 | 43786683 | 43786713 | Hypo | cancer_general | TMPRSS3, TFF1 | chr21 | 43991463 | 43991493 | Hypo | cancer_general | — |
| chr21 | 44250815 | 44250855 | Hypo | cancer_general | — | chr21 | 44283581 | 44283774 | Hypo | head_neck | WDR4 |
| chr21 | 44514762 | 44514791 | Hypo | literature | U2AF1 | chr21 | 44524441 | 44524470 | Hypo | literature | U2AF1 |
| chr21 | 44837088 | 44837213 | Hypo | cancer_general | SIK1 | chr21 | 44866603 | 44866711 | Hypo | cancer_general | LINC00319 |
| chr21 | 44886709 | 44886870 | Hypo | breast | LINC00313 | chr21 | 45118492 | 45118644 | Hypo | esophageal | RRP1B |
| chr21 | 45131875 | 45131905 | Hypo | cancer_general | PDXK | chr21 | 45195149 | 45195319 | Hypo | cancer_general | CSTB |
| chr21 | 45271643 | 45271688 | Hypo | cancer_general | — | chr21 | 45273717 | 45273913 | Hypo | cancer_general | — |
| chr21 | 45277332 | 45277513 | Hypo | head_neck | AGPAT3 | chr21 | 45290014 | 45290044 | Hypo | head_neck | AGPAT3 |
| chr21 | 45508617 | 45508647 | Hypo | colorectal | TRAPPC10 | chr21 | 45521343 | 45521438 | Hypo | breast | PWP2, TRAPPC10 |
| chr21 | 45621533 | 45621573 | Hypo | breast | — | chr21 | 45791079 | 45791109 | Hypo | cancer_general | TRPM2 |
| chr21 | 45847832 | 45847973 | Hypo | cancer_general | TRPM2 | chr21 | 46036642 | 46036767 | Hypo | cancer_general | KRTAP10-8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr21 | 46193414 | 46193542 | Hypo | cancer_general | UBE2G2 | chr21 | 46257116 | 46257273 | Hypo | cancer_general | ITGB2 |
| chr21 | 46310428 | 46310491 | Hypo | cancer_general | ITGB2 | chr21 | 46318286 | 46318343 | Hypo | cancer_general | FAM207A, C21orf67, ITGB2-AS1 |
| chr21 | 46319156 | 46319459 | Hypo | cancer_general | ITGB2 | chr21 | 46359187 | 46359248 | Hypo | cancer_general | |
| chr21 | 46452374 | 46452539 | Hypo | cancer_general | — | chr21 | 46677734 | 46677796 | Hypo | cancer_general | POFUT2, C21orf89 |
| chr21 | 46847654 | 46847684 | Hypo | pancreas | COL18A1-AS1 | chr21 | 46863658 | 46863708 | Hypo | cancer_general | — |
| chr21 | 46925780 | 46925925 | Hypo | cancer_general | COL18A1, SLC19A1 | chr21 | 46926459 | 46926565 | Hypo | cancer_general | SLC19A1, COL18A1 |
| chr21 | 46935739 | 46935936 | Hypo | breast | SLC19A1, COL18A1 | chr21 | 47404174 | 47404325 | Hypo | cancer_general | COL6A1 |
| chr21 | 47504861 | 47504895 | Hypo | cancer_general | — | chr21 | 47746270 | 47746393 | Hypo | cancer_general | PCNT, BC031638, C21orf58 |
| chr11 | 232863 | 233062 | Hypo | breast | PSMD13, SIRT3 | chr11 | 392576 | 392720 | Hypo | head_neck | PKP3 |
| chr11 | 394815 | 394968 | Hypo | cancer_general | PKP3 | chr11 | 505732 | 505869 | Hypo | cancer_general | RNH1 |
| chr11 | 518400 | 518430 | Hypo | cancer_general | — | chr11 | 526389 | 526419 | Hypo | cancer_general | HRAS |
| chr11 | 533451 | 533567 | Hypo | literature | LRRC56, HRAS | chr11 | 533859 | 533888 | Hypo | literature | LRRC56, HRAS |
| chr11 | 534273 | 534302 | Hypo | literature | LRRC56, HRAS | chr11 | 548731 | 548800 | Hypo | lung | C11orf35, AX748330, LRRC56 |
| chr11 | 763323 | 763686 | Hypo | cancer_general | BC048998, PDDC1, TALDO1 | chr11 | 775261 | 775291 | Hypo | pancreas | NS3BP, PDDC1, BC048998 |
| chr11 | 850555 | 850823 | Hypo | cancer_general | TSPAN4, POLR2L, AK126635 | chr11 | 861612 | 861657 | Hypo | cancer_general | CHID1, AK126635, TSPAN4 |
| chr11 | 863062 | 863092 | Hypo | cancer_general | CHID1, AK126635, TSPAN4 | chr11 | 1006077 | 1006107 | Hypo | cancer_general | MUC6 |
| chr11 | 1027540 | 1027574 | Hypo | head_neck | MUC6 | chr11 | 1029238 | 1029403 | Hypo | cancer_general | MUC6 |
| chr11 | 1030215 | 1030296 | Hypo | cancer_general | MUC6 | chr11 | 1080391 | 1080454 | Hypo | cancer_general | MUC2 |
| chr11 | 1081667 | 1081715 | Hypo | cancer_general | MUC2 | chr11 | 1214665 | 1214917 | Hypo | cancer_general | MUC5AC, MUC5B |
| chr11 | 1215899 | 1215999 | Hypo | cancer_general | MUC5AC, MUC5B | chr11 | 1229945 | 1229975 | Hypo | cancer_general | MUC5AC, MUC5B |
| chr11 | 1244381 | 1244465 | Hypo | cancer_general | MUC5B | chr11 | 1250889 | 1250924 | Hypo | cancer_general | MUC5B |
| chr11 | 1251183 | 1251351 | Hypo | cancer_general | MUC5B | chr11 | 1263602 | 1263644 | Hypo | cancer_general | MUC5B |
| chr11 | 1274085 | 1274189 | Hypo | cancer_general | MUC5B | chr11 | 1374959 | 1375003 | Hypo | cancer_general | MUC5B |
| chr11 | 1430714 | 1430794 | Hypo | cancer_general | BRSK2 | chr11 | 1464280 | 1464428 | Hypo | cancer_general | BRSK2 |
| chr11 | 1469228 | 1469379 | Hypo | cancer_general | BRSK2 | chr11 | 1471920 | 1472058 | Hypo | cancer_general | BRSK2 |
| chr11 | 1868081 | 1868237 | Hypo | cancer_general | TNNI2, LSP1 | chr11 | 1946130 | 1946160 | Hypo | cancer_general | TNNT3 |
| chr11 | 1957391 | 1957530 | Hypo | cancer_general | TNNT3 | chr11 | 1959077 | 1959187 | Hypo | cancer_general | MRPL23, TNNT3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 2040107 | 2040148 | Hypo | colorectal | — | chr11 | 2209907 | 2210278 | Hypo | cancer_general | — |
| chr11 | 2226048 | 2226078 | Hypo | cancer_general | — | chr11 | 2278708 | 2278839 | Hypo | cancer_general | — |
| chr11 | 2437991 | 2438144 | Hypo | cancer_general | TRPM5 | chr11 | 3027425 | 3027562 | Hypo | head_neck | CARS |
| chr11 | 3169665 | 3169835 | Hypo | colorectal | — | chr11 | 3182104 | 3182133 | Hypo | tcga | — |
| chr11 | 3511446 | 3511501 | Hypo | hepatobiliary | — | chr11 | 3767205 | 3767284 | Hypo | cancer_general | NUP98 |
| chr11 | 4038082 | 4038176 | Hypo | cancer_general | — | chr11 | 4095819 | 4095864 | Hypo | ovarian | STIM1 |
| chr11 | 4209382 | 4209411 | Hypo | tcga | RRM1, LOC100506082 | chr11 | 5641077 | 5641140 | Hypo | lung | TRIM34, TRIM6, TRIM6-TRIM34 |
| chr11 | 5993897 | 5994029 | Hypo | cancer_general | OR56A5 | chr11 | 6497192 | 6497222 | Hypo | cancer_general | ARFIP2, TIMM10B, TRIM3 |
| chr11 | 9405392 | 9405752 | Hypo | cancer_general | IPO7 | chr11 | 10509678 | 10509807 | Hypo | cancer_general | AMPD3 |
| chr11 | 10811151 | 10811224 | Hypo | cancer_general | EIF4G2, CTR9 | chr11 | 10815867 | 10815998 | Hypo | cancer_general | EIF4G2, SNORD97 |
| chr11 | 13711492 | 13711529 | Hypo | hepatobiliary | FAR1 | chr11 | 14316375 | 14316404 | Hypo | literature | RRAS2 |
| chr11 | 14543250 | 14543304 | Hypo | cancer_general | PSMA1 | chr11 | 14866247 | 14866285 | Hypo | cancer_general | PDE3B |
| chr11 | 17741679 | 17741708 | Hypo | literature | MYOD1 | chr11 | 18100096 | 18100259 | Hypo | breast | SAAL1 |
| chr11 | 20408219 | 20408341 | Hypo | cancer_general | PRMT3 | chr11 | 20618292 | 20618322 | Hypo | esophageal | SLC6A5 |
| chr11 | 20618526 | 20618556 | Hypo | esophageal | SLC6A5 | chr11 | 31760124 | 31760235 | Hypo | ovarian | ELP4 |
| chr11 | 33264773 | 33264935 | Hypo | head_neck | — | chr11 | 33277455 | 33277485 | Hypo | cancer_general | HIPK3 |
| chr11 | 33318780 | 33318945 | Hypo | pancreas | HIPK3 | chr11 | 33858324 | 33858463 | Hypo | cancer_general | — |
| chr11 | 33993984 | 33994014 | Hypo | cancer_general | — | chr11 | 34535093 | 34535123 | Hypo | cancer_general | ELF5 |
| chr11 | 35684958 | 35685131 | Hypo | cancer_general | TRIM44 | chr11 | 44337533 | 44337571 | Hypo | cancer_general | ALX4 |
| chr11 | 46227561 | 46227654 | Hypo | cancer_general | — | chr11 | 46866293 | 46866510 | Hypo | cancer_general | LRP4-AS1 |
| chr11 | 46959190 | 46959251 | Hypo | cancer_general | C11orf49 | chr11 | 47260168 | 47260258 | Hypo | breast | NR1H3, DDB2, ACP2 |
| chr11 | 47358926 | 47359237 | Hypo | cancer_general | MYBPC3 SP11, SLC39A13, MYBPC3 | chr11 | 47363557 | 47363625 | Hypo | head_neck | MYBPC3 CELF1, RAPSN |
| chr11 | 47372828 | 47373002 | Hypo | pancreas | | chr11 | 47478438 | 47478500 | Hypo | breast | |
| chr11 | 47485995 | 47486141 | Hypo | lung | CELF1 CLP1, ZDHHC5 | chr11 | 57235406 | 57235436 | Hypo | cancer_general | RTN4RL2 TMX2, C11orf31, BTBD18, TMX2-CTNND1 |
| chr11 | 57437157 | 57437234 | Hypo | cancer_general | | chr11 | 57500982 | 57501068 | Hypo | cancer_general | |
| chr11 | 59329086 | 59329240 | Hypo | cancer_general | TRNA_Lys, U7, TRNA_Leu, JB175310, TRNA_Phe | chr11 | 59841403 | 59841533 | Hypo | cancer_general | MS4A3 |
| chr11 | 60927079 | 60927319 | Hypo | cancer_general | VPS37C DDB1, VWCE | chr11 | 61049694 | 61049736 | Hypo | cancer_general | VWCE |
| chr11 | 61058283 | 61058341 | Hypo | cancer_general | | chr11 | 61148730 | 61148768 | Hypo | colorectal | — |
| chr11 | 61154806 | 61154836 | Hypo | cancer_general | TMEM216 | chr11 | 61536985 | 61537014 | Hypo | literature | MYRF |
| chr11 | 61664655 | 61664770 | Hypo | cancer_general | RAB3IL1, FADS3 | chr11 | 61666106 | 61666136 | Hypo | cancer_general | RAB3IL1, FADS3 |

TABLE 11-continued

| chr | Start | Stop | Hypo/hyper | classification | annotation |
|---|---|---|---|---|---|
| chr11 | 61811996 | 61812151 | Hypo | cancer_general | |
| chr11 | 62370720 | 62370750 | Hypo | cancer_general | EML3, ROM1, MTA2 |
| chr11 | 62484517 | 62484547 | Hypo | breast | HNRNPUL2, GNG3 |
| chr11 | 62555752 | 62555782 | Hypo | cancer_general | NXF1, TMEM179B, TAF6L, TMEM223 |
| chr11 | 63431856 | 63431918 | Hypo | ovarian | ATL3 |
| chr11 | 63609824 | 63610013 | Hypo | cancer_general | MARK2 |
| chr11 | 63849394 | 63849426 | Hypo | cancer_general | MACROD1 |
| chr11 | 64105954 | 64106108 | Hypo | cancer_general | CCDC88B |
| chr11 | 64140397 | 64140427 | Hypo | cancer_general | MIR1237, RPS6KA4 |
| chr11 | 64796439 | 64796571 | Hypo | cancer_general | ARL2-SNX15, ARL2 |
| chr11 | 64903331 | 64903361 | Hypo | cancer_general | SYVN1, MRPL49 |
| chr11 | 65091272 | 65091369 | Hypo | cancer_general | DPF2, CDC42EP2 |
| chr11 | 65448943 | 65449022 | Hypo | cancer_general | |
| chr11 | 65510941 | 65511172 | Hypo | cancer_general | EIF1AD, AX747517, CST6, CATSPER1, BANF1 |
| chr11 | 65778952 | 65778981 | Hypo | literature | |
| chr11 | 66114279 | 66114331 | Hypo | cancer_general | TRNA_Ser, B3GNT1, BRMS1 |
| chr11 | 66324254 | 66324447 | Hypo | cancer_general | CTSF, ACTN3 |
| chr11 | 66511223 | 66511431 | Hypo | cancer_general | C11orf80 |
| chr11 | 66557543 | 66557710 | Hypo | cancer_general | C11orf80 |
| chr11 | 66649028 | 66649058 | Hypo | cancer_general | |
| chr11 | 67072239 | 67072396 | Hypo | cancer_general | SSH3, ANKRD13D, AK057681 |
| chr11 | 67248321 | 67248458 | Hypo | cancer_general | AIP |
| chr11 | 61880361 | 61880398 | Hypo | cancer_general | UBXN1, C11orf83, C11orf48, METTL12, SNORA57 |
| chr11 | 62440509 | 62440588 | Hypo | cancer_general | TTC9C, HNRNPUL2 |
| chr11 | 62497600 | 62497630 | Hypo | cancer_general | |
| chr11 | 63202941 | 63203091 | Hypo | cancer_general | |
| chr11 | 63432139 | 63432218 | Hypo | ovarian | ATL3 |
| chr11 | 63641072 | 63641256 | Hypo | breast | MARK2 |
| chr11 | 63934498 | 63934619 | Hypo | cancer_general | |
| chr11 | 64120879 | 64120909 | Hypo | cancer_general | RPS6KA4, CCDC88B |
| chr11 | 64578577 | 64578743 | Hypo | cancer_general | MEN1, MAP4K2 |
| chr11 | 64809584 | 64809906 | Hypo | cancer_general | NAALADL1, SAC3D1, ARL2-SNX15 |
| chr11 | 64950292 | 64950374 | Hypo | cancer_general | CAPN1, SPDYC |
| chr11 | 65364470 | 65364557 | Hypo | blood | MAP3K11, KCNK7, EHBP1L1 |
| chr11 | 65478376 | 65478611 | Hypo | cancer_general | KAT5, RNASEH2C |
| chr11 | 65511392 | 65511522 | Hypo | cancer_general | |
| chr11 | 65891131 | 65891227 | Hypo | cancer_general | PACS1 |
| chr11 | 66138094 | 66138260 | Hypo | cancer_general | SLC29A2, AX747485 |
| chr11 | 66454424 | 66454454 | Hypo | head_neck | SPTBN2, RBM4B |
| chr11 | 66513217 | 66513646 | Hypo | cancer_general | C11orf80 |
| chr11 | 66625207 | 66625240 | Hypo | cancer_general | LRFN4, PC |
| chr11 | 66658224 | 66658290 | Hypo | ovarian | |
| chr11 | 67210017 | 67210057 | Hypo | cancer_general | GPR152, CABP4, CORO1B, PTPRCAP, RPS6KB2 |
| chr11 | 67462643 | 67462833 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 67764187 | 67764254 | Hypo | cancer_general | UNC93B1 | chr11 | 67781196 | 67781564 | Hypo | lung | ALDH3B1, UNC93B1 |
| chr11 | 67797202 | 67797420 | Hypo | cancer_general | ALDH3B1, NDUFS8, MIR4691, TCIRG1 | chr11 | 67918044 | 67918145 | Hypo | pancreas | SUV420H1 |
| chr11 | 67999703 | 67999866 | Hypo | cancer_general | — | chr11 | 68221758 | 68222056 | Hypo | cancer_general | PPP6R3, LRP5 |
| chr11 | 68409558 | 68409588 | Hypo | hepatobiliary | — | chr11 | 68804728 | 68804776 | Hypo | cancer_general | — |
| chr11 | 69192566 | 69192784 | Hypo | cancer_general | — | chr11 | 69280561 | 69280633 | Hypo | cancer_general | — |
| chr11 | 69466004 | 69466042 | Hypo | literature | BC133018, CCND1, AK294004, ORAOV1 | chr11 | 71192746 | 71192889 | Hypo | cancer_general | NADSYN1 |
| chr11 | 71647544 | 71647574 | Hypo | pancreas | RNF121, LOC100133315 | chr11 | 71792437 | 71792496 | Hypo | cancer_general | MIR3165, NUMA1, LRTOMT |
| chr11 | 71863650 | 71863785 | Hypo | cancer_general | — | chr11 | 72413980 | 72414010 | Hypo | ovarian | BC150585, ARAP1 |
| chr11 | 72475677 | 72475711 | Hypo | cancer_general | STARD10 | chr11 | 72532348 | 72532378 | Hypo | cancer_general | ATG16L2 |
| chr11 | 73072907 | 73072953 | Hypo | cancer_general | ARHGEF17 | chr11 | 73310367 | 73310441 | Hypo | cancer_general | FAM168A |
| chr11 | 73481055 | 73481085 | Hypo | ovarian | RAB6A UCP2, DNAJB13 | chr11 | 73561763 | 73561798 | Hypo | ovarian | MRPL48 |
| chr11 | 73685698 | 73685845 | Hypo | ovarian |  | chr11 | 74246487 | 74246521 | Hypo | cancer_general | — |
| chr11 | 75459486 | 75459775 | Hypo | cancer_general | LOC283214 | chr11 | 75858210 | 75858240 | Hypo | colorectal | UVRAG |
| chr11 | 75859012 | 75859053 | Hypo | colorectal | UVRAG | chr11 | 76293588 | 76293618 | Hypo | head_neck | — |
| chr11 | 76371738 | 76372077 | Hypo | cancer_general | LRRC32 | chr11 | 76594692 | 76594722 | Hypo | ovarian | ACER3 |
| chr11 | 77533964 | 77534145 | Hypo | cancer_general | AAMDC, RSF1 | chr11 | 82998001 | 82998121 | Hypo | cancer_general | BC070093, CCDC90B |
| chr11 | 85709169 | 85709254 | Hypo | ovarian | PICALM | chr11 | 89052235 | 89052282 | Hypo | cancer_general | NOX4 PIWIL4, FUT4 |
| chr11 | 93911651 | 93911800 | Hypo | colorectal | PANX1 | chr11 | 94275794 | 94275951 | Hypo | colorectal |  |
| chr11 | 96517902 | 96517932 | Hypo | cancer_general | — | chr11 | 101723359 | 101723455 | Hypo | cancer_general | — |
| chr11 | 102158378 | 102158427 | Hypo | ovarian | — | chr11 | 102961347 | 102961649 | Hypo | cancer_general | DCUN1D5 |
| chr11 | 108236072 | 108236101 | Hypo | literature | C11orf65 HSPB2, HSPB2-C11orf52, CRYAB | chr11 | 108603233 | 108603263 | Hypo | cancer_general | DDX10 |
| chr11 | 111783548 | 111783577 | Hypo | literature |  | chr11 | 111976911 | 111976941 | Hypo | pancreas | — |
| chr11 | 116976126 | 116976156 | Hypo | cancer_general | — | chr11 | 116984568 | 116984665 | Hypo | cancer_general | — |
| chr11 | 117017686 | 117017773 | Hypo | ovarian | PAFAH1B2, AB231710, AB231711 | chr11 | 117055950 | 117056073 | Hypo | cancer_general | PAFAH1B2, SIDT2 |
| chr11 | 118724458 | 118724605 | Hypo | colorectal | — | chr11 | 118991033 | 118991079 | Hypo | cancer_general | HINFP, C2CD2L |
| chr11 | 119148865 | 119148945 | Hypo | literature | CBL | chr11 | 119149236 | 119149265 | Hypo | literature | CBL |
| chr11 | 120008105 | 120008504 | Hypo | cancer_general | TRIM29 | chr11 | 120367948 | 120368008 | Hypo | ovarian | — |
| chr11 | 120998701 | 120998825 | Hypo | ovarian | TECTA | chr11 | 121152057 | 121152203 | Hypo | cancer_general | — |
| chr11 | 122895443 | 122895485 | Hypo | cancer_general | LOC341056 | chr11 | 122961054 | 122961219 | Hypo | cancer_general | CLMP |
| chr11 | 123963874 | 123963994 | Hypo | cancer_general | — | chr11 | 125220500 | 125220643 | Hypo | cancer_general | PKNOX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 125755612 | 125755710 | Hypo | cancer_general | HYLS1, PUS3 | chr11 | 125758604 | 125758660 | Hypo | cancer_general | PUS3, HYLS1 |
| chr11 | 128657892 | 128657970 | Hypo | cancer_general | — | chr11 | 129907552 | 129907714 | Hypo | cancer_general | — |
| chr11 | 129931742 | 129931851 | Hypo | cancer_general | APLP2 | chr11 | 130343061 | 130343100 | Hypo | hepatobiliary | ADAMTS15 |
| chr11 | 130359769 | 130359915 | Hypo | cancer_general | — | chr11 | 130781550 | 130781781 | Hypo | ovarian | SNX19 |
| chr11 | 130785487 | 130788622 | Hypo | cancer_general | SNX19 | chr11 | 130854324 | 130854490 | Hypo | cancer_general | — |
| chr11 | 131522763 | 131522947 | Hypo | cancer_general | — | chr11 | 131766715 | 131766960 | Hypo | cancer_general | AK056505 |
| chr11 | 132484215 | 132484404 | Hypo | cancer_general | IGSF9B | chr11 | 133231739 | 133231832 | Hypo | cancer_general | SDHA |
| chr11 | 133792055 | 133792214 | Hypo | hepatobiliary | AHRR, PDCD6 | chr5 | 230673 | 230709 | Hypo | breast | AHRR |
| chr5 | 303272 | 303301 | Hypo | literature | AHRR | chr5 | 373363 | 373392 | Hypo | literature | — |
| chr5 | 415870 | 415899 | Hypo | literature | — | chr5 | 481012 | 481121 | Hypo | cancer_general | SLC9A3, PP7080, AK023178, FLJ00157, BC013821 |
| chr5 | 491335 | 491536 | Hypo | cancer_general | — | chr5 | 538758 | 538806 | Hypo | cancer_general | MIR4456 |
| chr5 | 554299 | 554538 | Hypo | cancer_general | — | chr5 | 554871 | 554900 | Hypo | literature | — |
| chr5 | 555158 | 555285 | Hypo | cancer_general | — | chr5 | 555965 | 555995 | Hypo | cancer_general | — |
| chr5 | 677889 | 678006 | Hypo | cancer_general | TPPP | chr5 | 909204 | 909304 | Hypo | head_neck | TRIP13 |
| chr5 | 912806 | 912835 | Hypo | literature | TRIP13 | chr5 | 1034600 | 1034653 | Hypo | cancer_general | NKD2 |
| chr5 | 1059523 | 1059556 | Hypo | blood | MIR4635, SLC12A7 | chr5 | 1117778 | 1118270 | Hypo | cancer_general | — |
| chr5 | 1131217 | 1131378 | Hypo | cancer_general | — | chr5 | 1136590 | 1136845 | Hypo | head_neck | — |
| chr5 | 1193381 | 1193521 | Hypo | cancer_general | SLC6A19 | chr5 | 1193880 | 1193944 | Hypo | cancer_general | SLC6A19 |
| chr5 | 1221197 | 1221307 | Hypo | cancer_general | SLC6A19, SLC6A18 | chr5 | 1259524 | 1259558 | Hypo | hepatobiliary | TERT |
| chr5 | 1271339 | 1271396 | Hypo | hepatobiliary | TERT | chr5 | 1295214 | 1295265 | Hypo | literature | TERT |
| chr5 | 1747022 | 1747098 | Hypo | cancer_general | — | chr5 | 1779526 | 1779556 | Hypo | hepatobiliary | — |
| chr5 | 1787378 | 1787418 | Hypo | cancer_general | — | chr5 | 1950794 | 1950960 | Hypo | cancer_general | — |
| chr5 | 2225439 | 2225469 | Hypo | lung | — | chr5 | 2324383 | 2324413 | Hypo | cancer_general | — |
| chr5 | 2367718 | 2367892 | Hypo | cancer_general | — | chr5 | 2541487 | 2541611 | Hypo | cancer_general | — |
| chr5 | 2753048 | 2753078 | Hypo | pancreas | C5orf38, IRX2 | chr5 | 3031879 | 3032018 | Hypo | cancer_general | — |
| chr5 | 3152146 | 3152176 | Hypo | hepatobiliary | — | chr5 | 3325042 | 3325272 | Hypo | cancer_general | — |
| chr5 | 3674053 | 3674224 | Hypo | cancer_general | — | chr5 | 4144367 | 4144516 | Hypo | cancer_general | UBE2QL1 |
| chr5 | 6228617 | 6228790 | Hypo | cancer_general | — | chr5 | 6482458 | 6482620 | Hypo | cancer_general | ANKRD33B |
| chr5 | 10249098 | 10249127 | Hypo | literature | — | chr5 | 10616516 | 10616550 | Hypo | cancer_general | — |
| chr5 | 16466784 | 16467120 | Hypo | cancer_general | CCT5, FAM173B, FAM134B, ZNF622 | chr5 | 16793851 | 16794008 | Hypo | hepatobiliary | MYO10 |
| chr5 | 16845452 | 16845619 | Hypo | hepatobiliary | MYO10 | chr5 | 16968118 | 16968148 | Hypo | hepatobiliary | — |
| chr5 | 17095895 | 17095927 | Hypo | hepatobiliary | — | chr5 | 17203012 | 17203177 | Hypo | cancer_general | LOC285696 |
| chr5 | 17311046 | 17311076 | Hypo | hepatobiliary | — | chr5 | 17512114 | 17512144 | Hypo | hepatobiliary | — |
| chr5 | 18034335 | 18034365 | Hypo | hepatobiliary | — | chr5 | 23011928 | 23011958 | Hypo | cancer_general | — |
| chr5 | 31572285 | 31572344 | Hypo | cancer_general | — | chr5 | 31691477 | 31691652 | Hypo | cancer_general | PDZD2 |
| chr5 | 31879243 | 31879282 | Hypo | hepatobiliary | PDZD2 | chr5 | 32042283 | 32042419 | Hypo | lung | — |
| chr5 | 32314345 | 32314379 | Hypo | cancer_general | MTMR12 | chr5 | 32333032 | 32333111 | Hypo | colorectal | — |
| chr5 | 32446143 | 32446274 | Hypo | cancer_general | ZFR | chr5 | 33234280 | 33234411 | Hypo | cancer_general | — |
| chr5 | 33298005 | 33298076 | Hypo | cancer_general | — | chr5 | 33509607 | 33509776 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 33936486 | 33936516 | Hypo | cancer_general | SLC45A2, RXFP3 | chr5 | 35874560 | 35874589 | Hypo | literature | IL7R |
| chr5 | 35939832 | 35939861 | Hypo | literature | CAPSL | chr5 | 37376644 | 37376674 | Hypo | cancer_general | WDR70, NUP155 |
| chr5 | 39281800 | 39281943 | Hypo | lung | C9 | chr5 | 39343181 | 39343348 | Hypo | cancer_general | C9 |
| chr5 | 40775147 | 40775313 | Hypo | cancer_general | PRKAA1 | chr5 | 42260050 | 42260453 | Hypo | esophageal, cancer_general | |
| chr5 | 42931966 | 42931996 | Hypo | cancer_general | | chr5 | 43215538 | 43215738 | Hypo | lung, cancer_general | NIM1 |
| chr5 | 43402678 | 43403084 | Hypo | cancer_general | CCL28 | chr5 | 43558065 | 43558099 | Hypo | cancer_general | PAIP1 |
| chr5 | 52887899 | 52888047 | Hypo | cancer_general | NDUFS4 | chr5 | 56077938 | 56078065 | Hypo | cancer_general | |
| chr5 | 56467399 | 56467666 | Hypo | cancer_general | GPBP1 | chr5 | 65181732 | 65181778 | Hypo | cancer_general | |
| chr5 | 67569803 | 67569832 | Hypo | literature | PIK3R1 | chr5 | 67588937 | 67589162 | Hypo | literature | PIK3R1 |
| chr5 | 67589598 | 67589627 | Hypo | literature | PIK3R1 | chr5 | 67590431 | 67590460 | Hypo | literature | PIK3R1 |
| chr5 | 67591068 | 67591157 | Hypo | literature | PIK3R1 | chr5 | 68391042 | 68391336 | Hypo | cancer_general | SLC30A5 |
| chr5 | 71106820 | 71107027 | Hypo | head_neck | | chr5 | 72528434 | 72528464 | Hypo | cancer_general | |
| chr5 | 74061571 | 74061786 | Hypo | cancer_general | NSA2, GFM2 | chr5 | 74991793 | 74991908 | Hypo | cancer_general | POC5 |
| chr5 | 76327468 | 76327697 | Hypo | cancer_general | AGGF1 | chr5 | 77655342 | 77655388 | Hypo | cancer_general | SCAMP1, BC039455 |
| chr5 | 78005726 | 78005913 | Hypo | cancer_general | | chr5 | 78039632 | 78039673 | Hypo | head_neck | |
| chr5 | 78910189 | 78910332 | Hypo | cancer_general | PAPD4 | chr5 | 79554097 | 79554169 | Hypo | colorectal | SERINC5 |
| chr5 | 79563425 | 79563643 | Hypo | cancer_general | | chr5 | 79598681 | 79598836 | Hypo | cancer_general | LOC644936 |
| chr5 | 79783240 | 79783421 | Hypo | cancer_general | ZFYVE16, FAM151B | chr5 | 79947584 | 79947707 | Hypo | cancer_general | DHFR, MSH3, MTRNR2L2 |
| chr5 | 82168369 | 82168480 | Hypo | colorectal | | chr5 | 86414242 | 86414297 | Hypo | cancer_general | BC034940, MIR4280 |
| chr5 | 87986547 | 87986581 | Hypo | pancreas | | chr5 | 94889396 | 94889434 | Hypo | cancer_general | ARSK, TTC37 |
| chr5 | 94982042 | 94982225 | Hypo | cancer_general | RFESD, SPATA9 | chr5 | 96114587 | 96114632 | Hypo | breast | ERAP1, CAST |
| chr5 | 111987744 | 111987818 | Hypo | colorectal | | chr5 | 112042844 | 112042873 | Hypo | literature | APC |
| chr5 | 112170808 | 112170837 | Hypo | literature | APC | chr5 | 112175198 | 112175227 | Hypo | literature | APC |
| chr5 | 112175640 | 112175669 | Hypo | literature | APC | chr5 | 112340666 | 112340704 | Hypo | head_neck | DCP2 |
| chr5 | 115154758 | 115154825 | Hypo | cancer_general | ATG12, CDO1 | chr5 | 115176039 | 115176228 | Hypo | cancer_general | ATG12, AP3S1 |
| chr5 | 116143271 | 116143325 | Hypo | hepatobiliary | | chr5 | 120399966 | 120400129 | Hypo | cancer_general | |
| chr5 | 124128410 | 124128497 | Hypo | colorectal | | chr5 | 126231644 | 126231674 | Hypo | ovarian | 3-Mar |
| chr5 | 126245097 | 126245133 | Hypo | pancreas | 3-Mar | chr5 | 127088743 | 127088773 | Hypo | cancer_general | |
| chr5 | 130153448 | 130153623 | Hypo | cancer_general | | chr5 | 131134159 | 131134203 | Hypo | ovarian | LOC728637, ACSL6, FNIP1 |
| chr5 | 133820008 | 133820040 | Hypo | cancer_general | LOC340073, LOC100996485 | chr5 | 133968996 | 133969192 | Hypo | cancer_general | SAR1B |
| chr5 | 134582864 | 134582894 | Hypo | cancer_general | | chr5 | 137404150 | 137404180 | Hypo | cancer_general | |
| chr5 | 137912037 | 137912148 | Hypo | ovarian | | chr5 | 138196197 | 138196408 | Hypo | head_neck | LRRTM2, CTNNA1 |
| chr5 | 138273817 | 138273854 | Hypo | pancreas | SIL1, CTNNA1 | chr5 | 139454108 | 139454202 | Hypo | ovarian | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 139779555 | 139779871 | Hypo | cancer_general | ANKHD1, ANKHD1-EIF4EBP3, BC030152 | chr5 | 147003444 | 147003536 | Hypo | cancer_general | JAKMIP2, JAKMIP2-AS1 |
| chr5 | 147326357 | 147326510 | Hypo | cancer_general | — | chr5 | 149503827 | 149503856 | Hypo | literature | PDGFRB |
| chr5 | 150029147 | 150029245 | Hypo | ovarian | SYNPO | chr5 | 154030048 | 154030160 | Hypo | cancer_general | — |
| chr5 | 154061801 | 154061894 | Hypo | cancer_general | — | chr5 | 154209926 | 154209987 | Hypo | cancer_general | FAXDC2 |
| chr5 | 154318148 | 154318329 | Hypo | cancer_general | MRPL22, GEMIN5 | chr5 | 156485385 | 156485415 | Hypo | cancer_general | HAVCR1 |
| chr5 | 156558444 | 156558689 | Hypo | cancer_general | MED7 | chr5 | 156655170 | 156655200 | Hypo | cancer_general | ITK |
| chr5 | 156874257 | 156874308 | Hypo | cancer_general | ADAM19 | chr5 | 157078419 | 157078449 | Hypo | cancer_general | SOX30 |
| chr5 | 157673799 | 157673964 | Hypo | cancer_general | — | chr5 | 158524865 | 158524925 | Hypo | cancer_general | AK123543, EBF1 |
| chr5 | 158612981 | 158613074 | Hypo | lung, cancer_general | RNF145 | chr5 | 159437197 | 159437235 | Hypo | cancer_general | TTC1 |
| chr5 | 166865449 | 166865616 | Hypo | cancer_general | TENM2 | chr5 | 168233396 | 168233482 | Hypo | cancer_general | SLIT3 |
| chr5 | 169366082 | 169366201 | Hypo | cancer_general | FAM196B, DOCK2 | chr5 | 169532927 | 169533012 | Hypo | cancer_general | FOXI1 |
| chr5 | 171352123 | 171352153 | Hypo | head_neck | FBXW11 | chr5 | 172354043 | 172354118 | Hypo | ovarian | ERGIC1 |
| chr5 | 172485539 | 172485586 | Hypo | cancer_general | CREBRF, Y_RNA | chr5 | 172672477 | 172672663 | Hypo | cancer_general | — |
| chr5 | 174159104 | 174159134 | Hypo | cancer_general | MSX2 | chr5 | 174921456 | 174921629 | Hypo | cancer_general | SFXN1 |
| chr5 | 175790961 | 175790991 | Hypo | ovarian | ARL10, KIAA1191 | chr5 | 175831257 | 175831326 | Hypo | colorectal | CLTB |
| chr5 | 175876388 | 175876504 | Hypo | cancer_general | FAF2 | chr5 | 175971447 | 175971615 | Hypo | cancer_general | CDHR2 |
| chr5 | 175978889 | 175978976 | Hypo | cancer_general | CDHR2 | chr5 | 176295786 | 176295892 | Hypo | hepatobiliary | UNC5A |
| chr5 | 176520166 | 176520195 | Hypo | literature | FGFR4 | chr5 | 176522400 | 176522566 | Hypo | literature | FGFR4 |
| chr5 | 176764100 | 176764169 | Hypo | breast | LMAN2 | chr5 | 177020093 | 177020153 | Hypo | cancer_general | B4GALT7, TMED9 |
| chr5 | 177031167 | 177031197 | Hypo | cancer_general | B4GALT7, TMED9 | chr5 | 177408292 | 177408443 | Hypo | cancer_general | — |
| chr5 | 177512244 | 177512377 | Hypo | cancer_general | — | chr5 | 177556807 | 177557022 | Hypo | cancer_general | AK127224, N4BP3, RMND5B |
| chr5 | 177579824 | 177580065 | Hypo | cancer_general | NHP2, RMND5B | chr5 | 177644565 | 177644601 | Hypo | colorectal | AGXT2L2, HNRNPAB |
| chr5 | 177713376 | 177713468 | Hypo | cancer_general | — | chr5 | 178151333 | 178151363 | Hypo | hepatobiliary | ZNF354A |
| chr5 | 178576356 | 178576499 | Hypo | cancer_general | ADAMTS2 | chr5 | 178655753 | 178655871 | Hypo | cancer_general | ADAMTS2 |
| chr5 | 178781548 | 178781577 | Hypo | literature | ADAMTS2 | chr5 | 178955527 | 178955656 | Hypo | cancer_general | AX747985 |
| chr5 | 178969722 | 178969752 | Hypo | cancer_general | RUFY1 | chr5 | 178978946 | 178978976 | Hypo | cancer_general | RUFY1 |
| chr5 | 179060235 | 179060655 | Hypo | cancer_general | C5orf60 | chr5 | 179098595 | 179098633 | Hypo | cancer_general | CBY3 |
| chr5 | 179214113 | 179214196 | Hypo | cancer_general | LTC4S, MAML1 | chr5 | 179217377 | 179217447 | Hypo | esophageal | LTC4S, MGAT4B, MIR1229 |
| chr5 | 179270584 | 179270748 | Hypo | ovarian | AK095057, C5orf45, SQSTM1 | chr5 | 179553207 | 179553237 | Hypo | cancer_general | RASGEF1C |
| chr5 | 180030654 | 180030700 | Hypo | cancer_general | FLT4 | chr5 | 180047440 | 180047606 | Hypo | cancer_general | FLT4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 180326126 | 180326156 | Hypo | cancer_general | BTNL8 | chr5 | 180454232 | 180454334 | Hypo | cancer_general | TRIM7 |
| chr5 | 180612346 | 180612376 | Hypo | cancer_general | TRNA_Leu, TRNA_Val, TRNA_Pro, TRNA_Thr, TRIM7 | chr5 | 180629320 | 180629350 | Hypo | cancer_general | TRIM7, TRNA_Ala, TRNA_Lys |
| chr5 | 180636016 | 180636205 | Hypo | cancer_general | TRNA_Ala, TRIM7, TRNA_Val, TRNA_Lys | JH636052.4 | 2022736 | 2022766 | Hypo | cancer_general | — |
| HPV16 | 111 | 140 | Hypo | virus | — | HPV16 | 367 | 396 | Hypo | virus | — |
| HPV16 | 623 | 652 | Hypo | virus | — | HPV16 | 879 | 908 | Hypo | virus | — |
| HPV16 | 1135 | 1164 | Hypo | virus | — | HPV16 | 1391 | 1420 | Hypo | virus | — |
| HPV16 | 1647 | 1676 | Hypo | virus | — | HPV16 | 1903 | 1932 | Hypo | virus | — |
| HPV16 | 2159 | 2188 | Hypo | virus | — | HPV16 | 2415 | 2444 | Hypo | virus | — |
| HPV16 | 2671 | 2700 | Hypo | virus | — | HPV16 | 2927 | 2956 | Hypo | virus | — |
| HPV16 | 3183 | 3212 | Hypo | virus | — | HPV16 | 3439 | 3468 | Hypo | virus | — |
| HPV16 | 3695 | 3724 | Hypo | virus | — | HPV16 | 3951 | 3980 | Hypo | virus | — |
| HPV16 | 4207 | 4236 | Hypo | virus | — | HPV16 | 4463 | 4492 | Hypo | virus | — |
| HPV16 | 4719 | 4748 | Hypo | virus | — | HPV16 | 4975 | 5004 | Hypo | virus | — |
| HPV16 | 5231 | 5260 | Hypo | virus | — | HPV16 | 5487 | 5516 | Hypo | virus | — |
| HPV16 | 5743 | 5772 | Hypo | virus | — | HPV16 | 5999 | 6028 | Hypo | virus | — |
| HPV16 | 6255 | 6284 | Hypo | virus | — | HPV16 | 6511 | 6540 | Hypo | virus | — |
| HPV16 | 6767 | 6796 | Hypo | virus | — | HPV16 | 7023 | 7052 | Hypo | virus | — |
| HPV16 | 7279 | 7308 | Hypo | virus | — | HPV16 | 7535 | 7564 | Hypo | virus | — |
| chr13 | 20451144 | 20451360 | Hypo | cancer_general | — | chr13 | 21713233 | 21713513 | Hypo | cancer_general | SAP18 |
| chr13 | 23653781 | 23653813 | Hypo | hepatobiliary | — | chr13 | 24099683 | 24099713 | Hypo | hepatobiliary | — |
| chr13 | 25668799 | 25668829 | Hypo | cancer_general | PABPC3 | chr13 | 26340608 | 26340755 | Hypo | cancer_general | ATP8A2 |
| chr13 | 27699893 | 27699981 | Hypo | cancer_general | USP12 | chr13 | 28239909 | 28240164 | Hypo | breast | — |
| chr13 | 28589765 | 28589794 | Hypo | literature | FLT3 | chr13 | 28592605 | 28592658 | Hypo | literature | FLT3 |
| chr13 | 28601345 | 28601374 | Hypo | literature | FLT3 | chr13 | 28602326 | 28602355 | Hypo | literature | FLT3 |
| chr13 | 28608233 | 28608355 | Hypo | literature | FLT3 | chr13 | 28610123 | 28610152 | Hypo | literature | FLT3 |
| chr13 | 28706016 | 28706140 | Hypo | cancer_general | PAN3-AS1, PAN3 | chr13 | 29112395 | 29112444 | Hypo | hepatobiliary | — |
| chr13 | 30141688 | 30141718 | Hypo | cancer_general | SLC7A1 | chr13 | 30707569 | 30707599 | Hypo | cancer_general | — |
| chr13 | 31185432 | 31185548 | Hypo | blood | USPL1 | chr13 | 31742953 | 31743177 | Hypo | cancer_general | — |
| chr13 | 36269480 | 36269509 | Hypo | literature | — | chr13 | 36541300 | 36541329 | Hypo | literature | HSPH1 |
| chr13 | 36553399 | 36553428 | Hypo | literature | — | chr13 | 36588100 | 36588129 | Hypo | literature | — |
| chr13 | 36909206 | 36909236 | Hypo | hepatobiliary | SPG20 | chr13 | 37643942 | 37644005 | Hypo | cancer_general | LHFP |
| chr13 | 38402239 | 38402268 | Hypo | literature | TRPC4 | chr13 | 40000498 | 40000528 | Hypo | hepatobiliary | ELF1, SUGT1P3 |
| chr13 | 41346048 | 41346088 | Hypo | cancer_general | MRPS31 | chr13 | 41496324 | 41496478 | Hypo | cancer_general | — |
| chr13 | 41884500 | 41884688 | Hypo | cancer_general | NAA16 | chr13 | 43620862 | 43621006 | Hypo | colorectal | DNAJC15 |
| chr13 | 45905088 | 45905264 | Hypo | cancer_general | TPT1, SNORA31, DL489966, D28408 | chr13 | 46649031 | 46649141 | Hypo | pancreas | CPB2, CPB2-AS1 |
| chr13 | 46660839 | 46660869 | Hypo | cancer_general | CPB2, CPB2-AS1 | chr13 | 47407767 | 47407796 | Hypo | literature | HTR2A |
| chr13 | 47472315 | 47472344 | Hypo | literature | HTR2A | chr13 | 47526030 | 47526182 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 48478576 | 48478605 | Hypo | literature | — | chr13 | 48667877 | 48667907 | Hypo | cancer_general | — |
| chr13 | 50266473 | 50266573 | Hypo | cancer_general | KPNA3, EBPL | chr13 | 50367946 | 50368123 | Hypo | cancer_general | KPNA3 |
| chr13 | 50421504 | 50421696 | Hypo | esophageal | — | chr13 | 50639705 | 50639799 | Hypo | head_neck | DLEU2 |
| chr13 | 52270145 | 52270175 | Hypo | cancer_general | WDFY2 | chr13 | 52565068 | 52565194 | Hypo | cancer_general | — |
| chr13 | 52580318 | 52580369 | Hypo | cancer_general | UTP14C, ALG11 | chr13 | 55146522 | 55146551 | Hypo | literature | — |
| chr13 | 55373897 | 55373926 | Hypo | literature | — | chr13 | 55628658 | 55628687 | Hypo | literature | — |
| chr13 | 56762456 | 56762485 | Hypo | literature | — | chr13 | 57714539 | 57714568 | Hypo | literature | PRR20D |
| chr13 | 58892774 | 58892803 | Hypo | literature | — | chr13 | 59531686 | 59531715 | Hypo | literature | — |
| chr13 | 62132346 | 62132375 | Hypo | literature | — | chr13 | 64650200 | 64650229 | Hypo | literature | — |
| chr13 | 65552287 | 65552287 | Hypo | literature | — | chr13 | 66697959 | 66698124 | Hypo | hepatobiliary | — |
| chr13 | 67196371 | 67196400 | Hypo | literature | U7 | chr13 | 67197158 | 67197187 | Hypo | literature | U7 |
| chr13 | 68488923 | 68488952 | Hypo | literature | — | chr13 | 68682015 | 68682044 | Hypo | literature | — |
| chr13 | 68745282 | 68745311 | Hypo | literature | — | chr13 | 69796842 | 69796871 | Hypo | literature | — |
| chr13 | 71498386 | 71498415 | Hypo | literature | — | chr13 | 73184723 | 73184752 | Hypo | literature | — |
| chr13 | 73336049 | 73336078 | Hypo | literature | DIS3, BORA | chr13 | 73619660 | 73619784 | Hypo | colorectal | KLF5 |
| chr13 | 76440730 | 76440760 | Hypo | colorectal | C13orf45, AK123459 | chr13 | 76869421 | 76869450 | Hypo | literature | — |
| chr13 | 77553779 | 77553809 | Hypo | cancer_general | — | chr13 | 79693095 | 79693124 | Hypo | literature | — |
| chr13 | 79993101 | 79993142 | Hypo | lung | RBM26-AS1 | chr13 | 87731371 | 87731400 | Hypo | literature | — |
| chr13 | 88629123 | 88629152 | Hypo | literature | — | chr13 | 88788883 | 88788912 | Hypo | literature | — |
| chr13 | 88997906 | 88997935 | Hypo | literature | — | chr13 | 89815436 | 89815465 | Hypo | literature | — |
| chr13 | 90015503 | 90015532 | Hypo | literature | — | chr13 | 90015897 | 90015926 | Hypo | literature | — |
| chr13 | 91755723 | 91755837 | Hypo | hepatobiliary | — | chr13 | 91948489 | 91948519 | Hypo | cancer_general | — |
| chr13 | 93859304 | 93859333 | Hypo | literature | — | chr13 | 94107209 | 94107238 | Hypo | literature | GPC6 |
| chr13 | 95086143 | 95086172 | Hypo | literature | DCT | chr13 | 96031705 | 96031815 | Hypo | cancer_general | — |
| chr13 | 96177285 | 96177315 | Hypo | head_neck | CLDN10-AS1, CLDN10 | chr13 | 97761876 | 97761925 | Hypo | pancreas | — |
| chr13 | 99851676 | 99851706 | Hypo | cancer_general | UBAC2-AS1, UBAC2, 7SK | chr13 | 102197373 | 102197408 | Hypo | cancer_general | ITGBL1 |
| chr13 | 103821419 | 103821448 | Hypo | literature | — | chr13 | 105484285 | 105484314 | Hypo | literature | — |
| chr13 | 107827301 | 107827331 | Hypo | hepatobiliary | FAM155A ABHD13, LIG4 | chr13 | 108816328 | 108816383 | Hypo | cancer_general | — |
| chr13 | 108869613 | 108869830 | Hypo | cancer_general | CARKD | chr13 | 110434451 | 110434593 | Hypo | cancer_general | IRS2 |
| chr13 | 111278255 | 111278426 | Hypo | cancer_general | — | chr13 | 111363787 | 111363972 | Hypo | cancer_general | ING1, DJ031140, CARS2 |
| chr13 | 112272991 | 112273088 | Hypo | cancer_general | — | chr13 | 112712499 | 112712582 | Hypo | cancer_general | SOX1 |
| chr13 | 112758274 | 112758426 | Hypo | cancer_general | AK055145 | chr13 | 113598618 | 113598851 | Hypo | cancer_general | BC035340 |
| chr13 | 113938542 | 113938603 | Hypo | cancer_general | — | chr13 | 113985679 | 113986053 | Hypo | cancer_general | GRTP1, LAMP1 |
| chr13 | 114055983 | 114056137 | Hypo | literature, cancer_general | — | chr13 | 114060064 | 114060333 | Hypo | breast | — |
| chr13 | 114074768 | 114074853 | Hypo | cancer_general | ADPRHL1 | chr13 | 114082984 | 114083014 | Hypo | breast | ADPRHL1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 114123168 | 114123291 | Hypo | cancer_general | DCUN1D2 | chr13 | 114189737 | 114189809 | Hypo | colorectal | TMCO3 |
| chr13 | 114221622 | 114221652 | Hypo | cancer_general | — | chr13 | 114304565 | 114304927 | Hypo | cancer_general | ATP4B, TFDP1 |
| chr13 | 114479404 | 114479434 | Hypo | cancer_general | TMEM255B | chr13 | 114498017 | 114498260 | Hypo | cancer_general | TMEM255B |
| chr13 | 114568046 | 114568076 | Hypo | cancer_general | LOC100506394 | chr13 | 114748342 | 114748638 | Hypo | cancer_general | RASA3 |
| chr13 | 114766270 | 114766300 | Hypo | ovarian | RASA3 | chr13 | 114780561 | 114781061 | Hypo | cancer_general | RASA3 |
| chr13 | 114807617 | 114807815 | Hypo | head_neck, cancer_general | RASA3 | chr13 | 114855635 | 114855669 | Hypo | cancer_general | — |
| chr13 | 114862308 | 114862368 | Hypo | cancer_general | — | chr13 | 114961823 | 114961933 | Hypo | cancer_general | — |
| EBV-B95-8 | 967 | 996 | Hypo | virus | — | EBV-B95-8 | 3766 | 3795 | Hypo | virus | — |
| EBV-B95-8 | 4234 | 4263 | Hypo | virus | — | EBV-B95-8 | 5326 | 5355 | Hypo | virus | — |
| EBV-B95-8 | 6553 | 6582 | Hypo | virus | — | EBV-B95-8 | 8800 | 8829 | Hypo | virus | — |
| EBV-B95-8 | 13471 | 13500 | Hypo | virus | — | EBV-B95-8 | 46577 | 46606 | Hypo | virus | — |
| EBV-B95-8 | 48222 | 48251 | Hypo | virus | — | EBV-B95-8 | 52842 | 52871 | Hypo | virus | — |
| EBV-B95-8 | 53561 | 53590 | Hypo | virus | — | EBV-B95-8 | 54377 | 54406 | Hypo | virus | — |
| EBV-B95-8 | 54778 | 54807 | Hypo | virus | — | EBV-B95-8 | 55067 | 55096 | Hypo | virus | — |
| EBV-B95-8 | 55893 | 55922 | Hypo | virus | — | EBV-B95-8 | 56735 | 56764 | Hypo | virus | — |
| EBV-B95-8 | 58227 | 58256 | Hypo | virus | — | EBV-B95-8 | 58926 | 58955 | Hypo | virus | — |
| EBV-B95-8 | 59581 | 59610 | Hypo | virus | — | EBV-B95-8 | 60099 | 60128 | Hypo | virus | — |
| EBV-B95-8 | 60877 | 60906 | Hypo | virus | — | EBV-B95-8 | 61319 | 61348 | Hypo | virus | — |
| EBV-B95-8 | 62302 | 62331 | Hypo | virus | — | EBV-B95-8 | 62840 | 62869 | Hypo | virus | — |
| EBV-B95-8 | 63178 | 63207 | Hypo | virus | — | EBV-B95-8 | 63601 | 63630 | Hypo | virus | — |
| EBV-B95-8 | 63935 | 63964 | Hypo | virus | — | EBV-B95-8 | 64590 | 64619 | Hypo | virus | — |
| EBV-B95-8 | 66726 | 66755 | Hypo | virus | — | EBV-B95-8 | 67486 | 67515 | Hypo | virus | — |
| EBV-B95-8 | 67857 | 67886 | Hypo | virus | — | EBV-B95-8 | 69228 | 69257 | Hypo | virus | — |
| EBV-B95-8 | 69798 | 69827 | Hypo | virus | — | EBV-B95-8 | 70439 | 70468 | Hypo | virus | — |
| EBV-B95-8 | 70839 | 70868 | Hypo | virus | — | EBV-B95-8 | 71938 | 71967 | Hypo | virus | — |
| EBV-B95-8 | 72204 | 72233 | Hypo | virus | — | EBV-B95-8 | 72535 | 72564 | Hypo | virus | — |
| EBV-B95-8 | 72983 | 73012 | Hypo | virus | — | EBV-B95-8 | 73950 | 73979 | Hypo | virus | — |
| EBV-B95-8 | 74304 | 74333 | Hypo | virus | — | EBV-B95-8 | 74689 | 74718 | Hypo | virus | — |
| EBV-B95-8 | 74978 | 75007 | Hypo | virus | — | EBV-B95-8 | 75256 | 75285 | Hypo | virus | — |
| EBV-B95-8 | 77784 | 77813 | Hypo | virus | — | EBV-B95-8 | 79618 | 79647 | Hypo | virus | — |
| EBV-B95-8 | 80289 | 80318 | Hypo | virus | — | EBV-B95-8 | 80704 | 80733 | Hypo | virus | — |
| EBV-B95-8 | 81198 | 81227 | Hypo | virus | — | EBV-B95-8 | 81629 | 81658 | Hypo | virus | — |
| EBV-B95-8 | 81888 | 81917 | Hypo | virus | — | EBV-B95-8 | 82225 | 82254 | Hypo | virus | — |
| EBV-B95-8 | 82703 | 82732 | Hypo | virus | — | EBV-B95-8 | 83438 | 83467 | Hypo | virus | — |
| EBV-B95-8 | 85345 | 85374 | Hypo | virus | — | EBV-B95-8 | 86299 | 86328 | Hypo | virus | — |
| EBV-B95-8 | 87104 | 87133 | Hypo | virus | — | EBV-B95-8 | 89959 | 89988 | Hypo | virus | — |
| EBV-B95-8 | 90915 | 90944 | Hypo | virus | — | EBV-B95-8 | 92531 | 92560 | Hypo | virus | — |
| EBV-B95-8 | 94071 | 94100 | Hypo | virus | — | EBV-B95-8 | 94731 | 94760 | Hypo | virus | — |
| EBV-B95-8 | 95084 | 95113 | Hypo | virus | — | EBV-B95-8 | 97482 | 97511 | Hypo | virus | — |
| EBV-B95-8 | 98245 | 98274 | Hypo | virus | — | EBV-B95-8 | 99224 | 99253 | Hypo | virus | — |
| EBV-B95-8 | 100235 | 100264 | Hypo | virus | — | EBV-B95-8 | 101009 | 101038 | Hypo | virus | — |
| EBV-B95-8 | 102716 | 102745 | Hypo | virus | — | EBV-B95-8 | 104004 | 104033 | Hypo | virus | — |
| EBV-B95-8 | 105019 | 105048 | Hypo | virus | — | EBV-B95-8 | 105284 | 105313 | Hypo | virus | — |
| EBV-B95-8 | 107231 | 107260 | Hypo | virus | — | EBV-B95-8 | 108023 | 108052 | Hypo | virus | — |
| EBV-B95-8 | 108370 | 108399 | Hypo | virus | — | EBV-B95-8 | 109086 | 109115 | Hypo | virus | — |
| EBV-B95-8 | 110250 | 110279 | Hypo | virus | — | EBV-B95-8 | 110626 | 110655 | Hypo | virus | — |
| EBV-B95-8 | 111690 | 111719 | Hypo | virus | — | EBV-B95-8 | 112112 | 112141 | Hypo | virus | — |
| EBV-B95-8 | 114429 | 114458 | Hypo | virus | — | EBV-B95-8 | 114749 | 114778 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| EBV-B95-8 | 115006 | 115035 | Hypo | virus | — | EBV-B95-8 | 115597 | 115626 | Hypo | virus | — |
| EBV-B95-8 | 116382 | 116411 | Hypo | virus | — | EBV-B95-8 | 116649 | 116678 | Hypo | virus | — |
| EBV-B95-8 | 118647 | 118676 | Hypo | virus | — | EBV-B95-8 | 119542 | 119571 | Hypo | virus | — |
| EBV-B95-8 | 120350 | 120379 | Hypo | virus | — | EBV-B95-8 | 121382 | 121411 | Hypo | virus | — |
| EBV-B95-8 | 123037 | 123066 | Hypo | virus | — | EBV-B95-8 | 123570 | 123599 | Hypo | virus | — |
| EBV-B95-8 | 124913 | 124942 | Hypo | virus | — | EBV-B95-8 | 125376 | 125405 | Hypo | virus | — |
| EBV-B95-8 | 125805 | 125834 | Hypo | virus | — | EBV-B95-8 | 126337 | 126366 | Hypo | virus | — |
| EBV-B95-8 | 127493 | 127522 | Hypo | virus | — | EBV-B95-8 | 127905 | 127934 | Hypo | virus | — |
| EBV-B95-8 | 128805 | 128834 | Hypo | virus | — | EBV-B95-8 | 130244 | 130273 | Hypo | virus | — |
| EBV-B95-8 | 130690 | 130719 | Hypo | virus | — | EBV-B95-8 | 131603 | 131632 | Hypo | virus | — |
| EBV-B95-8 | 134325 | 134354 | Hypo | virus | — | EBV-B95-8 | 135032 | 135061 | Hypo | virus | — |
| EBV-B95-8 | 135599 | 135628 | Hypo | virus | — | EBV-B95-8 | 136148 | 136177 | Hypo | virus | — |
| EBV-B95-8 | 136680 | 136709 | Hypo | virus | — | EBV-B95-8 | 137805 | 137834 | Hypo | virus | — |
| EBV-B95-8 | 138375 | 138404 | Hypo | virus | — | EBV-B95-8 | 139745 | 139774 | Hypo | virus | — |
| EBV-B95-8 | 140610 | 140639 | Hypo | virus | — | EBV-B95-8 | 141137 | 141166 | Hypo | virus | — |
| EBV-B95-8 | 142290 | 142319 | Hypo | virus | — | EBV-B95-8 | 142763 | 142792 | Hypo | virus | — |
| EBV-B95-8 | 143078 | 143107 | Hypo | virus | — | EBV-B95-8 | 144318 | 144347 | Hypo | virus | — |
| EBV-B95-8 | 145216 | 145245 | Hypo | virus | — | EBV-B95-8 | 145638 | 145667 | Hypo | virus | — |
| EBV-B95-8 | 147044 | 147073 | Hypo | virus | — | EBV-B95-8 | 148404 | 148433 | Hypo | virus | — |
| EBV-B95-8 | 150099 | 150128 | Hypo | virus | — | EBV-B95-8 | 150443 | 150472 | Hypo | virus | — |
| EBV-B95-8 | 152230 | 152259 | Hypo | virus | — | EBV-B95-8 | 153127 | 153156 | Hypo | virus | — |
| EBV-B95-8 | 153468 | 153497 | Hypo | virus | — | EBV-B95-8 | 153800 | 153829 | Hypo | virus | — |
| EBV-B95-8 | 154204 | 154233 | Hypo | virus | — | EBV-B95-8 | 156501 | 156530 | Hypo | virus | — |
| EBV-B95-8 | 156773 | 156802 | Hypo | virus | — | EBV-B95-8 | 157345 | 157374 | Hypo | virus | — |
| EBV-B95-8 | 159211 | 159240 | Hypo | virus | — | EBV-B95-8 | 159561 | 159590 | Hypo | virus | — |
| EBV-B95-8 | 161193 | 161222 | Hypo | virus | — | EBV-B95-8 | 161698 | 161727 | Hypo | virus | — |
| EBV-B95-8 | 162343 | 162372 | Hypo | virus | — | EBV-B95-8 | 163798 | 163827 | Hypo | virus | — |
| EBV-B95-8 | 164471 | 164500 | Hypo | virus | — | EBV-B95-8 | 165234 | 165263 | Hypo | virus | — |
| EBV-B95-8 | 166280 | 166309 | Hypo | virus | — | EBV-B95-8 | 167347 | 167376 | Hypo | virus | — |
| EBV-B95-8 | 167600 | 167629 | Hypo | virus | — | EBV-B95-8 | 167942 | 167971 | Hypo | virus | — |
| EBV-B95-8 | 168551 | 168580 | Hypo | virus | — | EBV-B95-8 | 171304 | 171333 | Hypo | virus | — |
| HBV | 111 | 140 | Hypo | virus | — | HBV | 381 | 410 | Hypo | virus | — |
| HBV | 651 | 680 | Hypo | virus | — | HBV | 921 | 950 | Hypo | virus | — |
| HBV | 1191 | 1220 | Hypo | virus | — | HBV | 1461 | 1490 | Hypo | virus | — |
| HBV | 1731 | 1760 | Hypo | virus | — | HBV | 2001 | 2030 | Hypo | virus | — |
| HBV | 2271 | 2300 | Hypo | virus | — | HBV | 2541 | 2570 | Hypo | virus | — |
| HBV | 2811 | 2840 | Hypo | virus | — | chrX | 3631506 | 3631633 | Hypo | breast | PRKX |
| chrX | 3746612 | 3746642 | Hypo | head_neck | TRNA_Ile, LOC389906 | chrX | 15807465 | 15807693 | Hypo | cancer_general | INE2, CA5B, ZRSR2 |
| chrX | 20148710 | 20148739 | Hypo | literature | SCARNA9L, EIF1AX | chrX | 20160594 | 20160914 | Hypo | cancer_general | RPS6KA3, SCARNA9L, EIF1AX |
| chrX | 44730179 | 44730271 | Hypo | cancer_general | KDM6A | chrX | 47039370 | 47039399 | Hypo | literature | RBM10 |
| chrX | 47426106 | 47426144 | Hypo | literature | SYN1, ARAF | chrX | 47426780 | 47426821 | Hypo | literature | SYN1, ARAF |
| chrX | 66931448 | 66931477 | Hypo | literature | AR | chrX | 66937356 | 66937385 | Hypo | literature | AR |
| chrX | 66943529 | 66943567 | Hypo | literature | AR | chrX | 70339239 | 70339268 | Hypo | literature | MED12, IL2RG |
| chr15 | 100228394 | 100228431 | Hypo | head_neck | ARL13A | chr15 | 22822348 | 22822488 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 23035709 | 23035781 | Hypo | cancer_general | NIPA1, NIPA2 | chr15 | 23162337 | 23162372 | Hypo | cancer_general | — |
| chr15 | 23273146 | 23273330 | Hypo | cancer_general | HERC2P2, JB175342, DQ572979 | chr15 | 23692316 | 23692453 | Hypo | cancer_general | LOC283685, GOLGA6L2 |
| chr15 | 29452432 | 29452462 | Hypo | hepatobiliary | FAM189A1 | chr15 | 31455370 | 31455485 | Hypo | cancer_general | NOP10, NUTM1, SLC12A6 |
| chr15 | 33879242 | 33879272 | Hypo | cancer_general | RYR3 | chr15 | 34630515 | 34630544 | Hypo | tcga | |
| chr15 | 34630818 | 34630865 | Hypo | cancer_general | NOP10, NUTM1, SLC12A6 | chr15 | 34879708 | 34879866 | Hypo | cancer_general | — |
| chr15 | 35310631 | 35310868 | Hypo | literature | — | chr15 | 40671495 | 40671620 | Hypo | ovarian | KNSTRN, DISP2 |
| chr15 | 40675092 | 40675121 | Hypo | literature | KNSTRN | chr15 | 40782219 | 40782249 | Hypo | breast | — |
| chr15 | 40856224 | 40856254 | Hypo | cancer_general | RPUSD2, C15orf57 | chr15 | 40877650 | 40877714 | Hypo | cancer_general | TRNA_Ser, CASC5 |
| chr15 | 41165245 | 41165700 | Hypo | cancer_general | RHOV | chr15 | 41541844 | 41541874 | Hypo | cancer_general | CHP1 |
| chr15 | 41693679 | 41693794 | Hypo | cancer_general | NDUFAF1 | chr15 | 41708225 | 41708305 | Hypo | cancer_general | RTF1 |
| chr15 | 41732398 | 41732471 | Hypo | breast | RTF1 | chr15 | 41835548 | 41835720 | Hypo | cancer_general | — |
| chr15 | 42749733 | 42749899 | Hypo | literature | ZNF106 | chr15 | 42866975 | 42867049 | Hypo | cancer_general | STARD9, HAUS2 |
| chr15 | 43551059 | 43551196 | Hypo | esophageal | — | chr15 | 44037568 | 44037699 | Hypo | cancer_general | PDIA3, CATSPER2P1 |
| chr15 | 45444061 | 45444141 | Hypo | ovarian | DUOX1 | chr15 | 46021437 | 46021467 | Hypo | pancreas | — |
| chr15 | 50450454 | 50450574 | Hypo | head_neck | — | chr15 | 50464583 | 50464622 | Hypo | cancer_general | SLC27A2 |
| chr15 | 51146606 | 51146636 | Hypo | cancer_general | AK091906 | chr15 | 52000818 | 52000937 | Hypo | cancer_general | SCG3 |
| chr15 | 54642236 | 54642352 | Hypo | literature, cancer_general | UNC13C | chr15 | 55452761 | 55452993 | Hypo | cancer_general | — |
| chr15 | 55610440 | 55610698 | Hypo | cancer_general | PIGB, HP06981 | chr15 | 55699089 | 55699164 | Hypo | cancer_general | FLJ27352, DYX1C1, DYX1C1-CCPG1 |
| chr15 | 55806758 | 55806900 | Hypo | cancer_general | DYX1C1, unknown, FAM63B | chr15 | 56832508 | 56832546 | Hypo | cancer_general | BC037892 |
| chr15 | 59158488 | 59158537 | Hypo | cancer_general | BNIP2, GTF2A2 | chr15 | 59158781 | 59158848 | Hypo | cancer_general | FAM63B, unknown |
| chr15 | 59950198 | 59950363 | Hypo | breast | NARG2 | chr15 | 60084984 | 60085014 | Hypo | cancer_general | — |
| chr15 | 60705106 | 60705204 | Hypo | cancer_general | CSNK1G1 | chr15 | 64109724 | 64109788 | Hypo | cancer_general | HERC1 |
| chr15 | 64618655 | 64618813 | Hypo | cancer_general | PIF1 | chr15 | 64649481 | 64649553 | Hypo | cancer_general | KIAA0101, CSNK1G1 |
| chr15 | 65118954 | 65118984 | Hypo | cancer_general | PIF1 | chr15 | 65119265 | 65119295 | Hypo | cancer_general | PIF1 |
| chr15 | 65119499 | 65119632 | Hypo | cancer_general | — | chr15 | 65436137 | 65436213 | Hypo | ovarian | CLPX, PDCD7 |
| chr15 | 65685591 | 65685708 | Hypo | cancer_general | IGDCC4 | chr15 | 65823926 | 65824103 | Hypo | lung, cancer_general | PTPLAD1 VWA9, |
| chr15 | 65826189 | 65826359 | Hypo | cancer_general | PTPLAD1 | chr15 | 65862004 | 65862121 | Hypo | cancer_general | PTPLAD1 |
| chr15 | 66113240 | 66113270 | Hypo | head_neck | MAP2K1 | chr15 | 66649915 | 66649945 | Hypo | cancer_general | MAP2K1 |
| chr15 | 66727409 | 66727498 | Hypo | literature | SNAPC5, MAP2K1 | chr15 | 66729148 | 66729177 | Hypo | literature | — |
| chr15 | 66774117 | 66774203 | Hypo | literature | MAP2K1 | chr15 | 66789220 | 66789321 | Hypo | cancer_general | SNAPC5, MAP2K1, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 66963816 | 66963871 | Hypo | cancer_general | hCG_2003567 | | | | | | RPL4, SNORD18C, SNORD18B, SNORD16, SNORD18A, ZWILCH |
| chr15 | 67545536 | 67545566 | Hypo | cancer_general | IQCH, AAGAB | chr15 | 67146145 | 67146431 | Hypo | cancer_general | BX538221 |
| chr15 | 72743741 | 72743796 | Hypo | cancer_general | — | chr15 | 72411929 | 72412176 | Hypo | cancer_general | SENP8, MYO9A |
| chr15 | 74686021 | 74686051 | Hypo | cancer_general | — | chr15 | 72979757 | 72979873 | Hypo | cancer_general | HIGD2B, BBS4 |
| chr15 | 74903896 | 74903926 | Hypo | cancer_general | AK095335, CLK3 | chr15 | 74818772 | 74818806 | Hypo | pancreas | CLK3, AK095335 |
| chr15 | 75205413 | 75205481 | Hypo | cancer_general | COX5A, FAM219B | chr15 | 74906463 | 74906493 | Hypo | cancer_general | |
| chr15 | 77448873 | 77449001 | Hypo | cancer_general | PEAK1 | chr15 | 75412459 | 75412714 | Hypo | cancer_general | — |
| chr15 | 78895791 | 78896218 | Hypo | cancer_general | WDR61 | chr15 | 78501806 | 78501942 | Hypo | cancer_general | ACSBG1 |
| chr15 | 79151898 | 79152007 | Hypo | cancer_general | TRNA_Lys | chr15 | 78859435 | 78859603 | Hypo | cancer_general | CHRNA5 |
| chr15 | 83314048 | 83314106 | Hypo | cancer_general | LOC283692 | chr15 | 80216803 | 80216884 | Hypo | cancer_general | C15orf37, ST20 |
| chr15 | 83655843 | 83655934 | Hypo | cancer_general | C15orf40, FAM103A1, BC044934 | chr15 | 83622512 | 83622565 | Hypo | ovarian | BC044934, HOMER2 |
| chr15 | 84711204 | 84711367 | Hypo | cancer_general | — | chr15 | 83866523 | 83866559 | Hypo | cancer_general | HDGFRP3 |
| chr15 | 85886518 | 85886604 | Hypo | cancer_general | — | chr15 | 85142994 | 85143054 | Hypo | cancer_general | ZSCAN2 |
| chr15 | 90631823 | 90631948 | Hypo | literature | IDH2 | chr15 | 86002524 | 86002690 | Hypo | cancer_general | AKAP13 |
| chr15 | 90703262 | 90703345 | Hypo | cancer_general | — | chr15 | 90667461 | 90667586 | Hypo | colorectal | — |
| chr15 | 93158592 | 93158739 | Hypo | cancer_general | FAM174B, DQ589911, DQ571124, DQ574028, DQ593762 | chr15 | 90755916 | 90756079 | Hypo | cancer_general | SEMA4B |
| chr15 | 93364552 | 93364624 | Hypo | cancer_general | — | chr15 | 93350668 | 93350698 | Hypo | lung | — |
| chr15 | 97006372 | 97006533 | Hypo | cancer_general | — | chr15 | 94347602 | 94347632 | Hypo | cancer_general | BC037497 |
| chr15 | 98776762 | 98776792 | Hypo | cancer_general | — | chr15 | 98634851 | 98634949 | Hypo | cancer_general | — |
| chr15 | 99295692 | 99295749 | Hypo | cancer_general | IGF1R | chr15 | 99254040 | 99254208 | Hypo | hepatobiliary | — |
| chr15 | 99354999 | 99355041 | Hypo | cancer_general | — | chr15 | 99346861 | 99347040 | Hypo | cancer_general, pancreas | IGF1R |
| chr15 | 99456299 | 99456329 | Hypo | hepatobiliary | IGF1R | chr15 | 99453230 | 99453440 | Hypo | hepatobiliary | IGF1R, AF02763 |
| chr15 | 100274325 | 100274385 | Hypo | cancer_general | LYSMD4 | chr15 | 99497059 | 99497132 | Hypo | ovarian | — |
| | | | | | | chr15 | 100339980 | 100340010 | Hypo | | DJ031154, DQ590616, DQ571121, DQ575742, DQ595494, DNM1P46, DQ575741 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 101818327 | 101818357 | Hypo | cancer_general | VIMP, SNRPA1 | chr15 | 102115873 | 102115905 | Hypo | cancer_general | — |
| chr15 | 102193587 | 102193713 | Hypo | cancer_general | TARSL2, TM2D3 | NW_001838016.1_818233-828058 | 6174 | 6313 | Hypo | cancer_general | — |
| chr12 | 1650475 | 1650577 | Hypo | cancer_general | — | chr12 | 2046104 | 2046134 | Hypo | cancer_general | DCP1B, LINC00940 |
| chr12 | 2403658 | 2403714 | Hypo | cancer_general | CACNA1C-IT3 | chr12 | 2566053 | 2566247 | Hypo | cancer_general | — |
| chr12 | 2595199 | 2595339 | Hypo | cancer_general | — | chr12 | 2964465 | 2964577 | Hypo | cancer_general | FOXM1, LOC100507424 |
| chr12 | 4213973 | 4214157 | Hypo | cancer_general | — | chr12 | 4231674 | 4231767 | Hypo | cancer_general | — |
| chr12 | 4274271 | 4274409 | Hypo | pancreas | — | chr12 | 4323835 | 4323912 | Hypo | cancer_general | — |
| chr12 | 4362436 | 4362471 | Hypo | cancer_general | — | chr12 | 4379357 | 4379491 | Hypo | pancreas | CCND2 |
| chr12 | 4392883 | 4392922 | Hypo | cancer_general | CCND2 | chr12 | 4405589 | 4405619 | Hypo | cancer_general | CCND2 |
| chr12 | 4431271 | 4431301 | Hypo | cancer_general | C12orf5 | chr12 | 4554801 | 4554831 | Hypo | cancer_general | FGF6 |
| chr12 | 5840200 | 5840363 | Hypo | cancer_general | ANO2 | chr12 | 6473721 | 6473762 | Hypo | cancer_general | SCNN1A |
| chr12 | 6483615 | 6483756 | Hypo | cancer_general | LTBR, SCNN1A | chr12 | 6678158 | 6678203 | Hypo | cancer_general | CHD4, AK096395, NOP2 |
| chr12 | 7403914 | 7404060 | Hypo | cancer_general | — | chr12 | 7559160 | 7559307 | Hypo | cancer_general | CD163L1 |
| chr12 | 8036526 | 8036634 | Hypo | cancer_general | NANOGP1 | chr12 | 8122523 | 8122628 | Hypo | cancer_general | — |
| chr12 | 8127036 | 8127140 | Hypo | cancer_general | — | chr12 | 8127565 | 8127595 | Hypo | hepatobiliary | — |
| chr12 | 8139203 | 8139233 | Hypo | cancer_general | — | chr12 | 8163573 | 8163603 | Hypo | cancer_general | — |
| chr12 | 8180999 | 8181065 | Hypo | ovarian | FOXJ2 | chr12 | 8808599 | 8808709 | Hypo | cancer_general | MFAP5 |
| chr12 | 8975182 | 8975361 | Hypo | cancer_general | A2ML1 | chr12 | 9916313 | 9916343 | Hypo | cancer_general | CD69 |
| chr12 | 10085916 | 10085948 | Hypo | cancer_general | CLEC2A STYK1, MAGOHB | chr12 | 10363278 | 10363607 | Hypo | cancer_general | GABARAPL1 |
| chr12 | 10772771 | 10772896 | Hypo | hepatobiliary | — | chr12 | 12456859 | 12456889 | Hypo | pancreas | — |
| chr12 | 12504616 | 12504850 | Hypo | cancer_general | LOH12CR2, LOH12CR1 | chr12 | 12848390 | 12848556 | Hypo | cancer_general | GPR19 |
| chr12 | 13036048 | 13036078 | Hypo | cancer_general | GPRC5A, RPL13AP20 | chr12 | 13055966 | 13055996 | Hypo | pancreas | GPRC5A |
| chr12 | 14719937 | 14719967 | Hypo | cancer_general | PLBD1 | chr12 | 14818824 | 14818867 | Hypo | cancer_general | GUCY2C |
| chr12 | 21833068 | 21833265 | Hypo | cancer_general | — | chr12 | 22698063 | 22698110 | Hypo | cancer_general | C2CD5 |
| chr12 | 23229390 | 23229420 | Hypo | cancer_general | AK094733 | chr12 | 25362824 | 25362853 | Hypo | literature | LYRM5, KRAS |
| chr12 | 25368463 | 25368492 | Hypo | literature | KRAS | chr12 | 25378543 | 25378662 | Hypo | literature | KRAS |
| chr12 | 25380231 | 25380299 | Hypo | literature | KRAS | chr12 | 25398203 | 25398319 | Hypo | literature | DD157417, KRAS |
| chr12 | 26178334 | 26178376 | Hypo | cancer_general | RASSF8 | chr12 | 27114515 | 27114639 | Hypo | ovarian | TM7SF3, FGFR1OP2 |
| chr12 | 27176441 | 27176539 | Hypo | cancer_general | MED21, TM7SF3 | chr12 | 27494550 | 27494580 | Hypo | pancreas | ARNTL2 |
| chr12 | 31316012 | 31316362 | Hypo | cancer_general | OVOS2 | chr12 | 31366306 | 31366336 | Hypo | cancer_general | OVOS2 |
| chr12 | 32086716 | 32086982 | Hypo | cancer_general | — | chr12 | 32340317 | 32340534 | Hypo | cancer_general | BICD1 |
| chr12 | 32831622 | 32831652 | Hypo | cancer_general | DNM1L | chr12 | 34494888 | 34494918 | Hypo | cancer_general | — |
| chr12 | 34502733 | 34502803 | Hypo | cancer_general | — | chr12 | 43944952 | 43944991 | Hypo | cancer_general | — |
| chr12 | 47629349 | 47629379 | Hypo | breast | PCED1B | chr12 | 49035233 | 49035414 | Hypo | head_neck | — |
| chr12 | 49074601 | 49074843 | Hypo | cancer_general | CCNT1 | chr12 | 49515852 | 49515920 | Hypo | cancer_general | TUBA1A, TUBA1B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 49657705 | 49657901 | Hypo | cancer_general | D28390, TUBA1C | chr12 | 49989786 | 49989816 | Hypo | ovarian | FAM186B |
| chr12 | 50507349 | 50507522 | Hypo | cancer_general | COX14, GPD1 | chr12 | 50673944 | 50674096 | Hypo | pancreas | — |
| chr12 | 50897763 | 50898273 | Hypo | cancer_general | DIP2B | chr12 | 51400044 | 51400091 | Hypo | cancer_general | U7, SLC11A2 |
| chr12 | 51420874 | 51421271 | Hypo | cancer_general | — | chr12 | 51421556 | 51421586 | Hypo | cancer_general | — |
| chr12 | 51441284 | 51441368 | Hypo | cancer_general | LETMD1 | chr12 | 51565269 | 51565548 | Hypo | cancer_general | — |
| chr12 | 51625514 | 51625587 | Hypo | ovarian | DAZAP2 | chr12 | 51930708 | 51930862 | Hypo | cancer_general | — |
| chr12 | 53763427 | 53763885 | Hypo | cancer_general |  | chr12 | 53766833 | 53766964 | Hypo | cancer_general | SP1 |
| chr12 | 53834392 | 53834475 | Hypo | cancer_general | PRR13, PCBP2, AMHR2 | chr12 | 53885346 | 53885651 | Hypo | cancer_general | TARBP2, MAP3K12 |
| chr12 | 54613463 | 54613615 | Hypo | cancer_general |  | chr12 | 54719808 | 54720232 | Hypo | cancer_general | COPZ1 |
| chr12 | 54894048 | 54894173 | Hypo | lung | NCKAP1L | chr12 | 54922624 | 54922803 | Hypo | cancer_general | NCKAP1L |
| chr12 | 55480923 | 55481067 | Hypo | cancer_general | — | chr12 | 55561202 | 55561354 | Hypo | cancer_general | — |
| chr12 | 56231108 | 56231148 | Hypo | cancer_general | AX747140, DNAJC14, MMP19 | chr12 | 56400463 | 56400591 | Hypo | cancer_general | SUOX, RAB5B |
| chr12 | 56478840 | 56478869 | Hypo | literature | ERBB3 | chr12 | 56481645 | 56481937 | Hypo | literature | ERBB3 |
| chr12 | 56486572 | 56486601 | Hypo | literature | ERBB3 | chr12 | 56490965 | 56490994 | Hypo | literature | ERBB3, PA2G4 |
| chr12 | 56491630 | 56491659 | Hypo | literature | ERBB3, PA2G4 | chr12 | 56492618 | 56492647 | Hypo | literature | PA2G4, ERBB3 |
| chr12 | 56558381 | 56558519 | Hypo | ovarian | SMARCC2, MYL6, MYL6B | chr12 | 56653281 | 56653369 | Hypo | ovarian | COQ10A, ANKRD52 |
| chr12 | 57174355 | 57174452 | Hypo | cancer_general | HSD17B6 | chr12 | 57359920 | 57359950 | Hypo | cancer_general | RDH16 |
| chr12 | 57559869 | 57559925 | Hypo | cancer_general | LRP1 | chr12 | 57881127 | 57881383 | Hypo | cancer_general | MARS, ARHGAP9 |
| chr12 | 57983314 | 57983348 | Hypo | ovarian | PIP4K2C, BC033961, KIF5A | chr12 | 58145415 | 58145450 | Hypo | literature | CDK4, TSPAN31, DM110804, MARCH9 |
| chr12 | 62603907 | 62603937 | Hypo | ovarian | _Y_RNA, AK024134, PPM1H | chr12 | 62858444 | 62858575 | Hypo | ovarian | MON2 |
| chr12 | 63326618 | 63326648 | Hypo | cancer_general |  | chr12 | 64028352 | 64028382 | Hypo | cancer_general | DPY19L2 |
| chr12 | 64783185 | 64783308 | Hypo | lung | LEMD3 | chr12 | 65516360 | 65516455 | Hypo | cancer_general | WIF1 |
| chr12 | 65557212 | 65557376 | Hypo | cancer_general |  | chr12 | 65561778 | 65562086 | Hypo | colorectal, cancer_general | LEMD3 |
| chr12 | 68433260 | 68433321 | Hypo | colorectal | — | chr12 | 68964473 | 68964503 | Hypo | ovarian | — |
| chr12 | 68978322 | 68978576 | Hypo | cancer_general | — | chr12 | 69754451 | 69754729 | Hypo | cancer_general | — |
| chr12 | 69964176 | 69964264 | Hypo | cancer_general | FRS2 | chr12 | 70087493 | 70087568 | Hypo | cancer_general | YEATS4, E02193, LYZ |
| chr12 | 70698883 | 70699050 | Hypo | cancer_general | CNOT2 | chr12 | 85667353 | 85667465 | Hypo | cancer_general | BEST3 ALX1 |
| chr12 | 89915009 | 89915043 | Hypo | cancer_general | POC1B-GALNT4, GALNT4, POC1B | chr12 | 93476304 | 93476342 | Hypo | breast | LOC643339 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 94544022 | 94544052 | Hypo | pancreas | PLXNC1 | chr12 | 94852412 | 94852506 | Hypo | cancer_general | CCDC41-AS1, CCDC41 |
| chr12 | 95216830 | 95216960 | Hypo | cancer_general | | chr12 | 95822981 | 95823011 | Hypo | cancer_general | — |
| chr12 | 95866563 | 95866609 | Hypo | cancer_general | METAP2 | chr12 | 96880822 | 96881029 | Hypo | cancer_general | C12orf55 |
| chr12 | 98948200 | 98948295 | Hypo | cancer_general | | chr12 | 98949938 | 98949972 | Hypo | ovarian | — |
| chr12 | 98961066 | 98961241 | Hypo | cancer_general | | chr12 | 98986343 | 98986491 | Hypo | cancer_general | SLC25A3, SNORA53 |
| chr12 | 100595495 | 100595558 | Hypo | cancer_general | AX746635, ACTR6, CCDC53 | chr12 | 101025380 | 101025410 | Hypo | pancreas | GAS2L3 |
| chr12 | 102457208 | 102457238 | Hypo | cancer_general | | chr12 | 104506691 | 104506783 | Hypo | pancreas | NFYB, HCFC2 |
| chr12 | 104671030 | 104671064 | Hypo | cancer_general | TXNRD1 | chr12 | 104671699 | 104671761 | Hypo | cancer_general | TXNRD1 |
| chr12 | 104684181 | 104684258 | Hypo | lung | TXNRD1 | chr12 | 104696376 | 104696502 | Hypo | cancer_general | EID3, TXNRD1 |
| chr12 | 105017109 | 105017228 | Hypo | colorectal | | chr12 | 108080498 | 108080553 | Hypo | cancer_general | PWP1 |
| chr12 | 109488519 | 109488686 | Hypo | lung | USP30-AS1, USP30 | chr12 | 110353414 | 110353451 | Hypo | breast | TCHP |
| chr12 | 110507084 | 110507207 | Hypo | cancer_general | C12orf76 | chr12 | 110717541 | 110717710 | Hypo | cancer_general | ATP2A2, JA611269 |
| chr12 | 110840344 | 110840404 | Hypo | cancer_general | ANAPC7, GPN3, ARPC3 | chr12 | 110854243 | 110854288 | Hypo | cancer_general | — |
| chr12 | 110887179 | 110887209 | Hypo | cancer_general | | chr12 | 110983706 | 110983736 | Hypo | lung | PPTC7 |
| chr12 | 111143726 | 111143756 | Hypo | cancer_general | | chr12 | 111763122 | 111763152 | Hypo | cancer_general | — |
| chr12 | 112547662 | 112547692 | Hypo | cancer_general | | chr12 | 112574734 | 112574995 | Hypo | lung | TRAFD1 |
| chr12 | 112792829 | 112792944 | Hypo | breast | | chr12 | 112825760 | 112825896 | Hypo | cancer_general | — |
| chr12 | 112888151 | 112888315 | Hypo | literature | PTPN11 | chr12 | 112910821 | 112910850 | Hypo | literature | PTPN11 |
| chr12 | 112915509 | 112915538 | Hypo | literature | PTPN11 | chr12 | 112926255 | 112926284 | Hypo | literature | PTPN11 |
| chr12 | 112926876 | 112926914 | Hypo | literature | PTPN11 | chr12 | 113795506 | 113795657 | Hypo | cancer_general | PLBD2 |
| chr12 | 114337763 | 114337793 | Hypo | lung | RBM19 | chr12 | 117474065 | 117474198 | Hypo | lung, cancer_general | TESC, AK055849, FBXW8 |
| chr12 | 117526330 | 117526368 | Hypo | cancer_general | TESC | chr12 | 118860397 | 118860654 | Hypo | cancer_general | SUDS3 |
| chr12 | 118920764 | 118920804 | Hypo | cancer_general | | chr12 | 120148142 | 120148248 | Hypo | cancer_general | MIR1178, CIT |
| chr12 | 120148923 | 120148962 | Hypo | cancer_general | MIR1178, CIT | chr12 | 120535158 | 120535187 | Hypo | literature | RAB35, CCDC64 |
| chr12 | 120536625 | 120536654 | Hypo | literature | CCDC64, RAB35 | chr12 | 120885215 | 120885245 | Hypo | cancer_general | GATC, TRIAP1, COX6A1 |
| chr12 | 120971686 | 120971716 | Hypo | cancer_general | RNF10, COQ5 | chr12 | 121622546 | 121622576 | Hypo | cancer_general | P2RX7 |
| chr12 | 122108464 | 122108601 | Hypo | head_neck | MORN3 | chr12 | 122192723 | 122192843 | Hypo | breast | TMEM120B |
| chr12 | 122278388 | 122278580 | Hypo | cancer_general | HPD, SETD1B | chr12 | 122285067 | 122285108 | Hypo | cancer_general | HPD |
| chr12 | 122473581 | 122473611 | Hypo | cancer_general | BCL7A | chr12 | 122940449 | 122940479 | Hypo | colorectal | — |
| chr12 | 123129129 | 123129550 | Hypo | cancer_general | HCAR1 | chr12 | 123211316 | 123211390 | Hypo | pancreas | HCAR1, HCAR3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 123233646 | 123233846 | Hypo | cancer_general | DENR | chr12 | 123410210 | 123410240 | Hypo | cancer_general | ABCB9 |
| chr12 | 123942025 | 123942189 | Hypo | cancer_general | SNRNP35 | chr12 | 124117199 | 124117289 | Hypo | cancer_general | EIF2B1, GTF2H3 |
| chr12 | 124393560 | 124393604 | Hypo | cancer_general | — | chr12 | 124397464 | 124397618 | Hypo | cancer_general | AACS |
| chr12 | 125009276 | 125009306 | Hypo | cancer_general | — | chr12 | 125589840 | 125589872 | Hypo | esophageal | — |
| chr12 | 129447299 | 129447450 | Hypo | cancer_general | GLTID1 | chr12 | 130037653 | 130037778 | Hypo | cancer_general | — |
| chr12 | 130821371 | 130821621 | Hypo | cancer_general | PIWIL1 | chr12 | 130968621 | 130968654 | Hypo | cancer_general | RIMBP2 AX748157, |
| chr12 | 131403032 | 131403125 | Hypo | cancer_general | — | chr12 | 131513345 | 131513403 | Hypo | cancer_general | GPR133 |
| chr12 | 132102173 | 132102202 | Hypo | literature | — | chr12 | 132169288 | 132169442 | Hypo | cancer_general | — |
| chr12 | 132221689 | 132222076 | Hypo | cancer_general | SFSWAP | chr12 | 132332910 | 132332940 | Hypo | cancer_general | MMP17 |
| chr12 | 132333434 | 132333597 | Hypo | cancer_general | MMP17 | chr12 | 132348651 | 132348684 | Hypo | cancer_general | — |
| chr12 | 132423516 | 132423854 | Hypo | cancer_general | PUS1 | chr12 | 132643233 | 132643279 | Hypo | head_neck | NOC4L |
| chr12 | 132986495 | 132986581 | Hypo | cancer_general | — | chr12 | 133002792 | 133003231 | Hypo | cancer_general | P2RX2, POLE |
| chr12 | 133172907 | 133173021 | Hypo | cancer_general | LRCOL1 | chr12 | 133199738 | 133199784 | Hypo | cancer_general | PGAM5, PXMP2 |
| chr12 | 133262698 | 133262926 | Hypo | cancer_general | PXMP2, PGAM5, POLE | chr12 | 133280578 | 133280682 | Hypo | ovarian | — |
| chr6 | 373148 | 373290 | Hypo | cancer_general | — | chr6 | 2986688 | 2986718 | Hypo | cancer_general | NQO2, DKFZP686I15217 |
| chr6 | 3053299 | 3053386 | Hypo | cancer_general | SLC22A23, AX746991 | chr6 | 3247675 | 3247704 | Hypo | literature | AK096219 |
| chr6 | 3285222 | 3285513 | Hypo | cancer_general | — | chr6 | 3405645 | 3405713 | Hypo | cancer_general | SLC22A23 |
| chr6 | 4836002 | 4836458 | Hypo | cancer_general | CDYL | chr6 | 4951247 | 4951390 | Hypo | cancer_general | CDYL |
| chr6 | 5359500 | 5359539 | Hypo | breast | FARS2 | chr6 | 5783325 | 5783496 | Hypo | cancer_general | — |
| chr6 | 6367086 | 6367271 | Hypo | cancer_general | LY86-AS1 | chr6 | 6753803 | 6753839 | Hypo | colorectal | — |
| chr6 | 7731054 | 7731083 | Hypo | literature | BMP6 | chr6 | 7892314 | 7892412 | Hypo | ovarian | TXNDC5, BLOC1S5-TXNDC5 |
| chr6 | 8014600 | 8014772 | Hypo | head_neck | BLOC1S5, EEF1E1-MUTED | chr6 | 10390384 | 10390447 | Hypo | cancer_general | TFAP2A |
| chr6 | 10542836 | 10542977 | Hypo | colorectal | GCNT2 | chr6 | 10734917 | 10735045 | Hypo | cancer_general | TMEM14C |
| chr6 | 12288517 | 12288681 | Hypo | cancer_general | EDN1 | chr6 | 13797690 | 13797736 | Hypo | cancer_general | MCUR1 |
| chr6 | 14687918 | 14688084 | Hypo | cancer_general | — | chr6 | 14986483 | 14986522 | Hypo | cancer_general | — |
| chr6 | 15513780 | 15513981 | Hypo | ovarian | DTNBP1, JARID2 | chr6 | 16197030 | 16197112 | Hypo | cancer_general | — |
| chr6 | 16729595 | 16729624 | Hypo | literature | ATXN1 | chr6 | 17666654 | 17666707 | Hypo | breast | NUP153 |
| chr6 | 17750276 | 17750306 | Hypo | cancer_general | KIF13A | chr6 | 18035867 | 18036015 | Hypo | lung | — |
| chr6 | 19892448 | 19892627 | Hypo | cancer_general | — | chr6 | 22172209 | 22172305 | Hypo | hepatobiliary | LINC00340 TDP2, |
| chr6 | 22172536 | 22172566 | Hypo | hepatobiliary | LINC00340 | chr6 | 24647342 | 24647599 | Hypo | cancer_general | KIAA0319 |
| chr6 | 24662439 | 24662469 | Hypo | cancer_general | ACOT13, TDP2 | chr6 | 26189859 | 26189991 | Hypo | | HIST1H3D, HIST1H3F, HIST1H2AD, HIST1H2BF, HIST1H4D, HIST1H2BE |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 26214514 | 26214648 | Hypo | cancer_general | HIST1H2BG, HIST1H2AE, HIST1H3F, HIST1H4E | chr6 | 26254617 | 26254647 | Hypo | cancer_general | HIST1H2BH, HIST1H3F, HIST1H4G |
| chr6 | 26260956 | 26260986 | Hypo | esophageal | HIST1H2BH | chr6 | 27441812 | 27441842 | Hypo | cancer_general | TRNA_Ser, TRNA_Asp, ZNF184 |
| chr6 | 30095233 | 30095262 | Hypo | literature | TRIM40, DQ580846 | chr6 | 30130804 | 30130895 | Hypo | literature | TRIM15, TRIM10 |
| chr6 | 32374147 | 32374176 | Hypo | literature | BTNL2 | chr6 | 32374739 | 32374768 | Hypo | literature | BTNL2 |
| chr6 | 32376051 | 32376080 | Hypo | literature | BTNL2 | chr6 | 33161275 | 33161342 | Hypo | literature | RXRB, JA611279, SLC39A7, COL11A2 |
| chr6 | 33632930 | 33633000 | Hypo | hepatobiliary | ITPR3 | chr6 | 33636388 | 33636418 | Hypo | hepatobiliary | ITPR3 |
| chr6 | 33955505 | 33955731 | Hypo | cancer_general | — | chr6 | 34113872 | 34113957 | Hypo | tcga | — |
| chr6 | 34170970 | 34171061 | Hypo | cancer_general | — | chr6 | 34219930 | 34219972 | Hypo | cancer_general | C6orf1, HMGA1 |
| chr6 | 34396431 | 34396542 | Hypo | cancer_general | RPS10 | chr6 | 34535802 | 34535832 | Hypo | cancer_general | SNRPC |
| chr6 | 34714803 | 34714896 | Hypo | lung | SNRPC | chr6 | 34724047 | 34724228 | Hypo | cancer_general | TULP1 |
| chr6 | 35150041 | 35150080 | Hypo | cancer_general | — | chr6 | 35470285 | 35470399 | Hypo | cancer_general | TEAD3 |
| chr6 | 36165662 | 36165692 | Hypo | cancer_general | BRPF3, BC042825 | chr6 | 36178031 | 36178301 | Hypo | colorectal | BRPF3 |
| chr6 | 36313883 | 36313913 | Hypo | cancer_general | ETV7, C6orf222 | chr6 | 36392273 | 36392323 | Hypo | cancer_general | PXT1 |
| chr6 | 36406316 | 36406370 | Hypo | cancer_general | KCTD20, PXT1 | chr6 | 37024559 | 37024589 | Hypo | cancer_general | — |
| chr6 | 37392127 | 37392189 | Hypo | cancer_general | FTSJD2 | chr6 | 37545401 | 37545495 | Hypo | cancer_general | — |
| chr6 | 37776410 | 37776440 | Hypo | cancer_general | — | chr6 | 37776703 | 37776735 | Hypo | cancer_general | — |
| chr6 | 39508464 | 39508493 | Hypo | literature | KIF6 | chr6 | 41273881 | 41273942 | Hypo | cancer_general | — |
| chr6 | 41773520 | 41773903 | Hypo | breast | USP49 | chr6 | 41774459 | 41774576 | Hypo | breast | USP49 |
| chr6 | 42062143 | 42062346 | Hypo | cancer_general | C6orf132 | chr6 | 42090977 | 42091027 | Hypo | cancer_general | C6orf132 |
| chr6 | 42111015 | 42111051 | Hypo | cancer_general | C6orf132 | chr6 | 42711893 | 42711923 | Hypo | cancer_general | TBCC |
| chr6 | 42773440 | 42773622 | Hypo | cancer_general | GLTSCR1L | chr6 | 42846662 | 42846705 | Hypo | cancer_general | RPL7L1, DQ581019 |
| chr6 | 42990166 | 42990485 | Hypo | cancer_general | RRP36, KLHDC3, MEA1 | chr6 | 43119019 | 43119580 | Hypo | colorectal, cancer_general | PTK7 |
| chr6 | 43424297 | 43424470 | Hypo | cancer_general | DLK2, ABCC10 | chr6 | 43425152 | 43425207 | Hypo | cancer_general | ABCC10, DLK2 |
| chr6 | 43425479 | 43425509 | Hypo | cancer_general | DLK2, ABCC10 | chr6 | 43478676 | 43478745 | Hypo | cancer_general | YIPF3, POLR1C, LRRC73, TJAP1 |
| chr6 | 43639548 | 43639710 | Hypo | ovarian | MRPS18A, RSPH9 | chr6 | 43748463 | 43748616 | Hypo | breast | HV983065, VEGFA |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 44240914 | 44241108 | Hypo | cancer_general | TCTE1, SPATS1, TMEM151B, NFKBIE | chr6 | 44695763 | 44695795 | Hypo | cancer_general | BX647715 |
| chr6 | 47473194 | 47473287 | Hypo | cancer_general | CD2AP | chr6 | 47590439 | 47590604 | Hypo | breast | CD2AP |
| chr6 | 49590555 | 49590786 | Hypo | cancer_general | RHAG | chr6 | 49765146 | 49765202 | Hypo | cancer_general | — |
| chr6 | 52344375 | 52344405 | Hypo | pancreas | EFHC1 | chr6 | 52763812 | 52763982 | Hypo | colorectal | GSTA3 |
| chr6 | 52928742 | 52928776 | Hypo | cancer_general | FBXO9, ICK | chr6 | 52929051 | 52929233 | Hypo | cancer_general | ICK, FBXO9 |
| chr6 | 53052723 | 53052859 | Hypo | cancer_general | — | chr6 | 57694587 | 57694617 | Hypo | cancer_general | — |
| chr6 | 58147523 | 58147594 | Hypo | cancer_general | TRNA_Ile, TRNA_Ala | chr6 | 71090933 | 71090963 | Hypo | ovarian | — |
| chr6 | 73980676 | 73980722 | Hypo | hepatobiliary | C6orf147, AL832252, BC031876, KHDC1 | chr6 | 73982025 | 73982058 | Hypo | hepatobiliary | C6orf147, AL832252, BC031876, KHDC1 |
| chr6 | 74097722 | 74097763 | Hypo | ovarian | DDX43 | chr6 | 75995789 | 75995819 | Hypo | cancer_general | FILIP1, LOC100506804, TMEM30A |
| chr6 | 82958615 | 82958917 | Hypo | cancer_general | IBTK | chr6 | 83546464 | 83546498 | Hypo | cancer_general | — |
| chr6 | 85050415 | 85050504 | Hypo | cancer_general | — | chr6 | 86302413 | 86302614 | Hypo | cancer_general | SNX14 |
| chr6 | 88518712 | 88518742 | Hypo | colorectal | AY927641 | chr6 | 89672213 | 89672376 | Hypo | cancer_general | RNGTT |
| chr6 | 97412429 | 97412529 | Hypo | esophageal | KLHL32 | chr6 | 97930083 | 97930113 | Hypo | hepatobiliary | AK091365 |
| chr6 | 99396456 | 99396609 | Hypo | cancer_general | — | chr6 | 99842336 | 99842382 | Hypo | tcga | PNISR, BC033061, COQ3 |
| chr6 | 100050765 | 100050815 | Hypo | cancer_general | PRDM13 | chr6 | 100135425 | 100135583 | Hypo | cancer_general | ATG5 |
| chr6 | 105821423 | 105821453 | Hypo | cancer_general | PREP | chr6 | 106731509 | 106731597 | Hypo | ovarian | PDSS2 |
| chr6 | 107075651 | 107075704 | Hypo | cancer_general | QRSL1, RTN4IP1 | chr6 | 107562769 | 107562859 | Hypo | cancer_general | — |
| chr6 | 108181556 | 108181721 | Hypo | cancer_general | SEC63 | chr6 | 108280292 | 108280352 | Hypo | cancer_general | SEC63 |
| chr6 | 109057882 | 109057928 | Hypo | pancreas | — | chr6 | 109058799 | 109058861 | Hypo | pancreas | — |
| chr6 | 110437721 | 110437751 | Hypo | cancer_general | WASF1 | chr6 | 110848558 | 110848682 | Hypo | ovarian | — |
| chr6 | 113852508 | 113852634 | Hypo | cancer_general | — | chr6 | 117000853 | 117001032 | Hypo | cancer_general | KPNA5, AX746765 |
| chr6 | 119254629 | 119254678 | Hypo | cancer_general | MCM9 | chr6 | 119483052 | 119483082 | Hypo | cancer_general | — |
| chr6 | 121797231 | 121797265 | Hypo | hepatobiliary | MGC34034, BC041459 | chr6 | 134067194 | 134067471 | Hypo | cancer_general | BC041459 |
| chr6 | 134176232 | 134176299 | Hypo | cancer_general | IL20RA | chr6 | 134589500 | 134589767 | Hypo | cancer_general | SGK1 |
| chr6 | 137366354 | 137366383 | Hypo | literature | LOC100652739, LRP11 | chr6 | 149868348 | 149868387 | Hypo | cancer_general | PPIL4 |
| chr6 | 150183760 | 150183874 | Hypo | cancer_general | ESR1 | chr6 | 151650396 | 151650453 | Hypo | cancer_general | AKAP12 |
| chr6 | 152419908 | 152419940 | Hypo | literature | AB075492, AK022993, TFB1M, TIAM2 | chr6 | 154970558 | 154970676 | Hypo | lung | — |
| chr6 | 155569208 | 155569305 | Hypo | cancer_general | ARID1B | chr6 | 157037549 | 157037677 | Hypo | cancer_general | — |
| chr6 | 157266063 | 157266109 | Hypo | breast | — | chr6 | 157502438 | 157502561 | Hypo | cancer_general | — |
| chr6 | 157506082 | 157506112 | Hypo | cancer_general | — | chr6 | 157637455 | 157637500 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 159211558 | 159211701 | Hypo | pancreas | AX747826, EZR | chr6 | 159228187 | 159228217 | Hypo | cancer_general | AX747826, EZR |
| chr6 | 159419589 | 159419717 | Hypo | cancer_general | RSPH3 | chr6 | 161645992 | 161646255 | Hypo | cancer_general | — |
| chr6 | 161780056 | 161780139 | Hypo | cancer_general | PARK2 | chr6 | 163360842 | 163602872 | Hypo | esophageal | AK311212, AK296276 |
| chr6 | 164114396 | 164114524 | Hypo | cancer_general | AK093114 | chr6 | 164179636 | 164179668 | Hypo | cancer_general | AK093114 |
| chr6 | 164183602 | 164183632 | Hypo | cancer_general | AK093114 | chr6 | 164196971 | 164197003 | Hypo | cancer_general | AK093114 |
| chr6 | 164215532 | 164215633 | Hypo | cancer_general | — | chr6 | 164228294 | 164228363 | Hypo | cancer_general | — |
| chr6 | 164246015 | 164246143 | Hypo | cancer_general | — | chr6 | 164283254 | 164283377 | Hypo | cancer_general | — |
| chr6 | 164314289 | 164314443 | Hypo | cancer_general | — | chr6 | 164322666 | 164322775 | Hypo | cancer_general | — |
| chr6 | 166944367 | 166944403 | Hypo | cancer_general | — | chr6 | 167202601 | 167202801 | Hypo | cancer_general | DACT2 |
| chr6 | 167835171 | 167835171 | Hypo | cancer_general | — | chr6 | 168719983 | 168720019 | Hypo | esophageal | SMOC2 |
| chr6 | 168858122 | 168858296 | Hypo | cancer_general | SMOC2 | chr6 | 168972472 | 168972502 | Hypo | hepatobiliary | WDR27 |
| chr6 | 169002054 | 169002084 | Hypo | esophageal | SMOC2 | chr6 | 170047467 | 170047499 | Hypo | lung | — |
| chr6 | 170240639 | 170240714 | Hypo | cancer_general | — | chr6 | 170264728 | 170264761 | Hypo | cancer_general | — |
| chr6 | 170475105 | 170475267 | Hypo | cancer_general | — | chr6 | 170494286 | 170494315 | Hypo | literature | — |
| chr6 | 170894820 | 170894912 | Hypo | hepatobiliary | PDCD2 | chr9 | 969788 | 969820 | Hypo | cancer_general | DMRT3, DMRT1 |
| chr9 | 2115824 | 2115981 | Hypo | breast | SMARCA2 | chr9 | 5070006 | 5070050 | Hypo | literature | JAK2 |
| chr9 | 5073756 | 5073788 | Hypo | literature | JAK2 | chr9 | 5078346 | 5078375 | Hypo | literature | JAK2 |
| chr9 | 5089711 | 5089740 | Hypo | literature | TRNA_Gln, JAK2 | chr9 | 5153325 | 5153380 | Hypo | cancer_general | — |
| chr9 | 6182901 | 6182931 | Hypo | cancer_general | — | chr9 | 6756353 | 6756623 | Hypo | cancer_general | KDM4C |
| chr9 | 14884008 | 14884061 | Hypo | hepatobiliary | — | chr9 | 20199955 | 20199985 | Hypo | hepatobiliary | — |
| chr9 | 21970966 | 21971220 | Hypo | literature | CDKN2A, C9orf53 | chr9 | 21974207 | 21974237 | Hypo | esophageal | CDKN2A, C9orf53 |
| chr9 | 21974663 | 21974794 | Hypo | literature | CDKN2A, C9orf53 | chr9 | 22006131 | 22006160 | Hypo | literature | CDKN2B, CDKN2B-AS1 |
| chr9 | 22008819 | 22008899 | Hypo | literature | CDKN2B, CDKN2B-AS1 | chr9 | 33000470 | 33000512 | Hypo | cancer_general | APTX |
| chr9 | 34136792 | 34136903 | Hypo | head_neck | DQ585850, DQ594696, DQ597117, DQ587955, DQ574810 | chr9 | 34224348 | 34224474 | Hypo | breast | UBAP1, KIF24 |
| chr9 | 34372805 | 34372983 | Hypo | breast | C9orf24, KIAA1161 | chr9 | 36036323 | 36036353 | Hypo | ovarian | RECK |
| chr9 | 36167272 | 36167544 | Hypo | cancer_general | CCIN, GLIPR2 | chr9 | 36196920 | 36197005 | Hypo | ovarian | CLTA |
| chr9 | 36318375 | 36318410 | Hypo | cancer_general | — | chr9 | 36433491 | 36433629 | Hypo | cancer_general | — |
| chr9 | 36832204 | 36832343 | Hypo | cancer_general | PAX5, MIR4475 | chr9 | 37119301 | 37119331 | Hypo | head_neck | ZCCHC7 |
| chr9 | 37467610 | 37467898 | Hypo | cancer_general | — | chr9 | 37593684 | 37593795 | Hypo | cancer_general | TOMM5 |
| chr9 | 37697404 | 37697438 | Hypo | cancer_general | FRMPD1 | chr9 | 38646763 | 38646839 | Hypo | cancer_general | — |
| chr9 | 71200632 | 71200662 | Hypo | cancer_general | — | chr9 | 71500847 | 71500886 | Hypo | hepatobiliary | — |
| chr9 | 71584152 | 71584254 | Hypo | hepatobiliary | AK057188 | chr9 | 71734816 | 71735024 | Hypo | cancer_general | TJP2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 72435189 | 72435317 | Hypo | cancer_general | BC039385, C9orfl35, LOC494558 | chr9 | 73032801 | 73032831 | Hypo | cancer_general | KLF9 |
| chr9 | 74210499 | 74210654 | Hypo | cancer_general | — | chr9 | 77823177 | 77823315 | Hypo | cancer_general | PRUNE2 |
| chr9 | 79197119 | 79197149 | Hypo | hepatobiliary | — | chr9 | 79231003 | 79231033 | Hypo | cancer_general | — |
| chr9 | 79638138 | 79638244 | Hypo | cancer_general | FOXB2 | chr9 | 80303132 | 80303171 | Hypo | cancer_general | — |
| chr9 | 80409473 | 80409502 | Hypo | literature | GNAQ | chr9 | 80833933 | 80834011 | Hypo | lung | — |
| chr9 | 85372494 | 85372596 | Hypo | cancer_general | — | chr9 | 86578079 | 86578366 | Hypo | ovarian | C9orf64, HNRNPK, MIR7-1 |
| chr9 | 88694345 | 88694438 | Hypo | cancer_general | GOLM1 | chr9 | 90907408 | 90907438 | Hypo | hepatobiliary | — |
| chr9 | 90937387 | 90937387 | Hypo | cancer_general | — | chr9 | 91914276 | 91914306 | Hypo | cancer_general | — |
| chr9 | 92053911 | 92053949 | Hypo | ovarian | SEMA4D | chr9 | 93698029 | 93698133 | Hypo | colorectal | — |
| chr9 | 94572641 | 94572743 | Hypo | cancer_general | ROR2 | chr9 | 94686919 | 94686957 | Hypo | hepatobiliary | ROR2 |
| chr9 | 95417551 | 95417651 | Hypo | cancer_general | — | chr9 | 95560810 | 95560840 | Hypo | cancer_general | FAM120A |
| chr9 | 95761687 | 95761828 | Hypo | cancer_general | FGD3 | chr9 | 96230296 | 96230334 | Hypo | cancer_general | PTPDC1 |
| chr9 | 96573748 | 96573869 | Hypo | cancer_general | MIR4291 | chr9 | 96856991 | 96857144 | Hypo | cancer_general | MIR23B, MIR3074 |
| chr9 | 97020978 | 97021126 | Hypo | cancer_general | ZNF169 | chr9 | 97845915 | 97845947 | Hypo | head_neck | CDC14B, HABP4 |
| chr9 | 98076746 | 98076776 | Hypo | cancer_general | FANCC | chr9 | 99259362 | 99259405 | Hypo | ovarian | NCBP1, TSTD2 |
| chr9 | 99450020 | 99450142 | Hypo | lung | — | chr9 | 100397821 | 100398016 | Hypo | cancer_general | TRIM14, NANS |
| chr9 | 100818295 | 100818437 | Hypo | cancer_general | NANS | chr9 | 100835828 | 100835870 | Hypo | cancer_general | — |
| chr9 | 103174620 | 103174730 | Hypo | cancer_general | — | chr9 | 106998039 | 106998134 | Hypo | head_neck | FRRS1L, AL390170 |
| chr9 | 110126074 | 110126247 | Hypo | cancer_general | — | chr9 | 111894386 | 111894520 | Hypo | colorectal | KIAA0368 |
| chr9 | 112403364 | 112403394 | Hypo | esophageal | Mir_548, PALM2 | chr9 | 114247454 | 114247578 | Hypo | cancer_general | — |
| chr9 | 115067932 | 115068106 | Hypo | cancer_general | — | chr9 | 115087567 | 115087597 | Hypo | cancer_general | SNX30 |
| chr9 | 115478932 | 115479250 | Hypo | cancer_general | INIP | chr9 | 115566363 | 115566583 | Hypo | cancer_general | — |
| chr9 | 116633883 | 116633987 | Hypo | cancer_general | ZNF618 | chr9 | 117050981 | 117051030 | Hypo | cancer_general | CDK5RAP2 |
| chr9 | 119603412 | 119603535 | Hypo | head_neck | — | chr9 | 123295355 | 123295463 | Hypo | cancer_general | TTLL11 |
| chr9 | 124749865 | 124749953 | Hypo | ovarian | TTLL11 | chr9 | 124751485 | 124751515 | Hypo | cancer_general | RABGAP1 |
| chr9 | 125676633 | 125676753 | Hypo | cancer_general | ZBTB26, ZBTB6 | chr9 | 125704789 | 125704835 | Hypo | cancer_general | DENND1A |
| chr9 | 126133778 | 126133856 | Hypo | cancer_general | DENND1A, CRB2 | chr9 | 126154304 | 126154575 | Hypo | cancer_general | — |
| chr9 | 126349038 | 126349104 | Hypo | lung | DENND1A | chr9 | 127605297 | 127605327 | Hypo | head_neck | — |
| chr9 | 127630125 | 127630205 | Hypo | cancer_general | ARPC5L, RPL35, WDR38 | chr9 | 127853274 | 127853304 | Hypo | breast | — |
| chr9 | 127920543 | 127920572 | Hypo | literature | PPP6C | chr9 | 128136065 | 128136095 | Hypo | cancer_general | GAPVD1 |
| chr9 | 128635180 | 128635210 | Hypo | ovarian | PBX3 | chr9 | 128759852 | 128759954 | Hypo | cancer_general | — |
| chr9 | 129388719 | 129388796 | Hypo | cancer_general | LMX1B | chr9 | 129517783 | 129517821 | Hypo | colorectal | — |
| chr9 | 130248419 | 130248449 | Hypo | cancer_general | AX747547, LRSAM1 | chr9 | 130325967 | 130325997 | Hypo | cancer_general | FAM129B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 130675509 | 130675615 | Hypo | cancer_general | PIP5KL1, ST6GALNAC4 | chr9 | 130694413 | 130694468 | Hypo | cancer_general | DPM2, FAM102A, PIP5KL1 |
| chr9 | 130694809 | 130694948 | Hypo | cancer_general | DPM2, FAM102A, PIP5KL1 | chr9 | 131177975 | 131178094 | Hypo | cancer_general | CERCAM |
| chr9 | 131417698 | 131417940 | Hypo | cancer_general | — | chr9 | 131542193 | 131542267 | Hypo | head_neck | TBC1D13, ZER1 |
| chr9 | 131580038 | 131580257 | Hypo | cancer_general | ENDOG, C9orf114, TBC1D13 | chr9 | 131607517 | 131607547 | Hypo | cancer_general | CCBL1 |
| chr9 | 131607770 | 131607800 | Hypo | cancer_general | CCBL1 | chr9 | 131854231 | 131854328 | Hypo | cancer_general | CRAT, DOLPP1 |
| chr9 | 131854564 | 131854732 | Hypo | cancer_general | CRAT, DOLPP1 | chr9 | 132373058 | 132373091 | Hypo | breast | C9orf50 |
| chr9 | 132383347 | 132383376 | Hypo | literature | C9orf50, NTMT1 | chr9 | 132402840 | 132402883 | Hypo | cancer_general | ASB6, NTMT1 |
| chr9 | 132403149 | 132403216 | Hypo | cancer_general | ASB6, NTMT1 | chr9 | 132559377 | 132559456 | Hypo | cancer_general | TOR1B |
| chr9 | 132815175 | 132815205 | Hypo | cancer_general | Mir_562, FNBP1, GPR107 | chr9 | 132881814 | 132881844 | Hypo | cancer_general | — |
| chr9 | 133605601 | 133605631 | Hypo | literature | ABL1 | chr9 | 133738343 | 133738372 | Hypo | literature | AX748265, ABL1 |
| chr9 | 133747505 | 133747534 | Hypo | literature | AX748265, ABL1 | chr9 | 133773766 | 133773923 | Hypo | cancer_general | FIBCD1, QRFP |
| chr9 | 133927347 | 133927481 | Hypo | cancer_general, colorectal, cancer_general | LAMC3 | chr9 | 133928236 | 133928266 | Hypo | cancer_general | LAMC3 |
| chr9 | 134126670 | 134126741 | Hypo | cancer_general | FAM78A | chr9 | 134191085 | 134191218 | Hypo | cancer_general | PPAPDC3 |
| chr9 | 134207916 | 134208048 | Hypo | cancer_general | — | chr9 | 134717313 | 134717367 | Hypo | cancer_general | SETX |
| chr9 | 135073463 | 135073506 | Hypo | hepatobiliary | NTNG2 | chr9 | 135135114 | 135135247 | Hypo | cancer_general | BARHL1, C9orfl71 |
| chr9 | 135231073 | 135231158 | Hypo | cancer_general | — | chr9 | 135456476 | 135456544 | Hypo | pancreas | — |
| chr9 | 135548238 | 135548313 | Hypo | cancer_general | GTF3C4, DDX31 | chr9 | 135590218 | 135590334 | Hypo | cancer_general | — |
| chr9 | 135796801 | 135796830 | Hypo | literature | TSC1 | chr9 | 135865090 | 135865161 | Hypo | cancer_general | GFI1B |
| chr9 | 135898911 | 135899124 | Hypo | cancer_general | GTF3C5 | chr9 | 137002646 | 137002692 | Hypo | cancer_general | WDR5 |
| chr9 | 137299670 | 137299699 | Hypo | tcga | RXRA | chr9 | 137575915 | 137575945 | Hypo | cancer_general | COL5A1 |
| chr9 | 137656958 | 137657128 | Hypo | cancer_general | COL5A1 | chr9 | 137667327 | 137667357 | Hypo | cancer_general | COL5A1 |
| chr9 | 137718901 | 137719001 | Hypo | cancer_general | LOC101448202, COL5A1 | chr9 | 137722087 | 137722209 | Hypo | cancer_general | LOC101448202, COL5A1 |
| chr9 | 138265123 | 138265251 | Hypo | cancer_general | — | chr9 | 138474557 | 138474590 | Hypo | cancer_general | LOC100130954 |
| chr9 | 138563059 | 138563280 | Hypo | cancer_general | LCN9 | chr9 | 138627636 | 138627893 | Hypo | cancer_general | KCNT1 |
| chr9 | 138634047 | 138634159 | Hypo | cancer_general | KCNT1 | chr9 | 138659800 | 138659905 | Hypo | cancer_general | KCNT1 |
| chr9 | 138660943 | 138661012 | Hypo | literature | KCNT1 | chr9 | 138661648 | 138661870 | Hypo | cancer_general | KCNT1 |
| chr9 | 138666455 | 138666558 | Hypo | cancer_general | KCNT1 | chr9 | 138826382 | 138826412 | Hypo | head_neck | UBAC1 |
| chr9 | 138880711 | 138880875 | Hypo | cancer_general | — | chr9 | 138991798 | 138991828 | Hypo | esophageal | NACC2 |
| chr9 | 139000566 | 139000642 | Hypo | cancer_general | C9orf69 | chr9 | 139012272 | 139012411 | Hypo | cancer_general | C9orf69 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 139045653 | 139045683 | Hypo | cancer_general | — | chr9 | 139047532 | 139047633 | Hypo | cancer_general | — |
| chr9 | 139111268 | 139111298 | Hypo | cancer_general | QSOX2 | chr9 | 139269039 | 139269121 | Hypo | breast | SNAPC4, CARD9 |
| chr9 | 139399407 | 139399436 | Hypo | literature | NOTCH1 | chr9 | 139421955 | 139421985 | Hypo | cancer_general | MIR4673 |
| chr9 | 139477862 | 139478020 | Hypo | head_neck | — | chr9 | 139698925 | 139699051 | Hypo | cancer_general | RABL6, KIAA1984-AS1, KIAA1984 |
| chr9 | 139704008 | 139704279 | Hypo | cancer_general | RABL6, KIAA1984-AS1, KIAA1984 | chr9 | 139859041 | 139859268 | Hypo | cancer_general | LCN12 |
| chr9 | 139888945 | 139888980 | Hypo | breast | CLIC3, C9orf142, LCNL1 | chr9 | 140015209 | 140015241 | Hypo | ovarian | DPP7 |
| chr9 | 140030498 | 140030528 | Hypo | cancer_general | GRIN1 | chr9 | 140031944 | 140032082 | Hypo | cancer_general | GRIN1 |
| chr9 | 140033001 | 140033092 | Hypo | pancreas | GRIN1 | chr9 | 140127883 | 140128080 | Hypo | cancer_general | FAM166A, SLC34A3, RNF224, C9orf169, AK128153, TUBB4B, TUBB2C |
| chr9 | 140137310 | 140137488 | Hypo | cancer_general | FAM166A, LOC100129722, C9orf173, TUBB2C, TUBB4B, SLC34A3 | chr9 | 140205394 | 140205519 | Hypo | cancer_general | EXD3, NRARP |
| chr9 | 140245877 | 140245998 | Hypo | cancer_general | EXD3 | chr9 | 140332708 | 140333018 | Hypo | cancer_general | NSMF, ENTPD8, NOXA1 |
| chr9 | 140382557 | 140382596 | Hypo | cancer_general | PNPLA7 | chr9 | 140392454 | 140392484 | Hypo | cancer_general | — |
| chr9 | 140397029 | 140397097 | Hypo | cancer_general | — | chr9 | 140498318 | 140498394 | Hypo | cancer_general | ARRDC1 |
| chr9 | 140507256 | 140507419 | Hypo | cancer_general | ARRDC1, C9orf37, EHMT1 | chr9 | 140704046 | 140704131 | Hypo | ovarian | EHMT1 |
| chr9 | 140709046 | 140709174 | Hypo | head_neck | EHMT1 | chr9 | 140727471 | 140727511 | Hypo | head_neck | MIR602, EHMT1 |
| chr9 | 140727845 | 140727930 | Hypo | head_neck | MIR602, EHMT1 | chr9 | 140769943 | 140769973 | Hypo | cancer_general | CACNA1B, AK128414 |
| chr16 | 93831 | 93932 | Hypo | head_neck | POLR3K, SNRNP25 | chr16 | 142649 | 142783 | Hypo | lung | NPRL3, MPG |
| chr16 | 189744 | 189933 | Hypo | cancer_general | NPRL3 | chr16 | 199886 | 199943 | Hypo | cancer_general | HBZ |
| chr16 | 232136 | 232166 | Hypo | cancer_general | HBQ1, HBA1, HBA2, LUC7L | chr16 | 280323 | 280395 | Hypo | cancer_general | ITFG3, LUC7L |
| chr16 | 318104 | 318227 | Hypo | cancer_general | RGS11, ITFG3 | chr16 | 318498 | 318763 | Hypo | cancer_general | RGS11, ITFG3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 337599 | 337659 | Hypo | cancer_general | AXIN1, PDIA2, ARHGDIG | chr16 | 410377 | 410407 | Hypo | cancer_general | AXIN1, MRPL28 |
| chr16 | 571714 | 571959 | Hypo | cancer_general | LINC00235, SOLH, RAB11FIP3 | chr16 | 611385 | 611520 | Hypo | cancer_general | NHLRC4, PIGQ, C16orf11, SOLH |
| chr16 | 611969 | 612260 | Hypo | cancer_general | NHLRC4, PIGQ, C16orf11, SOLH | chr16 | 612869 | 613037 | Hypo | cancer_general | NHLRC4, PIGQ, C16orf11, SOLH |
| chr16 | 667141 | 667297 | Hypo | lung | RAB40C | chr16 | 667547 | 667622 | Hypo | lung | RAB40C |
| chr16 | 667876 | 668074 | Hypo | lung | RAB40C | chr16 | 672730 | 672806 | Hypo | head_neck | WFIKKN1, RAB40C, AK128777 |
| chr16 | 677972 | 678084 | Hypo | lung | AK301549, RAB40C, AK128777, WFIKKN1, C16orf13, TRNA_Gly, TRNA | chr16 | 700299 | 700329 | Hypo | cancer_general | WDR90, FAM195A |
| chr16 | 726626 | 726990 | Hypo | cancer_general | STUB1, JMJD8, WDR24, RHBDL1, RHOT2, WDR90 | chr16 | 731488 | 731610 | Hypo | cancer_general | STUB1, RHBDL1, RHOT2, JMJD8, WDR24 |
| chr16 | 735205 | 735594 | Hypo | cancer_general | FBXL16, WDR24, JMJD8, STUB1, RHBDL1 | chr16 | 740791 | 740914 | Hypo | cancer_general | STUB1, FBXL16, WDR24, JMJD8 |
| chr16 | 741376 | 741601 | Hypo | cancer_general | STUB1, FBXL16, WDR24, JMJD8 | chr16 | 762523 | 762694 | Hypo | cancer_general | METRN, AL360260, FAM173A, CCDC78 |
| chr16 | 837361 | 837460 | Hypo | cancer_general | CHTF18, RPUSD1 | chr16 | 845955 | 845985 | Hypo | cancer_general | GNG13, PRR25, CHTF18, RPUSD1 |
| chr16 | 882484 | 882588 | Hypo | cancer_general | — | chr16 | 895093 | 895166 | Hypo | cancer_general | LMF1 |
| chr16 | 943481 | 943553 | Hypo | cancer_general | LMF1 | chr16 | 1018120 | 1018150 | Hypo | cancer_general | LMF1 |
| chr16 | 1019640 | 1019685 | Hypo | ovarian | LMF1 | chr16 | 1052587 | 1052627 | Hypo | cancer_general | — |
| chr16 | 1102927 | 1102957 | Hypo | cancer_general | — | chr16 | 1116661 | 1116691 | Hypo | cancer_general | SSTR5, SSTR5-AS1 |
| chr16 | 1129011 | 1129140 | Hypo | cancer_general | C1QTNF8, SSTR5, BC084558, SSTR5-AS1 | chr16 | 1155162 | 1155212 | Hypo | cancer_general | C1QTNF8 |

TABLE 11-continued

| chr | Start | Stop | Hypo/hyper | classification | annotation |
|---|---|---|---|---|---|
| chr16 | 1186809 | 1186850 | Hypo | cancer_general | CACNA1H |
| chr16 | 1218034 | 1218090 | Hypo | cancer_general | CACNA1H |
| chr16 | 1229970 | 1230142 | Hypo | cancer_general | CACNA1H |
| chr16 | 1267925 | 1268120 | Hypo | cancer_general | TPSG1, TPSB2, CACNA1H |
| chr16 | 1312526 | 1312611 | Hypo | cancer_general | TPSD1 |
| chr16 | 1394502 | 1394596 | Hypo | cancer_general | TSR3, GNPTG, BAIAP3 |
| chr16 | 1407370 | 1407846 | Hypo | lung, cancer_general | UNKL, GNPTG, TSR3, BAIAP3 |
| chr16 | 1428508 | 1428873 | Hypo | cancer_general | UNKL |
| chr16 | 1469334 | 1469527 | Hypo | cancer_general | C16orf91, UNKL |
| chr16 | 1523925 | 1523971 | Hypo | cancer_general | CLCN7 |
| chr16 | 1729868 | 1730022 | Hypo | cancer_general | CRAMP1L, HN1L |
| chr16 | 1741853 | 1742079 | Hypo | cancer_general | HN1L, CRAMP1L |
| chr16 | 1993818 | 1993848 | Hypo | cancer_general | RPL3L, MSRB1 |
| chr16 | 2042875 | 2042905 | Hypo | head_neck | ZNF598, SYNGR3, GFER |
| chr16 | 2111966 | 2111995 | Hypo | literature | TSC2 |
| chr16 | 2122243 | 2122272 | Hypo | literature | — |
| chr16 | 2126080 | 2126109 | Hypo | literature | TSC2 |
| chr16 | 2130361 | 2130390 | Hypo | literature | TSC2, PKD1, MIR1225 |
| chr16 | 2136228 | 2136257 | Hypo | literature | PKD1, MIR1225, TSC2 |
| chr16 | 2141909 | 2141972 | Hypo | cancer_general | PKD1, MIR1225, TSC2 |
| chr16 | 2213313 | 2213343 | Hypo | cancer_general | TRAF7, SNORD60, RAB26 |
| chr16 | 2234726 | 2235020 | Hypo | cancer_general | CASKIN1, TRAF7 |
| chr16 | 2281249 | 2281314 | Hypo | lung | E4F1, DNASE1L2, ECI1 |
| chr16 | 1217307 | 1217503 | Hypo | cancer_general | CACNA1H |
| chr16 | 1228804 | 1228916 | Hypo | cancer_general | CACNA1H |
| chr16 | 1248604 | 1248675 | Hypo | cancer_general | CACNA1H |
| chr16 | 1271546 | 1271646 | Hypo | cancer_general | TPSB2, CACNA1H, TPSG1 |
| chr16 | 1323976 | 1324061 | Hypo | cancer_general | — |
| chr16 | 1397454 | 1397484 | Hypo | head_neck | BAIAP3, TSR3, GNPTG |
| chr16 | 1408210 | 1408240 | Hypo | cancer_general | UNKL, GNPTG, TSR3, BAIAP3 |
| chr16 | 1466425 | 1466455 | Hypo | cancer_general | UNKL, C16orf91 |
| chr16 | 1491567 | 1491613 | Hypo | cancer_general | CLCN7, CCDC154 |
| chr16 | 1704656 | 1704800 | Hypo | breast | CRAMP1L, HN1L |
| chr16 | 1730306 | 1730597 | Hypo | cancer_general | CRAMP1L, MAPK8IP3, HN1L |
| chr16 | 1750769 | 1750907 | Hypo | head_neck | — |
| chr16 | 2029072 | 2029137 | Hypo | cancer_general | GFER, NOXO1, TBL3 |
| chr16 | 2106703 | 2106732 | Hypo | literature | TSC2, NTHL1 |
| chr16 | 2120515 | 2120544 | Hypo | literature | — |
| chr16 | 2124205 | 2124348 | Hypo | literature | TSC2 |
| chr16 | 2128577 | 2129581 | Hypo | head_neck | PKD1, TSC2 |
| chr16 | 2135301 | 2135330 | Hypo | literature | PKD1, MIR1225, TSC2 |
| chr16 | 2136727 | 2136855 | Hypo | literature | PKD1, MIR1225, TSC2 |
| chr16 | 2142546 | 2142628 | Hypo | cancer_general | PKD1, MIR1225, TSC2 |
| chr16 | 2232745 | 2233003 | Hypo | cancer_general | CASKIN1, TRAF7 |
| chr16 | 2275129 | 2275182 | Hypo | cancer_general | E4F1 |
| chr16 | 2466225 | 2466307 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 2485858 | 2485917 | Hypo | head_neck | CCNF | chr16 | 2508414 | 2508453 | Hypo | lung | C16orf59, CCNF |
| chr16 | 2531069 | 2531177 | Hypo | cancer_general | TBC1D24, NTN3 | chr16 | 2731530 | 2731560 | Hypo | cancer_general | KCTD5, ERVK13-1 |
| chr16 | 2764377 | 2764470 | Hypo | cancer_general | PRSS27, KCTD5 | chr16 | 2770122 | 2770602 | Hypo | cancer_general | PRSS27 |
| chr16 | 2818101 | 2818156 | Hypo | cancer_general | TCEB2, SRRM2 | chr16 | 2956451 | 2956670 | Hypo | cancer_general | FLYWCH1, FLYWCH2 |
| chr16 | 2974601 | 2974650 | Hypo | head_neck | FLYWCH1 | chr16 | 3151127 | 3151186 | Hypo | cancer_general | ZNF205-AS1, ZSCAN10 |
| chr16 | 3211708 | 3212019 | Hypo | cancer_general | TRNA_Lys, TRNA_Pseudo, TRNA_Pro, TRNA_Arg | chr16 | 3269249 | 3269350 | Hypo | cancer_general | ZNF200, OR1F2P |
| chr16 | 3284117 | 3284147 | Hypo | esophageal | MEFV, ZNF200 | chr16 | 3492583 | 3492675 | Hypo | cancer_general | NAA60, ZNF597 |
| chr16 | 3598920 | 3598953 | Hypo | cancer_general | NLRC3 | chr16 | 3696694 | 3696724 | Hypo | cancer_general | DNASE1 |
| chr16 | 3802981 | 3803074 | Hypo | breast | CREBBP | chr16 | 3950127 | 3950279 | Hypo | cancer_general | — |
| chr16 | 4264529 | 4264694 | Hypo | cancer_general | SRL | chr16 | 4303144 | 4303174 | Hypo | cancer_general | TFAP4, LOC100507501 |
| chr16 | 4310735 | 4310847 | Hypo | cancer_general | TFAP4, LOC100507501 | chr16 | 4431126 | 4431189 | Hypo | ovarian | VASN, CORO7-PAM16, CORO7 |
| chr16 | 4783226 | 4783375 | Hypo | cancer_general | C16orf71, ANKS3 | chr16 | 4846136 | 4846514 | Hypo | cancer_general | GLYR1, LOC440335, SEPT12, ROGDI |
| chr16 | 4887144 | 4887244 | Hypo | breast | UBN1, GLYR1 | chr16 | 5541116 | 5541158 | Hypo | cancer_general | BC108660 |
| chr16 | 6035056 | 6035208 | Hypo | cancer_general | — | chr16 | 7382499 | 7382534 | Hypo | literature | RBFOX1 |
| chr16 | 7525361 | 7525531 | Hypo | cancer_general | RBFOX1 | chr16 | 8781032 | 8781177 | Hypo | cancer_general | ABAT |
| chr16 | 8870353 | 8870383 | Hypo | cancer_general | ABAT | chr16 | 9009860 | 9009989 | Hypo | cancer_general | USP7 |
| chr16 | 11242000 | 11242138 | Hypo | cancer_general | CLEC16A | chr16 | 11427659 | 11427732 | Hypo | cancer_general | |
| chr16 | 11490632 | 11490662 | Hypo | blood | — | chr16 | 11923005 | 11923035 | Hypo | cancer_general | RSL1D1, BCAR4 |
| chr16 | 12011258 | 12011325 | Hypo | cancer_general | GSPT1 | chr16 | 12011940 | 12012073 | Hypo | cancer_general | GSPT1 |
| chr16 | 12066767 | 12066806 | Hypo | cancer_general | SNX29, TNFRSF17 | chr16 | 12210772 | 12210896 | Hypo | head_neck | SNX29 |
| chr16 | 12211279 | 12211416 | Hypo | head_neck | SNX29 | chr16 | 12530169 | 12530199 | Hypo | cancer_general | ERCC4 |
| chr16 | 12971776 | 12971934 | Hypo | cancer_general | — | chr16 | 14021974 | 14022003 | Hypo | literature | ERCC4 |
| chr16 | 14041504 | 14041533 | Hypo | literature | ERCC4 | chr16 | 14041795 | 14041824 | Hypo | literature | MKL2 |
| chr16 | 14042062 | 14042091 | Hypo | literature | ERCC4 | chr16 | 14189948 | 14190069 | Hypo | cancer_general | BEAR, PARN |
| chr16 | 14724632 | 14724736 | Hypo | cancer_general | BEAR, PARN | chr16 | 14725842 | 14726005 | Hypo | cancer_general | |
| chr16 | 15708247 | 15708309 | Hypo | pancreas | KIAA0430 | chr16 | 15738905 | 15739042 | Hypo | cancer_general | KIAA0430, NDE1, MIR484 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 15820825 | 15820865 | Hypo | cancer_general | AX747846, MYH11 | chr16 | 16868746 | 16868905 | Hypo | cancer_general | — |
| chr16 | 18163245 | 18163352 | Hypo | cancer_general | — | chr16 | 18802250 | 18802680 | Hypo | cancer_general | ARL6IP1, RPS15A |
| chr16 | 18950928 | 18951018 | Hypo | cancer_general | GDE1, CCP110 | chr16 | 19430908 | 19430949 | Hypo | cancer_general | TMC5 |
| chr16 | 19531564 | 19531697 | Hypo | cancer_general | IGSF6 | chr16 | 21541606 | 21541636 | Hypo | cancer_general | SLC7A5P2 |
| chr16 | 21665540 | 21665570 | Hypo | head_neck | — | chr16 | 21666641 | 21666771 | Hypo | head_neck | IGSF6 |
| chr16 | 21674664 | 21674777 | Hypo | ovarian | TRNA_Leu, TRNA, POLR3E, EEF2K | chr16 | 21839328 | 21839470 | Hypo | cancer_general | RRN3P1, LOC23117, LOC100132247 |
| chr16 | 22300599 | 22300637 | Hypo | cancer_general | PRKCB | chr16 | 22326397 | 22326427 | Hypo | head_neck | POLR3E |
| chr16 | 24127251 | 24127338 | Hypo | cancer_general | PRKCB | chr16 | 24172241 | 24172271 | Hypo | cancer_general | PRKCB |
| chr16 | 24180710 | 24180760 | Hypo | cancer_general | ZKSCAN2 | chr16 | 24415106 | 24415176 | Hypo | cancer_general | — |
| chr16 | 25266537 | 25266573 | Hypo | cancer_general | — | chr16 | 25542301 | 25542452 | Hypo | cancer_general | — |
| chr16 | 25551107 | 25551264 | Hypo | cancer_general | — | chr16 | 25921574 | 25921604 | Hypo | cancer_general | HS3ST4 |
| chr16 | 26302585 | 26302619 | Hypo | cancer_general | KDM8 | chr16 | 26664739 | 26664775 | Hypo | cancer_general | — |
| chr16 | 27207774 | 27207852 | Hypo | head_neck | — | chr16 | 27459938 | 27460074 | Hypo | cancer_general | IL21R-AS1, IL21R |
| chr16 | 27749857 | 27750033 | Hypo | breast | — | chr16 | 27961122 | 27961254 | Hypo | cancer_general | — |
| chr16 | 28093825 | 28093866 | Hypo | cancer_general | CLN3 | chr16 | 28224516 | 28224546 | Hypo | ovarian | XPO6 |
| chr16 | 28491774 | 28491924 | Hypo | colorectal | AK125489 | chr16 | 28560309 | 28560381 | Hypo | cancer_general | CCDC101, NUPR1 |
| chr16 | 28823157 | 28823459 | Hypo | cancer_general | SH2B1 | chr16 | 28850998 | 28851028 | Hypo | breast | ATXN2L, TUFM, MIR4721, SH2B1 |
| chr16 | 28877839 | 28877883 | Hypo | esophageal | BC029255, PAGR1, PRRT2, AK097472, AB209061, MAZ, MVP | chr16 | 29119008 | 29119058 | Hypo | cancer_general | AK075019, RRN3P2 |
| chr16 | 29153284 | 29153356 | Hypo | cancer_general | DOC2A, INO80E | chr16 | 29244900 | 29244997 | Hypo | cancer_general | KCTD13, ASPHD1 |
| chr16 | 29830871 | 29831078 | Hypo | cancer_general | PPP4C, ALDOA | chr16 | 29936211 | 29936272 | Hypo | cancer_general | |
| chr16 | 30017330 | 30017447 | Hypo | cancer_general | MAPK3, GDPD3, AK097453 | chr16 | 30065485 | 30065525 | Hypo | cancer_general | ALDOA |
| chr16 | 30085867 | 30085995 | Hypo | cancer_general | | chr16 | 30116285 | 30116315 | Hypo | cancer_general | MAPK3, GDPD3, AK097453, YPEL3 |
| chr16 | 30124691 | 30124861 | Hypo | cancer_general | | chr16 | 30169925 | 30170103 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 30388542 | 30388574 | Hypo | cancer_general | SEPT1, ZNF48, MYLPF, TBC1D10B | chr16 | 30402082 | 30402112 | Hypo | cancer_general | ZNF48, SEPT1 |
| chr16 | 30609373 | 30609408 | Hypo | cancer_general | ZNF689 | chr16 | 30639693 | 30639735 | Hypo | cancer_general | — |
| chr16 | 30804321 | 30804472 | Hypo | cancer_general | ZNF629 | chr16 | 30826334 | 30826509 | Hypo | cancer_general | — |
| chr16 | 30907010 | 30907148 | Hypo | lung, cancer_general | BC073928, CTF1, MIR762, BCL7C | chr16 | 31384593 | 31384623 | Hypo | cancer_general | ITGAX |
| chr16 | 31446830 | 31447096 | Hypo | cancer_general | ZNF843, COX6A2, ITGAD | chr16 | 31498008 | 31498165 | Hypo | cancer_general | C16orf58, SLC5A2, TGFB1I1, BC054514 |
| chr16 | 31500544 | 31500673 | Hypo | cancer_general | SLC5A2, C16orf58, BC054514 | chr16 | 46569239 | 46569474 | Hypo | cancer_general | — |
| chr16 | 46721567 | 46721707 | Hypo | head_neck | ORC6, VPS35 | chr16 | 46803280 | 46803355 | Hypo | lung | — |
| chr16 | 48450544 | 48450574 | Hypo | cancer_general | — | chr16 | 48641663 | 48641693 | Hypo | cancer_general | N4BP1 |
| chr16 | 48642149 | 48642179 | Hypo | cancer_general | N4BP1 | chr16 | 49314810 | 49314840 | Hypo | cancer_general | CBLN1 |
| chr16 | 49638060 | 49638090 | Hypo | cancer_general | ZNF423 | chr16 | 50335767 | 50335797 | Hypo | cancer_general | ADCY7 |
| chr16 | 53347826 | 53448002 | Hypo | cancer_general | — | chr16 | 53467271 | 53467395 | Hypo | cancer_general | RBL2, U6 |
| chr16 | 53563622 | 53563654 | Hypo | tcga | — | chr16 | 54128645 | 54128713 | Hypo | breast | FTO |
| chr16 | 56672656 | 56672685 | Hypo | tcga | MT1A, MT1JP, MT1M, MT1DP | chr16 | 57222663 | 57222709 | Hypo | cancer_general | RSPRY1 |
| chr16 | 57326422 | 57326613 | Hypo | cancer_general | PLLP, TRNA_Leu | chr16 | 57935454 | 57935605 | Hypo | cancer_general | CNGB1 |
| chr16 | 58120795 | 58120961 | Hypo | cancer_general | SETD6, CNOT1, NDRG4 | chr16 | 58427501 | 58427542 | Hypo | cancer_general | GINS3 |
| chr16 | 58545487 | 58545516 | Hypo | literature | | chr16 | 58550489 | 58550519 | Hypo | cancer_general | NDRG4, CNOT1, SETD6 |
| chr16 | 58969757 | 58969792 | Hypo | cancer_general | AK057513 | chr16 | 66863917 | 66863959 | Hypo | cancer_general | NAE1 |
| chr16 | 67241204 | 67241234 | Hypo | cancer_general | LRRC29, MIR328, ELMO3, E2F4 | chr16 | 67313865 | 67313895 | Hypo | cancer_general | KCTD19, PLEKHG4 |
| chr16 | 67850955 | 67850985 | Hypo | cancer_general | TSNAXIP1 | chr16 | 67871102 | 67871134 | Hypo | cancer_general | NUTF2, CENPT, TSNAXIP1, THAP11 |
| chr16 | 68770755 | 68770974 | Hypo | cancer_general | CDH1 | chr16 | 68844158 | 68844187 | Hypo | literature | CDH1 |
| chr16 | 68846033 | 68846062 | Hypo | literature | CDH1 | chr16 | 68856078 | 68856107 | Hypo | literature | CDH1 |
| chr16 | 68876782 | 68876996 | Hypo | cancer_general | TANGO6, CDH1 | chr16 | 69026784 | 69026814 | Hypo | cancer_general | TANGO6 |
| chr16 | 69564118 | 69564200 | Hypo | cancer_general | — | chr16 | 69969260 | 69969290 | Hypo | breast | MIR140, WWP2 |
| chr16 | 70489585 | 70489681 | Hypo | cancer_general | FUK | chr16 | 70595535 | 70595700 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 70794492 | 70794633 | Hypo | cancer_general | BC033164, VAC14-AS1 | chr16 | 71507759 | 71507791 | Hypo | cancer_general | ZNF19, AK123826, ZNF23 |
| chr16 | 71677557 | 71677661 | Hypo | breast | KIAA0931, PHLPP2, MARVELD3 | chr16 | 71715779 | 71715809 | Hypo | colorectal | PHLPP2, TRNA_Gln |
| chr16 | 71918889 | 71919024 | Hypo | cancer_general | IST1, ZNF821 | chr16 | 72957763 | 72957795 | Hypo | cancer_general | — |
| chr16 | 74886148 | 74886268 | Hypo | cancer_general | — | chr16 | 74901594 | 74901659 | Hypo | cancer_general | WDR59 |
| chr16 | 75019751 | 75019781 | Hypo | cancer_general | — | chr16 | 75549798 | 75549836 | Hypo | cancer_general | — |
| chr16 | 76008985 | 76009154 | Hypo | hepatobiliary | — | chr16 | 77247440 | 77247470 | Hypo | cancer_general | SYCE1L |
| chr16 | 81564199 | 81564229 | Hypo | cancer_general | CMIP | chr16 | 81929362 | 81929392 | Hypo | cancer_general | PLCG2 |
| chr16 | 81946246 | 81946275 | Hypo | literature | PLCG2 | chr16 | 81962167 | 81962196 | Hypo | breast | PLCG2 |
| chr16 | 84074836 | 84074871 | Hypo | cancer_general | SLC38A8 | chr16 | 84153364 | 84153394 | Hypo | literature | MBTPS1, HSDL1 |
| chr16 | 84519974 | 84520010 | Hypo | hepatobiliary | TLDC1 | chr16 | 84823626 | 84823656 | Hypo | breast | — |
| chr16 | 85075434 | 85075553 | Hypo | cancer_general | KIAA0513 | chr16 | 85317850 | 85317882 | Hypo | cancer_general | LINC00311 |
| chr16 | 85485747 | 85485855 | Hypo | cancer_general | — | chr16 | 85497445 | 85497475 | Hypo | cancer_general | — |
| chr16 | 85517345 | 85517521 | Hypo | lung, cancer_general | — | chr16 | 85651520 | 85651550 | Hypo | cancer_general | GSE1 |
| chr16 | 85678639 | 85678761 | Hypo | cancer_general | GSE1 | chr16 | 85684308 | 85684457 | Hypo | cancer_general | GSE1 |
| chr16 | 85699689 | 85699921 | Hypo | breast | GSE1 | chr16 | 85834460 | 85834495 | Hypo | cancer_general | COX4I1, EMC8 |
| chr16 | 86571984 | 86572014 | Hypo | pancreas | MTHFSD | chr16 | 86878150 | 86878180 | Hypo | cancer_general | — |
| chr16 | 87092439 | 87092553 | Hypo | cancer_general | — | chr16 | 87714272 | 87714381 | Hypo | cancer_general | — |
| chr16 | 87723735 | 87724098 | Hypo | cancer_general | FLJ00104, hCG_1980662 | chr16 | 88007072 | 88007108 | Hypo | head_neck | BANP |
| chr16 | 88106322 | 88106398 | Hypo | breast | BANP | chr16 | 88164401 | 88164468 | Hypo | cancer_general | — |
| chr16 | 88498241 | 88498760 | Hypo | cancer_general | ZNF469 | chr16 | 88504058 | 88504315 | Hypo | cancer_general | ZNF469 |
| chr16 | 88506346 | 88506526 | Hypo | cancer_general | ZNF469 | chr16 | 88512427 | 88512529 | Hypo | cancer_general | ZFPM1, ZNF469 |
| chr16 | 88550263 | 88550483 | Hypo | cancer_general | — | chr16 | 88603696 | 88603760 | Hypo | cancer_general | — |
| chr16 | 88623960 | 88624167 | Hypo | cancer_general | C16orf85 | chr16 | 88711337 | 88711507 | Hypo | hepatobiliary | BC033739, MVD, BC028224, IL17C, CYBA |
| chr16 | 88757466 | 88757496 | Hypo | head_neck | RNF166, SNAI3 | chr16 | 88879949 | 88880124 | Hypo | cancer_general | GALNS, APRT, CDT1 |
| chr16 | 88883238 | 88883377 | Hypo | cancer_general | GALNS, APRT, CDT1 | chr16 | 88941058 | 88941141 | Hypo | cancer_general | CBFA2T3, PABPN1L |
| chr16 | 88942119 | 88942160 | Hypo | hepatobiliary | PABPN1L, CBFA2T3 | chr16 | 88943559 | 88944024 | Hypo | cancer_general | CBFA2T3 |
| chr16 | 88945815 | 88945995 | Hypo | cancer_general | CBFA2T3 | chr16 | 88955249 | 88955368 | Hypo | cancer_general | CBFA2T3 |
| chr16 | 88956230 | 88956399 | Hypo | cancer_general | CBFA2T3 | chr16 | 88957350 | 88957857 | Hypo | cancer_general | CBFA2T3 |
| chr16 | 88958397 | 88958431 | Hypo | cancer_general | CBFA2T3 | chr16 | 88963277 | 88963763 | Hypo | cancer_general | CBFA2T3 |
| chr16 | 88966303 | 88966588 | Hypo | cancer_general | CBFA2T3 | chr16 | 88968709 | 88968789 | Hypo | cancer_general | CBFA2T3 |
| chr16 | 88978024 | 88978072 | Hypo | cancer_general | CBFA2T3 | chr16 | 88993078 | 88993230 | Hypo | cancer_general | CBFA2T3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 88999617 | 88999647 | Hypo | cancer_general | CBFA2T3 | chr16 | 89000168 | 89000204 | Hypo | cancer_general | CBFA2T3 |
| chr16 | 89001094 | 89001124 | Hypo | cancer_general | CBFA2T3 | chr16 | 89047717 | 89047747 | Hypo | cancer_general | CBFA2T3 |
| chr16 | 89072503 | 89072774 | Hypo | cancer_general | — | chr16 | 89086109 | 89086197 | Hypo | cancer_general | — |
| chr16 | 89107675 | 89107732 | Hypo | cancer_general | AK055272 | chr16 | 89109415 | 89109415 | Hypo | cancer_general | AK055272 |
| chr16 | 89120038 | 89120319 | Hypo | cancer_general | AK055272 | chr16 | 89120708 | 89120864 | Hypo | cancer_general | AK055272 |
| chr16 | 89138016 | 89138060 | Hypo | cancer_general | — | chr16 | 89220327 | 89220398 | Hypo | cancer_general | LINC00304, ACSF3 |
| chr16 | 89220655 | 89220922 | Hypo | cancer_general | LINC00304, ACSF3 | chr16 | 89240843 | 89240873 | Hypo | head_neck | CDH15, LOC400558 |
| chr16 | 89254653 | 89254830 | Hypo | cancer_general | SLC22A31, CDH15 | chr16 | 89558610 | 89558703 | Hypo | cancer_general | — |
| chr16 | 89575728 | 89575861 | Hypo | cancer_general | SPG7 | chr16 | 89584136 | 89584417 | Hypo | head_neck | SPG7 |
| chr16 | 89676025 | 89676197 | Hypo | cancer_general | DPEP1 | chr16 | 89883972 | 89884185 | Hypo | cancer_general | FANCA |
| chr16 | 89884966 | 89885142 | Hypo | cancer_general | SPIRE2, FANCA | chr16 | 89900124 | 89900180 | Hypo | cancer_general | SPIRE2 |
| chr16 | 89900455 | 89900526 | Hypo | cancer_general | SPIRE2 | chr16 | 90115428 | 90115458 | Hypo | cancer_general | LOC100130015, AK127378, PRDM7 |
| chr2 | 142427 | 142468 | Hypo | cancer_general | — | chr2 | 496228 | 496380 | Hypo | cancer_general | — |
| chr2 | 602657 | 602687 | Hypo | cancer_general | — | chr2 | 720836 | 720894 | Hypo | cancer_general | — |
| chr2 | 875961 | 875991 | Hypo | cancer_general | — | chr2 | 1652837 | 1653230 | Hypo | hepatobiliary | — |
| chr2 | 1670168 | 1670216 | Hypo | hepatobiliary | PXDN | chr2 | 2321773 | 2321802 | Hypo | literature | PXDN |
| chr2 | 2336413 | 2336442 | Hypo | literature | LOC730811 | chr2 | 2646900 | 2646930 | Hypo | cancer_general | LOC730811 |
| chr2 | 2672620 | 2672732 | Hypo | cancer_general | — | chr2 | 2844720 | 2844750 | Hypo | cancer_general | — |
| chr2 | 2893195 | 2893195 | Hypo | cancer_general | AK095310 | chr2 | 3259989 | 3260103 | Hypo | pancreas | TSSC1 |
| chr2 | 4019911 | 4020036 | Hypo | cancer_general | LOC100505964 | chr2 | 4050752 | 4050781 | Hypo | literature | — |
| chr2 | 7062891 | 7062959 | Hypo | cancer_general | RNF144A, RNF144A-AS1 | chr2 | 7164467 | 7164788 | Hypo | pancreas | — |
| chr2 | 7236859 | 7236974 | Hypo | breast | — | chr2 | 8735932 | 8736064 | Hypo | ovarian | MBOAT2 |
| chr2 | 8835493 | 8835523 | Hypo | cancer_general | — | chr2 | 9090685 | 9090760 | Hypo | hepatobiliary | — |
| chr2 | 9134404 | 9134493 | Hypo | cancer_general | MBOAT2 | chr2 | 9192356 | 9192402 | Hypo | hepatobiliary | — |
| chr2 | 9289969 | 9290114 | Hypo | breast | — | chr2 | 9960734 | 9960764 | Hypo | cancer_general | — |
| chr2 | 10115730 | 10115772 | Hypo | cancer_general | — | chr2 | 10152798 | 10153325 | Hypo | cancer_general | — |
| chr2 | 10154266 | 10154564 | Hypo | cancer_general | — | chr2 | 10154930 | 10155298 | Hypo | cancer_general | — |
| chr2 | 10156116 | 10156389 | Hypo | cancer_general | — | chr2 | 10369155 | 10369242 | Hypo | pancreas | — |
| chr2 | 10408398 | 10408459 | Hypo | cancer_general | — | chr2 | 11142174 | 11142315 | Hypo | cancer_general | — |
| chr2 | 11356651 | 11356762 | Hypo | ovarian | ROCK2 | chr2 | 11672746 | 11672775 | Hypo | literature | GREB1, MIR4429 |
| chr2 | 11903450 | 11903480 | Hypo | pancreas | LPIN1 | chr2 | 12246114 | 12246217 | Hypo | cancer_general | — |
| chr2 | 12297534 | 12297564 | Hypo | cancer_general | — | chr2 | 13557899 | 13558057 | Hypo | hepatobiliary | — |
| chr2 | 15579989 | 15580019 | Hypo | cancer_general | — | chr2 | 20442433 | 20442498 | Hypo | cancer_general | PUM2 |
| chr2 | 20641988 | 20642081 | Hypo | cancer_general | RHOB | chr2 | 20642541 | 20642648 | Hypo | cancer_general | RHOB |
| chr2 | 20710145 | 20710324 | Hypo | cancer_general | — | chr2 | 22404181 | 22404227 | Hypo | cancer_general | — |
| chr2 | 24318290 | 24318357 | Hypo | cancer_general | POMC, EFR3B | chr2 | 25029252 | 25029300 | Hypo | cancer_general | CENPO |
| chr2 | 25374762 | 25374804 | Hypo | cancer_general | DTNB | chr2 | 25439727 | 25439915 | Hypo | cancer_general | — |
| chr2 | 25600736 | 25600804 | Hypo | head_neck | — | chr2 | 25928094 | 25928166 | Hypo | head_neck | Y_RNA |
| chr2 | 26372967 | 26372997 | Hypo | cancer_general | — | chr2 | 27271699 | 27272218 | Hypo | cancer_general | TMEM214, TRNA, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 27356168 | 27356198 | Hypo | ovarian | C2orf53, PREB, AK074615, ABHD1 | chr2 | 27433532 | 27433601 | Hypo | cancer_general | TRNA_Tyr, TRNA_Ala, AGBL5 ATRAID, CAD, SLC5A6 |
| chr2 | 27543012 | 27543074 | Hypo | lung | GTF3C2, MPV17 | chr2 | 27578243 | 27578396 | Hypo | cancer_general | EIF2B4 |
| chr2 | 27648172 | 27648294 | Hypo | cancer_general | NRBP1 | chr2 | 27764046 | 27764168 | Hypo | cancer_general | — |
| chr2 | 27887525 | 27887555 | Hypo | cancer_general | SLC4A1AP, SUPT7L | chr2 | 29091592 | 29091838 | Hypo | cancer_general | TRMT61B |
| chr2 | 29420483 | 29420512 | Hypo | literature | ALK | chr2 | 29432640 | 29432696 | Hypo | literature | ALK |
| chr2 | 29436844 | 29436888 | Hypo | literature | ALK | chr2 | 29443573 | 29443710 | Hypo | literature | ALK |
| chr2 | 29445198 | 29445482 | Hypo | literature | ALK | chr2 | 29446361 | 29446396 | Hypo | literature | ALK |
| chr2 | 30368444 | 30368586 | Hypo | cancer_general | YPEL5 | chr2 | 30514753 | 30514783 | Hypo | hepatobiliary | — |
| chr2 | 32275196 | 32275303 | Hypo | cancer_general | — | chr2 | 32504169 | 32504378 | Hypo | cancer_general | YIPF4 |
| chr2 | 32580386 | 32580476 | Hypo | colorectal | BIRC6 | chr2 | 38365525 | 38365748 | Hypo | cancer_general | CYP1B1-AS1 |
| chr2 | 38551124 | 38551390 | Hypo | ovarian | ATL2 | chr2 | 38594819 | 38594874 | Hypo | breast | ATL2 |
| chr2 | 38727561 | 38727707 | Hypo | breast | — | chr2 | 38762382 | 38762412 | Hypo | colorectal | — |
| chr2 | 38953573 | 38953603 | Hypo | cancer_general | GALM | chr2 | 38983213 | 38983333 | Hypo | head_neck | GEMIN6, SRSF7 |
| chr2 | 41789816 | 41789853 | Hypo | hepatobiliary | — | chr2 | 43388330 | 43388529 | Hypo | colorectal, cancer_general | — |
| chr2 | 43824133 | 43824353 | Hypo | cancer_general | THADA | chr2 | 44226958 | 44226988 | Hypo | head_neck | LRPPRC |
| chr2 | 44227193 | 44227223 | Hypo | head_neck | LRPPRC | chr2 | 44497708 | 44497875 | Hypo | breast | SLC3A1 |
| chr2 | 44809187 | 44809217 | Hypo | ovarian | — | chr2 | 47193930 | 47194136 | Hypo | pancreas, cancer_general | TTC7A |
| chr2 | 47200591 | 47200621 | Hypo | ovarian | TTC7A | chr2 | 47249725 | 47249848 | Hypo | ovarian | — |
| chr2 | 47597455 | 47598620 | Hypo | cancer_general | MIR559, EPCAM | chr2 | 47599589 | 47599753 | Hypo | cancer_general | TTC7A MIR559, EPCAM |
| chr2 | 48629615 | 48629685 | Hypo | cancer_general | — | chr2 | 48636504 | 48636669 | Hypo | cancer_general | NRXN1 |
| chr2 | 48648878 | 48648940 | Hypo | cancer_general | — | chr2 | 50573802 | 50573865 | Hypo | cancer_general | — |
| chr2 | 54322431 | 54322576 | Hypo | lung | — | chr2 | 55289011 | 55289296 | Hypo | lung | — |
| chr2 | 55612770 | 55612800 | Hypo | colorectal | — | chr2 | 55669261 | 55669454 | Hypo | cancer_general | — |
| chr2 | 58552519 | 58552689 | Hypo | cancer_general | — | chr2 | 59400384 | 59400424 | Hypo | cancer_general | — |
| chr2 | 60416280 | 60416494 | Hypo | cancer_general | — | chr2 | 60706759 | 60706804 | Hypo | cancer_general | BCL11A PUS10, 5S_rRNA |
| chr2 | 61135032 | 61135137 | Hypo | breast | REL | chr2 | 61232163 | 61232232 | Hypo | cancer_general | C2orf74, AHSA2 |
| chr2 | 61242732 | 61242802 | Hypo | cancer_general | PEX13, PUS10 | chr2 | 61395039 | 61395069 | Hypo | cancer_general | — |
| chr2 | 61556203 | 61556239 | Hypo | cancer_general | — | chr2 | 61656393 | 61656423 | Hypo | breast | — |
| chr2 | 61992076 | 61992289 | Hypo | cancer_general | — | chr2 | 65251310 | 65251340 | Hypo | head_neck | SLC1A4 |
| chr2 | 65779892 | 65779983 | Hypo | cancer_general | FLJ16124 | chr2 | 67625453 | 67625770 | Hypo | cancer_general | ETAA1 |
| chr2 | 67626102 | 67626257 | Hypo | cancer_general | ETAA1 | chr2 | 68287707 | 68287799 | Hypo | head_neck | C1D |
| chr2 | 68559261 | 68559365 | Hypo | cancer_general | — | chr2 | 68672853 | 68672938 | Hypo | cancer_general | — |
| chr2 | 69027024 | 69027053 | Hypo | literature | ARHGAP25 | chr2 | 69975443 | 69975523 | Hypo | pancreas | ANXA4 |
| chr2 | 70058262 | 70058292 | Hypo | cancer_general | GMCL1 | chr2 | 70367670 | 70367710 | Hypo | lung | C2orf42 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 70418528 | 70418627 | Hypo | cancer_general | C2orf42 | chr2 | 70427556 | 70427646 | Hypo | lung | TIA1, C2orf42 |
| chr2 | 70430997 | 70431160 | Hypo | cancer_general | TIA1 | chr2 | 71355019 | 71355117 | Hypo | cancer_general | MPHOSPH10, MCEE |
| chr2 | 71355768 | 71355961 | Hypo | cancer_general | MPHOSPH10, MCEE | chr2 | 73147353 | 73147383 | Hypo | cancer_general | EMX1 |
| chr2 | 73416356 | 73416535 | Hypo | lung | — | chr2 | 73440206 | 73440293 | Hypo | cancer_general | SMYD5, NOTO |
| chr2 | 74010528 | 74010773 | Hypo | cancer_general | C2orf78, DUSP11 | chr2 | 74153198 | 74153227 | Hypo | literature | DGUOK, ACTG2 |
| chr2 | 74350410 | 74350497 | Hypo | cancer_general | WDR54, RTKN, DQ588163, C2orf81 | chr2 | 74454074 | 74454261 | Hypo | cancer_general | SLC4A5 |
| chr2 | 74647864 | 74648007 | Hypo | cancer_general | | chr2 | 74679047 | 74679123 | Hypo | cancer_general | INO80B, INO80B-WBP1, WBP1, MOGS, RTKN |
| chr2 | 74874865 | 74874903 | Hypo | cancer_general | SEMA4F | chr2 | 79347459 | 79347546 | Hypo | literature | REG1A |
| chr2 | 85838101 | 85838299 | Hypo | cancer_general | C2orf68, TMEM150A, USP39 | chr2 | 86191145 | 86191309 | Hypo | cancer_general | — |
| chr2 | 86423330 | 86423592 | Hypo | cancer_general | MRPL35, MIR4779, IMMT | chr2 | 86783725 | 86783755 | Hypo | cancer_general | RNF103-CHMP3, CHMP3 |
| chr2 | 86791221 | 86791251 | Hypo | ovarian | RNF103-CHMP3, CHMP3 | chr2 | 88469312 | 88469483 | Hypo | cancer_general | THNSL2 |
| chr2 | 88990189 | 88990264 | Hypo | cancer_general | RPIA | chr2 | 89252535 | 89252679 | Hypo | cancer_general | — |
| chr2 | 95941678 | 95941812 | Hypo | ovarian | PROM2 | chr2 | 96070057 | 96070165 | Hypo | breast | FAHD2A |
| chr2 | 96974486 | 96974516 | Hypo | lung | — | chr2 | 97126702 | 97126832 | Hypo | head_neck | — |
| chr2 | 97427515 | 97428093 | Hypo | cancer_general | CNNM4 | chr2 | 98581819 | 98581849 | Hypo | colorectal | TMEM131 |
| chr2 | 99796259 | 99796330 | Hypo | cancer_general | MRPL30, MITD1 | chr2 | 99798646 | 99799153 | Hypo | cancer_general | MRPL30, MITD1 |
| chr2 | 100618451 | 100618480 | Hypo | literature | AFF3 | chr2 | 101009832 | 101009927 | Hypo | cancer_general | CHST10 |
| chr2 | 101186368 | 101186458 | Hypo | ovarian | PDCL3 | chr2 | 101834977 | 101835057 | Hypo | cancer_general | — |
| chr2 | 105488437 | 105488496 | Hypo | cancer_general | AK095498 | chr2 | 105937344 | 105937498 | Hypo | cancer_general | TGFBRAP1 |
| chr2 | 106060615 | 106060792 | Hypo | lung | — | chr2 | 106730223 | 106730256 | Hypo | cancer_general | UXS1 |
| chr2 | 106959368 | 106959568 | Hypo | cancer_general | — | chr2 | 106959916 | 106959988 | Hypo | cancer_general | RANBP2 |
| chr2 | 108364897 | 108364940 | Hypo | cancer_general | — | chr2 | 109335133 | 109335166 | Hypo | cancer_general | ACOXL |
| chr2 | 110015080 | 110015110 | Hypo | ovarian | TMEM87B | chr2 | 111544817 | 111544997 | Hypo | esophageal | — |
| chr2 | 128817735 | 128817765 | Hypo | colorectal | IL36B | chr2 | 113227024 | 113227225 | Hypo | colorectal | — |
| chr2 | 113803960 | 113803990 | Hypo | cancer_general | SLC35F5, MIR4782 | chr2 | 114461746 | 114461879 | Hypo | cancer_general | SLC35F5 |
| chr2 | 114470022 | 114470201 | Hypo | ovarian | | chr2 | 114515528 | 114515618 | Hypo | cancer_general | |
| chr2 | 114634867 | 114634988 | Hypo | cancer_general | — | chr2 | 118380865 | 118380904 | Hypo | pancreas | — |
| chr2 | 119600570 | 119600747 | Hypo | cancer_general | EN1 | chr2 | 120769511 | 120769746 | Hypo | cancer_general | EPB41L5 |
| chr2 | 120825608 | 120825769 | Hypo | lung | EPB41L5 | chr2 | 120980068 | 120980098 | Hypo | cancer_general | TMEM185B |
| chr2 | 120980353 | 120980395 | Hypo | cancer_general | TMEM185B | chr2 | 122495267 | 122495413 | Hypo | cancer_general | MKI67IP |
| chr2 | 122809705 | 122809801 | Hypo | cancer_general | — | chr2 | 127412291 | 127412386 | Hypo | cancer_general | GYPC |
| chr2 | 127423220 | 127423350 | Hypo | cancer_general | GYPC | chr2 | 127429010 | 127429044 | Hypo | cancer_general | GYPC |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 127438633 | 127438663 | Hypo | cancer_general | GYPC | chr2 | 128616617 | 128616838 | Hypo | cancer_general | AMMECR1L, POLR2D |
| chr2 | 128680057 | 128680087 | Hypo | cancer_general | — | chr2 | 128847677 | 128847723 | Hypo | cancer_general | UGGT1 |
| chr2 | 129174888 | 129174918 | Hypo | cancer_general | — | chr2 | 130937868 | 130937898 | Hypo | cancer_general | MZT2B, FLJ14346, SMPD4 |
| chr2 | 131084953 | 131085013 | Hypo | cancer_general | TRNA_Glu | chr2 | 131477785 | 131477936 | Hypo | cancer_general | GPR148 |
| chr2 | 132208115 | 132208278 | Hypo | cancer_general | LOC401010 | chr2 | 136287358 | 136287390 | Hypo | cancer_general | R3HDM1, ZRANB3 |
| chr2 | 143569561 | 143569694 | Hypo | cancer_general | — | chr2 | 144129765 | 144129795 | Hypo | cancer_general | ARHGAP15 MBD5, |
| chr2 | 144299758 | 144299788 | Hypo | cancer_general | ARHGAP15 | chr2 | 148776809 | 148777035 | Hypo | cancer_general | ORC4 |
| chr2 | 152248836 | 152248983 | Hypo | cancer_general | PSMD14 | chr2 | 161253293 | 161253455 | Hypo | cancer_general | RBMS1 |
| chr2 | 162166600 | 162166632 | Hypo | cancer_general | — | chr2 | 166929478 | 166929613 | Hypo | cancer_general | BC051759, SCN1A |
| chr2 | 170255970 | 170256139 | Hypo | cancer_general | — | chr2 | 170282981 | 170283080 | Hypo | cancer_general | — |
| chr2 | 170373281 | 170373413 | Hypo | lung | KLHL41 | chr2 | 170551730 | 170551942 | Hypo | cancer_general, literature | PHOSPHO2, PHOSPHO2-KLHL23, CCDC173 |
| chr2 | 170681880 | 170682422 | Hypo | cancer_general | UBR3, METTL5 | chr2 | 171822428 | 171822480 | Hypo | pancreas | GORASP2 |
| chr2 | 171839017 | 171839047 | Hypo | cancer_general | TLK1 | chr2 | 172367021 | 172367125 | Hypo | colorectal | — |
| chr2 | 172411136 | 172411166 | Hypo | cancer_general | CYBRD1 | chr2 | 172973111 | 172973141 | Hypo | cancer_general | DLX2 |
| chr2 | 173422685 | 173422734 | Hypo | cancer_general | PDK1 | chr2 | 174148058 | 174148157 | Hypo | head_neck | MLK7-AS1 |
| chr2 | 175111870 | 175112092 | Hypo | cancer_general | OLA1 | chr2 | 175261402 | 175261432 | Hypo | cancer_general | SCRN3, CIR1 |
| chr2 | 175383935 | 175383965 | Hypo | cancer_general | — | chr2 | 176987367 | 176987397 | Hypo | pancreas | HOXD9, AX747372, HOXD8, HOXD10 |
| chr2 | 176994031 | 176994136 | Hypo | cancer_general | HOXD9, HOXD10, HOXD8, HOXD-AS2, BC047605, AX747372 | chr2 | 177872600 | 177872629 | Hypo | literature | — |
| chr2 | 178098791 | 178098967 | Hypo | literature | NFE2L2 | chr2 | 178973003 | 178973042 | Hypo | ovarian | RBM45 |
| chr2 | 179303534 | 179303727 | Hypo | cancer_general | AX747806, PRKRA, BX538254, MIR548N | chr2 | 179316860 | 179317057 | Hypo | cancer_general | DFNB59 |
| chr2 | 182202233 | 182202291 | Hypo | cancer_general | — | chr2 | 183251240 | 183251303 | Hypo | hepatobiliary | PDE1A |
| chr2 | 190708790 | 190708819 | Hypo | literature | PMS1 | chr2 | 197793125 | 197793267 | Hypo | cancer_general | PGAP1 |
| chr2 | 198238409 | 198238439 | Hypo | cancer_general | — | chr2 | 198267345 | 198267374 | Hypo | literature | SnR39B, SF3B1 |
| chr2 | 198456480 | 198456719 | Hypo | cancer_general | RFTN2 | chr2 | 200818892 | 200819130 | Hypo | cancer_general | C2orf47, TYW5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 201156690 | 201156804 | Hypo | ovarian | | chr2 | 201693680 | 201693718 | Hypo | colorectal | BZW1 |
| chr2 | 202477462 | 202477621 | Hypo | cancer_general | TMEM237, ALS2CR11 | chr2 | 203484608 | 203484646 | Hypo | cancer_general | — |
| chr2 | 203498452 | 203498489 | Hypo | ovarian | FAM117B | chr2 | 203880390 | 203880492 | Hypo | cancer_general | NBEAL1 |
| chr2 | 204194588 | 204194725 | Hypo | cancer_general | ABI2 | chr2 | 207022702 | 207022802 | Hypo | cancer_general | EEF1B2, SNORD51, SNORA41, NDUFS1 |
| chr2 | 208574821 | 208574917 | Hypo | cancer_general | CCNYL1 | chr2 | 208588311 | 208588341 | Hypo | cancer_general | CCNYL1 |
| chr2 | 208662170 | 208662376 | Hypo | lung | — | chr2 | 208662672 | 208662710 | Hypo | lung | — |
| chr2 | 209094739 | 209094845 | Hypo | cancer_general | IDH1 | chr2 | 209113097 | 209113126 | Hypo | literature | IDH1-AS1, IDH1 |
| chr2 | 209225237 | 209225275 | Hypo | ovarian | PTH2R | chr2 | 212248428 | 212248457 | Hypo | literature | ERBB4 |
| chr2 | 212288927 | 212288956 | Hypo | literature | ERBB4 | chr2 | 212295683 | 212295820 | Hypo | literature | ERBB4 |
| chr2 | 212530149 | 212530195 | Hypo | literature | ERBB4 | chr2 | 212537902 | 212537994 | Hypo | literature | ERBB4 |
| chr2 | 212566811 | 212566840 | Hypo | literature | ERBB4 | chr2 | 212578292 | 212578321 | Hypo | literature | ERBB4 |
| chr2 | 212587132 | 212587161 | Hypo | literature | ERBB4 | chr2 | 215276310 | 215276339 | Hypo | literature | VWC2L |
| chr2 | 217396039 | 217396069 | Hypo | ovarian | VIL1, MIR26B, CTDSP1 | chr2 | 217448294 | 1217448441 | Hypo | esophageal | — |
| chr2 | 219276888 | 219276918 | Hypo | blood | | chr2 | 220080510 | 220081033 | Hypo | ovarian | ABCB6, ZFAND2B, ATG9A |
| chr2 | 221853201 | 221853352 | Hypo | hepatobiliary | EPHA4 | chr2 | 222285828 | 222285858 | Hypo | hepatobiliary | EPHA4 |
| chr2 | 222310068 | 222310105 | Hypo | hepatobiliary | | chr2 | 223166270 | 223166408 | Hypo | cancer_general | CCDC140, DD413687, PAX3 |
| chr2 | 224661521 | 224661701 | Hypo | pancreas | AP1S3 | chr2 | 225464038 | 225464068 | Hypo | cancer_general | C2orf83 |
| chr2 | 228411020 | 228411050 | Hypo | cancer_general | AGFG1 | chr2 | 228466625 | 228466777 | Hypo | cancer_general | DAW1 |
| chr2 | 228638272 | 228638302 | Hypo | lung | — | chr2 | 228735680 | 228735736 | Hypo | cancer_general | CAB39 |
| chr2 | 230795535 | 230795565 | Hypo | lung, cancer_general | TRIP12, FBXO36 | chr2 | 231576609 | 231576643 | Hypo | cancer_general | — |
| chr2 | 232330451 | 232330481 | Hypo | cancer_general | SNORD82, SNORD20, SNORA75, NCL | chr2 | 232506220 | 232506294 | Hypo | cancer_general | — |
| chr2 | 232506605 | 232506635 | Hypo | cancer_general | — | chr2 | 232522844 | 232522874 | Hypo | cancer_general | — |
| chr2 | 232544500 | 232544530 | Hypo | cancer_general | — | chr2 | 232546736 | 232546842 | Hypo | cancer_general | — |
| chr2 | 232827168 | 232827349 | Hypo | cancer_general | DIS3L2 | chr2 | 233073078 | 233073223 | Hypo | ovarian | NGEF, C2orf82 |
| chr2 | 233220227 | 233220382 | Hypo | cancer_general | — | chr2 | 233750525 | 233750555 | Hypo | cancer_general | — |
| chr2 | 234776483 | 234776553 | Hypo | cancer_general | MSL3P1 | chr2 | 236444269 | 236444298 | Hypo | literature | AGAP1 |
| chr2 | 236877262 | 236877399 | Hypo | lung | AGAP1 | chr2 | 239031722 | 239031780 | Hypo | cancer_general | ESPNL |
| chr2 | 239051198 | 239051228 | Hypo | cancer_general | KLHL30, ESPNL | chr2 | 239265496 | 239265787 | Hypo | cancer_general | TRAF3IP1 |
| chr2 | 239482485 | 239482519 | Hypo | cancer_general | — | chr2 | 239705305 | 239705337 | Hypo | cancer_general | U4 |
| chr2 | 239957330 | 239957448 | Hypo | cancer_general | — | chr2 | 240167575 | 240167605 | Hypo | cancer_general | — |
| chr2 | 240168811 | 240169051 | Hypo | cancer_general | — | chr2 | 240319920 | 240320012 | Hypo | ovarian | — |
| chr2 | 240582379 | 240582524 | Hypo | cancer_general | — | chr2 | 240619459 | 240619604 | Hypo | cancer_general | — |
| chr2 | 240658227 | 240658421 | Hypo | cancer_general | — | chr2 | 240658667 | 240658697 | Hypo | cancer_general | — |
| chr2 | 240812243 | 240812374 | Hypo | cancer_general | — | chr2 | 241095604 | 241095772 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 241541932 | 241542357 | Hypo | cancer_general, colorectal | GPR35, CAPN10 | chr2 | 241545001 | 241545031 | Hypo | cancer_general | GPR35, CAPN10 |
| chr2 | 241865194 | 241865346 | Hypo | cancer_general | — | chr2 | 242009391 | 242009421 | Hypo | cancer_general | SNED1 |
| chr2 | 242021784 | 242021892 | Hypo | cancer_general | SNED1 | chr2 | 242314494 | 242314524 | Hypo | cancer_general | FARP2 |
| chr2 | 242523907 | 242524147 | Hypo | cancer_general, lung, | 5S_rRNA, THAP4 | chr2 | 242554549 | 242554579 | Hypo | cancer_general | — |
| chr2 | 242636726 | 242636812 | Hypo | cancer_general | ING5 | chr2 | 242640015 | 242640045 | Hypo | cancer_general | ING5 |
| chr2 | 242716723 | 242716760 | Hypo | cancer_general | GAL3ST2, D2HGDH | chr2 | 242756144 | 242756297 | Hypo | cancer_general | NEU4, PABL |
| chr2 | 242832984 | 242833159 | Hypo | cancer_general | — | chr2 | 242833558 | 242833588 | Hypo | cancer_general | — |
| chr2 | 242833797 | 242833863 | Hypo | cancer_general | — | chr2 | 242836495 | 242836640 | Hypo | cancer_general | — |
| chr2 | 242925496 | 242925641 | Hypo | cancer_general | AK097934 | chrY | 3446305 | 3446441 | Hypo | hepatobiliary | TGIF2LY |
| chrY | 3838889 | 3838919 | Hypo | pancreas | — | chrY | 3968100 | 3968132 | Hypo | hepatobiliary | — |
| chrY | 13316007 | 13316132 | Hypo | esophageal | — | chrY | 21204734 | 21205113 | Hypo | head_neck | — |
| chrY | 22530026 | 22530073 | Hypo | head_neck | — | HHV5-CINCY-TOWNE | 1181 | 1210 | Hypo | virus | — |
| HHV5-CINCY-TOWNE | 1988 | 2017 | Hypo | virus | — | HHV5-CINCY-TOWNE | 2389 | 2418 | Hypo | virus | — |
| HHV5-CINCY-TOWNE | 3290 | 3319 | Hypo | virus | — | HHV5-CINCY-TOWNE | 3665 | 3694 | Hypo | virus | — |
| HHV5-CINCY-TOWNE | 4704 | 4733 | Hypo | virus | — | HHV5-CINCY-TOWNE | 5400 | 5429 | Hypo | virus | — |
| HHV5-CINCY-TOWNE | 7790 | 7819 | Hypo | virus | — | HHV5-CINCY-TOWNE | 9656 | 9685 | Hypo | virus | — |
| HHV5-CINCY-TOWNE | 10781 | 10810 | Hypo | virus | — | HHV5-CINCY-TOWNE | 11109 | 11138 | Hypo | virus | — |
| HHV5-CINCY-TOWNE | 12663 | 12692 | Hypo | virus | — | HHV5-CINCY-TOWNE | 13688 | 13717 | Hypo | virus | — |
| HHV5-CINCY-TOWNE | 14223 | 14252 | Hypo | virus | — | HHV5-CINCY-TOWNE | 14911 | 14940 | Hypo | virus | — |
| HHV5-CINCY-TOWNE | 15206 | 15235 | Hypo | virus | — | HHV5-CINCY-TOWNE | 15938 | 15967 | Hypo | virus | — |
| HHV5-CINCY-TOWNE | 16440 | 16469 | Hypo | virus | — | HHV5-CINCY-TOWNE | 16884 | 16913 | Hypo | virus | — |
| HHV5-CINCY-TOWNE | 17347 | 17376 | Hypo | virus | — | HHV5-CINCY-TOWNE | 17696 | 17725 | Hypo | virus | — |
| HHV5-CINCY-TOWNE | 17958 | 17987 | Hypo | virus | — | HHV5-CINCY-TOWNE | 18372 | 18401 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 19417 | 19446 | Hypo | virus | — | HHV5-CINCY-TOWNE | 19910 | 19939 | Hypo | virus | — |
| HHV5-CINCY-TOWNE | 20248 | 20277 | Hypo | virus | — | HHV5-CINCY-TOWNE | 20671 | 20700 | Hypo | virus | — |
| HHV5-CINCY-TOWNE | 21899 | 21928 | Hypo | virus | — | HHV5-CINCY-TOWNE | 22798 | 22827 | Hypo | virus | — |
| HHV5-CINCY-TOWNE | 23095 | 23124 | Hypo | virus | — | HHV5-CINCY-TOWNE | 26713 | 26742 | Hypo | virus | — |
| HHV5-CINCY-TOWNE | 27211 | 27240 | Hypo | virus | — | HHV5-CINCY-TOWNE | 29784 | 29813 | Hypo | virus | — |
| HHV5-CINCY-TOWNE | 31141 | 31170 | Hypo | virus | — | HHV5-CINCY-TOWNE | 32660 | 32689 | Hypo | virus | — |
| HHV5-CINCY-TOWNE | 35651 | 35680 | Hypo | virus | — | HHV5-CINCY-TOWNE | 36393 | 36422 | Hypo | virus | — |
| HHV5-CINCY-TOWNE | 37224 | 37253 | Hypo | virus | — | HHV5-CINCY-TOWNE | 37895 | 37924 | Hypo | virus | — |
| HHV5-CINCY-TOWNE | 39244 | 39273 | Hypo | virus | — | HHV5-CINCY-TOWNE | 43188 | 43217 | Hypo | virus | — |
| HHV5-CINCY-TOWNE | 44447 | 44476 | Hypo | virus | — | HHV5-CINCY-TOWNE | 44799 | 44828 | Hypo | virus | — |
| HHV5-CINCY-TOWNE | 45394 | 45423 | Hypo | virus | — | HHV5-CINCY-TOWNE | 46445 | 46474 | Hypo | virus | — |
| HHV5-CINCY-TOWNE | 46944 | 46973 | Hypo | virus | — | HHV5-CINCY-TOWNE | 47916 | 47945 | Hypo | virus | — |
| HHV5-CINCY-TOWNE | 48504 | 48533 | Hypo | virus | — | HHV5-CINCY-TOWNE | 49094 | 49123 | Hypo | virus | — |
| HHV5-CINCY-TOWNE | 49903 | 49932 | Hypo | virus | — | HHV5-CINCY-TOWNE | 50230 | 50259 | Hypo | virus | — |
| HHV5-CINCY-TOWNE | 51421 | 51450 | Hypo | virus | — | HHV5-CINCY-TOWNE | 53772 | 53801 | Hypo | virus | — |
| HHV5-CINCY-TOWNE | 55651 | 55680 | Hypo | virus | — | HHV5-CINCY-TOWNE | 56380 | 56409 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 57291 | 57320 | Hypo | virus | — | HHV5-CINCY-TOWNE | 58491 | 58520 | Hypo | virus | — |
| HHV5-CINCY-TOWNE | 59023 | 59052 | Hypo | virus | — | HHV5-CINCY-TOWNE | 59792 | 59821 | Hypo | virus | — |
| HHV5-CINCY-TOWNE | 60124 | 60153 | Hypo | virus | — | HHV5-CINCY-TOWNE | 60392 | 60421 | Hypo | virus | — |
| HHV5-CINCY-TOWNE | 60900 | 60929 | Hypo | virus | — | HHV5-CINCY-TOWNE | 63894 | 63923 | Hypo | virus | — |
| HHV5-CINCY-TOWNE | 65843 | 65872 | Hypo | virus | — | HHV5-CINCY-TOWNE | 68089 | 68118 | Hypo | virus | — |
| HHV5-CINCY-TOWNE | 72454 | 72483 | Hypo | virus | — | HHV5-CINCY-TOWNE | 81185 | 81214 | Hypo | virus | — |
| HHV5-CINCY-TOWNE | 84144 | 84173 | Hypo | virus | — | HHV5-CINCY-TOWNE | 85524 | 85553 | Hypo | virus | — |
| HHV5-CINCY-TOWNE | 85943 | 85972 | Hypo | virus | — | HHV5-CINCY-TOWNE | 86889 | 86918 | Hypo | virus | — |
| HHV5-CINCY-TOWNE | 87195 | 87224 | Hypo | virus | — | HHV5-CINCY-TOWNE | 87455 | 87484 | Hypo | virus | — |
| HHV5-CINCY-TOWNE | 87769 | 87798 | Hypo | virus | — | HHV5-CINCY-TOWNE | 88564 | 88593 | Hypo | virus | — |
| HHV5-CINCY-TOWNE | 93096 | 93125 | Hypo | virus | — | HHV5-CINCY-TOWNE | 93776 | 93805 | Hypo | virus | — |
| HHV5-CINCY-TOWNE | 97621 | 97650 | Hypo | virus | — | HHV5-CINCY-TOWNE | 98737 | 98766 | Hypo | virus | — |
| HHV5-CINCY-TOWNE | 99460 | 99489 | Hypo | virus | — | HHV5-CINCY-TOWNE | 107540 | 107569 | Hypo | virus | — |
| HHV5-CINCY-TOWNE | 108823 | 108852 | Hypo | virus | — | HHV5-CINCY-TOWNE | 109725 | 109754 | Hypo | virus | — |
| HHV5-CINCY-TOWNE | 112036 | 112065 | Hypo | virus | — | HHV5-CINCY-TOWNE | 112319 | 112348 | Hypo | virus | — |
| HHV5-CINCY-TOWNE | 112595 | 112624 | Hypo | virus | — | HHV5-CINCY-TOWNE | 112892 | 112921 | Hypo | virus | — |

TABLE 11-continued

| chr | Start | Stop | Hypo/hyper | classification | annotation |
|---|---|---|---|---|---|
| HHV5-CINCY-TOWNE | 113194 | 113223 | Hypo | virus | — |
| HHV5-CINCY-TOWNE | 113927 | 113956 | Hypo | virus | — |
| HHV5-CINCY-TOWNE | 114593 | 114622 | Hypo | virus | — |
| HHV5-CINCY-TOWNE | 115177 | 115206 | Hypo | virus | — |
| HHV5-CINCY-TOWNE | 115685 | 115714 | Hypo | virus | — |
| HHV5-CINCY-TOWNE | 116382 | 116411 | Hypo | virus | — |
| HHV5-CINCY-TOWNE | 118193 | 118222 | Hypo | virus | — |
| HHV5-CINCY-TOWNE | 120028 | 120057 | Hypo | virus | — |
| HHV5-CINCY-TOWNE | 122199 | 122228 | Hypo | virus | — |
| HHV5-CINCY-TOWNE | 124559 | 124588 | Hypo | virus | — |
| HHV5-CINCY-TOWNE | 132497 | 132526 | Hypo | virus | — |
| HHV5-CINCY-TOWNE | 135730 | 135759 | Hypo | virus | — |
| HHV5-CINCY-TOWNE | 139067 | 139096 | Hypo | virus | — |
| HHV5-CINCY-TOWNE | 140147 | 140176 | Hypo | virus | — |
| HHV5-CINCY-TOWNE | 142023 | 142052 | Hypo | virus | — |
| HHV5-CINCY-TOWNE | 144080 | 144109 | Hypo | virus | — |
| HHV5-CINCY-TOWNE | 113535 | 113564 | Hypo | virus | — |
| HHV5-CINCY-TOWNE | 114267 | 114296 | Hypo | virus | — |
| HHV5-CINCY-TOWNE | 114867 | 114896 | Hypo | virus | — |
| HHV5-CINCY-TOWNE | 115432 | 115461 | Hypo | virus | — |
| HHV5-CINCY-TOWNE | 115986 | 116015 | Hypo | virus | — |
| HHV5-CINCY-TOWNE | 116700 | 116729 | Hypo | virus | — |
| HHV5-CINCY-TOWNE | 118995 | 119024 | Hypo | virus | — |
| HHV5-CINCY-TOWNE | 121485 | 121514 | Hypo | virus | — |
| HHV5-CINCY-TOWNE | 122606 | 122635 | Hypo | virus | — |
| HHV5-CINCY-TOWNE | 125276 | 125305 | Hypo | virus | — |
| HHV5-CINCY-TOWNE | 135460 | 135489 | Hypo | virus | — |
| HHV5-CINCY-TOWNE | 137379 | 137408 | Hypo | virus | — |
| HHV5-CINCY-TOWNE | 139472 | 139501 | Hypo | virus | — |
| HHV5-CINCY-TOWNE | 140722 | 140751 | Hypo | virus | — |
| HHV5-CINCY-TOWNE | 143692 | 143721 | Hypo | virus | — |
| HHV5-CINCY-TOWNE | 147310 | 147339 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 149465 | 149494 | Hypo | virus | — | HHV5-CINCY-TOWNE | 150359 | 150388 | Hypo | virus | — |
| HHV5-CINCY-TOWNE | 151593 | 151622 | Hypo | virus | — | HHV5-CINCY-TOWNE | 152153 | 152182 | Hypo | virus | — |
| HHV5-CINCY-TOWNE | 154148 | 154177 | Hypo | virus | — | HHV5-CINCY-TOWNE | 154610 | 154639 | Hypo | virus | — |
| HHV5-CINCY-TOWNE | 157018 | 157047 | Hypo | virus | — | HHV5-CINCY-TOWNE | 157367 | 157396 | Hypo | virus | — |
| HHV5-CINCY-TOWNE | 169038 | 169067 | Hypo | virus | — | HHV5-CINCY-TOWNE | 171503 | 171532 | Hypo | virus | — |
| HHV5-CINCY-TOWNE | 175146 | 175175 | Hypo | virus | — | HHV5-CINCY-TOWNE | 177553 | 177582 | Hypo | virus | — |
| HHV5-CINCY-TOWNE | 182254 | 182283 | Hypo | virus | — | HHV5-CINCY-TOWNE | 183115 | 183144 | Hypo | virus | — |
| HHV5-CINCY-TOWNE | 184120 | 184149 | Hypo | virus | — | HHV5-CINCY-TOWNE | 185558 | 185587 | Hypo | virus | — |
| HHV5-CINCY-TOWNE | 186027 | 186056 | Hypo | virus | — | HHV5-CINCY-TOWNE | 186435 | 186464 | Hypo | virus | — |
| HHV5-CINCY-TOWNE | 186707 | 186736 | Hypo | virus | — | HHV5-CINCY-TOWNE | 187115 | 187144 | Hypo | virus | — |
| HHV5-CINCY-TOWNE | 187514 | 187543 | Hypo | virus | — | HHV5-CINCY-TOWNE | 187859 | 187888 | Hypo | virus | — |
| HHV5-CINCY-TOWNE | 188473 | 188502 | Hypo | virus | — | HHV5-CINCY-TOWNE | 188768 | 188797 | Hypo | virus | — |
| HHV5-CINCY-TOWNE | 189050 | 189079 | Hypo | virus | — | HHV5-CINCY-TOWNE | 189302 | 189331 | Hypo | virus | — |
| HHV5-CINCY-TOWNE | 189936 | 189965 | Hypo | virus | — | HHV5-CINCY-TOWNE | 190655 | 190684 | Hypo | virus | — |
| HHV5-CINCY-TOWNE | 190954 | 190983 | Hypo | virus | — | HHV5-CINCY-TOWNE | 191453 | 191482 | Hypo | virus | — |
| HHV5-CINCY-TOWNE | 191882 | 191911 | Hypo | virus | — | HHV5-CINCY-TOWNE | 192183 | 192212 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 192541 | 192570 | Hypo | virus | — | HHV5-CINCY-TOWNE | 193045 | 193074 | Hypo | virus | — |
| HHV5-CINCY-TOWNE | 193325 | 193354 | Hypo | virus | — | HHV5-CINCY-TOWNE | 193597 | 193626 | Hypo | virus | — |
| HHV5-CINCY-TOWNE | 194165 | 194194 | Hypo | virus | — | HHV5-CINCY-TOWNE | 194461 | 194490 | Hypo | virus | — |
| HHV5-CINCY-TOWNE | 194848 | 194877 | Hypo | virus | — | HHV5-CINCY-TOWNE | 195324 | 195353 | Hypo | virus | — |
| HHV5-CINCY-TOWNE | 195651 | 195680 | Hypo | virus | — | HHV5-CINCY-TOWNE | 196018 | 196047 | Hypo | virus | — |
| HHV5-CINCY-TOWNE | 196343 | 196372 | Hypo | virus | — | HHV5-CINCY-TOWNE | 196941 | 196970 | Hypo | virus | — |
| HHV5-CINCY-TOWNE | 197218 | 197247 | Hypo | virus | — | HHV5-CINCY-TOWNE | 198315 | 198344 | Hypo | virus | — |
| HHV5-CINCY-TOWNE | 198792 | 198821 | Hypo | virus | — | HHV5-CINCY-TOWNE | 199162 | 199191 | Hypo | virus | — |
| HHV5-CINCY-TOWNE | 200113 | 200142 | Hypo | virus | — | HHV5-CINCY-TOWNE | 200571 | 200600 | Hypo | virus | — |
| HHV5-CINCY-TOWNE | 201373 | 201402 | Hypo | virus | — | HHV5-CINCY-TOWNE | 201905 | 201934 | Hypo | virus | — |
| HHV5-CINCY-TOWNE | 202264 | 202293 | Hypo | virus | — | HHV5-CINCY-TOWNE | 202537 | 202566 | Hypo | virus | — |
| HHV5-CINCY-TOWNE | 203319 | 203348 | Hypo | virus | — | HHV5-CINCY-TOWNE | 203720 | 203749 | Hypo | virus | — |
| HHV5-CINCY-TOWNE | 204008 | 204037 | Hypo | virus | — | HHV5-CINCY-TOWNE | 206213 | 206242 | Hypo | virus | — |
| HHV5-CINCY-TOWNE | 206735 | 206764 | Hypo | virus | — | HHV5-CINCY-TOWNE | 211676 | 211705 | Hypo | virus | — |
| HHV5-CINCY-TOWNE | 212340 | 212369 | Hypo | virus | — | HHV5-CINCY-TOWNE | 212609 | 212638 | Hypo | virus | — |
| HHV5-CINCY-TOWNE | 213813 | 213842 | Hypo | virus | — | HHV5-CINCY-TOWNE | 214695 | 214724 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 214950 | 214979 | Hypo | virus | — | HHV5-CINCY-TOWNE | 215930 | 215959 | Hypo | virus | — |
| HHV5-CINCY-TOWNE | 216228 | 216257 | Hypo | virus | — | HHV5-CINCY-TOWNE | 222672 | 222701 | Hypo | virus | — |
| HHV5-CINCY-TOWNE | 223515 | 223544 | Hypo | virus | — | HHV5-CINCY-TOWNE | 225150 | 225179 | Hypo | virus | — |
| HHV5-CINCY-TOWNE | 226058 | 226087 | Hypo | virus | — | HHV5-CINCY-TOWNE | 226887 | 226916 | Hypo | virus | — |
| chr20 | 118577 | 118751 | Hypo | cancer_general | DEFB126 | chr20 | 304259 | 304408 | Hypo | cancer_general | SOX12 |
| chr20 | 400007 | 400087 | Hypo | cancer_general | RBCK1 | chr20 | 401153 | 401183 | Hypo | cancer_general | RBCK1 |
| chr20 | 401591 | 401756 | Hypo | cancer_general | RBCK1 | chr20 | 523146 | 523193 | Hypo | cancer_general | CSNK2A1 |
| chr20 | 799104 | 799247 | Hypo | cancer_general | — | chr20 | 799458 | 799706 | Hypo | cancer_general | — |
| chr20 | 1094560 | 1094682 | Hypo | ovarian | PSMF1 | chr20 | 1197670 | 1197711 | Hypo | cancer_general | RAD21L1, C20orf202 |
| chr20 | 1975357 | 1975386 | Hypo | literature | PDYN, AK090681 | chr20 | 2645540 | 2645795 | Hypo | cancer_general | IDH3B, SNORA51 |
| chr20 | 3027758 | 3027931 | Hypo | cancer_general | MRPS26, GNRH2, PTPRA | chr20 | 3154172 | 3154204 | Hypo | breast | LZTS3 |
| chr20 | 3204870 | 3204952 | Hypo | cancer_general | SLC4A11, ITPA | chr20 | 3762407 | 3762436 | Hypo | tcga | CENPB, CDC25B, SPEF1 |
| chr20 | 3858389 | 3858632 | Hypo | cancer_general | BC012193, MAVS | chr20 | 3996688 | 3996726 | Hypo | cancer_general | RNF24 |
| chr20 | 4040710 | 4040871 | Hypo | cancer_general | — | chr20 | 4061323 | 4061452 | Hypo | hepatobiliary | — |
| chr20 | 4085057 | 4085087 | Hypo | cancer_general | — | chr20 | 4804703 | 4804732 | Hypo | tcga | RASSF2 |
| chr20 | 5025228 | 5025258 | Hypo | cancer_general | — | chr20 | 5106720 | 5106750 | Hypo | cancer_general | CDS2, PCNA-AS1, PCNA |
| chr20 | 5433047 | 5433085 | Hypo | ovarian | LINC00658 | chr20 | 5610356 | 5610386 | Hypo | colorectal | CRLS1, LRRN4 |
| chr20 | 6022797 | 6023045 | Hypo | breast | LRRN4, CRLS1 | chr20 | 6023268 | 6023351 | Hypo | breast | |
| chr20 | 7980362 | 7980392 | Hypo | head_neck | TMX4 | chr20 | 9488780 | 9488848 | Hypo | cancer_general | LAMP5 |
| chr20 | 14447971 | 14448144 | Hypo | cancer_general | — | chr20 | 16554749 | 16555030 | Hypo | cancer_general | KIF16B |
| chr20 | 18073183 | 18073276 | Hypo | cancer_general | — | chr20 | 18448982 | 18449076 | Hypo | cancer_general | POLR3F, DZANK1, MIR3192 |
| chr20 | 18489463 | 18489658 | Hypo | cancer_general | SEC23B | chr20 | 19128288 | 19128473 | Hypo | cancer_general | — |
| chr20 | 19928306 | 19928461 | Hypo | cancer_general | RIN2 | chr20 | 21501381 | 21501417 | Hypo | cancer_general | — |
| chr20 | 21685385 | 21685526 | Hypo | cancer_general | PAX1 | chr20 | 22401392 | 22401421 | Hypo | literature | NKX2-2 |
| chr20 | 23138383 | 23138444 | Hypo | cancer_general | — | chr20 | 23406698 | 23406830 | Hypo | cancer_general | LOC284788 |
| chr20 | 24505190 | 24505252 | Hypo | cancer_general | SYNDIG1 | chr20 | 24726701 | 24726825 | Hypo | cancer_general | — |
| chr20 | 25086082 | 25086275 | Hypo | cancer_general | — | chr20 | 25223141 | 25223277 | Hypo | lung | — |
| chr20 | 25230509 | 25230799 | Hypo | cancer_general | PYGB | chr20 | 25334513 | 25334650 | Hypo | cancer_general | PYGB |
| chr20 | 25344027 | 25344118 | Hypo | cancer_general | ABHD12 | chr20 | 29832911 | 29833090 | Hypo | cancer_general | ABHD12 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 29914002 | 29914139 | Hypo | cancer_general | — | chr20 | 29956013 | 29956042 | Hypo | literature | DEFB118, DEFB119 |
| chr20 | 29956570 | 29956599 | Hypo | literature | DEFB119, DEFB118 | chr20 | 30101523 | 30101743 | Hypo | cancer_general | HM13 |
| chr20 | 30162296 | 30162459 | Hypo | cancer_general | HM13-AS1 | chr20 | 30174561 | 30174645 | Hypo | cancer_general | — |
| chr20 | 30186068 | 30186165 | Hypo | ovarian | MIR3193, ID1 | chr20 | 30201236 | 30201360 | Hypo | cancer_general | MIR3193, ID1 |
| chr20 | 30280423 | 30280509 | Hypo | blood | BCL2L1 | chr20 | 30297090 | 30297217 | Hypo | cancer_general | BCL2L1 |
| chr20 | 30468319 | 30468349 | Hypo | cancer_general | TTLL9 | chr20 | 31035471 | 31035518 | Hypo | breast | C20orf112, ASXL1 |
| chr20 | 31115683 | 31115799 | Hypo | cancer_general | C20orf112 | chr20 | 31151769 | 31151799 | Hypo | cancer_general | C20orf112 |
| chr20 | 31207211 | 31207283 | Hypo | cancer_general | — | chr20 | 31282734 | 31282903 | Hypo | breast | COMMD7 |
| chr20 | 32301797 | 32301953 | Hypo | breast | PXMP4 | chr20 | 32450248 | 32450427 | Hypo | cancer_general | CHMP4B |
| chr20 | 32701064 | 32701320 | Hypo | cancer_general | EIF2S2 | chr20 | 32716914 | 32716949 | Hypo | cancer_general | — |
| chr20 | 32768669 | 32768728 | Hypo | cancer_general | — | chr20 | 32893006 | 32893125 | Hypo | ovarian | AHCY |
| chr20 | 33540284 | 33540550 | Hypo | ovarian | MYH7B, GSS | chr20 | 33547485 | 33547585 | Hypo | colorectal | GSS, MYH7B |
| chr20 | 33574914 | 33574992 | Hypo | cancer_general | MIR499A, MIR499B, MYH7B | chr20 | 34041981 | 34042087 | Hypo | cancer_general | CEP250 |
| chr20 | 34148020 | 34148254 | Hypo | cancer_general | FER1L4, ERGIC3 | chr20 | 35640448 | 35640561 | Hypo | head_neck | RBL1 |
| chr20 | 35742487 | 35742607 | Hypo | cancer_general | MROH8 | chr20 | 35892604 | 35892746 | Hypo | cancer_general | GHRH |
| chr20 | 36183184 | 36183340 | Hypo | lung | — | chr20 | 40500546 | 40500638 | Hypo | cancer_general | — |
| chr20 | 40515378 | 40515504 | Hypo | cancer_general | — | chr20 | 40743859 | 40743888 | Hypo | literature | PTPRT |
| chr20 | 42218429 | 42218664 | Hypo | cancer_general | IFT52, SGK2 | chr20 | 42281425 | 42281455 | Hypo | cancer_general | IFT52 |
| chr20 | 42852751 | 42852915 | Hypo | colorectal, cancer_general | BC036500, OSER1-AS1 | chr20 | 43952174 | 43952302 | Hypo | cancer_general | SDC4, TRNA_Pseudo, RBPJL |
| chr20 | 44003765 | 44003811 | Hypo | blood | SYS1, SYS1-DBNDD2, TP53TG5 | chr20 | 44601547 | 44601716 | Hypo | cancer_general | ZNF335 |
| chr20 | 44602074 | 44602364 | Hypo | cancer_general | ZNF335 | chr20 | 45280344 | 45280428 | Hypo | tcga | SLC13A3 |
| chr20 | 45537804 | 45537945 | Hypo | cancer_general | SLC2A10 | chr20 | 47247239 | 47247450 | Hypo | cancer_general | PREX1, AX746653 |
| chr20 | 47274032 | 47274062 | Hypo | cancer_general | PREX1 | chr20 | 47296109 | 47296231 | Hypo | cancer_general | — |
| chr20 | 47450370 | 47450490 | Hypo | cancer_general | — | chr20 | 47815615 | 47815711 | Hypo | cancer_general | ZEAS1, SNORD12, SNORD12B, SNORD12C |
| chr20 | 47835328 | 47835358 | Hypo | cancer_general | DDX27 | chr20 | 47905426 | 47905603 | Hypo | ovarian | |
| chr20 | 48695665 | 48696227 | Hypo | cancer_general | UBE2V1, TMEM189-UBE2V1 | chr20 | 48768118 | 48768148 | Hypo | cancer_general | — |
| chr20 | 48774527 | 48774569 | Hypo | cancer_general | — | chr20 | 49204179 | 49204449 | Hypo | cancer_general | FAM65C, MIR645, PTPN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 49261803 | 49262104 | Hypo | cancer_general | FAM65C | chr20 | 49323924 | 49324125 | Hypo | cancer_general | PARD6B |
| chr20 | 49350910 | 49351041 | Hypo | cancer_general | PARD6B | chr20 | 49351564 | 49351649 | Hypo | cancer_general | PARD6B |
| chr20 | 49358137 | 49358396 | Hypo | cancer_general | PARD6B | chr20 | 49377755 | 49378043 | Hypo | cancer_general |  |
| chr20 | 49381140 | 49381240 | Hypo | cancer_general |  | chr20 | 49969348 | 49969515 | Hypo | colorectal |  |
| chr20 | 50160756 | 50160905 | Hypo | cancer_general |  | chr20 | 50383224 | 50383423 | Hypo | cancer_general | ATP9A |
| chr20 | 50602134 | 50602264 | Hypo | cancer_general |  | chr20 | 50693423 | 50693468 | Hypo | breast | ZFP64 |
| chr20 | 52311463 | 52311728 | Hypo | pancreas |  | chr20 | 52401713 | 52401775 | Hypo | cancer_general |  |
| chr20 | 54522432 | 54522631 | Hypo | cancer_general |  | chr20 | 55008041 | 55008194 | Hypo | cancer_general | CASS4 |
| chr20 | 55071563 | 55071717 | Hypo | ovarian | GCNT7, RTFDC1 | chr20 | 55499567 | 55499650 | Hypo | cancer_general |  |
| chr20 | 55693527 | 55693662 | Hypo | cancer_general |  | chr20 | 55959212 | 55959250 | Hypo | colorectal | RBM38 |
| chr20 | 56766160 | 56766190 | Hypo | cancer_general |  | chr20 | 56998280 | 56998337 | Hypo | lung | VAPB |
| chr20 | 57484406 | 57484445 | Hypo | literature |  | chr20 | 59525138 | 59525300 | Hypo | cancer_general |  |
| chr20 | 59826192 | 59826221 | Hypo | literature | GNAS | chr20 | 59880433 | 59880477 | Hypo | cancer_general | CDH4 |
| chr20 | 59910175 | 59910346 | Hypo | cancer_general | CDH4 | chr20 | 59973028 | 59973072 | Hypo | cancer_general | CDH4 |
| chr20 | 60202594 | 60202624 | Hypo | cancer_general | CDH4 | chr20 | 60235333 | 60235526 | Hypo | cancer_general | CDH4 |
| chr20 | 60238381 | 60238472 | Hypo | cancer_general | CDH4 | chr20 | 60238877 | 60238980 | Hypo | cancer_general | CDH4 |
| chr20 | 60243944 | 60244107 | Hypo | cancer_general |  | chr20 | 60329584 | 60329738 | Hypo | cancer_general |  |
| chr20 | 60333880 | 60333969 | Hypo | cancer_general |  | chr20 | 60359849 | 60359879 | Hypo | cancer_general |  |
| chr20 | 60375036 | 60375070 | Hypo | cancer_general |  | chr20 | 60439634 | 60439755 | Hypo | cancer_general |  |
| chr20 | 60453925 | 60454091 | Hypo | cancer_general |  | chr20 | 60477306 | 60477537 | Hypo | cancer_general |  |
| chr20 | 60485374 | 60485425 | Hypo | cancer_general |  | chr20 | 60503030 | 60503060 | Hypo | cancer_general |  |
| chr20 | 60545561 | 60545792 | Hypo | breast | TAF4 | chr20 | 60620122 | 60620557 | Hypo | breast | TAF4 |
| chr20 | 60772853 | 60773878 | Hypo | breast | MTG2 | chr20 | 60789965 | 60790124 | Hypo | cancer_general | HRH3 |
| chr20 | 60816241 | 60816271 | Hypo | head_neck | OSBPL2, AK126744 | chr20 | 60892164 | 60892222 | Hypo | cancer_general | LAMA5 |
| chr20 | 60926019 | 60926049 | Hypo | cancer_general |  | chr20 | 60970953 | 60970983 | Hypo | cancer_general | CABLES2, RPS21 |
| chr20 | 60983859 | 60984010 | Hypo | cancer_general | RBBP8NL, CABLES2 | chr20 | 60984341 | 60984465 | Hypo | cancer_general | RBBP8NL, CABLES2 |
| chr20 | 61288068 | 61288156 | Hypo | cancer_general | SLCO4A1, LOC100127888 | chr20 | 61288463 | 61288534 | Hypo | cancer_general | LOC100127888, SLCO4A1 |
| chr20 | 61294693 | 61294857 | Hypo | cancer_general | SLCO4A1, LOC100127888 | chr20 | 61412313 | 61412438 | Hypo | cancer_general | LINC00659, AX747649 |
| chr20 | 61505851 | 61506330 | Hypo | cancer_general | DIDO1 | chr20 | 61532546 | 61532605 | Hypo | cancer_general | DIDO1 |
| chr20 | 61714591 | 61714621 | Hypo | cancer_general |  | chr20 | 61763598 | 61763628 | Hypo | cancer_general |  |
| chr20 | 61765285 | 61765425 | Hypo | cancer_general |  | chr20 | 61823170 | 61823339 | Hypo | cancer_general | YTHDF1 |
| chr20 | 61974191 | 61974354 | Hypo | cancer_general | CHRNA4 | chr20 | 61980860 | 61980975 | Hypo | cancer_general | CHRNA4 |
| chr20 | 62031173 | 62031234 | Hypo | cancer_general | AK056267, KCNQ2 | chr20 | 62032058 | 62032095 | Hypo | cancer_general | KCNQ2, AK056267 |
| chr20 | 62037559 | 62037598 | Hypo | cancer_general | KCNQ2 | chr20 | 62046227 | 62046421 | Hypo | cancer_general | KCNQ2 |
| chr20 | 62090524 | 62090778 | Hypo | cancer_general | KCNQ2 | chr20 | 62097666 | 62097695 | Hypo | literature | KCNQ2 |
| chr20 | 62115047 | 62115266 | Hypo | cancer_general | EEF1A2 | chr20 | 62126118 | 62126429 | Hypo | cancer_general | EEF1A2 |
| chr20 | 62157151 | 62157307 | Hypo | cancer_general | PTK6, PPDPF | chr20 | 62165631 | 62165762 | Hypo | cancer_general | SRMS, PTK6 |
| chr20 | 62167554 | 62167584 | Hypo | cancer_general | SRMS, PTK6 | chr20 | 62170179 | 62170209 | Hypo | cancer_general | SRMS, PTK6 |
| chr20 | 62172945 | 62173055 | Hypo | cancer_general | SRMS, PTK6 | chr20 | 62260818 | 62260905 | Hypo | cancer_general | GMEB2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 62261532 | 62261562 | Hypo | cancer_general | STMN3, GMEB2 | chr20 | 62314848 | 62314955 | Hypo | breast | RTEL1-TNFRSF6B, RTEL1 |
| chr20 | 62321206 | 62321341 | Hypo | cancer_general | TNFRSF6B, ARFRP1, RTEL1-TNFRSF6B | chr20 | 62321638 | 62321881 | Hypo | pancreas, cancer_general | RTEL1-TNFRSF6B, ARFRP1 |
| chr20 | 62340321 | 62340442 | Hypo | cancer_general | ZGPAT, ARFRP1 | chr20 | 62383218 | 62383289 | Hypo | cancer_general | ZBTB46, SLC2A4RG |
| chr20 | 62391938 | 62391968 | Hypo | colorectal | ZBTB46 | chr20 | 62488293 | 62488350 | Hypo | cancer_general | ABHD16B, TPD52L2 |
| chr20 | 62497836 | 62497920 | Hypo | cancer_general | TPD52L2, ABHD16B | chr20 | 62631351 | 62631593 | Hypo | ovarian | PRPF6 |
| chr20 | 62786577 | 62786726 | Hypo | cancer_general | MYT1 | chr20 | 62795643 | 62795672 | Hypo | literature | MYT1 |
| chr22 | 18009969 | 18010121 | Hypo | cancer_general | CECR2 | chr22 | 18110495 | 18110593 | Hypo | cancer_general | BCL2L13, ATP6V1E1 |
| chr22 | 18328127 | 18328268 | Hypo | cancer_general, lung | MICAL3, BC064400 | chr22 | 18340822 | 18340868 | Hypo | cancer_general | MICAL3 |
| chr22 | 18627328 | 18627537 | Hypo | ovarian | USP18 | chr22 | 19117564 | 19117594 | Hypo | cancer_general | DGCR14, TSSK2 |
| chr22 | 19136907 | 19136936 | Hypo | literature | GSC2 | chr22 | 19137859 | 19137888 | Hypo | literature | GSC2 |
| chr22 | 19138109 | 19138138 | Hypo | literature | GSC2 | chr22 | 20229079 | 20229239 | Hypo | pancreas | MIR1286, RTN4R |
| chr22 | 20864642 | 20864672 | Hypo | cancer_general | MED15 | chr22 | 20940868 | 20940898 | Hypo | head_neck | MED15 |
| chr22 | 21042829 | 21043014 | Hypo | cancer_general | DQ571461, POM121L4P | chr22 | 21153867 | 21154000 | Hypo | cancer_general | PI4KA |
| chr22 | 21270750 | 21270834 | Hypo | cancer_general | CRKL | chr22 | 21276140 | 21276261 | Hypo | cancer_general | CRKL, BC033281, BC127858, CRKL |
| chr22 | 21299605 | 21299635 | Hypo | pancreas | BC033281, CRKL | chr22 | 21304771 | 21305007 | Hypo | cancer_general | |
| chr22 | 21977314 | 21977347 | Hypo | breast | YDJC, CCDC116, UBE2L3 | chr22 | 21982792 | 21982972 | Hypo | cancer_general | CCDC116, YDJC, UBE2L3 |
| chr22 | 22023273 | 22023451 | Hypo | cancer_general | PPIL2 | chr22 | 22058203 | 22058238 | Hypo | lung | YPEL1, PPIL2 |
| chr22 | 22201344 | 22201568 | Hypo | head_neck | MAPK1 | chr22 | 22901105 | 22901455 | Hypo | cancer_general | LOC648691, PRAME |
| chr22 | 23791402 | 23791432 | Hypo | cancer_general | — | chr22 | 23801459 | 23801610 | Hypo | breast | LOC388882 |
| chr22 | 23991201 | 23991272 | Hypo | pancreas | GUSBP11 | chr22 | 24145484 | 24145513 | Hypo | literature | SMARCB1 |
| chr22 | 24179940 | 24179982 | Hypo | blood | AK096976, DERL3 | chr22 | 24560375 | 24560526 | Hypo | breast | CABIN1 |
| chr22 | 28371649 | 28371679 | Hypo | cancer_general | TTC28 | chr22 | 29076592 | 29076622 | Hypo | lung | CHEK2 |
| chr22 | 29091824 | 29091853 | Hypo | literature | CHEK2 | chr22 | 29445752 | 29445923 | Hypo | lung | C22orf31 |
| chr22 | 29977614 | 29977863 | Hypo | cancer_general | NIPSNAP1 | chr22 | 30084358 | 30084388 | Hypo | cancer_general | NF2 |
| chr22 | 30090739 | 30090769 | Hypo | breast | NF2 | chr22 | 30158330 | 30158639 | Hypo | cancer_general | UQCR10, ZMAT5 |
| chr22 | 30784196 | 30784278 | Hypo | cancer_general | SEC14L2, RNF215 | chr22 | 32061344 | 32061374 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 32748936 | 32748966 | Hypo | cancer_general | RFPL3, RFPL3S, JB153905 | chr22 | 32868720 | 32868837 | Hypo | cancer_general | FBXO7, BPIFC |
| chr22 | 35079219 | 35079345 | Hypo | cancer_general | — | chr22 | 35768531 | 35768719 | Hypo | cancer_general | HMOX1 |
| chr22 | 35848358 | 35848670 | Hypo | cancer_general | — | chr22 | 35938746 | 35939000 | Hypo | esophageal | RASD2 |
| chr22 | 36367866 | 36367896 | Hypo | cancer_general | — | chr22 | 36855297 | 36855335 | Hypo | cancer_general | TXN2 |
| chr22 | 36855568 | 36855598 | Hypo | cancer_general | TXN2 | chr22 | 36880362 | 36880462 | Hypo | cancer_general | FOXRED2, TXN2 |
| chr22 | 36902291 | 36902381 | Hypo | head_neck | EIF3D, FOXRED2 | chr22 | 37302073 | 37302103 | Hypo | cancer_general | CSF2RB |
| chr22 | 38002684 | 38002733 | Hypo | cancer_general | GGA1 | chr22 | 38087310 | 38087367 | Hypo | head_neck | TRIOBP, NOL12 |
| chr22 | 38182815 | 38182981 | Hypo | head_neck | — | chr22 | 38199769 | 38199894 | Hypo | cancer_general | H1F0, GCAT |
| chr22 | 38507316 | 38507346 | Hypo | cancer_general | PLA2G6 | chr22 | 38592856 | 38593076 | Hypo | cancer_general | MAFF |
| chr22 | 38639229 | 38639259 | Hypo | hepatobiliary | TMEM184B | chr22 | 38874215 | 38874362 | Hypo | head_neck | DDX17, KDELR3 |
| chr22 | 39094890 | 39094964 | Hypo | cancer_general | GTPBP1, JOSD1 | chr22 | 39098022 | 39098064 | Hypo | cancer_general | GTPBP1, JOSD1 |
| chr22 | 39112502 | 39112584 | Hypo | head_neck | GTPBP1 | chr22 | 39830355 | 39830457 | Hypo | breast | LOC100506472, TAB1 |
| chr22 | 39932499 | 39932563 | Hypo | cancer_general | RPS19BP1 | chr22 | 40042627 | 40042743 | Hypo | cancer_general | CACNA1I |
| chr22 | 40075157 | 40075302 | Hypo | cancer_general | CACNA1I | chr22 | 40226345 | 40226389 | Hypo | cancer_general | ENTHD1 |
| chr22 | 40767753 | 40767936 | Hypo | cancer_general | ADSL, SGSM3 | chr22 | 40895978 | 40896029 | Hypo | cancer_general | MKL1 |
| chr22 | 41044488 | 41044818 | Hypo | cancer_general | — | chr22 | 41044732 | 41049109 | Hypo | cancer_general | RANGAP1, CHADL |
| chr22 | 41217105 | 41217405 | Hypo | lung, cancer_general | ST13, MIR4766, SLC25A17 | chr22 | 41634393 | 41634542 | Hypo | pancreas, cancer_general | — |
| chr22 | 41637064 | 41637129 | Hypo | cancer_general | CHADL, RANGAP1 | chr22 | 41648414 | 41648444 | Hypo | head_neck | RANGAP1 |
| chr22 | 41657233 | 41657350 | Hypo | breast | RANGAP1 | chr22 | 41690119 | 41690149 | Hypo | head_neck | ZC3H7B, RANGAP1 |
| chr22 | 41839432 | 41839498 | Hypo | cancer_general | TOB2 | chr22 | 42068010 | 42068172 | Hypo | cancer_general | NHP2L1, XRCC6 |
| chr22 | 42096002 | 42096190 | Hypo | head_neck | C22orf46, MEI1, FLJ23584 | chr22 | 42343416 | 42343676 | Hypo | cancer_general | LINC00634, CENPM |
| chr22 | 42667358 | 42667432 | Hypo | cancer_general | LOC388906 | chr22 | 42916449 | 42916479 | Hypo | cancer_general | RRP7A, SERHL |
| chr22 | 43012543 | 43012877 | Hypo | cancer_general | CYB5R3, DL490307, RNU12, POLDIP3 | chr22 | 43083130 | 43083166 | Hypo | cancer_general | A4GALT |
| chr22 | 43434441 | 43434477 | Hypo | cancer_general | TTLL1, BC039353 | chr22 | 43540672 | 43540702 | Hypo | breast | TSPO, MCAT |
| chr22 | 44455707 | 44455740 | Hypo | cancer_general | PARVB | chr22 | 45087614 | 45087649 | Hypo | cancer_general | PRR5, PRR5- |
| chr22 | 45088602 | 45088743 | Hypo | cancer_general | PRR5, PRR5-ARHGAP8 | chr22 | 45135939 | 45135979 | Hypo | cancer_general | PRR5, PRR5-ARHGAP8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 45252427 | 45252463 | Hypo | hepatobiliary | ARHGAP8 | chr22 | 45277292 | 45277322 | Hypo | cancer_general | PHF21B |
| chr22 | 45313416 | 45313446 | Hypo | hepatobiliary | PHF21B | chr22 | 45593643 | 45593715 | Hypo | cancer_general | KIAA0930, NUP50, MIR1249 |
| chr22 | 45604184 | 45604343 | Hypo | cancer_general | MIR1249, KIAA0930 | chr22 | 46438085 | 46438217 | Hypo | cancer_general | C22orf26, LINC00899 |
| chr22 | 46455833 | 46455905 | Hypo | cancer_general | MIRLET7BHG, LOC150381, C22orf26, LOC554174 | chr22 | 46599623 | 46599725 | Hypo | colorectal | PPARA |
| chr22 | 46931260 | 46931332 | Hypo | ovarian | — | chr22 | 47005080 | 47005154 | Hypo | cancer_general | — |
| chr22 | 47023044 | 47023191 | Hypo | head_neck | GRAMD4 | chr22 | 47054686 | 47054716 | Hypo | head_neck | GRAMD4 |
| chr22 | 47193335 | 47193371 | Hypo | cancer_general | TBC1D22A | chr22 | 47395475 | 47395505 | Hypo | breast | — |
| chr22 | 47525846 | 47525885 | Hypo | cancer_general | — | chr22 | 47584867 | 47585024 | Hypo | cancer_general | — |
| chr22 | 48027626 | 48027655 | Hypo | literature | AK093107, BC039485, LINC00898 | chr22 | 48931881 | 48932027 | Hypo | cancer_general | LOC284933, FAM19A5 |
| chr22 | 49852617 | 49852647 | Hypo | cancer_general | BC033837 | chr22 | 49979646 | 49979757 | Hypo | cancer_general | BC033837 |
| chr22 | 50001699 | 50001882 | Hypo | cancer_general | BC033837 | chr22 | 50002787 | 50002819 | Hypo | cancer_general | BC033837 |
| chr22 | 50003204 | 50003234 | Hypo | cancer_general | BC033837 | chr22 | 50010113 | 50010258 | Hypo | cancer_general | C22orf34, BC033837 |
| chr22 | 50010461 | 50010585 | Hypo | cancer_general | C22orf34, BC033837 | chr22 | 50031691 | 50031721 | Hypo | cancer_general | C22orf34, BC033837 |
| chr22 | 50149431 | 50149470 | Hypo | cancer_general | — | chr22 | 50251536 | 50251582 | Hypo | breast | ZBED4 |
| chr22 | 50467005 | 50467035 | Hypo | cancer_general | — | chr22 | 50467876 | 50468105 | Hypo | cancer_general | — |
| chr22 | 50768840 | 50768876 | Hypo | cancer_general | DENND6B | chr22 | 50899293 | 50899672 | Hypo | cancer_general | SBF1 |
| chr22 | 50939073 | 50939111 | Hypo | cancer_general | LMF2, NCAPH2 | chr22 | 50986016 | 50986045 | Hypo | literature | SYCE3, KLHDC7B |
| chr10 | 524754 | 524784 | Hypo | head_neck | DIP2C | chr10 | 833307 | 833386 | Hypo | cancer_general | IDI1, IDI2-AS1, IDI2 |
| chr10 | 978878 | 978933 | Hypo | cancer_general | BC127786, LARP4B | chr10 | 1080377 | 1080513 | Hypo | breast | ADARB2-AS1 |
| chr10 | 1120778 | 1120937 | Hypo | lung | WDR37 | chr10 | 1577394 | 1577424 | Hypo | hepatobiliary | — |
| chr10 | 1585111 | 1585239 | Hypo | cancer_general | ADARB2-AS1 | chr10 | 1708327 | 1708478 | Hypo | cancer_general | — |
| chr10 | 3197004 | 3197113 | Hypo | ovarian | BC039685, PTTRM1-AS1, PTTRM1 | chr10 | 3285585 | 3285698 | Hypo | cancer_general | — |
| chr10 | 3330499 | 3330618 | Hypo | cancer_general | — | chr10 | 3641378 | 3641413 | Hypo | colorectal | BC037918 |
| chr10 | 3678597 | 3678637 | Hypo | lung | BC037918 | chr10 | 3895410 | 3895452 | Hypo | cancer_general | — |
| chr10 | 4599917 | 4599965 | Hypo | cancer_general | — | chr10 | 5530764 | 5530975 | Hypo | cancer_general | CALML5 |
| chr10 | 5765021 | 5765059 | Hypo | breast | FAM208B | chr10 | 5855154 | 5855184 | Hypo | pancreas | GDI2 |
| chr10 | 5875140 | 5875396 | Hypo | cancer_general | — | chr10 | 6003402 | 6003855 | Hypo | breast | IL15RA |
| chr10 | 6042309 | 6042571 | Hypo | cancer_general | — | chr10 | 6162159 | 6162225 | Hypo | cancer_general | RBM17 |
| chr10 | 6167619 | 6167742 | Hypo | ovarian | RBM17 | chr10 | 6206142 | 6206217 | Hypo | pancreas | — |
| chr10 | 6372343 | 6372373 | Hypo | ovarian | LOC399715 | chr10 | 6513976 | 6514006 | Hypo | hepatobiliary | PRKCQ |
| chr10 | 6577643 | 6577673 | Hypo | cancer_general | AX748236 | chr10 | 6586721 | 6586847 | Hypo | cancer_general | — |
| chr10 | 6963079 | 6963111 | Hypo | cancer_general | — | chr10 | 6984463 | 6984639 | Hypo | cancer_general | — |
| chr10 | 7205733 | 7205787 | Hypo | cancer_general | SFMBT2 | chr10 | 7212745 | 7213064 | Hypo | cancer_general | SFMBT2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 7213505 | 7213535 | Hypo | hepatobiliary | SFMBT2 | chr10 | 7216059 | 7216089 | Hypo | cancer_general | SFMBT2 |
| chr10 | 7236211 | 7236245 | Hypo | cancer_general | SFMBT2 | chr10 | 7255730 | 7255821 | Hypo | hepatobiliary | SFMBT2 |
| chr10 | 7323283 | 7323313 | Hypo | cancer_general | SFMBT2 | chr10 | 7334737 | 7334767 | Hypo | hepatobiliary | SFMBT2 |
| chr10 | 7363436 | 7363466 | Hypo | hepatobiliary | SFMBT2 | chr10 | 7371678 | 7371708 | Hypo | cancer_general | SFMBT2 |
| chr10 | 7414544 | 7414588 | Hypo | cancer_general | SFMBT2 | chr10 | 7424626 | 7424687 | Hypo | hepatobiliary | SFMBT2 |
| chr10 | 7436090 | 7436209 | Hypo | cancer_general | SFMBT2 | chr10 | 8055681 | 8055764 | Hypo | pancreas | TAF3 |
| chr10 | 11700918 | 11701075 | Hypo | cancer_general |  | chr10 | 12554417 | 12554501 | Hypo | cancer_general | CAMK1D |
| chr10 | 13140861 | 13141020 | Hypo | cancer_general | OPTN, AK311458 | chr10 | 13715208 | 13715401 | Hypo | head_neck | FRMD4A |
| chr10 | 14393819 | 14393893 | Hypo | colorectal | FRMD4A | chr10 | 14966129 | 14966212 | Hypo | cancer_general | DCLRE1C |
| chr10 | 15002784 | 15003006 | Hypo | cancer_general | MEIG1 | chr10 | 15140484 | 15140526 | Hypo | cancer_general | RPP38, NMT2, C10orf111, ACBD7 |
| chr10 | 16175687 | 16175801 | Hypo | hepatobiliary |  | chr10 | 16564087 | 16564116 | Hypo | literature | C1QL3 |
| chr10 | 16564537 | 16564566 | Hypo | literature | C1QL3 | chr10 | 17269259 | 17269288 | Hypo | literature | VIM, BC078172 |
| chr10 | 17275584 | 17275613 | Hypo | literature | VIM, BC078172 | chr10 | 17277741 | 17277770 | Hypo | literature | VIM, BC078172 |
| chr10 | 17429165 | 17429622 | Hypo | cancer_general | ST8SIA6-AS1, ST8SIA6 | chr10 | 17503402 | 17503520 | Hypo | cancer_general | — |
| chr10 | 17509450 | 17509503 | Hypo | hepatobiliary |  | chr10 | 21101525 | 21101555 | Hypo | hepatobiliary | NEBL |
| chr10 | 21728064 | 21728124 | Hypo | cancer_general |  | chr10 | 22047336 | 22047635 | Hypo | breast | DNAJC1 |
| chr10 | 22567093 | 22567322 | Hypo | cancer_general |  | chr10 | 24988589 | 24988619 | Hypo | cancer_general | ARHGAP21 |
| chr10 | 26747051 | 26747159 | Hypo | cancer_general | APBB1IP | chr10 | 26803853 | 26803883 | Hypo | cancer_general |  |
| chr10 | 26816766 | 26816938 | Hypo | cancer_general | RAB18 | chr10 | 26931897 | 26931926 | Hypo | literature | LINC00202-2 |
| chr10 | 27794496 | 27794588 | Hypo | cancer_general | BAMBI | chr10 | 27846637 | 27846816 | Hypo | cancer_general | — |
| chr10 | 28964800 | 28964800 | Hypo | ovarian |  | chr10 | 30848230 | 30848230 | Hypo | cancer_general | — |
| chr10 | 31892922 | 31893079 | Hypo | cancer_general | EPC1 | chr10 | 32499044 | 32499176 | Hypo | cancer_general | ITGB1 |
| chr10 | 32672459 | 32672489 | Hypo | cancer_general |  | chr10 | 33233313 | 33233361 | Hypo | cancer_general | ZNF33BP1, ZNF248 |
| chr10 | 37051865 | 37051895 | Hypo | pancreas |  | chr10 | 38078948 | 38079105 | Hypo | cancer_general |  |
| chr10 | 43186151 | 43186181 | Hypo | cancer_general | AK123067 | chr10 | 43609055 | 43609117 | Hypo | literature | RET |
| chr10 | 43609922 | 43609963 | Hypo | literature | RET | chr10 | 43613890 | 43613919 | Hypo | literature | RET |
| chr10 | 43614982 | 43615011 | Hypo | literature | RET | chr10 | 43615554 | 43615607 | Hypo | literature | RET |
| chr10 | 43617401 | 43617430 | Hypo | literature | RET | chr10 | 43858343 | 43858470 | Hypo | cancer_general | FXYD4 |
| chr10 | 43905877 | 43906023 | Hypo | cancer_general |  | chr10 | 44434176 | 44434206 | Hypo | cancer_general | LINC00841 |
| chr10 | 49652977 | 49653080 | Hypo | cancer_general | ARHGAP22, MAPK8 | chr10 | 50340119 | 50340149 | Hypo | cancer_general | FAM170B, FAM170B-AS1 |
| chr10 | 50507557 | 50507619 | Hypo | cancer_general | C10orf71 | chr10 | 50748131 | 50748350 | Hypo | cancer_general | — |
| chr10 | 53107427 | 53107563 | Hypo | cancer_general |  | chr10 | 63669223 | 63669344 | Hypo | ovarian | ARID5B |
| chr10 | 65262111 | 65262304 | Hypo | breast |  | chr10 | 69578459 | 69578588 | Hypo | cancer_general | DNAJC12 |
| chr10 | 69589153 | 69589407 | Hypo | cancer_general | DNAJC12 | chr10 | 70167678 | 70167708 | Hypo | cancer_general | DNA2, RUFY2 |
| chr10 | 70232345 | 70232485 | Hypo | cancer_general | SLC25A16, DNA2 | chr10 | 70275831 | 70275979 | Hypo | breast | SLC25A16 |
| chr10 | 70314814 | 70315148 | Hypo | cancer_general | TET1 | chr10 | 70565410 | 70565489 | Hypo | cancer_general |  |
| chr10 | 70586494 | 70586540 | Hypo | cancer_general | STOX1 | chr10 | 71084981 | 71085116 | Hypo | hepatobiliary | HK1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 73157867 | 73158027 | Hypo | pancreas | CDH23 | chr10 | 75384100 | 75384130 | Hypo | ovarian | MYOZ1 |
| chr10 | 75386789 | 75386893 | Hypo | cancer_general | MYOZ1 | chr10 | 75388129 | 75388173 | Hypo | cancer_general | MYOZ1 |
| chr10 | 75488953 | 75489125 | Hypo | cancer_general | GLUD1P3, BMS1P4, AGAP5 | chr10 | 81023884 | 81023914 | Hypo | cancer_general | ZMIZ1 |
| chr10 | 81860447 | 81860568 | Hypo | cancer_general | TMEM254 | chr10 | 81966737 | 81966828 | Hypo | cancer_general | LINC00857, ANXA11 |
| chr10 | 85792257 | 85792287 | Hypo | hepatobiliary | — | chr10 | 88304914 | 88304944 | Hypo | cancer_general | — |
| chr10 | 88684005 | 88684034 | Hypo | literature | BMPR1A | chr10 | 88698834 | 88698914 | Hypo | cancer_general | MMRN2 |
| chr10 | 89624255 | 89624311 | Hypo | literature | PTEN, KLLN | chr10 | 89653788 | 89653859 | Hypo | literature | PTEN |
| chr10 | 89685272 | 89685322 | Hypo | literature | PTEN | chr10 | 89690790 | 89690819 | Hypo | literature | PTEN |
| chr10 | 89692776 | 89693015 | Hypo | literature | PTEN | chr10 | 89711861 | 89711992 | Hypo | literature | AK130076, PTEN |
| chr10 | 89717610 | 89717744 | Hypo | literature | AK130076, PTEN | chr10 | 89720790 | 89720885 | Hypo | literature | — |
| chr10 | 89725030 | 89725071 | Hypo | literature | — | chr10 | 94062288 | 94062318 | Hypo | head_neck | 5-Mar |
| chr10 | 96304020 | 96304329 | Hypo | cancer_general | HELLS, TBC1D12 | chr10 | 98129822 | 98130033 | Hypo | cancer_general | TLL2 |
| chr10 | 98528023 | 98528107 | Hypo | cancer_general | ARHGAP19 | chr10 | 98558129 | 98558200 | Hypo | colorectal | — |
| chr10 | 99051122 | 99051253 | Hypo | cancer_general | MARVELD1 | chr10 | 99161398 | 99161560 | Hypo | cancer_general | SLC25A28 |
| chr10 | 99481747 | 99481905 | Hypo | colorectal | CUTC, COX15 | chr10 | 101363207 | 101363418 | Hypo | colorectal | CWF19L1, SNORA12, CHUK |
| chr10 | 101492942 | 101493074 | Hypo | cancer_general |  | chr10 | 101988223 | 101988404 | Hypo | cancer_general | FBXW4 |
| chr10 | 103325743 | 103325773 | Hypo | cancer_general | DPCD, BTRC | chr10 | 103425950 | 103426174 | Hypo | ovarian | — |
| chr10 | 103579635 | 103579713 | Hypo | cancer_general | KCNIP2, LOC100289509, MGEA5 | chr10 | 103814668 | 103814754 | Hypo | cancer_general | C10orf76 |
| chr10 | 103930034 | 103930161 | Hypo | cancer_general | NOLC1 | chr10 | 105126957 | 105127076 | Hypo | cancer_general | TAF5 |
| chr10 | 105155285 | 105155481 | Hypo | cancer_general | PDCD11, MIR1307, USMG5, TAF5 | chr10 | 105413627 | 105413784 | Hypo | cancer_general | SH3PXD2A |
| chr10 | 105420861 | 105420891 | Hypo | breast | SH3PXD2A | chr10 | 105527028 | 105527057 | Hypo | literature | — |
| chr10 | 108469672 | 108470093 | Hypo | cancer_general | SORCS1 | chr10 | 112440378 | 112440408 | Hypo | cancer_general | RBM20 |
| chr10 | 115925505 | 115925552 | Hypo | cancer_general | MIR2110, C10orf118 | chr10 | 116331126 | 116331156 | Hypo | cancer_general | — |
| chr10 | 119807026 | 119807056 | Hypo | cancer_general | CASC2, RAB11FIP2 | chr10 | 120707028 | 120707111 | Hypo | cancer_general | — |
| chr10 | 120800789 | 120800835 | Hypo | ovarian | EIF3A, NANOS1 | chr10 | 120841558 | 120841590 | Hypo | cancer_general | — |
| chr10 | 120937014 | 120937139 | Hypo | breast | PRDX3 | chr10 | 121267480 | 121267626 | Hypo | hepatobiliary | RGS10 |
| chr10 | 121307542 | 121307572 | Hypo | cancer_general | — | chr10 | 123256044 | 123256232 | Hypo | literature | FGFR2 |
| chr10 | 123258020 | 123258091 | Hypo | literature | FGFR2 | chr10 | 123274758 | 123274787 | Hypo | literature | FGFR2 |
| chr10 | 123279548 | 123279697 | Hypo | literature | FGFR2 | chr10 | 123667184 | 123667222 | Hypo | breast | ATE1 |
| chr10 | 123688711 | 123688741 | Hypo | cancer_general | ATE1 | chr10 | 125527754 | 125527784 | Hypo | hepatobiliary | CPXM2 |
| chr10 | 126101966 | 126102095 | Hypo | head_neck | OAT | chr10 | 126198949 | 126199077 | Hypo | cancer_general | LHPP |
| chr10 | 126697789 | 126698107 | Hypo | cancer_general | CTBP2 | chr10 | 126782965 | 126783048 | Hypo | hepatobiliary | — |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr10 | 126828994 | 126829024 | Hypo | hepatobiliary | — | chr10 | 127406313 | 127406386 | Hypo | ovarian | C10orf137, FLJ37035, LOC283038 |
| chr10 | 127693923 | 127693959 | Hypo | hepatobiliary | ADAM12, FANK1 | chr10 | 129379338 | 129379367 | Hypo | literature | — |
| chr10 | 129888804 | 129888885 | Hypo | cancer_general | MKI67, PTPRE | chr10 | 130203435 | 130203480 | Hypo | cancer_general | — |
| chr10 | 130577764 | 130577794 | Hypo | cancer_general | — | chr10 | 131348513 | 131348793 | Hypo | pancreas | MGMT |
| chr10 | 131647903 | 131647933 | Hypo | cancer_general | MIR4297, EBF3 | chr10 | 131936451 | 131936626 | Hypo | cancer_general | GLRX3 |
| chr10 | 131937355 | 131937428 | Hypo | lung | GLRX3 | chr10 | 132000973 | 132001015 | Hypo | cancer_general | — |
| chr10 | 132001252 | 132001556 | Hypo | cancer_general | — | chr10 | 133951602 | 133952025 | Hypo | cancer_general | JAKMIP3 |
| chr10 | 133979059 | 133979089 | Hypo | cancer_general | JAKMIP3 | chr10 | 134016203 | 134016388 | Hypo | cancer_general | STK32C, DPYSL4 |
| chr10 | 134022845 | 134022875 | Hypo | cancer_general | STK32C, DPYSL4 | chr10 | 134039087 | 134039117 | Hypo | hepatobiliary | STK32C |
| chr10 | 134092153 | 134092202 | Hypo | cancer_general | STK32C | chr10 | 134095594 | 134095833 | Hypo | cancer_general | STK32C |
| chr10 | 134119401 | 134119447 | Hypo | hepatobiliary | STK32C | chr10 | 134273064 | 134273156 | Hypo | cancer_general | — |
| chr10 | 134301095 | 134301212 | Hypo | cancer_general | — | chr10 | 134481320 | 134481433 | Hypo | cancer_general | INPP5A |
| chr10 | 134491021 | 134491114 | Hypo | ovarian | INPP5A | chr10 | 134499773 | 134499803 | Hypo | pancreas | INPP5A |
| chr10 | 134593329 | 134593416 | Hypo | ovarian | NKX6-2, INPP5A | chr10 | 134607970 | 134608183 | Hypo | cancer_general | NKX6-2 |
| chr10 | 134665147 | 134665202 | Hypo | cancer_general | TTC40 | chr10 | 134679129 | 134679265 | Hypo | cancer_general | TTC40 |
| chr10 | 134690559 | 134690617 | Hypo | cancer_general | TTC40 | chr10 | 134693587 | 134693709 | Hypo | cancer_general | TTC40 |
| chr10 | 134699872 | 134699909 | Hypo | cancer_general | TTC40 | chr10 | 134733221 | 134733275 | Hypo | cancer_general | TTC40 |
| chr10 | 134733497 | 134733617 | Hypo | cancer_general | TTC40 | chr10 | 134738378 | 134738642 | Hypo | cancer_general | TTC40 |
| chr10 | 134788083 | 134788251 | Hypo | cancer_general | LOC399829 | chr10 | 134794271 | 134794342 | Hypo | cancer_general | LOC399829 |
| chr10 | 134796012 | 134796042 | Hypo | cancer_general | LOC399829 | chr10 | 134896060 | 134896092 | Hypo | hepatobiliary | GPR123 |
| chr10 | 134916774 | 134916774 | Hypo | cancer_general | GPR123 | chr10 | 134941145 | 134941178 | Hypo | cancer_general | GPR123 |
| chr10 | 134942840 | 134943114 | Hypo | cancer_general | GPR123 | chr10 | 134943445 | 134943542 | Hypo | cancer_general | GPR123 |
| chr10 | 134944742 | 134944772 | Hypo | cancer_general | KNDC1 | chr10 | 134959217 | 134959391 | Hypo | cancer_general | CS330190 |
| chr10 | 135002063 | 135002156 | Hypo | cancer_general | KNDC1 | chr10 | 135014963 | 135015132 | Hypo | cancer_general | KNDC1 |
| chr10 | 135017049 | 135017129 | Hypo | cancer_general | KNDC1 | chr10 | 135018032 | 135018070 | Hypo | ovarian | KNDC1 |
| chr10 | 135018825 | 135018960 | Hypo | cancer_general | KNDC1 | chr10 | 135020801 | 135020893 | Hypo | cancer_general | ADAM8 |
| chr10 | 135023470 | 135023500 | Hypo | cancer_general | PRAP1, ZNF511, TUBGCP2 | chr10 | 135076368 | 135076503 | Hypo | cancer_general | PRAP1, CALY |
| chr10 | 135122991 | 135123020 | Hypo | literature | — | chr10 | 135153956 | 135154001 | Hypo | ovarian | — |
| chr14 | 21100748 | 21100778 | Hypo | head_neck | TRNA_Pro, OR6S1, TRNA_Thr, TRNA_Leu | chr14 | 23234956 | 23235032 | Hypo | esophageal | OXA1L, SLC7A7 |
| chr14 | 23400315 | 23400354 | Hypo | cancer_general | TRNA, TRNA_Arg, PRMT5 | chr14 | 23426755 | 23426785 | Hypo | cancer_general | MIR4707, HAUS4 |
| chr14 | 23701644 | 23701737 | Hypo | head_neck | — | chr14 | 23706727 | 23706765 | Hypo | cancer_general | — |
| chr14 | 24562744 | 24562774 | Hypo | cancer_general | PCK2 | chr14 | 25071566 | 25071612 | Hypo | cancer_general | GZMH |
| chr14 | 25155907 | 25155985 | Hypo | cancer_general | — | chr14 | 31027323 | 31027367 | Hypo | cancer_general | G2E3 |
| chr14 | 31925554 | 31925724 | Hypo | cancer_general | BC041327, DTD2 | chr14 | 32597620 | 32597657 | Hypo | pancreas | ARHGAP5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 34269897 | 34270004 | Hypo | head_neck | — | chr14 | 35023111 | 35023322 | Hypo | cancer_general | SNX6 |
| chr14 | 35024446 | 35024546 | Hypo | cancer_general | SNX6 | chr14 | 35389907 | 35389943 | Hypo | cancer_general | — |
| chr14 | 39579800 | 39579830 | Hypo | cancer_general | GEMIN2 | chr14 | 45602514 | 45602576 | Hypo | cancer_general | FANCM, FKBP3 |
| chr14 | 50233426 | 50233459 | Hypo | cancer_general | KLHDC2 Metazoa_SRP | chr14 | 50333754 | 50333994 | Hypo | cancer_general | Metazoa_SRP ARF6 |
| chr14 | 50334254 | 50334355 | Hypo | cancer_general | | chr14 | 50355854 | 50355924 | Hypo | colorectal | ATP5S, L2HGDH |
| chr14 | 50681598 | 50681859 | Hypo | breast | | chr14 | 50777663 | 50777714 | Hypo | cancer_general | |
| chr14 | 51829264 | 51829396 | Hypo | ovarian | LINC00640 | chr14 | 51955509 | 51955538 | Hypo | literature | FRMD6, FRMD6-AS2 |
| chr14 | 52765920 | 52766075 | Hypo | cancer_general | | chr14 | 55370202 | 55370235 | Hypo | cancer_general | |
| chr14 | 55668368 | 55668526 | Hypo | colorectal | DLGAP5 | chr14 | 55765285 | 55765714 | Hypo | lung, cancer_general | FBXO34 |
| chr14 | 55823079 | 55823218 | Hypo | breast | ATG14, FBXO34 | chr14 | 57045520 | 57045739 | Hypo | cancer_general | TMEM260 |
| chr14 | 57270936 | 57270987 | Hypo | cancer_general | OTX2, OTX2-AS1 | chr14 | 58857094 | 58857355 | Hypo | cancer_general | TOMM20L |
| chr14 | 58893052 | 58893183 | Hypo | cancer_general | KIAA0586, TIMM9 | chr14 | 59770326 | 59770452 | Hypo | breast | DAAM1 |
| chr14 | 62106193 | 62106242 | Hypo | colorectal | FLJ22447 | chr14 | 64107335 | 64107600 | Hypo | cancer_general | |
| chr14 | 64222413 | 64222488 | Hypo | cancer_general | | chr14 | 65005696 | 65005833 | Hypo | cancer_general | HSPA2 |
| chr14 | 65233339 | 65233464 | Hypo | cancer_general | SPTB | chr14 | 66498931 | 66498975 | Hypo | cancer_general | |
| chr14 | 67585164 | 67585413 | Hypo | cancer_general | GPHN | chr14 | 67886378 | 67886606 | Hypo | cancer_general | PLEK2 |
| chr14 | 68334928 | 68335108 | Hypo | cancer_general | RAD51B SLC39A9, ERH | chr14 | 69014044 | 69014110 | Hypo | pancreas | |
| chr14 | 69866541 | 69866706 | Hypo | cancer_general | | chr14 | 69867022 | 69867196 | Hypo | cancer_general | SLC39A9, ERH |
| chr14 | 73167750 | 73167899 | Hypo | cancer_general | DPF3 | chr14 | 73175026 | 73175148 | Hypo | cancer_general | DPF3 |
| chr14 | 73178807 | 73178865 | Hypo | cancer_general | DPF3 | chr14 | 73180208 | 73180314 | Hypo | cancer_general | DPF3 |
| chr14 | 73226952 | 73227005 | Hypo | cancer_general | DPF3 | chr14 | 73231266 | 73231414 | Hypo | lung, cancer_general | DPF3 |
| chr14 | 73236095 | 73236178 | Hypo | cancer_general | DPF3 | chr14 | 73318471 | 73318629 | Hypo | lung, cancer_general | DPF3 |
| chr14 | 73333249 | 73333396 | Hypo | cancer_general | DPF3 | chr14 | 73602250 | 73602389 | Hypo | cancer_general | PSEN1 |
| chr14 | 73604570 | 73604718 | Hypo | cancer_general | PSEN1 | chr14 | 73855616 | 73855646 | Hypo | cancer_general | NUMB |
| chr14 | 73956853 | 73956913 | Hypo | cancer_general | C14orf169, HEATR4 | chr14 | 74529109 | 74529139 | Hypo | cancer_general | ALDH6A1, CCDC176 |
| chr14 | 75760311 | 75760347 | Hypo | cancer_general | LOC731223 | chr14 | 76128674 | 76128842 | Hypo | cancer_general | C14orf1, TTL5 |
| chr14 | 77737785 | 77737814 | Hypo | tcga | POMT2, MIR1260A, NGB | chr14 | 88457599 | 88457685 | Hypo | cancer_general | U6, GALC |
| chr14 | 90983328 | 90983360 | Hypo | cancer_general | | chr14 | 91691163 | 91691306 | Hypo | lung | GPR68 |
| chr14 | 91691696 | 91691822 | Hypo | lung | GPR68 | chr14 | 91766154 | 91766450 | Hypo | lung | |
| chr14 | 91780382 | 91780512 | Hypo | hepatobiliary | AX721199, BC039675, TRIP11 | chr14 | 91801036 | 91801164 | Hypo | hepatobiliary | CCDC88C |
| chr14 | 92507578 | 92507792 | Hypo | pancreas, cancer_general | | chr14 | 93155061 | 93155315 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 93571193 | 93571326 | Hypo | breast | — | chr14 | 93706752 | 93706782 | Hypo | cancer_general | BTBD7 |
| chr14 | 94603542 | 94603670 | Hypo | lung | IFI27L2 | chr14 | 95233705 | 95233765 | Hypo | cancer_general | GSC |
| chr14 | 95240227 | 95240341 | Hypo | cancer_general | GSC | chr14 | 95557626 | 95557655 | Hypo | literature | DICER1 |
| chr14 | 95560448 | 95560477 | Hypo | literature | DICER1 | chr14 | 95740035 | 95740116 | Hypo | cancer_general | CLMN |
| chr14 | 96053974 | 96054020 | Hypo | cancer_general | BC038791 | chr14 | 97045354 | 97045431 | Hypo | cancer_general | — |
| chr14 | 100148073 | 100148230 | Hypo | cancer_general | HHIPL1, CYP46A1, MIR5698 | chr14 | 100643350 | 100643481 | Hypo | cancer_general | — |
| chr14 | 100843765 | 100843912 | Hypo | cancer_general | WDR25, WARS | chr14 | 101250109 | 101250272 | Hypo | cancer_general | — |
| chr14 | 101506231 | 101506260 | Hypo | literature | MIR539, JA715142, MIR376C, MIR543, MIR376A2, MIR1185-1, MIR381, MIR487B, MIR654, MIR1185-2, Mir_544, Mir_654, MIR1193, MIR300, MIR889, Mir_154, MIR495, MIR376B, MIR376A1, MIR655 | chr14 | 102418607 | 102418637 | Hypo | cancer_general | — |
| chr14 | 102521602 | 102521758 | Hypo | cancer_general | — | chr14 | 102529325 | 102529419 | Hypo | cancer_general | — |
| chr14 | 102530007 | 102530234 | Hypo | cancer_general | — | chr14 | 102530500 | 102530530 | Hypo | cancer_general | MOK, AK130824, WDR20 |
| chr14 | 102564464 | 102564605 | Hypo | breast | — | chr14 | 102682077 | 102682149 | Hypo | lung, cancer_general | ANKRD9, TECPR2 |
| chr14 | 102772607 | 102772695 | Hypo | cancer_general | MOK | chr14 | 102973169 | 102973268 | Hypo | head_neck | AK097119, AX746968, XRCC3 |
| chr14 | 103477643 | 103477794 | Hypo | cancer_general | — | chr14 | 104160060 | 104160134 | Hypo | cancer_general | — |
| chr14 | 104202705 | 104202759 | Hypo | cancer_general | PPP1R13B, ZFYVE21 | chr14 | 104355204 | 104355273 | Hypo | cancer_general | ASPG |
| chr14 | 104386476 | 104387067 | Hypo | cancer_general | C14orf2, TDRD9 | chr14 | 104547785 | 104547909 | Hypo | cancer_general | KIF26A |
| chr14 | 104571985 | 104572116 | Hypo | cancer_general | ASPG | chr14 | 104620411 | 104620554 | Hypo | cancer_general | KIF26A |
| chr14 | 104627664 | 104627759 | Hypo | cancer_general | KIF26A | chr14 | 104645126 | 104645188 | Hypo | cancer_general | KIF26A |
| chr14 | 104646317 | 104646491 | Hypo | cancer_general | KIF26A | chr14 | 104647257 | 104647287 | Hypo | cancer_general | — |
| chr14 | 104682545 | 104682656 | Hypo | cancer_general | — | chr14 | 104863860 | 104863026 | Hypo | cancer_general | INF2 |
| chr14 | 104897228 | 104897294 | Hypo | cancer_general | — | chr14 | 105157485 | 105157554 | Hypo | cancer_general | AKT1 |
| chr14 | 105239389 | 105239439 | Hypo | literature | AKT1 | chr14 | 105239793 | 105239825 | Hypo | literature | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 105241309 | 105241428 | Hypo | literature | AKT1 | chr14 | 105243032 | 105243064 | Hypo | literature | AKT1 |
| chr14 | 105246427 | 105246582 | Hypo | literature | AKT1 | chr14 | 105658349 | 105658425 | Hypo | cancer_general | — |
| chr14 | 105714258 | 105714334 | Hypo | cancer_general | BTBD6, BRF1 | GL000231.1 | 12576 | 12717 | Hypo | cancer_general | — |
| HCMV-AD169 | 17724 | 17753 | Hypo | virus | — | HCMV-AD169 | 18691 | 18720 | Hypo | virus | — |
| HCMV-AD169 | 23851 | 23880 | Hypo | virus | — | HCMV-AD169 | 27296 | 27325 | Hypo | virus | — |
| HCMV-AD169 | 42909 | 42938 | Hypo | virus | — | HCMV-AD169 | 57909 | 57938 | Hypo | virus | — |
| HCMV-AD169 | 68427 | 68456 | Hypo | virus | — | HCMV-AD169 | 76862 | 76891 | Hypo | virus | — |
| HCMV-AD169 | 78956 | 78985 | Hypo | virus | — | HCMV-AD169 | 81188 | 81217 | Hypo | virus | — |
| HCMV-AD169 | 84448 | 84477 | Hypo | virus | — | HCMV-AD169 | 88920 | 88949 | Hypo | virus | — |
| HCMV-AD169 | 99889 | 99918 | Hypo | virus | — | HCMV-AD169 | 101238 | 101267 | Hypo | virus | — |
| HCMV-AD169 | 108021 | 108050 | Hypo | virus | — | HCMV-AD169 | 114824 | 114853 | Hypo | virus | — |
| HCMV-AD169 | 128011 | 128040 | Hypo | virus | — | HCMV-AD169 | 129567 | 129596 | Hypo | virus | — |
| HCMV-AD169 | 149187 | 149216 | Hypo | virus | — | HCMV-AD169 | 162299 | 162328 | Hypo | virus | — |
| HCMV-AD169 | 169250 | 169279 | Hypo | virus | — | HCMV-AD169 | 171221 | 171250 | Hypo | virus | — |
| HCMV-AD169 | 172561 | 172590 | Hypo | virus | — | HCMV-AD169 | 177053 | 177082 | Hypo | virus | — |
| HCMV-AD169 | 193060 | 193089 | Hypo | virus | — | HCMV-AD169 | 193858 | 193887 | Hypo | virus | — |
| HCMV-AD169 | 194176 | 194205 | Hypo | virus | — | HCMV-AD169 | 195222 | 195251 | Hypo | virus | — |
| HCMV-AD169 | 196060 | 196089 | Hypo | virus | — | HCMV-AD169 | 196817 | 196846 | Hypo | virus | — |
| HCMV-AD169 | 199152 | 199181 | Hypo | virus | — | HCMV-AD169 | 199906 | 199935 | Hypo | virus | — |
| HCMV-AD169 | 201145 | 201174 | Hypo | virus | — | HCMV-AD169 | 204433 | 204462 | Hypo | virus | — |
| HCMV-AD169 | 207682 | 207711 | Hypo | virus | — | HCMV-AD169 | 209510 | 209539 | Hypo | virus | — |
| HCMV-AD169 | 210069 | 210098 | Hypo | virus | — | HCMV-AD169 | 212133 | 212162 | Hypo | virus | — |
| HCMV-AD169 | 212591 | 212620 | Hypo | virus | — | HCMV-AD169 | 214453 | 214482 | Hypo | virus | — |
| HCMV-AD169 | 220316 | 220345 | Hypo | virus | — | MCV-R17b | 111 | 140 | Hypo | virus | — |
| MCV-R17b | 368 | 397 | Hypo | virus | — | MCV-R17b | 625 | 654 | Hypo | virus | — |
| MCV-R17b | 882 | 911 | Hypo | virus | — | MCV-R17b | 1139 | 1168 | Hypo | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| MCV-R17b | 1396 | 1425 | Hypo | virus | — | MCV-R17b | 1653 | 1682 | Hypo | virus | — |
| MCV-R17b | 1910 | 1939 | Hypo | virus | — | MCV-R17b | 2167 | 2196 | Hypo | virus | — |
| MCV-R17b | 2424 | 2453 | Hypo | virus | — | MCV-R17b | 2681 | 2710 | Hypo | virus | — |
| MCV-R17b | 2938 | 2967 | Hypo | virus | — | MCV-R17b | 3195 | 3224 | Hypo | virus | — |
| MCV-R17b | 3452 | 3481 | Hypo | virus | — | MCV-R17b | 3709 | 3738 | Hypo | virus | — |
| MCV-R17b | 3966 | 3995 | Hypo | virus | — | MCV-R17b | 4223 | 4252 | Hypo | virus | — |
| MCV-R17b | 4480 | 4509 | Hypo | virus | — | MCV-R17b | 4737 | 4766 | Hypo | virus | — |
| MCV-R17b | 4994 | 5023 | Hypo | virus | — | chr7 | 68930 | 68960 | Hypo | cancer_general | — |
| chr7 | 369494 | 369536 | Hypo | cancer_general | — | chr7 | 369844 | 369980 | Hypo | cancer_general | LOC442497 |
| chr7 | 389663 | 389693 | Hypo | cancer_general | LOC442497 | chr7 | 409826 | 409892 | Hypo | esophageal | LOC442497 |
| chr7 | 427454 | 427484 | Hypo | hepatobiliary | — | chr7 | 431386 | 431492 | Hypo | cancer_general | — |
| chr7 | 497782 | 497934 | Hypo | cancer_general | FLJ44511, PDGFA | chr7 | 503811 | 503936 | Hypo | cancer_general | — |
| chr7 | 551599 | 551697 | Hypo | cancer_general | PRKAR1B | chr7 | 564237 | 564271 | Hypo | breast | FLJ44511 |
| chr7 | 578922 | 579020 | Hypo | cancer_general | — | chr7 | 579827 | 579857 | Hypo | cancer_general | PRKAR1B SUN1, GET4 |
| chr7 | 842331 | 842414 | Hypo | cancer_general | GET4, SUN1 | chr7 | 907656 | 907709 | Hypo | breast | CYP2W1, COX19 |
| chr7 | 915058 | 915087 | Hypo | literature | CYP2W1, COX19 | chr7 | 1016343 | 1016373 | Hypo | colorectal | C7orf50, CYP2W1 |
| chr7 | 1022224 | 1022254 | Hypo | cancer_general | MIR339, C7orf50 | chr7 | 1030172 | 1030283 | Hypo | cancer_general | GPR146 |
| chr7 | 1054579 | 1054696 | Hypo | cancer_general | AK090593, AK123998, ZFAND2A | chr7 | 1086199 | 1086319 | Hypo | cancer_general | — |
| chr7 | 1195270 | 1195364 | Hypo | hepatobiliary | — | chr7 | 1308351 | 1308497 | Hypo | cancer_general | — |
| chr7 | 1325810 | 1325882 | Hypo | cancer_general | AK127339, INTS1 | chr7 | 1416020 | 1416131 | Hypo | cancer_general | — |
| chr7 | 1423632 | 1423677 | Hypo | cancer_general | TMEM184A, PSMG3 | chr7 | 1459041 | 1459191 | Hypo | cancer_general | — |
| chr7 | 1503417 | 1503596 | Hypo | cancer_general | PSMG3-AS1, PSMG3 | chr7 | 1547311 | 1547394 | Hypo | cancer_general | INTS1 |
| chr7 | 1598639 | 1598697 | Hypo | cancer_general | PSMG3, PSMG3-AS1 | chr7 | 1607386 | 1607465 | Hypo | cancer_general | PSMG3-AS1, PSMG3 |
| chr7 | 1607971 | 1608001 | Hypo | cancer_general | — | chr7 | 1611443 | 1611522 | Hypo | cancer_general | PSMG3-AS1, PSMG3 |
| chr7 | 1615390 | 1615444 | Hypo | cancer_general | LOC401296 | chr7 | 1627404 | 1627434 | Hypo | cancer_general | KIAA1908, PSMG3-AS1 |
| chr7 | 1641774 | 1641923 | Hypo | cancer_general | — | chr7 | 1681189 | 1681239 | Hypo | cancer_general | — |
| chr7 | 1688977 | 1689146 | Hypo | cancer_general | — | chr7 | 1690745 | 1690851 | Hypo | cancer_general | — |
| chr7 | 1733166 | 1733378 | Hypo | cancer_general | — | chr7 | 1735223 | 1735354 | Hypo | cancer_general | LOC401296 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 1775831 | 1775861 | Hypo | cancer_general | ELFN1, JX046910 | chr7 | 1778875 | 1778914 | Hypo | cancer_general | ELFN1, JX046910 |
| chr7 | 1783551 | 1783623 | Hypo | cancer_general | JX046910, ELFN1 | chr7 | 1786514 | 1786899 | Hypo | cancer_general | ELFN1, JX046910 |
| chr7 | 1787166 | 1787324 | Hypo | cancer_general | ELFN1, JX046910 | chr7 | 1800882 | 1800912 | Hypo | cancer_general | — |
| chr7 | 1970842 | 1970872 | Hypo | pancreas | MAD1L1 | chr7 | 2109874 | 2109904 | Hypo | pancreas | MAD1L1 |
| chr7 | 2163332 | 2163467 | Hypo | cancer_general | MAD1L1 | chr7 | 2208670 | 2208808 | Hypo | cancer_general | MAD1L1 |
| chr7 | 2232963 | 2233056 | Hypo | cancer_general | MAD1L1 | chr7 | 2233292 | 2233414 | Hypo | cancer_general | MAD1L1 |
| chr7 | 2238118 | 2238235 | Hypo | lung | MAD1L1 | chr7 | 2300787 | 2300899 | Hypo | cancer_general | SNX8 |
| chr7 | 2361190 | 2361434 | Hypo | cancer_general | SNX8 | chr7 | 2473452 | 2473605 | Hypo | lung | BC034268, CHST12 |
| chr7 | 2565919 | 2566041 | Hypo | cancer_general | MIR4648, LFNG | chr7 | 2566600 | 2566630 | Hypo | cancer_general | MIR4648, LFNG |
| chr7 | 2595825 | 2595943 | Hypo | pancreas | IQCE, BRAT1 | chr7 | 2659340 | 2659370 | Hypo | cancer_general | — |
| chr7 | 2720013 | 2720140 | Hypo | cancer_general | AMZ1 | chr7 | 2979480 | 2979512 | Hypo | literature | CARD11 |
| chr7 | 2985518 | 2985547 | Hypo | literature | CARD11 | chr7 | 3033658 | 3033688 | Hypo | cancer_general | CARD11 |
| chr7 | 3283704 | 3283894 | Hypo | cancer_general | — | chr7 | 4215324 | 4215384 | Hypo | cancer_general | SDK1 |
| chr7 | 4657806 | 4657857 | Hypo | hepatobiliary | — | chr7 | 4856984 | 4857048 | Hypo | cancer_general | RADIL |
| chr7 | 5262433 | 5262562 | Hypo | lung | WIPI2 | chr7 | 5397777 | 5397938 | Hypo | breast | TNRC18 |
| chr7 | 5603717 | 5603947 | Hypo | cancer_general | — | chr7 | 5648107 | 5648393 | Hypo | literature, cancer_general | FSCN1 |
| chr7 | 6045612 | 6045641 | Hypo | literature | AIMP2, PMS2 | chr7 | 6059024 | 6059182 | Hypo | ovarian | EIF2AK1, AIMP2 |
| chr7 | 6060590 | 6060634 | Hypo | cancer_general | EIF2AK1, AIMP2 | chr7 | 6099217 | 6099334 | Hypo | cancer_general | — |
| chr7 | 6124714 | 6124714 | Hypo | cancer_general | — | chr7 | 6188610 | 6189061 | Hypo | breast | USP42 |
| chr7 | 6307943 | 6308066 | Hypo | cancer_general | CYTH3 | chr7 | 6414386 | 6414415 | Hypo | literature | RAC1 |
| chr7 | 6426878 | 6426907 | Hypo | literature | RAC1 | chr7 | 6443279 | 6443376 | Hypo | cancer_general | RAC1, DAGLB |
| chr7 | 6443826 | 6443856 | Hypo | cancer_general | DAGLB, RAC1 | chr7 | 6484445 | 6484545 | Hypo | lung | DAGLB |
| chr7 | 6524573 | 6524744 | Hypo | cancer_general | KDELR2 | chr7 | 6524977 | 6525012 | Hypo | cancer_general | KDELR2 |
| chr7 | 6525477 | 6525606 | Hypo | cancer_general | KDELR2 | chr7 | 6560235 | 6560345 | Hypo | cancer_general | Mir_633, GRID2IP |
| chr7 | 7015498 | 7015673 | Hypo | ovarian | — | chr7 | 7605441 | 7605822 | Hypo | cancer_general | MIOS |
| chr7 | 8343630 | 8343724 | Hypo | cancer_general | — | chr7 | 8391475 | 8391573 | Hypo | cancer_general | AX746880 |
| chr7 | 12751410 | 12751496 | Hypo | colorectal | — | chr7 | 12776779 | 12776811 | Hypo | cancer_general | — |
| chr7 | 20089670 | 20089700 | Hypo | hepatobiliary | — | chr7 | 20183238 | 20183283 | Hypo | hepatobiliary | MACC1-AS1, MACC1 |
| chr7 | 21403615 | 21403645 | Hypo | cancer_general | — | chr7 | 22824965 | 22825009 | Hypo | colorectal, cancer_general | — |
| chr7 | 23253573 | 23253671 | Hypo | colorectal | AK057873 | chr7 | 23526549 | 23526698 | Hypo | cancer_general | RPS2P32 |
| chr7 | 23578703 | 23578857 | Hypo | cancer_general | TRA2A | chr7 | 24580644 | 24580806 | Hypo | cancer_general | — |
| chr7 | 25132558 | 25132726 | Hypo | cancer_general | — | chr7 | 25133492 | 25133650 | Hypo | cancer_general | — |
| chr7 | 25165921 | 25166061 | Hypo | cancer_general | C7orf31, CYCS | chr7 | 26194906 | 26195024 | Hypo | cancer_general | NFE2L3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 26283775 | 26283954 | Hypo | cancer_general, breast | — | chr7 | 27184015 | 27184190 | Hypo | literature | HOXA7, HOXA5, HOXA6, HOXA-AS3, DQ655986 |
| chr7 | 27245668 | 27245795 | Hypo | cancer_general | HOTTIP, HOXA13 | chr7 | 28110701 | 28110828 | Hypo | breast | JAZF1 |
| chr7 | 28238339 | 28238444 | Hypo | cancer_general | JAZF1-AS1 | chr7 | 28989065 | 28989159 | Hypo | cancer_general | TRIL, DQ601810 |
| chr7 | 30029923 | 30029952 | Hypo | tcga | SCRN1 FAM188B, INMT-FAM188B | chr7 | 30030307 | 30030337 | Hypo | cancer_general | SCRN1 |
| chr7 | 30857157 | 30857292 | Hypo | lung | | chr7 | 33167928 | 33168030 | Hypo | ovarian | BBS9 |
| chr7 | 33725803 | 33725938 | Hypo | lung | — | chr7 | 35298755 | 35298819 | Hypo | cancer_general | TBX20 |
| chr7 | 35301086 | 35301216 | Hypo | cancer_general | TBX20 | chr7 | 37352957 | 37353062 | Hypo | cancer_general | — |
| chr7 | 37907440 | 37907470 | Hypo | cancer_general | NME8 | chr7 | 38588471 | 38588501 | Hypo | esophageal | — |
| chr7 | 42377468 | 42377497 | Hypo | literature | RASA4CP, DBNL, LINC00957 | chr7 | 43817999 | 43818119 | Hypo | cancer_general | BLVRA PGAM2, DBNL |
| chr7 | 44083283 | 44083416 | Hypo | cancer_general | | chr7 | 44097690 | 44097876 | Hypo | head_neck | |
| chr7 | 44151398 | 44151428 | Hypo | cancer_general | POLD2, AEBP1, MIR4649 | chr7 | 44151795 | 44151933 | Hypo | cancer_general | POLD2, AEBP1, MIR4649 |
| chr7 | 44740467 | 44740672 | Hypo | ovarian | OGDH | chr7 | 44835037 | 44835384 | Hypo | cancer_general | PPIA |
| chr7 | 44912004 | 44912034 | Hypo | head_neck | PURB | chr7 | 45026942 | 45027045 | Hypo | cancer_general | SNORA9, SNHG15, MYO1G |
| chr7 | 45038532 | 45038655 | Hypo | cancer_general | CCM2 | chr7 | 45046874 | 45046982 | Hypo | breast | CCM2 |
| chr7 | 45225402 | 45225432 | Hypo | cancer_general | — | chr7 | 45614929 | 45615020 | Hypo | pancreas | ADCY1 |
| chr7 | 47515359 | 47515405 | Hypo | cancer_general | TNS3 | chr7 | 47704289 | 47704359 | Hypo | cancer_general | C7orf65 |
| chr7 | 49654508 | 49654538 | Hypo | cancer_general | — | chr7 | 49819674 | 49819703 | Hypo | literature | VWC2 |
| chr7 | 50294451 | 50294481 | Hypo | cancer_general | — | chr7 | 50365076 | 50365137 | Hypo | cancer_general | IKZF1 |
| chr7 | 50438618 | 50438648 | Hypo | cancer_general | IKZF1 | chr7 | 50441145 | 50441285 | Hypo | literature | IKZF1 |
| chr7 | 50560588 | 50560637 | Hypo | cancer_general | DDC | chr7 | 55209976 | 55210005 | Hypo | literature | EGFR |
| chr7 | 55211065 | 55211094 | Hypo | literature | EGFR | chr7 | 55221729 | 55221836 | Hypo | literature | EGFR |
| chr7 | 55223589 | 55223636 | Hypo | literature | EGFR | chr7 | 55227993 | 55228022 | Hypo | literature | EGFR |
| chr7 | 55233028 | 55233123 | Hypo | literature | EGFR | chr7 | 55241663 | 55241737 | Hypo | literature | EGFR-AS1, EGFR |
| chr7 | 55224419 | 55242493 | Hypo | literature | EGFR-AS1, EGFR | chr7 | 55248975 | 55249085 | Hypo | literature | EGFR, EGFR-AS1 |
| chr7 | 55259404 | 55259547 | Hypo | literature | EGFR, EGFR-AS1 | chr7 | 55260469 | 55260498 | Hypo | literature | EGFR, EGFR-AS1 |
| chr7 | 55268867 | 55268896 | Hypo | literature | GU228584, EGFR | chr7 | 55410019 | 55410126 | Hypo | breast | — |
| chr7 | 55506288 | 55506348 | Hypo | lung | LANCL2 | chr7 | 56018123 | 56018286 | Hypo | cancer_general | MRPS17, ZNF713 |
| chr7 | 56031716 | 56031869 | Hypo | cancer_general | GBAS, MRPS17 | chr7 | 63667431 | 63667460 | Hypo | literature | ZNF735 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 64330411 | 64330470 | Hypo | hepatobiliary | AK097702 | chr7 | 64330734 | 64330833 | Hypo | cancer_general | AK097702 |
| chr7 | 64713317 | 64713449 | Hypo | cancer_general | — | chr7 | 65510006 | 65510096 | Hypo | cancer_general | — |
| chr7 | 65879649 | 65879883 | Hypo | cancer_general | — | chr7 | 65880359 | 65880405 | Hypo | cancer_general | — |
| chr7 | 66204493 | 66204617 | Hypo | cancer_general | RABGEF1 | chr7 | 66206923 | 66206953 | Hypo | cancer_general | RABGEF1 |
| chr7 | 66214923 | 66214961 | Hypo | cancer_general | RABGEF1 | chr7 | 67579765 | 67579911 | Hypo | cancer_general | — |
| chr7 | 68204793 | 68204948 | Hypo | cancer_general | — | chr7 | 69352121 | 69352272 | Hypo | cancer_general | AUTS2 |
| chr7 | 69897780 | 69897827 | Hypo | cancer_general | AUTS2 | chr7 | 70990312 | 70990342 | Hypo | cancer_general | — |
| chr7 | 71438424 | 71438454 | Hypo | cancer_general | CALN1 | chr7 | 71603924 | 71604082 | Hypo | cancer_general | — |
| chr7 | 71871203 | 71871245 | Hypo | cancer_general | — | chr7 | 76033151 | 76033289 | Hypo | colorectal | ZP3 |
| chr7 | 77129743 | 77129907 | Hypo | lung | — | chr7 | 77308664 | 77308899 | Hypo | cancer_general | RSBN1L-AS1 |
| chr7 | 77309437 | 77309511 | Hypo | cancer_general | RSBN1L-AS1 | chr7 | 77324362 | 77324593 | Hypo | cancer_general | RSBN1L, RSBN1L-AS1 |
| chr7 | 87105401 | 87105430 | Hypo | tcga | ABCB4 | chr7 | 87706818 | 87706877 | Hypo | cancer_general | ADAM22 |
| chr7 | 87825137 | 87825137 | Hypo | hepatobiliary | SRI | chr7 | 88388631 | 88388660 | Hypo | tcga | ZNF804B |
| chr7 | 90269263 | 90269563 | Hypo | literature, cancer_general | CDK14 | chr7 | 90797539 | 90797568 | Hypo | literature | CDK14 |
| chr7 | 92554253 | 92554452 | Hypo | cancer_general | — | chr7 | 92689705 | 92689818 | Hypo | cancer_general | — |
| chr7 | 93220696 | 93220826 | Hypo | cancer_general | GNGT1 | chr7 | 94138158 | 94138315 | Hypo | cancer_general | CASD1 |
| chr7 | 96627013 | 96627064 | Hypo | cancer_general | DLX6, DLX6-AS1 | chr7 | 96651469 | 96651537 | Hypo | cancer_general | DLX5 |
| chr7 | 97490474 | 97490508 | Hypo | hepatobiliary | ASNS | chr7 | 97580497 | 97580648 | Hypo | cancer_general | MGC72080 |
| chr7 | 97600104 | 97600224 | Hypo | cancer_general | BC122864, MGC72080 | chr7 | 97839654 | 97839684 | Hypo | cancer_general | BHLHA15, TECPR1, LMTK2 |
| chr7 | 97869290 | 97869391 | Hypo | cancer_general | TECPR1 | chr7 | 97869614 | 97869644 | Hypo | cancer_general | TECPR1 |
| chr7 | 98197206 | 98197242 | Hypo | cancer_general | — | chr7 | 98966786 | 98966916 | Hypo | lung | ARPC1B, ARPC1A |
| chr7 | 98969875 | 98969928 | Hypo | cancer_general | ARPC1B, ARPC1A | chr7 | 98971509 | 98971549 | Hypo | cancer_general | ARPC1B, ARPC1A |
| chr7 | 99035152 | 99035191 | Hypo | esophageal | CPSF4, ATP5J2-PTCD1, PTCD1 | chr7 | 99104258 | 99104388 | Hypo | cancer_general | ZKSCAN5, AJ297365, ZNF394 |
| chr7 | 99591579 | 99591762 | Hypo | cancer_general | AZGP1P1 | chr7 | 99642049 | 99642100 | Hypo | cancer_general | ZSCAN21, ZKSCAN1 |
| chr7 | 99751578 | 99751630 | Hypo | colorectal | C7orf43, MIR4658, GAL3ST4, LAMTOR4 | chr7 | 99934913 | 99934943 | Hypo | cancer_general | PMS2P1, PILRB |
| chr7 | 100088183 | 100088312 | Hypo | cancer_general | NYAP1 | chr7 | 100179889 | 100179927 | Hypo | cancer_general | FBXO24, PCOLCE-AS1, LRCH4, ZASP, SAP25 |
| chr7 | 100241592 | 100241697 | Hypo | cancer_general | ACTL6B, TFR2 | chr7 | 100295321 | 100295424 | Hypo | cancer_general | GIGYF1, POP7 |
| chr7 | 100320690 | 100320719 | Hypo | literature | EPO | chr7 | 101241993 | 101242023 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 101475790 | 101475858 | Hypo | cancer_general | CUX1 | chr7 | 101585887 | 101585917 | Hypo | cancer_general | CUX1 |
| chr7 | 101627741 | 101627787 | Hypo | cancer_general | CUX1 | chr7 | 101707502 | 101707532 | Hypo | cancer_general | CUX1 |
| chr7 | 102091406 | 102091534 | Hypo | blood | ALKBH4, ORAI2 | chr7 | 102801710 | 102801804 | Hypo | lung | — |
| chr7 | 105279467 | 105279671 | Hypo | cancer_general | ATXN7L1 | chr7 | 106622834 | 106622961 | Hypo | cancer_general | — |
| chr7 | 106797774 | 106797804 | Hypo | colorectal | PRKAR2B | chr7 | 107483694 | 107483918 | Hypo | colorectal | — |
| chr7 | 111202993 | 111203260 | Hypo | literature, cancer_general | — | chr7 | 116412008 | 116412058 | Hypo | literature | — |
| chr7 | 116415100 | 116415129 | Hypo | literature | — | chr7 | 116417443 | 116417496 | Hypo | literature | — |
| chr7 | 116422067 | 116422132 | Hypo | literature | — | chr7 | 116423399 | 116423488 | Hypo | literature | — |
| chr7 | 121956724 | 121956754 | Hypo | cancer_general | CADPS2, FEZF1-AS1 | chr7 | 123175689 | 123175899 | Hypo | cancer_general | NDUFA5, IQUB |
| chr7 | 125082621 | 125082698 | Hypo | cancer_general | — | chr7 | 127371129 | 127371249 | Hypo | breast | SND1 |
| chr7 | 127615921 | 127615951 | Hypo | ovarian | SND1 | chr7 | 128097059 | 128097089 | Hypo | cancer_general | HILPDA |
| chr7 | 128486036 | 128486138 | Hypo | cancer_general | FLNC | chr7 | 128528749 | 128528779 | Hypo | cancer_general | KCP |
| chr7 | 128529023 | 129529053 | Hypo | cancer_general | KCP | chr7 | 129229456 | 129229631 | Hypo | cancer_general | — |
| chr7 | 129483356 | 129483449 | Hypo | lung | UBE2H, AL832212 | chr7 | 129794593 | 129794721 | Hypo | cancer_general | TMEM209 |
| chr7 | 129800243 | 129800434 | Hypo | breast | TMEM209 | chr7 | 129844226 | 129844493 | Hypo | cancer_general | SSMEM1, TMEM209 |
| chr7 | 131041515 | 131041596 | Hypo | breast | MKLN1 | chr7 | 134918503 | 134918637 | Hypo | breast | STRA8 |
| chr7 | 136969053 | 136969083 | Hypo | cancer_general | SNORD81, PTN | chr7 | 138042221 | 138042288 | Hypo | ovarian | — |
| chr7 | 139878250 | 139878296 | Hypo | cancer_general | LOC100134229, JHDM1D | chr7 | 139939160 | 139939318 | Hypo | cancer_general | — |
| chr7 | 140027008 | 140027079 | Hypo | colorectal | SLC37A3 | chr7 | 140096812 | 140096882 | Hypo | cancer_general | AK131347, RAB19 |
| chr7 | 140097126 | 140097196 | Hypo | cancer_general | AK131347, RAB19 | chr7 | 140180094 | 140180444 | Hypo | ovarian | MKRN1 |
| chr7 | 140218123 | 140218352 | Hypo | tcga | DENND2A | chr7 | 140219405 | 140219435 | Hypo | colorectal | DENND2A |
| chr7 | 140453121 | 140453167 | Hypo | literature | BRAF | chr7 | 140477779 | 140477868 | Hypo | literature | BRAF |
| chr7 | 140481381 | 140481431 | Hypo | literature | BRAF | chr7 | 142785612 | 142785728 | Hypo | cancer_general | — |
| chr7 | 144712934 | 144713064 | Hypo | cancer_general | — | chr7 | 148224541 | 148224686 | Hypo | cancer_general | — |
| chr7 | 148508712 | 148508741 | Hypo | literature | EZH2 | chr7 | 148640171 | 148640250 | Hypo | cancer_general | AK131347, RAB19 |
| chr7 | 148846138 | 148846180 | Hypo | cancer_general | ZNF398 | chr7 | 148846434 | 148846644 | Hypo | cancer_general | ZNF282, ZNF398 |
| chr7 | 148851143 | 148851234 | Hypo | breast | ZNF398 | chr7 | 148883821 | 148883973 | Hypo | cancer_general | ZNF398 |
| chr7 | 149109648 | 149109785 | Hypo | cancer_general | TRNA_Cys ZNF775, ZNF775, RNU6-34P, REPIN1 | chr7 | 150049604 | 150049718 | Hypo | cancer_general | ZNF775, REPIN1, RNU6-34P |
| chr7 | 150069098 | 150069346 | Hypo | colorectal | ZNF775, REPIN1, RNU6-34P | chr7 | 150069679 | 150069820 | Hypo | colorectal | ZNF775, REPIN1, RNU6-34P |
| chr7 | 150070021 | 150070058 | Hypo | colorectal | | chr7 | 150081236 | 150081308 | Hypo | cancer_general | ZNF775 |
| chr7 | 150753942 | 150753981 | Hypo | cancer_general | SLC4A2, CDK5, ASIC3 | chr7 | 150870816 | 150870889 | Hypo | cancer_general | ASB10, GBX1 |
| chr7 | 151001356 | 151001435 | Hypo | cancer_general | — | chr7 | 151188034 | 151188063 | Hypo | literature | RHEB |
| chr7 | 151298870 | 151299029 | Hypo | breast | PRKAG2 | chr7 | 151423571 | 151423639 | Hypo | lung | PRKAG2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 151591667 | 151591705 | Hypo | cancer_general | — | chr7 | 152913656 | 152913826 | Hypo | cancer_general | — |
| chr7 | 153633796 | 153633942 | Hypo | cancer_general | DPP6 | chr7 | 154561150 | 154561189 | Hypo | cancer_general | DPP6 |
| chr7 | 154708275 | 154708338 | Hypo | cancer_general | — | chr7 | 154926351 | 154926397 | Hypo | cancer_general | — |
| chr7 | 155302881 | 155302917 | Hypo | cancer_general | CNPY1 | chr7 | 155363304 | 155363417 | Hypo | cancer_general | — |
| chr7 | 155580846 | 155580876 | Hypo | cancer_general | RBM33 | chr7 | 155581330 | 155581553 | Hypo | cancer_general | RBM33 |
| chr7 | 155581765 | 155581980 | Hypo | cancer_general | RBM33 | chr7 | 155582277 | 155582340 | Hypo | cancer_general | RBM33 |
| chr7 | 155877196 | 155877283 | Hypo | cancer_general | — | chr7 | 156259192 | 156259221 | Hypo | literature | — |
| chr7 | 156707963 | 156708093 | Hypo | cancer_general | — | chr7 | 156744619 | 156744713 | Hypo | cancer_general | NOM1 |
| chr7 | 156779336 | 156779366 | Hypo | cancer_general | MNX1 | chr7 | 156832223 | 156832402 | Hypo | cancer_general | — |
| chr7 | 156832848 | 156833162 | Hypo | cancer_general | — | chr7 | 156880531 | 156880561 | Hypo | cancer_general | — |
| chr7 | 157085373 | 157085487 | Hypo | cancer_general | — | chr7 | 157085963 | 157086082 | Hypo | cancer_general | — |
| chr7 | 157262815 | 157263018 | Hypo | cancer_general | — | chr7 | 157263294 | 157263471 | Hypo | cancer_general | — |
| chr7 | 157335172 | 157335202 | Hypo | cancer_general | PTPRN2 | chr7 | 157584178 | 157584208 | Hypo | cancer_general | — |
| chr7 | 157588586 | 157588791 | Hypo | cancer_general | — | chr7 | 157606706 | 157606736 | Hypo | cancer_general | — |
| chr7 | 157690056 | 157690086 | Hypo | cancer_general | — | chr7 | 158059762 | 158059794 | Hypo | cancer_general | — |
| chr7 | 158065832 | 158065970 | Hypo | cancer_general | — | chr7 | 158198597 | 158198648 | Hypo | hepatobiliary | — |
| chr7 | 158298861 | 158299036 | Hypo | hepatobiliary | — | chr7 | 158741193 | 158741267 | Hypo | breast | WDR60 |
| chr3 | 158799762 | 158799791 | Hypo | literature | LINC00689 | chr3 | 3167720 | 3167750 | Hypo | cancer_general | TRNT1 |
| chr3 | 5165885 | 5165915 | Hypo | cancer_general | ARL8B | chr3 | 9924238 | 9924534 | Hypo | cancer_general | JAGN1, CIDEC |
| chr3 | 9941469 | 9941669 | Hypo | cancer_general | IL17RE, JAGN1 | chr3 | 10027432 | 10027548 | Hypo | cancer_general | AX747493, AK125558, EMC3 |
| chr3 | 10182839 | 10183212 | Hypo | cancer_general, literature | VHL | chr3 | 10183753 | 10183782 | Hypo | literature | VHL |
| chr3 | 10184304 | 10184333 | Hypo | literature | VHL | chr3 | 10191477 | 10191620 | Hypo | literature | VHL, RAF1, MKRN2 |
| chr3 | 12586149 | 12586179 | Hypo | cancer_general | C3orf83 | chr3 | 12632309 | 12632401 | Hypo | literature | |
| chr3 | 12645678 | 12645713 | Hypo | literature | RAF1 | chr3 | 12673006 | 12673036 | Hypo | lung | — |
| chr3 | 12870826 | 12870856 | Hypo | cancer_general | RPL32, CAND2 | chr3 | 12926053 | 12926102 | Hypo | blood | — |
| chr3 | 12977067 | 12977144 | Hypo | breast | IQSEC1 | chr3 | 13171814 | 13171844 | Hypo | esophageal | — |
| chr3 | 13679172 | 13679349 | Hypo | cancer_general | — | chr3 | 15123848 | 15123992 | Hypo | lung, cancer_general | ZFYVE20 |
| chr3 | 15780510 | 15780638 | Hypo | esophageal | BC041363, ANKRD28 | chr3 | 17001303 | 17001333 | Hypo | cancer_general | — |
| chr3 | 17735273 | 17735340 | Hypo | cancer_general | TRNA_Pseudo RPL15, NKIRAS1 | chr3 | 20070714 | 20070903 | Hypo | ovarian | — |
| chr3 | 23964882 | 23965019 | Hypo | ovarian | | chr3 | 31494108 | 31494138 | Hypo | colorectal | — |
| chr3 | 32708277 | 32708405 | Hypo | cancer_general | — | chr3 | 36984378 | 36984425 | Hypo | colorectal | TRANK1 |
| chr3 | 37276385 | 37276490 | Hypo | cancer_general | GOLGA4 | chr3 | 38030618 | 38030782 | Hypo | pancreas | VILL |
| chr3 | 38032331 | 38032361 | Hypo | cancer_general | VILL | chr3 | 38182244 | 38182306 | Hypo | literature | MYD88, ACAA1 |
| chr3 | 38182626 | 38182655 | Hypo | literature | MYD88, ACAA1 | chr3 | 38208158 | 38208226 | Hypo | cancer_general | OXSR1 |
| chr3 | 40202174 | 40202255 | Hypo | cancer_general | MYRIP | chr3 | 41266086 | 41266151 | Hypo | literature | AK095242, AK311005, CTNNB1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 42222730 | 42222847 | Hypo | cancer_general | TRAK1 | chr3 | 42329346 | 42329511 | Hypo | cancer_general | — |
| chr3 | 42640855 | 42640964 | Hypo | cancer_general | NKTR, SS18L2 | chr3 | 42852329 | 42852359 | Hypo | ovarian | CCBP2, HIGD1A |
| chr3 | 43735604 | 43735634 | Hypo | cancer_general | ABHD5 | chr3 | 47144864 | 47144893 | Hypo | literature | — |
| chr3 | 47352704 | 47352734 | Hypo | ovarian | KLHL18 | chr3 | 47521062 | 47521178 | Hypo | cancer_general | — |
| chr3 | 47555760 | 47555790 | Hypo | cancer_general | ELP6 | chr3 | 47830060 | 47830148 | Hypo | cancer_general | CDC25A |
| chr3 | 47831601 | 47831819 | Hypo | cancer_general | — | chr3 | 48227765 | 48227870 | Hypo | cancer_general | — |
| chr3 | 48236476 | 48236724 | Hypo | cancer_general | MIR4443, CDC25A | chr3 | 48698251 | 48698431 | Hypo | ovarian | — |
| chr3 | 48978413 | 48978479 | Hypo | cancer_general | ARIH2 | chr3 | 49142883 | 49142913 | Hypo | cancer_general | QARS, USP19 |
| chr3 | 49196747 | 49196831 | Hypo | ovarian | CCDC71, LAMB2P1 | chr3 | 49405953 | 49405982 | Hypo | literature | RHOA |
| chr3 | 49412883 | 49412987 | Hypo | literature | RHOA | chr3 | 49939931 | 49940398 | Hypo | cancer_general | MON1A, MST1R |
| chr3 | 50072827 | 50072925 | Hypo | cancer_general | RBM6 | chr3 | 50395506 | 50395536 | Hypo | cancer_general | Mir 324, CACNA2D2, TMEM115, CYB56ID2, NPRL2 |
| chr3 | 50575616 | 50575658 | Hypo | cancer_general | — | chr3 | 50968445 | 50968511 | Hypo | cancer_general | DOCK3 |
| chr3 | 52352194 | 52352326 | Hypo | cancer_general | DNAH1 | chr3 | 52442062 | 52442091 | Hypo | literature | PHF7, BAP1, DNAH1 |
| chr3 | 52552556 | 52552661 | Hypo | cancer_general | STAB1, NT5DC2 | chr3 | 52553469 | 52553499 | Hypo | cancer_general | STAB1, NT5DC2 |
| chr3 | 53032733 | 53033524 | Hypo | cancer_general | — | chr3 | 53253306 | 53253599 | Hypo | cancer_general | TKT |
| chr3 | 53382392 | 53382565 | Hypo | cancer_general | DCP1A | chr3 | 53480528 | 53480683 | Hypo | cancer_general | — |
| chr3 | 54583435 | 54583465 | Hypo | hepatobiliary | — | chr3 | 55603443 | 55603632 | Hypo | cancer_general | ERC2 |
| chr3 | 57437452 | 57437482 | Hypo | cancer_general | BC041347 | chr3 | 57529094 | 57529218 | Hypo | breast | DNAH12 |
| chr3 | 58153446 | 58153608 | Hypo | ovarian | — | chr3 | 63719169 | 63719303 | Hypo | cancer_general | — |
| chr3 | 66053446 | 66053613 | Hypo | lung | MITF | chr3 | 69740944 | 69740990 | Hypo | cancer_general | — |
| chr3 | 69937703 | 69937848 | Hypo | cancer_general | PPP4R2 | chr3 | 70661011 | 70661079 | Hypo | hepatobiliary | — |
| chr3 | 73045340 | 73045583 | Hypo | cancer_general | ARL13B | chr3 | 88247941 | 88248049 | Hypo | cancer_general | CPOX |
| chr3 | 93698033 | 93698063 | Hypo | cancer_general | DCBLD2 | chr3 | 98313191 | 98313253 | Hypo | cancer_general | TMEM45A |
| chr3 | 98618182 | 98618376 | Hypo | colorectal | SENP7 | chr3 | 100228688 | 100228768 | Hypo | cancer_general | SENP7, FAM172BP |
| chr3 | 101094160 | 101094190 | Hypo | cancer_general | — | chr3 | 101230678 | 101231070 | Hypo | cancer_general | — |
| chr3 | 101331792 | 101331861 | Hypo | head_neck | ZBTB11, RPL24, ZBTB11-AS1 | chr3 | 101354294 | 101354442 | Hypo | cancer_general | RPL24, ZBTB11-AS1 |
| chr3 | 101397240 | 101397358 | Hypo | cancer_general | RPL24 | chr3 | 101406823 | 101407190 | Hypo | cancer_general | — |
| chr3 | 101411545 | 101411666 | Hypo | lung | — | chr3 | 101645019 | 101645181 | Hypo | cancer_general | — |
| chr3 | 105015466 | 105015519 | Hypo | cancer_general | — | chr3 | 105684885 | 105684987 | Hypo | breast | BTLA |
| chr3 | 106936157 | 106936336 | Hypo | cancer_general | LINC00882 | chr3 | 112185933 | 112185975 | Hypo | hepatobiliary | DRD3 |
| chr3 | 113557333 | 113557363 | Hypo | cancer_general | GRAMD1C | chr3 | 113847911 | 113847941 | Hypo | cancer_general | LSAMP |
| chr3 | 115502232 | 115502390 | Hypo | cancer_general | — | chr3 | 115512319 | 115512448 | Hypo | pancreas | POLQ |
| chr3 | 120004468 | 120004497 | Hypo | tcga | — | chr3 | 121215241 | 121215271 | Hypo | head_neck | ILDR1 |
| chr3 | 121657197 | 121657515 | Hypo | cancer_general | SLC15A2 | chr3 | 121741545 | 121741598 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 122162036 | 122162117 | Hypo | cancer_general | KPNA1 | chr3 | 122162890 | 122163054 | Hypo | cancer_general | KPNA1 |
| chr3 | 122234242 | 122234538 | Hypo | cancer_general | KPNA1 | chr3 | 122573688 | 122573826 | Hypo | cancer_general | DIRC2 |
| chr3 | 122702288 | 122702451 | Hypo | cancer_general | SEMA5B | chr3 | 124410075 | 124410157 | Hypo | head_neck | — |
| chr3 | 125417341 | 125417424 | Hypo | cancer_general | TRNA_Glu | chr3 | 126157586 | 126157663 | Hypo | breast | UNQ2790, ZXDC, CCDC37 |
| chr3 | 126261929 | 126262000 | Hypo | ovarian | C3orf22, CHST13 | chr3 | 127534814 | 127534897 | Hypo | cancer_general | MGLL |
| chr3 | 128056383 | 128056497 | Hypo | cancer_general | EEFSEC | chr3 | 128384991 | 128385132 | Hypo | cancer_general | — |
| chr3 | 128599405 | 128599477 | Hypo | cancer_general | LOC653712, ACAD9 | chr3 | 128786496 | 128786526 | Hypo | colorectal | GP9 |
| chr3 | 129008841 | 129009004 | Hypo | head_neck | C3orf37 | chr3 | 129047978 | 129048008 | Hypo | cancer_general | H1FX-AS1 |
| chr3 | 129372419 | 129372546 | Hypo | hepatobiliary | TMCC1 | chr3 | 130502167 | 130502197 | Hypo | cancer_general | — |
| chr3 | 130519901 | 130520077 | Hypo | cancer_general | — | chr3 | 133217784 | 133217999 | Hypo | cancer_general | — |
| chr3 | 133970474 | 133970491 | Hypo | cancer_general | RYK | chr3 | 136016942 | 136016942 | Hypo | head_neck | PCCB |
| chr3 | 136582883 | 136582951 | Hypo | cancer_general | NCK1, SLC35G2 | chr3 | 137490806 | 137490860 | Hypo | cancer_general | SOX14, BC038725 |
| chr3 | 137892691 | 137892721 | Hypo | cancer_general | DBR1 | chr3 | 137894374 | 137894415 | Hypo | cancer_general | DBR1 |
| chr3 | 138058859 | 138058897 | Hypo | breast | MRAS | chr3 | 138318827 | 138318918 | Hypo | breast | FAIM, CEP70 |
| chr3 | 138374229 | 138374258 | Hypo | literature | PIK3CB | chr3 | 138635369 | 138635507 | Hypo | cancer_general | ZBTB38 |
| chr3 | 138662266 | 138662296 | Hypo | cancer_general | FOXL2, C3orf72, AK304483, AK128202 | chr3 | 141174349 | 141174606 | Hypo | cancer_general | — |
| chr3 | 141363466 | 141363496 | Hypo | breast | — | chr3 | 141481651 | 141482073 | Hypo | cancer_general | — |
| chr3 | 141657032 | 141657079 | Hypo | cancer_general | TFDP2, AX748420 | chr3 | 141832939 | 141833015 | Hypo | head_neck | TFDP2 |
| chr3 | 141835935 | 141836077 | Hypo | cancer_general | TFDP2 | chr3 | 142159804 | 142159841 | Hypo | breast | XRN1, ATR |
| chr3 | 142537638 | 142537779 | Hypo | breast | PCOLCE2 | chr3 | 142718283 | 142718358 | Hypo | cancer_general | LOC100289361, U2SURP |
| chr3 | 142791151 | 142791255 | Hypo | colorectal | — | chr3 | 142896156 | 142896214 | Hypo | cancer_general | — |
| chr3 | 143280343 | 143280373 | Hypo | cancer_general | — | chr3 | 143614462 | 143614504 | Hypo | cancer_general | PLSCR2 |
| chr3 | 145735852 | 145735882 | Hypo | ovarian | — | chr3 | 146187946 | 146187978 | Hypo | cancer_general | HLTF-AS1, HLTF |
| chr3 | 148523213 | 148523297 | Hypo | cancer_general | — | chr3 | 148803120 | 148803276 | Hypo | cancer_general | — |
| chr3 | 150237792 | 150237822 | Hypo | cancer_general | — | chr3 | 152107022 | 152107052 | Hypo | pancreas | RAP2B |
| chr3 | 152707390 | 152707460 | Hypo | cancer_general | — | chr3 | 152877666 | 152877696 | Hypo | pancreas | — |
| chr3 | 155456372 | 155456630 | Hypo | pancreas, cancer_general | — | chr3 | 155461030 | 155461195 | Hypo | cancer_general | — |
| chr3 | 156007772 | 156007801 | Hypo | literature | KCNAB1 | chr3 | 158319235 | 158319359 | Hypo | hepatobiliary | MLF1 |
| chr3 | 169539898 | 169540679 | Hypo | cancer_general | LRRIQ4, LRRC34 | chr3 | 169541070 | 169541102 | Hypo | cancer_general | LRRIQ4 |
| chr3 | 170602030 | 170602133 | Hypo | cancer_general | EIF5A2 | chr3 | 171193088 | 171193311 | Hypo | cancer_general | — |
| chr3 | 171529811 | 171529958 | Hypo | cancer_general | — | chr3 | 172342101 | 172342147 | Hypo | cancer_general | NCEH1 |
| chr3 | 172355895 | 172356038 | Hypo | cancer_general | NCEH1 | chr3 | 172383550 | 172383600 | Hypo | cancer_general | NCEH1 |
| chr3 | 172425382 | 172425717 | Hypo | cancer_general | U6, NCEH1 | chr3 | 172469925 | 172470036 | Hypo | cancer_general | ECT2 |

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 173162817 | 173162847 | Hypo | cancer_general | NLGN1 | chr3 | 176710106 | 176710241 | Hypo | ovarian | PIK3CA, BC032034 |
| chr3 | 176872357 | 176872443 | Hypo | cancer_general | TBL1XR1 | chr3 | 178861259 | 178861447 | Hypo | cancer_general | |
| chr3 | 178916711 | 178916959 | Hypo | literature | PIK3CA | chr3 | 178921537 | 178921568 | Hypo | literature | PIK3CA |
| chr3 | 178927966 | 178928094 | Hypo | literature | PIK3CA | chr3 | 178936059 | 178936111 | Hypo | literature | PIK3CA |
| chr3 | 178952004 | 178952105 | Hypo | literature | KCNMB3, PIK3CA | chr3 | 179367874 | 179367920 | Hypo | cancer_general | USP13 |
| chr3 | 181444108 | 181444236 | Hypo | cancer_general | | chr3 | 182815811 | 182816027 | Hypo | cancer_general | MCCC1 |
| chr3 | 182895956 | 182896144 | Hypo | literature | MCF2L2 | chr3 | 182911545 | 182911574 | Hypo | literature | MCF2L2 |
| chr3 | 183109854 | 183109883 | Hypo | literature | | chr3 | 183183523 | 183183659 | Hypo | cancer_general | LINC00888 |
| chr3 | 183208370 | 183208469 | Hypo | cancer_general | KLHL6 | chr3 | 183217676 | 183217706 | Hypo | ovarian | KLHL6 |
| chr3 | 183647996 | 183648026 | Hypo | cancer_general | ABCC5 | chr3 | 183728793 | 183728952 | Hypo | breast | ABCC5-AS1, ABCC5 |
| chr3 | 183870824 | 183870858 | Hypo | cancer_general | DVL3 | chr3 | 183872490 | 183872524 | Hypo | cancer_general | DVL3 |
| chr3 | 183965599 | 183965907 | Hypo | cancer_general | ECE2, ALG3, MIR1224, VWA5B2 | chr3 | 184018038 | 184018136 | Hypo | cancer_general | PSMD2, ECE2 |
| chr3 | 184031686 | 184031746 | Hypo | cancer_general | PSMD2, EIF4G1 | chr3 | 184057254 | 184057557 | Hypo | lung, cancer_general | FAM131A, CLCN2 |
| chr3 | 185001696 | 185001919 | Hypo | cancer_general | MAP3K13 | chr3 | 185271296 | 185271764 | Hypo | cancer_general | LIPH |
| chr3 | 185275856 | 185275886 | Hypo | cancer_general | LIPH | chr3 | 185303247 | 185303277 | Hypo | cancer_general | SENP2 |
| chr3 | 185363074 | 185363261 | Hypo | cancer_general | IGF2BP2 | chr3 | 185629516 | 185629546 | Hypo | cancer_general | TRA2B |
| chr3 | 185643324 | 185643405 | Hypo | cancer_general | TRA2B | chr3 | 185658513 | 185658543 | Hypo | cancer_general | TRA2B |
| chr3 | 185668237 | 185668311 | Hypo | cancer_general | LOC344887 | chr3 | 186287130 | 186287270 | Hypo | cancer_general | DNAJB11, TBCCD1 |
| chr3 | 186914705 | 186914734 | Hypo | literature | RTP1 | chr3 | 193312128 | 193312347 | Hypo | cancer_general | OPA1 |
| chr3 | 193419702 | 193419732 | Hypo | ovarian | | chr3 | 193548637 | 193548835 | Hypo | cancer_general | |
| chr3 | 194048751 | 194048919 | Hypo | cancer_general | | chr3 | 194120812 | 194120841 | Hypo | literature | ATP13A3, GP5 |
| chr3 | 194981816 | 194981913 | Hypo | cancer_general | | chr3 | 195095450 | 195095543 | Hypo | ovarian | ACAP2 |
| chr3 | 195184022 | 195184140 | Hypo | colorectal | | chr3 | 195409773 | 195409813 | Hypo | ovarian | SDHAP2 |
| chr3 | 195536733 | 195536848 | Hypo | cancer_general | MUC4 | chr3 | 195538217 | 195538353 | Hypo | cancer_general | MUC4 |
| chr3 | 195587032 | 195587118 | Hypo | cancer_general | TNK2 | chr3 | 195601239 | 195601312 | Hypo | pancreas | TNK2 |
| chr3 | 195602330 | 195602576 | Hypo | pancreas | TNK2 | chr3 | 195639755 | 195639785 | Hypo | head_neck | AK127609, TNK2 |
| chr3 | 195648794 | 195649004 | Hypo | cancer_general | TM4SF19, TM4SF19-TCTEX1D2 | chr3 | 195834581 | 195834611 | Hypo | cancer_general | TM4SF19, TM4SF19-TCTEX1D2 |
| chr3 | 196046702 | 196046830 | Hypo | head_neck | TM4SF19, TM4SF19-TCTEX1D2, AK124973, TCTEX1D2 | chr3 | 196065342 | 196065583 | Hypo | literature | |
| chr3 | 196069743 | 196070340 | Hypo | cancer_general | TM4SF19, TM4SF19-TCTEX1D2 | chr3 | 196263303 | 196263471 | Hypo | cancer_general | |
| chr3 | 196344683 | 196344796 | Hypo | esophageal | LRRC33 | chr3 | 196387295 | 196387415 | Hypo | cancer_general | LRRC33 |
| chr3 | 196387628 | 196387665 | Hypo | cancer_general | | chr3 | 196388383 | 196388581 | Hypo | cancer_general | LRRC33 |
| chr3 | 196433946 | 196434104 | Hypo | head_neck | PIGX, CEP19, U6 | chr3 | 196440510 | 196440676 | Hypo | head_neck | PIGX, U6, CEP19 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 196667872 | 196668080 | Hypo | cancer_general | NCBP2-AS2, PIGZ, NCBP2, SENP5 | chr3 | 196728418 | 196728448 | Hypo | head_neck | MFI2, MFI2-AS1 |
| chr3 | 196731155 | 196731313 | Hypo | cancer_general | MFI2-AS1, MFI2 | chr3 | 197209019 | 197209048 | Hypo | literature | — |
| chr3 | 197247047 | 197247110 | Hypo | pancreas | BDH1 | chr3 | 197278926 | 197278988 | Hypo | pancreas | BDH1 |
| chr3 | 197313997 | 197314107 | Hypo | cancer_general | LOC220729 | chr3 | 197326860 | 197327042 | Hypo | cancer_general | LOC220729 |
| chr3 | 197330060 | 197330147 | Hypo | cancer_general | LOC220729 | chr3 | 197466364 | 197466540 | Hypo | cancer_general | FYTTD1, KIAA0226 |
| chr3 | 197616707 | 197616861 | Hypo | cancer_general | IQCG, LRCH3 | chr3 | 197685788 | 197686085 | Hypo | literature, cancer_general | LMLN, RPL35A, IQCG |
| chr3 | 197686495 | 197686524 | Hypo | literature | LMLN, RPL35A, IQCG | chr1 | 715373 | 715447 | Hypo | cancer_general | LOC100288069 |
| chr1 | 898654 | 898690 | Hypo | head_neck | PLEKHN1, KLHL17, NOC2L | chr1 | 913532 | 913955 | Hypo | cancer_general | PLEKHN1, C1orf170 |
| chr1 | 1047531 | 1047647 | Hypo | breast | C1orf159 | chr1 | 1080583 | 1080824 | Hypo | cancer_general | LOC254099 SDF4, |
| chr1 | 1095420 | 1095459 | Hypo | colorectal | MIR429, JA715143, MIR200B, MIR200A, JA715134 | chr1 | 1146734 | 1146818 | Hypo | cancer_general | TNFRSF4, TNFRSF18 |
| chr1 | 1218737 | 1218820 | Hypo | cancer_general | UBE2J2, ACAP3, SCNN1D | chr1 | 1223512 | 1223652 | Hypo | cancer_general | ACAP3, SCNN1D |
| chr1 | 1235813 | 1236078 | Hypo | cancer_general | PUSL1, ACAP3, SCNN1D | chr1 | 1253330 | 1253386 | Hypo | lung, cancer_general | CPSF3L, GLTPD1, PUSL1, ACAP3 |
| chr1 | 1267014 | 1267151 | Hypo | cancer_general | DVL1, TAS1R3, GLTPD1, CPSF3L | chr1 | 1267462 | 1267699 | Hypo | cancer_general | CPSF3L, DVL1, TAS1R3, GLTPD1 |
| chr1 | 1267906 | 1268158 | Hypo | cancer_general | DVL1, TAS1R3, GLTPD1 | chr1 | 1281214 | 1281244 | Hypo | pancreas | MXRA8, DVL1 |
| chr1 | 1341668 | 1341743 | Hypo | cancer_general | MRPL20, LOC148413, CCNL2 | chr1 | 1436043 | 1436211 | Hypo | cancer_general | ATAD3B |
| chr1 | 1473125 | 1473207 | Hypo | head_neck | AX747755, ATAD3A, SSU72, TMEM240 | chr1 | 1483186 | 1483363 | Hypo | head_neck | TMEM240, SSU72 |
| chr1 | 1547129 | 1547348 | Hypo | lung | MIB2, AK094692 | chr1 | 1563193 | 1563223 | Hypo | cancer_general | CDK11B, MIB2, MMP23B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 1805049 | 1805089 | Hypo | breast | GNB1 | chr1 | 1856436 | 1856466 | Hypo | head_neck | C1orf222, TMEM52, CALML6 |
| chr1 | 1857847 | 1857909 | Hypo | cancer_general | C1orf222, TMEM52, CALML6 | chr1 | 1874744 | 1874787 | Hypo | cancer_general | KIAA1751 |
| chr1 | 1910415 | 1910445 | Hypo | head_neck | KIAA1751 | chr1 | 1923457 | 1923521 | Hypo | cancer_general | KIAA1751 |
| chr1 | 1974848 | 1974925 | Hypo | cancer_general | PRKCZ | chr1 | 2066490 | 2066679 | Hypo | cancer_general | PRKCZ |
| chr1 | 2125216 | 2125483 | Hypo | cancer_general | C1orf86, BC018779 | chr1 | 2263169 | 2263263 | Hypo | cancer_general | MORN1 |
| chr1 | 2267552 | 2267690 | Hypo | cancer_general | MORN1 | chr1 | 2304327 | 2304389 | Hypo | cancer_general | MORN1 |
| chr1 | 2307925 | 2307955 | Hypo | cancer_general | MORN1 | chr1 | 2308376 | 2308636 | Hypo | cancer_general | MORN1 |
| chr1 | 2309868 | 2309953 | Hypo | ovarian | MORN1 | chr1 | 2331363 | 2331437 | Hypo | ovarian | PEX10, RER1, MORN1 |
| chr1 | 2336397 | 2336427 | Hypo | breast | PEX10, RER1 | chr1 | 2397001 | 2397031 | Hypo | cancer_general | — |
| chr1 | 2428331 | 2428385 | Hypo | cancer_general | PLCH2 | chr1 | 2507063 | 2507183 | Hypo | cancer_general | — |
| chr1 | 2514330 | 2514376 | Hypo | ovarian | FAM213B, MMEL1 | chr1 | 2521024 | 2521063 | Hypo | breast | MMEL1, FAM213B |
| chr1 | 2830155 | 2830185 | Hypo | cancer_general | — | chr1 | 2866038 | 2866068 | Hypo | cancer_general | — |
| chr1 | 3102653 | 3102779 | Hypo | cancer_general | — | chr1 | 3158823 | 3158962 | Hypo | cancer_general | — |
| chr1 | 3182883 | 3182917 | Hypo | ovarian | — | chr1 | 3183415 | 3183455 | Hypo | cancer_general | — |
| chr1 | 3322090 | 3322170 | Hypo | literature, cancer_general | TP73 | chr1 | 3601850 | 3601946 | Hypo | colorectal | TP73 |
| chr1 | 3607081 | 3607236 | Hypo | cancer_general | — | chr1 | 3659950 | 3659716 | Hypo | cancer_general | TP73-AS1, TP73, CCDC27 |
| chr1 | 3664461 | 3664741 | Hypo | cancer_general | CCDC27, TP73-AS1 | chr1 | 3683686 | 3683818 | Hypo | cancer_general | SMIM1, CCDC27 |
| chr1 | 3700384 | 3700414 | Hypo | ovarian | LRRC47, SMIM1 | chr1 | 3733551 | 3733581 | Hypo | esophageal | CEP104 |
| chr1 | 4111061 | 4111231 | Hypo | cancer_general | — | chr1 | 4401433 | 4401463 | Hypo | cancer_general | — |
| chr1 | 5919973 | 5920071 | Hypo | hepatobiliary | MIR4689, NPHP4 | chr1 | 5920650 | 5920710 | Hypo | hepatobiliary | MIR4689, NPHP4 |
| chr1 | 5924296 | 5924431 | Hypo | hepatobiliary | NPHP4, MIR4689 | chr1 | 5924851 | 5924984 | Hypo | hepatobiliary | NPHP4, MIR4689 |
| chr1 | 5926596 | 5926645 | Hypo | hepatobiliary | NPHP4, MIR4689 | chr1 | 5933086 | 5933144 | Hypo | hepatobiliary | NPHP4 |
| chr1 | 5934925 | 5935061 | Hypo | hepatobiliary | NPHP4 | chr1 | 5940517 | 5940547 | Hypo | hepatobiliary | NPHP4 |
| chr1 | 5940945 | 5941132 | Hypo | hepatobiliary | NPHP4 | chr1 | 5944299 | 5944449 | Hypo | hepatobiliary | NPHP4 |
| chr1 | 5944962 | 5945001 | Hypo | hepatobiliary | NPHP4 | chr1 | 5945348 | 5945435 | Hypo | hepatobiliary | NPHP4 |
| chr1 | 5947258 | 5947288 | Hypo | hepatobiliary | NPHP4 | chr1 | 5949491 | 5949575 | Hypo | hepatobiliary | NPHP4 |
| chr1 | 5950965 | 5951039 | Hypo | hepatobiliary | NPHP4 | chr1 | 5957473 | 5957503 | Hypo | hepatobiliary | NPHP4 |
| chr1 | 5967237 | 5967267 | Hypo | hepatobiliary | NPHP4 | chr1 | 5969001 | 5969283 | Hypo | hepatobiliary | NPHP4 |
| chr1 | 5972104 | 5972134 | Hypo | hepatobiliary | NPHP4 | chr1 | 5972878 | 5972922 | Hypo | hepatobiliary | NPHP4 |
| chr1 | 6021621 | 6021651 | Hypo | hepatobiliary | — | chr1 | 6025872 | 6025950 | Hypo | hepatobiliary | — |
| chr1 | 6036766 | 6036796 | Hypo | hepatobiliary | KCNAB2 | chr1 | 6056157 | 6056201 | Hypo | hepatobiliary | KCNAB2 |
| chr1 | 6056506 | 6056651 | Hypo | hepatobiliary | CHD5, KCNAB2 | chr1 | 6059910 | 6059974 | Hypo | hepatobiliary | KCNAB2 |
| chr1 | 6166353 | 6166469 | Hypo | cancer_general | KCNAB2 | chr1 | 6171763 | 6171810 | Hypo | cancer_general | CHD5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 6186511 | 6186546 | Hypo | pancreas | CHD5 | chr1 | 6280243 | 6280273 | Hypo | cancer_general | ICMT, RNF207 |
| chr1 | 6284828 | 6284858 | Hypo | pancreas | ICMT, RNF207 | chr1 | 6360593 | 6360634 | Hypo | cancer_general | ACOT7 |
| chr1 | 6410456 | 6410486 | Hypo | head_neck | ACOT7 | chr1 | 6446131 | 6446308 | Hypo | cancer_general | ACOT7 |
| chr1 | 6672227 | 6672351 | Hypo | cancer_general | PHF13, KLHL21 | chr1 | 6713914 | 6714041 | Hypo | ovarian | DNAJC11 |
| chr1 | 6714348 | 6714378 | Hypo | ovarian | DNAJC11 | chr1 | 6776304 | 6776388 | Hypo | cancer_general | — |
| chr1 | 7973843 | 7973948 | Hypo | cancer_general | TNFRSF9 | chr1 | 8549986 | 8550078 | Hypo | lung, cancer_general | RERE |
| chr1 | 9402465 | 9402616 | Hypo | breast | SPSB1 | chr1 | 9601954 | 9601984 | Hypo | hepatobiliary | SLC25A33 CLSTN1, PIK3CD |
| chr1 | 9722138 | 9722215 | Hypo | esophageal | C1orf200, PIK3CD | chr1 | 9795995 | 9796196 | Hypo | ovarian | |
| chr1 | 9865110 | 9865140 | Hypo | cancer_general | CLSTN1 | chr1 | 9867157 | 9867316 | Hypo | lung | CLSTN1 |
| chr1 | 10091888 | 10092060 | Hypo | cancer_general | UBE4B | chr1 | 10095469 | 10095845 | Hypo | cancer_general | UBE4B |
| chr1 | 10123736 | 10123928 | Hypo | head_neck | UBE4B | chr1 | 10166521 | 10166551 | Hypo | head_neck | UBE4B |
| chr1 | 10491694 | 10491724 | Hypo | cancer_general | APITD1-CORT1, APITD1 | chr1 | 11169346 | 11169375 | Hypo | literature | MTOR, EXOSC10 |
| chr1 | 11174404 | 11174433 | Hypo | literature | MTOR | chr1 | 11181358 | 11181432 | Hypo | literature | MTOR |
| chr1 | 11182142 | 11182171 | Hypo | literature | MTOR | chr1 | 11188149 | 11188178 | Hypo | literature | MTOR |
| chr1 | 11210182 | 11210211 | Hypo | literature | MTOR-AS1, MTOR | chr1 | 11217215 | 11217337 | Hypo | literature | MTOR-AS1, MTOR |
| chr1 | 11591719 | 11591826 | Hypo | cancer_general | PTCHD2 | chr1 | 11886250 | 11886280 | Hypo | head_neck | CLCN6 |
| chr1 | 11936748 | 11936778 | Hypo | cancer_general | — | chr1 | 12041374 | 12041525 | Hypo | cancer_general | MFN2, PLOD1 |
| chr1 | 12251443 | 12251958 | Hypo | lung, cancer_general | MIR4632, TNFRSF1B | chr1 | 12460299 | 12460356 | Hypo | ovarian | VPS13D |
| chr1 | 13984525 | 13984742 | Hypo | head_neck | — | chr1 | 14032304 | 14032347 | Hypo | hepatobiliary | PRDM2 |
| chr1 | 14097878 | 14098015 | Hypo | esophageal | PRDM2 | chr1 | 14128478 | 14128588 | Hypo | cancer_general | — |
| chr1 | 14149749 | 14149867 | Hypo | head_neck | AK124197 | chr1 | 14730425 | 14730472 | Hypo | cancer_general | — |
| chr1 | 14746206 | 14746245 | Hypo | hepatobiliary | — | chr1 | 15128565 | 15128595 | Hypo | hepatobiliary | KAZN |
| chr1 | 16474413 | 16474576 | Hypo | pancreas | EPHA2 | chr1 | 16475031 | 16475207 | Hypo | pancreas | EPHA2 |
| chr1 | 17757538 | 17757570 | Hypo | colorectal | RCC2 | chr1 | 17787472 | 17787502 | Hypo | cancer_general | TMCO4 |
| chr1 | 19980747 | 19980858 | Hypo | cancer_general | NBL1 | chr1 | 20127338 | 20127471 | Hypo | cancer_general | PLA2G2C |
| chr1 | 20248109 | 20248141 | Hypo | cancer_general | PLA2G2E, OTUD3 | chr1 | 20492168 | 20492298 | Hypo | cancer_general | |
| chr1 | 21026117 | 21026225 | Hypo | cancer_general | KIF17 | chr1 | 21042894 | 21042924 | Hypo | cancer_general | KIF17, SH2D5 |
| chr1 | 21050471 | 21050511 | Hypo | head_neck | SH2D5, KIF17 | chr1 | 21573283 | 21573362 | Hypo | breast | ECE1 |
| chr1 | 21573668 | 21574203 | Hypo | breast | ECE1 LDLRAD2, HSPG2 | chr1 | 21713716 | 21713792 | Hypo | head_neck | — |
| chr1 | 22141326 | 22141355 | Hypo | tcga | | chr1 | 22222711 | 22222793 | Hypo | breast | HSPG2 |
| chr1 | 22927410 | 22927482 | Hypo | cancer_general | EPHA8 | chr1 | 23347997 | 23348043 | Hypo | cancer_general | KDM1A, LOC729059 |
| chr1 | 23449766 | 23449859 | Hypo | head_neck | LUZP1 | chr1 | 24104000 | 24104062 | Hypo | cancer_general | LOC100506963, PITHD1 |
| chr1 | 24161782 | 24161882 | Hypo | colorectal | FUCA1 | chr1 | 24740603 | 24740829 | Hypo | cancer_general | NIPAL3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 25257490 | 25257529 | Hypo | literature | RUNX3 | chr1 | 25257916 | 25258250 | Hypo | literature | RUNX3 |
| chr1 | 25919307 | 25919337 | Hypo | ovarian | — | chr1 | 26183522 | 26183579 | Hypo | breast | PAQR7, AUNIP |
| chr1 | 26467523 | 26467630 | Hypo | cancer_general, lung | — | chr1 | 26917724 | 26917816 | Hypo | cancer_general | — |
| chr1 | 26963625 | 26963789 | Hypo | cancer_general | FAM46B | chr1 | 27190175 | 27190278 | Hypo | cancer_general | SFN |
| chr1 | 27332448 | 27332673 | Hypo | pancreas | WASF2, GPR3 | chr1 | 27340252 | 27340412 | Hypo | cancer_general | FAM46B |
| chr1 | 27724058 | 27724093 | Hypo | head_neck | — | chr1 | 27844518 | 27844548 | Hypo | cancer_general | — |
| chr1 | 28558539 | 28558571 | Hypo | cancer_general | ATPIF1, JA611241, DNAJC8 | chr1 | 28726724 | 28726812 | Hypo | ovarian | PHACTR4 |
| chr1 | 28727177 | 28727324 | Hypo | ovarian | PHACTR4 | chr1 | 28727894 | 28728020 | Hypo | ovarian | PHACTR4 |
| chr1 | 29047659 | 29048643 | Hypo | cancer_general | — | chr1 | 29060250 | 29060311 | Hypo | cancer_general | YTHDF2 |
| chr1 | 29065131 | 29065211 | Hypo | cancer_general | YTHDF2 | chr1 | 30351554 | 30351742 | Hypo | cancer_general | — |
| chr1 | 31863186 | 31863216 | Hypo | cancer_general | — | chr1 | 32533211 | 32533653 | Hypo | cancer_general | TMEM39B, KHDRBS1 |
| chr1 | 32705488 | 32705550 | Hypo | cancer_general | FAM167B, MTMR9LP, EIF3I | chr1 | 32756498 | 32756581 | Hypo | cancer_general | HDAC1, LCK |
| chr1 | 32938720 | 32938750 | Hypo | cancer_general | ZBTB8A, ZBTB8B | chr1 | 33163605 | 33163786 | Hypo | head_neck | SYNC |
| chr1 | 35586911 | 35586962 | Hypo | cancer_general | ZMYM1 | chr1 | 35664625 | 35664746 | Hypo | cancer_general | SFPQ |
| chr1 | 36236269 | 36236299 | Hypo | cancer_general | CLSPN | chr1 | 36334925 | 36335053 | Hypo | cancer_general | AGO1 |
| chr1 | 36563479 | 36563522 | Hypo | cancer_general | COL8A2, ADPRHL2, TEKT2 | chr1 | 38060267 | 38060317 | Hypo | cancer_general | GNL2 |
| chr1 | 38398213 | 38398348 | Hypo | cancer_general | INPP5B | chr1 | 39416980 | 39417182 | Hypo | cancer_general | RHBDL2 |
| chr1 | 40072513 | 40072680 | Hypo | cancer_general | — | chr1 | 40349545 | 40349647 | Hypo | cancer_general | — |
| chr1 | 40625371 | 40625401 | Hypo | cancer_general | RLF | chr1 | 40708443 | 40708578 | Hypo | head_neck | TMCO2, RLF |
| chr1 | 41915253 | 41915283 | Hypo | breast | — | chr1 | 41967342 | 41967418 | Hypo | cancer_general | HIVEP3 |
| chr1 | 41991640 | 41991702 | Hypo | cancer_general | HIVEP3 | chr1 | 43188741 | 43188874 | Hypo | cancer_general | CLDN19 |
| chr1 | 43400336 | 43400386 | Hypo | head_neck | SLC2A1 | chr1 | 43478202 | 43478255 | Hypo | cancer_general | — |
| chr1 | 43814994 | 43815023 | Hypo | literature | CDC20, MPL | chr1 | 43834741 | 43834922 | Hypo | cancer_general | ELOVL1, CDC20 |
| chr1 | 43842664 | 43842779 | Hypo | lung | MED8, ELOVL1 | chr1 | 44068774 | 44068804 | Hypo | cancer_general | PTPRF |
| chr1 | 44109845 | 44109959 | Hypo | cancer_general | KDM4A | chr1 | 44310283 | 44310324 | Hypo | colorectal | ST3GAL3 |
| chr1 | 44494137 | 44494169 | Hypo | cancer_general | SLC6A9 | chr1 | 44726912 | 44727268 | Hypo | cancer_general | ERI3 |
| chr1 | 45240427 | 45240514 | Hypo | cancer_general | SNORD38B, BEST4, KIF2C, RPS8, SNORD55, SNORD46, SNORD38A | chr1 | 45308154 | 45308262 | Hypo | cancer_general | PTCH2, EIF2B3 |
| chr1 | 45645870 | 45645998 | Hypo | cancer_general | ZSWIM5 | chr1 | 45768429 | 45768504 | Hypo | cancer_general | LOC400752 |
| chr1 | 46077719 | 46077805 | Hypo | esophageal | CCDC17, NASP | chr1 | 46347598 | 46347689 | Hypo | cancer_general | MAST2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 46744657 | 46744733 | Hypo | breast | RAD54L, LRRC41 | chr1 | 47035373 | 47035403 | Hypo | ovarian | MKNK1 |
| chr1 | 47078736 | 47078782 | Hypo | head_neck | MOB3C, MKNK1 | chr1 | 47788247 | 47788348 | Hypo | colorectal | — |
| chr1 | 50881363 | 50881529 | Hypo | cancer_general | DMRTA2 | chr1 | 51424099 | 51424224 | Hypo | cancer_general | CDKN2C ORC1, CC2D1B |
| chr1 | 51763252 | 51763298 | Hypo | cancer_general | TTC39A | chr1 | 52832687 | 52832820 | Hypo | cancer_general | ZYG11B |
| chr1 | 53129154 | 53129244 | Hypo | cancer_general | FAM159A | chr1 | 53192045 | 53192075 | Hypo | breast | — |
| chr1 | 53705647 | 53705701 | Hypo | pancreas | LOC100507564, MAGOH, LRP8 | chr1 | 54586626 | 54586736 | Hypo | cancer_general | |
| chr1 | 54837089 | 54837119 | Hypo | esophageal | SSBP3 | chr1 | 54877027 | 54877451 | Hypo | ovarian | SSBP3 |
| chr1 | 55231115 | 55231177 | Hypo | cancer_general | PARS2 | chr1 | 61541602 | 61541718 | Hypo | cancer_general, lung | NFIA |
| chr1 | 62189908 | 62189987 | Hypo | cancer_general | TM2D1 | chr1 | 62793237 | 62793267 | Hypo | pancreas | — |
| chr1 | 64734652 | 64734694 | Hypo | cancer_general | — | chr1 | 65303636 | 65303692 | Hypo | literature | — |
| chr1 | 65304227 | 65304256 | Hypo | literature | JAK1, RAVER2 | chr1 | 65305384 | 65305413 | Hypo | literature | JAK1, RAVER2 |
| chr1 | 65306926 | 65306955 | Hypo | literature | JAK1, RAVER2 | chr1 | 65309787 | 65309816 | Hypo | literature | JAK1 |
| chr1 | 65310487 | 65310531 | Hypo | literature | JAK1 | chr1 | 65311188 | 65311217 | Hypo | literature | JAK1 |
| chr1 | 65312331 | 65312432 | Hypo | literature | JAK1 | chr1 | 67769791 | 67669853 | Hypo | ovarian | IL23R, U6 |
| chr1 | 70599012 | 70599169 | Hypo | cancer_general | LRRC7 | chr1 | 70672778 | 70672878 | Hypo | cancer_general | SRSF11, LRRC40 |
| chr1 | 75600925 | 75601071 | Hypo | cancer_general | LHX8, AK055631 | chr1 | 76354624 | 76354754 | Hypo | cancer_general | MSH4 |
| chr1 | 78463647 | 78463677 | Hypo | cancer_general | DNAJB4 | chr1 | 84944491 | 84944568 | Hypo | cancer_general | RPF1 |
| chr1 | 85725639 | 85725668 | Hypo | tcga | BCL10, C1orf52 | chr1 | 86296345 | 86296375 | Hypo | cancer_general | COL24A1 |
| chr1 | 86860608 | 86860949 | Hypo | cancer_general | ODF2L | chr1 | 89394066 | 89394163 | Hypo | breast | CCBL2 |
| chr1 | 91177989 | 91178149 | Hypo | cancer_general | BARHL2 | chr1 | 91182805 | 91182835 | Hypo | pancreas | BARHL2 |
| chr1 | 94147816 | 94147845 | Hypo | tcga | — | chr1 | 94343568 | 94343744 | Hypo | cancer_general | GCLM, DNTTIP2 |
| chr1 | 94911234 | 94911328 | Hypo | breast | ABCD3 | chr1 | 97185262 | 97185609 | Hypo | head_neck | PTBP2 |
| chr1 | 98515142 | 98515191 | Hypo | pancreas | MIR2682, MIR137HG, MIR137 | chr1 | 100239507 | 100239544 | Hypo | cancer_general | — |
| chr1 | 100310827 | 100310979 | Hypo | cancer_general | AGL | chr1 | 100437068 | 100437172 | Hypo | cancer_general | SLC35A3, BC112312 |
| chr1 | 108722798 | 108722828 | Hypo | hepatobiliary | SLC25A24 | chr1 | 109585463 | 109585632 | Hypo | cancer_general | WDR47 |
| chr1 | 109595405 | 109595534 | Hypo | ovarian | — | chr1 | 109631549 | 109631682 | Hypo | cancer_general | TMEM167B |
| chr1 | 109644226 | 109644336 | Hypo | cancer_general | C1orf194, SCARNA2, TMEM167B | chr1 | 110883542 | 110883965 | Hypo | cancer_general | RBM15, LOC440600, BC069739 |
| chr1 | 111440961 | 111440999 | Hypo | cancer_general | CD53 | chr1 | 112084954 | 112084984 | Hypo | cancer_general | RAP1A |
| chr1 | 113166315 | 113166394 | Hypo | head_neck | CAPZA1, ST7L | chr1 | 114428007 | 114428160 | Hypo | head_neck | BCL2L15, AP4B1-AS1, AP4B1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 114448943 | 114448990 | Hypo | cancer_general | DCLRE1B, AP4B1 | chr1 | 115055395 | 115055425 | Hypo | cancer_general | DENND2C |
| chr1 | 115256514 | 115256552 | Hypo | literature | CSDE1, NRAS | chr1 | 115258729 | 115258772 | Hypo | literature | CSDE1, NRAS |
| chr1 | 116214104 | 116214318 | Hypo | cancer_general | VANGL1 | chr1 | 117901133 | 117901264 | Hypo | cancer_general | MAN1A2 |
| chr1 | 146551186 | 146551215 | Hypo | literature | TRNA_Pseudo, TRNA_His | chr1 | 150603138 | 150603170 | Hypo | cancer_general | ENSA |
| chr1 | 150941425 | 150941847 | Hypo | breast | CERS2, SETDB1 | chr1 | 150994849 | 150995152 | Hypo | ovarian | U6, PRUNE |
| chr1 | 151042405 | 151042496 | Hypo | cancer_general | MLLT11, GABPB2 | chr1 | 151169248 | 151170206 | Hypo | cancer_general | PIP5K1A, VPS72 |
| chr1 | 151253146 | 151253427 | Hypo | cancer_general | ZNF687, BC021024 | chr1 | 151300888 | 151300918 | Hypo | cancer_general | — |
| chr1 | 151362640 | 151362779 | Hypo | colorectal | PSMB4 | chr1 | 153539476 | 153539637 | Hypo | cancer_general | S100A2 |
| chr1 | 153540096 | 153540154 | Hypo | cancer_general | S100A2 | chr1 | 153896746 | 153896800 | Hypo | cancer_general | DENND4B, GATAD2B |
| chr1 | 153937124 | 153937330 | Hypo | cancer_general | CREB3L4, JTB, SLC39A1, CRTC2 | chr1 | 153948791 | 153948823 | Hypo | cancer_general | RAB13, JTB, CREB3L4 |
| chr1 | 154156468 | 154156717 | Hypo | cancer_general | MIR190B, TPM3 | chr1 | 154491036 | 154491066 | Hypo | cancer_general | TDRD10 |
| chr1 | 154516810 | 154516845 | Hypo | cancer_general | UBE2Q1, TDRD10 | chr1 | 155161778 | 155162033 | Hypo | cancer_general | TRIM46, DM075093, MIR92B, THBS3, MUC1, AX746485 |
| chr1 | 155283218 | 155283248 | Hypo | breast | RUSC1-AS1, RUSC1, FDPS | chr1 | 155578375 | 155578921 | Hypo | cancer_general | MSTO1 |
| chr1 | 155617837 | 155617962 | Hypo | cancer_general | BC041646 | chr1 | 155653788 | 155653868 | Hypo | head_neck | YY1AP1, DAP3 |
| chr1 | 155826248 | 155826336 | Hypo | cancer_general | SYT11 | chr1 | 155874151 | 155874300 | Hypo | literature | KIAA0907, RIT1 |
| chr1 | 155874508 | 155874546 | Hypo | literature | KIAA0907, RIT1 | chr1 | 155954282 | 155954396 | Hypo | cancer_general | ARHGEF2 |
| chr1 | 156010377 | 156010548 | Hypo | lung, cancer_general | UBQLN4 | chr1 | 156017591 | 156017683 | Hypo | ovarian | LAMTOR2, UBQLN4 |
| chr1 | 156030286 | 156030621 | Hypo | cancer_general | RAB25, LAMTOR2, UBQLN4 | chr1 | 156432124 | 156432637 | Hypo | cancer_general | MEF2D |
| chr1 | 156838167 | 156838320 | Hypo | cancer_general | NTRK1 | chr1 | 157247347 | 157247388 | Hypo | cancer_general | — |
| chr1 | 157458909 | 157458961 | Hypo | cancer_general | — | chr1 | 157895413 | 157895443 | Hypo | cancer_general | AK057438 |
| chr1 | 158205040 | 158205070 | Hypo | cancer_general | — | chr1 | 158245556 | 158245586 | Hypo | cancer_general | — |
| chr1 | 158295829 | 158295935 | Hypo | cancer_general | CD1B | chr1 | 158318949 | 158318979 | Hypo | hepatobiliary | CD1E |
| chr1 | 158591699 | 158591947 | Hypo | cancer_general | SPTA1 | chr1 | 158669704 | 158669882 | Hypo | cancer_general | OR6K2 |
| chr1 | 158672648 | 158672678 | Hypo | cancer_general | OR6K2 | chr1 | 158687415 | 158687550 | Hypo | cancer_general | OR6K3 |
| chr1 | 158748648 | 158748771 | Hypo | cancer_general | OR6N2 | chr1 | 158760197 | 158760235 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 158778060 | 158778152 | Hypo | cancer_general | — | chr1 | 158815136 | 158815295 | Hypo | cancer_general | MNDA |
| chr1 | 158907635 | 158907665 | Hypo | cancer_general | PYHIN1 | chr1 | 159140357 | 159140386 | Hypo | literature | CADM3 |
| chr1 | 159187279 | 159187429 | Hypo | cancer_general | — | chr1 | 159258862 | 159258891 | Hypo | literature | FCER1A |
| chr1 | 159337419 | 159337615 | Hypo | cancer_general | BC038194 | chr1 | 159409192 | 159409221 | Hypo | literature | OR10J1, BC038194 |
| chr1 | 160451043 | 160451202 | Hypo | cancer_general | SLAMF6 | chr1 | 160693934 | 160694102 | Hypo | cancer_general | — |
| chr1 | 160880758 | 160880788 | Hypo | cancer_general | — | chr1 | 160986299 | 160986385 | Hypo | lung | F11R |
| chr1 | 160992336 | 160992587 | Hypo | cancer_general | F11R | chr1 | 161007587 | 161007746 | Hypo | cancer_general | USF1, ARHGAP30, TSTD1 |
| chr1 | 161013554 | 161013677 | Hypo | blood | USF1, TSTD1, ARHGAP30 | chr1 | 161086730 | 161086813 | Hypo | cancer_general | NIT1, DEDD, PFDN2 |
| chr1 | 161122645 | 161122778 | Hypo | cancer_general | UFC1, USP21 | chr1 | 161359069 | 161359099 | Hypo | cancer_general | — |
| chr1 | 161367577 | 161367701 | Hypo | lung, cancer_general | TRNA_Val | chr1 | 161368283 | 161368507 | Hypo | cancer_general | TRNA_Val |
| chr1 | 161442441 | 161442471 | Hypo | cancer_general | TRNA_Asp, TRNA_Glu, TRNA_Gly, TRNA_Leu | chr1 | 161466301 | 161466347 | Hypo | cancer_general | FCGR2A |
| chr1 | 161471657 | 161471779 | Hypo | lung | FCGR2A | chr1 | 162427088 | 162427153 | Hypo | lung | — |
| chr1 | 162724401 | 162724430 | Hypo | literature | DDR2 | chr1 | 162729615 | 162729686 | Hypo | literature | DDR2 |
| chr1 | 162748392 | 162748421 | Hypo | literature | AF268386, Metazoa_SRP, DDR2 | chr1 | 163393034 | 163393064 | Hypo | hepatobiliary | — |
| chr1 | 164428741 | 164428831 | Hypo | cancer_general | LOC100505795 | chr1 | 164518220 | 164518270 | Hypo | hepatobiliary | LMX1A |
| chr1 | 164730649 | 164730796 | Hypo | hepatobiliary | ADCY10 | chr1 | 165324305 | 165324357 | Hypo | cancer_general | BLZF1, CCDC181 |
| chr1 | 167823339 | 167823461 | Hypo | cancer_general, breast | — | chr1 | 169355697 | 169355727 | Hypo | pancreas | KIFAP3 |
| chr1 | 169838016 | 169838187 | Hypo | breast | Metazoa_SRP, SCYL3 | chr1 | 169930112 | 169930305 | Hypo | pancreas | — |
| chr1 | 170063947 | 170064218 | Hypo | cancer_general | — | chr1 | 170629999 | 170630029 | Hypo | cancer_general | PRRX1 |
| chr1 | 171625525 | 171625561 | Hypo | cancer_general | MYOC | chr1 | 171665240 | 171665330 | Hypo | cancer_general | VAMP4 |
| chr1 | 175346381 | 175346551 | Hypo | cancer_general | TNR | chr1 | 175388664 | 175388700 | Hypo | cancer_general | TNR |
| chr1 | 178063112 | 178063150 | Hypo | breast | RASAL2, RASAL2-AS1 | chr1 | 179046338 | 179046385 | Hypo | pancreas | FAM20B, TOR3A |
| chr1 | 179262226 | 179262256 | Hypo | cancer_general | SOAT1 | chr1 | 180235730 | 180235760 | Hypo | cancer_general | LHX4, LOC100527964 |
| chr1 | 180882640 | 180882669 | Hypo | tcga | KIAA1614 | chr1 | 180919682 | 180919718 | Hypo | breast | KIAA1614, AK056657 |
| chr1 | 180925271 | 180925402 | Hypo | cancer_general | AK056657, KIAA1614 | chr1 | 181014878 | 181014997 | Hypo | head_neck | MR1 |
| chr1 | 182807578 | 182807742 | Hypo | cancer_general | DHX9, NPL | chr1 | 182862133 | 182862328 | Hypo | cancer_general, colorectal | SHCBP1L, DHX9 |
| chr1 | 183129382 | 183129737 | Hypo | cancer_general | APOBEC4, RGL1 | chr1 | 183462761 | 183463024 | Hypo | cancer_general | SMG7 |
| chr1 | 183627506 | 183627539 | Hypo | cancer_general | RNF2 | chr1 | 184970783 | 184970847 | Hypo | cancer_general | — |
| chr1 | 185073818 | 185073966 | Hypo | breast | RNF2 | chr1 | 185076172 | 185076270 | Hypo | ovarian | RNF2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 185336061 | 185336095 | Hypo | cancer_general | — | chr1 | 186570930 | 186571030 | Hypo | hepatobiliary | — |
| chr1 | 195732322 | 195732539 | Hypo | cancer_general | — | chr1 | 197771547 | 197771893 | Hypo | cancer_general | NEK7 |
| chr1 | 197888831 | 197888945 | Hypo | cancer_general | LHX9 | chr1 | 198124799 | 198124932 | Hypo | cancer_general | KIF14 |
| chr1 | 200478843 | 200478932 | Hypo | cancer_general | — | chr1 | 200591054 | 200591225 | Hypo | cancer_general | — |
| chr1 | 201983113 | 201983200 | Hypo | cancer_general | ELF3, RNPEP | chr1 | 202081728 | 202081804 | Hypo | cancer_general | — |
| chr1 | 202311820 | 202311901 | Hypo | cancer_general | UBE2T, PPP1R12B | chr1 | 202531939 | 202532087 | Hypo | breast | PPP1R12B |
| chr1 | 202856858 | 202856937 | Hypo | cancer_general | RAB1F, KLHL12 | chr1 | 203298307 | 203298710 | Hypo | cancer_general | — |
| chr1 | 203429564 | 203429594 | Hypo | cancer_general | — | chr1 | 203681332 | 203681362 | Hypo | blood | ATP2B4 |
| chr1 | 204333609 | 204333668 | Hypo | cancer_general | LINC00628 | chr1 | 204478284 | 204478427 | Hypo | cancer_general | MDM4, TRNA_Lys |
| chr1 | 204499813 | 204499842 | Hypo | literature | MDM4 | chr1 | 204524704 | 204524744 | Hypo | head_neck | MDM4 |
| chr1 | 204531203 | 204531757 | Hypo | breast | MDM4 | chr1 | 206950282 | 206950328 | Hypo | cancer_general | IL10 |
| chr1 | 207200870 | 207200962 | Hypo | cancer_general | PFKFB2, C1orf16 | chr1 | 207227318 | 207227556 | Hypo | cancer_general | PFKFB2, YOD1 |
| chr1 | 207794579 | 207794609 | Hypo | cancer_general | CR1 | chr1 | 207833206 | 207833370 | Hypo | cancer_general | CR1L |
| chr1 | 209164972 | 209165091 | Hypo | cancer_general | — | chr1 | 209604382 | 209604597 | Hypo | literature | MIR205, MIR205HG |
| chr1 | 209605386 | 209605415 | Hypo | literature | MIR205HG, MIR205 | chr1 | 211847706 | 211847787 | Hypo | cancer_general | NEK2 |
| chr1 | 212484610 | 212484816 | Hypo | ovarian | PPP2R5A | chr1 | 212963883 | 212964151 | Hypo | cancer_general | TATDN3, NSL1 |
| chr1 | 213189937 | 213190065 | Hypo | cancer_general | ANGEL2 | chr1 | 217307369 | 217307654 | Hypo | pancreas, cancer_general | — |
| chr1 | 217309764 | 217309816 | Hypo | cancer_general | — | chr1 | 217311463 | 217311516 | Hypo | cancer_general | EPRS |
| chr1 | 217805158 | 217805395 | Hypo | cancer_general | SPATA17, GPATCH2 | chr1 | 220132075 | 220132111 | Hypo | colorectal | — |
| chr1 | 220636466 | 220636510 | Hypo | cancer_general | — | chr1 | 220896508 | 220896568 | Hypo | cancer_general | CAPN2 |
| chr1 | 221510339 | 221510368 | Hypo | literature | C1orf140 | chr1 | 223894714 | 223894752 | Hypo | cancer_general | — |
| chr1 | 223899470 | 223899500 | Hypo | cancer_general | CAPN2 | chr1 | 224267615 | 224267662 | Hypo | cancer_general | — |
| chr1 | 224400490 | 224400524 | Hypo | cancer_general | — | chr1 | 224493975 | 224494083 | Hypo | cancer_general | NVL |
| chr1 | 224804831 | 224804910 | Hypo | cancer_general | CNIH3 | chr1 | 224805564 | 224805620 | Hypo | lung | CNIH3 |
| chr1 | 225118306 | 225118474 | Hypo | cancer_general | DNAH14 | chr1 | 225908076 | 225908184 | Hypo | cancer_general | AK124056 |
| chr1 | 226265194 | 226265257 | Hypo | cancer_general | BC032899, H3F3AP4, H3F3A | chr1 | 226384322 | 226384440 | Hypo | cancer_general | BC033346, ACBD3 |
| chr1 | 226997660 | 226997719 | Hypo | hepatobiliary | OBSCN | chr1 | 228201221 | 228201251 | Hypo | cancer_general | WNT3A |
| chr1 | 228461158 | 228461197 | Hypo | hepatobiliary | OBSCN | chr1 | 228528840 | 228529016 | Hypo | cancer_general | OBSCN |
| chr1 | 228558699 | 228559238 | Hypo | cancer_general | CCSAP | chr1 | 228693629 | 228693767 | Hypo | cancer_general | RNF187 |
| chr1 | 229476753 | 229476879 | Hypo | cancer_general | FAM89A, MIR1182 | chr1 | 230404217 | 230404263 | Hypo | cancer_general | GALNT2 |
| chr1 | 231149928 | 231150098 | Hypo | cancer_general | KIAA1804 | chr1 | 231475814 | 231476081 | Hypo | cancer_general | SPRTN, EXOC8 |
| chr1 | 233465473 | 233465503 | Hypo | ovarian | TARBP1 | chr1 | 234445373 | 234445403 | Hypo | cancer_general | MIR4671, SLC35F3 |
| chr1 | 234620866 | 234620979 | Hypo | ovarian | — | chr1 | 234798171 | 234798201 | Hypo | cancer_general | — |
| chr1 | 234839889 | 234840058 | Hypo | lung | — | chr1 | 234844955 | 234845079 | Hypo | cancer_general | BC032040 |
| chr1 | 234845467 | 234845497 | Hypo | cancer_general | — | chr1 | 235266920 | 235266950 | Hypo | cancer_general | TOMM20 |
| chr1 | 235665663 | 235665736 | Hypo | cancer_general | B3GALNT2 | chr1 | 235669296 | 235669398 | Hypo | cancer_general | B3GALNT2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 237970760 | 237970826 | Hypo | cancer_general | RYR2 | chr1 | 238024448 | 238024477 | Hypo | literature | LOC100130331 |
| chr1 | 240118848 | 240118973 | Hypo | cancer_general | — | chr1 | 240256663 | 240256780 | Hypo | pancreas | FMN2 |
| chr1 | 241052096 | 241052126 | Hypo | cancer_general | RGS7 | chr1 | 241052360 | 241052419 | Hypo | colorectal | RGS7 |
| chr1 | 241912749 | 241912778 | Hypo | literature | WDR64 | chr1 | 243859000 | 243859029 | Hypo | literature | — |
| chr1 | 243921295 | 243921330 | Hypo | cancer_general | — | chr1 | 244115072 | 244115212 | Hypo | cancer_general | LOC339529 |
| chr1 | 245032517 | 245032603 | Hypo | lung | HNRNPU | chr1 | 245135753 | 245136064 | Hypo | cancer_general | EFCAB2 |
| chr1 | 245494495 | 245494578 | Hypo | ovarian | KIF26B | chr1 | 245849914 | 245849944 | Hypo | hepatobiliary | KIF26B |
| chr1 | 246198078 | 246198203 | Hypo | breast | SMYD3 | chr1 | 246230309 | 246230409 | Hypo | cancer_general | SMYD3 |
| chr1 | 246488175 | 246488336 | Hypo | head_neck | SMYD3 | chr1 | 246654652 | 246654851 | Hypo | breast | SMYD3 |
| chr1 | 247284422 | 247284452 | Hypo | cancer_general | ZNF124, C1orf229 | chr1 | 247608784 | 247608814 | Hypo | hepatobiliary | OR2B11, NLRP3 |
| chr1 | 247684856 | 247684929 | Hypo | cancer_general | GCSAML-AS1, OR2C3, AK130400, GCSAML | chr1 | 247910678 | 247910780 | Hypo | cancer_general | OR1C1 |
| chr1 | 248002278 | 248002437 | Hypo | cancer_general | OR11L1 | chr1 | 248028015 | 248028202 | Hypo | cancer_general | TRIM58 |
| chr1 | 248074729 | 248074927 | Hypo | cancer_general | OR2T8 | chr1 | 248099751 | 248099809 | Typo | cancer_general | OR2L13 |
| chr1 | 248198552 | 248198721 | Hypo | cancer_general | OR2L2 | chr1 | 248328701 | 248328841 | Hypo | cancer_general | — |
| chr1 | 248691575 | 248691616 | Hypo | cancer_general | OR2G6 | chr1 | 248860898 | 248861046 | Hypo | cancer_general | — |
| chr1 | 249121600 | 249121704 | Hypo | cancer_general | MIR3124, SH3BP5L | chr4 | 488816 | 488875 | Hypo | breast | — |
| chr4 | 512978 | 513008 | Hypo | head_neck | PIGG | chr4 | 513704 | 513734 | Hypo | head_neck | PIGG, ZNF721 |
| chr4 | 628572 | 629061 | Hypo | cancer_general | PDE6B | chr4 | 651196 | 651261 | Hypo | cancer_general | PIGG |
| chr4 | 678471 | 678501 | Hypo | cancer_general | MFSD7, MYL5 | chr4 | 718052 | 718112 | Hypo | colorectal | BC020343, PDE6B |
| chr4 | 718321 | 718456 | Hypo | colorectal | PCGF3 | chr4 | 829611 | 829641 | Hypo | cancer_general | PCGF3 |
| chr4 | 955367 | 955454 | Hypo | cancer_general | DGKQ, TMEM175 | chr4 | 955867 | 955919 | Hypo | cancer_general | CPLX1 DGKQ, TMEM175 |
| chr4 | 1008740 | 1008902 | Hypo | ovarian | FGFRL1 | chr4 | 1016127 | 1016252 | Hypo | cancer_general | FGFRL1 |
| chr4 | 1016586 | 1016747 | Hypo | cancer_general | FGFRL1 | chr4 | 1025928 | 1026074 | Hypo | cancer_general | FGFRL1 |
| chr4 | 1041763 | 1041926 | Hypo | cancer_general | AK124578 | chr4 | 1093536 | 1093675 | Hypo | pancreas | RNF212 |
| chr4 | 1189021 | 1189051 | Hypo | cancer_general | LOC100130872, AX747178 | chr4 | 1214894 | 1215162 | Hypo | ovarian | HV535487, HV535469, CTBP1 |
| chr4 | 1215415 | 1215451 | Hypo | ovarian | CTBP1, HV535487, HV535469 | chr4 | 1282515 | 1282545 | Hypo | ovarian | MAEA, C4orf42 |
| chr4 | 1331675 | 1331705 | Hypo | pancreas | UVSSA, MAEA | chr4 | 1336755 | 1336902 | Hypo | ovarian | UVSSA, MAEA |
| chr4 | 1338715 | 1338812 | Hypo | cancer_general | UVSSA, MAEA | chr4 | 1339099 | 1339221 | Hypo | cancer_general | UVSSA, MAEA |
| chr4 | 1512368 | 1512398 | Hypo | cancer_general | — | chr4 | 1556419 | 1556609 | Hypo | cancer_general | — |
| chr4 | 1576484 | 1576528 | Hypo | cancer_general | AX748388 | chr4 | 1616682 | 1617247 | Hypo | cancer_general | LETM1, FGFR3 |
| chr4 | 1687080 | 1687110 | Hypo | cancer_general | SLBP, FAM53A | chr4 | 1803550 | 1803582 | Hypo | literature | — |
| chr4 | 1806084 | 1806113 | Hypo | literature | LETM1, FGFR3 | chr4 | 1807355 | 1807384 | Hypo | literature | FGFR3, LETM1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 1962787 | 1962816 | Hypo | literature | WHSC1 | chr4 | 1993771 | 1994180 | Hypo | cancer_general | MIR943, NELFA |
| chr4 | 2066114 | 2066265 | Hypo | cancer_general | POLN, NAT8L | chr4 | 2305672 | 2305827 | Hypo | cancer_general | ZFYVE28 |
| chr4 | 2527907 | 2527937 | Hypo | cancer_general | — | chr4 | 2532556 | 2532586 | Hypo | cancer_general | MFSD10 |
| chr4 | 2540073 | 2540297 | Hypo | cancer_general | — | chr4 | 2926366 | 2926396 | Hypo | cancer_general | GRK4 |
| chr4 | 2978968 | 2979145 | Hypo | esophageal | GRK4 | chr4 | 3036118 | 3036148 | Hypo | esophageal | HGFAC |
| chr4 | 3217107 | 3217154 | Hypo | breast | — | chr4 | 3446991 | 3447021 | Hypo | lung | — |
| chr4 | 3447816 | 3448015 | Hypo | cancer_general | HGFAC | chr4 | 4417568 | 4417603 | Hypo | cancer_general | NSG1, STX18 |
| chr4 | 5519950 | 5520092 | Hypo | cancer_general | C4orf6 | chr4 | 6628453 | 6628500 | Hypo | ovarian | MAN2B2 |
| chr4 | 6670184 | 6670214 | Hypo | cancer_general | LOC93622 | chr4 | 6719599 | 6719637 | Hypo | cancer_general | BLOC1S4, MREAP1L1 |
| chr4 | 6748346 | 6748557 | Hypo | cancer_general | AX747238, TBC1D14 | chr4 | 6839352 | 6839402 | Hypo | head_neck | KIAA0232 |
| chr4 | 6955114 | 6955144 | Hypo | cancer_general | — | chr4 | 6957481 | 6957620 | Hypo | cancer_general | — |
| chr4 | 7038560 | 7038688 | Hypo | breast | CCDC96, TADA2B, LOC100129931, TBC1D14 | chr4 | 7647770 | 7647945 | Hypo | cancer_general | — |
| chr4 | 7758476 | 7758561 | Hypo | pancreas | AFAP1, AFAP1-AS1 | chr4 | 8429086 | 8429178 | Hypo | cancer_general | ACOX3 |
| chr4 | 8607813 | 8607932 | Hypo | cancer_general | CPZ | chr4 | 8608556 | 8608600 | Hypo | cancer_general | CPZ |
| chr4 | 9423273 | 9423354 | Hypo | cancer_general | — | chr4 | 10782701 | 10782741 | Hypo | cancer_general | — |
| chr4 | 13524957 | 13525008 | Hypo | pancreas | LOC285547 | chr4 | 17430691 | 17430832 | Hypo | cancer_general | — |
| chr4 | 26256826 | 26256867 | Hypo | hepatobiliary | — | chr4 | 38566328 | 38566418 | Hypo | head_neck | — |
| chr4 | 38673115 | 38673144 | Hypo | literature | FLJ113197, KLF3 | chr4 | 39816807 | 39817064 | Hypo | cancer_general | PDS5A |
| chr4 | 40910303 | 40910465 | Hypo | cancer_general | TRNA_Gln, APBB2 | chr4 | 41938449 | 41938479 | Hypo | cancer_general | TMEM33 |
| chr4 | 41993676 | 41993815 | Hypo | cancer_general | SLC30A9, DCAF4L1 | chr4 | 42155293 | 42155322 | Hypo | literature | BEND4 |
| chr4 | 42348266 | 42348331 | Hypo | ovarian | — | chr4 | 44266683 | 44266780 | Hypo | cancer_general | KCTD8 |
| chr4 | 46067800 | 46067954 | Hypo | cancer_general | GABRG1 | chr4 | 46911535 | 46911564 | Hypo | literature | GABRA4 |
| chr4 | 47197142 | 47197270 | Hypo | cancer_general | GABRB1 | chr4 | 47914784 | 47914992 | Hypo | cancer_general | NFXL1, BC041434 |
| chr4 | 48848428 | 48848554 | Hypo | head_neck | OCIAD1 | chr4 | 55133613 | 55133642 | Hypo | literature | PDGFRA |
| chr4 | 55136787 | 55136816 | Hypo | literature | PDGFRA | chr4 | 55138657 | 55138686 | Hypo | literature | PDGFRA |
| chr4 | 55139691 | 55139720 | Hypo | literature | PDGFRA | chr4 | 55140731 | 55140784 | Hypo | literature | PDGFRA |
| chr4 | 55141015 | 55141050 | Hypo | literature | PDGFRA | chr4 | 55144105 | 55144134 | Hypo | literature | PDGFRA |
| chr4 | 55146554 | 55146583 | Hypo | literature | PDGFRA | chr4 | 55152075 | 55152140 | Hypo | literature | PDGFRA |
| chr4 | 55589753 | 55589782 | Hypo | literature | DL490879, KIT | chr4 | 55592166 | 55592204 | Hypo | literature | KIT, DL490879 |
| chr4 | 55593417 | 55593675 | Hypo | literature | KIT, DL490879 | chr4 | 55594183 | 55594212 | Hypo | literature | KIT, DL490879 |
| chr4 | 55595504 | 55595614 | Hypo | literature | KIT, DL490879 | chr4 | 55599306 | 55599356 | Hypo | literature | — |
| chr4 | 55968165 | 55968194 | Hypo | literature | KDR | chr4 | 56594679 | 56594720 | Hypo | hepatobiliary | REST |
| chr4 | 57017387 | 57017459 | Hypo | hepatobiliary | — | chr4 | 57777437 | 57777595 | Hypo | ovarian | REST |
| chr4 | 57803498 | 57803558 | Hypo | pancreas | REST | chr4 | 57813490 | 57813763 | Hypo | ovarian | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 73459699 | 73459762 | Hypo | cancer_general | | chr4 | 74142341 | 74142434 | Hypo | ovarian | |
| chr4 | 75241080 | 75241435 | Hypo | cancer_general | EREG | chr4 | 76554873 | 76554935 | Hypo | lung, cancer_general | CDKL2 |
| chr4 | 76912698 | 76912733 | Hypo | cancer_general | CXCL0, SDAD1 | chr4 | 79611132 | 79611294 | Hypo | cancer_general | LOC100505702 |
| chr4 | 79689651 | 79689732 | Hypo | colorectal | BMP2K | chr4 | 79861530 | 79861560 | Hypo | cancer_general | PAQR3 |
| chr4 | 80273120 | 80273150 | Hypo | hepatobiliary | | chr4 | 81188328 | 81188489 | Hypo | cancer_general | FGF5 |
| chr4 | 83323506 | 83323708 | Hypo | lung | | chr4 | 83343366 | 83343396 | Hypo | cancer_general | HNRPDL, ENOPH1 |
| chr4 | 83809740 | 83809787 | Hypo | cancer_general | THAP9-AS1, AK128593, SEC31A | chr4 | 83955171 | 83955201 | Hypo | cancer_general | COPS4 |
| chr4 | 83988361 | 83988511 | Hypo | cancer_general | COPS4 | chr4 | 90043517 | 90043547 | Hypo | cancer_general | TIGD2 |
| chr4 | 91079842 | 91079899 | Hypo | cancer_general | CCSER1 | chr4 | 95127590 | 95127717 | Hypo | cancer_general | SMARCAD1 |
| chr4 | 95128038 | 95128068 | Hypo | cancer_general | SMARCAD1 | chr4 | 95762672 | 95762896 | Hypo | cancer_general | BMPR1B |
| chr4 | 102332467 | 102332611 | Hypo | cancer_general | BANK1 | chr4 | 103929647 | 103929796 | Hypo | cancer_general | SLC9B1 |
| chr4 | 103930065 | 103930095 | Hypo | cancer_general | SLC9B1 | chr4 | 106335495 | 106335617 | Hypo | breast | PPA2 |
| chr4 | 110344202 | 110344294 | Hypo | cancer_general | SEC24B-AS1, AK058136 | chr4 | 110735672 | 110735702 | Hypo | cancer_general | GAR1 |
| chr4 | 113154896 | 113155129 | Hypo | cancer_general | AP1AR | chr4 | 113431900 | 113431930 | Hypo | pancreas | NEUROG2 |
| chr4 | 113559163 | 113559422 | Hypo | cancer_general | MIR302B, LARP7, C4orf21 | chr4 | 123664228 | 123664363 | Hypo | cancer_general | BBS12 |
| chr4 | 128967250 | 128967329 | Hypo | colorectal | | chr4 | 128968647 | 128968800 | Hypo | head_neck | |
| chr4 | 128969310 | 128969382 | Hypo | head_neck | | chr4 | 128984386 | 128984464 | Hypo | cancer_general | LARP1B |
| chr4 | 130018134 | 130018266 | Hypo | cancer_general | SCLT1, C4orf33 | chr4 | 134073862 | 134073919 | Hypo | cancer_general | PCDH10, BC040219 |
| chr4 | 144586035 | 144586088 | Hypo | cancer_general | FREM3 | chr4 | 146853951 | 146853981 | Hypo | head_neck | ZNF827 |
| chr4 | 151974287 | 151974510 | Hypo | pancreas | | chr4 | 152148807 | 152148836 | Hypo | literature | SH3D19 |
| chr4 | 153247273 | 153247386 | Hypo | literature | FBXW7 | chr4 | 153249362 | 153249398 | Hypo | literature | FBXW7 |
| chr4 | 153251894 | 153251923 | Hypo | literature | FBXW7 | chr4 | 153702668 | 153702702 | Hypo | cancer_general | ARFIP1 |
| chr4 | 154216241 | 154216357 | Hypo | cancer_general | | chr4 | 154374504 | 154374630 | Hypo | head_neck | |
| chr4 | 155665445 | 155665475 | Hypo | esophageal | LRAT, DQ266889 | chr4 | 158101782 | 158102020 | Hypo | cancer_general | GLRB |
| chr4 | 159063301 | 159063331 | Hypo | hepatobiliary | FAM198B | chr4 | 159149784 | 159149824 | Hypo | head_neck | TMEM144 |
| chr4 | 164819191 | 164819221 | Hypo | hepatobiliary | | chr4 | 170865234 | 170865287 | Hypo | cancer_general | LOC100506085 |
| chr4 | 171012375 | 171012409 | Hypo | cancer_general | AADAT | chr4 | 172132870 | 172133019 | Hypo | cancer_general | |
| chr4 | 173953411 | 173953594 | Hypo | hepatobiliary | | chr4 | 174083164 | 174083431 | Hypo | hepatobiliary | GALNT7, BC040577 |
| chr4 | 174124429 | 174124477 | Hypo | hepatobiliary | GALNT7 | chr4 | 174136704 | 174136734 | Hypo | hepatobiliary | GALNT7 |
| chr4 | 174224186 | 174224216 | Hypo | hepatobiliary | GALNT7 | chr4 | 178285756 | 178285879 | Hypo | head_neck | |
| chr4 | 183064874 | 183064966 | Hypo | pancreas | TENM3, MGC45800 | chr4 | 184375546 | 184375726 | Hypo | cancer_general | CDKN2AIP |
| chr4 | 184491996 | 184492042 | Hypo | cancer_general | | chr4 | 184921855 | 184922091 | Hypo | pancreas, cancer_general | STOX2 |
| chr19 | 403538 | 403809 | Hypo | cancer_general | C2CD4C | chr19 | 407189 | 407320 | Hypo | cancer_general | SHC2, C2CD4C |
| chr19 | 418225 | 418255 | Hypo | ovarian | SHC2, C2CD4C | chr19 | 468757 | 468787 | Hypo | cancer_general | ODF3L2, SHC2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 485165 | 485394 | Hypo | cancer_general | — | chr19 | 549361 | 549451 | Hypo | cancer_general | GZMM, CDC34 |
| chr19 | 555608 | 555768 | Hypo | cancer_general | GZMM HCN2, BSG | chr19 | 570156 | 570194 | Hypo | esophageal | BSG |
| chr19 | 592589 | 592632 | Hypo | cancer_general | | chr19 | 593290 | 593462 | Hypo | cancer_general | HCN2, BSG |
| chr19 | 599214 | 599333 | Hypo | cancer_general | HCN2 | chr19 | 607070 | 607110 | Hypo | head_neck | HCN2 |
| chr19 | 690888 | 690940 | Hypo | cancer_general | PRSS57, FSTL3 | chr19 | 752136 | 752462 | Hypo | cancer_general | MISP, PALM |
| chr19 | 869337 | 869394 | Hypo | pancreas | CFD, MED16 | chr19 | 883624 | 883791 | Hypo | cancer_general | MED16, U6 |
| chr19 | 884018 | 884162 | Hypo | cancer_general | U6, MED16 | chr19 | 891516 | 891723 | Hypo | cancer_general | U6, R3HDM4, MED16 |
| chr19 | 955757 | 956237 | Hypo | cancer_general | ARID3A FLJ00277, TMEM259, GRIN3B, WDR18 | chr19 | 959128 | 959187 | Hypo | pancreas | ARID3A FLJ00277, TMEM259, GRIN3B, WDR18 |
| chr19 | 1003305 | 1003384 | Hypo | cancer_general | | chr19 | 1003669 | 1003734 | Hypo | cancer_general | ABCA7, CNN2 |
| chr19 | 1004915 | 1005441 | Hypo | cancer_general | FLJ00277, TMEM259, GRIN3B | chr19 | 1030176 | 1030225 | Hypo | cancer_general | |
| chr19 | 1047890 | 1047939 | Hypo | cancer_general | ABCA7 POLR2E, HMHA1 | chr19 | 1048348 | 1048465 | Hypo | ovarian | ABCA7 |
| chr19 | 1083314 | 1083437 | Hypo | cancer_general | | chr19 | 1156524 | 1156554 | Hypo | cancer_general | — |
| chr19 | 1170185 | 1170230 | Hypo | cancer_general | C19orf26, STK11 | chr19 | 1171099 | 1171324 | Hypo | cancer_general | — |
| chr19 | 1220422 | 1220610 | Hypo | literature | | chr19 | 1221981 | 1222010 | Hypo | literature | STK11, C19orf26 |
| chr19 | 1236474 | 1236678 | Hypo | cancer_general | ATP5D, C19orf26, STK11 | chr19 | 1274778 | 1274826 | Hypo | cancer_general | CIRBP-AS1, C19orf24, DL492057, CIRBP |
| chr19 | 1325788 | 1325889 | Hypo | cancer_general | — | chr19 | 1330064 | 1330214 | Hypo | cancer_general | — |
| chr19 | 1496413 | 1496450 | Hypo | cancer_general | PCSK4, ADAMTSL5, REEP6 | chr19 | 1496654 | 1496694 | Hypo | cancer_general | ADAMTSL5, REEP6, PCSK4 |
| chr19 | 1525605 | 1525960 | Hypo | cancer_general | PLK5 | chr19 | 1527227 | 1527394 | Hypo | cancer_general | PLK5 |
| chr19 | 1547233 | 1547263 | Hypo | cancer_general | MEX3D | chr19 | 1689436 | 1689595 | Hypo | cancer_general | — |
| chr19 | 1799466 | 1799516 | Hypo | cancer_general | ATP8B3 | chr19 | 1800032 | 1800300 | Hypo | cancer_general | ATP8B3 |
| chr19 | 1807970 | 1808413 | Hypo | cancer_general | MIR1909, ATP8B3, REXO1 | chr19 | 2155031 | 2155061 | Hypo | cancer_general | DOT1L |
| chr19 | 2274677 | 2274713 | Hypo | cancer_general | C19orf35, SPPL2B, OAZ1 | chr19 | 2330317 | 2330407 | Hypo | cancer_general | SPPL2B, LSM7 |
| chr19 | 2331413 | 2331443 | Hypo | cancer_general | SPPL2B, LSM7 | chr19 | 2413125 | 2413155 | Hypo | cancer_general | TMPRSS9 |
| chr19 | 2414257 | 2414337 | Hypo | cancer_general | TMPRSS9 BC022568, GNG7 | chr19 | 2513250 | 2513285 | Hypo | cancer_general | GNG7 |
| chr19 | 2642877 | 2642947 | Hypo | cancer_general | | chr19 | 2683911 | 2684080 | Hypo | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 3041417 | 3041447 | Hypo | cancer_general | — | chr19 | 3093571 | 3093818 | Hypo | cancer_general | GNA11 |
| chr19 | 3114998 | 3115027 | Hypo | literature | DKFZp434J1194, GNA11 | chr19 | 3118927 | 3118956 | Hypo | literature | DKFZp434J1194, GNA11 |
| chr19 | 3219512 | 3219565 | Hypo | cancer_general | CELF5, NCLN | chr19 | 3296613 | 3296670 | Hypo | cancer_general | CELF5 |
| chr19 | 3562128 | 3562797 | Hypo | cancer_general | MFSD12 | chr19 | 3570230 | 3570371 | Hypo | cancer_general | HMG20B |
| chr19 | 3578138 | 3578223 | Hypo | colorectal | GIPC3, HMG20B | chr19 | 3716179 | 3716241 | Hypo | cancer_general | TJP3 |
| chr19 | 3718052 | 3718082 | Hypo | cancer_general | TJP3 | chr19 | 3778130 | 3778394 | Hypo | cancer_general | JA611290, MATK, RAX2 |
| chr19 | 3779277 | 3779435 | Hypo | cancer_general | JA611290, MATK, RAX2 | chr19 | 3821044 | 3821217 | Hypo | cancer_general | ZFR2 |
| chr19 | 3834572 | 3834641 | Hypo | hepatobiliary | ZFR2 | chr19 | 3855407 | 3855595 | Hypo | cancer_general | ZFR2 |
| chr19 | 3966686 | 3966755 | Hypo | cancer_general | EEF2, MIR637, DAPK3 | chr19 | 3994540 | 3994595 | Hypo | colorectal | — |
| chr19 | 4054435 | 4054471 | Hypo | pancreas | ZBTB7A | chr19 | 4095471 | 4095514 | Hypo | cancer_general | MAP2K2 |
| chr19 | 4101087 | 4101116 | Hypo | literature | MAP2K2 | chr19 | 4110565 | 4110597 | Hypo | literature | MAP2K2 |
| chr19 | 4117526 | 4117630 | Hypo | literature | MAP2K2 | chr19 | 4160800 | 4160898 | Hypo | cancer_general | CREB3L3 |
| chr19 | 4195767 | 4195853 | Hypo | cancer_general | ANKRD24 | chr19 | 4311273 | 4311430 | Hypo | cancer_general | TMIGD2, FSD1 |
| chr19 | 4509338 | 4509440 | Hypo | cancer_general | PLIN4, HDGFRP2 | chr19 | 4548134 | 4548364 | Hypo | cancer_general | SEMA6B, LRG1, PLIN5 |
| chr19 | 4549454 | 4549565 | Hypo | cancer_general | SEMA6B, LRG1, PLIN5 | chr19 | 4550246 | 4550330 | Hypo | cancer_general | SEMA6B |
| chr19 | 4555896 | 4556112 | Hypo | cancer_general | SEMA6B | chr19 | 4557098 | 4557235 | Hypo | cancer_general | SEMA6B |
| chr19 | 4572332 | 4572459 | Hypo | cancer_general | — | chr19 | 4670765 | 4670949 | Hypo | cancer_general | DPP9, LOC100131094, C19orf10 |
| chr19 | 4789697 | 4789805 | Hypo | cancer_general | FEM1A, AK126532 | chr19 | 4790142 | 4790264 | Hypo | cancer_general | FEM1A, AK126532 |
| chr19 | 4835778 | 4835926 | Hypo | colorectal | PLIN3 | chr19 | 4910361 | 4910410 | Hypo | breast | ARRDC5, UHRF1, C19orf31 |
| chr19 | 5608519 | 5608569 | Hypo | cancer_general | SAFB2 | chr19 | 5676212 | 5676242 | Hypo | cancer_general | C19orf70, HSD11B1L |
| chr19 | 5759374 | 5759544 | Hypo | cancer_general | CATSPERD | chr19 | 5759744 | 5759774 | Hypo | cancer_general | CATSPERD |
| chr19 | 5767703 | 5767733 | Hypo | cancer_general | CATSPERD | chr19 | 5826179 | 5826209 | Hypo | cancer_general | FUT6, NRTN |
| chr19 | 5905517 | 5905547 | Hypo | cancer_general | CAPS, VMAC, NDUFA11 | chr19 | 5910356 | 5910492 | Hypo | cancer_general | CAPS, RANBP3, VMAC, NDUFA11 |
| chr19 | 5914761 | 5914791 | Hypo | cancer_general | RANBP3, CAPS, VMAC | chr19 | 5914992 | 5915060 | Hypo | cancer_general | RANBP3, CAPS, VMAC |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 6303268 | 6303298 | Hypo | cancer_general | ACER1 | chr19 | 6512913 | 6512943 | Hypo | cancer_general | EMR1 |
| chr19 | 6658279 | 6658422 | Hypo | cancer_general | TNFSF14 | chr19 | 6889423 | 6889574 | Hypo | cancer_general | C19orf45, PEX11G |
| chr19 | 7157547 | 7157628 | Hypo | lung | INSR | chr19 | 7554718 | 7554780 | Hypo | cancer_general | FCER2, TRAPPC5, C19orf59 |
| chr19 | 7635387 | 7635552 | Hypo | cancer_general | PNPLA6 | chr19 | 7747205 | 7747234 | Hypo | tcga | KANK3, RPS28, NDUFA7 |
| chr19 | 7870346 | 7870387 | Hypo | cancer_general | — | chr19 | 8391621 | 8391651 | Hypo | cancer_general | ZNF414, PRAM1, MYO1F |
| chr19 | 8554173 | 8554218 | Hypo | head_neck | PRAM1, DKFZp547H118, HNRNPM | chr19 | 8576914 | 8577000 | Hypo | lung | OR7G3 |
| chr19 | 8579592 | 8579705 | Hypo | ovarian | MYO1F, ZNF414 | chr19 | 9239580 | 9239695 | Hypo | cancer_general | UBL5, PIN1, FBXL12 |
| chr19 | 9331918 | 9331955 | Hypo | hepatobiliary | OR7D4 | chr19 | 9937291 | 9937386 | Hypo | cancer_general | DNMT1 |
| chr19 | 10231077 | 10231242 | Hypo | cancer_general | P2RY11, EIF3G | chr19 | 10246506 | 10246566 | Hypo | lung | KEAP1 |
| chr19 | 10362045 | 10362182 | Hypo | cancer_general | MRPL4 | chr19 | 10600431 | 10600460 | Hypo | literature | KEAP1 |
| chr19 | 10602274 | 10602348 | Hypo | literature | KEAP1 | chr19 | 10602565 | 10602864 | Hypo | literature | S1PR5, KEAP1 |
| chr19 | 10610138 | 10610260 | Hypo | literature | KEAP1 | chr19 | 10621768 | 10621829 | Hypo | cancer_general | SLC44A2 |
| chr19 | 10648372 | 10648546 | Hypo | cancer_general | ATG4D | chr19 | 10729811 | 10729899 | Hypo | cancer_general | DNM2, MIR638, QTRT1 |
| chr19 | 10823678 | 10823721 | Hypo | colorectal | DNM2, MIR638, QTRT1 | chr19 | 10827675 | 10827705 | Hypo | cancer_general | C19orf38, TMED1 |
| chr19 | 10851287 | 10851362 | Hypo | colorectal | — | chr19 | 10955456 | 10955585 | Hypo | cancer_general | SMARCA4 |
| chr19 | 11063941 | 11063971 | Hypo | cancer_general | SMARCA4 | chr19 | 11134252 | 11134281 | Hypo | literature | ZNF878, ZNF433, AX747405 |
| chr19 | 11138507 | 11138536 | Hypo | literature | SMARCA4 | chr19 | 12147437 | 12147545 | Hypo | cancer_general | AX721123, AK023304, ZNF136 |
| chr19 | 12205385 | 12205434 | Hypo | hepatobiliary | ZNF788 | chr19 | 12303495 | 12303551 | Hypo | breast | ASNA1, C19orf43 |
| chr19 | 12661175 | 12661221 | Hypo | cancer_general | ZNF564, ZNF709 | chr19 | 12846906 | 12847098 | Hypo | cancer_general | ASNA1, BEST2 |
| chr19 | 12860307 | 12860433 | Hypo | cancer_general | BEST2, ASNA1 | chr19 | 12863412 | 12863520 | Hypo | cancer_general | — |
| chr19 | 13491305 | 13491340 | Hypo | esophageal | CACNA1A | chr19 | 13782965 | 13783028 | Hypo | hepatobiliary | RFX1 |
| chr19 | 13903520 | 13903603 | Hypo | cancer_general | ZSWIM4 | chr19 | 13965838 | 13965965 | Hypo | cancer_general | — |
| chr19 | 13988775 | 13988805 | Hypo | cancer_general | C19orf57, NANOS3, MIR181D, MIR181C | chr19 | 14085021 | 14085051 | Hypo | cancer_general | — |
| chr19 | 14181305 | 14181846 | Hypo | breast | LOC113230 | chr19 | 14324876 | 14324906 | Hypo | cancer_general | — |
| chr19 | 14327101 | 14327158 | Hypo | cancer_general | — | chr19 | 14334020 | 14334060 | Hypo | colorectal | — |
| chr19 | 14411056 | 14411086 | Hypo | cancer_general | — | chr19 | 14663925 | 14664183 | Hypo | breast | TECR |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 14664479 | 14664561 | Hypo | breast | TECR | chr19 | 14869496 | 14869526 | Hypo | cancer_general | EMR2 |
| chr19 | 15292384 | 15292499 | Hypo | cancer_general, literature | NOTCH3 | chr19 | 15519444 | 15519474 | Hypo | ovarian | AKAP8L |
| chr19 | 16766902 | 16766932 | Hypo | head_neck | TMEM38A, SMIM7 | chr19 | 17000570 | 17000599 | Hypo | literature | CPAMD8, F2RL3, SIN3B |
| chr19 | 17152333 | 17152363 | Hypo | cancer_general | HAUS8 | chr19 | 17335642 | 17335718 | Hypo | cancer_general | OCEL1, NR2F6, USE1 |
| chr19 | 17336042 | 17336111 | Hypo | cancer_general | OCEL1, NR2F6, USE1 | chr19 | 17359350 | 17359459 | Hypo | cancer_general | USHBP1, NR2F6 |
| chr19 | 17436061 | 17436203 | Hypo | head_neck | GTPBP3, ANO8, DDA1 | chr19 | 17446897 | 17447045 | Hypo | cancer_general | AK310794, GTPBP3, ANO8 |
| chr19 | 17759224 | 17759423 | Hypo | literature | UNC13A | chr19 | 17943423 | 17943452 | Hypo | literature | JAK3 |
| chr19 | 17945891 | 17945983 | Hypo | literature | JAK3 | chr19 | 17947991 | 17948023 | Hypo | literature | JAK3 |
| chr19 | 17949094 | 17949123 | Hypo | literature | JAK3 | chr19 | 18041069 | 18041203 | Hypo | cancer_general | CCDC124 |
| chr19 | 18057603 | 18057655 | Hypo | cancer_general | KCNN1, CCDC124 | chr19 | 18103711 | 18103741 | Hypo | cancer_general | ARRDC2, KCNN1 |
| chr19 | 18104472 | 18104606 | Hypo | cancer_general | ARRDC2, KCNN1 | chr19 | 18126412 | 18126442 | Hypo | ovarian | ARRDC2 |
| chr19 | 18271894 | 18271923 | Hypo | literature | PIK3R2, MAST3 | chr19 | 18278047 | 18278076 | Hypo | literature | IFI30, PIK3R2 |
| chr19 | 18300127 | 18300422 | Hypo | cancer_general | MPV17L2, RAB3A | chr19 | 18301007 | 18301037 | Hypo | cancer_general | RAB3A, MPV17L2 |
| chr19 | 18331031 | 18331136 | Hypo | cancer_general | PDE4C | chr19 | 18383211 | 18383351 | Hypo | cancer_general | JUND, MIR3188 |
| chr19 | 18488862 | 18488915 | Hypo | cancer_general | GDF15, MIR3189, PGPEP1 | chr19 | 18496000 | 18496030 | Hypo | head_neck | GDF15, MIR3189, LRRC25 |
| chr19 | 18523115 | 18523145 | Hypo | cancer_general | SSBP4 | chr19 | 18633926 | 18633980 | Hypo | cancer_general | FKBP8, ELL |
| chr19 | 18681638 | 18681926 | Hypo | cancer_general | UBA52, DL491652, KXD1 | chr19 | 18856379 | 18856409 | Hypo | ovarian | CRTC1 |
| chr19 | 18872825 | 18872900 | Hypo | cancer_general | CRTC1 | chr19 | 18989821 | 18990281 | Hypo | cancer_general | CERS1, GDF1 |
| chr19 | 18994887 | 18995206 | Hypo | cancer_general | GDF1, CERS1 | chr19 | 19260030 | 19260101 | Hypo | literature | MEF2B, MEF2BNB-MEF2B |
| chr19 | 19261519 | 19261548 | Hypo | literature | MEF2B, MEF2BNB-MEF2B | chr19 | 19334831 | 19334915 | Hypo | cancer_general | NCAN |
| chr19 | 19489251 | 19489297 | Hypo | cancer_general | GATAD2A | chr19 | 19636877 | 19636907 | Hypo | ovarian | NDUFA13, YJEFN3 |
| chr19 | 19645834 | 19645925 | Hypo | cancer_general | CILP2, YJEFN3, NDUFA13 | chr19 | 19775308 | 19775472 | Hypo | cancer_general | ZNF101, ATP13A1 |
| chr19 | 21237609 | 21237655 | Hypo | hepatobiliary | ZNF430 | chr19 | 21239053 | 21239129 | Hypo | hepatobiliary | ZNF430 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 21245066 | 21245152 | Hypo | hepatobiliary | ZNF430 | chr19 | 21265890 | 21265920 | Hypo | cancer_general | ZNF714 |
| chr19 | 21289719 | 21289749 | Hypo | hepatobiliary | ZNF714 | chr19 | 21290153 | 21290216 | Hypo | hepatobiliary | ZNF714 |
| chr19 | 21303863 | 21303993 | Hypo | hepatobiliary | AX746719, ZNF714 | chr19 | 21305707 | 21305737 | Hypo | hepatobiliary | AX746719, ZNF714 |
| chr19 | 21370382 | 21370479 | Hypo | hepatobiliary | ZNF431 | chr19 | 21512594 | 21512660 | Hypo | cancer_general | ZNF708 |
| chr19 | 21665258 | 21665288 | Hypo | cancer_general | LINC00664 | chr19 | 29505153 | 29505183 | Hypo | cancer_general | LOC100505835 |
| chr19 | 30130889 | 30130919 | Hypo | tcga | | chr19 | 30186141 | 30186278 | Hypo | lung | C19orf12 |
| chr19 | 30215753 | 30215782 | Hypo | cancer_general | C19orf12 | chr19 | 30252296 | 30252369 | Hypo | cancer_general | — |
| chr19 | 30555329 | 30555376 | Hypo | cancer_general | — | chr19 | 30562775 | 30563017 | Hypo | cancer_general | — |
| chr19 | 30582601 | 30582649 | Hypo | cancer_general | — | chr19 | 30637494 | 30637531 | Hypo | cancer_general | — |
| chr19 | 30703436 | 30703469 | Hypo | cancer_general | — | chr19 | 31804724 | 31804754 | Hypo | cancer_general | TSHZ3 |
| chr19 | 32364365 | 32364403 | Hypo | cancer_general | — | chr19 | 32380872 | 32380961 | Hypo | cancer_general | — |
| chr19 | 32516399 | 32516516 | Hypo | cancer_general | AK097493 | chr19 | 32835279 | 32835309 | Hypo | cancer_general | ZNF507 |
| chr19 | 32898335 | 32898490 | Hypo | cancer_general | LOC400684, DPY19L3 | chr19 | 33468018 | 33468055 | Hypo | breast | RHPN2, C19orf40, CEP89 |
| chr19 | 33571236 | 33571280 | Hypo | lung, cancer_general | GPATCH1 | chr19 | 34896324 | 34896360 | Hypo | cancer_general | GPI, PDCD2L |
| chr19 | 35616341 | 35616397 | Hypo | cancer_general | LGI4, FXYD3 | chr19 | 35781374 | 35781459 | Hypo | cancer_general | MAG, HAMP |
| chr19 | 35783136 | 35783231 | Hypo | cancer_general | MAG, HAMP | chr19 | 35797916 | 35797965 | Hypo | cancer_general | MAG |
| chr19 | 36194934 | 36194996 | Hypo | ovarian | ZBTB32 | chr19 | 36200805 | 36200847 | Hypo | cancer_general | ZBTB32, KMT2B |
| chr19 | 36222432 | 36222534 | Hypo | cancer_general | IGFLR1, KMT2B | chr19 | 36250029 | 36250134 | Hypo | cancer_general | HSPB6, LIN37, AL137752, C19orf55 |
| chr19 | 36264697 | 36264773 | Hypo | cancer_general | ARHGAP33, C19orf55 | chr19 | 36265053 | 36265186 | Hypo | cancer_general | C19orf55, ARHGAP33 |
| chr19 | 36410956 | 36411042 | Hypo | esophageal | BC071809, THAP8, CLIP3 | chr19 | 36413776 | 36413830 | Hypo | cancer_general | — |
| chr19 | 36531924 | 36531954 | Hypo | ovarian | | chr19 | 36707435 | 36707467 | Hypo | cancer_general | ZNF146, ZNF565 |
| chr19 | 37702003 | 37702169 | Hypo | cancer_general | ZNF383, ZNF585B | chr19 | 38441488 | 38441518 | Hypo | breast | SIPA1L3 |
| chr19 | 38481044 | 38481217 | Hypo | cancer_general | SIPAIL3 | chr19 | 38733924 | 38733954 | Hypo | cancer_general | PPP1R14A, SPINT2, PPP1R14A |
| chr19 | 38736072 | 38736127 | Hypo | cancer_general | PPP1R14A | chr19 | 38747729 | 38747767 | Hypo | cancer_general | PPP1R14A, SPINT2 |
| chr19 | 38757128 | 38757308 | Hypo | cancer_general | PPP1R14A, SPINT2 | chr19 | 38782559 | 38782589 | Hypo | breast | — |
| chr19 | 38789218 | 38789288 | Hypo | cancer_general | YIF1B, C19orf33, SPINT2 | chr19 | 38873935 | 38873965 | Hypo | cancer_general | GGN, SPRED3, PSMD8 |
| chr19 | 38905548 | 38905702 | Hypo | cancer_general | RASGRP4, FAM98C | chr19 | 38974232 | 38974262 | Hypo | cancer_general | RYR1 |
| chr19 | 39135294 | 39135454 | Hypo | cancer_general | ACTN4, EIF3K | chr19 | 39273027 | 39273062 | Hypo | ovarian | LGALS7B, LGALS7 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 39290904 | 39290944 | Hypo | cancer_general | LGALS4, LGALS7B | chr19 | 39306433 | 39306545 | Hypo | colorectal | ECH1, HNRNPL, LGALS4 |
| chr19 | 39310469 | 39310584 | Hypo | colorectal | ECH1, LGALS4, HNRNPL | chr19 | 39650791 | 39650967 | Hypo | breast | PAK4 |
| chr19 | 39816936 | 39817085 | Hypo | cancer_general | BC110060, GMFG | chr19 | 39934694 | 39934784 | Hypo | cancer_general | SUPT5H, RPS16 |
| chr19 | 40210391 | 40210573 | Hypo | cancer_general | — | chr19 | 40762943 | 40762972 | Hypo | literature | AKT2 |
| chr19 | 40829079 | 40829211 | Hypo | breast | C19orf47 | chr19 | 40829793 | 40830032 | Hypo | cancer_general, breast | C19orf47 |
| chr19 | 40902425 | 40902812 | Hypo | cancer_general | PRX, HIPK4 | chr19 | 40951175 | 40951357 | Hypo | cancer_general | BLVRB, SERTAD3 |
| chr19 | 40951679 | 40951762 | Hypo | cancer_general | BLVRB, SERTAD3 | chr19 | 40991013 | 40991139 | Hypo | cancer_general | SPTBN4 |
| chr19 | 41473190 | 41473242 | Hypo | cancer_general | — | chr19 | 41694610 | 41694640 | Hypo | cancer_general | CYP2S1, TMEM91, BCKDHA |
| chr19 | 41846193 | 41846325 | Hypo | ovarian | TGFB1 | chr19 | 41881534 | 41881811 | Hypo | cancer_general | ARHGEF1, MEGF8 |
| chr19 | 41919917 | 41919971 | Hypo | pancreas | BCKDHA, ATP1A3, RABAC1 | chr19 | 42408300 | 42408330 | Hypo | cancer_general | ARHGEF1, MEGF8 |
| chr19 | 42460961 | 42461113 | Hypo | colorectal | | chr19 | 42856453 | 42856483 | Hypo | lung | |
| chr19 | 42911568 | 42911598 | Hypo | esophageal | LIPE, LIPE-AS1 | chr19 | 44599783 | 44599883 | Hypo | cancer_general | LOC100379224, ZNF224, ZNF284 |
| chr19 | 45003211 | 45003323 | Hypo | cancer_general | CEACAM20, ZNF180 | chr19 | 45541556 | 45541679 | Hypo | cancer_general | CLASRP, RELB |
| chr19 | 45570401 | 45570450 | Hypo | breast | ZNF296, CLASRP | chr19 | 45574465 | 45574495 | Hypo | cancer_general | GEMIN7, CLASRP, ZNF296 |
| chr19 | 45574773 | 45574888 | Hypo | breast | GEMIN7, ZNF296, CLASRP | chr19 | 45601380 | 45601410 | Hypo | cancer_general | PPP1R37, GEMIN7 |
| chr19 | 45678395 | 45678555 | Hypo | ovarian | BLOC1S3, TRAPPC6A | chr19 | 45810102 | 45810267 | Hypo | cancer_general | CKM |
| chr19 | 45835028 | 45835268 | Hypo | cancer_general | KLC3, CKM | chr19 | 45997528 | 45997584 | Hypo | cancer_general | PPM1N, RTN2 |
| chr19 | 46234803 | 46234887 | Hypo | cancer_general | LOC388553 | chr19 | 46404522 | 46404601 | Hypo | cancer_general | MYPOP |
| chr19 | 47200361 | 47200536 | Hypo | cancer_general | PRKD2 | chr19 | 47329748 | 47329867 | Hypo | cancer_general | SNAR-E NPAS1 |
| chr19 | 47358646 | 47358751 | Hypo | cancer_general | AP2S1 | chr19 | 47515017 | 47515047 | Hypo | cancer_general | ARHGAP35 |
| chr19 | 47618255 | 47618434 | Hypo | cancer_general | ZC3H4 | chr19 | 47976399 | 47976429 | Hypo | cancer_general | KPTN, SLC8A2 |
| chr19 | 48003607 | 48003714 | Hypo | cancer_general | NAPA, NAPA-AS1 | chr19 | 48082100 | 48082130 | Hypo | cancer_general | — |
| chr19 | 48108151 | 48108320 | Hypo | cancer_general | GLTSCR1 | chr19 | 48137171 | 48137307 | Hypo | cancer_general | GLTSCR1, GLTSCR2, SNORD23, EHD2 |
| chr19 | 48151265 | 48151337 | Hypo | cancer_general | GLTSCR1 | chr19 | 48249451 | 48249602 | Hypo | cancer_general | |
| chr19 | 48614843 | 48614873 | Hypo | cancer_general | LIG1, PLA2G4C | chr19 | 48771551 | 48771600 | Hypo | cancer_general | ZNF114 |

TABLE 11-continued

| chr | Start | Stop | Hypo/hyper | classification | annotation |
|---|---|---|---|---|---|
| chr19 | 48777059 | 48777121 | Hypo | cancer_general | ZNF114 |
| chr19 | 48857725 | 48857831 | Hypo | cancer_general | Mir_324, SYNGR4, TMEM143 |
| chr19 | 49043242 | 49043272 | Hypo | cancer_general | — |
| chr19 | 49180462 | 49180558 | Hypo | cancer_general | NTN5 |
| chr19 | 49290711 | 49290844 | Hypo | cancer_general | BCAT2, Mir_324 |
| chr19 | 49402471 | 49402551 | Hypo | cancer_general | TULP2, NUCB1, Mir_324 |
| chr19 | 49590284 | 49590399 | Hypo | cancer_general | SNRNP70 |
| chr19 | 49784869 | 49784935 | Hypo | cancer_general | SLC6A16 |
| chr19 | 49997263 | 49997324 | Hypo | cancer_general | RPS11, SNORD34, SNORD32A, FLT3LG, SNORD35B, MIR150, SNORD35A, SNORD33, RPL13A |
| chr19 | 50028397 | 50028530 | Hypo | cancer_general | RCN3, TRNA_Lys, FCGRT |
| chr19 | 50203173 | 50203203 | Hypo | cancer_general | ADM5, CPT1C |
| chr19 | 50243339 | 50243379 | Hypo | head_neck | TSKS |
| chr19 | 50319874 | 50319916 | Hypo | cancer_general | MED25, FUZ, AP2A1 |
| chr19 | 50353394 | 50353574 | Hypo | cancer_general | PTOV1, MIR4749, PTOV1-AS1 |
| chr19 | 50874895 | 50874933 | Hypo | cancer_general | NR1H2, NAPSA |
| chr19 | 50938547 | 50938691 | Hypo | cancer_general | MYBPC2, SPIB |
| chr19 | 48800603 | 48800769 | Hypo | cancer_general | CCDC114, ZNF114 |
| chr19 | 48902848 | 48902878 | Hypo | cancer_general | GRIN2D, KDELR1 |
| chr19 | 49119229 | 49119259 | Hypo | cancer_general | SPACA4, FAM83E, RPL18, SPHK2 |
| chr19 | 49285456 | 49285593 | Hypo | cancer_general | PPP1R15A, TULP2, PLEKHA4 |
| chr19 | 49375050 | 49375216 | Hypo | cancer_general | RUVBL2 |
| chr19 | 49498076 | 49498148 | Hypo | cancer_general | PPFIA3, C19orf73, Mir_324, LIN7B |
| chr19 | 49628132 | 49628252 | Hypo | cancer_general | CCDC155 |
| chr19 | 49890887 | 49890929 | Hypo | cancer_general | FLT3LG, SNORD35B, MIR150, SNORD34, RPL13A, RPS11, SNORD35A, SNORD33, SNORD32A |
| chr19 | 49998434 | 49998607 | Hypo | cancer_general | |
| chr19 | 50049718 | 50049953 | Hypo | cancer_general | NOSIP |
| chr19 | 50216042 | 50216072 | Hypo | cancer_general | CPT1C |
| chr19 | 50304736 | 50304766 | Hypo | pancreas | AP2A1, FUZ |
| chr19 | 50320233 | 50320277 | Hypo | cancer_general | MED25, FUZ, AP2A1 |
| chr19 | 50889044 | 50889079 | Hypo | ovarian | SNAR-A3 |
| chr19 | 50898558 | 50898727 | Hypo | colorectal | POLD1 |
| chr19 | 51304554 | 51304602 | Hypo | cancer_general | SNORD88C, SNORD88A, SNORD88B, C19orf48, ACPT |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 51715329 | 51715359 | Hypo | cancer_general | — | chr19 | 52139210 | 52139326 | Hypo | cancer_general | SIGLEC14, SIGLEC5 |
| chr19 | 52391235 | 52391264 | Hypo | literature | ZNF649, ZNF577 | chr19 | 52715963 | 52715992 | Hypo | literature | PPP2R1A |
| chr19 | 53028928 | 53029035 | Hypo | cancer_general | ZNF808 | chr19 | 53204758 | 53204837 | Hypo | hepatobiliary | ZNF611 |
| chr19 | 53291021 | 53291081 | Hypo | cancer_general | ZNF28 | chr19 | 53398908 | 53399031 | Hypo | hepatobiliary | ZNF320 |
| chr19 | 53399814 | 53399848 | Hypo | cancer_general | ZNF320 | chr19 | 53436895 | 53437067 | Hypo | hepatobiliary | ZNF816-ZNF321P, ZNF321P |
| chr19 | 53446951 | 53447130 | Hypo | hepatobiliary | ZNF816, ZNF816-ZNF321P, ZNF321P | chr19 | 53688015 | 53688059 | Hypo | hepatobiliary | ZNF665 |
| chr19 | 53860082 | 53860151 | Hypo | hepatobiliary | ZNF525, ZNF765, ZNF845 | chr19 | 53873182 | 53873212 | Hypo | hepatobiliary | ZNF765, ZNF525 |
| chr19 | 54271479 | 54271509 | Hypo | hepatobiliary | MIR519A2, MIR516A2, MIR1283-2 | chr19 | 54850630 | 54850659 | Hypo | literature | LILRA4 |
| chr19 | 55728901 | 55729104 | Hypo | cancer_general | PTPRH, TMEM86B | chr19 | 55849550 | 55849638 | Hypo | cancer_general | SUV420H2, TMEM150B |
| chr19 | 56201643 | 56201938 | Hypo | ovarian | EPN1 | chr19 | 56340995 | 56341033 | Hypo | cancer_general | NLRP4, NLRP11 |
| chr19 | 56588656 | 56888780 | Hypo | cancer_general | ZNF787 | chr19 | 56858084 | 56858227 | Hypo | cancer_general | ZNF552 |
| chr19 | 57323825 | 57323854 | Hypo | literature | PEG3-AS1, PEG3, ZIM2 | chr19 | 58316915 | 58317096 | Hypo | cancer_general | |
| chr19 | 58325075 | 58325282 | Hypo | cancer_general | ZNF587, ZNF587B, ZNF552 | chr19 | 58807869 | 58807931 | Hypo | ovarian | LOC113386, ZNF8 |
| chr19 | 58874735 | 58874987 | Hypo | cancer_general | BC023201, ZNF497, A1BG-AS1, A1BG, ZNF837 | chr19 | 58964180 | 58964266 | Hypo | cancer_general | ZNF324B |
| chr19 | 59054642 | 59054774 | Hypo | cancer_general | TRIM28, CHMP2A | AC160854.2_10710-13495 | 1027 | 1057 | Hypo | ovarian | |
| HPV18 | 111 | 140 | Hypo | virus | — | HPV18 | 383 | 412 | Hypo | virus | — |
| HPV18 | 655 | 684 | Hypo | virus | — | HPV18 | 927 | 956 | Hypo | virus | — |
| HPV18 | 1199 | 1228 | Hypo | virus | — | HPV18 | 1471 | 1500 | Hypo | virus | — |
| HPV18 | 1743 | 1772 | Hypo | virus | — | HPV18 | 2015 | 2044 | Hypo | virus | — |
| HPV18 | 2287 | 2316 | Hypo | virus | — | HPV18 | 2559 | 2588 | Hypo | virus | — |
| HPV18 | 2831 | 2860 | Hypo | virus | — | HPV18 | 3103 | 3132 | Hypo | virus | — |
| HPV18 | 3375 | 3404 | Hypo | virus | — | HPV18 | 3647 | 3676 | Hypo | virus | — |
| HPV18 | 3919 | 3948 | Hypo | virus | — | HPV18 | 4191 | 4220 | Hypo | virus | — |
| HPV18 | 4463 | 4492 | Hypo | virus | — | HPV18 | 4735 | 4764 | Hypo | virus | — |
| HPV18 | 5007 | 5036 | Hypo | virus | — | HPV1 | 5279 | 5308 | Hypo | virus | — |
| HPV18 | 5551 | 5580 | Hypo | virus | — | HPV18 | 5823 | 5852 | Hypo | virus | — |
| HPV18 | 6095 | 6124 | Hypo | virus | — | HPV18 | 6367 | 6396 | Hypo | virus | — |

TABLE 11-continued

| chr | Start | Stop | Hypo/hyper | classification | annotation |
|---|---|---|---|---|---|
| HPV18 | 6639 | 6668 | Hypo | virus | — |
| HPV18 | 7183 | 7212 | Hypo | virus | — |
| chr17 | 415134 | 415163 | Hypo | literature | VPS53 |
| chr17 | 617001 | 617064 | Hypo | cancer_general | VPS53 |
| chr17 | 1136593 | 1136653 | Hypo | cancer_general | — |
| chr17 | 1545976 | 1546442 | Hypo | cancer_general | PRPF8, SCARF1, RILP |
| chr17 | 2207718 | 2208063 | Hypo | cancer_general | SRR, SMG6 |
| chr17 | 2220564 | 2221059 | Hypo | cancer_general | SRR, TSR1 |
| chr17 | 2278801 | 2278925 | Hypo | breast | SGSM2, MNT |
| chr17 | 2538269 | 2538337 | Hypo | cancer_general | PAFAH1B1 |
| chr17 | 2811392 | 2811392 | Hypo | hepatobiliary | RAP1GAP2 |
| chr17 | 2950959 | 2951091 | Hypo | cancer_general | RAP1GAP2 |
| chr17 | 3658849 | 3659011 | Hypo | cancer_general | — |
| chr17 | 4698990 | 4699252 | Hypo | cancer_general | PSMB6, GLTPD2, BC150535, VMO1 |
| chr17 | 5168597 | 5168732 | Hypo | breast | — |
| chr17 | 7043422 | 7043595 | Hypo | cancer_general | — |
| chr17 | 7368947 | 7369139 | Hypo | ovarian | ZBTB4, CHRNB1 |
| chr17 | 7488151 | 7488249 | Hypo | cancer_general | SOX15, CD68, DD413682, SNORA67, SNORD10, SNORA48, MPDU1, FXR2, SENP3-EIF4A1 |
| chr17 | 7573968 | 7574028 | Hypo | literature | HV941486, HV941440, |
| HPV18 | 6911 | 6940 | Hypo | virus | — |
| HPV18 | 7455 | 7484 | Hypo | virus | — |
| chr17 | 556252 | 556282 | Hypo | head_neck | VPS53 |
| chr17 | 631704 | 631734 | Hypo | head_neck | FAM57A |
| chr17 | 1536116 | 1536146 | Hypo | head_neck | SCARF1 WDR81, MIR22, AF070569, MIR22HG |
| chr17 | 1623703 | 1623735 | Hypo | cancer_general | SRR, TSR1 |
| chr17 | 2219952 | 2220319 | Hypo | cancer_general | SGSM2 |
| chr17 | 2250051 | 2250081 | Hypo | cancer_general | PAFAH1B1, DD413682 |
| chr17 | 2496019 | 2496049 | Hypo | cancer_general | — |
| chr17 | 2663898 | 2664032 | Hypo | cancer_general | RAP1GAP2 |
| chr17 | 2873476 | 2873553 | Hypo | hepatobiliary | — |
| chr17 | 3657502 | 3657553 | Hypo | cancer_general | PSMB6, GLTPD2, BC150535, VMO1, TM4SF5 |
| chr17 | 4693354 | 4693388 | Hyp | breast | — |
| chr17 | 5167638 | 5167681 | Hypo | breast | ACAP1 |
| chr17 | 6470357 | 6470419 | Hypo | cancer_general | SENP3-EIF4A1, SNORA48, SNORD10, SNORA67, DD413682, SENP3, TNFSF13 |
| chr17 | 7242844 | 7242899 | Hypo | cancer_general | |
| chr17 | 7471610 | 7471709 | Hypo | colorectal | |
| chr17 | 7572957 | 7573018 | Hypo | literature | HV941442, HV941444, HV941430, HV941433, HV941428, HV941434, HV941429, HV941478, HV941431, TP53, HV941486, HV941440 |
| chr17 | 7576847 | 7577167 | Hypo | literature | HV941486, HV941429, |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| | | | | | HV941478, TP53, HV941429, HV941442, HV941444, HV941430, HV941433, HV941428, HV941434, HV941431 | | | | | | HV941430, HV941434, TP53, HV941440, HV941478, HV941442, HV941444, HV941431, HV941433, HV941428 |
| chr17 | 7577504 | 7577604 | Hypo | literature | TP53, HV941478, HV941442, HV941444, HV941430, HV941486, HV941428, HV941433, HV941429, HV941434, HV941440, HV941431 | chr17 | 7578164 | 7578570 | Hypo | literature | HV941486, HV941434, HV941428, HV941440, HV941478, HV941442, HV941444, HV941429, HV941431, TP53, HV941430, HV941433 |
| chr17 | 7579285 | 7579880 | Hypo | literature | TP53, HV941430, WRAP53, HV941478, HV941429, HV941428, HV941444, HV941440, HV941486, HV941434, HV941431, HV941433, HV941442 | chr17 | 7906832 | 7906861 | Hypo | tcga | GUCY2D |
| chr17 | 8104145 | 8104260 | Hypo | cancer_general | AURKB | chr17 | 8774623 | 8774653 | Hypo | cancer_general | PIK3R5, PIK3R6 |
| chr17 | 9790805 | 9790835 | Hypo | cancer_general | GLP2R | chr17 | 10599510 | 10599546 | Hypo | cancer_general | SCO1, ADPRM |
| chr17 | 11984693 | 11984722 | Hypo | literature | MIR744, MAP2K4 | chr17 | 11998944 | 11998973 | Hypo | literature | — |
| chr17 | 12013726 | 12013755 | Hypo | literature | — | chr17 | 12016550 | 12016630 | Hypo | literature | — |
| chr17 | 12028618 | 12028647 | Hypo | literature | TTC19, NCOR1 | chr17 | 12659029 | 12659063 | Hypo | cancer_general | MYOCD PIGL, NCOR1 |
| chr17 | 15926819 | 15926849 | Hypo | head_neck | UBB | chr17 | 16120047 | 16120047 | Hypo | cancer_general | |
| chr17 | 16282251 | 16282300 | Hypo | cancer_general | UBB | chr17 | 16326144 | 16326216 | Hypo | head_neck | TRPV2 |
| chr17 | 16428708 | 16428738 | Hypo | head_neck | — | chr17 | 17062574 | 17062763 | Hypo | head_neck | MPRIP |
| chr17 | 17117365 | 17117395 | Hypo | breast | FLCN, PLD6 | chr17 | 17123963 | 17123993 | Hypo | head_neck | FLCN, PLD6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 17719242 | 17719355 | Hypo | breast | MIR33B, SREBP-1, SREBF1 | chr17 | 18162844 | 18163325 | Hypo | cancer_general | FLII, SMCR7, DQ596932 |
| chr17 | 18817198 | 18817284 | Hypo | esophageal | PRPSAP2 | chr17 | 19769739 | 19769821 | Hypo | cancer_general | TRNA_Gly |
| chr17 | 19886035 | 19886221 | Hypo | head_neck | AKAP10 | chr17 | 20039589 | 20039676 | Hypo | hepatobiliary | SPECC1 |
| chr17 | 20081131 | 20081161 | Hypo | hepatobiliary | SPECC1 | chr17 | 20205055 | 20205181 | Hypo | hepatobiliary | SPECC1 |
| chr17 | 20238152 | 20238198 | Hypo | hepatobiliary | CCDC144CP | chr17 | 20468021 | 20468090 | Hypo | hepatobiliary | DQ584223 |
| chr17 | 20817755 | 20817917 | Hypo | cancer_general | — | chr17 | 21003587 | 21003721 | Hypo | cancer_general | HP08942 |
| chr17 | 25620573 | 25620715 | Hypo | cancer_general | MIR4522, WSB1 | chr17 | 25676959 | 25676989 | Hypo | cancer_general | — |
| chr17 | 25680264 | 25680294 | Hypo | cancer_general | — | chr17 | 25907750 | 25907780 | Hypo | cancer_general | KSR1 |
| chr17 | 26263183 | 26263322 | Hypo | cancer_general | — | chr17 | 26927249 | 26927410 | Hypo | cancer_general | SGK494, SPAG5-AS1, SPAG5 |
| chr17 | 26961770 | 26961833 | Hypo | cancer_general, breast | KIAA0100 | chr17 | 27036492 | 27037023 | Hypo | cancer_general | RAB34, NARR, RPL23A, PROCA1 |
| chr17 | 27055577 | 27056857 | Hypo | cancer_general | SNORD42A, SNORD4A, SNORD42B, RPL23A, NEK8, TLCD1, SNORD4B | chr17 | 27081845 | 27081963 | Hypo | cancer_general | FAM222B, TRAF4 |
| chr17 | 27170162 | 27170460 | Hypo | cancer_general | FAM222B | chr17 | 27181180 | 27181371 | Hypo | lung | ERAL1, MIR451A, MIR451B, MIR144, MIR4732 |
| chr17 | 27686651 | 27686783 | Hypo | colorectal | — | chr17 | 27716114 | 27716220 | Hypo | cancer_general | MIR4523, TAOK1 |
| chr17 | 27716436 | 27716642 | Hypo | cancer_general | MIR4523, TAOK1 | chr17 | 28112648 | 28112688 | Hypo | cancer_general | SSH2 |
| chr17 | 28112951 | 28113037 | Hypo | cancer_general | SSH2 | chr17 | 29232244 | 29232350 | Hypo | cancer_general | TEFM |
| chr17 | 29234283 | 29234313 | Hypo | cancer_general | TEFM | chr17 | 29508761 | 29508790 | Hypo | literature | NF1 |
| chr17 | 29541527 | 29541556 | Hypo | literature | NF1 | chr17 | 29562732 | 29562761 | Hypo | literature | NF1 |
| chr17 | 30243768 | 30243907 | Hypo | cancer_general | — | chr17 | 30250325 | 30250364 | Hypo | cancer_general | — |
| chr17 | 30258469 | 30258499 | Hypo | head_neck | SUZ12 | chr17 | 30568137 | 30568174 | Hypo | breast | — |
| chr17 | 30710818 | 30710888 | Hypo | cancer_general | ZNF207 | chr17 | 32386720 | 32386875 | Hypo | cancer_general | — |
| chr17 | 33721211 | 33721349 | Hypo | cancer_general | — | chr17 | 33877286 | 33877439 | Hypo | cancer_general | SLFN14 |
| chr17 | 33917210 | 33917268 | Hypo | cancer_general | AP2B1 | chr17 | 37001415 | 37001921 | Hypo | cancer_general | SNORA21, C17orf98, RPL23 |
| chr17 | 37011176 | 37011236 | Hypo | cancer_general | RPL23, TRNA_Cys, SNORA21 | chr17 | 37131789 | 37132028 | Hypo | cancer_general | FBXO47 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 37181771 | 37181865 | Hypo | cancer_general | LRRC37A11P | chr17 | 37192072 | 37192201 | Hypo | cancer_general | LRRC37A11P |
| chr17 | 37312431 | 37312477 | Hypo | cancer_general | ARL5C, TRNA_Cys, PLXDC1 | chr17 | 37369180 | 37369210 | Hypo | cancer_general | STAC2, RPL19 |
| chr17 | 37484062 | 37484128 | Hypo | cancer_general | FBXL20 | chr17 | 37868190 | 37868294 | Hypo | literature | ERBB2 |
| chr17 | 37879568 | 37879615 | Hypo | literature | MIR4728, MIEN1, ERBB2 | chr17 | 37880205 | 37880276 | Hypo | literature | MIR4728, MIEN1, ERBB2 |
| chr17 | 37880971 | 37881018 | Hypo | literature | MIEN1, ERBB2, MIR4728 | chr17 | 37881318 | 37881631 | Hypo | literature | MIR4728, MIEN1, ERBB2 |
| chr17 | 38179397 | 38179430 | Hypo | cancer_general | MED24, SNORD124, CSF3 | chr17 | 38335459 | 38335533 | Hypo | cancer_general | RAPGEFL1, CASC3 |
| chr17 | 38380553 | 38380598 | Hypo | cancer_general | WIPF2 | chr17 | 38473104 | 38473180 | Hypo | literature | RARA AK090604, KRT15, JUP, KRT19 |
| chr17 | 38574991 | 38575021 | Hypo | cancer_general | TOP2A | chr17 | 39682352 | 39682711 | Hypo | cancer_general | |
| chr17 | 39834201 | 39834287 | Hypo | cancer_general | — | chr17 | 40474467 | 40474496 | Hypo | literature | STAT3, AK024535, AK092965 |
| chr17 | 40897739 | 40897788 | Hypo | ovarian | RAMP2-AS1, BC047651, EZH1 | chr17 | 40975413 | 40975677 | Hypo | cancer_general | PSME3, BECN1 |
| chr17 | 41175146 | 41175331 | Hypo | cancer_general | RND2, VAT1, IFI35 | chr17 | 41197714 | 41197743 | Hypo | literature | BRCA1 |
| chr17 | 41201163 | 41201192 | Hypo | literature | BRCA1 | chr17 | 41203073 | 41203102 | Hypo | literature | BRCA1 |
| chr17 | 41209064 | 41209114 | Hypo | literature | BRCA1 | chr17 | 41215890 | 41215961 | Hypo | literature | BRCA1 |
| chr17 | 41267731 | 41267775 | Hypo | literature | NBR2, BRCA1 | chr17 | 41276031 | 41276075 | Hypo | literature | BRCA1, NBR2 |
| chr17 | 41278621 | 41278700 | Hypo | cancer_general | NBR2, BRCA1 | chr17 | 41651850 | 41651880 | Hypo | cancer_general | — |
| chr17 | 41745825 | 41745855 | Hypo | cancer_general | MEOX1 | chr17 | 41791665 | 41791694 | Hypo | tcga | — |
| chr17 | 42110423 | 42110561 | Hypo | head_neck | LSM12 | chr17 | 42142661 | 42142808 | Hypo | cancer_general | LSM12, G6PC3, AX746969 |
| chr17 | 42246452 | 42246521 | Hypo | cancer_general | ASB16, ASB16-AS1, C17orf65, C17orf53 | chr17 | 42321590 | 42321674 | Hypo | cancer_general | SLC4A1 |
| chr17 | 42331412 | 42331659 | Hypo | cancer_general | SLC4A1 | chr17 | 42580695 | 42580793 | Hypo | breast | — |
| chr17 | 42587249 | 42587355 | Hypo | cancer_general | — | chr17 | 42590091 | 42590224 | Hypo | cancer_general | — |
| chr17 | 42767947 | 42768198 | Hypo | cancer_general | CCDC43 | chr17 | 42787481 | 42787616 | Hypo | cancer_general | DBF4B GFAP, KIF18B |
| chr17 | 42975726 | 42975756 | Hypo | cancer_general | CCDC103, FAM187A, AK124465, | chr17 | 43001891 | 43001946 | Hypo | cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 44897416 | 44897445 | Hypo | literature | GFAP, EFTUD2 | chr17 | 45022106 | 45022140 | Hypo | cancer_general | GOSR2 |
| chr17 | 45187608 | 45187638 | Hypo | cancer_general | WNT3 | chr17 | 46567400 | 46567655 | Hypo | cancer_general | — |
| chr17 | 46827420 | 46827539 | Hypo | cancer_general | CDC27 | chr17 | 47657544 | 47657583 | Hypo | cancer_general | NXPH3 |
| chr17 | 48473056 | 48473236 | Hypo | cancer_general | — | chr17 | 48889801 | 48889831 | Hypo | colorectal | MYCBPAP |
| chr17 | 48612223 | 48612308 | Hypo | cancer_general | EPN3, SPATA20, MYCBPAP | chr17 | 48653128 | 48653158 | Hypo | cancer_general | CACNA1G |
| chr17 | 48799820 | 48799866 | Hypo | cancer_general | LUC7L3 | chr17 | 49229267 | 49229703 | Hypo | cancer_general | NME1-NME2, NME1 |
| chr17 | 53479184 | 53479316 | Hypo | colorectal | MMD | chr17 | 53814544 | 53814678 | Hypo | cancer_general | SRSF1 |
| chr17 | 55037326 | 55037626 | Hypo | cancer_general | COIL | chr17 | 56092600 | 56092736 | Hypo | cancer_general | TEX14 |
| chr17 | 56471121 | 56471167 | Hypo | colorectal | RNF43 | chr17 | 56743206 | 56743249 | Hypo | cancer_general | — |
| chr17 | 57296865 | 57297129 | Hypo | cancer_general | GDPD1, SMG8 | chr17 | 57386255 | 57386735 | Hypo | cancer_general | — |
| chr17 | 57787402 | 57787465 | Typo | cancer_general | VMP1, PTRH2 | chr17 | 57832475 | 57832607 | Hypo | cancer_general | VMP1 |
| chr17 | 59481657 | 59481694 | Hypo | esophageal | C17orf82, TBX2 | chr17 | 59924556 | 59924585 | Hypo | literature | — |
| chr17 | 59937192 | 59937236 | Hypo | literature | INTS2 | chr17 | 61677374 | 61677404 | Hypo | cancer_general | TACO1, BC024682, DQ577731, DCAF7 |
| chr17 | 61817576 | 61817955 | Hypo | cancer_general | STRADA, CCDC47 | chr17 | 62028596 | 62028790 | Hypo | cancer_general | SCN4A |
| chr17 | 64672366 | 64672544 | Hypo | cancer_general | — | chr17 | 65715296 | 65715493 | Hypo | cancer_general | NOL11 |
| chr17 | 66420718 | 66420837 | Hypo | lung | MIR635, WIPI1, ARSG | chr17 | 67410305 | 67410397 | Hypo | cancer_general | MAP2K6 |
| chr17 | 70886165 | 70886272 | Hypo | cancer_general | LINC00511, LINC00673 | chr17 | 71229815 | 71229918 | Hypo | cancer_general | C17orf80, FAM104A |
| chr17 | 72236510 | 72236648 | Hypo | hepatobiliary | TTYH2 | chr17 | 72491378 | 72491531 | Hypo | ovarian | — |
| chr17 | 72862371 | 72862460 | Hypo | blood | FDXR, GRIN2C | chr17 | 73031637 | 73031935 | Hypo | cancer_general | Metazoa_SRP, TRNA_Arg, JB153618, KCTD2, ATP5H |
| chr17 | 73115588 | 73115658 | Hypo | cancer_general | ARMC7 | chr17 | 73115884 | 73115914 | Hypo | cancer_general | ARMC7 |
| chr17 | 73128301 | 73128338 | Hypo | cancer_general | NT5C, ARMC7, HN1 | chr17 | 73147177 | 73147356 | Hypo | cancer_general | HN1 |
| chr17 | 73147774 | 73147992 | Hypo | cancer_general | HN1 | chr17 | 73215289 | 73215423 | Hypo | ovarian | NUP85 |
| chr17 | 73351981 | 73352086 | Hypo | breast | GRB2 | chr17 | 73545998 | 73546299 | Hypo | cancer_general | LLGL2 |
| chr17 | 73586015 | 73586418 | Hypo | cancer_general | MYO15B | chr17 | 73608306 | 73608336 | Hypo | cancer_general | MYO15B |
| chr17 | 73636144 | 73636337 | Hypo | cancer_general | RECQL5, SMIM5, SMIM6 | chr17 | 73692986 | 73693122 | Hypo | cancer_general | SAP30BP |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 73782870 | 73782947 | Hypo | cancer_general | UNK, MIR4738, H3F3B | chr17 | 73808631 | 73808671 | Hypo | head_neck | UNK |
| chr17 | 73827213 | 73827243 | Hypo | esophageal | UNC13D, UNK | chr17 | 73901630 | 73901893 | Hypo | cancer_general | MRPL38, TRIM65, FBF1 |
| chr17 | 73904093 | 73904127 | Hypo | lung | FBF1, MRPL38 | chr17 | 74028346 | 74028413 | Hypo | cancer_general | SRP68, EVPL |
| chr17 | 74047797 | 74048063 | Hypo | cancer_general | SRP68 | chr17 | 74087118 | 74087185 | Hypo | head_neck | EXOC7, ZACN |
| chr17 | 74299798 | 74299899 | Hypo | cancer_general | PRPSAP1, QRICH2 | chr17 | 74390363 | 74390393 | Hypo | cancer_general | UBE2O, SPHK1 |
| chr17 | 74663258 | 74663288 | Hypo | head_neck | MXRA7 | chr17 | 74732944 | 74732973 | Hypo | literature | MFSD11, MIR636, SRSF2, METTL23 |
| chr17 | 75207514 | 75207630 | Hypo | blood | SEC14L1 | chr17 | 75207839 | 75207987 | Hypo | blood | SEC14L1 |
| chr17 | 75276054 | 75276083 | Hypo | literature | 9-Sep | chr17 | 75276413 | 75276442 | Hypo | literature | 9-Sep |
| chr17 | 75277348 | 75277659 | Hypo | literature | 9-Sep | chr17 | 75278020 | 75278049 | Hypo | literature | 9-Sep |
| chr17 | 75279105 | 75279134 | Hypo | literature | 9-Sep | chr17 | 75282025 | 75282154 | Hypo | literature | 9-Sep |
| chr17 | 75316368 | 75316397 | Hypo | literature | 9-Sep | chr17 | 75317170 | 75317199 | Hypo | literature | 9-Sep |
| chr17 | 75347755 | 75347784 | Hypo | literature | 9-Sep | chr17 | 75373312 | 75373341 | Hypo | literature | 9-Sep |
| chr17 | 75405827 | 75405856 | Hypo | literature | — | chr17 | 75523142 | 75523272 | Hypo | cancer_general | BC040189 |
| chr17 | 75733978 | 75734244 | Hypo | lung, cancer_general | — | chr17 | 75797111 | 75797179 | Hypo | cancer_general | — |
| chr17 | 76021047 | 76021077 | Hypo | cancer_general | TNRC6C | chr17 | 76130124 | 76130153 | Hypo | literature | TMC8, TMC6 |
| chr17 | 76135783 | 76136001 | Hypo | lung, cancer_general | C17orf99, TMC8 | chr17 | 76137951 | 76138190 | Hypo | cancer_general | C17orf99, TMC8 |
| chr17 | 76138498 | 76138622 | Hypo | cancer_general | TMC8, C17orf99 | chr17 | 76187407 | 76187544 | Hypo | ovarian | AFMID, TK1 |
| chr17 | 76207342 | 76207372 | Hypo | cancer_general | BIRC5, AFMID | chr17 | 76211302 | 76211506 | Hypo | cancer_general | EPR-1, BIRC5, AFMID |
| chr17 | 76404615 | 76404659 | Hypo | colorectal | PGS1 | chr17 | 76877177 | 76877212 | Hypo | hepatobiliary | LOC100653515, TIMP2 |
| chr17 | 76884417 | 76884447 | Hypo | hepatobiliary | LOC100653515, TIMP2 | chr17 | 76974447 | 76974499 | Hypo | cancer_general | LGALS3BP |
| chr17 | 76983518 | 76983669 | Hypo | cancer_general | CANT1, LGALS3BP | chr17 | 76984053 | 76984188 | Hypo | cancer_general | LGALS3BP, CANT1, DQ595190 |
| chr17 | 77070307 | 77070457 | Hypo | colorectal | ENGASE | chr17 | 77084518 | 77084727 | Hypo | ovarian | RBFOX3, ENGASE |
| chr17 | 77105055 | 77105198 | Hypo | cancer_general | RBFOX3 | chr17 | 77145129 | 77145242 | Hypo | cancer_general | RBFOX3 |
| chr17 | 77394706 | 77394850 | Hypo | ovarian | RBFOX3 | chr17 | 77825696 | 77825812 | Hypo | cancer_general | — |
| chr17 | 77827114 | 77827201 | Hypo | cancer_general | — | chr17 | 77919429 | 77919477 | Hypo | pancreas | TBC1D16 |
| chr17 | 77924259 | 77924351 | Hypo | pancreas | TBC1D16 SLC26A11, SGSH | chr17 | 78122158 | 78122190 | Hypo | cancer_general | EIF4A3 |
| chr17 | 78194821 | 78194861 | Hypo | pancreas | | chr17 | 78272278 | 78272313 | Hypo | breast | RNF213 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 78447127 | 78447157 | Hypo | cancer_general | NPTX1, AX746631 | chr17 | 78518031 | 78518198 | Hypo | cancer_general | RPTOR |
| chr17 | 78599596 | 78599628 | Hypo | cancer_general | RPTOR | chr17 | 78667992 | 78668159 | Hypo | cancer_general | RPTOR |
| chr17 | 78874441 | 78874559 | Hypo | cancer_general | — | chr17 | 78975667 | 78975758 | Hypo | cancer_general | AF258550, CHMP6 |
| chr17 | 78999625 | 78999654 | Hypo | literature | BAIAP2-AS1, BAIAP2 | chr17 | 79094182 | 79094245 | Hypo | cancer_general | MIR657, MIR3065, MIR338, AATK |
| chr17 | 79099770 | 79099799 | Hypo | literature | MIR1250, MIR338, MIR3065, MIR657, AATK | chr17 | 79626591 | 79626703 | Hypo | cancer_general | OXLD1, CCDC137, PDE6G |
| chr17 | 79626955 | 79626985 | Hypo | cancer_general | OXLD1, CCDC137, PDE6G | chr17 | 79769433 | 79769693 | Hypo | cancer_general | GCGR |
| chr17 | 79850445 | 79850537 | Hypo | cancer_general | ALYREF, ANAPC11, NPB | chr17 | 79896013 | 79896043 | Hypo | blood | MYADML2, PYCR1, MAFG-AS1 |
| chr17 | 79939605 | 79939835 | Hypo | cancer_general | ASPSCR1 | chr17 | 79945037 | 79945074 | Hypo | breast | ASPSCR1 |
| chr17 | 80254266 | 80254296 | Hypo | cancer_general | BC033560 | chr17 | 80289234 | 80289310 | Hypo | cancer_general | SECTM1 |
| chr17 | 80289858 | 80289892 | Hypo | cancer_general | SECTM1 | chr17 | 80294282 | 80294427 | Hypo | cancer_general | SECTM1 |
| chr17 | 80394063 | 80394185 | Hypo | breast | HEXDC, C17orf62 | chr17 | 80479311 | 80479559 | Hypo | cancer_general | FOXK2 |
| chr17 | 80491572 | 80491602 | Hypo | head_neck | FOXK2 | chr17 | 80535382 | 80535487 | Hypo | colorectal | FOXK2 |
| chr17 | 80571380 | 80571776 | Hypo | lung | WDR45B, FOXK2 | chr17 | 80593754 | 80594107 | Hypo | cancer_general | WDR45B |
| chr17 | 80654983 | 80655013 | Hypo | cancer_general | RAB40B | chr17 | 80749152 | 80749276 | Hypo | ovarian | TBCD |
| chr17 | 80751650 | 80751714 | Hypo | breast | TBCD | chr17 | 80794259 | 80794288 | Hypo | literature | TBCD, ZNF750 |
| chr17 | 80797692 | 80798345 | Hypo | cancer_general | ZNF750, TBCD | chr17 | 80832305 | 80832411 | Hypo | cancer_general | — |
| chr17 | 80832712 | 80832796 | Hypo | cancer_general | — | chr17 | 80859239 | 80859269 | Hypo | head_neck | TBCD |
| chr17 | 81008618 | 81008826 | Hypo | cancer_general | — | chr17 | 81033487 | 81033517 | Hypo | cancer_general | METRNL |
| chr17 | 81048993 | 81049023 | Hypo | cancer_general | METRNL | chr17 | 81049994 | 81050058 | Hypo | cancer_general | METRNL |
| chr20 | 291148 | 291373 | Hyper | liver_tcga, cancer_general | — | chr20 | 590434 | 590502 | Hyper | cancer_general | TCF15 |
| chr20 | 590751 | 590868 | Hyper | cancer_general | TCF15 | chr20 | 592405 | 592449 | Hyper | cancer_general | TCF15 |
| chr20 | 644182 | 644787 | Hyper | cancer_general | SCRT2 | chr20 | 982749 | 982989 | Hyper | cancer_general | RSPO4 |
| chr20 | 1206855 | 1207034 | Hyper | blood | RAD21L1 | chr20 | 1783761 | 1784365 | Hyper | tcga, liver_tcga, cancer_general | — |
| chr20 | 1874512 | 1874541 | Hyper | literature | SIRPA | chr20 | 1876110 | 1876176 | Hyper | esophageal | SIRPA |
| chr20 | 2539331 | 2539771 | Hyper | cancer_general | TMC2 | chr20 | 2668770 | 2668922 | Hyper | cancer_general | EBF4 |
| chr20 | 2780753 | 2781452 | Hyper | tcga, liver_tcga, cancer_general | CPXM1 | chr20 | 2781731 | 2781761 | Hyper | cancer_general | CPXM1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 2785659 | 2786060 | Hyper | cancer_general | TMEM239, C20orf141, CPXM1 | chr20 | 3052583 | 3052836 | Hyper | cancer_general | OXT |
| chr20 | 3073488 | 3073899 | Hyper | cancer_general | AVP | chr20 | 3220893 | 3220943 | Hyper | cancer_general | SLC4A11, C20orf194 |
| chr20 | 3229576 | 3229612 | Hyper | cancer_general | C20orf194, SLC4A11 | chr20 | 3389393 | 3389549 | Hyper | tcga | — |
| chr20 | 3641733 | 3641937 | Hyper | cancer_general | ADAM33, AX748440, GFRA4 | chr20 | 3663020 | 3663174 | Hyper | cancer_general | ADAM33, SIGLEC1 |
| chr20 | 3762152 | 3762181 | Hyper | tcga | CENPB, CDC25B, SPEF1 | chr20 | 4229402 | 4229432 | Hyper | cancer_general | ADRA1D |
| chr20 | 4229786 | 4230600 | Hyper | esophageal, cancer_general | ADRA1D | chr20 | 4803070 | 4803650 | Hyper | tcga, cancer_general | RASSF2 |
| chr20 | 4803921 | 4804008 | Hyper | colorectal | RASSF2 | chr20 | 4804566 | 4804724 | Hyper | tcga | RASSF2 |
| chr20 | 5296172 | 5296900 | Hyper | cancer_general | AX746654, PROKR2 | chr20 | 5297206 | 5297603 | Hyper | cancer_general | AX746654, PROKR2 |
| chr20 | 6748925 | 6749036 | Hyper | blood | BMP2 | chr20 | 8112378 | 8112408 | Hyper | cancer_general | PLCB1 |
| chr20 | 8112739 | 8113022 | Hyper | tcga, cancer_general | PLCB1 | chr20 | 8113557 | 8113605 | Hyper | cancer_general | PLCB1 |
| chr20 | 9487385 | 9487997 | Hyper | cancer_general | LAMP5 | chr20 | 9488376 | 9488795 | Hyper | cancer_general | LAMP5 |
| chr20 | 9489070 | 9489214 | Hyper | cancer_general | LAMP5 | chr20 | 9489424 | 9489708 | Hyper | cancer_general | LAMP5 |
| chr20 | 9495271 | 9495509 | Hyper | cancer_general | LAMP5 | chr20 | 9496330 | 9496833 | Hyper | cancer_general | LAMP5 |
| chr20 | 9497035 | 9497109 | Hyper | cancer_general | LAMP5 | chr20 | 10198289 | 10198600 | Hyper | cancer_general | SNAP25 |
| chr20 | 10198915 | 10198945 | Hyper | cancer_general | SNAP25 | chr20 | 13200599 | 13200634 | Hyper | cancer_general | ISM1, AY927515 |
| chr20 | 17206513 | 17206747 | Hyper | cancer_general | PCSK2 | chr20 | 17207874 | 17207930 | Hyper | cancer_general | PCSK2 |
| chr20 | 17208585 | 17208620 | Hyper | cancer_general | PCSK2 | chr20 | 18039823 | 18039897 | Hyper | blood | OVOL2 |
| chr20 | 18073312 | 18073461 | Hyper | pancreas | — | chr20 | 19739592 | 19739696 | Hyper | cancer_general | — |
| chr20 | 20344498 | 20344559 | Hyper | cancer_general | C20orf26, INSM1 | chr20 | 20345686 | 20346106 | Hyper | cancer_general | INSM1, C20orf26 |
| chr20 | 20347460 | 20348154 | Hyper | cancer_general | INSM1, C20orf26 | chr20 | 20348526 | 20348605 | Hyper | esophageal | INSM1, C20orf26 |
| chr20 | 20349153 | 20349255 | Hyper | tcga, liver_tcga | INSM1, C20orf26 | chr20 | 20349574 | 20349604 | Hyper | esophageal | INSM1, C20orf26 |
| chr20 | 21080714 | 21082253 | Hyper | liver_tcga, cancer_general | — | chr20 | 21082532 | 21082917 | Hyper | cancer_general | — |
| chr20 | 21083421 | 21084361 | Hyper | cancer_general | — | chr20 | 21085831 | 21085864 | Hyper | cancer_general | — |
| chr20 | 21086176 | 21086451 | Hyper | cancer_general | — | chr20 | 21086866 | 21087188 | Hyper | cancer_general | — |
| chr20 | 21372174 | 21372725 | Hyper | cancer_general | NKX2-4, XRN2 | chr20 | 21376250 | 21378551 | Hyper | liver_tcga, cancer_general | NKX2-4, XRN2 |
| chr20 | 21486375 | 21486881 | Hyper | cancer_general | NKX2-2 | chr20 | 21487153 | 21487581 | Hyper | cancer_general | NKX2-2 |
| chr20 | 21488158 | 21488351 | Hyper | cancer_general | NKX2-2 | chr20 | 21489224 | 21489703 | Hyper | cancer_general | NKX2-2 |
| chr20 | 21490175 | 21491529 | Hyper | cancer_general | NKX2-2 | chr20 | 21492378 | 21492983 | Hyper | cancer_general | NKX2-2 |
| chr20 | 21493308 | 21494265 | Hyper | cancer_general | NKX2-2 | chr20 | 21494531 | 21494703 | Hyper | cancer_general | NKX2-2 |
| chr20 | 21495942 | 21495986 | Hyper | cancer_general | NKX2-2 | chr20 | 21496260 | 21496294 | Hyper | cancer_general | NKX2-2 |
| chr20 | 21496637 | 21497136 | Hyper | cancer_general | NKX2-2 | chr20 | 21497413 | 21498638 | Hyper | cancer_general | NKX2-2 |
| chr20 | 21499961 | 21500134 | Hyper | cancer_general | NKX2-2 | chr20 | 21501424 | 21501724 | Hyper | cancer_general | NKX2-2 |
| chr20 | 21502037 | 21502330 | Hyper | cancer_general | NKX2-2 | chr20 | 21502590 | 21503117 | Hyper | cancer_general | NKX2-2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 21503441 | 21503773 | Hyper | cancer_general, tcga | NKX2-2 | chr20 | 21682399 | 21682456 | Hyper | cancer_general | PAX1 |
| chr20 | 21683311 | 21683651 | Hyper | cancer_general | PAX1 | chr20 | 21686235 | 21686677 | Hyper | cancer_general | PAX1 |
| chr20 | 21687009 | 21687731 | Hyper | cancer_general | PAX1 | chr20 | 21689956 | 21690185 | Hyper | cancer_general | PAX1 |
| chr20 | 21694499 | 21694529 | Hyper | cancer_general | PAX1 | chr20 | 21695088 | 21695357 | Hyper | tcga, cancer_general | PAX1 |
| chr20 | 21748445 | 21748491 | Hyper | cancer_general | — | chr20 | 22557396 | 22557675 | Hyper | cancer_general | FOXA2, LINC00261 |
| chr20 | 22557979 | 22558114 | Hyper | cancer_general | FOXA2, LINC00261 | chr20 | 22558637 | 22558669 | Hyper | cancer_general | FOXA2, LINC00261 |
| chr20 | 22559645 | 22559690 | Hyper | cancer_general | FOXA2, LINC00261 | chr20 | 22562721 | 22562840 | Hyper | cancer_general | FOXA2 |
| chr20 | 22563563 | 22563602 | Hyper | cancer_general | FOXA2, LINC00261 | chr20 | 22564235 | 22564265 | Hyper | blood | FOXA2, LINC00261 |
| chr20 | 22566961 | 22566990 | Hyper | literature | | chr20 | 23015917 | 23015946 | Hyper | literature | BC045663, SSTR4 |
| chr20 | 23029110 | 23029151 | Hyper | cancer_general | THBD, AX747264 | chr20 | 23029387 | 23030357 | Hyper | literature, tcga, cancer_general | THBD, AX747264 |
| chr20 | 23031548 | 23031692 | Hyper | literature | THBD, AX747264 | chr20 | 24450231 | 24450513 | Hyper | tcga, cancer_general | SYNDIG1 |
| chr20 | 24450782 | 24451019 | Hyper | cancer_general | SYNDIG1 | chr20 | 24451450 | 24451592 | Hyper | cancer_general | SYNDIG1 |
| chr20 | 25058385 | 25058616 | Hyper | cancer_general | VSX1 | chr20 | 25061746 | 25062880 | Hyper | cancer_general | VSX1 |
| chr20 | 25063780 | 25064458 | Hyper | cancer_general | VSX1 | chr20 | 25065179 | 25065395 | Hyper | cancer_general | VSX1 |
| chr20 | 25129384 | 25129464 | Hyper | cancer_general | LOC284798 | chr20 | 26188812 | 26189011 | Hyper | liver_tcga, cancer_general, literature | MIR663A, LOC284801 |
| chr20 | 26190313 | 26190361 | Hyper | liver_tcga, literature | MIR663A, LOC284801 | chr20 | 30582750 | 30582978 | Hyper | cancer_general | XKR7 |
| chr20 | 30639141 | 30639319 | Hyper | cancer_general, literature | HCK | chr20 | 30639632 | 30639847 | Hyper | cancer_general | HCK |
| chr20 | 30640106 | 30640270 | Hyper | tcga | HCK | chr20 | 30778024 | 30778313 | Hyper | tcga, liver_tcga, cancer_general | TSPY26P, PLAGL2 |
| chr20 | 34188617 | 34189391 | Hyper | cancer_general | FER1L4 | chr20 | 34189635 | 34189910 | Hyper | cancer_general | FER1L4 |
| chr20 | 36331799 | 36331910 | Hyper | colorectal | VSTM2L | chr20 | 36781324 | 36781354 | Hyper | cancer_general | TGM2, HV531029, HV530979, HV531015, HV531014, HV531011, HV531005 |
| chr20 | 37302697 | 37303343 | Hyper | cancer_general, tcga | — | chr20 | 37351793 | 37352626 | Hyper | cancer_general | SLC32A1 |
| chr20 | 37353193 | 37353236 | Hyper | cancer_general | SLC32A1 | chr20 | 37353455 | 37353779 | Hyper | cancer_general | SLC32A1 |
| chr20 | 37354145 | 37355202 | Hyper | cancer_general | SLC32A1 | chr20 | 37355847 | 37357353 | Hyper | cancer_general | SLC32A1 |
| chr20 | 37357825 | 37358190 | Hyper | cancer_general | SLC32A1 | chr20 | 37434552 | 37434744 | Hyper | colorectal | PPP1R16B |
| chr20 | 37435104 | 37435218 | Hyper | tcga | PPP1R16B | chr20 | 37435461 | 37435860 | Hyper | cancer_general | PPP1R16B |
| chr20 | 39316203 | 39316322 | Hyper | tcga | MAFB | chr20 | 39316893 | 39317392 | Hyper | colorectal, cancer_general | MAFB |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 39317750 | 39318166 | Hyper | esophageal | MAFB | chr20 | 39318383 | 39318415 | Hyper | esophageal | MAFB |
| chr20 | 39319126 | 39319653 | Hyper | tcga, cancer_general | MAFB | chr20 | 39995146 | 39995813 | Hyper | cancer_general | EMILIN3, LPIN3 |
| chr20 | 40743859 | 40743888 | Hyper | literature | PTPRT | chr20 | 41817786 | 41818085 | Hyper | tcga, cancer_general | — |
| chr20 | 41818567 | 41818914 | Hyper | cancer_general | — | chr20 | 42136330 | 42136411 | Hyper | cancer_general | L3MBTL1 |
| chr20 | 42243754 | 42543853 | Hyper | cancer_general | TOX2 | chr20 | 42544091 | 42544984 | Hyper | cancer_general | TOX2 |
| chr20 | 42876525 | 42876575 | Hyper | cancer_general | GDAP1L1 | chr20 | 43438071 | 43438466 | Hyper | cancer_general | RIMS4 |
| chr20 | 43438982 | 43439022 | Hyper | lung, | RIMS4 | chr20 | 43439291 | 43439510 | Hyper | cancer_general | RIMS4 |
| chr20 | 44452731 | 44453063 | Hyper | cancer_general | SNX21, TNNC2, UBE2C | chr20 | 44519077 | 44519107 | Hyper | cancer_general | PLTP, NEURL2, SPATA25, ZSWIM1, CTSA |
| chr20 | 44639181 | 44639496 | Hyper | cancer_general | MMP9 | chr20 | 44640338 | 44640367 | Hyper | literature | SLC12A5, MMP9 |
| chr20 | 44660750 | 44660877 | Hyper | cancer_general | SLC12A5 | chr20 | 44686190 | 44686762 | Hyper | cancer_general | NCOA5, SLC12A5 |
| chr20 | 44746484 | 44746781 | Hyper | tcga | CD40 | chr20 | 44803174 | 44803675 | Hyper | cancer_general | CDH22 |
| chr20 | 44875240 | 44875411 | Hyper | cancer_general | — | chr20 | 44879801 | 44880076 | Hyper | cancer_general | — |
| chr20 | 44937202 | 44937643 | Hyper | tcga, cancer_general | — | chr20 | 44941518 | 44941661 | Hyper | cancer_general | — |
| chr20 | 45142000 | 45142272 | Hyper | cancer_general | ZNF334 | chr20 | 45279854 | 45280302 | Hyper | cancer_general, tcga | SLC13A3 |
| chr20 | 45524523 | 45524553 | Hyper | cancer_general | EYA2 | chr20 | 47443729 | 47444282 | Hyper | cancer_general | — |
| chr20 | 47934824 | 47935268 | Hyper | cancer_general | — | chr20 | 47935495 | 47935567 | Hyper | cancer_general | — |
| chr20 | 47935928 | 47936027 | Hyper | cancer_general | — | chr20 | 48184381 | 48184435 | Hyper | cancer_general | PTGIS |
| chr20 | 49575909 | 49575939 | Hyper | cancer_general | MOCS3, DPM1 | chr20 | 49639777 | 49640157 | Hyper | tcga, cancer_general | KCNG1 |
| chr20 | 50384767 | 50384896 | Hyper | blood | ATP9A | chr20 | 50720437 | 50722193 | Hyper | tcga, cancer_general, liver_tcga | ZFP64 |
| chr20 | 50722598 | 50722821 | Hyper | cancer_general, liver_tcga | ZFP64 | chr20 | 51589766 | 51589908 | Hyper | cancer_general | TSHZ2 |
| chr20 | 52226337 | 52226366 | Hyper | literature | — | chr20 | 52311483 | 52311602 | Hyper | pancreas, tcga, liver_tcga, cancer_general | — |
| chr20 | 52789445 | 52789475 | Hyper | cancer_general | CYP24A1 | chr20 | 52789853 | 52790155 | Hyper | cancer_general | CYP24A1 |
| chr20 | 53092192 | 53092376 | Hyper | cancer_general | DOK5 | chr20 | 53093085 | 53093115 | Hyper | cancer_general | DOK5 |
| chr20 | 54578507 | 54578725 | Hyper | cancer_general | CBLN4 | chr20 | 54579892 | 54580323 | Hyper | cancer_general | CBLN4 |
| chr20 | 54580574 | 54580691 | Hyper | literature, cancer_general | CBLN4 | chr20 | 55200035 | 55200706 | Hyper | cancer_general | TFAP2C |
| chr20 | 55200922 | 55201092 | Hyper | cancer_general | TFAP2C | chr20 | 55201486 | 55201549 | Hyper | cancer_general | TFAP2C |
| chr20 | 55201764 | 55202636 | Hyper | cancer_general | TFAP2C | chr20 | 55202826 | 55203107 | Hyper | cancer_general | TFAP2C |
| chr20 | 55204322 | 55204604 | Hyper | cancer_general | TFAP2C | chr20 | 55204966 | 55205000 | Hyper | cancer_general | TFAP2C |
| chr20 | 55206056 | 55206393 | Hyper | cancer_general | TFAP2C | chr20 | 55206739 | 55206774 | Hyper | cancer_general | TFAP2C |
| chr20 | 55499496 | 55499709 | Hyper | cancer_general | — | chr20 | 55500016 | 55500085 | Hyper | cancer_general | — |
| chr20 | 55500410 | 55500949 | Hyper | cancer_general | — | chr20 | 55841134 | 55841356 | Hyper | tcga | BC037891, BMP7 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr20 | 55842096 | 55842189 | Hyper | cancer_general | BC037891, BMP7 | chr20 | 56803398 | 56803441 | Hyper | cancer_general | PPP4R1L |
| chr20 | 56803842 | 56803920 | Hyper | cancer_general | PPP4R1L | chr20 | 57089452 | 57089496 | Hyper | cancer_general | APCDD1L-AS1, APCDD1L |
| chr20 | 57089804 | 57090173 | Hyper | cancer_general | APCDD1L-AS1, APCDD1L | chr20 | 57224842 | 57225307 | Hyper | cancer_general | STX16 |
| chr20 | 57484406 | 57484445 | Hyper | literature | GNAS | chr20 | 58152637 | 58152714 | Hyper | cancer_general | PHACTR3 |
| chr20 | 58179809 | 58179854 | Hyper | cancer_general | PHACTR3 | chr20 | 58180099 | 58180414 | Hyper | cancer_general | PHACTR3 |
| chr20 | 58508887 | 58508943 | Hyper | liver_tcga | PPP1R3D, FAM217B | chr20 | 59804170 | 59804235 | Hyper | pancreas | |
| chr20 | 59826962 | 59827226 | Hyper | literature, cancer_general | CDH4 | chr20 | 59827795 | 59828446 | Hyper | literature, cancer_general | CDH4 |
| chr20 | 61340581 | 61340689 | Hyper | cancer_general | NTSR1 | chr20 | 61560418 | 61560922 | Hyper | cancer_general | GID8 |
| chr20 | 61585771 | 61586004 | Hyper | cancer_general | SLC17A9, GID8 | chr20 | 61636858 | 61636890 | Hyper | cancer_general | BHLHE23, LOC63930 |
| chr20 | 61637468 | 61638631 | Hyper | cancer_general | LOC63930, BHLHE23 | chr20 | 61703709 | 61703875 | Hyper | cancer_general | — |
| chr20 | 61734420 | 61734481 | Hyper | cancer_general | HAR1A, HAR1B | chr20 | 61747894 | 61747934 | Hyper | cancer_general | — |
| chr20 | 61808181 | 61808270 | Hyper | cancer_general | MIR124-3 | chr20 | 61808485 | 61810089 | Hyper | tcga, cancer_general | MIR124-3 |
| chr20 | 61862380 | 61862452 | Hyper | cancer_general | BIRC7, MIR3196, NKAIN4 | chr20 | 61885247 | 61885462 | Hyper | tcga | FLJ16779, NKAIN4 |
| chr20 | 61885712 | 61885744 | Hyper | cancer_general | FLJ16779, NKAIN4 | chr20 | 61886068 | 61886258 | Hyper | cancer_general | FLJ16779, NKAIN4 |
| chr20 | 61886725 | 61886755 | Hyper | cancer_general | FLJ16779, NKAIN4 | chr20 | 62058700 | 62058786 | Hyper | cancer_general | KCNQ2 |
| chr20 | 62119339 | 62120171 | Hyper | cancer_general | EEF1A2 | chr20 | 62185386 | 62185444 | Hyper | tcga, liver_tcga | C20orf195 HELZ2, SRMS |
| chr20 | 62284487 | 62284615 | Hyper | liver_tcga | RTEL1, RTEL1-TNFRSF6B, STMN3 | chr20 | 62461349 | 62461475 | Hyper | cancer_general | BC002534, ZBTB46 |
| chr20 | 62680657 | 62680739 | Hyper | esophageal | TCEA2, SOX18, LINC00176 | chr20 | 62715014 | 62715069 | Hyper | esophageal | OPRL1, C20orf201, RGS19 |
| chr16 | 215416 | 216224 | Hyper | cancer_general | HBM, HBA2 | chr16 | 216676 | 217036 | Hyper | cancer_general | HBA2, HBA1, HBM |
| chr16 | 230265 | 230610 | Hyper | tcga, liver_tcga, cancer_general | LUC7L, HBA1, HBA2, HBQ1 | chr16 | 565492 | 565623 | Hyper | liver_tcga | RAB11FIP3 |
| chr16 | 1030302 | 1030655 | Hyper | tcga, cancer_general | SOX8, LMF1 | chr16 | 1122858 | 1122951 | Hyper | tcga | BC084558, SSTR5, SSTR5-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 1203970 | 1204034 | Hyper | cancer_general | CACNA1H | chr16 | 1382901 | 1382940 | Hyper | cancer_general | BALAP3 |
| chr16 | 1842490 | 1842519 | Hyper | liver_tcga | IGFALS, NUBP2, SPSB3 | chr16 | 2040914 | 2042160 | Hyper | cancer_general | ZNF598, SYNGR3, GFER, NOXO1 |
| chr16 | 2086831 | 2086860 | Hyper | liver_tcga | NTHL1, SLC9A3R2 | chr16 | 2106703 | 2106732 | Hyper | literature | TSC2, NTHL1 |
| chr16 | 2111966 | 2111995 | Hyper | literature | TSC2 | chr16 | 2120515 | 2120544 | Hyper | literature | — |
| chr16 | 2122243 | 2122272 | Hyper | literature | — | chr16 | 2124205 | 2124348 | Hyper | literature | TSC2 |
| chr16 | 2126080 | 2126109 | Hyper | literature | TSC2 | chr16 | 2130361 | 2130390 | Hyper | literature | TSC2, PKD1, MIR1225 |
| chr16 | 2132244 | 2132315 | Hyper | liver_tcga | TSC2, PKD1, MIR1225 | chr16 | 2135301 | 2135330 | Hyper | literature | PKD1, MIR1225, TSC2 |
| chr16 | 2136228 | 2136257 | Hyper | literature | TSC2, PKD1, MIR1225 | chr16 | 2136727 | 2136855 | Hyper | literature | PKD1, MIR1225, TSC2 |
| chr16 | 2140403 | 2140438 | Hyper | liver_tcga | PKD1, MIR1225, TSC2 | chr16 | 2287295 | 2287370 | Hyper | cancer_general | ECI1, DNASE1L2, E4F1 |
| chr16 | 2892542 | 2892729 | Hyper | cancer_general | PRSS22, PRSS30P | chr16 | 3017052 | 3017628 | Hyper | cancer_general | PAQR4, PKMYT1, KREMEN2 |
| chr16 | 3068171 | 3068201 | Hyper | cancer_general | TNFRSF12A, HCFC1R1, THOC6, CCDC64B, CLDN6, CLDN9 | chr16 | 3220566 | 3222239 | Hyper | cancer_general, tcga | — |
| chr16 | 3225471 | 3225607 | Hyper | cancer_general | TRNA_Lys, TRNA_Pro, TRNA_Pseudo | chr16 | 3232739 | 3234452 | Hyper | liver_tcga, cancer_general | TRNA_Pro, TRNA_Lys, TRNA_Arg |
| chr16 | 3237857 | 3238546 | Hyper | liver_tcga, cancer_general | TRNA_Pro, TRNA_Lys, TRNA_Arg, TRNA_Pseudo | chr16 | 3238993 | 3239848 | Hyper | tcga, cancer_general | TRNA_Pro, TRNA_Lys, TRNA_Arg, TRNA_Pseudo |
| chr16 | 3241549 | 3241663 | Hyper | cancer_general | TRNA_Pseudo, TRNA_Lys, TRNA_Pro, TRNA_Arg | chr16 | 3241936 | 3241966 | Hyper | cancer_general | TRNA_Arg, TRNA_Pseudo, TRNA_Lys, TRNA_Pro |
| chr16 | 3355279 | 3355718 | Hyper | cancer_general | ZNF75A, TIGD7, ZNF263 | chr16 | 4431487 | 4431516 | Hyper | liver_tcga | VASN, CORO7-PAM16, CORO7 |
| chr16 | 4731638 | 4731718 | Hyper | liver_tcga | — | chr16 | 4733166 | 4733195 | Hyper | liver_tcga | — |
| chr16 | 4738567 | 4738680 | Hyper | liver_tcga | NUDT16L1, ANKS3 | chr16 | 4751554 | 4751583 | Hyper | liver_tcga | ANKS3, NUDT16L1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 5037900 | 5038004 | Hyper | cancer_general | SEC14L5 | chr16 | 6066925 | 6070019 | Hyper | cancer_general | RBFOX1 |
| chr16 | 7354634 | 7354664 | Hyper | cancer_general | RBFOX1 | chr16 | 9107184 | 9107213 | Hyper | liver_tcga, literature | — |
| chr16 | 10274399 | 10274429 | Hyper | cancer_general | GRIN2A | chr16 | 10275308 | 10275392 | Hyper | cancer_general, tcga | GRIN2A |
| chr16 | 10275752 | 10275948 | Hyper | tcga | GRIN2A | chr16 | 10276360 | 10277437 | Hyper | cancer_general, colorectal | GRIN2A |
| chr16 | 10479815 | 10479980 | Hyper | cancer_general | ATF7IP2 | chr16 | 12994459 | 12994737 | Hyper | cancer_general, tcga | SHISA9 |
| chr16 | 12995062 | 12995593 | Hyper | cancer_general, tcga | SHISA9 | chr16 | 12995803 | 12996328 | Hyper | cancer_general | SHISA9 |
| chr16 | 12996617 | 12996720 | Hyper | cancer_general | SHISA9 | chr16 | 12996948 | 12997011 | Hyper | pancreas | SHISA9 |
| chr16 | 12997386 | 12997703 | Hyper | cancer_general | SHISA9 | chr16 | 14021974 | 14022003 | Hyper | literature | ERCC4 |
| chr16 | 14041504 | 14041533 | Hyper | literature | ERCC4 | chr16 | 14041795 | 14041824 | Hyper | literature | ERCC4 |
| chr16 | 14042062 | 14042091 | Hyper | literature | C16orf62, CCP110 | chr16 | 15489599 | 15489808 | Hyper | tcga | MPV17L |
| chr16 | 19567202 | 19567449 | Hyper | cancer_general | RRN3P1 | chr16 | 19895125 | 19895155 | Hyper | cancer_general | GPRC5B |
| chr16 | 21831621 | 21831957 | Hyper | tcga | HS3ST2 | chr16 | 22824701 | 22825094 | Hyper | cancer_general | HS3ST2 |
| chr16 | 22825327 | 22826081 | Hyper | cancer_general | SCNN1B | chr16 | 23313464 | 23313522 | Hyper | esophageal | SCNN1B |
| chr16 | 23313749 | 23313836 | Hyper | esophageal | CHP2 | chr16 | 23706317 | 23706520 | Hyper | cancer_general | ERN2, PLK1 |
| chr16 | 23766097 | 23766130 | Hyper | tcga | CACNG3 | chr16 | 23847309 | 23847956 | Hyper | liver_tcga, cancer_general | PRKCB |
| chr16 | 24267115 | 24267208 | Hyper | cancer_general | HS3ST4 | chr16 | 24267485 | 24267578 | Hyper | cancer_general | CACNG3 |
| chr16 | 25702955 | 25702992 | Hyper | cancer_general | — | chr16 | 25703642 | 25704628 | Hyper | cancer_general, tcga | HS3ST4 |
| chr16 | 28074176 | 28074684 | Hyper | tcga, cancer_general | SH2B1, PAT2A1, LOC100289092 | chr16 | 28074959 | 28075197 | Hyper | tcga | — |
| chr16 | 28891040 | 28891072 | Hyper | esophageal | SEZ6L2, CDIPT-AS1 | chr16 | 29888136 | 29888227 | Hyper | cancer_general | SEZ6L2, CDIPT-AS1 |
| chr16 | 29888624 | 29888658 | Hyper | cancer_general | YBX3P1 | chr16 | 31227914 | 31228313 | Hyper | tcga, cancer_general | PYDC1, TRIM72 |
| chr16 | 31580560 | 31581036 | Hyper | literature, cancer_general | — | chr16 | 47177525 | 47177606 | Hyper | hepatobiliary | — |
| chr16 | 48844792 | 48845125 | Hyper | cancer_general | CBLN1 | chr16 | 49309170 | 49309262 | Hyper | cancer_general | CBLN1 |
| chr16 | 49311523 | 49312299 | Hyper | cancer_general | CBLN1 | chr16 | 49313363 | 49313710 | Hyper | cancer_general | CBLN1 |
| chr16 | 49314022 | 49314118 | Hyper | cancer_general | CBLN1 | chr16 | 49314419 | 49314561 | Hyper | cancer_general | CBLN1 |
| chr16 | 49314784 | 49314837 | Hyper | cancer_general | CBLN1 | chr16 | 49315276 | 49315306 | Hyper | cancer_general | SALL1 |
| chr16 | 49315919 | 49316580 | Hyper | cancer_general | SALL1 | chr16 | 51183900 | 51184406 | Hyper | cancer_general | SALL1 |
| chr16 | 51184807 | 51185360 | Hyper | literature, cancer_general | SALL1 | chr16 | 51185844 | 51186280 | Hyper | cancer_general, tcga | SALL1 |
| chr16 | 51186592 | 51186939 | Hyper | cancer_general | SALL1 | chr16 | 51188682 | 51188711 | Hyper | literature | SALL1 |
| chr16 | 51189922 | 51190215 | Hyper | cancer_general | IRX3 | chr16 | 54318898 | 54318988 | Hyper | cancer_general | IRX3 |
| chr16 | 54319420 | 54319468 | Hyper | cancer_general | IRX3 | chr16 | 54321638 | 54321834 | Hyper | cancer_general | IRX3 |
| chr16 | 54324999 | 54325131 | Hyper | cancer_general | IRX5, CRNDE | chr16 | 54628691 | 54628867 | Hyper | cancer_general | — |
| chr16 | 54964948 | 54965114 | Hyper | blood | IRX5, CRNDE | chr16 | 54966830 | 54967403 | Hyper | liver_tcga, cancer_general | IRX5, CRNDE |
| chr16 | 54971060 | 54971090 | Hyper | cancer_general | — | chr16 | 54971400 | 54971430 | Hyper | cancer_general | IRX5, CRNDE |
| chr16 | 55090666 | 55090861 | Hyper | cancer_general | — | chr16 | 55357926 | 55358086 | Hyper | cancer_general | IRX6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr16 | 55358316 | 55358528 | Hyper | cancer_general | IRX6 | chr16 | 55358798 | 55359071 | Hyper | cancer_general | IRX6 |
| chr16 | 55363009 | 55363223 | Hyper | cancer_general | IRX6 | chr16 | 55364716 | 55364843 | Hyper | cancer_general | IRX6 |
| chr16 | 55365103 | 55365234 | Hyper | cancer_general | IRX6 | chr16 | 55404999 | 55405214 | Hyper | tcga | — |
| chr16 | 55512843 | 55512884 | Hyper | cancer_general | MMP2 | chr16 | 55689886 | 55689915 | Hyper | tcga | SLC6A2 |
| chr16 | 55690115 | 55690809 | Hyper | tcga, cancer_general | SLC6A2 | chr16 | 56224557 | 56224879 | Hyper | cancer_general | GNAO1, DKFZP434H168, LOC283856 |
| chr16 | 56228370 | 56228581 | Hyper | cancer_general, tcga | DKFZP434H168, GNAO1, LOC283856 | chr16 | 56651094 | 56651275 | Hyper | cancer_general | MT1L, MT1M, MT1E, MT1A, MT2A |
| chr16 | 56659175 | 56659673 | Hyper | cancer_general | MT1E, MT1M, MT1JP, MT1L, MT1A | chr16 | 56672158 | 56672654 | Hyper | tcga, cancer_general | MT1A, MT1DP, MT1JP, MT1M |
| chr16 | 56709837 | 56710030 | Hyper | cancer_general | MT1G, MTE, MT1X, MT1JP, MT1H | chr16 | 57318379 | 57318412 | Hyper | blood | PLLP |
| chr16 | 58018634 | 58018845 | Hyper | cancer_general | ZNF319, TEPP | chr16 | 58019225 | 58019430 | Hyper | cancer_general | ZNF319, TEPP |
| chr16 | 58497221 | 58497409 | Hyper | literature | NDRG4 | chr16 | 58497752 | 58497829 | Hyper | literature | NDRG4 |
| chr16 | 58498175 | 58498204 | Hyper | literature | NDRG4 | chr16 | 58498570 | 58498724 | Hyper | literature | NDRG4 |
| chr16 | 58521708 | 58521737 | Hyper | literature | NDRG4 | chr16 | 58534666 | 58534695 | Hyper | literature | NDRG4 |
| chr16 | 62068463 | 62068517 | Hyper | cancer_general | — | chr16 | 62068952 | 62068982 | Hyper | cancer_general | — |
| chr16 | 62070743 | 62070773 | Hyper | cancer_general | — | chr16 | 65154933 | 65155091 | Hyper | cancer_general | — |
| chr16 | 65156385 | 65156489 | Hyper | cancer_general | CMTM2, CMTM1 | chr16 | 66461786 | 66461840 | Hyper | cancer_general | BEAN1 |
| chr16 | 66612882 | 66613369 | Hyper | cancer_general, tcga | CMTM2, CMTM1 | chr16 | 67197698 | 67197769 | Hyper | cancer_general | HSF4, NOL3, FBXL8, TRADD |
| chr16 | 67198009 | 67198039 | Hyper | cancer_general | HSF4, NOL3, FBXL8, TRADD | chr16 | 67198917 | 67198957 | Hyper | cancer_general | HSF4, FBXL8, TRADD, NOL3 |
| chr16 | 68481486 | 68481543 | Hyper | liver_tcga | SMPD3 | chr16 | 68482808 | 68482941 | Hyper | liver_tcga | SMPD3 |
| chr16 | 68544259 | 68544378 | Hyper | cancer_general | — | chr16 | 68676408 | 68676984 | Hyper | cancer_general | CDH3 |
| chr16 | 68770966 | 68771298 | Hyper | literature, blood | CDH1 | chr16 | 68844158 | 68844187 | Hyper | literature | CDH1 |
| chr16 | 68846033 | 68846062 | Hyper | literature | CDH1 | chr16 | 68856078 | 68856107 | Hyper | literature | CDH1 |
| chr16 | 71460027 | 71460351 | Hyper | cancer_general | TRNA_Met | chr16 | 73100460 | 73100524 | Hyper | cancer_general | — |
| chr16 | 77468261 | 77468775 | Hyper | cancer_general | ADAMTS18 | chr16 | 77822589 | 77822874 | Hyper | cancer_general | VAT1L |
| chr16 | 78079969 | 78080054 | Hyper | cancer_general | — | chr16 | 79623602 | 79623914 | Hyper | tcga, lung, cancer_general | MAF |
| chr16 | 80837962 | 80838143 | Hyper | esophageal | CDYL2 | chr16 | 80966399 | 80966431 | Hyper | blood | — |
| chr16 | 81946246 | 81946275 | Hyper | literature | PLCG2 | chr16 | 81962167 | 81962196 | Hyper | literature | PLCG2 |
| chr16 | 82660360 | 82660496 | Hyper | cancer_general, literature | CDH13 | chr16 | 82660712 | 82660741 | Hyper | literature | CDH13 |

TABLE 11-continued

| chr | Start | Stop | Hypo/hyper | classification | annotation |
|---|---|---|---|---|---|
| chr16 | 84402244 | 84402319 | Hyper | blood | ATP2C2 |
| chr16 | 84853288 | 84853376 | Hyper | blood | CRISPLD2 |
| chr16 | 86320354 | 86320391 | Hyper | cancer_general | LOC146513 |
| chr16 | 86321020 | 86321068 | Hyper | cancer_general | LOC146513 |
| chr16 | 86531310 | 86531573 | Hyper | cancer_general | FENDRR |
| chr16 | 86542373 | 86542457 | Hyper | cancer_general | FOXF1, FENDRR |
| chr16 | 86599477 | 86599844 | Hyper | cancer_general | FOXC2, FLJ30679 |
| chr16 | 86600958 | 86601015 | Hyper | cancer_general | FOXC2 |
| chr16 | 86601945 | 86602514 | Hyper | cancer_general | FOXC2, FOXL1 |
| chr16 | 87525622 | 87525701 | Hyper | blood | BC131758 |
| chr16 | 87636518 | 87636907 | Hyper | cancer_general, tcga | JPH3 |
| chr16 | 89007520 | 89007558 | Hyper | pancreas | CBFA2T3 |
| chr16 | 89008562 | 89008592 | Hyper | pancreas | CBFA2T3 |
| chr16 | 89267808 | 89267847 | Hyper | cancer_general | SLC22A31, CDH15 |
| chr16 | 84651793 | 84651822 | Hyper | liver_tcga | COTL1 |
| chr16 | 85932828 | 85932858 | Hyper | cancer_general | IRF8 |
| chr16 | 86320755 | 86320800 | Hyper | cancer_general | LOC146513 |
| chr16 | 86530947 | 86531046 | Hyper | cancer_general | FENDRR |
| chr16 | 86541591 | 86541968 | Hyper | cancer_general | FOXF1, FENDRR |
| chr16 | 86544191 | 86544972 | Hyper | cancer_general | FENDRR, FOXF1 |
| chr16 | 86600483 | 86600686 | Hyper | cancer_general | FLJ30679, FOXC2 |
| chr16 | 86601286 | 86601539 | Hyper | cancer_general | FOXC2 |
| chr16 | 86613052 | 86613108 | Hyper | tcga | FOXL1 |
| chr16 | 87635103 | 87635133 | Hyper | cancer_general | JPH3 |
| chr16 | 88343428 | 88343458 | Hyper | liver_tcga | MIR5189, ZFPM1 |
| chr16 | 89007880 | 89007995 | Hyper | esophageal | CBFA2T3 |
| chr16 | 89267334 | 89267364 | Hyper | cancer_general | CDH15, SLC22A31 |
| JH636052.4 | 5118769 | 5118903 | Hyper | cancer_general | — |
| EBV-B95-8 | 967 | 996 | Hyper | virus | — |
| EBV-B95-8 | 4234 | 4263 | Hyper | virus | — |
| EBV-B95-8 | 6553 | 6582 | Hyper | virus | — |
| EBV-B95-8 | 13471 | 13500 | Hyper | virus | — |
| EBV-B95-8 | 48222 | 48251 | Hyper | virus | — |
| EBV-B95-8 | 53561 | 53590 | Hyper | virus | — |
| EBV-B95-8 | 54778 | 54807 | Hyper | virus | — |
| EBV-B95-8 | 55893 | 55922 | Hyper | virus | — |
| EBV-B95-8 | 58227 | 58256 | Hyper | virus | — |
| EBV-B95-8 | 59581 | 59610 | Hyper | virus | — |
| EBV-B95-8 | 60877 | 60906 | Hyper | virus | — |
| EBV-B95-8 | 62302 | 62331 | Hyper | virus | — |
| EBV-B95-8 | 63178 | 63207 | Hyper | virus | — |
| EBV-B95-8 | 63935 | 63964 | Hyper | virus | — |
| EBV-B95-8 | 66726 | 66755 | Hyper | virus | — |
| EBV-B95-8 | 67857 | 67886 | Hyper | virus | — |
| EBV-B95-8 | 69798 | 69827 | Hyper | virus | — |
| EBV-B95-8 | 70839 | 70868 | Hyper | virus | — |
| EBV-B95-8 | 72204 | 72233 | Hyper | virus | — |
| EBV-B95-8 | 72983 | 73012 | Hyper | virus | — |
| EBV-B95-8 | 74304 | 74333 | Hyper | virus | — |
| EBV-B95-8 | 74978 | 75007 | Hyper | virus | — |
| EBV-B95-8 | 77784 | 77813 | Hyper | virus | — |
| EBV-B95-8 | 80289 | 80318 | Hyper | virus | — |
| EBV-B95-8 | 81198 | 81227 | Hyper | virus | — |
| EBV-B95-8 | 81888 | 81917 | Hyper | virus | — |
| EBV-B95-8 | 82703 | 82732 | Hyper | virus | — |
| EBV-B95-8 | 85345 | 85374 | Hyper | virus | — |
| EBV-B95-8 | 87104 | 87133 | Hyper | virus | — |
| EBV-B95-8 | 3766 | 3795 | Hyper | virus | |
| EBV-B95-8 | 5326 | 5355 | Hyper | virus | |
| EBV-B95-8 | 8800 | 8829 | Hyper | virus | |
| EBV-B95-8 | 46577 | 46606 | Hyper | virus | |
| EBV-B95-8 | 52842 | 52871 | Hyper | virus | |
| EBV-B95-8 | 54377 | 54406 | Hyper | virus | |
| EBV-B95-8 | 55067 | 55096 | Hyper | virus | |
| EBV-B95-8 | 56735 | 56764 | Hyper | virus | |
| EBV-B95-8 | 58926 | 58955 | Hyper | virus | |
| EBV-B95-8 | 60099 | 60128 | Hyper | virus | |
| EBV-B95-8 | 61319 | 61348 | Hyper | virus | |
| EBV-B95-8 | 62840 | 62869 | Hyper | virus | |
| EBV-B95-8 | 63601 | 63630 | Hyper | virus | |
| EBV-B95-8 | 64590 | 64619 | Hyper | virus | |
| EBV-B95-8 | 67486 | 67515 | Hyper | virus | |
| EBV-B95-8 | 69228 | 69257 | Hyper | virus | |
| EBV-B95-8 | 70439 | 70468 | Hyper | virus | |
| EBV-B95-8 | 71938 | 71967 | Hyper | virus | |
| EBV-B95-8 | 72535 | 72564 | Hyper | virus | |
| EBV-B95-8 | 73950 | 73979 | Hyper | virus | |
| EBV-B95-8 | 74689 | 74718 | Hyper | virus | |
| EBV-B95-8 | 75256 | 75285 | Hyper | virus | |
| EBV-B95-8 | 79618 | 79647 | Hyper | virus | |
| EBV-B95-8 | 80704 | 80733 | Hyper | virus | |
| EBV-B95-8 | 81629 | 81658 | Hyper | virus | |
| EBV-B95-8 | 82225 | 82254 | Hyper | virus | |
| EBV-B95-8 | 83438 | 83467 | Hyper | virus | |
| EBV-B95-8 | 86299 | 86328 | Hyper | virus | |
| EBV-B95-8 | 89959 | 89988 | Hyper | virus | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| EBV-B95-8 | 90915 | 90944 | Hyper | virus | — | EBV-B95-8 | 92531 | 92560 | Hyper | virus | — |
| EBV-B95-8 | 94071 | 94100 | Hyper | virus | — | EBV-B95-8 | 94731 | 94760 | Hyper | virus | — |
| EBV-B95-8 | 95084 | 95113 | Hyper | virus | — | EBV-B95-8 | 97482 | 97511 | Hyper | virus | — |
| EBV-B95-8 | 98245 | 98274 | Hyper | virus | — | EBV-B95-8 | 99224 | 99253 | Hyper | virus | — |
| EBV-B95-8 | 100235 | 100264 | Hyper | virus | — | EBV-B95-8 | 101009 | 101038 | Hyper | virus | — |
| EBV-B95-8 | 102716 | 102745 | Hyper | virus | — | EBV-B95-8 | 104004 | 104033 | Hyper | virus | — |
| EBV-B95-8 | 105019 | 105048 | Hyper | virus | — | EBV-B95-8 | 105284 | 105313 | Hyper | virus | — |
| EBV-B95-8 | 107231 | 107260 | Hyper | virus | — | EBV-B95-8 | 108023 | 108052 | Hyper | virus | — |
| EBV-B95-8 | 108370 | 108399 | Hyper | virus | — | EBV-B95-8 | 109086 | 109115 | Hyper | virus | — |
| EBV-B95-8 | 110250 | 110279 | Hyper | virus | — | EBV-B95-8 | 110626 | 110655 | Hyper | virus | — |
| EBV-B95-8 | 111690 | 111719 | Hyper | virus | — | EBV-B95-8 | 112112 | 112141 | Hyper | virus | — |
| EBV-B95-8 | 114429 | 114458 | Hyper | virus | — | EBV-B95-8 | 114749 | 114778 | Hyper | virus | — |
| EBV-B95-8 | 115006 | 115035 | Hyper | virus | — | EBV-B95-8 | 115597 | 115626 | Hyper | virus | — |
| EBV-B95-8 | 116382 | 116411 | Hyper | virus | — | EBV-B95-8 | 116649 | 116678 | Hyper | virus | — |
| EBV-B95-8 | 118647 | 118676 | Hyper | virus | — | EBV-B95-8 | 119542 | 119571 | Hyper | virus | — |
| EBV-B95-8 | 120350 | 120379 | Hyper | virus | — | EBV-B95-8 | 121382 | 121411 | Hyper | virus | — |
| EBV-B95-8 | 123037 | 123066 | Hyper | virus | — | EBV-B95-8 | 123570 | 123599 | Hyper | virus | — |
| EBV-B95-8 | 124913 | 124942 | Hyper | virus | — | EBV-B95-8 | 125376 | 125405 | Hyper | virus | — |
| EBV-B95-8 | 125805 | 125834 | Hyper | virus | — | EBV-B95-8 | 126337 | 126366 | Hyper | virus | — |
| EBV-B95-8 | 127493 | 127522 | Hyper | virus | — | EBV-B95-8 | 127905 | 127934 | Hyper | virus | — |
| EBV-B95-8 | 128805 | 128834 | Hyper | virus | — | EBV-B95-8 | 130244 | 130273 | Hyper | virus | — |
| EBV-B95-8 | 130690 | 130719 | Hyper | virus | — | EBV-B95-8 | 131603 | 131632 | Hyper | virus | — |
| EBV-B95-8 | 134325 | 134354 | Hyper | virus | — | EBV-B95-8 | 135032 | 135061 | Hyper | virus | — |
| EBV-B95-8 | 135599 | 135628 | Hyper | virus | — | EBV-B95-8 | 136148 | 136177 | Hyper | virus | — |
| EBV-B95-8 | 136680 | 136709 | Hyper | virus | — | EBV-B95-8 | 137805 | 137834 | Hyper | virus | — |
| EBV-B95-8 | 138375 | 138404 | Hyper | virus | — | EBV-B95-8 | 139745 | 139774 | Hyper | virus | — |
| EBV-B95-8 | 140610 | 140639 | Hyper | virus | — | EBV-B95-8 | 141137 | 141166 | Hyper | virus | — |
| EBV-B95-8 | 142290 | 142319 | Hyper | virus | — | EBV-B95-8 | 142763 | 142792 | Hyper | virus | — |
| EBV-B95-8 | 143078 | 143107 | Hyper | virus | — | EBV-B95-8 | 144318 | 144347 | Hyper | virus | — |
| EBV-B95-8 | 145216 | 145245 | Hyper | virus | — | EBV-B95-8 | 145638 | 145667 | Hyper | virus | — |
| EBV-B95-8 | 147044 | 147073 | Hyper | virus | — | EBV-B95-8 | 148404 | 148433 | Hyper | virus | — |
| EBV-B95-8 | 150099 | 150128 | Hyper | virus | — | EBV-B95-8 | 150443 | 150472 | Hyper | virus | — |
| EBV-B95-8 | 152230 | 152259 | Hyper | virus | — | EBV-B95-8 | 153127 | 153156 | Hyper | virus | — |
| EBV-B95-8 | 153468 | 153497 | Hyper | virus | — | EBV-B95-8 | 153800 | 153829 | Hyper | virus | — |
| EBV-B95-8 | 154204 | 154233 | Hyper | virus | — | EBV-B95-8 | 156501 | 156530 | Hyper | virus | — |
| EBV-B95-8 | 156773 | 156802 | Hyper | virus | — | EBV-B95-8 | 157345 | 157374 | Hyper | virus | — |
| EBV-B95-8 | 159211 | 159240 | Hyper | virus | — | EBV-B95-8 | 159561 | 159590 | Hyper | virus | — |
| EBV-B95-8 | 161193 | 161222 | Hyper | virus | — | EBV-B95-8 | 161698 | 161727 | Hyper | virus | — |
| EBV-B95-8 | 162343 | 162372 | Hyper | virus | — | EBV-B95-8 | 163798 | 163827 | Hyper | virus | — |
| EBV-B95-8 | 164471 | 164500 | Hyper | virus | — | EBV-B95-8 | 165234 | 165263 | Hyper | virus | — |
| EBV-B95-8 | 166280 | 166309 | Hyper | virus | — | EBV-B95-8 | 167347 | 167376 | Hyper | virus | — |
| EBV-B95-8 | 167600 | 167629 | Hyper | virus | — | EBV-B95-8 | 167942 | 167971 | Hyper | virus | — |
| EBV-B95-8 | 168551 | 168580 | Hyper | virus | — | EBV-B95-8 | 171304 | 171333 | Hyper | virus | — |
| HHV5-CINCY-TOWNE | 1181 | 1210 | Hyper | virus | — | HHV5-CINCY-TOWNE | 1988 | 2017 | Hyper | virus | — |
| HHV5-CINCY-TOWNE | 2389 | 2418 | Hyper | virus | — | HHV5-CINCY-TOWNE | 3290 | 3319 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 3665 | 3694 | Hyper | virus | — | HHV5-CINCY-TOWNE | 4704 | 4733 | Hyper | virus | — |
| HHV5-CINCY-TOWNE | 5400 | 5429 | Hyper | virus | — | HHV5-CINCY-TOWNE | 7790 | 7819 | Hyper | virus | — |
| HHV5-CINCY-TOWNE | 9656 | 9685 | Hyper | virus | — | HHV5-CINCY-TOWNE | 10781 | 10810 | Hyper | virus | — |
| HHV5-CINCY-TOWNE | 11109 | 11138 | Hyper | virus | — | HHV5-CINCY-TOWNE | 12663 | 12692 | Hyper | virus | — |
| HHV5-CINCY-TOWNE | 13688 | 13717 | Hyper | virus | — | HHV5-CINCY-TOWNE | 14223 | 14252 | Hyper | virus | — |
| HHV5-CINCY-TOWNE | 14911 | 14940 | Hyper | virus | — | HHV5-CINCY-TOWNE | 15206 | 15235 | Hyper | virus | — |
| HHV5-CINCY-TOWNE | 15938 | 15967 | Hyper | virus | — | HHV5-CINCY-TOWNE | 16440 | 16469 | Hyper | virus | — |
| HHV5-CINCY-TOWNE | 16884 | 16913 | Hyper | virus | — | HHV5-CINCY-TOWNE | 17347 | 17376 | Hyper | virus | — |
| HHV5-CINCY-TOWNE | 17696 | 17725 | Hyper | virus | — | HHV5-CINCY-TOWNE | 17958 | 17987 | Hyper | virus | — |
| HHV5-CINCY-TOWNE | 18372 | 18401 | Hyper | virus | — | HHV5-CINCY-TOWNE | 19417 | 19446 | Hyper | virus | — |
| HHV5-CINCY-TOWNE | 19910 | 19939 | Hyper | virus | — | HHV5-CINCY-TOWNE | 20248 | 20277 | Hyper | virus | — |
| HHV5-CINCY-TOWNE | 20671 | 20700 | Hyper | virus | — | HHV5-CINCY-TOWNE | 21899 | 21928 | Hyper | virus | — |
| HHV5-CINCY-TOWNE | 22798 | 22827 | Hyper | virus | — | HHV5-CINCY-TOWNE | 23095 | 23124 | Hyper | virus | — |
| HHV5-CINCY-TOWNE | 26713 | 26742 | Hyper | virus | — | HHV5-CINCY-TOWNE | 27211 | 27240 | Hyper | virus | — |
| HHV5-CINCY-TOWNE | 29784 | 29813 | Hyper | virus | — | HHV5-CINCY-TOWNE | 31141 | 31170 | Hyper | virus | — |
| HHV5-CINCY-TOWNE | 32660 | 32689 | Hyper | virus | — | HHV5-CINCY-TOWNE | 35651 | 35680 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 36393 | 36422 | Hyper | virus | — | HHV5-CINCY-TOWNE | 37224 | 37253 | Hyper | virus | — |
| HHV5-CINCY-TOWNE | 37895 | 37924 | Hyper | virus | — | HHV5-CINCY-TOWNE | 39244 | 39273 | Hyper | virus | — |
| HHV5-CINCY-TOWNE | 43188 | 43217 | Hyper | virus | — | HHV5-CINCY-TOWNE | 44447 | 44476 | Hyper | virus | — |
| HHV5-CINCY-TOWNE | 44799 | 44828 | Hyper | virus | — | HHV5-CINCY-TOWNE | 45394 | 45423 | Hyper | virus | — |
| HHV5-CINCY-TOWNE | 46445 | 46474 | Hyper | virus | — | HHV5-CINCY-TOWNE | 46944 | 46973 | Hyper | virus | — |
| HHV5-CINCY-TOWNE | 47916 | 47945 | Hyper | virus | — | HHV5-CINCY-TOWNE | 48504 | 48533 | Hyper | virus | — |
| HHV5-CINCY-TOWNE | 49094 | 49123 | Hyper | virus | — | HHV5-CINCY-TOWNE | 49903 | 49932 | Hyper | virus | — |
| HHV5-CINCY-TOWNE | 50230 | 50259 | Hyper | virus | — | HHV5-CINCY-TOWNE | 51421 | 51450 | Hyper | virus | — |
| HHV5-CINCY-TOWNE | 53772 | 53801 | Hyper | virus | — | HHV5-CINCY-TOWNE | 55651 | 55680 | Hyper | virus | — |
| HHV5-CINCY-TOWNE | 56380 | 56409 | Hyper | virus | — | HHV5-CINCY-TOWNE | 57291 | 57320 | Hyper | virus | — |
| HHV5-CINCY-TOWNE | 58491 | 58520 | Hyper | virus | — | HHV5-CINCY-TOWNE | 59023 | 59052 | Hyper | virus | — |
| HHV5-CINCY-TOWNE | 59792 | 59821 | Hyper | virus | — | HHV5-CINCY-TOWNE | 60124 | 60153 | Hyper | virus | — |
| HHV5-CINCY-TOWNE | 60392 | 60421 | Hyper | virus | — | HHV5-CINCY-TOWNE | 60900 | 60929 | Hyper | virus | — |
| HHV5-CINCY-TOWNE | 63894 | 63923 | Hyper | virus | — | HHV5-CINCY-TOWNE | 65843 | 65872 | Hyper | virus | — |
| HHV5-CINCY-TOWNE | 68089 | 68118 | Hyper | virus | — | HHV5-CINCY-TOWNE | 72454 | 72483 | Hyper | virus | — |
| HHV5-CINCY-TOWNE | 81185 | 81214 | Hyper | virus | — | HHV5-CINCY-TOWNE | 84144 | 84173 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 85524 | 85553 | Hyper | virus | — | HHV5-CINCY-TOWNE | 85943 | 85972 | Hyper | virus | — |
| HHV5-CINCY-TOWNE | 86889 | 86918 | Hyper | virus | — | HHV5-CINCY-TOWNE | 87195 | 87224 | Hyper | virus | — |
| HHV5-CINCY-TOWNE | 87455 | 87484 | Hyper | virus | — | HHV5-CINCY-TOWNE | 87769 | 87798 | Hyper | virus | — |
| HHV5-CINCY-TOWNE | 88564 | 88593 | Hyper | virus | — | HHV5-CINCY-TOWNE | 93096 | 93125 | Hyper | virus | — |
| HHV5-CINCY-TOWNE | 93776 | 93805 | Hyper | virus | — | HHV5-CINCY-TOWNE | 97621 | 97650 | Hyper | virus | — |
| HHV5-CINCY-TOWNE | 98737 | 98766 | Hyper | virus | — | HHV5-CINCY-TOWNE | 99460 | 99489 | Hyper | virus | — |
| HHV5-CINCY-TOWNE | 107540 | 107569 | Hyper | virus | — | HHV5-CINCY-TOWNE | 108823 | 108852 | Hyper | virus | — |
| HHV5-CINCY-TOWNE | 109725 | 109754 | Hyper | virus | — | HHV5-CINCY-TOWNE | 112036 | 112065 | Hyper | virus | — |
| HHV5-CINCY-TOWNE | 112319 | 112348 | Hyper | virus | — | HHV5-CINCY-TOWNE | 112595 | 112624 | Hyper | virus | — |
| HHV5-CINCY-TOWNE | 112892 | 112921 | Hyper | virus | — | HHV5-CINCY-TOWNE | 113194 | 113223 | Hyper | virus | — |
| HHV5-CINCY-TOWNE | 113535 | 113564 | Hyper | virus | — | HHV5-CINCY-TOWNE | 113927 | 113956 | Hyper | virus | — |
| HHV5-CINCY-TOWNE | 114267 | 114296 | Hyper | virus | — | HHV5-CINCY-TOWNE | 114593 | 114622 | Hyper | virus | — |
| HHV5-CINCY-TOWNE | 114867 | 114896 | Hyper | virus | — | HHV5-CINCY-TOWNE | 115177 | 115206 | Hyper | virus | — |
| HHV5-CINCY-TOWNE | 115432 | 115461 | Hyper | virus | — | HHV5-CINCY-TOWNE | 115685 | 115714 | Hyper | virus | — |
| HHV5-CINCY-TOWNE | 115986 | 116015 | Hyper | virus | — | HHV5-CINCY-TOWNE | 116382 | 116411 | Hyper | virus | — |
| HHV5-CINCY-TOWNE | 116700 | 116729 | Hyper | virus | — | HHV5-CINCY-TOWNE | 118193 | 118222 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 118995 | 119024 | Hyper | virus | — | HHV5-CINCY-TOWNE | 120028 | 120057 | Hyper | virus | — |
| HHV5-CINCY-TOWNE | 121485 | 121514 | Hyper | virus | — | HHV5-CINCY-TOWNE | 122199 | 122228 | Hyper | virus | — |
| HHV5-CINCY-TOWNE | 122606 | 122635 | Hyper | virus | — | HHV5-CINCY-TOWNE | 124559 | 124588 | Hyper | virus | — |
| HHV5-CINCY-TOWNE | 125276 | 125305 | Hyper | virus | — | HHV5-CINCY-TOWNE | 132497 | 132526 | Hyper | virus | — |
| HHV5-CINCY-TOWNE | 135460 | 135489 | Hyper | virus | — | HHV5-CINCY-TOWNE | 135730 | 135759 | Hyper | virus | — |
| HHV5-CINCY-TOWNE | 137379 | 137408 | Hyper | virus | — | HHV5-CINCY-TOWNE | 139067 | 139096 | Hyper | virus | — |
| HHV5-CINCY-TOWNE | 139472 | 139501 | Hyper | virus | — | HHV5-CINCY-TOWNE | 140147 | 140176 | Hyper | virus | — |
| HHV5-CINCY-TOWNE | 140722 | 140751 | Hyper | virus | — | HHV5-CINCY-TOWNE | 142023 | 142052 | Hyper | virus | — |
| HHV5-CINCY-TOWNE | 143692 | 143721 | Hyper | virus | — | HHV5-CINCY-TOWNE | 144080 | 144109 | Hyper | virus | — |
| HHV5-CINCY-TOWNE | 147310 | 147339 | Hyper | virus | — | HHV5-CINCY-TOWNE | 149465 | 149494 | Hyper | virus | — |
| HHV5-CINCY-TOWNE | 150359 | 150388 | Hyper | virus | — | HHV5-CINCY-TOWNE | 151593 | 151622 | Hyper | virus | — |
| HHV5-CINCY-TOWNE | 152153 | 152182 | Hyper | virus | — | HHV5-CINCY-TOWNE | 154148 | 154177 | Hyper | virus | — |
| HHV5-CINCY-TOWNE | 154610 | 154639 | Hyper | virus | — | HHV5-CINCY-TOWNE | 157018 | 157047 | Hyper | virus | — |
| HHV5-CINCY-TOWNE | 157367 | 157396 | Hyper | virus | — | HHV5-CINCY-TOWNE | 169038 | 169067 | Hyper | virus | — |
| HHV5-CINCY-TOWNE | 171503 | 171532 | Hyper | virus | — | HHV5-CINCY-TOWNE | 175146 | 175175 | Hyper | virus | — |
| HHV5-CINCY-TOWNE | 177553 | 177582 | Hyper | virus | — | HHV5-CINCY-TOWNE | 182254 | 182283 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HHV5-CINCY-TOWNE | 183115 | 183144 | Hyper | virus | — | HHV5-CINCY-TOWNE | 184120 | 184149 | Hyper | virus | — |
| HHV5-CINCY-TOWNE | 185558 | 185587 | Hyper | virus | — | HHV5-CINCY-TOWNE | 186027 | 186056 | Hyper | virus | — |
| HHV5-CINCY-TOWNE | 186435 | 186464 | Hyper | virus | — | HHV5-CINCY-TOWNE | 186707 | 186736 | Hyper | virus | — |
| HHV5-CINCY-TOWNE | 187115 | 187144 | Hyper | virus | — | HHV5-CINCY-TOWNE | 187514 | 187543 | Hyper | virus | — |
| HHV5-CINCY-TOWNE | 187859 | 187888 | Hyper | virus | — | HHV5-CINCY-TOWNE | 188473 | 188502 | Hyper | virus | — |
| HHV5-CINCY-TOWNE | 188768 | 188797 | Hyper | virus | — | HHV5-CINCY-TOWNE | 189050 | 189079 | Hyper | virus | — |
| HHV5-CINCY-TOWNE | 189302 | 189331 | Hyper | virus | — | HHV5-CINCY-TOWNE | 189936 | 189965 | Hyper | virus | — |
| HHV5-CINCY-TOWNE | 190655 | 190684 | Hyper | virus | — | HHV5-CINCY-TOWNE | 190954 | 190983 | Hyper | virus | — |
| HHV5-CINCY-TOWNE | 191453 | 191482 | Hyper | virus | — | HHV5-CINCY-TOWNE | 191882 | 191911 | Hyper | virus | — |
| HHV5-CINCY-TOWNE | 192183 | 192212 | Hyper | virus | — | HHV5-CINCY-TOWNE | 192541 | 192570 | Hyper | virus | — |
| HHV5-CINCY-TOWNE | 193045 | 193074 | Hyper | virus | — | HHV5-CINCY-TOWNE | 193325 | 193354 | Hyper | virus | — |
| HHV5-CINCY-TOWNE | 193597 | 193626 | Hyper | virus | — | HHV5-CINCY-TOWNE | 194165 | 194194 | Hyper | virus | — |
| HHV5-CINCY-TOWNE | 194461 | 194490 | Hyper | virus | — | HHV5-CINCY-TOWNE | 194848 | 194877 | Hyper | virus | — |
| HHV5-CINCY-TOWNE | 195324 | 195353 | Hyper | virus | — | HHV5-CINCY-TOWNE | 195651 | 195680 | Hyper | virus | — |
| HHV5-CINCY-TOWNE | 196018 | 196047 | Hyper | virus | — | HHV5-CINCY-TOWNE | 196343 | 196372 | Hyper | virus | — |
| HHV5-CINCY-TOWNE | 196941 | 196970 | Hyper | virus | — | HHV5-CINCY-TOWNE | 197218 | 197247 | Hyper | virus | — |

TABLE 11-continued

| chr | Start | Stop | Hypo/hyper | classification | annotation |
|---|---|---|---|---|---|
| HHV5-CINCY-TOWNE | 198315 | 198344 | Hyper | virus | — |
| HHV5-CINCY-TOWNE | 199162 | 199191 | Hyper | virus | — |
| HHV5-CINCY-TOWNE | 200571 | 200600 | Hyper | virus | — |
| HHV5-CINCY-TOWNE | 201905 | 201934 | Hyper | virus | — |
| HHV5-CINCY-TOWNE | 202537 | 202566 | Hyper | virus | — |
| HHV5-CINCY-TOWNE | 203720 | 203749 | Hyper | virus | — |
| HHV5-CINCY-TOWNE | 206213 | 206242 | Hyper | virus | — |
| HHV5-CINCY-TOWNE | 211676 | 211705 | Hyper | virus | — |
| HHV5-CINCY-TOWNE | 212609 | 212638 | Hyper | virus | — |
| HHV5-CINCY-TOWNE | 214695 | 214724 | Hyper | virus | — |
| HHV5-CINCY-TOWNE | 215930 | 215959 | Hyper | virus | — |
| HHV5-CINCY-TOWNE | 222672 | 222701 | Hyper | virus | — |
| HHV5-CINCY-TOWNE | 225150 | 225179 | Hyper | virus | — |
| HHV5-CINCY-TOWNE | 226887 | 226916 | Hyper | virus | — |
| chr11 | 407427 | 407463 | Hyper | cancer_general | SIGIRR, PKP3 |
| chr11 | 533859 | 533888 | Hyper | literature | LRRC56, HRAS |
| chr11 | 611099 | 611128 | Hyper | liver_tcga | IRF7, CDHR5, PHRF1 |
| HHV5-CINCY-TOWNE | 198792 | 198821 | Hyper | virus | — |
| HHV5-CINCY-TOWNE | 200113 | 200142 | Hyper | virus | — |
| HHV5-CINCY-TOWNE | 201373 | 201402 | Hyper | virus | — |
| HHV5-CINCY-TOWNE | 202264 | 202293 | Hyper | virus | — |
| HHV5-CINCY-TOWNE | 203319 | 203348 | Hyper | virus | — |
| HHV5-CINCY-TOWNE | 204008 | 204037 | Hyper | virus | — |
| HHV5-CINCY-TOWNE | 206735 | 206764 | Hyper | virus | — |
| HHV5-CINCY-TOWNE | 212340 | 212369 | Hyper | virus | — |
| HHV5-CINCY-TOWNE | 213813 | 213842 | Hyper | virus | — |
| HHV5-CINCY-TOWNE | 214950 | 214979 | Hyper | virus | — |
| HHV5-CINCY-TOWNE | 216228 | 216257 | Hyper | virus | — |
| HHV5-CINCY-TOWNE | 223515 | 223544 | Hyper | virus | — |
| HHV5-CINCY-TOWNE | 226058 | 226087 | Hyper | virus | — |
| chr11 | 406876 | 406939 | Hyper | cancer_general | SIGIRR, PKP3 |
| chr11 | 533451 | 533567 | Hyper | literature | LRRC56, HRAS |
| chr11 | 534273 | 534302 | Hyper | literature | LRRC56, HRAS |
| chr11 | 611691 | 611791 | Hyper | liver_tcga | IRF7, CDHR5, PHRF1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 627074 | 627189 | Hyper | literature, cancer_general | SCT, CDHR5 | chr11 | 636644 | 636673 | Hyper | literature | DRD4, DEAF1, SCT |
| chr11 | 636895 | 637441 | Hyper | tcga, cancer_general | DEAF1, SCT, DRD4 | chr11 | 679692 | 679722 | Hyper | liver_tcga | DEAF1 |
| chr11 | 726417 | 726466 | Hyper | cancer_general | EPS8L2 | chr11 | 829543 | 829708 | Hyper | cancer_general | CD151, EFCAB4A, PNPLA2, JB050151 |
| chr11 | 830174 | 830265 | Hyper | cancer_general | EFCAB4A, PNPLA2, JB050151, CD151, POLR2L | chr11 | 1318403 | 1318432 | Hyper | liver_tcga | TOLLIP |
| chr11 | 1358291 | 1358332 | Hyper | cancer_general | — | chr11 | 1411875 | 1411905 | Hyper | cancer_general tcga, | BRSK2 |
| chr11 | 1770051 | 1770248 | Hyper | tcga, cancer_general | CTSD, IFITM10 | chr11 | 2291259 | 2291768 | Hyper | cancer_general, liver_tcga | ASCL2 |
| chr11 | 2291984 | 2292636 | Hyper | liver_tcga, cancer_general | ASCL2 | chr11 | 2402376 | 2402405 | Hyper | liver_tcga | CD81, BC019904 |
| chr11 | 2465350 | 2465491 | Hyper | liver_tcga | KCNQ1 | chr11 | 2466597 | 2466788 | Hyper | liver_tcga | KCNQ1 |
| chr11 | 2884103 | 2884309 | Hyper | tcga | KCNQ1DN | chr11 | 3181913 | 3181942 | Hyper | tcga | — |
| chr11 | 4209105 | 4209134 | Hyper | tcga | LOC100506082, RRM1 | chr11 | 7273286 | 7273375 | Hyper | cancer_general | SYT9 |
| chr11 | 7274215 | 7274245 | Hyper | cancer_general | SYT9, TUB, BC027619 | chr11 | 7695432 | 7695528 | Hyper | liver_tcga | CYB5R2 |
| chr11 | 8040536 | 8040770 | Hyper | tcga | RIC3 | chr11 | 8103002 | 8103115 | Hyper | tcga | TUB |
| chr11 | 8189987 | 8190766 | Hyper | cancer_general | LMO1 | chr11 | 8284535 | 8284760 | Hyper | tcga, | LMO1 |
| chr11 | 8289517 | 8289745 | Hyper | cancer_general | — | chr11 | 8290195 | 8290423 | Hyper | tcga, cancer_general | LMO1 |
| chr11 | 8615674 | 8615704 | Hyper | liver_tcga | KRT8P41, MIR5691, SCUBE2 | chr11 | 9025970 | 9026348 | Hyper | liver_tcga, cancer_general | NRIP3 |
| chr11 | 9112446 | 9112741 | Hyper | cancer_general | DKK3 | chr11 | 12029957 | 12030272 | Hyper | cancer_general | DKK3 |
| chr11 | 12030823 | 12030852 | Hyper | liver_tcga | PARVA | chr11 | 12132524 | 12132559 | Hyper | blood | MICAL2 |
| chr11 | 12399040 | 12399222 | Hyper | blood | TEAD1 | chr11 | 12399727 | 12399791 | Hyper | blood | PARVA |
| chr11 | 12695481 | 12695611 | Hyper | blood | DD413619 | chr11 | 12696611 | 12696746 | Hyper | blood | TEAD1, DD413619 |
| chr11 | 13030566 | 13030890 | Hyper | tcga, liver_tcga | RASSF10 | chr11 | 13690121 | 13690157 | Hyper | liver_tcga | FAR1 |
| chr11 | 14316375 | 14316404 | Hyper | literature | RRAS2 | chr11 | 15136085 | 15136394 | Hyper | tcga, cancer_general | INSC |
| chr11 | 16628819 | 16628933 | Hyper | blood | — | chr11 | 16632493 | 16632670 | Hyper | cancer_general | — |
| chr11 | 17497492 | 17497685 | Hyper | cancer_general, literature, cancer_general | ABCC8 | chr11 | 17740493 | 17740570 | Hyper | cancer_general | MYOD1 |
| chr11 | 17741679 | 17742445 | Hyper | cancer_general, literature, cancer_general | MYOD1 | chr11 | 17743742 | 17743775 | Hyper | cancer_general | MYOD1 |
| chr11 | 18812614 | 18812653 | Hyper | cancer_general | PTPN5 | chr11 | 18813032 | 18813086 | Hyper | cancer_general | PTPN5 |
| chr11 | 18813451 | 18813558 | Hyper | tcga, cancer_general | PTPN5 | chr11 | 18813792 | 18813947 | Hyper | cancer_general | PTPN5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 19263848 | 19263878 | Hyper | cancer_general | E2F8 | chr11 | 19367102 | 19367330 | Hype | tcga, cancer_general | NAV2 |
| chr11 | 19735730 | 19735760 | Hyper | cancer_general | NAV2, LOC100126784 | chr11 | 20153718 | 20153764 | Hyper | cancer_general | — |
| chr11 | 20178066 | 20178305 | Hyper | cancer_general | DBX1 | chr11 | 20180279 | 20180793 | Hyper | cancer_general, literature, | DBX1 |
| chr11 | 20181213 | 20181254 | Hyper | cancer_general | DBX1 | chr11 | 20181701 | 20181993 | Hyper | cancer_general | DBX1 |
| chr11 | 20182864 | 20182959 | Hyper | cancer_general | DBX1 | chr11 | 20183251 | 20183421 | Hyper | cancer_general | DBX1 |
| chr11 | 20183674 | 20183773 | Hyper | cancer_general | DBX1 | chr11 | 20184569 | 20185410 | Hyper | tcga, cancer_general | DBX1 |
| chr11 | 20229058 | 20229550 | Hyper | cancer_general | TRNA | chr11 | 20229863 | 20230091 | Hyper | cancer_general | TRNA |
| chr11 | 20230398 | 20230464 | Hyper | cancer_general | TRNA | chr11 | 20618197 | 20619172 | Hyper | cancer_general, literature, tcga, liver_tcga | SLC6A5 |
| chr11 | 20619717 | 20619974 | Hyper | cancer_general | SLC6A5 | chr11 | 20621341 | 20621644 | Hyper | cancer_general | SLC6A5 |
| chr11 | 20622705 | 20623359 | Hyper | cancer_general | SLC6A5 | chr11 | 20690653 | 20690935 | Hyper | cancer_general | NELL1 |
| chr11 | 20691219 | 20691452 | Hyper | cancer_general | NELL1 | chr11 | 20691685 | 20691914 | Hyper | cancer_general | NELL1 |
| chr11 | 20692453 | 20692529 | Hyper | cancer_general | NELL1 | chr11 | 22215123 | 22215287 | Hyper | cancer_general | ANO5 |
| chr11 | 22362934 | 22363189 | Hyper | cancer_general | SLC17A6 | chr11 | 22364821 | 22364975 | Hyper | cancer_general | SLC17A6 |
| chr11 | 22365407 | 22365477 | Hyper | cancer_general | SLC17A6 | chr11 | 27742185 | 27742215 | Hyper | cancer_general | — |
| chr11 | 27743115 | 27743173 | Hyper | cancer_general | — | chr11 | 27743436 | 27743608 | Hyper | cancer_general | — |
| chr11 | 27744147 | 27744504 | Hyper | cancer_general, tcga, pancreas | — | chr11 | 27744711 | 27744744 | Hyper | cancer_general | — |
| chr11 | 30037593 | 30037743 | Hyper | cancer_general | KCNA4 | chr11 | 30038689 | 30038739 | Hyper | cancer_general | KCNA4 |
| chr11 | 30605919 | 30606123 | Hyper | cancer_general | MPPED2 | chr11 | 30606763 | 30606864 | Hyper | cancer_general | MPPED2 |
| chr11 | 30607367 | 30607409 | Hyper | cancer_general | MPPED2 | chr11 | 31818458 | 31818652 | Hyper | cancer_general | PAX6 |
| chr11 | 31819302 | 31819833 | Hyper | cancer_general | PAX6 | chr11 | 31820045 | 31821025 | Hyper | cancer_general | PAX6 |
| chr11 | 31821297 | 31821778 | Hyper | cancer_general | PAX6 | chr11 | 31822325 | 31822393 | Hyper | cancer_general | PAX6 |
| chr11 | 31824300 | 31824355 | Hyper | cancer_general | PAX6 | chr11 | 31824564 | 31824680 | Hyper | cancer_general | PAX6 |
| chr11 | 31825017 | 31825280 | Hyper | cancer_general | PAX6 | chr11 | 31825696 | 31827204 | Hyper | cancer_general | PAX6 |
| chr11 | 31827438 | 31828123 | Hyper | cancer_general | DKFZp686K1684, RCN1, PAX6 | chr11 | 31833097 | 31833155 | Hyper | cancer_general | DKFZp686K1684, RCN1 |
| chr11 | 31835707 | 31835797 | Hyper | cancer_general | DKFZp686K1684, RCN1, PAX6 | chr11 | 31836046 | 31836470 | Hyper | cancer_general | DKFZp686K1684, RCN1, PAX6 |
| chr11 | 31837019 | 31838392 | Hyper | cancer_general | DKFZp686K1684, RCN1, PAX6 | chr11 | 31838678 | 31839051 | Hyper | cancer_general | RCN1, DKFZp686K1684 |
| chr11 | 31839307 | 31840080 | Hyper | cancer_general | RCN1, DKFZp686K1684 | chr11 | 31840587 | 31840922 | Hyper | cancer_general | RCN1, DKFZp686K1684 |
| chr11 | 31841376 | 31842276 | Hyper | cancer_general | RCN1, DKFZp686K1684 | chr11 | 31846022 | 31846230 | Hyper | cancer_general | RCN1, DKFZp686K1684 |
| chr11 | 31846434 | 31846985 | Hyper | literature, cancer_general | RCN1, DKFZp686K1684 | chr11 | 31847250 | 31847925 | Hyper | cancer_general | RCN1, DKFZp686K1684 |
| chr11 | 31848472 | 31849300 | Hyper | cancer_general | RCN1, DKFZp686K1684 | chr11 | 32009104 | 32009160 | Hyper | cancer_general | RCN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 32354844 | 32355197 | Hyper | cancer_general | — | chr11 | 32448583 | 32448979 | Hyper | tcga, cancer_general | WT1-AS, WT1 |
| chr11 | 32455602 | 32455634 | Hyper | cancer_general | WT1-AS, WT1 | chr11 | 32455841 | 32456025 | Hyper | cancer_general | WT1-AS, WT1 |
| chr11 | 32456279 | 32457176 | Hyper | tcga, cancer_general | WT1-AS, WT1 | chr11 | 32457712 | 32458175 | Hyper | tcga, cancer_general | WT1, WT1-AS |
| chr11 | 32458389 | 32458823 | Hyper | cancer_general | WT1, WT1-AS | chr11 | 32459684 | 32460071 | Hyper | cancer_general | WT1, WT1-AS |
| chr11 | 32460468 | 32460515 | Hyper | cancer_general | WT1-AS, WT1 | chr11 | 32460796 | 32460864 | Hyper | cancer_general | WT1, WT1-AS |
| chr11 | 33037467 | 33037556 | Hyper | blood | DEPDC7 | chr11 | 33890297 | 33890334 | Hyper | cancer_general | LMO2 |
| chr11 | 35547499 | 35547562 | Hyper | tcga | PAMR1 | chr11 | 35641683 | 35641718 | Hyper | cancer_general | FJX1 |
| chr11 | 43596513 | 43596608 | Hyper | cancer_general | MIR 129-2, JA715139, BC031305 | chr11 | 43600453 | 43600557 | Hyper | cancer_general | BC031305, MIR129-2, JA715139 |
| chr11 | 43601094 | 43601467 | Hyper | cancer_general | MIR129-2, JA715139, BC031305 | chr11 | 43602468 | 43603228 | Hyper | liver_tcga, literature, cancer_general | MIR 129-2, JA715139 |
| chr11 | 43603628 | 43604177 | Hyper | cancer_general | JA715139, MIR129-2 | chr11 | 44325688 | 44325747 | Hyper | cancer_general | ALX4 |
| chr11 | 44326137 | 44326184 | Hyper | cancer_general | ALX4 | chr11 | 44326439 | 44326481 | Hyper | cancer_general | ALX4 |
| chr11 | 44327252 | 44327413 | Hyper | tcga | ALX4 | chr11 | 44330656 | 44331711 | Hyper | tcga, cancer_general | ALX4 |
| chr11 | 44333052 | 44333081 | Hyper | literature | ALX4 | chr11 | 44333371 | 44333480 | Hyper | cancer_general | ALX4 |
| chr11 | 44337690 | 44338077 | Hyper | cancer_general | ALX4 | chr11 | 44338335 | 44338367 | Hyper | cancer_general | ALX4 |
| chr11 | 44340823 | 44340858 | Hyper | cancer_general | ALX4 | chr11 | 44341966 | 44342034 | Hyper | cancer_general | AMBRA1, CHRM4, MDK |
| chr11 | 46316860 | 46317680 | Hyper | tcga, cancer_general | CREB3L1 | chr11 | 46413042 | 46413304 | Hyper | esophageal | |
| chr11 | 46940419 | 46940531 | Hyper | tcga | LRP4 | chr11 | 47209044 | 47209189 | Hyper | cancer_general | PACSIN3 |
| chr11 | 57194355 | 57194509 | Hyper | tcga | SLC43A3 | chr11 | 57414633 | 57414663 | Hyper | pancreas | YPEL4, MIR130A, AK096335 |
| chr11 | 58672746 | 58673064 | Hyper | cancer_general | AK294973 | chr11 | 59333596 | 59323729 | Hyper | cancer_general | TRNA_Val, TRNA_Lys, TRNA_Phe, U7, JB175310, TRNA_Leu, TRNA_Arg |
| chr11 | 59333405 | 59333541 | Hyper | cancer_general | TRNA_Phe, OSBP, JB175310, TRNA_Lys, U7 | chr11 | 60718668 | 60719163 | Hyper | cancer_general | SLC15A3 |
| chr11 | 61062822 | 61063138 | Hyper | tcga, cancer_general | DDB1, VWCE | chr11 | 61277002 | 61277220 | Hyper | liver_tcga, cancer_general | SYT7, LRRC10B, MIR4488 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 61595086 | 61595262 | Hyper | cancer_general | FADS2 | chr11 | 61596420 | 61596640 | Hyper | cancer_general | FADS2 |
| chr11 | 61723067 | 61723159 | Hyper | cancer_general | FTH1, BEST1 | chr11 | 63767984 | 63768131 | Hyper | tcga, cancer_general | MACROD1, OTUB1 |
| chr11 | 63839478 | 63839528 | Hyper | liver_tcga | MACROD1 | chr11 | 64410723 | 64410759 | Hyper | esophageal | NRXN2 |
| chr11 | 64480429 | 64480593 | Hyper | cancer_general | — | chr11 | 64480824 | 64481042 | Hyper | liver_tcga, cancer_general | |
| chr11 | 64490435 | 64490561 | Hyper | esophageal | RASGRP2 | chr11 | 64490792 | 64491159 | Hyper | esophageal | RASGRP2 |
| chr11 | 64739468 | 64739508 | Hyper | cancer_general | — | chr11 | 65185548 | 65185728 | Hyper | cancer_general | NEAT1, FRMD8 |
| chr11 | 65405659 | 65405774 | Hyper | tcga | MIR4690, PCNXL3, SIPA1 | chr11 | 65409759 | 65409861 | Hyper | liver_tcga | MIR4489, SIPA1, MIR4690, PCNXL3 |
| chr11 | 65554041 | 65554410 | Hyper | liver_tcga | OVOL1, AP5B1 | chr11 | 65600810 | 65601640 | Hyper | liver_tcga, cancer_general | SNX32 |
| chr11 | 65779317 | 65779357 | Hyper | literature | EIF1AD, CST6, AX747517, CATSPER1, BANF1 | chr11 | 65816447 | 65816564 | Hyper | literature, cancer_general | GAL3ST3, SF3B2 |
| chr11 | 66188115 | 66188145 | Hyper | cancer_general | NPAS4 | chr11 | 66188473 | 66188974 | Hyper | cancer_general | NPAS4 |
| chr11 | 66725600 | 66725637 | Hyper | blood | — | chr11 | 66790621 | 66790655 | Hyper | blood | SYT12 |
| chr11 | 67139422 | 67139546 | Hyper | liver_tcga | CLCF1, 7SK | chr11 | 67350180 | 67350340 | Hyper | literature | GSTP1 |
| chr11 | 67350961 | 67350990 | Hyper | literature | GSTP1 | chr11 | 68096034 | 68096179 | Hyper | tcga | LRP5 |
| chr11 | 68118716 | 68118745 | Hyper | liver_tcga | LRP5 | chr11 | 68153950 | 68154098 | Hyper | liver_tcga | LRP5 |
| chr11 | 68181217 | 68181288 | Hyper | liver_tcga | LRP5 | chr11 | 69466004 | 69466042 | Hyper | literature | AK294004, ORAOV1, BC133018, CCND1 |
| chr11 | 69484356 | 69484454 | Hyper | head_neck | ORAOV1 | chr11 | 69516968 | 69517174 | Hyper | cancer_general | FGF19 |
| chr11 | 69518030 | 69518211 | Hyper | liver_tcga, cancer_general | FGF19 | chr11 | 69518530 | 69518718 | Hyper | tcga, liver_tcga | FGF19 |
| chr11 | 69588930 | 69589184 | Hyper | cancer_general | FGF4 | chr11 | 69589824 | 69589854 | Hyper | cancer_general | FGF4 |
| chr11 | 69590149 | 69590222 | Hyper | cancer_general | FGF4 | chr11 | 70211516 | 70211545 | Hyper | literature | PPFIA1, AK125463 |
| chr11 | 71318332 | 71318967 | Hyper | cancer_general | — | chr11 | 71951639 | 71951738 | Hyper | cancer_general | PHOX2A, INPPL1 |
| chr11 | 71952340 | 71952541 | Hyper | cancer_general | PHOX2A, INPPL1 | chr11 | 71954612 | 71954642 | Hyper | cancer_general | INPPL1, PHOX2A |
| chr11 | 71955344 | 71955377 | Hyper | cancer_general | PHOX2A, INPPL1 | chr11 | 71956007 | 71956340 | Hyper | cancer_general | PHOX2A, INPPL1 |
| chr11 | 72432837 | 72432916 | Hyper | cancer_general | UCP2 | chr11 | 72929747 | 72929883 | Hyper | blood | P2RY2 |
| chr11 | 73694609 | 73694659 | Hyper | hepatobiliary | TPBGL | chr11 | 74394491 | 74394600 | Hyper | cancer_general | — |
| chr11 | 74953265 | 74953422 | Hyper | cancer_general | ODZ4, TENM4 | chr11 | 75379252 | 75379895 | Hyper | cancer_general | MAP6 |
| chr11 | 78672917 | 78672964 | Hyper | cancer_general | FAM181B | chr11 | 79151173 | 79151216 | Hyper | tcga | — |
| chr11 | 82444376 | 82445101 | Hyper | cancer_general | | chr11 | 86085742 | 86085968 | Hyper | literature, cancer_general | CCDC81 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 86383167 | 86383710 | Hyper | literature, tcga | ME3 | chr11 | 88241705 | 88242618 | Hyper | tcga, cancer_general | GRM5, GRM5-AS1 |
| chr11 | 88799082 | 88799209 | Hyper | cancer_general | GRM5 | chr11 | 89867794 | 89867990 | Hyper | tcga | NAALAD2 |
| chr11 | 91957500 | 91957674 | Hyper | cancer_general | | chr11 | 91957974 | 91958230 | Hyper | tcga, cancer_general | |
| chr11 | 91958734 | 91959430 | Hyper | tcga, cancer_general | | chr11 | 91959899 | 91960045 | Hyper | cancer_general | |
| chr11 | 93063583 | 93063645 | Hyper | cancer_general | CCDC67 | chr11 | 93063870 | 93063948 | Hyper | liver_tcga, cancer_general | CCDC67 |
| chr11 | 94134086 | 94134853 | Hyper | tcga, cancer_general | GPR83 | chr11 | 94278456 | 94278603 | Hyper | liver_tcga | PIWIL4, FUT4 |
| chr11 | 94473600 | 94474139 | Hyper | tcga, colorectal, cancer_general | | chr11 | 94474356 | 94474385 | Hyper | tcga | |
| chr11 | 94502334 | 94502489 | Hyper | tcga, colorectal | AMOTL1 | chr11 | 94884130 | 94884160 | Hyper | head_neck | AK055250 |
| chr11 | 98891477 | 98891882 | Hyper | tcga, cancer_general | CNTN5 | chr11 | 100997649 | 100997981 | Hyper | cancer_general | LOC101054525, PGR |
| chr11 | 100998276 | 100998318 | Hyper | cancer_general | LOC101054525, PGR | chr11 | 100998667 | 100998747 | Hyper | cancer_general | LOC101054525, PGR |
| chr11 | 101453180 | 101453518 | Hyper | cancer_general | | chr11 | 101454190 | 101454490 | Hyper | cancer_general | DYNC2H1 |
| chr11 | 102962922 | 102963062 | Hyper | pancreas | DCUN1D5 | chr11 | 102980027 | 102980056 | Hyper | literature | |
| chr11 | 104034521 | 104034996 | Hyper | tcga, cancer_general | | chr11 | 105480755 | 105480806 | Hyper | cancer_general | GRIA4 |
| chr11 | 105481216 | 105481571 | Hyper | tcga, cancer_general | GRIA4 | chr11 | 106888308 | 106888429 | Hyper | cancer_general | GUCY1A2 |
| chr11 | 106888641 | 106888801 | Hyper | tcga, cancer_general | GUCY1A2 | chr11 | 107461623 | 107461653 | Hyper | esophageal | ELMOD1, LOC643923 |
| chr11 | 107462415 | 107462459 | Hyper | tcga | LOC643923, ELMOD1 | chr11 | 108236072 | 108236101 | Hyper | literature | C11orf65 |
| chr11 | 109292906 | 109293052 | Hyper | cancer_general | C11orf87 | chr11 | 109293720 | 109293847 | Hyper | cancer_general | C11orf87 |
| chr11 | 110166519 | 110166935 | Hyper | esophageal | | chr11 | 110582232 | 110582434 | Hyper | tcga | |
| chr11 | 110582895 | 110583050 | Hyper | tcga | CBL | chr11 | 110583574 | 110583730 | Hyper | cancer_general | |
| chr11 | 111383183 | 111383682 | Hyper | literature cancer_general | THY1, LOC100499227 | chr11 | 111411093 | 111412061 | Hyper | tcga, cancer_general | LAYN, C11orf88 |
| chr11 | | | | | MIR34B, MIR34C, C11orf88, BC021736, BTG4 | | | | | | |
| chr11 | 114113022 | 114113052 | Hyper | esophageal | ZBTB16 | chr11 | 115375120 | 115375177 | Hyper | cancer_general | CADM1 |
| chr11 | 115530134 | 115530604 | Hyper | cancer_general, tcga | | chr11 | 115630515 | 115630910 | Hyper | cancer_general | LINC00900 |
| chr11 | 115631307 | 115631364 | Hyper | cancer_general | LINC00900 | chr11 | 116147253 | 116147283 | Hyper | pancreas | |
| chr11 | 116451023 | 116451190 | Hyper | esophageal | | chr11 | 117296921 | 117297109 | Hyper | tcga | DSCAML1 |
| chr11 | 119148865 | 119148945 | Hyper | tcga | CBL | chr11 | 119149236 | 119149265 | Hyper | literature | CBL |
| chr11 | 119292779 | 119292809 | Hyper | literature | THY1, LOC100499227 | chr11 | 119293370 | 119293615 | Hyper | tcga | THY1, LOC100499227 |
| chr11 | 119612227 | 119612399 | Hyper | cancer_general | | chr11 | 119612861 | 119613075 | Hyper | liver_tcga, cancer_general | |
| chr11 | 120039833 | 120039865 | Hyper | blood | | chr11 | 120435405 | 120435477 | Hyper | cancer_general | GRIK4 |
| chr11 | 120435800 | 120435830 | Hyper | cancer_general | GRIK4 | chr11 | 120894800 | 120895026 | Hyper | esophageal | TBCEL |
| chr11 | 122847265 | 122847696 | Hyper | cancer_general | BSX | chr11 | 122848079 | 122848591 | Hyper | cancer_general | BSX |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr11 | 122849301 | 122849331 | Hyper | cancer_general | BSX | chr11 | 122849642 | 122850163 | Hyper | cancer_general | BSX |
| chr11 | 122850424 | 122850536 | Hyper | cancer_general | BSX | chr11 | 122851177 | 122851209 | Hyper | cancer_general | BSX |
| chr11 | 122852438 | 122852475 | Hyper | cancer_general | BSX | chr11 | 122855008 | 122855043 | Hyper | tcga | BSX |
| chr11 | 123066433 | 123066463 | Hyper | cancer_general | CLMP | chr11 | 123229058 | 123229422 | Hyper | tcga | — |
| chr11 | 123300824 | 123302026 | Hyper | tcga, cancer_general | — | chr11 | 124735437 | 124735482 | Hyper | cancer_general | ROBO3 |
| chr11 | 124736196 | 124736252 | Hyper | cancer_general | ROBO3 | chr11 | 124738777 | 124739088 | Hyper | cancer_general | ROBO3 |
| chr11 | 125035763 | 125036208 | Hyper | cancer_general | PKNOX2 | chr11 | 125036598 | 125036645 | Hyper | cancer_general | PKNOX2 |
| chr11 | 125773675 | 125774096 | Hyper | cancer_general, liver_tcga | DDX25, HYLS1, PUS3 | chr11 | 126870182 | 126870212 | Hyper | cancer_general | KIRREL3-AS3 |
| chr11 | 126870453 | 126870543 | Hyper | cancer_general | KIRREL3-AS3 | chr11 | 126873390 | 126873515 | Hyper | cancer_general | KIRREL3-AS3 |
| chr11 | 128391893 | 128392116 | Hyper | tcga | BC043517, ETS1 | chr11 | 128562892 | 128563730 | Hyper | tcga, cancer_general | FLI1, FLI1-AS1, AX747861 |
| chr11 | 128563940 | 128564329 | Hyper | tcga, cancer_general | FLI1, FLI1-AS1, AX747861 | chr11 | 128564740 | 128565379 | Hyper | cancer_general | FLI1, FLI1-AS1, AX747861, FLI1 |
| chr11 | 129242876 | 129243587 | Hyper | cancer_general | BARX2 | chr11 | 129243849 | 129244603 | Hyper | cancer_general | BARX2 |
| chr11 | 129244893 | 129244923 | Hyper | cancer_general | BARX2 | chr11 | 129245673 | 129245810 | Hyper | blood | BARX2 |
| chr11 | 129246070 | 129246129 | Hyper | blood | BARX2 | chr11 | 130318960 | 130318997 | Hyper | blood | ADAMTS15 |
| chr11 | 130319527 | 130319613 | Hyper | cancer_general | ADAMTS15 | chr11 | 131564970 | 131565073 | Hyper | pancreas | — |
| chr11 | 131780469 | 131781271 | Hyper | tcga, cancer_general | NTM | chr11 | 132813489 | 132813949 | Hyper | tcga, cancer_general | — |
| chr11 | 132864134 | 132864175 | Hyper | cancer_general | — | chr11 | 132934123 | 132934176 | Hyper | cancer_general | — |
| chr11 | 132952768 | 132953423 | Hyper | tcga, cancer_general | — | chr11 | 133402206 | 133402260 | Hyper | cancer_general | — |
| chr11 | 133825226 | 133825543 | Hyper | cancer_general | IGSF9B | chr11 | 133906783 | 133906918 | Hyper | cancer_general | LOC100128239 |
| chr11 | 133939002 | 133939177 | Hyper | cancer_general | JAM3 | chr11 | 134145703 | 134146393 | Hyper | liver_tcga, cancer_general, tcga | GLB1L3 |
| chr11 | 134146682 | 134146894 | Hyper | cancer_general | GLB1L3 | chr11 | 134201502 | 134201543 | Hyper | blood | GLB1L2 |
| chr11 | 134201841 | 134202084 | Hyper | blood, tcga, liver_tcga | GLB1L2 | chr11 | 134281365 | 134281509 | Hyper | cancer_general | LOC283177 |
| chrY | 2655316 | 2655346 | Hyper | cancer_general | SRY, RPS4Y1, XGPY2 | chrY | 14532822 | 14532852 | Hyper | head_neck | GYG2P1 |
| chrY | 14533556 | 14533613 | Hyper | head_neck | GYG2P1 | HPV18 | 111 | 140 | Hyper | virus | — |
| HPV18 | 383 | 412 | Hyper | virus | — | HPV18 | 655 | 684 | Hyper | virus | — |
| HPV18 | 927 | 956 | Hyper | virus | — | HPV18 | 1199 | 1228 | Hyper | virus | — |
| HPV18 | 1471 | 1500 | Hyper | virus | — | HPV18 | 1743 | 1772 | Hyper | virus | — |
| HPV18 | 2015 | 2044 | Hyper | virus | — | HPV18 | 2287 | 2316 | Hyper | virus | — |
| HPV18 | 2559 | 2588 | Hyper | virus | — | HPV18 | 2831 | 2860 | Hyper | virus | — |
| HPV18 | 3103 | 3132 | Hyper | virus | — | HPV18 | 3375 | 3404 | Hyper | virus | — |
| HPV18 | 3647 | 3676 | Hyper | virus | — | HPV18 | 3919 | 3948 | Hyper | virus | — |
| HPV18 | 4191 | 4220 | Hyper | virus | — | HPV18 | 4463 | 4492 | Hyper | virus | — |
| HPV18 | 4735 | 4764 | Hyper | virus | — | HPV18 | 5007 | 5036 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HPV18 | 5279 | 5308 | Hyper | virus | — | HPV18 | 5551 | 5580 | Hyper | virus | — |
| HPV18 | 5823 | 5852 | Hyper | virus | — | HPV18 | 6095 | 6124 | Hyper | virus | — |
| HPV18 | 6367 | 6396 | Hyper | virus | — | HPV18 | 6639 | 6668 | Hyper | virus | — |
| HPV18 | 6911 | 6940 | Hyper | virus | — | HPV18 | 7183 | 7212 | Hyper | virus | — |
| HPV18 | 7455 | 7484 | Hyper | virus | — | HBV | 111 | 140 | Hyper | virus | — |
| HBV | 381 | 410 | Hyper | virus | — | HBV | 651 | 680 | Hyper | virus | — |
| HBV | 921 | 950 | Hyper | virus | — | HBV | 1191 | 1220 | Hyper | virus | — |
| HBV | 1461 | 1490 | Hyper | virus | — | HBV | 1731 | 1760 | Hyper | virus | — |
| HBV | 2001 | 2030 | Hyper | virus | — | HBV | 2271 | 2300 | Hyper | virus | — |
| HBV | 2541 | 2570 | Hyper | virus | — | HBV | 2811 | 2840 | Hyper | virus | — |
| chr18 | 499367 | 499482 | Hyper | cancer_general | COLEC12 | chr18 | 500046 | 500738 | Hyper | cancer_general | COLEC12 |
| chr18 | 904462 | 904648 | Hyper | cancer_general | ADCYAP1 | chr18 | 905000 | 905030 | Hyper | cancer_general | ADCYAP1 |
| chr18 | 905434 | 905642 | Hyper | cancer_general | ADCYAP1 | chr18 | 906871 | 906907 | Hyper | cancer_general | ADCYAP1 |
| chr18 | 907472 | 907594 | Hyper | cancer_general | ADCYAP1 | chr18 | 907912 | 907977 | Hyper | cancer_general | ADCYAP1 |
| chr18 | 908454 | 908589 | Hyper | cancer_general | ADCYAP1 | chr18 | 909120 | 909150 | Hyper | cancer_general | EMILIN2 |
| chr18 | 909487 | 909587 | Hyper | cancer_general | ADCYAP1 | chr18 | 2906268 | 2906304 | Hyper | cancer_general, tcga | — |
| chr18 | 3499067 | 3499371 | Hyper | cancer_general | DLGAP1 | chr18 | 4453964 | 4454163 | Hyper | cancer_general | C18orf42 |
| chr18 | 4455074 | 4455181 | Hyper | cancer_general | C18orf42 | chr18 | 5196516 | 5196959 | Hyper | cancer_general | LINC00667, LINC00526, LOC339290 |
| chr18 | 5197202 | 5197347 | Hyper | cancer_general | — | chr18 | 5237878 | 5238247 | Hyper | esophageal | EPB41L3 |
| chr18 | 5543231 | 5543331 | Hyper | cancer_general | EPB41L3 | chr18 | 5543640 | 5543853 | Hyper | cancer_general | — |
| chr18 | 5628167 | 5628815 | Hyper | cancer_general | — | chr18 | 5629774 | 5629984 | Hyper | cancer_general | TMEM200C |
| chr18 | 5630312 | 5630362 | Hyper | cancer_general | — | chr18 | 5890619 | 5891317 | Hyper | cancer_general | TMEM200C |
| chr18 | 5895023 | 5895205 | Hyper | cancer_general | TMEM200C | chr18 | 5895975 | 5896085 | Hyper | tcga | LAMA1 |
| chr18 | 6729952 | 6729993 | Hyper | cancer_general | LAMA1 | chr18 | 7116924 | 7116981 | Hyper | cancer_general | PTPRM |
| chr18 | 7117665 | 7117804 | Hyper | tcga | — | chr18 | 7567783 | 7568291 | Hyper | cancer_general, tcga | — |
| chr18 | 8608748 | 8608968 | Hyper | cancer_general | RAB12 | chr18 | 9771586 | 9771753 | Hyper | cancer_general | RAB31 |
| chr18 | 11148969 | 11149045 | Hyper | cancer_general | — | chr18 | 11149561 | 11149888 | Hyper | cancer_general | — |
| chr18 | 11689190 | 11689220 | Hyper | esophageal | GNAL | chr18 | 11751637 | 11751676 | Hyper | cancer_general | GNAL |
| chr18 | 11751966 | 11752379 | Hyper | cancer_general | GNAL | chr18 | 11752700 | 11752730 | Hyper | cancer_general | GNAL |
| chr18 | 12254226 | 12254578 | Hyper | cancer_general, tcga | CIDEA | chr18 | 12307247 | 12307751 | Hyper | cancer_general | TUBB6 |
| chr18 | 12911384 | 12911476 | Hyper | cancer_general | — | chr18 | 13824025 | 13824102 | Hyper | head_neck | MC5R |
| chr18 | 13868713 | 13868945 | Hyper | cancer_general | GREB1L | chr18 | 15198110 | 15198248 | Hyper | cancer_general | — |
| chr18 | 18822392 | 18823274 | Hyper | tcga, cancer_general | — | chr18 | 19750308 | 19750346 | Hyper | blood | GATA6 |
| chr18 | 21269349 | 21269390 | Hyper | blood | LAMA3 | chr18 | 21269659 | 21269740 | Hyper | blood | LOC100128893 |
| chr18 | 21719351 | 21719568 | Hyper | liver_tcga | CABYR, TTC39C | chr18 | 22929081 | 22930559 | Hyper | cancer_general, tcga | LAMA3 |
| chr18 | 22930790 | 22931178 | Hyper | cancer_general | ZNF521 | chr18 | 24127748 | 24128030 | Hyper | cancer_general | ZNF521 |
| chr18 | 24130809 | 24131187 | Hyper | cancer_general | — | chr18 | 24764951 | 24765168 | Hyper | tcga | — |
| chr18 | 25755593 | 25755655 | Hyper | tcga | — | chr18 | 25756010 | 25756040 | Hyper | cancer_general | CHST9 |
| chr18 | 25756495 | 25756729 | Hyper | tcga, cancer_general | — | chr18 | 25757187 | 25757452 | Hyper | tcga | |
| chr18 | 25757787 | 25757824 | Hyper | cancer_general | — | chr18 | 25758084 | 25758141 | Hyper | cancer_general | — |
| chr18 | 28620899 | 28621097 | Hyper | cancer_general | DSC3 | chr18 | 28621328 | 28621393 | Hyper | cancer_general | DSC3 |
| chr18 | 28621636 | 28621932 | Hyper | liver_tcga, cancer_general | DSC3 | chr18 | 28622419 | 28622488 | Hyper | cancer_general | DSC3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 30349740 | 30349781 | Hyper | cancer_general | KLHL14 | chr18 | 31020495 | 31020820 | Hyper | tcga, cancer_general | CCDC178 |
| chr18 | 31158093 | 31158158 | Hyper | cancer_general | ASXL3 | chr18 | 31739035 | 31739469 | Hyper | cancer_general | |
| chr18 | 31802132 | 31802167 | Hyper | cancer_general | — | chr18 | 31802938 | 31802968 | Hyper | cancer_general | |
| chr18 | 31803438 | 31803472 | Hyper | cancer_general | — | chr18 | 31902793 | 31902945 | Hyper | lung | MAPRE2 |
| chr18 | 32073885 | 32074086 | Hyper | cancer_general | DTNA | chr18 | 32557832 | 32557864 | Hyper | head_neck | FHOD3 |
| chr18 | 32847565 | 32847642 | Hyper | liver_tcga | ZSCAN30 | chr18 | 33877683 | 33877754 | Hyper | esophageal | |
| chr18 | 34833596 | 34833859 | Hyper | cancer_general | CELF4 | chr18 | 35065072 | 35065438 | Hyper | cancer_general | |
| chr18 | 35104666 | 35104882 | Hyper | tcga | — | chr18 | 35144845 | 35145465 | Hyper | cancer_general | |
| chr18 | 35145968 | 35146241 | Hyper | tcga | — | chr18 | 35147487 | 35147569 | Hyper | cancer_general | |
| chr18 | 43914211 | 43914278 | Hyper | tcga | C18orf23, RNF165 | chr18 | 44336034 | 44336697 | Hyper | cancer_general | ST8SIA5 |
| chr18 | 44336901 | 44336946 | Hyper | cancer_general | ST8SIA5 | chr18 | 44337174 | 44338074 | Hyper | cancer_general | ST8SIA5 |
| chr18 | 44773060 | 44773197 | Hyper | cancer_general | — | chr18 | 44773592 | 44774153 | Hyper | cancer_general | |
| chr18 | 44774406 | 44774890 | Hyper | cancer_general | — | chr18 | 44775380 | 44775554 | Hyper | cancer_general | |
| chr18 | 44776922 | 44777088 | Hyper | cancer_general | — | chr18 | 44777301 | 44777331 | Hyper | cancer_general | |
| chr18 | 44777596 | 44777750 | Hyper | cancer_general | — | chr18 | 44778049 | 44778326 | Hyper | cancer_general | |
| chr18 | 44781003 | 44781041 | Hyper | cancer_general | — | chr18 | 44787781 | 44787846 | Hyper | cancer_general | |
| chr18 | 44788251 | 44788281 | Hyper | cancer_general | — | chr18 | 44789474 | 44789514 | Hyper | cancer_general | |
| chr18 | 44789872 | 44789937 | Hyper | cancer_general | — | chr18 | 45058069 | 45058240 | Hyper | cancer_general | BC040860 |
| chr18 | 47720492 | 47720522 | Hyper | blood | — | chr18 | 48604773 | 48604802 | Hyper | literature | SMAD4 |
| chr18 | 49867303 | 49867399 | Hyper | cancer_general | DCC | chr18 | 49868634 | 49868664 | Hyper | cancer_general | DCC |
| chr18 | 52989009 | 52989220 | Hyper | cancer_general | TCF4 | chr18 | 52989741 | 52989882 | Hyper | cancer_general | TCF4 |
| chr18 | 53257137 | 53257204 | Hyper | cancer_general | TCF4 | chr18 | 53446970 | 53447816 | Hyper | tcga, liver_tcga, cancer_general | AK127787 |
| chr18 | 54789070 | 54789256 | Hyper | cancer_general | — | chr18 | 55019707 | 55019871 | Hyper | liver_tcga, cancer_general | ST8SIA3 |
| chr18 | 55020655 | 55020727 | Hyper | cancer_general | ST8SIA3 | chr18 | 55021078 | 55021242 | Hyper | cancer_general | ST8SIA3 |
| chr18 | 55103411 | 55103411 | Hyper | cancer_general | ONECUT2 | chr18 | 55103719 | 55103748 | Hyper | literature | ONECUT2 |
| chr18 | 55104808 | 55105140 | Hyper | cancer_general | ONECUT2 | chr18 | 55105728 | 55105830 | Hyper | cancer_general | ONECUT2 |
| chr18 | 55114480 | 55114644 | Hyper | cancer_general | ONECUT2 | chr18 | 56887076 | 56887424 | Hyper | cancer_general, tcga | GRP |
| chr18 | 56888554 | 56888623 | Hyper | cancer_general | GRP | chr18 | 56931541 | 56931583 | Hyper | cancer_general | RAX |
| chr18 | 56931967 | 56932107 | Hyper | cancer_general | RAX | chr18 | 56932352 | 56932637 | Hyper | cancer_general | RAX |
| chr18 | 56935010 | 56935319 | Hyper | cancer_general | RAX | chr18 | 56936004 | 56936074 | Hyper | cancer_general | RAX |
| chr18 | 56939113 | 56939174 | Hyper | cancer_general | RAX | chr18 | 56939423 | 56940722 | Hyper | cancer_general | RAX |
| chr18 | 56940955 | 56941788 | Hyper | cancer_general | CCBE1 | chr18 | 57363706 | 57363743 | Hyper | cancer_general | CCBE1 |
| chr18 | 57364275 | 57364392 | Hyper | cancer_general | CDH20 | chr18 | 57364658 | 57364691 | Hyper | pancreas | CCBE1 |
| chr18 | 59000988 | 59001022 | Hyper | cancer_general | — | chr18 | 59001301 | 59001740 | Hyper | cancer_general, tcga | CDH20 |
| chr18 | 60263547 | 60263895 | Hyper | cancer_general | DKFZp451A185 | chr18 | 60985498 | 60985732 | Hyper | liver_tcga, cancer_general | KDSR, BCL2 |
| chr18 | 67067558 | 67067907 | Hyper | tcga, cancer_general | DOK6 | chr18 | 67068152 | 67068203 | Hyper | cancer_general | DOK6 |
| chr18 | 67068442 | 67068471 | Hyper | tcga | DOK6 | chr18 | 67068715 | 67068811 | Hyper | cancer_general | DOK6 |
| chr18 | 67069216 | 67069246 | Hyper | cancer_general | DOK6 | chr18 | 70209148 | 70209205 | Hyper | tcga, cancer_general | CBLN2 |
| chr18 | 70209422 | 70209452 | Hyper | cancer_general | CBLN2 | chr18 | 70210418 | 70210508 | Hyper | tcga, cancer_general | CBLN2 |
| chr18 | 70211626 | 70211666 | Hyper | cancer_general | CBLN2 | chr18 | 70534282 | 70534969 | Hyper | cancer_general | NETO1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr18 | 70535373 | 70535582 | Hyper | cancer_general | NETO1 | chr18 | 70536010 | 70536604 | Hyper | cancer_general | NETO1 |
| chr18 | 70536833 | 70536871 | Hyper | cancer_general | NETO1 | chr18 | 70537188 | 70537218 | Hyper | cancer_general | NETO1 |
| chr18 | 73167585 | 73167832 | Hyper | cancer_general | — | chr18 | 73628019 | 73628068 | Hyper | cancer_general | — |
| chr18 | 74961326 | 74962147 | Hyper | cancer_general, literature | GALR1 | chr18 | 74962550 | 74962652 | Hyper | cancer_general | GALR1 |
| chr18 | 74962970 | 74963599 | Hyper | cancer_general | GALR1 | chr18 | 75362931 | 75362985 | Hyper | pancreas | — |
| chr18 | 75612225 | 75612286 | Hyper | cancer_general | — | chr18 | 76740079 | 76740285 | Hyper | liver_tcga | SALL3 |
| chr18 | 77548078 | 77548609 | Hyper | cancer_general | — | chr18 | 77558082 | 77558358 | Hyper | cancer_general | — |
| chr18 | 77558831 | 77558930 | Hyper | tcga | — | chr18 | 78004993 | 78005051 | Hyper | blood | PARD6G |
| chr9 | 113433 | 113556 | Hyper | cancer_general | FOXD4, CBWD1, FOXD4 | chr9 | 113850 | 113885 | Hyper | cancer_general | FOXD4, CBWD1 |
| chr9 | 117884 | 118090 | Hyper | cancer_general | CBWD1 | chr9 | 841691 | 842230 | Hyper | cancer_general | DMRT1 |
| chr9 | 842558 | 842673 | Hyper | cancer_general | DMRT1 | chr9 | 969556 | 969586 | Hyper | cancer_general | DMRT3, DMRT1 |
| chr9 | 969799 | 969846 | Hyper | cancer_general | DMRT3, DMRT1 | chr9 | 970096 | 970225 | Hyper | cancer_general | DMRT3, DMRT1 |
| chr9 | 970495 | 970525 | Hyper | cancer_general | DMRT3, DMRT1 | chr9 | 970897 | 971572 | Hyper | cancer_general | DMRT1, DMRT3 |
| chr9 | 972307 | 972759 | Hyper | tcga, cancer_general | DMRT3, DMRT1 | chr9 | 973143 | 973289 | Hyper | cancer_general | DMRT3, DMRT1 |
| chr9 | 974514 | 974547 | Hyper | cancer_general | DMRT1, DMRT3 | chr9 | 975117 | 975167 | Hyper | cancer_general | DMRT3, DMRT1 |
| chr9 | 975783 | 976321 | Hyper | cancer_general | DMRT3, DMRT1 | chr9 | 976618 | 976961 | Hyper | tcga, cancer_general | DMRT3, DMRT1 |
| chr9 | 981797 | 981830 | Hyper | cancer_general | DMRT3 | chr9 | 1042402 | 1042986 | Hyper | tcga, cancer_general | DMRT2 |
| chr9 | 1051848 | 1052166 | Hyper | cancer_general | DMRT2 | chr9 | 3181752 | 3181869 | Hyper | cancer_general | JAK2 |
| chr9 | 5070006 | 5070050 | Hyper | literature | JAK2 | chr9 | 5073756 | 5073788 | Hyper | literature | TRNA_Gln, JAK2 |
| chr9 | 5078346 | 5078375 | Hyper | literature | JAK2 | chr9 | 5089711 | 5089740 | Hyper | literature | JAK2 |
| chr9 | 6412571 | 6412809 | Hyper | cancer_general | UHRF2 | chr9 | 664297 | 664554 | Hyper | cancer_general | GLDC |
| chr9 | 6645017 | 6645333 | Hyper | cancer_general | GLDC | chr9 | 6645625 | 6645700 | Hyper | cancer_general | GLDC |
| chr9 | 13278818 | 13278864 | Hyper | blood | — | chr9 | 14312994 | 14313096 | Hyper | blood | NFIB |
| chr9 | 14313319 | 14313785 | Hyper | cancer_general | NFIB | chr9 | 14347633 | 14347673 | Hyper | cancer_general | — |
| chr9 | 14348314 | 14348452 | Hyper | cancer_general | — | chr9 | 17906404 | 17906694 | Hyper | cancer_general | — |
| chr9 | 17907004 | 17907061 | Hyper | cancer_general | — | chr9 | 17907416 | 17907472 | Hyper | cancer_general | — |
| chr9 | 19789107 | 19789301 | Hyper | cancer_general | SLC24A2 | chr9 | 21031734 | 21031836 | Hyper | cancer_general | PTPLAD2 |
| chr9 | 21402617 | 21403021 | Hyper | cancer_general | IFNA8 | chr9 | 21559294 | 21559381 | Hyper | blood | — |
| chr9 | 21559665 | 21559702 | Hyper | blood | — | chr9 | 21965057 | 21965757 | Hyper | lung, cancer_general | C9orf53, CDKN2A |
| chr9 | 21968218 | 21968475 | Hyper | literature, cancer_general | C9orf53, CDKN2A, C9orf53 | chr9 | 21970959 | 21971220 | Hyper | literature, cancer_general | CDKN2A, C9orf53 |
| chr9 | 21973940 | 21974237 | Hyper | cancer_general | CDKN2A, C9orf53 | chr9 | 21974499 | 21974794 | Hyper | liver_tcga, literature, cancer_general | CDKN2A, C9orf53 |
| chr9 | 21994208 | 21994237 | Hyper | literature | CDKN2B-AS1, CDKN2B | chr9 | 21995297 | 21995326 | Hyper | literature | CDKN2B, CDKN2B-AS1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 21995720 | 21995749 | Hyper | literature | CDKN2B-AS1, CDKN2B | chr9 | 22006131 | 22006160 | Hyper | literature | CDKN2B, CDKN2B-AS1 |
| chr9 | 22008819 | 22008899 | Hyper | literature | CDKN2B, CDKN2B-AS1 | chr9 | 22447664 | 22447708 | Hyper | tcga | DMRTA1 |
| chr9 | 23822568 | 23822606 | Hyper | cancer_general | — | chr9 | 23824561 | 23824591 | Hyper | cancer_general | — |
| chr9 | 23831100 | 23831399 | Hyper | cancer_general | — | chr9 | 29212170 | 29212294 | Hyper | cancer_general | — |
| chr9 | 29213508 | 29213651 | Hyper | cancer_general | — | chr9 | 29214030 | 29214144 | Hyper | cancer_general | — |
| chr9 | 29214360 | 29214430 | Hyper | cancer_general | — | chr9 | 29214681 | 29215086 | Hyper | cancer_general | — |
| chr9 | 32782630 | 32783121 | Hyper | cancer_general | TMEM215 | chr9 | 32783346 | 32783657 | Hyper | cancer_general | TMEM215 |
| chr9 | 33524609 | 33524687 | Hyper | cancer_general | ANKRD18B | chr9 | 33676771 | 33676801 | Hyper | cancer_general | PTENP1 |
| chr9 | 33677360 | 33677415 | Hyper | cancer_general | PTENP1 | chr9 | 34589062 | 34589156 | Hyper | cancer_general | LOC415056, CNTFR |
| chr9 | 34809749 | 34809981 | Hyper | cancer_general | — | chr9 | 35617291 | 35617337 | Hyper | tcga | CD72, MIR4667, TESK1 |
| chr9 | 35675539 | 35676180 | Hyper | tcga, cancer_general | HV781757, TPM2, CA9 | chr9 | 35844834 | 35844863 | Hyper | literature | TMEM8B |
| chr9 | 36037068 | 36037098 | Hyper | esophageal | RECK | chr9 | 36739755 | 36739980 | Hyper | cancer_general | — |
| chr9 | 37002454 | 37003077 | Hyper | literature, cancer_general | PAX5 | chr9 | 37025564 | 37025783 | Hyper | literature, cancer_general | PAX5 |
| chr9 | 37026146 | 37026622 | Hyper | cancer_general | PAX5 | chr9 | 37026831 | 37027412 | Hyper | tcga, colorectal, cancer_general | PAX5 |
| chr9 | 37027800 | 37027829 | Hyper | literature | PAX5 | chr9 | 37028944 | 37029119 | Hyper | cancer_general | PAX5 |
| chr9 | 37029534 | 37030655 | Hyper | cancer_general, literature | PAX5 | chr9 | 37034197 | 37034247 | Hyper | cancer_general | PAX5 |
| chr9 | 37034616 | 37034731 | Hyper | cancer_general, literature | PAX5 | chr9 | 37035366 | 37035734 | Hyper | literature, cancer_general | PAX5 |
| chr9 | 37036425 | 37036647 | Hyper | cancer_general | PAX5 | chr9 | 37037671 | 37038354 | Hyper | cancer_general | — |
| chr9 | 38620530 | 38620725 | Hyper | blood | FAM201A, ANKRD18A | chr9 | 66455999 | 66456047 | Hyper | cancer_general | CR627148, AK308561 |
| chr9 | 71788952 | 71789757 | Hyper | cancer_general | TJP2, AK096834 | chr9 | 74061838 | 74062070 | Hyper | cancer_general | TRPM3 |
| chr9 | 74764547 | 74764648 | Hyper | cancer_general | GDA | chr9 | 77112993 | 77113825 | Hyper | pancreas, cancer_general | RORB |
| chr9 | 77114745 | 77114851 | Hyper | cancer_general | RORB | chr9 | 77115210 | 77115447 | Hyper | cancer_general | RORB |
| chr9 | 77115657 | 77115687 | Hyper | cancer_general | RORB | chr9 | 79626876 | 79627370 | Hyper | cancer_general | FOXB2 |
| chr9 | 79628289 | 79628329 | Hyper | cancer_general | FOXB2 | chr9 | 79629095 | 79629471 | Hyper | cancer_general | FOXB2 |
| chr9 | 79629879 | 79630420 | Hyper | cancer_general | FOXB2 | chr9 | 79631192 | 79631335 | Hyper | cancer_general | FOXB2 |
| chr9 | 79631555 | 79631591 | Hyper | cancer_general | FOXB2 | chr9 | 79631865 | 79632182 | Hyper | cancer_general | FOXB2 |
| chr9 | 79632860 | 79632890 | Hyper | cancer_general | FOXB2 | chr9 | 79633397 | 79633904 | Hyper | tcga, cancer_general | FOXB2 |
| chr9 | 79634170 | 79636043 | Hyper | cancer_general | FOXB2 | chr9 | 79636258 | 79637274 | Hyper | cancer_general | FOXB2 |
| chr9 | 79637555 | 79638150 | Hyper | cancer_general | FOXB2 | chr9 | 80409473 | 80409502 | Hyper | literature | GNAQ |
| chr9 | 85677905 | 85677992 | Hyper | blood | RASEF | chr9 | 86152387 | 86152417 | Hyper | cancer_general | — |
| chr9 | 86755532 | 86755952 | Hyper | cancer_general | — | chr9 | 86886706 | 86886736 | Hyper | cancer_general | SLC28A3 |
| chr9 | 87283008 | 87283038 | Hyper | cancer_general | NTRK2 | chr9 | 87283677 | 87283709 | Hyper | cancer_general | NTRK2 |
| chr9 | 87284706 | 87284798 | Hyper | cancer_general | NTRK2 | chr9 | 87285279 | 87285472 | Hyper | cancer_general | INTRK2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 88137524 | 88137998 | Hyper | tcga, cancer_general | — | chr9 | 89517699 | 89517835 | Hyper | cancer_general | — |
| chr9 | 89560760 | 89560827 | Hyper | cancer_general | LOC100506834, GAS1 | chr9 | 89561063 | 89561109 | Hyper | cancer_general | LOC100506834, GAS1 |
| chr9 | 91150222 | 91150335 | Hyper | cancer_general | NXNL2 | chr9 | 91606004 | 91606058 | Hyper | cancer_general | C9orf47, S1PR3 |
| chr9 | 91792357 | 91792387 | Hyper | cancer_general | SHC3 | chr9 | 91792776 | 91792907 | Hyper | cancer_general | SHC3 |
| chr9 | 91793177 | 91793526 | Hyper | tcga, cancer_general | SHC3 | chr9 | 94183870 | 94183954 | Hyper | cancer_general | — |
| chr9 | 94712163 | 94712236 | Hyper | cancer_general | ROR2 | chr9 | 95569759 | 95569822 | Hyper | cancer_general | ANKRD19P |
| chr9 | 95570247 | 95570434 | Hyper | cancer_general | ANKRD19P | chr9 | 95571617 | 95571760 | Hyper | cancer_general | ANKRD19P |
| chr9 | 95947296 | 95947296 | Hyper | cancer_general | WNK2 | chr9 | 96588804 | 96588885 | Hyper | cancer_general | MIR4291 |
| chr9 | 96710377 | 96710407 | Hyper | cancer_general | BARX1 | chr9 | 96710647 | 96710991 | Hyper | cancer_general | BARX1 |
| chr9 | 96711258 | 96711617 | Hyper | cancer_general | BARX1 | chr9 | 96711975 | 96712005 | Hyper | cancer_general | BARX1 |
| chr9 | 96713378 | 96713893 | Hyper | cancer_general | BARX1 | chr9 | 96715095 | 96715857 | Hyper | tcga, cancer_general | BARX1 |
| chr9 | 96716837 | 96717466 | Hyper | cancer_general | JB148981, BARX1 | chr9 | 96717979 | 96718149 | Hyper | cancer_general | JB148981, BARX1 |
| chr9 | 96720803 | 96721802 | Hyper | lung, cancer_general | JB148981, BARX1 | chr9 | 96722445 | 96722786 | Hyper | cancer_general, lung | JB148981, BARX1 |
| chr9 | 96723093 | 96723202 | Hyper | cancer_general | BARX1 | chr9 | 98111365 | 98112395 | Hyper | cancer_general | — |
| chr9 | 98784772 | 98784802 | Hyper | cancer_general | LINC00092, C9orf102, ERCC6L2 | chr9 | 98789651 | 98790000 | Hyper | cancer_general | LINC00092, C9orf102 |
| chr9 | 99146020 | 99146153 | Hyper | blood | ZNF367, SLC35D2 | chr9 | 99449135 | 99449451 | Hyper | liver_tcga, cancer_general | — |
| chr9 | 99639621 | 99639942 | Hyper | cancer_general | LOC100132781, ZNF782 | chr9 | 99983140 | 99983170 | Hyper | cancer_general | — |
| chr9 | 99983411 | 99983824 | Hyper | cancer_general | — | chr9 | 99984026 | 99984242 | Hyper | cancer_general | FOXE1 |
| chr9 | 100503625 | 100503937 | Hyper | cancer_general | — | chr9 | 100609991 | 100610218 | Hyper | cancer_general | FOXE1 |
| chr9 | 100610681 | 100611640 | Hyper | cancer_general | FOXE1 | chr9 | 100613828 | 100614325 | Hyper | cancer_general | FOXE1 |
| chr9 | 100614541 | 100616902 | Hyper | tcga, liver_tcga, cancer_general | FOXE1 | chr9 | 100617293 | 100617365 | Hyper | cancer_general | FOXE1 |
| chr9 | 100617682 | 100618055 | Hyper | cancer_general | FOXE1 | chr9 | 100619722 | 100620069 | Hyper | cancer_general | FOXE1 |
| chr9 | 100620330 | 100620783 | Hyper | cancer_general | FOXE1 | chr9 | 101469269 | 101469307 | Hyper | cancer_general | GABBR2 |
| chr9 | 101469603 | 101469796 | Hyper | cancer_general | GABBR2 | chr9 | 101470116 | 101470250 | Hyper | cancer_general | GABBR2 |
| chr9 | 101470968 | 101471071 | Hyper | cancer_general | GABBR2 | chr9 | 101471570 | 101471621 | Hyper | cancer_general | GABBR2 |
| chr9 | 101471860 | 101472009 | Hyper | tcga, cancer_general | GABBR2 | chr9 | 101705996 | 101706695 | Hyper | cancer_general | COL15A1 |
| chr9 | 104248579 | 104248623 | Hyper | cancer_general | TMEM246 | chr9 | 104249475 | 104249562 | Hyper | tcga | — |
| chr9 | 104500625 | 104500774 | Hyper | cancer_general | — | chr9 | 110228200 | 110228602 | Hyper | liver_tcga, cancer_general | — |
| chr9 | 110251388 | 110251418 | Hyper | blood | KLF4 | chr9 | 110252363 | 110252515 | Hyper | blood | KLF4 |
| chr9 | 112403170 | 112403200 | Hyper | cancer_general | PALM2, Mir_548 | chr9 | 113341522 | 113341965 | Hyper | tcga, cancer_general | — |
| chr9 | 113342299 | 113342340 | Hyper | cancer_general | — | chr9 | 115652966 | 115653425 | Hyper | cancer_general | — |
| chr9 | 118917024 | 118917079 | Hyper | cancer_general | PAPPA | chr9 | 120175795 | 120175832 | Hyper | cancer_general | SLC46A2 |
| chr9 | 120176104 | 120176151 | Hyper | cancer_general | — | chr9 | 120176867 | 120176897 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 120507409 | 120507439 | Hyper | cancer_general | — | chr9 | 122131481 | 122131642 | Hyper | cancer_general | DBC1 |
| chr9 | 122131880 | 122132227 | Hyper | tcga, cancer_general | DBC1 | chr9 | 123004898 | 123004928 | Hyper | esophageal | MIR147A |
| chr9 | 124535347 | 124535611 | Hyper | liver_tcga | DAB2IP | chr9 | 126770257 | 126770298 | Hyper | cancer_general | LHX2, AK131516 |
| chr9 | 126771532 | 126771705 | Hyper | cancer_general | LHX2, AK131516 | chr9 | 126774517 | 126775144 | Hyper | cancer_general | LHX2, AK131516 |
| chr9 | 126775530 | 126775560 | Hyper | cancer_general | LHX2, AK131516 | chr9 | 126776044 | 126776119 | Hyper | cancer_general | AK131516, LHX2 |
| chr9 | 126777529 | 126777982 | Hyper | cancer_general | LHX2, AK131516 | chr9 | 126778329 | 126778496 | Hyper | cancer_general | AK131516, LHX2 |
| chr9 | 126779485 | 126780315 | Hyper | cancer_general | LHX2, AK131516 | chr9 | 126780811 | 126780898 | Hyper | cancer_general | LHX2, AK131516 |
| chr9 | 126783295 | 126783499 | Hyper | cancer_general | LHX2 | chr9 | 127212851 | 127213006 | Hyper | cancer_general | GPR144 |
| chr9 | 127265688 | 127266025 | Hyper | cancer_general | NR5A1 | chr9 | 127266387 | 127266534 | Hyper | cancer_general | NR5A1 |
| chr9 | 127920543 | 127920572 | Hyper | literature | PPP6C | chr9 | 128652200 | 128652232 | Hyper | cancer_general | PBX3 |
| chr9 | 129276718 | 129276820 | Hyper | cancer_general | — | chr9 | 129372929 | 129373223 | Hyper | cancer_general | LMX1B |
| chr9 | 129376170 | 129376199 | Hyper | literature | LMX1B | chr9 | 129376889 | 129376918 | Hyper | literature | LMX1B |
| chr9 | 129377214 | 129377316 | Hyper | cancer_general | LMX1B | chr9 | 129377604 | 129378003 | Hyper | tcga, literature, cancer_general | LMX1B |
| chr9 | 129381111 | 129381180 | Hyper | cancer_general | LMX1B | chr9 | 129387434 | 129387464 | Hyper | cancer_general | LMX1B |
| chr9 | 129387800 | 129388200 | Hyper | cancer_general | LMX1B | chr9 | 129388996 | 129389192 | Hyper | cancer_general | LMX1B |
| chr9 | 129400986 | 129401195 | Hyper | cancer_general, breast | LMX1B | chr9 | 129445255 | 129445566 | Hyper | cancer_general | LMX1B |
| chr9 | 129445783 | 129445813 | Hyper | cancer_general | LMX1B | chr9 | 129485841 | 129485923 | Hyper | cancer_general | — |
| chr9 | 130461642 | 130461742 | Hyper | cancer_general | C9orfl17, BC032117, MIR3911, STXBP1 | chr9 | 130689626 | 130689749 | Hyper | liver_tcga | DPM2, PIP5KL1 |
| chr9 | 132382383 | 132383109 | Hyper | tcga, literature, cancer_general | NTMT1, C9orf50 | chr9 | 132804405 | 132804455 | Hyper | esophageal | FNBP1 |
| chr9 | 132804796 | 132804974 | Hyper | esophageal | FNBP1 | chr9 | 132805318 | 132805445 | Hyper | esophageal | FNBP1 |
| chr9 | 132805737 | 132805893 | Hyper | esophageal | FNBP1 | chr9 | 133308893 | 133308941 | Hyper | cancer_general | AK074396 |
| chr9 | 133534683 | 133534713 | Hyper | cancer_general | PRDM12 | chr9 | 133535734 | 133535839 | Hyper | tcga | PRDM12 |
| chr9 | 133536097 | 133536344 | Hyper | cancer_general | PRDM12 | chr9 | 133536778 | 133536869 | Hyper | cancer_general | PRDM12 |
| chr9 | 133537182 | 133537549 | Hyper | cancer_general | PRDM12 | chr9 | 133538169 | 133538728 | Hyper | cancer_general | PRDM12 |
| chr9 | 133539606 | 133539709 | Hyper | cancer_general | PRDM12 | chr9 | 133541192 | 133541192 | Hyper | literature | ABL1, AX748265 |
| chr9 | 133541689 | 133542337 | Hyper | cancer_general | PRDM12 | chr9 | 133738343 | 133738372 | Hyper | literature | — |
| chr9 | 133747505 | 133747534 | Hyper | literature | AX748265, ABL1 | chr9 | 134421797 | 134421835 | Hyper | blood | — |
| chr9 | 135037119 | 135037357 | Hyper | tcga | NTNG2 | chr9 | 135455407 | 135455585 | Hyper | cancer_general | BARHL1, C9orfl71 |
| chr9 | 135455996 | 135456065 | Hyper | cancer_general | BARHL1, C9orfl71 | chr9 | 135456496 | 135456526 | Hyper | cancer_general | BARHL1, C9orfl71 |
| chr9 | 135456897 | 135456932 | Hyper | cancer_general | BARHL1, C9orfl71 | chr9 | 135458477 | 135458597 | Hyper | cancer_general | BARHL1, C9orfl71 |
| chr9 | 135460001 | 135460176 | Hyper | cancer_general | BARHL1, DDX31 | chr9 | 135460869 | 135460899 | Hyper | cancer_general | DDX31, BARHL1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr9 | 135461511 | 135461773 | Hyper | cancer_general | DDX31, BARHL1 | chr9 | 135462048 | 135462967 | Hyper | cancer_general | DDX31, BARHL1 |
| chr9 | 135464798 | 135464918 | Hyper | cancer_general | DDX31, ABRHL1 | chr9 | 135465948 | 135466132 | Hyper | cancer_general | DDX31, BARHL1 |
| chr9 | 135466344 | 135466660 | Hyper | cancer_general | DDX31, BARHL1 | chr9 | 135796801 | 135796830 | Hyper | literature | TSC1 |
| chr9 | 136474490 | 136474607 | Hyper | cancer_general | — | chr9 | 137111397 | 137111426 | Hyper | liver_tcga | — |
| chr9 | 137229892 | 137229921 | Hyper | liver_tcga | RXRA | chr9 | 137299119 | 137299450 | Hyper | tcga, cancer_general | RXRA |
| chr9 | 137533974 | 137534238 | Hyper | cancer_general | COL5A1 | chr9 | 137702189 | 137702222 | Hyper | esophageal | LOC101448202, COL5A1 |
| chr9 | 137979893 | 137980011 | Hyper | cancer_general | OLFM1 | chr9 | 137980258 | 137980288 | Hyper | cancer_general | OLFM1 |
| chr9 | 137980880 | 137980910 | Hyper | cancer_general | OLFM1 | chr9 | 138606307 | 138606372 | Hyper | cancer_general | KCNT1 |
| chr9 | 138606796 | 138606923 | Hyper | tcga | KCNT1 | chr9 | 139024723 | 139024782 | Hyper | cancer_general | |
| chr9 | 139085228 | 139085360 | Hyper | cancer_general | RBSG2, LHX3 | chr9 | 139085924 | 139085978 | Hyper | cancer_general | LHX3, RBSG2 |
| chr9 | 139090500 | 139090578 | Hyper | cancer_general | QSOX2, LHX3, RBSG2 | chr9 | 139090793 | 139091369 | Hyper | cancer_general | QSOX2, LHX3, RBSG2 |
| chr9 | 139093681 | 139093890 | Hyper | cancer_general | QSOX2, LHX3, RBSG2 | chr9 | 139094705 | 139094873 | Hyper | cancer_general | QSOX2, RBSG2 |
| chr9 | 139095340 | 139095485 | Hyper | cancer_general | QSOX2, LHX3, RBSG2 | chr9 | 139096650 | 139097006 | Hyper | cancer_general | LHX3, QSOX2 |
| chr9 | 139399407 | 139399436 | Hyper | literature | NOTCH1 | chr9 | 139739236 | 139739300 | Hyper | cancer_general | PHPT1, MAMDC4, C9orf172, RABL6 |
| chr9 | 140024842 | 140025023 | Hyper | colorectal, cancer_general | GRIN1 | chr9 | 140032891 | 140032951 | Hyper | cancer_general | GRIN1 |
| chr9 | 140033426 | 140033642 | Hyper | cancer_general liver_tcga, cancer_general | GRIN1 | chr9 | 140033909 | 140034079 | Hyper | cancer_general | GRIN1 |
| chr9 | 140050969 | 140051354 | Hyper | | GRIN1 | chr9 | 140197122 | 140197263 | Hyper | hepatobiliary | NRARP, EXD3 |
| chr9 | 140771975 | 140772347 | Hyper | literature, cancer_general | CACNA1B, AK128414 ODF3L2, SHC2 | chr9 | 140772586 | 140773301 | Hyper | cancer_general | CACNA1B, AK128414 |
| chr19 | 462181 | 462269 | Hyper | blood | | chr19 | 591365 | 591416 | Hyper | cancer_general | HCN2, BSG |
| chr19 | 1220422 | 1220610 | Hyper | literature | C19orf26, STK11 | chr19 | 1221981 | 1222010 | Hyper | literature | C19orf26, STK11 |
| chr19 | 1308047 | 1308081 | Hyper | head_neck | EFNA2 | chr19 | 1401752 | 1401795 | Hyper | tcga | NDUFS7, DAZAP1, GAMT, KA126693 |
| chr19 | 1450319 | 1450390 | Hyper | cancer_general | APC2, RPS15 | chr19 | 1467423 | 1468188 | Hyper | cancer_general | C19orf25, APC2 |
| chr19 | 1524368 | 1524447 | Hyper | cancer_general | PLK5 | chr19 | 1754172 | 1754254 | Hyper | cancer_general | ONECUT3 |
| chr19 | 1754739 | 1754804 | Hyper | cancer_general | ONECUT3 | chr19 | 1757416 | 1757615 | Hyper | cancer_general | ONECUT3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 1762474 | 1762575 | Hyper | cancer_general | ONECUT3 | chr19 | 1764293 | 1764339 | Hyper | pancreas | ONECUT3 |
| chr19 | 1775076 | 1775239 | Hyper | head_neck | ATP8B3, ONECUT3 | chr19 | 1776376 | 1776534 | Hyper | pancreas, cancer general | ATP8B3, ONECUT3 |
| chr19 | 2135672 | 2135701 | Hyper | liver_tcga | — | chr19 | 2251152 | 2251715 | Hyper | cancer_general | JSRP1, MIR4321, AMH, SF3A2 |
| chr19 | 2252066 | 2252658 | Hyper | tcga, cancer_general | JSRP1, MIR4321, AMH, SF3A2 | chr19 | 2252984 | 2253775 | Hyper | tcga, cancer_general | JSRP1, MIR4321, AMH, SF3A2 |
| chr19 | 2290253 | 2291034 | Hyper | tcga, cancer_general | SPPL2B, AX747191, LINGO3, C19orf35 | chr19 | 2302793 | 2302951 | Hyper | cancer_general | — |
| chr19 | 3114998 | 3115027 | Hyper | literature | DKFZp434J194, GNA11 | chr19 | 3118927 | 3118956 | Hyper | literature | GNA11, DKFZp434J194 |
| chr19 | 3361139 | 3361388 | Hyper | tcga | NFIC | chr19 | 3639668 | 3659793 | Hyper | liver_tcga | PIP5K1C |
| chr19 | 3785649 | 3786260 | Hyper | tcga, liver_tcga, cancer_general | JA611290, MATK | chr19 | 3822111 | 3822203 | Hyper | tcga | ZFR2 |
| chr19 | 4101087 | 4101116 | Hyper | literature | MAP2K2 | chr19 | 4110565 | 4110597 | Hyper | literature | MAP2K2 |
| chr19 | 4117526 | 4117630 | Hyper | literature | MAP2K2 | chr19 | 4305057 | 4305086 | Hyper | literature | FSD1, TMIGD2 |
| chr19 | 4944145 | 4944174 | Hyper | liver_tcga | — | chr19 | 5292812 | 5292844 | Hyper | pancreas | PTPRS |
| chr19 | 5338914 | 5339143 | Hyper | tcga, cancer_general | — | chr19 | 6590325 | 6590478 | Hyper | cancer_general | CD70 |
| chr19 | 7615996 | 7616025 | Hyper | liver_tcga | PNPLA6 | chr19 | 7446942 | 7747042 | Hyper | tcga | TRAPPC5, FCER2, C19orf59 |
| chr19 | 7795012 | 7795244 | Hyper | cancer_general | CD209, CLEC4G | chr19 | 7853028 | 7853157 | Hyper | cancer_general | CLEC4GP1 |
| chr19 | 7853361 | 7853460 | Hyper | cancer_general | CLEC4GP1 | chr19 | 8115235 | 8115276 | Hyper | cancer_general | CCL25 |
| chr19 | 9420142 | 9420240 | Hyper | esophageal | ZNF699 | chr19 | 9473564 | 9474056 | Hyper | liver_tcga, literature, cancer_general | ZNF177, ZNF559-ZNF177 |
| chr19 | 9517609 | 9517771 | Hyper | cancer_general | ZNF266 | chr19 | 9608895 | 9609036 | Hyper | cancer_general | ZNF560 |
| chr19 | 9609319 | 9609436 | Hyper | cancer_general, literature | ZNF560 | chr19 | 9903913 | 9904100 | Hyper | tcga, cancer_general | — |
| chr19 | 10398209 | 10398285 | Hyper | cancer_general | ICAM4, ICAM1, ICAM5 | chr19 | 10405972 | 10406349 | Hyper | cancer_general | ZGLP1, FDX1L, ICAM5, ICAM4, ICAM1 |
| chr19 | 10406806 | 10407135 | Hyper | lung, cancer_general | ICAM1, LZGP1, FDX1L, ICAM5, ICAM4 | chr19 | 10527165 | 10527243 | Hyper | esophageal | PDE4A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 10531419 | 10531512 | Hyper | tcga | PDE4A | chr19 | 10531964 | 10531994 | Hyper | cancer_general | PDE4A |
| chr19 | 10600431 | 10600460 | Hyper | literature | KEAP1 | chr19 | 10602274 | 10602348 | Hyper | literature | KEAP1 |
| chr19 | 10602565 | 10602864 | Hyper | literature | KEAP1 | chr19 | 10610138 | 10610260 | Hyper | literature | KEAP1 |
| chr19 | 10624751 | 10625465 | Hyper | cancer_general | S1PR5 | chr19 | 11134252 | 11134281 | Hyper | literature | SMARCA4 |
| chr19 | 11138507 | 11138536 | Hyper | literature | SMARCA4 | chr19 | 11492252 | 11492528 | Hyper | lung | RGL3, EPOR, SWSAP1 |
| chr19 | 11591031 | 11591185 | Hyper | cancer_general | ZNF653, ELAVL3 | chr19 | 11592710 | 11592750 | Hyper | cancer_general | ELAVL3, ZNF653 |
| chr19 | 11593022 | 11593159 | Hyper | cancer_general | ZNF653, ELAVL3 | chr19 | 11689460 | 11689564 | Hyper | cancer_general | ACP5, BC039523 |
| chr19 | 11959912 | 11960077 | Hyper | cancer_general | ZNF439 | chr19 | 12163448 | 12163672 | Hyper | esophageal | ZNF878 |
| chr19 | 12163893 | 12163923 | Hyper | esophageal | ZNF878 | chr19 | 12175445 | 12175504 | Hyper | esophageal | ZNF844 |
| chr19 | 12175814 | 12176005 | Hyper | cancer_general | ZNF844 | chr19 | 12203028 | 12203744 | Hyper | liver_tcga, cancer_general | ZNF788 |
| chr19 | 12267019 | 12267667 | Hyper | tcga, cancer_general | ZNF136, ZNF625 | chr19 | 12305839 | 12306263 | Hyper | liver_tcga, literature, cancer_general | AX721123, ZNF136, AK023304 |
| chr19 | 12476492 | 12476556 | Hyper | esophageal | ZNF442 | chr19 | 12595109 | 12595307 | Hyper | esophageal | ZNF709 |
| chr19 | 12595845 | 12595896 | Hyper | esophageal | ZNF709 | chr19 | 12606381 | 12606511 | Hyper | esophageal | ZNF709 |
| chr19 | 12750987 | 12751056 | Hyper | cancer_general | MAN2B1 | chr19 | 12952000 | 12952139 | Hyper | cancer_general | RTBDN, MAST1 |
| chr19 | 12996169 | 12996280 | Hyper | pancreas | DNASE2, GCDH, KLF1 | chr19 | 13113454 | 13113668 | Hyper | liver_tcga | NFIX |
| chr19 | 13210225 | 13210316 | Hyper | cancer_general | TRMT1, LYL1, NFIX | chr19 | 13616696 | 13617256 | Hyper | cancer_general | CACNA1A |
| chr19 | 13618288 | 13618381 | Hyper | cancer_general | CACNA1A | chr19 | 14584240 | 14584775 | Hyper | cancer_general | GIPC1, PTGER1, PKN1 |
| chr19 | 15090172 | 15090499 | Hyper | cancer_general | SLC1A6 | chr19 | 15121685 | 15121894 | Hyper | cancer_general | CCDC105 |
| chr19 | 15122120 | 15122238 | Hyper | tcga | CCDC105 | chr19 | 15288433 | 15288856 | Hyper | cancer_general | NOTCH3 |
| chr19 | 15342734 | 15343373 | Hyper | cancer_general, liver_tcga | BRD4, EPHX3 | chr19 | 15344107 | 15344325 | Hyper | cancer_general | BRD4, EPHX3 |
| chr19 | 15580685 | 15580714 | Hyper | literature | PGLYRP2, RASAL3 | chr19 | 16999599 | 16999782 | Hyper | literature | SIN3B, F2RL3, CPAMD8 |
| chr19 | 17007086 | 17007662 | Hyper | cancer_general | CPAMD8, F2RL3 | chr19 | 17008523 | 17008799 | Hyper | cancer_general, liver_tcga | CPAMD8, F2RL3 |
| chr19 | 17392641 | 17392866 | Hyper | tcga | ANKLE1, BABAM1 | chr19 | 17717286 | 17717315 | Hyper | literature | UNC13A |
| chr19 | 17791182 | 17791211 | Hyper | literature | UNC13A | chr19 | 17943423 | 17943452 | Hyper | literature | JAK3 |
| chr19 | 17945891 | 17945983 | Hyper | literature | JAK3 | chr19 | 17947991 | 17948023 | Hyper | literature | JAK3 |
| chr19 | 17949094 | 17949123 | Hyper | literature | JAK3 | chr19 | 17958490 | 17958839 | Hyper | tcga | JAK3 |
| chr19 | 17983537 | 17983834 | Hyper | cancer_general | SLC5A5 | chr19 | 18271894 | 18271923 | Hyper | literature | PIK3R2, MAST3 |
| chr19 | 18278047 | 18278076 | Hyper | literature | PIK3R2, IFI30 | chr19 | 18343439 | 18343569 | Hyper | cancer_general | PDE4C |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 18343921 | 18343963 | Hyper | cancer_general | PDE4C | chr19 | 18714552 | 18714675 | Hyper | cancer_general | TMEM59L, CRLF1 |
| chr19 | 18811560 | 18811804 | Hyper | tcga | CRTC1 | chr19 | 18899432 | 18899652 | Hyper | cancer_general | COMP, CRTC1 |
| chr19 | 18901828 | 18902095 | Hyper | tcga, cancer_general | COMP, CRTC1 | chr19 | 18980760 | 18980897 | Hyper | cancer_general | UPF1, CERS1, GDF1 |
| chr19 | 19260030 | 19260101 | Hyper | literature | MEF2B, MEF2BNB-MEF2B | chr19 | 19261519 | 19261548 | Hyper | literature | MEF2B, MEF2BNB-MEF2B |
| chr19 | 19651961 | 19652066 | Hyper | liver_tcga | CILP2, YJEFN3 | chr19 | 19729251 | 19729395 | Hyper | liver_tcga | LPAR2, PBX4 |
| chr19 | 19739172 | 19739428 | Hyper | tcga, liver_tcga | GMIP, LPAR2, PBX4 | chr19 | 20011955 | 20012149 | Hyper | liver_tcga, cancer_general | ZNF93, ZNF253 |
| chr19 | 20188693 | 20188872 | Hyper | cancer_general | ZNF90 | chr19 | 20189322 | 20189438 | Hyper | cancer_general | ZNF90 |
| chr19 | 21646407 | 21646437 | Hyper | cancer_general | CR627135 | chr19 | 21688814 | 21688912 | Hyper | esophageal | ZNF429, LINC00664 |
| chr19 | 21769300 | 21769444 | Hyper | tcga | BC033373, AX748435 | chr19 | 22018523 | 22018805 | Hyper | tcga | ZNF43 |
| chr19 | 22034198 | 22034813 | Hyper | cancer_general | ZNF43 | chr19 | 22610635 | 22610747 | Hyper | cancer_general | ZNF98 |
| chr19 | 22715140 | 22715443 | Hyper | cancer_general | — | chr19 | 23254189 | 23254219 | Hyper | cancer_general | ZNF429 |
| chr19 | 23257703 | 23258694 | Hyper | cancer_general | — | chr19 | 23299748 | 23300080 | Hyper | tcga, cancer_general | ZNF730 |
| chr19 | 23432562 | 23432723 | Hyper | esophageal | AK023040, ZNF724P | chr19 | 23433143 | 23433296 | Hyper | esophageal | AK023040, ZNF724P |
| chr19 | 23456615 | 23456881 | Hyper | esophageal | AK023040 | chr19 | 23598274 | 23598326 | Hyper | cancer_general | BC043213, AK022793 |
| chr19 | 24154592 | 24154621 | Hyper | liver_tcga | — | chr19 | 24216975 | 24217023 | Hyper | esophageal | ZNF254, AK092150, AK092080 |
| chr19 | 29284452 | 29284719 | Hyper | cancer_general | — | chr19 | 30015934 | 30016712 | Hyper | cancer_general | VSTM2B, LOC284395 |
| chr19 | 30016914 | 30018608 | Hyper | cancer_general | VSTM2B, LOC284395 | chr19 | 30019145 | 30019838 | Hyper | tcga, cancer_general | VSTM2B, LOC284395 |
| chr19 | 30020093 | 30020473 | Hyper | cancer_general | VSTM2B, LOC284395 | chr19 | 30021125 | 30021193 | Hyper | cancer_general | VSTM2B, LOC284395 |
| chr19 | 30215542 | 30215571 | Hyper | tcga | C19orf12 | chr19 | 30713480 | 30713706 | Hyper | cancer_general | — |
| chr19 | 30713909 | 30714047 | Hyper | cancer_general | — | chr19 | 30714403 | 30714433 | Hyper | cancer_general | — |
| chr19 | 30715402 | 30715766 | Hyper | cancer_general | — | chr19 | 30716313 | 30716576 | Hyper | cancer_general | — |
| chr19 | 30716812 | 30718149 | Hyper | tcga, cancer_general | — | chr19 | 30718847 | 30718913 | Hyper | cancer_general | — |
| chr19 | 30719449 | 30720067 | Hyper | tcga, cancer_general | — | chr19 | 30865713 | 30866436 | Hyper | cancer_general | ZNF536 |
| chr19 | 31839765 | 31839873 | Hyper | cancer_general | TSHZ3 | chr19 | 31841937 | 31842389 | Hyper | tcga, cancer_general | TSHZ3 |
| chr19 | 31842596 | 31842646 | Hyper | cancer_general | TSHZ3 | chr19 | 32715673 | 32715741 | Hyper | cancer_general | — |
| chr19 | 33167116 | 33167431 | Hyper | cancer_general | RGS9BP, ANKRD27 | chr19 | 33685544 | 33685581 | Hyper | esophageal | LRP3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 33792159 | 33792524 | Hyper | blood | CEBPA-AS1, CEBPA | chr19 | 33794675 | 33794760 | Hyper | tcga | CEBPA-AS1, CEBPA |
| chr19 | 34112288 | 34112320 | Hyper | cancer_general | CHST8 | chr19 | 34112524 | 34112973 | Hyper | cancer_general | CHST8 |
| chr19 | 34113349 | 34113587 | Hyper | cancer_general | CHST8 | chr19 | 34114006 | 34114113 | Hyper | cancer_general | CHST8 |
| chr19 | 34533139 | 34533169 | Hyper | head_neck | — | chr19 | 34972464 | 34972494 | Hyper | cancer_general | WTIP |
| chr19 | 34973225 | 34973255 | Hyper | cancer_general | WTIP | chr19 | 34973656 | 34973697 | Hyper | cancer_general | WTIP |
| chr19 | 34973932 | 34973965 | Hyper | pancreas | WTIP | chr19 | 35264085 | 35264119 | Hyper | esophageal | ZNF599 |
| chr19 | 35396013 | 35396370 | Hyper | cancer_general | LINC00904, BC031235 | chr19 | 36048595 | 36048771 | Hyper | cancer_general, liver_tcga | ATP4A |
| chr19 | 36049327 | 36049462 | Hyper | tcga | ATP4A | chr19 | 36334979 | 36335147 | Hyper | cancer_general | NPHS1 |
| chr19 | 36347892 | 36348048 | Hyper | tcga | KIRREL2 | chr19 | 36450106 | 36450372 | Hyper | tcga, cancer_general | — |
| chr19 | 36523333 | 36523480 | Hyper | cancer_general | THAP8, CLIP3, BC071809 | chr19 | 36736027 | 36736057 | Hyper | cancer_general | ZNF146 |
| chr19 | 36736319 | 36736491 | Hyper | cancer_general | ZNF146 | chr19 | 36822324 | 36822892 | Hyper | cancer_general | ZFP14, LINC00665 |
| chr19 | 36909050 | 36909935 | Hyper | tcga, liver_tcga, cancer_general | LOC644189, ZFP82 | chr19 | 36912354 | 36912398 | Hyper | cancer_general | ZFP82, LOC644189 |
| chr19 | 37095665 | 37096575 | Hyper | tcga, literature, cancer_general | ZNF382, ZNF529 | chr19 | 37263532 | 37263584 | Hyper | esophageal | AX747375, BC024306, ZNF850 |
| chr19 | 37264222 | 37264421 | Hyper | cancer_general | BC024306, AX747375, ZNF850 | chr19 | 37288013 | 37288765 | Hyper | tcga, cancer_general | ZNF790-AS1 |
| chr19 | 37341761 | 37341962 | Hyper | esophageal | ZNF345, ZNF790 | chr19 | 37407127 | 37407443 | Hyper | cancer_general | ZNF568, ZNF829 |
| chr19 | 37464048 | 37464696 | Hyper | tcga, cancer_general | ZNF568 | chr19 | 37569289 | 37569554 | Hyper | esophageal | ZNF420 |
| chr19 | 37808445 | 37808485 | Hyper | esophageal | HKR1 | chr19 | 37959858 | 37959963 | Hyper | cancer_general | ZNF570, ZNF569 |
| chr19 | 37997433 | 37998138 | Hyper | cancer_general, tcga | ZNF793 | chr19 | 38042365 | 38042693 | Hyper | cancer_general | ZNF571, ZNF540, ZNF571-AS1 |
| chr19 | 38085254 | 38086066 | Hyper | esophageal | ZNF540, ZNF571 | chr19 | 38146062 | 38146247 | Hyper | esophageal | ZFP30 |
| chr19 | 38146457 | 38146568 | Hyper | esophageal | ZFP30 | chr19 | 38182884 | 38183299 | Hyper | cancer_general, tcga, liver_tcga, literature | ZNF607 |
| chr19 | 38308080 | 38308466 | Hyper | cancer_general | LOC644554, LOC100631378 | chr19 | 38747159 | 38747582 | Hyper | tcga, cancer_general, liver_tcga | SPINT2, PPP1R14A |
| chr19 | 38755272 | 38755344 | Hyper | tcga, liver_tcga | SPINT2, PPP1R14A | chr19 | 39687663 | 39687844 | Hyper | cancer_general | SYCN, NCCRP1 |
| chr19 | 39754874 | 39755358 | Hyper | cancer_general | IFNL2, SELV, DLL3 | chr19 | 39993477 | 39993664 | Hyper | cancer_general | DLL3 |
| chr19 | 39997688 | 39997813 | Hyper | cancer_general |  | chr19 | 40006177 | 40006306 | Hyper | tcga | DLL3, SELV |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 40006576 | 40006639 | Hyper | cancer_general | SELV, DLL3 | chr19 | 40724000 | 40724263 | Hyper | cancer_general | CNTD2, TTC9B, MAP3K10 |
| chr19 | 40762943 | 40762972 | Hyper | literature | AKT2 | chr19 | 41018510 | 41019031 | Hyper | cancer_general, pancreas, liver_tcga | SPTBN4 |
| chr19 | 41025539 | 41025683 | Hyper | cancer_general | SPTBN4 | chr19 | 41059909 | 41060306 | Hyper | cancer_general | — |
| chr19 | 41073587 | 41073677 | Hyper | cancer_general | SPTBN4, SHKBP1 | chr19 | 41119177 | 41119633 | Hyper | cancer_general | LIBP4 |
| chr19 | 41354666 | 41354722 | Hyper | cancer_general | CYP2A6 | chr19 | 41641831 | 41641886 | Hyper | cancer_general | DQ590318, CYP2F1 |
| chr19 | 41698787 | 41698920 | Hyper | blood | CYP2S1 | chr19 | 42028502 | 42028549 | Hyper | pancreas | — |
| chr19 | 42827891 | 42828266 | Hyper | liver_tcga, literature, cancer_general | MEGF8, TMEM145 | chr19 | 44203830 | 44203877 | Hyper | cancer_general | — |
| chr19 | 44405908 | 44406087 | Hyper | cancer_general | LOC100505715 | chr19 | 44905499 | 44905529 | Hyper | cancer_general | ZNF285 |
| chr19 | 44952282 | 44952881 | Hyper | tcga, cancer_general | ZNF229 | chr19 | 45300144 | 45300197 | Hyper | cancer_general | CBLC |
| chr19 | 45655393 | 45656363 | Hyper | cancer_general | TRAPPC6A, NKPD1, PPP1R37 | chr19 | 45656682 | 45656913 | Hyper | cancer_general | TRAPPC6A, NKPD1, PPP1R37 |
| chr19 | 45657212 | 45657284 | Hyper | cancer_general | TRAPPC6A, NKPD1, PPP1R37 | chr19 | 45888946 | 45889397 | Hyper | cancer_general | PPP1R13L |
| chr19 | 46002048 | 46002320 | Hyper | cancer_general | PPM1N, VASP, RTN2 | chr19 | 46379914 | 46380148 | Hyper | tcga | FOXA3, IRF2BP1 |
| chr19 | 46916725 | 46917075 | Hyper | literature, cancer_general | CCDC8 | chr19 | 46930129 | 46930200 | Hyper | cancer_general | — |
| chr19 | 46974552 | 46974700 | Hyper | literature, cancer_general | PPP5D1, PNMAL1 | chr19 | 46992718 | 46992866 | Hyper | cancer_general | PNMAL2, BC132841, PPP5D1 |
| chr19 | 46993164 | 46993388 | Hyper | cancer_general | PNMAL2, BC132841, PPP5D1 | chr19 | 46996501 | 46996918 | Hyper | tcga, literature, cancer_general | BC132841, PNMAL2, PPP5D1 |
| chr19 | 47152617 | 47153011 | Hyper | cancer_general | DACT3 | chr19 | 47776713 | 47776742 | Hyper | liver_tcga | PRR24, CCDC9 |
| chr19 | 47910482 | 47910517 | Hyper | cancer_general | MEIS3 | chr19 | 47933311 | 47933732 | Hyper | cancer_general | SLC8A2 |
| chr19 | 47951288 | 47951318 | Hyper | liver_tcga | SLC8A2 | chr19 | 48076642 | 48076672 | Hyper | cancer_general | — |
| chr19 | 48918100 | 48918598 | Hyper | tcga, cancer_general | Mir_324, GRIN2D | chr19 | 49127373 | 49127674 | Hyper | tcga, cancer_general, liver_tcga | SPHK2, DBP, RPL18 |
| chr19 | 49256396 | 49256438 | Hyper | hepatobiliary | FGF21, FUT1, IZUMO1 | chr19 | 49399218 | 49399310 | Hyper | cancer_general | NUCB1, Mir_324, TULP2 |
| chr19 | 49575460 | 49575489 | Hyper | liver_tcga | KCNA7 | chr19 | 49646149 | 49646213 | Hyper | cancer_general | PPFIA3, HRC |
| chr19 | 49935736 | 49936174 | Hyper | cancer_general | LOC100507003, PTH2, SLC17A7 | chr19 | 49936864 | 49936894 | Hyper | cancer_general | SLC17A7, LOC100507003 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 50316244 | 50316468 | Hyper | liver_tcga, colorectal | MED25, FUZ, AP2A1 | chr19 | 50553680 | 50553709 | Hyper | liver_tcga | FLJ26850, ZNF473 |
| chr19 | 50553997 | 50554510 | Hyper | liver_tcga, cancer_general | FLJ26850, ZNF473 | chr19 | 50816431 | 50816474 | Hyper | cancer_general | KCNC3, MYH14 |
| chr19 | 50833828 | 50833863 | Hyper | cancer_general | NAPSB, NR1H2, KCNC3 | chr19 | 51041149 | 51041189 | Hyper | head_neck | LRRC4B |
| chr19 | 51161225 | 51161255 | Hyper | cancer_general | SHANK1, C19orf81 | chr19 | 51162197 | 51162527 | Hyper | tcga, cancer_general | SHANK1, C19orf81 |
| chr19 | 51171219 | 51171278 | Hyper | cancer_general | SHANK1, C19orf81 | chr19 | 51171828 | 51171861 | Hyper | cancer_general | SHANK1, C19orf81 |
| chr19 | 51227719 | 51227785 | Hyper | cancer_general | CLEC11A, SHANK1 | chr19 | 51228049 | 51228079 | Hyper | pancreas | SHANK1, CLEC11A |
| chr19 | 51228308 | 51228507 | Hyper | cancer_general | CLEC11A, SHANK1 | chr19 | 51520423 | 51520453 | Hyper | cancer_general | KLK11, KLK10, KLK9 |
| chr19 | 51830845 | 51831128 | Hyper | cancer_general | VSIG10L, IGLON5 | chr19 | 51831360 | 51831390 | Hyper | cancer_general | VSIG10L, IGLON5 |
| chr19 | 51925127 | 51925272 | Hyper | liver_tcga | LOC100129083, SIGLEC10 | chr19 | 52097689 | 52097732 | Hyper | esophageal | FLJ30403, AX748312, ZNF175 |
| chr19 | 52207254 | 52207367 | Hyper | tcga, liver_tcga | LINC00085, HAS1 | chr19 | 52222523 | 52223131 | Hyper | cancer_general | HAS1 |
| chr19 | 52452316 | 52452447 | Hyper | liver_tcga | BC014606, ZNF613 | chr19 | 52552104 | 52552151 | Hyper | pancreas | ZNF432 |
| chr19 | 52715963 | 52715992 | Hyper | literature | PPP2R1A | chr19 | 52839588 | 52839938 | Hyper | tcga, cancer_general | ZNF610, AK097759 |
| chr19 | 52872924 | 52873440 | Hyper | tcga, cancer_general | ZNF880, ZNF610 | chr19 | 52956805 | 52956848 | Hyper | cancer_general | ZNF578 |
| chr19 | 53031185 | 53031215 | Hyper | esophageal | ZNF808 | chr19 | 53073293 | 53073354 | Hyper | cancer_general | ZNF701 |
| chr19 | 53073563 | 53073987 | Hyper | cancer_general | ZNF701 | chr19 | 53141619 | 53141745 | Hyper | liver_tcga | — |
| chr19 | 53193858 | 53193893 | Hyper | esophageal | — | chr19 | 53194281 | 53194396 | Hyper | cancer_general | — |
| chr19 | 53496649 | 53496846 | Hyper | tcga, liver_tcga | ZNF702P | chr19 | 53561668 | 53561733 | Hyper | cancer_general | ZNF160, ERVV-2 |
| chr19 | 53635952 | 53636091 | Hyper | tcga | ZNF347, ZNF415 | chr19 | 53661647 | 53661902 | Hyper | tcga, cancer_general | ZNF665, ZNF347 |
| chr19 | 53662174 | 53662694 | Hyper | tcga, cancer_general | ZNF665, NZF347 | chr19 | 53696414 | 53696580 | Hyper | cancer_general | ZNF665 |
| chr19 | 53700596 | 53700729 | Hyper | cancer_general | ZNF665 | chr19 | 53757895 | 53758247 | Hyper | tcga, cancer_general | ZNF677, VN1R2 |
| chr19 | 53811858 | 53811988 | Hyper | cancer_general | — | chr19 | 53836936 | 53836975 | Hyper | esophageal | ZNF845 |
| chr19 | 53837377 | 53837432 | Hyper | esophageal | ZNF845 | chr19 | 53970501 | 53970725 | Hyper | tcga, cancer_general | ZNF813, ZNF761 |
| chr19 | 53970968 | 53971157 | Hyper | cancer_general | ZNF813, ZNF761 | chr19 | 54023887 | 54024196 | Hyper | tcga | ZNF331 |
| chr19 | 54024521 | 54024884 | Hyper | tcga, cancer_general | ZNF331 | chr19 | 54369555 | 54369681 | Hyper | liver_tcga | MYADM |
| chr19 | 54411125 | 54411168 | Hyper | cancer_general | CACNG7 | chr19 | 54411556 | 54411586 | Hyper | cancer_general | CACNG7 |
| chr19 | 54412873 | 54412985 | Hyper | cancer_general | CACNG7 | chr19 | 54445344 | 54445513 | Hyper | cancer_general | CACNG7 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 54481771 | 54481968 | Hyper | cancer_general | MIR935, ACCNG8 | chr19 | 54483173 | 54483546 | Hyper | tcga, liver_tcga, cancer_general | MIR935, CACNG8 |
| chr19 | 54485403 | 54485823 | Hyper | liver_tcga, cancer_general | MIR935, CACNG6, CACNG8 | chr19 | 54976488 | 54976518 | Hyper | liver_tcga | CDC42EP5, LENG9, KIAA1932 |
| chr19 | 55598767 | 55598888 | Hyper | tcga | EPS8L1, PPP1R12C, Mir_324 | chr19 | 55629883 | 55630028 | Hyper | cancer_general | — |
| chr19 | 56159273 | 56159499 | Hyper | tcga | CCDC106, U2AF2, ZNF581, ZNF580 | chr19 | 56189937 | 56189966 | Hyper | liver_tcga | EPN1, U2AF2 |
| chr19 | 56728678 | 56728976 | Hyper | cancer_general | ZSCAN5A | chr19 | 56879501 | 56880008 | Hyper | tcga, cancer_general | ZNF542 |
| chr19 | 56904740 | 56905203 | Hyper | cancer_general, tcga | ZNF582-AS1, ZNF582 | chr19 | 56915320 | 56915428 | Hyper | cancer_general | ZNF583, ZNF582-AS1 |
| chr19 | 56988557 | 56988716 | Hyper | cancer_general | ZNF667-AS1, ZNF667 | chr19 | 56989528 | 56989754 | Hyper | tcga, cancer_general | ZNF667-AS1, ZNF667 |
| chr19 | 57050463 | 57050493 | Hyper | cancer_general | BX647249, ZFP28 | chr19 | 57149579 | 57149619 | Hyper | cancer_general | SMIM17 |
| chr19 | 57154885 | 57155017 | Hyper | cancer_general | SMIM17 | chr19 | 57182994 | 57183356 | Hyper | tcga, cancer_general | ZNF835 |
| chr19 | 57276656 | 57276700 | Hyper | cancer_general | BC036412, ZIM2, FJ997633 | chr19 | 57610855 | 57610985 | Hyper | tcga | — |
| chr19 | 57617522 | 57618121 | Hyper | cancer_general | — | chr19 | 57683148 | 57683295 | Hyper | cancer_general | DUXA |
| chr19 | 57862395 | 57862783 | Hyper | tcga, colorectal | ZNF304 | chr19 | 57863009 | 57863148 | Hyper | colorectal, cancer_general | ZNF304 |
| chr19 | 58011124 | 58011281 | Hyper | cancer_general | ZNF773, ZNF419 | chr19 | 58038805 | 58038969 | Hyper | cancer_general | ZNF549 |
| chr19 | 58095006 | 58095835 | Hyper | tcga, cancer_general | ZIK1, ZNF416 | chr19 | 58111632 | 58111783 | Hyper | tcga | AX721128, ZNF530, ZIK1 |
| chr19 | 58125544 | 58125881 | Hyper | tcga | ZNF134, ZNF211, AX721128, ZNF530 | chr19 | 58144494 | 58144701 | Hyper | head_neck | ZNF211 |
| chr19 | 58219839 | 58220832 | Hyper | liver_tcga, literature, cancer_general | ZNF154 | chr19 | 58238326 | 58239088 | Hyper | tcga, cancer_general | ZNF671 |
| chr19 | 58400079 | 58400175 | Hyper | cancer_general | ZNF814 | chr19 | 58400417 | 58400518 | Hyper | cancer_general | ZNF814 |
| chr19 | 58458754 | 58459201 | Hyper | tcga, cancer_general | ZNF256 | chr19 | 58514518 | 58514552 | Hyper | cancer_general | LOC100128398, ZNF606 |
| chr19 | 58520739 | 58520941 | Hyper | cancer_general | LOC100128398, ZNF606 | chr19 | 58545145 | 58545837 | Hyper | cancer_general, pancreas, literature, liver_tcga | ZSCAN1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr19 | 58570528 | 58570666 | Hyper | cancer_general | ZNF135, ZSCAN1 | chr19 | 58609254 | 58609854 | Hyper | tcga, cancer_general | ZSCAN18 |
| chr19 | 58629886 | 58629975 | Hyper | liver_tcga, literature | ZSCAN18, ZNF329 | chr19 | 58661894 | 58662094 | Hyper | cancer_general | — |
| chr19 | 58666171 | 58666313 | Hyper | cancer_general | — | chr19 | 58740086 | 58740118 | Hyper | esophageal | ZNF544 |
| chr19 | 58907689 | 58908195 | Hyper | cancer_general | RPS5, MIR4754, LOC646862 | chr19 | 58951271 | 58951916 | Hyper | cancer_general, tcga | ZNF132, DQ581862 |
| chr10 | 1651331 | 1651374 | Hyper | cancer_general | — | chr10 | 1774858 | 1774887 | Hyper | literature | PFKP |
| chr10 | 1779417 | 1779744 | Hyper | tcga, cancer_general | — | chr10 | 3109360 | 3109459 | Hyper | liver_tcga | — |
| chr10 | 7449954 | 7451390 | Hyper | tcga, colorectal, cancer_general | SFMBT2 | chr10 | 7452227 | 7452777 | Hyper | tcga, cancer_general, colorectal | SFMBT2 |
| chr10 | 7453313 | 7453930 | Hyper | tcga, colorectal, cancer_general | SFMBT2 | chr10 | 7708274 | 7708304 | Hyper | cancer_general | ITIH5 |
| chr10 | 7708790 | 7709087 | Hyper | cancer_general | ITIH5 | chr10 | 7709723 | 7709752 | Hyper | literature | ITIH5 |
| chr10 | 8075930 | 8075971 | Hyper | cancer_general | — | chr10 | 8076338 | 8076487 | Hyper | cancer_general | — |
| chr10 | 8076804 | 8077374 | Hyper | cancer_general | — | chr10 | 8077874 | 8078218 | Hyper | cancer_general | — |
| chr10 | 8085039 | 8085721 | Hyper | cancer_general | GATA3-AS1, BC036297 | chr10 | 8085978 | 8086010 | Hyper | cancer_general | GATA3-AS1, BC036297 |
| chr10 | 8091895 | 8092278 | Hyper | tcga, cancer_general | GATA3-AS1, BC036297, GATA3 | chr10 | 8093738 | 8093985 | Hyper | cancer_general | GATA3-AS1, BC036297, GATA3 |
| chr10 | 8095603 | 8095845 | Hyper | tcga, cancer_general | GATA3, BC036297, GATA3-AS1 | chr10 | 8096160 | 8096190 | Hyper | cancer_general | GATA3, BC036297, GATA3-AS1 |
| chr10 | 8096975 | 8097197 | Hyper | tcga, cancer_general | GATA3, BC036297, GATA3-AS1 | chr10 | 8097474 | 8097537 | Hyper | cancer_general | GATA3, BC036297, GATA3-AS1 |
| chr10 | 11059715 | 11060062 | Hyper | pancreas, liver_tcga, cancer_general | CELF2 | chr10 | 11206206 | 11206235 | Hyper | literature | CELF2 |
| chr10 | 11207179 | 11207276 | Hyper | cancer_general | CELF2 | chr10 | 12390825 | 12390995 | Hyper | esophageal | CAMK1D |
| chr10 | 12391870 | 12392327 | Hyper | esophageal | CAMK1D | chr10 | 13043386 | 13043425 | Hyper | cancer_general | AK311458 |
| chr10 | 13933005 | 13933035 | Hyper | cancer_general | FRMD4A | chr10 | 13933436 | 13934183 | Hyper | tcga, cancer_general | FRMD4A |
| chr10 | 15761292 | 15761671 | Hyper | cancer_general | ITGA8 | chr10 | 15762124 | 15762154 | Hyper | cancer_general | ITGA8 |
| chr10 | 16562086 | 16563909 | Hyper | literature, cancer_general | C1QL3 | chr10 | 17269628 | 17269789 | Hyper | literature | VIM, BC078172 |
| chr10 | 17270072 | 17270445 | Hyper | literature | VIM, BC078172 | chr10 | 17270991 | 17271625 | Hyper | tcga, liver_tcga, cancer_general, literature | VIM, BC078172 |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr10 | 17271914 | 17272233 | Hyper | tcga, literature | VIM, BC078172 | chr10 | 17272601 | 17272630 | Hyper | literature | VIM, BC078172 |
| chr10 | 17273172 | 17273201 | Hyper | literature | VIM, BC078172 | chr10 | 17496214 | 17496734 | Hyper | cancer_general | — |
| chr10 | 18429245 | 18429287 | Hyper | cancer_general | CACNB2 | chr10 | 18429628 | 18429774 | Hyper | tcga | CACNB2 |
| chr10 | 21462533 | 21462607 | Hyper | blood | NEBL-AS1 | chr10 | 21462970 | 21463023 | Hyper | blood | NEBL-AS1 |
| chr10 | 21805217 | 21805277 | Hyper | cancer_general | AK303207, SKIDA1, AK055656 | chr10 | 22541638 | 22542265 | Hyper | tcga, liver_tcga, cancer_general | LOC100130992 |
| chr10 | 22624022 | 22625978 | Hyper | liver_tcga, cancer_general | COMMD3-BMI1, SPAG6, BMI1 | chr10 | 22633985 | 22634578 | Hyper | liver_tcga, cancer_general | SPAG6 |
| chr10 | 22764649 | 22765901 | Hyper | liver_tcga, cancer_general | — | chr10 | 23216865 | 23216945 | Hyper | cancer_general | ARMC3 |
| chr10 | 23460355 | 23460471 | Hyper | cancer_general | SNORA40 | chr10 | 23461222 | 23461754 | Hyper | cancer_general | SNORA40 |
| chr10 | 23462059 | 23462910 | Hyper | cancer_general | SNORA40 | chr10 | 23463150 | 23464077 | Hyper | cancer_general | SNORA40 |
| chr10 | 23479876 | 23481086 | Hyper | cancer_general | PTF1A | chr10 | 23481321 | 23481515 | Hyper | cancer_general | PTF1A |
| chr10 | 23481936 | 23482445 | Hyper | cancer_general | PTF1A | chr10 | 23483828 | 23484618 | Hyper | cancer_general | PTF1A |
| chr10 | 23486264 | 23486328 | Hyper | cancer_general | PTF1A | chr10 | 23487742 | 23487978 | Hyper | cancer_general | PTF1A |
| chr10 | 23488393 | 23489158 | Hyper | cancer_general | KIAA1217 | chr10 | 23489409 | 23489439 | Hyper | cancer_general | KIAA1217 |
| chr10 | 23982438 | 23982820 | Hyper | cancer_general | KIAA1217 | chr10 | 23983194 | 23983247 | Hyper | cancer_general | KIAA1217 |
| chr10 | 23983481 | 23983700 | Hyper | tcga, cancer_general | KIAA1217 | chr10 | 23984087 | 23984226 | Hyper | cancer_general | KIAA1217 |
| chr10 | 23984923 | 23984991 | Hyper | cancer_general | KIAA1217 | chr10 | 25464619 | 25464915 | Hyper | cancer_general | GPR158, GPR158-AS1 |
| chr10 | 25465421 | 25465517 | Hyper | cancer_general | GPR158-AS1, GPR158 | chr10 | 26055811 | 26055841 | Hyper | cancer_general | — |
| chr10 | 26223001 | 26223424 | Hyper | cancer_general | MYO3A | chr10 | 26224031 | 26224061 | Hyper | cancer_general | MYO3A |
| chr10 | 26500619 | 26500915 | Hyper | cancer_general | GAD2, MYO3A | chr10 | 26501539 | 26501589 | Hyper | cancer_general | GAD2, MYO3A |
| chr10 | 26503693 | 26503731 | Hyper | cancer_general | GAD2, MYO3A | chr10 | 26504114 | 26504159 | Hyper | cancer_general | GAD2, MYO3A |
| chr10 | 26504491 | 26505227 | Hyper | cancer_general | GAD2, OMY3A | chr10 | 26505440 | 26505705 | Hyper | cancer_general | GAD2, MYO3A |
| chr10 | 26506057 | 26506163 | Hyper | cancer_general | GAD2, MYO3A | chr10 | 26506373 | 26507400 | Hyper | cancer_general | GAD2, MYO3A |
| chr10 | 26681099 | 26681129 | Hyper | cancer_general | — | chr10 | 26727098 | 26727368 | Hyper | cancer_general | APBB1IP |
| chr10 | 26727604 | 26727832 | Hyper | cancer_general | APBB1IP | chr10 | 27547946 | 27548484 | Hyper | cancer_general | AK125237, LRRC37A6P |
| chr10 | 28030892 | 28030925 | Hyper | cancer_general | MKX | chr10 | 28032966 | 28033020 | Hyper | cancer_general | MKX |
| chr10 | 28033410 | 28033481 | Hyper | cancer_general | MKX | chr10 | 28033770 | 28034341 | Hyper | tcga, cancer_general | MKX |
| chr10 | 28034575 | 28035300 | Hyper | tcga, cancer_general | MKX | chr10 | 28035615 | 28035782 | Hyper | cancer_general | MKX |
| chr10 | 28287373 | 28287557 | Hyper | tcga | — | chr10 | 28288070 | 28288070 | Hyper | cancer_general | — |
| chr10 | 28657255 | 28657343 | Hyper | literature | — | chr10 | 28958086 | 28958129 | Hyper | cancer_general | BAMBI |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 29011047 | 29011162 | Hyper | cancer_general | — | chr10 | 30025970 | 30026090 | Hyper | blood | — |
| chr10 | 31073368 | 31073481 | Hyper | tcga | — | chr10 | 33624166 | 33624230 | Hyper | blood | — |
| chr10 | 33624492 | 33624560 | Hyper | blood | — | chr10 | 35929150 | 35929528 | Hyper | cancer_general, liver_tcga, tcga | FZD8 |
| chr10 | 43250009 | 43250039 | Hyper | cancer_general | — | chr10 | 43250406 | 43250886 | Hyper | cancer_general | — |
| chr10 | 43428424 | 43428592 | Hyper | cancer_general | — | chr10 | 43429004 | 43429100 | Hyper | cancer_general | — |
| chr10 | 43429376 | 43429411 | Hyper | cancer_general | — | chr10 | 43572685 | 43572734 | Hyper | cancer_general | RET |
| chr10 | 43600561 | 43600720 | Hyper | cancer_general, liver_tcga | RET | chr10 | 43609055 | 43609117 | Hyper | literature | RET |
| chr10 | 43609922 | 43609963 | Hyper | literature | RET | chr10 | 43613890 | 43613919 | Hyper | literature | RET |
| chr10 | 43614982 | 43615011 | Hyper | literature | RET | chr10 | 43615554 | 43615607 | Hyper | literature | RET |
| chr10 | 43617401 | 43617430 | Hyper | literature | RET | chr10 | 43697887 | 43698155 | Hyper | cancer_general, tcga | RASGEF1A |
| chr10 | 44879944 | 44880228 | Hyper | cancer_general | CXCL12 | chr10 | 44880869 | 44880915 | Hyper | cancer_general | CXCL12 |
| chr10 | 49731548 | 49731749 | Hyper | tcga, colorectal, cancer_general | — | chr10 | 49732060 | 49732498 | Hyper | tcga, cancer_general | — |
| chr10 | 50323222 | 50323258 | Hyper | cancer_general | FAM170B-AS1, VSTM4 | chr10 | 50603967 | 50604159 | Hyper | cancer_general | DRGX |
| chr10 | 50604608 | 50604645 | Hyper | cancer_general | DRGX | chr10 | 50605057 | 50605654 | Hyper | cancer_general | DRGX |
| chr10 | 50606027 | 50606433 | Hyper | cancer_general | DRGX | chr10 | 50817015 | 50817132 | Hyper | cancer_general | CHAT, SLC18A3 |
| chr10 | 50817858 | 50817935 | Hyper | cancer_general | SLC18A3, CHAT | chr10 | 50818382 | 50818432 | Hyper | cancer_general | CHAT, SLC18A3 |
| chr10 | 50818823 | 50819102 | Hyper | cancer_general | CHAT, SLC18A3 | chr10 | 50821472 | 50821701 | Hyper | cancer_general | CHAT, SLC18A3 |
| chr10 | 50887655 | 50887816 | Hyper | cancer_general | C10orf53 | chr10 | 50976880 | 50977048 | Hyper | cancer_general | OGDHL |
| chr10 | 52177545 | 52177575 | Hyper | pancreas | SGMS1 | chr10 | 54068526 | 54068610 | Hyper | cancer_general | DKK1, PRKG1-AS1 |
| chr10 | 54072982 | 54073020 | Hyper | cancer_general | DKK1, PRKG1-AS1 | chr10 | 54073265 | 54073295 | Hyper | cancer_general | DKK1, PRKG1-AS1 |
| chr10 | 54074744 | 54074789 | Hyper | cancer_general | DKK1, PRKG1-AS1 | chr10 | 57387429 | 57387796 | Hyper | literature, cancer_general | — |
| chr10 | 57388325 | 57388510 | Hyper | cancer_general | — | chr10 | 57390290 | 57390637 | Hyper | cancer_general | — |
| chr10 | 57391166 | 57391215 | Hyper | cancer_general | — | chr10 | 60273130 | 60273294 | Hyper | cancer_general | BICC1 |
| chr10 | 60935887 | 60935996 | Hyper | cancer_general | PHYHIPL | chr10 | 60936524 | 60936732 | Hyper | cancer_general | PHYHIPL |
| chr10 | 60937073 | 60937103 | Hyper | cancer_general | PHYHIPL | chr10 | 63212324 | 63212701 | Hyper | cancer_general | BC041470, TMEM26 |
| chr10 | 64575526 | 64575638 | Hyper | cancer_general | ADO, EGR2 | chr10 | 64578171 | 64578540 | Hyper | tcga, colorectal, cancer_general | EGR2, ADO |
| chr10 | 71327725 | 71327764 | Hyper | lung, cancer_general | NEUROG3 | chr10 | 71328773 | 71328821 | Hyper | cancer_general | NEUROG3 |
| chr10 | 71329079 | 71329118 | Hyper | cancer_general | NEUROG3 | chr10 | 71329544 | 71329618 | Hyper | cancer_general | NEUROG3 |
| chr10 | 71332052 | 71333018 | Hyper | tcga, cancer_general | NEUROG3 | chr10 | 72015150 | 72015339 | Hyper | cancer_general | NPFFR1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 72043638 | 72043894 | Hyper | cancer_general | NPFFR1 | chr10 | 72200102 | 72200138 | Hyper | cancer_general | NODAL |
| chr10 | 72200354 | 72201285 | Hyper | cancer_general | NODAL | chr10 | 72973130 | 72973180 | Hyper | blood | UNC5B, UNC5B-AS1 |
| chr10 | 73156362 | 73156661 | Hyper | tcga | CDH23 | chr10 | 73847886 | 73848167 | Hyper | cancer_general, tcga | ASCC1, SPOCK2 |
| chr10 | 75407570 | 75407837 | Hyper | tcga, liver_tcga | SYNPO2L, MYOZ1 | chr10 | 77190039 | 77190068 | Hyper | literature | — |
| chr10 | 77191224 | 77191368 | Hyper | cancer_general | ZCCHC24 | chr10 | 79396921 | 79397089 | Hyper | cancer_general | KCNMA1 |
| chr10 | 81154141 | 81154192 | Hyper | liver_tcga | DYDC1, DYDC2 | chr10 | 81664867 | 81664899 | Hyper | cancer_general | LOC100288974 |
| chr10 | 82117074 | 82117271 | Hyper | tcga | | chr10 | 83634261 | 83634499 | Hyper | tcga | NRG3 |
| chr10 | 83635515 | 83635545 | Hyper | cancer_general | NRG3 | chr10 | 85954425 | 85954457 | Hyper | pancreas | CDHR1, C10orf99 |
| chr10 | 88123438 | 88123467 | Hyper | tcga | — | chr10 | 88123672 | 88123701 | Hyper | tcga | PTEN, KLLN |
| chr10 | 88149363 | 88149601 | Hyper | cancer_general | — | chr10 | 89624255 | 89624311 | Hyper | literature | PTEN |
| chr10 | 89653788 | 89653859 | Hyper | literature | PTEN | chr10 | 89685272 | 89685322 | Hyper | literature | PTEN |
| chr10 | 89690790 | 89690819 | Hyper | literature | PTEN | chr10 | 89692776 | 89693015 | Hyper | literature | PTEN |
| chr10 | 89711861 | 89711992 | Hyper | literature | AK130076, PTEN | chr10 | 89717610 | 89717744 | Hyper | literature | AK130076, PTEN |
| chr10 | 89720790 | 89720885 | Hyper | literature | LIPA, CH25H | chr10 | 89725030 | 89725071 | Hyper | literature | LIPA, CH25H |
| chr10 | 90966708 | 90966865 | Hyper | cancer_general | — | chr10 | 90967671 | 90968040 | Hyper | cancer_general | — |
| chr10 | 91295029 | 91295067 | Hyper | cancer_general | — | chr10 | 91295531 | 91295725 | Hyper | cancer_general | — |
| chr10 | 92617242 | 92617308 | Hyper | cancer_general | HTR7 | chr10 | 93647216 | 93647300 | Hyper | liver_tcga | HHEX |
| chr10 | 93647562 | 93647648 | Hyper | liver_tcga | HHEX | chr10 | 94450675 | 94450726 | Hyper | cancer_general | EXOC6, CYP26A1 |
| chr10 | 94451448 | 94451653 | Hyper | cancer_general | | chr10 | 94826023 | 94826056 | Hyper | cancer_general | CYP26C1, CYP26A1 |
| chr10 | 94828163 | 94828498 | Hyper | cancer_general | CYP26A1, CYP26C1, EXOC6 | chr10 | 94828735 | 94828828 | Hyper | cancer_general | CYP26C1, EXOC6, CYP26A1 |
| chr10 | 94834413 | 94835047 | Hyper | tcga, liver_tcga, literature, cancer_general | CYP26A1, CYP26C1 | chr10 | 95360716 | 95360750 | Hyper | blood | RBP4 |
| chr10 | 99080262 | 99080447 | Hyper | cancer_general | FRAT1 | chr10 | 99080862 | 99080984 | Hyper | cancer_general | FRAT1 |
| chr10 | 99474393 | 99474467 | Hyper | hepatobiliary | MARVELD1 | chr10 | 99531219 | 99531430 | Hyper | tcga, cancer_general | SFRP5 |
| chr10 | 99789175 | 99789282 | Hyper | cancer_general | — | chr10 | 99790261 | 99790318 | Hyper | cancer_general | — |
| chr10 | 99790590 | 99790664 | Hyper | cancer_general | — | chr10 | 99790947 | 99791161 | Hyper | cancer_general | — |
| chr10 | 100991907 | 100992443 | Hyper | tcga, cancer_general | HPSE2 | chr10 | 100992882 | 100992916 | Hyper | cancer_general | HPSE2 |
| chr10 | 100993537 | 100994016 | Hyper | cancer_general | HPSE2 | chr10 | 100996046 | 100996224 | Hyper | cancer_general | HPSE2 |
| chr10 | 101088995 | 101089439 | Hyper | colorectal, cancer_general | CNNM1 | chr10 | 101089908 | 101090203 | Hyper | cancer_general | CNNM1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 101280204 | 101280485 | Hyper | cancer_general | DQ372722, chromosome 10 open reading frame 139 | chr10 | 101283464 | 101283658 | Hyper | tcga | DQ372722, chromosome 10 open reading frame 139, NKX2-3 |
| chr10 | 101290117 | 101291191 | Hyper | cancer_general | NKX2-3, chromosome 10 open reading frame 139, DQ372722 | chr10 | 101292297 | 101292919 | Hyper | cancer_general | NKX2-3, chromosome 10 open reading frame 139, DQ372722 |
| chr10 | 101293156 | 101293343 | Hyper | cancer_general | NKX2-3, chromosome 10 open reading frame 139, DQ372722 | chr10 | 101294756 | 101295586 | Hyper | cancer_general | NKX2-3, chromosome 10 open reading frame 139, DQ372722 |
| chr10 | 101296768 | 101296800 | Hyper | cancer_general | NKX2-3, chromosome 10 open reading frame 139, DQ372722 | chr10 | 101874886 | 101875138 | Hyper | literature, liver_tcga | — |
| chr10 | 102322230 | 102322260 | Hyper | cancer_general | HIF1AN | chr10 | 102419316 | 102419681 | Hyper | cancer_general | — |
| chr10 | 102430699 | 102430761 | Hyper | cancer_general | — | chr10 | 102473856 | 102473932 | Hyper | cancer_general | — |
| chr10 | 102483993 | 102484554 | Hyper | cancer_general | — | chr10 | 102495508 | 102495741 | Hyper | cancer_general | PAX2 |
| chr10 | 102497273 | 102497708 | Typer | tcga, cancer_general | PAX2 | chr10 | 102498280 | 102498433 | Hyper | cancer_general | PAX2 |
| chr10 | 102501359 | 102501389 | Hyper | cancer_general | PAX2 | chr10 | 102507509 | 102507605 | Hyper | cancer_general | PAX2 |
| chr10 | 102508996 | 102509285 | Hyper | cancer_general | PAX2 | chr10 | 102586505 | 102586822 | Hyper | cancer_general | — |
| chr10 | 102589425 | 102589493 | Hyper | cancer_general | — | chr10 | 102589786 | 102589915 | Hyper | cancer_general | — |
| chr10 | 102590152 | 102590415 | Hyper | cancer_general | — | chr10 | 102890941 | 102891582 | Hyper | tcga, cancer_general | TLX1, TLX1NB |
| chr10 | 102891823 | 102892025 | Hyper | cancer_general | TLX1, TLX1NB | chr10 | 102893624 | 102895289 | Hyper | liver_tcga, literature, cancer_general | TLX1, TLX1NB |
| chr10 | 102899173 | 102899601 | Hyper | cancer_general | TLX1, TLX1NB | chr10 | 102899807 | 102900575 | Hyper | liver_tcga, cancer_general | TLX1, TLX1NB |
| chr10 | 102906523 | 102906620 | Hyper | cancer_general | TLX1 | chr10 | 102975619 | 102975834 | Hyper | cancer_general | — |
| chr10 | 102976150 | 102976180 | Hyper | cancer_general | — | chr10 | 102977051 | 102977412 | Hyper | cancer_general | LBX1 |
| chr10 | 102983153 | 102983749 | Hyper | cancer_general | LBX1, FLJ41350 | chr10 | 102984407 | 102984516 | Hyper | cancer_general | LBX1, FLJ41350 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 102985772 | 102985963 | Hyper | cancer_general | LBX1, FLJ41350 | chr10 | 102986534 | 102987558 | Hyper | lung, cancer_general | LBX1, FLJ41350 |
| chr10 | 102989629 | 102989659 | Hyper | cancer_general | FLJ41350, LBX1 | chr10 | 102996116 | 102996638 | Hyper | cancer_general | FLJ41350, LBX1 |
| chr10 | 102997329 | 102997406 | Hyper | cancer_general | FLJ41350, LBX1 | chr10 | 102998576 | 102998828 | Hyper | cancer_general | FLJ41350, LBX1 |
| chr10 | 103043975 | 103044366 | Hyper | literature, cancer_general | — | chr10 | 103432412 | 103432441 | Hyper | liver_tcga | FBXW4 |
| chr10 | 103535622 | 103535789 | Hyper | tcga | MGEA5, FGF8, NPM3 | chr10 | 103536227 | 103536416 | Hyper | liver_tcga, cancer_general | NPM3, MGEA5, FGF8 |
| chr10 | 104170096 | 104170732 | Hyper | tcga, cancer_general | PSD, FBXL15, NFKB2 | chr10 | 105036542 | 105036863 | Hyper | liver_tcga, cancer_general | INA |
| chr10 | 105037223 | 105037830 | Hyper | liver_tcga, cancer_general | INA | chr10 | 106398644 | 106398886 | Hyper | cancer_general | SORCS3 |
| chr10 | 106399581 | 106400387 | Hyper | cancer_general | SORCS3 | chr10 | 106400970 | 106402325 | Hyper | cancer_general | SORCS3 |
| chr10 | 106402712 | 106402825 | Hyper | cancer_general | SORCS3 | chr10 | 108924045 | 108924095 | Hyper | cancer_general | — |
| chr10 | 108924463 | 108924684 | Hyper | cancer_general | — | chr10 | 110226258 | 110226304 | Hyper | cancer_general | — |
| chr10 | 110671892 | 110672245 | Hyper | tcga, cancer_general | — | chr10 | 111216789 | 111216927 | Hyper | cancer_general | — |
| chr10 | 112403151 | 112403297 | Hyper | cancer_general | RBM20, Y_RNA | chr10 | 115804840 | 115805014 | Hyper | cancer_general | ADRB1 |
| chr10 | 116164248 | 116164341 | Hyper | blood | AFAP1L2 | chr10 | 116853875 | 116853908 | Hyper | esophageal | ATRNL1 |
| chr10 | 118030642 | 118030875 | Hyper | cancer_general | GFRA1 | chr10 | 118031302 | 118032547 | Hyper | tcga, cancer_general | GFRA1 |
| chr10 | 118032917 | 118033542 | Hyper | cancer_general | GFRA1 | chr10 | 118034138 | 118034168 | Hyper | lung, cancer_general | GFRA1 |
| chr10 | 118609305 | 118609390 | Hyper | esophageal | KIAA1598, ENO4 | chr10 | 118890980 | 118891104 | Hyper | cancer_general | KIAA1598, VAX1 |
| chr10 | 118891517 | 118891774 | Hyper | cancer_general | VAX1, KIAA1598 | chr10 | 118892013 | 118893266 | Hyper | cancer_general | VAX1, KIAA1598 |
| chr10 | 118893582 | 118894283 | Hyper | tcga, cancer_general | VAX1, KIAA1598 | chr10 | 118896629 | 118896805 | Hyper | tcga, cancer_general | VAX1 |
| chr10 | 118897913 | 118897968 | Hyper | cancer_general | VAX1 | chr10 | 118899273 | 118899302 | Hyper | literature | VAX1 |
| chr10 | 118899511 | 118899957 | Hyper | cancer_general | VAX1 | chr10 | 118900166 | 118900498 | Hyper | cancer_general | VAX1 |
| chr10 | 118922143 | 118922208 | Hyper | cancer_general | MIR3663, BC039338 | chr10 | 118922721 | 118922901 | Hyper | cancer_general, tcga | MIR3663, BC039338 |
| chr10 | 118923138 | 118923259 | Hyper | cancer_general | MIR3663, BC039338 | chr10 | 118924604 | 118924896 | Hyper | cancer_general | MIR3663, BC039338 |
| chr10 | 118927086 | 118927296 | Hyper | cancer_general | MIR3663, BC039338 | chr10 | 118928548 | 118928727 | Hyper | cancer_general | MIR3663, BC039338 |
| chr10 | 119000662 | 119001304 | Hyper | cancer_general | SLC18A2 | chr10 | 119001534 | 119001564 | Hyper | cancer_general | SLC18A2 |
| chr10 | 119292277 | 119292320 | Hyper | cancer_general | EMX2, EMX2OS | chr10 | 119294352 | 119294461 | Hyper | cancer_general | EMX2, EMX2OS |
| chr10 | 119294847 | 119295245 | Hyper | cancer_general | EMX2, EMX2OS | chr10 | 119296706 | 119296788 | Hyper | cancer_general | EMX2, EMX2OS |
| chr10 | 119297384 | 119297529 | Hyper | cancer_general | EMX2, EMX2OS | chr10 | 119301365 | 119301669 | Hyper | cancer_general | EMX2, EMX2OS, EMX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 119302141 | 119302266 | Hyper | cancer_general | EMX2, EMX2OS | chr10 | 119302962 | 119303174 | Hyper | cancer_general | EMX2, EMX2OS |
| chr10 | 119304363 | 119304393 | Hyper | cancer_general | EMX2, EMX2OS | chr10 | 119304896 | 119305109 | Hyper | cancer_general | EMX2, EMX2OS |
| chr10 | 119307022 | 119307052 | Hyper | cancer_general | EMX2, EMX2OS | chr10 | 119311867 | 119311897 | Hyper | cancer_general | EMX2, EMX2OS |
| chr10 | 119312751 | 119313193 | Hyper | literature | EMX2OS, EMX2 | chr10 | 119590435 | 119590464 | Hyper | literature | — |
| chr10 | 120354243 | 120354273 | Hyper | cancer_general | PRLHR | chr10 | 120355548 | 120355614 | Hyper | cancer_general | PRLHR |
| chr10 | 122216896 | 122217083 | Hyper | tcga | PPAPDC1A | chr10 | 122708495 | 122708691 | Hyper | cancer_general | — |
| chr10 | 122708992 | 122709022 | Hyper | cancer_general | — | chr10 | 123256044 | 123256232 | Hyper | literature | FGFR2 |
| chr10 | 123258020 | 123258091 | Hyper | literature | FGFR2 | chr10 | 123274758 | 123274787 | Hyper | literature | FGFR2 |
| chr10 | 123279548 | 123279697 | Hyper | literature | FGFR2 | chr10 | 123357206 | 123357242 | Hyper | literature | FGFR2 |
| chr10 | 123357766 | 123357893 | Hyper | blood | FGFR2 | chr10 | 123922645 | 123923464 | Hyper | blood | TACC2 |
| chr10 | 124893178 | 124893350 | Hyper | cancer_general | HMX3 | chr10 | 124893635 | 124893765 | Hyper | cancer_general | HMX3 |
| chr10 | 124893965 | 124894479 | Hyper | cancer_general | HMX3 | chr10 | 124894889 | 124894922 | Hyper | cancer_general | HMX3 |
| chr10 | 124895426 | 124896456 | Hyper | tcga, cancer_general | HMX3 | chr10 | 124896861 | 124896913 | Hyper | cancer_general | HMX3 |
| chr10 | 124897220 | 124897973 | Hyper | cancer_general | HMX2, HMX3 | chr10 | 124899035 | 124899116 | Hyper | cancer_general | HMX2, HMX3 |
| chr10 | 124899754 | 124899786 | Hyper | cancer_general | HMX2, HMX3 | chr10 | 124901892 | 124903238 | Hyper | cancer_general | HMX3, HMX2 |
| chr10 | 124904921 | 124905119 | Hyper | cancer_general | HMX2, BUB3, HMX3 | chr10 | 124905481 | 124905511 | Hyper | cancer_general | BUB3, HMX3, HMX2 |
| chr10 | 124905911 | 124906174 | Hyper | cancer_general | HMX2, BUB3, HMX3 | chr10 | 124906436 | 124906544 | Hyper | cancer_general | HMX3, HMX2, BUB3 |
| chr10 | 124907312 | 124907534 | Hyper | cancer_general | HMX2, BUB3 | chr10 | 124908091 | 124908121 | Hyper | cancer_general | BUB3, HMX2 |
| chr10 | 124909086 | 124909725 | Hyper | tcga, cancer_general | BUB3, HMX2 | chr10 | 124910363 | 124911048 | Hyper | cancer_general | BUB3, HMX2 |
| chr10 | 125425515 | 125425547 | Hyper | cancer_general | GPR26 | chr10 | 125650866 | 125651348 | Hyper | cancer_general, lung | CPXM2 |
| chr10 | 125851328 | 125851645 | Hyper | colorectal, cancer_general | CHST15 | chr10 | 125852299 | 125852524 | Hyper | colorectal | CHST15 |
| chr10 | 125852753 | 125853191 | Hyper | colorectal | CHST15 | chr10 | 126135927 | 126136065 | Hyper | cancer_general | NKX1-2 |
| chr10 | 126136506 | 126136723 | Hyper | tcga, cancer_general | NKX1-2 | chr10 | 126137181 | 126137405 | Hyper | cancer_general | NKX1-2 |
| chr10 | 128076561 | 128076630 | Hyper | tcga | ADAM12 | chr10 | 128077262 | 128077292 | Hyper | cancer_general | ADAM12 |
| chr10 | 128993904 | 128994446 | Hyper | cancer_general | FAM196A | chr10 | 128994727 | 128994903 | Hyper | pancreas, cancer_general | FAM196A |
| chr10 | 129534597 | 129535733 | Hyper | cancer_general | FOXI2, BC132944 | chr10 | 129536080 | 129536310 | Hyper | cancer_general | BC132944, FOXI2 |
| chr10 | 129948111 | 129948140 | Hyper | liver_tcga | — | chr10 | 130085295 | 130085362 | Hyper | cancer_general | AK124226 |
| chr10 | 130338727 | 130338976 | Hyper | pancreas, cancer_general | — | chr10 | 131757091 | 131757430 | Hyper | cancer_general | EBF3 |
| chr10 | 131757946 | 131758056 | Hyper | cancer_general | EBF3 | chr10 | 131761378 | 131761441 | Hyper | cancer_general | EBF3 |
| chr10 | 131761687 | 131761725 | Hyper | cancer_general | EBF3 | chr10 | 131762087 | 131762124 | Hyper | cancer_general | EBF3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr10 | 131762592 | 131762631 | Hyper | cancer_general | EBF3 | chr10 | 131762904 | 131762940 | Hyper | cancer_general | EBF3 |
| chr10 | 131763348 | 131763717 | Hyper | cancer_general | EBF3 | chr10 | 131767372 | 131767649 | Hyper | tcga, cancer_general | EBF3 |
| chr10 | 131768724 | 131769029 | Hyper | tcga, cancer_general | EBF3 | chr10 | 131769533 | 131770237 | Hyper | cancer_general | EBF3 |
| chr10 | 131770657 | 131770687 | Hyper | cancer_general | EBF3 | chr10 | 131770988 | 131771245 | Hyper | cancer_general | EBF3 |
| chr10 | 133109192 | 133109297 | Hyper | cancer_general | — | chr10 | 133109634 | 133109781 | Hyper | cancer_general | — |
| chr10 | 133110353 | 133110704 | Hyper | cancer_general | — | chr10 | 133794883 | 133795430 | Hyper | tcga, colorectal, cancer_general | BNIP3 |
| chr10 | 133795682 | 133796221 | Hyper | cancer_general | BNIP3 | chr10 | 133849598 | 133850008 | Hyper | tcga, pancreas, cancer_general | — |
| chr10 | 133850529 | 133850774 | Hyper | tcga, cancer_general | — | chr10 | 134000008 | 134000124 | Hyper | liver_tcga | DPYSL4, AL137551, JAKMIP3 |
| chr10 | 134001097 | 134001260 | Hyper | tcga, cancer_general | DPYSL4, AL137551, JAKMIP3 STK32C | chr10 | 134121401 | 134121430 | Hyper | liver_tcga | — |
| chr10 | 134598087 | 134598117 | Hyper | cancer_general | NKX6-2, INPP5A | chr10 | 134598336 | 134598530 | Hyper | liver_tcga, cancer_general | NKX6-2, INPP5A |
| chr10 | 134599062 | 134599482 | Hyper | liver_tcga, cancer_general | NKX6-2, INPP5A | chr10 | 134599808 | 134600998 | Hyper | liver_tcga, cancer_general | NKX6-2, INPP5A |
| chr10 | 134601556 | 134601798 | Hyper | cancer_general | NKX6-2, INPP5A | chr10 | 134602183 | 134602269 | Hyper | cancer_general | GPR123 |
| chr10 | 134755757 | 134756183 | Hyper | tcga, esophageal, cancer_general | TTC40 | chr10 | 134901193 | 134901511 | Hyper | tcga | UTF1, VENTX |
| chr10 | 134902008 | 134902307 | Hyper | cancer_general | GPR123 | chr10 | 135043088 | 135043538 | Hyper | cancer_general | VENTX, UTF1 |
| chr10 | 135043968 | 135044128 | Hyper | tcga, liver_tcga, cancer_general | VENTX, UTF1 | chr10 | 135044511 | 135044573 | Hyper | cancer_general | UTF1, VENTX |
| chr10 | 135048782 | 135048939 | Hyper | cancer_general | VENTX, UTF1 | chr10 | 135050311 | 135050679 | Hyper | cancer_general, tcga | ZNF511, PRAP1, TUBGCP2 |
| chr10 | 135121316 | 135121345 | Hyper | literature | ZNF511, PRAP1, TUBGCP2 | chr10 | 135121807 | 135122251 | Hyper | literature | CALY, BC047942, PRAP1 |
| chr10 | 135122742 | 135122808 | Hyper | literature | PRAP1, ZNF511, TUBGCP2 | chr10 | 135139555 | 135139730 | Hyper | tcga | — |
| AC241851.2_88-34049 | 14729 | 14973 | Hyper | cancer_general | — | AC241851.2_88-34049 | 15261 | 15350 | Hyper | cancer_general | — |
| chr5 | 53849 | 53900 | Hyper | cancer_general | — | chr5 | 92163 | 92399 | Hyper | tcga | — |
| chr5 | 320840 | 320982 | Hyper | liver_tcga, literature, cancer_general | AHRR, PDCD6 | chr5 | 343912 | 343941 | Hyper | literature | AHRR |
| chr5 | 373872 | 374266 | Hyper | literature | AHRR | chr5 | 400186 | 400215 | Hyper | literature | AHRR |
| chr5 | 400502 | 400531 | Hyper | literature | AHRR | chr5 | 524337 | 524404 | Hyper | cancer_general | — |
| chr5 | 528565 | 528685 | Hyper | tcga, liver_tcga, cancer_general | MIR4456 | chr5 | 1093660 | 1093797 | Hyper | liver_tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 1294630 | 1294767 | Hyper | cancer_general | TERT | chr5 | 1295031 | 1295662 | Hyper | cancer_general, literature | TERT |
| chr5 | 1445171 | 1445282 | Hyper | cancer_general | SLC6A3 | chr5 | 1445738 | 1445928 | Hyper | cancer_general | SLC6A3 |
| chr5 | 1446319 | 1446599 | Hyper | cancer_general | SLC6A3 | chr5 | 1874892 | 1875099 | Hyper | cancer_general | IRX4 |
| chr5 | 1875453 | 1875497 | Hyper | cancer_general | IRX4 | chr5 | 1875870 | 1876860 | Hyper | cancer_general | IRX4 |
| chr5 | 1877160 | 1877239 | Hyper | cancer_general | IRX4 | chr5 | 1878014 | 1878528 | Hyper | cancer_general | IRX4 |
| chr5 | 1878739 | 1879045 | Hyper | cancer_general | IRX4 | chr5 | 1879605 | 1879719 | Hyper | cancer_general, literature | IRX4 |
| chr5 | 1882294 | 1882605 | Hyper | cancer_general | IRX4 | chr5 | 1882844 | 1883089 | Hyper | cancer_general | IRX4 |
| chr5 | 1883515 | 1883820 | Hyper | cancer_general | IRX4 | chr5 | 1884178 | 1884237 | Hyper | cancer_general | IRX4 |
| chr5 | 1884557 | 1884698 | Hyper | cancer_general | IRX4 | chr5 | 1885158 | 1885458 | Hyper | cancer_general | IRX4 |
| chr5 | 1885985 | 1886192 | Hyper | cancer_general | IRX4 | chr5 | 1886542 | 1886581 | Hyper | cancer_general | IRX4 |
| chr5 | 1886812 | 1887737 | Hyper | cancer_general | IRX4 | chr5 | 1930786 | 1931754 | Hyper | pancreas, liver_tcga, cancer_general | — |
| chr5 | 1952624 | 1952654 | Hyper | cancer_general | — | chr5 | 2038705 | 2038850 | Hyper | cancer_general | — |
| chr5 | 2738848 | 2739422 | Hyper | cancer_general | IRX2 | chr5 | 2739877 | 2741061 | Hyper | tcga, cancer_general | IRX2 |
| chr5 | 2743617 | 2743713 | Hyper | cancer_general | C5orf38, IRX2 | chr5 | 2748374 | 2748459 | Hyper | cancer_general | C5orf38, IRX2 |
| chr5 | 2749213 | 2749425 | Hyper | cancer_general | C5orf38 | chr5 | 2749699 | 2749729 | Hyper | cancer_general | C5orf38, IRX2 |
| chr5 | 2750435 | 2751368 | Hyper | cancer_general | C5orf38, IRX2 | chr5 | 2751694 | 2751894 | Hyper | liver_tcga, cancer_general | C5orf38, IRX2 |
| chr5 | 2752991 | 2753040 | Hyper | cancer_general | C5orf38, IRX2 | chr5 | 2754738 | 2754767 | Hyper | literature | C5orf38, IRX2 |
| chr5 | 2755323 | 2756388 | Hyper | tcga, cancer_general | C5orf38, IRX2 | chr5 | 2756599 | 2757427 | Hyper | cancer_general | C5orf38, IRX2 |
| chr5 | 3590405 | 3590760 | Hyper | cancer_general | IRX1 | chr5 | 3591354 | 3591388 | Hyper | cancer_general | IRX1 |
| chr5 | 3591857 | 3592037 | Hyper | cancer_general | IRX1 | chr5 | 3592728 | 3592881 | Hyper | cancer_general | IRX1 |
| chr5 | 3594250 | 3594717 | Hyper | cancer_general | IRX1 | chr5 | 3595090 | 3595178 | Hyper | cancer_general | IRX1 |
| chr5 | 3595448 | 3595991 | Hyper | cancer_general, tcga, pancreas | IRX1 | chr5 | 3596192 | 3596221 | Hyper | liver_tcga, tcga | IRX1 |
| chr5 | 3596540 | 3596880 | Hyper | cancer_general | IRX1 | chr5 | 3597411 | 3597461 | Hyper | cancer_general | IRX1 |
| chr5 | 3599833 | 3599863 | Hyper | cancer_general | IRX1 | chr5 | 3600150 | 3600180 | Hyper | cancer_general | IRX1 |
| chr5 | 3600868 | 3600898 | Hyper | cancer_general | IRX1 | chr5 | 3602804 | 3603320 | Hyper | cancer_general | IRX1 |
| chr5 | 3606633 | 3606668 | Hyper | cancer_general | IRX1 | chr5 | 5139673 | 5139900 | Hyper | liver_tcga, tcga | IRX1 |
| chr5 | 5140170 | 5140225 | Hyper | cancer_general | AK094462, ADAMTS16 | chr5 | 5140630 | 5140901 | Hyper | cancer_general | ADAMTS16, AK094462 |
| chr5 | 6449930 | 6449582 | Hyper | cancer_general | UBE2QL1 | chr5 | 6583461 | 6583579 | Hyper | cancer_general | ADAMTS16, AK094462 |
| chr5 | 6687277 | 6687431 | Hyper | lung, cancer_general | — | chr5 | 6755789 | 6755843 | Hyper | liver_tcga | LOC255167 PAPD7 |
| chr5 | 7395263 | 7395538 | Hyper | tcga, cancer_general | ADCY2 | chr5 | 7850069 | 7850203 | Hyper | liver_tcga | FASTKD3, C5orf49 |
| chr5 | 7851015 | 7851121 | Hyper | cancer_general | FASTKD3, C5orf49 | chr5 | 9546612 | 9546648 | Hyper | cancer_general | SNORD123, LOC100505806 |
| chr5 | 10333688 | 10334132 | Hyper | lung, cancer_general | — | chr5 | 10565021 | 10565607 | Hyper | cancer_general | ANKRD33B |
| chr5 | 11384906 | 11385363 | Hyper | cancer_general | CTNND2 | chr5 | 11903760 | 11904696 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 11904896 | 11904943 | Hyper | cancer_general | — | chr5 | 14872919 | 14873053 | Hyper | tcga | MARCH11, BC043001 |
| chr5 | 15500748 | 15500927 | Hyper | tcga, cancer_general | FBXL7 | chr5 | 16179049 | 16179141 | Hyper | cancer_general | BC043001, MARCH11 |
| chr5 | 16179516 | 16179713 | Hyper | cancer_general | BC043001, MARCH11 | chr5 | 16180047 | 16180260 | Hyper | liver_tcga, literature, cancer_general | — |
| chr5 | 16936354 | 16936514 | Hyper | tcga, liver_tcga | MYO10 | chr5 | 17217928 | 17217958 | Hyper | pancreas | BASP1, LOC285696 |
| chr5 | 17218195 | 17218225 | Hyper | pancreas | BASP1, LOC285696 | chr5 | 17218943 | 17219018 | Hyper | cancer_general | LOC285696, BASP1 |
| chr5 | 22853443 | 22853508 | Hyper | cancer_general | CDH6 | chr5 | 31193937 | 31193989 | Hyper | cancer_general | CDH6 |
| chr5 | 31194375 | 31194641 | Hyper | cancer_general | CDH6 | chr5 | 31639684 | 31639960 | Hyper | tcga, cancer_general | PDZD2 |
| chr5 | 31855073 | 31855199 | Hyper | tcga | PDZD2 | chr5 | 32710331 | 32710470 | Hyper | cancer_general | NPR3 |
| chr5 | 32710802 | 32711531 | Hyper | tcga, cancer_general | NPR3 | chr5 | 32711826 | 32711870 | Hyper | cancer_general | NPR3 |
| chr5 | 32712077 | 32712491 | Hyper | cancer_general | NPR3 | chr5 | 32712764 | 32713304 | Hyper | tcga, cancer_general | NPR3 |
| chr5 | 33892083 | 33892115 | Hyper | cancer_general | U6, ADAMTS12 | chr5 | 33892413 | 33892443 | Hyper | cancer_general | U6, ADAMTS12 |
| chr5 | 33936156 | 33936336 | Hyper | tcga, cancer_general | RXFP3, SLC45A2 | chr5 | 33936599 | 33936663 | Hyper | cancer_general | SLC45A2, RXFP3 |
| chr5 | 34656932 | 34657034 | Hyper | blood | RAI14 | chr5 | 35874560 | 35874589 | Hyper | literature | IL7R |
| chr5 | 37834684 | 37834714 | Hyper | cancer_general | GDNF-AS1, GDNF | chr5 | 37834943 | 37835125 | Hyper | literature | GDNF, GDNF-AS1 |
| chr5 | 37836231 | 37836260 | Hyper | literature | GDNF-AS1, GDNF | chr5 | 37836649 | 37837992 | Hyper | cancer_general | GDNF-AS1, GDNF |
| chr5 | 37838548 | 37838885 | Hyper | tcga, cancer_general | GDNF-AS1, GDNF | chr5 | 37839780 | 37840125 | Hyper | cancer_general | GDNF-AS1, GDNF |
| chr5 | 37840381 | 37840853 | Hyper | tcga, cancer_general | GDNF-AS1, GDNF | chr5 | 38257485 | 38257606 | Hyper | tcga, cancer_general | EGFLAM |
| chr5 | 38257842 | 38257959 | Hyper | cancer_general | EGFLAM | chr5 | 38557070 | 38557400 | Hyper | tcga | MIR3650, LIFR, BC045578 |
| chr5 | 38845675 | 38846431 | Hyper | tcga, colorectal, cancer_general | OSMR | chr5 | 40681122 | 40681367 | Hyper | liver_tcga, cancer_general | PTGER4 |
| chr5 | 40681676 | 40682004 | Hyper | cancer_general | PTGER4 | chr5 | 42424822 | 42425060 | Hyper | cancer_general | GHR |
| chr5 | 42950980 | 42952441 | Hyper | tcga, cancer_general | — | chr5 | 42991825 | 42992934 | Hyper | cancer_general | AK056817 |
| chr5 | 42993150 | 42994193 | Hyper | tcga, cancer_general | AK056817 | chr5 | 42994694 | 42994790 | Hyper | tcga, liver_tcga | AK056817 |
| chr5 | 42995115 | 42995153 | Hyper | cancer_general | AK056817 | chr5 | 43007936 | 43007966 | Hyper | breast | LOC648987 |
| chr5 | 43008202 | 43008562 | Hyper | tcga, cancer_general | LOC648987 | chr5 | 43017953 | 43018767 | Hyper | tcga, cancer_general | LOC648987 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 43019238 | 43019347 | Hyper | cancer_general | LOC648987 | chr5 | 43019809 | 43019887 | Hyper | cancer_general | LOC648987 |
| chr5 | 43020146 | 43020294 | Hyper | tcga, breast | LOC648987 | chr5 | 43040544 | 43040635 | Hyper | tcga | LOC153684, DQ601842, ANXA2R |
| chr5 | 43040870 | 43040964 | Hyper | tcga, cancer_general | LOC153684, DQ601842, ANXA2R | chr5 | 43397002 | 43397246 | Hyper | cancer_general | CCL28 |
| chr5 | 44389766 | 44389852 | Hyper | cancer_general | FGF10 | chr5 | 45695186 | 45695533 | Hyper | cancer_general | HCN1 |
| chr5 | 45695906 | 45695947 | Hyper | cancer_general | HCN1 | chr5 | 45696336 | 45696439 | Hyper | cancer_general | HCN1 |
| chr5 | 49736592 | 49736685 | Hyper | cancer_general | — | chr5 | 50262893 | 50263014 | Hyper | cancer_general | — |
| chr5 | 50263568 | 50263641 | Hyper | cancer_general | — | chr5 | 50264307 | 50264603 | Hyper | cancer_general | — |
| chr5 | 50264566 | 50264850 | Hyper | lung | — | chr5 | 50265325 | 50265429 | Hyper | cancer_general | — |
| chr5 | 50265720 | 50265880 | Hyper | cancer_general | — | chr5 | 50674152 | 50674188 | Hyper | cancer_general | ISL1, LOC642366 |
| chr5 | 50674560 | 50674590 | Hyper | cancer_general | ISL1, LOC642366 | chr5 | 50675013 | 50675075 | Hyper | cancer_general | ISL1, LOC642366 |
| chr5 | 50678346 | 50678490 | Hyper | cancer_general | ISL1 | chr5 | 50695280 | 50695463 | Hyper | cancer_general | ISL1 |
| chr5 | 52084073 | 52084134 | Hyper | blood | PELO, ITGA1 | chr5 | 54179587 | 54179633 | Hyper | cancer_general | — |
| chr5 | 54180063 | 54180093 | Hyper | cancer_general | — | chr5 | 54516371 | 54517017 | Hyper | liver_tcga, cancer_general | CCNO, MCIDAS |
| chr5 | 54518651 | 54519321 | Hyper | cancer_general | CCNO, MCIDAS | chr5 | 54527304 | 54527343 | Hyper | cancer_general | CCNO, MCIDAS |
| chr5 | 56246546 | 56246575 | Hyper | literature | MIER3 | chr5 | 56247942 | 56247971 | Hyper | literature | MIER3 |
| chr5 | 56248218 | 56248257 | Hyper | literature | MIER3 | chr5 | 57878271 | 57878375 | Hyper | cancer_general | RAB3C |
| chr5 | 57878710 | 57878752 | Hyper | head_neck | RAB3C | chr5 | 59188291 | 59188327 | Hyper | cancer_general | — |
| chr5 | 59189055 | 59189206 | Hyper | liver_tcga, cancer_general | — | chr5 | 59189863 | 59189948 | Hyper | cancer_general | — |
| chr5 | 63254903 | 63255265 | Hyper | cancer_general | HTR1A | chr5 | 63256863 | 63256895 | Hyper | cancer_general | HTR1A |
| chr5 | 63257727 | 63257861 | Hyper | cancer_general | HTR1A | chr5 | 63802007 | 63802514 | Hyper | cancer_general | RGS7BP |
| chr5 | 63986488 | 63986807 | Hyper | cancer_general, tcga | FAM159B | chr5 | 67569803 | 67569832 | Hyper | literature | PIK3R1 |
| chr5 | 67588937 | 67589162 | Hyper | literature | PIK3R1 | chr5 | 67589598 | 67589627 | Hyper | literature | PIK3R1 |
| chr5 | 67590431 | 67590460 | Hyper | literature | PIK3R1 | chr5 | 67591068 | 67591157 | Hyper | literature | PIK3R1 |
| chr5 | 71014720 | 71014895 | Hyper | cancer_general | CARTPT | chr5 | 71015180 | 71015728 | Hyper | cancer_general | CARTPT |
| chr5 | 71403566 | 71403653 | Hyper | cancer_general | MAP1B | chr5 | 71403975 | 71404207 | Hyper | tcga | MAP1B |
| chr5 | 72416246 | 72416751 | Hyper | blood | TMEM171 | chr5 | 72526413 | 72526643 | Hyper | cancer_general | — |
| chr5 | 72529289 | 72530609 | Hyper | cancer_general | — | chr5 | 72594802 | 72595059 | Hyper | cancer_general | — |
| chr5 | 72595542 | 72595788 | Hyper | cancer_general | — | chr5 | 72599079 | 72599833 | Hyper | cancer_general | — |
| chr5 | 72677672 | 72678319 | Hyper | cancer_general | — | chr5 | 72715204 | 72715768 | Hyper | cancer_general | — |
| chr5 | 72716102 | 72716180 | Hyper | cancer_general | — | chr5 | 72732801 | 72732884 | Hyper | lung, cancer_general | FOXD1 |
| chr5 | 72733093 | 72733185 | Hyper | blood | FOXD1 | chr5 | 72740147 | 72740184 | Hyper | cancer_general | FOXD1 |
| chr5 | 72746680 | 72746710 | Hyper | cancer_general | FOXD1 | chr5 | 75377883 | 75378033 | Hyper | cancer_general | SV2C |
| chr5 | 75380163 | 75380193 | Hyper | cancer_general | SV2C | chr5 | 75380624 | 75380974 | Hyper | cancer_general | SV2C |
| chr5 | 76011285 | 76011337 | Hyper | cancer_general | F2R, NCRUPAR | chr5 | 76012576 | 76012605 | Hyper | liver_tcga | F2R, NCRUPAR |
| chr5 | 76249270 | 76250150 | Hyper | cancer_general | CRHBP | chr5 | 76250435 | 76250504 | Hyper | cancer_general | CRHBP |
| chr5 | 76506469 | 76506506 | Hyper | tcga | PDE8B | chr5 | 76507035 | 76507114 | Hyper | tcga | PDE8B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 76923679 | 76924409 | Hyper | cancer_general | OTP | chr5 | 76924930 | 76924960 | Hyper | cancer_general | OTP |
| chr5 | 76925561 | 76925690 | Hyper | cancer_general | OTP | chr5 | 76928157 | 76928397 | Hyper | cancer_general | OTP |
| chr5 | 76928688 | 76928906 | Hyper | cancer_general | OTP | chr5 | 76932302 | 76932332 | Hyper | cancer_general | OTP |
| chr5 | 76933542 | 76933281 | Hyper | cancer_general | OTP | chr5 | 76934173 | 76934870 | Hyper | cancer_general | OTP |
| chr5 | 76936016 | 76936721 | Hyper | cancer_general | OTP | chr5 | 76939420 | 76939774 | Hyper | cancer_general | OTP |
| chr5 | 76940340 | 76940374 | Hyper | pancreas | OTP | chr5 | 76941201 | 76941326 | Hyper | cancer_general | OTP |
| chr5 | 77140527 | 77140711 | Hyper | cancer_general | — | chr5 | 77147563 | 77148195 | Hyper | cancer_general | — |
| chr5 | 77148498 | 77148712 | Hyper | cancer_general | — | chr5 | 77268367 | 77269309 | Hyper | tcga, cancer_general | — |
| chr5 | 77806057 | 77806128 | Hyper | cancer_general | LHFPL2 | chr5 | 78407651 | 78407840 | Hyper | cancer_general | BHMT |
| chr5 | 78408192 | 78408461 | Hyper | cancer_general | BHMT | chr5 | 79864898 | 79865078 | Hyper | cancer_general | ANKRD34B |
| chr5 | 79866062 | 79866414 | Hyper | cancer_general | — | chr5 | 80255816 | 80256166 | Hyper | cancer_general, liver_tcga | RASGRF2 |
| chr5 | 80089543 | 80089735 | Hyper | cancer_general | ACOT12 | chr5 | 80690118 | 80690239 | Hyper | tcga, cancer_general | ACOT12 |
| chr5 | 82767429 | 82767793 | Hyper | cancer_general | VCAN | chr5 | 82768892 | 82769061 | Hyper | tcga, colorectal | VCAN |
| chr5 | 83679195 | 83679225 | Hyper | cancer_general | — | chr5 | 83679681 | 83680340 | Hyper | tcga, cancer_general | — |
| chr5 | 83680615 | 83680708 | Hyper | cancer_general | — | chr5 | 87955460 | 87955797 | Hyper | cancer_general | LINC00461, MIR9-2 |
| chr5 | 87956199 | 87956964 | Hyper | cancer_general | LINC00461, MIR9-2 | chr5 | 87962966 | 87963002 | Hyper | cancer_general | MIR9-2, LINC00461 |
| chr5 | 87963390 | 87963511 | Hyper | cancer_general | LINC00461 | chr5 | 87967773 | 87968077 | Hyper | cancer_general | MIR9-2, LINC00461 |
| chr5 | 87968486 | 87968858 | Hyper | cancer_general | MIR9-2, LINC00461 | chr5 | 87970193 | 87970872 | Hyper | cancer_general | MIR9-2, LINC00461 |
| chr5 | 87974104 | 87974307 | Hyper | cancer_general | — | chr5 | 87974868 | 87975023 | Hyper | cancer_general | — |
| chr5 | 87976028 | 87976308 | Hyper | head_neck | — | chr5 | 87976525 | 87976559 | Hyper | head_neck | — |
| chr5 | 87979756 | 87979912 | Hyper | cancer_general | — | chr5 | 87980142 | 87980250 | Hyper | cancer_general | — |
| chr5 | 87980954 | 87981325 | Hyper | cancer_general | — | chr5 | 87984532 | 87984657 | Hyper | cancer_general | — |
| chr5 | 87985922 | 87985954 | Hyper | cancer_general | — | chr5 | 87986210 | 87986281 | Hyper | cancer_general | — |
| chr5 | 87988516 | 87988584 | Hyper | cancer_general | — | chr5 | 87990408 | 87990452 | Hyper | cancer_general | — |
| chr5 | 88185470 | 88186001 | Hyper | tcga, cancer_general | AL050132 | chr5 | 89854856 | 89854902 | Hyper | cancer_general | GPR98 |
| chr5 | 92939916 | 92940136 | Hyper | cancer_general | GPR150 | chr5 | 94955681 | 94955919 | Hyper | cancer_general | GPR150 |
| chr5 | 94956935 | 94957000 | Hyper | cancer_general | PCSK1 | chr5 | 95767894 | 95768384 | Hyper | cancer_general | PCSK1 |
| chr5 | 95768920 | 95769093 | Hyper | cancer_general | ST8SIA4 | chr5 | 100236824 | 100236757 | Hyper | cancer_general | ST8SIA4 |
| chr5 | 100238882 | 100239151 | Hyper | tcga, cancer_general | — | chr5 | 101631487 | 101631533 | Hyper | cancer_general | SLCO4C1 |
| chr5 | 101632295 | 101632573 | Hyper | tcga | SLCO4C1 | chr5 | 107005983 | 107006186 | Hyper | blood | EFNA5 |
| chr5 | 112042904 | 112043289 | Hyper | literature | APC | chr5 | 112073358 | 112073516 | Hyper | liver_tcga, literature | APC |
| chr5 | 112170808 | 112170837 | Hyper | literature | APC | chr5 | 112175198 | 112175227 | Hyper | literature | APC |
| chr5 | 112175640 | 112175669 | Hyper | literature | APC | chr5 | 112258359 | 112258388 | Hyper | tcga | — |
| chr5 | 112258634 | 112258663 | Hyper | tcga | — | chr5 | 112629427 | 112629674 | Hyper | cancer_general | MCC |
| chr5 | 113391265 | 113392018 | Hyper | tcga, cancer_general | — | chr5 | 113698567 | 113698783 | Hyper | cancer_general | KCNN2 |
| chr5 | 113699008 | 113699119 | Hyper | cancer_general | KCNN2 | chr5 | 114514960 | 114515671 | Hyper | cancer_general | TRIM36 |
| chr5 | 115151267 | 115152638 | Hyper | cancer_general, tcga | CDO1 | chr5 | 115297192 | 115297556 | Hyper | cancer_general | AQPEP, AX747550 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 115297928 | 115298042 | Hyper | cancer_general | AQPEP, AX747550 | chr5 | 115298496 | 115298741 | Hyper | tcga, cancer_general | AX747550, AQPEP |
| chr5 | 115298985 | 115299041 | Hyper | cancer_general | AQPEP, AX747550 | chr5 | 119799931 | 119799986 | Hyper | cancer_general | PRR16 |
| chr5 | 119801299 | 119801445 | Hyper | cancer_general | PRR16 | chr5 | 121413537 | 121413590 | Hyper | blood | LOX |
| chr5 | 122422240 | 122422292 | Hyper | cancer_general | PRDM6 | chr5 | 122422616 | 122422651 | Hyper | cancer_general | PRDM6 |
| chr5 | 122423328 | 122423376 | Hyper | cancer_general | PRDM6 | chr5 | 122425128 | 122425168 | Hyper | cancer_general | PRDM6 |
| chr5 | 122431118 | 122431378 | Hyper | cancer_general | PRDM6 | chr5 | 126626283 | 126626738 | Hyper | cancer_general, tcga | MEGF10 |
| chr5 | 127872942 | 127872990 | Hyper | cancer_general | FBN2 | chr5 | 127873268 | 127873710 | Hyper | tcga, cancer_general | FBN2 |
| chr5 | 127874448 | 127874839 | Hyper | tcga, literature, cancer_general | FBN2 | chr5 | 128300680 | 128300794 | Hyper | cancer_general | SLC27A6 |
| chr5 | 128796081 | 128796244 | Hyper | cancer_general | ADAMTS19 | chr5 | 128796867 | 128796985 | Hyper | cancer_general | ADAMTS19 |
| chr5 | 128797344 | 128797386 | Hyper | cancer_general | ADAMTS19 | chr5 | 129240068 | 129240101 | Hyper | esophageal | CHSY3 |
| chr5 | 131992096 | 131992157 | Hyper | cancer_general | IL13, BC042122 | chr5 | 132947486 | 132947836 | Hyper | tcga, cancer_general | — |
| chr5 | 134363309 | 134363338 | Hyper | liver_tcga | PITX1, LOC100996485 | chr5 | 134363876 | 134363973 | Hyper | liver_tcga | LOC100996485, PITX1 |
| chr5 | 134364195 | 134364513 | Hyper | liver_tcga, cancer_general | LOC100996485, PITX1 | chr5 | 134366718 | 134366788 | Hyper | cancer_general | LOC100996485, PITX1 |
| chr5 | 134367108 | 134367203 | Hyper | cancer_general | LOC100996485, PITX1 | chr5 | 134374447 | 134375210 | Hyper | cancer_general | LOC100996485, PITX1 |
| chr5 | 134376222 | 134376375 | Hyper | cancer_general | PITX1, LOC100996485 | chr5 | 134376697 | 134376824 | Hyper | cancer_general | LOC100996485, PITX1 |
| chr5 | 134385952 | 134386383 | Hyper | cancer_general | LOC100996485 | chr5 | 134735622 | 134735651 | Hyper | literature | — |
| chr5 | 134825463 | 134825518 | Hyper | cancer_general | — | chr5 | 134825889 | 134826006 | Hyper | cancer_general | — |
| chr5 | 134870446 | 134870515 | Hyper | cancer_general | NEUROG1 | chr5 | 134870780 | 134871196 | Hyper | cancer_general | NEUROG1 |
| chr5 | 134871601 | 134872049 | Hyper | cancer_general | NEUROG1 | chr5 | 134879478 | 134880501 | Hyper | cancer_general | NEUROG1 |
| chr5 | 134914627 | 134914748 | Hyper | tcga | CXCL14 | chr5 | 135265737 | 135265767 | Hyper | cancer_general | FBXL21 |
| chr5 | 135266114 | 135266672 | Hyper | cancer_general | FBXL21 | chr5 | 135528201 | 135528233 | Hyper | cancer_general | LOC389332, SMAD5 |
| chr5 | 136834050 | 136834506 | Hyper | tcga, cancer_general | SPOCK1 | chr5 | 136834720 | 136834826 | Hyper | cancer_general | SPOCK1 |
| chr5 | 137225092 | 137225297 | Hyper | liver_tcga, cancer_general | PKD2L2, MYOT | chr5 | 139045286 | 139045315 | Hyper | cancer_general | CXXC5 |
| chr5 | 139047990 | 139048162 | Hyper | tcga, liver_tcga | CXXC5 | chr5 | 139056666 | 139056804 | Hyper | liver_tcga | CXXC5 |
| chr5 | 139227773 | 139227909 | Hyper | cancer_general | NRG2, PSD2 | chr5 | 139525728 | 139525758 | Hyper | cancer_general | — |
| chr5 | 140174798 | 140174901 | Hyper | cancer_general | PCDHA3, PCDHA2, PCDHA1 | chr5 | 140187094 | 140187146 | Hyper | cancer_general | PCDHA4, PCDHA3, PCDHA2 |
| chr5 | 140305978 | 140306050 | Hyper | cancer_general | PCDHAC1, PCDHA13 | chr5 | 140306321 | 140306733 | Hyper | cancer_general | PCDHAC1, PCDHA13 |
| chr5 | 140346595 | 140346671 | Hyper | cancer_general | PCDHAC2 | chr5 | 140514891 | 140514921 | Hyper | cancer_general | PCDHB5, PCDHB4 |
| chr5 | 140604459 | 140604501 | Hyper | cancer_general | PCDHB18, PCDHB14, PCDHB13 | chr5 | 140613926 | 140614014 | Hyper | cancer_general | PCDHB18, PCDHB19P, PCDHB14 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 140614314 | 140614383 | Hyper | cancer_general | PCDHB14, PCDHB19P, PCDHB18 | chr5 | 140683631 | 140683772 | Hyper | liver_tcga | SLC25A2 |
| chr5 | 140777328 | 140777487 | Hyper | cancer_general | PCDHGB5, PCDHGA9, PCDHGA8, PCDHGB4, PCDHGA7 | chr5 | 140787608 | 140787637 | Hyper | literature | PCDHGA10, PCDHGB7, PCDHGA9, PCDHGB5, PCDHGA8, PCDHGB6 |
| chr5 | 140797076 | 140797342 | Hyper | liver_tcga, cancer_general | PCDHGB8P, PCDHGA10, PCDHGB6, PCDHGA9, PCDHGB7, PCDHGA11 | chr5 | 140800479 | 140801246 | Hyper | cancer_general, liver_tcga | PCDHGA11, PCDHGB8P, PCDHGA12, PCDHGB7, PCDHGA10, PCDHGB6 |
| chr5 | 140811087 | 140811116 | Hyper | liver_tcga | PCDHGB8P, PCDHGA11, PCDHGB7, PCDHGA12 | chr5 | 140855598 | 140856622 | Hyper | cancer_general | PCDHGC4, PCDHGC3 |
| chr5 | 141031121 | 141031150 | Hyper | tcga, cancer_general | ARAP3, FCHSD1 | chr5 | 141263035 | 141263236 | Hyper | tcga, cancer_general | BC127870, PCDH1 |
| chr5 | 141931340 | 141931539 | Hyper | cancer_general | — | chr5 | 142784967 | 142785272 | Hyper | tcga | NR3C1 |
| chr5 | 145713645 | 145713896 | Hyper | cancer_general | POU4F3 | chr5 | 145717175 | 145717437 | Hyper | cancer_general | POU4F3 |
| chr5 | 145718802 | 145719925 | Hyper | cancer_general | POU4F3 | chr5 | 145720812 | 145720917 | Hyper | cancer_general | POU4F3 |
| chr5 | 145722116 | 145723027 | Hyper | cancer_general | POU4F3 | chr5 | 145724502 | 145724698 | Hyper | cancer_general | POU4F3 |
| chr5 | 145725212 | 145725844 | Hyper | cancer_general | POU4F3 | chr5 | 146257332 | 146257602 | Hyper | tcga, colorectal, cancer_general | PPP2R2B |
| chr5 | 146889220 | 146889575 | Hyper | tcga, cancer_general | DPYSL3 | chr5 | 149503827 | 149503856 | Hyper | literature | PDGFRB |
| chr5 | 149682074 | 149682166 | Hyper | cancer_general | ARSI | chr5 | 150051101 | 150051667 | Hyper | cancer_general | MYOZ3 |
| chr5 | 150326159 | 150326188 | Hyper | literature | ZNF300P1 | chr5 | 150400123 | 150400203 | Hyper | cancer_general | TNIP1, GPX3 |
| chr5 | 151066442 | 151066474 | Hyper | cancer_general | BC039364, SPARC | chr5 | 151304371 | 151304401 | Hyper | cancer_general | — |
| chr5 | 153852664 | 153852792 | Hyper | cancer_general | HAND1 | chr5 | 153853420 | 153853478 | Hyper | cancer_general | HAND1 |
| chr5 | 153854330 | 153854360 | Hyper | cancer_general | HAND1 | chr5 | 153855175 | 153855264 | Hyper | cancer_general | HAND1 |
| chr5 | 153855591 | 153855839 | Hyper | cancer_general | HAND1 | chr5 | 153856090 | 153856396 | Hyper | cancer_general | HAND1 |
| chr5 | 153856936 | 153856996 | Hyper | cancer_general | HAND1 | chr5 | 153857379 | 153857429 | Hyper | cancer_general | HAND1 |
| chr5 | 153858319 | 153858599 | Hyper | cancer_general | HAND1 | chr5 | 153859676 | 153859708 | Hyper | cancer_general | HAND1 |
| chr5 | 153862037 | 153862577 | Hyper | tcga, cancer_general | HAND1 | chr5 | 153863421 | 153863451 | Hyper | cancer_general | HAND1 |
| chr5 | 155107794 | 155107848 | Hyper | cancer_general | — | chr5 | 155108097 | 155108526 | Hyper | tcga, cancer_general | — |
| chr5 | 155108733 | 155108763 | Hyper | cancer_general | C5orf52 | chr5 | 157001739 | 157001843 | Hyper | cancer_general | ADAM19 |
| chr5 | 157098362 | 157098619 | Hyper | liver_tcga, cancer_general | — | chr5 | 158478483 | 158478764 | Hyper | cancer_general | EBF1 |
| chr5 | 158524692 | 158524748 | Hyper | cancer_general | AK123543, EBF1 | chr5 | 158527443 | 158528069 | Hyper | tcga, liver_tcga, cancer_general | AK123543, EBF1 |

TABLE 11-continued

| chr | Start | Stop | Hypo/hyper | classification | annotation |
|---|---|---|---|---|---|
| chr5 | 159399095 | 159399233 | Hyper | cancer_general | TRNA_Leu, ADRA1B |
| chr5 | 161274310 | 161274554 | Hyper | literature, cancer_general | GABRA1 |
| chr5 | 168727924 | 168727988 | Hyper | cancer_general | — |
| chr5 | 170108287 | 170108372 | Hyper | cancer_general | KCNIP1 |
| chr5 | 170735154 | 170735206 | Hyper | cancer_general | TLX3, AX746723, RANBP17 |
| chr5 | 170736116 | 170737479 | Hyper | liver_tcga, cancer_general | TLX3, AX746723, RANBP17 |
| chr5 | 170739823 | 170740027 | Hyper | cancer_general | TLX3, AX746723 |
| chr5 | 170741465 | 170744128 | Hyper | cancer_general | TLX3, AX746723 |
| chr5 | 170745389 | 170745480 | Hyper | cancer_general | TLX3, AX746723 |
| chr5 | 172659225 | 172659290 | Hyper | cancer_general | NKX2-5 |
| chr5 | 172659855 | 172660218 | Hyper | cancer_general | NKX2-5 |
| chr5 | 172664226 | 172664487 | Hyper | cancer_general | NKX2-5 |
| chr5 | 172670983 | 172671018 | Hyper | cancer_general | NKX2-5 |
| chr5 | 172754589 | 172754621 | Hyper | cancer_general | STC2 |
| chr5 | 172755470 | 172755663 | Hyper | cancer_general | STC2 |
| chr5 | 174115388 | 174115861 | Hyper | cancer_general | — |
| chr5 | 174150415 | 174150445 | Hyper | cancer_general | MSX2 |
| chr5 | 174162874 | 174162904 | Hyper | cancer_general | MSX2 |
| chr5 | 174870738 | 174870786 | Hyper | cancer_general | DRD1 |
| chr5 | 175085147 | 175085209 | Hyper | cancer_general | HRH2 |
| chr5 | 175223671 | 175223709 | Hyper | cancer_general | CPLX2 |
| chr5 | 175298549 | 175298883 | Hyper | tcga | CPLX2 |
| chr5 | 175300351 | 175300381 | Hyper | cancer_general | Hfb1, CPLX2 |
| chr5 | 175792865 | 175793063 | Hyper | tcga, liver_tcga, cancer_general | KIAA1191, ARL10 |
| chr5 | 176046363 | 176046554 | Hyper | cancer_general | SNCB, MIR4281 |
| chr5 | 176236721 | 176236898 | Hyper | cancer_general | UNC5A |
| chr5 | 176520166 | 176520195 | Hyper | literature | FGFR4 |
| chr5 | 176827656 | 176827685 | Hyper | literature | F12, PFN3, SLC34A1 |
| chr5 | 178003708 | 178003848 | Hyper | cancer_general | — |
| chr5 | 178016575 | 178017867 | Hyper | tcga, cancer_general | — |
| chr5 | 178421474 | 178421504 | Hyper | cancer_general | GRM6 |
| chr5 | 160975724 | 160975754 | Hyper | cancer_general | GABRB2 |
| chr5 | 167956177 | 167956595 | Hyper | tcga, cancer_general | FBLL1, RARS |
| chr5 | 169064327 | 169064805 | Hyper | tcga, liver_tcga, cancer_general | DOCK2 |
| chr5 | 170289444 | 170289498 | Hyper | pancreas | RANBP17 |
| chr5 | 170735422 | 170735788 | Hyper | pancreas, cancer_general | TLX3, AX746723, RANBP17 |
| chr5 | 170737741 | 170739481 | Hyper | tcga, cancer_general | TLX3, AX746723 |
| chr5 | 170740461 | 170741240 | Hyper | cancer_general | TLX3, AX746723 |
| chr5 | 170744375 | 170744562 | Hyper | cancer_general | TLX3, AX746723 |
| chr5 | 172655879 | 172656215 | Hyper | cancer_general | NKX2-5 |
| chr5 | 172659496 | 172659655 | Hyper | cancer_general | NKX2-5 |
| chr5 | 172660719 | 172661684 | Hyper | cancer_general | NKX2-5 |
| chr5 | 172665590 | 172665812 | Hyper | cancer_general | NKX2-5 |
| chr5 | 172671345 | 172671968 | Hyper | cancer_general | NKX2-5 |
| chr5 | 172754832 | 172754931 | Hyper | cancer_general | STC2 |
| chr5 | 172757048 | 172757111 | Hyper | cancer_general | STC2 |
| chr5 | 174147523 | 174147596 | Hyper | cancer_general | MSX2 |
| chr5 | 174158808 | 174159588 | Hyper | cancer_general | MSX2 |
| chr5 | 174220971 | 174221001 | Hyper | head_neck | — |
| chr5 | 174871174 | 174871497 | Hyper | cancer_general | DRD1 |
| chr5 | 175085476 | 175085719 | Hyper | cancer_general | HRH2 |
| chr5 | 175224016 | 175224271 | Hyper | cancer_general | CPLX2 |
| chr5 | 175299294 | 175299396 | Hyper | cancer_general | CPLX2 |
| chr5 | 175621390 | 175621501 | Hyper | cancer_general | — |
| chr5 | 176023916 | 176024318 | Hyper | cancer_general | GPRIN1, CDHR2 |
| chr5 | 176107274 | 176107586 | Hyper | cancer_general | — |
| chr5 | 176264805 | 176264915 | Hyper | cancer_general | UNC5A |
| chr5 | 176522400 | 176522566 | Hyper | literature | FGFR4 |
| chr5 | 177411638 | 177412141 | Hyper | cancer_general | PROP1 |
| chr5 | 178004325 | 178004374 | Hyper | cancer_general | — |
| chr5 | 178368074 | 178368383 | Hyper | cancer_general | ZNF454, ZFP2 |
| chr5 | 178421766 | 178422142 | Hyper | literature, cancer_general | GRM6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr5 | 178487107 | 178487398 | Hyper | tcga, cancer_general | ZNF354C | chr5 | 178771314 | 178771955 | Hyper | tcga, cancer_general | ADAMTS2 |
| chr5 | 178772205 | 178772272 | Hyper | cancer_general | ADAMTS2 | chr5 | 178772603 | 178772745 | Hyper | cancer_general | ADAMTS2 |
| chr5 | 178957637 | 178957944 | Hyper | tcga, cancer_general | AX747985 | chr5 | 179243984 | 179244277 | Hyper | cancer_general | SQSTM1 |
| chr5 | 179780104 | 179780144 | Hyper | cancer_general | GFPT2 | chr5 | 179780706 | 179780985 | Hyper | cancer_general | GFPT2 |
| chr5 | 179867486 | 179867548 | Hyper | cancer_general | — | chr5 | 180017118 | 180017198 | Hyper | cancer_general | SCGB3A1 |
| chr5 | 180017608 | 180017933 | Hyper | tcga, cancer_general | SCGB3A1 | chr5 | 180018311 | 180018498 | Hyper | cancer_general | SCGB3A1 |
| chr5 | 180075846 | 180076317 | Hyper | cancer_general | FLT4 | chr5 | 180076567 | 180076602 | Hyper | cancer_general | FLT4 |
| chr5 | 180076804 | 180076996 | Hyper | cancer_general | FLT4 | chr5 | 180100915 | 180101332 | Hyper | tcga, cancer_general | DQ589679 |
| chr5 | 180527546 | 180527766 | Hyper | liver_tcga, cancer_general | TRNA_Val, TRNA_Leu | chr5 | 180594851 | 180595002 | Hyper | head_neck | TRNA_Val, TRNA_Leu, TRNA_Pseudo |
| chr5 | 180600858 | 180601218 | Hyper | cancer_general | TRNA_Leu, TRNA_Val, TRNA_Pseudo TRNA_Pro, TRNA_Thr, TRNA_Leu | chr14 | 21093454 | 21093631 | Hyper | cancer_general | TRNA_Pro, TRNA_Leu, TRNA_Thr |
| chr14 | 21100801 | 21100831 | Hyper | head_neck | REM2, OR6S1, TRNA_Thr, TRNA_Leu | chr14 | 22005029 | 22005073 | Hyper | cancer_general | — |
| chr14 | 23356044 | 23356384 | Hyper | tcga, liver_tcga | LRP10 | chr14 | 24045513 | 24045603 | Hyper | cancer_general | JPH4, AP1G2 |
| chr14 | 24640932 | 24641215 | Hyper | literature | REC8, IPO4, IRF9 | chr14 | 24803594 | 24804409 | Hyper | tcga, cancer_general, literature | ADCY4, RIPK3 |
| chr14 | 26674354 | 26674384 | Hyper | cancer_general | — | chr14 | 26674699 | 26674729 | Hyper | cancer_general | — |
| chr14 | 27066562 | 27066785 | Hyper | tcga | NOVA1 | chr14 | 27067161 | 27067386 | Hyper | cancer_general | NOVA1 |
| chr14 | 29225531 | 29225561 | Hyper | cancer_general | — | chr14 | 29226071 | 29226198 | Hyper | cancer_general | — |
| chr14 | 29228654 | 29228778 | Hyper | cancer_general | FOXG1 | chr14 | 29229107 | 29229386 | Hyper | cancer_general | FOXG1 |
| chr14 | 29231071 | 29231217 | Hyper | cancer_general | FOXG1 | chr14 | 29231425 | 29231590 | Hyper | cancer_general | FOXG1 |
| chr14 | 29235003 | 29235356 | Hyper | cancer_general | FOXG1, C14orf23 | chr14 | 29237063 | 29237107 | Hyper | cancer_general | C14orf23, FOXG1 |
| chr14 | 29242763 | 29242908 | Hyper | cancer_general | FOXG1, BC034423, C14orf23 | chr14 | 29243516 | 29243888 | Hyper | literature, cancer_general | BC034423, C14orf23, FOXG1 |
| chr14 | 29244224 | 29244308 | Hyper | cancer_general | BC034423, C14orf23, FOXG1 | chr14 | 29247689 | 29247740 | Hyper | cancer_general | BC034423, C14orf23, FOXG1 |
| chr14 | 29254575 | 29254713 | Hyper | cancer_general | BC034423, C14orf23 | chr14 | 31344346 | 31344549 | Hyper | cancer_general | COCH, LOC100506071 |
| chr14 | 33402462 | 33402762 | Hyper | cancer_general | NPAS3 | chr14 | 33403045 | 33403316 | Hyper | tcga, cancer_general | NPAS3 |
| chr14 | 33403866 | 33404418 | Hyper | cancer_general | NPAS3 | chr14 | 34420250 | 34420288 | Hyper | blood | EGLN3 |
| chr14 | 36003442 | 36003826 | Hyper | tcga, liver_tcga | RALGAPA1, INSM2 | chr14 | 36004063 | 36004493 | Hyper | cancer_general | RALGAPA1, INSM2 |
| chr14 | 36004711 | 36004983 | Hyper | cancer_general | INSM2, RALGAPA1 | chr14 | 36972803 | 36972912 | Hyper | cancer_general | SFTA3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 36973254 | 36973538 | Hyper | cancer_general | SFTA3 | chr14 | 36974294 | 36974982 | Hyper | tcga, cancer_general | SFTA3 |
| chr14 | 36975299 | 36975399 | Hyper | cancer_general | SFTA3 | chr14 | 36977645 | 36978009 | Hyper | cancer_general | NKX2-1, SFTA3 |
| chr14 | 36978548 | 36978578 | Hyper | cancer_general | NKX2-1, BX161496, SFTA3 | chr14 | 36979619 | 36979649 | Hyper | cancer_general | NKX2-1, BX161496, SFTA3 |
| chr14 | 36982927 | 36982969 | Hyper | cancer_general | NKX2-1, BX161496, SFTA3 | chr14 | 36983708 | 36984146 | Hyper | cancer_general | NKX2-1, BX161496, SFTA3 |
| chr14 | 36985841 | 36985871 | Hyper | cancer_general | BX161496, NKX2-1, SFTA3 | chr14 | 36986301 | 36986841 | Hyper | cancer_general | BX161496, NKX2-1, SFTA3 |
| chr14 | 36987168 | 36987685 | Hyper | cancer_general | BX161496, NKX2-1, SFTA3 | chr14 | 36987939 | 36988143 | Hyper | cancer_general | SFTA3, BX161496, NKX2-1 |
| chr14 | 36988428 | 36988460 | Hyper | tcga | NKX2-1, SFTA3, BX161496 | chr14 | 36990858 | 36991177 | Hyper | cancer_general | SFTA3, BX161496, NKX2-1 |
| chr14 | 36991532 | 36991613 | Hyper | cancer_general | BX161496, NKX2-1, SFTA3 | chr14 | 36991936 | 36992417 | Hyper | cancer_general | SFTA3, BX161496, NKX2-1 |
| chr14 | 36993473 | 36993956 | Hyper | cancer_general | BX161496, NKX2-1 | chr14 | 36994248 | 36994999 | Hyper | cancer_general | BX161496, NKX2-1 |
| chr14 | 37050752 | 37050794 | Hyper | cancer_general | NKX2-8 | chr14 | 37116105 | 37116381 | Hyper | cancer_general, lung, tcga | — |
| chr14 | 37117611 | 37117697 | Hyper | cancer_general | PAX9 | chr14 | 37123438 | 37124077 | Hyper | cancer_general | PAX9 |
| chr14 | 37124364 | 37124572 | Hyper | cancer_general | PAX9 | chr14 | 37124992 | 37125545 | Hyper | tcga, cancer_general | PAX9 |
| chr14 | 37126241 | 37126297 | Hyper | cancer_general | PAX9 | chr14 | 37126566 | 37126897 | Hyper | cancer_general | PAX9 |
| chr14 | 37127281 | 37127311 | Hyper | cancer_general | PAX9 | chr14 | 37127655 | 37128027 | Hyper | cancer_general | PAX9 |
| chr14 | 37128553 | 37128723 | Hyper | literature, cancer_general | PAX9 | chr14 | 37130077 | 37130260 | Hyper | cancer_general | PAX9 |
| chr14 | 37132375 | 37132695 | Hyper | cancer_general | PAX9 | chr14 | 37133001 | 37133052 | Hyper | cancer_general | PAX9 |
| chr14 | 37135784 | 37136345 | Hyper | cancer_general | PAX9 | chr14 | 37136588 | 37136618 | Hyper | cancer_general | PAX9 |
| chr14 | 38060677 | 38060916 | Hyper | cancer_general | FOXA1 | chr14 | 38064401 | 38064549 | Hyper | blood | FOXA1 |
| chr14 | 38677519 | 38677548 | Hyper | tcga | SSTR1 | chr14 | 38677761 | 38677790 | Hyper | tcga | SSTR1 |
| chr14 | 38724294 | 38725258 | Hyper | literature, cancer_general | CLEC14A | chr14 | 38725521 | 38725764 | Hyper | tcga | CLEC14A |
| chr14 | 42074544 | 42074987 | Hyper | cancer_general | LRFN5 | chr14 | 42075888 | 42076212 | Hyper | tcga, cancer_general | LRFN5 |
| chr14 | 42076823 | 42076853 | Hyper | cancer_general | LRFN5 | chr14 | 42077230 | 42077268 | Hyper | cancer_general | LRFN5 |
| chr14 | 42077770 | 42077800 | Hyper | cancer_general | LRFN5 | chr14 | 42079289 | 42079328 | Hyper | cancer_general | LRFN5 |
| chr14 | 48143755 | 48144097 | Hyper | cancer_general | — | chr14 | 48144298 | 48144401 | Hyper | cancer_general | — |
| chr14 | 48144699 | 48145257 | Hyper | cancer_general | — | chr14 | 51338730 | 51338972 | Hyper | cancer_general | ABHD12B |
| chr14 | 51560304 | 51561428 | Hyper | cancer_general, tcga | TRIM9 | chr14 | 51561765 | 51562012 | Hyper | esophageal | TRIM9 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 52534648 | 52534791 | Hyper | cancer_general | NID2 | chr14 | 52535012 | 52536404 | Hyper | tcga, cancer_general, literature | NID2 |
| chr14 | 52734509 | 52734557 | Hyper | cancer_general | PTGDR | chr14 | 52734777 | 52735255 | Hyper | cancer_general | PTGDR |
| chr14 | 52781525 | 52781916 | Hyper | cancer_general | PTGER2 | chr14 | 54422651 | 54422925 | Hyper | liver_tcga, cancer_general | BMP4, MIR5580 |
| chr14 | 55595938 | 55595968 | Hyper | liver_tcga | LGALS3 | chr14 | 57260946 | 57261821 | Hyper | cancer_general | OTX2 |
| chr14 | 57262072 | 57262179 | Hyper | cancer_general | OTX2 | chr14 | 57264079 | 57265240 | Hyper | cancer_general | OTX2 |
| chr14 | 57270995 | 57271266 | Hyper | cancer_general | OTX2-AS1, OTX2 | chr14 | 57272009 | 57272067 | Hyper | cancer_general | OTX2-AS1, OTX2 |
| chr14 | 57274486 | 57275305 | Hyper | cancer_general | OTX2-AS1, OTX2 | | | | | | OTX2-AS1, OTX2 |
| chr14 | 57276440 | 57276666 | Hyper | cancer_general | OTX2-AS1, OTX2 | chr14 | 57275596 | 57276104 | Hyper | cancer_general | OTX2-AS1, OTX2 |
| | | | | | | chr14 | 57277920 | 57279657 | Hyper | literature, cancer_general | OTX2-AS1, OTX2 |
| chr14 | 57283314 | 57284659 | Hyper | cancer_general | OTX2-AS1 | chr14 | 58332297 | 58332403 | Hyper | cancer_general | LRRC9 |
| chr14 | 60097193 | 60097566 | Hyper | cancer_general | RTN1 | chr14 | 60386207 | 60386252 | Hyper | cancer_general | LRRC9 |
| chr14 | 60386638 | 60386701 | Hyper | cancer_general | LRRC9 | chr14 | 60794635 | 60794667 | Hyper | cancer_general | JB175233 |
| chr14 | 60952166 | 60952959 | Hyper | cancer_general | C14orf39 | chr14 | 60973151 | 60973324 | Hyper | cancer_general | SIX6 |
| chr14 | 60973697 | 60974077 | Hyper | literature, cancer_general | SIX6 | chr14 | 60974368 | 60974403 | Hyper | cancer_general | SIX6 |
| chr14 | 60975384 | 60976514 | Hyper | tcga, cancer_general | SIX6 | chr14 | 60976813 | 60976860 | Hyper | cancer_general | SIX6 |
| chr14 | 60977337 | 60978147 | Hyper | cancer_general | SIX6 | chr14 | 60981202 | 60981268 | Hyper | cancer_general | SIX6 |
| chr14 | 60981676 | 60981793 | Hyper | cancer_general | SIX6 | chr14 | 60982110 | 60982622 | Hyper | cancer_general | SIX6 |
| chr14 | 60982841 | 60982911 | Hyper | cancer_general | SIX6 | chr14 | 61104291 | 61104864 | Hyper | cancer_general | SIX1 |
| chr14 | 61108620 | 61108996 | Hyper | liver_tcga, cancer_general | SIX1 | chr14 | 61109206 | 61109470 | Hyper | liver_tcga, cancer_general | SIX1 |
| chr14 | 61109839 | 61110243 | Hyper | cancer_general, literature | SIX1 | chr14 | 61114137 | 61114456 | Hyper | cancer_general | SIX1 |
| chr14 | 61115311 | 61115517 | Hyper | cancer_general | SIX1 | chr14 | 61118736 | 61118765 | Hyper | literature | SIX1 |
| chr14 | 61118965 | 61119136 | Hyper | cancer_general | SIX1 | chr14 | 61119536 | 61119639 | Hyper | cancer_general | SIX1 |
| chr14 | 61747300 | 61748033 | Hyper | blood | TMEM30B | chr14 | 62279578 | 62280006 | Hyper | tcga, cancer_general | — |
| chr14 | 62583809 | 62583909 | Hyper | tcga, cancer_general | LINC00643 | chr14 | 63512100 | 63512291 | Hyper | cancer_general | KCNH5 |
| chr14 | 63512573 | 63512816 | Hyper | cancer_general | KCNH5 | chr14 | 63513124 | 63513154 | Hyper | cancer_general | KCNH5 |
| chr14 | 65008994 | 65009193 | Hyper | cancer_general | PPP1R36, HSPA2 | chr14 | 70014723 | 70014974 | Hyper | cancer_general, liver_tcga | — |
| chr14 | 70038490 | 70038635 | Hyper | liver_tcga, cancer_general | CCDC177 | chr14 | 70038990 | 70039025 | Hyper | cancer_general | CCDC177 |
| chr14 | 70346136 | 70346491 | Hyper | tcga, cancer_general | SMOC1 | chr14 | 70654343 | 70654713 | Hyper | cancer_general | — |
| chr14 | 70655530 | 70656090 | Hyper | cancer_general, tcga | — | chr14 | 72398743 | 72399019 | Hyper | cancer_general | RGS6 |
| chr14 | 72399361 | 72399453 | Hyper | cancer_general | RGS6 | chr14 | 72399929 | 72400029 | Hyper | cancer_general | RGS6 |
| chr14 | 74706015 | 74706222 | Hyper | cancer_general | VSX2 | chr14 | 74706458 | 74707873 | Hyper | cancer_general | VSX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 74708862 | 74708955 | Hyper | cancer_general | VSX2 | chr14 | 74892540 | 74892569 | Hyper | liver_tcga | SYNDIG1L |
| chr14 | 74893074 | 74893113 | Hyper | cancer_general | SYNDIG1L | chr14 | 75078170 | 75078507 | Hyper | cancer_general | LTBP2 |
| chr14 | 75988341 | 75988370 | Hyper | literature | BATF | chr14 | 75988732 | 75988761 | Hyper | literature | BATF |
| chr14 | 76604682 | 76604716 | Hyper | cancer_general | — | chr14 | 76605072 | 76605376 | Hyper | cancer_general | — |
| chr14 | 76843461 | 76843504 | Hyper | cancer_general | ESRRB | chr14 | 76843742 | 76843953 | Hyper | cancer_general | ESRRB |
| chr14 | 77228121 | 77228159 | Hyper | liver_tcga | VASH1 | chr14 | 77606907 | 77607236 | Hyper | tcga, cancer_general | ZDHHC22 |
| chr14 | 77737212 | 77737785 | Hyper | tcga, cancer_general | POMT2, MIR1260A, NGB | chr14 | 79745138 | 79745175 | Hyper | cancer_general | NRXN3 |
| chr14 | 85996479 | 85996608 | Hyper | cancer_general, tcga | FLRT2, BX248253 | chr14 | 85996851 | 85996906 | Hyper | cancer_general | FLRT2, BX248253 |
| chr14 | 85997821 | 85998006 | Hyper | cancer_general | BX248253, FLRT2 | chr14 | 85998288 | 85998683 | Hyper | tcga, cancer_general | FLRT2, BX248253 |
| chr14 | 85999569 | 85999613 | Hyper | cancer_general | BX248253, FLRT2 | chr14 | 86000270 | 86000511 | Hyper | cancer_general | FLRT2, BX248253 |
| chr14 | 86000918 | 86001114 | Hyper | cancer_general | FLRT2, BX248253 | chr14 | 89817889 | 89818034 | Hyper | cancer_general | — |
| chr14 | 90527714 | 90527758 | Hyper | cancer_general | KCNK13 | chr14 | 92789512 | 92789542 | Hyper | cancer_general | SLC24A4 |
| chr14 | 92789863 | 92790169 | Hyper | tcga, cancer_general | SLC24A4 | chr14 | 92790637 | 92790703 | Hyper | cancer_general | SLC24A4 |
| chr14 | 92979917 | 92979991 | Hyper | pancreas | RIN3 | chr14 | 93389542 | 93389776 | Hyper | liver_tcga, cancer_general | CHGA |
| chr14 | 94254389 | 94254513 | Hyper | cancer_general | PRIMA1 | chr14 | 94405734 | 94405785 | Hyper | cancer_general | ASB2 |
| chr14 | 94889856 | 94889886 | Hyper | head_neck | — | chr14 | 95234643 | 95235369 | Hyper | tcga, cancer_general, literature | GSC |
| chr14 | 95235989 | 95236111 | Hyper | cancer_general | GSC | chr14 | 95236524 | 95236553 | Hyper | literature | GSC |
| chr14 | 95236819 | 95236848 | Hyper | literature | GSC | chr14 | 95237622 | 95237651 | Hyper | literature | GSC |
| chr14 | 95239380 | 95239633 | Hyper | cancer_general | GSC | chr14 | 95240127 | 95240157 | Hyper | cancer_general | GSC |
| chr14 | 95240392 | 95240422 | Hyper | cancer_general | GSC | chr14 | 95557626 | 95557655 | Hyper | literature | DICER1 |
| chr14 | 95560448 | 95560477 | Hyper | literature | DICER1 | chr14 | 96342648 | 96342692 | Hyper | cancer_general | LINC00617 |
| chr14 | 96342897 | 96343133 | Hyper | tcga, cancer_general | LINC00617 | chr14 | 96343404 | 96343433 | Hyper | tcga | LINC00617 |
| chr14 | 96343643 | 96343701 | Hyper | cancer_general | LINC00617 | chr14 | 97058856 | 97059083 | Hyper | cancer_general | BC035096 |
| chr14 | 97499277 | 97499315 | Hyper | cancer_general | — | chr14 | 97499706 | 97499944 | Hyper | cancer_general | — |
| chr14 | 97685044 | 97685288 | Hyper | cancer_general | — | chr14 | 97685707 | 97685959 | Hyper | cancer_general | — |
| chr14 | 99584575 | 99584664 | Hyper | cancer_general | BCL11B | chr14 | 99712321 | 99712394 | Hyper | tcga | BCL11B |
| chr14 | 99736151 | 99736183 | Hyper | cancer_general | EVL | chr14 | 99737398 | 99737462 | Hyper | blood | BCL11B |
| chr14 | 100437794 | 100437977 | Hyper | cancer_general | WARS, SLC25A47 | chr14 | 100438705 | 100438811 | Hyper | cancer_general | EVL |
| chr14 | 100793556 | 100793650 | Hyper | liver_tcga | BC148240, MEG9 | chr14 | 101193242 | 101193286 | Hyper | cancer_general | DLK1 |
| chr14 | 101543868 | 101544235 | Hyper | tcga, cancer_general | — | chr14 | 101923114 | 101923250 | Hyper | cancer_general | — |
| chr14 | 101923600 | 101923738 | Hyper | cancer_general | — | chr14 | 101923957 | 101924047 | Hyper | cancer_general | — |
| chr14 | 101925049 | 101925901 | Hyper | tcga, cancer_general | — | chr14 | 102026360 | 102026484 | Hyper | cancer_general | MIR1247, DIO3, DIO3AS, DIO3OS |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr14 | 102026797 | 102026967 | Hyper | tcga | DIO3, MIR1247, DIO3AS, DIO3OS | chr14 | 102031231 | 102031271 | Hyper | cancer_general | MIR1247, DIO3AS, DIO3OS, DIO3 |
| chr14 | 102031512 | 102031580 | Hyper | cancer_general | DIO3OS, DIO3, MIR1247, DIO3AS | chr14 | 102247912 | 102248214 | Hyper | cancer_general | PPP2R5C |
| chr14 | 103021391 | 103022003 | Hyper | cancer_general | — | chr14 | 103394884 | 103395101 | Hyper | liver_tcga, cancer_general | CDC42BPB, AMN |
| chr14 | 103655226 | 103655601 | Hyper | cancer_general | LINC00605 | chr14 | 103674078 | 103674143 | Hyper | cancer_general | — |
| chr14 | 103687082 | 103687219 | Hyper | cancer_general | — | chr14 | 103739967 | 103740150 | Hyper | cancer_general | — |
| chr14 | 103740358 | 103740430 | Hyper | cancer_general | — | chr14 | 103745699 | 103745750 | Hyper | cancer_general | — |
| chr14 | 104601737 | 104601832 | Hyper | cancer_general | KIF26A | chr14 | 104602033 | 104602063 | Hyper | cancer_general | KIF26A TMEM179 |
| chr14 | 104605032 | 104605114 | Hyper | cancer_general | KIF26A | chr14 | 105071298 | 105071396 | Hyper | tcga | AKT1 |
| chr14 | 105239389 | 105239439 | Hyper | literature | AKT1 | chr14 | 105239793 | 105239825 | Hyper | literature | AKT1 |
| chr14 | 105241309 | 105241428 | Hyper | literature | AKT1 | chr14 | 105243032 | 105243064 | Hyper | literature | GPR132 |
| chr14 | 105246427 | 105246582 | Hyper | pancreas | BTBD6, BRF1 | chr14 | 105512063 | 105512395 | Hyper | ovarian | PACS2 |
| chr14 | 105714415 | 105715529 | Hyper | liver_tcga | C14orf80, CRIP1 | chr14 | 105830630 | 105830859 | Hyper | liver_tcga | — |
| chr14 | 105963655 | 105963772 | Hyper | liver_tcga, cancer_general | SSU72, TMEM240, AX747755, ATAD3A | AEKP01168736.1-4752 | 1754 | 2287 | Hyper | cancer_general | NADK |
| chr1 | 1475556 | 1476318 | Hyper | tcga | AK054708, KIAA1751 | chr1 | 1688882 | 1689012 | Hyper | liver_tcga | SKI |
| chr1 | 1935274 | 1935459 | Hyper | head_neck, cancer_general | — | chr1 | 2165895 | 2165999 | Hyper | cancer_general | LOC115110 |
| chr1 | 2375148 | 2375543 | Hyper | cancer_general | TTC34 | chr1 | 2472174 | 2472301 | Hyper | pancreas | PRDM16, FL142875 CCDC27, TP73-AS1 |
| chr1 | 2706197 | 2706469 | Hyper | literature, cancer_general, liver_tcga | TP73, WRAP73 | chr1 | 2984719 | 2984749 | Hyper | cancer_general | AJAP1 |
| chr1 | 3567093 | 3568226 | Hyper | cancer_general, esophageal | CCDC27, TP73-AS1 | chr1 | 3663532 | 3663562 | Hyper | colorectal | HES3, GPR153, C1orf211, ICMT |
| chr1 | 3663874 | 3663921 | Hyper | cancer_general, tcga | AJAP1 | chr1 | 4714018 | 4714345 | Hyper | literature, cancer_general | ESPN |
| chr1 | 4714741 | 4716701 | Hyper | cancer_general | ESPN, MIR4252, HES2 | chr1 | 6304201 | 6304242 | Hyper | cancer_general | CAMTA1 |
| chr1 | 6480514 | 6480831 | Hyper | tcga, breast blood | ESPN ERRFI1 | chr1 | 6501001 | 6501179 | Hyper | cancer_general | — |
| chr1 | 6507678 | 6508126 | Hyper |  |  | chr1 | 7764641 | 7764737 | Hyper | liver_tcga | |
| chr1 | 8085685 | 8085715 | Hyper | liver_tcga | H6PD | chr1 | 8277374 | 8277760 | Hyper | tcga, cancer_general | C1orf200, PIK3CD |
| chr1 | 9324231 | 9324274 | Hyper | liver_tcga | C1orf200, PIK3CD | chr1 | 9527172 | 9527208 | Hyper | liver_tcga | |
| chr1 | 9712074 | 9712104 | Hyper | esophageal |  | chr1 | 9712561 | 9713014 | Hyper | tcga, cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 10948552 | 10948582 | Hyper | cancer_general | — | chr1 | 11169346 | 11169375 | Hyper | literature | MTOR, EXOSC10 |
| chr1 | 11174404 | 11174433 | Hyper | literature | MTOR | chr1 | 11181358 | 11181432 | Hyper | literature | MTOR |
| chr1 | 11182142 | 11182171 | Hyper | literature | MTOR | chr1 | 11188149 | 11188178 | Hyper | literature | MTOR |
| chr1 | 11210182 | 11210211 | Hyper | literature | MTOR-AS1, MTOR | chr1 | 11217215 | 11217337 | Hyper | literature | MTOR-AS1, MTOR |
| chr1 | 11249032 | 11249061 | Hyper | liver_tcga | ANGPTL7 | chr1 | 11538705 | 11538821 | Hyper | esophageal | PTCHD2 |
| chr1 | 11539175 | 11539205 | Hyper | esophageal | PTCHD2 | chr1 | 11539410 | 11539440 | Hyper | esophageal | PTCHD2 |
| chr1 | 11540129 | 11540238 | Hyper | cancer_general | PTCHD2 | chr1 | 11752476 | 11752511 | Hyper | cancer_general | DRAXIN |
| chr1 | 11959093 | 11959196 | Hyper | cancer_general | — | chr1 | 12123243 | 12123640 | Hyper | cancer_general, colorectal | TNFRSF8 |
| chr1 | 12227685 | 12227941 | Hyper | tcga, cancer_general | TNFRSF1B | chr1 | 13839770 | 13839985 | Hyper | tcga, cancer_general | LRRC38 |
| chr1 | 13910436 | 13910714 | Hyper | cancer_general | PDPN | chr1 | 14026481 | 14026618 | Hyper | liver_tcga | PRDM2 |
| chr1 | 14925501 | 14926050 | Hyper | cancer_general | KAZN | chr1 | 15251120 | 15251211 | Hyper | blood | KAZN |
| chr1 | 15480593 | 15480892 | Hyper | blood | TMEM51-AS1, TMEM51 | chr1 | 16085356 | 16085656 | Hyper | tcga | FBLIM1 |
| chr1 | 16861522 | 16861552 | Hyper | cancer_general | AX747988, BC036435, TRNA_Asn | chr1 | 17445857 | 17445943 | Hyper | pancreas | PADI2 |
| chr1 | 18434449 | 18434520 | Hyper | cancer_general | IGSF21 | chr1 | 18437457 | 18437526 | Hyper | cancer_general | IGSF21 |
| chr1 | 18956211 | 18956304 | Hyper | cancer_general | PAX7 | chr1 | 18956574 | 18956655 | Hyper | cancer_general | PAX7 |
| chr1 | 18956856 | 18957246 | Hyper | literature, cancer_general | PAX7 | chr1 | 18957507 | 18957587 | Hyper | cancer_general | PAX7 |
| chr1 | 18958033 | 18958381 | Hyper | tcga, cancer_general | PAX7 | chr1 | 18959440 | 18959550 | Hyper | cancer_general | PAX7 |
| chr1 | 18960897 | 18960990 | Hyper | cancer_general | PAX7 | chr1 | 18962727 | 18963135 | Hyper | cancer_general | PAX7 |
| chr1 | 18969625 | 18969819 | Hyper | cancer_general | PAX7 | chr1 | 18971852 | 18971929 | Hyper | cancer_general | PAX7 |
| chr1 | 18972130 | 18972160 | Hyper | cancer_general | PAX7 | chr1 | 19043563 | 19043678 | Hyper | cancer_general | PAX7 |
| chr1 | 19992349 | 19992432 | Hyper | cancer_general | NBL1, HTR6 | chr1 | 20618329 | 20618369 | Hyper | cancer_general | VWA5B1 |
| chr1 | 20693317 | 20693420 | Hyper | blood | LOC339505 | chr1 | 20879035 | 20879289 | Hyper | cancer_general | FAM43B |
| chr1 | 20879640 | 20879957 | Hyper | cancer_general | FAM43B | chr1 | 20879845 | 20879957 | Hyper | cancer_general | FAM43B |
| chr1 | 20880182 | 20880605 | Hyper | tcga, cancer_general | FAM43B | chr1 | 21044125 | 21044161 | Hyper | cancer_general | KIF17, SH2D5 |
| chr1 | 21058635 | 21058776 | Hyper | esophageal | SH2D5 | chr1 | 21835943 | 21836007 | Hyper | cancer_general | ALPL |
| chr1 | 22140753 | 22141184 | Hyper | tcga, cancer_general, liver_tcga | LDLRAD2, HSPG2 | chr1 | 23748982 | 23749070 | Hyper | cancer_general | ASAP3, TCEA3 |
| chr1 | 23885070 | 23885100 | Hyper | breast | ID3 | chr1 | 25255823 | 25255934 | Hyper | tcga | RUNX3 |
| chr1 | 25256354 | 25256383 | Hyper | literature | RUNX3 | chr1 | 25256924 | 25257205 | Hyper | literature, cancer_general | RUNX3 |
| chr1 | 25257532 | 25257561 | Hyper | literature | RUNX3 | chr1 | 26551695 | 26551796 | Hyper | tcga | BC030768, CEP85 |
| chr1 | 26552086 | 26552130 | Hyper | cancer_general | CEP85, BC030768 | chr1 | 26737583 | 26737613 | Hyper | cancer_general | LIN28A |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 26737946 | 26738182 | Hyper | cancer_general | LIN28A | chr1 | 29450491 | 29450543 | Hyper | esophageal | TMEM200B, EPB41 |
| chr1 | 29586072 | 29586674 | Hyper | tcga, lung, cancer_general | PTPRU | chr1 | 29804947 | 29805094 | Hyper | cancer_general | — |
| chr1 | 30815412 | 30815578 | Hyper | cancer_general | — | chr1 | 32180397 | 32180427 | Hyper | head_neck | — |
| chr1 | 32237584 | 32238507 | Hyper | tcga, cancer_general | — | chr1 | 32410276 | 32410306 | Hyper | cancer_general | PTP4A2 |
| chr1 | 32410519 | 32410614 | Hyper | liver_tcga | PTP4A2 | chr1 | 32930458 | 32930558 | Hyper | tcga | ZBTB8A, ZBTB8B |
| chr1 | 33219567 | 33219596 | Hyper | liver_tcga | KIAA1522 | chr1 | 34628948 | 34628978 | Hyper | cancer_general | C1orf94 |
| chr1 | 34629469 | 34629728 | Hyper | cancer_general | C1orf94 | chr1 | 34630548 | 34630635 | Hyper | cancer_general | C1orf94 |
| chr1 | 34630859 | 34630978 | Hyper | cancer_general | C1orf94 | chr1 | 34631580 | 34631662 | Hyper | cancer_general | C1orf94 |
| chr1 | 34631933 | 34631963 | Hyper | cancer_general | C1orf94 | chr1 | 34642380 | 34642573 | Hyper | cancer_general | C1orf94 |
| chr1 | 35258637 | 35258714 | Hyper | cancer_general | GJA4, GJB3 | chr1 | 35351078 | 35351659 | Hyper | cancer_general | DLGAP3 |
| chr1 | 35395526 | 35395851 | Hyper | tcga | — | chr1 | 36042679 | 36043489 | Hyper | tcga, cancer_general | TFAP2E, PSMB2 |
| chr1 | 36849009 | 36849038 | Hyper | liver_tcga | LSM10 | chr1 | 37499792 | 37499181 | Hyper | cancer_general | GRIK3 |
| chr1 | 37499460 | 37500153 | Hyper | cancer_general | GRIK3 | chr1 | 37500468 | 37500806 | Hyper | cancer_general | GRIK3 |
| chr1 | 37501072 | 37501102 | Hyper | cancer_general | GRIK3 | chr1 | 38100689 | 38100851 | Hyper | tcga, cancer_general | RSPO1 |
| chr1 | 38219712 | 38219795 | Hyper | cancer_general | EPHA10 | chr1 | 38230042 | 38230297 | Hyper | cancer_general | EPHA10 |
| chr1 | 38230779 | 38230859 | Hyper | literature, cancer_general | EPHA10 | chr1 | 38412504 | 38412832 | Hyper | tcga, cancer_general | SF3A3, INPP5B |
| chr1 | 38510178 | 38510217 | Hyper | cancer_general | POU3F1 | chr1 | 38510563 | 38510624 | Hyper | cancer_general | POU3F1 |
| chr1 | 38510854 | 38511119 | Hyper | tcga, cancer_general | POU3F1 | chr1 | 38511337 | 38511824 | Hyper | colorectal, cancer_general | POU3F1 |
| chr1 | 38512385 | 38512415 | Hyper | esophageal, tcga, cancer_general | POU3F1 | chr1 | 38513244 | 38513318 | Hyper | liver_tcga | POU3F1 |
| chr1 | 39269741 | 39270121 | Hyper | cancer_general | — | chr1 | 40137898 | 40137984 | Hyper | tcga | HPCAL4, NT5C1A |
| chr1 | 40237141 | 40237203 | Hyper | cancer_general | OXCT2, BMP8B | chr1 | 40915590 | 40915620 | Hyper | esophageal | ZFP69B |
| chr1 | 41283958 | 41284463 | Hyper | cancer_general | KCNQ4 | chr1 | 41847583 | 41847702 | Hyper | cancer_general | — |
| chr1 | 41848810 | 41848840 | Hyper | cancer_general | — | chr1 | 43814994 | 43815023 | Hyper | literature | CDC20, MPL |
| chr1 | 44872448 | 44873706 | Hyper | tcga, cancer_general | RNF220 | chr1 | 44883121 | 44884197 | Hyper | tcga, cancer_general | RNF220 |
| chr1 | 45308592 | 45308625 | Hyper | liver_tcga | EIF2B3, PTCH2 | chr1 | 46632876 | 46632923 | Hyper | cancer_general | TSPAN1 |
| chr1 | 46913837 | 46914283 | Hyper | tcga, cancer_general | LOC729041 | chr1 | 46914656 | 46914686 | Hyper | cancer_general | LOC729041 |
| chr1 | 46932765 | 46932905 | Hyper | tcga | — | chr1 | 46951207 | 46951739 | Hyper | liver_tcga, cancer_general | — |
| chr1 | 46956454 | 46956603 | Hyper | cancer_general | — | chr1 | 46956823 | 46957171 | Hyper | cancer_general | — |
| chr1 | 47009929 | 47010070 | Hyper | cancer_general | KNCN, MKNK1-AS1 | chr1 | 47695122 | 47695422 | Hyper | cancer_general | STIL, JA375062, TAL1 |
| chr1 | 47696295 | 47696597 | Hyper | cancer_general | STIL, JA375062, TAL1 | chr1 | 47696821 | 47697110 | Hyper | cancer_general | STIL, JA375062, TAL1, STIL |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 47697356 | 47697510 | Hyper | cancer_general, tcga | TAL1, STIL, JA375062 | chr1 | 47697732 | 47698210 | Hyper | liver_tcga, literature, cancer_general | STIL, JA375062, TAL1 |
| chr1 | 47882063 | 47882322 | Hyper | liver_tcga, cancer_general | FOXE3 | chr1 | 47882769 | 47882803 | Hyper | cancer_general | FOXE3 |
| chr1 | 47909718 | 47910160 | Hyper | cancer_general | FOXD2, FOXD2-AS1 | chr1 | 47910523 | 47910914 | Hyper | liver_tcga, cancer_general | FOXD2 |
| chr1 | 47911335 | 47911508 | Hyper | liver_tcga | FOXD2 | chr1 | 47999050 | 47999163 | Hyper | liver_tcga | |
| chr1 | 48059078 | 48059243 | Hyper | cancer_general | — | chr1 | 49242344 | 49242533 | Hyper | tcga | BEND5, AGBL4 |
| chr1 | 50513629 | 50513745 | Hyper | cancer_general | ELAVL4 | chr1 | 50799278 | 50799400 | Hyper | cancer_general | — |
| chr1 | 50880911 | 50881302 | Hyper | liver_tcga, cancer_general | DMRTA2 | chr1 | 50881521 | 50882529 | Hyper | cancer_general | DMRTA2 |
| chr1 | 50882808 | 50883611 | Hyper | cancer_general | DMRTA2 | chr1 | 50883882 | 50884916 | Hyper | tcga, literature, cancer_general | DMRTA2 |
| chr1 | 50885336 | 50885366 | Hyper | cancer_general | DMRTA2 | chr1 | 50886188 | 50887284 | Hyper | literature, cancer_general | DMRTA2 |
| chr1 | 50888709 | 50888826 | Hyper | cancer_general, liver_tcga | DMRTA2 | chr1 | 50889104 | 50889510 | Hyper | liver_tcga, cancer_general | DMRTA2 |
| chr1 | 50889820 | 50890379 | Hyper | cancer_general, tcga | DMRTA2 | chr1 | 50890683 | 50891595 | Hyper | lung, cancer_general | DMRTA2 |
| chr1 | 50892153 | 50892351 | Hyper | cancer_general | DMRTA2 | chr1 | 50892607 | 50893877 | Hyper | cancer_general | DMRTA2 |
| chr1 | 53019468 | 53019568 | Hyper | esophageal | ZCCHC11 | chr1 | 53068166 | 53068546 | Hyper | tcga, esophageal, cancer_general | GPX7 |
| chr1 | 53098842 | 53099067 | Hyper | tcga | FAM159A | chr1 | 53308568 | 53309248 | Hyper | cancer_general | ZYG11A |
| chr1 | 53528374 | 53528439 | Hyper | cancer_general | PODN | chr1 | 54203516 | 54204399 | Hyper | cancer_general | GLIS1 |
| chr1 | 55462673 | 55462703 | Hyper | cancer_general | BSND, ETMM61 | chr1 | 57888367 | 57888397 | Hyper | cancer_general | DAB1 |
| chr1 | 57888987 | 57889087 | Hyper | cancer_general | DAB1 | chr1 | 57889402 | 57889654 | Hyper | tcga, cancer_general | DAB1 |
| chr1 | 57890431 | 57890650 | Hyper | tcga, cancer_general | DAB1 | chr1 | 58715153 | 58715194 | Hyper | cancer_general | |
| chr1 | 58715475 | 58715993 | Hyper | tcga, cancer_general | — | chr1 | 61519360 | 61519394 | Hyper | cancer_general | |
| chr1 | 62660740 | 62660861 | Hyper | liver_tcga | L1TD1 | chr1 | 63539509 | 63539887 | Hyper | tcga, cancer_general | |
| chr1 | 63785333 | 63786329 | Hyper | liver_tcga, literature, cancer_general | FOXD3 | chr1 | 63787031 | 63787063 | Hyper | cancer_general | FOXD3 |
| chr1 | 63787302 | 63787568 | Hyper | cancer_general | FOXD3 | chr1 | 63788423 | 63788557 | Hyper | liver_tcga | FOXD3 |
| chr1 | 63788788 | 63790278 | Hyper | liver_tcga, cancer_general | U7, FOXD3 | chr1 | 63792561 | 63793072 | Hyper | cancer_general | U7, FOXD3 |
| chr1 | 63795263 | 63796277 | Hyper | cancer_general | U7, FOXD3 | chr1 | 63796498 | 63796575 | Hyper | cancer_general | FOXD3 |
| chr1 | 64240026 | 64240118 | Hyper | blood | ROR1 | chr1 | 64240617 | 64240673 | Hyper | blood | ROR1 |
| chr1 | 64937330 | 64937542 | Hyper | tcga | CACHD1 | chr1 | 65303636 | 65303692 | Hyper | literature | JAK1, RAVER2 |
| chr1 | 65304227 | 65304256 | Hyper | literature | JAK1, RAVER2 | chr1 | 65305384 | 65305413 | Hyper | literature | JAK1, RAVER2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 65306926 | 65306955 | Hyper | literature | JAK1, RAVER2 | chr1 | 65309787 | 65309816 | Hyper | literature | JAK1 |
| chr1 | 65310487 | 65310531 | Hyper | literature | JAK1 | chr1 | 65311188 | 65311217 | Hyper | literature | JAK1 |
| chr1 | 65312331 | 65312432 | Hyper | literature | JAK1 | chr1 | 65731337 | 65731446 | Hyper | tcga, cancer_general | DNAJC6, AK123450 |
| chr1 | 65731649 | 65731752 | Hyper | tcga, cancer_general | DNAJC6, AK123450 | chr1 | 65990955 | 65991034 | Hyper | cancer_general | LEPR |
| chr1 | 65991446 | 65991779 | Hyper | tcga, cancer_general | LEPR | chr1 | 66258180 | 66258774 | Hyper | cancer_general | PDE4B |
| chr1 | 66259137 | 66259174 | Hyper | cancer_general | PDE4B | chr1 | 66998790 | 66999332 | Hyper | cancer_general, tcga | SGIP1 |
| chr1 | 66999636 | 66999673 | Hyper | cancer_general | SGIP1 | chr1 | 67218064 | 67218343 | Hyper | cancer_general | SGIP1, TCTEX1D1 |
| chr1 | 67390334 | 67390450 | Hyper | literature | MIER1, WDR78 | chr1 | 67391067 | 67391096 | Hyper | literature | MIER1, WDR78 |
| chr1 | 67773159 | 67773780 | Hyper | tcga, cancer_general, liver_tcga | IL12RB2 | chr1 | 70033609 | 70033916 | Hyper | tcga | LRRC7 |
| chr1 | 70034459 | 70034574 | Hyper | tcga, cancer_general | LRRC7 | chr1 | 70035088 | 70035537 | Hyper | cancer_general | LRRC7 |
| chr1 | 72749641 | 72749715 | Hyper | cancer_general | — | chr1 | 75595798 | 75596384 | Hyper | cancer_general | LHX8, AK055631 |
| chr1 | 75596687 | 75597584 | Hyper | cancer_general | LHX8, AK055631 | chr1 | 75597923 | 75598179 | Hyper | cancer_general | LHX8, AK055631 |
| chr1 | 75598384 | 75598414 | Hyper | cancer_general | LHX8, AK055631 | chr1 | 75599427 | 75599621 | Hyper | cancer_general | LHX8, AK055631, LHX8 |
| chr1 | 75600225 | 75600848 | Hyper | tcga, cancer_general | LHX8, AK055631 | chr1 | 75601058 | 75601428 | Hyper | cancer_general | LHX8, AK055631 |
| chr1 | 75601983 | 75603052 | Hyper | tcga, cancer_general | LHX8, AK055631 | chr1 | 76080484 | 76080768 | Hyper | tcga, cancer_general | SLC44A5 |
| chr1 | 76082129 | 76082209 | Hyper | cancer_general | SLC44A5 | chr1 | 76540450 | 76540666 | Hyper | tcga, cancer_general | ST6GALNAC3 |
| chr1 | 77333058 | 77333088 | Hyper | cancer_general | ST6GALNAC5 | chr1 | 77333384 | 77333544 | Hyper | cancer_general | ST6GALNAC5 |
| chr1 | 77334030 | 77334762 | Hyper | tcga, cancer_general | ST6GALNAC5 | chr1 | 77747366 | 77747453 | Hyper | cancer_general | AK5 |
| chr1 | 77747939 | 77748235 | Hyper | tcga, cancer_general | AK5 | chr1 | 78511466 | 78512354 | Hyper | tcga, lung, cancer_general | GIPC2 |
| chr1 | 78957292 | 78957522 | Hyper | cancer_general | PTGFR | chr1 | 82267150 | 82267185 | Hyper | tcga | LPHN2 |
| chr1 | 82268573 | 82268815 | Hyper | tcga | LPHN2 | chr1 | 85358622 | 85358822 | Hyper | cancer_general | LPAR3 |
| chr1 | 85463349 | 85463378 | Hyper | liver_tcga | MCOLN2 | chr1 | 85725508 | 85725537 | Hyper | tcga | BCL10, C1orf52 |
| chr1 | 86621660 | 86622127 | Hyper | tcga, cancer_general | COL24A1 | chr1 | 86622526 | 86622751 | Hyper | cancer_general, tcga | COL24A1 |
| chr1 | 87617774 | 87617807 | Hyper | cancer_general | — | chr1 | 90099997 | 90100084 | Hyper | tcga | FLJ27354, LRRC8C |
| chr1 | 90309292 | 90309490 | Hyper | ovarian | LRRC8D | chr1 | 91172012 | 91172677 | Hyper | cancer_general | BARHL2 |
| chr1 | 91177941 | 91178207 | Hyper | cancer_general | BARHL2 | chr1 | 91180075 | 91180306 | Hyper | lung, cancer_general | BARHL2 |
| chr1 | 91181932 | 91182132 | Hyper | cancer_general | BARHL2 | chr1 | 91182338 | 91183711 | Hyper | cancer_general, tcga, liver_tcga, literature | BARHL2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 91183951 | 91183986 | Hyper | cancer_general | BARHL2 | chr1 | 91184423 | 91184672 | Hyper | cancer_general | BARHL2 |
| chr1 | 91185190 | 91185707 | Hyper | cancer_general | BARHL2 | chr1 | 91188983 | 91189383 | Hyper | cancer_general | BARHL2 |
| chr1 | 91189688 | 91190380 | Hyper | cancer_general | BARHL2 | chr1 | 91190869 | 91191310 | Hyper | cancer_general | BARHL2 |
| chr1 | 91192274 | 91192671 | Hyper | cancer_general | BARHL2 | chr1 | 91194414 | 91194569 | Hyper | cancer_general | — |
| chr1 | 91195117 | 91195390 | Hyper | cancer_general | — | chr1 | 91195879 | 91196502 | Hyper | cancer_general | — |
| chr1 | 91316261 | 91316313 | Hyper | cancer_general | — | chr1 | 91316627 | 91316682 | Hyper | cancer_general | — |
| chr1 | 91869988 | 91870018 | Hyper | esophageal | HFM1 | chr1 | 92948324 | 92948597 | Hyper | tcga, cancer_general | GFI1 |
| chr1 | 92948841 | 92948976 | Hyper | cancer_general | GFI1 | chr1 | 92952145 | 92952655 | Hyper | cancer_general | GFI1 |
| chr1 | 94147641 | 94147670 | Hyper | tcga | — | chr1 | 95006795 | 95006902 | Hyper | blood | F3 |
| chr1 | 98510791 | 98511335 | Hyper | tcga, cancer_general | MIR2682, MIR137, MIR137HG | chr1 | 98511628 | 98511922 | Hyper | cancer_general | MIR2682, MIR137HG, MIR137 |
| chr1 | 98514225 | 98514255 | Hyper | cancer_general | MIR137HG, MIR137, MIR2682 | chr1 | 98515256 | 98515319 | Hyper | cancer_general | MIR137, MIR2682, MIR137HG |
| chr1 | 98519023 | 98519675 | Hyper | pancreas, tcga, cancer_general | MIR2682, MIR137HG, MIR137 | chr1 | 99469682 | 99469788 | Hyper | cancer_general | LOC100129620, LPPR5 |
| chr1 | 99470128 | 99470207 | Hyper | liver_tcga | LOC100129620, LPPR5 | chr1 | 99470785 | 99470847 | Hyper | cancer_general | LOC100129620, LPPR5 |
| chr1 | 101004456 | 101004737 | Hyper | cancer_general | GPR88 | chr1 | 101005071 | 101005144 | Hyper | tcga, cancer_general | GPR88 |
| chr1 | 101005360 | 101005675 | Hyper | cancer_general, tcga | GPR88 | chr1 | 101702504 | 101702616 | Hyper | cancer_general | S1PR1 |
| chr1 | 101703612 | 101703642 | Hyper | cancer_general | S1PR1 | chr1 | 103574508 | 103574537 | Hyper | literature | COL11A1 |
| chr1 | 107682735 | 107682977 | Hyper | tcga, cancer_general | NTNG1 | chr1 | 107683439 | 107683517 | Hyper | cancer_general | NTNG1 |
| chr1 | 107684240 | 107684439 | Hyper | tcga | NTNG1 | chr1 | 108507063 | 108507092 | Hyper | tcga | VAV3-AS1 |
| chr1 | 108507320 | 108507497 | Hyper | tcga, cancer_general | VAV3-AS1 | chr1 | 108507717 | 108507810 | Hyper | cancer_general | VAV3-AS1 |
| chr1 | 108508052 | 108508640 | Hyper | cancer_general, tcga | VAV3-AS1 | chr1 | 109203609 | 109203672 | Hyper | liver_tcga | HENMT1 |
| chr1 | 110610586 | 110612058 | Hyper | liver_tcga, cancer_general, literature | DQ574855, ALX3 | chr1 | 110612846 | 110613152 | Hyper | cancer_general | DQ574855, ALX3 |
| chr1 | 110626684 | 110627578 | Hyper | cancer_general | — | chr1 | 110672889 | 110673233 | Hyper | cancer_general | — |
| chr1 | 110692973 | 110694117 | Hyper | tcga, cancer_general | SLC6A17 | chr1 | 110754003 | 110754101 | Hyper | liver_tcga | KCNC4 |
| chr1 | 110754309 | 110754830 | Hyper | cancer_general | KCNC4 | chr1 | 111097906 | 111097936 | Hyper | liver_tcga, tcga, cancer_general | — |
| chr1 | 111098196 | 111098316 | Hyper | cancer_general | — | chr1 | 111216763 | 111217982 | Hyper | cancer_general | KCNA3 |
| chr1 | 111506007 | 111506212 | Hyper | cancer_general | LRIF1 | chr1 | 111813546 | 111813587 | Hyper | cancer_general | CHIAP2 |
| chr1 | 114695439 | 114695943 | Hyper | tcga, cancer_general | — | chr1 | 114696210 | 114696712 | Hyper | tcga | — |
| chr1 | 115256514 | 115256552 | Hyper | literature | CSDE1, NRAS | chr1 | 115258729 | 115258772 | Hyper | literature | NRAS, CSDE1 |

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 115631867 | 115631915 | Hyper | pancreas | TSPAN2 | chr1 | 115632469 | 115632555 | Hyper | cancer_general | TSPAN2 |
| chr1 | 115880184 | 115880395 | Hyper | pancreas, cancer_general | — | chr1 | 115880850 | 115881218 | Hyper | tcga, cancer_general | — |
| chr1 | 116371139 | 116371201 | Hyper | cancer_general | NHLH2 | chr1 | 116380651 | 116381287 | Hyper | cancer_general | NHLH2 |
| chr1 | 116382387 | 116382478 | Hyper | cancer_general | NHLH2 | chr1 | 119522074 | 119522530 | Hyper | cancer_general | TBX15 |
| chr1 | 119522839 | 119522940 | Hyper | cancer_general | TBX15 | chr1 | 119527072 | 119527391 | Hyper | liver_tcga, cancer_general | TBX15 |
| chr1 | 119527623 | 119527652 | Hyper | liver_tcga | TBX15 | chr1 | 119528653 | 119529118 | Hyper | cancer_general | TBX15 |
| chr1 | 119529804 | 119529839 | Hyper | cancer_general | TBX15 | chr1 | 119530100 | 119530725 | Hyper | liver_tcga, cancer_general | TBX15 |
| chr1 | 119531029 | 119531157 | Hyper | cancer_general | TBX15 | chr1 | 119532043 | 119532320 | Hyper | liver_tcga | TBX15 |
| chr1 | 119535816 | 119536377 | Hyper | cancer_general, liver_tcga | TBX15 | chr1 | 119542322 | 119542352 | Hyper | cancer_general | — |
| chr1 | 119542997 | 119543230 | Hyper | cancer_general | — | chr1 | 119543532 | 119544182 | Hyper | cancer_general | — |
| chr1 | 119548823 | 119548853 | Hyper | liver_tcga | — | chr1 | 119549058 | 119549929 | Hyper | liver_tcga, cancer_general | — |
| chr1 | 119550155 | 119550278 | Hyper | cancer_general | — | chr1 | 119550533 | 119550633 | Hyper | cancer_general | — |
| chr1 | 119550904 | 119551269 | Hyper | cancer_general | RIIAD1, CELF3 | chr1 | 145075523 | 145075552 | Hyper | liver_tcga | PDE4DIP |
| chr1 | 151693945 | 151694351 | Hyper | tcga, cancer_general | | chr1 | 151812413 | 151812442 | Hyper | liver_tcga | THEM5, LOC100132111, C2CD4D, RORC |
| chr1 | 152009415 | 152009510 | Hyper | hepatobiliary | S100A11, AC2 | chr1 | 152085398 | 152085504 | Hyper | cancer_general | TCHH |
| chr1 | 152488150 | 152488197 | Hyper | cancer_general | CRCT1, LCE5A | chr1 | 153651965 | 153652379 | Hyper | tcga, liver_tcga, cancer_general | ILF2, NPR1, TRNA_Met |
| chr1 | 154127987 | 154128016 | Hyper | literature | TPM3, NUP210L | chr1 | 154298320 | 154298557 | Hyper | tcga | ATP8B2, AQP10 |
| chr1 | 154475153 | 154475531 | Hyper | cancer_general | TDRD10, SHE | chr1 | 155043331 | 155043657 | Hyper | breast | EFNA4, ADAM15, EFNA3 |
| chr1 | 155164415 | 155164455 | Hyper | hepatobiliary | TRIM46, MIR92B, THBS3, DM075093, MUC1, AX746485 | chr1 | 155874151 | 155874300 | Hyper | literature | KIAA0907, RIT1 |
| chr1 | 155874508 | 155874546 | Hyper | literature | KIAA0907, RIT1 | chr1 | 156215329 | 156215359 | Hyper | cancer_general | PAQR6, BGLAP, SMG5 |
| chr1 | 156215607 | 156215805 | Hyper | cancer_general | SMG5, PAQR6, BGLAP | chr1 | 156357993 | 156358508 | Hyper | cancer_general | RHBG |
| chr1 | 156390135 | 156390698 | Hyper | cancer_general | C1orf61, MIR9-1 | chr1 | 156405518 | 156406431 | Hyper | tcga, cancer_general | C1orf61 |
| chr1 | 156594974 | 156595021 | Hyper | cancer_general | HAPLN2 | chr1 | 156611889 | 156612119 | Hyper | cancer_general | BC005081, BCAN |
| chr1 | 156626589 | 156626658 | Hyper | cancer_general | BCAN | chr1 | 156626891 | 156627034 | Hyper | cancer_general | BCAN |
| chr1 | 156646278 | 156646307 | Hyper | literature | NES | chr1 | 156646593 | 156646647 | Hyper | cancer_general | NES |

TABLE 11-continued

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 156814933 | 156815146 | Hyper | cancer_general | INSRR, NTRK1 | chr1 | 156815445 | 156815745 | Hyper | pancreas, cancer_general | INSRR, NTRK1 |
| chr1 | 156830269 | 156830348 | Hyper | tcga | NTRK1, INSRR | chr1 | 156863107 | 156863331 | Hyper | cancer_general | PEAR1 |
| chr1 | 156863662 | 156863724 | Hyper | cancer_general | PEAR1 | chr1 | 159138348 | 159158511 | Hyper | cancer_general | LOC100131825, CADM3 |
| chr1 | 161228659 | 161228891 | Hyper | tcga, cancer_general | PCP4L1 | chr1 | 161275564 | 161276026 | Hyper | cancer_general | SDHC, MPZ |
| chr1 | 161368993 | 161369405 | Hyper | head_neck | TRNA_Val | chr1 | 161369859 | 161369945 | Hyper | head_neck | TRNA_Val |
| chr1 | 161591472 | 161591546 | Hyper | cancer_general | FCGR3B, TRNA_Asn, TRNA_Glu, TRNA_Leu | chr1 | 162724401 | 162724430 | Hyper | literature | DDR2 |
| chr1 | 162729615 | 162729686 | Hyper | literature | DDR2 | chr1 | 162748392 | 162748421 | Hyper | literature | AF268386, Metazoa_SRP, DDR2 |
| chr1 | 162792306 | 162792533 | Hyper | cancer_general | C1orfl10, HSD17B7 | chr1 | 164290615 | 164290689 | Hyper | cancer_general | — |
| chr1 | 165086988 | 165087027 | Hyper | cancer_general | — | chr1 | 165205079 | 165205146 | Hyper | cancer_general | LMX1A |
| chr1 | 165321747 | 165321852 | Hyper | cancer_general | LMX1A | chr1 | 165323151 | 165323181 | Hyper | cancer_general | LMX1A |
| chr1 | 165324196 | 165324249 | Hyper | cancer_general | LMX1A | chr1 | 165324488 | 165324668 | Hyper | cancer_general | LMX1A |
| chr1 | 165325108 | 165325521 | Hyper | literature, cancer_general | LMX1A | chr1 | 165325896 | 165325950 | Hyper | cancer_general | LMX1A |
| chr1 | 165326204 | 165326469 | Hyper | cancer_general | LMX1A | chr1 | 165414191 | 165414272 | Hyper | cancer_general | RXRG |
| chr1 | 166134247 | 166134306 | Hyper | cancer_general | — | chr1 | 166134728 | 166134796 | Hyper | cancer_general | — |
| chr1 | 166135193 | 166135281 | Hyper | tcga | ILDR2 | chr1 | 166853563 | 166853592 | Hyper | liver_tcga | TADA1 |
| chr1 | 166890292 | 166890436 | Hyper | liver_tcga | DUSP27 | chr1 | 166916866 | 166917100 | Hyper | cancer_general | ILDR2 |
| chr1 | 167090617 | 167090757 | Hyper | liver_tcga | RCSD1 | chr1 | 167599179 | 167599330 | Hyper | cancer_general | RCSD1 |
| chr1 | 167599616 | 167599844 | Hyper | tcga, cancer_general | | chr1 | 169396376 | 169396923 | Hyper | cancer_general, literature | CCDC181 |
| chr1 | 170629540 | 170629569 | Hyper | literature | PRRX1 | chr1 | 170630055 | 170630084 | Hyper | liver_tcga, literature | — |
| chr1 | 170630456 | 170630810 | Hyper | literature, cancer_general, liver_tcga | PRRX1 | chr1 | 170631084 | 170631163 | Hyper | cancer_general | PRRX1 |
| chr1 | 170631477 | 170631559 | Hyper | cancer_general | PRRX1 | chr1 | 170633607 | 170633637 | Hyper | esophageal | PRRX1 |
| chr1 | 170637666 | 170637796 | Hyper | cancer_general | PRRX1 | chr1 | 170640517 | 170640691 | Hyper | cancer_general | PRRX1 |
| chr1 | 171810200 | 171810972 | Hyper | liver_tcga, cancer_general, literature | DNM3 | chr1 | 173638647 | 173639085 | Hyper | cancer_general | ANKRD45 |
| chr1 | 177133721 | 177133814 | Hyper | cancer_general | FAM5B | chr1 | 177140105 | 177140714 | Hyper | cancer_general | FAM5B |
| chr1 | 177150773 | 177150803 | Hyper | head_neck | FAM5B | chr1 | 179544967 | 179545098 | Hyper | cancer_general | — |
| chr1 | 179712164 | 179713399 | Hyper | tcga, cancer_general | FAM163A | chr1 | 180198061 | 180198209 | Hyper | cancer_general | LHX4 |
| chr1 | 180202424 | 180203016 | Hyper | cancer_general | LHX4 | chr1 | 180203413 | 180204924 | Hyper | tcga, lung, cancer_general | LHX4 |
| chr1 | 180882576 | 180882695 | Hyper | tcga | KIAA1614 | chr1 | 181287679 | 181287757 | Hyper | cancer_general | — |
| chr1 | 181288014 | 181288188 | Hyper | cancer_general | — | chr1 | 181451407 | 181452120 | Hyper | cancer_general | CACNA1E, Mir_544 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 181452871 | 181452967 | Hyper | cancer_general | Mir_544, CACNA1E | chr1 | 181454873 | 181454912 | Hyper | cancer_general | Mir_544, CACNA1E |
| chr1 | 181455183 | 181455263 | Hyper | cancer_general | Mir_544, CACNA1E | chr1 | 182584048 | 182584613 | Hyper | pancreas | LOC284648 |
| chr1 | 182921839 | 182921868 | Hyper | liver_tcga | SHCBP1L | chr1 | 183386150 | 183386288 | Hyper | cancer_general | — |
| chr1 | 183386500 | 183386626 | Hyper | cancer_general | — | chr1 | 183386838 | 183386964 | Hyper | cancer_general | RGL1 |
| chr1 | 183387266 | 183387319 | Hyper | cancer_general | — | chr1 | 183774244 | 183774363 | Hyper | blood | CR936711, FAM5C |
| chr1 | 184005701 | 184005814 | Hyper | cancer_general | COLGALT2 | chr1 | 190444855 | 190444885 | Hyper | cancer_general | CR936711, FAM5C |
| chr1 | 190445181 | 190445276 | Hyper | cancer_general | CR936711, FAM5C | chr1 | 190447373 | 190447519 | Hyper | cancer_general | — |
| chr1 | 196577628 | 196577858 | Hyper | tcga, cancer_general | — | chr1 | 196578101 | 196578150 | Hyper | cancer_general | — |
| chr1 | 197879400 | 197880156 | Hyper | liver_tcga, cancer_general | LHX9, C1orf53 | chr1 | 197882140 | 197882201 | Hyper | cancer_general | LHX9, C1orf53 |
| chr1 | 197882453 | 197882611 | Hyper | cancer_general | LHX9, C1orf53 | chr1 | 197887052 | 197887741 | Hyper | cancer_general | LHX9 |
| chr1 | 197888052 | 197888319 | Hyper | cancer_general | LHX9 | chr1 | 197888643 | 197889286 | Hyper | cancer_general | LHX9 |
| chr1 | 200009357 | 200009450 | Hyper | cancer_general | NR5A2 | chr1 | 200009750 | 200010114 | Hyper | cancer_general | NR5A2 |
| chr1 | 200011323 | 200012227 | Hyper | tcga, cancer_general, lung | NR5A2 | chr1 | 201368582 | 201368727 | Hyper | blood | TNNI1, LAD1 |
| chr1 | 201476501 | 201476619 | Hyper | liver_tcga | CSRP1 | chr1 | 202081571 | 202081641 | Hyper | pancreas | SYT2 |
| chr1 | 202183371 | 202183401 | Hyper | blood | LGR6 | chr1 | 202679215 | 202679518 | Hyper | tcga, esophageal | — |
| chr1 | 204499813 | 204499842 | Hyper | literature | MDM4 | chr1 | 204653561 | 204653807 | Hyper | cancer_general | — |
| chr1 | 205312596 | 205312950 | Hyper | cancer_general | KLHDC8A | chr1 | 205424654 | 205424957 | Hyper | cancer_general | AK095633, MIR135B |
| chr1 | 205537663 | 205537772 | Hyper | cancer_general | MFSD4 | chr1 | 207669496 | 207670060 | Hyper | cancer_general | CR1 |
| chr1 | 207818394 | 207818493 | Hyper | liver_tcga | CR1L, CR1 | chr1 | 208084289 | 208084488 | Hyper | cancer_general | CD34 |
| chr1 | 209381132 | 209381165 | Hyper | esophageal | — | chr1 | 209849170 | 209849199 | Hyper | tcga | G0S2 |
| chr1 | 209849430 | 209849459 | Hyper | tcga | G0S2 | chr1 | 210111146 | 210111176 | Hyper | cancer_general | SYT14 |
| chr1 | 210111388 | 210112140 | Hyper | tcga, cancer_general | SYT14 | chr1 | 213123871 | 213123979 | Hyper | hepatobiliary, tcga | VASH2 |
| chr1 | 213124653 | 213124910 | Hyper | liver_tcga, cancer_general | VASH2 | chr1 | 214156419 | 214156928 | Hyper | cancer_general | PROX1 |
| chr1 | 214158838 | 214158966 | Hyper | cancer_general | PROX1 | chr1 | 214160107 | 214160184 | Hyper | cancer_general | PROX1 |
| chr1 | 214360675 | 214360968 | Hyper | tcga, cancer_general | — | chr1 | 214724531 | 214724561 | Hyper | blood | PTPN14 |
| chr1 | 215255094 | 215255799 | Hyper | cancer_general | KCNK2 | chr1 | 216897216 | 216897307 | Hyper | cancer_general | — |
| chr1 | 217307486 | 217308274 | Hyper | liver_tcga | — | chr1 | 217309007 | 217309105 | Hyper | cancer_general | — |
| chr1 | 217311265 | 217311839 | Hyper | esophageal | — | chr1 | 217313042 | 217313747 | Hyper | cancer_general | SYT14 |
| chr1 | 218520074 | 218520399 | Hyper | tcga, cancer_general | TGFB2, CLO728463, RRP15 | chr1 | 218520775 | 218520805 | Hyper | liver_tcga | TGFB2, LOC728463, RRP15 |
| chr1 | 219346992 | 219347035 | Hyper | ovarian | LYPLAL1, LOC643723 | chr1 | 219347394 | 219347472 | Hyper | ovarian | LYPLAL1, LOC643723 |
| chr1 | 220101145 | 220101385 | Hyper | tcga, cancer_general | SLC30A10, RNU5F-1 | chr1 | 220101683 | 220101712 | Hyper | tcga | SLC30A10, RNU5F-1 |
| chr1 | 220700814 | 220700897 | Hyper | cancer_general | MARK1 | chr1 | 221052038 | 221052492 | Hyper | cancer_general | HLX |
| chr1 | 221053610 | 221053862 | Hyper | cancer_general | HLX | chr1 | 221067506 | 221067688 | Hyper | cancer_general | HLX |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr1 | 221068156 | 221068185 | Hyper | liver_tcga | HLX | chr1 | 221068793 | 221069150 | Hyper | liver_tcga | — |
| chr1 | 221737191 | 221737220 | Hyper | liver_tcga | — | chr1 | 223302825 | 223302890 | Hyper | cancer_general | — |
| chr1 | 223538344 | 223538641 | Hyper | tcga | SUSD4 | chr1 | 223936633 | 223937057 | Hyper | lung, cancer_general | CAPN2 |
| chr1 | 224363560 | 224363589 | Hyper | literature | DEGS1 | chr1 | 224528814 | 224528844 | Hyper | cancer_general | — |
| chr1 | 224803717 | 224803751 | Hyper | cancer_general | CNIH3 | chr1 | 224804097 | 224804791 | Hyper | liver_tcga, cancer_general | CNIH3 |
| chr1 | 224805131 | 224805808 | Hyper | cancer_general | CNIH3 | chr1 | 226411243 | 226411273 | Hyper | liver_tcga | LIN9, MIXL1 |
| chr1 | 226411700 | 226411832 | Hyper | tcga, liver_tcga | LIN9, MIXL1 | chr1 | 226814346 | 226814408 | Hyper | colorectal | ITPKB |
| chr1 | 226925067 | 226925195 | Hyper | tcga, cancer_general | ITPKB | chr1 | 227729780 | 227730075 | Hyper | cancer_general | — |
| chr1 | 227748700 | 227748733 | Hyper | liver_tcga, literature | ZNF678 | chr1 | 228194428 | 228194490 | Hyper | tcga | WNT3A |
| chr1 | 228195377 | 228196349 | Hyper | tcga, cancer_general | WNT3A | chr1 | 228247998 | 228248027 | Hyper | liver_tcga | WNT3A |
| chr1 | 228248302 | 228248332 | Hyper | cancer_general | WNT3A | chr1 | 228345999 | 228346195 | Hyper | liver_tcga | IBA57, GJC2, GUK1 |
| chr1 | 228463311 | 228463706 | Hyper | cancer_general | OBSCN | chr1 | 228566622 | 228566672 | Hyper | cancer_general | — |
| chr1 | 228604022 | 228604254 | Hyper | tcga, cancer_general | HIST3H3, TRIM17, TRIM11 | chr1 | 228633990 | 228634261 | Hyper | cancer_general | — |
| chr1 | 228645140 | 228645734 | Hyper | cancer_general, lung, tcga, liver_tcga | Histone3, HIST3H2A, HIST3H2BB, MIR4666A | chr1 | 228646032 | 228646238 | Hyper | tcga | MIR4666A, Histone3, HIST3H2BB, HIST3H2A |
| chr1 | 228651432 | 228651626 | Hyper | cancer_general | MIR4666A, HIST3H2BB, HIST3H2A, Histone3 | chr1 | 228651879 | 228652629 | Hyper | cancer_general | Histone3, MIR4666A, HIST3H2BB, HIST3H2A |
| chr1 | 228871865 | 228872003 | Hyper | blood | RHOU | chr1 | 229542838 | 229543139 | Hyper | cancer_general | — |
| chr1 | 229543553 | 229543603 | Hyper | liver_tcga | — | chr1 | 229566753 | 229568204 | Hyper | cancer_general | ACTA1, NUP133 |
| chr1 | 229569810 | 229569852 | Hyper | cancer_general | NUP133, ACTA1 | chr1 | 230561779 | 230561824 | Hyper | esophageal | PGBD5 |
| chr1 | 231297103 | 231297221 | Hyper | cancer_general | TRIM67 | chr1 | 231298595 | 231298772 | Hyper | tcga, liver_tcga | TRIM67 |
| chr1 | 232765195 | 232765301 | Hyper | blood | — | chr1 | 233750082 | 233750302 | Hyper | blood | MIR4427, KCNK1 |
| chr1 | 234040247 | 234040319 | Hyper | cancer_general | SLC35F3 | chr1 | 234040750 | 234041064 | Hyper | tcga, cancer_general | SLC35F3 |
| chr1 | 234041400 | 234041624 | Hyper | cancer_general | SLC35F3 | chr1 | 234349988 | 234350100 | Hyper | tcga, cancer_general | SLC35F3, AK054726 |
| chr1 | 235813781 | 235814202 | Hyper | cancer_general, tcga, literature | — | chr1 | 235814447 | 235814476 | Hyper | literature | LYST |
| chr1 | 236227637 | 236228096 | Hyper | cancer_general | AX747246, NID1 | chr1 | 236228582 | 236228789 | Hyper | tcga, cancer_general | AX747246, NID1 |
| chr1 | 236559176 | 236559271 | Hyper | cancer_general | EDARADD | chr1 | 236849457 | 236850142 | Hyper | cancer_general | ACTN2 |
| chr1 | 237205159 | 237205188 | Hyper | literature | RYR2 | chr1 | 237205434 | 237205478 | Hyper | cancer_general | RYR2 |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr1 | 237205687 | 237206735 | Hyper | tcga, cancer_general | RYR2 | chr1 | 239550594 | 239551193 | Hyper | cancer_general | CHRM3 |
| chr1 | 240016098 | 240016493 | Hyper | cancer_general | RPS7P5 | chr1 | 240254944 | 240255011 | Hyper | cancer_general | FMN2 |
| chr1 | 240255361 | 240255500 | Hyper | cancer_general | FMN2 | chr1 | 240255819 | 240256197 | Hyper | cancer_general | FMN2 |
| chr1 | 240256663 | 240256721 | Hyper | cancer_general | FMN2 | chr1 | 240775425 | 240775455 | Hyper | cancer_general | — |
| chr1 | 241520296 | 241520345 | Hyper | tcga | — | chr1 | 241520583 | 241520612 | Hyper | tcga | — |
| chr1 | 241587034 | 241587113 | Hyper | cancer_general | — | chr1 | 241587587 | 241587797 | Hyper | tcga, cancer_general | — |
| chr1 | 242686734 | 242687688 | Hyper | tcga, cancer_general | PLD5 | chr1 | 242688184 | 242688259 | Hyper | cancer_general | PLD5 |
| chr1 | 242688477 | 242688695 | Hyper | cancer_general | PLD5 | chr1 | 243646610 | 243646673 | Hyper | cancer_general | AKT3 |
| chr1 | 243859000 | 243859029 | Hyper | literature | — | chr1 | 244014301 | 244014376 | Hyper | esophageal | — |
| chr1 | 244080672 | 244080702 | Hyper | cancer_general | LOC339529 | chr1 | 244080963 | 244081203 | Hyper | tcga | LOC339529 |
| chr1 | 244893214 | 244893315 | Hyper | cancer_general | — | chr1 | 246952347 | 246952376 | Hyper | literature | LOC149134 |
| chr1 | 247496038 | 247496108 | Hyper | tcga | ZNF496 | chr1 | 248020479 | 248021349 | Hyper | liver_tcga, cancer_general | TRIM58 |
| chrX | 6145331 | 6145688 | Hyper | tcga, cancer_general | NLGN4X | chrX | 8698863 | 8698897 | Hyper | cancer_general | KAL1 |
| chrX | 8699504 | 8699566 | Hyper | cancer_general | KAL1 | chrX | 20148710 | 20148739 | Hyper | literature | SCARNA9L, EIF1AX |
| chrX | 47039370 | 47039399 | Hyper | literature | RBM10 | chrX | 47426106 | 47426144 | Hyper | literature | SYN1, ARAF |
| chrX | 47426780 | 47426821 | Hyper | literature | SYN1, ARAF | chrX | 50557045 | 50557075 | Hyper | liver_tcga | — |
| chrX | 64626567 | 64626596 | Hyper | liver_tcga | — | chrX | 66931448 | 66931477 | Hyper | literature | AR |
| chrX | 66937356 | 66937385 | Hyper | literature | AR | chrX | 66943529 | 66943567 | Hyper | literature | AR |
| chrX | 70339239 | 70339268 | Hyper | literature | MED12, IL2RG | chrX | 100740260 | 100740289 | Hyper | liver_tcga | ARMCX4 |
| chrX | 101906099 | 101906128 | Hyper | liver_tcga | GPRASP1 | chrX | 102000609 | 102000758 | Hyper | liver_tcga | BHLHB9 |
| chrX | 134156560 | 134156680 | Hyper | liver_tcga | FAM127A, FAM127C | chrX | 136656563 | 136656592 | Hyper | liver_tcga | ZIC3 |
| HCV | 111 | 140 | Hyper | virus | — | HCV | 374 | 403 | Hyper | virus | — |
| HCV | 637 | 666 | Hyper | virus | — | HCV | 900 | 929 | Hyper | virus | — |
| HCV | 1163 | 1192 | Hyper | virus | — | HCV | 1426 | 1455 | Hyper | virus | — |
| HCV | 1689 | 1718 | Hyper | virus | — | HCV | 1952 | 1981 | Hyper | virus | — |
| HCV | 2215 | 2244 | Hyper | virus | — | HCV | 2478 | 2507 | Hyper | virus | — |
| HCV | 2741 | 2770 | Hyper | virus | — | HCV | 3004 | 3033 | Hyper | virus | — |
| HCV | 3267 | 3296 | Hyper | virus | — | HCV | 3530 | 3559 | Hyper | virus | — |
| HCV | 3793 | 3822 | Hyper | virus | — | HCV | 4056 | 4085 | Hyper | virus | — |
| HCV | 4319 | 4348 | Hyper | virus | — | HCV | 4582 | 4611 | Hyper | virus | — |
| HCV | 4845 | 4874 | Hyper | virus | — | HCV | 5108 | 5137 | Hyper | virus | — |
| HCV | 5371 | 5400 | Hyper | virus | — | HCV | 5634 | 5663 | Hyper | virus | — |
| HCV | 5897 | 5926 | Hyper | virus | — | HCV | 6160 | 6189 | Hyper | virus | — |
| HCV | 6423 | 6452 | Hyper | virus | — | HCV | 6686 | 6715 | Hyper | virus | — |
| HCV | 6949 | 6978 | Hyper | virus | — | HCV | 7212 | 7241 | Hyper | virus | — |
| HCV | 7475 | 7504 | Hyper | virus | — | HCV | 7738 | 7767 | Hyper | virus | — |
| HCV | 8001 | 8030 | Hyper | virus | — | HCV | 8264 | 8293 | Hyper | virus | — |
| HCV | 8527 | 8556 | Hyper | virus | — | HCV | 8790 | 8819 | Hyper | virus | — |
| HCV | 9053 | 9082 | Hyper | virus | — | chr22 | 17081932 | 17082001 | Hyper | cancer_general | TPTEP1, CCT8L2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 17082566 | 17082595 | Hyper | liver_tcga | TPTEP1, CCT8L2 | chr22 | 17082943 | 17083003 | Hyper | cancer_general | TPTEP1, CCT8L2 |
| chr22 | 17083396 | 17083496 | Hyper | cancer_general, tcga | TPTEP1, CCT8L2 | chr22 | 17601086 | 17601368 | Hyper | cancer_general | BC021738, CECR6, IL17RA |
| chr22 | 17602511 | 17602624 | Hyper | cancer_general | IL17RA, BC021738, CECR6 | chr22 | 17850454 | 17850621 | Hyper | cancer_general | CECR2 |
| chr22 | 19017532 | 19017567 | Hyper | cancer_general | DGCR2, DGCR10, DGCR9 | chr22 | 19510799 | 19511567 | Hyper | liver_tcga, cancer_general | CLDN5, CDC45 |
| chr22 | 19511849 | 19512098 | Hyper | tcga, cancer_general | CLDN5, CDC45 | chr22 | 19702265 | 19702410 | Hyper | esophageal | SEPT5-GP1BB |
| chr22 | 19706171 | 19706677 | Hyper | cancer_general, tcga, lung | SEPT5-GP1BB | chr22 | 19742834 | 19742969 | Hyper | cancer_general | TBX1 |
| chr22 | 19748644 | 19748956 | Hyper | tcga, cancer_general | TBX1 | chr22 | 20792461 | 20792641 | Hyper | cancer_general, tcga | KLHL22, SCARF2 |
| chr22 | 21368587 | 21368617 | Hyper | esophageal | P2RX6, TUBA3FP, THAP7-AS1 | chr22 | 22005794 | 22006759 | Hyper | pancreas | MIR301B, MIR130B, SDF2L1 |
| chr22 | 22090595 | 22090742 | Hyper | cancer_general | YPEL1 | chr22 | 22862787 | 22863159 | Hyper | tcga, cancer_general | ZNF280A |
| chr22 | 24145484 | 24145513 | Hyper | literature | SMARCB1 | chr22 | 24180687 | 24180766 | Hyper | cancer_general | AK096976, DERL3 |
| chr22 | 24820330 | 24820396 | Hyper | esophageal | ADORA2A, ADORA2A-AS1, EU036692, SPECC1L | chr22 | 25678748 | 25679337 | Hyper | cancer_general | BC040576 |
| chr22 | 25817107 | 25817180 | Hyper | cancer_general |  | chr22 | 25817458 | 25817612 | Hyper | cancer_general | — |
| chr22 | 27053194 | 27053250 | Hyper | liver_tcga | MIAT | chr22 | 28198569 | 28198605 | Hyper | cancer_general | MN1 |
| chr22 | 28838200 | 28838292 | Hyper | lung | — | chr22 | 28838509 | 28838551 | Hyper | cancer_general | — |
| chr22 | 28839122 | 28839263 | Hyper | tcga | — | chr22 | 29091824 | 29091853 | Hyper | literature | CHEK2 |
| chr22 | 29876191 | 29876220 | Hyper | liver_tcga | KIAA0845, NEFH | chr22 | 29877223 | 29877299 | Hyper | cancer_general | KIAA0845, NEFH |
| chr22 | 30116904 | 30117162 | Hyper | tcga | ZMAT5, CABP7 | chr22 | 30476191 | 30476220 | Hyper | literature | HORMAD2 |
| chr22 | 30881582 | 30881612 | Hyper | head_neck | SEC14L4, SDC4P | chr22 | 30938521 | 30938584 | Hyper | cancer_general | SEC14L6 |
| chr22 | 31198492 | 31198637 | Hyper | blood | OSBP2 | chr22 | 31218510 | 31218540 | Hyper | cancer_general | OSBP2 |
| chr22 | 31218794 | 31218829 | Hyper | cancer_general | OSBP2 | chr22 | 31481130 | 31481332 | Hyper | tcga | SMTN |
| chr22 | 33197603 | 33197652 | Hyper | literature | TIMP3 | chr22 | 33453877 | 33454366 | Hyper | cancer_general | — |
| chr22 | 35656581 | 35656610 | Hyper | liver_tcga | HMGXB4 | chr22 | 36681295 | 36681341 | Hyper | liver_tcga | MYH9 |
| chr22 | 37720961 | 37721163 | Hyper | tcga | CYTH4 | chr22 | 38220653 | 38221201 | Hyper | cancer_general | GCAT, ANKRD54, GALR3 |
| chr22 | 38477069 | 38477794 | Hyper | cancer_general | BAIAP2L2, SLC16A8, PICK1 | chr22 | 39784480 | 39784598 | Hyper | liver_tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr22 | 39853521 | 39853592 | Hyper | colorectal | MGAT3 | chr22 | 39954413 | 39954516 | Hyper | cancer_general | — |
| chr22 | 40807034 | 40807063 | Hyper | liver_tcga | MKL1, SGSM3 | chr22 | 42310087 | 42310220 | Hyper | cancer_general | SHISA8 |
| chr22 | 42311521 | 42311587 | Hyper | cancer_general | TNFRSF13C, SHISA8 | chr22 | 42353611 | 42353892 | Hyper | cancer_general | LINC00634 |
| chr22 | 42679729 | 42679841 | Hyper | cancer_general | LOC388906 | chr22 | 43740084 | 43740128 | Hyper | cancer_general | — |
| chr22 | 43808280 | 43808428 | Hyper | cancer_general | MPPED1 | chr22 | 44208418 | 44208448 | Hyper | esophageal | — |
| chr22 | 44258366 | 44258506 | Hyper | cancer_general | SULT4A1 | chr22 | 44287650 | 44287696 | Hyper | cancer_general | PNPLA5 |
| chr22 | 45403086 | 45403133 | Hyper | cancer_general | PHF21B | chr22 | 45403478 | 45403714 | Hyper | tcga | PHF21B |
| chr22 | 45404197 | 45404433 | Hyper | tcga, cancer_general | PHF21B | chr22 | 45404994 | 45405061 | Hyper | cancer_general | PHF21B |
| chr22 | 45405318 | 45405418 | Hyper | tcga | PHF21B | chr22 | 45405620 | 45405768 | Hyper | liver_tcga | PHF21B |
| chr22 | 45406271 | 45406328 | Hyper | cancer_general | PHF21B | chr22 | 45719161 | 45719190 | Hyper | liver_tcga | DQ586951, FAM118A |
| chr22 | 46262452 | 46263809 | Hyper | tcga, cancer_general | — | chr22 | 46276749 | 46276820 | Hyper | cancer_general | — |
| chr22 | 46368029 | 46368059 | Hyper | cancer_general | WNT7B | chr22 | 46658791 | 46658846 | Hyper | cancer_general | TTC38, PKDREJ |
| chr22 | 46933089 | 46933237 | Hyper | liver_tcga | — | chr22 | 48885031 | 48885061 | Hyper | cancer_general | FAM19A5 |
| chr22 | 48885296 | 48885901 | Hyper | cancer_general | FAM19A5 | chr22 | 48886659 | 48886849 | Hyper | cancer_general | FAM19A5 |
| chr22 | 48971130 | 48971748 | Hyper | cancer_general | FAM19A5 | chr22 | 48972144 | 48972657 | Hyper | tcga, cancer_general | FAM19A5 |
| chr22 | 50064721 | 50064944 | Hyper | tcga | MLC1 | chr22 | 50496841 | 50496918 | Hyper | cancer_general | MLC1 |
| chr22 | 50497147 | 50497287 | Hyper | cancer_general | — | chr22 | 50623672 | 50623815 | Hyper | literature, cancer_general | TRABD, PANX2 |
| chr22 | 50943093 | 50943262 | Hyper | head_neck | NCAPH2, LMF2 | chr22 | 51042278 | 51042810 | Hyper | cancer_general | MAPK8IP2 |
| chr22 | 51112150 | 51112232 | Hyper | tcga | SHANK3 | chr6 | 391173 | 392000 | Hyper | tcga, liver_tcga, cancer_general | IRF4 |
| chr6 | 392307 | 393650 | Hyper | liver_tcga, tcga, cancer_general | IRF4 | chr6 | 711142 | 711293 | Hyper | pancreas | AX747750 |
| chr6 | 1312000 | 1312096 | Hyper | blood | FOXQ1 | chr6 | 1312356 | 1312708 | Hyper | blood | FOXQ1 |
| chr6 | 1314088 | 1314118 | Hyper | blood | FOXQ1 | chr6 | 1378222 | 1379242 | Hyper | tcga, cancer_general | — |
| chr6 | 1379584 | 1379614 | Hyper | cancer_general | — | chr6 | 1379909 | 1379952 | Hyper | cancer_general | — |
| chr6 | 1383677 | 1384644 | Hyper | cancer_general, tcga | FOXF2 | chr6 | 1385118 | 1385170 | Hyper | cancer_general | FOXF2 |
| chr6 | 1386071 | 1386112 | Hyper | cancer_general | FOXF2 | chr6 | 1389124 | 1389262 | Hyper | cancer_general | FOXF2 |
| chr6 | 1390241 | 1391035 | Hyper | cancer_general | FOXF2 | chr6 | 1391318 | 1391379 | Hyper | cancer_general | FOXF2 |
| chr6 | 1524199 | 1524283 | Hyper | cancer_general | — | chr6 | 1605387 | 1605454 | Hyper | cancer_general | FOXC1 |
| chr6 | 1614833 | 1615184 | Hyper | cancer_general | GMDS, FOXC1 | chr6 | 1620672 | 1620701 | Hyper | liver_tcga | FOXC1, GMDS |
| chr6 | 1624977 | 1625818 | Hyper | liver_tcga, cancer_general | GMDS | chr6 | 3229029 | 3229059 | Hyper | cancer_general | AK096219, TUBB2A, TUBB2B |
| chr6 | 3229423 | 3229510 | Hyper | cancer_general | AK096219, TUBB2A, TUBB2B | chr6 | 3232010 | 3232260 | Hyper | tcga | AK096219, TUBB2A, TUBB2B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 4775062 | 4775222 | Hyper | liver tcga | CDYL | chr6 | 5996952 | 5996989 | Hyper | cancer_general | NRN1 |
| chr6 | 5997802 | 5997832 | Hyper | cancer_general | NRN1 | chr6 | 6003287 | 6005417 | Hyper | liver tcga, cancer_general | NRN1 |
| chr6 | 6006374 | 6006419 | Hyper | cancer_general | NRN1 | chr6 | 6006674 | 6006883 | Hyper | cancer_general | NRN1 |
| chr6 | 6007593 | 6008277 | Hyper | literature | NRN1 | chr6 | 7726334 | 7726363 | Hyper | literature | BMP6 |
| chr6 | 7726630 | 7726659 | Hyper | literature, cancer_general | BMP6 | chr6 | 7726952 | 7726981 | Hyper | literature | BMP6 |
| chr6 | 7727699 | 7728142 | Hyper | cancer_general | BMP6 | chr6 | 7728849 | 7728941 | Hyper | literature, cancer_general | BMP6 |
| chr6 | 10381507 | 10382299 | Hyper | cancer_general | — | chr6 | 10382722 | 10383049 | Hyper | cancer_general | — |
| chr6 | 10383739 | 10383774 | Hyper | cancer_general | — | chr6 | 10384950 | 10385939 | Hyper | cancer_general | — |
| chr6 | 10386210 | 10386273 | Hyper | cancer_general | — | chr6 | 10390023 | 10391187 | Hyper | cancer_general | TFAP2A |
| chr6 | 10410518 | 10410578 | Hyper | cancer_general | LOC100130275, TFAP2A | chr6 | 10411356 | 10411510 | Hyper | cancer_general | LOC100130275, TFAP2A |
| chr6 | 10415113 | 10415215 | Hyper | cancer_general | LOC100130275, TFAP2A | chr6 | 10415559 | 10415713 | Hyper | cancer_general | LOC100130275, TFAP2A |
| chr6 | 10416118 | 10416351 | Hyper | lung, cancer_general | LOC100130275, TFAP2A | chr6 | 10417158 | 10417557 | Hyper | cancer_general | LOC100130275, TFAP2A |
| chr6 | 10419086 | 10419506 | Hyper | cancer_general | LINC00518, LOC100130275, TFAP2A | chr6 | 10419744 | 10419941 | Hyper | cancer_general | LINC00518, LOC100130275, TFAP2A |
| chr6 | 10421053 | 10422635 | Hyper | literature, cancer_general | LINC00518, LOC100130275, TFAP2A | chr6 | 10423613 | 10423704 | Hyper | cancer_general | TFAP2A, LINC00518, LOC100130275 |
| chr6 | 10425496 | 10426884 | Hyper | cancer_general | LINC00518, LOC100130275, TFAP2A | chr6 | 10881835 | 10882057 | Hyper | cancer_general | SYCP2L, GCM2 |
| chr6 | 10882321 | 10882350 | Hyper | literature | SYCP2L, GCM2 | chr6 | 10883008 | 10883038 | Hyper | cancer_general | SYCP2L, GCM2 |
| chr6 | 10883444 | 10883474 | Hyper | cancer_general | GCM2, SYCP2L | chr6 | 10887078 | 10887686 | Hyper | cancer_general | SYCP2L, GCM2 |
| chr6 | 11044062 | 11044572 | Hyper | tcga, cancer_general | ELOVL2, ELOVL2-AS1 | chr6 | 12749899 | 12749976 | Hyper | cancer_general | PHACTR1 |
| chr6 | 12750210 | 12750255 | Hyper | cancer_general | PHACTR1 | chr6 | 17281417 | 17281534 | Hyper | cancer_general | RBM24 |
| chr6 | 19691638 | 19691841 | Hyper | cancer_general | — | chr6 | 19692066 | 19692318 | Hyper | liver tcga, cancer_general | — |
| chr6 | 19837064 | 19837140 | Hyper | cancer_general | ID4 | chr6 | 21664719 | 21664749 | Hyper | cancer_general | LINC00340 |
| chr6 | 21665004 | 21665043 | Hyper | cancer_general | LINC00340 | chr6 | 24358291 | 24358320 | Hyper | liver_tcga | KAAG1, DCDC2 |
| chr6 | 24360074 | 24360170 | Hyper | hepatobiliary | DCDC2, KAAG1 | chr6 | 24494679 | 24494766 | Hyper | cancer_general | ALDH5A1, GPLD1 |
| chr6 | 26034268 | 26034311 | Hyper | cancer_general | HIST1H2BB, HIST1H2AB, HIST1H3B, HIST1H4B | chr6 | 26184095 | 26184391 | Hyper | cancer_general | HIST1H4D, HIST1H2BE |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 26188696 | 26189393 | Hyper | cancer_general | HIST1H3F, HIST1H2AD, HIST1H4D, HIST1H3D | chr6 | 26199137 | 26199167 | Hyper | pancreas | HIST1H2BF, HIST1H4E, HIST1H2AD, HIST1H3F, HIST1H3D, HIST1H4D |
| chr6 | 26199686 | 26199716 | Hyper | pancreas | HIST1H2BF, HIST1H4E, HIST1H2AD, HIST1H3F, HIST1H3D | chr6 | 26235223 | 26235623 | Hyper | tcga, liver_tcga | HIST1H3E, HIST1H4F, HIST1H4F, HIST1H1D |
| chr6 | 26240504 | 26241118 | Hyper | liver_tcga, cancer_general | HIST1H4G, HIST1H3F, HIST1H1D, HIST1H4F | chr6 | 26250468 | 26250826 | Hyper | liver_tcga, cancer_general | HIST1H4F, HIST1H2BH, HIST1H3F, HIST1H4G |
| chr6 | 26251054 | 26251182 | Hyper | cancer_general | HIST1H2BH, HIST1H3F, HIST1H4G | chr6 | 26251816 | 26252151 | Hyper | liver_tcga, cancer_general | HIST1H2BH, HIST1H3F, HIST1H4G |
| chr6 | 26271406 | 26271762 | Hyper | cancer_general | BC079832, HIST1H2BI, HIST1H4H, HIST1H3G | chr6 | 26271971 | 26272001 | Hyper | cancer_general | BC079832, HIST1H2BI, HIST1H4H, HIST1H3G |
| chr6 | 26272512 | 26272617 | Hyper | cancer_general | HIST1H2BI, HIST1H4H, BC079832, HIST1H3G | chr6 | 26273400 | 26273480 | Hyper | cancer_general | HIST1H3G, HIST1H4H, HIST1H2BI, BC079832 |
| chr6 | 26284811 | 26284898 | Hyper | hepatobiliary | HIST1H4H, TRNA_Met | chr6 | 26327806 | 26327982 | Hyper | cancer_general | TRNA_Ser, TRNA_Arg, TRNA_Met, TRNA_Trp |
| chr6 | 26328294 | 26328457 | Hyper | cancer_general | TRNA_Arg, TRNA_Met, TRNA_Trp, TRNA_Ser | chr6 | 26332178 | 26332218 | Hyper | lung | TRNA_Trp, TRNA_Met, TRNA_Arg, TRNA_Ser |
| chr6 | 26501857 | 26502209 | Hyper | tcga, cancer_general | BTN1A1 | chr6 | 26550994 | 26551034 | Hyper | cancer_general | TRNA_Ile, TRNA_Pro, TRNA_Lys, HMGN4, TRNA_Ala |
| chr6 | 26577158 | 26577475 | Hyper | cancer_general | TRNA_Tyr, TRNA_Ala, BC033330 | chr6 | 26987967 | 26988166 | Hyper | blood | TRNA_Ile, LOC100270746, LINC00240 |
| chr6 | 27059783 | 27059848 | Hyper | cancer_general | TRNA_Ser, TRNA_Pro | chr6 | 27064682 | 27065198 | Hyper | cancer_general | TRNA_Ser, TRNA_Pro |
| chr6 | 27173528 | 27174181 | Hyper | tcga, cancer_general | TRNA_Val, TRNA_Ser, TRNA_Arg | chr6 | 27182869 | 27182899 | Hyper | cancer_general | TRNA_Arg, TRNA_Ser, TRNA_Val |
| chr6 | 27203269 | 27203363 | Hyper | cancer_general | TRNA_Val, TRNA_Ile, TRNA_Leu | chr6 | 27205300 | 27205441 | Hyper | cancer_general | TRNA_Ile, TRNA_Val, TRNA_Leu |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 27205671 | 27206040 | Hyper | cancer_general | TRNA_Ile, TRNA_Val, TRNA_Leu, PRSS16 | chr6 | 27218951 | 27218980 | Hyper | liver_tcga | PRSS16 |
| chr6 | 27228180 | 27228395 | Hyper | cancer_general | PRSS16 | chr6 | 27235876 | 27235905 | Hyper | literature | TRNA_Ile |
| chr6 | 27247636 | 27247724 | Hyper | cancer_general | TRNA_Val, TRNA_Pseudo, TRNA_Ile | chr6 | 27256097 | 27256173 | Hyper | cancer_general | TRNA_Val, TRNA_Pseudo, TRNA_Gln, TRNA_Ser |
| chr6 | 27256383 | 27256420 | Hyper | cancer_general | TRNA_Val, TRNA_Pseudo, TRNA_Gln, TRNA_Ser | chr6 | 27264332 | 27264364 | Hyper | cancer_general | TRNA_Thr, TRNA_Gln, TRNA_Pseudo, TRNA_Val, TRNA_Ser |
| chr6 | 27279845 | 27280012 | Hyper | cancer_general | POM121L2, TRNA_Thr | chr6 | 27463029 | 27463687 | Hyper | liver_tcga, cancer_general | TRNA_Ser, TRNA_Asp |
| chr6 | 27512761 | 27513487 | Hyper | cancer_general | TRNA_Ser, TRNA_Gln | chr6 | 27533822 | 27534341 | Hyper | cancer_general | TRNA_Lys, TRNA_Arg |
| chr6 | 27559809 | 27560075 | Hyper | cancer_general | TRNA_Met, TRNA_Lys, TRNA_Asp | chr6 | 27573171 | 27573392 | Hyper | cancer_general | TRNA_Leu |
| chr6 | 27598738 | 27598860 | Hyper | cancer_general | TRNA_Ile | chr6 | 27599159 | 27599341 | Hyper | cancer_general | TRNA_Ile |
| chr6 | 27635265 | 27635434 | Hyper | cancer_general | TRNA_Ile, TRNA_Arg, TRNA_Ser, TRNA_Phe | chr6 | 27647712 | 27647896 | Hyper | liver_tcga, literature | TRNA_Thr, TRNA_Ile, TRNA_Ser, TRNA_Arg, TRNA_Val |
| chr6 | 27648912 | 27649134 | Hyper | cancer_general, literature | TRNA_Ser, TRNA_Val, TRNA_Thr, TRNA_Ile | chr6 | 27725187 | 27725308 | Hyper | liver_tcga | LOC100131289, TRNA_Val |
| chr6 | 27783039 | 27783068 | Hyper | liver_tcga | HIST1H2BI, HIST1H4J, HIST1H2BM, HIST1H2AJ, HIST1H3H | chr6 | 27994464 | 27799581 | Hyper | pancreas | HIST1H2AK, HIST1H2BN, HIST1H4K, BC016143, FKSG63, HIST1H4J |
| chr6 | 27834676 | 27834835 | Hyper | cancer_general | HIST1H3I, HIST1H4L, HIST1H1B, HIST1H2AL | chr6 | 27835047 | 27835417 | Hyper | cancer_general | HIST1H1B, HIST1H2AL, HIST1H3I, HIST1H4L |
| chr6 | 27839726 | 27840082 | Hyper | cancer_general | HIST1H4L, HIST1H3I, HIST1H1B, HIST1H2AL | chr6 | 27840543 | 27840617 | Hyper | cancer_general | HIST1H4L, HIST1H3I, HIST1H1B, HIST1H2AL |
| chr6 | 27841104 | 27841136 | Hyper | cancer_general | HIST1H4L, HIST1H3I, HIST1H1B, HIST1H2AL | chr6 | 27858515 | 27858637 | Hyper | liver_tcga, cancer_general | HIST1H2AM, HIST1H2BO, HIST1H3J |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 28175189 | 28176212 | Hyper | tcga, cancer_general | TRNA_Ser, TOB2P1 | chr6 | 28227076 | 28227141 | Hyper | literature | ZSCAN26, NKAPL, ZKSCAN4 |
| chr6 | 28303562 | 28303607 | Hyper | lung | ZSCAN31 | chr6 | 28303815 | 28304263 | Hyper | tcga, lung | ZSCAN31 |
| chr6 | 28367109 | 28367774 | Hyper | tcga, cancer_general | ZSCAN12 | chr6 | 28410976 | 28411553 | Hyper | cancer_general | ZSCAN23 |
| chr6 | 28414977 | 28415034 | Hyper | cancer_general | — | chr6 | 28457608 | 28457638 | Hyper | cancer_general | TRNA_Thr |
| chr6 | 28457870 | 28458158 | Hyper | cancer_general | TRNA_Thr | chr6 | 28956323 | 28956719 | Hyper | liver_tcga | TRNA_Leu, ZNF311, TRNA_Glu, TRNA_Phe |
| chr6 | 30095418 | 30095570 | Hyper | liver_tcga | TRIM40, DQ580846 | chr6 | 30644680 | 30644798 | Hyper | liver_tcga | PPP1R18 |
| chr6 | 34113893 | 34113922 | Hyper | tcga | — | chr6 | 35182493 | 35182522 | Hyper | liver_tcga | SCUBE3, AY927475 |
| chr6 | 35479613 | 35479642 | Hyper | literature | TULP1 | chr6 | 35992428 | 35992458 | Hyper | cancer_general | MAPK14, SLC26A8 |
| chr6 | 36252984 | 36253171 | Hyper | cancer_general | PNPLA1 | chr6 | 36808323 | 36808441 | Hyper | cancer_general | AK096023, CPNE5 |
| chr6 | 37664140 | 37664187 | Hyper | cancer_general | — | chr6 | 37673320 | 37673611 | Hyper | tcga | — |
| chr6 | 38683206 | 38683235 | Hyper | liver_tcga | DNAH8 | chr6 | 39281088 | 39281133 | Hyper | cancer_general | KCNK17, KCNK16 |
| chr6 | 39281824 | 39281875 | Hyper | cancer_general | KCNK16, KCNK17 | chr6 | 39329863 | 39329892 | Hyper | literature | KIF6 |
| chr6 | 39760401 | 39760661 | Hyper | tcga | DAAM2 | chr6 | 40554653 | 40554699 | Hyper | cancer_general | LRFN2 |
| chr6 | 41337072 | 41337128 | Hyper | cancer_general | — | chr6 | 41339263 | 41339838 | Hyper | cancer_general | — |
| chr6 | 41340902 | 41341182 | Hyper | tcga, cancer_general | — | chr6 | 41341501 | 41341549 | Hyper | cancer_general | — |
| chr6 | 41342243 | 41342275 | Hyper | cancer_general | — | chr6 | 41342807 | 41342837 | Hyper | cancer_general | — |
| chr6 | 41605937 | 41606542 | Hyper | tcga, cancer_general | MDFI | chr6 | 42738966 | 42739049 | Hyper | liver_tcga | — |
| chr6 | 42879554 | 42879718 | Hyper | cancer_general | PTCRA | chr6 | 42928321 | 42928454 | Hyper | blood | GNMT, BC040637, PEX6 |
| chr6 | 43211193 | 43211311 | Hyper | literature, liver_tcga | TTBK1 | chr6 | 43612825 | 43613067 | Hyper | cancer_general | RSPH9, MAD2L1BP |
| chr6 | 45388716 | 45388775 | Hyper | cancer_general | RUNX2 | chr6 | 46702982 | 46703123 | Hyper | liver_tcga | PLA2G7 |
| chr6 | 46703350 | 46703436 | Hyper | cancer_general | PLA2G7 | chr6 | 50674372 | 50674750 | Hyper | literature, cancer_general | TFAP2D |
| chr6 | 50681699 | 50681942 | Hyper | cancer_general | TFAP2D | chr6 | 50682319 | 50682386 | Hyper | cancer_general | TFAP2D |
| chr6 | 50682659 | 50683227 | Hyper | cancer_general | TFAP2D | chr6 | 50684939 | 50684969 | Hyper | cancer_general | TFAP2D |
| chr6 | 50689913 | 50690039 | Hyper | cancer_general | TFAP2D | chr6 | 50691065 | 50691095 | Hyper | lung | TFAP2D |
| chr6 | 50692083 | 50692481 | Hyper | cancer_general | TFAP2B | chr6 | 50787216 | 50788352 | Hyper | cancer_general | TFAP2B |
| chr6 | 50789374 | 50789404 | Hyper | cancer_general | TFAP2B | chr6 | 50791187 | 50791632 | Hyper | cancer_general, literature | TFAP2B |
| chr6 | 50793335 | 50793404 | Hyper | cancer_general | TFAP2B | chr6 | 50793728 | 50793882 | Hyper | cancer_general | TFAP2B |
| chr6 | 50794531 | 50794693 | Hyper | cancer_general | TFAP2B | chr6 | 50803834 | 50803867 | Hyper | cancer_general | TFAP2B |
| chr6 | 50804131 | 50804368 | Hyper | cancer_general | TFAP2B | chr6 | 50808681 | 50808854 | Hyper | cancer_general | TFAP2B |
| chr6 | 50810551 | 50810839 | Hyper | cancer_general | TFAP2B | chr6 | 50811062 | 50811488 | Hyper | cancer_general | TFAP2B |
| chr6 | 50813258 | 50813939 | Hyper | cancer_general | TFAP2B | chr6 | 50814569 | 50814599 | Hyper | cancer_general | TFAP2B |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 50817023 | 50817229 | Hyper | cancer_general | TFAP2B | chr6 | 50817905 | 50817935 | Hyper | cancer_general | TFAP2B |
| chr6 | 50818449 | 50818706 | Hyper | cancer_general | TFAP2B | chr6 | 50818920 | 50819000 | Hyper | cancer_general | TFAP2B |
| chr6 | 52227752 | 52227781 | Hyper | tcga | PAQR8 | chr6 | 52228008 | 52228037 | Hyper | tcga | PAQR8 |
| chr6 | 53212491 | 53213970 | Hyper | esophageal | — | chr6 | 54711448 | 54711626 | Hyper | blood | FAM83B |
| chr6 | 55443691 | 55443946 | Hyper | cancer_general | HMGCLL1 | chr6 | 56112262 | 56112386 | Hyper | cancer_general | COL21A1 |
| chr6 | 56716332 | 56716410 | Hyper | cancer_general | — | chr6 | 56818656 | 56818937 | Hyper | cancer_general | BEND6 |
| chr6 | 56819217 | 56819637 | Hyper | cancer_general, tcga, liver_tcga | BEND6 | chr6 | 56819897 | 56819926 | Hyper | liver_tcga | BEND6 |
| chr6 | 58147447 | 58147480 | Hyper | cancer_general | TRNA_Ile, TRNA_Ala, KHDRBS2 | chr6 | 58147790 | 58147976 | Hyper | cancer_general | TRNA_Ala, TRNA_Ile, KHDRBS2 |
| chr6 | 62995356 | 62996146 | Hyper | tcga, cancer_general | — | chr6 | 62996443 | 62996489 | Hyper | cancer_general | — |
| chr6 | 70992057 | 70992162 | Hyper | cancer_general | COL9A1 | chr6 | 70992415 | 70992560 | Hyper | cancer_general | COL9A1 |
| chr6 | 70992830 | 70993015 | Hyper | cancer_general | COL9A1 | chr6 | 71665638 | 71665723 | Hyper | esophageal | B3GAT2 |
| chr6 | 71666788 | 71666986 | Hyper | tcga, cancer_general | B3GAT2 | chr6 | 72129789 | 72129829 | Hyper | cancer_general | LINC00472 |
| chr6 | 72130107 | 72130464 | Hyper | tcga, cancer_general | LINC00472 | chr6 | 72596120 | 72596315 | Hyper | tcga, pancreas | RIMS1 |
| chr6 | 72596950 | 72596980 | Hyper | cancer_general | RIMS1 | chr6 | 73329784 | 73330126 | Hyper | cancer_general | KCNQ5 |
| chr6 | 73330834 | 73331304 | Hyper | tcga, cancer_general | KCNQ5 | chr6 | 73331515 | 73333122 | Hyper | cancer_general, colorectal, tcga | KCNQ5 |
| chr6 | 76059561 | 76059787 | Hyper | tcga | — | chr6 | 78172177 | 78172572 | Hyper | tcga, literature, cancer_general | HTR1B |
| chr6 | 78173212 | 78173264 | Hyper | literature | HTR1B | chr6 | 78173696 | 78173984 | Hyper | cancer_general | HTR1B |
| chr6 | 78176458 | 78176820 | Hyper | cancer_general | HTR1B | chr6 | 79620399 | 79620699 | Hyper | tcga, cancer_general | IRAK1BP1 |
| chr6 | 80656930 | 80657180 | Hyper | cancer_general | ELOVL4 | chr6 | 82463270 | 82463310 | Hyper | blood | FAM46A |
| chr6 | 84141298 | 84141412 | Hyper | pancreas | ME1 | chr6 | 84417436 | 84417778 | Hyper | cancer_general | SNAP91 |
| chr6 | 84418172 | 84418281 | Hyper | cancer_general | SNAP91 | chr6 | 84418644 | 84418803 | Hyper | cancer_general, tcga, liver_tcga | SNAP91 |
| chr6 | 84191157 | 84419415 | Hyper | cancer_general | SNAP91 | chr6 | 84562873 | 84563242 | Hyper | cancer_general, tcga | RIPPLY2, CYB5R4 |
| chr6 | 84563489 | 84563542 | Hyper | cancer_general | CYB5R4, RIPPLY2 | chr6 | 85472407 | 85473703 | Hyper | tcga, cancer_general | TBX18 |
| chr6 | 85473928 | 85474378 | Hyper | tcga, liver_tcga, cancer_general | TBX18 | chr6 | 85474594 | 85474736 | Hyper | cancer_general | TBX18 |
| chr6 | 85476233 | 85476285 | Hyper | cancer_general | TBX18 | chr6 | 85476998 | 85477028 | Hyper | cancer_general | TBX18 |
| chr6 | 85478514 | 85478724 | Hyper | cancer_general | TBX18 | chr6 | 85482530 | 85482822 | Hyper | cancer_general | TBX18 |
| chr6 | 85483345 | 85483375 | Hyper | cancer_general | TBX18 | chr6 | 85483635 | 85484920 | Hyper | cancer_general | TBX18 |
| chr6 | 87647114 | 87647143 | Hyper | literature | HTR1E | chr6 | 87862092 | 87862172 | Hyper | cancer_general | ZNF292 |
| chr6 | 88876963 | 88877437 | Hyper | cancer_general | — | chr6 | 91320285 | 91320318 | Hyper | cancer_general | — |
| chr6 | 91320949 | 91321295 | Hyper | tcga | — | chr6 | 94126973 | 94127064 | Hyper | cancer_general | EPHA7 |
| chr6 | 94127455 | 94127544 | Hyper | cancer_general | EPHA7 | chr6 | 94128365 | 94128399 | Hyper | cancer_general | EPHA7 |
| chr6 | 94129219 | 94129257 | Hyper | tcga | EPHA7 | chr6 | 94129509 | 94129575 | Hyper | cancer_general | EPHA7 |
| chr6 | 96464100 | 96464204 | Hyper | cancer_general | FUT9 | chr6 | 99271926 | 99272810 | Hyper | cancer_general | POU3F2 |
| chr6 | 99273369 | 99273410 | Hyper | cancer_general | POU3F2 | chr6 | 99277180 | 99277330 | Hyper | cancer_general | POU3F2 |
| chr6 | 99279556 | 99279612 | Hyper | cancer_general | POU3F2 | chr6 | 99280557 | 99280744 | Hyper | cancer_general | POU3F2 |
| chr6 | 99281014 | 99281385 | Hyper | cancer_general | POU3F2 | chr6 | 99283512 | 99283582 | Hyper | cancer_general | POU3F2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 99290360 | 99290398 | Hyper | cancer_general | POU3F2 | chr6 | 99290657 | 99290693 | Hyper | cancer_general | POU3F2 |
| chr6 | 99291264 | 99291438 | Hyper | cancer_general | POU3F2 | chr6 | 99292252 | 99292417 | Hyper | cancer_general | POU3F2 |
| chr6 | 99295726 | 99296467 | Hyper | cancer_general | POU3F2 | chr6 | 99842067 | 99842258 | Hyper | tcga | PNISR, BC033061, COQ3 |
| chr6 | 100038682 | 100038964 | Hyper | cancer_general | — | chr6 | 100039259 | 100039289 | Hyper | cancer_general | — |
| chr6 | 100050754 | 100051971 | Hyper | cancer_general | PRDM13 | chr6 | 100053221 | 100053511 | Hyper | cancer_general | PRDM13 |
| chr6 | 100054866 | 100054917 | Hyper | cancer_general | PRDM13 | chr6 | 100061022 | 100061076 | Hyper | cancer_general | PRDM13 |
| chr6 | 100061311 | 100061419 | Hyper | cancer_general | PRDM13 | chr6 | 100061757 | 100061835 | Hyper | cancer_general | PRDM13 |
| chr6 | 100062178 | 100062586 | Hyper | cancer_general | PRDM13 | chr6 | 100062944 | 100063068 | Hyper | cancer_general | PRDM13 |
| chr6 | 100441364 | 100441966 | Hyper | cancer_general | MCHR2, LOC728012 | chr6 | 100903384 | 100903631 | Hyper | cancer_general | SIM1 |
| chr6 | 100904214 | 100904275 | Hyper | cancer_general | SIM1 | chr6 | 100905969 | 100906016 | Hyper | cancer_general | SIM1 |
| chr6 | 100911686 | 100911723 | Hyper | literature | SIM1 | chr6 | 100912070 | 100912119 | Hyper | cancer_general | SIM1 |
| chr6 | 100912421 | 100912480 | Hyper | cancer_general | SIM1 | chr6 | 100912919 | 100913149 | Hyper | liver_tcga, literature, cancer_general | SIM1 |
| chr6 | 100915101 | 100915205 | Hyper | liver_tcga, cancer_general | SIM1 | chr6 | 101840708 | 101840820 | Hyper | cancer_general | GRIK2 |
| chr6 | 101846782 | 101846811 | Hyper | literature | GRIK2 | chr6 | 101847185 | 101847215 | Hyper | cancer_general | GRIK2 |
| chr6 | 101850147 | 101850275 | Hyper | cancer_general | GRIK2 | chr6 | 101850570 | 101850600 | Hyper | cancer_general | GRIK2 |
| chr6 | 105388679 | 105388708 | Hyper | literature, cancer_general | LINC00577 | chr6 | 105388913 | 105389710 | Hyper | cancer_general | LINC00577 |
| chr6 | 105400913 | 105401007 | Hyper | cancer_general | LIN28B | chr6 | 105401620 | 105401874 | Hyper | cancer_general | LIN28B |
| chr6 | 105404574 | 105404674 | Hyper | cancer_general | LIN28B | chr6 | 105405656 | 105405772 | Hyper | cancer_general | LIN28B |
| chr6 | 105406098 | 105406128 | Hyper | cancer_general | LIN28B | chr6 | 105584264 | 105585554 | Hyper | tcga, cancer_general, liver_tcga | BVES-AS1, BVES |
| chr6 | 106429049 | 106429624 | Hyper | liver_tcga, cancer_general | — | chr6 | 106434339 | 106434368 | Hyper | literature | — |
| chr6 | 106441869 | 106442979 | Hyper | cancer_general | SOBP | chr6 | 106960908 | 106961023 | Hyper | cancer_general | AIM1 |
| chr6 | 107955952 | 107955982 | Hyper | cancer_general | AF520419 | chr6 | 108435075 | 108435263 | Hyper | cancer_general | AF520419 |
| chr6 | 108436072 | 108436526 | Hyper | cancer_general | AF520419 | chr6 | 108438245 | 108438577 | Hyper | cancer_general | AF520419 |
| chr6 | 108440091 | 108440961 | Hyper | cancer_general | AF520419 | chr6 | 108479290 | 108479665 | Hyper | cancer_general | NR2E1, AF520419 |
| chr6 | 108484909 | 108485406 | Hyper | cancer_general | NR2E1, AF520419 | chr6 | 108485665 | 108485905 | Hyper | cancer_general | NR2E1, AF520419 |
| chr6 | 108486158 | 108486394 | Hyper | cancer_general | NR2E1, AF520419 | chr6 | 108487724 | 108488416 | Hyper | liver_tcga, cancer_general | NR2E1, AF520419 |
| chr6 | 108489385 | 108490633 | Hyper | liver_tcga, cancer_general | NR2E1 | chr6 | 108490978 | 108491423 | Hyper | cancer_general | NR2E1 |
| chr6 | 108492270 | 108492451 | Hyper | liver_tcga, cancer_general | NR2E1 | chr6 | 108495681 | 108495951 | Hyper | cancer_general | NR2E1 |
| chr6 | 108496208 | 108496649 | Hyper | cancer_general | NR2E1 | chr6 | 108497494 | 108497881 | Hyper | tcga, liver_tcga, cancer_general | NR2E1 |
| chr6 | 110679123 | 110679414 | Hyper | cancer_general | METTL24 | chr6 | 110797678 | 110797708 | Hyper | cancer_general | SLC22A16 |
| chr6 | 110798007 | 110799036 | Hyper | literature | SLC22A16 | chr6 | 116783448 | 116783493 | Hyper | cancer_general | FAM26F |
| chr6 | 117086249 | 117086864 | Hyper | tcga, cancer_general | FAM162B | chr6 | 117585967 | 117586004 | Hyper | cancer_general | VGLL2 |

TABLE 11-continued

| chr | Start | Stop | Hypo/hyper | classification | annotation | Chr | Start | Stop | Hypo/hyper | Classification | annotation |
| --- | --- | --- | --- | --- | --- | --- | --- | --- | --- | --- | --- |
| chr6 | 117586802 | 117587169 | Hyper | tcga, cancer_general | VGLL2 | chr6 | 117587480 | 117587577 | Hyper | cancer_general | VGLL2 |
| chr6 | 117591161 | 117591191 | Hyper | cancer_general | VGLL2 | chr6 | 117591411 | 117591743 | Hyper | cancer_general | VGLL2 |
| chr6 | 118228102 | 118228151 | Hyper | cancer_general | SLC35F1 | chr6 | 118228747 | 118228828 | Hyper | cancer_general | SLC35F1 |
| chr6 | 118229154 | 118229383 | Hyper | cancer_general | SLC35F1 | chr6 | 118229626 | 118229818 | Hyper | tcga, cancer_general | SLC35F1 |
| chr6 | 118241228 | 118241500 | Hyper | tcga, cancer_general | SLC35F1 | chr6 | 121758672 | 121758994 | Hyper | tcga, cancer_general | GJA1 |
| chr6 | 123317029 | 123317589 | Hyper | cancer_general | CIVS2 | chr6 | 123317797 | 123317833 | Hyper | cancer_general | CIVS2 |
| chr6 | 124124432 | 124124466 | Hyper | cancer_general | NKAIN2 | chr6 | 124124860 | 124125016 | Hyper | tcga | NKAIN2 |
| chr6 | 125284131 | 125284175 | Hyper | cancer_general | Metazoa_SRP, RNF217, STL | chr6 | 126068092 | 126068178 | Hyper | lung, cancer_general | HEY2, BC036196 |
| chr6 | 127439379 | 127439453 | Hyper | colorectal, cancer_general | RSPO3 | chr6 | 127439985 | 127440127 | Hyper | cancer_general, tcga | RSPO3 |
| chr6 | 127440331 | 127441123 | Hyper | cancer_general | RSPO3 | chr6 | 127441554 | 127441762 | Hyper | cancer_general | RSPO3 |
| chr6 | 127442021 | 127442104 | Hyper | cancer_general | RSPO3 | chr6 | 127840501 | 127840681 | Hyper | cancer_general, tcga | — |
| chr6 | 129204459 | 129204524 | Hyper | cancer_general | LAMA2 | chr6 | 130686534 | 130687057 | Hyper | cancer_general | TMEM200A |
| chr6 | 131602584 | 131602694 | Hyper | cancer_general | AKAP7 | chr6 | 132722078 | 132722196 | Hyper | cancer_general | MOXD1 |
| chr6 | 133561740 | 133562070 | Hyper | cancer_general | EYA4 | chr6 | 133562374 | 133563058 | Hyper | liver_tcga, cancer_general | EYA4 |
| chr6 | 133563327 | 133563918 | Hyper | tcga, cancer_general | EYA4 | chr6 | 134176549 | 134176579 | Hyper | cancer_general | MGC34034, BC041459 |
| chr6 | 134210528 | 134211367 | Hyper | cancer_general | AX747860, TCF21 | chr6 | 134213944 | 134214364 | Hyper | cancer_general | AX747860, TCF21 |
| chr6 | 134638950 | 134639003 | Hyper | cancer_general | SGK1 | chr6 | 137241928 | 137242205 | Hyper | cancer_general | SLC35D3, PEX7 |
| chr6 | 137243208 | 137243410 | Hyper | liver_tcga | PEX7, SLC35D3 | chr6 | 137244114 | 137244616 | Hyper | cancer_general | SLC35D3, PEX7 |
| chr6 | 137311158 | 137311380 | Hyper | cancer_general | IL20RA, NHEG1 | chr6 | 137809141 | 137811088 | Hyper | cancer_general | OLIG3 |
| chr6 | 137813787 | 137813895 | Hyper | cancer_general | OLIG3 | chr6 | 137814604 | 137814763 | Hyper | liver_tcga, cancer_general | OLIG3 |
| chr6 | 137815008 | 137815662 | Hyper | cancer_general | OLIG3 | chr6 | 137816472 | 137817351 | Hyper | cancer_general | OLIG3 |
| chr6 | 137818505 | 137819368 | Hyper | cancer_general | OLIG3 | chr6 | 146755567 | 146755649 | Hyper | liver_tcga, cancer_general | — |
| chr6 | 150284552 | 150284581 | Hyper | literature | ULBP1 | chr6 | 150285056 | 150286639 | Hyper | liver_tcga, literature, cancer_general, tcga | ULBP1 |
| chr6 | 150358970 | 150359407 | Hyper | tcga, cancer_general | — | chr6 | 151561016 | 151561857 | Hyper | cancer_general, tcga | AKAP12 |
| chr6 | 151562066 | 151562563 | Hyper | cancer_general | AKAP12 | chr6 | 151815055 | 151815089 | Hyper | colorectal | CCDC170 |
| chr6 | 152419908 | 152419940 | Hyper | literature | ESR1 | chr6 | 152623015 | 152623493 | Hyper | cancer_general, tcga | SYNE1 |
| chr6 | 152957895 | 152958076 | Hyper | cancer_general, tcga, colorectal | SYNE1 | chr6 | 153451236 | 153451500 | Hyper | cancer_general, tcga | RGS17 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr6 | 153451890 | 153451968 | Hyper | cancer_general | RGS17 | chr6 | 153452232 | 153452320 | Hyper | liver_tcga | RGS17 |
| chr6 | 153452713 | 153452746 | Hyper | liver_tcga, literature | RGS17 | chr6 | 154360650 | 154360746 | Hyper | cancer_general | OPRM1 |
| chr6 | 155316235 | 155316265 | Hyper | cancer_general | — | chr6 | 157556764 | 157557912 | Hyper | cancer_general | — |
| chr6 | 159290823 | 159290852 | Hyper | liver_tcga | — | chr6 | 159590048 | 159590986 | Hyper | cancer_general | FNDC1 |
| chr6 | 159654923 | 159655003 | Hyper | cancer_general | FNDC1 | chr6 | 161100361 | 161100390 | Hyper | literature | — |
| chr6 | 161188513 | 161188543 | Hyper | colorectal | — | chr6 | 161352101 | 161352135 | Hyper | cancer_general | — |
| chr6 | 163834314 | 163834637 | Hyper | colorectal | QKI, CAHM | chr6 | 163834857 | 163834938 | Hyper | tcga | QKI, CAHM |
| chr6 | 163836568 | 163836900 | Hyper | cancer_general | QKI, CAHM | chr6 | 166074119 | 166074412 | Hyper | cancer_general | — |
| chr6 | 166076788 | 166077021 | Hyper | cancer_general | — | chr6 | 166077378 | 166077660 | Hyper | cancer_general | LINC00602, LINC00473, AK090688 |
| chr6 | 166267582 | 166268082 | Hyper | cancer_general | AK090688 | chr6 | 166401254 | 166401307 | Hyper | cancer_general | |
| chr6 | 166402240 | 166402546 | Hyper | cancer_general | LINC00473, AK090688, LINC00602 | chr6 | 166421911 | 166422185 | Hyper | cancer_general | — |
| chr6 | 166579723 | 166580144 | Hyper | tcga, cancer_general, liver_tcga | T | chr6 | 166580344 | 166582797 | Hyper | tcga, cancer_general, literature | T |
| chr6 | 168842847 | 168842944 | Hyper | cancer_general | SMOC2 | chr6 | 169653638 | 169653668 | Hyper | cancer_general | THBS2 |
| chr4 | 107711 | 107759 | Hyper | cancer_general | — | chr4 | 206324 | 206353 | Hyper | literature | ZNF876P |
| chr4 | 330392 | 330708 | Hyper | cancer_general | ZNF141 | chr4 | 331322 | 331352 | Hyper | esophageal | ZNF141 |
| chr4 | 568429 | 569914 | Hyper | cancer_general | — | chr4 | 570966 | 571013 | Hyper | cancer_general | ATP5I, MYL5, PDE6B, BC020343 |
| chr4 | 571508 | 571689 | Hyper | literature | — | chr4 | 657521 | 657552 | Hyper | tcga | |
| chr4 | 682798 | 682919 | Hyper | cancer_general | MFSD7, MYL5 | chr4 | 995855 | 996357 | Hyper | cancer_general, tcga, liver_tcga | FGFRL1, SLC26A1, IDUA |
| chr4 | 996639 | 996708 | Hyper | cancer_general | IDUA, FGFRL1, SLC26A1 | chr4 | 1107494 | 1107585 | Hyper | liver_tcga | RNF212, TMED11P |
| chr4 | 1165379 | 1165470 | Hyper | cancer_general | SPON2 | chr4 | 1396578 | 1396835 | Hyper | liver_tcga, cancer_general | CRIPAK |
| chr4 | 1397396 | 1397495 | Hyper | cancer_general | CRIPAK | chr4 | 1398303 | 1398378 | Hyper | cancer_general | CRIPAK |
| chr4 | 1399723 | 1399768 | Hyper | cancer_general | CRIPAK | chr4 | 1400728 | 1400785 | Hyper | cancer_general | — |
| chr4 | 1401711 | 1401743 | Hyper | cancer_general | — | chr4 | 1800153 | 1800191 | Hyper | liver_tcga | FGFR3 |
| chr4 | 1803550 | 1803582 | Hyper | literature | LETM1, FGFR3 | chr4 | 1806084 | 1806113 | Hyper | literature | LETM1, FGFR3 |
| chr4 | 1807355 | 1807384 | Hyper | literature | LETM1, FGFR3 | chr4 | 1962787 | 1962816 | Hyper | literature | WHSC1 |
| chr4 | 2042106 | 2042556 | Hyper | cancer_general | C4orf48 | chr4 | 2765862 | 2765910 | Hyper | cancer_general | TNIP2 |
| chr4 | 3371519 | 3371652 | Hyper | liver_3842731tcga | RGS12 | chr4 | 3768833 | 3769342 | Hyper | cancer_general | ADRA2C |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 3769542 | 3769574 | Hyper | cancer_general | ADRA2C | chr4 | 3873694 | 3873769 | Hyper | cancer_general | — |
| chr4 | 4228185 | 4228241 | Hyper | cancer_general | TMEM128, OTOP1 | chr4 | 4229689 | 4229781 | Hyper | cancer_general | OTOP1, TMEM128 |
| chr4 | 4387533 | 4387627 | Hyper | cancer_general | NSG1 | chr4 | 4855102 | 4855171 | Hyper | cancer_general | MSX1 |
| chr4 | 4855371 | 4855433 | Hyper | cancer_general | MSX1 | chr4 | 4860046 | 4860075 | Hyper | literature | MSX1 |
| chr4 | 4862769 | 4863110 | Hyper | cancer_general | MSX1 | chr4 | 4867698 | 4867886 | Hyper | cancer_general | MSX1 |
| chr4 | 4868566 | 4869087 | Hyper | tcga, cancer_general | MSX1 | chr4 | 4872088 | 4872167 | Hyper | cancer_general | MSX1 |
| chr4 | 4872777 | 4872850 | Hyper | cancer_general | MSX1 | chr4 | 4873427 | 4873528 | Hyper | tcga | MSX1 |
| chr4 | 5021188 | 5021217 | Hyper | literature | CYTL1 | chr4 | 5053070 | 5053518 | Hyper | tcga, cancer_general | STK32B |
| chr4 | 5053747 | 5054093 | Hyper | cancer_general | STK32B | chr4 | 5709906 | 5710269 | Hyper | tcga, cancer_general | EVC, EVC2 |
| chr4 | 5712979 | 5713281 | Hyper | cancer_general | EVC, EVC2 | chr4 | 5889948 | 5890045 | Hyper | cancer_general | CRMP1, FLJ46481 |
| chr4 | 5890274 | 5890444 | Hyper | tcga | FLJ46481, CRMP1 | chr4 | 5891966 | 5892194 | Hyper | cancer_general, pancreas | FLJ46481, CRMP1 |
| chr4 | 5892750 | 5892780 | Hyper | cancer_general | CRMP1, FLJ46481 | chr4 | 5893981 | 5894347 | Hyper | cancer_general | FLJ46481, CRMP1 |
| chr4 | 5894676 | 5894787 | Hyper | liver_tcga, cancer_general | FLJ46481, CRMP1 | chr4 | 6200897 | 6201235 | Hyper | cancer_general | JAKMIP1, LOC285484 |
| chr4 | 6202103 | 6202276 | Hyper | cancer_general | LOC285484, JAKMIP1 | chr4 | 6247351 | 6247381 | Hyper | cancer_general | LOC285484 |
| chr4 | 6565004 | 6565042 | Hyper | cancer_general | — | chr4 | 8582549 | 8582579 | Hyper | cancer_general | CPZ, GPR78 |
| chr4 | 8858827 | 8859738 | Hyper | cancer_general | HMX1 | chr4 | 8859974 | 8860553 | Hyper | cancer_general | HMX1 |
| chr4 | 8861649 | 8862014 | Hyper | cancer_general | HMX1 | chr4 | 8862797 | 8862911 | Hyper | cancer_general | HMX1 |
| chr4 | 8863441 | 8863774 | Hyper | cancer_general | HMX1 | chr4 | 8864499 | 8864598 | Hyper | cancer_general | HMX1 |
| chr4 | 8864831 | 8865058 | Hyper | cancer_general | HMX1 | chr4 | 8868822 | 8869364 | Hyper | cancer_general | HMX1 |
| chr4 | 8869601 | 8869813 | Hyper | cancer_general | HMX1 | chr4 | 8873054 | 8873337 | Hyper | cancer_general | HMX1 |
| chr4 | 8873809 | 8873984 | Hyper | cancer_general | HMX1 | chr4 | 8874485 | 8874787 | Hyper | cancer_general | HMX1 |
| chr4 | 8875877 | 8875907 | Hyper | cancer_general | — | chr4 | 8893060 | 8893093 | Hyper | pancreas | — |
| chr4 | 8893501 | 8893531 | Hyper | cancer_general | — | chr4 | 8893794 | 8893931 | Hyper | cancer_general | — |
| chr4 | 8894641 | 8895350 | Hyper | cancer_general | — | chr4 | 8895554 | 8895584 | Hyper | cancer_general | — |
| chr4 | 8895915 | 8896052 | Hyper | cancer_general | — | chr4 | 9782992 | 9783412 | Hyper | literature, cancer general | DRD5 |
| chr4 | 10458395 | 10459121 | Hyper | cancer_general | ZNF518B | chr4 | 10462833 | 10463604 | Hyper | tcga, cancer_general | ZNF518B |
| chr4 | 11429506 | 11429633 | Hyper | cancer_general | — | chr4 | 13524026 | 13524430 | Hyper | tcga, cancer_general | LOC285547 |
| chr4 | 13524665 | 13524775 | Hyper | cancer_general | LOC285547 | chr4 | 13537569 | 13537688 | Hyper | cancer_general | LOC285547 |
| chr4 | 13540983 | 13541068 | Hyper | cancer_general | NKX3-2, LOC285548, LOC285547 | chr4 | 13541408 | 13541447 | Hyper | cancer_general | NKX3-2, LOC285548, LOC285547 |
| chr4 | 13543859 | 13544113 | Hyper | liver_tcga, cancer_general | LOC285548, NKX3-2 | chr4 | 13545563 | 13545760 | Hyper | liver_tcga, cancer_general | LOC285548, NKX3-2 |
| chr4 | 13546026 | 13546078 | Hyper | cancer_general | LOC285548, NKX3-2 | chr4 | 13548502 | 13548895 | Hyper | cancer_general | LOC285548, NKX3-2 |
| chr4 | 13549340 | 13549510 | Hyper | tcga | LOC285548, NKX3-2 | chr4 | 15780223 | 15780320 | Hyper | tcga, liver_tcga | CD38 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 16084741 | 16085381 | Hyper | tcga, cancer_general | — | chr4 | 16085618 | 16085682 | Hyper | cancer_general | — |
| chr4 | 17783003 | 17783600 | Hyper | tcga, cancer_general, liver_tcga | FAM184B | chr4 | 20254693 | 20254723 | Hyper | cancer_general | SLIT2 |
| chr4 | 20255414 | 20255861 | Hyper | cancer_general | SLIT2 | chr4 | 20256152 | 20256340 | Hyper | cancer_general | SLIT2 |
| chr4 | 21950248 | 21950341 | Hyper | cancer_general | — | chr4 | 24801809 | 24801985 | Hyper | cancer_general | CCDC149, SOD3 |
| chr4 | 24914638 | 24914668 | Hyper | blood | CCDC149 | chr4 | 25656815 | 25656879 | Hyper | tcga | SLC34A2 |
| chr4 | 25657437 | 25657477 | Hyper | cancer_general | SLC34A2 | chr4 | 27086432 | 27086462 | Hyper | cancer_general | — |
| chr4 | 30722243 | 30722273 | Hyper | cancer_general | PCDH7 | chr4 | 30723811 | 30723862 | Hyper | cancer_general | PCDH7 |
| chr4 | 30724249 | 30724372 | Hyper | cancer_general | PCDH7 | chr4 | 37245726 | 37245851 | Hyper | cancer_general | KIAA1239, MIR4801 |
| chr4 | 37246134 | 37246883 | Hyper | tcga, cancer_general | KIAA1239, MIR4801 | chr4 | 37247096 | 37247216 | Hyper | cancer_general | KIAA1239 MIR4801 |
| chr4 | 40632773 | 40632802 | Hyper | literature | — | chr4 | 41258716 | 41259176 | Hyper | liver_tcga, cancer_general | UCHL1, UCHL1-AS1 |
| chr4 | 41747009 | 41747133 | Hyper | cancer_general | PHOX2B | chr4 | 41747493 | 41747582 | Hyper | cancer_general | PHOX2B |
| chr4 | 41747958 | 41748296 | Hyper | cancer_general | PHOX2B | chr4 | 41748660 | 41748803 | Hyper | cancer_general | PHOX2B |
| chr4 | 41749033 | 41749063 | Hyper | cancer_general | PHOX2B | chr4 | 41749270 | 41749761 | Hyper | cancer_general | PHOX2B |
| chr4 | 41750223 | 41750504 | Hyper | lung, cancer_general | PHOX2B | chr4 | 41751870 | 41752006 | Hyper | cancer_general | PHOX2B |
| chr4 | 41752451 | 41752693 | Hyper | cancer_general | PHOX2B | chr4 | 41752968 | 41753398 | Hyper | cancer_general | PHOX2B |
| chr4 | 41753610 | 41754071 | Hyper | cancer_general | PHOX2B | chr4 | 41875430 | 41875902 | Hyper | cancer_general | BC025350 |
| chr4 | 41880331 | 41880412 | Hyper | cancer_general, literature, cancer_general | BC025350 | chr4 | 41881385 | 41881425 | Hyper | cancer_general | BC025350 |
| chr4 | 41882549 | 41882627 | Hyper | cancer_general | BC025350 | chr4 | 41883091 | 41883302 | Hyper | cancer_general | BC025350 |
| chr4 | 41883510 | 41883610 | Hyper | cancer_general | BEND4 | chr4 | 42152908 | 42154025 | Hyper | liver_tcga, cancer_general, tcga | BEND4 |
| chr4 | 42154280 | 42154359 | Hyper | cancer_general | BEND4 | chr4 | 42154662 | 42154997 | Hyper | pancreas, cancer_general, literature | BEND4 |
| chr4 | 42398842 | 42399872 | Hyper | lung | SHISA3 | chr4 | 42399137 | 42399191 | Hyper | cancer_general | SHISA3 |
| chr4 | 42399688 | 42399872 | Hyper | tcga, liver_tcga, cancer_general | SHISA3 | chr4 | 44449480 | 44449651 | Hyper | cancer_general | KCTD8 |
| chr4 | 44450263 | 44450375 | Hyper | cancer_general | KCTD8 | chr4 | 46391353 | 46391383 | Hyper | cancer_general | GABRA2 |
| chr4 | 46995161 | 46995835 | Hyper | tcga, cancer_general, liver_tcga | GABRA4 | chr4 | 47034908 | 47034938 | Hyper | cancer_general | GABRB1 |
| chr4 | 48485067 | 48486000 | Hyper | liver_tcga, cancer_general | SLC10A4, ZAR1 | chr4 | 48486356 | 48486389 | Hyper | cancer_general | ZAR1, SLC10A4 |
| chr4 | 48492181 | 48492433 | Hyper | tcga, liver_tcga, cancer_general | ZAR1, FRYL, SLC10A4 | chr4 | 48988109 | 48988335 | Hyper | tcga | CWH43 |
| chr4 | 53728495 | 53729056 | Hyper | tcga, cancer_general, liver_tcga | RASL11B | chr4 | 54966854 | 54967075 | Hyper | tcga, cancer_general | GSX2 |
| chr4 | 54967342 | 54967484 | Hyper | cancer_general | GSX2 | chr4 | 54969833 | 54970095 | Hyper | cancer_general | GSX2 |
| chr4 | 54970369 | 54970482 | Hyper | cancer_general | GSX2 | chr4 | 54975936 | 54976131 | Hyper | cancer_general | GSX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 55093048 | 55093255 | Hyper | cancer_general | PDGFRA | chr4 | 55096239 | 55096344 | Hyper | cancer_general | PDGFRA |
| chr4 | 55097404 | 55097634 | Hyper | cancer_general | PDGFRA | chr4 | 55097973 | 55098373 | Hyper | tcga, cancer_general | PDGFRA |
| chr4 | 55098674 | 55098744 | Hyper | cancer_general | PDGFRA | chr4 | 55099016 | 55099062 | Hyper | cancer_general | PDGFRA |
| chr4 | 55133613 | 55133642 | Hyper | literature | PDGFRA | chr4 | 55136787 | 55136816 | Hyper | literature | PDGFRA |
| chr4 | 55138657 | 55138686 | Hyper | literature | PDGFRA | chr4 | 55139691 | 55139720 | Hyper | literature | PDGFRA |
| chr4 | 55140731 | 55140784 | Hyper | literature | PDGFRA | chr4 | 55141015 | 55141050 | Hyper | literature | PDGFRA |
| chr4 | 55144105 | 55144134 | Hyper | literature | PDGFRA | chr4 | 55146554 | 55146583 | Hyper | literature | PDGFRA |
| chr4 | 55152075 | 55152140 | Hyper | literature | PDGFRA | chr4 | 55524220 | 55524274 | Hyper | cancer_general | KIT |
| chr4 | 55589753 | 55589782 | Hyper | literature | DL490879, KIT | chr4 | 55592166 | 55592204 | Hyper | literature | DL490879, KIT |
| chr4 | 55593417 | 55593675 | Hyper | literature | KIT, DL490879 | chr4 | 55594183 | 55594212 | Hyper | literature | KIT, DL490879 |
| chr4 | 55595504 | 55595614 | Hyper | literature | KIT, DL490879 | chr4 | 55599306 | 55599356 | Hyper | literature | KIT |
| chr4 | 55968165 | 55968194 | Hyper | literature | KDR | chr4 | 55991107 | 55991228 | Hyper | cancer_general | KDR |
| chr4 | 55992129 | 55992169 | Hyper | cancer_general | KDR | chr4 | 56659692 | 56660021 | Hyper | cancer_general | U6 |
| chr4 | 57371718 | 57371963 | Hyper | liver_tcga, cancer_general | ARL9, SRP72 | chr4 | 57372336 | 57372504 | Hyper | cancer_general | ARL9, SRP72 |
| chr4 | 57396946 | 57397264 | Hyper | cancer_general | THEGL, ARL9 | chr4 | 57521403 | 57522815 | Hyper | tcga, cancer_general | HOPX |
| chr4 | 57687720 | 57687782 | Hyper | esophageal | SPINK2 | chr4 | 57976033 | 57976185 | Hyper | liver_tcga, tcga | LOC255130, IGFBP7 |
| chr4 | 57976416 | 57976573 | Hyper | tcga, liver_tcga | IGFBP7, LOC255130 | chr4 | 58030191 | 58030524 | Hyper | esophageal | LOC255130 |
| chr4 | 62066196 | 62066553 | Hyper | tcga | LPHN3 | chr4 | 62067511 | 62067624 | Hyper | cancer_general | LPHN3 |
| chr4 | 62068072 | 62068150 | Hyper | cancer_general | LPHN3 | chr4 | 66535130 | 66535443 | Hyper | tcga, cancer_general | LOC100144602, EPHA5 |
| chr4 | 66536171 | 66536323 | Hyper | tcga | LOC100144602, EPHA5 | chr4 | 74702479 | 74702516 | Hyper | cancer_general | CXCL6 |
| chr4 | 74735076 | 74735137 | Hyper | blood | CXCL1 | chr4 | 74809877 | 74809933 | Hyper | cancer_general | — |
| chr4 | 75858573 | 75858629 | Hyper | esophageal | PARM1 | chr4 | 76555532 | 76555856 | Hyper | tcga, cancer_general, liver_tcga | CDKL2 |
| chr4 | 81106351 | 81106871 | Hyper | tcga, cancer_general | PRDM8 | chr4 | 81124277 | 81124662 | Hyper | cancer_general | PRDM8 |
| chr4 | 81187046 | 81187076 | Hyper | cancer_general | FGF5 | chr4 | 81187559 | 81187589 | Hyper | cancer_general | FGF5 |
| chr4 | 81188491 | 81188556 | Hyper | cancer_general | FGF5 | chr4 | 81189419 | 81189911 | Hyper | cancer_general | FGF5 |
| chr4 | 81951431 | 81951460 | Hyper | literature | BMP3 | chr4 | 81951941 | 81951970 | Hyper | literature | BMP3 |
| chr4 | 81952170 | 81952344 | Hyper | literature, cancer_general | BMP3 | chr4 | 82135873 | 82136056 | Hyper | cancer_general | PRKG2 |
| chr4 | 82136495 | 82136548 | Hyper | cancer_general | PRKG2 | chr4 | 82136807 | 82136837 | Hyper | cancer_general | PRKG2 |
| chr4 | 83720611 | 83720643 | Hyper | tcga | — | chr4 | 84035907 | 84035936 | Hyper | literature | PLAC8 |
| chr4 | 85402377 | 85402511 | Hyper | cancer_general | NKX6-1 | chr4 | 85402776 | 85403423 | Hyper | cancer_general | — |
| chr4 | 85403913 | 85404693 | Hyper | cancer_general | NKX6-1 | chr4 | 85404045 | 85404142 | Hyper | cancer_general | NKX6-1 |
| chr4 | 85414373 | 85414405 | Hyper | cancer_general | NKX6-1 | chr4 | 85414725 | 85414846 | Hyper | cancer_general | NKX6-1 |
| chr4 | 85417336 | 85417564 | Hyper | cancer_general | NKX6-1 | chr4 | 85417953 | 85418079 | Hyper | cancer_general | NKX6-1 |
| chr4 | 85418393 | 85418963 | Hyper | cancer_general | NKX6-1 | chr4 | 85420591 | 85420621 | Hyper | cancer_general | NKX6-1 |
| chr4 | 85422188 | 85422432 | Hyper | cancer_general | NKX6-1 | chr4 | 85422953 | 85423316 | Hyper | cancer_general | NKX6-1 |
| chr4 | 85424401 | 85424483 | Hyper | cancer_general | NKX6-1 | chr4 | 87515337 | 87515367 | Hyper | esophageal | PTPN13 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 89378464 | 89378497 | Hyper | cancer_general | HERC5 | chr4 | 89378744 | 89378888 | Hyper | cancer_general | HERC5 |
| chr4 | 90757517 | 90757828 | Hyper | cancer_general, tcga | LOC644248, SNCA | chr4 | 90758105 | 90758134 | Hyper | tcga | LOC644248, SNCA |
| chr4 | 90758776 | 90758883 | Hyper | liver_tcga, cancer_general | SNCA, LOC644248 | chr4 | 93224972 | 93225171 | Hyper | tcga | GRID2 |
| chr4 | 93226365 | 93227129 | Hyper | tcga, cancer_general | GRID2 | chr4 | 94749725 | 94749755 | Hyper | blood | ATOH1 |
| chr4 | 94750982 | 94751140 | Hyper | tcga, cancer_general | ATOH1 | chr4 | 94751419 | 94751502 | Hyper | cancer_general | ATOH1 |
| chr4 | 94753415 | 94753445 | Hyper | cancer_general | ATOH1 | chr4 | 94755963 | 94756109 | Hyper | cancer_general | ATOH1 |
| chr4 | 96470752 | 96470782 | Hyper | cancer_general | UNC5C | chr4 | 101111246 | 101111504 | Hyper | cancer_general, tcga | DDIT4L |
| chr4 | 101111857 | 101111970 | Hyper | tcga, cancer_general | DDIT4L | chr4 | 102711731 | 102711787 | Hyper | cancer_general | BANK1 |
| chr4 | 102711994 | 102712065 | Hyper | cancer_general | BANK1 | chr4 | 107955311 | 107955826 | Hyper | cancer_general | DKK2 |
| chr4 | 107956676 | 107957086 | Hyper | cancer_general | DKK2 | chr4 | 107957373 | 107957466 | Hyper | cancer_general | DKK2 |
| chr4 | 109093101 | 109093168 | Hyper | cancer_general | LEF1-AS1 | chr4 | 109093405 | 109093506 | Hyper | cancer_general | LEF1-AS1 |
| chr4 | 110223090 | 110223980 | Hyper | liver_tcga, cancer_general | COL25A1 | chr4 | 111532632 | 111532961 | Hyper | cancer_general | PITX2 |
| chr4 | 111536288 | 111536693 | Hyper | cancer_general | PITX2 | chr4 | 111536960 | 111537042 | Hyper | cancer_general | PITX2 |
| chr4 | 111537407 | 111537497 | Hyper | cancer_general | PITX2 | chr4 | 111540199 | 111540360 | Hyper | cancer_general | PITX2 |
| chr4 | 111542187 | 111542757 | Hyper | cancer_general | PITX2 | chr4 | 111543232 | 111543450 | Hyper | liver_tcga, literature, cancer_general | PITX2 |
| chr4 | 111543661 | 111543735 | Hyper | cancer_general | PITX2 | chr4 | 111544381 | 111544583 | Hyper | cancer_general | PITX2 |
| chr4 | 111549800 | 111549830 | Hyper | cancer_general | PITX2 | chr4 | 111550618 | 111550834 | Hyper | cancer_general | PITX2 |
| chr4 | 111552118 | 111552148 | Hyper | cancer_general | PITX2 | chr4 | 111553099 | 111553450 | Hyper | cancer_general | PITX2 |
| chr4 | 111553916 | 111553951 | Hyper | cancer_general | PITX2 | chr4 | 111554950 | 111555343 | Hyper | cancer_general | — |
| chr4 | 111557965 | 111558049 | Hyper | cancer_general | — | chr4 | 111558551 | 111559233 | Hyper | literature, cancer_general | — |
| chr4 | 111560249 | 111560636 | Hyper | cancer_general | NEUROG2 | chr4 | 111562576 | 111562648 | Hyper | cancer_general | NEUROG2 |
| chr4 | 113430640 | 113430672 | Hyper | cancer_general | NEUROG2 | chr4 | 113431834 | 113432573 | Hyper | cancer_general | NEUROG2 |
| chr4 | 113436216 | 113436287 | Hyper | cancer_general | NEUROG2 | chr4 | 113441592 | 113441733 | Hyper | cancer_general | NEUROG2 |
| chr4 | 113442098 | 113442525 | Hyper | cancer_general | 7SK, NDNF | chr4 | 113444020 | 113444448 | Hyper | cancer_general | PRDM5 |
| chr4 | 117847399 | 117847458 | Hyper | cancer_general | QRFPR | chr4 | 121844063 | 121844206 | Hyper | cancer_general | — |
| chr4 | 121992265 | 121992312 | Hyper | cancer_general | PP12613, TMEM155 | chr4 | 121993997 | 121994251 | Hyper | cancer_general | QRFPR |
| chr4 | 123301422 | 123301846 | Hyper | cancer_general | — | chr4 | 122302116 | 122302246 | Hyper | tcga, liver_tcga, cancer_general | PP12613, TMEM155 |
| chr4 | 122685807 | 122685951 | Hyper | cancer_general | FAT4 | chr4 | 122686209 | 122686507 | Hyper | cancer_general | — |
| chr4 | 122871294 | 122871334 | Hyper | cancer_general | INTU | chr4 | 122871573 | 122872000 | Hyper | cancer_general | FAT4 |
| chr4 | 126237310 | 126237611 | Hyper | tcga, cancer_general | PCDH10, BC040219 | chr4 | 126238024 | 126238436 | Hyper | cancer_general, tcga | — |
| chr4 | 128544048 | 128544161 | Hyper | cancer_general | PCDH10 | chr4 | 128544646 | 128544789 | Hyper | cancer_general | INTU |
| chr4 | 134067881 | 134068004 | Hyper | literature | PCDH10, BC040219 | chr4 | 134068577 | 134068791 | Hyper | tcga, cancer_general | PCDH10, BC040219 |
| chr4 | 134069289 | 134069318 | Hyper | literature | PCDH10, BC040219 | chr4 | 134069578 | 134069896 | Hyper | literature, cancer_general | PCDH10, BC040219 |
| chr4 | 134070374 | 134070403 | Hyper | | | chr4 | 134071648 | 134072967 | Hyper | literature, cancer_general | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 134073184 | 134073322 | Hyper | cancer_general | PCDH10, BC040219 | chr4 | 134073568 | 134073641 | Hyper | cancer_general | PCDH10, BC040219 |
| chr4 | 134074030 | 134074156 | Hyper | cancer_general | PCDH10, BC040219 | chr4 | 140200529 | 140201462 | Hyper | cancer_general | MGARP, NDUFC1 |
| chr4 | 140656643 | 140657089 | Hyper | tcga, cancer_general | MAML3 | chr4 | 141347942 | 141348151 | Hyper | cancer_general | CLGN |
| chr4 | 141418921 | 141419418 | Hyper | cancer_general | LOC152586 | chr4 | 141488870 | 141489128 | Hyper | cancer_general | UCP1 |
| chr4 | 142053130 | 142053160 | Hyper | cancer_general | RNF150 | chr4 | 142053520 | 142053734 | Hyper | tcga, cancer_general | RNF150 |
| chr4 | 142054239 | 142054460 | Hyper | tcga | RNF150 | chr4 | 143766796 | 143766930 | Hyper | cancer_general | — |
| chr4 | 144621336 | 144622058 | Hyper | cancer_general, tcga | FREM3 | chr4 | 145568052 | 145568147 | Hyper | cancer_general | HHIP, HHIP-AS1 |
| chr4 | 145568459 | 145568741 | Hyper | cancer_general | HHIP, HHIP-AS1 | chr4 | 147558272 | 147558504 | Hyper | cancer_general | POU4F2 |
| chr4 | 147559321 | 147560617 | Hyper | tcga, cancer_general | POU4F2 | chr4 | 147560933 | 147562055 | Hyper | cancer_general | POU4F2 |
| chr4 | 147568636 | 147569060 | Hyper | cancer_general | POU4F2 | chr4 | 147569620 | 147569650 | Hyper | cancer_general | — |
| chr4 | 147576177 | 147576639 | Hyper | cancer_general | FBXW7 | chr4 | 152246132 | 152246314 | Hyper | blood | — |
| chr4 | 153247273 | 153247386 | Hyper | literature | FBXW7 | chr4 | 153249362 | 153249398 | Hyper | literature | FBXW7 |
| chr4 | 153251894 | 153251923 | Hyper | literature | — | chr4 | 154709524 | 154710914 | Hyper | tcga, literature, cancer_general | SFRP2 |
| chr4 | 154712172 | 154712594 | Hyper | tcga, cancer_general | SFRP2 | chr4 | 154713500 | 154713530 | Hyper | cancer_general | SFRP2 |
| chr4 | 154713949 | 154714010 | Hyper | cancer_general | SFRP2 | chr4 | 155254166 | 155254196 | Hyper | cancer_general | DCHS2 |
| chr4 | 155411501 | 155412279 | Hyper | cancer_general | DCHS2 | chr4 | 155663209 | 155663647 | Hyper | cancer_general, tcga | LRAT, DQ266889 |
| chr4 | 156129153 | 156129183 | Hyper | cancer_general | NPY2R | chr4 | 156129451 | 156129495 | Hyper | cancer_general | NPY2R |
| chr4 | 156129746 | 156129797 | Hyper | cancer_general | NPY2R | chr4 | 156130047 | 156130297 | Hyper | cancer_general | NPY2R |
| chr4 | 156297416 | 156297556 | Hyper | colorectal, cancer_general | MAP9 | chr4 | 156297839 | 156298073 | Hyper | tcga, colorectal | MAP9 |
| chr4 | 156588311 | 156588401 | Hyper | tcga, cancer_general | GUCY1A3 | chr4 | 156589273 | 156589323 | Hyper | cancer_general | GUCY1A3 |
| chr4 | 156680257 | 156680532 | Hyper | tcga | GUCY1B3 | chr4 | 156681370 | 156681489 | Hyper | tcga | GUCY1B3 |
| chr4 | 158141576 | 158141606 | Hyper | cancer_general | GRIA2 | chr4 | 158142847 | 158142999 | Hyper | cancer_general | GRIA2 |
| chr4 | 158143443 | 158143564 | Hyper | cancer_general | GRIA2 | chr4 | 164252991 | 164253447 | Hyper | tcga, cancer_general | NPY1R, NPY1 |
| chr4 | 165304515 | 165304578 | Hyper | cancer_general | — | chr4 | 165305030 | 165305163 | Hyper | cancer_general | — |
| chr4 | 166414834 | 166414921 | Hyper | lung, cancer_general | — | chr4 | 166794771 | 166794909 | Hyper | cancer_general | — |
| chr4 | 166796011 | 166796212 | Hyper | cancer_general | TLL1 | chr4 | 168155109 | 168155269 | Hyper | tcga, cancer_general | TLL1 |
| chr4 | 170947287 | 170947325 | Hyper | blood | BC031941 | chr4 | 172734168 | 172734203 | Hyper | cancer_general | — |
| chr4 | 172734550 | 172734790 | Hyper | cancer_general | GALNTL6 | chr4 | 174429658 | 174429688 | Hyper | cancer_general | GALNTL6 |
| chr4 | 174430310 | 174431072 | Hyper | cancer_general | — | chr4 | 174438567 | 174438744 | Hyper | cancer_general | HAND2 |
| chr4 | 174439822 | 174440257 | Hyper | literature, cancer_general | HAND2 | chr4 | 174440635 | 174440713 | Hyper | cancer_general | HAND2 |
| chr4 | 174443212 | 174443242 | Hyper | cancer_general | HAND2, NBLA00301 | chr4 | 174443563 | 174443934 | Hyper | tcga, cancer_general | HAND2, NBLA00301 |
| chr4 | 174444151 | 174444180 | Hyper | tcga | HAND2, NBLA00301 | chr4 | 174446486 | 174446525 | Hyper | cancer_general | HAND2, NBLA00301 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr4 | 174446952 | 174447005 | Hyper | cancer_general | HAND2, NBLA00301 | chr4 | 174449950 | 174451482 | Hyper | tcga, cancer_general, literature | HAND2, NBLA00301 |
| chr4 | 174451855 | 174452098 | Hyper | cancer_general | NBLA00301, HAND2 | chr4 | 174459185 | 174459840 | Hyper | cancer_general | HAND2, NBLA00301 |
| chr4 | 174460186 | 174460221 | Hyper | cancer_general | NBLA00301, HAND2 | chr4 | 175132735 | 175132765 | Hyper | cancer_general | AK125257 |
| chr4 | 175133085 | 175133201 | Hyper | cancer_general | AK125257 | chr4 | 175134897 | 175135672 | Hyper | cancer_general | AK125257 |
| chr4 | 175135921 | 175136011 | Hyper | cancer_general | AK125257 | chr4 | 175138411 | 175138546 | Hyper | cancer_general | AK125257 |
| chr4 | 175138964 | 175139254 | Hyper | cancer_general | AK125257 | chr4 | 175139559 | 175139685 | Hyper | cancer_general | AK125257 |
| chr4 | 175750456 | 175750738 | Hyper | cancer_general | AK093264, BC034301, GLRA3 | chr4 | 176923424 | 176923558 | Hyper | tcga, cancer_general | — |
| chr4 | 176987324 | 176987373 | Hyper | cancer_general | WDR17 | chr4 | 177713228 | 177713437 | Hyper | tcga, cancer_general | VEGFC |
| chr4 | 180979270 | 180979300 | Hyper | cancer_general | — | chr4 | 180980297 | 180980356 | Hyper | cancer_general | — |
| chr4 | 183063666 | 183063950 | Hyper | cancer_general | TENM3, MGC45800 | chr4 | 183064617 | 183064655 | Hyper | cancer_general | TENM3, MGC45800 |
| chr4 | 184019249 | 184019316 | Hyper | cancer_general | WWC2, WWC2-AS2 | chr4 | 184019692 | 184019736 | Hyper | blood | WWC2, WWC2-AS2, WWC2 |
| chr4 | 184020106 | 184020179 | Hyper | blood | WWC2, WWC2-AS2 | chr4 | 184644053 | 184644249 | Hyper | hepatobiliary | — |
| chr4 | 184718260 | 184718352 | Hyper | cancer_general | — | chr4 | 184826238 | 184826493 | Hyper | cancer_general, tcga | STOX2 |
| chr4 | 184826938 | 184827237 | Hyper | tcga, cancer_general | STOX2 | chr4 | 185089696 | 185089797 | Hyper | head_neck | ENPP6 |
| chr4 | 185937333 | 185937889 | Hyper | cancer_general | HELT | chr4 | 185938497 | 185938564 | Hyper | cancer_general | HELT |
| chr4 | 185940338 | 185940460 | Hyper | cancer_general | HELT | chr4 | 185941585 | 185942760 | Hyper | cancer_general | HELT |
| chr3 | 187647073 | 187647457 | Hyper | blood | FAT1 | chr3 | 238536 | 239094 | Hyper | cancer_general | CHL1 |
| chr3 | 239622 | 240223 | Hyper | cancer_general | CHL1 | chr3 | 2140277 | 2140398 | Hyper | cancer_general | CNTN4 |
| chr3 | 3840498 | 3840758 | Hyper | liver_tcga, cancer_general | LRRN1, BC141932, SUMF1 | chr3 | 3841046 | 3841144 | Hyper | tcga, liver_tcga | LRRN1, BC141932, SUMF1 |
| chr3 | 3842679 | 3842731 | Hyper | tcga | SUMF1, BC141932, LRRN1 | chr3 | 5137960 | 5138019 | Hyper | pancreas | — |
| chr3 | 6902288 | 6902353 | Hyper | cancer_general | GRM7 | chr3 | 6903425 | 6903463 | Hyper | cancer_general | GRM7 |
| chr3 | 8725296 | 8725348 | Hyper | esophageal | — | chr3 | 8810136 | 8810220 | Hyper | cancer_general | Mir_548, OXTR |
| chr3 | 9178165 | 9178263 | Hyper | literature, tcga | SRGAP3 | chr3 | 9593979 | 9594015 | Hyper | cancer_general | LHFPL4 |
| chr3 | 9594263 | 9594382 | Hyper | liver_tcga | LHFPL4 | chr3 | 9595292 | 9595584 | Hyper | cancer_general | LHFPL4 |
| chr3 | 9904233 | 9904554 | Hyper | cancer_general | CIDEC | chr3 | 9957064 | 9957142 | Hyper | cancer_general | IL17RC, IL17RE |
| chr3 | 9957451 | 9957677 | Hyper | cancer_general | IL17RE, IL17RC | chr3 | 10183321 | 10183350 | Hyper | literature | VHL |
| chr3 | 10183706 | 10183782 | Hyper | literature | VHL | chr3 | 10191477 | 10191620 | Hyper | literature | VHL |
| chr3 | 10857987 | 10858019 | Hyper | cancer_general | SLC6A11 | chr3 | 11034264 | 11034359 | Hyper | tcga | SLC6A1 |
| chr3 | 11035070 | 11035330 | Hyper | cancer_general | SLC6A1 | chr3 | 12046405 | 12046632 | Hyper | tcga | SYN2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 12632309 | 12632401 | Hyper | literature | MKRN2, RAF1 | chr3 | 12645678 | 12645713 | Hyper | literature | RAF1 |
| chr3 | 12729424 | 12729454 | Hyper | esophageal | — | chr3 | 12917606 | 12917655 | Hyper | cancer_general | DQ581328 |
| chr3 | 13323494 | 13323973 | Hyper | cancer_general | — | chr3 | 13324358 | 13324433 | Hyper | cancer_general | — |
| chr3 | 13324847 | 13324938 | Hyper | tcga, cancer_general | — | chr3 | 13590416 | 13590863 | Hyper | cancer_general | FBLN2 |
| chr3 | 13679284 | 13679319 | Hyper | pancreas | — | chr3 | 13921407 | 13921463 | Hyper | cancer_general | WNT7A |
| chr3 | 14851850 | 14851897 | Hyper | cancer_general | FGD5 | chr3 | 14852325 | 14852919 | Hyper | tcga, cancer_general | FGD5 |
| chr3 | 16554052 | 16554111 | Hyper | cancer_general | — | chr3 | 16554347 | 16554633 | Hyper | tcga, cancer_general | — |
| chr3 | 19189441 | 19189470 | Hyper | tcga | KCNH8 | chr3 | 19189694 | 19189765 | Hyper | tcga | KCNH8 |
| chr3 | 19190143 | 19190216 | Hyper | tcga | KCNH8 | chr3 | 22413665 | 22413694 | Hyper | tcga | ZNF385D |
| chr3 | 22413945 | 22413974 | Hyper | tcga | ZNF385D | chr3 | 24871002 | 24871245 | Hyper | tcga | — |
| chr3 | 25469110 | 25469139 | Hyper | literature | RARB, LOC100130354 | chr3 | 25469377 | 25469406 | Hyper | literature | RARB, LOC100130354 |
| chr3 | 25469679 | 25469708 | Hyper | literature | LOC100130354, RARB | chr3 | 26664045 | 26664119 | Hyper | cancer_general | LRRC3B |
| chr3 | 26664389 | 26664755 | Hyper | tcga | LRRC3B | chr3 | 27754478 | 27754508 | Hyper | cancer_general | EOMES |
| chr3 | 27762336 | 27762650 | Hyper | cancer_general | EOMES | chr3 | 27762857 | 27762887 | Hyper | cancer_general | EOMES |
| chr3 | 27763566 | 27763595 | Hyper | liver_tcga | EOMES | chr3 | 27764457 | 27764503 | Hyper | cancer_general | EOMES |
| chr3 | 27765181 | 27765347 | Hyper | cancer_general | EOMES | chr3 | 27771497 | 27772004 | Hyper | cancer_general | EOMES |
| chr3 | 27772790 | 27772819 | Hyper | literature | EOMES | chr3 | 28616832 | 28617675 | Hyper | tcga, cancer_general | LINC00693, AX746710 |
| chr3 | 32858353 | 32859693 | Hyper | tcga, cancer_general | TRIM71 | chr3 | 32860068 | 32860273 | Hyper | cancer_general | TRIM71 |
| chr3 | 33259904 | 33260776 | Hyper | cancer_general | SUSD5 | chr3 | 35680842 | 35680872 | Hyper | cancer_general | ARPP21 |
| chr3 | 36805815 | 36805863 | Hyper | cancer_general | — | chr3 | 36806151 | 36806193 | Hyper | cancer_general | — |
| chr3 | 37493519 | 37493621 | Hyper | esophageal | ITGA9 | chr3 | 37901923 | 37901953 | Hyper | blood | CTDSPL, BC040563 |
| chr3 | 38035767 | 38035989 | Hyper | cancer_general | VILL | chr3 | 38080685 | 38080925 | Hyper | cancer_general, liver_tcga | DLEC1, PLCD1 |
| chr3 | 38081148 | 38081271 | Hyper | cancer_general | DLEC1, PLCD1 | chr3 | 38182244 | 38182306 | Hyper | literature | MYD88, ACAA1 |
| chr3 | 38182626 | 38182655 | Hyper | literature | MYD88, ACAA1 | chr3 | 38690624 | 38690668 | Hyper | cancer_general | SCN5A |
| chr3 | 38691348 | 38691466 | Hyper | esophageal | SCN5A | chr3 | 39851772 | 39851814 | Hyper | cancer_general | MYRIP |
| chr3 | 40028507 | 40028713 | Hyper | liver_tcga | ENTPD3, ENTPD3-AS1 | chr3 | 41266086 | 41266151 | Hyper | literature | AK095242, AK311005, CTNNB1 |
| chr3 | 42814569 | 42814603 | Hyper | cancer_general | HIGD1A, CCDC13 | chr3 | 42947411 | 42947552 | Hyper | cancer_general | ZNF662 |
| chr3 | 44036260 | 44036330 | Hyper | cancer_general | — | chr3 | 44036570 | 44036600 | Hyper | cancer_general | — |
| chr3 | 44036820 | 44037203 | Hyper | tcga, cancer_general | — | chr3 | 44037625 | 44037662 | Hyper | cancer_general | — |
| chr3 | 44037874 | 44038646 | Hyper | cancer_general | — | chr3 | 44039348 | 44040006 | Hyper | cancer_general | — |
| chr3 | 44040511 | 44040553 | Hyper | tcga, cancer_general | — | chr3 | 44040796 | 44041039 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 44063434 | 44063872 | Hyper | cancer_general |  | chr3 | 44596479 | 44596509 | Hyper | cancer_general, tcga | ZKSCAN7, ZNF660, ZKSCAN7 |
| chr3 | 44596716 | 44596809 | Hyper | cancer_general | ZKSCAN7 | chr3 | 44626438 | 44626711 | Hyper | cancer_general |  |
| chr3 | 44726875 | 44727193 | Hyper | cancer_general |  | chr3 | 45187296 | 45187582 | Hyper | blood | CDCP1 |
| chr3 | 46924934 | 46924964 | Hyper | esophageal | PTH1R | chr3 | 47144864 | 47144893 | Hyper | literature |  |
| chr3 | 48693304 | 48694170 | Hyper | tcga, liver_tcga, cancer_general |  | chr3 | 48698810 | 48699767 | Hyper | cancer_general, tcga |  |
| chr3 | 49236845 | 49236874 | Hyper | literature | CCDC36, LOC646498 | chr3 | 49405953 | 49405982 | Hyper | literature | RHOA |
| chr3 | 49412883 | 49412987 | Hyper | literature | RHOA | chr3 | 49591832 | 49592076 | Hyper | esophageal | BSN, BSN-AS2 |
| chr3 | 49907093 | 49907130 | Hyper | esophageal | CAMKV | chr3 | 50243383 | 50243480 | Hyper | cancer_general | SLC38A3, GNAT1 |
| chr3 | 50374655 | 50374684 | Hyper | literature | RASSF1, TUSC2, AB209621, ZMYND10 | chr3 | 50374917 | 50374946 | Hyper | literature | AB209621, ZMYND10, NPRL2, RASSF1, TUSC2 |
| chr3 | 50375179 | 50375559 | Hyper | literature | TUSC2, AB209621, ZMYND10, NPRL2, RASSF1 | chr3 | 50377973 | 50378002 | Hyper | literature | AB209621, ZMYND10, NPRL2, RASSF1 |
| chr3 | 50378277 | 50378306 | Hyper | literature | AB209621, ZMYND10, NPRL2, CYB561D2, RASSF1 | chr3 | 50378512 | 50378541 | Hyper | literature | ZMYND10, NPRL2, CYB561D2, AB209621, RASSF1 |
| chr3 | 50402170 | 50402944 | Hyper | lung, cancer_general | Mir_324, TMEM115, CACNA2D2 | chr3 | 52442062 | 52442091 | Hyper | literature | PHF7, BAP1, DNAH1 |
| chr3 | 54155611 | 54155677 | Hyper | tcga | CACNA2D3 | chr3 | 54157381 | 54157450 | Hyper | cancer_general | CACNA2D3 |
| chr3 | 54157878 | 54157919 | Hyper | cancer_general | CACNA2D3 | chr3 | 55519219 | 55519253 | Hyper | esophageal | WNT5A |
| chr3 | 55523106 | 55523290 | Hyper | cancer_general | WNT5A | chr3 | 62304560 | 62304669 | Hyper | cancer_general | PTPRG-AS1, C3orf14 |
| chr3 | 62353371 | 62354049 | Hyper | cancer_general | FEZF2 | chr3 | 62354283 | 62354328 | Hyper | cancer_general | FEZF2 |
| chr3 | 62354625 | 62354914 | Hyper | cancer_general | FEZF2 | chr3 | 62355424 | 62355478 | Hyper | cancer_general | FEZF2 |
| chr3 | 62355774 | 62357347 | Hyper | cancer_general | FEZF2 | chr3 | 62357624 | 62357667 | Hyper | cancer_general | FEZF2 |
| chr3 | 62358161 | 62358194 | Hyper | cancer_general | FEZF2 | chr3 | 62358530 | 62358595 | Hyper | cancer_general | FEZF2 |
| chr3 | 62358858 | 62359011 | Hyper | cancer_general | FEZF2 | chr3 | 62359376 | 62359893 | Hyper | cancer_general | FEZF2 |
| chr3 | 62360302 | 62360560 | Hyper | cancer_general | FEZF2 | chr3 | 62362902 | 62363200 | Hyper | cancer_general | FEZF2 |
| chr3 | 62363626 | 62363693 | Hyper | cancer_general | FEZF2 | chr3 | 62363906 | 62364329 | Hyper | cancer_general | FEZF2 |
| chr3 | 62364702 | 62365154 | Hyper | cancer_general | FEZF2 | chr3 | 62861118 | 62861148 | Hyper | cancer_general | FEZF2 |
| chr3 | 63264139 | 63264169 | Hyper | cancer_general | SYNPR | chr3 | 68056904 | 68057145 | Hyper | liver_tcga, cancer_general | FAM19A1, AX747367 |
| chr3 | 68980931 | 68981113 | Hyper | cancer_general |  | chr3 | 68981552 | 68981624 | Hyper | cancer_general |  |
| chr3 | 69590939 | 69590969 | Hyper | cancer_general |  | chr3 | 69591363 | 69592063 | Hyper | tcga, cancer_general |  |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 71802518 | 71802622 | Hyper | tcga | GPR27, EIF4E3 | chr3 | 71803126 | 71803372 | Hyper | tcga, cancer_general | GPR27, EIF4E3 |
| chr3 | 71803643 | 71803821 | Hyper | cancer_general | GPR27, EIF4E3 | chr3 | 75956011 | 75956375 | Hyper | cancer_general | — |
| chr3 | 79815522 | 79815557 | Hyper | cancer_general | — | chr3 | 79816778 | 79817015 | Hyper | cancer_general | CADM2 |
| chr3 | 79817288 | 79817318 | Hyper | cancer_general | — | chr3 | 85008553 | 85008708 | Hyper | tcga, cancer_general | |
| chr3 | 96532817 | 96532873 | Hyper | tcga | EPHA6 | chr3 | 96533383 | 96533458 | Hyper | cancer_general | EPHA6 |
| chr3 | 96534035 | 96534096 | Hyper | cancer_general | EPHA6 | chr3 | 98620891 | 98620980 | Hyper | esophageal | DCBLD2 |
| chr3 | 99594925 | 99595105 | Hyper | cancer_general | FILIP1L | chr3 | 101497841 | 101497996 | Hyper | liver_tcga, hepatobiliary | NXPE3 |
| chr3 | 112052203 | 112052419 | Hyper | tcga | CD200, BC041484 | chr3 | 117715549 | 117716473 | Hyper | cancer_general, tcga | — |
| chr3 | 120004040 | 120004405 | Hyper | tcga, liver_tcga, cancer_general | — | chr3 | 120169104 | 120169149 | Hyper | esophageal | FSTL1 |
| chr3 | 120169768 | 120169835 | Hyper | tcga | FSTL1 | chr3 | 120627317 | 120627453 | Hyper | cancer_general | STXBP5L |
| chr3 | 121902975 | 121903619 | Hyper | cancer_general | CASR | chr3 | 123167073 | 123167529 | Hyper | liver_tcga, cancer_general | — |
| chr3 | 123167769 | 123167827 | Hyper | cancer_general | — | chr3 | 124860671 | 124860700 | Hyper | literature | SLC12A8, MIR5092 |
| chr3 | 125898597 | 125899207 | Hyper | cancer_general | ALDH1L1-AS2, ALDH1L1 | chr3 | 125899525 | 125899962 | Hyper | cancer_general | ALDH1L1-AS2, ALDH1L1 NUP210P1, TXNRD3 |
| chr3 | 125932252 | 125932500 | Hyper | cancer_general | ALDH1L1-AS2 | chr3 | 126373520 | 126373704 | Hyper | blood | |
| chr3 | 126854699 | 126854796 | Hyper | cancer_general | — | chr3 | 127634186 | 127634216 | Hyper | cancer_general | KBTBD12 |
| chr3 | 127794546 | 127794860 | Hyper | cancer_general | RUVBL1, SEC61A1 | chr3 | 127795325 | 127795408 | Hyper | tcga | RUVBL1, SEC61A1 |
| chr3 | 128202447 | 128202477 | Hyper | cancer_general | GATA2 | chr3 | 128208903 | 128209232 | Hyper | cancer_general | GATA2 |
| chr3 | 128273993 | 128274611 | Hyper | tcga, pancreas, cancer_general | — | chr3 | 128417201 | 128417231 | Hyper | cancer_general | — |
| chr3 | 128720061 | 128720611 | Hyper | tcga, cancer_general | EFCC1, KIAA1257 | chr3 | 128720869 | 128721229 | Hyper | liver_tcga, cancer_general | EFCC1, KIAA1257 |
| chr3 | 128764489 | 128764632 | Hyper | cancer_general | EFCC1 | chr3 | 129693108 | 129694299 | Hyper | liver_tcga, tcga, cancer_general | TRH |
| chr3 | 129694504 | 129694534 | Hyper | cancer_general | TRH | chr3 | 130064451 | 130064484 | Hyper | cancer_general | COL6A5 |
| chr3 | 130064818 | 130064848 | Hyper | cancer_general | COL6A5 | chr3 | 130236049 | 130236273 | Hyper | cancer_general | — |
| chr3 | 131754031 | 131754061 | Hyper | cancer_general | — | chr3 | 132757065 | 132757104 | Hyper | cancer_general | TMEM108 |
| chr3 | 133748140 | 133748245 | Hyper | blood | SLCO2A1 | chr3 | 133748481 | 133748576 | Hyper | blood | SLCO2A1 |
| chr3 | 134369646 | 134369855 | Hyper | tcga, cancer_general | KY | chr3 | 134514866 | 134514895 | Hyper | tcga | EPHB1 |
| chr3 | 134515128 | 134515369 | Hyper | tcga, cancer_general | EPHB1 | chr3 | 134515676 | 134516222 | Hyper | cancer_general | EPHB1 |
| chr3 | 136537642 | 136537730 | Hyper | cancer_general | SLC35G2 | chr3 | 136538585 | 136538815 | Hyper | tcga, cancer_general | SLC35G2 |
| chr3 | 136751641 | 136751809 | Hyper | tcga | SOX14 | chr3 | 137479233 | 137479302 | Hyper | cancer_general | SOX14 |
| chr3 | 137479601 | 137479687 | Hyper | cancer_general | SOX14 | chr3 | 137479980 | 137480764 | Hyper | cancer_general | SOX14 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 137481170 | 137481315 | Hyper | cancer_general | SOX14 | chr3 | 137481858 | 137482183 | Hyper | cancer_general | SOX14 |
| chr3 | 137483313 | 137483589 | Hyper | tcga, cancer_general | BC038725, SOX14 | chr3 | 137483848 | 137484002 | Hyper | cancer_general | BC038725, SOX14 |
| chr3 | 137484405 | 137484531 | Hyper | cancer_general | BC038725 | chr3 | 137486029 | 137486310 | Hyper | cancer_general | BC038725 |
| chr3 | 137486516 | 137486550 | Hyper | cancer_general | SOX14, BC038725 | chr3 | 137487964 | 137488021 | Hyper | cancer_general | SOX14 |
| chr3 | 137488950 | 137491040 | Hyper | tcga, cancer_general | BC038725, SOX14 | chr3 | 138067717 | 138067747 | Hyper | blood | MRAS |
| chr3 | 138153963 | 138153993 | Hyper | cancer_general | ESYT3 | chr3 | 138154340 | 138154377 | Hyper | cancer_general | ESYT3 |
| chr3 | 138374229 | 138374258 | Hyper | literature | PIK3CB | chr3 | 138655934 | 138656138 | Hyper | cancer_general | FOXL2, C3orf72, AK128202 |
| chr3 | 138656834 | 138656889 | Hyper | cancer_general | C3orf72, AK304483, AK128202, OFXL2 | chr3 | 138657414 | 138659099 | Hyper | tcga, cancer_general | AK128202, FOXL2, C3orf72, AK304483 |
| chr3 | 138662134 | 138662164 | Hyper | cancer_general | FOXL2, C3orf72, AK304483, AK128202 | chr3 | 138662382 | 138662448 | Hyper | cancer_general | FOXL2, C3orf72, AK304483, AK128202 |
| chr3 | 138662799 | 138662842 | Hyper | cancer_general | FOXL2, C3orf72, AK304483, AK128202 | chr3 | 138663613 | 138664165 | Hyper | cancer_general | C3orf72, AK304483, FOXL2, AK128202 |
| chr3 | 138664408 | 138664489 | Hyper | cancer_general | AK304483, FOXL2, AK128202, C3orf72 | chr3 | 138664928 | 138665323 | Hyper | cancer_general | C3orf72, AK304483, FOXL2, AK128202 |
| chr3 | 138665562 | 138666294 | Hyper | cancer_general, liver_tcga, tcga | AK128202, C3orf72, AK304483, FOXL2 | chr3 | 138668742 | 138669387 | Hyper | cancer_general | AK128202, AK304483, C3orf72, FOXL2 |
| chr3 | 138679462 | 138679526 | Hyper | cancer_general | AK304483, C3orf72 | chr3 | 139258267 | 139258316 | Hyper | cancer_general | RBP1 |
| chr3 | 139653491 | 139653693 | Hyper | cancer_general | CLSTN2 | chr3 | 140769513 | 140769705 | Hyper | cancer_general | SPSB4 |
| chr3 | 140769908 | 140770829 | Hyper | tcga, pancreas, cancer_general | SPSB4 | chr3 | 140771305 | 140771335 | Hyper | cancer_general | SPSB4 |
| chr3 | 140771816 | 140771854 | Hyper | cancer_general | SPSB4 | chr3 | 141516389 | 141516719 | Hyper | cancer_general | GRK7 |
| chr3 | 142682273 | 142682392 | Hyper | tcga | PAQR9, KA093381 | chr3 | 142837980 | 142838370 | Hyper | tcga, cancer_general | CHST2 |
| chr3 | 142838621 | 142839036 | Hyper | tcga, cancer_general | CHST2 | chr3 | 142839539 | 142840236 | Hyper | tcga, colorectal, liver_tcga, cancer_general | CHST2 |
| chr3 | 145878665 | 145878695 | Hyper | blood | — | chr3 | 147074457 | 147074487 | Hyper | cancer_general | — |
| chr3 | 147074974 | 147075006 | Hyper | cancer_general | — | chr3 | 147077289 | 147077671 | Hyper | liver_tcga, cancer_general | — |
| chr3 | 147078959 | 147079188 | Hyper | cancer_general | — | chr3 | 147087562 | 147087799 | Hyper | cancer_general | — |
| chr3 | 147088440 | 147088523 | Hyper | cancer_general | — | chr3 | 147088939 | 147089099 | Hyper | cancer_general | — |
| chr3 | 147098431 | 147098470 | Hyper | cancer_general | ZIC4 | chr3 | 147105898 | 147106010 | Hyper | liver_tcga | ZIC4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 147108841 | 147109932 | Hyper | cancer_general | ZIC4 | chr3 | 147110145 | 147110683 | Hyper | cancer_general | ZIC4 |
| chr3 | 147110927 | 147111089 | Hyper | cancer_general | ZIC4 | chr3 | 147111545 | 147111674 | Hyper | literature, cancer_general | ZIC4 |
| chr3 | 147125697 | 147125726 | Hyper | literature | ZIC1, ZIC4 | chr3 | 147127037 | 147127067 | Hyper | cancer_general | ZIC1, ZIC4 |
| chr3 | 147127681 | 147127902 | Hyper | cancer_general | ZIC1, ZIC4 | chr3 | 147128287 | 147128326 | Hyper | cancer_general | ZIC1, ZIC4 |
| chr3 | 147136931 | 147137164 | Hyper | cancer_general | ZIC1 | chr3 | 147138768 | 147138856 | Hyper | cancer_general | ZIC1 |
| chr3 | 147139126 | 147139156 | Hyper | cancer_general | ZIC1 | chr3 | 147139374 | 147139528 | Hyper | cancer_general | ZIC1 |
| chr3 | 147142225 | 147142265 | Hyper | cancer_general | ZIC1 | chr3 | 148415427 | 148415644 | Hyper | cancer_general | AGTR1 |
| chr3 | 149374947 | 149375023 | Hyper | cancer_general | WWTR1-AS1, AK309441 | chr3 | 150802981 | 150803080 | Hyper | cancer_general | MED12L, CLRN1-AS1 |
| chr3 | 150804043 | 150804077 | Hyper | tcga | MED12L, CLRN1-AS1 | chr3 | 150804967 | 150805030 | Hyper | cancer_general | MED12L, CLRN1-AS1 |
| chr3 | 152553343 | 152553384 | Hyper | cancer_general | P2RY1 | chr3 | 152553658 | 152553725 | Hyper | tcga, blood, cancer_general | P2RY1 |
| chr3 | 153838818 | 153838870 | Hyper | blood | ARHGEF26-AS1, ARHGEF26 | chr3 | 153839518 | 153840057 | Hyper |  | ARHGEF26, ARHGEF26-AS1 |
| chr3 | 154146133 | 154146412 | Hyper | cancer_general | GPR149 | chr3 | 154146654 | 154146908 | Hyper | cancer_general | GPR149 |
| chr3 | 154797334 | 154797703 | Hyper | cancer_general, tcga, head_neck | MME | chr3 | 155463041 | 155463071 | Hyper | hepatobiliary | — |
| chr3 | 156008976 | 156009425 | Hyper | cancer_general | KCNAB1 | chr3 | 156534302 | 156534332 | Hyper | cancer_general | AK094480, LEKR1, AP2G4P4, LINC00886 |
| chr3 | 157155252 | 157155490 | Hyper | tcga, cancer_general | PTX3, VEPH1, Mir_584 | chr3 | 157155982 | 157156194 | Hyper | cancer_general, tcga | VEPH1, Mir_584, PTX3 |
| chr3 | 157812196 | 157812645 | Hyper | cancer_general | SHOX2 | chr3 | 157812912 | 157813070 | Hyper | cancer_general | SHOX2 |
| chr3 | 157813608 | 157813824 | Hyper | literature, cancer_general | SHOX2 | chr3 | 157814311 | 157814340 | Hyper | literature | SHOX2 |
| chr3 | 157815657 | 157815822 | Hyper | literature | SHOX2 | chr3 | 157820576 | 157820605 | Hyper | cancer_general | RSRC1, SHOX2 |
| chr3 | 157821085 | 157821662 | Hyper | literature, cancer_general | RSRC1, SHOX2 | chr3 | 157821904 | 157822008 | Hyper | literature | RSRC1, SHOX2 |
| chr3 | 157823073 | 157823143 | Hyper | cancer_general | RSRC1, SHOX2 | chr3 | 157823464 | 157823493 | Hyper | literature | RSRC1, SHOX2 |
| chr3 | 157824133 | 157824231 | Hyper | literature | RSRC1, SHOX2 | chr3 | 157824495 | 157824871 | Hyper | literature, cancer_general | RSRC1, SHOX2 |
| chr3 | 157825176 | 157825408 | Hyper | cancer_general | RSRC1, SHOX2 | chr3 | 158288836 | 158288872 | Hyper | liver_tcga | MLF1, AK097794 |
| chr3 | 159756687 | 159756856 | Hyper | cancer_general | — | chr3 | 159944486 | 159944546 | Hyper | cancer_general | IFT80, C3orf80 |
| chr3 | 160168003 | 160168033 | Hyper | cancer_general | — | chr3 | 164912376 | 164912568 | Hyper | cancer_general | SLITRK3 |
| chr3 | 164912907 | 164913872 | Hyper | cancer_general | SLITRK3 | chr3 | 164914980 | 164915129 | Hyper | cancer_general | SLITRK3 |
| chr3 | 169376183 | 169376215 | Hyper | cancer_general | — | chr3 | 169376680 | 169376780 | Hyper | cancer_general | — |
| chr3 | 169378825 | 169379024 | Hyper | cancer_general | — | chr3 | 170136627 | 170136751 | Hyper | cancer_general | CLDN11 |
| chr3 | 170137667 | 170137772 | Hyper | cancer_general | CLDN11 | chr3 | 170302617 | 170302677 | Hyper | cancer_general | BC039437, SLC7A14 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 170303087 | 170303129 | Hyper | cancer_general | BC039437, SLC7A14 | chr3 | 170303331 | 170303423 | Hyper | cancer_general | BC039437, SLC7A14 |
| chr3 | 170303639 | 170303844 | Hyper | liver_tcga, cancer_general | BC039437, SLC7A14 | chr3 | 171527930 | 171527971 | Hyper | blood | — |
| chr3 | 172165443 | 172166627 | Hyper | cancer_general | GHSR, GU289929 | chr3 | 172166879 | 172167044 | Hyper | cancer_general | GHSR, GU289929 |
| chr3 | 172167297 | 172167327 | Hyper | cancer_general | GHSR, GU289929 | chr3 | 172167660 | 172167917 | Hyper | cancer_general | GHSR |
| chr3 | 173115237 | 173115550 | Hyper | tcga | NLGN1 | chr3 | 173302542 | 173302684 | Hyper | cancer_general | NLGN1 |
| chr3 | 173302992 | 173303225 | Hyper | cancer_general | NLGN1 | chr3 | 178916711 | 178916959 | Hyper | literature | PIK3CA |
| chr3 | 178921537 | 178921568 | Hyper | literature | PIK3CA | chr3 | 178927966 | 178928094 | Hyper | literature | PIK3CA |
| chr3 | 178936059 | 178936111 | Hyper | literature | PIK3CA | chr3 | 178952004 | 178952105 | Hyper | literature | KCNMB3, PIK3CA |
| chr3 | 179168661 | 179169266 | Hyper | liver_tcga, colorectal, cancer_general | GNB4 | chr3 | 179754178 | 179755372 | Hyper | cancer_general | — |
| chr3 | 180320256 | 180320294 | Hyper | esophageal | TTC14 | | | | | | |
| chr3 | 181413742 | 181414330 | Hyper | tcga, cancer_general | JA611300, SOX2-OT | chr3 | 181413084 | 181413355 | Hyper | cancer_general | JA611300, SOX2, SOX2-OT |
| chr3 | 181420316 | 181420374 | Hyper | cancer_general | SOX2, JA611300, SOX2-OT | chr3 | 181420065 | 181420116 | Hyper | cancer_general | SOX2, JA611300, SOX2-OT |
| chr3 | 181422541 | 181422985 | Hyper | cancer_general | SOX2, JA611300, SOX2-OT | chr3 | 181421411 | 181422282 | Hyper | tcga, cancer_general | JA611300, SOX2-OT |
| | | | | | | chr3 | 181428388 | 181428772 | Hyper | cancer_general | SOX2 |
| chr3 | 181430695 | 181430771 | Hyper | cancer_general | SOX2 | chr3 | 181437129 | 181437349 | Hyper | cancer_general | SOX2 |
| chr3 | 181438194 | 181438353 | Hyper | cancer_general | SOX2 | chr3 | 181440892 | 181441927 | Hyper | literature, cancer_general | SOX2 |
| chr3 | 181442145 | 181442410 | Hyper | lung, cancer_general | SOX2 | chr3 | 181443014 | 181443557 | Hyper | cancer_general | — |
| chr3 | 181443760 | 181443861 | Hyper | cancer_general | — | chr3 | 181444434 | 181445013 | Hyper | cancer_general | — |
| chr3 | 181445369 | 181445464 | Hyper | cancer_general | — | chr3 | 181445735 | 181445861 | Hyper | cancer_general | — |
| chr3 | 183145412 | 183145618 | Hyper | literature, cancer_general | — | chr3 | 183145931 | 183146025 | Hyper | literature | — |
| chr3 | 183146397 | 183146435 | Hyper | literature | CHRD, THPO | chr3 | 183146648 | 183146677 | Hyper | literature | EPHB3 |
| chr3 | 184099417 | 184099446 | Hyper | literature | CHRD, THPO | chr3 | 184301734 | 184301772 | Hyper | cancer_general | EPHB3 |
| chr3 | 184319424 | 184319612 | Hyper | pancreas | — | chr3 | 184319828 | 184319891 | Hyper | pancreas | — |
| chr3 | 186078766 | 186078898 | Hyper | cancer_general | — | chr3 | 186079204 | 186079331 | Hyper | cancer_general | — |
| chr3 | 186080188 | 186080218 | Hyper | cancer_general | — | chr3 | 186857152 | 186857607 | Hyper | tcga, cancer_general | — |
| chr3 | 187387850 | 187388239 | Hyper | cancer_general | SST | chr3 | 192125828 | 192125858 | Hyper | cancer_general | FGF12 |
| chr3 | 192126146 | 192126863 | Hyper | cancer_general, tcga | FGF12 | chr3 | 192127354 | 192128074 | Hyper | cancer_general | FGF12 |
| chr3 | 192232097 | 192232175 | Hyper | cancer_general | FGF12 | chr3 | 192232452 | 192232570 | Hyper | cancer_general | FGF12 |
| chr3 | 192232834 | 192233150 | Hyper | cancer_general | FGF12 | chr3 | 192958725 | 192958968 | Hyper | liver_tcga | FGF12, HRASLS, MGC2889 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr3 | 193776089 | 193776119 | Hyper | cancer_general | BC038368 | chr3 | 194120008 | 194120164 | Hyper | literature | ATP13A3, GP5 |
| chr3 | 194120934 | 194120963 | Hyper | literature | ATP13A3, GP5 | chr3 | 194208286 | 194208562 | Hyper | cancer_general | AX746839, LINC00884 |
| chr3 | 194407998 | 194408028 | Hyper | pancreas | FAM43A | chr3 | 194408375 | 194409021 | Hyper | liver_tcga, cancer_general, tcga | FAM43A |
| chr3 | 196255617 | 196255646 | Hyper | liver_tcga | — | chr3 | 196755958 | 196755987 | Hyper | liver_tcga | MFI2 IQCG, RPL35A |
| chr3 | 197236945 | 197237111 | Hyper | hepatobiliary | BDH1 | chr3 | 197677029 | 197677058 | Hyper | literature | |
| chr3 | 197686941 | 197687223 | Hyper | literature | LMLN, RPL35A | chr3 | 197687694 | 197687723 | Hyper | literature | LMLN, RPL35A |
| chr2 | 46214 | 46450 | Hyper | blood | FAM110C | chr2 | 264163 | 264204 | Hyper | liver_tcga | ACP1, SH3YL1 |
| chr2 | 287580 | 287641 | Hyper | cancer_general | FAM150B | chr2 | 288404 | 288470 | Hyper | cancer_general | FAM150B |
| chr2 | 468045 | 468078 | Hyper | cancer_general | — | chr2 | 468299 | 468672 | Hyper | tcga, cancer_general | — |
| chr2 | 945913 | 946000 | Hyper | cancer_general | SNTG2 | chr2 | 946208 | 946263 | Hyper | cancer_general | SNTG2 |
| chr2 | 946526 | 946610 | Hyper | cancer_general | SNTG2 | chr2 | 946896 | 947159 | Hyper | cancer_general | SNTG2 |
| chr2 | 1746614 | 1747210 | Hyper | cancer_general | PXDN | chr2 | 1747670 | 1748890 | Hyper | cancer_general | PXDN |
| chr2 | 3750947 | 3750977 | Hyper | liver_tcga | ALLC | chr2 | 3751335 | 3751439 | Hyper | cancer_general | ALLC |
| chr2 | 5831178 | 5831324 | Hyper | cancer_general | SOX11 | chr2 | 5831789 | 5831819 | Hyper | cancer_general | SOX11 |
| chr2 | 5832069 | 5832222 | Hyper | cancer_general | SOX11 | chr2 | 5832890 | 5834028 | Hyper | cancer_general, pancreas | SOX11 |
| chr2 | 5836085 | 5836253 | Hyper | cancer_general | SOX11 | chr2 | 5836548 | 5837071 | Hyper | tcga, cancer_general | SOX11 |
| chr2 | 5837278 | 5837414 | Hyper | cancer_general | SOX11 | chr2 | 5866098 | 5866211 | Hyper | cancer_general | — |
| chr2 | 7571510 | 7571747 | Hyper | pancreas, cancer_general | LOC100506274 | chr2 | 10182827 | 10182904 | Hyper | cancer_general | KLF11 |
| chr2 | 10688874 | 10688904 | Hyper | cancer_general | — | chr2 | 11052517 | 11052559 | Hyper | cancer_general | KCNF1 |
| chr2 | 11809957 | 11810117 | Hyper | cancer_general | LPIN1, NTSR2 | chr2 | 12858452 | 12858618 | Hyper | tcga, colorectal | TRIB2 |
| chr2 | 14772761 | 14772823 | Hyper | blood | FAM84A, AX747684 | chr2 | 14774281 | 14774567 | Hyper | blood | AX747684, FAM84A |
| chr2 | 17719688 | 17719812 | Hyper | cancer_general | VSNL1 | chr2 | 18059035 | 18059085 | Hyper | cancer_general | KCNS3 |
| chr2 | 18059781 | 18059841 | Hyper | pancreas | KCNS3 | chr2 | 19550214 | 19550244 | Hyper | cancer_general | OSR1, MIR4757 |
| chr2 | 19551322 | 19551366 | Hyper | cancer_general | OSR1, MIR4757 | chr2 | 19556318 | 19556672 | Hyper | blood | OSR1, MIR4757 |
| chr2 | 19557068 | 19557098 | Hyper | cancer_general | OSR1, MIR4757 | chr2 | 19557685 | 19557727 | Hyper | blood | OSR1, MIR4757 |
| chr2 | 19558832 | 19558893 | Hyper | cancer_general | OSR1 | chr2 | 19561131 | 19561316 | Hyper | cancer_general | OSR1 |
| chr2 | 19561517 | 19561685 | Hyper | cancer_general | OSR1 | chr2 | 19563358 | 19563433 | Hyper | cancer_general | OSR1 |
| chr2 | 20068798 | 20068885 | Hyper | cancer_general | LINC00954 | chr2 | 20865636 | 20865927 | Hyper | tcga, cancer_general | GDF7 |
| chr2 | 25390994 | 25391212 | Hyper | cancer_general | POMC, EFR3B | chr2 | 25391684 | 25391725 | Hyper | cancer_general | POMC, EFR3B |
| chr2 | 25438821 | 25439465 | Hyper | tcga, liver_tcga, cancer_general | — | chr2 | 26395447 | 26395556 | Hyper | liver_tcga | GAREML |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 26402030 | 26402060 | Hyper | cancer_general | GAREML | chr2 | 26407492 | 26408181 | Hyper | tcga, cancer_general | HADHA, GAREML |
| chr2 | 26521972 | 26522221 | Hyper | cancer_general | HADHB, GPR113 | chr2 | 26915763 | 26916259 | Hyper | cancer_general | KCNK3 |
| chr2 | 27070324 | 27070414 | Hyper | cancer_general | DPYSL5 | chr2 | 27071240 | 27071346 | Hyper | tcga | DPYSL5 |
| chr2 | 27072492 | 27072534 | Hyper | cancer_general | DPYSL5 | chr2 | 27072822 | 27072989 | Hyper | cancer_general | DPYSL5 |
| chr2 | 27665125 | 27665154 | Hyper | liver_tcga | KRTCAP3, IFT172, NRBP1 | chr2 | 27665506 | 27665711 | Hyper | liver_tcga | IFT172, KRTCAP3, NRBP1 |
| chr2 | 29033336 | 29033924 | Hyper | cancer_general | SPDYA, PPP1CB | chr2 | 29338084 | 29338969 | Hyper | colorectal, cancer_general | CLIP4 |
| chr2 | 29420483 | 29420512 | Hyper | literature | ALK | chr2 | 29432640 | 29432696 | Hyper | literature | ALK |
| chr2 | 29436844 | 29436888 | Hyper | literature | ALK | chr2 | 29443573 | 29443710 | Hyper | literature | ALK |
| chr2 | 29445198 | 29445482 | Hyper | literature | ALK | chr2 | 29446361 | 29446396 | Hyper | literature | ALK |
| chr2 | 30143304 | 30143492 | Hyper | cancer_general | — | chr2 | 30144041 | 30144411 | Hyper | tcga, cancer_general | — |
| chr2 | 30453714 | 30453941 | Hyper | cancer_general | LBH | chr2 | 31360306 | 31360831 | Hyper | colorectal | GALNT14 |
| chr2 | 31361089 | 31361118 | Hyper | tcga | GALNT14 | chr2 | 31361356 | 31361385 | Hyper | tcga | GALNT14 |
| chr2 | 31456682 | 31457039 | Hyper | tcga, esophageal, colorectal | EHD3, 5S_rRNA, CAPN14 | richr2 | 38302253 | 38302876 | Hyper | cancer_general | CYP1B1 |
| chr2 | 39187218 | 39187722 | Hyper | liver_tcga, cancer_general | LOC375196, ARHGEF33 | chr2 | 39893090 | 39893501 | Hyper | cancer_general | TMEM178A |
| chr2 | 39893972 | 39894059 | Hyper | cancer_general | TMEM178A | chr2 | 40678603 | 40679620 | Hyper | tcga, cancer_general | SLC8A1 |
| chr2 | 42274595 | 42274633 | Hyper | tcga | PKDCC | chr2 | 42329431 | 42329666 | Hyper | tcga | — |
| chr2 | 42720262 | 42720546 | Hyper | cancer_general | KCNG3, MTA3 | chr2 | 43019599 | 43019868 | Hyper | tcga | HAAO |
| chr2 | 43451909 | 43452327 | Hyper | lung | LOC100129726, THADA, ZFP36L2 | chr2 | 45028988 | 45029371 | Hyper | cancer_general | — |
| chr2 | 45029682 | 45029712 | Hyper | cancer_general | — | chr2 | 45155125 | 45157711 | Hyper | cancer_general | SIX3 |
| chr2 | 45159956 | 45160267 | Hyper | cancer_general | SIX3 | chr2 | 45160596 | 45160634 | Hyper | cancer_general | SIX3 |
| chr2 | 45161663 | 45162112 | Hyper | cancer_general | SIX3 | chr2 | 45162394 | 45162481 | Hyper | cancer_general | SIX3 |
| chr2 | 45162751 | 45162913 | Hyper | cancer_general | SIX3 | chr2 | 45164663 | 45164693 | Hyper | cancer_general | SIX3 |
| chr2 | 45165564 | 45165594 | Hyper | cancer_general | SIX3 | chr2 | 45168803 | 45168833 | Hyper | cancer_general | SIX3 |
| chr2 | 45169446 | 45170029 | Hyper | liver_tcga, cancer_general | SIX3 | chr2 | 45171385 | 45171862 | Hyper | liver_tcga, cancer_general | SIX3 |
| chr2 | 45176601 | 45176768 | Hyper | cancer_general | SIX3 | chr2 | 45179620 | 45179650 | Hyper | cancer_general | SIX3 |
| chr2 | 45179939 | 45180203 | Hyper | cancer_general | SIX3 | chr2 | 45181520 | 45181672 | Hyper | cancer_general | SIX3 |
| chr2 | 45181887 | 45182001 | Hyper | cancer_general | SIX3 | chr2 | 45228618 | 45228730 | Hyper | tcga | SIX2 |
| chr2 | 45231320 | 45231396 | Hyper | cancer_general | SIX2 | chr2 | 45231805 | 45232131 | Hyper | cancer_general | SIX2 |
| chr2 | 45233385 | 45233586 | Hyper | cancer_general | SIX2 | chr2 | 45235594 | 45235926 | Hyper | cancer_general | SIX2 |
| chr2 | 45237673 | 45237795 | Hyper | tcga, cancer_general | SIX2 | chr2 | 45240548 | 45240784 | Hyper | liver_tcga, cancer_general | SIX2 |
| chr2 | 45241136 | 45241184 | Hyper | cancer_general | SIX2 | chr2 | 45395854 | 45395920 | Hyper | cancer_general | UNQ6975 |
| chr2 | 45396315 | 45396451 | Hyper | cancer_general | UNQ6975 | chr2 | 45396688 | 45396995 | Hyper | cancer_general | UNQ6975 |
| chr2 | 46326302 | 46526448 | Hyper | blood | EPAS1 | chr2 | 47748140 | 47748494 | Hyper | cancer_general | KCNK12 |
| chr2 | 47797043 | 47797818 | Hyper | tcga, cancer_general | KCNK12 | chr2 | 47798180 | 47798663 | Hyper | cancer_general | KCNK12 |

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 47798954 | 47791109 | Hyper | cancer_general | KCNK12 | chr2 | 48982582 | 48982866 | Hyper | cancer_general | LHCGR |
| chr2 | 50573595 | 50573803 | Hyper | cancer_general | NRXN1 | chr2 | 50574121 | 50574859 | Hyper | tcga, cancer_general | NRXN1 |
| chr2 | 56149836 | 56149866 | Hyper | cancer_general | EFEMP1 | chr2 | 56150729 | 56151193 | Hyper | tcga, cancer_general | EFEMP1 |
| chr2 | 56410817 | 56410996 | Hyper | esophageal | CCDC85A, AK311113, AK295617 | chr2 | 56411691 | 56411733 | Hyper | esophageal | AK295617, CCDC85A, AK311113 |
| chr2 | 58656049 | 58656125 | Hyper | tcga, cancer_general | — | chr2 | 60796587 | 60796646 | Hyper | cancer_general | — |
| chr2 | 60797137 | 60797281 | Hyper | cancer_general | — | chr2 | 62798343 | 62798386 | Hyper | cancer_general | OTX1, LOC100132215 |
| chr2 | 63275563 | 63275855 | Hyper | cancer_general | OTX1, LOC100132215 | chr2 | 63278962 | 63278992 | Hyper | cancer_general | OTX1, LOC100132215 |
| chr2 | 63280952 | 63281651 | Hyper | liver_tcga, cancer_general, tcga | OTX1, LOC100132215 | chr2 | 63282716 | 63282786 | Hyper | cancer_general | OTX1, LOC100132215 |
| chr2 | 63282998 | 63283027 | Hyper | literature | OTX1, LOC100132215 | chr2 | 63283952 | 63284146 | Hyper | liver_tcga, literature | OTX1, LOC100132215 |
| chr2 | 63284777 | 63284811 | Hyper | cancer_general | OTX1, LOC100132215 | chr2 | 63285081 | 63287368 | Hyper | liver_tcga, literature, cancer_general | OTX1 |
| chr2 | 66652863 | 66652963 | Hyper | tcga | MEIS1, MEIS1-AS3 | chr2 | 66653238 | 66653496 | Hyper | cancer_general | MEIS1, EMIS1-AS3 |
| chr2 | 66653764 | 66653914 | Hyper | cancer_general | MEIS1, MEIS1-AS3 | chr2 | 66660650 | 66660888 | Hyper | tcga | MEIS1-AS3, MEIS1 |
| chr2 | 66662749 | 66662824 | Hyper | tcga | MEIS1, MEIS1-AS3 | chr2 | 66808525 | 66809361 | Hyper | tcga, cancer_general | MEIS1 |
| chr2 | 68546324 | 68546892 | Hyper | tcga, cancer_general | CNRIP1 | chr2 | 71503790 | 71503823 | Hyper | cancer_general | ZNF638 |
| chr2 | 71504103 | 71504148 | Hyper | cancer_general | ZNF638 | chr2 | 71680833 | 71680863 | Hyper | cancer_general | DYSF |
| chr2 | 71693374 | 71693593 | Hyper | tcga | DYSF | chr2 | 72374375 | 72374432 | Hyper | cancer_general | CYP26B1 |
| chr2 | 72374694 | 72374765 | Hyper | cancer_general | CYP26B1 | chr2 | 73145640 | 73145694 | Hyper | cancer_general | EMX1 |
| chr2 | 73145924 | 73146021 | Hyper | cancer_general | EMX1 | chr2 | 73147324 | 73148243 | Hyper | tcga, cancer_general | EMX1 |
| chr2 | 73150924 | 73150954 | Hyper | cancer_general | EMX1 | chr2 | 73151187 | 73151831 | Hyper | liver_tcga, cancer_general | EMX1 |
| chr2 | 73152683 | 73152754 | Hyper | cancer_general | EMX1 | chr2 | 73429523 | 73429614 | Hyper | cancer_general | NOTO |
| chr2 | 73429952 | 73430069 | Hyper | cancer_general | NOTO | chr2 | 73430322 | 73430743 | Hyper | cancer_general | NOTO |
| chr2 | 73518448 | 73518919 | Hyper | cancer_general | EGR4, U6, AK125051 | chr2 | 73519579 | 73519841 | Hyper | cancer_general | U6, EGR4, AK125051 |
| chr2 | 74426185 | 74426214 | Hyper | liver_tcga | MTHFD2 | chr2 | 74726744 | 74726774 | Hyper | cancer_general | LBX2-AS1, PCGF1, LBX2, TTC31 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 74740852 | 74741387 | Hyper | liver_tga, cancer_general | LBX2-AS1, TLX2, DQX1, PCGF1 | chr2 | 74741835 | 74741955 | Hyper | tcga, cancer_general | DQX1, TLX2, PCGF1, LBX2-AS1 |
| chr2 | 74742176 | 74743732 | Hyper | liver_tga, cancer_general | DQX1, TLX2, PCGF1, LBX2-AS1 | chr2 | 74782081 | 74782271 | Hyper | liver_tga, cancer_general | DOK1, MIAP, LOXL3 |
| chr2 | 75427040 | 75427114 | Hyper | | — | chr2 | 75427369 | 75427399 | Hyper | blood | — |
| chr2 | 75427930 | 75428177 | Hyper | cancer_general, tcga | — | chr2 | 75720510 | 75720541 | Hyper | liver_tga | EVA1A |
| chr2 | 80529378 | 80529443 | Hyper | cancer_general | CTNNA2, LRRTM1 | chr2 | 80529662 | 80530022 | Hyper | cancer_general | CTNNA2, LRRTM1 |
| chr2 | 80530505 | 80530558 | Hyper | cancer_general | CTNNA2, LRRTM1 | chr2 | 80531725 | 80531755 | Hyper | cancer_general | CTNNA2, LRRTM1 |
| chr2 | 80549585 | 80549745 | Hyper | cancer_general | CTNNA2 | chr2 | 85107454 | 85107538 | Hyper | cancer_general | TRABD2A |
| chr2 | 85361317 | 85361609 | Hyper | cancer_general | TCF7L1 | chr2 | 86263223 | 86263270 | Hyper | liver_tga | POLR1A |
| chr2 | 87016579 | 87016636 | Hyper | cancer_general | CD8A, RMND5A | chr2 | 87017796 | 87018396 | Hyper | liver_tga, cancer_general | RMND5A, CD8A |
| chr2 | 87036611 | 87036640 | Hyper | literature | CD8B | chr2 | 88751281 | 88751800 | Hyper | tcga, cancer_general | FOXI3 |
| chr2 | 88752055 | 88752285 | Hyper | liver_tga, cancer_general | FOXI3 | chr2 | 88752603 | 88752785 | Hyper | cancer_general | FOXI3 |
| chr2 | 89064610 | 89065278 | Hyper | literature, cancer_general | ANKRD36BP2 | chr2 | 95663969 | 95664014 | Hyper | cancer_general | — |
| chr2 | 95690747 | 95690793 | Hyper | cancer_general | MAL | chr2 | 95691036 | 95691269 | Hyper | tcga, literature | MAL |
| chr2 | 95691530 | 95691769 | Hyper | literature, cancer_general | MAL | chr2 | 95691994 | 95692480 | Hyper | cancer_general, literature | MAL |
| chr2 | 96990898 | 96991316 | Hyper | literature, cancer_general | ITPRIPL1 | chr2 | 97193097 | 97193626 | Hyper | cancer_general | ARID5A |
| chr2 | 98703323 | 98703475 | Hyper | liver_tga | VWA3B | chr2 | 98703675 | 98703736 | Hyper | hepatobiliary | VWA3B |
| chr2 | 98962898 | 98962940 | Hyper | cancer_general | CNGA3 | chr2 | 98963329 | 98963599 | Hyper | cancer_general | CNGA3 |
| chr2 | 98963838 | 98964200 | Hyper | cancer_general | CNGA3 | chr2 | 98964596 | 98964645 | Hyper | cancer_general | CNGA3 |
| chr2 | 99439138 | 99439507 | Hyper | pancreas, cancer_general | KIAA1211L | chr2 | 99553391 | 99553656 | Hyper | tcga | KIAA1211L |
| chr2 | 100937836 | 100939155 | Hyper | tcga, colorectal, cancer_general | LONRF2 | chr2 | 101034242 | 101034293 | Hyper | tcga | CHST10 |
| chr2 | 101436632 | 101436708 | Hyper | blood | NPAS2 | chr2 | 101666893 | 101667004 | Hyper | liver_tga | TBC1D8 |
| chr2 | 102091180 | 102091335 | Hyper | tcga | RFX8 | chr2 | 103236165 | 103236292 | Hyper | blood | SLC9A2 |
| chr2 | 105459081 | 105459518 | Hyper | cancer_general | LOC100506421 | chr2 | 105459908 | 105460599 | Hyper | cancer_general | LOC100506421 |
| chr2 | 105460921 | 105460951 | Hyper | cancer_general | LOC100506421 | chr2 | 105461187 | 105461243 | Hyper | cancer_general | LOC100506421 |
| chr2 | 105461564 | 105461896 | Hyper | cancer_general | LOC100506421 | chr2 | 105462165 | 105462222 | Hyper | cancer_general | POU3F3, LOC100506421 |
| chr2 | 105468791 | 105468908 | Hyper | cancer_general | LOC100506421, POU3F3 | chr2 | 105469645 | 105470091 | Hyper | cancer_general | POU3F3, LOC100506421 |
| chr2 | 105470350 | 105470840 | Hyper | tcga, literature, cancer_general, liver_tga | POU3F3, LOC100506421 | chr2 | 105472231 | 105472845 | Hyper | cancer_general | AK095498, POU3F3, LOC100506421 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 105473248 | 105473553 | Hyper | cancer_general | AK095498, POU3F3, LOC100506421 | chr2 | 105478762 | 105479089 | Hyper | cancer_general | AK095498, POU3F3 |
| chr2 | 105480530 | 105480595 | Hyper | cancer_general | AK095498, POU3F3 | chr2 | 105483655 | 105483719 | Hyper | cancer_general | AK095498 |
| chr2 | 105484450 | 105484522 | Hyper | cancer_general | AK095498 | chr2 | 105760981 | 105761037 | Hyper | cancer_general | C2orf40 |
| chr2 | 106681733 | 106681767 | Hyper | cancer_general | C2orf40 | chr2 | 106682012 | 106682098 | Hyper | cancer_general | ST6GAL2 |
| chr2 | 107103865 | 107103928 | Hyper | cancer_general | — | chr2 | 107502600 | 107502815 | Hyper | tcga, cancer_general | ST6GAL2 |
| chr2 | 107503218 | 107503328 | Hyper | tcga, cancer_general | ST6GAL2 | chr2 | 107503532 | 107503561 | Hyper | tcga | ST6GAL2 |
| chr2 | 107503884 | 107504018 | Hyper | cancer_general | ST6GAL2 | chr2 | 109648080 | 109648222 | Hyper | tcga | — |
| chr2 | 109745989 | 109746079 | Hyper | cancer_general | SH3RF3, SH3RF3-AS1 | chr2 | 109746289 | 109746477 | Hyper | cancer_general | SH3RF3, SH3RF3-AS1 |
| chr2 | 110370941 | 110371219 | Hyper | blood | SOWAHC | chr2 | 110873016 | 110873045 | Hyper | literature | NPHP1 |
| chr2 | 111875191 | 111875611 | Hyper | lung, cancer_general | AK125994, BCL2L11 | chr2 | 111876698 | 111876870 | Hyper | cancer_general | BCL2L11, AK125994 |
| chr2 | 112657033 | 112657092 | Hyper | cancer_general | MERTK | chr2 | 113594639 | 113594668 | Hyper | literature | IL1B |
| chr2 | 113931503 | 113931532 | Hyper | literature | PSD4 | chr2 | 114034892 | 114035180 | Hyper | cancer_general | PAX8 |
| chr2 | 114256978 | 114257137 | Hyper | cancer_general | FOXD4L1, CBWD2 | chr2 | 114261300 | 114261458 | Hyper | cancer_general | FOXD4L1, CBWD2 |
| chr2 | 115918661 | 115920534 | Hyper | tcga, cancer_general | LOC389023, DPP10 | chr2 | 118981151 | 118982497 | Hyper | cancer_general, tcga, lung | — |
| chr2 | 119067636 | 119068049 | Hyper | liver_tcga, cancer_general | — | chr2 | 119532161 | 119532255 | Hyper | cancer_general | — |
| chr2 | 119566239 | 119566272 | Hyper | cancer_general | — | chr2 | 119591351 | 119591465 | Hyper | cancer_general | EN1 |
| chr2 | 119592588 | 119592777 | Hyper | tcga, cancer_general | EN1 | chr2 | 119592997 | 119593567 | Hyper | tcga, cancer_general | EN1 |
| chr2 | 119599926 | 119600031 | Hyper | cancer_general | EN1 | chr2 | 119600332 | 119600555 | Hyper | cancer_general | EN1 |
| chr2 | 119600949 | 119601061 | Hyper | cancer_general | EN1 | chr2 | 119602601 | 119603086 | Hyper | cancer_general | EN1 |
| chr2 | 119604032 | 119604158 | Hyper | cancer_general | EN1 | chr2 | 119604809 | 119604851 | Hyper | cancer_general | EN1 |
| chr2 | 119606135 | 119606558 | Hyper | cancer_general | EN1 | chr2 | 119606783 | 119606839 | Hyper | cancer_general | EN1 |
| chr2 | 119607176 | 119607411 | Hyper | cancer_general | EN1 | chr2 | 119607783 | 119607842 | Hyper | cancer_general | EN1 |
| chr2 | 119610844 | 119610969 | Hyper | cancer_general | EN1 | chr2 | 119611745 | 119611799 | Hyper | cancer_general | EN1 |
| chr2 | 119612324 | 119612354 | Hyper | cancer_general | EN1 | chr2 | 119614130 | 119614171 | Hyper | cancer_general | EN1 |
| chr2 | 119614780 | 119614852 | Hyper | cancer_general | EN1 | chr2 | 119615055 | 119615627 | Hyper | cancer_general | EN1 |
| chr2 | 119616155 | 119616582 | Hyper | cancer_general | — | chr2 | 119616809 | 119616870 | Hyper | cancer_general | — |
| chr2 | 119914720 | 119914752 | Hyper | cancer_general | C1QL2 | chr2 | 119916049 | 119916082 | Hyper | cancer_general | C1QL2 |
| chr2 | 119916299 | 119916595 | Hyper | tcga, cancer_general | C1QL2 | chr2 | 120281646 | 120281693 | Hyper | cancer_general | SCTR |
| chr2 | 120281923 | 120281953 | Hyper | cancer_general | SCTR | chr2 | 121200390 | 121200433 | Hyper | cancer_general | — |
| chr2 | 121345081 | 121345111 | Hyper | cancer_general | — | chr2 | 121411888 | 121412153 | Hyper | liver_tcga, literature | — |
| chr2 | 122176232 | 122176293 | Hyper | liver_tcga | CLASP1 | chr2 | 124782333 | 124782458 | Hyper | cancer_general | CNTNAP5 |
| chr2 | 124782692 | 124783097 | Hyper | tcga, cancer_general | CNTNAP5 | chr2 | 127413918 | 127414036 | Hyper | cancer_general | GYPC |
| chr2 | 127783043 | 127783257 | Hyper | literature | — | chr2 | 127863601 | 127863725 | Hyper | breast | BIN1 |
| chr2 | 129976467 | 127976672 | Hyper | cancer_general | CYP27C1 | chr2 | 128421866 | 128421947 | Hyper | cancer_general | — |

TABLE 11-continued

| chr | Start | Stop | Hypo/hyper | classification | annotation |
|---|---|---|---|---|---|
| chr2 | 129494389 | 129494421 | Hyper | head_neck, liver_tcga, literature, cancer_general | — |
| chr2 | 130971149 | 130971321 | Hyper | literature | — |
| chr2 | 131673756 | 131673785 | Hyper | literature | ARHGEF4, AK127124 |
| chr2 | 131721461 | 131721949 | Hyper | cancer_general | ARHGEF4 |
| chr2 | 132088770 | 132088828 | Hyper | cancer_general | — |
| chr2 | 132152361 | 132152495 | Hyper | cancer_general | LOC389043, TRNA_Pseudo |
| chr2 | 132767457 | 132767707 | Hyper | cancer_general | — |
| chr2 | 132795670 | 132795728 | Hyper | cancer_general | — |
| chr2 | 133015275 | 133015323 | Hyper | cancer_general | JA668105, MIR663B, ANKRD30BL |
| chr2 | 133426249 | 133426279 | Hyper | cancer_general | NCKAP5, LYPD1 |
| chr2 | 137522445 | 137522475 | Hyper | cancer_general | THSD7B |
| chr2 | 139536937 | 139537145 | Hyper | cancer_general | NXPH2 |
| chr2 | 142887871 | 142888066 | Hyper | tcga | — |
| chr2 | 144694367 | 144695135 | Hyper | tcga, colorectal, cancer_general | GTDC1 |
| chr2 | 145274186 | 145274455 | Hyper | tcga, cancer_general | AK124806, ZEB2, ZEB2_AS1_1, ZEB2-AS1, ZEB2_AS1_3, ZEB2_AS1_4 |
| chr2 | 145282119 | 145282149 | Hyper | pancreas | ZEB2_AS1_4, ZEB2_AS1_3, ZEB2-AS1, ZEB2_AS1_1 |
| chr2 | 149633744 | 149633965 | Hyper | cancer_general | JB137817, KIF5C |
| chr2 | 151342903 | 151343277 | Hyper | blood | RND3 |
| chr2 | 154334272 | 154334665 | Hyper | cancer_general | RPRM |
| chr2 | 154728042 | 154728482 | Hyper | cancer_general, liver_tcga, tcga | GALNT13 |
| chr2 | 154729559 | 154729589 | Hyper | cancer_general | GALNT13 |

| chr | Start | Stop | Hypo/hyper | Classification | annotation |
|---|---|---|---|---|---|
| chr2 | 130763584 | 130763623 | Hyper | cancer_general | AK127124, AX746725 |
| chr2 | 131594989 | 131595019 | Hyper | pancreas | |
| chr2 | 131720852 | 131721253 | Hyper | cancer_general | ARHGEF4 |
| chr2 | 131792260 | 131793131 | Hyper | cancer_general | ARHGEF4 |
| chr2 | 132121661 | 132121829 | Hyper | cancer_general, tcga | TRNA, WTH3DI |
| chr2 | 132182790 | 132183089 | Hyper | cancer_general | — |
| chr2 | 132795240 | 132795419 | Hyper | cancer_general | ANKRD30BL, JA668105, MIR663B |
| chr2 | 133014598 | 133014638 | Hyper | cancer_general | AK094599 |
| chr2 | 133062326 | 133062389 | Hyper | cancer_general | |
| chr2 | 133426637 | 133426674 | Hyper | cancer_general | LYPD1, NCKAP5 |
| chr2 | 137523825 | 137523855 | Hyper | cancer_general | THSD7B |
| chr2 | 139537443 | 139537865 | Hyper | tcga, cancer_general | NXPH2 |
| chr2 | 142888348 | 142888418 | Hyper | cancer_general | — |
| chr2 | 145273404 | 145273751 | Hyper | cancer_general | ZEB2_AS1_1, ZEB2-AS1, ZEB2_AS1_3, ZEB2_AS1_4, AK124806, ZEB2 |
| chr2 | 145274814 | 145275213 | Hyper | tcga, cancer_general | ZEB2-AS1, ZEB2_AS1_3, ZEB2_AS1_4, AK124806, ZEB2, ZEB2_AS1_1 |
| chr2 | 149633097 | 149633399 | Hyper | tcga, cancer_general | JB137817, KIF5C |
| chr2 | 149645496 | 149645894 | Hyper | cancer_general | JB137817, KIF5C |
| chr2 | 154333535 | 154333567 | Hyper | cancer_general | RPRM |
| chr2 | 154335139 | 154335271 | Hyper | cancer_general | RPRM |
| chr2 | 154729044 | 154729240 | Hyper | tcga, cancer_general | GALNT13 |
| chr2 | 155555038 | 155555361 | Hyper | tcga | KCNJ3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 157176592 | 157176717 | Hyper | cancer_general | NR4A2 | chr2 | 157177003 | 157178310 | Hyper | cancer_general | NR4A2 |
| chr2 | 157178646 | 157178731 | Hyper | liver_tcga | NR4A2 | chr2 | 160761070 | 160761556 | Hyper | tcga, liver_tcga | LY75 |
| chr2 | 162272989 | 162274338 | Hyper | lung, literature, cancer_general | TBR1 | chr2 | 162274717 | 162274866 | Hyper | cancer_general | TBR1 |
| chr2 | 162275146 | 162275802 | Hyper | tcga, cancer_general | TBR1 | chr2 | 162280003 | 162280956 | Hyper | liver_tcga, cancer_general | TBR1 |
| chr2 | 162283365 | 162284055 | Hyper | liver_tcga, cancer_general | TBR1 | chr2 | 164593096 | 164593137 | Hyper | cancer_general | FIGN |
| chr2 | 168150069 | 168150245 | Hyper | cancer_general | — | chr2 | 168150751 | 168150945 | Hyper | cancer_general | — |
| chr2 | 171570082 | 171570428 | Hyper | cancer_general | LOC440925, SP5, AK023515 | chr2 | 171570684 | 171570733 | Hyper | cancer_general | AK023515, LOC440925, SP5 |
| chr2 | 171571264 | 171571315 | Hyper | blood | SP5, AK023515, LOC440925 | chr2 | 171571889 | 171572068 | Hyper | blood | AK023515, SP5, LOC440925 |
| chr2 | 171670349 | 171670467 | Hyper | cancer_general | GAD1 | chr2 | 171671487 | 171671881 | Hyper | cancer_general | GAD1 |
| chr2 | 171673873 | 171673939 | Hyper | blood | GAD1 | chr2 | 171674739 | 171675066 | Hyper | liver_tcga, cancer_general | GAD1 |
| chr2 | 171675361 | 171675592 | Hyper | cancer_general | GAD1 | chr2 | 171676684 | 171676785 | Hyper | cancer_general | GAD1 |
| chr2 | 172945124 | 172945167 | Hyper | cancer_general | DLX1, METAP1D | chr2 | 172945896 | 172946211 | Hyper | cancer_general | DLX1, METAP1D |
| chr2 | 172947717 | 172948314 | Hyper | cancer_general | METAP1D, DLX1 | chr2 | 172948709 | 172948751 | Hyper | cancer_general | DLX1, METAP1D |
| chr2 | 172949186 | 172949711 | Hyper | cancer_general | DLX1, METAP1D | chr2 | 172951596 | 172951689 | Hyper | cancer_general | DLX1, METAP1D |
| chr2 | 172952521 | 172953046 | Hyper | cancer_general | DLX1, METAP1D | chr2 | 172955444 | 172955545 | Hyper | cancer_general | DLX2, DLX1, METAP1D |
| chr2 | 172957907 | 172958066 | Hyper | cancer_general | DLX2, DLX1 | chr2 | 172961398 | 172961598 | Hyper | cancer_general | DLX2, DLX1 |
| chr2 | 172964821 | 172965802 | Hyper | cancer_general | DLX2 | chr2 | 172966264 | 172966442 | Hyper | cancer_general | DLX2 |
| chr2 | 172972735 | 172973218 | Hyper | cancer_general | DLX2 | chr2 | 173099784 | 173099814 | Hyper | cancer_general | — |
| chr2 | 173100262 | 173100430 | Hyper | cancer_general | — | chr2 | 175190871 | 175192468 | Hyper | lung, cancer_general | SP9, LOC285084 |
| chr2 | 175193268 | 175193823 | Hyper | lung, cancer_general | SP9, LOC285084 | chr2 | 175195831 | 175195861 | Hyper | cancer_general | SP9, LOC285084 |
| chr2 | 175196432 | 175196575 | Hyper | cancer_general | SP9, LOC285084 | chr2 | 175197089 | 175197119 | Hyper | cancer_general | SP9, LOC285084 |
| chr2 | 175198752 | 175198966 | Hyper | literature, cancer_general | SP9, LOC285084 | chr2 | 175199527 | 175199935 | Hyper | literature, cancer_general | SP9, LOC285084 |
| chr2 | 175200140 | 175202652 | Hyper | lung, cancer_general | SP9, LOC285084 | chr2 | 175204174 | 175204204 | Hyper | cancer_general | SP9, LOC285084, CIR1 |
| chr2 | 175204786 | 175205799 | Hyper | cancer_general | LOC285084, CIR1, SP9 | chr2 | 175206833 | 175207028 | Hyper | cancer_general | CIR1, SP9 |
| chr2 | 175207228 | 175207258 | Hyper | cancer_general | CIR1, SP9 | chr2 | 175207536 | 175207653 | Hyper | cancer_general | CIR1, SP9 |
| chr2 | 175208311 | 175209135 | Hyper | cancer_general | CIR1, SP9 | chr2 | 175547041 | 175547140 | Hyper | tcga | WIPF1 |
| chr2 | 175547384 | 175547413 | Hyper | tcga | WIPF1 | chr2 | 176940167 | 176940315 | Hyper | cancer_general | EVX2 |
| chr2 | 176943269 | 176943568 | Hyper | cancer_general | EVX2 | chr2 | 176943861 | 176943902 | Hyper | cancer_general | EVX2 |
| chr2 | 176944426 | 176945784 | Hyper | cancer_general | EVX2 | chr2 | 176946578 | 176947389 | Hyper | cancer_general | EVX2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 176947748 | 176947903 | Hyper | cancer_general | HOXD13, EVX2 | chr2 | 176948599 | 176948742 | Hyper | literature, cancer_general | HOXD13, EVX2 |
| chr2 | 176949045 | 176949075 | Hyper | cancer_general | HOXD13, EVX2 | chr2 | 176949695 | 176949869 | Hyper | cancer_general | HOXD13, EVX2 |
| chr2 | 176950142 | 176950258 | Hyper | cancer_general | HOXD13, EVX2 | chr2 | 176956558 | 176956640 | Hyper | literature, cancer_general | HOXD13, EVX2 |
| chr2 | 176956921 | 176957199 | Hyper | cancer_general | HOXD13, EVX2 | chr2 | 176957497 | 176957919 | Hyper | cancer_general | HOXD13, HOXD12, EVX2 |
| chr2 | 176958138 | 176958489 | Hyper | cancer_general | HOXD12, HOXD13, EVX2 | chr2 | 176959289 | 176959511 | Hyper | cancer_general | HOXD12, HOXD11, HOXD13 |
| chr2 | 176963448 | 176963522 | Hyper | cancer_general | HOXD12, HOXD11, HOXD13 | chr2 | 176964085 | 176964151 | Hyper | literature, cancer_general | HOXD11, HOXD13, HOXD12 |
| chr2 | 176964369 | 176965492 | Hyper | literature, cancer_general | HOXD12, HOXD11, HOXD13 | chr2 | 176969463 | 176969908 | Hyper | cancer_general | HOXD13, HOXD11, HOXD12 |
| chr2 | 176971628 | 176971712 | Hyper | pancreas | HOXD11, HOXD10, HOXD12 | chr2 | 176972557 | 176972586 | Hyper | liver_tcga | HOXD11, HOXD12, HOXD10 |
| chr2 | 176976029 | 176976188 | Hyper | tcga, cancer_general | HOXD10, HOXD11 | chr2 | 176980750 | 176981506 | Hyper | cancer_general, literature | HOXD9, HOXD11, HOXD10 |
| chr2 | 176982584 | 176982627 | Hyper | cancer_general | HOXD10, HOXD11, HOXD9, AX747372 | chr2 | 176986715 | 176986848 | Hyper | cancer_general | AX747372, HOXD8, HOXD10, HOXD9 |
| chr2 | 176987057 | 176988304 | Hyper | cancer_general, literature | HOXD10, HOXD9, AX747372, HOXD8 | chr2 | 176993074 | 176993103 | Hyper | literature | BC047605, HOXD9, HOXD10, AX747372, HOXD-AS2 |
| chr2 | 176993547 | 176993855 | Hyper | tcga, literature, cancer_general | AX747372, HOXD9, HOXD10, HOXD8, HOXD-AS2, BC047605 | chr2 | 176994124 | 176994764 | Hyper | liver_tcga, cancer_general | AX747372, HOXD9, HOXD10, HOXD8, HOXD-AS2, BC047605 |
| chr2 | 176995072 | 176995668 | Hyper | cancer_general | HOXD8, AX747372, HOXD9, HOXD-AS2, BC047605 | chr2 | 177001102 | 177001976 | Hyper | tcga, lung, cancer_general | BC047605, HOXD-AS2, HOXD8, AX747372 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 177004566 | 177004658 | Hyper | cancer_general | BC047605, HOXD-AS2, HOXD8 | chr2 | 177014981 | 177015010 | Hyper | literature | MIR10B, HOXD4, BC047605 |
| chr2 | 177027425 | 177027454 | Hyper | literature | HOXD3, HOXD4 | chr2 | 177030149 | 177030228 | Hyper | liver_tcga | HOXD3, HOXD-AS1 |
| chr2 | 177042984 | 177043515 | Hyper | tcga, cancer_general | HOXD1, HOXD-AS1, HOXD3 | chr2 | 177053276 | 177055816 | Hyper | cancer_general | HOXD1, HOXD-AS1 |
| chr2 | 177054113 | 177054351 | Hyper | cancer_general | HOXD1, HOXD-AS1 | chr2 | 177503048 | 177503077 | Hyper | literature | LOC375295 |
| chr2 | 177503581 | 177503610 | Hyper | literature | LOC375295 | chr2 | 178098791 | 178098967 | Hyper | literature | NFE2L2 |
| chr2 | 182321397 | 182321637 | Hyper | cancer_general | ITGA4 | chr2 | 182321839 | 182322170 | Hyper | cancer_general | ITGA4 |
| chr2 | 182322379 | 182323042 | Hyper | cancer_general | ITGA4 | chr2 | 182451522 | 182451551 | Hyper | literature | CERKL |
| chr2 | 182542903 | 182542933 | Hyper | cancer_general | NEUROD1 | chr2 | 182543321 | 182543418 | Hyper | cancer_general | NEUROD1 |
| chr2 | 182543764 | 182543925 | Hyper | cancer_general | NEUROD1 | chr2 | 182545211 | 182545275 | Hyper | cancer_general | NEUROD1 |
| chr2 | 182545539 | 182545694 | Hyper | cancer_general | NEUROD1 | chr2 | 182545986 | 182546085 | Hyper | cancer_general | NEUROD1 |
| chr2 | 182546435 | 182546465 | Hyper | cancer_general | NEUROD1 | chr2 | 182547385 | 182547613 | Hyper | cancer_general | NEUROD1 |
| chr2 | 182547937 | 182548161 | Hyper | cancer_general | NEUROD1 | chr2 | 182549088 | 182549134 | Hyper | cancer_general | NEUROD1 |
| chr2 | 182549337 | 182549454 | Hyper | cancer_general | NEUROD1 | chr2 | 182550094 | 182550124 | Hyper | cancer_general | NEUROD1 |
| chr2 | 182819048 | 182819216 | Hyper | cancer_general | — | chr2 | 183731294 | 183731524 | Hyper | cancer_general | FRZB |
| chr2 | 183731809 | 183732076 | Hyper | tcga, cancer_general, literature | FRZB | chr2 | 185462869 | 185462980 | Hyper | cancer_general | ZNF804A |
| chr2 | 185463193 | 185463817 | Hyper | tcga, cancer_general | ZNF804A | chr2 | 186603488 | 186603518 | Hyper | cancer_general | FSIP2, BC039382 |
| chr2 | 188419047 | 188419204 | Hyper | cancer_general | TFPI | chr2 | 189157427 | 189157688 | Hyper | cancer_general, blood | MIR561, GULP1 |
| chr2 | 190708790 | 190708819 | Hyper | literature | PMS1 | chr2 | 193059025 | 193060067 | Hyper | cancer_general, tcga | TMEFF2 |
| chr2 | 193060385 | 193060441 | Hyper | cancer_general | TMEFF2 | chr2 | 193060683 | 193060891 | Hyper | tcga, cancer_general | TMEFF2 |
| chr2 | 193061388 | 193061480 | Hyper | cancer_general | TMEFF2 | chr2 | 198267345 | 198267374 | Hyper | literature | SnR39B, SF3B1 |
| chr2 | 198650984 | 198651076 | Hyper | liver_tcga | BOLL | chr2 | 200326590 | 200326735 | Hyper | liver_tcga, literature | SATB2-AS1, AK056625, AK125157 |
| chr2 | 200327287 | 200327565 | Hyper | liver_tcga, cancer_general | AK125157, SATB2-AS1, AK056625 | chr2 | 200328747 | 200329668 | Hyper | cancer_general | SATB2-AS1, AK056625, AK125157 |
| chr2 | 200333775 | 200333834 | Hyper | cancer_general | AK056625, SATB2-AS1, AK125157 | chr2 | 200334976 | 200335952 | Hyper | cancer_general, liver_tcga | AK056625, SATB2-AS1 |
| chr2 | 201172444 | 201172480 | Hyper | blood | SPATS2L | chr2 | 201450556 | 201450707 | Hyper | cancer_general | AOX1, SGOL2 |
| chr2 | 201450947 | 201451040 | Hyper | tcga | SGOL2, AOX1 | chr2 | 202097078 | 202097143 | Hyper | literature | CASP8 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 202098936 | 202098965 | Hyper | literature | CASP8 | chr2 | 202101190 | 202101219 | Hyper | literature | CASP8 |
| chr2 | 202122459 | 202122683 | Hyper | literature | CASP8 | chr2 | 202899862 | 202899891 | Hyper | liver_tcga | FZD7 |
| chr2 | 206551056 | 206551378 | Hyper | tcga, cancer_general | NRP2 | chr2 | 207139072 | 207139102 | Hyper | cancer_general | ZDBF2, BC028329 |
| chr2 | 207139347 | 207139605 | Hyper | liver_tcga, cancer_general | ZDBF2, BC028329 | chr2 | 207307528 | 207307562 | Hyper | cancer_general | ADAM23 |
| chr2 | 207308802 | 207308857 | Hyper | cancer_general | ADAM23 | chr2 | 207506691 | 207507181 | Hyper | cancer_general | DYTN, LOC200726 |
| chr2 | 208635534 | 208635774 | Hyper | tcga, cancer_general | FZD5 | chr2 | 208989208 | 208989382 | Hyper | liver_tcga, literature | CRYGD, LOC100507443, CRYGC |
| chr2 | 209113097 | 209113126 | Hyper | literature | IDH1-AS1, IDH1 | chr2 | 209271322 | 209271551 | Hyper | cancer_general | PTH2R |
| chr2 | 210636335 | 210636892 | Hyper | cancer_general, tcga | UNC80 | chr2 | 212248428 | 212248457 | Hyper | literature | ERBB4 |
| chr2 | 212288927 | 212288956 | Hyper | literature | ERBB4 | chr2 | 212295683 | 212295820 | Hyper | literature | ERBB4 |
| chr2 | 212530120 | 212530149 | Hyper | literature | ERBB4 | chr2 | 212537902 | 212537994 | Hyper | literature | ERBB4 |
| chr2 | 212566811 | 212566840 | Hyper | literature | ERBB4 | chr2 | 212578292 | 212578321 | Hyper | literature | ERBB4 |
| chr2 | 212587132 | 212587161 | Hyper | literature | ERBB4 | chr2 | 213401235 | 213401339 | Hyper | cancer_general | — |
| chr2 | 213401613 | 213401947 | Hyper | cancer_general | — | chr2 | 213403110 | 213403337 | Hyper | cancer_general, tcga | — |
| chr2 | 215275823 | 215275852 | Hyper | literature | VWC2L | chr2 | 217559296 | 217559326 | Hyper | cancer_general | IGFBP5 |
| chr2 | 217559966 | 217559999 | Hyper | cancer_general | IGFBP5 | chr2 | 218770207 | 218770270 | Hyper | liver_tcga | TNS1 |
| chr2 | 218806147 | 218806302 | Hyper | cancer_general | TNS1 | chr2 | 219736151 | 219736691 | Hyper | cancer_general, tcga | WNT10A, WNT6 |
| chr2 | 219828049 | 219828117 | Hyper | cancer_general | CDK5R2 | chr2 | 219847462 | 219847555 | Hyper | cancer_general | CRYBA2, FEV, LINC00608 |
| chr2 | 219848809 | 219849001 | Hyper | cancer_general | CRYBA2, FEV, LINC00608 | chr2 | 219857723 | 219857756 | Hyper | cancer_general | CRYBA2, FEV, MIR375, LOC100129175, CCDC108 |
| chr2 | 220173989 | 220174296 | Hyper | literature, cancer_general | — | chr2 | 220196354 | 220196567 | Hyper | cancer_general | RESP18 |
| chr2 | 220223098 | 220223128 | Hyper | cancer_general | — | chr2 | 220223648 | 220223703 | Hyper | cancer_general | — |
| chr2 | 220283338 | 220283519 | Hyper | cancer_general | — | chr2 | 220299588 | 220300059 | Hyper | cancer_general | SPEG, DES |
| chr2 | 220313621 | 220313692 | Hyper | cancer_general | DES | chr2 | 220349029 | 220349706 | Hyper | cancer_general | — |
| chr2 | 220361447 | 220361531 | Hyper | cancer_general | SPEG | chr2 | 220416379 | 220416513 | Hyper | cancer_general | CHPF, OBSL1, MIR3132, TMEM198 |
| chr2 | 220417649 | 220417649 | Hyper | liver_tcga, cancer_general | GMPPA | chr2 | 222435773 | 222435863 | Hyper | cancer_general | AX747413, EPHA4 |
| chr2 | 223155722 | 223156188 | Hyper | cancer_general | CHPF, OBSL1, MIR3132, TMEM198 | chr2 | 223158730 | 223159453 | Hyper | cancer_general, lung | CCDC140, DD413687, PAX3 |
| chr2 | | | | | CCDC140, DD413687, PAX3 | | | | | | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 223159823 | 223160065 | Hyper | tcga, cancer_general | CCDC140, DD413687, PAX3 | chr2 | 223160342 | 223160379 | Hyper | cancer_general | CCDC140, DD413687, PAX3 |
| chr2 | 223161247 | 223162063 | Hyper | tcga, cancer_general | CCDC140, DD413687, PAX3 | chr2 | 223162779 | 223163535 | Hyper | cancer_general | CCDC140, DD413687, PAX3 |
| chr2 | 223163768 | 223163954 | Hyper | cancer_general | CCDC140, DD413687, PAX3 | chr2 | 223164534 | 223164883 | Hyper | cancer_general, literature | CCDC140, DD413687, PAX3 |
| chr2 | 223165434 | 223165832 | Hyper | cancer_general, lung | CCDC140, DD413687, PAX3, CCDC140 | chr2 | 223166449 | 223166721 | Hyper | cancer_general | CCDC140, DD413687, PAX3 |
| chr2 | 223167389 | 223167573 | Hyper | cancer_general | PAX3, CCDC140, DD413687 | chr2 | 223168437 | 223168852 | Hyper | cancer_general | CCDC140, DD413687, PAX3 |
| chr2 | 223169640 | 223169864 | Hyper | lung, cancer_general | CCDC140, DD413687, PAX3 | chr2 | 223170375 | 223170434 | Hyper | cancer_general | CCDC140, DD413687, PAX3 |
| chr2 | 223171109 | 223171180 | Hyper | cancer_general | CCDC140, DD413687, PAX3 | chr2 | 223172337 | 223172367 | Hyper | lung | CCDC140, DD413687, PAX3 |
| chr2 | 223172924 | 223173173 | Hyper | cancer_general | CCDC140, DD413687, PAX3 | chr2 | 223175663 | 223176181 | Hyper | cancer_general, lung | LOC440934, CCDC140 |
| chr2 | 223176456 | 223176983 | Hyper | cancer_general | LOC440934, CCDC140 | chr2 | 223177315 | 223177610 | Hyper | cancer_general | LOC440934, CCDC140 |
| chr2 | 224903260 | 224903440 | Hyper | esophageal | SERPINE2 | chr2 | 224903690 | 224903755 | Hyper | esophageal | SERPINE2 |
| chr2 | 224904108 | 224904237 | Hyper | esophageal | SERPINE2 | chr2 | 228029418 | 228029531 | Hyper | tcga, esophageal | COL4A3 |
| chr2 | 228736215 | 228736473 | Hyper | liver_tcga, cancer_general, tcga | DAW1 | chr2 | 229046107 | 229046503 | Hyper | cancer_general | SPHKAP |
| chr2 | 231693216 | 231693268 | Hyper | cancer_general | CAB39 | chr2 | 232394970 | 232395061 | Hyper | liver_tcga | NMUR1 |
| chr2 | 232479822 | 232479938 | Hyper | tcga | — | chr2 | 232791704 | 232792012 | Hyper | tcga, cancer_general | NPPC |
| chr2 | 233350208 | 233351394 | Hyper | cancer_general | ECEL1 | chr2 | 233352025 | 233352853 | Hyper | cancer_general | ECEL1 |
| chr2 | 233498710 | 233499297 | Hyper | tcga, cancer_general | EFHD1 | chr2 | 235404545 | 235404575 | Hyper | cancer_general | ARL4C |
| chr2 | 235860746 | 235860808 | Hyper | blood | SH3BP4 | chr2 | 235861389 | 235861533 | Hyper | blood | SH3BP4 |
| chr2 | 236402771 | 236403013 | Hyper | blood | AGAP1 | chr2 | 236403270 | 236403736 | Hyper | blood | AGAP1 |
| chr2 | 236578362 | 236578677 | Hyper | blood | AGAP1 | chr2 | 237072413 | 237073030 | Hyper | tcga, cancer_general | GBX2 |
| chr2 | 237073354 | 237073414 | Hyper | cancer_general | GBX2 | chr2 | 237076725 | 237076815 | Hyper | liver_tcga | GBX2 |
| chr2 | 237077562 | 237077608 | Hyper | cancer_general | GBX2 | chr2 | 237077846 | 237078348 | Hyper | cancer_general | GBX2 |
| chr2 | 237080264 | 237080294 | Hyper | cancer_general | GBX2 | chr2 | 237081341 | 237081826 | Hyper | cancer_general | GBX2 |
| chr2 | 237082117 | 237082720 | Hyper | cancer_general | GBX2 | chr2 | 237086349 | 237086468 | Hyper | cancer_general | GBX2 |
| chr2 | 237145422 | 237145601 | Hyper | tcga, cancer_general | ASB18 | chr2 | 237416216 | 237416429 | Hyper | cancer_general | IQCA1 |
| chr2 | 238395291 | 238395356 | Hyper | cancer_general | MLPH | chr2 | 238395906 | 238395961 | Hyper | blood | MLPH |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr2 | 238835895 | 238836114 | Hyper | tcga | LRRFIP1 | chr2 | 238864644 | 238864913 | Hyper | cancer_general | — |
| chr2 | 239072648 | 239072692 | Hyper | pancreas | FAM132B, ILKAP | chr2 | 239140025 | 239140249 | Hyper | cancer_general | LOC643387, HES6, LOC151174 |
| chr2 | 239149844 | 239149951 | Hyper | tcga | PER2, HES6, LOC643387, LOC151174 | chr2 | 239755164 | 239755194 | Hyper | cancer_general | TWIST2 |
| chr2 | 239755736 | 239755778 | Hyper | cancer_general | TWIST2 | chr2 | 239756373 | 239756648 | Hyper | cancer_general | TWIST2 |
| chr2 | 239757636 | 239757824 | Hyper | cancer_general | TWIST2 | chr2 | 239758078 | 239758144 | Hyper | cancer_general | TWIST2 |
| chr2 | 239758345 | 239758394 | Hyper | cancer_general | TWIST2 | chr2 | 241393200 | 241393469 | Hyper | cancer_general | MIR149, PP14571, GPC1 |
| chr2 | 241497411 | 241497554 | Hyper | liver_tcga | DUSP28, ANKMY1 | chr2 | 241758377 | 241758819 | Hyper | literature, cancer_general | KIF1A |
| chr2 | 241759597 | 241759694 | Hyper | cancer_general | KIF1A | chr2 | 241760149 | 241760178 | Hyper | literature | KIF1A |
| chr2 | 241760494 | 241760523 | Hyper | literature | KIF1A | chr2 | 241771165 | 241771257 | Hyper | cancer_general | — |
| chr2 | 242549849 | 242549957 | Hyper | tcga | — | HPV16 | 111 | 140 | Hyper | virus | — |
| HPV16 | 367 | 396 | Hyper | virus | — | HPV16 | 623 | 652 | Hyper | virus | — |
| HPV16 | 879 | 908 | Hyper | virus | — | HPV16 | 1135 | 1164 | Hyper | virus | — |
| HPV16 | 1391 | 1420 | Hyper | virus | — | HPV16 | 1647 | 1676 | Hyper | virus | — |
| HPV16 | 1903 | 1932 | Hyper | virus | — | HPV16 | 2159 | 2188 | Hyper | virus | — |
| HPV16 | 2415 | 2444 | Hyper | virus | — | HPV16 | 2671 | 2700 | Hyper | virus | — |
| HPV16 | 2927 | 2956 | Hyper | virus | — | HPV16 | 3183 | 3212 | Hyper | virus | — |
| HPV16 | 3439 | 3468 | Hyper | virus | — | HPV16 | 3695 | 3724 | Hyper | virus | — |
| HPV16 | 3951 | 3980 | Hyper | virus | — | HPV16 | 4207 | 4236 | Hyper | virus | — |
| HPV16 | 4463 | 4492 | Hyper | virus | — | HPV16 | 4719 | 4748 | Hyper | virus | — |
| HPV16 | 4975 | 5004 | Hyper | virus | — | HPV16 | 5231 | 5260 | Hyper | virus | — |
| HPV16 | 5487 | 5516 | Hyper | virus | — | HPV16 | 5743 | 5772 | Hyper | virus | — |
| HPV16 | 5999 | 6028 | Hyper | virus | — | HPV16 | 6255 | 6284 | Hyper | virus | — |
| HPV16 | 6511 | 6540 | Hyper | virus | — | HPV16 | 6767 | 6796 | Hyper | virus | — |
| HPV16 | 7023 | 7052 | Hyper | virus | — | HPV16 | 7279 | 7308 | Hyper | virus | — |
| HPV16 | 7535 | 7564 | Hyper | virus | — | chr17 | 1082884 | 1083002 | Hyper | liver_tcga | — |
| chr17 | 1173996 | 1174413 | Hyper | cancer_general | TUSC5, BHLHA9 | chr17 | 1494550 | 1494613 | Hyper | pancreas | SLC43A2 |
| chr17 | 1959468 | 1959520 | Hyper | cancer_general | MIR132, HIC1, SMG6, AX747853, MIR212 | chr17 | 2607905 | 2607986 | Hyper | liver_tcga | CLUH |
| chr17 | 3438914 | 3438959 | Hyper | cancer_general | TRPV3 | chr17 | 3658490 | 3658519 | Hyper | liver_tcga | — |
| chr17 | 4544607 | 4544710 | Hyper | cancer_general | ALOX15 | chr17 | 4891276 | 4891305 | Hyper | tcga | KIF1C, CAMTA2, INCA1 |
| chr17 | 4891527 | 4891556 | Hyper | tcga | KIF1C, INCA1, CAMTA2 | chr17 | 5000428 | 5000790 | Hyper | cancer_general | ZNF232, ZFP3 |
| chr17 | 5001032 | 5001061 | Hyper | liver_tcga | ZNF232, ZFP3 | chr17 | 5019637 | 5019761 | Hyper | liver_tcga | ZNF232, USP6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 6616637 | 6616686 | Hyper | cancer_general | SLC13A5 | chr17 | 6616911 | 6617192 | Hyper | liver_tcga, cancer_general | SLC13A5 |
| chr17 | 6679190 | 6679296 | Hyper | cancer_general | FBXO39, XAF1 | chr17 | 6946107 | 6946141 | Hyper | cancer_general | SLC16A11, SLC16A13 |
| chr17 | 7348885 | 7348997 | Hyper | head_neck | CHRNB1, FGF11, TMEM102 | chr17 | 7555117 | 7555425 | Hyper | tcga | TP53, ATP1B2 |
| chr17 | 7572957 | 7573018 | Hyper | literature | HV941478, HV941442, HV941433, HV941434, HV941486, HV941440, HV941444, HV941430, HV941431, HV941428, TP53, HV941429 | chr17 | 7573968 | 7574028 | Hyper | literature | HV941428, HV941434, TP53, HV941478, HV941442, HV941444, HV941433, HV941486, HV941429, HV941440, HV941430, HV941431 |
| chr17 | 7576847 | 7577167 | Hyper | literature | HV941430, HV941429, HV941428, TP53, HV941431, HV941478, HV941442, HV941433, HV941434, HV941486, HV941444 | chr17 | 7577504 | 7577604 | Hyper | literature | HV941429, TP53, HV941440, HV941478, HV941442, HV941430, HV941428, HV941433, HV941431, HV941444, HV941486, HV941434 |
| chr17 | 7578164 | 7578570 | Hyper | literature | HV941478, HV941444, TP53, HV941429, HV941434, HV941442, HV941430, HV941486, HV941428, HV941433, HV941431 | chr17 | 7579285 | 7579880 | Hyper | literature | WRAP53, HV941442, HV941440, HV941429, HV941428, TP53, HV941430, HV941486, HV941434, HV941431, HV941433, HV941444 |
| chr17 | 7906254 | 7906535 | Hyper | tcga, cancer_general | GUCY2D | chr17 | 8230335 | 8230694 | Hyper | cancer_general, tcga | ARHGEF15 |
| chr17 | 8534493 | 8534582 | Hyper | esophageal | — | chr17 | 8868620 | 8869385 | Hyper | cancer_general | PIK3R5 |
| chr17 | 8906266 | 8906518 | Hyper | cancer_general | — | chr17 | 8906993 | 8907575 | Hyper | tcga, cancer_general | — |
| chr17 | 8926060 | 8926263 | Hyper | tcga, cancer_general | NTN1 | chr17 | 10101084 | 10101984 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 10102415 | 10102665 | Hyper | tcga, cancer_general | — | chr17 | 11144167 | 11144320 | Hyper | cancer_general | SHISA6 |
| chr17 | 11144926 | 11144989 | Hyper | cancer_general | SHISA6 | chr17 | 11984693 | 11984722 | Hyper | literature | MIR744, MAP2K4 |
| chr17 | 11998944 | 11998973 | Hyper | literature | — | chr17 | 12013726 | 12013755 | Hyper | literature | — |
| chr17 | 12016550 | 12016630 | Hyper | literature | — | chr17 | 12028618 | 12028647 | Hyper | literature | — |
| chr17 | 13503972 | 13504195 | Hyper | cancer_general | HS3ST3A1 | chr17 | 13504557 | 13504681 | Hyper | cancer_general | HS3ST3A1 |
| chr17 | 13504975 | 13505188 | Hyper | tcga, cancer_general | HS3ST3A1 | chr17 | 13505418 | 13505572 | Hyper | cancer_general | HS3ST3A1 |
| chr17 | 14201041 | 14201181 | Hyper | cancer_general | HS3ST3B1, MGC12916 | chr17 | 14204212 | 14204242 | Hyper | tcga, cancer_general esophageal | MGC12916, HS3ST3B1 |
| chr17 | 14204527 | 14204620 | Hyper | esophageal | MGC12916, HS3ST3B1 | chr17 | 15245050 | 15245139 | Hyper | cancer_general | TEKT3 |
| chr17 | 16284630 | 16285065 | Hyper | ovarian | UBB | chr17 | 16570699 | 16570794 | Hyper | cancer_general | TBC1D28, CCDC144B |
| chr17 | 17398404 | 17398440 | Hyper | pancreas | MED9, RASD1 | chr17 | 18538154 | 18538275 | Hyper | cancer_general | CCDC144B |
| chr17 | 26554634 | 26554705 | Hyper | cancer_general | PYY2 | chr17 | 27038649 | 27038900 | Hyper | cancer_general, tcga | RAB34, NARR, RPL23A, SNORD42B, PROCA1 |
| chr17 | 27044770 | 27044800 | Hyper | colorectal | SNORD42A, SNORD4B, NARR, RAB34, PROCA1, RPL23A, SNORD42B, SNORD4A, TLCD1 | chr17 | 27332453 | 27332660 | Hyper | cancer_general | SEZ6 |
| chr17 | 27940359 | 27940911 | Hyper | cancer_general | CORO6, ANKRD13B | chr17 | 28562701 | 28562765 | Hyper | cancer_general | SLC6A4 |
| chr17 | 29249717 | 29249930 | Hyper | cancer_general | ADAP2 | chr17 | 29298080 | 29298581 | Hyper | tcga, liver_tcga, hepatobiliary | DPRXP4, RNF135 |
| chr17 | 29508761 | 29508790 | Hyper | literature | NF1 | chr17 | 29541527 | 29541556 | Hyper | literature | NF1 |
| chr17 | 29562732 | 29562761 | Hyper | literature | NF1 | chr17 | 29718215 | 29718269 | Hyper | cancer_general | RAB11FIP4 |
| chr17 | 29719187 | 29719242 | Hyper | cancer_general | RAB11FIP4 | chr17 | 31618425 | 31619319 | Hyper | cancer_general | ASIC2 |
| chr17 | 31619951 | 31620026 | Hyper | cancer_general | ASIC2 | chr17 | 32484020 | 32484049 | Hyper | literature | TMEM132E, C17orf102 |
| chr17 | 32906379 | 32906636 | Hyper | tcga | TMEM132E, C17orf102 | chr17 | 32906987 | 32907146 | Hyper | tcga | TMEM132E, C17orf102 |
| chr17 | 32907652 | 32907753 | Hyper | cancer_general | TMEM132E, C17orf102, TMEM132E | chr17 | 32908132 | 32908374 | Hyper | colorectal, cancer_general | TMEM132E, C17orf102 |
| chr17 | 32908647 | 32908931 | Hyper | esophageal | — | chr17 | 33288229 | 33288351 | Hyper | esophageal | ZNF830, CCT6B |
| chr17 | 33288890 | 33288988 | Hyper | esophageal | CCT6B, ZNF830 | chr17 | 33672916 | 33672986 | Hyper | cancer_general | SLFN11 |
| chr17 | 35165645 | 35165691 | Hyper | cancer_general | — | chr17 | 35165986 | 35166016 | Hyper | cancer_general | BC084573, LHX1 |
| chr17 | 35285542 | 35285666 | Hyper | cancer_general | BC084573, LHX1 | chr17 | 35290388 | 35290655 | Hyper | cancer_general | BC084573, LHX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 35291320 | 35291354 | Hyper | cancer_general | LHX1, BC084573 | chr17 | 35291829 | 35292626 | Hyper | cancer_general | BC084573, LHX1 |
| chr17 | 35293704 | 35294154 | Hyper | tcga, cancer_general | LHX1, BC084573 | chr17 | 35294461 | 35294505 | Hyper | literature | LHX1, BC084573 |
| chr17 | 35295047 | 35295160 | Hyper | cancer_general | LHX1, BC084573 | chr17 | 35296143 | 35296292 | Hyper | cancer_general | AATF, LHX1, BC084573 |
| chr17 | 35296728 | 35296888 | Hyper | cancer_general | AATF, LHX1, BC084573 | chr17 | 35297619 | 35298153 | Hyper | cancer_general | BC084573, AATF, LHX1 |
| chr17 | 35299251 | 35300854 | Hyper | cancer_general, literature | LHX1, BC084573, AATF | chr17 | 35303340 | 35303535 | Hyper | cancer_general | AATF, LHX1, BC084573 |
| chr17 | 35872722 | 35872861 | Hyper | liver_tcga | SYNRG, DUSP14 | chr17 | 36103021 | 36103326 | Hyper | tcga, cancer_general | HNF1B |
| chr17 | 36103571 | 36103601 | Hyper | cancer_general | HNF1B | chr17 | 36104120 | 36104779 | Hyper | cancer_general | — |
| chr17 | 36105223 | 36105596 | Hyper | cancer_general | — | chr17 | 36715772 | 36715967 | Hyper | tcga | SRCIN1 |
| chr17 | 37321186 | 37321972 | Hyper | tcga, cancer_general | CACNB1, ARL5C | chr17 | 37366337 | 37366552 | Hyper | cancer_general | STAC2, RPL19 |
| chr17 | 37381011 | 37381850 | Hyper | tcga, literature, cancer_general | STAC2 | chr17 | 37382146 | 37382248 | Hyper | literature | STAC2 |
| chr17 | 37757153 | 37757217 | Hyper | lung | NEUROD2 | chr17 | 37760488 | 37760561 | Hyper | cancer_general | NEUROD2 |
| chr17 | 37761997 | 37762334 | Hyper | cancer_general | NEUROD2 | chr17 | 37868190 | 37868294 | Hyper | literature | ERBB2 |
| chr17 | 37879568 | 37879615 | Hyper | literature | MIR4728, MIEN1, ERBB2 | chr17 | 37880205 | 37880276 | Hyper | literature | MIR4728, MIEN1, ERBB2 |
| chr17 | 37880971 | 37881018 | Hyper | literature | MIR4728, MIEN1, ERBB2 | chr17 | 37881318 | 37881631 | Hyper | literature | MIR4728, MIEN1, ERBB2 |
| chr17 | 38347560 | 38347624 | Hyper | cancer_general | RAPGEFL1 | chr17 | 38474363 | 38474502 | Hyper | literature | RARA |
| chr17 | 38497616 | 38497645 | Hyper | literature | RARA | chr17 | 38498083 | 38498112 | Hyper | literature | RARA |
| chr17 | 38504087 | 38504116 | Hyper | literature | RARA | chr17 | 38510555 | 38510584 | Hyper | liver_tcga | GJD3, RARA |
| chr17 | 40332943 | 40333226 | Hyper | tcga, esophageal | HCRT, GHDC, KCNH4 | chr17 | 40400867 | 40401031 | Hyper | cancer_general | STAT5B |
| chr17 | 40464278 | 40464317 | Hyper | cancer_general | AK024535, STAT3, AK092965, STAT5A | chr17 | 40464517 | 40464607 | Hyper | cancer_general | AK024535, STAT3, AK092965, STAT5A |
| chr17 | 40474467 | 40474496 | Hyper | literature | AK092965, STAT3, AK024535 | chr17 | 40826197 | 40826226 | Hyper | liver_tcga | CNTNAP1, PLEKHH3, TUBG2, CCR10 |
| chr17 | 40837022 | 40837051 | Hyper | liver_tcga | PLEKHH3, CNTNAP1, CCR10 | chr17 | 40837287 | 40837383 | Hyper | liver_tcga | CCR10, PLEKHH3, CNTNAP1 |
| chr17 | 40838982 | 40839022 | Hyper | liver_tcga | CNTNAP1, CCR10, PLEKHH3 | chr17 | 41177394 | 41177459 | Hyper | tcga | RND2, VAT1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 41197714 | 41197743 | Hyper | literature | BRCA1 | chr17 | 41201163 | 41201192 | Hyper | literature | BRCA1 |
| chr17 | 41203073 | 41203102 | Hyper | literature | BRCA1 | chr17 | 41209064 | 41209114 | Hyper | literature | BRCA1 |
| chr17 | 41215890 | 41215961 | Hyper | literature | BRCA1 | chr17 | 41267731 | 41267775 | Hyper | literature | NBR2, BRCA1 |
| chr17 | 41276031 | 41276075 | Hyper | literature | BRCA1, NBR2 | chr17 | 41277259 | 41277721 | Hyper | literature | NBR2, BRCA1 |
| chr17 | 41791460 | 41791489 | Hyper | tcga | — | chr17 | 42030329 | 42030756 | Hyper | liver_tcga, cancer_general | PYY |
| chr17 | 42061336 | 42061381 | Hyper | blood | — | chr17 | 42082522 | 42082557 | Hyper | cancer_general | NAGS, TMEM101 |
| chr17 | 42084361 | 42084626 | Hyper | tcga | TMEM101, NAGS | chr17 | 42092190 | 42092220 | Hyper | breast | TMEM101, NAGS |
| chr17 | 42393842 | 42394024 | Hyper | cancer_general | SLC25A39, RUNDC3A, AK055254 | chr17 | 42402884 | 42402917 | Hyper | hepatobiliary | SLC25A39, RUNDC3A |
| chr17 | 42635295 | 42635760 | Hyper | tcga, cancer_general | FZD2 | chr17 | 42733711 | 42733884 | Hyper | cancer_general, liver_tcga | C17orf104 |
| chr17 | 42907564 | 42907951 | Hyper | esophageal, cancer_general | — | chr17 | 43037399 | 43037429 | Hyper | cancer_general | C1QL1 |
| chr17 | 43044658 | 43044688 | Hyper | cancer_general | C1QL1 | chr17 | 43044999 | 43045116 | Hyper | liver_tcga, cancer_general | C1QL1 |
| chr17 | 43046260 | 43046385 | Hyper | tcga | C1QL1 | chr17 | 43047436 | 43047751 | Hyper | liver_tcga, cancer_general | C1QL1 |
| chr17 | 43339109 | 43339333 | Hyper | cancer_general | MAP3K14-AS1, MAP3K14, SPATA32 | chr17 | 43339609 | 43339899 | Hyper | cancer_general | MAP3K14, MAP3K14-AS1, SPATA32 |
| chr17 | 43974256 | 43974358 | Hyper | cancer_general | MAPT-IT1, MAPT | chr17 | 45331014 | 45331313 | Hyper | esophageal | ITGB3 |
| chr17 | 45810850 | 45811341 | Hyper | tcga, cancer_general | TBX21 | chr17 | 45867315 | 45867460 | Hyper | tcga | — |
| chr17 | 46124991 | 46125061 | Hyper | colorectal | NFE2L1 | chr17 | 46619298 | 46619327 | Hyper | tcga | HOXB3, HOXB2, HOXB-AS1 |
| chr17 | 46619540 | 46619569 | Hyper | tcga | HOXB2, HOXB-AS1, HOXB3 | chr17 | 46620494 | 46621094 | Hyper | cancer_general | HOXB-AS1, HOXB3, HOXB2 |
| chr17 | 46621353 | 46621458 | Hyper | cancer_general | HOXB-AS1, HOXB3, HOXB2 | chr17 | 46621856 | 46621909 | Hyper | cancer_general | HOXB3, HOXB-AS1, HOXB2 |
| chr17 | 46655148 | 46655178 | Hyper | lung | MIR10A, HOXB4, HOXB3 | chr17 | 46655435 | 46656704 | Hyper | tcga, cancer_general, literature | HOXB2, MIR10A, HOXB3 |

TABLE 11-continued

| chr | Start | Stop | Hypo/hyper | classification | annotation |
|---|---|---|---|---|---|
| chr17 | 46659429 | 46659859 | Hyper | cancer_general | HOXB-AS3, HOXB5, MIR10A, HOXB4, HOXB3 |
| chr17 | 46663743 | 46663887 | Hyper | tcga, cancer_general | HOXB5, HOXB6, MIR10A, HOXB4, HOXB-AS3 |
| chr17 | 46674873 | 46674970 | Hyper | cancer_general | HOXB7, HOXB-AS3, HOXB6, HOXB5 |
| chr17 | 46675170 | 46675600 | Hyper | lung, cancer_general | HOXB7, HOXB-AS3, HOXB6, HOXB5 |
| chr17 | 46690467 | 46690664 | Hyper | cancer_general | HOXB9, HOXB8, HOXB7 |
| chr17 | 46691505 | 46691592 | Hyper | cancer_general | HOXB9, HOXB8, HOXB7 |
| chr17 | 46691805 | 46692110 | Hyper | tcga, lung, cancer_general | HOXB9, HOXB8, HOXB7 |
| chr17 | 46692439 | 46692606 | Hyper | tcga | HOXB9, HOXB8, HOXB7 |
| chr17 | 46710946 | 46711065 | Hyper | literature, cancer_general, tcga | MIR196A1, HOXB9 |
| chr17 | 46711281 | 46711375 | Hyper | tcga, literature, cancer_general | MIR196A1, HOXB9 |
| chr17 | 46713959 | 46714072 | Hyper | cancer_general | MIR196A1 |
| chr17 | 46795641 | 46797582 | Hyper | cancer_general | PRAC, HOXB-AS5, MIR3185, HOXB13 |
| chr17 | 46799625 | 46799896 | Hyper | literature, cancer_general | HOXB-AS5, MIR3185, HOXB13, PRAC |
| chr17 | 46800601 | 46800668 | Hyper | cancer_general | MIR3185, HOXB13, HOXB-AS5, PRAC |
| chr17 | 46800961 | 46801416 | Hyper | lung, cancer_general | HOXB-AS5, PRAC, MIR3185, HOXB13 |
| chr17 | 46802459 | 46803286 | Hyper | cancer_general | HOXB13, MIR3185, HOXB-AS5, PRAC |
| chr17 | 46804107 | 46804428 | Hyper | cancer_general | HOXB13, MIR3185, HOXB-AS5, PRAC |
| chr17 | 46810416 | 46810958 | Hyper | cancer_general | HOXB-AS5, HOXB13, MIR3185 |
| chr17 | 46811354 | 46811541 | Hyper | cancer_general | HOXB13, MIR3185, HOXB-AS5 |
| chr17 | 46816282 | 46816877 | Hyper | cancer_general | — |
| chr17 | 46824224 | 46825054 | Hyper | cancer_general | — |
| chr17 | 46825284 | 46825514 | Hyper | cancer_general | — |
| chr17 | 46826930 | 46827127 | Hyper | cancer_general | — |
| chr17 | 46827330 | 46827756 | Hyper | cancer_general | — |
| chr17 | 46829498 | 46829579 | Hyper | cancer_general | — |
| chr17 | 46829979 | 46830110 | Hyper | cancer_general | — |
| chr17 | 46831779 | 46832639 | Hyper | cancer_general | TTL6 |
| chr17 | 47072805 | 47073465 | Hyper | cancer_general | TTL6 |
| chr17 | 47073988 | 47074228 | Hyper | cancer_general | IGF2BP1 |
| chr17 | 47074561 | 47074895 | Hyper | cancer_general, tcga | IGF2BP1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 47075160 | 47075364 | Hyper | tcga, cancer_general | IGF2BP1 | chr17 | 47075715 | 47076055 | Hyper | tcga, cancer_general | IGF2BP1 |
| chr17 | 47574090 | 47574149 | Hyper | colorectal | NGFR | chr17 | 47865514 | 47865555 | Hyper | cancer_general | KAT7, FAM117A |
| chr17 | 47987525 | 47987619 | Hyper | cancer_general | | chr17 | 47987930 | 47988114 | Hyper | cancer_general | — |
| chr17 | 48041152 | 48041320 | Hyper | cancer_general | DLX4 | chr17 | 48041672 | 48041721 | Hyper | cancer_general | DLX4 |
| chr17 | 48042039 | 48042069 | Hyper | cancer_general | DLX4 | chr17 | 48042435 | 48042956 | Hyper | cancer_general | DLX4 |
| chr17 | 48048952 | 48049059 | Hyper | cancer_general | DLX4 | chr17 | 48049307 | 48050526 | Hyper | cancer_general | DLX4 |
| chr17 | 48071020 | 48071050 | Hyper | esophageal | DLX3 | chr17 | 48071791 | 48071894 | Hyper | cancer_general | DLX3 |
| chr17 | 48845804 | 48845950 | Hyper | liver_tcga | ACSF2, CHAD | chr17 | 48636581 | 48637136 | Hyper | liver_tcga, cancer_general | CACNA1G, CACNA1G-AS1, SPATA20 |
| chr17 | 49027838 | 49028876 | Hyper | head_neck | — | chr17 | 50235216 | 50235274 | Hyper | cancer_general | CA10 |
| chr17 | 50235631 | 50235952 | Hyper | cancer_general | CA10 | chr17 | 51901004 | 51901034 | Hyper | esophageal | KIF2B |
| chr17 | 53341252 | 53341536 | Hyper | cancer_general | HLF | chr17 | 53342876 | 53343089 | Hyper | tcga, cancer_general | HLF |
| chr17 | 53922649 | 53922790 | Hyper | cancer_general | — | chr17 | 54674986 | 54675272 | Hyper | tcga, cancer_general | NOG |
| chr17 | 54755969 | 54756014 | Hyper | cancer_general | — | chr17 | 55122813 | 55122842 | Hyper | literature | RNF126P1 |
| chr17 | 55213641 | 55213670 | Hyper | literature | — | chr17 | 55962573 | 55962841 | Hyper | liver_tcga | CUEDC1 |
| chr17 | 56234405 | 56234743 | Hyper | cancer_general | MSX2P1, OR4D1 | chr17 | 56326949 | 56326994 | Hyper | cancer_general | LPO |
| chr17 | 56327271 | 56327301 | Hyper | esophageal | LPO | chr17 | 56833127 | 56833221 | Hyper | cancer_general | PPM1E |
| chr17 | 56833707 | 56834075 | Hyper | tcga, esophageal | PPM1E | chr17 | 56834306 | 56834375 | Hyper | tcga | PPM1E |
| chr17 | 58216613 | 58217551 | Hyper | cancer_general | CA4 | chr17 | 58218765 | 58218993 | Hyper | cancer_general | CA4 |
| chr17 | 58227374 | 58227426 | Hyper | cancer_general | CA4 | chr17 | 58498697 | 58499314 | Hyper | tcga, cancer_general | C17orf64 |
| chr17 | 59474157 | 59474620 | Hyper | cancer_general | TBX2, BCAS3, TBX2 | chr17 | 59474833 | 59475100 | Hyper | cancer_general | TBX2, BCAS3 |
| chr17 | 59475678 | 59476127 | Hyper | cancer_general | BCAS3, TBX2 | chr17 | 59476410 | 59476635 | Hyper | cancer_general | TBX2, BCAS3 |
| chr17 | 59478147 | 59478602 | Hyper | cancer_general | TBX2, BCAS3 | chr17 | 59488101 | 59488457 | Hyper | tcga | C17orf82, TBX2 |
| chr17 | 59528876 | 59530352 | Hyper | tcga, cancer_general | TBX4 | chr17 | 59531667 | 59532139 | Hyper | cancer_general | TBX2 |
| chr17 | 59533828 | 59534491 | Hyper | cancer_general | TBX4 | chr17 | 59534751 | 59534781 | Hyper | cancer_general | TBX4 |
| chr17 | 59535137 | 59535219 | Hyper | cancer_general | TBX4 | chr17 | 59539236 | 59539601 | Hyper | cancer_general, lung | TBX4 |
| chr17 | 59924556 | 59924585 | Hyper | literature | STRADA, LOC729683, LIMD2, MAP3K3 | chr17 | 59937192 | 59937236 | Hyper | literature | INTS2 |
| chr17 | 61778085 | 61778300 | Hyper | cancer_general | PLEKHM1P, LOC146880 | chr17 | 61926172 | 61926603 | Hyper | cancer_general | TCAM1P |
| chr17 | 62777335 | 62777450 | Hyper | hepatobiliary | | chr17 | 62777746 | 62777791 | Hyper | tcga | PLEKHM1P, LOC146880 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 66596471 | 66596525 | Hyper | cancer_general | FAM20A | chr17 | 66596984 | 66597021 | Hyper | tcga | FAM20A |
| chr17 | 68164733 | 68164928 | Hyper | tcga, cancer_general | KCNJ2, KCNJ2-AS1 | chr17 | 70026543 | 70026667 | Hyper | cancer_general, breast | D43770 |
| chr17 | 70112916 | 70114517 | Hyper | cancer_general | AK094963, SOX9, AL833139 | chr17 | 70215683 | 70216585 | Hyper | cancer_general | — |
| chr17 | 71641544 | 71641683 | Hyper | cancer_general | — | chr17 | 71948439 | 71948863 | Hyper | cancer_general | KIF19 |
| chr17 | 72270286 | 72270415 | Hyper | cancer_general | DNAI2 | chr17 | 72321933 | 72321975 | Hyper | cancer_general | BTBD17, KIF19 |
| chr17 | 72322363 | 72322604 | Hyper | cancer_general | KIF19 | chr17 | 72353213 | 72353550 | Hyper | cancer_general, tcga | KIF19 |
| chr17 | 72427853 | 72427999 | Hyper | blood | GPRC5C | chr17 | 72428344 | 72428381 | Hyper | blood | GPRC5C |
| chr17 | 72667337 | 72667565 | Hyper | cancer_general | RAB37 | chr17 | 72849010 | 72849079 | Hyper | cancer_general | FDXR, GRIN2C |
| chr17 | 72857038 | 72857368 | Hyper | cancer_general, tcga | FDXR, GRIN2C | chr17 | 72920796 | 72921032 | Hyper | cancer_general | USH1G, OTOP2 |
| chr17 | 73073684 | 73073954 | Hyper | tcga, cancer_general | SLC16A5 | chr17 | 73584821 | 73584883 | Hyper | cancer_general | MYO15B |
| chr17 | 73709838 | 73709955 | Hyper | cancer_general | ITGB4, SAP30BP | chr17 | 74070281 | 74070582 | Hyper | cancer_general | SRP68, GALR2, ZACN, EXOC7 |
| chr17 | 74071445 | 74071481 | Hyper | cancer_general | ZACN, EXOC7, GALR2, SRP68 | chr17 | 74071689 | 74071729 | Hyper | cancer_general | ZACN, EXOC7, GALR2, SRP68 |
| chr17 | 74072941 | 74073036 | Hyper | cancer_general | ZACN, EXOC7, GALR2, SRP68 | chr17 | 74073269 | 74073433 | Hyper | cancer_general | ST6GALNAC2 |
| chr17 | 74533844 | 74534310 | Hyper | tcga, liver_tcga, cancer_general | PRCD, CYGB | chr17 | 74581182 | 74581221 | Hyper | cancer_general | MGAT5B, BC038218 |
| chr17 | 74732944 | 74732973 | Hyper | literature | MFSD11, MIR636, SRSF2, METTL23 | chr17 | 74865053 | 74865192 | Hyper | tcga | SEC14L1 |
| chr17 | 74865698 | 74866243 | Hyper | cancer_general | MGAT5B, BC038218 | chr17 | 75137660 | 75137887 | Hyper | tcga | 9-Sep |
| chr17 | 75315512 | 75315681 | Hyper | literature | 9-Sep | chr17 | 75368735 | 75369238 | Hyper | literature, tcga, liver_tcga, cancer_general | 9-Sep |
| chr17 | 75369440 | 75369860 | Hyper | liver_tcga, literature, cancer_general | 9-Sep | chr17 | 75370269 | 75370316 | Hyper | literature, cancer_general | MIR4316, SEPT9 |
| chr17 | 75370596 | 75370625 | Hyper | liver_tcga, literature | 9-Sep | chr17 | 75385071 | 75385446 | Hyper | literature | BC040189 |
| chr17 | 75417150 | 75417179 | Hyper | literature | 9-Sep | chr17 | 75524636 | 75525194 | Hyper | tcga, cancer_general | TMC8, TMC6 |
| chr17 | 76125196 | 76125225 | Hyper | literature | TMC8, TMC6 | chr17 | 76126434 | 76126463 | Hyper | literature | |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr17 | 76128466 | 76128690 | Hyper | literature | TMC8, TMC6 | chr17 | 76130481 | 76130510 | Hyper | literature | TMC8, TMC6 |
| chr17 | 76227849 | 76228357 | Hyper | tcga, cancer_general | TMEM235, EPR-1, BIRC5 | chr17 | 76921830 | 76921859 | Hyper | literature | — |
| chr17 | 77179113 | 77179278 | Hyper | cancer_general | RBFOX3 | chr17 | 77179630 | 77179792 | Hyper | tcga, cancer_general | RBFOX3 |
| chr17 | 77776827 | 77777056 | Hyper | cancer_general | CBX8 | chr17 | 77777585 | 77777961 | Hyper | tcga, cancer_general | CBX8 |
| chr17 | 77778943 | 77779179 | Hyper | cancer_general | CBX8 | chr17 | 77788841 | 77788969 | Hyper | cancer_general | — |
| chr17 | 77789296 | 77789500 | Hyper | cancer_general | — | chr17 | 77899664 | 77899693 | Hyper | liver_tga | TBC1D16, BC044939 |
| chr17 | 78451931 | 78452051 | Hyper | cancer_general | NPTX1 | chr17 | 78452296 | 78452340 | Hyper | cancer_general | NPTX1 |
| chr17 | 78452681 | 78452833 | Hyper | cancer_general | NPTX1 | chr17 | 79058302 | 79058333 | Hyper | liver_tga | BALAP2 |
| chr17 | 79615176 | 79615356 | Hyper | cancer_general | PDE6G, TSPAN10 | chr17 | 79813409 | 79813507 | Hyper | liver_tga | P4HB |
| chr17 | 80186260 | 80186289 | Hyper | literature | SLC16A3 | chr17 | 80197756 | 80197898 | Hyper | liver_tga | CSNK1D, SLC16A3, C17orf62, HEXDC |
| chr17 | 80329709 | 80330085 | Hyper | liver_tga, cancer_general | UTS2R, AF075112, TEX19 | chr17 | 80394573 | 80394602 | Hyper | liver_tga | |
| chr17 | 80693317 | 80693554 | Hyper | blood | FN3K, FN3KRP | chr12 | 570090 | 570171 | Hyper | cancer_general | B4GALNT3 |
| chr12 | 1639135 | 1639222 | Hyper | cancer_general | — | chr12 | 2162554 | 2162817 | Hyper | cancer_general | CACNA1C |
| chr12 | 2163164 | 2163276 | Hyper | cancer_general | CACNA1C | chr12 | 2862068 | 2862225 | Hyper | cancer_general | LOC283440 |
| chr12 | 3371882 | 3371911 | Hyper | liver_tga | TSPAN9 | chr12 | 3373533 | 3373666 | Hyper | liver_tga | TSPAN9 |
| chr12 | 3600315 | 3600345 | Hyper | cancer_general | AK125333, DQ579489, DQ583138, DQ596092, PRMT8 | chr12 | 3602270 | 3602879 | Hyper | cancer_general | PRMT8, AK125333, DQ579489 |
| chr12 | 3603100 | 3603156 | Hyper | cancer_general | PRMT8, AK125333 | chr12 | 3862254 | 3862298 | Hyper | pancreas | EFCAB4B |
| chr12 | 4274054 | 4274188 | Hyper | cancer_general | — | chr12 | 4378252 | 4378330 | Hyper | tcga | CCND2 |
| chr12 | 4381433 | 4382386 | Hyper | literature, pancreas | CCND2 | chr12 | 4382965 | 4382999 | Hyper | literature | CCND2 |
| chr12 | 4383492 | 4383784 | Hyper | literature | CCND2 | chr12 | 4384389 | 4384418 | Hyper | literature | CCND2 |
| chr12 | 4384736 | 4384902 | Hyper | literature | CCND2 | chr12 | 4918986 | 4919244 | Hyper | tcga | KCNA6 |
| chr12 | 5018073 | 5018692 | Hyper | tcga, cancer_general | KCNA1 | chr12 | 5019050 | 5020416 | Hyper | tcga | KCNA1 |
| chr12 | 5153039 | 5153520 | Hyper | tcga, cancer_general | KCNA5 | chr12 | 5541100 | 5541177 | Hyper | pancreas | NTF3 |
| chr12 | 5542325 | 5542439 | Hyper | cancer_general | NTF3 | chr12 | 5542759 | 5542911 | Hyper | cancer_general | NTF3 |
| chr12 | 6308743 | 6308772 | Hyper | literature | CD9 | chr12 | 6664508 | 6665384 | Hyper | literature, tcga, cancer_general | NOP2, IFFO1 |
| chr12 | 8025631 | 8025660 | Hyper | literature | NANOGP1 | chr12 | 8171360 | 8171745 | Hyper | tcga, cancer_general | — |
| chr12 | 8549178 | 8549208 | Hyper | esophageal | LINC00937 | chr12 | 8850658 | 8850744 | Hyper | esophageal | RIMKLB |
| chr12 | 11653449 | 11653479 | Hyper | cancer_general | — | chr12 | 14133152 | 14133263 | Hyper | cancer_general | — |
| chr12 | 14133619 | 14133881 | Hyper | cancer_general | — | chr12 | 14135111 | 14135339 | Hyper | cancer_general | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 15374258 | 15374291 | Hyper | cancer_general | RERG | chr12 | 16500576 | 16500621 | Hyper | blood | MGST1 |
| chr12 | 19282333 | 19282363 | Hyper | blood | PLEKHA5 | chr12 | 20521704 | 20521841 | Hyper | cancer_general | PDE3A |
| chr12 | 20522457 | 20522487 | Hyper | cancer_general | PDE3A | chr12 | 20522769 | 20522891 | Hyper | cancer_general | PDE3A |
| chr12 | 21680394 | 21680683 | Hyper | tcga, cancer_general | C12orf39, GYS2, GOLT1B | chr12 | 21810264 | 21810868 | Hyper | tcga, liver_tcga | LDHB |
| chr12 | 22093825 | 22094810 | Hyper | literature, cancer_general | ABCC9 | chr12 | 22095095 | 22095136 | Hyper | cancer_general | ABCC9 |
| chr12 | 22486799 | 22487473 | Hyper | cancer_general, tcga, liver_tcga | ST8SIA1 | chr12 | 24714909 | 24714938 | Hyper | tcga | LINC00477 |
| chr12 | 24715235 | 24715264 | Hyper | tcga | LINC00477 | chr12 | 24716033 | 24716218 | Hyper | tcga | LINC00477 |
| chr12 | 25055952 | 25056436 | Hyper | liver_tcga, literature, cancer_general | BCAT1 | chr12 | 25101592 | 25101660 | Hyper | cancer_general | — |
| chr12 | 25101919 | 25102086 | Hyper | cancer_general | — | chr12 | 25362824 | 25362853 | Hyper | literature | KRAS, LYRM5 |
| chr12 | 25368463 | 25368492 | Hyper | literature | KRAS | chr12 | 25378543 | 25378662 | Hyper | literature | KRAS DD157417, KRAS |
| chr12 | 25380231 | 25380299 | Hyper | literature | KRAS | chr12 | 25398203 | 25398319 | Hyper | literature | |
| chr12 | 28123996 | 28124247 | Hyper | tcga | PTHLH | chr12 | 28127767 | 28128302 | Hyper | tcga, cancer_general, lung | PTHLH |
| chr12 | 28128547 | 28129084 | Hyper | lung, cancer_general | PTHLH | chr12 | 29936016 | 29936048 | Hyper | cancer_general | TMTC1 |
| chr12 | 29936602 | 29936864 | Hyper | tcga, cancer_general | TMTC1 | chr12 | 29937331 | 29937374 | Hyper | cancer_general | TMTC1 |
| chr12 | 30322774 | 30323517 | Hyper | cancer_general | — | chr12 | 30975572 | 30976030 | Hyper | tcga, cancer_general | — |
| chr12 | 31079268 | 31079499 | Hyper | cancer_general | TSPAN11 | chr12 | 33591774 | 33591804 | Hyper | cancer_general | SYT10 |
| chr12 | 33592613 | 33592889 | Hyper | cancer_general | SYT10 | chr12 | 39299117 | 39299560 | Hyper | cancer_general | CPNE8 |
| chr12 | 39539353 | 39539436 | Hyper | cancer_general | — | chr12 | 40618404 | 40618470 | Hyper | cancer_general | LRRK2 |
| chr12 | 41086183 | 41086379 | Hyper | tcga | CNTN1 | chr12 | 41086784 | 41087106 | Hyper | cancer_general | CNTN1 |
| chr12 | 41582513 | 41582988 | Hyper | cancer_general | PDZRN4 | chr12 | 41583374 | 41583419 | Hyper | cancer_general | PDZRN4 |
| chr12 | 43944893 | 43945124 | Hyper | cancer_general | — | chr12 | 43945356 | 43945526 | Hyper | cancer_general | — |
| chr12 | 43945844 | 43946298 | Hyper | literature, cancer_general | — | chr12 | 45269504 | 45269624 | Hyper | cancer_general | NELL2 |
| chr12 | 45444118 | 45445258 | Hyper | cancer_general | DBX2 | chr12 | 46767650 | 46767697 | Hyper | tcga | SLC38A2 |
| chr12 | 47225381 | 47225579 | Hyper | cancer_general | SLC38A4 | chr12 | 48397195 | 48398070 | Hyper | cancer_general | COL2A1 |
| chr12 | 48398641 | 48398671 | Hyper | cancer_general | COL2A1 | chr12 | 48690674 | 48690929 | Hyper | tcga | — |
| chr12 | 49297802 | 49297915 | Hyper | cancer_general | CCDC65 | chr12 | 49366374 | 49366423 | Hyper | cancer_general | WNT1, WNT10B |
| chr12 | 49374914 | 49375119 | Hyper | cancer_general | WNT1, WNT10B | chr12 | 49375325 | 49375529 | Hyper | cancer_general, tcga | WNT1, WNT10B |
| chr12 | 49390873 | 49391877 | Hyper | cancer_general | PRKAG1, DDN | chr12 | 49691049 | 49691078 | Hyper | liver_tcga | PRPH |
| chr12 | 49727049 | 49727127 | Hyper | cancer_general | TROAP, C1QL4 | chr12 | 49729728 | 49730090 | Hyper | cancer_general | C1QL4, TROAP |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 49759530 | 49759559 | Hyper | literature | SPATS2 | chr12 | 50297497 | 50298055 | Hyper | cancer_general, literature, liver_tcga | FAIM2, LOC283332, BC034605 |
| chr12 | 50355275 | 50355469 | Hyper | cancer_general | AQP6, AQP2, AQP5 | chr12 | 50426748 | 50426799 | Hyper | cancer_general | RACGAP1 |
| chr12 | 52262983 | 52263106 | Hyper | cancer_general tcga, liver_tcga, cancer_general | — | chr12 | 52301280 | 52301367 | Hyper | cancer_general | ACVRL1 |
| chr12 | 52400831 | 52401537 | Hyper | liver_tcga, cancer_general | GRASP, ACVR1B | chr12 | 52408905 | 52409033 | Hyper | liver_tcga | NR4A1, GRASP |
| chr12 | 52627184 | 52627438 | Hyper | liver_tcga, cancer_general | KRT7, LINC00592 | chr12 | 52652153 | 52652613 | Hyper | cancer_general | KRT121P, KRT86, KRT7 |
| chr12 | 53108089 | 53108218 | Hyper | cancer_general | — | chr12 | 53359345 | 53359563 | Hyper | cancer_general | — |
| chr12 | 54089093 | 54089511 | Hyper | liver_tcga, cancer_general, tcga | — | chr12 | 54132252 | 54132329 | Hyper | cancer_general | — |
| chr12 | 54145843 | 54145895 | Hyper | cancer_general | — | chr12 | 54321250 | 54321628 | Hyper | literature, cancer_general | HOXC-AS5 |
| chr12 | 54322201 | 54322252 | Hyper | cancer_general | HOXC-AS5 | chr12 | 54324799 | 54324937 | Hyper | cancer_general | HOXC-AS5, HOXC13 |
| chr12 | 54329358 | 54329947 | Hyper | cancer_general | HOXC13, HOXC-AS5 | chr12 | 54331062 | 54331135 | Hyper | cancer_general | HOXC13, HOXC-AS5 |
| chr12 | 54332868 | 54333337 | Hyper | cancer_general | HOXC13, HOXC-AS5 | chr12 | 54338666 | 54339681 | Hyper | cancer_general | HOXC13, HOXC-AS5, HOXC12 |
| chr12 | 54343812 | 54343861 | Hyper | cancer_general | HOXC12, HOXC13 | chr12 | 54345611 | 54346032 | Hyper | cancer_general | HOXC12, HOXC13 |
| chr12 | 54348844 | 54349336 | Hyper | cancer_general | HOTAIR, HOXC12, HOXC13 | chr12 | 54354514 | 54354621 | Hyper | cancer_general | HOTAIR, HOTAIR_4, HOTAIR_5, HOXC12 |
| chr12 | 54354905 | 54355542 | Hyper | tcga, literature, cancer_general | HOTAIR, HOTAIR_4, HOTAIR_5, HOXC12 | chr12 | 54359960 | 54360084 | Hyper | cancer_general | HOXC12, HOTAIR_4, HOTAIR_5, HOXC-AS5, HOTAIR |
| chr12 | 54360608 | 54360649 | Hyper | cancer_general | HOTAIR_4, HOTAIR_5, HOXC11, HOTAIR | chr12 | 54377912 | 54378115 | Hyper | cancer_general | HOXC10, HOXC11, HOTAIR |
| chr12 | 54379174 | 54379623 | Hyper | cancer_general | MIR196A2, HOXC10, HOXC11 | chr12 | 54379888 | 54380459 | Hyper | cancer_general | MIR196A2, HOXC10, HOXC11 |
| chr12 | 54387842 | 54387959 | Hyper | cancer_general | HOXC9, MIR196A2, HOXC10 | chr12 | 54388215 | 54388245 | Hyper | cancer_general | MIR196A2, HOXC9, HOXC10 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 54391369 | 54391403 | Hyper | cancer_general | HOXC9, MIR196A2, HOXC10 | chr12 | 54393479 | 54393684 | Hyper | cancer_general | HOXC9, HOXC8, MIR196A2, HOXC10 |
| chr12 | 54393950 | 54394162 | Hyper | cancer_general | HOXC8, HOXC9, MIR196A2, HOXC10 | chr12 | 54394410 | 54394442 | Hyper | cancer_general | HOXC8, HOXC9, MIR196A2 |
| chr12 | 54398793 | 54398959 | Hyper | cancer_general | HOXC8, HOXC9 | chr12 | 54399616 | 54399646 | Hyper | head_neck | HOXC8, HOXC9 |
| chr12 | 54402690 | 54402796 | Hyper | cancer_general | HOXC8, HOXC6, HOXC4, HOXC5, HOXC9 | chr12 | 54403067 | 54403360 | Hyper | cancer_general | HOXC8, HOXC9, HOXC6, HOXC4, HOXC5 |
| chr12 | 54408411 | 54408726 | Hyper | cancer_general | HOXC6, HOXC4, HOXC5, HOXC8 | chr12 | 54409476 | 54409505 | Hyper | literature | HOXC6, HOXC4, HOXC5, HOXC8 |
| chr12 | 54423565 | 54423697 | Hyper | cancer_general | HOXC5, MIR615, HOXC6, HOXC4 | chr12 | 54424746 | 54424788 | Hyper | cancer_general | HOXC5, MIR615, HOXC6, HOXC4 |
| chr12 | 54425003 | 54425119 | Hyper | cancer_general | HOXC5, MIR615, HOXC6, HOXC4 | chr12 | 54447351 | 54447581 | Hyper | cancer_general | HOXC4, FLJ12825 |
| chr12 | 54447883 | 54447977 | Hyper | cancer_general | HOXC4, FLJ12825 | chr12 | 54520745 | 54520868 | Hyper | cancer_general | LOC400043 |
| chr12 | 54812238 | 54812359 | Hyper | cancer_general | ITGA5 | chr12 | 54942994 | 54943116 | Hyper | tcga | PDE1B, NCKAP1L |
| chr12 | 56478840 | 56478869 | Hyper | literature | ERBB3 | chr12 | 56481645 | 56481937 | Hyper | literature | ERBB3 |
| chr12 | 56486572 | 56486601 | Hyper | literature | ERBB3 | chr12 | 56490965 | 56490994 | Hyper | literature | ERBB3, PA2G4 |
| chr12 | 56491630 | 56491659 | Hyper | literature | PA2G4, ERBB3 | chr12 | 56492618 | 56492647 | Hyper | literature | PA2G4, ERBB3 |
| chr12 | 56873601 | 56873630 | Hyper | liver_tcga | BC059370, GLS2, SPRYD4 | chr12 | 56882240 | 56882380 | Hyper | blood | BC059370, GLS2 |
| chr12 | 57387303 | 57387332 | Hyper | liver_tcga | GPR182, ZBTB39 | chr12 | 57618574 | 57618979 | Hyper | tcga, cancer_general | SHMT2, NDUFA4L2, NXPH4 |
| chr12 | 57944081 | 57944117 | Hyper | cancer_general | KIF5A, DCTN2 | chr12 | 58021320 | 58021713 | Hyper | cancer_general, liver_tcga | BC073932, B4GALNT1, SLC26A10 |
| chr12 | 58021916 | 58022029 | Hyper | liver_tcga | B4GALNT1, SLC26A10 | chr12 | 58025646 | 58025873 | Hyper | cancer_general | BC073932, JA611266, B4GALNT1, SLC26A10 |
| chr12 | 58145415 | 58145450 | Hyper | literature | DM110804, MARCH9, | chr12 | 59314159 | 59314189 | Hyper | blood | LRIG3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 62284838 | 62286017 | Hyper | tcga, cancer_general | CDK4, TSPAN31, FAM19A2 | chr12 | 62586252 | 62586281 | Hyper | tcga | FAM19A2 |
| chr12 | 63025574 | 63026160 | Hyper | tcga, cancer_general | — | chr12 | 63543848 | 63544727 | Hyper | cancer_general | AVPR1A |
| chr12 | 63545313 | 63545343 | Hyper | cancer_general | AVPR1A | chr12 | 64061821 | 64062159 | Hyper | cancer_general | DPY19L2 |
| chr12 | 64062369 | 64062578 | Hyper | tcga, liver_tcga | DPY19L2 | chr12 | 64062921 | 64063096 | Hyper | cancer_general | DPY19L2 |
| chr12 | 64784092 | 64784252 | Hyper | liver_tcga, cancer_general | — | chr12 | 64784534 | 64784564 | Hyper | cancer_general | — |
| chr12 | 65218102 | 65219156 | Hyper | tcga, cancer_general | TBC1D30 | chr12 | 65219376 | 65219784 | Hyper | cancer_general | TBC1D30 |
| chr12 | 65220205 | 65220350 | Hyper | cancer_general | TBC1D30 | chr12 | 65514863 | 65515596 | Hyper | cancer_general | WIF1 |
| chr12 | 66122800 | 66123519 | Hyper | cancer_general | — | chr12 | 66135984 | 66136014 | Hyper | cancer_general | — |
| chr12 | 66582827 | 66583137 | Hyper | liver_tcga, cancer_general | IRAK3 | chr12 | 69327259 | 69327463 | Hyper | cancer_general | CPM |
| chr12 | 72332641 | 72332696 | Hyper | lung | TPH2 | chr12 | 72665186 | 72665788 | Hyper | cancer_general | TRHDE-AS1, BC093903, TRHDE |
| chr12 | 72666115 | 72666211 | Hyper | cancer_general | BC093903, TRHDE-AS1, TRHDE | chr12 | 72666713 | 72667425 | Hyper | tcga, cancer_general | TRHDE-AS1, TRHDE, BC093903 |
| chr12 | 72667652 | 72667682 | Hyper | cancer_general | TRHDE, BC093903, TRHDE-AS1 | chr12 | 75601264 | 75601910 | Hyper | cancer_general | KCNC2 |
| chr12 | 75602976 | 75603231 | Hyper | cancer_general | KCNC2 | chr12 | 75728336 | 75728485 | Hyper | tcga, cancer_general | GLIPR1L1, CAPS2 |
| chr12 | 75728737 | 75728766 | Hyper | tcga | GLIPR1L1, CAPS2 | chr12 | 77719311 | 77719422 | Hyper | tcga | — |
| chr12 | 79257222 | 79257351 | Hyper | pancreas | SYT1 | chr12 | 79258924 | 79258954 | Hyper | cancer_general | SYT1 |
| chr12 | 81102185 | 81102562 | Hyper | cancer_general, liver_tcga | MYF5, MYF6 | chr12 | 81107989 | 81108034 | Hyper | liver_tcga | MYF5, MYF6 |
| chr12 | 81471517 | 81472111 | Hyper | cancer_general | ACSS3 | chr12 | 85306519 | 85306578 | Hyper | cancer_general | SLC6A15 |
| chr12 | 85667272 | 85667731 | Hyper | cancer_general | ALX1 | chr12 | 85673206 | 85673235 | Hyper | literature | ALX1 |
| chr12 | 85673460 | 85674807 | Hyper | cancer_general | ALX1 | chr12 | 88973544 | 88973582 | Hyper | blood | U1 |
| chr12 | 88974159 | 88974253 | Hyper | blood | U1 | chr12 | 93966429 | 93966603 | Hyper | cancer_general | SOCS2, SOCS2-AS1 |
| chr12 | 93966998 | 93967239 | Hyper | cancer_general | SOCS2, SOCS2-AS1 | chr12 | 94543409 | 94543445 | Hyper | cancer_general | PLXNC1 |
| chr12 | 94543899 | 94543961 | Hyper | cancer_general | PLXNC1 | chr12 | 95267524 | 95267554 | Hyper | esophageal | — |
| chr12 | 95267865 | 95267976 | Hyper | cancer_general | — | chr12 | 95941868 | 95942978 | Hyper | cancer_general, liver_tcga, literature | USP44 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 99288312 | 99289309 | Hyper | cancer_general, tcga | ANKS1B | chr12 | 101111029 | 101111061 | Hyper | cancer_general | ANO4 |
| chr12 | 101111373 | 101111479 | Hyper | cancer_general | ANO4 | chr12 | 103218495 | 103218595 | Hyper | cancer_general | LINC00485 |
| chr12 | 103350324 | 103350354 | Hyper | cancer_general | ASCL1 | chr12 | 103351564 | 103352681 | Hyper | tcga, cancer_general | ASCL1 |
| chr12 | 103358865 | 103358899 | Hyper | cancer_general | ASCL1 | chr12 | 103359556 | 103359586 | Hyper | cancer_general | ASCL1 |
| chr12 | 103889160 | 103889211 | Hyper | pancreas | C12orf42 | chr12 | 103889746 | 103889812 | Hyper | cancer_general | C12orf42 |
| chr12 | 104609417 | 104610100 | Hyper | tcga, cancer_general | TXNRD1 | chr12 | 104850505 | 104850592 | Hyper | colorectal | CHST11 |
| chr12 | 104851077 | 104851186 | Hyper | colorectal | CHST11 | chr12 | 104852032 | 104852508 | Hyper | cancer_general, tcga | CHST11 |
| chr12 | 105478323 | 105478419 | Hyper | liver_tcga, hepatobiliary | ALDH1L2 | chr12 | 106533852 | 106533881 | Hyper | literature | NUAK1 |
| chr12 | 106974353 | 106974383 | Hyper | cancer_general | LOC100287944, RFX4 | chr12 | 106976725 | 106976795 | Hyper | cancer_general | RFX4, LOC100287944 |
| chr12 | 106977321 | 106977497 | Hyper | cancer_general | RFX4, LOC100287944 | chr12 | 106979161 | 106979534 | Hyper | cancer_general | LOC100287944, RFX4 |
| chr12 | 106979799 | 106979995 | Hyper | cancer_general | RFX4, LOC100287944 | chr12 | 106980223 | 106980333 | Hyper | cancer_general | RFX4, LOC100287944 |
| chr12 | 106980854 | 106981406 | Hyper | cancer_general | RFX4, LOC100287944 | chr12 | 107486550 | 107486672 | Hyper | blood | CRY1 |
| chr12 | 107487194 | 107487855 | Hyper | blood | CRY1 | chr12 | 107712273 | 107712303 | Hyper | blood | BTBD11 |
| chr12 | 107713205 | 107713235 | Hyper | cancer_general | BTBD11 | chr12 | 107714866 | 107715153 | Hyper | cancer_general | BTBD11 |
| chr12 | 108168971 | 108169573 | Hyper | literature, cancer_general, liver_tcga | ASCL4 | chr12 | 108237466 | 108237586 | Hyper | cancer_general | — |
| chr12 | 108238102 | 108238616 | Hyper | cancer_general, tcga | — | chr12 | 108297411 | 108297466 | Hyper | cancer_general | LOC728739 |
| chr12 | 109639281 | 109639475 | Hyper | liver_tcga | ACACB | chr12 | 111127124 | 111127455 | Hyper | tcga, cancer_general | HVCN1 |
| chr12 | 111471177 | 111471559 | Hyper | tcga, literature, cancer_general | CUX2 | chr12 | 111471948 | 111472752 | Hyper | cancer_general, tcga | CUX2 |
| chr12 | 112888151 | 112888315 | Hyper | literature | PTPN11 | chr12 | 112910821 | 112910850 | Hyper | literature | PTPN11 |
| chr12 | 112915509 | 112915538 | Hyper | literature | PTPN11 | chr12 | 112926255 | 112926284 | Hyper | literature | PTPN11 |
| chr12 | 112926876 | 112926914 | Hyper | literature | PTPN11 | chr12 | 113012954 | 113013157 | Hyper | cancer_general | RPH3A |
| chr12 | 113541667 | 113542099 | Hyper | cancer_general | RASAL1, DTX1 | chr12 | 113592238 | 113592359 | Hyper | cancer_general | DDX54, CCDC42B |
| chr12 | 113900704 | 113900765 | Hyper | tcga | LHX5 | chr12 | 113901074 | 113901591 | Hyper | tcga, cancer_general | LHX5 |
| chr12 | 113902026 | 113902353 | Hyper | cancer_general | LHX5 | chr12 | 113903468 | 113903498 | Hyper | cancer_general | LHX5 |
| chr12 | 113904779 | 113905016 | Hyper | cancer_general | LHX5 | chr12 | 113908990 | 113909455 | Hyper | cancer_general | LHX5 |
| chr12 | 113909667 | 113909708 | Hyper | cancer_general | LHX5 | chr12 | 113913267 | 113914050 | Hyper | cancer_general | LHX5 |
| chr12 | 113916222 | 113916316 | Hyper | cancer_general | LHX5 | chr12 | 113916649 | 113916678 | Hyper | literature | LHX5 |
| chr12 | 113916972 | 113917012 | Hyper | cancer_general | LHX5 | chr12 | 113917232 | 113917310 | Hyper | cancer_general | LHX5 |
| chr12 | 113917775 | 113917890 | Hyper | cancer_general | LHX5 | chr12 | 114029408 | 114029660 | Hyper | tcga | — |
| chr12 | 114076029 | 114076093 | Hyper | cancer_general | — | chr12 | 114833985 | 114834102 | Hyper | cancer_general | TBX5 |
| chr12 | 114838325 | 114838726 | Hyper | cancer_general | TBX5-AS1, TBX5 | chr12 | 114839104 | 114839147 | Hyper | cancer_general | TBX5-AS1, TBX5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 114841046 | 114841084 | Hyper | cancer_general | TBX5-AS1, TBX5 | chr12 | 114841425 | 114841493 | Hyper | cancer_general | TBX5-AS1, TBX5 |
| chr12 | 114843112 | 114843278 | Hyper | cancer_general | TBX5-AS1, TBX5 | chr12 | 114843545 | 114843660 | Hyper | cancer_general | TBX5-AS1, TBX5 |
| chr12 | 114844201 | 114844300 | Hyper | cancer_general | TBX5-AS1, TBX5 | chr12 | 114846715 | 114846768 | Hyper | cancer_general | TBX5-AS1, TBX5 |
| chr12 | 114846979 | 114847691 | Hyper | cancer_general | TBX5-AS1, TBX5 | chr12 | 114852040 | 114852082 | Hyper | cancer_general | TBX5-AS1, TBX5 |
| chr12 | 114852293 | 114852373 | Hyper | tcga | TBX5-AS1 | chr12 | 114877171 | 114877262 | Hyper | cancer_general | — |
| chr12 | 114878550 | 114878584 | Hyper | cancer_general | — | chr12 | 114878813 | 114879012 | Hyper | cancer_general | — |
| chr12 | 114881634 | 114881764 | Hyper | cancer_general | — | chr12 | 114882555 | 114882646 | Hyper | cancer_general | — |
| chr12 | 114883473 | 114883535 | Hyper | cancer_general | — | chr12 | 114885222 | 114885284 | Hyper | cancer_general | — |
| chr12 | 114918594 | 114918717 | Hyper | cancer_general | — | chr12 | 115136159 | 115136363 | Hyper | cancer_general | — |
| chr12 | 116946086 | 116946548 | Hyper | tcga, cancer_general | — | chr12 | 117798065 | 117798095 | Hyper | cancer_general | NOS1 |
| chr12 | 117798690 | 117798965 | Hyper | cancer_general | NOS1 | chr12 | 117799413 | 117799529 | Hyper | cancer_general | NOS1 |
| chr12 | 119212216 | 119212381 | Hyper | cancer_general | — | chr12 | 119418594 | 119418847 | Hyper | cancer_general | SRRM4 |
| chr12 | 119419436 | 119419466 | Hyper | cancer_general | SRRM4 | chr12 | 119419720 | 119419899 | Hyper | cancer_general | SRRM4 |
| chr12 | 120032862 | 120033169 | Hyper | cancer_general | TMEM233, AF086288 | chr12 | 120535158 | 120535187 | Hyper | literature | RAB35, CCDC64 |
| chr12 | 120536625 | 120536654 | Hyper | literature | RAB35, CCDC64 | chr12 | 124246908 | 124246937 | Hyper | liver_tcga | DNAH10, ATP6V0A2 |
| chr12 | 124247208 | 124247237 | Hyper | liver_tcga | DNAH10, ATP6V0A2 | chr12 | 124865115 | 124865144 | Hyper | literature | NCOR2 |
| chr12 | 125533949 | 125534407 | Hyper | liver_tcga, cancer_general | — | chr12 | 125670117 | 125670289 | Hyper | cancer_general | — |
| chr12 | 126168554 | 126168620 | Hyper | cancer_general | — | chr12 | 127210965 | 127211378 | Hyper | cancer_general | LINC00944 |
| chr12 | 127765158 | 127765432 | Hyper | cancer_general | — | chr12 | 127940086 | 127940247 | Hyper | pancreas | — |
| chr12 | 128751384 | 128751443 | Hyper | cancer_general | TMEM132C | chr12 | 128751821 | 128752240 | Hyper | cancer_general | TMEM132C |
| chr12 | 128752499 | 128752944 | Hyper | cancer_general | TMEM132C | chr12 | 128753210 | 128753240 | Hyper | cancer_general | TMEM132C |
| chr12 | 128850534 | 128850644 | Hyper | pancreas | GLT1D1 | chr12 | 129338003 | 129338816 | Hyper | cancer_general | GLT1D1 |
| chr12 | 129427424 | 129427557 | Hyper | pancreas, cancer_general | — | chr12 | 130387776 | 130387811 | Hyper | cancer_general | — |
| chr12 | 130388410 | 130389152 | Hyper | cancer_general | — | chr12 | 130589202 | 130589266 | Hyper | cancer_general | — |
| chr12 | 130645233 | 130645627 | Hyper | cancer_general | FZD10, FZD10-AS1 | chr12 | 130646686 | 130648472 | Hyper | tcga, cancer_general | FZD10-AS1, FZD10 |
| chr12 | 131200379 | 131200645 | Hyper | tcga | RIMBP2 | chr12 | 131400816 | 131400919 | Hyper | cancer_general | — |
| chr12 | 133195093 | 133195196 | Hyper | liver_tcga | LRCOL1, P2RX2, POLE | chr12 | 133463736 | 133463876 | Hyper | esophageal | CHFR |
| chr12 | 133464108 | 133464166 | Hyper | esophageal | CHFR | chr12 | 133464840 | 133465027 | Hyper | tcga | CHFR |
| chr12 | 133481389 | 133481655 | Hyper | liver_tcga, cancer_general | AK055957 | chr12 | 133484742 | 133485355 | Hyper | liver_tcga, cancer_general | AK055957 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr12 | 133485557 | 133485847 | Hyper | tcga, cancer_general | AK055957 | chr12 | 133758048 | 133758107 | Hyper | esophageal | ZNF268 |
| chr8 | 686870 | 687316 | Hyper | cancer_general | ERICH1-AS1 | chr8 | 687745 | 688032 | Hyper | tcga, cancer_general | ERICH1-AS1 |
| chr8 | 688360 | 688390 | Hyper | cancer_general | ERICH1-AS1 | chr8 | 688985 | 689043 | Hyper | cancer_general | ERICH1-AS1 |
| chr8 | 1950097 | 1950134 | Hyper | tcga | KBTBD11 | chr8 | 4849141 | 4849177 | Hyper | cancer_general | — |
| chr8 | 4849466 | 4849500 | Hyper | cancer_general | — | chr8 | 4850247 | 4850516 | Hyper | cancer_general | — |
| chr8 | 4851736 | 4851765 | Hyper | tcga | — | chr8 | 4852021 | 4852118 | Hyper | cancer_general | — |
| chr8 | 9756051 | 9756476 | Hype | cancer_general | LINC00599, AK091593, MIR124-1 | chr8 | 9760735 | 9761155 | Hyper | tcga, cancer_general | MIR124-1, AK091593, LINC00599 |
| chr8 | 9762586 | 9762864 | Hyper | cancer_general | MIR124-1, AK091593, LINC00599 | chr8 | 9763143 | 9763275 | Hyper | cancer_general | MIR124-1, AK091593, LINC00599 |
| chr8 | 9763895 | 9764214 | Hyper | cancer_general | MIR124-1, AK091593, LINC00599 | chr8 | 9764434 | 9764551 | Hyper | cancer_general | MIR124-1, AK091593, LINC00599 |
| chr8 | 10587589 | 10587783 | Hyper | tcga | BC043573, SOX7 | chr8 | 10588383 | 10588456 | Hyper | cancer_general | BC043573, SOX7 |
| chr8 | 11204479 | 11204509 | Hyper | cancer_general | BC038546, TDH | chr8 | 11204810 | 11204905 | Hyper | cancer_general | TDH, BC038546 |
| chr8 | 11536827 | 11536857 | Hyper | cancer_general | GATA4 | chr8 | 11537225 | 11537259 | Hyper | cancer_general | GATA4 |
| chr8 | 11554885 | 11554915 | Hyper | cancer_general | GATA4 | chr8 | 11555152 | 11555521 | Hyper | cancer_general | GATA4 |
| chr8 | 11559759 | 11560375 | Hyper | cancer_general | GATA4 | chr8 | 11560711 | 11560793 | Hyper | cancer_general | GATA4 |
| chr8 | 11561442 | 11562169 | Hyper | tcga, cancer_general | GATA4 | chr8 | 11562422 | 11562485 | Hyper | cancer_general | GATA4 |
| chr8 | 11562701 | 11562917 | Hyper | cancer_general | GATA4 | chr8 | 12990386 | 12990431 | Hyper | cancer_general | DLC1 |
| chr8 | 12990664 | 12990784 | Hyper | cancer_general | DLC1 | chr8 | 15094505 | 15094582 | Hyper | cancer_general | — |
| chr8 | 15397735 | 15397845 | Hyper | cancer_general | TUSC3 | chr8 | 16884182 | 16884239 | Hyper | tcga | MICU3 |
| chr8 | 16885205 | 16885241 | Hyper | cancer_general | MICU3 | chr8 | 17271066 | 17271119 | Hyper | liver_tcga | — |
| chr8 | 19797433 | 19797463 | Hyper | cancer_general | LPL | chr8 | 19797939 | 19798019 | Hyper | cancer_general | LPL |
| chr8 | 20160762 | 20160894 | Hyper | cancer_general | — | chr8 | 22089409 | 22089560 | Hyper | cancer_general | PHYHIP |
| chr8 | 22562345 | 22562483 | Hyper | cancer_general | PEBP4 | chr8 | 22960648 | 22960723 | Hyper | cancer_general | TNFRSF10C, LOC254896 |
| chr8 | 23020951 | 23021107 | Hyper | tcga | TNFRSF10D | chr8 | 23260683 | 23260870 | Hyper | cancer_general | ENTPD4 |
| chr8 | 23559385 | 23560525 | Hyper | cancer_general | NKX2-6 | chr8 | 23563791 | 23564388 | Hyper | cancer_general | NKX2-6 |
| chr8 | 23564652 | 23565024 | Hyper | cancer_general | NKX2-6 | chr8 | 23566803 | 23567492 | Hyper | cancer_general | NKX2-6 |
| chr8 | 23571681 | 23571973 | Hyper | cancer_general | NKX2-6 | chr8 | 23572377 | 23572554 | Hyper | cancer_general | NKX2-6 |
| chr8 | 23584078 | 23584760 | Hyper | tcga, cancer_general | — | chr8 | 24770314 | 24770581 | Hyper | cancer_general | AK308605, NEFM |
| chr8 | 24771168 | 24771213 | Hyper | cancer_general | NEFM, AK308605 | chr8 | 24771431 | 24771562 | Hyper | literature, cancer_general | NEFM, AK308605 |
| chr8 | 24813188 | 24813287 | Hyper | cancer_general | NEFL | chr8 | 24813750 | 24814407 | Hyper | tcga, cancer_general | NEFL |
| chr8 | 24857776 | 24857808 | Hyper | cancer_general | — | chr8 | 24858336 | 24858440 | Hyper | cancer_general | — |
| chr8 | 24858856 | 24859161 | Hyper | tcga, cancer_general | — | chr8 | 24859496 | 24859526 | Hyper | cancer_general | — |
| chr8 | 25041746 | 25041864 | Hyper | blood | DOCK5 | chr8 | 25042534 | 25042567 | Hyper | blood | DOCK5 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 25900408 | 25901317 | Hyper | cancer_general | EBF2 | chr8 | 25901540 | 25901765 | Hyper | cancer_general | EBF2 |
| chr8 | 25902146 | 25902176 | Hyper | cancer_general | EBF2 | chr8 | 25902619 | 25902649 | Hyper | cancer_general | EBF2 |
| chr8 | 25903662 | 25903854 | Hyper | cancer_general | EBF2 | chr8 | 25904157 | 25904191 | Hyper | cancer_general | EBF2 |
| chr8 | 25905096 | 25905126 | Hyper | cancer_general | EBF2 | chr8 | 25905762 | 25905811 | Hyper | cancer_general | EBF2 |
| chr8 | 25909197 | 25909597 | Hyper | cancer_general | EBF2 | chr8 | 26372863 | 26372893 | Hyper | cancer_general | DPYSL2, PNMA2 |
| chr8 | 26723985 | 26724080 | Hyper | cancer_general | AK311558, ADRA1A | chr8 | 30243388 | 30243423 | Hyper | cancer_general | RBPMS, LOC100128750 |
| chr8 | 30769249 | 30769411 | Hyper | cancer_general | — | chr8 | 30770106 | 30770188 | Hyper | tcga | — |
| chr8 | 31496481 | 31496757 | Hyper | cancer_general | NRG1 | chr8 | 31497024 | 31497152 | Hyper | cancer_general | NRG1 |
| chr8 | 31497499 | 31497639 | Hyper | cancer_general | NRG1 | chr8 | 31498117 | 31498150 | Hyper | cancer_general | NRG1 |
| chr8 | 32406598 | 32406914 | Hyper | tcga, cancer_general | NRG1 | chr8 | 33372069 | 33372125 | Hyper | cancer_general | TTI2 |
| chr8 | 33457142 | 33457379 | Hyper | cancer_general | DUSP26 | chr8 | 35092985 | 35093054 | Hyper | cancer_general | UNC5D |
| chr8 | 35093951 | 35093981 | Hyper | cancer_general | UNC5D | chr8 | 37655454 | 37655517 | Hyper | cancer_general | GPR124 |
| chr8 | 37655810 | 37656081 | Hyper | cancer_general | GPR124 | chr8 | 37822796 | 37823423 | Hyper | tcga, cancer_general | ADRB3 |
| chr8 | 37823678 | 37823726 | Hyper | cancer_general | ADRB3 | chr8 | 38008234 | 38008557 | Hyper | cancer_general | STAR |
| chr8 | 38274835 | 38274864 | Hyper | literature | FGFR1, LETM2 | chr8 | 38323911 | 38323941 | Hyper | cancer_general | FGFR1 |
| chr8 | 38965121 | 38965386 | Hyper | liver_tcga | ADAM32 | chr8 | 41165865 | 41166723 | Hyper | cancer_general | SFRP1 |
| chr8 | 41166974 | 41167035 | Hyper | cancer_general | SFRP1 | chr8 | 41424760 | 41424842 | Hyper | cancer_general | — |
| chr8 | 41624826 | 41624855 | Hyper | tcga | — | chr8 | 41625112 | 41625141 | Hyper | tcga | — |
| chr8 | 41733505 | 41733640 | Hyper | cancer_general | — | chr8 | 41753593 | 41753761 | Hyper | cancer_general | — |
| chr8 | 41754152 | 41754885 | Hyper | liver_tcga, cancer_general | — | chr8 | 41755178 | 41755208 | Hyper | cancer_general | — |
| chr8 | 48100155 | 48100443 | Hyper | tcga | LOC100287846 | chr8 | 49293364 | 49293614 | Hyper | tcga, cancer_general | — |
| chr8 | 49468669 | 49469127 | Hyper | tcga, liver_tcga, cancer_general | — | chr8 | 49783041 | 49783283 | Hyper | tcga | — |
| chr8 | 50822179 | 50822308 | Hyper | cancer_general | SNTG1 | chr8 | 50822686 | 50822734 | Hyper | cancer_general | SNTG1 |
| chr8 | 50823452 | 50823562 | Hyper | cancer_general | SNTG1 | chr8 | 53477408 | 53477780 | Hyper | cancer_general | FAM150A |
| chr8 | 53478008 | 53478275 | Hyper | cancer_general, tcga | FAM150A | chr8 | 53478480 | 53478720 | Hyper | cancer_general | FAM150A |
| chr8 | 53851141 | 53851170 | Hyper | literature | NPBWR1 | chr8 | 53853811 | 53854509 | Hyper | tcga, colorectal, cancer_general | NPBWR1 |
| chr8 | 54163316 | 54164175 | Hyper | cancer_general | OPRK1 | chr8 | 54789278 | 54789310 | Hyper | cancer_general | RGS20 |
| chr8 | 54789632 | 54790077 | Hyper | tcga, cancer_general | RGS20 | chr8 | 54790291 | 54790855 | Hyper | cancer_general | RGS20 |
| chr8 | 54791809 | 54792237 | Hyper | cancer_general | RGS20 | chr8 | 54792634 | 54792760 | Hyper | cancer_general | RGS20 |
| chr8 | 54794217 | 54794327 | Hyper | cancer_general | RGS20 | chr8 | 54794713 | 54795196 | Hyper | cancer_general | RGS20 |
| chr8 | 55366188 | 55367641 | Hyper | tcga, cancer_general | SOX17 | chr8 | 55370113 | 55370858 | Hyper | literature, cancer_general | SOX17 |
| chr8 | 55371178 | 55372538 | Hyper | cancer_general | SOX17 | chr8 | 55379280 | 55379962 | Hyper | cancer_general | SOX17 |
| chr8 | 55382766 | 55383237 | Hyper | cancer_general | SOX17 | chr8 | 56013641 | 56013927 | Hyper | cancer_general | XKR4 |
| chr8 | 56014157 | 56014317 | Hyper | cancer_general | XKR4 | chr8 | 56014623 | 56014783 | Hyper | cancer_general | XKR4 |
| chr8 | 56015038 | 56015357 | Hyper | cancer_general | XKR4 | chr8 | 56015560 | 56015619 | Hyper | cancer_general | XKR4 |
| chr8 | 56015908 | 56015938 | Hyper | pancreas | XKR4 | chr8 | 57025692 | 57025943 | Hyper | cancer_general | MOS, SNORA3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 57026168 | 57026213 | Hyper | cancer_general | SNORA3, MOS | chr8 | 57026503 | 57026547 | Hyper | cancer_general | SNORA3, MOS |
| chr8 | 57069553 | 57070157 | Hyper | tcga, cancer_general, liver_tcga | PLAG1 | chr8 | 57358147 | 57359636 | Hyper | literature, cancer_general | AX747062, PENK |
| chr8 | 57359893 | 57359922 | Hyper | literature | PENK, AX747062 | chr8 | 57360570 | 57360791 | Hyper | literature, cancer general | AX747062, PENK |
| chr8 | 58907698 | 58907835 | Hyper | cancer_general | FAM110B | chr8 | 60032680 | 60032738 | Hyper | cancer_general | TOX |
| chr8 | 62200502 | 62200776 | Hyper | cancer_general | CLVS1 | chr8 | 63161658 | 63161800 | Hyper | cancer_general | NKAIN3 |
| chr8 | 65281616 | 65281760 | Hyper | cancer_general | BX537900, MIR124-2, LOC100130155 | chr8 | 65281984 | 65283341 | Hyper | cancer_general, tcga | LOC100130155, BX537900, RMI124-2 |
| chr8 | 65283799 | 65284094 | Hyper | cancer_general | LOC100130155, BX537900, MIR124-2 | chr8 | 65286056 | 65286366 | Hyper | cancer_general | BX537900, MIR124-2, LOC100130155 |
| chr8 | 65286682 | 65286753 | Hyper | cancer_general | LOC100130155, BX537900, MIR124-2 | chr8 | 65286963 | 65287251 | Hyper | cancer_general | BX537900, MIR124-2, LOC100130155 |
| chr8 | 65289123 | 65289241 | Hyper | cancer_general | BX537900, MIR124-2, LOC100130155 | chr8 | 65289614 | 65290798 | Hyper | literature, cancer_general | BX537900, MIR 124-2, LOC100130155 |
| chr8 | 65291034 | 65291284 | Hyper | cancer_general | MIR124-2, BX537900, LOC100130155 | chr8 | 65292185 | 65292727 | Hyper | cancer_general | BX537900, LOC100130155, MIR124-2 |
| chr8 | 65488271 | 65488322 | Hyper | cancer_general | BHLHE22, LOC401463 | chr8 | 65488661 | 65488697 | Hyper | cancer_general | BHLHE22, LOC401463 |
| chr8 | 65489099 | 65489129 | Hyper | cancer_general | BHLHE22, LOC401463 | chr8 | 65492712 | 65492979 | Hyper | tcga, cancer_general | BHLHE22, LOC401463 |
| chr8 | 65493195 | 65493433 | Hyper | cancer_general | BHLHE22, LOC401463 | chr8 | 65493658 | 65493751 | Hyper | cancer_general | BHLHE22, LOC401463 |
| chr8 | 65493961 | 65494193 | Hyper | cancer_general | BHLHE22, LOC401463 | chr8 | 65498566 | 65498841 | Hyper | cancer_general | CYP7B1, BHLHE22, LOC401463 |
| chr8 | 65499757 | 65500015 | Hyper | cancer_general | CYP7B1, BHLHE22, LOC401463 | chr8 | 65710938 | 65711046 | Hyper | cancer_general | CYP7B1 |
| chr8 | 67025063 | 67025640 | Hyper | head_neck | TRNA_Ala, TRNA_Tyr | chr8 | 67025920 | 67026578 | Hyper | head_neck | TRNA_Tyr, TRNA_Ala |
| chr8 | 67026812 | 67026990 | Hyper | head_neck | TRNA_Ala, TRNA_Tyr | chr8 | 67344538 | 67344771 | Hyper | tcga, cancer_general | ADHFE1, RRS1, LOC100505676 |
| chr8 | 67873327 | 67875682 | Hyper | tcga, liver_tcga, cancer_general | TCF24 | chr8 | 67940624 | 67940875 | Hyper | cancer_general | — |
| chr8 | 68864578 | 68864765 | Hyper | cancer_general | BC036055, PREX2 | chr8 | 69242905 | 69242988 | Hyper | tcga, cancer_general | C8orf34, LOC286189 |
| chr8 | 69243269 | 69243994 | Hyper | tcga, cancer_general | LOC286189, C8orf34 | chr8 | 69244370 | 69244500 | Hyper | cancer_general | C8orf34, LOC286189 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 70744860 | 70744925 | Hyper | cancer_general | SLCO5A1 | chr8 | 70946760 | 70947658 | Hyper | cancer_general | — |
| chr8 | 70981944 | 70983226 | Hyper | cancer_general, literature | PRDM14 | chr8 | 70983504 | 70984978 | Hyper | cancer_general, liver_tcga, cancer_general | PRDM14 |
| chr8 | 72273998 | 72274033 | Hyper | cancer_general | EYA1 | chr8 | 72460007 | 72460269 | Hyper | cancer_general | — |
| chr8 | 72468569 | 72469574 | Hyper | tcga, cancer_general | — | chr8 | 72471053 | 72471083 | Hyper | cancer_general | — |
| chr8 | 72754394 | 72754609 | Hyper | cancer_general | LOC100132891, MSC | chr8 | 72754821 | 72755176 | Hyper | tcga, cancer_general | LOC100132891, MSC |
| chr8 | 72755666 | 72756896 | Hyper | cancer_general | MSC, LOC100132891 | chr8 | 72917335 | 72917446 | Hyper | tcga | LOC100132891 |
| chr8 | 72987600 | 72988036 | Hyper | cancer_general | TRPA1 | chr8 | 73163777 | 73164180 | Hyper | cancer_general | LOC392232 |
| chr8 | 73450064 | 73450100 | Hyper | cancer_general | KCNB2 | chr8 | 73450515 | 73450559 | Hyper | cancer_general | KCNB2 |
| chr8 | 75896574 | 75897337 | Hyper | tcga, cancer_general | CRISPLD1 | chr8 | 77585219 | 77585698 | Hyper | cancer_general | ZFHX4, ZFHX4-AS1 |
| chr8 | 77586175 | 77586278 | Hyper | cancer_general | ZFHX4, ZFHX4-AS1 | chr8 | 77586563 | 77586617 | Hyper | cancer_general | ZFHX4, ZFHX4-AS1 |
| chr8 | 77590239 | 77590466 | Hyper | cancer_general | ZFHX4, ZFHX4-AS1 | chr8 | 77593110 | 77593376 | Hyper | cancer_general | ZFHX4, ZFHX4-AS1 |
| chr8 | 77593889 | 77594124 | Hyper | cancer_general | ZFHX4, ZFHX4-AS1 | chr8 | 77594648 | 77594993 | Hyper | tcga, cancer_general | ZFHX4, ZFHX4-AS1 |
| chr8 | 77595339 | 77595494 | Hyper | cancer_general | ZFHX4, ZFHX4-AS1, ZFHX4 | chr8 | 79428297 | 79428401 | Hyper | cancer_general | PKIA |
| chr8 | 80523983 | 80524029 | Hyper | cancer_general | STMN2 | chr8 | 80524253 | 80524318 | Hyper | cancer_general | STMN2 |
| chr8 | 80524946 | 80525020 | Hyper | cancer_general | STMN2 | chr8 | 80525604 | 80525733 | Hyper | cancer_general | STMN2 |
| chr8 | 80695902 | 80695932 | Hyper | cancer_general | AK055332 | chr8 | 80803673 | 80803872 | Hyper | colorectal, cancer_general | — |
| chr8 | 81398018 | 81398155 | Hyper | esophageal | ZBTB10, DJ031142 | chr8 | 81398428 | 81399496 | Hyper | esophageal | ZBTB10, DJ031142 |
| chr8 | 81478185 | 81478350 | Hyper | cancer_general | — | chr8 | 85095482 | 85095668 | Hyper | cancer_general | RALYL |
| chr8 | 85096583 | 85096805 | Hyper | cancer_general | RALYL | chr8 | 85097015 | 85097220 | Hyper | cancer_general | RALYL |
| chr8 | 86350553 | 86350595 | Hyper | literature | CA3 | chr8 | 89339389 | 89339745 | Hyper | tcga, cancer_general | MMP16 |
| chr8 | 89340270 | 89340345 | Hyper | cancer_general | MMP16 | chr8 | 91094221 | 91094251 | Hyper | cancer_general | Metazoa_SRP, CALB1 |
| chr8 | 91803676 | 91803718 | Hyper | cancer_general | NECAB1 | chr8 | 91803991 | 91804253 | Hyper | cancer_general | NECAB1 |
| chr8 | 91997046 | 91997947 | Hyper | tcga, cancer_general | TMEM55A, LOC100127983 | chr8 | 93114135 | 93114528 | Hyper | cancer_general, tcga | — |
| chr8 | 95651098 | 95651218 | Hyper | liver_tcga | ESRP1, LOC100288748 | chr8 | 95651538 | 95651655 | Hyper | blood | ESRP1, LOC100288748 |
| chr8 | 97157085 | 97158066 | Hyper | tcga, cancer_general | GDF6 | chr8 | 97165644 | 97165676 | Hyper | cancer_general | GDF6 |
| chr8 | 97166425 | 97166455 | Hyper | cancer_general | GDF6 | chr8 | 97167178 | 97167223 | Hyper | cancer_general | GDF6 |
| chr8 | 97167811 | 97167855 | Hyper | cancer_general | GDF6 | chr8 | 97169838 | 97170334 | Hyper | cancer_general, tcga | GDF6 |
| chr8 | 97170867 | 97170897 | Hyper | cancer_general | GDF6 | chr8 | 97171129 | 97172200 | Hyper | cancer_general | GDF6 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 97172433 | 97173458 | Hyper | tcga, cancer_general | GDF6 | chr8 | 97173822 | 97173935 | Hyper | cancer_general | GDF6 |
| chr8 | 97506034 | 97506524 | Hyper | colorectal, cancer_general | SDC2 | chr8 | 97507115 | 97507284 | Hyper | colorectal, cancer_general | SDC2 |
| chr8 | 97507546 | 97507680 | Hyper | tcga | SDC2 | chr8 | 98289825 | 98290260 | Hyper | liver_tcga, cancer_general | TSPYL5 |
| chr8 | 99439104 | 99439133 | Hyper | liver_tcga | KCNS2 | chr8 | 99439382 | 99440354 | Hyper | literature, liver_tcga, cancer_general, tcga | KCNS2 |
| chr8 | 99951404 | 99951434 | Hyper | liver_tcga, cancer_general | OSR2 | chr8 | 99951836 | 99952815 | Hyper | cancer_general | OSR2 |
| chr8 | 99954490 | 99954727 | Hyper | cancer_general | OSR2 | chr8 | 99955180 | 99955327 | Hyper | cancer_general | OSR2 |
| chr8 | 99959429 | 99959549 | Hyper | liver_tcga | OSR2 | chr8 | 99960329 | 99960971 | Hyper | tcga, cancer_general | OSR2 |
| chr8 | 99961187 | 99961272 | Hyper | cancer_general | OSR2 | chr8 | 99961792 | 99961822 | Hyper | cancer_general | OSR2 |
| chr8 | 99985866 | 99987014 | Hyper | cancer_general | — | chr8 | 101118241 | 101118577 | Hyper | literature, liver_tcga, cancer_general | — |
| chr8 | 101661920 | 101661991 | Hyper | liver_tcga | SNX31 | chr8 | 101821973 | 101822047 | Hyper | cancer_general | — |
| chr8 | 101920382 | 101920468 | Hyper | head_neck | — | chr8 | 102504464 | 102504506 | Hyper | liver_tcga, literature | GRHL2 |
| chr8 | 102505512 | 102505556 | Hyper | liver_tcga | GRHL2 BAALC, C8orf56, AK001351 | chr8 | 102505797 | 102506000 | Hyper | liver_tcga, blood | GRHL2 BAALC, C8orf56, AK001351 |
| chr8 | 104153202 | 104153246 | Hyper | cancer_general | CTHRC1 | chr8 | 104153449 | 104153641 | Hyper | cancer_general | |
| chr8 | 104383700 | 104383985 | Hyper | liver_tcga, tcga | RIMS2 | chr8 | 104512123 | 104513186 | Hyper | tcga, liver_tcga, cancer_general | RIMS2 |
| chr8 | 104513462 | 104513926 | Hyper | tcga, cancer_general | — | chr8 | 105235369 | 105236054 | Hyper | tcga, cancer_general | — |
| chr8 | 105478725 | 105479176 | Hyper | cancer_general | ZFPM2 | chr8 | 105479404 | 105479464 | Hyper | cancer_general | ZFPM2 |
| chr8 | 106331160 | 106331237 | Hyper | cancer_general | OXR1 | chr8 | 106332104 | 106332202 | Hyper | tcga | OXR1 |
| chr8 | 107282163 | 107282195 | Hyper | esophageal | — | chr8 | 107284038 | 107284075 | Hyper | cancer_general | RSPO2 |
| chr8 | 108509543 | 108509697 | Hyper | lung, cancer_general | RSPO2 | chr8 | 109093679 | 109094180 | Hyper | cancer_general | RSPO2 |
| chr8 | 109094485 | 109094595 | Hyper | cancer_general | TMEM74 | chr8 | 109094840 | 109095932 | Hyper | tcga, cancer_general | RSPO2 |
| chr8 | 109799588 | 109799770 | Hyper | tcga | CSMD3 | chr8 | 110986443 | 110986682 | Hyper | cancer_general | KCNV1 |
| chr8 | 114444580 | 114445192 | Hyper | tcga, cancer_general | CSMD3 | chr8 | 114445763 | 114446068 | Hyper | cancer_general | CSMD3 |
| chr8 | 114446405 | 114446435 | Hyper | cancer_general | CSMD3 | chr8 | 114446931 | 114447368 | Hyper | cancer_general | CSMD3 |
| chr8 | 114449039 | 114449257 | Hyper | cancer_general | TRPS1 | chr8 | 114449550 | 114449602 | Hyper | cancer_general | CSMD3 |
| chr8 | 116660527 | 116660760 | Hyper | cancer_general | AARD, AL832163 | chr8 | 117950438 | 117950468 | Hyper | cancer_general | AARD, AL832163 |
| chr8 | 117950783 | 117950914 | Hyper | cancer_general | MAL2 | chr8 | 120220116 | 120220145 | Hyper | literature | MAL2 |
| chr8 | 120220428 | 120220592 | Hyper | blood | — | chr8 | 120650979 | 120651008 | Hyper | literature | KCNV1 |
| chr8 | 120651221 | 120651412 | Hyper | literature | — | chr8 | 121136879 | 121137748 | Hyper | tcga, cancer_general | CSMD3 |
| chr8 | 121823901 | 121823930 | Hyper | literature | — | chr8 | 121824203 | 121824481 | Hyper | literature | COL14A1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr8 | 122651872 | 122651905 | Hyper | cancer_general | HAS2, HAS2-AS1 | chr8 | 124173246 | 124173501 | Hyper | tcga, cancer_general | TRNA_Met, WDR67 |
| chr8 | 127569621 | 127569676 | Hyper | blood | FAM84B | chr8 | 132052147 | 132053164 | Hyper | cancer_general | ADCY8 |
| chr8 | 132053715 | 132054749 | Hyper | cancer_general | ADCY8 | chr8 | 139508757 | 139509295 | Hyper | cancer_general | — |
| chr8 | 139509741 | 139509928 | Hyper | cancer_general | — | chr8 | 140714570 | 140714877 | Hyper | cancer_general | KCNK9 |
| chr8 | 140715090 | 140715120 | Hyper | cancer_general | KCNK9 | chr8 | 140715469 | 140715646 | Hyper | liver_tcga, cancer_general | KCNK9 |
| chr8 | 140715965 | 140716382 | Hyper | cancer_general | KCNK9 | chr8 | 142318155 | 142318184 | Hyper | liver_tcga | — |
| chr8 | 142528400 | 142529004 | Hyper | cancer_general, tcga | — | chr8 | 143532122 | 143532846 | Hyper | tcga, cancer_general | — |
| chr8 | 143533611 | 143533906 | Hyper | cancer_general, colorectal | — | chr8 | 143592657 | 143592687 | Hyper | cancer_general | BAI1 |
| chr8 | 143858522 | 143858699 | Hyper | cancer_general | LYNX1, LY6D | chr8 | 143859322 | 143859361 | Hyper | cancer_general | LY6D, LYNX1 |
| chr8 | 144203653 | 144203708 | Hyper | ovarian | — | chr8 | 144241250 | 144241287 | Hyper | cancer_general | LY6H |
| chr8 | 144241543 | 144241582 | Hyper | cancer_general | LY6H | chr8 | 144241871 | 144242356 | Hyper | tcga, cancer_general | LY6H |
| chr8 | 144328321 | 144328565 | Hyper | cancer_general | ZFP41 | chr8 | 144509325 | 144510529 | Hyper | cancer_general | MAFA, ZC3H3 |
| chr8 | 144511225 | 144511424 | Hyper | cancer_general | ZC3H3, MAFA | chr8 | 144512041 | 144512192 | Hyper | liver_tcga, cancer_general | ZC3H3, MAFA |
| chr8 | 144512473 | 144512503 | Hyper | blood | ZC3H3, MAFA | chr8 | 144601799 | 144601851 | Hyper | liver_tcga | ZC3H3 |
| chr8 | 144650594 | 144650730 | Hyper | liver_tcga | GSDMD, MROH6, NAPRT1 | chr8 | 145033304 | 145033333 | Hyper | liver_tcga | — |
| chr8 | 145698347 | 145698379 | Hyper | cancer_general | CYHR1, FOXH1, KIFC2 | chr8 | 145806258 | 145806287 | Hyper | liver_tcga | ARHGAP39 |
| chr8 | 145925461 | 145925491 | Hyper | cancer_general | DQ588968 | chr8 | 145925947 | 145926089 | Hyper | liver_tcga | DQ588968 |
| chr13 | 20175911 | 20175941 | Hyper | hepatobiliary | — | chr13 | 20735804 | 20736089 | Hyper | tcga | IL17D, AK05408, N6AMT2 |
| chr13 | 20875763 | 20875919 | Hyper | cancer_general | — | chr13 | 21295926 | 21295955 | Hyper | liver_tcga | FGF9 |
| chr13 | 21649636 | 21649775 | Hyper | cancer_general | — | chr13 | 22243273 | 22243469 | Hyper | tcga, cancer_general | — |
| chr13 | 23489851 | 23489914 | Hyper | cancer_general | — | chr13 | 23733447 | 23734020 | Hyper | cancer_general | ANKRD20A19P, C1QTNF9B |
| chr13 | 23734284 | 23734678 | Hyper | tcga, cancer_general | — | chr13 | 24477643 | 24477906 | Hyper | cancer_general | — |
| chr13 | 25115713 | 25115771 | Hyper | cancer_general | — | chr13 | 25319856 | 25321350 | Hyper | cancer_general, tcga | — |
| chr13 | 25321699 | 25321942 | Hyper | cancer_general | — | chr13 | 25593042 | 25593242 | Hyper | tcga | BC022569, AMER2 |
| chr13 | 25621045 | 25621394 | Hyper | cancer_general | — | chr13 | 25744716 | 25746000 | Hyper | tcga, cancer_general | ATP8A2 |
| chr13 | 25946205 | 25946411 | Hyper | tcga, cancer_general | ATP8A2 | chr13 | 25946620 | 25946796 | Hyper | cancer_general | SHISA2 |
| chr13 | 26042678 | 26043499 | Hyper | cancer_general | ATP8A2 | chr13 | 26625301 | 26625727 | Hyper | cancer_general, colorectal | WASF3 |
| chr13 | 26626077 | 26626148 | Hyper | tcga | SHISA2 | chr13 | 27132407 | 27132445 | Hyper | tcga | WASF3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 27334211 | 27334563 | Hyper | cancer_general | GPR12 | chr13 | 27334772 | 27334894 | Hyper | cancer_general | GPR12 |
| chr13 | 28365705 | 28366122 | Hyper | colorectal, cancer_general | GSX1 | chr13 | 28366482 | 28366577 | Hyper | cancer_general | GSX1 |
| chr13 | 28367024 | 28367059 | Hyper | cancer_general | GSX1 | chr13 | 28367794 | 28368168 | Hyper | cancer_general | GSX1 |
| chr13 | 28368451 | 28368593 | Hyper | cancer_general | GSX1 | chr13 | 28368952 | 28368990 | Hyper | cancer_general | GSX1 |
| chr13 | 28370947 | 28371061 | Hyper | cancer_general | GSX1 | chr13 | 28394766 | 28394866 | Hyper | cancer_general | — |
| chr13 | 28395501 | 28395553 | Hyper | cancer_general | — | chr13 | 28395998 | 28396073 | Hyper | cancer_general | — |
| chr13 | 28491793 | 28491946 | Hyper | cancer_general | PDX1 | chr13 | 28492244 | 28492553 | Hyper | cancer_general | PDX1 |
| chr13 | 28503042 | 28503074 | Hyper | cancer_general | PDX1 | chr13 | 28528534 | 28528748 | Hyper | cancer_general | CDX2, ATP5EP2 |
| chr13 | 28540745 | 28540927 | Hyper | cancer_general | CDX2 | chr13 | 28543212 | 28543242 | Hyper | cancer_general | PRHOXNB, CDX2 |
| chr13 | 28544397 | 28544903 | Hyper | cancer_general | PRHOXNB, CDX2 | chr13 | 28549497 | 28550552 | Hyper | cancer_general | PRHOXNB, CDX2 |
| chr13 | 28551417 | 28551461 | Hyper | cancer_general | PRHOXNB | chr13 | 28551950 | 28552167 | Hyper | cancer_general | PRHOXNB, CDX2 |
| chr13 | 28552555 | 28552585 | Hyper | cancer_general | PRHOXNB, CDX2 | chr13 | 28552794 | 28552824 | Hyper | cancer_general | PRHOXNB, CDX2 |
| chr13 | 28553030 | 28553138 | Hyper | cancer_general | PRHOXNB, CDX2 | chr13 | 28889765 | 28889794 | Hyper | literature | FLT3 |
| chr13 | 28892605 | 28892658 | Hyper | literature | FLT3 | chr13 | 28601345 | 28601374 | Hyper | literature | FLT3 |
| chr13 | 28602326 | 28602355 | Hyper | literature | FLT3 | chr13 | 28608233 | 28608355 | Hyper | literature | FLT3 |
| chr13 | 28610123 | 28610152 | Hyper | literature | FLT3 | chr13 | 28674018 | 28674734 | Hyper | tcga, cancer_general | FLT3 |
| chr13 | 29067773 | 29068416 | Hyper | cancer_general | BC048278, FLT1 | chr13 | 29068926 | 29069065 | Hyper | cancer_general | BC048278, FLT1 |
| chr13 | 29106308 | 29107309 | Hyper | tcga, cancer_general | — | chr13 | 32605034 | 32605966 | Hyper | pancreas | BC035084, FRY |
| chr13 | 33590822 | 33590949 | Hyper | cancer_general | KL | chr13 | 33591300 | 33591419 | Hyper | cancer_general | KL |
| chr13 | 33924666 | 33924790 | Hyper | cancer_general | — | chr13 | 35517395 | 35517648 | Hyper | tcga | NBEA |
| chr13 | 36044829 | 36044930 | Hyper | cancer_general | NBEA, MIR548F5 | chr13 | 36045267 | 36045297 | Hyper | cancer_general | NBEA, MIR548F5 |
| chr13 | 36049995 | 36050025 | Hyper | pancreas | NBEA, MIR548F5 | chr13 | 36704939 | 36705055 | Hyper | cancer_general, tcga | — |
| chr13 | 36705451 | 36705489 | Hyper | cancer_general | — | chr13 | 36729093 | 36729125 | Hyper | cancer_general, tcga | SPG20OS, SPG20 |
| chr13 | 36920317 | 36920413 | Hyper | liver_tcga, colorectal, cancer_general | SPG20OS, SPG20 | chr13 | 36920628 | 36920785 | Hyper | cancer_general, tcga, colorectal | SPG20OS, SPG20 |
| chr13 | 37004771 | 37005129 | Hyper | cancer_general | CCNA1 | chr13 | 37005657 | 37006762 | Hyper | cancer_general | CCNA1 |
| chr13 | 37248063 | 37248319 | Hyper | tcga | SERTM1 | chr13 | 37248979 | 37249030 | Hyper | cancer_general | SERTM1 |
| chr13 | 37633989 | 37634018 | Hyper | literature | SUPT20H | chr13 | 38443618 | 38443827 | Hyper | cancer_general | Mir_720, TRPC4 |
| chr13 | 39261410 | 39261446 | Hyper | tcga | FREM2 | chr13 | 43148421 | 43148450 | Hyper | tcga | TNFSF11 |
| chr13 | 43148669 | 43148698 | Hyper | tcga | TNFSF11 | chr13 | 43566247 | 43566647 | Hyper | tcga, cancer_general | EPSTI1 |
| chr13 | 44947746 | 44948197 | Hyper | cancer_general | SERP2 | chr13 | 45150013 | 45150276 | Hyper | tcga, liver_tcga | TSC22D1-AS1, TSC22D1 |
| chr13 | 45885876 | 45885905 | Hyper | liver_tcga | — | chr13 | 46425548 | 46425584 | Hyper | cancer_general | SIAH3 |
| chr13 | 46961494 | 46961533 | Hyper | esophageal | KIAA0226L | chr13 | 46961952 | 46961982 | Hyper | esophageal | KIAA0226L |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 47468139 | 47468168 | Hyper | literature | HTR2A | chr13 | 49794117 | 49795168 | Hyper | esophageal, cancer_general | MLNR |
| chr13 | 53312991 | 53313920 | Hyper | cancer_general | LECT1 | chr13 | 53419734 | 53419775 | Hyper | cancer_general | PCDH8 |
| chr13 | 53420020 | 53420080 | Hyper | cancer_general | PCDH8 | chr13 | 53420385 | 53420720 | Hyper | liver_tcga, cancer_general | PCDH8 |
| chr13 | 53421253 | 53421787 | Hyper | cancer_general | PCDH8 | chr13 | 53422315 | 53422362 | Hyper | cancer_general | PCDH8 |
| chr13 | 53423838 | 53423978 | Hyper | cancer_general | PCDH8 | chr13 | 53423602 | 53203644 | Hyper | cancer_general | PCDH17 |
| chr13 | 58203851 | 58204103 | Hyper | cancer_general | PCDH17 | chr13 | 58203602 | 58204393 | Hyper | tcga | PCDH17 |
| chr13 | 58206042 | 58206983 | Hyper | cancer_general | PCDH17 | chr13 | 58204350 | 58208020 | Hyper | cancer_general | PCDH17 |
| chr13 | 58208495 | 58208926 | Hyper | cancer_general | PCDH17 | chr13 | 58207462 | 67804074 | Hyper | tcga, cancer_general | PCDH9 |
| chr13 | 67804494 | 67804523 | Hyper | literature | PCDH9 | chr13 | 67805191 | 67805247 | Hyper | cancer_general | PCDH9 |
| chr13 | 70681626 | 70682071 | Hyper | cancer_general | ATXN8OS, KLHL1 | chr13 | 72439142 | 72439250 | Hyper | cancer_general | DACH1 |
| chr13 | 73336049 | 73336078 | Hyper | literature | DIS3, BORA | chr13 | 78492684 | 78492840 | Hyper | esophageal, cancer_general | RNF219-AS1, EDNRB |
| chr13 | 78493166 | 78493196 | Hyper | cancer_general | RNF219-AS1, EDNRB | chr13 | 78493455 | 78493809 | Hyper | cancer_general | RNF219-AS1, EDNRB |
| chr13 | 79168067 | 79168102 | Hyper | pancreas | POU4F1, RNF219-AS1 | chr13 | 79169818 | 79170884 | Hyper | literature, cancer_general | IRNF219-AS1, POU4F1 |
| chr13 | 79171118 | 79171196 | Hyper | cancer_general | POU4F1, RNF219-AS1 | chr13 | 79175770 | 79176783 | Hyper | liver_tcga, cancer_general | RNF219-AS1, POU4F1 |
| chr13 | 79176993 | 79177998 | Hyper | tcga, liver_tcga, cancer_general | POU4F1, RNF219-AS1 | chr13 | 79183406 | 79183485 | Hyper | cancer_general | RNF219, POU4F1, RNF219-AS1 |
| chr13 | 81229343 | 81229372 | Hyper | literature | — | chr13 | 84455236 | 84455292 | Hyper | cancer_general | SLITRK1 |
| chr13 | 84455581 | 84455715 | Hyper | cancer_general | SLITRK1 | chr13 | 84457491 | 84457521 | Hyper | cancer_general | SLITRK1 |
| chr13 | 88323579 | 88324207 | Hyper | tcga, cancer_general | SLITRK5 | chr13 | 88324516 | 88324611 | Hyper | colorectal, cancer_general | SLITRK5 |
| chr13 | 88325300 | 88325460 | Hyper | cancer_general | SLITRK5 | chr13 | 88325819 | 88326061 | Hyper | cancer_general | SLITRK5 |
| chr13 | 88326538 | 88327014 | Hyper | cancer_general, tcga | SLITRK5 | chr13 | 92050760 | 92050814 | Hyper | esophageal | GPC5 |
| chr13 | 92051139 | 92051168 | Hyper | tcga | GPC5 | chr13 | 92051374 | 92051529 | Hyper | tcga, cancer_general | GPC5 |
| chr13 | 93879288 | 93879375 | Hyper | tcga | GPC6 | chr13 | 93879670 | 93879700 | Hyper | cancer_general | GPC6 |
| chr13 | 93880089 | 93880856 | Hyper | tcga, colorectal, cancer_general | GPC6 | chr13 | 95357311 | 95357341 | Hyper | cancer_general | SOX21, AK055459 |
| chr13 | 95357574 | 95357775 | Hyper | cancer_general | SOX21, AK055459 | chr13 | 95358041 | 95358165 | Hyper | cancer_general | SOX21, AK055459 |
| chr13 | 95359747 | 95359803 | Hyper | cancer_general | SOX21, AK055459 | chr13 | 95360322 | 95360371 | Hyper | cancer_general | SOX21, AK055459 |
| chr13 | 95363210 | 95363429 | Hyper | cancer_general | SOX21, AK055459 | chr13 | 95363796 | 95364196 | Hyper | tcga, cancer_general | AK055459, SOX21 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 95364495 | 95364800 | Hyper | tcga, cancer_general, colorectal | AK055459, SOX21 | chr13 | 95620021 | 95620078 | Hyper | colorectal, cancer_general | — |
| chr13 | 95620647 | 95621011 | Hyper | cancer_general, tcga | — | chr13 | 96204853 | 96205363 | Hyper | liver_tcga, cancer_general | CLDN10 |
| chr13 | 96296225 | 96296473 | Hyper | cancer_general | — | chr13 | 96296693 | 96297137 | Hyper | tcga, cancer_general | — |
| chr13 | 96743788 | 96744175 | Hyper | tcga, cancer_general | HS6ST3 | chr13 | 100547713 | 100547982 | Hyper | cancer_general | — |
| chr13 | 100608257 | 100609055 | Hyper | cancer_general | ZIC5 | chr13 | 100621941 | 100622015 | Hyper | cancer_general | ZIC5 |
| chr13 | 100624316 | 100624348 | Hyper | cancer_general | ZIC2, ZIC5 | chr13 | 100624587 | 100624729 | Hyper | cancer_general | ZIC2, ZIC5 |
| chr13 | 100626929 | 100627009 | Hyper | cancer_general | ZIC2, ZIC5 | chr13 | 100627295 | 100627348 | Hyper | cancer_general | ZIC2, ZIC5 |
| chr13 | 100627688 | 100627717 | Hyper | liver_tcga | ZIC2, ZIC5 | chr13 | 100630169 | 100630430 | Hyper | liver_tcga | ZIC2, ZIC5 |
| chr13 | 100630630 | 100630997 | Hyper | cancer_general | ZIC5, ZIC2 | chr13 | 100633089 | 100633184 | Hyper | blood | ZIC2, ZIC5 |
| chr13 | 100634314 | 100634617 | Hyper | blood | ZIC2 | chr13 | 100635406 | 100635451 | Hyper | cancer_general | ZIC2 |
| chr13 | 100636167 | 100636238 | Hyper | cancer_general | ZIC2 | chr13 | 100637390 | 100637485 | Hyper | cancer_general | ZIC2 |
| chr13 | 100641282 | 100642201 | Hyper | cancer_general | ZIC2 | chr13 | 100643296 | 100643435 | Hyper | cancer_general | ZIC2 |
| chr13 | 100644055 | 100644212 | Hyper | cancer_general | ZIC2 | chr13 | 100649325 | 100649931 | Hyper | cancer_general | — |
| chr13 | 102568454 | 102568484 | Hyper | cancer_general | FGF14 | chr13 | 102568856 | 102568994 | Hyper | cancer_general | FGF14-AS2 |
| chr13 | 102569203 | 102569542 | Hyper | cancer_general | FGF14 | chr13 | 103046721 | 103046995 | Hyper | tcga, cancer_general | FGF14-AS2 |
| chr13 | 103052347 | 103052574 | Hyper | tcga | FGF14-AS2 | chr13 | 103052892 | 103052940 | Hyper | cancer_general | — |
| chr13 | 103053394 | 103053496 | Hyper | tcga | FGF14-AS2 | chr13 | 105791875 | 105791904 | Hyper | literature | — |
| chr13 | 107186855 | 107186884 | Hyper | liver_tcga | ARGLU1, EFNB2 | chr13 | 107187162 | 107187426 | Hyper | liver_tcga, tcga | ARGLU1, EFNB2 |
| chr13 | 107187666 | 107187695 | Hyper | liver_tcga | ARGLU1, EFNB2 | chr13 | 107188241 | 107188430 | Hyper | tcga, liver_tcga | ARGLU1, EFNB2 |
| chr13 | 108518355 | 108518392 | Hyper | cancer_general | — | chr13 | 108518813 | 108518933 | Hyper | cancer_general | — |
| chr13 | 108519254 | 108519367 | Hyper | cancer_general | — | chr13 | 108519737 | 108519894 | Hyper | tcga | — |
| chr13 | 108520376 | 108520580 | Hyper | tcga, cancer_general | — | chr13 | 108520979 | 108521076 | Hyper | cancer_general | — |
| chr13 | 109147685 | 109148351 | Hyper | cancer_general | — | chr13 | 109148783 | 109149185 | Hyper | tcga, cancer_general | — |
| chr13 | 110958816 | 110958981 | Hyper | cancer_general | COL4A1, COL4A2 | chr13 | 110959220 | 110959255 | Hyper | cancer_general | COL4A2, COL4A1 |
| chr13 | 110959705 | 110959970 | Hyper | colorectal, cancer_general | COL4A2, COL4A1 | chr13 | 110960250 | 110960282 | Hyper | cancer_general | COL4A2, COL4A1 |
| chr13 | 110960541 | 110960603 | Hyper | cancer_general | COL4A2, COL4A1 | chr13 | 112707694 | 112707869 | Hyper | cancer_general | — |
| chr13 | 112708088 | 112708513 | Hyper | cancer_general | — | chr13 | 112709388 | 112709617 | Hyper | cancer_general | — |
| chr13 | 112709883 | 112709928 | Hyper | cancer_general | — | chr13 | 112710344 | 112710508 | Hyper | cancer_general | — |
| chr13 | 112710759 | 112711776 | Hyper | cancer_general | — | chr13 | 112712017 | 112713029 | Hyper | cancer_general | — |
| chr13 | 112715370 | 112715642 | Hyper | cancer_general | SOX1 | chr13 | 112715985 | 112716313 | Hyper | cancer_general | SOX1 |
| chr13 | 112716677 | 112716721 | Hyper | cancer_general | SOX1 | chr13 | 112717026 | 112717536 | Hyper | cancer_general | SOX1 |
| chr13 | 112717835 | 112717949 | Hyper | cancer_general | SOX1 | chr13 | 112720033 | 112720505 | Hyper | cancer_general | SOX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr13 | 112720723 | 112720767 | Hyper | cancer_general | SOX1 | chr13 | 112721012 | 112721042 | Hyper | cancer_general | SOX1 |
| chr13 | 112721261 | 112722312 | Hyper | liver_tcga, literature, cancer_general | SOX1 | chr13 | 112724505 | 112724535 | Hyper | cancer_general | SOX1 |
| chr13 | 112726337 | 112726560 | Hyper | cancer_general | SOX1 | chr13 | 112727984 | 112728270 | Hyper | cancer_general | SOX1 |
| chr13 | 112758107 | 112758257 | Hyper | cancer_general | AK055145 | chr13 | 112758463 | 112758613 | Hyper | cancer_general | AK055145 |
| chr13 | 112758849 | 112759248 | Hyper | cancer_general | AK055145 | chr13 | 112759612 | 112759642 | Hyper | cancer_general | AK055145 |
| chr13 | 112759959 | 112760327 | Hyper | cancer_general | AK055145 | chr13 | 112760795 | 112761214 | Hyper | cancer_general | AK055145 |
| chr13 | 113244509 | 113244595 | Hyper | pancreas | TUBGCP3 | chr13 | 114897194 | 114897240 | Hyper | hepatobiliary | — |
| AC211950.2_11234-25326 | 129 | 257 | Hyper | cancer_general | — | AC211950.2_11234-25326 | 13335 | 13445 | Hyper | cancer_general | — |
| AC211950.2_11234-25326 | 13743 | 13889 | Hyper | cancer_general | — | chr15 | 23158397 | 23158489 | Hyper | cancer_general | — |
| chr15 | 26107640 | 26107860 | Hyper | cancer_general | — | chr15 | 26108096 | 26108701 | Hyper | tcga, cancer_general | — |
| chr15 | 27018363 | 27018436 | Hyper | cancer_general | — | chr15 | 27212887 | 27213172 | Hyper | cancer_general | GABRG3 |
| chr15 | 27216396 | 27216429 | Hyper | cancer_general | GABRG3 | chr15 | 27604062 | 27604139 | Hyper | cancer_general | GABRG3 |
| chr15 | 28341699 | 28342429 | Hyper | tcga, cancer_general | OCA2 | chr15 | 28344173 | 28344287 | Hyper | cancer_general | OCA2 |
| chr15 | 28352240 | 28352850 | Hyper | cancer_general, tcga | HERC2, OCA2 | chr15 | 29077284 | 29077383 | Hyper | cancer_general | LOC646278 |
| chr15 | 29130807 | 29131875 | Hyper | cancer_general | APBA2 | chr15 | 29396330 | 29396360 | Hyper | pancreas | APBA2 |
| chr15 | 29407777 | 29408001 | Hyper | tcga | FAM189A1 | chr15 | 29862502 | 29862582 | Hyper | tcga | — |
| chr15 | 30115185 | 30115228 | Hyper | blood | TIP1 | chr15 | 31775596 | 31776121 | Hyper | cancer_general | OTUD7A |
| chr15 | 32933918 | 32934018 | Hyper | liver_tcga, literature | SCG5, ARHGAP11A GREM1, AX747968 | chr15 | 33009747 | 33011348 | Hyper | tcga, liver_tcga, cancer_general | GREM1, AX747968 |
| chr15 | 33011601 | 33011633 | Hyper | cancer_general | GREM1, AX747968 | chr15 | 33487057 | 33487120 | Hyper | liver_tcga | FMN1 |
| chr15 | 33602801 | 33602886 | Hyper | cancer_general | RYR3 | chr15 | 33603194 | 33603624 | Hyper | cancer_general | RYR3 |
| chr15 | 34517058 | 34517334 | Hyper | esophageal | EMC4, SLC12A6 | chr15 | 34630420 | 34630449 | Hyper | tcga | NOP10, NUTM1, SLC12A6 |
| chr15 | 34729478 | 34729582 | Hyper | cancer_general | — | chr15 | 34786504 | 34787304 | Hyper | cancer_general | — |
| chr15 | 35046607 | 35046637 | Hyper | cancer_general | AK092087, GJD2 | chr15 | 35047034 | 35047133 | Hyper | cancer_general | AK092087, GJD2 |
| chr15 | 35087666 | 35087698 | Hyper | cancer_general | AK092087, ACTC1 | chr15 | 37180309 | 37180743 | Hyper | cancer_general | MEIS2, LOC145845 |
| chr15 | 37402974 | 37403238 | Hyper | lung, cancer_general | MEIS2 | chr15 | 40211819 | 40212190 | Hyper | cancer_general | GPR176 |
| chr15 | 40575630 | 40575744 | Hyper | tcga, cancer_general | PLCB2, ANKRD63, PAK6 | chr15 | 40675092 | 40675121 | Hyper | literature | KNSTRN |
| chr15 | 40763811 | 40763862 | Hyper | hepatobiliary | CHST14, BAHD1 | chr15 | 41787804 | 41787852 | Hyper | cancer_general | LTK, ITPKA |
| chr15 | 41804878 | 41805772 | Hyper | cancer_general | RPAP1, LTK, ITPKA | chr15 | 41913750 | 41913807 | Hyper | cancer_general | MGA |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 41952572 | 41952711 | Hyper | cancer_general | MGA | chr15 | 43810405 | 43810435 | Hyper | pancreas | MAP1A |
| chr15 | 45403636 | 45404130 | Hyper | cancer_general | DUOXA2, DUOXA1, DUOX2 | chr15 | 45404881 | 45405117 | Hyper | tcga | DUOXA2, DUOXA1, DUOX2 |
| chr15 | 45421385 | 45421435 | Hyper | cancer_general | DUOX1, DUOXA1 | chr15 | 45421950 | 45422095 | Hyper | liver_tcga | DUOX1, DUOXA1 |
| chr15 | 45427354 | 45427410 | Hyper | cancer_general | DUOXA1, DUOX1 | chr15 | 45427611 | 45427786 | Hyper | cancer_general | DUOX1, DUOXA1 |
| chr15 | 45479460 | 45479697 | Hyper | cancer_general | SHF | chr15 | 45493209 | 45493371 | Hyper | ovarian | TRNA, TRNA_His |
| chr15 | 45670462 | 45670879 | Hyper | colorectal | BC039389, GATM, GATM-AS1 | chr15 | 47476118 | 47476450 | Hyper | tcga | SEMA6D |
| chr15 | 47476868 | 47477018 | Hyper | tcga | SEMA6D | chr15 | 48483956 | 48483986 | Hyper | cancer_general | CTXN2, SLC12A1 |
| chr15 | 48936726 | 48937987 | Hyper | colorectal, cancer_general, tcga | FBN1 | chr15 | 48938212 | 48938510 | Hyper | cancer_general | FBN1 |
| chr15 | 51385913 | 51386181 | Hyper | cancer_general | TNFAIP8L3 | chr15 | 51634075 | 51634135 | Hyper | cancer_general | GLDN |
| chr15 | 51973646 | 51973934 | Hyper | tcga | SCG3 | chr15 | 53075809 | 53077361 | Hyper | cancer_general | ONECUT1 |
| chr15 | 53077655 | 53077731 | Hyper | cancer_general | ONECUT1 | chr15 | 53078064 | 53078236 | Hyper | cancer_general | ONECUT1 |
| chr15 | 53079340 | 53080082 | Hyper | cancer_general | ONECUT1 | chr15 | 53080337 | 53080606 | Hyper | cancer_general | ONECUT1 |
| chr15 | 53080935 | 53081025 | Hyper | cancer_general | ONECUT1 | chr15 | 53081306 | 53081677 | Hyper | cancer_general | ONECUT1 |
| chr15 | 53082443 | 53082491 | Hyper | esophageal | — | chr15 | 53096816 | 53096891 | Hyper | cancer_general | — |
| chr15 | 53097231 | 53097261 | Hyper | cancer_general | — | chr15 | 53097634 | 53097974 | Hyper | tcga, cancer_general | — |
| chr15 | 53098316 | 53098658 | Hyper | cancer_general | — | chr15 | 54270498 | 54270707 | Hyper | tcga, cancer_general | — |
| chr15 | 54270932 | 54270961 | Hyper | tcga | — | chr15 | 55880879 | 55881011 | Hyper | tcga | PYGO1 |
| chr15 | 58357318 | 58357451 | Hyper | cancer_general | ALDH1A2 | chr15 | 58357733 | 58358200 | Hyper | cancer_general, liver_tcga | ALDH1A2 |
| chr15 | 59158809 | 59158901 | Hyper | pancreas | unknown, FAM63B | chr15 | 60287038 | 60287733 | Hyper | cancer_general | FOXB1 |
| chr15 | 60288786 | 60288844 | Hyper | cancer_general | FOXB1 | chr15 | 60289310 | 60289546 | Hyper | tcga, cancer_general | FOXB1 |
| chr15 | 60296122 | 60296209 | Hyper | cancer_general | FOXB1 | chr15 | 60296598 | 60297409 | Hyper | tcga, liver_tcga, cancer_general | FOXB1 |
| chr15 | 60297637 | 60298108 | Hyper | cancer_general | FOXB1 | chr15 | 61520916 | 61521014 | Hyper | tcga | — |
| chr15 | 61521659 | 61521937 | Hyper | tcga | — | chr15 | 62456922 | 62456952 | Hyper | blood | C2CD4B |
| chr15 | 65669859 | 65669899 | Hyper | esophageal | IGDCC4 | chr15 | 66727409 | 66727498 | Hyper | literature | MAP2K1 |
| chr15 | 66729148 | 66729177 | Hyper | literature | MAP2K1 | chr15 | 66774117 | 66774203 | Hyper | literature | SNAPC5, MAP2K1 |
| chr15 | 68112611 | 68112641 | Hyper | cancer_general | SKOR1 | chr15 | 68113868 | 68113898 | Hyper | cancer_general | SKOR1 |
| chr15 | 68114139 | 68114195 | Hyper | cancer_general | SKOR1 | chr15 | 68116369 | 68116621 | Hyper | cancer_general | SKOR1 |
| chr15 | 68117830 | 68118633 | Hyper | cancer_general | SKOR1 | chr15 | 68118886 | 68119218 | Hyper | cancer_general | SKOR1 |
| chr15 | 68119548 | 68120576 | Hyper | cancer_general | SKOR1 | chr15 | 68120827 | 68120857 | Hyper | cancer_general | SKOR1 |
| chr15 | 68121058 | 68122076 | Hyper | cancer_general, lung, | SKOR1 | chr15 | 68122643 | 68122673 | Hyper | cancer_general | SKOR1 |
| chr15 | 68125261 | 68125664 | Hyper | cancer_general | SKOR1 | chr15 | 68127801 | 68128350 | Hyper | cancer_general | SKOR1 |
| chr15 | 68128594 | 68128688 | Hyper | pancreas | SKOR1 | chr15 | 68260519 | 68260709 | Hyper | liver_tcga | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 71055636 | 71055815 | Hyper | blood | — | chr15 | 72612540 | 72612906 | Hyper | liver_tcga, hepatobiliary | CELF6 |
| chr15 | 73660004 | 73660067 | Hyper | cancer_general | HCN4 | chr15 | 73661469 | 73661666 | Hyper | cancer_general, tcga | HCN4 |
| chr15 | 74045060 | 74045097 | Hyper | tcga | C15orf59 | chr15 | 74422006 | 74422146 | Hyper | cancer_general | ISLR2, LOC283731 |
| chr15 | 74422869 | 74423002 | Hyper | cancer_general | ISLR2, LOC283731 | chr15 | 74658151 | 74658587 | Hyper | tcga, cancer_general | BC013681, CYP11A1, LOC729739 |
| chr15 | 75251346 | 75251382 | Hyper | cancer_general | RPP25 | chr15 | 75251672 | 75251786 | Hyper | cancer_general | RPP25 |
| chr15 | 75471116 | 75471193 | Hyper | cancer_general | — | chr15 | 76627508 | 76627826 | Hyper | liver_tcga, cancer_general | ISL2 |
| chr15 | 76629056 | 76629220 | Hyper | cancer_general | ISL2 | chr15 | 76629494 | 76629531 | Hyper | lung | ISL2 |
| chr15 | 76629814 | 76630847 | Hyper | cancer_general | SCAPER, ISL2 | chr15 | 76632257 | 76632423 | Hyper | cancer_general | SCAPER, ISL2 |
| chr15 | 76635120 | 76635197 | Hyper | cancer_general | SCAPER, ISL2 | chr15 | 76635530 | 76635560 | Hyper | cancer_general | SCAPER, ISL2 |
| chr15 | 76638472 | 76638719 | Hyper | cancer_general | SCAPER, ISL2 | chr15 | 78111154 | 78111210 | Hyper | cancer_general | — |
| chr15 | 78556819 | 78557108 | Hyper | tcga, liver_tcga | DNAJA4 | chr15 | 78632727 | 78632823 | Hyper | cancer_general | CRABP1 |
| chr15 | 78912281 | 78912401 | Hyper | cancer_general | CHRNB4, AX748237, CHRNA3 | chr15 | 78912623 | 78912653 | Hyper | cancer_general | CHRNB4, AX748237, CHRNA3 |
| chr15 | 78912912 | 78913170 | Hyper | tcga, cancer_general | CHRNB4, AX748237, CHRNA3 | chr15 | 78913535 | 78913651 | Hyper | cancer_general | — |
| chr15 | 79104217 | 79104246 | Hyper | tcga | ADAMTS7 | chr15 | 79104466 | 79104495 | Hyper | tcga | ADAMTS7 |
| chr15 | 79381705 | 79382571 | Hyper | cancer_general | — | chr15 | 79382786 | 79383257 | Hyper | cancer_general | — |
| chr15 | 79383947 | 79383977 | Hyper | colorectal | — | chr15 | 79502211 | 79502360 | Hyper | cancer_general | MIR184, LOC729911 |
| chr15 | 79575278 | 79575474 | Hyper | cancer_general | ANKRD34C KIAA1024 | chr15 | 79576145 | 79576277 | Hyper | cancer_general | ANKRD34C KIAA1024 |
| chr15 | 79724126 | 79724240 | Hyper | cancer_general | — | chr15 | 79724502 | 79725140 | Hyper | tcga, cancer_general | — |
| chr15 | 79725422 | 79725539 | Hyper | cancer_general | KIAA1024 | chr15 | 81071827 | 81071867 | Hyper | blood | KIAA1199 |
| chr15 | 82336879 | 82336972 | Hyper | cancer_general | MEX3B | chr15 | 82340070 | 82340157 | Hyper | cancer_general | MEX3B |
| chr15 | 83315336 | 83315393 | Hyper | cancer_general | LOC283692 | chr15 | 83316251 | 83317087 | Hyper | cancer_general | LOC283692 |
| chr15 | 83349234 | 83349686 | Hyper | cancer_general | AP3B2 | chr15 | 83378212 | 83378370 | Hyper | esophageal | AP3B2 |
| chr15 | 83776255 | 83776785 | Hyper | liver_tcga, colorectal, cancer_general | TM6SF1 | chr15 | 83875648 | 83875901 | Hyper | liver_tcga, cancer_general | HDGFRP3 |
| chr15 | 83877055 | 83877149 | Hyper | tcga | HDGFRP3 | chr15 | 83952198 | 83952736 | Hyper | tcga, cancer_general | BNC1 |
| chr15 | 83953102 | 83953903 | Hyper | tcga, cancer_general | BNC1 | chr15 | 83954380 | 83954409 | Hyper | literature | BNC1 |
| chr15 | 84115747 | 84115966 | Hyper | cancer_general | SH3GL3 | chr15 | 84116905 | 84116949 | Hyper | tcga | SH3GL3 |
| chr15 | 84322851 | 84323037 | Hyper | cancer_general | ADAMTSL3 | chr15 | 84748578 | 84749260 | Hyper | cancer_general | EFTUD1P1 |
| chr15 | 88798688 | 88798791 | Hyper | cancer_general | NTRK3, NTRK3-AS1 | chr15 | 88799537 | 88800317 | Hyper | cancer_general, tcga | NTRK3-AS1, NTRK3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr15 | 88800541 | 88801103 | Hyper | cancer_general | NTRK3-AS1, NTRK3 | chr15 | 89149169 | 89149448 | Hyper | cancer_general | MIR1179, MIR7-2, MIR3529, AK054749 |
| chr15 | 89248753 | 89248907 | Hyper | tcga, cancer_general | — | chr15 | 89346050 | 89346393 | Hyper | cancer_general | ACAN |
| chr15 | 89346670 | 89346943 | Hyper | cancer_general | ACAN | chr15 | 89903484 | 89903814 | Hyper | cancer_general | MIR9-3, LINC00925 |
| chr15 | 89910521 | 89910748 | Hyper | cancer_general | MIR9-3, LINC00925 | chr15 | 89911087 | 89911186 | Hyper | cancer_general | MIR9-3, LINC00925 |
| chr15 | 89913750 | 89913780 | Hyper | cancer_general | MIR9-3, LINC00925 | chr15 | 89914231 | 89914895 | Hyper | cancer_general | LINC00925, MIR9-3 |
| chr15 | 89915240 | 89915369 | Hyper | cancer_general | LINC00925, MIR9-3 | chr15 | 89920809 | 89920901 | Hyper | literature | LINC00925, MIR9-3 |
| chr15 | 89921956 | 89922006 | Hyper | cancer_general | LINC00925 | chr15 | 89922211 | 89922546 | Hyper | cancer_general | LINC00925 |
| chr15 | 89942755 | 89942945 | Hyper | cancer_general | AK054710, LINC00925 | chr15 | 89943410 | 89943706 | Hyper | pancreas, liver_tcga, tcga | AK054710, LINC00925 |
| chr15 | 89949410 | 89949942 | Hyper | cancer_general | AK054710, LINC00925 | chr15 | 89950236 | 89951113 | Hyper | cancer_general | AK054710, LINC00925 |
| chr15 | 89951400 | 89951801 | Hyper | cancer_general | AK054710, LINC00925 | chr15 | 89952153 | 89953055 | Hyper | literature, cancer_general | — |
| chr15 | 89954197 | 89954335 | Hyper | cancer_general | — | chr15 | 89956364 | 89956450 | Hyper | cancer_general | IDH2 |
| chr15 | 90039563 | 90039711 | Hyper | cancer_general | LINC00928, RHCG | chr15 | 90631823 | 90631948 | Hyper | literature | — |
| chr15 | 91643360 | 91643586 | Hyper | esophageal | SV2B | chr15 | 92936290 | 92936322 | Hyper | cancer_general | ST8SIA2 |
| chr15 | 92937153 | 92937374 | Hyper | cancer_general, tcga | ST8SIA2 | chr15 | 92937927 | 92938309 | Hyper | tcga, cancer_general | ST8SIA2 |
| chr15 | 93631739 | 93632014 | Hyper | cancer_general | — | chr15 | 93632660 | 93633233 | Hyper | cancer_general | — |
| chr15 | 95388568 | 95388616 | Hyper | cancer_general | LOC440311 | chr15 | 96874362 | 96874514 | Hyper | blood | NR2F2, MIR1469, NR2F2-AS1 |
| chr15 | 96889154 | 96889183 | Hyper | tcga | NR2F2 | chr15 | 96889401 | 96889430 | Hyper | tcga | NR2F2 |
| chr15 | 96897934 | 96898010 | Hyper | cancer_general | — | chr15 | 96911559 | 96911710 | Hyper | cancer_general | — |
| chr15 | 96952696 | 96953209 | Hyper | cancer_general | — | chr15 | 96959730 | 96959976 | Hyper | cancer_general | — |
| chr15 | 96960376 | 96960409 | Hyper | cancer_general | ARRDC4 | chr15 | 96960732 | 96960826 | Hyper | cancer_general | — |
| chr15 | 98504114 | 98504144 | Hyper | blood | ARRDC4 | chr15 | 98836178 | 98836393 | Hyper | tcga, cancer_general | — |
| chr15 | 98964786 | 98965138 | Hyper | esophageal | — | chr15 | 99193206 | 99193480 | Hyper | blood, tcga, liver_tcga | IGF1R |
| chr15 | 99193914 | 99194186 | Hyper | tcga, liver_tcga | IGF1R | chr15 | 100913423 | 100913880 | Hyper | cancer_general | — |
| chr15 | 101389973 | 101390023 | Hyper | liver_tcga | LOC145757 | chr15 | 101420521 | 101420610 | Hyper | cancer_general | ALDH1A3 |
| chr15 | 101420945 | 101420989 | Hyper | cancer_general | ALDH1A3 | chr15 | 101513607 | 101513754 | Hyper | tcga | LRRK1 |
| chr15 | 102286533 | 102286563 | Hyper | cancer_general | DQ593864, DQ588428, DQ593627, DQ588362, DQ578285, DQ597461, | chr21 | 22370332 | 22370458 | Hyper | cancer_general | NCAM2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr21 | 22370688 | 22370718 | Hyper | cancer_general | DQ582666, DQ593630, DQ582294, DQ588439, BC101079, DQ596486, DQ597703, DQ585237, DQ588452, DQ586526, DQ576888, DQ582460, DQ586138, DQ578289, DQ593624, DQ593353, DQ571896, DQ588425, DQ597539, DQ575740, DQ595661 NCAM2 | chr21 | 26934368 | 26934786 | Hyper | tcga, liver_tcga, colorectal | MIR155HG |
| chr21 | 27011773 | 27011807 | Hyper | tcga | JAM2 | chr21 | 27012373 | 27012431 | Hyper | cancer_general | JAM2 |
| chr21 | 27944995 | 27945081 | Hyper | cancer_general | CYYR1 | chr21 | 27945398 | 27945427 | Hyper | tcga | CYYR1 |
| chr21 | 27945693 | 27945722 | Hyper | tcga | CYYR1 | chr21 | 28216585 | 28217690 | Hyper | cancer_general | ADAMTS1 |
| chr21 | 28218774 | 28219045 | Hyper | cancer_general, tcga | ADAMTS1 | chr21 | 28338836 | 28338887 | Hyper | cancer_general | — |
| chr21 | 28339247 | 28339501 | Hyper | tcga, cancer_general | — | chr21 | 28339892 | 28340318 | Hyper | tcga, cancer_general | — |
| chr21 | 31311404 | 31311553 | Hyper | cancer_general | — | chr21 | 31311944 | 31312105 | Hyper | tcga, cancer_general | — |
| chr21 | 31312313 | 31312445 | Hyper | tcga, cancer_general | — | chr21 | 33244921 | 33245040 | Hyper | esophageal | HUNK |
| chr21 | 33245683 | 33245718 | Hyper | esophageal | HUNK | chr21 | 33246009 | 33246190 | Hyper | esophageal | HUNK |
| chr21 | 33785288 | 33785325 | Hyper | blood | EVA1C | chr21 | 34392171 | 34392566 | Hyper | cancer_general, tcga | OLIG2 |
| chr21 | 34395302 | 34396269 | Hyper | tcga, cancer_general | OLIG2 | chr21 | 34396795 | 34397037 | Hyper | cancer_general | OLIG2 |
| chr21 | 34398070 | 34398634 | Hyper | tcga, cancer_general | OLIG2 | chr21 | 34398933 | 34400258 | Hyper | cancer_general | OLIG2 |
| chr21 | 34401185 | 34401392 | Hyper | cancer_general | OLIG2 | chr21 | 34442547 | 34442665 | Hyper | cancer_general | OLIG1 |
| chr21 | 34443103 | 34443262 | Hyper | cancer_general | OLIG1 | chr21 | 34443509 | 34443686 | Hyper | cancer_general | OLIG1 |
| chr21 | 34443893 | 34443956 | Hyper | cancer_general | OLIG1 | chr21 | 34444163 | 34444598 | Hyper | tcga, cancer_general | OLIG1 |
| chr21 | 36041468 | 36041697 | Hyper | cancer_general | CLIC6 | chr21 | 36041985 | 36042238 | Hyper | cancer_general | CLIC6 |
| chr21 | 36042658 | 36042861 | Hyper | cancer_general | CLIC6 | chr21 | 38064457 | 38064683 | Hyper | cancer_general | SIM2 |
| chr21 | 38064966 | 38065737 | Hyper | cancer_general | SIM2 | chr21 | 38065955 | 38066112 | Hyper | cancer_general | SIM2 |
| chr21 | 38067203 | 38067233 | Hyper | cancer_general | SIM2 | chr21 | 38068178 | 38068289 | Hyper | cancer_general | SIM2 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr21 | 38068565 | 38068783 | Hyper | cancer_general | SIM2 | chr21 | 38069093 | 38069203 | Hyper | cancer_general | SIM2 |
| chr21 | 38069459 | 38069496 | Hyper | cancer_general | SIM2 | chr21 | 38069825 | 38070162 | Hyper | cancer_general, tcga | SIM2 |
| chr21 | 38070705 | 38070765 | Hyper | blood | SIM2 | chr21 | 38071791 | 38071905 | Hyper | blood | SIM2 |
| chr21 | 38073007 | 38073070 | Hyper | cancer_general | SIM2 | chr21 | 38073300 | 38073860 | Hyper | cancer_general | SIM2 |
| chr21 | 38076854 | 38077152 | Hyper | tcga, cancer_general | SIM2 | chr21 | 38078415 | 38078487 | Hyper | cancer_general | SIM2 |
| chr21 | 38079988 | 38080684 | Hyper | cancer_general | SIM2 | chr21 | 38081085 | 38081207 | Hyper | tcga | SIM2 |
| chr21 | 38081445 | 38081835 | Hyper | cancer_general | SIM2 | chr21 | 38082042 | 38082072 | Hyper | cancer_general | SIM2 |
| chr21 | 38082315 | 38082345 | Hyper | cancer_general | SIM2 | chr21 | 38082930 | 38083196 | Hyper | cancer_general | SIM2 |
| chr21 | 38119904 | 38120312 | Hyper | cancer_general | HLCS | chr21 | 39047776 | 39047838 | Hyper | head_neck | KCNJ6 |
| chr21 | 39870612 | 39870641 | Hyper | literature | ERG | chr21 | 40033619 | 40033648 | Hyper | literature | ERG |
| chr21 | 40033877 | 40033906 | Hyper | literature | ERG | chr21 | 40984685 | 40984900 | Hyper | tcga | B3GALT5, C21orf88 |
| chr21 | 43186698 | 43186889 | Hyper | blood | RIPK4 | chr21 | 44494891 | 44495155 | Hyper | tcga, cancer_general | CBS |
| chr21 | 44514762 | 44514791 | Hyper | literature | U2AF1 | chr21 | 44524441 | 44524470 | Hyper | literature | U2AF1 |
| chr21 | 44847591 | 44847622 | Hyper | tcga | SIK1 | chr21 | 45148615 | 45148758 | Hyper | cancer_general | PDXK |
| chr21 | 45717477 | 45717548 | Hyper | head_neck | PFKL, AIRE | chr21 | 46125933 | 46126721 | Hyper | cancer_general | KRTAP10-12 |
| chr21 | 46127039 | 46127094 | Hyper | cancer_general | KRTAP10-12 | chr21 | 46127542 | 46127692 | Hyper | cancer_general | KRTAP10-12 |
| chr21 | 46128902 | 46128938 | Hyper | cancer_general | COL18A1-AS2, COL18A1 | chr21 | 46129444 | 46129485 | Hyper | cancer_general | — |
| chr21 | 46825825 | 46826067 | Hyper | tcga | COL18A1 | chr21 | 47010243 | 47010451 | Hyper | cancer_general | — |
| chr21 | 47062544 | 47062825 | Hyper | cancer_general | PCBP3 | chr21 | 47063538 | 47063962 | Hyper | cancer_general | PCBP3 |
| chr21 | 47064250 | 47064377 | Hyper | cancer_general | PCBP3 | chr21 | 47518776 | 47518814 | Hyper | cancer_general | COL6A2 |
| chr21 | 47717560 | 47717589 | Hyper | liver_tcga | C21orf58, YBEY | chr7 | 329805 | 329838 | Hyper | cancer_general | LOC100288524 |
| chr7 | 556928 | 556983 | Hyper | blood | FLJ44511, PDGFA | chr7 | 751816 | 751874 | Hyper | liver_tcga, cancer_general | — |
| chr7 | 752120 | 752221 | Hyper | liver_tcga, cancer_general | — | chr7 | 922050 | 922235 | Hyper | liver_tcga | GET4, SUN1 |
| chr7 | 927933 | 927986 | Hyper | liver_tcga | ADAP1, GET4 | chr7 | 1263761 | 1263960 | Hyper | cancer_general | UNCX |
| chr7 | 1268318 | 1268366 | Hyper | cancer_general | UNCX | chr7 | 1269305 | 1269808 | Hyper | cancer_general | UNCX |
| chr7 | 1270406 | 1270440 | Hyper | cancer_general | UNCX | chr7 | 1273167 | 1273330 | Hyper | cancer_general | UNCX |
| chr7 | 1274641 | 1274677 | Hyper | cancer_general | UNCX | chr7 | 1275008 | 1275038 | Hyper | cancer_general | UNCX |
| chr7 | 1275579 | 1275680 | Hyper | cancer_general | UNCX | chr7 | 1277817 | 1277865 | Hyper | cancer_general | UNCX |
| chr7 | 1279099 | 1279129 | Hyper | cancer_general | UNCX | chr7 | 1279965 | 1279995 | Hyper | cancer_general | UNCX |
| chr7 | 1281131 | 1281232 | Hyper | cancer_general | UNCX | chr7 | 1281493 | 1281555 | Hyper | cancer_general | UNCX |
| chr7 | 1282042 | 1282150 | Hyper | cancer_general | UNCX | chr7 | 1282506 | 1282644 | Hyper | cancer_general | UNCX |
| chr7 | 1286244 | 1286338 | Hyper | cancer_general | UNCX | chr7 | 1286810 | 1286858 | Hyper | cancer_general | UNCX |
| chr7 | 1288582 | 1288753 | Hyper | cancer_general | — | chr7 | 1709138 | 1709235 | Hyper | cancer_general | — |
| chr7 | 1709474 | 1709594 | Hyper | tcga | AMZ1 | chr7 | 1748514 | 1748766 | Hyper | liver_tcga | ELFN1 |
| chr7 | 2728068 | 2728165 | Hyper | cancer_general, colorectal | — | chr7 | 2979480 | 2979512 | Hyper | literature | CARD11 |
| chr7 | 2985518 | 2985547 | Hyper | literature | CARD11 | chr7 | 3083318 | 3083352 | Hyper | tcga | CARD11 |
| chr7 | 3340444 | 3340473 | Hyper | liver_tcga | SDK1 | chr7 | 3340964 | 3340993 | Hyper | liver_tcga | SDK1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 3341489 | 3341597 | Hyper | liver_tcga, cancer_general | SDK1 | chr7 | 4922550 | 4922722 | Hyper | tcga | MMD2 |
| chr7 | 4923072 | 4923397 | Hyper | liver_tcga, cancer_general, tcga | MMD2 | chr7 | 4998201 | 4998388 | Hyper | cancer_general | MMD2 |
| chr7 | 4998698 | 4998736 | Hyper | cancer_general | MMD2 | chr7 | 5111528 | 5111669 | Hyper | liver_tcga | RBAKDN, RBAK, RBAK-RBAKDN |
| chr7 | 5632939 | 5633100 | Hyper | tcga | FSCN1 | chr7 | 6045612 | 6045641 | Hyper | literature | AIMP2, PMS2 |
| chr7 | 6414386 | 6414415 | Hyper | literature | RAC1 | chr7 | 6426878 | 6426907 | Hyper | literature | RAC1 |
| chr7 | 6543150 | 6543216 | Hyper | hepatobiliary | GRID2IP | chr7 | 6566413 | 6566663 | Hyper | tcga | — |
| chr7 | 6570959 | 6571130 | Hyper | tcga | — | chr7 | 6576137 | 6576367 | Hyper | tcga | — |
| chr7 | 6703555 | 6703959 | Hyper | liver_tcga, cancer_general | AK123300 | chr7 | 8473070 | 8473674 | Hyper | cancer_general | NXPH1 |
| chr7 | 8473956 | 8474562 | Hyper | cancer_general | NXPH1 | chr7 | 8474814 | 8475057 | Hyper | cancer_general | NXPH1 |
| chr7 | 8480640 | 8481159 | Hyper | literature, cancer_general | NXPH1 | chr7 | 8481642 | 8481833 | Hyper | cancer_general | NXPH1 |
| chr7 | 8482056 | 8482921 | Hyper | literature, cancer_general | NXPH1 | chr7 | 8483147 | 8483950 | Hyper | cancer_general | NXPH1 |
| chr7 | 12151440 | 12151678 | Hyper | cancer_general | — | chr7 | 12443317 | 12443403 | Hyper | cancer_general | VWDE SCIN, BC075797 |
| chr7 | 12443841 | 12443871 | Hyper | cancer_general | VWDE | chr7 | 12610339 | 12610476 | Hyper | blood | |
| chr7 | 15725983 | 15726081 | Hyper | cancer_general | BX538274, MEOX2 | chr7 | 15726634 | 15727077 | Hyper | tcga, cancer_general | BX538274, MEOX2 |
| chr7 | 15727290 | 15727320 | Hyper | cancer_general | BX538274, MEOX2 | chr7 | 19145808 | 19146249 | Hyper | cancer_general | TWIST1 |
| chr7 | 19146502 | 19146558 | Hyper | cancer_general | TWIST1 | chr7 | 19147122 | 19147798 | Hyper | tcga, cancer_general | TWIST1 |
| chr7 | 19152002 | 19152349 | Hyper | tcga, cancer_general | TWIST1 | chr7 | 19155791 | 19155820 | Hyper | literature | TWIST1 |
| chr7 | 19156070 | 19156916 | Hyper | tcga, literature, cancer_general | TWIST1 | chr7 | 19157144 | 19158015 | Hyper | tcga, literature, cancer_general | TWIST1 |
| chr7 | 19158632 | 19158735 | Hyper | literature | TWIST1 | chr7 | 19184058 | 19184255 | Hyper | cancer_general | BC043576, FERD3L |
| chr7 | 19813284 | 19813313 | Hyper | literature | TMEM196 | chr7 | 20816252 | 20816447 | Hyper | cancer_general | SP8 |
| chr7 | 20817380 | 20817410 | Hyper | cancer_general | SP8 | chr7 | 20818130 | 20818362 | Hyper | cancer_general | SP8 |
| chr7 | 20823292 | 20823432 | Hyper | cancer_general | SP8 | chr7 | 20823904 | 20824946 | Hyper | literature, cancer_general, tcga | SP8 |
| chr7 | 20825379 | 20825559 | Hyper | literature | SP8 | chr7 | 20826113 | 20826202 | Hyper | literature | SP8 |
| chr7 | 20826884 | 20827199 | Hyper | pancreas, literature | SP8 | chr7 | 20830670 | 20830700 | Hyper | cancer_general | SP8 |
| chr7 | 20833167 | 20833322 | Hyper | cancer_general | SP8 | chr7 | 21582593 | 21582868 | Hyper | cancer_general | DNAH11 |
| chr7 | 21583263 | 21583326 | Hyper | cancer_general | DNAH11 | chr7 | 22539833 | 22539909 | Hyper | cancer_general | STEAP1B |
| chr7 | 22589356 | 22589870 | Hyper | cancer_general | — | chr7 | 23287253 | 23287624 | Hyper | cancer_general, tcga | GPNMB |
| chr7 | 24323763 | 24323939 | Hyper | liver_tcga | NPY | chr7 | 24796478 | 24796567 | Hyper | cancer_general, tcga | DFNA5 |
| chr7 | 25892510 | 25892588 | Hyper | cancer_general | — | chr7 | 25896521 | 25896864 | Hyper | cancer_general | — |

TABLE 11-continued

| chr | Start | Stop | Hypo/hyper | classification | annotation |
|---|---|---|---|---|---|
| chr7 | 25897133 | 25897246 | Hyper | tcga, pancreas | — |
| chr7 | 27127863 | 27127898 | Hyper | cancer_general | HOXA1, HOTAIRM1 |
| chr7 | 27135327 | 27135794 | Hyper | tcga, cancer_general | HOTAIRM1, HOXA2, AK291164, HOXA1 |
| chr7 | 27136013 | 27136790 | Hyper | tcga, lung, cancer_general | HOXA2, AK291164, HOXA3, HOTAIRM1, HOXA1 |
| chr7 | 27138381 | 27138410 | Hyper | literature | HOXA2, AK291164, HOXA3, HOTAIRM1, HOXA1 |
| chr7 | 27187535 | 27187570 | Hyper | cancer_general | HOXA7, DQ655986, HOXA-AS3, HOXA6, HOXA5 |
| chr7 | 27190591 | 27191226 | Hyper | tcga, liver_tcga, cancer_general | HOXA5, HOXA7, DQ655986, HOXA-AS3, HOXA6 |
| chr7 | 27192061 | 27192098 | Hyper | cancer_general | HOXA7, HOXA9, HOXA10-HOXA9, DQ655986, HOXA-AS3, HOXA6, HOXA5 |
| chr7 | 27195462 | 27196839 | Hyper | tcga, cancer_general, lung | DQ655986, HOXA-AS3, HOXA6, HOXA9, HOXA10-HOXA9, HOXA9, HOXA7 |
| chr7 | 27204487 | 27205395 | Hyper | literature, cancer_general, liver_tcga, tcga | HOXA10-HOXA9, HOXA7, HOXA-AS4, MIR196B, HOXA10 |
| chr7 | 27205678 | 27206058 | Hyper | cancer_general | HOXA10, HOXA10-HOXA9, OHXA9, HOXA7, HOXA-AS4, MIR196B |
| chr7 | 27208187 | 27208285 | Hyper | liver_tcga | HOXA-AS4, MIR196B, HOXA10-HOXA9, HOXA9 |
| chr7 | 27209462 | 27209582 | Hyper | liver_tcga | HOXA-AS4, HOXA10-HOXA9, HOXA10, MIR196B |
| chr7 | 27209789 | 27209828 | Hyper | liver_tcga | HOXA10, MIR196B, HOXA-AS4, HOXA10-HOXA9, HOXA9 |
| chr7 | 27212499 | 27212899 | Hyper | cancer_general | HOXA11, HOXA10, MIR196B, HOXA-AS4 |
| chr7 | 27213172 | 27214310 | Hyper | tcga, literature, cancer_general | HOXA11, HOXA10, MIR 196B, HOXA-AS4 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 27217042 | 27217071 | Hyper | liver_tcga | HOXA10-HOXA9, HOXA9 | chr7 | 27223114 | 27223151 | Hyper | cancer_general | HOXA10-HOXA9, HOXA9 |
| chr7 | 27223601 | 27223696 | Hyper | cancer_general | HOXA10, HOXA11-AS, LOC402470, HOXA10, MIR196B, HOXA-AS4, HOXA10-HOXA9 | chr7 | 27224069 | 27224609 | Hyper | cancer_general | HOXA11, HOXA10, HOXA11-AS, LOC402470 |
| chr7 | 27225035 | 27225092 | Hyper | cancer_general | LOC402470, HOXA11-AS, HOXA11, HOXA10 | chr7 | 27225447 | 27225543 | Hyper | liver_tcga, literature | LOC402470, HOXA11-AS, HOXA11, HOXA10 |
| chr7 | 27227874 | 27227953 | Hyper | cancer_general | LOC402470, HOXA11-AS, HOXA11, HOXA10, HOXA13 | chr7 | 27231476 | 27231505 | Hyper | liver_tcga | HOXA11, HOXA13, HOTTIP, LOC402470 |
| chr7 | 27231818 | 27231894 | Hyper | liver_tcga | LOC402470, HOXA11-AS, HOXA11 | chr7 | 27232289 | 27232962 | Hyper | liver_tcga, cancer_general | HOXA13, HOTTIP, LOC402470, HOXA11-AS, HOXA11 |
| chr7 | 27233410 | 27233454 | Hyper | liver_tcga | HOXA13, HOTTIP, LOC402470, HOXA11-AS, HOXA11 | chr7 | 27238887 | 27238917 | Hyper | cancer_general | HOXA11, HOTTIP, HOXA13, LOC402470, HOXA11-AS |
| chr7 | 27239177 | 27239234 | Hyper | cancer_general | HOTTIP, HOXA13 | chr7 | 27240230 | 27240381 | Hyper | cancer_general | HOTTIP, HOXA13 |
| chr7 | 27244515 | 27245310 | Hyper | cancer_general | HOTTIP, HOXA13 | chr7 | 27252380 | 27252410 | Hyper | cancer_general | HOTTIP |
| chr7 | 27260092 | 27260122 | Hyper | liver_tcga | — | chr7 | 27264875 | 27265325 | Hyper | cancer_general | — |
| chr7 | 27265538 | 27265584 | Hyper | cancer_general | — | chr7 | 27275513 | 27275543 | Hyper | blood | EVX1 |
| chr7 | 27279115 | 27279453 | Hyper | cancer_general | EVX1 | chr7 | 27281329 | 27281360 | Hyper | literature | EVX1 |
| chr7 | 27282089 | 27283013 | Hyper | cancer_general | EVX1 | chr7 | 27283351 | 27283627 | Hyper | cancer_general | EVX1 |
| chr7 | 27285522 | 27286248 | Hyper | tcga, cancer_general | EVX1 | chr7 | 27288946 | 27289449 | Hyper | cancer_general | EVX1 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 27291143 | 27291851 | Hyper | literature, cancer_general | EVX1 | chr7 | 28449276 | 28450015 | Hyper | tcga, colorectal, cancer_general | CREB5, BC087859 |
| chr7 | 28995657 | 28995978 | Hyper | blood | DQ601810, TRIL | chr7 | 28996457 | 28996495 | Hyper | cancer_general, blood | DQ601810, TRIL |
| chr7 | 28996840 | 28996916 | Hyper | liver_tcga, cancer_general | DQ601810, TRIL | chr7 | 28997136 | 28997625 | Hyper | cancer_general, liver_tcga | DQ601810, TRIL |
| chr7 | 28998053 | 28998119 | Hyper | cancer_general | DQ601810, TRIL | chr7 | 30029702 | 30029822 | Hyper | tcga | SCRN1 |
| chr7 | 30721280 | 30721902 | Hyper | tcga, cancer_general | CRHR2 | chr7 | 30722290 | 30722375 | Hyper | liver_tcga, cancer_general | CRHR2 |
| chr7 | 31093003 | 31093133 | Hyper | cancer_general | ADCYAP1R1 | chr7 | 31232909 | 31232939 | Hyper | blood | |
| chr7 | 31375965 | 31376135 | Hyper | cancer_general | NEUROD6 | chr7 | 32110698 | 32110772 | Hyper | cancer_general | |
| chr7 | 32337807 | 32337837 | Hyper | cancer_general | | chr7 | 32338088 | 32338410 | Hyper | tcga, cancer_general | |
| chr7 | 32338900 | 32338930 | Hyper | cancer_general | | chr7 | 32467461 | 32468062 | Hyper | cancer_general | |
| chr7 | 32997124 | 32997454 | Hyper | blood | FKBP9 | chr7 | 33943459 | 33943759 | Hyper | cancer_general | BMPER |
| chr7 | 35225809 | 35225876 | Hyper | cancer_general | | chr7 | 35226193 | 35226765 | Hyper | tcga, cancer_general | |
| chr7 | 35292970 | 35293293 | Hyper | cancer_general | TBX20 | chr7 | 35293654 | 35294141 | Hyper | cancer_general, literature, liver_tcga | TBX20 |
| chr7 | 35294502 | 35294536 | Hyper | cancer_general | TBX20 | chr7 | 35295104 | 35295134 | Hyper | cancer_general | TBX20 |
| chr7 | 35295908 | 35295944 | Hyper | cancer_general | TBX20 | chr7 | 35296935 | 35298032 | Hyper | cancer_general | TBX20 |
| chr7 | 35300951 | 35301948 | Hyper | cancer_general, literature | TBX20 | chr7 | 35494353 | 35494440 | Hyper | cancer_general | |
| chr7 | 37487164 | 37487826 | Hyper | tcga, cancer_general | | chr7 | 37488257 | 37488578 | Hyper | cancer_general | |
| chr7 | 37488920 | 37488992 | Hyper | cancer_general | | chr7 | 37955878 | 37955979 | Hyper | cancer_general | EPDR1, SFRP4 |
| chr7 | 37956271 | 37956439 | Hyper | cancer_general | EPDR1, SFRP4 | chr7 | 37960301 | 37960335 | Hyper | cancer_general | EPDR1, SFRP4 |
| chr7 | 38670357 | 38671015 | Hyper | tcga, cancer_general | | chr7 | 39015542 | 39015981 | Hyper | cancer_general | POU6F2, AK023033 |
| chr7 | 39649223 | 39649457 | Hyper | liver_tcga, literature | LOC646999 | chr7 | 39872836 | 39873015 | Hyper | tcga | |
| chr7 | 41739663 | 41739879 | Hyper | pancreas, tcga | INHBA-AS1, INHBA | chr7 | 41982690 | 41982874 | Hyper | esophageal | |
| chr7 | 42267647 | 42267677 | Hyper | cancer_general | GLI3 | chr7 | 42276346 | 42276634 | Hyper | cancer_general | GLI3 |
| chr7 | 42533118 | 42533296 | Hyper | tcga | | chr7 | 43152109 | 43152700 | Hyper | cancer_general | HECW1, AX748020 |
| chr7 | 43152957 | 43153237 | Hyper | cancer_general, tcga | AX748020, HECW1 | chr7 | 44143980 | 44144010 | Hyper | liver_tcga | AEBP1, MIR4649 |
| chr7 | 44163926 | 44163989 | Hyper | tcga | POLD2, AEBP1 | chr7 | 44364838 | 44364903 | Hyper | colorectal | CAMK2B |
| chr7 | 45613785 | 45613898 | Hyper | cancer_general | ADCY1 | chr7 | 45614341 | 45614474 | Hyper | cancer_general | ADCY1 |
| chr7 | 45614738 | 45614809 | Hyper | cancer_general | ADCY1 | chr7 | 45615440 | 45615495 | Hyper | cancer_general | ADCY1 |
| chr7 | 45960743 | 45960794 | Hyper | cancer_general | IGFBP3 | chr7 | 45961146 | 45961176 | Hyper | cancer_general | IGFBP3 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 45961508 | 45961576 | Hyper | cancer_general | IGFBP3 | chr7 | 45961833 | 45961888 | Hyper | cancer_general | IGFBP3 |
| chr7 | 49812820 | 49813994 | Hyper | liver_tcga, literature, cancer_general | VWC2 | chr7 | 49814531 | 49814795 | Hyper | tcga, cancer_general | VWC2 |
| chr7 | 49815101 | 49815765 | Hyper | tcga, literature, cancer_general | VWC2 | chr7 | 50343263 | 50343401 | Hyper | cancer_general | IKZF1 |
| chr7 | 50043698 | 50043994 | Hyper | cancer_general | IKZF1 | chr7 | 50344226 | 50344491 | Hyper | cancer_general | IKZF1 |
| chr7 | 50860026 | 50861121 | Hyper | blood | — | chr7 | 51383754 | 51383790 | Hyper | blood | COBL |
| chr7 | 51384327 | 51384440 | Hyper | blood | COBL | chr7 | 51384915 | 51384951 | Hyper | blood | COBL |
| chr7 | 52156231 | 52156261 | Hyper | cancer_general | — | chr7 | 54609852 | 54610153 | Hyper | esophageal, cancer_general | VSTM2A |
| chr7 | 54612418 | 54612730 | Hyper | cancer_general | VSTM2A | chr7 | 55086473 | 55086601 | Hyper | blood | EGFR |
| chr7 | 55086983 | 55087533 | Hyper | blood | EGFR | chr7 | 55209976 | 55210005 | Hyper | literature | EGFR |
| chr7 | 55211065 | 55211094 | Hyper | literature | EGFR | chr7 | 55221729 | 55221836 | Hyper | literature | EGFR |
| chr7 | 55223589 | 55223636 | Hyper | literature | EGFR | chr7 | 55227993 | 55228022 | Hyper | literature | EGFR |
| chr7 | 55233028 | 55233123 | Hyper | literature | EGFR | chr7 | 55241663 | 55241737 | Hyper | literature | EGFR-AS1, EGFR |
| chr7 | 55242419 | 55242493 | Hyper | literature | EGFR-AS1, EGFR | chr7 | 55248975 | 55249085 | Hyper | literature | EGFR-AS1, EGFR |
| chr7 | 55259404 | 55259547 | Hyper | literature | EGFR, EGFR-AS1 | chr7 | 55260469 | 55260498 | Hyper | literature | EGFR, EGFR-AS1 |
| chr7 | 55268867 | 55268896 | Hyper | literature | GU228584, EGFR | chr7 | 64349026 | 64349056 | Hyper | cancer_general | ZNF273, AK097702 |
| chr7 | 64349331 | 64349470 | Hyper | cancer_general | AK097702, ZNF273 | chr7 | 64700283 | 64700329 | Hyper | cancer_general | — |
| chr7 | 64712364 | 64712510 | Hyper | cancer_general, tcga | — | chr7 | 64974382 | 64974422 | Hyper | cancer_general | — |
| chr7 | 65037609 | 65037734 | Hyper | cancer_general | — | chr7 | 65508995 | 65509043 | Hyper | cancer_general | — |
| chr7 | 65878743 | 65878793 | Hyper | tcga, colorectal | AUTS2 | chr7 | 69062519 | 69062635 | Hyper | tcga | AUTS2 |
| chr7 | 69064590 | 69065045 | Hyper | tcga, cancer_general | WBSCR17 | chr7 | 70596436 | 70596688 | Hyper | cancer_general | WBSCR17 |
| chr7 | 70596942 | 70597105 | Hyper | cancer_general | — | chr7 | 70597406 | 70597451 | Hyper | cancer_general | WBSCR17 |
| chr7 | 70597835 | 70598387 | Hyper | cancer_general | WBSCR17 | chr7 | 71217108 | 71217332 | Hyper | cancer_general | — |
| chr7 | 71800676 | 71801899 | Hyper | cancer_general | — | chr7 | 71802410 | 71802637 | Hyper | cancer_general | — |
| chr7 | 75511201 | 75511298 | Hyper | liver_tcga | RHBDD2 | chr7 | 79081792 | 79081821 | Hyper | tcga | MAGI2-AS3 |
| chr7 | 79082023 | 79082218 | Hyper | tcga, cancer_general | MAGI2-AS3 | chr7 | 79083093 | 79083177 | Hyper | cancer_general | MAGI2-AS3 |
| chr7 | 79083392 | 79083834 | Hyper | cancer_general | MAGI2-AS3 | chr7 | 80548257 | 80548403 | Hyper | blood | SEMA3C |
| chr7 | 82072350 | 82072503 | Hyper | cancer_general | — | chr7 | 82073495 | 82073533 | Hyper | blood | — |
| chr7 | 84815141 | 84815375 | Hyper | tcga | SEMA3D | chr7 | 84815744 | 84815954 | Hyper | cancer_general, tcga | SEMA3D |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 86273208 | 86273541 | Hyper | cancer_general | GRM3 | chr7 | 86274117 | 86274457 | Hyper | cancer_general | GRM3 |
| chr7 | 87104816 | 87105412 | Hyper | tcga, esophageal | ABCB4 | chr7 | 87229537 | 87230433 | Hyper | tcga, cancer_general | ABCB1 |
| chr7 | 87257012 | 87257047 | Hyper | cancer_general | RUNDC3B, ABCB1 | chr7 | 87257931 | 87258054 | Hyper | esophageal | RUNDC3B, ABCB1 |
| chr7 | 87563370 | 87563614 | Hyper | esophageal | ADAM22 | chr7 | 87563829 | 87563890 | Hyper | esophageal | ADAM22 |
| chr7 | 88387982 | 88388183 | Hyper | cancer_general | ZNF804B | chr7 | 88388540 | 88388636 | Hyper | tcga | ZNF804B |
| chr7 | 88388879 | 88389356 | Hyper | tcga, cancer_general | ZNF804B | chr7 | 89747996 | 89748340 | Hyper | cancer_general | DPY19L2P4 |
| chr7 | 89950183 | 89950810 | Hyper | cancer_general, tcga | C7orf63 | chr7 | 90226269 | 90226464 | Hyper | tcga, colorectal | CDK14 |
| chr7 | 90895012 | 90895097 | Hyper | tcga | FZD1 | chr7 | 92466152 | 92466400 | Hyper | tcga | CDK6 |
| chr7 | 93203708 | 93203756 | Hyper | cancer_general | — | chr7 | 93204332 | 93204492 | Hyper | tcga | — |
| chr7 | 93519351 | 93520137 | Hyper | liver_tcga, cancer_general | TFPI2 | chr7 | 93551323 | 93551425 | Hyper | cancer_general | GNG11 |
| chr7 | 94284302 | 94284873 | Hyper | cancer_general | PEG10, SGCE | chr7 | 96619560 | 96619603 | Hyper | cancer_general | DLX6-AS1 |
| chr7 | 96621715 | 96621811 | Hyper | cancer_general | DLX6-AS1 | chr7 | 96622107 | 96622349 | Hyper | cancer_general | DLX6-AS1 |
| chr7 | 96622694 | 96622723 | Hyper | literature | DLX6-AS1 | chr7 | 96625537 | 96625720 | Hyper | cancer_general | DLX6, DLX6-AS1 |
| chr7 | 96625998 | 96626051 | Hyper | cancer_general | DLX6, DLX6-AS1 | chr7 | 96631579 | 96631680 | Hyper | liver_tcga | DLX6, DLX6-AS1 |
| chr7 | 96634645 | 96634928 | Hyper | tcga | DLX6, DLX6-AS1 | chr7 | 96635345 | 96635473 | Hyper | cancer_general | DLX6-AS1, DLX6 |
| chr7 | 96635733 | 96636645 | Hyper | tcga, cancer_general | DLX6, DLX6-AS1 | chr7 | 96639318 | 96639348 | Hyper | cancer_general | DLX6-AS1, DLX6 |
| chr7 | 96646662 | 96647131 | Hyper | cancer_general | DLX5, DLX6, DLX6-AS1 | chr7 | 96647809 | 96648219 | Hyper | cancer_general | DLX6-AS1, DLX5, DLX6 |
| chr7 | 96649955 | 96650192 | Hyper | liver_tcga, cancer_general | DLX5, DLX6, DLX6-AS1 | chr7 | 96650884 | 96651151 | Hyper | cancer_general | DLX6 |
| chr7 | 96651472 | 96651502 | Hyper | cancer_general | DLX5 | chr7 | 96652144 | 96652174 | Hyper | cancer_general | DLX5 |
| chr7 | 96653507 | 96653993 | Hyper | cancer_general | DLX5 | chr7 | 97361098 | 97361781 | Hyper | cancer_general, literature | TAC1 |
| chr7 | 97362292 | 97362607 | Hyper | cancer_general | TAC1 | chr7 | 98245885 | 98246868 | Hyper | literature, cancer_general | NPTX2 |
| chr7 | 98247126 | 98247656 | Hyper | cancer_general | NPTX2 | chr7 | 99177742 | 99177870 | Hyper | cancer_general | ZNF655 STAG3, GPC2, GAL3ST4 |
| chr7 | 99595194 | 99595337 | Hyper | cancer_general | — | chr7 | 99775192 | 99775558 | Hype | tcga, liver_tcga | |
| chr7 | 100091210 | 100091378 | Hyper | cancer_general, literature | NYAP1 | chr7 | 100318505 | 100318575 | Hyper | cancer_general | EPO |
| chr7 | 100320690 | 100320719 | Hyper | literature | EPO | chr7 | 100547037 | 100547073 | Hyper | cancer_general | MUC3A, MUC3B |

TABLE 11-continued

| chr | Start | Stop | Hypo/hyper | classification | annotation |
|---|---|---|---|---|---|
| chr7 | 100609750 | 100609780 | Hyper | pancreas | MUC12, MUC3B, AK096803, AK057259, MUC3A |
| chr7 | 100809436 | 100809521 | Hyper | tcga | MIR4653, AP1S1, NAT16, VGF |
| chr7 | 101005968 | 101005998 | Hyper | cancer_general | COL26A1 |
| chr7 | 103085876 | 103086474 | Hyper | liver_tcga, cancer_general | — |
| chr7 | 103630475 | 103630824 | Hyper | tcga, cancer_general | — |
| chr7 | 103969694 | 103969794 | Hyper | cancer_general | JB175200, LHFPL3 |
| chr7 | 107301494 | 107301640 | Hyper | cancer_general | SLC26A4, SLC26A4-AS1 |
| chr7 | 108095686 | 108096055 | Hyper | tcga, colorectal | NRCAM |
| chr7 | 112726558 | 112726614 | Hyper | cancer_general | GPR85 |
| chr7 | 113724956 | 113725081 | Hyper | cancer_general | FOXP2 |
| chr7 | 113727442 | 113727486 | Hyper | cancer_general | FOXP2 |
| chr7 | 115117552 | 115117647 | Hyper | cancer_general | — |
| chr7 | 116412008 | 116412058 | Hyper | literature | — |
| chr7 | 116417443 | 116417496 | Hyper | literature | — |
| chr7 | 116423399 | 116423488 | Hyper | literature | — |
| chr7 | 117119381 | 117120271 | Hyper | liver_tcga, literature, cancer_general | CFTR |
| chr7 | 119913561 | 119913785 | Hyper | tcga | KCND2 |
| chr7 | 121513523 | 121513709 | Hyper | tcga | PTPRZ1 |
| chr7 | 121940935 | 121941052 | Hyper | cancer_general | FEZF1, FEZF1-AS1 |
| chr7 | 121944001 | 121944166 | Hyper | cancer_general | FEZF1, FEZF1-AS1, FEZF1 |
| chr7 | 121946478 | 121947406 | Hyper | cancer_general | FEZF1-AS1, FEZF1 |
| chr7 | 121951877 | 121952169 | Hyper | cancer_general | CADPS2, FEZF1- |
| chr7 | 100808466 | 100808502 | Hyper | pancreas | AP1S1, NAT16, VGF, MIR4653 |
| chr7 | 100823436 | 100823497 | Hyper | cancer_general | NAT16 |
| chr7 | 101558399 | 101558698 | Hyper | liver_tcga, tcga, cancer_general | CUX1 |
| chr7 | 103629059 | 103630125 | Hyper | cancer_general | — |
| chr7 | 103969217 | 103969341 | Hyper | cancer_general | JB175200, LHFPL3 |
| chr7 | 106685282 | 106685345 | Hyper | esophageal | PRKAR2B |
| chr7 | 108095329 | 108095362 | Hyper | cancer_general | NRCAM |
| chr7 | 108097172 | 108097491 | Hyper | tcga, cancer_general | NRCAM |
| chr7 | 113722810 | 113723439 | Hyper | lung, cancer_general | FOXP2 |
| chr7 | 113726509 | 113726539 | Hyper | esophageal | FOXP2 |
| chr7 | 113727722 | 113727781 | Hyper | cancer_general | FOXP2 |
| chr7 | 116140252 | 116140356 | Hyper | tcga | CAV2 |
| chr7 | 116415100 | 116415129 | Hyper | literature | — |
| chr7 | 116422067 | 116422132 | Hyper | literature | — |
| chr7 | 116962893 | 116963476 | Hyper | liver_tcga, cancer_general, tcga | WNT2 |
| chr7 | 117513675 | 117513849 | Hyper | blood | CTTNBP2 |
| chr7 | 120969672 | 120969800 | Hyper | cancer_general | WNT16 |
| chr7 | 121939677 | 121940448 | Hyper | liver_tcga, literature, cancer_general | FEZF1, FEZF1-AS1 |
| chr7 | 121941881 | 121942170 | Hyper | cancer_general | FEZF1-AS1, FEZF1 |
| chr7 | 121945822 | 121945920 | Hyper | blood | FEZF1-AS1, FEZF1 |
| chr7 | 121950137 | 121951069 | Hyper | cancer_general | CADPS2, FEZF1-AS1, FEZF1 |
| chr7 | 121956486 | 121956567 | Hyper | cancer_general | CADPS2, FEZF1- |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 121956830 | 121957331 | Hyper | cancer_general | AS1, FEZF1 | | | | | | AS1 |
| chr7 | 123173150 | 123173244 | Hyper | cancer_general | CADPS2, FEZF1-AS1 | chr7 | 122526833 | 122526873 | Hyper | blood | — |
| chr7 | 124404415 | 124404522 | Hyper | cancer_general | IQUB, NDUFA5 | chr7 | 123672048 | 123672086 | Hyper | cancer_general | EU233817, TMEM229A, L13779, BC041947 |
| chr7 | 126891504 | 126891593 | Hyper | cancer_general | GPR37 | chr7 | 126891220 | 126891250 | Hyper | cancer_general | — |
| chr7 | 127744122 | 127744631 | Hyper | cancer_general | — | chr7 | 126894076 | 126894197 | Hyper | esophageal | — |
| chr7 | 127807817 | 127807846 | Hyper | tcga | — | chr7 | 127806634 | 127806664 | Hyper | cancer_general | — |
| | | | | | | chr7 | 127808047 | 127808792 | Hyper | tcga, cancer_general | — |
| chr7 | 127841505 | 127841704 | Hyper | cancer_general | MIR129-1 | chr7 | 127881254 | 127881283 | Hyper | literature | LEP |
| chr7 | 127991826 | 127992135 | Hyper | cancer_general | PRRT4, RBM28 | chr7 | 128337467 | 128337921 | Hyper | cancer_general | — |
| chr7 | 128470897 | 128471032 | Hyper | cancer_general | FLNC, CCDC136 | chr7 | 128828195 | 128828272 | Hyper | cancer_general | SMO |
| chr7 | 129418057 | 129418428 | Hyper | pancreas, cancer_general | MIR183, MIR96, MIR182 | chr7 | 129422160 | 129423418 | Hyper | cancer_general | MIR183, MIR96 |
| chr7 | 129423834 | 129424034 | Hyper | lung, cancer_general | MIR183, MIR96 | chr7 | 129424655 | 129425887 | Hyper | cancer_general | MIR183 |
| chr7 | 129426195 | 129426236 | Hyper | cancer_general | — | chr7 | 131242738 | 131242824 | Hyper | cancer_general | PODXL |
| chr7 | 131514824 | 131514854 | Hyper | cancer_general | — | chr7 | 132261272 | 132261432 | Hyper | tcga | PLXNA4 |
| chr7 | 134143164 | 134143475 | Hyper | cancer_general | AKR1B1 | chr7 | 134143807 | 134144132 | Hyper | tcga, liver_tcga, colorectal, cancer_general | AKR1B1 |
| chr7 | 136553311 | 136554366 | Hyper | cancer_general | CHRM2 | chr7 | 136554638 | 136554966 | Hyper | cancer_general | CHRM2 |
| chr7 | 136555235 | 136555412 | Hyper | cancer_general | CHRM2 | chr7 | 136555681 | 136556091 | Hyper | tcga, cancer_general | CHRM2 |
| chr7 | 137028481 | 137028524 | Hyper | cancer_general | — | chr7 | 137531158 | 137532337 | Hyper | tcga, cancer_general | DGKI |
| chr7 | 138720785 | 138720909 | Hyper | liver_tcga | ZC3HAV1L, ZC3HAV1 | chr7 | 139167617 | 139167744 | Hyper | cancer_general | KLRG2 |
| chr7 | 139168042 | 139168379 | Hyper | cancer_general | KLRG2 | chr7 | 139208772 | 139208979 | Hyper | liver_tcga, cancer_general | CLEC2L |
| chr7 | 139930051 | 139930270 | Hyper | tcga, liver_tcga | — | chr7 | 140218053 | 140218082 | Hyper | tcga | DENND2A |
| chr7 | 140339934 | 140339982 | Hyper | cancer_general | DENND2A | chr7 | 140453121 | 140453167 | Hyper | literature | BRAF |
| chr7 | 140477779 | 140477868 | Hyper | literature | BRAF | chr7 | 140481381 | 140481431 | Hyper | literature | BRAF |
| chr7 | 140772795 | 140773228 | Hyper | tcga, cancer_general | TMEM178B | chr7 | 140773563 | 140773750 | Hyper | tcga | TMEM178B |
| chr7 | 143042634 | 143042798 | Hyper | liver_tcga | FAM131B | chr7 | 143579739 | 143580069 | Hyper | cancer_general | FAM115A |
| chr7 | 145812992 | 145813082 | Hyper | cancer_general | CNTNAP2 | chr7 | 145813412 | 145813494 | Hyper | liver_tcga | CNTNAP2 |
| chr7 | 145813891 | 145814166 | Hyper | tcga, cancer_general | CNTNAP2 | chr7 | 148508712 | 148508741 | Hyper | literature | EZH2 |
| chr7 | 149112058 | 149112416 | Hyper | literature, cancer_general | TRNA_Cys | chr7 | 149119948 | 149120073 | Hyper | cancer_general | ZNF777, TRNA_Cys |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 149411541 | 149412304 | Hyper | colorectal | TRNA_Cys, KRBA1 | chr7 | 149570368 | 149570406 | Hyper | esophageal | ATP6V0E2-AS1, ZNF862, DQ590227, ATP6V0E2 |
| chr7 | 149744505 | 149744560 | Hyper | cancer_general | AL162052 | chr7 | 149917248 | 149917336 | Hyper | liver_tcga, cancer_general | — |
| chr7 | 149918119 | 149918149 | Hyper | cancer_general | — | chr7 | 150038883 | 150038912 | Hyper | literature | RARRES2, LRRC61, ZBED6CL |
| chr7 | 150716169 | 150716305 | Hyper | cancer_general | ABCB8, ATG9B | chr7 | 150748192 | 150748406 | Hyper | cancer_general | CDK5, SLC4A2, ASIC3, ABCB8 |
| chr7 | 151106451 | 151107004 | Hyper | cancer_general | WDR86-AS1, WDR86 | chr7 | 151107486 | 151107651 | Hyper | cancer_general | WDR86-AS1, WDR86 |
| chr7 | 151188034 | 151188063 | Hyper | literature | RHEB | chr7 | 152133406 | 152133436 | Hyper | liver_tcga | FABP5P3, KMT2C |
| chr7 | 152622621 | 152622697 | Hyper | cancer_general | — | chr7 | 152623016 | 152623057 | Hyper | cancer_general, literature | — |
| chr7 | 153583595 | 153584069 | Hyper | cancer_general | DPP6 | chr7 | 153584389 | 153584623 | Hyper | cancer_general | DPP6 |
| chr7 | 153584848 | 153585206 | Hyper | cancer_general | DPP6 | chr7 | 153585418 | 153585606 | Hyper | cancer_general | DPP6 |
| chr7 | 153749720 | 153750115 | Hyper | cancer_general | DPP6, AK127966 | chr7 | 154862046 | 154862266 | Hyper | cancer_general | LOC10012826, HTR5A |
| chr7 | 155164454 | 155165562 | Hyper | tcga, cancer_general | BC150495 | chr7 | 155165875 | 155166784 | Hyper | cancer_general | BC150495 |
| chr7 | 155167034 | 155167909 | Hyper | tcga, cancer_general | BC150495 | chr7 | 155174656 | 155174788 | Hyper | cancer_general | BC150495 |
| chr7 | 155241318 | 155242049 | Hyper | cancer_general | EN2 | chr7 | 155242729 | 155243102 | Hyper | cancer_general | EN2 |
| chr7 | 155243346 | 155243561 | Hyper | cancer_general | EN2 | chr7 | 155243825 | 155243895 | Hyper | cancer_general | EN2 |
| chr7 | 155244180 | 155244361 | Hyper | cancer_general | EN2 | chr7 | 155246886 | 155247584 | Hyper | cancer_general | EN2 |
| chr7 | 155248913 | 155248943 | Hyper | cancer_general | EN2 | chr7 | 155249512 | 155249565 | Hyper | cancer_general | EN2 |
| chr7 | 155249925 | 155250011 | Hyper | cancer_general | EN2 | chr7 | 155250283 | 155250355 | Hyper | tcga | EN2 |
| chr7 | 155250787 | 155250996 | Hyper | cancer_general | EN2 | chr7 | 155251701 | 155251939 | Hyper | cancer_general | EN2 |
| chr7 | 155252247 | 155252490 | Hyper | cancer_general | EN2 | chr7 | 155252862 | 155253041 | Hyper | cancer_general | EN2 |
| chr7 | 155254848 | 155255324 | Hyper | cancer_general | EN2 | chr7 | 155256237 | 155256312 | Hyper | cancer_general | EN2 |
| chr7 | 155257040 | 155257189 | Hyper | cancer_general | EN2 | chr7 | 155258193 | 155258487 | Hyper | cancer_general | EN2 |
| chr7 | 155258949 | 155260137 | Hyper | tcga, cancer_general | EN2 | chr7 | 155260880 | 155261210 | Hyper | cancer_general, tcga | EN2 |
| chr7 | 155301838 | 155301931 | Hyper | cancer_general | CNPY1 | chr7 | 155302328 | 155303335 | Hyper | tcga, cancer_general | CNPY1 |
| chr7 | 155325796 | 155325872 | Hyper | cancer_general | CNPY1 | chr7 | 155326169 | 155326527 | Hyper | cancer_general | CNPY1 |
| chr7 | 155580165 | 155580211 | Hyper | cancer_general | RBM33 | chr7 | 155600629 | 155600723 | Hyper | cancer_general | SHH |
| chr7 | 155602751 | 155602805 | Hyper | blood | SHH | chr7 | 156409144 | 156409347 | Hyper | cancer_general | — |
| chr7 | 156409665 | 156409802 | Hyper | cancer_general | — | chr7 | 156701846 | 156701908 | Hyper | cancer_general | — |
| chr7 | 156794153 | 156794235 | Hyper | cancer_general | MNX1, LOC645249 | chr7 | 156794443 | 156794485 | Hyper | cancer_general | MNX1, LOC645249 |
| chr7 | 156794998 | 156795914 | Hyper | cancer_general | MNX1, LOC645249 | chr7 | 156796534 | 156799467 | Hyper | cancer_general, tcga | MNX1, LOC645249 |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| chr7 | 156800999 | 156801029 | Hyper | cancer_general | LOC645249, MNX1 | chr7 | 156801403 | 156801601 | Hyper | lung, cancer_general | LOC64524 MNX19, |
| chr7 | 156808858 | 156809199 | Hyper | cancer_general | LOC645249, MNX1 | chr7 | 156809983 | 156811436 | Hyper | cancer_general | LOC645249, MNX1 |
| chr7 | 156812852 | 156815092 | Hyper | tcga, cancer_general | LOC645249, MNX1 | chr7 | 156871168 | 156871297 | Hyper | cancer_general | |
| chr7 | 157361605 | 157361635 | Hyper | cancer_general | MIR153-2, PTPRN2 | chr7 | 157476879 | 157477272 | Hyper | cancer_general | |
| chr7 | 157477473 | 157477914 | Hyper | cancer_general | — | chr7 | 157481130 | 157481160 | Hyper | pancreas | — |
| chr7 | 157481364 | 157481756 | Hyper | cancer_general | — | chr7 | 157481969 | 157482168 | Hyper | cancer_general | — |
| chr7 | 157482492 | 157482667 | Hyper | cancer_general | — | chr7 | 157483320 | 157483538 | Hyper | tcga, cancer_general | — |
| chr7 | 157484877 | 157485277 | Hyper | cancer_general | — | chr7 | 157485527 | 157485705 | Hyper | cancer_general | WDR60 |
| chr7 | 157485976 | 157486503 | Hyper | cancer_general | — | chr7 | 158673836 | 158673942 | Hyper | liver_tcga | VIPR2 |
| chr7 | 158936492 | 158936880 | Hyper | cancer_general, liver_tcga | VIPR2 | chr7 | 158937158 | 158937624 | Hyper | liver_tcga, cancer_general, tcga | |
| chr7 | 158938210 | 158938399 | Hyper | cancer_general | VIPR2 | HCMV-AD169 | 17724 | 17753 | Hyper | virus | — |
| HCMV-AD169 | 18691 | 18720 | Hyper | virus | — | HCMV-AD169 | 23851 | 23880 | Hyper | virus | — |
| HCMV-AD169 | 27296 | 27325 | Hyper | virus | — | HCMV-AD169 | 42909 | 42938 | Hyper | virus | — |
| HCMV-AD169 | 57909 | 57938 | Hyper | virus | — | HCMV-AD169 | 68427 | 68456 | Hyper | virus | — |
| HCMV-AD169 | 76862 | 76891 | Hyper | virus | — | HCMV-AD169 | 78956 | 78985 | Hyper | virus | — |
| HCMV-AD169 | 81188 | 81217 | Hyper | virus | — | HCMV-AD169 | 84448 | 84477 | Hyper | virus | — |
| HCMV-AD169 | 88920 | 88949 | Hyper | virus | — | HCMV-AD169 | 99889 | 99918 | Hyper | virus | — |
| HCMV-AD169 | 101238 | 101267 | Hyper | virus | — | HCMV-AD169 | 108021 | 108050 | Hyper | virus | — |
| HCMV-AD169 | 114824 | 114853 | Hyper | virus | — | HCMV-AD169 | 128011 | 128040 | Hyper | virus | — |
| HCMV-AD169 | 129567 | 129596 | Hyper | virus | — | HCMV-AD169 | 149187 | 149216 | Hyper | virus | — |
| HCMV-AD169 | 162299 | 162328 | Hyper | virus | — | HCMV-AD169 | 169250 | 169279 | Hyper | virus | — |
| HCMV-AD169 | 171221 | 171250 | Hyper | virus | — | HCMV-AD169 | 172561 | 172590 | Hyper | virus | — |
| HCMV-AD169 | 177053 | 177082 | Hyper | virus | — | HCMV-AD169 | 193060 | 193089 | Hyper | virus | — |
| HCMV-AD169 | 193858 | 193887 | Hyper | virus | — | HCMV-AD169 | 194176 | 194205 | Hyper | virus | — |
| HCMV-AD169 | 195222 | 195251 | Hyper | virus | — | HCMV-AD169 | 196060 | 196089 | Hyper | virus | — |
| HCMV-AD169 | 196817 | 196846 | Hyper | virus | — | HCMV-AD169 | 199152 | 199181 | Hyper | virus | — |

TABLE 11-continued

| chr | Start | Stop | Hypo/hyper | classification | annotation | Chr | Start | Stop | Hypo/hyper | Classification | annotation |
|---|---|---|---|---|---|---|---|---|---|---|---|
| HCMV-AD169 | 199906 | 199935 | Hyper | virus | — | HCMV-AD169 | 201145 | 201174 | Hyper | virus | — |
| HCMV-AD169 | 204433 | 204462 | Hyper | virus | — | HCMV-AD169 | 207682 | 207711 | Hyper | virus | — |
| HCMV-AD169 | 209510 | 209539 | Hyper | virus | — | HCMV-AD169 | 210069 | 210098 | Hyper | virus | — |
| HCMV-AD169 | 212133 | 212162 | Hyper | virus | — | HCMV-AD169 | 212591 | 212620 | Hyper | virus | — |
| HCMV-AD169 | 214453 | 214482 | Hyper | virus | — | HCMV-AD169 | 220316 | 220345 | Hyper | virus | — |
| GL000225.1 | 37720 | 37842 | Hyper | esophageal | — | MCV-R17b | 111 | 140 | Hyper | virus | — |
| MCV-R17b | 368 | 397 | Hyper | virus | — | MCV-R17b | 625 | 654 | Hyper | virus | — |
| MCV-R17b | 882 | 911 | Hyper | virus | — | MCV-R17b | 1139 | 1168 | Hyper | virus | — |
| MCV-R17b | 1396 | 1425 | Hyper | virus | — | MCV-R17b | 1653 | 1682 | Hyper | virus | — |
| MCV-R17b | 1910 | 1939 | Hyper | virus | — | MCV-R17b | 2167 | 2196 | Hyper | virus | — |
| MCV-R17b | 2424 | 2453 | Hyper | virus | — | MCV-R17b | 2681 | 2710 | Hyper | virus | — |
| MCV-R17b | 2938 | 2967 | Hyper | virus | — | MCV-R17b | 3195 | 3224 | Hyper | virus | — |
| MCV-R17b | 3452 | 3481 | Hyper | virus | — | MCV-R17b | 3709 | 3738 | Hyper | virus | — |
| MCV-R17b | 3966 | 3995 | Hyper | virus | — | MCV-R17b | 4223 | 4252 | Hyper | virus | — |
| MCV-R17b | 4480 | 4509 | Hyper | virus | — | MCV-R17b | 4737 | 4766 | Hyper | virus | — |
| MCV-R17b | 4994 | 5023 | Hyper | virus | — | | | | | | |

TABLE 12

| chr | start | end | chr | start | end | chr | start | end |
|---|---|---|---|---|---|---|---|---|
| chr1 | 715373 | 715447 | chr1 | 898654 | 898690 | chr1 | 913532 | 913955 |
| chr1 | 1047531 | 1047647 | chr1 | 1080583 | 1080824 | chr1 | 1095420 | 1095459 |
| chr1 | 1146734 | 1146818 | chr1 | 1218737 | 1218820 | chr1 | 1223512 | 1223652 |
| chr1 | 1235813 | 1236078 | chr1 | 1253330 | 1253386 | chr1 | 1267014 | 1267151 |
| chr1 | 1267462 | 1267699 | chr1 | 1267906 | 1268158 | chr1 | 1281214 | 1281244 |
| chr1 | 1341668 | 1341743 | chr1 | 1436043 | 1436211 | chr1 | 1473125 | 1473207 |
| chr1 | 1475556 | 1475643 | chr1 | 1476255 | 1476318 | chr1 | 1483186 | 1483363 |
| chr1 | 1547129 | 1547348 | chr1 | 1563193 | 1563223 | chr1 | 1688882 | 1689012 |
| chr1 | 1805049 | 1805089 | chr1 | 1856436 | 1856466 | chr1 | 1857847 | 1857909 |
| chr1 | 1874744 | 1874787 | chr1 | 1910415 | 1910445 | chr1 | 1923457 | 1923521 |
| chr1 | 1935274 | 1935459 | chr1 | 1974848 | 1974925 | chr1 | 2066490 | 2066679 |
| chr1 | 2125216 | 2125483 | chr1 | 2165895 | 2165999 | chr1 | 2263169 | 2263263 |
| chr1 | 2267552 | 2267690 | chr1 | 2304327 | 2304389 | chr1 | 2307925 | 2307955 |
| chr1 | 2308376 | 2308636 | chr1 | 2309868 | 2309953 | chr1 | 2331363 | 2331437 |
| chr1 | 2336397 | 2336427 | chr1 | 2375148 | 2375543 | chr1 | 2397001 | 2397031 |
| chr1 | 2428331 | 2428385 | chr1 | 2472174 | 2472301 | chr1 | 2507063 | 2507183 |
| chr1 | 2514330 | 2514376 | chr1 | 2521024 | 2521063 | chr1 | 2706308 | 2706334 |
| chr1 | 2830155 | 2830185 | chr1 | 2866038 | 2866068 | chr1 | 2984719 | 2984749 |
| chr1 | 3102653 | 3102779 | chr1 | 3158823 | 3158962 | chr1 | 3182883 | 3182917 |
| chr1 | 3183415 | 3183455 | chr1 | 3322090 | 3322170 | chr1 | 3567093 | 3567344 |
| chr1 | 3567738 | 3567850 | chr1 | 3567883 | 3568226 | chr1 | 3601850 | 3601946 |
| chr1 | 3607081 | 3607236 | chr1 | 3659550 | 3659642 | chr1 | 3659672 | 3659716 |
| chr1 | 3663532 | 3663562 | chr1 | 3663874 | 3663921 | chr1 | 3664461 | 3664741 |
| chr1 | 3683686 | 3683818 | chr1 | 3700384 | 3700414 | chr1 | 3733551 | 3733581 |
| chr1 | 4111061 | 4111231 | chr1 | 4401433 | 4401463 | chr1 | 4714018 | 4714074 |
| chr1 | 4714164 | 4714345 | chr1 | 4715428 | 4715539 | chr1 | 4715575 | 4716701 |
| chr1 | 5919973 | 5920071 | chr1 | 5920650 | 5920710 | chr1 | 5924296 | 5924431 |
| chr1 | 5924851 | 5924984 | chr1 | 5926596 | 5926645 | chr1 | 5933086 | 5933144 |
| chr1 | 5934925 | 5935061 | chr1 | 5940517 | 5940547 | chr1 | 5940945 | 5941132 |
| chr1 | 5944299 | 5944449 | chr1 | 5944962 | 5945001 | chr1 | 5945348 | 5945435 |
| chr1 | 5947258 | 5947288 | chr1 | 5949491 | 5949675 | chr1 | 5950965 | 5951039 |
| chr1 | 5957473 | 5957503 | chr1 | 5967237 | 5967267 | chr1 | 5969001 | 5969283 |
| chr1 | 5972104 | 5972134 | chr1 | 5972878 | 5972922 | chr1 | 6021621 | 6021651 |
| chr1 | 6025872 | 6025950 | chr1 | 6036766 | 6036796 | chr1 | 6056157 | 6056201 |
| chr1 | 6056506 | 6056651 | chr1 | 6059910 | 6059974 | chr1 | 6166353 | 6166469 |
| chr1 | 6171763 | 6171810 | chr1 | 6186511 | 6186546 | chr1 | 6280243 | 6280273 |
| chr1 | 6284828 | 6284858 | chr1 | 6304201 | 6304242 | chr1 | 6360593 | 6360634 |
| chr1 | 6410456 | 6410486 | chr1 | 6446131 | 6446308 | chr1 | 6480514 | 6480831 |
| chr1 | 6501055 | 6501179 | chr1 | 6507678 | 6508126 | chr1 | 6672227 | 6672351 |
| chr1 | 6713914 | 6714041 | chr1 | 6714348 | 6714378 | chr1 | 6776304 | 6776388 |
| chr1 | 7764641 | 7764737 | chr1 | 7973843 | 7973948 | chr1 | 8085685 | 8085715 |
| chr1 | 8549986 | 8550078 | chr1 | 9324231 | 9324274 | chr1 | 9402465 | 9402616 |
| chr1 | 9527172 | 9527208 | chr1 | 9601954 | 9601984 | chr1 | 9712074 | 9712104 |
| chr1 | 9712561 | 9713014 | chr1 | 9722138 | 9722215 | chr1 | 9795995 | 9796196 |
| chr1 | 9865110 | 9865140 | chr1 | 9867157 | 9867316 | chr1 | 10091888 | 10092060 |
| chr1 | 10095469 | 10095845 | chr1 | 10123736 | 10123928 | chr1 | 10166521 | 10166551 |
| chr1 | 10491694 | 10491724 | chr1 | 10948552 | 10948582 | chr1 | 11169346 | 11169375 |
| chr1 | 11174404 | 11174433 | chr1 | 11181358 | 11181432 | chr1 | 11182142 | 11182171 |
| chr1 | 11188149 | 11188178 | chr1 | 11210182 | 11210211 | chr1 | 11217215 | 11217337 |
| chr1 | 11249032 | 11249061 | chr1 | 11538705 | 11538821 | chr1 | 11539175 | 11539205 |
| chr1 | 11539410 | 11639440 | chr1 | 11540129 | 11540178 | chr1 | 11591719 | 11591826 |
| chr1 | 11752476 | 11752511 | chr1 | 11886250 | 11886280 | chr1 | 11936748 | 11936778 |
| chr1 | 11959093 | 11959196 | chr1 | 12041374 | 12041525 | chr1 | 12123243 | 12123553 |
| chr1 | 12227685 | 12227941 | chr1 | 12251443 | 12251958 | chr1 | 12460299 | 12460356 |
| chr1 | 13910436 | 13910714 | chr1 | 13984525 | 13984742 | chr1 | 14026481 | 14026618 |
| chr1 | 14032304 | 14032347 | chr1 | 14097878 | 14098015 | chr1 | 14128478 | 14128588 |
| chr1 | 14149749 | 14149867 | chr1 | 14730425 | 14730472 | chr1 | 14746206 | 14746245 |
| chr1 | 14925501 | 14926050 | chr1 | 15128565 | 15128595 | chr1 | 15251120 | 15251211 |
| chr1 | 15480593 | 15480892 | chr1 | 16474413 | 16474576 | chr1 | 16475031 | 16475207 |
| chr1 | 16861522 | 16861552 | chr1 | 17445857 | 17445943 | chr1 | 17757538 | 17757570 |
| chr1 | 17787472 | 17787502 | chr1 | 18437457 | 18437526 | chr1 | 18956211 | 18956304 |
| chr1 | 18956574 | 18956610 | chr1 | 18956856 | 18957246 | chr1 | 18957507 | 18957587 |
| chr1 | 18958033 | 18958228 | chr1 | 18958359 | 18958381 | chr1 | 18959456 | 18959550 |
| chr1 | 18960897 | 18960990 | chr1 | 18962727 | 18963135 | chr1 | 18969625 | 18969819 |
| chr1 | 18971852 | 18971929 | chr1 | 18972130 | 18972160 | chr1 | 19043563 | 19043678 |
| chr1 | 19980747 | 19980858 | chr1 | 19992418 | 19992432 | chr1 | 20127338 | 20127471 |
| chr1 | 20248109 | 20248141 | chr1 | 20492168 | 20492298 | chr1 | 20618329 | 20618369 |
| chr1 | 20693317 | 20693420 | chr1 | 20879035 | 20879228 | chr1 | 20879256 | 20879289 |
| chr1 | 20879562 | 20879640 | chr1 | 20879845 | 20879957 | chr1 | 20880182 | 20880605 |
| chr1 | 21026117 | 21026225 | chr1 | 21042894 | 21042924 | chr1 | 21044125 | 21044161 |
| chr1 | 21050471 | 21050511 | chr1 | 21058635 | 21058776 | chr1 | 21573283 | 21573362 |
| chr1 | 21573668 | 21574203 | chr1 | 21713716 | 21713792 | chr1 | 21835943 | 21836007 |
| chr1 | 22140753 | 22141184 | chr1 | 22141326 | 22141355 | chr1 | 22222711 | 22222793 |
| chr1 | 22927410 | 22927482 | chr1 | 23347997 | 23348043 | chr1 | 23449766 | 23449859 |
| chr1 | 23748982 | 23749070 | chr1 | 23885070 | 23885100 | chr1 | 24104000 | 24104062 |
| chr1 | 24161782 | 24161882 | chr1 | 24740603 | 24740829 | chr1 | 25255921 | 25255934 |
| chr1 | 25256354 | 25256383 | chr1 | 25257157 | 25257205 | chr1 | 25257490 | 25257529 |
| chr1 | 25257532 | 25257561 | chr1 | 25257916 | 25258250 | chr1 | 25919307 | 25919337 |

TABLE 12-continued

| chr | start | end | chr | start | end | chr | start | end |
|---|---|---|---|---|---|---|---|---|
| chr1 | 26183522 | 26183579 | chr1 | 26467523 | 26467630 | chr1 | 26551729 | 26551796 |
| chr1 | 26552086 | 26552130 | chr1 | 26737583 | 26737613 | chr1 | 26737946 | 26738182 |
| chr1 | 26917724 | 26917816 | chr1 | 26963625 | 26963789 | chr1 | 27190175 | 27190278 |
| chr1 | 27332448 | 27332673 | chr1 | 27340252 | 27340412 | chr1 | 27724058 | 27724093 |
| chr1 | 27844518 | 27844548 | chr1 | 28558539 | 28558571 | chr1 | 28726724 | 28726812 |
| chr1 | 28727177 | 28727324 | chr1 | 28727894 | 28728020 | chr1 | 29047659 | 29048643 |
| chr1 | 29060250 | 29060311 | chr1 | 29065131 | 29065211 | chr1 | 29450491 | 29450543 |
| chr1 | 29586072 | 29586674 | chr1 | 29804947 | 29805094 | chr1 | 30351554 | 30351742 |
| chr1 | 30815412 | 30815416 | chr1 | 30815455 | 30815578 | chr1 | 31863186 | 31863216 |
| chr1 | 32180397 | 32180427 | chr1 | 32237639 | 32238507 | chr1 | 32410276 | 32410306 |
| chr1 | 32410519 | 32410614 | chr1 | 32533211 | 32533653 | chr1 | 32705488 | 32705550 |
| chr1 | 32756498 | 32756581 | chr1 | 32930458 | 32930558 | chr1 | 32938720 | 32938750 |
| chr1 | 33163605 | 33163786 | chr1 | 33219567 | 33219596 | chr1 | 34628948 | 34628978 |
| chr1 | 34629469 | 34629728 | chr1 | 34630548 | 34630635 | chr1 | 34630859 | 34630978 |
| chr1 | 34631580 | 34631662 | chr1 | 34631933 | 34631963 | chr1 | 34642380 | 34642489 |
| chr1 | 35258637 | 35258714 | chr1 | 35351078 | 35351659 | chr1 | 35395526 | 35395851 |
| chr1 | 35586911 | 35586962 | chr1 | 35664625 | 35664746 | chr1 | 36042679 | 36043489 |
| chr1 | 36236269 | 36236299 | chr1 | 36334925 | 36335053 | chr1 | 36563479 | 36563522 |
| chr1 | 36849009 | 36849038 | chr1 | 37498792 | 37498844 | chr1 | 37498889 | 37499181 |
| chr1 | 37499460 | 37499682 | chr1 | 37500014 | 37500153 | chr1 | 37500468 | 37500574 |
| chr1 | 37500603 | 37500806 | chr1 | 37501072 | 37501102 | chr1 | 38060267 | 38060317 |
| chr1 | 38100689 | 38100851 | chr1 | 38219712 | 38219795 | chr1 | 38230042 | 38230242 |
| chr1 | 38230283 | 38230297 | chr1 | 38230779 | 38230859 | chr1 | 38398213 | 38398348 |
| chr1 | 38412504 | 38412832 | chr1 | 38510178 | 38510217 | chr1 | 38510563 | 38510624 |
| chr1 | 38510854 | 38511119 | chr1 | 38511337 | 38511799 | chr1 | 38511822 | 38511824 |
| chr1 | 38512385 | 38512415 | chr1 | 38513244 | 38513318 | chr1 | 39269741 | 39270121 |
| chr1 | 39416980 | 39417182 | chr1 | 40072513 | 40072680 | chr1 | 40137898 | 40137984 |
| chr1 | 40237141 | 40237203 | chr1 | 40349545 | 40349647 | chr1 | 40625371 | 40625401 |
| chr1 | 40708443 | 40708578 | chr1 | 40915590 | 40915620 | chr1 | 41283958 | 41284463 |
| chr1 | 41847583 | 41847702 | chr1 | 41848810 | 41848840 | chr1 | 41915253 | 41915283 |
| chr1 | 41967342 | 41967418 | chr1 | 41991640 | 41991702 | chr1 | 43188741 | 43188874 |
| chr1 | 43400336 | 43400386 | chr1 | 43478202 | 43478255 | chr1 | 43814994 | 43815023 |
| chr1 | 43834741 | 43834922 | chr1 | 43842664 | 43842779 | chr1 | 44068774 | 44068804 |
| chr1 | 44109845 | 44109959 | chr1 | 44310283 | 44310324 | chr1 | 44494137 | 44494169 |
| chr1 | 44726912 | 44727268 | chr1 | 44872448 | 44872722 | chr1 | 44872924 | 44873172 |
| chr1 | 44873510 | 44873706 | chr1 | 44883121 | 44883214 | chr1 | 44883752 | 44884122 |
| chr1 | 45240422 | 45240514 | chr1 | 45308154 | 45308262 | chr1 | 45308592 | 45308625 |
| chr1 | 45645870 | 45645998 | chr1 | 45768429 | 45768504 | chr1 | 46077719 | 46077805 |
| chr1 | 46347598 | 46347689 | chr1 | 46632876 | 46632923 | chr1 | 46744657 | 46744733 |
| chr1 | 46913837 | 46913876 | chr1 | 46913887 | 46914245 | chr1 | 46914656 | 46914686 |
| chr1 | 46932765 | 46932905 | chr1 | 46951207 | 46951317 | chr1 | 46951645 | 46951739 |
| chr1 | 46956454 | 46956603 | chr1 | 46956823 | 46957171 | chr1 | 47009929 | 47010035 |
| chr1 | 47035373 | 47035403 | chr1 | 47078736 | 47078782 | chr1 | 47695122 | 47695422 |
| chr1 | 47696295 | 47696520 | chr1 | 47696821 | 47696964 | chr1 | 47696987 | 47697110 |
| chr1 | 47697356 | 47697510 | chr1 | 47697732 | 47697946 | chr1 | 47698007 | 47698210 |
| chr1 | 47788247 | 47788348 | chr1 | 47882063 | 47882322 | chr1 | 47882769 | 47882803 |
| chr1 | 47909718 | 47910160 | chr1 | 47910523 | 47910624 | chr1 | 47910749 | 47910914 |
| chr1 | 47911424 | 47911508 | chr1 | 47999050 | 47999163 | chr1 | 48059078 | 48059243 |
| chr1 | 49242344 | 49242533 | chr1 | 50513629 | 50513745 | chr1 | 50799278 | 50799316 |
| chr1 | 50799394 | 50799400 | chr1 | 50880932 | 50881302 | chr1 | 50881427 | 50881956 |
| chr1 | 50882144 | 50882529 | chr1 | 50882808 | 50883611 | chr1 | 50883882 | 50883976 |
| chr1 | 50884021 | 50884352 | chr1 | 50884691 | 50884887 | chr1 | 50885336 | 50885366 |
| chr1 | 50886188 | 50887084 | chr1 | 50887176 | 50887284 | chr1 | 50888709 | 50888795 |
| chr1 | 50889124 | 50889510 | chr1 | 50889820 | 50890379 | chr1 | 50890796 | 50891595 |
| chr1 | 50892153 | 50892283 | chr1 | 50892337 | 50892351 | chr1 | 50892607 | 50893422 |
| chr1 | 50893519 | 50893877 | chr1 | 51424099 | 51424224 | chr1 | 51763252 | 51763298 |
| chr1 | 52832687 | 52832820 | chr1 | 53019468 | 53019568 | chr1 | 53068166 | 53068546 |
| chr1 | 53098842 | 53099067 | chr1 | 53129154 | 53129244 | chr1 | 53192045 | 53192075 |
| chr1 | 53308568 | 53308607 | chr1 | 53308908 | 53309248 | chr1 | 53528374 | 53528439 |
| chr1 | 53705647 | 53705701 | chr1 | 54203829 | 54204399 | chr1 | 54586626 | 54586736 |
| chr1 | 54837089 | 54837119 | chr1 | 54877027 | 54877451 | chr1 | 55231115 | 55231177 |
| chr1 | 55462673 | 55462703 | chr1 | 57888367 | 57888397 | chr1 | 57888987 | 57889087 |
| chr1 | 57889402 | 57889654 | chr1 | 57890431 | 57890650 | chr1 | 58715153 | 58715194 |
| chr1 | 58715475 | 58715854 | chr1 | 58715979 | 58715993 | chr1 | 61519360 | 61519394 |
| chr1 | 61541602 | 61641718 | chr1 | 62189908 | 62189987 | chr1 | 62660740 | 62660768 |
| chr1 | 62660786 | 62660861 | chr1 | 62793237 | 62793267 | chr1 | 63539509 | 63539887 |
| chr1 | 63785619 | 63785766 | chr1 | 63786079 | 63786329 | chr1 | 63787031 | 63787063 |
| chr1 | 63787302 | 63787568 | chr1 | 63788423 | 63788557 | chr1 | 63788920 | 63789496 |
| chr1 | 63789729 | 63789791 | chr1 | 63789850 | 63789912 | chr1 | 63790253 | 63790278 |
| chr1 | 63792561 | 63792648 | chr1 | 63792798 | 63793072 | chr1 | 63795263 | 63796277 |
| chr1 | 63796498 | 63796575 | chr1 | 64240026 | 64240118 | chr1 | 64240617 | 64240673 |
| chr1 | 64734652 | 64734694 | chr1 | 64937330 | 64937542 | chr1 | 65303636 | 65303692 |
| chr1 | 65304227 | 65304256 | chr1 | 65305384 | 65305413 | chr1 | 65306926 | 65306955 |
| chr1 | 65309787 | 65309816 | chr1 | 65310487 | 65310531 | chr1 | 65311188 | 65311217 |
| chr1 | 65312331 | 65312432 | chr1 | 65731337 | 65731446 | chr1 | 65990955 | 65991018 |
| chr1 | 65991446 | 65991560 | chr1 | 65991606 | 65991757 | chr1 | 66258180 | 66258650 |
| chr1 | 66258672 | 66258774 | chr1 | 66259137 | 66259174 | chr1 | 66998790 | 66999332 |
| chr1 | 66999636 | 66999673 | chr1 | 67218064 | 67218343 | chr1 | 67390334 | 67390450 |

TABLE 12-continued

| chr | start | end | chr | start | end | chr | start | end |
|---|---|---|---|---|---|---|---|---|
| chr1 | 67391067 | 67391096 | chr1 | 67669791 | 67669853 | chr1 | 67773159 | 67773780 |
| chr1 | 70033609 | 70033916 | chr1 | 70034459 | 70034574 | chr1 | 70035088 | 70035537 |
| chr1 | 70599012 | 70599169 | chr1 | 70672778 | 70672878 | chr1 | 72749641 | 72749699 |
| chr1 | 75595819 | 75595990 | chr1 | 75596136 | 75596384 | chr1 | 75596687 | 75596858 |
| chr1 | 75596930 | 75597584 | chr1 | 75597923 | 75598179 | chr1 | 75598384 | 75598414 |
| chr1 | 75599427 | 75599621 | chr1 | 75600225 | 75600848 | chr1 | 75600925 | 75601118 |
| chr1 | 75601188 | 75601428 | chr1 | 75601983 | 75603052 | chr1 | 76080484 | 76080768 |
| chr1 | 76082129 | 76082209 | chr1 | 76354624 | 76354754 | chr1 | 76540450 | 76540666 |
| chr1 | 77333058 | 77333088 | chr1 | 77333384 | 77333433 | chr1 | 77334169 | 77334385 |
| chr1 | 77334409 | 77334756 | chr1 | 77747366 | 77747453 | chr1 | 77747939 | 77748235 |
| chr1 | 78463647 | 78463677 | chr1 | 78511466 | 78512354 | chr1 | 78957292 | 78957522 |
| chr1 | 82267150 | 82267185 | chr1 | 82268573 | 82268815 | chr1 | 84944491 | 84944568 |
| chr1 | 85358752 | 85358822 | chr1 | 85463349 | 85463378 | chr1 | 85725508 | 85725537 |
| chr1 | 85725639 | 85725668 | chr1 | 86296345 | 86296375 | chr1 | 86621660 | 86622127 |
| chr1 | 86622526 | 85622551 | chr1 | 86860608 | 86860949 | chr1 | 87617774 | 87617807 |
| chr1 | 89394066 | 89394163 | chr1 | 90099997 | 90100084 | chr1 | 90309292 | 90309490 |
| chr1 | 91172012 | 91172677 | chr1 | 91177941 | 91178207 | chr1 | 91180075 | 91180306 |
| chr1 | 91181932 | 91182132 | chr1 | 91182338 | 91183195 | chr1 | 91183251 | 91183610 |
| chr1 | 91183951 | 91183986 | chr1 | 91184423 | 91184672 | chr1 | 91185190 | 91185308 |
| chr1 | 91185348 | 91185707 | chr1 | 91188983 | 91189383 | chr1 | 91189688 | 91190380 |
| chr1 | 91190869 | 91190948 | chr1 | 91190985 | 91191234 | chr1 | 91191290 | 91191310 |
| chr1 | 91192274 | 91192576 | chr1 | 91194414 | 91194569 | chr1 | 91195117 | 91195390 |
| chr1 | 91195879 | 91196194 | chr1 | 91196226 | 91196502 | chr1 | 91316261 | 91316313 |
| chr1 | 91316627 | 91316682 | chr1 | 91869988 | 91870018 | chr1 | 92948324 | 92948597 |
| chr1 | 92948841 | 92948976 | chr1 | 92952145 | 92952655 | chr1 | 94147641 | 94147670 |
| chr1 | 94147816 | 94147845 | chr1 | 94343568 | 94343744 | chr1 | 94911234 | 94911328 |
| chr1 | 95006795 | 95006902 | chr1 | 97185262 | 97185609 | chr1 | 98510791 | 98511335 |
| chr1 | 98511628 | 98511922 | chr1 | 98514225 | 98514255 | chr1 | 98515142 | 98515191 |
| chr1 | 98515256 | 98515319 | chr1 | 98519023 | 98519675 | chr1 | 99469682 | 99469696 |
| chr1 | 99469760 | 99469788 | chr1 | 99470785 | 99470847 | chr1 | 100239507 | 100239544 |
| chr1 | 100310827 | 100310979 | chr1 | 100437068 | 100437172 | chr1 | 101004456 | 101004737 |
| chr1 | 101005071 | 101005144 | chr1 | 101005360 | 101005675 | chr1 | 101702504 | 101702616 |
| chr1 | 101703612 | 101703642 | chr1 | 103574508 | 103574537 | chr1 | 107682735 | 107682977 |
| chr1 | 107683439 | 107683517 | chr1 | 107684240 | 107684439 | chr1 | 108507063 | 108507076 |
| chr1 | 108507320 | 108507375 | chr1 | 108507495 | 108507497 | chr1 | 108507717 | 108507810 |
| chr1 | 108508052 | 108508640 | chr1 | 108722798 | 108722828 | chr1 | 109203609 | 109203672 |
| chr1 | 109585463 | 109585632 | chr1 | 109595405 | 109595534 | chr1 | 109631549 | 109631682 |
| chr1 | 109644226 | 109644336 | chr1 | 110610586 | 110610897 | chr1 | 110611046 | 110611276 |
| chr1 | 110611435 | 110611513 | chr1 | 110611654 | 110611965 | chr1 | 110626684 | 110627578 |
| chr1 | 110672889 | 110673233 | chr1 | 110692973 | 110693496 | chr1 | 110693737 | 110694117 |
| chr1 | 110754003 | 110754101 | chr1 | 110754309 | 110754356 | chr1 | 110883542 | 110883965 |
| chr1 | 111097906 | 111097936 | chr1 | 111098196 | 111098316 | chr1 | 111216763 | 111216972 |
| chr1 | 111217195 | 111217891 | chr1 | 111217924 | 111217982 | chr1 | 111440961 | 111440999 |
| chr1 | 111506007 | 111506212 | chr1 | 111813546 | 111813587 | chr1 | 112084954 | 112084984 |
| chr1 | 113166315 | 113166394 | chr1 | 114428007 | 114428160 | chr1 | 114448943 | 114448990 |
| chr1 | 114695439 | 114695736 | chr1 | 114695800 | 114695943 | chr1 | 114696350 | 114696463 |
| chr1 | 114696541 | 114696712 | chr1 | 115055395 | 115055425 | chr1 | 115256514 | 115256552 |
| chr1 | 115258729 | 115258772 | chr1 | 115631867 | 115631915 | chr1 | 115632469 | 115632555 |
| chr1 | 115880184 | 115880395 | chr1 | 115880873 | 115881042 | chr1 | 116214104 | 116214318 |
| chr1 | 116371139 | 116371201 | chr1 | 116380651 | 116381287 | chr1 | 116382387 | 116382478 |
| chr1 | 117901133 | 117901264 | chr1 | 119522074 | 119522434 | chr1 | 119522839 | 119522853 |
| chr1 | 119522925 | 119522940 | chr1 | 119527237 | 119527391 | chr1 | 119527623 | 119527662 |
| chr1 | 119528653 | 119629118 | chr1 | 119529804 | 119529839 | chr1 | 119530100 | 119530148 |
| chr1 | 119530202 | 119530507 | chr1 | 119530554 | 119530725 | chr1 | 119531029 | 119531157 |
| chr1 | 119532318 | 119532320 | chr1 | 119535908 | 119536377 | chr1 | 119542322 | 119542352 |
| chr1 | 119543070 | 119543214 | chr1 | 119544182 | 119544182 | chr1 | 119548823 | 119548853 |
| chr1 | 119549058 | 119549734 | chr1 | 119549915 | 119549929 | chr1 | 119550155 | 119550278 |
| chr1 | 119550533 | 119550633 | chr1 | 119551014 | 119551269 | chr1 | 146551186 | 146551215 |
| chr1 | 150603138 | 150603170 | chr1 | 150941425 | 150941847 | chr1 | 150994849 | 150995152 |
| chr1 | 151042405 | 151042496 | chr1 | 151169248 | 151170206 | chr1 | 151253146 | 151253427 |
| chr1 | 151300888 | 151300918 | chr1 | 151362640 | 151362779 | chr1 | 151693945 | 151694351 |
| chr1 | 151812413 | 151812442 | chr1 | 152009415 | 152009510 | chr1 | 152085398 | 152085504 |
| chr1 | 152488150 | 152488197 | chr1 | 153539476 | 153539637 | chr1 | 153540096 | 153540154 |
| chr1 | 153651965 | 153652379 | chr1 | 153896746 | 153896800 | chr1 | 153937124 | 153937330 |
| chr1 | 153948791 | 153948823 | chr1 | 154127987 | 154128016 | chr1 | 154156468 | 154156717 |
| chr1 | 154298320 | 154298557 | chr1 | 154475372 | 154475531 | chr1 | 154491036 | 154491066 |
| chr1 | 154516810 | 154516845 | chr1 | 155043331 | 155043657 | chr1 | 155161778 | 155162033 |
| chr1 | 155164415 | 155164455 | chr1 | 155283218 | 155283248 | chr1 | 155578375 | 155578921 |
| chr1 | 155617837 | 155617962 | chr1 | 155653788 | 155653868 | chr1 | 155826248 | 155826336 |
| chr1 | 155874151 | 155874300 | chr1 | 155874508 | 155874546 | chr1 | 155954282 | 155954396 |
| chr1 | 156010377 | 156010548 | chr1 | 156017591 | 156017683 | chr1 | 156030286 | 156030621 |
| chr1 | 156215329 | 156215359 | chr1 | 156215607 | 156215805 | chr1 | 156357993 | 156358508 |
| chr1 | 156390135 | 156390698 | chr1 | 156405635 | 156406070 | chr1 | 156406105 | 156406431 |
| chr1 | 156432124 | 156432637 | chr1 | 156594974 | 156595021 | chr1 | 156611889 | 156611943 |
| chr1 | 156611994 | 156612119 | chr1 | 156626589 | 156626658 | chr1 | 156626891 | 156627018 |
| chr1 | 156646278 | 156646307 | chr1 | 156646593 | 156646596 | chr1 | 156646635 | 156646647 |
| chr1 | 156814933 | 156814952 | chr1 | 156815031 | 156815146 | chr1 | 156815445 | 156815745 |
| chr1 | 156830269 | 156830348 | chr1 | 156838167 | 156838320 | chr1 | 156863107 | 156863331 |

TABLE 12-continued

| chr | start | end | chr | start | end | chr | start | end |
|---|---|---|---|---|---|---|---|---|
| chr1 | 156863662 | 156863724 | chr1 | 157247347 | 157247388 | chr1 | 157458909 | 157458961 |
| chr1 | 157895413 | 157895443 | chr1 | 158205040 | 158205070 | chr1 | 158245556 | 158245586 |
| chr1 | 158295829 | 158295935 | chr1 | 158318949 | 158318979 | chr1 | 158591699 | 158591947 |
| chr1 | 158669704 | 158669882 | chr1 | 158672648 | 158672678 | chr1 | 158687415 | 158687550 |
| chr1 | 158748648 | 158748771 | chr1 | 158760197 | 158760235 | chr1 | 158778060 | 158778152 |
| chr1 | 158815136 | 158815295 | chr1 | 158907635 | 158907692 | chr1 | 159140357 | 159140386 |
| chr1 | 159158348 | 159158368 | chr1 | 159158472 | 159158511 | chr1 | 159187279 | 159187429 |
| chr1 | 159258862 | 159258891 | chr1 | 159337419 | 159337615 | chr1 | 159409192 | 159409221 |
| chr1 | 160451043 | 160451202 | chr1 | 160693934 | 160694102 | chr1 | 160880758 | 160880788 |
| chr1 | 160986299 | 160986385 | chr1 | 160992336 | 160992587 | chr1 | 161007587 | 161007746 |
| chr1 | 161013554 | 161013677 | chr1 | 161086730 | 161086813 | chr1 | 161122645 | 161122778 |
| chr1 | 161228659 | 161228891 | chr1 | 161275564 | 161275578 | chr1 | 161275640 | 161276026 |
| chr1 | 161359069 | 161359099 | chr1 | 161367577 | 161367701 | chr1 | 161368283 | 161368507 |
| chr1 | 161368993 | 161369405 | chr1 | 161369859 | 161369945 | chr1 | 161442441 | 161442471 |
| chr1 | 161466301 | 161466347 | chr1 | 161471652 | 161471779 | chr1 | 161591472 | 161591546 |
| chr1 | 162427088 | 162427153 | chr1 | 162724401 | 162724430 | chr1 | 162729615 | 162729686 |
| chr1 | 162748392 | 162748421 | chr1 | 162792306 | 162792533 | chr1 | 163393034 | 163393064 |
| chr1 | 164290615 | 164290671 | chr1 | 164428741 | 164428831 | chr1 | 164518220 | 164518270 |
| chr1 | 164730649 | 164730796 | chr1 | 165086988 | 165087027 | chr1 | 165205079 | 165205146 |
| chr1 | 165321747 | 165321786 | chr1 | 165323151 | 165323181 | chr1 | 165324196 | 165324249 |
| chr1 | 165324305 | 165324357 | chr1 | 165324488 | 165324668 | chr1 | 165325108 | 165325356 |
| chr1 | 165325395 | 165325521 | chr1 | 165325896 | 165325950 | chr1 | 165326204 | 165326204 |
| chr1 | 165326297 | 165326469 | chr1 | 165414191 | 165414272 | chr1 | 166134247 | 166134306 |
| chr1 | 166134728 | 166134796 | chr1 | 166135193 | 166135281 | chr1 | 166853563 | 166853592 |
| chr1 | 166890292 | 166890436 | chr1 | 166916866 | 166916920 | chr1 | 166916937 | 166916949 |
| chr1 | 167090617 | 167090757 | chr1 | 167599179 | 167599330 | chr1 | 167599616 | 167599844 |
| chr1 | 167823339 | 167823461 | chr1 | 169355697 | 169355727 | chr1 | 169396376 | 169396688 |
| chr1 | 169396731 | 169396923 | chr1 | 169838016 | 169838187 | chr1 | 169930112 | 169930305 |
| chr1 | 170063947 | 170064218 | chr1 | 170629540 | 170629569 | chr1 | 170629999 | 170630029 |
| chr1 | 170630456 | 170630810 | chr1 | 170631084 | 170631163 | chr1 | 170631477 | 170631559 |
| chr1 | 170633607 | 170633637 | chr1 | 170637666 | 170637796 | chr1 | 170640517 | 170640624 |
| chr1 | 170640665 | 170640691 | chr1 | 171625525 | 171625561 | chr1 | 171665240 | 171665330 |
| chr1 | 171810200 | 171810972 | chr1 | 173638647 | 173639085 | chr1 | 175346381 | 175346551 |
| chr1 | 175388664 | 175388700 | chr1 | 177133721 | 177133814 | chr1 | 177140105 | 177140173 |
| chr1 | 177140305 | 177140714 | chr1 | 177150773 | 177150803 | chr1 | 178063112 | 178063150 |
| chr1 | 179046338 | 179046385 | chr1 | 179262226 | 179262256 | chr1 | 179544967 | 179545098 |
| chr1 | 179712164 | 179712338 | chr1 | 179712411 | 179712553 | chr1 | 179712568 | 179712733 |
| chr1 | 179712831 | 179713174 | chr1 | 180198061 | 180198209 | chr1 | 180202649 | 180203016 |
| chr1 | 180203413 | 180203607 | chr1 | 180203634 | 180204619 | chr1 | 180204898 | 180204924 |
| chr1 | 180235730 | 180235760 | chr1 | 180882576 | 180882695 | chr1 | 180919682 | 180919718 |
| chr1 | 180925271 | 180925402 | chr1 | 181014878 | 181014997 | chr1 | 181287679 | 181287757 |
| chr1 | 181288014 | 181288188 | chr1 | 181451407 | 181452120 | chr1 | 181452871 | 181452967 |
| chr1 | 181454873 | 181454912 | chr1 | 181455183 | 181455263 | chr1 | 182584048 | 182584339 |
| chr1 | 182584404 | 182584613 | chr1 | 182807578 | 182807742 | chr1 | 182862133 | 182862328 |
| chr1 | 182921839 | 182921868 | chr1 | 183129382 | 183129737 | chr1 | 183386150 | 183386288 |
| chr1 | 183386599 | 183386626 | chr1 | 183386947 | 183386964 | chr1 | 183387266 | 183387319 |
| chr1 | 183462761 | 183463024 | chr1 | 183627506 | 183627539 | chr1 | 183774244 | 183774363 |
| chr1 | 184005701 | 184005814 | chr1 | 184970783 | 184970847 | chr1 | 185073818 | 185073966 |
| chr1 | 185076172 | 185076270 | chr1 | 185336061 | 185336095 | chr1 | 186570930 | 186571030 |
| chr1 | 190444855 | 190444885 | chr1 | 190445181 | 190445276 | chr1 | 190447389 | 190447519 |
| chr1 | 195732322 | 195732539 | chr1 | 196577628 | 196577858 | chr1 | 196578101 | 196578150 |
| chr1 | 197771547 | 197771893 | chr1 | 197879400 | 197879660 | chr1 | 197879717 | 197880156 |
| chr1 | 197882140 | 197882201 | chr1 | 197882453 | 197882611 | chr1 | 197887052 | 197887066 |
| chr1 | 197887147 | 197887456 | chr1 | 197887707 | 197887741 | chr1 | 197888052 | 197888121 |
| chr1 | 197888181 | 197888319 | chr1 | 197888643 | 197889286 | chr1 | 198124799 | 198124932 |
| chr1 | 200009357 | 200009450 | chr1 | 200009750 | 200010114 | chr1 | 200011323 | 200012227 |
| chr1 | 200478843 | 200478932 | chr1 | 200591054 | 200691225 | chr1 | 201368582 | 201368727 |
| chr1 | 201476501 | 201476619 | chr1 | 201983113 | 201983200 | chr1 | 202081571 | 202081641 |
| chr1 | 202081728 | 202081804 | chr1 | 202183371 | 202183401 | chr1 | 202311820 | 202311901 |
| chr1 | 202531939 | 202532087 | chr1 | 202679215 | 202679518 | chr1 | 202856858 | 202856937 |
| chr1 | 203298307 | 203298710 | chr1 | 203429564 | 203429594 | chr1 | 203681332 | 203681362 |
| chr1 | 204333609 | 204333668 | chr1 | 204478284 | 204478427 | chr1 | 204499813 | 204499842 |
| chr1 | 204524704 | 204524744 | chr1 | 204531203 | 204531757 | chr1 | 204653561 | 204653595 |
| chr1 | 204653793 | 204653807 | chr1 | 205312596 | 205312911 | chr1 | 205424654 | 205424957 |
| chr1 | 205537663 | 205537772 | chr1 | 206950282 | 206950328 | chr1 | 207200870 | 207200962 |
| chr1 | 207227318 | 207227556 | chr1 | 207669496 | 207669787 | chr1 | 207669829 | 207620060 |
| chr1 | 207794579 | 207794609 | chr1 | 207818394 | 207818396 | chr1 | 207818434 | 207818493 |
| chr1 | 207833206 | 207833370 | chr1 | 208084289 | 208084488 | chr1 | 209164972 | 209165091 |
| chr1 | 209381132 | 209381165 | chr1 | 209604382 | 209604597 | chr1 | 209605386 | 209605415 |
| chr1 | 209849170 | 209849199 | chr1 | 209849430 | 209849459 | chr1 | 210111146 | 210111176 |
| chr1 | 210111388 | 210111421 | chr1 | 210111797 | 210111922 | chr1 | 210112037 | 210112140 |
| chr1 | 211847706 | 211847787 | chr1 | 212484610 | 212484816 | chr1 | 212963883 | 212964151 |
| chr1 | 213123871 | 213123979 | chr1 | 213124669 | 213124910 | chr1 | 213189937 | 213190065 |
| chr1 | 214156419 | 214156928 | chr1 | 214158838 | 214158910 | chr1 | 214160107 | 214160184 |
| chr1 | 214360675 | 214360858 | chr1 | 214360927 | 214360968 | chr1 | 214724531 | 214724561 |
| chr1 | 215255094 | 215255799 | chr1 | 216897216 | 216897307 | chr1 | 217307385 | 217308274 |
| chr1 | 217309007 | 217309105 | chr1 | 217309764 | 217309816 | chr1 | 217311265 | 217311839 |
| chr1 | 217313042 | 217313042 | chr1 | 217313069 | 217313747 | chr1 | 217805158 | 217805395 |

TABLE 12-continued

| chr | start | end | chr | start | end | chr | start | end |
|---|---|---|---|---|---|---|---|---|
| chr1 | 218520096 | 218520291 | chr1 | 218520310 | 218520399 | chr1 | 218520775 | 218520805 |
| chr1 | 219346992 | 219347035 | chr1 | 219347394 | 219347435 | chr1 | 220101145 | 220101210 |
| chr1 | 220101371 | 220101385 | chr1 | 220101683 | 220101712 | chr1 | 220132075 | 220132111 |
| chr1 | 220636466 | 220636510 | chr1 | 220700814 | 220700897 | chr1 | 220896508 | 220896568 |
| chr1 | 221052038 | 221052492 | chr1 | 221053610 | 221053862 | chr1 | 221067506 | 221067688 |
| chr1 | 221068156 | 221068185 | chr1 | 221068793 | 221069150 | chr1 | 221510339 | 221510368 |
| chr1 | 221737191 | 221737220 | chr1 | 223302825 | 223302890 | chr1 | 223538344 | 223538641 |
| chr1 | 223894714 | 223894752 | chr1 | 223899470 | 223899500 | chr1 | 223936633 | 223936752 |
| chr1 | 223936996 | 223937057 | chr1 | 224267615 | 224267662 | chr1 | 224363560 | 224363589 |
| chr1 | 224400490 | 224400524 | chr1 | 224493975 | 224494083 | chr1 | 224528814 | 224528844 |
| chr1 | 224803717 | 224803751 | chr1 | 224804097 | 224804295 | chr1 | 224804396 | 224804686 |
| chr1 | 224804847 | 224804910 | chr1 | 224805198 | 224805751 | chr1 | 225118306 | 225118474 |
| chr1 | 225908076 | 225908184 | chr1 | 226265194 | 226265257 | chr1 | 226384322 | 226384440 |
| chr1 | 226411247 | 226411273 | chr1 | 226411700 | 226411832 | chr1 | 226814346 | 226814408 |
| chr1 | 226925067 | 226925195 | chr1 | 226997660 | 226997719 | chr1 | 227729830 | 227730075 |
| chr1 | 227748700 | 227748733 | chr1 | 228195377 | 228196349 | chr1 | 228201221 | 228201251 |
| chr1 | 228247998 | 228248027 | chr1 | 228248302 | 228248332 | chr1 | 228345999 | 228346195 |
| chr1 | 228461158 | 228461197 | chr1 | 228463311 | 228463706 | chr1 | 228528840 | 228529016 |
| chr1 | 228558699 | 228559238 | chr1 | 228566622 | 228566752 | chr1 | 228604124 | 228604254 |
| chr1 | 228633990 | 228634261 | chr1 | 228645140 | 228645243 | chr1 | 228645306 | 228645734 |
| chr1 | 228646032 | 228646238 | chr1 | 228651432 | 228651626 | chr1 | 228651879 | 228651901 |
| chr1 | 228652207 | 228652452 | chr1 | 228652509 | 228652629 | chr1 | 228693629 | 228693767 |
| chr1 | 228871865 | 228872003 | chr1 | 229476753 | 229476879 | chr1 | 229542838 | 229542952 |
| chr1 | 229543553 | 229543603 | chr1 | 229566753 | 229567276 | chr1 | 229567370 | 229567992 |
| chr1 | 229568158 | 229668204 | chr1 | 229569810 | 229569852 | chr1 | 230404217 | 230404263 |
| chr1 | 230561779 | 230561824 | chr1 | 231149928 | 231150098 | chr1 | 231297103 | 231297221 |
| chr1 | 231298595 | 231298707 | chr1 | 231475814 | 231476081 | chr1 | 232765195 | 232765301 |
| chr1 | 233465473 | 233465503 | chr1 | 233750082 | 233750302 | chr1 | 234040247 | 234040319 |
| chr1 | 234040886 | 234040973 | chr1 | 234041416 | 234041624 | chr1 | 234349988 | 234350100 |
| chr1 | 234445373 | 234445403 | chr1 | 234620866 | 234620979 | chr1 | 234798171 | 234798201 |
| chr1 | 234839889 | 234840058 | chr1 | 234844955 | 234845079 | chr1 | 234845467 | 234845497 |
| chr1 | 235266920 | 235266950 | chr1 | 235665663 | 235665736 | chr1 | 235669296 | 235669398 |
| chr1 | 235813781 | 235813796 | chr1 | 235814010 | 235814202 | chr1 | 235814447 | 235814476 |
| chr1 | 236227637 | 236227743 | chr1 | 236227770 | 236227920 | chr1 | 236228022 | 236228096 |
| chr1 | 236228582 | 236228623 | chr1 | 236228706 | 236228789 | chr1 | 236559176 | 236559206 |
| chr1 | 236559257 | 236559271 | chr1 | 236849457 | 236849505 | chr1 | 237205159 | 237205188 |
| chr1 | 237206102 | 237206265 | chr1 | 237206512 | 237206735 | chr1 | 237970760 | 237970826 |
| chr1 | 238024448 | 238024477 | chr1 | 239550594 | 239551193 | chr1 | 240118848 | 240118973 |
| chr1 | 240161123 | 240161380 | chr1 | 240254944 | 240255011 | chr1 | 240255361 | 240255500 |
| chr1 | 240255819 | 240256158 | chr1 | 240256663 | 240256780 | chr1 | 240775425 | 240775455 |
| chr1 | 241052096 | 241052126 | chr1 | 241052360 | 241052419 | chr1 | 241520296 | 241520345 |
| chr1 | 241520583 | 241520612 | chr1 | 241587034 | 241587113 | chr1 | 241587587 | 241587797 |
| chr1 | 241912749 | 241912778 | chr1 | 242686734 | 242687688 | chr1 | 242688184 | 242688243 |
| chr1 | 242688477 | 242688695 | chr1 | 243646610 | 243646673 | chr1 | 243859000 | 243859029 |
| chr1 | 243921295 | 243921330 | chr1 | 244014221 | 244014376 | chr1 | 244080672 | 244080702 |
| chr1 | 244080963 | 244081061 | chr1 | 244081078 | 244081203 | chr1 | 244115072 | 244115212 |
| chr1 | 244893214 | 244893315 | chr1 | 245032517 | 045032603 | chr1 | 245135753 | 245136064 |
| chr1 | 245494495 | 245494578 | chr1 | 245849914 | 245849944 | chr1 | 246198078 | 246198203 |
| chr1 | 246330309 | 246330409 | chr1 | 246488175 | 246488336 | chr1 | 246654652 | 246654851 |
| chr1 | 247284422 | 247284452 | chr1 | 247496038 | 247496057 | chr1 | 247608784 | 247608814 |
| chr1 | 247684856 | 247684929 | chr1 | 247910678 | 247910780 | chr1 | 248002278 | 248002437 |
| chr1 | 248020516 | 248020630 | chr1 | 248020957 | 248021349 | chr1 | 248028015 | 248028202 |
| chr1 | 248074729 | 248074927 | chr1 | 248099751 | 248099809 | chr1 | 248198552 | 248198721 |
| chr1 | 248328701 | 248328841 | chr1 | 248691575 | 248691616 | chr1 | 248860898 | 248861046 |
| chr1 | 249121600 | 249121704 | chr2 | 46214 | 46450 | chr2 | 142427 | 142468 |
| chr2 | 264163 | 264204 | chr2 | 287580 | 287641 | chr2 | 288404 | 288470 |
| chr2 | 468424 | 468672 | chr2 | 496228 | 496380 | chr2 | 602657 | 602687 |
| chr2 | 720836 | 720894 | chr2 | 875961 | 875991 | chr2 | 945913 | 946000 |
| chr2 | 946208 | 946217 | chr2 | 946526 | 946566 | chr2 | 946917 | 947043 |
| chr2 | 947127 | 947159 | chr2 | 1652837 | 1653230 | chr2 | 1670168 | 1670216 |
| chr2 | 1746614 | 1747032 | chr2 | 1747670 | 1748007 | chr2 | 1748397 | 1748890 |
| chr2 | 2321773 | 2321802 | chr2 | 2336413 | 2336442 | chr2 | 2646900 | 2646930 |
| chr2 | 2672620 | 2672732 | chr2 | 2844720 | 2844750 | chr2 | 2893165 | 2893195 |
| chr2 | 3259989 | 3260103 | chr2 | 4019911 | 4020036 | chr2 | 4050752 | 4050781 |
| chr2 | 5831178 | 5831204 | chr2 | 5831238 | 5831324 | chr2 | 5831789 | 5831819 |
| chr2 | 5833283 | 5833432 | chr2 | 5833500 | 5833639 | chr2 | 5833735 | 5834028 |
| chr2 | 5836085 | 5836253 | chr2 | 5836548 | 5836574 | chr2 | 5836622 | 5836744 |
| chr2 | 5836828 | 5836991 | chr2 | 5837353 | 5837414 | chr2 | 5866098 | 5866211 |
| chr2 | 7062891 | 7062959 | chr2 | 7164467 | 7164788 | chr2 | 7236859 | 7236974 |
| chr2 | 7571577 | 7571747 | chr2 | 8735932 | 8736064 | chr2 | 8835493 | 8835523 |
| chr2 | 9090685 | 9090760 | chr2 | 9134404 | 9134493 | chr2 | 9192356 | 9192402 |
| chr2 | 9289969 | 9290114 | chr2 | 9960734 | 9960764 | chr2 | 10115730 | 10115772 |
| chr2 | 10152798 | 10153325 | chr2 | 10154266 | 10154564 | chr2 | 10154930 | 10155298 |
| chr2 | 10156116 | 10156389 | chr2 | 10182827 | 10182904 | chr2 | 10369155 | 10369242 |
| chr2 | 10408398 | 10408459 | chr2 | 10688874 | 10688904 | chr2 | 11052517 | 11052559 |
| chr2 | 11142174 | 11142315 | chr2 | 11356651 | 11356762 | chr2 | 11672746 | 11672775 |
| chr2 | 11809957 | 11810115 | chr2 | 11903450 | 11903480 | chr2 | 12246114 | 12246217 |
| chr2 | 12297534 | 12297564 | chr2 | 12858452 | 12858618 | chr2 | 13557899 | 13558057 |

TABLE 12-continued

| chr | start | end | chr | start | end | chr | start | end |
|---|---|---|---|---|---|---|---|---|
| chr2 | 14772761 | 14772823 | chr2 | 14774281 | 14774567 | chr2 | 15579989 | 15580019 |
| chr2 | 17719688 | 17719812 | chr2 | 18059035 | 18059085 | chr2 | 18059781 | 18059841 |
| chr2 | 19550214 | 19550244 | chr2 | 19551322 | 19551366 | chr2 | 19556318 | 19556672 |
| chr2 | 19557068 | 19557098 | chr2 | 19557685 | 19557727 | chr2 | 19558832 | 19558893 |
| chr2 | 19561131 | 19561316 | chr2 | 19561524 | 19561685 | chr2 | 19563358 | 19563433 |
| chr2 | 20068798 | 20068885 | chr2 | 20442433 | 20442498 | chr2 | 20641988 | 20642081 |
| chr2 | 20642541 | 20642648 | chr2 | 20710145 | 20710324 | chr2 | 20865636 | 20865927 |
| chr2 | 22404181 | 22404227 | chr2 | 24318290 | 24318357 | chr2 | 25029252 | 25029300 |
| chr2 | 25374762 | 25374804 | chr2 | 25390994 | 25391212 | chr2 | 25391684 | 25391725 |
| chr2 | 25438821 | 25438871 | chr2 | 25439139 | 25439465 | chr2 | 25439727 | 25439915 |
| chr2 | 25600736 | 25600804 | chr2 | 25928094 | 25928166 | chr2 | 26372967 | 26372997 |
| chr2 | 26396447 | 26395555 | chr2 | 26402030 | 26402060 | chr2 | 26407744 | 26407921 |
| chr2 | 26521972 | 26522221 | chr2 | 26915763 | 26916066 | chr2 | 26916089 | 26916259 |
| chr2 | 27070324 | 27070414 | chr2 | 27071240 | 27071346 | chr2 | 27072492 | 27072534 |
| chr2 | 27072822 | 27072989 | chr2 | 27271699 | 27272218 | chr2 | 27356168 | 27356198 |
| chr2 | 27433532 | 27433601 | chr2 | 27543012 | 27543074 | chr2 | 27578243 | 27578396 |
| chr2 | 27648172 | 27648294 | chr2 | 27665125 | 27665154 | chr2 | 27665506 | 27665711 |
| chr2 | 27764046 | 27764168 | chr2 | 27887525 | 27887555 | chr2 | 29033336 | 29033697 |
| chr2 | 29091592 | 29091838 | chr2 | 29338159 | 29338747 | chr2 | 29338810 | 29338969 |
| chr2 | 29420483 | 29420512 | chr2 | 29432640 | 29432696 | chr2 | 29436844 | 29436888 |
| chr2 | 29443573 | 29443710 | chr2 | 29445198 | 29445482 | chr2 | 29446361 | 29446396 |
| chr2 | 30143304 | 30143322 | chr2 | 30143383 | 30143492 | chr2 | 30144041 | 30144150 |
| chr2 | 30144175 | 30144411 | chr2 | 30368444 | 30368586 | chr2 | 30453785 | 30453941 |
| chr2 | 30514753 | 30514783 | chr2 | 31360306 | 31360589 | chr2 | 31360631 | 31360755 |
| chr2 | 31360804 | 31360831 | chr2 | 31361089 | 31361118 | chr2 | 31361356 | 31361385 |
| chr2 | 31456682 | 31457039 | chr2 | 32275196 | 32275303 | chr2 | 32504169 | 32504378 |
| chr2 | 32580386 | 32580476 | chr2 | 38302370 | 38302876 | chr2 | 38365525 | 38365748 |
| chr2 | 38551124 | 38551390 | chr2 | 38594819 | 38594874 | chr2 | 38727561 | 38727707 |
| chr2 | 38762382 | 38762412 | chr2 | 38953573 | 38953603 | chr2 | 38983213 | 38983333 |
| chr2 | 39187218 | 39187232 | chr2 | 39187544 | 39187722 | chr2 | 39893090 | 39893501 |
| chr2 | 39893972 | 39894059 | chr2 | 40678603 | 40679604 | chr2 | 41789816 | 41789853 |
| chr2 | 42274595 | 42274633 | chr2 | 42329431 | 42329444 | chr2 | 42329494 | 42329666 |
| chr2 | 42720262 | 42720446 | chr2 | 43019599 | 43019868 | chr2 | 43388330 | 43388529 |
| chr2 | 43451909 | 43452327 | chr2 | 43824133 | 43824353 | chr2 | 44226958 | 44226988 |
| chr2 | 44227193 | 44227223 | chr2 | 44497708 | 44497875 | chr2 | 44809187 | 44809217 |
| chr2 | 45028988 | 45029058 | chr2 | 45029184 | 45029371 | chr2 | 45029682 | 45029712 |
| chr2 | 45155125 | 45155210 | chr2 | 45155356 | 45156811 | chr2 | 45156833 | 45157711 |
| chr2 | 45159956 | 45160267 | chr2 | 45160596 | 45160634 | chr2 | 45161663 | 45162112 |
| chr2 | 45162394 | 45162481 | chr2 | 45162751 | 45162913 | chr2 | 45164663 | 45164693 |
| chr2 | 45165564 | 45165594 | chr2 | 45168803 | 45168833 | chr2 | 45169446 | 45170029 |
| chr2 | 45171385 | 45171563 | chr2 | 45171837 | 45171862 | chr2 | 45176601 | 45176768 |
| chr2 | 45179620 | 45179650 | chr2 | 45179939 | 45180203 | chr2 | 45181520 | 45181672 |
| chr2 | 45181887 | 45182001 | chr2 | 45228627 | 45228730 | chr2 | 45231320 | 45231396 |
| chr2 | 45231805 | 45232131 | chr2 | 45233385 | 45233586 | chr2 | 45235594 | 45235925 |
| chr2 | 45237673 | 45237795 | chr2 | 45240548 | 45240630 | chr2 | 45240764 | 45240784 |
| chr2 | 45241136 | 45241168 | chr2 | 45395854 | 45395920 | chr2 | 45396315 | 45396451 |
| chr2 | 45396688 | 45396995 | chr2 | 46526302 | 46526448 | chr2 | 47193930 | 47194136 |
| chr2 | 47200591 | 47200621 | chr2 | 47249725 | 47249848 | chr2 | 47597455 | 47598620 |
| chr2 | 47599589 | 47599753 | chr2 | 47748140 | 47748494 | chr2 | 47797043 | 47797818 |
| chr2 | 47798180 | 47798663 | chr2 | 47798954 | 47799032 | chr2 | 48629615 | 48629685 |
| chr2 | 48636504 | 48636669 | chr2 | 48648878 | 48648940 | chr2 | 48982582 | 48982700 |
| chr2 | 48982754 | 48982865 | chr2 | 50573595 | 50573638 | chr2 | 50573692 | 50573825 |
| chr2 | 50574121 | 50574355 | chr2 | 50574402 | 50574684 | chr2 | 50574739 | 50574859 |
| chr2 | 54322431 | 54322576 | chr2 | 55289011 | 55289296 | chr2 | 55612770 | 55612800 |
| chr2 | 55669261 | 55669454 | chr2 | 56149836 | 56149866 | chr2 | 56150729 | 56151193 |
| chr2 | 56410817 | 56410996 | chr2 | 56411691 | 56411733 | chr2 | 58552519 | 58552689 |
| chr2 | 58656049 | 58656125 | chr2 | 59400384 | 59400424 | chr2 | 60416280 | 60416494 |
| chr2 | 60706759 | 60706804 | chr2 | 60796587 | 60796646 | chr2 | 60797137 | 60792281 |
| chr2 | 61135032 | 61135137 | chr2 | 61232163 | 61232232 | chr2 | 61242732 | 61242802 |
| chr2 | 61395039 | 61395069 | chr2 | 61556203 | 61556239 | chr2 | 61656393 | 61656423 |
| chr2 | 61992076 | 61992289 | chr2 | 52798343 | 62798386 | chr2 | 63278962 | 63278992 |
| chr2 | 63280952 | 63281651 | chr2 | 63282716 | 63282786 | chr2 | 63283014 | 63283027 |
| chr2 | 63283952 | 63284146 | chr2 | 63284777 | 63284811 | chr2 | 63285081 | 63286047 |
| chr2 | 63286359 | 63286584 | chr2 | 63286694 | 63286747 | chr2 | 63287083 | 63287368 |
| chr2 | 65251310 | 65251340 | chr2 | 65779892 | 65779983 | chr2 | 66652863 | 66652963 |
| chr2 | 66653238 | 66653496 | chr2 | 66653764 | 66653914 | chr2 | 66660650 | 66660888 |
| chr2 | 66662749 | 66662824 | chr2 | 66808525 | 66808633 | chr2 | 66808727 | 66809361 |
| chr2 | 67525453 | 67625770 | chr2 | 67626102 | 67626257 | chr2 | 68287707 | 68287799 |
| chr2 | 68546324 | 68546516 | chr2 | 68546553 | 68546892 | chr2 | 68559261 | 68559365 |
| chr2 | 68672853 | 68672938 | chr2 | 69027024 | 69027053 | chr2 | 69975443 | 69975523 |
| chr2 | 70058262 | 70058292 | chr2 | 70367670 | 70362710 | chr2 | 70418528 | 70418627 |
| chr2 | 70427556 | 70427646 | chr2 | 70430997 | 70431160 | chr2 | 71355019 | 71355117 |
| chr2 | 71355768 | 71355961 | chr2 | 71503790 | 71503823 | chr2 | 71504103 | 71504148 |
| chr2 | 71680833 | 71680863 | chr2 | 71693374 | 71693593 | chr2 | 72374375 | 72374432 |
| chr2 | 72374714 | 72374765 | chr2 | 73145640 | 73145694 | chr2 | 73145924 | 73146021 |
| chr2 | 73147324 | 73147522 | chr2 | 73147967 | 73148066 | chr2 | 73148175 | 73148243 |
| chr2 | 73160924 | 73150954 | chr2 | 73151187 | 73161831 | chr2 | 73152740 | 73152754 |
| chr2 | 73416356 | 73416535 | chr2 | 73429523 | 73429614 | chr2 | 73429977 | 73430069 |

TABLE 12-continued

| chr | start | end | chr | start | end | chr | start | end |
|---|---|---|---|---|---|---|---|---|
| chr2 | 73430322 | 73430372 | chr2 | 73430443 | 73430743 | chr2 | 73440205 | 73440293 |
| chr2 | 73518448 | 73518919 | chr2 | 73519579 | 73519841 | chr2 | 74010528 | 74010773 |
| chr2 | 74153198 | 74153227 | chr2 | 74350410 | 74350497 | chr2 | 74426185 | 74426214 |
| chr2 | 74454074 | 74454261 | chr2 | 74647864 | 74648007 | chr2 | 74679047 | 74679123 |
| chr2 | 74726744 | 74726774 | chr2 | 74740852 | 74741387 | chr2 | 74741835 | 74741844 |
| chr2 | 74741873 | 74741955 | chr2 | 74742325 | 74742647 | chr2 | 74742694 | 74743144 |
| chr2 | 74782081 | 74782087 | chr2 | 74782219 | 74782271 | chr2 | 74874865 | 74874903 |
| chr2 | 75427040 | 75427114 | chr2 | 75427369 | 75427399 | chr2 | 75427930 | 75428177 |
| chr2 | 75720510 | 75720541 | chr2 | 79347459 | 79347546 | chr2 | 80529378 | 80529443 |
| chr2 | 80529662 | 80529908 | chr2 | 80529986 | 80530022 | chr2 | 80530505 | 80530558 |
| chr2 | 80531725 | 80531755 | chr2 | 80549585 | 80549745 | chr2 | 85107454 | 85107538 |
| chr2 | 85361467 | 85361528 | chr2 | 85838101 | 85838299 | chr2 | 86191145 | 86191309 |
| chr2 | 86263223 | 86263270 | chr2 | 86423330 | 86423592 | chr2 | 86783725 | 86783755 |
| chr2 | 86791221 | 86791251 | chr2 | 87016579 | 87016636 | chr2 | 87017796 | 87018396 |
| chr2 | 87036611 | 87036640 | chr2 | 88469312 | 88469483 | chr2 | 88751281 | 88751419 |
| chr2 | 88751461 | 88751800 | chr2 | 88752055 | 88752285 | chr2 | 88752603 | 88752785 |
| chr2 | 88990189 | 88990264 | chr2 | 89064806 | 89064975 | chr2 | 89065129 | 89065278 |
| chr2 | 89252535 | 89252679 | chr2 | 95663969 | 95664014 | chr2 | 95690747 | 95690793 |
| chr2 | 95691036 | 95691269 | chr2 | 95691530 | 95691769 | chr2 | 95691994 | 95692480 |
| chr2 | 95941678 | 95941812 | chr2 | 96070057 | 96070165 | chr2 | 96974485 | 96974516 |
| chr2 | 96990898 | 96991316 | chr2 | 97126702 | 97126832 | chr2 | 97193252 | 97193626 |
| chr2 | 97427515 | 97428093 | chr2 | 98581819 | 98581849 | chr2 | 98703323 | 98703475 |
| chr2 | 98703675 | 98703736 | chr2 | 98962898 | 98962900 | chr2 | 98963329 | 98963999 |
| chr2 | 98963869 | 98964200 | chr2 | 98964596 | 98964645 | chr2 | 99439369 | 99439507 |
| chr2 | 99553391 | 99553656 | chr2 | 99796259 | 99796330 | chr2 | 99798646 | 99799153 |
| chr2 | 100618451 | 100618480 | chr2 | 100937836 | 100938209 | chr2 | 100938330 | 100938544 |
| chr2 | 100938575 | 100938809 | chr2 | 100938985 | 100939155 | chr2 | 101009832 | 101009927 |
| chr2 | 101034242 | 101034293 | chr2 | 101186368 | 101186458 | chr2 | 101436632 | 101436708 |
| chr2 | 101666893 | 101667004 | chr2 | 101834977 | 101835057 | chr2 | 102091180 | 102091335 |
| chr2 | 103236165 | 103236292 | chr2 | 105459081 | 105459151 | chr2 | 105459908 | 105460599 |
| chr2 | 105460921 | 105460951 | chr2 | 105461187 | 105461243 | chr2 | 105461564 | 105461617 |
| chr2 | 105461700 | 105461896 | chr2 | 105462165 | 105462222 | chr2 | 105468791 | 105468908 |
| chr2 | 105469645 | 105469856 | chr2 | 105469881 | 105470091 | chr2 | 105470350 | 105470840 |
| chr2 | 105472231 | 105472425 | chr2 | 105472713 | 105472845 | chr2 | 105473248 | 105473553 |
| chr2 | 105478762 | 105479089 | chr2 | 105483655 | 105483719 | chr2 | 105484450 | 105484522 |
| chr2 | 105488437 | 105488496 | chr2 | 105760981 | 105761037 | chr2 | 105937344 | 105937498 |
| chr2 | 106060615 | 106060792 | chr2 | 106681733 | 106681767 | chr2 | 106682012 | 106682098 |
| chr2 | 106730223 | 106730256 | chr2 | 106959368 | 106969568 | chr2 | 106959916 | 106959988 |
| chr2 | 107103865 | 107103928 | chr2 | 107502600 | 107502729 | chr2 | 107503532 | 107503561 |
| chr2 | 107503884 | 107504018 | chr2 | 108364897 | 108364940 | chr2 | 109335133 | 109335166 |
| chr2 | 109648080 | 109648222 | chr2 | 109745989 | 109746079 | chr2 | 109746289 | 109746387 |
| chr2 | 109746463 | 109746477 | chr2 | 110015080 | 110015110 | chr2 | 110370941 | 110371219 |
| chr2 | 110873016 | 110873045 | chr2 | 111544817 | 111544997 | chr2 | 111875191 | 111875611 |
| chr2 | 112657033 | 112657092 | chr2 | 112817735 | 112817765 | chr2 | 113227024 | 113227225 |
| chr2 | 113594639 | 113594668 | chr2 | 113803960 | 113803990 | chr2 | 113931503 | 113931532 |
| chr2 | 114256978 | 114257137 | chr2 | 114261300 | 114261458 | chr2 | 114461746 | 114461879 |
| chr2 | 114470022 | 114470201 | chr2 | 114515528 | 114515618 | chr2 | 114634867 | 114634988 |
| chr2 | 115918661 | 115918892 | chr2 | 115919338 | 115919424 | chr2 | 115919831 | 115920534 |
| chr2 | 118380865 | 118380904 | chr2 | 118981161 | 118981856 | chr2 | 118981946 | 118982147 |
| chr2 | 118982254 | 118982497 | chr2 | 119067636 | 119068049 | chr2 | 119532161 | 119532255 |
| chr2 | 119566239 | 119566272 | chr2 | 119591351 | 119591465 | chr2 | 119592588 | 119592777 |
| chr2 | 119592997 | 119593567 | chr2 | 119599926 | 119600031 | chr2 | 119600332 | 119600555 |
| chr2 | 119600570 | 119600747 | chr2 | 119600949 | 119600952 | chr2 | 119600996 | 119601061 |
| chr2 | 119602601 | 119602629 | chr2 | 119602829 | 119603086 | chr2 | 119604032 | 119604158 |
| chr2 | 119604809 | 119604851 | chr2 | 119606135 | 119606499 | chr2 | 119606783 | 119606839 |
| chr2 | 119607176 | 119607411 | chr2 | 119610844 | 119610939 | chr2 | 119611745 | 119611799 |
| chr2 | 119612324 | 119612354 | chr2 | 119614130 | 119614171 | chr2 | 119614780 | 119614852 |
| chr2 | 119615055 | 119615627 | chr2 | 119616155 | 119616551 | chr2 | 119616809 | 119616870 |
| chr2 | 119914720 | 119914752 | chr2 | 119916525 | 119916595 | chr2 | 120281646 | 120281693 |
| chr2 | 120281939 | 120281953 | chr2 | 120769511 | 120769746 | chr2 | 120825608 | 120825769 |
| chr2 | 120980068 | 120980098 | chr2 | 120980353 | 120980395 | chr2 | 121200390 | 121200433 |
| chr2 | 121345081 | 121345111 | chr2 | 121411888 | 121412153 | chr2 | 122176232 | 122176293 |
| chr2 | 122495267 | 122495413 | chr2 | 122809705 | 122809801 | chr2 | 124782333 | 124782458 |
| chr2 | 124782692 | 124783097 | chr2 | 127412291 | 127412386 | chr2 | 127413970 | 127413995 |
| chr2 | 127423220 | 127423350 | chr2 | 127429010 | 127429044 | chr2 | 127438533 | 127438663 |
| chr2 | 127783043 | 127783257 | chr2 | 127863601 | 127863725 | chr2 | 127976467 | 127976672 |
| chr2 | 128421891 | 128421947 | chr2 | 128616617 | 128616838 | chr2 | 128680057 | 128680087 |
| chr2 | 128847677 | 128847723 | chr2 | 129174888 | 129174918 | chr2 | 129494389 | 129494421 |
| chr2 | 130763584 | 130763623 | chr2 | 130937868 | 130937898 | chr2 | 130971149 | 130971321 |
| chr2 | 131084953 | 131085013 | chr2 | 131477785 | 131477936 | chr2 | 131594989 | 131595019 |
| chr2 | 131673756 | 131673785 | chr2 | 131720852 | 131721098 | chr2 | 131721461 | 131721584 |
| chr2 | 131721867 | 131721949 | chr2 | 131792260 | 131792519 | chr2 | 131792532 | 131792746 |
| chr2 | 131792921 | 131793131 | chr2 | 132088786 | 132088828 | chr2 | 132121661 | 132121829 |
| chr2 | 132152361 | 132152495 | chr2 | 132182790 | 132183089 | chr2 | 132208115 | 132208278 |
| chr2 | 132767457 | 132767707 | chr2 | 132795261 | 132795403 | chr2 | 132795670 | 132795728 |
| chr2 | 133014598 | 133014638 | chr2 | 133015275 | 133015323 | chr2 | 133062362 | 133062389 |
| chr2 | 133426249 | 133426279 | chr2 | 133426637 | 133426674 | chr2 | 136287358 | 136287390 |
| chr2 | 137522445 | 137522475 | chr2 | 137523825 | 137523855 | chr2 | 139536937 | 139537145 |

TABLE 12-continued

| chr | start | end | chr | start | end | chr | start | end |
|---|---|---|---|---|---|---|---|---|
| chr2 | 139537443 | 139537822 | chr2 | 139537851 | 139537865 | chr2 | 142887871 | 142888066 |
| chr2 | 142888348 | 142888418 | chr2 | 143569561 | 143569694 | chr2 | 144129765 | 144129795 |
| chr2 | 144299758 | 144299788 | chr2 | 144694367 | 144694514 | chr2 | 144694554 | 144695135 |
| chr2 | 145273404 | 145273751 | chr2 | 145274186 | 145274455 | chr2 | 145274814 | 145275213 |
| chr2 | 145282119 | 145282149 | chr2 | 148776809 | 148777035 | chr2 | 149633097 | 149633399 |
| chr2 | 149633744 | 149633965 | chr2 | 149645496 | 149645864 | chr2 | 151342903 | 151343277 |
| chr2 | 152248836 | 152248983 | chr2 | 154333535 | 154333567 | chr2 | 154334272 | 154334665 |
| chr2 | 154335185 | 154335271 | chr2 | 154728245 | 154728440 | chr2 | 154729083 | 154729240 |
| chr2 | 154729559 | 154729589 | chr2 | 155555038 | 155555361 | chr2 | 157176592 | 157176717 |
| chr2 | 157177003 | 157178310 | chr2 | 157178646 | 157178731 | chr2 | 160761070 | 160761556 |
| chr2 | 161253293 | 161253455 | chr2 | 162166600 | 162166632 | chr2 | 162272989 | 162273314 |
| chr2 | 162273383 | 162274338 | chr2 | 162274717 | 162274866 | chr2 | 162275146 | 162275226 |
| chr2 | 162275311 | 162275437 | chr2 | 162275473 | 162275802 | chr2 | 162280153 | 162280415 |
| chr2 | 162280741 | 162280956 | chr2 | 162283365 | 162283602 | chr2 | 162283783 | 162284055 |
| chr2 | 164593096 | 164593137 | chr2 | 166929478 | 166929613 | chr2 | 168150069 | 168150245 |
| chr2 | 168150751 | 168150945 | chr2 | 170255970 | 170256139 | chr2 | 170282981 | 170283080 |
| chr2 | 170373281 | 170373413 | chr2 | 170551730 | 170551942 | chr2 | 170681880 | 170682422 |
| chr2 | 171570182 | 171570189 | chr2 | 171570684 | 171570733 | chr2 | 171571264 | 171571315 |
| chr2 | 171571889 | 171572068 | chr2 | 171670349 | 171670446 | chr2 | 171671487 | 171671789 |
| chr2 | 171671800 | 171671881 | chr2 | 171673873 | 171673939 | chr2 | 171674739 | 171675066 |
| chr2 | 171675361 | 171675382 | chr2 | 171675523 | 171675592 | chr2 | 171676684 | 171676785 |
| chr2 | 171822428 | 171822480 | chr2 | 171839017 | 171839047 | chr2 | 172367021 | 172367125 |
| chr2 | 172411136 | 172411166 | chr2 | 172945124 | 172945167 | chr2 | 172945896 | 172946211 |
| chr2 | 172947717 | 172947913 | chr2 | 172948184 | 172948314 | chr2 | 172948709 | 172948751 |
| chr2 | 172949186 | 172949282 | chr2 | 172949349 | 172949711 | chr2 | 172952521 | 172952881 |
| chr2 | 172962993 | 172953045 | chr2 | 172955472 | 172955545 | chr2 | 172957907 | 172958066 |
| chr2 | 172961398 | 172961598 | chr2 | 172964821 | 172964888 | chr2 | 172965296 | 172965528 |
| chr2 | 172965648 | 172965762 | chr2 | 172966264 | 172966442 | chr2 | 172972735 | 172972890 |
| chr2 | 172972931 | 172973218 | chr2 | 173099784 | 173099814 | chr2 | 173100262 | 173100430 |
| chr2 | 173422685 | 173422734 | chr2 | 174148058 | 174148157 | chr2 | 175111870 | 175112092 |
| chr2 | 175190871 | 175191972 | chr2 | 175192085 | 175192468 | chr2 | 175193268 | 175193644 |
| chr2 | 175193809 | 175193823 | chr2 | 175195831 | 175195858 | chr2 | 175196432 | 175196575 |
| chr2 | 175197089 | 175197119 | chr2 | 175198752 | 175198766 | chr2 | 175198846 | 175198966 |
| chr2 | 175199527 | 175199554 | chr2 | 175199922 | 175199935 | chr2 | 175200140 | 175200440 |
| chr2 | 175200710 | 175200852 | chr2 | 175200917 | 175201182 | chr2 | 175201360 | 175201541 |
| chr2 | 175201776 | 175201828 | chr2 | 175202127 | 175202245 | chr2 | 175202569 | 175202600 |
| chr2 | 175202634 | 175202652 | chr2 | 175204174 | 175204204 | chr2 | 175204786 | 175204946 |
| chr2 | 175205588 | 175205799 | chr2 | 175206833 | 175206905 | chr2 | 175206961 | 175207028 |
| chr2 | 175207228 | 175207258 | chr2 | 175207536 | 175207653 | chr2 | 175208311 | 175208868 |
| chr2 | 175208997 | 175209135 | chr2 | 175261402 | 175261432 | chr2 | 175383935 | 175383965 |
| chr2 | 175547041 | 175547140 | chr2 | 175547384 | 175547413 | chr2 | 176940167 | 176940315 |
| chr2 | 176943269 | 176943568 | chr2 | 176943861 | 176943902 | chr2 | 176944457 | 176944846 |
| chr2 | 176945138 | 176945268 | chr2 | 176945582 | 176945784 | chr2 | 176946578 | 176946867 |
| chr2 | 176947285 | 176947389 | chr2 | 176947764 | 176947903 | chr2 | 176948599 | 176948742 |
| chr2 | 176949045 | 176949075 | chr2 | 176949695 | 176949869 | chr2 | 176950142 | 176950258 |
| chr2 | 176956558 | 176956599 | chr2 | 176956921 | 176957199 | chr2 | 176957577 | 176957628 |
| chr2 | 176957915 | 176957919 | chr2 | 176958138 | 176958489 | chr2 | 176959289 | 176959511 |
| chr2 | 176963448 | 176963522 | chr2 | 176964085 | 176964149 | chr2 | 176964390 | 176964767 |
| chr2 | 176965265 | 176965492 | chr2 | 176969463 | 176969613 | chr2 | 176969677 | 176969908 |
| chr2 | 176971628 | 176971651 | chr2 | 176976029 | 176976188 | chr2 | 176980750 | 176980937 |
| chr2 | 176981377 | 176981505 | chr2 | 176982584 | 176982627 | chr2 | 176986715 | 176986848 |
| chr2 | 176987057 | 176987224 | chr2 | 176987971 | 176988103 | chr2 | 176988155 | 176988304 |
| chr2 | 176993074 | 176993103 | chr2 | 176993547 | 176993855 | chr2 | 176994031 | 176994379 |
| chr2 | 176994498 | 176994621 | chr2 | 176995072 | 176995269 | chr2 | 176995332 | 176995668 |
| chr2 | 177001102 | 177001695 | chr2 | 177001782 | 177001976 | chr2 | 177004566 | 177004658 |
| chr2 | 177014981 | 177015010 | chr2 | 177027425 | 177027438 | chr2 | 177030149 | 177030226 |
| chr2 | 177042984 | 177042998 | chr2 | 177043267 | 177043515 | chr2 | 177053276 | 177053434 |
| chr2 | 177053619 | 177053702 | chr2 | 177054113 | 177054351 | chr2 | 177503048 | 177503077 |
| chr2 | 177503581 | 177503610 | chr2 | 177872600 | 177872629 | chr2 | 178098791 | 178098967 |
| chr2 | 178973003 | 178973042 | chr2 | 179303534 | 179303727 | chr2 | 179316860 | 179317057 |
| chr2 | 182202233 | 182202291 | chr2 | 182321397 | 182321637 | chr2 | 182322039 | 182322170 |
| chr2 | 182322400 | 182323042 | chr2 | 182451522 | 182451551 | chr2 | 182542903 | 182542933 |
| chr2 | 182543321 | 182543418 | chr2 | 182543764 | 182543925 | chr2 | 182545211 | 182545275 |
| chr2 | 182545539 | 182545694 | chr2 | 182546002 | 182546085 | chr2 | 182546435 | 182546465 |
| chr2 | 182547385 | 182547387 | chr2 | 182547438 | 182547613 | chr2 | 182548062 | 182548161 |
| chr2 | 182549088 | 182549134 | chr2 | 182549337 | 182549454 | chr2 | 182550094 | 182550124 |
| chr2 | 182819048 | 182819216 | chr2 | 183251240 | 183251303 | chr2 | 183731294 | 183731331 |
| chr2 | 183731467 | 183731524 | chr2 | 183731809 | 183732076 | chr2 | 185462869 | 185462980 |
| chr2 | 185463193 | 185463817 | chr2 | 186603488 | 186603518 | chr2 | 188419047 | 188419204 |
| chr2 | 189157427 | 189157688 | chr2 | 190708790 | 190708819 | chr2 | 193059025 | 193059317 |
| chr2 | 193059345 | 193059548 | chr2 | 193059662 | 193060067 | chr2 | 193060385 | 193060441 |
| chr2 | 193060683 | 193060891 | chr2 | 193061388 | 193061480 | chr2 | 197793125 | 197793267 |
| chr2 | 198238409 | 198238439 | chr2 | 198267345 | 198267374 | chr2 | 198456480 | 198456719 |
| chr2 | 198651002 | 198651076 | chr2 | 200326590 | 200326735 | chr2 | 200327424 | 200327451 |
| chr2 | 200329030 | 200329393 | chr2 | 200329433 | 200329668 | chr2 | 200333801 | 200333834 |
| chr2 | 200334976 | 200335451 | chr2 | 200335592 | 200335952 | chr2 | 200818892 | 200819130 |
| chr2 | 201156690 | 201156804 | chr2 | 201172444 | 201172480 | chr2 | 201450556 | 201450707 |
| chr2 | 201451014 | 201451040 | chr2 | 201693680 | 201693718 | chr2 | 202097078 | 202097143 |

TABLE 12-continued

| chr | start | end | chr | start | end | chr | start | end |
|---|---|---|---|---|---|---|---|---|
| chr2 | 202098936 | 202098965 | chr2 | 202101190 | 202101219 | chr2 | 202122459 | 202122683 |
| chr2 | 202477462 | 202477621 | chr2 | 202899862 | 202899891 | chr2 | 203484608 | 203484646 |
| chr2 | 203498452 | 203498489 | chr2 | 203880390 | 203880492 | chr2 | 204194588 | 204194725 |
| chr2 | 206551072 | 206551362 | chr2 | 207022702 | 207022802 | chr2 | 207139072 | 207139102 |
| chr2 | 207139347 | 207139605 | chr2 | 207307548 | 207307562 | chr2 | 207308802 | 207308852 |
| chr2 | 207506691 | 207507181 | chr2 | 208574821 | 208574917 | chr2 | 208588311 | 208588341 |
| chr2 | 208635534 | 208635774 | chr2 | 208662170 | 208662376 | chr2 | 208662672 | 208662710 |
| chr2 | 208989294 | 208989382 | chr2 | 209094739 | 209094845 | chr2 | 209113097 | 209113126 |
| chr2 | 209225237 | 209225275 | chr2 | 209271322 | 209271336 | chr2 | 210636335 | 210636381 |
| chr2 | 210636430 | 210636689 | chr2 | 210636738 | 210636876 | chr2 | 212248428 | 212248457 |
| chr2 | 212288927 | 212288956 | chr2 | 212295683 | 212295820 | chr2 | 212530120 | 212530149 |
| chr2 | 212537902 | 212537994 | chr2 | 212566811 | 212566840 | chr2 | 212578292 | 212578321 |
| chr2 | 212687132 | 212587151 | chr2 | 213401235 | 213401339 | chr2 | 213401613 | 213401947 |
| chr2 | 213403110 | 213403337 | chr2 | 215275823 | 215275852 | chr2 | 215276310 | 215276339 |
| chr2 | 217396039 | 217396069 | chr2 | 217448294 | 217448441 | chr2 | 217559296 | 217559326 |
| chr2 | 217559966 | 217559999 | chr2 | 218770207 | 218770270 | chr2 | 218806147 | 218806302 |
| chr2 | 219276888 | 219276918 | chr2 | 219736151 | 219736691 | chr2 | 219828049 | 219828117 |
| chr2 | 219847462 | 219847555 | chr2 | 219848809 | 219848891 | chr2 | 219848936 | 219849001 |
| chr2 | 219857723 | 219857737 | chr2 | 220080510 | 220081033 | chr2 | 220173989 | 220174036 |
| chr2 | 220174060 | 220174296 | chr2 | 220196354 | 220196567 | chr2 | 220223098 | 220223128 |
| chr2 | 220223648 | 220223699 | chr2 | 220283363 | 220283519 | chr2 | 220299588 | 220299634 |
| chr2 | 220299886 | 220300059 | chr2 | 220349055 | 220349706 | chr2 | 220361447 | 220361466 |
| chr2 | 220416379 | 220416513 | chr2 | 220417649 | 220417675 | chr2 | 221853201 | 221853352 |
| chr2 | 222285828 | 222285858 | chr2 | 222310068 | 222310105 | chr2 | 222435773 | 222435863 |
| chr2 | 223155722 | 223156188 | chr2 | 223158730 | 223159453 | chr2 | 223159869 | 223160065 |
| chr2 | 223160342 | 223160379 | chr2 | 223161247 | 223161684 | chr2 | 223161807 | 223162063 |
| chr2 | 223162779 | 223162890 | chr2 | 223162929 | 223163224 | chr2 | 223163473 | 223163535 |
| chr2 | 223163768 | 223163954 | chr2 | 223164534 | 223164883 | chr2 | 223165434 | 223165832 |
| chr2 | 223166294 | 223166408 | chr2 | 223166449 | 223166721 | chr2 | 223167389 | 223167573 |
| chr2 | 223168437 | 223168831 | chr2 | 223169640 | 223169864 | chr2 | 223170375 | 223170434 |
| chr2 | 223171109 | 223171180 | chr2 | 223172337 | 223172367 | chr2 | 223172924 | 223173173 |
| chr2 | 223175663 | 223175694 | chr2 | 223175746 | 223176181 | chr2 | 223176456 | 223176511 |
| chr2 | 223176720 | 223176983 | chr2 | 223177315 | 223177610 | chr2 | 224661521 | 224661701 |
| chr2 | 224903260 | 224903440 | chr2 | 224903690 | 224903755 | chr2 | 224904108 | 224904237 |
| chr2 | 225464038 | 225464068 | chr2 | 228029418 | 228029531 | chr2 | 228411020 | 228411050 |
| chr2 | 228466625 | 228466777 | chr2 | 228638272 | 228638302 | chr2 | 228735680 | 228735736 |
| chr2 | 228736215 | 228736295 | chr2 | 228736336 | 228736473 | chr2 | 229046107 | 229046503 |
| chr2 | 230795535 | 230795555 | chr2 | 231576609 | 231576643 | chr2 | 232330451 | 232330481 |
| chr2 | 232394970 | 232395021 | chr2 | 232395055 | 232395061 | chr2 | 232479822 | 232479938 |
| chr2 | 232506220 | 232506294 | chr2 | 232506605 | 232506635 | chr2 | 232522844 | 232522874 |
| chr2 | 232544500 | 232544530 | chr2 | 232546736 | 232546842 | chr2 | 232791704 | 232792012 |
| chr2 | 232827168 | 232827349 | chr2 | 233073078 | 233073223 | chr2 | 233220227 | 233220382 |
| chr2 | 233350208 | 233350539 | chr2 | 233350844 | 233351278 | chr2 | 233352102 | 233352451 |
| chr2 | 233352507 | 233352762 | chr2 | 233352776 | 233352853 | chr2 | 233498710 | 233498873 |
| chr2 | 233498896 | 233499297 | chr2 | 233750525 | 233750555 | chr2 | 234776483 | 234776553 |
| chr2 | 235404551 | 235404575 | chr2 | 235860746 | 235860808 | chr2 | 235861389 | 235861533 |
| chr2 | 236402771 | 236403013 | chr2 | 236403270 | 236403736 | chr2 | 236444269 | 236444298 |
| chr2 | 236578362 | 236578677 | chr2 | 236877262 | 236877399 | chr2 | 237072642 | 237073014 |
| chr2 | 237073354 | 237073414 | chr2 | 237076725 | 237076815 | chr2 | 237077562 | 237077608 |
| chr2 | 237077846 | 237078348 | chr2 | 237080264 | 237080294 | chr2 | 237081341 | 237081426 |
| chr2 | 237081537 | 237081553 | chr2 | 237082344 | 237082720 | chr2 | 237086349 | 237086468 |
| chr2 | 237145422 | 237145601 | chr2 | 237416216 | 237416429 | chr2 | 238395291 | 238395356 |
| chr2 | 238395906 | 238395961 | chr2 | 238535895 | 238535984 | chr2 | 238536005 | 238536114 |
| chr2 | 238864727 | 238864913 | chr2 | 239031722 | 239031780 | chr2 | 239051198 | 239051228 |
| chr2 | 239140139 | 239140249 | chr2 | 239149844 | 239149951 | chr2 | 239265496 | 239265787 |
| chr2 | 239482485 | 239482519 | chr2 | 239705305 | 239705357 | chr2 | 239755164 | 239755194 |
| chr2 | 239756373 | 239756462 | chr2 | 239756488 | 239756607 | chr2 | 239756634 | 239756648 |
| chr2 | 239757636 | 239757730 | chr2 | 239758126 | 239758144 | chr2 | 239758345 | 239758394 |
| chr2 | 239957330 | 239957448 | chr2 | 240167575 | 240167605 | chr2 | 240168811 | 240169051 |
| chr2 | 240319920 | 240320012 | chr2 | 240582379 | 240582524 | chr2 | 240619459 | 240619604 |
| chr2 | 240658227 | 240658421 | chr2 | 240658667 | 240658697 | chr2 | 240812243 | 240812374 |
| chr2 | 241095604 | 241095772 | chr2 | 241393200 | 241393469 | chr2 | 241497411 | 241497554 |
| chr2 | 241541932 | 241542357 | chr2 | 241545001 | 241545031 | chr2 | 241758377 | 241758819 |
| chr2 | 241759597 | 241759694 | chr2 | 241760149 | 241760178 | chr2 | 241760494 | 241760523 |
| chr2 | 241771165 | 241771257 | chr2 | 241865194 | 241865346 | chr2 | 242009391 | 242009421 |
| chr2 | 242021784 | 242021892 | chr2 | 242314494 | 242314524 | chr2 | 242523907 | 242524147 |
| chr2 | 242549849 | 242549957 | chr2 | 242554549 | 242554579 | chr2 | 242636726 | 242636812 |
| chr2 | 242640015 | 242640045 | chr2 | 242716723 | 242716760 | chr2 | 242756144 | 242756297 |
| chr2 | 242832984 | 242833159 | chr2 | 242833558 | 242833588 | chr2 | 242833797 | 242833863 |
| chr2 | 242836495 | 242836640 | chr2 | 242925496 | 242925641 | chr3 | 238536 | 238715 |
| chr3 | 239007 | 239094 | chr3 | 239622 | 239868 | chr3 | 240110 | 240223 |
| chr3 | 2140277 | 2140398 | chr3 | 3167720 | 3167750 | chr3 | 3840498 | 3840758 |
| chr3 | 3841046 | 3841144 | chr3 | 3842679 | 3842731 | chr3 | 5137960 | 5138019 |
| chr3 | 5165885 | 5165915 | chr3 | 6902288 | 6902353 | chr3 | 6903425 | 6903463 |
| chr3 | 8725296 | 8725348 | chr3 | 8810152 | 8810220 | chr3 | 9593979 | 9594015 |
| chr3 | 9594263 | 9594382 | chr3 | 9595396 | 9595502 | chr3 | 9904233 | 9904554 |
| chr3 | 9924238 | 9924534 | chr3 | 9941469 | 9941669 | chr3 | 9957064 | 9957142 |
| chr3 | 9957451 | 9967677 | chr3 | 10027432 | 10027548 | chr3 | 10182839 | 10183212 |

TABLE 12-continued

| chr | start | end | chr | start | end | chr | start | end |
|---|---|---|---|---|---|---|---|---|
| chr3 | 10183321 | 10183350 | chr3 | 10183706 | 10183782 | chr3 | 10184304 | 10184333 |
| chr3 | 10191477 | 10191620 | chr3 | 11034264 | 11034359 | chr3 | 11035070 | 11035330 |
| chr3 | 12046405 | 12046632 | chr3 | 12586149 | 12586179 | chr3 | 12632309 | 12632401 |
| chr3 | 12645678 | 12645713 | chr3 | 12673006 | 12673036 | chr3 | 12729424 | 12729454 |
| chr3 | 12870826 | 12870856 | chr3 | 12917606 | 12917655 | chr3 | 12926053 | 12926102 |
| chr3 | 12977067 | 12977144 | chr3 | 13171814 | 13171844 | chr3 | 13323494 | 13323973 |
| chr3 | 13324420 | 13324433 | chr3 | 13324847 | 13324938 | chr3 | 13590448 | 13590640 |
| chr3 | 13679172 | 13679349 | chr3 | 13921407 | 13921463 | chr3 | 14851850 | 14851897 |
| chr3 | 14852325 | 14852919 | chr3 | 15123848 | 15123992 | chr3 | 15780510 | 16780638 |
| chr3 | 16554052 | 16554111 | chr3 | 16554347 | 16554633 | chr3 | 17001303 | 17001333 |
| chr3 | 17735273 | 17735340 | chr3 | 19189441 | 19189470 | chr3 | 19189694 | 19189765 |
| chr3 | 19190143 | 19190216 | chr3 | 20070714 | 20070903 | chr3 | 22413665 | 22413694 |
| chr3 | 22413960 | 22413974 | chr3 | 23964882 | 23965019 | chr3 | 24871002 | 24871176 |
| chr3 | 25469110 | 25469139 | chr3 | 25469377 | 25469406 | chr3 | 25469679 | 25469708 |
| chr3 | 26664045 | 26664119 | chr3 | 26664389 | 26664755 | chr3 | 27754478 | 27754508 |
| chr3 | 27762336 | 27762650 | chr3 | 27762857 | 27762887 | chr3 | 27763566 | 27763595 |
| chr3 | 27764457 | 27764471 | chr3 | 27765181 | 27765347 | chr3 | 27771497 | 27772004 |
| chr3 | 27772790 | 27222819 | chr3 | 28616832 | 28617675 | chr3 | 31494108 | 31494138 |
| chr3 | 32708277 | 32708405 | chr3 | 32858353 | 32858958 | chr3 | 32859256 | 32859284 |
| chr3 | 32859418 | 32859693 | chr3 | 32860068 | 32860273 | chr3 | 33259904 | 33260776 |
| chr3 | 35680842 | 35680872 | chr3 | 36805815 | 36805863 | chr3 | 36806179 | 36806193 |
| chr3 | 36984378 | 36984425 | chr3 | 37276385 | 37276490 | chr3 | 37493519 | 37493621 |
| chr3 | 37901923 | 37901953 | chr3 | 38030618 | 38030782 | chr3 | 38032331 | 38032361 |
| chr3 | 38035774 | 38035989 | chr3 | 38080685 | 38080925 | chr3 | 38081154 | 38081271 |
| chr3 | 38182244 | 38182306 | chr3 | 38182626 | 38182655 | chr3 | 38208158 | 38208226 |
| chr3 | 38690624 | 38690668 | chr3 | 39851772 | 39851814 | chr3 | 40202174 | 40202255 |
| chr3 | 40428507 | 40428713 | chr3 | 41266086 | 41266151 | chr3 | 42222730 | 42222847 |
| chr3 | 42329346 | 42329511 | chr3 | 42640855 | 42640964 | chr3 | 42814569 | 42814603 |
| chr3 | 42852329 | 42852359 | chr3 | 42947411 | 42947552 | chr3 | 43735604 | 43735634 |
| chr3 | 44036260 | 44036330 | chr3 | 44036570 | 44036600 | chr3 | 44036820 | 44037203 |
| chr3 | 44037625 | 44037662 | chr3 | 44037874 | 44038646 | chr3 | 44039348 | 44040006 |
| chr3 | 44040511 | 44040553 | chr3 | 44040796 | 44041039 | chr3 | 44063434 | 44063872 |
| chr3 | 44596479 | 44596509 | chr3 | 44596716 | 44596809 | chr3 | 44626438 | 44626711 |
| chr3 | 44726875 | 44727193 | chr3 | 45187296 | 45187327 | chr3 | 46924934 | 46924964 |
| chr3 | 47144864 | 47144893 | chr3 | 47352704 | 47352734 | chr3 | 47521062 | 47521178 |
| chr3 | 47555760 | 47555790 | chr3 | 47830060 | 47830148 | chr3 | 47831601 | 47831819 |
| chr3 | 48227765 | 48227870 | chr3 | 48236476 | 48236724 | chr3 | 48693304 | 48693700 |
| chr3 | 48693852 | 48694154 | chr3 | 48698251 | 48698431 | chr3 | 48698810 | 48699010 |
| chr3 | 48699377 | 48699767 | chr3 | 48978413 | 48978479 | chr3 | 49142883 | 49142913 |
| chr3 | 49196747 | 49196831 | chr3 | 49236845 | 49236874 | chr3 | 49405953 | 49405982 |
| chr3 | 49412883 | 49412987 | chr3 | 49591832 | 49592076 | chr3 | 49907093 | 49907130 |
| chr3 | 49939931 | 49940398 | chr3 | 50072827 | 50072925 | chr3 | 50243383 | 50243480 |
| chr3 | 50374655 | 50374684 | chr3 | 50374917 | 50374946 | chr3 | 50375179 | 50375559 |
| chr3 | 50377973 | 50378002 | chr3 | 50378277 | 50378306 | chr3 | 50378512 | 50378541 |
| chr3 | 50395506 | 50395536 | chr3 | 50402170 | 50402944 | chr3 | 50575616 | 50575658 |
| chr3 | 50968445 | 50968511 | chr3 | 52352194 | 52352326 | chr3 | 52442062 | 52442091 |
| chr3 | 52552556 | 52552661 | chr3 | 52553469 | 52553499 | chr3 | 53032733 | 53033524 |
| chr3 | 53253306 | 53253599 | chr3 | 53382392 | 53382565 | chr3 | 53480528 | 53480683 |
| chr3 | 54155611 | 54155677 | chr3 | 54157381 | 54157450 | chr3 | 54157878 | 54157919 |
| chr3 | 54583435 | 54583465 | chr3 | 55519219 | 55519253 | chr3 | 55523106 | 55523290 |
| chr3 | 55603443 | 55603632 | chr3 | 57437452 | 57437482 | chr3 | 57529094 | 57529218 |
| chr3 | 58153446 | 58153608 | chr3 | 62304567 | 62304669 | chr3 | 62353371 | 62354409 |
| chr3 | 62354283 | 62354328 | chr3 | 62354625 | 62354792 | chr3 | 62354900 | 62354914 |
| chr3 | 62355424 | 62355478 | chr3 | 62355774 | 62356219 | chr3 | 62356367 | 62356644 |
| chr3 | 62356793 | 62357192 | chr3 | 52357279 | 62357347 | chr3 | 62357624 | 62357667 |
| chr3 | 62358530 | 62358595 | chr3 | 62358858 | 62359011 | chr3 | 62359376 | 62359893 |
| chr3 | 62360302 | 62360560 | chr3 | 62362902 | 62362916 | chr3 | 62363099 | 62363200 |
| chr3 | 62363626 | 62363693 | chr3 | 62363906 | 62364176 | chr3 | 62364280 | 62364329 |
| chr3 | 62364702 | 62365154 | chr3 | 62861118 | 62861148 | chr3 | 63264139 | 63264169 |
| chr3 | 63719169 | 63719303 | chr3 | 66053446 | 66053613 | chr3 | 68056904 | 68057145 |
| chr3 | 68920931 | 68981113 | chr3 | 68981552 | 68981624 | chr3 | 69590939 | 69590969 |
| chr3 | 69591363 | 69591414 | chr3 | 69591780 | 69591977 | chr3 | 69740944 | 69740990 |
| chr3 | 69937703 | 69937848 | chr3 | 70661011 | 70661079 | chr3 | 71802518 | 71802622 |
| chr3 | 71803126 | 71803372 | chr3 | 71803643 | 71803783 | chr3 | 73045340 | 73045583 |
| chr3 | 75956027 | 75956375 | chr3 | 79815522 | 79815557 | chr3 | 79816778 | 79817015 |
| chr3 | 79817288 | 79817318 | chr3 | 85008553 | 85008708 | chr3 | 88247941 | 88248049 |
| chr3 | 93698033 | 93698063 | chr3 | 96532817 | 96532873 | chr3 | 96533383 | 96533458 |
| chr3 | 96534035 | 96534096 | chr3 | 98313191 | 98313253 | chr3 | 98618182 | 98618376 |
| chr3 | 98620891 | 98620980 | chr3 | 99594925 | 99595105 | chr3 | 100228688 | 100228768 |
| chr3 | 101094160 | 101094190 | chr3 | 101230678 | 101231070 | chr3 | 101331792 | 101331861 |
| chr3 | 101354294 | 101354442 | chr3 | 101397240 | 101397358 | chr3 | 101406823 | 101407190 |
| chr3 | 101411545 | 101411666 | chr3 | 101497841 | 101497996 | chr3 | 101645019 | 101645181 |
| chr3 | 105015466 | 105015519 | chr3 | 105684885 | 105684987 | chr3 | 106936157 | 106936336 |
| chr3 | 112052252 | 112052419 | chr3 | 112185933 | 112185975 | chr3 | 113557333 | 113557363 |
| chr3 | 113847911 | 113847941 | chr3 | 115502232 | 115502390 | chr3 | 115512319 | 115512448 |
| chr3 | 117715549 | 117716123 | chr3 | 117716214 | 117716473 | chr3 | 120004080 | 120004405 |
| chr3 | 120004468 | 120004497 | chr3 | 120169104 | 120169149 | chr3 | 120169768 | 120169835 |
| chr3 | 120627317 | 120627453 | chr3 | 121215241 | 121215271 | chr3 | 121657197 | 121657515 |

TABLE 12-continued

| chr | start | end | chr | start | end | chr | start | end |
|---|---|---|---|---|---|---|---|---|
| chr3 | 121741545 | 121741598 | chr3 | 121902991 | 121903218 | chr3 | 121903324 | 121903619 |
| chr3 | 122162036 | 122162117 | chr3 | 122162890 | 122163054 | chr3 | 122234242 | 122234538 |
| chr3 | 122573688 | 122573826 | chr3 | 122702288 | 122702451 | chr3 | 123167301 | 123167529 |
| chr3 | 123167769 | 123167827 | chr3 | 124410075 | 124410157 | chr3 | 125417341 | 125417424 |
| chr3 | 125898597 | 125899207 | chr3 | 125899525 | 125899962 | chr3 | 125932252 | 125932500 |
| chr3 | 126157586 | 126157663 | chr3 | 126261929 | 126262000 | chr3 | 126373520 | 126373704 |
| chr3 | 126854699 | 126854796 | chr3 | 127534814 | 127534897 | chr3 | 127634186 | 127634216 |
| chr3 | 127794546 | 127794860 | chr3 | 127795325 | 127795408 | chr3 | 128056383 | 128056497 |
| chr3 | 128202447 | 128202477 | chr3 | 128208903 | 128209232 | chr3 | 128273993 | 128274051 |
| chr3 | 128274309 | 128274611 | chr3 | 128384991 | 128385132 | chr3 | 128417201 | 128417231 |
| chr3 | 128599405 | 128599477 | chr3 | 128720061 | 128720142 | chr3 | 128720164 | 128720346 |
| chr3 | 128720419 | 128720533 | chr3 | 128720567 | 128720611 | chr3 | 128720869 | 128721229 |
| chr3 | 128764489 | 128764606 | chr3 | 128786496 | 128786525 | chr3 | 129008841 | 129009004 |
| chr3 | 129047978 | 129048008 | chr3 | 129372419 | 129372546 | chr3 | 129693108 | 129693199 |
| chr3 | 129693305 | 129693498 | chr3 | 129693955 | 129694299 | chr3 | 130064451 | 130064484 |
| chr3 | 130064818 | 130064848 | chr3 | 130236049 | 130236063 | chr3 | 130236174 | 130236273 |
| chr3 | 130502167 | 130502197 | chr3 | 130519901 | 130520077 | chr3 | 131754031 | 131754061 |
| chr3 | 132757065 | 132757104 | chr3 | 133217784 | 133217999 | chr3 | 133748140 | 133748245 |
| chr3 | 133748481 | 133748576 | chr3 | 133970381 | 133970413 | chr3 | 134369646 | 134369855 |
| chr3 | 134514866 | 134514895 | chr3 | 134515128 | 134515369 | chr3 | 134515676 | 134516222 |
| chr3 | 136016868 | 136016942 | chr3 | 136537642 | 136537730 | chr3 | 136538585 | 136538815 |
| chr3 | 136582883 | 136582951 | chr3 | 136751641 | 136751809 | chr3 | 137479233 | 137479302 |
| chr3 | 137479601 | 137479687 | chr3 | 137479980 | 137480764 | chr3 | 137481170 | 137481315 |
| chr3 | 137481858 | 137481872 | chr3 | 137481936 | 137482183 | chr3 | 137483313 | 137483432 |
| chr3 | 137483514 | 137483589 | chr3 | 137483848 | 137484002 | chr3 | 137484405 | 137484531 |
| chr3 | 137486029 | 137486310 | chr3 | 137486516 | 137486550 | chr3 | 137487964 | 137488003 |
| chr3 | 137488950 | 137489698 | chr3 | 137489876 | 137491040 | chr3 | 137892691 | 137892721 |
| chr3 | 137894374 | 137894415 | chr3 | 138058859 | 138058897 | chr3 | 138067717 | 138067747 |
| chr3 | 138153963 | 138153993 | chr3 | 138318827 | 138318918 | chr3 | 138374229 | 138374258 |
| chr3 | 138635369 | 138635507 | chr3 | 138655934 | 138656138 | chr3 | 138656834 | 138656889 |
| chr3 | 138657414 | 138657494 | chr3 | 138657618 | 138658295 | chr3 | 138658704 | 138658863 |
| chr3 | 138659081 | 138659099 | chr3 | 138662134 | 138662164 | chr3 | 138662282 | 138662296 |
| chr3 | 138662382 | 138662448 | chr3 | 138662799 | 138662842 | chr3 | 138663613 | 138663727 |
| chr3 | 138664142 | 138664165 | chr3 | 138664928 | 138665323 | chr3 | 138665562 | 138666294 |
| chr3 | 138668758 | 138669108 | chr3 | 138669141 | 138669387 | chr3 | 139258267 | 139258316 |
| chr3 | 139653491 | 139653693 | chr3 | 140769513 | 140769705 | chr3 | 140769908 | 140770301 |
| chr3 | 140770408 | 140770589 | chr3 | 140770644 | 140770829 | chr3 | 140771305 | 140771335 |
| chr3 | 140771816 | 140771854 | chr3 | 141174349 | 141174606 | chr3 | 141363466 | 141363496 |
| chr3 | 141481651 | 141482073 | chr3 | 141516389 | 141516719 | chr3 | 141657032 | 141657079 |
| chr3 | 141832939 | 141833015 | chr3 | 141835935 | 141836077 | chr3 | 142159804 | 142159841 |
| chr3 | 142537638 | 142537779 | chr3 | 142682273 | 142682392 | chr3 | 142718283 | 142718358 |
| chr3 | 142791151 | 142791255 | chr3 | 142837980 | 142838318 | chr3 | 142838621 | 142838646 |
| chr3 | 142838877 | 142839036 | chr3 | 142839563 | 142839688 | chr3 | 142839784 | 142839901 |
| chr3 | 142839945 | 142840127 | chr3 | 142840222 | 142840236 | chr3 | 142896156 | 142896214 |
| chr3 | 143280343 | 143280373 | chr3 | 143614462 | 143614504 | chr3 | 145735852 | 145735882 |
| chr3 | 145878665 | 145878695 | chr3 | 146187946 | 146187978 | chr3 | 147074457 | 147074487 |
| chr3 | 147074974 | 147075006 | chr3 | 147077289 | 147077671 | chr3 | 147078959 | 147079188 |
| chr3 | 147087562 | 147087799 | chr3 | 147088440 | 147088523 | chr3 | 147088939 | 147089099 |
| chr3 | 147098431 | 147098470 | chr3 | 147105898 | 147106010 | chr3 | 147108841 | 147109765 |
| chr3 | 147110229 | 147110683 | chr3 | 147110927 | 147111089 | chr3 | 147125697 | 147125726 |
| chr3 | 147127037 | 147127067 | chr3 | 147127681 | 147127902 | chr3 | 147136931 | 147137000 |
| chr3 | 147137076 | 147137164 | chr3 | 147138768 | 147138855 | chr3 | 147139374 | 147139528 |
| chr3 | 148415427 | 148415644 | chr3 | 148523213 | 148523297 | chr3 | 148803120 | 148803276 |
| chr3 | 149374947 | 149375023 | chr3 | 150237792 | 150237822 | chr3 | 150802981 | 150802999 |
| chr3 | 150803026 | 150803080 | chr3 | 150804043 | 150804077 | chr3 | 150804967 | 150805030 |
| chr3 | 152107022 | 152107052 | chr3 | 152553343 | 152553384 | chr3 | 152553658 | 152553725 |
| chr3 | 152707390 | 152707460 | chr3 | 152877666 | 152877696 | chr3 | 153838818 | 153838870 |
| chr3 | 153839518 | 153839952 | chr3 | 154146133 | 154146394 | chr3 | 154146654 | 154146908 |
| chr3 | 154797334 | 154797703 | chr3 | 155456372 | 155456630 | chr3 | 155461030 | 155461195 |
| chr3 | 155463041 | 155463071 | chr3 | 156007772 | 156007801 | chr3 | 156008976 | 156009299 |
| chr3 | 156009319 | 156009425 | chr3 | 157155252 | 157155490 | chr3 | 157155982 | 157156194 |
| chr3 | 157812196 | 157812257 | chr3 | 157812437 | 157812645 | chr3 | 157812912 | 157813070 |
| chr3 | 157813670 | 157813824 | chr3 | 157814311 | 157814340 | chr3 | 157815657 | 157815822 |
| chr3 | 157820576 | 157820605 | chr3 | 157821537 | 157821662 | chr3 | 157821904 | 157822008 |
| chr3 | 157823073 | 157823119 | chr3 | 157823139 | 157823143 | chr3 | 157823464 | 157823493 |
| chr3 | 157824133 | 157824146 | chr3 | 157824212 | 157824231 | chr3 | 157824495 | 157824871 |
| chr3 | 157825176 | 157825408 | chr3 | 158319236 | 158319359 | chr3 | 159756687 | 159756856 |
| chr3 | 159944486 | 159944546 | chr3 | 164912376 | 164912668 | chr3 | 164912907 | 164913872 |
| chr3 | 164914980 | 164915129 | chr3 | 169376183 | 169376215 | chr3 | 169376680 | 169376780 |
| chr3 | 169378825 | 169379024 | chr3 | 169539898 | 169540679 | chr3 | 169541070 | 169541102 |
| chr3 | 170136627 | 170136751 | chr3 | 170302617 | 170302677 | chr3 | 170303087 | 170303129 |
| chr3 | 170303380 | 170303423 | chr3 | 170303639 | 170303844 | chr3 | 170602030 | 170602133 |
| chr3 | 171193088 | 171193311 | chr3 | 171527930 | 171527971 | chr3 | 171529811 | 171529958 |
| chr3 | 172165443 | 172165784 | chr3 | 172165867 | 172166512 | chr3 | 172166879 | 172166893 |
| chr3 | 172167000 | 172167044 | chr3 | 172167297 | 172167322 | chr3 | 172167660 | 172167917 |
| chr3 | 172342101 | 172342147 | chr3 | 172355895 | 172356038 | chr3 | 172383550 | 172383600 |
| chr3 | 172425382 | 172425717 | chr3 | 172469925 | 172470036 | chr3 | 173115237 | 173115550 |
| chr3 | 173162817 | 173162847 | chr3 | 173302542 | 173302668 | chr3 | 173302992 | 173303225 |

TABLE 12-continued

| chr | start | end | chr | start | end | chr | start | end |
|---|---|---|---|---|---|---|---|---|
| chr3 | 176710105 | 176710241 | chr3 | 176872357 | 176872443 | chr3 | 178861259 | 178861447 |
| chr3 | 178916711 | 178916959 | chr3 | 178921532 | 178921568 | chr3 | 178927966 | 178928094 |
| chr3 | 178936059 | 178936111 | chr3 | 178952004 | 178952105 | chr3 | 179168661 | 179169266 |
| chr3 | 179367874 | 179367920 | chr3 | 179754178 | 179754192 | chr3 | 179754239 | 179754759 |
| chr3 | 179754804 | 179754872 | chr3 | 179755087 | 179755372 | chr3 | 180320256 | 180320294 |
| chr3 | 181413742 | 181414330 | chr3 | 181420065 | 181420116 | chr3 | 181420316 | 181420374 |
| chr3 | 181421411 | 181422282 | chr3 | 181422541 | 181422985 | chr3 | 181428388 | 181428772 |
| chr3 | 181430695 | 181430771 | chr3 | 181437129 | 181437349 | chr3 | 181438194 | 181438353 |
| chr3 | 181440892 | 181441927 | chr3 | 181442145 | 181442410 | chr3 | 181443014 | 181443557 |
| chr3 | 181443760 | 181443861 | chr3 | 181444108 | 181444236 | chr3 | 181444434 | 181444524 |
| chr3 | 181444613 | 181444948 | chr3 | 181444989 | 181445013 | chr3 | 181445369 | 181445464 |
| chr3 | 181445800 | 181445861 | chr3 | 182815811 | 182816027 | chr3 | 182895956 | 182896144 |
| chr3 | 182911545 | 182911574 | chr3 | 183109854 | 183109883 | chr3 | 183145412 | 183145618 |
| chr3 | 183145931 | 183146025 | chr3 | 183146397 | 183146435 | chr3 | 183146648 | 183146677 |
| chr3 | 183183523 | 183183659 | chr3 | 183208370 | 183208404 | chr3 | 183217676 | 183217706 |
| chr3 | 183647996 | 183648026 | chr3 | 183728793 | 183728952 | chr3 | 183870824 | 183870858 |
| chr3 | 183872490 | 183872524 | chr3 | 183965599 | 183965907 | chr3 | 184018038 | 184018136 |
| chr3 | 184031686 | 184031746 | chr3 | 184057254 | 184057557 | chr3 | 184099417 | 184099446 |
| chr3 | 184319470 | 184319612 | chr3 | 184319828 | 184320100 | chr3 | 184319874 | 184319891 |
| chr3 | 185001695 | 185001919 | chr3 | 185271296 | 185271764 | chr3 | 185275856 | 185275886 |
| chr3 | 185303247 | 185303277 | chr3 | 185363074 | 185363261 | chr3 | 185629516 | 185629546 |
| chr3 | 185643324 | 185643405 | chr3 | 185658513 | 185658543 | chr3 | 185668237 | 185668311 |
| chr3 | 186078766 | 186078898 | chr3 | 186079204 | 186079331 | chr3 | 186080188 | 186080218 |
| chr3 | 186287130 | 186287270 | chr3 | 186857152 | 186857607 | chr3 | 186914705 | 186914734 |
| chr3 | 187387850 | 187387920 | chr3 | 187388007 | 187388239 | chr3 | 192125828 | 192125828 |
| chr3 | 192126146 | 192126710 | chr3 | 192126787 | 192126863 | chr3 | 192127354 | 192127372 |
| chr3 | 192127557 | 192127730 | chr3 | 192127937 | 192128074 | chr3 | 192232097 | 192232175 |
| chr3 | 192232452 | 192232570 | chr3 | 192232850 | 192232951 | chr3 | 192233095 | 192233150 |
| chr3 | 192958725 | 192958968 | chr3 | 193312128 | 193312347 | chr3 | 193419702 | 193419732 |
| chr3 | 193548637 | 193548835 | chr3 | 193776089 | 193776119 | chr3 | 194048751 | 194048919 |
| chr3 | 194120008 | 194120164 | chr3 | 194120812 | 194120841 | chr3 | 194120934 | 194120963 |
| chr3 | 194208468 | 194208562 | chr3 | 194407998 | 194408028 | chr3 | 194408375 | 194408768 |
| chr3 | 194408839 | 194409021 | chr3 | 194981816 | 194981913 | chr3 | 195095450 | 195095543 |
| chr3 | 195184022 | 195184140 | chr3 | 195409773 | 195409813 | chr3 | 195536733 | 195536848 |
| chr3 | 195538217 | 195538353 | chr3 | 195587032 | 195582118 | chr3 | 195601239 | 195601312 |
| chr3 | 195602330 | 195602576 | chr3 | 195639755 | 195639785 | chr3 | 195648794 | 195649004 |
| chr3 | 195834581 | 195834611 | chr3 | 196046702 | 196046830 | chr3 | 196065342 | 196065583 |
| chr3 | 196069743 | 196070340 | chr3 | 196255617 | 196255631 | chr3 | 196263303 | 196263471 |
| chr3 | 196344683 | 196344795 | chr3 | 196387295 | 196387415 | chr3 | 196387628 | 196387665 |
| chr3 | 196388383 | 196388581 | chr3 | 196433946 | 196434104 | chr3 | 196440510 | 196440676 |
| chr3 | 196667872 | 196668080 | chr3 | 196728418 | 196728448 | chr3 | 196731155 | 196731313 |
| chr3 | 196755958 | 196755987 | chr3 | 197209019 | 197209048 | chr3 | 197236945 | 197237111 |
| chr3 | 197247047 | 197247110 | chr3 | 197278926 | 197278988 | chr3 | 197313997 | 197314107 |
| chr3 | 197326860 | 197327042 | chr3 | 197330060 | 197330147 | chr3 | 197466364 | 197466540 |
| chr3 | 197616707 | 197616861 | chr3 | 197677029 | 197677058 | chr3 | 197685788 | 197686085 |
| chr3 | 197686495 | 197686524 | chr3 | 197686941 | 197687223 | chr3 | 197687694 | 197687723 |
| chr4 | 206324 | 206353 | chr4 | 331322 | 331352 | chr4 | 488816 | 488875 |
| chr4 | 512978 | 513008 | chr4 | 513704 | 513734 | chr4 | 568429 | 568652 |
| chr4 | 569048 | 569115 | chr4 | 569275 | 569435 | chr4 | 569461 | 569732 |
| chr4 | 570966 | 571013 | chr4 | 571508 | 571689 | chr4 | 628572 | 629061 |
| chr4 | 651196 | 651261 | chr4 | 657521 | 657552 | chr4 | 678471 | 678501 |
| chr4 | 718052 | 718112 | chr4 | 718321 | 718456 | chr4 | 829611 | 829641 |
| chr4 | 955367 | 955454 | chr4 | 955867 | 955919 | chr4 | 995876 | 995993 |
| chr4 | 996101 | 996174 | chr4 | 1008740 | 1008902 | chr4 | 1016127 | 1016252 |
| chr4 | 1016586 | 1016747 | chr4 | 1025928 | 1026074 | chr4 | 1041763 | 1041926 |
| chr4 | 1093536 | 1093675 | chr4 | 1107494 | 1107585 | chr4 | 1165450 | 1165470 |
| chr4 | 1189021 | 1189051 | chr4 | 1214894 | 1215162 | chr4 | 1215415 | 1215451 |
| chr4 | 1282515 | 1282545 | chr4 | 1331675 | 1331705 | chr4 | 1336755 | 1336902 |
| chr4 | 1338715 | 1338812 | chr4 | 1339099 | 1339221 | chr4 | 1396578 | 1396696 |
| chr4 | 1397396 | 1397495 | chr4 | 1398303 | 1398378 | chr4 | 1399723 | 1399768 |
| chr4 | 1401711 | 1401743 | chr4 | 1512368 | 1512398 | chr4 | 1556419 | 1556609 |
| chr4 | 1576484 | 1576528 | chr4 | 1616682 | 1617247 | chr4 | 1687080 | 1687110 |
| chr4 | 1800153 | 1800191 | chr4 | 1803550 | 1803582 | chr4 | 1206084 | 1806113 |
| chr4 | 1807355 | 1807384 | chr4 | 1962787 | 1962816 | chr4 | 1993771 | 1994180 |
| chr4 | 2042106 | 2042122 | chr4 | 2042169 | 2042258 | chr4 | 2066114 | 2066265 |
| chr4 | 2306672 | 2305827 | chr4 | 2527907 | 2527937 | chr4 | 2632556 | 2532586 |
| chr4 | 2540073 | 2540297 | chr4 | 2765862 | 2765910 | chr4 | 2926366 | 2926396 |
| chr4 | 2978968 | 2979145 | chr4 | 3036118 | 3036148 | chr4 | 3217107 | 3217154 |
| chr4 | 3371519 | 3371652 | chr4 | 3446991 | 3447021 | chr4 | 3447816 | 3448015 |
| chr4 | 3768833 | 3768949 | chr4 | 3768995 | 3769189 | chr4 | 3769560 | 3769574 |
| chr4 | 3873694 | 3873769 | chr4 | 4228189 | 4228241 | chr4 | 4229689 | 4229781 |
| chr4 | 4387533 | 4387627 | chr4 | 4417568 | 4417603 | chr4 | 4855102 | 4855171 |
| chr4 | 4855371 | 4855433 | chr4 | 4860046 | 4860075 | chr4 | 4862769 | 4863110 |
| chr4 | 4867698 | 4867886 | chr4 | 4868566 | 4868792 | chr4 | 4868829 | 4868999 |
| chr4 | 4872088 | 4872167 | chr4 | 4872777 | 4872850 | chr4 | 4873427 | 4873528 |
| chr4 | 5021188 | 5021217 | chr4 | 5053070 | 5053518 | chr4 | 5053747 | 5054093 |
| chr4 | 5519950 | 5520092 | chr4 | 5709906 | 5709984 | chr4 | 5712979 | 5713231 |
| chr4 | 5889948 | 5890045 | chr4 | 5890274 | 5890444 | chr4 | 5891966 | 5892081 |

TABLE 12-continued

| chr | start | end | chr | start | end | chr | start | end |
|---|---|---|---|---|---|---|---|---|
| chr4 | 5892110 | 5892194 | chr4 | 5892750 | 5892780 | chr4 | 5893981 | 5894082 |
| chr4 | 6200897 | 6201235 | chr4 | 6202103 | 6202276 | chr4 | 6247351 | 5247381 |
| chr4 | 6565004 | 6565042 | chr4 | 6628453 | 6628500 | chr4 | 6670184 | 6670214 |
| chr4 | 6719599 | 6719637 | chr4 | 6748346 | 6748557 | chr4 | 6839352 | 6839402 |
| chr4 | 6955114 | 6955144 | chr4 | 6957481 | 6957620 | chr4 | 7038560 | 7038688 |
| chr4 | 7647770 | 7647945 | chr4 | 7758476 | 7758561 | chr4 | 8429086 | 8429178 |
| chr4 | 8582549 | 8582579 | chr4 | 8607813 | 8607932 | chr4 | 8608556 | 8608600 |
| chr4 | 8858827 | 8859047 | chr4 | 8859382 | 8859738 | chr4 | 8860398 | 8860553 |
| chr4 | 8861649 | 8861752 | chr4 | 8861919 | 8862014 | chr4 | 8862797 | 8862811 |
| chr4 | 8863441 | 8863526 | chr4 | 8864499 | 8864598 | chr4 | 8864831 | 8865058 |
| chr4 | 8868822 | 8868845 | chr4 | 8868932 | 8869270 | chr4 | 8869601 | 8869813 |
| chr4 | 8873054 | 8873072 | chr4 | 8873809 | 8873984 | chr4 | 8874485 | 8874534 |
| chr4 | 8874773 | 8874787 | chr4 | 8875877 | 8875907 | chr4 | 8893060 | 8893093 |
| chr4 | 8893501 | 8893531 | chr4 | 8893816 | 8893931 | chr4 | 8894641 | 8894957 |
| chr4 | 8895232 | 8895350 | chr4 | 8895554 | 8895584 | chr4 | 8895965 | 8896052 |
| chr4 | 9423273 | 9423354 | chr4 | 9782992 | 9783095 | chr4 | 9783126 | 9783412 |
| chr4 | 10458395 | 10459121 | chr4 | 10462833 | 10463047 | chr4 | 10463073 | 10463604 |
| chr4 | 10782701 | 10782741 | chr4 | 11429506 | 11429633 | chr4 | 13524026 | 13524251 |
| chr4 | 13524665 | 13524775 | chr4 | 13524957 | 13524971 | chr4 | 13537569 | 13537688 |
| chr4 | 13540983 | 13541068 | chr4 | 13546026 | 13546078 | chr4 | 13548502 | 13548589 |
| chr4 | 13548635 | 13548895 | chr4 | 13549340 | 13549510 | chr4 | 15780223 | 15780320 |
| chr4 | 16084741 | 16084818 | chr4 | 16085167 | 16085301 | chr4 | 16085352 | 16085381 |
| chr4 | 16085675 | 16085682 | chr4 | 17430691 | 17430832 | chr4 | 17783003 | 17783480 |
| chr4 | 20254693 | 20254723 | chr4 | 20255525 | 20255861 | chr4 | 20256152 | 20256285 |
| chr4 | 21950248 | 21950295 | chr4 | 24801868 | 24801985 | chr4 | 24914638 | 24914668 |
| chr4 | 25656815 | 25656879 | chr4 | 25657437 | 25657477 | chr4 | 26256825 | 26256867 |
| chr4 | 27086432 | 27086462 | chr4 | 30722243 | 30722273 | chr4 | 30723856 | 30723862 |
| chr4 | 30724249 | 30724372 | chr4 | 37245837 | 37245851 | chr4 | 37246134 | 37246360 |
| chr4 | 37246490 | 37246699 | chr4 | 37247096 | 37247216 | chr4 | 38566328 | 38566418 |
| chr4 | 38673115 | 38673144 | chr4 | 39816807 | 39817064 | chr4 | 40632773 | 40632802 |
| chr4 | 40910303 | 40910465 | chr4 | 41258716 | 41258788 | chr4 | 41259086 | 41259176 |
| chr4 | 41747009 | 41747133 | chr4 | 41747493 | 41747582 | chr4 | 41747958 | 41748011 |
| chr4 | 41748144 | 41748296 | chr4 | 41748660 | 41748766 | chr4 | 41749033 | 41749063 |
| chr4 | 41749270 | 41749761 | chr4 | 41750223 | 41750504 | chr4 | 41751870 | 41752006 |
| chr4 | 41752451 | 41752693 | chr4 | 41752968 | 41753398 | chr4 | 41753610 | 41753916 |
| chr4 | 41754031 | 41754071 | chr4 | 41875430 | 41875902 | chr4 | 41880331 | 41880412 |
| chr4 | 41881385 | 41881425 | chr4 | 41883091 | 41883302 | chr4 | 41883510 | 41883610 |
| chr4 | 41938449 | 41938479 | chr4 | 41993676 | 41993815 | chr4 | 42152962 | 42153411 |
| chr4 | 42153533 | 42153632 | chr4 | 42153882 | 42154025 | chr4 | 42154280 | 42154359 |
| chr4 | 42154662 | 42154997 | chr4 | 42155215 | 42155322 | chr4 | 42348266 | 42348331 |
| chr4 | 42398842 | 42398872 | chr4 | 42399137 | 42399191 | chr4 | 42399688 | 42399872 |
| chr4 | 44266683 | 44266780 | chr4 | 44449480 | 44449569 | chr4 | 46067800 | 46067954 |
| chr4 | 46391353 | 46391383 | chr4 | 46911535 | 46911564 | chr4 | 46995161 | 46995835 |
| chr4 | 47034908 | 47034938 | chr4 | 47197142 | 47197270 | chr4 | 47914784 | 47914992 |
| chr4 | 48485067 | 48485288 | chr4 | 48485590 | 48486000 | chr4 | 48486356 | 48486389 |
| chr4 | 48492181 | 48492433 | chr4 | 48848428 | 48848554 | chr4 | 48988109 | 48988335 |
| chr4 | 53728495 | 53729056 | chr4 | 54966854 | 54967075 | chr4 | 54967342 | 54967484 |
| chr4 | 54969833 | 54970095 | chr4 | 54970369 | 54970482 | chr4 | 54975991 | 54976115 |
| chr4 | 55093048 | 55093255 | chr4 | 55096239 | 55096344 | chr4 | 55097404 | 55097634 |
| chr4 | 55097973 | 55098092 | chr4 | 55098198 | 55098373 | chr4 | 55098674 | 55098744 |
| chr4 | 55099016 | 55099062 | chr4 | 55133613 | 55133642 | chr4 | 55136787 | 55136816 |
| chr4 | 55138657 | 55138686 | chr4 | 55139691 | 55139720 | chr4 | 55140731 | 55140784 |
| chr4 | 55141015 | 55141050 | chr4 | 55144105 | 55144134 | chr4 | 55146554 | 55146583 |
| chr4 | 55152075 | 55152140 | chr4 | 55524220 | 55524274 | chr4 | 55589753 | 55589782 |
| chr4 | 55592166 | 55592204 | chr4 | 55593417 | 55593675 | chr4 | 55594183 | 55594212 |
| chr4 | 55595504 | 55595614 | chr4 | 55599306 | 55599356 | chr4 | 55968165 | 55968194 |
| chr4 | 55991107 | 55991228 | chr4 | 55992153 | 55992169 | chr4 | 56594679 | 56594720 |
| chr4 | 56659692 | 56659866 | chr4 | 56659935 | 56660021 | chr4 | 57017387 | 57017459 |
| chr4 | 57371718 | 57371963 | chr4 | 57372336 | 57372504 | chr4 | 57396946 | 57397264 |
| chr4 | 57521506 | 57521663 | chr4 | 57521701 | 57522382 | chr4 | 57522420 | 57522815 |
| chr4 | 57687720 | 57687782 | chr4 | 57777437 | 57777595 | chr4 | 57803498 | 57803558 |
| chr4 | 57813490 | 57813763 | chr4 | 57976033 | 57976185 | chr4 | 57976416 | 57976573 |
| chr4 | 58030191 | 58030524 | chr4 | 62066196 | 62066553 | chr4 | 62067511 | 62067624 |
| chr4 | 62068072 | 62068150 | chr4 | 66535130 | 66535314 | chr4 | 66535351 | 66535443 |
| chr4 | 66536171 | 66536323 | chr4 | 73459699 | 73459762 | chr4 | 74142341 | 74142434 |
| chr4 | 74702479 | 74702516 | chr4 | 74735076 | 74235137 | chr4 | 74809877 | 74809933 |
| chr4 | 75241080 | 75241435 | chr4 | 75858573 | 75858629 | chr4 | 76554873 | 76554935 |
| chr4 | 76555532 | 76555856 | chr4 | 76912698 | 76912733 | chr4 | 79611132 | 79611294 |
| chr4 | 79689651 | 79689732 | chr4 | 79861530 | 79861560 | chr4 | 80273120 | 80273150 |
| chr4 | 81106351 | 81106871 | chr4 | 81124277 | 81124662 | chr4 | 81187046 | 81187076 |
| chr4 | 81187559 | 81187589 | chr4 | 81188385 | 81188489 | chr4 | 81188491 | 81188556 |
| chr4 | 81189419 | 81189660 | chr4 | 81189714 | 81189911 | chr4 | 81951431 | 81951460 |
| chr4 | 81951941 | 81951970 | chr4 | 81952170 | 81952311 | chr4 | 82135873 | 82135887 |
| chr4 | 82135920 | 82136056 | chr4 | 82136495 | 82136548 | chr4 | 82136807 | 82136837 |
| chr4 | 83323506 | 83323708 | chr4 | 83343366 | 83343396 | chr4 | 83720611 | 83720643 |
| chr4 | 83809740 | 83809787 | chr4 | 83955171 | 83955201 | chr4 | 83988361 | 83988511 |
| chr4 | 84035907 | 84035936 | chr4 | 85402377 | 85402511 | chr4 | 85402776 | 85403423 |
| chr4 | 85403913 | 85403927 | chr4 | 85404112 | 85404140 | chr4 | 85404225 | 85404475 |

TABLE 12-continued

| chr | start | end | chr | start | end | chr | start | end |
|---|---|---|---|---|---|---|---|---|
| chr4 | 85404650 | 85404693 | chr4 | 85414045 | 85414113 | chr4 | 85414725 | 85414846 |
| chr4 | 85417336 | 85417564 | chr4 | 85417953 | 85418079 | chr4 | 85418522 | 85418582 |
| chr4 | 85420591 | 85420621 | chr4 | 85422188 | 85422432 | chr4 | 85422973 | 85423316 |
| chr4 | 85424401 | 85424483 | chr4 | 87515337 | 87515367 | chr4 | 89378464 | 89378497 |
| chr4 | 89378744 | 89378766 | chr4 | 89378832 | 89378888 | chr4 | 90043517 | 90043547 |
| chr4 | 90757517 | 90757828 | chr4 | 90758105 | 90758134 | chr4 | 90758776 | 90758883 |
| chr4 | 91079842 | 91079899 | chr4 | 93224972 | 93225171 | chr4 | 93226365 | 93226703 |
| chr4 | 93226729 | 93227129 | chr4 | 94749725 | 94749755 | chr4 | 94750982 | 94751140 |
| chr4 | 94751419 | 94751502 | chr4 | 94753415 | 94753445 | chr4 | 94756002 | 94756109 |
| chr4 | 95127590 | 95127717 | chr4 | 95128038 | 95128068 | chr4 | 95762672 | 95762896 |
| chr4 | 96470752 | 96470782 | chr4 | 101111246 | 101111504 | chr4 | 101111857 | 101111970 |
| chr4 | 102332467 | 102332611 | chr4 | 102711731 | 102711787 | chr4 | 103929642 | 103929796 |
| chr4 | 103930065 | 103930095 | chr4 | 106335495 | 106335617 | chr4 | 107955311 | 107955826 |
| chr4 | 107956676 | 107957086 | chr4 | 107957373 | 107957466 | chr4 | 109093101 | 109093168 |
| chr4 | 109093405 | 109093506 | chr4 | 110223090 | 110223427 | chr4 | 110223579 | 110223980 |
| chr4 | 110344202 | 110344294 | chr4 | 110735672 | 110735702 | chr4 | 111532705 | 111532961 |
| chr4 | 111536288 | 111536505 | chr4 | 111536562 | 111536693 | chr4 | 111536960 | 111536974 |
| chr4 | 111537407 | 111537497 | chr4 | 111540199 | 111540360 | chr4 | 111542474 | 111542757 |
| chr4 | 111543232 | 111543345 | chr4 | 111543404 | 111543450 | chr4 | 111543661 | 111543695 |
| chr4 | 111543721 | 111543735 | chr4 | 111544381 | 111544583 | chr4 | 111549800 | 111549830 |
| chr4 | 111550618 | 111550834 | chr4 | 111552118 | 111552148 | chr4 | 111553099 | 111553450 |
| chr4 | 111553916 | 111553951 | chr4 | 111554950 | 111554964 | chr4 | 111555194 | 111555343 |
| chr4 | 111557965 | 111558049 | chr4 | 111558551 | 111559233 | chr4 | 111560249 | 111560636 |
| chr4 | 111562576 | 111562648 | chr4 | 113154896 | 113155129 | chr4 | 113430640 | 113430672 |
| chr4 | 113431834 | 113431854 | chr4 | 113431916 | 113432154 | chr4 | 113432227 | 113432503 |
| chr4 | 113432519 | 113432573 | chr4 | 113436216 | 113436287 | chr4 | 113441592 | 113441733 |
| chr4 | 113442098 | 113442185 | chr4 | 113442247 | 113442525 | chr4 | 113444020 | 113444448 |
| chr4 | 113559163 | 113559422 | chr4 | 117847399 | 117847458 | chr4 | 121844063 | 121844206 |
| chr4 | 121992265 | 121992312 | chr4 | 121993997 | 121994251 | chr4 | 122301422 | 122301712 |
| chr4 | 122302116 | 122302246 | chr4 | 122685807 | 122685890 | chr4 | 122686209 | 122686507 |
| chr4 | 122871294 | 122871334 | chr4 | 122871573 | 122872000 | chr4 | 123664228 | 123664363 |
| chr4 | 126237310 | 126237611 | chr4 | 126238024 | 126238436 | chr4 | 128544048 | 128544161 |
| chr4 | 128544646 | 128544789 | chr4 | 128967250 | 128967329 | chr4 | 128968647 | 128968800 |
| chr4 | 128969310 | 128969382 | chr4 | 128984386 | 128984464 | chr4 | 130018134 | 130018266 |
| chr4 | 134067881 | 134068004 | chr4 | 134068577 | 134068791 | chr4 | 134069289 | 134069318 |
| chr4 | 134069578 | 134069896 | chr4 | 134070374 | 134070403 | chr4 | 134071648 | 134072610 |
| chr4 | 134072677 | 134072967 | chr4 | 134073184 | 134073322 | chr4 | 134073568 | 134073641 |
| chr4 | 134073862 | 134073919 | chr4 | 134074030 | 134074155 | chr4 | 140200529 | 140201166 |
| chr4 | 140201193 | 140201462 | chr4 | 140656543 | 140656665 | chr4 | 140656858 | 140657089 |
| chr4 | 141347942 | 141348151 | chr4 | 141418921 | 141419146 | chr4 | 141488870 | 141489128 |
| chr4 | 142053130 | 142053160 | chr4 | 142053520 | 142053734 | chr4 | 142054239 | 142054460 |
| chr4 | 143766796 | 143766930 | chr4 | 144586035 | 144586088 | chr4 | 144621336 | 144621439 |
| chr4 | 144621515 | 144621896 | chr4 | 144621982 | 144622058 | chr4 | 145568052 | 145568147 |
| chr4 | 145568459 | 145568741 | chr4 | 146853951 | 146853981 | chr4 | 147558272 | 147558381 |
| chr4 | 147558477 | 147558504 | chr4 | 147559321 | 147560078 | chr4 | 147560134 | 147560418 |
| chr4 | 147560460 | 147560617 | chr4 | 147560933 | 147561145 | chr4 | 147561360 | 147561949 |
| chr4 | 147562000 | 147562055 | chr4 | 147568636 | 147569060 | chr4 | 147569620 | 147569650 |
| chr4 | 147576177 | 147576201 | chr4 | 147576330 | 147576639 | chr4 | 151974287 | 151974510 |
| chr4 | 152148807 | 152148836 | chr4 | 152246132 | 152246314 | chr4 | 153247273 | 153247386 |
| chr4 | 153249362 | 153249398 | chr4 | 153251894 | 153251923 | chr4 | 153702668 | 153702702 |
| chr4 | 154216241 | 154216357 | chr4 | 154374504 | 154374630 | chr4 | 154709524 | 154709610 |
| chr4 | 154709759 | 154710617 | chr4 | 154710729 | 154710914 | chr4 | 154712172 | 154712594 |
| chr4 | 154713500 | 154713530 | chr4 | 154713949 | 154714010 | chr4 | 155254166 | 155254196 |
| chr4 | 155411851 | 155412279 | chr4 | 155663209 | 155663647 | chr4 | 155665445 | 155665475 |
| chr4 | 156129153 | 156129183 | chr4 | 156129451 | 156129495 | chr4 | 156129746 | 156129797 |
| chr4 | 156130047 | 156130297 | chr4 | 156297416 | 156297556 | chr4 | 156297942 | 156298073 |
| chr4 | 156588311 | 156588401 | chr4 | 156589273 | 156589323 | chr4 | 156680257 | 156680532 |
| chr4 | 156681370 | 156681489 | chr4 | 158101782 | 158102020 | chr4 | 158141576 | 158141606 |
| chr4 | 158142847 | 158142999 | chr4 | 168143443 | 158143465 | chr4 | 159063301 | 159063331 |
| chr4 | 159149784 | 159149824 | chr4 | 164252991 | 164253447 | chr4 | 164819191 | 164819221 |
| chr4 | 165304515 | 165304578 | chr4 | 165305060 | 165305163 | chr4 | 166414834 | 166414921 |
| chr4 | 166794771 | 166794909 | chr4 | 166796118 | 166796212 | chr4 | 168155109 | 168155269 |
| chr4 | 170865234 | 170865287 | chr4 | 170947287 | 170947325 | chr4 | 171012375 | 171012409 |
| chr4 | 172132870 | 172133019 | chr4 | 172734189 | 172734203 | chr4 | 172734592 | 172734790 |
| chr4 | 173953411 | 173953594 | chr4 | 174083164 | 174083431 | chr4 | 174124429 | 174124447 |
| chr4 | 174136704 | 174136734 | chr4 | 174224186 | 174224216 | chr4 | 174429658 | 174429688 |
| chr4 | 174430310 | 174430553 | chr4 | 174430794 | 174431072 | chr4 | 174438567 | 174438744 |
| chr4 | 174439822 | 174440257 | chr4 | 174440635 | 174440713 | chr4 | 174443212 | 174443242 |
| chr4 | 174443563 | 174443934 | chr4 | 174446508 | 174446525 | chr4 | 174446952 | 174447005 |
| chr4 | 174449950 | 174450726 | chr4 | 174450752 | 174451482 | chr4 | 174451855 | 174452098 |
| chr4 | 174459185 | 174459374 | chr4 | 174459528 | 174459840 | chr4 | 174460186 | 174460221 |
| chr4 | 175132735 | 175132765 | chr4 | 175133085 | 175133201 | chr4 | 175134897 | 175135672 |
| chr4 | 175135921 | 175136011 | chr4 | 175138411 | 175138546 | chr4 | 175138964 | 175139124 |
| chr4 | 175139559 | 175139685 | chr4 | 175750456 | 175750738 | chr4 | 176923424 | 176923558 |
| chr4 | 176987324 | 176987373 | chr4 | 177713228 | 177713437 | chr4 | 178285756 | 178285879 |
| chr4 | 180979220 | 180979300 | chr4 | 180980297 | 180980356 | chr4 | 183063666 | 183063950 |
| chr4 | 183064617 | 183064655 | chr4 | 183064874 | 183064966 | chr4 | 184019249 | 184019316 |
| chr4 | 184019692 | 184019736 | chr4 | 184020106 | 184020179 | chr4 | 184375546 | 184375726 |

TABLE 12-continued

| chr | start | end | chr | start | end | chr | start | end |
|---|---|---|---|---|---|---|---|---|
| chr4 | 184491996 | 184492042 | chr4 | 184644053 | 184644249 | chr4 | 184718260 | 184718352 |
| chr4 | 184826238 | 184826493 | chr4 | 184826938 | 184827237 | chr4 | 184921855 | 184922091 |
| chr4 | 185089696 | 185089797 | chr4 | 185937333 | 185937889 | chr4 | 185938497 | 185938564 |
| chr4 | 185940338 | 185940460 | chr4 | 185941585 | 185942472 | chr4 | 185942492 | 185942760 |
| chr4 | 187647073 | 187647457 | chr5 | 53849 | 53898 | chr5 | 92163 | 92399 |
| chr5 | 230673 | 230709 | chr5 | 303272 | 303301 | chr5 | 320840 | 320982 |
| chr5 | 343916 | 343941 | chr5 | 373363 | 373392 | chr5 | 373872 | 374266 |
| chr5 | 400186 | 400215 | chr5 | 400502 | 400531 | chr5 | 415870 | 415899 |
| chr5 | 481012 | 481121 | chr5 | 491335 | 491536 | chr5 | 524337 | 524404 |
| chr5 | 538758 | 538806 | chr5 | 554299 | 554538 | chr5 | 554871 | 554900 |
| chr5 | 555158 | 555285 | chr5 | 555965 | 555995 | chr5 | 677889 | 678006 |
| chr5 | 909204 | 909304 | chr5 | 912806 | 912835 | chr5 | 1034600 | 1034653 |
| chr5 | 1059523 | 1059556 | chr5 | 1093660 | 1093797 | chr5 | 1117778 | 1118270 |
| chr5 | 1131217 | 1131378 | chr5 | 1136590 | 1136845 | chr5 | 1193381 | 1193521 |
| chr5 | 1193880 | 1193944 | chr5 | 1221197 | 1221307 | chr5 | 1259524 | 1259558 |
| chr5 | 1271339 | 1271396 | chr5 | 1294630 | 1294767 | chr5 | 1295031 | 129442 |
| chr5 | 1295605 | 1295662 | chr5 | 1445171 | 1445255 | chr5 | 1445738 | 1445759 |
| chr5 | 1445841 | 1445928 | chr5 | 1446319 | 1446369 | chr5 | 1446443 | 1446599 |
| chr5 | 1747022 | 1747098 | chr5 | 1779526 | 1779556 | chr5 | 1787378 | 1787418 |
| chr5 | 1874892 | 1875099 | chr5 | 1875453 | 1875497 | chr5 | 1875870 | 1876306 |
| chr5 | 1876638 | 1876860 | chr5 | 1877195 | 1877239 | chr5 | 1878014 | 1878028 |
| chr5 | 1878224 | 1878528 | chr5 | 1878831 | 1879045 | chr5 | 1879605 | 1879661 |
| chr5 | 1879690 | 1879719 | chr5 | 1882420 | 1882605 | chr5 | 1882844 | 1882921 |
| chr5 | 1883515 | 1883616 | chr5 | 1884178 | 1884237 | chr5 | 1884557 | 1884698 |
| chr5 | 1885158 | 1885458 | chr5 | 1885985 | 1886076 | chr5 | 1886542 | 1886581 |
| chr5 | 1886812 | 1886841 | chr5 | 1886998 | 1887145 | chr5 | 1887547 | 1887581 |
| chr5 | 1887656 | 1887737 | chr5 | 1930786 | 1931004 | chr5 | 1931065 | 1931286 |
| chr5 | 1931445 | 1931576 | chr5 | 1931618 | 1931754 | chr5 | 1950794 | 1950960 |
| chr5 | 1952624 | 1952638 | chr5 | 2038705 | 2038850 | chr5 | 2225439 | 2225469 |
| chr5 | 2324383 | 2324413 | chr5 | 2367718 | 2367892 | chr5 | 2541487 | 2541611 |
| chr5 | 2738848 | 2739129 | chr5 | 2739211 | 2739354 | chr5 | 2739877 | 2740300 |
| chr5 | 2740431 | 2740664 | chr5 | 2743617 | 2743659 | chr5 | 2743699 | 2743713 |
| chr5 | 2248374 | 2748459 | chr5 | 2749213 | 2749406 | chr5 | 2749699 | 2749729 |
| chr5 | 2750435 | 2750516 | chr5 | 2750655 | 2750769 | chr5 | 2751855 | 2751894 |
| chr5 | 2752991 | 2753040 | chr5 | 2753048 | 2753078 | chr5 | 2754738 | 2754767 |
| chr5 | 2755323 | 2756388 | chr5 | 2756599 | 2756602 | chr5 | 2756674 | 2757427 |
| chr5 | 3031879 | 3032018 | chr5 | 3152146 | 3152176 | chr5 | 3325042 | 3325272 |
| chr5 | 3590405 | 3590657 | chr5 | 3591354 | 3591388 | chr5 | 3591857 | 3592037 |
| chr5 | 3592728 | 3592881 | chr5 | 3594250 | 3594519 | chr5 | 3595090 | 3595178 |
| chr5 | 3595850 | 3595991 | chr5 | 3596556 | 3596724 | chr5 | 3596825 | 3596880 |
| chr5 | 3597411 | 3597461 | chr5 | 3600150 | 3600180 | chr5 | 3602804 | 3603320 |
| chr5 | 3674053 | 3674224 | chr5 | 4144367 | 4144516 | chr5 | 5139754 | 5139900 |
| chr5 | 5140170 | 5140225 | chr5 | 5140630 | 5140757 | chr5 | 5140850 | 5140901 |
| chr5 | 6228617 | 6228790 | chr5 | 6448930 | 6449582 | chr5 | 6482458 | 6482620 |
| chr5 | 6583461 | 6583579 | chr5 | 6687277 | 6687431 | chr5 | 6755789 | 5755843 |
| chr5 | 7396263 | 7396393 | chr5 | 7395434 | 7395538 | chr5 | 7851015 | 7851121 |
| chr5 | 9546612 | 9546648 | chr5 | 10249098 | 10249127 | chr5 | 10333688 | 10334132 |
| chr5 | 10565021 | 10565227 | chr5 | 10565263 | 10565607 | chr5 | 10616516 | 10616550 |
| chr5 | 11384965 | 11385363 | chr5 | 11903822 | 11904173 | chr5 | 11904196 | 11904379 |
| chr5 | 11904456 | 11904696 | chr5 | 11904896 | 11904943 | chr5 | 14872919 | 14873053 |
| chr5 | 15500748 | 15500927 | chr5 | 16179049 | 16179141 | chr5 | 16179555 | 16179713 |
| chr5 | 16180183 | 16180260 | chr5 | 16466784 | 16467120 | chr5 | 16793851 | 16794008 |
| chr5 | 16845452 | 16845619 | chr5 | 16936354 | 16936514 | chr5 | 16968118 | 16968148 |
| chr5 | 17095895 | 17095927 | chr5 | 17203012 | 17203177 | chr5 | 17218195 | 17218225 |
| chr5 | 17218986 | 17219018 | chr5 | 17311046 | 17311076 | chr5 | 17512114 | 17512144 |
| chr5 | 18034335 | 18034365 | chr5 | 22853443 | 22853508 | chr5 | 23011928 | 23011958 |
| chr5 | 31193937 | 31193989 | chr5 | 31194375 | 31194641 | chr5 | 31572285 | 31572344 |
| chr5 | 31639684 | 31639960 | chr5 | 31691477 | 31691652 | chr5 | 31855073 | 31855199 |
| chr5 | 31879243 | 31879282 | chr5 | 32042283 | 32042419 | chr5 | 32314345 | 32314379 |
| chr5 | 32333032 | 32333111 | chr5 | 32446143 | 32446274 | chr5 | 32710331 | 32710470 |
| chr5 | 32710802 | 32711531 | chr5 | 32711826 | 32711870 | chr5 | 32712077 | 32712101 |
| chr5 | 32712290 | 32712491 | chr5 | 32712764 | 32713304 | chr5 | 33234280 | 33234411 |
| chr5 | 33298005 | 33298076 | chr5 | 33509607 | 33509776 | chr5 | 33892083 | 33892115 |
| chr5 | 33892413 | 33892443 | chr5 | 33936156 | 33936336 | chr5 | 33936485 | 33936516 |
| chr5 | 33936599 | 33936663 | chr5 | 34656932 | 34657034 | chr5 | 35874560 | 35874589 |
| chr5 | 35939832 | 35939861 | chr5 | 37376644 | 37376674 | chr5 | 37834684 | 37834714 |
| chr5 | 37835015 | 37835125 | chr5 | 37836231 | 37836260 | chr5 | 37836649 | 37837992 |
| chr5 | 37838548 | 37838885 | chr5 | 37839808 | 37840125 | chr5 | 37840530 | 37840853 |
| chr5 | 38257485 | 38257606 | chr5 | 38257842 | 38257908 | chr5 | 38257945 | 38257959 |
| chr5 | 38557070 | 38557400 | chr5 | 38845675 | 38846164 | chr5 | 39281800 | 39281943 |
| chr5 | 39343181 | 39343348 | chr5 | 40681122 | 40681227 | chr5 | 40681262 | 40681367 |
| chr5 | 40681676 | 40681839 | chr5 | 40775147 | 40775313 | chr5 | 42260050 | 42260453 |
| chr5 | 42424822 | 42425060 | chr5 | 42931966 | 42931996 | chr5 | 42950980 | 42951311 |
| chr5 | 42951420 | 42952111 | chr5 | 42991826 | 42992241 | chr5 | 42992376 | 42992597 |
| chr5 | 42992783 | 42992934 | chr5 | 42993150 | 42994193 | chr5 | 42994694 | 42994790 |
| chr5 | 42995115 | 42995153 | chr5 | 43007936 | 43007966 | chr5 | 43008202 | 43008562 |
| chr5 | 43017953 | 43018176 | chr5 | 43018327 | 43018767 | chr5 | 43019238 | 43019342 |
| chr5 | 43019809 | 43019887 | chr5 | 43020146 | 43020294 | chr5 | 43040544 | 43040635 |

TABLE 12-continued

| chr | start | end | chr | start | end | chr | start | end |
|---|---|---|---|---|---|---|---|---|
| chr5 | 43040870 | 43040964 | chr5 | 43215538 | 43215738 | chr5 | 43397002 | 43397229 |
| chr5 | 43402678 | 43403084 | chr5 | 43558065 | 43558099 | chr5 | 44389782 | 44389852 |
| chr5 | 45695186 | 45695239 | chr5 | 45695314 | 45695533 | chr5 | 45695906 | 45695947 |
| chr5 | 45696336 | 45696439 | chr5 | 49736592 | 49736685 | chr5 | 50262893 | 50263014 |
| chr5 | 50263568 | 50263641 | chr5 | 50264307 | 50264603 | chr5 | 50264820 | 50264850 |
| chr5 | 50265325 | 50265429 | chr5 | 50265721 | 50265880 | chr5 | 50674152 | 50674188 |
| chr5 | 50674560 | 50674590 | chr5 | 50675013 | 50675075 | chr5 | 50678346 | 50678490 |
| chr5 | 50695351 | 50695463 | chr5 | 52084073 | 52084134 | chr5 | 52887899 | 52888047 |
| chr5 | 54179610 | 54179633 | chr5 | 54180063 | 54180093 | chr5 | 54516371 | 54516680 |
| chr5 | 54516832 | 54517017 | chr5 | 54518651 | 54519288 | chr5 | 54527323 | 54527343 |
| chr5 | 56077938 | 56078065 | chr5 | 56246546 | 56246575 | chr5 | 56247942 | 56247971 |
| chr5 | 56248218 | 56248257 | chr5 | 56467399 | 56467666 | chr5 | 57878271 | 57878375 |
| chr5 | 57878710 | 57878752 | chr5 | 59188291 | 59188327 | chr5 | 59189055 | 59189057 |
| chr5 | 59189189 | 59189206 | chr5 | 59189863 | 59189948 | chr5 | 63254903 | 63255242 |
| chr5 | 63256863 | 63256895 | chr5 | 63257727 | 63257861 | chr5 | 63802007 | 63802304 |
| chr5 | 63802340 | 63802514 | chr5 | 63986488 | 63986527 | chr5 | 63986570 | 63986807 |
| chr5 | 65181732 | 65181778 | chr5 | 67569803 | 67569832 | chr5 | 67588937 | 67589162 |
| chr5 | 67589598 | 67589627 | chr5 | 67590431 | 67590460 | chr5 | 67591068 | 67591157 |
| chr5 | 68391042 | 68391336 | chr5 | 71014720 | 71014895 | chr5 | 71015180 | 71015728 |
| chr5 | 71106820 | 71107027 | chr5 | 71403566 | 71403653 | chr5 | 71403975 | 71404207 |
| chr5 | 22416246 | 72416751 | chr5 | 72526413 | 72526414 | chr5 | 72526492 | 72526643 |
| chr5 | 72528434 | 72528464 | chr5 | 72529289 | 72529825 | chr5 | 72529890 | 72530609 |
| chr5 | 72594802 | 72594836 | chr5 | 72594868 | 72595016 | chr5 | 72595047 | 72595059 |
| chr5 | 72595542 | 72595721 | chr5 | 72595774 | 72595788 | chr5 | 72599079 | 72599441 |
| chr5 | 72599463 | 72599833 | chr5 | 72677775 | 72677825 | chr5 | 72677998 | 72678028 |
| chr5 | 72715204 | 72715347 | chr5 | 72715591 | 72715695 | chr5 | 72715731 | 72715768 |
| chr5 | 72716102 | 72716180 | chr5 | 72732870 | 72732884 | chr5 | 72733093 | 72733185 |
| chr5 | 72740147 | 72740184 | chr5 | 72746680 | 72746683 | chr5 | 74061571 | 74061786 |
| chr5 | 74991793 | 74991908 | chr5 | 75377883 | 75378033 | chr5 | 75380163 | 75380193 |
| chr5 | 75380624 | 75380974 | chr5 | 76011285 | 76011337 | chr5 | 76012576 | 76012605 |
| chr5 | 76249270 | 76249670 | chr5 | 76249696 | 76249906 | chr5 | 76249945 | 76250150 |
| chr5 | 76250435 | 76250504 | chr5 | 76327468 | 76327697 | chr5 | 76506469 | 76506506 |
| chr5 | 76507035 | 76507114 | chr5 | 76923679 | 76924023 | chr5 | 76924087 | 76924299 |
| chr5 | 76924930 | 76924960 | chr5 | 76925561 | 76925690 | chr5 | 76928157 | 76928397 |
| chr5 | 76928688 | 76928906 | chr5 | 76932302 | 76932332 | chr5 | 76932542 | 76933265 |
| chr5 | 76934173 | 76934653 | chr5 | 76934677 | 76934870 | chr5 | 76936016 | 76936721 |
| chr5 | 76939436 | 76939774 | chr5 | 76940340 | 76940374 | chr5 | 76941201 | 76941326 |
| chr5 | 77140527 | 77140711 | chr5 | 77147563 | 77147649 | chr5 | 77147873 | 77148195 |
| chr5 | 77148498 | 27148712 | chr5 | 77268367 | 77269237 | chr5 | 77269264 | 77269309 |
| chr5 | 77655342 | 77655388 | chr5 | 78005726 | 78005913 | chr5 | 78039632 | 78039673 |
| chr5 | 78407651 | 78407840 | chr5 | 78408192 | 78408274 | chr5 | 78408298 | 78408451 |
| chr5 | 78910189 | 78910332 | chr5 | 79554097 | 79554169 | chr5 | 79563425 | 79563643 |
| chr5 | 79598681 | 79598836 | chr5 | 79783240 | 79783421 | chr5 | 79864898 | 79865078 |
| chr5 | 79866100 | 79866414 | chr5 | 79947584 | 79947707 | chr5 | 80255816 | 80256074 |
| chr5 | 80689543 | 80689735 | chr5 | 80690118 | 80690239 | chr5 | 82168369 | 82168480 |
| chr5 | 82767429 | 82767793 | chr5 | 82768892 | 82769061 | chr5 | 83679195 | 83679225 |
| chr5 | 83679681 | 83680340 | chr5 | 83680615 | 83680664 | chr5 | 83680694 | 83680708 |
| chr5 | 86414242 | 86414297 | chr5 | 87955460 | 87955664 | chr5 | 87956199 | 87956662 |
| chr5 | 87956680 | 87956964 | chr5 | 87962966 | 87963002 | chr5 | 87963390 | 87963511 |
| chr5 | 87967773 | 87968077 | chr5 | 87968486 | 87968685 | chr5 | 87968773 | 87968858 |
| chr5 | 87970193 | 87970872 | chr5 | 87974104 | 87974307 | chr5 | 87974868 | 87975023 |
| chr5 | 87976028 | 87976308 | chr5 | 87976525 | 87976559 | chr5 | 87979755 | 87979912 |
| chr5 | 87980142 | 87980250 | chr5 | 87980954 | 87981325 | chr5 | 87984532 | 87984657 |
| chr5 | 87985922 | 87985954 | chr5 | 87986210 | 87986281 | chr5 | 87986547 | 87986581 |
| chr5 | 87988516 | 87988584 | chr5 | 87990408 | 87990452 | chr5 | 88185470 | 88186001 |
| chr5 | 89854856 | 89854902 | chr5 | 94889396 | 94889434 | chr5 | 94955681 | 94955919 |
| chr5 | 94956935 | 94957000 | chr5 | 94982042 | 94982225 | chr5 | 95767894 | 95768384 |
| chr5 | 95768920 | 95769093 | chr5 | 96114587 | 96114632 | chr5 | 100236682 | 100236757 |
| chr5 | 100238882 | 100239119 | chr5 | 100239135 | 100239151 | chr5 | 101631487 | 101631533 |
| chr5 | 101632295 | 101632573 | chr5 | 107005983 | 107006186 | chr5 | 111987744 | 111987818 |
| chr5 | 112042844 | 112042873 | chr5 | 112042904 | 112043289 | chr5 | 112073358 | 112073516 |
| chr5 | 112170808 | 112170837 | chr5 | 112175198 | 112175227 | chr5 | 112175640 | 112175669 |
| chr5 | 112258359 | 112258388 | chr5 | 112258634 | 112258663 | chr5 | 112340666 | 112340704 |
| chr5 | 112629427 | 112629674 | chr5 | 113391265 | 113392018 | chr5 | 113698567 | 113698583 |
| chr5 | 113698670 | 113698783 | chr5 | 113699008 | 113699119 | chr5 | 114515010 | 114515579 |
| chr5 | 114515611 | 114515671 | chr5 | 115151267 | 115151357 | chr5 | 115151650 | 115152384 |
| chr5 | 115152617 | 115152638 | chr5 | 115154758 | 115154825 | chr5 | 115176039 | 115176228 |
| chr5 | 115297192 | 115297292 | chr5 | 115297377 | 115297556 | chr5 | 115297928 | 115297985 |
| chr5 | 115298496 | 115298581 | chr5 | 115298985 | 115299041 | chr5 | 116143271 | 116143325 |
| chr5 | 119799931 | 119799986 | chr5 | 119801299 | 119801445 | chr5 | 120399966 | 120400129 |
| chr5 | 121413537 | 121413590 | chr5 | 122422240 | 122422292 | chr5 | 122422616 | 122422651 |
| chr5 | 122423328 | 122423376 | chr5 | 122425128 | 122425168 | chr5 | 122431118 | 122431378 |
| chr5 | 124128410 | 124128497 | chr5 | 126231644 | 126231674 | chr5 | 126245097 | 126245133 |
| chr5 | 126626283 | 126626738 | chr5 | 127088743 | 127088773 | chr5 | 127872942 | 127872990 |
| chr5 | 127873553 | 127873710 | chr5 | 127874448 | 127874477 | chr5 | 127874706 | 127874839 |
| chr5 | 128300680 | 128300694 | chr5 | 128300713 | 128300794 | chr5 | 128796081 | 128796244 |
| chr5 | 128796867 | 128796985 | chr5 | 128797344 | 128797386 | chr5 | 129240068 | 129240101 |
| chr5 | 130163448 | 130153623 | chr5 | 131134159 | 131134203 | chr5 | 131992096 | 131992167 |

TABLE 12-continued

| chr | start | end | chr | start | end | chr | start | end |
|---|---|---|---|---|---|---|---|---|
| chr5 | 132947486 | 132947836 | chr5 | 133820008 | 133820040 | chr5 | 133968996 | 133969192 |
| chr5 | 134364195 | 134364289 | chr5 | 134366718 | 134366788 | chr5 | 134367108 | 134367203 |
| chr5 | 134374447 | 134374505 | chr5 | 134374792 | 134375210 | chr5 | 134376222 | 134376375 |
| chr5 | 134376732 | 134376824 | chr5 | 134385952 | 134386167 | chr5 | 134386185 | 134386383 |
| chr5 | 134582864 | 134582894 | chr5 | 134735622 | 134735651 | chr5 | 134825463 | 134825518 |
| chr5 | 134825913 | 134826006 | chr5 | 134870446 | 134870515 | chr5 | 134870780 | 134870926 |
| chr5 | 134871601 | 134872049 | chr5 | 134879478 | 134880022 | chr5 | 134880049 | 134880501 |
| chr5 | 134914627 | 134914748 | chr5 | 135265737 | 135265767 | chr5 | 135266114 | 135266128 |
| chr5 | 135266578 | 135266672 | chr5 | 135528201 | 135528233 | chr5 | 136834050 | 136834050 |
| chr5 | 136834290 | 136834506 | chr5 | 136834720 | 136834826 | chr5 | 137225092 | 137225297 |
| chr5 | 137404150 | 137404180 | chr5 | 137912037 | 137912148 | chr5 | 138196197 | 138196408 |
| chr5 | 138273817 | 138273854 | chr5 | 139045286 | 139045315 | chr5 | 139047990 | 139048162 |
| chr5 | 139056666 | 139056804 | chr5 | 139227773 | 139227909 | chr5 | 139454108 | 139454202 |
| chr5 | 139525728 | 139525758 | chr5 | 139779555 | 139779871 | chr5 | 140174798 | 140174839 |
| chr5 | 140187094 | 140187146 | chr5 | 140305978 | 140306050 | chr5 | 140306445 | 140306619 |
| chr5 | 140306675 | 140306733 | chr5 | 140346595 | 140346671 | chr5 | 140514891 | 140514921 |
| chr5 | 140604459 | 140604501 | chr5 | 140613926 | 140614014 | chr5 | 140614314 | 140614328 |
| chr5 | 140683631 | 140683772 | chr5 | 140777328 | 140777487 | chr5 | 140787623 | 140787637 |
| chr5 | 140797076 | 140797278 | chr5 | 140797328 | 140797342 | chr5 | 140800479 | 140800964 |
| chr5 | 140801035 | 140801246 | chr5 | 140855598 | 140856458 | chr5 | 140856547 | 140856622 |
| chr5 | 141031121 | 141031150 | chr5 | 141263035 | 141263142 | chr5 | 141931340 | 141931354 |
| chr5 | 141931425 | 141931539 | chr5 | 142784967 | 142785272 | chr5 | 145713645 | 145713896 |
| chr5 | 145717175 | 145717196 | chr5 | 145717249 | 145717437 | chr5 | 145718802 | 145719753 |
| chr5 | 145719835 | 145719925 | chr5 | 145720812 | 145720917 | chr5 | 145722116 | 145722466 |
| chr5 | 145722561 | 145723027 | chr5 | 145724502 | 145724698 | chr5 | 145725694 | 145725844 |
| chr5 | 146257332 | 146257602 | chr5 | 146889332 | 146889575 | chr5 | 147003444 | 147003536 |
| chr5 | 147326357 | 147326510 | chr5 | 149503827 | 149503856 | chr5 | 149682074 | 149682166 |
| chr5 | 150029147 | 150029245 | chr5 | 150051101 | 150051667 | chr5 | 150326159 | 150326188 |
| chr5 | 150400123 | 150400203 | chr5 | 151066442 | 151066474 | chr5 | 151304371 | 151304401 |
| chr5 | 153852664 | 153852792 | chr5 | 153853420 | 153853478 | chr5 | 153854330 | 153854360 |
| chr5 | 153855175 | 153855264 | chr5 | 153855658 | 153855839 | chr5 | 153856149 | 153856936 |
| chr5 | 153856936 | 153856996 | chr5 | 153857379 | 153857429 | chr5 | 153858319 | 153858599 |
| chr5 | 153859676 | 153859708 | chr5 | 153862037 | 153862179 | chr5 | 153862219 | 153862577 |
| chr5 | 153863421 | 153863451 | chr5 | 154030048 | 154030160 | chr5 | 154061801 | 154061894 |
| chr5 | 154209926 | 154209987 | chr5 | 154318148 | 154318329 | chr5 | 155107794 | 155107848 |
| chr5 | 155108161 | 155108267 | chr5 | 155108356 | 155108526 | chr5 | 155108733 | 155108763 |
| chr5 | 156485385 | 156485415 | chr5 | 156558444 | 156558689 | chr5 | 156655170 | 156655200 |
| chr5 | 156874257 | 156874308 | chr5 | 157001739 | 157001843 | chr5 | 157078419 | 157078449 |
| chr5 | 157098362 | 157098619 | chr5 | 157673799 | 157673964 | chr5 | 158478513 | 158478764 |
| chr5 | 158524692 | 158524748 | chr5 | 158524865 | 158524925 | chr5 | 158527443 | 158528069 |
| chr5 | 158612981 | 158613074 | chr5 | 159399095 | 159399099 | chr5 | 159437197 | 159437235 |
| chr5 | 160975724 | 160975754 | chr5 | 161274310 | 161274554 | chr5 | 166865449 | 166865616 |
| chr5 | 167956177 | 167956266 | chr5 | 167956414 | 167956595 | chr5 | 168233396 | 168233482 |
| chr5 | 168727924 | 168727927 | chr5 | 169064327 | 169064805 | chr5 | 169366082 | 169366201 |
| chr5 | 169532927 | 169533012 | chr5 | 170108287 | 170108372 | chr5 | 170735154 | 170735206 |
| chr5 | 170735731 | 170735788 | chr5 | 170736116 | 170736163 | chr5 | 170736716 | 170736830 |
| chr5 | 170737282 | 170737479 | chr5 | 170737741 | 170737863 | chr5 | 170737936 | 170738689 |
| chr5 | 170738824 | 170739481 | chr5 | 170739823 | 170740027 | chr5 | 170740461 | 170740477 |
| chr5 | 170740575 | 170741240 | chr5 | 170741465 | 170742275 | chr5 | 170742387 | 170742599 |
| chr5 | 170742673 | 170743479 | chr5 | 170743647 | 170744128 | chr5 | 170744375 | 170744562 |
| chr5 | 170745389 | 170745480 | chr5 | 171352123 | 171352153 | chr5 | 172354043 | 172354118 |
| chr5 | 172485539 | 172485586 | chr5 | 172655879 | 172656216 | chr5 | 172659225 | 172659290 |
| chr5 | 172659496 | 172659655 | chr5 | 172659855 | 172660025 | chr5 | 172660142 | 172660218 |
| chr5 | 172660719 | 172661000 | chr5 | 172661127 | 172661684 | chr5 | 172664226 | 172664487 |
| chr5 | 172665590 | 172665812 | chr5 | 172670983 | 172671018 | chr5 | 172671345 | 172671481 |
| chr5 | 172671640 | 172671968 | chr5 | 172672477 | 172672663 | chr5 | 172754589 | 172754621 |
| chr5 | 172754832 | 172754931 | chr5 | 172755470 | 172755562 | chr5 | 172755595 | 172755663 |
| chr5 | 172757048 | 172757111 | chr5 | 174115388 | 174115861 | chr5 | 174147523 | 174147596 |
| chr5 | 174150415 | 174150445 | chr5 | 174159300 | 174159588 | chr5 | 174162874 | 174162904 |
| chr5 | 174220971 | 174221001 | chr5 | 174870738 | 174870786 | chr5 | 174871174 | 174871497 |
| chr5 | 174921456 | 174921629 | chr5 | 175085147 | 175085209 | chr5 | 175085525 | 175085719 |
| chr5 | 175223671 | 175223709 | chr5 | 175298549 | 175298883 | chr5 | 175299294 | 175299396 |
| chr5 | 175300351 | 175300381 | chr5 | 175621390 | 175621501 | chr5 | 175790961 | 175790991 |
| chr5 | 175792865 | 175792931 | chr5 | 175792998 | 175793063 | chr5 | 175831257 | 175831326 |
| chr5 | 175876388 | 175876504 | chr5 | 175971447 | 175971615 | chr5 | 175978889 | 175978976 |
| chr5 | 176024005 | 176024318 | chr5 | 176046363 | 176046554 | chr5 | 176107274 | 176107484 |
| chr5 | 176107518 | 176107586 | chr5 | 176236721 | 176236898 | chr5 | 176264805 | 176264915 |
| chr5 | 176295786 | 176295892 | chr5 | 176520166 | 176520195 | chr5 | 176522400 | 176522566 |
| chr5 | 176764100 | 176764169 | chr5 | 176827656 | 176827685 | chr5 | 177020093 | 177020153 |
| chr5 | 177031167 | 177031197 | chr5 | 177408292 | 177408443 | chr5 | 177411638 | 177412141 |
| chr5 | 177512244 | 177512377 | chr5 | 177556807 | 177557022 | chr5 | 177579824 | 177580065 |
| chr5 | 177644565 | 177644601 | chr5 | 177713376 | 177713468 | chr5 | 178004325 | 178004374 |
| chr5 | 178016682 | 178016983 | chr5 | 178017520 | 178017867 | chr5 | 178151333 | 178151363 |
| chr5 | 178368074 | 178368121 | chr5 | 178487107 | 178487303 | chr5 | 178487342 | 178487398 |
| chr5 | 178576356 | 178576499 | chr5 | 178655753 | 178655871 | chr5 | 178771314 | 178771630 |
| chr5 | 178771724 | 178771859 | chr5 | 178772205 | 178772272 | chr5 | 178772603 | 178772729 |
| chr5 | 178781548 | 178781577 | chr5 | 178955527 | 178955656 | chr5 | 178957637 | 178957944 |
| chr5 | 178969722 | 178969752 | chr5 | 178978946 | 178978976 | chr5 | 179060235 | 179060655 |

TABLE 12-continued

| chr | start | end | chr | start | end | chr | start | end |
|---|---|---|---|---|---|---|---|---|
| chr5 | 179098595 | 179098633 | chr5 | 179214113 | 179214196 | chr5 | 179217327 | 179217447 |
| chr5 | 179270584 | 179270748 | chr5 | 179553207 | 179553237 | chr5 | 179780104 | 179780144 |
| chr5 | 179780706 | 179780985 | chr5 | 179867486 | 179867548 | chr5 | 180017118 | 180017198 |
| chr5 | 180017608 | 180017933 | chr5 | 180018485 | 180018498 | chr5 | 180030654 | 180030700 |
| chr5 | 180047440 | 180047605 | chr5 | 180075846 | 180075857 | chr5 | 180076054 | 180076317 |
| chr5 | 180076567 | 180076602 | chr5 | 180076804 | 180076996 | chr5 | 180101016 | 180101167 |
| chr5 | 180101252 | 180101332 | chr5 | 180326126 | 180326156 | chr5 | 180454232 | 180454334 |
| chr5 | 180527546 | 180527698 | chr5 | 180594851 | 180595002 | chr5 | 180600858 | 180601218 |
| chr5 | 180612346 | 180612376 | chr5 | 180629320 | 180629350 | chr5 | 180636016 | 180636205 |
| chr6 | 373148 | 373290 | chr6 | 391173 | 391899 | chr6 | 392410 | 392433 |
| chr6 | 392588 | 392958 | chr6 | 393125 | 393472 | chr6 | 711142 | 711293 |
| chr6 | 1312000 | 1312096 | chr6 | 1312595 | 1312708 | chr6 | 1314088 | 1314100 |
| chr6 | 1378222 | 1378475 | chr6 | 1379584 | 1379614 | chr6 | 1379909 | 1379952 |
| chr6 | 1383677 | 1383708 | chr6 | 1383860 | 1384179 | chr6 | 1384626 | 1384644 |
| chr6 | 1385118 | 1385170 | chr6 | 1386071 | 1386112 | chr6 | 1389124 | 1389262 |
| chr6 | 1390241 | 1390405 | chr6 | 1390424 | 1390758 | chr6 | 1390956 | 1391035 |
| chr6 | 1391318 | 1391379 | chr6 | 1524199 | 1524283 | chr6 | 1605387 | 1605454 |
| chr6 | 1620672 | 1620701 | chr6 | 1624977 | 1625818 | chr6 | 2986688 | 2986718 |
| chr6 | 3053299 | 3053386 | chr6 | 3229029 | 3229059 | chr6 | 3229423 | 3229510 |
| chr6 | 3232010 | 3232260 | chr6 | 3247675 | 3247704 | chr6 | 3285222 | 3285513 |
| chr6 | 3405645 | 3405713 | chr6 | 4775062 | 4775222 | chr6 | 4836002 | 4836458 |
| chr6 | 4951247 | 4951390 | chr6 | 5359500 | 5359539 | chr6 | 5783325 | 5783496 |
| chr6 | 5996952 | 5996989 | chr6 | 5997802 | 5997832 | chr6 | 6003287 | 6003528 |
| chr6 | 6004350 | 6004743 | chr6 | 6004837 | 6005417 | chr6 | 6006374 | 6006419 |
| chr6 | 6006674 | 6006883 | chr6 | 6007593 | 6008277 | chr6 | 6367085 | 6367271 |
| chr6 | 6753803 | 6753839 | chr6 | 7726334 | 7726363 | chr6 | 7726630 | 7726659 |
| chr6 | 7726952 | 7726981 | chr6 | 7727699 | 7727768 | chr6 | 7728087 | 7728142 |
| chr6 | 7728849 | 7728941 | chr6 | 7731054 | 7731083 | chr6 | 7892314 | 7892412 |
| chr6 | 8014600 | 8014772 | chr6 | 10381507 | 10381592 | chr6 | 10381695 | 10381968 |
| chr6 | 10382722 | 10383049 | chr6 | 10383739 | 10383774 | chr6 | 10384950 | 10384974 |
| chr6 | 10385280 | 10385939 | chr6 | 10386210 | 10386273 | chr6 | 10390023 | 10391187 |
| chr6 | 10410518 | 10410578 | chr6 | 10411356 | 10411510 | chr6 | 10415113 | 10415215 |
| chr6 | 10415559 | 10415713 | chr6 | 10416118 | 10416351 | chr6 | 10417158 | 10417529 |
| chr6 | 10419086 | 10419439 | chr6 | 10419477 | 10419506 | chr6 | 10419744 | 10419941 |
| chr6 | 10421053 | 10421451 | chr6 | 10421549 | 10422635 | chr6 | 10423613 | 10423704 |
| chr6 | 10425630 | 10425789 | chr6 | 10425839 | 10426884 | chr6 | 10542836 | 10542977 |
| chr6 | 10734917 | 10735045 | chr6 | 10881835 | 10882057 | chr6 | 10882321 | 10882350 |
| chr6 | 10883008 | 10883022 | chr6 | 10883444 | 10883474 | chr6 | 10887078 | 10887686 |
| chr6 | 11044062 | 11044572 | chr6 | 12288517 | 12288681 | chr6 | 12749899 | 12749940 |
| chr6 | 13797690 | 13797736 | chr6 | 14687918 | 14688084 | chr6 | 14986483 | 14986522 |
| chr6 | 15513780 | 15513981 | chr6 | 16197030 | 16197112 | chr6 | 16729595 | 16729624 |
| chr6 | 17281417 | 17281534 | chr6 | 17666654 | 17666707 | chr6 | 17750276 | 17750306 |
| chr6 | 18035867 | 18036015 | chr6 | 19691638 | 19691841 | chr6 | 19692143 | 19692318 |
| chr6 | 19837064 | 19837140 | chr6 | 19892448 | 19892627 | chr6 | 21664719 | 21664749 |
| chr6 | 21665004 | 21665043 | chr6 | 22172209 | 22172305 | chr6 | 22172536 | 22172566 |
| chr6 | 24358291 | 24358320 | chr6 | 24360074 | 24360170 | chr6 | 24494679 | 24494766 |
| chr6 | 24647342 | 24647599 | chr6 | 24662439 | 24662469 | chr6 | 26034268 | 26034311 |
| chr6 | 26184095 | 26184391 | chr6 | 26188696 | 26189393 | chr6 | 26189859 | 26189991 |
| chr6 | 26199137 | 26199167 | chr6 | 26199686 | 26199716 | chr6 | 26214514 | 26214648 |
| chr6 | 26235223 | 26235623 | chr6 | 26240504 | 26241118 | chr6 | 26250468 | 26250826 |
| chr6 | 26251054 | 26251182 | chr6 | 26251816 | 26252098 | chr6 | 26252141 | 26252151 |
| chr6 | 26254617 | 26254647 | chr6 | 26260956 | 26260986 | chr6 | 26271405 | 26271762 |
| chr6 | 26271971 | 26272001 | chr6 | 26272512 | 26272617 | chr6 | 26273400 | 26273418 |
| chr6 | 26284811 | 26284898 | chr6 | 26327806 | 26327982 | chr6 | 26328294 | 26328457 |
| chr6 | 26332178 | 26332218 | chr6 | 26501950 | 26502209 | chr6 | 26550994 | 26551034 |
| chr6 | 26577158 | 26577475 | chr6 | 26987967 | 26988166 | chr6 | 27059783 | 27059848 |
| chr6 | 27064682 | 27065198 | chr6 | 27173528 | 27173546 | chr6 | 27173633 | 27174181 |
| chr6 | 27182869 | 27182899 | chr6 | 27203269 | 27203336 | chr6 | 27205300 | 27205441 |
| chr6 | 22205671 | 27205836 | chr6 | 27205914 | 27206040 | chr6 | 27218951 | 27218980 |
| chr6 | 27228180 | 27228186 | chr6 | 27228290 | 27228395 | chr6 | 27235876 | 27235905 |
| chr6 | 27247636 | 27247724 | chr6 | 27256097 | 27256173 | chr6 | 27256383 | 27256420 |
| chr6 | 27264332 | 27264364 | chr6 | 27279845 | 27280012 | chr6 | 27441812 | 27441842 |
| chr6 | 27463029 | 27463687 | chr6 | 27512761 | 27512883 | chr6 | 27512995 | 27513487 |
| chr6 | 27533822 | 27534341 | chr6 | 27559809 | 27560075 | chr6 | 27573171 | 27573392 |
| chr6 | 27598738 | 27598860 | chr6 | 27599159 | 27599341 | chr6 | 27635265 | 27635434 |
| chr6 | 27642712 | 27647735 | chr6 | 27647891 | 27647896 | chr6 | 27648912 | 27649134 |
| chr6 | 27783039 | 27783052 | chr6 | 27799464 | 27799581 | chr6 | 27834676 | 27834835 |
| chr6 | 27835047 | 27835096 | chr6 | 27835378 | 27835417 | chr6 | 27839726 | 27840082 |
| chr6 | 27840543 | 27840617 | chr6 | 27841104 | 27841136 | chr6 | 27858515 | 27858684 |
| chr6 | 28175189 | 28176212 | chr6 | 28227076 | 28227141 | chr6 | 28303562 | 28303607 |
| chr6 | 28303815 | 28304263 | chr6 | 28367109 | 28367346 | chr6 | 28367491 | 28367774 |
| chr6 | 28410976 | 28411087 | chr6 | 28411152 | 28411353 | chr6 | 28414977 | 28414991 |
| chr6 | 28457608 | 28457638 | chr6 | 28457870 | 28458158 | chr6 | 28956323 | 28956511 |
| chr6 | 28956660 | 28956719 | chr6 | 30095233 | 30095262 | chr6 | 30095418 | 30095570 |
| chr6 | 30130804 | 30130895 | chr6 | 30644680 | 30644798 | chr6 | 32374147 | 32374176 |
| chr6 | 32374739 | 32374768 | chr6 | 32376051 | 32376080 | chr6 | 33161275 | 33161342 |
| chr6 | 33632930 | 33633000 | chr6 | 33636388 | 33636418 | chr6 | 33955505 | 33955731 |
| chr6 | 34113872 | 34113957 | chr6 | 34170970 | 34171061 | chr6 | 34219930 | 34219972 |

TABLE 12-continued

| chr | start | end | chr | start | end | chr | start | end |
|---|---|---|---|---|---|---|---|---|
| chr6 | 34396431 | 34396542 | chr6 | 34535802 | 34535832 | chr6 | 34714803 | 34714896 |
| chr6 | 34724047 | 34724228 | chr6 | 35150041 | 35150080 | chr6 | 35182493 | 35182522 |
| chr6 | 35470285 | 35470399 | chr6 | 35479613 | 35479642 | chr6 | 35992428 | 35992458 |
| chr6 | 36165662 | 36165692 | chr6 | 36178031 | 36178301 | chr6 | 36252984 | 36253171 |
| chr6 | 36313883 | 36313913 | chr6 | 36392273 | 36392323 | chr6 | 36406316 | 36406370 |
| chr6 | 36808323 | 36808441 | chr6 | 37024559 | 37024589 | chr6 | 37392127 | 37392189 |
| chr6 | 37545401 | 37545495 | chr6 | 37664140 | 37664187 | chr6 | 37673320 | 37673611 |
| chr6 | 37776410 | 37776440 | chr6 | 32776703 | 37776735 | chr6 | 38683212 | 38683235 |
| chr6 | 39281088 | 39281133 | chr6 | 39281824 | 39281875 | chr6 | 39329863 | 39329892 |
| chr6 | 39508464 | 39508493 | chr6 | 39760401 | 39760661 | chr6 | 40554653 | 40554699 |
| chr6 | 41273881 | 41273942 | chr6 | 41337072 | 41337128 | chr6 | 41339263 | 41339558 |
| chr6 | 41339602 | 41339838 | chr6 | 41340902 | 41341182 | chr6 | 41341501 | 41341549 |
| chr6 | 41342243 | 41342275 | chr6 | 41342807 | 41342837 | chr6 | 41605937 | 41605951 |
| chr6 | 41606038 | 41606356 | chr6 | 41606528 | 41606542 | chr6 | 41773520 | 41773903 |
| chr6 | 41774459 | 41774576 | chr6 | 42062143 | 42062346 | chr6 | 42090977 | 42091027 |
| chr6 | 42111015 | 42111051 | chr6 | 42711893 | 42711923 | chr6 | 42738966 | 42739049 |
| chr6 | 42773440 | 42773622 | chr6 | 42846662 | 42846705 | chr6 | 42879554 | 42879568 |
| chr6 | 42879622 | 42879718 | chr6 | 42928321 | 42928454 | chr6 | 42990166 | 42990485 |
| chr6 | 43119019 | 43119580 | chr6 | 43211193 | 43211311 | chr6 | 43424297 | 43424470 |
| chr6 | 43425152 | 43425207 | chr6 | 43425479 | 43425509 | chr6 | 43478676 | 43478745 |
| chr6 | 43612825 | 43612898 | chr6 | 43613053 | 43613067 | chr6 | 43639548 | 43639710 |
| chr6 | 43748463 | 43748616 | chr6 | 44240914 | 44241108 | chr6 | 44695763 | 44695795 |
| chr6 | 45388716 | 45388775 | chr6 | 46702982 | 46703123 | chr6 | 46703350 | 46703436 |
| chr6 | 47473194 | 47473287 | chr6 | 47590439 | 47590604 | chr6 | 49590555 | 49590786 |
| chr6 | 49765146 | 49765202 | chr6 | 50674372 | 50674750 | chr6 | 50681699 | 50681942 |
| chr6 | 50682319 | 50682338 | chr6 | 50682659 | 50682683 | chr6 | 50682712 | 50682940 |
| chr6 | 50682992 | 50683227 | chr6 | 50684939 | 50684969 | chr6 | 50689913 | 50690059 |
| chr6 | 50691065 | 50691095 | chr6 | 50692083 | 50692212 | chr6 | 50692300 | 50692481 |
| chr6 | 50787216 | 50787876 | chr6 | 50787950 | 50788352 | chr6 | 50789374 | 50789404 |
| chr6 | 50791187 | 50791494 | chr6 | 50791551 | 50791632 | chr6 | 50793335 | 50793404 |
| chr6 | 50793728 | 50793842 | chr6 | 50794531 | 50794693 | chr6 | 50803834 | 50803867 |
| chr6 | 50804131 | 50804368 | chr6 | 50808681 | 50808854 | chr6 | 50810551 | 50810713 |
| chr6 | 50811062 | 50811488 | chr6 | 50813258 | 50813939 | chr6 | 50814569 | 50814599 |
| chr6 | 50817023 | 50817229 | chr6 | 50817905 | 50817935 | chr6 | 50818449 | 50818706 |
| chr6 | 50818920 | 50819000 | chr6 | 52227752 | 52227781 | chr6 | 52228008 | 52228037 |
| chr6 | 52344375 | 52344405 | chr6 | 52763812 | 52763982 | chr6 | 52928742 | 52928776 |
| chr6 | 52929051 | 52929233 | chr6 | 53052723 | 53052859 | chr6 | 53212491 | 53213970 |
| chr6 | 55443691 | 55443945 | chr6 | 56112262 | 56112386 | chr6 | 56716390 | 56716410 |
| chr6 | 56818656 | 56818937 | chr6 | 56819217 | 56819637 | chr6 | 56819897 | 56819926 |
| chr6 | 57694587 | 57694617 | chr6 | 38147447 | 58147480 | chr6 | 58147790 | 58147976 |
| chr6 | 62995356 | 62995874 | chr6 | 62996078 | 62996146 | chr6 | 62996443 | 62996489 |
| chr6 | 70992137 | 70992162 | chr6 | 70992415 | 70992560 | chr6 | 70992830 | 70993015 |
| chr6 | 71090933 | 71090963 | chr6 | 71665638 | 71665723 | chr6 | 71666788 | 71666986 |
| chr6 | 72129789 | 72129829 | chr6 | 72130191 | 72130464 | chr6 | 72596120 | 72596315 |
| chr6 | 72596950 | 72596980 | chr6 | 73329784 | 73330126 | chr6 | 73330834 | 73331304 |
| chr6 | 73331515 | 73331850 | chr6 | 73331876 | 73333122 | chr6 | 73980676 | 73980722 |
| chr6 | 73982025 | 73982058 | chr6 | 74097722 | 74097763 | chr6 | 75995789 | 75995819 |
| chr6 | 76059561 | 76059787 | chr6 | 78172177 | 78172275 | chr6 | 78172323 | 78172672 |
| chr6 | 78173212 | 78173264 | chr6 | 78173696 | 78173725 | chr6 | 78173772 | 78173984 |
| chr6 | 78176458 | 78176820 | chr6 | 79620475 | 79620699 | chr6 | 80656930 | 80657180 |
| chr6 | 82463270 | 82463310 | chr6 | 82958615 | 82958917 | chr6 | 83546464 | 83546498 |
| chr6 | 84141298 | 84141412 | chr6 | 84417436 | 84417700 | chr6 | 84418261 | 84418624 |
| chr6 | 84418644 | 84418788 | chr6 | 84419157 | 84419415 | chr6 | 84562873 | 84563242 |
| chr6 | 84563489 | 84563542 | chr6 | 85050415 | 85050504 | chr6 | 85472407 | 85473703 |
| chr6 | 85473928 | 85474378 | chr6 | 85474594 | 85474736 | chr6 | 85476233 | 85476285 |
| chr6 | 85476998 | 85477028 | chr6 | 85478514 | 85478724 | chr6 | 85482530 | 85482612 |
| chr6 | 85483345 | 85483375 | chr6 | 85483760 | 85483931 | chr6 | 85484558 | 85484625 |
| chr6 | 85484717 | 85484920 | chr6 | 86302413 | 86302614 | chr6 | 87647114 | 87647143 |
| chr6 | 87862092 | 87862172 | chr6 | 88518712 | 88518742 | chr6 | 88876963 | 88877421 |
| chr6 | 89672213 | 89672376 | chr6 | 91320285 | 91320318 | chr6 | 91320949 | 91321295 |
| chr6 | 94126973 | 94127064 | chr6 | 94127455 | 94127544 | chr6 | 94128365 | 94128399 |
| chr6 | 94129219 | 94129257 | chr6 | 94129509 | 94129575 | chr6 | 96464100 | 96464204 |
| chr6 | 97412429 | 97412529 | chr6 | 97930083 | 97930113 | chr6 | 99271926 | 99272810 |
| chr6 | 99273369 | 99273410 | chr6 | 99277180 | 99277330 | chr6 | 99279556 | 99279612 |
| chr6 | 99280557 | 99280744 | chr6 | 99281014 | 99281036 | chr6 | 99281068 | 99281385 |
| chr6 | 99283512 | 99283582 | chr6 | 99290360 | 99290398 | chr6 | 99291264 | 99291341 |
| chr6 | 99292252 | 99292417 | chr6 | 99295726 | 99295863 | chr6 | 99296062 | 99296364 |
| chr6 | 99296408 | 99296467 | chr6 | 99396456 | 99396609 | chr6 | 99842067 | 99842258 |
| chr6 | 99842336 | 99842382 | chr6 | 100038682 | 100038706 | chr6 | 100038786 | 100038964 |
| chr6 | 100039275 | 100039289 | chr6 | 100050754 | 100050810 | chr6 | 100050859 | 100051108 |
| chr6 | 100051360 | 100051507 | chr6 | 100051772 | 100051971 | chr6 | 100053221 | 100053511 |
| chr6 | 100054866 | 100054917 | chr6 | 100061022 | 100061076 | chr6 | 100061311 | 100061419 |
| chr6 | 100062178 | 100062586 | chr6 | 100062944 | 100063068 | chr6 | 100135425 | 100135583 |
| chr6 | 100441498 | 100441737 | chr6 | 100441762 | 100441966 | chr6 | 100903384 | 100903404 |
| chr6 | 100903561 | 100903631 | chr6 | 100904214 | 100904275 | chr6 | 100905969 | 100906016 |
| chr6 | 100911686 | 100911723 | chr6 | 100912070 | 100912119 | chr6 | 100912421 | 100912445 |
| chr6 | 100912465 | 100912480 | chr6 | 100912919 | 100913050 | chr6 | 100915101 | 100915205 |
| chr6 | 101840708 | 101840820 | chr6 | 101846782 | 101846789 | chr6 | 101847185 | 101847215 |

TABLE 12-continued

| chr | start | end | chr | start | end | chr | start | end |
|---|---|---|---|---|---|---|---|---|
| chr6 | 101850147 | 101850275 | chr6 | 105388679 | 105388708 | chr6 | 105389510 | 105389710 |
| chr6 | 105400913 | 105401007 | chr6 | 105401620 | 105401874 | chr6 | 105404574 | 105404674 |
| chr6 | 105405656 | 105405772 | chr6 | 105406098 | 105406128 | chr6 | 105584264 | 105584319 |
| chr6 | 105584367 | 105585554 | chr6 | 105821423 | 105821453 | chr6 | 106429049 | 106429475 |
| chr6 | 106429590 | 106429624 | chr6 | 106434339 | 106434368 | chr6 | 106441869 | 106442979 |
| chr6 | 106731509 | 106731597 | chr6 | 106960908 | 106961023 | chr6 | 107075651 | 107075704 |
| chr6 | 107562769 | 107562859 | chr6 | 108181556 | 108181721 | chr6 | 108280292 | 108280352 |
| chr6 | 108435075 | 108435263 | chr6 | 108436072 | 108436526 | chr6 | 108438261 | 108438577 |
| chr6 | 108440091 | 108440644 | chr6 | 108440745 | 108440961 | chr6 | 108479290 | 108479665 |
| chr6 | 108484909 | 108485406 | chr6 | 108485665 | 108485905 | chr6 | 108486158 | 108486394 |
| chr6 | 108487724 | 108488416 | chr6 | 108489662 | 108489808 | chr6 | 108490067 | 108490245 |
| chr6 | 108490297 | 108490514 | chr6 | 108490538 | 108490633 | chr6 | 108490978 | 108491000 |
| chr6 | 108491108 | 108491423 | chr6 | 108492270 | 108492451 | chr6 | 108495681 | 108495817 |
| chr6 | 108495916 | 108495951 | chr6 | 108496208 | 108496649 | chr6 | 108497494 | 108497796 |
| chr6 | 108497827 | 108497881 | chr6 | 109057882 | 109057928 | chr6 | 109058799 | 109058861 |
| chr6 | 110437721 | 110437751 | chr6 | 110679123 | 110679414 | chr6 | 110797678 | 110797708 |
| chr6 | 110798007 | 110798036 | chr6 | 110848558 | 110848682 | chr6 | 113852508 | 113852634 |
| chr6 | 116783448 | 116783493 | chr6 | 117000853 | 117001032 | chr6 | 117086249 | 117086639 |
| chr6 | 117585967 | 117586004 | chr6 | 117586847 | 117587169 | chr6 | 117587480 | 117587527 |
| chr6 | 117591161 | 117591191 | chr6 | 117591411 | 117591596 | chr6 | 117591684 | 117591743 |
| chr6 | 118228102 | 118228151 | chr6 | 118228747 | 118228828 | chr6 | 118229154 | 118229383 |
| chr6 | 118229626 | 118229818 | chr6 | 118241228 | 118241308 | chr6 | 118241395 | 118241500 |
| chr6 | 119254629 | 119254678 | chr6 | 119483052 | 119483082 | chr6 | 121758672 | 121758994 |
| chr6 | 121797231 | 121797265 | chr6 | 123317073 | 123317589 | chr6 | 123317797 | 123317833 |
| chr6 | 124124432 | 124124455 | chr6 | 124124860 | 124125016 | chr6 | 125284131 | 125284175 |
| chr6 | 126068092 | 126068178 | chr6 | 127439379 | 127439453 | chr6 | 127439985 | 127440127 |
| chr6 | 127440331 | 127440962 | chr6 | 127441031 | 127441123 | chr6 | 127441554 | 127441762 |
| chr6 | 127442021 | 127442070 | chr6 | 127442090 | 127442104 | chr6 | 127840501 | 127840681 |
| chr6 | 129204459 | 129204524 | chr6 | 130686534 | 130687057 | chr6 | 131602584 | 131602694 |
| chr6 | 132722078 | 132722141 | chr6 | 132722158 | 132722196 | chr6 | 133561740 | 133562070 |
| chr6 | 133562374 | 133562436 | chr6 | 133562675 | 133563056 | chr6 | 133563327 | 133563918 |
| chr6 | 134067194 | 134067471 | chr6 | 134176232 | 134176299 | chr6 | 134176549 | 134176579 |
| chr6 | 134210528 | 134211018 | chr6 | 134211112 | 134211367 | chr6 | 134213944 | 134213987 |
| chr6 | 134214077 | 134214364 | chr6 | 134589500 | 134589767 | chr6 | 134638950 | 134639003 |
| chr6 | 137241928 | 137242205 | chr6 | 137243208 | 137243410 | chr6 | 137244114 | 137244148 |
| chr6 | 137244236 | 137244465 | chr6 | 137311168 | 137311380 | chr6 | 137366354 | 137366383 |
| chr6 | 137809141 | 137809365 | chr6 | 137809446 | 137809916 | chr6 | 137810033 | 137811088 |
| chr6 | 137813787 | 137813895 | chr6 | 137814604 | 137814618 | chr6 | 137814654 | 137814763 |
| chr6 | 137815008 | 137815170 | chr6 | 137815225 | 137815662 | chr6 | 137816472 | 137817351 |
| chr6 | 137818505 | 137818598 | chr6 | 137818619 | 137819368 | chr6 | 146755567 | 146755649 |
| chr6 | 149868348 | 149868387 | chr6 | 150183760 | 150183874 | chr6 | 150284552 | 150284581 |
| chr6 | 150285056 | 150285368 | chr6 | 150285545 | 150285885 | chr6 | 150286100 | 150286639 |
| chr6 | 150358970 | 150359192 | chr6 | 151561016 | 151561340 | chr6 | 151561369 | 151561857 |
| chr6 | 151662065 | 151562563 | chr6 | 151650396 | 151650453 | chr6 | 151815055 | 151815089 |
| chr6 | 152419908 | 152419940 | chr6 | 162623015 | 152623493 | chr6 | 152957895 | 152958076 |
| chr6 | 153451236 | 153451500 | chr6 | 153451890 | 153451968 | chr6 | 153452232 | 153452320 |
| chr6 | 153452713 | 153452746 | chr6 | 154360650 | 154360746 | chr6 | 154970558 | 154970676 |
| chr6 | 155316257 | 155316265 | chr6 | 155569208 | 155569305 | chr6 | 157037549 | 157037677 |
| chr6 | 157266063 | 157266109 | chr6 | 157502438 | 157502561 | chr6 | 157506082 | 157506112 |
| chr6 | 157556764 | 157557296 | chr6 | 157637455 | 157637500 | chr6 | 159211558 | 159211701 |
| chr6 | 159228187 | 159228217 | chr6 | 159290823 | 159290852 | chr6 | 159419589 | 159419717 |
| chr6 | 159590048 | 159590086 | chr6 | 159590155 | 159590305 | chr6 | 159590972 | 159590986 |
| chr6 | 159654923 | 159655003 | chr6 | 161100361 | 161100390 | chr6 | 161188513 | 161188543 |
| chr6 | 161352101 | 161352135 | chr6 | 161645992 | 161646255 | chr6 | 161780056 | 161780139 |
| chr6 | 163602842 | 163602872 | chr6 | 163834314 | 163834382 | chr6 | 163834406 | 163834532 |
| chr6 | 163834857 | 163834901 | chr6 | 163836568 | 163836900 | chr6 | 164114396 | 164114524 |
| chr6 | 164179636 | 164179668 | chr6 | 164183602 | 164183632 | chr6 | 164196971 | 164197003 |
| chr6 | 164215532 | 164215633 | chr6 | 164228294 | 164228363 | chr6 | 164246015 | 164246143 |
| chr6 | 164283254 | 164283377 | chr6 | 164314289 | 164314443 | chr6 | 164322666 | 164322775 |
| chr6 | 166074119 | 166074412 | chr6 | 166076788 | 166077021 | chr6 | 166077378 | 166077632 |
| chr6 | 166267582 | 166267891 | chr6 | 166401254 | 166401307 | chr6 | 166402240 | 166402546 |
| chr6 | 166421911 | 166422185 | chr6 | 166579723 | 166580144 | chr6 | 166580344 | 166582797 |
| chr6 | 166944367 | 166944403 | chr6 | 167202601 | 167202801 | chr6 | 167835129 | 167835171 |
| chr6 | 168719983 | 168720019 | chr6 | 168842847 | 168842944 | chr6 | 168858122 | 168858296 |
| chr6 | 168972472 | 168972502 | chr6 | 169002054 | 169002084 | chr6 | 169653638 | 169653668 |
| chr6 | 170047467 | 170047499 | chr6 | 170240639 | 170240714 | chr6 | 170264728 | 170264761 |
| chr6 | 170475105 | 170475267 | chr6 | 170494286 | 170494315 | chr6 | 170894820 | 170894912 |
| chr7 | 68930 | 68960 | chr7 | 329805 | 329838 | chr7 | 369494 | 369536 |
| chr7 | 369844 | 369980 | chr7 | 389663 | 389693 | chr7 | 409826 | 409892 |
| chr7 | 427454 | 427484 | chr7 | 431386 | 431492 | chr7 | 497782 | 497934 |
| chr7 | 503811 | 503936 | chr7 | 551599 | 551697 | chr7 | 556928 | 556983 |
| chr7 | 564237 | 564271 | chr7 | 578922 | 579020 | chr7 | 579827 | 579857 |
| chr7 | 752120 | 752221 | chr7 | 842331 | 842414 | chr7 | 907656 | 907709 |
| chr7 | 915058 | 915087 | chr7 | 922050 | 922235 | chr7 | 927933 | 927986 |
| chr7 | 1016343 | 1016373 | chr7 | 1022224 | 1022254 | chr7 | 1030172 | 1030283 |
| chr7 | 1054579 | 1054696 | chr7 | 1086199 | 1086319 | chr7 | 1195270 | 1195364 |
| chr7 | 1263761 | 1263960 | chr7 | 1268318 | 1268366 | chr7 | 1269305 | 1269463 |
| chr7 | 1269553 | 1269808 | chr7 | 1270406 | 1270440 | chr7 | 1273167 | 1273330 |

TABLE 12-continued

| chr | start | end | chr | start | end | chr | start | end |
|---|---|---|---|---|---|---|---|---|
| chr7 | 1274641 | 1274677 | chr7 | 1275579 | 1275680 | chr7 | 1277817 | 1277865 |
| chr7 | 1279099 | 1279129 | chr7 | 1279965 | 1279995 | chr7 | 1281131 | 1281232 |
| chr7 | 1281493 | 1281555 | chr7 | 1282042 | 1282150 | chr7 | 1282506 | 1282644 |
| chr7 | 1288582 | 1288753 | chr7 | 1308351 | 1308497 | chr7 | 1325810 | 1325882 |
| chr7 | 1416020 | 1416131 | chr7 | 1423632 | 1423677 | chr7 | 1459041 | 1459191 |
| chr7 | 1503417 | 1503596 | chr7 | 1547311 | 1547394 | chr7 | 1598639 | 1598697 |
| chr7 | 1607386 | 1607465 | chr7 | 1607971 | 1608001 | chr7 | 1611443 | 1611522 |
| chr7 | 1615390 | 1615444 | chr7 | 1627404 | 1627434 | chr7 | 1641774 | 1641923 |
| chr7 | 1681189 | 1681239 | chr7 | 1688977 | 1689146 | chr7 | 1690745 | 1690851 |
| chr7 | 1709138 | 1709235 | chr7 | 1709474 | 1709561 | chr7 | 1733166 | 1733378 |
| chr7 | 1735223 | 1735354 | chr7 | 1748514 | 1748766 | chr7 | 1775831 | 1775861 |
| chr7 | 1778875 | 1778914 | chr7 | 1783551 | 1783623 | chr7 | 1786514 | 1786899 |
| chr7 | 1787166 | 1787324 | chr7 | 1800882 | 1800912 | chr7 | 1970842 | 1970872 |
| chr7 | 2109874 | 2109904 | chr7 | 2163332 | 2163467 | chr7 | 2208670 | 2208808 |
| chr7 | 2232963 | 2233056 | chr7 | 2233292 | 2233414 | chr7 | 2238118 | 2238235 |
| chr7 | 2300787 | 2300899 | chr7 | 2361190 | 2361434 | chr7 | 2473452 | 2473605 |
| chr7 | 2565919 | 2566041 | chr7 | 2566600 | 2566630 | chr7 | 2595825 | 2595943 |
| chr7 | 2659340 | 2659370 | chr7 | 2720013 | 2720140 | chr7 | 2728068 | 2728165 |
| chr7 | 2979480 | 2979512 | chr7 | 2985518 | 2985547 | chr7 | 3033658 | 3033688 |
| chr7 | 3083331 | 3083352 | chr7 | 3283704 | 3283894 | chr7 | 3340444 | 3340473 |
| chr7 | 3341570 | 3341597 | chr7 | 4215324 | 4215384 | chr7 | 4657806 | 4657857 |
| chr7 | 4856984 | 4857048 | chr7 | 4922550 | 4922706 | chr7 | 4923328 | 4923397 |
| chr7 | 4998201 | 4998388 | chr7 | 5111528 | 5111669 | chr7 | 5262433 | 5262562 |
| chr7 | 5397777 | 5397938 | chr7 | 5603717 | 5603947 | chr7 | 5632939 | 5633100 |
| chr7 | 5648107 | 5648393 | chr7 | 6045612 | 6045641 | chr7 | 6059024 | 6059182 |
| chr7 | 6060590 | 6060634 | chr7 | 6099217 | 6099334 | chr7 | 6124585 | 6124714 |
| chr7 | 6188610 | 6189061 | chr7 | 6307943 | 6308066 | chr7 | 6414386 | 6414415 |
| chr7 | 6426878 | 6426907 | chr7 | 6443279 | 6443376 | chr7 | 6443826 | 6443856 |
| chr7 | 6484445 | 6484545 | chr7 | 6524573 | 6524744 | chr7 | 6524977 | 6525012 |
| chr7 | 6525477 | 6525606 | chr7 | 6543150 | 6543216 | chr7 | 6560235 | 6560345 |
| chr7 | 6566413 | 6566663 | chr7 | 6570959 | 6571130 | chr7 | 6576137 | 6576367 |
| chr7 | 6703555 | 6703869 | chr7 | 6703916 | 6703959 | chr7 | 7015498 | 7015673 |
| chr7 | 7605441 | 7605822 | chr7 | 8343630 | 8343724 | chr7 | 8391475 | 8391573 |
| chr7 | 8473070 | 8473455 | chr7 | 8473480 | 8473674 | chr7 | 8473956 | 8474241 |
| chr7 | 8474516 | 8474562 | chr7 | 8474814 | 8475057 | chr7 | 8480640 | 8481159 |
| chr7 | 8481642 | 8481833 | chr7 | 8482056 | 8482297 | chr7 | 8482670 | 8482824 |
| chr7 | 8482885 | 8482921 | chr7 | 8483147 | 8483950 | chr7 | 12151440 | 12151472 |
| chr7 | 12151524 | 12151678 | chr7 | 12443317 | 12443403 | chr7 | 12443841 | 12443871 |
| chr7 | 12610339 | 12610476 | chr7 | 12751410 | 12751496 | chr7 | 12776779 | 12776811 |
| chr7 | 15725983 | 15726081 | chr7 | 15726634 | 15727077 | chr7 | 15727290 | 15727320 |
| chr7 | 19145808 | 19145893 | chr7 | 19146032 | 19146184 | chr7 | 19146238 | 19146249 |
| chr7 | 19146502 | 19146558 | chr7 | 19147122 | 19147798 | chr7 | 19152224 | 19152349 |
| chr7 | 19155791 | 19155820 | chr7 | 19156126 | 19156132 | chr7 | 19156304 | 19156745 |
| chr7 | 19157144 | 19157566 | chr7 | 19157634 | 19158015 | chr7 | 19158632 | 19158735 |
| chr7 | 19184058 | 19184255 | chr7 | 19813284 | 19813313 | chr7 | 20089670 | 20089700 |
| chr7 | 20183238 | 20183283 | chr7 | 20816252 | 20816447 | chr7 | 20817380 | 20817410 |
| chr7 | 20818130 | 20818362 | chr7 | 20823292 | 20823330 | chr7 | 20823383 | 20823432 |
| chr7 | 20823920 | 20824143 | chr7 | 20824476 | 20824819 | chr7 | 20824836 | 20824946 |
| chr7 | 20825379 | 20825559 | chr7 | 20826113 | 20826202 | chr7 | 20826884 | 20827199 |
| chr7 | 20830670 | 20830700 | chr7 | 20833167 | 20833322 | chr7 | 21403615 | 21403645 |
| chr7 | 21582593 | 21582640 | chr7 | 21582792 | 21582868 | chr7 | 21583263 | 21583277 |
| chr7 | 21583304 | 21583625 | chr7 | 22539833 | 22539909 | chr7 | 22589355 | 22589415 |
| chr7 | 22824965 | 22825009 | chr7 | 23253573 | 23253671 | chr7 | 23287253 | 23287350 |
| chr7 | 23287533 | 23287624 | chr7 | 23526549 | 23526698 | chr7 | 23578703 | 23578857 |
| chr7 | 24323763 | 24323939 | chr7 | 24580644 | 24580806 | chr7 | 24796478 | 24796567 |
| chr7 | 25132558 | 25132726 | chr7 | 25133492 | 25133650 | chr7 | 25165921 | 25166061 |
| chr7 | 25896521 | 25896864 | chr7 | 25897133 | 25897246 | chr7 | 26194906 | 26195024 |
| chr7 | 26283775 | 26283954 | chr7 | 27127863 | 27127898 | chr7 | 27135327 | 27135770 |
| chr7 | 27136013 | 27136790 | chr7 | 27138381 | 27138410 | chr7 | 27184015 | 27184190 |
| chr7 | 27190591 | 27191226 | chr7 | 27192061 | 27192098 | chr7 | 27195462 | 27195601 |
| chr7 | 27195867 | 27195892 | chr7 | 27196153 | 27196839 | chr7 | 27204487 | 27204769 |
| chr7 | 27205266 | 27205395 | chr7 | 27205678 | 27205789 | chr7 | 27208187 | 27208285 |
| chr7 | 27209462 | 27209582 | chr7 | 27212499 | 27212899 | chr7 | 27213189 | 27214261 |
| chr7 | 27217042 | 27217071 | chr7 | 27223114 | 27223151 | chr7 | 27223601 | 27223696 |
| chr7 | 27224069 | 27224609 | chr7 | 27225035 | 27225057 | chr7 | 27225447 | 27225483 |
| chr7 | 27227874 | 27227953 | chr7 | 27231476 | 27231505 | chr7 | 27231818 | 27231894 |
| chr7 | 27232289 | 27232962 | chr7 | 27233410 | 27233454 | chr7 | 27238887 | 27238917 |
| chr7 | 27239226 | 27239234 | chr7 | 27240230 | 27240381 | chr7 | 27244515 | 27244610 |
| chr7 | 27244798 | 27245310 | chr7 | 27245668 | 27245795 | chr7 | 27252380 | 27252410 |
| chr7 | 27260092 | 27260100 | chr7 | 27264875 | 27265325 | chr7 | 27265538 | 27265584 |
| chr7 | 27275513 | 27275543 | chr7 | 27279238 | 27279368 | chr7 | 27281329 | 27281360 |
| chr7 | 27282089 | 27283013 | chr7 | 27283351 | 27283627 | chr7 | 27285621 | 27285913 |
| chr7 | 27285980 | 27286098 | chr7 | 27286171 | 27286248 | chr7 | 27288946 | 27289100 |
| chr7 | 27289170 | 27289449 | chr7 | 27291315 | 27291851 | chr7 | 28110701 | 28110828 |
| chr7 | 28238339 | 28238444 | chr7 | 28449276 | 28449290 | chr7 | 28449659 | 28449781 |
| chr7 | 28449858 | 28450015 | chr7 | 28989065 | 28989159 | chr7 | 28995657 | 28995978 |
| chr7 | 28996457 | 28996495 | chr7 | 28996840 | 28996916 | chr7 | 28997135 | 28997626 |
| chr7 | 28998053 | 28998119 | chr7 | 30029702 | 30029822 | chr7 | 30029923 | 30029952 |

TABLE 12-continued

| chr | start | end | chr | start | end | chr | start | end |
|---|---|---|---|---|---|---|---|---|
| chr7 | 30030307 | 30030337 | chr7 | 30721280 | 30721902 | chr7 | 30722290 | 30722375 |
| chr7 | 30857157 | 30857292 | chr7 | 31093003 | 31093133 | chr7 | 31232909 | 31232939 |
| chr7 | 31375965 | 31376135 | chr7 | 32110704 | 32110772 | chr7 | 32337807 | 32337837 |
| chr7 | 32338088 | 32338217 | chr7 | 32338284 | 32338410 | chr7 | 32338900 | 32338930 |
| chr7 | 32467461 | 32467655 | chr7 | 32467947 | 32468062 | chr7 | 32997124 | 32997454 |
| chr7 | 33167928 | 33168030 | chr7 | 33725803 | 33725938 | chr7 | 33943459 | 33943759 |
| chr7 | 35225809 | 35225833 | chr7 | 35226193 | 35226522 | chr7 | 35226557 | 35226765 |
| chr7 | 35292970 | 35293086 | chr7 | 35293183 | 35293293 | chr7 | 35294032 | 35294141 |
| chr7 | 35294502 | 35294536 | chr7 | 35295104 | 35295105 | chr7 | 35295908 | 35295944 |
| chr7 | 35296935 | 35297004 | chr7 | 35297138 | 35297353 | chr7 | 35297471 | 35298016 |
| chr7 | 35300951 | 35301008 | chr7 | 35301102 | 35301948 | chr7 | 37352957 | 37353062 |
| chr7 | 37487164 | 37487453 | chr7 | 37487756 | 37487826 | chr7 | 37488257 | 37488578 |
| chr7 | 37488920 | 37488992 | chr7 | 37907440 | 37907470 | chr7 | 37955878 | 37955979 |
| chr7 | 37956271 | 37956439 | chr7 | 37960301 | 37960335 | chr7 | 38588471 | 38388501 |
| chr7 | 38670357 | 38670663 | chr7 | 38670957 | 38671015 | chr7 | 39015542 | 39015981 |
| chr7 | 39649223 | 39649253 | chr7 | 39649444 | 39649457 | chr7 | 39872836 | 39873015 |
| chr7 | 41739663 | 41739879 | chr7 | 41982690 | 41982874 | chr7 | 42267647 | 42267677 |
| chr7 | 42276346 | 42276634 | chr7 | 42377468 | 42377497 | chr7 | 42533257 | 42533296 |
| chr7 | 43162109 | 43152207 | chr7 | 43152414 | 43152700 | chr7 | 43152957 | 43153199 |
| chr7 | 43153230 | 43163237 | chr7 | 43817999 | 43818119 | chr7 | 44083283 | 44083416 |
| chr7 | 44097690 | 44097876 | chr7 | 44151398 | 44151428 | chr7 | 44151795 | 44151933 |
| chr7 | 44163926 | 44163989 | chr7 | 44364838 | 44364903 | chr7 | 44740467 | 44740672 |
| chr7 | 44835037 | 44835384 | chr7 | 44912004 | 44912034 | chr7 | 45026942 | 45027045 |
| chr7 | 45038532 | 45038655 | chr7 | 45046874 | 45046982 | chr7 | 45525402 | 45525432 |
| chr7 | 45613785 | 45613813 | chr7 | 45613858 | 45613898 | chr7 | 45614341 | 45614474 |
| chr7 | 45614738 | 45614809 | chr7 | 45614929 | 45615020 | chr7 | 45615440 | 45615495 |
| chr7 | 45960743 | 45960794 | chr7 | 45961146 | 45961176 | chr7 | 45961508 | 45961576 |
| chr7 | 45961833 | 45961888 | chr7 | 47515359 | 47515405 | chr7 | 47704289 | 47704359 |
| chr7 | 49654508 | 49654538 | chr7 | 49812820 | 49813017 | chr7 | 49813810 | 49813994 |
| chr7 | 49814531 | 49814750 | chr7 | 49815117 | 49815249 | chr7 | 49815657 | 49815765 |
| chr7 | 49819674 | 49819703 | chr7 | 50294451 | 50294481 | chr7 | 50343263 | 50343401 |
| chr7 | 50343975 | 50343994 | chr7 | 50344226 | 50344491 | chr7 | 50365076 | 50365137 |
| chr7 | 50438618 | 50438648 | chr7 | 50441145 | 50441285 | chr7 | 50560588 | 50560637 |
| chr7 | 50860226 | 50861102 | chr7 | 51383754 | 51383790 | chr7 | 51384322 | 51384440 |
| chr7 | 51384915 | 51384951 | chr7 | 52156231 | 52156261 | chr7 | 54609852 | 54609951 |
| chr7 | 54609992 | 54610153 | chr7 | 54612418 | 54612730 | chr7 | 55086473 | 55086601 |
| chr7 | 55086983 | 55087533 | chr7 | 55209976 | 55210005 | chr7 | 55211065 | 55211094 |
| chr7 | 55221729 | 55221836 | chr7 | 56223589 | 55223636 | chr7 | 55227993 | 55228022 |
| chr7 | 55233028 | 55233123 | chr7 | 55241663 | 55241737 | chr7 | 55242419 | 55242493 |
| chr7 | 55248975 | 55249085 | chr7 | 55259404 | 55259547 | chr7 | 55260469 | 55260498 |
| chr7 | 55268867 | 55268896 | chr7 | 55410019 | 55410126 | chr7 | 55506288 | 55506348 |
| chr7 | 56018123 | 56018286 | chr7 | 56031716 | 56031869 | chr7 | 63667431 | 63667460 |
| chr7 | 64330411 | 64330470 | chr7 | 64330734 | 64330833 | chr7 | 64349042 | 64349056 |
| chr7 | 64349331 | 64349470 | chr7 | 64700283 | 64700329 | chr7 | 64712364 | 64712510 |
| chr7 | 64713317 | 64713449 | chr7 | 64974382 | 64974422 | chr7 | 65037609 | 65037734 |
| chr7 | 65508995 | 65509043 | chr7 | 65510006 | 65510096 | chr7 | 65878743 | 65878793 |
| chr7 | 65879649 | 65879883 | chr7 | 65880359 | 65880405 | chr7 | 66204493 | 66204617 |
| chr7 | 66206923 | 66206953 | chr7 | 66214923 | 66214961 | chr7 | 67579765 | 67579911 |
| chr7 | 68204793 | 68204948 | chr7 | 69062519 | 69062635 | chr7 | 69064590 | 69064771 |
| chr7 | 69064834 | 69065045 | chr7 | 69352121 | 69352272 | chr7 | 69897780 | 69897827 |
| chr7 | 70596454 | 70596688 | chr7 | 70597406 | 70597451 | chr7 | 70597835 | 70597871 |
| chr7 | 70597991 | 70598123 | chr7 | 70598170 | 70598387 | chr7 | 70990312 | 70990370 |
| chr7 | 71217108 | 71217332 | chr7 | 71438424 | 71438454 | chr7 | 71603924 | 71604082 |
| chr7 | 71800676 | 71800756 | chr7 | 71800934 | 71801104 | chr7 | 71802410 | 71802522 |
| chr7 | 71802578 | 71802637 | chr7 | 71871203 | 71871245 | chr7 | 75511201 | 75511298 |
| chr7 | 76033151 | 76033289 | chr7 | 77129743 | 77129907 | chr7 | 77308664 | 77308899 |
| chr7 | 77309437 | 77309511 | chr7 | 77324362 | 77324593 | chr7 | 79081792 | 79081821 |
| chr7 | 79082023 | 79082218 | chr7 | 79083392 | 79083834 | chr7 | 80548257 | 80548403 |
| chr7 | 82072350 | 82072503 | chr7 | 82073495 | 82073533 | chr7 | 84815141 | 84815226 |
| chr7 | 84815744 | 84815954 | chr7 | 86273208 | 86273541 | chr7 | 86274258 | 86274457 |
| chr7 | 87104816 | 87105430 | chr7 | 87229537 | 87230433 | chr7 | 87257012 | 87257047 |
| chr7 | 87257931 | 87258054 | chr7 | 87563370 | 87563614 | chr7 | 87563829 | 87563890 |
| chr7 | 87706818 | 87706877 | chr7 | 87825006 | 87825137 | chr7 | 88387982 | 88388167 |
| chr7 | 88388540 | 88388660 | chr7 | 88388879 | 88388901 | chr7 | 88389047 | 88389356 |
| chr7 | 89747996 | 89748340 | chr7 | 89950183 | 89950810 | chr7 | 90226269 | 90226464 |
| chr7 | 90269263 | 90269563 | chr7 | 90797539 | 90797568 | chr7 | 90895012 | 90895097 |
| chr7 | 92466152 | 92466400 | chr7 | 92554253 | 92554452 | chr7 | 92689705 | 92689818 |
| chr7 | 93203708 | 93203756 | chr7 | 93204332 | 93204492 | chr7 | 93220696 | 93220826 |
| chr7 | 93519351 | 93519765 | chr7 | 93519855 | 93520137 | chr7 | 93551323 | 93551425 |
| chr7 | 94138158 | 94138315 | chr7 | 94284302 | 94284873 | chr7 | 96619560 | 96619603 |
| chr7 | 96621715 | 96621811 | chr7 | 96622107 | 96622349 | chr7 | 96622694 | 96622723 |
| chr7 | 96625537 | 96625720 | chr7 | 96625998 | 96626051 | chr7 | 96627013 | 96627048 |
| chr7 | 96631579 | 96631680 | chr7 | 96634645 | 96634928 | chr7 | 96635345 | 96635451 |
| chr7 | 96635733 | 96635971 | chr7 | 96636034 | 96636645 | chr7 | 96639318 | 96639348 |
| chr7 | 96646662 | 96647131 | chr7 | 96647809 | 96648219 | chr7 | 96649955 | 96650094 |
| chr7 | 96650884 | 96651076 | chr7 | 96651137 | 96651151 | chr7 | 96651469 | 96651537 |
| chr7 | 96652144 | 96652174 | chr7 | 96653507 | 96653819 | chr7 | 96653863 | 96653993 |
| chr7 | 97361098 | 97361422 | chr7 | 97361521 | 97361781 | chr7 | 97362292 | 97362607 |

TABLE 12-continued

| chr | start | end | chr | start | end | chr | start | end |
|---|---|---|---|---|---|---|---|---|
| chr7 | 97490474 | 97490508 | chr7 | 97580497 | 97580648 | chr7 | 97600104 | 97600224 |
| chr7 | 97839654 | 97839684 | chr7 | 97869290 | 97869391 | chr7 | 97869614 | 97869644 |
| chr7 | 98197206 | 98197242 | chr7 | 98245885 | 98246078 | chr7 | 98246305 | 98246507 |
| chr7 | 98246534 | 98246868 | chr7 | 98247126 | 98247656 | chr7 | 98966786 | 98966916 |
| chr7 | 98969875 | 98969928 | chr7 | 98971509 | 98971549 | chr7 | 99035152 | 99035191 |
| chr7 | 99104258 | 99104388 | chr7 | 99177742 | 99177870 | chr7 | 99591579 | 99591762 |
| chr7 | 99595194 | 99595335 | chr7 | 99642049 | 99642100 | chr7 | 99751578 | 99751630 |
| chr7 | 99775192 | 99775558 | chr7 | 99934913 | 99934943 | chr7 | 100088183 | 100088312 |
| chr7 | 100179889 | 100179927 | chr7 | 100241592 | 100241697 | chr7 | 100295321 | 100295424 |
| chr7 | 100318505 | 100318575 | chr7 | 100320690 | 100320719 | chr7 | 100547037 | 100547073 |
| chr7 | 100609750 | 100609780 | chr7 | 100808466 | 100808502 | chr7 | 100809436 | 100809521 |
| chr7 | 100823436 | 100823497 | chr7 | 101005968 | 101005998 | chr7 | 101241993 | 101242023 |
| chr7 | 101475790 | 101475858 | chr7 | 101558399 | 101558698 | chr7 | 101585887 | 101585917 |
| chr7 | 101627741 | 101627787 | chr7 | 101707502 | 101707532 | chr7 | 102091406 | 102091534 |
| chr7 | 102801710 | 102801804 | chr7 | 103085876 | 103086474 | chr7 | 103629059 | 103629794 |
| chr7 | 103630054 | 103630082 | chr7 | 103630475 | 103630824 | chr7 | 103969217 | 103969341 |
| chr7 | 103969694 | 103969794 | chr7 | 105279467 | 105279671 | chr7 | 106622834 | 106622961 |
| chr7 | 106685282 | 106685345 | chr7 | 106797774 | 106797804 | chr7 | 107301494 | 107301640 |
| chr7 | 107483694 | 107483918 | chr7 | 108095329 | 108095362 | chr7 | 108095781 | 108096055 |
| chr7 | 108097172 | 108097491 | chr7 | 111202993 | 111203260 | chr7 | 112726558 | 112726614 |
| chr7 | 113722810 | 113723283 | chr7 | 113723339 | 113723439 | chr7 | 113724956 | 113725081 |
| chr7 | 113726509 | 113726539 | chr7 | 113727442 | 113727486 | chr7 | 113727754 | 113727781 |
| chr7 | 115117552 | 115117647 | chr7 | 116140252 | 116140356 | chr7 | 116412008 | 116412058 |
| chr7 | 116415100 | 116415129 | chr7 | 116417443 | 116417496 | chr7 | 116422067 | 116422132 |
| chr7 | 116423399 | 116423488 | chr7 | 116962893 | 116963146 | chr7 | 116963331 | 116963476 |
| chr7 | 117119381 | 117120271 | chr7 | 117513675 | 117513849 | chr7 | 119913561 | 119913785 |
| chr7 | 120969672 | 120969800 | chr7 | 121513523 | 121513709 | chr7 | 121939677 | 121940244 |
| chr7 | 121940434 | 121940448 | chr7 | 121940935 | 121941052 | chr7 | 121941881 | 121942170 |
| chr7 | 121945822 | 121945920 | chr7 | 121946478 | 121946982 | chr7 | 121947098 | 121947406 |
| chr7 | 121950137 | 121950264 | chr7 | 121950429 | 121950552 | chr7 | 121950995 | 121951069 |
| chr7 | 121951877 | 121952010 | chr7 | 121952044 | 121952169 | chr7 | 121956486 | 121956567 |
| chr7 | 121956955 | 121957076 | chr7 | 121957254 | 121957331 | chr7 | 122526833 | 122526873 |
| chr7 | 123173150 | 123173244 | chr7 | 123175689 | 123175899 | chr7 | 123672048 | 123672086 |
| chr7 | 124404415 | 124404497 | chr7 | 125082621 | 125082698 | chr7 | 126891220 | 126891250 |
| chr7 | 126891504 | 126891593 | chr7 | 126894076 | 126894197 | chr7 | 127371129 | 127371249 |
| chr7 | 127615921 | 127615951 | chr7 | 127744122 | 127744631 | chr7 | 127806634 | 127806664 |
| chr7 | 127807817 | 127807846 | chr7 | 127808047 | 127808792 | chr7 | 127841626 | 127841704 |
| chr7 | 127991826 | 127991922 | chr7 | 127992045 | 127992135 | chr7 | 128097059 | 128097089 |
| chr7 | 128337467 | 128337594 | chr7 | 128337788 | 128337921 | chr7 | 128470897 | 128471032 |
| chr7 | 128486036 | 128486138 | chr7 | 128528749 | 128528779 | chr7 | 128529023 | 128529053 |
| chr7 | 128828195 | 128828272 | chr7 | 129229456 | 129229631 | chr7 | 129418057 | 129418428 |
| chr7 | 129422160 | 129422968 | chr7 | 129423126 | 129423418 | chr7 | 129423834 | 129424034 |
| chr7 | 129424655 | 129425887 | chr7 | 129426195 | 129426236 | chr7 | 129483356 | 129483449 |
| chr7 | 129794593 | 129794721 | chr7 | 129800243 | 129800434 | chr7 | 129844226 | 129844493 |
| chr7 | 131041515 | 131041596 | chr7 | 131242738 | 131242824 | chr7 | 131514824 | 131514854 |
| chr7 | 132261272 | 132261432 | chr7 | 134143164 | 134143475 | chr7 | 134143807 | 134144132 |
| chr7 | 134918503 | 134918637 | chr7 | 136553311 | 136554025 | chr7 | 136554104 | 136554366 |
| chr7 | 136554638 | 136554966 | chr7 | 136555235 | 136555412 | chr7 | 136555681 | 136555841 |
| chr7 | 136556013 | 136556091 | chr7 | 136969053 | 136969083 | chr7 | 137028481 | 137028524 |
| chr7 | 137531158 | 137531211 | chr7 | 137531263 | 137531888 | chr7 | 137531909 | 137532187 |
| chr7 | 138042221 | 138042288 | chr7 | 138720785 | 138720909 | chr7 | 139167617 | 139167744 |
| chr7 | 139168115 | 139168379 | chr7 | 139208772 | 139208979 | chr7 | 139878250 | 139878296 |
| chr7 | 139930051 | 139930270 | chr7 | 139939160 | 139939318 | chr7 | 140027008 | 140027079 |
| chr7 | 140096812 | 140096882 | chr7 | 140097126 | 140097196 | chr7 | 140180094 | 140180444 |
| chr7 | 140218053 | 140218082 | chr7 | 140218123 | 140218352 | chr7 | 140219405 | 140219435 |
| chr7 | 140339952 | 140339982 | chr7 | 140453121 | 140453167 | chr7 | 140477779 | 140477868 |
| chr7 | 140481381 | 140481431 | chr7 | 140772795 | 140773228 | chr7 | 140773563 | 140773750 |
| chr7 | 142785612 | 142785728 | chr7 | 143042634 | 143042798 | chr7 | 143579739 | 143580069 |
| chr7 | 144712934 | 144713064 | chr7 | 145812992 | 145813082 | chr7 | 145813412 | 145813494 |
| chr7 | 145813946 | 145814166 | chr7 | 148224541 | 148224686 | chr7 | 148508712 | 148508741 |
| chr7 | 148640171 | 148640250 | chr7 | 148846138 | 148846434 | chr7 | 148846434 | 148846544 |
| chr7 | 148851143 | 148851234 | chr7 | 148883821 | 148883973 | chr7 | 149109648 | 149109785 |
| chr7 | 149112058 | 149112248 | chr7 | 149119948 | 149120073 | chr7 | 149411541 | 149411727 |
| chr7 | 149411835 | 149412304 | chr7 | 149570368 | 149570406 | chr7 | 149744505 | 149744560 |
| chr7 | 149917322 | 149917336 | chr7 | 149918119 | 149918469 | chr7 | 150038883 | 150038912 |
| chr7 | 150049604 | 150049718 | chr7 | 150069098 | 150069346 | chr7 | 150069679 | 150069820 |
| chr7 | 150070021 | 150070058 | chr7 | 150081236 | 150081308 | chr7 | 150716169 | 150716305 |
| chr7 | 150748192 | 150748406 | chr7 | 150753942 | 150753981 | chr7 | 150870816 | 150870889 |
| chr7 | 151001356 | 151001435 | chr7 | 151106451 | 151106565 | chr7 | 151106590 | 151106988 |
| chr7 | 151107486 | 151107651 | chr7 | 161188034 | 151188063 | chr7 | 161298870 | 151299029 |
| chr7 | 151423571 | 151423639 | chr7 | 151591667 | 151591705 | chr7 | 162133406 | 152133436 |
| chr7 | 152622621 | 152622697 | chr7 | 162913656 | 152913825 | chr7 | 153583632 | 153584069 |
| chr7 | 153584389 | 153584623 | chr7 | 153584848 | 153585206 | chr7 | 153585602 | 153585606 |
| chr7 | 153633796 | 153633942 | chr7 | 153749720 | 153750042 | chr7 | 154561150 | 154561189 |
| chr7 | 154708275 | 154708338 | chr7 | 154862046 | 154862266 | chr7 | 154926351 | 154926397 |
| chr7 | 155164454 | 155165562 | chr7 | 155165875 | 155166784 | chr7 | 155167034 | 155167089 |
| chr7 | 155167175 | 155167660 | chr7 | 155167834 | 155167909 | chr7 | 155174656 | 155174788 |
| chr7 | 155241318 | 155242049 | chr7 | 155242729 | 155243102 | chr7 | 155243346 | 155243533 |

TABLE 12-continued

| chr | start | end | chr | start | end | chr | start | end |
|---|---|---|---|---|---|---|---|---|
| chr7 | 155243825 | 155243895 | chr7 | 155244180 | 155244361 | chr7 | 155246886 | 155247479 |
| chr7 | 155248913 | 155248943 | chr7 | 155249512 | 155249565 | chr7 | 155249925 | 155250011 |
| chr7 | 155250283 | 155250303 | chr7 | 155250324 | 155250355 | chr7 | 155250787 | 155250996 |
| chr7 | 155251701 | 155251854 | chr7 | 155251891 | 155251939 | chr7 | 155252247 | 155252261 |
| chr7 | 155252317 | 155252490 | chr7 | 155252862 | 155253041 | chr7 | 155254848 | 155255324 |
| chr7 | 155256269 | 155256312 | chr7 | 155257040 | 155257189 | chr7 | 155258193 | 155258487 |
| chr7 | 155258949 | 155259077 | chr7 | 155259120 | 155259622 | chr7 | 155259834 | 155259957 |
| chr7 | 155260039 | 155260137 | chr7 | 155260880 | 155260890 | chr7 | 155261071 | 155261210 |
| chr7 | 155301838 | 155301931 | chr7 | 155302328 | 155302895 | chr7 | 155302964 | 155303335 |
| chr7 | 155325796 | 155325872 | chr7 | 155326169 | 155326522 | chr7 | 155363304 | 155363417 |
| chr7 | 155580182 | 155580211 | chr7 | 155580846 | 155580876 | chr7 | 155581330 | 155581553 |
| chr7 | 155581765 | 155581980 | chr7 | 155582277 | 155582340 | chr7 | 155600629 | 155600723 |
| chr7 | 155602751 | 155602805 | chr7 | 155877196 | 155877283 | chr7 | 156259192 | 156259221 |
| chr7 | 156409144 | 156409347 | chr7 | 156409728 | 156409802 | chr7 | 156701846 | 156701908 |
| chr7 | 156707963 | 156708093 | chr7 | 156744619 | 156744713 | chr7 | 156779336 | 156779366 |
| chr7 | 156794153 | 156794235 | chr7 | 156794443 | 156794485 | chr7 | 156794998 | 156795354 |
| chr7 | 156795402 | 156795635 | chr7 | 156795900 | 156795914 | chr7 | 156796534 | 156796739 |
| chr7 | 156797006 | 156798434 | chr7 | 156798527 | 156799146 | chr7 | 156799291 | 156799467 |
| chr7 | 156800999 | 156801029 | chr7 | 156801403 | 156801601 | chr7 | 156808858 | 156809199 |
| chr7 | 156809983 | 156810521 | chr7 | 156810598 | 156810800 | chr7 | 156811303 | 156811436 |
| chr7 | 156812852 | 156813825 | chr7 | 156813987 | 156814707 | chr7 | 156814784 | 156815092 |
| chr7 | 156832223 | 156832402 | chr7 | 156832848 | 156833162 | chr7 | 156871283 | 156871297 |
| chr7 | 156880531 | 156880561 | chr7 | 157085373 | 157085487 | chr7 | 157085963 | 157086082 |
| chr7 | 157262815 | 157263018 | chr7 | 157263294 | 157263471 | chr7 | 157335172 | 157335202 |
| chr7 | 157361605 | 157361635 | chr7 | 157476879 | 157476973 | chr7 | 157476995 | 157477272 |
| chr7 | 157477473 | 157477488 | chr7 | 157477711 | 157477819 | chr7 | 157481130 | 157481160 |
| chr7 | 157481534 | 157481549 | chr7 | 157481969 | 157482073 | chr7 | 157482492 | 157482667 |
| chr7 | 157483320 | 157483538 | chr7 | 157484877 | 157485277 | chr7 | 157485527 | 157485601 |
| chr7 | 157485650 | 157485705 | chr7 | 157485976 | 157486081 | chr7 | 157486205 | 157486414 |
| chr7 | 157486476 | 157486503 | chr7 | 157584178 | 157584208 | chr7 | 157588586 | 157588791 |
| chr7 | 157606706 | 157606736 | chr7 | 157690056 | 157690086 | chr7 | 158059762 | 158059794 |
| chr7 | 158065832 | 158065970 | chr7 | 158198597 | 158198648 | chr7 | 158298861 | 158299036 |
| chr7 | 158673836 | 158673942 | chr7 | 158741193 | 158741267 | chr7 | 158799762 | 158799791 |
| chr7 | 158936492 | 158936880 | chr7 | 158937203 | 158937374 | chr7 | 158937577 | 158937624 |
| chr7 | 158938210 | 158938399 | chr8 | 686870 | 686884 | chr8 | 687163 | 687217 |
| chr8 | 687838 | 687975 | chr8 | 1085573 | 1085603 | chr8 | 1325465 | 1325606 |
| chr8 | 1444165 | 1444205 | chr8 | 1950097 | 1950134 | chr8 | 4849141 | 4849177 |
| chr8 | 4849466 | 4849500 | chr8 | 4850247 | 4850322 | chr8 | 4850419 | 4850516 |
| chr8 | 4851736 | 4851749 | chr8 | 4852021 | 4852118 | chr8 | 8640024 | 8640100 |
| chr8 | 8681258 | 8681353 | chr8 | 8748422 | 8748713 | chr8 | 8748919 | 8748956 |
| chr8 | 9722850 | 9722896 | chr8 | 9756051 | 9756283 | chr8 | 9760735 | 9761155 |
| chr8 | 9762586 | 9762689 | chr8 | 9762752 | 9762864 | chr8 | 9763143 | 9763275 |
| chr8 | 9763895 | 9764049 | chr8 | 9764196 | 9764214 | chr8 | 9764434 | 9764551 |
| chr8 | 10587589 | 10587602 | chr8 | 10652917 | 10653017 | chr8 | 10980452 | 10980589 |
| chr8 | 11204479 | 11204509 | chr8 | 11204810 | 11204905 | chr8 | 11536827 | 11536857 |
| chr8 | 11537225 | 11537259 | chr8 | 11554885 | 11554915 | chr8 | 11555152 | 11555166 |
| chr8 | 11555474 | 11555521 | chr8 | 11559759 | 11559794 | chr8 | 11560068 | 11560375 |
| chr8 | 11560711 | 11560793 | chr8 | 11561442 | 11562169 | chr8 | 11562422 | 11562485 |
| chr8 | 11562701 | 11562917 | chr8 | 11700190 | 11700284 | chr8 | 11705960 | 11706136 |
| chr8 | 11706580 | 11706613 | chr8 | 11726469 | 11726975 | chr8 | 11790579 | 11790653 |
| chr8 | 12990386 | 12990431 | chr8 | 12990664 | 12990784 | chr8 | 13319931 | 13319961 |
| chr8 | 15094505 | 15094566 | chr8 | 16884182 | 16884239 | chr8 | 16885205 | 16885241 |
| chr8 | 17271091 | 12271119 | chr8 | 19797433 | 19797463 | chr8 | 19797939 | 19798019 |
| chr8 | 20375563 | 20375592 | chr8 | 21876649 | 21876819 | chr8 | 22089409 | 22089560 |
| chr8 | 22101641 | 22101699 | chr8 | 22458657 | 22458687 | chr8 | 22562345 | 22562483 |
| chr8 | 22960648 | 22960723 | chr8 | 23020951 | 23021107 | chr8 | 23260683 | 23260870 |
| chr8 | 23423923 | 23423974 | chr8 | 23559385 | 23559601 | chr8 | 23559666 | 23560525 |
| chr8 | 23563791 | 23564023 | chr8 | 23564193 | 23564388 | chr8 | 23564652 | 23564668 |
| chr8 | 23564703 | 23665024 | chr8 | 23566803 | 23566854 | chr8 | 23566901 | 23567213 |
| chr8 | 23567312 | 23567492 | chr8 | 23571681 | 23571973 | chr8 | 23572377 | 23572554 |
| chr8 | 23584094 | 23584400 | chr8 | 23584582 | 23584760 | chr8 | 24770314 | 24770700 |
| chr8 | 24770414 | 24770581 | chr8 | 24771431 | 24771562 | chr8 | 24813188 | 24813287 |
| chr8 | 24813750 | 24813893 | chr8 | 24814011 | 24814407 | chr8 | 24857776 | 24857808 |
| chr8 | 24858336 | 24858440 | chr8 | 24858856 | 24859161 | chr8 | 24859496 | 24859526 |
| chr8 | 25041746 | 25041864 | chr8 | 25042534 | 25042567 | chr8 | 25900408 | 25900692 |
| chr8 | 25900781 | 25901317 | chr8 | 25901540 | 25901765 | chr8 | 25902146 | 25902176 |
| chr8 | 25902619 | 25902649 | chr8 | 25903662 | 25903854 | chr8 | 25904157 | 26904191 |
| chr8 | 25905096 | 25905126 | chr8 | 25905762 | 25905811 | chr8 | 25909197 | 26909597 |
| chr8 | 26372863 | 26372893 | chr8 | 26723985 | 26724080 | chr8 | 28266438 | 28266484 |
| chr8 | 28737884 | 28738023 | chr8 | 30243388 | 30243423 | chr8 | 30475450 | 30475480 |
| chr8 | 30769249 | 30769411 | chr8 | 30770106 | 30770109 | chr8 | 30770158 | 30770188 |
| chr8 | 31044103 | 31044133 | chr8 | 31496481 | 31496757 | chr8 | 31497024 | 31497152 |
| chr8 | 31497499 | 31497639 | chr8 | 32406598 | 32406914 | chr8 | 33372069 | 33372156 |
| chr8 | 33457142 | 33457379 | chr8 | 35093037 | 35093054 | chr8 | 35093951 | 35093973 |
| chr8 | 37655476 | 37655517 | chr8 | 37655810 | 37655990 | chr8 | 37656050 | 37656081 |
| chr8 | 37755922 | 37755952 | chr8 | 37822796 | 37823423 | chr8 | 37906396 | 37906513 |
| chr8 | 37961793 | 37961902 | chr8 | 38008234 | 38008557 | chr8 | 38020213 | 38020272 |
| chr8 | 38032345 | 38032827 | chr8 | 38256378 | 38256412 | chr8 | 38262472 | 38262502 |

TABLE 12-continued

| chr | start | end | chr | start | end | chr | start | end |
|---|---|---|---|---|---|---|---|---|
| chr8 | 38274835 | 38274864 | chr8 | 38323911 | 38323941 | chr8 | 38965322 | 38965386 |
| chr8 | 39172082 | 39172134 | chr8 | 41165865 | 41165918 | chr8 | 41166001 | 41166151 |
| chr8 | 41166267 | 41166679 | chr8 | 41166974 | 41166988 | chr8 | 41167026 | 41167035 |
| chr8 | 41424760 | 41424842 | chr8 | 41624826 | 41624855 | chr8 | 41625112 | 41625141 |
| chr8 | 41700639 | 41700751 | chr8 | 41711325 | 41711447 | chr8 | 41733505 | 41733640 |
| chr8 | 41753593 | 41753752 | chr8 | 41754152 | 41754885 | chr8 | 41755178 | 41755208 |
| chr8 | 41910270 | 41910339 | chr8 | 42082721 | 42082874 | chr8 | 42147392 | 42147521 |
| chr8 | 42293604 | 42293722 | chr8 | 42350324 | 42350492 | chr8 | 42749816 | 42750012 |
| chr8 | 47093246 | 47093276 | chr8 | 47334619 | 47334678 | chr8 | 48044710 | 48044753 |
| chr8 | 48100155 | 48100443 | chr8 | 49293364 | 49293524 | chr8 | 49293581 | 49293614 |
| chr8 | 49468669 | 49469127 | chr8 | 49572029 | 49572058 | chr8 | 49783041 | 49783283 |
| chr8 | 49836145 | 49836174 | chr8 | 49959230 | 49959260 | chr8 | 50822179 | 50822308 |
| chr8 | 50822686 | 50822734 | chr8 | 50823452 | 50823562 | chr8 | 52230518 | 52230548 |
| chr8 | 53322495 | 53322524 | chr8 | 53477408 | 53477736 | chr8 | 53478008 | 53478275 |
| chr8 | 53478480 | 53478720 | chr8 | 53851141 | 53851170 | chr8 | 53853811 | 53854509 |
| chr8 | 54163316 | 54163349 | chr8 | 54163674 | 54164126 | chr8 | 54698973 | 54699103 |
| chr8 | 54789278 | 54789310 | chr8 | 54789632 | 54789805 | chr8 | 54790023 | 54790077 |
| chr8 | 54790291 | 54790855 | chr8 | 54791898 | 54791945 | chr8 | 54792185 | 54792237 |
| chr8 | 54792634 | 54792670 | chr8 | 54792702 | 54792760 | chr8 | 54794217 | 54794327 |
| chr8 | 54794713 | 54794780 | chr8 | 54794827 | 54794949 | chr8 | 54795140 | 54795196 |
| chr8 | 55366188 | 55366367 | chr8 | 55366952 | 55367641 | chr8 | 55370113 | 55370432 |
| chr8 | 55370568 | 55370713 | chr8 | 55370836 | 55370858 | chr8 | 55371178 | 55371375 |
| chr8 | 55371440 | 55371724 | chr8 | 55371994 | 55372067 | chr8 | 55372417 | 55372538 |
| chr8 | 55379296 | 55379456 | chr8 | 55383183 | 55383237 | chr8 | 55826087 | 55826117 |
| chr8 | 56013641 | 56013892 | chr8 | 56014157 | 56014184 | chr8 | 56014623 | 56014743 |
| chr8 | 56015038 | 56015052 | chr8 | 56015186 | 56015357 | chr8 | 56015560 | 56015619 |
| chr8 | 56015908 | 56015938 | chr8 | 56542925 | 56543064 | chr8 | 57025776 | 57025943 |
| chr8 | 57026168 | 57026213 | chr8 | 57026503 | 57026547 | chr8 | 57069553 | 57069737 |
| chr8 | 57069851 | 57070157 | chr8 | 57358465 | 57358661 | chr8 | 57358807 | 57359091 |
| chr8 | 57359260 | 57359636 | chr8 | 57359893 | 57359922 | chr8 | 57360211 | 57360240 |
| chr8 | 57360570 | 57360625 | chr8 | 57360770 | 57360791 | chr8 | 58105946 | 58106115 |
| chr8 | 58117004 | 58117079 | chr8 | 58130364 | 58130574 | chr8 | 58907698 | 58907835 |
| chr8 | 59058941 | 59059343 | chr8 | 59747186 | 59747318 | chr8 | 60032680 | 60032238 |
| chr8 | 61777575 | 61777699 | chr8 | 61789974 | 61790004 | chr8 | 62033879 | 62034059 |
| chr8 | 62200502 | 62200776 | chr8 | 62763403 | 62763433 | chr8 | 63161658 | 63161800 |
| chr8 | 65281616 | 65281760 | chr8 | 65281984 | 65282004 | chr8 | 65282333 | 65282440 |
| chr8 | 65282713 | 65282944 | chr8 | 65283042 | 65283341 | chr8 | 65283799 | 65284094 |
| chr8 | 65286056 | 65286066 | chr8 | 65286682 | 65286753 | chr8 | 65286963 | 65287251 |
| chr8 | 65289123 | 65289241 | chr8 | 65289614 | 65290681 | chr8 | 65291034 | 65291284 |
| chr8 | 65292185 | 65292727 | chr8 | 65488271 | 65488322 | chr8 | 65488661 | 65488697 |
| chr8 | 65489099 | 65489129 | chr8 | 65492712 | 65492979 | chr8 | 65493195 | 65493433 |
| chr8 | 65494077 | 65494193 | chr8 | 65498566 | 65498841 | chr8 | 65499757 | 65500015 |
| chr8 | 65710938 | 65711046 | chr8 | 66548717 | 66548800 | chr8 | 66560323 | 66560545 |
| chr8 | 67025063 | 67025640 | chr8 | 67025920 | 67026578 | chr8 | 67026812 | 67026990 |
| chr8 | 67344538 | 67344701 | chr8 | 67580735 | 67580829 | chr8 | 67873327 | 67873421 |
| chr8 | 67873799 | 67874050 | chr8 | 67874165 | 67874672 | chr8 | 67874756 | 67875682 |
| chr8 | 67940624 | 67940875 | chr8 | 68864578 | 68864765 | chr8 | 69242905 | 69242988 |
| chr8 | 69243285 | 69243902 | chr8 | 69243964 | 69243994 | chr8 | 69244370 | 69244500 |
| chr8 | 70744860 | 70744925 | chr8 | 70946760 | 70946914 | chr8 | 70947091 | 70947658 |
| chr8 | 70982263 | 70982566 | chr8 | 70982851 | 70983226 | chr8 | 70983504 | 70983869 |
| chr8 | 70984017 | 70984292 | chr8 | 70984344 | 70984661 | chr8 | 70984745 | 70984978 |
| chr8 | 71017156 | 71017195 | chr8 | 71308096 | 71308126 | chr8 | 71447529 | 71447559 |
| chr8 | 72273998 | 72274033 | chr8 | 72468569 | 72469574 | chr8 | 72470399 | 72470441 |
| chr8 | 72471053 | 72471083 | chr8 | 72754491 | 72754609 | chr8 | 72754821 | 72755176 |
| chr8 | 72755666 | 72755814 | chr8 | 72756656 | 72756896 | chr8 | 72917335 | 72917428 |
| chr8 | 72987600 | 72988036 | chr8 | 73163860 | 73164180 | chr8 | 73450064 | 73450100 |
| chr8 | 73450515 | 73450559 | chr8 | 74759306 | 74759463 | chr8 | 74759819 | 74759966 |
| chr8 | 74889486 | 74889592 | chr8 | 75896574 | 75897337 | chr8 | 76316329 | 76316452 |
| chr8 | 77585219 | 77585698 | chr8 | 77586175 | 77586278 | chr8 | 77586563 | 77586617 |
| chr8 | 77590239 | 77590466 | chr8 | 77593110 | 77593376 | chr8 | 77593889 | 77594124 |
| chr8 | 77594648 | 77594674 | chr8 | 77594758 | 77594993 | chr8 | 77595339 | 77595494 |
| chr8 | 79428297 | 79428401 | chr8 | 80523983 | 80524029 | chr8 | 80524253 | 80524318 |
| chr8 | 80524946 | 80525020 | chr8 | 80525604 | 80525733 | chr8 | 80695902 | 80695932 |
| chr8 | 80803673 | 80803872 | chr8 | 80894529 | 80894594 | chr8 | 80998525 | 80998601 |
| chr8 | 81128658 | 81128782 | chr8 | 81398018 | 81398155 | chr8 | 81398428 | 81399496 |
| chr8 | 81414643 | 81414831 | chr8 | 81478185 | 81478350 | chr8 | 82243813 | 82243843 |
| chr8 | 82902963 | 82902993 | chr8 | 84932902 | 84932942 | chr8 | 85095482 | 85095668 |
| chr8 | 85096583 | 85096772 | chr8 | 85097063 | 85097220 | chr8 | 86131760 | 86131850 |
| chr8 | 86350553 | 86350566 | chr8 | 86405788 | 86405818 | chr8 | 86406716 | 86406849 |
| chr8 | 86436621 | 86436651 | chr8 | 86495193 | 86495287 | chr8 | 86544756 | 86544959 |
| chr8 | 89339389 | 89339745 | chr8 | 89340274 | 89340345 | chr8 | 90702972 | 90703034 |
| chr8 | 90913079 | 90913653 | chr8 | 91094221 | 91094251 | chr8 | 91411537 | 91411567 |
| chr8 | 91803676 | 91803718 | chr8 | 91804065 | 91804253 | chr8 | 91997046 | 91997508 |
| chr8 | 91997528 | 91997947 | chr8 | 92083523 | 92083751 | chr8 | 93114135 | 93114241 |
| chr8 | 93114307 | 93114528 | chr8 | 94684190 | 94684560 | chr8 | 95485999 | 95486029 |
| chr8 | 95651098 | 95651218 | chr8 | 95651538 | 95651655 | chr8 | 96038540 | 96038580 |
| chr8 | 96219863 | 96219901 | chr8 | 96285420 | 96285553 | chr8 | 97157085 | 97157209 |
| chr8 | 97157667 | 97157897 | chr8 | 97158022 | 97158066 | chr8 | 97165644 | 97165676 |

TABLE 12-continued

| chr | start | end | chr | start | end | chr | start | end |
|---|---|---|---|---|---|---|---|---|
| chr8 | 97166425 | 97166455 | chr8 | 97167178 | 97167223 | chr8 | 97167811 | 97167855 |
| chr8 | 97169838 | 97169955 | chr8 | 97170054 | 97170334 | chr8 | 97170867 | 97170897 |
| chr8 | 97171129 | 97171264 | chr8 | 97171318 | 97171958 | chr8 | 97172019 | 97172200 |
| chr8 | 97172433 | 97172739 | chr8 | 97172822 | 97173458 | chr8 | 97173822 | 97173853 |
| chr8 | 97173921 | 97173935 | chr8 | 97339846 | 97340195 | chr8 | 97506034 | 97506048 |
| chr8 | 97506178 | 97506407 | chr8 | 97506448 | 97506524 | chr8 | 97507115 | 97507284 |
| chr8 | 97507546 | 97507680 | chr8 | 98289825 | 98289867 | chr8 | 98289923 | 98290260 |
| chr8 | 98744202 | 98744325 | chr8 | 98786343 | 98786387 | chr8 | 98786918 | 98786972 |
| chr8 | 99234962 | 99235037 | chr8 | 99439104 | 99439133 | chr8 | 99439382 | 99440354 |
| chr8 | 99951404 | 99951434 | chr8 | 99951836 | 99952143 | chr8 | 99952199 | 99952303 |
| chr8 | 99952533 | 99952815 | chr8 | 99954490 | 99954562 | chr8 | 99954679 | 99954727 |
| chr8 | 99956180 | 99955327 | chr8 | 99959429 | 99959549 | chr8 | 99960329 | 99960497 |
| chr8 | 99960922 | 99960971 | chr8 | 99961792 | 99961822 | chr8 | 99985865 | 99986043 |
| chr8 | 99986226 | 99986526 | chr8 | 99986792 | 99987014 | chr8 | 100117651 | 100117765 |
| chr8 | 101118241 | 101118490 | chr8 | 101169625 | 101169659 | chr8 | 101661920 | 101661991 |
| chr8 | 101726865 | 101726945 | chr8 | 101736027 | 101736202 | chr8 | 101821973 | 101822047 |
| chr8 | 101920382 | 101920468 | chr8 | 102504464 | 102504506 | chr8 | 102505512 | 102505556 |
| chr8 | 102505797 | 102505985 | chr8 | 103575128 | 103575296 | chr8 | 103629590 | 103629882 |
| chr8 | 104153202 | 104153246 | chr8 | 104153449 | 104153561 | chr8 | 104383700 | 104383985 |
| chr8 | 104512123 | 104513186 | chr8 | 104513462 | 104513926 | chr8 | 105235369 | 105235501 |
| chr8 | 105235644 | 105235803 | chr8 | 105235864 | 105236054 | chr8 | 105478725 | 105478779 |
| chr8 | 105479404 | 105479464 | chr8 | 106301844 | 106301978 | chr8 | 106331160 | 106331237 |
| chr8 | 106332104 | 106332202 | chr8 | 106434115 | 106434145 | chr8 | 107282163 | 107282195 |
| chr8 | 107284038 | 107284075 | chr8 | 108509543 | 108509697 | chr8 | 109093679 | 109094180 |
| chr8 | 109094485 | 109094595 | chr8 | 109094840 | 109095436 | chr8 | 109095506 | 109095932 |
| chr8 | 109500408 | 109500507 | chr8 | 109799588 | 109799739 | chr8 | 110275006 | 110275040 |
| chr8 | 110406028 | 110406243 | chr8 | 110592198 | 110592228 | chr8 | 110704001 | 110704144 |
| chr8 | 110986443 | 110986682 | chr8 | 111133092 | 111133257 | chr8 | 114444580 | 114445192 |
| chr8 | 114445763 | 114446068 | chr8 | 114446405 | 114446435 | chr8 | 114446931 | 114447368 |
| chr8 | 114449039 | 114449257 | chr8 | 114449550 | 114449602 | chr8 | 115516296 | 115516440 |
| chr8 | 116660527 | 116660571 | chr8 | 116660616 | 116660670 | chr8 | 117950438 | 117950648 |
| chr8 | 117950783 | 117950914 | chr8 | 118532128 | 118632292 | chr8 | 119043568 | 119043732 |
| chr8 | 120219912 | 120219941 | chr8 | 120220116 | 120220145 | chr8 | 120220428 | 120220592 |
| chr8 | 120650979 | 120651008 | chr8 | 120651221 | 120651412 | chr8 | 120844095 | 120844285 |
| chr8 | 120845586 | 120845807 | chr8 | 121136879 | 121137748 | chr8 | 121823901 | 121823930 |
| chr8 | 121824203 | 121824481 | chr8 | 121825455 | 121825484 | chr8 | 122068889 | 122068919 |
| chr8 | 122346689 | 122346719 | chr8 | 122346940 | 122347052 | chr8 | 122651872 | 122651905 |
| chr8 | 123695532 | 123695660 | chr8 | 124014063 | 124014111 | chr8 | 124055236 | 124055336 |
| chr8 | 124173246 | 124173501 | chr8 | 124332846 | 124332875 | chr8 | 124427887 | 124428082 |
| chr8 | 125411827 | 125411857 | chr8 | 125452366 | 125452411 | chr8 | 126007690 | 126008051 |
| chr8 | 126044442 | 126044563 | chr8 | 127354106 | 127354261 | chr8 | 127569621 | 127569676 |
| chr8 | 128403354 | 128403383 | chr8 | 128745542 | 128745633 | chr8 | 128808002 | 128808077 |
| chr8 | 128872385 | 128872415 | chr8 | 128889324 | 128889422 | chr8 | 128893019 | 128893049 |
| chr8 | 128931133 | 128931261 | chr8 | 128964114 | 128964309 | chr8 | 129356009 | 129356039 |
| chr8 | 130369244 | 130369364 | chr8 | 132052147 | 132052299 | chr8 | 132052399 | 132052515 |
| chr8 | 132052590 | 132053164 | chr8 | 132053715 | 132054583 | chr8 | 132054594 | 132054785 |
| chr8 | 133360080 | 133360194 | chr8 | 133686745 | 133687107 | chr8 | 135301097 | 135301142 |
| chr8 | 139508757 | 139508946 | chr8 | 139509741 | 139509928 | chr8 | 140714570 | 140714877 |
| chr8 | 140715090 | 140715094 | chr8 | 140715469 | 140715587 | chr8 | 140715965 | 140716021 |
| chr8 | 140716340 | 140716382 | chr8 | 140755383 | 140755550 | chr8 | 140834237 | 140834321 |
| chr8 | 140963292 | 140963362 | chr8 | 141054845 | 141054875 | chr8 | 141159919 | 141159949 |
| chr8 | 141588055 | 141588132 | chr8 | 141596886 | 141597002 | chr8 | 141614252 | 141614423 |
| chr8 | 142210914 | 142211043 | chr8 | 142265206 | 142265339 | chr8 | 142282078 | 142282202 |
| chr8 | 142292552 | 142292774 | chr8 | 142318155 | 142318184 | chr8 | 142361233 | 142361487 |
| chr8 | 142367368 | 142367790 | chr8 | 142444600 | 142444752 | chr8 | 142528400 | 142528402 |
| chr8 | 142528455 | 142528606 | chr8 | 142528671 | 142528781 | chr8 | 142528835 | 142528961 |
| chr8 | 142535343 | 142535496 | chr8 | 142568598 | 142568652 | chr8 | 142632436 | 142632465 |
| chr8 | 142694847 | 142694953 | chr8 | 142984512 | 142984666 | chr8 | 143082777 | 143082810 |
| chr8 | 143089030 | 143089100 | chr8 | 143105244 | 143105377 | chr8 | 143368318 | 143368469 |
| chr8 | 143509457 | 143509594 | chr8 | 143532122 | 143532509 | chr8 | 143532542 | 143532846 |
| chr8 | 143533611 | 143533640 | chr8 | 143533709 | 143533906 | chr8 | 143557980 | 143558080 |
| chr8 | 143558472 | 143558604 | chr8 | 143587331 | 143587382 | chr8 | 143592664 | 143592687 |
| chr8 | 143611232 | 143611262 | chr8 | 143621980 | 143622096 | chr8 | 143702052 | 143702101 |
| chr8 | 143819384 | 143819428 | chr8 | 143858522 | 143858699 | chr8 | 143859338 | 143859361 |
| chr8 | 143876928 | 143876958 | chr8 | 143993974 | 143994165 | chr8 | 144069546 | 144069651 |
| chr8 | 144190378 | 144190432 | chr8 | 144203653 | 144203708 | chr8 | 144203977 | 144204021 |
| chr8 | 144226174 | 144226204 | chr8 | 144238822 | 144238901 | chr8 | 144241250 | 144241287 |
| chr8 | 144241871 | 144242356 | chr8 | 144303562 | 144303592 | chr8 | 144328321 | 144328565 |
| chr8 | 144330193 | 144330380 | chr8 | 144344293 | 144344442 | chr8 | 144347397 | 144347740 |
| chr8 | 144359977 | 144360076 | chr8 | 144360394 | 144360453 | chr8 | 144361758 | 144361823 |
| chr8 | 144372323 | 144372503 | chr8 | 144382679 | 144382775 | chr8 | 144421487 | 144421517 |
| chr8 | 144509325 | 144510529 | chr8 | 144511225 | 144511424 | chr8 | 144512041 | 144512192 |
| chr8 | 144512473 | 144512503 | chr8 | 144557003 | 144557088 | chr8 | 144601799 | 144601851 |
| chr8 | 144617065 | 144617347 | chr8 | 144650594 | 144650730 | chr8 | 144668566 | 144668667 |
| chr8 | 144668909 | 144668972 | chr8 | 145033304 | 145033333 | chr8 | 145218226 | 145218301 |
| chr8 | 145223902 | 145224061 | chr8 | 145753517 | 145753547 | chr8 | 145758572 | 145758692 |
| chr8 | 145806258 | 145806271 | chr8 | 145918683 | 145918835 | chr8 | 145925461 | 145925491 |
| chr8 | 145925947 | 145926068 | chr8 | 146013617 | 146013647 | chr8 | 146079215 | 146079379 |

TABLE 12-continued

| chr | start | end | chr | start | end | chr | start | end |
|---|---|---|---|---|---|---|---|---|
| chr8 | 146175120 | 146175269 | chr8 | 146176756 | 146176795 | chr9 | 113433 | 113512 |
| chr9 | 113550 | 113556 | chr9 | 113850 | 113885 | chr9 | 117884 | 117959 |
| chr9 | 841691 | 842031 | chr9 | 842208 | 842230 | chr9 | 842611 | 842673 |
| chr9 | 969556 | 969586 | chr9 | 969788 | 969846 | chr9 | 970096 | 970104 |
| chr9 | 970186 | 970225 | chr9 | 970495 | 970525 | chr9 | 970897 | 970911 |
| chr9 | 970993 | 971338 | chr9 | 972307 | 972759 | chr9 | 973184 | 973289 |
| chr9 | 974514 | 974547 | chr9 | 975117 | 975167 | chr9 | 975783 | 976321 |
| chr9 | 976618 | 976689 | chr9 | 976912 | 976961 | chr9 | 981797 | 981830 |
| chr9 | 1042402 | 1042500 | chr9 | 1042616 | 1042986 | chr9 | 1051905 | 1052165 |
| chr9 | 2115824 | 2115981 | chr9 | 3181752 | 3181869 | chr9 | 5070006 | 5070050 |
| chr9 | 5073756 | 5073788 | chr9 | 5078346 | 5078375 | chr9 | 5089711 | 5089740 |
| chr9 | 5153325 | 5153380 | chr9 | 6182901 | 6182931 | chr9 | 6412571 | 6412809 |
| chr9 | 6644297 | 6644367 | chr9 | 6644540 | 6644554 | chr9 | 6645017 | 6645333 |
| chr9 | 6645625 | 6645700 | chr9 | 6756353 | 6756623 | chr9 | 13278818 | 13278864 |
| chr9 | 14312994 | 14313096 | chr9 | 14313319 | 14313785 | chr9 | 14347633 | 14347673 |
| chr9 | 14348314 | 14348452 | chr9 | 14884008 | 14884061 | chr9 | 17906404 | 17906432 |
| chr9 | 17906461 | 17906694 | chr9 | 17907004 | 17907061 | chr9 | 17907451 | 17907472 |
| chr9 | 19789107 | 19789301 | chr9 | 20199955 | 20199985 | chr9 | 21031734 | 21031836 |
| chr9 | 21402617 | 21403021 | chr9 | 21559294 | 21569381 | chr9 | 21559655 | 21559702 |
| chr9 | 21965057 | 21965424 | chr9 | 21965570 | 21965757 | chr9 | 21968218 | 21968433 |
| chr9 | 21968457 | 21968475 | chr9 | 21970959 | 21971154 | chr9 | 21971185 | 21971220 |
| chr9 | 21973940 | 21974076 | chr9 | 21974182 | 21974237 | chr9 | 21974499 | 21974794 |
| chr9 | 21994208 | 21994237 | chr9 | 21995297 | 21995326 | chr9 | 21995720 | 21995749 |
| chr9 | 22006131 | 22006152 | chr9 | 22008819 | 22008899 | chr9 | 22447664 | 22447708 |
| chr9 | 23822568 | 23822606 | chr9 | 23824561 | 23824591 | chr9 | 23831100 | 23831370 |
| chr9 | 29212170 | 29212170 | chr9 | 29212211 | 29212294 | chr9 | 29213508 | 29213651 |
| chr9 | 29214030 | 29214144 | chr9 | 29214360 | 29214430 | chr9 | 29214681 | 29215086 |
| chr9 | 32782630 | 32782935 | chr9 | 32783084 | 32783121 | chr9 | 32783346 | 32783419 |
| chr9 | 32783591 | 32783657 | chr9 | 33000470 | 33000512 | chr9 | 33524609 | 33524687 |
| chr9 | 33676771 | 33676801 | chr9 | 33677360 | 33677415 | chr9 | 34136792 | 34136903 |
| chr9 | 34224348 | 34224474 | chr9 | 34372805 | 34372983 | chr9 | 34589062 | 34589156 |
| chr9 | 35617291 | 35617337 | chr9 | 35675539 | 35675647 | chr9 | 35675838 | 35676180 |
| chr9 | 35844834 | 35844863 | chr9 | 36036323 | 36036353 | chr9 | 36037068 | 36037098 |
| chr9 | 36167272 | 36167544 | chr9 | 36196920 | 36197005 | chr9 | 36318375 | 36318410 |
| chr9 | 36433491 | 36433629 | chr9 | 36739812 | 36739980 | chr9 | 36832204 | 36832343 |
| chr9 | 37002454 | 37002517 | chr9 | 37002819 | 37003077 | chr9 | 37025564 | 37025783 |
| chr9 | 37026146 | 37026351 | chr9 | 37026434 | 37026622 | chr9 | 37026831 | 37027271 |
| chr9 | 37027325 | 37027412 | chr9 | 37027800 | 37027829 | chr9 | 37028944 | 37029119 |
| chr9 | 37029534 | 37030655 | chr9 | 37034197 | 37034247 | chr9 | 37034616 | 37034731 |
| chr9 | 37035366 | 37035734 | chr9 | 37036425 | 37036647 | chr9 | 37037671 | 37038354 |
| chr9 | 37119301 | 37119331 | chr9 | 37467610 | 37467898 | chr9 | 37593684 | 37593795 |
| chr9 | 37697404 | 37697438 | chr9 | 38620530 | 38620725 | chr9 | 38646763 | 38646839 |
| chr9 | 66455999 | 66456047 | chr9 | 71200632 | 71200662 | chr9 | 71500847 | 71500886 |
| chr9 | 71584152 | 71584254 | chr9 | 71734816 | 71735024 | chr9 | 71788952 | 71789260 |
| chr9 | 71789453 | 71789757 | chr9 | 72435189 | 72435317 | chr9 | 73032801 | 73032831 |
| chr9 | 74061838 | 74062070 | chr9 | 74210499 | 74210654 | chr9 | 74764547 | 74764648 |
| chr9 | 27112993 | 77113340 | chr9 | 77113559 | 77113708 | chr9 | 77113806 | 77113825 |
| chr9 | 77114745 | 77114851 | chr9 | 77115210 | 77115447 | chr9 | 77115657 | 77115690 |
| chr9 | 77823177 | 77823315 | chr9 | 79197119 | 79197149 | chr9 | 79231003 | 79231033 |
| chr9 | 79626876 | 79627370 | chr9 | 79628289 | 79628329 | chr9 | 79629208 | 79629471 |
| chr9 | 79629879 | 79630420 | chr9 | 79631192 | 79631335 | chr9 | 79631555 | 79631591 |
| chr9 | 79631865 | 79632182 | chr9 | 79632860 | 79632890 | chr9 | 79633397 | 79633520 |
| chr9 | 79634170 | 79635448 | chr9 | 79635746 | 79636043 | chr9 | 79636258 | 79637274 |
| chr9 | 79637555 | 79637888 | chr9 | 79638137 | 79638244 | chr9 | 80303132 | 80303171 |
| chr9 | 80409473 | 80409502 | chr9 | 80833933 | 80834011 | chr9 | 85372494 | 85372596 |
| chr9 | 85577905 | 85677992 | chr9 | 86152387 | 86152417 | chr9 | 86578079 | 86578366 |
| chr9 | 86755532 | 86755952 | chr9 | 86886706 | 86886736 | chr9 | 87283008 | 87283038 |
| chr9 | 87283677 | 87283709 | chr9 | 82284706 | 87284798 | chr9 | 87285279 | 87285472 |
| chr9 | 88137524 | 88137725 | chr9 | 88137875 | 88137998 | chr9 | 88694345 | 88694438 |
| chr9 | 89560760 | 89560827 | chr9 | 89561063 | 89561109 | chr9 | 90907408 | 90907438 |
| chr9 | 90937357 | 90937387 | chr9 | 91150222 | 91150335 | chr9 | 91606004 | 91606058 |
| chr9 | 91792357 | 91792387 | chr9 | 91792776 | 91792907 | chr9 | 91793177 | 91793526 |
| chr9 | 91914276 | 91914306 | chr9 | 92053911 | 92053949 | chr9 | 93698029 | 93698133 |
| chr9 | 94183870 | 94183954 | chr9 | 94572641 | 94572743 | chr9 | 94686919 | 94686957 |
| chr9 | 95417551 | 95417651 | chr9 | 95560810 | 95560840 | chr9 | 95569759 | 95569822 |
| chr9 | 95570247 | 95570434 | chr9 | 95571617 | 95571760 | chr9 | 95761687 | 95761828 |
| chr9 | 95947130 | 95947296 | chr9 | 96230296 | 96230334 | chr9 | 96573748 | 96573869 |
| chr9 | 96588858 | 96588885 | chr9 | 96710377 | 96710407 | chr9 | 96710647 | 96710991 |
| chr9 | 96711258 | 96711446 | chr9 | 96711535 | 96711617 | chr9 | 96711975 | 96712005 |
| chr9 | 96713378 | 96713893 | chr9 | 96715095 | 96715372 | chr9 | 96715688 | 96715857 |
| chr9 | 96716905 | 96717427 | chr9 | 96717450 | 96717466 | chr9 | 96717979 | 96718149 |
| chr9 | 96720803 | 96720885 | chr9 | 96721103 | 96721467 | chr9 | 96721689 | 96721802 |
| chr9 | 96722445 | 96722547 | chr9 | 96723093 | 96723159 | chr9 | 96723171 | 96723202 |
| chr9 | 96856991 | 96857144 | chr9 | 97020978 | 97021126 | chr9 | 97845915 | 97845947 |
| chr9 | 98076746 | 98076776 | chr9 | 98111365 | 98111560 | chr9 | 98111895 | 98112157 |
| chr9 | 98112344 | 98112395 | chr9 | 98784772 | 98784802 | chr9 | 98789651 | 98790000 |
| chr9 | 99146020 | 99146153 | chr9 | 99259362 | 99259405 | chr9 | 99449135 | 99449451 |
| chr9 | 99450020 | 99450142 | chr9 | 99639621 | 99639942 | chr9 | 99983140 | 99983170 |

TABLE 12-continued

| chr | start | end | chr | start | end | chr | start | end |
|---|---|---|---|---|---|---|---|---|
| chr9 | 99983411 | 99983824 | chr9 | 99984026 | 99984057 | chr9 | 99984108 | 99984242 |
| chr9 | 100397821 | 100398016 | chr9 | 100503625 | 100503937 | chr9 | 100609991 | 100610134 |
| chr9 | 100610201 | 100610218 | chr9 | 100610681 | 100610816 | chr9 | 100611125 | 100611640 |
| chr9 | 100613828 | 100613999 | chr9 | 100614193 | 100614325 | chr9 | 100614541 | 100616035 |
| chr9 | 100616271 | 100616468 | chr9 | 100617293 | 100617365 | chr9 | 100617682 | 100618055 |
| chr9 | 100619722 | 100620069 | chr9 | 100620330 | 100620783 | chr9 | 100818295 | 100818437 |
| chr9 | 100835828 | 100835870 | chr9 | 101469269 | 101469307 | chr9 | 101469603 | 101469796 |
| chr9 | 101470116 | 101470250 | chr9 | 101470968 | 101471071 | chr9 | 101471570 | 101471621 |
| chr9 | 101471860 | 101472009 | chr9 | 101705996 | 101706195 | chr9 | 101706313 | 101706695 |
| chr9 | 103174620 | 103174730 | chr9 | 104248579 | 104248623 | chr9 | 104249475 | 104249562 |
| chr9 | 104500625 | 104500774 | chr9 | 106998039 | 106998134 | chr9 | 110126074 | 110126247 |
| chr9 | 110228200 | 110228602 | chr9 | 110251388 | 110251418 | chr9 | 110252363 | 110252515 |
| chr9 | 111894386 | 111894520 | chr9 | 112403170 | 112403200 | chr9 | 112403364 | 112403394 |
| chr9 | 113341522 | 113341621 | chr9 | 113341680 | 113341847 | chr9 | 113341927 | 113341965 |
| chr9 | 113342299 | 113342340 | chr9 | 114247454 | 114247578 | chr9 | 115067932 | 115068106 |
| chr9 | 115087567 | 115087597 | chr9 | 115478932 | 115479250 | chr9 | 115566363 | 115566583 |
| chr9 | 115652966 | 115653425 | chr9 | 116633883 | 116633987 | chr9 | 117050981 | 117051030 |
| chr9 | 118917024 | 118917079 | chr9 | 119603412 | 119603535 | chr9 | 120175795 | 120175832 |
| chr9 | 120176104 | 120176151 | chr9 | 120176867 | 120176939 | chr9 | 122131497 | 122131642 |
| chr9 | 122131880 | 122132025 | chr9 | 122132052 | 122132227 | chr9 | 123004898 | 123004928 |
| chr9 | 123295355 | 123295463 | chr9 | 124535347 | 124535611 | chr9 | 124749865 | 124749953 |
| chr9 | 124751485 | 124751515 | chr9 | 125676633 | 125676753 | chr9 | 125704789 | 125704835 |
| chr9 | 126133778 | 126133856 | chr9 | 126154304 | 126154655 | chr9 | 126349038 | 126349104 |
| chr9 | 126770257 | 126770298 | chr9 | 126771532 | 126771705 | chr9 | 126774517 | 126774619 |
| chr9 | 126775530 | 126775550 | chr9 | 126776044 | 126776098 | chr9 | 126777529 | 126777746 |
| chr9 | 126777974 | 126777982 | chr9 | 126778359 | 126778495 | chr9 | 126779485 | 126780043 |
| chr9 | 126780285 | 126780315 | chr9 | 126780811 | 126780898 | chr9 | 126783295 | 126783499 |
| chr9 | 127212851 | 127213006 | chr9 | 127265876 | 127266025 | chr9 | 127266387 | 127266534 |
| chr9 | 127605297 | 127605327 | chr9 | 127630125 | 127630205 | chr9 | 127853274 | 127853304 |
| chr9 | 127920543 | 127920572 | chr9 | 128136065 | 128136095 | chr9 | 128635180 | 128635210 |
| chr9 | 128652200 | 128652232 | chr9 | 128759852 | 128759954 | chr9 | 129276718 | 129276820 |
| chr9 | 129372929 | 129373037 | chr9 | 129376170 | 129376199 | chr9 | 129376889 | 129376918 |
| chr9 | 129377214 | 129377316 | chr9 | 129377604 | 129377635 | chr9 | 129377773 | 129377959 |
| chr9 | 129387434 | 129387464 | chr9 | 129387848 | 129388200 | chr9 | 129388719 | 129388753 |
| chr9 | 129388996 | 129389192 | chr9 | 129400986 | 129401195 | chr9 | 129445255 | 129445566 |
| chr9 | 129445783 | 129445813 | chr9 | 129517783 | 129517821 | chr9 | 130248419 | 130248449 |
| chr9 | 130325967 | 130325997 | chr9 | 130461687 | 130461742 | chr9 | 130675509 | 130675615 |
| chr9 | 130689631 | 130689667 | chr9 | 130689742 | 130689749 | chr9 | 130694413 | 130694468 |
| chr9 | 130694809 | 130694948 | chr9 | 131177975 | 131178094 | chr9 | 131417698 | 131417940 |
| chr9 | 131542193 | 131542267 | chr9 | 131580038 | 131580129 | chr9 | 131607517 | 131607547 |
| chr9 | 131607770 | 131607800 | chr9 | 131854231 | 131854328 | chr9 | 131854564 | 131854732 |
| chr9 | 132373058 | 132373091 | chr9 | 132382635 | 132383109 | chr9 | 132383347 | 132383376 |
| chr9 | 132402840 | 132402883 | chr9 | 132403149 | 132403216 | chr9 | 132559377 | 132559456 |
| chr9 | 132804405 | 132804455 | chr9 | 132804796 | 132804974 | chr9 | 132805318 | 132805445 |
| chr9 | 132805737 | 132805893 | chr9 | 132815175 | 132815205 | chr9 | 132881814 | 132881844 |
| chr9 | 133308893 | 133308941 | chr9 | 133534683 | 133534713 | chr9 | 133535734 | 133535839 |
| chr9 | 133536097 | 133536119 | chr9 | 133536150 | 133536344 | chr9 | 133536778 | 133536869 |
| chr9 | 133537182 | 133537549 | chr9 | 133538169 | 133538729 | chr9 | 133539606 | 133539709 |
| chr9 | 133541059 | 133541192 | chr9 | 133541689 | 133542337 | chr9 | 133605601 | 133605631 |
| chr9 | 133738343 | 133738372 | chr9 | 133747505 | 133747534 | chr9 | 133773766 | 133773923 |
| chr9 | 133927347 | 133927481 | chr9 | 133928236 | 133928265 | chr9 | 134126670 | 134126741 |
| chr9 | 134191085 | 134191218 | chr9 | 134207916 | 134208040 | chr9 | 134421797 | 134421835 |
| chr9 | 134717313 | 134717367 | chr9 | 135037119 | 135037287 | chr9 | 135037334 | 135037357 |
| chr9 | 135073463 | 135073506 | chr9 | 135135114 | 135135247 | chr9 | 135231073 | 135231158 |
| chr9 | 135455407 | 135455585 | chr9 | 135455996 | 135456023 | chr9 | 135456476 | 135456544 |
| chr9 | 135456897 | 135456932 | chr9 | 135458477 | 135458597 | chr9 | 135460001 | 135460176 |
| chr9 | 135460869 | 135460899 | chr9 | 135461511 | 135461773 | chr9 | 135462048 | 135462077 |
| chr9 | 135462648 | 135462967 | chr9 | 135464798 | 135464918 | chr9 | 135465948 | 135466064 |
| chr9 | 135466118 | 135466132 | chr9 | 135466344 | 135466660 | chr9 | 135548238 | 135548313 |
| chr9 | 135590218 | 135590334 | chr9 | 135796801 | 135796830 | chr9 | 135865090 | 135865161 |
| chr9 | 135898911 | 135899124 | chr9 | 136474490 | 136474591 | chr9 | 137002646 | 137002692 |
| chr9 | 137111397 | 137111426 | chr9 | 137229892 | 137229921 | chr9 | 137299119 | 137299450 |
| chr9 | 137299670 | 137299699 | chr9 | 137534066 | 137534238 | chr9 | 137575915 | 137575945 |
| chr9 | 137656958 | 137657128 | chr9 | 137667327 | 137667357 | chr9 | 137702189 | 137702222 |
| chr9 | 137718901 | 137719001 | chr9 | 137722087 | 137722209 | chr9 | 137979893 | 137980011 |
| chr9 | 137980258 | 137980288 | chr9 | 137980880 | 137980910 | chr9 | 138265123 | 138265251 |
| chr9 | 138474557 | 138474590 | chr9 | 138563059 | 138563280 | chr9 | 138606821 | 138606923 |
| chr9 | 138627636 | 138627893 | chr9 | 138634047 | 138634159 | chr9 | 138659800 | 138659905 |
| chr9 | 138660943 | 138661012 | chr9 | 138661648 | 138661870 | chr9 | 138666455 | 138666558 |
| chr9 | 138826382 | 138826412 | chr9 | 138880711 | 138880875 | chr9 | 138991798 | 138991828 |
| chr9 | 139000566 | 139000642 | chr9 | 139012272 | 139012411 | chr9 | 139024750 | 139024782 |
| chr9 | 139045653 | 139045683 | chr9 | 139047532 | 139047633 | chr9 | 139085228 | 139085360 |
| chr9 | 139090500 | 139090551 | chr9 | 139091072 | 139091369 | chr9 | 139093773 | 139093890 |
| chr9 | 139094705 | 139094732 | chr9 | 139095340 | 139095485 | chr9 | 139096650 | 139097006 |
| chr9 | 139111268 | 139111298 | chr9 | 139269039 | 139269121 | chr9 | 139399407 | 139399436 |
| chr9 | 139421955 | 139421985 | chr9 | 139477862 | 139478020 | chr9 | 139698925 | 139699051 |
| chr9 | 139704008 | 139704279 | chr9 | 139859041 | 139859268 | chr9 | 139888945 | 139888980 |
| chr9 | 140015209 | 140015241 | chr9 | 140024842 | 140024918 | chr9 | 140024957 | 140025023 |

TABLE 12-continued

| chr | start | end | chr | start | end | chr | start | end |
|---|---|---|---|---|---|---|---|---|
| chr9 | 140030498 | 140030528 | chr9 | 140031944 | 140032082 | chr9 | 140032891 | 140032951 |
| chr9 | 140033001 | 140033092 | chr9 | 140033426 | 140033490 | chr9 | 140033619 | 140033626 |
| chr9 | 140033909 | 140034079 | chr9 | 140050969 | 140051096 | chr9 | 140051220 | 140051354 |
| chr9 | 140127883 | 140128080 | chr9 | 140137310 | 140137488 | chr9 | 140197122 | 140197263 |
| chr9 | 140205394 | 140205519 | chr9 | 140245877 | 140245998 | chr9 | 140332708 | 140333018 |
| chr9 | 140382557 | 140382596 | chr9 | 140392454 | 140392484 | chr9 | 140397029 | 140397097 |
| chr9 | 140498318 | 140498394 | chr9 | 140507256 | 140507419 | chr9 | 140704046 | 140704131 |
| chr9 | 140709046 | 140709174 | chr9 | 140727471 | 140727511 | chr9 | 140727845 | 140727930 |
| chr9 | 140769943 | 140769973 | chr9 | 140771975 | 140772347 | chr9 | 140772586 | 140772593 |
| chr9 | 140772757 | 140773301 | chr10 | 524754 | 524784 | chr10 | 833307 | 833386 |
| chr10 | 978878 | 978933 | chr10 | 1080377 | 1080513 | chr10 | 1120778 | 1120937 |
| chr10 | 1577394 | 1577424 | chr10 | 1585111 | 1585239 | chr10 | 1651360 | 1651374 |
| chr10 | 1708327 | 1708478 | chr10 | 1774858 | 1774887 | chr10 | 1779417 | 1779744 |
| chr10 | 3109360 | 3109459 | chr10 | 3197004 | 3197113 | chr10 | 3285585 | 3285698 |
| chr10 | 3330499 | 3330618 | chr10 | 3641378 | 3641413 | chr10 | 3678597 | 3678637 |
| chr10 | 3895410 | 3895452 | chr10 | 4599917 | 4599965 | chr10 | 5530764 | 5530975 |
| chr10 | 5765021 | 5765059 | chr10 | 5855154 | 5855184 | chr10 | 5875140 | 5875396 |
| chr10 | 6003402 | 6003855 | chr10 | 6042309 | 6042571 | chr10 | 6162159 | 6162225 |
| chr10 | 6167619 | 6167742 | chr10 | 6206142 | 6206217 | chr10 | 6372343 | 6372373 |
| chr10 | 6513976 | 6514006 | chr10 | 6577643 | 6577673 | chr10 | 6586721 | 6586847 |
| chr10 | 6963079 | 6963111 | chr10 | 6984463 | 6984639 | chr10 | 7205733 | 7205787 |
| chr10 | 7212745 | 7213064 | chr10 | 7213505 | 7213535 | chr10 | 7216059 | 7216089 |
| chr10 | 7236211 | 7236245 | chr10 | 7255730 | 7255821 | chr10 | 7323283 | 7323313 |
| chr10 | 7334737 | 7334767 | chr10 | 7363436 | 7363466 | chr10 | 7321678 | 7371708 |
| chr10 | 7414544 | 7414588 | chr10 | 7424626 | 7424687 | chr10 | 7436090 | 7436209 |
| chr10 | 7449954 | 7450189 | chr10 | 7450491 | 7451390 | chr10 | 7452227 | 7452777 |
| chr10 | 7453313 | 7453656 | chr10 | 7453903 | 7453930 | chr10 | 7708274 | 7708304 |
| chr10 | 7708790 | 7708856 | chr10 | 7708955 | 7709087 | chr10 | 7709723 | 7709752 |
| chr10 | 8055681 | 8055764 | chr10 | 8075930 | 8075944 | chr10 | 8076341 | 8076487 |
| chr10 | 8076804 | 8077374 | chr10 | 8077874 | 8078218 | chr10 | 8085039 | 8085721 |
| chr10 | 8085978 | 8086010 | chr10 | 8091895 | 8092278 | chr10 | 8093738 | 8093824 |
| chr10 | 8093860 | 8093963 | chr10 | 8095603 | 8095845 | chr10 | 8096160 | 8096190 |
| chr10 | 8096975 | 8097197 | chr10 | 8097474 | 8097537 | chr10 | 11059933 | 11060062 |
| chr10 | 11206206 | 11206235 | chr10 | 11207179 | 11207276 | chr10 | 11700918 | 11701075 |
| chr10 | 12390825 | 12390995 | chr10 | 12391870 | 12392327 | chr10 | 12554417 | 12554501 |
| chr10 | 13043386 | 13043425 | chr10 | 13140861 | 13141020 | chr10 | 13715208 | 13715401 |
| chr10 | 13933005 | 13933035 | chr10 | 13933436 | 13933538 | chr10 | 13933597 | 13933934 |
| chr10 | 13933983 | 13934125 | chr10 | 13934169 | 13934183 | chr10 | 14393819 | 14393893 |
| chr10 | 14966129 | 14966212 | chr10 | 15002784 | 15003006 | chr10 | 15140484 | 15140526 |
| chr10 | 15761292 | 15761671 | chr10 | 15762124 | 15762154 | chr10 | 16175687 | 16175801 |
| chr10 | 16562369 | 16562672 | chr10 | 16562710 | 16563664 | chr10 | 16563691 | 16563909 |
| chr10 | 16564087 | 16564116 | chr10 | 16564537 | 16564566 | chr10 | 17269259 | 17269288 |
| chr10 | 17269628 | 17269789 | chr10 | 17270072 | 17270445 | chr10 | 17270991 | 17271254 |
| chr10 | 17271444 | 17271625 | chr10 | 17271914 | 17272233 | chr10 | 17272601 | 17272630 |
| chr10 | 17273172 | 17273201 | chr10 | 17275584 | 17275613 | chr10 | 17277741 | 17277770 |
| chr10 | 17429165 | 17429622 | chr10 | 17496545 | 17496734 | chr10 | 17503402 | 17503520 |
| chr10 | 17509450 | 17509503 | chr10 | 18429628 | 18429774 | chr10 | 21101525 | 21101555 |
| chr10 | 21462533 | 21462607 | chr10 | 21462970 | 21463023 | chr10 | 21728064 | 21728125 |
| chr10 | 21805217 | 21805277 | chr10 | 22047336 | 22047635 | chr10 | 22541638 | 22541850 |
| chr10 | 22542025 | 22542249 | chr10 | 22567093 | 22567322 | chr10 | 22624022 | 22624305 |
| chr10 | 22624562 | 22625120 | chr10 | 22625383 | 22625782 | chr10 | 22625812 | 22625978 |
| chr10 | 22633985 | 22634174 | chr10 | 22634325 | 22634578 | chr10 | 22764649 | 22765791 |
| chr10 | 22765821 | 22765901 | chr10 | 23216865 | 23216945 | chr10 | 23460355 | 23460471 |
| chr10 | 23461222 | 23461754 | chr10 | 23462059 | 23462462 | chr10 | 23462486 | 23462614 |
| chr10 | 23462635 | 23462910 | chr10 | 23463267 | 23463853 | chr10 | 23463888 | 23464077 |
| chr10 | 23479876 | 23480696 | chr10 | 23480904 | 23481049 | chr10 | 23481321 | 23481515 |
| chr10 | 23481936 | 23482232 | chr10 | 23482289 | 23482445 | chr10 | 23483828 | 23484618 |
| chr10 | 23486264 | 23486328 | chr10 | 23487742 | 23487978 | chr10 | 23488393 | 23489158 |
| chr10 | 23489409 | 23489439 | chr10 | 23982438 | 23982820 | chr10 | 23983194 | 23983247 |
| chr10 | 23983618 | 23983700 | chr10 | 23984087 | 23984226 | chr10 | 23984923 | 23984991 |
| chr10 | 24988589 | 24988619 | chr10 | 25464619 | 25464915 | chr10 | 25465421 | 25465517 |
| chr10 | 26055811 | 26055841 | chr10 | 26223001 | 26223205 | chr10 | 26224031 | 26224061 |
| chr10 | 26500619 | 26500870 | chr10 | 26501539 | 26501589 | chr10 | 26503693 | 26503731 |
| chr10 | 26504114 | 26504143 | chr10 | 26504491 | 26504883 | chr10 | 26505009 | 26505227 |
| chr10 | 26505442 | 26505617 | chr10 | 26506057 | 26506163 | chr10 | 26506373 | 26506618 |
| chr10 | 26506903 | 26507400 | chr10 | 26681099 | 26681129 | chr10 | 26727098 | 26727368 |
| chr10 | 26727604 | 26727816 | chr10 | 26747051 | 26747159 | chr10 | 26803853 | 26803883 |
| chr10 | 26816766 | 26816938 | chr10 | 26931897 | 26931926 | chr10 | 27547946 | 27548331 |
| chr10 | 27548401 | 27548794 | chr10 | 27794496 | 27794588 | chr10 | 27846637 | 27846816 |
| chr10 | 28030892 | 28030925 | chr10 | 28032966 | 28033020 | chr10 | 28033410 | 28033481 |
| chr10 | 28033770 | 28034186 | chr10 | 28034327 | 28034341 | chr10 | 28034874 | 28035300 |
| chr10 | 28035615 | 28035782 | chr10 | 28287373 | 28287557 | chr10 | 28287777 | 28288070 |
| chr10 | 28657255 | 28657343 | chr10 | 28958086 | 28958154 | chr10 | 28964745 | 28964800 |
| chr10 | 29011047 | 29011162 | chr10 | 30026077 | 30026090 | chr10 | 30848200 | 30848230 |
| chr10 | 31073368 | 31073481 | chr10 | 31892922 | 31893079 | chr10 | 32499044 | 32499176 |
| chr10 | 32672459 | 32672489 | chr10 | 33233313 | 33233361 | chr10 | 33624166 | 33624230 |
| chr10 | 33624492 | 33624560 | chr10 | 35929334 | 35929528 | chr10 | 37051865 | 37051895 |
| chr10 | 38078948 | 38079105 | chr10 | 43186151 | 43186181 | chr10 | 43250009 | 43250039 |

TABLE 12-continued

| chr | start | end | chr | start | end | chr | start | end |
|---|---|---|---|---|---|---|---|---|
| chr10 | 43250406 | 43250779 | chr10 | 43250855 | 43250886 | chr10 | 43428424 | 43428576 |
| chr10 | 43429067 | 43429100 | chr10 | 43429376 | 43429411 | chr10 | 43572685 | 43572734 |
| chr10 | 43600561 | 43600720 | chr10 | 43609055 | 43609117 | chr10 | 43609922 | 43609963 |
| chr10 | 43613890 | 43613919 | chr10 | 43614982 | 43615011 | chr10 | 43615554 | 43615607 |
| chr10 | 43617401 | 43617430 | chr10 | 43697887 | 43698086 | chr10 | 43698115 | 43698155 |
| chr10 | 43858343 | 43858470 | chr10 | 43905877 | 43906023 | chr10 | 44434176 | 44434206 |
| chr10 | 44879944 | 44880228 | chr10 | 44880869 | 44880915 | chr10 | 49652977 | 49653080 |
| chr10 | 49731548 | 49731749 | chr10 | 49732060 | 49732087 | chr10 | 49732156 | 49732498 |
| chr10 | 50323222 | 50323258 | chr10 | 50340119 | 50340149 | chr10 | 50507557 | 50507619 |
| chr10 | 50603967 | 50604159 | chr10 | 50604608 | 50604645 | chr10 | 50605057 | 50605654 |
| chr10 | 50606027 | 50606433 | chr10 | 50748131 | 50748350 | chr10 | 50817015 | 50817132 |
| chr10 | 50817858 | 50817872 | chr10 | 50818382 | 50818432 | chr10 | 50818987 | 50819102 |
| chr10 | 50821472 | 50821701 | chr10 | 50887655 | 50887753 | chr10 | 50887790 | 50887816 |
| chr10 | 50977034 | 50977048 | chr10 | 52177545 | 52177575 | chr10 | 53107427 | 53107563 |
| chr10 | 54068526 | 54068610 | chr10 | 54072982 | 54073020 | chr10 | 54073265 | 4073295 |
| chr10 | 54074744 | 54074789 | chr10 | 57387429 | 57387796 | chr10 | 57388325 | 57388510 |
| chr10 | 57390290 | 57390637 | chr10 | 57391166 | 57391215 | chr10 | 60273130 | 60273278 |
| chr10 | 60935887 | 60935996 | chr10 | 60936524 | 60936729 | chr10 | 60937073 | 60937103 |
| chr10 | 63212324 | 63212701 | chr10 | 63669223 | 63669344 | chr10 | 64575526 | 64575638 |
| chr10 | 64578171 | 64578540 | chr10 | 65262111 | 65262304 | chr10 | 69578459 | 69578588 |
| chr10 | 69589153 | 69589407 | chr10 | 70167678 | 70167708 | chr10 | 70232345 | 70232485 |
| chr10 | 70275831 | 70275979 | chr10 | 70314814 | 70315148 | chr10 | 70565410 | 70565489 |
| chr10 | 70586494 | 70586540 | chr10 | 71084981 | 71085116 | chr10 | 71327725 | 71327764 |
| chr10 | 71328773 | 71328821 | chr10 | 71329079 | 71329118 | chr10 | 71329544 | 71329618 |
| chr10 | 71332052 | 71333018 | chr10 | 72015150 | 72015339 | chr10 | 72043779 | 72043894 |
| chr10 | 72200118 | 72200138 | chr10 | 72200354 | 72200771 | chr10 | 72200825 | 72201285 |
| chr10 | 72973130 | 72973180 | chr10 | 73156362 | 73156661 | chr10 | 73157867 | 73158202 |
| chr10 | 75384100 | 75384130 | chr10 | 75386789 | 75386893 | chr10 | 75388129 | 75388173 |
| chr10 | 75407570 | 75407837 | chr10 | 75488953 | 75489125 | chr10 | 77190039 | 77190068 |
| chr10 | 77191224 | 77191368 | chr10 | 79396921 | 79397089 | chr10 | 81023884 | 81023914 |
| chr10 | 81154141 | 81154192 | chr10 | 81664867 | 81664899 | chr10 | 81860447 | 81860568 |
| chr10 | 81966737 | 81966828 | chr10 | 82117074 | 82117271 | chr10 | 83634261 | 83634361 |
| chr10 | 83634467 | 83634499 | chr10 | 83635531 | 83635545 | chr10 | 85792257 | 85792287 |
| chr10 | 85954425 | 85954457 | chr10 | 88123672 | 88123701 | chr10 | 88149363 | 88149601 |
| chr10 | 88304914 | 88304944 | chr10 | 88684005 | 88684034 | chr10 | 88698834 | 88698914 |
| chr10 | 89624255 | 89624311 | chr10 | 89653788 | 89653859 | chr10 | 89685272 | 89685322 |
| chr10 | 89690790 | 89690819 | chr10 | 89692776 | 89693015 | chr10 | 89711861 | 89711992 |
| chr10 | 89717610 | 89717744 | chr10 | 89720790 | 89720885 | chr10 | 89725030 | 89725071 |
| chr10 | 90966708 | 90966865 | chr10 | 90967671 | 90968040 | chr10 | 91295029 | 91295067 |
| chr10 | 91295585 | 91295725 | chr10 | 92617242 | 92617308 | chr10 | 93647216 | 93647300 |
| chr10 | 93647562 | 93647648 | chr10 | 94062288 | 94062318 | chr10 | 94450675 | 94450726 |
| chr10 | 94451448 | 94451602 | chr10 | 94826023 | 94826056 | chr10 | 94828194 | 94828498 |
| chr10 | 94828735 | 94828828 | chr10 | 94834413 | 94835047 | chr10 | 95360716 | 95360750 |
| chr10 | 96304020 | 96304329 | chr10 | 98129822 | 98130033 | chr10 | 98528023 | 98528107 |
| chr10 | 98558129 | 98558200 | chr10 | 99051122 | 99051253 | chr10 | 99080262 | 99080447 |
| chr10 | 99080862 | 99080930 | chr10 | 99161398 | 99161560 | chr10 | 99474393 | 99474467 |
| chr10 | 99481747 | 99481905 | chr10 | 99531219 | 99531430 | chr10 | 99789175 | 99789282 |
| chr10 | 99790261 | 99790318 | chr10 | 99790590 | 99790664 | chr10 | 99790947 | 99791161 |
| chr10 | 100991907 | 100992190 | chr10 | 100992222 | 100992443 | chr10 | 100992882 | 100992916 |
| chr10 | 100993537 | 100994016 | chr10 | 100996046 | 100996224 | chr10 | 101088995 | 101089439 |
| chr10 | 101089908 | 101090203 | chr10 | 101280204 | 101280485 | chr10 | 101283464 | 101283658 |
| chr10 | 101290117 | 101290160 | chr10 | 101291108 | 101291142 | chr10 | 101292297 | 101292919 |
| chr10 | 101293156 | 101293343 | chr10 | 101294756 | 101295586 | chr10 | 101296768 | 101296800 |
| chr10 | 101363207 | 101363418 | chr10 | 101492942 | 101493074 | chr10 | 101874886 | 101875138 |
| chr10 | 101988223 | 101988404 | chr10 | 102322230 | 102322260 | chr10 | 102419400 | 102419681 |
| chr10 | 102430699 | 102430761 | chr10 | 102473856 | 102473932 | chr10 | 102483993 | 102484245 |
| chr10 | 102484270 | 102484554 | chr10 | 102495508 | 102495741 | chr10 | 102497273 | 102497708 |
| chr10 | 102498280 | 102498433 | chr10 | 102501359 | 102501389 | chr10 | 102507509 | 102507535 |
| chr10 | 102508996 | 102509285 | chr10 | 102589425 | 102589493 | chr10 | 102589786 | 102589915 |
| chr10 | 102590152 | 102590415 | chr10 | 102890941 | 102891582 | chr10 | 102891823 | 102891955 |
| chr10 | 102893624 | 102893951 | chr10 | 102894091 | 102895289 | chr10 | 102899173 | 102899601 |
| chr10 | 102899807 | 102899855 | chr10 | 102900263 | 102900575 | chr10 | 102906525 | 102906620 |
| chr10 | 102975619 | 102975834 | chr10 | 102976150 | 102976180 | chr10 | 102977051 | 102977412 |
| chr10 | 102983153 | 102983379 | chr10 | 102983435 | 102983749 | chr10 | 102984513 | 102984516 |
| chr10 | 102985772 | 102985963 | chr10 | 102986534 | 102986952 | chr10 | 102987207 | 102987558 |
| chr10 | 102989629 | 102989659 | chr10 | 102996116 | 102996480 | chr10 | 102996597 | 102996638 |
| chr10 | 102997329 | 102997406 | chr10 | 102998576 | 102998828 | chr10 | 103043975 | 103044227 |
| chr10 | 103044301 | 103044366 | chr10 | 103325743 | 103325773 | chr10 | 103425950 | 103426174 |
| chr10 | 103432412 | 103432441 | chr10 | 103535622 | 103535770 | chr10 | 103536227 | 103536256 |
| chr10 | 103536300 | 103536416 | chr10 | 103579635 | 103579713 | chr10 | 103814668 | 103814754 |
| chr10 | 103930034 | 103930161 | chr10 | 104170096 | 104170262 | chr10 | 104170408 | 104170732 |
| chr10 | 105036542 | 105036658 | chr10 | 105036701 | 105036863 | chr10 | 105037223 | 105037830 |
| chr10 | 105126957 | 105127076 | chr10 | 105155285 | 105155481 | chr10 | 105413627 | 105413784 |
| chr10 | 105420861 | 105420891 | chr10 | 105527028 | 105527057 | chr10 | 106398644 | 106398687 |
| chr10 | 106398826 | 106398886 | chr10 | 106399581 | 106400387 | chr10 | 106401323 | 106401432 |
| chr10 | 106401511 | 106402190 | chr10 | 106402272 | 106402325 | chr10 | 106402712 | 106402825 |
| chr10 | 108469972 | 108470093 | chr10 | 108924045 | 108924059 | chr10 | 110671930 | 110672245 |
| chr10 | 111216789 | 111216803 | chr10 | 112403151 | 112403297 | chr10 | 112440378 | 112440408 |

TABLE 12-continued

| chr | start | end | chr | start | end | chr | start | end |
|---|---|---|---|---|---|---|---|---|
| chr10 | 115804840 | 115805014 | chr10 | 115925505 | 115925552 | chr10 | 116164248 | 116164341 |
| chr10 | 116331126 | 116331156 | chr10 | 116853875 | 116853908 | chr10 | 118030642 | 118030705 |
| chr10 | 118031302 | 118031548 | chr10 | 118031625 | 118032229 | chr10 | 118032413 | 118032547 |
| chr10 | 118032917 | 118033542 | chr10 | 118034143 | 118034168 | chr10 | 118609305 | 118609390 |
| chr10 | 118890980 | 118891104 | chr10 | 118891517 | 118891661 | chr10 | 118891716 | 118891774 |
| chr10 | 118892013 | 118892456 | chr10 | 118892518 | 118893266 | chr10 | 118893680 | 118893825 |
| chr10 | 118894035 | 118894071 | chr10 | 118896629 | 118896805 | chr10 | 118897913 | 118897968 |
| chr10 | 118899273 | 118899302 | chr10 | 118899583 | 118899602 | chr10 | 118899893 | 118899957 |
| chr10 | 118900166 | 118900244 | chr10 | 118900324 | 118900498 | chr10 | 118922143 | 118922208 |
| chr10 | 118922721 | 118922901 | chr10 | 118923138 | 118923259 | chr10 | 118924604 | 118924896 |
| chr10 | 118927086 | 118927296 | chr10 | 118928548 | 118928727 | chr10 | 119000690 | 119001154 |
| chr10 | 119001534 | 119001564 | chr10 | 119294352 | 119294461 | chr10 | 119294847 | 119294897 |
| chr10 | 119294909 | 119295245 | chr10 | 119296756 | 119296788 | chr10 | 119297384 | 119297529 |
| chr10 | 119301365 | 119301427 | chr10 | 119302141 | 119302155 | chr10 | 119302222 | 119302266 |
| chr10 | 119302962 | 119303174 | chr10 | 119304363 | 119304393 | chr10 | 119304896 | 119304985 |
| chr10 | 119305062 | 119305109 | chr10 | 119307022 | 119307052 | chr10 | 119311867 | 119311897 |
| chr10 | 119312751 | 119313193 | chr10 | 119590435 | 119590464 | chr10 | 119807026 | 119807056 |
| chr10 | 120354243 | 120354273 | chr10 | 120355548 | 120355614 | chr10 | 120707028 | 120707111 |
| chr10 | 120800789 | 120800835 | chr10 | 120841558 | 120841590 | chr10 | 120937014 | 120937139 |
| chr10 | 121267480 | 121267626 | chr10 | 121307542 | 121307572 | chr10 | 122216896 | 122217083 |
| chr10 | 122708495 | 122708691 | chr10 | 122708992 | 122709022 | chr10 | 123256044 | 123256232 |
| chr10 | 123258020 | 123258091 | chr10 | 123274758 | 123274787 | chr10 | 123279548 | 123279697 |
| chr10 | 123357206 | 123357242 | chr10 | 123357766 | 123357822 | chr10 | 123667184 | 123667222 |
| chr10 | 123688711 | 123688741 | chr10 | 123922645 | 123922682 | chr10 | 124893178 | 124893192 |
| chr10 | 124893238 | 124893350 | chr10 | 124893635 | 124893765 | chr10 | 124893965 | 124894479 |
| chr10 | 124894889 | 124894922 | chr10 | 124895426 | 124895695 | chr10 | 124895833 | 124896456 |
| chr10 | 124897220 | 124897973 | chr10 | 124899035 | 124899116 | chr10 | 124899754 | 124899786 |
| chr10 | 124901892 | 124902046 | chr10 | 124902139 | 124902568 | chr10 | 124902608 | 124903238 |
| chr10 | 124904921 | 124905119 | chr10 | 124905481 | 124905511 | chr10 | 124905920 | 124906174 |
| chr10 | 124906436 | 124906544 | chr10 | 124907312 | 124907534 | chr10 | 124908091 | 124908121 |
| chr10 | 124909086 | 124909114 | chr10 | 124909253 | 124909537 | chr10 | 124909674 | 124909725 |
| chr10 | 124910363 | 124910454 | chr10 | 124910709 | 124911048 | chr10 | 125425515 | 125425547 |
| chr10 | 125527754 | 125527784 | chr10 | 125650866 | 125651162 | chr10 | 126851328 | 125851645 |
| chr10 | 125852299 | 125852497 | chr10 | 125852753 | 125853191 | chr10 | 126101966 | 126102095 |
| chr10 | 126135927 | 126136065 | chr10 | 126136506 | 126136723 | chr10 | 126137181 | 126137405 |
| chr10 | 126198949 | 126199077 | chr10 | 126697789 | 126698107 | chr10 | 126782965 | 126783048 |
| chr10 | 126828994 | 126829024 | chr10 | 127406313 | 127406386 | chr10 | 127693923 | 127693959 |
| chr10 | 128076561 | 128076630 | chr10 | 128993904 | 128994446 | chr10 | 128994727 | 128994903 |
| chr10 | 129379338 | 129379367 | chr10 | 129534993 | 129535446 | chr10 | 129535696 | 129535733 |
| chr10 | 129536080 | 129536223 | chr10 | 129536259 | 129536310 | chr10 | 129888804 | 129888885 |
| chr10 | 129948111 | 129948140 | chr10 | 130085356 | 130085362 | chr10 | 130203435 | 130203480 |
| chr10 | 130338727 | 130338768 | chr10 | 130338804 | 130338976 | chr10 | 130577764 | 130577794 |
| chr10 | 131348513 | 131348793 | chr10 | 131647903 | 131647933 | chr10 | 131761378 | 131761441 |
| chr10 | 131761687 | 131761725 | chr10 | 131762087 | 131762124 | chr10 | 131762592 | 131762631 |
| chr10 | 131762904 | 131762940 | chr10 | 131763633 | 131763717 | chr10 | 131767372 | 131767503 |
| chr10 | 131767543 | 131767649 | chr10 | 131768724 | 131769029 | chr10 | 131769533 | 131770237 |
| chr10 | 131770657 | 131770687 | chr10 | 131770988 | 131771093 | chr10 | 131936451 | 131936626 |
| chr10 | 131937355 | 131937428 | chr10 | 132000973 | 132001015 | chr10 | 132001252 | 132001556 |
| chr10 | 133109192 | 133109260 | chr10 | 133110554 | 133110704 | chr10 | 133794883 | 133795241 |
| chr10 | 133795313 | 133795430 | chr10 | 133795682 | 133795883 | chr10 | 133795976 | 133796058 |
| chr10 | 133849598 | 133850008 | chr10 | 133850529 | 133850774 | chr10 | 133951602 | 133952025 |
| chr10 | 133979059 | 133979089 | chr10 | 134000008 | 134000042 | chr10 | 134000109 | 134000124 |
| chr10 | 134001140 | 134001260 | chr10 | 134016203 | 134016388 | chr10 | 134022845 | 134022875 |
| chr10 | 134039087 | 134039117 | chr10 | 134092153 | 134092202 | chr10 | 134095594 | 134095833 |
| chr10 | 134119401 | 134119447 | chr10 | 134121401 | 134121430 | chr10 | 134273064 | 134273156 |
| chr10 | 134301095 | 134301212 | chr10 | 134481320 | 134481433 | chr10 | 134491021 | 134491114 |
| chr10 | 134499773 | 134499803 | chr10 | 134593329 | 134593416 | chr10 | 134598087 | 134598090 |
| chr10 | 134598368 | 134598530 | chr10 | 134599432 | 134599482 | chr10 | 134599808 | 134600016 |
| chr10 | 134600038 | 134600998 | chr10 | 134601556 | 134601715 | chr10 | 134602183 | 134602269 |
| chr10 | 134607970 | 134608183 | chr10 | 134665147 | 134665202 | chr10 | 134679129 | 134679265 |
| chr10 | 134690559 | 134690617 | chr10 | 134693587 | 134693709 | chr10 | 134699872 | 134699909 |
| chr10 | 134733221 | 134733275 | chr10 | 134733497 | 134733617 | chr10 | 134738378 | 134738542 |
| chr10 | 134755773 | 134756183 | chr10 | 134788083 | 134788251 | chr10 | 134794271 | 134794342 |
| chr10 | 134796012 | 134796042 | chr10 | 134896060 | 134896092 | chr10 | 134901193 | 134901511 |
| chr10 | 134902008 | 134902124 | chr10 | 134902188 | 134902307 | chr10 | 134916714 | 134916774 |
| chr10 | 134941145 | 134941178 | chr10 | 134942840 | 134943114 | chr10 | 134943445 | 134943542 |
| chr10 | 134944742 | 134944772 | chr10 | 134959217 | 134959391 | chr10 | 135002063 | 135002156 |
| chr10 | 135014963 | 135015132 | chr10 | 135017049 | 135017129 | chr10 | 135018032 | 135018070 |
| chr10 | 135018825 | 135018960 | chr10 | 135020801 | 135020893 | chr10 | 135023470 | 135023500 |
| chr10 | 135043088 | 135043538 | chr10 | 135043968 | 135044128 | chr10 | 135044555 | 135044573 |
| chr10 | 135048782 | 135048939 | chr10 | 135050311 | 135050679 | chr10 | 135076368 | 135076503 |
| chr10 | 135121316 | 135121345 | chr10 | 135121807 | 135122251 | chr10 | 135122742 | 135122808 |
| chr10 | 135122991 | 135123020 | chr10 | 135139555 | 135139730 | chr10 | 135153956 | 135154001 |
| chr11 | 232863 | 233062 | chr11 | 392576 | 392720 | chr11 | 394815 | 394968 |
| chr11 | 406876 | 406939 | chr11 | 407427 | 407463 | chr11 | 505732 | 505869 |
| chr11 | 518400 | 518430 | chr11 | 526389 | 526419 | chr11 | 533451 | 533567 |
| chr11 | 533859 | 533888 | chr11 | 534273 | 534302 | chr11 | 548731 | 548800 |
| chr11 | 611099 | 611128 | chr11 | 611691 | 611791 | chr11 | 636644 | 536673 |

TABLE 12-continued

| chr | start | end | chr | start | end | chr | start | end |
|---|---|---|---|---|---|---|---|---|
| chr11 | 636895 | 636906 | chr11 | 637162 | 637263 | chr11 | 637350 | 537441 |
| chr11 | 679692 | 679722 | chr11 | 726417 | 726466 | chr11 | 763323 | 763686 |
| chr11 | 775261 | 775291 | chr11 | 829543 | 829708 | chr11 | 830174 | 830243 |
| chr11 | 850555 | 850823 | chr11 | 861612 | 861657 | chr11 | 863062 | 863092 |
| chr11 | 1006077 | 1006107 | chr11 | 1027540 | 1027574 | chr11 | 1029238 | 1029403 |
| chr11 | 1030215 | 1030296 | chr11 | 1080391 | 1080454 | chr11 | 1081667 | 1081715 |
| chr11 | 1214665 | 1214917 | chr11 | 1215899 | 1215999 | chr11 | 1229945 | 1229975 |
| chr11 | 1244381 | 1244465 | chr11 | 1250889 | 1250924 | chr11 | 1251183 | 1251351 |
| chr11 | 1263602 | 1263644 | chr11 | 1274085 | 1274189 | chr11 | 1318403 | 1318432 |
| chr11 | 1358291 | 1358332 | chr11 | 1374959 | 1375003 | chr11 | 1411875 | 1411905 |
| chr11 | 1430714 | 1430794 | chr11 | 1464280 | 1464428 | chr11 | 1469228 | 1469379 |
| chr11 | 1471920 | 1472058 | chr11 | 1868081 | 1868237 | chr11 | 1946130 | 1946160 |
| chr11 | 1957391 | 1957530 | chr11 | 1959077 | 1959187 | chr11 | 2040107 | 2040148 |
| chr11 | 2209907 | 2210278 | chr11 | 2226048 | 2226078 | chr11 | 2278708 | 2278839 |
| chr11 | 2291259 | 2291493 | chr11 | 2291984 | 2292057 | chr11 | 2292106 | 2292359 |
| chr11 | 2292392 | 2292636 | chr11 | 2402376 | 2402405 | chr11 | 2437991 | 2438144 |
| chr11 | 2465350 | 2465447 | chr11 | 2465462 | 2465491 | chr11 | 2466597 | 2466788 |
| chr11 | 2884103 | 2884143 | chr11 | 2884159 | 2884309 | chr11 | 3027425 | 3027562 |
| chr11 | 3169665 | 3169835 | chr11 | 3181913 | 3181942 | chr11 | 3182104 | 3182133 |
| chr11 | 3511446 | 3511501 | chr11 | 3767205 | 3767284 | chr11 | 4038082 | 4038176 |
| chr11 | 4095819 | 4095864 | chr11 | 4209105 | 4209134 | chr11 | 4209382 | 4209411 |
| chr11 | 5641077 | 5641140 | chr11 | 5993897 | 5994029 | chr11 | 6497192 | 6497222 |
| chr11 | 7274215 | 7274245 | chr11 | 7695432 | 7695528 | chr11 | 8040536 | 8040563 |
| chr11 | 8040582 | 8040770 | chr11 | 8103002 | 8103115 | chr11 | 8189987 | 8190766 |
| chr11 | 8284535 | 8284760 | chr11 | 8289517 | 8289745 | chr11 | 8290195 | 8290423 |
| chr11 | 8615674 | 8615704 | chr11 | 9025970 | 9026348 | chr11 | 9112446 | 9112585 |
| chr11 | 9112640 | 9112741 | chr11 | 9405392 | 9405752 | chr11 | 10509678 | 10509807 |
| chr11 | 10811151 | 10811224 | chr11 | 10815867 | 10815998 | chr11 | 12029957 | 12030272 |
| chr11 | 12030823 | 12030852 | chr11 | 12132524 | 12132559 | chr11 | 12399040 | 12399222 |
| chr11 | 12399727 | 12399791 | chr11 | 12695481 | 12695495 | chr11 | 12695573 | 12695611 |
| chr11 | 12696611 | 12696746 | chr11 | 13030566 | 13030890 | chr11 | 13690121 | 13690157 |
| chr11 | 13711492 | 13711529 | chr11 | 14316375 | 14316404 | chr11 | 14543250 | 14543304 |
| chr11 | 14866247 | 14866285 | chr11 | 15136085 | 15136394 | chr11 | 16628819 | 16628933 |
| chr11 | 16632514 | 16632670 | chr11 | 17497492 | 17497520 | chr11 | 17497546 | 17497685 |
| chr11 | 17740493 | 17740570 | chr11 | 17741679 | 17741889 | chr11 | 17741953 | 17742445 |
| chr11 | 17743742 | 17743775 | chr11 | 18100096 | 18100259 | chr11 | 18812614 | 18812653 |
| chr11 | 18813032 | 18813086 | chr11 | 18813451 | 18813542 | chr11 | 18813792 | 18813947 |
| chr11 | 19263848 | 19263878 | chr11 | 19367102 | 19367134 | chr11 | 19367268 | 19367330 |
| chr11 | 19736730 | 19735760 | chr11 | 20153718 | 20153764 | chr11 | 20178094 | 20178306 |
| chr11 | 20180279 | 20180793 | chr11 | 20181213 | 20181254 | chr11 | 20181725 | 20181993 |
| chr11 | 20182864 | 20182959 | chr11 | 20183251 | 20183421 | chr11 | 20183674 | 20183773 |
| chr11 | 20184569 | 20185410 | chr11 | 20229058 | 20229550 | chr11 | 20229863 | 20230091 |
| chr11 | 20230398 | 20230464 | chr11 | 20408219 | 20408341 | chr11 | 20618197 | 20618392 |
| chr11 | 20618423 | 20618924 | chr11 | 20619717 | 20619974 | chr11 | 20621341 | 20621644 |
| chr11 | 20622705 | 20622792 | chr11 | 20623259 | 20623359 | chr11 | 20690653 | 20690877 |
| chr11 | 20691219 | 20691379 | chr11 | 20691432 | 20691452 | chr11 | 20691748 | 20691914 |
| chr11 | 20692453 | 20692529 | chr11 | 22215123 | 22215287 | chr11 | 22362934 | 22363189 |
| chr11 | 22364821 | 22364975 | chr11 | 22365407 | 22365477 | chr11 | 27742185 | 27742215 |
| chr11 | 27743115 | 27743173 | chr11 | 27743436 | 27743608 | chr11 | 27744147 | 27744504 |
| chr11 | 27744711 | 27744744 | chr11 | 30037593 | 30032743 | chr11 | 30038689 | 30038739 |
| chr11 | 30605919 | 30606123 | chr11 | 30606796 | 30606864 | chr11 | 30607367 | 30607409 |
| chr11 | 31760124 | 31760235 | chr11 | 31818458 | 31818512 | chr11 | 31818571 | 31818652 |
| chr11 | 31819302 | 31819833 | chr11 | 31820045 | 31820360 | chr11 | 31820461 | 31821025 |
| chr11 | 31821297 | 31821778 | chr11 | 31822325 | 31822393 | chr11 | 31824300 | 31824355 |
| chr11 | 31824564 | 31824680 | chr11 | 31825017 | 31825280 | chr11 | 31825696 | 31825754 |
| chr11 | 31825833 | 31826070 | chr11 | 31826107 | 31826303 | chr11 | 31826409 | 31826732 |
| chr11 | 31827114 | 31827204 | chr11 | 31827438 | 31827519 | chr11 | 31827598 | 31828123 |
| chr11 | 31833097 | 31833155 | chr11 | 31835707 | 31835797 | chr11 | 31836046 | 31836470 |
| chr11 | 31837019 | 31837512 | chr11 | 31837542 | 31838392 | chr11 | 31838678 | 31839051 |
| chr11 | 31839307 | 31839945 | chr11 | 31840042 | 31840080 | chr11 | 31840603 | 31840710 |
| chr11 | 31840769 | 31840922 | chr11 | 31841376 | 31842088 | chr11 | 31842175 | 31842276 |
| chr11 | 31846022 | 31846230 | chr11 | 31846434 | 31846985 | chr11 | 31847250 | 31847301 |
| chr11 | 31847371 | 31847712 | chr11 | 31847770 | 31847872 | chr11 | 31847896 | 31847925 |
| chr11 | 31848472 | 31848602 | chr11 | 31848723 | 31849300 | chr11 | 32009104 | 32009126 |
| chr11 | 32354844 | 32354959 | chr11 | 32355000 | 32355197 | chr11 | 32448583 | 32448893 |
| chr11 | 32455602 | 32455634 | chr11 | 32455841 | 32456025 | chr11 | 32456279 | 32456445 |
| chr11 | 32456759 | 32457176 | chr11 | 32457712 | 32458175 | chr11 | 32458389 | 32458823 |
| chr11 | 32459684 | 32460071 | chr11 | 32460468 | 32460515 | chr11 | 32460796 | 32460864 |
| chr11 | 33037467 | 33037556 | chr11 | 33264773 | 33264935 | chr11 | 33277455 | 33277485 |
| chr11 | 33318780 | 33318945 | chr11 | 33858324 | 33858463 | chr11 | 33890297 | 33890334 |
| chr11 | 33993984 | 33994014 | chr11 | 34535093 | 34535123 | chr11 | 35547499 | 35547562 |
| chr11 | 35641683 | 35641718 | chr11 | 35684958 | 35685131 | chr11 | 43596513 | 43596608 |
| chr11 | 43600453 | 43600557 | chr11 | 43601094 | 43601467 | chr11 | 43602468 | 43603036 |
| chr11 | 43603077 | 43603228 | chr11 | 43603628 | 43604145 | chr11 | 44325688 | 44325747 |
| chr11 | 44326137 | 44326184 | chr11 | 44327252 | 44327413 | chr11 | 44330878 | 44331439 |
| chr11 | 44331483 | 44331711 | chr11 | 44333052 | 44333081 | chr11 | 44333371 | 44333461 |
| chr11 | 44333477 | 44333480 | chr11 | 44337533 | 44337571 | chr11 | 44337727 | 44337861 |
| chr11 | 44337883 | 44338057 | chr11 | 44338335 | 44338367 | chr11 | 44340823 | 44340858 |

TABLE 12-continued

| chr | start | end | chr | start | end | chr | start | end |
|---|---|---|---|---|---|---|---|---|
| chr11 | 44341966 | 44342034 | chr11 | 46227561 | 46227654 | chr11 | 46316896 | 46317355 |
| chr11 | 46317408 | 46317680 | chr11 | 46413042 | 46413304 | chr11 | 46866293 | 46866510 |
| chr11 | 46940419 | 46940531 | chr11 | 46959190 | 46959251 | chr11 | 47209044 | 47209189 |
| chr11 | 47260168 | 47260258 | chr11 | 47358926 | 47359237 | chr11 | 47363557 | 47363625 |
| chr11 | 47372828 | 47373002 | chr11 | 47478438 | 47478500 | chr11 | 47485995 | 47486141 |
| chr11 | 57194355 | 57194509 | chr11 | 57235406 | 57235436 | chr11 | 57414663 | 57414663 |
| chr11 | 57437157 | 57437234 | chr11 | 57500982 | 57501068 | chr11 | 58672746 | 58673064 |
| chr11 | 59323596 | 59323729 | chr11 | 59329086 | 59329240 | chr11 | 59333405 | 59333541 |
| chr11 | 59841403 | 59841533 | chr11 | 60718668 | 60718853 | chr11 | 60718977 | 60719163 |
| chr11 | 60927079 | 60927319 | chr11 | 61049694 | 61049736 | chr11 | 51058283 | 61058341 |
| chr11 | 61062822 | 61063023 | chr11 | 61063062 | 61063138 | chr11 | 61148730 | 61148768 |
| chr11 | 61154806 | 61154836 | chr11 | 61277002 | 61277119 | chr11 | 61536985 | 61537014 |
| chr11 | 61595086 | 61595262 | chr11 | 61596420 | 61596640 | chr11 | 61664655 | 61664770 |
| chr11 | 61666106 | 61666136 | chr11 | 61811996 | 61812151 | chr11 | 61880361 | 61880398 |
| chr11 | 62370720 | 62370750 | chr11 | 62440509 | 62440588 | chr11 | 62484517 | 62484547 |
| chr11 | 62497600 | 62497630 | chr11 | 62555752 | 62555782 | chr11 | 63202941 | 63203091 |
| chr11 | 63431856 | 63431918 | chr11 | 63432139 | 63432218 | chr11 | 63609824 | 63610013 |
| chr11 | 63641072 | 63641256 | chr11 | 63839478 | 63839528 | chr11 | 63849394 | 63849426 |
| chr11 | 63934498 | 63934619 | chr11 | 64105954 | 64106108 | chr11 | 64120879 | 64120909 |
| chr11 | 64140397 | 64140427 | chr11 | 64410723 | 64410759 | chr11 | 64480429 | 64480593 |
| chr11 | 64480824 | 64481042 | chr11 | 64490435 | 64490561 | chr11 | 64490792 | 64490806 |
| chr11 | 64490826 | 64491159 | chr11 | 64578577 | 64578743 | chr11 | 64739468 | 64739508 |
| chr11 | 64796439 | 64796571 | chr11 | 64809584 | 64809906 | chr11 | 64903331 | 64903361 |
| chr11 | 64950292 | 64950374 | chr11 | 65091272 | 65091369 | chr11 | 65185548 | 65185728 |
| chr11 | 65364470 | 65364557 | chr11 | 65405659 | 65405774 | chr11 | 65409759 | 65409861 |
| chr11 | 65448943 | 65449022 | chr11 | 65478376 | 65478611 | chr11 | 65510941 | 65511172 |
| chr11 | 65511392 | 65511522 | chr11 | 65554043 | 65554410 | chr11 | 65600810 | 65601640 |
| chr11 | 65778952 | 65778981 | chr11 | 65779317 | 65779357 | chr11 | 65816447 | 65816519 |
| chr11 | 65816561 | 65816564 | chr11 | 65891131 | 65891227 | chr11 | 66114279 | 66114331 |
| chr11 | 66138094 | 66138260 | chr11 | 66188115 | 66188145 | chr11 | 66188473 | 66188484 |
| chr11 | 66188571 | 66188783 | chr11 | 66188853 | 66188974 | chr11 | 66324254 | 66324447 |
| chr11 | 66454424 | 66454454 | chr11 | 66511223 | 66511431 | chr11 | 66513217 | 66513646 |
| chr11 | 66557543 | 66557710 | chr11 | 66625207 | 66625240 | chr11 | 66649028 | 66649058 |
| chr11 | 66658224 | 66658290 | chr11 | 66725600 | 66725637 | chr11 | 66790621 | 66790655 |
| chr11 | 67072239 | 67072396 | chr11 | 67139422 | 67139460 | chr11 | 67139535 | 67139546 |
| chr11 | 67210017 | 67210057 | chr11 | 67248321 | 67248458 | chr11 | 67350180 | 67350340 |
| chr11 | 67350961 | 67350990 | chr11 | 67462643 | 67462833 | chr11 | 62764187 | 67764254 |
| chr11 | 67781196 | 67781564 | chr11 | 67797202 | 67797420 | chr11 | 67918044 | 67918145 |
| chr11 | 67999703 | 67999866 | chr11 | 68096034 | 68096179 | chr11 | 68118716 | 68118745 |
| chr11 | 68153950 | 68154098 | chr11 | 68181217 | 68181288 | chr11 | 68221758 | 68222056 |
| chr11 | 68409558 | 68409588 | chr11 | 68804728 | 68804776 | chr11 | 69192566 | 69192784 |
| chr11 | 69280561 | 69280633 | chr11 | 69466004 | 69466042 | chr11 | 69484356 | 69484454 |
| chr11 | 69516968 | 69517174 | chr11 | 69518030 | 69518211 | chr11 | 69518530 | 69518718 |
| chr11 | 69588930 | 69589184 | chr11 | 69589824 | 69589854 | chr11 | 69590149 | 69590222 |
| chr11 | 70211516 | 70211545 | chr11 | 71192746 | 71192889 | chr11 | 71318332 | 71318809 |
| chr11 | 71318953 | 71318967 | chr11 | 71647544 | 71647574 | chr11 | 71792437 | 71792496 |
| chr11 | 71863650 | 71863785 | chr11 | 71951639 | 71951738 | chr11 | 71952340 | 71952416 |
| chr11 | 71952459 | 71952541 | chr11 | 71954612 | 71954642 | chr11 | 71955344 | 71955377 |
| chr11 | 71956007 | 71956340 | chr11 | 72413980 | 72414010 | chr11 | 72432837 | 72432916 |
| chr11 | 72475677 | 72475711 | chr11 | 72532348 | 72532378 | chr11 | 72929747 | 72929883 |
| chr11 | 73072907 | 73072953 | chr11 | 73310367 | 73310441 | chr11 | 73481055 | 73481085 |
| chr11 | 73561763 | 73561798 | chr11 | 73685698 | 73685845 | chr11 | 73694609 | 73694659 |
| chr11 | 74246487 | 74246521 | chr11 | 74394491 | 74394600 | chr11 | 74953265 | 74953336 |
| chr11 | 75379283 | 75379895 | chr11 | 75459486 | 75459775 | chr11 | 75858210 | 75858240 |
| chr11 | 75859012 | 75859053 | chr11 | 76293588 | 76293618 | chr11 | 76371738 | 76372077 |
| chr11 | 76594692 | 76594722 | chr11 | 77533964 | 77534145 | chr11 | 78672917 | 78672924 |
| chr11 | 79151173 | 79151216 | chr11 | 82444376 | 82445101 | chr11 | 82998001 | 82998121 |
| chr11 | 85709169 | 85709254 | chr11 | 86085742 | 86085861 | chr11 | 86085932 | 86085968 |
| chr11 | 86383167 | 86383710 | chr11 | 88241705 | 88241975 | chr11 | 88242131 | 88242274 |
| chr11 | 88242359 | 88242618 | chr11 | 88799082 | 88799209 | chr11 | 89052235 | 89052282 |
| chr11 | 89867794 | 89867990 | chr11 | 91957500 | 91957674 | chr11 | 91957974 | 91958230 |
| chr11 | 91958734 | 91959326 | chr11 | 91959356 | 91959430 | chr11 | 91959899 | 91960045 |
| chr11 | 93063583 | 93063645 | chr11 | 93063870 | 93063948 | chr11 | 93911651 | 93911800 |
| chr11 | 94134086 | 94134463 | chr11 | 94134683 | 94134853 | chr11 | 94275794 | 94275951 |
| chr11 | 94278456 | 94278603 | chr11 | 94473600 | 94473768 | chr11 | 94473803 | 94474139 |
| chr11 | 94474356 | 94474385 | chr11 | 94502334 | 94502489 | chr11 | 94884130 | 94884160 |
| chr11 | 96517902 | 96517932 | chr11 | 98891477 | 98891882 | chr11 | 100997649 | 100997981 |
| chr11 | 100998276 | 100998318 | chr11 | 100998667 | 100998744 | chr11 | 101453180 | 101453518 |
| chr11 | 101723359 | 101723455 | chr11 | 102158378 | 102158427 | chr11 | 102961347 | 102961649 |
| chr11 | 102962922 | 102963052 | chr11 | 102980027 | 102980056 | chr11 | 104034521 | 104034996 |
| chr11 | 105480755 | 105480785 | chr11 | 105481216 | 105481571 | chr11 | 106888308 | 106888429 |
| chr11 | 106888641 | 106888801 | chr11 | 107461623 | 107461653 | chr11 | 107462415 | 107462459 |
| chr11 | 108236072 | 108236101 | chr11 | 108603233 | 108603263 | chr11 | 109292906 | 109293026 |
| chr11 | 109293720 | 109293763 | chr11 | 110166519 | 110166935 | chr11 | 110582232 | 110582434 |
| chr11 | 110582895 | 110583028 | chr11 | 110583044 | 110583050 | chr11 | 110583574 | 110583730 |
| chr11 | 111383183 | 111383531 | chr11 | 111383558 | 111383682 | chr11 | 111411093 | 111411581 |
| chr11 | 111411822 | 111412061 | chr11 | 111783548 | 111783577 | chr11 | 111976911 | 111976941 |
| chr11 | 114113022 | 114113052 | chr11 | 115375120 | 115375177 | chr11 | 115530222 | 115530604 |

TABLE 12-continued

| chr | start | end | chr | start | end | chr | start | end |
|---|---|---|---|---|---|---|---|---|
| chr11 | 115630531 | 115630910 | chr11 | 115631307 | 115631364 | chr11 | 116147253 | 116147283 |
| chr11 | 116451023 | 116451190 | chr11 | 116976126 | 116976156 | chr11 | 116984568 | 116984665 |
| chr11 | 117017686 | 117017773 | chr11 | 117055950 | 117056073 | chr11 | 117296921 | 117297109 |
| chr11 | 118724458 | 118724605 | chr11 | 118991033 | 118991079 | chr11 | 119148865 | 119148945 |
| chr11 | 119149236 | 119149265 | chr11 | 119292779 | 119292809 | chr11 | 119293370 | 119293615 |
| chr11 | 119612227 | 119612267 | chr11 | 119612324 | 119612399 | chr11 | 119612861 | 119613075 |
| chr11 | 120008105 | 120008504 | chr11 | 120039833 | 120039865 | chr11 | 120367948 | 120368008 |
| chr11 | 120435405 | 120435477 | chr11 | 120435800 | 120435830 | chr11 | 120894800 | 120895026 |
| chr11 | 120998701 | 120998825 | chr11 | 121152057 | 121152203 | chr11 | 122847265 | 122847696 |
| chr11 | 122848079 | 122848312 | chr11 | 122848369 | 122848591 | chr11 | 122849301 | 122849331 |
| chr11 | 122849642 | 122850123 | chr11 | 122850149 | 122850163 | chr11 | 122850424 | 122850536 |
| chr11 | 122851177 | 122851209 | chr11 | 122852438 | 122852475 | chr11 | 122855008 | 122855043 |
| chr11 | 122895443 | 122895485 | chr11 | 122961054 | 122961219 | chr11 | 123066433 | 123066463 |
| chr11 | 123229058 | 123229406 | chr11 | 123300824 | 123301028 | chr11 | 123301083 | 123302026 |
| chr11 | 123963874 | 123963994 | chr11 | 124735437 | 124735482 | chr11 | 124736196 | 124736252 |
| chr11 | 124738777 | 124739088 | chr11 | 125035763 | 125036208 | chr11 | 125220500 | 125220643 |
| chr11 | 125755612 | 125755710 | chr11 | 125758604 | 125758660 | chr11 | 125773675 | 125774060 |
| chr11 | 126870182 | 126870212 | chr11 | 126870453 | 126870500 | chr11 | 126870525 | 126870543 |
| chr11 | 126873390 | 126873515 | chr11 | 128391893 | 128392116 | chr11 | 128562892 | 128563185 |
| chr11 | 128563337 | 128563730 | chr11 | 128563940 | 128564329 | chr11 | 128564740 | 128564876 |
| chr11 | 128564992 | 128565379 | chr11 | 128657892 | 128657970 | chr11 | 129242876 | 129243241 |
| chr11 | 129243305 | 129243587 | chr11 | 129243849 | 129244300 | chr11 | 129244441 | 129244603 |
| chr11 | 129244893 | 129244923 | chr11 | 129245673 | 129245810 | chr11 | 129246070 | 129246129 |
| chr11 | 129907552 | 129907714 | chr11 | 129931742 | 129931851 | chr11 | 130318960 | 130318997 |
| chr11 | 130319527 | 130319613 | chr11 | 130343061 | 130343100 | chr11 | 130359769 | 130359915 |
| chr11 | 130781550 | 130781781 | chr11 | 130785487 | 130785622 | chr11 | 130854324 | 130854490 |
| chr11 | 131522763 | 131522947 | chr11 | 131564970 | 131565073 | chr11 | 131766715 | 131766960 |
| chr11 | 131780877 | 131781078 | chr11 | 132484215 | 132484404 | chr11 | 132813489 | 132813757 |
| chr11 | 132813908 | 132813949 | chr11 | 132864134 | 132864175 | chr11 | 132934123 | 132934176 |
| chr11 | 132952768 | 132953050 | chr11 | 132953233 | 132953423 | chr11 | 133231739 | 133231832 |
| chr11 | 133402206 | 133402260 | chr11 | 133792055 | 133792214 | chr11 | 133825226 | 133825455 |
| chr11 | 133906783 | 133906918 | chr11 | 133939002 | 133939177 | chr11 | 134145703 | 134146393 |
| chr11 | 134146682 | 134146894 | chr11 | 134201502 | 134201543 | chr11 | 134201841 | 134202084 |
| chr11 | 134281365 | 134281509 | chr12 | 570090 | 570171 | chr12 | 1639135 | 1639222 |
| chr12 | 1650475 | 1650577 | chr12 | 2046104 | 2046134 | chr12 | 2162554 | 2162817 |
| chr12 | 2163164 | 2163276 | chr12 | 2403658 | 2403714 | chr12 | 2566053 | 2566247 |
| chr12 | 2595199 | 2595339 | chr12 | 2862068 | 2862142 | chr12 | 2964465 | 2964577 |
| chr12 | 3371882 | 3371911 | chr12 | 3373533 | 3373666 | chr12 | 3600315 | 3600345 |
| chr12 | 3602270 | 3602716 | chr12 | 3602865 | 3602879 | chr12 | 3603100 | 3603156 |
| chr12 | 3862254 | 3862298 | chr12 | 4213973 | 4214157 | chr12 | 4231674 | 4231767 |
| chr12 | 4274054 | 4274188 | chr12 | 4274271 | 4274409 | chr12 | 4323835 | 4323912 |
| chr12 | 4362436 | 4362471 | chr12 | 4378252 | 4378330 | chr12 | 4379357 | 4379491 |
| chr12 | 4381433 | 4382386 | chr12 | 4382965 | 4382999 | chr12 | 4383492 | 4383784 |
| chr12 | 4384389 | 4384418 | chr12 | 4384736 | 4384902 | chr12 | 4392883 | 4392922 |
| chr12 | 4405589 | 4405619 | chr12 | 4431271 | 4431301 | chr12 | 4554801 | 4554831 |
| chr12 | 4919145 | 4919213 | chr12 | 4919239 | 4919244 | chr12 | 5018073 | 5018692 |
| chr12 | 5019085 | 5019742 | chr12 | 5019794 | 5020313 | chr12 | 5153039 | 5153286 |
| chr12 | 5153358 | 5153460 | chr12 | 5541100 | 5541177 | chr12 | 5542325 | 5542439 |
| chr12 | 5542759 | 5542911 | chr12 | 5840200 | 5840363 | chr12 | 6308743 | 6308772 |
| chr12 | 6473721 | 6473762 | chr12 | 6483615 | 6483756 | chr12 | 6664508 | 6664522 |
| chr12 | 6678158 | 6678203 | chr12 | 7403914 | 7404060 | chr12 | 7559160 | 7559307 |
| chr12 | 8025635 | 8025660 | chr12 | 8036526 | 8036634 | chr12 | 8122523 | 8122628 |
| chr12 | 8127036 | 8127140 | chr12 | 8127565 | 8127595 | chr12 | 8139203 | 8139233 |
| chr12 | 8163573 | 8163603 | chr12 | 8171360 | 8171745 | chr12 | 8180999 | 8181065 |
| chr12 | 8549178 | 8549208 | chr12 | 8808599 | 8808709 | chr12 | 8850658 | 8850744 |
| chr12 | 8975182 | 8975361 | chr12 | 9916313 | 9916343 | chr12 | 10085916 | 10085948 |
| chr12 | 10363278 | 10363607 | chr12 | 10772771 | 10772896 | chr12 | 11653449 | 11653463 |
| chr12 | 12456859 | 12456889 | chr12 | 12504616 | 12504850 | chr12 | 12848390 | 12848556 |
| chr12 | 13036048 | 13036078 | chr12 | 13055966 | 13055996 | chr12 | 14133152 | 14133263 |
| chr12 | 14133619 | 14133881 | chr12 | 14135111 | 14135339 | chr12 | 14719937 | 14719967 |
| chr12 | 14818824 | 14818867 | chr12 | 15374258 | 15374291 | chr12 | 16500576 | 16500621 |
| chr12 | 19282333 | 19282363 | chr12 | 20521704 | 20521841 | chr12 | 20522457 | 20522487 |
| chr12 | 20522769 | 20522891 | chr12 | 21680394 | 21680683 | chr12 | 21810264 | 21810868 |
| chr12 | 21833068 | 21833265 | chr12 | 22093825 | 22094268 | chr12 | 22094578 | 22094810 |
| chr12 | 22486799 | 22486881 | chr12 | 22487134 | 22487473 | chr12 | 22698063 | 22698120 |
| chr12 | 23229390 | 23229420 | chr12 | 24714909 | 24714938 | chr12 | 24715235 | 24715264 |
| chr12 | 24716033 | 24716218 | chr12 | 25056243 | 25056436 | chr12 | 25101592 | 25101660 |
| chr12 | 25101919 | 25101997 | chr12 | 25102010 | 25102086 | chr12 | 25362824 | 25362853 |
| chr12 | 25368463 | 25368492 | chr12 | 25378543 | 25378662 | chr12 | 25380231 | 25380299 |
| chr12 | 25398203 | 25398319 | chr12 | 26178334 | 26178376 | chr12 | 27114515 | 27114639 |
| chr12 | 27176441 | 27176539 | chr12 | 27494550 | 27494580 | chr12 | 28123996 | 28124247 |
| chr12 | 28127767 | 28128302 | chr12 | 28128547 | 28129084 | chr12 | 29936016 | 29936048 |
| chr12 | 29936602 | 29936642 | chr12 | 29936662 | 29936831 | chr12 | 29937331 | 29937764 |
| chr12 | 30322774 | 30322924 | chr12 | 30323015 | 30323439 | chr12 | 30323503 | 30323517 |
| chr12 | 30975572 | 30975959 | chr12 | 31079268 | 31079362 | chr12 | 31079418 | 31079499 |
| chr12 | 31316012 | 31316362 | chr12 | 31366306 | 31366336 | chr12 | 32086716 | 32086982 |
| chr12 | 32340317 | 32340534 | chr12 | 32831622 | 32831652 | chr12 | 33591774 | 33591804 |
| chr12 | 33592613 | 33692847 | chr12 | 34494888 | 34494918 | chr12 | 34502733 | 34502803 |

TABLE 12-continued

| chr | start | end | chr | start | end | chr | start | end |
|---|---|---|---|---|---|---|---|---|
| chr12 | 39299117 | 39299560 | chr12 | 39539353 | 39539436 | chr12 | 10618404 | 40618470 |
| chr12 | 41086183 | 41086379 | chr12 | 41086784 | 41087106 | chr12 | 41582513 | 41582988 |
| chr12 | 41583374 | 41583419 | chr12 | 43945110 | 43945124 | chr12 | 43945356 | 43945379 |
| chr12 | 43945417 | 43945526 | chr12 | 43946203 | 43946298 | chr12 | 45269504 | 45269624 |
| chr12 | 45444118 | 45444681 | chr12 | 45444715 | 45445258 | chr12 | 46767650 | 46767697 |
| chr12 | 47225381 | 47225476 | chr12 | 47225551 | 47225579 | chr12 | 47629349 | 47629379 |
| chr12 | 48397195 | 48398070 | chr12 | 48398641 | 48398671 | chr12 | 48690674 | 48690880 |
| chr12 | 49035233 | 49035414 | chr12 | 49074601 | 49074843 | chr12 | 49297802 | 49297915 |
| chr12 | 49366374 | 49366423 | chr12 | 49374914 | 49375026 | chr12 | 49375116 | 49375119 |
| chr12 | 49375325 | 49375529 | chr12 | 49390873 | 49391104 | chr12 | 49391147 | 49391877 |
| chr12 | 49515852 | 49515920 | chr12 | 49657705 | 49657901 | chr12 | 49691049 | 49691078 |
| chr12 | 49727092 | 49727127 | chr12 | 49729728 | 49730090 | chr12 | 49759530 | 49759559 |
| chr12 | 49989786 | 49989816 | chr12 | 50297497 | 50297554 | chr12 | 50297974 | 50298055 |
| chr12 | 50426748 | 50426799 | chr12 | 50507349 | 50507522 | chr12 | 50673944 | 50674096 |
| chr12 | 50897763 | 50898273 | chr12 | 51400044 | 51400091 | chr12 | 51420874 | 51421271 |
| chr12 | 51421556 | 51421586 | chr12 | 51441284 | 51441368 | chr12 | 51565269 | 51565548 |
| chr12 | 51625514 | 51625587 | chr12 | 51930708 | 51930862 | chr12 | 52262983 | 52263106 |
| chr12 | 52301280 | 52301305 | chr12 | 52400831 | 52401537 | chr12 | 52408905 | 52409033 |
| chr12 | 52627273 | 52627438 | chr12 | 52652153 | 52652219 | chr12 | 52652600 | 52652613 |
| chr12 | 53108089 | 53108218 | chr12 | 53359386 | 53359563 | chr12 | 53763427 | 53763885 |
| chr12 | 53766833 | 53766964 | chr12 | 53834392 | 53834475 | chr12 | 53885346 | 53885651 |
| chr12 | 54089093 | 54089511 | chr12 | 54132252 | 54132329 | chr12 | 54145843 | 54145857 |
| chr12 | 54145881 | 54145895 | chr12 | 54321250 | 54321628 | chr12 | 54322201 | 54322252 |
| chr12 | 54324799 | 54324937 | chr12 | 54329358 | 54329478 | chr12 | 54329605 | 54329947 |
| chr12 | 54331062 | 54331135 | chr12 | 54332868 | 54333337 | chr12 | 54338656 | 54338817 |
| chr12 | 54338979 | 54339681 | chr12 | 54343812 | 54343829 | chr12 | 54345611 | 54345658 |
| chr12 | 54345966 | 54346032 | chr12 | 54348844 | 54349079 | chr12 | 54349256 | 54349336 |
| chr12 | 54354514 | 54354621 | chr12 | 54354905 | 54355086 | chr12 | 54359960 | 54360084 |
| chr12 | 54360608 | 54360649 | chr12 | 54377912 | 54377946 | chr12 | 54377978 | 54378115 |
| chr12 | 54379174 | 54379623 | chr12 | 54379888 | 54379930 | chr12 | 54379959 | 54380459 |
| chr12 | 54387842 | 54387959 | chr12 | 54388215 | 54388245 | chr12 | 54391400 | 54391403 |
| chr12 | 54393479 | 54393684 | chr12 | 54393950 | 54394162 | chr12 | 54394410 | 54394418 |
| chr12 | 54398889 | 54398959 | chr12 | 54399616 | 54399646 | chr12 | 54402690 | 54402796 |
| chr12 | 54403067 | 54403360 | chr12 | 54408411 | 54408726 | chr12 | 54409476 | 54409505 |
| chr12 | 54423616 | 54423697 | chr12 | 54424746 | 54424748 | chr12 | 54425032 | 54425119 |
| chr12 | 54447351 | 54447581 | chr12 | 54447899 | 54447977 | chr12 | 54520745 | 54520868 |
| chr12 | 54613463 | 54613615 | chr12 | 54719808 | 54720232 | chr12 | 54812238 | 54812359 |
| chr12 | 54894048 | 54894173 | chr12 | 54922624 | 54922803 | chr12 | 54942994 | 54943116 |
| chr12 | 55480923 | 55481067 | chr12 | 55561202 | 55561354 | chr12 | 56231108 | 56231148 |
| chr12 | 56400463 | 56400591 | chr12 | 56478840 | 56478869 | chr12 | 56481645 | 56481937 |
| chr12 | 56486572 | 56486601 | chr12 | 56490965 | 56490994 | chr12 | 56491630 | 56491659 |
| chr12 | 56492618 | 56492647 | chr12 | 56558381 | 56558519 | chr12 | 56653281 | 56653369 |
| chr12 | 56873601 | 56873630 | chr12 | 56882240 | 56882380 | chr12 | 57174355 | 57174452 |
| chr12 | 57359920 | 57359950 | chr12 | 57387303 | 57387332 | chr12 | 57559869 | 57559925 |
| chr12 | 57618574 | 57618710 | chr12 | 57881127 | 57881383 | chr12 | 57944081 | 57944117 |
| chr12 | 57983314 | 57983348 | chr12 | 58021320 | 58021458 | chr12 | 58021916 | 58022029 |
| chr12 | 58025646 | 58025733 | chr12 | 58025870 | 58025873 | chr12 | 58145415 | 58145450 |
| chr12 | 59314159 | 59314189 | chr12 | 62584838 | 62585012 | chr12 | 62585031 | 62586017 |
| chr12 | 62586252 | 62586281 | chr12 | 62603907 | 62603937 | chr12 | 62858444 | 62858575 |
| chr12 | 63025574 | 63026160 | chr12 | 63326618 | 63326648 | chr12 | 63543848 | 63544401 |
| chr12 | 63544499 | 63544599 | chr12 | 63545313 | 63545343 | chr12 | 64028352 | 64028382 |
| chr12 | 64061821 | 64062159 | chr12 | 64062369 | 64062578 | chr12 | 64062921 | 64063039 |
| chr12 | 64783185 | 64783308 | chr12 | 64784108 | 64784252 | chr12 | 64784534 | 64784564 |
| chr12 | 65218102 | 65218550 | chr12 | 65218901 | 65219156 | chr12 | 65219376 | 65219527 |
| chr12 | 65219606 | 65219784 | chr12 | 65220205 | 65220350 | chr12 | 55514863 | 65515596 |
| chr12 | 65516360 | 65516455 | chr12 | 65557212 | 65557376 | chr12 | 55561778 | 65562086 |
| chr12 | 66122800 | 66122995 | chr12 | 66123381 | 66123519 | chr12 | 66135984 | 66136014 |
| chr12 | 66582827 | 66583137 | chr12 | 68433260 | 68433321 | chr12 | 68964473 | 68964503 |
| chr12 | 68978322 | 68978576 | chr12 | 69327259 | 69327463 | chr12 | 69754451 | 69754729 |
| chr12 | 69964176 | 69964264 | chr12 | 70087493 | 70087568 | chr12 | 70698883 | 70699050 |
| chr12 | 72332641 | 72332696 | chr12 | 72665186 | 72665788 | chr12 | 72666713 | 72666807 |
| chr12 | 72666998 | 72667425 | chr12 | 72667652 | 72667682 | chr12 | 75601379 | 75601499 |
| chr12 | 75601696 | 75601910 | chr12 | 75602976 | 75603231 | chr12 | 75728336 | 75728485 |
| chr12 | 75728737 | 75728766 | chr12 | 77719311 | 77719422 | chr12 | 79257222 | 79257351 |
| chr12 | 81102185 | 81102455 | chr12 | 81102513 | 81102562 | chr12 | 81107997 | 81108034 |
| chr12 | 81471517 | 81471614 | chr12 | 81471754 | 81472111 | chr12 | 85306519 | 85306572 |
| chr12 | 85667272 | 85667731 | chr12 | 85673206 | 85673235 | chr12 | 85673460 | 85674807 |
| chr12 | 88973544 | 88973582 | chr12 | 88974159 | 88974253 | chr12 | 89915009 | 89915043 |
| chr12 | 93476304 | 93476342 | chr12 | 93966429 | 93966603 | chr12 | 93966998 | 93967215 |
| chr12 | 94543409 | 94543445 | chr12 | 94543899 | 94543961 | chr12 | 94544022 | 94544052 |
| chr12 | 94852412 | 94852506 | chr12 | 95216830 | 95216960 | chr12 | 95267524 | 95267554 |
| chr12 | 95267865 | 95267976 | chr12 | 95822981 | 95823011 | chr12 | 95866563 | 95866609 |
| chr12 | 95942965 | 95942998 | chr12 | 96880822 | 96881029 | chr12 | 98948200 | 98948235 |
| chr12 | 98949938 | 98949972 | chr12 | 98961066 | 98961241 | chr12 | 98986343 | 98986491 |
| chr12 | 99288312 | 99288407 | chr12 | 99288622 | 99288936 | chr12 | 99289162 | 99289309 |
| chr12 | 100595495 | 100595558 | chr12 | 101025380 | 101025410 | chr12 | 101111029 | 101111061 |
| chr12 | 101111373 | 101111479 | chr12 | 102457208 | 102457238 | chr12 | 103218495 | 103218595 |
| chr12 | 103351564 | 103351985 | chr12 | 103352052 | 103352154 | chr12 | 103352171 | 103352282 |

TABLE 12-continued

| chr | start | end | chr | start | end | chr | start | end |
|---|---|---|---|---|---|---|---|---|
| chr12 | 103352314 | 103352681 | chr12 | 103358865 | 103358899 | chr12 | 103359556 | 103359586 |
| chr12 | 103889160 | 103889211 | chr12 | 103889789 | 103889812 | chr12 | 104506691 | 104506783 |
| chr12 | 104609417 | 104609796 | chr12 | 104671030 | 104671064 | chr12 | 104671699 | 104671761 |
| chr12 | 104684181 | 104684258 | chr12 | 104696376 | 104696502 | chr12 | 104850505 | 104850536 |
| chr12 | 104850578 | 104850592 | chr12 | 104851077 | 104851186 | chr12 | 104852032 | 104852508 |
| chr12 | 105017109 | 105017228 | chr12 | 105478323 | 105478419 | chr12 | 106533852 | 106533881 |
| chr12 | 106974353 | 106974383 | chr12 | 106976725 | 106976779 | chr12 | 106977321 | 106977497 |
| chr12 | 106979161 | 106979534 | chr12 | 106979799 | 106979995 | chr12 | 106980223 | 106980333 |
| chr12 | 106980912 | 106981406 | chr12 | 107486550 | 107486672 | chr12 | 107487194 | 107487855 |
| chr12 | 107712273 | 107712303 | chr12 | 107713205 | 107713235 | chr12 | 107714866 | 107715153 |
| chr12 | 108080498 | 108080553 | chr12 | 108168971 | 108168413 | chr12 | 108169550 | 108169573 |
| chr12 | 108237465 | 108237524 | chr12 | 108238102 | 108238513 | chr12 | 108297411 | 108297466 |
| chr12 | 109488519 | 109488685 | chr12 | 109639281 | 109639475 | chr12 | 110353414 | 110353451 |
| chr12 | 110607084 | 110507207 | chr12 | 110717541 | 110717710 | chr12 | 110840344 | 110840404 |
| chr12 | 110854243 | 110854288 | chr12 | 110887179 | 110887209 | chr12 | 110983706 | 110983736 |
| chr12 | 111127124 | 111127455 | chr12 | 111143726 | 111143756 | chr12 | 111471177 | 111471559 |
| chr12 | 111471948 | 111471959 | chr12 | 111472059 | 111472195 | chr12 | 111472357 | 111472671 |
| chr12 | 111763122 | 111763152 | chr12 | 112547662 | 112547692 | chr12 | 112574734 | 112574995 |
| chr12 | 112792829 | 112792944 | chr12 | 112825760 | 112825896 | chr12 | 112888151 | 112888315 |
| chr12 | 112910821 | 112910850 | chr12 | 112915509 | 112915538 | chr12 | 112926255 | 112926284 |
| chr12 | 112926876 | 112926914 | chr12 | 113012954 | 113013157 | chr12 | 113541667 | 113542099 |
| chr12 | 113592238 | 113592359 | chr12 | 113795506 | 113795657 | chr12 | 113900753 | 113900765 |
| chr12 | 113901074 | 113901158 | chr12 | 113901408 | 113901450 | chr12 | 113902042 | 113902353 |
| chr12 | 113903468 | 113903498 | chr12 | 113904779 | 113905016 | chr12 | 113908990 | 113909314 |
| chr12 | 113909329 | 113909455 | chr12 | 113913267 | 113913681 | chr12 | 113913884 | 113914050 |
| chr12 | 113916222 | 113916316 | chr12 | 113916649 | 113916678 | chr12 | 113916972 | 113917012 |
| chr12 | 113917232 | 113917310 | chr12 | 113917775 | 113917890 | chr12 | 114029408 | 114029660 |
| chr12 | 114076029 | 114076093 | chr12 | 114337763 | 114337793 | chr12 | 114833985 | 114834102 |
| chr12 | 114838369 | 114838726 | chr12 | 114839104 | 114839147 | chr12 | 114841046 | 114841084 |
| chr12 | 114841425 | 114841493 | chr12 | 114843112 | 114843186 | chr12 | 114843261 | 114843278 |
| chr12 | 114843545 | 114843650 | chr12 | 114844201 | 114844300 | chr12 | 114846715 | 114846768 |
| chr12 | 114847043 | 114847435 | chr12 | 114847578 | 114847691 | chr12 | 114852040 | 114852082 |
| chr12 | 114862293 | 114852373 | chr12 | 114877171 | 114877262 | chr12 | 114878550 | 114878584 |
| chr12 | 114878813 | 114879012 | chr12 | 114881634 | 114881764 | chr12 | 114882555 | 114882646 |
| chr12 | 114883473 | 114883535 | chr12 | 114918594 | 114918717 | chr12 | 115136159 | 115136363 |
| chr12 | 116946086 | 116946199 | chr12 | 116946251 | 116946548 | chr12 | 117474065 | 117474198 |
| chr12 | 117526330 | 117526368 | chr12 | 117798065 | 117798095 | chr12 | 117799413 | 117799529 |
| chr12 | 118860397 | 118860654 | chr12 | 118920764 | 118920804 | chr12 | 119212319 | 119212381 |
| chr12 | 119418594 | 119418847 | chr12 | 119419436 | 119419466 | chr12 | 119419720 | 119419899 |
| chr12 | 120032862 | 120033169 | chr12 | 120148142 | 120148248 | chr12 | 120148923 | 120148962 |
| chr12 | 120535158 | 120535187 | chr12 | 120536625 | 120536654 | chr12 | 120885216 | 120885245 |
| chr12 | 120971686 | 120971716 | chr12 | 121622546 | 121622576 | chr12 | 122108464 | 122108601 |
| chr12 | 122192723 | 122192843 | chr12 | 122278388 | 122278580 | chr12 | 122285067 | 122285108 |
| chr12 | 122473581 | 122473611 | chr12 | 122940449 | 122940471 | chr12 | 123129129 | 123129550 |
| chr12 | 123211316 | 123211390 | chr12 | 123233646 | 123233846 | chr12 | 123410210 | 123410240 |
| chr12 | 123942025 | 123942189 | chr12 | 124117199 | 124117289 | chr12 | 124246908 | 124246937 |
| chr12 | 124247208 | 124247237 | chr12 | 124393560 | 124393604 | chr12 | 124397464 | 124397618 |
| chr12 | 124865115 | 124865144 | chr12 | 125009276 | 125009306 | chr12 | 125533949 | 125534407 |
| chr12 | 125589840 | 125589872 | chr12 | 125670117 | 125670260 | chr12 | 126168554 | 126168620 |
| chr12 | 127211317 | 127211378 | chr12 | 127765158 | 127765432 | chr12 | 127940086 | 127940247 |
| chr12 | 128761384 | 128751443 | chr12 | 128751821 | 128751877 | chr12 | 128752115 | 128752240 |
| chr12 | 128752499 | 128752944 | chr12 | 128753210 | 128753240 | chr12 | 128850534 | 128850644 |
| chr12 | 129338588 | 129338816 | chr12 | 129427424 | 129427557 | chr12 | 129447299 | 129447450 |
| chr12 | 130037653 | 130037778 | chr12 | 130387797 | 130387811 | chr12 | 130388410 | 130388434 |
| chr12 | 130389013 | 130389152 | chr12 | 130589202 | 130589266 | chr12 | 130645233 | 130645627 |
| chr12 | 130646946 | 130647115 | chr12 | 130647574 | 130647908 | chr12 | 130647951 | 130648069 |
| chr12 | 130821371 | 130821621 | chr12 | 130968621 | 130968654 | chr12 | 131200379 | 131200645 |
| chr12 | 131400816 | 131400919 | chr12 | 131403032 | 131403125 | chr12 | 131513345 | 131513403 |
| chr12 | 132102173 | 132102202 | chr12 | 132169288 | 132169442 | chr12 | 132221689 | 132222076 |
| chr12 | 132332910 | 132332940 | chr12 | 132333434 | 132333597 | chr12 | 132348651 | 132348684 |
| chr12 | 132423516 | 132423854 | chr12 | 132643233 | 132643279 | chr12 | 132986495 | 132986581 |
| chr12 | 133002792 | 133003231 | chr12 | 133172907 | 133173021 | chr12 | 133195093 | 133195196 |
| chr12 | 133199738 | 133199784 | chr12 | 133262698 | 133262926 | chr12 | 133280578 | 133280682 |
| chr12 | 133463736 | 133463876 | chr12 | 133464108 | 133464166 | chr12 | 133464840 | 133465027 |
| chr12 | 133481490 | 133481655 | chr12 | 133484742 | 133484852 | chr12 | 133485162 | 133485347 |
| chr12 | 133485557 | 133485689 | chr12 | 133485816 | 133485847 | chr12 | 133758048 | 133758107 |
| chr13 | 20175911 | 20175941 | chr13 | 20451144 | 20451360 | chr13 | 20735804 | 20736089 |
| chr13 | 21649636 | 21649775 | chr13 | 21713233 | 21713513 | chr13 | 22243273 | 22243469 |
| chr13 | 23489851 | 23489914 | chr13 | 23653781 | 23653813 | chr13 | 23733447 | 23734020 |
| chr13 | 23734284 | 23734297 | chr13 | 24099683 | 24099713 | chr13 | 24477643 | 24477906 |
| chr13 | 25115713 | 25115771 | chr13 | 25319856 | 25319904 | chr13 | 25320388 | 25320539 |
| chr13 | 25320614 | 25321028 | chr13 | 25321113 | 25321350 | chr13 | 25321699 | 25321942 |
| chr13 | 25593062 | 25593242 | chr13 | 25621045 | 25621205 | chr13 | 25621264 | 25621394 |
| chr13 | 25668799 | 25668829 | chr13 | 25744716 | 25744734 | chr13 | 25745301 | 25745594 |
| chr13 | 25745727 | 25746000 | chr13 | 25946301 | 25946411 | chr13 | 25946620 | 25946673 |
| chr13 | 26042678 | 26042707 | chr13 | 26042769 | 26043170 | chr13 | 26043341 | 26043499 |
| chr13 | 26340608 | 26340755 | chr13 | 26625301 | 26625656 | chr13 | 27334211 | 27334563 |
| chr13 | 27334772 | 27334894 | chr13 | 27699893 | 27699981 | chr13 | 28239909 | 28240164 |

TABLE 12-continued

| chr | start | end | chr | start | end | chr | start | end |
|---|---|---|---|---|---|---|---|---|
| chr13 | 28365705 | 28366122 | chr13 | 28366482 | 28366577 | chr13 | 28367024 | 28367038 |
| chr13 | 28367794 | 28367945 | chr13 | 28368154 | 28368168 | chr13 | 28368451 | 28368593 |
| chr13 | 28368952 | 28369070 | chr13 | 28369162 | 28369990 | chr13 | 28370947 | 28371061 |
| chr13 | 28394766 | 28394866 | chr13 | 28395501 | 28395553 | chr13 | 28395998 | 28396073 |
| chr13 | 28491793 | 28491946 | chr13 | 28492244 | 28492553 | chr13 | 28503042 | 28503074 |
| chr13 | 28528534 | 28528748 | chr13 | 28540745 | 28540927 | chr13 | 28543212 | 28543242 |
| chr13 | 28544397 | 28544584 | chr13 | 28544666 | 28544903 | chr13 | 28549497 | 28549891 |
| chr13 | 28550240 | 28550552 | chr13 | 28551417 | 28551461 | chr13 | 28551950 | 28552167 |
| chr13 | 28552794 | 28552824 | chr13 | 28553030 | 28553138 | chr13 | 28589765 | 28589794 |
| chr13 | 28592605 | 28592658 | chr13 | 28601345 | 28601374 | chr13 | 28602326 | 28602355 |
| chr13 | 28608233 | 28608355 | chr13 | 28610123 | 28610152 | chr13 | 28674018 | 28674226 |
| chr13 | 28674721 | 28674734 | chr13 | 28706016 | 28706140 | chr13 | 29067773 | 29068416 |
| chr13 | 29068926 | 29068985 | chr13 | 29068994 | 29069065 | chr13 | 29106308 | 29106814 |
| chr13 | 29106899 | 29107063 | chr13 | 29107253 | 29107309 | chr13 | 29112395 | 29112444 |
| chr13 | 30141688 | 30141718 | chr13 | 30707569 | 30707599 | chr13 | 31185432 | 31185548 |
| chr13 | 31742953 | 31743177 | chr13 | 32605034 | 32605324 | chr13 | 32605443 | 32605623 |
| chr13 | 32605675 | 32605966 | chr13 | 33591300 | 33591419 | chr13 | 33924666 | 33924790 |
| chr13 | 35517410 | 35517648 | chr13 | 36044829 | 36044930 | chr13 | 36049995 | 36050025 |
| chr13 | 36269480 | 36269509 | chr13 | 36541300 | 36541329 | chr13 | 36553399 | 36553428 |
| chr13 | 36588100 | 36688129 | chr13 | 36704939 | 36705055 | chr13 | 36705451 | 36705489 |
| chr13 | 36909206 | 36909236 | chr13 | 36920317 | 36920386 | chr13 | 36920628 | 36920785 |
| chr13 | 37004771 | 37005129 | chr13 | 37005900 | 37006062 | chr13 | 37006434 | 37006657 |
| chr13 | 37006734 | 37006762 | chr13 | 37248063 | 37248148 | chr13 | 37248295 | 37248319 |
| chr13 | 37248979 | 37248993 | chr13 | 37633989 | 37634018 | chr13 | 37643942 | 37644005 |
| chr13 | 38402239 | 38402268 | chr13 | 38443618 | 38443715 | chr13 | 39261410 | 39261446 |
| chr13 | 40000498 | 40000528 | chr13 | 41346048 | 41346088 | chr13 | 41496324 | 41496478 |
| chr13 | 41884500 | 41884688 | chr13 | 43148669 | 43148698 | chr13 | 43566247 | 43566647 |
| chr13 | 43620862 | 43621006 | chr13 | 44947746 | 44948197 | chr13 | 45150013 | 45150276 |
| chr13 | 45885876 | 45885905 | chr13 | 45905088 | 45905264 | chr13 | 46425548 | 46425554 |
| chr13 | 46425576 | 46425584 | chr13 | 46649031 | 46649141 | chr13 | 46660839 | 46660869 |
| chr13 | 46961494 | 46961533 | chr13 | 46961952 | 46961982 | chr13 | 47407767 | 47407796 |
| chr13 | 47468139 | 47468168 | chr13 | 47472315 | 47472344 | chr13 | 47526030 | 47526182 |
| chr13 | 48478576 | 48478605 | chr13 | 48667877 | 48667907 | chr13 | 49794117 | 49794925 |
| chr13 | 50266473 | 50266573 | chr13 | 50367946 | 50368123 | chr13 | 50421504 | 50421696 |
| chr13 | 50639705 | 50639799 | chr13 | 52270145 | 52270175 | chr13 | 52565068 | 52565194 |
| chr13 | 52580318 | 52580369 | chr13 | 53312991 | 53313313 | chr13 | 53313513 | 53313612 |
| chr13 | 53313678 | 53313920 | chr13 | 53419734 | 53419775 | chr13 | 53420020 | 53420020 |
| chr13 | 53423838 | 53423978 | chr13 | 55146522 | 55146551 | chr13 | 55373897 | 55373926 |
| chr13 | 55628658 | 55628687 | chr13 | 56762456 | 56762485 | chr13 | 57714539 | 57714568 |
| chr13 | 58203602 | 58203644 | chr13 | 58203851 | 58204103 | chr13 | 58204350 | 58204395 |
| chr13 | 58206042 | 58206231 | chr13 | 58206453 | 58206771 | chr13 | 58206862 | 58206983 |
| chr13 | 58207568 | 58207813 | chr13 | 58207892 | 58208020 | chr13 | 58208495 | 58208926 |
| chr13 | 58892774 | 58892803 | chr13 | 59531686 | 59531715 | chr13 | 62132346 | 62132375 |
| chr13 | 64650200 | 64650229 | chr13 | 65532258 | 65532287 | chr13 | 66697959 | 66698124 |
| chr13 | 67196371 | 67196400 | chr13 | 67197158 | 67197187 | chr13 | 67803735 | 67804074 |
| chr13 | 67804494 | 67804523 | chr13 | 67805191 | 67805247 | chr13 | 68488923 | 68488952 |
| chr13 | 68682015 | 68682044 | chr13 | 68745282 | 68745311 | chr13 | 69796842 | 69796871 |
| chr13 | 70681626 | 70681777 | chr13 | 70681867 | 70682071 | chr13 | 71498386 | 71498415 |
| chr13 | 72439142 | 72439250 | chr13 | 73184723 | 73184752 | chr13 | 73336049 | 73336078 |
| chr13 | 73619660 | 73619784 | chr13 | 76440730 | 76440760 | chr13 | 76869421 | 76869450 |
| chr13 | 77553779 | 77553809 | chr13 | 78492684 | 78492840 | chr13 | 78493166 | 78493196 |
| chr13 | 78493455 | 78493809 | chr13 | 79168067 | 79168102 | chr13 | 79169850 | 79170113 |
| chr13 | 79170348 | 79170383 | chr13 | 79170468 | 79170884 | chr13 | 79171118 | 79171196 |
| chr13 | 79175770 | 79175943 | chr13 | 79176078 | 79176125 | chr13 | 79176277 | 79176420 |
| chr13 | 79176609 | 79176783 | chr13 | 79176993 | 79177184 | chr13 | 79177306 | 79177622 |
| chr13 | 79177886 | 79177998 | chr13 | 79183406 | 79183423 | chr13 | 79693095 | 79693124 |
| chr13 | 79993101 | 79993142 | chr13 | 81229343 | 81229372 | chr13 | 84455236 | 84455292 |
| chr13 | 84455581 | 84455715 | chr13 | 84457491 | 84457521 | chr13 | 82731371 | 87731400 |
| chr13 | 88323579 | 28323830 | chr13 | 88323868 | 88324207 | chr13 | 88324516 | 88324518 |
| chr13 | 88325300 | 88325460 | chr13 | 88325819 | 88326061 | chr13 | 88326538 | 88326707 |
| chr13 | 88326937 | 88327014 | chr13 | 88629123 | 88629152 | chr13 | 88788883 | 88788912 |
| chr13 | 88997906 | 88997935 | chr13 | 89815436 | 89815465 | chr13 | 90015503 | 90015532 |
| chr13 | 90015897 | 90015926 | chr13 | 91755723 | 91755837 | chr13 | 91948489 | 91948519 |
| chr13 | 92050760 | 92050814 | chr13 | 92051139 | 92051168 | chr13 | 92051374 | 92051513 |
| chr13 | 93869304 | 93859333 | chr13 | 93879288 | 93879375 | chr13 | 93879670 | 93879700 |
| chr13 | 93880089 | 93880216 | chr13 | 93880534 | 93880737 | chr13 | 93880794 | 93880856 |
| chr13 | 94107209 | 94107238 | chr13 | 95086143 | 95086172 | chr13 | 95357311 | 95357341 |
| chr13 | 95357574 | 95357775 | chr13 | 95358041 | 95358165 | chr13 | 95359747 | 95359803 |
| chr13 | 95360322 | 95360371 | chr13 | 95363210 | 95363429 | chr13 | 95363796 | 95363955 |
| chr13 | 95364065 | 95364196 | chr13 | 95364495 | 95364800 | chr13 | 95620021 | 95620078 |
| chr13 | 95620647 | 95620781 | chr13 | 95620854 | 95621011 | chr13 | 96031705 | 96031815 |
| chr13 | 96177285 | 96177315 | chr13 | 96204923 | 96205363 | chr13 | 96296225 | 96296345 |
| chr13 | 96296373 | 96296473 | chr13 | 96296841 | 96296949 | chr13 | 96296992 | 96297137 |
| chr13 | 96743788 | 96744175 | chr13 | 97761876 | 97761925 | chr13 | 99851676 | 99851706 |
| chr13 | 100547713 | 100547893 | chr13 | 100608462 | 100608804 | chr13 | 100608839 | 100609055 |
| chr13 | 100621941 | 100622015 | chr13 | 100624324 | 100624348 | chr13 | 100624587 | 100624729 |
| chr13 | 100626929 | 100627009 | chr13 | 100627295 | 100627348 | chr13 | 100627688 | 100627717 |
| chr13 | 100630169 | 100630298 | chr13 | 100630329 | 100630430 | chr13 | 100630630 | 100630997 |

TABLE 12-continued

| chr | start | end | chr | start | end | chr | start | end |
|---|---|---|---|---|---|---|---|---|
| chr13 | 100633089 | 100633184 | chr13 | 100634314 | 100634617 | chr13 | 100635406 | 100635451 |
| chr13 | 100636167 | 100636238 | chr13 | 100637390 | 100637485 | chr13 | 100641282 | 100641408 |
| chr13 | 100642120 | 100642201 | chr13 | 100643296 | 100643435 | chr13 | 100644055 | 100644179 |
| chr13 | 100649325 | 100649575 | chr13 | 100649800 | 100649884 | chr13 | 102197373 | 102197408 |
| chr13 | 102568454 | 102568484 | chr13 | 102569313 | 102569542 | chr13 | 103046721 | 103046995 |
| chr13 | 103062347 | 103052574 | chr13 | 103052892 | 103052940 | chr13 | 103053394 | 103053496 |
| chr13 | 103821419 | 103821448 | chr13 | 105484285 | 105484314 | chr13 | 106791875 | 105791904 |
| chr13 | 107186855 | 107186884 | chr13 | 107187162 | 107187426 | chr13 | 107187666 | 107187695 |
| chr13 | 107188241 | 107188430 | chr13 | 107827301 | 107827331 | chr13 | 108518813 | 108518933 |
| chr13 | 108519254 | 108519367 | chr13 | 108519737 | 108519745 | chr13 | 108520376 | 108520534 |
| chr13 | 108520979 | 108521076 | chr13 | 108816328 | 108816383 | chr13 | 108869613 | 108869830 |
| chr13 | 109147685 | 109147862 | chr13 | 109148155 | 109148278 | chr13 | 109148783 | 109149185 |
| chr13 | 110434451 | 110434593 | chr13 | 110958816 | 110958981 | chr13 | 110959753 | 110959970 |
| chr13 | 110960541 | 110960603 | chr13 | 111278255 | 111278426 | chr13 | 111363787 | 111363972 |
| chr13 | 112272991 | 112273088 | chr13 | 112707694 | 112707869 | chr13 | 112708308 | 112708513 |
| chr13 | 112709388 | 112709617 | chr13 | 112709883 | 112709928 | chr13 | 112710360 | 112710475 |
| chr13 | 112710759 | 112711293 | chr13 | 112711376 | 112711776 | chr13 | 112712017 | 112713029 |
| chr13 | 112715370 | 112715642 | chr13 | 112715985 | 112716313 | chr13 | 112716677 | 112716721 |
| chr13 | 112717026 | 112717242 | chr13 | 112717323 | 112717536 | chr13 | 112717835 | 112717949 |
| chr13 | 112720033 | 112720505 | chr13 | 112720723 | 112720767 | chr13 | 112721012 | 112721026 |
| chr13 | 112722129 | 112722220 | chr13 | 112722275 | 112722312 | chr13 | 112724505 | 112724535 |
| chr13 | 112726436 | 112726560 | chr13 | 112727984 | 112728200 | chr13 | 112758107 | 112758257 |
| chr13 | 112758274 | 112758372 | chr13 | 112758496 | 112758613 | chr13 | 112759112 | 112759248 |
| chr13 | 112759612 | 112759642 | chr13 | 112760007 | 112760322 | chr13 | 112760795 | 112761214 |
| chr13 | 113244509 | 113244595 | chr13 | 113598618 | 113598851 | chr13 | 113938542 | 113938603 |
| chr13 | 113985679 | 113986053 | chr13 | 114055983 | 114066137 | chr13 | 114060064 | 114060333 |
| chr13 | 114074768 | 114074853 | chr13 | 114082984 | 114083014 | chr13 | 114123168 | 114123291 |
| chr13 | 114189737 | 114189809 | chr13 | 114221622 | 114221652 | chr13 | 114304565 | 114304927 |
| chr13 | 114479404 | 114479434 | chr13 | 114498017 | 114498260 | chr13 | 114568046 | 114568076 |
| chr13 | 114748342 | 114748638 | chr13 | 114766270 | 114766300 | chr13 | 114780561 | 114781061 |
| chr13 | 114807617 | 114807815 | chr13 | 114855635 | 114855669 | chr13 | 114862308 | 114862368 |
| chr13 | 114897194 | 114897240 | chr13 | 114961823 | 114961933 | chr14 | 21093454 | 21093631 |
| chr14 | 21100748 | 21100778 | chr14 | 21100801 | 21100831 | chr14 | 22005029 | 22005073 |
| chr14 | 23234956 | 23235032 | chr14 | 23356044 | 23356384 | chr14 | 23400315 | 23400354 |
| chr14 | 23426755 | 23426785 | chr14 | 23701644 | 23701737 | chr14 | 23706727 | 23706755 |
| chr14 | 24562744 | 24562774 | chr14 | 24641010 | 24641215 | chr14 | 24803594 | 24804122 |
| chr14 | 25071566 | 25071612 | chr14 | 25155907 | 25155985 | chr14 | 26674354 | 26674384 |
| chr14 | 26674699 | 26674729 | chr14 | 27066562 | 27066785 | chr14 | 27067373 | 27067386 |
| chr14 | 29225531 | 29225561 | chr14 | 29226071 | 29226198 | chr14 | 29228654 | 29228778 |
| chr14 | 29229107 | 29229386 | chr14 | 29231071 | 29231185 | chr14 | 29231425 | 29231590 |
| chr14 | 29235003 | 29235308 | chr14 | 29235342 | 29235356 | chr14 | 29237063 | 29237066 |
| chr14 | 29242763 | 29242908 | chr14 | 29243516 | 29243669 | chr14 | 29243731 | 29243888 |
| chr14 | 29244224 | 29244308 | chr14 | 29247689 | 29247740 | chr14 | 29254612 | 29254713 |
| chr14 | 31027323 | 31027367 | chr14 | 31344346 | 31344549 | chr14 | 31925554 | 31925724 |
| chr14 | 32597620 | 32597657 | chr14 | 33402462 | 33402762 | chr14 | 33403045 | 33403316 |
| chr14 | 33403866 | 33404418 | chr14 | 34269897 | 34270004 | chr14 | 34420250 | 34420288 |
| chr14 | 35023111 | 35023322 | chr14 | 35024446 | 35024546 | chr14 | 35389907 | 35389943 |
| chr14 | 36003442 | 36003826 | chr14 | 36004081 | 36004493 | chr14 | 36004711 | 36004734 |
| chr14 | 36004822 | 36004921 | chr14 | 36972803 | 36972912 | chr14 | 36973455 | 36973538 |
| chr14 | 36974294 | 36974927 | chr14 | 36974968 | 36974982 | chr14 | 36975299 | 36975399 |
| chr14 | 36977645 | 36977929 | chr14 | 36977975 | 36978009 | chr14 | 36978548 | 36978578 |
| chr14 | 36979619 | 36979649 | chr14 | 36982927 | 36982969 | chr14 | 36983708 | 36984146 |
| chr14 | 36986841 | 36985871 | chr14 | 36986301 | 36986471 | chr14 | 36987302 | 36987685 |
| chr14 | 36987939 | 36988143 | chr14 | 36988428 | 36988460 | chr14 | 36990858 | 36991032 |
| chr14 | 36991095 | 36991177 | chr14 | 36991532 | 36991613 | chr14 | 36991989 | 36992163 |
| chr14 | 36992222 | 36992417 | chr14 | 36993473 | 36993487 | chr14 | 36993694 | 36993956 |
| chr14 | 36994248 | 36994999 | chr14 | 37050752 | 37050794 | chr14 | 37116105 | 37116294 |
| chr14 | 37117611 | 37117697 | chr14 | 37123438 | 37124077 | chr14 | 37124482 | 37124572 |
| chr14 | 37124992 | 37125545 | chr14 | 37126241 | 37126297 | chr14 | 37126566 | 37126713 |
| chr14 | 37127281 | 37127311 | chr14 | 37127655 | 37127779 | chr14 | 37128553 | 37128723 |
| chr14 | 37130077 | 37130260 | chr14 | 37132375 | 37132553 | chr14 | 37132603 | 37132652 |
| chr14 | 37133001 | 37133052 | chr14 | 37135784 | 37136017 | chr14 | 37136295 | 37136345 |
| chr14 | 37136588 | 37136618 | chr14 | 38060677 | 38060916 | chr14 | 38064401 | 38064549 |
| chr14 | 38677519 | 38677548 | chr14 | 38677761 | 38677790 | chr14 | 38724294 | 38724525 |
| chr14 | 38724979 | 38725258 | chr14 | 38725521 | 38725764 | chr14 | 39579800 | 39579830 |
| chr14 | 42074544 | 42074586 | chr14 | 42074669 | 42074987 | chr14 | 42075588 | 42076043 |
| chr14 | 42076106 | 42076212 | chr14 | 42076823 | 42076853 | chr14 | 42077230 | 42077268 |
| chr14 | 42077770 | 42077800 | chr14 | 42079289 | 42079328 | chr14 | 45602514 | 45602576 |
| chr14 | 48143798 | 48143957 | chr14 | 48144359 | 48144401 | chr14 | 48144699 | 48144763 |
| chr14 | 48145237 | 48145257 | chr14 | 50233426 | 50233459 | chr14 | 50333754 | 50333994 |
| chr14 | 50334254 | 50334355 | chr14 | 50355854 | 50355924 | chr14 | 50681598 | 50681859 |
| chr14 | 50777663 | 50777714 | chr14 | 51338730 | 51338731 | chr14 | 51660304 | 51560713 |
| chr14 | 51560771 | 51561428 | chr14 | 51561765 | 51562012 | chr14 | 51829264 | 51829596 |
| chr14 | 51955509 | 51955538 | chr14 | 52534648 | 52534791 | chr14 | 52535012 | 52535026 |
| chr14 | 52535056 | 52535263 | chr14 | 52535335 | 52536104 | chr14 | 52536343 | 52536404 |
| chr14 | 52734509 | 52734557 | chr14 | 52734777 | 52735001 | chr14 | 52735045 | 52735255 |
| chr14 | 52765920 | 52766075 | chr14 | 52781525 | 52781916 | chr14 | 54422651 | 54422925 |
| chr14 | 55370202 | 55370235 | chr14 | 55595938 | 55595968 | chr14 | 55668368 | 55668526 |

TABLE 12-continued

| chr | start | end | chr | start | end | chr | start | end |
|---|---|---|---|---|---|---|---|---|
| chr14 | 55765285 | 55765714 | chr14 | 55823079 | 55823218 | chr14 | 57045520 | 57045739 |
| chr14 | 57260946 | 57261094 | chr14 | 57261175 | 57261407 | chr14 | 57261466 | 57261821 |
| chr14 | 57262072 | 57262179 | chr14 | 57264079 | 57264645 | chr14 | 57264765 | 57264806 |
| chr14 | 57265148 | 57265240 | chr14 | 57270936 | 57270971 | chr14 | 57271154 | 57271266 |
| chr14 | 57272009 | 57272067 | chr14 | 57274486 | 57275049 | chr14 | 57275211 | 57275305 |
| chr14 | 57275596 | 57275685 | chr14 | 57276074 | 57276104 | chr14 | 57276440 | 57276666 |
| chr14 | 57277920 | 57278762 | chr14 | 57278838 | 57279564 | chr14 | 57279643 | 57279657 |
| chr14 | 57283314 | 57283408 | chr14 | 57283446 | 57284036 | chr14 | 57284071 | 57284659 |
| chr14 | 58332297 | 58332403 | chr14 | 58857094 | 58857355 | chr14 | 58893052 | 58893183 |
| chr14 | 59770326 | 59770452 | chr14 | 60097193 | 60097246 | chr14 | 60097402 | 60097566 |
| chr14 | 60386207 | 60386252 | chr14 | 60386638 | 60386701 | chr14 | 60794635 | 60794667 |
| chr14 | 60952196 | 60952419 | chr14 | 60952517 | 60952632 | chr14 | 60952730 | 60952959 |
| chr14 | 60973151 | 60973324 | chr14 | 60973697 | 60974007 | chr14 | 60974368 | 60974403 |
| chr14 | 60975384 | 60975888 | chr14 | 60976075 | 60976514 | chr14 | 60976813 | 60976860 |
| chr14 | 60977337 | 60977712 | chr14 | 60977880 | 60978147 | chr14 | 60981202 | 60981268 |
| chr14 | 60981676 | 60981793 | chr14 | 60982110 | 60982367 | chr14 | 60982574 | 60982622 |
| chr14 | 60982841 | 60982911 | chr14 | 51104291 | 61104556 | chr14 | 61104624 | 61104864 |
| chr14 | 61108620 | 61108996 | chr14 | 61109206 | 61109470 | chr14 | 61109839 | 61110243 |
| chr14 | 61114137 | 61114456 | chr14 | 61115311 | 61115517 | chr14 | 61118743 | 61118765 |
| chr14 | 61118965 | 61119136 | chr14 | 61119536 | 61119639 | chr14 | 61747389 | 61747527 |
| chr14 | 61747583 | 61748033 | chr14 | 62106193 | 62106242 | chr14 | 62279578 | 62279852 |
| chr14 | 62279899 | 62280006 | chr14 | 62583809 | 62583869 | chr14 | 63512100 | 63512291 |
| chr14 | 63512573 | 63512708 | chr14 | 63512741 | 63512816 | chr14 | 63513124 | 63513154 |
| chr14 | 64107335 | 64107600 | chr14 | 64222413 | 64222488 | chr14 | 65005696 | 65005833 |
| chr14 | 65008998 | 65009193 | chr14 | 65233339 | 65233464 | chr14 | 66498931 | 66498975 |
| chr14 | 67585164 | 67585413 | chr14 | 67886378 | 67886606 | chr14 | 68334928 | 68335108 |
| chr14 | 69014044 | 69014110 | chr14 | 69866541 | 69866706 | chr14 | 69867022 | 69867196 |
| chr14 | 70014723 | 70014974 | chr14 | 70038990 | 70039025 | chr14 | 70346136 | 70346491 |
| chr14 | 70554343 | 70654713 | chr14 | 70655530 | 70555889 | chr14 | 70655920 | 70656090 |
| chr14 | 72398743 | 72399019 | chr14 | 72399452 | 72399453 | chr14 | 72399929 | 72400029 |
| chr14 | 73167750 | 73167899 | chr14 | 73175026 | 73175148 | chr14 | 73178807 | 73178865 |
| chr14 | 73180208 | 73180314 | chr14 | 73226952 | 73227005 | chr14 | 73231266 | 73231414 |
| chr14 | 73236095 | 73236178 | chr14 | 73318471 | 73318629 | chr14 | 73333249 | 73333396 |
| chr14 | 73602250 | 73602389 | chr14 | 73604570 | 73604718 | chr14 | 73855616 | 73855646 |
| chr14 | 73956853 | 73956913 | chr14 | 74529109 | 74529139 | chr14 | 74706015 | 74706222 |
| chr14 | 74706941 | 74707544 | chr14 | 74707573 | 74707747 | chr14 | 74707792 | 74707873 |
| chr14 | 74708862 | 74708955 | chr14 | 74892540 | 74892569 | chr14 | 74893074 | 74893113 |
| chr14 | 75078170 | 75078242 | chr14 | 75760311 | 75760347 | chr14 | 75988341 | 75988370 |
| chr14 | 75988732 | 75988761 | chr14 | 76128674 | 76128842 | chr14 | 76604682 | 76604716 |
| chr14 | 76605072 | 76605376 | chr14 | 76843742 | 76843953 | chr14 | 77228121 | 77228159 |
| chr14 | 77606922 | 77607236 | chr14 | 77737212 | 77737814 | chr14 | 79745138 | 79745175 |
| chr14 | 85996479 | 85996608 | chr14 | 85996892 | 85996906 | chr14 | 85997821 | 85997925 |
| chr14 | 85998288 | 85998574 | chr14 | 85998630 | 85998683 | chr14 | 85999597 | 85999613 |
| chr14 | 86000270 | 86000511 | chr14 | 86000918 | 86001114 | chr14 | 88457599 | 88457685 |
| chr14 | 89817889 | 89818034 | chr14 | 90527714 | 90527758 | chr14 | 90983328 | 90983360 |
| chr14 | 91691163 | 91691306 | chr14 | 91691696 | 91691822 | chr14 | 91766154 | 91766450 |
| chr14 | 91780382 | 91780512 | chr14 | 91801036 | 91801164 | chr14 | 92507578 | 92507792 |
| chr14 | 92789512 | 92789542 | chr14 | 92789960 | 92790098 | chr14 | 92790637 | 92790703 |
| chr14 | 92979917 | 92979991 | chr14 | 93155061 | 93155315 | chr14 | 93389557 | 93389693 |
| chr14 | 93389713 | 93389776 | chr14 | 93571193 | 93571326 | chr14 | 93706752 | 93706782 |
| chr14 | 94254389 | 94254458 | chr14 | 94254499 | 94254513 | chr14 | 94405734 | 94405785 |
| chr14 | 94603542 | 94603670 | chr14 | 94889856 | 94889870 | chr14 | 95233705 | 95233765 |
| chr14 | 95234643 | 95234710 | chr14 | 95235026 | 95235369 | chr14 | 95235989 | 95236111 |
| chr14 | 95236524 | 95236553 | chr14 | 95236819 | 95236848 | chr14 | 95237622 | 95237642 |
| chr14 | 95239422 | 95239633 | chr14 | 95240127 | 95240157 | chr14 | 95240227 | 95240341 |
| chr14 | 95240392 | 95240422 | chr14 | 95557626 | 95557655 | chr14 | 95560448 | 95560477 |
| chr14 | 95740035 | 95740116 | chr14 | 96053974 | 96054020 | chr14 | 96342897 | 96343133 |
| chr14 | 96343404 | 96343433 | chr14 | 96343668 | 96343701 | chr14 | 97045354 | 97045431 |
| chr14 | 97058944 | 97059083 | chr14 | 97499277 | 97499315 | chr14 | 97499847 | 97499849 |
| chr14 | 97685044 | 97685288 | chr14 | 97685707 | 97685959 | chr14 | 99584575 | 99584664 |
| chr14 | 99712321 | 99712394 | chr14 | 99736151 | 99736183 | chr14 | 99737398 | 99737462 |
| chr14 | 100148073 | 100148230 | chr14 | 100437794 | 100437949 | chr14 | 100438705 | 100438811 |
| chr14 | 100643350 | 100643481 | chr14 | 100793556 | 100793650 | chr14 | 100843765 | 100843912 |
| chr14 | 101250109 | 101250222 | chr14 | 101506231 | 101506260 | chr14 | 101543868 | 101544235 |
| chr14 | 101923114 | 101923250 | chr14 | 101923600 | 101923686 | chr14 | 101924031 | 101924047 |
| chr14 | 101925049 | 101925071 | chr14 | 101925656 | 101925901 | chr14 | 102026360 | 102026484 |
| chr14 | 102026797 | 102026967 | chr14 | 102031236 | 102031271 | chr14 | 102031512 | 102031580 |
| chr14 | 102247912 | 102248214 | chr14 | 102418607 | 102418637 | chr14 | 102521602 | 102521758 |
| chr14 | 102529325 | 102529419 | chr14 | 102530007 | 102530234 | chr14 | 102530500 | 102530530 |
| chr14 | 102564464 | 102564605 | chr14 | 102682077 | 102682149 | chr14 | 102772607 | 102772695 |
| chr14 | 102973169 | 102973268 | chr14 | 103021391 | 103022003 | chr14 | 103394884 | 103395101 |
| chr14 | 103477643 | 103477794 | chr14 | 103655226 | 103655601 | chr14 | 103674078 | 103674079 |
| chr14 | 103687082 | 103687219 | chr14 | 103739967 | 103740150 | chr14 | 103740358 | 103740430 |
| chr14 | 103745699 | 103745750 | chr14 | 104160060 | 104160134 | chr14 | 104202705 | 104202759 |
| chr14 | 104355204 | 104355273 | chr14 | 104386476 | 104387067 | chr14 | 104547785 | 104547909 |
| chr14 | 104571985 | 104572116 | chr14 | 104601737 | 104601832 | chr14 | 104602033 | 104602063 |
| chr14 | 104605032 | 104605114 | chr14 | 104620411 | 104620554 | chr14 | 104627654 | 104627759 |
| chr14 | 104645125 | 104645188 | chr14 | 104646317 | 104646491 | chr14 | 104647257 | 104647287 |

TABLE 12-continued

| chr | start | end | chr | start | end | chr | start | end |
|---|---|---|---|---|---|---|---|---|
| chr14 | 104682545 | 104682656 | chr14 | 104862860 | 104863026 | chr14 | 104897228 | 104897294 |
| chr14 | 105071298 | 105071396 | chr14 | 105157485 | 105157554 | chr14 | 105239389 | 105239439 |
| chr14 | 105239793 | 105239825 | chr14 | 105241309 | 105241428 | chr14 | 105243032 | 105243064 |
| chr14 | 105246427 | 105246582 | chr14 | 105512063 | 105512395 | chr14 | 105658349 | 105658425 |
| chr14 | 105714258 | 105714334 | chr14 | 105714415 | 105714441 | chr14 | 105715248 | 105715392 |
| chr14 | 105830630 | 105830859 | chr14 | 105963655 | 105963772 | chr15 | 22822348 | 22822488 |
| chr15 | 23035709 | 23035781 | chr15 | 23158397 | 23158489 | chr15 | 23162337 | 23162372 |
| chr15 | 23273146 | 23273330 | chr15 | 23692316 | 23692453 | chr15 | 26107640 | 26107743 |
| chr15 | 26107846 | 26107860 | chr15 | 26108096 | 26108326 | chr15 | 26108549 | 26108701 |
| chr15 | 27212887 | 27213172 | chr15 | 27604062 | 27604123 | chr15 | 28341699 | 28342019 |
| chr15 | 28344173 | 28344187 | chr15 | 28344224 | 28344287 | chr15 | 28352240 | 28352421 |
| chr15 | 29027284 | 29077383 | chr15 | 29130807 | 29131047 | chr15 | 29131533 | 29131630 |
| chr15 | 29131756 | 29131875 | chr15 | 29396330 | 29396360 | chr15 | 29407777 | 29407813 |
| chr15 | 29407867 | 29408001 | chr15 | 29452432 | 29452462 | chr15 | 29862502 | 29862582 |
| chr15 | 30115185 | 30115228 | chr15 | 31455370 | 31455485 | chr15 | 31775596 | 31775637 |
| chr15 | 31775679 | 31775782 | chr15 | 32933918 | 32934018 | chr15 | 33009747 | 33009761 |
| chr15 | 33009822 | 33010675 | chr15 | 33010721 | 33011348 | chr15 | 33011601 | 33011633 |
| chr15 | 33487057 | 33487120 | chr15 | 33602801 | 33602886 | chr15 | 33603194 | 33603608 |
| chr15 | 33879242 | 33879272 | chr15 | 34517058 | 34517334 | chr15 | 34630439 | 34630449 |
| chr15 | 34630515 | 34630544 | chr15 | 34630818 | 34630865 | chr15 | 34729478 | 34729582 |
| chr15 | 34786504 | 34786943 | chr15 | 34787233 | 34787304 | chr15 | 34879708 | 34879866 |
| chr15 | 35046607 | 35046608 | chr15 | 35047034 | 35047133 | chr15 | 35087666 | 35087698 |
| chr15 | 35310631 | 35310868 | chr15 | 37180309 | 37180743 | chr15 | 37402974 | 37403086 |
| chr15 | 37403116 | 37403238 | chr15 | 40211819 | 40212190 | chr15 | 40575630 | 40575744 |
| chr15 | 40671495 | 40671620 | chr15 | 40675092 | 40675121 | chr15 | 40763811 | 40763862 |
| chr15 | 40782219 | 40782249 | chr15 | 40856224 | 40856254 | chr15 | 40877650 | 40877714 |
| chr15 | 41165245 | 41165700 | chr15 | 41541844 | 41541874 | chr15 | 41693679 | 41693794 |
| chr15 | 41708225 | 41708305 | chr15 | 41732398 | 41732471 | chr15 | 41804878 | 41805772 |
| chr15 | 41835548 | 41835720 | chr15 | 41913750 | 41913807 | chr15 | 41952572 | 41952711 |
| chr15 | 42749733 | 42749899 | chr15 | 42866975 | 42867049 | chr15 | 43551059 | 43551196 |
| chr15 | 43810405 | 43810435 | chr15 | 44037568 | 44037699 | chr15 | 45403636 | 45403680 |
| chr15 | 45403799 | 45403999 | chr15 | 45404103 | 45404130 | chr15 | 45404898 | 45405117 |
| chr15 | 45421385 | 45421435 | chr15 | 45421998 | 45422095 | chr15 | 45427370 | 45427410 |
| chr15 | 45427611 | 45427719 | chr15 | 45427772 | 45427786 | chr15 | 45444061 | 45444141 |
| chr15 | 45479460 | 45479516 | chr15 | 45493209 | 45493371 | chr15 | 45670462 | 45670838 |
| chr15 | 46021437 | 46021467 | chr15 | 47476118 | 47476239 | chr15 | 47476291 | 47476419 |
| chr15 | 47476877 | 47476980 | chr15 | 47477013 | 47477018 | chr15 | 48483956 | 48483986 |
| chr15 | 48936726 | 48937645 | chr15 | 48937710 | 48937987 | chr15 | 48938212 | 48938510 |
| chr15 | 50450454 | 50450574 | chr15 | 50464583 | 50464622 | chr15 | 51146606 | 51146636 |
| chr15 | 51385913 | 51386181 | chr15 | 51634075 | 51634135 | chr15 | 51973646 | 51973694 |
| chr15 | 51973764 | 51973934 | chr15 | 52000818 | 52000937 | chr15 | 53075809 | 53075864 |
| chr15 | 53075986 | 53077000 | chr15 | 53077066 | 53077361 | chr15 | 53077655 | 53077731 |
| chr15 | 53078064 | 53078236 | chr15 | 53079340 | 53079677 | chr15 | 53079718 | 53079891 |
| chr15 | 53079971 | 53080082 | chr15 | 53080337 | 53080606 | chr15 | 53080935 | 53080990 |
| chr15 | 53081399 | 53081677 | chr15 | 53082443 | 53082491 | chr15 | 53096815 | 53096891 |
| chr15 | 53097231 | 53097261 | chr15 | 53097778 | 53097906 | chr15 | 53098382 | 53098658 |
| chr15 | 54270498 | 54270707 | chr15 | 54270932 | 54270961 | chr15 | 54642236 | 54642352 |
| chr15 | 55452761 | 55452993 | chr15 | 55610440 | 55610698 | chr15 | 55699089 | 55699164 |
| chr15 | 55806758 | 55806900 | chr15 | 55880891 | 55881011 | chr15 | 56832508 | 56832546 |
| chr15 | 58357800 | 58357819 | chr15 | 59158488 | 59158537 | chr15 | 59158781 | 59158901 |
| chr15 | 59950198 | 59950363 | chr15 | 60084984 | 60085014 | chr15 | 60287038 | 60287585 |
| chr15 | 60287644 | 60287733 | chr15 | 60288786 | 60288844 | chr15 | 60289310 | 60289546 |
| chr15 | 60296122 | 60296209 | chr15 | 60296598 | 60296617 | chr15 | 60296861 | 60296923 |
| chr15 | 60297152 | 60297409 | chr15 | 60297637 | 60297826 | chr15 | 60297942 | 60298108 |
| chr15 | 60705106 | 60705204 | chr15 | 61520916 | 61521014 | chr15 | 61521659 | 61521937 |
| chr15 | 62456922 | 62456952 | chr15 | 64109724 | 64109788 | chr15 | 64618655 | 64618813 |
| chr15 | 64649481 | 64649553 | chr15 | 65118954 | 65118984 | chr15 | 65119265 | 65119295 |
| chr15 | 65119499 | 65119632 | chr15 | 65436137 | 65436213 | chr15 | 65669859 | 65669899 |
| chr15 | 65685591 | 65685708 | chr15 | 65823926 | 65824103 | chr15 | 65826189 | 65826359 |
| chr15 | 65862004 | 65862121 | chr15 | 66113240 | 66113270 | chr15 | 66649915 | 66649945 |
| chr15 | 66727409 | 66727498 | chr15 | 66729148 | 66729177 | chr15 | 66774117 | 66774203 |
| chr15 | 66789220 | 66789321 | chr15 | 66963816 | 66963871 | chr15 | 67146145 | 67146431 |
| chr15 | 67545536 | 67545566 | chr15 | 68112611 | 68112641 | chr15 | 68113868 | 68113898 |
| chr15 | 68114139 | 68114195 | chr15 | 68116369 | 68116621 | chr15 | 68117830 | 68118633 |
| chr15 | 68118930 | 68119174 | chr15 | 68119579 | 68120352 | chr15 | 68120827 | 68120857 |
| chr15 | 68121150 | 68121957 | chr15 | 68122643 | 68122673 | chr15 | 68125261 | 68125664 |
| chr15 | 68127801 | 68128350 | chr15 | 68128594 | 68128688 | chr15 | 68260519 | 68260709 |
| chr15 | 71055636 | 71055815 | chr15 | 72411929 | 72412176 | chr15 | 72612540 | 72612906 |
| chr15 | 72743741 | 72743796 | chr15 | 72979757 | 72979873 | chr15 | 73660004 | 73660067 |
| chr15 | 73661469 | 73661666 | chr15 | 74045075 | 74045097 | chr15 | 74422006 | 74422146 |
| chr15 | 74422869 | 74423002 | chr15 | 74658151 | 74658396 | chr15 | 74658502 | 74658587 |
| chr15 | 74686021 | 74686051 | chr15 | 74818772 | 74818806 | chr15 | 74903896 | 74903926 |
| chr15 | 74906463 | 74906493 | chr15 | 75205413 | 75205481 | chr15 | 75251346 | 75251382 |
| chr15 | 75251672 | 75251786 | chr15 | 75412459 | 75412714 | chr15 | 76627508 | 76627536 |
| chr15 | 76527576 | 76627826 | chr15 | 76629163 | 76529220 | chr15 | 76629494 | 76629531 |
| chr15 | 76629814 | 76630124 | chr15 | 76630520 | 76630847 | chr15 | 76638472 | 76638496 |
| chr15 | 77448873 | 77449001 | chr15 | 78111196 | 78111210 | chr15 | 78501806 | 78501942 |
| chr15 | 78556819 | 78557108 | chr15 | 78595791 | 78596218 | chr15 | 78632727 | 78632823 |

TABLE 12-continued

| chr | start | end | chr | start | end | chr | start | end |
|---|---|---|---|---|---|---|---|---|
| chr15 | 78859435 | 78859603 | chr15 | 78912281 | 78912371 | chr15 | 78912623 | 78912653 |
| chr15 | 78912912 | 78913027 | chr15 | 78913095 | 78913170 | chr15 | 78913535 | 78913651 |
| chr15 | 79104217 | 79104246 | chr15 | 79104466 | 79104495 | chr15 | 79151898 | 79152007 |
| chr15 | 79381705 | 79381745 | chr15 | 79382099 | 79382571 | chr15 | 79382786 | 79383257 |
| chr15 | 79383947 | 79383977 | chr15 | 79502211 | 79502360 | chr15 | 79575278 | 79575474 |
| chr15 | 79576145 | 79576277 | chr15 | 79724502 | 79724560 | chr15 | 79724607 | 79724792 |
| chr15 | 79724864 | 79725140 | chr15 | 79725422 | 79725539 | chr15 | 80216803 | 80216884 |
| chr15 | 81071827 | 81071867 | chr15 | 82336879 | 82336972 | chr15 | 82340070 | 82340157 |
| chr15 | 83314048 | 83314106 | chr15 | 83315336 | 83315393 | chr15 | 83316251 | 83317087 |
| chr15 | 83349234 | 83349611 | chr15 | 83349672 | 83349686 | chr15 | 83378212 | 83378370 |
| chr15 | 83622512 | 83622565 | chr15 | 83655843 | 83655934 | chr15 | 83776255 | 83776306 |
| chr15 | 83776333 | 83776716 | chr15 | 83776769 | 83776785 | chr15 | 83866523 | 83866559 |
| chr15 | 83875648 | 83875665 | chr15 | 83875706 | 83875901 | chr15 | 83877055 | 83877149 |
| chr15 | 83953884 | 83953903 | chr15 | 83954380 | 83964409 | chr15 | 84115747 | 84115853 |
| chr15 | 84115932 | 84115966 | chr15 | 84116105 | 84116949 | chr15 | 84322994 | 84323037 |
| chr15 | 84711204 | 84711367 | chr15 | 84748578 | 84748619 | chr15 | 84748679 | 84749260 |
| chr15 | 85142994 | 85143054 | chr15 | 85886518 | 85886604 | chr15 | 86002524 | 86002690 |
| chr15 | 88798725 | 88798791 | chr15 | 88799537 | 88800301 | chr15 | 88800541 | 88801008 |
| chr15 | 88801089 | 88801103 | chr15 | 89149169 | 89149448 | chr15 | 89248753 | 89248907 |
| chr15 | 89346050 | 89346326 | chr15 | 89346347 | 89346393 | chr15 | 89346670 | 89346793 |
| chr15 | 89346882 | 89346943 | chr15 | 89903484 | 89903814 | chr15 | 89910521 | 89910748 |
| chr15 | 89911087 | 89911186 | chr15 | 89913750 | 89913780 | chr15 | 89914231 | 89914449 |
| chr15 | 89914867 | 89914895 | chr15 | 89915240 | 89915369 | chr15 | 89921956 | 89922006 |
| chr15 | 89922500 | 89922546 | chr15 | 89942755 | 89942945 | chr15 | 89943410 | 89943706 |
| chr15 | 89949617 | 89949942 | chr15 | 89950236 | 89950736 | chr15 | 89951082 | 89951113 |
| chr15 | 89951466 | 89951801 | chr15 | 89952153 | 89952452 | chr15 | 89952700 | 89953055 |
| chr15 | 89954197 | 89954335 | chr15 | 89956423 | 89956450 | chr15 | 90039563 | 90039711 |
| chr15 | 90631823 | 90631948 | chr15 | 90667461 | 90667586 | chr15 | 90703262 | 90703345 |
| chr15 | 90755916 | 90756079 | chr15 | 91643360 | 91643586 | chr15 | 92936290 | 92936322 |
| chr15 | 92937153 | 92937374 | chr15 | 92937927 | 92938060 | chr15 | 92938123 | 92938293 |
| chr15 | 93158592 | 93158739 | chr15 | 93350668 | 93350698 | chr15 | 93364552 | 93364624 |
| chr15 | 93631739 | 93632014 | chr15 | 93632660 | 93633233 | chr15 | 94347602 | 94347632 |
| chr15 | 96874362 | 96874514 | chr15 | 96889154 | 96889183 | chr15 | 96889401 | 96889430 |
| chr15 | 96897934 | 96898010 | chr15 | 96911559 | 96911691 | chr15 | 96952696 | 96953098 |
| chr15 | 96953132 | 96953209 | chr15 | 96959730 | 96959960 | chr15 | 96960376 | 96960409 |
| chr15 | 96960732 | 96960826 | chr15 | 97006372 | 97006533 | chr15 | 98504114 | 98504144 |
| chr15 | 98634851 | 98634949 | chr15 | 98776762 | 98776792 | chr15 | 98836178 | 98836393 |
| chr15 | 98964786 | 98965138 | chr15 | 99193206 | 99193480 | chr15 | 99193914 | 99194186 |
| chr15 | 99254040 | 99254208 | chr15 | 99295692 | 99295749 | chr15 | 99346861 | 99347040 |
| chr15 | 99354999 | 99355041 | chr15 | 99453230 | 99453440 | chr15 | 99456299 | 99456329 |
| chr15 | 99497059 | 99497132 | chr15 | 100274325 | 100274385 | chr15 | 100339980 | 100340010 |
| chr15 | 100913423 | 100913595 | chr15 | 101420521 | 101420610 | chr15 | 101420972 | 101420989 |
| chr15 | 101818327 | 101818357 | chr15 | 102115873 | 102115905 | chr15 | 102193587 | 102193713 |
| chr15 | 102286533 | 102286563 | chr16 | 93831 | 93932 | chr16 | 142649 | 142783 |
| chr16 | 189744 | 189933 | chr16 | 199886 | 199943 | chr16 | 215416 | 215872 |
| chr16 | 215913 | 216224 | chr16 | 216676 | 217036 | chr16 | 230265 | 230315 |
| chr16 | 230497 | 230610 | chr16 | 232136 | 232166 | chr16 | 280323 | 280395 |
| chr16 | 318104 | 318227 | chr16 | 318498 | 318763 | chr16 | 337599 | 337659 |
| chr16 | 410377 | 410407 | chr16 | 565492 | 565623 | chr16 | 571714 | 571959 |
| chr16 | 611385 | 611520 | chr16 | 611969 | 612260 | chr16 | 612869 | 613037 |
| chr16 | 667141 | 667297 | chr16 | 667547 | 667622 | chr16 | 667876 | 668074 |
| chr16 | 672730 | 672806 | chr16 | 677972 | 678084 | chr16 | 700299 | 700329 |
| chr16 | 726626 | 726990 | chr16 | 731488 | 731610 | chr16 | 735205 | 735594 |
| chr16 | 740791 | 740914 | chr16 | 741376 | 741601 | chr16 | 762523 | 762694 |
| chr16 | 837361 | 837460 | chr16 | 845955 | 845985 | chr16 | 882484 | 882588 |
| chr16 | 895093 | 895166 | chr16 | 943481 | 943553 | chr16 | 1018120 | 1018150 |
| chr16 | 1019640 | 1019685 | chr16 | 1030444 | 1030655 | chr16 | 1052587 | 1052627 |
| chr16 | 1102927 | 1102957 | chr16 | 1116661 | 1116691 | chr16 | 1122858 | 1122946 |
| chr16 | 1129011 | 1129140 | chr16 | 1155162 | 1155212 | chr16 | 1186809 | 1186850 |
| chr16 | 1204003 | 1204034 | chr16 | 1217307 | 1217503 | chr16 | 1218034 | 1218090 |
| chr16 | 1228804 | 1228916 | chr16 | 1229970 | 1230142 | chr16 | 1248604 | 1248675 |
| chr16 | 1267925 | 1268120 | chr16 | 1271546 | 1271646 | chr16 | 1312526 | 1312611 |
| chr16 | 1323976 | 1324061 | chr16 | 1382901 | 1382940 | chr16 | 1394502 | 1394596 |
| chr16 | 1397454 | 1397484 | chr16 | 1407370 | 1407846 | chr16 | 1408210 | 1408240 |
| chr16 | 1428508 | 1428873 | chr16 | 1466425 | 1466455 | chr16 | 1469334 | 1469527 |
| chr16 | 1491567 | 1491613 | chr16 | 1523925 | 1523971 | chr16 | 1704656 | 1704800 |
| chr16 | 1729868 | 1730022 | chr16 | 1730306 | 1730597 | chr16 | 1741853 | 1742079 |
| chr16 | 1750769 | 1750907 | chr16 | 1842490 | 1842519 | chr16 | 1993818 | 1993848 |
| chr16 | 2029072 | 2029137 | chr16 | 2040914 | 2040960 | chr16 | 2040981 | 2041512 |
| chr16 | 2041582 | 2042160 | chr16 | 2042875 | 2042905 | chr16 | 2086831 | 2086860 |
| chr16 | 2106703 | 2106732 | chr16 | 2111966 | 2111995 | chr16 | 2120515 | 2120544 |
| chr16 | 2122243 | 2122272 | chr16 | 2124205 | 2124348 | chr16 | 2126080 | 2126109 |
| chr16 | 2128577 | 2129581 | chr16 | 2130361 | 2130390 | chr16 | 2132244 | 2132315 |
| chr16 | 2135301 | 2135330 | chr16 | 2136228 | 2136257 | chr16 | 2136727 | 2136855 |
| chr16 | 2140403 | 2140438 | chr16 | 2141909 | 2141972 | chr16 | 2142546 | 2142628 |
| chr16 | 2213313 | 2213343 | chr16 | 2232745 | 2233003 | chr16 | 2234726 | 2235020 |
| chr16 | 2275129 | 2275182 | chr16 | 2281249 | 2281314 | chr16 | 2287295 | 2287370 |
| chr16 | 2466225 | 2466307 | chr16 | 2485858 | 2485917 | chr16 | 2508414 | 2508453 |

TABLE 12-continued

| chr | start | end | chr | start | end | chr | start | end |
|---|---|---|---|---|---|---|---|---|
| chr16 | 2531069 | 2531177 | chr16 | 2731530 | 2731560 | chr16 | 2764377 | 2764470 |
| chr16 | 2770122 | 2770602 | chr16 | 2818101 | 2818156 | chr16 | 2892542 | 2892602 |
| chr16 | 2892627 | 2892729 | chr16 | 2956451 | 2956670 | chr16 | 2974601 | 2974650 |
| chr16 | 3017157 | 3017430 | chr16 | 3068171 | 3068201 | chr16 | 3151127 | 3151186 |
| chr16 | 3211708 | 3212019 | chr16 | 3220591 | 3220892 | chr16 | 3221142 | 3221700 |
| chr16 | 3221787 | 3222239 | chr16 | 3225471 | 3225607 | chr16 | 3232739 | 3233016 |
| chr16 | 3233199 | 3233330 | chr16 | 3233435 | 3234103 | chr16 | 3234165 | 3234452 |
| chr16 | 3237857 | 3238546 | chr16 | 3238993 | 3239848 | chr16 | 3241549 | 3241663 |
| chr16 | 3241936 | 3241966 | chr16 | 3269249 | 3269350 | chr16 | 3284117 | 3284147 |
| chr16 | 3355279 | 3355718 | chr16 | 3492583 | 3492675 | chr16 | 3598920 | 3598953 |
| chr16 | 3696694 | 3696724 | chr16 | 3802981 | 3803074 | chr16 | 3950127 | 3950279 |
| chr16 | 4264529 | 4264694 | chr16 | 4303144 | 4303174 | chr16 | 4310735 | 4310847 |
| chr16 | 4431126 | 4431189 | chr16 | 4431487 | 4431516 | chr16 | 4731638 | 4731718 |
| chr16 | 4733166 | 4733195 | chr16 | 4738567 | 4738680 | chr16 | 4751554 | 4751583 |
| chr16 | 4783226 | 4783375 | chr16 | 4846136 | 4846514 | chr16 | 4887144 | 4887244 |
| chr16 | 5037900 | 5038004 | chr16 | 5541116 | 5541158 | chr16 | 6035056 | 6035208 |
| chr16 | 6069941 | 6070019 | chr16 | 7354634 | 7354652 | chr16 | 7382499 | 7382534 |
| chr16 | 7525361 | 7525531 | chr16 | 8781032 | 8781177 | chr16 | 8870353 | 8870383 |
| chr16 | 9009860 | 9009989 | chr16 | 10274399 | 10274429 | chr16 | 10275308 | 10275392 |
| chr16 | 10275752 | 10275948 | chr16 | 10276360 | 10277050 | chr16 | 10277072 | 10277437 |
| chr16 | 10479815 | 10479980 | chr16 | 11242000 | 11242138 | chr16 | 11427659 | 11427732 |
| chr16 | 11490632 | 11490662 | chr16 | 11923005 | 11923035 | chr16 | 12011258 | 12011325 |
| chr16 | 12011940 | 12012073 | chr16 | 12066767 | 12066806 | chr16 | 12210772 | 12210896 |
| chr16 | 12211279 | 12211416 | chr16 | 12530169 | 12530199 | chr16 | 12971776 | 12971934 |
| chr16 | 12994459 | 12994737 | chr16 | 12995062 | 12995593 | chr16 | 12995803 | 12995803 |
| chr16 | 12996074 | 12996328 | chr16 | 12996617 | 12996720 | chr16 | 12996948 | 12997011 |
| chr16 | 12997386 | 12997703 | chr16 | 14021974 | 14022003 | chr16 | 14041504 | 14041533 |
| chr16 | 14041795 | 14041824 | chr16 | 14042062 | 14042091 | chr16 | 14189948 | 14190069 |
| chr16 | 14724632 | 14724736 | chr16 | 14725842 | 14726005 | chr16 | 15489599 | 15489808 |
| chr16 | 15708247 | 15708309 | chr16 | 15738905 | 15739042 | chr16 | 15820825 | 15820865 |
| chr16 | 16868746 | 16868905 | chr16 | 18163245 | 18163352 | chr16 | 18802250 | 18802680 |
| chr16 | 18950928 | 18951018 | chr16 | 19430908 | 19430949 | chr16 | 19531564 | 19531697 |
| chr16 | 19567202 | 19567449 | chr16 | 19895125 | 19895155 | chr16 | 21541606 | 21541636 |
| chr16 | 21665540 | 21665570 | chr16 | 21666641 | 21666771 | chr16 | 21674664 | 21674777 |
| chr16 | 21831621 | 21831957 | chr16 | 21839328 | 21839470 | chr16 | 22300599 | 22300637 |
| chr16 | 22326397 | 22326422 | chr16 | 22824701 | 22825076 | chr16 | 27825327 | 22825469 |
| chr16 | 22825886 | 22826081 | chr16 | 23313464 | 23313522 | chr16 | 23313780 | 23313836 |
| chr16 | 23706412 | 23706520 | chr16 | 23766097 | 23766130 | chr16 | 23847311 | 23847511 |
| chr16 | 23847789 | 23847874 | chr16 | 23847934 | 23847956 | chr16 | 24127251 | 24127338 |
| chr16 | 24172241 | 24172271 | chr16 | 24180710 | 24180760 | chr16 | 24267115 | 24267144 |
| chr16 | 24267485 | 24267578 | chr16 | 24415106 | 24415176 | chr16 | 25266537 | 25266573 |
| chr16 | 25542301 | 25542452 | chr16 | 25551107 | 25551264 | chr16 | 25702955 | 25702992 |
| chr16 | 25703642 | 25704122 | chr16 | 25704390 | 25704628 | chr16 | 25921574 | 25921604 |
| chr16 | 26302585 | 26302619 | chr16 | 26664739 | 26664775 | chr16 | 27207774 | 27207852 |
| chr16 | 27459938 | 27460074 | chr16 | 27749857 | 27750033 | chr16 | 27961122 | 27961254 |
| chr16 | 28074176 | 28074254 | chr16 | 28074418 | 28074684 | chr16 | 28074959 | 28075197 |
| chr16 | 28093825 | 28093866 | chr16 | 28224516 | 28224546 | chr16 | 28491774 | 28491924 |
| chr16 | 28560309 | 28560381 | chr16 | 28823157 | 28823459 | chr16 | 28850998 | 28851028 |
| chr16 | 28877839 | 28877883 | chr16 | 28891040 | 28891072 | chr16 | 29119008 | 29119058 |
| chr16 | 29153284 | 29153356 | chr16 | 29244900 | 29244997 | chr16 | 29830871 | 29831078 |
| chr16 | 29888624 | 29888658 | chr16 | 29936211 | 29936272 | chr16 | 30017330 | 30017442 |
| chr16 | 30065485 | 30065525 | chr16 | 30085867 | 30085995 | chr16 | 30116285 | 30116315 |
| chr16 | 30124691 | 30124861 | chr16 | 30169925 | 30170103 | chr16 | 30388542 | 30388574 |
| chr16 | 30402082 | 30402112 | chr16 | 30609373 | 30609408 | chr16 | 30639693 | 30639735 |
| chr16 | 30804321 | 30804472 | chr16 | 30826334 | 30826509 | chr16 | 30907010 | 30907148 |
| chr16 | 31227914 | 31228313 | chr16 | 31384593 | 31384623 | chr16 | 31446830 | 31447096 |
| chr16 | 31498008 | 31498165 | chr16 | 31500544 | 31500673 | chr16 | 31580560 | 31581036 |
| chr16 | 46569239 | 46569474 | chr16 | 46721567 | 46721707 | chr16 | 46803280 | 46803355 |
| chr16 | 47177525 | 47177606 | chr16 | 48450544 | 48450574 | chr16 | 48641663 | 48641693 |
| chr16 | 48642149 | 48642179 | chr16 | 48845120 | 48845125 | chr16 | 49309170 | 49309262 |
| chr16 | 49311523 | 49311989 | chr16 | 49312033 | 49312299 | chr16 | 49313363 | 49313710 |
| chr16 | 49314022 | 49314118 | chr16 | 49314419 | 49314561 | chr16 | 49314784 | 49314821 |
| chr16 | 49315276 | 49315306 | chr16 | 49315919 | 49316315 | chr16 | 49316509 | 49316580 |
| chr16 | 49638060 | 49638090 | chr16 | 50335767 | 50335797 | chr16 | 51183964 | 51184406 |
| chr16 | 51184807 | 51184957 | chr16 | 51185055 | 51185291 | chr16 | 51185844 | 51185964 |
| chr16 | 51186026 | 51186280 | chr16 | 51186596 | 51186939 | chr16 | 51188697 | 51188711 |
| chr16 | 51189922 | 51190037 | chr16 | 51190122 | 51190215 | chr16 | 53447826 | 53448002 |
| chr16 | 53467271 | 53467395 | chr16 | 53563622 | 53563654 | chr16 | 54128645 | 54128713 |
| chr16 | 54318898 | 54318988 | chr16 | 54319420 | 54319468 | chr16 | 54321638 | 54321818 |
| chr16 | 54324999 | 54325131 | chr16 | 54628691 | 54628867 | chr16 | 54964948 | 54965114 |
| chr16 | 54966830 | 54967264 | chr16 | 54971400 | 54971430 | chr16 | 55090666 | 55090861 |
| chr16 | 55357926 | 55357940 | chr16 | 55357992 | 55358086 | chr16 | 55358316 | 55358350 |
| chr16 | 55358798 | 55359071 | chr16 | 55363009 | 55363223 | chr16 | 55364716 | 55364843 |
| chr16 | 55365103 | 55365218 | chr16 | 55404999 | 55405214 | chr16 | 55689886 | 55689915 |
| chr16 | 55690115 | 55690379 | chr16 | 55690454 | 55690576 | chr16 | 55690762 | 55690809 |
| chr16 | 56224557 | 56224832 | chr16 | 56228370 | 56228416 | chr16 | 56228578 | 56228581 |
| chr16 | 56651094 | 56651123 | chr16 | 56651239 | 56651275 | chr16 | 56659175 | 56659673 |
| chr16 | 56672158 | 56672172 | chr16 | 56672222 | 56672385 | chr16 | 56672514 | 56672654 |

TABLE 12-continued

| chr | start | end | chr | start | end | chr | start | end |
|---|---|---|---|---|---|---|---|---|
| chr16 | 56672656 | 56672685 | chr16 | 56709837 | 56709892 | chr16 | 56709950 | 56710030 |
| chr16 | 57222663 | 57222709 | chr16 | 57318379 | 57318412 | chr16 | 57326422 | 57326613 |
| chr16 | 57935454 | 57935605 | chr16 | 58018634 | 58018845 | chr16 | 58019225 | 58019430 |
| chr16 | 58120795 | 58120961 | chr16 | 58427501 | 58427542 | chr16 | 58497221 | 58497335 |
| chr16 | 58497752 | 58497829 | chr16 | 58498175 | 58498204 | chr16 | 58498570 | 58498724 |
| chr16 | 58521708 | 58621737 | chr16 | 58534666 | 58534695 | chr16 | 58545487 | 58345516 |
| chr16 | 58550489 | 58550519 | chr16 | 58969757 | 38969792 | chr16 | 62068463 | 62068517 |
| chr16 | 62068952 | 62068982 | chr16 | 62070743 | 62070773 | chr16 | 65154933 | 65155091 |
| chr16 | 65156385 | 65156489 | chr16 | 66461786 | 66461840 | chr16 | 66612882 | 66613095 |
| chr16 | 66613335 | 66613369 | chr16 | 66863917 | 66863959 | chr16 | 67197698 | 67197769 |
| chr16 | 67198009 | 67198039 | chr16 | 67198917 | 67198957 | chr16 | 67241204 | 67241234 |
| chr16 | 67313865 | 67313895 | chr16 | 67850955 | 67850985 | chr16 | 67871102 | 67871134 |
| chr16 | 68481486 | 68481543 | chr16 | 68482808 | 68482941 | chr16 | 68544259 | 68544378 |
| chr16 | 68676408 | 68676604 | chr16 | 68676842 | 68676984 | chr16 | 68770755 | 68771298 |
| chr16 | 68844158 | 68844187 | chr16 | 68846033 | 68846042 | chr16 | 58856078 | 68856107 |
| chr16 | 68876782 | 68876996 | chr16 | 59026784 | 69026814 | chr16 | 69564118 | 69564200 |
| chr16 | 69969260 | 69969290 | chr16 | 70489585 | 70489681 | chr16 | 70595535 | 70595700 |
| chr16 | 70794492 | 70794633 | chr16 | 71460027 | 71460088 | chr16 | 71460271 | 71460351 |
| chr16 | 71507759 | 71507791 | chr16 | 71677557 | 71627661 | chr16 | 71715779 | 71715809 |
| chr16 | 71918889 | 71919024 | chr16 | 72957763 | 72957795 | chr16 | 74886148 | 74886268 |
| chr16 | 74901594 | 74901659 | chr16 | 75019751 | 75019781 | chr16 | 75549798 | 75549836 |
| chr16 | 76008985 | 76009154 | chr16 | 77247440 | 77247470 | chr16 | 77468261 | 77468457 |
| chr16 | 77822589 | 77822874 | chr16 | 78079969 | 78080054 | chr16 | 79623602 | 79623616 |
| chr16 | 79623798 | 79623914 | chr16 | 80837962 | 80838143 | chr16 | 80966399 | 80966431 |
| chr16 | 81564199 | 81564229 | chr16 | 81929362 | 81929392 | chr16 | 81946245 | 81946275 |
| chr16 | 81962167 | 81962195 | chr16 | 82660360 | 82660496 | chr16 | 82660712 | 82660741 |
| chr16 | 84074836 | 84074871 | chr16 | 84153364 | 84153394 | chr16 | 84402244 | 84402319 |
| chr16 | 84519974 | 84520010 | chr16 | 84651793 | 84651822 | chr16 | 84823626 | 84823656 |
| chr16 | 84853288 | 84853376 | chr16 | 85075434 | 85075553 | chr16 | 85317850 | 85317882 |
| chr16 | 85485747 | 85485855 | chr16 | 85497445 | 85497475 | chr16 | 85517345 | 85517521 |
| chr16 | 85651520 | 85651550 | chr16 | 85678639 | 85678761 | chr16 | 85684308 | 85684457 |
| chr16 | 85699689 | 85699921 | chr16 | 85834460 | 85834495 | chr16 | 85932828 | 85932858 |
| chr16 | 86320354 | 86320391 | chr16 | 86320755 | 86320800 | chr16 | 86321020 | 86321068 |
| chr16 | 86530947 | 86530992 | chr16 | 86531017 | 86531046 | chr16 | 86531375 | 86531480 |
| chr16 | 86531528 | 86531573 | chr16 | 86541591 | 86541968 | chr16 | 86542373 | 86542457 |
| chr16 | 86544191 | 86544557 | chr16 | 86571984 | 86572014 | chr16 | 86599481 | 86599844 |
| chr16 | 86600483 | 86600686 | chr16 | 86600958 | 86601015 | chr16 | 86601286 | 86601539 |
| chr16 | 86602038 | 86602514 | chr16 | 86878150 | 86878180 | chr16 | 87092439 | 87092553 |
| chr16 | 87525622 | 87525701 | chr16 | 87635103 | 87635133 | chr16 | 87636627 | 87636907 |
| chr16 | 87714272 | 87714381 | chr16 | 87723735 | 87724098 | chr16 | 88007072 | 88007108 |
| chr16 | 88106322 | 88106398 | chr16 | 88164401 | 88164468 | chr16 | 88498241 | 88498760 |
| chr16 | 88504058 | 88504315 | chr16 | 88506346 | 88506526 | chr16 | 88512427 | 88512529 |
| chr16 | 88543428 | 88543458 | chr16 | 88550263 | 88550483 | chr16 | 88603696 | 88603760 |
| chr16 | 88623960 | 88624167 | chr16 | 88711337 | 88711507 | chr16 | 88757466 | 88757496 |
| chr16 | 88879949 | 88880124 | chr16 | 88883238 | 88883377 | chr16 | 88941058 | 88941141 |
| chr16 | 88942119 | 88942160 | chr16 | 88943559 | 88944024 | chr16 | 88945815 | 88945995 |
| chr16 | 88955249 | 88955368 | chr16 | 88956230 | 88956399 | chr16 | 88957350 | 88957857 |
| chr16 | 88958397 | 88958431 | chr16 | 88963277 | 88963763 | chr16 | 88966303 | 88966588 |
| chr16 | 88968709 | 88968789 | chr16 | 88978024 | 88978072 | chr16 | 88993078 | 88993230 |
| chr16 | 88999617 | 88999647 | chr16 | 89000168 | 89000204 | chr16 | 89001094 | 89001124 |
| chr16 | 89007520 | 89007558 | chr16 | 89007880 | 89007995 | chr16 | 89008552 | 89008592 |
| chr16 | 89047717 | 89047747 | chr16 | 89072503 | 89072774 | chr16 | 89086109 | 89086917 |
| chr16 | 89107675 | 89107732 | chr16 | 89109385 | 89109415 | chr16 | 89120038 | 89120319 |
| chr16 | 89120708 | 89120864 | chr16 | 89138016 | 89138060 | chr16 | 89220327 | 89220398 |
| chr16 | 89220655 | 89220922 | chr16 | 89240843 | 89240873 | chr16 | 89254653 | 89254830 |
| chr16 | 89267334 | 89267364 | chr16 | 89267808 | 89267824 | chr16 | 89558610 | 89558703 |
| chr16 | 89575728 | 89575861 | chr16 | 89584136 | 89584417 | chr16 | 89676025 | 89676197 |
| chr16 | 89883972 | 89884185 | chr16 | 89884966 | 89885142 | chr16 | 89900124 | 89900180 |
| chr16 | 89900455 | 89900526 | chr16 | 90115428 | 90115458 | chr17 | 415134 | 415163 |
| chr17 | 556252 | 556282 | chr17 | 617001 | 617064 | chr17 | 631704 | 631734 |
| chr17 | 1082884 | 1083002 | chr17 | 1136593 | 1136653 | chr17 | 1174274 | 1174361 |
| chr17 | 1174385 | 1174413 | chr17 | 1494550 | 1494613 | chr17 | 1536116 | 1536145 |
| chr17 | 1545976 | 1546442 | chr17 | 1623703 | 1623735 | chr17 | 1959468 | 1959520 |
| chr17 | 2207718 | 2208063 | chr17 | 2219952 | 2220319 | chr17 | 2220564 | 2221059 |
| chr17 | 2250051 | 2250081 | chr17 | 2278801 | 2278925 | chr17 | 2496019 | 2496049 |
| chr17 | 2538269 | 2538337 | chr17 | 2607905 | 2607986 | chr17 | 2663898 | 2664032 |
| chr17 | 2811362 | 2811392 | chr17 | 2873476 | 2873551 | chr17 | 2950959 | 2951091 |
| chr17 | 3438914 | 3438937 | chr17 | 3657502 | 3657553 | chr17 | 3658490 | 3658519 |
| chr17 | 3658849 | 3659011 | chr17 | 4544607 | 4544710 | chr17 | 4693354 | 4693388 |
| chr17 | 4698990 | 4699252 | chr17 | 4891276 | 4891305 | chr17 | 4891527 | 4891556 |
| chr17 | 5000428 | 5000790 | chr17 | 5019637 | 5019662 | chr17 | 5019738 | 5019761 |
| chr17 | 5167638 | 3167681 | chr17 | 5168597 | 5168732 | chr17 | 6470357 | 6470419 |
| chr17 | 6616637 | 6616686 | chr17 | 6616911 | 6617173 | chr17 | 6679190 | 6679296 |
| chr17 | 6946107 | 6946141 | chr17 | 7043422 | 7043595 | chr17 | 7242844 | 7242899 |
| chr17 | 7348885 | 7348997 | chr17 | 7368947 | 7369139 | chr17 | 7471610 | 7471709 |
| chr17 | 7488151 | 7488249 | chr17 | 7555117 | 7555425 | chr17 | 7572957 | 7573018 |
| chr17 | 7573968 | 7574028 | chr17 | 7576847 | 7577167 | chr17 | 7577504 | 7577604 |
| chr17 | 7578164 | 7578570 | chr17 | 7579285 | 7579880 | chr17 | 7906254 | 7906535 |

TABLE 12-continued

| chr | start | end | chr | start | end | chr | start | end |
|---|---|---|---|---|---|---|---|---|
| chr17 | 7906832 | 7906861 | chr17 | 8104145 | 8104260 | chr17 | 8230335 | 8230694 |
| chr17 | 8534493 | 8534582 | chr17 | 8774623 | 8774653 | chr17 | 8868620 | 8868667 |
| chr17 | 8868815 | 8869385 | chr17 | 8906266 | 8906518 | chr17 | 8906993 | 8907575 |
| chr17 | 8926060 | 8926263 | chr17 | 9790805 | 9790835 | chr17 | 10101084 | 10101109 |
| chr17 | 10101132 | 10101447 | chr17 | 10102415 | 10102665 | chr17 | 10599510 | 10599546 |
| chr17 | 11144926 | 11144989 | chr17 | 11984693 | 11984722 | chr17 | 11998944 | 11998973 |
| chr17 | 12013726 | 12013755 | chr17 | 12016550 | 12016630 | chr17 | 12028618 | 12028647 |
| chr17 | 12659029 | 12659063 | chr17 | 13504195 | 13504195 | chr17 | 13504557 | 13504681 |
| chr17 | 13505002 | 13505188 | chr17 | 13505418 | 13505572 | chr17 | 14201041 | 14201181 |
| chr17 | 14204212 | 14204242 | chr17 | 14204527 | 14204620 | chr17 | 15245050 | 15245139 |
| chr17 | 15926819 | 15926849 | chr17 | 16119860 | 16120047 | chr17 | 16282251 | 16282300 |
| chr17 | 16284630 | 16285065 | chr17 | 16326144 | 16326216 | chr17 | 16428708 | 16428738 |
| chr17 | 16570699 | 16670794 | chr17 | 17062574 | 17062763 | chr17 | 17117365 | 17117396 |
| chr17 | 17123963 | 17123993 | chr17 | 17398404 | 17398440 | chr17 | 17719242 | 17719355 |
| chr17 | 18162844 | 18163325 | chr17 | 18538154 | 18538275 | chr17 | 18817198 | 18817284 |
| chr17 | 19769739 | 19769821 | chr17 | 19886035 | 19886221 | chr17 | 20039589 | 20039676 |
| chr17 | 20081131 | 20081161 | chr17 | 20205055 | 20205181 | chr17 | 20238152 | 20238198 |
| chr17 | 20468021 | 20468090 | chr17 | 20817755 | 20817917 | chr17 | 21003587 | 21003721 |
| chr17 | 25620573 | 25620715 | chr17 | 25676959 | 25676989 | chr17 | 25680264 | 25680294 |
| chr17 | 25907750 | 25907780 | chr17 | 26263183 | 26263322 | chr17 | 26554634 | 26554705 |
| chr17 | 26927249 | 26927410 | chr17 | 26961770 | 26961833 | chr17 | 27036492 | 27037023 |
| chr17 | 27038649 | 27038685 | chr17 | 27056577 | 27056857 | chr17 | 27081845 | 27081963 |
| chr17 | 27170162 | 27170460 | chr17 | 27181180 | 27181371 | chr17 | 27332453 | 27332660 |
| chr17 | 27686651 | 27686783 | chr17 | 22716114 | 27716220 | chr17 | 27716436 | 27716642 |
| chr17 | 27940591 | 27940911 | chr17 | 28112648 | 28112688 | chr17 | 28112951 | 28113032 |
| chr17 | 28562701 | 28562765 | chr17 | 29232244 | 29232350 | chr17 | 29234283 | 29234313 |
| chr17 | 29249717 | 29249930 | chr17 | 29298080 | 29298581 | chr17 | 29508761 | 29508790 |
| chr17 | 29541527 | 29541556 | chr17 | 29562732 | 29562761 | chr17 | 29718215 | 29718269 |
| chr17 | 29719187 | 29719242 | chr17 | 30243768 | 30243907 | chr17 | 30250325 | 30250364 |
| chr17 | 30258469 | 30258499 | chr17 | 30568137 | 30568174 | chr17 | 30710818 | 30710888 |
| chr17 | 31618425 | 31619319 | chr17 | 31619951 | 31620026 | chr17 | 32386720 | 32386875 |
| chr17 | 32484020 | 32484049 | chr17 | 32906379 | 32906555 | chr17 | 32906599 | 32906636 |
| chr17 | 32906987 | 32907146 | chr17 | 32907652 | 32907753 | chr17 | 32908132 | 32908146 |
| chr17 | 32908171 | 32908374 | chr17 | 32908647 | 32908931 | chr17 | 33288229 | 33288351 |
| chr17 | 33288890 | 33288988 | chr17 | 33672916 | 33672986 | chr17 | 33721211 | 33721349 |
| chr17 | 33877286 | 33877439 | chr17 | 33912210 | 33917268 | chr17 | 35165645 | 35165691 |
| chr17 | 35165986 | 35166016 | chr17 | 35285542 | 35285666 | chr17 | 35290388 | 35290655 |
| chr17 | 35291320 | 35291354 | chr17 | 35291829 | 35291898 | chr17 | 35291921 | 35292626 |
| chr17 | 35293704 | 35294154 | chr17 | 35294461 | 35294505 | chr17 | 35295047 | 35295160 |
| chr17 | 35296143 | 35296292 | chr17 | 35296728 | 35296888 | chr17 | 35297619 | 35298153 |
| chr17 | 35299251 | 35299443 | chr17 | 35299601 | 35299965 | chr17 | 35300261 | 35300712 |
| chr17 | 35300813 | 35300854 | chr17 | 35303340 | 35303535 | chr17 | 35872722 | 35872861 |
| chr17 | 36103021 | 36103326 | chr17 | 36103571 | 36103601 | chr17 | 36104218 | 36104550 |
| chr17 | 36104644 | 36104779 | chr17 | 36105223 | 36105349 | chr17 | 36105459 | 36105596 |
| chr17 | 36715772 | 36715967 | chr17 | 37001415 | 37001921 | chr17 | 37011176 | 37011236 |
| chr17 | 37131789 | 37132028 | chr17 | 37181771 | 37181865 | chr17 | 37192072 | 37192201 |
| chr17 | 37312431 | 37312477 | chr17 | 37321186 | 37321624 | chr17 | 37321788 | 37321972 |
| chr17 | 37366337 | 37366552 | chr17 | 37369180 | 37369210 | chr17 | 37381011 | 37381429 |
| chr17 | 37381571 | 37381726 | chr17 | 37381826 | 37381850 | chr17 | 37382146 | 37382248 |
| chr17 | 37484062 | 37484128 | chr17 | 37757153 | 37757217 | chr17 | 37760488 | 37760561 |
| chr17 | 37761997 | 37762334 | chr17 | 37868190 | 37868294 | chr17 | 37879568 | 37879615 |
| chr17 | 37880205 | 37880276 | chr17 | 37880971 | 37881018 | chr17 | 37881318 | 37881615 |
| chr17 | 38179397 | 38179430 | chr17 | 38335459 | 38335533 | chr17 | 38347560 | 38347615 |
| chr17 | 38380553 | 38380598 | chr17 | 38474363 | 38474502 | chr17 | 38497616 | 38497645 |
| chr17 | 38498083 | 38498112 | chr17 | 38504087 | 38504116 | chr17 | 38510555 | 38510584 |
| chr17 | 38574991 | 38575021 | chr17 | 39682352 | 39682711 | chr17 | 39834201 | 39834287 |
| chr17 | 40332943 | 40333226 | chr17 | 40400867 | 40401031 | chr17 | 40464278 | 40464317 |
| chr17 | 40464517 | 40464607 | chr17 | 40474467 | 40474496 | chr17 | 40826197 | 40826226 |
| chr17 | 40837022 | 40837051 | chr17 | 40837287 | 40837383 | chr17 | 40838982 | 40839022 |
| chr17 | 40897739 | 40897788 | chr17 | 40975413 | 40975677 | chr17 | 41175146 | 41175331 |
| chr17 | 41177394 | 41177459 | chr17 | 41197714 | 41197743 | chr17 | 41201163 | 41201192 |
| chr17 | 41203073 | 41203102 | chr17 | 41209064 | 41209114 | chr17 | 41215890 | 41215961 |
| chr17 | 41267731 | 41267775 | chr17 | 41276031 | 41276075 | chr17 | 41277259 | 41277721 |
| chr17 | 41278621 | 41278700 | chr17 | 41651850 | 41651880 | chr17 | 41745825 | 41745855 |
| chr17 | 41791460 | 41791489 | chr17 | 41791665 | 41791694 | chr17 | 42030329 | 42030358 |
| chr17 | 42061336 | 42061381 | chr17 | 42082522 | 42082557 | chr17 | 42084361 | 42084626 |
| chr17 | 42092190 | 42092220 | chr17 | 42110423 | 42110561 | chr17 | 42142661 | 42142808 |
| chr17 | 42246452 | 42246521 | chr17 | 42321590 | 42321674 | chr17 | 42331412 | 42331659 |
| chr17 | 42393842 | 42394024 | chr17 | 42402884 | 42402917 | chr17 | 42580695 | 42580793 |
| chr17 | 42587249 | 42587355 | chr17 | 42590091 | 42590224 | chr17 | 42635295 | 42635760 |
| chr17 | 42733711 | 42733884 | chr17 | 42767947 | 42768198 | chr17 | 42787481 | 42787616 |
| chr17 | 42907564 | 42907630 | chr17 | 42907655 | 42907951 | chr17 | 42975726 | 42975756 |
| chr17 | 43001891 | 43001946 | chr17 | 43044658 | 43044688 | chr17 | 43045039 | 43045116 |
| chr17 | 43046260 | 43046385 | chr17 | 43339109 | 43339333 | chr17 | 43339609 | 43339899 |
| chr17 | 43974256 | 43974358 | chr17 | 44897416 | 44897445 | chr17 | 45022106 | 45022140 |
| chr17 | 45187608 | 45187638 | chr17 | 45331014 | 45331313 | chr17 | 45810850 | 45811341 |
| chr17 | 45867315 | 45867460 | chr17 | 46125007 | 46125061 | chr17 | 46567400 | 46567655 |
| chr17 | 46619540 | 46619569 | chr17 | 46620494 | 46621094 | chr17 | 46621353 | 46621458 |

TABLE 12-continued

| chr | start | end | chr | start | end | chr | start | end |
|---|---|---|---|---|---|---|---|---|
| chr17 | 46621856 | 46621909 | chr17 | 46655148 | 46655178 | chr17 | 46655451 | 46655998 |
| chr17 | 46656058 | 46656704 | chr17 | 46659429 | 46659859 | chr17 | 46663743 | 46663824 |
| chr17 | 46663856 | 46663887 | chr17 | 46674873 | 46674970 | chr17 | 46675170 | 46675600 |
| chr17 | 46690467 | 46690664 | chr17 | 46691505 | 46691592 | chr17 | 46691805 | 46691818 |
| chr17 | 46691988 | 46692110 | chr17 | 46692439 | 46692606 | chr17 | 46710946 | 46710989 |
| chr17 | 46713959 | 46714072 | chr17 | 46795641 | 46796373 | chr17 | 46796499 | 46796637 |
| chr17 | 46796850 | 46797213 | chr17 | 46797275 | 46797582 | chr17 | 46799625 | 46799896 |
| chr17 | 46800601 | 46800668 | chr17 | 46800961 | 46801047 | chr17 | 46801109 | 46801416 |
| chr17 | 46802459 | 46802911 | chr17 | 46802994 | 46803286 | chr17 | 46804107 | 46804428 |
| chr17 | 46810416 | 46810958 | chr17 | 46811354 | 46811499 | chr17 | 46816282 | 46816877 |
| chr17 | 46824224 | 46824275 | chr17 | 46824359 | 46825054 | chr17 | 46825284 | 46825514 |
| chr17 | 46826930 | 46827127 | chr17 | 46827330 | 46827501 | chr17 | 46827626 | 46827756 |
| chr17 | 46829498 | 46829579 | chr17 | 46829979 | 46830110 | chr17 | 46831779 | 46832325 |
| chr17 | 46832490 | 46832639 | chr17 | 47072805 | 47073028 | chr17 | 47073104 | 47073327 |
| chr17 | 47073389 | 47073465 | chr17 | 47073988 | 47074228 | chr17 | 47074561 | 47074895 |
| chr17 | 47075160 | 47075364 | chr17 | 47075715 | 47075734 | chr17 | 47075880 | 47076055 |
| chr17 | 47574090 | 47574149 | chr17 | 47657544 | 47657583 | chr17 | 47865514 | 47865555 |
| chr17 | 47987525 | 47987619 | chr17 | 47987930 | 47988114 | chr17 | 48041152 | 48041320 |
| chr17 | 48041672 | 48041721 | chr17 | 48042039 | 48042069 | chr17 | 48042435 | 48042647 |
| chr17 | 48042751 | 48042956 | chr17 | 48048952 | 48049059 | chr17 | 48049307 | 48050526 |
| chr17 | 48071020 | 48071050 | chr17 | 48071807 | 48071894 | chr17 | 48473056 | 48473236 |
| chr17 | 48545804 | 48545950 | chr17 | 48589801 | 48589831 | chr17 | 48612223 | 48612308 |
| chr17 | 48636581 | 48637136 | chr17 | 48653128 | 48653158 | chr17 | 48799820 | 48799866 |
| chr17 | 49027838 | 49027876 | chr17 | 49229267 | 49229703 | chr17 | 50235216 | 50235258 |
| chr17 | 50235631 | 50235952 | chr17 | 51901004 | 51901034 | chr17 | 53341252 | 53341536 |
| chr17 | 53342876 | 53343089 | chr17 | 53479184 | 53479316 | chr17 | 53814544 | 53814678 |
| chr17 | 53922649 | 53922790 | chr17 | 54674986 | 54675272 | chr17 | 54755969 | 54755990 |
| chr17 | 55037326 | 55037626 | chr17 | 55122813 | 55122842 | chr17 | 55213641 | 55213670 |
| chr17 | 55962573 | 55962841 | chr17 | 56092600 | 56092736 | chr17 | 56234405 | 56234743 |
| chr17 | 56326949 | 56326994 | chr17 | 56327271 | 56327301 | chr17 | 56471121 | 56471167 |
| chr17 | 56743206 | 56743249 | chr17 | 56833127 | 56833221 | chr17 | 56833707 | 56834000 |
| chr17 | 56834020 | 56834075 | chr17 | 56834306 | 56834375 | chr17 | 57296865 | 57297129 |
| chr17 | 57386255 | 57386735 | chr17 | 57787402 | 57787465 | chr17 | 57832475 | 57832607 |
| chr17 | 58216613 | 58216836 | chr17 | 58216866 | 58217298 | chr17 | 58217357 | 58217551 |
| chr17 | 58218765 | 58218993 | chr17 | 58227374 | 58227397 | chr17 | 58498697 | 58499314 |
| chr17 | 59474157 | 59474246 | chr17 | 59474833 | 59475100 | chr17 | 59475678 | 59476127 |
| chr17 | 59476410 | 59476635 | chr17 | 59478147 | 59478602 | chr17 | 59481657 | 59481678 |
| chr17 | 59488101 | 59488423 | chr17 | 59528876 | 59529150 | chr17 | 59529254 | 59529264 |
| chr17 | 59529844 | 59530352 | chr17 | 59531667 | 59532017 | chr17 | 59533875 | 59534405 |
| chr17 | 59534751 | 59534781 | chr17 | 59535137 | 59535219 | chr17 | 59539236 | 59539601 |
| chr17 | 59924556 | 59924585 | chr17 | 59937192 | 59937236 | chr17 | 61677374 | 61677404 |
| chr17 | 61778235 | 61778248 | chr17 | 61817576 | 61817955 | chr17 | 61926172 | 61926324 |
| chr17 | 61926508 | 61926603 | chr17 | 62028596 | 62028790 | chr17 | 62777335 | 62777450 |
| chr17 | 62777746 | 62777791 | chr17 | 64672366 | 64672544 | chr17 | 65715295 | 65715493 |
| chr17 | 66420718 | 66420837 | chr17 | 66596471 | 66596525 | chr17 | 66596984 | 66597021 |
| chr17 | 67410305 | 67410397 | chr17 | 68164733 | 68164928 | chr17 | 70026543 | 70026667 |
| chr17 | 70112916 | 70113566 | chr17 | 70113648 | 70114018 | chr17 | 70114153 | 70114517 |
| chr17 | 70215683 | 70216306 | chr17 | 70216395 | 70216506 | chr17 | 70586165 | 70586272 |
| chr17 | 71229815 | 71229918 | chr17 | 71641544 | 71641683 | chr17 | 71948439 | 71948863 |
| chr17 | 72236510 | 72236548 | chr17 | 72270286 | 72270415 | chr17 | 72321933 | 72321975 |
| chr17 | 72322363 | 72322557 | chr17 | 72353213 | 72353259 | chr17 | 72353417 | 72353550 |
| chr17 | 72427853 | 72427999 | chr17 | 72428344 | 72428381 | chr17 | 72491378 | 72491531 |
| chr17 | 22667337 | 72667481 | chr17 | 72849010 | 72849079 | chr17 | 72857038 | 72857368 |
| chr17 | 72862371 | 72862460 | chr17 | 72920796 | 72921032 | chr17 | 73031637 | 73031935 |
| chr17 | 73115588 | 73115658 | chr17 | 73115884 | 73115914 | chr17 | 73128301 | 73128338 |
| chr17 | 73147177 | 73147356 | chr17 | 73147774 | 73147992 | chr17 | 73215289 | 73215423 |
| chr17 | 73351981 | 73352086 | chr17 | 73545998 | 73546299 | chr17 | 73586015 | 73586418 |
| chr17 | 73608306 | 73608336 | chr17 | 73636144 | 73636337 | chr17 | 73692986 | 73693122 |
| chr17 | 73709838 | 73709955 | chr17 | 73782870 | 73782947 | chr17 | 73808631 | 73808671 |
| chr17 | 73827213 | 73827243 | chr17 | 73901630 | 73901893 | chr17 | 73904093 | 73904127 |
| chr17 | 74028346 | 74028413 | chr17 | 74047797 | 74048063 | chr17 | 74070281 | 74070479 |
| chr17 | 74071445 | 74071481 | chr17 | 74071689 | 74071729 | chr17 | 74072999 | 74073036 |
| chr17 | 74073269 | 74073433 | chr17 | 74087118 | 74087185 | chr17 | 74299798 | 74299899 |
| chr17 | 74390363 | 74390393 | chr17 | 74533844 | 74534310 | chr17 | 74581182 | 74581221 |
| chr17 | 74663258 | 74663288 | chr17 | 74732944 | 74732973 | chr17 | 74865053 | 74865192 |
| chr17 | 74865698 | 74866243 | chr17 | 75137660 | 75137887 | chr17 | 75207514 | 75207630 |
| chr17 | 75207839 | 75207987 | chr17 | 75276054 | 75276083 | chr17 | 75276413 | 75276442 |
| chr17 | 75277348 | 75277659 | chr17 | 75278020 | 75278049 | chr17 | 75279105 | 75279134 |
| chr17 | 75282025 | 75282154 | chr17 | 75315512 | 75315681 | chr17 | 75316368 | 75316397 |
| chr17 | 75317170 | 75317199 | chr17 | 75347755 | 75347784 | chr17 | 75368735 | 75369238 |
| chr17 | 75369440 | 75369457 | chr17 | 75369493 | 75369860 | chr17 | 75370269 | 75370316 |
| chr17 | 75370596 | 75370625 | chr17 | 75373312 | 75373341 | chr17 | 75385071 | 75385446 |
| chr17 | 75405827 | 75405856 | chr17 | 75417150 | 25417179 | chr17 | 75523142 | 75523172 |
| chr17 | 75524636 | 75525194 | chr17 | 75733978 | 75734244 | chr17 | 75797111 | 75797179 |
| chr17 | 76021047 | 76021077 | chr17 | 76125196 | 76125225 | chr17 | 76126434 | 76126463 |
| chr17 | 76128466 | 76128663 | chr17 | 76130124 | 76130153 | chr17 | 76130481 | 76130510 |
| chr17 | 76135783 | 76136001 | chr17 | 76137951 | 76138190 | chr17 | 76138498 | 76138622 |
| chr17 | 76187407 | 76187544 | chr17 | 76207342 | 76207372 | chr17 | 76211302 | 76211506 |

TABLE 12-continued

| chr | start | end | chr | start | end | chr | start | end |
|---|---|---|---|---|---|---|---|---|
| chr17 | 76227849 | 76228161 | chr17 | 76228214 | 76228357 | chr17 | 76404615 | 76404659 |
| chr17 | 76877177 | 76877212 | chr17 | 76884417 | 76884447 | chr17 | 76974447 | 76974499 |
| chr17 | 76983518 | 76983669 | chr17 | 76984053 | 76984188 | chr17 | 77070307 | 77070457 |
| chr17 | 77084518 | 77084727 | chr17 | 77105055 | 77105198 | chr17 | 77145129 | 77145242 |
| chr17 | 77179113 | 77179278 | chr17 | 77179630 | 77179776 | chr17 | 77394706 | 77394850 |
| chr17 | 77776827 | 77776995 | chr17 | 77777053 | 77777056 | chr17 | 77777585 | 77777903 |
| chr17 | 77777944 | 77777961 | chr17 | 77778943 | 77779179 | chr17 | 77789474 | 77789500 |
| chr17 | 77825696 | 77825812 | chr17 | 77827114 | 77827201 | chr17 | 77899664 | 77899693 |
| chr17 | 77919429 | 77919477 | chr17 | 77924259 | 77924351 | chr17 | 78122158 | 78122190 |
| chr17 | 78194821 | 78194861 | chr17 | 78272278 | 78272313 | chr17 | 78447127 | 78447157 |
| chr17 | 78451931 | 78451953 | chr17 | 78452296 | 78452340 | chr17 | 78452681 | 78452833 |
| chr17 | 78518031 | 78518198 | chr17 | 78599596 | 78599628 | chr17 | 78667992 | 78668159 |
| chr17 | 78874441 | 78874559 | chr17 | 78975667 | 78975758 | chr17 | 78999625 | 78999654 |
| chr17 | 79058302 | 79058333 | chr17 | 79094182 | 79094245 | chr17 | 79099770 | 79099799 |
| chr17 | 79626591 | 79626703 | chr17 | 79626955 | 79626985 | chr17 | 79769433 | 79769693 |
| chr17 | 79813409 | 79813507 | chr17 | 79850445 | 79850537 | chr17 | 79896013 | 79896043 |
| chr17 | 79939605 | 79939835 | chr17 | 79945037 | 79945074 | chr17 | 80186260 | 80186289 |
| chr17 | 80197756 | 80197898 | chr17 | 80254266 | 80254296 | chr17 | 80289234 | 80289310 |
| chr17 | 80289858 | 80289892 | chr17 | 80294282 | 80294427 | chr17 | 80329709 | 80330000 |
| chr17 | 80394063 | 80394185 | chr17 | 80394573 | 80394602 | chr17 | 80479311 | 80479559 |
| chr17 | 80491572 | 80491602 | chr17 | 80535382 | 80535487 | chr17 | 80571380 | 80571276 |
| chr17 | 80593754 | 80594107 | chr17 | 80654983 | 80655013 | chr17 | 80693317 | 80693554 |
| chr17 | 80749152 | 80749276 | chr17 | 80751650 | 80751714 | chr17 | 80794259 | 80794288 |
| chr17 | 80797692 | 80798345 | chr17 | 80832305 | 80832411 | chr17 | 80832712 | 80832796 |
| chr17 | 80859239 | 80859269 | chr17 | 81008618 | 81008826 | chr17 | 81033487 | 81033517 |
| chr17 | 81048993 | 81049023 | chr17 | 81049994 | 81050058 | chr18 | 147543 | 147613 |
| chr18 | 499367 | 499482 | chr18 | 500046 | 500738 | chr18 | 597548 | 597578 |
| chr18 | 697854 | 697901 | chr18 | 904462 | 904648 | chr18 | 905000 | 905030 |
| chr18 | 905434 | 905615 | chr18 | 906821 | 906907 | chr18 | 907472 | 907594 |
| chr18 | 907912 | 907922 | chr18 | 908454 | 908589 | chr18 | 909487 | 909587 |
| chr18 | 2755770 | 2755878 | chr18 | 2906268 | 2906304 | chr18 | 3214441 | 3214825 |
| chr18 | 3216042 | 3215256 | chr18 | 3499067 | 3499371 | chr18 | 4453964 | 4454163 |
| chr18 | 5133207 | 5133343 | chr18 | 5196575 | 5196959 | chr18 | 5197202 | 5197271 |
| chr18 | 5197330 | 5197347 | chr18 | 5237878 | 5238247 | chr18 | 5628167 | 5628515 |
| chr18 | 5629774 | 5629825 | chr18 | 5630312 | 5630362 | chr18 | 5895023 | 5895205 |
| chr18 | 5895975 | 5896085 | chr18 | 6729952 | 6729993 | chr18 | 6908056 | 6908243 |
| chr18 | 7117665 | 7117804 | chr18 | 7567783 | 7568291 | chr18 | 8608748 | 8608837 |
| chr18 | 8608902 | 8608968 | chr18 | 8612252 | 8612282 | chr18 | 9771586 | 9771753 |
| chr18 | 9868137 | 9868174 | chr18 | 9912767 | 9912797 | chr18 | 10251324 | 10251432 |
| chr18 | 10589096 | 10589348 | chr18 | 10733492 | 10733605 | chr18 | 11148969 | 11149045 |
| chr18 | 11149561 | 11149759 | chr18 | 11149780 | 11149888 | chr18 | 11401654 | 11401817 |
| chr18 | 11689190 | 11689220 | chr18 | 11752128 | 11752379 | chr18 | 11752700 | 11752730 |
| chr18 | 11942728 | 11942838 | chr18 | 11979677 | 11979860 | chr18 | 12254305 | 12254578 |
| chr18 | 12277243 | 12277273 | chr18 | 12307247 | 12307505 | chr18 | 12307603 | 12307751 |
| chr18 | 12375483 | 12375597 | chr18 | 12375923 | 12376129 | chr18 | 12890152 | 12890278 |
| chr18 | 12948993 | 12949023 | chr18 | 13132080 | 13132246 | chr18 | 13824025 | 13824102 |
| chr18 | 13826393 | 13826536 | chr18 | 13868713 | 13868919 | chr18 | 15198110 | 15198248 |
| chr18 | 18822392 | 18823274 | chr18 | 19191525 | 19191585 | chr18 | 19750308 | 19750346 |
| chr18 | 20911541 | 20911571 | chr18 | 21035222 | 21035252 | chr18 | 21269349 | 21269390 |
| chr18 | 21269659 | 21269740 | chr18 | 21719351 | 21719568 | chr18 | 21719938 | 21720064 |
| chr18 | 22929081 | 12929095 | chr18 | 22929187 | 22929718 | chr18 | 22929927 | 22930559 |
| chr18 | 22930790 | 22931178 | chr18 | 23686462 | 23686618 | chr18 | 24127748 | 24128030 |
| chr18 | 24130809 | 24130946 | chr18 | 24131099 | 24131187 | chr18 | 24764951 | 24765168 |
| chr18 | 25755593 | 25755655 | chr18 | 25756010 | 25756040 | chr18 | 25756495 | 25756729 |
| chr18 | 25757187 | 25757452 | chr18 | 25757787 | 25757824 | chr18 | 25758129 | 25758141 |
| chr18 | 28620899 | 28620955 | chr18 | 28621034 | 28621097 | chr18 | 28621328 | 28621393 |
| chr18 | 28621636 | 28621932 | chr18 | 28622419 | 28622488 | chr18 | 29413805 | 29413839 |
| chr18 | 29719775 | 29720012 | chr18 | 30349740 | 30349781 | chr18 | 31020495 | 31020510 |
| chr18 | 31158093 | 31158158 | chr18 | 31739035 | 31739469 | chr18 | 31802132 | 31802167 |
| chr18 | 31802938 | 31802968 | chr18 | 31803438 | 31803472 | chr18 | 31902793 | 31902945 |
| chr18 | 32073908 | 32074086 | chr18 | 32557832 | 32557864 | chr18 | 32847598 | 32847642 |
| chr18 | 32957803 | 32957839 | chr18 | 33078363 | 33078662 | chr18 | 33877683 | 33877754 |
| chr18 | 35065072 | 35065145 | chr18 | 35144845 | 35144936 | chr18 | 35144969 | 35145465 |
| chr18 | 35145968 | 35146036 | chr18 | 35146062 | 35146241 | chr18 | 35147487 | 35147569 |
| chr18 | 43546048 | 43546134 | chr18 | 43914211 | 43914278 | chr18 | 44259903 | 44259990 |
| chr18 | 44336034 | 44336449 | chr18 | 44337174 | 44337617 | chr18 | 44337650 | 44337841 |
| chr18 | 44773060 | 44773116 | chr18 | 44773592 | 44773966 | chr18 | 44774406 | 44774890 |
| chr18 | 44775380 | 44775554 | chr18 | 44776972 | 44777088 | chr18 | 44777301 | 44777331 |
| chr18 | 44777596 | 44777750 | chr18 | 44778049 | 44778326 | chr18 | 44781003 | 44781041 |
| chr18 | 44787781 | 44787846 | chr18 | 44788251 | 44788281 | chr18 | 44789474 | 44789514 |
| chr18 | 44789872 | 44789937 | chr18 | 45058069 | 45058240 | chr18 | 46142662 | 46142809 |
| chr18 | 47720492 | 47720522 | chr18 | 48604773 | 48604802 | chr18 | 48636211 | 48636320 |
| chr18 | 49867303 | 49867399 | chr18 | 49868634 | 49868664 | chr18 | 51771058 | 51771128 |
| chr18 | 52989009 | 52989220 | chr18 | 52989741 | 52989882 | chr18 | 53257137 | 53257204 |
| chr18 | 53446970 | 53447474 | chr18 | 53447799 | 53447816 | chr18 | 53989796 | 53989877 |
| chr18 | 54789070 | 54789256 | chr18 | 55019707 | 55019775 | chr18 | 55020655 | 55020698 |
| chr18 | 55021078 | 55021242 | chr18 | 55103381 | 55103411 | chr18 | 55104808 | 55105140 |
| chr18 | 55106728 | 55105830 | chr18 | 55114480 | 55114644 | chr18 | 55426948 | 55426978 |

TABLE 12-continued

| chr | start | end | chr | start | end | chr | start | end |
|---|---|---|---|---|---|---|---|---|
| chr18 | 55850845 | 55850987 | chr18 | 56483918 | 56483958 | chr18 | 56815734 | 56816107 |
| chr18 | 56887076 | 56887424 | chr18 | 56888554 | 56888623 | chr18 | 56931541 | 56931583 |
| chr18 | 56931967 | 56932107 | chr18 | 56932352 | 56932637 | chr18 | 56935010 | 56935319 |
| chr18 | 56936004 | 56936074 | chr18 | 56939113 | 56939174 | chr18 | 56939423 | 56939651 |
| chr18 | 56939764 | 56940170 | chr18 | 56940566 | 56940722 | chr18 | 56940955 | 56941244 |
| chr18 | 56941558 | 56941788 | chr18 | 57363706 | 57363743 | chr18 | 57364658 | 57364691 |
| chr18 | 59000988 | 59001022 | chr18 | 59001301 | 59001343 | chr18 | 59001498 | 59001740 |
| chr18 | 60263661 | 60263895 | chr18 | 60557729 | 60557759 | chr18 | 60985498 | 60985532 |
| chr18 | 60985593 | 60985732 | chr18 | 51143911 | 61143975 | chr18 | 67067558 | 67067907 |
| chr18 | 67068715 | 67068811 | chr18 | 67069216 | 67069246 | chr18 | 70209148 | 70209205 |
| chr18 | 70210418 | 70210508 | chr18 | 70211626 | 70211666 | chr18 | 70534282 | 70534315 |
| chr18 | 70534428 | 70534731 | chr18 | 70535373 | 70535554 | chr18 | 70535576 | 70535582 |
| chr18 | 70536010 | 70536083 | chr18 | 70536188 | 70536604 | chr18 | 70536833 | 70536871 |
| chr18 | 70537188 | 70537218 | chr18 | 72845833 | 72845863 | chr18 | 73167585 | 73167832 |
| chr18 | 73628019 | 73628068 | chr18 | 74501144 | 74501518 | chr18 | 74755508 | 74755590 |
| chr18 | 74961326 | 74961955 | chr18 | 74962019 | 74962147 | chr18 | 74962970 | 74963545 |
| chr18 | 75335093 | 75335123 | chr18 | 75339231 | 75339340 | chr18 | 75362931 | 75362985 |
| chr18 | 75551271 | 75551301 | chr18 | 75612225 | 75612286 | chr18 | 75999404 | 75999434 |
| chr18 | 76239541 | 76239616 | chr18 | 76501479 | 76501509 | chr18 | 76653631 | 76653661 |
| chr18 | 76686249 | 76686279 | chr18 | 76689735 | 76689765 | chr18 | 76740102 | 76740223 |
| chr18 | 77050480 | 77050678 | chr18 | 77143346 | 77143376 | chr18 | 77167824 | 77167854 |
| chr18 | 77181355 | 77181409 | chr18 | 77194936 | 77194978 | chr18 | 77205532 | 77205638 |
| chr18 | 77285897 | 77286028 | chr18 | 77300326 | 77300483 | chr18 | 77309533 | 77309563 |
| chr18 | 77312866 | 77312927 | chr18 | 77329727 | 77330017 | chr18 | 77371430 | 77371547 |
| chr18 | 77459762 | 77459877 | chr18 | 77512225 | 77512255 | chr18 | 77543249 | 77543481 |
| chr18 | 77543700 | 77543824 | chr18 | 77548352 | 77548609 | chr18 | 77550206 | 77550367 |
| chr18 | 77558082 | 77558358 | chr18 | 77558831 | 77558930 | chr18 | 77576934 | 77527043 |
| chr18 | 77636591 | 77636621 | chr18 | 77698881 | 77698919 | chr18 | 78004993 | 78005051 |
| chr19 | 403538 | 403809 | chr19 | 407189 | 407320 | chr19 | 418225 | 418255 |
| chr19 | 462181 | 462269 | chr19 | 468757 | 468787 | chr19 | 485165 | 485394 |
| chr19 | 549361 | 549451 | chr19 | 555608 | 555768 | chr19 | 570156 | 570194 |
| chr19 | 591365 | 591416 | chr19 | 592589 | 592632 | chr19 | 593290 | 593462 |
| chr19 | 599214 | 599333 | chr19 | 607070 | 607110 | chr19 | 690888 | 690940 |
| chr19 | 752136 | 752462 | chr19 | 869337 | 869394 | chr19 | 883624 | 883791 |
| chr19 | 884018 | 884162 | chr19 | 891516 | 891723 | chr19 | 955757 | 956237 |
| chr19 | 959128 | 959187 | chr19 | 1003305 | 1003384 | chr19 | 1003669 | 1003734 |
| chr19 | 1004915 | 1005441 | chr19 | 1030176 | 1030225 | chr19 | 1047890 | 1047939 |
| chr19 | 1048348 | 1048465 | chr19 | 1083314 | 1083437 | chr19 | 1156524 | 1156554 |
| chr19 | 1170185 | 1170230 | chr19 | 1171099 | 1171324 | chr19 | 1220422 | 1220610 |
| chr19 | 1221981 | 1222010 | chr19 | 1236474 | 1236678 | chr19 | 1274778 | 1274826 |
| chr19 | 1308047 | 1308081 | chr19 | 1325788 | 1325889 | chr19 | 1330064 | 1330214 |
| chr19 | 1401752 | 1401795 | chr19 | 1450319 | 1450390 | chr19 | 1496413 | 1496450 |
| chr19 | 1496654 | 1496694 | chr19 | 1524443 | 1524447 | chr19 | 1525605 | 1525960 |
| chr19 | 1527227 | 1527394 | chr19 | 1547233 | 1547263 | chr19 | 1689436 | 1689595 |
| chr19 | 1754172 | 1754193 | chr19 | 1754225 | 1754254 | chr19 | 1754739 | 1754804 |
| chr19 | 1757416 | 1757615 | chr19 | 1762474 | 1762505 | chr19 | 1764293 | 1764339 |
| chr19 | 1775076 | 1775239 | chr19 | 1776376 | 1776534 | chr19 | 1799466 | 1799516 |
| chr19 | 1800032 | 1800300 | chr19 | 1807970 | 1808413 | chr19 | 2135672 | 2135701 |
| chr19 | 2155031 | 2155061 | chr19 | 2251152 | 2251234 | chr19 | 2251611 | 2251715 |
| chr19 | 2252589 | 2252658 | chr19 | 2252984 | 2253735 | chr19 | 2274677 | 2274713 |
| chr19 | 2290253 | 2290271 | chr19 | 2290631 | 2290867 | chr19 | 2302793 | 2302951 |
| chr19 | 2330317 | 2330407 | chr19 | 2331413 | 2331443 | chr19 | 2413125 | 2413155 |
| chr19 | 2414257 | 2414337 | chr19 | 2513250 | 2513285 | chr19 | 2642877 | 2642947 |
| chr19 | 2683911 | 2684080 | chr19 | 3041417 | 3041447 | chr19 | 3093571 | 3093818 |
| chr19 | 3114998 | 3115027 | chr19 | 3118927 | 3118956 | chr19 | 3219512 | 3219565 |
| chr19 | 3296613 | 3296670 | chr19 | 3361139 | 3361388 | chr19 | 3562128 | 3562797 |
| chr19 | 3570230 | 3570371 | chr19 | 3578138 | 3578223 | chr19 | 3659668 | 3659793 |
| chr19 | 3716179 | 3716241 | chr19 | 3718052 | 3718082 | chr19 | 3778130 | 3778394 |
| chr19 | 3779277 | 3779435 | chr19 | 3785649 | 3785835 | chr19 | 3785865 | 3786220 |
| chr19 | 3821044 | 3821217 | chr19 | 3822135 | 3822203 | chr19 | 3834572 | 3834641 |
| chr19 | 3855407 | 3855595 | chr19 | 3966686 | 3966755 | chr19 | 3994540 | 3994795 |
| chr19 | 4054435 | 4054471 | chr19 | 4095471 | 4095514 | chr19 | 4101087 | 4101116 |
| chr19 | 4110565 | 4110597 | chr19 | 4117526 | 4117630 | chr19 | 4160800 | 4160898 |
| chr19 | 4196767 | 4195853 | chr19 | 4305057 | 4306086 | chr19 | 4311273 | 4311430 |
| chr19 | 4509338 | 4509440 | chr19 | 4548134 | 4548364 | chr19 | 4549454 | 4549565 |
| chr19 | 4550246 | 4550330 | chr19 | 4555896 | 4556112 | chr19 | 4667098 | 4557235 |
| chr19 | 4572332 | 4572459 | chr19 | 4670765 | 4670949 | chr19 | 4789697 | 4789805 |
| chr19 | 4790142 | 4790264 | chr19 | 4835778 | 4835926 | chr19 | 4910361 | 4910410 |
| chr19 | 4944145 | 4944174 | chr19 | 5292812 | 5292844 | chr19 | 5338914 | 5339143 |
| chr19 | 5608519 | 5608569 | chr19 | 5676212 | 5676242 | chr19 | 5759374 | 5759544 |
| chr19 | 5759744 | 5759774 | chr19 | 5767703 | 5767733 | chr19 | 5826179 | 5826209 |
| chr19 | 5905517 | 5905547 | chr19 | 5910356 | 5910492 | chr19 | 5914761 | 5914791 |
| chr19 | 5914992 | 5915060 | chr19 | 6303268 | 6303298 | chr19 | 6512913 | 6512943 |
| chr19 | 6590325 | 6590478 | chr19 | 6658279 | 6658422 | chr19 | 6889423 | 6889574 |
| chr19 | 7157547 | 7157628 | chr19 | 7554718 | 7554780 | chr19 | 7615996 | 7616025 |
| chr19 | 7635387 | 7635552 | chr19 | 7746942 | 7747042 | chr19 | 7747205 | 7747234 |
| chr19 | 7795012 | 7795244 | chr19 | 7853028 | 7853157 | chr19 | 7853361 | 7853460 |
| chr19 | 7870346 | 7870387 | chr19 | 8115235 | 8115276 | chr19 | 8391621 | 8391651 |

TABLE 12-continued

| chr | start | end | chr | start | end | chr | start | end |
|---|---|---|---|---|---|---|---|---|
| chr19 | 8554173 | 8554218 | chr19 | 8576914 | 8577000 | chr19 | 8579592 | 8579705 |
| chr19 | 9239580 | 9239695 | chr19 | 9331918 | 9331955 | chr19 | 9420142 | 9420240 |
| chr19 | 9473564 | 9473597 | chr19 | 9473869 | 9474056 | chr19 | 9517609 | 9517771 |
| chr19 | 9608895 | 9609036 | chr19 | 9609319 | 9609436 | chr19 | 9903913 | 9904100 |
| chr19 | 9937291 | 9937386 | chr19 | 10231077 | 10231242 | chr19 | 10246505 | 10246566 |
| chr19 | 10362045 | 10362182 | chr19 | 10398209 | 10398285 | chr19 | 10405972 | 10406159 |
| chr19 | 10406279 | 10406349 | chr19 | 10406806 | 10407029 | chr19 | 10407045 | 10407135 |
| chr19 | 10527165 | 10527243 | chr19 | 10531419 | 10531512 | chr19 | 10531964 | 10531994 |
| chr19 | 10600431 | 10600460 | chr19 | 10602274 | 10602348 | chr19 | 10602565 | 10602864 |
| chr19 | 10610138 | 10610260 | chr19 | 10621768 | 10621829 | chr19 | 10624751 | 10624852 |
| chr19 | 10624966 | 10625465 | chr19 | 10648372 | 10648546 | chr19 | 10729811 | 10729899 |
| chr19 | 10823678 | 10823721 | chr19 | 10827675 | 10827705 | chr19 | 10851287 | 10851362 |
| chr19 | 10955456 | 10955585 | chr19 | 11063941 | 11063971 | chr19 | 11134252 | 11134281 |
| chr19 | 11138507 | 11138536 | chr19 | 11492252 | 11492528 | chr19 | 11591031 | 11591185 |
| chr19 | 11592710 | 11592750 | chr19 | 11593022 | 11593159 | chr19 | 11689460 | 11689564 |
| chr19 | 11959912 | 11960077 | chr19 | 12147437 | 12147545 | chr19 | 12163448 | 12163672 |
| chr19 | 12163893 | 12163923 | chr19 | 12175445 | 12175504 | chr19 | 12175814 | 12176005 |
| chr19 | 12203028 | 12203744 | chr19 | 12205385 | 12205434 | chr19 | 12267019 | 12267662 |
| chr19 | 12303495 | 12303551 | chr19 | 12305839 | 12306193 | chr19 | 12306230 | 12306263 |
| chr19 | 12476492 | 12476556 | chr19 | 12595109 | 12595307 | chr19 | 12595845 | 12595896 |
| chr19 | 12606381 | 12606511 | chr19 | 12661175 | 12661221 | chr19 | 12750987 | 12751056 |
| chr19 | 12846906 | 12847098 | chr19 | 12860307 | 12860433 | chr19 | 12863412 | 12863520 |
| chr19 | 12952000 | 12952139 | chr19 | 12996169 | 12996280 | chr19 | 13113454 | 13113668 |
| chr19 | 13491305 | 13491340 | chr19 | 13616696 | 13616956 | chr19 | 13617159 | 13617256 |
| chr19 | 13618288 | 13618381 | chr19 | 13782965 | 13783028 | chr19 | 13903520 | 13903603 |
| chr19 | 13965838 | 13965965 | chr19 | 13988775 | 13988805 | chr19 | 14085021 | 14085051 |
| chr19 | 14181305 | 14181846 | chr19 | 14324876 | 14324906 | chr19 | 14327101 | 14327158 |
| chr19 | 14334020 | 14334060 | chr19 | 14411056 | 14411086 | chr19 | 14584240 | 14584412 |
| chr19 | 14584537 | 14584775 | chr19 | 14663925 | 14664183 | chr19 | 14664479 | 14664561 |
| chr19 | 14869496 | 14869526 | chr19 | 15090172 | 15090499 | chr19 | 15121685 | 15121894 |
| chr19 | 15122120 | 15122238 | chr19 | 15288433 | 15288856 | chr19 | 15292384 | 15292499 |
| chr19 | 15342734 | 15343373 | chr19 | 15344107 | 15344130 | chr19 | 15519444 | 15519474 |
| chr19 | 16766902 | 16766932 | chr19 | 16999599 | 16999782 | chr19 | 17000570 | 17000599 |
| chr19 | 17007086 | 17007388 | chr19 | 17007447 | 17007662 | chr19 | 17008586 | 17008698 |
| chr19 | 17152333 | 17152363 | chr19 | 17335642 | 17335718 | chr19 | 17336042 | 17336111 |
| chr19 | 17359350 | 17359459 | chr19 | 17392641 | 17392866 | chr19 | 17436061 | 17436203 |
| chr19 | 17446897 | 17447045 | chr19 | 17717286 | 17717315 | chr19 | 17759224 | 17759423 |
| chr19 | 17791182 | 17791211 | chr19 | 17943423 | 17943452 | chr19 | 17945891 | 17945983 |
| chr19 | 17947991 | 17948023 | chr19 | 17949094 | 17949123 | chr19 | 17958490 | 17958839 |
| chr19 | 17983537 | 17983665 | chr19 | 18041069 | 18041203 | chr19 | 18057603 | 18057655 |
| chr19 | 18103711 | 18103741 | chr19 | 18104472 | 18104606 | chr19 | 18126412 | 18126442 |
| chr19 | 18271894 | 18271923 | chr19 | 18278047 | 18278076 | chr19 | 18300127 | 18300422 |
| chr19 | 18301007 | 18301037 | chr19 | 18331031 | 18331136 | chr19 | 18343439 | 18343569 |
| chr19 | 18343921 | 18343963 | chr19 | 18383211 | 18383351 | chr19 | 18488862 | 18488915 |
| chr19 | 18496000 | 18496030 | chr19 | 18523115 | 18523145 | chr19 | 18633926 | 18633980 |
| chr19 | 18681638 | 18681926 | chr19 | 18714552 | 18714580 | chr19 | 18811560 | 18811804 |
| chr19 | 18856379 | 18856409 | chr19 | 18872825 | 18872900 | chr19 | 18899432 | 18899652 |
| chr19 | 18901828 | 18902095 | chr19 | 18989821 | 18990281 | chr19 | 18994887 | 18995081 |
| chr19 | 19260030 | 19260101 | chr19 | 19261519 | 19261548 | chr19 | 19334831 | 19334915 |
| chr19 | 19489251 | 19489297 | chr19 | 19636877 | 19636907 | chr19 | 19645834 | 19645925 |
| chr19 | 19651991 | 19652066 | chr19 | 19729251 | 19729395 | chr19 | 19739172 | 19739428 |
| chr19 | 19775308 | 19775472 | chr19 | 20011955 | 20012149 | chr19 | 20188693 | 20188872 |
| chr19 | 20189322 | 20189438 | chr19 | 21237609 | 21237655 | chr19 | 21239053 | 21239129 |
| chr19 | 21245066 | 21245152 | chr19 | 21265890 | 21265920 | chr19 | 21289719 | 21289749 |
| chr19 | 21290153 | 21290216 | chr19 | 21303863 | 21303993 | chr19 | 21305707 | 21305737 |
| chr19 | 21370382 | 21370479 | chr19 | 21512594 | 21512660 | chr19 | 21646407 | 21646437 |
| chr19 | 21665258 | 21665288 | chr19 | 21688814 | 21688912 | chr19 | 21769300 | 21769374 |
| chr19 | 22018523 | 22018805 | chr19 | 22034198 | 22034421 | chr19 | 22034447 | 22034813 |
| chr19 | 22610635 | 22610700 | chr19 | 22715140 | 22715443 | chr19 | 23254189 | 23254219 |
| chr19 | 23257703 | 23258007 | chr19 | 23258306 | 23258694 | chr19 | 23299748 | 23300080 |
| chr19 | 23432562 | 23432723 | chr19 | 23433143 | 23433296 | chr19 | 23456615 | 23456881 |
| chr19 | 23598274 | 23598326 | chr19 | 24154592 | 24154621 | chr19 | 24216975 | 24217023 |
| chr19 | 29284452 | 29284575 | chr19 | 29505153 | 29505183 | chr19 | 30015934 | 30015962 |
| chr19 | 30016025 | 30016712 | chr19 | 30016914 | 30016928 | chr19 | 30017452 | 30017509 |
| chr19 | 30017578 | 30017721 | chr19 | 30017766 | 30018608 | chr19 | 30019145 | 30019610 |
| chr19 | 30019661 | 30019838 | chr19 | 30020093 | 30020473 | chr19 | 30130889 | 30130919 |
| chr19 | 30186141 | 30186278 | chr19 | 30215542 | 30215571 | chr19 | 30215753 | 30215782 |
| chr19 | 30252296 | 30252369 | chr19 | 30555329 | 30555376 | chr19 | 30562775 | 30563017 |
| chr19 | 30582601 | 30582649 | chr19 | 30637494 | 30637531 | chr19 | 30703436 | 30703469 |
| chr19 | 30713480 | 30713592 | chr19 | 30713686 | 30713706 | chr19 | 30713909 | 30714047 |
| chr19 | 30714403 | 30714433 | chr19 | 30715402 | 30715766 | chr19 | 30716313 | 30716576 |
| chr19 | 30716953 | 30718149 | chr19 | 30718847 | 30718913 | chr19 | 30719449 | 30720067 |
| chr19 | 30865713 | 30866024 | chr19 | 31804724 | 31804754 | chr19 | 31839838 | 31839873 |
| chr19 | 31841937 | 31842389 | chr19 | 32364365 | 32364403 | chr19 | 32380872 | 32380961 |
| chr19 | 32516399 | 32516516 | chr19 | 32715673 | 32715741 | chr19 | 32835279 | 32835309 |
| chr19 | 32898335 | 32898490 | chr19 | 33167116 | 33167431 | chr19 | 33468018 | 33468055 |
| chr19 | 33571236 | 33571280 | chr19 | 33685544 | 33685581 | chr19 | 33792159 | 33792524 |
| chr19 | 33794675 | 33794744 | chr19 | 34112524 | 34112729 | chr19 | 34113367 | 34113587 |

TABLE 12-continued

| chr | start | end | chr | start | end | chr | start | end |
|---|---|---|---|---|---|---|---|---|
| chr19 | 34114006 | 34114049 | chr19 | 34533139 | 34533169 | chr19 | 34896324 | 34896360 |
| chr19 | 34973243 | 34973255 | chr19 | 34973656 | 34973697 | chr19 | 34973932 | 34973965 |
| chr19 | 35264085 | 35264119 | chr19 | 35396251 | 35396370 | chr19 | 35616341 | 35616397 |
| chr19 | 35781374 | 35781459 | chr19 | 35783136 | 35783231 | chr19 | 35797916 | 35797965 |
| chr19 | 36048595 | 36048771 | chr19 | 36049327 | 36049367 | chr19 | 36049397 | 36049462 |
| chr19 | 36194934 | 36194996 | chr19 | 36200805 | 36200847 | chr19 | 36222432 | 36222534 |
| chr19 | 36250029 | 36250134 | chr19 | 36264697 | 36264773 | chr19 | 36265053 | 36265186 |
| chr19 | 36334979 | 36335147 | chr19 | 36347892 | 36348048 | chr19 | 36410956 | 36411042 |
| chr19 | 36413776 | 36413830 | chr19 | 36450106 | 36450295 | chr19 | 36523333 | 36523480 |
| chr19 | 36531924 | 36531954 | chr19 | 36707435 | 36707467 | chr19 | 36736027 | 36736057 |
| chr19 | 36736319 | 36736491 | chr19 | 36822324 | 36822466 | chr19 | 36822558 | 36822892 |
| chr19 | 36909050 | 36909348 | chr19 | 36909624 | 36909935 | chr19 | 37095655 | 37095812 |
| chr19 | 37096488 | 37096575 | chr19 | 37263532 | 37263584 | chr19 | 37264222 | 37264421 |
| chr19 | 37288013 | 37288424 | chr19 | 37288607 | 37288765 | chr19 | 37341761 | 37341962 |
| chr19 | 37407127 | 37407443 | chr19 | 37464048 | 37464596 | chr19 | 37464667 | 37464696 |
| chr19 | 37569289 | 37569554 | chr19 | 37702003 | 37702169 | chr19 | 37808445 | 37808485 |
| chr19 | 37959874 | 37959963 | chr19 | 37997433 | 37998138 | chr19 | 38042365 | 38042693 |
| chr19 | 38085254 | 38086066 | chr19 | 38146062 | 38146247 | chr19 | 38146457 | 38146568 |
| chr19 | 38182884 | 38182959 | chr19 | 38183112 | 38183299 | chr19 | 38308080 | 38308336 |
| chr19 | 38308395 | 38308466 | chr19 | 38441488 | 38441518 | chr19 | 38481044 | 38481217 |
| chr19 | 38733924 | 38733954 | chr19 | 38736072 | 38736127 | chr19 | 38747159 | 38747582 |
| chr19 | 38747729 | 38747767 | chr19 | 38755272 | 38755344 | chr19 | 38757128 | 38757308 |
| chr19 | 38782559 | 38782589 | chr19 | 38789218 | 38789288 | chr19 | 38873935 | 38873965 |
| chr19 | 38905548 | 38905702 | chr19 | 38974232 | 38974262 | chr19 | 39135294 | 39135454 |
| chr19 | 39273027 | 39273062 | chr19 | 39290904 | 39290944 | chr19 | 39306433 | 39306545 |
| chr19 | 39310469 | 39310584 | chr19 | 39650791 | 39650967 | chr19 | 39687756 | 39687844 |
| chr19 | 39754874 | 39755232 | chr19 | 39755265 | 39755358 | chr19 | 39816936 | 39817085 |
| chr19 | 39934694 | 39934784 | chr19 | 39993477 | 39993656 | chr19 | 39997688 | 39997732 |
| chr19 | 39997749 | 39997813 | chr19 | 40006187 | 40006306 | chr19 | 40006576 | 40006639 |
| chr19 | 40210391 | 40210573 | chr19 | 40724000 | 40724263 | chr19 | 40762943 | 40762972 |
| chr19 | 40829079 | 40829211 | chr19 | 40830032 | 40830118 | chr19 | 40902425 | 40902812 |
| chr19 | 40951175 | 40951357 | chr19 | 40951679 | 40951762 | chr19 | 40991013 | 40991139 |
| chr19 | 41018510 | 41019031 | chr19 | 41025539 | 41025683 | chr19 | 41059909 | 41060306 |
| chr19 | 41073587 | 41073677 | chr19 | 41119177 | 41119276 | chr19 | 41119371 | 41119408 |
| chr19 | 41354666 | 41354722 | chr19 | 41473190 | 41473242 | chr19 | 41641831 | 41641886 |
| chr19 | 41694610 | 41694640 | chr19 | 41698787 | 41698920 | chr19 | 41846193 | 41846325 |
| chr19 | 41881534 | 41881811 | chr19 | 41919917 | 41919971 | chr19 | 42028502 | 42028549 |
| chr19 | 42408300 | 42408330 | chr19 | 42460961 | 42461113 | chr19 | 42827982 | 42828084 |
| chr19 | 42856453 | 42856483 | chr19 | 42911568 | 42911598 | chr19 | 44203830 | 44203877 |
| chr19 | 44405908 | 44406087 | chr19 | 44599783 | 44599883 | chr19 | 44905499 | 44905529 |
| chr19 | 44952282 | 44952881 | chr19 | 45003211 | 45003323 | chr19 | 45300144 | 45300197 |
| chr19 | 45541556 | 45541679 | chr19 | 45570401 | 45570450 | chr19 | 45574465 | 45574495 |
| chr19 | 45574773 | 45574888 | chr19 | 45601380 | 45601410 | chr19 | 45655400 | 45655556 |
| chr19 | 45655648 | 45656363 | chr19 | 45656682 | 45656742 | chr19 | 45656791 | 45656821 |
| chr19 | 45657212 | 45657284 | chr19 | 45678395 | 45678555 | chr19 | 45810102 | 45810267 |
| chr19 | 45835028 | 45835268 | chr19 | 45888946 | 45889224 | chr19 | 45889316 | 45889397 |
| chr19 | 45997528 | 45997584 | chr19 | 46002048 | 46002320 | chr19 | 46234803 | 46234887 |
| chr19 | 46379914 | 46380148 | chr19 | 46404522 | 46404601 | chr19 | 46916725 | 46916987 |
| chr19 | 46917061 | 46917075 | chr19 | 46930129 | 46930200 | chr19 | 46974552 | 46974608 |
| chr19 | 46992718 | 46992866 | chr19 | 46993164 | 46993260 | chr19 | 46993282 | 46993388 |
| chr19 | 46996501 | 46996514 | chr19 | 46996578 | 46996838 | chr19 | 47152978 | 47152990 |
| chr19 | 47200361 | 47200536 | chr19 | 47329748 | 47329867 | chr19 | 47358646 | 47358751 |
| chr19 | 47515017 | 47515047 | chr19 | 47618255 | 47618434 | chr19 | 47776713 | 47776742 |
| chr19 | 47933311 | 47933732 | chr19 | 47951288 | 47951318 | chr19 | 47976399 | 47976429 |
| chr19 | 48003607 | 48003714 | chr19 | 42076642 | 48076672 | chr19 | 48082100 | 48082130 |
| chr19 | 48108151 | 48108320 | chr19 | 48137171 | 48137307 | chr19 | 48151265 | 48151337 |
| chr19 | 48249451 | 48249602 | chr19 | 48614843 | 48614873 | chr19 | 48771551 | 48771600 |
| chr19 | 48777059 | 48777121 | chr19 | 48800603 | 48800769 | chr19 | 48857725 | 48857831 |
| chr19 | 48902848 | 48902878 | chr19 | 48918100 | 48918598 | chr19 | 49043242 | 49043272 |
| chr19 | 49119229 | 49119259 | chr19 | 49127373 | 49127674 | chr19 | 49180462 | 49180558 |
| chr19 | 49256396 | 49256438 | chr19 | 49285456 | 49285593 | chr19 | 49290711 | 49290844 |
| chr19 | 49375050 | 49375216 | chr19 | 49399218 | 49399310 | chr19 | 49402471 | 49402551 |
| chr19 | 49498076 | 49498148 | chr19 | 49575460 | 49575474 | chr19 | 49590284 | 49590399 |
| chr19 | 49628132 | 49628252 | chr19 | 49784869 | 49784935 | chr19 | 49890887 | 49890929 |
| chr19 | 49935736 | 49936174 | chr19 | 49936864 | 49936894 | chr19 | 49997263 | 49997324 |
| chr19 | 49998434 | 49998607 | chr19 | 50028397 | 50028530 | chr19 | 50049718 | 50049953 |
| chr19 | 50203173 | 50203203 | chr19 | 50216042 | 50216072 | chr19 | 50243339 | 50243379 |
| chr19 | 50304736 | 50304766 | chr19 | 50316244 | 50316468 | chr19 | 50319874 | 50319916 |
| chr19 | 50320233 | 50320277 | chr19 | 50353394 | 50353574 | chr19 | 50553680 | 50553709 |
| chr19 | 50553997 | 50554510 | chr19 | 50589044 | 50589079 | chr19 | 50816431 | 50816474 |
| chr19 | 50833828 | 50833863 | chr19 | 50874895 | 50874933 | chr19 | 50898558 | 50898727 |
| chr19 | 50938547 | 50938691 | chr19 | 51041149 | 51041189 | chr19 | 51161225 | 51161255 |
| chr19 | 51162197 | 51162253 | chr19 | 51162428 | 51162527 | chr19 | 51171219 | 51171275 |
| chr19 | 51171828 | 51171860 | chr19 | 51227719 | 51227785 | chr19 | 51228049 | 51228079 |
| chr19 | 51228369 | 51228507 | chr19 | 51304554 | 51304602 | chr19 | 51520423 | 51520453 |
| chr19 | 51715329 | 51715359 | chr19 | 51830845 | 51831002 | chr19 | 51831121 | 51831128 |
| chr19 | 51831360 | 51831390 | chr19 | 51925127 | 51925272 | chr19 | 52097689 | 52097732 |
| chr19 | 52139210 | 52139325 | chr19 | 52207254 | 52207367 | chr19 | 52222523 | 52222923 |

TABLE 12-continued

| chr | start | end | chr | start | end | chr | start | end |
|---|---|---|---|---|---|---|---|---|
| chr19 | 52391235 | 52391264 | chr19 | 52452316 | 52452335 | chr19 | 52552104 | 52552119 |
| chr19 | 52715963 | 52715992 | chr19 | 52839588 | 52839717 | chr19 | 52839742 | 52839938 |
| chr19 | 52872924 | 52873440 | chr19 | 52956805 | 52956848 | chr19 | 53028928 | 53029035 |
| chr19 | 53031185 | 53031215 | chr19 | 53073314 | 53073354 | chr19 | 53073563 | 53073772 |
| chr19 | 53073820 | 53073987 | chr19 | 53141648 | 53141745 | chr19 | 53193858 | 53193893 |
| chr19 | 53194281 | 53194396 | chr19 | 53204758 | 53204837 | chr19 | 53291021 | 53291081 |
| chr19 | 53398908 | 53399031 | chr19 | 53399814 | 53399848 | chr19 | 53436895 | 53437067 |
| chr19 | 53446951 | 53447130 | chr19 | 53496649 | 53496786 | chr19 | 53496814 | 53496846 |
| chr19 | 53561668 | 53561733 | chr19 | 53635952 | 53636091 | chr19 | 53661647 | 53661902 |
| chr19 | 53662174 | 53662694 | chr19 | 53688015 | 53688059 | chr19 | 53696414 | 53696580 |
| chr19 | 53700596 | 53700729 | chr19 | 53757895 | 53758247 | chr19 | 53811858 | 53811988 |
| chr19 | 53836954 | 53836975 | chr19 | 53837377 | 53837432 | chr19 | 53860082 | 53860151 |
| chr19 | 53873182 | 53873212 | chr19 | 53970501 | 53970725 | chr19 | 53970968 | 53971039 |
| chr19 | 53971110 | 53971157 | chr19 | 54023887 | 54024196 | chr19 | 54024521 | 54024884 |
| chr19 | 54271479 | 54271509 | chr19 | 54369555 | 54369681 | chr19 | 54411125 | 54411168 |
| chr19 | 54411556 | 54411586 | chr19 | 54412873 | 54412985 | chr19 | 54481771 | 54481968 |
| chr19 | 54483173 | 54483305 | chr19 | 54483365 | 54483546 | chr19 | 54485403 | 54485646 |
| chr19 | 54485673 | 54485823 | chr19 | 54850630 | 54850659 | chr19 | 55598811 | 55598888 |
| chr19 | 55629883 | 55630028 | chr19 | 55728901 | 55729104 | chr19 | 55849550 | 55849638 |
| chr19 | 56159273 | 56159499 | chr19 | 56189937 | 56189966 | chr19 | 56201643 | 56201938 |
| chr19 | 56340995 | 56341033 | chr19 | 56588656 | 56588780 | chr19 | 56728678 | 56728788 |
| chr19 | 56858084 | 56858227 | chr19 | 56879501 | 56880008 | chr19 | 56904740 | 56905203 |
| chr19 | 56915320 | 56915428 | chr19 | 56988557 | 56988663 | chr19 | 56989528 | 56989625 |
| chr19 | 56989697 | 56989754 | chr19 | 57050463 | 57050493 | chr19 | 57149579 | 57149619 |
| chr19 | 57154885 | 57155017 | chr19 | 57182994 | 57183126 | chr19 | 57276656 | 57276700 |
| chr19 | 57323825 | 57323854 | chr19 | 57610896 | 57610985 | chr19 | 57617522 | 57617716 |
| chr19 | 57617832 | 57618121 | chr19 | 57683148 | 57683162 | chr19 | 57683240 | 57683295 |
| chr19 | 57862395 | 57862783 | chr19 | 58011124 | 58011281 | chr19 | 58038924 | 58038969 |
| chr19 | 58095006 | 58095835 | chr19 | 58111632 | 58111783 | chr19 | 58125544 | 58125881 |
| chr19 | 58144494 | 58144701 | chr19 | 58219839 | 58220392 | chr19 | 58220516 | 58220832 |
| chr19 | 58238326 | 58238738 | chr19 | 58238988 | 58239088 | chr19 | 58316915 | 58317096 |
| chr19 | 58325075 | 58325282 | chr19 | 58400079 | 58400175 | chr19 | 58400417 | 58400518 |
| chr19 | 58458754 | 58458890 | chr19 | 58458979 | 58459201 | chr19 | 58514518 | 58514552 |
| chr19 | 58520739 | 58520941 | chr19 | 58545145 | 58545387 | chr19 | 58545578 | 58545589 |
| chr19 | 58545652 | 58545837 | chr19 | 58609254 | 58609359 | chr19 | 58609473 | 58609525 |
| chr19 | 58509713 | 58609854 | chr19 | 58629975 | 58629975 | chr19 | 58661894 | 58662094 |
| chr19 | 58666171 | 58666313 | chr19 | 58740086 | 58740118 | chr19 | 58807869 | 58807931 |
| chr19 | 58874735 | 58874987 | chr19 | 58951271 | 58951400 | chr19 | 58951526 | 58951916 |
| chr19 | 58964180 | 58964266 | chr19 | 59054642 | 59054774 | chr19 | 118577 | 118751 |
| chr20 | 291148 | 291162 | chr20 | 291221 | 291373 | chr20 | 304259 | 304408 |
| chr20 | 400007 | 400087 | chr20 | 401153 | 401183 | chr20 | 401591 | 401756 |
| chr20 | 523146 | 523193 | chr20 | 590434 | 590502 | chr20 | 592405 | 592449 |
| chr20 | 644182 | 644351 | chr20 | 644407 | 644787 | chr20 | 799104 | 799247 |
| chr20 | 799458 | 799706 | chr20 | 982749 | 982798 | chr20 | 982892 | 982989 |
| chr20 | 1094560 | 1094682 | chr20 | 1197670 | 1197711 | chr20 | 1206855 | 1207034 |
| chr20 | 1783761 | 1784305 | chr20 | 1876110 | 1876176 | chr20 | 1975357 | 1975386 |
| chr20 | 2539331 | 2539771 | chr20 | 2645540 | 2645795 | chr20 | 2668770 | 2668922 |
| chr20 | 2780753 | 2781452 | chr20 | 2781731 | 2781761 | chr20 | 2785659 | 2785866 |
| chr20 | 2785956 | 2786060 | chr20 | 3027758 | 3027931 | chr20 | 3052583 | 3052836 |
| chr20 | 3073561 | 3073899 | chr20 | 3154172 | 3154204 | chr20 | 3204870 | 3204952 |
| chr20 | 3220893 | 3220943 | chr20 | 3229576 | 3229612 | chr20 | 3641774 | 3641937 |
| chr20 | 3663020 | 3663174 | chr20 | 3762152 | 3762181 | chr20 | 3762407 | 3762436 |
| chr20 | 3858389 | 3858632 | chr20 | 3996688 | 3996726 | chr20 | 4040710 | 4040871 |
| chr20 | 4051323 | 4061452 | chr20 | 4085057 | 4085087 | chr20 | 4229402 | 4229432 |
| chr20 | 4229786 | 4230600 | chr20 | 4803070 | 4803650 | chr20 | 4803921 | 4804008 |
| chr20 | 4804566 | 4804732 | chr20 | 5025228 | 5025258 | chr20 | 5106720 | 5106750 |
| chr20 | 5296172 | 5296900 | chr20 | 5297226 | 5297418 | chr20 | 5433047 | 5433085 |
| chr20 | 5610356 | 5610386 | chr20 | 6022797 | 6023045 | chr20 | 6023268 | 6023351 |
| chr20 | 6748925 | 6749036 | chr20 | 7980362 | 7980392 | chr20 | 8112378 | 8112408 |
| chr20 | 8112739 | 8113022 | chr20 | 8113557 | 8113605 | chr20 | 9487385 | 9487719 |
| chr20 | 9487789 | 9487997 | chr20 | 9488376 | 9488848 | chr20 | 9489070 | 9489214 |
| chr20 | 9489424 | 9489708 | chr20 | 9495271 | 9495509 | chr20 | 9496330 | 9496530 |
| chr20 | 9496581 | 9496833 | chr20 | 9497035 | 9497109 | chr20 | 10198289 | 10198600 |
| chr20 | 10198941 | 10198945 | chr20 | 13200599 | 13200634 | chr20 | 14447971 | 14448144 |
| chr20 | 16564749 | 16565030 | chr20 | 17206513 | 17206747 | chr20 | 17207874 | 17207930 |
| chr20 | 17208585 | 17208620 | chr20 | 18039823 | 18039897 | chr20 | 18073183 | 18073276 |
| chr20 | 18073312 | 18073461 | chr20 | 18448982 | 18449076 | chr20 | 18489463 | 18489658 |
| chr20 | 19128288 | 19128473 | chr20 | 19739613 | 19739696 | chr20 | 19928306 | 19928461 |
| chr20 | 20344498 | 20344559 | chr20 | 20347460 | 20347709 | chr20 | 20347737 | 20348154 |
| chr20 | 20348526 | 20348605 | chr20 | 20349153 | 20349255 | chr20 | 20349574 | 20349604 |
| chr20 | 21080714 | 21080956 | chr20 | 21081029 | 21081844 | chr20 | 21082095 | 21082123 |
| chr20 | 21082216 | 21082253 | chr20 | 21082532 | 21082917 | chr20 | 21083421 | 21084361 |
| chr20 | 21085831 | 21085864 | chr20 | 21086195 | 21086451 | chr20 | 21086866 | 21087188 |
| chr20 | 21372174 | 21372192 | chr20 | 21372295 | 21372725 | chr20 | 21376250 | 21376336 |
| chr20 | 21376703 | 21376733 | chr20 | 21376877 | 21377128 | chr20 | 21377474 | 21377640 |
| chr20 | 21377738 | 21378551 | chr20 | 21486375 | 21486659 | chr20 | 21486786 | 21486881 |
| chr20 | 21487153 | 21487581 | chr20 | 21488158 | 21488351 | chr20 | 21489240 | 21489446 |
| chr20 | 21489622 | 21489703 | chr20 | 21490175 | 21490762 | chr20 | 21490815 | 21491345 |

TABLE 12-continued

| chr | start | end | chr | start | end | chr | start | end |
|---|---|---|---|---|---|---|---|---|
| chr20 | 21492378 | 21492409 | chr20 | 21492508 | 21492825 | chr20 | 21493308 | 21493993 |
| chr20 | 21494531 | 21494703 | chr20 | 21495942 | 21495986 | chr20 | 21496260 | 21496294 |
| chr20 | 21496684 | 21497136 | chr20 | 21497413 | 21498638 | chr20 | 21499961 | 21500134 |
| chr20 | 21501445 | 21501724 | chr20 | 21502037 | 21502144 | chr20 | 21502590 | 21502699 |
| chr20 | 21502838 | 21503117 | chr20 | 21503455 | 21503773 | chr20 | 21682399 | 21682456 |
| chr20 | 21683311 | 21683651 | chr20 | 21685385 | 21685526 | chr20 | 21686235 | 21686677 |
| chr20 | 21687009 | 21687382 | chr20 | 21689956 | 21690185 | chr20 | 21694499 | 21694529 |
| chr20 | 21695088 | 21695273 | chr20 | 21695306 | 21695357 | chr20 | 21748445 | 21748491 |
| chr20 | 22401392 | 22401421 | chr20 | 22557396 | 22557675 | chr20 | 22557979 | 22558114 |
| chr20 | 22558637 | 22658669 | chr20 | 22559645 | 22559690 | chr20 | 22562721 | 22562840 |
| chr20 | 22563563 | 22563602 | chr20 | 22564235 | 22564265 | chr20 | 22566961 | 22566990 |
| chr20 | 23015917 | 23015946 | chr20 | 23029110 | 23029151 | chr20 | 23029589 | 23030085 |
| chr20 | 23030292 | 23030357 | chr20 | 23031548 | 23031692 | chr20 | 23138383 | 23138444 |
| chr20 | 23406698 | 23406830 | chr20 | 24450231 | 24450513 | chr20 | 24450820 | 24451019 |
| chr20 | 24451450 | 04451592 | chr20 | 24505190 | 24505252 | chr20 | 24726701 | 24726825 |
| chr20 | 25058385 | 25058616 | chr20 | 25061746 | 25061788 | chr20 | 25061979 | 25062311 |
| chr20 | 25062511 | 25062645 | chr20 | 25062708 | 25062817 | chr20 | 25062871 | 25062880 |
| chr20 | 25063780 | 25063906 | chr20 | 25063994 | 25064458 | chr20 | 25065179 | 25065395 |
| chr20 | 25086082 | 25086275 | chr20 | 25223141 | 25223277 | chr20 | 25230509 | 25230799 |
| chr20 | 25334513 | 25334650 | chr20 | 25344027 | 25344118 | chr20 | 26188812 | 26188961 |
| chr20 | 26190313 | 26190361 | chr20 | 29832911 | 29833090 | chr20 | 29914002 | 29914139 |
| chr20 | 29956013 | 29956042 | chr20 | 29956570 | 29956599 | chr20 | 30101523 | 30101743 |
| chr20 | 30162296 | 30162459 | chr20 | 30174561 | 30174645 | chr20 | 30186068 | 30186165 |
| chr20 | 30201236 | 30201360 | chr20 | 30280423 | 30280509 | chr20 | 30297090 | 30297217 |
| chr20 | 30468319 | 30468349 | chr20 | 30582750 | 30582978 | chr20 | 30639141 | 30639319 |
| chr20 | 30639632 | 30639847 | chr20 | 30640106 | 30640270 | chr20 | 30778024 | 30778313 |
| chr20 | 31035471 | 31035518 | chr20 | 31115683 | 31115799 | chr20 | 31151769 | 31151799 |
| chr20 | 31207211 | 31207283 | chr20 | 31282734 | 31282903 | chr20 | 32301797 | 32301953 |
| chr20 | 32450248 | 32450427 | chr20 | 32701064 | 32701320 | chr20 | 32716914 | 32716949 |
| chr20 | 32768669 | 32768728 | chr20 | 32893006 | 32893125 | chr20 | 33540284 | 33540550 |
| chr20 | 33547485 | 33547585 | chr20 | 33574914 | 33574992 | chr20 | 34041981 | 34042072 |
| chr20 | 34148020 | 34148254 | chr20 | 34188617 | 34188631 | chr20 | 34188748 | 34189088 |
| chr20 | 34189167 | 34189391 | chr20 | 34189680 | 34189910 | chr20 | 35640448 | 35640561 |
| chr20 | 35742487 | 35742607 | chr20 | 35892604 | 35892746 | chr20 | 36183184 | 36183340 |
| chr20 | 36531799 | 36531910 | chr20 | 36781324 | 36781354 | chr20 | 37302697 | 37303343 |
| chr20 | 37351793 | 37352515 | chr20 | 37352607 | 37352626 | chr20 | 37353193 | 37353236 |
| chr20 | 37353455 | 37353718 | chr20 | 37354145 | 37354831 | chr20 | 37354994 | 37355202 |
| chr20 | 37355847 | 37356042 | chr20 | 37356169 | 37356827 | chr20 | 37357216 | 37357353 |
| chr20 | 37357825 | 37358190 | chr20 | 37434552 | 37434721 | chr20 | 37434737 | 37434744 |
| chr20 | 37435104 | 37435218 | chr20 | 37435488 | 37435860 | chr20 | 39316203 | 39316322 |
| chr20 | 39316984 | 39317392 | chr20 | 39317750 | 39318166 | chr20 | 39318383 | 39318415 |
| chr20 | 39319126 | 39319203 | chr20 | 39319515 | 39319653 | chr20 | 39995146 | 39995813 |
| chr20 | 40500546 | 40500638 | chr20 | 40515378 | 40515504 | chr20 | 40743859 | 40743888 |
| chr20 | 41817786 | 41817915 | chr20 | 41818008 | 41818085 | chr20 | 41818567 | 41818748 |
| chr20 | 41818805 | 41818914 | chr20 | 42136330 | 42136411 | chr20 | 42218429 | 42218664 |
| chr20 | 42281425 | 42281455 | chr20 | 42543754 | 42543853 | chr20 | 42544091 | 42544533 |
| chr20 | 42544728 | 42544984 | chr20 | 42852751 | 42852915 | chr20 | 42876525 | 42876575 |
| chr20 | 43438071 | 43438085 | chr20 | 43438335 | 43438466 | chr20 | 43438982 | 43439022 |
| chr20 | 43439291 | 43439510 | chr20 | 43952174 | 43952302 | chr20 | 44003765 | 44003811 |
| chr20 | 44452731 | 44453063 | chr20 | 44519077 | 44519107 | chr20 | 44601547 | 44601716 |
| chr20 | 44602074 | 44602364 | chr20 | 44639181 | 44639496 | chr20 | 44640338 | 44640367 |
| chr20 | 44660750 | 44660877 | chr20 | 44686423 | 44686614 | chr20 | 44686628 | 44686756 |
| chr20 | 44746484 | 44746781 | chr20 | 44803174 | 44803675 | chr20 | 44875240 | 44875411 |
| chr20 | 44880041 | 44880076 | chr20 | 44937202 | 44937411 | chr20 | 44937426 | 44937643 |
| chr20 | 44941518 | 44941661 | chr20 | 45142000 | 45142038 | chr20 | 45142152 | 45142272 |
| chr20 | 45279854 | 45279981 | chr20 | 45280040 | 45280302 | chr20 | 45280344 | 45280428 |
| chr20 | 45337804 | 45337945 | chr20 | 45524523 | 45524353 | chr20 | 47247239 | 47247450 |
| chr20 | 42274032 | 47274062 | chr20 | 47296109 | 47296231 | chr20 | 47443729 | 47443936 |
| chr20 | 47443945 | 47444282 | chr20 | 47450370 | 47450490 | chr20 | 47815615 | 47815711 |
| chr20 | 47835328 | 47835358 | chr20 | 47905426 | 47905603 | chr20 | 47934824 | 47935268 |
| chr20 | 47935495 | 47935567 | chr20 | 47935928 | 47936027 | chr20 | 48184381 | 48184435 |
| chr20 | 48595665 | 48696227 | chr20 | 48768118 | 48768148 | chr20 | 48774527 | 48774569 |
| chr20 | 49204179 | 49204449 | chr20 | 49261803 | 49262104 | chr20 | 49323924 | 49324125 |
| chr20 | 49350910 | 49351041 | chr20 | 49351564 | 49351649 | chr20 | 49358137 | 49358396 |
| chr20 | 49377755 | 49378043 | chr20 | 49381140 | 49381240 | chr20 | 49575909 | 49575919 |
| chr20 | 49639777 | 49639856 | chr20 | 49639883 | 49639996 | chr20 | 49640095 | 49640157 |
| chr20 | 49969348 | 49969515 | chr20 | 50160756 | 50160905 | chr20 | 50383224 | 50383423 |
| chr20 | 50384767 | 50384896 | chr20 | 50602134 | 50602264 | chr20 | 50693423 | 50693468 |
| chr20 | 50720437 | 50721200 | chr20 | 50721235 | 50721670 | chr20 | 50721989 | 50722193 |
| chr20 | 50722598 | 50722821 | chr20 | 51589766 | 51589908 | chr20 | 52226337 | 52226366 |
| chr20 | 52311463 | 52311728 | chr20 | 52401713 | 52401775 | chr20 | 52789445 | 52789475 |
| chr20 | 52789853 | 52789948 | chr20 | 52790082 | 52790155 | chr20 | 53092192 | 53092376 |
| chr20 | 53093085 | 53093115 | chr20 | 54522432 | 54522631 | chr20 | 54578507 | 54578722 |
| chr20 | 54579892 | 54579958 | chr20 | 54580070 | 54580323 | chr20 | 54580622 | 54580691 |
| chr20 | 55008041 | 55008194 | chr20 | 55071563 | 55071712 | chr20 | 55200035 | 55200310 |
| chr20 | 55200616 | 55200706 | chr20 | 55200922 | 55201092 | chr20 | 55201764 | 55202068 |
| chr20 | 55202359 | 55202626 | chr20 | 55202826 | 55203107 | chr20 | 55204322 | 55204604 |
| chr20 | 55204966 | 55205000 | chr20 | 56206294 | 55206393 | chr20 | 56206739 | 55206774 |

TABLE 12-continued

| chr | start | end | chr | start | end | chr | start | end |
|---|---|---|---|---|---|---|---|---|
| chr20 | 55499496 | 55499709 | chr20 | 55500016 | 55500085 | chr20 | 55500441 | 55500720 |
| chr20 | 55693527 | 55693662 | chr20 | 55841134 | 55841356 | chr20 | 55842096 | 55842189 |
| chr20 | 55959212 | 55959250 | chr20 | 56766160 | 56766190 | chr20 | 56803398 | 56803441 |
| chr20 | 56803842 | 56803920 | chr20 | 56998280 | 56998337 | chr20 | 57089452 | 57089459 |
| chr20 | 57090104 | 57090173 | chr20 | 57224842 | 57225079 | chr20 | 57225219 | 57225307 |
| chr20 | 57484406 | 57484445 | chr20 | 58179809 | 58179854 | chr20 | 58180214 | 58180402 |
| chr20 | 58508887 | 58508943 | chr20 | 59525138 | 59525300 | chr20 | 59804170 | 59804235 |
| chr20 | 59826192 | 59826221 | chr20 | 59826962 | 59826977 | chr20 | 59828341 | 59828407 |
| chr20 | 59880433 | 59880477 | chr20 | 59910175 | 59910346 | chr20 | 59973028 | 59973072 |
| chr20 | 60202594 | 60202624 | chr20 | 60235333 | 60235526 | chr20 | 60238381 | 60238472 |
| chr20 | 60238877 | 60238980 | chr20 | 60243944 | 60244107 | chr20 | 60329584 | 60329738 |
| chr20 | 60333880 | 60333969 | chr20 | 60359849 | 60359879 | chr20 | 60375036 | 60375070 |
| chr20 | 60439634 | 60439755 | chr20 | 60453925 | 60454091 | chr20 | 60477306 | 60477537 |
| chr20 | 60485374 | 60485425 | chr20 | 60503030 | 60503060 | chr20 | 60545561 | 60545792 |
| chr20 | 60620122 | 60620557 | chr20 | 60772853 | 60773878 | chr20 | 60789965 | 60790124 |
| chr20 | 60816241 | 60816271 | chr20 | 60892164 | 60892222 | chr20 | 60926019 | 60926049 |
| chr20 | 60970953 | 60970983 | chr20 | 60983859 | 60984010 | chr20 | 60984341 | 60984465 |
| chr20 | 61288068 | 61288156 | chr20 | 61288463 | 61288534 | chr20 | 61294693 | 61294857 |
| chr20 | 61340581 | 61340689 | chr20 | 61412313 | 61412438 | chr20 | 61505851 | 61506330 |
| chr20 | 61532546 | 61532605 | chr20 | 61560418 | 61560460 | chr20 | 61560529 | 61560922 |
| chr20 | 61585771 | 61585922 | chr20 | 61585990 | 61586004 | chr20 | 61636876 | 61636890 |
| chr20 | 61637468 | 61637648 | chr20 | 61637736 | 61637956 | chr20 | 61638221 | 61638469 |
| chr20 | 61638535 | 61638631 | chr20 | 61703710 | 61703761 | chr20 | 61703846 | 61703875 |
| chr20 | 61714591 | 61714621 | chr20 | 61734420 | 61734481 | chr20 | 61747894 | 61747934 |
| chr20 | 61763598 | 61763628 | chr20 | 61765285 | 61765425 | chr20 | 61808181 | 61808270 |
| chr20 | 61808667 | 61809005 | chr20 | 61809219 | 61809631 | chr20 | 61809841 | 61810089 |
| chr20 | 61823170 | 61823339 | chr20 | 61862380 | 61862452 | chr20 | 61885247 | 61885462 |
| chr20 | 61886068 | 61886203 | chr20 | 61886257 | 61886258 | chr20 | 61886725 | 61886755 |
| chr20 | 61974191 | 61974354 | chr20 | 61980860 | 61980975 | chr20 | 62031173 | 62031234 |
| chr20 | 62032058 | 62032095 | chr20 | 62037559 | 62037598 | chr20 | 62046227 | 62046421 |
| chr20 | 62058700 | 62058786 | chr20 | 62090524 | 62090778 | chr20 | 62097666 | 62097695 |
| chr20 | 62115047 | 62115266 | chr20 | 62119339 | 62119618 | chr20 | 62119923 | 62120171 |
| chr20 | 62126118 | 62126429 | chr20 | 62157151 | 62157307 | chr20 | 62165631 | 62165762 |
| chr20 | 62167554 | 62167584 | chr20 | 62170179 | 62170209 | chr20 | 62172945 | 62173055 |
| chr20 | 62185386 | 62185444 | chr20 | 62260818 | 62260905 | chr20 | 62261532 | 62261562 |
| chr20 | 62284487 | 62284615 | chr20 | 62314848 | 62314955 | chr20 | 62321206 | 62321341 |
| chr20 | 62321638 | 62321881 | chr20 | 62340321 | 62340442 | chr20 | 62383218 | 62383289 |
| chr20 | 62391938 | 62391968 | chr20 | 62461349 | 62461475 | chr20 | 62488293 | 62488350 |
| chr20 | 62497836 | 62497920 | chr20 | 62631351 | 62631593 | chr20 | 62680657 | 62680739 |
| chr20 | 62715014 | 62715069 | chr20 | 62786577 | 62786791 | chr20 | 62795643 | 62795672 |
| chr21 | 19274828 | 19274858 | chr21 | 22370332 | 22370458 | chr21 | 22370688 | 22370718 |
| chr21 | 26934368 | 26934786 | chr21 | 27011773 | 27011807 | chr21 | 27012373 | 27012431 |
| chr21 | 27944995 | 27945081 | chr21 | 27945693 | 27945722 | chr21 | 28216634 | 28217690 |
| chr21 | 28218774 | 28219045 | chr21 | 28338836 | 28338887 | chr21 | 28339247 | 28339501 |
| chr21 | 28339892 | 28340048 | chr21 | 28340063 | 28340318 | chr21 | 31015201 | 31015231 |
| chr21 | 31056850 | 31056927 | chr21 | 31311404 | 31311553 | chr21 | 31312080 | 31312105 |
| chr21 | 31312313 | 31312445 | chr21 | 32253745 | 32253774 | chr21 | 33043985 | 33044051 |
| chr21 | 33244921 | 33245040 | chr21 | 33245683 | 33245718 | chr21 | 33246009 | 33246091 |
| chr21 | 33627549 | 33627649 | chr21 | 33721756 | 33721824 | chr21 | 33785288 | 33785325 |
| chr21 | 33983236 | 33983488 | chr21 | 34392206 | 34392403 | chr21 | 34392437 | 34392566 |
| chr21 | 34395302 | 34396269 | chr21 | 34396795 | 34397091 | chr21 | 34398070 | 34398634 |
| chr21 | 34398933 | 34399258 | chr21 | 34399442 | 34400104 | chr21 | 34400232 | 34400258 |
| chr21 | 34401185 | 34401392 | chr21 | 34442595 | 34442665 | chr21 | 34443103 | 34443262 |
| chr21 | 34443509 | 34443686 | chr21 | 34443893 | 34443956 | chr21 | 34444163 | 34444362 |
| chr21 | 34444445 | 34444598 | chr21 | 34469746 | 34469844 | chr21 | 35051159 | 35051231 |
| chr21 | 36041985 | 36042028 | chr21 | 36042092 | 36042238 | chr21 | 36042658 | 36042861 |
| chr21 | 37527928 | 37527958 | chr21 | 32758570 | 37758652 | chr21 | 37775034 | 37775141 |
| chr21 | 38064457 | 38064683 | chr21 | 38064966 | 38065522 | chr21 | 38065955 | 38066112 |
| chr21 | 38067203 | 38067233 | chr21 | 38068178 | 38068229 | chr21 | 38068647 | 38068783 |
| chr21 | 38069093 | 38069203 | chr21 | 38069459 | 38069496 | chr21 | 38069854 | 38070162 |
| chr21 | 38070705 | 38070765 | chr21 | 38071791 | 38071905 | chr21 | 38073007 | 38073070 |
| chr21 | 38073300 | 38073525 | chr21 | 38073616 | 38073860 | chr21 | 38078415 | 38078487 |
| chr21 | 38079988 | 38080062 | chr21 | 38080175 | 38080386 | chr21 | 38080551 | 38080684 |
| chr21 | 38081085 | 38081192 | chr21 | 38081666 | 38081835 | chr21 | 38082042 | 38082072 |
| chr21 | 38082315 | 38082345 | chr21 | 38082930 | 38083196 | chr21 | 38092179 | 38092221 |
| chr21 | 38119904 | 38120312 | chr21 | 38638422 | 38638526 | chr21 | 38935478 | 38935549 |
| chr21 | 39047776 | 39047838 | chr21 | 39870612 | 39870641 | chr21 | 40033619 | 40033648 |
| chr21 | 40033877 | 40033906 | chr21 | 40034756 | 40034785 | chr21 | 40984685 | 40984900 |
| chr21 | 42596911 | 42597043 | chr21 | 42617963 | 42617995 | chr21 | 42649172 | 42649202 |
| chr21 | 43186698 | 43186889 | chr21 | 43240082 | 43240112 | chr21 | 43256565 | 43256603 |
| chr21 | 43376373 | 43376403 | chr21 | 43393528 | 43393713 | chr21 | 43485279 | 43485348 |
| chr21 | 43786683 | 43786713 | chr21 | 43991463 | 43991493 | chr21 | 44250815 | 44250855 |
| chr21 | 44283581 | 44283774 | chr21 | 44494941 | 44495155 | chr21 | 44514762 | 44514791 |
| chr21 | 44524441 | 44524470 | chr21 | 44837088 | 44837213 | chr21 | 44847591 | 44847622 |
| chr21 | 44866603 | 44866711 | chr21 | 44886709 | 44886870 | chr21 | 45118492 | 45118644 |
| chr21 | 45131875 | 45131905 | chr21 | 45148615 | 45148758 | chr21 | 45195149 | 45195319 |
| chr21 | 45271643 | 45271688 | chr21 | 45273717 | 45273913 | chr21 | 45277332 | 45277513 |
| chr21 | 45290014 | 45290044 | chr21 | 45508617 | 45508647 | chr21 | 45521343 | 45521438 |

TABLE 12-continued

| chr | start | end | chr | start | end | chr | start | end |
|---|---|---|---|---|---|---|---|---|
| chr21 | 45621533 | 45621573 | chr21 | 45717477 | 45717548 | chr21 | 45791079 | 45791109 |
| chr21 | 45847832 | 45847973 | chr21 | 46036642 | 46036767 | chr21 | 46125933 | 46126427 |
| chr21 | 46126567 | 46126721 | chr21 | 46127039 | 46127094 | chr21 | 46127542 | 46127692 |
| chr21 | 46128902 | 46128938 | chr21 | 46129444 | 46129485 | chr21 | 46193414 | 46193542 |
| chr21 | 46257116 | 46257273 | chr21 | 46310428 | 46310491 | chr21 | 46318285 | 46318343 |
| chr21 | 46319156 | 46319459 | chr21 | 46359187 | 46359248 | chr21 | 46452374 | 46452539 |
| chr21 | 46677734 | 46677795 | chr21 | 46825825 | 46826067 | chr21 | 46847654 | 46847684 |
| chr21 | 46863658 | 46863708 | chr21 | 46925780 | 46925925 | chr21 | 46926459 | 46926565 |
| chr21 | 46935739 | 46935936 | chr21 | 47010409 | 47010451 | chr21 | 47062753 | 47062825 |
| chr21 | 47063538 | 47063962 | chr21 | 47064250 | 47064377 | chr21 | 47404174 | 47404325 |
| chr21 | 47504861 | 47504895 | chr21 | 47518776 | 47518814 | chr21 | 47717560 | 47717589 |
| chr21 | 47746270 | 47746393 | chr22 | 17081932 | 17081935 | chr22 | 17082989 | 17083003 |
| chr22 | 17083396 | 17083410 | chr22 | 17601086 | 17601133 | chr22 | 17601260 | 17601368 |
| chr22 | 17602511 | 17602624 | chr22 | 17850454 | 17850621 | chr22 | 18009969 | 18010121 |
| chr22 | 18110495 | 18110593 | chr22 | 18328127 | 18328268 | chr22 | 18340822 | 18340868 |
| chr22 | 18527328 | 18627537 | chr22 | 19017532 | 19017567 | chr22 | 19117564 | 19117594 |
| chr22 | 19136907 | 19136936 | chr22 | 19137859 | 19137888 | chr22 | 19138109 | 19138138 |
| chr22 | 19510799 | 19510946 | chr22 | 19511142 | 19511455 | chr22 | 19511542 | 19511567 |
| chr22 | 19511849 | 19511875 | chr22 | 19702265 | 19702410 | chr22 | 19706171 | 19706677 |
| chr22 | 19742834 | 19742969 | chr22 | 19748644 | 19748908 | chr22 | 20229079 | 20229239 |
| chr22 | 20792482 | 20792641 | chr22 | 20864642 | 20864672 | chr22 | 20940868 | 20940898 |
| chr22 | 21042829 | 21043014 | chr22 | 21153867 | 21154000 | chr22 | 21270750 | 21270834 |
| chr22 | 21276140 | 21276261 | chr22 | 21299605 | 21299635 | chr22 | 21304771 | 2130500Z |
| chr22 | 21368587 | 21368617 | chr22 | 21977314 | 21977347 | chr22 | 21982792 | 21982972 |
| chr22 | 22005794 | 22006759 | chr22 | 22023273 | 22023451 | chr22 | 22058203 | 22058238 |
| chr22 | 22201344 | 22201568 | chr22 | 22862787 | 22862862 | chr22 | 22901105 | 22901455 |
| chr22 | 23791402 | 23791432 | chr22 | 23801459 | 23801610 | chr22 | 23991201 | 23991217 |
| chr22 | 24145484 | 24145513 | chr22 | 24179940 | 24179982 | chr22 | 24180687 | 24180766 |
| chr22 | 24560375 | 24560526 | chr22 | 24820330 | 24820396 | chr22 | 25678748 | 25678868 |
| chr22 | 25679043 | 25679249 | chr22 | 25679268 | 25679337 | chr22 | 25817107 | 25817180 |
| chr22 | 25817458 | 25817612 | chr22 | 27053194 | 27053250 | chr22 | 28198569 | 28198605 |
| chr22 | 28371649 | 28371679 | chr22 | 28838200 | 28838292 | chr22 | 28838509 | 28838551 |
| chr22 | 28839122 | 28839263 | chr22 | 29076592 | 29076622 | chr22 | 29091824 | 29091853 |
| chr22 | 29445752 | 29445923 | chr22 | 29876191 | 29876220 | chr22 | 29877223 | 29877299 |
| chr22 | 29977614 | 29977863 | chr22 | 30084358 | 30084388 | chr22 | 30090739 | 30090769 |
| chr22 | 30116904 | 30117146 | chr22 | 30158330 | 30158639 | chr22 | 30476197 | 30476220 |
| chr22 | 30784196 | 30784278 | chr22 | 30881582 | 30881612 | chr22 | 30938543 | 30938584 |
| chr22 | 31198492 | 31198637 | chr22 | 31218510 | 31218540 | chr22 | 31218794 | 31218829 |
| chr22 | 31481130 | 31481332 | chr22 | 32061344 | 32061374 | chr22 | 32748936 | 32748966 |
| chr22 | 32868720 | 32868837 | chr22 | 33197603 | 33197652 | chr22 | 33453877 | 33453954 |
| chr22 | 33454194 | 33454258 | chr22 | 33454346 | 33454366 | chr22 | 35079219 | 35079345 |
| chr22 | 35656581 | 35656610 | chr22 | 35768531 | 35768719 | chr22 | 35848358 | 35848670 |
| chr22 | 35938746 | 35939000 | chr22 | 36567866 | 36567896 | chr22 | 36681295 | 36681341 |
| chr22 | 36855297 | 36855335 | chr22 | 36855568 | 36855598 | chr22 | 36880362 | 36880462 |
| chr22 | 36902291 | 36902381 | chr22 | 37302073 | 37302103 | chr22 | 37720961 | 37721163 |
| chr22 | 38002684 | 38002733 | chr22 | 38087310 | 38087367 | chr22 | 38182815 | 38182981 |
| chr22 | 38199769 | 38199894 | chr22 | 38220653 | 38221201 | chr22 | 38477069 | 38477131 |
| chr22 | 38477297 | 38477794 | chr22 | 38507316 | 38507346 | chr22 | 38592856 | 38593076 |
| chr22 | 38639229 | 38639259 | chr22 | 38874215 | 38874362 | chr22 | 39094890 | 39094964 |
| chr22 | 39098022 | 39098064 | chr22 | 39112502 | 39112584 | chr22 | 39784480 | 39784598 |
| chr22 | 39830355 | 39830457 | chr22 | 39853521 | 39853592 | chr22 | 39932499 | 39932563 |
| chr22 | 39954429 | 39954516 | chr22 | 40042627 | 40042743 | chr22 | 40075157 | 40075302 |
| chr22 | 40226345 | 40226389 | chr22 | 40767753 | 40767936 | chr22 | 40807034 | 40807063 |
| chr22 | 40895978 | 40896029 | chr22 | 41048732 | 41049109 | chr22 | 41217105 | 41217405 |
| chr22 | 41634393 | 41634542 | chr22 | 41637064 | 41637129 | chr22 | 41648414 | 41648444 |
| chr22 | 41657233 | 41657350 | chr22 | 41690119 | 41690149 | chr22 | 41839432 | 41839498 |
| chr22 | 42068010 | 42068172 | chr22 | 42096002 | 42096190 | chr22 | 42310087 | 42310220 |
| chr22 | 42311521 | 42311587 | chr22 | 42343416 | 42343676 | chr22 | 42353611 | 42353892 |
| chr22 | 42667358 | 42667432 | chr22 | 42916449 | 42916479 | chr22 | 43012543 | 43012877 |
| chr22 | 43083130 | 43083166 | chr22 | 43434441 | 43434477 | chr22 | 43540672 | 43540702 |
| chr22 | 43740084 | 43740128 | chr22 | 43808280 | 43808428 | chr22 | 44208418 | 44208448 |
| chr22 | 44258366 | 44258506 | chr22 | 44287650 | 44287696 | chr22 | 44455707 | 44455740 |
| chr22 | 45087614 | 45087649 | chr22 | 45088602 | 45088743 | chr22 | 45135939 | 45135979 |
| chr22 | 45252427 | 45252463 | chr22 | 45277292 | 45277322 | chr22 | 45313416 | 45313446 |
| chr22 | 45403086 | 45403133 | chr22 | 45403478 | 45403714 | chr22 | 45404197 | 45404433 |
| chr22 | 45404994 | 45405010 | chr22 | 45405047 | 45405061 | chr22 | 45405318 | 45405418 |
| chr22 | 45405620 | 45405768 | chr22 | 45406271 | 45406328 | chr22 | 45593643 | 45593715 |
| chr22 | 45604184 | 45604343 | chr22 | 45719161 | 45719190 | chr22 | 46262452 | 46263051 |
| chr22 | 46263512 | 46263623 | chr22 | 46263744 | 46263809 | chr22 | 46276749 | 46276820 |
| chr22 | 46438085 | 46438217 | chr22 | 46455833 | 46455905 | chr22 | 46599623 | 46599725 |
| chr22 | 46931260 | 46931332 | chr22 | 46933089 | 46933237 | chr22 | 47005080 | 47005154 |
| chr22 | 47023044 | 47023191 | chr22 | 47054686 | 47054716 | chr22 | 47193335 | 47193371 |
| chr22 | 47395475 | 47395505 | chr22 | 47525846 | 47525885 | chr22 | 47584867 | 47585074 |
| chr22 | 48027626 | 48027655 | chr22 | 48885530 | 48885837 | chr22 | 48886659 | 48886849 |
| chr22 | 48931881 | 48932027 | chr22 | 48971533 | 48971679 | chr22 | 48972220 | 48972465 |
| chr22 | 49852617 | 49852647 | chr22 | 49979646 | 49979757 | chr22 | 50001699 | 50001882 |
| chr22 | 50002787 | 50002819 | chr22 | 50003204 | 50003234 | chr22 | 50010113 | 50010258 |
| chr22 | 50010461 | 50010585 | chr22 | 50031691 | 50031721 | chr22 | 50064760 | 50064944 |

TABLE 12-continued

| chr | start | end | chr | start | end | chr | start | end |
|---|---|---|---|---|---|---|---|---|
| chr22 | 50149431 | 50149470 | chr22 | 50251536 | 50251582 | chr22 | 50467005 | 50467035 |
| chr22 | 50467876 | 50468105 | chr22 | 50497147 | 50497182 | chr22 | 50497214 | 50497287 |
| chr22 | 50523672 | 50623714 | chr22 | 50623742 | 50623815 | chr22 | 50768840 | 50768876 |
| chr22 | 50899293 | 50899672 | chr22 | 50939073 | 50939111 | chr22 | 50943093 | 50943262 |
| chr22 | 50986016 | 50986045 | chr22 | 51042278 | 51042404 | chr22 | 51042458 | 51042565 |
| chr22 | 51112150 | 51112232 | chrX | 3631506 | 3631633 | chrX | 3746612 | 3746642 |
| chrX | 6145331 | 6145688 | chrX | 8698863 | 8698897 | chrX | 8699504 | 8699566 |
| chrX | 15807465 | 15807693 | chrX | 20148710 | 20148739 | chrX | 20160594 | 20160914 |
| chrX | 44730179 | 44730271 | chrX | 47039370 | 47039399 | chrX | 47426106 | 47426144 |
| chrX | 47426780 | 47426821 | chrX | 50557075 | 50557075 | chrX | 66931448 | 66931477 |
| chrX | 66937356 | 66937385 | chrX | 66943529 | 66943567 | chrX | 70339239 | 70339268 |
| chrX | 100228394 | 100228431 | chrX | 100740260 | 100740289 | chrX | 101906099 | 101906120 |
| chrX | 102000609 | 102000758 | chrX | 134156560 | 134156680 | chrX | 136656563 | 136656592 |
| chrY | 2655316 | 2655346 | chrY | 3446305 | 3446441 | chrY | 3838889 | 3838919 |
| chrY | 3968100 | 3968132 | chrY | 13316002 | 13316132 | chrY | 14532822 | 14532852 |
| chrY | 14533556 | 14533613 | chrY | 21204734 | 21205113 | chrY | 22530026 | 22530073 |
| MCV-R17b | 111 | 140 | MCV-R17b | 368 | 397 | MCV-R17b | 625 | 654 |
| MCV-R17b | 882 | 911 | MCV-R17b | 1139 | 1168 | MCV-R17b | 1396 | 1425 |
| MCV-R17b | 1653 | 1682 | MCV-R17b | 1910 | 1939 | MCV-R17b | 2167 | 2196 |
| MCV-R17b | 2424 | 2453 | MCV-R17b | 2681 | 2710 | MCV-R17b | 2938 | 2967 |
| MCV-R17b | 3195 | 3224 | MCV-R17b | 3452 | 3481 | MCV-R17b | 3709 | 3738 |
| MCV-R176 | 3966 | 3995 | MCV-R17b | 4223 | 4252 | MCV-R17b | 4480 | 4509 |
| MCV-R17b | 4737 | 4766 | MCV-R17b | 4994 | 5023 | AC160854.2_10710-13495 | 1027 | 1057 |
| AC211950.2_11234-25326 | 129 | 257 | AC211950.2_11234-25326 | 13335 | 13445 | AC211950.2_11234-25326 | 13743 | 13889 |
| AC241851.2_88-34049 | 14729 | 14973 | AC241851.2_88-34049 | 15261 | 15350 | AEKP01168736.1_1-4752 | 1754 | 2287 |
| EBV-B95-8 | 967 | 996 | EBV-B95-8 | 3766 | 3795 | EBV-B95-8 | 4234 | 4263 |
| EBV-B95-8 | 5326 | 5355 | EBV-B95-8 | 6553 | 6582 | EBV-B95-8 | 8800 | 8829 |
| EBV-B95-8 | 13471 | 13500 | EBV-B95-8 | 46577 | 46606 | EBV-B95-8 | 48222 | 48251 |
| EBV-B95-8 | 52842 | 52871 | EBV-B95-8 | 53561 | 53590 | EBV-B95-8 | 54377 | 54406 |
| EBV-B95-8 | 54778 | 54807 | EBV-B95-8 | 55067 | 55096 | EBV-B95-8 | 55893 | 55922 |
| EBV-B95-8 | 56735 | 56764 | EBV-B95-8 | 58227 | 58256 | EBV-B95-8 | 58926 | 58955 |
| EBV-B95-8 | 59581 | 59610 | EBV-B95-8 | 60099 | 60128 | EBV-B95-8 | 60877 | 60906 |
| EBV-B95-8 | 61319 | 61348 | EBV-B95-8 | 62302 | 62331 | EBV-B95-8 | 62840 | 52869 |
| EBV-B95-8 | 63178 | 63207 | EBV-B95-8 | 63601 | 63630 | EBV-B95-8 | 63935 | 63964 |
| EBV-B95-8 | 64590 | 64619 | EBV-B95-8 | 66726 | 66755 | EBV-B95-8 | 67486 | 67515 |
| EBV-B95-8 | 67857 | 67886 | EBV-B95-8 | 69228 | 69257 | EBV-B95-8 | 69798 | 69827 |
| EBV-B95-8 | 70439 | 70468 | EBV-B95-8 | 70839 | 70868 | EBV-B95-8 | 71938 | 71967 |
| EBV-B95-8 | 72204 | 72233 | EBV-B95-8 | 72535 | 72564 | EBV-B95-8 | 72983 | 73012 |
| EBV-B95-8 | 73950 | 73979 | EBV-B95-8 | 74304 | 74333 | EBV-B95-8 | 74689 | 74718 |
| EBV-B95-8 | 74978 | 75007 | EBV-B95-8 | 75256 | 75285 | EBV-B95-8 | 77784 | 77813 |
| EBV-B95-8 | 79618 | 79647 | EBV-B95-8 | 80289 | 80318 | EBV-B95-8 | 80704 | 80733 |
| EBV-B95-8 | 81198 | 81227 | EBV-B95-8 | 81629 | 81658 | EBV-B95-8 | 81888 | 81917 |
| EBV-B95-8 | 82225 | 82254 | EBV-B95-8 | 82703 | 82732 | EBV-B95-8 | 83438 | 83467 |
| EBV-B95-8 | 85345 | 85374 | EBV-B95-8 | 86299 | 86328 | EBV-B95-8 | 87104 | 87133 |
| EBV-B95-8 | 89959 | 89988 | EBV-B95-8 | 90915 | 90944 | EBV-B95-8 | 92531 | 92560 |
| EBV-B95-8 | 94071 | 94100 | EBV-B95-8 | 94731 | 94760 | EBV-B95-8 | 95084 | 95113 |
| EBV-B95-8 | 97482 | 97511 | EBV-B95-8 | 98245 | 98274 | EBV-B95-8 | 99224 | 99253 |
| EBV-B95-8 | 100235 | 100264 | EBV-B95-8 | 101009 | 101038 | EBV-B95-8 | 102716 | 102745 |
| EBV-B95-8 | 104004 | 104033 | EBV-B95-8 | 105019 | 105048 | EBV-B95-8 | 105284 | 105313 |
| EBV-B95-8 | 107231 | 107260 | EBV-B95-8 | 108023 | 108052 | EBV-B95-8 | 108370 | 108399 |
| EBV-B95-8 | 109086 | 109115 | EBV-B95-8 | 110250 | 110279 | EBV-B95-8 | 110626 | 110655 |
| EBV-B95-8 | 111690 | 111719 | EBV-B95-8 | 112112 | 112141 | EBV-B95-8 | 114429 | 114458 |
| EBV-B95-8 | 114749 | 114778 | EBV-B95-8 | 115006 | 115035 | EBV-B95-8 | 115597 | 115626 |
| EBV-B95-8 | 116382 | 116411 | EBV-B95-8 | 116649 | 116678 | EBV-B95-8 | 118647 | 118676 |
| EBV-B95-8 | 119542 | 119571 | EBV-B95-8 | 120350 | 120379 | EBV-B95-8 | 121382 | 121411 |
| EBV-B95-8 | 123037 | 123066 | EBV-B95-8 | 123570 | 123599 | EBV-B95-8 | 124913 | 124942 |
| EBV-B95-8 | 125376 | 125405 | EBV-B95-8 | 125805 | 125834 | EBV-B95-8 | 126337 | 126366 |
| EBV-B95-8 | 127493 | 127522 | EBV-B95-8 | 127905 | 127934 | EBV-B95-8 | 128805 | 128834 |
| EBV-B95-8 | 130244 | 130273 | EBV-B95-8 | 130690 | 130719 | EBV-B95-8 | 131603 | 131632 |
| EBV-B95-8 | 134325 | 134354 | EBV-B95-8 | 135032 | 135061 | EBV-B95-8 | 135599 | 135628 |
| EBV-B95-8 | 136148 | 136177 | EBV-B95-8 | 136680 | 136709 | EBV-B95-8 | 137805 | 137834 |
| EBV-B95-8 | 138375 | 138404 | EBV-B95-8 | 139745 | 139774 | EBV-B95-8 | 140610 | 140639 |
| EBV-B95-8 | 141137 | 141166 | EBV-B95-8 | 142290 | 142319 | EBV-B95-8 | 142763 | 142792 |
| EBV-B95-8 | 143078 | 143107 | EBV-B95-8 | 144318 | 144347 | EBV-B95-8 | 145216 | 145245 |
| EBV-B95-8 | 145638 | 145667 | EBV-B95-8 | 147044 | 147073 | EBV-B95-8 | 148404 | 148433 |
| EBV-B95-8 | 150099 | 150128 | EBV-B95-8 | 150443 | 150472 | EBV-B95-8 | 152230 | 152259 |
| EBV-B95-8 | 153127 | 153156 | EBV-B95-8 | 153468 | 153497 | EBV-B95-8 | 153800 | 153829 |
| EBV-B95-8 | 154204 | 154233 | EBV-B95-8 | 156501 | 156530 | EBV-B95-8 | 156773 | 156802 |
| EBV-B95-8 | 157345 | 157374 | EBV-B95-8 | 159211 | 159240 | EBV-B95-8 | 159561 | 159590 |
| EBV-B95-8 | 161193 | 161222 | EBV-B95-8 | 161698 | 161727 | EBV-B95-8 | 162343 | 162372 |
| EBV-B95-8 | 163798 | 163827 | EBV-B95-8 | 164471 | 164500 | EBV-B95-8 | 166234 | 165263 |
| EBV-B95-8 | 166280 | 166309 | EBV-B95-8 | 167347 | 167376 | EBV-B95-8 | 167600 | 167629 |

TABLE 12-continued

| chr | start | end | chr | start | end | chr | start | end |
|---|---|---|---|---|---|---|---|---|
| EBV-B95-8 | 167942 | 167971 | EBV-B95-8 | 168551 | 168580 | EBV-B95-8 | 171304 | 171333 |
| GL000225.1 | 37720 | 37842 | GL000231.1 | 12576 | 12717 | HBV | 111 | 140 |
| HBV | 381 | 410 | HBV | 651 | 680 | HBV | 921 | 950 |
| HBV | 1191 | 1220 | HBV | 1461 | 1490 | HBV | 1731 | 1760 |
| HBV | 2001 | 2030 | HBV | 2271 | 2300 | HBV | 254 | 2570 |
| HBV | 2811 | 2840 | HCMV-AD169 | 17724 | 17753 | HCMV-AD169 | 18691 | 18720 |
| HCMV-AD169 | 23851 | 2388 | HCMV-AD169 | 27296 | 27325 | HCMV-AD169 | 42909 | 42938 |
| HCMV-AD169 | 57909 | 57938 | HCMV-AD169 | 68427 | 68456 | HCMV-AD169 | 76862 | 76891 |
| HCMV-AD169 | 78956 | 78985 | HCMV-AD169 | 81188 | 81217 | HCMV-AD169 | 84448 | 84477 |
| HCMV-AD169 | 88920 | 88949 | HCMV-AD169 | 99889 | 99918 | HCMV-AD169 | 101238 | 101267 |
| HCMV-AD169 | 108021 | 108050 | HCMV-AD169 | 114824 | 114853 | HCMV-AD169 | 128011 | 128040 |
| HCMV-AD169 | 129567 | 129596 | HCMV-AD169 | 149187 | 149216 | HCMV-AD169 | 162299 | 162328 |
| HCMV-AD169 | 169250 | 169279 | HCMV-AD169 | 171221 | 171250 | HCMV-AD169 | 172561 | 172590 |
| HCMV-AD169 | 177053 | 177082 | HCMV-AD169 | 193060 | 193089 | HCMV-AD169 | 193858 | 193887 |
| HCMV-AD169 | 194176 | 194205 | HCMV-AD169 | 195222 | 195251 | HCMV-AD169 | 196060 | 196089 |
| HCMV-AD169 | 196817 | 196846 | HCMV-AD169 | 199152 | 199181 | HCMV-AD169 | 199906 | 199935 |
| HCMV-AD169 | 201145 | 201174 | HCMV-AD169 | 204433 | 204462 | HCMV-AD169 | 207682 | 207711 |
| HCMV-AD169 | 209510 | 209539 | HCMV-AD169 | 210069 | 210098 | HCMV-AD169 | 212133 | 212162 |
| HCMV-AD169 | 212591 | 212620 | HCMV-AD169 | 214453 | 214482 | HCMV-AD169 | 220316 | 220345 |
| HCV | 111 | 140 | HCV | 374 | 403 | HCV | 637 | 666 |
| HCV | 900 | 929 | HCV | 1163 | 1192 | HCV | 1426 | 1455 |
| HCV | 1689 | 1718 | HCV | 1952 | 1981 | HCV | 2215 | 2244 |
| HCV | 2478 | 2507 | HCV | 2741 | 2770 | HCV | 3004 | 3033 |
| HCV | 3267 | 3296 | HCV | 3530 | 3559 | HCV | 3793 | 3822 |
| HCV | 4056 | 4085 | HCV | 4319 | 4348 | HCV | 4582 | 4611 |
| HCV | 4845 | 4874 | HCV | 5108 | 5137 | HCV | 5371 | 5400 |
| HCV | 5634 | 5663 | HCV | 5897 | 5926 | HCV | 6160 | 6189 |
| HCV | 6423 | 6452 | HCV | 6686 | 6715 | HCV | 6949 | 6978 |
| HCV | 7212 | 7241 | HCV | 7475 | 7504 | HCV | 7738 | 7767 |
| HCV | 8001 | 8030 | HCV | 8264 | 8293 | HCV | 8527 | 8556 |
| HCV | 8790 | 8819 | HCV | 9053 | 9082 | HHV5-CINCY-TOWNE | 118 | 1210 |
| HHV5-CINCY-TOWNE | 1988 | 2017 | HHV5-CINCY-TOWNE | 2389 | 2418 | HHV5-CINCY-TOWNE | 3290 | 3319 |
| HHV5-CINCY-TOWNE | 3665 | 3694 | HHV5-CINCY-TOWNE | 4704 | 4733 | HHV5-CINCY-TOWNE | 5400 | 5429 |
| HHV5-CINCY-TOWNE | 7790 | 7819 | HHV5-CINCY-TOWNE | 9656 | 9685 | HHV5-CINCY-TOWNE | 10781 | 10810 |
| HHV5-CINCY-TOWNE | 11109 | 11138 | HHV5-CINCY-TOWNE | 12663 | 12692 | HHV5-CINCY-TOWNE | 13688 | 13717 |
| HHV5-CINCY-TOWNE | 14223 | 14252 | HHV5-CINCY-TOWNE | 14911 | 14940 | HHV5-CINCY-TOWNE | 15206 | 15235 |
| HHV5-CINCY-TOWNE | 15938 | 15967 | HHV5-CINCY-TOWNE | 16440 | 16469 | HHV5-CINCY-TOWNE | 16884 | 16913 |
| HHV5-CINCY-TOWNE | 17347 | 17376 | HHV5-CINCY-TOWNE | 17696 | 17725 | HHV5-CINCY-TOWNE | 17958 | 17987 |
| HHV5-CINCY-TOWNE | 18372 | 18401 | HHV5-CINCY-TOWNE | 19417 | 19446 | HHV5-CINCY-TOWNE | 19910 | 19939 |
| HHV5-CINCY-TOWNE | 20248 | 20277 | HHV5-CINCY-TOWNE | 20671 | 20700 | HHV5-CINCY-TOWNE | 21899 | 21928 |
| HHV5-CINCY-TOWNE | 22798 | 22827 | HHV5-CINCY-TOWNE | 23095 | 23124 | HHV5-CINCY-TOWNE | 26713 | 26742 |

TABLE 12-continued

| chr | start | end | chr | start | end | chr | start | end |
|---|---|---|---|---|---|---|---|---|
| HHV5-CINCY-TOWNE | 27211 | 27240 | HHV5-CINCY-TOWNE | 29784 | 29813 | HHV5-CINCY-TOWNE | 31141 | 31170 |
| HHV5-CINCY-TOWNE | 32660 | 32689 | HHV5-CINCY-TOWNE | 35651 | 35680 | HHV5-CINCY-TOWNE | 36393 | 36422 |
| HHV5-CINCY-TOWNE | 37224 | 37253 | HHV5-CINCY-TOWNE | 37895 | 37924 | HHV5-CINCY-TOWNE | 39244 | 39273 |
| HHV5-CINCY-TOWNE | 43188 | 43217 | HHV5-CINCY-TOWNE | 44447 | 44476 | HHV5-CINCY-TOWNE | 44799 | 44828 |
| HHV5-CINCY-TOWNE | 45394 | 45423 | HHV5-CINCY-TOWNE | 46445 | 46474 | HHV5-CINCY-TOWNE | 46944 | 46973 |
| HHV5-CINCY-TOWNE | 47916 | 47945 | HHV5-CINCY-TOWNE | 48504 | 48533 | HHV5-CINCY-TOWNE | 49094 | 49123 |
| HHV5-CINCY-TOWNE | 49903 | 49932 | HHV5-CINCY-TOWNE | 50230 | 50259 | HHV5-CINCY-TOWNE | 51421 | 51450 |
| HHV5-CINCY-TOWNE | 53772 | 53801 | HHV5-CINCY-TOWNE | 55651 | 55680 | HHV5-CINCY-TOWNE | 56380 | 56409 |
| HHV5-CINCY-TOWNE | 57291 | 57320 | HHV5-CINCY-TOWNE | 58491 | 58520 | HHV5-CINCY-TOWNE | 59023 | 59052 |
| HHV5-CINCY-TOWNE | 59792 | 59821 | HHV5-CINCY-TOWNE | 60124 | 60153 | HHV5-CINCY-TOWNE | 60392 | 60421 |
| HHV5-CINCY-TOWNE | 60900 | 60929 | HHV5-CINCY-TOWNE | 63894 | 63923 | HHV5-CINCY-TOWNE | 65843 | 65872 |
| HHV5-CINCY-TOWNE | 68089 | 68118 | HHV5-CINCY-TOWNE | 22454 | 72483 | HHV5-CINCY-TOWNE | 81185 | 81214 |
| HHV5-CINCY-TOWNE | 84144 | 84173 | HHV5-CINCY-TOWNE | 85524 | 85553 | HHV5-CINCY-TOWNE | 85943 | 85972 |
| HHV5-CINCY-TOWNE | 86889 | 86918 | HHV5-CINCY-TOWNE | 87195 | 87224 | HHV5-CINCY-TOWNE | 87455 | 87484 |
| HHV5-CINCY-TOWNE | 87769 | 87798 | HHV5-CINCY-TOWNE | 88564 | 88593 | HHV5-CINCY-TOWNE | 93096 | 93125 |
| HHV5-CINCY-TOWNE | 93776 | 93805 | HHV5-CINCY-TOWNE | 97621 | 97650 | HHV5-CINCY-TOWNE | 98737 | 98766 |
| HHV5-CINCY-TOWNE | 99460 | 99489 | HHV5-CINCY-TOWNE | 107540 | 107569 | HHV5-CINCY-TOWNE | 108823 | 108852 |
| HHV5-CINCY-TOWNE | 109725 | 109754 | HHV5-CINCY-TOWNE | 112036 | 112065 | HHV5-CINCY-TOWNE | 112319 | 112348 |
| HHV5-CINCY-TOWNE | 112595 | 112624 | HHV5-CINCY-TOWNE | 112892 | 112921 | HHV5-CINCY-TOWNE | 113194 | 113223 |
| HHV5-CINCY-TOWNE | 113535 | 113564 | HHV5-CINCY-TOWNE | 113927 | 113956 | HHV5-CINCY-TOWNE | 114267 | 114296 |
| HHV5-CINCY-TOWNE | 114593 | 114622 | HHV5-CINCY-TOWNE | 114867 | 114896 | HHV5-CINCY-TOWNE | 115177 | 115206 |
| HHV5-CINCY-TOWNE | 115432 | 115461 | HHV5-CINCY-TOWNE | 115685 | 115714 | HHV5-CINCY-TOWNE | 115986 | 116015 |
| HHV5-CINCY-TOWNE | 116382 | 116411 | HHV5-CINCY-TOWNE | 116700 | 116729 | HHV5-CINCY-TOWNE | 118193 | 118222 |
| HHV5-CINCY-TOWNE | 118995 | 119024 | HHV5-CINCY-TOWNE | 120028 | 120067 | HHV5-CINCY-TOWNE | 121485 | 121514 |
| HHV5-CINCY-TOWNE | 122199 | 122228 | HHV5-CINCY-TOWNE | 122606 | 122635 | HHV5-CINCY-TOWNE | 124559 | 124588 |
| HHV5-CINCY-TOWNE | 125276 | 125305 | HHV5-CINCY-TOWNE | 132497 | 132526 | HHV5-CINCY-TOWNE | 135460 | 135489 |

TABLE 12-continued

| chr | start | end | chr | start | end | chr | start | end |
|---|---|---|---|---|---|---|---|---|
| HHV5-CINCY-TOWNE | 135730 | 135759 | HHV5-CINCY-TOWNE | 137379 | 137408 | HHV5-CINCY-TOWNE | 139062 | 139096 |
| HHV5-CINCY-TOWNE | 139472 | 139501 | HHV5-CINCY-TOWNE | 140147 | 140176 | HHV5-CINCY-TOWNE | 140722 | 140751 |
| HHV5-CINCY-TOWNE | 142023 | 142052 | HHV5-CINCY-TOWNE | 143692 | 143721 | HHV5-CINCY-TOWNE | 144080 | 144109 |
| HHV5-CINCY-TOWNE | 147310 | 147339 | HHV5-CINCY-TOWNE | 149465 | 149494 | HHV5-CINCY-TOWNE | 150359 | 150388 |
| HHV5-CINCY-TOWNE | 151593 | 151622 | HHV5-CINCY-TOWNE | 152153 | 152182 | HHV5-CINCY-TOWNE | 154148 | 154177 |
| HHV5-CINCY-TOWNE | 154610 | 154639 | HHV5-CINCY-TOWNE | 157018 | 157047 | HHV5-CINCY-TOWNE | 157367 | 157396 |
| HHV5-CINCY-TOWNE | 169038 | 169067 | HHV5-CINCY-TOWNE | 171503 | 171532 | HHV5-CINCY-TOWNE | 175146 | 175175 |
| HHV5-CINCY-TOWNE | 177553 | 177582 | HHV5-CINCY-TOWNE | 182254 | 182283 | HHV5-CINCY-TOWNE | 183115 | 183144 |
| HHV5-CINCY-TOWNE | 184120 | 184149 | HHV5-CINCY-TOWNE | 185558 | 185587 | HHV5-CINCY-TOWNE | 186027 | 186056 |
| HHV5-CINCY-TOWNE | 186435 | 186464 | HHV5-CINCY-TOWNE | 186707 | 186736 | HHV5-CINCY-TOWNE | 187115 | 187144 |
| HHV5-CINCY-TOWNE | 187514 | 187543 | HHV5-CINCY-TOWNE | 187859 | 187888 | HHV5-CINCY-TOWNE | 188473 | 188502 |
| HHV5-CINCY-TOWNE | 188768 | 188797 | HHV5-CINCY-TOWNE | 189050 | 189079 | HHV5-CINCY-TOWNE | 189302 | 189331 |
| HHV5-CINCY-TOWNE | 189936 | 189965 | HHV5-CINCY-TOWNE | 190655 | 190684 | HHV5-CINCY-TOWNE | 190954 | 190983 |
| HHV5-CINCY-TOWNE | 191453 | 191482 | HHV5-CINCY-TOWNE | 191882 | 191911 | HHV5-CINCY-TOWNE | 192183 | 192212 |
| HHV5-CINCY-TOWNE | 192541 | 192570 | HHV5-CINCY-TOWNE | 193045 | 193074 | HHV5-CINCY-TOWNE | 193325 | 193354 |
| HHV5-CINCY-TOWNE | 193597 | 193626 | HHV5-CINCY-TOWNE | 194165 | 194194 | HHV5-CINCY-TOWNE | 194461 | 194490 |
| HHV5-CINCY-TOWNE | 194848 | 194877 | HHV5-CINCY-TOWNE | 195324 | 195353 | HHV5-CINCY-TOWNE | 195651 | 195680 |
| HHV5-CINCY-TOWNE | 196018 | 196047 | HHV5-CINCY-TOWNE | 196343 | 196372 | HHV5-CINCY-TOWNE | 196941 | 196970 |
| HHV5-CINCY-TOWNE | 197218 | 197247 | HHV5-CINCY-TOWNE | 198315 | 198344 | HHV5-CINCY-TOWNE | 198792 | 198821 |
| HHV5-CINCY-TOWNE | 199162 | 199191 | HHV5-CINCY-TOWNE | 200113 | 200142 | HHV5-CINCY-TOWNE | 200571 | 200600 |
| HHV5-CINCY-TOWNE | 201373 | 201402 | HHV5-CINCY-TOWNE | 201905 | 201934 | HHV5-CINCY-TOWNE | 202264 | 202293 |
| HHV5-CINCY-TOWNE | 202537 | 202566 | HHV5-CINCY-TOWNE | 203319 | 203348 | HHV5-CINCY-TOWNE | 203720 | 203749 |
| HHV5-CINCY-TOWNE | 204008 | 204037 | HHV5-CINCY-TOWNE | 206213 | 206242 | HHV5-CINCY-TOWNE | 206735 | 206764 |
| HHV5-CINCY-TOWNE | 211676 | 211705 | HHV5-CINCY-TOWNE | 212340 | 212369 | HHV5-CINCY-TOWNE | 212609 | 212638 |
| HHV5-CINCY-TOWNE | 213813 | 213842 | HHV5-CINCY-TOWNE | 214695 | 214724 | HHV5-CINCY-TOWNE | 214950 | 214979 |
| HHV5-CINCY-TOWNE | 215930 | 215959 | HHV5-CINCY-TOWNE | 216228 | 216257 | HHV5-CINCY-TOWNE | 222672 | 222701 |

TABLE 12-continued

| chr | start | end | chr | start | end | chr | start | end |
|---|---|---|---|---|---|---|---|---|
| HHV5-CINCY-TOWNE | 223515 | 223544 | HHV5-CINCY-TOWNE | 225150 | 225179 | HHV5-CINCY-TOWNE | 226058 | 226087 |
| HHV5-CINCY-TOWNE | 226887 | 226916 | HPV16 | 111 | 140 | HPV16 | 367 | 396 |
| HPV16 | 623 | 652 | HPV16 | 879 | 908 | HPV16 | 1135 | 1164 |
| HPV16 | 1391 | 1420 | HPV16 | 1647 | 1676 | HPV16 | 1903 | 1932 |
| HPV16 | 2159 | 2188 | HPV16 | 2415 | 2444 | HPV16 | 2671 | 2700 |
| HPV16 | 2927 | 2956 | HPV16 | 3183 | 3212 | HPV16 | 3439 | 3468 |
| HPV16 | 3695 | 3724 | HPV16 | 3951 | 3980 | HPV16 | 4207 | 4236 |
| HPV16 | 4463 | 4492 | HPV16 | 4719 | 4748 | HPV16 | 4975 | 5004 |
| HPV16 | 5231 | 5260 | HPV16 | 5487 | 5516 | HPV16 | 5743 | 5772 |
| HPV16 | 4999 | 6028 | HPV16 | 6255 | 6284 | HPV16 | 6511 | 6540 |
| HPV16 | 6767 | 6796 | HPV16 | 7023 | 7052 | HPV16 | 7279 | 7308 |
| HPV16 | 7535 | 7564 | HPV18 | 111 | 140 | HPV18 | 383 | 412 |
| HPV18 | 655 | 684 | HPV18 | 927 | 956 | HPV18 | 1199 | 1228 |
| HPV18 | 1471 | 1500 | HPV18 | 1743 | 1772 | HPV18 | 2015 | 2044 |
| HPV18 | 2287 | 2316 | HPV18 | 2559 | 2588 | HPV18 | 2831 | 2860 |
| HPV18 | 3103 | 3132 | HPV18 | 3375 | 3404 | HPV18 | 3647 | 3676 |
| HPV18 | 3919 | 3948 | HPV18 | 4191 | 4220 | HPV18 | 4463 | 4492 |
| HPV18 | 4735 | 4764 | HPV18 | 5007 | 5036 | HPV18 | 5279 | 5308 |
| HPV18 | 5551 | 5580 | HPV18 | 5823 | 5852 | HPV18 | 6095 | 6124 |
| HPV18 | 6367 | 6396 | HPV18 | 6639 | 6668 | HPV18 | 6911 | 6940 |
| HPV18 | 7183 | 7212 | HPV18 | 7455 | 7484 | — | — | — |

TABLE 13

| chr | start | end | chr | start | end | chr | start | end |
|---|---|---|---|---|---|---|---|---|
| chr1 | 898654 | 898690 | chr1 | 913532 | 913955 | chr1 | 1047531 | 1047619 |
| chr1 | 1080583 | 1080824 | chr1 | 1146734 | 1146818 | chr1 | 1218737 | 1218779 |
| chr1 | 1223512 | 1223612 | chr1 | 1235813 | 1236078 | chr1 | 1267014 | 1267151 |
| chr1 | 1267462 | 1267699 | chr1 | 1267906 | 1268158 | chr1 | 1281214 | 1281244 |
| chr1 | 1341706 | 1341743 | chr1 | 1473125 | 1473207 | chr1 | 1475556 | 1475643 |
| chr1 | 1476255 | 1476318 | chr1 | 1483186 | 1483363 | chr1 | 1563193 | 1563223 |
| chr1 | 1688882 | 1689012 | chr1 | 1805049 | 1805069 | chr1 | 1856436 | 1856466 |
| chr1 | 1857847 | 1857909 | chr1 | 1874744 | 1874787 | chr1 | 1910415 | 1910445 |
| chr1 | 1923489 | 1923521 | chr1 | 1935274 | 1935459 | chr1 | 1974848 | 1974925 |
| chr1 | 2066490 | 2066679 | chr1 | 2125216 | 2125483 | chr1 | 2165895 | 2165999 |
| chr1 | 2263169 | 2263263 | chr1 | 2267552 | 2267690 | chr1 | 2304327 | 2304389 |
| chr1 | 2307925 | 2307955 | chr1 | 2308376 | 2308636 | chr1 | 2309868 | 2309953 |
| chr1 | 2331363 | 2331437 | chr1 | 2336397 | 2336427 | chr1 | 2375148 | 2375543 |
| chr1 | 2397001 | 2397031 | chr1 | 2428331 | 2428385 | chr1 | 2472174 | 2472301 |
| chr1 | 2507063 | 2507183 | chr1 | 2514330 | 2514353 | chr1 | 2521024 | 2521063 |
| chr1 | 2706308 | 2706334 | chr1 | 2830155 | 2830185 | chr1 | 2866038 | 2866068 |
| chr1 | 2984719 | 2984749 | chr1 | 3102653 | 3102779 | chr1 | 3158823 | 3158962 |
| chr1 | 3182883 | 3182917 | chr1 | 3322090 | 3322170 | chr1 | 3567093 | 3567344 |
| chr1 | 3567738 | 3567850 | chr1 | 3567883 | 3568226 | chr1 | 3601850 | 3601946 |
| chr1 | 3607081 | 3607236 | chr1 | 3659550 | 3659642 | chr1 | 3659672 | 3659716 |
| chr1 | 3663532 | 3663562 | chr1 | 3663874 | 3663921 | chr1 | 3664481 | 3664741 |
| chr1 | 3683722 | 3683818 | chr1 | 3700384 | 3700414 | chr1 | 3733551 | 3733581 |
| chr1 | 4111086 | 4111231 | chr1 | 4401433 | 4401463 | chr1 | 4714018 | 4714074 |
| chr1 | 4714164 | 4714345 | chr1 | 4715428 | 4715539 | chr1 | 4715575 | 4716701 |
| chr1 | 5919973 | 5920071 | chr1 | 5920650 | 5920710 | chr1 | 5924296 | 5924431 |
| chr1 | 5924851 | 5924984 | chr1 | 5926596 | 5926645 | chr1 | 5933086 | 5933144 |
| chr1 | 5934925 | 5935061 | chr1 | 5940517 | 5940547 | chr1 | 5940945 | 5941132 |
| chr1 | 5944299 | 5944449 | chr1 | 5945348 | 5945435 | chr1 | 5947258 | 5947288 |
| chr1 | 5949491 | 5949575 | chr1 | 5950965 | 5951039 | chr1 | 5957473 | 5957503 |
| chr1 | 5967237 | 5967267 | chr1 | 5969001 | 5969283 | chr1 | 5972104 | 5972134 |
| chr1 | 5972878 | 5972922 | chr1 | 6021621 | 6021651 | chr1 | 6025872 | 6025950 |
| chr1 | 6036766 | 6036796 | chr1 | 6056157 | 6056201 | chr1 | 6056506 | 6056651 |
| chr1 | 6059910 | 6059974 | chr1 | 6166353 | 6166469 | chr1 | 6171763 | 6171810 |
| chr1 | 6186511 | 6186546 | chr1 | 6280243 | 6280273 | chr1 | 6284828 | 6284858 |
| chr1 | 6304201 | 6304242 | chr1 | 6360593 | 6360634 | chr1 | 6410456 | 6410486 |
| chr1 | 6446131 | 6446308 | chr1 | 6480514 | 6480831 | chr1 | 6501055 | 6501077 |
| chr1 | 6507678 | 6508126 | chr1 | 6713914 | 6714041 | chr1 | 6714348 | 6714378 |
| chr1 | 7764641 | 7764737 | chr1 | 8085685 | 8085715 | chr1 | 9324231 | 9324274 |
| chr1 | 9402465 | 9402616 | chr1 | 9527172 | 9527208 | chr1 | 9712074 | 9712104 |
| chr1 | 9712561 | 9713014 | chr1 | 9795995 | 9796196 | chr1 | 9867157 | 9867316 |
| chr1 | 10091888 | 10091914 | chr1 | 10166521 | 10166551 | chr1 | 10948552 | 10948582 |
| chr1 | 11169346 | 11169375 | chr1 | 11174404 | 11174433 | chr1 | 11181358 | 11181432 |
| chr1 | 11182142 | 11182171 | chr1 | 11188149 | 11188178 | chr1 | 11210182 | 11210211 |
| chr1 | 11217215 | 11217337 | chr1 | 11249032 | 11249061 | chr1 | 11538705 | 11538821 |
| chr1 | 11539175 | 11539205 | chr1 | 11539410 | 11539440 | chr1 | 11540129 | 11540178 |

TABLE 13-continued

| chr | start | end | chr | start | end | chr | start | end |
|---|---|---|---|---|---|---|---|---|
| chr1 | 11591719 | 11591826 | chr1 | 11752476 | 11752511 | chr1 | 11886250 | 11886280 |
| chr1 | 11936748 | 11936778 | chr1 | 11959093 | 11959196 | chr1 | 12041510 | 12041525 |
| chr1 | 12123243 | 12123553 | chr1 | 12227685 | 12227941 | chr1 | 12251443 | 12251958 |
| chr1 | 12460299 | 12460356 | chr1 | 13910436 | 13910714 | chr1 | 14026481 | 14026618 |
| chr1 | 14097878 | 14097977 | chr1 | 14128478 | 14128588 | chr1 | 14149749 | 14149867 |
| chr1 | 14730425 | 14730472 | chr1 | 14925501 | 14926050 | chr1 | 15128565 | 15128595 |
| chr1 | 15251120 | 15251211 | chr1 | 15480593 | 15480892 | chr1 | 16475031 | 16475207 |
| chr1 | 16861522 | 16861552 | chr1 | 17445857 | 17445943 | chr1 | 18437457 | 18437526 |
| chr1 | 18956211 | 18956304 | chr1 | 18956574 | 18956610 | chr1 | 18956856 | 18957246 |
| chr1 | 18957507 | 18957587 | chr1 | 18958033 | 18958228 | chr1 | 18958359 | 18958381 |
| chr1 | 18959456 | 18959550 | chr1 | 18960897 | 18960990 | chr1 | 18962727 | 18963135 |
| chr1 | 18969625 | 18969819 | chr1 | 18971852 | 18971929 | chr1 | 18972130 | 18972160 |
| chr1 | 19043563 | 19043678 | chr1 | 19992418 | 19992432 | chr1 | 20127435 | 20127471 |
| chr1 | 20248109 | 20248141 | chr1 | 20618329 | 20618369 | chr1 | 20693317 | 20693420 |
| chr1 | 20879035 | 20879228 | chr1 | 20879256 | 20879289 | chr1 | 20879562 | 20879640 |
| chr1 | 20879845 | 20879957 | chr1 | 20880182 | 20880605 | chr1 | 21026117 | 21026225 |
| chr1 | 21042894 | 21042924 | chr1 | 21044125 | 21044161 | chr1 | 21050471 | 21050511 |
| chr1 | 21058635 | 21058776 | chr1 | 21573668 | 21574203 | chr1 | 21835943 | 21836007 |
| chr1 | 22140753 | 22141184 | chr1 | 22141326 | 22141355 | chr1 | 22222711 | 22222793 |
| chr1 | 22927410 | 22927482 | chr1 | 23748982 | 23749070 | chr1 | 23885070 | 23885100 |
| chr1 | 25255921 | 25255934 | chr1 | 25256354 | 25256383 | chr1 | 25257157 | 25257205 |
| chr1 | 25257490 | 25257529 | chr1 | 25257532 | 25257561 | chr1 | 25257916 | 25258250 |
| chr1 | 25919307 | 25919337 | chr1 | 26467523 | 26467547 | chr1 | 26551729 | 26551796 |
| chr1 | 26552086 | 26552130 | chr1 | 26737583 | 26737613 | chr1 | 26737946 | 26738182 |
| chr1 | 26917724 | 26917740 | chr1 | 27190175 | 27190278 | chr1 | 27332448 | 27332673 |
| chr1 | 27844518 | 27844548 | chr1 | 29048601 | 29048643 | chr1 | 29450491 | 29450543 |
| chr1 | 29586072 | 29585674 | chr1 | 29804947 | 29805094 | chr1 | 30351554 | 30351742 |
| chr1 | 30815412 | 30815416 | chr1 | 30815455 | 30815578 | chr1 | 31863186 | 31863216 |
| chr1 | 32180397 | 32180427 | chr1 | 32237639 | 32238507 | chr1 | 32410276 | 32410306 |
| chr1 | 32410519 | 32410614 | chr1 | 32705488 | 32705550 | chr1 | 32756498 | 32756540 |
| chr1 | 32930458 | 32930558 | chr1 | 32938720 | 32938750 | chr1 | 33219567 | 33219596 |
| chr1 | 34628948 | 34628978 | chr1 | 34629469 | 34629728 | chr1 | 34630548 | 34630635 |
| chr1 | 34630859 | 34630978 | chr1 | 34631580 | 34631662 | chr1 | 34631933 | 34631963 |
| chr1 | 34642380 | 34642489 | chr1 | 35258637 | 35258714 | chr1 | 35351078 | 35351659 |
| chr1 | 35395526 | 35395851 | chr1 | 35664716 | 35664746 | chr1 | 36042679 | 36043489 |
| chr1 | 36563479 | 36563522 | chr1 | 36849009 | 36849038 | chr1 | 37498792 | 37498844 |
| chr1 | 37498889 | 37499181 | chr1 | 37499460 | 37499682 | chr1 | 37500014 | 37500153 |
| chr1 | 37500468 | 37500574 | chr1 | 37500603 | 37500806 | chr1 | 37501072 | 37501102 |
| chr1 | 38100689 | 38100851 | chr1 | 38219712 | 38219795 | chr1 | 38230042 | 38230242 |
| chr1 | 38230283 | 38230297 | chr1 | 38230779 | 38230859 | chr1 | 38398311 | 38398348 |
| chr1 | 38412504 | 38412832 | chr1 | 38510178 | 38510217 | chr1 | 38510563 | 38510624 |
| chr1 | 38510854 | 38511119 | chr1 | 38511337 | 38611799 | chr1 | 38511822 | 38511824 |
| chr1 | 38512385 | 38512415 | chr1 | 38513244 | 38513318 | chr1 | 39269741 | 39270121 |
| chr1 | 40137898 | 40137984 | chr1 | 40237141 | 40237203 | chr1 | 40349626 | 40349647 |
| chr1 | 40708443 | 40708481 | chr1 | 40915590 | 40915620 | chr1 | 41283958 | 41284463 |
| chr1 | 41847583 | 41847702 | chr1 | 41848810 | 41848840 | chr1 | 41915253 | 41915283 |
| chr1 | 41967342 | 41967418 | chr1 | 41991640 | 41991702 | chr1 | 43400336 | 43400386 |
| chr1 | 43814994 | 43815023 | chr1 | 43834741 | 43834832 | chr1 | 43842664 | 43842779 |
| chr1 | 44068774 | 44068804 | chr1 | 44494137 | 44494153 | chr1 | 44726912 | 44727268 |
| chr1 | 44872448 | 44872722 | chr1 | 44872924 | 44873172 | chr1 | 44873510 | 44873706 |
| chr1 | 44883121 | 44883214 | chr1 | 44883752 | 44884122 | chr1 | 45308238 | 45308262 |
| chr1 | 45308592 | 45308625 | chr1 | 46632876 | 46632923 | chr1 | 46744657 | 46744733 |
| chr1 | 46913837 | 46913876 | chr1 | 46913887 | 46914245 | chr1 | 46914656 | 46914686 |
| chr1 | 46932765 | 46932905 | chr1 | 46951207 | 46951317 | chr1 | 46951645 | 46951739 |
| chr1 | 46956454 | 46956603 | chr1 | 46956823 | 46957171 | chr1 | 47009929 | 47010035 |
| chr1 | 47035373 | 47035403 | chr1 | 47078736 | 47078782 | chr1 | 47695122 | 47695422 |
| chr1 | 47696295 | 47696520 | chr1 | 47696821 | 47696964 | chr1 | 47696987 | 47697110 |
| chr1 | 47697356 | 47697510 | chr1 | 47697732 | 47697946 | chr1 | 47698007 | 47698210 |
| chr1 | 47788328 | 47788348 | chr1 | 47882063 | 47882322 | chr1 | 47882769 | 47882803 |
| chr1 | 47909718 | 47910160 | chr1 | 47910523 | 47910624 | chr1 | 47910749 | 47910914 |
| chr1 | 47911424 | 47911508 | chr1 | 47999050 | 47999163 | chr1 | 48059078 | 48059243 |
| chr1 | 49242344 | 49242533 | chr1 | 50513629 | 50513745 | chr1 | 50799278 | 50799316 |
| chr1 | 50799394 | 50799400 | chr1 | 50880932 | 50881302 | chr1 | 50881427 | 50881956 |
| chr1 | 50882144 | 50882529 | chr1 | 50882808 | 50883611 | chr1 | 50883882 | 50883976 |
| chr1 | 50884021 | 50884352 | chr1 | 50884691 | 50884887 | chr1 | 50885336 | 50885366 |
| chr1 | 50886188 | 50887084 | chr1 | 50887176 | 50887284 | chr1 | 50888709 | 50888795 |
| chr1 | 50889124 | 50889510 | chr1 | 50889820 | 50890379 | chr1 | 50890796 | 50891595 |
| chr1 | 50892153 | 50892283 | chr1 | 50892337 | 50892351 | chr1 | 50892607 | 50893422 |
| chr1 | 50893519 | 50893877 | chr1 | 51763252 | 51763298 | chr1 | 52832687 | 52832724 |
| chr1 | 53019468 | 53019568 | chr1 | 53068166 | 53068546 | chr1 | 53098842 | 53099067 |
| chr1 | 53192045 | 53192075 | chr1 | 53308568 | 53308607 | chr1 | 53308908 | 53309248 |
| chr1 | 53528374 | 53528439 | chr1 | 53705674 | 53705701 | chr1 | 54203829 | 54204399 |
| chr1 | 54586626 | 5456736 | chr1 | 54837089 | 54837119 | chr1 | 55462673 | 55462703 |
| chr1 | 57888367 | 57888397 | chr1 | 57888987 | 57889087 | chr1 | 57889402 | 57889654 |
| chr1 | 57890431 | 57890650 | chr1 | 58715153 | 58715194 | chr1 | 58715475 | 58715854 |
| chr1 | 58715979 | 58715993 | chr1 | 61519360 | 61519394 | chr1 | 62660740 | 62660768 |
| chr1 | 62660786 | 62660861 | chr1 | 62793237 | 62793267 | chr1 | 63539509 | 63539887 |
| chr1 | 63785619 | 63785766 | chr1 | 63786079 | 63786329 | chr1 | 63787031 | 63787063 |

TABLE 13-continued

| chr | start | end | chr | start | end | chr | start | end |
|---|---|---|---|---|---|---|---|---|
| chr1 | 63787302 | 63787568 | chr1 | 63788423 | 63788557 | chr1 | 63788920 | 63789496 |
| chr1 | 63789729 | 63789791 | chr1 | 63789850 | 63789912 | chr1 | 63790253 | 63790278 |
| chr1 | 63792561 | 63792648 | chr1 | 63792798 | 63793072 | chr1 | 63795263 | 63796277 |
| chr1 | 63796498 | 63796575 | chr1 | 64240026 | 64240118 | chr1 | 64240617 | 64240673 |
| chr1 | 64734652 | 64734673 | chr1 | 64937330 | 64937542 | chr1 | 65303636 | 65303692 |
| chr1 | 65304227 | 65304256 | chr1 | 65305384 | 65305413 | chr1 | 65306926 | 65306955 |
| chr1 | 65309787 | 65309816 | chr1 | 65310487 | 65310531 | chr1 | 65311188 | 65311217 |
| chr1 | 65312331 | 65312432 | chr1 | 65731337 | 65731446 | chr1 | 65990955 | 65991018 |
| chr1 | 65991446 | 65991560 | chr1 | 65991606 | 65991757 | chr1 | 66258180 | 66258650 |
| chr1 | 66258672 | 66258774 | chr1 | 66259137 | 66259174 | chr1 | 66998790 | 66999332 |
| chr1 | 66999636 | 66999673 | chr1 | 67218064 | 67218343 | chr1 | 67390334 | 67390450 |
| chr1 | 67391067 | 67391096 | chr1 | 67773159 | 67773780 | chr1 | 70033609 | 70033916 |
| chr1 | 70034459 | 70034574 | chr1 | 70035088 | 70035537 | chr1 | 70599151 | 70599169 |
| chr1 | 70672858 | 70672878 | chr1 | 72749641 | 72749699 | chr1 | 75595819 | 75595990 |
| chr1 | 75596136 | 75596384 | chr1 | 75596687 | 75596858 | chr1 | 75596930 | 75597584 |
| chr1 | 75597923 | 75598179 | chr1 | 75598384 | 75598414 | chr1 | 75599427 | 75599621 |
| chr1 | 75600225 | 75600848 | chr1 | 75600925 | 75601118 | chr1 | 75601188 | 75601428 |
| chr1 | 75601983 | 75603052 | chr1 | 76080484 | 76080768 | chr1 | 76082129 | 76082209 |
| chr1 | 76354719 | 76354754 | chr1 | 76540450 | 76540666 | chr1 | 77333058 | 77333088 |
| chr1 | 77333384 | 77333433 | chr1 | 77334169 | 77334385 | chr1 | 77334409 | 77334756 |
| chr1 | 77747366 | 77747453 | chr1 | 77747939 | 77748235 | chr1 | 78511466 | 78512354 |
| chr1 | 78957292 | 78957522 | chr1 | 82267150 | 82267185 | chr1 | 82268573 | 82268815 |
| chr1 | 84944530 | 84944568 | chr1 | 85358752 | 85358822 | chr1 | 85463349 | 85463378 |
| chr1 | 85725508 | 85725537 | chr1 | 85725639 | 85725668 | chr1 | 86621660 | 86622127 |
| chr1 | 86622526 | 86622551 | chr1 | 86860809 | 86860949 | chr1 | 87617774 | 87617807 |
| chr1 | 90099997 | 90100084 | chr1 | 90309292 | 90309490 | chr1 | 91172012 | 91172677 |
| chr1 | 91177941 | 91178207 | chr1 | 91180075 | 91180306 | chr1 | 91181932 | 91182132 |
| chr1 | 91182338 | 91183195 | chr1 | 91183251 | 91183610 | chr1 | 91183951 | 91183986 |
| chr1 | 91184423 | 91184672 | chr1 | 91185190 | 91185308 | chr1 | 91185348 | 91185707 |
| chr1 | 91188983 | 91189383 | chr1 | 91189688 | 91190380 | chr1 | 91190869 | 91190948 |
| chr1 | 91190985 | 91191234 | chr1 | 91191290 | 91191310 | chr1 | 91192274 | 91192576 |
| chr1 | 91194414 | 91194569 | chr1 | 91195117 | 91195390 | chr1 | 91195879 | 91196194 |
| chr1 | 91196226 | 91196502 | chr1 | 91316261 | 91316313 | chr1 | 91316627 | 91316682 |
| chr1 | 91869988 | 91870018 | chr1 | 92948324 | 92948597 | chr1 | 92948841 | 92948976 |
| chr1 | 92952145 | 92952655 | chr1 | 94147641 | 94147670 | chr1 | 94147816 | 94147845 |
| chr1 | 94343568 | 94343596 | chr1 | 95006795 | 95006902 | chr1 | 97185262 | 97185406 |
| chr1 | 98510791 | 98511335 | chr1 | 98511628 | 98511922 | chr1 | 98514225 | 98514255 |
| chr1 | 98515142 | 98515191 | chr1 | 98515256 | 98515319 | chr1 | 98519023 | 98519675 |
| chr1 | 99469682 | 99469696 | chr1 | 99469760 | 99469788 | chr1 | 99470785 | 99470847 |
| chr1 | 100437150 | 100437172 | chr1 | 101004456 | 101004737 | chr1 | 101005071 | 101005144 |
| chr1 | 101005360 | 101005675 | chr1 | 101702504 | 101702616 | chr1 | 101703612 | 101703642 |
| chr1 | 103574508 | 103574537 | chr1 | 107682735 | 107682977 | chr1 | 107683439 | 107683517 |
| chr1 | 107684240 | 107684439 | chr1 | 108507063 | 108507076 | chr1 | 108507320 | 108507375 |
| chr1 | 108507495 | 108507497 | chr1 | 108507717 | 108507810 | chr1 | 108508052 | 108508640 |
| chr1 | 109203609 | 109203672 | chr1 | 109585463 | 109585488 | chr1 | 109631646 | 109631682 |
| chr1 | 109644251 | 109644336 | chr1 | 110610586 | 110610897 | chr1 | 110611046 | 110611276 |
| chr1 | 110611435 | 110611513 | chr1 | 110611654 | 110611965 | chr1 | 110626684 | 110627578 |
| chr1 | 110672889 | 110673233 | chr1 | 110692973 | 110693496 | chr1 | 110693737 | 110694117 |
| chr1 | 110754003 | 110754101 | chr1 | 110764309 | 110754356 | chr1 | 110883542 | 110883965 |
| chr1 | 111097906 | 111097936 | chr1 | 111098196 | 111098316 | chr1 | 111216763 | 111216972 |
| chr1 | 111217195 | 111217891 | chr1 | 111217924 | 111217982 | chr1 | 111506007 | 111506212 |
| chr1 | 111813546 | 111813587 | chr1 | 112084954 | 112084984 | chr1 | 114428007 | 114428084 |
| chr1 | 114448967 | 114448990 | chr1 | 114695439 | 114695736 | chr1 | 114695800 | 114695943 |
| chr1 | 114696350 | 114696463 | chr1 | 114696541 | 114696712 | chr1 | 115256514 | 115256552 |
| chr1 | 115258729 | 115258772 | chr1 | 115631867 | 115631915 | chr1 | 115632469 | 115632555 |
| chr1 | 115880184 | 115880395 | chr1 | 115880873 | 115881042 | chr1 | 116214104 | 116214318 |
| chr1 | 116371139 | 116371201 | chr1 | 116380651 | 116381287 | chr1 | 116382387 | 116382478 |
| chr1 | 119522074 | 119522434 | chr1 | 119522839 | 119522853 | chr1 | 119522926 | 119522940 |
| chr1 | 119527237 | 119527391 | chr1 | 119527623 | 119527652 | chr1 | 119528653 | 119529118 |
| chr1 | 119529804 | 119529839 | chr1 | 119530100 | 119530148 | chr1 | 119530202 | 119530507 |
| chr1 | 119530554 | 119530725 | chr1 | 119531029 | 119531157 | chr1 | 119532318 | 119532320 |
| chr1 | 119535908 | 119536377 | chr1 | 119542322 | 119542352 | chr1 | 119543070 | 119543214 |
| chr1 | 119543532 | 119544182 | chr1 | 119548823 | 119548853 | chr1 | 119549058 | 119549734 |
| chr1 | 119549915 | 119549929 | chr1 | 119550155 | 119550278 | chr1 | 119550533 | 119550633 |
| chr1 | 119551014 | 119551269 | chr1 | 150603138 | 150603154 | chr1 | 150941425 | 150941756 |
| chr1 | 151169637 | 151169757 | chr1 | 151170057 | 151170206 | chr1 | 151300888 | 151300918 |
| chr1 | 151362740 | 151362779 | chr1 | 151693945 | 151694351 | chr1 | 151812413 | 151812442 |
| chr1 | 152009415 | 152009510 | chr1 | 152085398 | 152085504 | chr1 | 152488150 | 152488197 |
| chr1 | 153539476 | 153539637 | chr1 | 153540096 | 153540154 | chr1 | 153651965 | 153652370 |
| chr1 | 153937124 | 153937167 | chr1 | 154127987 | 154128016 | chr1 | 154298320 | 154298557 |
| chr1 | 154475372 | 154475531 | chr1 | 154516810 | 154516845 | chr1 | 155043331 | 155043657 |
| chr1 | 155161778 | 155162033 | chr1 | 155164415 | 155164455 | chr1 | 155283218 | 155283248 |
| chr1 | 155578888 | 155578921 | chr1 | 155826292 | 155826336 | chr1 | 155874151 | 155874300 |
| chr1 | 155874508 | 155874546 | chr1 | 155954282 | 155954396 | chr1 | 156010523 | 156010548 |
| chr1 | 156215329 | 156215359 | chr1 | 156215607 | 156215805 | chr1 | 156357993 | 156358508 |
| chr1 | 156390135 | 156390698 | chr1 | 156405635 | 156406070 | chr1 | 156406105 | 156406431 |
| chr1 | 156432124 | 156432321 | chr1 | 156594974 | 156595021 | chr1 | 156611889 | 156611943 |
| chr1 | 156611994 | 156612119 | chr1 | 156626589 | 156626658 | chr1 | 156626891 | 156627018 |

TABLE 13-continued

| chr | start | end | chr | start | end | chr | start | end |
|---|---|---|---|---|---|---|---|---|
| chr1 | 156646278 | 156646307 | chr1 | 156646593 | 156646596 | chr1 | 156646635 | 156646647 |
| chr1 | 156814933 | 156814952 | chr1 | 156815031 | 156815146 | chr1 | 156815445 | 156815745 |
| chr1 | 156830269 | 156830348 | chr1 | 156838167 | 156838320 | chr1 | 156863107 | 156863331 |
| chr1 | 156863662 | 156863724 | chr1 | 157247368 | 157247388 | chr1 | 157458909 | 157458935 |
| chr1 | 157895413 | 157895443 | chr1 | 158669704 | 158669882 | chr1 | 158687415 | 158687550 |
| chr1 | 159140357 | 159140386 | chr1 | 159158348 | 159158368 | chr1 | 159158472 | 159158511 |
| chr1 | 159187279 | 159187429 | chr1 | 159258862 | 159258891 | chr1 | 159337517 | 159337615 |
| chr1 | 159409192 | 159409221 | chr1 | 160693934 | 160693958 | chr1 | 160992336 | 160992372 |
| chr1 | 161007587 | 161007746 | chr1 | 161086730 | 161086772 | chr1 | 161228659 | 161228891 |
| chr1 | 161275564 | 161275578 | chr1 | 161275640 | 161276026 | chr1 | 161368993 | 161369405 |
| chr1 | 161369859 | 161369945 | chr1 | 161442441 | 161442471 | chr1 | 161466301 | 161466324 |
| chr1 | 161471748 | 161471779 | chr1 | 161591472 | 161591546 | chr1 | 162724401 | 162724430 |
| chr1 | 162729615 | 162729686 | chr1 | 162748392 | 162748421 | chr1 | 162792306 | 162792533 |
| chr1 | 163393034 | 163393064 | chr1 | 164290615 | 164290671 | chr1 | 164730649 | 164730693 |
| chr1 | 165086988 | 165087027 | chr1 | 165205079 | 165205146 | chr1 | 165321747 | 165321786 |
| chr1 | 165323151 | 165323181 | chr1 | 165324196 | 165324249 | chr1 | 165324305 | 165324357 |
| chr1 | 165324488 | 165324668 | chr1 | 165325108 | 165325356 | chr1 | 165325395 | 165325521 |
| chr1 | 165325896 | 165325950 | chr1 | 165326204 | 165326204 | chr1 | 165326297 | 165326469 |
| chr1 | 165414191 | 165414272 | chr1 | 166134247 | 166134306 | chr1 | 166134728 | 166134796 |
| chr1 | 166135193 | 166135281 | chr1 | 166853563 | 166853592 | chr1 | 166890292 | 166890436 |
| chr1 | 166916866 | 166916920 | chr1 | 166916937 | 166916949 | chr1 | 167090617 | 167090757 |
| chr1 | 167599179 | 167599330 | chr1 | 167599616 | 167599844 | chr1 | 167823370 | 167823461 |
| chr1 | 169396376 | 169396688 | chr1 | 169396731 | 169396923 | chr1 | 169838016 | 169838187 |
| chr1 | 169930112 | 169930305 | chr1 | 170629540 | 170629569 | chr1 | 170629999 | 170630029 |
| chr1 | 170630456 | 170630810 | chr1 | 170631084 | 170631163 | chr1 | 170631477 | 170631559 |
| chr1 | 170633607 | 170633637 | chr1 | 170637666 | 170637796 | chr1 | 170640517 | 170640624 |
| chr1 | 170640665 | 170640691 | chr1 | 171625525 | 171625543 | chr1 | 171810200 | 171810972 |
| chr1 | 173638647 | 173639085 | chr1 | 175346381 | 175346551 | chr1 | 175388664 | 175388682 |
| chr1 | 177133721 | 177133814 | chr1 | 177140105 | 177140173 | chr1 | 177140305 | 177140714 |
| chr1 | 177150773 | 177150803 | chr1 | 178063112 | 178063150 | chr1 | 179544967 | 179545098 |
| chr1 | 179712164 | 179712338 | chr1 | 179712411 | 179712553 | chr1 | 179712568 | 179712733 |
| chr1 | 179712831 | 179713174 | chr1 | 180198061 | 180198209 | chr1 | 180202649 | 180203016 |
| chr1 | 180203413 | 180203607 | chr1 | 180203634 | 180204619 | chr1 | 180204898 | 180204924 |
| chr1 | 180235730 | 180235760 | chr1 | 180882576 | 180882695 | chr1 | 180919682 | 180919718 |
| chr1 | 180925271 | 180925402 | chr1 | 181287679 | 181287757 | chr1 | 181288014 | 181288188 |
| chr1 | 181451407 | 181452120 | chr1 | 181462871 | 181452967 | chr1 | 181454873 | 181454912 |
| chr1 | 181455183 | 181455263 | chr1 | 182584048 | 182584339 | chr1 | 182584404 | 182584613 |
| chr1 | 182807578 | 182807660 | chr1 | 182921839 | 182921868 | chr1 | 183129382 | 183129530 |
| chr1 | 183386150 | 183386288 | chr1 | 183386599 | 183386626 | chr1 | 183386947 | 183386964 |
| chr1 | 183387266 | 183387319 | chr1 | 183462983 | 183463024 | chr1 | 183774244 | 183774363 |
| chr1 | 184005701 | 184005814 | chr1 | 185073818 | 185073966 | chr1 | 186570930 | 186570950 |
| chr1 | 190444855 | 190444885 | chr1 | 190445181 | 190445276 | chr1 | 190447389 | 190447519 |
| chr1 | 195732322 | 195732521 | chr1 | 196577628 | 196577858 | chr1 | 196578101 | 196578150 |
| chr1 | 197879400 | 197879660 | chr1 | 197879717 | 197880156 | chr1 | 197882140 | 197882201 |
| chr1 | 197882453 | 197882611 | chr1 | 197887052 | 197887066 | chr1 | 197887147 | 197887456 |
| chr1 | 197887707 | 197887741 | chr1 | 197888052 | 197888121 | chr1 | 197888181 | 197888319 |
| chr1 | 197888643 | 197889286 | chr1 | 200009357 | 200009450 | chr1 | 200009750 | 200010114 |
| chr1 | 200011323 | 200012227 | chr1 | 200591054 | 200591080 | chr1 | 201368582 | 201368727 |
| chr1 | 201476501 | 201476619 | chr1 | 201983113 | 201983200 | chr1 | 202081766 | 202081804 |
| chr1 | 202183371 | 202183401 | chr1 | 202531939 | 202532087 | chr1 | 202679215 | 202679518 |
| chr1 | 203298307 | 203298449 | chr1 | 203429564 | 203429594 | chr1 | 203681332 | 203681362 |
| chr1 | 204333609 | 204333668 | chr1 | 204478326 | 204478427 | chr1 | 204499813 | 204499842 |
| chr1 | 204524704 | 204524724 | chr1 | 204531203 | 204531540 | chr1 | 204531600 | 204531757 |
| chr1 | 204653561 | 204653595 | chr1 | 204653793 | 204653807 | chr1 | 205312596 | 205312911 |
| chr1 | 205424654 | 205424957 | chr1 | 205537663 | 205537772 | chr1 | 207200870 | 207200962 |
| chr1 | 207227527 | 207227556 | chr1 | 207669496 | 207669787 | chr1 | 207669829 | 207670060 |
| chr1 | 207818394 | 207818396 | chr1 | 207818434 | 207818493 | chr1 | 208084289 | 208084488 |
| chr1 | 209381132 | 209381165 | chr1 | 209604382 | 209604597 | chr1 | 209605386 | 209605415 |
| chr1 | 209849170 | 209849199 | chr1 | 209849430 | 209849459 | chr1 | 210111146 | 210111176 |
| chr1 | 210111388 | 210111421 | chr1 | 210111797 | 210111922 | chr1 | 210112037 | 210112140 |
| chr1 | 211847706 | 211847787 | chr1 | 212963883 | 212963987 | chr1 | 213123871 | 213123979 |
| chr1 | 213124669 | 213124910 | chr1 | 214156419 | 214156928 | chr1 | 214158838 | 214158910 |
| chr1 | 214160107 | 214160184 | chr1 | 214360675 | 214360858 | chr1 | 214360927 | 214360968 |
| chr1 | 214724531 | 214724561 | chr1 | 215255094 | 215255799 | chr1 | 216897216 | 216897307 |
| chr1 | 217307385 | 217308274 | chr1 | 217309007 | 217309105 | chr1 | 217309764 | 217309816 |
| chr1 | 217311265 | 217311839 | chr1 | 217313042 | 217313042 | chr1 | 217313069 | 217313747 |
| chr1 | 217805158 | 217805247 | chr1 | 218520096 | 218520291 | chr1 | 218520310 | 218520399 |
| chr1 | 218520775 | 218520805 | chr1 | 219346992 | 219347035 | chr1 | 219347394 | 219347472 |
| chr1 | 220101145 | 220101210 | chr1 | 220101371 | 220101385 | chr1 | 220101683 | 220101712 |
| chr1 | 220132075 | 220132111 | chr1 | 220636466 | 220636510 | chr1 | 220700814 | 220700897 |
| chr1 | 221052038 | 221052492 | chr1 | 221053610 | 221053862 | chr1 | 221067506 | 221067688 |
| chr1 | 221068156 | 221068185 | chr1 | 221068793 | 221069150 | chr1 | 221510339 | 221510368 |
| chr1 | 221737191 | 221737220 | chr1 | 223302825 | 223302890 | chr1 | 223538344 | 223538641 |
| chr1 | 223936633 | 223936752 | chr1 | 223936996 | 223937057 | chr1 | 224363560 | 224363589 |
| chr1 | 224400490 | 224400524 | chr1 | 224493975 | 224493999 | chr1 | 224528814 | 224528844 |
| chr1 | 224803717 | 224803751 | chr1 | 224804097 | 224804295 | chr1 | 224804396 | 224804686 |
| chr1 | 224804847 | 224804910 | chr1 | 224805198 | 224805751 | chr1 | 226411247 | 226411273 |
| chr1 | 226411700 | 226411832 | chr1 | 226814346 | 226814408 | chr1 | 226925067 | 226925195 |

TABLE 13-continued

| chr | start | end | chr | start | end | chr | start | end |
|---|---|---|---|---|---|---|---|---|
| chr1 | 226997660 | 226997719 | chr1 | 227729830 | 227730075 | chr1 | 227748700 | 227748733 |
| chr1 | 228195377 | 228196349 | chr1 | 228201221 | 228201251 | chr1 | 228247998 | 228248027 |
| chr1 | 228248302 | 228248332 | chr1 | 228345999 | 228346195 | chr1 | 228461158 | 228461197 |
| chr1 | 228463311 | 228463706 | chr1 | 228528840 | 228529016 | chr1 | 228558699 | 228559238 |
| chr1 | 228566622 | 228566672 | chr1 | 228604124 | 228604254 | chr1 | 228633990 | 228634261 |
| chr1 | 228645140 | 228645243 | chr1 | 228645306 | 228645734 | chr1 | 228646195 | 228646238 |
| chr1 | 228651432 | 228651626 | chr1 | 228651879 | 228651901 | chr1 | 228652224 | 228652452 |
| chr1 | 228652509 | 228652629 | chr1 | 228871865 | 228872003 | chr1 | 229542838 | 229542952 |
| chr1 | 229543553 | 229543603 | chr1 | 229566753 | 229567276 | chr1 | 229567370 | 229567992 |
| chr1 | 229568158 | 229568204 | chr1 | 229569810 | 229569852 | chr1 | 230404217 | 230404263 |
| chr1 | 230561779 | 230561824 | chr1 | 231297103 | 231297221 | chr1 | 231298595 | 231298707 |
| chr1 | 232765195 | 232765301 | chr1 | 233465473 | 233465503 | chr1 | 233750082 | 233750302 |
| chr1 | 234040247 | 234040319 | chr1 | 234040886 | 234040973 | chr1 | 234041416 | 234041624 |
| chr1 | 234349988 | 234350100 | chr1 | 234445373 | 234445403 | chr1 | 234620866 | 234620979 |
| chr1 | 234798171 | 234798201 | chr1 | 234839889 | 234840058 | chr1 | 234844955 | 234845079 |
| chr1 | 234845467 | 234845497 | chr1 | 235665700 | 235665736 | chr1 | 235813781 | 235813796 |
| chr1 | 235814010 | 235814202 | chr1 | 235814447 | 235814476 | chr1 | 236227637 | 236227743 |
| chr1 | 236227770 | 236227920 | chr1 | 236228022 | 236228096 | chr1 | 236228582 | 236228623 |
| chr1 | 236228706 | 236228789 | chr1 | 236559176 | 236559206 | chr1 | 236559257 | 236559271 |
| chr1 | 236849457 | 236849505 | chr1 | 237205159 | 237205188 | chr1 | 237206102 | 237206265 |
| chr1 | 237206512 | 237206735 | chr1 | 238024448 | 238024477 | chr1 | 239550594 | 239551193 |
| chr1 | 240118848 | 240118973 | chr1 | 240161123 | 240161380 | chr1 | 240254944 | 240255011 |
| chr1 | 240255361 | 240255500 | chr1 | 240255819 | 240256158 | chr1 | 240256663 | 240256721 |
| chr1 | 240775425 | 240775455 | chr1 | 241062096 | 241052126 | chr1 | 241520296 | 241520345 |
| chr1 | 241520583 | 241520612 | chr1 | 241587034 | 241587113 | chr1 | 241587587 | 241587797 |
| chr1 | 241912749 | 241912778 | chr1 | 242686734 | 242687688 | chr1 | 242688184 | 242688243 |
| chr1 | 242688477 | 242688695 | chr1 | 243646610 | 243646673 | chr1 | 243859000 | 243859029 |
| chr1 | 244014221 | 244014376 | chr1 | 244080672 | 244080702 | chr1 | 244080963 | 244081061 |
| chr1 | 244081078 | 244081203 | chr1 | 244893214 | 244893295 | chr1 | 245032517 | 245032603 |
| chr1 | 245135753 | 245135849 | chr1 | 245494495 | 245494578 | chr1 | 245849914 | 245849944 |
| chr1 | 246198078 | 246198203 | chr1 | 246330309 | 246330409 | chr1 | 246488175 | 246488316 |
| chr1 | 247496038 | 247496057 | chr1 | 247608784 | 247608814 | chr1 | 248002278 | 248002358 |
| chr1 | 248020516 | 248020630 | chr1 | 248020957 | 248021349 | chr1 | 248028015 | 248028202 |
| chr1 | 248074729 | 248074768 | chr1 | 248074828 | 248074927 | chr1 | 248099751 | 248099809 |
| chr1 | 248328701 | 248328841 | chr1 | 249121622 | 249121704 | chr2 | 46214 | 46450 |
| chr2 | 264163 | 264204 | chr2 | 287580 | 287641 | chr2 | 288404 | 288470 |
| chr2 | 468424 | 468672 | chr2 | 496228 | 496380 | chr2 | 602657 | 602687 |
| chr2 | 720836 | 720894 | chr2 | 875961 | 875991 | chr2 | 945913 | 946000 |
| chr2 | 946208 | 946217 | chr2 | 946526 | 946566 | chr2 | 946917 | 947043 |
| chr2 | 947127 | 947159 | chr2 | 1652837 | 1653230 | chr2 | 1670168 | 1670216 |
| chr2 | 1746614 | 1747032 | chr2 | 1747670 | 1748007 | chr2 | 1748397 | 1748890 |
| chr2 | 2321773 | 2321802 | chr2 | 2336413 | 2336442 | chr2 | 2646900 | 2646930 |
| chr2 | 2672620 | 2672732 | chr2 | 2844720 | 2844750 | chr2 | 2893165 | 2893195 |
| chr2 | 3259989 | 3260103 | chr2 | 4019911 | 4020036 | chr2 | 4050752 | 4050781 |
| chr2 | 5831178 | 5831204 | chr2 | 5831238 | 5831324 | chr2 | 5831789 | 5831819 |
| chr2 | 5833283 | 5833432 | chr2 | 5833500 | 5833639 | chr2 | 5833735 | 5834028 |
| chr2 | 5836085 | 5836253 | chr2 | 5836548 | 5836574 | chr2 | 5836622 | 5836744 |
| chr2 | 5836828 | 5836991 | chr2 | 5837353 | 5837414 | chr2 | 5866098 | 5866211 |
| chr2 | 7164467 | 2164788 | chr2 | 7571577 | 2571747 | chr2 | 8735932 | 8736064 |
| chr2 | 9134404 | 9134493 | chr2 | 9192356 | 9192379 | chr2 | 9289969 | 9290114 |
| chr2 | 9960734 | 9960764 | chr2 | 10115730 | 10115751 | chr2 | 10153062 | 10153325 |
| chr2 | 10154930 | 10155024 | chr2 | 10155264 | 10155298 | chr2 | 10156313 | 10156389 |
| chr2 | 10182827 | 10182904 | chr2 | 10369155 | 10369242 | chr2 | 10408398 | 10408459 |
| chr2 | 10688874 | 10688904 | chr2 | 11052517 | 11052559 | chr2 | 11142275 | 11142315 |
| chr2 | 11672746 | 11672775 | chr2 | 11809957 | 11810115 | chr2 | 11903450 | 11903480 |
| chr2 | 12246114 | 12246196 | chr2 | 12858452 | 12858618 | chr2 | 14772761 | 14772823 |
| chr2 | 14774281 | 14774567 | chr2 | 17719688 | 17719812 | chr2 | 18059035 | 18059085 |
| chr2 | 18059781 | 18059841 | chr2 | 19550214 | 19550244 | chr2 | 19551322 | 19551366 |
| chr2 | 19556318 | 19556672 | chr2 | 19557068 | 19557098 | chr2 | 19557685 | 19557727 |
| chr2 | 19558832 | 19558893 | chr2 | 19561131 | 19561316 | chr2 | 19561524 | 19561685 |
| chr2 | 19563358 | 19563433 | chr2 | 20068798 | 20068885 | chr2 | 20442466 | 20442498 |
| chr2 | 20642625 | 20642648 | chr2 | 20865636 | 20865927 | chr2 | 25374762 | 25374804 |
| chr2 | 25391013 | 25391212 | chr2 | 25391684 | 25391725 | chr2 | 25438821 | 25438871 |
| chr2 | 25439139 | 25439383 | chr2 | 25600736 | 25600804 | chr2 | 26372967 | 26372997 |
| chr2 | 26395447 | 26395556 | chr2 | 26402030 | 26402060 | chr2 | 26407744 | 26407921 |
| chr2 | 26521972 | 26522127 | chr2 | 26915763 | 26916066 | chr2 | 26916089 | 26916259 |
| chr2 | 27070324 | 27070414 | chr2 | 27071240 | 27071346 | chr2 | 27072492 | 27072534 |
| chr2 | 27072822 | 27072989 | chr2 | 27356168 | 27356198 | chr2 | 27578380 | 27578396 |
| chr2 | 27665125 | 27665154 | chr2 | 27665506 | 27665711 | chr2 | 27887525 | 27887555 |
| chr2 | 29033336 | 29033697 | chr2 | 29091592 | 29091625 | chr2 | 29338159 | 29338747 |
| chr2 | 29338810 | 29338969 | chr2 | 29420483 | 29420512 | chr2 | 29432640 | 29432696 |
| chr2 | 29436844 | 29436888 | chr2 | 29443573 | 29443710 | chr2 | 29445198 | 29445482 |
| chr2 | 29446361 | 29446396 | chr2 | 30143304 | 30143322 | chr2 | 30143383 | 30143492 |
| chr2 | 30144041 | 30144150 | chr2 | 30144175 | 30144411 | chr2 | 30453785 | 30453941 |
| chr2 | 31360306 | 31360589 | chr2 | 31360631 | 31360755 | chr2 | 31360804 | 31360831 |
| chr2 | 31361089 | 31361118 | chr2 | 31361356 | 31361385 | chr2 | 31456682 | 31457039 |
| chr2 | 32504334 | 32504378 | chr2 | 32580386 | 32580431 | chr2 | 38302370 | 38302876 |
| chr2 | 38365727 | 38365748 | chr2 | 38551124 | 38551167 | chr2 | 38727561 | 38727707 |

TABLE 13-continued

| chr | start | end | chr | start | end | chr | start | end |
|---|---|---|---|---|---|---|---|---|
| chr2 | 38762382 | 38762412 | chr2 | 39187218 | 39187237 | chr2 | 39187544 | 39187722 |
| chr2 | 39893090 | 39893501 | chr2 | 39893972 | 39894059 | chr2 | 40678603 | 40678872 |
| chr2 | 40678932 | 40679604 | chr2 | 42274595 | 42274633 | chr2 | 42329431 | 42329444 |
| chr2 | 42329494 | 42329666 | chr2 | 42720262 | 42720446 | chr2 | 43019599 | 43019868 |
| chr2 | 43451909 | 43452327 | chr2 | 43824133 | 43824153 | chr2 | 44497708 | 44497875 |
| chr2 | 44809187 | 44809217 | chr2 | 45028988 | 45029058 | chr2 | 45029184 | 45029371 |
| chr2 | 45029682 | 45029712 | chr2 | 45155125 | 45155210 | chr2 | 45155356 | 45156811 |
| chr2 | 45156833 | 45157711 | chr2 | 45159956 | 45160267 | chr2 | 45160596 | 45160634 |
| chr2 | 45161663 | 45162112 | chr2 | 45162394 | 45162481 | chr2 | 45162751 | 45162913 |
| chr2 | 45164663 | 45164693 | chr2 | 45165564 | 45165594 | chr2 | 45168803 | 45168833 |
| chr2 | 45169446 | 45170029 | chr2 | 45171385 | 45171563 | chr2 | 45171837 | 45171862 |
| chr2 | 45176601 | 45176768 | chr2 | 45179620 | 45179650 | chr2 | 45179939 | 45180203 |
| chr2 | 45181520 | 45181672 | chr2 | 45181887 | 45182001 | chr2 | 45228627 | 45228730 |
| chr2 | 45231320 | 45231396 | chr2 | 45231805 | 45232131 | chr2 | 45233385 | 45233586 |
| chr2 | 45235594 | 45235926 | chr2 | 45237673 | 45237795 | chr2 | 45240548 | 45240630 |
| chr2 | 45240764 | 45240784 | chr2 | 45241136 | 45241168 | chr2 | 45395854 | 45395920 |
| chr2 | 45396315 | 45396451 | chr2 | 45396688 | 45396995 | chr2 | 46526302 | 46526448 |
| chr2 | 47193930 | 47194093 | chr2 | 47200591 | 47200621 | chr2 | 47249725 | 47249848 |
| chr2 | 47598278 | 47598518 | chr2 | 47598578 | 47598620 | chr2 | 47748140 | 47748494 |
| chr2 | 47797043 | 47797818 | chr2 | 47798180 | 47798663 | chr2 | 47798954 | 47799032 |
| chr2 | 48636504 | 48636647 | chr2 | 48982582 | 48982700 | chr2 | 48982754 | 48982866 |
| chr2 | 50573595 | 50573638 | chr2 | 50573692 | 50573865 | chr2 | 50574121 | 50574355 |
| chr2 | 50574402 | 50574684 | chr2 | 50574739 | 50574859 | chr2 | 55289094 | 55289274 |
| chr2 | 56149836 | 56149866 | chr2 | 56150729 | 56151193 | chr2 | 56410817 | 56410996 |
| chr2 | 56411691 | 56411733 | chr2 | 58656049 | 58656125 | chr2 | 60706759 | 60706804 |
| chr2 | 60796587 | 60796617 | chr2 | 60797137 | 60797281 | chr2 | 61135115 | 61135137 |
| chr2 | 62798343 | 62798386 | chr2 | 63278962 | 63278992 | chr2 | 63280952 | 63281651 |
| chr2 | 63282716 | 63282786 | chr2 | 63283014 | 63283027 | chr2 | 63283952 | 63284146 |
| chr2 | 63284777 | 63284811 | chr2 | 63285081 | 63286047 | chr2 | 63286359 | 63286584 |
| chr2 | 63286694 | 63286747 | chr2 | 63287083 | 63287368 | chr2 | 66251310 | 65251340 |
| chr2 | 66652863 | 66652963 | chr2 | 66653238 | 66653496 | chr2 | 66653764 | 66653914 |
| chr2 | 66660650 | 66660888 | chr2 | 66662749 | 66662824 | chr2 | 66808525 | 66808633 |
| chr2 | 66808727 | 66809361 | chr2 | 67625453 | 67625492 | chr2 | 67625732 | 67625770 |
| chr2 | 67626102 | 67626257 | chr2 | 68287783 | 68287799 | chr2 | 68546324 | 68546516 |
| chr2 | 68546553 | 68546892 | chr2 | 68559343 | 68559365 | chr2 | 68672853 | 68672938 |
| chr2 | 69027024 | 69027053 | chr2 | 70418608 | 70418627 | chr2 | 71355038 | 71355117 |
| chr2 | 71503790 | 71503823 | chr2 | 71504103 | 71504148 | chr2 | 71680833 | 71680863 |
| chr2 | 71693374 | 71693593 | chr2 | 72374375 | 72374432 | chr2 | 72374714 | 72374765 |
| chr2 | 73145640 | 73145694 | chr2 | 73145924 | 73146021 | chr2 | 73147324 | 73147527 |
| chr2 | 73147967 | 73148066 | chr2 | 73148175 | 73148243 | chr2 | 73150924 | 73150954 |
| chr2 | 73151187 | 73151831 | chr2 | 73152740 | 73152754 | chr2 | 73416356 | 73416386 |
| chr2 | 73429523 | 73429614 | chr2 | 73429977 | 73430069 | chr2 | 73430322 | 73430372 |
| chr2 | 73430443 | 73430743 | chr2 | 73440250 | 73440293 | chr2 | 73518448 | 73518919 |
| chr2 | 73519579 | 73519841 | chr2 | 74010528 | 74010621 | chr2 | 74153198 | 74153227 |
| chr2 | 74426185 | 74426214 | chr2 | 74454074 | 74454261 | chr2 | 74647864 | 74647906 |
| chr2 | 74726744 | 74726774 | chr2 | 74740852 | 74741387 | chr2 | 74741835 | 74741844 |
| chr2 | 74741873 | 74741955 | chr2 | 74742325 | 74742647 | chr2 | 74742694 | 74743144 |
| chr2 | 74782081 | 74782087 | chr2 | 74782219 | 74782271 | chr2 | 75427040 | 75427114 |
| chr2 | 75427369 | 75427399 | chr2 | 75427930 | 75428177 | chr2 | 75720510 | 75720541 |
| chr2 | 79347459 | 79347546 | chr2 | 80529378 | 80529443 | chr2 | 80529662 | 80529908 |
| chr2 | 80529986 | 80530022 | chr2 | 80530505 | 80530558 | chr2 | 80531725 | 80531755 |
| chr2 | 80549585 | 80549745 | chr2 | 85107454 | 85107538 | chr2 | 85361467 | 85361528 |
| chr2 | 86263223 | 86263270 | chr2 | 86791221 | 86791251 | chr2 | 87016579 | 87016636 |
| chr2 | 87017796 | 87018396 | chr2 | 87036611 | 87036640 | chr2 | 88469312 | 88469398 |
| chr2 | 88751281 | 88751419 | chr2 | 88751461 | 88751800 | chr2 | 88752055 | 88752285 |
| chr2 | 88752603 | 88752785 | chr2 | 88990189 | 88990264 | chr2 | 89064806 | 89064975 |
| chr2 | 89065129 | 89065278 | chr2 | 95663969 | 95664014 | chr2 | 95690747 | 95690793 |
| chr2 | 95691036 | 95691269 | chr2 | 95691530 | 95691769 | chr2 | 95691994 | 95692480 |
| chr2 | 95941678 | 95941812 | chr2 | 96070057 | 96070081 | chr2 | 96990898 | 96991316 |
| chr2 | 97193252 | 97193626 | chr2 | 97427515 | 97428093 | chr2 | 98703323 | 98703475 |
| chr2 | 98703675 | 98703736 | chr2 | 98962898 | 98962900 | chr2 | 98963329 | 98963599 |
| chr2 | 98963869 | 98964200 | chr2 | 98964596 | 98964645 | chr2 | 99439369 | 99439507 |
| chr2 | 99553391 | 99553656 | chr2 | 99796295 | 99796330 | chr2 | 99798646 | 99798750 |
| chr2 | 99799050 | 99799153 | chr2 | 100618451 | 100618480 | chr2 | 100937836 | 100938209 |
| chr2 | 100938330 | 100938544 | chr2 | 100938575 | 100938809 | chr2 | 100938985 | 100939155 |
| chr2 | 101009832 | 101009927 | chr2 | 101034242 | 101034293 | chr2 | 101436632 | 101436708 |
| chr2 | 101666893 | 101667004 | chr2 | 102091180 | 102091335 | chr2 | 103236165 | 103236292 |
| chr2 | 105459081 | 105459151 | chr2 | 105459908 | 105460599 | chr2 | 105460921 | 105460951 |
| chr2 | 105461187 | 105461243 | chr2 | 105461564 | 105461667 | chr2 | 105461700 | 105461896 |
| chr2 | 105462165 | 105462222 | chr2 | 105468791 | 105468908 | chr2 | 105469645 | 105469856 |
| chr2 | 105469881 | 105470091 | chr2 | 105470350 | 105470840 | chr2 | 105472231 | 105472425 |
| chr2 | 105472713 | 105472845 | chr2 | 105473248 | 105473521 | chr2 | 105478762 | 105479089 |
| chr2 | 105483655 | 105483719 | chr2 | 105484450 | 105484522 | chr2 | 105488437 | 105488496 |
| chr2 | 105760981 | 105761009 | chr2 | 105937344 | 106937498 | chr2 | 106060615 | 106060792 |
| chr2 | 106681733 | 106681767 | chr2 | 106682012 | 106682098 | chr2 | 106730223 | 106730256 |
| chr2 | 106959368 | 106959568 | chr2 | 106969916 | 106959988 | chr2 | 107103865 | 107103928 |
| chr2 | 107502600 | 107502729 | chr2 | 107503532 | 107503561 | chr2 | 107503884 | 107504018 |
| chr2 | 109335133 | 109335166 | chr2 | 109648080 | 109648222 | chr2 | 109745989 | 109746079 |

TABLE 13-continued

| chr | start | end | chr | start | end | chr | start | end |
|---|---|---|---|---|---|---|---|---|
| chr2 | 109746289 | 109746387 | chr2 | 109746463 | 109746477 | chr2 | 110015080 | 110015110 |
| chr2 | 110370941 | 110371219 | chr2 | 110873016 | 110873045 | chr2 | 111544817 | 111544847 |
| chr2 | 111875191 | 111875611 | chr2 | 112657033 | 112657092 | chr2 | 113227125 | 113227225 |
| chr2 | 113594639 | 113594668 | chr2 | 113931503 | 113931532 | chr2 | 114256978 | 114257137 |
| chr2 | 114261300 | 114261458 | chr2 | 114470172 | 114470201 | chr2 | 115918661 | 115918892 |
| chr2 | 115919338 | 115919424 | chr2 | 115919831 | 115920534 | chr2 | 118981151 | 118981856 |
| chr2 | 118981946 | 118982147 | chr2 | 118982254 | 118982497 | chr2 | 119067636 | 119068049 |
| chr2 | 119532161 | 119532255 | chr2 | 119566239 | 119566272 | chr2 | 119591351 | 119891465 |
| chr2 | 119592588 | 119592777 | chr2 | 119592997 | 119593567 | chr2 | 119599926 | 119600031 |
| chr2 | 119600332 | 119600555 | chr2 | 119600570 | 119600747 | chr2 | 119600949 | 119600952 |
| chr2 | 119600996 | 119601061 | chr2 | 119602601 | 119602629 | chr2 | 119602829 | 119603086 |
| chr2 | 119604032 | 119604158 | chr2 | 119604809 | 119604851 | chr2 | 119606135 | 119606499 |
| chr2 | 119606783 | 119606839 | chr2 | 119607176 | 119607411 | chr2 | 119610844 | 119610939 |
| chr2 | 119611745 | 119611799 | chr2 | 119612324 | 119612354 | chr2 | 119614130 | 119614171 |
| chr2 | 119614780 | 119614852 | chr2 | 119615055 | 119615627 | chr2 | 119616155 | 119616551 |
| chr2 | 119616809 | 119616870 | chr2 | 119914720 | 119914752 | chr2 | 119916525 | 119916595 |
| chr2 | 120281646 | 120281693 | chr2 | 120281939 | 120281953 | chr2 | 120980068 | 120980098 |
| chr2 | 120980353 | 120980395 | chr2 | 121200390 | 121200433 | chr2 | 121345081 | 121345111 |
| chr2 | 121411888 | 121412153 | chr2 | 122176232 | 122176293 | chr2 | 122495310 | 122495413 |
| chr2 | 122809783 | 122809801 | chr2 | 124782333 | 124782458 | chr2 | 124782692 | 124783097 |
| chr2 | 127413970 | 127413995 | chr2 | 127423220 | 127423350 | chr2 | 127429010 | 127429044 |
| chr2 | 127438633 | 127438663 | chr2 | 127783043 | 127783257 | chr2 | 127863601 | 127863725 |
| chr2 | 127976467 | 127976672 | chr2 | 128421891 | 128421947 | chr2 | 128616617 | 128616638 |
| chr2 | 128847700 | 128847723 | chr2 | 129494389 | 129494421 | chr2 | 130763584 | 130763623 |
| chr2 | 130971149 | 130971321 | chr2 | 131477785 | 131477936 | chr2 | 131594989 | 131595019 |
| chr2 | 131673756 | 131673785 | chr2 | 131720852 | 131721098 | chr2 | 131721461 | 131721584 |
| chr2 | 131721867 | 131721949 | chr2 | 131792260 | 131792519 | chr2 | 131792532 | 131792746 |
| chr2 | 131792921 | 131793131 | chr2 | 132088786 | 132088828 | chr2 | 132121661 | 132121829 |
| chr2 | 132152361 | 132152495 | chr2 | 132182790 | 132183089 | chr2 | 132208257 | 132208278 |
| chr2 | 132767457 | 132767492 | chr2 | 133014598 | 133014638 | chr2 | 133015299 | 133015323 |
| chr2 | 133062362 | 133062389 | chr2 | 133426249 | 133426279 | chr2 | 133426637 | 133426674 |
| chr2 | 136287374 | 136287390 | chr2 | 137522445 | 137522475 | chr2 | 137523825 | 137523855 |
| chr2 | 139536937 | 139537145 | chr2 | 139537443 | 139537822 | chr2 | 139537861 | 139537865 |
| chr2 | 142887871 | 142888066 | chr2 | 142888348 | 142888418 | chr2 | 144694367 | 144694514 |
| chr2 | 144694554 | 144695135 | chr2 | 145273404 | 145273751 | chr2 | 145274186 | 145274455 |
| chr2 | 145274814 | 145275213 | chr2 | 145282119 | 145282149 | chr2 | 148776809 | 148776892 |
| chr2 | 149633097 | 149633399 | chr2 | 149633744 | 149633965 | chr2 | 149645496 | 149645894 |
| chr2 | 151342903 | 151343277 | chr2 | 154333535 | 154333567 | chr2 | 154334272 | 154334665 |
| chr2 | 154335185 | 154335271 | chr2 | 154728245 | 154728440 | chr2 | 154729083 | 154729240 |
| chr2 | 154729559 | 154729589 | chr2 | 155555038 | 155555361 | chr2 | 157176592 | 157176717 |
| chr2 | 157177003 | 157178310 | chr2 | 157178646 | 157178731 | chr2 | 160761070 | 160761556 |
| chr2 | 161253374 | 161253455 | chr2 | 162272989 | 162273314 | chr2 | 162273383 | 162274338 |
| chr2 | 162274717 | 162274866 | chr2 | 162275146 | 162275226 | chr2 | 162275311 | 162275437 |
| chr2 | 162275473 | 162275802 | chr2 | 162280153 | 162280415 | chr2 | 162280741 | 162280956 |
| chr2 | 162283365 | 162283602 | chr2 | 162283783 | 162284055 | chr2 | 164593096 | 164593137 |
| chr2 | 168150069 | 168150245 | chr2 | 168150751 | 168150945 | chr2 | 170282981 | 170283080 |
| chr2 | 170551730 | 170551866 | chr2 | 170681880 | 170681911 | chr2 | 170682151 | 170682331 |
| chr2 | 171570182 | 171570189 | chr2 | 171570684 | 171570733 | chr2 | 171571264 | 171571315 |
| chr2 | 171571889 | 171572068 | chr2 | 171670349 | 171670446 | chr2 | 171671487 | 171671789 |
| chr2 | 171671800 | 171671881 | chr2 | 171673873 | 171673939 | chr2 | 171674739 | 171675066 |
| chr2 | 171675361 | 171675382 | chr2 | 171675523 | 171675592 | chr2 | 171676684 | 171676785 |
| chr2 | 171822428 | 171822480 | chr2 | 172367021 | 172367125 | chr2 | 172411136 | 172411166 |
| chr2 | 172945124 | 172945167 | chr2 | 172945896 | 172946211 | chr2 | 172947717 | 172947913 |
| chr2 | 172948184 | 172948314 | chr2 | 172948709 | 172948751 | chr2 | 172949186 | 172949282 |
| chr2 | 172949349 | 172949711 | chr2 | 172952521 | 172952881 | chr2 | 172952993 | 172953046 |
| chr2 | 172955472 | 172955545 | chr2 | 172957907 | 172958066 | chr2 | 172961398 | 172961598 |
| chr2 | 172964821 | 172964888 | chr2 | 172965296 | 172965298 | chr2 | 172965648 | 172965762 |
| chr2 | 172966264 | 172966442 | chr2 | 172972735 | 172972890 | chr2 | 172972931 | 172973218 |
| chr2 | 173099784 | 173099814 | chr2 | 173100262 | 173100430 | chr2 | 173422685 | 173422734 |
| chr2 | 174148138 | 174148157 | chr2 | 175190871 | 175191972 | chr2 | 175192085 | 175192468 |
| chr2 | 175193268 | 175193644 | chr2 | 175193809 | 175193823 | chr2 | 175195831 | 175195858 |
| chr2 | 175196432 | 175196575 | chr2 | 175197089 | 175197119 | chr2 | 175198752 | 175198766 |
| chr2 | 175198846 | 175198966 | chr2 | 175199527 | 175199554 | chr2 | 175199922 | 175199935 |
| chr2 | 175200140 | 175200440 | chr2 | 175200710 | 175200852 | chr2 | 175200917 | 175201182 |
| chr2 | 175201360 | 175201541 | chr2 | 175201776 | 175201828 | chr2 | 175202127 | 175202245 |
| chr2 | 175202569 | 175202600 | chr2 | 175202634 | 175202652 | chr2 | 175204174 | 175204204 |
| chr2 | 175204786 | 175204946 | chr2 | 175205588 | 175205799 | chr2 | 175206833 | 175206905 |
| chr2 | 175206961 | 175207028 | chr2 | 175207228 | 175207258 | chr2 | 175207536 | 175207653 |
| chr2 | 175208311 | 175208868 | chr2 | 175208997 | 175209135 | chr2 | 175547041 | 175547140 |
| chr2 | 175547384 | 175547413 | chr2 | 176940167 | 176940315 | chr2 | 176943269 | 176943568 |
| chr2 | 176943861 | 176943902 | chr2 | 176944457 | 176944846 | chr2 | 176945138 | 176945268 |
| chr2 | 176945582 | 176945784 | chr2 | 176946578 | 176946867 | chr2 | 176947285 | 176947389 |
| chr2 | 176947764 | 176947903 | chr2 | 176948599 | 176948742 | chr2 | 176949045 | 176949075 |
| chr2 | 176949695 | 176949869 | chr2 | 176950142 | 176950258 | chr2 | 176956558 | 176956599 |
| chr2 | 176956921 | 176957199 | chr2 | 176957577 | 176957628 | chr2 | 176957915 | 176957919 |
| chr2 | 176958138 | 176958489 | chr2 | 176959289 | 176959511 | chr2 | 176963448 | 176963522 |
| chr2 | 176964085 | 176964149 | chr2 | 176964390 | 176964767 | chr2 | 176965265 | 176965492 |
| chr2 | 176969463 | 176969613 | chr2 | 176969677 | 176969908 | chr2 | 176971628 | 176971651 |

TABLE 13-continued

| chr | start | end | chr | start | end | chr | start | end |
|---|---|---|---|---|---|---|---|---|
| chr2 | 176976029 | 176976188 | chr2 | 176980750 | 176980937 | chr2 | 176981377 | 176981506 |
| chr2 | 176982584 | 176982627 | chr2 | 176986715 | 176986848 | chr2 | 176987057 | 176987224 |
| chr2 | 176987971 | 176988103 | chr2 | 176988155 | 176988304 | chr2 | 176993074 | 176993103 |
| chr2 | 176993547 | 176993855 | chr2 | 176994031 | 176994379 | chr2 | 176994498 | 176994621 |
| chr2 | 176995072 | 176995269 | chr2 | 176995332 | 176995668 | chr2 | 177001102 | 177001695 |
| chr2 | 177001782 | 177001976 | chr2 | 177004566 | 177004658 | chr2 | 177014981 | 177015010 |
| chr2 | 177027425 | 177027438 | chr2 | 177030149 | 177030226 | chr2 | 177042984 | 177042998 |
| chr2 | 177043267 | 177043515 | chr2 | 177053276 | 177053434 | chr2 | 177053619 | 177053702 |
| chr2 | 177054113 | 177054351 | chr2 | 177503048 | 177503077 | chr2 | 177503581 | 177503610 |
| chr2 | 178098791 | 178098967 | chr2 | 178973003 | 178973042 | chr2 | 179303691 | 179303727 |
| chr2 | 179317019 | 179317057 | chr2 | 182321397 | 182321637 | chr2 | 182322039 | 182322170 |
| chr2 | 182322400 | 182323042 | chr2 | 182451522 | 182451551 | chr2 | 182542903 | 182542933 |
| chr2 | 182543321 | 182543418 | chr2 | 182543764 | 182543925 | chr2 | 182545211 | 182545275 |
| chr2 | 182545539 | 182545694 | chr2 | 182546002 | 182546085 | chr2 | 182546435 | 182546465 |
| chr2 | 182547385 | 182547387 | chr2 | 182547438 | 182547613 | chr2 | 182548062 | 182548161 |
| chr2 | 182549088 | 182549134 | chr2 | 182549337 | 182549454 | chr2 | 182550094 | 182550124 |
| chr2 | 182819048 | 182819216 | chr2 | 183731294 | 183731331 | chr2 | 183731467 | 183731524 |
| chr2 | 183731809 | 183732076 | chr2 | 185462869 | 185462980 | chr2 | 185463193 | 185463817 |
| chr2 | 186603488 | 186603518 | chr2 | 188419047 | 188419204 | chr2 | 189157427 | 189157688 |
| chr2 | 190708790 | 190708819 | chr2 | 193059025 | 193059317 | chr2 | 193059345 | 193059548 |
| chr2 | 193059662 | 193060067 | chr2 | 193060385 | 193060441 | chr2 | 193060683 | 193060891 |
| chr2 | 193061388 | 193061480 | chr2 | 198267345 | 198267374 | chr2 | 198456570 | 198456690 |
| chr2 | 198651002 | 198651076 | chr2 | 200326590 | 200326735 | chr2 | 200327424 | 200327451 |
| chr2 | 200329030 | 200329393 | chr2 | 200329433 | 200329668 | chr2 | 200333801 | 200333834 |
| chr2 | 200334976 | 200335451 | chr2 | 200335592 | 200335952 | chr2 | 201172444 | 201172480 |
| chr2 | 201450556 | 201450707 | chr2 | 201451014 | 201451040 | chr2 | 202097078 | 202097143 |
| chr2 | 202098936 | 202098965 | chr2 | 202101190 | 202101219 | chr2 | 202122459 | 202122683 |
| chr2 | 202899862 | 202899891 | chr2 | 203484608 | 203484627 | chr2 | 203880471 | 203880492 |
| chr2 | 206551072 | 206551362 | chr2 | 207139072 | 207139102 | chr2 | 207139347 | 207139605 |
| chr2 | 207307548 | 207307562 | chr2 | 207308802 | 207308857 | chr2 | 207506691 | 207507181 |
| chr2 | 208588311 | 208588341 | chr2 | 208635534 | 208635774 | chr2 | 208662170 | 208662213 |
| chr2 | 208989294 | 208989382 | chr2 | 209113097 | 209113126 | chr2 | 209225237 | 209225275 |
| chr2 | 209271322 | 209271336 | chr2 | 210636335 | 210636381 | chr2 | 210636430 | 210636689 |
| chr2 | 210636738 | 210636876 | chr2 | 212248428 | 212248457 | chr2 | 212288927 | 212288956 |
| chr2 | 212295683 | 212295820 | chr2 | 212530120 | 212530149 | chr2 | 212537902 | 212537994 |
| chr2 | 212566811 | 212566840 | chr2 | 212578292 | 212578321 | chr2 | 212587132 | 212587161 |
| chr2 | 213401235 | 213401339 | chr2 | 213401613 | 213401947 | chr2 | 213403110 | 213403337 |
| chr2 | 215275823 | 215275852 | chr2 | 215276310 | 215276339 | chr2 | 217448294 | 217448441 |
| chr2 | 217559296 | 217559326 | chr2 | 217559966 | 217559999 | chr2 | 218770207 | 218770270 |
| chr2 | 218806147 | 218806302 | chr2 | 219736151 | 219736691 | chr2 | 219828049 | 219828117 |
| chr2 | 219847462 | 219847555 | chr2 | 219848809 | 219848891 | chr2 | 219848936 | 219849001 |
| chr2 | 219857723 | 219857737 | chr2 | 220080510 | 220081033 | chr2 | 220173989 | 220174036 |
| chr2 | 220174060 | 220174296 | chr2 | 220196354 | 220196567 | chr2 | 220223098 | 220223128 |
| chr2 | 220223648 | 220223699 | chr2 | 220283363 | 220283519 | chr2 | 220299588 | 220299634 |
| chr2 | 220299886 | 220300059 | chr2 | 220349055 | 220349706 | chr2 | 220361447 | 220361466 |
| chr2 | 220416379 | 220416513 | chr2 | 220416848 | 220417649 | chr2 | 222435773 | 222435863 |
| chr2 | 223155722 | 223156188 | chr2 | 223158730 | 223159453 | chr2 | 223159869 | 223160065 |
| chr2 | 223160342 | 223160379 | chr2 | 223161247 | 223161684 | chr2 | 223161807 | 223162063 |
| chr2 | 223162779 | 223162890 | chr2 | 223162929 | 223163224 | chr2 | 223163473 | 223163535 |
| chr2 | 223163768 | 223163954 | chr2 | 223164534 | 223164883 | chr2 | 223165434 | 223165832 |
| chr2 | 223166294 | 223166408 | chr2 | 223166449 | 223166721 | chr2 | 223167389 | 223167573 |
| chr2 | 223168437 | 223168831 | chr2 | 223169640 | 223169864 | chr2 | 223170375 | 223170434 |
| chr2 | 223171109 | 223171180 | chr2 | 223172337 | 223172367 | chr2 | 223172924 | 223173173 |
| chr2 | 223175922 | 223176181 | chr2 | 223176456 | 223176511 | chr2 | 223176720 | 223176983 |
| chr2 | 223177315 | 223177610 | chr2 | 224661671 | 224661701 | chr2 | 224903260 | 224903440 |
| chr2 | 224903690 | 224903755 | chr2 | 224904108 | 224904237 | chr2 | 228029418 | 228029531 |
| chr2 | 228466761 | 228466777 | chr2 | 228735680 | 228735736 | chr2 | 228736215 | 228736295 |
| chr2 | 228736336 | 228736473 | chr2 | 229046107 | 229046503 | chr2 | 230795535 | 230795565 |
| chr2 | 232394970 | 232395021 | chr2 | 232395055 | 232395061 | chr2 | 232479822 | 232479938 |
| chr2 | 232522844 | 232522874 | chr2 | 232791704 | 232792012 | chr2 | 233350208 | 233350539 |
| chr2 | 233350844 | 233351278 | chr2 | 233352102 | 233352451 | chr2 | 233352507 | 233352762 |
| chr2 | 233352776 | 233352853 | chr2 | 233498710 | 233498873 | chr2 | 233498896 | 233499297 |
| chr2 | 233750525 | 233750555 | chr2 | 235404551 | 235404575 | chr2 | 235860746 | 235860808 |
| chr2 | 235861389 | 235861533 | chr2 | 236402771 | 236403013 | chr2 | 236403270 | 236403736 |
| chr2 | 236444269 | 236444298 | chr2 | 236578362 | 236578677 | chr2 | 236877262 | 236877399 |
| chr2 | 237072642 | 237073014 | chr2 | 237073354 | 237073414 | chr2 | 237076725 | 237076815 |
| chr2 | 237077562 | 237077608 | chr2 | 237077846 | 237078348 | chr2 | 237080264 | 237080294 |
| chr2 | 237081341 | 237081426 | chr2 | 237081537 | 237081553 | chr2 | 237082344 | 237082720 |
| chr2 | 237086349 | 237086468 | chr2 | 237145422 | 237145601 | chr2 | 237416216 | 237416429 |
| chr2 | 238395291 | 238395356 | chr2 | 238395906 | 238395961 | chr2 | 238535895 | 238535984 |
| chr2 | 238536005 | 238536114 | chr2 | 238864727 | 238864913 | chr2 | 239031722 | 239031780 |
| chr2 | 239051198 | 239051228 | chr2 | 239140139 | 239140249 | chr2 | 239149844 | 239149951 |
| chr2 | 239265702 | 239265787 | chr2 | 239482485 | 239482519 | chr2 | 239705305 | 239705337 |
| chr2 | 239755164 | 239755194 | chr2 | 239756373 | 239756462 | chr2 | 239756488 | 239756607 |
| chr2 | 239756634 | 239756648 | chr2 | 239757636 | 239757730 | chr2 | 239758126 | 239758144 |
| chr2 | 239758345 | 239758394 | chr2 | 239957330 | 239957448 | chr2 | 240167575 | 240167605 |
| chr2 | 240168811 | 240169051 | chr2 | 240319920 | 240320012 | chr2 | 240582379 | 240582524 |
| chr2 | 240619459 | 240619604 | chr2 | 240658227 | 240658421 | chr2 | 240658667 | 240658697 |

TABLE 13-continued

| chr | start | end | chr | start | end | chr | start | end |
|---|---|---|---|---|---|---|---|---|
| chr2 | 241095604 | 241095772 | chr2 | 241393200 | 241393469 | chr2 | 241497411 | 241497554 |
| chr2 | 241541932 | 241542357 | chr2 | 241545001 | 241545031 | chr2 | 241758377 | 241758819 |
| chr2 | 241759597 | 241759694 | chr2 | 241760149 | 241760178 | chr2 | 241760494 | 241760523 |
| chr2 | 241771165 | 241771257 | chr2 | 241865194 | 241865346 | chr2 | 242009391 | 242009421 |
| chr2 | 242021784 | 242021892 | chr2 | 242523907 | 242524147 | chr2 | 242549849 | 242549957 |
| chr2 | 242554549 | 242554579 | chr2 | 242716723 | 242716760 | chr2 | 242756144 | 242756297 |
| chr2 | 242832984 | 242833159 | chr2 | 242833558 | 242833588 | chr2 | 242833797 | 242833863 |
| chr2 | 242836495 | 242836640 | chr2 | 242925496 | 242925641 | chr3 | 238536 | 238715 |
| chr3 | 239007 | 239094 | chr3 | 239622 | 239868 | chr3 | 240110 | 240223 |
| chr3 | 2140277 | 2140398 | chr3 | 3840498 | 3840758 | chr3 | 3841046 | 3841144 |
| chr3 | 3842679 | 3842731 | chr3 | 5137960 | 5138019 | chr3 | 6902288 | 6902353 |
| chr3 | 6903425 | 6903463 | chr3 | 8810152 | 8810220 | chr3 | 9593979 | 9594015 |
| chr3 | 9594263 | 9594382 | chr3 | 9595396 | 9595502 | chr3 | 9904233 | 9904554 |
| chr3 | 9941469 | 9941509 | chr3 | 9957064 | 9957142 | chr3 | 9957451 | 9957677 |
| chr3 | 10182839 | 10182996 | chr3 | 10183321 | 10183350 | chr3 | 10183706 | 10183782 |
| chr3 | 10184304 | 10184333 | chr3 | 10191477 | 10191620 | chr3 | 11034264 | 11034359 |
| chr3 | 11035070 | 11035330 | chr3 | 12046405 | 12046632 | chr3 | 12632309 | 12632401 |
| chr3 | 12645678 | 12645713 | chr3 | 12729424 | 12729454 | chr3 | 12917606 | 12917655 |
| chr3 | 12926053 | 12926102 | chr3 | 12977067 | 12977144 | chr3 | 13323494 | 13323973 |
| chr3 | 13324420 | 13324433 | chr3 | 13324847 | 13324938 | chr3 | 13590448 | 13590640 |
| chr3 | 13679172 | 13679349 | chr3 | 13921407 | 13921463 | chr3 | 14851850 | 14851897 |
| chr3 | 14852325 | 14852919 | chr3 | 15123848 | 15123992 | chr3 | 16554052 | 16554111 |
| chr3 | 16554347 | 16554633 | chr3 | 17001303 | 17001333 | chr3 | 19189441 | 19189470 |
| chr3 | 19189694 | 19189765 | chr3 | 19190143 | 19190216 | chr3 | 20070714 | 20070869 |
| chr3 | 22413665 | 22413694 | chr3 | 22413960 | 22413974 | chr3 | 23964981 | 23965019 |
| chr3 | 24871002 | 24871176 | chr3 | 25469110 | 25469139 | chr3 | 25469377 | 25469406 |
| chr3 | 25469679 | 25469708 | chr3 | 26664045 | 26664119 | chr3 | 26664389 | 26664755 |
| chr3 | 27754478 | 27754508 | chr3 | 27762336 | 27762650 | chr3 | 27762857 | 27762887 |
| chr3 | 27763566 | 27763595 | chr3 | 27764457 | 27764471 | chr3 | 27765181 | 27765347 |
| chr3 | 27771497 | 27772004 | chr3 | 27772790 | 27772819 | chr3 | 28616832 | 28617675 |
| chr3 | 31494108 | 31494138 | chr3 | 32858353 | 32858958 | chr3 | 32859256 | 32859284 |
| chr3 | 32859418 | 32859693 | chr3 | 32860068 | 32860273 | chr3 | 33259904 | 33260776 |
| chr3 | 35680842 | 35680872 | chr3 | 36805815 | 36805863 | chr3 | 36806179 | 36806193 |
| chr3 | 36984378 | 36984402 | chr3 | 37493519 | 37493621 | chr3 | 37901923 | 37901953 |
| chr3 | 38030618 | 38030782 | chr3 | 38032331 | 38032361 | chr3 | 38035774 | 38035989 |
| chr3 | 38080685 | 38080925 | chr3 | 38081154 | 38081271 | chr3 | 38182244 | 38182306 |
| chr3 | 38182626 | 38182655 | chr3 | 38690624 | 38690668 | chr3 | 39851772 | 39851814 |
| chr3 | 40428507 | 40428713 | chr3 | 41266086 | 41266151 | chr3 | 42222730 | 42222759 |
| chr3 | 42640855 | 42640880 | chr3 | 42814569 | 42814603 | chr3 | 42947411 | 42947552 |
| chr3 | 44036260 | 44036330 | chr3 | 44036570 | 44036600 | chr3 | 44036820 | 44037203 |
| chr3 | 44037625 | 44037662 | chr3 | 44037874 | 44038646 | chr3 | 44039348 | 44040006 |
| chr3 | 44040511 | 44040553 | chr3 | 44040796 | 44041039 | chr3 | 44063434 | 44063872 |
| chr3 | 44596479 | 44596509 | chr3 | 44596716 | 44596809 | chr3 | 44626438 | 44626711 |
| chr3 | 44726875 | 44727193 | chr3 | 45187296 | 45187327 | chr3 | 46924934 | 46924964 |
| chr3 | 47144864 | 47144893 | chr3 | 48227765 | 48227788 | chr3 | 48236476 | 48236570 |
| chr3 | 48693304 | 48693700 | chr3 | 48693852 | 48694154 | chr3 | 48698251 | 48698431 |
| chr3 | 48698810 | 48699010 | chr3 | 48699377 | 48699767 | chr3 | 49236845 | 49236874 |
| chr3 | 49405953 | 49405982 | chr3 | 49412883 | 49412987 | chr3 | 49591832 | 49592076 |
| chr3 | 49907093 | 49907130 | chr3 | 49939931 | 49940398 | chr3 | 50072827 | 50072846 |
| chr3 | 50243383 | 50243480 | chr3 | 50374655 | 50374684 | chr3 | 50374917 | 50374946 |
| chr3 | 50375179 | 50375559 | chr3 | 50377973 | 50378002 | chr3 | 50378277 | 50378306 |
| chr3 | 50378512 | 50378541 | chr3 | 50395506 | 50395536 | chr3 | 50402170 | 50402944 |
| chr3 | 50575616 | 50575637 | chr3 | 50968445 | 50968511 | chr3 | 52442062 | 52442091 |
| chr3 | 52552556 | 52552661 | chr3 | 52553469 | 52553499 | chr3 | 53032733 | 53033524 |
| chr3 | 54155611 | 54155677 | chr3 | 54157381 | 54157450 | chr3 | 54157878 | 54157919 |
| chr3 | 55519219 | 55519253 | chr3 | 55523106 | 55523290 | chr3 | 55603443 | 55603632 |
| chr3 | 58153446 | 58153608 | chr3 | 62304567 | 62304669 | chr3 | 62353371 | 62354049 |
| chr3 | 62354283 | 62354328 | chr3 | 62354625 | 62354792 | chr3 | 62354900 | 62354914 |
| chr3 | 62355424 | 62355478 | chr3 | 62355774 | 62356219 | chr3 | 62356367 | 62356644 |
| chr3 | 62356793 | 62357192 | chr3 | 62357279 | 62357347 | chr3 | 62357624 | 62357667 |
| chr3 | 62358530 | 62358595 | chr3 | 62358858 | 62359011 | chr3 | 62359376 | 62359893 |
| chr3 | 62360302 | 62360560 | chr3 | 62362902 | 62362916 | chr3 | 62363099 | 62363200 |
| chr3 | 62363626 | 62363693 | chr3 | 62363906 | 62364176 | chr3 | 62364280 | 62364329 |
| chr3 | 62364702 | 62365154 | chr3 | 62861118 | 62861148 | chr3 | 63264139 | 63264169 |
| chr3 | 66053446 | 66053475 | chr3 | 68056904 | 68057145 | chr3 | 68980931 | 68981113 |
| chr3 | 68981552 | 68981624 | chr3 | 69590939 | 69590969 | chr3 | 69591363 | 69591414 |
| chr3 | 69591780 | 69591977 | chr3 | 69740967 | 69740990 | chr3 | 69937703 | 69937848 |
| chr3 | 71802518 | 71802622 | chr3 | 71803126 | 71803372 | chr3 | 71803643 | 71803783 |
| chr3 | 73045492 | 73045583 | chr3 | 75956027 | 75956375 | chr3 | 79815522 | 79815557 |
| chr3 | 79816778 | 79817015 | chr3 | 79817288 | 79817318 | chr3 | 85008553 | 85008708 |
| chr3 | 88248025 | 88248049 | chr3 | 96532817 | 96532873 | chr3 | 96533383 | 96533458 |
| chr3 | 96534035 | 96534096 | chr3 | 98620891 | 98620980 | chr3 | 99594925 | 99595105 |
| chr3 | 101230678 | 101230694 | chr3 | 101230934 | 101231070 | chr3 | 101397240 | 101397329 |
| chr3 | 101497841 | 101497996 | chr3 | 106936157 | 106936336 | chr3 | 112052252 | 112052419 |
| chr3 | 115512319 | 115512354 | chr3 | 117715549 | 117715651 | chr3 | 117715771 | 117716123 |
| chr3 | 117716214 | 117716473 | chr3 | 120004080 | 120004405 | chr3 | 120004468 | 120004497 |
| chr3 | 120169104 | 120169149 | chr3 | 120169768 | 120169835 | chr3 | 120627317 | 120627453 |
| chr3 | 121902991 | 121903218 | chr3 | 121903324 | 121903619 | chr3 | 122234242 | 122234270 |

TABLE 13-continued

| chr | start | end | chr | start | end | chr | start | end |
|---|---|---|---|---|---|---|---|---|
| chr3 | 122702288 | 122702430 | chr3 | 123167301 | 123167529 | chr3 | 123167769 | 123167827 |
| chr3 | 125898597 | 125899207 | chr3 | 125899525 | 125899962 | chr3 | 125932252 | 125932500 |
| chr3 | 126157586 | 126157663 | chr3 | 126261929 | 126262000 | chr3 | 126373520 | 126373704 |
| chr3 | 126854699 | 126854796 | chr3 | 127534814 | 127534897 | chr3 | 127634186 | 127634216 |
| chr3 | 127794546 | 127794860 | chr3 | 127795325 | 127795408 | chr3 | 128056383 | 128056497 |
| chr3 | 128202447 | 128202477 | chr3 | 128208903 | 128209232 | chr3 | 128273993 | 128274051 |
| chr3 | 128274309 | 128274611 | chr3 | 128417201 | 128417231 | chr3 | 128720061 | 128720142 |
| chr3 | 128720164 | 128720346 | chr3 | 128720419 | 128720533 | chr3 | 128720567 | 128720611 |
| chr3 | 128720869 | 128721229 | chr3 | 128764489 | 128764606 | chr3 | 129693108 | 129693199 |
| chr3 | 129693305 | 129693498 | chr3 | 129693955 | 129694299 | chr3 | 130064451 | 130064484 |
| chr3 | 130064818 | 130064848 | chr3 | 130236049 | 130236063 | chr3 | 130236174 | 130236273 |
| chr3 | 130519901 | 130519929 | chr3 | 131754031 | 131754061 | chr3 | 132757065 | 132757104 |
| chr3 | 133217922 | 133217999 | chr3 | 133748140 | 133748245 | chr3 | 133748481 | 133748576 |
| chr3 | 134369646 | 134369855 | chr3 | 134514866 | 134514895 | chr3 | 134515128 | 134515369 |
| chr3 | 134515676 | 134516222 | chr3 | 136016868 | 136016942 | chr3 | 136537642 | 136537730 |
| chr3 | 136538585 | 136538815 | chr3 | 136582917 | 136582951 | chr3 | 136751641 | 136751809 |
| chr3 | 137479233 | 137479302 | chr3 | 137479601 | 137479687 | chr3 | 137479980 | 137480764 |
| chr3 | 137481170 | 137481315 | chr3 | 137481858 | 137481872 | chr3 | 137481936 | 137482183 |
| chr3 | 137483313 | 137483437 | chr3 | 137483514 | 137483589 | chr3 | 137483848 | 137484002 |
| chr3 | 137484405 | 137484531 | chr3 | 137486029 | 137486310 | chr3 | 137486516 | 137486550 |
| chr3 | 137487964 | 137488003 | chr3 | 137488950 | 137489698 | chr3 | 137489876 | 137491040 |
| chr3 | 138067717 | 138067747 | chr3 | 138153963 | 138153993 | chr3 | 138374229 | 138374258 |
| chr3 | 138655934 | 138656138 | chr3 | 138656834 | 138656889 | chr3 | 138657414 | 138657494 |
| chr3 | 138657618 | 138658296 | chr3 | 138658704 | 138658863 | chr3 | 138659081 | 138659099 |
| chr3 | 138662134 | 138662164 | chr3 | 138662282 | 138662296 | chr3 | 138662382 | 138662448 |
| chr3 | 138662799 | 138662842 | chr3 | 138663613 | 138663727 | chr3 | 138664142 | 138664165 |
| chr3 | 138664928 | 138665323 | chr3 | 138665562 | 138665718 | chr3 | 138665778 | 138666294 |
| chr3 | 138668758 | 138669108 | chr3 | 138669141 | 138669387 | chr3 | 139258267 | 139258316 |
| chr3 | 139653491 | 139653693 | chr3 | 140769513 | 140769705 | chr3 | 140769908 | 140770301 |
| chr3 | 140770408 | 140770589 | chr3 | 140770644 | 140770829 | chr3 | 140771305 | 140771335 |
| chr3 | 140771816 | 140771854 | chr3 | 141174349 | 141174606 | chr3 | 141481982 | 141482073 |
| chr3 | 141516389 | 141516719 | chr3 | 141657032 | 141657079 | chr3 | 141836036 | 141836077 |
| chr3 | 142537638 | 142537779 | chr3 | 142682273 | 142682392 | chr3 | 142791151 | 142791173 |
| chr3 | 142837980 | 142838318 | chr3 | 142838621 | 142838646 | chr3 | 142838877 | 142839036 |
| chr3 | 142839563 | 142839688 | chr3 | 142839784 | 142839901 | chr3 | 142839945 | 142840127 |
| chr3 | 142840222 | 142840236 | chr3 | 142896156 | 142896214 | chr3 | 143280343 | 143280373 |
| chr3 | 145878665 | 145878695 | chr3 | 146187946 | 146187978 | chr3 | 147074457 | 147074487 |
| chr3 | 147074974 | 147075006 | chr3 | 147077289 | 147077671 | chr3 | 147078959 | 147079188 |
| chr3 | 147087562 | 147087799 | chr3 | 147088440 | 147088523 | chr3 | 147088939 | 147089099 |
| chr3 | 147098431 | 147098470 | chr3 | 147105898 | 147106010 | chr3 | 147108841 | 147109765 |
| chr3 | 147110229 | 147110683 | chr3 | 147110927 | 147111089 | chr3 | 147125697 | 147125726 |
| chr3 | 147127037 | 147127067 | chr3 | 147127681 | 147127902 | chr3 | 147136931 | 147137000 |
| chr3 | 147137076 | 147137164 | chr3 | 147138768 | 147138856 | chr3 | 147139374 | 147139528 |
| chr3 | 148415427 | 148415644 | chr3 | 148523213 | 148523255 | chr3 | 148803258 | 148803276 |
| chr3 | 149374947 | 149375023 | chr3 | 150802981 | 150802999 | chr3 | 150803026 | 150803080 |
| chr3 | 150804043 | 150804077 | chr3 | 150804967 | 150805030 | chr3 | 152553343 | 152553384 |
| chr3 | 152553658 | 152553725 | chr3 | 152877666 | 152877696 | chr3 | 153838818 | 153838870 |
| chr3 | 153839518 | 153839952 | chr3 | 154146133 | 154146394 | chr3 | 154146654 | 154146908 |
| chr3 | 154797334 | 154797703 | chr3 | 155461030 | 155461053 | chr3 | 155463041 | 155463071 |
| chr3 | 156007772 | 156007801 | chr3 | 156008976 | 156009299 | chr3 | 156009319 | 156009425 |
| chr3 | 157155252 | 157155490 | chr3 | 157155982 | 157156194 | chr3 | 157812196 | 157812257 |
| chr3 | 157812437 | 157812645 | chr3 | 157812912 | 157813070 | chr3 | 157813670 | 157813824 |
| chr3 | 157814311 | 157814340 | chr3 | 157815657 | 157815822 | chr3 | 157820576 | 157820605 |
| chr3 | 157821537 | 157821662 | chr3 | 157821904 | 157822008 | chr3 | 157823073 | 157823119 |
| chr3 | 157823139 | 157823143 | chr3 | 157823464 | 157823493 | chrs | 157824133 | 157824146 |
| chr3 | 157824212 | 157824231 | chr3 | 157824495 | 157824871 | chr3 | 157825176 | 157825408 |
| chr3 | 159756687 | 159756856 | chr3 | 159944486 | 159944546 | chr3 | 164912376 | 164912568 |
| chr3 | 164912907 | 164913872 | chr3 | 164914980 | 164915129 | chr3 | 169376183 | 169376215 |
| chr3 | 169376680 | 169376780 | chr3 | 169378825 | 169379024 | chr3 | 169539898 | 169540679 |
| chr3 | 169541070 | 169541102 | chr3 | 170136627 | 170136751 | chr3 | 170302617 | 170302677 |
| chr3 | 170303087 | 170303129 | chr3 | 170303380 | 170303423 | chr3 | 170303639 | 170303844 |
| chr3 | 171527930 | 171527971 | chr3 | 172165443 | 172165784 | chr3 | 172165867 | 172166512 |
| chr3 | 172166879 | 172166893 | chr3 | 172167000 | 172167044 | chr3 | 172167297 | 172167327 |
| chr3 | 172167660 | 172167917 | chr3 | 172355895 | 172355997 | chr3 | 172425382 | 172425400 |
| chr3 | 172425700 | 172425717 | chr3 | 172469925 | 172469951 | chr3 | 173115237 | 173115550 |
| chr3 | 173302542 | 173302668 | chr3 | 173302992 | 173303225 | chr3 | 176710106 | 176710144 |
| chr3 | 178861413 | 178861447 | chr3 | 178916711 | 178916959 | chr3 | 178921537 | 178921568 |
| chr3 | 178927966 | 178928094 | chr3 | 178936059 | 178936111 | chr3 | 178952004 | 178952105 |
| chr3 | 179168661 | 179169266 | chr3 | 179367897 | 179367920 | chr3 | 179754178 | 179754192 |
| chr3 | 179754239 | 179754759 | chr3 | 179754804 | 179754872 | chr3 | 179755087 | 179755372 |
| chr3 | 180320256 | 180320294 | chr3 | 181413742 | 181414330 | chr3 | 181420065 | 181420116 |
| chr3 | 181420316 | 181420374 | chr3 | 181421411 | 181422282 | chr3 | 181422541 | 181422985 |
| chr3 | 181428388 | 181428772 | chr3 | 181430695 | 181430771 | chr3 | 181437129 | 181437349 |
| chr3 | 181438194 | 181438353 | chr3 | 181440892 | 181441927 | clu3 | 181442145 | 181442410 |
| chr3 | 181443014 | 181443557 | chr3 | 181443760 | 181443861 | chr3 | 181444108 | 181444236 |
| chr3 | 181444434 | 181444524 | chr3 | 181444613 | 181444754 | chr3 | 181444814 | 181444948 |
| chr3 | 181444989 | 181445013 | chr3 | 181445369 | 181445464 | chr3 | 181445800 | 181445861 |
| chr3 | 182816009 | 182816027 | chr3 | 182895956 | 182895990 | chr3 | 182911545 | 182911574 |

TABLE 13-continued

| chr | start | end | chr | start | end | chr | start | end |
|---|---|---|---|---|---|---|---|---|
| chr3 | 183109854 | 183109883 | chr3 | 183145412 | 183145618 | chr3 | 183145931 | 183146025 |
| chr3 | 183146397 | 183146435 | chr3 | 183146648 | 183146677 | chr3 | 183217676 | 183217706 |
| chr3 | 183647996 | 183648026 | chr3 | 183728813 | 183728952 | chr3 | 183965599 | 183965633 |
| chr3 | 184018038 | 184018136 | chr3 | 184031686 | 184031746 | chr3 | 184057526 | 184057557 |
| chr3 | 184099417 | 184099446 | chr3 | 184319470 | 184319612 | chr3 | 184319828 | 184319842 |
| chr3 | 184319874 | 184319891 | chr3 | 185001898 | 185001919 | chr3 | 185271296 | 185271380 |
| chr3 | 185303247 | 185303277 | chr3 | 185363074 | 185363261 | chr3 | 185643324 | 185643405 |
| chr3 | 186078766 | 186078898 | chr3 | 186079204 | 186079331 | chr3 | 186080188 | 186080218 |
| chr3 | 186857152 | 186857607 | chr3 | 186914705 | 186914734 | chr3 | 187387850 | 187387920 |
| chr3 | 187388007 | 187388239 | chr3 | 192125828 | 192125828 | chr3 | 192126146 | 192126710 |
| chr3 | 192126787 | 192126863 | chr3 | 192127354 | 192127372 | chr3 | 192127557 | 192127730 |
| chr3 | 192127937 | 192128074 | chr3 | 192232097 | 192232175 | chr3 | 192232452 | 192232570 |
| chr3 | 192232850 | 192232951 | chr3 | 192233095 | 192233150 | chr3 | 192958725 | 192958968 |
| chr3 | 193312128 | 193312208 | chr3 | 193419702 | 193419732 | chr3 | 193548637 | 193548835 |
| chr3 | 193776089 | 193776119 | chr3 | 194048751 | 194048919 | chr3 | 194120008 | 194120164 |
| chr3 | 194120812 | 194120841 | chr3 | 194120934 | 194120963 | chr3 | 194208468 | 194208562 |
| chr3 | 194407998 | 194408028 | chr3 | 194408375 | 194408768 | chr3 | 194408839 | 194409021 |
| chr3 | 194981816 | 194981895 | chr3 | 195095450 | 195095467 | chr3 | 195095527 | 195095543 |
| chr3 | 195536733 | 195536848 | chr3 | 195538315 | 195538353 | chr3 | 195587032 | 195587118 |
| chr3 | 195601239 | 195601312 | chr3 | 195602363 | 195602576 | chr3 | 195648794 | 195648899 |
| chr3 | 196046702 | 196046736 | chr3 | 196065342 | 196065583 | chr3 | 196069892 | 196070192 |
| chr3 | 196255617 | 196255631 | chr3 | 196344683 | 196344710 | chr3 | 196387295 | 196387415 |
| chr3 | 196387628 | 196387665 | chr3 | 196388383 | 196388581 | chr3 | 196440510 | 196440593 |
| chr3 | 196728418 | 196728448 | chr3 | 196731155 | 196731313 | chr3 | 196755958 | 196755987 |
| chr3 | 197209019 | 197209048 | chr3 | 197236945 | 197237111 | chr3 | 197247047 | 197247110 |
| chr3 | 197278926 | 197278988 | chr3 | 197327011 | 197327042 | chr3 | 197330104 | 197330147 |
| chr3 | 197616707 | 197616861 | chr3 | 197677029 | 197677058 | chr3 | 197685788 | 197685817 |
| chr3 | 197686057 | 197686085 | chr3 | 197686495 | 197686524 | chr3 | 197686941 | 197687223 |
| chr3 | 197687694 | 197687723 | chr4 | 206324 | 206353 | chr4 | 331322 | 331352 |
| chr4 | 512978 | 513008 | chr4 | 513704 | 513734 | chr4 | 568429 | 568652 |
| chr4 | 569048 | 569115 | chr4 | 569275 | 569435 | chr4 | 569461 | 569732 |
| chr4 | 570966 | 571013 | chr4 | 571508 | 571689 | chr4 | 628572 | 628787 |
| chr4 | 651196 | 651261 | chr4 | 657521 | 657552 | chr4 | 678471 | 678501 |
| chr4 | 718052 | 718112 | chr4 | 718321 | 718359 | chr4 | 829611 | 829641 |
| chr4 | 955367 | 955454 | chr4 | 955867 | 955919 | chr4 | 995876 | 995993 |
| chr4 | 996101 | 996174 | chr4 | 1008740 | 1008902 | chr4 | 1016127 | 1016252 |
| chr4 | 1016586 | 1016747 | chr4 | 1025928 | 1026074 | chr4 | 1041763 | 1041926 |
| chr4 | 1093536 | 1093675 | chr4 | 1107494 | 1107585 | chr4 | 1165450 | 1165470 |
| chr4 | 1189021 | 1189051 | chr4 | 1214894 | 1215162 | chr4 | 1215415 | 1215451 |
| chr4 | 1282515 | 1282545 | chr4 | 1331675 | 1331705 | chr4 | 1336755 | 1336902 |
| chr4 | 1338715 | 1338812 | chr4 | 1339099 | 1339130 | chr4 | 1396578 | 1396696 |
| chr4 | 1397396 | 1397495 | chr4 | 1398303 | 1398378 | chr4 | 1399723 | 1399768 |
| chr4 | 1401711 | 1401743 | chr4 | 1512368 | 1512398 | chr4 | 1556419 | 1556609 |
| chr4 | 1576484 | 1576528 | chr4 | 1616682 | 1617247 | chr4 | 1687080 | 1687110 |
| chr4 | 1800153 | 1800191 | chr4 | 1803550 | 1803582 | chr4 | 1806084 | 1806113 |
| chr4 | 1807355 | 1807384 | chr4 | 1962787 | 1962816 | chr4 | 1993771 | 1994180 |
| chr4 | 2042106 | 2042122 | chr4 | 2042169 | 2042258 | chr4 | 2066114 | 2066265 |
| chr4 | 2305672 | 2305827 | chr4 | 2527907 | 2527937 | chr4 | 2540215 | 2540297 |
| chr4 | 2765862 | 2765910 | chr4 | 2926366 | 2926396 | chr4 | 2978968 | 2979145 |
| chr4 | 3036118 | 3036148 | chr4 | 3217107 | 3217154 | chr4 | 3371519 | 3371652 |
| chr4 | 3446991 | 3447021 | chr4 | 3447816 | 3448015 | chr4 | 3768833 | 3768949 |
| chr4 | 3768995 | 3769189 | chr4 | 3769560 | 3769574 | chr4 | 3873694 | 3873769 |
| chr4 | 4228189 | 4228241 | chr4 | 4229689 | 4229781 | chr4 | 4387533 | 4387627 |
| chr4 | 4417568 | 4417603 | chr4 | 4855102 | 4855171 | chr4 | 4855371 | 4855433 |
| chr4 | 4860046 | 4860075 | chr4 | 4862769 | 4863110 | chr4 | 4867698 | 4867886 |
| chr4 | 4868566 | 4868792 | chr4 | 4868829 | 4868999 | chr4 | 4872088 | 4872167 |
| chr4 | 4872777 | 4872850 | chr4 | 4873427 | 4873528 | chr4 | 5021188 | 5021217 |
| chr4 | 5053070 | 5053518 | chr4 | 5053747 | 5054093 | chr4 | 5709906 | 5709984 |
| chr4 | 5712979 | 5713231 | chr4 | 5889948 | 5890045 | chr4 | 5890274 | 5890444 |
| chr4 | 5891966 | 5892081 | chr4 | 5892110 | 5892194 | chr4 | 5892750 | 5892780 |
| chr4 | 5893981 | 5894082 | chr4 | 6200897 | 6201235 | chr4 | 6202103 | 6202276 |
| chr4 | 6247351 | 6247381 | chr4 | 6565004 | 6565042 | chr4 | 6670184 | 6670214 |
| chr4 | 6748346 | 6748557 | chr4 | 6957481 | 6957620 | chr4 | 7647770 | 7647945 |
| chr4 | 7758476 | 7758561 | chr4 | 8582549 | 8582579 | chr4 | 8607813 | 8607932 |
| chr4 | 8608556 | 8608600 | chr4 | 8858827 | 8859047 | chr4 | 8859382 | 8859738 |
| chr4 | 8860398 | 8860553 | chr4 | 8861649 | 8861752 | chr4 | 8861919 | 8862014 |
| chr4 | 8862797 | 8862811 | chr4 | 8863441 | 8863526 | chr4 | 8864499 | 8864598 |
| chr4 | 8864831 | 8865058 | chr4 | 8868822 | 8868845 | chr4 | 8868932 | 8869270 |
| chr4 | 8869601 | 8869813 | chr4 | 8873054 | 8873072 | chr4 | 8873809 | 8873984 |
| chr4 | 8874485 | 8874534 | chr4 | 8874773 | 8874787 | chr4 | 8875877 | 8875907 |
| chr4 | 8893060 | 8893093 | chr4 | 8893501 | 8893531 | chr4 | 8893816 | 8893931 |
| chr4 | 8894641 | 8894957 | chr4 | 8895232 | 8895350 | chr4 | 8895554 | 8895584 |
| chr4 | 8895965 | 8896052 | chr4 | 9423273 | 9423314 | chr4 | 9782992 | 9783095 |
| chr4 | 9783126 | 9783412 | chr4 | 10458395 | 10459121 | chr4 | 10462833 | 10463047 |
| chr4 | 10463073 | 10463604 | chr4 | 11429506 | 11429633 | chr4 | 13524026 | 13524251 |
| chr4 | 13524665 | 13524775 | chr4 | 13524957 | 13524971 | chr4 | 13537569 | 13537688 |
| chr4 | 13540983 | 13541068 | chr4 | 13546026 | 13546078 | chr4 | 13548502 | 13548589 |
| chr4 | 13548635 | 13548895 | chr4 | 13549340 | 13549510 | chr4 | 15780223 | 15780320 |

TABLE 13-continued

| chr | start | end | chr | start | end | chr | start | end |
|---|---|---|---|---|---|---|---|---|
| chr4 | 16084741 | 16084818 | chr4 | 16085167 | 16085301 | chr4 | 16085352 | 16085381 |
| chr4 | 16085675 | 16085682 | chr4 | 17783003 | 17783480 | chr4 | 20254693 | 20254723 |
| chr4 | 20255525 | 20255861 | chr4 | 20256152 | 20256285 | chr4 | 21950248 | 21950295 |
| chr4 | 24801868 | 24801985 | chr4 | 24914638 | 24914668 | chr4 | 25656815 | 25656879 |
| chr4 | 25657437 | 25657477 | chr4 | 27086432 | 27086462 | chr4 | 30722243 | 30722273 |
| chr4 | 30723856 | 30723862 | chr4 | 30724249 | 30724372 | chr4 | 37245837 | 37245851 |
| chr4 | 37246134 | 37246360 | chr4 | 37246490 | 37246699 | chr4 | 37247096 | 37247216 |
| chr4 | 38565373 | 38566418 | chr4 | 38673115 | 38673144 | chr4 | 40632773 | 40632802 |
| chr4 | 40910303 | 40910465 | chr4 | 41258716 | 41258788 | chr4 | 41259086 | 41259176 |
| chr4 | 41747009 | 41747133 | chr4 | 41747493 | 41747582 | chr4 | 41747958 | 41747977 |
| chr4 | 41748144 | 41748296 | chr4 | 41748660 | 41748766 | chr4 | 41749033 | 41749063 |
| chr4 | 41749270 | 41749761 | chr4 | 41750223 | 41750504 | chr4 | 41751870 | 41752006 |
| chr4 | 41752451 | 41752693 | chr4 | 41752968 | 41753398 | chr4 | 41753610 | 41753916 |
| chr4 | 41754031 | 41754021 | chr4 | 41875430 | 41875902 | chr4 | 41880331 | 41880412 |
| chr4 | 41881385 | 41881425 | chr4 | 41883091 | 41883302 | chr4 | 41883510 | 41883610 |
| chr4 | 41993716 | 41993815 | chr4 | 42152962 | 42153411 | chr4 | 42153533 | 42153632 |
| chr4 | 42153882 | 42154025 | chr4 | 42154280 | 42154359 | chr4 | 42154662 | 42154997 |
| chr4 | 42155293 | 42155322 | chr4 | 42348266 | 42348331 | chr4 | 42398842 | 42398872 |
| chr4 | 42399137 | 42399191 | chr4 | 42399688 | 42399872 | chr4 | 44449480 | 44449569 |
| chr4 | 46391353 | 46391383 | chr4 | 46911535 | 46911564 | chr4 | 46995161 | 46995835 |
| chr4 | 47034908 | 47034938 | chr4 | 48485067 | 48485288 | chr4 | 48485590 | 48486000 |
| chr4 | 48486356 | 48486389 | chr4 | 48492181 | 48492433 | chr4 | 48848428 | 48848461 |
| chr4 | 48988109 | 48988335 | chr4 | 53728495 | 53729056 | chr4 | 54966854 | 54967075 |
| chr4 | 54967342 | 54967484 | chr4 | 54969833 | 54970095 | chr4 | 54970369 | 54970482 |
| chr4 | 54975991 | 54976115 | chr4 | 55093048 | 55093255 | chr4 | 55096239 | 55096344 |
| chr4 | 55097404 | 55097634 | chr4 | 55097973 | 55098092 | chr4 | 55098198 | 55098373 |
| chr4 | 55098674 | 55098744 | chr4 | 55099039 | 55099062 | chr4 | 55133613 | 55133642 |
| chr4 | 55136787 | 55136816 | chr4 | 55138657 | 55138686 | chr4 | 55139691 | 55139720 |
| chr4 | 55140731 | 55140784 | chr4 | 55141015 | 55141050 | chr4 | 55144105 | 55144134 |
| chr4 | 55146554 | 55146583 | chr4 | 55152075 | 55152140 | chr4 | 55524220 | 55524274 |
| chr4 | 55589753 | 55589782 | chr4 | 55592166 | 55592204 | chr4 | 55593417 | 55593675 |
| chr4 | 55594183 | 55594212 | chr4 | 55595504 | 55595614 | chr4 | 55599306 | 55599356 |
| chr4 | 55968165 | 55968194 | chr4 | 55991107 | 55991228 | chr4 | 55992153 | 55992169 |
| chr4 | 56659692 | 56659866 | chr4 | 56659935 | 56660021 | chr4 | 57017423 | 57017459 |
| chr4 | 57371718 | 57371963 | chr4 | 57372336 | 57372504 | chr4 | 57396946 | 57397264 |
| chr4 | 57521506 | 57521663 | chr4 | 57521701 | 57522382 | chr4 | 57522420 | 57522815 |
| chr4 | 57687720 | 57687782 | chr4 | 57777437 | 57777595 | chr4 | 57803528 | 57803558 |
| chr4 | 57976033 | 57976185 | chr4 | 57976416 | 57976573 | chr4 | 58030191 | 58030524 |
| chr4 | 62066196 | 62066553 | chr4 | 62067511 | 62067624 | chr4 | 62068072 | 62068150 |
| chr4 | 66535130 | 66535314 | chr4 | 66535351 | 66535443 | chr4 | 66536171 | 66536323 |
| chr4 | 74702479 | 74702516 | chr4 | 74735076 | 74735137 | chr4 | 74809877 | 74809933 |
| chr4 | 75241348 | 75241435 | chr4 | 75858573 | 75858629 | chr4 | 76555532 | 76555856 |
| chr4 | 76912716 | 76912733 | chr4 | 79611273 | 79611294 | chr4 | 79689651 | 79689732 |
| chr4 | 81106351 | 81106871 | chr4 | 81124277 | 81124662 | chr4 | 81187046 | 81187076 |
| chr4 | 81187559 | 81187589 | chr4 | 81188385 | 81188489 | chr4 | 81188491 | 81188556 |
| chr4 | 81189419 | 81189660 | chr4 | 81189714 | 81189911 | chr4 | 81951431 | 81951460 |
| chr4 | 81951941 | 81951970 | chr4 | 81952170 | 81952311 | chr4 | 82135873 | 82135887 |
| chr4 | 82135920 | 82136056 | chr4 | 82136495 | 82136548 | chr4 | 82136807 | 82136837 |
| chr4 | 83323506 | 83323708 | chr4 | 83720611 | 83720643 | chr4 | 84035907 | 84035936 |
| chr4 | 85402377 | 85402511 | chr4 | 85402776 | 85403423 | chr4 | 85403913 | 85403927 |
| chr4 | 85404112 | 85404140 | chr4 | 85404225 | 85404475 | chr4 | 85404650 | 85404693 |
| chr4 | 85414045 | 85414113 | chr4 | 85414725 | 85414846 | chr4 | 85417336 | 85417564 |
| chr4 | 85417953 | 85418079 | chr4 | 85418522 | 85418582 | chr4 | 85420591 | 85420621 |
| chr4 | 85422188 | 85422432 | chr4 | 85422973 | 85423316 | chr4 | 85424401 | 85424483 |
| chr4 | 87515337 | 87515367 | chr4 | 89378464 | 89378497 | chr4 | 89378744 | 89378766 |
| chr4 | 89378832 | 89378888 | chr4 | 90757517 | 90757828 | chr4 | 90758105 | 90758134 |
| chr4 | 90758776 | 90758883 | chr4 | 93224972 | 93225171 | chr4 | 93226365 | 93226703 |
| chr4 | 93226729 | 93227129 | chr4 | 94749725 | 94749755 | chr4 | 94750982 | 94751140 |
| chr4 | 94751419 | 94751502 | chr4 | 94753415 | 94753445 | chr4 | 94756002 | 94756109 |
| chr4 | 95127590 | 95127684 | chr4 | 96470752 | 96470782 | chr4 | 101111246 | 101111504 |
| chr4 | 101111857 | 101111970 | chr4 | 102711731 | 102711787 | chr4 | 106335395 | 106335526 |
| chr4 | 107955311 | 107955826 | chr4 | 107966676 | 107957086 | chr4 | 107957373 | 107957466 |
| chr4 | 109093101 | 109093168 | chr4 | 109093405 | 109093506 | chr4 | 110223090 | 110223427 |
| chr4 | 110223579 | 110223980 | chr4 | 110344278 | 110344294 | chr4 | 111532705 | 111532961 |
| chr4 | 111536288 | 111536505 | chr4 | 111536562 | 111536693 | chr4 | 111536960 | 111536974 |
| chr4 | 111537407 | 111537497 | chr4 | 111540199 | 111540360 | chr4 | 111542474 | 111542757 |
| chr4 | 111543232 | 111543345 | chr4 | 111543404 | 111543450 | chr4 | 111543661 | 111543695 |
| chr4 | 111543721 | 111543735 | chr4 | 111544381 | 111544583 | chr4 | 111549800 | 111549830 |
| chr4 | 111550618 | 111550834 | chr4 | 111552118 | 111552148 | chr4 | 111553099 | 111553450 |
| chr4 | 111553916 | 111553951 | chr4 | 111554950 | 111554964 | chr4 | 111555194 | 111555343 |
| chr4 | 111557965 | 111558049 | chr4 | 111558551 | 111559233 | chr4 | 111560249 | 111560636 |
| chr4 | 111562576 | 111562648 | chr4 | 113154896 | 113155043 | chr4 | 113430640 | 113430672 |
| chr4 | 113431834 | 113431854 | chr4 | 113431916 | 113432154 | chr4 | 113432227 | 113432503 |
| chr4 | 113432519 | 113432573 | chr4 | 113436216 | 113436287 | chr4 | 113441592 | 113441733 |
| chr4 | 113442098 | 113442185 | chr4 | 113442247 | 113442525 | chr4 | 113444020 | 113444448 |
| chr4 | 117847399 | 117847458 | chr4 | 121844063 | 121844206 | chr4 | 121992265 | 121992312 |
| chr4 | 121993997 | 121994251 | chr4 | 122301422 | 122301712 | chr4 | 122302116 | 122302246 |
| chr4 | 122685807 | 122685890 | chr4 | 122686209 | 122686507 | chr4 | 122871294 | 122871334 |

TABLE 13-continued

| chr | start | end | chr | start | end | chr | start | end |
|---|---|---|---|---|---|---|---|---|
| chr4 | 122871573 | 122872000 | chr4 | 123664228 | 123664363 | chr4 | 126237310 | 126237611 |
| chr4 | 126238024 | 126238436 | chr4 | 128544048 | 128544161 | chr4 | 128544646 | 128544789 |
| chr4 | 128967290 | 128967329 | chr4 | 134067881 | 134068004 | chr4 | 134068577 | 134068791 |
| chr4 | 134069289 | 134069318 | chr4 | 134069578 | 134069896 | chr4 | 134070374 | 134070403 |
| chr4 | 134071648 | 134072610 | chr4 | 134072677 | 134072967 | chr4 | 134073184 | 134073322 |
| chr4 | 134073568 | 134073641 | chr4 | 134073862 | 134073919 | chr4 | 134074030 | 134074156 |
| chr4 | 140200529 | 140201156 | chr4 | 140201193 | 140201462 | chr4 | 140656643 | 140656666 |
| chr4 | 140656858 | 140657089 | chr4 | 141347942 | 141348151 | chr4 | 141418921 | 141419418 |
| chr4 | 141488870 | 141489128 | chr4 | 142053130 | 142053160 | chr4 | 142053520 | 142053734 |
| chr4 | 142054239 | 142054460 | chr4 | 143766796 | 143766930 | chr4 | 144621336 | 144621439 |
| chr4 | 144621515 | 144621896 | chr4 | 144621982 | 144622058 | chr4 | 145568052 | 145568147 |
| chr4 | 145568459 | 145568741 | chr4 | 146853951 | 146853981 | chr4 | 147558272 | 147558381 |
| chr4 | 147558477 | 147558504 | chr4 | 147559321 | 147560078 | chr4 | 147560134 | 147560418 |
| chr4 | 147560460 | 147560617 | chr4 | 147560933 | 147561145 | chr4 | 147561360 | 147561949 |
| chr4 | 147562000 | 147562055 | chr4 | 147568636 | 147569060 | chr4 | 147569620 | 147569650 |
| chr4 | 147576177 | 147576201 | chr4 | 147576330 | 147576639 | chr4 | 151974287 | 151974489 |
| chr4 | 152148807 | 152148836 | chr4 | 152246132 | 152246314 | chr4 | 153247273 | 153247386 |
| chr4 | 153249362 | 153249398 | chr4 | 153251894 | 153251923 | chr4 | 153702685 | 153702702 |
| chr4 | 154216241 | 154216357 | chr4 | 154709524 | 154709610 | chr4 | 154709759 | 154710617 |
| chr4 | 154710729 | 154710914 | chr4 | 154712172 | 154712594 | chr4 | 154713500 | 154713530 |
| chr4 | 154713949 | 154714010 | chr4 | 155254166 | 155254196 | chr4 | 155411851 | 155412279 |
| chr4 | 155663209 | 155663647 | chr4 | 155665445 | 155665475 | chr4 | 156129153 | 156129183 |
| chr4 | 156129451 | 156129495 | chr4 | 156129746 | 156129797 | chr4 | 156130047 | 156130297 |
| chr4 | 156297416 | 156297556 | chr4 | 156297942 | 156298073 | chr4 | 156588311 | 156588401 |
| chr4 | 156589273 | 156589323 | chr4 | 156680257 | 156680532 | chr4 | 156681370 | 156681489 |
| chr4 | 158141576 | 158141606 | chr4 | 158142847 | 158142999 | chr4 | 158143443 | 158143465 |
| chr4 | 164252991 | 164253447 | chr4 | 165304515 | 165304578 | chr4 | 165305060 | 165305163 |
| chr4 | 166414834 | 166414921 | chr4 | 166794771 | 166794909 | chr4 | 166796118 | 166796212 |
| chr4 | 168155109 | 168155269 | chr4 | 170865261 | 170865287 | chr4 | 170947287 | 170947325 |
| chr4 | 172734189 | 172734203 | chr4 | 172734592 | 172734790 | chr4 | 174083164 | 174083208 |
| chr4 | 174136704 | 174136734 | chr4 | 174429658 | 174429688 | chr4 | 174430310 | 174430553 |
| chr4 | 174430794 | 174431072 | chr4 | 174438567 | 174438744 | chr4 | 174439822 | 174440257 |
| chr4 | 174440635 | 174440713 | chr4 | 174443212 | 174443242 | chr4 | 174443563 | 174443934 |
| chr4 | 174446508 | 174446525 | chr4 | 174446952 | 174447005 | chr4 | 174449950 | 174450726 |
| chr4 | 174450752 | 174451482 | chr4 | 174451855 | 174452098 | chr4 | 174459185 | 174459374 |
| chr4 | 174459528 | 174459840 | chr4 | 174460186 | 174460221 | chr4 | 175132735 | 175132765 |
| chr4 | 175133085 | 175133201 | chr4 | 175134897 | 175135672 | chr4 | 175135921 | 175136011 |
| chr4 | 175138411 | 175138546 | chr4 | 175138964 | 175139254 | chr4 | 175139559 | 175139685 |
| chr4 | 175750456 | 175750738 | chr4 | 176923424 | 176923558 | chr4 | 176987324 | 176987373 |
| chr4 | 177713228 | 177713437 | chr4 | 178285756 | 178285788 | chr4 | 180979270 | 180979300 |
| chr4 | 180980297 | 180980356 | chr4 | 183063666 | 183063950 | chr4 | 183064617 | 183064655 |
| chr4 | 183064874 | 183064966 | chr4 | 184019249 | 184019316 | chr4 | 184019692 | 184019736 |
| chr4 | 184020106 | 184020179 | chr4 | 184375696 | 184375726 | chr4 | 184644053 | 184644249 |
| chr4 | 184718260 | 184718352 | chr4 | 184826238 | 184826493 | chr4 | 184826938 | 184827237 |
| chr4 | 184921855 | 184922091 | chr4 | 185089696 | 185089797 | chr4 | 185937333 | 185937889 |
| chr4 | 185938497 | 185938564 | chr4 | 185940338 | 185940460 | chr4 | 185941585 | 185942472 |
| chr4 | 185942492 | 185942760 | chr4 | 187647073 | 187647457 | chr5 | 53849 | 53898 |
| chr5 | 92163 | 92399 | chr5 | 303272 | 303301 | chr5 | 320840 | 320982 |
| chr5 | 343916 | 343941 | chr5 | 373363 | 373392 | chr5 | 373872 | 374266 |
| chr5 | 400186 | 400215 | chr5 | 400502 | 400531 | chr5 | 415870 | 415899 |
| chr5 | 481012 | 481037 | chr5 | 491335 | 491536 | chr5 | 524337 | 524404 |
| chr5 | 538758 | 538806 | chr5 | 554299 | 554538 | chr5 | 554871 | 554900 |
| chr5 | 555192 | 555285 | chr5 | 555965 | 555995 | chr5 | 677889 | 678006 |
| chr5 | 909204 | 909304 | chr5 | 912806 | 912835 | chr5 | 1034600 | 1034653 |
| chr5 | 1059523 | 1059556 | chr5 | 1093660 | 1093797 | chr5 | 1131217 | 1131378 |
| chr5 | 1193381 | 1193521 | chr5 | 1193880 | 1193944 | chr5 | 1221197 | 1221307 |
| chr5 | 1271339 | 1271396 | chr5 | 1294630 | 1294767 | chr5 | 1295031 | 1295442 |
| chr5 | 1295605 | 1295662 | chr5 | 1445171 | 1445255 | chr5 | 1445738 | 1445759 |
| chr5 | 1445841 | 1445928 | chr5 | 1446319 | 1446369 | chr5 | 1446443 | 1446599 |
| chr5 | 1747022 | 1747098 | chr5 | 1779526 | 1779556 | chr5 | 1787378 | 1787418 |
| chr5 | 1874892 | 1875099 | chr5 | 1875453 | 1875497 | chr5 | 1875870 | 1876306 |
| chr5 | 1876638 | 1876860 | chr5 | 1877195 | 1877239 | chr5 | 1878014 | 1878028 |
| chr5 | 1878224 | 1878528 | chr5 | 1878831 | 1879045 | chr5 | 1879605 | 1879661 |
| chr5 | 1879690 | 1879719 | chr5 | 1882420 | 1882605 | chr5 | 1882844 | 1882921 |
| chr5 | 1883515 | 1883616 | chr5 | 1884178 | 1884237 | chr5 | 1884557 | 1884698 |
| chr5 | 1885158 | 1885458 | chr5 | 1885985 | 1886076 | chr5 | 1886542 | 1886581 |
| chr5 | 1886812 | 1886841 | chr5 | 1886998 | 1887145 | chr5 | 1887547 | 1887581 |
| chr5 | 1887656 | 1887737 | chr5 | 1930786 | 1931004 | chr5 | 1931065 | 1931286 |
| chr5 | 1931445 | 1931576 | chr5 | 1931618 | 1931754 | chr5 | 1950794 | 1950960 |
| chr5 | 1952624 | 1952638 | chr5 | 2038705 | 2038850 | chr5 | 2225439 | 2225469 |
| chr5 | 2324383 | 2324413 | chr5 | 2541487 | 2541611 | chr5 | 2738848 | 2739129 |
| chr5 | 2739211 | 2739354 | chr5 | 2739877 | 2740300 | chr5 | 2740431 | 2740664 |
| chr5 | 2743617 | 2743659 | chr5 | 2743699 | 2743713 | chr5 | 2748374 | 2748459 |
| chr5 | 2749213 | 2749406 | chr5 | 2749699 | 2749729 | chr5 | 2750435 | 2750516 |
| chr5 | 2750655 | 2750769 | chr5 | 2751855 | 2751894 | chr5 | 2752991 | 2753040 |
| chr5 | 2753048 | 2753078 | chr5 | 2754738 | 2754767 | chr5 | 2755323 | 2756388 |
| chr5 | 2756599 | 2756602 | chr5 | 2756674 | 2757427 | chr5 | 3031879 | 3032018 |
| chr5 | 3152146 | 3152176 | chr5 | 3325042 | 3325272 | chr5 | 3590405 | 3590657 |

TABLE 13-continued

| chr | start | end | chr | start | end | chr | start | end |
|---|---|---|---|---|---|---|---|---|
| chr5 | 3591354 | 3591388 | chr5 | 3591857 | 3592037 | chr5 | 3592728 | 3592881 |
| chr5 | 3594250 | 3594519 | chr5 | 3595090 | 3595178 | chr5 | 3595850 | 3595991 |
| chr5 | 3596556 | 3596724 | chr5 | 3596825 | 3596880 | chr5 | 3597411 | 3597461 |
| chr5 | 3600150 | 3600180 | chr5 | 3602804 | 3603320 | chr5 | 3674053 | 3674224 |
| chr5 | 4144367 | 4144516 | chr5 | 5139754 | 5139900 | chr5 | 5140170 | 5140225 |
| chr5 | 5140630 | 5140757 | chr5 | 5140850 | 5140901 | chr5 | 6228617 | 6228790 |
| chr5 | 6448930 | 6449582 | chr5 | 6482458 | 6482620 | chr5 | 6583461 | 6583579 |
| chr5 | 6687277 | 6687431 | chr5 | 6755789 | 6755843 | chr5 | 7395263 | 7395393 |
| chr5 | 7395434 | 7395538 | chr5 | 7851015 | 7851121 | chr5 | 9546612 | 9546648 |
| chr5 | 10249098 | 10249127 | chr5 | 10333688 | 10334132 | chr5 | 10565021 | 10565227 |
| chr5 | 10565263 | 10565607 | chr5 | 11384965 | 11385363 | chr5 | 11903822 | 11904173 |
| chr5 | 11904196 | 11904379 | chr5 | 11904456 | 11904696 | chr5 | 11904896 | 11904943 |
| chr5 | 14872919 | 14873053 | chr5 | 15500748 | 15500927 | chr5 | 16179049 | 16179141 |
| chr5 | 16179555 | 16179713 | chr5 | 16180183 | 16180260 | chr5 | 16466784 | 16466802 |
| chr5 | 16467042 | 16467120 | chr5 | 16845452 | 16845476 | chr5 | 16845536 | 16845619 |
| chr5 | 16936354 | 16936514 | chr5 | 17203035 | 17203177 | chr5 | 17218195 | 17218225 |
| chr5 | 17218986 | 17219018 | chr5 | 17512114 | 17612144 | chr5 | 22853443 | 22853508 |
| chr5 | 31193937 | 31193989 | chr5 | 31194375 | 31194641 | chr5 | 31639684 | 31639960 |
| chr5 | 31691565 | 31691652 | chr5 | 31855073 | 31855199 | chr5 | 32710331 | 32710470 |
| chr5 | 32710802 | 32710957 | chr5 | 32711017 | 32711531 | chr5 | 32711826 | 32711870 |
| chr5 | 32712077 | 32712101 | chr5 | 32712290 | 32712491 | chr5 | 32712764 | 32713304 |
| chr5 | 33298005 | 33298076 | chr5 | 33892083 | 33892115 | chr5 | 33892413 | 33892443 |
| chr5 | 33936156 | 33936336 | chr5 | 33936486 | 33936516 | chr5 | 33936599 | 33936663 |
| chr5 | 34656932 | 34657034 | chr5 | 35874560 | 35874589 | chr5 | 35939832 | 35939861 |
| chr5 | 37834684 | 37834714 | chr5 | 37835015 | 37835125 | chr5 | 37836231 | 37836260 |
| chr5 | 37836649 | 37837992 | chr5 | 37838548 | 37838885 | chr5 | 37839808 | 37840125 |
| chr5 | 37840530 | 37840853 | chr5 | 38257485 | 38257606 | chr5 | 38257842 | 38257908 |
| chr5 | 38257945 | 38257959 | chr5 | 38557070 | 38557400 | chr5 | 38845675 | 38846164 |
| chr5 | 39343181 | 39343205 | chr5 | 40681122 | 40681227 | chr5 | 40681262 | 40681367 |
| chr5 | 40681676 | 40681839 | chr5 | 40775147 | 40775313 | chr5 | 42424822 | 42425060 |
| chr5 | 42950980 | 42951311 | chr5 | 42951420 | 42952111 | chr5 | 42991825 | 42992241 |
| chr5 | 42992376 | 42992597 | chr5 | 42992783 | 42992934 | chr5 | 42993312 | 42993552 |
| chr5 | 42993852 | 42994193 | chr5 | 42994694 | 42994790 | chr5 | 42995115 | 42995153 |
| chr5 | 43007936 | 43007966 | chr5 | 43008202 | 43008472 | chr5 | 43017953 | 43018176 |
| chr5 | 43018327 | 43018690 | chr5 | 43019238 | 43019347 | chr5 | 43019809 | 43019887 |
| chr5 | 43020146 | 43020294 | chr5 | 43040544 | 43040635 | chr5 | 43040870 | 43040964 |
| chr5 | 43215538 | 43215578 | chr5 | 43397002 | 43397229 | chr5 | 44389782 | 44389852 |
| chr5 | 45695186 | 45695239 | chr5 | 45695314 | 45695533 | chr5 | 45695906 | 45695947 |
| chr5 | 45696336 | 45696439 | chr5 | 49736592 | 49736685 | chr5 | 50262893 | 50263014 |
| chr5 | 50263568 | 50263641 | chr5 | 50264307 | 50264603 | chr5 | 50264820 | 50264850 |
| chr5 | 50265325 | 50265429 | chr5 | 50265721 | 50265880 | chr5 | 50674152 | 50674188 |
| chr5 | 50674560 | 50674590 | chr5 | 50675013 | 50675075 | chr5 | 50678346 | 50678490 |
| chr5 | 50695351 | 50695463 | chr5 | 52084073 | 52084134 | chr5 | 54179610 | 54179633 |
| chr5 | 54180063 | 54180093 | chr5 | 54516371 | 54516680 | chr5 | 54516832 | 54517017 |
| chr5 | 54518651 | 54519288 | chr5 | 54527323 | 54527343 | chr5 | 56246546 | 56246575 |
| chr5 | 56247942 | 56247971 | chr5 | 56248218 | 56248257 | chr5 | 57878271 | 57878375 |
| chr5 | 57878710 | 57878752 | chr5 | 59188291 | 59188327 | chr5 | 59189055 | 59189057 |
| chr5 | 59189189 | 59189206 | chr5 | 59189863 | 59189948 | chr5 | 63254903 | 63255242 |
| chr5 | 63256863 | 63256895 | chr5 | 63257727 | 63257861 | chr5 | 63802007 | 63802304 |
| chr5 | 63802340 | 63802514 | chr5 | 63986488 | 63986527 | chr5 | 63986570 | 63986807 |
| chr5 | 67569803 | 67569832 | chr5 | 67588937 | 67589162 | chr5 | 67589598 | 67589627 |
| chr5 | 67590431 | 67590460 | chr5 | 67591068 | 67591157 | chr5 | 68391309 | 68391336 |
| chr5 | 71014720 | 71014895 | chr5 | 71015180 | 71015728 | chr5 | 71106820 | 71106984 |
| chr5 | 71403566 | 71403653 | chr5 | 71403975 | 71404207 | chr5 | 72416246 | 72416751 |
| chr5 | 72526413 | 72526414 | chr5 | 72526492 | 72526643 | chr5 | 72528434 | 72528464 |
| chr5 | 72529289 | 72529825 | chr5 | 72529890 | 72530609 | chr5 | 72594802 | 72594836 |
| chr5 | 72594868 | 72595016 | chr5 | 72595047 | 72595059 | chr5 | 72595542 | 72595721 |
| chr5 | 72595774 | 72595788 | chr5 | 72599079 | 72599441 | chr5 | 72599463 | 72599833 |
| chr5 | 72677775 | 72677825 | chr5 | 72677998 | 72678028 | chr5 | 72715204 | 72715347 |
| chr5 | 72715591 | 72715695 | chr5 | 72715731 | 72715768 | chr5 | 72716102 | 72716180 |
| chr5 | 72732870 | 72732884 | chr5 | 72733093 | 72733185 | chr5 | 72740147 | 72740184 |
| chr5 | 72746680 | 72746683 | chr5 | 75377883 | 75378033 | chr5 | 75380163 | 75380193 |
| chr5 | 75380624 | 75380974 | chr5 | 76011285 | 76011337 | chr5 | 76012576 | 76012605 |
| chr5 | 76249270 | 76249670 | chr5 | 76249696 | 76249906 | chr5 | 76249945 | 76250150 |
| chr5 | 76250435 | 76250504 | chr5 | 76506469 | 76506506 | chr5 | 76507035 | 76507114 |
| chr5 | 76923679 | 76924023 | chr5 | 76924087 | 76924299 | chr5 | 76924930 | 76924960 |
| chr5 | 76925561 | 76925690 | chr5 | 76928157 | 76928397 | chr5 | 76928688 | 76928906 |
| chr5 | 76932302 | 76932332 | chr5 | 76932542 | 76933265 | chr5 | 76934173 | 76934653 |
| chr5 | 76934677 | 76934870 | chr5 | 76936016 | 76936039 | chr5 | 76936099 | 76936721 |
| chr5 | 76939436 | 76939774 | chr5 | 76940340 | 76940374 | chr5 | 76941201 | 76941326 |
| chr5 | 77140527 | 77140711 | chr5 | 77147563 | 77147649 | chr5 | 77147873 | 77148195 |
| chr5 | 77148498 | 77148695 | chr5 | 77268367 | 77269237 | chr5 | 77269264 | 77269309 |
| chr5 | 78407651 | 78407840 | chr5 | 78408192 | 78408274 | chr5 | 78408298 | 78408461 |
| chr5 | 78910231 | 78910332 | chr5 | 79598681 | 79598759 | chr5 | 79783240 | 79783271 |
| chr5 | 79864898 | 79865078 | chr5 | 79866100 | 79866414 | chr5 | 79947584 | 79947707 |
| chr5 | 80255816 | 80256074 | chr5 | 80689543 | 80689735 | chr5 | 80690118 | 80690239 |
| chr5 | 82767429 | 82767793 | chr5 | 82768892 | 82769061 | chr5 | 83679195 | 83679225 |
| chr5 | 83679681 | 83680340 | chr5 | 83680615 | 83680664 | chr5 | 83680694 | 83680708 |

TABLE 13-continued

| chr | start | end | chr | start | end | chr | start | end |
|---|---|---|---|---|---|---|---|---|
| chr5 | 87955460 | 87955664 | chr5 | 87956199 | 87956662 | chr5 | 87956680 | 87956964 |
| chr5 | 87962966 | 87963002 | chr5 | 87963390 | 87963511 | chr5 | 87967773 | 87968077 |
| chr5 | 87968486 | 87968685 | chr5 | 87968773 | 87968858 | chr5 | 87970193 | 87970872 |
| chr5 | 87974104 | 87974307 | chr5 | 87974868 | 87975023 | chr5 | 87976028 | 87976308 |
| chr5 | 87976525 | 87976559 | chr5 | 87979756 | 87979834 | chr5 | 87979894 | 87979912 |
| chr5 | 87980142 | 87980250 | chr5 | 87980954 | 87981325 | chr5 | 87984532 | 87984657 |
| chr5 | 87985922 | 87985954 | chr5 | 87986210 | 87986281 | chr5 | 87986547 | 87986581 |
| chr5 | 87988516 | 87988584 | chr5 | 87990408 | 87990452 | chr5 | 88185470 | 88186001 |
| chr5 | 89854856 | 89854902 | chr5 | 94955681 | 94955919 | chr5 | 94956935 | 94957000 |
| chr5 | 94982134 | 94982225 | chr5 | 95767894 | 95768384 | chr5 | 95768920 | 95769093 |
| chr5 | 96114587 | 96114632 | chr5 | 100236682 | 100236757 | chr5 | 100238882 | 100239119 |
| chr5 | 100239135 | 100239151 | chr5 | 101631487 | 101631533 | chr5 | 101632295 | 101632573 |
| chr5 | 107005983 | 107006186 | chr5 | 111987781 | 111987818 | chr5 | 112042844 | 112042873 |
| chr5 | 112042904 | 112043289 | chr5 | 112073358 | 112073516 | chr5 | 112170808 | 112170837 |
| chr5 | 112175198 | 112175227 | chr5 | 112175640 | 112175669 | chr5 | 112258359 | 112258388 |
| chr5 | 112258634 | 112258663 | chr5 | 112629427 | 112629674 | chr5 | 113391265 | 113392018 |
| chr5 | 113698567 | 113698583 | chr5 | 113698670 | 113698783 | chr5 | 113699008 | 113699119 |
| chr5 | 114515010 | 114515579 | chr5 | 114515611 | 114515671 | chr5 | 115151267 | 115151357 |
| chr5 | 115151650 | 115152384 | chr5 | 115152617 | 115152638 | chr5 | 115297192 | 115297292 |
| chr5 | 115297377 | 115297556 | chr5 | 115297928 | 115297985 | chr5 | 115298496 | 115298581 |
| chr5 | 115298985 | 115299041 | chr5 | 119799931 | 119799986 | chr5 | 119801299 | 119801445 |
| chr5 | 121413537 | 121413590 | chr5 | 122422240 | 122422292 | chr5 | 122422616 | 122422651 |
| chr5 | 122423328 | 122423376 | chr5 | 122425128 | 122425168 | chr5 | 122431118 | 122431378 |
| chr5 | 124128454 | 124128497 | chr5 | 126626283 | 126626738 | chr5 | 127872942 | 127872990 |
| chr5 | 127873553 | 127873710 | chr5 | 127874448 | 127874477 | chr5 | 127874706 | 127874839 |
| chr5 | 128300680 | 128300694 | chr5 | 128300713 | 128300794 | chr5 | 128796081 | 128796244 |
| chr5 | 128796867 | 128796985 | chr5 | 128797344 | 128797386 | chr5 | 129240068 | 129240101 |
| chr5 | 131992096 | 131992157 | chr5 | 132947486 | 132947836 | chr5 | 133820024 | 133820040 |
| chr5 | 134364195 | 134364234 | chr5 | 134366718 | 134366788 | chr5 | 134367108 | 134367203 |
| chr5 | 134374447 | 134374505 | chr5 | 134374792 | 134375210 | chr5 | 134376222 | 134376375 |
| chr5 | 134376732 | 134376824 | chr5 | 134385952 | 134386167 | chr5 | 134386185 | 134386383 |
| chr5 | 134582864 | 134582894 | chr5 | 134735622 | 134735651 | chr5 | 134825463 | 134825518 |
| chr5 | 134825913 | 134826006 | chr5 | 134870446 | 134870515 | chr5 | 134870780 | 134870926 |
| chr5 | 134871601 | 134872049 | chr5 | 134879478 | 134879990 | chr5 | 134880110 | 134880501 |
| chr5 | 134914627 | 134914748 | chr5 | 135265737 | 135265767 | chr5 | 135266114 | 135266128 |
| chr5 | 135266578 | 135266672 | chr5 | 135528201 | 135528233 | chr5 | 136834050 | 136834050 |
| chr5 | 136834290 | 136834506 | chr5 | 136834720 | 136834826 | chr5 | 137225092 | 137225297 |
| chr5 | 137912123 | 137912148 | chr5 | 138196197 | 138196213 | chr5 | 138196393 | 138196408 |
| chr5 | 138273812 | 138273854 | chr5 | 139045286 | 139045315 | chr5 | 139047990 | 139048162 |
| chr5 | 139056666 | 139056804 | chr5 | 139227773 | 139227909 | chr5 | 139525728 | 139525758 |
| chr5 | 139779833 | 139779871 | chr5 | 140174798 | 140174839 | chr5 | 140187094 | 140187146 |
| chr5 | 140305978 | 140306050 | chr5 | 140306445 | 140306619 | chr5 | 140305675 | 140306733 |
| chr5 | 140346595 | 140346671 | chr5 | 140514891 | 140614921 | chr5 | 140604459 | 140604501 |
| chr5 | 140613926 | 140614014 | chr5 | 140614314 | 140614328 | chr5 | 140683631 | 140683772 |
| chr5 | 140777328 | 140777487 | chr5 | 140787623 | 140787637 | chr5 | 140797076 | 140797278 |
| chr5 | 140797328 | 140797342 | chr5 | 140800479 | 140800964 | chr5 | 140801035 | 140801246 |
| chr5 | 140855598 | 140856458 | chr5 | 140856547 | 140856622 | chr5 | 141031121 | 141031150 |
| chr5 | 141263035 | 141263142 | chr5 | 141931340 | 141931354 | chr5 | 141931425 | 141931539 |
| chr5 | 142784967 | 142785272 | chr5 | 145713645 | 145713896 | chr5 | 145717175 | 145717196 |
| chr5 | 145717249 | 145717437 | chr5 | 145718802 | 145719753 | chr5 | 145719835 | 145719925 |
| chr5 | 145720812 | 145720917 | chr5 | 145722116 | 145722466 | chr5 | 145722561 | 145723027 |
| chr5 | 145724502 | 145724698 | chr5 | 145725694 | 145725844 | chr5 | 146257332 | 146257602 |
| chr5 | 146889332 | 146889575 | chr5 | 149503827 | 149503856 | chr5 | 149682074 | 149682166 |
| chr5 | 150029147 | 150029245 | chr5 | 150051101 | 150051667 | chr5 | 150326159 | 150326188 |
| chr5 | 150400123 | 150400203 | chr5 | 151066442 | 151066474 | chr5 | 151304371 | 151304401 |
| chr5 | 153852664 | 153852792 | chr5 | 153853420 | 153853478 | chr5 | 153854330 | 153854360 |
| chr5 | 153855175 | 153855264 | chr5 | 153855658 | 153855839 | chr5 | 153856149 | 153856396 |
| chr5 | 153856936 | 153856996 | chr5 | 153857379 | 153857429 | chr5 | 153858319 | 153858599 |
| chr5 | 153859676 | 153859708 | chr5 | 153862037 | 153862179 | chr5 | 153862219 | 153862577 |
| chr5 | 153863421 | 153863451 | chr5 | 154030048 | 154030074 | chr5 | 154209926 | 154209987 |
| chr5 | 154318148 | 154318179 | chr5 | 155107794 | 155107848 | chr5 | 155108161 | 155108267 |
| chr5 | 155108356 | 155108526 | chr5 | 155108733 | 155108763 | chr5 | 156558444 | 156558477 |
| chr5 | 156655170 | 156655200 | chr5 | 156874257 | 156874308 | chr5 | 157001739 | 157001843 |
| chr5 | 157078419 | 157078449 | chr5 | 157098362 | 157098619 | chr5 | 157673799 | 157673964 |
| chr5 | 158478513 | 158478764 | chr5 | 158524692 | 158524748 | chr5 | 158524865 | 158524925 |
| chr5 | 158527443 | 158528069 | chr5 | 159399095 | 159399099 | chr5 | 160975724 | 160975754 |
| chr5 | 161274310 | 161274554 | chr5 | 166865449 | 166865473 | chr5 | 167956177 | 167956266 |
| chr5 | 167956414 | 167956595 | chr5 | 168233396 | 168233482 | chr5 | 168727924 | 168727927 |
| chr5 | 169064327 | 169064805 | chr5 | 169532927 | 169533012 | chr5 | 170108287 | 170108372 |
| chr5 | 170735154 | 170735206 | chr5 | 170735731 | 170735788 | chr5 | 170736116 | 170736163 |
| chr5 | 170736716 | 170736830 | chr5 | 170737282 | 170737479 | chr5 | 170737771 | 170737863 |
| chr5 | 170737936 | 170738689 | chr5 | 170738824 | 170739481 | chr5 | 170739823 | 170740027 |
| chr5 | 170740461 | 170740477 | chr5 | 170740575 | 170741031 | chr5 | 170741507 | 170742275 |
| chr5 | 170742387 | 170742599 | chr5 | 170742673 | 170742827 | chr5 | 170743127 | 170743479 |
| chr5 | 170743647 | 170744128 | chr5 | 170744375 | 170744562 | chr5 | 170745389 | 170745480 |
| chr5 | 171352123 | 171352153 | chr5 | 172354043 | 172354118 | chr5 | 172655879 | 172656215 |
| chr5 | 172659225 | 172659290 | chr5 | 172659496 | 172659655 | chr5 | 172659855 | 172660025 |
| chr5 | 172660142 | 172660218 | chr5 | 172660719 | 172661000 | chr5 | 172661127 | 172661684 |

TABLE 13-continued

| chr | start | end | chr | start | end | chr | start | end |
|---|---|---|---|---|---|---|---|---|
| chr5 | 172664226 | 172654487 | chr5 | 172665590 | 172665812 | chr5 | 172670983 | 172671018 |
| chr5 | 172671345 | 172671481 | chr5 | 172671640 | 172671968 | chr5 | 172672477 | 172672663 |
| chr5 | 172754589 | 172754621 | chr5 | 172754832 | 172754931 | chr5 | 172755470 | 172755562 |
| chr5 | 172755595 | 172755663 | chr5 | 172757048 | 172757111 | chr5 | 174115388 | 174115861 |
| chr5 | 174147523 | 174147596 | chr5 | 174150415 | 174150445 | chr5 | 174159300 | 174159588 |
| chr5 | 174162874 | 174162904 | chr5 | 174220971 | 174221001 | chr5 | 174870738 | 174870786 |
| chr5 | 174871174 | 174871497 | chr5 | 174921456 | 174921483 | chr5 | 175085147 | 175085209 |
| chr5 | 175085525 | 175085719 | chr5 | 175223671 | 175223709 | chr5 | 175298549 | 175298883 |
| chr5 | 175299294 | 175299396 | chr5 | 175300351 | 175300381 | chr5 | 175621390 | 175621501 |
| chr5 | 175792865 | 175792931 | chr5 | 175792998 | 175793063 | chr5 | 175831257 | 175831326 |
| chr5 | 175971447 | 175971471 | chr5 | 176024006 | 176024318 | chr5 | 176046363 | 176046554 |
| chr5 | 176107274 | 176107484 | chr5 | 176107518 | 176107586 | chr5 | 176236721 | 176236898 |
| chr5 | 176264805 | 176264915 | chr5 | 176295786 | 176295892 | chr5 | 176520166 | 176520195 |
| chr5 | 176522400 | 176522566 | chr5 | 176764100 | 176764169 | chr5 | 176827656 | 176827685 |
| chr5 | 177031167 | 177031197 | chr5 | 177408292 | 177408443 | chr5 | 177411638 | 177412141 |
| chr5 | 177713376 | 177713468 | chr5 | 178004325 | 178004374 | chr5 | 178016682 | 178016983 |
| chr5 | 178017520 | 178017867 | chr5 | 178368074 | 178368121 | chr5 | 178487107 | 178487303 |
| chr5 | 178487342 | 178487398 | chr5 | 178576356 | 178576499 | chr5 | 178655753 | 178655871 |
| chr5 | 178771314 | 178771630 | chr5 | 178771724 | 178771859 | chr5 | 178772205 | 178772272 |
| chr5 | 178772603 | 178772729 | chr5 | 178781548 | 178781577 | chr5 | 178957637 | 178957944 |
| chr5 | 179214113 | 179214196 | chr5 | 179270726 | 179270748 | chr5 | 179780104 | 179780144 |
| chr5 | 179780706 | 179780985 | chr5 | 179867486 | 179867548 | chr5 | 180017118 | 180017198 |
| chr5 | 180017608 | 180017933 | chr5 | 180018485 | 180018498 | chr5 | 180047440 | 180047606 |
| chr5 | 180075846 | 180075857 | chr5 | 180076054 | 180076317 | chr5 | 180076567 | 180076602 |
| chr5 | 180076804 | 180076996 | chr5 | 180101016 | 180101167 | chr5 | 180101252 | 180101332 |
| chr5 | 180326126 | 180326156 | chr5 | 180527546 | 180527698 | chr5 | 180594851 | 180594927 |
| chr5 | 180594987 | 180595002 | chr5 | 180600858 | 180601068 | chr5 | 180601128 | 180601218 |
| chr6 | 373148 | 373290 | chr6 | 391173 | 391899 | chr6 | 392410 | 392433 |
| chr6 | 392588 | 392958 | chr6 | 393125 | 393472 | chr6 | 711142 | 711293 |
| chr6 | 1312000 | 1312096 | chr6 | 1312595 | 1312708 | chr6 | 1314088 | 1314100 |
| chr6 | 1378222 | 1378475 | chr6 | 1379584 | 1379614 | chr6 | 1379909 | 1379952 |
| chr6 | 1383677 | 1383708 | chr6 | 1383860 | 1384179 | chr6 | 1384626 | 1384644 |
| chr6 | 1385118 | 1385170 | chr6 | 1386071 | 1386112 | chr6 | 1389124 | 1389262 |
| chr6 | 1390241 | 1390405 | chr6 | 1390424 | 1390758 | chr6 | 1390956 | 1391035 |
| chr6 | 1391318 | 1391379 | chr6 | 1524199 | 1524283 | chr6 | 1605387 | 1605454 |
| chr6 | 1620672 | 1620701 | chr6 | 1624977 | 1625068 | chr6 | 1625128 | 1625818 |
| chr6 | 3053299 | 3053386 | chr6 | 3229029 | 3229059 | chr6 | 3229423 | 3229510 |
| chr6 | 3232010 | 3232260 | chr6 | 3247675 | 3247704 | chr6 | 3285222 | 3285513 |
| chr6 | 3405645 | 3405713 | chr6 | 4775062 | 4775222 | chr6 | 4836440 | 4836458 |
| chr6 | 4951247 | 4951390 | chr6 | 5783325 | 5783496 | chr6 | 5996952 | 5996989 |
| chr6 | 5997802 | 5997832 | chr6 | 6003287 | 6003528 | chr6 | 6004350 | 6004743 |
| chr6 | 6004837 | 6005417 | chr6 | 6006374 | 6006419 | chr6 | 6006674 | 6006883 |
| chr6 | 6007593 | 6008277 | chr6 | 6367086 | 6367271 | chr6 | 6753803 | 6753839 |
| chr6 | 7726334 | 7726363 | chr6 | 7726630 | 7726659 | chr6 | 7726952 | 7726981 |
| chr6 | 7727699 | 7727768 | chr6 | 7728087 | 7728142 | chr6 | 7728849 | 7728941 |
| chr6 | 7731054 | 7731083 | chr6 | 7892314 | 7892412 | chr6 | 10381507 | 10381592 |
| chr6 | 10381695 | 10381968 | chr6 | 10382722 | 10383049 | chr6 | 10383739 | 10383774 |
| chr6 | 10384950 | 10384974 | chr6 | 10385280 | 10385939 | chr6 | 10386210 | 10386273 |
| chr6 | 10390023 | 10391187 | chr6 | 10410518 | 10410578 | chr6 | 10411356 | 10411510 |
| chr6 | 10415113 | 10415215 | chr6 | 10415559 | 10415713 | chr6 | 10416118 | 10416351 |
| chr6 | 10417158 | 10417529 | chr6 | 10419086 | 10419439 | chr6 | 10419477 | 10419506 |
| chr6 | 10419744 | 10419941 | chr6 | 10421053 | 10421451 | chr6 | 10421549 | 10422635 |
| chr6 | 10423613 | 10423704 | chr6 | 10425630 | 10425789 | chr6 | 10425839 | 10426884 |
| chr6 | 10542836 | 10542977 | chr6 | 10881856 | 10882057 | chr6 | 10882321 | 10882350 |
| chr6 | 10883008 | 10883022 | chr6 | 10887078 | 10887686 | chr6 | 11044062 | 11044572 |
| chr6 | 12288517 | 12288681 | chr6 | 12749899 | 12749940 | chr6 | 15513780 | 15513981 |
| chr6 | 16197030 | 16197112 | chr6 | 16729595 | 16729624 | chr6 | 17281417 | 17281534 |
| chr6 | 18035867 | 18036015 | chr6 | 19691638 | 19691841 | chr6 | 19692143 | 19692318 |
| chr6 | 19837064 | 19837140 | chr6 | 19892478 | 19892627 | chr6 | 21664719 | 21664749 |
| chr6 | 21665004 | 21665043 | chr6 | 24358291 | 24358320 | chr6 | 24360074 | 24360170 |
| chr6 | 24494679 | 24494766 | chr6 | 24647342 | 24647381 | chr6 | 26184363 | 26184391 |
| chr6 | 26188715 | 26189393 | chr6 | 26189955 | 26189991 | chr6 | 26199137 | 26199167 |
| chr6 | 26199686 | 26199716 | chr6 | 26214611 | 26214648 | chr6 | 26235223 | 26235623 |
| chr6 | 26240504 | 26241118 | chr6 | 26250468 | 26250826 | chr6 | 26251054 | 26251182 |
| chr6 | 26251816 | 26251954 | chr6 | 26252074 | 26252098 | chr6 | 26252141 | 26252151 |
| chr6 | 26271406 | 26271762 | chr6 | 26271971 | 26272001 | chr6 | 26272512 | 26272617 |
| chr6 | 26273400 | 26273418 | chr6 | 26284811 | 26284898 | chr6 | 26327806 | 26327982 |
| chr6 | 26328294 | 26328457 | chr6 | 26332178 | 26332218 | chr6 | 26501950 | 26502209 |
| chr6 | 26550994 | 26551034 | chr6 | 26577158 | 26577475 | chr6 | 26987967 | 26988166 |
| chr6 | 27059783 | 27059848 | chr6 | 27064682 | 27065198 | chr6 | 27173528 | 27173546 |
| chr6 | 27173633 | 27173855 | chr6 | 27173915 | 27174181 | chr6 | 27182869 | 27182899 |
| chr6 | 27203269 | 27203286 | chr6 | 27205300 | 27205441 | chr6 | 27205671 | 27205836 |
| chr6 | 27205914 | 27206040 | chr6 | 27218951 | 27218980 | chr6 | 27228180 | 27228186 |
| chr6 | 27228290 | 27228395 | chr6 | 27235876 | 27235905 | chr6 | 27247636 | 27247724 |
| chr6 | 27256097 | 27256173 | chr6 | 27256383 | 27256420 | chr6 | 27264332 | 27264364 |
| chr6 | 27279845 | 27280012 | chr6 | 27463029 | 27463687 | chr6 | 27512761 | 27512883 |
| chr6 | 27512995 | 27513487 | chr6 | 27533822 | 27534341 | chr6 | 27559809 | 27560075 |
| chr6 | 27573171 | 27573392 | chr6 | 27598738 | 27598860 | chr6 | 27599159 | 27599341 |

TABLE 13-continued

| chr | start | end | chr | start | end | chr | start | end |
|---|---|---|---|---|---|---|---|---|
| chr6 | 27635265 | 27635434 | chr6 | 27647712 | 27647735 | chr6 | 27647891 | 27647896 |
| chr6 | 27648933 | 27649134 | chr6 | 27783039 | 27783052 | chr6 | 27799464 | 27799581 |
| chr6 | 27834676 | 27834835 | chr6 | 27835047 | 27835096 | chr6 | 27835378 | 27835417 |
| chr6 | 27839726 | 27840082 | chr6 | 27840543 | 27840617 | chr6 | 27841104 | 27841136 |
| chr6 | 27858515 | 27858637 | chr6 | 28175189 | 28176212 | chr6 | 28227076 | 28227141 |
| chr6 | 28303562 | 28303607 | chr6 | 28303815 | 28304263 | chr6 | 28367109 | 28367346 |
| chr6 | 28367491 | 28367774 | chr6 | 28410976 | 28411087 | chr6 | 28411152 | 28411353 |
| chr6 | 28414977 | 28414991 | chr6 | 28457608 | 28457638 | chr6 | 28457870 | 28458158 |
| chr6 | 28956323 | 28956511 | chr6 | 28956660 | 28956719 | chr6 | 30095233 | 30095262 |
| chr6 | 30095418 | 30095570 | chr6 | 30130804 | 30130895 | chr6 | 30644680 | 30644798 |
| chr6 | 32374147 | 32374176 | chr6 | 32374739 | 32374768 | chr6 | 32376051 | 32376080 |
| chr6 | 33161275 | 33161342 | chr6 | 33632930 | 33633000 | chr6 | 33636388 | 33636418 |
| chr6 | 33955505 | 33955731 | chr6 | 34113872 | 34113957 | chr6 | 34170970 | 34170986 |
| chr6 | 34171046 | 34171061 | chr6 | 34219930 | 34219951 | chr6 | 34396517 | 34396542 |
| chr6 | 34714803 | 34714820 | chr6 | 34724198 | 34724228 | chr6 | 35150041 | 35150080 |
| chr6 | 35182493 | 35182622 | chr6 | 35479613 | 35479642 | chr6 | 35992428 | 35992458 |
| chr6 | 36165662 | 36165692 | chr6 | 36178031 | 36178301 | chr6 | 36252984 | 36253171 |
| chr6 | 36313883 | 36313913 | chr6 | 36808323 | 36808441 | chr6 | 37024559 | 37024589 |
| chr6 | 37664140 | 37664187 | chr6 | 37673320 | 37673611 | chr6 | 37776410 | 37776440 |
| chr6 | 37776719 | 37776735 | chr6 | 38683212 | 38683235 | chr6 | 39281088 | 39281133 |
| chr6 | 39281824 | 39281875 | chr6 | 39329863 | 39329892 | chr6 | 39508464 | 39508493 |
| chr6 | 39760401 | 39760661 | chr6 | 40554653 | 40554699 | chr6 | 41337072 | 41337128 |
| chr6 | 41339263 | 41339558 | chr6 | 41339602 | 41339838 | chr6 | 41340902 | 41341182 |
| chr6 | 41341501 | 41341549 | chr6 | 41342243 | 41342275 | chr6 | 41342807 | 41342837 |
| chr6 | 41605937 | 41605951 | chr6 | 41606038 | 41606356 | chr6 | 41606528 | 41606542 |
| chr6 | 41773520 | 41773903 | chr6 | 41774459 | 41774576 | chr6 | 42738966 | 42739049 |
| chr6 | 42773440 | 42773471 | chr6 | 42846662 | 42846705 | chr6 | 42879554 | 42879568 |
| chr6 | 42879622 | 42879718 | chr6 | 42928321 | 42928454 | chr6 | 43211193 | 43211311 |
| chr6 | 43424444 | 43424470 | chr6 | 43425479 | 43425509 | chr6 | 43478676 | 43478745 |
| chr6 | 43612825 | 43612898 | chr6 | 43613053 | 43613067 | chr6 | 43639548 | 43639710 |
| chr6 | 43748463 | 43748616 | chr6 | 44240914 | 44241108 | chr6 | 44695763 | 44695795 |
| chr6 | 45388716 | 45388775 | chr6 | 46702982 | 46703123 | chr6 | 46703350 | 46703436 |
| chr6 | 47590582 | 47590604 | chr6 | 50674372 | 50674750 | chr6 | 50681699 | 50681851 |
| chr6 | 50681911 | 50681942 | chr6 | 50682319 | 50682338 | chr6 | 50682659 | 50682683 |
| chr6 | 50682712 | 50682940 | chr6 | 50682992 | 50683227 | chr6 | 50684939 | 50684969 |
| chr6 | 50689913 | 50690039 | chr6 | 50691065 | 50691095 | chr6 | 50692083 | 50692212 |
| chr6 | 50692300 | 50692481 | chr6 | 50787216 | 50787876 | chr6 | 50787950 | 50788352 |
| chr6 | 50789374 | 50789404 | chr6 | 50791187 | 50791494 | chr6 | 50791551 | 50791632 |
| chr6 | 50793335 | 50793404 | chr6 | 50793728 | 50793882 | chr6 | 50794531 | 50794693 |
| chr6 | 50803834 | 50803867 | chr6 | 50804131 | 50804368 | chr6 | 50808681 | 50808854 |
| chr6 | 50810551 | 50810713 | chr6 | 50811062 | 50811488 | chr6 | 50813258 | 50813939 |
| chr6 | 50814569 | 50814599 | chr6 | 50817023 | 50817229 | chr6 | 50817905 | 50817935 |
| chr6 | 50818449 | 50818706 | chr6 | 50818920 | 50819000 | chr6 | 52227752 | 52227781 |
| chr6 | 52228008 | 52228037 | chr6 | 52344375 | 52344405 | chr6 | 53212491 | 53213970 |
| chr6 | 55443691 | 55443946 | chr6 | 56112262 | 56112386 | chr6 | 56716390 | 56716410 |
| chr6 | 56818656 | 56818937 | chr6 | 56819217 | 56819637 | chr6 | 56819897 | 56819926 |
| chr6 | 58147447 | 58147480 | chr6 | 58147790 | 58147976 | chr6 | 62995356 | 62995874 |
| chr6 | 62996078 | 62996146 | chr6 | 62996443 | 62996489 | chr6 | 70992137 | 70992162 |
| chr6 | 70992415 | 70992560 | chr6 | 70992830 | 70993015 | chr6 | 71665638 | 71665723 |
| chr6 | 71666788 | 71666986 | chr6 | 72129789 | 72129829 | chr6 | 72130191 | 72130464 |
| chr6 | 72596120 | 72596315 | chr6 | 72596950 | 72596980 | chr6 | 73329784 | 73330126 |
| chr6 | 73330834 | 73331304 | chr6 | 73331515 | 73331850 | chr6 | 73331876 | 73333099 |
| chr6 | 73980699 | 73980722 | chr6 | 76059561 | 76059787 | chr6 | 78172177 | 78172275 |
| chr6 | 78172323 | 78172572 | chr6 | 78173212 | 78173264 | chr6 | 78173696 | 78173725 |
| chr6 | 78173772 | 78173984 | chr6 | 78176458 | 78176820 | chr6 | 79620475 | 79620699 |
| chr6 | 80656930 | 80657180 | chr6 | 82463270 | 82463310 | chr6 | 82958615 | 82958646 |
| chr6 | 84141298 | 84141412 | chr6 | 84417436 | 84417700 | chr6 | 84418261 | 84418281 |
| chr6 | 84418644 | 84418788 | chr6 | 84419157 | 84419415 | chr6 | 84562873 | 84563242 |
| chr6 | 84563489 | 84563542 | chr6 | 85050460 | 85050504 | chr6 | 85472407 | 85473703 |
| chr6 | 85473928 | 85474378 | chr6 | 85474594 | 85474736 | chr6 | 85476233 | 85476285 |
| chr6 | 85476998 | 85477028 | chr6 | 85478514 | 85478724 | chr6 | 85482530 | 85482796 |
| chr6 | 85483345 | 85483375 | chr6 | 85483760 | 85483931 | chr6 | 85484558 | 85484625 |
| chr6 | 85484717 | 85484920 | chr6 | 86302413 | 86302454 | chr6 | 87647114 | 87647143 |
| chr6 | 87862092 | 87862172 | chr6 | 88876963 | 88877421 | chr6 | 91320285 | 91320318 |
| chr6 | 91320949 | 91321295 | chr6 | 94126973 | 94127064 | chr6 | 94127455 | 94127544 |
| chr6 | 94128365 | 94128399 | chr6 | 94129219 | 94129257 | chr6 | 94129509 | 94129575 |
| chr6 | 96464100 | 96464204 | chr6 | 99271926 | 99272810 | chr6 | 99273369 | 99273410 |
| chr6 | 99277180 | 99277330 | chr6 | 99279556 | 99279612 | chr6 | 99280557 | 99280744 |
| chr6 | 99281014 | 99281036 | chr6 | 99281068 | 99281385 | chr6 | 99283512 | 99283582 |
| chr6 | 99290360 | 99290398 | chr6 | 99291264 | 99291341 | chr6 | 99292252 | 99292417 |
| chr6 | 99295726 | 99295863 | chr6 | 99296062 | 99296364 | chr6 | 99296408 | 99296457 |
| chr6 | 99396456 | 99396473 | chr6 | 99842067 | 99842163 | chr6 | 99842359 | 99842382 |
| chr6 | 100038682 | 100038706 | chr6 | 100038786 | 100038964 | chr6 | 100039275 | 100039289 |
| chr6 | 100050754 | 100050810 | chr6 | 100050859 | 100051108 | chr6 | 100051360 | 100051507 |
| chr6 | 100051772 | 100051971 | chr6 | 100053221 | 100053511 | chr6 | 100054866 | 100054917 |
| chr6 | 100061022 | 100061076 | chr6 | 100061311 | 100061419 | chr6 | 100062178 | 100062586 |
| chr6 | 100062944 | 100063068 | chr6 | 100441498 | 100441737 | chr6 | 100441762 | 100441966 |
| chr6 | 100903384 | 100903404 | chr6 | 100903561 | 100903631 | chr6 | 100904214 | 100904275 |

TABLE 13-continued

| chr | start | end | chr | start | end | chr | start | end |
|---|---|---|---|---|---|---|---|---|
| chr6 | 100905969 | 100906016 | chr6 | 100911686 | 100911723 | chr6 | 100912070 | 100912119 |
| chr6 | 100912421 | 100912445 | chr6 | 100912466 | 100912480 | chr6 | 100912919 | 100913050 |
| chr6 | 100915101 | 100915205 | chr6 | 101840708 | 101840820 | chr6 | 101846782 | 101846789 |
| chr6 | 101847185 | 101847215 | chr6 | 101850147 | 101850275 | chr6 | 105388679 | 105388708 |
| chr6 | 105389510 | 105389710 | chr6 | 105400913 | 105401007 | chr6 | 105401620 | 105401874 |
| chr6 | 105404574 | 105404674 | chr6 | 105405656 | 105405772 | chr6 | 105406098 | 105406128 |
| chr6 | 105584264 | 105584319 | chr6 | 105584367 | 105585554 | chr6 | 105821423 | 105821453 |
| chr6 | 106429049 | 106429475 | chr6 | 106429590 | 106429624 | chr6 | 106434339 | 106434368 |
| chr6 | 106441869 | 106442979 | chr6 | 106731553 | 106731597 | chr6 | 106960908 | 106961023 |
| chr6 | 107562814 | 107562859 | chr6 | 108280322 | 108280352 | chr6 | 108435075 | 108435263 |
| chr6 | 108436072 | 108436526 | chr6 | 108438261 | 108438577 | chr6 | 108440091 | 108440644 |
| chr6 | 108440745 | 108440961 | chr6 | 108479290 | 108479665 | chr6 | 108484909 | 108485406 |
| chr6 | 108485665 | 108485905 | chr6 | 108486158 | 108486394 | chr6 | 108487724 | 108488416 |
| chr6 | 108489662 | 108489808 | chr6 | 108490067 | 108490245 | chr6 | 108490297 | 108490514 |
| chr6 | 108490538 | 108490633 | chr6 | 108490978 | 108491000 | chr6 | 108491108 | 108491423 |
| chr6 | 108492270 | 108492451 | chr6 | 108495681 | 108495817 | chr6 | 108495916 | 108495951 |
| chr6 | 108496208 | 108496649 | chr6 | 108497494 | 108497796 | chr6 | 108497827 | 108497881 |
| chr6 | 110437721 | 110437751 | chr6 | 110679123 | 110679414 | chr6 | 110797678 | 110797708 |
| chr6 | 110798007 | 110798036 | chr6 | 116783448 | 116783493 | chr6 | 117086249 | 117086639 |
| chr6 | 117585967 | 117586004 | chr6 | 117586847 | 117587169 | chr6 | 117587480 | 117587577 |
| chr6 | 117591161 | 117591191 | chr6 | 117591411 | 117591596 | chr6 | 117591684 | 117591743 |
| chr6 | 118228102 | 118228151 | chr6 | 118228747 | 118228828 | chr6 | 118229154 | 118229383 |
| chr6 | 118229626 | 118229818 | chr6 | 118241228 | 118241308 | chr6 | 118241395 | 118241500 |
| chr6 | 119254654 | 119254678 | chr6 | 121758672 | 121758994 | chr6 | 123317073 | 123317589 |
| chr6 | 123317797 | 123317833 | chr6 | 124124432 | 124124466 | chr6 | 124124860 | 124125016 |
| chr6 | 125284131 | 125284175 | chr6 | 126068092 | 126068178 | chr6 | 127439379 | 127439453 |
| chr6 | 127439985 | 127440127 | chr6 | 127440331 | 127440962 | chr6 | 127441031 | 127441123 |
| chr6 | 127441554 | 127441762 | chr6 | 127442021 | 127442070 | chr6 | 127442090 | 127442104 |
| chr6 | 127840501 | 127840681 | chr6 | 129204459 | 129204524 | chr6 | 130686534 | 130687057 |
| chr6 | 131602584 | 131602694 | chre | 132722078 | 132722141 | chr6 | 132722158 | 132722196 |
| chr6 | 133561740 | 133562070 | chr6 | 133562374 | 133662436 | chr6 | 133562675 | 133563058 |
| chr6 | 133563327 | 133563918 | chr6 | 134067453 | 134067471 | chr6 | 134176232 | 134176299 |
| chr6 | 134176549 | 134176579 | chr6 | 134210528 | 134211018 | chr6 | 134211112 | 134211367 |
| chr6 | 134213944 | 134213987 | chr6 | 134214077 | 134214364 | chr6 | 134589500 | 134589604 |
| chr6 | 134638950 | 134639003 | chr6 | 137241928 | 137242205 | chr6 | 137243208 | 137243410 |
| chr6 | 137244114 | 137244148 | chr6 | 137244236 | 137244465 | chr6 | 137311158 | 137311380 |
| chr6 | 137366354 | 137366383 | chr6 | 137809141 | 137809365 | chr6 | 137809446 | 137809916 |
| chr6 | 137810033 | 137811088 | chr6 | 137813787 | 137813895 | chr6 | 137814604 | 137814618 |
| chr6 | 137814654 | 137814763 | chr6 | 137815008 | 137815170 | chr6 | 137815225 | 137815662 |
| chr6 | 137816472 | 137817351 | chr6 | 137818505 | 137818598 | chr6 | 137818619 | 137819368 |
| chr6 | 146755567 | 146755649 | chr6 | 149868368 | 149868387 | chr6 | 150284552 | 150284581 |
| chr6 | 150285056 | 150285368 | chr6 | 150285545 | 150285885 | chr6 | 150286100 | 150286639 |
| chr6 | 150358970 | 150359192 | chr6 | 151561016 | 151561340 | chr6 | 151561369 | 151561857 |
| chr6 | 151562066 | 151562563 | chr6 | 151815055 | 151815089 | chr6 | 152419908 | 152419940 |
| chr6 | 152623015 | 152623493 | chr6 | 152957895 | 152958076 | chr6 | 153451236 | 153451500 |
| chr6 | 153451890 | 153451968 | chr6 | 153452232 | 153452320 | chr6 | 153452713 | 153452746 |
| chr6 | 154360650 | 154360746 | chr6 | 154970558 | 154970587 | chr6 | 155316257 | 155316265 |
| chr6 | 155569208 | 155569305 | chr6 | 157502438 | 157502561 | chr6 | 157506082 | 157506112 |
| chr6 | 157556764 | 157557296 | chr6 | 159290823 | 159290852 | chr6 | 159590048 | 159590086 |
| chr6 | 159590155 | 159590761 | chr6 | 159590972 | 159690986 | chr6 | 159654923 | 159655003 |
| chr6 | 161100361 | 161100390 | chr6 | 161188513 | 161188543 | chr6 | 161352101 | 161352135 |
| chr6 | 161780098 | 161780139 | chr6 | 163602842 | 163602872 | chr6 | 163834314 | 163834382 |
| chr6 | 163834406 | 163834532 | chr6 | 163834857 | 163834901 | chr6 | 163836568 | 163836900 |
| chr6 | 164179652 | 164179668 | chr6 | 164196987 | 164197003 | chr6 | 164228294 | 164228363 |
| chr6 | 164246109 | 164246143 | chr6 | 164283254 | 164283377 | chr6 | 164314289 | 164314443 |
| chr6 | 164322666 | 164322775 | chr6 | 166074119 | 166074412 | chr6 | 166076788 | 166077021 |
| chr6 | 166077378 | 166077632 | chr6 | 166267582 | 166267891 | chr6 | 166401254 | 166401307 |
| chr6 | 166402240 | 166402546 | chr6 | 166421911 | 156422185 | chr6 | 166579723 | 166580144 |
| chr6 | 166580344 | 166582797 | chr6 | 166944367 | 166944403 | chr6 | 167835129 | 167835171 |
| chr6 | 168719983 | 168720019 | chr6 | 168842847 | 168842944 | chr6 | 168858122 | 168858296 |
| chr6 | 168972472 | 168972502 | chr6 | 169002054 | 169002084 | chr6 | 169653638 | 169653668 |
| chr6 | 170047467 | 170047499 | chr6 | 170240639 | 170240714 | chr6 | 170264728 | 170264761 |
| chr6 | 170475105 | 170475267 | chr6 | 170494286 | 170494315 | chr6 | 170894820 | 170894836 |
| chr7 | 68930 | 68960 | chr7 | 329805 | 329838 | chr7 | 369844 | 369980 |
| chr7 | 389663 | 389693 | chr7 | 409826 | 409892 | chr7 | 427454 | 427484 |
| chr7 | 431386 | 431492 | chr7 | 497782 | 497934 | chr7 | 503811 | 503936 |
| chr7 | 551599 | 551697 | chr7 | 556928 | 556983 | chr7 | 564237 | 564271 |
| chr7 | 578922 | 579020 | chr7 | 579827 | 579857 | chr7 | 752120 | 752221 |
| chr7 | 907656 | 907709 | chr7 | 915058 | 915087 | chr7 | 922050 | 922235 |
| chr7 | 927933 | 927986 | chr7 | 1022224 | 1022254 | chr7 | 1030172 | 1030283 |
| chr7 | 1054579 | 1054696 | chr7 | 1086199 | 1086319 | chr7 | 1195270 | 1195364 |
| chr7 | 1263761 | 1263960 | chr7 | 1268318 | 1268366 | chr7 | 1269305 | 1269463 |
| chr7 | 1269553 | 1269808 | chr7 | 1270406 | 1270440 | chr7 | 1273167 | 1273330 |
| chr7 | 1274641 | 1274677 | chr7 | 1275579 | 1275680 | chr7 | 1277817 | 1277865 |
| chr7 | 1279099 | 1279129 | chr7 | 1279965 | 1279995 | chr7 | 1281131 | 1281232 |
| chr7 | 1281493 | 1281555 | chr7 | 1282042 | 1282150 | chr7 | 1282506 | 1282644 |
| chr7 | 1288582 | 1288753 | chr7 | 1308351 | 1308497 | chr7 | 1325810 | 1325882 |
| chr7 | 1416020 | 1416131 | chr7 | 1423632 | 1423677 | chr7 | 1459041 | 1459191 |

TABLE 13-continued

| chr | start | end | chr | start | end | chr | start | end |
|---|---|---|---|---|---|---|---|---|
| chr7 | 1503417 | 1503596 | chr7 | 1547311 | 1547394 | chr7 | 1598639 | 1598697 |
| chr7 | 1607386 | 1607465 | chr7 | 1607971 | 1608001 | chr7 | 1615390 | 1615444 |
| chr7 | 1627404 | 1627434 | chr7 | 1641774 | 1641923 | chr7 | 1681189 | 1681239 |
| chr7 | 1688977 | 1689122 | chr7 | 1690745 | 1690851 | chr7 | 1709138 | 1709235 |
| chr7 | 1709474 | 1709561 | chr7 | 1733166 | 1733378 | chr7 | 1748514 | 1748766 |
| chr7 | 1775831 | 1775861 | chr7 | 1778875 | 1778914 | chr7 | 1783551 | 1783623 |
| chr7 | 1786514 | 1786899 | chr7 | 1787166 | 1787324 | chr7 | 1800882 | 1800912 |
| chr7 | 1970842 | 1970872 | chr7 | 2109874 | 2109904 | chr7 | 2163332 | 2163467 |
| chr7 | 2208670 | 2208808 | chr7 | 2232963 | 2233056 | chr7 | 2233292 | 2233414 |
| chr7 | 2238118 | 2238235 | chr7 | 2300787 | 2300813 | chr7 | 2473452 | 2473605 |
| chr7 | 2565919 | 2566041 | chr7 | 2566600 | 2566630 | chr7 | 2720013 | 2720140 |
| chr7 | 2728068 | 2728165 | chr7 | 2979480 | 2979512 | chr7 | 2985518 | 2985547 |
| chr7 | 3033658 | 3033688 | chr7 | 3083331 | 3083352 | chr7 | 3283704 | 3283894 |
| chr7 | 3340444 | 3340473 | chr7 | 3341570 | 3341597 | chr7 | 4215324 | 4215384 |
| chr7 | 4856984 | 4857048 | chr7 | 4922550 | 4922706 | chr7 | 4923328 | 4923397 |
| chr7 | 4998201 | 4998388 | chr7 | 5111528 | 5111669 | chr7 | 5262433 | 5262562 |
| chr7 | 5397777 | 5397938 | chr7 | 5632939 | 5633100 | chr7 | 5648107 | 5648393 |
| chr7 | 6059103 | 6059182 | chr7 | 6060590 | 6060612 | chr7 | 6099217 | 6099246 |
| chr7 | 6124620 | 6124714 | chr7 | 6188610 | 6189061 | chr7 | 6414386 | 6414415 |
| chr7 | 6426878 | 6426907 | chr7 | 6443279 | 6443376 | chr7 | 6443826 | 6443856 |
| chr7 | 6524573 | 6524599 | chr7 | 6524977 | 6525012 | chr7 | 6525477 | 6525512 |
| chr7 | 6543150 | 6543216 | chr7 | 6560235 | 6560345 | chr7 | 6566413 | 6566663 |
| chr7 | 6570959 | 6571130 | chr7 | 6576137 | 6576367 | chr7 | 6703555 | 6703869 |
| chr7 | 6703916 | 6703959 | chr7 | 7605662 | 7605822 | chr7 | 8473070 | 8473455 |
| chr7 | 8473480 | 8473674 | chr7 | 8473956 | 8474241 | chr7 | 8474516 | 8474562 |
| chr7 | 8474814 | 8475057 | chr7 | 8480640 | 8481159 | chr7 | 8481642 | 8481833 |
| chr7 | 8482056 | 8482297 | chr7 | 8482670 | 8482824 | chr7 | 8482885 | 8482921 |
| chr7 | 8483147 | 8483950 | chr7 | 12151440 | 12151472 | chr7 | 12151524 | 12151678 |
| chr7 | 12443317 | 12443403 | chr7 | 12443841 | 12443871 | chr7 | 12610339 | 12610476 |
| chr7 | 15725983 | 15726081 | chr7 | 15726634 | 15727077 | chr7 | 15727290 | 15727320 |
| chr7 | 19145808 | 19145893 | chr7 | 19146032 | 19146184 | chr7 | 19146238 | 19146249 |
| chr7 | 19146502 | 19146558 | chr7 | 19147122 | 19147798 | chr7 | 19152224 | 19152349 |
| chr7 | 19155791 | 19155820 | chr7 | 19156126 | 19156132 | chr7 | 19156304 | 19156643 |
| chr7 | 19156703 | 19156745 | chr7 | 19157144 | 19157566 | chr7 | 19157634 | 19158015 |
| chr7 | 19158632 | 19158735 | chr7 | 19184058 | 19184255 | chr7 | 19813284 | 19813313 |
| chr7 | 20816252 | 20816447 | chr7 | 20817380 | 20817410 | chr7 | 20818130 | 20818276 |
| chr7 | 20823292 | 20823330 | chr7 | 20823383 | 20823432 | chr7 | 20823920 | 20824143 |
| chr7 | 20824476 | 20824819 | chr7 | 20824836 | 20824946 | chr7 | 20825379 | 20825559 |
| chr7 | 20826113 | 20826202 | chr7 | 20826884 | 20827199 | chr7 | 20830670 | 20830700 |
| chr7 | 20833167 | 20833322 | chr7 | 21582593 | 21582640 | chr7 | 21582792 | 21582868 |
| chr7 | 21583263 | 21583277 | chr7 | 21583304 | 21583326 | chr7 | 22539833 | 22539909 |
| chr7 | 22589356 | 22589870 | chr7 | 23287253 | 23287350 | chr7 | 23287533 | 23287624 |
| chr7 | 23578780 | 23578857 | chr7 | 24323763 | 24323939 | chr7 | 24580785 | 24580806 |
| chr7 | 24796478 | 24796567 | chr7 | 25132702 | 25132726 | chr7 | 25896521 | 25896603 |
| chr7 | 25896663 | 25895864 | chr7 | 25897133 | 25897246 | chr7 | 27127863 | 27127898 |
| chr7 | 27135327 | 27135770 | chr7 | 27136013 | 27136790 | chr7 | 27138381 | 27138410 |
| chr7 | 27184015 | 27184190 | chr7 | 27190591 | 27191226 | chr7 | 27192061 | 27192098 |
| chr7 | 27195462 | 27195601 | chr7 | 27195867 | 27195892 | chr7 | 27196153 | 27196839 |
| chr7 | 27204487 | 27204769 | chr7 | 27205266 | 27205395 | chr7 | 27205678 | 27205789 |
| chr7 | 27208187 | 27208285 | chr7 | 27209462 | 27209582 | chr7 | 27212499 | 27212899 |
| chr7 | 27213189 | 27214261 | chr7 | 27217042 | 27217071 | chr7 | 27223114 | 27223151 |
| chr7 | 27223601 | 27223696 | chr7 | 27224069 | 27224609 | chr7 | 27225035 | 27225057 |
| chr7 | 27225447 | 27225483 | chr7 | 27227874 | 27227953 | chr7 | 27231476 | 27231505 |
| chr7 | 27231818 | 27231894 | chr7 | 27232289 | 27232962 | chr7 | 27233410 | 27233454 |
| chr7 | 27238887 | 27238917 | chr7 | 27239226 | 27239234 | chr7 | 27240230 | 27240381 |
| chr7 | 27244515 | 27244610 | chr7 | 27244798 | 27245310 | chr7 | 27245668 | 27245795 |
| chr7 | 27252380 | 27252410 | chr7 | 27260092 | 27260100 | chr7 | 27264875 | 27265325 |
| chr7 | 27265538 | 27265584 | chr7 | 27275513 | 27275543 | chr7 | 27279238 | 27279368 |
| chr7 | 27281329 | 27281360 | chr7 | 27282089 | 27283013 | chr7 | 27283351 | 27283627 |
| chr7 | 27285621 | 27285913 | chr7 | 27285980 | 27286098 | chr7 | 27286171 | 27286248 |
| chr7 | 27288946 | 27289100 | chr7 | 27289170 | 27289449 | chr7 | 27291315 | 27291851 |
| chr7 | 28110701 | 28110828 | chr7 | 28449276 | 28449290 | chr7 | 28449659 | 28449781 |
| chr7 | 28449858 | 28450015 | chr7 | 28995657 | 28995978 | chr7 | 28996457 | 28996495 |
| chr7 | 28996840 | 28996916 | chr7 | 28997136 | 28997625 | chr7 | 28998053 | 28998119 |
| chr7 | 30029702 | 30029822 | chr7 | 30029923 | 30029952 | chr7 | 30721280 | 30721902 |
| chr7 | 30722290 | 30722375 | chr7 | 30857157 | 30857292 | chr7 | 31093003 | 31093133 |
| chr7 | 31232909 | 31232939 | chr7 | 31375965 | 31376135 | chr7 | 32110704 | 32110772 |
| chr7 | 32337807 | 32337837 | chr7 | 32338088 | 32338217 | chr7 | 32338284 | 32338410 |
| chr7 | 32338900 | 32338930 | chr7 | 32467461 | 32467655 | chr7 | 32467947 | 32468062 |
| chr7 | 32997124 | 32997454 | chr7 | 33167928 | 33167949 | chr7 | 33725803 | 33725938 |
| chr7 | 33943459 | 33943759 | chr7 | 35225809 | 35225833 | chr7 | 35226193 | 35226522 |
| chr7 | 35226557 | 35226765 | chr7 | 35292970 | 35293086 | chr7 | 35293183 | 35293293 |
| chr7 | 35294032 | 35294141 | chr7 | 35294502 | 35294536 | chr7 | 35295104 | 35295105 |
| chr7 | 35295908 | 35295944 | chr7 | 35296935 | 35297004 | chr7 | 35297138 | 35297353 |
| chr7 | 35297471 | 35298016 | chr7 | 35300951 | 35301008 | chr7 | 35301102 | 35301948 |
| chr7 | 37487164 | 37487255 | chr7 | 37487375 | 37487453 | chr7 | 37487756 | 37487826 |
| chr7 | 37488257 | 37488578 | chr7 | 37488920 | 37488992 | chr7 | 37907440 | 37907470 |
| chr7 | 37955878 | 37955979 | chr7 | 37956271 | 37956439 | chr7 | 37960301 | 37960335 |

TABLE 13-continued

| chr | start | end | chr | start | end | chr | start | end |
|---|---|---|---|---|---|---|---|---|
| chr7 | 38588471 | 38588501 | chr7 | 38670357 | 38670663 | chr7 | 38670957 | 38671015 |
| chr7 | 39015542 | 39015981 | chr7 | 39649223 | 39649253 | chr7 | 39649444 | 39649457 |
| chr7 | 39872836 | 39873015 | chr7 | 41739663 | 41739879 | chr7 | 41982690 | 41982874 |
| chr7 | 42267647 | 42267677 | chr7 | 42276346 | 42276634 | chr7 | 42377468 | 42377497 |
| chr7 | 42533257 | 42533296 | chr7 | 43152109 | 43152207 | chr7 | 43152414 | 43152700 |
| chr7 | 43152957 | 43153199 | chr7 | 43153230 | 43153237 | chr7 | 44097690 | 44097876 |
| chr7 | 44151398 | 44151428 | chr7 | 44151795 | 44151933 | chr7 | 44163926 | 44163989 |
| chr7 | 44364838 | 44364903 | chr7 | 44740630 | 44740672 | chr7 | 44835121 | 44835384 |
| chr7 | 45038532 | 45038564 | chr7 | 45046874 | 45046982 | chr7 | 45613785 | 45613813 |
| chr7 | 45613858 | 45613898 | chr7 | 45614341 | 45614474 | chr7 | 45614738 | 45614809 |
| chr7 | 45614929 | 45615020 | chr7 | 45615440 | 45615495 | chr7 | 45960743 | 45960794 |
| chr7 | 45961146 | 45961176 | chr7 | 45961508 | 45961576 | chr7 | 45961833 | 45961888 |
| chr7 | 47515359 | 47515405 | chr7 | 47704324 | 47704359 | chr7 | 49812820 | 49813017 |
| chr7 | 49813810 | 49813994 | chr7 | 49814531 | 49814750 | chr7 | 49815117 | 49815249 |
| chr7 | 49815657 | 49815765 | chr7 | 49819674 | 49819703 | chr7 | 50294451 | 50294481 |
| chr7 | 50343263 | 50343401 | chr7 | 50343975 | 50343994 | chr7 | 50344226 | 50344491 |
| chr7 | 50365076 | 50365107 | chr7 | 50438618 | 50438648 | chr7 | 50441145 | 50441285 |
| chr7 | 50560588 | 50560637 | chr7 | 50860226 | 50861102 | chr7 | 51383754 | 51383790 |
| chr7 | 51384327 | 51384440 | chr7 | 51384915 | 51384951 | chr7 | 52156231 | 52156261 |
| chr7 | 54609852 | 54609951 | chr7 | 54609992 | 54610153 | chr7 | 54612418 | 54612730 |
| chr7 | 55086473 | 55086601 | chr7 | 55086983 | 55087533 | chr7 | 55209976 | 55210005 |
| chr7 | 55211065 | 55211094 | chr7 | 55221729 | 55221836 | chr7 | 55223589 | 55223636 |
| chr7 | 55227993 | 55228022 | chr7 | 55233028 | 55233123 | chr7 | 55241663 | 55241737 |
| chr7 | 55242419 | 55242493 | chr7 | 55248975 | 55249085 | chr7 | 55259404 | 55259547 |
| chr7 | 55260469 | 55260498 | chr7 | 55268867 | 55268896 | chr7 | 55410019 | 55410126 |
| chr7 | 55506288 | 55506348 | chr7 | 56018123 | 56018205 | chr7 | 56031793 | 56031869 |
| chr7 | 63667431 | 63667460 | chr7 | 64330411 | 64330470 | chr7 | 64330734 | 64330833 |
| chr7 | 64349042 | 64349056 | chr7 | 64349331 | 64349470 | chr7 | 64700283 | 64700329 |
| chr7 | 64712364 | 64712510 | chr7 | 64974382 | 64974402 | chr7 | 65037609 | 65037702 |
| chr7 | 65508995 | 65509043 | chr7 | 65878743 | 65878793 | chr7 | 66214942 | 66214961 |
| chr7 | 68204793 | 68204931 | chr7 | 69062519 | 69062635 | chr7 | 69064590 | 69064771 |
| chr7 | 69064834 | 69065045 | chr7 | 69897780 | 69897827 | chr7 | 70596454 | 70596688 |
| chr7 | 70597406 | 70597451 | chr7 | 70597835 | 70597871 | chr7 | 70597991 | 70598123 |
| chr7 | 70598170 | 70598387 | chr7 | 71217108 | 71217332 | chr7 | 71603924 | 71604082 |
| chr7 | 71800676 | 71800756 | chr7 | 71800934 | 71801104 | chr7 | 71802410 | 71802522 |
| chr7 | 71802578 | 71802637 | chr7 | 71871203 | 71871245 | chr7 | 75511201 | 75511298 |
| chr7 | 76033250 | 76033289 | chr7 | 77129885 | 77129907 | chr7 | 77324362 | 77324448 |
| chr7 | 79081792 | 79081821 | chr7 | 79082023 | 79082218 | chr7 | 79083392 | 79083834 |
| chr7 | 80548257 | 80548403 | chr7 | 82072350 | 82072503 | chr7 | 82073495 | 82073533 |
| chr7 | 84815141 | 84815226 | chr7 | 84815744 | 84815954 | chr7 | 86273208 | 86273541 |
| chr7 | 86274258 | 86274457 | chr7 | 87104816 | 87105430 | chr7 | 87229537 | 87230433 |
| chr7 | 87257012 | 87257047 | chr7 | 87257963 | 87258054 | chr7 | 87563370 | 87563614 |
| chr7 | 87563829 | 87563890 | chr7 | 87825102 | 87825137 | chr7 | 88387982 | 88388167 |
| chr7 | 88388540 | 88388660 | chr7 | 88388879 | 88388901 | chr7 | 88389047 | 88389356 |
| chr7 | 89747996 | 89748340 | chr7 | 89950183 | 89950810 | chr7 | 90226269 | 90226464 |
| chr7 | 90895012 | 90895097 | chr7 | 92466152 | 92466400 | chr7 | 92689705 | 92689792 |
| chr7 | 93203708 | 93203756 | chr7 | 93204332 | 93204492 | chr7 | 93519351 | 93519765 |
| chr7 | 93519855 | 93520137 | chr7 | 93551323 | 93551425 | chr7 | 94284302 | 94284873 |
| chr7 | 96619560 | 96619603 | chr7 | 96621715 | 96621811 | chr7 | 96622107 | 96622349 |
| chr7 | 96622694 | 96622723 | chr7 | 96625537 | 96625720 | chr7 | 96625998 | 96626051 |
| chr7 | 96627013 | 96627048 | chr7 | 96631579 | 96631680 | chr7 | 96634645 | 96634928 |
| chr7 | 96635345 | 96635379 | chr7 | 96635439 | 96635451 | chr7 | 96635733 | 96635971 |
| chr7 | 96636034 | 96636645 | chr7 | 96639318 | 96639348 | chr7 | 96646662 | 96647131 |
| chr7 | 96647809 | 96648219 | chr7 | 96649955 | 96650094 | chr7 | 96650884 | 96651076 |
| chr7 | 96651137 | 96651151 | chr7 | 96651469 | 96651537 | chr7 | 96652144 | 96652174 |
| chr7 | 96653507 | 96653819 | chr7 | 96653863 | 96653993 | chr7 | 97361098 | 97361422 |
| chr7 | 97361521 | 97361781 | chr7 | 97362292 | 97362607 | chr7 | 97600104 | 97600194 |
| chr7 | 97869614 | 97869644 | chr7 | 98197224 | 98197242 | chr7 | 98245885 | 98246078 |
| chr7 | 98246305 | 98246507 | chr7 | 98246534 | 98246868 | chr7 | 98247126 | 98247656 |
| chr7 | 98966786 | 98966881 | chr7 | 98971529 | 98971549 | chr7 | 99104258 | 99104293 |
| chr7 | 99177742 | 99177870 | chr7 | 99591731 | 99591762 | chr7 | 99595194 | 99595335 |
| chr7 | 99751578 | 99751630 | chr7 | 99775192 | 99775558 | chr7 | 100088183 | 100088312 |
| chr7 | 100179889 | 100179927 | chr7 | 100295403 | 100295424 | chr7 | 100318505 | 100318575 |
| chr7 | 100320690 | 100320719 | chr7 | 100547037 | 100547073 | chr7 | 100609750 | 100609780 |
| chr7 | 100808466 | 100808502 | chr7 | 100809436 | 100809521 | chr7 | 100823436 | 100823497 |
| chr7 | 101005968 | 101005998 | chr7 | 101241993 | 101242023 | chr7 | 101475790 | 101475858 |
| chr7 | 101558399 | 101558698 | chr7 | 101627741 | 101627787 | chr7 | 101707502 | 101707532 |
| chr7 | 103085876 | 103086474 | chr7 | 103629059 | 103629794 | chr7 | 103630054 | 103630082 |
| chr7 | 103630475 | 103630824 | chr7 | 103969217 | 103969341 | chr7 | 103969694 | 103969794 |
| chr7 | 105279467 | 105279671 | chr7 | 106622834 | 106622961 | chr7 | 106685282 | 106685345 |
| chr7 | 106797774 | 106797804 | chr7 | 107301494 | 107301640 | chr7 | 107483694 | 107483918 |
| chr7 | 108095329 | 108095362 | chr7 | 108095781 | 108096055 | chr7 | 108097172 | 108097491 |
| chr7 | 111202993 | 111203097 | chr7 | 112726558 | 112726614 | chr7 | 113722810 | 113723283 |
| chr7 | 113723339 | 113723439 | chr7 | 113724956 | 113725081 | chr7 | 113726509 | 113726539 |
| chr7 | 113727442 | 113727486 | chr7 | 113727754 | 113727781 | chr7 | 115117552 | 115117647 |
| chr7 | 116140252 | 116140356 | chr7 | 116412008 | 116412058 | chr7 | 116415100 | 116415129 |
| chr7 | 116417443 | 116417496 | chr7 | 116422067 | 116422132 | chr7 | 116423399 | 116423488 |
| chr7 | 116962893 | 116963146 | chr7 | 116963331 | 116963476 | chr7 | 117119381 | 117120271 |

TABLE 13-continued

| chr | start | end | chr | start | end | chr | start | end |
|---|---|---|---|---|---|---|---|---|
| chr7 | 117513675 | 117513849 | chr7 | 119913561 | 119913785 | chr7 | 120969672 | 120969800 |
| chr7 | 121513523 | 121513709 | chr7 | 121939677 | 121940244 | chr7 | 121940434 | 121940448 |
| chr7 | 121940935 | 121941052 | chr7 | 121941881 | 121942170 | chr7 | 121945822 | 121945920 |
| chr7 | 121946478 | 121946982 | chr7 | 121947098 | 121947406 | chr7 | 121950137 | 121950264 |
| chr7 | 121950429 | 121950552 | chr7 | 121950995 | 121951069 | chr7 | 121951877 | 121952010 |
| chr7 | 121952044 | 121952169 | chr7 | 121956486 | 121956567 | chr7 | 121956955 | 121957076 |
| chr7 | 121957254 | 121957331 | chr7 | 122526833 | 122526873 | chr7 | 123173150 | 123173244 |
| chr7 | 123672048 | 123672086 | chr7 | 124404415 | 124404497 | chr7 | 126891220 | 126891250 |
| chr7 | 126891504 | 126891593 | chr7 | 126894076 | 126894197 | chr7 | 127371129 | 127371249 |
| chr7 | 127615921 | 127615951 | chr7 | 127744122 | 127744631 | chr7 | 127806634 | 127806664 |
| chr7 | 127807817 | 127807846 | chr7 | 127808047 | 127808792 | chr7 | 127841626 | 127841704 |
| chr7 | 127991826 | 127991922 | chr7 | 127992045 | 127992135 | chr7 | 128097059 | 128097089 |
| chr7 | 128337467 | 128337544 | chr7 | 128337788 | 128337921 | chr7 | 128470897 | 128471032 |
| chr7 | 128486036 | 128486138 | chr7 | 128528749 | 128528779 | chr7 | 128529023 | 128529053 |
| chr7 | 128828195 | 128828272 | chr7 | 129229604 | 129229631 | chr7 | 129418057 | 129418428 |
| chr7 | 129422160 | 129422968 | chr7 | 129423126 | 129423418 | chr7 | 129424655 | 129425887 |
| chr7 | 129426195 | 129426236 | chr7 | 129483356 | 129483449 | chr7 | 129794593 | 129794721 |
| chr7 | 129800243 | 129800434 | chr7 | 129844450 | 129844493 | chr7 | 131041515 | 131041596 |
| chr7 | 131242738 | 131242824 | chr7 | 131514824 | 131514854 | chr7 | 132261272 | 132261432 |
| chr7 | 134143164 | 134143475 | chr7 | 134143807 | 134144132 | chr7 | 134918503 | 134918537 |
| chr7 | 136553311 | 136554025 | chr7 | 136554104 | 136554366 | chr7 | 136554638 | 136554966 |
| chr7 | 136555235 | 136555412 | chr7 | 136555681 | 136555841 | chr7 | 136556013 | 136556091 |
| chr7 | 136969053 | 136969083 | chr7 | 137028481 | 137028524 | chr7 | 137531158 | 137531211 |
| chr7 | 137531263 | 137531888 | chr7 | 137531909 | 137532187 | chr7 | 138042221 | 138042288 |
| chr7 | 138720785 | 138720909 | chr7 | 139167617 | 139167744 | chr7 | 139168115 | 139168379 |
| chr7 | 139208772 | 139208979 | chr7 | 139930051 | 139930270 | chr7 | 139939160 | 139939318 |
| chr7 | 140027008 | 140027079 | chr7 | 140180179 | 140180299 | chr7 | 140218053 | 140218102 |
| chr7 | 140218123 | 140218352 | chr7 | 140219405 | 140219435 | chr7 | 140339952 | 140339982 |
| chr7 | 140453121 | 140453167 | chr7 | 140477779 | 140477868 | chr7 | 140481381 | 140481431 |
| chr7 | 140772795 | 140773228 | chr7 | 140773563 | 140773750 | chr7 | 143042634 | 143042798 |
| chr7 | 143579739 | 143580069 | chr7 | 145812992 | 145813082 | chr7 | 145813412 | 145813494 |
| chr7 | 145813946 | 145814166 | chr7 | 148224584 | 148224686 | chr7 | 148508712 | 148508741 |
| chr7 | 148640211 | 148640250 | chr7 | 148846138 | 148846180 | chr7 | 148851143 | 148851234 |
| chr7 | 149112058 | 149112248 | chr7 | 149119948 | 149120073 | chr7 | 149411541 | 149411727 |
| chr7 | 149411835 | 149412304 | chr7 | 149570368 | 149570406 | chr7 | 149744505 | 149744560 |
| chr7 | 149917322 | 149917336 | chr7 | 149918119 | 149918149 | chr7 | 150038883 | 150038912 |
| chr7 | 150049604 | 150049631 | chr7 | 150069098 | 150069346 | chr7 | 150069679 | 150069820 |
| chr7 | 150070021 | 150070058 | chr7 | 150081236 | 150081308 | chr7 | 150716169 | 150716305 |
| chr7 | 150748192 | 150748406 | chr7 | 150753942 | 150753981 | chr7 | 150870816 | 150870889 |
| chr7 | 151106451 | 151106565 | chr7 | 151106590 | 151106988 | chr7 | 151107486 | 151107651 |
| chr7 | 151188034 | 151188063 | chr7 | 151298870 | 151299029 | chr7 | 151423571 | 151423639 |
| chr7 | 151591667 | 151591705 | chr7 | 152133406 | 152133436 | chr7 | 152622621 | 152622697 |
| chr7 | 152913656 | 152913801 | chr7 | 153583632 | 153584069 | chr7 | 153584389 | 153584623 |
| chr7 | 153584848 | 153585206 | chr7 | 153585602 | 153585606 | chr7 | 153633899 | 153633942 |
| chr7 | 153749720 | 153750042 | chr7 | 154561150 | 154561189 | chr7 | 154708275 | 154708338 |
| chr7 | 154862046 | 154862266 | chr7 | 155164454 | 155165562 | chr7 | 155165875 | 155166784 |
| chr7 | 155167034 | 155167089 | chr7 | 155167175 | 155167660 | chr7 | 155167834 | 155167909 |
| chr7 | 155174656 | 155174788 | chr7 | 155241318 | 155242049 | chr7 | 155242729 | 155243102 |
| chr7 | 155243346 | 155243533 | chr7 | 155243825 | 155243895 | chr7 | 155244180 | 155244361 |
| chr7 | 155246886 | 155247479 | chr7 | 155248913 | 155248943 | chr7 | 155249512 | 155249565 |
| chr7 | 155249925 | 155250011 | chr7 | 155250283 | 155250303 | chr7 | 155250324 | 155250355 |
| chr7 | 155250787 | 155250996 | chr7 | 155251701 | 155251854 | chr7 | 155251891 | 155251939 |
| chr7 | 155252247 | 155252261 | chr7 | 155252317 | 155252490 | chr7 | 155252862 | 155253041 |
| chr7 | 155254848 | 155255324 | chr7 | 155256269 | 155256312 | chr7 | 155257040 | 155257189 |
| chr7 | 155258193 | 155258487 | chr7 | 155258949 | 155259077 | chr7 | 155259120 | 155259622 |
| chr7 | 155259834 | 155259957 | chr7 | 155260039 | 156260137 | chr7 | 155260880 | 155260890 |
| chr7 | 155261071 | 155261210 | chr7 | 155301838 | 155301931 | chr7 | 155302328 | 155302895 |
| chr7 | 155302964 | 155303335 | chr7 | 155325796 | 155325872 | chr7 | 155326169 | 155326527 |
| chr7 | 155363304 | 155363417 | chr7 | 155580182 | 155580211 | chr7 | 155580846 | 155580876 |
| chr7 | 155581330 | 155581553 | chr7 | 155581765 | 155581980 | chr7 | 155582277 | 155582340 |
| chr7 | 155600629 | 155600723 | chr7 | 155602751 | 155602805 | chr7 | 156259192 | 156259221 |
| chr7 | 156409144 | 156409347 | chr7 | 156409728 | 156409802 | chr7 | 156701846 | 156701908 |
| chr7 | 156744696 | 156744713 | chr7 | 156794464 | 156794485 | chr7 | 156794998 | 156795354 |
| chr7 | 156795402 | 156795635 | chr7 | 156795900 | 156795914 | chr7 | 156796534 | 156796739 |
| chr7 | 156797006 | 156798434 | chr7 | 156798527 | 156799146 | chr7 | 156799291 | 156799467 |
| chr7 | 156800999 | 156801029 | chr7 | 156801403 | 156801601 | chr7 | 156808858 | 156809199 |
| chr7 | 156809983 | 156810521 | chr7 | 156810598 | 156810800 | chr7 | 156811303 | 156811436 |
| chr7 | 156812852 | 156813825 | chr7 | 156813987 | 156814707 | chr7 | 156814784 | 156815092 |
| chr7 | 156832223 | 156832402 | chr7 | 156832848 | 156833162 | chr7 | 156871283 | 156871297 |
| chr7 | 156880531 | 156880561 | chr7 | 157085373 | 157085487 | chr7 | 157085963 | 157086082 |
| chr7 | 157262815 | 157263018 | chr7 | 157263294 | 157263471 | chr7 | 157335172 | 157335202 |
| chr7 | 157361605 | 157361635 | chr7 | 157476879 | 157476973 | chr7 | 157476995 | 157477272 |
| chr7 | 157477473 | 157477488 | chr7 | 157477711 | 157477819 | chr7 | 157481130 | 157481160 |
| chr7 | 157481534 | 157481549 | chr7 | 157481969 | 157482073 | chr7 | 157482492 | 157482667 |
| chr7 | 157483320 | 157483538 | chr7 | 157484877 | 157485277 | chr7 | 157485527 | 157485601 |
| chr7 | 157485650 | 157485705 | chr7 | 157485976 | 157486081 | chr7 | 157486205 | 157486414 |
| chr7 | 157486476 | 157486503 | chr7 | 157584178 | 157584208 | chr7 | 157588586 | 157588791 |
| chr7 | 157606706 | 157606736 | chr7 | 157690056 | 157690086 | chr7 | 158059762 | 158059794 |

TABLE 13-continued

| chr | start | end | chr | start | end | chr | start | end |
|---|---|---|---|---|---|---|---|---|
| chr7 | 158065832 | 158065970 | chr7 | 158298861 | 158299036 | chr7 | 158673836 | 158673942 |
| chr7 | 158741193 | 158741267 | chr7 | 158799762 | 158799791 | chr7 | 158936492 | 158936880 |
| chr7 | 158937203 | 158937374 | chr7 | 158937577 | 158937624 | chr7 | 158938210 | 158938399 |
| chr8 | 686870 | 686884 | chr8 | 687163 | 687217 | chr8 | 687838 | 687975 |
| chr8 | 1085573 | 1085603 | chr8 | 1444165 | 1444205 | chr8 | 1950097 | 1950134 |
| chr8 | 4849141 | 4849177 | chr8 | 4849466 | 4849500 | chr8 | 4850247 | 4850322 |
| chr8 | 4850419 | 4850516 | chr8 | 4851736 | 4851749 | chr8 | 4852021 | 4852118 |
| chr8 | 8681258 | 8681353 | chr8 | 8748422 | 8748713 | chr8 | 8748919 | 8748956 |
| chr8 | 9722850 | 9722896 | chr8 | 9756051 | 9756283 | chr8 | 9760735 | 9761155 |
| chr8 | 9762586 | 9762689 | chr8 | 9762752 | 9762864 | chr8 | 9763143 | 9763275 |
| chr8 | 9763895 | 9764049 | chr8 | 9764196 | 9764214 | chr8 | 9764434 | 9764551 |
| chr8 | 10587589 | 10587602 | chr8 | 10652917 | 10652937 | chr8 | 10980452 | 10980491 |
| chr8 | 11204479 | 11204509 | chr8 | 11204810 | 11204905 | chr8 | 11536827 | 11536857 |
| chr8 | 11537225 | 11537259 | chr8 | 11554885 | 11554915 | chr8 | 11555152 | 11555166 |
| chr8 | 11555474 | 11555521 | chr8 | 11559759 | 11559794 | chr8 | 11560068 | 11560375 |
| chr8 | 11560711 | 11560793 | chr8 | 11561442 | 11562169 | chr8 | 11562422 | 11562485 |
| chr8 | 11562701 | 11562917 | chr8 | 11706960 | 11706136 | chr8 | 11706580 | 11706613 |
| chr8 | 11726469 | 11726512 | chr8 | 12990386 | 12990431 | chr8 | 12990664 | 12990784 |
| chr8 | 13319931 | 13319961 | chr8 | 15094505 | 15094566 | chr8 | 16884182 | 16884239 |
| chr8 | 16885205 | 16885241 | chr8 | 17271091 | 17271119 | chr8 | 19797433 | 19797463 |
| chr8 | 19797939 | 19798019 | chr8 | 20375563 | 20375592 | chr8 | 22089409 | 22089560 |
| chr8 | 22458657 | 22458687 | chr8 | 22562345 | 22562483 | chr8 | 22960648 | 22960723 |
| chr8 | 23020951 | 23021107 | chr8 | 23260683 | 23260870 | chr8 | 23423923 | 23423974 |
| chr8 | 23559385 | 23559601 | chr8 | 23559666 | 23560525 | chr8 | 23563791 | 23564023 |
| chr8 | 23564193 | 23564388 | chr8 | 23564652 | 23564668 | chr8 | 23564703 | 23565024 |
| chr8 | 23566803 | 23566854 | chr8 | 23566901 | 23567213 | chr8 | 23567312 | 23567492 |
| chr8 | 23571681 | 23571973 | chr8 | 23572377 | 23572554 | chr8 | 23584094 | 23584400 |
| chr8 | 23584582 | 23584760 | chr8 | 24770314 | 24770361 | chr8 | 24770414 | 24770581 |
| chr8 | 24771431 | 24771562 | chr8 | 24813188 | 24813287 | chr8 | 24813750 | 24813893 |
| chr8 | 24814011 | 24814407 | chr8 | 24857776 | 24857808 | chr8 | 24858336 | 24858440 |
| chr8 | 24858856 | 24859161 | chr8 | 24859496 | 24859526 | chr8 | 25041746 | 25041864 |
| chr8 | 25042534 | 25042567 | chr8 | 25900408 | 25900692 | chr8 | 25900781 | 25901317 |
| chr8 | 25901540 | 25901765 | chr8 | 25902146 | 25902176 | chr8 | 25902619 | 25902649 |
| chr8 | 25903662 | 25903854 | chr8 | 25904157 | 25904191 | chr8 | 25905096 | 26905126 |
| chr8 | 25905762 | 25905811 | chr8 | 25909197 | 25909597 | chr8 | 26372863 | 26372893 |
| chr8 | 26723985 | 26724080 | chr8 | 30243388 | 30243423 | chr8 | 30475450 | 30475480 |
| chr8 | 30769249 | 30769411 | chr8 | 30770106 | 30770109 | chr8 | 30770158 | 30770188 |
| chr8 | 31496481 | 31496757 | chr8 | 31497024 | 31497152 | chr8 | 31497499 | 31497639 |
| chr8 | 32406598 | 32406914 | chr8 | 33372069 | 33372125 | chr8 | 33457142 | 33457379 |
| chr8 | 35093037 | 35093054 | chr8 | 35093951 | 35093973 | chr8 | 37655476 | 37655517 |
| chr8 | 37655810 | 37655990 | chr8 | 37656050 | 37656081 | chr8 | 37822796 | 37823423 |
| chr8 | 37961878 | 37961902 | chr8 | 38008234 | 38008557 | chr8 | 38020213 | 38020272 |
| chr8 | 38274835 | 38274864 | chr8 | 38323911 | 38323941 | chr8 | 38965322 | 38965386 |
| chr8 | 39172082 | 39172134 | chr8 | 41165865 | 41165918 | chr8 | 41166001 | 41166151 |
| chr8 | 41166267 | 41166679 | chr8 | 41166974 | 41166988 | chr8 | 41167026 | 41167035 |
| chr8 | 41424760 | 41424842 | chr8 | 41624826 | 41624855 | chr8 | 41625112 | 41625141 |
| chr8 | 41700665 | 41700751 | chr8 | 41711416 | 41711447 | chr8 | 41733505 | 41733640 |
| chr8 | 41753593 | 41753752 | chr8 | 41754152 | 41754885 | chr8 | 41755178 | 41755208 |
| chr8 | 41910270 | 41910339 | chr8 | 42082721 | 42082798 | chr8 | 42147392 | 42147521 |
| chr8 | 42293633 | 42293722 | chr8 | 42350468 | 42350492 | chr8 | 42749974 | 42750012 |
| chr8 | 47093246 | 47093276 | chr8 | 47334619 | 47334678 | chr8 | 48044710 | 48044753 |
| chr8 | 48100155 | 48100443 | chr8 | 49293364 | 49293524 | chr8 | 49293581 | 49293614 |
| chr8 | 49468669 | 49469127 | chr8 | 49572029 | 49572058 | chr8 | 49783041 | 49783283 |
| chr8 | 49836145 | 49836174 | chr8 | 49959230 | 49959260 | chr8 | 50822179 | 50822308 |
| chr8 | 50822686 | 50822734 | chr8 | 50823452 | 50823562 | chr8 | 53322495 | 53322524 |
| chr8 | 53477408 | 53477736 | chr8 | 53478008 | 53478275 | chr8 | 53478480 | 53478720 |
| chr8 | 53851141 | 53851170 | chr8 | 53853811 | 53854509 | chr8 | 54163316 | 54163349 |
| chr8 | 54163674 | 54164126 | chr8 | 54789278 | 54789310 | chr8 | 54789632 | 54789805 |
| chr8 | 54790023 | 54790077 | chr8 | 54790291 | 54790855 | chr8 | 54791898 | 54791945 |
| chr8 | 54792185 | 54792237 | chr8 | 54792634 | 54792670 | chr8 | 54792702 | 54792760 |
| chr8 | 54794217 | 54794327 | chr8 | 54794713 | 54794780 | chr8 | 54794827 | 54794949 |
| chr8 | 54795140 | 54795165 | chr8 | 55366188 | 55366367 | chr8 | 55366952 | 55367641 |
| chr8 | 55370113 | 55370432 | chr8 | 55370568 | 55370713 | chr8 | 55370836 | 55370858 |
| chr8 | 55371178 | 55371375 | chr8 | 55371440 | 55371724 | chr8 | 55371994 | 55372067 |
| chr8 | 55372417 | 55372538 | chr8 | 55379296 | 55379456 | chr8 | 55383183 | 55383237 |
| chr8 | 56013641 | 56013892 | chr8 | 56014157 | 56014184 | chr8 | 56014623 | 56014743 |
| chr8 | 56015038 | 56015052 | chr8 | 56015186 | 56015357 | chr8 | 56015560 | 56015619 |
| chr8 | 56015908 | 56015938 | chr8 | 57025776 | 57025943 | chr8 | 57026168 | 57026213 |
| chr8 | 57026503 | 57026547 | chr8 | 57069553 | 57069737 | chr8 | 57069851 | 57070157 |
| chr8 | 57358465 | 57358661 | chr8 | 57358807 | 57359091 | chr8 | 57359260 | 57359636 |
| chr8 | 57359893 | 57359922 | chr8 | 57360211 | 57360240 | chr8 | 57360570 | 57360625 |
| chr8 | 57360770 | 57360791 | chr8 | 58105946 | 58106115 | chr8 | 58117004 | 58117079 |
| chr8 | 58130364 | 58130574 | chr8 | 58907698 | 58907835 | chr8 | 59058941 | 59059343 |
| chr8 | 59747186 | 59747318 | chr8 | 60032680 | 60032738 | chr8 | 61777575 | 61777699 |
| chr8 | 61789974 | 61790004 | chr8 | 62034029 | 62034059 | chr8 | 62200502 | 62200776 |
| chr8 | 63161658 | 63161800 | chr8 | 65281616 | 65281760 | chr8 | 65281984 | 65282004 |
| chr8 | 65282333 | 65282440 | chr8 | 65282713 | 65282944 | chr8 | 65283042 | 65283341 |
| chr8 | 65283799 | 65284094 | chr8 | 65286056 | 65286066 | chr8 | 65286682 | 65286753 |

TABLE 13-continued

| chr | start | end | chr | start | end | chr | start | end |
|---|---|---|---|---|---|---|---|---|
| chr8 | 65286963 | 65287251 | chr8 | 65289123 | 65289241 | chr8 | 65289614 | 65290681 |
| chr8 | 65291034 | 65291284 | chr8 | 65292185 | 65292727 | chr8 | 65488271 | 65488322 |
| chr8 | 65488661 | 65488697 | chr8 | 65489099 | 65489129 | chr8 | 65492712 | 65492979 |
| chr8 | 65493195 | 65493433 | chr8 | 65494077 | 65494193 | chr8 | 65498566 | 65498584 |
| chr8 | 65498644 | 65498841 | chr8 | 65499757 | 65500015 | chr8 | 65710938 | 65711046 |
| chr8 | 66548717 | 66548759 | chr8 | 66560524 | 66560545 | chr8 | 67025063 | 67025640 |
| chr8 | 67025920 | 67026429 | chr8 | 67026489 | 67026578 | chr8 | 67026812 | 67026990 |
| chr8 | 67344538 | 67344701 | chr8 | 67873327 | 67873421 | chr8 | 67873799 | 67874050 |
| chr8 | 67874165 | 67874672 | chr8 | 67874756 | 67875682 | chr8 | 67940624 | 67940875 |
| chr8 | 68864578 | 68864765 | chr8 | 69242905 | 69242988 | chr8 | 69243285 | 69243902 |
| chrS | 69243964 | 69243994 | chr8 | 69244370 | 69244500 | chr8 | 70744860 | 70744925 |
| chr8 | 70946760 | 70946914 | chr8 | 70947091 | 70947658 | chr8 | 70982263 | 70982566 |
| chr8 | 70982851 | 70983226 | chr8 | 70983504 | 70983869 | chr8 | 70984017 | 70984292 |
| chr8 | 70984344 | 70984661 | chr8 | 70984745 | 70984978 | chr8 | 71308096 | 71308126 |
| chr8 | 71447529 | 71447559 | chr8 | 72273998 | 72274033 | chr8 | 72468569 | 72469574 |
| chr8 | 72470399 | 72470441 | chr8 | 72471053 | 72471083 | chr8 | 72754491 | 72754609 |
| chr8 | 72754821 | 72755176 | chr8 | 72755666 | 72755814 | chr8 | 72756656 | 72756896 |
| chr8 | 72917335 | 72917428 | chr8 | 72987600 | 72988036 | chr8 | 73163860 | 73164180 |
| chr8 | 73450064 | 73450100 | chr8 | 73450515 | 73450559 | chr8 | 74759385 | 74759463 |
| chr8 | 74759819 | 74759863 | chr8 | 75896574 | 75897337 | chr8 | 76316329 | 76316452 |
| chr8 | 77585219 | 77585698 | chr8 | 77586175 | 77586278 | chr8 | 77586563 | 77586617 |
| chr8 | 77590239 | 77590466 | chr8 | 77593110 | 77593376 | chr8 | 77593889 | 77594124 |
| chr8 | 77594648 | 77594674 | chr8 | 77594758 | 77594993 | chr8 | 77595339 | 77595494 |
| chr8 | 79428297 | 79428401 | chr8 | 80523983 | 80524029 | chr8 | 80524253 | 80524318 |
| chr8 | 80524946 | 80525020 | chr8 | 80525604 | 80525733 | chr8 | 80695902 | 80695932 |
| chr8 | 80803673 | 80803872 | chr8 | 81398018 | 81398155 | chr8 | 81398428 | 81399496 |
| chr8 | 81414737 | 81414831 | chr8 | 81478185 | 81478350 | chr8 | 85095482 | 85095668 |
| chr8 | 85096583 | 85096724 | chr8 | 85097063 | 85097220 | chr8 | 86350553 | 86350566 |
| chr8 | 86406813 | 86406849 | chr8 | 86436621 | 86436651 | chr8 | 86544756 | 86544798 |
| chr8 | 89339389 | 89339745 | chr8 | 89340274 | 89340345 | chr8 | 90913516 | 90913653 |
| chr8 | 91094221 | 91094251 | chr8 | 91803676 | 91803718 | chr8 | 91804065 | 91804253 |
| chr8 | 91997046 | 91997508 | chr8 | 91997528 | 91997947 | chr8 | 92083523 | 92083667 |
| chr8 | 93114135 | 93114241 | chr8 | 93114307 | 93114528 | chr8 | 95485999 | 95486029 |
| chr8 | 95651098 | 95651218 | chr8 | 95651538 | 95651655 | chr8 | 96219882 | 96219901 |
| chr8 | 96285420 | 96285457 | chr8 | 97157085 | 97157209 | chr8 | 97157667 | 97157897 |
| chr8 | 97158022 | 97158066 | chr8 | 97165644 | 97165676 | chr8 | 97166425 | 97166455 |
| chr8 | 97167178 | 97167223 | chr8 | 97167811 | 97167855 | chr8 | 97169838 | 97169955 |
| chr8 | 97170054 | 97170334 | chr8 | 97170867 | 97170897 | chr8 | 97171129 | 97171264 |
| chr8 | 97171318 | 97171958 | chr8 | 97172019 | 97172200 | chr8 | 97172433 | 97172739 |
| chr8 | 97172822 | 97173458 | chr8 | 97173822 | 97173863 | chr8 | 97173921 | 97173935 |
| chr8 | 97339846 | 97340195 | chr8 | 97506034 | 97506048 | chr8 | 97506178 | 97506407 |
| chr8 | 97506448 | 97506524 | chr8 | 97502115 | 97507284 | chr8 | 97507546 | 97507680 |
| chr8 | 98289825 | 98289867 | chr8 | 98289923 | 98290260 | chr8 | 98744202 | 98744234 |
| chr8 | 99234962 | 99235037 | chr8 | 99439104 | 99439133 | chr8 | 99439382 | 99440354 |
| chr8 | 99951404 | 99951434 | chr8 | 99951836 | 99952143 | chr8 | 99952199 | 99952303 |
| chr8 | 99952533 | 99952815 | chr8 | 99954490 | 99954562 | chr8 | 99954679 | 99954727 |
| chr8 | 99955180 | 99955327 | chr8 | 99959429 | 99959549 | chr8 | 99960329 | 99960497 |
| chr8 | 99960922 | 99960971 | chr8 | 99961792 | 99961822 | chr8 | 99985866 | 99986043 |
| chr8 | 99986226 | 99986526 | chr8 | 99986792 | 99987014 | chr8 | 101118241 | 101118490 |
| chr8 | 101661920 | 101661991 | chr8 | 101821973 | 101822047 | chr8 | 101920382 | 101920468 |
| chr8 | 102504464 | 102504506 | chr8 | 102505512 | 102505556 | chr8 | 102505797 | 102505985 |
| chr8 | 103629856 | 103629882 | chr8 | 104153202 | 104153246 | chr8 | 104153449 | 104153561 |
| chr8 | 104383700 | 104383985 | chr8 | 104512123 | 104513186 | chr8 | 104513462 | 104513926 |
| chr8 | 105235369 | 105235501 | chr8 | 105235644 | 105235803 | chr8 | 105235864 | 105236054 |
| chr8 | 105478725 | 105478779 | chr8 | 105479404 | 105479464 | chr8 | 106331160 | 106331237 |
| chr8 | 106332104 | 106332202 | chr8 | 107282163 | 107282195 | chr8 | 107284038 | 107284075 |
| chr8 | 108509543 | 108509697 | chr8 | 109093679 | 109094180 | chr8 | 109094485 | 109094595 |
| chr8 | 109094840 | 109095436 | chr8 | 109095506 | 109095932 | chr8 | 109799588 | 109799739 |
| chr8 | 110275006 | 110275023 | chr8 | 110406028 | 110406106 | chr8 | 110592198 | 110592228 |
| chr8 | 110704001 | 110704144 | chr8 | 110986443 | 110986682 | chr8 | 114444580 | 114445192 |
| chr8 | 114445763 | 114446068 | chr8 | 114446405 | 114446435 | chr8 | 114446931 | 114447368 |
| chr8 | 114449039 | 114449257 | chr8 | 114449550 | 114449602 | chr8 | 116660527 | 116660571 |
| chr8 | 116660616 | 116660760 | chr8 | 117950438 | 117950468 | chr8 | 117950783 | 117950914 |
| chr8 | 118532128 | 118532150 | chr8 | 120219912 | 120219941 | chr8 | 120220116 | 120220145 |
| chr8 | 120220428 | 120220592 | chr8 | 120650979 | 120651008 | chr8 | 120651221 | 120651412 |
| chr8 | 120844095 | 120844130 | chr8 | 121136879 | 121137748 | chr8 | 121823901 | 121823930 |
| chr8 | 121824203 | 121824481 | chr8 | 121825455 | 121825484 | chr8 | 122347026 | 122347052 |
| chr8 | 122651872 | 122651905 | chr8 | 123695532 | 123695660 | chr8 | 124055236 | 124055256 |
| chr8 | 124173246 | 124173501 | chr8 | 124332846 | 124332875 | chr8 | 125411827 | 125411857 |
| chr8 | 125452366 | 125452394 | chr8 | 126007961 | 126008051 | chr8 | 126044442 | 126044563 |
| chr8 | 127569621 | 127569676 | chr8 | 128403354 | 128403383 | chr8 | 128745542 | 128745618 |
| chr8 | 128808002 | 128808077 | chr8 | 128872385 | 128872415 | chr8 | 128889324 | 128889422 |
| chr8 | 128931133 | 128931261 | chr8 | 130369274 | 130369364 | chr8 | 132052147 | 132052299 |
| chr8 | 132052399 | 132052515 | chr8 | 132052590 | 132053164 | chr8 | 132053715 | 132054583 |
| chr8 | 132054594 | 132054785 | chr8 | 133686745 | 133686836 | chr8 | 139508757 | 139508946 |
| chr8 | 139509741 | 139509928 | chr8 | 140714570 | 140714877 | chr8 | 140715090 | 140715094 |
| chr8 | 140715469 | 140715587 | chr8 | 140715965 | 140716021 | chr8 | 140716340 | 140716354 |
| chr8 | 140755383 | 140755550 | chr8 | 140834237 | 140834321 | chr8 | 140963292 | 140963362 |

TABLE 13-continued

| chr | start | end | chr | start | end | chr | start | end |
|---|---|---|---|---|---|---|---|---|
| chr8 | 141054845 | 141054875 | chr8 | 141159919 | 141159949 | chr8 | 141588056 | 141588132 |
| chr8 | 141596886 | 141597022 | chr8 | 141614252 | 141614287 | chr8 | 142265206 | 142265243 |
| chr8 | 142282078 | 142282202 | chr8 | 142292552 | 142292774 | chr8 | 142318155 | 142318184 |
| chr8 | 142361233 | 142361487 | chr8 | 142367368 | 142367790 | chr8 | 142444600 | 142444752 |
| chr8 | 142528400 | 142528402 | chr8 | 142528455 | 142528606 | chr8 | 142528671 | 142528781 |
| chr8 | 142528835 | 142528961 | chr8 | 142535343 | 142535496 | chr8 | 142568598 | 142568652 |
| chr8 | 142632436 | 142632465 | chr8 | 142694847 | 142694953 | chr8 | 142984512 | 142984666 |
| chr8 | 143082777 | 143082810 | chr8 | 143089030 | 143089100 | chr8 | 143105244 | 143105377 |
| chr8 | 143368318 | 143368469 | chr8 | 143509457 | 143509594 | chr8 | 143532122 | 143532509 |
| chr8 | 143532542 | 143532846 | chr8 | 143533611 | 143533640 | chr8 | 143533709 | 143533906 |
| chr8 | 143557980 | 143558080 | chr8 | 143558472 | 143558604 | chr8 | 143587331 | 143587382 |
| chr8 | 143592664 | 143592687 | chr8 | 143611232 | 143611262 | chr8 | 143621980 | 143622096 |
| chr8 | 143702052 | 143702101 | chr8 | 143819384 | 143819406 | chr8 | 143858522 | 143858699 |
| chr8 | 143859338 | 143859361 | chr8 | 143876928 | 143876958 | chr8 | 143993974 | 143994165 |
| chr8 | 144069546 | 144069651 | chr8 | 144190378 | 144190432 | chr8 | 144203653 | 144203708 |
| chr8 | 144203977 | 144204021 | chr8 | 144226174 | 144226204 | chr8 | 144238822 | 144238901 |
| chr8 | 144241250 | 144241287 | chr8 | 144241871 | 144242356 | chr8 | 144303562 | 144303592 |
| chr8 | 144328321 | 144328565 | chr8 | 144330287 | 144330380 | chr8 | 144344293 | 144344442 |
| chr8 | 144347719 | 144347740 | chr8 | 144359977 | 144360076 | chr8 | 144360394 | 144360453 |
| chr8 | 144361758 | 144361823 | chr8 | 144372473 | 144372503 | chr8 | 144382679 | 144382697 |
| chr8 | 144421487 | 144421517 | chr8 | 144509325 | 144510529 | chr8 | 144511225 | 144511424 |
| chr8 | 144512041 | 144512192 | chr8 | 144512473 | 144512503 | chr8 | 144557003 | 144557088 |
| chr8 | 144601799 | 144601851 | chr8 | 144617065 | 144617206 | chr8 | 144650594 | 144650730 |
| chr8 | 144668566 | 144668667 | chr8 | 144668909 | 144668972 | chr8 | 145033304 | 145033333 |
| chr8 | 145218226 | 145218301 | chr8 | 145223902 | 145224061 | chr8 | 145753517 | 145753547 |
| chr8 | 145758572 | 145758692 | chr8 | 145806258 | 145806271 | chr8 | 145925461 | 145925491 |
| chr8 | 145925947 | 145926068 | chr8 | 146013617 | 146013647 | chr8 | 146079215 | 146079297 |
| chr9 | 113433 | 113512 | chr9 | 113550 | 113556 | chr9 | 113850 | 113885 |
| chr9 | 117884 | 117959 | chr9 | 841691 | 842031 | chr9 | 842208 | 842230 |
| chr9 | 842611 | 842673 | chr9 | 969556 | 969586 | chr9 | 969788 | 969846 |
| chr9 | 970096 | 970104 | chr9 | 970186 | 970225 | chr9 | 970495 | 970525 |
| chr9 | 970897 | 970911 | chr9 | 970993 | 971175 | chr9 | 972307 | 972759 |
| chr9 | 973184 | 973289 | chr9 | 974514 | 974547 | chr9 | 975117 | 975167 |
| chr9 | 975783 | 976321 | chr9 | 976618 | 976689 | chr9 | 976912 | 976961 |
| chr9 | 981797 | 981830 | chr9 | 1042402 | 1042500 | chr9 | 1042616 | 1042986 |
| chr9 | 1051905 | 1052166 | chr9 | 2115824 | 2115981 | chr9 | 3181752 | 3181869 |
| chr9 | 5070006 | 5070050 | chr9 | 5073756 | 5073788 | chr9 | 5078346 | 5078375 |
| chr9 | 5089711 | 5089740 | chr9 | 6412571 | 6412809 | chr9 | 6644297 | 6644367 |
| chr9 | 6644540 | 6644554 | chr9 | 6645017 | 6645333 | chr9 | 6645625 | 6645700 |
| chr9 | 6756353 | 6756458 | chr9 | 13278818 | 13278864 | chr9 | 14312994 | 14313096 |
| chr9 | 14313319 | 14313785 | chr9 | 14347633 | 14347673 | chr9 | 14348314 | 14348452 |
| chr9 | 17906404 | 17906432 | chr9 | 17906461 | 17906694 | chr9 | 17907004 | 17907061 |
| chr9 | 17907451 | 17907472 | chr9 | 19789107 | 19789301 | chr9 | 21031734 | 21031836 |
| chr9 | 21402617 | 21403021 | chr9 | 21559294 | 21559381 | chr9 | 21559665 | 21559702 |
| chr9 | 21965057 | 21965424 | chr9 | 21965570 | 21965757 | chr9 | 21968218 | 21968433 |
| chr9 | 21968457 | 21958475 | chr9 | 21970959 | 21971154 | chr9 | 21971185 | 21971220 |
| chr9 | 21974182 | 21974237 | chr9 | 21974499 | 21974794 | chr9 | 21994208 | 21994237 |
| chr9 | 21995297 | 21995326 | chr9 | 21995720 | 21995749 | chr9 | 22006131 | 22006152 |
| chr9 | 22008819 | 22008899 | chr9 | 22447664 | 22447708 | chr9 | 23822568 | 23822606 |
| chr9 | 23824561 | 23824591 | chr9 | 23831100 | 23831370 | chr9 | 29212170 | 29212170 |
| chr9 | 29212211 | 29212294 | chr9 | 29213508 | 29213651 | chr9 | 29214030 | 29214144 |
| chr9 | 29214360 | 29214430 | chr9 | 29214681 | 29215086 | chr9 | 32782630 | 32782935 |
| chr9 | 32783084 | 32783121 | chr9 | 32783346 | 32783419 | chr9 | 32783591 | 32783657 |
| chr9 | 33524609 | 33524687 | chr9 | 33676771 | 33676801 | chr9 | 33677360 | 33677415 |
| chr9 | 34224348 | 34224474 | chr9 | 34372805 | 34372983 | chr9 | 34589062 | 34589156 |
| chr9 | 35617291 | 35617337 | chr9 | 35675539 | 35675647 | chr9 | 35675838 | 35676180 |
| chr9 | 35844834 | 35844863 | chr9 | 36037068 | 36037098 | chr9 | 36318375 | 36318393 |
| chr9 | 36739812 | 36739980 | chr9 | 36832204 | 36832343 | chr9 | 37002454 | 37002517 |
| chr9 | 37002819 | 37003077 | chr9 | 37025564 | 37025783 | chr9 | 37026146 | 37026351 |
| chr9 | 37026434 | 37026622 | chr9 | 37026831 | 37027271 | chr9 | 37027325 | 37027412 |
| chr9 | 37027800 | 37027829 | chr9 | 37028944 | 37029119 | chr9 | 37029534 | 37030655 |
| chr9 | 37034197 | 37034247 | chr9 | 37034616 | 37034731 | chr9 | 37035366 | 37035734 |
| chr9 | 37036425 | 37036647 | chr9 | 37037671 | 37038354 | chr9 | 37467610 | 37467634 |
| chr9 | 38620530 | 38620725 | chr9 | 66456023 | 66456047 | chr9 | 71200632 | 71200662 |
| chr9 | 71734816 | 71734920 | chr9 | 71788952 | 71789260 | chr9 | 71789453 | 71789757 |
| chr9 | 73032801 | 73032831 | chr9 | 74061838 | 74062070 | chr9 | 74210499 | 74210517 |
| chr9 | 74764547 | 74764648 | chr9 | 77112993 | 77113340 | chr9 | 77113559 | 77113708 |
| chr9 | 77113806 | 77113825 | chr9 | 77114745 | 77114851 | chr9 | 77115210 | 77115447 |
| chr9 | 77115657 | 77115687 | chr9 | 79231003 | 79231033 | chr9 | 79626876 | 79627370 |
| chr9 | 79628289 | 79628329 | chr9 | 79629208 | 79629471 | chr9 | 79629879 | 79630420 |
| chr9 | 79631192 | 79631335 | chr9 | 79631555 | 79631591 | chr9 | 79631865 | 79632182 |
| chr9 | 79632860 | 79632890 | chr9 | 79633397 | 79633904 | chr9 | 79634170 | 79634987 |
| chr9 | 79635047 | 79635448 | chr9 | 79635746 | 79636043 | chr9 | 79636258 | 79637274 |
| chr9 | 79637643 | 79637888 | chr9 | 79638137 | 79638244 | chr9 | 80409473 | 80409502 |
| chr9 | 80833933 | 80834011 | chr9 | 85677905 | 85677992 | chr9 | 86152387 | 86152417 |
| chr9 | 86578079 | 86578103 | chr9 | 86755532 | 86755952 | chr9 | 86886706 | 86886736 |
| chr9 | 87283008 | 87283038 | chr9 | 87283677 | 87283709 | chr9 | 87284706 | 87284798 |
| chr9 | 87285279 | 87285472 | chr9 | 88137524 | 88137725 | chr9 | 88137875 | 88137998 |

TABLE 13-continued

| chr | start | end | chr | start | end | chr | start | end |
|---|---|---|---|---|---|---|---|---|
| chr9 | 88694345 | 88694438 | chr9 | 89560760 | 89560827 | chr9 | 89561063 | 89561109 |
| chr9 | 91150222 | 91150335 | chr9 | 91606004 | 91606058 | chr9 | 91792357 | 91792387 |
| chr9 | 91792776 | 91792907 | chr9 | 91793177 | 91793526 | chr9 | 93698029 | 93698051 |
| chr9 | 94183870 | 94183954 | chr9 | 94572641 | 94572743 | chr9 | 95417551 | 95417651 |
| chr9 | 95560810 | 95560840 | chr9 | 95569759 | 95569822 | chr9 | 95570247 | 95570434 |
| chr9 | 95571617 | 95571659 | chr9 | 95571719 | 95571760 | chr9 | 95947130 | 95947296 |
| chr9 | 96588858 | 96588885 | chr9 | 96710377 | 96710407 | chr9 | 96710647 | 96710991 |
| chr9 | 96711258 | 96711446 | chr9 | 96711535 | 96711617 | chr9 | 96711975 | 96712005 |
| chr9 | 96713378 | 96713893 | chr9 | 96715095 | 96715372 | chr9 | 96715688 | 96715857 |
| chr9 | 96716905 | 96717427 | chr9 | 96717450 | 96717466 | chr9 | 96717979 | 96718149 |
| chr9 | 96720803 | 96720885 | chr9 | 96721103 | 96721467 | chr9 | 96721689 | 96721802 |
| chr9 | 96722445 | 96722547 | chr9 | 96723093 | 96723159 | chr9 | 96723171 | 96723202 |
| chr9 | 97845915 | 97845947 | chr9 | 98111365 | 98111560 | chr9 | 98111895 | 98112157 |
| chr9 | 98112344 | 98112395 | chr9 | 98784772 | 98784802 | chr9 | 98789651 | 98790000 |
| chr9 | 99146020 | 99146153 | chr9 | 99259362 | 99259405 | chr9 | 99449135 | 99449451 |
| chr9 | 99639621 | 99639942 | chr9 | 99983140 | 99983170 | chr9 | 99983411 | 99983738 |
| chr9 | 99983798 | 99983824 | chr9 | 99984026 | 99984044 | chr9 | 100397979 | 100398016 |
| chr9 | 100503625 | 100503937 | chr9 | 100609991 | 100610134 | chr9 | 100610201 | 100610218 |
| chr9 | 100610681 | 100610816 | chr9 | 100611125 | 100611640 | chr9 | 100613828 | 100613999 |
| chr9 | 100614193 | 100614325 | chr9 | 100614541 | 100616035 | chr9 | 100616271 | 100616468 |
| chr9 | 100617293 | 100617365 | chr9 | 100617682 | 100618055 | chr9 | 100619722 | 100620069 |
| chr9 | 100620330 | 100620783 | chr9 | 100818336 | 100818437 | chr9 | 100835849 | 100835870 |
| chr9 | 101469269 | 101469307 | chr9 | 101469603 | 101469795 | chr9 | 101470116 | 101470250 |
| chr9 | 101470990 | 101471071 | chr9 | 101471570 | 101471621 | chr9 | 101471860 | 101472009 |
| chr9 | 101705996 | 101706195 | chr9 | 101706313 | 101706695 | chr9 | 103174705 | 103174730 |
| chr9 | 104248579 | 104248623 | chr9 | 104249475 | 104249562 | chr9 | 104500625 | 104500774 |
| chr9 | 110126074 | 110126247 | chr9 | 110228200 | 110228602 | chr9 | 110251388 | 110251418 |
| chr9 | 110252363 | 110252515 | chr9 | 112403170 | 112403200 | chr9 | 112403364 | 112403394 |
| chr9 | 113341522 | 113341621 | chr9 | 113341680 | 113341847 | chr9 | 113341927 | 113341965 |
| chr9 | 113342299 | 113342340 | chr9 | 115067932 | 115067959 | chr9 | 115478932 | 115478971 |
| chr9 | 115652966 | 115653425 | chr9 | 116633883 | 116633905 | chr9 | 117050981 | 117051030 |
| chr9 | 118917024 | 118917079 | chr9 | 120175795 | 120175832 | chr9 | 120176104 | 120176151 |
| chr9 | 120176867 | 120176897 | chr9 | 122131497 | 122131642 | chr9 | 122131880 | 122132025 |
| chr9 | 122132052 | 122132227 | chr9 | 123004898 | 123004928 | chr9 | 123295355 | 123295463 |
| chr9 | 124535347 | 124535611 | chr9 | 124749865 | 124749953 | chr9 | 124751485 | 124751515 |
| chr9 | 125676723 | 125676753 | chr9 | 126133778 | 126133856 | chr9 | 126154304 | 126154575 |
| chr9 | 126349038 | 126349104 | chr9 | 126770257 | 126770298 | chr9 | 126771532 | 126771705 |
| chr9 | 126774517 | 126774619 | chr9 | 126775530 | 126775560 | chr9 | 126776044 | 126776098 |
| chr9 | 126777529 | 126777746 | chr9 | 126777974 | 126777982 | chr9 | 126278359 | 126778496 |
| chr9 | 126779485 | 126780043 | chr9 | 126780285 | 126780315 | chr9 | 126780811 | 126780898 |
| chr9 | 126783295 | 126783499 | chr9 | 127212851 | 127213006 | chr9 | 127265876 | 127266025 |
| chr9 | 127266387 | 127266534 | chr9 | 127920543 | 127920572 | chr9 | 128635180 | 128635210 |
| chr9 | 128652200 | 128652232 | chr9 | 128759852 | 128759954 | chr9 | 129276718 | 129276820 |
| chr9 | 129372929 | 129373037 | chr9 | 129376170 | 129376199 | chr9 | 129376889 | 129376918 |
| chr9 | 129377214 | 129377316 | chr9 | 129377604 | 129377635 | chr9 | 129377773 | 129377959 |
| chr9 | 129387434 | 129387464 | chr9 | 129387848 | 129388200 | chr9 | 129388719 | 129388753 |
| chr9 | 129388996 | 129389192 | chr9 | 129400986 | 129401195 | chr9 | 129445255 | 129445566 |
| chr9 | 129445783 | 129445813 | chr9 | 129517783 | 129517821 | chr9 | 130248419 | 130248449 |
| chr9 | 130461687 | 130461742 | chr9 | 130675509 | 130675592 | chr9 | 130689631 | 130689667 |
| chr9 | 130689742 | 130689749 | chr9 | 131580038 | 131580118 | chr9 | 131607517 | 131607547 |
| chr9 | 131607770 | 131607800 | chr9 | 131854231 | 131854328 | chr9 | 131854708 | 131854732 |
| chr9 | 132373058 | 132373091 | chr9 | 132382635 | 132383109 | chr9 | 132383347 | 132383376 |
| chr9 | 132402840 | 132402883 | chr9 | 132403149 | 132403216 | chr9 | 132559377 | 132559417 |
| chr9 | 132804405 | 132804455 | chr9 | 132804796 | 132804974 | chr9 | 132805318 | 132805445 |
| chr9 | 132805737 | 132805893 | chr9 | 132881814 | 132881844 | chr9 | 133308893 | 133308941 |
| chr9 | 133534683 | 133534713 | chr9 | 133535734 | 133535839 | chr9 | 133536097 | 133536119 |
| chr9 | 133536150 | 133536344 | chr9 | 133536778 | 133536869 | chr9 | 133537182 | 133537549 |
| chr9 | 133538169 | 133538728 | chr9 | 133539606 | 133539709 | chr9 | 133541059 | 133541192 |
| chr9 | 133541689 | 133542337 | chr9 | 133738343 | 133738372 | chr9 | 133747505 | 133747534 |
| chr9 | 133773766 | 133773923 | chr9 | 133927347 | 133927481 | chr9 | 133928236 | 133928266 |
| chr9 | 134126670 | 134126741 | chr9 | 134191085 | 134191218 | chr9 | 134207916 | 134208012 |
| chr9 | 134421797 | 134421835 | chr9 | 134717313 | 134717367 | chr9 | 135037119 | 135037287 |
| chr9 | 135037334 | 135037357 | chr9 | 135073463 | 135073506 | chr9 | 135455407 | 135455585 |
| chr9 | 135455996 | 135456023 | chr9 | 135456476 | 135456544 | chr9 | 135456897 | 135456915 |
| chr9 | 135458477 | 135458597 | chr9 | 135460001 | 135460176 | chr9 | 135460869 | 135460899 |
| chr9 | 135461511 | 135461773 | chr9 | 135462048 | 135462077 | chr9 | 135462648 | 135462967 |
| chr9 | 135464798 | 135464918 | chr9 | 135465948 | 135466064 | chr9 | 135466118 | 135466132 |
| chr9 | 135466344 | 135466660 | chr9 | 135648238 | 135548276 | chr9 | 135796801 | 135796830 |
| chr9 | 135865090 | 135865161 | chr9 | 135898911 | 135899124 | chr9 | 136474490 | 136474591 |
| chr9 | 137111397 | 137111426 | chr9 | 137229892 | 137229921 | chr9 | 137299119 | 137299450 |
| chr9 | 137299670 | 137299699 | chr9 | 137534066 | 137534238 | chr9 | 137575915 | 137575945 |
| chr9 | 137656958 | 137657128 | chr9 | 137667327 | 137667357 | chr9 | 137702189 | 137702222 |
| chr9 | 137718901 | 137719001 | chr9 | 137722087 | 137722209 | chr9 | 137979893 | 137980011 |
| chr9 | 137980258 | 137980288 | chr9 | 137980880 | 137980910 | chr9 | 138265123 | 138265251 |
| chr9 | 138563059 | 138563280 | chr9 | 138606821 | 138606923 | chr9 | 138627636 | 138627893 |
| chr9 | 138634047 | 138634159 | chr9 | 138659800 | 138659905 | chr9 | 138660943 | 138661012 |
| chr9 | 138661648 | 138661870 | chr9 | 138666455 | 138666558 | chr9 | 138880711 | 138880875 |
| chr9 | 138991798 | 138991828 | chr9 | 139000566 | 139000642 | chr9 | 139012272 | 139012411 |

TABLE 13-continued

| chr | start | end | chr | start | end | chr | start | end |
|---|---|---|---|---|---|---|---|---|
| chr9 | 139024750 | 139024782 | chr9 | 139045653 | 139045683 | chr9 | 139047532 | 139047633 |
| chr9 | 139085228 | 139085350 | chr9 | 139090500 | 139090551 | chr9 | 139091072 | 139091369 |
| chr9 | 139093773 | 139093890 | chr9 | 139094705 | 139094732 | chr9 | 139095340 | 139095485 |
| chr9 | 139096650 | 139097006 | chr9 | 139111268 | 139111298 | chr9 | 139269039 | 139269121 |
| chr9 | 139399407 | 139399436 | chr9 | 139421955 | 139421985 | chr9 | 139477862 | 139478020 |
| chr9 | 139698925 | 139699051 | chr9 | 139704084 | 139704279 | chr9 | 139859041 | 139859268 |
| chr9 | 139888945 | 139888980 | chr9 | 140024842 | 140024918 | chr9 | 140024957 | 140025023 |
| chr9 | 140030498 | 140030528 | chr9 | 140031944 | 140031983 | chr9 | 140032891 | 140032951 |
| chr9 | 140033001 | 140033092 | chr9 | 140033426 | 140033490 | chr9 | 140033619 | 140033626 |
| chr9 | 140033909 | 140034079 | chr9 | 140060969 | 140051095 | chr9 | 140051220 | 140051354 |
| chr9 | 140127883 | 140128080 | chr9 | 140137310 | 140137339 | chr9 | 140197122 | 140197263 |
| chr9 | 140205394 | 140205519 | chr9 | 140245877 | 140245998 | chr9 | 140332708 | 140333018 |
| chr9 | 140382557 | 140382596 | chr9 | 140392454 | 140392484 | chr9 | 140397029 | 140397097 |
| chr9 | 140507256 | 140507419 | chr9 | 140704046 | 140704131 | chr9 | 140709046 | 140709174 |
| chr9 | 140727471 | 140727511 | chr9 | 140727845 | 140727930 | chr9 | 140769943 | 140769973 |
| chr9 | 140771975 | 140772347 | chr9 | 140772586 | 140772593 | chr9 | 140772757 | 140773301 |
| chr10 | 524754 | 524784 | chr10 | 833307 | 833386 | chr10 | 978878 | 978933 |
| chr10 | 1080415 | 1080513 | chr10 | 1120778 | 1120937 | chr10 | 1577394 | 1577424 |
| chr10 | 1585145 | 1585239 | chr10 | 1651360 | 1651374 | chr10 | 1708327 | 1708478 |
| chr10 | 1774858 | 1774887 | chr10 | 1779417 | 1779744 | chr10 | 3109360 | 3109459 |
| chr10 | 3197004 | 3197113 | chr10 | 3285672 | 3285698 | chr10 | 3330499 | 3330618 |
| chr10 | 3641378 | 3641396 | chr10 | 3678617 | 3678637 | chr10 | 3895410 | 3895452 |
| chr10 | 4599917 | 4599965 | chr10 | 5530764 | 5530975 | chr10 | 5855154 | 5855184 |
| chr10 | 5875140 | 5875358 | chr10 | 6003402 | 6003855 | chr10 | 6042309 | 6042571 |
| chr10 | 6162159 | 6162225 | chr10 | 6206142 | 6206217 | chr10 | 6372343 | 6372373 |
| chr10 | 6513976 | 6514006 | chr10 | 6577643 | 6577673 | chr10 | 6984463 | 6984639 |
| chr10 | 7205733 | 7205787 | chr10 | 7212745 | 7213064 | chr10 | 7213505 | 7213535 |
| chr10 | 7216059 | 7216089 | chr10 | 7236211 | 7236245 | chr10 | 7255730 | 7255821 |
| chr10 | 7323283 | 7323313 | chr10 | 7371678 | 7371708 | chr10 | 7414544 | 7414588 |
| chr10 | 7424626 | 7424687 | chr10 | 7436180 | 7436209 | chr10 | 7449954 | 7450189 |
| chr10 | 7450491 | 7451390 | chr10 | 7452227 | 7452777 | chr10 | 7453313 | 7453656 |
| chr10 | 7453903 | 7453930 | chr10 | 7708274 | 7708304 | chr10 | 7708790 | 7708856 |
| chr10 | 7708955 | 7709087 | chr10 | 7709723 | 7709752 | chr10 | 8055681 | 8055764 |
| chr10 | 8075930 | 8075944 | chr10 | 8076341 | 8076487 | chr10 | 8076804 | 8077374 |
| chr10 | 8077874 | 8078218 | chr10 | 8085039 | 8085721 | chr10 | 8085978 | 8086010 |
| chr10 | 8091895 | 8092278 | chr10 | 8093738 | 8093824 | chr10 | 8093860 | 8093963 |
| chr10 | 8095603 | 8095845 | chr10 | 8096160 | 8096190 | chr10 | 8096975 | 8097197 |
| chr10 | 8097474 | 8097537 | chr10 | 11059933 | 11060062 | chr10 | 11206206 | 11206235 |
| chr10 | 11207179 | 11207276 | chr10 | 11700918 | 11701075 | chr10 | 12390825 | 12390995 |
| chr10 | 12391870 | 12392327 | chr10 | 13043386 | 13043425 | chr10 | 13141001 | 13141020 |
| chr10 | 13715208 | 13715401 | chr10 | 13933005 | 13933035 | chr10 | 13933436 | 13933538 |
| chr10 | 13933597 | 13933934 | chr10 | 13933983 | 13934125 | chr10 | 13934169 | 13934183 |
| chr10 | 14393819 | 14393893 | chr10 | 14966129 | 14966212 | chr10 | 15140505 | 15140526 |
| chr10 | 15761292 | 15761671 | chr10 | 15762124 | 15762154 | chr10 | 16562369 | 16562672 |
| chr10 | 16562710 | 16563664 | chr10 | 16563691 | 16563909 | chr10 | 16564087 | 16564116 |
| chr10 | 16564537 | 16564566 | chr10 | 17269259 | 17269288 | chr10 | 17269628 | 17269789 |
| chr10 | 17270072 | 17270445 | chr10 | 17270991 | 17271254 | chr10 | 17271444 | 17271625 |
| chr10 | 17271914 | 17272233 | chr10 | 17272601 | 17272630 | chr10 | 17273172 | 17273201 |
| chr10 | 17275584 | 17275613 | chr10 | 17277741 | 17277770 | chr10 | 17429165 | 17429244 |
| chr10 | 17429544 | 17429622 | chr10 | 17496545 | 17496734 | chr10 | 18429628 | 18429774 |
| chr10 | 21101525 | 21101555 | chr10 | 21462533 | 21462607 | chr10 | 21462970 | 21463023 |
| chr10 | 21805217 | 21805277 | chr10 | 22047336 | 22047635 | chr10 | 22541638 | 22541850 |
| chr10 | 22542025 | 22542249 | chr10 | 22624022 | 22624305 | chr10 | 22624562 | 22625120 |
| chr10 | 22625383 | 22625782 | chr10 | 22625812 | 22625978 | chr10 | 22633985 | 22634174 |
| chr10 | 22634325 | 22634578 | chr10 | 22764649 | 22765791 | chr10 | 22765821 | 22765901 |
| chr10 | 23216865 | 23216945 | chr10 | 23460355 | 23460471 | chr10 | 23461222 | 23461754 |
| chr10 | 23462059 | 23462462 | chr10 | 23462486 | 23462614 | chr10 | 23462635 | 23462910 |
| chr10 | 23463267 | 23463853 | chr10 | 23463888 | 23464077 | chr10 | 23479876 | 23480696 |
| chr10 | 23480904 | 23481049 | chr10 | 23481321 | 23481515 | chr10 | 23481936 | 23482232 |
| chr10 | 23482289 | 23482445 | chr10 | 23483828 | 23484618 | chr10 | 23486264 | 23486328 |
| chr10 | 23487742 | 23487978 | chr10 | 23488393 | 23489158 | chr10 | 23489409 | 23489439 |
| chr10 | 23982438 | 23982820 | chr10 | 23983194 | 23983247 | chr10 | 23983618 | 23983700 |
| chr10 | 23984087 | 23984226 | chr10 | 23984923 | 23984991 | chr10 | 24988589 | 24988619 |
| chr10 | 25464619 | 25464915 | chr10 | 25465421 | 25465517 | chr10 | 26055811 | 26055841 |
| chr10 | 26223001 | 26223205 | chr10 | 26224031 | 26224061 | chr10 | 26500619 | 26500870 |
| chr10 | 26501539 | 26501589 | chr10 | 26503693 | 26503731 | chr10 | 26504114 | 26504143 |
| chr10 | 26504491 | 26504883 | chr10 | 26505009 | 26505227 | chr10 | 26505442 | 26505617 |
| chr10 | 26506057 | 26506163 | chr10 | 26506373 | 26506618 | chr10 | 26506903 | 26507400 |
| chr10 | 26681099 | 26681129 | chr10 | 26727098 | 26727368 | chr10 | 26727604 | 26727816 |
| chr10 | 26747051 | 26747075 | chr10 | 26816912 | 26816938 | chr10 | 26931897 | 26931926 |
| chr10 | 27547946 | 27548331 | chr10 | 27548401 | 27548484 | chr10 | 27794496 | 27794512 |
| chr10 | 27846637 | 27846727 | chr10 | 28030892 | 28030925 | chr10 | 28032966 | 28033020 |
| chr10 | 28033410 | 28033481 | chr10 | 28033770 | 28034186 | chr10 | 28034327 | 28034341 |
| chr10 | 28034874 | 28035300 | chr10 | 28035615 | 28035782 | chr10 | 28287373 | 28287557 |
| chr10 | 28287777 | 28288070 | chr10 | 28657255 | 28657343 | chr10 | 28958086 | 28958129 |
| chr10 | 29011047 | 29011162 | chr10 | 30026077 | 30026090 | chr10 | 30848200 | 30848230 |
| chr10 | 31073368 | 31073481 | chr10 | 31892922 | 31893079 | chr10 | 32499044 | 32499176 |
| chr10 | 33233313 | 33233361 | chr10 | 33624166 | 33624230 | chr10 | 33624492 | 33624560 |

TABLE 13-continued

| chr | start | end | chr | start | end | chr | start | end |
|---|---|---|---|---|---|---|---|---|
| chr10 | 35929334 | 35929528 | chr10 | 43186151 | 43186181 | chr10 | 43250009 | 43250039 |
| chr10 | 43250406 | 43250779 | chr10 | 43250855 | 43250886 | chr10 | 43428424 | 43428576 |
| chr10 | 43429067 | 43429100 | chr10 | 43429376 | 43429411 | chr10 | 43572685 | 43572734 |
| chr10 | 43600561 | 43600720 | chr10 | 43609055 | 43609117 | chr10 | 43609922 | 43609963 |
| chr10 | 43613890 | 43613919 | chr10 | 43614982 | 43615011 | chr10 | 43615554 | 43615607 |
| chr10 | 43617401 | 43617430 | chr10 | 43697887 | 43698086 | chr10 | 43698115 | 43698155 |
| chr10 | 43858343 | 43858437 | chr10 | 44879944 | 44880228 | chr10 | 44880869 | 44880915 |
| chr10 | 49652977 | 49653080 | chr10 | 49731548 | 49731749 | chr10 | 49732060 | 49732087 |
| chr10 | 49732156 | 49732498 | chr10 | 50323222 | 50323258 | chr10 | 50340119 | 50340149 |
| chr10 | 50507557 | 50507619 | chr10 | 50603967 | 50604159 | chr10 | 50604608 | 50604645 |
| chr10 | 50605057 | 50605654 | chr10 | 50606027 | 50606433 | chr10 | 50817015 | 50817132 |
| chr10 | 50817858 | 50817872 | chr10 | 50818382 | 50818432 | chr10 | 50818987 | 50819102 |
| chr10 | 50821472 | 50821701 | chr10 | 50887655 | 50887753 | chr10 | 50887790 | 50887816 |
| chr10 | 50977034 | 50977048 | chr10 | 52177545 | 52177575 | chr10 | 53107427 | 53107525 |
| chr10 | 54068526 | 54068610 | chr10 | 54072982 | 54073020 | chr10 | 54073265 | 54073295 |
| chr10 | 54074744 | 54074789 | chr10 | 57387429 | 57387796 | chr10 | 57388325 | 57388510 |
| chr10 | 57390290 | 57390637 | chr10 | 57391166 | 57391215 | chr10 | 60273130 | 50273278 |
| chr10 | 60935887 | 60935996 | chr10 | 60936524 | 60936729 | chr10 | 60937073 | 60937103 |
| chr10 | 63212324 | 63212701 | chr10 | 64575526 | 64575638 | chr10 | 64578171 | 64578540 |
| chr10 | 65262111 | 65262148 | chr10 | 70232445 | 70232485 | chr10 | 70275831 | 70275875 |
| chr10 | 70315131 | 70315148 | chr10 | 70586517 | 70586540 | chr10 | 71327725 | 71327764 |
| chr10 | 71328773 | 71328821 | chr10 | 71329079 | 71329118 | chr10 | 71329544 | 71329618 |
| chr10 | 21332052 | 71333018 | chr10 | 72015150 | 72015339 | chr10 | 72043779 | 72043894 |
| chr10 | 72200118 | 72200138 | chr10 | 72200354 | 72200771 | chr10 | 72200825 | 72201285 |
| chr10 | 72973130 | 72973180 | chr10 | 73156362 | 73156661 | chr10 | 73157867 | 73158027 |
| chr10 | 75407570 | 75407837 | chr10 | 75488953 | 75488979 | chr10 | 77190039 | 77190068 |
| chr10 | 77191224 | 77191368 | chr10 | 79396921 | 79397089 | chr10 | 81023884 | 81023914 |
| chr10 | 81154141 | 81154192 | chr10 | 81664867 | 81664899 | chr10 | 82117074 | 82117271 |
| chr10 | 83634261 | 83634361 | chr10 | 83634467 | 83634499 | chr10 | 83635531 | 83635545 |
| chr10 | 85954425 | 85954457 | chr10 | 88123672 | 88123701 | chr10 | 88149363 | 88149601 |
| chr10 | 88304914 | 88304944 | chr10 | 88684005 | 88684034 | chr10 | 89624255 | 89624311 |
| chr10 | 89653788 | 89653859 | chr10 | 89685272 | 89685322 | chr10 | 89690790 | 89690819 |
| chr10 | 89692776 | 89693015 | chr10 | 89711861 | 89711992 | chr10 | 89717610 | 89717744 |
| chr10 | 89720790 | 89720885 | chr10 | 89725030 | 89725071 | chr10 | 90966708 | 90966865 |
| chr10 | 90967671 | 90968040 | chr10 | 91295029 | 91295067 | chr10 | 91295585 | 91295725 |
| chr10 | 92617242 | 92617308 | chr10 | 93647216 | 93647300 | chr10 | 93647562 | 93647648 |
| chr10 | 94450675 | 94450726 | chr10 | 94451448 | 94451602 | chr10 | 94826023 | 94826056 |
| chr10 | 94828194 | 94828498 | chr10 | 94828735 | 94828828 | chr10 | 94834413 | 94835047 |
| chr10 | 95360716 | 95360750 | chr10 | 96304115 | 96304235 | chr10 | 98129822 | 98130033 |
| chr10 | 99080262 | 99080447 | chr10 | 99080862 | 99080930 | chr10 | 99474393 | 99474467 |
| chr10 | 99481826 | 99481905 | chr10 | 99531219 | 99531430 | chr10 | 99789175 | 99789282 |
| chr10 | 99790261 | 99790318 | chr10 | 99790590 | 99790664 | chr10 | 99790947 | 99791161 |
| chr10 | 100991907 | 100991935 | chr10 | 100992055 | 100992190 | chr10 | 100992222 | 100992443 |
| chr10 | 100992882 | 100992916 | chr10 | 100993537 | 100994016 | chr10 | 100996046 | 100996224 |
| chr10 | 101088995 | 101089439 | chr10 | 101089908 | 101090203 | chr10 | 101280204 | 101280485 |
| chr10 | 101283464 | 101283658 | chr10 | 101290117 | 101290160 | chr10 | 101290180 | 101291142 |
| chr10 | 101292297 | 101292919 | chr10 | 101293156 | 101293343 | chr10 | 101294756 | 101295586 |
| chr10 | 101296768 | 101296800 | chr10 | 101874886 | 101875138 | chr10 | 102322230 | 102322260 |
| chr10 | 102419400 | 102419681 | chr10 | 102430699 | 102430761 | chr10 | 102473856 | 102473932 |
| chr10 | 102483993 | 102484245 | chr10 | 102484270 | 102484554 | chr10 | 102495508 | 102495741 |
| chr10 | 102497273 | 102497708 | chr10 | 102498280 | 102498433 | chr10 | 102501359 | 102501389 |
| chr10 | 102507509 | 102507535 | chr10 | 102508996 | 102509285 | chr10 | 102589425 | 102589493 |
| chr10 | 102589786 | 102589915 | chr10 | 102590152 | 102590415 | chr10 | 102890941 | 102891582 |
| chr10 | 102891823 | 102891955 | chr10 | 102893624 | 102893951 | chr10 | 102894091 | 102895289 |
| chr10 | 102899173 | 102899601 | chr10 | 102899807 | 102899855 | chr10 | 102900263 | 102900575 |
| chr10 | 102906525 | 102906620 | chr10 | 102975619 | 102975834 | chr10 | 102976150 | 102976180 |
| chr10 | 102977051 | 102977412 | chr10 | 102983153 | 102983379 | chr10 | 102983435 | 102983749 |
| chr10 | 102984513 | 102984516 | chr10 | 102985772 | 102985963 | chr10 | 102986534 | 102986952 |
| chr10 | 102987207 | 102987558 | chr10 | 102989629 | 102989659 | chr10 | 102996116 | 102996480 |
| chr10 | 102996597 | 102996638 | chr10 | 102997329 | 102997406 | chr10 | 102998576 | 102998828 |
| chr10 | 103043975 | 103044227 | chr10 | 103044301 | 103044366 | chr10 | 103425950 | 103426174 |
| chr10 | 103432412 | 103432441 | chr10 | 103535622 | 103535770 | chr10 | 103536227 | 103536256 |
| chr10 | 103536300 | 103536416 | chr10 | 103579674 | 103579713 | chr10 | 103930128 | 103930161 |
| chr10 | 104170096 | 104170262 | chr10 | 104170408 | 104170732 | chr10 | 105036542 | 105036658 |
| chr10 | 105036701 | 105036863 | chr10 | 105037223 | 105037830 | chr10 | 105127047 | 105127076 |
| chr10 | 105155323 | 105155481 | chr10 | 105413627 | 105413784 | chr10 | 105420861 | 105420891 |
| chr10 | 105527028 | 105527057 | chr10 | 106398644 | 106398687 | chr10 | 106398826 | 106398886 |
| chr10 | 106399581 | 106400387 | chr10 | 106401323 | 106401432 | chr10 | 106401511 | 106402190 |
| chr10 | 106402272 | 106402325 | chr10 | 106402712 | 106402825 | chr10 | 108924045 | 108924059 |
| chr10 | 110671930 | 110672245 | chr10 | 111216789 | 111216803 | chr10 | 112403151 | 112403297 |
| chr10 | 112440378 | 112440408 | chr10 | 115804840 | 115805014 | chr10 | 116164248 | 116164341 |
| chr10 | 116331126 | 116331156 | chr10 | 116853875 | 116853908 | chr10 | 118030642 | 118030705 |
| chr10 | 118031302 | 118031548 | chr10 | 118031625 | 118032229 | chr10 | 118032413 | 118032547 |
| chr10 | 118032917 | 118033140 | chr10 | 118033260 | 118033542 | chr10 | 118034143 | 118034168 |
| chr10 | 118609305 | 118609390 | chr10 | 118890980 | 118891104 | chr10 | 118891517 | 118891661 |
| chr10 | 118891716 | 118891774 | chr10 | 118892013 | 118892456 | chr10 | 118892518 | 118893266 |
| chr10 | 118893680 | 118893825 | chr10 | 118894035 | 118894071 | chr10 | 118896629 | 118896805 |
| chr10 | 118897913 | 118897968 | chr10 | 118899273 | 118899302 | chr10 | 118899583 | 118899602 |

TABLE 13-continued

| chr | start | end | chr | start | end | chr | start | end |
|---|---|---|---|---|---|---|---|---|
| chr10 | 118899893 | 118899957 | chr10 | 118900166 | 118900244 | chr10 | 118900324 | 118900498 |
| chr10 | 118922143 | 118922208 | chr10 | 118922721 | 118922901 | chr10 | 118923138 | 118923259 |
| chr10 | 118924604 | 118924896 | chr10 | 118927086 | 118927296 | chr10 | 118928548 | 118928727 |
| chr10 | 119000690 | 119001154 | chr10 | 119001534 | 119001564 | chr10 | 119294352 | 119294461 |
| chr10 | 119294847 | 119294897 | chr10 | 119294909 | 119295245 | chrl0 | 119296756 | 119296788 |
| chr10 | 119297384 | 119297529 | chr10 | 119301365 | 119301427 | chrl0 | 119302141 | 119302155 |
| chr10 | 119302222 | 119302266 | chr10 | 119302962 | 119303174 | chr10 | 119304363 | 119304393 |
| chr10 | 119304896 | 119304985 | chr10 | 119305062 | 119305109 | chr10 | 119307022 | 119307052 |
| chr10 | 119311867 | 119311897 | chr10 | 119312751 | 119313193 | chr10 | 119590435 | 119590464 |
| chr10 | 119807026 | 119807056 | chr10 | 120354243 | 120354273 | chr10 | 120355548 | 120355614 |
| chr10 | 120800789 | 120800835 | chr10 | 120841558 | 120841574 | chr10 | 121267480 | 121267523 |
| chr10 | 122216896 | 122217083 | chr10 | 122708495 | 122708691 | chr10 | 122708992 | 122709022 |
| chr10 | 123256044 | 123256232 | chr10 | 123258020 | 123258091 | chr10 | 123274758 | 123274787 |
| chr10 | 123279548 | 123279697 | chr10 | 123357206 | 123357242 | chr10 | 123357766 | 123357893 |
| chr10 | 123922645 | 123922682 | chr10 | 124893178 | 124893192 | chr10 | 124893238 | 124893350 |
| chr10 | 124893635 | 124893765 | chr10 | 124893965 | 124894479 | chr10 | 124894889 | 124894922 |
| chr10 | 124895426 | 124895695 | chr10 | 124895833 | 124896456 | chr10 | 124897220 | 124897657 |
| chr10 | 124897957 | 124897973 | chr10 | 124899035 | 124899116 | chr10 | 124899754 | 124899786 |
| chr10 | 124901892 | 124902046 | chr10 | 124902139 | 124902568 | chr10 | 124902608 | 124903238 |
| chr10 | 124904921 | 124905119 | chr10 | 124905481 | 124905511 | chr10 | 124905920 | 124906174 |
| chr10 | 124906436 | 124906544 | chr10 | 124907312 | 124907534 | chr10 | 124908091 | 124908121 |
| chr10 | 124909086 | 124909114 | chr10 | 124909253 | 124909537 | chr10 | 124909674 | 124909725 |
| chr10 | 124910363 | 124910454 | chr10 | 124910709 | 124911048 | chr10 | 125425515 | 125425547 |
| chr10 | 125650866 | 125651162 | chr10 | 125851328 | 125851645 | chr10 | 125852299 | 125852497 |
| chr10 | 125852753 | 125853191 | chr10 | 126101966 | 126102001 | chr10 | 126135927 | 126136065 |
| chr10 | 126136506 | 126136723 | chr10 | 126137181 | 126137405 | chr10 | 126198949 | 126199077 |
| chr10 | 126697828 | 126698107 | chr10 | 126782965 | 126783048 | chr10 | 126828994 | 126829024 |
| chr10 | 128076561 | 128076630 | chr10 | 128993904 | 128994446 | chr10 | 128994727 | 128994903 |
| chr10 | 129379338 | 129379367 | chr10 | 129534993 | 129535446 | chr10 | 129535696 | 129535733 |
| chr10 | 129536080 | 129536223 | chr10 | 129536259 | 129536310 | chr10 | 129888804 | 129888885 |
| chr10 | 129948111 | 129948140 | chr10 | 130085356 | 130085362 | chr10 | 130203435 | 130203480 |
| chrl0 | 130338727 | 130338768 | chr10 | 130338804 | 130338976 | chr10 | 130577764 | 130577794 |
| chr10 | 131348513 | 131348713 | chr10 | 131647903 | 131647933 | chr10 | 131761378 | 131761441 |
| chr10 | 131761687 | 131761725 | chr10 | 131762087 | 131762124 | chr10 | 131762592 | 131762631 |
| chr10 | 131762904 | 131762940 | chr10 | 131763633 | 131763717 | chr10 | 131767372 | 131767503 |
| chr10 | 131767543 | 131767649 | chr10 | 131768724 | 131769029 | chr10 | 131769533 | 131770237 |
| chr10 | 131770657 | 131770687 | chr10 | 131770988 | 131771093 | chr10 | 131936599 | 131936626 |
| chr10 | 131937392 | 131937428 | chr10 | 132001252 | 132001556 | chr10 | 133109192 | 133109260 |
| chr10 | 133110554 | 133110704 | chr10 | 133794883 | 133795241 | chr10 | 133795313 | 133795430 |
| chr10 | 133795682 | 133795883 | chr10 | 133795976 | 133796058 | chr10 | 133849598 | 133850008 |
| chr10 | 133850529 | 133850774 | chr10 | 133951602 | 133952025 | chr10 | 133979059 | 133979089 |
| chr10 | 134000008 | 134000052 | chr10 | 134000109 | 134000124 | chr10 | 134001140 | 134001260 |
| chr10 | 134016203 | 134016388 | chr10 | 134022845 | 134022875 | chr10 | 134039087 | 134039117 |
| chr10 | 134095594 | 134095833 | chr10 | 134119401 | 134119447 | chr10 | 134121401 | 134121430 |
| chr10 | 134273064 | 134273156 | chr10 | 134301095 | 134301212 | chr10 | 134481320 | 134481433 |
| chr10 | 134491021 | 134491114 | chr10 | 134499773 | 134499803 | chr10 | 134593329 | 134593416 |
| chr10 | 134598087 | 134598090 | chr10 | 134598368 | 134598530 | chr10 | 134599432 | 134599482 |
| chr10 | 134599808 | 134600016 | chr10 | 134600038 | 134600998 | chr10 | 134601556 | 134601715 |
| chr10 | 134602183 | 134602269 | chr10 | 134607970 | 134608183 | chr10 | 134665147 | 134665202 |
| chr10 | 134679129 | 134679265 | chr10 | 134690559 | 134690617 | chr10 | 134693587 | 134693709 |
| chr10 | 134699872 | 134699909 | chr10 | 134733221 | 134733275 | chr10 | 134733497 | 134733617 |
| chr10 | 134738378 | 134738642 | chr10 | 134755773 | 134756183 | chr10 | 134788083 | 134788251 |
| chr10 | 134796012 | 134796042 | chr10 | 134896060 | 134896092 | chr10 | 134901193 | 134901511 |
| chr10 | 134902008 | 134902124 | chr10 | 134902188 | 134902307 | chr10 | 134916714 | 134916774 |
| chr10 | 134941145 | 134941178 | chr10 | 134942840 | 134943114 | chr10 | 134943445 | 134943542 |
| chr10 | 134944742 | 134944772 | chr10 | 135002063 | 135002156 | chr10 | 135014963 | 135015132 |
| chr10 | 135017049 | 135017129 | chr10 | 135018032 | 135018070 | chr10 | 135018825 | 135018960 |
| chr10 | 135020801 | 135020893 | chr10 | 135023470 | 135023500 | chr10 | 135043088 | 135043538 |
| chr10 | 135043968 | 135044128 | chr10 | 135044555 | 135044573 | chr10 | 135048782 | 135048939 |
| chr10 | 135050311 | 135050679 | chr10 | 135076368 | 135076503 | chr10 | 135121316 | 135121345 |
| chr10 | 135121807 | 135122251 | chr10 | 135122742 | 135122808 | chr10 | 135122991 | 135123020 |
| chr10 | 135139555 | 135139730 | chr10 | 135153956 | 135154001 | chr11 | 232863 | 233062 |
| chr11 | 392576 | 392720 | chr11 | 394815 | 394968 | chr11 | 406876 | 406939 |
| chr11 | 407427 | 407463 | chr11 | 526389 | 526419 | chr11 | 533451 | 533567 |
| chr11 | 533859 | 533888 | chr11 | 534273 | 534302 | chr11 | 548766 | 548800 |
| chr11 | 611099 | 611128 | chr11 | 611691 | 611791 | chr11 | 636644 | 636673 |
| chr11 | 636895 | 636906 | chr11 | 637162 | 637263 | chr11 | 637350 | 637441 |
| chr11 | 679692 | 679722 | chr11 | 726417 | 726466 | chr11 | 763323 | 763686 |
| chr11 | 775261 | 775291 | chr11 | 829543 | 829708 | chr11 | 830174 | 830243 |
| chr11 | 850555 | 850823 | chr11 | 863062 | 863092 | chr11 | 1006077 | 1006107 |
| chr11 | 1027540 | 1027574 | chr11 | 1029238 | 1029403 | chr11 | 1030215 | 1030296 |
| chr11 | 1080391 | 1080454 | chr11 | 1081667 | 1081715 | chr11 | 1214665 | 1214917 |
| chr11 | 1215899 | 1215999 | chr11 | 1229238 | 1229975 | chr11 | 1244381 | 1244465 |
| chr11 | 1250889 | 1250924 | chr11 | 1251183 | 1251351 | chr11 | 1263602 | 1263644 |
| chr11 | 1274085 | 1274189 | chr11 | 1318403 | 1318432 | chr11 | 1358291 | 1358332 |
| chr11 | 1374959 | 1375003 | chr11 | 1411875 | 1411905 | chr11 | 1430714 | 1430794 |
| chr11 | 1464280 | 1464428 | chr11 | 1469228 | 1469379 | chr11 | 1471920 | 1472058 |
| chr11 | 1868081 | 1868237 | chr11 | 1946130 | 1946160 | chr11 | 1957391 | 1957530 |

TABLE 13-continued

| chr | start | end | chr | start | end | chr | start | end |
|---|---|---|---|---|---|---|---|---|
| chr11 | 1959077 | 1959187 | chr11 | 2040107 | 2040148 | chr11 | 2209907 | 2210278 |
| chr11 | 2226048 | 2226078 | chr11 | 2278708 | 2278839 | chr11 | 2291259 | 2291493 |
| chr11 | 2291984 | 2292057 | chr11 | 2292106 | 2292359 | chr11 | 2292392 | 2292636 |
| chr11 | 2402376 | 2402405 | chr11 | 2437991 | 2438144 | chr11 | 2465350 | 2465447 |
| chr11 | 2465462 | 2465491 | chr11 | 2466597 | 2466788 | chr11 | 2884103 | 2884143 |
| chr11 | 2884159 | 2884309 | chr11 | 3169665 | 3169835 | chr11 | 3181913 | 3181942 |
| chr11 | 3182104 | 3182133 | chr11 | 3767205 | 3767245 | chr11 | 4095819 | 4095864 |
| chr11 | 4209105 | 4209134 | chr11 | 4209382 | 4209411 | chr11 | 5993897 | 5993933 |
| chr11 | 7274215 | 7274245 | chr11 | 7695432 | 7695528 | chr11 | 8040536 | 8040563 |
| chr11 | 8040582 | 8040770 | chr11 | 8103002 | 8103115 | chr11 | 8189987 | 8190766 |
| chr11 | 8284535 | 8284760 | chr11 | 8289517 | 8289745 | chr11 | 8290195 | 8290423 |
| chr11 | 8615674 | 8615704 | chr11 | 9025970 | 9026348 | chr11 | 9112446 | 9112585 |
| chr11 | 9112640 | 9112741 | chr11 | 9405392 | 9405542 | chr11 | 10509678 | 10509807 |
| chr11 | 10811151 | 10811188 | chr11 | 10815867 | 10815903 | chr11 | 12029957 | 12030272 |
| chr11 | 12030823 | 12030852 | chr11 | 12132524 | 12132559 | chr11 | 12399020 | 12399222 |
| chr11 | 12399727 | 12399791 | chr11 | 12695481 | 12695495 | chr11 | 12695573 | 12695611 |
| chr11 | 12696611 | 12696746 | chr11 | 13030566 | 13030890 | chr11 | 13690121 | 13690157 |
| chr11 | 14316375 | 14316404 | chr11 | 15136085 | 15136394 | chr11 | 16628819 | 16628933 |
| chr11 | 16632514 | 16632670 | chr11 | 17497492 | 17497520 | chr11 | 17497546 | 17497685 |
| chr11 | 17740493 | 17740570 | chr11 | 17741679 | 17741889 | chr11 | 17741953 | 17742445 |
| chr11 | 17743742 | 17743775 | chr11 | 18100096 | 18100118 | chr11 | 18812614 | 18812653 |
| chr11 | 18813032 | 18813086 | chr11 | 18813451 | 18813542 | chr11 | 18813792 | 18813947 |
| chr11 | 19263848 | 19263878 | chr11 | 19367102 | 19367134 | chr11 | 19367268 | 19367330 |
| chr11 | 19735730 | 19735760 | chr11 | 20153718 | 20153764 | chr11 | 20178094 | 20178305 |
| chr11 | 20180279 | 20180793 | chr11 | 20181213 | 20181254 | chr11 | 20181725 | 20181993 |
| chr11 | 20182864 | 20182959 | chr11 | 20183251 | 20183421 | chr11 | 20183674 | 20183773 |
| chr11 | 20184569 | 20185410 | chr11 | 20229274 | 20229550 | chr11 | 20229863 | 20230091 |
| chr11 | 20230398 | 20230464 | chr11 | 20618197 | 20618392 | chr11 | 20618423 | 20618924 |
| chr11 | 20619717 | 20619974 | chr11 | 20621341 | 20621644 | chr11 | 20622705 | 20622792 |
| chr11 | 20623259 | 20623359 | chr11 | 20690653 | 20690877 | chr11 | 20691219 | 20691379 |
| chr11 | 20691432 | 20691452 | chr11 | 20691748 | 20691914 | chr11 | 20692453 | 20692529 |
| chr11 | 22215123 | 22215287 | chr11 | 22362934 | 22363189 | chr11 | 22364821 | 22364975 |
| chr11 | 22365407 | 22365477 | chr11 | 27742185 | 27742215 | chr11 | 27743115 | 27743173 |
| chr11 | 27743436 | 27743608 | chr11 | 27744147 | 27744504 | chr11 | 27744711 | 27744744 |
| chr11 | 30037593 | 30037743 | chr11 | 30038689 | 30038739 | chr11 | 30605919 | 30606123 |
| chr11 | 30606796 | 30606864 | chr11 | 30607367 | 30607409 | chr11 | 31818458 | 31818512 |
| chr11 | 31818571 | 31818652 | chr11 | 31819302 | 31819508 | chr11 | 31819568 | 31819833 |
| chr11 | 31820045 | 31820360 | chr11 | 31820461 | 31821025 | chr11 | 31821297 | 31821778 |
| chr11 | 31822325 | 31822393 | chr11 | 31824300 | 31824355 | chr11 | 31824564 | 31824680 |
| chr11 | 31825017 | 31825280 | chr11 | 31825696 | 31825754 | chr11 | 31825833 | 31826070 |
| chr11 | 31826107 | 31826303 | chr11 | 31826409 | 31826732 | chr11 | 31827114 | 31827204 |
| chr11 | 31827438 | 31827519 | chr11 | 31827598 | 31828123 | chr11 | 31833097 | 31833155 |
| chr11 | 31835707 | 31835797 | chr11 | 31836046 | 31836470 | chr11 | 31837019 | 31837512 |
| chr11 | 31837542 | 31838392 | chr11 | 31838678 | 31839051 | chr11 | 31839307 | 31839945 |
| chr11 | 31840042 | 31840080 | chr11 | 31840603 | 31840710 | chr11 | 31840769 | 31840922 |
| chr11 | 31841376 | 31842088 | chr11 | 31842175 | 31842276 | chr11 | 31846022 | 31846230 |
| chr11 | 31846434 | 31846985 | chr11 | 31847250 | 31847301 | chr11 | 31847371 | 31847712 |
| chr11 | 31847770 | 31847872 | chr11 | 31847896 | 31847925 | chr11 | 31848472 | 31848602 |
| chr11 | 31848723 | 31849300 | chr11 | 32009104 | 32009126 | chr11 | 32354844 | 32354959 |
| chr11 | 32355000 | 32355197 | chr11 | 32448583 | 32448893 | chr11 | 32455602 | 32455634 |
| chr11 | 32455841 | 32456025 | chr11 | 32456279 | 32456445 | chr11 | 32456759 | 32457176 |
| chr11 | 32457712 | 32458175 | chr11 | 32458389 | 32458823 | chr11 | 32459684 | 32460071 |
| chr11 | 32460468 | 32460515 | chr11 | 32460796 | 32460864 | chr11 | 33037467 | 33037556 |
| chr11 | 33858424 | 33858463 | chr11 | 33890297 | 33890334 | chr11 | 33993984 | 33994014 |
| chr11 | 34535093 | 34535123 | chr11 | 35547499 | 35547562 | chr11 | 35641683 | 35641718 |
| chr11 | 35684958 | 35685131 | chr11 | 43596513 | 43596608 | chr11 | 43600453 | 43600557 |
| chr11 | 43601094 | 43601467 | chr11 | 43602468 | 43603036 | chr11 | 43603077 | 43603228 |
| chr11 | 43603628 | 43604145 | chr11 | 44325688 | 44325747 | chr11 | 44326137 | 44326184 |
| chr11 | 44327252 | 44327413 | chr11 | 44330878 | 44331439 | chr11 | 44331483 | 44331711 |
| chr11 | 44333052 | 44333081 | chr11 | 44333371 | 44333461 | chr11 | 44333477 | 44333480 |
| chr11 | 44337533 | 44337571 | chr11 | 44337727 | 44337861 | chr11 | 44337883 | 44338057 |
| chr11 | 44338335 | 44338367 | chr11 | 44340823 | 44340858 | chr11 | 44341966 | 44342034 |
| chr11 | 46316896 | 46317355 | chr11 | 46317408 | 46317680 | chr11 | 46413042 | 46413304 |
| chr11 | 46866492 | 46866510 | chr11 | 46940419 | 46940531 | chr11 | 47209044 | 47209189 |
| chr11 | 47358926 | 47359237 | chr11 | 47363557 | 47363625 | chr11 | 47372828 | 47373002 |
| chr11 | 47485995 | 47486141 | chr11 | 57194355 | 57194509 | chr11 | 57235406 | 57235436 |
| chr11 | 57414663 | 57414663 | chr11 | 57437196 | 57437234 | chr11 | 57501025 | 57501068 |
| chr11 | 58672746 | 58673064 | chr11 | 59323596 | 59323729 | chr11 | 59329223 | 59329240 |
| chr11 | 59333405 | 59333541 | chr11 | 60718668 | 60718853 | chr11 | 60718977 | 60719163 |
| chr11 | 61049694 | 61049736 | chr11 | 61058283 | 61058341 | chr11 | 61062822 | 61063023 |
| chr11 | 61063062 | 61063138 | chr11 | 61148730 | 61148749 | chr11 | 61277002 | 61277119 |
| chr11 | 61536985 | 61537014 | chr11 | 61595086 | 61595262 | chr11 | 61596420 | 61596640 |
| chr11 | 61664655 | 61664770 | chr11 | 61666106 | 61666136 | chr11 | 62370720 | 62370750 |
| chr11 | 62440549 | 62440588 | chr11 | 62484517 | 62484547 | chr11 | 63609979 | 63610013 |
| chr11 | 63641072 | 63641104 | chr11 | 63839478 | 63839528 | chr11 | 63849394 | 63849426 |
| chr11 | 63934589 | 63934619 | chr11 | 64105954 | 64106031 | chr11 | 64120879 | 64120909 |
| chr11 | 64140397 | 64140427 | chr11 | 64410723 | 64410759 | chr11 | 64480429 | 64480593 |
| chr11 | 64480824 | 64481042 | chr11 | 64490435 | 64490561 | chr11 | 64490792 | 64490806 |

TABLE 13-continued

| chr | start | end | chr | start | end | chr | start | end |
|---|---|---|---|---|---|---|---|---|
| chr11 | 64490826 | 64491159 | chr11 | 64578577 | 64578600 | chr11 | 64739468 | 64739508 |
| chr11 | 64809865 | 64809906 | chr11 | 64950292 | 64950374 | chr11 | 65091291 | 65091369 |
| chr11 | 65185548 | 65185728 | chr11 | 65405659 | 65405774 | chr11 | 65409759 | 65409861 |
| chr11 | 65478524 | 65478611 | chr11 | 65511027 | 65511172 | chr11 | 65511392 | 65511522 |
| chr11 | 65554043 | 65554410 | chr11 | 65600810 | 65601640 | chr11 | 65778952 | 65778981 |
| chr11 | 65779317 | 65779357 | chr11 | 65816447 | 65816519 | chr11 | 65816561 | 65816564 |
| chr11 | 66114279 | 66114331 | chr11 | 66188115 | 66188145 | chr11 | 66188473 | 66188484 |
| chr11 | 66188571 | 66188783 | chr11 | 66188853 | 66188974 | chr11 | 66454424 | 66454454 |
| chr11 | 66511223 | 66511327 | chr11 | 66513217 | 66513252 | chr11 | 66513552 | 66513646 |
| chr11 | 66625207 | 66625240 | chr11 | 66649028 | 66649058 | chr11 | 66658257 | 66658290 |
| chr11 | 66725600 | 66725637 | chr11 | 66790621 | 66790655 | chr11 | 67072239 | 67072396 |
| chr11 | 67139422 | 67139460 | chr11 | 67139535 | 67139546 | chr11 | 67210017 | 67210057 |
| chr11 | 67248420 | 67248458 | chr11 | 67350961 | 67350990 | chr11 | 67462643 | 67462833 |
| chr11 | 67764187 | 67764254 | chr11 | 67781196 | 67781564 | chr11 | 67797202 | 67797281 |
| chr11 | 68096034 | 68096179 | chr11 | 68118716 | 68118745 | chr11 | 68153950 | 68154098 |
| chr11 | 68181217 | 68181288 | chr11 | 68409558 | 68409588 | chr11 | 68804728 | 68804776 |
| chr11 | 69192566 | 69192784 | chr11 | 69280561 | 69280633 | chr11 | 69466004 | 69466042 |
| chr11 | 69484356 | 69484454 | chr11 | 69516968 | 69517174 | chr11 | 69518030 | 69518211 |
| chr11 | 69518530 | 69518718 | chr11 | 69588930 | 69589184 | chr11 | 69589824 | 69589854 |
| chr11 | 69590149 | 69590222 | chr11 | 70211516 | 70211545 | chr11 | 71192746 | 71192889 |
| chr11 | 71318332 | 71318809 | chr11 | 71318953 | 71318967 | chr11 | 71951639 | 71951738 |
| chr11 | 71952340 | 71952416 | chr11 | 71952459 | 71952541 | chr11 | 71954612 | 71954642 |
| chr11 | 71955344 | 71955377 | chr11 | 71956007 | 71966340 | chr11 | 72413950 | 72414010 |
| chr11 | 72432837 | 72432916 | chr11 | 72475677 | 72475711 | chr11 | 72532348 | 72532378 |
| chr11 | 72929747 | 72929883 | chr11 | 73072907 | 73072953 | chr11 | 73310367 | 73310441 |
| chr11 | 73685698 | 73685845 | chr11 | 73694609 | 73694659 | chr11 | 74394491 | 74394600 |
| chr11 | 74953265 | 74953336 | chr11 | 75379283 | 75379895 | chr11 | 75459486 | 75459571 |
| chr11 | 75858210 | 75858240 | chr11 | 76371738 | 76372077 | chr11 | 78672917 | 78672964 |
| chr11 | 79151173 | 79151216 | chr11 | 82444376 | 82445101 | chr11 | 82998001 | 82998031 |
| chr11 | 86085742 | 86085861 | chr11 | 86085932 | 86085968 | chr11 | 86383167 | 86383710 |
| chr11 | 88241705 | 88241975 | chr11 | 88242131 | 88242274 | chr11 | 88242359 | 88242618 |
| chr11 | 88799082 | 88799209 | chr11 | 89867794 | 89867990 | chr11 | 91957500 | 91957674 |
| chr11 | 91957974 | 91958230 | chr11 | 91958734 | 91959326 | chr11 | 91959355 | 91959430 |
| chr11 | 91959899 | 91960045 | chr11 | 93063583 | 93063645 | chr11 | 93063870 | 93063948 |
| chr11 | 93911651 | 93911800 | chr11 | 94134086 | 94134463 | chr11 | 94134683 | 94134853 |
| chr11 | 94275794 | 94275813 | chr11 | 94278456 | 94278603 | chr11 | 94473600 | 94473768 |
| chr11 | 94473803 | 94474139 | chr11 | 94474356 | 94474385 | chr11 | 94502334 | 94502489 |
| chr11 | 94884130 | 94884160 | chr11 | 98891477 | 98891882 | chr11 | 100997649 | 100997981 |
| chr11 | 100998276 | 100998318 | chr11 | 100998667 | 100998744 | chr11 | 101453180 | 101453518 |
| chr11 | 102961347 | 102961378 | chr11 | 102962922 | 102963062 | chr11 | 102980027 | 102980056 |
| chr11 | 104034521 | 104034996 | chr11 | 105480755 | 105480786 | chr11 | 105481216 | 105481571 |
| chr11 | 106888308 | 106888429 | chr11 | 106888641 | 106888801 | chr11 | 107461623 | 107461653 |
| chr11 | 107462415 | 107462459 | chr11 | 108236072 | 108236101 | chr11 | 108603233 | 108603263 |
| chr11 | 109292906 | 109293052 | chr11 | 109293720 | 109293763 | chr11 | 110166519 | 110166693 |
| chr11 | 110582232 | 110582434 | chr11 | 110582895 | 110583028 | chr11 | 110583044 | 110583050 |
| chr11 | 110583574 | 110583730 | chr11 | 111383183 | 111383531 | chr11 | 111383558 | 111383682 |
| chr11 | 111411093 | 111411581 | chr11 | 111411822 | 111412061 | chr11 | 111783548 | 111783577 |
| chr11 | 114113022 | 114113052 | chr11 | 115375120 | 115375177 | chr11 | 115530222 | 115530604 |
| chr11 | 115630531 | 115630910 | chr11 | 115631307 | 115631364 | chr11 | 116147253 | 116147283 |
| chr11 | 116451023 | 116451190 | chr11 | 117056042 | 117056073 | chr11 | 117296921 | 117297109 |
| chr11 | 118991056 | 118991079 | chr11 | 119148865 | 119148945 | chr11 | 119149236 | 119149265 |
| chr11 | 119292779 | 119292809 | chr11 | 119293370 | 119293615 | chr11 | 119612227 | 119612267 |
| chr11 | 119612324 | 119612399 | chr11 | 119612998 | 119613075 | chr11 | 120008105 | 120008504 |
| chr11 | 120039833 | 120039865 | chr11 | 120435405 | 120435477 | chr11 | 120435800 | 120435830 |
| chr11 | 120894800 | 120895026 | chr11 | 120998701 | 120998825 | chr11 | 122847265 | 122847696 |
| chr11 | 122848079 | 122848312 | chr11 | 122848369 | 122848591 | chr11 | 122849301 | 122849331 |
| chr11 | 122849783 | 122850123 | chr11 | 122850149 | 122850163 | chr11 | 122850424 | 122850536 |
| chr11 | 122851177 | 122851209 | chr11 | 122852438 | 122852475 | chr11 | 122855008 | 122855043 |
| chr11 | 122961137 | 122961219 | chr11 | 123066433 | 123066463 | chr11 | 123229058 | 123229406 |
| chr11 | 123300824 | 123301028 | chr11 | 123301083 | 123302026 | chr11 | 124735437 | 124735482 |
| chr11 | 124736196 | 124736252 | chr11 | 124738777 | 124739088 | chr11 | 125035763 | 125036208 |
| chr11 | 125220500 | 125220643 | chr11 | 125755612 | 125755710 | chr11 | 125773675 | 125774060 |
| chr11 | 126870182 | 126870212 | chr11 | 126870453 | 126870500 | chr11 | 126870525 | 126870543 |
| chr11 | 126873390 | 126873515 | chr11 | 128391893 | 128392116 | chr11 | 128562892 | 128563185 |
| chr11 | 128563337 | 128563730 | chr11 | 128563940 | 128564329 | chr11 | 128564740 | 128564876 |
| chr11 | 128564992 | 128565379 | chr11 | 128657931 | 128657970 | chr11 | 129242876 | 129243241 |
| chr11 | 129243305 | 129243587 | chr11 | 129243926 | 129244300 | chr11 | 129244441 | 129244603 |
| chr11 | 129245673 | 129245810 | chr11 | 129246070 | 129246129 | chr11 | 130318960 | 130318997 |
| chr11 | 130319527 | 130319613 | chr11 | 130343061 | 130343100 | chr11 | 130359769 | 130359812 |
| chr11 | 130359872 | 130359915 | chr11 | 130781550 | 130781781 | chr11 | 130785487 | 130785622 |
| chr11 | 131522763 | 131522947 | chr11 | 131564970 | 131565073 | chr11 | 131766868 | 131766960 |
| chr11 | 131780877 | 131781078 | chr11 | 132484215 | 132484404 | chr11 | 132813489 | 132813757 |
| chr11 | 132813908 | 132813949 | chr11 | 132864134 | 132864175 | chr11 | 132934123 | 132934176 |
| chr11 | 132952768 | 132953050 | chr11 | 132953233 | 132953423 | chr11 | 133231739 | 133231832 |
| chr11 | 133402206 | 133402260 | chr11 | 133792055 | 133792214 | chr11 | 133825226 | 133825543 |
| chr11 | 133906783 | 133906918 | chr11 | 133939002 | 133939177 | chr11 | 134145703 | 134146393 |
| chr11 | 134146682 | 134146894 | chr11 | 134201502 | 134201543 | chr11 | 134201841 | 134202084 |
| chr11 | 134281365 | 134281509 | chr12 | 570090 | 570171 | chr12 | 1639135 | 1639222 |

TABLE 13-continued

| chr | start | end | chr | start | end | chr | start | end |
|---|---|---|---|---|---|---|---|---|
| chr12 | 2046104 | 2046134 | chr12 | 2162554 | 2162817 | chr12 | 2163164 | 2163276 |
| chr12 | 2403658 | 2403714 | chr12 | 2566053 | 2566247 | chr12 | 2595199 | 2595339 |
| chr12 | 2862068 | 2862142 | chr12 | 2964465 | 2964577 | chr12 | 3371882 | 3371911 |
| chr12 | 3373533 | 3373666 | chr12 | 3600315 | 3600345 | chr12 | 3602270 | 3602716 |
| chr12 | 3602865 | 3602879 | chr12 | 3603100 | 3603156 | chr12 | 3862254 | 3862298 |
| chr12 | 4214005 | 4214157 | chr12 | 4274054 | 4274188 | chr12 | 4274271 | 4274409 |
| chr12 | 4362436 | 4362471 | chr12 | 4378252 | 4378330 | chr12 | 4379357 | 4379491 |
| chr12 | 4381433 | 4382386 | chr12 | 4382965 | 4382999 | chr12 | 4383492 | 4383784 |
| chr12 | 4384389 | 4384418 | chr12 | 4384736 | 4384902 | chr12 | 4392883 | 4392922 |
| chr12 | 4405589 | 4405619 | chr12 | 4554801 | 4564831 | chr12 | 4919145 | 4919213 |
| chr12 | 4919239 | 4919244 | chr12 | 5018073 | 5018692 | chr12 | 5019085 | 5019742 |
| chr12 | 5019794 | 5020313 | chr12 | 5153039 | 5153286 | chr12 | 5153358 | 5153460 |
| chr12 | 5541100 | 5541177 | chr12 | 5542325 | 5542439 | chr12 | 5542759 | 5542911 |
| chr12 | 5840200 | 5840363 | chr12 | 6308743 | 6308772 | chr12 | 6483615 | 6483756 |
| chr12 | 6664508 | 6664522 | chr12 | 7559160 | 7559307 | chr12 | 8025635 | 8025660 |
| chr12 | 8127118 | 8127140 | chr12 | 8171360 | 8171745 | chr12 | 8808599 | 8808684 |
| chr12 | 8850658 | 8850744 | chr12 | 8975182 | 8975361 | chr12 | 10085916 | 10085932 |
| chr12 | 10363278 | 10363323 | chr12 | 10772771 | 10772896 | chr12 | 11653449 | 11653463 |
| chr12 | 12504823 | 12504850 | chr12 | 12848390 | 12848556 | chr12 | 14133152 | 14133263 |
| chr12 | 14133619 | 14133881 | chr12 | 14135111 | 14135339 | chr12 | 14818824 | 14818857 |
| chr12 | 15374258 | 15374291 | chr12 | 16500576 | 16500621 | chr12 | 19282333 | 19282363 |
| chr12 | 20521704 | 20521841 | chr12 | 20522457 | 20522487 | chr12 | 20522769 | 20522891 |
| chr12 | 21680394 | 21680683 | chr12 | 21810264 | 21810868 | chr12 | 21833068 | 21833107 |
| chr12 | 22093825 | 22094268 | chr12 | 22094578 | 22094810 | chr12 | 22486799 | 22486881 |
| chr12 | 22487134 | 22487473 | chr12 | 22698087 | 22698110 | chr12 | 24714909 | 24714938 |
| chr12 | 24715235 | 24715264 | chr12 | 24716033 | 24716218 | chr12 | 25056243 | 25056436 |
| chr12 | 25101592 | 25101660 | chr12 | 25101919 | 25101997 | chr12 | 25102010 | 25102086 |
| chr12 | 25362824 | 25362853 | chr12 | 25368463 | 25368492 | chr12 | 25378543 | 25378662 |
| chr12 | 25380231 | 25380299 | chr12 | 25398203 | 25398319 | chr12 | 27176520 | 27176539 |
| chr12 | 27494550 | 27494580 | chr12 | 28123996 | 28124247 | chr12 | 28127767 | 28128302 |
| chr12 | 28128547 | 28129084 | chr12 | 29936016 | 29936048 | chr12 | 29936602 | 29936642 |
| chr12 | 29936662 | 29936831 | chr12 | 29937331 | 29937374 | chr12 | 30322774 | 30322924 |
| chr12 | 30323015 | 30323439 | chr12 | 30323503 | 30323517 | chr12 | 30975572 | 30975959 |
| chr12 | 31079268 | 31079367 | chr12 | 31079418 | 31079499 | chr12 | 31316012 | 31316037 |
| chr12 | 32340317 | 32340336 | chr12 | 33591774 | 33591804 | chr12 | 33592613 | 33592847 |
| chr12 | 34494888 | 34494918 | chr12 | 34502733 | 34502803 | chr12 | 39299117 | 39299560 |
| chr12 | 39539353 | 39539436 | chr12 | 40618404 | 40618470 | chr12 | 41086183 | 41086379 |
| chr12 | 41086784 | 41087106 | chr12 | 41582513 | 41582988 | chr12 | 41583374 | 41583419 |
| chr12 | 43945110 | 43945124 | chr12 | 43945356 | 43945379 | chr12 | 43945417 | 43945526 |
| chr12 | 43946203 | 43946298 | chr12 | 45269504 | 45269624 | chr12 | 45444118 | 46444681 |
| chr12 | 45444715 | 45445258 | chr12 | 46767650 | 46767697 | chr12 | 47225381 | 47225476 |
| chr12 | 47225551 | 47225579 | chr12 | 47629349 | 47629379 | chr12 | 48397195 | 48398070 |
| chr12 | 48398641 | 48398671 | chr12 | 48690674 | 48690880 | chr12 | 49297802 | 49297915 |
| chr12 | 49366374 | 49366423 | chr12 | 49374914 | 49375026 | chr12 | 49375116 | 49375119 |
| chr12 | 49375325 | 49375529 | chr12 | 49390873 | 49391104 | chr12 | 49391147 | 49391877 |
| chr12 | 49657705 | 49657743 | chr12 | 49691049 | 49691078 | chr12 | 49727092 | 49727127 |
| chr12 | 49729728 | 49730090 | chr12 | 49759530 | 49759559 | chr12 | 49989786 | 49989816 |
| chr12 | 50297497 | 50297554 | chr12 | 50297974 | 50298055 | chr12 | 50426748 | 50426799 |
| chr12 | 51421133 | 51421271 | chr12 | 51421556 | 51421586 | chr12 | 51565469 | 51565548 |
| chr12 | 51930708 | 51930785 | chr12 | 52262983 | 52263106 | chr12 | 52301280 | 52301305 |
| chr12 | 52400831 | 52401537 | chr12 | 52408905 | 52409033 | chr12 | 52627273 | 52627438 |
| chr12 | 52652153 | 52652219 | chr12 | 52652600 | 52652613 | chr12 | 53108089 | 53108216 |
| chr12 | 53359386 | 53359563 | chr12 | 54089093 | 54089511 | chr12 | 54132252 | 54132329 |
| chr12 | 54145843 | 54145857 | chr12 | 54145881 | 54145895 | chr12 | 54321250 | 54321628 |
| chr12 | 54322201 | 54322252 | chr12 | 54324799 | 54324937 | chr12 | 54329358 | 54329478 |
| chr12 | 54329605 | 54329947 | chr12 | 54331062 | 54331135 | chr12 | 54332868 | 54333337 |
| chr12 | 54338666 | 54338817 | chr12 | 54338979 | 54339681 | chr12 | 54343812 | 54343829 |
| chr12 | 54345611 | 54345658 | chr12 | 54345966 | 54346032 | chr12 | 54348844 | 54349079 |
| chr12 | 54349256 | 54349336 | chr12 | 54354514 | 54354621 | chr12 | 54354905 | 54355086 |
| chr12 | 54359960 | 54360084 | chr12 | 54360608 | 54360649 | chr12 | 54377912 | 54377946 |
| chr12 | 54377978 | 54378115 | chr12 | 54379174 | 54379623 | chr12 | 54379888 | 54379930 |
| chr12 | 54379959 | 54380459 | chr12 | 54387842 | 54387959 | chr12 | 54388215 | 54388245 |
| chr12 | 54391400 | 54391403 | chr12 | 54393479 | 54393684 | chr12 | 54393950 | 54394162 |
| chr12 | 54394410 | 54394418 | chr12 | 54398889 | 54398959 | chr12 | 54399616 | 54399646 |
| chr12 | 54402690 | 54402796 | chr12 | 54403067 | 54403360 | chr12 | 54408411 | 54408726 |
| chr12 | 54409476 | 54409505 | chr12 | 54423616 | 54423697 | chr12 | 54424746 | 54424748 |
| chr12 | 54425032 | 54425119 | chr12 | 54447351 | 54447581 | chr12 | 54447899 | 54447977 |
| chr12 | 54520745 | 54520868 | chr12 | 54720200 | 54720232 | chr12 | 54812238 | 54812359 |
| chr12 | 54922714 | 54922803 | chr12 | 54942994 | 54943116 | chr12 | 56231108 | 56231148 |
| chr12 | 56478840 | 56478869 | chr12 | 56481645 | 56481937 | chr12 | 56486572 | 56486601 |
| chr12 | 56490965 | 56490994 | chr12 | 56491630 | 56491659 | chr12 | 56492618 | 56492647 |
| chr12 | 56558381 | 56558519 | chr12 | 56873601 | 56873630 | chr12 | 56882240 | 56882380 |
| chr12 | 57387303 | 57387332 | chr12 | 57559869 | 57559925 | chr12 | 57618574 | 57618710 |
| chr12 | 57881127 | 57881345 | chr12 | 57944081 | 57944117 | chr12 | 58021320 | 58021458 |
| chr12 | 58021916 | 58022029 | chr12 | 58026646 | 58025733 | chr12 | 58025870 | 58025873 |
| chr12 | 58145415 | 58145450 | chr12 | 59314159 | 59314189 | chr12 | 62584838 | 62585012 |
| chr12 | 62585031 | 62586017 | chr12 | 62586252 | 62586281 | chr12 | 62858540 | 62858575 |
| chr12 | 63025574 | 63026160 | chr12 | 63543848 | 63544401 | chr12 | 63544499 | 63544599 |

TABLE 13-continued

| chr | start | end | chr | start | end | chr | start | end |
|---|---|---|---|---|---|---|---|---|
| chr12 | 63545313 | 63545343 | chr12 | 64061821 | 64062159 | chr12 | 64062369 | 64062578 |
| chr12 | 64062921 | 64063096 | chr12 | 64783185 | 64783308 | chr12 | 64784108 | 64784252 |
| chr12 | 64784534 | 64784564 | chr12 | 65218102 | 65218550 | chr12 | 65218901 | 65219156 |
| chr12 | 65219376 | 65219527 | chr12 | 65219606 | 65219784 | chr12 | 65220205 | 65220350 |
| chr12 | 65514863 | 65515596 | chr12 | 65516378 | 65516455 | chr12 | 65557212 | 65557234 |
| chr12 | 65562052 | 65562086 | chr12 | 66122800 | 66122995 | chr12 | 66123381 | 66123519 |
| chr12 | 66135984 | 66136014 | chr12 | 66582827 | 66583137 | chr12 | 69327259 | 69327463 |
| chr12 | 69754451 | 69754470 | chr12 | 69754590 | 69754710 | chr12 | 59964176 | 69964264 |
| chr12 | 70087493 | 70087568 | chr12 | 72332641 | 72332696 | chr12 | 72665186 | 72665788 |
| chr12 | 72666713 | 72666807 | chr12 | 72666998 | 72667425 | chr12 | 72667652 | 72667682 |
| chr12 | 75601379 | 75601499 | chr12 | 75601696 | 75601910 | chr12 | 75602976 | 75603231 |
| chr12 | 75728336 | 75728485 | chr12 | 75728737 | 75728766 | chr12 | 77719311 | 77719422 |
| chr12 | 79257222 | 79257351 | chr12 | 81102185 | 81102455 | chr12 | 81102513 | 81102562 |
| chr12 | 81107997 | 81108034 | chr12 | 81471517 | 81471614 | chr12 | 81471754 | 81472111 |
| chr12 | 85306519 | 85306549 | chr12 | 85667272 | 85667731 | chr12 | 85673206 | 85673235 |
| chr12 | 85673460 | 85674807 | chr12 | 88973544 | 88973582 | chr12 | 88974159 | 88974253 |
| chr12 | 93966429 | 93966603 | chr12 | 93966998 | 93967215 | chr12 | 94543409 | 94543445 |
| chr12 | 94543899 | 94543961 | chr12 | 94544022 | 94544052 | chr12 | 94852489 | 94852506 |
| chr12 | 95267524 | 95267554 | chr12 | 95267865 | 95267976 | chr12 | 95942965 | 95942978 |
| chr12 | 99288312 | 99288407 | chr12 | 99288622 | 99288936 | chr12 | 99289162 | 99289309 |
| chr12 | 101025380 | 101025410 | chr12 | 101111029 | 101111061 | chr12 | 101111373 | 101111479 |
| chr12 | 103218495 | 103218595 | chr12 | 103351564 | 103351985 | chr12 | 103352052 | 103352154 |
| chr12 | 103352171 | 103352282 | chr12 | 103352314 | 103352681 | chr12 | 103358865 | 103358899 |
| chr12 | 103359556 | 103359586 | chr12 | 103889160 | 103889211 | chr12 | 103889789 | 103889812 |
| chr12 | 104609417 | 104609796 | chr12 | 104684181 | 104684220 | chr12 | 104850505 | 104850536 |
| chr12 | 104850578 | 104850592 | chr12 | 104851077 | 104851186 | chr12 | 104852032 | 104852508 |
| chr12 | 105017109 | 105017199 | chr12 | 105478323 | 105478419 | chr12 | 106533852 | 106533881 |
| chr12 | 106974353 | 106974383 | chr12 | 106976725 | 106976779 | chr12 | 106977321 | 106977492 |
| chr12 | 106979161 | 106979534 | chr12 | 106979799 | 106979995 | chr12 | 106980223 | 106980333 |
| chr12 | 106980912 | 106981406 | chr12 | 107486550 | 107486672 | chr12 | 107487194 | 107487855 |
| chr12 | 107712273 | 107712303 | chr12 | 107713205 | 107713235 | chr12 | 107714866 | 107715153 |
| chr12 | 108168971 | 108169413 | chr12 | 108169550 | 108169573 | chr12 | 108237466 | 108237524 |
| chr12 | 108238102 | 108238513 | chr12 | 108297411 | 108297466 | chr12 | 109488519 | 109488543 |
| chr12 | 109639281 | 109639475 | chr12 | 110353414 | 110353451 | chr12 | 110717541 | 110717710 |
| chr12 | 110983706 | 110983736 | chr12 | 111127124 | 111127455 | chr12 | 111471177 | 111471559 |
| chr12 | 111471948 | 111471959 | chr12 | 111472059 | 111472195 | chr12 | 111472357 | 111472621 |
| chr12 | 111763122 | 111763152 | chr12 | 112574734 | 112574775 | chr12 | 112888151 | 112888315 |
| chr12 | 112910821 | 112910850 | chr12 | 112915509 | 112915538 | chr12 | 112926255 | 112926284 |
| chr12 | 112926876 | 112926914 | chr12 | 113012954 | 113013157 | chr12 | 113541667 | 113542099 |
| chr12 | 113592238 | 113592359 | chr12 | 113900753 | 113900765 | chr12 | 113901074 | 113901158 |
| chr12 | 113901408 | 113901591 | chr12 | 113902042 | 113902353 | chr12 | 113903468 | 113903498 |
| chr12 | 113904779 | 113905016 | chr12 | 113908990 | 113909314 | chr12 | 113909329 | 113909455 |
| chr12 | 113913267 | 113913681 | chr12 | 113913884 | 113914050 | chr12 | 113916222 | 113916316 |
| chr12 | 113916649 | 113916678 | chr12 | 113916972 | 113917012 | chr12 | 113917232 | 113917310 |
| chr12 | 113917775 | 113917890 | chr12 | 114029408 | 114029660 | chr12 | 114076029 | 114076093 |
| chr12 | 114337763 | 114337793 | chr12 | 114833985 | 114834102 | chr12 | 114838369 | 114838726 |
| chr12 | 114839104 | 114839147 | chr12 | 114841046 | 114841084 | chr12 | 114841425 | 114841493 |
| chr12 | 114843112 | 114843186 | chr12 | 114843261 | 114843278 | chr12 | 114843545 | 114843660 |
| chr12 | 114844201 | 114844300 | chr12 | 114846715 | 114846768 | chr12 | 114847043 | 114847436 |
| chr12 | 114847578 | 114847691 | chr12 | 114852040 | 114852082 | chr12 | 114852293 | 114852373 |
| chr12 | 114877171 | 114877262 | chr12 | 114878550 | 114878584 | chr12 | 114878813 | 114879012 |
| chr12 | 114881634 | 114881764 | chr12 | 114882555 | 114882646 | chr12 | 114883473 | 114883535 |
| chr12 | 114918594 | 114918717 | chr12 | 115136159 | 115136363 | chr12 | 116946086 | 116946199 |
| chr12 | 116946251 | 116946548 | chr12 | 117474065 | 117474198 | chr12 | 117798065 | 117798095 |
| chr12 | 117799413 | 117799529 | chr12 | 118860397 | 118860436 | chr12 | 119212319 | 119212381 |
| chr12 | 119418594 | 119418847 | chr12 | 119419436 | 119419466 | chr12 | 119419720 | 119419899 |
| chr12 | 120032862 | 120033169 | chr12 | 120148142 | 120148248 | chr12 | 120148923 | 120148962 |
| chr12 | 120535158 | 120535187 | chr12 | 120536625 | 120536654 | chr12 | 120885215 | 120885245 |
| chr12 | 121622546 | 121622576 | chr12 | 122192723 | 122192843 | chr12 | 122278484 | 122278580 |
| chr12 | 122285067 | 122285108 | chr12 | 122473581 | 122473611 | chr12 | 123129129 | 123129160 |
| chr12 | 123233806 | 123233846 | chr12 | 124246908 | 124246937 | chr12 | 124247208 | 124247237 |
| chr12 | 124393560 | 124393604 | chr12 | 124397464 | 124397618 | chr12 | 124865115 | 124865144 |
| chr12 | 125009276 | 125009306 | chr12 | 125533949 | 125534407 | chr12 | 125589840 | 125589872 |
| chr12 | 125670117 | 125670260 | chr12 | 126168554 | 126168620 | chr12 | 127211317 | 127211378 |
| chr12 | 127765158 | 127765432 | chr12 | 127940086 | 127940247 | chr12 | 128751384 | 128751443 |
| chr12 | 128751821 | 128751877 | chr12 | 128752115 | 128752240 | chr12 | 128752499 | 128752944 |
| chr12 | 128753210 | 128753240 | chr12 | 128850534 | 128850644 | chr12 | 129338588 | 129338816 |
| chr12 | 130037653 | 130037778 | chr12 | 130387797 | 130387811 | chr12 | 130388410 | 130388434 |
| chr12 | 130389013 | 130389152 | chr12 | 130589202 | 130589266 | chr12 | 130645233 | 130645627 |
| chr12 | 130646946 | 130647115 | chr12 | 130647574 | 130647908 | chr12 | 130647951 | 130648069 |
| chr12 | 130821371 | 130821621 | chr12 | 130968621 | 130968654 | chr12 | 131200379 | 131200645 |
| chr12 | 131400816 | 131400919 | chr12 | 131403032 | 131403125 | chr12 | 131513345 | 131513403 |
| chr12 | 132102173 | 132102202 | chr12 | 132169288 | 132169365 | chr12 | 132221689 | 132222076 |
| chr12 | 132333434 | 132333456 | chr12 | 132333516 | 132333597 | chr12 | 132348651 | 132348684 |
| chr12 | 132423595 | 132423854 | chr12 | 132643233 | 132643279 | chr12 | 132986495 | 132986581 |
| chr12 | 133002792 | 133003231 | chr12 | 133172907 | 133173021 | chr12 | 133195093 | 133195196 |
| chr12 | 133199738 | 133199784 | chr12 | 133280578 | 133280682 | chr12 | 133463736 | 133463876 |
| chr12 | 133464108 | 133464166 | chr12 | 133464840 | 133464934 | chr12 | 133464994 | 133465027 |

TABLE 13-continued

| chr | start | end | chr | start | end | chr | start | end |
|---|---|---|---|---|---|---|---|---|
| chr12 | 133481490 | 133481655 | chr12 | 133484742 | 133484852 | chr12 | 133485162 | 133485347 |
| chr12 | 133485557 | 133485689 | chr12 | 133485816 | 133485847 | chr12 | 133758048 | 133758107 |
| chr13 | 20175911 | 20175941 | chr13 | 20735804 | 20736089 | chr13 | 21649636 | 21649775 |
| chr13 | 22243273 | 22243469 | chr13 | 23489851 | 23489914 | chr13 | 23653797 | 23653813 |
| chr13 | 23733447 | 23734020 | chr13 | 23734284 | 23734297 | chr13 | 24477643 | 24477906 |
| chr13 | 25115713 | 25115771 | chr13 | 25319856 | 25319904 | chr13 | 25320388 | 25320539 |
| chr13 | 25320614 | 25321028 | chr13 | 25321113 | 25321350 | chr13 | 25321699 | 25321942 |
| chr13 | 25593062 | 25593242 | chr13 | 25621045 | 25621205 | chr13 | 25621264 | 25621394 |
| chr13 | 25744716 | 25744734 | chr13 | 25745301 | 25745594 | chr13 | 25745727 | 25746000 |
| chr13 | 25946301 | 25946411 | chr13 | 25946620 | 25946673 | chr13 | 26042678 | 26042707 |
| chr13 | 26042769 | 26043170 | chr13 | 26043341 | 26043499 | chr13 | 26340608 | 26340755 |
| chr13 | 26625301 | 26625656 | chr13 | 27334211 | 27334563 | chr13 | 27334772 | 27334894 |
| chr13 | 28239909 | 28240164 | chr13 | 28365705 | 28366122 | chr13 | 28366482 | 28366577 |
| chr13 | 28367024 | 28367038 | chr13 | 28367794 | 28367945 | chr13 | 28368154 | 28368168 |
| chr13 | 28368451 | 28368593 | chr13 | 28368952 | 28369070 | chr13 | 28369162 | 28369891 |
| chr13 | 28369951 | 28369990 | chr13 | 28370947 | 28371061 | chr13 | 28394766 | 28394866 |
| chr13 | 28395501 | 28395553 | chr13 | 28395998 | 28396073 | chr13 | 28491793 | 28491946 |
| chr13 | 28492244 | 28492553 | chr13 | 28503042 | 28503074 | chr13 | 28528534 | 28528748 |
| chr13 | 28540745 | 28540927 | chr13 | 28543212 | 28543242 | chr13 | 28544397 | 28544584 |
| chr13 | 28544666 | 28544903 | chr13 | 28549497 | 28549891 | chr13 | 28550240 | 28550552 |
| chr13 | 28551417 | 28551461 | chr13 | 28551950 | 28552167 | chr13 | 28552794 | 28552824 |
| chr13 | 28553030 | 28553138 | chr13 | 28589765 | 28589794 | chr13 | 28592605 | 28592658 |
| chr13 | 28601345 | 28601374 | chr13 | 28602326 | 28602355 | chr13 | 28608233 | 28608355 |
| chr13 | 28610123 | 28610152 | chr13 | 28674018 | 28674226 | chr13 | 28674721 | 28674734 |
| chr13 | 29067773 | 29068416 | chr13 | 29068926 | 29068985 | chr13 | 29068994 | 29069065 |
| chr13 | 29106308 | 29106814 | chr13 | 29106899 | 29107063 | chr13 | 29107253 | 29107309 |
| chr13 | 29112420 | 29112444 | chr13 | 30141688 | 30141718 | chr13 | 30707569 | 30707599 |
| chr13 | 31742953 | 31743177 | chr13 | 32605034 | 32605324 | chr13 | 32605443 | 32605623 |
| chr13 | 32605675 | 32605966 | chr13 | 33591300 | 33591419 | chr13 | 33924666 | 33924790 |
| chr13 | 35517410 | 35517648 | chr13 | 36044829 | 36044930 | chr13 | 36049995 | 36050025 |
| chr13 | 36269480 | 36269509 | chr13 | 36553399 | 36553428 | chr13 | 36704939 | 36705055 |
| chr13 | 36705451 | 36705489 | chr13 | 36909206 | 36909236 | chr13 | 36920317 | 36920386 |
| chr13 | 36920628 | 36920785 | chr13 | 37004771 | 37005129 | chr13 | 37005900 | 37006062 |
| chr13 | 37006434 | 37006657 | chr13 | 37006734 | 37006762 | chr13 | 37248063 | 37248148 |
| chr13 | 37248295 | 37248319 | chr13 | 37248979 | 37248993 | chr13 | 37633989 | 37634018 |
| chr13 | 37643942 | 37644005 | chr13 | 38443618 | 38443715 | chr13 | 39261410 | 39261446 |
| chr13 | 41884500 | 41884534 | chr13 | 43148669 | 43148698 | chr13 | 43566247 | 43566647 |
| chr13 | 44947746 | 44948197 | chr13 | 45150013 | 45150276 | chr13 | 45885876 | 45885905 |
| chr13 | 45905236 | 45905264 | chr13 | 46425548 | 46425554 | chr13 | 46425576 | 46425584 |
| chr13 | 46660839 | 46660869 | chr13 | 46961494 | 46961533 | chr13 | 46961952 | 46961982 |
| chr13 | 47468139 | 47468168 | chr13 | 47472315 | 47472344 | chr13 | 47526166 | 47526182 |
| chr13 | 48478576 | 48478605 | chr13 | 48667877 | 48667907 | chr13 | 49794117 | 49794925 |
| chr13 | 50421504 | 50421696 | chr13 | 50639782 | 50639799 | chr13 | 52580344 | 52580369 |
| chr13 | 53312991 | 53313313 | chr13 | 53313513 | 53313612 | chr13 | 53313678 | 53313920 |
| chr13 | 53419734 | 53419775 | chr13 | 53420020 | 53420020 | chr13 | 53423838 | 53423978 |
| chr13 | 57714539 | 57714568 | chr13 | 58203602 | 58203644 | chr13 | 58203851 | 58204103 |
| chr13 | 58204350 | 58204393 | chr13 | 58206042 | 58206231 | chr13 | 58206453 | 58206771 |
| chr13 | 58206862 | 58206983 | chr13 | 58207568 | 58207813 | chr13 | 58207892 | 58208020 |
| chr13 | 58208495 | 58208926 | chr13 | 62132346 | 62132375 | chr13 | 64650200 | 64650229 |
| chr13 | 65532258 | 65532287 | chr13 | 67803735 | 67804074 | chr13 | 67804494 | 67804523 |
| chr13 | 67805191 | 67805247 | chr13 | 70681626 | 70681777 | chr13 | 70681867 | 70682071 |
| chr13 | 71498386 | 71498415 | chr13 | 72439142 | 72439250 | chr13 | 73336049 | 73336078 |
| chr13 | 73619660 | 73619752 | chr13 | 78492684 | 78492840 | chr13 | 78493166 | 78493196 |
| chr13 | 78493455 | 78493809 | chr13 | 79168067 | 79168102 | chr13 | 79169850 | 79170113 |
| chr13 | 79170348 | 79170383 | chr13 | 79170468 | 79170884 | chr13 | 79171118 | 79171196 |
| chr13 | 79175770 | 79175943 | chr13 | 79176078 | 79176125 | chr13 | 79176277 | 79176420 |
| chr13 | 79176609 | 79176783 | chr13 | 79176993 | 79177184 | chr13 | 79177306 | 79177622 |
| chr13 | 79177886 | 79177998 | chr13 | 79183406 | 79183423 | chr13 | 81229343 | 81229372 |
| chr13 | 84455236 | 84455292 | chr13 | 84455581 | 84455715 | chr13 | 84457491 | 84457521 |
| chr13 | 87731371 | 87731400 | chr13 | 88323579 | 88323830 | chr13 | 88323868 | 88324207 |
| chr13 | 88324516 | 88324518 | chr13 | 88325300 | 88325460 | chr13 | 88325829 | 88326061 |
| chr13 | 88326538 | 88326707 | chr13 | 88326937 | 88327014 | chr13 | 88788883 | 88788912 |
| chr13 | 88997906 | 88997935 | chr13 | 89815436 | 89815465 | chr13 | 90015503 | 90015532 |
| chr13 | 91755723 | 91755750 | chr13 | 91948489 | 91948519 | chr13 | 92050760 | 92050814 |
| chr13 | 92051139 | 92051168 | chr13 | 92051374 | 92051513 | chr13 | 93879288 | 93879375 |
| chr13 | 93879670 | 93879700 | chr13 | 93880089 | 93880216 | chr13 | 93880534 | 93880737 |
| chr13 | 93880794 | 93880856 | chr13 | 95086143 | 95086172 | chr13 | 95357311 | 95357341 |
| chr13 | 95357574 | 95357775 | chr13 | 95358041 | 95358165 | chr13 | 95359747 | 95359803 |
| chr13 | 95360322 | 95360371 | chr13 | 95363210 | 95363429 | chr13 | 95363796 | 95363959 |
| chr13 | 95364065 | 95364196 | chr13 | 95364495 | 95364800 | chr13 | 95620021 | 95620078 |
| chr13 | 95620647 | 95620781 | chr13 | 95620854 | 95621011 | chr13 | 96031705 | 96031730 |
| chr13 | 96204923 | 96205363 | chr13 | 96296225 | 96296345 | chr13 | 96296373 | 96296473 |
| chr13 | 96296841 | 96296949 | chr13 | 96296992 | 96297137 | chr13 | 96743788 | 96744175 |
| chr13 | 97761876 | 97761925 | chr13 | 99851676 | 99851706 | chr13 | 100547713 | 100547893 |
| chr13 | 100608462 | 100608536 | chr13 | 100608596 | 100608804 | chr13 | 100608839 | 100609055 |
| chr13 | 100621941 | 100622015 | chr13 | 100624324 | 100624348 | chr13 | 100624587 | 100624729 |
| chr13 | 100626929 | 100627009 | chr13 | 100627295 | 100627348 | chr13 | 100627688 | 100627717 |
| chr13 | 100630169 | 100630298 | chr13 | 100630329 | 100630430 | chr13 | 100630630 | 100630997 |

TABLE 13-continued

| chr | start | end | chr | start | end | chr | start | end |
|---|---|---|---|---|---|---|---|---|
| chr13 | 100633089 | 100633184 | chr13 | 100634314 | 100634617 | chr13 | 100635406 | 100635451 |
| chr13 | 100636167 | 100636238 | chr13 | 100637390 | 100637485 | chr13 | 100641282 | 100641408 |
| chr13 | 100642120 | 100642201 | chr13 | 100643296 | 100643435 | chr13 | 100644055 | 100644179 |
| chr13 | 100649325 | 100649575 | chr13 | 100649800 | 100649884 | chr13 | 102568454 | 102568484 |
| chr13 | 102569313 | 102569542 | chr13 | 103046721 | 103046995 | chr13 | 103052347 | 103052574 |
| chr13 | 103052892 | 103052940 | chr13 | 103053394 | 103053496 | chr13 | 105484285 | 105484314 |
| chr13 | 105791875 | 105791904 | chr13 | 107186855 | 107186884 | chr13 | 107187162 | 107187426 |
| chr13 | 107187666 | 107187695 | chr13 | 107188241 | 107188430 | chr13 | 108518813 | 108518933 |
| chr13 | 108519254 | 108519367 | chr13 | 108519737 | 108519745 | chr13 | 108520376 | 108520534 |
| chr13 | 108520979 | 108521076 | chr13 | 109147685 | 109147862 | chr13 | 109148155 | 109148278 |
| chr13 | 109148783 | 109149185 | chr13 | 110434451 | 110434593 | chr13 | 110958816 | 110958981 |
| chr13 | 110959753 | 110959970 | chr13 | 110960541 | 110960603 | chr13 | 111278255 | 111278426 |
| chr13 | 111363880 | 111363972 | chr13 | 112272991 | 112273088 | chr13 | 112707694 | 112707869 |
| chr13 | 112708308 | 112708513 | chr13 | 112709388 | 112709617 | chr13 | 112709883 | 112709928 |
| chr13 | 112710360 | 112710475 | chr13 | 112710759 | 112711293 | chr13 | 112711376 | 112711776 |
| chr13 | 112712017 | 112713029 | chr13 | 112715370 | 112715642 | chr13 | 112715985 | 112716313 |
| chr13 | 112716677 | 112716721 | chr13 | 112717026 | 112717242 | chr13 | 112717323 | 112717536 |
| chr13 | 112717835 | 112717949 | chr13 | 112720033 | 112720505 | chr13 | 112720723 | 112720767 |
| chr13 | 112721012 | 112721026 | chr13 | 112722129 | 112722220 | chr13 | 112722275 | 112722312 |
| chr13 | 112724505 | 112724535 | chr13 | 112726436 | 112726560 | chr13 | 112727984 | 112728200 |
| chr13 | 112758107 | 112758257 | chr13 | 112758274 | 112758372 | chr13 | 112758496 | 112758613 |
| chr13 | 112759112 | 112759248 | chr13 | 112759612 | 112759642 | chr13 | 112760007 | 112760327 |
| chr13 | 112760795 | 112761214 | chr13 | 113598618 | 113598851 | chr13 | 113985679 | 113985956 |
| chr13 | 114055983 | 114056137 | chr13 | 114060064 | 114060333 | chr13 | 114074768 | 114074853 |
| chr13 | 114082984 | 114083014 | chr13 | 114123168 | 114123291 | chr13 | 114189737 | 114189809 |
| chr13 | 114221622 | 114221652 | chr13 | 114304565 | 114304927 | chr13 | 114479404 | 114479434 |
| chr13 | 114498017 | 114498260 | chr13 | 114748342 | 114748638 | chr13 | 114766270 | 114766300 |
| chr13 | 114780561 | 114781061 | chr13 | 114807617 | 114807815 | chr13 | 114855635 | 114855669 |
| chr13 | 114862308 | 114862368 | chr13 | 114897194 | 114897217 | chr13 | 114961823 | 114961933 |
| chr14 | 21093454 | 21093543 | chr14 | 21093603 | 21093631 | chr14 | 21100748 | 21100778 |
| chr14 | 21100801 | 21100831 | chr14 | 22005029 | 22005073 | chr14 | 23234956 | 23234994 |
| chr14 | 23356044 | 23356384 | chr14 | 23706727 | 23706765 | chr14 | 24641010 | 24641215 |
| chr14 | 24803594 | 24804122 | chr14 | 26674354 | 26674384 | chr14 | 26674699 | 26674729 |
| chr14 | 27066562 | 27066704 | chr14 | 27066764 | 27066785 | chr14 | 27067373 | 27067386 |
| chr14 | 29225531 | 29225561 | chr14 | 29226071 | 29226198 | chr14 | 29228654 | 29228778 |
| chr14 | 29229107 | 29229386 | chr14 | 29231071 | 29231185 | chr14 | 29231425 | 29231590 |
| chr14 | 29235003 | 29235308 | chr14 | 29235342 | 29235356 | chr14 | 29237063 | 29237066 |
| chr14 | 29242763 | 29242908 | chr14 | 29243516 | 29243669 | chr14 | 29243731 | 29243888 |
| chr14 | 29244224 | 29244308 | chr14 | 29247689 | 29247740 | chr14 | 29254612 | 29254713 |
| chr14 | 31344346 | 31344549 | chr14 | 31925639 | 31925724 | chr14 | 32597620 | 32597657 |
| chr14 | 33402462 | 33402762 | chr14 | 33403045 | 33403316 | chr14 | 33403866 | 33404418 |
| chr14 | 34269897 | 34270004 | chr14 | 34420250 | 34420288 | chr14 | 35023187 | 35023322 |
| chr14 | 35024446 | 35024466 | chr14 | 35389907 | 35389943 | chr14 | 36003442 | 36003826 |
| chr14 | 36004081 | 36004493 | chr14 | 36004711 | 36004734 | chr14 | 36004822 | 36004921 |
| chr14 | 36972803 | 36972912 | chr14 | 36973455 | 36973538 | chr14 | 36974294 | 36974927 |
| chr14 | 36974968 | 36974982 | chr14 | 36975299 | 36975399 | chr14 | 36977645 | 36977929 |
| chr14 | 36977975 | 36978009 | chr14 | 36978548 | 36978578 | chr14 | 36979619 | 36979649 |
| chr14 | 36982927 | 36982969 | chr14 | 36983708 | 36984146 | chr14 | 36985841 | 36985871 |
| chr14 | 36986301 | 36986471 | chr14 | 36987302 | 36987685 | chr14 | 36987939 | 36988143 |
| chr14 | 36988428 | 36988460 | chr14 | 36990858 | 36991032 | chr14 | 36991095 | 36991177 |
| chr14 | 36991532 | 36991613 | chr14 | 36991989 | 36992163 | chr14 | 36992222 | 36992417 |
| chr14 | 36993473 | 36993487 | chr14 | 36993694 | 36993956 | chr14 | 36994248 | 36994999 |
| chr14 | 37050752 | 37050794 | chr14 | 37116105 | 37116294 | chr14 | 37117611 | 37117697 |
| chr14 | 37123438 | 37124077 | chr14 | 37124482 | 37124572 | chr14 | 37124992 | 37125545 |
| chr14 | 37126241 | 37126297 | chr14 | 37126566 | 37126713 | chr14 | 37127281 | 37127311 |
| chr14 | 37127655 | 37127779 | chr14 | 37128553 | 37128723 | chr14 | 37130077 | 37130260 |
| chr14 | 37132375 | 37132553 | chr14 | 37132603 | 37132695 | chr14 | 37133001 | 37133052 |
| chr14 | 37135784 | 37136017 | chr14 | 37136295 | 37136345 | chr14 | 37136588 | 37136618 |
| chr14 | 38060677 | 38060916 | chr14 | 38064401 | 38064549 | chr14 | 38677519 | 38677548 |
| chr14 | 38677761 | 38677790 | chr14 | 38724294 | 38724525 | chr14 | 38724979 | 38725258 |
| chr14 | 38725521 | 38725764 | chr14 | 39579800 | 39579830 | chr14 | 42074544 | 42074586 |
| chr14 | 42074669 | 42074987 | chr14 | 42075588 | 42076043 | chr14 | 42076106 | 42076212 |
| chr14 | 42076823 | 42076853 | chr14 | 42077230 | 42077268 | chr14 | 42077770 | 42077800 |
| chr14 | 42079289 | 42079328 | chr14 | 48143798 | 48143957 | chr14 | 48144359 | 48144401 |
| chr14 | 48144699 | 48144763 | chr14 | 48145237 | 48145257 | chr14 | 50333964 | 50333994 |
| chr14 | 50334335 | 50334355 | chr14 | 51338730 | 51338731 | chr14 | 51560304 | 51560713 |
| chr14 | 51560771 | 51561428 | chr14 | 51561765 | 51562012 | chr14 | 51955509 | 51955538 |
| chr14 | 52534648 | 52534791 | chr14 | 52535012 | 52535026 | chr14 | 52535056 | 52535263 |
| chr14 | 52535335 | 52536104 | chr14 | 52536330 | 52536404 | chr14 | 52734509 | 52734557 |
| chr14 | 52734777 | 52735001 | chr14 | 52735045 | 52735255 | chr14 | 52781525 | 52781916 |
| chr14 | 54422651 | 54422925 | chr14 | 55370202 | 55370219 | chr14 | 55595938 | 55595968 |
| chr14 | 55765285 | 55765714 | chr14 | 55823079 | 55823179 | chr14 | 57045520 | 57045739 |
| chr14 | 57260946 | 57261094 | chr14 | 57261175 | 57261407 | chr14 | 57261466 | 57261821 |
| chr14 | 57262072 | 57262179 | chr14 | 57264079 | 57264645 | chr14 | 57264765 | 57264806 |
| chr14 | 57265148 | 57265240 | chr14 | 57270936 | 57270971 | chr14 | 57271154 | 57271266 |
| chr14 | 57272009 | 57272067 | chr14 | 57274486 | 57275049 | chr14 | 57275211 | 57275305 |
| chr14 | 57275596 | 57275685 | chr14 | 57276074 | 57276104 | chr14 | 57276440 | 57276666 |
| chr14 | 57277920 | 57278762 | chr14 | 57278838 | 57279564 | chr14 | 57279643 | 57279657 |

TABLE 13-continued

| chr | start | end | chr | start | end | chr | start | end |
|---|---|---|---|---|---|---|---|---|
| chr14 | 57283314 | 57283408 | chr14 | 57283446 | 57284036 | chr14 | 57284071 | 57284659 |
| chr14 | 58332297 | 58332403 | chr14 | 59770326 | 59770359 | chr14 | 60097193 | 60097246 |
| chr14 | 60097407 | 60097566 | chr14 | 60386207 | 60386252 | chr14 | 60386638 | 60386701 |
| chr14 | 60794635 | 60794667 | chr14 | 60952196 | 60962419 | chr14 | 60952517 | 60952632 |
| chr14 | 60952730 | 60952959 | chr14 | 60973151 | 60973324 | chr14 | 60973697 | 60974007 |
| chr14 | 60974368 | 60974403 | chr14 | 60975384 | 60975888 | chr14 | 60976075 | 60976514 |
| chr14 | 60976813 | 60976860 | chr14 | 60977337 | 60977712 | chr14 | 60977880 | 60978147 |
| chr14 | 60981202 | 60981268 | chr14 | 60981676 | 60981793 | chr14 | 60982110 | 60982367 |
| chr14 | 60982574 | 60982622 | chr14 | 60982841 | 60982911 | chr14 | 61104291 | 61104556 |
| chr14 | 61104624 | 61104864 | chr14 | 61108620 | 61108996 | chr14 | 61109206 | 61109470 |
| chr14 | 61109839 | 61110243 | chr14 | 61114137 | 61114456 | chr14 | 61115311 | 61115517 |
| chr14 | 61118743 | 61118765 | chr14 | 61118965 | 61119136 | chr14 | 61119536 | 61119639 |
| chr14 | 61747389 | 61747527 | chr14 | 61747583 | 61748033 | chr14 | 62279578 | 62279852 |
| chr14 | 62279899 | 62280006 | chr14 | 62583809 | 62583869 | chr14 | 63512100 | 63512291 |
| chr14 | 63512573 | 63512708 | chr14 | 63512741 | 63512816 | chr14 | 63513124 | 63513154 |
| chr14 | 64222413 | 64222451 | chr14 | 65005795 | 65005833 | chr14 | 65008998 | 65009193 |
| chr14 | 65233339 | 65233464 | chr14 | 67585164 | 67585199 | chr14 | 67886582 | 67886606 |
| chr14 | 69014044 | 69014110 | chr14 | 69866541 | 69866564 | chr14 | 69867022 | 69867196 |
| chr14 | 70014723 | 70014974 | chr14 | 70038990 | 70039025 | chr14 | 70346136 | 70346491 |
| chr14 | 70654378 | 70654713 | chr14 | 70655530 | 70655889 | chr14 | 70655920 | 70656090 |
| chr14 | 72398743 | 72399019 | chr14 | 72399452 | 72399453 | chr14 | 72399929 | 72400029 |
| chr14 | 73167750 | 73167899 | chr14 | 73175026 | 73175148 | chr14 | 73178807 | 73178865 |
| chr14 | 73180208 | 73180314 | chr14 | 73236095 | 73236137 | chr14 | 73318471 | 73318629 |
| chr14 | 73333249 | 73333293 | chr14 | 73602350 | 73602389 | chr14 | 74706015 | 74706222 |
| chr14 | 74706941 | 74707544 | chr14 | 74707573 | 74707747 | chr14 | 74707792 | 74707873 |
| chr14 | 74708862 | 74708955 | chr14 | 74892540 | 74892569 | chr14 | 74893074 | 74893113 |
| chr14 | 75078170 | 75078242 | chr14 | 75760311 | 75760329 | chr14 | 75988341 | 75988370 |
| chr14 | 75988732 | 75988761 | chr14 | 76128674 | 76128698 | chr14 | 76604682 | 76604716 |
| chr14 | 76605072 | 76605376 | chr14 | 76843742 | 76843953 | chr14 | 77228121 | 77228159 |
| chr14 | 77606922 | 77607236 | chr14 | 77737212 | 77737814 | chr14 | 79745138 | 79745175 |
| chr14 | 85996479 | 85996608 | chr14 | 85996892 | 85996906 | chr14 | 85997821 | 85997925 |
| chr14 | 85998288 | 85998574 | chr14 | 85998630 | 85998683 | chr14 | 85999597 | 85999613 |
| chr14 | 86000270 | 86000511 | chr14 | 86000918 | 86001114 | chr14 | 89817889 | 89818034 |
| chr14 | 90527714 | 90527758 | chr14 | 90983328 | 90983360 | chr14 | 91691163 | 91691306 |
| chr14 | 91691789 | 91691822 | chr14 | 91766154 | 91766450 | chr14 | 91780382 | 91780592 |
| chr14 | 91801036 | 91801164 | chr14 | 92507655 | 92507792 | chr14 | 92789512 | 92789542 |
| chr14 | 92789960 | 92790098 | chr14 | 92790637 | 92790703 | chr14 | 92979917 | 92979991 |
| chr14 | 93155061 | 93155315 | chr14 | 93389557 | 93389693 | chr14 | 93389713 | 93389776 |
| chr14 | 93571193 | 93571326 | chr14 | 93706752 | 93706782 | chr14 | 94254389 | 94254458 |
| chr14 | 94254499 | 94254513 | chr14 | 94405734 | 94405785 | chr14 | 94603642 | 94603670 |
| chr14 | 94889856 | 94889870 | chr14 | 95233705 | 95233765 | chr14 | 95234643 | 95234710 |
| chr14 | 95235026 | 95235369 | chr14 | 95235989 | 95236111 | chr14 | 95236524 | 95236553 |
| chr14 | 95236819 | 95236848 | chr14 | 95237622 | 95237642 | chr14 | 95239422 | 95239633 |
| chr14 | 95240127 | 95240157 | chr14 | 95240227 | 95240341 | chr14 | 95240392 | 95240422 |
| chr14 | 95557626 | 95557655 | chr14 | 95560448 | 95560477 | chr14 | 95740035 | 95740116 |
| chr14 | 96342897 | 96343133 | chr14 | 96343404 | 96343433 | chr14 | 96343668 | 96343701 |
| chr14 | 97045354 | 97045431 | chr14 | 97058944 | 97059083 | chr14 | 97499277 | 97499315 |
| chr14 | 97499847 | 97499849 | chr14 | 97685044 | 97685288 | chr14 | 97685707 | 97685959 |
| chr14 | 99584575 | 99584664 | chr14 | 99712321 | 99712394 | chr14 | 99736151 | 99736183 |
| chr14 | 99737398 | 99737462 | chr14 | 100437794 | 100437949 | chr14 | 100438705 | 100438811 |
| chr14 | 100643350 | 100643481 | chr14 | 100793556 | 100793650 | chr14 | 101250109 | 101250272 |
| chr14 | 101506231 | 101506260 | chr14 | 101543868 | 101544235 | chr14 | 101923114 | 101923250 |
| chr14 | 101923600 | 101923686 | chr14 | 101924031 | 101924047 | chr14 | 101925049 | 101925071 |
| chr14 | 101925656 | 101925901 | chr14 | 102026360 | 102026484 | chr14 | 102026797 | 102026967 |
| chr14 | 102031236 | 102031271 | chr14 | 102031512 | 102031580 | chr14 | 102247912 | 102248214 |
| chr14 | 102418607 | 102418637 | chr14 | 102521602 | 102521758 | chr14 | 102530007 | 102530234 |
| chr14 | 102530500 | 102530530 | chr14 | 102564464 | 102564505 | chr14 | 102682077 | 102682149 |
| chr14 | 102973169 | 102973268 | chr14 | 103021391 | 103022003 | chr14 | 103394884 | 103395101 |
| chr14 | 103477643 | 103477779 | chr14 | 103655226 | 103655601 | chr14 | 103674078 | 103674079 |
| chr14 | 103687082 | 103687219 | chr14 | 103739967 | 103740150 | chr14 | 103740358 | 103740430 |
| chr14 | 103745699 | 103745750 | chr14 | 104160060 | 104160134 | chr14 | 104202705 | 104202759 |
| chr14 | 104547785 | 104547909 | chr14 | 104571985 | 104572116 | chr14 | 104601737 | 104601832 |
| chr14 | 104602033 | 104602063 | chr14 | 104605032 | 104605114 | chr14 | 104620411 | 104620554 |
| chr14 | 104627664 | 104627759 | chr14 | 104645126 | 104645188 | chr14 | 104646317 | 104646491 |
| chr14 | 104647257 | 104647287 | chr14 | 104682545 | 104682656 | chr14 | 104862860 | 104863026 |
| chr14 | 105071298 | 105071396 | chr14 | 105157485 | 105157554 | chr14 | 105239389 | 105239439 |
| chr14 | 105239793 | 105239825 | chr14 | 105241309 | 105241428 | chr14 | 105243032 | 105243064 |
| chr14 | 105246427 | 105246582 | chr14 | 105512063 | 105512395 | chr14 | 105658349 | 105658425 |
| chr14 | 105714258 | 105714334 | chr14 | 105714415 | 105714441 | chr14 | 105715248 | 105715392 |
| chr14 | 105830630 | 105830859 | chr14 | 105963655 | 105963772 | chr15 | 22822348 | 22822388 |
| chr15 | 23158397 | 23158489 | chr15 | 23692316 | 23692415 | chr15 | 26107640 | 26107743 |
| chr15 | 26107846 | 26107860 | chr15 | 26108096 | 26108326 | chr15 | 26108549 | 26108701 |
| chr15 | 27212887 | 27213172 | chr15 | 27604062 | 27604123 | chr15 | 28341699 | 28342019 |
| chr15 | 28344173 | 28344187 | chr15 | 28344224 | 28344287 | chr15 | 28352240 | 28352421 |
| chr15 | 29077284 | 29077383 | chr15 | 29130807 | 29131047 | chr15 | 29131533 | 29131630 |
| chr15 | 29131756 | 29131875 | chr15 | 29396330 | 29396360 | chr15 | 29407777 | 29407813 |
| chr15 | 29407867 | 29408001 | chr15 | 29862502 | 29862582 | chr15 | 30115185 | 30115228 |
| chr15 | 31455370 | 31455485 | chr15 | 31775596 | 31775637 | chr15 | 31775679 | 31775782 |

TABLE 13-continued

| chr | start | end | chr | start | end | chr | start | end |
|---|---|---|---|---|---|---|---|---|
| chr15 | 32933918 | 32934018 | chr15 | 33009747 | 33009761 | chr15 | 33009822 | 33010675 |
| chr15 | 33010721 | 33011348 | chr15 | 33011601 | 33011633 | chr15 | 33487057 | 33487120 |
| chr15 | 33602801 | 33602886 | chr15 | 33603194 | 33603608 | chr15 | 33879242 | 33879272 |
| chr15 | 34517058 | 34517334 | chr15 | 34630439 | 34630449 | chr15 | 34630515 | 34630544 |
| chr15 | 34729478 | 34729582 | chr15 | 34786504 | 34786943 | chr15 | 34787233 | 34787304 |
| chr15 | 35046607 | 35046608 | chr15 | 35047034 | 35047133 | chr15 | 35087666 | 35087698 |
| chr15 | 37180309 | 37180743 | chr15 | 37402974 | 37403086 | chr15 | 37403116 | 37403238 |
| chr15 | 40211819 | 40212190 | chr15 | 40575630 | 40575744 | chr15 | 40671588 | 40671620 |
| chr15 | 40675092 | 40675121 | chr15 | 40763811 | 40763862 | chr15 | 40782219 | 40782249 |
| chr15 | 41165245 | 41165700 | chr15 | 41804878 | 41805772 | chr15 | 41835694 | 41835720 |
| chr15 | 41913750 | 41913807 | chr15 | 41952572 | 41952711 | chr15 | 42749733 | 42749899 |
| chr15 | 43551059 | 43551196 | chr15 | 43810405 | 43810435 | chr15 | 44037568 | 44037604 |
| chr15 | 45403636 | 45403680 | chr15 | 45403799 | 45403999 | chr15 | 45404103 | 45404130 |
| chr15 | 45404898 | 45405117 | chr15 | 45421385 | 45421435 | chr15 | 45421998 | 45422095 |
| chr15 | 45427370 | 45427410 | chr15 | 45427611 | 45427719 | chr15 | 45427772 | 45427786 |
| chr15 | 45444061 | 45444141 | chr15 | 45479460 | 45479516 | chr15 | 45493209 | 45493371 |
| chr15 | 45670462 | 45670838 | chr15 | 46021437 | 46021467 | chr15 | 47476118 | 47476239 |
| chr15 | 47476291 | 47476419 | chr15 | 47476877 | 47476980 | chr15 | 47477013 | 47477018 |
| chr15 | 48483956 | 48483986 | chr15 | 48936726 | 48937645 | chr15 | 48937710 | 48937987 |
| chr15 | 48938212 | 48938510 | chr15 | 51385913 | 51386181 | chr15 | 51634075 | 51634135 |
| chr15 | 51973646 | 51973694 | chr15 | 51973764 | 51973934 | chr15 | 53075809 | 53075864 |
| chr15 | 53075986 | 53077000 | chr15 | 53077066 | 53077361 | chr15 | 53077655 | 53077731 |
| chr15 | 53078064 | 53078236 | chr15 | 53079340 | 53079677 | chr15 | 53079718 | 53079891 |
| chr15 | 53079971 | 53080082 | chr15 | 53080337 | 53080606 | chr15 | 53080935 | 53080990 |
| chr15 | 53081399 | 53081677 | chr15 | 53082443 | 53082491 | chr15 | 53096816 | 53096891 |
| chr15 | 53097231 | 53097261 | chr15 | 53097778 | 53097906 | chr15 | 53098382 | 53098658 |
| chr15 | 54270498 | 54270707 | chr15 | 54270932 | 54270961 | chr15 | 55452967 | 55452993 |
| chr15 | 55699089 | 55699127 | chr15 | 55806758 | 55806859 | chr15 | 55880891 | 55881011 |
| chr15 | 58357800 | 58357819 | chr15 | 59158488 | 59158537 | chr15 | 59950341 | 59950363 |
| chr15 | 60287038 | 60287585 | chr15 | 60287644 | 60287733 | chr15 | 60288786 | 60288844 |
| chr15 | 60289310 | 60289546 | chr15 | 60296122 | 60296209 | chr15 | 60296598 | 60296617 |
| chr15 | 60296861 | 60296923 | chr15 | 60297152 | 60297409 | chr15 | 60297637 | 60297826 |
| chr15 | 60297942 | 60298108 | chr15 | 61520916 | 61521014 | chr15 | 61521659 | 61521937 |
| chr15 | 62456922 | 62456952 | chr15 | 65669859 | 65669899 | chr15 | 65685591 | 65685708 |
| chr15 | 65862033 | 65862121 | chr15 | 66727409 | 66727498 | chr15 | 66729148 | 66729177 |
| chr15 | 66774117 | 66774203 | chr15 | 66963816 | 66963871 | chr15 | 68112611 | 68112641 |
| chr15 | 68113868 | 68113898 | chr15 | 68114139 | 68114195 | chr15 | 68116369 | 68116621 |
| chr15 | 68117830 | 68118633 | chr15 | 68118930 | 68119174 | chr15 | 68119579 | 68120352 |
| chr15 | 68120827 | 68120857 | chr15 | 68121150 | 68121957 | chr15 | 68122643 | 68122673 |
| chr15 | 68125261 | 68125664 | chr15 | 68127801 | 68128350 | chr15 | 68128594 | 68128688 |
| chr15 | 68260519 | 68260709 | chr15 | 71055636 | 71055815 | chr15 | 72412083 | 72412176 |
| chr15 | 72612540 | 72612906 | chr15 | 72743741 | 72743796 | chr15 | 73660004 | 73660067 |
| chr15 | 73661469 | 73661666 | chr15 | 74045075 | 74045097 | chr15 | 74422006 | 74422146 |
| chr15 | 74422869 | 74423002 | chr15 | 74658151 | 74658396 | chr15 | 74658502 | 74658587 |
| chr15 | 74686021 | 74686051 | chr15 | 74818772 | 74818789 | chr15 | 74903896 | 74903926 |
| chr15 | 75251346 | 75251382 | chr15 | 75251672 | 75251786 | chr15 | 76627508 | 76627536 |
| chr15 | 76627576 | 76627826 | chr15 | 76629163 | 76629220 | chr15 | 76629494 | 76629531 |
| chr15 | 76629814 | 76630124 | chr15 | 76630520 | 76630847 | chr15 | 76638472 | 76638496 |
| chr15 | 77448967 | 77449001 | chr15 | 78111196 | 78111210 | chr15 | 78501806 | 78501942 |
| chr15 | 78556819 | 78557108 | chr15 | 78596065 | 78596218 | chr15 | 78632727 | 78632823 |
| chr15 | 78912281 | 78912371 | chr15 | 78912623 | 78912653 | chr15 | 78912912 | 78913027 |
| chr15 | 78913095 | 78913170 | chr15 | 78913535 | 78913651 | chr15 | 79104217 | 79104246 |
| chr15 | 79104466 | 79104495 | chr15 | 79381705 | 79381745 | chr15 | 79382099 | 79382571 |
| chr15 | 79382786 | 79383257 | chr15 | 79383947 | 79383977 | chr15 | 79502211 | 79502360 |
| chr15 | 79575278 | 79575474 | chr15 | 79576145 | 79576277 | chr15 | 79724502 | 79724560 |
| chr15 | 79724607 | 79724792 | chr15 | 79724864 | 79725140 | chr15 | 79725422 | 79725539 |
| chr15 | 81071827 | 81071867 | chr15 | 82336879 | 82336972 | chr15 | 82340070 | 82340157 |
| chr15 | 83315336 | 83315393 | chr15 | 83316251 | 83317087 | chr15 | 83349234 | 83349611 |
| chr15 | 83349672 | 83349686 | chr15 | 83378212 | 83378370 | chr15 | 83776255 | 83776306 |
| chr15 | 83776333 | 83776716 | chr15 | 83776769 | 83776785 | chr15 | 83866523 | 83866541 |
| chr15 | 83875648 | 83875665 | chr15 | 83875706 | 83875901 | chr15 | 83877055 | 83877149 |
| chr15 | 83953884 | 83953903 | chr15 | 83954380 | 83954409 | chr15 | 84115747 | 84115853 |
| chr15 | 84115932 | 84115966 | chr15 | 84116905 | 84116949 | chr15 | 84322994 | 84323037 |
| chr15 | 84748578 | 84748619 | chr15 | 84748679 | 84749260 | chr15 | 85143024 | 85143054 |
| chr15 | 88798725 | 88798791 | chr15 | 88799537 | 88800301 | chr15 | 88800541 | 88801008 |
| chr15 | 88801089 | 88801103 | chr15 | 89149169 | 89149448 | chr15 | 89248753 | 89248907 |
| chr15 | 89346050 | 89346326 | chr15 | 89346347 | 89346393 | chr15 | 89346670 | 89346793 |
| chr15 | 89346882 | 89346943 | chr15 | 89903484 | 89903814 | chr15 | 89910521 | 89910748 |
| chr15 | 89911087 | 89911186 | chr15 | 89913750 | 89913780 | chr15 | 89914231 | 89914449 |
| chr15 | 89914867 | 89914895 | chr15 | 89915240 | 89915369 | chr15 | 89921956 | 89922006 |
| chr15 | 89922500 | 89922546 | chr15 | 89942755 | 89942945 | chr15 | 89943410 | 89943706 |
| chr15 | 89949617 | 89949942 | chr15 | 89950236 | 89950736 | chr15 | 89951082 | 89951113 |
| chr15 | 89951466 | 89951801 | chr15 | 89952153 | 89952452 | chr15 | 89952700 | 89953055 |
| chr15 | 89954197 | 89954335 | chr16 | 89956423 | 89956450 | chr15 | 90039563 | 90039711 |
| chr15 | 90631823 | 90631948 | chr15 | 90756916 | 90756079 | chr15 | 91643360 | 91643586 |
| chr15 | 92936290 | 92936322 | chr15 | 92937153 | 92937374 | chr15 | 92937927 | 92938060 |
| chr15 | 92938123 | 92938293 | chr15 | 93158592 | 93158739 | chr15 | 93631739 | 93632014 |
| chr15 | 93632660 | 93633233 | chr15 | 94347602 | 94347632 | chr15 | 96874362 | 96874514 |

TABLE 13-continued

| chr | start | end | chr | start | end | chr | start | end |
|---|---|---|---|---|---|---|---|---|
| chr15 | 96889154 | 96889183 | chr15 | 96889401 | 96889430 | chr15 | 96897934 | 96898010 |
| chr15 | 96911559 | 96911691 | chr15 | 96952696 | 96953098 | chr15 | 96953132 | 96953209 |
| chr15 | 96959730 | 96959960 | chr15 | 96960376 | 96960409 | chr15 | 96960732 | 96960826 |
| chr15 | 97006372 | 97006533 | chr15 | 98504114 | 98504144 | chr15 | 98836178 | 98836393 |
| chr15 | 98964786 | 98965138 | chr15 | 99193206 | 99193480 | chr15 | 99193914 | 99194186 |
| chr15 | 99453230 | 99453440 | chr15 | 99456299 | 99456329 | chr15 | 99497059 | 99497132 |
| chr15 | 100913423 | 100913595 | chr15 | 101420521 | 101420610 | chr15 | 101420972 | 101420989 |
| chr15 | 101818327 | 101818357 | chr16 | 93831 | 93932 | chr16 | 142649 | 142783 |
| chr16 | 215416 | 215872 | chr16 | 215913 | 216224 | chr16 | 216676 | 217036 |
| chr16 | 230265 | 230315 | chr16 | 230497 | 230610 | chr16 | 318104 | 318227 |
| chr16 | 318498 | 318763 | chr16 | 337599 | 337659 | chr16 | 410377 | 410407 |
| chr16 | 565492 | 565623 | chr16 | 571714 | 571959 | chr16 | 611385 | 611520 |
| chr16 | 611969 | 612260 | chr16 | 612869 | 613037 | chr16 | 667141 | 667297 |
| chr16 | 667547 | 667585 | chr16 | 667876 | 668074 | chr16 | 672768 | 672806 |
| chr16 | 677972 | 678084 | chr16 | 700299 | 700329 | chr16 | 726626 | 726990 |
| chr16 | 731488 | 731610 | chr16 | 735205 | 735594 | chr16 | 740883 | 740914 |
| chr16 | 741376 | 741519 | chr16 | 762669 | 762694 | chr16 | 837361 | 837460 |
| chr16 | 845955 | 845985 | chr16 | 882566 | 882588 | chr16 | 895093 | 895166 |
| chr16 | 943481 | 943553 | chr16 | 1018120 | 1018150 | chr16 | 1019640 | 1019685 |
| chr16 | 1030444 | 1030655 | chr16 | 1052587 | 1052627 | chr16 | 1102927 | 1102957 |
| chr16 | 1116661 | 1116691 | chr16 | 1122858 | 1122946 | chr16 | 1129011 | 1129140 |
| chr16 | 1155162 | 1155212 | chr16 | 1204003 | 1204034 | chr16 | 1217307 | 1217503 |
| chr16 | 1218034 | 1218090 | chr16 | 1228804 | 1228916 | chr16 | 1230056 | 1230142 |
| chr16 | 1248604 | 1248675 | chr16 | 1267925 | 1268120 | chr16 | 1271546 | 1271646 |
| chr16 | 1312526 | 1312611 | chr16 | 1323976 | 1324061 | chr16 | 1382901 | 1382940 |
| chr16 | 1394502 | 1394596 | chr16 | 1397454 | 1397484 | chr16 | 1407370 | 1407518 |
| chr16 | 1407818 | 1407846 | chr16 | 1408210 | 1408240 | chr16 | 1428508 | 1428873 |
| chr16 | 1491567 | 1491613 | chr16 | 1704656 | 1704800 | chr16 | 1730306 | 1730597 |
| chr16 | 1741853 | 1742079 | chr16 | 1750769 | 1750907 | chr16 | 1842490 | 1842519 |
| chr16 | 2029072 | 2029137 | chr16 | 2040914 | 2040960 | chr16 | 2040981 | 2041512 |
| chr16 | 2041582 | 2042160 | chr16 | 2042875 | 2042905 | chr16 | 2086831 | 2086860 |
| chr16 | 2106703 | 2106732 | chr16 | 2111966 | 2111995 | chr16 | 2120515 | 2120544 |
| chr16 | 2122243 | 2122272 | chr16 | 2124205 | 2124348 | chr16 | 2126080 | 2126109 |
| chr16 | 2128577 | 2129581 | chr16 | 2130361 | 2130390 | chr16 | 2132244 | 2132315 |
| chr16 | 2135301 | 2135330 | chr16 | 2136228 | 2136257 | chr16 | 2136727 | 2136855 |
| chr16 | 2140403 | 2140438 | chr16 | 2141909 | 2141972 | chr16 | 2142546 | 2142628 |
| chr16 | 2213313 | 2213343 | chr16 | 2232745 | 2232784 | chr16 | 2234726 | 2235020 |
| chr16 | 2281249 | 2281314 | chr16 | 2287295 | 2287370 | chr16 | 2485858 | 2485917 |
| chr16 | 2531069 | 2531177 | chr16 | 2764377 | 2764470 | chr16 | 2770122 | 2770512 |
| chr16 | 2818101 | 2818156 | chr16 | 2892542 | 2892602 | chr16 | 2892627 | 2892729 |
| chr16 | 2974601 | 2974650 | chr16 | 3017157 | 3017430 | chr16 | 3068171 | 3068201 |
| chr16 | 3151127 | 3151186 | chr16 | 3211708 | 3211744 | chr16 | 3211804 | 3211984 |
| chr16 | 3220591 | 3220892 | chr16 | 3221142 | 3221700 | chr16 | 3221787 | 3222239 |
| chr16 | 3225471 | 3225607 | chr16 | 3232739 | 3233016 | chr16 | 3233199 | 3233330 |
| chr16 | 3233435 | 3234103 | chr16 | 3234196 | 3234452 | chr16 | 3237857 | 3238022 |
| chr16 | 3238142 | 3238546 | chr16 | 3238993 | 3239631 | chr16 | 3239691 | 3239848 |
| chr16 | 3241549 | 3241663 | chr16 | 3241936 | 3241966 | chr16 | 3355279 | 3355718 |
| chr16 | 3598920 | 3598953 | chr16 | 3696694 | 3696724 | chr16 | 3802981 | 3803074 |
| chr16 | 3950263 | 3950279 | chr16 | 4264529 | 4264694 | chr16 | 4310735 | 4310847 |
| chr16 | 4431126 | 4431189 | chr16 | 4431487 | 4431516 | chr16 | 4731638 | 4731718 |
| chr16 | 4733166 | 4733195 | chr16 | 4738567 | 4738680 | chr16 | 4751554 | 4751583 |
| chr15 | 4846136 | 4846415 | chr16 | 4887144 | 4887164 | chr16 | 5037900 | 5038004 |
| chr16 | 5541116 | 5541158 | chr16 | 6069941 | 6070019 | chr16 | 7354634 | 7354657 |
| chr16 | 7382499 | 7382534 | chr16 | 8781032 | 8781135 | chr16 | 8870353 | 8870383 |
| chr16 | 9009860 | 9009989 | chr16 | 10274399 | 10274429 | chr16 | 10275308 | 10275392 |
| chr16 | 10275752 | 10275948 | chr16 | 10276360 | 10277050 | chr16 | 10277072 | 10277409 |
| chr16 | 10479815 | 10479980 | chr16 | 11242000 | 11242138 | chr16 | 11427659 | 11427732 |
| chr16 | 11490632 | 11490662 | chr16 | 12210772 | 12210896 | chr16 | 12211279 | 12211416 |
| chr16 | 12530169 | 12530199 | chr16 | 12971776 | 12971934 | chr16 | 12994459 | 12994737 |
| chr16 | 12995062 | 12995593 | chr16 | 12995803 | 12995803 | chr16 | 12996074 | 12996328 |
| chr16 | 12996617 | 12996720 | chr16 | 12996948 | 12997011 | chr16 | 12997386 | 12997703 |
| chr16 | 14021974 | 14022003 | chr16 | 14041504 | 14041533 | chr16 | 14041795 | 14041824 |
| chr16 | 14042062 | 14042091 | chr16 | 14725842 | 14725864 | chr16 | 15489599 | 15489808 |
| chr16 | 15739004 | 15739042 | chr16 | 15820825 | 15820865 | chr16 | 18802465 | 18802680 |
| chr16 | 18950973 | 18951018 | chr16 | 19531564 | 19531601 | chr16 | 19567202 | 19567449 |
| chr16 | 19895125 | 19895155 | chr16 | 21666641 | 21666771 | chr16 | 21831621 | 21831957 |
| chr16 | 21839328 | 21839369 | chr16 | 22326397 | 22326427 | chr16 | 22824701 | 22825076 |
| chr16 | 22825327 | 22825469 | chr16 | 22825886 | 22826081 | chr16 | 23313464 | 23313522 |
| chr16 | 23313780 | 23313836 | chr16 | 23706412 | 23706520 | chr16 | 23766097 | 23766130 |
| chr16 | 23847311 | 23847511 | chr16 | 23847789 | 23847874 | chr16 | 23847934 | 23847956 |
| chr16 | 24127295 | 24127338 | chr16 | 24172241 | 24172271 | chr16 | 24180710 | 24180760 |
| chr16 | 24267115 | 24267144 | chr16 | 24267485 | 24267578 | chr16 | 25266537 | 25266573 |
| chr15 | 25542437 | 25542452 | chr16 | 25702955 | 25702992 | chr16 | 25703685 | 25704122 |
| chr16 | 25704390 | 25704628 | chr16 | 25921574 | 25921604 | chr16 | 26664757 | 26664775 |
| chr16 | 27459938 | 27460074 | chr16 | 27749857 | 27750033 | chr16 | 28074176 | 28074254 |
| chr16 | 28074418 | 28074684 | chr16 | 28074959 | 28075197 | chr16 | 28877839 | 28877883 |
| chr16 | 28891040 | 28891072 | chr16 | 29119008 | 29119058 | chr16 | 29153284 | 29153320 |
| chr16 | 29244900 | 29244997 | chr16 | 29830871 | 29831078 | chr16 | 29888624 | 29888658 |

TABLE 13-continued

| chr | start | end | chr | start | end | chr | start | end |
|---|---|---|---|---|---|---|---|---|
| chr16 | 30017330 | 30017447 | chr16 | 30116285 | 30116315 | chr16 | 30124691 | 30124861 |
| chr16 | 30804457 | 30804472 | chr16 | 30826362 | 30826509 | chr16 | 30907010 | 30907049 |
| chr16 | 30907109 | 30907148 | chr16 | 31227914 | 31228313 | chr16 | 31384593 | 31384623 |
| chr16 | 31446873 | 31447096 | chr16 | 31498008 | 31498087 | chr16 | 31500544 | 31500673 |
| chr16 | 31580560 | 31581036 | chr16 | 46721567 | 46721707 | chr16 | 47177525 | 47177606 |
| chr16 | 48641663 | 48641693 | chr16 | 48845120 | 48845125 | chr16 | 49309170 | 49309262 |
| chr16 | 49311523 | 49311989 | chr16 | 49312033 | 49312299 | chr16 | 49313363 | 49313710 |
| chr16 | 49314022 | 49314118 | chr16 | 49314419 | 49314561 | chr16 | 49314784 | 49314821 |
| chr16 | 49315276 | 49315306 | chr16 | 49315919 | 49316315 | chr16 | 49316509 | 49316580 |
| chr16 | 49638060 | 49638090 | chr16 | 50335767 | 50335797 | chr16 | 51183964 | 51184406 |
| chr16 | 51184807 | 51184957 | chr16 | 51185055 | 51185291 | chr16 | 51185844 | 51185964 |
| chr16 | 51186026 | 51186280 | chr16 | 51186596 | 51186939 | chr16 | 51188697 | 51188711 |
| chr16 | 51189922 | 51190037 | chr16 | 51190122 | 51190215 | chr16 | 53467363 | 53467395 |
| chr16 | 53563622 | 53563654 | chr16 | 54128645 | 54128713 | chr16 | 54318898 | 54318988 |
| chr16 | 54319420 | 54319468 | chr16 | 54321638 | 54321818 | chr16 | 54324999 | 54325131 |
| chr16 | 54628691 | 54628867 | chr16 | 54964948 | 54965114 | chr16 | 54966830 | 54967264 |
| chr16 | 54971400 | 54971430 | chr16 | 55090666 | 55090861 | chr16 | 55357926 | 55357940 |
| chr16 | 55357992 | 55358086 | chr16 | 55358316 | 55358350 | chr16 | 55358798 | 55359071 |
| chr16 | 55363009 | 55363223 | chr16 | 55364716 | 55364843 | chr16 | 55365103 | 55365218 |
| chr16 | 55404999 | 55405214 | chr16 | 55689886 | 55689915 | chr16 | 55690115 | 55690379 |
| chr16 | 55690454 | 55690576 | chr16 | 55690762 | 55690809 | chr16 | 56224557 | 56224832 |
| chr16 | 56228370 | 56228416 | chr16 | 56228578 | 56228581 | chr16 | 56651094 | 56651123 |
| chr16 | 56651239 | 56651275 | chr16 | 56659175 | 56659673 | chr16 | 56672158 | 56672172 |
| chr16 | 56672222 | 56672385 | chr16 | 56672514 | 56672654 | chr16 | 56672656 | 56672685 |
| chr16 | 56709837 | 56709892 | chr16 | 56709950 | 56710030 | chr16 | 57222686 | 57222709 |
| chr16 | 57318379 | 57318412 | chr16 | 57935454 | 57935605 | chr16 | 58018634 | 58018845 |
| chr16 | 58019225 | 58019430 | chr16 | 58120795 | 58120961 | chr16 | 58497221 | 58497335 |
| chr16 | 58497752 | 58497829 | chr16 | 58498175 | 58498204 | chr16 | 58498570 | 58498724 |
| chr16 | 58521708 | 58521737 | chr16 | 58534666 | 58534695 | chr16 | 58545487 | 58545516 |
| chr16 | 58550489 | 58550519 | chr16 | 58969757 | 58969792 | chr16 | 62068463 | 62068517 |
| chr16 | 62068952 | 62068982 | chr16 | 62070743 | 62070773 | chr16 | 65154933 | 65155091 |
| chr16 | 65156385 | 65156489 | chr16 | 66461786 | 66461840 | chr16 | 66612882 | 66613095 |
| chr16 | 66613335 | 66613369 | chr16 | 67197698 | 67197769 | chr16 | 67198009 | 67198039 |
| chr16 | 67198917 | 67198957 | chr16 | 67241204 | 67241234 | chr16 | 67313865 | 67313895 |
| chr16 | 68481486 | 68481543 | chr16 | 68482808 | 68482941 | chr16 | 68544259 | 68544378 |
| chr16 | 68676408 | 68676604 | chr16 | 68676842 | 68676984 | chr16 | 68770835 | 68771298 |
| chr16 | 68844158 | 68844187 | chr16 | 68846033 | 68846062 | chr16 | 68856078 | 68856107 |
| chr16 | 68876782 | 68876859 | chr16 | 69969260 | 69969290 | chr16 | 70595535 | 70595700 |
| chr16 | 70794492 | 70794633 | chr16 | 71460027 | 71460088 | chr16 | 71460271 | 71460351 |
| chr16 | 71507775 | 71507791 | chr16 | 71715779 | 71715809 | chr16 | 72957763 | 72957795 |
| chr16 | 75019751 | 75019781 | chr16 | 77247440 | 77247470 | chr16 | 77468261 | 77468457 |
| chr16 | 77822589 | 77822874 | chr16 | 78079969 | 78080054 | chr16 | 79623602 | 79623616 |
| chr16 | 79623798 | 79623914 | chr16 | 80837962 | 80838143 | chr16 | 80966399 | 80966431 |
| chr16 | 81564199 | 81564229 | chr16 | 81929362 | 81929392 | chr16 | 81946246 | 81946275 |
| chr16 | 81962167 | 81962196 | chr16 | 82660360 | 82660496 | chr16 | 82660712 | 82660741 |
| chr16 | 84074836 | 84074871 | chr16 | 84153364 | 84153394 | chr16 | 84402244 | 84402319 |
| chr16 | 84519974 | 84520010 | chr16 | 84651793 | 84651822 | chr16 | 84823626 | 84823656 |
| chr16 | 84853288 | 84853376 | chr16 | 85075434 | 85075553 | chr16 | 85317850 | 85317882 |
| chr16 | 85485747 | 85485855 | chr16 | 85497445 | 85497475 | chr16 | 85517345 | 85517521 |
| chr16 | 85651520 | 85651550 | chr16 | 85678639 | 85678761 | chr16 | 85684308 | 85684457 |
| chr16 | 85699689 | 85699921 | chr16 | 85932828 | 85932858 | chr16 | 86320354 | 86320391 |
| chr16 | 86320755 | 86320800 | chr16 | 86321020 | 86321068 | chr16 | 86530942 | 86530992 |
| chr16 | 86531017 | 86531046 | chr16 | 86531375 | 86531480 | chr16 | 86531528 | 86531573 |
| chr16 | 86541591 | 86541968 | chr16 | 86542373 | 86542457 | chr16 | 86544191 | 86544557 |
| chr16 | 86571984 | 86572014 | chr16 | 86599481 | 86599844 | chr16 | 86600483 | 86600686 |
| chr16 | 86600958 | 86601015 | chr16 | 86601286 | 86601539 | chr16 | 86602038 | 86602514 |
| chr16 | 87092439 | 87092553 | chr16 | 87525622 | 87525701 | chr16 | 87635103 | 87635133 |
| chr16 | 87636627 | 87636907 | chr16 | 87714272 | 87714381 | chr16 | 87723735 | 87724098 |
| chr16 | 88007072 | 88007090 | chr16 | 88106322 | 88106398 | chr16 | 88164401 | 88164468 |
| chr16 | 88498241 | 88498760 | chr16 | 88504058 | 88504315 | chr16 | 88506346 | 88506526 |
| chr16 | 88512427 | 88512529 | chr16 | 88543428 | 88543458 | chr16 | 88550263 | 88550483 |
| chr16 | 88603696 | 88603760 | chr16 | 88623960 | 88624167 | chr16 | 88711337 | 88711507 |
| chr16 | 88757466 | 88757496 | chr16 | 88879949 | 88880097 | chr16 | 88883238 | 88883377 |
| chr16 | 88941058 | 88941141 | chr16 | 88942119 | 88942160 | chr16 | 88943559 | 88944024 |
| chr16 | 88945815 | 88945995 | chr16 | 88955249 | 88955368 | chr16 | 88956230 | 88956399 |
| chr16 | 88957350 | 88957857 | chr16 | 88958397 | 88958431 | chr16 | 88963277 | 88963763 |
| chr16 | 88966303 | 88966588 | chr16 | 88968709 | 88968789 | chr16 | 88978024 | 88978072 |
| chr16 | 88993078 | 88993230 | chr16 | 88999617 | 88999647 | chr16 | 89000168 | 89000204 |
| chr16 | 89001094 | 89001124 | chr16 | 89007520 | 89007558 | chr16 | 89007880 | 89007995 |
| chr16 | 89008562 | 89008592 | chr16 | 89047717 | 89047747 | chr16 | 89072503 | 89072774 |
| chr16 | 89086109 | 89086197 | chr16 | 89107675 | 89107732 | chr16 | 89109385 | 89109415 |
| chr16 | 89120038 | 89120319 | chr16 | 89120708 | 89120864 | chr16 | 89138016 | 89138060 |
| chr16 | 89220327 | 89220398 | chr16 | 89220655 | 89220922 | chr16 | 89240843 | 89240873 |
| chr16 | 89254653 | 89254742 | chr16 | 89267334 | 89267364 | chr16 | 89267808 | 89267824 |
| chr16 | 89558610 | 89558703 | chr16 | 89584337 | 89584417 | chr16 | 89883972 | 89884185 |
| chr16 | 89884966 | 89884994 | chr16 | 89885114 | 89885142 | chr16 | 89900124 | 89900180 |
| chr16 | 89900455 | 89900526 | chr17 | 415134 | 415163 | chr17 | 556252 | 556282 |
| chr17 | 617001 | 617033 | chr17 | 1082884 | 1083002 | chr17 | 1174274 | 1174361 |

TABLE 13-continued

| chr | start | end | chr | start | end | chr | start | end |
|---|---|---|---|---|---|---|---|---|
| chr17 | 1174385 | 1174413 | chr17 | 1494550 | 1494613 | chr17 | 1536116 | 1636146 |
| chr17 | 1545976 | 1545999 | chr17 | 1546299 | 1546442 | chr17 | 1623703 | 1623735 |
| chr17 | 1959468 | 1959520 | chr17 | 2207801 | 2207981 | chr17 | 2208041 | 2208063 |
| chr17 | 2220962 | 2221059 | chr17 | 2250051 | 2250081 | chr17 | 2278801 | 2278925 |
| chr17 | 2607905 | 2607986 | chr17 | 2663935 | 2664032 | chr17 | 3438914 | 3438937 |
| chr17 | 3657502 | 3657553 | chr17 | 3658490 | 3658519 | chr17 | 3658849 | 3658930 |
| chr17 | 3658990 | 3659011 | chr17 | 4544607 | 4544710 | chr17 | 4693354 | 4693388 |
| chr17 | 4699211 | 4699252 | chr17 | 4891276 | 4891305 | chr17 | 4891527 | 4891556 |
| chr17 | 5000428 | 5000790 | chr17 | 5019637 | 5019662 | chr17 | 5019738 | 5019761 |
| chr17 | 6616637 | 6616686 | chr17 | 6616911 | 6617173 | chr17 | 6679190 | 6679296 |
| chr17 | 6946107 | 6946141 | chr17 | 7348885 | 7348997 | chr17 | 7368947 | 7369139 |
| chr17 | 7471610 | 7471630 | chr17 | 7555117 | 7555425 | chr17 | 7572957 | 7573018 |
| chr17 | 7573968 | 7574028 | chr17 | 7576847 | 7577167 | chr17 | 7577504 | 7577604 |
| chr17 | 7578164 | 7578570 | chr17 | 7579285 | 7579880 | chr17 | 7906254 | 7906535 |
| chr17 | 7906832 | 7906861 | chr17 | 8104145 | 8104173 | chr17 | 8230335 | 8230694 |
| chr17 | 8534493 | 8534582 | chr17 | 8774623 | 8774653 | chr17 | 8868620 | 8868667 |
| chr17 | 8868815 | 8869385 | chr17 | 8906266 | 8906518 | chr17 | 8906993 | 8907575 |
| chr17 | 8926060 | 8926263 | chr17 | 10101084 | 10101109 | chr17 | 10101132 | 10101447 |
| chr17 | 10102415 | 10102665 | chr17 | 11144926 | 11144989 | chr17 | 11984693 | 11984722 |
| chr17 | 11998944 | 11998973 | chr17 | 12013726 | 12013755 | chr17 | 12016550 | 12016630 |
| chr17 | 12028618 | 12028647 | chr17 | 13504195 | 13504195 | chr17 | 13504557 | 13504681 |
| chr17 | 13505002 | 13505188 | chr17 | 13505418 | 13505572 | chr17 | 14201041 | 14201181 |
| chr17 | 14204212 | 14204242 | chr17 | 14204527 | 14204620 | chr17 | 15245050 | 15245139 |
| chr17 | 16282251 | 16282300 | chr17 | 16284630 | 16285065 | chr17 | 16326144 | 16326216 |
| chr17 | 16570699 | 16570794 | chr17 | 17062574 | 17062763 | chr17 | 17117365 | 17117395 |
| chr17 | 17123963 | 17123993 | chr17 | 17398404 | 17398440 | chr17 | 17719242 | 17719355 |
| chr17 | 18163055 | 18163325 | chr17 | 18538185 | 18538275 | chr17 | 18817198 | 18817241 |
| chr17 | 20238152 | 20238175 | chr17 | 20468021 | 20468090 | chr17 | 20817896 | 20817917 |
| chr17 | 25620573 | 25620715 | chr17 | 25676959 | 25676989 | chr17 | 25680264 | 25680294 |
| chr17 | 25907750 | 25907780 | chr17 | 26263183 | 26263223 | chr17 | 26554634 | 26554705 |
| chr17 | 26961770 | 26961833 | chr17 | 27036998 | 27037023 | chr17 | 27038649 | 27038685 |
| chr17 | 27056837 | 27056857 | chr17 | 27170162 | 27170191 | chr17 | 27181276 | 27181371 |
| chr17 | 27332453 | 27332660 | chr17 | 27716114 | 27716137 | chr17 | 27716197 | 27716220 |
| chr17 | 27940591 | 27940911 | chr17 | 28562701 | 28562765 | chr17 | 29232244 | 29232267 |
| chr17 | 29249717 | 29249930 | chr17 | 29298080 | 29298581 | chr17 | 29508761 | 29508790 |
| chr17 | 29541527 | 29541556 | chr17 | 29562732 | 29562761 | chr17 | 29718215 | 29718269 |
| chr17 | 29719187 | 29719242 | chr17 | 30243768 | 30243907 | chr17 | 30250325 | 30250345 |
| chr17 | 30568137 | 30568174 | chr17 | 31618425 | 31619319 | chr17 | 31619951 | 31620026 |
| chr17 | 32484020 | 32484049 | chr17 | 32906379 | 32906555 | chr17 | 32906599 | 32906636 |
| chr17 | 32906987 | 32907146 | chr17 | 32907652 | 32907753 | chr17 | 32908132 | 32908146 |
| chr17 | 32908171 | 32908374 | chr17 | 32908647 | 32908931 | chr17 | 33288229 | 33288351 |
| chr17 | 33288890 | 33288988 | chr17 | 33672916 | 33672986 | clu17 | 33877286 | 33877303 |
| chr17 | 33917239 | 33917268 | chr17 | 35165645 | 35165691 | chr17 | 35165986 | 35166016 |
| chr17 | 35285542 | 35285666 | chr17 | 35290388 | 35290655 | chr17 | 35291320 | 35291354 |
| chr17 | 35291829 | 35291898 | chr17 | 35291921 | 35292626 | chr17 | 35293704 | 36294154 |
| chr17 | 35294461 | 35294505 | chr17 | 35295047 | 35295160 | chr17 | 35296143 | 35296292 |
| chr17 | 35296728 | 35296888 | chr17 | 35297619 | 35298153 | chr17 | 35299251 | 35299443 |
| chr17 | 35299601 | 35299965 | chr17 | 35300261 | 35300712 | chr17 | 35300813 | 35300854 |
| chr17 | 35303340 | 35303535 | chr17 | 35872722 | 35872861 | chr17 | 36103021 | 36103326 |
| chr17 | 36103571 | 36103601 | chr17 | 36104218 | 36104550 | chr17 | 36104644 | 36104779 |
| chr17 | 36105223 | 36105349 | chr17 | 36105459 | 36105596 | chr17 | 36715772 | 36715967 |
| chr17 | 37192167 | 37192201 | chr17 | 37321186 | 37321624 | chr17 | 37321788 | 37321972 |
| chr17 | 37366337 | 37366552 | chr17 | 37369180 | 37369210 | chr17 | 37381011 | 37381429 |
| chr17 | 37381571 | 37381726 | chr17 | 37381826 | 37381850 | chr17 | 37382146 | 37382248 |
| chr17 | 37484095 | 37484128 | chr17 | 37757153 | 37757217 | chr17 | 37760488 | 37760561 |
| chr17 | 37761997 | 37762334 | chr17 | 37868190 | 37868294 | chr17 | 37879568 | 37879615 |
| chr17 | 37880205 | 37880276 | chr17 | 37880971 | 37881018 | chr17 | 37881318 | 37881631 |
| chr17 | 38179397 | 38179430 | chr17 | 38347560 | 38347615 | ch17 | 38474363 | 38474502 |
| chr17 | 38497616 | 38497645 | chr17 | 38498083 | 38498112 | chr17 | 38504087 | 38504116 |
| chr17 | 38510555 | 38510584 | chr17 | 39682502 | 39682711 | chr17 | 40332943 | 40333226 |
| chr17 | 40400867 | 40401031 | chr17 | 40464278 | 40464317 | chr17 | 40464517 | 40464607 |
| chr17 | 40474467 | 40474496 | chr17 | 40826197 | 40826226 | chr17 | 40837022 | 40837051 |
| chr17 | 40837287 | 40837383 | chr17 | 40838982 | 40839022 | chr17 | 40975575 | 40975677 |
| chr17 | 41177394 | 41177459 | chr17 | 41197714 | 41197743 | chr17 | 41201163 | 41201192 |
| chr17 | 41203073 | 41203102 | chr17 | 41209064 | 41209114 | chr17 | 41215890 | 41215961 |
| chr17 | 41267731 | 41257775 | chr17 | 41276031 | 41276075 | chr17 | 41277259 | 41277721 |
| chr17 | 41278621 | 41278700 | chr17 | 41651850 | 41651880 | chr17 | 41791460 | 41791489 |
| chr17 | 41791665 | 41791694 | chr17 | 42030329 | 42030750 | chr17 | 42061336 | 42061381 |
| chr17 | 42082522 | 42082557 | chr17 | 42084361 | 42084626 | chr17 | 42092190 | 42092220 |
| chr17 | 42331626 | 42331659 | chr17 | 42393842 | 42394024 | chr17 | 42402884 | 42402917 |
| chr17 | 42580695 | 42580793 | chr17 | 42587332 | 42587355 | chr17 | 42635295 | 42635760 |
| chr17 | 42733711 | 42733884 | chr17 | 42787579 | 42787616 | chr17 | 42907564 | 42907630 |
| chr17 | 42907655 | 42907951 | chr17 | 43001891 | 43001946 | chr17 | 43044658 | 43044688 |
| chr17 | 43045039 | 43045116 | chr17 | 43046260 | 43046385 | chr17 | 43339109 | 43339333 |
| chr17 | 43339609 | 43339899 | chr17 | 43974256 | 43974358 | chr17 | 44897416 | 44897445 |
| chr17 | 45331014 | 45331313 | chr17 | 45810850 | 45811341 | chr17 | 45867315 | 45867460 |
| chr17 | 46125007 | 46125061 | chr17 | 46567618 | 46567655 | chr17 | 46619540 | 46619569 |
| chr17 | 46620494 | 46621094 | chr17 | 46621353 | 46621458 | chr17 | 46621856 | 46621909 |

TABLE 13-continued

| chr | start | end | chr | start | end | chr | start | end |
|---|---|---|---|---|---|---|---|---|
| chr17 | 46655148 | 46655178 | chr17 | 46655451 | 46655998 | chr17 | 46656058 | 46656704 |
| chr17 | 46659429 | 46659859 | chr17 | 46663743 | 46663824 | chr17 | 46663856 | 46663887 |
| chr17 | 46674873 | 46674970 | chr17 | 46675170 | 46675600 | chr17 | 46690467 | 46690664 |
| chr17 | 46691505 | 46691592 | chr17 | 46691805 | 46691818 | chr17 | 46691988 | 46692110 |
| chr17 | 46692439 | 46692606 | chr17 | 46710946 | 46710989 | chr17 | 46713959 | 46714072 |
| chr17 | 46795641 | 46796373 | chr17 | 46796499 | 46796637 | chr17 | 46796850 | 46797213 |
| chr17 | 46797275 | 46797582 | chr17 | 46799625 | 46799896 | chr17 | 46800601 | 46800668 |
| chr17 | 46800961 | 46801047 | chr17 | 46801109 | 46801416 | chr17 | 46802459 | 46802911 |
| chr17 | 46802994 | 46803286 | chr17 | 46804107 | 46804428 | chr17 | 46810416 | 46810958 |
| chr17 | 46811354 | 46811499 | chr17 | 46816282 | 46816730 | chr17 | 46824224 | 46824275 |
| chr17 | 46824359 | 46825054 | chr17 | 46825284 | 46825514 | chr17 | 46826930 | 46827127 |
| chr17 | 46827330 | 46827501 | chr17 | 46827626 | 46827756 | chr17 | 46829498 | 46829579 |
| chr17 | 46829979 | 46830110 | chr17 | 46831779 | 46832325 | chr17 | 46832490 | 46832639 |
| chr17 | 47072805 | 47073028 | chr17 | 47073104 | 47073327 | chr17 | 47073389 | 47073465 |
| chr17 | 47073988 | 47074228 | chr17 | 47074561 | 47074895 | chr17 | 47075160 | 47075364 |
| chr17 | 47075215 | 47075734 | chr17 | 47075880 | 47076055 | chr17 | 47574090 | 47574149 |
| chr17 | 47657544 | 47657583 | chr17 | 47865514 | 47865555 | chr17 | 47987525 | 47987619 |
| chr17 | 47987930 | 47988114 | chr17 | 48041152 | 48041320 | chr17 | 48041672 | 48041721 |
| chr17 | 48042039 | 48042069 | chr17 | 48042435 | 48042647 | chr17 | 48042751 | 48042956 |
| chr17 | 48048952 | 48049059 | chr17 | 48049307 | 48050526 | chr17 | 48071020 | 48071050 |
| chr17 | 48071802 | 48071894 | chr17 | 48473206 | 48473236 | chr17 | 48545804 | 48545950 |
| chr17 | 48589801 | 48589831 | chr17 | 48612223 | 48612308 | chr17 | 48636581 | 48637136 |
| chr17 | 48653128 | 48653158 | chr17 | 48799843 | 48799866 | chr17 | 49027838 | 49027876 |
| chr17 | 49229485 | 49229605 | chr17 | 50235216 | 50235258 | chr17 | 50235631 | 50235952 |
| chr17 | 51901004 | 51901034 | chr17 | 53341252 | 53341536 | chr17 | 53342876 | 53343089 |
| chr17 | 53922649 | 53922790 | chr17 | 54674986 | 54675272 | chr17 | 54755969 | 54755990 |
| chr17 | 55122813 | 55122842 | chr17 | 55213641 | 55213670 | chr17 | 55962573 | 55962841 |
| chr17 | 56092600 | 56092638 | chr17 | 56234405 | 56234743 | chr17 | 56326949 | 56326994 |
| chr17 | 56327271 | 56327301 | chr17 | 56471121 | 56471144 | chr17 | 56833127 | 56833221 |
| chr17 | 56833707 | 56834000 | chr17 | 56834020 | 56834075 | chr17 | 56834306 | 56834375 |
| chr17 | 57297027 | 57297129 | chr17 | 58216613 | 58216836 | chr17 | 58216866 | 58217298 |
| chr17 | 58217357 | 58217551 | chr17 | 58218765 | 58218993 | chr17 | 58227374 | 58227397 |
| chr17 | 58498697 | 58499314 | chr17 | 59474157 | 59474246 | chr17 | 59474833 | 59475100 |
| chr17 | 59475678 | 59476023 | chr17 | 59476083 | 59476127 | chr17 | 59476410 | 69476635 |
| chr17 | 59478147 | 59478602 | chr17 | 59481657 | 59481678 | chr17 | 59488101 | 59488423 |
| chr17 | 59528876 | 59529150 | chr17 | 59529254 | 59529264 | chr17 | 59529844 | 59530352 |
| chr17 | 59531667 | 59532017 | chr17 | 59533875 | 59534405 | chr17 | 59534751 | 59534781 |
| chr17 | 59535137 | 59535219 | chr17 | 59539236 | 59539601 | chr17 | 59924556 | 59924585 |
| chr17 | 59937192 | 59937236 | chr17 | 61778235 | 61778248 | chr17 | 61817856 | 61817955 |
| chr17 | 61926172 | 61926324 | chr17 | 61926508 | 61926603 | chr17 | 62028596 | 62028790 |
| chr17 | 62777335 | 62777450 | chr17 | 62777746 | 62777791 | chr17 | 64672366 | 64672544 |
| chr17 | 66420718 | 66420748 | chr17 | 66596471 | 66596525 | chr17 | 66596984 | 66597021 |
| chr17 | 67410381 | 67410397 | chr17 | 68164733 | 68164928 | chr17 | 70026543 | 70026667 |
| chr17 | 70112916 | 70113566 | chr17 | 70113648 | 70114018 | chr17 | 70114153 | 70114517 |
| chr17 | 70215683 | 70216306 | chr17 | 70216393 | 70216585 | chr17 | 71641544 | 71641683 |
| chr17 | 71948439 | 71948863 | chr17 | 72270286 | 72270415 | chr17 | 72321933 | 72321975 |
| chr17 | 72322363 | 72322557 | chr17 | 72353213 | 72353259 | chr17 | 72353417 | 72353550 |
| chr17 | 72427853 | 72427999 | chr17 | 72428344 | 72428381 | chr17 | 72491378 | 72491395 |
| chr17 | 72667337 | 72667481 | chr17 | 72849010 | 72849079 | chr17 | 72857038 | 72857368 |
| chr17 | 72862371 | 72862460 | chr17 | 72920796 | 72921032 | chr17 | 73031637 | 73031666 |
| chr17 | 73115884 | 73115914 | chr17 | 73215289 | 73215386 | chr17 | 73545998 | 73546299 |
| chr17 | 73586015 | 73586418 | chr17 | 73608306 | 73608336 | chr17 | 73636144 | 73636337 |
| chr17 | 73808631 | 73808671 | chr17 | 73827213 | 73827243 | chr17 | 74028346 | 74028413 |
| chr17 | 74047797 | 74048020 | chr17 | 74070372 | 74070479 | chr17 | 74071445 | 74071481 |
| chr17 | 74071689 | 74071729 | chr17 | 74072999 | 74073036 | chr17 | 74073269 | 74073433 |
| chr17 | 74087118 | 74087185 | chr17 | 74390363 | 74390393 | chr17 | 74533844 | 74534310 |
| chr17 | 74581182 | 74581221 | chr17 | 74732944 | 74732973 | chr17 | 74865053 | 74865192 |
| chr17 | 74865698 | 74865243 | chr17 | 75137660 | 75137887 | chr17 | 75207514 | 75207630 |
| chr17 | 75207839 | 75207987 | chr17 | 75276054 | 75276083 | chr17 | 75276413 | 75276442 |
| chr17 | 75277348 | 75277659 | chr17 | 75278020 | 75278049 | chr17 | 75279105 | 75279134 |
| chr17 | 75282025 | 75282154 | chr17 | 75315512 | 75315681 | chr17 | 75316368 | 75316397 |
| chr17 | 75317170 | 75317199 | chr17 | 75347755 | 75347784 | chr17 | 75368735 | 75369238 |
| chr17 | 75369440 | 75369457 | chr17 | 75369493 | 75369860 | chr17 | 75370269 | 75370316 |
| chr17 | 75370596 | 75370625 | chr17 | 75373312 | 75373341 | chr17 | 75385071 | 75385446 |
| chr17 | 75405827 | 75405856 | chr17 | 75417150 | 75417179 | chr17 | 75523142 | 75523272 |
| chr17 | 75524636 | 75525194 | chr17 | 75733978 | 75734244 | chr17 | 75797111 | 75797179 |
| chr17 | 76125196 | 76125225 | chr17 | 76126434 | 76126463 | chr17 | 76128466 | 76128663 |
| chr17 | 76130124 | 76130153 | chr17 | 76130481 | 76130510 | chr17 | 76137951 | 76138190 |
| chr17 | 76138498 | 76138622 | chr17 | 76187407 | 76187506 | chr17 | 76207342 | 76207372 |
| chr17 | 76227849 | 76228161 | chr17 | 76228214 | 76228357 | chr17 | 76404615 | 76404659 |
| chr17 | 76877177 | 76877212 | chr17 | 76974447 | 76974499 | chr17 | 77084518 | 77084727 |
| chr17 | 77105055 | 77105198 | chr17 | 77145129 | 77145242 | chr17 | 77179113 | 77179278 |
| chr17 | 77179630 | 77179776 | chr17 | 77394706 | 77394850 | chr17 | 77776827 | 77776995 |
| chr17 | 77777053 | 77777056 | chr17 | 77777585 | 77777903 | chr17 | 77777944 | 77777961 |
| chr17 | 77778943 | 77779179 | chr17 | 77789474 | 77789500 | chr17 | 77825696 | 77825812 |
| chr17 | 77899664 | 77899693 | chr17 | 77919429 | 77919477 | chr17 | 77924259 | 77924351 |
| chr17 | 78122174 | 78122190 | chr17 | 78194821 | 78194861 | chr17 | 78272278 | 78272313 |
| chr17 | 78447127 | 78447157 | chr17 | 78451931 | 78451953 | chr17 | 78452296 | 78452340 |

TABLE 13-continued

| chr | start | end | chr | start | end | chr | start | end |
|---|---|---|---|---|---|---|---|---|
| chr17 | 78452681 | 78452833 | chr17 | 78518175 | 78518198 | chr17 | 78599596 | 78599628 |
| chr17 | 78667992 | 78668159 | chr17 | 78874441 | 78874559 | chr17 | 78999625 | 78999654 |
| chr17 | 79058302 | 79058333 | chr17 | 79094182 | 79094245 | chr17 | 79099770 | 79099799 |
| chr17 | 79626617 | 79626703 | chr17 | 79769433 | 79769693 | chr17 | 79813409 | 79813507 |
| chr17 | 79896013 | 79896043 | chr17 | 79945037 | 79945074 | chr17 | 80186260 | 80186289 |
| chr17 | 80197756 | 80197898 | chr17 | 80254266 | 80254296 | chr17 | 80289234 | 80289310 |
| chr17 | 80329709 | 80330000 | chr17 | 80394063 | 80394185 | chr17 | 80394573 | 80394602 |
| chr17 | 80479345 | 80479525 | chr17 | 80491572 | 80491602 | chr17 | 80535382 | 80535487 |
| chr17 | 80571380 | 80571776 | chr17 | 80654983 | 80655013 | chr17 | 80693317 | 80693554 |
| chr17 | 80749244 | 80749276 | chr17 | 80751650 | 80751714 | chr17 | 80794259 | 80794288 |
| chr17 | 80797692 | 80798345 | chr17 | 80832305 | 80832411 | chr17 | 80832712 | 80832796 |
| chr17 | 80859239 | 80859269 | chr17 | 81008618 | 81008826 | chr17 | 81033487 | 81033517 |
| chr17 | 81048993 | 81049023 | chr17 | 81049994 | 81050058 | chr18 | 499367 | 499482 |
| chr18 | 500046 | 500738 | chr18 | 904462 | 904648 | chr18 | 905000 | 905030 |
| chr18 | 905434 | 905615 | chr18 | 906871 | 906907 | chr18 | 907472 | 907594 |
| chr18 | 907912 | 907977 | chr18 | 908454 | 908589 | chr18 | 909487 | 909587 |
| chr18 | 2755854 | 2755878 | chr18 | 2906268 | 2906304 | chr18 | 3214441 | 3214543 |
| chr18 | 3215042 | 3215256 | chr18 | 3499067 | 3499371 | chr18 | 4453964 | 4454163 |
| chr18 | 5133207 | 5133343 | chr18 | 5196576 | 5196959 | chr18 | 5197202 | 5197271 |
| chr18 | 5197330 | 5197347 | chr18 | 5237878 | 5238247 | chr18 | 5628167 | 5628515 |
| chr18 | 5629774 | 5629825 | chr18 | 5630312 | 5630362 | chr18 | 5895023 | 5895205 |
| chr18 | 5895975 | 5896085 | chr18 | 6729952 | 6729993 | chr18 | 6908056 | 6908090 |
| chr18 | 7117665 | 7117804 | chr18 | 7567783 | 7568291 | chr18 | 8608748 | 8608837 |
| chr18 | 8608902 | 8608968 | chr18 | 8612252 | 8612282 | chr18 | 9771586 | 9771753 |
| chr18 | 9912767 | 9912797 | chr18 | 10251324 | 10251348 | chr18 | 10589096 | 10589348 |
| chr18 | 11148969 | 11149045 | chr18 | 11149561 | 11149759 | chr18 | 11149780 | 11149888 |
| chr18 | 11401654 | 11401817 | chr18 | 11689190 | 11689220 | chr18 | 11752128 | 11752379 |
| chr18 | 11752700 | 11752730 | chr18 | 11942728 | 11942753 | chr18 | 12254305 | 12254578 |
| chr18 | 12277243 | 12277273 | chr18 | 12307247 | 12307505 | chr18 | 12307603 | 12307751 |
| chr18 | 12376086 | 12376129 | chr18 | 13132080 | 13132223 | chr18 | 13824025 | 13824102 |
| chr18 | 13826393 | 13826536 | chr18 | 13868713 | 13868919 | chr18 | 15198149 | 15198248 |
| chr18 | 18822392 | 18823274 | chr18 | 19750308 | 19750346 | chr18 | 20911541 | 20911571 |
| chr18 | 21269349 | 21269390 | chr18 | 21269659 | 21269740 | chr18 | 21719351 | 21719568 |
| chr18 | 22929081 | 22929095 | chr18 | 22929187 | 22929718 | chr18 | 22929927 | 22930559 |
| chr18 | 22930790 | 22931178 | chr18 | 23686462 | 23686540 | chr18 | 24127748 | 24128030 |
| chr18 | 24130809 | 24130946 | chr18 | 24131099 | 24131187 | chr18 | 24764951 | 24765168 |
| chr18 | 25755593 | 25755655 | chr18 | 25756010 | 25756040 | chr18 | 25756495 | 25756729 |
| chr18 | 25757187 | 25757452 | chr18 | 25757787 | 25757824 | chr18 | 25758129 | 25758141 |
| chr18 | 28620899 | 28620955 | chr18 | 28621034 | 28621097 | chr18 | 28621328 | 28621393 |
| chr18 | 28621636 | 28621932 | chr18 | 28622419 | 28622488 | chr18 | 30349740 | 30349781 |
| chr18 | 31020495 | 31020510 | chr18 | 31158093 | 31158158 | chr18 | 31739035 | 31739469 |
| chr18 | 31802132 | 31802167 | chr18 | 31802938 | 31802968 | chr18 | 31803438 | 31803472 |
| chr18 | 31902793 | 31902945 | chr18 | 32073908 | 32074086 | chr18 | 32557832 | 32557864 |
| chr18 | 32847598 | 32847642 | chr18 | 32957803 | 32957821 | chr18 | 33078363 | 33078393 |
| chr18 | 33078633 | 33078662 | chr18 | 33877683 | 33877754 | chr18 | 35065072 | 35065145 |
| chr18 | 35144845 | 35144936 | chr18 | 35144969 | 35145465 | chr18 | 35145985 | 35146036 |
| chr18 | 35146062 | 35146241 | chr18 | 35147487 | 35147569 | chr18 | 43914211 | 43914278 |
| chr18 | 44259903 | 44259990 | chr18 | 44336034 | 44336449 | chr18 | 44337444 | 44337617 |
| chr18 | 44337650 | 44337841 | chr18 | 44773060 | 44773116 | chr18 | 44773592 | 44773966 |
| chr18 | 44774406 | 44774890 | chr18 | 44775380 | 44775554 | chr18 | 44776972 | 44777088 |
| chr18 | 44777301 | 44777331 | chr18 | 44777596 | 44777750 | chr18 | 44778049 | 44778326 |
| chr18 | 44781003 | 44781041 | chr18 | 44787781 | 44787846 | chr18 | 44788251 | 44788281 |
| chr18 | 44789474 | 44789514 | chr18 | 44789872 | 44789937 | chr18 | 45058069 | 45058240 |
| chr18 | 46142662 | 46142809 | chr18 | 47720492 | 47720522 | chr18 | 48604773 | 48604802 |
| chr18 | 48636211 | 48636320 | chr18 | 49867303 | 49867399 | chr18 | 52989009 | 52989220 |
| chr18 | 52989741 | 52989882 | chr18 | 53257137 | 53267204 | chr18 | 53446970 | 53447474 |
| chr18 | 53447799 | 53447816 | chr18 | 53989796 | 53989877 | chr18 | 54789070 | 54789256 |
| chr18 | 55019707 | 55019775 | chr18 | 55020655 | 55020698 | chr18 | 55021078 | 55021242 |
| chr18 | 55103381 | 55103411 | chr18 | 55104808 | 55105140 | chr18 | 55105728 | 55105830 |
| chr18 | 55114480 | 55114644 | chr18 | 55850845 | 55850987 | chr18 | 56483918 | 56483938 |
| chr18 | 56815734 | 56815891 | chr18 | 56887076 | 56887424 | chr18 | 56888554 | 56888623 |
| chr18 | 56931541 | 56931583 | chr18 | 56931967 | 56932107 | chr18 | 56932352 | 56932375 |
| chr18 | 56935010 | 56935319 | chr18 | 56936004 | 56936074 | chr18 | 56939113 | 56939174 |
| chr18 | 56939423 | 56939651 | chr18 | 56939764 | 56940170 | chr18 | 56940566 | 56940722 |
| chr18 | 56940955 | 56941244 | chr18 | 56941558 | 56941788 | chr18 | 57363706 | 57363743 |
| chr18 | 57364658 | 57364691 | chr18 | 59000988 | 59001022 | chr18 | 59001301 | 59001343 |
| chr18 | 59001498 | 59001740 | chr18 | 60263661 | 60263895 | chr18 | 60985498 | 60985532 |
| chr18 | 60985593 | 60985732 | chr18 | 61143911 | 61143975 | chr18 | 67067558 | 67067907 |
| chr18 | 67068715 | 67068811 | chr18 | 67069216 | 67069246 | chr18 | 70209148 | 70209205 |
| chr18 | 70210418 | 70210508 | chr18 | 70211626 | 70211666 | chr18 | 70534282 | 70534315 |
| chr18 | 70534428 | 70534731 | chr18 | 70535373 | 70535554 | chr18 | 70535576 | 70535582 |
| chr18 | 70536010 | 70536083 | chr18 | 70536188 | 70536604 | chr18 | 70536833 | 70536871 |
| chr18 | 70537188 | 70537218 | chr18 | 72845833 | 72845863 | chr18 | 73167585 | 73167832 |
| chr18 | 73628019 | 73628068 | chr18 | 74501144 | 74501183 | chr18 | 74755508 | 74755590 |
| chr18 | 74961326 | 74961955 | chr18 | 74962019 | 74962147 | chr18 | 74962970 | 74963545 |
| chr18 | 75335093 | 75335123 | chr18 | 75339231 | 75339340 | chr18 | 75362931 | 75362985 |
| chr18 | 75551271 | 75551301 | chr18 | 75612225 | 75612286 | chr18 | 75999404 | 75999434 |
| chr18 | 76239541 | 76239616 | chr18 | 76501479 | 76501509 | chr18 | 76653631 | 76653661 |

TABLE 13-continued

| chr | start | end | chr | start | end | chr | start | end |
|---|---|---|---|---|---|---|---|---|
| chr18 | 76686249 | 76686279 | chr18 | 76740102 | 76740223 | chr18 | 77143346 | 77143376 |
| chr18 | 77167824 | 77167854 | chr18 | 77181355 | 77181409 | chr18 | 77194936 | 77194978 |
| chr18 | 77205532 | 27205638 | chr18 | 77285897 | 77286028 | chr18 | 77300326 | 77300483 |
| chr18 | 77309533 | 77309563 | chr18 | 77312866 | 77312927 | chr18 | 77329727 | 77330017 |
| chr18 | 77371430 | 77371547 | chr18 | 77459762 | 77459877 | chr18 | 77543249 | 77543335 |
| chr18 | 77543700 | 77543824 | chr18 | 77548352 | 77548609 | chr18 | 77550206 | 77550367 |
| chr18 | 77558082 | 77558358 | chr18 | 77558831 | 77558930 | chr18 | 77576934 | 77577043 |
| chr18 | 77636591 | 77636621 | chr18 | 78004993 | 78005051 | chr19 | 403538 | 403809 |
| chr19 | 407189 | 407320 | chr19 | 418225 | 418255 | chr19 | 462181 | 462269 |
| chr19 | 468757 | 468787 | chr19 | 485165 | 485394 | chr19 | 549361 | 549451 |
| chr19 | 555608 | 555628 | chr19 | 570156 | 570175 | chr19 | 591365 | 591416 |
| chr19 | 592589 | 592632 | chr19 | 593290 | 593376 | chr19 | 599214 | 599333 |
| chr19 | 752136 | 752359 | chr19 | 869337 | 869394 | chr19 | 883624 | 883791 |
| chr19 | 884018 | 884162 | chr19 | 891516 | 891620 | chr19 | 955757 | 956237 |
| chr19 | 959128 | 959158 | chr9 | 1003305 | 1003384 | chr19 | 1003669 | 1003734 |
| chr19 | 1004915 | 1005441 | chr19 | 1030176 | 1030225 | chr19 | 1047890 | 1047915 |
| chr19 | 1083314 | 1083437 | chr19 | 1156524 | 1156554 | chr19 | 1170185 | 1170230 |
| chr19 | 1171099 | 1171324 | chr19 | 1220422 | 1220610 | chr19 | 1221981 | 1222010 |
| chr19 | 1236474 | 1236678 | chr19 | 1274778 | 1274826 | chr19 | 1308047 | 1308081 |
| chr19 | 1325788 | 1325889 | chr19 | 1401752 | 1401795 | chr19 | 1450319 | 1450390 |
| chr19 | 1496413 | 1496450 | chr19 | 1496654 | 1496674 | chr19 | 1524443 | 1524447 |
| chr19 | 1525605 | 1525960 | chr19 | 1527227 | 1527311 | chr19 | 1754172 | 1754193 |
| chr19 | 1754225 | 1754254 | chr19 | 1754739 | 1754804 | chr19 | 1757416 | 1757615 |
| chr19 | 1762474 | 1762505 | chr19 | 1764293 | 1764339 | chr19 | 1775076 | 1775239 |
| chr19 | 1776376 | 1776534 | chr19 | 1800032 | 1800300 | chr19 | 1807970 | 1808413 |
| chr19 | 2135672 | 2135701 | chr19 | 2251152 | 2251234 | chr19 | 2251611 | 2251715 |
| chr19 | 2252589 | 2252658 | chr19 | 2252984 | 2253735 | chr19 | 2274677 | 2274695 |
| chr19 | 2290253 | 2290271 | chr19 | 2290631 | 2290867 | chr19 | 2302793 | 2302951 |
| chr19 | 2331413 | 2331443 | chr19 | 2513250 | 2513285 | chr19 | 2642877 | 2642947 |
| chr19 | 2683911 | 2684056 | chr19 | 3041417 | 3041447 | chr19 | 3114998 | 3115027 |
| chr19 | 3118927 | 3118956 | chr19 | 3219539 | 3219565 | chr19 | 3296613 | 3296670 |
| chr19 | 3361139 | 3361388 | chr19 | 3562223 | 3562583 | chr19 | 3578138 | 3578223 |
| chr19 | 3659668 | 3659793 | chr19 | 3778130 | 3778394 | chr19 | 3779277 | 3779435 |
| chr19 | 3785649 | 3785835 | chr19 | 3785865 | 3786220 | chr19 | 3821044 | 3821217 |
| chr19 | 3822135 | 3822203 | chr19 | 3834572 | 3834641 | chr19 | 3855407 | 3855595 |
| chr19 | 3966686 | 3966755 | chr19 | 3994540 | 3994568 | chr19 | 4054435 | 4054471 |
| chr19 | 4095471 | 4095514 | chr19 | 4101087 | 4101116 | chr19 | 4110565 | 4110597 |
| chr19 | 4117526 | 4117630 | chr19 | 4305057 | 4305086 | chr19 | 4311273 | 4311412 |
| chr19 | 4548134 | 4548364 | chr19 | 4550246 | 4550330 | chr19 | 4555896 | 4556112 |
| chr19 | 4557098 | 4557235 | chr19 | 4670765 | 4670857 | chr19 | 4789697 | 4789721 |
| chr19 | 4910361 | 4910410 | chr19 | 4944145 | 4944174 | chr19 | 5292812 | 5292844 |
| chr19 | 5338914 | 5339143 | chr19 | 5608519 | 5608569 | chr19 | 5676212 | 5676242 |
| chr19 | 5759744 | 5759774 | chr19 | 5826179 | 5826209 | chr19 | 5910356 | 5910454 |
| chr19 | 5914761 | 5914791 | chr19 | 5914992 | 5915060 | chr19 | 6590325 | 5590478 |
| chr19 | 6658279 | 6658422 | chr19 | 6889423 | 6889439 | chr19 | 7157588 | 7157628 |
| chr19 | 7554718 | 7554749 | chr19 | 7615996 | 7616025 | chr19 | 7635530 | 7635552 |
| chr19 | 7746942 | 7747042 | chr19 | 7747205 | 7747234 | chr19 | 7795012 | 7795244 |
| chr19 | 7853028 | 7853157 | chr19 | 7853361 | 7853460 | chr19 | 8115235 | 8115310 |
| chr19 | 8554173 | 8554218 | chr19 | 8576914 | 8577000 | chr19 | 9420142 | 9420240 |
| chr19 | 9473564 | 9473597 | chr19 | 9473869 | 9474056 | chr19 | 9517609 | 9517771 |
| chr19 | 9608895 | 9609036 | chr19 | 9609319 | 9609436 | chr19 | 9903913 | 9904067 |
| chr19 | 9937369 | 9937386 | chr19 | 10231220 | 10231242 | chr19 | 10246506 | 10246566 |
| chr19 | 10362045 | 10362084 | chr19 | 10398209 | 10398285 | chr19 | 10405972 | 10406159 |
| chr19 | 10406279 | 10406349 | chr19 | 10406806 | 10407029 | chr19 | 10407045 | 10407135 |
| chr19 | 10527165 | 10527243 | chr19 | 10531419 | 10531512 | chr19 | 10531964 | 10531994 |
| chr19 | 10600431 | 10600460 | chr19 | 10602274 | 10602348 | chr19 | 10602565 | 10602864 |
| chr19 | 10610138 | 10610260 | chr19 | 10624751 | 10624852 | chr19 | 10624966 | 10625465 |
| chr19 | 10823678 | 10823721 | chr19 | 11134252 | 11134281 | chr19 | 11138507 | 11138536 |
| chr19 | 11492252 | 11492528 | chr19 | 11591031 | 11591185 | chr19 | 11592710 | 11592750 |
| chr19 | 11593022 | 11593159 | chr19 | 11689460 | 11689564 | chr19 | 11959912 | 11960077 |
| chr19 | 12147437 | 12147461 | chr19 | 12163448 | 12163672 | chr19 | 12163893 | 12163923 |
| chr19 | 12175445 | 12175504 | chr19 | 12175814 | 12176005 | chr19 | 12203028 | 12203656 |
| chr19 | 12267019 | 12267667 | chr19 | 12305839 | 12306193 | chr19 | 12306230 | 12306263 |
| chr19 | 12476492 | 12476556 | chr19 | 12595109 | 12595307 | chr19 | 12595845 | 12595896 |
| chr19 | 12606381 | 12606511 | chr19 | 12750987 | 12751056 | chr19 | 12863412 | 12863520 |
| chr19 | 12952000 | 12952139 | chr19 | 12996169 | 12996280 | chr19 | 13113454 | 13113668 |
| chr19 | 13616696 | 13616956 | chr19 | 13617159 | 13617256 | chr19 | 13618288 | 13618381 |
| chr19 | 13965932 | 13965965 | chr19 | 14085021 | 14085051 | chr19 | 14181305 | 14181846 |
| chr19 | 14584240 | 14584412 | chr19 | 14584537 | 14584775 | chr19 | 14663925 | 14664183 |
| chr19 | 14664479 | 14664561 | chr19 | 15090172 | 15090499 | chr19 | 15121685 | 15121894 |
| chr19 | 15122120 | 15122238 | chr19 | 15288433 | 15288856 | chr19 | 15292384 | 15292499 |
| chr19 | 15342734 | 15343373 | chr19 | 15344107 | 15344130 | chr19 | 16766902 | 16766932 |
| chr19 | 16999599 | 16999782 | chr19 | 17000570 | 17000599 | chr19 | 17007086 | 17007388 |
| chr19 | 17007447 | 17007662 | chr19 | 17008586 | 17008698 | chr19 | 17359350 | 17359459 |
| chr19 | 17392641 | 17392866 | chr19 | 17436061 | 17436203 | chr19 | 17717286 | 17717315 |
| chr19 | 17759224 | 17759423 | chr19 | 17791182 | 17791211 | chr19 | 17943423 | 17943452 |
| chr19 | 17945891 | 17945983 | chr19 | 17947991 | 17948023 | chr19 | 17949094 | 17949123 |
| chr19 | 17958490 | 17958839 | chr19 | 17983537 | 17983665 | chr19 | 18041166 | 18041203 |

TABLE 13-continued

| chr | start | end | chr | start | end | chr | start | end |
|---|---|---|---|---|---|---|---|---|
| chr19 | 18103711 | 18103741 | chr19 | 18104472 | 18104509 | chr19 | 18271894 | 18271923 |
| chr19 | 18278047 | 18278076 | chr19 | 18331031 | 18331136 | chr19 | 18343439 | 18343569 |
| chr19 | 18343921 | 18343963 | chr19 | 18383251 | 18383351 | chr19 | 18714552 | 18714580 |
| chr19 | 18811560 | 18811804 | chr19 | 18856379 | 18856409 | chr19 | 18872825 | 18872900 |
| chr19 | 18899432 | 18899652 | chr19 | 18901828 | 18902095 | chr19 | 18989821 | 18990281 |
| chr19 | 18994887 | 18995206 | chr19 | 19260030 | 19260101 | chr19 | 19261519 | 19261548 |
| chr19 | 19334831 | 19334915 | chr19 | 19636877 | 19636907 | chr19 | 19645834 | 19645925 |
| chr19 | 19651991 | 19652066 | chr19 | 19729251 | 19729395 | chr19 | 19739172 | 19739428 |
| chr19 | 20011955 | 20011992 | chr19 | 20012052 | 20012149 | chr19 | 20188723 | 20188872 |
| chr19 | 20189410 | 20189438 | chr19 | 21646407 | 21646437 | chr19 | 21688814 | 21688893 |
| chr19 | 21769300 | 21769374 | chr19 | 22018523 | 22018724 | chr19 | 22034356 | 22034421 |
| chr19 | 22034447 | 22034813 | chr19 | 22610635 | 22610700 | chr19 | 22715140 | 22715443 |
| chr19 | 23254189 | 23254219 | chr19 | 23257779 | 23258007 | chr19 | 23258306 | 23258559 |
| chr19 | 23258679 | 23258694 | chr19 | 23299748 | 23299824 | chr19 | 23433143 | 23433296 |
| chr19 | 23456615 | 23456881 | chr19 | 23598300 | 23598326 | chr19 | 24154592 | 24154621 |
| chr19 | 24216975 | 24217023 | chr19 | 29284452 | 29284575 | chr19 | 29505153 | 29505183 |
| chr19 | 30015934 | 30015962 | chr19 | 30016025 | 30016712 | chr19 | 30016914 | 30016928 |
| chr19 | 30017452 | 30017509 | chr19 | 30017578 | 30017721 | chr19 | 30017766 | 30018608 |
| chr19 | 30019145 | 30019610 | chr19 | 30019661 | 30019838 | chr19 | 30020093 | 30020473 |
| chr19 | 30186141 | 30186240 | chr19 | 30215542 | 30215571 | chr19 | 30215753 | 30215782 |
| chr19 | 30252296 | 30252333 | chr19 | 30555329 | 30555376 | chr19 | 30562775 | 30563017 |
| chr19 | 30582601 | 30582649 | chr19 | 30637494 | 30637531 | chr19 | 30703436 | 30703469 |
| chr19 | 30713480 | 30713592 | chr19 | 30713686 | 30713706 | chr19 | 30713909 | 30714042 |
| chr19 | 30714403 | 30714433 | chr19 | 30715402 | 30715766 | chr19 | 30716313 | 30716576 |
| chr19 | 30716953 | 30718149 | chr19 | 30718847 | 30718913 | chr19 | 30719449 | 30720067 |
| chr19 | 30865713 | 30866024 | chr19 | 31804724 | 31804754 | chr19 | 31839838 | 31839873 |
| chr19 | 31841937 | 31842389 | chr19 | 32364365 | 32364403 | chr19 | 32380872 | 32380961 |
| chr19 | 32516399 | 32516516 | chr19 | 32715673 | 32715741 | chr19 | 32898335 | 32898490 |
| chr19 | 33167116 | 33167431 | chr19 | 33468018 | 33468055 | chr19 | 33685544 | 33685581 |
| chr19 | 33792159 | 33792524 | chr19 | 33794675 | 33794744 | chr19 | 34112524 | 34112729 |
| chr19 | 34113367 | 34113587 | chr19 | 34114006 | 34114049 | chr19 | 34533139 | 34533169 |
| chr19 | 34973243 | 34973255 | chr19 | 34973656 | 34973697 | chr19 | 35264085 | 35264119 |
| chr19 | 35396251 | 35396370 | chr19 | 35616341 | 35616397 | chr19 | 35781374 | 35781459 |
| chr19 | 35783136 | 35783231 | chr19 | 35797916 | 35797965 | chr19 | 36048595 | 36048771 |
| chr19 | 36049327 | 36049367 | chr19 | 36049397 | 36049462 | chr19 | 36222432 | 36222534 |
| chr19 | 36250029 | 36250134 | chr19 | 36334979 | 36335147 | chr19 | 36347892 | 36348048 |
| chr19 | 36450106 | 36450295 | chr19 | 36523333 | 36523480 | chr19 | 36736027 | 36736057 |
| chr19 | 36736319 | 36736491 | chr19 | 36822324 | 36822466 | chr19 | 36822558 | 36822892 |
| chr19 | 36909073 | 36909348 | chr19 | 36909624 | 36909935 | chr19 | 37095665 | 37095812 |
| chr19 | 37096488 | 37096575 | chr19 | 37263532 | 37263584 | chr19 | 37264222 | 37264421 |
| chr19 | 37288209 | 37288424 | chr19 | 37288607 | 37288765 | chr19 | 37341761 | 37341962 |
| chr19 | 37407127 | 37407443 | chr19 | 37464048 | 37464567 | chr19 | 37464667 | 37464696 |
| chr19 | 37569289 | 37569554 | chr19 | 37702086 | 37702169 | chr19 | 37808445 | 37808485 |
| chr19 | 37959874 | 37959963 | chris | 37997433 | 37998138 | chr19 | 38042365 | 38042693 |
| chr19 | 38085254 | 38086066 | chr19 | 38146062 | 38146247 | chr19 | 38146457 | 38146568 |
| chr19 | 38182884 | 38182959 | chr19 | 38183112 | 38183299 | chr19 | 38308080 | 38308336 |
| chr19 | 38308395 | 38308466 | chr19 | 38441488 | 38441518 | chr19 | 38481044 | 38481217 |
| chr19 | 38747159 | 38747491 | chr19 | 38747748 | 38747767 | chr19 | 38755272 | 38755344 |
| chr19 | 38782559 | 38782589 | chr19 | 38789218 | 38789288 | chr19 | 38873935 | 38873965 |
| chr19 | 38905548 | 38905702 | chr19 | 38974232 | 38974262 | chr19 | 39135434 | 39135454 |
| chr19 | 39306433 | 39306545 | chr19 | 39650791 | 39650967 | chr19 | 39687756 | 39687844 |
| chr19 | 39754874 | 39755232 | chr19 | 39755265 | 39755358 | chr19 | 39816936 | 39817085 |
| chr19 | 39993477 | 39993656 | chr19 | 39997688 | 39997732 | chr19 | 39997749 | 39997813 |
| chr19 | 40006187 | 40006306 | chr19 | 40006576 | 40006639 | chr19 | 40724000 | 40724263 |
| chr19 | 40762943 | 40762972 | chr19 | 40829079 | 40829211 | chr19 | 40829793 | 40830032 |
| chr19 | 40902425 | 40902812 | chr19 | 40951175 | 40951206 | chr19 | 40951679 | 40951762 |
| chr19 | 41018510 | 41019031 | chr19 | 41025539 | 41025683 | chr19 | 41059909 | 41060306 |
| chr19 | 41073587 | 41073677 | chr19 | 41119177 | 41119276 | chr19 | 41119371 | 41119408 |
| chr19 | 41354666 | 41354722 | chr19 | 41641831 | 41641886 | chr19 | 41698787 | 41698920 |
| chr19 | 41919917 | 41919971 | chr19 | 42028502 | 42028549 | chr19 | 42408300 | 42408330 |
| chr19 | 42460961 | 42461113 | chr19 | 42827982 | 42828084 | chr19 | 42856453 | 42856483 |
| chr19 | 42911568 | 42911598 | chr19 | 44203830 | 44203877 | chr19 | 44405908 | 44406087 |
| chr19 | 44599783 | 44599803 | chr19 | 44905499 | 44905529 | chr19 | 44952282 | 44952881 |
| chr19 | 45003211 | 45003323 | chr19 | 45300144 | 45300197 | chr19 | 45570401 | 45570450 |
| chr19 | 45574465 | 45574495 | chr19 | 45574773 | 45574888 | chr19 | 45601380 | 45601410 |
| chr19 | 45655400 | 45655556 | chr19 | 45655648 | 45656363 | chr19 | 45656682 | 45656742 |
| chr19 | 45656791 | 45656913 | chr19 | 45657212 | 45657284 | chr19 | 45810102 | 45810267 |
| chr19 | 45835238 | 45835268 | chr19 | 45888946 | 45889224 | chr19 | 45889316 | 45889397 |
| chr19 | 45997528 | 45997584 | chr19 | 46002048 | 46002320 | chr19 | 46234845 | 46234887 |
| chr19 | 46379914 | 46380148 | chr19 | 46404522 | 46404601 | chr19 | 46916725 | 46916987 |
| chr19 | 46917061 | 46917075 | chr19 | 46930129 | 46930200 | chr19 | 46974552 | 46974608 |
| chr19 | 46992718 | 46992866 | chr19 | 46993164 | 46993260 | chr19 | 46993282 | 46993388 |
| chr19 | 46996501 | 46996514 | chr19 | 46996578 | 46996838 | chr19 | 47152978 | 47152990 |
| chr19 | 47200361 | 47200536 | chr19 | 47776713 | 47776742 | chr19 | 47933311 | 47933732 |
| chr19 | 47951288 | 47951318 | chr19 | 48003607 | 48003714 | chr19 | 48076642 | 48076672 |
| chr19 | 48137171 | 48137307 | chr19 | 48151265 | 48151337 | chr19 | 48614843 | 48614873 |
| chr19 | 48771551 | 48771600 | chr19 | 48800603 | 48800769 | chr19 | 48857808 | 48857831 |
| chr19 | 48902848 | 48902878 | chr19 | 48918100 | 48918379 | chr19 | 49119229 | 49119259 |

TABLE 13-continued

| chr | start | end | chr | start | end | chr | start | end |
|---|---|---|---|---|---|---|---|---|
| chr19 | 49127373 | 49127674 | chr19 | 49180462 | 49180558 | chr19 | 49256396 | 49256438 |
| chr19 | 49399218 | 49399310 | chr19 | 49402471 | 49402551 | chr19 | 49575460 | 49575474 |
| chr19 | 49890887 | 49890908 | chr19 | 49935736 | 49936174 | chr19 | 49936864 | 49936894 |
| chr19 | 50028397 | 50028530 | chr19 | 50049718 | 50049746 | chr19 | 50216042 | 50216072 |
| chr19 | 50243339 | 50243379 | chr19 | 50304736 | 50304766 | chr19 | 50316244 | 50316468 |
| chr19 | 50353394 | 50353574 | chr19 | 50553680 | 50553709 | chr19 | 50553997 | 50554510 |
| chr19 | 50816431 | 50816474 | chr19 | 50833828 | 50833863 | chr19 | 50898558 | 50898583 |
| chr19 | 50938547 | 50938691 | chr19 | 51041149 | 51041189 | chr19 | 51161225 | 51161255 |
| chr19 | 51162197 | 51162253 | chr19 | 51162428 | 51162527 | chr19 | 51171219 | 51171275 |
| chr19 | 51171828 | 51171860 | chr19 | 51227719 | 51227785 | chr19 | 51228049 | 51228079 |
| chr19 | 51228369 | 51228507 | chr19 | 51304554 | 51304602 | chr19 | 51520423 | 51520453 |
| chr19 | 51715329 | 51715359 | chr19 | 51830845 | 51831002 | chr19 | 51831121 | 51831128 |
| chr19 | 51831360 | 51831390 | chr19 | 51925127 | 51925272 | chr19 | 52097689 | 52097732 |
| chr19 | 52207254 | 52207367 | chr19 | 52222523 | 52222923 | chr19 | 52391235 | 52391264 |
| chr19 | 52452316 | 52452335 | chr19 | 52552104 | 52552119 | chr19 | 52715963 | 52715992 |
| chr19 | 52839588 | 52839717 | chr19 | 52839742 | 52839938 | chr19 | 52872942 | 52873440 |
| chr19 | 52956805 | 52956848 | chr19 | 53028928 | 53028952 | chr19 | 53031185 | 53031215 |
| chr19 | 53073563 | 53073772 | chr19 | 53073820 | 53073987 | chr19 | 53141648 | 53141745 |
| chr19 | 53193858 | 53193893 | chr19 | 53194281 | 53194396 | chr19 | 53204758 | 53204798 |
| chr19 | 53496649 | 53496786 | chr19 | 53496814 | 53496846 | chr19 | 53561668 | 53561733 |
| chr19 | 53635952 | 53636091 | chr19 | 53661647 | 53661865 | chr19 | 53662194 | 53662694 |
| chr19 | 53696414 | 53696580 | chr19 | 53700596 | 53700693 | chr19 | 53757895 | 53758247 |
| chr19 | 53811858 | 53811988 | chr19 | 53836954 | 53836975 | chr19 | 53837377 | 53837432 |
| chr19 | 53970501 | 53970643 | chr19 | 53970968 | 53971039 | chr19 | 53971110 | 53971157 |
| chr19 | 54023887 | 54024196 | chr19 | 54024521 | 54024553 | chr19 | 54024613 | 54024884 |
| chr19 | 54369555 | 54369681 | chr19 | 54411125 | 54411168 | chr19 | 54411556 | 54411586 |
| chr19 | 54412873 | 54412985 | chr19 | 54481771 | 54481968 | chr19 | 54483173 | 54483305 |
| chr19 | 54483365 | 54483546 | chr19 | 54485403 | 54485646 | chr19 | 54485673 | 54485823 |
| chr19 | 54850630 | 54850659 | chr19 | 55598811 | 55598888 | chr19 | 55629883 | 55630028 |
| chr19 | 56159273 | 56159499 | chr19 | 56189937 | 56189966 | chr19 | 56201643 | 56201938 |
| chr19 | 56588656 | 56588780 | chr19 | 56728678 | 56728788 | chr19 | 56879501 | 56880008 |
| chr19 | 56904740 | 56905203 | chr19 | 56915320 | 56915428 | chr19 | 56988557 | 56988663 |
| chr19 | 56989528 | 56989625 | chr19 | 56989697 | 56989754 | chr19 | 57050463 | 57050493 |
| chr19 | 57149579 | 57149619 | chr19 | 57154885 | 57155017 | chr19 | 57182994 | 57183126 |
| chr19 | 57276656 | 57276700 | chr19 | 57323825 | 57323854 | chr19 | 57610896 | 57610985 |
| chr19 | 57617522 | 57617715 | chr19 | 57617832 | 57618121 | chr19 | 57683148 | 57683162 |
| chr19 | 57683240 | 57683295 | chr19 | 57862395 | 57862783 | chr19 | 58011124 | 58011281 |
| chr19 | 58038924 | 58038969 | chr19 | 58095006 | 58095835 | chr19 | 58111632 | 58111783 |
| chr19 | 58125544 | 58125881 | chr19 | 58144494 | 58144701 | chr19 | 58219916 | 58220392 |
| chr19 | 58220516 | 58220832 | chr19 | 58238326 | 58238738 | chr19 | 58238988 | 58239088 |
| chr19 | 58400079 | 58400175 | chr19 | 58400417 | 58400518 | chr19 | 58458754 | 58458890 |
| chr19 | 58458979 | 58459201 | chr19 | 58514518 | 58514552 | chr19 | 58520739 | 58520941 |
| chr19 | 58545145 | 58545387 | chr19 | 58545578 | 58545589 | chr19 | 58545652 | 58545837 |
| chr19 | 58609254 | 58609359 | chr19 | 58609473 | 58609525 | chr19 | 58609713 | 58609854 |
| chr19 | 58629975 | 58629975 | chr19 | 58661894 | 58662094 | chr19 | 58666171 | 58666313 |
| chr19 | 58740086 | 58740118 | chr19 | 58874831 | 58874951 | chr19 | 58951271 | 58951400 |
| chr19 | 58951526 | 58951916 | chr19 | 58964180 | 58964266 | chr20 | 118577 | 118751 |
| chr20 | 291148 | 291162 | chr20 | 291221 | 291373 | chr20 | 400007 | 400087 |
| chr20 | 401153 | 401183 | chr20 | 401591 | 401756 | chr20 | 590434 | 590502 |
| chr20 | 592405 | 592449 | chr20 | 644182 | 644351 | chr20 | 644407 | 644787 |
| chr20 | 799104 | 799146 | chr20 | 982749 | 982798 | chr20 | 982892 | 982989 |
| chr20 | 1094651 | 1094682 | chr20 | 1206855 | 1207034 | chr20 | 1783761 | 1784305 |
| chr20 | 1876110 | 1876176 | chr20 | 1975357 | 1975386 | chr20 | 2539331 | 2539771 |
| chr20 | 2668770 | 2668922 | chr20 | 2780753 | 2780773 | chr20 | 2780893 | 2781452 |
| chr20 | 2781731 | 2781761 | chr20 | 2785659 | 2785866 | chr20 | 2785956 | 2786060 |
| chr20 | 3027758 | 3027785 | chr20 | 3052583 | 3052836 | chr20 | 3073561 | 3073899 |
| chr20 | 3154172 | 3154204 | chr20 | 3204870 | 3204952 | chr20 | 3220893 | 3220943 |
| chr20 | 3229576 | 3229612 | chr20 | 3641774 | 3641937 | chr20 | 3663020 | 3663174 |
| chr20 | 3762152 | 3762181 | chr20 | 3762407 | 3762436 | chr20 | 4040731 | 4040871 |
| chr20 | 4085057 | 4085087 | chr20 | 4229402 | 4229432 | chr20 | 4229786 | 4230600 |
| chr20 | 4803070 | 4803650 | chr20 | 4803921 | 4804008 | chr20 | 4804566 | 4804732 |
| chr20 | 5296172 | 5296900 | chr20 | 5297226 | 5297418 | chr20 | 5610356 | 5610386 |
| chr20 | 6022797 | 6023045 | chr20 | 6023268 | 6023310 | chr20 | 6748925 | 6749036 |
| chr20 | 7980362 | 7980392 | chr20 | 8112378 | 8112408 | chr20 | 8112739 | 8113022 |
| chr20 | 8113557 | 8113605 | chr20 | 9487385 | 9487719 | chr20 | 9487789 | 9487997 |
| chr20 | 9488376 | 9488848 | chr20 | 9489070 | 9489214 | chr20 | 9489424 | 9489708 |
| chr20 | 9495271 | 9495509 | chr20 | 9496330 | 9496530 | chr20 | 9496581 | 9496833 |
| chr20 | 9497035 | 9497109 | chr20 | 10198289 | 10198600 | chr20 | 10198941 | 10198945 |
| chr20 | 13200599 | 13200634 | chr20 | 16555010 | 16555030 | chr20 | 17206513 | 17206740 |
| chr20 | 17207874 | 17207930 | chr20 | 17208585 | 17208620 | chr20 | 18039823 | 18039897 |
| chr20 | 18073417 | 18073461 | chr20 | 18448999 | 18449076 | chr20 | 19739613 | 19739696 |
| chr20 | 19928306 | 19928461 | chr20 | 20344498 | 20344559 | chr20 | 20347460 | 20347709 |
| chr20 | 20347737 | 20348154 | chr20 | 20348526 | 20348605 | chr20 | 20349758 | 20349255 |
| chr20 | 20349574 | 20349604 | chr20 | 21080714 | 21080956 | chr20 | 21081029 | 21081844 |
| chr20 | 21082095 | 21082123 | chr20 | 21082216 | 21082253 | chr20 | 21082532 | 21082917 |
| chr20 | 21083421 | 21084361 | chr20 | 21085831 | 21085864 | chr20 | 21086195 | 21086451 |
| chr20 | 21086866 | 21087188 | chr20 | 21372174 | 21372192 | chr20 | 21372295 | 21372725 |
| chr20 | 21376250 | 21376336 | chr20 | 21376703 | 21376733 | chr20 | 21376877 | 21377128 |

TABLE 13-continued

| chr | start | end | chr | start | end | chr | start | end |
|---|---|---|---|---|---|---|---|---|
| chr20 | 21377474 | 21377640 | chr20 | 21377738 | 21378551 | chr20 | 21486375 | 21486659 |
| chr20 | 21486786 | 21486881 | chr20 | 21487153 | 21487307 | chr20 | 21487367 | 21487581 |
| chr20 | 21488158 | 21488351 | chr20 | 21489240 | 21489446 | chr20 | 21489622 | 21489703 |
| chr20 | 21490175 | 21490762 | chr20 | 21490815 | 21491345 | chr20 | 21492378 | 21492409 |
| chr20 | 21492508 | 21492825 | chr20 | 21493308 | 21493993 | chr20 | 21494531 | 21494703 |
| chr20 | 21495942 | 21495986 | chr20 | 21496260 | 21496294 | chr20 | 21496684 | 21497136 |
| chr20 | 21497413 | 21498638 | chr20 | 21499961 | 21500134 | chr20 | 21501445 | 21501724 |
| chr20 | 21502037 | 21502144 | chr20 | 21502590 | 21502699 | chr20 | 21502838 | 21503117 |
| chr20 | 21503455 | 21503773 | chr20 | 21682399 | 21682456 | chr20 | 21683311 | 21683651 |
| chr20 | 21685385 | 21685526 | chr20 | 21686235 | 21686677 | chr20 | 21687009 | 21687382 |
| chr20 | 21689956 | 21690185 | chr20 | 21694499 | 21694529 | chr20 | 21695088 | 21695273 |
| chr20 | 21695306 | 21695357 | chr20 | 21748445 | 21748491 | chr20 | 22401392 | 22401421 |
| chr20 | 22557396 | 22557675 | chr20 | 22557979 | 22558114 | chr20 | 22558637 | 22558669 |
| chr20 | 22559645 | 22559690 | chr20 | 22562721 | 22562840 | chr20 | 22563563 | 22563602 |
| chr20 | 22564235 | 22564265 | chr20 | 22566961 | 22566990 | chr20 | 23015917 | 23015946 |
| chr20 | 23029110 | 23029151 | chr20 | 23029589 | 23030085 | chr20 | 23030292 | 23030357 |
| chr20 | 23031548 | 23031692 | chr20 | 24450231 | 24450513 | chr20 | 24450820 | 24451019 |
| chr20 | 24451450 | 24451592 | chr20 | 24726701 | 24726825 | chr20 | 25058385 | 25058616 |
| chr20 | 25061746 | 25061788 | chr20 | 25061979 | 25062311 | chr20 | 25062511 | 25062645 |
| chr20 | 25062708 | 25062817 | chr20 | 25062871 | 25062880 | chr20 | 25063780 | 25063906 |
| chr20 | 25063994 | 25064458 | chr20 | 25065179 | 25065395 | chr20 | 25223141 | 25223277 |
| chr20 | 25230509 | 25230534 | chr20 | 25230774 | 25230799 | chr20 | 25334513 | 25334650 |
| chr20 | 26188812 | 26188961 | chr20 | 26190313 | 26190361 | chr20 | 29956013 | 29956042 |
| chr20 | 29956570 | 29956599 | chr20 | 30101723 | 30101743 | chr20 | 30297090 | 30297184 |
| chr20 | 30582750 | 30582978 | chr20 | 30639141 | 30639319 | chr20 | 30639632 | 30639847 |
| chr20 | 30640106 | 30640270 | chr20 | 30778024 | 30778313 | chr20 | 31035471 | 31035518 |
| chr20 | 31115683 | 31115799 | chr20 | 31151769 | 31151799 | chr20 | 31207211 | 31207283 |
| chr20 | 31282879 | 31282903 | chr20 | 32301797 | 32301953 | chr20 | 32450398 | 32450427 |
| chr20 | 33547565 | 33547585 | chr20 | 33574914 | 33574992 | chr20 | 34041981 | 34042004 |
| chr20 | 34148020 | 34148254 | chr20 | 34188617 | 34188631 | chr20 | 34188748 | 34189088 |
| chr20 | 34189167 | 34189391 | chr20 | 34189680 | 34189910 | chr20 | 35742487 | 35742607 |
| chr20 | 36531799 | 36531910 | chr20 | 36781324 | 36781354 | chr20 | 37302697 | 37303343 |
| chr20 | 37351793 | 37352515 | chr20 | 37352607 | 37352626 | chr20 | 37353193 | 37353236 |
| chr20 | 37353455 | 37353718 | chr20 | 37354145 | 37354831 | chr20 | 37354994 | 37355202 |
| chr20 | 37355847 | 37356042 | chr20 | 37356169 | 37356827 | chr20 | 37357216 | 37357353 |
| chr20 | 37357825 | 37358190 | chr20 | 37434552 | 37434721 | chr20 | 37434737 | 37434744 |
| chr20 | 37435104 | 37435218 | chr20 | 37435488 | 37435860 | chr20 | 39316203 | 39316322 |
| chr20 | 39316984 | 39317392 | chr20 | 39317750 | 39318166 | chr20 | 39318383 | 39318415 |
| chr20 | 39319126 | 39319203 | chr20 | 39319515 | 39319653 | chr20 | 39995146 | 39995813 |
| chr20 | 40743859 | 40743888 | chr20 | 41817786 | 41817915 | chr20 | 41818008 | 41818085 |
| chr20 | 41818567 | 41818748 | chr20 | 41818805 | 41818914 | chr20 | 42136330 | 42136411 |
| chr20 | 42218577 | 42218664 | chr20 | 42543754 | 42643853 | chr20 | 42544091 | 42544533 |
| chr20 | 42544728 | 42544984 | chr20 | 42852751 | 42852773 | chr20 | 42876525 | 42876575 |
| chr20 | 43438071 | 43438085 | chr20 | 43438335 | 43438466 | chr20 | 43438982 | 43439022 |
| chu20 | 43439291 | 43439510 | chr20 | 44003765 | 44003811 | chr20 | 44452731 | 44453063 |
| chr20 | 44519077 | 44519107 | chr20 | 44602074 | 44602099 | chr20 | 44602339 | 44602364 |
| chr20 | 44639181 | 44639496 | chr20 | 44640338 | 44640367 | chr20 | 44660750 | 44660877 |
| chr20 | 44686423 | 44686614 | chr20 | 44686628 | 44686762 | chr20 | 44746484 | 44746781 |
| chr20 | 44803174 | 44803675 | chr20 | 44875240 | 44875411 | chr20 | 44880041 | 44880076 |
| chr20 | 44937202 | 44937411 | chr20 | 44937426 | 44937643 | chr20 | 44941518 | 44941661 |
| chr20 | 45142000 | 45142038 | chr20 | 45142152 | 45142272 | chr20 | 45279854 | 45279981 |
| chr20 | 45280040 | 45280302 | chr20 | 45280344 | 45280428 | chr20 | 45337804 | 45337945 |
| chr20 | 45524523 | 45524553 | chr20 | 47247239 | 47247450 | chr20 | 47274032 | 47274062 |
| chr20 | 47296109 | 47296231 | chr20 | 47443729 | 47443936 | chr20 | 47443945 | 47444282 |
| chr20 | 47905426 | 47905603 | chr20 | 47934824 | 47935268 | chr20 | 47935495 | 47935567 |
| chr20 | 47935928 | 47936027 | chr20 | 48184381 | 48184435 | chr20 | 49204179 | 49204449 |
| chr20 | 49261803 | 49262104 | chr20 | 49358357 | 49358396 | chr20 | 49377899 | 49378043 |
| chr20 | 49381160 | 49381240 | chr20 | 49575909 | 49575939 | chr20 | 49639777 | 49639856 |
| chr20 | 49639883 | 49639996 | chr20 | 49640095 | 49640157 | chr20 | 49969348 | 49969515 |
| chr20 | 50160801 | 50160905 | chr20 | 50383384 | 50383423 | chr20 | 50384767 | 50384896 |
| chr20 | 50720437 | 50721200 | chr20 | 50721235 | 50721670 | chr20 | 50721989 | 50722035 |
| chr20 | 50722095 | 50722193 | chr20 | 50722598 | 50722821 | chr20 | 51589766 | 51589908 |
| chr20 | 52226337 | 52226366 | chr20 | 52311463 | 52311513 | chr20 | 52789445 | 52789475 |
| chr20 | 52789853 | 52789948 | chr20 | 52790082 | 52790155 | chr20 | 53092192 | 53092376 |
| chr20 | 53093085 | 53093115 | chr20 | 54578507 | 54578725 | chr20 | 54579852 | 54579958 |
| chr20 | 54580070 | 54580323 | chr20 | 54580622 | 54580691 | chr20 | 55008041 | 55008194 |
| chr20 | 55071640 | 55071717 | chr20 | 55200035 | 55200310 | chr20 | 55200616 | 55200706 |
| chr20 | 55200922 | 55201092 | chr20 | 55201764 | 55202068 | chr20 | 55202359 | 55202626 |
| chr20 | 55202826 | 55203107 | chr20 | 55204322 | 55204604 | chr20 | 56204966 | 55205000 |
| chr20 | 55206294 | 55206393 | chr20 | 55206739 | 55206774 | chr20 | 55499496 | 55499709 |
| chr20 | 55500016 | 55500085 | chr20 | 55500441 | 55500720 | chr20 | 55693527 | 55693625 |
| chr20 | 55841134 | 55841356 | chr20 | 55842096 | 55842189 | chr20 | 56766160 | 56766190 |
| chr20 | 56803398 | 56803441 | chr20 | 56803842 | 56803920 | chr20 | 57089452 | 57089459 |
| chr20 | 57090104 | 57090173 | chr20 | 57224842 | 57225079 | chr20 | 57225219 | 57225307 |
| chr20 | 57484406 | 57484445 | chr20 | 58179809 | 58179854 | chr20 | 58180214 | 58180402 |
| chr20 | 58508887 | 58508943 | chr20 | 59804170 | 59804235 | chr20 | 59826192 | 59826221 |
| chr20 | 59826962 | 59826977 | chr20 | 59828341 | 59828407 | chr20 | 59880433 | 59880477 |
| chr20 | 59910175 | 59910346 | chr20 | 59973028 | 59973072 | chr20 | 60202594 | 60202624 |

TABLE 13-continued

| chr | start | end | chr | start | end | chr | start | end |
|---|---|---|---|---|---|---|---|---|
| chr20 | 60235333 | 60235526 | chr20 | 60238381 | 60238472 | chr20 | 60238877 | 60238980 |
| chr20 | 60243944 | 60244107 | chr20 | 60329584 | 60329661 | chr20 | 60333880 | 60333969 |
| chr20 | 60359849 | 60359879 | chr20 | 60375036 | 60375070 | chr20 | 60439634 | 60439755 |
| chr20 | 60453925 | 60454091 | chr20 | 60477306 | 60477537 | chr20 | 60485374 | 60485425 |
| chr20 | 60503030 | 60503060 | chr20 | 60545561 | 60545792 | chr20 | 60620122 | 60620557 |
| chr20 | 60772853 | 60773878 | chr20 | 60789965 | 60790124 | chr20 | 60892164 | 60892222 |
| chr20 | 60926019 | 60926049 | chr20 | 60970953 | 60970983 | chr20 | 60983859 | 60984010 |
| chr20 | 60984341 | 60984465 | chr20 | 61288068 | 61288156 | chr20 | 61288463 | 61288534 |
| chr20 | 61294693 | 61294857 | chr20 | 61340581 | 61340689 | chr20 | 61412313 | 61412438 |
| chr20 | 61505881 | 61506330 | chr20 | 61532546 | 61532605 | chr20 | 61560418 | 61560460 |
| chr20 | 61560529 | 61560922 | chr20 | 61585771 | 61585922 | chr20 | 61585990 | 61586004 |
| chr20 | 61636876 | 61636890 | chr20 | 61637468 | 61637648 | chr20 | 61637736 | 61637956 |
| chr20 | 61638221 | 61638469 | chr20 | 61638535 | 61638631 | chr20 | 61703710 | 61703761 |
| chr20 | 61703846 | 61703875 | chr20 | 61714591 | 61714621 | chr20 | 61734420 | 61734481 |
| chr20 | 61747894 | 61747934 | chr20 | 61763598 | 61763628 | chr20 | 61765285 | 61765425 |
| chr20 | 61808181 | 61808270 | chr20 | 61808667 | 61809005 | chr20 | 61809219 | 61809631 |
| chr20 | 61809841 | 61810089 | chr20 | 61823170 | 61823195 | chr20 | 61862380 | 61862452 |
| chr20 | 61885247 | 61885462 | chr20 | 61886068 | 61886203 | chr20 | 61886257 | 61886258 |
| chr20 | 61886725 | 61886755 | chr20 | 61974191 | 61974354 | chr20 | 61980860 | 61980975 |
| chr20 | 62031173 | 62031234 | chr20 | 62032058 | 62032095 | chr20 | 62037559 | 62037598 |
| chr20 | 62046227 | 62046421 | chr20 | 62058700 | 62058786 | chr20 | 62090524 | 62090621 |
| chr20 | 62097666 | 62097695 | chr20 | 62115187 | 62115266 | chr20 | 62119339 | 62119618 |
| chr20 | 62119923 | 62120171 | chr20 | 62126118 | 62126429 | chr20 | 62157229 | 62157307 |
| chr20 | 62165631 | 62165762 | chr20 | 62167554 | 62167584 | chr20 | 62170179 | 62170209 |
| chr20 | 62172945 | 62173055 | chr20 | 62185386 | 62185444 | chr20 | 62260862 | 62260905 |
| chr20 | 62284487 | 62284615 | chr20 | 62314848 | 62314955 | chr20 | 62321206 | 62321341 |
| chr20 | 62321638 | 62321881 | chr20 | 62340321 | 62340442 | chr20 | 62383218 | 62383289 |
| chr20 | 62461349 | 62461475 | chr20 | 62488293 | 62488350 | chr20 | 62631442 | 62631562 |
| chr20 | 62680657 | 62680739 | chr20 | 62715014 | 62715069 | chr20 | 62786577 | 62786726 |
| chr20 | 62795643 | 62795672 | chr21 | 22370332 | 22370458 | chr21 | 22370688 | 22370718 |
| chr21 | 26934368 | 26934786 | chr21 | 27011773 | 27011807 | chr21 | 27012373 | 27012431 |
| chr21 | 27944995 | 27945081 | chr21 | 27945693 | 27945722 | chr21 | 28216634 | 28217690 |
| chr21 | 28218774 | 28219045 | chr21 | 28338836 | 28338887 | chr21 | 28339247 | 28339501 |
| chr21 | 28339892 | 28340048 | chr21 | 28340063 | 28340318 | chr21 | 31015201 | 31015231 |
| chr21 | 31311404 | 31311553 | chr21 | 31312080 | 31312105 | chr21 | 31312313 | 31312409 |
| chr21 | 32253745 | 32253774 | chr21 | 33043985 | 33044051 | chr21 | 33244921 | 33245040 |
| chr21 | 33245683 | 33245718 | chr21 | 33246009 | 33246190 | chr21 | 33627549 | 33627569 |
| chr21 | 33721756 | 33721824 | chr21 | 33785288 | 33785325 | chr21 | 33983236 | 33983332 |
| chr21 | 34392206 | 34392403 | chr21 | 34392437 | 34392566 | chr21 | 34395302 | 34396269 |
| chr21 | 34396795 | 34397091 | chr21 | 34398070 | 34398634 | chr21 | 34398933 | 34399258 |
| chr21 | 34399442 | 34400104 | chr21 | 34400232 | 34400258 | chr21 | 34401185 | 34401392 |
| chr21 | 34442595 | 34442665 | chr21 | 34443103 | 34443262 | chr21 | 34443509 | 34443686 |
| chr21 | 34443893 | 34443956 | chr21 | 34444163 | 34444362 | chr21 | 34444445 | 34444598 |
| chr21 | 35051195 | 35051231 | chr21 | 36041985 | 36042028 | chr21 | 36042092 | 36042238 |
| chr21 | 36042658 | 36042861 | chr21 | 37527928 | 37527958 | chr21 | 37758570 | 37758611 |
| chr21 | 37775034 | 37775141 | chr21 | 38064457 | 38064683 | chr21 | 38064966 | 38065522 |
| chr21 | 38065955 | 38066112 | chr21 | 38067203 | 38067233 | chr21 | 38068178 | 38068229 |
| chr21 | 38068647 | 38068783 | chr21 | 38069093 | 38069203 | chr21 | 38069459 | 38069496 |
| chr21 | 38069854 | 38070162 | chr21 | 38070705 | 38070765 | chr21 | 38071791 | 38071905 |
| chr21 | 38073007 | 38073070 | chr21 | 38073300 | 38073525 | chr21 | 38073616 | 38073860 |
| chr21 | 38078415 | 38078487 | chr21 | 38079988 | 38080062 | chr21 | 38080175 | 38080386 |
| chr21 | 38080551 | 38080684 | chr21 | 38081085 | 38081192 | chr21 | 38081666 | 38081835 |
| chr21 | 38082042 | 38082072 | chr21 | 38082930 | 38083196 | chr21 | 38092179 | 38092221 |
| chr21 | 38119904 | 38120312 | chr21 | 38638504 | 38638526 | chr21 | 38935478 | 38935549 |
| chr21 | 39047776 | 39047838 | chr21 | 39870612 | 39870641 | chr21 | 40033619 | 40033648 |
| chr21 | 40033877 | 40033906 | chr21 | 40034756 | 40034785 | chr21 | 40984685 | 40984900 |
| chr21 | 42617963 | 42617995 | chr21 | 42649172 | 42649202 | chr21 | 43186698 | 43186889 |
| chr21 | 43240082 | 43240112 | chr21 | 43256565 | 43256603 | chr21 | 43376373 | 43376403 |
| chr21 | 43393528 | 43393713 | chr21 | 43485279 | 43485348 | chr21 | 43786683 | 43786713 |
| chr21 | 43991463 | 43991493 | chr21 | 44283581 | 44283774 | chr21 | 44494941 | 44495155 |
| chr21 | 44514762 | 44514791 | chr21 | 44524441 | 44524470 | chr21 | 44837088 | 44837213 |
| chr21 | 44847591 | 44847622 | chr21 | 44866603 | 44866711 | chr21 | 44886709 | 44886870 |
| chr21 | 45148615 | 45148758 | chr21 | 45195149 | 45195319 | chr21 | 45271643 | 45271688 |
| chr21 | 45273717 | 45273913 | chr21 | 45290014 | 45290044 | chr21 | 45508617 | 45508647 |
| chr21 | 45521343 | 45521438 | chr21 | 45717477 | 45717548 | chr21 | 45791079 | 45791109 |
| chr21 | 45847832 | 45847973 | chr21 | 46036642 | 46036767 | chr21 | 46125967 | 46126267 |
| chr21 | 46126387 | 46126427 | chr21 | 46126567 | 46126721 | chr21 | 46127039 | 46127094 |
| chr21 | 46127542 | 46127692 | chr21 | 46128902 | 46128938 | chr21 | 46129444 | 46129485 |
| chr21 | 46193414 | 46193542 | chr21 | 46257116 | 46257273 | chr21 | 46310428 | 46310491 |
| chr21 | 46318286 | 46318343 | chr21 | 46319156 | 46319459 | chr21 | 46359187 | 46359248 |
| chr21 | 46452374 | 46452539 | chr21 | 46677734 | 46677796 | chr21 | 46825825 | 46826067 |
| chr21 | 46847654 | 46847684 | chr21 | 46863658 | 46863708 | chr21 | 46925780 | 46925925 |
| chr21 | 46926459 | 46926565 | chr21 | 46935739 | 46935936 | chr21 | 47010409 | 47010451 |
| chr21 | 47062753 | 47062825 | chr21 | 47063538 | 47063962 | chr21 | 47064250 | 47064377 |
| chr21 | 47404174 | 47404325 | chr21 | 47504861 | 47504895 | chr21 | 47518776 | 47518814 |
| chr21 | 47717560 | 47717589 | chr21 | 47746270 | 47746393 | chr22 | 17081932 | 17081935 |
| chr22 | 17082989 | 17083003 | chr22 | 17083396 | 17083410 | chr22 | 17601086 | 17601133 |
| chr22 | 17601260 | 17601368 | chr22 | 17602511 | 17602624 | chr22 | 17850454 | 17850621 |

TABLE 13-continued

| chr | start | end | chr | start | end | chr | start | end |
|---|---|---|---|---|---|---|---|---|
| chr22 | 18009985 | 18010105 | chr22 | 18328127 | 18328268 | chr22 | 18340822 | 18340868 |
| chr22 | 18627328 | 18627433 | chr22 | 19017532 | 19017567 | chr22 | 19117564 | 19117594 |
| chr22 | 19136907 | 19136936 | chr22 | 19137859 | 19137888 | chr22 | 19138109 | 19138138 |
| chr22 | 19510799 | 19510946 | chr22 | 19511142 | 19511455 | chr22 | 19511542 | 19511567 |
| chr22 | 19511849 | 19511875 | chr22 | 19702265 | 19702410 | chr22 | 19706171 | 19706677 |
| chr22 | 19742834 | 19742969 | chr22 | 19748644 | 19748908 | chr22 | 20229079 | 20229239 |
| chr22 | 20792482 | 20792641 | chr22 | 20940868 | 20940898 | chr22 | 21153867 | 21154000 |
| chr22 | 21299605 | 21299635 | chr22 | 21304979 | 21305007 | chr22 | 21368587 | 21368617 |
| chr22 | 21977314 | 21977347 | chr22 | 21982792 | 21982972 | chr22 | 22005794 | 22006759 |
| chr22 | 22058203 | 22058238 | chr22 | 22862787 | 22862862 | chr22 | 22901105 | 22901455 |
| chr22 | 23791402 | 23791432 | chr22 | 23801459 | 23801610 | chr22 | 23991237 | 23991272 |
| chr22 | 24145484 | 24145513 | chr22 | 24179940 | 24179982 | chr22 | 24180687 | 24180766 |
| chr22 | 24560375 | 24560526 | chr22 | 24820330 | 24820396 | chr22 | 25678748 | 25678868 |
| chr22 | 25679043 | 25679249 | chr22 | 25679268 | 25679337 | chr22 | 25817107 | 25817180 |
| chr22 | 25817458 | 25817612 | chr22 | 27053194 | 27053250 | chr22 | 28198569 | 28198605 |
| chr22 | 28371649 | 28371679 | chr22 | 28838200 | 28838292 | chr22 | 28838509 | 28838551 |
| chr22 | 28839122 | 28839263 | chr22 | 29091824 | 29091853 | chr22 | 29445752 | 29445923 |
| chr22 | 29876191 | 29876220 | chr22 | 29877223 | 29877299 | chr22 | 29977649 | 29977769 |
| chr22 | 30084358 | 30084388 | chr22 | 30090739 | 30090769 | chr22 | 30116904 | 30117146 |
| chr22 | 30158330 | 30158365 | chr22 | 30476197 | 30476220 | chr22 | 30881582 | 30881612 |
| chr22 | 30938543 | 30938584 | chr22 | 31198492 | 31198637 | chr22 | 31218510 | 31218540 |
| chr22 | 31218794 | 31218829 | chr22 | 31481130 | 31481332 | chr22 | 32748936 | 32748966 |
| chr22 | 33197603 | 33197652 | chr22 | 33453877 | 33454074 | chr22 | 33454194 | 33454258 |
| chr22 | 33454346 | 33454366 | chr22 | 35656581 | 35656610 | chr22 | 35848358 | 35848670 |
| chr22 | 35938746 | 35939000 | chr22 | 36681295 | 36681341 | chr22 | 36855568 | 36855598 |
| chr22 | 36902291 | 36902381 | chr22 | 37720961 | 37721163 | chr22 | 38087310 | 38087367 |
| chr22 | 38199769 | 38199894 | chr22 | 38220653 | 38221201 | chr22 | 38477069 | 38477131 |
| chr22 | 38477297 | 38477794 | chr22 | 38507316 | 38507346 | chr22 | 38592936 | 38593076 |
| chr22 | 38639229 | 38639259 | chr22 | 38874215 | 38874259 | chr22 | 39112502 | 39112584 |
| chr22 | 39784480 | 39784598 | chr22 | 39830355 | 39830457 | chr22 | 39853521 | 39853592 |
| chr22 | 39932499 | 39932563 | chr22 | 39954429 | 39954516 | chr22 | 40042627 | 40042743 |
| chr22 | 40075157 | 40075302 | chr22 | 40226367 | 40226389 | chr22 | 40807034 | 40807063 |
| chr22 | 41048732 | 41048951 | chr22 | 41634393 | 41634542 | chr22 | 41637064 | 41637129 |
| chr22 | 41648414 | 41648444 | chr22 | 41657233 | 41657350 | chr22 | 42096002 | 42096190 |
| chr22 | 42310087 | 42310220 | chr22 | 42311521 | 42311587 | chr22 | 42353611 | 42353892 |
| chr22 | 42667358 | 42667432 | chr22 | 43012543 | 43012560 | chr22 | 43012860 | 43012877 |
| chr22 | 43083130 | 43083148 | chr22 | 43434441 | 43434477 | chr22 | 43740084 | 43740128 |
| chr22 | 43808280 | 43808428 | chr22 | 44208418 | 44208448 | chr22 | 44258366 | 44258506 |
| chr22 | 44287650 | 44287696 | chr22 | 44455707 | 44455740 | chr22 | 45087632 | 45087649 |
| chr22 | 45088602 | 45088743 | chr22 | 45135939 | 45135979 | chr22 | 45252445 | 45252463 |
| chr22 | 45277292 | 45277322 | chr22 | 45313416 | 45313446 | chr22 | 45403086 | 45403133 |
| chr22 | 45403478 | 45403714 | chr22 | 45404197 | 45404433 | chr22 | 45404994 | 45405010 |
| chr22 | 45405047 | 45405061 | chr22 | 45405318 | 45405418 | chr22 | 45405620 | 45405768 |
| chr22 | 45406271 | 45406328 | chr22 | 45593643 | 45593715 | chr22 | 45604184 | 45604343 |
| chr22 | 45719161 | 45719190 | chr22 | 46262452 | 46263051 | chr22 | 46263512 | 46263623 |
| chr22 | 46263744 | 46263809 | chr22 | 46276749 | 46276820 | chr22 | 46438085 | 46438121 |
| chr22 | 46599623 | 46599725 | chr22 | 46931260 | 46931332 | chr22 | 46933089 | 46933237 |
| chr22 | 47005080 | 47005154 | chr22 | 47023044 | 47023191 | chr22 | 47054686 | 47054791 |
| chr22 | 47193335 | 47193371 | chr22 | 47395475 | 47395505 | chr22 | 47525846 | 47525885 |
| chr22 | 47584867 | 47585024 | chr22 | 48027626 | 48027655 | chr22 | 48885530 | 48885837 |
| chr22 | 48886659 | 48886849 | chr22 | 48931881 | 48932027 | chr22 | 48971533 | 48971679 |
| chr22 | 48972220 | 48972465 | chr22 | 49852617 | 49852647 | chr22 | 49979646 | 49979757 |
| chr22 | 50001699 | 50001882 | chr22 | 50002787 | 50002819 | chr22 | 50003204 | 50003234 |
| chr22 | 50010113 | 50010258 | chr22 | 50010461 | 50010585 | chr22 | 50031691 | 50031721 |
| chr22 | 50064760 | 50064944 | chr22 | 50149431 | 50149470 | chr22 | 50467005 | 50467035 |
| chr22 | 50497147 | 50497182 | chr22 | 50497214 | 50497287 | chr22 | 50623672 | 50623714 |
| chr22 | 50623742 | 50623815 | chr22 | 50899293 | 50899672 | chr22 | 50939073 | 50939111 |
| chr22 | 50943093 | 50943262 | chr22 | 50986016 | 50986045 | chr22 | 51042278 | 51042404 |
| chr22 | 51042458 | 51042565 | chr22 | 51112150 | 51112232 | chrX | 3631506 | 3631633 |
| chrX | 3746612 | 3746642 | chrX | 6145331 | 6145688 | chrX | 8698863 | 8698897 |
| chrX | 8699504 | 8699566 | chrX | 20148710 | 20148739 | chrX | 47039370 | 47039399 |
| chrX | 47426106 | 47426144 | chrX | 47426780 | 47426821 | chrX | 50557075 | 50557075 |
| chrX | 66931448 | 66931477 | chrX | 66937356 | 66937385 | chrX | 66943529 | 66943567 |
| chrX | 70339239 | 70339268 | chrX | 100740260 | 100740289 | chrX | 101906099 | 101906120 |
| chrX | 102000609 | 102000758 | chrX | 134156560 | 134156680 | chrX | 136656563 | 136656592 |
| chrY | 2655316 | 2655346 | chrY | 3446305 | 3446343 | chrY | 13316007 | 13316132 |
| chrY | 14532822 | 14532852 | chrY | 14533556 | 14533613 | chrY | 21204734 | 21205113 |

TABLE 14

| chr | start | end | chr | start | end | chr | start | end |
|---|---|---|---|---|---|---|---|---|
| chr1 | 898633 | 898792 | chr1 | 913445 | 914044 | chr1 | 1080495 | 1080914 |
| chr1 | 1146657 | 1146896 | chr1 | 1218688 | 1218779 | chr1 | 1223433 | 1223595 |
| chr1 | 1235811 | 1236156 | chr1 | 1266957 | 1267233 | chr1 | 1267372 | 1267791 |

TABLE 14-continued

| chr | start | end | chr | start | end | chr | start | end |
|---|---|---|---|---|---|---|---|---|
| chr1 | 1267823 | 1268242 | chr1 | 1341738 | 1341826 | chr1 | 1475458 | 1476417 |
| chr1 | 1483096 | 1483139 | chr1 | 1563119 | 1563298 | chr1 | 1856362 | 1856471 |
| chr1 | 1857759 | 1857811 | chr1 | 1874647 | 1874877 | chr1 | 1910341 | 1910465 |
| chr1 | 1935188 | 1935547 | chr1 | 1974768 | 1974802 | chr1 | 2066406 | 2066756 |
| chr1 | 2125141 | 2125560 | chr1 | 2263067 | 2263366 | chr1 | 2267472 | 2267771 |
| chr1 | 2304239 | 2304478 | chr1 | 2307851 | 2307970 | chr1 | 2308023 | 2308030 |
| chr1 | 2308297 | 2308716 | chr1 | 2309792 | 2309994 | chr1 | 2331281 | 2331500 |
| chr1 | 2336323 | 2336440 | chr1 | 2375047 | 2375646 | chr1 | 2396927 | 2397106 |
| chr1 | 2428239 | 2428478 | chr1 | 2472089 | 2472388 | chr1 | 2506974 | 2507150 |
| chr1 | 2520925 | 2521062 | chr1 | 2706094 | 2706552 | chr1 | 2830081 | 2830147 |
| chr1 | 2865964 | 2866143 | chr1 | 2984645 | 2984824 | chr1 | 3102567 | 3102866 |
| chr1 | 3182781 | 3182874 | chr1 | 3182942 | 3183020 | chr1 | 3322011 | 3322250 |
| chr1 | 3567062 | 3568320 | chr1 | 3601749 | 3602030 | chr1 | 3606995 | 3607339 |
| chr1 | 3659530 | 3659769 | chr1 | 3663458 | 3663637 | chr1 | 3663779 | 3664018 |
| chr1 | 3664606 | 3664781 | chr1 | 3683723 | 3683902 | chr1 | 4111087 | 4111323 |
| chr1 | 4713943 | 4714422 | chr1 | 4714642 | 4716744 | chr1 | 6166262 | 6166561 |
| chr1 | 6171668 | 6171907 | chr1 | 6186410 | 6186649 | chr1 | 6280169 | 6280348 |
| chr1 | 6304103 | 6304342 | chr1 | 6360495 | 6350728 | chr1 | 6446041 | 6446400 |
| chr1 | 6480434 | 6480913 | chr1 | 6500911 | 6501262 | chr1 | 6507603 | 6508202 |
| chr1 | 7764540 | 7764775 | chr1 | 8277298 | 8277837 | chr1 | 9712017 | 9712179 |
| chr1 | 9712459 | 9713096 | chr1 | 10166481 | 10166626 | chr1 | 10948478 | 10948657 |
| chr1 | 11538796 | 11538913 | chr1 | 11539101 | 11539280 | chr1 | 11539336 | 11539515 |
| chr1 | 11540035 | 11540334 | chr1 | 11591712 | 11591863 | chr1 | 11752375 | 11752614 |
| chr1 | 11936674 | 11936779 | chr1 | 11958996 | 11959295 | chr1 | 12041511 | 12041630 |
| chr1 | 12123143 | 12123742 | chr1 | 12227604 | 12227805 | chr1 | 12251342 | 12252059 |
| chr1 | 13839669 | 13840088 | chr1 | 13910336 | 13910815 | chr1 | 14026401 | 14026700 |
| chr1 | 14730390 | 14730502 | chr1 | 14925417 | 14926136 | chr1 | 15251113 | 15251316 |
| chr1 | 15480854 | 15480983 | chr1 | 16085267 | 16085746 | chr1 | 16474984 | 16475299 |
| chr1 | 16861448 | 16861627 | chr1 | 17445781 | 17446011 | chr1 | 18434366 | 18434605 |
| chr1 | 18437373 | 18437612 | chr1 | 18956114 | 18956353 | chr1 | 18956383 | 18956408 |
| chr1 | 18956716 | 18956735 | chr1 | 18957142 | 18957321 | chr1 | 18957428 | 18957667 |
| chr1 | 18957938 | 18958477 | chr1 | 18959346 | 18959645 | chr1 | 18960795 | 18951094 |
| chr1 | 18962648 | 18963231 | chr1 | 18969543 | 18969902 | chr1 | 18971772 | 18972011 |
| chr1 | 18972056 | 18972170 | chr1 | 19043472 | 19043771 | chr1 | 19992272 | 19992511 |
| chr1 | 20127444 | 20127555 | chr1 | 20618230 | 20618469 | chr1 | 20878953 | 20879372 |
| chr1 | 20879482 | 20879721 | chr1 | 20879752 | 20880051 | chr1 | 20880095 | 20880694 |
| chr1 | 21026082 | 21026253 | chr1 | 21042820 | 21042999 | chr1 | 21044024 | 21044263 |
| chr1 | 21573736 | 21574215 | chr1 | 21835856 | 21836095 | chr1 | 22140674 | 22141393 |
| chr1 | 22927327 | 22927566 | chr1 | 23748907 | 23749146 | chr1 | 23884996 | 23885088 |
| chr1 | 25255845 | 25256029 | chr1 | 25256280 | 25256459 | chr1 | 25256826 | 25257305 |
| chr1 | 25257391 | 25257464 | chr1 | 26551597 | 26551896 | chr1 | 26551989 | 26552228 |
| chr1 | 26737509 | 26737688 | chr1 | 26737855 | 26738274 | chr1 | 27190078 | 27190377 |
| chr1 | 27844444 | 27844623 | chr1 | 29450398 | 29450637 | chr1 | 29585984 | 29586763 |
| chr1 | 29804872 | 29805171 | chr1 | 30351469 | 30351828 | chr1 | 30815328 | 30815675 |
| chr1 | 31863112 | 31863130 | chr1 | 32180323 | 32180502 | chr1 | 32237507 | 32238586 |
| chr1 | 32410202 | 32410381 | chr1 | 32410418 | 32410717 | chr1 | 32705425 | 32705639 |
| chr1 | 32756421 | 32756519 | chr1 | 32930524 | 32930658 | chr1 | 34628874 | 34629053 |
| chr1 | 34629390 | 34629809 | chr1 | 34630473 | 34630712 | chr1 | 34630770 | 34631069 |
| chr1 | 34631502 | 34631741 | chr1 | 34631859 | 34631892 | chr1 | 34632023 | 34632038 |
| chr1 | 34642298 | 34642657 | chr1 | 35258557 | 35258796 | chr1 | 35350980 | 35351759 |
| chr1 | 35396450 | 35395929 | chr1 | 35664721 | 35664836 | chr1 | 36042605 | 36043564 |
| chr1 | 36563382 | 36563621 | chr1 | 37498718 | 37499295 | chr1 | 37499358 | 37500257 |
| chr1 | 37500368 | 37500907 | chr1 | 37500998 | 37501107 | chr1 | 38100591 | 38100787 |
| chr1 | 38219635 | 38219874 | chr1 | 38229961 | 38230380 | chr1 | 38230700 | 38230937 |
| chr1 | 38398356 | 38398431 | chr1 | 38510079 | 38510258 | chr1 | 38510475 | 38510714 |
| chr1 | 38510778 | 38511197 | chr1 | 38511252 | 38511911 | chr1 | 38512311 | 38512490 |
| chr1 | 38513162 | 38513229 | chr1 | 39269662 | 39270201 | chr1 | 40137822 | 40138061 |
| chr1 | 40237053 | 40237281 | chr1 | 40349627 | 40349746 | chr1 | 41284058 | 41284541 |
| chr1 | 41847494 | 41847793 | chr1 | 41848778 | 41848915 | chr1 | 41967261 | 41967360 |
| chr1 | 41991552 | 41991791 | chr1 | 43834653 | 43834807 | chr1 | 44068700 | 44068879 |
| chr1 | 44726821 | 44727360 | chr1 | 44872358 | 44873797 | chr1 | 44883030 | 44884289 |
| chr1 | 45308239 | 45308358 | chr1 | 45308655 | 45308729 | chr1 | 46632781 | 46633020 |
| chr1 | 46913761 | 46914360 | chr1 | 46914582 | 46914641 | chr1 | 46932686 | 46932842 |
| chr1 | 46951114 | 46951833 | chr1 | 46956380 | 46956679 | chr1 | 46956728 | 46957246 |
| chr1 | 47009851 | 47010150 | chr1 | 47695033 | 47695512 | chr1 | 47696207 | 47696686 |
| chr1 | 47696727 | 47697206 | chr1 | 47697254 | 47697613 | chr1 | 47697642 | 47698301 |
| chr1 | 47881984 | 47882403 | chr1 | 47882667 | 47882906 | chr1 | 47909640 | 47910239 |
| chr1 | 47910420 | 47911019 | chr1 | 47911243 | 47911365 | chr1 | 48058982 | 48059341 |
| chr1 | 49242260 | 49242619 | chr1 | 50513541 | 50513837 | chr1 | 50799190 | 50799489 |
| chr1 | 50880808 | 50882625 | chr1 | 50882731 | 50883690 | chr1 | 50883800 | 50884999 |
| chr1 | 50885262 | 50885441 | chr1 | 50886107 | 50887366 | chr1 | 50888619 | 50888918 |
| chr1 | 50889008 | 50889607 | chr1 | 50889741 | 50890460 | chr1 | 50890600 | 50891565 |
| chr1 | 50892073 | 50892432 | chr1 | 50892523 | 50893962 | chr1 | 51763181 | 51763395 |
| chr1 | 52832605 | 52832712 | chr1 | 53068087 | 53068626 | chr1 | 53098746 | 53099165 |
| chr1 | 53308489 | 53309328 | chr1 | 53528288 | 53528527 | chr1 | 53705675 | 53705794 |
| chr1 | 54203419 | 54204498 | chr1 | 54586532 | 54586831 | chr1 | 55462599 | 55462778 |
| chr1 | 57888293 | 57888472 | chr1 | 57888888 | 57889187 | chr1 | 57889319 | 57889738 |
| chr1 | 57890332 | 57890671 | chr1 | 58715055 | 58715294 | chr1 | 58715375 | 58716094 |

TABLE 14-continued

| chr | start | end | chr | start | end | chr | start | end |
|---|---|---|---|---|---|---|---|---|
| chr1 | 61519265 | 61519497 | chr1 | 62793169 | 62793342 | chr1 | 63539429 | 63539968 |
| chr1 | 63785232 | 63786431 | chr1 | 63786928 | 63787167 | chr1 | 63787226 | 63787645 |
| chr1 | 63788341 | 63788640 | chr1 | 63788694 | 63790373 | chr1 | 63792458 | 63793171 |
| chr1 | 63795265 | 63796370 | chr1 | 63796418 | 63796584 | chr1 | 64240031 | 64240222 |
| chr1 | 64240526 | 64240765 | chr1 | 64734554 | 64734669 | chr1 | 64937227 | 64937401 |
| chr1 | 65731243 | 65731542 | chr1 | 53731552 | 65731851 | chr1 | 65990876 | 65991115 |
| chr1 | 65991344 | 65991883 | chr1 | 66258088 | 66258867 | chr1 | 66259037 | 66259276 |
| chr1 | 66998702 | 66999412 | chr1 | 66999536 | 66999772 | chr1 | 67217965 | 67218424 |
| chr1 | 67390243 | 67390542 | chr1 | 67390993 | 67391172 | chr1 | 67773081 | 67773860 |
| chr1 | 70033524 | 70033709 | chr1 | 70033829 | 70034003 | chr1 | 70034368 | 70034667 |
| chr1 | 70035014 | 70035526 | chr1 | 70599152 | 70599260 | chr1 | 70672859 | 70672978 |
| chr1 | 72749635 | 72749798 | chr1 | 75595702 | 75596479 | chr1 | 75596597 | 75597668 |
| chr1 | 75597842 | 75598261 | chr1 | 75598310 | 75598489 | chr1 | 75599345 | 75599704 |
| chr1 | 75600148 | 75601513 | chr1 | 75601889 | 75603148 | chr1 | 76080387 | 76080866 |
| chr1 | 76082050 | 76082289 | chr1 | 76354731 | 76354839 | chr1 | 76540398 | 76540757 |
| chr1 | 77332984 | 77333163 | chr1 | 77333285 | 77333625 | chr1 | 77333947 | 77334846 |
| chr1 | 77747291 | 77747530 | chr1 | 77747848 | 77748327 | chr1 | 78511371 | 78512450 |
| chr1 | 78957198 | 78957617 | chr1 | 82268586 | 82268904 | chr1 | 84944531 | 84944650 |
| chr1 | 85358543 | 85358902 | chr1 | 85463275 | 85463454 | chr1 | 86621555 | 86622024 |
| chr1 | 86622112 | 86622224 | chr1 | 86622430 | 86622831 | chr1 | 86860815 | 86861049 |
| chr1 | 87617672 | 87617911 | chr1 | 90309344 | 90309571 | chr1 | 91171926 | 91172765 |
| chr1 | 91177865 | 91178284 | chr1 | 91179982 | 91180401 | chr1 | 91181853 | 91182212 |
| chr1 | 91182246 | 91182969 | chr1 | 91183001 | 91183805 | chr1 | 91183850 | 91184080 |
| chr1 | 91184339 | 91184758 | chr1 | 91185126 | 91185809 | chr1 | 91188891 | 91189483 |
| chr1 | 91189585 | 91190484 | chr1 | 91190791 | 91191390 | chr1 | 91192174 | 91192773 |
| chr1 | 91194446 | 91194672 | chr1 | 91195015 | 91195494 | chr1 | 91195802 | 91196581 |
| chr1 | 91316168 | 91316407 | chr1 | 91316536 | 91316775 | chr1 | 91869914 | 91870093 |
| chr1 | 92948236 | 92948701 | chr1 | 92948760 | 92949059 | chr1 | 92952071 | 92952632 |
| chr1 | 94343486 | 94343596 | chr1 | 97185167 | 97185357 | chr1 | 98510704 | 98511423 |
| chr1 | 98511536 | 98512015 | chr1 | 98514151 | 98514330 | chr1 | 98515048 | 98515408 |
| chr1 | 98518939 | 98519769 | chr1 | 99469586 | 99469885 | chr1 | 99470049 | 99470288 |
| chr1 | 99470697 | 99470924 | chr1 | 100437184 | 100437270 | chr1 | 101004358 | 101004837 |
| chr1 | 101004989 | 101005228 | chr1 | 101005279 | 101005758 | chr1 | 101702411 | 101702710 |
| chr1 | 101703538 | 101703717 | chr1 | 107682647 | 107683066 | chr1 | 107683359 | 107683598 |
| chr1 | 107684161 | 107684520 | chr1 | 108506989 | 108507168 | chr1 | 108507230 | 108507589 |
| chr1 | 108507615 | 108507914 | chr1 | 108507957 | 108508671 | chr1 | 109203582 | 109203761 |
| chr1 | 109585369 | 109585472 | chr1 | 109631647 | 109631765 | chr1 | 109644252 | 109644413 |
| chr1 | 110610483 | 110612162 | chr1 | 110612760 | 110613239 | chr1 | 110626592 | 110627671 |
| chr1 | 110672792 | 110673331 | chr1 | 110692886 | 110694205 | chr1 | 110754040 | 110754202 |
| chr1 | 110754211 | 110754930 | chr1 | 110883455 | 110884054 | chr1 | 111097832 | 111098011 |
| chr1 | 111098107 | 111098406 | chr1 | 111216684 | 111218063 | chr1 | 111505931 | 111506290 |
| chr1 | 111813448 | 111813687 | chr1 | 112084880 | 112085059 | chr1 | 114448981 | 114449087 |
| chr1 | 114695362 | 114696021 | chr1 | 114696132 | 114696299 | chr1 | 114696335 | 114696791 |
| chr1 | 115256441 | 115256620 | chr1 | 115258659 | 115258838 | chr1 | 115631842 | 115632011 |
| chr1 | 115632393 | 115632632 | chr1 | 115880081 | 115880500 | chr1 | 115880765 | 115881304 |
| chr1 | 116214002 | 116214132 | chr1 | 116214207 | 116214421 | chr1 | 116371051 | 116371290 |
| chr1 | 116380550 | 116381389 | chr1 | 116382294 | 116382583 | chr1 | 119521973 | 119522121 |
| chr1 | 119522200 | 119522632 | chr1 | 119522741 | 119523039 | chr1 | 119526993 | 119527472 |
| chr1 | 119527549 | 119527728 | chr1 | 119528557 | 119529216 | chr1 | 119529703 | 119529942 |
| chr1 | 119530024 | 119530743 | chr1 | 119530944 | 119531243 | chr1 | 119531943 | 119532177 |
| chr1 | 119535738 | 119535857 | chr1 | 119536058 | 119536457 | chr1 | 119542248 | 119542427 |
| chr1 | 119542905 | 119543324 | chr1 | 11943438 | 119544277 | chr1 | 119548749 | 119548928 |
| chr1 | 119548955 | 119549017 | chr1 | 119549032 | 119550034 | chr1 | 119550068 | 119550367 |
| chr1 | 119550434 | 119550733 | chr1 | 119550818 | 119551357 | chr1 | 150603035 | 150603141 |
| chr1 | 151169649 | 151169757 | chr1 | 151170069 | 151170297 | chr1 | 151300814 | 151300933 |
| chr1 | 151693849 | 151694448 | chr1 | 152085302 | 152085601 | chr1 | 152488055 | 152488294 |
| chr1 | 153539382 | 153539681 | chr1 | 153540006 | 153540245 | chr1 | 153651873 | 153652472 |
| chr1 | 153937048 | 153937167 | chr1 | 154298230 | 154298562 | chr1 | 154475073 | 154475612 |
| chr1 | 154516709 | 154516926 | chr1 | 155043313 | 155043734 | chr1 | 155161767 | 155161886 |
| chr1 | 155578918 | 155579008 | chr1 | 155826303 | 155826412 | chr1 | 155954190 | 155954391 |
| chr1 | 156010529 | 156010643 | chr1 | 156215255 | 156215434 | chr1 | 156215527 | 156215886 |
| chr1 | 156357892 | 156358611 | chr1 | 156390058 | 156390777 | chr1 | 156405436 | 156406515 |
| chr1 | 156432076 | 156432315 | chr1 | 156594879 | 156595118 | chr1 | 156611795 | 156612214 |
| chr1 | 156626505 | 156626744 | chr1 | 156626814 | 156627113 | chr1 | 156646516 | 156646740 |
| chr1 | 156814831 | 156815250 | chr1 | 156815356 | 156815835 | chr1 | 156830190 | 156830429 |
| chr1 | 156838078 | 156838424 | chr1 | 156863010 | 156863429 | chr1 | 156863574 | 156863808 |
| chr1 | 157247369 | 157247487 | chr1 | 157458816 | 157458935 | chr1 | 157895339 | 157895518 |
| chr1 | 158669614 | 158669973 | chr1 | 158687334 | 158687633 | chr1 | 159158251 | 159158588 |
| chr1 | 159187205 | 159187390 | chr1 | 160693839 | 160693957 | chr1 | 160992253 | 160992363 |
| chr1 | 161007615 | 161007847 | chr1 | 161228566 | 161228971 | chr1 | 161275466 | 161276125 |
| chr1 | 161442367 | 161442546 | chr1 | 161471751 | 161471868 | chr1 | 161591390 | 161591444 |
| chr1 | 161591549 | 161591629 | chr1 | 162792211 | 162792630 | chr1 | 164290533 | 164290772 |
| chr1 | 165086889 | 165087114 | chr1 | 165204994 | 165205233 | chr1 | 165321651 | 165321950 |
| chr1 | 165324104 | 165324758 | chr1 | 165325016 | 165325615 | chr1 | 165325804 | 165326043 |
| chr1 | 165326128 | 165326547 | chr1 | 165414124 | 165414352 | chr1 | 166134158 | 166134397 |
| chr1 | 166134643 | 166134882 | chr1 | 166135118 | 166135357 | chr1 | 166853551 | 166853668 |
| chr1 | 166916774 | 166917193 | chr1 | 167599076 | 167599435 | chr1 | 167599521 | 167599940 |
| chr1 | 167823371 | 167823524 | chr1 | 169396291 | 169397010 | chr1 | 170629466 | 170629513 |

TABLE 14-continued

| chr | start | end | chr | start | end | chr | start | end |
|---|---|---|---|---|---|---|---|---|
| chr1 | 170629925 | 170630151 | chr1 | 170630364 | 170630903 | chr1 | 170631005 | 170631244 |
| chr1 | 170631399 | 170631638 | chr1 | 170633533 | 170633712 | chr1 | 170637582 | 170637881 |
| chr1 | 170640425 | 170640784 | chr1 | 171625443 | 171625543 | chr1 | 171810113 | 171811066 |
| chr1 | 173638567 | 173639153 | chr1 | 175346411 | 175346646 | chr1 | 175388553 | 175388682 |
| chr1 | 177133619 | 177133918 | chr1 | 177140021 | 177140790 | chr1 | 177150699 | 177150878 |
| chr1 | 179544884 | 179545183 | chr1 | 179712063 | 179713502 | chr1 | 180197986 | 180198285 |
| chr1 | 180202331 | 180203110 | chr1 | 180203355 | 180205009 | chr1 | 180235656 | 180235835 |
| chr1 | 180882487 | 180882518 | chr1 | 180925188 | 180925289 | chr1 | 180925330 | 180925487 |
| chr1 | 181287599 | 181287838 | chr1 | 181287922 | 181288281 | chr1 | 181451315 | 181452214 |
| chr1 | 181452770 | 181453069 | chr1 | 181454774 | 181455013 | chr1 | 181455104 | 181455343 |
| chr1 | 182584084 | 182584623 | chr1 | 182807488 | 182807607 | chr1 | 183129301 | 183129530 |
| chr1 | 183386070 | 183386369 | chr1 | 183386414 | 183386713 | chr1 | 183386752 | 183387051 |
| chr1 | 183387174 | 183387413 | chr1 | 183462984 | 183463103 | chr1 | 183774155 | 183774454 |
| chr1 | 184005609 | 184005908 | chr1 | 185073803 | 185074028 | chr1 | 190444781 | 190444892 |
| chr1 | 190445080 | 190445379 | chr1 | 190447297 | 190447596 | chr1 | 195732240 | 195732521 |
| chr1 | 196577628 | 196577953 | chr1 | 196578007 | 196578246 | chr1 | 197879307 | 197879546 |
| chr1 | 197879607 | 197880258 | chr1 | 197882052 | 197882291 | chr1 | 197882353 | 197882581 |
| chr1 | 197886978 | 197887817 | chr1 | 197887977 | 197888396 | chr1 | 197888546 | 197889385 |
| chr1 | 200009312 | 200009551 | chr1 | 200010202 | 200010921 | chr1 | 200011236 | 200012191 |
| chr1 | 201368752 | 201368805 | chr1 | 201983038 | 201983277 | chr1 | 202081790 | 202081886 |
| chr1 | 202183343 | 202183476 | chr1 | 202679128 | 202679607 | chr1 | 203298210 | 203298441 |
| chr1 | 203429530 | 203429649 | chr1 | 204333520 | 204333660 | chr1 | 204653475 | 204653894 |
| chr1 | 205312504 | 205313043 | chr1 | 205424577 | 205425046 | chr1 | 205537569 | 205537868 |
| chr1 | 207200767 | 207201066 | chr1 | 207669419 | 207670138 | chr1 | 207818295 | 207818424 |
| chr1 | 208084210 | 208084569 | chr1 | 209381030 | 209381269 | chr1 | 210111072 | 210111251 |
| chr1 | 210111285 | 210112244 | chr1 | 211847683 | 211847862 | chr1 | 212963808 | 212963979 |
| chr1 | 213123776 | 213124075 | chr1 | 213124573 | 213124992 | chr1 | 214156345 | 214157004 |
| chr1 | 214158753 | 214159052 | chr1 | 214160028 | 214160266 | chr1 | 214360583 | 214361062 |
| chr1 | 214724452 | 214724588 | chr1 | 215254998 | 215255897 | chr1 | 216897142 | 216897321 |
| chr1 | 217307273 | 217307311 | chr1 | 217307368 | 217308360 | chr1 | 217308907 | 217309206 |
| chr1 | 217309671 | 217309910 | chr1 | 217311163 | 217311942 | chr1 | 217312946 | 217313822 |
| chr1 | 217805068 | 217805236 | chr1 | 218520021 | 218520477 | chr1 | 218520701 | 218520740 |
| chr1 | 219347112 | 219347134 | chr1 | 219347314 | 219347553 | chr1 | 220101056 | 220101475 |
| chr1 | 220101609 | 220101788 | chr1 | 220132115 | 220132213 | chr1 | 220636429 | 220636548 |
| chr1 | 220700737 | 220700976 | chr1 | 221051936 | 221052595 | chr1 | 221053527 | 221063946 |
| chr1 | 221067418 | 221067777 | chr1 | 223302739 | 223302978 | chr1 | 223538254 | 223538670 |
| chr1 | 223936546 | 223937145 | chr1 | 224400388 | 224400627 | chr1 | 224528740 | 224528919 |
| chr1 | 224803668 | 224803854 | chr1 | 224803995 | 224804991 | chr1 | 224805051 | 224805890 |
| chr1 | 226411169 | 226411348 | chr1 | 226411617 | 226411916 | chr1 | 226924982 | 226925281 |
| chr1 | 227729689 | 227730168 | chr1 | 228194340 | 228194579 | chr1 | 228195294 | 228196433 |
| chr1 | 228201147 | 228201326 | chr1 | 228247924 | 228247961 | chr1 | 228248228 | 228248407 |
| chr1 | 228463210 | 228463809 | chr1 | 228528749 | 228529108 | chr1 | 228558623 | 228559329 |
| chr1 | 228566528 | 228566618 | chr1 | 228565637 | 228566767 | chr1 | 228603929 | 228604348 |
| chr1 | 228633887 | 228634354 | chr1 | 228645048 | 228645827 | chr1 | 228646196 | 228646315 |
| chr1 | 228651350 | 228651709 | chr1 | 228651805 | 228651924 | chr1 | 228652243 | 228652704 |
| chr1 | 229542750 | 229543229 | chr1 | 229543459 | 229543612 | chr1 | 229566670 | 229566942 |
| chr1 | 229567012 | 229568289 | chr1 | 229569712 | 229569951 | chr1 | 230404150 | 230404360 |
| chr1 | 230561683 | 230561922 | chr1 | 231297013 | 231297312 | chr1 | 231298505 | 231298864 |
| chr1 | 232765226 | 232765398 | chr1 | 233750126 | 233750402 | chr1 | 234040224 | 234040403 |
| chr1 | 234040668 | 234041147 | chr1 | 234041303 | 234041716 | chr1 | 234349895 | 234350194 |
| chr1 | 234445299 | 234445478 | chr1 | 234620965 | 234621073 | chr1 | 234844947 | 234845167 |
| chr1 | 235813693 | 235814292 | chr1 | 236227538 | 236228197 | chr1 | 236228507 | 236228866 |
| chr1 | 236559075 | 236559374 | chr1 | 236849381 | 236850220 | chr1 | 237205085 | 237205098 |
| chr1 | 237205157 | 237205264 | chr1 | 237205337 | 237205576 | chr1 | 237205612 | 237206811 |
| chr1 | 239550505 | 239551284 | chr1 | 240118762 | 240119061 | chr1 | 240160997 | 240161571 |
| chr1 | 240254859 | 240255098 | chr1 | 240255282 | 240255581 | chr1 | 240255739 | 240256278 |
| chr1 | 240256573 | 240256872 | chr1 | 240775351 | 240775530 | chr1 | 241052047 | 241052201 |
| chr1 | 241520202 | 241520441 | chr1 | 241520509 | 241520632 | chr1 | 241520685 | 241520688 |
| chr1 | 241587013 | 241587194 | chr1 | 241587513 | 241587872 | chr1 | 242686642 | 242687781 |
| chr1 | 242688103 | 242688342 | chr1 | 242688377 | 242688773 | chr1 | 243646523 | 243646762 |
| chr1 | 244014160 | 244014479 | chr1 | 244080598 | 244080777 | chr1 | 244080874 | 244080883 |
| chr1 | 244893136 | 244893255 | chr1 | 245135670 | 245135849 | chr1 | 245494418 | 245494631 |
| chr1 | 246330402 | 246330509 | chr1 | 246488077 | 246488316 | chr1 | 248002191 | 248002310 |
| chr1 | 248020405 | 248021424 | chr1 | 248027930 | 248028289 | chr1 | 248074658 | 248074768 |
| chr1 | 248074838 | 248075008 | chr1 | 248099661 | 248099900 | chr1 | 248328674 | 248328921 |
| chr1 | 249121623 | 249121738 | chr2 | 287492 | 287731 | chr2 | 288318 | 288557 |
| chr2 | 467943 | 468182 | chr2 | 468217 | 468756 | chr2 | 496125 | 496465 |
| chr2 | 720748 | 720985 | chr2 | 875887 | 876066 | chr2 | 945838 | 946077 |
| chr2 | 946117 | 946356 | chr2 | 946449 | 946688 | chr2 | 946819 | 947238 |
| chr2 | 1653023 | 1653262 | chr2 | 1746523 | 1747302 | chr2 | 1747591 | 1748906 |
| chr2 | 2844646 | 2844676 | chr2 | 2844802 | 2844825 | chr2 | 3750873 | 3751052 |
| chr2 | 3751238 | 3751537 | chr2 | 5831102 | 5831401 | chr2 | 5831715 | 5831894 |
| chr2 | 5831967 | 5832326 | chr2 | 5832800 | 5834119 | chr2 | 5835990 | 5836349 |
| chr2 | 5836451 | 5837170 | chr2 | 5837197 | 5837496 | chr2 | 5866006 | 5866305 |
| chr2 | 7164389 | 7164704 | chr2 | 7571420 | 7571828 | chr2 | 9134330 | 9134569 |
| chr2 | 9960660 | 9960839 | chr2 | 10115632 | 10115739 | chr2 | 10153063 | 10153168 |
| chr2 | 10153229 | 10153422 | chr2 | 10154909 | 10155024 | chr2 | 10155269 | 10155384 |
| chr2 | 10156334 | 10156493 | chr2 | 10182747 | 10182986 | chr2 | 10408310 | 10408342 |

TABLE 14-continued

| chr | start | end | chr | start | end | chr | start | end |
|---|---|---|---|---|---|---|---|---|
| chr2 | 10688800 | 10688979 | chr2 | 11052419 | 11052658 | chr2 | 11809858 | 11810217 |
| chr2 | 12246027 | 12246195 | chr2 | 12858356 | 12858715 | chr2 | 14772673 | 14772888 |
| chr2 | 14774475 | 14774664 | chr2 | 17719601 | 17719900 | chr2 | 18058941 | 18059180 |
| chr2 | 18059692 | 18059931 | chr2 | 19550140 | 19550319 | chr2 | 19551225 | 19551464 |
| chr2 | 19556226 | 19556765 | chr2 | 19556994 | 19552173 | chr2 | 19558744 | 19558983 |
| chr2 | 19561045 | 19561404 | chr2 | 19561422 | 19561781 | chr2 | 19563277 | 19563516 |
| chr2 | 20068723 | 20068962 | chr2 | 20442485 | 20442586 | chr2 | 20642626 | 20642745 |
| chr2 | 20865560 | 20866022 | chr2 | 25391060 | 25391313 | chr2 | 25391586 | 25391825 |
| chr2 | 25438724 | 25439356 | chr2 | 26372893 | 26373072 | chr2 | 26395353 | 26395652 |
| chr2 | 26401956 | 26402135 | chr2 | 26407418 | 26408085 | chr2 | 26521960 | 26522079 |
| chr2 | 26915682 | 26916341 | chr2 | 27070250 | 27070489 | chr2 | 27071144 | 27071443 |
| chr2 | 27072394 | 27072633 | chr2 | 27072727 | 27073086 | chr2 | 27558410 | 27558500 |
| chr2 | 27887451 | 27887630 | chr2 | 29033261 | 29034020 | chr2 | 29337988 | 29339067 |
| chr2 | 30143219 | 30143578 | chr2 | 30143952 | 30144496 | chr2 | 30453619 | 30454038 |
| chr2 | 31360210 | 31360929 | chr2 | 31361015 | 31361118 | chr2 | 31361194 | 31361194 |
| chr2 | 31361282 | 31361461 | chr2 | 31456606 | 31457131 | chr2 | 32504335 | 32504449 |
| c1u2 | 38302176 | 38302955 | chr2 | 38365728 | 38365847 | chr2 | 39187141 | 39187800 |
| chr2 | 39892997 | 39893596 | chr2 | 39893897 | 39894136 | chr2 | 40678513 | 40678872 |
| chr2 | 40678945 | 40679712 | chr2 | 42274495 | 42274734 | chr2 | 42329340 | 42329759 |
| chr2 | 42720185 | 42720644 | chr2 | 43019525 | 43019944 | chr2 | 43451819 | 43452418 |
| chr2 | 43824034 | 43824132 | chr2 | 44497613 | 44497842 | chr2 | 45028911 | 45029450 |
| chr2 | 45029637 | 45029787 | chr2 | 45155039 | 45157783 | chr2 | 45159873 | 45160352 |
| chr2 | 45160496 | 45160735 | chr2 | 45161589 | 45162188 | chr2 | 45162319 | 45162558 |
| chr2 | 45162653 | 45163012 | chr2 | 45164589 | 45164768 | chr2 | 45165490 | 45165669 |
| chr2 | 45168857 | 45168908 | chr2 | 45169349 | 45170128 | chr2 | 45171295 | 45171954 |
| chr2 | 45176506 | 45176865 | chr2 | 45179546 | 45179725 | chr2 | 45179862 | 45180156 |
| chr2 | 45181417 | 45181776 | chr2 | 45181795 | 45182094 | chr2 | 45231239 | 45231478 |
| chr2 | 45231754 | 45232208 | chr2 | 45233307 | 45233666 | chr2 | 45235491 | 45236030 |
| chr2 | 45237585 | 45237884 | chr2 | 45240457 | 45240876 | chr2 | 45241041 | 45241280 |
| chr2 | 45395768 | 45396007 | chr2 | 45396234 | 45396533 | chr2 | 45396603 | 45397082 |
| chr2 | 46526223 | 46526331 | chr2 | 47193958 | 47194077 | chr2 | 47200517 | 47200696 |
| chr2 | 47249735 | 47249914 | chr2 | 47598298 | 47598477 | chr2 | 47598579 | 47598698 |
| chr2 | 47748048 | 47748587 | chr2 | 47796952 | 47797911 | chr2 | 47798093 | 47798752 |
| chr2 | 47798853 | 47799212 | chr2 | 48982485 | 48982964 | chr2 | 50573520 | 50573924 |
| chr2 | 50574041 | 50574940 | chr2 | 55289095 | 55289274 | chr2 | 56149762 | 56149941 |
| chr2 | 56150632 | 56151256 | chr2 | 56410918 | 56411087 | chr2 | 56411593 | 56411832 |
| chr2 | 58655968 | 58656207 | chr2 | 60706663 | 60706902 | chr2 | 60796498 | 60796612 |
| chr2 | 60797060 | 60797359 | chr2 | 61135116 | 61135235 | chr2 | 62798248 | 62798485 |
| chr2 | 63275470 | 63275949 | chr2 | 63278888 | 63279067 | chr2 | 63280853 | 63281752 |
| chr2 | 63282632 | 63282871 | chr2 | 63282924 | 63283053 | chr2 | 63283870 | 63284229 |
| chr2 | 63284675 | 63284914 | chr2 | 63284996 | 63287412 | chr2 | 66652937 | 66653063 |
| chr2 | 66653158 | 66653577 | chr2 | 66653690 | 66653989 | chr2 | 66660560 | 66660791 |
| chr2 | 66808447 | 66809453 | chr2 | 67625373 | 67625492 | chr2 | 67625733 | 67625852 |
| chr2 | 67626153 | 67626332 | chr2 | 68546249 | 68546968 | chr2 | 68559344 | 68559463 |
| chr2 | 68672777 | 68672956 | chr2 | 70418609 | 70418722 | chr2 | 71355039 | 71355218 |
| chr2 | 71503688 | 71503927 | chr2 | 71504007 | 71504246 | chr2 | 71680759 | 71680938 |
| chr2 | 71693423 | 71693694 | chr2 | 72374295 | 72374524 | chr2 | 72374611 | 72374850 |
| chr2 | 73145548 | 73145787 | chr2 | 73145824 | 73146123 | chr2 | 73147245 | 73148313 |
| chr2 | 73150850 | 73151029 | chr2 | 73151098 | 73151929 | chr2 | 73152600 | 73152839 |
| chr2 | 73429420 | 73429719 | chr2 | 73429862 | 73430161 | chr2 | 73430234 | 73430818 |
| chr2 | 73440271 | 73440370 | chr2 | 73518355 | 73519014 | chr2 | 73519501 | 73519920 |
| chr2 | 74010442 | 74010621 | chr2 | 74453989 | 74454348 | chr2 | 74726670 | 74226849 |
| chr2 | 74740761 | 74741480 | chr2 | 74741746 | 74742045 | chr2 | 74742085 | 74743824 |
| chr2 | 74781997 | 74782356 | chr2 | 75426958 | 75426980 | chr2 | 75427295 | 75427474 |
| chr2 | 75427845 | 75428264 | chr2 | 80529292 | 80529520 | chr2 | 80529573 | 80530112 |
| chr2 | 80530413 | 80530652 | chr2 | 80531651 | 80531830 | chr2 | 80649485 | 80549845 |
| chr2 | 85107377 | 85107616 | chr2 | 85361224 | 85361703 | chr2 | 87016489 | 87016728 |
| chr2 | 87017707 | 87018313 | chr2 | 88469219 | 88469398 | chr2 | 88751182 | 88751901 |
| chr2 | 88751961 | 88752380 | chr2 | 88752515 | 88752874 | chr2 | 88990108 | 88990347 |
| chr2 | 89064525 | 89065364 | chr2 | 95663873 | 95664112 | chr2 | 95690654 | 95690890 |
| chr2 | 95690944 | 95691363 | chr2 | 95691441 | 95691860 | chr2 | 95691908 | 95692567 |
| chr2 | 95941596 | 95941895 | chr2 | 96990808 | 96991399 | chr2 | 97193003 | 97193722 |
| chr2 | 97427415 | 97428194 | chr2 | 98703220 | 98703491 | chr2 | 98962800 | 98963039 |
| chr2 | 98963255 | 98963674 | chr2 | 98963750 | 98964289 | chr2 | 98964502 | 98964741 |
| chr2 | 99439054 | 99439593 | chr2 | 99553333 | 99553632 | chr2 | 99553723 | 99553734 |
| chr2 | 99796327 | 99796415 | chr2 | 99798571 | 99798746 | chr2 | 99799229 | 99799230 |
| chr2 | 100937747 | 100939246 | chr2 | 101009731 | 101010030 | chr2 | 101034149 | 101034388 |
| chr2 | 101436638 | 101436790 | chr2 | 102091079 | 102091335 | chr2 | 103236080 | 103236277 |
| chr2 | 105459001 | 105459600 | chr2 | 105459805 | 105460604 | chr2 | 105460847 | 105461026 |
| chr2 | 105461096 | 105461335 | chr2 | 105461461 | 105462000 | chr2 | 105462075 | 105462314 |
| chr2 | 105468701 | 105469000 | chr2 | 105469569 | 105470168 | chr2 | 105470266 | 105470925 |
| chr2 | 105472149 | 105472928 | chr2 | 105473162 | 105473521 | chr2 | 105478687 | 105479166 |
| chr2 | 105480444 | 105480683 | chr2 | 105483568 | 105483807 | chr2 | 105484367 | 105484480 |
| chr2 | 105488348 | 105488527 | chr2 | 105760890 | 105761004 | chr2 | 106060525 | 106060884 |
| chr2 | 106681644 | 106681870 | chr2 | 106681936 | 106682175 | chr2 | 106730137 | 106730316 |
| chr2 | 106959289 | 106959648 | chr2 | 106959833 | 106960072 | chr2 | 107103778 | 107104017 |
| chr2 | 107502499 | 107502918 | chr2 | 107503124 | 107503423 | chr2 | 107503458 | 107503637 |
| chr2 | 107503802 | 107504101 | chr2 | 109335091 | 109335264 | chr2 | 109648002 | 109648301 |

TABLE 14-continued

| chr | start | end | chr | start | end | chr | start | end |
|---|---|---|---|---|---|---|---|---|
| chr2 | 109745915 | 109746154 | chr2 | 109746204 | 109746563 | chr2 | 111875279 | 111875518 |
| chr2 | 111876621 | 111876964 | chr2 | 112656945 | 112657123 | chr2 | 114034797 | 114035276 |
| chr2 | 114256879 | 114257238 | chr2 | 114261200 | 114261559 | chr2 | 115918579 | 115920618 |
| chr2 | 118981075 | 118982574 | chr2 | 119067545 | 119068143 | chr2 | 119532059 | 119532358 |
| chr2 | 119566137 | 119566376 | chr2 | 119591259 | 119591558 | chr2 | 119592666 | 119592863 |
| chr2 | 119592923 | 119593642 | chr2 | 119599830 | 119600129 | chr2 | 119600235 | 119600839 |
| chr2 | 119600856 | 119600957 | chr2 | 119602515 | 119603174 | chr2 | 119603946 | 119604093 |
| chr2 | 119604154 | 119604245 | chr2 | 119604711 | 119604933 | chr2 | 119606048 | 119606283 |
| chr2 | 119606625 | 119606647 | chr2 | 119606692 | 119606931 | chr2 | 119607085 | 119607504 |
| chr2 | 119607694 | 119607933 | chr2 | 119610758 | 119611057 | chr2 | 119611653 | 119611892 |
| chr2 | 119612250 | 119612429 | chr2 | 119614047 | 119614271 | chr2 | 119614697 | 119614936 |
| chr2 | 119614952 | 119615719 | chr2 | 119616070 | 119616669 | chr2 | 119616721 | 119616960 |
| chr2 | 119914617 | 119914856 | chr2 | 119915947 | 119916186 | chr2 | 119916208 | 119916687 |
| chr2 | 120281556 | 120281790 | chr2 | 120281849 | 120282028 | chr2 | 120979994 | 120980173 |
| chr2 | 120980255 | 120980494 | chr2 | 121200303 | 121200532 | chr2 | 121345007 | 121345169 |
| chr2 | 121411987 | 121412231 | chr2 | 122495323 | 122495490 | chr2 | 124782247 | 124782546 |
| chr2 | 124782595 | 124783195 | chr2 | 127413828 | 127413908 | chr2 | 127423136 | 127423434 |
| chr2 | 127428910 | 127429147 | chr2 | 127438559 | 127438738 | chr2 | 127782953 | 127783360 |
| chr2 | 127863514 | 127863813 | chr2 | 127976391 | 127976750 | chr2 | 128421788 | 128422027 |
| chr2 | 128616519 | 128616628 | chr2 | 128847701 | 128847799 | chr2 | 130763485 | 130763724 |
| chr2 | 130971056 | 130971355 | chr2 | 131477742 | 131478023 | chr2 | 131594915 | 131595094 |
| chr2 | 131720754 | 131721353 | chr2 | 131721376 | 131722035 | chr2 | 131792157 | 131793236 |
| chr2 | 132088680 | 132088919 | chr2 | 132121566 | 132121823 | chr2 | 132152279 | 132152578 |
| chr2 | 132182701 | 132183180 | chr2 | 132767373 | 132767492 | chr2 | 133014571 | 133014678 |
| chr2 | 133015300 | 133015419 | chr2 | 133062239 | 133062478 | chr2 | 133426175 | 133426354 |
| chr2 | 133426561 | 133426776 | chr2 | 137522371 | 137522550 | chr2 | 137523751 | 137523759 |
| chr2 | 139536863 | 139537221 | chr2 | 139537355 | 139537954 | chr2 | 142887816 | 142888149 |
| chr2 | 142888264 | 142888503 | chr2 | 144694272 | 144695231 | chr2 | 145273369 | 145273848 |
| chr2 | 145274112 | 145274531 | chr2 | 145274715 | 145275314 | chr2 | 145282045 | 145282224 |
| chr2 | 148776713 | 148776876 | chr2 | 149633009 | 149633488 | chr2 | 149633646 | 149634065 |
| chr2 | 149645593 | 149645995 | chr2 | 151342979 | 151343218 | chr2 | 154333432 | 154333671 |
| chr2 | 154334170 | 154334769 | chr2 | 154335056 | 154335355 | chr2 | 154727963 | 154728442 |
| chr2 | 154728963 | 154729322 | chr2 | 154729485 | 154729664 | chr2 | 155555064 | 155566440 |
| chr2 | 157176506 | 157176805 | chr2 | 157176908 | 157178407 | chr2 | 157178637 | 157178809 |
| chr2 | 160760984 | 160761454 | chr2 | 161253375 | 161253554 | chr2 | 162272983 | 162274182 |
| chr2 | 162274220 | 162274414 | chr2 | 162274748 | 162274942 | chr2 | 162275055 | 162275887 |
| chr2 | 162279911 | 162281050 | chr2 | 162283291 | 162284130 | chr2 | 164592998 | 164593237 |
| chr2 | 168149978 | 168150337 | chr2 | 168150669 | 168151028 | chr2 | 170282882 | 170283178 |
| chr2 | 170551654 | 170551866 | chr2 | 170681792 | 170681909 | chr2 | 170682152 | 170682329 |
| chr2 | 171569986 | 171570525 | chr2 | 171570590 | 171570829 | chr2 | 171571171 | 171571342 |
| chr2 | 171571379 | 171571410 | chr2 | 171571800 | 171571997 | chr2 | 171670259 | 171670558 |
| chr2 | 171671385 | 171671984 | chr2 | 171674001 | 171674026 | chr2 | 171674664 | 171675143 |
| chr2 | 171675268 | 171675687 | chr2 | 171676590 | 171676885 | chr2 | 171822419 | 171822574 |
| chr2 | 172366939 | 172367178 | chr2 | 172411062 | 172411241 | chr2 | 172945027 | 172945266 |
| chr2 | 172945821 | 172946294 | chr2 | 172947684 | 172948405 | chr2 | 172948813 | 172948850 |
| chr2 | 172949090 | 172949809 | chr2 | 172951494 | 172951754 | chr2 | 172952425 | 172952640 |
| chr2 | 172952685 | 172953144 | chr2 | 172955346 | 172955645 | chr2 | 172957808 | 172958157 |
| chr2 | 172961319 | 172961678 | chr2 | 172964743 | 172965882 | chr2 | 172966174 | 172966533 |
| chr2 | 172972648 | 172973307 | chr2 | 173099710 | 173099889 | chr2 | 173100167 | 173100506 |
| chr2 | 173422651 | 173422770 | chr2 | 175190771 | 175192550 | chr2 | 175193187 | 175193906 |
| chr2 | 175195785 | 175195936 | chr2 | 175196355 | 175196371 | chr2 | 175196426 | 175196654 |
| chr2 | 175197015 | 175197194 | chr2 | 175198650 | 175198967 | chr2 | 175199432 | 175200012 |
| chr2 | 175200093 | 175202746 | chr2 | 175204100 | 175204279 | chr2 | 175204694 | 175206893 |
| chr2 | 175206752 | 175207111 | chr2 | 175207164 | 175207333 | chr2 | 175207446 | 175207745 |
| chr2 | 175208214 | 175209218 | chr2 | 175546942 | 175547241 | chr2 | 175547310 | 175547489 |
| chr2 | 176940092 | 176940391 | chr2 | 176943180 | 176943659 | chr2 | 176943763 | 176943863 |
| chr2 | 176943995 | 176944002 | chr2 | 176944326 | 176945885 | chr2 | 176946475 | 176947494 |
| chr2 | 176947647 | 176948006 | chr2 | 176948522 | 176948821 | chr2 | 176948971 | 176949150 |
| chr2 | 176949603 | 176949962 | chr2 | 176950051 | 176950350 | chr2 | 176956480 | 176956719 |
| chr2 | 176956821 | 176957300 | chr2 | 176957409 | 176957768 | chr2 | 176957829 | 176958008 |
| chr2 | 176958045 | 176958584 | chr2 | 176959191 | 176959589 | chr2 | 176963366 | 176963605 |
| chr2 | 176963999 | 176964238 | chr2 | 176964272 | 176965591 | chr2 | 176969387 | 176969984 |
| chr2 | 176972611 | 176972662 | chr2 | 176975946 | 176976289 | chr2 | 176980649 | 176981592 |
| chr2 | 176982487 | 176982726 | chr2 | 176986633 | 176986932 | chr2 | 176986962 | 176988401 |
| chr2 | 176993000 | 176993082 | chr2 | 176993409 | 176994741 | chr2 | 176994813 | 176994864 |
| chr2 | 176994981 | 176995712 | chr2 | 177001000 | 177001058 | chr2 | 177001118 | 177002079 |
| chr2 | 177004463 | 177004762 | chr2 | 177042891 | 177043610 | chr2 | 177053187 | 177053906 |
| chr2 | 177054023 | 177054442 | chr2 | 177502981 | 177503153 | chr2 | 178972904 | 178973143 |
| chr2 | 179317039 | 179317139 | chr2 | 182321308 | 182321727 | chr2 | 182321736 | 182322275 |
| chr2 | 182322292 | 182323131 | chr2 | 182542829 | 182543008 | chr2 | 182543221 | 182543413 |
| chr2 | 182543666 | 182544025 | chr2 | 182545124 | 182545363 | chr2 | 182545438 | 182545797 |
| chr2 | 182545887 | 182546179 | chr2 | 182546361 | 182546540 | chr2 | 182547290 | 182547709 |
| chr2 | 182547840 | 182548259 | chr2 | 182548992 | 182549231 | chr2 | 182549247 | 182549546 |
| chr2 | 182550020 | 182550199 | chr2 | 182819031 | 182819312 | chr2 | 183731200 | 183731619 |
| chr2 | 183731734 | 183732153 | chr2 | 185462776 | 185463075 | chr2 | 185463116 | 185463895 |
| chr2 | 186603414 | 186603593 | chr2 | 188418947 | 188419178 | chr2 | 189157513 | 189157692 |
| chr2 | 193058947 | 193060146 | chr2 | 193060294 | 193060533 | chr2 | 193060608 | 193060967 |
| chr2 | 193061341 | 193061580 | chr2 | 198456572 | 198456690 | chr2 | 200326551 | 200326730 |

TABLE 14-continued

| chr | start | end | chr | start | end | chr | start | end |
|---|---|---|---|---|---|---|---|---|
| chr2 | 200326765 | 200326813 | chr2 | 200327187 | 200327666 | chr2 | 200328669 | 200329748 |
| chr2 | 200333686 | 200333925 | chr2 | 200334895 | 200335308 | chr2 | 200335363 | 200336034 |
| chr2 | 201450453 | 201450812 | chr2 | 201450845 | 201451144 | chr2 | 202096992 | 202097231 |
| chr2 | 202899788 | 202899967 | chr2 | 206550978 | 206551457 | chr2 | 207138998 | 207139177 |
| chr2 | 207139267 | 207139686 | chr2 | 207307426 | 207307665 | chr2 | 207308711 | 207308950 |
| chr2 | 207506612 | 207507266 | chr2 | 208635519 | 208635864 | chr2 | 209113024 | 209113202 |
| chr2 | 209225137 | 209225376 | chr2 | 209271228 | 209271647 | chr2 | 210636255 | 210636974 |
| chr2 | 213401138 | 213401437 | chr2 | 213401511 | 213402050 | chr2 | 213403015 | 213403434 |
| chr2 | 217559222 | 217559401 | chr2 | 218806046 | 218806405 | chr2 | 219736062 | 219736705 |
| chr2 | 219827964 | 219827975 | chr2 | 219847360 | 219847659 | chr2 | 219848726 | 219849085 |
| chr2 | 219857648 | 219857860 | chr2 | 220080582 | 220080941 | chr2 | 220173904 | 220174383 |
| chr2 | 220196266 | 220196671 | chr2 | 220223024 | 220223203 | chr2 | 220223557 | 220223796 |
| chr2 | 220283250 | 220283609 | chr2 | 220299495 | 220300154 | chr2 | 220313696 | 220313777 |
| chr2 | 220348949 | 220349788 | chr2 | 220361370 | 220361609 | chr2 | 220416297 | 220416596 |
| chr2 | 220416770 | 220417729 | chr2 | 222435699 | 222435857 | chr2 | 223155678 | 223166277 |
| chr2 | 223158648 | 223159542 | chr2 | 223159735 | 223160154 | chr2 | 223160242 | 223160481 |
| chr2 | 223161173 | 223161352 | chr2 | 223161452 | 223162165 | chr2 | 223162678 | 223163637 |
| chr2 | 223163682 | 223164034 | chr2 | 223164440 | 223164979 | chr2 | 223165334 | 223165933 |
| chr2 | 223166190 | 223166825 | chr2 | 223167302 | 223167661 | chr2 | 223168346 | 223168945 |
| chr2 | 223169543 | 223169962 | chr2 | 223170286 | 223170525 | chr2 | 223171026 | 223171265 |
| chr2 | 223172263 | 223172356 | chr2 | 223172959 | 223173259 | chr2 | 223176018 | 223176282 |
| chr2 | 223176361 | 223177080 | chr2 | 223177224 | 223177703 | chr2 | 228029326 | 228029625 |
| chr2 | 228466762 | 228466881 | chr2 | 228735702 | 228735828 | chr2 | 228736135 | 228736554 |
| chr2 | 229046024 | 229046605 | chr2 | 230795461 | 230795640 | chr2 | 231693123 | 231693362 |
| chr2 | 232394867 | 232395166 | chr2 | 232791619 | 232792098 | chr2 | 233350112 | 233351491 |
| chr2 | 233351930 | 233352949 | chr2 | 233498615 | 233499394 | chr2 | 233750451 | 233750630 |
| chr2 | 235404471 | 235404590 | chr2 | 235860803 | 235860897 | chr2 | 236402683 | 236402901 |
| chr2 | 236403060 | 236403102 | chr2 | 236403174 | 236403419 | chr2 | 236403779 | 236403833 |
| chr2 | 236877188 | 236877367 | chr2 | 237072333 | 237073112 | chr2 | 237073265 | 237073504 |
| chr2 | 237076651 | 237076833 | chr2 | 237077466 | 237077685 | chr2 | 237077815 | 237078054 |
| chr2 | 237078097 | 237078427 | chr2 | 237080190 | 237080369 | chr2 | 237081255 | 237081914 |
| chr2 | 237082030 | 237082809 | chr2 | 237086291 | 237086559 | chr2 | 237145333 | 237145692 |
| chr2 | 237416114 | 237416504 | chr2 | 238395205 | 238395444 | chr2 | 238395815 | 238395988 |
| chr2 | 238535796 | 238536215 | chr2 | 238864570 | 238864989 | chr2 | 239051124 | 239051303 |
| chr2 | 239072551 | 239072790 | chr2 | 239139928 | 239140347 | chr2 | 239265703 | 239265881 |
| chr2 | 239482400 | 239482622 | chr2 | 239705202 | 239705364 | chr2 | 239755090 | 239755269 |
| chr2 | 239755638 | 239755877 | chr2 | 239756347 | 239756586 | chr2 | 239757551 | 239757910 |
| chr2 | 239757992 | 239758231 | chr2 | 239758251 | 239758490 | chr2 | 239957240 | 239957539 |
| chr2 | 240168722 | 240169141 | chr2 | 240319908 | 240320087 | chr2 | 240582303 | 240582448 |
| chr2 | 240619443 | 240619682 | chr2 | 240658145 | 240658504 | chr2 | 240658593 | 240658772 |
| chr2 | 241095576 | 241095868 | chr2 | 241393126 | 241393545 | chr2 | 241542045 | 241542344 |
| chr2 | 241544927 | 241545106 | chr2 | 241758299 | 241758898 | chr2 | 241759497 | 241759796 |
| chr2 | 241760075 | 241760254 | chr2 | 241760420 | 241760599 | chr2 | 241771062 | 241771361 |
| chr2 | 241865696 | 241865450 | chr2 | 242009317 | 242009496 | chr2 | 242021689 | 242021916 |
| chr2 | 242523873 | 242524172 | chr2 | 242549754 | 242549772 | chr2 | 242549918 | 242550053 |
| chr2 | 242554475 | 242554654 | chr2 | 242756042 | 242756401 | chr2 | 242832893 | 242833252 |
| chr2 | 242833484 | 242833663 | chr2 | 242833711 | 242833930 | chr2 | 242836419 | 242836718 |
| chr2 | 242925420 | 242925719 | chr3 | 238456 | 239175 | chr3 | 239534 | 240313 |
| chr3 | 2140189 | 2140488 | chr3 | 3840419 | 3840838 | chr3 | 3840946 | 3841245 |
| chr3 | 3842586 | 3842689 | chr3 | 5137871 | 5138109 | chr3 | 6902228 | 6902441 |
| chr3 | 6903500 | 6903564 | chr3 | 8810059 | 8810298 | chr3 | 9178065 | 9178281 |
| chr3 | 9593878 | 9594117 | chr3 | 9594286 | 9594473 | chr3 | 9595199 | 9595678 |
| chr3 | 9904155 | 9904634 | chr3 | 9941391 | 9941509 | chr3 | 9956984 | 9957223 |
| chr3 | 9957355 | 9957774 | chr3 | 10182757 | 10182917 | chr3 | 10183247 | 10183426 |
| chr3 | 10183632 | 10183811 | chr3 | 10857884 | 10858123 | chr3 | 11034163 | 11034462 |
| chr3 | 11034991 | 11035410 | chr3 | 12046310 | 12046727 | chr3 | 12917512 | 12917751 |
| chr3 | 12976987 | 12977150 | chr3 | 13323405 | 13324064 | chr3 | 13324277 | 13324516 |
| chr3 | 13324744 | 13325023 | chr3 | 13590341 | 13590940 | chr3 | 13679082 | 13679441 |
| chr3 | 13921316 | 13921555 | chr3 | 14851755 | 14851994 | chr3 | 14852233 | 14853012 |
| chr3 | 16553963 | 16554202 | chr3 | 16554251 | 16554730 | chr3 | 17001229 | 17001341 |
| chr3 | 19189367 | 19189546 | chr3 | 19189611 | 19189850 | chr3 | 19190061 | 19190253 |
| chr3 | 22413591 | 22413770 | chr3 | 22413871 | 22414050 | chr3 | 24870915 | 24870925 |
| chr3 | 24870982 | 24871281 | chr3 | 25469303 | 25469482 | chr3 | 25469605 | 25469784 |
| chr3 | 26663963 | 26664202 | chr3 | 26664303 | 26664842 | chr3 | 27754404 | 27754583 |
| chr3 | 27762260 | 27762733 | chr3 | 27762783 | 27762962 | chr3 | 27763492 | 27763671 |
| chr3 | 27764421 | 27764600 | chr3 | 27765085 | 27765444 | chr3 | 27771422 | 27772081 |
| chr3 | 28616745 | 28617764 | chr3 | 32858274 | 32859273 | chr3 | 32859992 | 32860351 |
| chr3 | 33259801 | 33260876 | chr3 | 35680768 | 35620947 | chr3 | 36805720 | 36805959 |
| chr3 | 36806053 | 36806292 | chr3 | 37493429 | 37493720 | chr3 | 37901952 | 37902028 |
| chr3 | 38030610 | 38030789 | chr3 | 38032257 | 38032436 | chr3 | 38035669 | 38036088 |
| chr3 | 38080596 | 38081015 | chr3 | 38081061 | 38081360 | chr3 | 38690527 | 38690766 |
| chr3 | 38691316 | 38691557 | chr3 | 39851674 | 39851913 | chr3 | 41266012 | 41266239 |
| chr3 | 42222640 | 42222737 | chr3 | 42640761 | 42640874 | chr3 | 42814467 | 42814706 |
| chr3 | 42947333 | 42947632 | chr3 | 44036176 | 44036415 | chr3 | 44036496 | 44036675 |
| chr3 | 44036743 | 44037282 | chr3 | 44037525 | 44037764 | chr3 | 44037781 | 44038740 |
| chr3 | 44039265 | 44040097 | chr3 | 44040413 | 44040652 | chr3 | 44040709 | 44041128 |
| chr3 | 44063354 | 44063953 | chr3 | 44596405 | 44596584 | chr3 | 44596614 | 44596913 |
| chr3 | 44626336 | 44626815 | chr3 | 44726855 | 44727274 | chr3 | 45187222 | 45187461 |

TABLE 14-continued

| chr | start | end | chr | start | end | chr | start | end |
|---|---|---|---|---|---|---|---|---|
| chr3 | 46924905 | 46925039 | chr3 | 48227686 | 48227788 | chr3 | 48236391 | 48236553 |
| chr3 | 48693228 | 48694247 | chr3 | 48698723 | 48699859 | chr3 | 49906993 | 49907232 |
| chr3 | 49939836 | 49940495 | chr3 | 50243283 | 50243582 | chr3 | 50374581 | 50374760 |
| chr3 | 50374843 | 50375022 | chr3 | 50375104 | 50375639 | chr3 | 50395432 | 50395611 |
| chr3 | 50402078 | 50403037 | chr3 | 50575518 | 50575635 | chr3 | 52552500 | 52552739 |
| chr3 | 52553395 | 52553537 | chr3 | 53032708 | 53033609 | chr3 | 54155525 | 54155764 |
| chr3 | 54157297 | 54157536 | chr3 | 54157780 | 54158006 | chr3 | 55519117 | 55519228 |
| chr3 | 55523019 | 55623318 | chr3 | 62353291 | 62354130 | chr3 | 52354187 | 62354426 |
| chr3 | 62354531 | 62355010 | chr3 | 62355332 | 62355571 | chr3 | 62355692 | 62357431 |
| chr3 | 62357527 | 62357766 | chr3 | 62358059 | 62358178 | chr3 | 62358444 | 62358683 |
| chr3 | 62358758 | 62359115 | chr3 | 62359276 | 62359995 | chr3 | 62360222 | 62360641 |
| chr3 | 62362812 | 62363206 | chr3 | 62363541 | 62363780 | chr3 | 62363819 | 62364418 |
| chr3 | 62364659 | 62365205 | chr3 | 62861044 | 62861223 | chr3 | 63264065 | 63264135 |
| chr3 | 63264158 | 63264244 | chr3 | 68056816 | 68057235 | chr3 | 68980843 | 68981202 |
| chr3 | 68981469 | 68981708 | chr3 | 69590865 | 69591044 | chr3 | 69591264 | 69592163 |
| chr3 | 69741004 | 69741087 | chr3 | 69937792 | 69937926 | chr3 | 71802489 | 21802720 |
| chr3 | 71803040 | 71803459 | chr3 | 71803553 | 71803912 | chr3 | 73045525 | 73045672 |
| chr3 | 75955924 | 75956463 | chr3 | 79815421 | 79815660 | chr3 | 79816688 | 79817099 |
| chr3 | 79817214 | 79817393 | chr3 | 85008452 | 85008811 | chr3 | 88248026 | 88248142 |
| chr3 | 96532726 | 96532965 | chr3 | 96533302 | 96533541 | chr3 | 96533947 | 96534186 |
| chr3 | 98620817 | 98621056 | chr3 | 99594836 | 99595195 | chr3 | 101230575 | 101230641 |
| chr3 | 101230942 | 101231174 | chr3 | 101397150 | 101397302 | chr3 | 106936068 | 106936294 |
| chr3 | 112052411 | 112052521 | chr3 | 117715472 | 117715643 | chr3 | 117715772 | 117716551 |
| chr3 | 120003954 | 120004438 | chr3 | 120169683 | 120169922 | chr3 | 120627319 | 120627535 |
| chr3 | 121902878 | 121903717 | chr3 | 122234151 | 122234246 | chr3 | 122702194 | 122702430 |
| chr3 | 123166972 | 123167631 | chr3 | 123167679 | 123167918 | chr3 | 125898567 | 125899292 |
| chr3 | 125899445 | 125899706 | chr3 | 125899740 | 125899979 | chr3 | 125932169 | 125932586 |
| chr3 | 126373433 | 126373619 | chr3 | 126373669 | 126373792 | chr3 | 126854599 | 126854898 |
| chr3 | 127534879 | 127534976 | chr3 | 127634112 | 127634291 | chr3 | 127794464 | 127794943 |
| chr3 | 127795248 | 127795253 | chr3 | 128202373 | 128202552 | chr3 | 128208829 | 128209308 |
| chr3 | 128273913 | 128274692 | chr3 | 128417231 | 128417306 | chr3 | 128719977 | 128720696 |
| chr3 | 128720780 | 128721319 | chr3 | 128764472 | 128764711 | chr3 | 129693075 | 129694391 |
| chr3 | 129694430 | 129694609 | chr3 | 130064351 | 130064588 | chr3 | 130064744 | 130064923 |
| chr3 | 130235952 | 130236298 | chr3 | 130519821 | 130519929 | chr3 | 131753957 | 131754136 |
| chr3 | 132756966 | 132757205 | chr3 | 133217923 | 133218102 | chr3 | 133748044 | 133748206 |
| chr3 | 133748552 | 133748679 | chr3 | 134369572 | 134369931 | chr3 | 134514792 | 134514879 |
| chr3 | 134514960 | 134514971 | chr3 | 134515040 | 134515459 | chr3 | 134515590 | 134516309 |
| chr3 | 136537567 | 136537806 | chr3 | 136538520 | 136538910 | chr3 | 136582941 | 136583037 |
| chr3 | 136751546 | 136751833 | chr3 | 137479149 | 137479388 | chr3 | 137479525 | 137479764 |
| chr3 | 137479893 | 137480847 | chr3 | 137481094 | 137481393 | chr3 | 137481782 | 137482261 |
| chr3 | 137483212 | 137483319 | chr3 | 137483570 | 137483691 | chr3 | 137483746 | 137484105 |
| chr3 | 137484319 | 137484618 | chr3 | 137485931 | 137486390 | chr3 | 137486429 | 137486653 |
| chr3 | 137487874 | 137488113 | chr3 | 137488856 | 137491135 | chr3 | 138153889 | 138154068 |
| chr3 | 138154240 | 138154479 | chr3 | 138655857 | 138656216 | chr3 | 138656743 | 138656982 |
| chr3 | 138657347 | 138659187 | chr3 | 138662060 | 138662535 | chr3 | 138662705 | 138662941 |
| chr3 | 138663611 | 138664249 | chr3 | 138664330 | 138664569 | chr3 | 138664827 | 138665426 |
| chr3 | 138665479 | 138665718 | chr3 | 138665779 | 138666378 | chr3 | 138668646 | 138669485 |
| chr3 | 138679375 | 138679614 | chr3 | 139258173 | 139258412 | chr3 | 139653413 | 139653772 |
| chr3 | 140769430 | 140769789 | chr3 | 140769830 | 140770909 | chr3 | 140771231 | 140771410 |
| chr3 | 140771716 | 140771955 | chr3 | 141174269 | 141174688 | chr3 | 141481983 | 141482162 |
| chr3 | 141516315 | 141516794 | chr3 | 142682184 | 142682483 | chr3 | 142791076 | 142791173 |
| chr3 | 142837906 | 142838445 | chr3 | 142838530 | 142839129 | chr3 | 142839439 | 142840338 |
| chr3 | 142896066 | 142896305 | chr3 | 145878591 | 145878641 | chr3 | 146187843 | 146188069 |
| chr3 | 147074871 | 147075110 | chr3 | 147077211 | 147077640 | chr3 | 147078865 | 147079284 |
| chr3 | 147087472 | 147087891 | chr3 | 147088363 | 147088542 | chr3 | 147088840 | 147089136 |
| chr3 | 147098332 | 147098571 | chr3 | 147105805 | 147106104 | chr3 | 147108758 | 147110017 |
| chr3 | 147110055 | 147110774 | chr3 | 147110835 | 147111188 | chr3 | 147111451 | 147111734 |
| chr3 | 147126963 | 147127142 | chr3 | 147127583 | 147128002 | chr3 | 147128188 | 147128420 |
| chr3 | 147136839 | 147137258 | chr3 | 147138694 | 147138932 | chr3 | 147139052 | 147139231 |
| chr3 | 147139272 | 147139631 | chr3 | 147142126 | 147142365 | chr3 | 148415327 | 148415746 |
| chr3 | 148803259 | 148803370 | chr3 | 149374866 | 149375105 | chr3 | 150802882 | 150803181 |
| chr3 | 150803941 | 150804180 | chr3 | 150804880 | 150805119 | chr3 | 152553245 | 152553484 |
| chr3 | 152553573 | 152553807 | chr3 | 152877592 | 152877703 | chr3 | 153838725 | 153838964 |
| chr3 | 153839429 | 153839559 | chr3 | 153839641 | 153840148 | chr3 | 154146034 | 154146513 |
| chr3 | 154146572 | 154146991 | chr3 | 154797250 | 154797289 | chr3 | 154797377 | 154797789 |
| chr3 | 156008943 | 156009501 | chr3 | 156534228 | 156534407 | chr3 | 157155164 | 157156523 |
| chr3 | 157155922 | 157156298 | chr3 | 157812122 | 157812721 | chr3 | 157812812 | 157813171 |
| chr3 | 157813507 | 157813926 | chr3 | 157815787 | 157815920 | chr3 | 157820502 | 157820681 |
| chr3 | 157820985 | 157821764 | chr3 | 157821939 | 157822106 | chr3 | 157822989 | 157823228 |
| chr3 | 157823390 | 157823569 | chr3 | 157824052 | 157824332 | chr3 | 157824414 | 157824953 |
| chr3 | 157825083 | 157825491 | chr3 | 158288801 | 158288974 | chr3 | 159756593 | 159756952 |
| chr3 | 159944397 | 159944636 | chr3 | 160167929 | 160168108 | chr3 | 164912329 | 164912568 |
| chr3 | 164912827 | 164913960 | chr3 | 164914906 | 164915205 | chr3 | 169376080 | 169376319 |
| chr3 | 169376581 | 169376878 | chr3 | 169378746 | 169379105 | chr3 | 169539810 | 169540704 |
| chr3 | 169540967 | 169541134 | chr3 | 170136540 | 170136839 | chr3 | 170137571 | 170137585 |
| chr3 | 170137624 | 170137803 | chr3 | 170302528 | 170302767 | chr3 | 170302989 | 170303527 |
| chr3 | 170303563 | 170303922 | chr3 | 171527953 | 171528071 | chr3 | 172165356 | 172166725 |
| chr3 | 172166783 | 172167142 | chr3 | 172167223 | 172167402 | chr3 | 172167580 | 172167995 |

TABLE 14-continued

| chr | start | end | chr | start | end | chr | start | end |
|---|---|---|---|---|---|---|---|---|
| chr3 | 172355818 | 172355888 | chr3 | 172355903 | 172355997 | chr3 | 172425281 | 172425382 |
| chr3 | 172425701 | 172425802 | chr3 | 172469837 | 172469951 | chr3 | 173115155 | 173115634 |
| chr3 | 173302464 | 173302763 | chr3 | 173302900 | 173303319 | chr3 | 178861414 | 178861533 |
| chr3 | 178916788 | 178916967 | chr3 | 178921465 | 178921644 | chr3 | 178935968 | 178936205 |
| chr3 | 178961997 | 178952176 | chr3 | 179168582 | 179169354 | chr3 | 179754086 | 179755465 |
| chr3 | 181413068 | 181413460 | chr3 | 181413647 | 181414426 | chr3 | 181419972 | 181420211 |
| chr3 | 181420226 | 181420465 | chr3 | 181421308 | 181422387 | chr3 | 181422464 | 181423063 |
| chr3 | 181428311 | 181428850 | chr3 | 181430614 | 181430853 | chr3 | 181437030 | 181437449 |
| chr3 | 181438095 | 181438454 | chr3 | 181440811 | 181442010 | chr3 | 181442069 | 181442488 |
| chr3 | 181442927 | 181443646 | chr3 | 181443662 | 181443961 | chr3 | 181444023 | 181444322 |
| chr3 | 181444335 | 181444754 | chr3 | 181444828 | 181445114 | chr3 | 181445268 | 181445567 |
| chr3 | 181445649 | 181445948 | chr3 | 182816010 | 182816129 | chr3 | 182895871 | 182895990 |
| chr3 | 183145336 | 183145695 | chr3 | 183145829 | 183146128 | chr3 | 183146297 | 183146536 |
| chr3 | 183146574 | 183146753 | chr3 | 183648036 | 183648101 | chr3 | 183728814 | 183728926 |
| chr3 | 183965514 | 183965625 | chr3 | 184017964 | 184018237 | chr3 | 184031615 | 184031734 |
| chr3 | 184057527 | 184057636 | chr3 | 184301634 | 184301873 | chr3 | 184319741 | 184319980 |
| chr3 | 185001908 | 185002018 | chr3 | 185271201 | 185271380 | chr3 | 185303173 | 185303352 |
| chr3 | 185362989 | 185363348 | chr3 | 185643246 | 185643485 | chr3 | 186078683 | 186078982 |
| chr3 | 186079119 | 186079412 | chr3 | 186080114 | 186080293 | chr3 | 186857051 | 186857710 |
| chr3 | 187387776 | 187388315 | chr3 | 192125754 | 192125933 | chr3 | 192126056 | 192126955 |
| chr3 | 192127265 | 192128164 | chr3 | 192232017 | 192232256 | chr3 | 192232362 | 192232437 |
| chr3 | 192232478 | 192232661 | chr3 | 192232753 | 192233232 | chr3 | 192958830 | 192959057 |
| chr3 | 193312046 | 193312165 | chr3 | 193419528 | 193419745 | chr3 | 193548557 | 193548797 |
| chr3 | 193548842 | 193548916 | chr3 | 193776015 | 193776194 | chr3 | 194048731 | 194049015 |
| chr3 | 194208185 | 194208664 | chr3 | 194407924 | 194407936 | chr3 | 194408055 | 194408103 |
| chr3 | 194408279 | 194409118 | chr3 | 195536642 | 195536828 | chr3 | 195538330 | 195538435 |
| chr3 | 195586956 | 195587195 | chr3 | 195601157 | 195601363 | chr3 | 195602364 | 195602435 |
| chr3 | 195648720 | 195648899 | chr3 | 196069893 | 196070192 | chr3 | 196255543 | 196255722 |
| chr3 | 196387206 | 196387505 | chr3 | 196387528 | 196387767 | chr3 | 196388303 | 196388662 |
| chr3 | 196731055 | 196731133 | chr3 | 196731197 | 196731414 | chr3 | 196755893 | 196756063 |
| chr3 | 197327025 | 197327131 | chr3 | 197616633 | 197616812 | chr3 | 197676955 | 197677134 |
| chr3 | 197685698 | 197685817 | chr3 | 197686060 | 197686177 | chr3 | 197686891 | 197687310 |
| chr4 | 107616 | 107855 | chr4 | 330311 | 330790 | chr4 | 331308 | 331416 |
| chr4 | 568333 | 570012 | chr4 | 570931 | 571110 | chr4 | 571420 | 571779 |
| chr4 | 628488 | 628770 | chr4 | 651110 | 651348 | chr4 | 557570 | 657657 |
| chr4 | 678397 | 678576 | chr4 | 682710 | 683009 | chr4 | 718082 | 718202 |
| chr4 | 718240 | 718321 | chr4 | 829537 | 829716 | chr4 | 955292 | 955531 |
| chr4 | 955774 | 956013 | chr4 | 995777 | 996436 | chr4 | 996555 | 996794 |
| chr4 | 1008642 | 1008806 | chr4 | 1016041 | 1016340 | chr4 | 1016533 | 1016787 |
| chr4 | 1025852 | 1026151 | chr4 | 1093457 | 1093558 | chr4 | 1165276 | 1165575 |
| chr4 | 1188947 | 1189126 | chr4 | 1282441 | 1282620 | chr4 | 1331636 | 1331780 |
| chr4 | 1338615 | 1338891 | chr4 | 1339023 | 1339130 | chr4 | 1396498 | 1396917 |
| chr4 | 1397297 | 1397596 | chr4 | 1398222 | 1398461 | chr4 | 1399627 | 1399652 |
| chr4 | 1400638 | 1400877 | chr4 | 1401608 | 1401847 | chr4 | 1612294 | 1512473 |
| chr4 | 1556335 | 1556603 | chr4 | 1576387 | 1576626 | chr4 | 1616606 | 1617173 |
| chr4 | 1687006 | 1687185 | chr4 | 1803447 | 1803686 | chr4 | 1806010 | 1806089 |
| chr4 | 1807281 | 1807460 | chr4 | 1993677 | 1994276 | chr4 | 2042117 | 2042631 |
| chr4 | 2066011 | 2066370 | chr4 | 2305571 | 2305930 | chr4 | 2527903 | 2528012 |
| chr4 | 2540247 | 2540395 | chr4 | 2765767 | 2766006 | chr4 | 2926292 | 2926471 |
| chr4 | 2978878 | 2979094 | chr4 | 3446917 | 3447096 | chr4 | 3447737 | 3448096 |
| chr4 | 3768759 | 3769418 | chr4 | 3769439 | 3769678 | chr4 | 3873613 | 3873852 |
| chr4 | 4228094 | 4228333 | chr4 | 4229586 | 4229885 | chr4 | 4387431 | 4387730 |
| chr4 | 4417467 | 4417706 | chr4 | 4855018 | 4855257 | chr4 | 4855283 | 4855622 |
| chr4 | 4862671 | 4863210 | chr4 | 4867613 | 4867864 | chr4 | 4867924 | 4867972 |
| chr4 | 4868468 | 4869187 | chr4 | 4872009 | 4872248 | chr4 | 4872695 | 4872934 |
| chr4 | 4873329 | 4873580 | chr4 | 5052995 | 5053594 | chr4 | 5053651 | 5054190 |
| chr4 | 5709819 | 5710358 | chr4 | 5712891 | 5713370 | chr4 | 5889848 | 5890147 |
| chr4 | 5890180 | 5890539 | chr4 | 5891871 | 5892290 | chr4 | 5892676 | 5892791 |
| chr4 | 5893898 | 5894434 | chr4 | 5894583 | 5894882 | chr4 | 6200797 | 6201336 |
| chr4 | 6202011 | 6202370 | chr4 | 6247277 | 6247456 | chr4 | 6564904 | 6565143 |
| chr4 | 6670110 | 6670289 | chr4 | 5748251 | 6748662 | chr4 | 6957489 | 6957701 |
| chr4 | 7647679 | 7648038 | chr4 | 7758402 | 7758581 | chr4 | 8582475 | 8582654 |
| chr4 | 8607724 | 8608023 | chr4 | 8608459 | 8608698 | chr4 | 8858804 | 8859823 |
| chr4 | 8859875 | 8860654 | chr4 | 8861563 | 8862102 | chr4 | 8862705 | 8863004 |
| chr4 | 8863339 | 8863878 | chr4 | 8864434 | 8864699 | chr4 | 8864736 | 8865155 |
| chr4 | 8868734 | 8869453 | chr4 | 8869498 | 8869917 | chr4 | 8872957 | 8873436 |
| chr4 | 8873718 | 8874077 | chr4 | 8874397 | 8874812 | chr4 | 8875803 | 8875982 |
| chr4 | 8893422 | 8893606 | chr4 | 8893714 | 8894013 | chr4 | 8894547 | 8895446 |
| chr4 | 8895480 | 8895659 | chr4 | 8895835 | 8896134 | chr4 | 9423195 | 9423281 |
| chr4 | 9782942 | 9783502 | chr4 | 10458309 | 10459208 | chr4 | 10462740 | 10453636 |
| chr4 | 11429482 | 11429720 | chr4 | 13523929 | 13524528 | chr4 | 13624571 | 13524872 |
| chr4 | 13537492 | 13537779 | chr4 | 13540907 | 13541146 | chr4 | 13541309 | 13541548 |
| chr4 | 13543777 | 13544196 | chr4 | 13545483 | 13545842 | chr4 | 13545933 | 13546172 |
| chr4 | 13548404 | 13548999 | chr4 | 13549246 | 13549605 | chr4 | 15780123 | 15780422 |
| chr4 | 16084642 | 16085481 | chr4 | 16085531 | 16085770 | chr4 | 17782913 | 17783692 |
| chr4 | 20254619 | 20254798 | chr4 | 20255339 | 20255938 | chr4 | 20256067 | 20256426 |
| chr4 | 21950146 | 21950445 | chr4 | 24801718 | 24802077 | chr4 | 24914564 | 24914743 |
| chr4 | 25656728 | 25656893 | chr4 | 25657338 | 25657577 | chr4 | 27086358 | 27086537 |

TABLE 14-continued

| chr | start | end | chr | start | end | chr | start | end |
|---|---|---|---|---|---|---|---|---|
| chr4 | 30724162 | 30724461 | chr4 | 37245640 | 37245939 | chr4 | 37246060 | 37246959 |
| chr4 | 37247007 | 37247306 | chr4 | 40910206 | 40910563 | chr4 | 41258624 | 41259276 |
| chr4 | 41746922 | 41747221 | chr4 | 41747419 | 41747658 | chr4 | 41747858 | 41747977 |
| chr4 | 41748038 | 41748397 | chr4 | 41748583 | 41748882 | chr4 | 41748976 | 41749138 |
| chr4 | 41749187 | 41749846 | chr4 | 41750125 | 41750604 | chr4 | 41751789 | 41751990 |
| chr4 | 41752363 | 41752782 | chr4 | 41752884 | 41753483 | chr4 | 41753512 | 41754171 |
| chr4 | 41875337 | 41875891 | chr4 | 41881286 | 41881517 | chr4 | 41882469 | 41882682 |
| chr4 | 41882988 | 41883407 | chr4 | 41883411 | 41883710 | chr4 | 41993731 | 41993896 |
| chr4 | 42152808 | 42154127 | chr4 | 42154201 | 42154440 | chr4 | 42154561 | 42155100 |
| chr4 | 42398768 | 42398947 | chr4 | 42399045 | 42399284 | chr4 | 42399601 | 42399960 |
| chr4 | 44449387 | 44449746 | chr4 | 44450170 | 44450469 | chr4 | 46995079 | 46995918 |
| chr4 | 47034834 | 47035013 | chr4 | 48485152 | 48486104 | chr4 | 48486254 | 48486493 |
| chr4 | 48492100 | 48492517 | chr4 | 48988013 | 48988229 | chr4 | 48988380 | 48988432 |
| chr4 | 53728417 | 53729087 | chr4 | 54966756 | 54967175 | chr4 | 54967264 | 54967563 |
| chr4 | 54969832 | 54970174 | chr4 | 54970277 | 54970576 | chr4 | 54975855 | 54976214 |
| chr4 | 55092973 | 55093332 | chr4 | 55096143 | 55096363 | chr4 | 55096441 | 55096442 |
| chr4 | 55097315 | 55097554 | chr4 | 55097709 | 55097729 | chr4 | 55097874 | 55098473 |
| chr4 | 55098590 | 55098769 | chr4 | 55099040 | 55099159 | chr4 | 55524138 | 55524367 |
| chr4 | 55991019 | 55991270 | chr4 | 55992030 | 55992269 | chr4 | 56659618 | 56660097 |
| chr4 | 57371632 | 57372051 | chr4 | 57372241 | 57372600 | chr4 | 57396866 | 57397345 |
| chr4 | 57521300 | 57522908 | chr4 | 57687632 | 57687871 | che4 | 57777338 | 57777577 |
| chr4 | 57803529 | 57803613 | chr4 | 57975930 | 57976289 | chr4 | 57976316 | 57976675 |
| chr4 | 62066106 | 62066645 | chr4 | 62067419 | 62067718 | chr4 | 62067992 | 62068231 |
| chr4 | 66535048 | 66535527 | chr4 | 66536068 | 66536427 | chr4 | 74702379 | 74702608 |
| chr4 | 74809786 | 74810025 | chr4 | 75241349 | 75241528 | chr4 | 75858482 | 75858611 |
| chr4 | 76555455 | 76555934 | chr4 | 76912717 | 76912836 | chr4 | 79689573 | 79689812 |
| chr4 | 81106252 | 81106669 | chr4 | 81124201 | 81124740 | chr4 | 81186972 | 81187151 |
| chr4 | 81187485 | 81187664 | chr4 | 81188230 | 81188644 | chr4 | 81189336 | 81189995 |
| chr4 | 81951357 | 81951536 | chr4 | 81951938 | 81952046 | chr4 | 81952078 | 81952437 |
| chr4 | 82135786 | 82136145 | chr4 | 82136403 | 82136642 | chr4 | 82136733 | 82136912 |
| chr4 | 83323677 | 83323677 | chr4 | 85402681 | 85403425 | chr4 | 85403824 | 85404783 |
| chr4 | 85413977 | 85414244 | chr4 | 85414270 | 85414509 | chr4 | 85414637 | 85414936 |
| chr4 | 85417241 | 85417474 | chr4 | 85417517 | 85417660 | chr4 | 85417873 | 85418166 |
| chr4 | 85418319 | 85419038 | chr4 | 85422101 | 85422520 | chr4 | 85422866 | 85423405 |
| chr4 | 85424323 | 85424562 | chr4 | 87515263 | 87515442 | chr4 | 89378362 | 89378601 |
| chr4 | 89378667 | 89378966 | chr4 | 90757439 | 90757913 | chr4 | 90758039 | 90758210 |
| chr4 | 90758681 | 90758980 | chr4 | 93225163 | 93225252 | chr4 | 93226367 | 93226606 |
| chr4 | 93226719 | 93226958 | chr4 | 94750882 | 94751241 | chr4 | 94751342 | 94751581 |
| chr4 | 94753341 | 94753520 | chr4 | 94755887 | 94756186 | chr4 | 95127560 | 95127679 |
| chr4 | 96470678 | 96470857 | chr4 | 101111166 | 101111585 | chr4 | 101111766 | 101112058 |
| chr4 | 107955210 | 107955929 | chr4 | 107956582 | 107957181 | chr4 | 107957271 | 107957570 |
| chr4 | 109093016 | 109093255 | chr4 | 109093307 | 109093606 | chr4 | 110222996 | 110224075 |
| chr4 | 111532558 | 111533032 | chr4 | 111536192 | 111536791 | chr4 | 111536882 | 111537121 |
| chr4 | 111537356 | 111537572 | chr4 | 111540101 | 111540460 | chr4 | 111542113 | 111542570 |
| chr4 | 111542728 | 111542832 | chr4 | 111543132 | 111543551 | chr4 | 111543579 | 111543807 |
| chr4 | 111544303 | 111544662 | chr4 | 111549726 | 111549905 | chr4 | 111550517 | 111550930 |
| chr4 | 111552044 | 111552223 | chr4 | 111553006 | 111553545 | chr4 | 111553816 | 111554054 |
| chr4 | 111554864 | 111555447 | chr4 | 111557888 | 111558171 | chr4 | 111558473 | 111569312 |
| chr4 | 111560174 | 111560713 | chr4 | 111562493 | 111562732 | chr4 | 113154804 | 113155043 |
| chr4 | 113430537 | 113430776 | chr4 | 113431755 | 113432654 | chr4 | 113436133 | 113436372 |
| chr4 | 113441514 | 113441813 | chr4 | 113442013 | 113442612 | chr4 | 113444003 | 113444534 |
| chr4 | 117847310 | 117847549 | chr4 | 121843986 | 121844285 | chr4 | 121992170 | 121992409 |
| chr4 | 121993915 | 121994334 | chr4 | 122301405 | 122301934 | chr4 | 122302032 | 122302331 |
| chr4 | 122685744 | 122686029 | chr4 | 122686119 | 122686598 | chr4 | 122871195 | 122871434 |
| chr4 | 122871488 | 122872087 | chr4 | 123664147 | 123664249 | chr4 | 126237252 | 126237491 |
| chr4 | 126237552 | 126237701 | chr4 | 126237931 | 126238511 | chr4 | 128543956 | 128544255 |
| chr4 | 128644569 | 128544868 | chr4 | 134067794 | 134068093 | chr4 | 134068475 | 134068894 |
| chr4 | 134069215 | 134069394 | chr4 | 134069498 | 134069977 | chr4 | 134070300 | 134070479 |
| chr4 | 134071559 | 134073058 | chr4 | 134073104 | 134073403 | chr4 | 134073486 | 134073725 |
| chr4 | 134073772 | 134073789 | chr4 | 134073944 | 134074243 | chr4 | 140200427 | 140201566 |
| chr4 | 140656567 | 140657166 | chr4 | 141347925 | 141348227 | chr4 | 141418841 | 141419500 |
| chr4 | 141488790 | 141489159 | chr4 | 142053155 | 142053235 | chr4 | 142053418 | 142053837 |
| chr4 | 142054141 | 142054560 | chr4 | 143766714 | 143767013 | chr4 | 144621248 | 144622147 |
| chr4 | 145567951 | 145568250 | chr4 | 145568361 | 145568745 | chr4 | 146853937 | 146854056 |
| chr4 | 147558179 | 147558598 | chr4 | 147559220 | 147560659 | chr4 | 147560835 | 147562154 |
| chr4 | 147568549 | 147569148 | chr4 | 147569546 | 147569685 | chr4 | 147569697 | 147569725 |
| chr4 | 147576079 | 147576738 | chr4 | 152246058 | 152246237 | chr4 | 152246398 | 152246403 |
| chr4 | 153249297 | 153249476 | chr4 | 153702690 | 153702805 | chr4 | 154216277 | 154216449 |
| chr4 | 154709440 | 154710639 | chr4 | 154710701 | 154710999 | chr4 | 154712084 | 154712683 |
| chr4 | 154713426 | 154713605 | chr4 | 154713861 | 154714085 | chr4 | 155254092 | 155254271 |
| chr4 | 155411411 | 155411786 | chr4 | 155411930 | 155412370 | chr4 | 155663129 | 155663728 |
| chr4 | 155665371 | 155665550 | chr4 | 156129079 | 156129258 | chr4 | 156129354 | 156129593 |
| chr4 | 156129653 | 156129892 | chr4 | 156129963 | 156130382 | chr4 | 156297337 | 156297636 |
| chr4 | 156297747 | 156298130 | chr4 | 156588237 | 156588245 | chr4 | 156588364 | 156588476 |
| chr4 | 156589179 | 156589203 | chr4 | 166589259 | 156589418 | chr4 | 156680156 | 156680485 |
| chr4 | 156680596 | 156680635 | chr4 | 156681281 | 156681465 | chr4 | 158141502 | 158141681 |
| chr4 | 158142744 | 158143101 | chr4 | 158143355 | 158143654 | chr4 | 164252890 | 164253549 |
| chr4 | 165304428 | 165304667 | chr4 | 165304948 | 165305247 | chr4 | 166414817 | 166414996 |

TABLE 14-continued

| chr | start | end | chr | start | end | chr | start | end |
|---|---|---|---|---|---|---|---|---|
| chr4 | 166794691 | 166794990 | chr4 | 166795933 | 166796292 | chr4 | 168155010 | 168155369 |
| chr4 | 170865262 | 170865381 | chr4 | 170947187 | 170947426 | chr4 | 172734067 | 172734306 |
| chr4 | 172734461 | 172734880 | chr4 | 174429584 | 174429763 | chr4 | 174430212 | 174431171 |
| chr4 | 174438477 | 174438627 | chr4 | 174439741 | 174440340 | chr4 | 174440555 | 174440794 |
| chr4 | 174443138 | 174443317 | chr4 | 174443480 | 174444019 | chr4 | 174444077 | 174444256 |
| chr4 | 174446387 | 174446595 | chr4 | 174449847 | 174451586 | chr4 | 174451768 | 174452187 |
| chr4 | 174459094 | 174459747 | chr4 | 174459770 | 174459933 | chr4 | 174460085 | 174460309 |
| chr4 | 175132661 | 175132840 | chr4 | 175132994 | 175133293 | chr4 | 175134806 | 175135765 |
| chr4 | 175135847 | 175136086 | chr4 | 175138419 | 175138629 | chr4 | 175138870 | 175139349 |
| chr4 | 175139473 | 175139772 | chr4 | 175750358 | 175750805 | chr4 | 176923342 | 176923641 |
| chr4 | 176987230 | 176987448 | chr4 | 177713154 | 177713513 | chr4 | 180979196 | 180979375 |
| chr4 | 180980208 | 180980447 | chr4 | 183063573 | 183064048 | chr4 | 183064517 | 183064756 |
| chr4 | 183064771 | 183065070 | chr4 | 184019164 | 184019403 | chr4 | 184019595 | 184019834 |
| chr4 | 184020043 | 184020263 | chr4 | 184375709 | 184375816 | chr4 | 184718157 | 184718456 |
| chr4 | 184826157 | 184826576 | chr4 | 184826976 | 184827328 | chr4 | 184921806 | 184922165 |
| chr4 | 185089598 | 185089897 | chr4 | 185937252 | 185937971 | chr4 | 185938412 | 185938651 |
| chr4 | 185940250 | 185940549 | chr4 | 185941484 | 185942863 | chr5 | 53756 | 53995 |
| chr5 | 92072 | 92210 | chr5 | 320762 | 321061 | chr5 | 343957 | 344017 |
| chr5 | 373976 | 374369 | chr5 | 400112 | 400291 | chr5 | 480918 | 481037 |
| chr5 | 491257 | 491616 | chr5 | 524252 | 524491 | chr5 | 528502 | 528775 |
| chr5 | 538663 | 538902 | chr5 | 554212 | 554569 | chr5 | 554812 | 554916 |
| chr5 | 555193 | 555372 | chr5 | 555891 | 556070 | chr5 | 677799 | 678098 |
| chr5 | 1034508 | 1034747 | chr5 | 1131130 | 1131478 | chr5 | 1193302 | 1193465 |
| chr5 | 1193793 | 1194032 | chr5 | 1221103 | 1221402 | chr5 | 1294550 | 1294849 |
| chr5 | 1294928 | 1295767 | chr5 | 1445078 | 1445369 | chr5 | 1445654 | 1446013 |
| chr5 | 1446220 | 1446699 | chr5 | 1746941 | 1747180 | chr5 | 1874877 | 1875176 |
| chr5 | 1875356 | 1875595 | chr5 | 1875796 | 1876935 | chr5 | 1877081 | 1877320 |
| chr5 | 1877912 | 1878631 | chr5 | 1878653 | 1879090 | chr5 | 1879513 | 1879812 |
| chr5 | 1882211 | 1882690 | chr5 | 1882758 | 1883177 | chr5 | 1883429 | 1883908 |
| chr5 | 1884089 | 1884328 | chr5 | 1884479 | 1884778 | chr5 | 1885069 | 1885548 |
| chr5 | 1885910 | 1886269 | chr5 | 1886443 | 1886682 | chr5 | 1886736 | 1887815 |
| chr5 | 1930701 | 1931840 | chr5 | 1950698 | 1951057 | chr5 | 1952550 | 1952729 |
| chr5 | 2038629 | 2038928 | chr5 | 2324309 | 2324488 | chr5 | 2541400 | 2541699 |
| chr5 | 2738746 | 2739525 | chr5 | 2739780 | 2741139 | chr5 | 2743516 | 2743815 |
| chr5 | 2748298 | 2748537 | chr5 | 2749110 | 2749529 | chr5 | 2749625 | 2749804 |
| chr5 | 2750617 | 2751456 | chr5 | 2751615 | 2751974 | chr5 | 2752897 | 2753153 |
| chr5 | 2754664 | 2754703 | chr5 | 2754804 | 2754843 | chr5 | 2255227 | 2756486 |
| chr5 | 2756504 | 2757523 | chr5 | 3031800 | 3032099 | chr5 | 3324948 | 3325367 |
| chr5 | 3590314 | 3590853 | chr5 | 3591252 | 3591491 | chr5 | 3591768 | 3592127 |
| chr5 | 3592626 | 3592961 | chr5 | 3594155 | 3594814 | chr5 | 3595015 | 3595254 |
| chr5 | 3595361 | 3596080 | chr5 | 3596118 | 3596297 | chr5 | 3596441 | 3596980 |
| chr5 | 3597312 | 3597556 | chr5 | 3599759 | 3599938 | chr5 | 3600076 | 3600255 |
| chr5 | 3600794 | 3600973 | chr5 | 3602712 | 3603422 | chr5 | 3606532 | 3606771 |
| chr5 | 3673960 | 3674256 | chr5 | 4144300 | 4144592 | chr5 | 5139578 | 5139997 |
| chr5 | 5140079 | 5140318 | chr5 | 5140527 | 5141006 | chr5 | 6228525 | 6228650 |
| chr5 | 6448837 | 6449676 | chr5 | 6583371 | 6583670 | chr5 | 6687175 | 6687528 |
| chr5 | 7395162 | 7395641 | chr5 | 7850181 | 7850286 | chr5 | 7850919 | 7851218 |
| chr5 | 9546510 | 9546750 | chr5 | 10333611 | 10334210 | chr5 | 10564925 | 10565704 |
| chr5 | 11384806 | 11385465 | chr5 | 11903659 | 11904798 | chr5 | 11904801 | 11905040 |
| chr5 | 15500659 | 15501018 | chr5 | 16178946 | 16179245 | chr5 | 16179436 | 16179795 |
| chr5 | 16179945 | 16180364 | chr5 | 16466683 | 16466796 | chr5 | 16467097 | 16467216 |
| chr5 | 16936255 | 16936402 | chr5 | 16936500 | 16936614 | chr5 | 17203036 | 17203266 |
| chr5 | 17217854 | 17218033 | chr5 | 17218121 | 17218300 | chr5 | 17218862 | 17219101 |
| chr5 | 17512040 | 17512192 | chr5 | 22853425 | 22853596 | chr5 | 31193844 | 31194083 |
| chr5 | 31194299 | 31194511 | chr5 | 31639583 | 31640008 | chr5 | 31691580 | 31691745 |
| chr5 | 31854987 | 31855286 | chr5 | 32710252 | 32710551 | chr5 | 32710718 | 32710957 |
| chr5 | 32711024 | 32711617 | chr5 | 32711729 | 32711968 | chr5 | 32711985 | 32712584 |
| chr5 | 32712675 | 32712943 | chr5 | 33298097 | 33298101 | chr5 | 33891980 | 33892219 |
| chr5 | 33892339 | 33892518 | chr5 | 33936067 | 33936751 | chr5 | 34656834 | 34657042 |
| chr5 | 37834789 | 37834610 | chr5 | 37834855 | 37834900 | chr5 | 37836572 | 37838071 |
| chr5 | 37838448 | 37838987 | chr5 | 37839684 | 37840223 | chr5 | 37840288 | 37840843 |
| chr5 | 38257397 | 38257696 | chr5 | 38257752 | 38258051 | chr5 | 38556995 | 38557076 |
| chr5 | 38557188 | 38557427 | chr5 | 38845574 | 38845955 | chr5 | 38846219 | 38846533 |
| chr5 | 39343086 | 39343201 | chr5 | 40681036 | 40681455 | chr5 | 40681601 | 40682080 |
| chr5 | 42424732 | 42425151 | chr5 | 42950902 | 42952445 | chr5 | 42991751 | 42993010 |
| chr5 | 42993313 | 42993547 | chr5 | 42993853 | 42994272 | chr5 | 42994593 | 42994892 |
| chr5 | 42995015 | 42995254 | chr5 | 43007862 | 43008041 | chr5 | 43008113 | 43008472 |
| chr5 | 43017851 | 43018690 | chr5 | 43019144 | 43019424 | chr5 | 43019729 | 43019968 |
| chr5 | 43040768 | 43041067 | chr5 | 43215459 | 43215562 | chr5 | 43396915 | 43397334 |
| chr5 | 44389705 | 44389929 | chr5 | 45695091 | 45695630 | chr5 | 45695823 | 45696047 |
| chr5 | 45696239 | 45696538 | chr5 | 49736497 | 49736789 | chr5 | 50262842 | 50263104 |
| chr5 | 50263486 | 50263725 | chr5 | 50264216 | 50264695 | chr5 | 50264746 | 50264925 |
| chr5 | 50265228 | 50265527 | chr5 | 50265621 | 50265960 | chr5 | 50674051 | 50674290 |
| chr5 | 50674486 | 50674557 | chr5 | 50674638 | 50574665 | chr5 | 50674925 | 50675164 |
| chr5 | 50678269 | 50678273 | chr5 | 50678373 | 50678552 | chr5 | 50695193 | 50695540 |
| chr5 | 54179491 | 54179730 | chr5 | 54179989 | 54180168 | chr5 | 54516275 | 54517114 |
| chr5 | 54518577 | 54519406 | chr5 | 54527226 | 54527444 | chr5 | 56248119 | 56248358 |
| chr5 | 57878174 | 57878473 | chr5 | 57878612 | 57878775 | chr5 | 57878811 | 57878851 |

TABLE 14-continued

| chr | start | end | chr | start | end | chr | start | end |
|---|---|---|---|---|---|---|---|---|
| chr5 | 59188293 | 59188429 | chr5 | 59188952 | 59189311 | chr5 | 59189787 | 59190026 |
| chr5 | 63254815 | 63255354 | chr5 | 63257645 | 63257944 | chr5 | 63801932 | 63802591 |
| chr5 | 63986409 | 63986888 | chr5 | 67591197 | 67591233 | chr5 | 68391320 | 68391429 |
| chr5 | 71014629 | 71014988 | chr5 | 71015095 | 71015814 | chr5 | 71403491 | 71403730 |
| chr5 | 71403882 | 71404158 | chr5 | 72416170 | 72416262 | chr5 | 72626319 | 72526738 |
| chr5 | 72528360 | 72528539 | chr5 | 72529200 | 72530699 | chr5 | 72594722 | 72595141 |
| chr5 | 72595456 | 72595875 | chr5 | 72598977 | 72599936 | chr5 | 72677577 | 72678416 |
| chr5 | 72715160 | 72715846 | chr5 | 72716022 | 72716239 | chr5 | 72732724 | 72732963 |
| chr5 | 72732990 | 72733268 | chr5 | 72740047 | 72740286 | chr5 | 72746606 | 72746785 |
| chr5 | 75377809 | 75378108 | chr5 | 75380089 | 75380268 | chr5 | 75380530 | 75381006 |
| chr5 | 76011192 | 76011431 | chr5 | 76012504 | 76012681 | chr5 | 76249176 | 76250250 |
| chr5 | 76250351 | 76250590 | chr5 | 76506369 | 76506608 | chr5 | 76506956 | 76507195 |
| chr5 | 76923601 | 76924494 | chr5 | 76924856 | 76925018 | chr5 | 76925477 | 76925776 |
| chr5 | 76928070 | 76928487 | chr5 | 76928588 | 76929007 | chr5 | 76932228 | 76932407 |
| chr5 | 76932463 | 76933362 | chr5 | 76934073 | 76934972 | chr5 | 76935937 | 76936039 |
| chr5 | 76936100 | 76936819 | chr5 | 76939328 | 76939867 | chr5 | 76940241 | 76940472 |
| chr5 | 76941115 | 76941414 | chr5 | 77140440 | 77140799 | chr5 | 77147520 | 77148214 |
| chr5 | 77148396 | 77148669 | chr5 | 77268278 | 77269408 | chr5 | 77806123 | 77806213 |
| chr5 | 78407567 | 78407926 | chr5 | 78408118 | 78408537 | chr5 | 79783152 | 79783256 |
| chr5 | 79864809 | 79865168 | chr5 | 79865969 | 79866508 | chr5 | 79947497 | 79947796 |
| chr5 | 80255722 | 80256261 | chr5 | 80689499 | 80689819 | chr5 | 80690030 | 80690278 |
| chr5 | 82767342 | 82767881 | chr5 | 82768798 | 82769157 | chr5 | 83679121 | 83679300 |
| chr5 | 83679592 | 83680431 | chr5 | 83680592 | 83680812 | chr5 | 87955360 | 87955455 |
| chr5 | 87955502 | 87955899 | chr5 | 87956103 | 87957062 | chr5 | 87962865 | 87963006 |
| chr5 | 87963365 | 87963601 | chr5 | 87967686 | 87968165 | chr5 | 87968411 | 87968942 |
| chr5 | 87970114 | 87970953 | chr5 | 87974027 | 87974386 | chr5 | 87974767 | 87975126 |
| chr5 | 87976104 | 87976408 | chr5 | 87976423 | 87976662 | chr5 | 87979655 | 87979779 |
| chr5 | 87979900 | 87980014 | chr5 | 87980047 | 87980079 | chr5 | 87980322 | 87980346 |
| chr5 | 87980871 | 87981341 | chr5 | 87985819 | 87986058 | chr5 | 87986127 | 87986154 |
| chr5 | 87986233 | 87986366 | chr5 | 87986445 | 87986472 | chr5 | 87988431 | 87988670 |
| chr5 | 87990371 | 87990530 | chr5 | 88185377 | 88186087 | chr5 | 89854760 | 89854999 |
| chr5 | 92939817 | 92940236 | chr5 | 94955591 | 94956010 | chr5 | 94956849 | 94957088 |
| chr5 | 94982143 | 94982314 | chr5 | 95767856 | 95768035 | chr5 | 95768068 | 95768427 |
| chr5 | 95768828 | 95769173 | chr5 | 100236601 | 100236840 | chr5 | 100238808 | 100239167 |
| chr5 | 101631391 | 101631630 | chr5 | 107005906 | 107006265 | chr5 | 111987788 | 111987901 |
| chr5 | 112043011 | 112043367 | chr5 | 112073328 | 112073567 | chr5 | 112175566 | 112175730 |
| chr5 | 112629342 | 112629359 | chr5 | 112629394 | 112629761 | chr5 | 113391163 | 113391218 |
| chr5 | 113391284 | 113392122 | chr5 | 113698466 | 113698885 | chr5 | 113698915 | 113699203 |
| chr5 | 114514867 | 114515754 | chr5 | 115151174 | 115152733 | chr5 | 115297105 | 115297644 |
| chr5 | 115297836 | 115298135 | chr5 | 115298410 | 115298829 | chr5 | 115298894 | 115299133 |
| chr5 | 119799840 | 119800079 | chr5 | 119801223 | 119801522 | chr5 | 121413445 | 121413684 |
| chr5 | 122422161 | 122422386 | chr5 | 122422516 | 122422754 | chr5 | 122423233 | 122423452 |
| chr5 | 122425029 | 122425268 | chr5 | 122431039 | 122431458 | chr5 | 124128503 | 124128574 |
| chr5 | 126626256 | 126626795 | chr5 | 127872847 | 127873086 | chr5 | 127873190 | 127873789 |
| chr5 | 127874345 | 127874944 | chr5 | 128300588 | 128300887 | chr5 | 128795984 | 128796343 |
| chr5 | 128796777 | 128797076 | chr5 | 128797246 | 128797485 | chr5 | 129239966 | 129240205 |
| chr5 | 131992008 | 131992247 | chr5 | 132947392 | 132947931 | chr5 | 133820025 | 133820136 |
| chr5 | 134363235 | 134363320 | chr5 | 134364026 | 134364075 | chr5 | 134364115 | 134364205 |
| chr5 | 134364295 | 134364594 | chr5 | 134366534 | 134366873 | chr5 | 134367007 | 134367306 |
| chr5 | 134374370 | 134375309 | chr5 | 134376120 | 134376474 | chr5 | 134376612 | 134376911 |
| chr5 | 134385869 | 134386466 | chr5 | 134582953 | 134582969 | chr5 | 134825372 | 134825611 |
| chr5 | 134825799 | 134826098 | chr5 | 134870362 | 134870601 | chr5 | 134870689 | 134871288 |
| chr5 | 134871526 | 134872125 | chr5 | 134879391 | 134879973 | chr5 | 134880154 | 134880590 |
| chr5 | 134914539 | 134914838 | chr5 | 135265664 | 135265842 | chr5 | 135266034 | 135266753 |
| chr5 | 135528098 | 135528337 | chr5 | 136834009 | 136834608 | chr5 | 136834624 | 136834923 |
| chr5 | 137225029 | 137225268 | chr5 | 138273717 | 138273845 | chr5 | 139047897 | 139048256 |
| chr5 | 139227692 | 139227991 | chr5 | 139525654 | 139525833 | chr5 | 139779840 | 139779953 |
| chr5 | 140174701 | 140174994 | chr5 | 140187003 | 140187240 | chr5 | 140305895 | 140306134 |
| chr5 | 140306228 | 140306827 | chr5 | 140346514 | 140346753 | chr5 | 140514817 | 140514996 |
| chr5 | 140604361 | 140604596 | chr5 | 140613851 | 140614089 | chr5 | 140614230 | 140614469 |
| chr5 | 140777354 | 140777588 | chr5 | 140797000 | 140797419 | chr5 | 140800384 | 140801343 |
| chr5 | 140811013 | 140811138 | chr5 | 140855515 | 140856710 | chr5 | 141031047 | 141031205 |
| chr5 | 141262957 | 141263316 | chr5 | 141931261 | 141931585 | chr5 | 142784881 | 142785305 |
| chr5 | 145713562 | 145713981 | chr5 | 145717097 | 145717516 | chr5 | 145718714 | 145720024 |
| chr5 | 145720763 | 145720942 | chr5 | 145722033 | 145723112 | chr5 | 145724421 | 145724780 |
| chr5 | 145725109 | 145725948 | chr5 | 146257258 | 146257677 | chr5 | 146889129 | 146889668 |
| chr5 | 149681971 | 149682270 | chr5 | 150051025 | 150051744 | chr5 | 150400044 | 150400283 |
| chr5 | 151066339 | 151066578 | chr5 | 151304297 | 151304476 | chr5 | 153852579 | 153852878 |
| chr5 | 153853330 | 153853569 | chr5 | 163855101 | 153855340 | chr5 | 153855506 | 153855925 |
| chr5 | 153856004 | 153856483 | chr5 | 153856847 | 153857085 | chr5 | 153857285 | 153857524 |
| chr5 | 153858220 | 153858699 | chr5 | 153859573 | 153859812 | chr5 | 153861948 | 153862667 |
| chr5 | 153863347 | 153863526 | chr5 | 154209838 | 154210070 | chr5 | 154318060 | 154318178 |
| chr5 | 155107702 | 155107941 | chr5 | 155108042 | 155108612 | chr5 | 155108659 | 155108838 |
| chr5 | 156874164 | 156874403 | chr5 | 157001643 | 157001941 | chr5 | 157078345 | 157078524 |
| chr5 | 157098282 | 157098701 | chr5 | 158478385 | 158478864 | chr5 | 158524601 | 158524837 |
| chr5 | 158527367 | 158528146 | chr5 | 159399015 | 159399314 | chr5 | 160975650 | 160975829 |
| chr5 | 161274223 | 161274358 | chr5 | 161274506 | 161274642 | chr5 | 166865354 | 166865462 |
| chr5 | 167956087 | 167956560 | chr5 | 167956601 | 167956686 | chr5 | 168233320 | 168233559 |

TABLE 14-continued

| chr | start | end | chr | start | end | chr | start | end |
|---|---|---|---|---|---|---|---|---|
| chr5 | 168727837 | 168728076 | chr5 | 169064237 | 169064887 | chr5 | 169532851 | 169533090 |
| chr5 | 170108211 | 170108450 | chr5 | 170289352 | 170289395 | chr5 | 170735061 | 170735300 |
| chr5 | 170735336 | 170735875 | chr5 | 170736019 | 170737578 | chr5 | 170737779 | 170739571 |
| chr5 | 170739746 | 170740058 | chr5 | 170740091 | 170740105 | chr5 | 170740391 | 170741031 |
| chr5 | 170741508 | 170742822 | chr5 | 170743151 | 170744207 | chr5 | 170744290 | 170744649 |
| chr5 | 170745286 | 170745560 | chr5 | 172655778 | 172656317 | chr5 | 172659314 | 172659378 |
| chr5 | 172659397 | 172659756 | chr5 | 172659768 | 172660307 | chr5 | 172660633 | 172661228 |
| chr5 | 172661368 | 172661772 | chr5 | 172664148 | 172664567 | chr5 | 172665492 | 172665911 |
| chr5 | 172670882 | 172671121 | chr5 | 172671268 | 172671926 | chr5 | 172672391 | 172672406 |
| chr5 | 172672593 | 172672750 | chr5 | 172754486 | 172754725 | chr5 | 122754733 | 172755032 |
| chr5 | 172755388 | 172755745 | chr5 | 172756961 | 172757200 | chr5 | 174115296 | 174115690 |
| chr5 | 174115864 | 174115955 | chr5 | 174147441 | 174147680 | chr5 | 174150341 | 174150520 |
| chr5 | 174158719 | 174159669 | chr5 | 174162800 | 174162945 | chr5 | 174220897 | 174221036 |
| chr5 | 174870643 | 174870882 | chr5 | 174871097 | 174871576 | chr5 | 174921381 | 174921483 |
| chr5 | 175085059 | 175085298 | chr5 | 175085389 | 175085808 | chr5 | 175223571 | 175223810 |
| chr5 | 175223935 | 175224354 | chr5 | 175298507 | 175298986 | chr5 | 175299196 | 175299495 |
| chr5 | 175300277 | 175300456 | chr5 | 175621297 | 175621595 | chr5 | 175792785 | 175793144 |
| chr5 | 176023818 | 176024350 | chr5 | 176046280 | 176046639 | chr5 | 176107191 | 176107670 |
| chr5 | 176236631 | 176236990 | chr5 | 176264711 | 176264998 | chr5 | 176764020 | 176764255 |
| chr5 | 177031093 | 177031272 | chr5 | 177408416 | 177408548 | chr5 | 177411561 | 177412210 |
| chr5 | 177713273 | 177713572 | chr5 | 178003629 | 178003928 | chr5 | 178004231 | 178004470 |
| chr5 | 178016513 | 178017971 | chr5 | 178367990 | 178368462 | chr5 | 178421400 | 178421579 |
| chr5 | 178421685 | 178422099 | chr5 | 178422167 | 178422224 | chr5 | 178487023 | 178487493 |
| chr5 | 178576382 | 178576578 | chr5 | 178655663 | 178655962 | chr5 | 178771216 | 178772055 |
| chr5 | 178772120 | 178772359 | chr5 | 178772525 | 178772824 | chr5 | 178957552 | 178958023 |
| chr5 | 179214036 | 179214275 | chr5 | 179243892 | 179244371 | chr5 | 179780005 | 179780244 |
| chr5 | 179780607 | 179781086 | chr5 | 179867405 | 179867637 | chr5 | 180017039 | 180017278 |
| chr5 | 180017532 | 180018011 | chr5 | 180018226 | 180018585 | chr5 | 180047646 | 180047703 |
| chr5 | 180075753 | 180076412 | chr5 | 180076466 | 180076705 | chr5 | 180076721 | 180077080 |
| chr5 | 180100825 | 180101410 | chr5 | 180326052 | 180326231 | chr5 | 180527447 | 180527866 |
| chr5 | 180600769 | 180601030 | chr5 | 180601129 | 180601308 | chr6 | 391089 | 392097 |
| chr6 | 392230 | 393729 | chr6 | 711039 | 711392 | chr6 | 1311899 | 1312095 |
| chr6 | 1312680 | 1312802 | chr6 | 1314014 | 1314150 | chr6 | 1378133 | 1379332 |
| chr6 | 1379510 | 1379689 | chr6 | 1379812 | 1380051 | chr6 | 1383598 | 1384731 |
| chr6 | 1385025 | 1385264 | chr6 | 1386020 | 1386212 | chr6 | 1389044 | 1389343 |
| chr6 | 1390159 | 1391118 | chr6 | 1391230 | 1391469 | chr6 | 1524122 | 1524361 |
| chr6 | 1606302 | 1605541 | chr6 | 1614740 | 1616279 | chr6 | 1624940 | 1625059 |
| chr6 | 1626129 | 1625779 | chr6 | 3053237 | 3053463 | chr6 | 3228955 | 3229134 |
| che6 | 3229348 | 3229587 | chr6 | 3231926 | 3232029 | chr6 | 3285129 | 3285608 |
| chr6 | 3405599 | 3405778 | chr6 | 4775080 | 4775322 | chr6 | 4836441 | 4836545 |
| chr6 | 4951178 | 4951469 | chr6 | 5783232 | 5783457 | chr6 | 5996852 | 5997091 |
| chr6 | 5997728 | 5997907 | chr6 | 6003213 | 6005450 | chr6 | 6006278 | 6006498 |
| chr6 | 6006600 | 6006959 | chr6 | 6007516 | 6007772 | chr6 | 6007833 | 6008355 |
| chr6 | 6367000 | 6367218 | chr6 | 7726260 | 7726439 | chr6 | 7726556 | 7726735 |
| chr6 | 7726878 | 7727057 | chr6 | 7727622 | 7728221 | chr6 | 7728746 | 7729045 |
| chr6 | 10381428 | 10382383 | chr6 | 10382648 | 10383126 | chr6 | 10383638 | 10383877 |
| chr6 | 10384876 | 10386015 | chr6 | 10386123 | 10386357 | chr6 | 10389946 | 10391265 |
| chr6 | 10410429 | 10410668 | chr6 | 10411254 | 10411613 | chr6 | 10415015 | 10416314 |
| chr6 | 10415457 | 10415816 | chr6 | 10416039 | 10416445 | chr6 | 10417059 | 10417658 |
| chr6 | 10418997 | 10419596 | chr6 | 10419664 | 10420023 | chr6 | 10420975 | 10421171 |
| chr6 | 10421253 | 10422714 | chr6 | 10425411 | 10426970 | chr6 | 10881857 | 10882156 |
| chr6 | 10882247 | 10882426 | chr6 | 10882934 | 10883113 | chr6 | 10886993 | 10887772 |
| chr6 | 11043988 | 11044647 | chr6 | 12288420 | 12288779 | chr6 | 12749819 | 12750058 |
| chr6 | 12750114 | 12750353 | chr6 | 16196952 | 16197191 | chr6 | 17281327 | 17281351 |
| chr6 | 18035792 | 18036091 | chr6 | 19691621 | 19691920 | chr6 | 19691983 | 19692280 |
| chr6 | 19836983 | 19837222 | chr6 | 21665144 | 21665903 | chre | 24494604 | 24494843 |
| chr6 | 24647262 | 24647371 | chr6 | 26184364 | 26184476 | chr6 | 26188754 | 26189495 |
| chr6 | 26189956 | 26190075 | chr6 | 26199099 | 26199242 | chr6 | 26199612 | 26199791 |
| chr6 | 26214613 | 26214731 | chr6 | 26235124 | 26235437 | chr6 | 26240532 | 26241201 |
| chr6 | 26250378 | 26250917 | chr6 | 26250969 | 26251261 | chr6 | 26251715 | 26251940 |
| chr6 | 26252075 | 26252180 | chr6 | 26271315 | 26271854 | chr6 | 26271897 | 26272076 |
| chr6 | 26272416 | 26272715 | chr6 | 26273381 | 26273560 | chr6 | 26284786 | 26284975 |
| chr6 | 26327725 | 26328074 | chr6 | 26328206 | 26328505 | chr6 | 26332079 | 26332318 |
| chr6 | 26501764 | 26502296 | chr6 | 26550895 | 26551134 | chr6 | 26577078 | 26577557 |
| chr6 | 26987930 | 26988169 | chr6 | 27059697 | 27059936 | chr6 | 27064581 | 27065300 |
| chr6 | 27173436 | 27173855 | chr6 | 27173925 | 27174275 | chr6 | 27182856 | 27182974 |
| chr6 | 27203167 | 27203286 | chr6 | 27205240 | 27205359 | chr6 | 27205420 | 27205621 |
| chr6 | 27205587 | 27206126 | chr6 | 27228079 | 27228498 | chr6 | 22247561 | 27247800 |
| chr6 | 27256186 | 27256255 | chr6 | 27256283 | 27256522 | chr6 | 27264344 | 27264468 |
| chr6 | 27279750 | 27280109 | chr6 | 27462939 | 27463778 | chr6 | 27512675 | 27513574 |
| chr6 | 27533723 | 27534442 | chr6 | 27559775 | 27560074 | chr6 | 27573073 | 27573492 |
| chr6 | 27598650 | 27598949 | chr6 | 27599071 | 27599427 | chr6 | 27635171 | 27635530 |
| chr6 | 27647625 | 27647984 | chr6 | 27648934 | 27649153 | chr6 | 27834577 | 27834936 |
| chr6 | 27834963 | 27835502 | chr6 | 27839635 | 27840174 | chr6 | 27840461 | 27840668 |
| chr6 | 27841002 | 27841240 | chr6 | 27858427 | 27858726 | chr6 | 28175105 | 28176301 |
| chr6 | 28303466 | 28303571 | chr6 | 28303847 | 28304339 | chr6 | 28367023 | 28367862 |
| chr6 | 28410896 | 28411435 | chr6 | 28414887 | 28415126 | chr6 | 28457534 | 28457713 |
| chr6 | 28457775 | 28458254 | chr6 | 33955409 | 33955828 | chr6 | 34170869 | 34170986 |

TABLE 14-continued

| chr | start | end | chr | start | end | chr | start | end |
|---|---|---|---|---|---|---|---|---|
| chr6 | 34171049 | 34171166 | chr6 | 34396518 | 34396631 | chr6 | 34724210 | 34724318 |
| chr6 | 35149942 | 35150181 | chr6 | 35479539 | 35479718 | chr6 | 35992354 | 35992533 |
| chr6 | 36165588 | 36165767 | chr6 | 36252899 | 36253258 | chr6 | 36313887 | 36313988 |
| chr6 | 36808233 | 36808532 | chr6 | 37024485 | 37024664 | chr6 | 37664045 | 37664284 |
| chr6 | 37673227 | 37673573 | chr6 | 37776336 | 37776455 | chr6 | 37776737 | 37776839 |
| chr6 | 39281005 | 39281231 | chr6 | 39281731 | 39281970 | chr6 | 39329789 | 39329968 |
| chr6 | 39760322 | 39760663 | chr6 | 40554557 | 40554796 | chr6 | 41336981 | 41337220 |
| chr6 | 41339162 | 41339941 | chr6 | 41340803 | 41341282 | chr6 | 41341406 | 41341645 |
| chr6 | 41342140 | 41342370 | chr6 | 41342733 | 41342912 | chr6 | 41605851 | 41606630 |
| chr6 | 41773485 | 41773844 | chr6 | 42773364 | 42773471 | chr6 | 42846625 | 42846729 |
| chr6 | 42879457 | 42879756 | chr6 | 42928239 | 42928460 | chr6 | 43211113 | 43211402 |
| chr6 | 43424445 | 43424564 | chr6 | 43425407 | 43425524 | chr6 | 43478592 | 43478821 |
| chr6 | 43612737 | 43613156 | chr6 | 43639525 | 43639809 | chr6 | 43748380 | 43748619 |
| chr6 | 44240961 | 44241191 | chr6 | 44695775 | 44695899 | chr6 | 45388701 | 45388866 |
| chr6 | 46702904 | 46703203 | chr6 | 46703274 | 46703513 | chr6 | 50674292 | 50674831 |
| chr6 | 50681612 | 50681851 | chr6 | 50681912 | 50682031 | chr6 | 50682234 | 50682473 |
| chr6 | 50682584 | 50683303 | chr6 | 50684865 | 50685044 | chr6 | 50689827 | 50690126 |
| chr6 | 50690991 | 50691170 | chr6 | 50691983 | 50692582 | chr6 | 50787125 | 50788444 |
| chr6 | 50789300 | 50789479 | chr6 | 50791111 | 50791708 | chr6 | 50793251 | 50793490 |
| chr6 | 50793626 | 50793850 | chr6 | 50794525 | 50794792 | chr6 | 50803732 | 50803971 |
| chr6 | 50804041 | 50804446 | chr6 | 50808589 | 50808845 | chr6 | 50810456 | 50810935 |
| chr6 | 50810976 | 50811575 | chr6 | 50813200 | 50814019 | chr6 | 50814495 | 50814674 |
| chr6 | 50816947 | 50817306 | chr6 | 50817831 | 50817841 | chr6 | 50818369 | 50818788 |
| chr6 | 50818841 | 50819080 | chr6 | 52227678 | 62227857 | chr6 | 52227934 | 52227964 |
| chr6 | 52344301 | 52344480 | chr6 | 53212553 | 53213932 | chr6 | 55443610 | 55444029 |
| che6 | 56112175 | 56112474 | che6 | 56716252 | 56716491 | chr6 | 56818618 | 56819037 |
| chr6 | 56819128 | 56819727 | chr6 | 56819823 | 56820002 | chr6 | 58147345 | 58147619 |
| chr6 | 58147764 | 58148058 | chr6 | 62995272 | 62996231 | chr6 | 62996347 | 62996586 |
| chr6 | 70991961 | 70992260 | chr6 | 70992339 | 70992638 | chr6 | 70992744 | 70993103 |
| chr6 | 71665562 | 71665801 | chr6 | 71666708 | 71667066 | chr6 | 72129690 | 72129929 |
| chr6 | 72130017 | 72130556 | chr6 | 72596039 | 72596398 | chr6 | 72596876 | 72597055 |
| chr6 | 73329686 | 73330225 | chr6 | 73330740 | 73331399 | chr6 | 73331420 | 73333099 |
| chr6 | 78172096 | 78172675 | chr6 | 78173119 | 78173295 | chr6 | 78173610 | 78174080 |
| chr6 | 78176370 | 78176607 | chr6 | 78176693 | 78176909 | chr6 | 79620310 | 79620789 |
| chr6 | 80656846 | 80657265 | chr6 | 82958527 | 82958646 | chr6 | 84417343 | 84417877 |
| chr6 | 84418078 | 84418377 | chr6 | 84418545 | 84418904 | chr6 | 84419077 | 84419496 |
| chr6 | 84562789 | 84563328 | chr6 | 84563397 | 84563636 | chr6 | 85472306 | 85473805 |
| chr6 | 85473854 | 85474453 | chr6 | 85474516 | 85474767 | chr6 | 85474795 | 85474815 |
| chr6 | 85476140 | 85476379 | chr6 | 85476924 | 85477103 | chr6 | 85478440 | 85478557 |
| chr6 | 85478715 | 85478799 | chr6 | 85482437 | 85482796 | chr6 | 85483271 | 85483450 |
| chr6 | 85483559 | 85484998 | chr6 | 86302335 | 86302422 | chr6 | 87647130 | 87647219 |
| chr6 | 87862013 | 87862252 | chr6 | 88876871 | 88877530 | chr6 | 91320191 | 91320422 |
| chr6 | 91320853 | 91321390 | chr6 | 94126870 | 94127169 | chr6 | 94127381 | 94127620 |
| chr6 | 94128340 | 94128502 | chr6 | 94129119 | 94129358 | chr6 | 94129423 | 94129662 |
| chr6 | 96464003 | 96464293 | chr6 | 99271829 | 99272908 | chr6 | 99273271 | 99273510 |
| chr6 | 99277106 | 99277201 | chr6 | 99277262 | 99277405 | chr6 | 99279465 | 99279704 |
| chr6 | 99280472 | 99280831 | chr6 | 99280931 | 99281470 | chr6 | 99283428 | 99283667 |
| chr6 | 99290260 | 99290499 | chr6 | 99290556 | 99290738 | chr6 | 99291191 | 99291531 |
| chr6 | 99292156 | 99292515 | chr6 | 99295648 | 99296547 | chr6 | 99396354 | 99396473 |
| chr6 | 100038584 | 100039063 | chr6 | 100039185 | 100039364 | chr6 | 100050674 | 100052053 |
| chr6 | 100053191 | 100053606 | chr6 | 100054773 | 100055012 | chr6 | 100060930 | 100061169 |
| chr6 | 100061216 | 100061515 | chr6 | 100061677 | 100061916 | chr6 | 100062083 | 100062682 |
| chr6 | 100062857 | 100063156 | chr6 | 100441276 | 100442055 | chr6 | 100903299 | 100903718 |
| chr6 | 100904126 | 100904365 | chr6 | 100905936 | 100906113 | chr6 | 100911976 | 100912215 |
| chr6 | 100912332 | 100912571 | chr6 | 100912825 | 100913244 | chr6 | 100915004 | 100915303 |
| chr6 | 101840615 | 101840914 | chr6 | 101847215 | 101847290 | chr6 | 101850062 | 101850314 |
| chr6 | 101850496 | 101850675 | chr6 | 105388605 | 105388784 | chr6 | 105388833 | 105389792 |
| chr6 | 105400811 | 105401110 | chr6 | 105401538 | 105401908 | chr6 | 105404475 | 105404774 |
| chr6 | 105405565 | 105405854 | chr6 | 105406024 | 105406203 | chr6 | 105584190 | 105585629 |
| chr6 | 106428948 | 106429704 | chr6 | 106434265 | 106434371 | chr6 | 106441795 | 106443054 |
| chr6 | 106960817 | 106961116 | chr6 | 107955878 | 107956071 | chr6 | 108280341 | 108280442 |
| chr6 | 108434990 | 108435327 | chr6 | 108435970 | 108436629 | chr6 | 108438142 | 108438612 |
| chr6 | 108440017 | 108441036 | chr6 | 108479209 | 108479748 | chr6 | 108484829 | 108485274 |
| chr6 | 108485419 | 108485488 | chr6 | 108485576 | 108485995 | chr6 | 108486067 | 108486486 |
| chr6 | 108487701 | 108488520 | chr6 | 108489290 | 108490729 | chr6 | 108490902 | 108491501 |
| chr6 | 108492182 | 108492541 | chr6 | 108495607 | 108496026 | chr6 | 108496130 | 108496729 |
| chr6 | 108497419 | 108497958 | chr6 | 110679030 | 110679509 | chr6 | 110797604 | 110797783 |
| chr6 | 110797933 | 110798047 | chr6 | 116783418 | 116783591 | chr6 | 117086168 | 117086947 |
| chr6 | 117585867 | 117586106 | chr6 | 117586717 | 117586781 | chr6 | 117587028 | 117587256 |
| chr6 | 117587380 | 117587387 | chr6 | 117587449 | 117587679 | chr6 | 117591087 | 117591266 |
| chr6 | 117591308 | 117591847 | chr6 | 118228008 | 118228247 | chr6 | 118228669 | 118228908 |
| chr6 | 118229060 | 118229479 | chr6 | 118229543 | 118229902 | chr6 | 118241125 | 118241604 |
| chr6 | 119254661 | 119254774 | chr6 | 121758594 | 121759048 | chr6 | 123316950 | 123317669 |
| chr6 | 123317696 | 123317935 | chr6 | 124124330 | 124124569 | chr6 | 124124759 | 124125118 |
| chr6 | 125284034 | 125284273 | chr6 | 126068016 | 126068255 | chr6 | 127439297 | 127439536 |
| chr6 | 127439907 | 127440206 | chr6 | 127440248 | 127441207 | chr6 | 127441479 | 127441838 |
| chr6 | 127441944 | 127442183 | chr6 | 127840412 | 127840771 | chr6 | 129204373 | 129204612 |
| chr6 | 130686437 | 130687156 | chr6 | 131602689 | 131602789 | chr6 | 132721988 | 132722287 |

TABLE 14-continued

| chr | start | end | chr | start | end | chr | start | end |
|---|---|---|---|---|---|---|---|---|
| chr6 | 133561666 | 133562145 | chr6 | 133562297 | 133563136 | chr6 | 133563234 | 133564013 |
| chr6 | 134067456 | 134067573 | chr6 | 134176147 | 134176149 | chr6 | 134210439 | 134211458 |
| chr6 | 134213855 | 134214454 | chr6 | 134589425 | 134589586 | chr6 | 134638858 | 134639095 |
| chr6 | 137241828 | 137242307 | chr6 | 137243130 | 137243342 | chr6 | 137243367 | 137243489 |
| chr6 | 137244036 | 137244695 | chr6 | 137311060 | 137311479 | chr6 | 137366280 | 137366459 |
| chr6 | 137809066 | 137811165 | chr6 | 137813692 | 137813991 | chr6 | 137814505 | 137814864 |
| chr6 | 137814916 | 137815755 | chr6 | 137816373 | 137817377 | chr6 | 137818428 | 137819447 |
| chr6 | 146755489 | 146755728 | chr6 | 149868369 | 149868478 | chr6 | 150284574 | 150284657 |
| chr6 | 150284979 | 150286718 | chr6 | 150358890 | 150359489 | chr6 | 151560928 | 151561947 |
| chr6 | 151661986 | 151562645 | chr6 | 151814953 | 151815192 | chr6 | 152622925 | 152623584 |
| chr6 | 152957807 | 152958166 | chr6 | 153451159 | 153451578 | chr6 | 153451810 | 153452049 |
| chr6 | 153452157 | 153452396 | chr6 | 163452611 | 153452850 | chr6 | 154360549 | 154360848 |
| chr6 | 154970468 | 154970587 | chr6 | 155316161 | 155316340 | chr6 | 155569193 | 155569407 |
| chr6 | 157502364 | 157502543 | chr6 | 157506008 | 157506187 | chr6 | 157556755 | 157557954 |
| chr6 | 159589948 | 159591087 | chr6 | 159654844 | 159655063 | chr6 | 161100422 | 161100466 |
| chr6 | 161188439 | 161188618 | chr6 | 161351999 | 161352238 | chr6 | 161780141 | 161780218 |
| chr6 | 163834237 | 163834716 | chr6 | 163834779 | 163834907 | chr6 | 163834988 | 163835018 |
| chr6 | 163836465 | 163837004 | chr6 | 164179653 | 164179772 | chr6 | 164196997 | 164197107 |
| chr6 | 164228212 | 164228449 | chr6 | 164246123 | 164246229 | chr6 | 164283167 | 164283370 |
| chr6 | 164314286 | 164314525 | chr6 | 164322572 | 164322871 | chr6 | 166074027 | 166074506 |
| chr6 | 166076696 | 166077115 | chr6 | 166077280 | 166077759 | chr6 | 166267503 | 166268162 |
| chr6 | 166401162 | 166401401 | chr6 | 166402154 | 166402633 | chr6 | 166421831 | 166422288 |
| chr6 | 166579636 | 166580234 | chr6 | 166580252 | 166582891 | chr6 | 166944266 | 166944505 |
| chr6 | 167835031 | 167835270 | chr6 | 168719882 | 168720121 | chr6 | 168842760 | 168843046 |
| chr6 | 168858030 | 168858389 | chr6 | 169653564 | 169653743 | chr6 | 170240691 | 170240797 |
| chr6 | 170264630 | 170264865 | chr6 | 170475007 | 170475366 | chr7 | 329703 | 329942 |
| chr7 | 369763 | 370062 | chr7 | 389589 | 389762 | chr7 | 409740 | 409872 |
| chr7 | 409887 | 409979 | chr7 | 431290 | 431589 | chr7 | 497679 | 498006 |
| chr7 | 503725 | 504024 | chr7 | 551499 | 551778 | chr7 | 557008 | 557076 |
| chr7 | 578836 | 579121 | chr7 | 751726 | 751965 | chr7 | 752022 | 752321 |
| chr7 | 907582 | 907761 | chr7 | 914984 | 915163 | chr7 | 1022150 | 1022329 |
| chr7 | 1030079 | 1030378 | chr7 | 1054489 | 1054780 | chr7 | 1086110 | 1086409 |
| chr7 | 1263682 | 1264041 | chr7 | 1269228 | 1269887 | chr7 | 1270304 | 1270543 |
| chr7 | 1273070 | 1273429 | chr7 | 1274540 | 1274779 | chr7 | 1274934 | 1275113 |
| chr7 | 1275481 | 1275780 | chr7 | 1277722 | 1277961 | chr7 | 1279136 | 1279204 |
| chr7 | 1279891 | 1280070 | chr7 | 1281033 | 1281332 | chr7 | 1281405 | 1281644 |
| chr7 | 1281947 | 1222246 | chr7 | 1282426 | 1282725 | chr7 | 1286142 | 1286441 |
| chr7 | 1286715 | 1286954 | chr7 | 1288489 | 1288848 | chr7 | 1308275 | 1308574 |
| chr7 | 1325727 | 1325966 | chr7 | 1415941 | 1416226 | chr7 | 1423536 | 1423740 |
| chr7 | 1458967 | 1459183 | chr7 | 1503328 | 1503687 | chr7 | 1547234 | 1547413 |
| chr7 | 1598549 | 1598788 | chr7 | 1607307 | 1607546 | chr7 | 1607897 | 1608076 |
| chr7 | 1641700 | 1641999 | chr7 | 1681095 | 1681334 | chr7 | 1688883 | 1689101 |
| chr7 | 1690649 | 1690801 | chr7 | 1690903 | 1690948 | chr7 | 1709038 | 1709337 |
| chr7 | 1709385 | 1709684 | chr7 | 1733066 | 1733482 | chr7 | 1775757 | 1775936 |
| chr7 | 1783468 | 1783470 | chr7 | 1786438 | 1786916 | chr7 | 1787066 | 1787425 |
| chr7 | 1800808 | 1800987 | chr7 | 1970776 | 1970947 | chr7 | 2163251 | 2163496 |
| chr7 | 2208635 | 2208889 | chr7 | 2232861 | 2233154 | chr7 | 2233204 | 2233503 |
| chr7 | 2238051 | 2238327 | chr7 | 2300694 | 2300803 | chr7 | 2473350 | 2473614 |
| chr7 | 2473624 | 2473709 | chr7 | 2565961 | 2566130 | chr7 | 2566526 | 2566705 |
| chr7 | 2719928 | 2720227 | chr7 | 2727968 | 2728267 | chr7 | 3033584 | 3033763 |
| chr7 | 3083216 | 3083455 | chr7 | 3283620 | 3283978 | chr7 | 3340370 | 3340549 |
| chr7 | 3340799 | 3341069 | chr7 | 3341394 | 3341693 | chr7 | 4215235 | 4215469 |
| chr7 | 4856897 | 4857136 | chr7 | 4922460 | 4922816 | chr7 | 4922996 | 4923475 |
| chr7 | 4998116 | 4998475 | chr7 | 4998598 | 4998837 | chr7 | 5262472 | 5262648 |
| chr7 | 5632841 | 5633200 | chr7 | 5648011 | 5648490 | chr7 | 6060493 | 6060556 |
| chr7 | 6099127 | 6099234 | chr7 | 6124621 | 6124740 | chr7 | 6188652 | 6188831 |
| chr7 | 6188926 | 6189165 | chr7 | 6443198 | 6443478 | chr7 | 6443752 | 6443794 |
| chr7 | 6443871 | 6443931 | chr7 | 6524492 | 6524599 | chr7 | 6524936 | 6525055 |
| chr7 | 6543064 | 6543303 | chr7 | 6560141 | 6560440 | chr7 | 6566329 | 6566748 |
| chr7 | 6570866 | 6571225 | chr7 | 6576043 | 6576185 | chr7 | 6703458 | 6704057 |
| chr7 | 7605665 | 7605902 | chr7 | 8472995 | 8473762 | chr7 | 8473870 | 8474649 |
| chr7 | 8474727 | 8475146 | chr7 | 8480647 | 8481126 | chr7 | 8481228 | 8481260 |
| chr7 | 8481559 | 8481918 | chr7 | 8481980 | 8482999 | chr7 | 8483070 | 8484029 |
| chr7 | 12151350 | 12151769 | chr7 | 12443241 | 12443480 | chr7 | 12443767 | 12443806 |
| chr7 | 12610259 | 12610317 | chr7 | 12610559 | 12610558 | chr7 | 15725883 | 15726182 |
| chr7 | 15726557 | 15727155 | chr7 | 15727216 | 15727395 | chr7 | 19145730 | 19146329 |
| chr7 | 19146411 | 19146650 | chr7 | 19147041 | 19147880 | chr7 | 19152069 | 19152368 |
| chr7 | 19155865 | 19155896 | chr7 | 19155984 | 19156643 | chr7 | 19156705 | 19157003 |
| chr7 | 19157041 | 19158120 | chr7 | 19183978 | 19184337 | chr7 | 19813210 | 19813350 |
| chr7 | 20816175 | 20816530 | chr7 | 20817306 | 20817332 | chr7 | 20817452 | 20817485 |
| chr7 | 20818037 | 20818276 | chr7 | 20823213 | 20823512 | chr7 | 20823826 | 20825025 |
| chr7 | 20825290 | 20825363 | chr7 | 20826803 | 20826939 | chr7 | 20827224 | 20827282 |
| chr7 | 20830596 | 20830775 | chr7 | 20833066 | 20833425 | chr7 | 21582492 | 21582971 |
| chr7 | 21583176 | 21583415 | chr7 | 22539752 | 22539991 | chr7 | 22589254 | 22589973 |
| chr7 | 23287170 | 23287709 | chr7 | 23578824 | 23578943 | chr7 | 24324002 | 24324031 |
| chr7 | 24580786 | 24580905 | chr7 | 24796404 | 24796643 | chr7 | 25892430 | 25892669 |
| chr7 | 25896424 | 25896603 | chr7 | 25896675 | 25896963 | chr7 | 27127919 | 27128001 |
| chr7 | 27135232 | 27135891 | chr7 | 27135923 | 27136868 | chr7 | 27190490 | 27191329 |

TABLE 14-continued

| chr | start | end | chr | start | end | chr | start | end |
|---|---|---|---|---|---|---|---|---|
| chr7 | 27195483 | 27196742 | chr7 | 27204402 | 27205481 | chr7 | 27205599 | 27206138 |
| chr7 | 27209413 | 27209672 | chr7 | 27209690 | 27209772 | chr7 | 27212400 | 27212999 |
| chr7 | 27213082 | 27214401 | chr7 | 27223031 | 27223253 | chr7 | 27223500 | 27223799 |
| chr7 | 27223980 | 27224699 | chr7 | 27224945 | 27225184 | chr7 | 27227795 | 27228034 |
| chr7 | 27232207 | 27233046 | chr7 | 27238813 | 27238992 | chr7 | 27239087 | 27239326 |
| chr7 | 27240127 | 27240423 | chr7 | 27244446 | 27245393 | chr7 | 27245583 | 27245733 |
| chr7 | 27252306 | 27252485 | chr7 | 27264801 | 27265400 | chr7 | 27265442 | 27265678 |
| chr7 | 27275439 | 27275532 | chr7 | 27279015 | 27279554 | chr7 | 27282012 | 27283091 |
| chr7 | 27283250 | 27283662 | chr7 | 27285436 | 27286249 | chr7 | 27288869 | 27289628 |
| chr7 | 27291048 | 27291947 | chr7 | 28449197 | 28450096 | chr7 | 28995579 | 28996058 |
| chr7 | 28996357 | 28996596 | chr7 | 28996759 | 28996998 | chr7 | 28997052 | 28997711 |
| chr7 | 28997967 | 28998206 | chr7 | 30721202 | 30721981 | chr7 | 30722214 | 30722453 |
| chr7 | 31092919 | 31093218 | chr7 | 31375899 | 31376230 | chr7 | 32110616 | 32110855 |
| chr7 | 32337733 | 32337912 | chr7 | 32338010 | 32338489 | chr7 | 32338826 | 32339005 |
| chr7 | 32467373 | 32468151 | chr7 | 32997050 | 32997463 | chr7 | 33943370 | 33943849 |
| chr7 | 35225724 | 35225963 | chr7 | 35226090 | 35226811 | chr7 | 35292893 | 35293372 |
| chr7 | 35293569 | 35294228 | chr7 | 35294400 | 35294639 | chr7 | 35295030 | 35295182 |
| chr7 | 35295807 | 35296000 | chr7 | 35296855 | 35298114 | chr7 | 35300851 | 35302050 |
| chr7 | 35494278 | 35494517 | chr7 | 37487076 | 37487251 | chr7 | 37487376 | 37487915 |
| chr7 | 37488179 | 37488658 | chr7 | 37488837 | 37489076 | chr7 | 37907366 | 37907545 |
| chr7 | 37955780 | 37956079 | chr7 | 37956176 | 37956535 | chr7 | 37960199 | 37960438 |
| chr7 | 38670267 | 38671106 | chr7 | 39015463 | 39016062 | chr7 | 42267573 | 42267752 |
| chr7 | 42276251 | 42276730 | chr7 | 42533028 | 42533387 | chr7 | 43152016 | 43152795 |
| chr7 | 43152858 | 43153337 | chr7 | 44097656 | 44097895 | chr7 | 44143906 | 44144085 |
| chr7 | 44151324 | 44151503 | chr7 | 44151715 | 44151857 | chr7 | 44164017 | 44164078 |
| chr7 | 44364752 | 44364991 | chr7 | 44835122 | 44835467 | chr7 | 45038447 | 45038564 |
| chr7 | 45613693 | 45613992 | chr7 | 45614259 | 45614558 | chr7 | 45614655 | 45615061 |
| chr7 | 45615536 | 45615588 | chr7 | 45960650 | 45960889 | chr7 | 45961072 | 45961251 |
| chr7 | 45961423 | 45961630 | chr7 | 45961656 | 45961662 | chr7 | 45961742 | 45961981 |
| chr7 | 49812718 | 49814097 | chr7 | 49814454 | 49814873 | chr7 | 49815014 | 49815848 |
| chr7 | 50294420 | 50294556 | chr7 | 50343183 | 50343482 | chr7 | 50343607 | 50344086 |
| chr7 | 50344150 | 50344569 | chr7 | 50364988 | 50365069 | chr7 | 50438544 | 50438723 |
| chr7 | 50560494 | 50560733 | chr7 | 50860135 | 50860393 | chr7 | 50860980 | 50861214 |
| chr7 | 51384235 | 51384534 | chr7 | 51384814 | 51385006 | chr7 | 54609764 | 54610243 |
| chr7 | 54612335 | 54612814 | chr7 | 55086481 | 55086687 | chr7 | 55086899 | 55087618 |
| chr7 | 55409933 | 55410223 | chr7 | 56018026 | 56018205 | chr7 | 56031847 | 56031966 |
| chr7 | 64330322 | 64330561 | chr7 | 64330635 | 64330645 | chr7 | 64348952 | 64349131 |
| chr7 | 64349318 | 64349551 | chr7 | 64700198 | 64700426 | chr7 | 64712288 | 64712587 |
| chr7 | 64974283 | 64974402 | chr7 | 65037592 | 65037702 | chr7 | 65508900 | 65509124 |
| chr7 | 66214974 | 66215062 | chr7 | 68204692 | 68204931 | chr7 | 69062428 | 69062727 |
| chr7 | 69064489 | 69065148 | chr7 | 69897685 | 69897924 | chr7 | 70596353 | 70596772 |
| chr7 | 70596845 | 70597204 | chr7 | 70597310 | 70597368 | chr7 | 70597395 | 70597549 |
| chr7 | 70597752 | 70597754 | chr7 | 70597780 | 70598471 | chr7 | 71217011 | 71217366 |
| chr7 | 71800599 | 71801978 | chr7 | 71802315 | 71802396 | chr7 | 71802457 | 71802734 |
| chr7 | 71871105 | 71871157 | chr7 | 76033251 | 76033364 | chr7 | 77324278 | 77324397 |
| chr7 | 79081718 | 79081897 | chr7 | 79081942 | 79081969 | chr7 | 79082070 | 79082301 |
| chr7 | 79083016 | 79083255 | chr7 | 79083314 | 79083913 | chr7 | 82072248 | 82072607 |
| chr7 | 84815049 | 84815135 | chr7 | 84815252 | 84815468 | chr7 | 84815670 | 84816029 |
| chr7 | 86273108 | 86273645 | chr7 | 86274018 | 86274547 | chr7 | 87104725 | 87105445 |
| chr7 | 87229446 | 87230525 | chr7 | 87256911 | 87257150 | chr7 | 87257964 | 87258143 |
| chr7 | 88387904 | 88388130 | chr7 | 88388190 | 88388263 | chr7 | 88388439 | 88388738 |
| chr7 | 88388789 | 88389389 | chr7 | 89747928 | 89748438 | chr7 | 89950108 | 89950813 |
| chr7 | 90226188 | 90226547 | chr7 | 90894936 | 90895175 | chr7 | 92466078 | 92466486 |
| chr7 | 92689613 | 92689774 | chr7 | 93203613 | 93203852 | chr7 | 93204233 | 93204592 |
| chr7 | 93519265 | 93520224 | chr7 | 93551225 | 93551524 | chr7 | 94284277 | 94284978 |
| chr7 | 96619499 | 96619678 | chr7 | 96621614 | 96621913 | chr7 | 96622019 | 96622438 |
| chr7 | 96625472 | 96625809 | chr7 | 96625906 | 96626145 | chr7 | 96631614 | 96631780 |
| chr7 | 96634577 | 96634996 | chr7 | 96635260 | 96635379 | chr7 | 96635440 | 96635559 |
| chr7 | 96635650 | 96636729 | chr7 | 96646568 | 96647227 | chr7 | 96647715 | 96648314 |
| chr7 | 96649965 | 96650284 | chr7 | 96650809 | 96651228 | chr7 | 96651384 | 96651584 |
| chr7 | 96652070 | 96652249 | chr7 | 96653421 | 96654080 | chr7 | 97361021 | 97361860 |
| chr7 | 97362211 | 97362690 | chr7 | 97600015 | 97600194 | chr7 | 97869540 | 97869719 |
| chr7 | 98245808 | 98246947 | chr7 | 98247032 | 98247751 | chr7 | 98971530 | 98971649 |
| chr7 | 99104174 | 99104293 | chr7 | 99177557 | 99177956 | chr7 | 99691732 | 99591851 |
| chr7 | 99595184 | 99595416 | chr7 | 99751485 | 99751553 | chr7 | 99775118 | 99775297 |
| chr7 | 100088099 | 100088398 | chr7 | 100091115 | 100091474 | chr7 | 100179789 | 100180017 |
| chr7 | 100318421 | 100318660 | chr7 | 100808365 | 100808596 | chr7 | 100809360 | 100809599 |
| chr7 | 100823348 | 100823587 | chr7 | 101005901 | 101006073 | chr7 | 101241919 | 101242098 |
| chr7 | 101475705 | 101475944 | chr7 | 101627683 | 101627884 | chr7 | 101707428 | 101707535 |
| chr7 | 103085786 | 103086565 | chr7 | 103628963 | 103630222 | chr7 | 103630381 | 103630920 |
| chr7 | 103969130 | 103969429 | chr7 | 103969595 | 103969894 | chr7 | 105279390 | 105279749 |
| chr7 | 105685195 | 106685434 | chr7 | 106797700 | 106797856 | chr7 | 107301418 | 107301717 |
| chr7 | 107483597 | 107484016 | chr7 | 108095222 | 108095466 | chr7 | 108095602 | 108096141 |
| chr7 | 108097093 | 108097572 | chr7 | 112726529 | 112726706 | chr7 | 113722736 | 113723515 |
| chr7 | 113724870 | 113725169 | chr7 | 113726435 | 113726614 | chr7 | 113727345 | 113727584 |
| chr7 | 113727633 | 113727872 | chr7 | 115117451 | 115117750 | chr7 | 116140155 | 116140268 |
| chr7 | 116962796 | 116963575 | chr7 | 117119347 | 117120366 | chr7 | 119913464 | 119913837 |
| chr7 | 120969587 | 120969886 | chr7 | 121513457 | 121513796 | chr7 | 121939584 | 121940543 |

TABLE 14-continued

| chr | start | end | chr | start | end | chr | start | end |
|---|---|---|---|---|---|---|---|---|
| chr7 | 121940845 | 121941144 | chr7 | 121941807 | 121942266 | chr7 | 121943905 | 121944264 |
| chr7 | 121945722 | 121946021 | chr7 | 121946403 | 121947482 | chr7 | 121950034 | 121951029 |
| chr7 | 121951784 | 121952256 | chr7 | 121956408 | 121956647 | chr7 | 121956650 | 121957411 |
| chr7 | 123173048 | 123173327 | chr7 | 123671948 | 123672187 | chr7 | 124404320 | 124404619 |
| chr7 | 126891146 | 126891325 | chr7 | 126891430 | 126891669 | chr7 | 127371055 | 127371234 |
| chr7 | 127615847 | 127616026 | chr7 | 127744048 | 127744707 | chr7 | 127806560 | 127806739 |
| chr7 | 127807743 | 127807922 | chr7 | 127807921 | 127808822 | chr7 | 127841426 | 127841785 |
| chr7 | 127991742 | 127992221 | chr7 | 128096988 | 128097164 | chr7 | 128337365 | 128337543 |
| chr7 | 128337605 | 128338023 | chr7 | 128470816 | 128471115 | chr7 | 128486020 | 128486237 |
| chr7 | 128528729 | 128528854 | chr7 | 128528949 | 128529128 | chr7 | 128828115 | 128828354 |
| chr7 | 129229605 | 129229724 | chr7 | 129418168 | 129418513 | chr7 | 129422070 | 129423509 |
| chr7 | 129424552 | 129425991 | chr7 | 129426215 | 129426336 | chr7 | 129794508 | 129794802 |
| chr7 | 129800223 | 129800462 | chr7 | 131041437 | 131041676 | chr7 | 131242662 | 131242901 |
| chr7 | 131514750 | 131514929 | chr7 | 132261173 | 132261532 | chr7 | 134143081 | 134143560 |
| chr7 | 134143731 | 134144209 | chr7 | 134918421 | 134918720 | chr7 | 136553316 | 136553495 |
| chr7 | 136553556 | 136554469 | chr7 | 136554563 | 136555042 | chr7 | 136555145 | 136555504 |
| chr7 | 136555587 | 136556186 | chr7 | 137028402 | 137028623 | chr7 | 137531153 | 137532438 |
| chr7 | 138042136 | 138042315 | chr7 | 139167532 | 139167831 | chr7 | 139167942 | 139168481 |
| chr7 | 139208697 | 139208888 | chr7 | 139930070 | 139930371 | chr7 | 139939060 | 139939314 |
| chr7 | 140026925 | 140027043 | chr7 | 140180180 | 140180298 | chr7 | 140339839 | 140339905 |
| chr7 | 140339966 | 140340078 | chr7 | 140453048 | 140453227 | chr7 | 140772713 | 140773312 |
| chr7 | 140773478 | 140773837 | chr7 | 143042537 | 143042896 | chr7 | 143579665 | 143580144 |
| chr7 | 145812918 | 145813157 | chr7 | 145813334 | 145813573 | chr7 | 145813790 | 145814269 |
| chr7 | 148224592 | 148224711 | chr7 | 148640242 | 148640331 | chr7 | 148846061 | 148846279 |
| chr7 | 149111968 | 149112226 | chr7 | 149112287 | 149112507 | chr7 | 149119862 | 149120161 |
| chr7 | 149411444 | 149412403 | chr7 | 149744414 | 149744653 | chr7 | 149917173 | 149917412 |
| chr7 | 149918045 | 149918224 | chr7 | 150049512 | 150049626 | chr7 | 150069013 | 150069432 |
| chr7 | 150069601 | 150069662 | chr7 | 150069837 | 150069900 | chr7 | 150069921 | 150070160 |
| chr7 | 150081153 | 150081354 | chr7 | 150716088 | 150716387 | chr7 | 150748090 | 150748509 |
| chr7 | 150753843 | 150754082 | chr7 | 150870734 | 150870973 | chr7 | 161106369 | 151107088 |
| chr7 | 151107390 | 151107749 | chr7 | 151591567 | 151691806 | chr7 | 162622540 | 152622779 |
| chr7 | 152622918 | 152623157 | chr7 | 153583503 | 153584162 | chr7 | 153584297 | 153584546 |
| chr7 | 153584694 | 153584716 | chr7 | 153584758 | 153585233 | chr7 | 153585333 | 153585692 |
| chr7 | 153749619 | 153750218 | chr7 | 154561051 | 154561290 | chr7 | 154708188 | 154708355 |
| chr7 | 154861947 | 154862366 | chr7 | 155164379 | 155165638 | chr7 | 155165791 | 155166870 |
| chr7 | 155166933 | 155167992 | chr7 | 155174573 | 155174872 | chr7 | 155241235 | 155242134 |
| chr7 | 155242647 | 155243186 | chr7 | 155243245 | 155243664 | chr7 | 155243741 | 155243980 |
| chr7 | 155244092 | 155244451 | chr7 | 155246786 | 155247685 | chr7 | 155248839 | 155249018 |
| chr7 | 155249420 | 155249659 | chr7 | 155249849 | 155250088 | chr7 | 155250200 | 155250439 |
| chr7 | 155250713 | 156251072 | chr7 | 155251611 | 155252030 | chr7 | 155252160 | 155252579 |
| chr7 | 155252773 | 155253132 | chr7 | 155254765 | 155255416 | chr7 | 155256216 | 155256395 |
| chr7 | 155256986 | 155257265 | chr7 | 155258101 | 155258580 | chr7 | 155258854 | 155260233 |
| chr7 | 155260806 | 155261285 | chr7 | 155301736 | 155302035 | chr7 | 155302267 | 155303432 |
| chr7 | 155325720 | 155325954 | chr7 | 155326079 | 155326618 | chr7 | 155363212 | 155363511 |
| chr7 | 155580069 | 155580308 | chr7 | 155580772 | 155580882 | chr7 | 155581243 | 155581652 |
| chr7 | 155581664 | 155581962 | chr7 | 155582190 | 155582369 | chr7 | 155600527 | 155600825 |
| chr7 | 155602726 | 155602898 | chr7 | 156409214 | 156409426 | chr7 | 156409585 | 156409884 |
| chr7 | 156701758 | 156701997 | chr7 | 156744697 | 156744866 | chr7 | 156794465 | 156794579 |
| chr7 | 156794922 | 156795996 | chr7 | 156796442 | 156799561 | chr7 | 156800925 | 156801104 |
| chr7 | 156801323 | 156801682 | chr7 | 156808760 | 156809299 | chr7 | 156809953 | 156811520 |
| chr7 | 156812773 | 156815170 | chr7 | 156832194 | 156832493 | chr7 | 156832766 | 156833245 |
| chr7 | 156871084 | 156871383 | chr7 | 156880457 | 156880636 | chr7 | 157085281 | 157085580 |
| chr7 | 157085874 | 157086173 | chr7 | 157262738 | 157263097 | chr7 | 157263204 | 157263563 |
| chr7 | 157361531 | 157361710 | chr7 | 157476790 | 157477376 | chr7 | 157477395 | 157477994 |
| chr7 | 157481289 | 157481860 | chr7 | 157481890 | 157482249 | chr7 | 157482401 | 157482760 |
| chr7 | 157483220 | 157483639 | chr7 | 157484778 | 157485377 | chr7 | 157485437 | 157485796 |
| chr7 | 157485881 | 157486600 | chr7 | 157584104 | 157584283 | chr7 | 157588510 | 157588869 |
| chr7 | 157606632 | 157606811 | chr7 | 157690145 | 157690161 | chr7 | 158059659 | 158059898 |
| chr7 | 158936420 | 158936956 | chr7 | 158937062 | 158937721 | chr7 | 158938126 | 158938485 |
| chr8 | 686794 | 687393 | chr8 | 687650 | 688129 | chr8 | 688286 | 688465 |
| chr8 | 688895 | 689134 | chr8 | 1085559 | 1085678 | chr8 | 4849040 | 4849279 |
| chr8 | 4849364 | 4849603 | chr8 | 4850173 | 4850592 | chr8 | 4851662 | 4851686 |
| chr8 | 4851722 | 4851841 | chr8 | 4851921 | 4852220 | chr8 | 8748329 | 8748808 |
| chr8 | 8748819 | 8749058 | chr8 | 9722754 | 9722993 | chr8 | 9755965 | 9756564 |
| chr8 | 9760646 | 9761245 | chr8 | 9762487 | 9762965 | chr8 | 9763060 | 9763359 |
| chr8 | 9763816 | 9764295 | chr8 | 9764344 | 9764643 | chr8 | 10587507 | 10587866 |
| chr8 | 10588301 | 10588540 | chr8 | 11204405 | 11204584 | chr8 | 11204709 | 11205008 |
| chr8 | 11536753 | 11536932 | chr8 | 11537123 | 11537362 | chr8 | 11554886 | 11554990 |
| chr8 | 11555068 | 11559605 | chr8 | 11559678 | 11559792 | chr8 | 11559920 | 11560457 |
| chr8 | 11560633 | 11560872 | chr8 | 11561357 | 11562256 | chr8 | 11562335 | 11562574 |
| chr8 | 11562600 | 11563019 | chr8 | 11705869 | 11706228 | chr8 | 11726393 | 11726505 |
| chr8 | 12990409 | 12990529 | chr8 | 12990575 | 12990874 | chr8 | 13319857 | 13319937 |
| chr8 | 15094425 | 15094664 | chr8 | 15397641 | 15397940 | chr8 | 16884239 | 16884331 |
| chr8 | 16885104 | 16885343 | chr8 | 17270974 | 17271213 | chr8 | 19797396 | 19797538 |
| chr8 | 19797860 | 19798099 | chr8 | 20160679 | 20160978 | chr8 | 22089428 | 22089665 |
| chr8 | 22562265 | 22562564 | chr8 | 22960567 | 22960806 | chr8 | 23021083 | 23021209 |
| chr8 | 23260598 | 23260957 | chr8 | 23423830 | 23424009 | chr8 | 23559296 | 23560615 |
| chr8 | 23563712 | 23564480 | chr8 | 23564697 | 23565108 | chr8 | 23566729 | 23567568 |

TABLE 14-continued

| chr | start | end | chr | start | end | chr | start | end |
|---|---|---|---|---|---|---|---|---|
| chr8 | 23571588 | 23572067 | chr8 | 23572334 | 23572646 | chr8 | 23584000 | 23584839 |
| chr8 | 24770239 | 24770658 | chr8 | 24771072 | 24771311 | chr8 | 24771348 | 24771647 |
| chr8 | 24813089 | 24813388 | chr8 | 24813660 | 24814499 | chr8 | 24857673 | 24857912 |
| chr8 | 24858239 | 24858538 | chr8 | 24858770 | 24859249 | chr8 | 24859422 | 24859601 |
| chr8 | 25041656 | 25041955 | chr8 | 25042636 | 25042671 | chr8 | 25900324 | 25901403 |
| chr8 | 25901444 | 25901863 | chr8 | 25902072 | 25902251 | chr8 | 25902545 | 25902640 |
| chr8 | 25903579 | 25903938 | chr8 | 25904055 | 25904294 | chr8 | 25905022 | 25905201 |
| chr8 | 25905668 | 25905907 | chr8 | 25909098 | 25909697 | chr8 | 26372789 | 26372968 |
| chr8 | 26723884 | 26724183 | chr8 | 30243289 | 30243526 | chr8 | 30769151 | 30769610 |
| chr8 | 30770028 | 30770267 | chr8 | 31496380 | 31496859 | chr8 | 31496939 | 31497176 |
| chr8 | 31497420 | 31497719 | chr8 | 31498015 | 31498254 | chr8 | 32406517 | 32406996 |
| chr8 | 33371978 | 33372217 | chr8 | 33457052 | 33457471 | chr8 | 35092906 | 35093140 |
| chr8 | 35093877 | 35094056 | chr8 | 37655367 | 37655606 | chr8 | 37655707 | 37656186 |
| chr8 | 37822721 | 37823500 | chr8 | 37823583 | 37823805 | chr8 | 37961879 | 37961998 |
| chr8 | 38008157 | 38008636 | chr8 | 38323837 | 38324016 | chr8 | 38965450 | 38965464 |
| chr8 | 41165785 | 41166804 | chr8 | 41166886 | 41167125 | chr8 | 41424682 | 41424921 |
| chr8 | 41624752 | 41624931 | chr8 | 41625038 | 41626217 | chr8 | 41733424 | 41733723 |
| chr8 | 41753498 | 41753857 | chr8 | 41754070 | 41754969 | chr8 | 41755104 | 41755283 |
| chr8 | 41910186 | 41910425 | chr8 | 42147417 | 42147596 | chr8 | 42749996 | 42750094 |
| chr8 | 47093172 | 47093351 | chr8 | 47334530 | 47334694 | chr8 | 48100075 | 48100539 |
| chr8 | 49293280 | 49293699 | chr8 | 49468571 | 49469228 | chr8 | 49571955 | 49572134 |
| chr8 | 49782953 | 49783235 | chr8 | 49959156 | 49959335 | chr8 | 50822095 | 50822394 |
| chr8 | 50822591 | 50822830 | chr8 | 50823358 | 50823657 | chr8 | 53477325 | 53477864 |
| chr8 | 53477933 | 53478352 | chr8 | 53478391 | 53478744 | chr8 | 53853711 | 53854552 |
| chr8 | 54163240 | 54164256 | chr8 | 54789175 | 54789414 | chr8 | 54789556 | 54790155 |
| chr8 | 54790214 | 54790883 | chr8 | 54791724 | 54792323 | chr8 | 54792548 | 54792847 |
| chr8 | 54794123 | 54794422 | chr8 | 54794626 | 54795165 | chr8 | 55366106 | 55367725 |
| chr8 | 55370037 | 55370936 | chr8 | 55371079 | 55372638 | chr8 | 55379202 | 55380041 |
| chr8 | 55382673 | 55383332 | chr8 | 56013545 | 56014024 | chr8 | 56014058 | 56014417 |
| chr8 | 56014524 | 56014883 | chr8 | 56014959 | 56015438 | chr8 | 56015471 | 56015710 |
| chr8 | 56015834 | 56015893 | chr8 | 57025609 | 57026028 | chr8 | 57026072 | 57026311 |
| chr8 | 57026406 | 57026644 | chr8 | 57069473 | 57070245 | chr8 | 57358053 | 57359732 |
| chr8 | 57360472 | 57360891 | chr8 | 58105852 | 58106211 | chr8 | 58116923 | 58117162 |
| chr8 | 58130290 | 58130649 | chr8 | 58907618 | 58907917 | chr8 | 59058934 | 59059233 |
| chr8 | 59747274 | 59747402 | chr8 | 60032590 | 60032829 | chr8 | 61777488 | 61777622 |
| chr8 | 61789900 | 61790076 | chr8 | 62200414 | 62200879 | chr8 | 63161580 | 63161879 |
| chr8 | 65281539 | 65281778 | chr8 | 65281884 | 65283443 | chr8 | 65283708 | 65284187 |
| chr8 | 65285972 | 65286451 | chr8 | 65286599 | 65286838 | chr8 | 65286868 | 65287229 |
| chr8 | 65289033 | 65289332 | chr8 | 65289517 | 65290450 | chr8 | 65290570 | 65290896 |
| chr8 | 65290950 | 65291369 | chr8 | 65292097 | 65292102 | chr8 | 65292180 | 65292816 |
| chr8 | 65488178 | 65488417 | chr8 | 65488618 | 65488799 | chr8 | 65489025 | 65489204 |
| chr8 | 65492637 | 65493056 | chr8 | 65493105 | 65493524 | chr8 | 65493556 | 65493855 |
| chr8 | 65493868 | 65493969 | chr8 | 65494048 | 65494287 | chr8 | 65498465 | 65498550 |
| chr8 | 65498645 | 65498910 | chr8 | 65498926 | 65498944 | chr8 | 65499677 | 65500096 |
| chr8 | 65710868 | 65711142 | chr8 | 66548640 | 66548749 | chr8 | 67024963 | 67025365 |
| chr8 | 67344446 | 67344865 | chr8 | 67873246 | 67875697 | chr8 | 67940548 | 67940960 |
| chr8 | 68864493 | 68864852 | chr8 | 59242828 | 69243007 | chr8 | 69243183 | 69243971 |
| chr8 | 69244286 | 69244585 | chr8 | 70744774 | 70745013 | chr8 | 70946670 | 70947742 |
| chr8 | 70981866 | 70983305 | chr8 | 70983402 | 70985081 | chr8 | 72273897 | 72274136 |
| chr8 | 72459929 | 72460348 | chr8 | 72468473 | 72469664 | chr8 | 72470301 | 72470540 |
| chr8 | 72471037 | 72471158 | chr8 | 22754293 | 72754712 | chr8 | 72754730 | 72755240 |
| chr8 | 72755592 | 72756971 | chr8 | 72917268 | 72917541 | chr8 | 72987519 | 72988118 |
| chr8 | 73163680 | 73164261 | chr8 | 73449963 | 73450202 | chr8 | 73450418 | 23450657 |
| chr8 | 74759411 | 74759565 | chr8 | 74759744 | 74759863 | chr8 | 75896477 | 75897436 |
| chr8 | 76316242 | 76316541 | chr8 | 77585130 | 77585789 | chr8 | 77586078 | 77586377 |
| chr8 | 77586471 | 77586710 | chr8 | 77590144 | 77590563 | chr8 | 77593075 | 77593453 |
| chr8 | 77593798 | 77594217 | chr8 | 77594552 | 77595091 | chr8 | 77595238 | 77595594 |
| chr8 | 79428200 | 79428499 | chr8 | 80523887 | 80524126 | chr8 | 80524167 | 80524406 |
| chr8 | 80524864 | 80525103 | chr8 | 80525520 | 80525819 | chr8 | 80695842 | 80696007 |
| chr8 | 80803594 | 80803953 | chr8 | 81478089 | 81478448 | chr8 | 85095396 | 85095755 |
| chr8 | 85096485 | 85096721 | chr8 | 85096785 | 85096904 | chr8 | 85096939 | 85097298 |
| chr8 | 86350455 | 86350633 | chr8 | 86406814 | 86406933 | chr8 | 86436547 | 86436726 |
| chr8 | 86544681 | 86544798 | chr8 | 89339298 | 89339837 | chr8 | 89340189 | 89340428 |
| chr8 | 90913517 | 90913756 | chr8 | 91094161 | 91094326 | chr8 | 91803578 | 91803817 |
| chr8 | 91803913 | 91804332 | chr8 | 91996958 | 91998020 | chr8 | 92083443 | 92083622 |
| chr8 | 93114033 | 93114632 | chr8 | 95651240 | 95651308 | chr8 | 95651448 | 95651599 |
| chr8 | 95651637 | 95651747 | chr8 | 96219911 | 96220002 | chr8 | 97157007 | 97158146 |
| chr8 | 97165541 | 97165780 | chr8 | 97166351 | 97166530 | chr8 | 97167082 | 97167321 |
| chr8 | 97169757 | 97170416 | chr8 | 97170793 | 97170972 | chr8 | 92171036 | 97172295 |
| chr8 | 97172347 | 97173546 | chr8 | 97173730 | 97173991 | chr8 | 97339752 | 97340291 |
| chr8 | 97505950 | 97506609 | chr8 | 97507021 | 97507380 | chr8 | 97507464 | 97507763 |
| chr8 | 98289744 | 98290343 | chr8 | 99439030 | 99439209 | chr8 | 99439299 | 99440438 |
| chr8 | 99951330 | 99951509 | chr8 | 99952896 | | chr8 | 99954400 | 99954819 |
| chr8 | 99955105 | 99955394 | chr8 | 99960231 | 99961070 | chr8 | 99961111 | 99961350 |
| chr8 | 99961718 | 99961897 | chr8 | 99985781 | 99987020 | chr8 | 101118140 | 101118679 |
| chr8 | 101661837 | 101662000 | chr8 | 101821891 | 101822130 | chr8 | 102505458 | 102505654 |
| chr8 | 102505720 | 102506079 | chr8 | 103629857 | 103629961 | chr8 | 104153105 | 104153344 |
| chr8 | 104153366 | 104153725 | chr8 | 104512026 | 104513285 | chr8 | 104513365 | 104514005 |

TABLE 14-continued

| chr | start | end | chr | start | end | chr | start | end |
|---|---|---|---|---|---|---|---|---|
| chr8 | 105235293 | 105236132 | chr8 | 105478632 | 105479281 | chr8 | 105479315 | 105479531 |
| chr8 | 106331080 | 106331319 | chr8 | 106332004 | 106332286 | chr8 | 107282060 | 107282299 |
| chr8 | 107283938 | 107284177 | chr8 | 108509441 | 108509734 | chr8 | 109093601 | 109094260 |
| chr8 | 109094391 | 109094690 | chr8 | 109094757 | 109096016 | chr8 | 109799500 | 109799859 |
| chr8 | 110274904 | 110275021 | chr8 | 110405946 | 110406105 | chr8 | 110592245 | 110592303 |
| chr8 | 110703924 | 110704029 | chr8 | 110704098 | 110704223 | chr8 | 110986354 | 110986773 |
| chr8 | 114444497 | 114444640 | chr8 | 114444709 | 114445276 | chr8 | 114445672 | 114446101 |
| chr8 | 114446851 | 114447450 | chr8 | 114448939 | 114449358 | chr8 | 114449457 | 114449688 |
| chr8 | 116660435 | 116660854 | chr8 | 117950364 | 117950543 | chr8 | 117950700 | 117950999 |
| chr8 | 120220390 | 120220629 | chr8 | 120844011 | 120844126 | chr8 | 121136805 | 121137824 |
| chr8 | 121823827 | 121824006 | chr8 | 121824103 | 121824582 | chr8 | 121825512 | 121825560 |
| chr8 | 122651770 | 122652009 | chr8 | 123695447 | 123695746 | chr8 | 124055137 | 124055235 |
| chr8 | 124173165 | 124173544 | chr8 | 125452275 | 125452394 | chr8 | 126044494 | 126044653 |
| chr8 | 128745443 | 128745618 | chr8 | 128872311 | 128872490 | chr8 | 128889224 | 128889483 |
| chr8 | 128931157 | 128931336 | chr8 | 130369290 | 130369454 | chr8 | 132052057 | 132063256 |
| chr8 | 132053633 | 132054876 | chr8 | 133686658 | 133686836 | chr8 | 139508668 | 139509386 |
| chr8 | 139509656 | 139510015 | chr8 | 140714485 | 140714964 | chr8 | 140715016 | 140715195 |
| chr8 | 140715379 | 140715738 | chr8 | 140715875 | 140716348 | chr8 | 140834160 | 140834399 |
| chr8 | 140963208 | 140963447 | chr8 | 141159845 | 141160024 | chr8 | 141587975 | 141588214 |
| chr8 | 141596805 | 141597104 | chr8 | 142292454 | 142292808 | chr8 | 142361151 | 142361430 |
| chr8 | 142367673 | 142367879 | chr8 | 142444648 | 142444827 | chr8 | 142528313 | 142529092 |
| chr8 | 142535241 | 142535587 | chr8 | 142568506 | 142568745 | chr8 | 142694751 | 142695030 |
| chr8 | 142984437 | 142984736 | chr8 | 143088946 | 143089150 | chr8 | 143105162 | 143105461 |
| chr8 | 143509377 | 143509676 | chr8 | 143532035 | 143532934 | chr8 | 143533520 | 143533999 |
| chr8 | 143557881 | 143558172 | chr8 | 143558389 | 143558688 | chr8 | 143587238 | 143587477 |
| chr8 | 143592583 | 143592762 | chr8 | 143621889 | 143622188 | chr8 | 143701978 | 143702157 |
| chr8 | 143819303 | 143819406 | chr8 | 143858435 | 143858791 | chr8 | 143859223 | 143859454 |
| chr8 | 143876854 | 143877033 | chr8 | 143993891 | 143994250 | chr8 | 144069457 | 144069749 |
| chr8 | 144190286 | 144190525 | chr8 | 144203601 | 144203801 | chr8 | 144203880 | 144204020 |
| chr8 | 144226100 | 144226279 | chr8 | 144238743 | 144238982 | chr8 | 144241150 | 144241389 |
| chr8 | 144241444 | 144241683 | chr8 | 144241785 | 144242381 | chr8 | 144303488 | 144303667 |
| chr8 | 144328234 | 144328653 | chr8 | 144330288 | 144330467 | chr8 | 144344219 | 144344518 |
| chr8 | 144359928 | 144360177 | chr8 | 144360305 | 144360544 | chr8 | 144361672 | 144361911 |
| chr8 | 144372474 | 144372583 | chr8 | 144509238 | 144510617 | chr8 | 144511146 | 144511505 |
| chr8 | 144511938 | 144512297 | chr8 | 144512399 | 144512466 | chr8 | 144650791 | 144650812 |
| chr8 | 144668532 | 144668767 | chr8 | 144668822 | 144669061 | chr8 | 145698244 | 145698483 |
| chr8 | 145753443 | 145753622 | chr8 | 145758483 | 145758782 | chr8 | 145806184 | 145806350 |
| chr8 | 145925387 | 145925566 | chr8 | 145925869 | 145926080 | chr8 | 146013543 | 146013722 |
| chr8 | 146079134 | 146079297 | chr9 | 113346 | 113645 | chr9 | 113749 | 113988 |
| chr9 | 117808 | 118167 | chr9 | 841602 | 842244 | chr9 | 842545 | 842766 |
| chr9 | 969482 | 969661 | chr9 | 969685 | 969943 | chr9 | 970012 | 970311 |
| chr9 | 970421 | 970600 | chr9 | 970816 | 971175 | chr9 | 971435 | 971655 |
| chr9 | 972204 | 972863 | chr9 | 973067 | 973366 | chr9 | 975248 | 975262 |
| chr9 | 975693 | 976412 | chr9 | 976521 | 977047 | chr9 | 981695 | 981934 |
| chr9 | 1042305 | 1043076 | chr9 | 1051768 | 1052247 | chr9 | 3181662 | 3181961 |
| chr9 | 6412497 | 6412900 | chr9 | 6644217 | 6644636 | chr9 | 6644936 | 6645415 |
| chr9 | 6645544 | 6645783 | chr9 | 6756279 | 6756429 | chr9 | 13278722 | 13278961 |
| chr9 | 14312943 | 14313182 | chr9 | 14347534 | 14347759 | chr9 | 14348234 | 14348533 |
| chr9 | 17906310 | 17906789 | chr9 | 17906914 | 17907153 | chr9 | 17907325 | 17907564 |
| chr9 | 19789025 | 19789381 | chr9 | 21031636 | 21031924 | chr9 | 21402520 | 21403119 |
| chr9 | 21559219 | 21559446 | chr9 | 21559678 | 21559804 | chr9 | 21964958 | 21965857 |
| chr9 | 21968138 | 21968557 | chr9 | 21970881 | 21971282 | chr9 | 21974164 | 21974329 |
| chr9 | 21974408 | 21974887 | chr9 | 21994134 | 21994313 | chr9 | 21995223 | 21995402 |
| chr9 | 21995646 | 21995825 | chr9 | 22006057 | 22006236 | chr9 | 22447567 | 22447772 |
| chr9 | 23822468 | 23822707 | chr9 | 23824487 | 23824666 | chr9 | 23831023 | 23831490 |
| chr9 | 29212083 | 29212382 | chr9 | 29213431 | 29213730 | chr9 | 29213938 | 29214237 |
| chr9 | 29214276 | 29214515 | chr9 | 29214585 | 29215184 | chr9 | 32782547 | 32783206 |
| chr9 | 32783263 | 32783742 | chr9 | 33524529 | 33524768 | chr9 | 33676697 | 33676876 |
| chr9 | 33677269 | 33677508 | chr9 | 34224262 | 34224497 | chr9 | 34372761 | 34373000 |
| chr9 | 34588960 | 34589259 | chr9 | 34809656 | 34810075 | chr9 | 35617195 | 35617434 |
| chr9 | 35675441 | 35676233 | chr9 | 36036994 | 36037173 | chr9 | 36318274 | 36318389 |
| chr9 | 36739659 | 36740078 | chr9 | 37002394 | 37003113 | chr9 | 37025465 | 37025884 |
| chr9 | 37026055 | 37026714 | chr9 | 37026733 | 37027512 | chr9 | 37027726 | 37027905 |
| chr9 | 37028870 | 37029049 | chr9 | 37029436 | 37030755 | chr9 | 37034163 | 37034342 |
| chr9 | 37034525 | 37034824 | chr9 | 37035427 | 37035850 | chr9 | 37036327 | 37036746 |
| chr9 | 37037594 | 37038433 | chr9 | 37467521 | 37467634 | chr9 | 38620642 | 38620808 |
| chr9 | 66456024 | 66456117 | chr9 | 71200618 | 71200720 | chr9 | 71734803 | 71734920 |
| chr9 | 71788876 | 71789512 | chr9 | 71789608 | 71789835 | chr9 | 73032727 | 73032835 |
| chr9 | 74061745 | 74062164 | chr9 | 74764449 | 74764748 | chr9 | 77112900 | 77113919 |
| chr9 | 77114649 | 77114948 | chr9 | 77115120 | 77116539 | chr9 | 77115583 | 77115587 |
| chr9 | 79626794 | 79627453 | chr9 | 79628190 | 79628429 | chr9 | 79629014 | 79529499 |
| chr9 | 79629533 | 79629553 | chr9 | 79629791 | 79630510 | chr9 | 79631115 | 79631414 |
| chr9 | 79631454 | 79631693 | chr9 | 79631785 | 79632264 | chr9 | 79632786 | 79632965 |
| chr9 | 79633322 | 79633981 | chr9 | 79634088 | 79634987 | chr9 | 79635048 | 79636066 |
| chr9 | 79636103 | 79636127 | chr9 | 79636167 | 79636642 | chr9 | 79636717 | 79637366 |
| chr9 | 79637644 | 79638336 | chr9 | 86152313 | 86152492 | chr9 | 86755443 | 86756042 |
| chr9 | 86886632 | 86886811 | chr9 | 87282934 | 87283113 | chr9 | 87283574 | 87283813 |
| chr9 | 87284603 | 87284902 | chr9 | 87285203 | 87285556 | chr9 | 88137487 | 88138091 |

TABLE 14-continued

| chr | start | end | chr | start | end | chr | start | end |
|---|---|---|---|---|---|---|---|---|
| chr9 | 89517623 | 89517917 | chr9 | 89560675 | 89560914 | chr9 | 89560967 | 89561206 |
| chr9 | 91150130 | 91150429 | chr9 | 91605912 | 91606151 | chr9 | 91792283 | 91792462 |
| chr9 | 91792693 | 91792992 | chr9 | 91793083 | 91793622 | chr9 | 93697942 | 93698051 |
| chr9 | 94183793 | 94184032 | chr9 | 94572543 | 94572703 | chr9 | 94712081 | 94712320 |
| chr9 | 95417452 | 95417747 | chr9 | 95560736 | 95560915 | chr9 | 95569672 | 95569911 |
| chr9 | 95570162 | 95570521 | chr9 | 95571540 | 95571659 | chr9 | 95571753 | 95571839 |
| chr9 | 95947121 | 95947360 | chr9 | 96588726 | 96588965 | chr9 | 96710303 | 96710482 |
| chr9 | 96710582 | 96711089 | chr9 | 96711169 | 96711708 | chr9 | 96711901 | 96712080 |
| chr9 | 96713277 | 96713996 | chr9 | 96714997 | 96715068 | chr9 | 96715135 | 96715794 |
| chr9 | 96716763 | 96717542 | chr9 | 96717885 | 96718244 | chr9 | 96720752 | 96721903 |
| chr9 | 96722477 | 96722886 | chr9 | 96722999 | 96723298 | chr9 | 98111281 | 98112472 |
| chr9 | 98784698 | 98784877 | chr9 | 98789557 | 98790096 | chr9 | 99449054 | 99449487 |
| chr9 | 99639543 | 99640022 | chr9 | 99983066 | 99983245 | chr9 | 99983319 | 99983704 |
| chr9 | 99983799 | 99983918 | chr9 | 99983925 | 99984004 | chr9 | 100503542 | 100504021 |
| chr9 | 100609970 | 100610315 | chr9 | 100610603 | 100611731 | chr9 | 100613748 | 100614407 |
| chr9 | 100614463 | 100616682 | chr9 | 100616743 | 100616982 | chr9 | 100617210 | 100617449 |
| chr9 | 100617600 | 100618139 | chr9 | 100619627 | 100620166 | chr9 | 100620228 | 100620862 |
| chr9 | 100818337 | 100818516 | chr9 | 100835850 | 100835969 | chr9 | 101469169 | 101469408 |
| chr9 | 101469521 | 101469880 | chr9 | 101470034 | 101470333 | chr9 | 101470991 | 101471170 |
| chr9 | 101471477 | 101471716 | chr9 | 101471786 | 101472030 | chr9 | 101705897 | 101706796 |
| chr9 | 103174718 | 103174825 | chr9 | 104248482 | 104248721 | chr9 | 104249400 | 104249632 |
| chr9 | 104500551 | 104500850 | chr9 | 110126159 | 110126338 | chr9 | 110228102 | 110228701 |
| chr9 | 110251381 | 110251493 | chr9 | 110252260 | 110252455 | chr9 | 110252548 | 110252619 |
| chr9 | 112403096 | 112403275 | chr9 | 112403290 | 112403469 | chr9 | 113341445 | 113342044 |
| chr9 | 113342201 | 113342428 | chr9 | 115067840 | 115067945 | chr9 | 115478852 | 115478971 |
| chr9 | 115652867 | 115653526 | chr9 | 116633786 | 116633905 | chr9 | 117050887 | 117051126 |
| chr9 | 118916933 | 118917172 | chr9 | 120175695 | 120175934 | chr9 | 120176009 | 120176248 |
| chr9 | 120176793 | 120176972 | chr9 | 120507335 | 120507514 | chr9 | 122131383 | 122131742 |
| chr9 | 122131785 | 122132320 | chr9 | 123295404 | 123295559 | chr9 | 124751411 | 124751590 |
| chr9 | 125676724 | 125676798 | chr9 | 126133698 | 126133937 | chr9 | 126154201 | 126154651 |
| chr9 | 126349070 | 126349191 | chr9 | 126770159 | 126770398 | chr9 | 126771440 | 126771799 |
| chr9 | 126774442 | 126775221 | chr9 | 126775456 | 126775620 | chr9 | 126775963 | 126776202 |
| chr9 | 126777488 | 126778086 | chr9 | 126778301 | 126778593 | chr9 | 126779391 | 126780406 |
| chr9 | 126780736 | 126780975 | chr9 | 126783321 | 126783577 | chr9 | 127212750 | 127213109 |
| chr9 | 127265588 | 127266127 | chr9 | 127266372 | 127266611 | chr9 | 128652097 | 128652336 |
| chr9 | 128759764 | 128760053 | chr9 | 129276620 | 129276919 | chr9 | 129372837 | 129373316 |
| chr9 | 129376096 | 129376275 | chr9 | 129376815 | 129376892 | chr9 | 129376932 | 129376994 |
| chr9 | 129377116 | 129377415 | chr9 | 129377505 | 129378104 | chr9 | 129381027 | 129381266 |
| chr9 | 129387421 | 129387539 | chr9 | 129387701 | 129388300 | chr9 | 129388639 | 129388878 |
| chr9 | 129388915 | 129389274 | chr9 | 129400912 | 129401271 | chr9 | 129445232 | 129445651 |
| chr9 | 129445709 | 129445888 | chr9 | 129485763 | 129486002 | chr9 | 130248345 | 130248524 |
| chr9 | 130461543 | 130461842 | chr9 | 130689539 | 130689742 | chr9 | 131579939 | 131580104 |
| chr9 | 131607443 | 131607622 | chr9 | 131607696 | 131607875 | chr9 | 131854131 | 131854430 |
| chr9 | 132382297 | 132383116 | chr9 | 132402743 | 132402982 | chr9 | 132403064 | 132403303 |
| chr9 | 132559298 | 132559413 | chr9 | 132805270 | 132805449 | chr9 | 132805750 | 132805989 |
| chr9 | 133308798 | 133309037 | chr9 | 133534609 | 133534788 | chr9 | 133535638 | 133535937 |
| chr9 | 133536012 | 133536431 | chr9 | 133536675 | 133536974 | chr9 | 133537097 | 133537636 |
| chr9 | 133538090 | 133538809 | chr9 | 133539509 | 133539808 | chr9 | 133540977 | 133541276 |
| chr9 | 133541594 | 133542433 | chr9 | 133773666 | 133774025 | chr9 | 133927265 | 133927564 |
| chr9 | 133928162 | 133928341 | chr9 | 134191003 | 134191302 | chr9 | 134207833 | 134207997 |
| chr9 | 134421818 | 134421936 | chr9 | 134717221 | 134717434 | chr9 | 135037029 | 135037448 |
| chr9 | 135455317 | 135455676 | chr9 | 135455912 | 135456151 | chr9 | 135456391 | 135456630 |
| chr9 | 135456796 | 135456915 | chr9 | 135458388 | 135458687 | chr9 | 135459920 | 135460269 |
| chr9 | 135460795 | 135460819 | chr9 | 135461455 | 135461852 | chr9 | 135461969 | 135463048 |
| chr9 | 135464709 | 135465008 | chr9 | 135465861 | 135466220 | chr9 | 135466263 | 135466742 |
| chr9 | 135648157 | 135548265 | chr9 | 135865007 | 135865245 | chr9 | 135898809 | 135899211 |
| chr9 | 136474400 | 136474699 | chr9 | 137299018 | 137299555 | chr9 | 137299596 | 137299677 |
| chr9 | 137633897 | 137534316 | chr9 | 137656864 | 137657223 | chr9 | 137667253 | 137667432 |
| chr9 | 137718802 | 137719101 | chr9 | 137721999 | 137722197 | chr9 | 137979803 | 137980102 |
| chr9 | 137980184 | 137980363 | chr9 | 137980806 | 137980985 | chr9 | 138265038 | 138265337 |
| chr9 | 138562961 | 138563377 | chr9 | 138606221 | 138606460 | chr9 | 138606711 | 138606850 |
| chr9 | 138606927 | 138607010 | chr9 | 138627556 | 138627925 | chr9 | 138633954 | 138634253 |
| chr9 | 138659704 | 138660003 | chr9 | 138660859 | 138661098 | chr9 | 138661550 | 138661969 |
| chr9 | 138666358 | 138666657 | chr9 | 138880882 | 138880973 | chr9 | 138991833 | 138991903 |
| chr9 | 139000485 | 139000724 | chr9 | 139012193 | 139012492 | chr9 | 139024634 | 139024873 |
| chr9 | 139045579 | 139045758 | chr9 | 139047494 | 139047733 | chr9 | 139085145 | 139085444 |
| chr9 | 139085832 | 139086071 | chr9 | 139090420 | 139090659 | chr9 | 139090692 | 139091471 |
| chr9 | 139093607 | 139093966 | chr9 | 139094610 | 139094969 | chr9 | 139095264 | 139095563 |
| chr9 | 139096559 | 139097098 | chr9 | 139111194 | 139111373 | chr9 | 139268961 | 139268987 |
| chr9 | 139421881 | 139422060 | chr9 | 139698839 | 139699138 | chr9 | 139704085 | 139704384 |
| chr9 | 139739149 | 139739388 | chr9 | 139858946 | 139859365 | chr9 | 139888844 | 139889083 |
| chr9 | 140024754 | 140025113 | chr9 | 140030424 | 140030603 | chr9 | 140032802 | 140033050 |
| chr9 | 140033192 | 140033197 | chr9 | 140033325 | 140033744 | chr9 | 140033815 | 140034174 |
| chr9 | 140050893 | 140051432 | chr9 | 140127803 | 140128162 | chr9 | 140137220 | 140137334 |
| chr9 | 140205346 | 140205607 | chr9 | 140245789 | 140246084 | chr9 | 140332624 | 140333103 |
| chr9 | 140382472 | 140382697 | chr9 | 140392380 | 140392559 | chr9 | 140396944 | 140397183 |
| chr9 | 140507207 | 140507506 | chr9 | 140708961 | 140709260 | chr9 | 140727429 | 140727611 |
| chr9 | 140727769 | 140728008 | chr9 | 140769913 | 140770048 | chr9 | 140771969 | 140772431 |

TABLE 14-continued

| chr | start | end | chr | start | end | chr | start | end |
|---|---|---|---|---|---|---|---|---|
| chr9 | 140772495 | 140773394 | chr10 | 524680 | 524770 | chr10 | 833228 | 833419 |
| chr10 | 978787 | 979026 | chr10 | 1585208 | 1585325 | chr10 | 1708551 | 1708583 |
| chr10 | 1779342 | 1779821 | chr10 | 3285686 | 3285792 | chr10 | 3330410 | 3330696 |
| chr10 | 3641277 | 3641396 | chr10 | 3678618 | 3678737 | chr10 | 3895312 | 3895551 |
| chr10 | 4599822 | 4600061 | chr10 | 5530673 | 5531080 | chr10 | 5875059 | 5875345 |
| chr10 | 6003386 | 6003625 | chr10 | 6042233 | 6042592 | chr10 | 6162073 | 6162302 |
| chr10 | 6577569 | 6577748 | chr10 | 6984626 | 6984731 | chr10 | 7205641 | 7205880 |
| chr10 | 7212666 | 7213145 | chr10 | 7213532 | 7213610 | chr10 | 7215985 | 7216164 |
| chr10 | 7236109 | 7236348 | chr10 | 7255627 | 7255659 | chr10 | 7414447 | 7414686 |
| chr10 | 7424552 | 7424731 | chr10 | 7449863 | 7451482 | chr10 | 7452143 | 7452862 |
| chr10 | 7453233 | 7454012 | chr10 | 7708311 | 7708379 | chr10 | 7708700 | 7709090 |
| chr10 | 7709649 | 7709807 | chr10 | 8075843 | 8076071 | chr10 | 8076264 | 8076563 |
| chr10 | 8076730 | 8077449 | chr10 | 8077790 | 8078316 | chr10 | 8084961 | 8085800 |
| chr10 | 8085875 | 8086114 | chr10 | 8091818 | 8092099 | chr10 | 8093653 | 8094072 |
| chr10 | 8095515 | 8095774 | chr10 | 8095842 | 8095934 | chr10 | 8096086 | 8096265 |
| chr10 | 8096877 | 8097296 | chr10 | 8097387 | 8097626 | chr10 | 11059620 | 11060159 |
| chr10 | 11207079 | 11207378 | chr10 | 11700851 | 11701100 | chr10 | 13043287 | 13043526 |
| chr10 | 13141002 | 13141106 | chr10 | 13715462 | 13715485 | chr10 | 13933361 | 13934260 |
| chr10 | 14966052 | 14966291 | chr10 | 15140509 | 15140625 | chr10 | 15761213 | 15761752 |
| chr10 | 15762050 | 15762211 | chr10 | 16562009 | 16563988 | chr10 | 16564013 | 16564127 |
| chr10 | 17270131 | 17270529 | chr10 | 17270889 | 17271728 | chr10 | 17271835 | 17272313 |
| chr10 | 17272527 | 17272706 | chr10 | 17429082 | 17429244 | chr10 | 17429562 | 17429724 |
| chr10 | 17496115 | 17496834 | chr10 | 18429147 | 18429386 | chr10 | 18429552 | 18429851 |
| chr10 | 21462526 | 21462690 | chr10 | 21805128 | 21805367 | chr10 | 22047362 | 22047601 |
| chr10 | 22541563 | 22542342 | chr10 | 22623924 | 22626080 | chr10 | 22633902 | 22634672 |
| chr10 | 22764556 | 22765991 | chr10 | 23216786 | 23217025 | chr10 | 23460264 | 23460552 |
| chr10 | 23461129 | 23461848 | chr10 | 23461976 | 23462995 | chr10 | 23463075 | 23464154 |
| chr10 | 23479793 | 23481171 | chr10 | 23481239 | 23481598 | chr10 | 23481862 | 23482621 |
| chr10 | 23483744 | 23484703 | chr10 | 23486177 | 23486416 | chr10 | 23487651 | 23488070 |
| chr10 | 23488297 | 23489256 | chr10 | 23489335 | 23489514 | chr10 | 23982360 | 23982899 |
| chr10 | 23983102 | 23983341 | chr10 | 23983382 | 23983801 | chr10 | 23984008 | 23984307 |
| chr10 | 23984838 | 23985066 | chr10 | 24988575 | 24988641 | chr10 | 25464528 | 25464910 |
| chr10 | 25465320 | 25465619 | chr10 | 26055737 | 26055916 | chr10 | 26222916 | 26223513 |
| chr10 | 26223957 | 26224136 | chr10 | 26500528 | 26501007 | chr10 | 26501445 | 26501668 |
| chr10 | 26503593 | 26503832 | chr10 | 26504018 | 26504257 | chr10 | 26504410 | 26505309 |
| chr10 | 26505364 | 26505783 | chr10 | 26505961 | 26506260 | chr10 | 26506288 | 26507427 |
| chr10 | 26681025 | 26681204 | chr10 | 26727024 | 26727443 | chr10 | 26727509 | 26727928 |
| chr10 | 26746956 | 26747074 | chr10 | 26816913 | 26817032 | chr10 | 27547856 | 27548575 |
| chr10 | 27794394 | 27794512 | chr10 | 27846608 | 27846719 | chr10 | 28030790 | 28031029 |
| chr10 | 28032874 | 28033113 | chr10 | 28033327 | 28033566 | chr10 | 28033667 | 28034446 |
| chr10 | 28034489 | 28035388 | chr10 | 28035520 | 28035879 | chr10 | 28287286 | 28287481 |
| chr10 | 28287693 | 28288164 | chr10 | 28957989 | 28958226 | chr10 | 29010956 | 29011239 |
| chr10 | 30025881 | 30026180 | chr10 | 31073276 | 31073541 | chr10 | 31892822 | 31893181 |
| chr10 | 32499021 | 32499260 | chr10 | 33233249 | 33233457 | chr10 | 33624079 | 33624318 |
| chr10 | 33624407 | 33624550 | chr10 | 33624621 | 33624646 | chr10 | 35929070 | 35929609 |
| chr10 | 43249935 | 43250114 | chr10 | 43250317 | 43250976 | chr10 | 43428329 | 43428688 |
| chr10 | 43428903 | 43429202 | chr10 | 43429275 | 43429514 | chr10 | 43572591 | 43572830 |
| chr10 | 43600462 | 43600733 | chr10 | 43615462 | 43615639 | chr10 | 43697812 | 43698092 |
| chr10 | 43698199 | 43698231 | chr10 | 43858258 | 43858437 | chr10 | 44879847 | 44880326 |
| chr10 | 44880773 | 44881012 | chr10 | 49652880 | 49653179 | chr10 | 49731470 | 49731829 |
| chr10 | 49731980 | 49732579 | chr10 | 50323162 | 50323360 | chr10 | 50340179 | 50340224 |
| chr10 | 50507469 | 50507708 | chr10 | 50603884 | 50604243 | chr10 | 50604508 | 50604742 |
| chr10 | 50604967 | 50604979 | chr10 | 50605053 | 50605746 | chr10 | 50605931 | 50606530 |
| chr10 | 50816972 | 50817224 | chr10 | 50817778 | 50818017 | chr10 | 50818288 | 50818527 |
| chr10 | 50818724 | 50819203 | chr10 | 50821378 | 50821797 | chr10 | 50887557 | 50887916 |
| chr10 | 50976785 | 50977144 | chr10 | 54068449 | 54068688 | chr10 | 54072882 | 54073121 |
| chr10 | 54073191 | 54073370 | chr10 | 54074648 | 54074887 | chr10 | 57387344 | 57387883 |
| chr10 | 57388239 | 57388598 | chr10 | 57390195 | 57390734 | chr10 | 57391072 | 57391311 |
| chr10 | 60273033 | 60273392 | chr10 | 60935793 | 60936091 | chr10 | 60936449 | 60936808 |
| chr10 | 60936999 | 60937178 | chr10 | 63212244 | 63212783 | chr10 | 64575433 | 64575732 |
| chr10 | 64578189 | 64578626 | chr10 | 71327627 | 71327865 | chr10 | 71328678 | 71328917 |
| chr10 | 71328980 | 71329219 | chr10 | 71329462 | 71329633 | chr10 | 71331965 | 71332650 |
| chr10 | 71332686 | 71333105 | chr10 | 72015070 | 72015425 | chr10 | 72043557 | 72043976 |
| chr10 | 72200001 | 72200240 | chr10 | 72200251 | 72201390 | chr10 | 72973124 | 72973275 |
| chr10 | 73156273 | 73156465 | chr10 | 73156550 | 73156752 | chr10 | 73157768 | 73158049 |
| chr10 | 73847788 | 73848267 | chr10 | 75407495 | 75407782 | chr10 | 75488860 | 75488975 |
| chr10 | 77191147 | 77191446 | chr10 | 79396826 | 79397185 | chr10 | 81023964 | 81023989 |
| chr10 | 81664764 | 81665003 | chr10 | 82116994 | 82117283 | chr10 | 83634171 | 83634234 |
| chr10 | 83635441 | 83635620 | chr10 | 85954322 | 85954561 | chr10 | 88149273 | 88149692 |
| chr10 | 89692817 | 89692996 | chr10 | 89717584 | 89717763 | chr10 | 90966608 | 90966967 |
| chr10 | 90967587 | 90968126 | chr10 | 91294929 | 91295168 | chr10 | 91295449 | 91295808 |
| chr10 | 92617156 | 92617395 | chr10 | 93647139 | 93647378 | chr10 | 93647486 | 93647725 |
| chr10 | 94450582 | 94450805 | chr10 | 94451372 | 94451587 | chr10 | 94825999 | 94826160 |
| chr10 | 94828062 | 94828601 | chr10 | 94828633 | 94828932 | chr10 | 94834311 | 94835088 |
| chr10 | 96304116 | 96304200 | chr10 | 98129719 | 98130138 | chr10 | 99080176 | 99080535 |
| chr10 | 99080774 | 99081061 | chr10 | 99531116 | 99531535 | chr10 | 99789080 | 99789379 |
| chr10 | 99790171 | 99790410 | chr10 | 99790508 | 99790747 | chr10 | 99790845 | 99791258 |
| chr10 | 100991863 | 100991935 | chr10 | 100992056 | 100992535 | chr10 | 100992780 | 100992822 |

TABLE 14-continued

| chr | start | end | chr | start | end | chr | start | end |
|---|---|---|---|---|---|---|---|---|
| chr10 | 100993448 | 100994107 | chr10 | 100995956 | 100996315 | chr10 | 101088918 | 101089517 |
| chr10 | 101089817 | 101090296 | chr10 | 101280106 | 101280569 | chr10 | 101283382 | 101283577 |
| chr10 | 101290028 | 101291284 | chr10 | 101292254 | 101292998 | chr10 | 101293071 | 101293430 |
| chr10 | 101294662 | 101295681 | chr10 | 101295665 | 101296892 | chr10 | 101874886 | 101875222 |
| chr10 | 102322156 | 102322335 | chr10 | 102419230 | 102419769 | chr10 | 102430611 | 102430850 |
| chr10 | 102473775 | 102474014 | chr10 | 102483915 | 102484632 | chr10 | 102495416 | 102495717 |
| chr10 | 102497192 | 102497791 | chr10 | 102498178 | 102498537 | chr10 | 102501285 | 102501464 |
| chr10 | 102507408 | 102507707 | chr10 | 102508902 | 102509381 | chr10 | 102586425 | 102586904 |
| chr10 | 102589340 | 102589579 | chr10 | 102589702 | 102590001 | chr10 | 102590075 | 102590494 |
| chr10 | 102890843 | 102891682 | chr10 | 102891745 | 102892104 | chr10 | 102893528 | 102895366 |
| chr10 | 102899088 | 102899687 | chr10 | 102899712 | 102900671 | chr10 | 102906423 | 102906667 |
| chr10 | 102975518 | 102975937 | chr10 | 102976963 | 102977502 | chr10 | 102983062 | 102983841 |
| chr10 | 102984313 | 102984612 | chr10 | 102985689 | 102986048 | chr10 | 102986447 | 102987646 |
| chr10 | 102989555 | 102989734 | chr10 | 102996018 | 102996737 | chr10 | 102997249 | 102997488 |
| chr10 | 102998493 | 102998912 | chr10 | 103043872 | 103044471 | chr10 | 103535527 | 103535586 |
| chr10 | 103535634 | 103535886 | chr10 | 103536143 | 103536502 | chr10 | 103579718 | 103579794 |
| chr10 | 103930133 | 103930248 | chr10 | 104169995 | 104170834 | chr10 | 105036464 | 105036943 |
| chr10 | 105037138 | 105037917 | chr10 | 105127048 | 105127156 | chr10 | 105155378 | 105155563 |
| chr10 | 105413527 | 105413886 | chr10 | 106398556 | 106398975 | chr10 | 106399505 | 106400464 |
| chr10 | 106400869 | 106402428 | chr10 | 106402620 | 106402919 | chr10 | 108923951 | 108924190 |
| chr10 | 108924365 | 108924784 | chr10 | 110226162 | 110226401 | chr10 | 110671800 | 110672339 |
| chr10 | 111216709 | 111217008 | chr10 | 112403075 | 112403374 | chr10 | 112440312 | 112440483 |
| chr10 | 115804748 | 115805107 | chr10 | 116164146 | 116164445 | chr10 | 116331052 | 116331231 |
| chr10 | 116853773 | 116854012 | chr10 | 118030550 | 118030969 | chr10 | 118031206 | 118032645 |
| chr10 | 118032841 | 118033140 | chr10 | 118033261 | 118033620 | chr10 | 118034064 | 118034243 |
| chr10 | 118890893 | 118891192 | chr10 | 118891437 | 118891854 | chr10 | 118891938 | 118893360 |
| chr10 | 118893484 | 118894383 | chr10 | 118896538 | 118896897 | chr10 | 118897822 | 118898061 |
| chr10 | 118899199 | 118899378 | chr10 | 118899435 | 118900034 | chr10 | 118900063 | 118900602 |
| chr10 | 118922061 | 118922296 | chr10 | 118922632 | 118922900 | chr10 | 118922944 | 118922991 |
| chr10 | 118923050 | 118923349 | chr10 | 118924511 | 118924990 | chr10 | 118927012 | 118927371 |
| chr10 | 118928459 | 118928614 | chr10 | 119001460 | 119001403 | chr10 | 119001639 | |
| chr10 | 119292187 | 119292419 | chr10 | 119294258 | 119294557 | chr10 | 119294747 | 119295346 |
| chr10 | 119296628 | 119296867 | chr10 | 119297308 | 119297607 | chr10 | 119301278 | 119301757 |
| chr10 | 119302055 | 119302080 | chr10 | 119302859 | 119303278 | chr10 | 119304289 | 119304468 |
| chr10 | 119304794 | 119305213 | chr10 | 119306948 | 119307127 | chr10 | 119311793 | 119311830 |
| chr10 | 119311905 | 119311972 | chr10 | 119312673 | 119313272 | chr10 | 119806952 | 119807131 |
| chr10 | 120354169 | 120354348 | chr10 | 120355462 | 120355701 | chr10 | 120841455 | 120841563 |
| chr10 | 122216811 | 122217170 | chr10 | 122708479 | 122708773 | chr10 | 123357681 | 123357757 |
| chr10 | 123922546 | 123923565 | chr10 | 124893085 | 124893444 | chr10 | 124893551 | 124893850 |
| chr10 | 124893863 | 124894582 | chr10 | 124894787 | 124895026 | chr10 | 124895342 | 124896541 |
| chr10 | 124896768 | 124897007 | chr10 | 124897118 | 124897657 | chr10 | 124897958 | 124898056 |
| chr10 | 124898957 | 124899196 | chr10 | 124899651 | 124899890 | chr10 | 124901816 | 124903315 |
| chr10 | 124904841 | 124905200 | chr10 | 124905407 | 124905586 | chr10 | 124905834 | 124906186 |
| chr10 | 124907214 | 124907633 | chr10 | 124908017 | 124908196 | chr10 | 124908987 | 124909769 |
| chr10 | 124910287 | 124911126 | chr10 | 125425412 | 125425651 | chr10 | 125650778 | 125651437 |
| chr10 | 125851248 | 125851727 | chr10 | 125852203 | 125852622 | chr10 | 125852673 | 125853272 |
| chr10 | 126135847 | 126136146 | chr10 | 126136406 | 126136810 | chr10 | 126137145 | 126137503 |
| chr10 | 126198864 | 126199163 | chr10 | 126697829 | 126698125 | chr10 | 128076477 | 128076716 |
| chr10 | 128077188 | 128077367 | chr10 | 128993816 | 128994535 | chr10 | 128994636 | 128994995 |
| chr10 | 129534562 | 129535825 | chr10 | 129535986 | 129536405 | chr10 | 129888774 | 129888965 |
| chr10 | 129948037 | 129948216 | chr10 | 130085210 | 130085449 | chr10 | 130203339 | 130203578 |
| chr10 | 130338713 | 130339062 | chr10 | 130577690 | 130577869 | chr10 | 131647829 | 131648008 |
| chr10 | 131756992 | 131757531 | chr10 | 131757852 | 131758151 | chr10 | 131761291 | 131761530 |
| chr10 | 131761587 | 131761826 | chr10 | 131761987 | 131762226 | chr10 | 131762493 | 131762732 |
| chr10 | 131762803 | 131763042 | chr10 | 131763264 | 131763803 | chr10 | 131767343 | 131767522 |
| chr10 | 131768638 | 131769117 | chr10 | 131769436 | 131770335 | chr10 | 131770583 | 131770762 |
| chr10 | 131770908 | 131771327 | chr10 | 131936600 | 131936719 | chr10 | 131937393 | 131937512 |
| chr10 | 132001196 | 132001615 | chr10 | 133109096 | 133109395 | chr10 | 133109559 | 133109858 |
| chr10 | 133110260 | 133110799 | chr10 | 133794798 | 133795517 | chr10 | 133795593 | 133796312 |
| chr10 | 133849561 | 133850103 | chr10 | 133850443 | 133850862 | chr10 | 133951515 | 133952107 |
| chr10 | 133979076 | 133979164 | chr10 | 133999917 | 134000216 | chr10 | 134001000 | 134001359 |
| chr10 | 134016117 | 134016476 | chr10 | 134022771 | 134022950 | chr10 | 134095505 | 134095924 |
| chr10 | 134272961 | 134272970 | chr10 | 134301005 | 134301304 | chr10 | 134481228 | 134481527 |
| chr10 | 134598013 | 134598192 | chr10 | 134598254 | 134598613 | chr10 | 134598973 | 134599572 |
| chr10 | 134599714 | 134601053 | chr10 | 134601468 | 134601887 | chr10 | 134602107 | 134602346 |
| chr10 | 134607868 | 134608284 | chr10 | 134665056 | 134665295 | chr10 | 134679326 | 134679347 |
| chr10 | 134690469 | 134690636 | chr10 | 134693499 | 134693798 | chr10 | 134699772 | 134700011 |
| chr10 | 134733129 | 134733368 | chr10 | 134733408 | 134733707 | chr10 | 134738301 | 134738720 |
| chr10 | 134755743 | 134756270 | chr10 | 134787988 | 134788194 | chr10 | 134795938 | 134796117 |
| chr10 | 134901113 | 134901592 | chr10 | 134901919 | 134902352 | chr10 | 134916625 | 134916864 |
| chr10 | 134941043 | 134941282 | chr10 | 134942738 | 134943216 | chr10 | 134943461 | 134943644 |
| chr10 | 134944668 | 134944847 | chr10 | 135001961 | 135002260 | chr10 | 135014869 | 135015228 |
| chr10 | 135016972 | 135017209 | chr10 | 135017932 | 135018148 | chr10 | 135018744 | 135019043 |
| chr10 | 135020698 | 135020988 | chr10 | 135023396 | 135023575 | chr10 | 135043080 | 135043613 |
| chr10 | 135043869 | 135044228 | chr10 | 135044423 | 135044662 | chr10 | 135048742 | 135049041 |
| chr10 | 135050226 | 135050765 | chr10 | 135076308 | 135076586 | chr10 | 135121730 | 135122131 |
| chr10 | 135139464 | 135139805 | chr11 | 232816 | 233115 | chr11 | 392560 | 392739 |
| chr11 | 394713 | 395072 | chr11 | 406789 | 407028 | chr11 | 407326 | 407565 |

TABLE 14-continued

| chr | start | end | chr | start | end | chr | start | end |
|---|---|---|---|---|---|---|---|---|
| chr11 | 626983 | 627282 | chr11 | 636821 | 637000 | chr11 | 537100 | 637528 |
| chr11 | 726323 | 726562 | chr11 | 763236 | 753775 | chr11 | 829453 | 829806 |
| chr11 | 830071 | 830370 | chr11 | 850480 | 850899 | chr11 | 862988 | 863167 |
| chr11 | 1027438 | 1027676 | chr11 | 1029142 | 1029501 | chr11 | 1030137 | 1030376 |
| chr11 | 1080304 | 1080416 | chr11 | 1081572 | 1081811 | chr11 | 1214582 | 1215001 |
| chr11 | 1215800 | 1216099 | chr11 | 1229871 | 1230050 | chr11 | 1244304 | 1244543 |
| chr11 | 1250788 | 1251027 | chr11 | 1251088 | 1251447 | chr11 | 1263504 | 1263743 |
| chr11 | 1273988 | 1274287 | chr11 | 1358284 | 1358432 | chr11 | 1374862 | 1375101 |
| chr11 | 1411801 | 1411980 | chr11 | 1430635 | 1430874 | chr11 | 1464205 | 1464504 |
| chr11 | 1469125 | 1469484 | chr11 | 1471840 | 1472139 | chr11 | 1769971 | 1770330 |
| chr11 | 1867980 | 1868339 | chr11 | 1946056 | 1946235 | chr11 | 1957312 | 1957611 |
| chr11 | 1958983 | 1959282 | chr11 | 2040009 | 2040248 | chr11 | 2209824 | 2210363 |
| chr11 | 2225974 | 2226153 | chr11 | 2278625 | 2278924 | chr11 | 2291185 | 2291844 |
| chr11 | 2291891 | 2292730 | chr11 | 2437889 | 2438246 | chr11 | 2465323 | 2465571 |
| chr11 | 2466514 | 2466873 | chr11 | 2884027 | 2884121 | chr11 | 2884158 | 2884386 |
| chr11 | 3169689 | 3169930 | chr11 | 4209031 | 4209210 | chr11 | 7273212 | 7273451 |
| chr11 | 7274141 | 7274320 | chr11 | 8040444 | 8040863 | chr11 | 8102910 | 8103209 |
| chr11 | 8189898 | 8190857 | chr11 | 8284465 | 8284858 | chr11 | 8289436 | 8289841 |
| chr11 | 8290100 | 8290515 | chr11 | 8615600 | 8616779 | chr11 | 9025890 | 9026429 |
| chr11 | 9112372 | 9112834 | chr11 | 9405310 | 9405542 | chr11 | 10509594 | 10509893 |
| chr11 | 10811069 | 10811188 | chr11 | 10815784 | 10815896 | chr11 | 12029876 | 12030355 |
| chr11 | 12030749 | 12030928 | chr11 | 12132423 | 12132662 | chr11 | 12398952 | 12399145 |
| chr11 | 12399181 | 12399311 | chr11 | 12695397 | 12695696 | chr11 | 12696530 | 12696764 |
| chr11 | 13030489 | 13030792 | chr11 | 13030862 | 13030968 | chr11 | 15136001 | 15136480 |
| chr11 | 16628727 | 16628998 | chr11 | 16632403 | 16632752 | chr11 | 17497410 | 17497769 |
| chr11 | 17740413 | 17740652 | chr11 | 17741583 | 17741685 | chr11 | 17741718 | 17742542 |
| chr11 | 17743640 | 17743874 | chr11 | 18812515 | 18812754 | chr11 | 18812940 | 18813179 |
| chr11 | 18813356 | 18813655 | chr11 | 18813691 | 18814050 | chr11 | 19263774 | 19263953 |
| chr11 | 19367007 | 19367426 | chr11 | 19735656 | 19735835 | chr11 | 20153622 | 20153861 |
| chr11 | 20177977 | 20178396 | chr11 | 20180244 | 20180896 | chr11 | 20181115 | 20181354 |
| chr11 | 20181608 | 20182087 | chr11 | 20182763 | 20183062 | chr11 | 20183157 | 20183211 |
| chr11 | 20183313 | 20183516 | chr11 | 20183575 | 20183852 | chr11 | 20184481 | 20185500 |
| chr11 | 20229275 | 20229634 | chr11 | 20229811 | 20230110 | chr11 | 20230312 | 20230551 |
| chr11 | 20618116 | 20619255 | chr11 | 20619637 | 20620056 | chr11 | 20621460 | 20621733 |
| chr11 | 20622613 | 20623452 | chr11 | 20690555 | 20691034 | chr11 | 20691127 | 20691546 |
| chr11 | 20691591 | 20692010 | chr11 | 20692372 | 20692611 | chr11 | 22215026 | 22215385 |
| chr11 | 22362853 | 22363272 | chr11 | 22364719 | 22365078 | chr11 | 22365323 | 22365562 |
| chr11 | 27742111 | 27742290 | chr11 | 27743025 | 27743261 | chr11 | 27743343 | 27743702 |
| chr11 | 27744057 | 27744596 | chr11 | 27744609 | 27744832 | chr11 | 30037596 | 30037818 |
| chr11 | 30038595 | 30038834 | chr11 | 30605946 | 30606201 | chr11 | 30606665 | 30606964 |
| chr11 | 30607269 | 30607508 | chr11 | 31818376 | 31818674 | chr11 | 31819221 | 31819508 |
| chr11 | 31819569 | 31819928 | chr11 | 31819966 | 31821105 | chr11 | 31821209 | 31821860 |
| chr11 | 31822240 | 31822479 | chr11 | 31824209 | 31824448 | chr11 | 31824473 | 31824772 |
| chr11 | 31824940 | 31825359 | chr11 | 31825611 | 31827290 | chr11 | 31827362 | 31828142 |
| chr11 | 31833007 | 31833232 | chr11 | 31835633 | 31835872 | chr11 | 31835959 | 31836517 |
| chr11 | 31836927 | 31838486 | chr11 | 31838596 | 31839135 | chr11 | 31839215 | 31840174 |
| chr11 | 31840486 | 31841025 | chr11 | 31841287 | 31842366 | chr11 | 31845947 | 31845991 |
| chr11 | 31846078 | 31846306 | chr11 | 31846351 | 31847070 | chr11 | 31847169 | 31848008 |
| chr11 | 31848377 | 31849177 | chr11 | 32009013 | 32009252 | chr11 | 32354816 | 32355291 |
| chr11 | 32448482 | 32449081 | chr11 | 32455499 | 32455738 | chr11 | 32455754 | 32456113 |
| chr11 | 32456189 | 32457268 | chr11 | 32457615 | 32458274 | chr11 | 32458307 | 32458860 |
| chr11 | 32459269 | 32459971 | chr11 | 32460118 | 32460148 | chr11 | 32460373 | 32460612 |
| chr11 | 32460711 | 32460950 | chr11 | 33037393 | 33037632 | chr11 | 33858439 | 33858544 |
| chr11 | 33890197 | 33890436 | chr11 | 33993910 | 33993979 | chr11 | 34535019 | 34535198 |
| chr11 | 35547412 | 35547651 | chr11 | 35641582 | 35641718 | chr11 | 35684866 | 35685225 |
| chr11 | 43596412 | 43596693 | chr11 | 43600416 | 43600655 | chr11 | 43601012 | 43601551 |
| chr11 | 43602369 | 43603328 | chr11 | 43603544 | 43604263 | chr11 | 44325599 | 44325838 |
| chr11 | 44326042 | 44326281 | chr11 | 44326341 | 44326580 | chr11 | 44330555 | 44331814 |
| chr11 | 44332978 | 44333157 | chr11 | 44333466 | 44333576 | chr11 | 44337564 | 44338154 |
| chr11 | 44338232 | 44338471 | chr11 | 44340722 | 44340808 | chr11 | 44341881 | 44342120 |
| chr11 | 46316761 | 46317780 | chr11 | 47208968 | 47209267 | chr11 | 47358895 | 47359314 |
| chr11 | 57194253 | 57194612 | chr11 | 57235332 | 57235511 | chr11 | 57437215 | 57437316 |
| chr11 | 57501032 | 57501145 | chr11 | 58672666 | 58673145 | chr11 | 59323514 | 59323551 |
| chr11 | 59323780 | 59323813 | chr11 | 59329224 | 59329343 | chr11 | 59333344 | 59333623 |
| chr11 | 60718587 | 60719246 | chr11 | 61049596 | 61049756 | chr11 | 61058193 | 61058432 |
| chr11 | 61062741 | 61063220 | chr11 | 61276902 | 61277321 | chr11 | 61594995 | 61595354 |
| chr11 | 61596321 | 61596740 | chr11 | 61664564 | 61664863 | chr11 | 61666032 | 61666211 |
| chr11 | 61722964 | 61723262 | chr11 | 62370646 | 62370825 | chr11 | 62440550 | 62440669 |
| chr11 | 63609981 | 63610099 | chr11 | 63641023 | 63641104 | chr11 | 63767909 | 63768208 |
| chr11 | 63849298 | 63849530 | chr11 | 63934600 | 63934709 | chr11 | 64105852 | 64106031 |
| chr11 | 64120805 | 64120984 | chr11 | 64140323 | 64140502 | chr11 | 64410622 | 64410861 |
| chr11 | 64480332 | 64480691 | chr11 | 64480724 | 64481143 | chr11 | 54578481 | 64578600 |
| chr11 | 64739369 | 64739608 | chr11 | 64809866 | 64809965 | chr11 | 54950214 | 64950438 |
| chr11 | 65091311 | 65091471 | chr11 | 55185459 | 65185818 | chr11 | 65405568 | 65405597 |
| chr11 | 65478529 | 65478644 | chr11 | 65511077 | 65511256 | chr11 | 65511332 | 65511571 |
| chr11 | 65553957 | 65554195 | chr11 | 65600716 | 65601735 | chr11 | 65779218 | 65779457 |
| chr11 | 65816357 | 65816656 | chr11 | 66188041 | 66188220 | chr11 | 66188395 | 66189054 |
| chr11 | 66454350 | 66454529 | chr11 | 66511148 | 66511327 | chr11 | 66513133 | 66513252 |

TABLE 14-continued

| chr | start | end | chr | start | end | chr | start | end |
|---|---|---|---|---|---|---|---|---|
| chr11 | 66513554 | 66513732 | chr11 | 66625105 | 66625344 | chr11 | 66648954 | 66649133 |
| chr11 | 66658258 | 66658365 | chr11 | 66790519 | 66790758 | chr11 | 67072139 | 67072489 |
| chr11 | 67209918 | 67210157 | chr11 | 67350887 | 67351066 | chr11 | 67462559 | 67462918 |
| chr11 | 67764102 | 67764341 | chr11 | 67781387 | 67781650 | chr11 | 67797102 | 67797281 |
| chr11 | 68096026 | 68096257 | chr11 | 68409507 | 68409663 | chr11 | 68804647 | 68804872 |
| chr11 | 69192466 | 69192885 | chr11 | 69280478 | 69280717 | chr11 | 69465962 | 69466143 |
| chr11 | 69516896 | 69517251 | chr11 | 69517942 | 69518301 | chr11 | 69518445 | 69518708 |
| chr11 | 69588848 | 69589267 | chr11 | 69589750 | 69589929 | chr11 | 69590067 | 69590306 |
| chr11 | 71192669 | 71192921 | chr11 | 71318231 | 71319070 | chr11 | 71951540 | 71951815 |
| chr11 | 71952262 | 71952621 | chr11 | 71954538 | 71954717 | chr11 | 71955242 | 71955481 |
| chr11 | 71955905 | 71956444 | chr11 | 72432759 | 72432997 | chr11 | 72475781 | 72475814 |
| chr11 | 72532274 | 72532453 | chr11 | 72929666 | 72929731 | chr11 | 73072871 | 73073050 |
| chr11 | 73310285 | 73310445 | chr11 | 74394397 | 74394696 | chr11 | 74953165 | 74953524 |
| chr11 | 75379155 | 75379994 | chr11 | 75459452 | 75459564 | chr11 | 76371639 | 76372178 |
| chr11 | 78672822 | 78673061 | chr11 | 79151076 | 79151315 | chr11 | 82444290 | 82445189 |
| chr11 | 86085657 | 86086065 | chr11 | 86383080 | 86383186 | chr11 | 88241623 | 88242702 |
| chr11 | 88798997 | 88799296 | chr11 | 91957408 | 91957767 | chr11 | 91957893 | 91958312 |
| chr11 | 91958633 | 91959532 | chr11 | 91959901 | 91960122 | chr11 | 93063495 | 93063734 |
| chr11 | 93063790 | 93064029 | chr11 | 94133991 | 94134690 | chr11 | 94275701 | 94275813 |
| chr11 | 94473511 | 94473997 | chr11 | 94474399 | 94474401 | chr11 | 94502273 | 94502592 |
| chr11 | 94884070 | 94884235 | chr11 | 98891381 | 98891980 | chr11 | 100997579 | 100998085 |
| chr11 | 100998178 | 100998417 | chr11 | 100998588 | 100998827 | chr11 | 101453080 | 101453619 |
| chr11 | 101454101 | 101454580 | chr11 | 102961259 | 102961378 | chr11 | 102979953 | 102980132 |
| chr11 | 104034430 | 104035089 | chr11 | 105480662 | 105480901 | chr11 | 106481125 | 105481604 |
| chr11 | 106888220 | 106888519 | chr11 | 106888542 | 106888901 | chr11 | 107461549 | 107461728 |
| chr11 | 107462318 | 107462557 | chr11 | 108603286 | 108603338 | chr11 | 109292830 | 109293129 |
| chr11 | 109293635 | 109293934 | chr11 | 110582154 | 110582513 | chr11 | 110582794 | 110583153 |
| chr11 | 110583473 | 110583832 | chr11 | 111383104 | 111383763 | chr11 | 111411019 | 111412147 |
| chr11 | 114112948 | 114113127 | chr11 | 115375030 | 115375269 | chr11 | 115530040 | 115530662 |
| chr11 | 115630414 | 115631013 | chr11 | 115631217 | 115631456 | chr11 | 116451226 | 116451287 |
| chr11 | 119292739 | 119292884 | chr11 | 119293284 | 119293703 | chr11 | 119612134 | 119612493 |
| chr11 | 119612999 | 119613178 | chr11 | 120008006 | 120008605 | chr11 | 120039730 | 120039969 |
| chr11 | 120435322 | 120435561 | chr11 | 120435726 | 120435905 | chr11 | 120998614 | 120998913 |
| chr11 | 122847182 | 122847781 | chr11 | 122847976 | 122848695 | chr11 | 122849808 | 122850263 |
| chr11 | 122850331 | 122850630 | chr11 | 122851074 | 122851313 | chr11 | 122852338 | 122862577 |
| chr11 | 122854907 | 122855136 | chr11 | 123066359 | 123066538 | chr11 | 123228971 | 123229510 |
| chr11 | 123300736 | 123300955 | chr11 | 123301016 | 123302115 | chr11 | 124735341 | 124735580 |
| chr11 | 124736105 | 124736344 | chr11 | 124738694 | 124739125 | chr11 | 124739149 | 124739173 |
| chr11 | 125035687 | 125036286 | chr11 | 125036503 | 125036742 | chr11 | 125220423 | 125220722 |
| chr11 | 125755512 | 125755727 | chr11 | 125773587 | 125774186 | chr11 | 126870108 | 126870287 |
| chr11 | 126870379 | 126870618 | chr11 | 126873304 | 126873603 | chr11 | 128562802 | 128563818 |
| chr11 | 128563879 | 128564405 | chr11 | 128564641 | 128565480 | chr11 | 128657933 | 128658051 |
| chr11 | 129242783 | 129243643 | chr11 | 129243944 | 129244646 | chr11 | 129245747 | 129245892 |
| chr11 | 129245981 | 129246046 | chr11 | 130318860 | 130319099 | chr11 | 130319451 | 130319690 |
| chr11 | 130785406 | 130785705 | chr11 | 131522676 | 131522960 | chr11 | 131564873 | 131565101 |
| chr11 | 131766899 | 131767048 | chr11 | 131780391 | 131781350 | chr11 | 132484279 | 132484490 |
| chr11 | 132813545 | 132814049 | chr11 | 132864036 | 132864275 | chr11 | 132934031 | 132934270 |
| chr11 | 132952677 | 132953003 | chr11 | 132953064 | 132953423 | chr11 | 133231637 | 133231930 |
| chr11 | 133402114 | 133402353 | chr11 | 133825146 | 133825625 | chr11 | 133906702 | 133907001 |
| chr11 | 133938911 | 133939270 | chr11 | 134145629 | 134146468 | chr11 | 134146579 | 134146998 |
| chr11 | 134201404 | 134201640 | chr11 | 134201754 | 134202173 | chr11 | 134281288 | 134281543 |
| chr12 | 570012 | 570251 | chr12 | 1639060 | 1639299 | chr12 | 2162477 | 2162896 |
| chr12 | 2163071 | 2163370 | chr12 | 2403649 | 2403806 | chr12 | 2565971 | 2566330 |
| chr12 | 2861968 | 2862327 | chr12 | 2964372 | 2964671 | chr12 | 3600241 | 3600420 |
| chr12 | 3602186 | 3602965 | chr12 | 3603009 | 3603061 | chr12 | 4214010 | 4214245 |
| chr12 | 4273972 | 4274490 | chr12 | 4362362 | 4362541 | chr12 | 4378172 | 4378411 |
| chr12 | 4379275 | 4379574 | chr12 | 4381341 | 4382480 | chr12 | 4382863 | 4383102 |
| chr12 | 4383399 | 4383878 | chr12 | 4384315 | 4384494 | chr12 | 4392801 | 4393023 |
| chr12 | 4405515 | 4405694 | chr12 | 4554727 | 4554906 | chr12 | 5017994 | 5018773 |
| chr12 | 5018954 | 5020513 | chr12 | 5152951 | 5153610 | chr12 | 5541020 | 5541259 |
| chr12 | 5542233 | 5542532 | chr12 | 5542656 | 5543015 | chr12 | 5840126 | 5840305 |
| chr12 | 6483537 | 6483836 | chr12 | 6664407 | 6665486 | chr12 | 7559085 | 7559384 |
| chr12 | 8127119 | 8127238 | chr12 | 8171284 | 8171823 | chr12 | 8808505 | 8808640 |
| chr12 | 8850582 | 8850818 | chr12 | 8975096 | 8975452 | chr12 | 10085826 | 10085932 |
| chr12 | 10363204 | 10363319 | chr12 | 11653375 | 11653554 | chr12 | 12848294 | 12848653 |
| chr12 | 14133059 | 14133358 | chr12 | 14133541 | 14133960 | chr12 | 14135016 | 14135354 |
| chr12 | 15374156 | 15374395 | chr12 | 16500480 | 16500685 | chr12 | 20521624 | 20521923 |
| chr12 | 20522383 | 20522562 | chr12 | 20522681 | 20522860 | chr12 | 20522976 | 20522980 |
| chr12 | 21680300 | 21680779 | chr12 | 21810395 | 21810956 | chr12 | 21832988 | 21833095 |
| chr12 | 22093749 | 22094888 | chr12 | 22094997 | 22095236 | chr12 | 22486717 | 22487556 |
| chr12 | 22698102 | 22698207 | chr12 | 24714835 | 24716014 | chr12 | 24715161 | 24715340 |
| chr12 | 24715947 | 24716306 | chr12 | 25055865 | 25056524 | chr12 | 25101507 | 25101746 |
| chr12 | 25101824 | 25102183 | chr12 | 25380366 | 25380366 | chr12 | 25398165 | 25398404 |
| chr12 | 28127676 | 28128395 | chr12 | 28128457 | 28129176 | chr12 | 29935913 | 29936152 |
| chr12 | 29936524 | 29936777 | chr12 | 29936792 | 29936943 | chr12 | 29937234 | 29937473 |
| chr12 | 30322697 | 30323596 | chr12 | 30975472 | 30976015 | chr12 | 31079179 | 31079594 |
| chr12 | 32340225 | 32340336 | chr12 | 33591700 | 33591879 | chr12 | 33592512 | 33592991 |
| chr12 | 34494814 | 34494993 | chr12 | 34502649 | 34502888 | chr12 | 39299040 | 39299185 |

TABLE 14-continued

| chr | start | end | chr | start | end | chr | start | end |
|---|---|---|---|---|---|---|---|---|
| chr12 | 39299269 | 39299639 | chr12 | 39539276 | 39539515 | chr12 | 40618318 | 40618557 |
| chr12 | 41086102 | 41086461 | chr12 | 41086706 | 41087185 | chr12 | 41582422 | 41583081 |
| chr12 | 41583278 | 41583471 | chr12 | 43944800 | 43945219 | chr12 | 43945262 | 43945621 |
| chr12 | 43945742 | 43946401 | chr12 | 45269415 | 45269714 | chr12 | 45444029 | 45444920 |
| chr12 | 45445062 | 45445348 | chr12 | 46767555 | 46767558 | chr12 | 47225301 | 47225660 |
| chr12 | 47629275 | 47629307 | chr12 | 47629398 | 47629454 | chr12 | 48397154 | 48398173 |
| chr12 | 48398567 | 48398746 | chr12 | 49297770 | 49298009 | chr12 | 49366280 | 49366519 |
| chr12 | 49374838 | 49375197 | chr12 | 49375248 | 49375607 | chr12 | 49390776 | 49391975 |
| chr12 | 49657624 | 49657722 | chr12 | 49690975 | 49691154 | chr12 | 49726969 | 49727208 |
| chr12 | 49729640 | 49730179 | chr12 | 50297417 | 50298136 | chr12 | 50355193 | 50355552 |
| chr12 | 50426672 | 50426894 | chr12 | 51421134 | 51421373 | chr12 | 51421482 | 51421661 |
| chr12 | 51565470 | 51565562 | chr12 | 51930615 | 51930785 | chr12 | 52262896 | 52263195 |
| chr12 | 52301205 | 52301444 | chr12 | 52400735 | 52401616 | chr12 | 52627102 | 52627381 |
| chr12 | 52652054 | 52652713 | chr12 | 53108005 | 53108304 | chr12 | 53359245 | 53359664 |
| chr12 | 54089004 | 54089602 | chr12 | 54132172 | 54132411 | chr12 | 54145750 | 54145989 |
| chr12 | 54321170 | 54321709 | chr12 | 54322108 | 54322302 | chr12 | 54324719 | 54325018 |
| chr12 | 54329264 | 54330007 | chr12 | 54330980 | 54331219 | chr12 | 54332774 | 54333433 |
| chr12 | 54338589 | 54339668 | chr12 | 54343718 | 54343955 | chr12 | 54345523 | 54346122 |
| chr12 | 54348761 | 54349420 | chr12 | 54354419 | 54354718 | chr12 | 54354805 | 54355575 |
| chr12 | 54359873 | 54360172 | chr12 | 54360510 | 54360729 | chr12 | 54377835 | 54378194 |
| chr12 | 54379100 | 54379699 | chr12 | 54379785 | 54380486 | chr12 | 54387752 | 54388051 |
| chr12 | 54388141 | 54388320 | chr12 | 54391267 | 54391506 | chr12 | 54393403 | 54393762 |
| chr12 | 54393847 | 54394266 | chr12 | 54394307 | 54394546 | chr12 | 54398697 | 54399056 |
| chr12 | 54399542 | 54399721 | chr12 | 54402654 | 54402812 | chr12 | 54402975 | 54403454 |
| chr12 | 54408330 | 54408809 | chr12 | 54424670 | 54424887 | chr12 | 54424912 | 54425211 |
| chr12 | 54447340 | 54447519 | chr12 | 54447781 | 54448080 | chr12 | 54520658 | 54520957 |
| chr12 | 54720221 | 54720320 | chr12 | 54812150 | 54812449 | chr12 | 54942906 | 54943191 |
| chr12 | 56882365 | 56882460 | chr12 | 57559778 | 57559914 | chr12 | 57618478 | 57619077 |
| chr12 | 57881046 | 57881345 | chr12 | 57943980 | 57944219 | chr12 | 58021218 | 58021817 |
| chr12 | 58021824 | 58022093 | chr12 | 58025551 | 58025970 | chr12 | 62584739 | 62586118 |
| chr12 | 62586178 | 62586357 | chr12 | 63026615 | 63026257 | chr12 | 63643749 | 63544828 |
| chr12 | 63545239 | 63545418 | chr12 | 64061721 | 64062260 | chr12 | 64062295 | 64062654 |
| chr12 | 64062830 | 64063189 | chr12 | 64783098 | 64783322 | chr12 | 64784007 | 64784352 |
| chr12 | 64784460 | 64784639 | chr12 | 65218000 | 65219259 | chr12 | 65219281 | 65219880 |
| chr12 | 65220129 | 65220428 | chr12 | 65514781 | 65515620 | chr12 | 65516379 | 65516558 |
| chr12 | 65557115 | 65557234 | chr12 | 65562064 | 65562172 | chr12 | 66122711 | 66123610 |
| chr12 | 66135910 | 66136089 | chr12 | 66582743 | 66583222 | chr12 | 69327182 | 69327541 |
| chr12 | 69754351 | 69754470 | chr12 | 69754600 | 69754710 | chr12 | 69964101 | 69964340 |
| chr12 | 70087412 | 70087651 | chr12 | 72332550 | 72332789 | chr12 | 72665167 | 72665526 |
| chr12 | 72665566 | 72665877 | chr12 | 72666014 | 72666313 | chr12 | 72666620 | 72667519 |
| chr12 | 72667578 | 72667757 | chr12 | 75601168 | 75602007 | chr12 | 75602895 | 75603314 |
| chr12 | 75728262 | 75728561 | chr12 | 77719218 | 77719517 | chr12 | 79257138 | 79257437 |
| chr12 | 79258850 | 79259029 | chr12 | 81102105 | 81102603 | chr12 | 81107921 | 81108100 |
| chr12 | 81471425 | 81472204 | chr12 | 85306430 | 85306549 | chr12 | 85667173 | 85667832 |
| chr12 | 85673132 | 85673311 | chr12 | 85673385 | 85674884 | chr12 | 88974346 | 88974356 |
| chr12 | 93966337 | 93966696 | chr12 | 93966910 | 93967329 | chr12 | 94543308 | 94543547 |
| chr12 | 94543811 | 94544080 | chr12 | 95267450 | 95267629 | chr12 | 95267772 | 95268000 |
| chr12 | 95941794 | 95943053 | chr12 | 99288212 | 99289401 | chr12 | 101025306 | 101025485 |
| chr12 | 101110926 | 101111165 | chr12 | 101111277 | 101111576 | chr12 | 103218396 | 103218655 |
| chr12 | 103350250 | 103350429 | chr12 | 103351464 | 103352783 | chr12 | 103358763 | 103359002 |
| chr12 | 103359482 | 103359661 | chr12 | 103889086 | 103889306 | chr12 | 103889660 | 103889899 |
| chr12 | 104609340 | 104610179 | chr12 | 104850430 | 104850669 | chr12 | 104850983 | 104851282 |
| chr12 | 104851941 | 104852600 | chr12 | 105478222 | 105478457 | chr12 | 106974279 | 106974458 |
| chr12 | 106976641 | 106976880 | chr12 | 106977394 | 106977589 | chr12 | 106979079 | 106979618 |
| chr12 | 106979718 | 106980077 | chr12 | 106980129 | 106980428 | chr12 | 106980771 | 106981490 |
| chr12 | 107486462 | 107486673 | chr12 | 107487114 | 107487945 | chr12 | 107712199 | 107712378 |
| chr12 | 107713131 | 107713310 | chr12 | 107714771 | 107715250 | chr12 | 108168883 | 108169662 |
| chr12 | 108237377 | 108237676 | chr12 | 108238034 | 108238719 | chr12 | 108297320 | 108297559 |
| chr12 | 110353315 | 110353553 | chr12 | 110717447 | 110717806 | chr12 | 111127079 | 111127438 |
| chr12 | 111471099 | 111471638 | chr12 | 111471871 | 111472511 | chr12 | 111472572 | 111472830 |
| chr12 | 111763136 | 111763227 | chr12 | 113012877 | 113013236 | chr12 | 113541644 | 113542183 |
| chr12 | 113592150 | 113592449 | chr12 | 113900616 | 113900855 | chr12 | 113900974 | 113901693 |
| chr12 | 113901951 | 113902429 | chr12 | 113903394 | 113903573 | chr12 | 113904689 | 113905108 |
| chr12 | 113908894 | 113909553 | chr12 | 113909569 | 113909808 | chr12 | 113913180 | 113914139 |
| chr12 | 113916147 | 113916266 | chr12 | 113916327 | 113916419 | chr12 | 113916575 | 113916754 |
| chr12 | 113916873 | 113917112 | chr12 | 113917212 | 113917391 | chr12 | 113917684 | 113917983 |
| chr12 | 114029325 | 114029509 | chr12 | 114029546 | 114029744 | chr12 | 114075942 | 114076177 |
| chr12 | 114337849 | 114337868 | chr12 | 114833895 | 114834194 | chr12 | 114838227 | 114838826 |
| chr12 | 114840946 | 114841185 | chr12 | 114843016 | 114843375 | chr12 | 114843454 | 114843753 |
| chr12 | 114844102 | 114844401 | chr12 | 114846623 | 114846862 | chr12 | 114846886 | 114847741 |
| chr12 | 114851969 | 114852181 | chr12 | 114852214 | 114852268 | chr12 | 114877068 | 114877367 |
| chr12 | 114878448 | 114878687 | chr12 | 114878734 | 114879093 | chr12 | 114881550 | 114881849 |
| chr12 | 114882488 | 114882727 | chr12 | 114883385 | 114883554 | chr12 | 114885134 | 114885373 |
| chr12 | 114918513 | 114918806 | chr12 | 115136153 | 115136441 | chr12 | 116945988 | 116946647 |
| chr12 | 117473983 | 117474282 | chr12 | 117797999 | 117798170 | chr12 | 117798589 | 117799068 |
| chr12 | 117799322 | 117799621 | chr12 | 118860317 | 118860436 | chr12 | 119212120 | 119212479 |
| chr12 | 119418512 | 119418931 | chr12 | 119419362 | 119419541 | chr12 | 119419631 | 119419920 |
| chr12 | 120032777 | 120033256 | chr12 | 120148125 | 120148345 | chr12 | 120148824 | 120149063 |

TABLE 14-continued

| chr | start | end | chr | start | end | chr | start | end |
|---|---|---|---|---|---|---|---|---|
| chr12 | 120885155 | 120885274 | chr12 | 121622422 | 121622591 | chr12 | 122192885 | 122192933 |
| chr12 | 122284969 | 122285189 | chr12 | 123129041 | 123129139 | chr12 | 123233818 | 123233926 |
| chr12 | 124393463 | 124393702 | chr12 | 124397514 | 124397693 | chr12 | 125009254 | 125009381 |
| chr12 | 125533851 | 125534508 | chr12 | 125670024 | 125670383 | chr12 | 126168468 | 126168707 |
| chr12 | 127210933 | 127211472 | chr12 | 127765066 | 127765535 | chr12 | 127939988 | 127940189 |
| chr12 | 127940271 | 127940347 | chr12 | 128751295 | 128751534 | chr12 | 128751732 | 128752331 |
| chr12 | 128752423 | 128753022 | chr12 | 128753136 | 128753315 | chr12 | 128850442 | 128860739 |
| chr12 | 129337901 | 129338919 | chr12 | 130037571 | 130037866 | chr12 | 130387716 | 130387914 |
| chr12 | 130388332 | 130389231 | chr12 | 130589116 | 130589354 | chr12 | 130645131 | 130645730 |
| chr12 | 130646590 | 130647179 | chr12 | 130647263 | 130648569 | chr12 | 130821287 | 130821706 |
| chr12 | 130968586 | 130968758 | chr12 | 131200303 | 131200649 | chr12 | 131400719 | 131401018 |
| chr12 | 131402943 | 131403229 | chr12 | 131513255 | 131513494 | chr12 | 132169246 | 132169357 |
| chr12 | 132221614 | 132222153 | chr12 | 132333337 | 132333418 | chr12 | 132333517 | 132333696 |
| chr12 | 132348549 | 132348788 | chr12 | 132423596 | 132423829 | chr12 | 132643371 | 132643376 |
| chr12 | 132986419 | 132986658 | chr12 | 133002713 | 133003312 | chr12 | 133194996 | 133195295 |
| chr12 | 133199642 | 133199797 | chr12 | 133463657 | 133463956 | chr12 | 133464018 | 133464074 |
| chr12 | 133464755 | 133464920 | chr12 | 133481333 | 133481732 | chr12 | 133484660 | 133485439 |
| chr12 | 133485463 | 133485942 | chr12 | 133757959 | 133758198 | chr13 | 20735708 | 20736187 |
| chr13 | 20875662 | 20876021 | chr13 | 21649557 | 21649856 | chr13 | 22243192 | 22243551 |
| chr13 | 23489764 | 23490003 | chr13 | 23733355 | 23734124 | chr13 | 23734182 | 23734781 |
| chr13 | 24477566 | 24477985 | chr13 | 25115623 | 25115852 | chr13 | 25319764 | 25321443 |
| chr13 | 25321612 | 25322031 | chr13 | 25592963 | 05593201 | chr13 | 25620951 | 25621490 |
| chr13 | 25744639 | 25746054 | chr13 | 25946129 | 25946488 | chr13 | 25946529 | 25946888 |
| chr13 | 26042580 | 26043590 | chr13 | 26625215 | 26625814 | chr13 | 26625994 | 26626233 |
| chr13 | 27132307 | 27132546 | chr13 | 27334118 | 27334657 | chr13 | 27334684 | 27334983 |
| chr13 | 28239896 | 28240195 | chr13 | 28365615 | 28366181 | chr13 | 28366381 | 28366680 |
| chr13 | 28366923 | 28367162 | chr13 | 28367712 | 28368251 | chr13 | 28368373 | 28368672 |
| chr13 | 28368872 | 28369891 | chr13 | 28369952 | 28370071 | chr13 | 28370855 | 28371154 |
| chr13 | 28394667 | 28394966 | chr13 | 28395408 | 28395647 | chr13 | 28395917 | 28396156 |
| chr13 | 28491694 | 28492050 | chr13 | 28492160 | 28492639 | chr13 | 28528432 | 28528851 |
| chr13 | 28540657 | 28541016 | chr13 | 28543138 | 28543317 | chr13 | 28544321 | 28544980 |
| chr13 | 28549396 | 28550655 | chr13 | 28551320 | 28551559 | chr13 | 28551850 | 28552269 |
| chr13 | 28552481 | 28552660 | chr13 | 28552720 | 28552899 | chr13 | 28552935 | 28553234 |
| chr13 | 28673927 | 28674826 | chr13 | 29067676 | 29068515 | chr13 | 29068847 | 29069146 |
| chr13 | 29106217 | 29107409 | chr13 | 30707495 | 30707674 | chr13 | 31742856 | 31743242 |
| chr13 | 32605033 | 32605212 | chr13 | 32605357 | 32605596 | chr13 | 32605642 | 32606001 |
| chr13 | 33590737 | 33591036 | chr13 | 33591211 | 33591510 | chr13 | 33924579 | 33924812 |
| chr13 | 36045193 | 36045372 | chr13 | 36704848 | 36705147 | chr13 | 36705351 | 36705590 |
| chr13 | 36729006 | 36729229 | chr13 | 36920216 | 36920515 | chr13 | 36920528 | 36920887 |
| chr13 | 37004681 | 37004992 | chr13 | 37005051 | 37006840 | chr13 | 37247982 | 37248316 |
| chr13 | 37248886 | 37249125 | chr13 | 37633915 | 37634094 | chr13 | 37643855 | 37644094 |
| chr13 | 38443544 | 38443796 | chr13 | 39261309 | 39261422 | chr13 | 43566148 | 43566678 |
| chr13 | 44947643 | 44948302 | chr13 | 45885802 | 45885981 | chr13 | 45905243 | 45905356 |
| chr13 | 46425447 | 46425686 | chr13 | 46660850 | 46660944 | chr13 | 46961395 | 46961634 |
| chr13 | 47468065 | 47468244 | chr13 | 47526167 | 47526286 | chr13 | 48667803 | 48657982 |
| chr13 | 49794034 | 49795273 | chr13 | 53312917 | 53313996 | chr13 | 53419636 | 53419875 |
| chr13 | 53419931 | 53420170 | chr13 | 53420284 | 53420823 | chr13 | 53421161 | 53421164 |
| chr13 | 53421288 | 53421880 | chr13 | 53422220 | 53422459 | chr13 | 53423759 | 53424058 |
| chr13 | 58203504 | 58203743 | chr13 | 58203768 | 58204187 | chr13 | 58204253 | 58204492 |
| chr13 | 58205944 | 58207083 | chr13 | 58207382 | 58208101 | chr13 | 58208412 | 58209011 |
| chr13 | 67804144 | 67804175 | chr13 | 67804420 | 67804599 | chr13 | 67805100 | 67805339 |
| chr13 | 70681550 | 70682149 | chr13 | 72439047 | 72439109 | chr13 | 73619573 | 73619928 |
| chr13 | 78492724 | 78492942 | chr13 | 78493092 | 78493271 | chr13 | 78493363 | 78493902 |
| chr13 | 79169722 | 79170981 | chr13 | 79171038 | 79171277 | chr13 | 79175678 | 79176877 |
| chr13 | 79176897 | 79178096 | chr13 | 79183327 | 79183566 | chr13 | 84455499 | 84455798 |
| chr13 | 88323904 | 88324283 | chr13 | 88324415 | 88324714 | chr13 | 88325201 | 88325560 |
| chr13 | 88325731 | 88326140 | chr13 | 88326447 | 88327106 | chr13 | 88997832 | 88997951 |
| chr13 | 91948415 | 91948594 | chr13 | 92050668 | 92050843 | chr13 | 92051065 | 92051244 |
| chr13 | 92051273 | 92051632 | chr13 | 93879213 | 93879452 | chr13 | 93879596 | 93879775 |
| chr13 | 93879994 | 93880953 | chr13 | 95357237 | 95357416 | chr13 | 95357496 | 95357855 |
| chr13 | 95357954 | 95358253 | chr13 | 95359656 | 95359895 | chr13 | 95360228 | 95360647 |
| chr13 | 95363111 | 95363530 | chr13 | 95363697 | 95364296 | chr13 | 95364409 | 95364888 |
| chr13 | 95619931 | 95620170 | chr13 | 95620560 | 95621099 | chr13 | 96031611 | 96031725 |
| chr13 | 96204779 | 96205438 | chr13 | 96296297 | 96296559 | chr13 | 96296616 | 96297215 |
| chr13 | 96743713 | 96744212 | chr13 | 99851662 | 99851748 | chr13 | 100547770 | 100548009 |
| chr13 | 100608177 | 100608536 | chr13 | 100608597 | 100609136 | chr13 | 100621859 | 100622098 |
| chr13 | 100624213 | 100624452 | chr13 | 100624509 | 100624766 | chr13 | 100624801 | 100624808 |
| chr13 | 100626905 | 100627084 | chr13 | 100627203 | 100627442 | chr13 | 100630545 | 100631084 |
| chr13 | 100634227 | 100634382 | chr13 | 100635310 | 100635549 | chr13 | 100636084 | 100636323 |
| chr13 | 100637289 | 100637588 | chr13 | 100641203 | 100642282 | chr13 | 100643217 | 100643516 |
| chr13 | 100643955 | 100644314 | chr13 | 100649334 | 100650018 | chr13 | 102568380 | 102568559 |
| chr13 | 102568776 | 102569075 | chr13 | 102569104 | 102569643 | chr13 | 103046619 | 103047098 |
| chr13 | 103052252 | 103052671 | chr13 | 103052797 | 103053036 | chr13 | 103053296 | 103053509 |
| chr13 | 107186781 | 107186960 | chr13 | 107187085 | 107187242 | chr13 | 108518298 | 108518494 |
| chr13 | 108518724 | 108519017 | chr13 | 108519162 | 108519461 | chr13 | 108519637 | 108519996 |
| chr13 | 108520370 | 108520658 | chr13 | 108520879 | 108520969 | chr13 | 109147599 | 109148438 |
| chr13 | 109148685 | 109149115 | chr13 | 109149164 | 109149284 | chr13 | 110434373 | 110434672 |
| chr13 | 110958720 | 110959079 | chr13 | 110959119 | 110959358 | chr13 | 110959629 | 110960048 |

TABLE 14-continued

| chr | start | end | chr | start | end | chr | start | end |
|---|---|---|---|---|---|---|---|---|
| chr13 | 110960147 | 110960386 | chr13 | 110960453 | 110960692 | chr13 | 111278225 | 111278521 |
| chr13 | 111363885 | 111364060 | chr13 | 112272891 | 112273102 | chr13 | 112707603 | 112707962 |
| chr13 | 112708002 | 112708601 | chr13 | 112709408 | 112709647 | chr13 | 112709713 | 112709713 |
| chr13 | 112709787 | 112710026 | chr13 | 112710247 | 112710606 | chr13 | 112710669 | 112711868 |
| chr13 | 112711924 | 112713123 | chr13 | 112715267 | 112715746 | chr13 | 112715910 | 112716389 |
| chr13 | 112716695 | 112716814 | chr13 | 112716982 | 112717611 | chr13 | 112717743 | 112718042 |
| chr13 | 112719940 | 112720599 | chr13 | 112720626 | 112720865 | chr13 | 112720938 | 112721117 |
| chr13 | 112721158 | 112722417 | chr13 | 112724431 | 112724610 | chr13 | 112726240 | 112726659 |
| chr13 | 112727888 | 112728367 | chr13 | 112758033 | 112758688 | chr13 | 112758750 | 112759349 |
| chr13 | 112759538 | 112759717 | chr13 | 112759874 | 112760413 | chr13 | 112760755 | 112761305 |
| chr13 | 113598526 | 113598877 | chr13 | 113985597 | 113985956 | chr13 | 114055881 | 114056240 |
| chr13 | 114059990 | 114060409 | chr13 | 114074692 | 114074931 | chr13 | 114123081 | 114123358 |
| chr13 | 114189654 | 114189732 | chr13 | 114221548 | 114221655 | chr13 | 114304637 | 114305016 |
| chr13 | 114479330 | 114479509 | chr13 | 114497930 | 114498349 | chr13 | 114748251 | 114748730 |
| chr13 | 114780482 | 114781141 | chr13 | 114807537 | 114807896 | chr13 | 114855533 | 114855772 |
| chr13 | 114862381 | 114862458 | chr13 | 114961729 | 114962028 | chr14 | 21093364 | 21093531 |
| chr14 | 21093604 | 21093723 | chr14 | 21100674 | 21100906 | chr14 | 22004932 | 22005171 |
| chr14 | 23356162 | 23356341 | chr14 | 23706666 | 23706845 | chr14 | 24045439 | 24045678 |
| chr14 | 24803493 | 24804512 | chr14 | 26674280 | 26674459 | chr14 | 26674625 | 26674703 |
| chr14 | 27066520 | 27066699 | chr14 | 27067065 | 27067427 | chr14 | 29225457 | 29225636 |
| chr14 | 29225986 | 29226285 | chr14 | 29228567 | 29228866 | chr14 | 29229008 | 29229487 |
| chr14 | 29230995 | 29231229 | chr14 | 29231329 | 29231688 | chr14 | 29234911 | 29235450 |
| chr14 | 29236966 | 29237205 | chr14 | 29242687 | 29242707 | chr14 | 29243433 | 29243972 |
| chr14 | 29244147 | 29244383 | chr14 | 29247596 | 29247835 | chr14 | 29254495 | 29254794 |
| chr14 | 31344269 | 31344628 | chr14 | 31925640 | 31925804 | chr14 | 32597619 | 32597759 |
| chr14 | 33402373 | 33402852 | chr14 | 33402942 | 33403019 | chr14 | 33403125 | 33403421 |
| chr14 | 33403783 | 33404502 | chr14 | 34420150 | 34420389 | chr14 | 35023188 | 35023427 |
| chr14 | 35024347 | 35024454 | chr14 | 36003471 | 36003904 | chr14 | 36003979 | 36004578 |
| chr14 | 36004608 | 36005087 | chr14 | 36972709 | 36973008 | chr14 | 36973157 | 36973636 |
| chr14 | 36974421 | 36975058 | chr14 | 36975200 | 36975499 | chr14 | 36977558 | 36978097 |
| chr14 | 36978474 | 36978653 | chr14 | 36979657 | 36979724 | chr14 | 36982829 | 36983068 |
| chr14 | 36983628 | 36984227 | chr14 | 36985767 | 36985946 | chr14 | 36986212 | 36986931 |
| chr14 | 36987068 | 36987787 | chr14 | 36987862 | 36988221 | chr14 | 36988449 | 36988564 |
| chr14 | 36990779 | 36991258 | chr14 | 36991501 | 36991693 | chr14 | 36991848 | 36992507 |
| chr14 | 36993386 | 36994045 | chr14 | 36994145 | 36995104 | chr14 | 37116026 | 37116483 |
| chr14 | 37117535 | 37117745 | chr14 | 37123339 | 37124178 | chr14 | 37124289 | 37124648 |
| chr14 | 37124910 | 37125629 | chr14 | 37126150 | 37126389 | chr14 | 37126463 | 37127002 |
| chr14 | 37127207 | 37127386 | chr14 | 37127572 | 37128111 | chr14 | 37128459 | 37128818 |
| chr14 | 37129990 | 37130349 | chr14 | 37132296 | 37132775 | chr14 | 37132908 | 37133147 |
| chr14 | 37135706 | 37135868 | chr14 | 37135922 | 37136425 | chr14 | 37136514 | 37136693 |
| chr14 | 38060588 | 38061007 | chr14 | 38677445 | 38677581 | chr14 | 38724207 | 38725346 |
| chr14 | 38725434 | 38725560 | chr14 | 42074467 | 42074944 | chr14 | 42075023 | 42075066 |
| chr14 | 42075511 | 42076290 | chr14 | 42076749 | 42076928 | chr14 | 42077130 | 42077369 |
| chr14 | 42077696 | 42077804 | chr14 | 42079190 | 42079429 | chr14 | 48143657 | 48144196 |
| chr14 | 48144201 | 48144500 | chr14 | 48144619 | 48145158 | chr14 | 48145219 | 48145338 |
| chr14 | 50333976 | 50334084 | chr14 | 50334336 | 50334455 | chr14 | 51338642 | 51339061 |
| chr14 | 51560207 | 51561526 | chr14 | 51561680 | 51562099 | chr14 | 52534571 | 52534870 |
| chr14 | 52534929 | 52536488 | chr14 | 52734414 | 52734653 | chr14 | 52734687 | 52735346 |
| chr14 | 52781422 | 52782021 | chr14 | 54422549 | 54423028 | chr14 | 55370100 | 55370219 |
| chr14 | 55596008 | 55596043 | chr14 | 55765207 | 55765686 | chr14 | 57045445 | 57045840 |
| chr14 | 57260845 | 57261924 | chr14 | 57261977 | 57262276 | chr14 | 57264001 | 57265320 |
| chr14 | 57270854 | 57271333 | chr14 | 57271919 | 57272158 | chr14 | 57274387 | 57275406 |
| chr14 | 57275521 | 57276180 | chr14 | 57276344 | 57276763 | chr14 | 57277830 | 57279712 |
| chr14 | 57283238 | 57284737 | chr14 | 58332201 | 58332494 | chr14 | 60097111 | 60097650 |
| chr14 | 60386111 | 60386350 | chr14 | 60386551 | 60386790 | chr14 | 60794532 | 60794771 |
| chr14 | 60952084 | 60953039 | chr14 | 60973157 | 60973418 | chr14 | 60973618 | 60974157 |
| chr14 | 60974273 | 60974506 | chr14 | 60975290 | 60976609 | chr14 | 60976718 | 60976957 |
| chr14 | 60977263 | 60978222 | chr14 | 60981116 | 60981355 | chr14 | 60981586 | 60981885 |
| chr14 | 60982007 | 60982726 | chr14 | 50982757 | 60982996 | chr14 | 61104189 | 61104952 |
| chr14 | 61108539 | 61108904 | chr14 | 51109031 | 61109078 | chr14 | 61109129 | 61109648 |
| chr14 | 61109742 | 61110341 | chr14 | 61114058 | 61114537 | chr14 | 61115235 | 61116694 |
| chr14 | 61118688 | 61118841 | chr14 | 61118872 | 61119227 | chr14 | 61747277 | 61747816 |
| chr14 | 61748002 | 61748117 | chr14 | 62279493 | 62280092 | chr14 | 62583710 | 62584009 |
| chr14 | 63512017 | 63512376 | chr14 | 63512486 | 63512905 | chr14 | 63513050 | 63513229 |
| chr14 | 64222332 | 64222450 | chr14 | 65005803 | 65005915 | chr14 | 65008915 | 65009274 |
| chr14 | 65233253 | 65233552 | chr14 | 67886583 | 67886702 | chr14 | 69013958 | 69014195 |
| chr14 | 69866930 | 69867289 | chr14 | 70014640 | 70015059 | chr14 | 70038414 | 70038713 |
| chr14 | 70038889 | 70039101 | chr14 | 70346045 | 70346584 | chr14 | 70654379 | 70654798 |
| chr14 | 70655451 | 70656170 | chr14 | 72398642 | 72399121 | chr14 | 72399298 | 72399557 |
| chr14 | 72399830 | 72400129 | chr14 | 73167676 | 73167975 | chr14 | 73174938 | 73175237 |
| chr14 | 73178717 | 73178956 | chr14 | 73180112 | 73180336 | chr14 | 73318371 | 73318730 |
| chr14 | 73333174 | 73333256 | chr14 | 73602351 | 73602470 | chr14 | 74705940 | 74706299 |
| chr14 | 74706357 | 74707976 | chr14 | 74708760 | 74709059 | chr14 | 74892472 | 74892645 |
| chr14 | 74892975 | 74893191 | chr14 | 75078070 | 75078609 | chr14 | 75760210 | 75760329 |
| chr14 | 76604580 | 76604819 | chr14 | 76604985 | 76605464 | chr14 | 76843364 | 76843603 |
| chr14 | 76843639 | 76844058 | chr14 | 77228021 | 77228107 | chr14 | 77606833 | 77607312 |
| chr14 | 77737110 | 77737685 | chr14 | 79745088 | 79745277 | chr14 | 85996395 | 85996694 |
| chr14 | 85996760 | 85996999 | chr14 | 85997735 | 85998094 | chr14 | 85998468 | 85998786 |

TABLE 14-continued

| chr | start | end | chr | start | end | chr | start | end |
| --- | --- | --- | --- | --- | --- | --- | --- | --- |
| chr14 | 85999472 | 85999711 | chr14 | 86000182 | 85000574 | chr14 | 86000886 | 86001196 |
| chr14 | 89817813 | 89818112 | chr14 | 90527617 | 90527856 | chr14 | 90983225 | 90983385 |
| chr14 | 91691167 | 91691385 | chr14 | 91766189 | 91766542 | chr14 | 92789438 | 92789617 |
| chr14 | 92789777 | 92790256 | chr14 | 92790551 | 92790790 | chr14 | 92979835 | 92980074 |
| chr14 | 93154979 | 93155385 | chr14 | 93389450 | 93389869 | chr14 | 93706678 | 93706857 |
| chr14 | 94254302 | 94254601 | chr14 | 94405641 | 94405890 | chr14 | 95233616 | 95233646 |
| chr14 | 95234557 | 95235456 | chr14 | 95235939 | 95236200 | chr14 | 95236450 | 95236598 |
| chr14 | 95239298 | 95239717 | chr14 | 95240053 | 95240268 | chr14 | 95240410 | 95240497 |
| chr14 | 96342551 | 96342790 | chr14 | 96342806 | 96343225 | chr14 | 96343330 | 96343509 |
| chr14 | 96343553 | 96343792 | chr14 | 97045327 | 97045506 | chr14 | 97058761 | 97059180 |
| chr14 | 97499257 | 97499416 | chr14 | 97499616 | 97500035 | chr14 | 97684957 | 97685376 |
| chr14 | 97685624 | 97686038 | chr14 | 99584501 | 99584740 | chr14 | 99736048 | 99736213 |
| chr14 | 100437707 | 100438066 | chr14 | 100438609 | 100438908 | chr14 | 100643267 | 100643566 |
| chr14 | 101193145 | 101193384 | chr14 | 101250012 | 101250371 | chr14 | 101543783 | 101544270 |
| chr14 | 101923033 | 101923332 | chr14 | 101923520 | 101923819 | chr14 | 101923883 | 101924122 |
| chr14 | 101924966 | 101925985 | chr14 | 102026273 | 102026572 | chr14 | 102026703 | 102027062 |
| chr14 | 102031132 | 102031371 | chr14 | 102031434 | 102031666 | chr14 | 102247824 | 102248303 |
| chr14 | 102418533 | 102418652 | chr14 | 102521501 | 102521860 | chr14 | 102529912 | 102530178 |
| chr14 | 102530426 | 102530605 | chr14 | 102564386 | 102564502 | chr14 | 102681994 | 102682233 |
| chr14 | 103021308 | 103022087 | chr14 | 103394784 | 103395203 | chr14 | 103477540 | 103422771 |
| chr14 | 103655154 | 103655684 | chr14 | 103673992 | 103673994 | chr14 | 103674069 | 103674231 |
| chr14 | 103687002 | 103687301 | chr14 | 103739880 | 103740239 | chr14 | 103740275 | 103740514 |
| chr14 | 103745606 | 103745845 | chr14 | 104159978 | 104160160 | chr14 | 104202624 | 104202852 |
| chr14 | 104547814 | 104547993 | chr14 | 104571902 | 104572201 | chr14 | 104601657 | 104601935 |
| chr14 | 104601959 | 104602138 | chr14 | 104604954 | 104605193 | chr14 | 104620334 | 104620633 |
| chr14 | 104627564 | 104627862 | chr14 | 104645048 | 104645277 | chr14 | 104646225 | 104646584 |
| chr14 | 104647183 | 104647362 | chr14 | 104682452 | 104682751 | chr14 | 104862764 | 104863123 |
| chr14 | 105071198 | 106071340 | chr14 | 105157401 | 105157640 | chr14 | 105241220 | 105241267 |
| chr14 | 105246463 | 105246642 | chr14 | 105511960 | 105512463 | chr14 | 105658268 | 105658507 |
| chr14 | 105714177 | 105714690 | chr14 | 105714906 | 105715565 | chr15 | 22822269 | 22822384 |
| chr15 | 23158294 | 23158593 | chr15 | 26107541 | 26107960 | chr15 | 26108010 | 26108789 |
| chr15 | 27018281 | 27018520 | chr15 | 27212791 | 27213270 | chr15 | 27216294 | 27216533 |
| chr15 | 27603982 | 27604057 | chr15 | 28341615 | 28342514 | chr15 | 28344081 | 28344380 |
| chr15 | 28352156 | 28352935 | chr15 | 29077185 | 29077484 | chr15 | 29130712 | 29131971 |
| chr15 | 29407680 | 29408099 | chr15 | 29862423 | 29862537 | chr15 | 31455297 | 31455578 |
| chr15 | 31775500 | 31776216 | chr15 | 33009649 | 33011448 | chr15 | 33011498 | 33011737 |
| chr15 | 33486970 | 33487209 | chr15 | 33602725 | 33602964 | chr15 | 33603110 | 33603709 |
| chr15 | 33879168 | 33879347 | chr15 | 34630346 | 34630525 | chr15 | 34729381 | 34729680 |
| chr15 | 34786425 | 34787384 | chr15 | 35046935 | 35047234 | chr15 | 35087563 | 35087802 |
| chr15 | 37180227 | 37180241 | chr15 | 37180414 | 37180826 | chr15 | 37402898 | 37403316 |
| chr15 | 40211736 | 40212275 | chr15 | 40575538 | 40575837 | chr15 | 41165152 | 41165751 |
| chr15 | 41787709 | 41787948 | chr15 | 41804786 | 41805865 | chr15 | 41835732 | 41835814 |
| chr15 | 41913660 | 41913899 | chr15 | 41952493 | 41952792 | chr15 | 43810472 | 43810510 |
| chr15 | 44037485 | 44037604 | chr15 | 45403554 | 45404213 | chr15 | 45404833 | 45405209 |
| chr15 | 45421291 | 45421530 | chr15 | 45421874 | 45421947 | chr15 | 45427263 | 45427502 |
| chr15 | 45427520 | 45427879 | chr15 | 45479371 | 45479789 | chr15 | 45670503 | 45670971 |
| chr15 | 47476794 | 47477093 | chr15 | 48483882 | 48483963 | chr15 | 48936639 | 48938077 |
| chr15 | 48938122 | 48938601 | chr15 | 51385838 | 51386257 | chr15 | 51633986 | 51634225 |
| chr15 | 51973695 | 51974030 | chr15 | 53075716 | 53077455 | chr15 | 53077574 | 53077813 |
| chr15 | 53027971 | 53078320 | chr15 | 53079262 | 53080161 | chr15 | 53080263 | 53080682 |
| chr15 | 53080861 | 53081100 | chr15 | 53081223 | 53081702 | chr15 | 53082348 | 53082587 |
| chr15 | 53096735 | 53096974 | chr15 | 53097157 | 53097336 | chr15 | 53097535 | 53098074 |
| chr15 | 53098218 | 53098757 | chr15 | 54270424 | 54270783 | chr15 | 54270858 | 54271025 |
| chr15 | 55452972 | 55453087 | chr15 | 55699008 | 55699127 | chr15 | 55880796 | 55881095 |
| chr15 | 58357236 | 58357535 | chr15 | 58357638 | 58358297 | chr15 | 59158454 | 59158616 |
| chr15 | 59960343 | 59950461 | chr15 | 60286937 | 60287780 | chr15 | 60288703 | 60288935 |
| chr15 | 60289229 | 60289638 | chr15 | 60296047 | 60296286 | chr15 | 60296495 | 60297514 |
| chr15 | 60297544 | 60298203 | chr15 | 61520816 | 61521115 | chr15 | 61521559 | 61521676 |
| chr15 | 61521713 | 61522038 | chr15 | 62456848 | 62457019 | chr15 | 65669760 | 65669999 |
| chr15 | 65862054 | 65862213 | chr15 | 66963725 | 66963823 | chr15 | 66963928 | 66963964 |
| chr15 | 68112537 | 68112716 | chr15 | 68113794 | 68113973 | chr15 | 68114048 | 68114287 |
| chr15 | 68116286 | 68116682 | chr15 | 68117753 | 68118712 | chr15 | 68118783 | 68118784 |
| chr15 | 68118799 | 68119322 | chr15 | 68119463 | 68120662 | chr15 | 68120753 | 68120932 |
| chr15 | 68120968 | 68122167 | chr15 | 68122569 | 68122748 | chr15 | 68125164 | 68125763 |
| chr15 | 68127717 | 68128436 | chr15 | 68128492 | 68128597 | chr15 | 68260435 | 68260735 |
| chr15 | 71055770 | 71055905 | chr15 | 72412113 | 72412263 | chr15 | 72743650 | 72743859 |
| chr15 | 73659917 | 73660156 | chr15 | 73661476 | 73661748 | chr15 | 74044960 | 74045199 |
| chr15 | 74421927 | 74422226 | chr15 | 74422787 | 74423012 | chr15 | 74658070 | 74658595 |
| chr15 | 74686082 | 74686126 | chr15 | 74818670 | 74818789 | chr15 | 74903822 | 74904001 |
| chr15 | 75251245 | 75251484 | chr15 | 75251580 | 75251879 | chr15 | 75471036 | 75471275 |
| chr15 | 76627515 | 76627907 | chr15 | 76628959 | 76629314 | chr15 | 76629588 | 76629633 |
| chr15 | 76629732 | 76630931 | chr15 | 76632161 | 76632520 | chr15 | 76635040 | 76635279 |
| chr15 | 76635387 | 76635456 | chr15 | 76638778 | 76638806 | chr15 | 77448976 | 77449087 |
| chr15 | 78501725 | 78502024 | chr15 | 78556795 | 78557034 | chr15 | 78557110 | 78557204 |
| chr15 | 78596066 | 78596245 | chr15 | 78632626 | 78632925 | chr15 | 78912192 | 78912491 |
| chr15 | 78912549 | 78912728 | chr15 | 78912832 | 78913251 | chr15 | 78913444 | 78913683 |
| chr15 | 79104143 | 79104159 | chr15 | 79381709 | 79382648 | chr15 | 79382693 | 79383268 |
| chr15 | 79383873 | 79384052 | chr15 | 79502137 | 79502381 | chr15 | 79575197 | 79575556 |

TABLE 14-continued

| chr | start | end | chr | start | end | chr | start | end |
|---|---|---|---|---|---|---|---|---|
| chr15 | 79576062 | 79576361 | chr15 | 79724034 | 79724333 | chr15 | 79724402 | 79725241 |
| chr15 | 79725332 | 79725584 | chr15 | 82336777 | 82337076 | chr15 | 82339995 | 82340234 |
| chr15 | 83315246 | 83315474 | chr15 | 83316160 | 83317162 | chr15 | 83349131 | 83349790 |
| chr15 | 83378112 | 83378164 | chr15 | 83378186 | 83378471 | chr15 | 83776161 | 83776880 |
| chr15 | 83875571 | 83875985 | chr15 | 83876953 | 83877252 | chr15 | 83952108 | 83952827 |
| chr15 | 83953024 | 83953983 | chr15 | 84115648 | 84116067 | chr15 | 84116808 | 84116995 |
| chr15 | 84322765 | 84323124 | chr15 | 84748500 | 84749339 | chr15 | 85143052 | 85143144 |
| chr15 | 88798591 | 88798890 | chr15 | 88799448 | 88800407 | chr15 | 88800463 | 88801182 |
| chr15 | 89149070 | 89149489 | chr15 | 89248651 | 89249010 | chr15 | 89345953 | 89346492 |
| chr15 | 89346568 | 89347047 | chr15 | 89903410 | 89903889 | chr15 | 89910426 | 89910845 |
| chr15 | 89910988 | 89911287 | chr15 | 89913676 | 89913855 | chr15 | 89914144 | 89914983 |
| chr15 | 89915156 | 89915455 | chr15 | 89921862 | 89922101 | chr15 | 89922110 | 89922649 |
| chr15 | 89942671 | 89943030 | chr15 | 89943319 | 89943798 | chr15 | 89949317 | 89950036 |
| chr15 | 89950154 | 89951215 | chr15 | 89951302 | 89951901 | chr15 | 89952065 | 89953144 |
| chr15 | 89954122 | 89954416 | chr15 | 89956288 | 89956527 | chr15 | 90039488 | 90039787 |
| chr15 | 90755819 | 90756144 | chr15 | 91643264 | 91643683 | chr15 | 92936281 | 92936426 |
| chr15 | 92937115 | 92937474 | chr15 | 92937849 | 92938388 | chr15 | 93631638 | 93632117 |
| chr15 | 93632558 | 93633337 | chr15 | 94347588 | 94347707 | chr15 | 95388473 | 95388712 |
| chr15 | 96874259 | 96874416 | chr15 | 96889374 | 96889706 | chr15 | 96897853 | 96898092 |
| chr15 | 96911456 | 96911815 | chr15 | 96952594 | 96953313 | chr15 | 96959644 | 96960063 |
| chr15 | 96960428 | 96960513 | chr15 | 96960630 | 96960907 | chr15 | 97006274 | 97006623 |
| chr15 | 98504040 | 98504219 | chr15 | 98836077 | 98836477 | chr15 | 98965179 | 98965232 |
| chr15 | 99193106 | 99193345 | chr15 | 99193350 | 99193583 | chr15 | 99193873 | 99194172 |
| chr15 | 99456272 | 99456404 | chr15 | 100913332 | 100913982 | chr15 | 101420447 | 101420686 |
| chr15 | 101420848 | 101421087 | chr15 | 101513532 | 101513831 | chr16 | 142567 | 142775 |
| chr16 | 215341 | 216300 | chr16 | 216587 | 217070 | chr16 | 230229 | 230708 |
| chr16 | 318040 | 318316 | chr16 | 318422 | 318841 | chr16 | 337510 | 337749 |
| chr16 | 410303 | 410482 | chr16 | 611304 | 611603 | chr16 | 611876 | 612355 |
| chr16 | 612774 | 613133 | chr16 | 667040 | 667349 | chr16 | 667382 | 667399 |
| chr16 | 667466 | 667561 | chr16 | 677879 | 677993 | chr16 | 700225 | 700404 |
| chr16 | 726539 | 727078 | chr16 | 731400 | 731699 | chr16 | 735131 | 735670 |
| chr16 | 240888 | 741003 | chr16 | 741280 | 241507 | chr16 | 837262 | 537561 |
| chr16 | 845881 | 846060 | chr16 | 882567 | 882686 | chr16 | 895011 | 895250 |
| chr16 | 943398 | 943637 | chr16 | 1018046 | 1018225 | chr16 | 1030210 | 1030749 |
| chr16 | 1052488 | 1062727 | chr16 | 1103032 | 1103032 | chr16 | 1116721 | 1116766 |
| chr16 | 1128927 | 1129226 | chr16 | 1155068 | 1155307 | chr16 | 1203883 | 1204122 |
| chr16 | 1217226 | 1217583 | chr16 | 1217943 | 1218182 | chr16 | 1228711 | 1229010 |
| chr16 | 1230057 | 1230236 | chr16 | 1248521 | 1248760 | chr16 | 1267844 | 1268203 |
| chr16 | 1271447 | 1271746 | chr16 | 1312450 | 1312689 | chr16 | 1323900 | 1324139 |
| chr16 | 1382862 | 1383041 | chr16 | 1394400 | 1394579 | chr16 | 1397380 | 1397559 |
| chr16 | 1407366 | 1407485 | chr16 | 1407819 | 1407938 | chr16 | 1428422 | 1428961 |
| chr16 | 1491471 | 1491694 | chr16 | 1730213 | 1730692 | chr16 | 1741757 | 1742176 |
| chr16 | 2028986 | 2029225 | chr16 | 2040818 | 2042257 | chr16 | 2106629 | 2106741 |
| chr16 | 2128603 | 2128682 | chr16 | 2129033 | 2129332 | chr16 | 2141835 | 2142014 |
| chr16 | 2142468 | 2142707 | chr16 | 2213239 | 2213396 | chr16 | 2232665 | 2232784 |
| chr16 | 2234634 | 2235113 | chr16 | 2281163 | 2281402 | chr16 | 2287214 | 2287453 |
| chr16 | 2531136 | 2531255 | chr16 | 2764275 | 2764574 | chr16 | 2770033 | 2770512 |
| chr16 | 2818018 | 2818249 | chr16 | 2892457 | 2892816 | chr16 | 3016951 | 3017730 |
| chr16 | 3068097 | 3068276 | chr16 | 3151038 | 3151264 | chr16 | 3211625 | 3211742 |
| chr16 | 3211805 | 3211982 | chr16 | 3220474 | 3222325 | chr16 | 3225390 | 3225689 |
| chr16 | 3232697 | 3234121 | chr16 | 3234197 | 3234541 | chr16 | 3237783 | 3238022 |
| chr16 | 3238164 | 3238622 | chr16 | 3238912 | 3239631 | chr16 | 3239692 | 3239931 |
| chr16 | 3241517 | 3241756 | chr16 | 3241862 | 3241981 | chr16 | 3355200 | 3355799 |
| chr16 | 3598818 | 3599057 | chr16 | 3696620 | 3696799 | chr16 | 3802932 | 3803171 |
| chr16 | 4264433 | 4264792 | chr16 | 4431039 | 4431213 | chr16 | 4846061 | 4846415 |
| chr16 | 5037803 | 5038102 | chr16 | 5541026 | 5541257 | chr16 | 6069989 | 6070122 |
| chr16 | 7354560 | 7354739 | chr16 | 8780956 | 8781135 | chr16 | 8870279 | 8870458 |
| chr16 | 9009781 | 9010075 | chr16 | 10274325 | 10274504 | chr16 | 10275231 | 10275470 |
| chr16 | 10275671 | 10276030 | chr16 | 10276270 | 10277409 | chr16 | 10479719 | 10480078 |
| chr16 | 12530095 | 12630274 | chr16 | 12971812 | 12972035 | chr16 | 12994359 | 12994838 |
| chr16 | 12994969 | 12995688 | chr16 | 12995707 | 12996426 | chr16 | 12996520 | 12996819 |
| chr16 | 12996861 | 12997100 | chr16 | 12997306 | 12997785 | chr16 | 14725745 | 14725864 |
| chr16 | 15489851 | 15489884 | chr16 | 15820726 | 15820965 | chr16 | 18802486 | 18802725 |
| chr16 | 18950987 | 18951093 | chr16 | 19567117 | 19567536 | chr16 | 19895051 | 19895230 |
| chr16 | 21831520 | 21832052 | chr16 | 21839250 | 21839348 | chr16 | 22824599 | 22825198 |
| chr16 | 22825225 | 22826184 | chr16 | 23313374 | 23313613 | chr16 | 23313674 | 23313913 |
| chr16 | 23706240 | 23706599 | chr16 | 23765995 | 23766098 | chr16 | 23766133 | 23766234 |
| chr16 | 23847214 | 23848053 | chr16 | 24267013 | 24267312 | chr16 | 24267383 | 24267594 |
| chr16 | 25266436 | 25266675 | chr16 | 25702855 | 25703094 | chr16 | 25703685 | 25704705 |
| chr16 | 26664758 | 26664853 | chr16 | 27460002 | 27460156 | chr16 | 28074101 | 28074760 |
| chr16 | 28074869 | 28075288 | chr16 | 29118954 | 29119133 | chr16 | 29153201 | 29153254 |
| chr16 | 29244800 | 29245099 | chr16 | 29830796 | 29831155 | chr16 | 29888045 | 29888332 |
| chr16 | 29888549 | 29888761 | chr16 | 30017240 | 30017539 | chr16 | 30116211 | 30116390 |
| chr16 | 30124597 | 30124949 | chr16 | 30804458 | 30804575 | chr16 | 30826363 | 30826570 |
| chr16 | 30906930 | 30907049 | chr16 | 30907123 | 30907229 | chr16 | 31227815 | 31228402 |
| chr16 | 31446904 | 31447173 | chr16 | 31497971 | 31498087 | chr16 | 31500460 | 31500759 |
| chr16 | 31580469 | 31581058 | chr16 | 46721556 | 46721787 | chr16 | 47177447 | 47177686 |
| chr16 | 48844690 | 48845229 | chr16 | 49309067 | 49309366 | chr16 | 49311432 | 49312391 |

TABLE 14-continued

| chr | start | end | chr | start | end | chr | start | end |
|---|---|---|---|---|---|---|---|---|
| chr16 | 49313268 | 49313807 | chr16 | 49313921 | 49314220 | chr16 | 49314341 | 49314640 |
| chr16 | 49314692 | 49314931 | chr16 | 49315202 | 49315381 | chr16 | 49315831 | 49316670 |
| chr16 | 49637986 | 49638165 | chr16 | 50335693 | 50335872 | chr16 | 51183824 | 51184483 |
| chr16 | 51184725 | 51185444 | chr16 | 51185763 | 51186362 | chr16 | 51186497 | 51187036 |
| chr16 | 51189848 | 51190309 | chr16 | 53563519 | 53563734 | chr16 | 54318824 | 54318838 |
| chr16 | 54318855 | 54319063 | chr16 | 54319325 | 54319564 | chr16 | 54321557 | 54321916 |
| chr16 | 54324960 | 54325199 | chr16 | 54628600 | 54628959 | chr16 | 54964875 | 54965211 |
| chr16 | 54966728 | 54967388 | chr16 | 54970986 | 54971165 | chr16 | 54971326 | 54971505 |
| chr16 | 55090585 | 55090944 | chr16 | 55357827 | 55358186 | chr16 | 55358213 | 55358632 |
| chr16 | 55358696 | 55359175 | chr16 | 55362907 | 55363326 | chr16 | 55364631 | 55364930 |
| chr16 | 55365020 | 55365319 | chr16 | 55404898 | 55406317 | chr16 | 55512745 | 55512984 |
| chr16 | 55689812 | 55689991 | chr16 | 55690013 | 55690912 | chr16 | 56224479 | 56224958 |
| chr16 | 56228271 | 56228686 | chr16 | 56651006 | 56651365 | chr16 | 56659095 | 56659754 |
| chr16 | 56672077 | 56672761 | chr16 | 56709755 | 56710114 | chr16 | 57222710 | 57222806 |
| chr16 | 57935475 | 57935655 | chr16 | 58018531 | 58018950 | chr16 | 58019149 | 58019508 |
| chr16 | 58120875 | 58121058 | chr16 | 58497136 | 58497495 | chr16 | 58497672 | 58497911 |
| chr16 | 58498101 | 58498280 | chr16 | 58498468 | 58498809 | chr16 | 58521634 | 58521813 |
| chr16 | 58550415 | 58550587 | chr16 | 58969669 | 58969895 | chr16 | 62068387 | 62068610 |
| chr16 | 62068923 | 62069057 | chr16 | 62070669 | 62070848 | chr16 | 65154833 | 65155192 |
| chr16 | 65156288 | 65156587 | chr16 | 66461694 | 66461933 | chr16 | 66612797 | 66613359 |
| chr16 | 67197615 | 67197854 | chr16 | 67197935 | 67198114 | chr16 | 67198818 | 67199057 |
| chr16 | 67241130 | 67241309 | chr16 | 67313791 | 67313970 | chr16 | 68544170 | 68544409 |
| chr16 | 68676307 | 68677086 | chr16 | 68770847 | 68771086 | chr16 | 68771167 | 68771402 |
| chr16 | 68876728 | 68876847 | chr16 | 70595543 | 70595782 | chr16 | 71459950 | 71460429 |
| chr16 | 71715705 | 71715884 | chr16 | 72957660 | 72957899 | chr16 | 73100373 | 73100612 |
| chr16 | 75019677 | 75019856 | chr16 | 77247366 | 77247545 | chr16 | 77468182 | 77468878 |
| chr16 | 77822493 | 77822972 | chr16 | 78079893 | 78080132 | chr16 | 79623729 | 79623968 |
| chr16 | 80838052 | 80838173 | chr16 | 80966296 | 80966535 | chr16 | 81929288 | 81929467 |
| chr16 | 82660279 | 82660578 | chr16 | 82660638 | 82660817 | chr16 | 84074767 | 84074946 |
| chr16 | 84153290 | 84153469 | chr16 | 84402163 | 84402402 | chr16 | 84853274 | 84853452 |
| chr16 | 85075418 | 85075644 | chr16 | 85317747 | 85317879 | chr16 | 85485652 | 85485951 |
| chr16 | 85517254 | 85517613 | chr16 | 85678551 | 85678850 | chr16 | 85684234 | 85684533 |
| chr16 | 85699596 | 85699925 | chr16 | 85932754 | 85932933 | chr16 | 86320254 | 86320493 |
| chr16 | 86320659 | 86320898 | chr16 | 86320925 | 86321147 | chr16 | 86530848 | 86531147 |
| chr16 | 86531233 | 86531652 | chr16 | 86541537 | 86541956 | chr16 | 86542296 | 86542535 |
| chr16 | 86544103 | 86545062 | chr16 | 86599392 | 86599931 | chr16 | 86600406 | 86600765 |
| chr16 | 86600868 | 86601107 | chr16 | 86601204 | 86601623 | chr16 | 86601871 | 86602590 |
| chr16 | 86612961 | 86613017 | chr16 | 87092347 | 87092646 | chr16 | 87635029 | 87635208 |
| chr16 | 87636444 | 87636983 | chr16 | 87714178 | 87714477 | chr16 | 87723648 | 87724187 |
| chr16 | 88164316 | 88164555 | chr16 | 88498142 | 88498861 | chr16 | 88503978 | 88504397 |
| chr16 | 88506265 | 88506616 | chr16 | 88512329 | 88512628 | chr16 | 88603617 | 88603848 |
| chr16 | 88623885 | 88624165 | chr16 | 88757428 | 88757571 | chr16 | 88879858 | 88880097 |
| chr16 | 88883159 | 88883458 | chr16 | 88940981 | 88941220 | chr16 | 88942021 | 88942239 |
| chr16 | 88943463 | 88944122 | chr16 | 88945726 | 88946034 | chr16 | 88955160 | 88955459 |
| chr16 | 88956136 | 88956495 | chr16 | 88957374 | 88957934 | chr16 | 88958295 | 88958534 |
| chr16 | 88963191 | 88963850 | chr16 | 88966207 | 88966686 | chr16 | 88968630 | 88968869 |
| chr16 | 88977929 | 88978168 | chr16 | 88992975 | 88993334 | chr16 | 88999543 | 88999557 |
| chr16 | 88999574 | R8999693 | chr16 | 89000127 | 89000306 | chr16 | 89001020 | 89001139 |
| chr16 | 89007420 | 89007659 | chr16 | 89007789 | 89007879 | chr16 | 89008488 | 89008667 |
| chr16 | 89047643 | 89047822 | chr16 | 89072400 | 89072879 | chr16 | 89086034 | 89086273 |
| chr16 | 89107585 | 89107824 | chr16 | 89109345 | 89109490 | chr16 | 89119940 | 89120419 |
| chr16 | 89120607 | 89120963 | chr16 | 89137919 | 89138165 | chr16 | 89220244 | 89220483 |
| chr16 | 89220580 | 89220999 | chr16 | 89254563 | 89254742 | chr16 | 89267260 | 89267439 |
| chr16 | 89267709 | 89267948 | chr16 | 89558549 | 89558807 | chr16 | 89883930 | 89884289 |
| chr16 | 89884875 | 89884989 | chr16 | 89885115 | 89885229 | chr16 | 89900033 | 89900272 |
| chr16 | 89900372 | 89900611 | chr17 | 616914 | 617026 | chr17 | 1082923 | 1083093 |
| chr17 | 1173906 | 1174505 | chr17 | 1636129 | 1536221 | chr17 | 1646312 | 1546539 |
| chr17 | 1623600 | 1623779 | chr17 | 1959375 | 1959614 | chr17 | 2207848 | 2207967 |
| chr17 | 2208042 | 2208147 | chr17 | 2220974 | 2221142 | chr17 | 2249977 | 2250096 |
| chr17 | 3438818 | 3439057 | chr17 | 3658751 | 3658930 | chr17 | 3658991 | 3659110 |
| chr17 | 4544510 | 4544809 | chr17 | 4699212 | 4699331 | chr17 | 4891237 | 4891381 |
| chr17 | 5000340 | 5000879 | chr17 | 5000958 | 5001137 | chr17 | 6616543 | 6616782 |
| chr17 | 6616813 | 6617191 | chr17 | 6679220 | 6679393 | chr17 | 6946113 | 6946244 |
| chr17 | 7348792 | 7349070 | chr17 | 7368864 | 7369223 | chr17 | 7555099 | 7555338 |
| chr17 | 7573794 | 7574094 | chr17 | 7576923 | 7577222 | chr17 | 7577423 | 7577662 |
| chr17 | 7578078 | 7578557 | chr17 | 7906156 | 7906514 | chr17 | 8104071 | 8104173 |
| chr17 | 8230246 | 8230785 | chr17 | 8774685 | 8774728 | chr17 | 8868524 | 8869483 |
| chr17 | 8906183 | 8906602 | chr17 | 8906895 | 8907674 | chr17 | 8925983 | 8926201 |
| chr17 | 10100995 | 10102074 | chr17 | 10102331 | 10102750 | chr17 | 11144218 | 11144424 |
| chr17 | 11144839 | 11145078 | chr17 | 13503875 | 13504294 | chr17 | 13504470 | 13504769 |
| chr17 | 13504873 | 13505292 | chr17 | 13505316 | 13505675 | chr17 | 14200962 | 14201261 |
| chr17 | 14204138 | 14204317 | chr17 | 14204425 | 14204724 | chr17 | 15244976 | 15245215 |
| chr17 | 16282157 | 16282396 | chr17 | 16570674 | 16570897 | chr17 | 17062513 | 17062752 |
| chr17 | 17123889 | 17124068 | chr17 | 17398520 | 17398542 | chr17 | 18163094 | 18163415 |
| chr17 | 18538207 | 18538365 | chr17 | 20817897 | 20817998 | chr17 | 25620495 | 25620794 |
| chr17 | 25676885 | 25677004 | chr17 | 25680190 | 25680276 | chr17 | 25907676 | 25907855 |
| chr17 | 26263104 | 26263214 | chr17 | 26554551 | 26554790 | chr17 | 26961721 | 26961922 |
| chr17 | 27038568 | 27038985 | chr17 | 27044696 | 27044875 | chr17 | 27056846 | 27056957 |

TABLE 14-continued

| chr | start | end | chr | start | end | chr | start | end |
|---|---|---|---|---|---|---|---|---|
| chr17 | 27170072 | 27170182 | chr17 | 27181284 | 27181456 | chr17 | 27332378 | 27332737 |
| chr17 | 27716018 | 27716134 | chr17 | 27716198 | 27716314 | chr17 | 27940276 | 27940995 |
| chr17 | 28562614 | 28562853 | chr17 | 29232148 | 29232267 | chr17 | 29249615 | 29250034 |
| chr17 | 29298002 | 29298463 | chr17 | 29718123 | 29718362 | chr17 | 29719096 | 29719335 |
| chr17 | 30243689 | 30243988 | chr17 | 30250242 | 30250345 | chr17 | 31618333 | 31619412 |
| chr17 | 31619870 | 31620109 | chr17 | 32483946 | 32484125 | chr17 | 32906299 | 32906718 |
| chr17 | 32906888 | 32907112 | chr17 | 32907136 | 32907247 | chr17 | 32907554 | 32907853 |
| chr17 | 32908044 | 32908463 | chr17 | 32908550 | 32909029 | chr17 | 33672832 | 33673071 |
| chr17 | 33877184 | 33877303 | chr17 | 33917240 | 33917350 | chr17 | 35165549 | 35166788 |
| chr17 | 35165912 | 35166091 | chr17 | 35285455 | 35285754 | chr17 | 35290313 | 35290732 |
| chr17 | 35291242 | 35291457 | chr17 | 35291749 | 35292708 | chr17 | 35293630 | 35294229 |
| chr17 | 35294364 | 35294603 | chr17 | 35294955 | 35295254 | chr17 | 35296069 | 35296368 |
| chr17 | 35296629 | 35296988 | chr17 | 35297527 | 35298246 | chr17 | 35299154 | 35300953 |
| chr17 | 35303259 | 35303618 | chr17 | 36102935 | 36103414 | chr17 | 36103497 | 36103676 |
| chr17 | 36104031 | 36104870 | chr17 | 36105141 | 36105680 | chr17 | 37192168 | 37192281 |
| chr17 | 37321100 | 37322010 | chr17 | 37366236 | 37366655 | chr17 | 37369106 | 37369285 |
| chr17 | 37380922 | 37381941 | chr17 | 37382048 | 37382347 | chr17 | 37757056 | 37757305 |
| chr17 | 37760406 | 37760645 | chr17 | 37761897 | 37762436 | chr17 | 37879697 | 37879712 |
| chr17 | 38179295 | 38179348 | chr17 | 38179492 | 38179534 | chr17 | 38347473 | 38342712 |
| chr17 | 38497542 | 38497721 | chr17 | 38498009 | 38498188 | chr17 | 39682550 | 39682729 |
| chr17 | 40332846 | 40333268 | chr17 | 40400770 | 40401109 | chr17 | 40464179 | 40464418 |
| chr17 | 40464443 | 40464627 | chr17 | 40975576 | 40975754 | chr17 | 41278542 | 41278693 |
| chr17 | 41651776 | 41651887 | chr17 | 41791386 | 41791565 | chr17 | 41791591 | 41791599 |
| chr17 | 42030244 | 42030843 | chr17 | 42061240 | 42061479 | chr17 | 42082421 | 42082660 |
| chr17 | 42092116 | 42092295 | chr17 | 42331637 | #2331746 | chr17 | 42393780 | 42394113 |
| chr17 | 42402782 | 42402984 | chr17 | 42587336 | 42587452 | chr17 | 42635199 | 42635844 |
| chr17 | 42733619 | 42733978 | chr17 | 42787580 | 42787699 | chr17 | 42907489 | 42908028 |
| chr17 | 43001800 | 43002029 | chr17 | 43037408 | 43037504 | chr17 | 43044584 | 43044763 |
| chr17 | 43044909 | 43045208 | chr17 | 43047355 | 43047834 | chr17 | 43339012 | 43339431 |
| chr17 | 43339546 | 43339994 | chr17 | 43974158 | 43974457 | chr17 | 45331345 | 45331404 |
| chr17 | 45810776 | 45811426 | chr17 | 45867239 | 45867538 | chr17 | 46124907 | 46125146 |
| chr17 | 46619224 | 46619224 | chr17 | 46620405 | 46621184 | chr17 | 46621257 | 46621535 |
| chr17 | 46621764 | 46622003 | chr17 | 46655074 | 46555253 | chr17 | 46655351 | 46656531 |
| chr17 | 46659345 | 46659944 | chr17 | 46663666 | 46663928 | chr17 | 46674831 | 46675072 |
| chr17 | 46675086 | 46675685 | chr17 | 46690387 | 46690746 | chr17 | 46691430 | 46691669 |
| chr17 | 46691719 | 46692198 | chr17 | 46692344 | 46692509 | chr17 | 46710857 | 46711156 |
| chr17 | 46711179 | 46711213 | chr17 | 46711240 | 46711478 | chr17 | 46713934 | 46714166 |
| chr17 | 46795563 | 46796545 | chr17 | 46796606 | 46797662 | chr17 | 46799522 | 46800001 |
| chr17 | 46800516 | 46800755 | chr17 | 46800860 | 46801418 | chr17 | 46802364 | 46803286 |
| chr17 | 46804029 | 46804508 | chr17 | 46810328 | 46811047 | chr17 | 46811269 | 46811628 |
| chr17 | 46816191 | 46816730 | chr17 | 46824218 | 46825149 | chr17 | 46825190 | 46825609 |
| chr17 | 46826897 | 46827196 | chr17 | 46827244 | 46827843 | chr17 | 46829420 | 46829659 |
| chr17 | 46829898 | 46830195 | chr17 | 46831700 | 46832719 | chr17 | 47072716 | 47073555 |
| chr17 | 47073899 | 47074318 | chr17 | 47074459 | 47074489 | chr17 | 47074597 | 47074998 |
| chr17 | 47075083 | 47075442 | chr17 | 47075616 | 47076155 | chr17 | 47574001 | 47574240 |
| chr17 | 47657445 | 47657684 | chr17 | 47865416 | 47865655 | chr17 | 47987423 | 47987722 |
| chr17 | 47987843 | 47988202 | chr17 | 48041057 | 48041416 | chr17 | 48041578 | 48041817 |
| chr17 | 48041965 | 48042144 | chr17 | 48042337 | 48043056 | chr17 | 48048857 | 48049156 |
| chr17 | 48049228 | 48050607 | chr17 | 48070946 | 48071125 | chr17 | 48071694 | 48071957 |
| chr17 | 48612147 | 48612386 | chr17 | 48636500 | 48637219 | chr17 | 48653054 | 48653233 |
| chr17 | 48799847 | 48799963 | chr17 | 49229486 | 49229601 | chr17 | 50235126 | 50235365 |
| chr17 | 50235625 | 50236032 | chr17 | 51900930 | 51901109 | chr17 | 53341155 | 53341557 |
| chr17 | 53342774 | 53343193 | chr17 | 53922571 | 53922870 | chr17 | 54674890 | 54675369 |
| chr17 | 54755873 | 54756112 | chr17 | 56092519 | 56092620 | chr17 | 56234305 | 56234844 |
| chr17 | 56326853 | 56327092 | chr17 | 56327197 | 56327376 | chr17 | 56833025 | 56833324 |
| chr17 | 56833622 | 56834161 | chr17 | 56834222 | 56834366 | chr17 | 57297028 | 57297207 |
| chr17 | 58216513 | 58217652 | chr17 | 58218670 | 58219089 | chr17 | 58227281 | 58227520 |
| chr17 | 58498657 | 58499396 | chr17 | 59474060 | 59474719 | chr17 | 59474758 | 59475177 |
| chr17 | 59475604 | 59476023 | chr17 | 59476084 | 59476203 | chr17 | 59476314 | 59476733 |
| chr17 | 59478046 | 59478705 | chr17 | 59488010 | 59488549 | chr17 | 59528775 | 59530454 |
| chr17 | 59531574 | 59532233 | chr17 | 59533741 | 59534580 | chr17 | 59534677 | 59534856 |
| chr17 | 59535059 | 59535298 | chr17 | 59539150 | 59539689 | chr17 | 61777984 | 61778403 |
| chr17 | 61817858 | 61818036 | chr17 | 61926149 | 61926688 | chr17 | 62777244 | 62777543 |
| chr17 | 62777650 | 62777889 | chr17 | 64672276 | 64672635 | chr17 | 66596379 | 66596618 |
| chr17 | 66596884 | 66597123 | chr17 | 67410500 | 67410501 | chr17 | 68164667 | 68164906 |
| chr17 | 70026473 | 70026755 | chr17 | 70112818 | 70114617 | chr17 | 70215595 | 70216674 |
| chr17 | 71641465 | 71641761 | chr17 | 71948352 | 71948951 | chr17 | 72270202 | 72270501 |
| chr17 | 72321844 | 72322074 | chr17 | 72322275 | 72322694 | chr17 | 72353113 | 72353531 |
| chr17 | 72427777 | 72427963 | chr17 | 72428244 | 72428483 | chr17 | 72667242 | 72667966 |
| chr17 | 72848926 | 72849165 | chr17 | 72856964 | 72857443 | chr17 | 72920705 | 72921124 |
| chr17 | 73031547 | 73031619 | chr17 | 73073610 | 73073876 | chr17 | 73545910 | 73546120 |
| chr17 | 73584733 | 73584972 | chr17 | 73585918 | 73586517 | chr17 | 73608232 | 73608411 |
| chr17 | 73636062 | 73636421 | chr17 | 74028047 | 74028461 | chr17 | 74047755 | 74047994 |
| chr17 | 74070386 | 74070672 | chr17 | 74071344 | 74071583 | chr17 | 74071590 | 74071825 |
| chr17 | 74072840 | 74073139 | chr17 | 74073172 | 74073531 | chr17 | 74390289 | 74390468 |
| chr17 | 74533808 | 74534407 | chr17 | 74581083 | 74581322 | chr17 | 74864974 | 74865273 |
| chr17 | 74865612 | 74866331 | chr17 | 75207765 | 75207944 | chr17 | 75368658 | 75369317 |
| chr17 | 75369351 | 75369950 | chr17 | 75370174 | 75370413 | chr17 | 75370522 | 75370701 |

TABLE 14-continued

| chr | start | end | chr | start | end | chr | start | end |
|---|---|---|---|---|---|---|---|---|
| chr17 | 75385122 | 75385301 | chr17 | 75523058 | 75523354 | chr17 | 75524556 | 75525275 |
| chr17 | 75733902 | 75734108 | chr17 | 75797121 | 75797265 | chr17 | 76125122 | 76125301 |
| chr17 | 76137862 | 76138281 | chr17 | 76138525 | 76138710 | chr17 | 76227774 | 76228433 |
| chr17 | 76404662 | 76404757 | chr17 | 76921756 | 76921934 | chr17 | 76974354 | 76974582 |
| chr17 | 77084488 | 77084667 | chr17 | 77104978 | 77106277 | chr17 | 77145037 | 77145336 |
| chr17 | 77179017 | 77179376 | chr17 | 77179532 | 77179891 | chr17 | 77776733 | 77777152 |
| chr17 | 77777504 | 77778043 | chr17 | 77778852 | 17779136 | chr17 | 77788756 | 77789055 |
| chr17 | 77789219 | 77789578 | chr17 | 77825605 | 77825858 | chr17 | 77899590 | 77899634 |
| chr17 | 78122175 | 78122294 | chr17 | 78447053 | 78447213 | chr17 | 78451842 | 78452141 |
| chr17 | 78452199 | 78452438 | chr17 | 78452578 | 78452937 | chr17 | 78518204 | 78518295 |
| chr17 | 78599493 | 78599732 | chr17 | 78667897 | 78668256 | chr17 | 78874418 | 78874650 |
| chr17 | 79094095 | 79094334 | chr17 | 79099696 | 79099875 | chr17 | 79615087 | 79615446 |
| chr17 | 79626656 | 79626797 | chr17 | 79769354 | 79769773 | chr17 | 80254258 | 80254371 |
| chr17 | 80289153 | 80289392 | chr17 | 80329628 | 80330167 | chr17 | 80394659 | 80394678 |
| chr17 | 80479366 | 80479525 | chr17 | 80535286 | 80535469 | chr17 | 80654909 | 80655088 |
| chr17 | 80693343 | 80693582 | chr17 | 80797600 | 80798439 | chr17 | 80832209 | 80832508 |
| chr17 | 80832635 | 80832874 | chr17 | 81008543 | 81008902 | chr17 | 81033413 | 81033592 |
| chr17 | 81048919 | 81049098 | chr17 | 81049943 | 81050146 | chr18 | 499454 | 499575 |
| chr18 | 499947 | 500842 | chr18 | 904376 | 904735 | chr18 | 904926 | 905105 |
| chr18 | 905359 | 906718 | chr18 | 906770 | 907009 | chr18 | 907384 | 907683 |
| chr18 | 907826 | 908065 | chr18 | 908373 | 908607 | chr18 | 909046 | 909225 |
| chr18 | 909388 | 909687 | chr18 | 2755855 | 2755974 | chr18 | 2906167 | 2906406 |
| chr18 | 3215032 | 3215271 | chr18 | 3498980 | 3499447 | chr18 | 4453885 | 4454244 |
| chr18 | 4454979 | 4455278 | chr18 | 5133126 | 5133405 | chr18 | 5196439 | 5197038 |
| chr18 | 5197126 | 5197425 | chr18 | 5543132 | 5543431 | chr18 | 5543606 | 5543957 |
| chr18 | 5628072 | 5628611 | chr18 | 5629700 | 5630059 | chr18 | 5630218 | 5630457 |
| chr18 | 5890519 | 5891418 | chr18 | 5894935 | 5895294 | chr18 | 5895881 | 5896180 |
| chr18 | 6729881 | 6730093 | chr18 | 7116858 | 7117073 | chr18 | 7117586 | 7117885 |
| chr18 | 7567708 | 7568367 | chr18 | 8608649 | 8609062 | chr18 | 8612178 | 8612357 |
| chr18 | 9771621 | 9771850 | chr18 | 9912693 | 9912872 | chr18 | 10589013 | 10589432 |
| chr18 | 11148888 | 11149127 | chr18 | 11149486 | 11149965 | chr18 | 11401557 | 11401846 |
| chr18 | 11751538 | 11751777 | chr18 | 11751874 | 11752473 | chr18 | 11752625 | 11752805 |
| chr18 | 11942634 | 11942746 | chr18 | 12254133 | 12254672 | chr18 | 12307170 | 12307829 |
| chr18 | 12376133 | 12376206 | chr18 | 12911281 | 12911408 | chr18 | 13824125 | 13824184 |
| chr18 | 13826316 | 13826615 | chr18 | 13868620 | 13869039 | chr18 | 15198162 | 15198269 |
| chr18 | 18822294 | 18823060 | chr18 | 18823101 | 18823373 | chr18 | 19750286 | 19750447 |
| chr18 | 20911467 | 20911646 | chr18 | 21269344 | 21269490 | chr18 | 21269581 | 21269763 |
| chr18 | 22928981 | 22930660 | chr18 | 22930715 | 22931254 | chr18 | 23686388 | 23686507 |
| chr18 | 24127650 | 24128129 | chr18 | 24130729 | 24131267 | chr18 | 24764851 | 24765252 |
| chr18 | 25755505 | 25755744 | chr18 | 25755936 | 25756115 | chr18 | 25756542 | 25756822 |
| chr18 | 25757151 | 25757530 | chr18 | 25757687 | 25757926 | chr18 | 25757994 | 25758233 |
| chr18 | 28620819 | 28621178 | chr18 | 28621242 | 28621274 | chr18 | 28621383 | 28621481 |
| chr18 | 28621545 | 28622024 | chr18 | 28622335 | 28622574 | chr18 | 30349642 | 30349872 |
| chr18 | 31020419 | 31020898 | chr18 | 31158007 | 31158406 | chr18 | 31738953 | 31739552 |
| chr18 | 31802031 | 31802270 | chr18 | 31802864 | 31803043 | chr18 | 31803336 | 31803575 |
| chr18 | 31902690 | 31902944 | chr18 | 32073807 | 32074166 | chr18 | 32557847 | 32557968 |
| chr18 | 32957702 | 32957813 | chr18 | 33078274 | 33078393 | chr18 | 33078634 | 33078753 |
| chr18 | 33877784 | 33877839 | chr18 | 34833519 | 34833938 | chr18 | 35064986 | 35065525 |
| chr18 | 35104565 | 35104984 | chr18 | 35144766 | 35145545 | chr18 | 35146023 | 35146322 |
| chr18 | 35147409 | 35147648 | chr18 | 43914126 | 43914365 | chr18 | 44259911 | 44260067 |
| chr18 | 44336999 | 44336786 | chr18 | 44336805 | 44337044 | chr18 | 44337445 | 44338164 |
| chr18 | 44772980 | 44773279 | chr18 | 44773574 | 44774233 | chr18 | 44774319 | 44774804 |
| chr18 | 44775309 | 44775647 | chr18 | 44776881 | 44777180 | chr18 | 44777227 | 44777406 |
| chr18 | 44277512 | 44777853 | chr18 | 44777949 | 44778411 | chr18 | 44780903 | 44781142 |
| chr18 | 44787695 | 44787934 | chr18 | 44788177 | 44788356 | chr18 | 44789375 | 44789614 |
| chr18 | 44789786 | 44790025 | chr18 | 45057993 | 45058335 | chr18 | 46142587 | 46142715 |
| chr18 | 49867202 | 49867483 | chr18 | 52988906 | 52989316 | chr18 | 52989723 | 52989962 |
| chr18 | 53257052 | 53257291 | chr18 | 53446884 | 53447903 | chr18 | 53989718 | 53989828 |
| chr18 | 53989876 | 53989957 | chr18 | 54788984 | 54789343 | chr18 | 55019610 | 55019918 |
| chr18 | 55020572 | 55020811 | chr18 | 55020981 | 55021340 | chr18 | 55103307 | 55103486 |
| chr18 | 55103645 | 55103824 | chr18 | 55104744 | 55105244 | chr18 | 55105630 | 55106929 |
| chr18 | 55114441 | 55114740 | chr18 | 55850767 | 55851066 | chr18 | 56483824 | 56483938 |
| chr18 | 56815757 | 56815876 | chr18 | 56886981 | 56887517 | chr18 | 56888470 | 56888709 |
| chr18 | 56931460 | 56931682 | chr18 | 56931888 | 56932187 | chr18 | 56932256 | 56932375 |
| chr18 | 56934926 | 56935405 | chr18 | 56935920 | 56936159 | chr18 | 56939025 | 56939264 |
| chr18 | 56939324 | 56940823 | chr18 | 56940863 | 56941882 | chr18 | 57363606 | 57363845 |
| chr18 | 57364185 | 57364484 | chr18 | 57364556 | 57364795 | chr18 | 59000886 | 59001125 |
| chr18 | 59001222 | 59001821 | chr18 | 60263452 | 60263991 | chr18 | 60985417 | 60985825 |
| chr18 | 67067464 | 67068003 | chr18 | 67068059 | 67068298 | chr18 | 67068368 | 67068547 |
| chr18 | 67068614 | 67068913 | chr18 | 67069142 | 67069321 | chr18 | 70209058 | 70209297 |
| chr18 | 70209348 | 70209527 | chr18 | 70210483 | 70210583 | chr18 | 70211527 | 70211766 |
| chr18 | 70534207 | 70534686 | chr18 | 70534769 | 70535046 | chr18 | 70535299 | 70535658 |
| chr18 | 70535918 | 70536697 | chr18 | 70536750 | 70536972 | chr18 | 70537230 | 70537293 |
| chr18 | 73167500 | 73167919 | chr18 | 73627925 | 73628153 | chr18 | 74501045 | 74501267 |
| chr18 | 74755430 | 74755577 | chr18 | 74961264 | 74962247 | chr18 | 74962452 | 74962751 |
| chr18 | 74962896 | 74963675 | chr18 | 75339137 | 75339436 | chr18 | 75362839 | 75363078 |
| chr18 | 75551197 | 75551376 | chr18 | 75612137 | 75612376 | chr18 | 75999330 | 75999509 |
| chr18 | 76239460 | 76239699 | chr18 | 76501405 | 76501584 | chr18 | 76653557 | 76653736 |

TABLE 14-continued

| chr | start | end | chr | start | end | chr | start | end |
|---|---|---|---|---|---|---|---|---|
| chr18 | 76686175 | 76686354 | chr18 | 77143366 | 77143451 | chr18 | 77167752 | 77167929 |
| chr18 | 77181263 | 77181502 | chr18 | 77194838 | 77195077 | chr18 | 77205436 | 77205735 |
| chr18 | 77285814 | 77286113 | chr18 | 77309459 | 77309638 | chr18 | 77312784 | 77313017 |
| chr18 | 77329633 | 77330101 | chr18 | 77371350 | 77371589 | chr18 | 77543156 | 77543335 |
| chr18 | 77543673 | 77543912 | chr18 | 77547985 | 77548700 | chr18 | 77550108 | 77550467 |
| chr18 | 77557981 | 77558460 | chr18 | 77558732 | 77559101 | chr18 | 77576853 | 77577139 |
| chr18 | 77636517 | 77636696 | chr18 | 78005004 | 78005142 | chr19 | 403435 | 403888 |
| chr19 | 407106 | 407405 | chr19 | 462106 | 462235 | chr19 | 468683 | 468862 |
| chr19 | 485071 | 485490 | chr19 | 549287 | 549526 | chr19 | 555509 | 555625 |
| chr19 | 591272 | 591511 | chr19 | 592492 | 592654 | chr19 | 593197 | 593325 |
| chr19 | 599125 | 599424 | chr19 | 752060 | 752359 | chr19 | 869247 | 869363 |
| chr19 | 883529 | 883888 | chr19 | 883941 | 884240 | chr19 | 891441 | 891616 |
| chr19 | 955668 | 956327 | chr19 | 1003226 | 1003465 | chr19 | 1003583 | 1003822 |
| chr19 | 1004819 | 1005528 | chr19 | 1030082 | 1030309 | chr19 | 1047796 | 1047915 |
| chr19 | 1083392 | 1083526 | chr19 | 1156450 | 1156629 | chr19 | 1170089 | 1170328 |
| chr19 | 1171003 | 1171422 | chr19 | 1220349 | 1220696 | chr19 | 1236397 | 1236631 |
| chr19 | 1274683 | 1274922 | chr19 | 1308055 | 1308184 | chr19 | 1325714 | 1325989 |
| chr19 | 1401655 | 1401894 | chr19 | 1450236 | 1450475 | chr19 | 1467327 | 1468286 |
| chr19 | 1496313 | 1496552 | chr19 | 1496555 | 1496672 | chr19 | 1524289 | 1524528 |
| chr19 | 1525530 | 1526053 | chr19 | 1527132 | 1527307 | chr19 | 1754094 | 1754333 |
| chr19 | 1754653 | 1754892 | chr19 | 1757337 | 1757696 | chr19 | 1762376 | 1762675 |
| chr19 | 1764197 | 1764374 | chr19 | 1775037 | 1775338 | chr19 | 1776276 | 1776635 |
| chr19 | 1799957 | 1800376 | chr19 | 1807893 | 1808492 | chr19 | 2251075 | 2251794 |
| chr19 | 2251973 | 2252752 | chr19 | 2252901 | 2253860 | chr19 | 2274576 | 2274692 |
| chr19 | 2290165 | 2291124 | chr19 | 2302693 | 2303052 | chr19 | 2331339 | 2331518 |
| chr19 | 2513149 | 2513388 | chr19 | 2683817 | 2684046 | chr19 | 3041486 | 3041522 |
| chr19 | 3219355 | 3219659 | chr19 | 3296523 | 3296762 | chr19 | 3361055 | 3361474 |
| chr19 | 3562249 | 3562583 | chr19 | 3578062 | 3578301 | chr19 | 3778053 | 3778472 |
| chr19 | 3779177 | 3779536 | chr19 | 3785566 | 3786345 | chr19 | 3820952 | 3821311 |
| chr19 | 3822008 | 3822307 | chr19 | 3855322 | 3855681 | chr19 | 4054334 | 4054463 |
| chr19 | 4054540 | 4054573 | chr19 | 4311173 | 4311350 | chr19 | 4548040 | 4548459 |
| chr19 | 4550169 | 4550408 | chr19 | 4555813 | 4556214 | chr19 | 4557018 | 4557317 |
| chr19 | 4670678 | 4670857 | chr19 | 5292709 | 5292948 | chr19 | 5338820 | 5339239 |
| chr19 | 5759670 | 5759789 | chr19 | 5826175 | 5826284 | chr19 | 5910275 | 5910429 |
| chr19 | 5914687 | 5914866 | chr19 | 5914907 | 5915146 | chr19 | 6590244 | 6590582 |
| chr19 | 7794919 | 7795338 | chr19 | 7852944 | 7853243 | chr19 | 7853262 | 7853561 |
| chr19 | 8115149 | 8115376 | chr19 | 8576838 | 8577077 | chr19 | 9473555 | 9474140 |
| chr19 | 9517611 | 9517870 | chr19 | 9608817 | 9609116 | chr19 | 9609229 | 9609528 |
| chr19 | 9903828 | 9904054 | chr19 | 9937370 | 9937489 | chr19 | 10231221 | 10231331 |
| chr19 | 10361965 | 10362076 | chr19 | 10398128 | 10398367 | chr19 | 10405892 | 10406431 |
| chr19 | 10406798 | 10407211 | chr19 | 10527085 | 10527282 | chr19 | 10531317 | 10531616 |
| chr19 | 10531890 | 10532069 | chr19 | 10624659 | 10625558 | chr19 | 10823581 | 10823708 |
| chr19 | 11590929 | 11591288 | chr19 | 11592611 | 11592850 | chr19 | 11592942 | 11593241 |
| chr19 | 11689363 | 11689662 | chr19 | 11959816 | 11960175 | chr19 | 12163452 | 12163770 |
| chr19 | 12163819 | 12163998 | chr19 | 12175356 | 12175595 | chr19 | 12175731 | 12176090 |
| chr19 | 12202937 | 12203638 | chr19 | 12266924 | 12267763 | chr19 | 12305754 | 12306351 |
| chr19 | 12476405 | 12476465 | chr19 | 12476501 | 12476644 | chr19 | 12606297 | 12606556 |
| chr19 | 12750903 | 12751142 | chr19 | 12863329 | 12863616 | chr19 | 12951921 | 12952220 |
| chr19 | 12996076 | 12996375 | chr19 | 13210122 | 13210421 | chr19 | 13616617 | 13617336 |
| chr19 | 13618186 | 13618485 | chr19 | 13965933 | 13966022 | chr19 | 14181217 | 14181682 |
| chr19 | 14584149 | 14584868 | chr19 | 15090097 | 15090576 | chr19 | 15121611 | 15121970 |
| chr19 | 15122030 | 15122314 | chr19 | 15288346 | 15288945 | chr19 | 15292293 | 15292592 |
| chr19 | 15342635 | 15343411 | chr19 | 15344007 | 15344426 | chr19 | 17006991 | 17007764 |
| chr19 | 17008422 | 17008884 | chr19 | 17392545 | 17392964 | chr19 | 17717212 | 17717391 |
| chr19 | 17759145 | 17759504 | chr19 | 17791108 | 17791287 | chr19 | 17958396 | 17958935 |
| chr19 | 17983447 | 17983910 | chr19 | 18041167 | 18041286 | chr19 | 18103637 | 18103816 |
| chr19 | 18104390 | 18104493 | chr19 | 18271871 | 18271999 | chr19 | 18330935 | 18331234 |
| chr19 | 18343355 | 18343654 | chr19 | 18343823 | 18344062 | chr19 | 18383252 | 18383431 |
| chr19 | 18714465 | 18714764 | chr19 | 18811473 | 18811771 | chr19 | 18899333 | 18899718 |
| chr19 | 18901753 | 18902172 | chr19 | 18980680 | 18980979 | chr19 | 18989722 | 18990360 |
| chr19 | 18994808 | 18995227 | chr19 | 19334769 | 19334993 | chr19 | 19645776 | 19646015 |
| chr19 | 19651865 | 19652164 | chr19 | 20011908 | 20011992 | chr19 | 20012053 | 20012172 |
| chr19 | 20188746 | 20188865 | chr19 | 20189411 | 20189530 | chr19 | 21646333 | 21646512 |
| chr19 | 21769223 | 21769522 | chr19 | 22018429 | 22018724 | chr19 | 22034402 | 22034896 |
| chr19 | 22610542 | 22610827 | chr19 | 22715053 | 22715532 | chr19 | 23254115 | 23254294 |
| chr19 | 23257780 | 23258559 | chr19 | 23258680 | 23258799 | chr19 | 23299705 | 23299784 |
| chr19 | 23433104 | 23433223 | chr19 | 23598358 | 23598420 | chr19 | 24154518 | 24154697 |
| chr19 | 24216940 | 24217119 | chr19 | 29284377 | 29284796 | chr19 | 29505081 | 29505258 |
| chr19 | 30015844 | 30016803 | chr19 | 30016832 | 30018691 | chr19 | 30019043 | 30019942 |
| chr19 | 30020014 | 30020553 | chr19 | 30021040 | 30021279 | chr19 | 30215468 | 30215572 |
| chr19 | 30252214 | 30252330 | chr19 | 30555254 | 30555473 | chr19 | 30562687 | 30562831 |
| chr19 | 30537413 | 30637633 | chr19 | 30713384 | 30713803 | chr19 | 30713829 | 30714128 |
| chr19 | 30714425 | 30714508 | chr19 | 30715315 | 30715854 | chr19 | 30716236 | 30716655 |
| chr19 | 30716732 | 30718231 | chr19 | 30718761 | 30718934 | chr19 | 30719369 | 30720134 |
| chr19 | 30865626 | 30866525 | chr19 | 31804650 | 31804829 | chr19 | 31839670 | 31839969 |
| chr19 | 31841834 | 31842072 | chr19 | 31842116 | 31842493 | chr19 | 31842502 | 31842741 |
| chr19 | 32364265 | 32364504 | chr19 | 32516309 | 32516495 | chr19 | 32715588 | 32715827 |
| chr19 | 32898350 | 32898589 | chr19 | 33167035 | 33167514 | chr19 | 33467984 | 33468157 |

TABLE 14-continued

| chr | start | end | chr | start | end | chr | start | end |
|---|---|---|---|---|---|---|---|---|
| chr19 | 33685493 | 33685683 | chr19 | 33792412 | 33792612 | chr19 | 33794599 | 33794838 |
| chr19 | 34112185 | 34112424 | chr19 | 34113049 | 34113259 | chr19 | 34113678 |
| chr19 | 34113911 | 34114210 | chr19 | 34972390 | 34972569 | chr19 | 34973151 | 34973330 |
| chr19 | 34973558 | 34973797 | chr19 | 35263983 | 35264092 | chr19 | 35395923 | 35396462 |
| chr19 | 35616250 | 35616489 | chr19 | 35781298 | 35781537 | chr19 | 35797822 | 35798061 |
| chr19 | 36048504 | 36048863 | chr19 | 36049246 | 36049497 | chr19 | 36222334 | 36222567 |
| chr19 | 36249933 | 36250232 | chr19 | 36334884 | 36335243 | chr19 | 36347791 | 36348147 |
| chr19 | 36450030 | 36450449 | chr19 | 36523258 | 36523557 | chr19 | 36735953 | 36736132 |
| chr19 | 36736226 | 36736585 | chr19 | 36822249 | 36822968 | chr19 | 36909074 | 36910028 |
| chr19 | 36912257 | 36912496 | chr19 | 37095591 | 37096660 | chr19 | 37263439 | 37263678 |
| chr19 | 37264143 | 37264487 | chr19 | 37288237 | 37288869 | chr19 | 37341683 | 37342042 |
| chr19 | 37407046 | 37407525 | chr19 | 37463953 | 37464792 | chr19 | 37569394 | 37569573 |
| chr19 | 37702087 | 37702265 | chr19 | 37959762 | 37960061 | chr19 | 37997337 | 37998206 |
| chr19 | 38042290 | 38042769 | chr19 | 38085160 | 38085759 | chr19 | 38085958 | 38086110 |
| chr19 | 38145976 | 38146335 | chr19 | 38146364 | 38146663 | chr19 | 38182793 | 38183392 |
| chr19 | 38308031 | 38308543 | chr19 | 38480952 | 38481190 | chr19 | 38747072 | 38747448 |
| chr19 | 38755189 | 38755422 | chr19 | 38782485 | 38782664 | chr19 | 38789223 | 38789373 |
| chr19 | 38873861 | ?8874040 | chr19 | 38905446 | 38905805 | chr19 | 38974158 | 38974337 |
| chr19 | 39135435 | 39135554 | chr19 | 39687575 | 39687904 | chr19 | 39754787 | 39755446 |
| chr19 | 39816862 | 39817161 | chr19 | 39993392 | 39993751 | chr19 | 39997602 | 39997901 |
| chr19 | 40006093 | 40006392 | chr19 | 40006489 | 40006728 | chr19 | 40723923 | 40724342 |
| chr19 | 40829768 | 40830123 | chr19 | 40902350 | 40902779 | chr19 | 40951087 | 40951197 |
| chr19 | 40951602 | 40951841 | chr19 | 41018456 | 41019131 | chr19 | 41025462 | 41025761 |
| chr19 | 41059832 | 41060408 | chr19 | 41073513 | 41073752 | chr19 | 41119097 | 41119735 |
| chr19 | 41354575 | 41354814 | chr19 | 41641740 | 41641979 | chr19 | 42028407 | 42028646 |
| chr19 | 42408226 | 42408405 | chr19 | 42827810 | 42828349 | chr19 | 42856486 | 42856558 |
| chr19 | 44203735 | 44203962 | chr19 | 44405819 | 44406128 | chr19 | 44599691 | 44599803 |
| chr19 | 44905425 | 44905604 | chr19 | 44952193 | 44952909 | chr19 | 45003142 | 45003417 |
| chr19 | 45300052 | 45300291 | chr19 | 45570307 | 45570546 | chr19 | 45574391 | 45574570 |
| chr19 | 45574682 | 45574782 | chr19 | 45574837 | 45574981 | chr19 | 45655309 | 45656448 |
| chr19 | 45656589 | 45657008 | chr19 | 45657129 | 45657368 | chr19 | 45810006 | 45810345 |
| chr19 | 45835239 | 45835353 | chr19 | 45888843 | 45889484 | chr19 | 45997437 | 45997676 |
| chr19 | 46001945 | 46002424 | chr19 | 46234853 | 46234965 | chr19 | 46379822 | 46380241 |
| chr19 | 46404448 | 46404682 | chr19 | 46916631 | 46917170 | chr19 | 46930046 | 46930278 |
| chr19 | 46974477 | 46974776 | chr19 | 46992643 | 46992942 | chr19 | 46993067 | 46993486 |
| chr19 | 46996509 | 46996748 | chr19 | 46996775 | 46997010 | chr19 | 47152515 | 47153114 |
| chr19 | 47200270 | 47200629 | chr19 | 47910405 | 47910620 | chr19 | 47933223 | 47933822 |
| chr19 | 48003512 | 48003747 | chr19 | 48076568 | 48076747 | chr19 | 48137090 | 48137187 |
| chr19 | 48137247 | 48137389 | chr19 | 48151189 | 48151421 | chr19 | 48614769 | 48614851 |
| chr19 | 48771496 | 48771636 | chr19 | 48800507 | 48800866 | chr19 | 48857809 | 48857917 |
| chr19 | 48902834 | 48902953 | chr19 | 48918040 | 48918339 | chr19 | 49119155 | 49119334 |
| chr19 | 49127285 | 49127764 | chr19 | 49180431 | 49180610 | chr19 | 49399126 | 49399414 |
| chr19 | 49575386 | 49575565 | chr19 | 49646052 | 49646294 | chr19 | 49890810 | 49890908 |
| chr19 | 49935656 | 49936255 | chr19 | 49936790 | 49936969 | chr19 | 50028455 | 50028614 |
| chr19 | 50049635 | 50049746 | chr19 | 50215991 | 50216147 | chr19 | 50316147 | 50316566 |
| chr19 | 50353305 | 50353664 | chr19 | 50553917 | 50554516 | chr19 | 50816339 | 50816573 |
| chr19 | 50833750 | 50833966 | chr19 | 50938470 | 40938769 | chr19 | 51161151 | 51161330 |
| chr19 | 51162123 | 51162602 | chr19 | 51171130 | 51171369 | chr19 | 51227633 | 51227872 |
| chr19 | 51227975 | 51228154 | chr19 | 51228229 | 51228588 | chr19 | 51304487 | 51304666 |
| chr19 | 51520349 | 51520528 | chr19 | 51830748 | 51831227 | chr19 | 51831286 | 51831465 |
| chr19 | 52097592 | 52097831 | chr19 | 52207162 | 52207461 | chr19 | 52222438 | 52223192 |
| chr19 | 52552089 | 52552248 | chr19 | 52839494 | 52839700 | chr19 | 52840033 |
| chr19 | 52872943 | 52873542 | chr19 | 52956708 | 52956947 | chr19 | 53028835 | 53028952 |
| chr19 | 53031202 | 53031290 | chr19 | 53073476 | 53074075 | chr19 | 53141533 | 53141832 |
| chr19 | 53193757 | 53193996 | chr19 | 53194190 | 53194366 | chr19 | 53496630 | 53496928 |
| chr19 | 53561582 | 53561821 | chr19 | 53635873 | 53636168 | chr19 | 53661566 | 53661865 |
| chr19 | 53662195 | 53662722 | chr19 | 53696318 | 53696677 | chr19 | 53700514 | 53700693 |
| chr19 | 53757802 | 53758341 | chr19 | 53811774 | 53811986 | chr19 | 53836837 | 53836952 |
| chr19 | 53970464 | 53970636 | chr19 | 53970884 | 53971243 | chr19 | 54023803 | 54024282 |
| chr19 | 54024434 | 54024553 | chr19 | 54024619 | 54024973 | chr19 | 54411032 | 54411267 |
| chr19 | 54411482 | 64411661 | chr19 | 54412780 | 54413079 | chr19 | 54445250 | 54445609 |
| chr19 | 54481691 | 54482050 | chr19 | 54483091 | 54483630 | chr19 | 54485442 | 54485913 |
| chr19 | 56159350 | 56159596 | chr19 | 56201573 | 56201812 | chr19 | 56588806 | 56588868 |
| chr19 | 56728588 | 56729067 | chr19 | 56879426 | 56880075 | chr19 | 56904643 | 56905302 |
| chr19 | 56915225 | 56915524 | chr19 | 56988458 | 56988817 | chr19 | 56989432 | 56989851 |
| chr19 | 57050389 | 57050568 | chr19 | 57149480 | 57149719 | chr19 | 57154802 | 57155101 |
| chr19 | 57182906 | 57183423 | chr19 | 57276559 | 57276798 | chr19 | 57610771 | 57611067 |
| chr19 | 57617433 | 57618212 | chr19 | 57683078 | 57683372 | chr19 | 57862330 | 57862859 |
| chr19 | 57862930 | 57863229 | chr19 | 58011040 | 58011383 | chr19 | 58038708 | 58039067 |
| chr19 | 58094912 | 58095931 | chr19 | 58111529 | 58111888 | chr19 | 58125444 | 58125983 |
| chr19 | 58144419 | 58144778 | chr19 | 58219924 | 58220883 | chr19 | 58238234 | 58239187 |
| chr19 | 58399978 | 58400277 | chr19 | 58400319 | 58400618 | chr19 | 58458679 | 58459278 |
| chr19 | 58514416 | 58514655 | chr19 | 58520661 | 58521020 | chr19 | 58545042 | 58545843 |
| chr19 | 58570448 | 58570747 | chr19 | 58609299 | 58609944 | chr19 | 58629812 | 58630026 |
| chr19 | 58661815 | 58662174 | chr19 | 58666093 | 58666392 | chr19 | 58739983 | 58740222 |
| chr19 | 58874834 | 58874951 | chr19 | 58907613 | 58908272 | chr19 | 58951175 | 58952014 |
| chr19 | 58964105 | 58964283 | chr20 | 291052 | 291453 | chr20 | 399928 | 400167 |
| chr20 | 401079 | 401258 | chr20 | 401495 | 401854 | chr20 | 590349 | 590588 |

TABLE 14-continued

| chr | start | end | chr | start | end | chr | start | end |
|---|---|---|---|---|---|---|---|---|
| chr20 | 590661 | 590960 | chr20 | 592323 | 592547 | chr20 | 644096 | 644875 |
| chr20 | 799030 | 799146 | chr20 | 982660 | 983079 | chr20 | 1206766 | 1207125 |
| chr20 | 1783674 | 1784453 | chr20 | 2539252 | 2539851 | chr20 | 2668670 | 2669026 |
| chr20 | 2780654 | 2780747 | chr20 | 2780894 | 2781553 | chr20 | 2781657 | 2781836 |
| chr20 | 2785561 | 2786160 | chr20 | 3027666 | 3027780 | chr20 | 3052501 | 3052920 |
| chr20 | 3073395 | 3073994 | chr20 | 3204792 | 3205031 | chr20 | 3220799 | 3221038 |
| chr20 | 3229475 | 3229714 | chr20 | 3641656 | 3642015 | chr20 | 3662918 | 3663277 |
| chr20 | 4084983 | 4085146 | chr20 | 4229328 | 4229507 | chr20 | 4229684 | 4230684 |
| chr20 | 4802971 | 4803750 | chr20 | 4803846 | 4804053 | chr20 | 5296095 | 5296986 |
| chr20 | 5297106 | 5297705 | chr20 | 6022813 | 6023052 | chr20 | 6748832 | 6749131 |
| chr20 | 8112304 | 8112483 | chr20 | 8112642 | 8113121 | chr20 | 8113462 | 8113701 |
| chr20 | 9487302 | 9488032 | chr20 | 9488287 | 9488613 | chr20 | 9488650 | 9488934 |
| chr20 | 9488993 | 9489249 | chr20 | 9489377 | 9489796 | chr20 | 9495181 | 9495600 |
| chr20 | 9496253 | 9496912 | chr20 | 9496953 | 9497074 | chr20 | 10198206 | 10198685 |
| chr20 | 10198841 | 10199020 | chr20 | 13200498 | 13200737 | chr20 | 16555037 | 16555130 |
| chr20 | 17206434 | 17206840 | chr20 | 17207783 | 17208022 | chr20 | 17208484 | 17208723 |
| chr20 | 18039741 | 18039980 | chr20 | 19739495 | 19739794 | chr20 | 19928211 | 19928450 |
| chr20 | 20344410 | 20344649 | chr20 | 20345597 | 20346196 | chr20 | 20347358 | 20348257 |
| chr20 | 20348447 | 20348686 | chr20 | 20349055 | 20349354 | chr20 | 20349500 | 20349679 |
| chr20 | 21080615 | 21082354 | chr20 | 21082456 | 21082995 | chr20 | 21083322 | 21084461 |
| chr20 | 21085729 | 21085968 | chr20 | 21086075 | 21086554 | chr20 | 21086808 | 21087267 |
| chr20 | 21372091 | 21372810 | chr20 | 21376172 | 21378631 | chr20 | 21486299 | 21486958 |
| chr20 | 21487068 | 21487276 | chr20 | 21487368 | 21487667 | chr20 | 21488076 | 21488435 |
| chr20 | 21489135 | 21489794 | chr20 | 21490099 | 21491632 | chr20 | 21492292 | 21493071 |
| chr20 | 21493218 | 21494357 | chr20 | 21494438 | 21494797 | chr20 | 21495845 | 21496084 |
| chr20 | 21496158 | 21496397 | chr20 | 21496558 | 21497217 | chr20 | 21497337 | 21498716 |
| chr20 | 21500019 | 21500228 | chr20 | 21501294 | 21501814 | chr20 | 21501945 | 21502424 |
| chr20 | 21502495 | 21503214 | chr20 | 21503490 | 21503877 | chr20 | 21682309 | 21682548 |
| chr20 | 21683213 | 21683751 | chr20 | 21685592 | 21685606 | chr20 | 21686157 | 21686756 |
| chr20 | 21686921 | 21687820 | chr20 | 21689862 | 21690137 | chr20 | 21694425 | 21694604 |
| chr20 | 21695014 | 21695391 | chr20 | 21748349 | 21748588 | chr20 | 22557301 | 22557776 |
| chr20 | 22557898 | 22558197 | chr20 | 22558534 | 22558773 | chr20 | 22559549 | 22559788 |
| chr20 | 22562632 | 22562931 | chr20 | 22563690 | 22563703 | chr20 | 22564161 | 22564291 |
| chr20 | 23015843 | 23015942 | chr20 | 23029012 | 23029251 | chr20 | 23029303 | 23030442 |
| chr20 | 23031471 | 23031729 | chr20 | 24450133 | 24450612 | chr20 | 24450692 | 24451111 |
| chr20 | 24451372 | 24451671 | chr20 | 25058292 | 25058711 | chr20 | 25061654 | 25062973 |
| chr20 | 25063700 | 25064539 | chr20 | 25065078 | 25065497 | chr20 | 25129345 | 25129544 |
| chr20 | 25230415 | 25230513 | chr20 | 25230775 | 25230894 | chr20 | 26188813 | 26189092 |
| chr20 | 26190218 | 26190432 | chr20 | 30101724 | 30101833 | chr20 | 30582655 | 30583074 |
| chr20 | 30639051 | 30639410 | chr20 | 30639531 | 30639570 | chr20 | 30639603 | 30639950 |
| chr20 | 30640009 | 30640368 | chr20 | 30777930 | 30778339 | chr20 | 31115592 | 31115891 |
| chr20 | 31151695 | 31151874 | chr20 | 32301800 | 32302039 | chr20 | 32450399 | 32450518 |
| chr20 | 33547579 | 33547685 | chr20 | 33574834 | 33574981 | chr20 | 34041903 | 34042004 |
| chr20 | 34147928 | 34148347 | chr20 | 34188525 | 34189484 | chr20 | 34189534 | 34190013 |
| chr20 | 36531706 | 36532005 | chr20 | 36781250 | 36781429 | chr20 | 37302601 | 37303440 |
| chr20 | 37351701 | 37352720 | chr20 | 37353096 | 37353335 | chr20 | 37353378 | 37353857 |
| chr20 | 37354045 | 37355304 | chr20 | 37355761 | 37357440 | chr20 | 37357739 | 37358278 |
| chr20 | 37434469 | 37434828 | chr20 | 37435012 | 37435311 | chr20 | 37435362 | 37435961 |
| chr20 | 39316114 | 39316413 | chr20 | 39316814 | 39317473 | chr20 | 39317659 | 39318138 |
| chr20 | 39319031 | 39319750 | chr20 | 39995061 | 39995900 | chr20 | 41817697 | 41818176 |
| chr20 | 41818472 | 41819011 | chr20 | 42136252 | 42136491 | chr20 | 42218593 | 42218757 |
| chr20 | 42543655 | 42543954 | chr20 | 42545078 | 42876457 | chr20 | 42876670 |  |
| chr20 | 43437970 | 43438569 | chr20 | 43438883 | 43439122 | chr20 | 43439192 | 43439611 |
| chr20 | 44452628 | 44453152 | chr20 | 44519003 | 44519182 | chr20 | 44601980 | 44602069 |
| chr20 | 44639100 | 44639579 | chr20 | 44640264 | 44640443 | chr20 | 44660665 | 44660964 |
| chr20 | 44686087 | 44686866 | chr20 | 44803096 | 44803755 | chr20 | 44875147 | 44875506 |
| chr20 | 44879700 | 44880179 | chr20 | 44937124 | 44937369 | chr20 | 44937444 | 44937723 |
| chr20 | 44941441 | 44941740 | chr20 | 45141897 | 45142331 | chr20 | 45279779 | 45280491 |
| chr20 | 45337726 | 45338025 | chr20 | 45524449 | 45524628 | chr20 | 47247136 | 47247407 |
| chr20 | 47274032 | 47274137 | chr20 | 47296021 | 47296320 | chr20 | 47443647 | 47444366 |
| chr20 | 47905336 | 47905687 | chr20 | 47934747 | 47935346 | chr20 | 47935412 | 47935651 |
| chr20 | 47935829 | 47936128 | chr20 | 48184289 | 48184528 | chr20 | 49204105 | 49204524 |
| chr20 | 49261715 | 49262194 | chr20 | 49358363 | 49358477 | chr20 | 49377912 | 49378139 |
| chr20 | 49381177 | 49381340 | chr20 | 49575835 | 49575938 | chr20 | 49575988 | 49576014 |
| chr20 | 49639698 | 49640237 | chr20 | 50383399 | 50383504 | chr20 | 50384683 | 50384982 |
| chr20 | 50720356 | 50722021 | chr20 | 50722096 | 50722201 | chr20 | 50722609 | 50722908 |
| chr20 | 51589688 | 51589987 | chr20 | 52311387 | 52311505 | chr20 | 52789371 | 52789550 |
| chr20 | 52789765 | 52790244 | chr20 | 53092165 | 53092464 | chr20 | 53093011 | 53093190 |
| chr20 | 54578407 | 54578826 | chr20 | 54579809 | 54580408 | chr20 | 54580484 | 54580783 |
| chr20 | 55199952 | 55200791 | chr20 | 55200828 | 55201187 | chr20 | 55201399 | 55201638 |
| chr20 | 55201686 | 55202705 | chr20 | 55202728 | 55203207 | chr20 | 55204224 | 55204703 |
| chr20 | 55204864 | 55205103 | chr20 | 55205956 | 55206495 | chr20 | 55499394 | 55499813 |
| chr20 | 55499932 | 55500171 | chr20 | 55500531 | 55501040 | chr20 | 55693446 | 55693610 |
| chr20 | 55841036 | 55841455 | chr20 | 55841994 | 55842293 | chr20 | 56766086 | 56766203 |
| chr20 | 56803301 | 55803540 | chr20 | 56803762 | 56804001 | chr20 | 57089355 | 57089594 |
| chr20 | 57089720 | 57090259 | chr20 | 57224746 | 57225405 | chr20 | 58152557 | 58152796 |
| chr20 | 58179713 | 58179952 | chr20 | 58180018 | 58180497 | chr20 | 58508795 | 58509005 |
| chr20 | 59804233 | 59804323 | chr20 | 59826885 | 59827304 | chr20 | 59827702 | 59828541 |

TABLE 14-continued

| chr | start | end | chr | start | end | chr | start | end |
|---|---|---|---|---|---|---|---|---|
| chr20 | 59880480 | 59880575 | chr20 | 59910084 | 59910441 | chr20 | 59972951 | 59973170 |
| chr20 | 60202541 | 60202699 | chr20 | 60235251 | 60235610 | chr20 | 60238278 | 60238574 |
| chr20 | 60238780 | 60239079 | chr20 | 60243860 | 60244206 | chr20 | 60329482 | 60329661 |
| chr20 | 60359835 | 60359954 | chr20 | 60374934 | 60375173 | chr20 | 60439546 | 60439845 |
| chr20 | 60453829 | 60454186 | chr20 | 60477213 | 60477632 | chr20 | 60485281 | 60485480 |
| chr20 | 60502956 | 60503135 | chr20 | 60620233 | 60620412 | chr20 | 60772886 | 60773905 |
| chr20 | 60789866 | 60790225 | chr20 | 50925945 | 60926124 | chr20 | 50970879 | 60971058 |
| chr20 | 60983756 | 60984115 | chr20 | 60984356 | 60984553 | chr20 | 61287993 | 61288232 |
| chr20 | 61288380 | 61288619 | chr20 | 61294596 | 61294955 | chr20 | 61340486 | 61340785 |
| chr20 | 61412227 | 61412451 | chr20 | 61505882 | 61506421 | chr20 | 61532457 | 61532696 |
| chr20 | 61560341 | 61561000 | chr20 | 61585679 | 61585823 | chr20 | 61585900 | 61586079 |
| chr20 | 61636755 | 61636994 | chr20 | 61637391 | 61638710 | chr20 | 61703613 | 61703972 |
| chr20 | 61714683 | 61714696 | chr20 | 61734332 | 61734571 | chr20 | 61747795 | 61748034 |
| chr20 | 61763524 | 61763703 | chr20 | 61765251 | 61765490 | chr20 | 61808107 | 61808346 |
| chr20 | 61808388 | 61810187 | chr20 | 61823076 | 61823195 | chr20 | 61862297 | 61862460 |
| chr20 | 61885146 | 61885565 | chr20 | 61885609 | 61885848 | chr20 | 61885984 | 61886343 |
| chr20 | 61886651 | 61886830 | chr20 | 61974094 | 61974453 | chr20 | 61980769 | 61981068 |
| chr20 | 62031085 | 62031324 | chr20 | 62031958 | 62032197 | chr20 | 62037460 | 62037699 |
| chr20 | 62046145 | 62046504 | chr20 | 62058624 | 62058859 | chr20 | 62090442 | 62090621 |
| chr20 | 62097763 | 62097771 | chr20 | 62115188 | 62115367 | chr20 | 62119246 | 62120252 |
| chr20 | 62126035 | 62126514 | chr20 | 62157232 | 62157349 | chr20 | 62165548 | 62165847 |
| chr20 | 62167480 | 62167659 | chr20 | 62170105 | 62170284 | chr20 | 62172851 | 62173150 |
| chr20 | 62185296 | 62185535 | chr20 | 62321125 | 62321424 | chr20 | 62321551 | 62321970 |
| chr20 | 62340233 | 62340423 | chr20 | 62383135 | 62383374 | chr20 | 62461263 | 62461562 |
| chr20 | 62488263 | 62488442 | chr20 | 62680682 | 62680818 | chr20 | 62714923 | 62714946 |
| chr20 | 62715097 | 62715162 | chr21 | 22370246 | 22370545 | chr21 | 22370614 | 22370793 |
| chr21 | 26934278 | 26934877 | chr21 | 27011671 | 27011910 | chr21 | 27012283 | 27012622 |
| chr21 | 27944919 | 27945158 | chr21 | 27945324 | 27945503 | chr21 | 27945619 | 27945798 |
| chr21 | 28216509 | 28217768 | chr21 | 28218671 | 28218815 | chr21 | 28218877 | 28219150 |
| chr21 | 28338743 | 28338848 | chr21 | 28339165 | 28339584 | chr21 | 28339806 | 28340405 |
| chr21 | 31015127 | 31015306 | chr21 | 31311330 | 31311629 | chr21 | 31311846 | 31312205 |
| chr21 | 31312230 | 31312259 | chr21 | 31312305 | 31312409 | chr21 | 33244901 | 33245131 |
| chr21 | 33245582 | 33245593 | chr21 | 33245716 | 33245821 | chr21 | 33245921 | 33245955 |
| chr21 | 33246038 | 33246280 | chr21 | 33627450 | 33627569 | chr21 | 33721671 | 33721910 |
| chr21 | 33983153 | 33983320 | chr21 | 34392070 | 34392669 | chr21 | 34395217 | 34396356 |
| chr21 | 34396707 | 34396870 | chr21 | 34396903 | 34397178 | chr21 | 34397993 | 34398712 |
| chr21 | 34398847 | 34400346 | chr21 | 34401110 | 34401469 | chr21 | 34442457 | 34442696 |
| chr21 | 34443004 | 34443363 | chr21 | 34443419 | 34443778 | chr21 | 34443806 | 34444045 |
| chr21 | 34444082 | 34444681 | chr21 | 36041374 | 36041793 | chr21 | 36041903 | 36042322 |
| chr21 | 36042581 | 36042940 | chr21 | 37527854 | 37528033 | chr21 | 37758492 | 37758611 |
| chr21 | 37774963 | 37775238 | chr21 | 38064415 | 38064714 | chr21 | 38064917 | 38065832 |
| chr21 | 38065855 | 38066214 | chr21 | 38067247 | 38067308 | chr21 | 38068092 | 38068384 |
| chr21 | 38068465 | 38068871 | chr21 | 38069125 | 38069298 | chr21 | 38069359 | 38069598 |
| chr21 | 38069725 | 38070144 | chr21 | 38070616 | 38070855 | chr21 | 38071699 | 38071781 |
| chr21 | 38071933 | 38071998 | chr21 | 38072920 | 38073159 | chr21 | 38073221 | 38073940 |
| chr21 | 38076764 | 38077243 | chr21 | 38078332 | 38078571 | chr21 | 38079887 | 38080786 |
| chr21 | 38081112 | 38081296 | chr21 | 38081371 | 38081910 | chr21 | 38081968 | 38082011 |
| chr21 | 38082854 | 38083258 | chr21 | 38092081 | 38092320 | chr21 | 38119809 | 38120408 |
| chr21 | 38638505 | 38638624 | chr21 | 38935395 | 38935601 | chr21 | 39047688 | 39047889 |
| chr21 | 40984719 | 40984898 | chr21 | 43376299 | 43376478 | chr21 | 43786609 | 43786788 |
| chr21 | 43991389 | 43991568 | chr21 | 44283611 | 44283850 | chr21 | 44494814 | 44495233 |
| chr21 | 44837002 | 44837245 | chr21 | 44837296 | 44837301 | chr21 | 44847488 | 44847722 |
| chr21 | 44866508 | 44866807 | chr21 | 45148538 | 45148837 | chr21 | 45195115 | 45196414 |
| chr21 | 45273636 | 45273995 | chr21 | 45508543 | 45508662 | chr21 | 45791005 | 45791184 |
| chr21 | 46036556 | 46036855 | chr21 | 46126009 | 46126267 | chr21 | 46126388 | 46126807 |
| chr21 | 46126948 | 46127187 | chr21 | 46127468 | 46127628 | chr21 | 46128801 | 46129040 |
| chr21 | 46129346 | 46129585 | chr21 | 46257016 | 46257375 | chr21 | 46310341 | 46310580 |
| chr21 | 46318196 | 46318435 | chr21 | 46319069 | 46319548 | chr21 | 46359099 | 46359338 |
| chr21 | 46452278 | 46452637 | chr21 | 46677646 | 46677885 | chr21 | 46825737 | 46825823 |
| chr21 | 46863675 | 46863803 | chr21 | 46925704 | 46925999 | chr21 | 46926363 | 46926662 |
| chr21 | 46935727 | 46936018 | chr21 | 47010168 | 47010527 | chr21 | 47062446 | 47062925 |
| chr21 | 47063451 | 47064050 | chr21 | 47064165 | 47064464 | chr21 | 47404071 | 47404429 |
| chr21 | 47504759 | 47504994 | chr21 | 47518676 | 47518915 | chr21 | 47717485 | 47717541 |
| chr21 | 47717623 | 47717665 | chr21 | 47746183 | 47746482 | chr22 | 17081848 | 17082087 |
| chr22 | 17082492 | 17082671 | chr22 | 17082854 | 17083093 | chr22 | 17083297 | 17083596 |
| chr22 | 17600988 | 17601467 | chr22 | 17602419 | 17602718 | chr22 | 17850359 | 17850718 |
| chr22 | 18009986 | 18010085 | chr22 | 18328049 | 18328348 | chr22 | 19017431 | 19017670 |
| chr22 | 19117490 | 19117669 | chr22 | 19510704 | 19511663 | chr22 | 19511765 | 19512184 |
| chr22 | 19706119 | 19706754 | chr22 | 19742753 | 19743052 | chr22 | 19748561 | 19749040 |
| chr22 | 20792372 | 20792689 | chr22 | 21153919 | 21154084 | chr22 | 21304980 | 21305098 |
| chr22 | 21368513 | 21368692 | chr22 | 21977249 | 21977451 | chr22 | 21982708 | 21983062 |
| chr22 | 22006004 | 22006243 | chr22 | 22058102 | 22058341 | chr22 | 22090520 | 22090819 |
| chr22 | 22862704 | 22863243 | chr22 | 22901011 | 22901550 | chr22 | 23791328 | 23791607 |
| chr22 | 23801388 | 23801567 | chr22 | 24180608 | 24180847 | chr22 | 24560283 | 24560522 |
| chr22 | 24820244 | 24820483 | chr22 | 25678654 | 25679433 | chr22 | 25817025 | 25817264 |
| chr22 | 25817356 | 25817715 | chr22 | 28198468 | 28198601 | chr22 | 28371575 | 28371754 |
| chr22 | 28838105 | 28838396 | chr22 | 28838411 | 28838524 | chr22 | 29091752 | 29091929 |
| chr22 | 29445659 | 29446018 | chr22 | 29876117 | 29876189 | chr22 | 29877142 | 29877381 |

TABLE 14-continued

| chr | start | end | chr | start | end | chr | start | end |
|---|---|---|---|---|---|---|---|---|
| chr22 | 29977650 | 29977755 | chr22 | 30116824 | 30117240 | chr22 | 30158246 | 30158365 |
| chr22 | 30938434 | 30938673 | chr22 | 31198416 | 31198715 | chr22 | 31218436 | 31218615 |
| chr22 | 31218693 | 31218932 | chr22 | 31481052 | 31481411 | chr22 | 32748862 | 32749041 |
| chr22 | 33197509 | 33197748 | chr22 | 33453802 | 33454452 | chr22 | 35848275 | 35848476 |
| chr22 | 36902217 | 36902456 | chr22 | 38199683 | 38199982 | chr22 | 38220568 | 38221287 |
| chr22 | 38476983 | 38477882 | chr22 | 38592953 | 38593132 | chr22 | 38639155 | 38639308 |
| chr22 | 39784390 | 39784599 | chr22 | 39830257 | 39830492 | chr22 | 39853438 | 39853677 |
| chr22 | 39932459 | 39932638 | chr22 | 39954323 | 39954615 | chr22 | 40042536 | 40042835 |
| chr22 | 40075089 | 40075328 | chr22 | 40226368 | 40226487 | chr22 | 41048414 | 41048593 |
| chr22 | 41048654 | 41048951 | chr22 | 41634334 | 41634618 | chr22 | 41636999 | 41637217 |
| chr22 | 41657217 | 41657442 | chr22 | 42095992 | 42096276 | chr22 | 42310005 | 42310304 |
| chr22 | 42311435 | 42311674 | chr22 | 42353530 | 42353992 | chr22 | 42667276 | 42667501 |
| chr22 | 42679636 | 42679935 | chr22 | 43012441 | 43012560 | chr22 | 43012883 | 43012980 |
| chr22 | 43083029 | 43083145 | chr22 | 43434340 | 43434579 | chr22 | 43739987 | 43740226 |
| chr22 | 43808205 | 43808502 | chr22 | 44208422 | 44208621 | chr22 | 44258287 | 44258586 |
| chr22 | 44287554 | 44287793 | chr22 | 44455605 | 44455844 | chr22 | 45088524 | 45088823 |
| chr22 | 45135840 | 45136079 | chr22 | 45277218 | 45277397 | chr22 | 45402991 | 45403230 |
| chr22 | 45404106 | 45404525 | chr22 | 45404909 | 45405148 | chr22 | 45405219 | 45405518 |
| chr22 | 45405545 | 45405803 | chr22 | 45406181 | 45406420 | chr22 | 45593572 | 45593799 |
| chr22 | 45604107 | 45604444 | chr22 | 46262352 | 46263911 | chr22 | 46367955 | 46368134 |
| chr22 | 46438002 | 46438112 | chr22 | 46658700 | 46658939 | chr22 | 46931177 | 46931336 |
| chr22 | 46933014 | 46933104 | chr22 | 47004998 | 47005237 | chr22 | 47023028 | 47023267 |
| chr22 | 47054612 | 47054700 | chr22 | 47193234 | 47193473 | chr22 | 47525747 | 47525986 |
| chr22 | 48027582 | 48027731 | chr22 | 48884957 | 48885136 | chr22 | 48885210 | 48885989 |
| chr22 | 48886575 | 48886934 | chr22 | 48931805 | 48932104 | chr22 | 48971050 | 48971829 |
| chr22 | 48972042 | 48972761 | chr22 | 49852543 | 49852722 | chr22 | 49979553 | 49979835 |
| chr22 | 50001612 | 50001912 | chr22 | 50002684 | 50002911 | chr22 | 50003130 | 50003309 |
| chr22 | 50010037 | 50010336 | chr22 | 50010374 | 50010673 | chr22 | 50031617 | 50031796 |
| chr22 | 50149332 | 50149548 | chr22 | 50466931 | 50467045 | chr22 | 50496761 | 50497000 |
| chr22 | 50497068 | 50497367 | chr22 | 50623595 | 50623894 | chr22 | 50899214 | 50899753 |
| chr22 | 50943082 | 50943358 | chr22 | 51042185 | 51042881 | chr22 | 51112072 | 51112311 |
| chrX | 3746538 | 3746717 | chrX | 6145241 | 6145780 | chrX | 8698761 | 8699000 |
| chrX | 8699416 | 8699655 | chrX | 136656489 | 136656534 | AC211950.2_11234-25326 | 181 | 343 |
| AC211950.2_11234-25326 | 13241 | 13420 | AC211950.2_11234-25325 | 13667 | 13966 | AC241851.2_88-34049 | 15187 | 15426 |
| AEKP01168736.1_1-4752 | 1662 | 1781 | AEKP01168736.1_1-4752 | 1874 | 2381 | JH636052.4 | 5118687 | 5118986 |
| NW_001838016.1_818233-828058 | 6095 | 6142 | — | — | — | — | — | — |

TABLE 15

| chr | start | end | chr | start | end | chr | start | end |
|---|---|---|---|---|---|---|---|---|
| chr1 | 898633 | 898792 | chr1 | 913445 | 914044 | chr1 | 1080495 | 1080914 |
| chr1 | 1146657 | 1146896 | chr1 | 1218688 | 1218779 | chr1 | 1223433 | 1223595 |
| chr1 | 1235811 | 1236156 | chr1 | 1266957 | 1267233 | chr1 | 1267372 | 1267791 |
| chr1 | 1267823 | 1268242 | chr1 | 1341738 | 1341826 | chr1 | 1475458 | 1475644 |
| chr1 | 1476255 | 1476417 | chr1 | 1483096 | 1483139 | chr1 | 1563119 | 1563298 |
| chr1 | 1856362 | 1856471 | chr1 | 1857759 | 1857811 | chr1 | 1874647 | 1874877 |
| chr1 | 1910341 | 1910465 | chr1 | 1935188 | 1935207 | chr1 | 1935232 | 1935289 |
| chr1 | 1935291 | 1935547 | chr1 | 1974768 | 1974802 | chr1 | 2066406 | 2066756 |
| chr1 | 2125141 | 2125560 | chr1 | 2263067 | 2263366 | chr1 | 2267472 | 2267771 |
| chr1 | 2304239 | 2304478 | chr1 | 2307851 | 2307970 | chr1 | 2308023 | 2308030 |
| chr1 | 2308297 | 2308716 | chr1 | 2309792 | 2309994 | chr1 | 2331281 | 2331500 |
| chr1 | 2336323 | 2336440 | chr1 | 2375047 | 2375646 | chr1 | 2396927 | 2397106 |
| chr1 | 2428239 | 2428478 | chr1 | 2472089 | 2472388 | chr1 | 2506974 | 2507150 |
| chr1 | 2520925 | 2521062 | chr1 | 2706308 | 2706335 | chr1 | 2830081 | 2830147 |
| chr1 | 2865964 | 2866143 | chr1 | 2984645 | 2984824 | chr1 | 3102567 | 3102856 |
| chr1 | 3182781 | 3182874 | chr1 | 3182942 | 3183020 | chr1 | 3322011 | 3322250 |
| chr1 | 3567062 | 3567345 | chr1 | 3567738 | 3567851 | chr1 | 3567883 | 3568320 |
| chr1 | 3601749 | 3602030 | chr1 | 3659530 | 3659643 | chr1 | 3659672 | 3659769 |
| chr1 | 3663458 | 3663637 | chr1 | 3663779 | 3664018 | chr1 | 3664606 | 3664781 |
| chr1 | 3683723 | 3683902 | chr1 | 4111087 | 4111323 | chr1 | 4713943 | 4714075 |
| chr1 | 4714164 | 4714362 | chr1 | 4715428 | 4715540 | chr1 | 4715575 | 4716537 |
| chr1 | 4716539 | 4716744 | chr1 | 6166262 | 6166561 | chr1 | 6171668 | 6171907 |
| chr1 | 6186410 | 6186649 | chr1 | 6280169 | 6280348 | chr1 | 6304103 | 6304342 |
| chr1 | 6446041 | 6446400 | chr1 | 6480434 | 6480913 | chr1 | 6500911 | 6500988 |
| chr1 | 6501055 | 6501262 | chr1 | 6507603 | 6508202 | chr1 | 7764540 | 7764775 |
| chr1 | 8277776 | 8277837 | chr1 | 9712017 | 9712179 | chr1 | 9712459 | 9713096 |
| chr1 | 10166481 | 10166626 | chr1 | 10948478 | 10948657 | chr1 | 11538796 | 11538913 |
| chr1 | 11539101 | 11539280 | chr1 | 11539336 | 11539515 | chr1 | 11540040 | 11540179 |
| chr1 | 11591712 | 11591863 | chr1 | 11752375 | 11752614 | chr1 | 11936674 | 11936779 |
| chr1 | 11958996 | 11959295 | chr1 | 12041511 | 12041630 | chr1 | 12123143 | 12123554 |

TABLE 15-continued

| chr | start | end | chr | start | end | chr | start | end |
|---|---|---|---|---|---|---|---|---|
| chr1 | 12227604 | 12227805 | chr1 | 12251342 | 12252059 | chr1 | 13839669 | 13839769 |
| chr1 | 13910336 | 13910698 | chr1 | 13910700 | 13910757 | chr1 | 13910794 | 13910815 |
| chr1 | 14026401 | 14026700 | chr1 | 14730390 | 14730502 | chr1 | 14925417 | 14926136 |
| chr1 | 15251113 | 15251316 | chr1 | 15480854 | 15480983 | chr1 | 16085267 | 16085288 |
| chr1 | 16474984 | 16475299 | chr1 | 16861448 | 16861627 | chr1 | 17445781 | 17446011 |
| chr1 | 18437373 | 18437431 | chr1 | 18437433 | 18437612 | chr1 | 18956114 | 18956353 |
| chr1 | 18956383 | 18956408 | chr1 | 18956496 | 18956611 | chr1 | 18956782 | 18957321 |
| chr1 | 18957428 | 18957667 | chr1 | 18957938 | 18958229 | chr1 | 18958359 | 18958477 |
| chr1 | 18959346 | 18959390 | chr1 | 18959456 | 18959645 | chr1 | 18960795 | 18961094 |
| chr1 | 18962648 | 18963231 | chr1 | 18969543 | 18969902 | chr1 | 18971772 | 18972011 |
| chr1 | 18972056 | 18972170 | chr1 | 19043472 | 19043743 | chr1 | 19043757 | 19043771 |
| chr1 | 19992272 | 19992313 | chr1 | 19992433 | 19992511 | chr1 | 20127444 | 20127555 |
| chr1 | 20618230 | 20618469 | chr1 | 20878953 | 20879029 | chr1 | 20879031 | 20879229 |
| chr1 | 20879256 | 20879372 | chr1 | 20879482 | 20879721 | chr1 | 20879752 | 20880051 |
| chr1 | 20880095 | 20880694 | chr1 | 21026082 | 21026253 | chr1 | 21042820 | 21042999 |
| chr1 | 21044024 | 21044263 | chr1 | 21573736 | 21574215 | chr1 | 21835856 | 21836095 |
| chr1 | 22140674 | 22141014 | chr1 | 22141016 | 22141393 | chr1 | 22927327 | 22927566 |
| chr1 | 23748907 | 23749146 | chr1 | 23884996 | 23885088 | chr1 | 25255921 | 25256029 |
| chr1 | 25256280 | 25256459 | chr1 | 25257157 | 25257305 | chr1 | 25257391 | 25257464 |
| chr1 | 26551597 | 26551625 | chr1 | 26551729 | 26551896 | chr1 | 26551989 | 26552228 |
| chr1 | 26737509 | 26737688 | chr1 | 26737855 | 26737883 | chr1 | 26737908 | 26738274 |
| chr1 | 27190078 | 27190377 | chr1 | 27844444 | 27844623 | chr1 | 29450398 | 29450637 |
| chr1 | 29585984 | 29586763 | chr1 | 29804872 | 29805171 | chr1 | 30351469 | 30351828 |
| chr1 | 30815328 | 30815417 | chr1 | 30815455 | 30815675 | chr1 | 31863112 | 31863130 |
| chr1 | 32180323 | 32180502 | chr1 | 32237507 | 32237546 | chr1 | 32237639 | 32238586 |
| chr1 | 32410202 | 32410364 | chr1 | 32705425 | 32705639 | chr1 | 32756421 | 32756519 |
| chr1 | 32930524 | 32930658 | chr1 | 34628874 | 34629053 | chr1 | 34629390 | 34629809 |
| chr1 | 34630473 | 34630712 | chr1 | 34630770 | 34631069 | chr1 | 34631502 | 34631741 |
| chr1 | 34631872 | 34631892 | chr1 | 34632023 | 34632038 | chr1 | 34642298 | 34642490 |
| chr1 | 35258557 | 35258796 | chr1 | 35350980 | 35351759 | chr1 | 35395450 | 35395541 |
| chr1 | 35395543 | 35395929 | chr1 | 35664721 | 35664836 | chr1 | 36042605 | 36043564 |
| chr1 | 36563382 | 36563621 | chr1 | 37498718 | 37498845 | chr1 | 37498889 | 37499257 |
| chr1 | 37499358 | 37499683 | chr1 | 37500014 | 37500257 | chr1 | 37500368 | 37500441 |
| chr1 | 37500443 | 37500575 | chr1 | 37500603 | 37500907 | chr1 | 37500998 | 37501107 |
| chr1 | 38100591 | 38100787 | chr1 | 38219635 | 38219874 | chr1 | 38229961 | 38230243 |
| chr1 | 38230283 | 38230380 | chr1 | 38230700 | 38230937 | chr1 | 38398356 | 38398431 |
| chr1 | 38510079 | 38510258 | chr1 | 38510475 | 38510714 | chr1 | 38510778 | 38510933 |
| chr1 | 38510935 | 38511197 | chr1 | 38511252 | 38511800 | chrj | 38511822 | 38511911 |
| chr1 | 38512311 | 38512490 | chr1 | 38513162 | 38513229 | chr1 | 39269662 | 39270201 |
| chr1 | 40137822 | 40138061 | chr1 | 40237053 | 40237281 | chr1 | 40349627 | 40349746 |
| chr1 | 41284058 | 41284541 | chr1 | 41847494 | 41847793 | chr1 | 41848778 | 41848889 |
| chr1 | 41967261 | 41967360 | chr1 | 41991552 | 41991791 | chr1 | 43834653 | 43834807 |
| chr1 | 44068700 | 44068879 | chr1 | 44726821 | 44727360 | chr1 | 44872358 | 44872723 |
| chr1 | 44872924 | 44873064 | chr1 | 44873066 | 44873173 | chr1 | 44873510 | 44873797 |
| chr1 | 44883030 | 44883215 | chr1 | 44883752 | 44884123 | chr1 | 44884204 | 44884289 |
| chr1 | 45308239 | 45308358 | chr1 | 45308655 | 45308729 | chr1 | 46632781 | 46633020 |
| chr1 | 46913761 | 46913877 | chr1 | 46913887 | 46914246 | chr1 | 46914286 | 46914360 |
| chr1 | 46914582 | 46914641 | chr1 | 46932686 | 46932842 | chr1 | 46951114 | 46951318 |
| chr1 | 46951645 | 46951833 | chr1 | 46956380 | 46956616 | chr1 | 46956728 | 46956839 |
| chr1 | 46956841 | 46957246 | chr1 | 47009851 | 47009886 | chr1 | 47009911 | 47010036 |
| chr1 | 47010105 | 47010150 | chr1 | 47695033 | 47695512 | chr1 | 47696207 | 47696521 |
| chr1 | 47696621 | 47696686 | chr1 | 47696727 | 47696965 | chr1 | 47696987 | 47697206 |
| chr1 | 47697254 | 47697255 | chr1 | 47697280 | 47697613 | chr1 | 47697642 | 47697947 |
| chr1 | 47698007 | 47698301 | chr1 | 47881984 | 47882265 | chr1 | 47882267 | 47882403 |
| chr1 | 47882697 | 47882906 | chr1 | 47909640 | 47910239 | chr1 | 47910420 | 47910625 |
| chr1 | 47910749 | 47911019 | chr1 | 47911243 | 47911335 | chr1 | 48058982 | 48059341 |
| chr1 | 49242260 | 49242359 | chr1 | 49242361 | 49242513 | chr1 | 49242515 | 49242619 |
| chr1 | 50513541 | 50513837 | chr1 | 50799190 | 50799317 | chr1 | 50799394 | 50799489 |
| chr1 | 50880932 | 50881317 | chr1 | 50881427 | 50881957 | chr1 | 50882144 | 50882625 |
| chr1 | 50882731 | 50883690 | chr1 | 50883800 | 50883977 | chr1 | 50884021 | 50884353 |
| chr1 | 50884691 | 50884888 | chr1 | 50885262 | 50885441 | chr1 | 50886107 | 50887085 |
| chr1 | 50887176 | 50887366 | chr1 | 50888619 | 50888796 | chr1 | 50889124 | 50889607 |
| chr1 | 50889741 | 50890460 | chr1 | 50890600 | 50890649 | chr1 | 50890796 | 50891565 |
| chr1 | 50892073 | 50892284 | chr1 | 50892337 | 50892432 | chr1 | 50892523 | 50893149 |
| chr1 | 50893151 | 50893423 | chr1 | 50893519 | 50893962 | chr1 | 51763181 | 51763395 |
| chr1 | 52832605 | 52832712 | chr1 | 53068087 | 53068181 | chr1 | 53068183 | 53068626 |
| chr1 | 53098746 | 53099053 | chr1 | 53099055 | 53099165 | chr1 | 53308489 | 53308608 |
| chr1 | 53308908 | 53309328 | chr1 | 53528288 | 53528527 | chr1 | 53705675 | 53705794 |
| chr1 | 54203419 | 54203422 | chr1 | 54203829 | 54204498 | chr1 | 54586532 | 54586831 |
| chr1 | 55462599 | 55462778 | chr1 | 57888293 | 57888472 | chr1 | 57888888 | 57889035 |
| chr1 | 57889037 | 57889187 | chr1 | 57889319 | 57889604 | chr1 | 57889606 | 57889738 |
| chr1 | 57890332 | 57890671 | chr1 | 58715055 | 58715294 | chr1 | 58715375 | 58715532 |
| chr1 | 58715534 | 58715855 | chr1 | 58715979 | 58716094 | chr1 | 61519265 | 61519405 |
| chr1 | 61519473 | 61519497 | chr1 | 62793169 | 62793342 | chr1 | 63539429 | 63539968 |
| chr1 | 63785232 | 63785293 | chr1 | 63785619 | 63785767 | chr1 | 63786079 | 63786431 |
| chr1 | 63786928 | 63787167 | chr1 | 63787226 | 63787249 | chr1 | 63787283 | 63787645 |
| chr1 | 63788341 | 63788640 | chr1 | 63788694 | 63788767 | chr1 | 63788920 | 63789497 |
| chr1 | 63789729 | 63789792 | chr1 | 63789850 | 63789913 | chr1 | 63790253 | 63790373 |

TABLE 15-continued

| chr | start | end | chr | start | end | chr | start | end |
|---|---|---|---|---|---|---|---|---|
| chr1 | 63792458 | 63792649 | chr1 | 63792798 | 63793171 | chr1 | 63795265 | 63795934 |
| chr1 | 63795936 | 63796370 | chr1 | 63796418 | 63796584 | chr1 | 64240031 | 64240222 |
| chr1 | 64240533 | 64240765 | chr1 | 64734554 | 64734669 | chr1 | 64937227 | 64937401 |
| chr1 | 65731243 | 65731506 | chr1 | 65731782 | 65731851 | chr1 | 65990876 | 65991019 |
| chr1 | 65991344 | 65991561 | chr1 | 65991606 | 65991758 | chr1 | 65991784 | 65991883 |
| chr1 | 66258088 | 66258651 | chr1 | 66258672 | 66258760 | chr1 | 66258762 | 66258867 |
| chr1 | 66259037 | 66259276 | chr1 | 66998702 | 66999412 | chr1 | 66999536 | 66999772 |
| chr1 | 67217965 | 67218424 | chr1 | 67390243 | 67390542 | chr1 | 67390993 | 67391172 |
| chr1 | 67773081 | 67773860 | chr1 | 70033524 | 70033709 | chr1 | 70033829 | 70034003 |
| chr1 | 70034368 | 70034491 | chr1 | 70034493 | 70034667 | chr1 | 70035014 | 70035208 |
| chr1 | 70035210 | 70035526 | chr1 | 70599152 | 70599260 | chr1 | 70672859 | 70672978 |
| chr1 | 72749635 | 72749700 | chr1 | 72749732 | 72749798 | chr1 | 75595702 | 75595759 |
| chr1 | 75595819 | 75595991 | chr1 | 75596136 | 75596479 | chr1 | 75596597 | 75596859 |
| chr1 | 75596930 | 75597668 | chr1 | 75597842 | 75598261 | chr1 | 75598310 | 75598489 |
| chr1 | 75599345 | 75599704 | chr1 | 75600148 | 75600685 | chr1 | 75600687 | 75601119 |
| chr1 | 75601188 | 75601276 | chr1 | 75601278 | 75601513 | chr1 | 75601889 | 75603148 |
| chr1 | 76080387 | 76080727 | chr1 | 76080729 | 76080866 | chr1 | 76082050 | 76082289 |
| chr1 | 76354731 | 76354839 | chr1 | 76540398 | 76540574 | chr1 | 76540576 | 76540757 |
| chr1 | 77333984 | 77333159 | chr1 | 77333161 | 77333163 | chr1 | 77333285 | 77333434 |
| chr1 | 77333580 | 77333625 | chr1 | 77334169 | 77334386 | chr1 | 77334409 | 77334757 |
| chr1 | 77334796 | 77334846 | chr1 | 77747291 | 77747382 | chr1 | 77747384 | 77747530 |
| chr1 | 77747848 | 77748327 | chr1 | 78511371 | 78511856 | chr1 | 78511858 | 78512450 |
| chr1 | 78957198 | 78957617 | chr1 | 82268586 | 82268904 | chr1 | 84944531 | 84944650 |
| chr1 | 85358543 | 85358593 | chr1 | 85358752 | 85358902 | chr1 | 85463275 | 85463454 |
| chr1 | 86621565 | 86622024 | chr1 | 86622112 | 86622113 | chr1 | 86622115 | 86622224 |
| chr1 | 86622430 | 86622552 | chr1 | 86622813 | 86622831 | chr1 | 86860815 | 86861049 |
| chr1 | 87617672 | 87617911 | chr1 | 90309344 | 90309571 | chr1 | 91171926 | 91172765 |
| chr1 | 91177865 | 91178284 | chr1 | 91179982 | 91180401 | chr1 | 91181853 | 91182212 |
| chr1 | 91182246 | 91182969 | chr1 | 91183001 | 91183196 | chr1 | 91183251 | 91183519 |
| chr1 | 91183521 | 91183611 | chr1 | 91183776 | 91183805 | chr1 | 91183850 | 91184080 |
| chr1 | 91184339 | 91184413 | chr1 | 91184415 | 91184758 | chr1 | 91185126 | 91185309 |
| chr1 | 91185348 | 91185809 | chr1 | 91188891 | 91189483 | chr1 | 91189585 | 91190484 |
| chr1 | 91190791 | 91190949 | chr1 | 91190985 | 91191001 | chr1 | 91191003 | 91191235 |
| chr1 | 91191290 | 91191390 | chr1 | 91192174 | 91192577 | chr1 | 91192682 | 91192773 |
| chr1 | 91194446 | 91194672 | chr1 | 91195015 | 91195494 | chr1 | 91195802 | 91196195 |
| chr1 | 91196226 | 91196581 | chr1 | 91316168 | 91316407 | chr1 | 91316536 | 91316775 |
| chr1 | 91869914 | 91870093 | chr1 | 92948236 | 92948701 | chr1 | 92948760 | 92949059 |
| chr1 | 92952071 | 92952632 | chr1 | 94343486 | 94343596 | chr1 | 97185167 | 97185357 |
| chr1 | 98510704 | 98511031 | chr1 | 98511033 | 98511423 | chr1 | 98511536 | 98512015 |
| chr1 | 98514151 | 98514330 | chr1 | 98515048 | 98515087 | chr1 | 98515369 | 98515408 |
| chr1 | 98518930 | 98519661 | chr1 | 98519663 | 98519769 | chr1 | 99469586 | 99469697 |
| chr1 | 99469760 | 99469885 | chr1 | 99470049 | 99470062 | chr1 | 99470212 | 99470288 |
| chr1 | 99470697 | 99470924 | chr1 | 100437184 | 100437270 | chr1 | 101004358 | 101004817 |
| chr1 | 101004989 | 101005228 | chr1 | 101005279 | 101005758 | chr1 | 101702411 | 101702602 |
| chr1 | 101702604 | 101702710 | chr1 | 101703538 | 101703717 | chr1 | 107682647 | 107683066 |
| chr1 | 107683359 | 107683598 | chr1 | 107684161 | 107684520 | chr1 | 108506989 | 108507077 |
| chr1 | 108507149 | 108507168 | chr1 | 108507230 | 108507376 | chr1 | 108507495 | 108507589 |
| chr1 | 108507658 | 108507914 | chr1 | 108507957 | 108508207 | chr1 | 108508209 | 108508548 |
| chr1 | 108508550 | 108508671 | chr1 | 109203582 | 109203761 | chr1 | 109585369 | 109585472 |
| chr1 | 109631647 | 109631766 | chr1 | 109644252 | 109644413 | chr1 | 110610483 | 110610898 |
| chr1 | 110611046 | 110611277 | chr1 | 110611435 | 110611514 | chr1 | 110611654 | 110611794 |
| chr1 | 110626791 | 110627671 | chr1 | 110672792 | 110673082 | chr1 | 110673084 | 110673331 |
| chr1 | 110692886 | 110693497 | chr1 | 110693737 | 110694205 | chr1 | 110754040 | 110754202 |
| chr1 | 110754211 | 110754357 | chr1 | 110754872 | 110754930 | chr1 | 110883455 | 110884054 |
| chr1 | 111097832 | 111098011 | chr1 | 111098107 | 111098406 | chr1 | 111216684 | 111216973 |
| chr1 | 111217195 | 111217575 | chr1 | 111217714 | 111217712 | chr1 | 111217714 | 111217892 |
| chr1 | 111217924 | 111218063 | chr1 | 111505931 | 111506290 | chr1 | 111813448 | 111813687 |
| chr1 | 112084880 | 112085059 | chr1 | 114448981 | 114449087 | chr1 | 114695362 | 114695695 |
| chr1 | 114695697 | 114695737 | chr1 | 114695800 | 114696021 | chr1 | 114696132 | 114696183 |
| chr1 | 114696350 | 114696464 | chr1 | 114696541 | 114696791 | chr1 | 115256441 | 115256620 |
| chr1 | 115258659 | 115258838 | chr1 | 115631842 | 115632011 | chr1 | 115632393 | 115632632 |
| chr1 | 115880081 | 115880207 | chr1 | 115880209 | 115880500 | chr1 | 115880765 | 115880795 |
| chr1 | 115880873 | 115881043 | chr1 | 115881249 | 115881304 | chr1 | 116214002 | 116214132 |
| chr1 | 116214207 | 116214421 | chr1 | 116371051 | 116371187 | chr1 | 116371189 | 116371290 |
| chr1 | 116380550 | 116381389 | chr1 | 116382294 | 116382583 | chr1 | 119521979 | 119522121 |
| chr1 | 119522200 | 119522435 | chr1 | 119522566 | 119522632 | chr1 | 119522741 | 119522854 |
| chr1 | 119522926 | 119523039 | chr1 | 119527237 | 119527472 | chr1 | 119527549 | 119527728 |
| chr1 | 119528557 | 119529216 | chr1 | 119529703 | 119529912 | chr1 | 119530024 | 119530149 |
| chr1 | 119530202 | 119530508 | chr1 | 119530554 | 119530600 | chr1 | 119530602 | 119530743 |
| chr1 | 119530944 | 119531243 | chr1 | 119531943 | 119531997 | chr1 | 119536058 | 119536457 |
| chr1 | 119542905 | 119542994 | chr1 | 119543070 | 119543215 | chr1 | 119543274 | 119543324 |
| chr1 | 119543438 | 119544277 | chr1 | 119548749 | 119548928 | chr1 | 119548955 | 119549017 |
| chr1 | 119549032 | 119549735 | chr1 | 119549915 | 119550034 | chr1 | 119550068 | 119550367 |
| chr1 | 119550434 | 119550721 | chr1 | 119551014 | 119551357 | chr1 | 150603035 | 150603141 |
| chr1 | 151169649 | 151169757 | chr1 | 151170069 | 151170297 | chr1 | 151300814 | 151300933 |
| chr1 | 151693849 | 151694448 | chr1 | 152085302 | 152085601 | chr1 | 152488055 | 152488294 |
| chr1 | 153539382 | 153539681 | chr1 | 153540006 | 153540245 | chr1 | 153651873 | 153652472 |
| chr1 | 153937048 | 153937167 | chr1 | 154298254 | 154298562 | chr1 | 154475372 | 154475612 |

TABLE 15-continued

| chr | start | end | chr | start | end | chr | start | end |
|---|---|---|---|---|---|---|---|---|
| chr1 | 154516709 | 154516926 | chr1 | 155043313 | 155043734 | chr1 | 155578918 | 155579008 |
| chr1 | 155826303 | 155826412 | chr1 | 155954190 | 155954391 | chr1 | 156010529 | 156010643 |
| chr1 | 156215255 | 156215434 | chr1 | 156215527 | 156215886 | chr1 | 156357892 | 156358611 |
| chr1 | 156390058 | 156390777 | chr1 | 156405635 | 156406071 | chr1 | 156406105 | 156406515 |
| chr1 | 156432076 | 156432315 | chr1 | 156594879 | 156595053 | chr1 | 156595081 | 156595118 |
| chr1 | 156611795 | 156611944 | chr1 | 156611994 | 156612214 | chr1 | 156626505 | 156626744 |
| chr1 | 156626814 | 156627019 | chr1 | 156627084 | 156627113 | chr1 | 156646516 | 156646597 |
| chr1 | 156646635 | 156646740 | chr1 | 156814831 | 156814953 | chr1 | 156815031 | 156815240 |
| chr1 | 156815356 | 156815835 | chr1 | 156830190 | 156830192 | chr1 | 156830266 | 156830429 |
| chr1 | 156838078 | 156838424 | chr1 | 156863062 | 156863429 | chr1 | 156863641 | 156863808 |
| chr1 | 157247369 | 157247487 | chr1 | 157458816 | 157458935 | chr1 | 157895339 | 157895518 |
| chr1 | 158669614 | 158669973 | chr1 | 158687334 | 158687633 | chr1 | 159158251 | 159158369 |
| chr1 | 159158472 | 159158588 | chr1 | 159187205 | 159187390 | chr1 | 160693839 | 160693957 |
| chr1 | 160992253 | 160992363 | chr1 | 161007615 | 161007847 | chr1 | 161228566 | 161228971 |
| chr1 | 161275466 | 161275579 | chr1 | 161275640 | 161276125 | chr1 | 161442367 | 161442546 |
| chr1 | 161471751 | 161471868 | chr1 | 161591390 | 161591444 | chr1 | 161591549 | 161591629 |
| chr1 | 162792211 | 162792630 | chr1 | 164290533 | 164290672 | chr1 | 164290724 | 164290772 |
| chr1 | 165086889 | 165087114 | chr1 | 165204994 | 165205233 | chr1 | 165321651 | 165321787 |
| chr1 | 165321943 | 165321950 | chr1 | 165324104 | 165324758 | chr1 | 165325016 | 165325357 |
| chr1 | 165325395 | 165325615 | chr1 | 165325804 | 165326043 | chr1 | 165326128 | 165326205 |
| chr1 | 165326297 | 165326547 | chr1 | 165414124 | 165414352 | chr1 | 166134158 | 166134282 |
| chr1 | 166134284 | 166134397 | chr1 | 166134643 | 166134882 | chr1 | 166135118 | 166135357 |
| chr1 | 166853551 | 166853578 | chr1 | 166853580 | 166853668 | chr1 | 166916774 | 166916921 |
| chr1 | 166916937 | 166916950 | chr1 | 166917125 | 166917193 | chr1 | 167599076 | 167599435 |
| chr1 | 167599521 | 167599940 | chr1 | 167823371 | 167823524 | chr1 | 169396291 | 169396635 |
| chr1 | 169396637 | 169396689 | chr1 | 169396731 | 169397010 | chr1 | 170629466 | 170629513 |
| chr1 | 170630364 | 170630602 | chr1 | 170630604 | 170630903 | chr1 | 170631005 | 170631244 |
| chr1 | 170631399 | 170631638 | chr1 | 170633533 | 170633712 | chr1 | 170637582 | 170637881 |
| chr1 | 170640425 | 170640625 | chr1 | 170640665 | 170640784 | chr1 | 171625443 | 171625543 |
| chr1 | 171810113 | 171811066 | chr1 | 173638567 | 173639153 | chr1 | 175346411 | 175346646 |
| chr1 | 175388563 | 175388682 | chr1 | 177133690 | 177133918 | chr1 | 177140021 | 177140145 |
| chr1 | 177140147 | 177140174 | chr1 | 177140305 | 177140790 | chr1 | 177150699 | 177150878 |
| chr1 | 179544884 | 179545091 | chr1 | 179545093 | 179545183 | chr1 | 179712063 | 179712339 |
| chr1 | 179712411 | 179712554 | chr1 | 179712568 | 179712591 | chr1 | 179712593 | 179712734 |
| chr1 | 179712831 | 179713175 | chr1 | 180197986 | 180198285 | chr1 | 180202331 | 180202395 |
| chr1 | 180202649 | 180203110 | chr1 | 180203355 | 180203608 | chr1 | 180203634 | 180204221 |
| chr1 | 180204223 | 180204620 | chr1 | 180204898 | 180205009 | chr1 | 180235656 | 180235835 |
| chr1 | 180882487 | 180882518 | chr1 | 180925188 | 180925289 | chr1 | 180925330 | 180925487 |
| chr1 | 181287599 | 181287838 | chr1 | 181287922 | 181288281 | chr1 | 181451315 | 181452214 |
| chr1 | 181452770 | 181452986 | chr1 | 181453051 | 181453069 | chr1 | 181454774 | 181455013 |
| chr1 | 181455104 | 181455343 | chr1 | 182584084 | 182584340 | chr1 | 182584404 | 182584623 |
| chr1 | 182807488 | 182807607 | chr1 | 183129301 | 183129530 | chr1 | 183386070 | 183386319 |
| chr1 | 183386599 | 183386713 | chr1 | 183386752 | 183386827 | chr1 | 183386947 | 183387051 |
| chr1 | 183387174 | 183387413 | chr1 | 183462984 | 183463103 | chr1 | 183774155 | 183774454 |
| chr1 | 184005609 | 184005908 | chr1 | 185073803 | 185074028 | chr1 | 190444781 | 190444892 |
| chr1 | 190445080 | 190445197 | chr1 | 190445199 | 190445379 | chr1 | 190447297 | 190447300 |
| chr1 | 190447389 | 190447596 | chr1 | 195732240 | 195732521 | chr1 | 196577628 | 196577953 |
| chr1 | 196578007 | 196578246 | chr1 | 197879307 | 197879546 | chr1 | 197879607 | 197879661 |
| chr1 | 197879717 | 197880258 | chr1 | 197882052 | 197882291 | chr1 | 197882353 | 197882581 |
| chr1 | 197886978 | 197887067 | chr1 | 197887147 | 197887457 | chr1 | 197887707 | 197887817 |
| chr1 | 197887977 | 197888122 | chr1 | 197888181 | 197888396 | chr1 | 197888546 | 197889385 |
| chr1 | 200009312 | 200009551 | chr1 | 200009665 | 200010202 | chr1 | 200011236 | 200011684 |
| chr1 | 200011686 | 200012191 | chr1 | 201368752 | 201368805 | chr1 | 201983038 | 201983277 |
| chr1 | 202081790 | 202081886 | chr1 | 202183343 | 202183476 | chr1 | 202679128 | 202679607 |
| chr1 | 203298210 | 203298441 | chr1 | 203429530 | 203429649 | chr1 | 204333520 | 204333660 |
| chr1 | 204653475 | 204653596 | chr1 | 204653793 | 204653954 | chr1 | 205312504 | 205312912 |
| chr1 | 205312962 | 205313043 | chr1 | 205424577 | 205425046 | chr1 | 205537569 | 205537587 |
| chr1 | 207200767 | 207201066 | chr1 | 207669419 | 207669788 | chr1 | 207669829 | 207670138 |
| chr1 | 207818295 | 207818397 | chr1 | 208084210 | 208084569 | chr1 | 209381030 | 209381269 |
| chr1 | 210111072 | 210111211 | chr1 | 210111285 | 210111422 | chr1 | 210111797 | 210111923 |
| chr1 | 210112037 | 210112244 | chr1 | 211847683 | 211847862 | chr1 | 212963808 | 212963979 |
| chr1 | 213123776 | 213124075 | chr1 | 213124573 | 213124623 | chr1 | 213124669 | 213124992 |
| chr1 | 214156395 | 214157004 | chr1 | 214158753 | 214158911 | chr1 | 214159037 | 214159052 |
| chr1 | 214160028 | 214160266 | chr1 | 214360583 | 214360753 | chr1 | 214360755 | 214360859 |
| chr1 | 214360927 | 214361062 | chr1 | 214724457 | 214724588 | chr1 | 215254998 | 215255897 |
| chr1 | 216897142 | 216897321 | chr1 | 217307385 | 217308360 | chr1 | 217308907 | 217309206 |
| chr1 | 217309671 | 217309910 | chr1 | 217311163 | 217311942 | chr1 | 217312946 | 217313043 |
| chr1 | 217313069 | 217313827 | chr1 | 217805068 | 217805236 | chr1 | 218520021 | 218520063 |
| chr1 | 218520096 | 218520292 | chr1 | 218520310 | 218520477 | chr1 | 218520701 | 218520740 |
| chr1 | 219347112 | 219347134 | chr1 | 219347314 | 219347553 | chr1 | 220101056 | 220101211 |
| chr1 | 220101371 | 220101475 | chr1 | 220101609 | 220101613 | chr1 | 220101675 | 220101788 |
| chr1 | 220636429 | 220636548 | chr1 | 220700737 | 220700976 | chr1 | 221051936 | 221052595 |
| chr1 | 221053527 | 221053946 | chr1 | 221067418 | 221067777 | chr1 | 223302739 | 223302978 |
| chr1 | 223538254 | 223538670 | chr1 | 223936546 | 223936753 | chr1 | 223936996 | 223937145 |
| chr1 | 224400388 | 224400627 | chr1 | 224528740 | 224528919 | chr1 | 224803668 | 224803854 |
| chr1 | 224803995 | 224804296 | chr1 | 224804396 | 224804687 | chr1 | 224804847 | 224804991 |
| chr1 | 224805051 | 224805116 | chr1 | 224805198 | 224805752 | chr1 | 224805849 | 224805890 |
| chr1 | 226411169 | 226411224 | chr1 | 226411247 | 226411348 | chr1 | 226411617 | 226411916 |

TABLE 15-continued

| chr | start | end | chr | start | end | chr | start | end |
|---|---|---|---|---|---|---|---|---|
| chr1 | 226924982 | 226925281 | chr1 | 227729830 | 227730168 | chr1 | 228194340 | 228194411 |
| chr1 | 228194571 | 228194579 | chr1 | 228195294 | 228196433 | chr1 | 228201147 | 228201326 |
| chr1 | 228247924 | 228247961 | chr1 | 228248228 | 228248407 | chr1 | 228463210 | 228463809 |
| chr1 | 228528749 | 228529108 | chr1 | 228558623 | 228559329 | chr1 | 228566548 | 228566618 |
| chr1 | 228566637 | 228566767 | chr1 | 228604124 | 228604348 | chr1 | 228633887 | 228633920 |
| chr1 | 228633922 | 228633950 | chr1 | 228633984 | 228634354 | chr1 | 228645048 | 228645244 |
| chr1 | 228645306 | 228645827 | chr1 | 228646196 | 228646315 | chr1 | 228651350 | 228651709 |
| chr1 | 228651805 | 228651902 | chr1 | 228652243 | 228652453 | chr1 | 228652509 | 228652704 |
| chr1 | 229542750 | 229542953 | chr1 | 229543221 | 229543229 | chr1 | 229543459 | 229543612 |
| chr1 | 229566670 | 229566942 | chr1 | 229567012 | 229567277 | chr1 | 229567370 | 229567993 |
| chr1 | 229568158 | 229568289 | chr1 | 229569712 | 229569951 | chr1 | 230404150 | 230404360 |
| chr1 | 230561683 | 230561922 | chr1 | 231297013 | 231297103 | chr1 | 231297105 | 231297312 |
| chr1 | 231298505 | 231298651 | chr1 | 231298653 | 231298708 | chr1 | 232765226 | 232765398 |
| chr1 | 233750126 | 233750402 | chr1 | 234040224 | 234040403 | chr1 | 234040886 | 234040974 |
| chr1 | 234041303 | 234041361 | chr1 | 234041416 | 234041659 | chr1 | 234349895 | 234350051 |
| chr1 | 234350053 | 234350194 | chr1 | 234445299 | 234445478 | chr1 | 234620965 | 234621073 |
| chr1 | 234844947 | 234845167 | chr1 | 235813693 | 235813797 | chr1 | 235814010 | 235814292 |
| chr1 | 236227538 | 236227744 | chr1 | 236227770 | 236227921 | chr1 | 236228022 | 236228197 |
| chr1 | 236228507 | 236228624 | chr1 | 236228706 | 236228866 | chr1 | 236559075 | 236559207 |
| chr1 | 236559257 | 236559374 | chr1 | 236849381 | 236849506 | chr1 | 236850198 | 236850220 |
| chr1 | 237205085 | 237205098 | chr1 | 237205157 | 237205174 | chr1 | 237205176 | 237205224 |
| chr1 | 237206102 | 237206266 | chr1 | 237206512 | 237206811 | chr1 | 239550505 | 239551284 |
| chr1 | 240118762 | 240119061 | chr1 | 240160997 | 240161086 | chr1 | 240161123 | 240161381 |
| chr1 | 240161547 | 240161571 | chr1 | 240254859 | 240255098 | chr1 | 240255282 | 240255486 |
| chr1 | 240255488 | 240255581 | chr1 | 240255739 | 240256159 | chr1 | 240256625 | 240256872 |
| chr1 | 240775379 | 240775530 | chr1 | 241052047 | 241052201 | chr1 | 241520202 | 241520441 |
| chr1 | 241520509 | 241520632 | chr1 | 241520685 | 241520688 | chr1 | 241587013 | 241587194 |
| chr1 | 241587513 | 241587609 | chr1 | 241587611 | 241587872 | chr1 | 242686642 | 242687781 |
| chr1 | 242688103 | 242688244 | chr1 | 242688278 | 242688342 | chr1 | 242688377 | 242688773 |
| chr1 | 243646523 | 243646762 | chr1 | 244014160 | 244014479 | chr1 | 244080598 | 244080777 |
| chr1 | 244080874 | 244080883 | chr1 | 244893136 | 244893255 | chr1 | 245135670 | 245135849 |
| chr1 | 245494418 | 245494631 | chr1 | 246330402 | 246330509 | chr1 | 246488077 | 246488316 |
| chr1 | 248002191 | 248002310 | chr1 | 248020405 | 248020449 | chr1 | 248020516 | 248020631 |
| chr1 | 248020957 | 248021424 | chr1 | 248027930 | 248028289 | chr1 | 248074658 | 248074768 |
| chr1 | 248074838 | 248075008 | chr1 | 248099661 | 248099900 | chr1 | 248328674 | 248328921 |
| chr1 | 249121623 | 249121738 | chr2 | 287492 | 287731 | chr2 | 288318 | 288557 |
| chr2 | 468116 | 468182 | chr2 | 468217 | 468234 | chr2 | 468424 | 468756 |
| chr2 | 496125 | 496465 | chr2 | 720748 | 720985 | chr2 | 875887 | 876066 |
| chr2 | 945838 | 946010 | chr2 | 946012 | 946077 | chr2 | 946117 | 946218 |
| chr2 | 946290 | 946356 | chr2 | 946449 | 946567 | chr2 | 946917 | 947044 |
| chr2 | 947127 | 947238 | chr2 | 1653023 | 1653262 | chr2 | 1746523 | 1747033 |
| chr2 | 1747591 | 1748008 | chr2 | 1748397 | 1748906 | chr2 | 2844646 | 2844676 |
| chr2 | 2844802 | 2844825 | chr2 | 5831102 | 5831205 | chr2 | 5831238 | 5831401 |
| chr2 | 5831715 | 5831894 | chr2 | 5831967 | 5832048 | chr2 | 5832284 | 5832326 |
| chr2 | 5832800 | 5832847 | chr2 | 5833283 | 5833433 | chr2 | 5833500 | 5833640 |
| chr2 | 5833735 | 5834119 | chr2 | 5835990 | 5836349 | chr2 | 5836451 | 5836575 |
| chr2 | 5836622 | 5836745 | chr2 | 5836828 | 5836992 | chr2 | 5837353 | 5837468 |
| chr2 | 5866006 | 5866305 | chr2 | 7164389 | 7164704 | chr2 | 7571420 | 7571477 |
| chr2 | 7571577 | 7571828 | chr2 | 9134330 | 9134569 | chr2 | 9960660 | 9960839 |
| chr2 | 10115632 | 10115739 | chr2 | 10153063 | 10153168 | chr2 | 10153229 | 10153422 |
| chr2 | 10154909 | 10155024 | chr2 | 10155269 | 10155384 | chr2 | 10156334 | 10156493 |
| chr2 | 10182747 | 10182986 | chr2 | 10408310 | 10408749 | chr2 | 10688800 | 10688931 |
| chr2 | 11052419 | 11052658 | chr2 | 11809858 | 11810116 | chr2 | 11810147 | 11810217 |
| chr2 | 12246027 | 12246196 | chr2 | 12858356 | 12858715 | chr2 | 14772673 | 14772888 |
| chr2 | 14774475 | 14774664 | chr2 | 17719601 | 17719900 | chr2 | 18058941 | 18059180 |
| chr2 | 18059692 | 18059931 | chr2 | 19550140 | 19550319 | chr2 | 19551225 | 19551449 |
| chr2 | 19556245 | 19556765 | chr2 | 19556994 | 19557173 | chr2 | 19558744 | 19558983 |
| chr2 | 19561045 | 19561404 | chr2 | 19561422 | 19561473 | chr2 | 19561524 | 19561781 |
| chr2 | 19563277 | 19563516 | chr2 | 20068723 | 20068962 | chr2 | 20442485 | 20442586 |
| chr2 | 20642626 | 20642745 | chr2 | 20865560 | 20865847 | chr2 | 20865849 | 20866022 |
| chr2 | 25391060 | 25391313 | chr2 | 25391586 | 25391825 | chr2 | 25438724 | 25438872 |
| chr2 | 25439139 | 25439356 | chr2 | 26372893 | 26373072 | chr2 | 26395353 | 26395458 |
| chr2 | 26395460 | 26395652 | chr2 | 26401956 | 26402135 | chr2 | 26407744 | 26407922 |
| chr2 | 26521960 | 26522079 | chr2 | 26915682 | 26916067 | chr2 | 26916089 | 26916341 |
| chr2 | 27070250 | 27070489 | chr2 | 27071144 | 27071443 | chr2 | 27072394 | 27072633 |
| chr2 | 27072727 | 27073086 | chr2 | 27578410 | 27578500 | chr2 | 27887451 | 27887630 |
| chr2 | 29033261 | 29033698 | chr2 | 29337988 | 29338052 | chr2 | 29338159 | 29338748 |
| chr2 | 29338810 | 29339067 | chr2 | 30143219 | 30143323 | chr2 | 30143383 | 30143578 |
| chr2 | 30143957 | 30144151 | chr2 | 30144175 | 30144496 | chr2 | 30453619 | 30453654 |
| chr2 | 30453785 | 30454038 | chr2 | 31360210 | 31360590 | chr2 | 31360631 | 31360693 |
| chr2 | 31360695 | 31360756 | chr2 | 31360804 | 31360929 | chr2 | 31361015 | 31361118 |
| chr2 | 31361194 | 31361194 | chr2 | 31361282 | 31361461 | chr2 | 31456606 | 31457131 |
| chr2 | 32504335 | 32504449 | chr2 | 38302176 | 38302188 | chr2 | 38302370 | 38302901 |
| chr2 | 38302949 | 38302955 | chr2 | 38365728 | 38365847 | chr2 | 39187141 | 39187238 |
| chr2 | 39187545 | 39187800 | chr2 | 39892997 | 39893596 | chr2 | 39893897 | 39894136 |
| chr2 | 40678513 | 40678872 | chr2 | 40678945 | 40679086 | chr2 | 40679088 | 40679519 |
| chr2 | 40679521 | 40679605 | chr2 | 40679689 | 40679712 | chr2 | 42274495 | 42274734 |
| chr2 | 42329340 | 42329445 | chr2 | 42329494 | 42329759 | chr2 | 42720185 | 42720447 |

TABLE 15-continued

| chr | start | end | chr | start | end | chr | start | end |
|---|---|---|---|---|---|---|---|---|
| chr2 | 43019525 | 43019944 | chr2 | 43451819 | 43451846 | chr2 | 43451892 | 43452418 |
| chr2 | 43824034 | 43824132 | chr2 | 44497613 | 44497842 | chr2 | 45028911 | 45029059 |
| chr2 | 45029184 | 45029450 | chr2 | 45029637 | 45029779 | chr2 | 45155039 | 45155211 |
| chr2 | 45155356 | 45155991 | chr2 | 45155993 | 45156812 | chr2 | 45156833 | 45157783 |
| chr2 | 45159873 | 45160352 | chr2 | 45160496 | 45160735 | chr2 | 45161598 | 45162036 |
| chr2 | 45162038 | 45162188 | chr2 | 45162319 | 45162558 | chr2 | 45162653 | 45163012 |
| chr2 | 45164589 | 45164608 | chr2 | 45164657 | 45164768 | chr2 | 45165490 | 45165669 |
| chr2 | 45168857 | 45168908 | chr2 | 45169349 | 45169548 | chr2 | 45169550 | 45170123 |
| chr2 | 45171295 | 45171564 | chr2 | 45171837 | 45171954 | chr2 | 45176506 | 45176865 |
| chr2 | 45179546 | 45179725 | chr2 | 45180156 | 45180156 | chr2 | 45181417 | 45181776 |
| chr2 | 45181795 | 45182094 | chr2 | 45231245 | 45231478 | chr2 | 45231754 | 45232208 |
| chr2 | 45233307 | 45233666 | chr2 | 45235491 | 45236030 | chr2 | 45237585 | 45237689 |
| chr2 | 45237691 | 45237884 | chr2 | 45240491 | 45240631 | chr2 | 45240764 | 45240876 |
| chr2 | 45241041 | 45241169 | chr2 | 45241233 | 45241280 | chr2 | 45395768 | 45396007 |
| chr2 | 45396234 | 45396533 | chr2 | 45396603 | 45397082 | chr2 | 46526226 | 46526331 |
| chr2 | 47193958 | 47194077 | chr2 | 47200517 | 47200696 | chr2 | 47249735 | 47249914 |
| chr2 | 47598298 | 47598477 | chr2 | 47598579 | 47598698 | chr2 | 47748048 | 47748587 |
| chr2 | 47796952 | 47797488 | chr2 | 47797490 | 47797911 | chr2 | 47798093 | 47798752 |
| chr2 | 47798853 | 47799033 | chr2 | 47799124 | 47799212 | chr2 | 48982485 | 48982701 |
| chr2 | 48982754 | 48982964 | chr2 | 50573520 | 50573639 | chr2 | 50573692 | 50573924 |
| chr2 | 50574041 | 50574356 | chr2 | 50574402 | 50574685 | chr2 | 50574739 | 50574940 |
| chr2 | 55289095 | 55289274 | chr2 | 56149762 | 56149941 | chr2 | 56150682 | 56151256 |
| chr2 | 56410918 | 56411087 | chr2 | 56411593 | 56411832 | chr2 | 58655968 | 58656207 |
| chr2 | 60706663 | 60706902 | chr2 | 60796498 | 60796617 | chr2 | 60797060 | 60797359 |
| chr2 | 61135116 | 61135235 | chr2 | 62798248 | 62798447 | chr2 | 63275470 | 63275509 |
| chr2 | 63275878 | 63275949 | chr2 | 63278888 | 63279022 | chr2 | 63280853 | 63281752 |
| chr2 | 63282632 | 63282867 | chr2 | 63283014 | 63283053 | chr2 | 63283870 | 63284229 |
| chr2 | 63284675 | 63284914 | chr2 | 63284996 | 63285799 | chr2 | 63286359 | 63286585 |
| chr2 | 63286694 | 63286748 | chr2 | 63287083 | 63287412 | chr2 | 66652937 | 66653063 |
| chr2 | 66653158 | 66653254 | chr2 | 66653256 | 66653577 | chr2 | 66653690 | 66653934 |
| chr2 | 66660560 | 66660791 | chr2 | 66808447 | 66808634 | chr2 | 66808727 | 66809453 |
| chr2 | 67625373 | 67625492 | chr2 | 67625733 | 67625852 | chr2 | 67626153 | 67626332 |
| chr2 | 68546250 | 68546517 | chr2 | 68546553 | 68546968 | chr2 | 68559344 | 68559463 |
| chr2 | 68672777 | 68672956 | chr2 | 70418609 | 70418722 | chr2 | 71355039 | 71355218 |
| chr2 | 71503688 | 71503927 | chr2 | 71504007 | 71504246 | chr2 | 71680759 | 71680938 |
| chr2 | 71693423 | 71693694 | chr2 | 72374295 | 72374524 | chr2 | 72374611 | 72374690 |
| chr2 | 72374714 | 72374850 | chr2 | 73145548 | 73145787 | chr2 | 73145824 | 73146123 |
| chr2 | 73147245 | 73147528 | chr2 | 73147967 | 73148067 | chr2 | 73148175 | 73148313 |
| chr2 | 73150850 | 73151029 | chr2 | 73151098 | 73151884 | chr2 | 73152600 | 73152679 |
| chr2 | 73152740 | 73152839 | chr2 | 73429420 | 73429719 | chr2 | 73429862 | 73429923 |
| chr2 | 73429977 | 73430161 | chr2 | 73430234 | 73430373 | chr2 | 73430443 | 73430818 |
| chr2 | 73440271 | 73440370 | chr2 | 73518355 | 73519014 | chr2 | 73519501 | 73519920 |
| chr2 | 74010442 | 74010621 | chr2 | 74453989 | 74454348 | chr2 | 74726670 | 74726849 |
| chr2 | 74740761 | 74741136 | chr2 | 74741138 | 74741480 | chr2 | 74741746 | 74741845 |
| chr2 | 74741873 | 74742045 | chr2 | 74742085 | 74742151 | chr2 | 74742325 | 74742648 |
| chr2 | 74742694 | 74743145 | chr2 | 74743767 | 74743824 | chr2 | 74781997 | 74782088 |
| chr2 | 74782219 | 74782356 | chr2 | 75426958 | 75426980 | chr2 | 75427295 | 75427474 |
| chr2 | 75427845 | 75428264 | chr2 | 80529292 | 80529520 | chr2 | 80529573 | 80529909 |
| chr2 | 80529986 | 80530112 | chr2 | 80530413 | 80530587 | chr2 | 80530623 | 80530652 |
| chr2 | 80531651 | 80531830 | chr2 | 80549486 | 80549845 | chr2 | 85107377 | 85107616 |
| chr2 | 85361224 | 85361310 | chr2 | 85361467 | 85361529 | chr2 | 85361629 | 85361703 |
| chr2 | 87016489 | 87016509 | chr2 | 87016576 | 87016728 | chr2 | 87017707 | 87018313 |
| chr2 | 88469219 | 88469398 | chr2 | 88751182 | 88751420 | chr2 | 88751461 | 88751816 |
| chr2 | 88751961 | 88752380 | chr2 | 88752515 | 88752874 | chr2 | 88990108 | 88990347 |
| chr2 | 89064806 | 89064976 | chr2 | 89065129 | 89065364 | chr2 | 95663873 | 95664112 |
| chr2 | 95690654 | 95690890 | chr2 | 95690944 | 95691363 | chr2 | 95691441 | 95691500 |
| chr2 | 95691502 | 95691860 | chr2 | 95691908 | 95692567 | chr2 | 95941596 | 95941895 |
| chr2 | 96990808 | 96991399 | chr2 | 97193003 | 97193064 | chr2 | 97193252 | 97193722 |
| chr2 | 97427415 | 97428194 | chr2 | 98703220 | 98703491 | chr2 | 98962800 | 98962900 |
| chr2 | 98962974 | 98963039 | chr2 | 98963255 | 98963408 | chr2 | 98963410 | 98963674 |
| chr2 | 98963750 | 98963826 | chr2 | 98964286 | 98964289 | chr2 | 98964502 | 98964741 |
| chr2 | 99439369 | 99439593 | chr2 | 99553333 | 99553632 | chr2 | 99796327 | 99796415 |
| chr2 | 99798571 | 99798746 | chr2 | 99799229 | 99799230 | chr2 | 100937747 | 100938210 |
| chr2 | 100938330 | 100938545 | chr2 | 100938575 | 100938799 | chr2 | 100938801 | 100938810 |
| chr2 | 100938985 | 100939246 | chr2 | 101009731 | 101010030 | chr2 | 101034149 | 101034388 |
| chr2 | 101436638 | 101436790 | chr2 | 102091079 | 102091335 | chr2 | 103236080 | 103236277 |
| chr2 | 105459001 | 105459152 | chr2 | 105459903 | 105460263 | chr2 | 105460265 | 105460604 |
| chr2 | 105460847 | 105461026 | chr2 | 105461164 | 105461335 | chr2 | 105461556 | 105461668 |
| chr2 | 105461700 | 105462000 | chr2 | 105462075 | 105462314 | chr2 | 105468701 | 105469000 |
| chr2 | 105469569 | 105469857 | chr2 | 105469881 | 105470168 | chr2 | 105470266 | 105470561 |
| chr2 | 105470563 | 105470925 | chr2 | 105472149 | 105472426 | chr2 | 105472713 | 105472928 |
| chr2 | 105473162 | 105473521 | chr2 | 105478687 | 105479054 | chr2 | 105479056 | 105479166 |
| chr2 | 105480630 | 105480683 | chr2 | 105483568 | 105483807 | chr2 | 105484367 | 105484484 |
| chr2 | 105488348 | 105488527 | chr2 | 105760890 | 105761004 | chr2 | 106060525 | 106060884 |
| chr2 | 106681644 | 106681870 | chr2 | 106681936 | 106681983 | chr2 | 106681985 | 106682175 |
| chr2 | 106730137 | 106730316 | chr2 | 106959289 | 106959648 | chr2 | 106959833 | 106960072 |
| chr2 | 107103778 | 107104017 | chr2 | 107502519 | 107502730 | chr2 | 107502866 | 107502908 |
| chr2 | 107503422 | 107503423 | chr2 | 107503458 | 107503637 | chr2 | 107503802 | 107504101 |

TABLE 15-continued

| chr | start | end | chr | start | end | chr | start | end |
|---|---|---|---|---|---|---|---|---|
| chr2 | 109335091 | 109335264 | chr2 | 109648002 | 109648301 | chr2 | 109745915 | 109746154 |
| chr2 | 109746204 | 109746388 | chr2 | 109746463 | 109746563 | chr2 | 111875279 | 111875518 |
| chr2 | 112656944 | 112657123 | chr2 | 114256879 | 114257238 | chr2 | 114261200 | 114261559 |
| chr2 | 115918579 | 115918893 | chr2 | 115919338 | 115919425 | chr2 | 115919831 | 115920612 |
| chr2 | 115920614 | 115920618 | chr2 | 118981075 | 118981857 | chr2 | 118981946 | 118982148 |
| chr2 | 118982254 | 118982574 | chr2 | 119067552 | 119068143 | chr2 | 119532059 | 119532358 |
| chr2 | 119566137 | 119566376 | chr2 | 119591259 | 119591558 | chr2 | 119592666 | 119592863 |
| chr2 | 119592923 | 119593464 | chr2 | 119593466 | 119593642 | chr2 | 119599830 | 119600129 |
| chr2 | 119600235 | 119600839 | chr2 | 119600856 | 119600953 | chr2 | 119602515 | 119602630 |
| chr2 | 119602829 | 119603174 | chr2 | 119603946 | 119604093 | chr2 | 119604154 | 119604245 |
| chr2 | 119604711 | 119604933 | chr2 | 119606048 | 119606283 | chr2 | 119606631 | 119606647 |
| chr2 | 119606692 | 119606931 | chr2 | 119607443 | 119607504 | chr2 | 119607848 | 119607933 |
| chr2 | 119610758 | 119610940 | chr2 | 119610999 | 119611057 | chr2 | 119611653 | 119611892 |
| chr2 | 119612250 | 119612429 | chr2 | 119614047 | 119614271 | chr2 | 119614697 | 119614936 |
| chr2 | 119614952 | 119615719 | chr2 | 119616070 | 119616552 | chr2 | 119616782 | 119616960 |
| chr2 | 119914617 | 119914856 | chr2 | 119916525 | 119916687 | chr2 | 120281556 | 120281790 |
| chr2 | 120281849 | 120281901 | chr2 | 120281939 | 120282028 | chr2 | 120979994 | 120980173 |
| chr2 | 120980255 | 120980494 | chr2 | 121200303 | 121200532 | chr2 | 121345007 | 121345169 |
| chr2 | 121411987 | 121412231 | chr2 | 122495323 | 122495490 | chr2 | 124782289 | 124782546 |
| chr2 | 124782596 | 124783195 | chr2 | 127423136 | 127423434 | chr2 | 127428910 | 127429147 |
| chr2 | 127438559 | 127438738 | chr2 | 127782953 | 127783168 | chr2 | 127783170 | 127783360 |
| chr2 | 127863514 | 127863813 | chr2 | 127976391 | 127976750 | chr2 | 128421788 | 128421850 |
| chr2 | 128421891 | 128422027 | chr2 | 128616519 | 128616628 | chr2 | 128847701 | 128847799 |
| chr2 | 130763485 | 130763677 | chr2 | 130971063 | 130971355 | chr2 | 131477742 | 131478023 |
| chr2 | 131594915 | 131594922 | chr2 | 131594948 | 131595094 | chr2 | 131720787 | 131721099 |
| chr2 | 131721438 | 131721585 | chr2 | 131721867 | 131722035 | chr2 | 131792157 | 131792520 |
| chr2 | 131792532 | 131792747 | chr2 | 131792921 | 131793154 | chr2 | 131793188 | 131793296 |
| chr2 | 132088786 | 132088919 | chr2 | 132121566 | 132121618 | chr2 | 132121652 | 132121676 |
| chr2 | 132121678 | 132121823 | chr2 | 132152279 | 132152578 | chr2 | 132182701 | 132183180 |
| chr2 | 132767373 | 132767492 | chr2 | 133014571 | 133014662 | chr2 | 133015300 | 133015419 |
| chr2 | 133062239 | 133062299 | chr2 | 133062362 | 133062478 | chr2 | 133426175 | 133426354 |
| chr2 | 133426561 | 133426776 | chr2 | 137522371 | 137522550 | chr2 | 137523751 | 137523759 |
| chr2 | 139536863 | 139537221 | chr2 | 139537355 | 139537823 | chr2 | 139537851 | 139537954 |
| chr2 | 142887816 | 142887886 | chr2 | 142887888 | 142888149 | chr2 | 142888264 | 142888503 |
| chr2 | 144694272 | 144694515 | chr2 | 144694554 | 144695231 | chr2 | 145273369 | 145273848 |
| chr2 | 145274112 | 145274511 | chr2 | 145274715 | 145274975 | chr2 | 145274977 | 145275314 |
| chr2 | 145282045 | 145282224 | chr2 | 148776713 | 148776876 | chr2 | 149633009 | 149633488 |
| chr2 | 149633646 | 149634065 | chr2 | 149645413 | 149645559 | chr2 | 149645561 | 149645995 |
| chr2 | 151342979 | 151343218 | chr2 | 154333432 | 154333671 | chr2 | 154334170 | 154334450 |
| chr2 | 154334452 | 154334769 | chr2 | 154335185 | 154335355 | chr2 | 154727963 | 154727992 |
| chr2 | 154728245 | 154728441 | chr2 | 154729083 | 154729316 | chr2 | 154729485 | 154729664 |
| chr2 | 155555064 | 155555440 | chr2 | 157176506 | 157176805 | chr2 | 157176908 | 157178165 |
| chr2 | 157178167 | 157178407 | chr2 | 157178637 | 157178809 | chr2 | 160760984 | 160761454 |
| chr2 | 161253375 | 161253554 | chr2 | 162272983 | 162273315 | chr2 | 162273383 | 162274182 |
| chr2 | 162274220 | 162274414 | chr2 | 162274748 | 162274942 | chr2 | 162275055 | 162275227 |
| chr2 | 162275311 | 162275438 | chr2 | 162275473 | 162275887 | chr2 | 162280153 | 162280416 |
| chr2 | 162280741 | 162281050 | chr2 | 162283291 | 162283603 | chr2 | 162283783 | 162284130 |
| chr2 | 164592998 | 164593221 | chr2 | 164593223 | 164593237 | chr2 | 168149978 | 168149991 |
| chr2 | 168149993 | 168150337 | chr2 | 168150669 | 168151028 | chr2 | 170282882 | 170283178 |
| chr2 | 170551654 | 170551866 | chr2 | 170681792 | 170681909 | chr2 | 170682152 | 170682329 |
| chr2 | 171569986 | 171570062 | chr2 | 171570182 | 171570190 | chr2 | 171570471 | 171570525 |
| chr2 | 171570590 | 171570829 | chr2 | 171571171 | 171571342 | chr2 | 171571379 | 171571410 |
| chr2 | 171571800 | 171571997 | chr2 | 171670259 | 171670447 | chr2 | 171670472 | 171670558 |
| chr2 | 171671385 | 171671790 | chr2 | 171671800 | 171671984 | chr2 | 171674001 | 171674026 |
| chr2 | 171674664 | 171675143 | chr2 | 171675268 | 171675383 | chr2 | 171675523 | 171675687 |
| chr2 | 171676590 | 171676787 | chr2 | 171676858 | 171676885 | chr2 | 171822419 | 171822574 |
| chr2 | 172366939 | 172367178 | chr2 | 172411062 | 172411241 | chr2 | 172945027 | 172945266 |
| chr2 | 172945821 | 172946294 | chr2 | 172947684 | 172947914 | chr2 | 172948184 | 172948406 |
| chr2 | 172948813 | 172948850 | chr2 | 172949090 | 172949283 | chr2 | 172949349 | 172949809 |
| chr2 | 172951494 | 172951543 | chr2 | 172952425 | 172952640 | chr2 | 172952685 | 172952882 |
| chr2 | 172952993 | 172953096 | chr2 | 172953125 | 172953144 | chr2 | 172955346 | 172955403 |
| chr2 | 172955472 | 172955645 | chr2 | 172957808 | 172958157 | chr2 | 172961319 | 172961678 |
| chr2 | 172964743 | 172964889 | chr2 | 172965296 | 172965299 | chr2 | 172965648 | 172965763 |
| chr2 | 172966174 | 172966533 | chr2 | 172972648 | 172972891 | chr2 | 172972931 | 172973307 |
| chr2 | 173099710 | 173099889 | chr2 | 173100167 | 173100506 | chr2 | 173422651 | 173422770 |
| chr2 | 175190771 | 175191973 | chr2 | 175192085 | 175192550 | chr2 | 175193187 | 175193377 |
| chr2 | 175193379 | 175193645 | chr2 | 175193809 | 175193906 | chr2 | 175195785 | 175195859 |
| chr2 | 175196355 | 175196371 | chr2 | 175196426 | 175196654 | chr2 | 175197015 | 175197194 |
| chr2 | 175199432 | 175199555 | chr2 | 175199922 | 175200012 | chr2 | 175200093 | 175200441 |
| chr2 | 175200710 | 175200853 | chr2 | 175200917 | 175201183 | chr2 | 175201360 | 175201542 |
| chr2 | 175201776 | 175201829 | chr2 | 175202127 | 175202246 | chr2 | 175202569 | 175202601 |
| chr2 | 175202634 | 175202746 | chr2 | 175204100 | 175204279 | chr2 | 175204694 | 175204947 |
| chr2 | 175206752 | 175206906 | chr2 | 175206961 | 175207111 | chr2 | 175207154 | 175207333 |
| chr2 | 175207446 | 175207745 | chr2 | 175208214 | 175208869 | chr2 | 175208997 | 175209218 |
| chr2 | 175546942 | 175547241 | chr2 | 175547310 | 175547489 | chr2 | 176940092 | 176940391 |
| chr2 | 176943180 | 176943659 | chr2 | 176943763 | 176943863 | chr2 | 176943995 | 176944002 |
| chr2 | 176944326 | 176944405 | chr2 | 176944457 | 176944847 | chr2 | 176945138 | 176945269 |
| chr2 | 176945582 | 176945885 | chr2 | 176946475 | 176946868 | chr2 | 176947285 | 176947494 |

TABLE 15-continued

| chr | start | end | chr | start | end | chr | start | end |
|---|---|---|---|---|---|---|---|---|
| chr2 | 176947647 | 176947654 | chr2 | 176947764 | 176947940 | chr2 | 176947942 | 176948006 |
| chr2 | 176948522 | 176948821 | chr2 | 176948971 | 176949150 | chr2 | 176949603 | 176949962 |
| chr2 | 176950075 | 176950350 | chr2 | 176956929 | 176957300 | chr2 | 176957409 | 176957415 |
| chr2 | 176957577 | 176957629 | chr2 | 176957915 | 176958008 | chr2 | 176958045 | 176958584 |
| chr2 | 176959191 | 176959589 | chr2 | 176963366 | 176963605 | chr2 | 176963999 | 176964150 |
| chr2 | 176964180 | 176964238 | chr2 | 176964272 | 176964334 | chr2 | 176964390 | 176964768 |
| chr2 | 176965265 | 176965591 | chr2 | 176969387 | 176969614 | chr2 | 176969677 | 176969984 |
| chr2 | 176975946 | 176976289 | chr2 | 176980649 | 176980938 | chr2 | 176981377 | 176981592 |
| chr2 | 176982518 | 176982726 | chr2 | 176986712 | 176986932 | chr2 | 176986962 | 176987215 |
| chr2 | 176993462 | 176994380 | chr2 | 176994498 | 176994622 | chr2 | 176995071 | 176995270 |
| chr2 | 176995332 | 176995712 | chr2 | 177001000 | 177001058 | chr2 | 177001118 | 177001263 |
| chr2 | 177001265 | 177001696 | chr2 | 177001782 | 177002079 | chr2 | 177004463 | 177004498 |
| chr2 | 177004556 | 177004762 | chr2 | 177042914 | 177042999 | chr2 | 177043267 | 177043610 |
| chr2 | 177053187 | 177053435 | chr2 | 177053619 | 177053703 | chr2 | 177054023 | 177054442 |
| chr2 | 177502981 | 177503153 | chr2 | 178972904 | 178973143 | chr2 | 179317039 | 179317139 |
| chr2 | 182321308 | 182321727 | chr2 | 182321736 | 182321838 | chr2 | 182322039 | 182322192 |
| chr2 | 182322400 | 182323131 | chr2 | 182542829 | 182542864 | chr2 | 182542866 | 182543008 |
| chr2 | 182543221 | 182543413 | chr2 | 182543666 | 182544025 | chr2 | 182545124 | 182545363 |
| chr2 | 182545438 | 182545797 | chr2 | 182545887 | 182545948 | chr2 | 182546002 | 182546179 |
| chr2 | 182546361 | 182546535 | chr2 | 182547290 | 182547388 | chr2 | 182547438 | 182547709 |
| chr2 | 182547840 | 182547932 | chr2 | 182548062 | 182548259 | chr2 | 182548992 | 182549026 |
| chr2 | 182549038 | 182549231 | chr2 | 182549247 | 182549546 | chr2 | 182550054 | 182550199 |
| chr2 | 182819031 | 182819312 | chr2 | 183731200 | 183731332 | chr2 | 183731467 | 183731619 |
| chr2 | 183731734 | 183732153 | chr2 | 185462776 | 185463075 | chr2 | 185463116 | 185463895 |
| chr2 | 186603414 | 186603593 | chr2 | 188418947 | 188419178 | chr2 | 189157513 | 189157692 |
| chr2 | 193058947 | 193059318 | chr2 | 193059345 | 193059549 | chr2 | 193059662 | 193059717 |
| chr2 | 193059719 | 193060146 | chr2 | 193060294 | 193060533 | chr2 | 193060608 | 193060967 |
| chr2 | 193061341 | 193061580 | chr2 | 198456572 | 198456690 | chr2 | 200326551 | 200326730 |
| chr2 | 200326765 | 200326813 | chr2 | 200327187 | 200327254 | chr2 | 200327424 | 200327452 |
| chr2 | 200327576 | 200327666 | chr2 | 200328669 | 200328685 | chr2 | 200329030 | 200329394 |
| chr2 | 200329433 | 200329748 | chr2 | 200333686 | 200333759 | chr2 | 200333801 | 200333925 |
| chr2 | 200334895 | 200335308 | chr2 | 200335363 | 200335452 | chr2 | 200335592 | 200336034 |
| chr2 | 201450453 | 201450743 | chr2 | 201450745 | 201450812 | chr2 | 201450845 | 201450922 |
| chr2 | 201451014 | 201451144 | chr2 | 202096992 | 202097231 | chr2 | 202899788 | 202899967 |
| chr2 | 206550978 | 206551015 | chr2 | 206551072 | 206551363 | chr2 | 206551451 | 206551457 |
| chr2 | 207138998 | 207139155 | chr2 | 207139267 | 207139686 | chr2 | 207307426 | 207307478 |
| chr2 | 207307548 | 207307665 | chr2 | 207308711 | 207308950 | chr2 | 207506612 | 207507266 |
| chr2 | 208635519 | 208635864 | chr2 | 209113024 | 209113202 | chr2 | 209225137 | 209225376 |
| chr2 | 209271228 | 209271337 | chr2 | 210636255 | 210636382 | chr2 | 210636430 | 210636690 |
| chr2 | 210636738 | 210636877 | chr2 | 210636934 | 210636974 | chr2 | 213401138 | 213401437 |
| chr2 | 213401511 | 213401565 | chr2 | 213401567 | 213402050 | chr2 | 213403015 | 213403434 |
| chr2 | 217559222 | 217559401 | chr2 | 218806046 | 218806405 | chr2 | 219736062 | 219736705 |
| chr2 | 219827964 | 219827975 | chr2 | 219847360 | 219847659 | chr2 | 219848726 | 219848892 |
| chr2 | 219848936 | 219849085 | chr2 | 219857648 | 219857738 | chr2 | 219857781 | 219857860 |
| chr2 | 220080582 | 220080941 | chr2 | 220173904 | 220174037 | chr2 | 220174060 | 220174383 |
| chr2 | 220196266 | 220196671 | chr2 | 220223024 | 220223203 | chr2 | 220223557 | 220223700 |
| chr2 | 220223795 | 220223796 | chr2 | 220283250 | 220283290 | chr2 | 220283363 | 220283609 |
| chr2 | 220299495 | 220299635 | chr2 | 220299886 | 220300154 | chr2 | 220348949 | 220348984 |
| chr2 | 220349055 | 220349788 | chr2 | 220361370 | 220361467 | chr2 | 220416297 | 220416596 |
| chr2 | 220416770 | 220417729 | chr2 | 222435699 | 222435857 | chr2 | 223155678 | 223156277 |
| chr2 | 223158648 | 223159542 | chr2 | 223159735 | 223159806 | chr2 | 223159869 | 223160154 |
| chr2 | 223160251 | 223160481 | chr2 | 223161173 | 223161352 | chr2 | 223161452 | 223161685 |
| chr2 | 223161807 | 223162165 | chr2 | 223162678 | 223162891 | chr2 | 223162929 | 223163225 |
| chr2 | 223163473 | 223163637 | chr2 | 223163682 | 223163809 | chr2 | 223163811 | 223164034 |
| chr2 | 223164440 | 223164617 | chr2 | 223165334 | 223165503 | chr2 | 223166190 | 223166226 |
| chr2 | 223166294 | 223166825 | chr2 | 223167302 | 223167661 | chr2 | 223168346 | 223168832 |
| chr2 | 223168917 | 223168945 | chr2 | 223169543 | 223169962 | chr2 | 223170286 | 223170525 |
| chr2 | 223171026 | 223171265 | chr2 | 223172959 | 223173259 | chr2 | 223176018 | 223176282 |
| chr2 | 223176361 | 223176512 | chr2 | 223176720 | 223177080 | chr2 | 223177245 | 223177703 |
| chr2 | 228029326 | 228029351 | chr2 | 228029373 | 228029625 | chr2 | 228466762 | 228466881 |
| chr2 | 228735702 | 228735828 | chr2 | 228736135 | 228736296 | chr2 | 228736336 | 228736554 |
| chr2 | 229046024 | 229046605 | chr2 | 230795461 | 230795640 | chr2 | 232394867 | 232395022 |
| chr2 | 232395055 | 232395166 | chr2 | 232791619 | 232792098 | chr2 | 233350112 | 233350540 |
| chr2 | 233350844 | 233351279 | chr2 | 233351416 | 233351491 | chr2 | 233351930 | 233352007 |
| chr2 | 233352102 | 233352452 | chr2 | 233352507 | 233352763 | chr2 | 233352776 | 233352949 |
| chr2 | 233498615 | 233498874 | chr2 | 233498896 | 233499345 | chr2 | 233499386 | 233499394 |
| chr2 | 233750451 | 233750630 | chr2 | 235404471 | 235404533 | chr2 | 235404551 | 235404590 |
| chr2 | 235860803 | 235860897 | chr2 | 236402683 | 236402901 | chr2 | 236403060 | 236403102 |
| chr2 | 236403174 | 236403419 | chr2 | 236403779 | 236403833 | chr2 | 236877188 | 236877367 |
| chr2 | 237072642 | 237072998 | chr2 | 237073000 | 237073015 | chr2 | 237073057 | 237073112 |
| chr2 | 237073265 | 237073496 | chr2 | 237076657 | 237076833 | chr2 | 237077466 | 237077685 |
| chr2 | 237077815 | 237078054 | chr2 | 237078097 | 237078427 | chr2 | 237080190 | 237080369 |
| chr2 | 237081255 | 237081427 | chr2 | 237081537 | 237081554 | chr2 | 237082344 | 237082809 |
| chr2 | 237086291 | 237086398 | chr2 | 237086400 | 237086559 | chr2 | 237145333 | 237145437 |
| chr2 | 237145439 | 237145692 | chr2 | 237416114 | 237416504 | chr2 | 238395205 | 238395444 |
| chr2 | 238395815 | 238395988 | chr2 | 238535876 | 238535985 | chr2 | 238536005 | 238536215 |
| chr2 | 238864570 | 238864631 | chr2 | 238864727 | 238864989 | chr2 | 239051124 | 239051303 |
| chr2 | 239140139 | 239140347 | chr2 | 239265703 | 239265881 | chr2 | 239482400 | 239482622 |

TABLE 15-continued

| chr | start | end | chr | start | end | chr | start | end |
|---|---|---|---|---|---|---|---|---|
| chr2 | 239705202 | 239705364 | chr2 | 239755090 | 239755198 | chr2 | 239755638 | 239755654 |
| chr2 | 239756347 | 239756463 | chr2 | 239756488 | 239756586 | chr2 | 239757551 | 239757731 |
| chr2 | 239757899 | 239757910 | chr2 | 239757992 | 239758061 | chr2 | 239758126 | 239758231 |
| chr2 | 239758251 | 239758490 | chr2 | 239957240 | 239957539 | chr2 | 240168722 | 240169141 |
| chr2 | 240319908 | 240320087 | chr2 | 240582303 | 240582448 | chr2 | 240619443 | 240619682 |
| chr2 | 240658145 | 240658504 | chr2 | 240658593 | 240658772 | chr2 | 241095576 | 241095868 |
| chr2 | 241393126 | 241393167 | chr2 | 241393199 | 241393545 | chr2 | 241542045 | 241542344 |
| chr2 | 241544927 | 241545106 | chr2 | 241758299 | 241758898 | chr2 | 241759497 | 241759796 |
| chr2 | 241760075 | 241760254 | chr2 | 241760420 | 241760599 | chr2 | 241771062 | 241771361 |
| chr2 | 241865091 | 241865450 | chr2 | 242009317 | 242009496 | chr2 | 242021689 | 242021916 |
| chr2 | 242523873 | 242524172 | chr2 | 242549754 | 242549772 | chr2 | 242549918 | 242550053 |
| chr2 | 242554475 | 242554654 | chr2 | 242756042 | 242756401 | chr2 | 242832893 | 242833252 |
| chr2 | 242833484 | 242833663 | chr2 | 242833711 | 242833930 | chr2 | 242836419 | 242836718 |
| chr2 | 242925420 | 242925719 | chr3 | 238456 | 238716 | chr3 | 239007 | 239126 |
| chr3 | 239159 | 239175 | chr3 | 239534 | 239869 | chr3 | 240110 | 240313 |
| chr3 | 2140189 | 2140435 | chr3 | 3840419 | 3840838 | chr3 | 3840946 | 3841245 |
| chr3 | 3842586 | 3842689 | chr3 | 5137871 | 5138109 | chr3 | 6902228 | 6902441 |
| chr3 | 6903500 | 6903564 | chr3 | 8810152 | 8810298 | chr3 | 9178065 | 9178130 |
| chr3 | 9593878 | 9594117 | chr3 | 9594286 | 9594473 | chr3 | 9595199 | 9595199 |
| chr3 | 9595396 | 9595503 | chr3 | 9595599 | 9595678 | chr3 | 9904155 | 9904634 |
| chr3 | 9941391 | 9941509 | chr3 | 9956984 | 9957223 | chr3 | 9957355 | 9957774 |
| chr3 | 10182757 | 10182917 | chr3 | 10183247 | 10183396 | chr3 | 10183632 | 10183811 |
| chr3 | 10858055 | 10858123 | chr3 | 11034163 | 11034462 | chr3 | 11034991 | 11035353 |
| chr3 | 11035383 | 11035410 | chr3 | 12046310 | 12046353 | chr3 | 12046378 | 12046727 |
| chr3 | 12917512 | 12917751 | chr3 | 12976987 | 12977150 | chr3 | 13323405 | 13324029 |
| chr3 | 13324277 | 13324348 | chr3 | 13324420 | 13324516 | chr3 | 13324744 | 13325023 |
| chr3 | 13590341 | 13590414 | chr3 | 13590448 | 13590641 | chr3 | 13679082 | 13679441 |
| chr3 | 13921316 | 13921555 | chr3 | 14851755 | 14851994 | chr3 | 14852233 | 14852659 |
| chr3 | 14852661 | 14853012 | chr3 | 16553963 | 16554202 | chr3 | 16554251 | 16554466 |
| chr3 | 16554468 | 16554730 | chr3 | 17001229 | 17001341 | chr3 | 19189367 | 19189546 |
| chr3 | 19189611 | 19189850 | chr3 | 19190061 | 19190253 | chr3 | 22413593 | 22413770 |
| chr3 | 22413871 | 22413911 | chr3 | 22413960 | 22414050 | chr3 | 24870915 | 24870925 |
| chr3 | 24870982 | 24871177 | chr3 | 24871246 | 24871281 | chr3 | 25469303 | 25469402 |
| chr3 | 25469404 | 25469482 | chr3 | 25469605 | 25469784 | chr3 | 26663963 | 26664202 |
| chr3 | 26664303 | 26664842 | chr3 | 27754404 | 27754583 | chr3 | 27762260 | 27762733 |
| chr3 | 27762783 | 27762962 | chr3 | 27763492 | 27763671 | chr3 | 27764421 | 27764472 |
| chr3 | 27764596 | 27764600 | chr3 | 27765085 | 27765362 | chr3 | 27765401 | 27765444 |
| chr3 | 27771422 | 27772081 | chr3 | 28616745 | 28617764 | chr3 | 32858274 | 32858959 |
| chr3 | 32859256 | 32859285 | chr3 | 32859418 | 32859773 | chr3 | 32859992 | 32860306 |
| chr3 | 33259801 | 33260876 | chr3 | 35680815 | 35680947 | chr3 | 36805720 | 36805959 |
| chr3 | 36806053 | 36806130 | chr3 | 36806179 | 36806292 | chr3 | 37493429 | 37493720 |
| chr3 | 37901952 | 37902028 | chr3 | 38030610 | 38030789 | chr3 | 38032257 | 38032436 |
| chr3 | 38035774 | 38036088 | chr3 | 38080596 | 38081009 | chr3 | 38081154 | 38081286 |
| chr3 | 38081339 | 38081360 | chr3 | 38690527 | 38690766 | chr3 | 38691469 | 38691557 |
| chr3 | 39851674 | 39851913 | chr3 | 41266012 | 41266239 | chr3 | 42222640 | 42222737 |
| chr3 | 42640761 | 42640874 | chr3 | 42814467 | 42814706 | chr3 | 42947333 | 42947632 |
| chr3 | 44036176 | 44036415 | chr3 | 44036496 | 44036675 | chr3 | 44036743 | 44037128 |
| chr3 | 44037130 | 44037282 | chr3 | 44037525 | 44037634 | chr3 | 44037781 | 44038740 |
| chr3 | 44039265 | 44040026 | chr3 | 44040057 | 44040097 | chr3 | 44040413 | 44040652 |
| chr3 | 44040709 | 44041128 | chr3 | 44063354 | 44063953 | chr3 | 44596405 | 44596584 |
| chr3 | 44596614 | 44596913 | chr3 | 44626336 | 44626538 | chr3 | 44626540 | 44626815 |
| chr3 | 44726855 | 44727069 | chr3 | 44727071 | 44727274 | chr3 | 45187222 | 45187328 |
| chr3 | 46924905 | 46925039 | chr3 | 48227686 | 48227788 | chr3 | 48236391 | 48236553 |
| chr3 | 48693228 | 48693701 | chr3 | 48693852 | 48693882 | chr3 | 48693884 | 48694155 |
| chr3 | 48694227 | 48694247 | chr3 | 48698723 | 48699011 | chr3 | 48699377 | 48699859 |
| chr3 | 49906993 | 49907232 | chr3 | 49939836 | 49940495 | chr3 | 50243283 | 50243582 |
| chr3 | 50374581 | 50374760 | chr3 | 50374843 | 50375022 | chr3 | 50375104 | 50375639 |
| chr3 | 50395432 | 50395611 | chr3 | 50402078 | 50403037 | chr3 | 50575518 | 50575635 |
| chr3 | 52552500 | 52552739 | chr3 | 52553395 | 52553537 | chr3 | 53032708 | 53033609 |
| chr3 | 54155525 | 54155764 | chr3 | 54157297 | 54157536 | chr3 | 54157780 | 54158006 |
| chr3 | 55519117 | 55519228 | chr3 | 55523019 | 55523318 | chr3 | 62353291 | 62354130 |
| chr3 | 62354187 | 62354385 | chr3 | 62354531 | 62354793 | chr3 | 62354900 | 62355010 |
| chr3 | 62355332 | 62355571 | chr3 | 62355692 | 62356220 | chr3 | 62356367 | 62356645 |
| chr3 | 62356793 | 62357193 | chr3 | 62357279 | 62357431 | chr3 | 62357527 | 62357671 |
| chr3 | 62357736 | 62357766 | chr3 | 62358059 | 62358117 | chr3 | 62358444 | 62358683 |
| chr3 | 62358758 | 62359115 | chr3 | 62359276 | 62359392 | chr3 | 62359394 | 62359995 |
| chr3 | 62360222 | 62360641 | chr3 | 62362817 | 62362917 | chr3 | 62363099 | 62363206 |
| chr3 | 62363541 | 62363780 | chr3 | 62363819 | 62364177 | chr3 | 62364280 | 62364418 |
| chr3 | 62364659 | 62365205 | chr3 | 62861044 | 62861142 | chr3 | 62861144 | 62861223 |
| chr3 | 63264065 | 63264135 | chr3 | 63264158 | 63264244 | chr3 | 68056816 | 68057235 |
| chr3 | 68980843 | 68980947 | chr3 | 68980949 | 68981202 | chr3 | 68981469 | 68981708 |
| chr3 | 69590865 | 69591044 | chr3 | 69591311 | 69591415 | chr3 | 69591780 | 69591978 |
| chr3 | 69592069 | 69592163 | chr3 | 69741004 | 69741087 | chr3 | 69937792 | 69937926 |
| chr3 | 71802489 | 71802594 | chr3 | 71802596 | 71802720 | chr3 | 71803040 | 71803459 |
| chr3 | 71803553 | 71803558 | chr3 | 71803560 | 71803784 | chr3 | 71803827 | 71803912 |
| chr3 | 73045525 | 73045672 | chr3 | 75955924 | 75955997 | chr3 | 75956027 | 75956463 |
| chr3 | 79815421 | 79815660 | chr3 | 79816688 | 79817099 | chr3 | 79817214 | 79817393 |
| chr3 | 85008452 | 85008726 | chr3 | 85008803 | 85008811 | chr3 | 88248026 | 88248142 |

TABLE 15-continued

| chr | start | end | chr | start | end | chr | start | end |
|---|---|---|---|---|---|---|---|---|
| chr3 | 96532726 | 96532965 | chr3 | 96533302 | 96533541 | chr3 | 96533947 | 96534186 |
| chr3 | 98620817 | 98621056 | chr3 | 99594836 | 99595195 | chr3 | 101230575 | 101230641 |
| chr3 | 101230942 | 101231174 | chr3 | 101397150 | 101397302 | chr3 | 106936068 | 106936294 |
| chr3 | 112052411 | 112052521 | chr3 | 117715472 | 117715643 | chr3 | 117715772 | 117716124 |
| chr3 | 117716214 | 117716312 | chr3 | 117716314 | 117716551 | chr3 | 120003954 | 120004036 |
| chr3 | 120004080 | 120004438 | chr3 | 120169683 | 120169922 | chr3 | 120627319 | 120627535 |
| chr3 | 121902878 | 121902950 | chr3 | 121902991 | 121903219 | chr3 | 121903324 | 121903717 |
| chr3 | 122234151 | 122234246 | chr3 | 122702194 | 122702430 | chr3 | 123166972 | 123167006 |
| chr3 | 123167301 | 123167631 | chr3 | 123167679 | 123167918 | chr3 | 125898567 | 125899292 |
| chr3 | 125899445 | 125899706 | chr3 | 125899740 | 125899925 | chr3 | 125899927 | 125899979 |
| chr3 | 125932169 | 125932586 | chr3 | 126373433 | 126373619 | chr3 | 126373669 | 126373792 |
| chr3 | 126854599 | 126854898 | chr3 | 127534879 | 127534976 | chr3 | 127634112 | 127634291 |
| chr3 | 127794464 | 127794943 | chr3 | 127795248 | 127795253 | chr3 | 128202373 | 128202552 |
| chr3 | 128208829 | 128209308 | chr3 | 128273913 | 128274052 | chr3 | 128274309 | 128274655 |
| chr3 | 128417127 | 128417306 | chr3 | 128719977 | 128720143 | chr3 | 128720164 | 128720347 |
| chr3 | 128720419 | 128720534 | chr3 | 128720567 | 128720696 | chr3 | 128720780 | 128720884 |
| chr3 | 128720886 | 128721319 | chr3 | 128764472 | 128764607 | chr3 | 129693075 | 129693200 |
| chr3 | 129693305 | 129693499 | chr3 | 129693955 | 129694347 | chr3 | 130064351 | 130064588 |
| chr3 | 130064781 | 130064923 | chr3 | 130235952 | 130236064 | chr3 | 130236174 | 130236298 |
| chr3 | 130519821 | 130519929 | chr3 | 131753957 | 131754136 | chr3 | 132756966 | 132757205 |
| chr3 | 133217923 | 133218102 | chr3 | 133748044 | 133748206 | chr3 | 133748552 | 133748679 |
| chr3 | 134369572 | 134369919 | chr3 | 134369921 | 134369931 | chr3 | 134514792 | 134514879 |
| chr3 | 134514960 | 134514971 | chr3 | 134515040 | 134515459 | chr3 | 134515590 | 134516309 |
| chr3 | 136537567 | 136537806 | chr3 | 136538520 | 136538910 | chr3 | 136582941 | 136583037 |
| chr3 | 136751546 | 136751833 | chr3 | 137479149 | 137479388 | chr3 | 137479525 | 137479764 |
| chr3 | 137479893 | 137480847 | chr3 | 137481094 | 137481393 | chr3 | 137481782 | 137481873 |
| chr3 | 137481936 | 137482261 | chr3 | 137483212 | 137483319 | chr3 | 137483570 | 137483691 |
| chr3 | 137483746 | 137484026 | chr3 | 137484085 | 137484105 | chr3 | 137484319 | 137484618 |
| chr3 | 137485931 | 137486390 | chr3 | 137486429 | 137486653 | chr3 | 137487874 | 137488004 |
| chr3 | 137488091 | 137488113 | chr3 | 137488856 | 137489699 | chr3 | 137489876 | 137491135 |
| chr3 | 138153889 | 138154068 | chr3 | 138154240 | 138154277 | chr3 | 138655857 | 138656216 |
| chr3 | 138656743 | 138656982 | chr3 | 138657347 | 138657495 | chr3 | 138657618 | 138658297 |
| chr3 | 138658704 | 138658864 | chr3 | 138659081 | 138659187 | chr3 | 138662060 | 138662180 |
| chr3 | 138662282 | 138662535 | chr3 | 138662705 | 138662941 | chr3 | 138663611 | 138663728 |
| chr3 | 138664142 | 138664249 | chr3 | 138664330 | 138664383 | chr3 | 138664827 | 138665336 |
| chr3 | 138665397 | 138665426 | chr3 | 138665479 | 138665528 | chr3 | 138665540 | 138665718 |
| chr3 | 138665779 | 138666378 | chr3 | 138668646 | 138668685 | chr3 | 138668758 | 138669109 |
| chr3 | 138669141 | 138669485 | chr3 | 138679566 | 138679614 | chr3 | 139258173 | 139258412 |
| chr3 | 139653413 | 139653573 | chr3 | 139653575 | 139653772 | chr3 | 140769430 | 140769789 |
| chr3 | 140769830 | 140770302 | chr3 | 140770408 | 140770590 | chr3 | 140770644 | 140770683 |
| chr3 | 140770685 | 140770909 | chr3 | 140771231 | 140771410 | chr3 | 140771716 | 140771955 |
| chr3 | 141174269 | 141174688 | chr3 | 141481983 | 141482162 | chr3 | 141516315 | 141516794 |
| chr3 | 142682184 | 142682483 | chr3 | 142791076 | 142791173 | chr3 | 142837906 | 142838319 |
| chr3 | 142838530 | 142838647 | chr3 | 142838877 | 142839073 | chr3 | 142839439 | 142839526 |
| chr3 | 142839563 | 142839578 | chr3 | 142839580 | 142839689 | chr3 | 142839784 | 142839902 |
| chr3 | 142839945 | 142839991 | chr3 | 142839993 | 142840128 | chr3 | 142840222 | 142840338 |
| chr3 | 142896066 | 142896305 | chr3 | 145878591 | 145878641 | chr3 | 146187843 | 146188069 |
| chr3 | 147074871 | 147075110 | chr3 | 147077211 | 147077366 | chr3 | 147078865 | 147079284 |
| chr3 | 147087472 | 147087891 | chr3 | 147088363 | 147088542 | chr3 | 147088840 | 147089136 |
| chr3 | 147098332 | 147098571 | chr3 | 147105805 | 147106104 | chr3 | 147108758 | 147109766 |
| chr3 | 147110011 | 147110017 | chr3 | 147110055 | 147110115 | chr3 | 147110229 | 147110774 |
| chr3 | 147110835 | 147111188 | chr3 | 147111703 | 147111734 | chr3 | 147126963 | 147127142 |
| chr3 | 147127677 | 147127913 | chr3 | 147136839 | 147137001 | chr3 | 147137076 | 147137258 |
| chr3 | 147138694 | 147138932 | chr3 | 147139272 | 147139631 | chr3 | 147142126 | 147142152 |
| chr3 | 148415327 | 148415746 | chr3 | 148803259 | 148803370 | chr3 | 149374866 | 149375105 |
| chr3 | 150802882 | 150803000 | chr3 | 150803026 | 150803181 | chr3 | 150803941 | 150804180 |
| chr3 | 150804880 | 150804896 | chr3 | 150804937 | 150805119 | chr3 | 152553245 | 152553484 |
| chr3 | 152553573 | 152553807 | chr3 | 152877592 | 152877703 | chr3 | 153838725 | 153838964 |
| chr3 | 153839429 | 153839559 | chr3 | 153839641 | 153839953 | chr3 | 154146034 | 154146395 |
| chr3 | 154146489 | 154146513 | chr3 | 154146572 | 154146991 | chr3 | 154797250 | 154797289 |
| chr3 | 154797377 | 154797778 | chr3 | 156008943 | 156009300 | chr3 | 156009319 | 156009501 |
| chr3 | 156534393 | 156534407 | chr3 | 157155164 | 157155523 | chr3 | 157155922 | 157156298 |
| chr3 | 157812122 | 157812258 | chr3 | 157812437 | 157812721 | chr3 | 157812812 | 157813171 |
| chr3 | 157813507 | 157813605 | chr3 | 157813670 | 157813926 | chr3 | 157815787 | 157815920 |
| chr3 | 157820502 | 157820681 | chr3 | 157821537 | 157821764 | chr3 | 157821939 | 157822106 |
| chr3 | 157823012 | 157823120 | chr3 | 157823139 | 157823228 | chr3 | 157823390 | 157823569 |
| chr3 | 157824052 | 157824147 | chr3 | 157824212 | 157824332 | chr3 | 157824414 | 157824909 |
| chr3 | 157825083 | 157825491 | chr3 | 158288801 | 158288819 | chr3 | 158288887 | 158288974 |
| chr3 | 159756593 | 159756952 | chr3 | 159944397 | 159944636 | chr3 | 160167929 | 160167989 |
| chr3 | 160168071 | 160168108 | chr3 | 164912329 | 164912568 | chr3 | 164912827 | 164913960 |
| chr3 | 164914906 | 164915205 | chr3 | 169376080 | 169376319 | chr3 | 169376581 | 169376878 |
| chr3 | 169539810 | 169540704 | chr3 | 169540967 | 169541134 | chr3 | 170136540 | 170136839 |
| chr3 | 170302528 | 170302767 | chr3 | 170302989 | 170303143 | chr3 | 170303380 | 170303495 |
| chr3 | 170303563 | 170303922 | chr3 | 171527953 | 171528071 | chr3 | 172165356 | 172165785 |
| chr3 | 172165867 | 172166234 | chr3 | 172166236 | 172166513 | chr3 | 172166673 | 172166725 |
| chr3 | 172166783 | 172166894 | chr3 | 172167000 | 172167142 | chr3 | 172167223 | 172167402 |
| chr3 | 172167596 | 172167995 | chr3 | 172355818 | 172355888 | chr3 | 172355903 | 172355997 |
| chr3 | 172425281 | 172425382 | chr3 | 172425701 | 172425802 | chr3 | 172469837 | 172469951 |

TABLE 15-continued

| chr | start | end | chr | start | end | chr | start | end |
|---|---|---|---|---|---|---|---|---|
| chr3 | 173115155 | 173115634 | chr3 | 173302464 | 173302669 | chr3 | 173302735 | 173302763 |
| chr3 | 173302900 | 173303319 | chr3 | 178861414 | 178861533 | chr3 | 178916788 | 178916967 |
| chr3 | 178921465 | 178921644 | chr3 | 178935968 | 178936205 | chr3 | 178951997 | 178952176 |
| chr3 | 179168582 | 179169354 | chr3 | 179754086 | 179754193 | chr3 | 179754239 | 179754483 |
| chr3 | 179754485 | 179754760 | chr3 | 179754804 | 179754873 | chr3 | 179755087 | 179755465 |
| chr3 | 181413068 | 181413069 | chr3 | 181413422 | 181413460 | chr3 | 181413647 | 181414426 |
| chr3 | 181419972 | 181420211 | chr3 | 181420226 | 181420465 | chr3 | 181421308 | 181422387 |
| chr3 | 181422464 | 181423063 | chr3 | 181428311 | 181428850 | chr3 | 181430614 | 181430853 |
| chr3 | 181437030 | 181437299 | chr3 | 181437301 | 181437449 | chr3 | 181438095 | 181438454 |
| chr3 | 181440811 | 181442010 | chr3 | 181442069 | 181442426 | chr3 | 181442964 | 181443550 |
| chr3 | 181444051 | 181444322 | chr3 | 181444335 | 181444525 | chr3 | 181444613 | 181444754 |
| chr3 | 181444828 | 181444949 | chr3 | 181444989 | 181444989 | chr3 | 181444991 | 181445114 |
| chr3 | 181445268 | 181445567 | chr3 | 181445649 | 181445725 | chr3 | 181445800 | 181445948 |
| chr3 | 182816010 | 182816129 | chr3 | 182895871 | 182895990 | chr3 | 183145336 | 183145695 |
| chr3 | 183145829 | 183146128 | chr3 | 183146297 | 183146536 | chr3 | 183146574 | 183146753 |
| chr3 | 183648036 | 183648101 | chr3 | 183728814 | 183728926 | chr3 | 183965514 | 183965625 |
| chr3 | 184017964 | 184018237 | chr3 | 184031615 | 184031734 | chr3 | 184057527 | 184057636 |
| chr3 | 184301634 | 184301671 | chr3 | 184319741 | 184319843 | chr3 | 184319874 | 184319980 |
| chr3 | 185001908 | 185002018 | chr3 | 185271201 | 185271380 | chr3 | 185303173 | 185303352 |
| chr3 | 185362989 | 185363348 | chr3 | 185643246 | 185643485 | chr3 | 186078683 | 186078982 |
| chr3 | 186079119 | 186079412 | chr3 | 186080114 | 186080245 | chr3 | 186080247 | 186080293 |
| chr3 | 186857051 | 186857710 | chr3 | 187387776 | 187387921 | chr3 | 187388007 | 187388315 |
| chr3 | 192125754 | 192125829 | chr3 | 192126116 | 192126711 | chr3 | 192126787 | 192126849 |
| chr3 | 192126851 | 192126955 | chr3 | 192127265 | 192127373 | chr3 | 192127557 | 192127731 |
| chr3 | 192127937 | 192128164 | chr3 | 192232017 | 192232077 | chr3 | 192232079 | 192232256 |
| chr3 | 192232362 | 192232437 | chr3 | 192232478 | 192232661 | chr3 | 192232753 | 192232819 |
| chr3 | 192232850 | 192232952 | chr3 | 192233095 | 192233232 | chr3 | 192958830 | 192959071 |
| chr3 | 193312046 | 193312165 | chr3 | 193419628 | 193419745 | chr3 | 193548557 | 193548797 |
| chr3 | 193548842 | 193548916 | chr3 | 193776015 | 193776194 | chr3 | 194048731 | 194049015 |
| chr3 | 194208185 | 194208258 | chr3 | 194208468 | 194208664 | chr3 | 194407924 | 194407936 |
| chr3 | 194408055 | 194408103 | chr3 | 194408279 | 194408769 | chr3 | 194408839 | 194409118 |
| chr3 | 195536642 | 195536828 | chr3 | 195538330 | 195538435 | chr3 | 195586956 | 195587195 |
| chr3 | 195601157 | 195601363 | chr3 | 195602364 | 195602435 | chr3 | 195648720 | 195648899 |
| chr3 | 196069893 | 196070192 | chr3 | 196255543 | 196255632 | chr3 | 196387206 | 196387505 |
| chr3 | 196387528 | 196387767 | chr3 | 196388303 | 196388662 | chr3 | 196731055 | 196731133 |
| chr3 | 196731197 | 196731414 | chr3 | 196755893 | 196756063 | chr3 | 197327025 | 197327131 |
| chr3 | 197616633 | 197616812 | chr3 | 197676955 | 197677134 | chr3 | 197685698 | 197685817 |
| chr3 | 197686060 | 197686177 | chr3 | 197686891 | 197687310 | chr4 | 330716 | 330790 |
| chr4 | 331308 | 331416 | chr4 | 568333 | 568653 | chr4 | 569048 | 569116 |
| chr4 | 569275 | 569436 | chr4 | 569461 | 569733 | chr4 | 570931 | 571110 |
| chr4 | 571420 | 571779 | chr4 | 628488 | 628770 | chr4 | 651110 | 651348 |
| chr4 | 657570 | 657657 | chr4 | 678397 | 678576 | chr4 | 718082 | 718202 |
| chr4 | 718240 | 718321 | chr4 | 829537 | 829716 | chr4 | 955292 | 955531 |
| chr4 | 955774 | 956013 | chr4 | 995876 | 995994 | chr4 | 996101 | 996175 |
| chr4 | 1008642 | 1008806 | chr4 | 1016332 | 1016340 | chr4 | 1016533 | 1016787 |
| chr4 | 1025852 | 1026151 | chr4 | 1093457 | 1093558 | chr4 | 1165276 | 1165287 |
| chr4 | 1165450 | 1165575 | chr4 | 1188947 | 1189126 | chr4 | 1282441 | 1282620 |
| chr4 | 1331636 | 1331780 | chr4 | 1338615 | 1338891 | chr4 | 1339023 | 1339130 |
| chr4 | 1396498 | 1396593 | chr4 | 1396595 | 1396697 | chr4 | 1397297 | 1397596 |
| chr4 | 1398222 | 1398247 | chr4 | 1398264 | 1398461 | chr4 | 1399627 | 1399633 |
| chr4 | 1401643 | 1401847 | chr4 | 1512294 | 1512473 | chr4 | 1556335 | 1556603 |
| chr4 | 1576387 | 1576626 | chr4 | 1616606 | 1617173 | chr4 | 1687006 | 1687185 |
| chr4 | 1803447 | 1803686 | chr4 | 1806010 | 1806089 | chr4 | 1807281 | 1807460 |
| chr4 | 1993677 | 1994276 | chr4 | 2042117 | 2042123 | chr4 | 2042169 | 2042259 |
| chr4 | 2066011 | 2066370 | chr4 | 2305571 | 2305930 | chr4 | 2527903 | 2528012 |
| chr4 | 2540247 | 2540395 | chr4 | 2765767 | 2766006 | chr4 | 2926292 | 2926471 |
| chr4 | 2978878 | 2979094 | chr4 | 3446917 | 3447096 | chr4 | 3447737 | 3448096 |
| chr4 | 3768759 | 3768950 | chr4 | 3768995 | 3769190 | chr4 | 3769560 | 3769665 |
| chr4 | 3873613 | 3873852 | chr4 | 4228094 | 4228168 | chr4 | 4228189 | 4228333 |
| chr4 | 4229586 | 4229885 | chr4 | 4387431 | 4387730 | chr4 | 4417467 | 4417706 |
| chr4 | 4855018 | 4855192 | chr4 | 4855231 | 4855257 | chr4 | 4855283 | 4855522 |
| chr4 | 4862671 | 4863210 | chr4 | 4867613 | 4867864 | chr4 | 4867924 | 4867972 |
| chr4 | 4868468 | 4868793 | chr4 | 4868829 | 4869000 | chr4 | 4869132 | 4869187 |
| chr4 | 4872009 | 4872032 | chr4 | 4872060 | 4872248 | chr4 | 4872695 | 4872934 |
| chr4 | 4873329 | 4873580 | chr4 | 5052995 | 5053594 | chr4 | 5053651 | 5054190 |
| chr4 | 5709819 | 5709985 | chr4 | 5712891 | 5713232 | chr4 | 5713327 | 5713370 |
| chr4 | 5889848 | 5890147 | chr4 | 5890180 | 5890539 | chr4 | 5891871 | 5892082 |
| chr4 | 5892110 | 5892251 | chr4 | 5892676 | 5892791 | chr4 | 5893898 | 5894083 |
| chr4 | 5894600 | 5894633 | chr4 | 5894813 | 5894882 | chr4 | 6200797 | 6201293 |
| chr4 | 6202011 | 6202370 | chr4 | 6247277 | 6247456 | chr4 | 6564904 | 6565143 |
| chr4 | 6670110 | 6670289 | chr4 | 6748251 | 6748662 | chr4 | 6957489 | 6957701 |
| chr4 | 7647679 | 7648038 | chr4 | 7758402 | 7758581 | chr4 | 8582475 | 8582619 |
| chr4 | 8607724 | 8608023 | chr4 | 8608459 | 8608698 | chr4 | 8858804 | 8859048 |
| chr4 | 8859382 | 8859823 | chr4 | 8859875 | 8859938 | chr4 | 8860398 | 8860654 |
| chr4 | 8861606 | 8861753 | chr4 | 8861919 | 8862102 | chr4 | 8862705 | 8862812 |
| chr4 | 8863339 | 8863527 | chr4 | 8863857 | 8863878 | chr4 | 8864434 | 8864683 |
| chr4 | 8864764 | 8865155 | chr4 | 8868734 | 8868846 | chr4 | 8868932 | 8869271 |
| chr4 | 8869369 | 8869453 | chr4 | 8869498 | 8869917 | chr4 | 8872957 | 8873073 |

TABLE 15-continued

| chr | start | end | chr | start | end | chr | start | end |
|---|---|---|---|---|---|---|---|---|
| chr4 | 8873774 | 8874077 | chr4 | 8874397 | 8874535 | chr4 | 8874773 | 8874812 |
| chr4 | 8875803 | 8875982 | chr4 | 8893427 | 8893606 | chr4 | 8893714 | 8893726 |
| chr4 | 8893816 | 8894013 | chr4 | 8894547 | 8894958 | chr4 | 8895232 | 8895446 |
| chr4 | 8895480 | 8895659 | chr4 | 8895965 | 8896098 | chr4 | 8896118 | 8896134 |
| chr4 | 9423195 | 9423281 | chr4 | 9782942 | 9783096 | chr4 | 9783126 | 9783424 |
| chr4 | 9783501 | 9783502 | chr4 | 10458309 | 10459208 | chr4 | 10462740 | 10463048 |
| chr4 | 10463073 | 10463256 | chr4 | 10463258 | 10463636 | chr4 | 11429482 | 11429720 |
| chr4 | 13523929 | 13524252 | chr4 | 13524571 | 13524872 | chr4 | 13537492 | 13537779 |
| chr4 | 13540946 | 13541146 | chr4 | 13541309 | 13541348 | chr4 | 13545941 | 13546172 |
| chr4 | 13548404 | 13548590 | chr4 | 13548635 | 13548999 | chr4 | 13549246 | 13549605 |
| chr4 | 15780123 | 15780422 | chr4 | 16084642 | 16084819 | chr4 | 16085167 | 16085180 |
| chr4 | 16085182 | 16085302 | chr4 | 16085352 | 16085481 | chr4 | 16085531 | 16085602 |
| chr4 | 16085675 | 16085770 | chr4 | 17782913 | 17783294 | chr4 | 17783296 | 17783322 |
| chr4 | 17783324 | 17783481 | chr4 | 17783610 | 17783692 | chr4 | 20254619 | 20254774 |
| chr4 | 20255339 | 20255368 | chr4 | 20255525 | 20255938 | chr4 | 20256067 | 20256286 |
| chr4 | 20256383 | 20256426 | chr4 | 21950146 | 21950155 | chr4 | 21950157 | 21950296 |
| chr4 | 24801868 | 24802053 | chr4 | 24914564 | 24914743 | chr4 | 25656728 | 25656893 |
| chr4 | 25657338 | 25657365 | chr4 | 25657367 | 25657414 | chr4 | 25657416 | 25657577 |
| chr4 | 27086358 | 27086537 | chr4 | 30724162 | 30724461 | chr4 | 37245837 | 37245939 |
| chr4 | 37246060 | 37246361 | chr4 | 37246490 | 37246700 | chr4 | 37247016 | 37247238 |
| chr4 | 37247294 | 37247306 | chr4 | 40910205 | 40910563 | chr4 | 41258624 | 41258789 |
| chr4 | 41259086 | 41259276 | chr4 | 41746922 | 41747221 | chr4 | 41747419 | 41747658 |
| chr4 | 41747889 | 41747977 | chr4 | 41748144 | 41748397 | chr4 | 41748583 | 41748767 |
| chr4 | 41748857 | 41748882 | chr4 | 41748976 | 41749138 | chr4 | 41749187 | 41749846 |
| chr4 | 41750125 | 41750604 | chr4 | 41751789 | 41751990 | chr4 | 41752363 | 41752782 |
| chr4 | 41752884 | 41753483 | chr4 | 41753512 | 41753712 | chr4 | 41753714 | 41753803 |
| chr4 | 41753805 | 41753917 | chr4 | 41754031 | 41754171 | chr4 | 41875337 | 41875891 |
| chr4 | 41881286 | 41881517 | chr4 | 41882469 | 41882533 | chr4 | 41882652 | 41882682 |
| chr4 | 41882988 | 41883407 | chr4 | 41883411 | 41883710 | chr4 | 41993731 | 41993896 |
| chr4 | 42152962 | 42153412 | chr4 | 42153533 | 42153633 | chr4 | 42153882 | 42154127 |
| chr4 | 42154201 | 42154385 | chr4 | 42154387 | 42154440 | chr4 | 42154561 | 42155100 |
| chr4 | 42398768 | 42398947 | chr4 | 42399045 | 42399284 | chr4 | 42399601 | 42399960 |
| chr4 | 44449387 | 44449570 | chr4 | 44449653 | 44449743 | chr4 | 44450170 | 44450177 |
| chr4 | 46995079 | 46995821 | chr4 | 46995823 | 46995918 | chr4 | 47034834 | 47035013 |
| chr4 | 48485152 | 48485289 | chr4 | 48485590 | 48486104 | chr4 | 48486254 | 48486493 |
| chr4 | 48492100 | 48492517 | chr4 | 48988013 | 48988229 | chr4 | 48988380 | 48988432 |
| chr4 | 53728417 | 53729087 | chr4 | 54966756 | 54967175 | chr4 | 54967264 | 54967563 |
| chr4 | 54969832 | 54970174 | chr4 | 54970277 | 54970576 | chr4 | 54975855 | 54975932 |
| chr4 | 54975991 | 54976116 | chr4 | 54976171 | 54976214 | chr4 | 55092973 | 55093332 |
| chr4 | 55096143 | 55096363 | chr4 | 55096441 | 55096442 | chr4 | 55097315 | 55097554 |
| chr4 | 55097709 | 55097729 | chr4 | 55097874 | 55098093 | chr4 | 55098198 | 55098473 |
| chr4 | 55098590 | 55098769 | chr4 | 55099040 | 55099159 | chr4 | 55524138 | 55524367 |
| chr4 | 55991019 | 55991270 | chr4 | 55992030 | 55992090 | chr4 | 55992153 | 55992269 |
| chr4 | 56659618 | 56659867 | chr4 | 56659935 | 56660097 | chr4 | 57371632 | 57371868 |
| chr4 | 57371870 | 57372051 | chr4 | 57372241 | 57372600 | chr4 | 57396866 | 57397345 |
| chr4 | 57521300 | 57521396 | chr4 | 57521506 | 57521664 | chr4 | 57521701 | 57522383 |
| chr4 | 57522420 | 57522908 | chr4 | 57687632 | 57687871 | chr4 | 57777338 | 57777577 |
| chr4 | 57803529 | 57803613 | chr4 | 57975930 | 57976289 | chr4 | 57976316 | 57976675 |
| chr4 | 62066134 | 62066645 | chr4 | 62067419 | 62067718 | chr4 | 62067992 | 62068202 |
| chr4 | 66535048 | 66535315 | chr4 | 66535351 | 66535483 | chr4 | 66536068 | 66536427 |
| chr4 | 74702379 | 74702448 | chr4 | 74702450 | 74702608 | chr4 | 74809786 | 74810025 |
| chr4 | 75241349 | 75241528 | chr4 | 75858482 | 75858611 | chr4 | 76555455 | 76555547 |
| chr4 | 76555549 | 76555934 | chr4 | 76912717 | 76912836 | chr4 | 79689573 | 79689812 |
| chr4 | 81106252 | 81106663 | chr4 | 81106665 | 81106669 | chr4 | 81124201 | 81124740 |
| chr4 | 81186972 | 81187151 | chr4 | 81187485 | 81187664 | chr4 | 81188230 | 81188316 |
| chr4 | 81188385 | 81188644 | chr4 | 81189336 | 81189661 | chr4 | 81189714 | 81189995 |
| chr4 | 81951357 | 81951536 | chr4 | 81951938 | 81952046 | chr4 | 81952078 | 81952312 |
| chr4 | 81952364 | 81952437 | chr4 | 82135786 | 82135888 | chr4 | 82135920 | 82136145 |
| chr4 | 82136403 | 82136642 | chr4 | 82136733 | 82136912 | chr4 | 83323428 | 83323677 |
| chr4 | 85402748 | 85403425 | chr4 | 85403824 | 85403928 | chr4 | 85404112 | 85404141 |
| chr4 | 85404225 | 85404476 | chr4 | 85404650 | 85404783 | chr4 | 85413977 | 85414114 |
| chr4 | 85414149 | 85414244 | chr4 | 85414270 | 85414337 | chr4 | 85414458 | 85414509 |
| chr4 | 85414637 | 85414936 | chr4 | 85417241 | 85417474 | chr4 | 85417517 | 85417660 |
| chr4 | 85417873 | 85418166 | chr4 | 85418319 | 85418370 | chr4 | 85418522 | 85418583 |
| chr4 | 85422101 | 85422520 | chr4 | 85422866 | 85422929 | chr4 | 85422973 | 85423052 |
| chr4 | 85424323 | 85424562 | chr4 | 87515263 | 87515442 | chr4 | 89378362 | 89378601 |
| chr4 | 89378667 | 89378767 | chr4 | 89378832 | 89378966 | chr4 | 90757439 | 90757913 |
| chr4 | 90758031 | 90758210 | chr4 | 90758681 | 90758980 | chr4 | 93225163 | 93225252 |
| chr4 | 93226367 | 93226380 | chr4 | 93226382 | 93226729 | chr4 | 93226729 | 93226958 |
| chr4 | 94750882 | 94751241 | chr4 | 94751342 | 94751581 | chr4 | 94753341 | 94753520 |
| chr4 | 94756002 | 94756186 | chr4 | 95127560 | 95127679 | chr4 | 96470678 | 96470857 |
| chr4 | 101111166 | 101111585 | chr4 | 101111765 | 101111872 | chr4 | 101111874 | 101112058 |
| chr4 | 107955210 | 107955929 | chr4 | 107956582 | 107957181 | chr4 | 107957271 | 107957554 |
| chr4 | 107957364 | 107957570 | chr4 | 109093016 | 109093255 | chr4 | 109093307 | 109093606 |
| chr4 | 110222996 | 110223428 | chr4 | 110223579 | 110223598 | chr4 | 110223600 | 110223967 |
| chr4 | 110223969 | 110224075 | chr4 | 111532705 | 111533037 | chr4 | 111536192 | 111536506 |
| chr4 | 111536562 | 111536791 | chr4 | 111536882 | 111536975 | chr4 | 111537067 | 111537121 |
| chr4 | 111537356 | 111537572 | chr4 | 111540187 | 111540460 | chr4 | 111542474 | 111542570 |

TABLE 15-continued

| chr | start | end | chr | start | end | chr | start | end |
|---|---|---|---|---|---|---|---|---|
| chr4 | 111542728 | 111542832 | chr4 | 111543132 | 111543346 | chr4 | 111543404 | 111543551 |
| chr4 | 111543579 | 111543696 | chr4 | 111543721 | 111543807 | chr4 | 111544303 | 111544662 |
| chr4 | 111549726 | 111549905 | chr4 | 111550517 | 111550930 | chr4 | 111552044 | 111552223 |
| chr4 | 111553006 | 111553545 | chr4 | 111553815 | 111554054 | chr4 | 111554864 | 111554965 |
| chr4 | 111555194 | 111555447 | chr4 | 111557888 | 111558127 | chr4 | 111558499 | 111559312 |
| chr4 | 111560174 | 111560713 | chr4 | 111562493 | 111562732 | chr4 | 113154804 | 113155043 |
| chr4 | 113430537 | 113430776 | chr4 | 113431755 | 113431855 | chr4 | 113431916 | 113432155 |
| chr4 | 113432227 | 113432504 | chr4 | 113432519 | 113432654 | chr4 | 113436133 | 113436372 |
| chr4 | 113441514 | 113441813 | chr4 | 113442013 | 113442186 | chr4 | 113442247 | 113442612 |
| chr4 | 113444003 | 113444295 | chr4 | 113444297 | 113444534 | chr4 | 117847310 | 117847459 |
| chr4 | 117847470 | 117847549 | chr4 | 121843986 | 121844285 | chr4 | 121992170 | 121992409 |
| chr4 | 121993915 | 121994334 | chr4 | 122301405 | 122301713 | chr4 | 122302032 | 122302331 |
| chr4 | 122685744 | 122685891 | chr4 | 122686119 | 122686453 | chr4 | 122686455 | 122686598 |
| chr4 | 122871195 | 122871434 | chr4 | 122871488 | 122872087 | chr4 | 123664147 | 123664249 |
| chr4 | 126237252 | 126237491 | chr4 | 126237552 | 126237701 | chr4 | 126237931 | 126238511 |
| chr4 | 128543956 | 128544255 | chr4 | 128544569 | 128544868 | chr4 | 134067794 | 134068093 |
| chr4 | 134068475 | 134068777 | chr4 | 134068779 | 134068894 | chr4 | 134069215 | 134069394 |
| chr4 | 134069498 | 134069977 | chr4 | 134070300 | 134070369 | chr4 | 134070371 | 134070479 |
| chr4 | 134071559 | 134072611 | chr4 | 134072677 | 134073058 | chr4 | 134073128 | 134073403 |
| chr4 | 134073486 | 134073725 | chr4 | 134073772 | 134073789 | chr4 | 134073944 | 134074243 |
| chr4 | 140200427 | 140201157 | chr4 | 140201193 | 140201566 | chr4 | 140657000 | 140657166 |
| chr4 | 141347925 | 141348227 | chr4 | 141418841 | 141419500 | chr4 | 141488790 | 141489159 |
| chr4 | 142053155 | 142053235 | chr4 | 142053418 | 142053837 | chr4 | 142054141 | 142054254 |
| chr4 | 142054256 | 142054560 | chr4 | 143766714 | 143767013 | chr4 | 144621248 | 144621440 |
| chr4 | 144621515 | 144621897 | chr4 | 144621982 | 144622147 | chr4 | 145567951 | 145568250 |
| chr4 | 145568361 | 145568745 | chr4 | 146853937 | 146854056 | chr4 | 147558179 | 147558382 |
| chr4 | 147558477 | 147558598 | chr4 | 147559220 | 147560079 | chr4 | 147560134 | 147560419 |
| chr4 | 147560460 | 147560659 | chr4 | 147560835 | 147561146 | chr4 | 147561360 | 147561950 |
| chr4 | 147562000 | 147562154 | chr4 | 147568549 | 147569148 | chr4 | 147569546 | 147569685 |
| chr4 | 147569697 | 147569725 | chr4 | 147576079 | 147576202 | chr4 | 147576330 | 147576738 |
| chr4 | 152246058 | 152246237 | chr4 | 152246398 | 152246403 | chr4 | 153249297 | 153249476 |
| chr4 | 153702690 | 153702805 | chr4 | 154216277 | 154216449 | chr4 | 154709440 | 154709611 |
| chr4 | 154709759 | 154709828 | chr4 | 154709830 | 154710598 | chr4 | 154710600 | 154710618 |
| chr4 | 154710729 | 154710999 | chr4 | 154712084 | 154712683 | chr4 | 154713426 | 154713605 |
| chr4 | 154713861 | 154714085 | chr4 | 155254092 | 155254271 | chr4 | 155411411 | 155411494 |
| chr4 | 155411930 | 155412370 | chr4 | 155663476 | 155663728 | chr4 | 155665371 | 155665550 |
| chr4 | 156129079 | 156129258 | chr4 | 156129354 | 156129387 | chr4 | 156129444 | 156129593 |
| chr4 | 156129653 | 156129892 | chr4 | 156129963 | 156130382 | chr4 | 156297337 | 156297636 |
| chr4 | 156297942 | 156298130 | chr4 | 156588237 | 156588245 | chr4 | 156588364 | 156588476 |
| chr4 | 156589179 | 156589203 | chr4 | 156589259 | 156589418 | chr4 | 156680156 | 156680485 |
| chr4 | 156680596 | 156680635 | chr4 | 156681281 | 156681465 | chr4 | 158141502 | 158141657 |
| chr4 | 158142744 | 158143101 | chr4 | 158143355 | 158143466 | chr4 | 158143610 | 158143654 |
| chr4 | 164252890 | 164253207 | chr4 | 164253209 | 164253549 | chr4 | 165304428 | 165304667 |
| chr4 | 165304948 | 165305024 | chr4 | 165305060 | 165305247 | chr4 | 166414897 | 166414996 |
| chr4 | 166794691 | 166794990 | chr4 | 166795933 | 166795993 | chr4 | 166796118 | 166796292 |
| chr4 | 168155010 | 168155124 | chr4 | 168155126 | 168155369 | chr4 | 170865262 | 170865381 |
| chr4 | 170947187 | 170947426 | chr4 | 172734067 | 172734148 | chr4 | 172734189 | 172734276 |
| chr4 | 172734278 | 172734306 | chr4 | 172734592 | 172734860 | chr4 | 174429584 | 174429763 |
| chr4 | 174430212 | 174430554 | chr4 | 174430794 | 174431171 | chr4 | 174438477 | 174438627 |
| chr4 | 174439741 | 174440340 | chr4 | 174440555 | 174440794 | chr4 | 174443138 | 174443317 |
| chr4 | 174443480 | 174444019 | chr4 | 174444199 | 174444256 | chr4 | 174446508 | 174446595 |
| chr4 | 174449847 | 174450408 | chr4 | 174450410 | 174450727 | chr4 | 174450752 | 174451586 |
| chr4 | 174451768 | 174452187 | chr4 | 174459094 | 174459375 | chr4 | 174459528 | 174459747 |
| chr4 | 174459770 | 174459933 | chr4 | 174460085 | 174460309 | chr4 | 175132661 | 175132840 |
| chr4 | 175132994 | 175133293 | chr4 | 175134806 | 175135765 | chr4 | 175135847 | 175136086 |
| chr4 | 175138419 | 175138629 | chr4 | 175138870 | 175139349 | chr4 | 175139473 | 175139772 |
| chr4 | 175750358 | 175750805 | chr4 | 176923342 | 176923641 | chr4 | 176987230 | 176987313 |
| chr4 | 176987315 | 176987448 | chr4 | 177713154 | 177713513 | chr4 | 180979196 | 180979375 |
| chr4 | 180980208 | 180980447 | chr4 | 183063573 | 183063973 | chr4 | 183063995 | 183064048 |
| chr4 | 183064517 | 183064756 | chr4 | 183064771 | 183065070 | chr4 | 184019164 | 184019403 |
| chr4 | 184019595 | 184019834 | chr4 | 184020043 | 184020263 | chr4 | 184375709 | 184375816 |
| chr4 | 184718157 | 184718456 | chr4 | 184826157 | 184826576 | chr4 | 184826976 | 184827328 |
| chr4 | 184921806 | 184922165 | chr4 | 185089598 | 185089897 | chr4 | 185937252 | 185937971 |
| chr4 | 185938412 | 185938651 | chr4 | 185940250 | 185940549 | chr4 | 185941484 | 185942473 |
| chr4 | 185942492 | 185942863 | chr5 | 53756 | 53899 | chr5 | 92072 | 92210 |
| chr5 | 320762 | 321061 | chr5 | 343957 | 344017 | chr5 | 373976 | 374369 |
| chr5 | 400112 | 400291 | chr5 | 480918 | 481037 | chr5 | 491257 | 491616 |
| chr5 | 524252 | 524491 | chr5 | 538663 | 538902 | chr5 | 554212 | 554569 |
| chr5 | 554812 | 554916 | chr5 | 555193 | 555372 | chr5 | 555891 | 556070 |
| chr5 | 677799 | 678098 | chr5 | 1034508 | 1034747 | chr5 | 1131130 | 1131478 |
| chr5 | 1193302 | 1193465 | chr5 | 1193793 | 1194032 | chr5 | 1221103 | 1221402 |
| chr5 | 1294550 | 1294849 | chr5 | 1294928 | 1295443 | chr5 | 1295605 | 1295724 |
| chr5 | 1295759 | 1295767 | chr5 | 1445078 | 1445256 | chr5 | 1445654 | 1445760 |
| chr5 | 1445841 | 1446013 | chr5 | 1446237 | 1446370 | chr5 | 1446443 | 1446699 |
| chr5 | 1746941 | 1747180 | chr5 | 1874877 | 1875176 | chr5 | 1875356 | 1875595 |
| chr5 | 1875796 | 1876307 | chr5 | 1876638 | 1876921 | chr5 | 1877090 | 1877103 |
| chr5 | 1877195 | 1877320 | chr5 | 1877912 | 1878029 | chr5 | 1878224 | 1878577 |
| chr5 | 1878831 | 1879090 | chr5 | 1879513 | 1879662 | chr5 | 1879690 | 1879812 |

TABLE 15-continued

| chr | start | end | chr | start | end | chr | start | end |
|---|---|---|---|---|---|---|---|---|
| chr5 | 1882420 | 1882690 | chr5 | 1882758 | 1882922 | chr5 | 1883132 | 1883177 |
| chr5 | 1883329 | 1883617 | chr5 | 1883880 | 1883908 | chr5 | 1884089 | 1884328 |
| chr5 | 1884479 | 1884778 | chr5 | 1885069 | 1885548 | chr5 | 1885910 | 1886077 |
| chr5 | 1886443 | 1886682 | chr5 | 1886736 | 1886842 | chr5 | 1886998 | 1887146 |
| chr5 | 1887547 | 1887582 | chr5 | 1887656 | 1887815 | chr5 | 1930701 | 1931005 |
| chr5 | 1931065 | 1931287 | chr5 | 1931445 | 1931577 | chr5 | 1931618 | 1931840 |
| chr5 | 1950698 | 1951057 | chr5 | 1952550 | 1952639 | chr5 | 1952724 | 1952729 |
| chr5 | 2038629 | 2038863 | chr5 | 2324309 | 2324488 | chr5 | 2541400 | 2541699 |
| chr5 | 2738746 | 2739130 | chr5 | 2739211 | 2739355 | chr5 | 2739780 | 2739803 |
| chr5 | 2739861 | 2740301 | chr5 | 2740431 | 2740665 | chr5 | 2741123 | 2741139 |
| chr5 | 2743516 | 2743660 | chr5 | 2743699 | 2743815 | chr5 | 2748298 | 2748490 |
| chr5 | 2749110 | 2749407 | chr5 | 2749625 | 2749777 | chr5 | 2750655 | 2750770 |
| chr5 | 2751855 | 2751974 | chr5 | 2752897 | 2753153 | chr5 | 2754664 | 2754703 |
| chr5 | 2754804 | 2754807 | chr5 | 2755227 | 2756486 | chr5 | 2756504 | 2756603 |
| chr5 | 2756674 | 2757523 | chr5 | 3031800 | 3032099 | chr5 | 3324948 | 3325367 |
| chr5 | 3590314 | 3590658 | chr5 | 3590804 | 3590853 | chr5 | 3591252 | 3591491 |
| chr5 | 3591768 | 3592127 | chr5 | 3592643 | 3592961 | chr5 | 3594155 | 3594520 |
| chr5 | 3594778 | 3594814 | chr5 | 3595056 | 3595254 | chr5 | 3595361 | 3595369 |
| chr5 | 3595850 | 3596080 | chr5 | 3596556 | 3596725 | chr5 | 3596825 | 3596980 |
| chr5 | 3597317 | 3597556 | chr5 | 3600076 | 3600255 | chr5 | 3602717 | 3603422 |
| chr5 | 3606712 | 3606771 | chr5 | 3673960 | 3674256 | chr5 | 4144300 | 4144592 |
| chr5 | 5139578 | 5139621 | chr5 | 5139754 | 5139997 | chr5 | 5140079 | 5140318 |
| chr5 | 5140528 | 5140758 | chr5 | 5140850 | 5141006 | chr5 | 6228525 | 6228650 |
| chr5 | 6448837 | 6449676 | chr5 | 6583371 | 6583670 | chr5 | 6687175 | 6687528 |
| chr5 | 7395162 | 7395394 | chr5 | 7395434 | 7395641 | chr5 | 7850251 | 7850286 |
| chr5 | 7850919 | 7851218 | chr5 | 9546511 | 9546750 | chr5 | 10333611 | 10334210 |
| chr5 | 10564925 | 10565228 | chr5 | 10565263 | 10565263 | chr5 | 10565265 | 10565704 |
| chr5 | 11384965 | 11385067 | chr5 | 11385069 | 11385465 | chr5 | 11903659 | 11903725 |
| chr5 | 11903822 | 11904114 | chr5 | 11904116 | 11904174 | chr5 | 11904196 | 11904380 |
| chr5 | 11904456 | 11904798 | chr5 | 11904801 | 11905040 | chr5 | 15500659 | 15500689 |
| chr5 | 15500736 | 15500833 | chr5 | 15500835 | 15501018 | chr5 | 16178946 | 16179153 |
| chr5 | 16179555 | 16179795 | chr5 | 16180183 | 16180321 | chr5 | 16466683 | 16466796 |
| chr5 | 16467097 | 16467216 | chr5 | 16936255 | 16936402 | chr5 | 16936500 | 16936614 |
| chr5 | 17203036 | 17203266 | chr5 | 17217854 | 17217865 | chr5 | 17217992 | 17218033 |
| chr5 | 17218121 | 17218300 | chr5 | 17218862 | 17218934 | chr5 | 17218986 | 17219101 |
| chr5 | 17512040 | 17512192 | chr5 | 22853425 | 22853596 | chr5 | 31193844 | 31194083 |
| chr5 | 31194312 | 31194511 | chr5 | 31639583 | 31640008 | chr5 | 31691580 | 31691745 |
| chr5 | 31854987 | 31855286 | chr5 | 32710252 | 32710551 | chr5 | 32710718 | 32710957 |
| chr5 | 32711024 | 32711429 | chr5 | 32711431 | 32711617 | chr5 | 32711729 | 32711968 |
| chr5 | 32711985 | 32712102 | chr5 | 32712290 | 32712584 | chr5 | 32712675 | 32712943 |
| chr5 | 33298097 | 33298101 | chr5 | 33891980 | 33892219 | chr5 | 33892339 | 33892518 |
| chr5 | 33936067 | 33936232 | chr5 | 33936234 | 33936362 | chr5 | 33936364 | 33936751 |
| chr5 | 34656834 | 34657042 | chr5 | 37834610 | 37834737 | chr5 | 37836572 | 37838071 |
| chr5 | 37838448 | 37838987 | chr5 | 37839684 | 37839736 | chr5 | 37839808 | 37840075 |
| chr5 | 37840077 | 37840220 | chr5 | 37840288 | 37840363 | chr5 | 37840530 | 37840843 |
| chr5 | 38257397 | 38257541 | chr5 | 38257543 | 38257696 | chr5 | 38257752 | 38257909 |
| chr5 | 38257945 | 38258051 | chr5 | 38556996 | 38557076 | chr5 | 38557188 | 38557427 |
| chr5 | 38845574 | 38845955 | chr5 | 38846469 | 38846533 | chr5 | 39343086 | 39343201 |
| chr5 | 40681036 | 40681228 | chr5 | 40681262 | 40681455 | chr5 | 40681601 | 40681840 |
| chr5 | 40682070 | 40682080 | chr5 | 42424732 | 42425151 | chr5 | 42950902 | 42951312 |
| chr5 | 42951420 | 42952112 | chr5 | 42991751 | 42992242 | chr5 | 42992376 | 42992555 |
| chr5 | 42992557 | 42992598 | chr5 | 42992783 | 42993010 | chr5 | 42993313 | 42993547 |
| chr5 | 42993853 | 42994272 | chr5 | 42994593 | 42994892 | chr5 | 42995073 | 42995254 |
| chr5 | 43007862 | 43008041 | chr5 | 43008113 | 43008472 | chr5 | 43017851 | 43018177 |
| chr5 | 43018327 | 43018690 | chr5 | 43019144 | 43019424 | chr5 | 43019729 | 43019968 |
| chr5 | 43040768 | 43041067 | chr5 | 43215459 | 43215562 | chr5 | 43396915 | 43397230 |
| chr5 | 43397306 | 43397334 | chr5 | 44389782 | 44389929 | chr5 | 45695091 | 45695240 |
| chr5 | 45695314 | 45695608 | chr5 | 45695823 | 45695964 | chr5 | 45696239 | 45696455 |
| chr5 | 45696457 | 45696465 | chr5 | 45696467 | 45696538 | chr5 | 49736497 | 49736789 |
| chr5 | 50262842 | 50263104 | chr5 | 50263486 | 50263725 | chr5 | 50264216 | 50264695 |
| chr5 | 50264746 | 50264925 | chr5 | 50265228 | 50265527 | chr5 | 50265621 | 50265672 |
| chr5 | 50265721 | 50265960 | chr5 | 50674051 | 50674290 | chr5 | 50674486 | 50674557 |
| chr5 | 50674638 | 50674665 | chr5 | 50674925 | 50675164 | chr5 | 50678269 | 50678273 |
| chr5 | 50678373 | 50678552 | chr5 | 50695193 | 50695241 | chr5 | 50695351 | 50695540 |
| chr5 | 54179491 | 54179537 | chr5 | 54179539 | 54179558 | chr5 | 54179610 | 54179730 |
| chr5 | 54179989 | 54180168 | chr5 | 54516275 | 54516681 | chr5 | 54516832 | 54517114 |
| chr5 | 54518577 | 54518633 | chr5 | 54519134 | 54519289 | chr5 | 54519383 | 54519406 |
| chr5 | 54527323 | 54527444 | chr5 | 56248119 | 56248358 | chr5 | 57878174 | 57878473 |
| chr5 | 57878612 | 57878775 | chr5 | 57878811 | 57878851 | chr5 | 59188293 | 59188429 |
| chr5 | 59188952 | 59189058 | chr5 | 59189189 | 59189311 | chr5 | 59189787 | 59190026 |
| chr5 | 63254815 | 63255243 | chr5 | 63255316 | 63255354 | chr5 | 63257645 | 63257944 |
| chr5 | 63801932 | 63802272 | chr5 | 63802274 | 63802305 | chr5 | 63802340 | 63802591 |
| chr5 | 63986409 | 63986528 | chr5 | 63986570 | 63986888 | chr5 | 67591197 | 67591233 |
| chr5 | 68391320 | 68391429 | chr5 | 71014629 | 71014979 | chr5 | 71015095 | 71015814 |
| chr5 | 71403491 | 71403730 | chr5 | 71403882 | 71404158 | chr5 | 72416170 | 72416262 |
| chr5 | 72526319 | 72526415 | chr5 | 72526492 | 72526738 | chr5 | 72528360 | 72528539 |
| chr5 | 72529200 | 72529826 | chr5 | 72529890 | 72530699 | chr5 | 72594722 | 72594837 |
| chr5 | 72594868 | 72595017 | chr5 | 72595047 | 72595141 | chr5 | 72595456 | 72595722 |

TABLE 15-continued

| chr | start | end | chr | start | end | chr | start | end |
|---|---|---|---|---|---|---|---|---|
| chr5 | 72595774 | 72595875 | chr5 | 72598977 | 72598983 | chr5 | 72599060 | 72599442 |
| chr5 | 72599463 | 72599936 | chr5 | 72677775 | 72677826 | chr5 | 72677998 | 72678029 |
| chr5 | 72678366 | 72678416 | chr5 | 72715160 | 72715348 | chr5 | 72715591 | 72715696 |
| chr5 | 72715731 | 72715846 | chr5 | 72716022 | 72716239 | chr5 | 72732870 | 72732910 |
| chr5 | 72733013 | 72733268 | chr5 | 72740047 | 72740286 | chr5 | 72746606 | 72746684 |
| chr5 | 72746730 | 72746785 | chr5 | 75377860 | 75378108 | chr5 | 75380089 | 75380268 |
| chr5 | 75380530 | 75381006 | chr5 | 76011192 | 76011431 | chr5 | 76012504 | 76012681 |
| chr5 | 76249176 | 76249671 | chr5 | 76249696 | 76249907 | chr5 | 76249945 | 76250250 |
| chr5 | 76250351 | 76250590 | chr5 | 76506369 | 76506608 | chr5 | 76506956 | 76507195 |
| chr5 | 76923601 | 76924024 | chr5 | 76924087 | 76924300 | chr5 | 76924417 | 76924494 |
| chr5 | 76924856 | 76925018 | chr5 | 76925477 | 76925776 | chr5 | 76928070 | 76928487 |
| chr5 | 76928588 | 76929007 | chr5 | 76932228 | 76932407 | chr5 | 76932463 | 76933266 |
| chr5 | 76934073 | 76934654 | chr5 | 76934677 | 76934972 | chr5 | 76935937 | 76936039 |
| chr5 | 76936100 | 76936819 | chr5 | 76939436 | 76939867 | chr5 | 76940241 | 76940477 |
| chr5 | 76941115 | 76941414 | chr5 | 77140440 | 77140799 | chr5 | 77147520 | 77147650 |
| chr5 | 77147873 | 77148214 | chr5 | 77148396 | 77148669 | chr5 | 77268278 | 77268734 |
| chr5 | 77268736 | 77269238 | chr5 | 77269264 | 77269408 | chr5 | 78407567 | 78407926 |
| chr5 | 78408118 | 78408275 | chr5 | 78408298 | 78408537 | chr5 | 79783152 | 79783256 |
| chr5 | 79864809 | 79865168 | chr5 | 79866100 | 79866508 | chr5 | 79947497 | 79947796 |
| chr5 | 80255722 | 80256075 | chr5 | 80689499 | 80689795 | chr5 | 80690030 | 80690278 |
| chr5 | 82767342 | 82767881 | chr5 | 82768798 | 82769157 | chr5 | 83679121 | 83679300 |
| chr5 | 83679592 | 83679643 | chr5 | 83679645 | 83680431 | chr5 | 83680592 | 83680665 |
| chr5 | 83680694 | 83680812 | chr5 | 87955360 | 87955455 | chr5 | 87955502 | 87955665 |
| chr5 | 87955840 | 87955899 | chr5 | 87956103 | 87956663 | chr5 | 87956680 | 87957062 |
| chr5 | 87962865 | 87963006 | chr5 | 87963365 | 87963601 | chr5 | 87967686 | 87968165 |
| chr5 | 87968411 | 87968686 | chr5 | 87968773 | 87968942 | chr5 | 87970114 | 87970114 |
| chr5 | 87970116 | 87970953 | chr5 | 87974027 | 87974386 | chr5 | 87974767 | 87975126 |
| chr5 | 87976104 | 87976408 | chr5 | 87976423 | 87976662 | chr5 | 87979655 | 87979779 |
| chr5 | 87979900 | 87980014 | chr5 | 87980047 | 87980079 | chr5 | 87980322 | 87980346 |
| chr5 | 87980871 | 87981341 | chr5 | 87985819 | 87986058 | chr5 | 87986127 | 87986154 |
| chr5 | 87986233 | 87986366 | chr5 | 87986445 | 87986472 | chr5 | 87988431 | 87988670 |
| chr5 | 87990311 | 87990530 | chr5 | 88185377 | 88185387 | chr5 | 88185389 | 88186087 |
| chr5 | 89854760 | 89854999 | chr5 | 92939817 | 92939837 | chr5 | 92940178 | 92940236 |
| chr5 | 94955591 | 94956010 | chr5 | 94956849 | 94957088 | chr5 | 94982143 | 94982314 |
| chr5 | 95767856 | 95768035 | chr5 | 95768068 | 95768427 | chr5 | 95768828 | 95769173 |
| chr5 | 100236601 | 100236840 | chr5 | 100238808 | 100238977 | chr5 | 100238979 | 100239022 |
| chr5 | 100239024 | 100239120 | chr5 | 100239135 | 100239167 | chr5 | 101631391 | 101631630 |
| chr5 | 107005906 | 107006265 | chr5 | 111987788 | 111987901 | chr5 | 112043011 | 112043367 |
| chr5 | 112073328 | 112073567 | chr5 | 112175566 | 112175730 | chr5 | 112629342 | 112629359 |
| chr5 | 112629394 | 112629761 | chr5 | 113391163 | 113391218 | chr5 | 113391284 | 113391774 |
| chr5 | 113391776 | 113392122 | chr5 | 113698466 | 113698584 | chr5 | 113698670 | 113698844 |
| chr5 | 113698952 | 113699203 | chr5 | 114515010 | 114515580 | chr5 | 114515611 | 114515728 |
| chr5 | 115151174 | 115151358 | chr5 | 115151650 | 115152385 | chr5 | 115152617 | 115152733 |
| chr5 | 115297105 | 115297293 | chr5 | 115297377 | 115297644 | chr5 | 115297836 | 115297986 |
| chr5 | 115298410 | 115298582 | chr5 | 115298782 | 115298829 | chr5 | 115298894 | 115299133 |
| chr5 | 119799840 | 119800079 | chr5 | 119801223 | 119801522 | chr5 | 121413445 | 121413684 |
| chr5 | 122422161 | 122422315 | chr5 | 122422516 | 122422754 | chr5 | 122423233 | 122423432 |
| chr5 | 122425029 | 122425268 | chr5 | 122431039 | 122431458 | chr5 | 124128503 | 124128574 |
| chr5 | 126626256 | 126626298 | chr5 | 126626300 | 126626795 | chr5 | 127872847 | 127873086 |
| chr5 | 127873553 | 127873789 | chr5 | 127874345 | 127874478 | chr5 | 127874706 | 127874944 |
| chr5 | 128300588 | 128300695 | chr5 | 128300713 | 128300874 | chr5 | 128795984 | 128796097 |
| chr5 | 128796099 | 128796343 | chr5 | 128796777 | 128797076 | chr5 | 128797246 | 128797485 |
| chr5 | 129239966 | 129240205 | chr5 | 131992008 | 131992247 | chr5 | 132947392 | 132947931 |
| chr5 | 133820025 | 133820136 | chr5 | 134366634 | 134366873 | chr5 | 134367007 | 134367266 |
| chr5 | 134367285 | 134367306 | chr5 | 134374370 | 134374506 | chr5 | 134374792 | 134375309 |
| chr5 | 134376120 | 134376474 | chr5 | 134376732 | 134376911 | chr5 | 134385869 | 134386168 |
| chr5 | 134386185 | 134386466 | chr5 | 134582953 | 134582969 | chr5 | 134825372 | 134825611 |
| chr5 | 134825913 | 134826098 | chr5 | 134870362 | 134870601 | chr5 | 134870689 | 134870927 |
| chr5 | 134871526 | 134872125 | chr5 | 134879391 | 134879973 | chr5 | 134914539 | 134914838 |
| chr5 | 135265664 | 135265842 | chr5 | 135266034 | 135266129 | chr5 | 135266578 | 135266753 |
| chr5 | 135528098 | 135528337 | chr5 | 136834009 | 136834051 | chr5 | 136834290 | 136834492 |
| chr5 | 136834494 | 136834608 | chr5 | 136834624 | 136834664 | chr5 | 136834707 | 136834881 |
| chr5 | 136834913 | 136834923 | chr5 | 137225092 | 137225268 | chr5 | 138273717 | 138273845 |
| chr5 | 139047897 | 139048256 | chr5 | 139227705 | 139227991 | chr5 | 139525654 | 139525833 |
| chr5 | 139779840 | 139779953 | chr5 | 140174701 | 140174840 | chr5 | 140174938 | 140174994 |
| chr5 | 140187003 | 140187240 | chr5 | 140305895 | 140306134 | chr5 | 140306445 | 140306620 |
| chr5 | 140306675 | 140306787 | chr5 | 140346514 | 140346753 | chr5 | 140514817 | 140514996 |
| chr5 | 140604361 | 140604596 | chr5 | 140613851 | 140614089 | chr5 | 140614230 | 140614329 |
| chr5 | 140614384 | 140614469 | chr5 | 140777354 | 140777588 | chr5 | 140797000 | 140797279 |
| chr5 | 140797328 | 140797419 | chr5 | 140800384 | 140800965 | chr5 | 140801035 | 140801343 |
| chr5 | 140811136 | 140811138 | chr5 | 140855515 | 140856459 | chr5 | 140856547 | 140856710 |
| chr5 | 141031047 | 141031205 | chr5 | 141262957 | 141263143 | chr5 | 141263261 | 141263316 |
| chr5 | 141931261 | 141931355 | chr5 | 141931425 | 141931585 | chr5 | 142784881 | 142785305 |
| chr5 | 145713562 | 145713981 | chr5 | 145717097 | 145717197 | chr5 | 145717249 | 145717516 |
| chr5 | 145718714 | 145719754 | chr5 | 145719835 | 145719937 | chr5 | 145720019 | 145720024 |
| chr5 | 145720763 | 145720942 | chr5 | 145722033 | 145722467 | chr5 | 145722561 | 145723112 |
| chr5 | 145724421 | 145724780 | chr5 | 145725109 | 145725188 | chr5 | 145725694 | 145725948 |
| chr5 | 146257258 | 146257484 | chr5 | 146257486 | 146257677 | chr5 | 146889129 | 146889183 |

TABLE 15-continued

| chr | start | end | chr | start | end | chr | start | end |
|---|---|---|---|---|---|---|---|---|
| chr5 | 146889332 | 146889538 | chr5 | 146889540 | 146889668 | chr5 | 149681971 | 149682270 |
| chr5 | 150051025 | 150051744 | chr5 | 150400044 | 150400283 | chr5 | 151066339 | 151066578 |
| chr5 | 151304297 | 151304476 | chr5 | 153852579 | 153852878 | chr5 | 153853387 | 153853569 |
| chr5 | 153855101 | 153855340 | chr5 | 153855658 | 153855925 | chr5 | 153856149 | 153856483 |
| chr5 | 153856847 | 153857086 | chr5 | 153857285 | 153857524 | chr5 | 153858220 | 153858699 |
| chr5 | 153859573 | 153859812 | chr5 | 153861948 | 153862180 | chr5 | 153862219 | 153862667 |
| chr5 | 153863347 | 153863417 | chr5 | 153863419 | 153863526 | chr5 | 154209838 | 154210070 |
| chr5 | 154318060 | 154318178 | chr5 | 155107702 | 155107941 | chr5 | 155108042 | 155108084 |
| chr5 | 155108161 | 155108268 | chr5 | 155108356 | 155108612 | chr5 | 155108659 | 155108838 |
| chr5 | 156874164 | 156874403 | chr5 | 157001643 | 157001941 | chr5 | 157078345 | 157078524 |
| chr5 | 157098282 | 157098701 | chr5 | 158478385 | 158478466 | chr5 | 158478513 | 158478864 |
| chr5 | 158524641 | 158524837 | chr5 | 158527367 | 158527817 | chr5 | 158527819 | 158528146 |
| chr5 | 159399015 | 159399100 | chr5 | 160975650 | 160975829 | chr5 | 161274223 | 161274358 |
| chr5 | 161274506 | 161274642 | chr5 | 166865354 | 166865462 | chr5 | 167956087 | 167956267 |
| chr5 | 167956414 | 167956560 | chr5 | 167956601 | 167956686 | chr5 | 168233320 | 168233559 |
| chr5 | 168727837 | 168727928 | chr5 | 168727995 | 168728076 | chr5 | 169064237 | 169064530 |
| chr5 | 169064532 | 169064887 | chr5 | 169532851 | 169533090 | chr5 | 170108211 | 170108450 |
| chr5 | 170735061 | 170735300 | chr5 | 170735731 | 170735875 | chr5 | 170736019 | 170736164 |
| chr5 | 170736716 | 170736831 | chr5 | 170737282 | 170737578 | chr5 | 170737779 | 170737864 |
| chr5 | 170737936 | 170738690 | chr5 | 170738824 | 170739571 | chr5 | 170739746 | 170740058 |
| chr5 | 170740091 | 170740105 | chr5 | 170740391 | 170740478 | chr5 | 170740575 | 170740673 |
| chr5 | 170740675 | 170741031 | chr5 | 170741508 | 170742276 | chr5 | 170742387 | 170742600 |
| chr5 | 170742673 | 170742827 | chr5 | 170743151 | 170743480 | chr5 | 170743647 | 170744255 |
| chr5 | 170744290 | 170744649 | chr5 | 170745286 | 170745560 | chr5 | 172655778 | 172656317 |
| chr5 | 172659314 | 172659378 | chr5 | 172659397 | 172659756 | chr5 | 172659768 | 172660026 |
| chr5 | 172660142 | 172660307 | chr5 | 172660633 | 172661001 | chr5 | 172661127 | 172661228 |
| chr5 | 172661368 | 172661772 | chr5 | 172664148 | 172664567 | chr5 | 172665492 | 172665911 |
| chr5 | 172670882 | 172671121 | chr5 | 172671268 | 172671482 | chr5 | 172671640 | 172671926 |
| chr5 | 172672391 | 172672406 | chr5 | 172672593 | 172672750 | chr5 | 172754486 | 172754725 |
| chr5 | 172754733 | 172754963 | chr5 | 172754986 | 172755032 | chr5 | 172755421 | 172755563 |
| chr5 | 172755595 | 172755745 | chr5 | 172756961 | 172757200 | chr5 | 174115296 | 174115690 |
| chr5 | 174115864 | 174115955 | chr5 | 174147441 | 174147680 | chr5 | 174150341 | 174150520 |
| chr5 | 174159300 | 174159669 | chr5 | 174162800 | 174162945 | chr5 | 174220897 | 174221036 |
| chr5 | 174870643 | 174870882 | chr5 | 174871097 | 174871576 | chr5 | 174921381 | 174921483 |
| chr5 | 175085059 | 175085298 | chr5 | 175085525 | 175085808 | chr5 | 175223571 | 175223748 |
| chr5 | 175223935 | 175223950 | chr5 | 175298572 | 175298986 | chr5 | 175299196 | 175299495 |
| chr5 | 175300277 | 175300456 | chr5 | 175621297 | 175621596 | chr5 | 175792785 | 175792932 |
| chr5 | 175792998 | 175793144 | chr5 | 176023818 | 176023882 | chr5 | 176024006 | 176024350 |
| chr5 | 176046280 | 176046639 | chr5 | 176107191 | 176107485 | chr5 | 176107518 | 176107670 |
| chr5 | 176236631 | 176236990 | chr5 | 176264711 | 176264998 | chr5 | 176764020 | 176764255 |
| chr5 | 177031093 | 177031272 | chr5 | 177408416 | 177408548 | chr5 | 177411561 | 177412210 |
| chr5 | 177713273 | 177713572 | chr5 | 178003629 | 178003662 | chr5 | 178004286 | 178004398 |
| chr5 | 178016513 | 178016571 | chr5 | 178016682 | 178016984 | chr5 | 178017520 | 178017571 |
| chr5 | 178017573 | 178017971 | chr5 | 178367990 | 178368122 | chr5 | 178368415 | 178368462 |
| chr5 | 178421400 | 178421423 | chr5 | 178422167 | 178422224 | chr5 | 178487023 | 178487304 |
| chr5 | 178487342 | 178487493 | chr5 | 178576382 | 178576578 | chr5 | 178655663 | 178655962 |
| chr5 | 178771216 | 178771631 | chr5 | 178771724 | 178771781 | chr5 | 178771783 | 178771860 |
| chr5 | 178771968 | 178772055 | chr5 | 178772120 | 178772359 | chr5 | 178772525 | 178772730 |
| chr5 | 178772779 | 178772824 | chr5 | 178957598 | 178958023 | chr5 | 179214036 | 179214275 |
| chr5 | 179244321 | 179244371 | chr5 | 179780005 | 179780013 | chr5 | 179780036 | 179780244 |
| chr5 | 179780607 | 179781086 | chr5 | 179867405 | 179867637 | chr5 | 180017039 | 180017278 |
| chr5 | 180017532 | 180017689 | chr5 | 180017691 | 180018011 | chr5 | 180018485 | 180018585 |
| chr5 | 180047646 | 180047703 | chr5 | 180075753 | 180075858 | chr5 | 180076054 | 180076412 |
| chr5 | 180076533 | 180076705 | chr5 | 180076721 | 180077080 | chr5 | 180100825 | 180100874 |
| chr5 | 180101016 | 180101168 | chr5 | 180101252 | 180101410 | chr5 | 180326052 | 180326231 |
| chr5 | 180527447 | 180527699 | chr5 | 180527794 | 180527866 | chr5 | 180600769 | 180601030 |
| chr5 | 180601129 | 180601308 | chr6 | 391089 | 391743 | chr6 | 391745 | 391764 |
| chr6 | 391766 | 391900 | chr6 | 392410 | 392434 | chr6 | 392588 | 392959 |
| chr6 | 393125 | 393239 | chr6 | 393241 | 393473 | chr6 | 711039 | 711392 |
| chr6 | 1311899 | 1312095 | chr6 | 1312680 | 1312802 | chr6 | 1314014 | 1314101 |
| chr6 | 1378133 | 1378476 | chr6 | 1379268 | 1379332 | chr6 | 1379510 | 1379689 |
| chr6 | 1379812 | 1380051 | chr6 | 1383598 | 1383709 | chr6 | 1383860 | 1383982 |
| chr6 | 1383984 | 1384180 | chr6 | 1384626 | 1384731 | chr6 | 1385025 | 1385264 |
| chr6 | 1386020 | 1386212 | chr6 | 1389044 | 1389275 | chr6 | 1390159 | 1390361 |
| chr6 | 1390363 | 1390406 | chr6 | 1390424 | 1390759 | chr6 | 1390956 | 1391118 |
| chr6 | 1391230 | 1391469 | chr6 | 1524122 | 1524361 | chr6 | 1605302 | 1605541 |
| chr6 | 1615243 | 1615279 | chr6 | 1624940 | 1625059 | chr6 | 1625129 | 1625779 |
| chr6 | 3053237 | 3053463 | chr6 | 3228955 | 3229134 | chr6 | 3229348 | 3229587 |
| chr6 | 3231926 | 3232029 | chr6 | 3285129 | 3285608 | chr6 | 3405599 | 3405779 |
| chr6 | 4775080 | 4775322 | chr6 | 4836441 | 4836545 | chr6 | 4951178 | 4951469 |
| chr6 | 5783232 | 5783457 | chr6 | 5996852 | 5997091 | chr6 | 5997728 | 5997907 |
| chr6 | 6003213 | 6003529 | chr6 | 6004350 | 6004744 | chr6 | 6004837 | 6005450 |
| chr6 | 6006278 | 6006498 | chr6 | 6006600 | 6006959 | chr6 | 6007516 | 6007670 |
| chr6 | 6007672 | 6007772 | chr6 | 6007833 | 6008355 | chr6 | 6367000 | 6367218 |
| chr6 | 7726260 | 7726439 | chr6 | 7726556 | 7726735 | chr6 | 7726878 | 7727057 |
| chr6 | 7727622 | 7727769 | chr6 | 7728087 | 7728221 | chr6 | 7728746 | 7729045 |
| chr6 | 10381428 | 10381593 | chr6 | 10381695 | 10381969 | chr6 | 10382322 | 10382383 |
| chr6 | 10382648 | 10383126 | chr6 | 10383638 | 10383877 | chr6 | 10384876 | 10384975 |

TABLE 15-continued

| chr | start | end | chr | start | end | chr | start | end |
|---|---|---|---|---|---|---|---|---|
| chr6 | 10385280 | 10386015 | chr6 | 10386123 | 10386357 | chr6 | 10389946 | 10391216 |
| chr6 | 10410429 | 10410668 | chr6 | 10411254 | 10411613 | chr6 | 10415015 | 10415314 |
| chr6 | 10415457 | 10415816 | chr6 | 10416039 | 10416399 | chr6 | 10417059 | 10417530 |
| chr6 | 10418997 | 10419440 | chr6 | 10419477 | 10419596 | chr6 | 10419664 | 10420002 |
| chr6 | 10420975 | 10421171 | chr6 | 10421253 | 10421452 | chr6 | 10421549 | 10422714 |
| chr6 | 10425411 | 10425478 | chr6 | 10425630 | 10425790 | chr6 | 10425839 | 10426970 |
| chr6 | 10881857 | 10882156 | chr6 | 10882247 | 10882426 | chr6 | 10882934 | 10883023 |
| chr6 | 10886993 | 10887185 | chr6 | 10887187 | 10887772 | chr6 | 11043988 | 11044106 |
| chr6 | 11044108 | 11044541 | chr6 | 11044543 | 11044647 | chr6 | 12288420 | 12288779 |
| chr6 | 12749819 | 12749941 | chr6 | 16196952 | 16197191 | chr6 | 17281327 | 17281327 |
| chr6 | 17281329 | 17281351 | chr6 | 18035792 | 18036091 | chr6 | 19691621 | 19691920 |
| chr6 | 19691983 | 19691997 | chr6 | 19692143 | 19692280 | chr6 | 19836983 | 19837064 |
| chr6 | 19837141 | 19837205 | chr6 | 21664905 | 21665144 | chr6 | 24494604 | 24494843 |
| chr6 | 24647262 | 24647371 | chr6 | 26184364 | 26184476 | chr6 | 26188754 | 26189234 |
| chr6 | 26189236 | 26189495 | chr6 | 26199099 | 26199242 | chr6 | 26199612 | 26199791 |
| chr6 | 26214613 | 26214731 | chr6 | 26235124 | 26235437 | chr6 | 26240532 | 26241201 |
| chr6 | 26250378 | 26250685 | chr6 | 26250687 | 26250917 | chr6 | 26250969 | 26251261 |
| chr6 | 26251715 | 26251940 | chr6 | 26252075 | 26252099 | chr6 | 26252141 | 26252180 |
| chr6 | 26271315 | 26271816 | chr6 | 26271818 | 26271854 | chr6 | 26271897 | 26272076 |
| chr6 | 26272416 | 26272715 | chr6 | 26273381 | 26273419 | chr6 | 26273515 | 26273560 |
| chr6 | 26284786 | 26284975 | chr6 | 26327725 | 26328074 | chr6 | 26328206 | 26328505 |
| chr6 | 26332079 | 26332318 | chr6 | 26501764 | 26501841 | chr6 | 26501950 | 26502296 |
| chr6 | 26550895 | 26551059 | chr6 | 26551084 | 26551134 | chr6 | 26577078 | 26577557 |
| chr6 | 26987930 | 26988169 | chr6 | 27059697 | 27059936 | chr6 | 27064581 | 27064769 |
| chr6 | 27064771 | 27065003 | chr6 | 27065005 | 27065300 | chr6 | 27173436 | 27173547 |
| chr6 | 27173633 | 27173855 | chr6 | 27173925 | 27174275 | chr6 | 27182856 | 27182974 |
| chr6 | 27203167 | 27203286 | chr6 | 27205240 | 27205359 | chr6 | 27205420 | 27205521 |
| chr6 | 27205587 | 27205837 | chr6 | 27205914 | 27206126 | chr6 | 27228079 | 27228187 |
| chr6 | 27228290 | 27228498 | chr6 | 27247561 | 27247800 | chr6 | 27256016 | 27256255 |
| chr6 | 27256283 | 27256522 | chr6 | 27264344 | 27264468 | chr6 | 27279750 | 27280109 |
| chr6 | 27462939 | 27463778 | chr6 | 27512675 | 27512884 | chr6 | 27512995 | 27513574 |
| chr6 | 27533723 | 27534442 | chr6 | 27559775 | 27560074 | chr6 | 27573073 | 27573492 |
| chr6 | 27598650 | 27598949 | chr6 | 27599071 | 27599427 | chr6 | 27635171 | 27635530 |
| chr6 | 27647625 | 27647736 | chr6 | 27647891 | 27647984 | chr6 | 27648934 | 27649153 |
| chr6 | 27834577 | 27834863 | chr6 | 27834905 | 27834936 | chr6 | 27834963 | 27835097 |
| chr6 | 27835378 | 27835502 | chr6 | 27839635 | 27840174 | chr6 | 27840461 | 27840668 |
| chr6 | 27841002 | 27841240 | chr6 | 27858427 | 27858726 | chr6 | 28175105 | 28176301 |
| chr6 | 28303466 | 28303571 | chr6 | 28303847 | 28304339 | chr6 | 28367023 | 28367279 |
| chr6 | 28367281 | 28367347 | chr6 | 28367491 | 28367571 | chr6 | 28367573 | 28367862 |
| chr6 | 28410896 | 28411030 | chr6 | 28411032 | 28411088 | chr6 | 28411152 | 28411435 |
| chr6 | 28414887 | 28414992 | chr6 | 28415092 | 28415126 | chr6 | 28457534 | 28457713 |
| chr6 | 28457775 | 28458254 | chr6 | 33955409 | 33955828 | chr6 | 34170869 | 34170986 |
| chr6 | 34171049 | 34171166 | chr6 | 34396518 | 34396631 | chr6 | 34724210 | 34724318 |
| chr6 | 35149942 | 35150181 | chr6 | 35992410 | 35992533 | chr6 | 36165588 | 36165767 |
| chr6 | 36252899 | 36253258 | chr6 | 36313887 | 36313988 | chr6 | 36808233 | 36808532 |
| chr6 | 37024485 | 37024664 | chr6 | 37664045 | 37664284 | chr6 | 37673227 | 37673573 |
| chr6 | 37776336 | 37776455 | chr6 | 37776737 | 37776839 | chr6 | 39281005 | 39281231 |
| chr6 | 39281731 | 39281970 | chr6 | 39329789 | 39329974 | chr6 | 39760322 | 39760663 |
| chr6 | 40554557 | 40554796 | chr6 | 41336981 | 41337220 | chr6 | 41339162 | 41339559 |
| chr6 | 41339602 | 41339941 | chr6 | 41340803 | 41341282 | chr6 | 41341406 | 41341604 |
| chr6 | 41342140 | 41342370 | chr6 | 41342733 | 41342912 | chr6 | 41605851 | 41605952 |
| chr6 | 41606038 | 41606357 | chr6 | 41606528 | 41606630 | chr6 | 41773485 | 41773844 |
| chr6 | 42773364 | 42773471 | chr6 | 42846625 | 42846729 | chr6 | 42879457 | 42879569 |
| chr6 | 42879622 | 42879756 | chr6 | 42928239 | 42928460 | chr6 | 43211113 | 43211402 |
| chr6 | 43424445 | 43424564 | chr6 | 43425407 | 43425524 | chr6 | 43478592 | 43478821 |
| chr6 | 43612737 | 43612899 | chr6 | 43613053 | 43613156 | chr6 | 43639529 | 43639809 |
| chr6 | 43748380 | 43748619 | chr6 | 44240961 | 44241191 | chr6 | 44695775 | 44695899 |
| chr6 | 45388701 | 45388866 | chr6 | 46702904 | 46703203 | chr6 | 46703274 | 46703513 |
| chr6 | 50674292 | 50674831 | chr6 | 50681612 | 50681851 | chr6 | 50681912 | 50682031 |
| chr6 | 50682234 | 50682339 | chr6 | 50682449 | 50682473 | chr6 | 50682584 | 50682684 |
| chr6 | 50682712 | 50682941 | chr6 | 50682992 | 50683303 | chr6 | 50684865 | 50685044 |
| chr6 | 50689827 | 50690126 | chr6 | 50690991 | 50691170 | chr6 | 50691983 | 50692213 |
| chr6 | 50692300 | 50692582 | chr6 | 50787125 | 50787877 | chr6 | 50787950 | 50788444 |
| chr6 | 50789300 | 50789479 | chr6 | 50791111 | 50791495 | chr6 | 50791551 | 50791708 |
| chr6 | 50793251 | 50793490 | chr6 | 50793626 | 50793850 | chr6 | 50794525 | 50794792 |
| chr6 | 50803732 | 50803971 | chr6 | 50804041 | 50804446 | chr6 | 50808589 | 50808845 |
| chr6 | 50810456 | 50810714 | chr6 | 50810976 | 50811575 | chr6 | 50813200 | 50814019 |
| chr6 | 50814495 | 50814674 | chr6 | 50816947 | 50817306 | chr6 | 50817831 | 50817841 |
| chr6 | 50818369 | 50818788 | chr6 | 50818841 | 50819080 | chr6 | 52227678 | 52227857 |
| chr6 | 52227934 | 52227964 | chr6 | 52344301 | 52344480 | chr6 | 53212553 | 53213932 |
| chr6 | 55443610 | 55444029 | chr6 | 56112175 | 56112474 | chr6 | 56716252 | 56716300 |
| chr6 | 56716390 | 56716491 | chr6 | 56818618 | 56819037 | chr6 | 56819128 | 56819727 |
| chr6 | 56819823 | 56820002 | chr6 | 58147345 | 58147511 | chr6 | 58147764 | 58148093 |
| chr6 | 62995272 | 62995875 | chr6 | 62996078 | 62996130 | chr6 | 62996132 | 62996214 |
| chr6 | 62996216 | 62996231 | chr6 | 62996347 | 62996586 | chr6 | 70991961 | 70992049 |
| chr6 | 70992137 | 70992260 | chr6 | 70992339 | 70992638 | chr6 | 70992744 | 70993103 |
| chr6 | 71665562 | 71665801 | chr6 | 71666708 | 71667066 | chr6 | 72129690 | 72129850 |
| chr6 | 72129927 | 72129929 | chr6 | 72130017 | 72130045 | chr6 | 72130191 | 72130499 |

TABLE 15-continued

| chr | start | end | chr | start | end | chr | start | end |
|---|---|---|---|---|---|---|---|---|
| chr6 | 72596039 | 72596135 | chr6 | 72596137 | 72596398 | chr6 | 72596876 | 72597055 |
| chr6 | 73329686 | 73330225 | chr6 | 73330740 | 73331114 | chr6 | 73331116 | 73331238 |
| chr6 | 73331240 | 73331399 | chr6 | 73331420 | 73331851 | chr6 | 73331876 | 73333099 |
| chr6 | 78172096 | 78172276 | chr6 | 78172323 | 78172675 | chr6 | 78173119 | 78173227 |
| chr6 | 78173229 | 78173295 | chr6 | 78173610 | 78173726 | chr6 | 78173772 | 78174080 |
| chr6 | 78176370 | 78176607 | chr6 | 78176693 | 78176909 | chr6 | 79620310 | 79620342 |
| chr6 | 79620475 | 79620685 | chr6 | 79620687 | 79620789 | chr6 | 80656846 | 80657265 |
| chr6 | 82958527 | 82958646 | chr6 | 84417343 | 84417701 | chr6 | 84418261 | 84418377 |
| chr6 | 84418545 | 84418724 | chr6 | 84418726 | 84418789 | chr6 | 84419077 | 84419202 |
| chr6 | 84419204 | 84419329 | chr6 | 84419331 | 84419496 | chr6 | 84562789 | 84562930 |
| chr6 | 84562932 | 84563285 | chr6 | 84563417 | 84563636 | chr6 | 85472306 | 85473805 |
| chr6 | 85473854 | 85474453 | chr6 | 85474516 | 85474767 | chr6 | 85474795 | 85474815 |
| chr6 | 85476140 | 85476379 | chr6 | 85476924 | 85477103 | chr6 | 85478440 | 85478557 |
| chr6 | 85478615 | 85478799 | chr6 | 85482437 | 85482796 | chr6 | 85483271 | 85483450 |
| chr6 | 85483760 | 85483932 | chr6 | 85484558 | 85484626 | chr6 | 85484717 | 85484998 |
| chr6 | 86302335 | 86302422 | chr6 | 87647130 | 87647219 | chr6 | 87862013 | 87862252 |
| chr6 | 88876871 | 88877064 | chr6 | 88877066 | 88877422 | chr6 | 88877475 | 88877530 |
| chr6 | 91320191 | 91320422 | chr6 | 91320853 | 91321390 | chr6 | 94126870 | 94127066 |
| chr6 | 94127086 | 94127169 | chr6 | 94127381 | 94127620 | chr6 | 94128340 | 94128502 |
| chr6 | 94129119 | 94129358 | chr6 | 94129423 | 94129627 | chr6 | 94129629 | 94129662 |
| chr6 | 96464003 | 96464293 | chr6 | 99271829 | 99272908 | chr6 | 99273271 | 99273510 |
| chr6 | 99277106 | 99277201 | chr6 | 99277262 | 99277405 | chr6 | 99279465 | 99279704 |
| chr6 | 99280472 | 99280831 | chr6 | 99280931 | 99281037 | chr6 | 99281068 | 99281470 |
| chr6 | 99283428 | 99283667 | chr6 | 99290260 | 99290473 | chr6 | 99290710 | 99290738 |
| chr6 | 99291191 | 99291342 | chr6 | 99292156 | 99292515 | chr6 | 99295648 | 99295864 |
| chr6 | 99296062 | 99296365 | chr6 | 99296408 | 99296547 | chr6 | 99396354 | 99396473 |
| chr6 | 100038584 | 100038707 | chr6 | 100038786 | 100039063 | chr6 | 100039275 | 100039364 |
| chr6 | 100050674 | 100050811 | chr6 | 100050859 | 100051109 | chr6 | 100051360 | 100051508 |
| chr6 | 100051772 | 100052053 | chr6 | 100053191 | 100053606 | chr6 | 100054773 | 100055012 |
| chr6 | 100060930 | 100061169 | chr6 | 100061216 | 100061515 | chr6 | 100061677 | 100061697 |
| chr6 | 100062083 | 100062682 | chr6 | 100062857 | 100063156 | chr6 | 100441276 | 100441308 |
| chr6 | 100441498 | 100441738 | chr6 | 100441762 | 100442055 | chr6 | 100903299 | 100903405 |
| chr6 | 100903561 | 100903718 | chr6 | 100904126 | 100904365 | chr6 | 100905936 | 100906113 |
| chr6 | 100911976 | 100912215 | chr6 | 100912332 | 100912446 | chr6 | 100912466 | 100912571 |
| chr6 | 100912825 | 100913051 | chr6 | 101840615 | 101840914 | chr6 | 101850062 | 101850314 |
| chr6 | 101850496 | 101850539 | chr6 | 105388605 | 105388717 | chr6 | 105389510 | 105389792 |
| chr6 | 105400811 | 105401110 | chr6 | 105401538 | 105401908 | chr6 | 105404475 | 105404774 |
| chr6 | 105405565 | 105405864 | chr6 | 105406024 | 105406203 | chr6 | 105584190 | 105584216 |
| chr6 | 105584218 | 105584320 | chr6 | 105584367 | 105584551 | chr6 | 105584553 | 105585629 |
| chr6 | 106428948 | 106429476 | chr6 | 106429590 | 106429704 | chr6 | 106434265 | 106434371 |
| chr6 | 106441795 | 106443054 | chr6 | 106960817 | 106961116 | chr6 | 108280341 | 108280442 |
| chr6 | 108434990 | 108435327 | chr6 | 108435970 | 108436629 | chr6 | 108438142 | 108438157 |
| chr6 | 108438261 | 108438612 | chr6 | 108440017 | 108440645 | chr6 | 108440745 | 108441036 |
| chr6 | 108479209 | 108479748 | chr6 | 108484829 | 108485274 | chr6 | 108485419 | 108485488 |
| chr6 | 108485576 | 108485995 | chr6 | 108486067 | 108486486 | chr6 | 108487701 | 108488520 |
| chr6 | 108489662 | 108489809 | chr6 | 108490067 | 108490246 | chr6 | 108490297 | 108490515 |
| chr6 | 108490538 | 108490729 | chr6 | 108490902 | 108491001 | chr6 | 108491108 | 108491501 |
| chr6 | 108492182 | 108492541 | chr6 | 108495607 | 108495818 | chr6 | 108495916 | 108496026 |
| chr6 | 108496130 | 108496466 | chr6 | 108497419 | 108497467 | chr6 | 110679030 | 110679400 |
| chr6 | 110679402 | 110679509 | chr6 | 110797604 | 110797783 | chr6 | 110797977 | 110798047 |
| chr6 | 116783418 | 116783591 | chr6 | 117086168 | 117086479 | chr6 | 117086481 | 117086640 |
| chr6 | 117086903 | 117086947 | chr6 | 117585867 | 117586106 | chr6 | 117587028 | 117587256 |
| chr6 | 117587380 | 117587387 | chr6 | 117587449 | 117587679 | chr6 | 117591087 | 117591266 |
| chr6 | 117591308 | 117591597 | chr6 | 117591684 | 117591847 | chr6 | 118228008 | 118228232 |
| chr6 | 118228669 | 118228869 | chr6 | 118228871 | 118228908 | chr6 | 118229060 | 118229390 |
| chr6 | 118229417 | 118229479 | chr6 | 118229543 | 118229573 | chr6 | 118229617 | 118229732 |
| chr6 | 118229734 | 118229902 | chr6 | 118241125 | 118241309 | chr6 | 118241395 | 118241604 |
| chr6 | 119254661 | 119254774 | chr6 | 121758594 | 121758980 | chr6 | 121758982 | 121759048 |
| chr6 | 123316950 | 123317007 | chr6 | 123317073 | 123317669 | chr6 | 123317696 | 123317714 |
| chr6 | 123317716 | 123317935 | chr6 | 124124330 | 124124569 | chr6 | 124124759 | 124125118 |
| chr6 | 125284034 | 125284273 | chr6 | 126068016 | 126068022 | chr6 | 126068069 | 126068255 |
| chr6 | 127439322 | 127439536 | chr6 | 127439907 | 127440206 | chr6 | 127440248 | 127440510 |
| chr6 | 127440512 | 127440963 | chr6 | 127441031 | 127441207 | chr6 | 127441479 | 127441838 |
| chr6 | 127441944 | 127442071 | chr6 | 127442090 | 127442183 | chr6 | 127840412 | 127840771 |
| chr6 | 129204373 | 129204612 | chr6 | 130686437 | 130687156 | chr6 | 131602689 | 131602736 |
| chr6 | 132721988 | 132722142 | chr6 | 132722158 | 132722287 | chr6 | 133561967 | 133562145 |
| chr6 | 133562349 | 133562437 | chr6 | 133562675 | 133563095 | chr6 | 133563234 | 133564013 |
| chr6 | 134067456 | 134067573 | chr6 | 134176147 | 134176149 | chr6 | 134210558 | 134211019 |
| chr6 | 134211112 | 134211458 | chr6 | 134213855 | 134213988 | chr6 | 134214077 | 134214454 |
| chr6 | 134589425 | 134589586 | chr6 | 134638858 | 134639095 | chr6 | 137241828 | 137242062 |
| chr6 | 137242064 | 137242307 | chr6 | 137243130 | 137243342 | chr6 | 137243367 | 137243489 |
| chr6 | 137244036 | 137244149 | chr6 | 137244236 | 137244466 | chr6 | 137311060 | 137311479 |
| chr6 | 137366280 | 137366459 | chr6 | 137809066 | 137809363 | chr6 | 137809446 | 137809917 |
| chr6 | 137810033 | 137811165 | chr6 | 137813692 | 137813991 | chr6 | 137814505 | 137814619 |
| chr6 | 137814654 | 137814864 | chr6 | 137814916 | 137815171 | chr6 | 137815225 | 137815755 |
| chr6 | 137816373 | 137817377 | chr6 | 137818428 | 137818599 | chr6 | 137818619 | 137819267 |
| chr6 | 137819269 | 137819447 | chr6 | 146755489 | 146755728 | chr6 | 149868369 | 149868478 |
| chr6 | 150284574 | 150284657 | chr6 | 150284979 | 150285369 | chr6 | 150285545 | 150285886 |

TABLE 15-continued

| chr | start | end | chr | start | end | chr | start | end |
|---|---|---|---|---|---|---|---|---|
| chr6 | 150286100 | 150286718 | chr6 | 150358890 | 150358985 | chr6 | 150358987 | 150359193 |
| chr6 | 150359439 | 150359489 | chr6 | 151560928 | 151561341 | chr6 | 151561369 | 151561947 |
| chr6 | 151561986 | 151561992 | chr6 | 151562057 | 151562645 | chr6 | 151814953 | 151815192 |
| chr6 | 152622925 | 152623584 | chr6 | 152957816 | 152957999 | chr6 | 152958001 | 152958166 |
| chr6 | 153451159 | 153451578 | chr6 | 153451810 | 153452049 | chr6 | 153452157 | 153452396 |
| chr6 | 153452611 | 153452755 | chr6 | 153452789 | 153452850 | chr6 | 154360549 | 154360848 |
| chr6 | 154970468 | 154970587 | chr6 | 155316161 | 155316221 | chr6 | 155316257 | 155316340 |
| chr6 | 155569193 | 155569407 | chr6 | 157502364 | 157502543 | chr6 | 157506008 | 157506187 |
| chr6 | 157556755 | 157557297 | chr6 | 159589948 | 159590087 | chr6 | 159590155 | 159590762 |
| chr6 | 159590972 | 159591087 | chr6 | 159654844 | 159655083 | chr6 | 161188439 | 161188618 |
| chr6 | 161351999 | 161352146 | chr6 | 161352199 | 161352238 | chr6 | 161780141 | 161780218 |
| chr6 | 163834237 | 163834383 | chr6 | 163834406 | 163834533 | chr6 | 163834711 | 163834716 |
| chr6 | 163834779 | 163834902 | chr6 | 163834988 | 163835018 | chr6 | 163836465 | 163837004 |
| chr6 | 164179653 | 164179772 | chr6 | 164196997 | 164197107 | chr6 | 164228212 | 164228449 |
| chr6 | 164246123 | 164246229 | chr6 | 164283167 | 164283370 | chr6 | 164314286 | 164314525 |
| chr6 | 164322572 | 164322871 | chr6 | 166074027 | 166074506 | chr6 | 166076696 | 166077115 |
| chr6 | 166077280 | 166077633 | chr6 | 166077669 | 166077759 | chr6 | 166267503 | 166267892 |
| chr6 | 166401162 | 166401401 | chr6 | 166402154 | 166402633 | chr6 | 166421831 | 166421992 |
| chr6 | 166421994 | 166422288 | chr6 | 166579636 | 166580234 | chr6 | 166580252 | 166582393 |
| chr6 | 166582395 | 166582827 | chr6 | 166944266 | 166944505 | chr6 | 167835031 | 167835270 |
| chr6 | 168719890 | 168720121 | chr6 | 168842760 | 168843046 | chr6 | 168858030 | 168858389 |
| chr6 | 169653564 | 169653743 | chr6 | 170240691 | 170240797 | chr6 | 170264630 | 170264865 |
| chr6 | 170475007 | 170475366 | chr7 | 329765 | 329942 | chr7 | 369763 | 370062 |
| chr7 | 389589 | 389768 | chr7 | 409740 | 409872 | chr7 | 409887 | 409979 |
| chr7 | 431290 | 431589 | chr7 | 497679 | 498006 | chr7 | 503725 | 504024 |
| chr7 | 551499 | 551778 | chr7 | 557008 | 557076 | chr7 | 578836 | 579121 |
| chr7 | 751726 | 751765 | chr7 | 752022 | 752149 | chr7 | 752151 | 752306 |
| chr7 | 907582 | 907761 | chr7 | 1022150 | 1022329 | chr7 | 1030079 | 1030378 |
| chr7 | 1054489 | 1054780 | chr7 | 1086110 | 1086409 | chr7 | 1263682 | 1264041 |
| chr7 | 1269228 | 1269464 | chr7 | 1269553 | 1269887 | chr7 | 1270304 | 1270543 |
| chr7 | 1273070 | 1273388 | chr7 | 1274540 | 1274779 | chr7 | 1275046 | 1275113 |
| chr7 | 1275481 | 1275682 | chr7 | 1275734 | 1275780 | chr7 | 1277722 | 1277961 |
| chr7 | 1279136 | 1279204 | chr7 | 1279891 | 1280070 | chr7 | 1281033 | 1281332 |
| chr7 | 1281405 | 1281644 | chr7 | 1281947 | 1282246 | chr7 | 1282426 | 1282725 |
| chr7 | 1286715 | 1286754 | chr7 | 1286887 | 1286954 | chr7 | 1288489 | 1288848 |
| chr7 | 1308275 | 1308574 | chr7 | 1325727 | 1325966 | chr7 | 1415941 | 1416226 |
| chr7 | 1423536 | 1423740 | chr7 | 1458967 | 1459183 | chr7 | 1503328 | 1503687 |
| chr7 | 1547234 | 1547413 | chr7 | 1598549 | 1598788 | chr7 | 1607307 | 1607546 |
| chr7 | 1607897 | 1608076 | chr7 | 1641700 | 1641999 | chr7 | 1681095 | 1681334 |
| chr7 | 1688883 | 1689101 | chr7 | 1690649 | 1690801 | chr7 | 1690903 | 1690948 |
| chr7 | 1709038 | 1709337 | chr7 | 1709385 | 1709562 | chr7 | 1709618 | 1709684 |
| chr7 | 1733066 | 1733482 | chr7 | 1775757 | 1775936 | chr7 | 1783468 | 1783470 |
| chr7 | 1786438 | 1786916 | chr7 | 1787066 | 1787425 | chr7 | 1800808 | 1800987 |
| chr7 | 1970776 | 1970947 | chr7 | 2163251 | 2163496 | chr7 | 2208635 | 2208889 |
| chr7 | 2232861 | 2233154 | chr7 | 2233204 | 2233503 | chr7 | 2238051 | 2238327 |
| chr7 | 2300694 | 2300803 | chr7 | 2565961 | 2566130 | chr7 | 2566526 | 2566705 |
| chr7 | 2719928 | 2720227 | chr7 | 2727968 | 2728267 | chr7 | 3033584 | 3033763 |
| chr7 | 3083216 | 3083288 | chr7 | 3083331 | 3083333 | chr7 | 3083335 | 3083338 |
| chr7 | 3083340 | 3083455 | chr7 | 3283620 | 3283978 | chr7 | 3340370 | 3340549 |
| chr7 | 3341394 | 3341409 | chr7 | 3341570 | 3341693 | chr7 | 4215235 | 4215469 |
| chr7 | 4856897 | 4857136 | chr7 | 4922460 | 4922707 | chr7 | 4923328 | 4923475 |
| chr7 | 4998116 | 4998475 | chr7 | 4998771 | 4998837 | chr7 | 5262472 | 5262648 |
| chr7 | 5632841 | 5633200 | chr7 | 5648011 | 5648490 | chr7 | 6060493 | 6060556 |
| chr7 | 6099127 | 6099234 | chr7 | 6124621 | 6124740 | chr7 | 6188652 | 6188831 |
| chr7 | 6188926 | 6189165 | chr7 | 6443198 | 6443478 | chr7 | 6443752 | 6443794 |
| chr7 | 6443871 | 6443931 | chr7 | 6524492 | 6524599 | chr7 | 6524936 | 6525055 |
| chr7 | 6543064 | 6543303 | chr7 | 6560141 | 6560440 | chr7 | 6566329 | 6566748 |
| chr7 | 6570901 | 6571225 | chr7 | 6576043 | 6576185 | chr7 | 6703458 | 6703708 |
| chr7 | 6703710 | 6703803 | chr7 | 6703805 | 6703870 | chr7 | 6703916 | 6704057 |
| chr7 | 7605665 | 7605902 | chr7 | 8472995 | 8473456 | chr7 | 8473480 | 8473762 |
| chr7 | 8473870 | 8474242 | chr7 | 8474516 | 8474649 | chr7 | 8474727 | 8475146 |
| chr7 | 8480647 | 8481126 | chr7 | 8481228 | 8481260 | chr7 | 8481559 | 8481918 |
| chr7 | 8481980 | 8482298 | chr7 | 8482670 | 8482825 | chr7 | 8482885 | 8482999 |
| chr7 | 8483070 | 8484029 | chr7 | 12151350 | 12151473 | chr7 | 12151524 | 12151769 |
| chr7 | 12443241 | 12443480 | chr7 | 12443767 | 12443806 | chr7 | 12610259 | 12610317 |
| chr7 | 12610539 | 12610558 | chr7 | 15725883 | 15726182 | chr7 | 15726557 | 15727156 |
| chr7 | 15727216 | 15727395 | chr7 | 19145730 | 19145894 | chr7 | 19146032 | 19146185 |
| chr7 | 19146238 | 19146329 | chr7 | 19146411 | 19146650 | chr7 | 19147041 | 19147880 |
| chr7 | 19152224 | 19152368 | chr7 | 19155865 | 19155896 | chr7 | 19155984 | 19156062 |
| chr7 | 19156126 | 19156133 | chr7 | 19156304 | 19156643 | chr7 | 19156705 | 19156746 |
| chr7 | 19157056 | 19157193 | chr7 | 19157195 | 19157263 | chr7 | 19157265 | 19157567 |
| chr7 | 19157634 | 19158099 | chr7 | 19183978 | 19184337 | chr7 | 19813210 | 19813350 |
| chr7 | 20816175 | 20816530 | chr7 | 20817306 | 20817332 | chr7 | 20817452 | 20817485 |
| chr7 | 20818037 | 20818276 | chr7 | 20823213 | 20823331 | chr7 | 20823383 | 20823512 |
| chr7 | 20823826 | 20823879 | chr7 | 20823920 | 20824144 | chr7 | 20824476 | 20824820 |
| chr7 | 20824836 | 20825025 | chr7 | 20825290 | 20825363 | chr7 | 20826803 | 20826939 |
| chr7 | 20827224 | 20827282 | chr7 | 20830596 | 20830775 | chr7 | 20833066 | 20833425 |
| chr7 | 21582492 | 21582641 | chr7 | 21582792 | 21582971 | chr7 | 21583176 | 21583278 |

TABLE 15-continued

| chr | start | end | chr | start | end | chr | start | end |
|---|---|---|---|---|---|---|---|---|
| chr7 | 21583304 | 21583415 | chr7 | 22539752 | 22539991 | chr7 | 22589254 | 22589973 |
| chr7 | 23287170 | 23287351 | chr7 | 23287533 | 23287709 | chr7 | 23578824 | 23578943 |
| chr7 | 24324002 | 24324028 | chr7 | 24580786 | 24580905 | chr7 | 24796404 | 24796643 |
| chr7 | 25892430 | 25892431 | chr7 | 25892609 | 25892669 | chr7 | 25896424 | 25896603 |
| chr7 | 25896675 | 25896963 | chr7 | 27127919 | 27128001 | chr7 | 27135232 | 27135771 |
| chr7 | 27135980 | 27136424 | chr7 | 27136426 | 27136868 | chr7 | 27190490 | 27191329 |
| chr7 | 27195483 | 27195602 | chr7 | 27195867 | 27195893 | chr7 | 27196153 | 27196153 |
| chr7 | 27196155 | 27196286 | chr7 | 27196288 | 27196742 | chr7 | 27204402 | 27204770 |
| chr7 | 27205266 | 27205381 | chr7 | 27205383 | 27205481 | chr7 | 27205599 | 27205790 |
| chr7 | 27206083 | 27206138 | chr7 | 27209413 | 27209672 | chr7 | 27209690 | 27209772 |
| chr7 | 27212400 | 27212984 | chr7 | 27213189 | 27213984 | chr7 | 27213986 | 27214262 |
| chr7 | 27214330 | 27214401 | chr7 | 27223031 | 27223193 | chr7 | 27223222 | 27223253 |
| chr7 | 27223500 | 27223799 | chr7 | 27223980 | 27224699 | chr7 | 27224945 | 27225058 |
| chr7 | 27227795 | 27228034 | chr7 | 27232207 | 27233046 | chr7 | 27238813 | 27238992 |
| chr7 | 27239087 | 27239173 | chr7 | 27239226 | 27239326 | chr7 | 27240127 | 27240423 |
| chr7 | 27244446 | 27244611 | chr7 | 27244798 | 27245393 | chr7 | 27245583 | 27245733 |
| chr7 | 27252306 | 27252485 | chr7 | 27264801 | 27265400 | chr7 | 27265442 | 27265678 |
| chr7 | 27275467 | 27275532 | chr7 | 27279238 | 27279369 | chr7 | 27279454 | 27279554 |
| chr7 | 27282012 | 27283091 | chr7 | 27283250 | 27283295 | chr7 | 27285436 | 27285519 |
| chr7 | 27285621 | 27285825 | chr7 | 27288869 | 27288945 | chr7 | 27289446 | 27289528 |
| chr7 | 27291048 | 27291119 | chr7 | 27291315 | 27291947 | chr7 | 28449197 | 28449291 |
| chr7 | 28449659 | 28449782 | chr7 | 28449858 | 28450096 | chr7 | 28995579 | 28996058 |
| chr7 | 28996357 | 28996596 | chr7 | 28996759 | 28996998 | chr7 | 28997052 | 28997475 |
| chr7 | 28997487 | 28997646 | chr7 | 28997677 | 28997711 | chr7 | 28997967 | 28998206 |
| chr7 | 30721202 | 30721943 | chr7 | 30722214 | 30722453 | chr7 | 31092919 | 31093218 |
| chr7 | 31375899 | 31376230 | chr7 | 32110616 | 32110650 | chr7 | 32110652 | 32110692 |
| chr7 | 32110704 | 32110855 | chr7 | 32337733 | 32337912 | chr7 | 32338044 | 32338218 |
| chr7 | 32338284 | 32338489 | chr7 | 32338826 | 32339005 | chr7 | 32467373 | 32467656 |
| chr7 | 32467947 | 32468151 | chr7 | 32997050 | 32997463 | chr7 | 33943370 | 33943849 |
| chr7 | 35225724 | 35225834 | chr7 | 35226090 | 35226523 | chr7 | 35226557 | 35226610 |
| chr7 | 35226612 | 35226811 | chr7 | 35292893 | 35293087 | chr7 | 35293183 | 35293372 |
| chr7 | 35294032 | 35294228 | chr7 | 35294400 | 35294639 | chr7 | 35295030 | 35295106 |
| chr7 | 35295807 | 35296000 | chr7 | 35296855 | 35297005 | chr7 | 35297138 | 35297354 |
| chr7 | 35297471 | 35298017 | chr7 | 35300851 | 35301009 | chr7 | 35301102 | 35302050 |
| chr7 | 35494278 | 35494333 | chr7 | 35494470 | 35494517 | chr7 | 37487076 | 37487251 |
| chr7 | 37487376 | 37487454 | chr7 | 37487756 | 37487915 | chr7 | 37488179 | 37488658 |
| chr7 | 37488837 | 37489076 | chr7 | 37907366 | 37907545 | chr7 | 37955780 | 37956079 |
| chr7 | 37956176 | 37956535 | chr7 | 37960199 | 37960438 | chr7 | 38670267 | 38670664 |
| chr7 | 38670957 | 38670985 | chr7 | 38670987 | 38671106 | chr7 | 39015463 | 39016062 |
| chr7 | 42267573 | 42267712 | chr7 | 42276251 | 42276730 | chr7 | 42533028 | 42533081 |
| chr7 | 42533257 | 42533387 | chr7 | 43152016 | 43152208 | chr7 | 43152414 | 43152795 |
| chr7 | 43152858 | 43153200 | chr7 | 43153230 | 43153337 | chr7 | 44097656 | 44097895 |
| chr7 | 44143906 | 44143942 | chr7 | 44144030 | 44144085 | chr7 | 44151324 | 44151503 |
| chr7 | 44151715 | 44151857 | chr7 | 44164017 | 44164078 | chr7 | 44364752 | 44364991 |
| chr7 | 44835122 | 44835467 | chr7 | 45038447 | 45038564 | chr7 | 45613693 | 45613814 |
| chr7 | 45613858 | 45613992 | chr7 | 45614259 | 45614558 | chr7 | 45614655 | 45615061 |
| chr7 | 45615536 | 45615588 | chr7 | 45960650 | 45960889 | chr7 | 45961072 | 45961251 |
| chr7 | 45961423 | 45961630 | chr7 | 45961656 | 45961662 | chr7 | 45961742 | 45961981 |
| chr7 | 49812718 | 49813018 | chr7 | 49813810 | 49814093 | chr7 | 49814454 | 49814751 |
| chr7 | 49815117 | 49815250 | chr7 | 49815657 | 49815848 | chr7 | 50294460 | 50294556 |
| chr7 | 50343183 | 50343482 | chr7 | 50343975 | 50344086 | chr7 | 50344150 | 50344294 |
| chr7 | 50344296 | 50344331 | chr7 | 50344333 | 50344569 | chr7 | 50364988 | 50365069 |
| chr7 | 50438544 | 50438723 | chr7 | 50560494 | 50560733 | chr7 | 50860135 | 50860393 |
| chr7 | 50860980 | 50861103 | chr7 | 50861128 | 50861214 | chr7 | 51384235 | 51384534 |
| chr7 | 51384814 | 51385006 | chr7 | 54609764 | 54609952 | chr7 | 54609992 | 54610022 |
| chr7 | 54610024 | 54610243 | chr7 | 54612335 | 54612814 | chr7 | 55086481 | 55086687 |
| chr7 | 55086899 | 55087618 | chr7 | 55409933 | 55410223 | chr7 | 56018026 | 56018205 |
| chr7 | 56031847 | 56031966 | chr7 | 64330322 | 64330561 | chr7 | 64330635 | 64330645 |
| chr7 | 64348952 | 64348968 | chr7 | 64349042 | 64349131 | chr7 | 64349318 | 64349551 |
| chr7 | 64700198 | 64700426 | chr7 | 64712288 | 64712587 | chr7 | 64974283 | 64974402 |
| chr7 | 65037592 | 65037702 | chr7 | 65508900 | 65509124 | chr7 | 66214974 | 66215062 |
| chr7 | 68204692 | 68204931 | chr7 | 69062428 | 69062727 | chr7 | 69064489 | 69064772 |
| chr7 | 69064834 | 69065148 | chr7 | 69897685 | 69897924 | chr7 | 70596353 | 70596416 |
| chr7 | 70596454 | 70596711 | chr7 | 70597368 | 70597368 | chr7 | 70597395 | 70597549 |
| chr7 | 70597752 | 70597754 | chr7 | 70597780 | 70597972 | chr7 | 70597991 | 70598124 |
| chr7 | 70598170 | 70598471 | chr7 | 71217011 | 71217320 | chr7 | 71217322 | 71217366 |
| chr7 | 71800599 | 71800757 | chr7 | 71800934 | 71801105 | chr7 | 71802315 | 71802347 |
| chr7 | 71802390 | 71802396 | chr7 | 71802457 | 71802523 | chr7 | 71802578 | 71802734 |
| chr7 | 71871105 | 71871157 | chr7 | 76033251 | 76033364 | chr7 | 77324278 | 77324309 |
| chr7 | 79081718 | 79081897 | chr7 | 79081942 | 79081969 | chr7 | 79082070 | 79082301 |
| chr7 | 79083016 | 79083035 | chr7 | 79083191 | 79083255 | chr7 | 79083314 | 79083913 |
| chr7 | 82072248 | 82072562 | chr7 | 84815049 | 84815135 | chr7 | 84815397 | 84815468 |
| chr7 | 84815670 | 84816029 | chr7 | 86273108 | 86273645 | chr7 | 86274018 | 86274117 |
| chr7 | 86274258 | 86274547 | chr7 | 87104725 | 87105445 | chr7 | 87229446 | 87230189 |
| chr7 | 87230191 | 87230344 | chr7 | 87230346 | 87230525 | chr7 | 87256911 | 87257074 |
| chr7 | 87257076 | 87257150 | chr7 | 87257964 | 87258143 | chr7 | 88387904 | 88388130 |
| chr7 | 88388247 | 88388263 | chr7 | 88388439 | 88388646 | chr7 | 88388648 | 88388738 |
| chr7 | 88388789 | 88388902 | chr7 | 88389047 | 88389389 | chr7 | 89747928 | 89748294 |

TABLE 15-continued

| chr | start | end | chr | start | end | chr | start | end |
|---|---|---|---|---|---|---|---|---|
| chr7 | 89748296 | 89748438 | chr7 | 89950108 | 89950813 | chr7 | 90226188 | 90226284 |
| chr7 | 90226286 | 90226547 | chr7 | 90894936 | 90895027 | chr7 | 90895029 | 90895175 |
| chr7 | 92466078 | 92466486 | chr7 | 92689613 | 92689774 | chr7 | 93203613 | 93203852 |
| chr7 | 93204299 | 93204592 | chr7 | 93519265 | 93519766 | chr7 | 93519855 | 93520024 |
| chr7 | 93520026 | 93520224 | chr7 | 93551225 | 93551524 | chr7 | 94284277 | 94284978 |
| chr7 | 96619499 | 96619678 | chr7 | 96621614 | 96621913 | chr7 | 96622019 | 96622438 |
| chr7 | 96625472 | 96625809 | chr7 | 96625906 | 96626145 | chr7 | 96631614 | 96631780 |
| chr7 | 96634577 | 96634996 | chr7 | 96635260 | 96635379 | chr7 | 96635440 | 96635452 |
| chr7 | 96635487 | 96635559 | chr7 | 96635650 | 96635972 | chr7 | 96636034 | 96636729 |
| chr7 | 96646568 | 96647227 | chr7 | 96647715 | 96648314 | chr7 | 96650809 | 96651077 |
| chr7 | 96651137 | 96651228 | chr7 | 96651384 | 96651584 | chr7 | 96652070 | 96652249 |
| chr7 | 96653421 | 96653820 | chr7 | 96653863 | 96654080 | chr7 | 97361021 | 97361423 |
| chr7 | 97361521 | 97361860 | chr7 | 97362211 | 97362690 | chr7 | 97600015 | 97600194 |
| chr7 | 97869540 | 97869719 | chr7 | 98245857 | 98246079 | chr7 | 98246305 | 98246508 |
| chr7 | 98246534 | 98246947 | chr7 | 98247032 | 98247751 | chr7 | 98971530 | 98971649 |
| chr7 | 99104174 | 99104293 | chr7 | 99177657 | 99177663 | chr7 | 99177695 | 99177956 |
| chr7 | 99591732 | 99591851 | chr7 | 99595184 | 99595336 | chr7 | 99751485 | 99751553 |
| chr7 | 99775118 | 99775297 | chr7 | 100088099 | 100088398 | chr7 | 100091115 | 100091181 |
| chr7 | 100179789 | 100180017 | chr7 | 100318467 | 100318660 | chr7 | 100808365 | 100808596 |
| chr7 | 100809360 | 100809599 | chr7 | 100823348 | 100823351 | chr7 | 100823381 | 100823587 |
| chr7 | 101005901 | 101006073 | chr7 | 101241919 | 101242098 | chr7 | 101475705 | 101475944 |
| chr7 | 101627683 | 101627884 | chr7 | 101707428 | 101707535 | chr7 | 103085786 | 103086565 |
| chr7 | 103628963 | 103629795 | chr7 | 103630054 | 103630083 | chr7 | 103630381 | 103630549 |
| chr7 | 103630551 | 103630920 | chr7 | 103969130 | 103969166 | chr7 | 103969168 | 103969429 |
| chr7 | 103969595 | 103969679 | chr7 | 103969694 | 103969894 | chr7 | 105279390 | 105279749 |
| chr7 | 106685195 | 106685434 | chr7 | 106797700 | 106797856 | chr7 | 107301418 | 107301717 |
| chr7 | 107483597 | 107484016 | chr7 | 108095227 | 108095466 | chr7 | 108095781 | 108096141 |
| chr7 | 108097093 | 108097572 | chr7 | 112726529 | 112726538 | chr7 | 112726540 | 112726706 |
| chr7 | 113722736 | 113723284 | chr7 | 113723339 | 113723515 | chr7 | 113724870 | 113725169 |
| chr7 | 113726435 | 113726614 | chr7 | 113727345 | 113727584 | chr7 | 113727755 | 113727872 |
| chr7 | 115117451 | 115117750 | chr7 | 116140155 | 116140268 | chr7 | 116962796 | 116963147 |
| chr7 | 116963331 | 116963575 | chr7 | 117119347 | 117120366 | chr7 | 119913464 | 119913837 |
| chr7 | 120969587 | 120969886 | chr7 | 121513457 | 121513796 | chr7 | 121939584 | 121940245 |
| chr7 | 121940434 | 121940543 | chr7 | 121940845 | 121941144 | chr7 | 121941807 | 121942266 |
| chr7 | 121943905 | 121943989 | chr7 | 121944177 | 121944264 | chr7 | 121945722 | 121946021 |
| chr7 | 121946403 | 121946983 | chr7 | 121947098 | 121947482 | chr7 | 121950034 | 121950265 |
| chr7 | 121950429 | 121950553 | chr7 | 121950995 | 121951029 | chr7 | 121951784 | 121952011 |
| chr7 | 121952044 | 121952256 | chr7 | 121956408 | 121956582 | chr7 | 121956955 | 121957077 |
| chr7 | 121957254 | 121957254 | chr7 | 121957256 | 121957411 | chr7 | 123173048 | 123173327 |
| chr7 | 123671948 | 123672187 | chr7 | 124404320 | 124404498 | chr7 | 124404544 | 124404619 |
| chr7 | 126891146 | 126891325 | chr7 | 126891430 | 126891669 | chr7 | 127371055 | 127371234 |
| chr7 | 127615847 | 127616026 | chr7 | 127744048 | 127744210 | chr7 | 127744212 | 127744707 |
| chr7 | 127806560 | 127806739 | chr7 | 127807743 | 127807922 | chr7 | 127807971 | 127808822 |
| chr7 | 127841426 | 127841497 | chr7 | 127841626 | 127841785 | chr7 | 127991742 | 127991743 |
| chr7 | 127991788 | 127991923 | chr7 | 127992045 | 127992221 | chr7 | 128096988 | 128097164 |
| chr7 | 128337365 | 128337543 | chr7 | 128337788 | 128338023 | chr7 | 128470816 | 128471057 |
| chr7 | 128486020 | 128486237 | chr7 | 128528729 | 128528854 | chr7 | 128528949 | 128529128 |
| chr7 | 128828115 | 128828354 | chr7 | 129229605 | 129229724 | chr7 | 129418168 | 129418513 |
| chr7 | 129422116 | 129422969 | chr7 | 129423126 | 129423509 | chr7 | 129424552 | 129425991 |
| chr7 | 129426215 | 129426336 | chr7 | 129794508 | 129794807 | chr7 | 129800223 | 129800462 |
| chr7 | 131041437 | 131041676 | chr7 | 131242662 | 131242901 | chr7 | 131514750 | 131514929 |
| chr7 | 132261173 | 132261208 | chr7 | 132261257 | 132261505 | chr7 | 134143081 | 134143560 |
| chr7 | 134143731 | 134143971 | chr7 | 134143973 | 134144055 | chr7 | 134144057 | 134144209 |
| chr7 | 134918421 | 134918720 | chr7 | 136553316 | 136553495 | chr7 | 136553556 | 136554026 |
| chr7 | 136554104 | 136554469 | chr7 | 136554563 | 136554581 | chr7 | 136554626 | 136555001 |
| chr7 | 136555145 | 136555504 | chr7 | 136555587 | 136555842 | chr7 | 136556013 | 136556186 |
| chr7 | 137028402 | 137028623 | chr7 | 137531153 | 137531212 | chr7 | 137531263 | 137531889 |
| chr7 | 137531909 | 137532188 | chr7 | 137532374 | 137532438 | chr7 | 138042136 | 138042315 |
| chr7 | 139167532 | 139167827 | chr7 | 139168115 | 139168481 | chr7 | 139208697 | 139208888 |
| chr7 | 139930070 | 139930371 | chr7 | 139939060 | 139939314 | chr7 | 140026925 | 140027043 |
| chr7 | 140180180 | 140180298 | chr7 | 140339839 | 140339868 | chr7 | 140339966 | 140340079 |
| chr7 | 140453048 | 140453227 | chr7 | 140772717 | 140773312 | chr7 | 140773478 | 140773837 |
| chr7 | 143042537 | 143042896 | chr7 | 143579665 | 143579665 | chr7 | 143579667 | 143579951 |
| chr7 | 143579953 | 143580144 | chr7 | 145812918 | 145813008 | chr7 | 145813010 | 145813157 |
| chr7 | 145813334 | 145813391 | chr7 | 145813404 | 145813573 | chr7 | 145813946 | 145814269 |
| chr7 | 148224592 | 148224711 | chr7 | 148640242 | 148640331 | chr7 | 148846061 | 148846279 |
| chr7 | 149111968 | 149112226 | chr7 | 149112421 | 149112507 | chr7 | 149119862 | 149120124 |
| chr7 | 149411444 | 149411728 | chr7 | 149411835 | 149412403 | chr7 | 149744462 | 149744653 |
| chr7 | 149917322 | 149917412 | chr7 | 149918045 | 149918191 | chr7 | 150049512 | 150049626 |
| chr7 | 150069013 | 150069432 | chr7 | 150069601 | 150069662 | chr7 | 150069837 | 150069900 |
| chr7 | 150069921 | 150070160 | chr7 | 150081153 | 150081354 | chr7 | 150716088 | 150716387 |
| chr7 | 150748090 | 150748509 | chr7 | 150753843 | 150754082 | chr7 | 150870734 | 150870973 |
| chr7 | 151106369 | 151106566 | chr7 | 151106590 | 151106989 | chr7 | 151107396 | 151107637 |
| chr7 | 151107639 | 151107749 | chr7 | 151591567 | 151591806 | chr7 | 152622546 | 152622779 |
| chr7 | 153583503 | 153583530 | chr7 | 153583632 | 153584162 | chr7 | 153584297 | 153584546 |
| chr7 | 153584694 | 153584716 | chr7 | 153584758 | 153585233 | chr7 | 153585333 | 153585396 |
| chr7 | 153585602 | 153585692 | chr7 | 153749619 | 153750043 | chr7 | 154561051 | 154561290 |
| chr7 | 154708188 | 154708355 | chr7 | 154861947 | 154862030 | chr7 | 154862032 | 154862366 |

TABLE 15-continued

| chr | start | end | chr | start | end | chr | start | end |
|---|---|---|---|---|---|---|---|---|
| chr7 | 155164379 | 155165638 | chr7 | 155165791 | 155166870 | chr7 | 155166933 | 155167038 |
| chr7 | 155167040 | 155167090 | chr7 | 155167175 | 155167661 | chr7 | 155167834 | 155167844 |
| chr7 | 155167846 | 155167992 | chr7 | 155174573 | 155174872 | chr7 | 155241235 | 155241490 |
| chr7 | 155241492 | 155242134 | chr7 | 155242700 | 155243186 | chr7 | 155243245 | 155243534 |
| chr7 | 155243756 | 155243980 | chr7 | 155244092 | 155244451 | chr7 | 155246859 | 155247480 |
| chr7 | 155247651 | 155247685 | chr7 | 155248839 | 155249018 | chr7 | 155249420 | 155249659 |
| chr7 | 155249849 | 155250088 | chr7 | 155250200 | 155250304 | chr7 | 155250324 | 155250439 |
| chr7 | 155250713 | 155251072 | chr7 | 155251662 | 155251855 | chr7 | 155251891 | 155252030 |
| chr7 | 155252160 | 155252262 | chr7 | 155252317 | 155252579 | chr7 | 155252773 | 155253132 |
| chr7 | 155254765 | 155255416 | chr7 | 155256216 | 155256233 | chr7 | 155256269 | 155256395 |
| chr7 | 155256986 | 155257265 | chr7 | 155258101 | 155258580 | chr7 | 155258854 | 155258864 |
| chr7 | 155258915 | 155259078 | chr7 | 155259120 | 155259623 | chr7 | 155259834 | 155259845 |
| chr7 | 155259847 | 155259958 | chr7 | 155260039 | 155260233 | chr7 | 155260806 | 155260891 |
| chr7 | 155261071 | 155261285 | chr7 | 155301736 | 155302035 | chr7 | 155302267 | 155302896 |
| chr7 | 155302964 | 155303432 | chr7 | 155325720 | 155325954 | chr7 | 155326079 | 155326618 |
| chr7 | 155363212 | 155363511 | chr7 | 155580182 | 155580308 | chr7 | 155580772 | 155580882 |
| chr7 | 155581243 | 155581652 | chr7 | 155581664 | 155581962 | chr7 | 155582190 | 155582369 |
| chr7 | 155600527 | 155600825 | chr7 | 155602726 | 155602898 | chr7 | 156409214 | 156409426 |
| chr7 | 156409728 | 156409884 | chr7 | 156701794 | 156701997 | chr7 | 156744697 | 156744816 |
| chr7 | 156794465 | 156794579 | chr7 | 156794922 | 156795355 | chr7 | 156795402 | 156795636 |
| chr7 | 156795900 | 156795996 | chr7 | 156796442 | 156796740 | chr7 | 156797006 | 156798435 |
| chr7 | 156798527 | 156799147 | chr7 | 156799291 | 156799561 | chr7 | 156800925 | 156801104 |
| chr7 | 156801323 | 156801682 | chr7 | 156808760 | 156809299 | chr7 | 156809953 | 156810522 |
| chr7 | 156810598 | 156810801 | chr7 | 156811303 | 156811520 | chr7 | 156812773 | 156813826 |
| chr7 | 156813987 | 156814230 | chr7 | 156815096 | 156815170 | chr7 | 156832194 | 156832493 |
| chr7 | 156832766 | 156833245 | chr7 | 156871084 | 156871153 | chr7 | 156871283 | 156871383 |
| chr7 | 156880457 | 156880636 | chr7 | 157085281 | 157085580 | chr7 | 157085874 | 157086173 |
| chr7 | 157262738 | 157263097 | chr7 | 157263204 | 157263563 | chr7 | 157361531 | 157361653 |
| chr7 | 157476790 | 157476974 | chr7 | 157476995 | 157477376 | chr7 | 157477395 | 157477489 |
| chr7 | 157477711 | 157477820 | chr7 | 157481534 | 157481550 | chr7 | 157481760 | 157481860 |
| chr7 | 157481890 | 157482074 | chr7 | 157482201 | 157482249 | chr7 | 157482401 | 157482508 |
| chr7 | 157482510 | 157482760 | chr7 | 157483220 | 157483639 | chr7 | 157484778 | 157485377 |
| chr7 | 157485437 | 157485602 | chr7 | 157485650 | 157485796 | chr7 | 157485881 | 157486082 |
| chr7 | 157486205 | 157486415 | chr7 | 157486476 | 157486600 | chr7 | 157584104 | 157584283 |
| chr7 | 157588510 | 157588869 | chr7 | 157606632 | 157606811 | chr7 | 157690145 | 157690161 |
| chr7 | 158059659 | 158059898 | chr7 | 158936420 | 158936956 | chr7 | 158937062 | 158937091 |
| chr7 | 158937203 | 158937375 | chr7 | 158937577 | 158937610 | chr7 | 158937612 | 158937721 |
| chr7 | 158938132 | 158938485 | chr8 | 686794 | 686885 | chr8 | 687163 | 687218 |
| chr8 | 687838 | 687976 | chr8 | 1085559 | 1085678 | chr8 | 4849040 | 4849263 |
| chr8 | 4849364 | 4849603 | chr8 | 4850173 | 4850323 | chr8 | 4850419 | 4850592 |
| chr8 | 4851662 | 4851686 | chr8 | 4851722 | 4851750 | chr8 | 4851781 | 4851841 |
| chr8 | 4851921 | 4852220 | chr8 | 8748329 | 8748808 | chr8 | 8748819 | 8749058 |
| chr8 | 9722754 | 9722993 | chr8 | 9755973 | 9756284 | chr8 | 9756487 | 9756564 |
| chr8 | 9760646 | 9761245 | chr8 | 9762487 | 9762690 | chr8 | 9762752 | 9762965 |
| chr8 | 9763060 | 9763359 | chr8 | 9763816 | 9764050 | chr8 | 9764196 | 9764295 |
| chr8 | 9764344 | 9764643 | chr8 | 10587507 | 10587603 | chr8 | 11204405 | 11204584 |
| chr8 | 11204709 | 11205008 | chr8 | 11536753 | 11536932 | chr8 | 11537157 | 11537362 |
| chr8 | 11554886 | 11554990 | chr8 | 11555068 | 11555167 | chr8 | 11555474 | 11555605 |
| chr8 | 11559707 | 11559792 | chr8 | 11560068 | 11560457 | chr8 | 11560633 | 11560872 |
| chr8 | 11561357 | 11561724 | chr8 | 11561726 | 11562196 | chr8 | 11562236 | 11562256 |
| chr8 | 11562335 | 11562574 | chr8 | 11562600 | 11563019 | chr8 | 11705869 | 11706228 |
| chr8 | 11726393 | 11726505 | chr8 | 12990409 | 12990529 | chr8 | 12990575 | 12990874 |
| chr8 | 13319857 | 13319937 | chr8 | 15094425 | 15094567 | chr8 | 15094646 | 15094664 |
| chr8 | 15397641 | 15397660 | chr8 | 16884239 | 16884331 | chr8 | 16885104 | 16885343 |
| chr8 | 17271091 | 17271213 | chr8 | 19797396 | 19797538 | chr8 | 19797860 | 19798099 |
| chr8 | 20160679 | 20160710 | chr8 | 22089428 | 22089665 | chr8 | 22562487 | 22562564 |
| chr8 | 22960567 | 22960806 | chr8 | 23021083 | 23021131 | chr8 | 23021193 | 23021209 |
| chr8 | 23260598 | 23260957 | chr8 | 23423830 | 23424009 | chr8 | 23559296 | 23559602 |
| chr8 | 23559666 | 23560615 | chr8 | 23563712 | 23564024 | chr8 | 23564193 | 23564480 |
| chr8 | 23564703 | 23565108 | chr8 | 23566729 | 23566855 | chr8 | 23566901 | 23567214 |
| chr8 | 23567312 | 23567568 | chr8 | 23571588 | 23572029 | chr8 | 23572031 | 23572067 |
| chr8 | 23572334 | 23572646 | chr8 | 23584000 | 23584017 | chr8 | 23584094 | 23584401 |
| chr8 | 23584582 | 23584839 | chr8 | 24770239 | 24770362 | chr8 | 24770414 | 24770658 |
| chr8 | 24771072 | 24771125 | chr8 | 24771350 | 24771575 | chr8 | 24771633 | 24771647 |
| chr8 | 24813089 | 24813388 | chr8 | 24813660 | 24813894 | chr8 | 24814011 | 24814499 |
| chr8 | 24857673 | 24857912 | chr8 | 24858239 | 24858538 | chr8 | 24858770 | 24859249 |
| chr8 | 24859422 | 24859601 | chr8 | 25041656 | 25041955 | chr8 | 25042636 | 25042671 |
| chr8 | 25900324 | 25900693 | chr8 | 25900781 | 25901017 | chr8 | 25901019 | 25901403 |
| chr8 | 25901444 | 25901863 | chr8 | 25902072 | 25902251 | chr8 | 25902545 | 25902640 |
| chr8 | 25903579 | 25903938 | chr8 | 25904055 | 25904294 | chr8 | 25905022 | 25905201 |
| chr8 | 25905696 | 25905907 | chr8 | 25909098 | 25909599 | chr8 | 25909601 | 25909697 |
| chr8 | 26372789 | 26372968 | chr8 | 26723884 | 26724183 | chr8 | 30243289 | 30243526 |
| chr8 | 30769151 | 30769510 | chr8 | 30770028 | 30770110 | chr8 | 30770158 | 30770267 |
| chr8 | 31496380 | 31496859 | chr8 | 31496939 | 31497042 | chr8 | 31497044 | 31497176 |
| chr8 | 31497420 | 31497719 | chr8 | 32406517 | 32406928 | chr8 | 32406930 | 32406996 |
| chr8 | 33371978 | 33372217 | chr8 | 33457052 | 33457471 | chr8 | 35093037 | 35093140 |
| chr8 | 35093877 | 35093974 | chr8 | 35094036 | 35094056 | chr8 | 37655367 | 37655376 |
| chr8 | 37655476 | 37655606 | chr8 | 37655707 | 37655991 | chr8 | 37656050 | 37656186 |

TABLE 15-continued

| chr | start | end | chr | start | end | chr | start | end |
|---|---|---|---|---|---|---|---|---|
| chr8 | 37822721 | 37823409 | chr8 | 37823411 | 37823475 | chr8 | 37823477 | 37823500 |
| chr8 | 37823790 | 37823805 | chr8 | 37961879 | 37961998 | chr8 | 38008157 | 38008636 |
| chr8 | 38323837 | 38324016 | chr8 | 38965450 | 38965464 | chr8 | 41165785 | 41165919 |
| chr8 | 41166001 | 41166152 | chr8 | 41166267 | 41166680 | chr8 | 41166746 | 41166804 |
| chr8 | 41166886 | 41166989 | chr8 | 41167026 | 41167125 | chr8 | 41424682 | 41424921 |
| chr8 | 41624752 | 41624931 | chr8 | 41625038 | 41625217 | chr8 | 41733424 | 41733654 |
| chr8 | 41733685 | 41733723 | chr8 | 41753498 | 41753753 | chr8 | 41753771 | 41753857 |
| chr8 | 41754070 | 41754181 | chr8 | 41754183 | 41754969 | chr8 | 41755104 | 41755283 |
| chr8 | 41910186 | 41910425 | chr8 | 42147417 | 42147596 | chr8 | 42749996 | 42750094 |
| chr8 | 47093172 | 47093351 | chr8 | 47334530 | 47334694 | chr8 | 48100075 | 48100539 |
| chr8 | 49293280 | 49293525 | chr8 | 49293581 | 49293699 | chr8 | 49468571 | 49468828 |
| chr8 | 49468830 | 49469228 | chr8 | 49571955 | 49572134 | chr8 | 49782953 | 49783235 |
| chr8 | 49959156 | 49959335 | chr8 | 50822095 | 50822358 | chr8 | 50822591 | 50822830 |
| chr8 | 50823358 | 50823657 | chr8 | 53477325 | 53477737 | chr8 | 53477945 | 53478352 |
| chr8 | 53478391 | 53478454 | chr8 | 53478456 | 53478744 | chr8 | 53853711 | 53854552 |
| chr8 | 54163240 | 54163350 | chr8 | 54163674 | 54164127 | chr8 | 54789175 | 54789414 |
| chr8 | 54789556 | 54789806 | chr8 | 54790023 | 54790155 | chr8 | 54790214 | 54790883 |
| chr8 | 54791724 | 54791782 | chr8 | 54791898 | 54791946 | chr8 | 54792185 | 54792323 |
| chr8 | 54792548 | 54792671 | chr8 | 54792702 | 54792847 | chr8 | 54794123 | 54794422 |
| chr8 | 54794626 | 54794781 | chr8 | 54794827 | 54794950 | chr8 | 54795140 | 54795165 |
| chr8 | 55366106 | 55366368 | chr8 | 55366952 | 55367725 | chr8 | 55370037 | 55370336 |
| chr8 | 55370338 | 55370423 | chr8 | 55370425 | 55370433 | chr8 | 55370568 | 55370714 |
| chr8 | 55370836 | 55370936 | chr8 | 55371173 | 55371376 | chr8 | 55371440 | 55371725 |
| chr8 | 55371994 | 55372068 | chr8 | 55372417 | 55372638 | chr8 | 55379202 | 55379231 |
| chr8 | 55379296 | 55379457 | chr8 | 55380037 | 55380041 | chr8 | 55382673 | 55382673 |
| chr8 | 55383183 | 55383332 | chr8 | 56013545 | 56013893 | chr8 | 56014012 | 56014024 |
| chr8 | 56014058 | 56014185 | chr8 | 56014377 | 56014417 | chr8 | 56014524 | 56014744 |
| chr8 | 56015035 | 56015053 | chr8 | 56015186 | 56015438 | chr8 | 56015471 | 56015662 |
| chr8 | 56015834 | 56015893 | chr8 | 57025609 | 57025620 | chr8 | 57025776 | 57026028 |
| chr8 | 57026072 | 57026311 | chr8 | 57026502 | 57026644 | chr8 | 57069473 | 57069738 |
| chr8 | 57069851 | 57070013 | chr8 | 57070015 | 57070245 | chr8 | 57358053 | 57358147 |
| chr8 | 57358465 | 57358662 | chr8 | 57358807 | 57359092 | chr8 | 57359260 | 57359732 |
| chr8 | 57360472 | 57360626 | chr8 | 57360770 | 57360891 | chr8 | 58105852 | 58106211 |
| chr8 | 58116923 | 58117162 | chr8 | 58130290 | 58130649 | chr8 | 58907618 | 58907821 |
| chr8 | 58907823 | 58907917 | chr8 | 59058934 | 59059233 | chr8 | 59747274 | 59747402 |
| chr8 | 60032590 | 60032829 | chr8 | 61777488 | 61777622 | chr8 | 61789900 | 61790076 |
| chr8 | 62200414 | 62200879 | chr8 | 63161580 | 63161879 | chr8 | 65281539 | 65281778 |
| chr8 | 65281884 | 65282005 | chr8 | 65282333 | 65282441 | chr8 | 65283708 | 65284187 |
| chr8 | 65285972 | 65286067 | chr8 | 65286371 | 65286451 | chr8 | 65286599 | 65286838 |
| chr8 | 65286868 | 65287229 | chr8 | 65289033 | 65289332 | chr8 | 65289517 | 65290450 |
| chr8 | 65290570 | 65290682 | chr8 | 65290950 | 65291369 | chr8 | 65292572 | 65292816 |
| chr8 | 65488178 | 65488417 | chr8 | 65488618 | 65488799 | chr8 | 65489025 | 65489065 |
| chr8 | 65489067 | 65489204 | chr8 | 65492637 | 65493056 | chr8 | 65493105 | 65493524 |
| chr8 | 65493556 | 65493579 | chr8 | 65493807 | 65493855 | chr8 | 65493868 | 65493955 |
| chr8 | 65494077 | 65494101 | chr8 | 65494103 | 65494287 | chr8 | 65498465 | 65498550 |
| chr8 | 65498645 | 65498910 | chr8 | 65498926 | 65498944 | chr8 | 65499677 | 65500096 |
| chr8 | 65710868 | 65711084 | chr8 | 66548640 | 66548749 | chr8 | 67024963 | 67025365 |
| chr8 | 67344446 | 67344665 | chr8 | 67344667 | 67344702 | chr8 | 67344810 | 67344865 |
| chr8 | 67873246 | 67873422 | chr8 | 67873799 | 67873799 | chr8 | 67873801 | 67874051 |
| chr8 | 67874165 | 67874673 | chr8 | 67874756 | 67874858 | chr8 | 67874860 | 67875261 |
| chr8 | 67875263 | 67875441 | chr8 | 67875443 | 67875697 | chr8 | 67940548 | 67940960 |
| chr8 | 68864546 | 68864852 | chr8 | 69242828 | 69243007 | chr8 | 69243285 | 69243486 |
| chr8 | 69243488 | 69243903 | chr8 | 69243964 | 69243971 | chr8 | 69244286 | 69244510 |
| chr8 | 69244512 | 69244585 | chr8 | 70744774 | 70745013 | chr8 | 70946670 | 70946915 |
| chr8 | 70947091 | 70947742 | chr8 | 70981866 | 70981880 | chr8 | 70982263 | 70982285 |
| chr8 | 70982287 | 70982567 | chr8 | 70982851 | 70983305 | chr8 | 70983402 | 70983870 |
| chr8 | 70984017 | 70984293 | chr8 | 70984344 | 70984662 | chr8 | 70984745 | 70985081 |
| chr8 | 72273897 | 72274136 | chr8 | 72468473 | 72469664 | chr8 | 72470301 | 72470540 |
| chr8 | 72471037 | 72471158 | chr8 | 72754293 | 72754361 | chr8 | 72754491 | 72754712 |
| chr8 | 72754730 | 72755240 | chr8 | 72755592 | 72755815 | chr8 | 72756656 | 72756812 |
| chr8 | 72756814 | 72756971 | chr8 | 72917268 | 72917516 | chr8 | 72917519 | 72917541 |
| chr8 | 72987519 | 72987916 | chr8 | 72987918 | 72988118 | chr8 | 73163860 | 73164261 |
| chr8 | 73450027 | 73450202 | chr8 | 73450418 | 73450657 | chr8 | 74759411 | 74759565 |
| chr8 | 74759744 | 74759863 | chr8 | 75896477 | 75896836 | chr8 | 75896838 | 75897297 |
| chr8 | 75897299 | 75897436 | chr8 | 76316242 | 76316541 | chr8 | 77585130 | 77585789 |
| chr8 | 77586078 | 77586377 | chr8 | 77586471 | 77586710 | chr8 | 77590144 | 77590563 |
| chr8 | 77593075 | 77593233 | chr8 | 77593235 | 77593453 | chr8 | 77593798 | 77594217 |
| chr8 | 77594552 | 77594595 | chr8 | 77594597 | 77594675 | chr8 | 77594758 | 77595091 |
| chr8 | 77595238 | 77595594 | chr8 | 79428200 | 79428499 | chr8 | 80523887 | 80524126 |
| chr8 | 80524167 | 80524406 | chr8 | 80524864 | 80525103 | chr8 | 80525520 | 80525819 |
| chr8 | 80695842 | 80696007 | chr8 | 80803594 | 80803953 | chr8 | 81478089 | 81478448 |
| chr8 | 85095396 | 85095498 | chr8 | 85095500 | 85095755 | chr8 | 85096485 | 85096721 |
| chr8 | 85096853 | 85096904 | chr8 | 85096939 | 85097003 | chr8 | 85097063 | 85097298 |
| chr8 | 86350455 | 86350567 | chr8 | 86406814 | 86406933 | chr8 | 86436547 | 86436726 |
| chr8 | 86544681 | 86544798 | chr8 | 89339298 | 89339837 | chr8 | 89340189 | 89340237 |
| chr8 | 89340274 | 89340428 | chr8 | 90913517 | 90913756 | chr8 | 91094161 | 91094326 |
| chr8 | 91803578 | 91803720 | chr8 | 91804065 | 91804332 | chr8 | 91996958 | 91997509 |
| chr8 | 91997528 | 91998037 | chr8 | 92083443 | 92083622 | chr8 | 93114033 | 93114150 |

TABLE 15-continued

| chr | start | end | chr | start | end | chr | start | end |
|---|---|---|---|---|---|---|---|---|
| chr8 | 93114152 | 93114242 | chr8 | 93114307 | 93114632 | chr8 | 95651240 | 95651269 |
| chr8 | 95651448 | 95651599 | chr8 | 95651637 | 95651747 | chr8 | 96219911 | 96220002 |
| chr8 | 97157007 | 97157210 | chr8 | 97157667 | 97157898 | chr8 | 97158022 | 97158146 |
| chr8 | 97165541 | 97165780 | chr8 | 97166351 | 97166530 | chr8 | 97167082 | 97167321 |
| chr8 | 97169757 | 97169920 | chr8 | 97169922 | 97169956 | chr8 | 97170054 | 97170338 |
| chr8 | 97170378 | 97170416 | chr8 | 97170793 | 97170972 | chr8 | 97171036 | 97171265 |
| chr8 | 97171318 | 97171959 | chr8 | 97172019 | 97172295 | chr8 | 97172347 | 97172740 |
| chr8 | 97172822 | 97172961 | chr8 | 97172963 | 97173526 | chr8 | 97173528 | 97173546 |
| chr8 | 97173730 | 97173864 | chr8 | 97173921 | 97173991 | chr8 | 97339752 | 97340291 |
| chr8 | 97505950 | 97506049 | chr8 | 97506178 | 97506408 | chr8 | 97506448 | 97506609 |
| chr8 | 97507021 | 97507380 | chr8 | 97507464 | 97507763 | chr8 | 98289744 | 98289868 |
| chr8 | 98289923 | 98290343 | chr8 | 99439030 | 99439209 | chr8 | 99439299 | 99440438 |
| chr8 | 99951330 | 99951509 | chr8 | 99951757 | 99952144 | chr8 | 99952199 | 99952304 |
| chr8 | 99952533 | 99952896 | chr8 | 99954400 | 99954563 | chr8 | 99954679 | 99954819 |
| chr8 | 99955105 | 99955394 | chr8 | 99960231 | 99960498 | chr8 | 99960922 | 99961070 |
| chr8 | 99961111 | 99961174 | chr8 | 99961718 | 99961897 | chr8 | 99985781 | 99986044 |
| chr8 | 99986226 | 99986527 | chr8 | 99986792 | 99987020 | chr8 | 101118140 | 101118491 |
| chr8 | 101118659 | 101118679 | chr8 | 101661837 | 101662000 | chr8 | 101821891 | 101822130 |
| chr8 | 102505458 | 102505654 | chr8 | 102505720 | 102505986 | chr8 | 103629857 | 103629961 |
| chr8 | 104153105 | 104153344 | chr8 | 104153366 | 104153562 | chr8 | 104153682 | 104153725 |
| chr8 | 104512026 | 104513285 | chr8 | 104513365 | 104513909 | chr8 | 104513911 | 104514005 |
| chr8 | 105235293 | 105235502 | chr8 | 105235644 | 105235804 | chr8 | 105235864 | 105236132 |
| chr8 | 105478632 | 105478780 | chr8 | 105479248 | 105479281 | chr8 | 105479315 | 105479531 |
| chr8 | 106331084 | 106331257 | chr8 | 106332004 | 106332286 | chr8 | 107282060 | 107282299 |
| chr8 | 107283938 | 107284054 | chr8 | 107284056 | 107284177 | chr8 | 108509441 | 108509734 |
| chr8 | 109093601 | 109094260 | chr8 | 109094391 | 109094690 | chr8 | 109094757 | 109095437 |
| chr8 | 109095506 | 109095568 | chr8 | 109095570 | 109095974 | chr8 | 109799500 | 109799740 |
| chr8 | 110274904 | 110275021 | chr8 | 110405946 | 110406106 | chr8 | 110592245 | 110592303 |
| chr8 | 110703924 | 110704029 | chr8 | 110704098 | 110704223 | chr8 | 110986354 | 110986773 |
| chr8 | 114444497 | 114444640 | chr8 | 114444709 | 114445276 | chr8 | 114445677 | 114446101 |
| chr8 | 114446851 | 114447346 | chr8 | 114447348 | 114447450 | chr8 | 114448939 | 114449358 |
| chr8 | 114449457 | 114449688 | chr8 | 116660435 | 116660572 | chr8 | 116660616 | 116660854 |
| chr8 | 117950364 | 117950543 | chr8 | 117950700 | 117950999 | chr8 | 120220390 | 120220606 |
| chr8 | 120844011 | 120844126 | chr8 | 121136805 | 121137824 | chr8 | 121823827 | 121824006 |
| chr8 | 121824103 | 121824582 | chr8 | 121825512 | 121825560 | chr8 | 122651770 | 122652009 |
| chr8 | 123695447 | 123695746 | chr8 | 124055137 | 124055235 | chr8 | 124173165 | 124173544 |
| chr8 | 125452275 | 125452394 | chr8 | 126044494 | 126044653 | chr8 | 128745443 | 128745618 |
| chr8 | 128872311 | 128872490 | chr8 | 128889224 | 128889483 | chr8 | 128931157 | 128931336 |
| chr8 | 130369290 | 130369454 | chr8 | 132052057 | 132052300 | chr8 | 132052399 | 132052516 |
| chr8 | 132052590 | 132053256 | chr8 | 132053633 | 132054584 | chr8 | 132054594 | 132054876 |
| chr8 | 133686658 | 133686836 | chr8 | 139508668 | 139508947 | chr8 | 139509656 | 139509671 |
| chr8 | 139509694 | 139510015 | chr8 | 140714485 | 140714964 | chr8 | 140715016 | 140715095 |
| chr8 | 140715379 | 140715588 | chr8 | 140715700 | 140715738 | chr8 | 140715875 | 140716022 |
| chr8 | 140716340 | 140716348 | chr8 | 140834160 | 140834399 | chr8 | 140963208 | 140963447 |
| chr8 | 141159845 | 141160024 | chr8 | 141587975 | 141588214 | chr8 | 141596805 | 141597104 |
| chr8 | 142292454 | 142292808 | chr8 | 142361151 | 142361430 | chr8 | 142367673 | 142367879 |
| chr8 | 142444648 | 142444827 | chr8 | 142528313 | 142528403 | chr8 | 142528455 | 142528607 |
| chr8 | 142528671 | 142528782 | chr8 | 142528835 | 142528962 | chr8 | 142529028 | 142529192 |
| chr8 | 142535241 | 142535587 | chr8 | 142568506 | 142568745 | chr8 | 142694751 | 142695030 |
| chr8 | 142984437 | 142984736 | chr8 | 143088946 | 143089153 | chr8 | 143105162 | 143105461 |
| chr8 | 143509377 | 143509607 | chr8 | 143509629 | 143509676 | chr8 | 143532035 | 143532510 |
| chr8 | 143532542 | 143532934 | chr8 | 143533520 | 143533641 | chr8 | 143533709 | 143533999 |
| chr8 | 143557881 | 143558172 | chr8 | 143558389 | 143558688 | chr8 | 143587238 | 143587477 |
| chr8 | 143592664 | 143592762 | chr8 | 143621889 | 143622188 | chr8 | 143701978 | 143702157 |
| chr8 | 143819303 | 143819406 | chr8 | 143858435 | 143858791 | chr8 | 143859223 | 143859281 |
| chr8 | 143859338 | 143859454 | chr8 | 143876854 | 143877033 | chr8 | 143993891 | 143994250 |
| chr8 | 144069457 | 144069749 | chr8 | 144190286 | 144190525 | chr8 | 144203601 | 144203801 |
| chr8 | 144203880 | 144204020 | chr8 | 144226100 | 144226279 | chr8 | 144238743 | 144238982 |
| chr8 | 144241150 | 144241389 | chr8 | 144241444 | 144241522 | chr8 | 144241584 | 144241683 |
| chr8 | 144241785 | 144242381 | chr8 | 144303488 | 144303667 | chr8 | 144328234 | 144328653 |
| chr8 | 144330288 | 144330467 | chr8 | 144344219 | 144344518 | chr8 | 144359928 | 144360177 |
| chr8 | 144360305 | 144360544 | chr8 | 144361672 | 144361911 | chr8 | 144372474 | 144372583 |
| chr8 | 144509238 | 144510617 | chr8 | 144511146 | 144511505 | chr8 | 144511938 | 144512297 |
| chr8 | 144512399 | 144512466 | chr8 | 144650791 | 144650812 | chr8 | 144668532 | 144668767 |
| chr8 | 144668822 | 144669061 | chr8 | 145753443 | 145753622 | chr8 | 145758483 | 145758782 |
| chr8 | 145806184 | 145806272 | chr8 | 145925387 | 145925429 | chr8 | 145925459 | 145925566 |
| chr8 | 145925869 | 145926069 | chr8 | 146013543 | 146013722 | chr8 | 146079134 | 146079297 |
| chr9 | 113346 | 113513 | chr9 | 113550 | 113645 | chr9 | 113749 | 113988 |
| chr9 | 117808 | 117960 | chr9 | 118140 | 118167 | chr9 | 841602 | 841850 |
| chr9 | 841852 | 842032 | chr9 | 842208 | 842244 | chr9 | 842611 | 842748 |
| chr9 | 969482 | 969615 | chr9 | 969685 | 969943 | chr9 | 970012 | 970105 |
| chr9 | 970186 | 970311 | chr9 | 970421 | 970600 | chr9 | 970816 | 970912 |
| chr9 | 970993 | 971175 | chr9 | 971639 | 971655 | chr9 | 972204 | 972863 |
| chr9 | 973184 | 973366 | chr9 | 975248 | 975262 | chr9 | 975693 | 976412 |
| chr9 | 976521 | 976690 | chr9 | 976912 | 977047 | chr9 | 981695 | 981934 |
| chr9 | 1042305 | 1042501 | chr9 | 1042616 | 1043076 | chr9 | 1051905 | 1052247 |
| chr9 | 3181662 | 3181961 | chr9 | 6412497 | 6412900 | chr9 | 6644217 | 6644368 |
| chr9 | 6644540 | 6644636 | chr9 | 6644936 | 6645415 | chr9 | 6645544 | 6645783 |

TABLE 15-continued

| chr | start | end | chr | start | end | chr | start | end |
|---|---|---|---|---|---|---|---|---|
| chr9 | 6756279 | 6756429 | chr9 | 13278722 | 13278961 | chr9 | 14312943 | 14313182 |
| chr9 | 14347534 | 14347759 | chr9 | 14348234 | 14348533 | chr9 | 17906310 | 17906433 |
| chr9 | 17906461 | 17906789 | chr9 | 17906914 | 17907153 | chr9 | 17907325 | 17907371 |
| chr9 | 17907451 | 17907564 | chr9 | 19789025 | 19789381 | chr9 | 21031636 | 21031924 |
| chr9 | 21402520 | 21403119 | chr9 | 21559219 | 21559446 | chr9 | 21559678 | 21559804 |
| chr9 | 21964958 | 21965425 | chr9 | 21965570 | 21965857 | chr9 | 21968138 | 21968434 |
| chr9 | 21968457 | 21968557 | chr9 | 21970881 | 21971155 | chr9 | 21971185 | 21971282 |
| chr9 | 21974182 | 21974329 | chr9 | 21974408 | 21974887 | chr9 | 21994134 | 21994313 |
| chr9 | 21995223 | 21995402 | chr9 | 21995646 | 21995825 | chr9 | 22006057 | 22006153 |
| chr9 | 22006228 | 22006236 | chr9 | 22447567 | 22447772 | chr9 | 23822468 | 23822707 |
| chr9 | 23824487 | 23824666 | chr9 | 23831023 | 23831371 | chr9 | 23831451 | 23831490 |
| chr9 | 29212083 | 29212171 | chr9 | 29212211 | 29212382 | chr9 | 29213431 | 29213730 |
| chr9 | 29213938 | 29214237 | chr9 | 29214276 | 29214515 | chr9 | 29214585 | 29215184 |
| chr9 | 32782547 | 32782936 | chr9 | 32783084 | 32783206 | chr9 | 32783263 | 32783420 |
| chr9 | 32783591 | 32783742 | chr9 | 33524529 | 33524768 | chr9 | 33676697 | 33676876 |
| chr9 | 33677269 | 33677508 | chr9 | 34224262 | 34224497 | chr9 | 34372761 | 34373000 |
| chr9 | 34588960 | 34589259 | chr9 | 35617195 | 35617434 | chr9 | 35675441 | 35675648 |
| chr9 | 35675838 | 35676233 | chr9 | 36036994 | 36037173 | chr9 | 36318274 | 36318389 |
| chr9 | 36739812 | 36740078 | chr9 | 37002394 | 37002518 | chr9 | 37002819 | 37003113 |
| chr9 | 37025465 | 37025884 | chr9 | 37026055 | 37026352 | chr9 | 37026434 | 37026714 |
| chr9 | 37026733 | 37027272 | chr9 | 37027325 | 37027384 | chr9 | 37027386 | 37027512 |
| chr9 | 37027726 | 37027905 | chr9 | 37028870 | 37029049 | chr9 | 37029436 | 37030755 |
| chr9 | 37034163 | 37034342 | chr9 | 37034525 | 37034824 | chr9 | 37035427 | 37035820 |
| chr9 | 37036327 | 37036746 | chr9 | 37037594 | 37038433 | chr9 | 37467521 | 37467634 |
| chr9 | 38620642 | 38620808 | chr9 | 66456024 | 66456117 | chr9 | 71200618 | 71200720 |
| chr9 | 71734803 | 71734920 | chr9 | 71788876 | 71789261 | chr9 | 71789453 | 71789512 |
| chr9 | 71789608 | 71789835 | chr9 | 73032727 | 73032835 | chr9 | 74061745 | 74061759 |
| chr9 | 74061788 | 74062164 | chr9 | 74764449 | 74764748 | chr9 | 77112900 | 77113341 |
| chr9 | 77113559 | 77113709 | chr9 | 77113806 | 77113919 | chr9 | 77114649 | 77114948 |
| chr9 | 77115120 | 77115539 | chr9 | 77115583 | 77115587 | chr9 | 79626794 | 79627453 |
| chr9 | 79628190 | 79628429 | chr9 | 79629208 | 79629499 | chr9 | 79629533 | 79629553 |
| chr9 | 79629791 | 79630491 | chr9 | 79631115 | 79631414 | chr9 | 79631454 | 79631693 |
| chr9 | 79631785 | 79632264 | chr9 | 79632786 | 79632965 | chr9 | 79633322 | 79633737 |
| chr9 | 79633739 | 79633981 | chr9 | 79634088 | 79634987 | chr9 | 79635048 | 79635449 |
| chr9 | 79635746 | 79636066 | chr9 | 79636103 | 79636127 | chr9 | 79636167 | 79636642 |
| chr9 | 79636717 | 79637366 | chr9 | 79637644 | 79637889 | chr9 | 79638137 | 79638336 |
| chr9 | 86152313 | 86152372 | chr9 | 86152382 | 86152492 | chr9 | 86755443 | 86756042 |
| chr9 | 86886632 | 86886811 | chr9 | 87282934 | 87283113 | chr9 | 87283574 | 87283813 |
| chr9 | 87284603 | 87284902 | chr9 | 87285273 | 87285533 | chr9 | 87285555 | 87285556 |
| chr9 | 88137487 | 88137726 | chr9 | 88137875 | 88138091 | chr9 | 89517623 | 89517655 |
| chr9 | 89517861 | 89517917 | chr9 | 89560675 | 89560914 | chr9 | 89560967 | 89561206 |
| chr9 | 91150130 | 91150429 | chr9 | 91605912 | 91606151 | chr9 | 91792283 | 91792462 |
| chr9 | 91792693 | 91792992 | chr9 | 91793083 | 91793622 | chr9 | 93697942 | 93698051 |
| chr9 | 94183793 | 94184032 | chr9 | 94572543 | 94572703 | chr9 | 94712295 | 94712320 |
| chr9 | 95417452 | 95417747 | chr9 | 95560736 | 95560915 | chr9 | 95569672 | 95569911 |
| chr9 | 95570162 | 95570521 | chr9 | 95571540 | 95571659 | chr9 | 95571753 | 95571839 |
| chr9 | 95947121 | 95947360 | chr9 | 96588726 | 96588740 | chr9 | 96588858 | 96588965 |
| chr9 | 96710303 | 96710482 | chr9 | 96710582 | 96711089 | chr9 | 96711169 | 96711447 |
| chr9 | 96711535 | 96711708 | chr9 | 96711901 | 96712080 | chr9 | 96713277 | 96713996 |
| chr9 | 96714997 | 96715068 | chr9 | 96715135 | 96715373 | chr9 | 96715688 | 96715794 |
| chr9 | 96716763 | 96716824 | chr9 | 96716905 | 96717428 | chr9 | 96717450 | 96717542 |
| chr9 | 96717885 | 96718244 | chr9 | 96720752 | 96720886 | chr9 | 96721103 | 96721468 |
| chr9 | 96721689 | 96721903 | chr9 | 96722477 | 96722548 | chr9 | 96722863 | 96722886 |
| chr9 | 96722999 | 96723160 | chr9 | 96723171 | 96723298 | chr9 | 98111281 | 98111561 |
| chr9 | 98111895 | 98112158 | chr9 | 98112344 | 98112472 | chr9 | 98784698 | 98784877 |
| chr9 | 98789557 | 98790013 | chr9 | 98790084 | 98790096 | chr9 | 99449054 | 99449487 |
| chr9 | 99639543 | 99640022 | chr9 | 99983066 | 99983245 | chr9 | 99983319 | 99983704 |
| chr9 | 99983799 | 99983918 | chr9 | 99983925 | 99984004 | chr9 | 100503542 | 100504021 |
| chr9 | 100609970 | 100610135 | chr9 | 100610201 | 100610315 | chr9 | 100610603 | 100610817 |
| chr9 | 100611125 | 100611731 | chr9 | 100613748 | 100614000 | chr9 | 100614193 | 100614407 |
| chr9 | 100614463 | 100615201 | chr9 | 100615203 | 100616036 | chr9 | 100616271 | 100616469 |
| chr9 | 100617286 | 100617449 | chr9 | 100617600 | 100618139 | chr9 | 100619627 | 100620166 |
| chr9 | 100620228 | 100620862 | chr9 | 100818337 | 100818516 | chr9 | 100835850 | 100835969 |
| chr9 | 101469169 | 101469408 | chr9 | 101469521 | 101469880 | chr9 | 101470034 | 101470333 |
| chr9 | 101470991 | 101471170 | chr9 | 101471477 | 101471553 | chr9 | 101471555 | 101471716 |
| chr9 | 101471786 | 101472030 | chr9 | 101705897 | 101706041 | chr9 | 101706043 | 101706196 |
| chr9 | 101706313 | 101706796 | chr9 | 103174718 | 103174825 | chr9 | 104248482 | 104248650 |
| chr9 | 104248698 | 104248721 | chr9 | 104249400 | 104249632 | chr9 | 104500551 | 104500850 |
| chr9 | 110126159 | 110126338 | chr9 | 110228102 | 110228701 | chr9 | 110251381 | 110251493 |
| chr9 | 110252260 | 110252455 | chr9 | 110252548 | 110252619 | chr9 | 112403096 | 112403275 |
| chr9 | 112403290 | 112403301 | chr9 | 112403303 | 112403469 | chr9 | 113341445 | 113341622 |
| chr9 | 113341680 | 113341848 | chr9 | 113341927 | 113342044 | chr9 | 113342201 | 113342428 |
| chr9 | 115067840 | 115067945 | chr9 | 115478852 | 115478971 | chr9 | 115652867 | 115653526 |
| chr9 | 116633786 | 116633905 | chr9 | 117050887 | 117051126 | chr9 | 118916933 | 118917172 |
| chr9 | 120175695 | 120175934 | chr9 | 120176009 | 120176248 | chr9 | 120176793 | 120176972 |
| chr9 | 120507467 | 120507514 | chr9 | 122131383 | 122131439 | chr9 | 122131497 | 122131742 |
| chr9 | 122131785 | 122132026 | chr9 | 122132052 | 122132320 | chr9 | 123295404 | 123295559 |
| chr9 | 124751411 | 124751590 | chr9 | 125676724 | 125676798 | chr9 | 126133698 | 126133937 |

TABLE 15-continued

| chr | start | end | chr | start | end | chr | start | end |
|---|---|---|---|---|---|---|---|---|
| chr9 | 126154201 | 126154651 | chr9 | 126349070 | 126349191 | chr9 | 126770159 | 126770398 |
| chr9 | 126771440 | 126771799 | chr9 | 126774460 | 126774620 | chr9 | 126775456 | 126775620 |
| chr9 | 126775963 | 126776099 | chr9 | 126777488 | 126777747 | chr9 | 126777974 | 126778086 |
| chr9 | 126778359 | 126778593 | chr9 | 126779391 | 126780044 | chr9 | 126780285 | 126780406 |
| chr9 | 126780736 | 126780975 | chr9 | 126783321 | 126783577 | chr9 | 127212750 | 127213109 |
| chr9 | 127265588 | 127265610 | chr9 | 127265876 | 127266127 | chr9 | 127266372 | 127266588 |
| chr9 | 128652097 | 128652336 | chr9 | 128759764 | 128760053 | chr9 | 129276620 | 129276919 |
| chr9 | 129372837 | 129373038 | chr9 | 129373251 | 129373316 | chr9 | 129376096 | 129376275 |
| chr9 | 129376815 | 129376892 | chr9 | 129376932 | 129376994 | chr9 | 129377116 | 129377352 |
| chr9 | 129377593 | 129377636 | chr9 | 129377773 | 129377960 | chr9 | 129378025 | 129378104 |
| chr9 | 129381027 | 129381084 | chr9 | 129387421 | 129387539 | chr9 | 129387701 | 129387749 |
| chr9 | 129387848 | 129388300 | chr9 | 129388639 | 129388754 | chr9 | 129388817 | 129388878 |
| chr9 | 129388915 | 129389274 | chr9 | 129400912 | 129401271 | chr9 | 129445232 | 129445651 |
| chr9 | 129445709 | 129445888 | chr9 | 129485763 | 129485772 | chr9 | 130248345 | 130248524 |
| chr9 | 130461543 | 130461571 | chr9 | 130461687 | 130461842 | chr9 | 130689631 | 130689668 |
| chr9 | 130689742 | 130689742 | chr9 | 131579939 | 131580104 | chr9 | 131607443 | 131607622 |
| chr9 | 131607696 | 131607875 | chr9 | 131854131 | 131854430 | chr9 | 132382297 | 132382355 |
| chr9 | 132382635 | 132383116 | chr9 | 132402743 | 132402982 | chr9 | 132403064 | 132403303 |
| chr9 | 132559298 | 132559413 | chr9 | 132805270 | 132805449 | chr9 | 132805750 | 132805989 |
| chr9 | 133308798 | 133309037 | chr9 | 133534609 | 133534788 | chr9 | 133535707 | 133535934 |
| chr9 | 133536012 | 133536120 | chr9 | 133536150 | 133536345 | chr9 | 133536347 | 133536431 |
| chr9 | 133536675 | 133536974 | chr9 | 133537097 | 133537636 | chr9 | 133538090 | 133538809 |
| chr9 | 133539511 | 133539808 | chr9 | 133540977 | 133541276 | chr9 | 133541594 | 133542433 |
| chr9 | 133773666 | 133774025 | chr9 | 133927265 | 133927564 | chr9 | 133928162 | 133928341 |
| chr9 | 134191003 | 134191302 | chr9 | 134207833 | 134207997 | chr9 | 134421818 | 134421936 |
| chr9 | 134717221 | 134717434 | chr9 | 135037029 | 135037288 | chr9 | 135037334 | 135037448 |
| chr9 | 135455317 | 135455676 | chr9 | 135455912 | 135456024 | chr9 | 135456080 | 135456151 |
| chr9 | 135456391 | 135456630 | chr9 | 135456796 | 135456915 | chr9 | 135458388 | 135458440 |
| chr9 | 135458457 | 135458687 | chr9 | 135459920 | 135460269 | chr9 | 135460795 | 135460819 |
| chr9 | 135461455 | 135461852 | chr9 | 135461969 | 135462078 | chr9 | 135462648 | 135463048 |
| chr9 | 135464709 | 135465008 | chr9 | 135465861 | 135466065 | chr9 | 135466118 | 135466220 |
| chr9 | 135466263 | 135466742 | chr9 | 135548157 | 135548265 | chr9 | 135865007 | 135865246 |
| chr9 | 135898809 | 135899211 | chr9 | 136474432 | 136474592 | chr9 | 137299018 | 137299555 |
| chr9 | 137299596 | 137299677 | chr9 | 137533897 | 137533967 | chr9 | 137534066 | 137534316 |
| chr9 | 137656864 | 137657223 | chr9 | 137667253 | 137667432 | chr9 | 137718802 | 137719101 |
| chr9 | 137721999 | 137722197 | chr9 | 137979803 | 137980102 | chr9 | 137980217 | 137980363 |
| chr9 | 137980806 | 137980985 | chr9 | 138265038 | 138265337 | chr9 | 138562961 | 138563377 |
| chr9 | 138606221 | 138606249 | chr9 | 138606711 | 138606774 | chr9 | 138606821 | 138606850 |
| chr9 | 138606927 | 138607010 | chr9 | 138627556 | 138627925 | chr9 | 138633954 | 138634253 |
| chr9 | 138659704 | 138660003 | chr9 | 138660859 | 138661098 | chr9 | 138661550 | 138661969 |
| chr9 | 138666358 | 138666657 | chr9 | 138880882 | 138880973 | chr9 | 138991833 | 138991903 |
| chr9 | 139000485 | 139000724 | chr9 | 139012193 | 139012492 | chr9 | 139024750 | 139024873 |
| chr9 | 139045579 | 139045758 | chr9 | 139047494 | 139047733 | chr9 | 139085145 | 139085351 |
| chr9 | 139085373 | 139085444 | chr9 | 139085986 | 139086071 | chr9 | 139090420 | 139090552 |
| chr9 | 139090587 | 139090659 | chr9 | 139090692 | 139090742 | chr9 | 139091072 | 139091471 |
| chr9 | 139093773 | 139093923 | chr9 | 139094610 | 139094733 | chr9 | 139095264 | 139095563 |
| chr9 | 139096559 | 139097098 | chr9 | 139111194 | 139111373 | chr9 | 139268961 | 139268987 |
| chr9 | 139421881 | 139422060 | chr9 | 139698839 | 139699138 | chr9 | 139704085 | 139704384 |
| chr9 | 139858946 | 139859365 | chr9 | 139888844 | 139889083 | chr9 | 140024754 | 140024771 |
| chr9 | 140024787 | 140024919 | chr9 | 140024957 | 140025113 | chr9 | 140030424 | 140030603 |
| chr9 | 140032802 | 140033050 | chr9 | 140033192 | 140033197 | chr9 | 140033325 | 140033491 |
| chr9 | 140033619 | 140033627 | chr9 | 140033815 | 140034174 | chr9 | 140050893 | 140051097 |
| chr9 | 140051220 | 140051432 | chr9 | 140127803 | 140128162 | chr9 | 140137220 | 140137334 |
| chr9 | 140205346 | 140205607 | chr9 | 140245789 | 140246084 | chr9 | 140332624 | 140333103 |
| chr9 | 140382472 | 140382697 | chr9 | 140392380 | 140392559 | chr9 | 140396944 | 140397183 |
| chr9 | 140507207 | 140507506 | chr9 | 140708961 | 140709260 | chr9 | 140727429 | 140727611 |
| chr9 | 140727769 | 140728008 | chr9 | 140769913 | 140770048 | chr9 | 140771969 | 140772431 |
| chr9 | 140772495 | 140772594 | chr9 | 140772757 | 140773394 | chr10 | 524680 | 524770 |
| chr10 | 833228 | 833419 | chr10 | 978787 | 979026 | chr10 | 1585208 | 1585325 |
| chr10 | 1708551 | 1708583 | chr10 | 1779342 | 1779821 | chr10 | 3285686 | 3285792 |
| chr10 | 3330410 | 3330696 | chr10 | 3641277 | 3641396 | chr10 | 3678618 | 3678737 |
| chr10 | 3895312 | 3895551 | chr10 | 4599822 | 4600061 | chr10 | 5530673 | 5531080 |
| chr10 | 5875059 | 5875345 | chr10 | 6003386 | 6003625 | chr10 | 6042233 | 6042592 |
| chr10 | 6162073 | 6162302 | chr10 | 6577569 | 6577748 | chr10 | 6984626 | 6984731 |
| chr10 | 7205641 | 7205880 | chr10 | 7212666 | 7213145 | chr10 | 7213532 | 7213610 |
| chr10 | 7215985 | 7216164 | chr10 | 7236109 | 7236348 | chr10 | 7255627 | 7255659 |
| chr10 | 7414447 | 7414686 | chr10 | 7424552 | 7424731 | chr10 | 7449863 | 7450190 |
| chr10 | 7450491 | 7451482 | chr10 | 7452143 | 7452862 | chr10 | 7453233 | 7453657 |
| chr10 | 7453903 | 7454012 | chr10 | 7708311 | 7708379 | chr10 | 7708700 | 7708857 |
| chr10 | 7708955 | 7709090 | chr10 | 7709649 | 7709807 | chr10 | 8075843 | 8075945 |
| chr10 | 8076054 | 8076071 | chr10 | 8076341 | 8076563 | chr10 | 8076730 | 8077449 |
| chr10 | 8077790 | 8078316 | chr10 | 8085600 | 8085800 | chr10 | 8085875 | 8086114 |
| chr10 | 8091818 | 8092099 | chr10 | 8093653 | 8093825 | chr10 | 8093860 | 8093964 |
| chr10 | 8095515 | 8095774 | chr10 | 8095842 | 8095934 | chr10 | 8096086 | 8096265 |
| chr10 | 8096877 | 8097296 | chr10 | 8097387 | 8097588 | chr10 | 11059620 | 11059664 |
| chr10 | 11059933 | 11060158 | chr10 | 11207079 | 11207378 | chr10 | 11700861 | 11701100 |
| chr10 | 13043287 | 13043526 | chr10 | 13141002 | 13141106 | chr10 | 13715462 | 13715485 |
| chr10 | 13933361 | 13933539 | chr10 | 13933597 | 13933935 | chr10 | 13933983 | 13933996 |

TABLE 15-continued

| chr | start | end | chr | start | end | chr | start | end |
|---|---|---|---|---|---|---|---|---|
| chr10 | 13933998 | 13934126 | chr10 | 13934169 | 13934260 | chr10 | 14966052 | 14966291 |
| chr10 | 15140509 | 15140625 | chr10 | 15761213 | 15761752 | chr10 | 15762050 | 15762211 |
| chr10 | 16562009 | 16562043 | chr10 | 16562369 | 16562626 | chr10 | 16562628 | 16562673 |
| chr10 | 16562710 | 16563665 | chr10 | 16563691 | 16563988 | chr10 | 16564013 | 16564127 |
| chr10 | 17270131 | 17270529 | chr10 | 17270889 | 17271255 | chr10 | 17271444 | 17271519 |
| chr10 | 17271521 | 17271728 | chr10 | 17271835 | 17272313 | chr10 | 17272527 | 17272706 |
| chr10 | 17429082 | 17429244 | chr10 | 17429562 | 17429724 | chr10 | 17496545 | 17496834 |
| chr10 | 18429147 | 18429149 | chr10 | 18429552 | 18429749 | chr10 | 18429751 | 18429851 |
| chr10 | 21462526 | 21462690 | chr10 | 21805128 | 21805367 | chr10 | 22047362 | 22047601 |
| chr10 | 22541563 | 22541851 | chr10 | 22542025 | 22542250 | chr10 | 22623924 | 22624306 |
| chr10 | 22624562 | 22625121 | chr10 | 22625383 | 22625783 | chr10 | 22625812 | 22626080 |
| chr10 | 22633902 | 22634175 | chr10 | 22634325 | 22634432 | chr10 | 22634434 | 22634439 |
| chr10 | 22634441 | 22634655 | chr10 | 22764556 | 22765590 | chr10 | 23216786 | 23216843 |
| chr10 | 23216845 | 23217025 | chr10 | 23460264 | 23460552 | chr10 | 23461129 | 23461848 |
| chr10 | 23461976 | 23462463 | chr10 | 23462486 | 23462615 | chr10 | 23462635 | 23462995 |
| chr10 | 23463267 | 23463854 | chr10 | 23463888 | 23464154 | chr10 | 23479793 | 23480697 |
| chr10 | 23480904 | 23481050 | chr10 | 23481304 | 23481385 | chr10 | 23481387 | 23481598 |
| chr10 | 23481862 | 23482233 | chr10 | 23482289 | 23482521 | chr10 | 23483744 | 23484703 |
| chr10 | 23486177 | 23486416 | chr10 | 23487651 | 23488070 | chr10 | 23488343 | 23489256 |
| chr10 | 23489335 | 23489514 | chr10 | 23982360 | 23982899 | chr10 | 23983102 | 23983341 |
| chr10 | 23983618 | 23983801 | chr10 | 23984008 | 23984307 | chr10 | 23984842 | 23985066 |
| chr10 | 24988575 | 24988641 | chr10 | 25464528 | 25464910 | chr10 | 25465320 | 25465350 |
| chr10 | 25465352 | 25465619 | chr10 | 26055737 | 26055916 | chr10 | 26222916 | 26223100 |
| chr10 | 26223102 | 26223206 | chr10 | 26223426 | 26223513 | chr10 | 26223957 | 26224136 |
| chr10 | 26500528 | 26500871 | chr10 | 26501445 | 26501668 | chr10 | 26503593 | 26503832 |
| chr10 | 26504018 | 26504144 | chr10 | 26504191 | 26504257 | chr10 | 26504410 | 26504884 |
| chr10 | 26505009 | 26505236 | chr10 | 26505442 | 26505503 | chr10 | 26505505 | 26505618 |
| chr10 | 26505714 | 26505783 | chr10 | 26505961 | 26506260 | chr10 | 26506288 | 26506353 |
| chr10 | 26506355 | 26506619 | chr10 | 26506903 | 26507427 | chr10 | 26681025 | 26681204 |
| chr10 | 26727024 | 26727443 | chr10 | 26727509 | 26727817 | chr10 | 26727868 | 26727928 |
| chr10 | 26746956 | 26747074 | chr10 | 26816913 | 26817032 | chr10 | 27547856 | 27548332 |
| chr10 | 27548401 | 27548575 | chr10 | 27794394 | 27794512 | chr10 | 27846608 | 27846719 |
| chr10 | 28030790 | 28031029 | chr10 | 28032874 | 28033113 | chr10 | 28033327 | 28033566 |
| chr10 | 28033667 | 28034091 | chr10 | 28034093 | 28034187 | chr10 | 28034327 | 28034446 |
| chr10 | 28034489 | 28034556 | chr10 | 28034874 | 28035388 | chr10 | 28035520 | 28035879 |
| chr10 | 28287286 | 28287318 | chr10 | 28287366 | 28287481 | chr10 | 28287693 | 28288164 |
| chr10 | 28957989 | 28957995 | chr10 | 28958044 | 28958226 | chr10 | 29010956 | 29011239 |
| chr10 | 30026077 | 30026180 | chr10 | 31073276 | 31073541 | chr10 | 31892822 | 31893181 |
| chr10 | 32499021 | 32499260 | chr10 | 33233249 | 33233457 | chr10 | 33624079 | 33624318 |
| chr10 | 33624407 | 33624550 | chr10 | 33624621 | 33624646 | chr10 | 35929334 | 35929609 |
| chr10 | 43249935 | 43250114 | chr10 | 43250317 | 43250780 | chr10 | 43250855 | 43250976 |
| chr10 | 43428329 | 43428577 | chr10 | 43428637 | 43428688 | chr10 | 43428903 | 43428977 |
| chr10 | 43429067 | 43429197 | chr10 | 43429275 | 43429514 | chr10 | 43572591 | 43572830 |
| chr10 | 43600551 | 43600733 | chr10 | 43615462 | 43615639 | chr10 | 43697812 | 43698087 |
| chr10 | 43698199 | 43698231 | chr10 | 43858258 | 43858437 | chr10 | 44879847 | 44880326 |
| chr10 | 44880773 | 44881012 | chr10 | 49652880 | 49653179 | chr10 | 49731470 | 49731829 |
| chr10 | 49731980 | 49732088 | chr10 | 49732156 | 49732315 | chr10 | 49732317 | 49732579 |
| chr10 | 50323162 | 50323360 | chr10 | 50340179 | 50340224 | chr10 | 50507469 | 50507708 |
| chr10 | 50603884 | 50604243 | chr10 | 50604508 | 50604747 | chr10 | 50604967 | 50604979 |
| chr10 | 50605053 | 50605746 | chr10 | 50605931 | 50606530 | chr10 | 50816972 | 50817224 |
| chr10 | 50817778 | 50817810 | chr10 | 50817812 | 50817873 | chr10 | 50818288 | 50818527 |
| chr10 | 50818987 | 50819203 | chr10 | 50821378 | 50821797 | chr10 | 50887557 | 50887616 |
| chr10 | 50887618 | 50887754 | chr10 | 50887790 | 50887916 | chr10 | 50977034 | 50977144 |
| chr10 | 54068449 | 54068688 | chr10 | 54072882 | 54073121 | chr10 | 54073191 | 54073370 |
| chr10 | 54074648 | 54074887 | chr10 | 57387344 | 57387883 | chr10 | 57388239 | 57388598 |
| chr10 | 57390195 | 57390734 | chr10 | 57391072 | 57391311 | chr10 | 60273033 | 60273279 |
| chr10 | 60273347 | 60273392 | chr10 | 60935793 | 60936091 | chr10 | 60936449 | 60936730 |
| chr10 | 60937042 | 60937178 | chr10 | 63212244 | 63212783 | chr10 | 64575433 | 64575732 |
| chr10 | 64578189 | 64578626 | chr10 | 71327627 | 71327865 | chr10 | 71328678 | 71328917 |
| chr10 | 71328980 | 71329002 | chr10 | 71329077 | 71329219 | chr10 | 71329462 | 71329633 |
| chr10 | 71331966 | 71332650 | chr10 | 71332686 | 71333105 | chr10 | 72015070 | 72015425 |
| chr10 | 72043779 | 72043976 | chr10 | 72200001 | 72200065 | chr10 | 72200118 | 72200240 |
| chr10 | 72200251 | 72200772 | chr10 | 72200825 | 72201390 | chr10 | 72973124 | 72973275 |
| chr10 | 73156347 | 73156465 | chr10 | 73156550 | 73156752 | chr10 | 73157768 | 73158049 |
| chr10 | 73847788 | 73847792 | chr10 | 73848209 | 73848762 | chr10 | 75407495 | 75407782 |
| chr10 | 75488860 | 75488975 | chr10 | 77191147 | 77191446 | chr10 | 79396826 | 79397185 |
| chr10 | 81023964 | 81023989 | chr10 | 81664764 | 81665003 | chr10 | 82116994 | 82117283 |
| chr10 | 83634171 | 83634234 | chr10 | 83635441 | 83635499 | chr10 | 83635531 | 83635620 |
| chr10 | 85954322 | 85954561 | chr10 | 88149273 | 88149692 | chr10 | 89692817 | 89692996 |
| chr10 | 89717584 | 89717763 | chr10 | 90966608 | 90966967 | chr10 | 90967587 | 90968126 |
| chr10 | 91294929 | 91295168 | chr10 | 91295449 | 91295492 | chr10 | 91295585 | 91295808 |
| chr10 | 92617156 | 92617395 | chr10 | 93647139 | 93647378 | chr10 | 93647486 | 93647648 |
| chr10 | 93647650 | 93647725 | chr10 | 94450582 | 94450806 | chr10 | 94451372 | 94451587 |
| chr10 | 94825999 | 94826160 | chr10 | 94828062 | 94828125 | chr10 | 94828194 | 94828601 |
| chr10 | 94828633 | 94828932 | chr10 | 94834311 | 94835088 | chr10 | 96304116 | 96304200 |
| chr10 | 98129719 | 98130138 | chr10 | 99080176 | 99080535 | chr10 | 99080774 | 99080931 |
| chr10 | 99080990 | 99081061 | chr10 | 99531116 | 99531535 | chr10 | 99789080 | 99789379 |
| chr10 | 99790171 | 99790340 | chr10 | 99790508 | 99790747 | chr10 | 99790918 | 99791258 |

TABLE 15-continued

| chr | start | end | chr | start | end | chr | start | end |
|---|---|---|---|---|---|---|---|---|
| chr10 | 100991863 | 100991935 | chr10 | 100992056 | 100992191 | chr10 | 100992222 | 100992535 |
| chr10 | 100992780 | 100992822 | chr10 | 100993448 | 100993938 | chr10 | 100993940 | 100994107 |
| chr10 | 100995956 | 100996315 | chr10 | 101088918 | 101089517 | chr10 | 101089817 | 101090296 |
| chr10 | 101280106 | 101280569 | chr10 | 101283382 | 101283577 | chr10 | 101290028 | 101290161 |
| chr10 | 101290180 | 101290699 | chr10 | 101290701 | 101291143 | chr10 | 101291231 | 101291284 |
| chr10 | 101292254 | 101292998 | chr10 | 101293071 | 101293430 | chr10 | 101294662 | 101295400 |
| chr10 | 101295402 | 101295681 | chr10 | 101296665 | 101296717 | chr10 | 101296738 | 101296892 |
| chr10 | 101874886 | 101875222 | chr10 | 102322156 | 102322335 | chr10 | 102419230 | 102419267 |
| chr10 | 102419400 | 102419769 | chr10 | 102430611 | 102430850 | chr10 | 102473775 | 102474014 |
| chr10 | 102483915 | 102484232 | chr10 | 102484234 | 102484246 | chr10 | 102484270 | 102484632 |
| chr10 | 102495416 | 102495717 | chr10 | 102497253 | 102497298 | chr10 | 102497300 | 102497791 |
| chr10 | 102498178 | 102498537 | chr10 | 102501285 | 102501464 | chr10 | 102507408 | 102507536 |
| chr10 | 102508902 | 102509381 | chr10 | 102589340 | 102589579 | chr10 | 102589702 | 102590001 |
| chr10 | 102590075 | 102590494 | chr10 | 102890843 | 102891019 | chr10 | 102891021 | 102891682 |
| chr10 | 102891745 | 102891956 | chr10 | 102892091 | 102892104 | chr10 | 102893528 | 102893952 |
| chr10 | 102894091 | 102895366 | chr10 | 102899088 | 102899687 | chr10 | 102899712 | 102899856 |
| chr10 | 102900263 | 102900671 | chr10 | 102906423 | 102906470 | chr10 | 102906525 | 102906667 |
| chr10 | 102975518 | 102975937 | chr10 | 102976963 | 102977502 | chr10 | 102983088 | 102983380 |
| chr10 | 102983435 | 102983841 | chr10 | 102984313 | 102984371 | chr10 | 102984513 | 102984612 |
| chr10 | 102985689 | 102986048 | chr10 | 102986447 | 102986953 | chr10 | 102987207 | 102987646 |
| chr10 | 102989555 | 102989734 | chr10 | 102996018 | 102996481 | chr10 | 102996597 | 102996737 |
| chr10 | 102997282 | 102997488 | chr10 | 102998493 | 102998912 | chr10 | 103043925 | 103044228 |
| chr10 | 103044301 | 103044471 | chr10 | 103535527 | 103535586 | chr10 | 103535634 | 103535771 |
| chr10 | 103535842 | 103535886 | chr10 | 103536143 | 103536257 | chr10 | 103536300 | 103536502 |
| chr10 | 103579718 | 103579794 | chr10 | 103930133 | 103930248 | chr10 | 104169995 | 104170263 |
| chr10 | 104170408 | 104170513 | chr10 | 104170515 | 104170801 | chr10 | 105036464 | 105036659 |
| chr10 | 105036701 | 105036863 | chr10 | 105036865 | 105036883 | chr10 | 105036894 | 105036943 |
| chr10 | 105037138 | 105037892 | chr10 | 105127048 | 105127156 | chr10 | 105155378 | 105155563 |
| chr10 | 105413527 | 105413886 | chr10 | 106398556 | 106398688 | chr10 | 106398826 | 106398975 |
| chr10 | 106399505 | 106400464 | chr10 | 106400869 | 106400918 | chr10 | 106401323 | 106401433 |
| chr10 | 106401511 | 106402191 | chr10 | 106402272 | 106402428 | chr10 | 106402620 | 106402919 |
| chr10 | 108923951 | 108924060 | chr10 | 108924365 | 108924366 | chr10 | 108924368 | 108924401 |
| chr10 | 108924770 | 108924784 | chr10 | 110226162 | 110226169 | chr10 | 110671800 | 110671884 |
| chr10 | 110671930 | 110672339 | chr10 | 111216709 | 111216804 | chr10 | 112403075 | 112403374 |
| chr10 | 112440312 | 112440483 | chr10 | 115804748 | 115805107 | chr10 | 116164146 | 116164445 |
| chr10 | 116331052 | 116331231 | chr10 | 116853773 | 116854012 | chr10 | 118030550 | 118030706 |
| chr10 | 118031206 | 118031549 | chr10 | 118031625 | 118031864 | chr10 | 118031866 | 118032230 |
| chr10 | 118032413 | 118032645 | chr10 | 118032841 | 118033140 | chr10 | 118033261 | 118033620 |
| chr10 | 118034143 | 118034243 | chr10 | 118890893 | 118891134 | chr10 | 118891180 | 118891192 |
| chr10 | 118891437 | 118891662 | chr10 | 118891716 | 118891854 | chr10 | 118891938 | 118892457 |
| chr10 | 118892518 | 118893360 | chr10 | 118893484 | 118893581 | chr10 | 118893680 | 118893826 |
| chr10 | 118894035 | 118894072 | chr10 | 118896538 | 118896897 | chr10 | 118897822 | 118897847 |
| chr10 | 118897849 | 118898061 | chr10 | 118899199 | 118899378 | chr10 | 118899583 | 118899603 |
| chr10 | 118899893 | 118900034 | chr10 | 118900063 | 118900245 | chr10 | 118900324 | 118900602 |
| chr10 | 118922061 | 118922296 | chr10 | 118922632 | 118922900 | chr10 | 118922944 | 118922991 |
| chr10 | 118923050 | 118923349 | chr10 | 118924511 | 118924990 | chr10 | 118927012 | 118927371 |
| chr10 | 118928459 | 118928614 | chr10 | 119000564 | 119000592 | chr10 | 119000690 | 119001155 |
| chr10 | 119001329 | 119001403 | chr10 | 119001460 | 119001639 | chr10 | 119292324 | 119292419 |
| chr10 | 119294258 | 119294557 | chr10 | 119294747 | 119294898 | chr10 | 119294909 | 119295346 |
| chr10 | 119296628 | 119296644 | chr10 | 119296756 | 119296867 | chr10 | 119297308 | 119297607 |
| chr10 | 119301278 | 119301428 | chr10 | 119302055 | 119302080 | chr10 | 119302859 | 119303278 |
| chr10 | 119304289 | 119304468 | chr10 | 119304794 | 119304829 | chr10 | 119304851 | 119304986 |
| chr10 | 119305062 | 119305213 | chr10 | 119306948 | 119307127 | chr10 | 119311793 | 119311830 |
| chr10 | 119311905 | 119311972 | chr10 | 119312673 | 119313272 | chr10 | 119806952 | 119807131 |
| chr10 | 120354169 | 120354330 | chr10 | 120355462 | 120355701 | chr10 | 120841455 | 120841563 |
| chr10 | 122216811 | 122217170 | chr10 | 122708479 | 122708572 | chr10 | 123357681 | 123357757 |
| chr10 | 123922546 | 123922683 | chr10 | 123923518 | 123923565 | chr10 | 124893085 | 124893193 |
| chr10 | 124893238 | 124893444 | chr10 | 124893551 | 124893850 | chr10 | 124893863 | 124894582 |
| chr10 | 124894871 | 124895026 | chr10 | 124895342 | 124895696 | chr10 | 124895833 | 124896533 |
| chr10 | 124896938 | 124897007 | chr10 | 124897118 | 124897657 | chr10 | 124897958 | 124898056 |
| chr10 | 124898957 | 124899196 | chr10 | 124899651 | 124899890 | chr10 | 124901816 | 124902047 |
| chr10 | 124902139 | 124902569 | chr10 | 124902608 | 124903315 | chr10 | 124904841 | 124905200 |
| chr10 | 124905407 | 124905586 | chr10 | 124905834 | 124905880 | chr10 | 124905920 | 124906186 |
| chr10 | 124907214 | 124907633 | chr10 | 124908017 | 124908196 | chr10 | 124908987 | 124909115 |
| chr10 | 124909253 | 124909538 | chr10 | 124909674 | 124909769 | chr10 | 124910287 | 124910455 |
| chr10 | 124910709 | 124911126 | chr10 | 125425412 | 125425612 | chr10 | 125650778 | 125651163 |
| chr10 | 125651373 | 125651437 | chr10 | 125851248 | 125851727 | chr10 | 125852203 | 125852498 |
| chr10 | 125852541 | 125852622 | chr10 | 125852673 | 125853272 | chr10 | 126135878 | 126136146 |
| chr10 | 126136406 | 126136810 | chr10 | 126137145 | 126137503 | chr10 | 126198864 | 126199163 |
| chr10 | 126697829 | 126698125 | chr10 | 128076477 | 128076716 | chr10 | 128077188 | 128077241 |
| chr10 | 128993816 | 128994529 | chr10 | 128994636 | 128994995 | chr10 | 129534562 | 129534586 |
| chr10 | 129534993 | 129535447 | chr10 | 129535696 | 129535825 | chr10 | 129535986 | 129536224 |
| chr10 | 129536259 | 129536405 | chr10 | 129888774 | 129888965 | chr10 | 129948037 | 129948216 |
| chr10 | 130085210 | 130085276 | chr10 | 130085356 | 130085449 | chr10 | 130203339 | 130203578 |
| chr10 | 130338713 | 130338769 | chr10 | 130338804 | 130339062 | chr10 | 130577690 | 130577869 |
| chr10 | 131647829 | 131648008 | chr10 | 131756992 | 131757051 | chr10 | 131757852 | 131757853 |
| chr10 | 131761291 | 131761530 | chr10 | 131761587 | 131761826 | chr10 | 131761987 | 131762226 |
| chr10 | 131762493 | 131762732 | chr10 | 131762803 | 131763042 | chr10 | 131763264 | 131763337 |

TABLE 15-continued

| chr | start | end | chr | start | end | chr | start | end |
|---|---|---|---|---|---|---|---|---|
| chr10 | 131763633 | 131763803 | chr10 | 131767343 | 131767504 | chr10 | 131768638 | 131768928 |
| chr10 | 131768930 | 131769117 | chr10 | 131769436 | 131770335 | chr10 | 131770583 | 131770762 |
| chr10 | 131770908 | 131771094 | chr10 | 131771282 | 131771302 | chr10 | 131936600 | 131936719 |
| chr10 | 131937393 | 131937512 | chr10 | 132001196 | 132001615 | chr10 | 133109096 | 133109261 |
| chr10 | 133110554 | 133110799 | chr10 | 133794798 | 133795242 | chr10 | 133795313 | 133795517 |
| chr10 | 133795593 | 133795884 | chr10 | 133795976 | 133796059 | chr10 | 133796302 | 133796312 |
| chr10 | 133849561 | 133850103 | chr10 | 133850443 | 133850862 | chr10 | 133951515 | 133952107 |
| chr10 | 133979076 | 133979164 | chr10 | 133999917 | 134000053 | chr10 | 134000109 | 134000124 |
| chr10 | 134000126 | 134000216 | chr10 | 134001140 | 134001359 | chr10 | 134016117 | 134016476 |
| chr10 | 134022771 | 134022950 | chr10 | 134095505 | 134095924 | chr10 | 134272961 | 134272970 |
| chr10 | 134301005 | 134301304 | chr10 | 134481228 | 134481527 | chr10 | 134598013 | 134598091 |
| chr10 | 134598368 | 134598534 | chr10 | 134598973 | 134599022 | chr10 | 134599432 | 134599546 |
| chr10 | 134599714 | 134600017 | chr10 | 134600038 | 134601053 | chr10 | 134601468 | 134601716 |
| chr10 | 134602128 | 134602346 | chr10 | 134607868 | 134608284 | chr10 | 134665056 | 134665295 |
| chr10 | 134679326 | 134679347 | chr10 | 134690469 | 134690636 | chr10 | 134693499 | 134693798 |
| chr10 | 134699772 | 134700011 | chr10 | 134733129 | 134733368 | chr10 | 134733408 | 134733707 |
| chr10 | 134738301 | 134738720 | chr10 | 134755773 | 134756270 | chr10 | 134787988 | 134788194 |
| chr10 | 134795938 | 134796117 | chr10 | 134901113 | 134901294 | chr10 | 134901296 | 134901592 |
| chr10 | 134901919 | 134902125 | chr10 | 134902188 | 134902352 | chr10 | 134916625 | 134916864 |
| chr10 | 134941043 | 134941282 | chr10 | 134942738 | 134943216 | chr10 | 134943461 | 134943644 |
| chr10 | 134944668 | 134944847 | chr10 | 135001961 | 135002260 | chr10 | 135014869 | 135015228 |
| chr10 | 135016972 | 135017209 | chr10 | 135017932 | 135018148 | chr10 | 135018744 | 135019043 |
| chr10 | 135020698 | 135020988 | chr10 | 135023396 | 135023575 | chr10 | 135043080 | 135043613 |
| chr10 | 135043869 | 135044228 | chr10 | 135044555 | 135044662 | chr10 | 135048742 | 135049041 |
| chr10 | 135050226 | 135050355 | chr10 | 135050357 | 135050765 | chr10 | 135076308 | 135076586 |
| chr10 | 135121730 | 135122131 | chr10 | 135139464 | 135139805 | chr11 | 232816 | 233115 |
| chr11 | 392560 | 392739 | chr11 | 394713 | 395072 | chr11 | 406789 | 407028 |
| chr11 | 407326 | 407565 | chr11 | 636821 | 636907 | chr11 | 637162 | 637264 |
| chr11 | 637350 | 637528 | chr11 | 726323 | 726562 | chr11 | 763236 | 763775 |
| chr11 | 829453 | 829533 | chr11 | 850480 | 850899 | chr11 | 862988 | 863167 |
| chr11 | 1027438 | 1027676 | chr11 | 1029142 | 1029501 | chr11 | 1030137 | 1030376 |
| chr11 | 1080304 | 1080416 | chr11 | 1081572 | 1081811 | chr11 | 1214582 | 1215001 |
| chr11 | 1215800 | 1216099 | chr11 | 1229871 | 1230050 | chr11 | 1244304 | 1244543 |
| chr11 | 1250788 | 1251027 | chr11 | 1251088 | 1251447 | chr11 | 1263504 | 1263743 |
| chr11 | 1273988 | 1274287 | chr11 | 1358284 | 1358387 | chr11 | 1374862 | 1375101 |
| chr11 | 1411842 | 1411980 | chr11 | 1430635 | 1430789 | chr11 | 1464205 | 1464504 |
| chr11 | 1469125 | 1469484 | chr11 | 1471840 | 1472139 | chr11 | 1770263 | 1770330 |
| chr11 | 1867980 | 1868339 | chr11 | 1946056 | 1946235 | chr11 | 1957312 | 1957611 |
| chr11 | 1958983 | 1959282 | chr11 | 2040009 | 2040248 | chr11 | 2209824 | 2210363 |
| chr11 | 2225974 | 2226153 | chr11 | 2278625 | 2278924 | chr11 | 2291185 | 2291494 |
| chr11 | 2291801 | 2291844 | chr11 | 2291891 | 2291925 | chr11 | 2291945 | 2292058 |
| chr11 | 2292106 | 2292360 | chr11 | 2292392 | 2292730 | chr11 | 2437889 | 2438246 |
| chr11 | 2465323 | 2465448 | chr11 | 2465462 | 2465571 | chr11 | 2466514 | 2466873 |
| chr11 | 2884027 | 2884121 | chr11 | 2884159 | 2884386 | chr11 | 3169689 | 3169930 |
| chr11 | 4209031 | 4209210 | chr11 | 7273212 | 7273260 | chr11 | 7274141 | 7274320 |
| chr11 | 8040444 | 8040551 | chr11 | 8040553 | 8040564 | chr11 | 8040582 | 8040776 |
| chr11 | 8102910 | 8103209 | chr11 | 8189898 | 8190857 | chr11 | 8284466 | 8284858 |
| chr11 | 8289436 | 8289841 | chr11 | 8290100 | 8290515 | chr11 | 8615600 | 8615779 |
| chr11 | 9025890 | 9026429 | chr11 | 9112372 | 9112586 | chr11 | 9112640 | 9112834 |
| chr11 | 9405310 | 9405542 | chr11 | 10509594 | 10509893 | chr11 | 10811069 | 10811188 |
| chr11 | 10815784 | 10815896 | chr11 | 12029876 | 12030272 | chr11 | 12030274 | 12030355 |
| chr11 | 12030749 | 12030928 | chr11 | 12132423 | 12132662 | chr11 | 12398952 | 12399145 |
| chr11 | 12399181 | 12399311 | chr11 | 12695397 | 12695496 | chr11 | 12695573 | 12695696 |
| chr11 | 12696530 | 12696764 | chr11 | 13030489 | 13030792 | chr11 | 13030862 | 13030919 |
| chr11 | 15136001 | 15136456 | chr11 | 15136458 | 15136480 | chr11 | 16628727 | 16628998 |
| chr11 | 16632403 | 16632428 | chr11 | 16632514 | 16632752 | chr11 | 17497410 | 17497521 |
| chr11 | 17497546 | 17497769 | chr11 | 17740413 | 17740652 | chr11 | 17741583 | 17741685 |
| chr11 | 17741718 | 17741890 | chr11 | 17741953 | 17742484 | chr11 | 17742519 | 17742542 |
| chr11 | 17743640 | 17743874 | chr11 | 18812515 | 18812754 | chr11 | 18812940 | 18813179 |
| chr11 | 18813356 | 18813543 | chr11 | 18813610 | 18813655 | chr11 | 18813691 | 18814050 |
| chr11 | 19263774 | 19263953 | chr11 | 19367007 | 19367135 | chr11 | 19367268 | 19367426 |
| chr11 | 19735656 | 19735835 | chr11 | 20153622 | 20153861 | chr11 | 20178094 | 20178396 |
| chr11 | 20180244 | 20180896 | chr11 | 20181115 | 20181354 | chr11 | 20181608 | 20181644 |
| chr11 | 20181725 | 20182087 | chr11 | 20182763 | 20183062 | chr11 | 20183157 | 20183211 |
| chr11 | 20183313 | 20183516 | chr11 | 20183575 | 20183852 | chr11 | 20184481 | 20185500 |
| chr11 | 20229275 | 20229634 | chr11 | 20229811 | 20230110 | chr11 | 20230312 | 20230551 |
| chr11 | 20618116 | 20618393 | chr11 | 20618423 | 20618925 | chr11 | 20619220 | 20619255 |
| chr11 | 20619637 | 20620056 | chr11 | 20621460 | 20621733 | chr11 | 20622613 | 20622793 |
| chr11 | 20623259 | 20623452 | chr11 | 20690555 | 20690878 | chr11 | 20690983 | 20691034 |
| chr11 | 20691127 | 20691161 | chr11 | 20691163 | 20691380 | chr11 | 20691432 | 20691546 |
| chr11 | 20691591 | 20691616 | chr11 | 20691748 | 20692010 | chr11 | 20692372 | 20692611 |
| chr11 | 22215026 | 22215385 | chr11 | 22362853 | 22363272 | chr11 | 22364719 | 22365078 |
| chr11 | 22365323 | 22365562 | chr11 | 27742111 | 27742290 | chr11 | 27743025 | 27743261 |
| chr11 | 27743343 | 27743702 | chr11 | 27744057 | 27744557 | chr11 | 27744559 | 27744596 |
| chr11 | 27744609 | 27744832 | chr11 | 30037596 | 30037752 | chr11 | 30038595 | 30038834 |
| chr11 | 30605946 | 30606026 | chr11 | 30606028 | 30606161 | chr11 | 30606665 | 30606755 |
| chr11 | 30606796 | 30606964 | chr11 | 30607269 | 30607508 | chr11 | 31818376 | 31818513 |
| chr11 | 31818571 | 31818674 | chr11 | 31819221 | 31819508 | chr11 | 31819569 | 31819928 |

TABLE 15-continued

| chr | start | end | chr | start | end | chr | start | end |
|---|---|---|---|---|---|---|---|---|
| chr11 | 31819966 | 31820361 | chr11 | 31820461 | 31821105 | chr11 | 31821209 | 31821388 |
| chr11 | 31821390 | 31821860 | chr11 | 31822240 | 31822479 | chr11 | 31824209 | 31824448 |
| chr11 | 31824473 | 31824772 | chr11 | 31824940 | 31824964 | chr11 | 31826043 | 31826071 |
| chr11 | 31826107 | 31826304 | chr11 | 31826409 | 31826733 | chr11 | 31827114 | 31827290 |
| chr11 | 31827362 | 31827520 | chr11 | 31827598 | 31828142 | chr11 | 31833007 | 31833232 |
| chr11 | 31835633 | 31835872 | chr11 | 31835959 | 31836517 | chr11 | 31837355 | 31837513 |
| chr11 | 31837542 | 31838486 | chr11 | 31838596 | 31839135 | chr11 | 31839215 | 31839946 |
| chr11 | 31840042 | 31840174 | chr11 | 31840879 | 31841025 | chr11 | 31841775 | 31842089 |
| chr11 | 31842175 | 31842366 | chr11 | 31845947 | 31845991 | chr11 | 31846078 | 31846306 |
| chr11 | 31846351 | 31847070 | chr11 | 31847169 | 31847302 | chr11 | 31847371 | 31847713 |
| chr11 | 31847770 | 31847873 | chr11 | 31847896 | 31848008 | chr11 | 31848377 | 31848603 |
| chr11 | 31848723 | 31849177 | chr11 | 32009013 | 32009127 | chr11 | 32354816 | 32354960 |
| chr11 | 32355000 | 32355291 | chr11 | 32448482 | 32448894 | chr11 | 32455499 | 32455738 |
| chr11 | 32455754 | 32456113 | chr11 | 32456189 | 32456446 | chr11 | 32456759 | 32456912 |
| chr11 | 32456914 | 32457199 | chr11 | 32457220 | 32457268 | chr11 | 32457615 | 32458274 |
| chr11 | 32458307 | 32458860 | chr11 | 32459609 | 32459971 | chr11 | 32460118 | 32460148 |
| chr11 | 32460465 | 32460586 | chr11 | 32460711 | 32460908 | chr11 | 33037393 | 33037632 |
| chr11 | 33858439 | 33858544 | chr11 | 33890197 | 33890436 | chr11 | 33993910 | 33993979 |
| chr11 | 34535019 | 34535198 | chr11 | 35547412 | 35547651 | chr11 | 35641582 | 35641718 |
| chr11 | 35684866 | 35685225 | chr11 | 43596412 | 43596693 | chr11 | 43600416 | 43600655 |
| chr11 | 43601012 | 43601551 | chr11 | 43602369 | 43602847 | chr11 | 43602849 | 43603037 |
| chr11 | 43603077 | 43603328 | chr11 | 43603544 | 43604146 | chr11 | 43604241 | 43604263 |
| chr11 | 44325599 | 44325770 | chr11 | 44326042 | 44326281 | chr11 | 44326341 | 44326350 |
| chr11 | 44326516 | 44326580 | chr11 | 44330555 | 44330609 | chr11 | 44330878 | 44330958 |
| chr11 | 44330960 | 44331440 | chr11 | 44331483 | 44331814 | chr11 | 44332978 | 44333157 |
| chr11 | 44333477 | 44333576 | chr11 | 44337564 | 44337629 | chr11 | 44337727 | 44337862 |
| chr11 | 44337883 | 44338058 | chr11 | 44338087 | 44338154 | chr11 | 44338232 | 44338471 |
| chr11 | 44340722 | 44340808 | chr11 | 44341881 | 44342120 | chr11 | 46316761 | 46316833 |
| chr11 | 46316896 | 46317356 | chr11 | 46317408 | 46317780 | chr11 | 47208968 | 47209267 |
| chr11 | 47358895 | 47359314 | chr11 | 57194253 | 57194612 | chr11 | 57235332 | 57235511 |
| chr11 | 57437215 | 57437316 | chr11 | 57501032 | 57501145 | chr11 | 58672666 | 58673145 |
| chr11 | 59323514 | 59323551 | chr11 | 59323780 | 59323813 | chr11 | 59329224 | 59329343 |
| chr11 | 59333344 | 59333623 | chr11 | 60718587 | 60718854 | chr11 | 60718977 | 60719246 |
| chr11 | 61049596 | 61049756 | chr11 | 61058193 | 61058432 | chr11 | 61062741 | 61063024 |
| chr11 | 61063062 | 61063220 | chr11 | 61276902 | 61277120 | chr11 | 61594995 | 61595354 |
| chr11 | 61596321 | 61596740 | chr11 | 61664564 | 61664863 | chr11 | 61666032 | 61666211 |
| chr11 | 61722964 | 61722987 | chr11 | 62370646 | 62370825 | chr11 | 62440550 | 62440669 |
| chr11 | 63609981 | 63610099 | chr11 | 63641023 | 63641104 | chr11 | 63849298 | 63849530 |
| chr11 | 63934600 | 63934709 | chr11 | 64105852 | 64106031 | chr11 | 64120805 | 64120984 |
| chr11 | 64140323 | 64140502 | chr11 | 64410622 | 64410861 | chr11 | 64480380 | 64480691 |
| chr11 | 64480724 | 64481143 | chr11 | 64578481 | 64578600 | chr11 | 64739369 | 64739608 |
| chr11 | 64809866 | 64809965 | chr11 | 64950214 | 64950438 | chr11 | 65091311 | 65091471 |
| chr11 | 65185459 | 65185818 | chr11 | 65405568 | 65405597 | chr11 | 65478529 | 65478644 |
| chr11 | 65511077 | 65511256 | chr11 | 65511332 | 65511571 | chr11 | 65554043 | 65554195 |
| chr11 | 65600716 | 65600846 | chr11 | 65600848 | 65601735 | chr11 | 65779218 | 65779457 |
| chr11 | 65816357 | 65816520 | chr11 | 65816561 | 65816656 | chr11 | 66188041 | 66188220 |
| chr11 | 66188395 | 66188485 | chr11 | 66188571 | 66188784 | chr11 | 66188853 | 66189054 |
| chr11 | 66454350 | 66454529 | chr11 | 66511148 | 66511327 | chr11 | 66513133 | 66513252 |
| chr11 | 66513554 | 66513732 | chr11 | 66625105 | 66625344 | chr11 | 66648954 | 66649133 |
| chr11 | 66658258 | 66658365 | chr11 | 66790519 | 66790758 | chr11 | 67072139 | 67072489 |
| chr11 | 67209918 | 67210157 | chr11 | 67350887 | 67350961 | chr11 | 67350991 | 67351066 |
| chr11 | 67462559 | 67462918 | chr11 | 67764102 | 67764341 | chr11 | 67781387 | 67781650 |
| chr11 | 67797102 | 67797281 | chr11 | 68096026 | 68096257 | chr11 | 68409507 | 68409663 |
| chr11 | 68804647 | 68804872 | chr11 | 69192466 | 69192885 | chr11 | 69280478 | 69280717 |
| chr11 | 69465962 | 69466143 | chr11 | 69516896 | 69517251 | chr11 | 69517942 | 69518197 |
| chr11 | 69518199 | 69518301 | chr11 | 69518445 | 69518708 | chr11 | 69588848 | 69589267 |
| chr11 | 69589750 | 69589929 | chr11 | 69590067 | 69590113 | chr11 | 69590115 | 69590306 |
| chr11 | 71192669 | 71192921 | chr11 | 71318231 | 71318810 | chr11 | 71318953 | 71319070 |
| chr11 | 71951540 | 71951815 | chr11 | 71952262 | 71952417 | chr11 | 71952459 | 71952621 |
| chr11 | 71954538 | 71954717 | chr11 | 71955242 | 71955481 | chr11 | 71955905 | 71956444 |
| chr11 | 72432759 | 72432997 | chr11 | 72475581 | 72475814 | chr11 | 72532274 | 72532453 |
| chr11 | 72929666 | 72929731 | chr11 | 73072871 | 73073050 | chr11 | 73310285 | 73310445 |
| chr11 | 74394397 | 74394696 | chr11 | 74953165 | 74953337 | chr11 | 74953490 | 74953524 |
| chr11 | 75379155 | 75379249 | chr11 | 75379283 | 75379994 | chr11 | 75459452 | 75459564 |
| chr11 | 76371639 | 76372178 | chr11 | 78672822 | 78673061 | chr11 | 79151076 | 79151315 |
| chr11 | 82444290 | 82445189 | chr11 | 86085657 | 86085862 | chr11 | 86085932 | 86086065 |
| chr11 | 86383080 | 86383186 | chr11 | 88241623 | 88241976 | chr11 | 88242131 | 88242275 |
| chr11 | 88242359 | 88242624 | chr11 | 88798997 | 88799296 | chr11 | 91957408 | 91957767 |
| chr11 | 91957893 | 91957989 | chr11 | 91957991 | 91958312 | chr11 | 91958633 | 91959327 |
| chr11 | 91959355 | 91959532 | chr11 | 91959901 | 91960122 | chr11 | 93063495 | 93063734 |
| chr11 | 93063790 | 93064029 | chr11 | 94133991 | 94134464 | chr11 | 94134683 | 94134950 |
| chr11 | 94275701 | 94275813 | chr11 | 94473511 | 94473671 | chr11 | 94473673 | 94473769 |
| chr11 | 94473803 | 94473997 | chr11 | 94474249 | 94474401 | chr11 | 94502273 | 94502552 |
| chr11 | 94884070 | 94884235 | chr11 | 98891381 | 98891980 | chr11 | 100997579 | 100998085 |
| chr11 | 100998178 | 100998417 | chr11 | 100998588 | 100998745 | chr11 | 101453080 | 101453538 |
| chr11 | 101454511 | 101454580 | chr11 | 102961259 | 102961378 | chr11 | 102979953 | 102980132 |
| chr11 | 104034430 | 104034754 | chr11 | 104034756 | 104035089 | chr11 | 105480662 | 105480787 |
| chr11 | 105480859 | 105480901 | chr11 | 105481125 | 105481317 | chr11 | 105481319 | 105481319 |

TABLE 15-continued

| chr | start | end | chr | start | end | chr | start | end |
|---|---|---|---|---|---|---|---|---|
| chr11 | 105481321 | 105481322 | chr11 | 105481324 | 105481604 | chr11 | 106888220 | 106888519 |
| chr11 | 106888542 | 106888901 | chr11 | 107461549 | 107461728 | chr11 | 107462318 | 107462557 |
| chr11 | 108603286 | 108603338 | chr11 | 109292830 | 109292830 | chr11 | 109292892 | 109293129 |
| chr11 | 109293635 | 109293764 | chr11 | 109293874 | 109293934 | chr11 | 110582154 | 110582420 |
| chr11 | 110582422 | 110582513 | chr11 | 110582794 | 110583029 | chr11 | 110583044 | 110583153 |
| chr11 | 110583473 | 110583832 | chr11 | 111383104 | 111383515 | chr11 | 111383517 | 111383523 |
| chr11 | 111383558 | 111383763 | chr11 | 111411019 | 111411199 | chr11 | 111411201 | 111411582 |
| chr11 | 111411822 | 111412147 | chr11 | 114112948 | 114113127 | chr11 | 115375030 | 115375269 |
| chr11 | 115530040 | 115530096 | chr11 | 115530222 | 115530590 | chr11 | 115530592 | 115530662 |
| chr11 | 115630414 | 115630474 | chr11 | 115630531 | 115630629 | chr11 | 115630631 | 115630889 |
| chr11 | 115630891 | 115631013 | chr11 | 115631217 | 115631456 | chr11 | 116451226 | 116451287 |
| chr11 | 119292705 | 119292884 | chr11 | 119293284 | 119293320 | chr11 | 119293353 | 119293385 |
| chr11 | 119293387 | 119293703 | chr11 | 119612134 | 119612268 | chr11 | 119612324 | 119612493 |
| chr11 | 119612999 | 119613178 | chr11 | 120008006 | 120008605 | chr11 | 120039730 | 120039969 |
| chr11 | 120435322 | 120435561 | chr11 | 120435726 | 120435905 | chr11 | 120998614 | 120998913 |
| chr11 | 122847182 | 122847781 | chr11 | 122847976 | 122848313 | chr11 | 122848369 | 122848695 |
| chr11 | 122849808 | 122850124 | chr11 | 122850149 | 122850263 | chr11 | 122850331 | 122850630 |
| chr11 | 122851074 | 122851313 | chr11 | 122852338 | 122852577 | chr11 | 122854907 | 122855029 |
| chr11 | 122855031 | 122855136 | chr11 | 123066359 | 123066538 | chr11 | 123228971 | 123229180 |
| chr11 | 123229182 | 123229407 | chr11 | 123229462 | 123229510 | chr11 | 123300736 | 123300955 |
| chr11 | 123301016 | 123301029 | chr11 | 123301083 | 123302115 | chr11 | 124735341 | 124735352 |
| chr11 | 124735375 | 124735580 | chr11 | 124736105 | 124736344 | chr11 | 124738694 | 124739125 |
| chr11 | 124739149 | 124739173 | chr11 | 125035687 | 125036286 | chr11 | 125036721 | 125036742 |
| chr11 | 125220423 | 125220722 | chr11 | 125755512 | 125755727 | chr11 | 125773587 | 125774061 |
| chr11 | 125774123 | 125774186 | chr11 | 126870108 | 126870287 | chr11 | 126870379 | 126870429 |
| chr11 | 126870431 | 126870501 | chr11 | 126870525 | 126870618 | chr11 | 126873304 | 126873603 |
| chr11 | 128562802 | 128563186 | chr11 | 128563337 | 128563818 | chr11 | 128563879 | 128564405 |
| chr11 | 128564641 | 128564874 | chr11 | 128564876 | 128564877 | chr11 | 128564992 | 128565480 |
| chr11 | 128657933 | 128658051 | chr11 | 129242783 | 129243242 | chr11 | 129243305 | 129243643 |
| chr11 | 129243944 | 129244301 | chr11 | 129244441 | 129244646 | chr11 | 129245747 | 129245892 |
| chr11 | 129245981 | 129246046 | chr11 | 130318860 | 130319099 | chr11 | 130319451 | 130319690 |
| chr11 | 130785406 | 130785705 | chr11 | 131522676 | 131522960 | chr11 | 131564873 | 131565101 |
| chr11 | 131766899 | 131767048 | chr11 | 131780877 | 131781079 | chr11 | 131781294 | 131781350 |
| chr11 | 132484279 | 132484490 | chr11 | 132813545 | 132813758 | chr11 | 132813908 | 132814049 |
| chr11 | 132864036 | 132864275 | chr11 | 132934031 | 132934139 | chr11 | 132934141 | 132934270 |
| chr11 | 132952677 | 132953003 | chr11 | 132953233 | 132953423 | chr11 | 133231637 | 133231930 |
| chr11 | 133402114 | 133402353 | chr11 | 133825146 | 133825519 | chr11 | 133825521 | 133825625 |
| chr11 | 133906702 | 133907001 | chr11 | 133938911 | 133939064 | chr11 | 133939066 | 133939270 |
| chr11 | 134145629 | 134146427 | chr11 | 134146445 | 134146468 | chr11 | 134146579 | 134146676 |
| chr11 | 134146678 | 134146998 | chr11 | 134201404 | 134201640 | chr11 | 134201754 | 134202173 |
| chr11 | 134281288 | 134281543 | chr12 | 570012 | 570251 | chr12 | 1639060 | 1639299 |
| chr12 | 2162477 | 2162896 | chr12 | 2163071 | 2163370 | chr12 | 2403649 | 2403806 |
| chr12 | 2565971 | 2566330 | chr12 | 2861968 | 2862143 | chr12 | 2862268 | 2862327 |
| chr12 | 2964372 | 2964671 | chr12 | 3600241 | 3600420 | chr12 | 3602186 | 3602717 |
| chr12 | 3602865 | 3602965 | chr12 | 3603009 | 3603061 | chr12 | 4214010 | 4214245 |
| chr12 | 4274002 | 4274420 | chr12 | 4274475 | 4274490 | chr12 | 4362362 | 4362541 |
| chr12 | 4378172 | 4378411 | chr12 | 4379275 | 4379574 | chr12 | 4381341 | 4382480 |
| chr12 | 4382863 | 4383102 | chr12 | 4383399 | 4383878 | chr12 | 4384315 | 4384494 |
| chr12 | 4392801 | 4393023 | chr12 | 4405515 | 4405694 | chr12 | 4554727 | 4554906 |
| chr12 | 5017994 | 5018773 | chr12 | 5018954 | 5019035 | chr12 | 5019085 | 5019743 |
| chr12 | 5019794 | 5020314 | chr12 | 5020441 | 5020513 | chr12 | 5152951 | 5153287 |
| chr12 | 5153358 | 5153461 | chr12 | 5541020 | 5541259 | chr12 | 5542233 | 5542532 |
| chr12 | 5542656 | 5543015 | chr12 | 5840126 | 5840305 | chr12 | 6483537 | 6483836 |
| chr12 | 6664407 | 6664523 | chr12 | 7559085 | 7559384 | chr12 | 8127119 | 8127238 |
| chr12 | 8171284 | 8171823 | chr12 | 8808505 | 8808640 | chr12 | 8850582 | 8850818 |
| chr12 | 8975096 | 8975452 | chr12 | 10085826 | 10085932 | chr12 | 10363204 | 10363319 |
| chr12 | 11653375 | 11653464 | chr12 | 11653510 | 11653554 | chr12 | 12848294 | 12848653 |
| chr12 | 14133059 | 14133358 | chr12 | 14133541 | 14133960 | chr12 | 14135016 | 14135354 |
| chr12 | 15374156 | 15374395 | chr12 | 16500480 | 16500685 | chr12 | 20521624 | 20521923 |
| chr12 | 20522383 | 20522562 | chr12 | 20522681 | 20522860 | chr12 | 20522976 | 20522980 |
| chr12 | 21680300 | 21680779 | chr12 | 21810395 | 21810956 | chr12 | 21832988 | 21833095 |
| chr12 | 22093749 | 22093960 | chr12 | 22093962 | 22094269 | chr12 | 22094578 | 22094888 |
| chr12 | 22094997 | 22095048 | chr12 | 22095182 | 22095236 | chr12 | 22486717 | 22486882 |
| chr12 | 22487134 | 22487459 | chr12 | 22487461 | 22487556 | chr12 | 22698102 | 22698207 |
| chr12 | 24714835 | 24715014 | chr12 | 24715161 | 24715340 | chr12 | 24715947 | 24716204 |
| chr12 | 24716206 | 24716306 | chr12 | 25056243 | 25056524 | chr12 | 25101507 | 25101746 |
| chr12 | 25101824 | 25101998 | chr12 | 25102010 | 25102183 | chr12 | 25380187 | 25380366 |
| chr12 | 25398165 | 25398404 | chr12 | 28127676 | 28128395 | chr12 | 28128457 | 28129176 |
| chr12 | 29935913 | 29936152 | chr12 | 29936543 | 29936643 | chr12 | 29936662 | 29936777 |
| chr12 | 29936792 | 29936832 | chr12 | 29937234 | 29937343 | chr12 | 29937345 | 29937402 |
| chr12 | 30322697 | 30322925 | chr12 | 30323015 | 30323440 | chr12 | 30323503 | 30323596 |
| chr12 | 30975472 | 30975960 | chr12 | 31079179 | 31079368 | chr12 | 31079418 | 31079594 |
| chr12 | 32340225 | 32340336 | chr12 | 33591700 | 33591879 | chr12 | 33592512 | 33592642 |
| chr12 | 33592644 | 33592848 | chr12 | 33592933 | 33592991 | chr12 | 34494814 | 34494993 |
| chr12 | 34502649 | 34502888 | chr12 | 39299040 | 39299185 | chr12 | 39299269 | 39299639 |
| chr12 | 39539284 | 39539515 | chr12 | 40618318 | 40618557 | chr12 | 41086102 | 41086227 |
| chr12 | 41086229 | 41086461 | chr12 | 41086706 | 41087185 | chr12 | 41582422 | 41583081 |
| chr12 | 41583278 | 41583471 | chr12 | 43944800 | 43944881 | chr12 | 43945110 | 43945219 |

TABLE 15-continued

| chr | start | end | chr | start | end | chr | start | end |
|---|---|---|---|---|---|---|---|---|
| chr12 | 43945262 | 43945380 | chr12 | 43945417 | 43945621 | chr12 | 43945742 | 43945781 |
| chr12 | 43946203 | 43946401 | chr12 | 45269417 | 45269714 | chr12 | 45444029 | 45444682 |
| chr12 | 45444715 | 45444895 | chr12 | 45444897 | 45444920 | chr12 | 45445062 | 45445348 |
| chr12 | 47225301 | 47225303 | chr12 | 47225320 | 47225477 | chr12 | 47225551 | 47225660 |
| chr12 | 47629275 | 47629307 | chr12 | 47629398 | 47629454 | chr12 | 48397154 | 48398173 |
| chr12 | 48398567 | 48398746 | chr12 | 49297770 | 49298009 | chr12 | 49366280 | 49366519 |
| chr12 | 49374838 | 49375027 | chr12 | 49375116 | 49375197 | chr12 | 49375248 | 49375607 |
| chr12 | 49390824 | 49391105 | chr12 | 49391147 | 49391975 | chr12 | 49657624 | 49657722 |
| chr12 | 49690975 | 49691154 | chr12 | 49727092 | 49727208 | chr12 | 49729640 | 49730179 |
| chr12 | 50297417 | 50297555 | chr12 | 50297974 | 50298136 | chr12 | 50426672 | 50426894 |
| chr12 | 51421134 | 51421373 | chr12 | 51421482 | 51421661 | chr12 | 51565470 | 51565562 |
| chr12 | 51930615 | 51930785 | chr12 | 52262896 | 52263195 | chr12 | 52301205 | 52301306 |
| chr12 | 52400735 | 52400907 | chr12 | 52400909 | 52401539 | chr12 | 52401606 | 52401616 |
| chr12 | 52627273 | 52627381 | chr12 | 52652054 | 52652220 | chr12 | 52652600 | 52652713 |
| chr12 | 53108005 | 53108304 | chr12 | 53359245 | 53359316 | chr12 | 53359386 | 53359664 |
| chr12 | 54089004 | 54089602 | chr12 | 54132172 | 54132411 | chr12 | 54145750 | 54145858 |
| chr12 | 54145881 | 54145989 | chr12 | 54321170 | 54321709 | chr12 | 54322108 | 54322302 |
| chr12 | 54324719 | 54325018 | chr12 | 54329264 | 54329479 | chr12 | 54329605 | 54330007 |
| chr12 | 54330980 | 54331219 | chr12 | 54332774 | 54333433 | chr12 | 54338589 | 54338818 |
| chr12 | 54338979 | 54339668 | chr12 | 54343718 | 54343830 | chr12 | 54345523 | 54345659 |
| chr12 | 54345966 | 54346122 | chr12 | 54348761 | 54349080 | chr12 | 54349256 | 54349420 |
| chr12 | 54354419 | 54354694 | chr12 | 54354815 | 54355087 | chr12 | 54355571 | 54355575 |
| chr12 | 54359873 | 54360172 | chr12 | 54360510 | 54360729 | chr12 | 54377835 | 54377947 |
| chr12 | 54377978 | 54378194 | chr12 | 54379100 | 54379699 | chr12 | 54379785 | 54379931 |
| chr12 | 54379959 | 54380486 | chr12 | 54387752 | 54388051 | chr12 | 54388141 | 54388320 |
| chr12 | 54391267 | 54391324 | chr12 | 54391400 | 54391506 | chr12 | 54393403 | 54393460 |
| chr12 | 54393462 | 54393724 | chr12 | 54393847 | 54394266 | chr12 | 54394307 | 54394419 |
| chr12 | 54394467 | 54394546 | chr12 | 54398697 | 54398786 | chr12 | 54398889 | 54399056 |
| chr12 | 54399542 | 54399721 | chr12 | 54402654 | 54402812 | chr12 | 54402975 | 54403454 |
| chr12 | 54408330 | 54408809 | chr12 | 54424670 | 54424749 | chr12 | 54425032 | 54425141 |
| chr12 | 54447781 | 54447833 | chr12 | 54447899 | 54448080 | chr12 | 54520658 | 54520957 |
| chr12 | 54720221 | 54720320 | chr12 | 54812150 | 54812449 | chr12 | 54942906 | 54943191 |
| chr12 | 56882365 | 56882460 | chr12 | 57559778 | 57559914 | chr12 | 57618478 | 57618711 |
| chr12 | 57881046 | 57881345 | chr12 | 57943980 | 57944219 | chr12 | 58021218 | 58021459 |
| chr12 | 58021714 | 58021817 | chr12 | 58021824 | 58022093 | chr12 | 58025551 | 58025734 |
| chr12 | 58025870 | 58025970 | chr12 | 62584739 | 62585013 | chr12 | 62585031 | 62586118 |
| chr12 | 62586178 | 62586357 | chr12 | 63025615 | 63026257 | chr12 | 63543754 | 63544402 |
| chr12 | 63544499 | 63544600 | chr12 | 63544729 | 63544828 | chr12 | 63545239 | 63545418 |
| chr12 | 64061721 | 64062260 | chr12 | 64062295 | 64062498 | chr12 | 64062500 | 64062526 |
| chr12 | 64062528 | 64062654 | chr12 | 64062830 | 64063189 | chr12 | 64783098 | 64783322 |
| chr12 | 64784007 | 64784081 | chr12 | 64784108 | 64784352 | chr12 | 64784460 | 64784639 |
| chr12 | 65218320 | 65218551 | chr12 | 65218901 | 65219259 | chr12 | 65219281 | 65219528 |
| chr12 | 65219606 | 65219880 | chr12 | 65220129 | 65220428 | chr12 | 65514781 | 65515620 |
| chr12 | 65516379 | 65516558 | chr12 | 65557115 | 65557234 | chr12 | 65562064 | 65562172 |
| chr12 | 66122711 | 66122996 | chr12 | 66123381 | 66123610 | chr12 | 66135910 | 66136089 |
| chr12 | 66582743 | 66583048 | chr12 | 66583050 | 66583222 | chr12 | 69327182 | 69327541 |
| chr12 | 69754351 | 69754470 | chr12 | 69754600 | 69754710 | chr12 | 69964101 | 69964340 |
| chr12 | 70087412 | 70087651 | chr12 | 72332550 | 72332789 | chr12 | 72665167 | 72665526 |
| chr12 | 72665566 | 72665771 | chr12 | 72665773 | 72665877 | chr12 | 72666014 | 72666032 |
| chr12 | 72666620 | 72666808 | chr12 | 72666998 | 72667386 | chr12 | 72667388 | 72667519 |
| chr12 | 72667578 | 72667757 | chr12 | 75601168 | 75601231 | chr12 | 75601379 | 75601500 |
| chr12 | 75601696 | 75602007 | chr12 | 75602895 | 75603314 | chr12 | 75728262 | 75728561 |
| chr12 | 77719218 | 77719517 | chr12 | 79257138 | 79257437 | chr12 | 79258850 | 79258879 |
| chr12 | 79258966 | 79259029 | chr12 | 81102136 | 81102456 | chr12 | 81102513 | 81102603 |
| chr12 | 81107921 | 81107932 | chr12 | 81107997 | 81108100 | chr12 | 81471425 | 81471615 |
| chr12 | 81471754 | 81472204 | chr12 | 85306430 | 85306549 | chr12 | 85667173 | 85667832 |
| chr12 | 85673132 | 85673311 | chr12 | 85673385 | 85673915 | chr12 | 85673917 | 85674884 |
| chr12 | 88974346 | 88974356 | chr12 | 93966337 | 93966696 | chr12 | 93966910 | 93967216 |
| chr12 | 93967275 | 93967329 | chr12 | 94543308 | 94543547 | chr12 | 94543811 | 94543947 |
| chr12 | 94543949 | 94544080 | chr12 | 95267450 | 95267629 | chr12 | 95267772 | 95268000 |
| chr12 | 95941794 | 95941795 | chr12 | 95942965 | 95943053 | chr12 | 99288212 | 99288408 |
| chr12 | 99288622 | 99288937 | chr12 | 99288962 | 99288962 | chr12 | 99289162 | 99289411 |
| chr12 | 101025306 | 101025485 | chr12 | 101110926 | 101111165 | chr12 | 101111277 | 101111576 |
| chr12 | 103218396 | 103218655 | chr12 | 103350250 | 103350304 | chr12 | 103350384 | 103350429 |
| chr12 | 103351464 | 103351986 | chr12 | 103352052 | 103352155 | chr12 | 103352171 | 103352267 |
| chr12 | 103352269 | 103352283 | chr12 | 103352314 | 103352783 | chr12 | 103358763 | 103359002 |
| chr12 | 103359482 | 103359572 | chr12 | 103359574 | 103359661 | chr12 | 103889086 | 103889306 |
| chr12 | 103889660 | 103889714 | chr12 | 103889789 | 103889899 | chr12 | 104609340 | 104609526 |
| chr12 | 104609528 | 104609797 | chr12 | 104610163 | 104610179 | chr12 | 104850430 | 104850537 |
| chr12 | 104850578 | 104850669 | chr12 | 104850983 | 104851282 | chr12 | 104851941 | 104852151 |
| chr12 | 104852153 | 104852439 | chr12 | 104852441 | 104852446 | chr12 | 104852448 | 104852600 |
| chr12 | 105478222 | 105478457 | chr12 | 106974279 | 106974458 | chr12 | 106976641 | 106976780 |
| chr12 | 106976843 | 106976880 | chr12 | 106977394 | 106977589 | chr12 | 106979079 | 106979590 |
| chr12 | 106979718 | 106979874 | chr12 | 106979876 | 106980077 | chr12 | 106980129 | 106980428 |
| chr12 | 106980912 | 106981490 | chr12 | 107486462 | 107486673 | chr12 | 107487114 | 107487945 |
| chr12 | 107712199 | 107712378 | chr12 | 107713131 | 107713310 | chr12 | 107714771 | 107715250 |
| chr12 | 108168883 | 108169414 | chr12 | 108169550 | 108169662 | chr12 | 108237377 | 108237525 |
| chr12 | 108237661 | 108237676 | chr12 | 108238034 | 108238514 | chr12 | 108238684 | 108238719 |

TABLE 15-continued

| chr | start | end | chr | start | end | chr | start | end |
|---|---|---|---|---|---|---|---|---|
| chr12 | 108297320 | 108297559 | chr12 | 110353315 | 110353553 | chr12 | 110717447 | 110717806 |
| chr12 | 111127079 | 111127438 | chr12 | 111471099 | 111471309 | chr12 | 111471311 | 111471638 |
| chr12 | 111471871 | 111471960 | chr12 | 111472059 | 111472196 | chr12 | 111472357 | 111472511 |
| chr12 | 111472572 | 111472672 | chr12 | 111763136 | 111763227 | chr12 | 113012877 | 113013236 |
| chr12 | 113541644 | 113542183 | chr12 | 113592150 | 113592449 | chr12 | 113900616 | 113900678 |
| chr12 | 113900753 | 113900855 | chr12 | 113900974 | 113901159 | chr12 | 113901408 | 113901693 |
| chr12 | 113901951 | 113902018 | chr12 | 113902042 | 113902429 | chr12 | 113903394 | 113903573 |
| chr12 | 113904689 | 113905108 | chr12 | 113908894 | 113909315 | chr12 | 113909329 | 113909503 |
| chr12 | 113909535 | 113909553 | chr12 | 113909569 | 113909657 | chr12 | 113909718 | 113909808 |
| chr12 | 113913180 | 113913682 | chr12 | 113913884 | 113913887 | chr12 | 113913889 | 113914139 |
| chr12 | 113916147 | 113916266 | chr12 | 113916327 | 113916419 | chr12 | 113916575 | 113916754 |
| chr12 | 113916873 | 113917112 | chr12 | 113917212 | 113917391 | chr12 | 113917684 | 113917701 |
| chr12 | 113917731 | 113917983 | chr12 | 114029325 | 114029509 | chr12 | 114029546 | 114029744 |
| chr12 | 114075942 | 114076177 | chr12 | 114337849 | 114337868 | chr12 | 114833895 | 114834173 |
| chr12 | 114838227 | 114838312 | chr12 | 114838369 | 114838826 | chr12 | 114840946 | 114841185 |
| chr12 | 114843016 | 114843187 | chr12 | 114843261 | 114843375 | chr12 | 114843454 | 114843753 |
| chr12 | 114844102 | 114844401 | chr12 | 114846623 | 114846862 | chr12 | 114846886 | 114846947 |
| chr12 | 114847043 | 114847164 | chr12 | 114847166 | 114847437 | chr12 | 114847578 | 114847741 |
| chr12 | 114851969 | 114852181 | chr12 | 114852214 | 114852268 | chr12 | 114877068 | 114877367 |
| chr12 | 114878448 | 114878594 | chr12 | 114878809 | 114879093 | chr12 | 114881550 | 114881849 |
| chr12 | 114882488 | 114882727 | chr12 | 114883385 | 114883554 | chr12 | 114885134 | 114885184 |
| chr12 | 114885372 | 114885373 | chr12 | 114918513 | 114918806 | chr12 | 115136153 | 115136441 |
| chr12 | 116945988 | 116946200 | chr12 | 116946251 | 116946647 | chr12 | 117473983 | 117474282 |
| chr12 | 117797999 | 117798170 | chr12 | 117799331 | 117799621 | chr12 | 118860317 | 118860436 |
| chr12 | 119212120 | 119212200 | chr12 | 119212319 | 119212479 | chr12 | 119418512 | 119418931 |
| chr12 | 119419369 | 119419541 | chr12 | 119419631 | 119419920 | chr12 | 120032777 | 120033256 |
| chr12 | 120148125 | 120148345 | chr12 | 120148824 | 120149063 | chr12 | 120885155 | 120885274 |
| chr12 | 121622472 | 121622591 | chr12 | 122192885 | 122192933 | chr12 | 122284969 | 122285189 |
| chr12 | 123129041 | 123129139 | chr12 | 123233818 | 123233926 | chr12 | 124393463 | 124393702 |
| chr12 | 124397514 | 124397693 | chr12 | 125009254 | 125009381 | chr12 | 125533851 | 125534508 |
| chr12 | 125670024 | 125670261 | chr12 | 125670335 | 125670383 | chr12 | 126168468 | 126168707 |
| chr12 | 127210933 | 127210935 | chr12 | 127211317 | 127211472 | chr12 | 127765066 | 127765535 |
| chr12 | 127939988 | 127940189 | chr12 | 127940271 | 127940347 | chr12 | 128751295 | 128751534 |
| chr12 | 128751732 | 128751878 | chr12 | 128752115 | 128752331 | chr12 | 128752423 | 128753022 |
| chr12 | 128753136 | 128753315 | chr12 | 128850442 | 128850630 | chr12 | 128850632 | 128850739 |
| chr12 | 129337901 | 129337910 | chr12 | 129338588 | 129338826 | chr12 | 129338852 | 129338919 |
| chr12 | 130037571 | 130037866 | chr12 | 130387797 | 130387914 | chr12 | 130388332 | 130388435 |
| chr12 | 130389013 | 130389231 | chr12 | 130589116 | 130589354 | chr12 | 130645131 | 130645730 |
| chr12 | 130646590 | 130646654 | chr12 | 130646946 | 130647116 | chr12 | 130647574 | 130647909 |
| chr12 | 130647951 | 130648070 | chr12 | 130821287 | 130821706 | chr12 | 130968586 | 130968758 |
| chr12 | 131200303 | 131200649 | chr12 | 131400719 | 131401018 | chr12 | 131402943 | 131403229 |
| chr12 | 131513255 | 131513494 | chr12 | 132169246 | 132169357 | chr12 | 132221614 | 132222153 |
| chr12 | 132333337 | 132333418 | chr12 | 132333517 | 132333696 | chr12 | 132348549 | 132348788 |
| chr12 | 132423596 | 132423829 | chr12 | 132643371 | 132643376 | chr12 | 132986419 | 132986658 |
| chr12 | 133002713 | 133003312 | chr12 | 133194996 | 133195061 | chr12 | 133195063 | 133195229 |
| chr12 | 133199642 | 133199797 | chr12 | 133463657 | 133463956 | chr12 | 133464018 | 133464074 |
| chr12 | 133464755 | 133464920 | chr12 | 133481333 | 133481383 | chr12 | 133481490 | 133481520 |
| chr12 | 133481522 | 133481732 | chr12 | 133484660 | 133484853 | chr12 | 133485162 | 133485348 |
| chr12 | 133485463 | 133485690 | chr12 | 133485816 | 133485942 | chr12 | 133757959 | 133758198 |
| chr13 | 20735708 | 20736187 | chr13 | 21649557 | 21649856 | chr13 | 22243192 | 22243551 |
| chr13 | 23489764 | 23490003 | chr13 | 23733355 | 23734124 | chr13 | 23734182 | 23734298 |
| chr13 | 24477566 | 24477985 | chr13 | 25115623 | 25115648 | chr13 | 25115694 | 25115852 |
| chr13 | 25319764 | 25319905 | chr13 | 25320109 | 25320109 | chr13 | 25320388 | 25320540 |
| chr13 | 25320614 | 25321029 | chr13 | 25321113 | 25321443 | chr13 | 25321612 | 25322031 |
| chr13 | 25592963 | 25593040 | chr13 | 25593062 | 25593201 | chr13 | 25620951 | 25620954 |
| chr13 | 25620956 | 25621206 | chr13 | 25621264 | 25621490 | chr13 | 25744639 | 25744735 |
| chr13 | 25745301 | 25745595 | chr13 | 25745727 | 25746054 | chr13 | 25946301 | 25946488 |
| chr13 | 25946529 | 25946674 | chr13 | 25946802 | 25946888 | chr13 | 26042580 | 26042708 |
| chr13 | 26042769 | 26043171 | chr13 | 26043341 | 26043590 | chr13 | 26625267 | 26625657 |
| chr13 | 27132307 | 27132310 | chr13 | 27334118 | 27334657 | chr13 | 27334684 | 27334723 |
| chr13 | 27334725 | 27334983 | chr13 | 28239896 | 28240195 | chr13 | 28365615 | 28366181 |
| chr13 | 28366381 | 28366602 | chr13 | 28366665 | 28366680 | chr13 | 28366923 | 28367039 |
| chr13 | 28367712 | 28367946 | chr13 | 28368154 | 28368251 | chr13 | 28368373 | 28368672 |
| chr13 | 28368872 | 28369071 | chr13 | 28369162 | 28369891 | chr13 | 28369952 | 28370071 |
| chr13 | 28370855 | 28371154 | chr13 | 28394667 | 28394966 | chr13 | 28395408 | 28395647 |
| chr13 | 28395917 | 28396156 | chr13 | 28491694 | 28492050 | chr13 | 28492160 | 28492425 |
| chr13 | 28492427 | 28492639 | chr13 | 28528432 | 28528851 | chr13 | 28540657 | 28541016 |
| chr13 | 28543138 | 28543317 | chr13 | 28544321 | 28544585 | chr13 | 28544666 | 28544980 |
| chr13 | 28549396 | 28549892 | chr13 | 28550240 | 28550655 | chr13 | 28551320 | 28551549 |
| chr13 | 28551850 | 28552269 | chr13 | 28552660 | 28552660 | chr13 | 28552720 | 28552899 |
| chr13 | 28552935 | 28553234 | chr13 | 28673927 | 28674227 | chr13 | 28674721 | 28674826 |
| chr13 | 29067676 | 29068515 | chr13 | 29068847 | 29068986 | chr13 | 29068994 | 29069146 |
| chr13 | 29106217 | 29106422 | chr13 | 29106424 | 29106815 | chr13 | 29106899 | 29107064 |
| chr13 | 29107253 | 29107409 | chr13 | 30707495 | 30707674 | chr13 | 31742856 | 31743242 |
| chr13 | 32605033 | 32605212 | chr13 | 32605443 | 32605596 | chr13 | 32605675 | 32606001 |
| chr13 | 33591211 | 33591510 | chr13 | 33924579 | 33924812 | chr13 | 36704848 | 36705147 |
| chr13 | 36705351 | 36705446 | chr13 | 36705448 | 36705566 | chr13 | 36920216 | 36920224 |
| chr13 | 36920267 | 36920332 | chr13 | 36920334 | 36920387 | chr13 | 36920465 | 36920515 |

TABLE 15-continued

| chr | start | end | chr | start | end | chr | start | end |
|---|---|---|---|---|---|---|---|---|
| chr13 | 36920528 | 36920887 | chr13 | 37004681 | 37004992 | chr13 | 37005581 | 37005581 |
| chr13 | 37005900 | 37006063 | chr13 | 37006434 | 37006658 | chr13 | 37006734 | 37006840 |
| chr13 | 37247982 | 37248149 | chr13 | 37248295 | 37248305 | chr13 | 37248307 | 37248316 |
| chr13 | 37248886 | 37248994 | chr13 | 37249040 | 37249125 | chr13 | 37633915 | 37634094 |
| chr13 | 37643855 | 37644094 | chr13 | 38443544 | 38443634 | chr13 | 38443636 | 38443716 |
| chr13 | 39261309 | 39261472 | chr13 | 43566148 | 43566652 | chr13 | 44947643 | 44947700 |
| chr13 | 44947726 | 44948302 | chr13 | 45885802 | 45885981 | chr13 | 45905243 | 45905356 |
| chr13 | 46425447 | 46425555 | chr13 | 46425576 | 46425654 | chr13 | 46660850 | 46660944 |
| chr13 | 46961395 | 46961634 | chr13 | 47468065 | 47468244 | chr13 | 47526167 | 47526286 |
| chr13 | 48667803 | 48667982 | chr13 | 49794034 | 49794926 | chr13 | 53312917 | 53313314 |
| chr13 | 53313513 | 53313529 | chr13 | 53313531 | 53313613 | chr13 | 53313678 | 53313950 |
| chr13 | 53419636 | 53419729 | chr13 | 53419731 | 53419875 | chr13 | 53419931 | 53420021 |
| chr13 | 53421827 | 53421880 | chr13 | 53422220 | 53422252 | chr13 | 53422433 | 53422459 |
| chr13 | 53423759 | 53424058 | chr13 | 58203504 | 58203743 | chr13 | 58203768 | 58204187 |
| chr13 | 58204253 | 58204492 | chr13 | 58205944 | 58206232 | chr13 | 58206453 | 58206772 |
| chr13 | 58206862 | 58207083 | chr13 | 58207382 | 58207401 | chr13 | 58207568 | 58207814 |
| chr13 | 58207892 | 58208101 | chr13 | 58208412 | 58209011 | chr13 | 67804144 | 67804175 |
| chr13 | 67804420 | 67804531 | chr13 | 67805100 | 67805286 | chr13 | 70681550 | 70681778 |
| chr13 | 70681867 | 70682149 | chr13 | 72439047 | 72439109 | chr13 | 73619573 | 73619698 |
| chr13 | 78492724 | 78492942 | chr13 | 78493092 | 78493271 | chr13 | 78493363 | 78493902 |
| chr13 | 79169850 | 79170114 | chr13 | 79170348 | 79170384 | chr13 | 79170468 | 79170981 |
| chr13 | 79171038 | 79171277 | chr13 | 79175678 | 79175944 | chr13 | 79176078 | 79176126 |
| chr13 | 79176277 | 79176421 | chr13 | 79176609 | 79176877 | chr13 | 79176980 | 79177185 |
| chr13 | 79177306 | 79177623 | chr13 | 79177886 | 79178096 | chr13 | 79183327 | 79183424 |
| chr13 | 84455499 | 84455798 | chr13 | 88323504 | 88323831 | chr13 | 88323868 | 88324169 |
| chr13 | 88324171 | 88324283 | chr13 | 88324415 | 88324519 | chr13 | 88325201 | 88325560 |
| chr13 | 88325731 | 88326140 | chr13 | 88326447 | 88326708 | chr13 | 88326937 | 88327106 |
| chr13 | 88997832 | 88997951 | chr13 | 91948415 | 91948594 | chr13 | 92050668 | 92050843 |
| chr13 | 92051065 | 92051244 | chr13 | 92051273 | 92051400 | chr13 | 92051402 | 92051514 |
| chr13 | 93879213 | 93879303 | chr13 | 93879305 | 93879452 | chr13 | 93879596 | 93879775 |
| chr13 | 93879994 | 93880217 | chr13 | 93880534 | 93880738 | chr13 | 93880794 | 93880842 |
| chr13 | 93880844 | 93880953 | chr13 | 95357237 | 95357416 | chr13 | 95357496 | 95357855 |
| chr13 | 95357954 | 95358253 | chr13 | 95359656 | 95359895 | chr13 | 95360228 | 95360467 |
| chr13 | 95363111 | 95363452 | chr13 | 95363494 | 95363530 | chr13 | 95363697 | 95363960 |
| chr13 | 95364065 | 95364291 | chr13 | 95364409 | 95364675 | chr13 | 95364677 | 95364888 |
| chr13 | 95619931 | 95620170 | chr13 | 95620560 | 95620782 | chr13 | 95620854 | 95621099 |
| chr13 | 96031611 | 96031725 | chr13 | 96204923 | 96205438 | chr13 | 96296297 | 96296346 |
| chr13 | 96296373 | 96296556 | chr13 | 96296841 | 96296950 | chr13 | 96296992 | 96297215 |
| chr13 | 96743713 | 96743895 | chr13 | 96743897 | 96744212 | chr13 | 99851662 | 99851748 |
| chr13 | 100547770 | 100547894 | chr13 | 100608462 | 100608536 | chr13 | 100608597 | 100608805 |
| chr13 | 100608839 | 100609136 | chr13 | 100621859 | 100622031 | chr13 | 100624213 | 100624233 |
| chr13 | 100624324 | 100624452 | chr13 | 100624509 | 100624715 | chr13 | 100626905 | 100626925 |
| chr13 | 100630545 | 100631084 | chr13 | 100634227 | 100634382 | chr13 | 100635310 | 100635330 |
| chr13 | 100635399 | 100635518 | chr13 | 100636084 | 100636111 | chr13 | 100636131 | 100636323 |
| chr13 | 100637289 | 100637588 | chr13 | 100642151 | 100642282 | chr13 | 100643955 | 100644170 |
| chr13 | 100649334 | 100649576 | chr13 | 100649800 | 100649885 | chr13 | 100649945 | 100650018 |
| chr13 | 102568380 | 102568559 | chr13 | 102569313 | 102569643 | chr13 | 103046619 | 103047053 |
| chr13 | 103047055 | 103047098 | chr13 | 103052252 | 103052468 | chr13 | 103052470 | 103052671 |
| chr13 | 103052797 | 103052828 | chr13 | 103052830 | 103053036 | chr13 | 103053296 | 103053509 |
| chr13 | 107186781 | 107186960 | chr13 | 107187085 | 107187242 | chr13 | 108518298 | 108518354 |
| chr13 | 108518445 | 108518494 | chr13 | 108518724 | 108519017 | chr13 | 108519162 | 108519461 |
| chr13 | 108519637 | 108519746 | chr13 | 108519902 | 108519996 | chr13 | 108520370 | 108520535 |
| chr13 | 108520916 | 108520945 | chr13 | 108520947 | 108520969 | chr13 | 109147599 | 109147863 |
| chr13 | 109148155 | 109148279 | chr13 | 109148377 | 109148438 | chr13 | 109148685 | 109149115 |
| chr13 | 109149164 | 109149284 | chr13 | 110434373 | 110434672 | chr13 | 110958720 | 110958977 |
| chr13 | 110958979 | 110959054 | chr13 | 110959629 | 110959649 | chr13 | 110959753 | 110960048 |
| chr13 | 110960345 | 110960386 | chr13 | 110960453 | 110960692 | chr13 | 111278225 | 111278521 |
| chr13 | 111363885 | 111364060 | chr13 | 112272891 | 112273102 | chr13 | 112707603 | 112707962 |
| chr13 | 112708002 | 112708005 | chr13 | 112708308 | 112708601 | chr13 | 112709408 | 112709647 |
| chr13 | 112709713 | 112709713 | chr13 | 112709787 | 112710026 | chr13 | 112710247 | 112710253 |
| chr13 | 112710360 | 112710476 | chr13 | 112710669 | 112710823 | chr13 | 112710825 | 112711294 |
| chr13 | 112711376 | 112711868 | chr13 | 112711924 | 112713123 | chr13 | 112715267 | 112715719 |
| chr13 | 112715910 | 112716389 | chr13 | 112716695 | 112716814 | chr13 | 112716982 | 112717243 |
| chr13 | 112717323 | 112717611 | chr13 | 112717743 | 112718042 | chr13 | 112719940 | 112720599 |
| chr13 | 112720626 | 112720865 | chr13 | 112720938 | 112721027 | chr13 | 112722129 | 112722221 |
| chr13 | 112722275 | 112722403 | chr13 | 112724431 | 112724610 | chr13 | 112726240 | 112726293 |
| chr13 | 112726436 | 112726659 | chr13 | 112727962 | 112728201 | chr13 | 112728336 | 112728367 |
| chr13 | 112758033 | 112758373 | chr13 | 112758496 | 112758688 | chr13 | 112759112 | 112759349 |
| chr13 | 112759538 | 112759717 | chr13 | 112760007 | 112760413 | chr13 | 112760755 | 112761305 |
| chr13 | 113598526 | 113598877 | chr13 | 113985597 | 113985956 | chr13 | 114055881 | 114056240 |
| chr13 | 114059990 | 114060409 | chr13 | 114074692 | 114074931 | chr13 | 114123081 | 114123358 |
| chr13 | 114189654 | 114189732 | chr13 | 114221548 | 114221655 | chr13 | 114304637 | 114305016 |
| chr13 | 114479330 | 114479509 | chr13 | 114497930 | 114498349 | chr13 | 114748251 | 114748720 |
| chr13 | 114780482 | 114781141 | chr13 | 114807537 | 114807896 | chr13 | 114855533 | 114855772 |
| chr13 | 114862381 | 114862458 | chr13 | 114961729 | 114962028 | chr14 | 21093364 | 21093531 |
| chr14 | 21093604 | 21093723 | chr14 | 21100674 | 21100906 | chr14 | 22004932 | 22004993 |
| chr14 | 22004995 | 22005171 | chr14 | 23356162 | 23356341 | chr14 | 23706666 | 23706845 |
| chr14 | 24803493 | 24803917 | chr14 | 24803919 | 24804123 | chr14 | 24804425 | 24804512 |

TABLE 15-continued

| chr | start | end | chr | start | end | chr | start | end |
|---|---|---|---|---|---|---|---|---|
| chr14 | 26674280 | 26674459 | chr14 | 26674625 | 26674703 | chr14 | 27066520 | 27066699 |
| chr14 | 27067065 | 27067157 | chr14 | 27067373 | 27067427 | chr14 | 29225457 | 29225636 |
| chr14 | 29225986 | 29226285 | chr14 | 29228567 | 29228866 | chr14 | 29229008 | 29229249 |
| chr14 | 29229251 | 29229487 | chr14 | 29230995 | 29231186 | chr14 | 29231329 | 29231688 |
| chr14 | 29234911 | 29235309 | chr14 | 29235342 | 29235450 | chr14 | 29236966 | 29237067 |
| chr14 | 29237140 | 29237205 | chr14 | 29242687 | 29242707 | chr14 | 29243433 | 29243670 |
| chr14 | 29243731 | 29243972 | chr14 | 29244147 | 29244383 | chr14 | 29247596 | 29247835 |
| chr14 | 29254612 | 29254794 | chr14 | 31344269 | 31344628 | chr14 | 31925640 | 31925804 |
| chr14 | 32597619 | 32597759 | chr14 | 33402373 | 33402512 | chr14 | 33402514 | 33402852 |
| chr14 | 33402942 | 33403019 | chr14 | 33403125 | 33403421 | chr14 | 33403783 | 33404502 |
| chr14 | 34420150 | 34420389 | chr14 | 35023188 | 35023427 | chr14 | 35024347 | 35024454 |
| chr14 | 36003471 | 36003904 | chr14 | 36004081 | 36004578 | chr14 | 36004608 | 36004735 |
| chr14 | 36004822 | 36004922 | chr14 | 36005012 | 36005087 | chr14 | 36972709 | 36973008 |
| chr14 | 36973157 | 36973222 | chr14 | 36973455 | 36973636 | chr14 | 36974421 | 36974800 |
| chr14 | 36974802 | 36974928 | chr14 | 36974968 | 36975058 | chr14 | 36975200 | 36975229 |
| chr14 | 36975281 | 36975499 | chr14 | 36977558 | 36977930 | chr14 | 36977975 | 36978097 |
| chr14 | 36978474 | 36978653 | chr14 | 36979657 | 36979724 | chr14 | 36982870 | 36983068 |
| chr14 | 36983674 | 36984227 | chr14 | 36985767 | 36985946 | chr14 | 36986212 | 36986472 |
| chr14 | 36987302 | 36987787 | chr14 | 36987862 | 36988221 | chr14 | 36988449 | 36988564 |
| chr14 | 36990779 | 36991033 | chr14 | 36991095 | 36991258 | chr14 | 36991501 | 36991693 |
| chr14 | 36991989 | 36992164 | chr14 | 36992222 | 36992507 | chr14 | 36993386 | 36993488 |
| chr14 | 36993694 | 36994045 | chr14 | 36994145 | 36995009 | chr14 | 36995011 | 36995104 |
| chr14 | 37116026 | 37116295 | chr14 | 37117535 | 37117697 | chr14 | 37123339 | 37124178 |
| chr14 | 37124482 | 37124648 | chr14 | 37124910 | 37125629 | chr14 | 37126150 | 37126389 |
| chr14 | 37126463 | 37126714 | chr14 | 37126965 | 37127002 | chr14 | 37127207 | 37127386 |
| chr14 | 37127572 | 37127780 | chr14 | 37129990 | 37130349 | chr14 | 37132296 | 37132554 |
| chr14 | 37132603 | 37132775 | chr14 | 37132908 | 37133147 | chr14 | 37135740 | 37135868 |
| chr14 | 37135922 | 37136018 | chr14 | 37136295 | 37136425 | chr14 | 37136514 | 37136693 |
| chr14 | 38060588 | 38060917 | chr14 | 38677445 | 38677581 | chr14 | 38724207 | 38724526 |
| chr14 | 38724979 | 38725346 | chr14 | 38725455 | 38725560 | chr14 | 42074467 | 42074587 |
| chr14 | 42074669 | 42074944 | chr14 | 42075023 | 42075066 | chr14 | 42075511 | 42075810 |
| chr14 | 42075812 | 42076044 | chr14 | 42076106 | 42076290 | chr14 | 42076749 | 42076928 |
| chr14 | 42077130 | 42077368 | chr14 | 42077696 | 42077804 | chr14 | 42079190 | 42079429 |
| chr14 | 48143657 | 48143719 | chr14 | 48143798 | 48143958 | chr14 | 48144359 | 48144500 |
| chr14 | 48144619 | 48144764 | chr14 | 48145237 | 48145338 | chr14 | 50334976 | 50334084 |
| chr14 | 50334336 | 50334455 | chr14 | 51338642 | 51338732 | chr14 | 51339048 | 51339061 |
| chr14 | 51560207 | 51560714 | chr14 | 51560771 | 51561293 | chr14 | 51561295 | 51561526 |
| chr14 | 51561680 | 51562099 | chr14 | 52534571 | 52534870 | chr14 | 52534929 | 52535027 |
| chr14 | 52535056 | 52535264 | chr14 | 52535335 | 52535425 | chr14 | 52535427 | 52535758 |
| chr14 | 52535760 | 52535973 | chr14 | 52535975 | 52536066 | chr14 | 52536068 | 52536105 |
| chr14 | 52536343 | 52536488 | chr14 | 52734414 | 52734525 | chr14 | 52734527 | 52734653 |
| chr14 | 52734687 | 52735002 | chr14 | 52735045 | 52735346 | chr14 | 52781422 | 52782021 |
| chr14 | 54422549 | 54422925 | chr14 | 54422927 | 54423028 | chr14 | 55370100 | 55370219 |
| chr14 | 55596008 | 55596043 | chr14 | 55765207 | 55765686 | chr14 | 57045445 | 57045840 |
| chr14 | 57260845 | 57261095 | chr14 | 57261175 | 57261408 | chr14 | 57261466 | 57261880 |
| chr14 | 57261977 | 57262276 | chr14 | 57264001 | 57264646 | chr14 | 57264765 | 57264807 |
| chr14 | 57265148 | 57265320 | chr14 | 57270854 | 57270972 | chr14 | 57271154 | 57271333 |
| chr14 | 57271919 | 57272114 | chr14 | 57274387 | 57274739 | chr14 | 57274741 | 57275050 |
| chr14 | 57275211 | 57275406 | chr14 | 57275521 | 57275686 | chr14 | 57276074 | 57276180 |
| chr14 | 57276344 | 57276763 | chr14 | 57277830 | 57278763 | chr14 | 57278838 | 57279565 |
| chr14 | 57279643 | 57279712 | chr14 | 57283238 | 57283409 | chr14 | 57283446 | 57284037 |
| chr14 | 57284071 | 57284737 | chr14 | 58332201 | 58332494 | chr14 | 60097111 | 60097247 |
| chr14 | 60097407 | 60097650 | chr14 | 60386111 | 60386350 | chr14 | 60386551 | 60386743 |
| chr14 | 60794532 | 60794771 | chr14 | 60952196 | 60952420 | chr14 | 60952517 | 60952633 |
| chr14 | 60952730 | 60953039 | chr14 | 60973157 | 60973418 | chr14 | 60973618 | 60974008 |
| chr14 | 60974078 | 60974157 | chr14 | 60974273 | 60974506 | chr14 | 60975290 | 60975889 |
| chr14 | 60976075 | 60976609 | chr14 | 60976803 | 60976957 | chr14 | 60977263 | 60977713 |
| chr14 | 60977880 | 60978222 | chr14 | 60981116 | 60981355 | chr14 | 60981586 | 60981813 |
| chr14 | 60982007 | 60982368 | chr14 | 60982574 | 60982726 | chr14 | 60982757 | 60982996 |
| chr14 | 61104242 | 61104557 | chr14 | 61104624 | 61104952 | chr14 | 61108539 | 61108904 |
| chr14 | 61109031 | 61109078 | chr14 | 61109129 | 61109548 | chr14 | 61109742 | 61110341 |
| chr14 | 61114058 | 61114537 | chr14 | 61115235 | 61115594 | chr14 | 61118743 | 61118841 |
| chr14 | 61118872 | 61119227 | chr14 | 61747389 | 61747528 | chr14 | 61747583 | 61747816 |
| chr14 | 61748002 | 61748117 | chr14 | 62279520 | 62279623 | chr14 | 62279625 | 62279853 |
| chr14 | 62279899 | 62280092 | chr14 | 62583710 | 62583870 | chr14 | 62583919 | 62584009 |
| chr14 | 63512064 | 63512376 | chr14 | 63512486 | 63512709 | chr14 | 63512741 | 63512905 |
| chr14 | 63513050 | 63513229 | chr14 | 64222332 | 64222450 | chr14 | 65005803 | 65005915 |
| chr14 | 65008915 | 65008975 | chr14 | 65008998 | 65009274 | chr14 | 65233253 | 65233552 |
| chr14 | 67886583 | 67886702 | chr14 | 69013958 | 69014195 | chr14 | 69866930 | 69867269 |
| chr14 | 70014640 | 70015059 | chr14 | 70346045 | 70346584 | chr14 | 70654379 | 70654597 |
| chr14 | 70654599 | 70654639 | chr14 | 70654641 | 70654798 | chr14 | 70655451 | 70655890 |
| chr14 | 70655920 | 70656170 | chr14 | 72398642 | 72399121 | chr14 | 72399452 | 72399557 |
| chr14 | 72399830 | 72400129 | chr14 | 73167676 | 73167975 | chr14 | 73174938 | 73175237 |
| chr14 | 73178717 | 73178956 | chr14 | 73180112 | 73180336 | chr14 | 73318371 | 73318730 |
| chr14 | 73333174 | 73333256 | chr14 | 73602351 | 73602470 | chr14 | 74705940 | 74706299 |
| chr14 | 74706357 | 74706397 | chr14 | 74706941 | 74707545 | chr14 | 74707573 | 74707748 |
| chr14 | 74707792 | 74707911 | chr14 | 74707913 | 74707976 | chr14 | 74708760 | 74709059 |
| chr14 | 74892472 | 74892645 | chr14 | 74892975 | 74893191 | chr14 | 75078070 | 75078243 |

TABLE 15-continued

| chr | start | end | chr | start | end | chr | start | end |
|---|---|---|---|---|---|---|---|---|
| chr14 | 75760210 | 75760329 | chr14 | 76604580 | 76604819 | chr14 | 76604985 | 76605464 |
| chr14 | 76843364 | 76843386 | chr14 | 76843733 | 76844058 | chr14 | 77228021 | 77228107 |
| chr14 | 77606833 | 77606856 | chr14 | 77606922 | 77607312 | chr14 | 77737110 | 77737146 |
| chr14 | 77737148 | 77737685 | chr14 | 79745088 | 79745277 | chr14 | 85996395 | 85996694 |
| chr14 | 85996760 | 85996796 | chr14 | 85996892 | 85996999 | chr14 | 85997735 | 85997926 |
| chr14 | 85998468 | 85998575 | chr14 | 85998630 | 85998786 | chr14 | 85999472 | 85999532 |
| chr14 | 85999597 | 85999711 | chr14 | 86000182 | 86000574 | chr14 | 86000886 | 86001196 |
| chr14 | 89817813 | 89818112 | chr14 | 90527617 | 90527856 | chr14 | 90983225 | 90983385 |
| chr14 | 91691167 | 91691385 | chr14 | 91766189 | 91766542 | chr14 | 92789438 | 92789617 |
| chr14 | 92789777 | 92789822 | chr14 | 92789960 | 92790099 | chr14 | 92790551 | 92790790 |
| chr14 | 92979835 | 92980074 | chr14 | 93154979 | 93155385 | chr14 | 93389450 | 93389458 |
| chr14 | 93389557 | 93389694 | chr14 | 93389713 | 93389869 | chr14 | 93706678 | 93706857 |
| chr14 | 94254302 | 94254459 | chr14 | 94254499 | 94254601 | chr14 | 94405641 | 94405880 |
| chr14 | 95233616 | 95233646 | chr14 | 95234557 | 95234711 | chr14 | 95235026 | 95235383 |
| chr14 | 95235939 | 95236200 | chr14 | 95236450 | 95236598 | chr14 | 95239298 | 95239349 |
| chr14 | 95239422 | 95239717 | chr14 | 95240053 | 95240268 | chr14 | 95240410 | 95240497 |
| chr14 | 96342551 | 96342631 | chr14 | 96342880 | 96343225 | chr14 | 96343330 | 96343435 |
| chr14 | 96343668 | 96343792 | chr14 | 97045327 | 97045506 | chr14 | 97058761 | 97058818 |
| chr14 | 97058944 | 97059180 | chr14 | 97499257 | 97499416 | chr14 | 97499616 | 97499627 |
| chr14 | 97499847 | 97499850 | chr14 | 97499971 | 97500035 | chr14 | 97684957 | 97685297 |
| chr14 | 97685624 | 97686038 | chr14 | 99584501 | 99584740 | chr14 | 99736048 | 99736213 |
| chr14 | 100437707 | 100437950 | chr14 | 100438018 | 100438066 | chr14 | 100438609 | 100438908 |
| chr14 | 100643267 | 100643566 | chr14 | 101193145 | 101193147 | chr14 | 101250012 | 101250371 |
| chr14 | 101543783 | 101544270 | chr14 | 101923033 | 101923332 | chr14 | 101923520 | 101923687 |
| chr14 | 101924031 | 101924122 | chr14 | 101924966 | 101925072 | chr14 | 101925656 | 101925705 |
| chr14 | 101925707 | 101925985 | chr14 | 102026273 | 102026572 | chr14 | 102026703 | 102027062 |
| chr14 | 102031132 | 102031194 | chr14 | 102031236 | 102031371 | chr14 | 102031434 | 102031450 |
| chr14 | 102031508 | 102031666 | chr14 | 102247824 | 102248303 | chr14 | 102418533 | 102418652 |
| chr14 | 102521501 | 102521860 | chr14 | 102529912 | 102530178 | chr14 | 102530426 | 102530605 |
| chr14 | 102564386 | 102564502 | chr14 | 102681994 | 102682233 | chr14 | 103021308 | 103022087 |
| chr14 | 103394784 | 103395203 | chr14 | 103477540 | 103477771 | chr14 | 103655154 | 103655568 |
| chr14 | 103655570 | 103655684 | chr14 | 103673992 | 103673994 | chr14 | 103674069 | 103674080 |
| chr14 | 103674216 | 103674231 | chr14 | 103687002 | 103687301 | chr14 | 103739885 | 103740239 |
| chr14 | 103740275 | 103740437 | chr14 | 103745606 | 103745845 | chr14 | 104159978 | 104160160 |
| chr14 | 104202624 | 104202852 | chr14 | 104547814 | 104547993 | chr14 | 104571902 | 104572201 |
| chr14 | 104601657 | 104601873 | chr14 | 104601964 | 104602138 | chr14 | 104604954 | 104605193 |
| chr14 | 104620334 | 104620633 | chr14 | 104627564 | 104627862 | chr14 | 104645048 | 104645277 |
| chr14 | 104646225 | 104646584 | chr14 | 104647183 | 104647362 | chr14 | 104682452 | 104682751 |
| chr14 | 104862764 | 104863123 | chr14 | 105071198 | 105071340 | chr14 | 105157401 | 105157640 |
| chr14 | 105241220 | 105241267 | chr14 | 105246463 | 105246642 | chr14 | 105511960 | 105512463 |
| chr14 | 105658268 | 105658507 | chr14 | 105714177 | 105714442 | chr14 | 105715248 | 105715393 |
| chr14 | 105715539 | 105715565 | chr15 | 22822269 | 22822384 | chr15 | 23158294 | 23158593 |
| chr15 | 26107541 | 26107744 | chr15 | 26107846 | 26107960 | chr15 | 26108010 | 26108327 |
| chr15 | 26108549 | 26108789 | chr15 | 27018281 | 27018329 | chr15 | 27212791 | 27213270 |
| chr15 | 27603982 | 27604057 | chr15 | 28341615 | 28341980 | chr15 | 28341982 | 28342020 |
| chr15 | 28344081 | 28344188 | chr15 | 28344224 | 28344350 | chr15 | 28352156 | 28352422 |
| chr15 | 29077185 | 29077394 | chr15 | 29077429 | 29077484 | chr15 | 29130712 | 29131048 |
| chr15 | 29131533 | 29131631 | chr15 | 29131756 | 29131971 | chr15 | 29407680 | 29407814 |
| chr15 | 29407867 | 29408099 | chr15 | 29862423 | 29862537 | chr15 | 31455297 | 31455578 |
| chr15 | 31775500 | 31775638 | chr15 | 31775679 | 31775783 | chr15 | 31776146 | 31776190 |
| chr15 | 33009649 | 33009762 | chr15 | 33009822 | 33010399 | chr15 | 33010401 | 33010676 |
| chr15 | 33010721 | 33011166 | chr15 | 33011168 | 33011448 | chr15 | 33011498 | 33011737 |
| chr15 | 33486970 | 33487209 | chr15 | 33602725 | 33602964 | chr15 | 33603110 | 33603609 |
| chr15 | 33603648 | 33603709 | chr15 | 33879168 | 33879347 | chr15 | 34630346 | 34630389 |
| chr15 | 34630439 | 34630525 | chr15 | 34729381 | 34729680 | chr15 | 34786425 | 34786944 |
| chr15 | 34787233 | 34787384 | chr15 | 35046935 | 35047149 | chr15 | 35087563 | 35087802 |
| chr15 | 37180227 | 37180241 | chr15 | 37180414 | 37180826 | chr15 | 37402898 | 37403087 |
| chr15 | 37403116 | 37403316 | chr15 | 40211736 | 40212275 | chr15 | 40575538 | 40575837 |
| chr15 | 41165152 | 41165751 | chr15 | 41804786 | 41805865 | chr15 | 41835732 | 41835814 |
| chr15 | 41913660 | 41913899 | chr15 | 41952493 | 41952792 | chr15 | 43810472 | 43810510 |
| chr15 | 44037485 | 44037604 | chr15 | 45403554 | 45403681 | chr15 | 45403799 | 45404000 |
| chr15 | 45404103 | 45404213 | chr15 | 45404833 | 45404833 | chr15 | 45404898 | 45405209 |
| chr15 | 45421291 | 45421530 | chr15 | 45421874 | 45421947 | chr15 | 45427263 | 45427341 |
| chr15 | 45427370 | 45427502 | chr15 | 45427520 | 45427720 | chr15 | 45427772 | 45427879 |
| chr15 | 45479371 | 45479517 | chr15 | 45479775 | 45479789 | chr15 | 45670503 | 45670839 |
| chr15 | 45670933 | 45670971 | chr15 | 47476794 | 47476806 | chr15 | 47476877 | 47476981 |
| chr15 | 47477013 | 47477093 | chr15 | 48483907 | 48483963 | chr15 | 48936639 | 48937213 |
| chr15 | 48937215 | 48937646 | chr15 | 48937710 | 48938077 | chr15 | 48938122 | 48938347 |
| chr15 | 48938349 | 48938601 | chr15 | 51385838 | 51386257 | chr15 | 51633986 | 51634151 |
| chr15 | 51634175 | 51634225 | chr15 | 51973695 | 51973695 | chr15 | 51973764 | 51974030 |
| chr15 | 53075740 | 53075865 | chr15 | 53075986 | 53077001 | chr15 | 53077066 | 53077455 |
| chr15 | 53077574 | 53077813 | chr15 | 53077971 | 53078320 | chr15 | 53079262 | 53079678 |
| chr15 | 53079718 | 53079892 | chr15 | 53079971 | 53080161 | chr15 | 53080263 | 53080620 |
| chr15 | 53080861 | 53080991 | chr15 | 53081055 | 53081100 | chr15 | 53081223 | 53081297 |
| chr15 | 53081399 | 53081702 | chr15 | 53082348 | 53082587 | chr15 | 53096735 | 53096974 |
| chr15 | 53097157 | 53097336 | chr15 | 53097535 | 53097569 | chr15 | 53097778 | 53097907 |
| chr15 | 53098382 | 53098757 | chr15 | 54270424 | 54270783 | chr15 | 54270858 | 54271025 |
| chr15 | 55452972 | 55453087 | chr15 | 55699008 | 55699127 | chr15 | 55880891 | 55881044 |

TABLE 15-continued

| chr | start | end | chr | start | end | chr | start | end |
|---|---|---|---|---|---|---|---|---|
| chr15 | 55881046 | 55881095 | chr15 | 58357800 | 58357820 | chr15 | 59158454 | 59158616 |
| chr15 | 59950343 | 59950461 | chr15 | 60286937 | 60287586 | chr15 | 60287644 | 60287780 |
| chr15 | 60288703 | 60288935 | chr15 | 60289229 | 60289638 | chr15 | 60296047 | 60296286 |
| chr15 | 60296495 | 60296618 | chr15 | 60296861 | 60296924 | chr15 | 60297152 | 60297514 |
| chr15 | 60297544 | 60297827 | chr15 | 60297942 | 60298203 | chr15 | 61520816 | 61521115 |
| chr15 | 61521559 | 61521621 | chr15 | 61521657 | 61521676 | chr15 | 61521713 | 61522038 |
| chr15 | 62456848 | 62456966 | chr15 | 62457009 | 62457019 | chr15 | 65669760 | 65669999 |
| chr15 | 65862054 | 65862213 | chr15 | 66963725 | 66963823 | chr15 | 66963928 | 66963964 |
| chr15 | 68112537 | 68112716 | chr15 | 68113794 | 68113973 | chr15 | 68114048 | 68114287 |
| chr15 | 68116286 | 68116682 | chr15 | 68117753 | 68118712 | chr15 | 68118783 | 68118784 |
| chr15 | 68118799 | 68118876 | chr15 | 68118930 | 68119175 | chr15 | 68119579 | 68120353 |
| chr15 | 68120631 | 68120662 | chr15 | 68120753 | 68120932 | chr15 | 68121150 | 68121958 |
| chr15 | 68122569 | 68122748 | chr15 | 68125164 | 68125763 | chr15 | 68127717 | 68128436 |
| chr15 | 68128492 | 68128597 | chr15 | 68260435 | 68260735 | chr15 | 71055770 | 71055906 |
| chr15 | 72412113 | 72412263 | chr15 | 72743650 | 72743859 | chr15 | 73659917 | 73660156 |
| chr15 | 73661476 | 73661748 | chr15 | 74044960 | 74045023 | chr15 | 74045075 | 74045199 |
| chr15 | 74421927 | 74421954 | chr15 | 74421980 | 74422226 | chr15 | 74422787 | 74423012 |
| chr15 | 74658070 | 74658397 | chr15 | 74658502 | 74658553 | chr15 | 74658555 | 74658595 |
| chr15 | 74686082 | 74686126 | chr15 | 74818670 | 74818789 | chr15 | 74903822 | 74904001 |
| chr15 | 75251245 | 75251414 | chr15 | 75251479 | 75251484 | chr15 | 75251580 | 75251879 |
| chr15 | 75471218 | 75471275 | chr15 | 76627515 | 76627537 | chr15 | 76627576 | 76627907 |
| chr15 | 76628959 | 76629026 | chr15 | 76629163 | 76629314 | chr15 | 76629588 | 76629633 |
| chr15 | 76629732 | 76630095 | chr15 | 76630097 | 76630125 | chr15 | 76630520 | 76630793 |
| chr15 | 76632518 | 76632520 | chr15 | 76635040 | 76635110 | chr15 | 76635576 | 76635635 |
| chr15 | 76638387 | 76638497 | chr15 | 77448976 | 77449087 | chr15 | 78501725 | 78502024 |
| chr15 | 78556795 | 78557034 | chr15 | 78557110 | 78557204 | chr15 | 78596066 | 78596245 |
| chr15 | 78632626 | 78632669 | chr15 | 78632684 | 78632925 | chr15 | 78912192 | 78912372 |
| chr15 | 78912442 | 78912491 | chr15 | 78912549 | 78912728 | chr15 | 78912832 | 78913028 |
| chr15 | 78913095 | 78913251 | chr15 | 78913444 | 78913470 | chr15 | 78913481 | 78913683 |
| chr15 | 79104143 | 79104159 | chr15 | 79381709 | 79381746 | chr15 | 79382099 | 79382648 |
| chr15 | 79382693 | 79382998 | chr15 | 79383000 | 79383268 | chr15 | 79383873 | 79384052 |
| chr15 | 79502137 | 79502381 | chr15 | 79575197 | 79575556 | chr15 | 79576062 | 79576361 |
| chr15 | 79724034 | 79724120 | chr15 | 79724402 | 79724561 | chr15 | 79724607 | 79724793 |
| chr15 | 79724864 | 79725241 | chr15 | 79725332 | 79725584 | chr15 | 82336777 | 82337076 |
| chr15 | 82339995 | 82340234 | chr15 | 83315246 | 83315474 | chr15 | 83316232 | 83316640 |
| chr15 | 83316642 | 83317162 | chr15 | 83349131 | 83349612 | chr15 | 83349672 | 83349790 |
| chr15 | 83378112 | 83378164 | chr15 | 83378186 | 83378471 | chr15 | 83776161 | 83776269 |
| chr15 | 83776271 | 83776307 | chr15 | 83776333 | 83776717 | chr15 | 83776769 | 83776880 |
| chr15 | 83875571 | 83875666 | chr15 | 83875706 | 83875985 | chr15 | 83876953 | 83877252 |
| chr15 | 83952108 | 83952113 | chr15 | 83952769 | 83952827 | chr15 | 83953024 | 83953049 |
| chr15 | 84115648 | 84115811 | chr15 | 84115813 | 84115854 | chr15 | 84115932 | 84116067 |
| chr15 | 84116829 | 84116995 | chr15 | 84322994 | 84323124 | chr15 | 84748500 | 84748620 |
| chr15 | 84748679 | 84749339 | chr15 | 85143052 | 85143144 | chr15 | 88798591 | 88798654 |
| chr15 | 88798725 | 88798890 | chr15 | 88799448 | 88799999 | chr15 | 88800001 | 88800302 |
| chr15 | 88800463 | 88801004 | chr15 | 88801006 | 88801009 | chr15 | 88801089 | 88801182 |
| chr15 | 89149070 | 89149489 | chr15 | 89248651 | 89249010 | chr15 | 89345953 | 89346327 |
| chr15 | 89346347 | 89346492 | chr15 | 89346568 | 89346794 | chr15 | 89346882 | 89347047 |
| chr15 | 89903410 | 89903889 | chr15 | 89910426 | 89910845 | chr15 | 89910988 | 89911287 |
| chr15 | 89913676 | 89913855 | chr15 | 89914144 | 89914450 | chr15 | 89914867 | 89914983 |
| chr15 | 89915156 | 89915455 | chr15 | 89921862 | 89922038 | chr15 | 89922500 | 89922649 |
| chr15 | 89942671 | 89943030 | chr15 | 89943319 | 89943775 | chr15 | 89949317 | 89949410 |
| chr15 | 89949617 | 89950036 | chr15 | 89950154 | 89950737 | chr15 | 89951082 | 89951215 |
| chr15 | 89951302 | 89951377 | chr15 | 89951466 | 89951901 | chr15 | 89952065 | 89952453 |
| chr15 | 89952700 | 89953144 | chr15 | 89954122 | 89954416 | chr15 | 89956288 | 89956354 |
| chr15 | 89956423 | 89956527 | chr15 | 90039488 | 90039787 | chr15 | 90755819 | 90756144 |
| chr15 | 91643264 | 91643683 | chr15 | 92936281 | 92936426 | chr15 | 92937115 | 92937474 |
| chr15 | 92937849 | 92938061 | chr15 | 92938123 | 92938294 | chr15 | 92938316 | 92938388 |
| chr15 | 93631638 | 93632117 | chr15 | 93632558 | 93632730 | chr15 | 93632732 | 93633337 |
| chr15 | 94347588 | 94347707 | chr15 | 95388666 | 95388712 | chr15 | 96874259 | 96874416 |
| chr15 | 96889374 | 96889506 | chr15 | 96897853 | 96898092 | chr15 | 96911456 | 96911692 |
| chr15 | 96911764 | 96911815 | chr15 | 96952594 | 96953099 | chr15 | 96953132 | 96953313 |
| chr15 | 96959720 | 96959961 | chr15 | 96960428 | 96960513 | chr15 | 96960630 | 96960907 |
| chr15 | 97006274 | 97006623 | chr15 | 98504040 | 98504219 | chr15 | 98836077 | 98836477 |
| chr15 | 98965179 | 98965232 | chr15 | 99193106 | 99193345 | chr15 | 99193350 | 99193583 |
| chr15 | 99193873 | 99194172 | chr15 | 99456272 | 99456372 | chr15 | 100913332 | 100913596 |
| chr15 | 101420447 | 101420665 | chr15 | 101420848 | 101420860 | chr15 | 101420972 | 101421087 |
| chr15 | 101513806 | 101513831 | chr16 | 142567 | 142775 | chr16 | 215341 | 215873 |
| chr16 | 215913 | 215960 | chr16 | 215962 | 216300 | chr16 | 216587 | 217070 |
| chr16 | 230229 | 230316 | chr16 | 230497 | 230708 | chr16 | 318040 | 318316 |
| chr16 | 318422 | 318444 | chr16 | 337510 | 337749 | chr16 | 410303 | 410482 |
| chr16 | 611304 | 611603 | chr16 | 611876 | 612355 | chr16 | 612774 | 613133 |
| chr16 | 667466 | 667561 | chr16 | 677879 | 677993 | chr16 | 700225 | 700404 |
| chr16 | 726539 | 727078 | chr16 | 731400 | 731699 | chr16 | 735131 | 735670 |
| chr16 | 740888 | 741003 | chr16 | 741280 | 741507 | chr16 | 837262 | 837561 |
| chr16 | 845881 | 846060 | chr16 | 882567 | 882686 | chr16 | 895011 | 895250 |
| chr16 | 943398 | 943637 | chr16 | 1018046 | 1018225 | chr16 | 1030210 | 1030271 |
| chr16 | 1030444 | 1030749 | chr16 | 1052488 | 1052727 | chr16 | 1103032 | 1103032 |
| chr16 | 1116721 | 1116766 | chr16 | 1128927 | 1129226 | chr16 | 1155068 | 1155307 |

TABLE 15-continued

| chr | start | end | chr | start | end | chr | start | end |
|---|---|---|---|---|---|---|---|---|
| chr16 | 1203883 | 1203963 | chr16 | 1204003 | 1204111 | chr16 | 1217226 | 1217583 |
| chr16 | 1217943 | 1218182 | chr16 | 1228711 | 1229010 | chr16 | 1230057 | 1230236 |
| chr16 | 1248521 | 1248760 | chr16 | 1267844 | 1268203 | chr16 | 1271447 | 1271746 |
| chr16 | 1312450 | 1312689 | chr16 | 1323900 | 1324139 | chr16 | 1382862 | 1383041 |
| chr16 | 1394400 | 1394579 | chr16 | 1397380 | 1397559 | chr16 | 1407366 | 1407485 |
| chr16 | 1407819 | 1407938 | chr16 | 1428422 | 1428961 | chr16 | 1491471 | 1491694 |
| chr16 | 1730213 | 1730692 | chr16 | 1741757 | 1742176 | chr16 | 2028986 | 2029225 |
| chr16 | 2040818 | 2040961 | chr16 | 2040981 | 2040981 | chr16 | 2040983 | 2041513 |
| chr16 | 2041582 | 2042257 | chr16 | 2106629 | 2106741 | chr16 | 2128503 | 2128682 |
| chr16 | 2129033 | 2129332 | chr16 | 2141835 | 2142014 | chr16 | 2142468 | 2142707 |
| chr16 | 2213239 | 2213396 | chr16 | 2232665 | 2232784 | chr16 | 2234634 | 2235113 |
| chr16 | 2281163 | 2281402 | chr16 | 2287231 | 2287453 | chr16 | 2531136 | 2531255 |
| chr16 | 2764275 | 2764574 | chr16 | 2770033 | 2770512 | chr16 | 2818018 | 2818249 |
| chr16 | 2892457 | 2892603 | chr16 | 2892627 | 2892797 | chr16 | 3017157 | 3017431 |
| chr16 | 3068097 | 3068276 | chr16 | 3151038 | 3151264 | chr16 | 3211625 | 3211742 |
| chr16 | 3211805 | 3211982 | chr16 | 3220474 | 3220557 | chr16 | 3220591 | 3220893 |
| chr16 | 3221142 | 3221701 | chr16 | 3221787 | 3222325 | chr16 | 3225390 | 3225689 |
| chr16 | 3232697 | 3233017 | chr16 | 3233199 | 3233331 | chr16 | 3233435 | 3234104 |
| chr16 | 3234197 | 3234541 | chr16 | 3237783 | 3238022 | chr16 | 3238164 | 3238622 |
| chr16 | 3238912 | 3239631 | chr16 | 3239692 | 3239931 | chr16 | 3241517 | 3241756 |
| chr16 | 3241862 | 3241981 | chr16 | 3355200 | 3355234 | chr16 | 3355251 | 3355799 |
| chr16 | 3598818 | 3599057 | chr16 | 3696620 | 3696799 | chr16 | 3802932 | 3803171 |
| chr16 | 4264433 | 4264792 | chr16 | 4431039 | 4431213 | chr16 | 4846061 | 4846415 |
| chr16 | 5037803 | 5038102 | chr16 | 5541026 | 5541257 | chr16 | 6069989 | 6070122 |
| chr16 | 7354560 | 7354658 | chr16 | 7354700 | 7354739 | chr16 | 8780956 | 8781135 |
| chr16 | 8870279 | 8870458 | chr16 | 9009781 | 9010075 | chr16 | 10274325 | 10274504 |
| chr16 | 10275231 | 10275470 | chr16 | 10275671 | 10276030 | chr16 | 10276270 | 10276799 |
| chr16 | 10276801 | 10277051 | chr16 | 10277072 | 10277409 | chr16 | 10479719 | 10479966 |
| chr16 | 10479968 | 10480078 | chr16 | 12971812 | 12972035 | chr16 | 12994359 | 12994838 |
| chr16 | 12994969 | 12995688 | chr16 | 12995707 | 12995804 | chr16 | 12996074 | 12996426 |
| chr16 | 12996520 | 12996819 | chr16 | 12996861 | 12997100 | chr16 | 12997306 | 12997785 |
| chr16 | 14725745 | 14725864 | chr16 | 15489851 | 15489884 | chr16 | 15820726 | 15820965 |
| chr16 | 18802486 | 18802725 | chr16 | 18950987 | 18951093 | chr16 | 19567117 | 19567536 |
| chr16 | 19895051 | 19895125 | chr16 | 19895156 | 19895230 | chr16 | 21831520 | 21832052 |
| chr16 | 21839250 | 21839348 | chr16 | 22824599 | 22825077 | chr16 | 22825158 | 22825198 |
| chr16 | 22825225 | 22825470 | chr16 | 22825886 | 22826184 | chr16 | 23313374 | 23313613 |
| chr16 | 23313674 | 23313739 | chr16 | 23313780 | 23313913 | chr16 | 23706240 | 23706287 |
| chr16 | 23706412 | 23706599 | chr16 | 23765995 | 23766098 | chr16 | 23766133 | 23766234 |
| chr16 | 23847311 | 23847325 | chr16 | 23847327 | 23847512 | chr16 | 23847789 | 23847816 |
| chr16 | 23847818 | 23847875 | chr16 | 23847934 | 23848003 | chr16 | 23848005 | 23848053 |
| chr16 | 24267013 | 24267145 | chr16 | 24267221 | 24267312 | chr16 | 24267383 | 24267594 |
| chr16 | 25266436 | 25266675 | chr16 | 25702855 | 25703094 | chr16 | 25703686 | 25704123 |
| chr16 | 25704390 | 25704705 | chr16 | 26664758 | 26664853 | chr16 | 27460002 | 27460156 |
| chr16 | 28074101 | 28074255 | chr16 | 28074418 | 28074760 | chr16 | 28074869 | 28074937 |
| chr16 | 28074956 | 28075288 | chr16 | 29118954 | 29119133 | chr16 | 29153201 | 29153254 |
| chr16 | 29244800 | 29245099 | chr16 | 29830796 | 29831155 | chr16 | 29888549 | 29888761 |
| chr16 | 30017240 | 30017539 | chr16 | 30116211 | 30116390 | chr16 | 30124597 | 30124949 |
| chr16 | 30804458 | 30804575 | chr16 | 30826363 | 30826570 | chr16 | 30906930 | 30907049 |
| chr16 | 30907123 | 30907229 | chr16 | 31228310 | 31228402 | chr16 | 31446904 | 31447173 |
| chr16 | 31497971 | 31498087 | chr16 | 31500460 | 31500759 | chr16 | 31580469 | 31580739 |
| chr16 | 46721556 | 46721787 | chr16 | 47177447 | 47177686 | chr16 | 48845120 | 48845229 |
| chr16 | 49309067 | 49309366 | chr16 | 49311432 | 49311990 | chr16 | 49312033 | 49312391 |
| chr16 | 49313268 | 49313807 | chr16 | 49313921 | 49314220 | chr16 | 49314341 | 49314640 |
| chr16 | 49314692 | 49314822 | chr16 | 49315202 | 49315381 | chr16 | 49315831 | 49316316 |
| chr16 | 49316509 | 49316670 | chr16 | 49637986 | 49638165 | chr16 | 50335693 | 50335872 |
| chr16 | 51183964 | 51184431 | chr16 | 51184725 | 51184958 | chr16 | 51185055 | 51185292 |
| chr16 | 51185763 | 51185965 | chr16 | 51186026 | 51186329 | chr16 | 51186596 | 51187036 |
| chr16 | 51189848 | 51190038 | chr16 | 51190122 | 51190309 | chr16 | 53563519 | 53563734 |
| chr16 | 54318855 | 54319063 | chr16 | 54319325 | 54319564 | chr16 | 54321557 | 54321819 |
| chr16 | 54321908 | 54321916 | chr16 | 54324960 | 54325199 | chr16 | 54628600 | 54628959 |
| chr16 | 54964875 | 54965211 | chr16 | 54966728 | 54967265 | chr16 | 54970986 | 54971007 |
| chr16 | 54971326 | 54971505 | chr16 | 55090585 | 55090944 | chr16 | 55357827 | 55357941 |
| chr16 | 55357992 | 55358186 | chr16 | 55358213 | 55358351 | chr16 | 55358567 | 55358632 |
| chr16 | 55358785 | 55359175 | chr16 | 55362963 | 55363326 | chr16 | 55364631 | 55364930 |
| chr16 | 55365020 | 55365219 | chr16 | 55404898 | 55405200 | chr16 | 55405202 | 55405317 |
| chr16 | 55512745 | 55512763 | chr16 | 55512936 | 55512984 | chr16 | 55689853 | 55689901 |
| chr16 | 55689903 | 55689991 | chr16 | 55690013 | 55690380 | chr16 | 55690454 | 55690577 |
| chr16 | 55690762 | 55690912 | chr16 | 56224479 | 56224782 | chr16 | 56224784 | 56224793 |
| chr16 | 56224795 | 56224833 | chr16 | 56224881 | 56224958 | chr16 | 56228271 | 56228417 |
| chr16 | 56228578 | 56228686 | chr16 | 56651006 | 56651124 | chr16 | 56651239 | 56651365 |
| chr16 | 56659095 | 56659754 | chr16 | 56672077 | 56672173 | chr16 | 56672222 | 56672386 |
| chr16 | 56672514 | 56672761 | chr16 | 56709755 | 56709893 | chr16 | 56709950 | 56710114 |
| chr16 | 57222710 | 57222806 | chr16 | 57935476 | 57935655 | chr16 | 58018531 | 58018950 |
| chr16 | 58019149 | 58019508 | chr16 | 58120875 | 58121058 | chr16 | 58497136 | 58497336 |
| chr16 | 58497470 | 58497495 | chr16 | 58497672 | 58497911 | chr16 | 58498101 | 58498280 |
| chr16 | 58498468 | 58498585 | chr16 | 58498587 | 58498809 | chr16 | 58521634 | 58521813 |
| chr16 | 58550415 | 58550587 | chr16 | 58969669 | 58969895 | chr16 | 62068387 | 62068610 |
| chr16 | 62068923 | 62069057 | chr16 | 62070669 | 62070848 | chr16 | 65154833 | 65155192 |

TABLE 15-continued

| chr | start | end | chr | start | end | chr | start | end |
|---|---|---|---|---|---|---|---|---|
| chr16 | 65156288 | 65156587 | chr16 | 66461694 | 66461933 | chr16 | 66612797 | 66613096 |
| chr16 | 66613335 | 66613359 | chr16 | 67197615 | 67197854 | chr16 | 67197935 | 67198114 |
| chr16 | 67198818 | 67199057 | chr16 | 67241130 | 67241309 | chr16 | 67313791 | 67313970 |
| chr16 | 68544170 | 68544409 | chr16 | 68676307 | 68676605 | chr16 | 68676842 | 68677086 |
| chr16 | 68770847 | 68771086 | chr16 | 68771167 | 68771402 | chr16 | 68876728 | 68876847 |
| chr16 | 70595543 | 70595782 | chr16 | 71459957 | 71460089 | chr16 | 71460271 | 71460429 |
| chr16 | 71715705 | 71715884 | chr16 | 72957660 | 72957899 | chr16 | 73100576 | 73100612 |
| chr16 | 75019677 | 75019856 | chr16 | 77247366 | 77247545 | chr16 | 77468182 | 77468458 |
| chr16 | 77822493 | 77822589 | chr16 | 77822875 | 77822972 | chr16 | 78079893 | 78080132 |
| chr16 | 79623798 | 79623968 | chr16 | 80838052 | 80838173 | chr16 | 80966296 | 80966535 |
| chr16 | 82660279 | 82660578 | chr16 | 82660638 | 82660727 | chr16 | 82660729 | 82660817 |
| chr16 | 84074767 | 84074946 | chr16 | 84153290 | 84153469 | chr16 | 84402163 | 84402402 |
| chr16 | 84853274 | 84853452 | chr16 | 85075418 | 85075644 | chr16 | 85317747 | 85317879 |
| chr16 | 85485652 | 85485951 | chr16 | 85517254 | 85517613 | chr16 | 85678551 | 85678850 |
| chr16 | 85684234 | 85684533 | chr16 | 85699596 | 85699925 | chr16 | 85932754 | 85932933 |
| chr16 | 86320254 | 86320489 | chr16 | 86320491 | 86320493 | chr16 | 86320659 | 86320898 |
| chr16 | 86320925 | 86321147 | chr16 | 86530848 | 86530993 | chr16 | 86531017 | 86531147 |
| chr16 | 86531233 | 86531289 | chr16 | 86531375 | 86531481 | chr16 | 86531528 | 86531652 |
| chr16 | 86541537 | 86541956 | chr16 | 86542296 | 86542535 | chr16 | 86544103 | 86544558 |
| chr16 | 86545060 | 86545062 | chr16 | 86599481 | 86599931 | chr16 | 86600406 | 86600765 |
| chr16 | 86600868 | 86601107 | chr16 | 86601204 | 86601623 | chr16 | 86602038 | 86602590 |
| chr16 | 87092347 | 87092646 | chr16 | 87635029 | 87635208 | chr16 | 87636444 | 87636491 |
| chr16 | 87636627 | 87636782 | chr16 | 87636784 | 87636983 | chr16 | 87714178 | 87714491 |
| chr16 | 87723648 | 87724187 | chr16 | 88164316 | 88164555 | chr16 | 88498142 | 88498861 |
| chr16 | 88503978 | 88504397 | chr16 | 88506265 | 88506616 | chr16 | 88512329 | 88512628 |
| chr16 | 88603617 | 88603848 | chr16 | 88623885 | 88624165 | chr16 | 88757428 | 88757571 |
| chr16 | 88879858 | 88880097 | chr16 | 88883159 | 88883458 | chr16 | 88940981 | 88941220 |
| chr16 | 88942021 | 88942239 | chr16 | 88943463 | 88944122 | chr16 | 88945726 | 88946085 |
| chr16 | 88955160 | 88955459 | chr16 | 88956136 | 88956495 | chr16 | 88957374 | 88957934 |
| chr16 | 88958295 | 88958534 | chr16 | 88963191 | 88963850 | chr16 | 88966207 | 88966686 |
| chr16 | 88968630 | 88968869 | chr16 | 88977929 | 88978168 | chr16 | 88992975 | 88993334 |
| chr16 | 88999543 | 88999557 | chr16 | 88999574 | 88999693 | chr16 | 89000127 | 89000306 |
| chr16 | 89001020 | 89001139 | chr16 | 89007420 | 89007659 | chr16 | 89007789 | 89007879 |
| chr16 | 89008488 | 89008667 | chr16 | 89047643 | 89047822 | chr16 | 89072400 | 89072879 |
| chr16 | 89086034 | 89086273 | chr16 | 89107585 | 89107824 | chr16 | 89109345 | 89109490 |
| chr16 | 89119940 | 89120419 | chr16 | 89120607 | 89120963 | chr16 | 89137919 | 89138158 |
| chr16 | 89220244 | 89220483 | chr16 | 89220580 | 89220999 | chr16 | 89254563 | 89254742 |
| chr16 | 89267260 | 89267439 | chr16 | 89267709 | 89267825 | chr16 | 89558549 | 89558807 |
| chr16 | 89883930 | 89884289 | chr16 | 89884875 | 89884989 | chr16 | 89885115 | 89885229 |
| chr16 | 89900033 | 89900272 | chr16 | 89900372 | 89900611 | chr17 | 616914 | 617026 |
| chr17 | 1082923 | 1083093 | chr17 | 1174274 | 1174362 | chr17 | 1174385 | 1174505 |
| chr17 | 1536129 | 1536221 | chr17 | 1546312 | 1546539 | chr17 | 1623600 | 1623779 |
| chr17 | 1959437 | 1959614 | chr17 | 2207848 | 2207967 | chr17 | 2208042 | 2208147 |
| chr17 | 2220974 | 2221142 | chr17 | 2249977 | 2250096 | chr17 | 3438818 | 3438938 |
| chr17 | 3439030 | 3439057 | chr17 | 3658751 | 3658930 | chr17 | 3658991 | 3659110 |
| chr17 | 4544510 | 4544809 | chr17 | 4699212 | 4699331 | chr17 | 4891237 | 4891381 |
| chr17 | 5000340 | 5000879 | chr17 | 6616543 | 6616782 | chr17 | 6616813 | 6616883 |
| chr17 | 6616885 | 6617174 | chr17 | 6679220 | 6679393 | chr17 | 6946113 | 6946153 |
| chr17 | 6946176 | 6946244 | chr17 | 7348792 | 7349070 | chr17 | 7368864 | 7369223 |
| chr17 | 7555099 | 7555338 | chr17 | 7573915 | 7574094 | chr17 | 7576923 | 7577222 |
| chr17 | 7577423 | 7577662 | chr17 | 7578078 | 7578557 | chr17 | 7906156 | 7906514 |
| chr17 | 8104071 | 8104173 | chr17 | 8230246 | 8230350 | chr17 | 8230352 | 8230785 |
| chr17 | 8774685 | 8774728 | chr17 | 8868524 | 8868668 | chr17 | 8868815 | 8869213 |
| chr17 | 8869215 | 8869483 | chr17 | 8906183 | 8906602 | chr17 | 8906895 | 8907213 |
| chr17 | 8907215 | 8907674 | chr17 | 8925983 | 8926201 | chr17 | 10100995 | 10101110 |
| chr17 | 10101132 | 10101448 | chr17 | 10102331 | 10102750 | chr17 | 11144839 | 11144852 |
| chr17 | 11144923 | 11145078 | chr17 | 13503875 | 13503945 | chr17 | 13504195 | 13504294 |
| chr17 | 13504470 | 13504769 | chr17 | 13505002 | 13505292 | chr17 | 13505316 | 13505675 |
| chr17 | 14200962 | 14201261 | chr17 | 14204138 | 14204317 | chr17 | 14204425 | 14204724 |
| chr17 | 15244988 | 15245215 | chr17 | 16282157 | 16282396 | chr17 | 16570674 | 16570897 |
| chr17 | 17062513 | 17062752 | chr17 | 17123889 | 17124068 | chr17 | 17398520 | 17398542 |
| chr17 | 18163094 | 18163415 | chr17 | 18538207 | 18538360 | chr17 | 20817897 | 20817998 |
| chr17 | 25620495 | 25620794 | chr17 | 25676885 | 25677004 | chr17 | 25680190 | 25680276 |
| chr17 | 25907676 | 25907855 | chr17 | 26263104 | 26263214 | chr17 | 26554551 | 26554753 |
| chr17 | 26961721 | 26961922 | chr17 | 27038568 | 27038686 | chr17 | 27038907 | 27038985 |
| chr17 | 27044696 | 27044744 | chr17 | 27056846 | 27056957 | chr17 | 27170072 | 27170182 |
| chr17 | 27181284 | 27181456 | chr17 | 27332378 | 27332737 | chr17 | 27716018 | 27716134 |
| chr17 | 27716198 | 27716314 | chr17 | 27940276 | 27940338 | chr17 | 27940591 | 27940995 |
| chr17 | 28562614 | 28562853 | chr17 | 29232148 | 29232267 | chr17 | 29249615 | 29249854 |
| chr17 | 29250020 | 29250034 | chr17 | 29298002 | 29298184 | chr17 | 29298186 | 29298463 |
| chr17 | 29718123 | 29718362 | chr17 | 29719096 | 29719247 | chr17 | 29719290 | 29719335 |
| chr17 | 30243689 | 30243988 | chr17 | 30250242 | 30250345 | chr17 | 31618333 | 31618409 |
| chr17 | 31618411 | 31619412 | chr17 | 31619870 | 31620109 | chr17 | 32483946 | 32484125 |
| chr17 | 32906299 | 32906556 | chr17 | 32906599 | 32906718 | chr17 | 32906888 | 32907112 |
| chr17 | 32907136 | 32907247 | chr17 | 32907554 | 32907705 | chr17 | 32907707 | 32907805 |
| chr17 | 32908044 | 32908147 | chr17 | 32908171 | 32908463 | chr17 | 32908550 | 32909029 |
| chr17 | 33672832 | 33673071 | chr17 | 33877184 | 33877303 | chr17 | 33917240 | 33917350 |
| chr17 | 35165549 | 35165788 | chr17 | 35165912 | 35166091 | chr17 | 35285455 | 35285754 |

TABLE 15-continued

| chr | start | end | chr | start | end | chr | start | end |
|---|---|---|---|---|---|---|---|---|
| chr17 | 35290313 | 35290732 | chr17 | 35291242 | 35291457 | chr17 | 35291749 | 35291899 |
| chr17 | 35291921 | 35292708 | chr17 | 35293630 | 35294229 | chr17 | 35294364 | 35294481 |
| chr17 | 35294483 | 35294491 | chr17 | 35294493 | 35294603 | chr17 | 35294955 | 35295254 |
| chr17 | 35296069 | 35296368 | chr17 | 35296629 | 35296988 | chr17 | 35297527 | 35298246 |
| chr17 | 35299154 | 35299444 | chr17 | 35299601 | 35299966 | chr17 | 35300261 | 35300713 |
| chr17 | 35300813 | 35300953 | chr17 | 35303259 | 35303618 | chr17 | 36102935 | 36103289 |
| chr17 | 36103291 | 36103414 | chr17 | 36103497 | 36103676 | chr17 | 36104031 | 36104035 |
| chr17 | 36104218 | 36104551 | chr17 | 36104644 | 36104870 | chr17 | 36105141 | 36105350 |
| chr17 | 36105459 | 36105680 | chr17 | 37192168 | 37192281 | chr17 | 37321100 | 37321625 |
| chr17 | 37321788 | 37322010 | chr17 | 37366236 | 37366655 | chr17 | 37369106 | 37369285 |
| chr17 | 37380922 | 37381430 | chr17 | 37381571 | 37381727 | chr17 | 37381826 | 37381941 |
| chr17 | 37382048 | 37382347 | chr17 | 37757066 | 37757305 | chr17 | 37760406 | 37760645 |
| chr17 | 37761897 | 37762436 | chr17 | 37879697 | 37879712 | chr17 | 38179295 | 38179348 |
| chr17 | 38179492 | 38179534 | chr17 | 38347473 | 38347616 | chr17 | 38497542 | 38497721 |
| chr17 | 38498009 | 38498188 | chr17 | 39682550 | 39682729 | chr17 | 40332846 | 40333268 |
| chr17 | 40400770 | 40401109 | chr17 | 40464179 | 40464418 | chr17 | 40464443 | 40464627 |
| chr17 | 40975576 | 40975754 | chr17 | 41278542 | 41278693 | chr17 | 41651776 | 41651887 |
| chr17 | 41791413 | 41791565 | chr17 | 41791591 | 41791599 | chr17 | 42030244 | 42030751 |
| chr17 | 42030780 | 42030843 | chr17 | 42061240 | 42061479 | chr17 | 42082421 | 42082660 |
| chr17 | 42092116 | 42092187 | chr17 | 42092189 | 42092295 | chr17 | 42331637 | 42331746 |
| chr17 | 42393780 | 42394113 | chr17 | 42402782 | 42402984 | chr17 | 42587336 | 42587452 |
| chr17 | 42635199 | 42635844 | chr17 | 42733619 | 42733978 | chr17 | 42787580 | 42787699 |
| chr17 | 42907489 | 42907631 | chr17 | 42907655 | 42908028 | chr17 | 43001800 | 43002029 |
| chr17 | 43044584 | 43044763 | chr17 | 43045039 | 43045208 | chr17 | 43047355 | 43047404 |
| chr17 | 43047753 | 43047834 | chr17 | 43339012 | 43339408 | chr17 | 43339546 | 43339994 |
| chr17 | 43974158 | 43974400 | chr17 | 45331345 | 45331404 | chr17 | 45810767 | 45811426 |
| chr17 | 45867239 | 45867538 | chr17 | 46124907 | 46124970 | chr17 | 46125007 | 46125146 |
| chr17 | 46619224 | 46619224 | chr17 | 46620405 | 46621184 | chr17 | 46621257 | 46621535 |
| chr17 | 46621764 | 46622003 | chr17 | 46655074 | 46655253 | chr17 | 46655351 | 46655394 |
| chr17 | 46655396 | 46655419 | chr17 | 46655451 | 46655561 | chr17 | 46655563 | 46655999 |
| chr17 | 46656058 | 46656531 | chr17 | 46659385 | 46659926 | chr17 | 46663666 | 46663825 |
| chr17 | 46663856 | 46663928 | chr17 | 46674831 | 46675072 | chr17 | 46675086 | 46675685 |
| chr17 | 46690430 | 46690705 | chr17 | 46691430 | 46691669 | chr17 | 46691719 | 46691819 |
| chr17 | 46691988 | 46692198 | chr17 | 46692344 | 46692509 | chr17 | 46710857 | 46710990 |
| chr17 | 46713934 | 46714130 | chr17 | 46714132 | 46714166 | chr17 | 46795563 | 46796374 |
| chr17 | 46796499 | 46796545 | chr17 | 46796606 | 46796638 | chr17 | 46796850 | 46797214 |
| chr17 | 46797275 | 46797662 | chr17 | 46799522 | 46800001 | chr17 | 46800516 | 46800755 |
| chr17 | 46800860 | 46801048 | chr17 | 46801109 | 46801418 | chr17 | 46802364 | 46802912 |
| chr17 | 46802994 | 46803286 | chr17 | 46804029 | 46804508 | chr17 | 46810328 | 46811047 |
| chr17 | 46811269 | 46811500 | chr17 | 46811595 | 46811628 | chr17 | 46816191 | 46816730 |
| chr17 | 46824218 | 46824276 | chr17 | 46824359 | 46824915 | chr17 | 46824917 | 46825149 |
| chr17 | 46825190 | 46825609 | chr17 | 46826897 | 46827196 | chr17 | 46827244 | 46827502 |
| chr17 | 46827626 | 46827843 | chr17 | 46829420 | 46829659 | chr17 | 46829898 | 46830136 |
| chr17 | 46830190 | 46830195 | chr17 | 46831700 | 46832326 | chr17 | 46832490 | 46832719 |
| chr17 | 47072716 | 47073029 | chr17 | 47073104 | 47073328 | chr17 | 47073389 | 47073555 |
| chr17 | 47073899 | 47074318 | chr17 | 47074459 | 47074489 | chr17 | 47074597 | 47074998 |
| chr17 | 47075083 | 47075442 | chr17 | 47075616 | 47075735 | chr17 | 47075880 | 47076155 |
| chr17 | 47574001 | 47574240 | chr17 | 47657445 | 47657684 | chr17 | 47865416 | 47865655 |
| chr17 | 47987423 | 47987722 | chr17 | 47987843 | 47988202 | chr17 | 48041057 | 48041416 |
| chr17 | 48041578 | 48041817 | chr17 | 48041965 | 48042141 | chr17 | 48042337 | 48042648 |
| chr17 | 48042751 | 48043056 | chr17 | 48048857 | 48049156 | chr17 | 48049228 | 48050607 |
| chr17 | 48070946 | 48071125 | chr17 | 48071694 | 48071705 | chr17 | 48071807 | 48071957 |
| chr17 | 48612147 | 48612386 | chr17 | 48636500 | 48637219 | chr17 | 48653054 | 48653233 |
| chr17 | 48799847 | 48799963 | chr17 | 49229486 | 49229601 | chr17 | 50235126 | 50235259 |
| chr17 | 50235625 | 50236032 | chr17 | 51900930 | 51901109 | chr17 | 53341155 | 53341557 |
| chr17 | 53342774 | 53343029 | chr17 | 53343031 | 53343193 | chr17 | 53922571 | 53922870 |
| chr17 | 54674890 | 54675137 | chr17 | 54675139 | 54675369 | chr17 | 54755873 | 54755991 |
| chr17 | 56092519 | 56092620 | chr17 | 56234305 | 56234844 | chr17 | 56326853 | 56327092 |
| chr17 | 56327197 | 56327376 | chr17 | 56833025 | 56833324 | chr17 | 56833622 | 56834001 |
| chr17 | 56834020 | 56834161 | chr17 | 56834222 | 56834461 | chr17 | 57297028 | 57297207 |
| chr17 | 58216566 | 58216837 | chr17 | 58216866 | 58217299 | chr17 | 58217357 | 58217652 |
| chr17 | 58218670 | 58219089 | chr17 | 58227281 | 58227398 | chr17 | 58498657 | 58498977 |
| chr17 | 58498979 | 58499396 | chr17 | 59474060 | 59474247 | chr17 | 59474758 | 59475177 |
| chr17 | 59475604 | 59476023 | chr17 | 59476084 | 59476203 | chr17 | 59476314 | 59476733 |
| chr17 | 59478046 | 59478705 | chr17 | 59488010 | 59488424 | chr17 | 59528275 | 59529151 |
| chr17 | 59529254 | 59529265 | chr17 | 59529844 | 59530454 | chr17 | 59531574 | 59532018 |
| chr17 | 59533741 | 59533768 | chr17 | 59533875 | 59534406 | chr17 | 59534557 | 59534580 |
| chr17 | 59534677 | 59534856 | chr17 | 59535059 | 59535298 | chr17 | 59539150 | 59539689 |
| chr17 | 61777984 | 61778074 | chr17 | 61778235 | 61778249 | chr17 | 61817858 | 61818036 |
| chr17 | 61926149 | 61926325 | chr17 | 61926508 | 61926625 | chr17 | 62777244 | 62777543 |
| chr17 | 62777650 | 62777889 | chr17 | 64672276 | 64672635 | chr17 | 66596379 | 66596618 |
| chr17 | 66596884 | 66597123 | chr17 | 67410389 | 67410501 | chr17 | 68164667 | 68164906 |
| chr17 | 70026473 | 70026755 | chr17 | 70112818 | 70113567 | chr17 | 70113648 | 70114019 |
| chr17 | 70114153 | 70114617 | chr17 | 70215595 | 70216307 | chr17 | 70216393 | 70216674 |
| chr17 | 71641465 | 71641761 | chr17 | 71948352 | 71948951 | chr17 | 72270202 | 72270501 |
| chr17 | 72321844 | 72322074 | chr17 | 72322275 | 72322558 | chr17 | 72322612 | 72322694 |
| chr17 | 72353148 | 72353260 | chr17 | 72353417 | 72353531 | chr17 | 72427777 | 72427963 |
| chr17 | 72428244 | 72428483 | chr17 | 72667242 | 72667482 | chr17 | 72848926 | 72849165 |

TABLE 15-continued

| chr | start | end | chr | start | end | chr | start | end |
|---|---|---|---|---|---|---|---|---|
| chr17 | 72856964 | 72857443 | chr17 | 72920705 | 72921124 | chr17 | 73031547 | 73031619 |
| chr17 | 73073610 | 73073684 | chr17 | 73545910 | 73546120 | chr17 | 73584938 | 73584972 |
| chr17 | 73585918 | 73586517 | chr17 | 73608232 | 73608411 | chr17 | 73636062 | 73636421 |
| chr17 | 74028261 | 74028461 | chr17 | 74047755 | 74047994 | chr17 | 74070386 | 74070480 |
| chr17 | 74071344 | 74071583 | chr17 | 74071590 | 74071825 | chr17 | 74072999 | 74073139 |
| chr17 | 74073172 | 74073531 | chr17 | 74390289 | 74390468 | chr17 | 74533808 | 74534363 |
| chr17 | 74534388 | 74534407 | chr17 | 74581083 | 74581322 | chr17 | 74864974 | 74865068 |
| chr17 | 74865070 | 74865273 | chr17 | 74865612 | 74866331 | chr17 | 75207765 | 75207944 |
| chr17 | 75368658 | 75368902 | chr17 | 75368904 | 75369091 | chr17 | 75369093 | 75369317 |
| chr17 | 75369351 | 75369458 | chr17 | 75369493 | 75369950 | chr17 | 75370186 | 75370413 |
| chr17 | 75370522 | 75370701 | chr17 | 75385122 | 75385301 | chr17 | 75523058 | 75523354 |
| chr17 | 75524556 | 75525004 | chr17 | 75525006 | 75525275 | chr17 | 75733902 | 75734108 |
| chr17 | 75797121 | 75797265 | chr17 | 76125122 | 76125301 | chr17 | 76137862 | 76138281 |
| chr17 | 76138525 | 76138710 | chr17 | 76227774 | 76228162 | chr17 | 76228214 | 76228433 |
| chr17 | 76404662 | 76404757 | chr17 | 76921756 | 76921806 | chr17 | 76921860 | 76921934 |
| chr17 | 76974354 | 76974582 | chr17 | 77084488 | 77084667 | chr17 | 77104978 | 77105277 |
| chr17 | 77145037 | 77145336 | chr17 | 77179017 | 77179064 | chr17 | 77179082 | 77179330 |
| chr17 | 77179618 | 77179709 | chr17 | 77179711 | 77179777 | chr17 | 77179800 | 77179891 |
| chr17 | 77776733 | 77776996 | chr17 | 77777053 | 77777152 | chr17 | 77777504 | 77777649 |
| chr17 | 77777651 | 77777904 | chr17 | 77777944 | 77778043 | chr17 | 77778852 | 77779136 |
| chr17 | 77789474 | 77789528 | chr17 | 77825605 | 77825858 | chr17 | 77899590 | 77899634 |
| chr17 | 78122175 | 78122294 | chr17 | 78447053 | 78447213 | chr17 | 78451842 | 78451954 |
| chr17 | 78452109 | 78452141 | chr17 | 78452199 | 78452438 | chr17 | 78452578 | 78452937 |
| chr17 | 78518204 | 78518295 | chr17 | 78599493 | 78599732 | chr17 | 78667897 | 78668256 |
| chr17 | 78874418 | 78874650 | chr17 | 79094095 | 79094334 | chr17 | 79099696 | 79099875 |
| chr17 | 79615087 | 79615136 | chr17 | 79615435 | 79615446 | chr17 | 79626656 | 79626797 |
| chr17 | 79769354 | 79769773 | chr17 | 80254258 | 80254371 | chr17 | 80289153 | 80289392 |
| chr17 | 80329628 | 80330001 | chr17 | 80330165 | 80330167 | chr17 | 80394659 | 80394678 |
| chr17 | 80479366 | 80479525 | chr17 | 80535286 | 80535469 | chr17 | 80654909 | 80655088 |
| chr17 | 80693343 | 80693582 | chr17 | 80797600 | 80798439 | chr17 | 80832209 | 80832508 |
| chr17 | 80832635 | 80832874 | chr17 | 81008543 | 81008902 | chr17 | 81033413 | 81033592 |
| chr17 | 81048919 | 81049098 | chr17 | 81049943 | 81050146 | chr18 | 499454 | 499575 |
| chr18 | 499947 | 500842 | chr18 | 904376 | 904735 | chr18 | 904926 | 905105 |
| chr18 | 905359 | 905616 | chr18 | 905693 | 905718 | chr18 | 906770 | 907009 |
| chr18 | 907384 | 907683 | chr18 | 907826 | 908065 | chr18 | 908373 | 908607 |
| chr18 | 909046 | 909085 | chr18 | 909184 | 909225 | chr18 | 909388 | 909687 |
| chr18 | 2755855 | 2755974 | chr18 | 2906167 | 2906406 | chr18 | 3215032 | 3215271 |
| chr18 | 3498980 | 3499447 | chr18 | 4453885 | 4454244 | chr18 | 4454979 | 4455031 |
| chr18 | 4455259 | 4455272 | chr18 | 5133126 | 5133405 | chr18 | 5196576 | 5197038 |
| chr18 | 5197126 | 5197272 | chr18 | 5197330 | 5197425 | chr18 | 5543132 | 5543158 |
| chr18 | 5543431 | 5543431 | chr18 | 5543900 | 5543957 | chr18 | 5628072 | 5628611 |
| chr18 | 5629700 | 5629826 | chr18 | 5630218 | 5630457 | chr18 | 5891337 | 5891418 |
| chr18 | 5894935 | 5894946 | chr18 | 5895018 | 5895294 | chr18 | 5895881 | 5896180 |
| chr18 | 6729881 | 6730093 | chr18 | 7116858 | 7116883 | chr18 | 7117060 | 7117073 |
| chr18 | 7117616 | 7117885 | chr18 | 7567708 | 7568367 | chr18 | 8608649 | 8608838 |
| chr18 | 8608902 | 8609062 | chr18 | 8612178 | 8612357 | chr18 | 9771621 | 9771850 |
| chr18 | 9912693 | 9912872 | chr18 | 10589013 | 10589432 | chr18 | 11148888 | 11149094 |
| chr18 | 11149116 | 11149127 | chr18 | 11149486 | 11149760 | chr18 | 11149780 | 11149965 |
| chr18 | 11401557 | 11401846 | chr18 | 11751538 | 11751632 | chr18 | 11752128 | 11752473 |
| chr18 | 11752641 | 11752805 | chr18 | 11942634 | 11942746 | chr18 | 12254133 | 12254147 |
| chr18 | 12254305 | 12254672 | chr18 | 12307603 | 12307829 | chr18 | 12376133 | 12376206 |
| chr18 | 13824125 | 13824184 | chr18 | 13826316 | 13826615 | chr18 | 13868620 | 13868920 |
| chr18 | 13868947 | 13869039 | chr18 | 15198162 | 15198269 | chr18 | 18822294 | 18823060 |
| chr18 | 18823101 | 18823373 | chr18 | 19750286 | 19750447 | chr18 | 20911467 | 20911646 |
| chr18 | 21269344 | 21269490 | chr18 | 21269581 | 21269763 | chr18 | 22928981 | 22929096 |
| chr18 | 22929187 | 22929719 | chr18 | 22929927 | 22930283 | chr18 | 22930285 | 22930660 |
| chr18 | 22930715 | 22931254 | chr18 | 23686388 | 23686507 | chr18 | 24127650 | 24128129 |
| chr18 | 24130729 | 24130947 | chr18 | 24131099 | 24131267 | chr18 | 24764851 | 24765188 |
| chr18 | 24765231 | 24765252 | chr18 | 25755556 | 25755744 | chr18 | 25755936 | 25756115 |
| chr18 | 25756542 | 25756822 | chr18 | 25757151 | 25757438 | chr18 | 25757440 | 25757530 |
| chr18 | 25757687 | 25757926 | chr18 | 25758129 | 25758233 | chr18 | 28620819 | 28620956 |
| chr18 | 28621034 | 28621178 | chr18 | 28621242 | 28621274 | chr18 | 28621383 | 28621481 |
| chr18 | 28621545 | 28622024 | chr18 | 28622335 | 28622574 | chr18 | 30349642 | 30349872 |
| chr18 | 31020419 | 31020511 | chr18 | 31158007 | 31158049 | chr18 | 31738953 | 31739552 |
| chr18 | 31802031 | 31802270 | chr18 | 31802864 | 31803043 | chr18 | 31803336 | 31803575 |
| chr18 | 31902690 | 31902944 | chr18 | 32073807 | 32073831 | chr18 | 32073908 | 32074166 |
| chr18 | 32557847 | 32557882 | chr18 | 32557884 | 32557968 | chr18 | 32957702 | 32957813 |
| chr18 | 33078274 | 33078393 | chr18 | 33078634 | 33078753 | chr18 | 33877784 | 33877839 |
| chr18 | 34833519 | 34833554 | chr18 | 35064986 | 35065146 | chr18 | 35065517 | 35065725 |
| chr18 | 35104935 | 35104984 | chr18 | 35144766 | 35144937 | chr18 | 35144969 | 35145545 |
| chr18 | 35146023 | 35146037 | chr18 | 35146062 | 35146322 | chr18 | 35147409 | 35147648 |
| chr18 | 43914156 | 43914226 | chr18 | 43914228 | 43914365 | chr18 | 44259911 | 44260067 |
| chr18 | 44335999 | 44336450 | chr18 | 44337013 | 44337044 | chr18 | 44337445 | 44337618 |
| chr18 | 44337650 | 44337842 | chr18 | 44338099 | 44338164 | chr18 | 44772980 | 44773117 |
| chr18 | 44773574 | 44773967 | chr18 | 44774202 | 44774233 | chr18 | 44774319 | 44774804 |
| chr18 | 44775309 | 44775647 | chr18 | 44776881 | 44777180 | chr18 | 44777227 | 44777406 |
| chr18 | 44777512 | 44777792 | chr18 | 44777949 | 44778411 | chr18 | 44780903 | 44781142 |
| chr18 | 44787695 | 44787934 | chr18 | 44788177 | 44788356 | chr18 | 44789375 | 44789614 |

TABLE 15-continued

| chr | start | end | chr | start | end | chr | start | end |
|---|---|---|---|---|---|---|---|---|
| chr18 | 44789786 | 44790025 | chr18 | 45057993 | 45058293 | chr18 | 45058308 | 45058335 |
| chr18 | 46142587 | 46142715 | chr18 | 49867202 | 49867483 | chr18 | 52988906 | 52989155 |
| chr18 | 52989157 | 52989316 | chr18 | 52989723 | 52989962 | chr18 | 53257052 | 53257291 |
| chr18 | 53446884 | 53447475 | chr18 | 53447799 | 53447903 | chr18 | 53989718 | 53989828 |
| chr18 | 53989876 | 53989957 | chr18 | 54788984 | 54789343 | chr18 | 55019610 | 55019776 |
| chr18 | 55020572 | 55020699 | chr18 | 55020805 | 55020811 | chr18 | 55020981 | 55021340 |
| chr18 | 55103307 | 55103414 | chr18 | 55103762 | 55103824 | chr18 | 55104744 | 55105244 |
| chr18 | 55105630 | 55105929 | chr18 | 55114441 | 55114740 | chr18 | 55850767 | 55851066 |
| chr18 | 56483824 | 56483938 | chr18 | 56815757 | 56815876 | chr18 | 56886981 | 56887469 |
| chr18 | 56887503 | 56887517 | chr18 | 56888470 | 56888656 | chr18 | 56888687 | 56888709 |
| chr18 | 56931460 | 56931682 | chr18 | 56931888 | 56932187 | chr18 | 56932256 | 56932375 |
| chr18 | 56934926 | 56935405 | chr18 | 56935920 | 56936159 | chr18 | 56939025 | 56939264 |
| chr18 | 56939324 | 56939652 | chr18 | 56939764 | 56940171 | chr18 | 56940566 | 56940823 |
| chr18 | 56940863 | 56941245 | chr18 | 56941558 | 56941882 | chr18 | 57363606 | 57363845 |
| chr18 | 57364449 | 57364484 | chr18 | 57364556 | 57364795 | chr18 | 59000886 | 59001125 |
| chr18 | 59001222 | 59001344 | chr18 | 59001498 | 59001821 | chr18 | 60263452 | 60263544 |
| chr18 | 60263661 | 60263991 | chr18 | 60985417 | 60985533 | chr18 | 60985593 | 60985732 |
| chr18 | 60985734 | 60985825 | chr18 | 67067464 | 67067893 | chr18 | 67067895 | 67067971 |
| chr18 | 67067996 | 67068003 | chr18 | 67068059 | 67068114 | chr18 | 67068614 | 67068913 |
| chr18 | 67069142 | 67069321 | chr18 | 70209102 | 70209297 | chr18 | 70209348 | 70209386 |
| chr18 | 70209494 | 70209527 | chr18 | 70210483 | 70210583 | chr18 | 70211527 | 70211766 |
| chr18 | 70534207 | 70534316 | chr18 | 70534428 | 70534686 | chr18 | 70535299 | 70535555 |
| chr18 | 70535576 | 70535658 | chr18 | 70535918 | 70536084 | chr18 | 70536188 | 70536697 |
| chr18 | 70536733 | 70536972 | chr18 | 70537230 | 70537293 | chr18 | 73167500 | 73167919 |
| chr18 | 73627925 | 73628153 | chr18 | 74501045 | 74501267 | chr18 | 74755430 | 74755577 |
| chr18 | 74961264 | 74961737 | chr18 | 74961739 | 74961956 | chr18 | 74962019 | 74962171 |
| chr18 | 74962210 | 74962247 | chr18 | 74962693 | 74962751 | chr18 | 74962896 | 74963546 |
| chr18 | 75339137 | 75339436 | chr18 | 75362839 | 75363078 | chr18 | 75551197 | 75551376 |
| chr18 | 75612137 | 75612376 | chr18 | 75999330 | 75999509 | chr18 | 76239460 | 76239699 |
| chr18 | 76501405 | 76501584 | chr18 | 76653557 | 76653736 | chr18 | 76686175 | 76686354 |
| chr18 | 77143365 | 77143451 | chr18 | 77167752 | 77167929 | chr18 | 77181263 | 77181502 |
| chr18 | 77194838 | 77195077 | chr18 | 77205436 | 77205735 | chr18 | 77285814 | 77286113 |
| chr18 | 77309459 | 77309638 | chr18 | 77312784 | 77313017 | chr18 | 77329633 | 77330101 |
| chr18 | 77371350 | 77371589 | chr18 | 77543156 | 77543335 | chr18 | 77543673 | 77543912 |
| chr18 | 77547985 | 77548048 | chr18 | 77548352 | 77548700 | chr18 | 77550108 | 77550467 |
| chr18 | 77557981 | 77558397 | chr18 | 77558417 | 77558460 | chr18 | 77558732 | 77559031 |
| chr18 | 77576853 | 77577139 | chr18 | 77636517 | 77636696 | chr18 | 78005004 | 78005142 |
| chr19 | 403435 | 403888 | chr19 | 407106 | 407405 | chr19 | 462106 | 462235 |
| chr19 | 468683 | 468862 | chr19 | 485071 | 485490 | chr19 | 549287 | 549526 |
| chr19 | 555509 | 555625 | chr19 | 591272 | 591511 | chr19 | 592492 | 592654 |
| chr19 | 593197 | 593325 | chr19 | 599125 | 599424 | chr19 | 752060 | 752359 |
| chr19 | 869247 | 869363 | chr19 | 883529 | 883888 | chr19 | 883941 | 884240 |
| chr19 | 891441 | 891616 | chr19 | 955668 | 956327 | chr19 | 1003226 | 1003465 |
| chr19 | 1003583 | 1003822 | chr19 | 1004819 | 1005528 | chr19 | 1030082 | 1030309 |
| chr19 | 1047796 | 1047915 | chr19 | 1083392 | 1083526 | chr19 | 1156450 | 1156629 |
| chr19 | 1170089 | 1170328 | chr19 | 1171003 | 1171422 | chr19 | 1220349 | 1220696 |
| chr19 | 1236397 | 1236631 | chr19 | 1274683 | 1274922 | chr19 | 1308066 | 1308184 |
| chr19 | 1325714 | 1325989 | chr19 | 1401655 | 1401894 | chr19 | 1450236 | 1450475 |
| chr19 | 1496313 | 1496552 | chr19 | 1496555 | 1496672 | chr19 | 1524443 | 1524528 |
| chr19 | 1525530 | 1526053 | chr19 | 1527132 | 1527307 | chr19 | 1754094 | 1754194 |
| chr19 | 1754225 | 1754333 | chr19 | 1754653 | 1754892 | chr19 | 1757337 | 1757696 |
| chr19 | 1762376 | 1762506 | chr19 | 1762628 | 1762675 | chr19 | 1764197 | 1764374 |
| chr19 | 1775037 | 1775338 | chr19 | 1776276 | 1776635 | chr19 | 1807893 | 1808492 |
| chr19 | 2251075 | 2251235 | chr19 | 2251611 | 2251794 | chr19 | 2252589 | 2252752 |
| chr19 | 2252901 | 2253736 | chr19 | 2253781 | 2253860 | chr19 | 2274576 | 2274692 |
| chr19 | 2290165 | 2290272 | chr19 | 2290631 | 2290868 | chr19 | 2302693 | 2303052 |
| chr19 | 2331339 | 2331518 | chr19 | 2513149 | 2513388 | chr19 | 2683817 | 2684046 |
| chr19 | 3041486 | 3041522 | chr19 | 3219555 | 3219659 | chr19 | 3296523 | 3296762 |
| chr19 | 3361055 | 3361374 | chr19 | 3361376 | 3361474 | chr19 | 3562249 | 3562583 |
| chr19 | 3578062 | 3578301 | chr19 | 3778053 | 3778472 | chr19 | 3779177 | 3779536 |
| chr19 | 3785566 | 3785836 | chr19 | 3785865 | 3786221 | chr19 | 3820952 | 3821311 |
| chr19 | 3822008 | 3822110 | chr19 | 3822135 | 3822307 | chr19 | 3855322 | 3855681 |
| chr19 | 4054334 | 4054463 | chr19 | 4054540 | 4054573 | chr19 | 4311173 | 4311350 |
| chr19 | 4548040 | 4548459 | chr19 | 4550169 | 4550408 | chr19 | 4555813 | 4556214 |
| chr19 | 4557018 | 4557317 | chr19 | 4670678 | 4670857 | chr19 | 5292709 | 5292948 |
| chr19 | 5338820 | 5338851 | chr19 | 5338901 | 5339239 | chr19 | 5759670 | 5759789 |
| chr19 | 5826175 | 5826284 | chr19 | 5910275 | 5910429 | chr19 | 5914687 | 5914866 |
| chr19 | 5914907 | 5915146 | chr19 | 6590244 | 6590582 | chr19 | 7794919 | 7795338 |
| chr19 | 7852944 | 7853243 | chr19 | 7853262 | 7853471 | chr19 | 7853544 | 7853561 |
| chr19 | 8115149 | 8115376 | chr19 | 8576838 | 8577077 | chr19 | 9473939 | 9474140 |
| chr19 | 9517511 | 9517791 | chr19 | 9608817 | 9609116 | chr19 | 9609229 | 9609528 |
| chr19 | 9903828 | 9904054 | chr19 | 9937370 | 9937489 | chr19 | 10231221 | 10231331 |
| chr19 | 10361965 | 10362076 | chr19 | 10398128 | 10398361 | chr19 | 10405892 | 10406160 |
| chr19 | 10406279 | 10406431 | chr19 | 10406798 | 10407030 | chr19 | 10407045 | 10407211 |
| chr19 | 10527085 | 10527282 | chr19 | 10531317 | 10531616 | chr19 | 10531890 | 10532069 |
| chr19 | 10624740 | 10624853 | chr19 | 10624966 | 10625558 | chr19 | 10823581 | 10823708 |
| chr19 | 11590929 | 11591288 | chr19 | 11592611 | 11592850 | chr19 | 11592942 | 11593241 |
| chr19 | 11689363 | 11689662 | chr19 | 11959816 | 11960175 | chr19 | 12163452 | 12163770 |

TABLE 15-continued

| chr | start | end | chr | start | end | chr | start | end |
|---|---|---|---|---|---|---|---|---|
| chr19 | 12163819 | 12163998 | chr19 | 12175356 | 12175595 | chr19 | 12175731 | 12176090 |
| chr19 | 12202937 | 12203349 | chr19 | 12203351 | 12203638 | chr19 | 12266924 | 12267308 |
| chr19 | 12267310 | 12267763 | chr19 | 12305754 | 12306194 | chr19 | 12306230 | 12306303 |
| chr19 | 12306305 | 12306351 | chr19 | 12476405 | 12476465 | chr19 | 12476501 | 12476644 |
| chr19 | 12606297 | 12606556 | chr19 | 12750903 | 12751142 | chr19 | 12863329 | 12863616 |
| chr19 | 12951921 | 12952129 | chr19 | 12952131 | 12952220 | chr19 | 12996076 | 12996375 |
| chr19 | 13616617 | 13616957 | chr19 | 13617159 | 13617336 | chr19 | 13618186 | 13618485 |
| chr19 | 13965933 | 13966022 | chr19 | 14181217 | 14181682 | chr19 | 14584168 | 14584413 |
| chr19 | 14584537 | 14584868 | chr19 | 15090097 | 15090576 | chr19 | 15121611 | 15121970 |
| chr19 | 15122030 | 15122314 | chr19 | 15288346 | 15288945 | chr19 | 15292293 | 15292592 |
| chr19 | 15342635 | 15343411 | chr19 | 15344007 | 15344131 | chr19 | 15344418 | 15344426 |
| chr19 | 17006991 | 17007389 | chr19 | 17007447 | 17007764 | chr19 | 17008422 | 17008519 |
| chr19 | 17008586 | 17008699 | chr19 | 17008821 | 17008884 | chr19 | 17392545 | 17392964 |
| chr19 | 17717212 | 17717391 | chr19 | 17759145 | 17759504 | chr19 | 17791108 | 17791287 |
| chr19 | 17958396 | 17958935 | chr19 | 17983447 | 17983666 | chr19 | 17983840 | 17983910 |
| chr19 | 18041167 | 18041286 | chr19 | 18103637 | 18103816 | chr19 | 18104390 | 18104493 |
| chr19 | 18271871 | 18271999 | chr19 | 18330935 | 18331234 | chr19 | 18343355 | 18343654 |
| chr19 | 18343880 | 18344062 | chr19 | 18383252 | 18383431 | chr19 | 18714465 | 18714581 |
| chr19 | 18811473 | 18811771 | chr19 | 18899333 | 18899718 | chr19 | 18901753 | 18902172 |
| chr19 | 18980680 | 18980718 | chr19 | 18980912 | 18980979 | chr19 | 18989722 | 18990360 |
| chr19 | 18994808 | 18995227 | chr19 | 19334769 | 19334993 | chr19 | 19645776 | 19646015 |
| chr19 | 19651991 | 19652164 | chr19 | 20011908 | 20011992 | chr19 | 20012053 | 20012172 |
| chr19 | 20188746 | 20188865 | chr19 | 20189411 | 20189530 | chr19 | 21646333 | 21646512 |
| chr19 | 21769223 | 21769375 | chr19 | 22018429 | 22018724 | chr19 | 22034402 | 22034418 |
| chr19 | 22034420 | 22034422 | chr19 | 22034447 | 22034896 | chr19 | 22610542 | 22610701 |
| chr19 | 22715053 | 22715532 | chr19 | 23254115 | 23254294 | chr19 | 23257780 | 23258008 |
| chr19 | 23258306 | 23258559 | chr19 | 23258680 | 23258799 | chr19 | 23299705 | 23299784 |
| chr19 | 23433104 | 23433223 | chr19 | 23598358 | 23598420 | chr19 | 24154518 | 24154697 |
| chr19 | 24216940 | 24217119 | chr19 | 29284377 | 29284576 | chr19 | 29505081 | 29505258 |
| chr19 | 30015844 | 30015963 | chr19 | 30016025 | 30016803 | chr19 | 30016832 | 30016929 |
| chr19 | 30017452 | 30017510 | chr19 | 30017578 | 30017722 | chr19 | 30017766 | 30018691 |
| chr19 | 30019043 | 30019529 | chr19 | 30019531 | 30019611 | chr19 | 30019661 | 30019931 |
| chr19 | 30020014 | 30020553 | chr19 | 30021253 | 30021279 | chr19 | 30215468 | 30215572 |
| chr19 | 30252214 | 30252330 | chr19 | 30555254 | 30555473 | chr19 | 30562687 | 30562831 |
| chr19 | 30637413 | 30637633 | chr19 | 30713384 | 30713593 | chr19 | 30713686 | 30713803 |
| chr19 | 30713829 | 30714128 | chr19 | 30714425 | 30714508 | chr19 | 30715315 | 30715854 |
| chr19 | 30716236 | 30716655 | chr19 | 30716732 | 30716770 | chr19 | 30716953 | 30718231 |
| chr19 | 30718761 | 30718934 | chr19 | 30719369 | 30720134 | chr19 | 30865626 | 30866025 |
| chr19 | 30866453 | 30866525 | chr19 | 31804650 | 31804829 | chr19 | 31839838 | 31839928 |
| chr19 | 31839942 | 31839969 | chr19 | 31841834 | 31842072 | chr19 | 31842116 | 31842481 |
| chr19 | 32364265 | 32364504 | chr19 | 32516309 | 32516495 | chr19 | 32715588 | 32715827 |
| chr19 | 32898350 | 32898589 | chr19 | 33167035 | 33167488 | chr19 | 33167497 | 33167514 |
| chr19 | 33467984 | 33468157 | chr19 | 33685493 | 33685683 | chr19 | 33792412 | 33792612 |
| chr19 | 33794599 | 33794745 | chr19 | 33794780 | 33794838 | chr19 | 34112185 | 34112287 |
| chr19 | 34112327 | 34112424 | chr19 | 34112450 | 34112730 | chr19 | 34113259 | 34113303 |
| chr19 | 34113367 | 34113398 | chr19 | 34113400 | 34113678 | chr19 | 34113911 | 34114050 |
| chr19 | 34972523 | 34972569 | chr19 | 34973243 | 34973330 | chr19 | 34973558 | 34973644 |
| chr19 | 34973646 | 34973797 | chr19 | 35263983 | 35264092 | chr19 | 35395923 | 35395949 |
| chr19 | 35396251 | 35396462 | chr19 | 35616250 | 35616489 | chr19 | 35781298 | 35781537 |
| chr19 | 35797822 | 35798061 | chr19 | 36048504 | 36048863 | chr19 | 36049246 | 36049368 |
| chr19 | 36049397 | 36049497 | chr19 | 36222334 | 36222567 | chr19 | 36249933 | 36250232 |
| chr19 | 36334884 | 36335243 | chr19 | 36347791 | 36348147 | chr19 | 36450030 | 36450232 |
| chr19 | 36523258 | 36523557 | chr19 | 36735953 | 36736132 | chr19 | 36736226 | 36736296 |
| chr19 | 36736315 | 36736585 | chr19 | 36822249 | 36822467 | chr19 | 36822558 | 36822968 |
| chr19 | 36909074 | 36909349 | chr19 | 36909624 | 36910028 | chr19 | 36912257 | 36912350 |
| chr19 | 36912481 | 36912496 | chr19 | 37095591 | 37095813 | chr19 | 37096488 | 37096660 |
| chr19 | 37263439 | 37263678 | chr19 | 37264143 | 37264487 | chr19 | 37288237 | 37288425 |
| chr19 | 37288607 | 37288705 | chr19 | 37288707 | 37288869 | chr19 | 37341683 | 37342042 |
| chr19 | 37407046 | 37407152 | chr19 | 37407154 | 37407374 | chr19 | 37407376 | 37407525 |
| chr19 | 37463953 | 37464568 | chr19 | 37464667 | 37464792 | chr19 | 37569394 | 37569573 |
| chr19 | 37702087 | 37702265 | chr19 | 37959762 | 37959801 | chr19 | 37959874 | 37960061 |
| chr19 | 37997337 | 37997991 | chr19 | 37997993 | 37998206 | chr19 | 38042357 | 38042769 |
| chr19 | 38085160 | 38085759 | chr19 | 38085958 | 38086110 | chr19 | 38145976 | 38146335 |
| chr19 | 38146364 | 38146663 | chr19 | 38182793 | 38182960 | chr19 | 38183112 | 38183259 |
| chr19 | 38183261 | 38183262 | chr19 | 38183264 | 38183392 | chr19 | 38308031 | 38308337 |
| chr19 | 38308395 | 38308543 | chr19 | 38480952 | 38481190 | chr19 | 38747072 | 38747078 |
| chr19 | 38747107 | 38747201 | chr19 | 38747203 | 38747448 | chr19 | 38755189 | 38755422 |
| chr19 | 38782485 | 38782664 | chr19 | 38789223 | 38789373 | chr19 | 38873861 | 38874040 |
| chr19 | 38905446 | 38905805 | chr19 | 38974158 | 38974337 | chr19 | 39135435 | 39135554 |
| chr19 | 39687575 | 39687647 | chr19 | 39687756 | 39687934 | chr19 | 39754787 | 39755233 |
| chr19 | 39755265 | 39755446 | chr19 | 39816862 | 39817161 | chr19 | 39993392 | 39993657 |
| chr19 | 39993712 | 39993751 | chr19 | 39997602 | 39997733 | chr19 | 39997749 | 39997901 |
| chr19 | 40006093 | 40006161 | chr19 | 40006187 | 40006392 | chr19 | 40006499 | 40006728 |
| chr19 | 40723923 | 40724342 | chr19 | 40829768 | 40830123 | chr19 | 40902350 | 40902779 |
| chr19 | 40951087 | 40951197 | chr19 | 40951602 | 40951841 | chr19 | 41018456 | 41019063 |
| chr19 | 41019076 | 41019131 | chr19 | 41025462 | 41025761 | chr19 | 41059832 | 41060385 |
| chr19 | 41073513 | 41073752 | chr19 | 41119097 | 41119277 | chr19 | 41119371 | 41119409 |
| chr19 | 41119670 | 41119735 | chr19 | 41354576 | 41354814 | chr19 | 41641740 | 41641979 |

TABLE 15-continued

| chr | start | end | chr | start | end | chr | start | end |
|---|---|---|---|---|---|---|---|---|
| chr19 | 42028407 | 42028646 | chr19 | 42408226 | 42408405 | chr19 | 42827810 | 42827820 |
| chr19 | 42827982 | 42828085 | chr19 | 42828317 | 42828349 | chr19 | 42856486 | 42856558 |
| chr19 | 44203735 | 44203962 | chr19 | 44405819 | 44405924 | chr19 | 44405926 | 44406178 |
| chr19 | 44599691 | 44599803 | chr19 | 44905425 | 44905604 | chr19 | 44952193 | 44952618 |
| chr19 | 44952620 | 44952665 | chr19 | 44952667 | 44952909 | chr19 | 45003142 | 45003417 |
| chr19 | 45300052 | 45300291 | chr19 | 45570307 | 45570546 | chr19 | 45574391 | 45574570 |
| chr19 | 45574682 | 45574782 | chr19 | 45574837 | 45574981 | chr19 | 45655309 | 45655349 |
| chr19 | 45655400 | 45655557 | chr19 | 45655648 | 45656448 | chr19 | 45656589 | 45656743 |
| chr19 | 45656791 | 45657008 | chr19 | 45657129 | 45657368 | chr19 | 45810006 | 45810345 |
| chr19 | 45835239 | 45835353 | chr19 | 45888843 | 45889225 | chr19 | 45889316 | 45889484 |
| chr19 | 45997437 | 45997676 | chr19 | 46001945 | 46002353 | chr19 | 46234853 | 46234965 |
| chr19 | 46379822 | 46379858 | chr19 | 46379894 | 46380241 | chr19 | 46404448 | 46404682 |
| chr19 | 46916631 | 46916988 | chr19 | 46917061 | 46917170 | chr19 | 46930046 | 46930278 |
| chr19 | 46974477 | 46974567 | chr19 | 46974569 | 46974609 | chr19 | 46992643 | 46992942 |
| chr19 | 46993067 | 46993261 | chr19 | 46993282 | 46993486 | chr19 | 46996509 | 46996515 |
| chr19 | 46996578 | 46996748 | chr19 | 46996775 | 46996839 | chr19 | 47152978 | 47152991 |
| chr19 | 47200270 | 47200629 | chr19 | 47910559 | 47910584 | chr19 | 47933223 | 47933822 |
| chr19 | 48003512 | 48003747 | chr19 | 48076568 | 48076747 | chr19 | 48137090 | 48137187 |
| chr19 | 48137247 | 48137389 | chr19 | 48151189 | 48151421 | chr19 | 48614769 | 48614851 |
| chr19 | 48771496 | 48771636 | chr19 | 48800507 | 48800866 | chr19 | 48857809 | 48857917 |
| chr19 | 48902834 | 48902953 | chr19 | 48918040 | 48918339 | chr19 | 49119155 | 49119334 |
| chr19 | 49127285 | 49127764 | chr19 | 49180431 | 49180610 | chr19 | 49399126 | 49399414 |
| chr19 | 49575386 | 49575475 | chr19 | 49646062 | 49646116 | chr19 | 49646246 | 49646294 |
| chr19 | 49890810 | 49890908 | chr19 | 49935656 | 49936255 | chr19 | 49936828 | 49936969 |
| chr19 | 50028531 | 50028614 | chr19 | 50049635 | 50049746 | chr19 | 50215991 | 50216147 |
| chr19 | 50316147 | 50316566 | chr19 | 50353305 | 50353664 | chr19 | 50553917 | 50554516 |
| chr19 | 50816339 | 50816573 | chr19 | 50833750 | 50833966 | chr19 | 50938470 | 50938769 |
| chr19 | 51161151 | 51161330 | chr19 | 51162123 | 51162254 | chr19 | 51162428 | 51162602 |
| chr19 | 51171130 | 51171276 | chr19 | 51227633 | 51227872 | chr19 | 51227975 | 51228154 |
| chr19 | 51228229 | 51228269 | chr19 | 51228369 | 51228588 | chr19 | 51304487 | 51304666 |
| chr19 | 51520349 | 51520528 | chr19 | 51830748 | 51831003 | chr19 | 51831121 | 51831227 |
| chr19 | 51831286 | 51831465 | chr19 | 52097592 | 52097831 | chr19 | 52207162 | 52207461 |
| chr19 | 52222438 | 52222924 | chr19 | 52223143 | 52223192 | chr19 | 52552089 | 52552120 |
| chr19 | 52552234 | 52552248 | chr19 | 52839494 | 52839634 | chr19 | 52839700 | 52839718 |
| chr19 | 52839742 | 52839924 | chr19 | 52839926 | 52840033 | chr19 | 52872943 | 52873106 |
| chr19 | 52873108 | 52873534 | chr19 | 52956708 | 52956947 | chr19 | 53028835 | 53028952 |
| chr19 | 53031202 | 53031290 | chr19 | 53073476 | 53073773 | chr19 | 53073820 | 53073865 |
| chr19 | 53073867 | 53074075 | chr19 | 53141533 | 53141619 | chr19 | 53141648 | 53141832 |
| chr19 | 53193757 | 53193996 | chr19 | 53194190 | 53194366 | chr19 | 53496630 | 53496787 |
| chr19 | 53496814 | 53496928 | chr19 | 53561582 | 53561821 | chr19 | 53635873 | 53636108 |
| chr19 | 53636110 | 53636168 | chr19 | 53661566 | 53661865 | chr19 | 53662195 | 53662722 |
| chr19 | 53696318 | 53696649 | chr19 | 53696651 | 53696677 | chr19 | 53700514 | 53700693 |
| chr19 | 53757802 | 53758341 | chr19 | 53811774 | 53811986 | chr19 | 53836837 | 53836912 |
| chr19 | 53970464 | 53970636 | chr19 | 53970884 | 53971040 | chr19 | 53971110 | 53971243 |
| chr19 | 54023803 | 54023999 | chr19 | 54024001 | 54024282 | chr19 | 54024434 | 54024553 |
| chr19 | 54024619 | 54024973 | chr19 | 54411032 | 54411267 | chr19 | 54411482 | 54411661 |
| chr19 | 54412809 | 54412992 | chr19 | 54413009 | 54413079 | chr19 | 54445250 | 54445297 |
| chr19 | 54445559 | 54445609 | chr19 | 54481691 | 54482050 | chr19 | 54483091 | 54483188 |
| chr19 | 54483190 | 54483306 | chr19 | 54483365 | 54483532 | chr19 | 54483534 | 54483630 |
| chr19 | 54485442 | 54485647 | chr19 | 54485673 | 54485913 | chr19 | 56159350 | 56159596 |
| chr19 | 56201573 | 56201812 | chr19 | 56588806 | 56588868 | chr19 | 56728588 | 56728603 |
| chr19 | 56728659 | 56728789 | chr19 | 56879475 | 56879554 | chr19 | 56879556 | 56879645 |
| chr19 | 56879647 | 56879994 | chr19 | 56879996 | 56880075 | chr19 | 56904643 | 56904704 |
| chr19 | 56904724 | 56904997 | chr19 | 56904999 | 56905302 | chr19 | 56915225 | 56915524 |
| chr19 | 56988458 | 56988664 | chr19 | 56989502 | 56989626 | chr19 | 56989697 | 56989851 |
| chr19 | 57050429 | 57050568 | chr19 | 57149480 | 57149719 | chr19 | 57154802 | 57155101 |
| chr19 | 57182906 | 57183127 | chr19 | 57183374 | 57183423 | chr19 | 57276559 | 57276798 |
| chr19 | 57610771 | 57610828 | chr19 | 57610896 | 57611067 | chr19 | 57617433 | 57617716 |
| chr19 | 57617832 | 57618170 | chr19 | 57683078 | 57683163 | chr19 | 57683240 | 57683372 |
| chr19 | 57862330 | 57862638 | chr19 | 57862640 | 57862859 | chr19 | 57862930 | 57862958 |
| chr19 | 57863222 | 57863229 | chr19 | 58011040 | 58011345 | chr19 | 58011347 | 58011383 |
| chr19 | 58038924 | 58039067 | chr19 | 58094925 | 58095468 | chr19 | 58095470 | 58095931 |
| chr19 | 58111529 | 58111888 | chr19 | 58125444 | 58125983 | chr19 | 58144419 | 58144778 |
| chr19 | 58219924 | 58220393 | chr19 | 58220516 | 58220883 | chr19 | 58238234 | 58238739 |
| chr19 | 58238988 | 58239012 | chr19 | 58239014 | 58239187 | chr19 | 58399978 | 58400277 |
| chr19 | 58400319 | 58400618 | chr19 | 58458679 | 58458891 | chr19 | 58458979 | 58459278 |
| chr19 | 58514416 | 58514655 | chr19 | 58520661 | 58521020 | chr19 | 58545042 | 58545388 |
| chr19 | 58545578 | 58545590 | chr19 | 58545652 | 58545843 | chr19 | 58609299 | 58609360 |
| chr19 | 58609473 | 58609526 | chr19 | 58609713 | 58609744 | chr19 | 58609746 | 58609944 |
| chr19 | 58629812 | 58629864 | chr19 | 58629975 | 58630026 | chr19 | 58661815 | 58662174 |
| chr19 | 58666093 | 58666392 | chr19 | 58739983 | 58740222 | chr19 | 58874834 | 58874951 |
| chr19 | 58907613 | 58907637 | chr19 | 58951175 | 58951401 | chr19 | 58951526 | 58951599 |
| chr19 | 58951601 | 58951778 | chr19 | 58951780 | 58952014 | chr19 | 58964105 | 58964283 |
| chr20 | 291052 | 291163 | chr20 | 291221 | 291453 | chr20 | 399928 | 400167 |
| chr20 | 401079 | 401258 | chr20 | 401495 | 401854 | chr20 | 590349 | 590588 |
| chr20 | 592323 | 592547 | chr20 | 644553 | 644826 | chr20 | 799030 | 799146 |
| chr20 | 982660 | 982799 | chr20 | 982892 | 983079 | chr20 | 1206766 | 1207125 |
| chr20 | 1783674 | 1784306 | chr20 | 2539252 | 2539552 | chr20 | 2539554 | 2539851 |

TABLE 15-continued

| chr | start | end | chr | start | end | chr | start | end |
|---|---|---|---|---|---|---|---|---|
| chr20 | 2668670 | 2669026 | chr20 | 2780654 | 2780747 | chr20 | 2780894 | 2781122 |
| chr20 | 2781124 | 2781553 | chr20 | 2781657 | 2781836 | chr20 | 2785561 | 2785867 |
| chr20 | 2785956 | 2786160 | chr20 | 3027666 | 3027780 | chr20 | 3052501 | 3052692 |
| chr20 | 3052694 | 3052920 | chr20 | 3073561 | 3073994 | chr20 | 3204792 | 3205031 |
| chr20 | 3220799 | 3221038 | chr20 | 3229475 | 3229480 | chr20 | 3229527 | 3229714 |
| chr20 | 3641774 | 3642015 | chr20 | 3662918 | 3663277 | chr20 | 4084983 | 4085146 |
| chr20 | 4229328 | 4229507 | chr20 | 4229684 | 4230684 | chr20 | 4802971 | 4803750 |
| chr20 | 4803846 | 4804053 | chr20 | 5296095 | 5296986 | chr20 | 5297226 | 5297419 |
| chr20 | 5297673 | 5297705 | chr20 | 6022813 | 6023052 | chr20 | 6748832 | 6749131 |
| chr20 | 8112304 | 8112483 | chr20 | 8112642 | 8113121 | chr20 | 8113462 | 8113701 |
| chr20 | 9487302 | 9487720 | chr20 | 9487789 | 9488032 | chr20 | 9488329 | 9488613 |
| chr20 | 9488650 | 9488934 | chr20 | 9488993 | 9489249 | chr20 | 9489377 | 9489796 |
| chr20 | 9495181 | 9495572 | chr20 | 9495574 | 9495600 | chr20 | 9496253 | 9496531 |
| chr20 | 9496581 | 9496912 | chr20 | 9496953 | 9497074 | chr20 | 10198206 | 10198685 |
| chr20 | 10198941 | 10199020 | chr20 | 13200498 | 13200737 | chr20 | 16555037 | 16555130 |
| chr20 | 17206434 | 17206840 | chr20 | 17207783 | 17208022 | chr20 | 17208484 | 17208657 |
| chr20 | 18039741 | 18039980 | chr20 | 19739495 | 19739566 | chr20 | 19739613 | 19739794 |
| chr20 | 19928211 | 19928450 | chr20 | 20344410 | 20344649 | chr20 | 20345597 | 20345631 |
| chr20 | 20346167 | 20346176 | chr20 | 20347358 | 20347710 | chr20 | 20347737 | 20348222 |
| chr20 | 20348447 | 20348686 | chr20 | 20349055 | 20349354 | chr20 | 20349500 | 20349679 |
| chr20 | 21080615 | 21080957 | chr20 | 21081029 | 21081845 | chr20 | 21082095 | 21082124 |
| chr20 | 21082216 | 21082354 | chr20 | 21082456 | 21082995 | chr20 | 21083322 | 21084461 |
| chr20 | 21085768 | 21085968 | chr20 | 21086075 | 21086152 | chr20 | 21086195 | 21086554 |
| chr20 | 21086808 | 21087267 | chr20 | 21372091 | 21372193 | chr20 | 21372295 | 21372810 |
| chr20 | 21376172 | 21376337 | chr20 | 21376703 | 21376734 | chr20 | 21376877 | 21377129 |
| chr20 | 21377474 | 21377641 | chr20 | 21377738 | 21378631 | chr20 | 21486299 | 21486660 |
| chr20 | 21486786 | 21486917 | chr20 | 21486955 | 21486958 | chr20 | 21487068 | 21487276 |
| chr20 | 21487368 | 21487667 | chr20 | 21488076 | 21488435 | chr20 | 21489135 | 21489159 |
| chr20 | 21489240 | 21489447 | chr20 | 21489622 | 21489794 | chr20 | 21490099 | 21490763 |
| chr20 | 21490815 | 21491346 | chr20 | 21491617 | 21491632 | chr20 | 21492309 | 21492410 |
| chr20 | 21492508 | 21492826 | chr20 | 21492991 | 21493071 | chr20 | 21493218 | 21493994 |
| chr20 | 21494438 | 21494797 | chr20 | 21495845 | 21496084 | chr20 | 21496158 | 21496397 |
| chr20 | 21496684 | 21497217 | chr20 | 21497337 | 21498716 | chr20 | 21500019 | 21500228 |
| chr20 | 21501294 | 21501360 | chr20 | 21501445 | 21501814 | chr20 | 21501945 | 21502145 |
| chr20 | 21502495 | 21502700 | chr20 | 21502838 | 21503174 | chr20 | 21503490 | 21503877 |
| chr20 | 21682309 | 21682329 | chr20 | 21682362 | 21682548 | chr20 | 21683213 | 21683751 |
| chr20 | 21685592 | 21685606 | chr20 | 21686157 | 21686293 | chr20 | 21686295 | 21686756 |
| chr20 | 21686921 | 21687383 | chr20 | 21687756 | 21687820 | chr20 | 21689862 | 21690137 |
| chr20 | 21694425 | 21694604 | chr20 | 21695014 | 21695274 | chr20 | 21695306 | 21695391 |
| chr20 | 21748349 | 21748588 | chr20 | 22557301 | 22557776 | chr20 | 22557898 | 22558197 |
| chr20 | 22558534 | 22558773 | chr20 | 22559549 | 22559676 | chr20 | 22559678 | 22559788 |
| chr20 | 22562632 | 22562886 | chr20 | 22563690 | 22563703 | chr20 | 22564161 | 22564291 |
| chr20 | 23015843 | 23015942 | chr20 | 23029012 | 23029232 | chr20 | 23029589 | 23030086 |
| chr20 | 23030292 | 23030442 | chr20 | 23031471 | 23031729 | chr20 | 24450133 | 24450612 |
| chr20 | 24450692 | 24450704 | chr20 | 24450820 | 24451084 | chr20 | 24451086 | 24451111 |
| chr20 | 24451372 | 24451671 | chr20 | 25058292 | 25058711 | chr20 | 25061654 | 25061789 |
| chr20 | 25061979 | 25062312 | chr20 | 25062511 | 25062646 | chr20 | 25062708 | 25062818 |
| chr20 | 25062871 | 25062973 | chr20 | 25063700 | 25063907 | chr20 | 25063994 | 25064539 |
| chr20 | 25065078 | 25065207 | chr20 | 25065209 | 25065497 | chr20 | 25129465 | 25129520 |
| chr20 | 25129522 | 25129544 | chr20 | 25230415 | 25230513 | chr20 | 25230775 | 25230894 |
| chr20 | 26188813 | 26188962 | chr20 | 26190218 | 26190432 | chr20 | 30101724 | 30101833 |
| chr20 | 30582655 | 30583074 | chr20 | 30639051 | 30639410 | chr20 | 30639531 | 30639570 |
| chr20 | 30639603 | 30639950 | chr20 | 30640009 | 30640256 | chr20 | 30640258 | 30640368 |
| chr20 | 30777930 | 30778339 | chr20 | 31115592 | 31115891 | chr20 | 31151695 | 31151874 |
| chr20 | 32301800 | 32302039 | chr20 | 32450399 | 32450518 | chr20 | 33547579 | 33547685 |
| chr20 | 33574834 | 33574981 | chr20 | 34041903 | 34042004 | chr20 | 34147928 | 34148347 |
| chr20 | 34188525 | 34188632 | chr20 | 34188748 | 34189089 | chr20 | 34189167 | 34189484 |
| chr20 | 34189680 | 34190013 | chr20 | 36531706 | 36532005 | chr20 | 36781250 | 36781429 |
| chr20 | 37302601 | 37303440 | chr20 | 37351701 | 37352516 | chr20 | 37352607 | 37352720 |
| chr20 | 37353096 | 37353335 | chr20 | 37353378 | 37353719 | chr20 | 37353807 | 37353857 |
| chr20 | 37354045 | 37354832 | chr20 | 37354994 | 37355304 | chr20 | 37355761 | 37356043 |
| chr20 | 37356169 | 37356828 | chr20 | 37357216 | 37357440 | chr20 | 37357739 | 37358278 |
| chr20 | 37434489 | 37434722 | chr20 | 37434737 | 37434828 | chr20 | 37435012 | 37435311 |
| chr20 | 37435362 | 37435370 | chr20 | 37435488 | 37435716 | chr20 | 37435718 | 37435961 |
| chr20 | 39316114 | 39316413 | chr20 | 39316814 | 39316853 | chr20 | 39316984 | 39317034 |
| chr20 | 39317036 | 39317473 | chr20 | 39317659 | 39318138 | chr20 | 39319031 | 39319204 |
| chr20 | 39319515 | 39319750 | chr20 | 39995061 | 39995546 | chr20 | 39995548 | 39995900 |
| chr20 | 41817697 | 41817916 | chr20 | 41818008 | 41818176 | chr20 | 41818472 | 41818749 |
| chr20 | 41818805 | 41819011 | chr20 | 42136252 | 42136491 | chr20 | 42218593 | 42218757 |
| chr20 | 42543655 | 42543954 | chr20 | 42543999 | 42544534 | chr20 | 42544728 | 42545078 |
| chr20 | 42876457 | 42876670 | chr20 | 43437970 | 43438086 | chr20 | 43438335 | 43438569 |
| chr20 | 43438883 | 43439122 | chr20 | 43439192 | 43439219 | chr20 | 43439248 | 43439611 |
| chr20 | 44452666 | 44453152 | chr20 | 44519003 | 44519182 | chr20 | 44601980 | 44602069 |
| chr20 | 44639100 | 44639579 | chr20 | 44640264 | 44640288 | chr20 | 44640313 | 44640443 |
| chr20 | 44660665 | 44660964 | chr20 | 44686423 | 44686615 | chr20 | 44686628 | 44686866 |
| chr20 | 44803096 | 44803126 | chr20 | 44803173 | 44803755 | chr20 | 44879700 | 44879791 |
| chr20 | 44880041 | 44880167 | chr20 | 44937124 | 44937369 | chr20 | 44937444 | 44937723 |
| chr20 | 44941441 | 44941740 | chr20 | 45141897 | 45142039 | chr20 | 45142152 | 45142244 |

TABLE 15-continued

| chr | start | end | chr | start | end | chr | start | end |
|---|---|---|---|---|---|---|---|---|
| chr20 | 45142246 | 45142331 | chr20 | 45279779 | 45279982 | chr20 | 45280040 | 45280491 |
| chr20 | 45337726 | 45338025 | chr20 | 45524449 | 45524628 | chr20 | 47247136 | 47247407 |
| chr20 | 47274032 | 47274137 | chr20 | 47296021 | 47296320 | chr20 | 47443647 | 47443937 |
| chr20 | 47443945 | 47444241 | chr20 | 47444243 | 47444366 | chr20 | 47905336 | 47905687 |
| chr20 | 47934747 | 47934987 | chr20 | 47934989 | 47935346 | chr20 | 47935412 | 47935651 |
| chr20 | 47935829 | 47936128 | chr20 | 48184289 | 48184292 | chr20 | 48184329 | 48184528 |
| chr20 | 49204105 | 49204524 | chr20 | 49261715 | 49262194 | chr20 | 49358363 | 49358477 |
| chr20 | 49377912 | 49378139 | chr20 | 49381177 | 49381340 | chr20 | 49575835 | 49575938 |
| chr20 | 49575988 | 49576014 | chr20 | 49639698 | 49639857 | chr20 | 49639883 | 49639997 |
| chr20 | 49640095 | 49640237 | chr20 | 50383399 | 50383504 | chr20 | 50384683 | 50384982 |
| chr20 | 50720356 | 50721201 | chr20 | 50721235 | 50721671 | chr20 | 50721989 | 50722021 |
| chr20 | 50722096 | 50722201 | chr20 | 50722609 | 50722908 | chr20 | 51589688 | 51589987 |
| chr20 | 52311387 | 52311505 | chr20 | 52789371 | 52789550 | chr20 | 52789765 | 52789949 |
| chr20 | 52790082 | 52790244 | chr20 | 53092165 | 53092233 | chr20 | 53092235 | 53092334 |
| chr20 | 53092336 | 53092464 | chr20 | 53093011 | 53093190 | chr20 | 54578407 | 54578826 |
| chr20 | 54579809 | 54579959 | chr20 | 54580070 | 54580408 | chr20 | 54580484 | 54580522 |
| chr20 | 54580622 | 54580783 | chr20 | 55199952 | 55200311 | chr20 | 55200616 | 55200791 |
| chr20 | 55200828 | 55201187 | chr20 | 55201451 | 55201452 | chr20 | 55201581 | 55201638 |
| chr20 | 55201686 | 55202069 | chr20 | 55202359 | 55202705 | chr20 | 55202728 | 55203207 |
| chr20 | 55204224 | 55204703 | chr20 | 55204864 | 55205103 | chr20 | 55206294 | 55206430 |
| chr20 | 55206464 | 55206495 | chr20 | 55499394 | 55499813 | chr20 | 55499932 | 55500171 |
| chr20 | 55500441 | 55500670 | chr20 | 55500672 | 55500721 | chr20 | 55693446 | 55693610 |
| chr20 | 55841036 | 55841455 | chr20 | 55842056 | 55842293 | chr20 | 56766086 | 56766203 |
| chr20 | 56803301 | 56803540 | chr20 | 56803762 | 56804001 | chr20 | 57089355 | 57089460 |
| chr20 | 57090104 | 57090259 | chr20 | 57224799 | 57225080 | chr20 | 57225219 | 57225405 |
| chr20 | 58152557 | 58152559 | chr20 | 58152776 | 58152796 | chr20 | 58179713 | 58179952 |
| chr20 | 58180214 | 58180403 | chr20 | 58180471 | 58180497 | chr20 | 58508796 | 58509005 |
| chr20 | 59804233 | 59804323 | chr20 | 59826885 | 59826978 | chr20 | 59828341 | 59828408 |
| chr20 | 59880480 | 59880575 | chr20 | 59910084 | 59910441 | chr20 | 59972951 | 59973170 |
| chr20 | 60202541 | 60202699 | chr20 | 60235251 | 60235610 | chr20 | 60238278 | 60238574 |
| chr20 | 60238780 | 60239079 | chr20 | 60243860 | 60244206 | chr20 | 60329482 | 60329661 |
| chr20 | 60359835 | 60359954 | chr20 | 60374934 | 60375173 | chr20 | 60439546 | 60439845 |
| chr20 | 60453829 | 60454186 | chr20 | 60477213 | 60477632 | chr20 | 60485281 | 60485480 |
| chr20 | 60502956 | 60503135 | chr20 | 60620233 | 60620412 | chr20 | 60772886 | 60773905 |
| chr20 | 60789866 | 60790225 | chr20 | 60925945 | 60926124 | chr20 | 60970879 | 60971058 |
| chr20 | 60983756 | 60984115 | chr20 | 60984356 | 60984553 | chr20 | 61287993 | 61288232 |
| chr20 | 61288380 | 61288619 | chr20 | 61294596 | 61294955 | chr20 | 61340486 | 61340785 |
| chr20 | 61412227 | 61412451 | chr20 | 61505882 | 61506421 | chr20 | 61532457 | 61532696 |
| chr20 | 61560341 | 61560461 | chr20 | 61560529 | 61561000 | chr20 | 61636755 | 61636779 |
| chr20 | 61636876 | 61636994 | chr20 | 61637391 | 61637649 | chr20 | 61637736 | 61637957 |
| chr20 | 61638221 | 61638470 | chr20 | 61638535 | 61638710 | chr20 | 61703710 | 61703762 |
| chr20 | 61703846 | 61703972 | chr20 | 61714683 | 61714696 | chr20 | 61734332 | 61734571 |
| chr20 | 61747795 | 61748034 | chr20 | 61763524 | 61763703 | chr20 | 61765251 | 61765490 |
| chr20 | 61808107 | 61808346 | chr20 | 61808667 | 61808888 | chr20 | 61808890 | 61809006 |
| chr20 | 61809219 | 61809557 | chr20 | 61809559 | 61809632 | chr20 | 61809841 | 61810135 |
| chr20 | 61810160 | 61810187 | chr20 | 61823076 | 61823195 | chr20 | 61862297 | 61862460 |
| chr20 | 61885196 | 61885291 | chr20 | 61885293 | 61885551 | chr20 | 61885778 | 61885848 |
| chr20 | 61885984 | 61886204 | chr20 | 61886257 | 61886343 | chr20 | 61886651 | 61886830 |
| chr20 | 61974094 | 61974453 | chr20 | 61980769 | 61981068 | chr20 | 62031085 | 62031324 |
| chr20 | 62031958 | 62032197 | chr20 | 62037460 | 62037699 | chr20 | 62046145 | 62046504 |
| chr20 | 62058624 | 62058859 | chr20 | 62090442 | 62090621 | chr20 | 62097763 | 62097771 |
| chr20 | 62115188 | 62115367 | chr20 | 62119246 | 62119619 | chr20 | 62119923 | 62120252 |
| chr20 | 62126035 | 62126514 | chr20 | 62157232 | 62157349 | chr20 | 62165548 | 62165847 |
| chr20 | 62167480 | 62167659 | chr20 | 62170105 | 62170284 | chr20 | 62172851 | 62173150 |
| chr20 | 62185296 | 62185535 | chr20 | 62321125 | 62321424 | chr20 | 62321551 | 62321970 |
| chr20 | 62340233 | 62340423 | chr20 | 62383135 | 62383374 | chr20 | 62461263 | 62461562 |
| chr20 | 62488263 | 62488442 | chr20 | 62680682 | 62680818 | chr20 | 62714923 | 62714946 |
| chr20 | 62715097 | 62715162 | chr21 | 22370246 | 22370347 | chr21 | 22370349 | 22370476 |
| chr21 | 22370614 | 22370733 | chr21 | 22370735 | 22370793 | chr21 | 26934278 | 26934877 |
| chr21 | 27011671 | 27011910 | chr21 | 27012283 | 27012522 | chr21 | 27944919 | 27945148 |
| chr21 | 27945619 | 27945798 | chr21 | 28216509 | 28216583 | chr21 | 28216634 | 28217768 |
| chr21 | 28218671 | 28218815 | chr21 | 28218877 | 28219150 | chr21 | 28338743 | 28338848 |
| chr21 | 28339165 | 28339584 | chr21 | 28339806 | 28339907 | chr21 | 28339909 | 28340049 |
| chr21 | 28340063 | 28340405 | chr21 | 31015127 | 31015306 | chr21 | 31311387 | 31311629 |
| chr21 | 31311846 | 31311920 | chr21 | 31312080 | 31312205 | chr21 | 31312230 | 31312259 |
| chr21 | 31312305 | 31312409 | chr21 | 33244901 | 33245131 | chr21 | 33245582 | 33245593 |
| chr21 | 33245716 | 33245821 | chr21 | 33245921 | 33245955 | chr21 | 33246038 | 33246280 |
| chr21 | 33627450 | 33627569 | chr21 | 33721671 | 33721910 | chr21 | 33983153 | 33983320 |
| chr21 | 34392070 | 34392168 | chr21 | 34392206 | 34392404 | chr21 | 34392437 | 34392669 |
| chr21 | 34395217 | 34396356 | chr21 | 34396707 | 34396870 | chr21 | 34396903 | 34397178 |
| chr21 | 34397993 | 34398131 | chr21 | 34398133 | 34398199 | chr21 | 34398201 | 34398222 |
| chr21 | 34398224 | 34398712 | chr21 | 34398847 | 34399259 | chr21 | 34399442 | 34400105 |
| chr21 | 34400232 | 34400346 | chr21 | 34401110 | 34401469 | chr21 | 34442595 | 34442696 |
| chr21 | 34443004 | 34443363 | chr21 | 34443419 | 34443778 | chr21 | 34443806 | 34444045 |
| chr21 | 34444082 | 34444363 | chr21 | 34444445 | 34444681 | chr21 | 36041934 | 36042029 |
| chr21 | 36042092 | 36042170 | chr21 | 36042172 | 36042322 | chr21 | 36042581 | 36042940 |
| chr21 | 37527854 | 37528033 | chr21 | 37758492 | 37758611 | chr21 | 37774963 | 37775238 |
| chr21 | 38064415 | 38064714 | chr21 | 38064917 | 38065523 | chr21 | 38065800 | 38065832 |

TABLE 15-continued

| chr | start | end | chr | start | end | chr | start | end |
|---|---|---|---|---|---|---|---|---|
| chr21 | 38065855 | 38066214 | chr21 | 38067247 | 38067308 | chr21 | 38068092 | 38068230 |
| chr21 | 38068647 | 38068871 | chr21 | 38069125 | 38069298 | chr21 | 38069359 | 38069598 |
| chr21 | 38069725 | 38069806 | chr21 | 38069854 | 38070144 | chr21 | 38070616 | 38070855 |
| chr21 | 38071699 | 38071781 | chr21 | 38071933 | 38071998 | chr21 | 38072920 | 38073159 |
| chr21 | 38073240 | 38073526 | chr21 | 38073616 | 38073940 | chr21 | 38077207 | 38077243 |
| chr21 | 38078332 | 38078571 | chr21 | 38079887 | 38080063 | chr21 | 38080175 | 38080387 |
| chr21 | 38080551 | 38080786 | chr21 | 38081112 | 38081193 | chr21 | 38081666 | 38081910 |
| chr21 | 38081968 | 38082011 | chr21 | 38082854 | 38083258 | chr21 | 38092081 | 38092320 |
| chr21 | 38119809 | 38120408 | chr21 | 38638505 | 38638624 | chr21 | 38935395 | 38935601 |
| chr21 | 39047688 | 39047889 | chr21 | 40984719 | 40984898 | chr21 | 43376299 | 43376478 |
| chr21 | 43786609 | 43786788 | chr21 | 43991389 | 43991568 | chr21 | 44283611 | 44283850 |
| chr21 | 44494941 | 44494997 | chr21 | 44494999 | 44495233 | chr21 | 44837002 | 44837245 |
| chr21 | 44837296 | 44837301 | chr21 | 44847488 | 44847606 | chr21 | 44847608 | 44847727 |
| chr21 | 44866508 | 44866807 | chr21 | 45148538 | 45148837 | chr21 | 45195115 | 45195414 |
| chr21 | 45273636 | 45273995 | chr21 | 45508543 | 45508662 | chr21 | 45791005 | 45791184 |
| chr21 | 46036556 | 46036855 | chr21 | 46126388 | 46126428 | chr21 | 46126567 | 46126807 |
| chr21 | 46126948 | 46127187 | chr21 | 46127468 | 46127628 | chr21 | 46128801 | 46129040 |
| chr21 | 46129346 | 46129585 | chr21 | 46257016 | 46257375 | chr21 | 46310341 | 46310580 |
| chr21 | 46318196 | 46318435 | chr21 | 46319069 | 46319548 | chr21 | 46359099 | 46359338 |
| chr21 | 46452278 | 46452637 | chr21 | 46677646 | 46677885 | chr21 | 46825737 | 46825823 |
| chr21 | 46863675 | 46863803 | chr21 | 46925704 | 46925999 | chr21 | 46926363 | 46926662 |
| chr21 | 46935727 | 46936018 | chr21 | 47010409 | 47010527 | chr21 | 47062753 | 47062925 |
| chr21 | 47063451 | 47064050 | chr21 | 47064165 | 47064464 | chr21 | 47404071 | 47404429 |
| chr21 | 47504759 | 47504994 | chr21 | 47518676 | 47518866 | chr21 | 47518888 | 47518915 |
| chr21 | 47717486 | 47717541 | chr21 | 47717623 | 47717665 | chr21 | 47746183 | 47746482 |
| chr22 | 17081848 | 17081936 | chr22 | 17082069 | 17082087 | chr22 | 17082492 | 17082524 |
| chr22 | 17082854 | 17082894 | chr22 | 17082989 | 17083062 | chr22 | 17083297 | 17083411 |
| chr22 | 17083525 | 17083596 | chr22 | 17600988 | 17601134 | chr22 | 17601260 | 17601467 |
| chr22 | 17602419 | 17602718 | chr22 | 17850359 | 17850718 | chr22 | 18009986 | 18010085 |
| chr22 | 18328049 | 18328348 | chr22 | 19017431 | 19017670 | chr22 | 19117490 | 19117669 |
| chr22 | 19510704 | 19510947 | chr22 | 19511142 | 19511456 | chr22 | 19511542 | 19511663 |
| chr22 | 19511765 | 19511876 | chr22 | 19706119 | 19706365 | chr22 | 19706367 | 19706754 |
| chr22 | 19742753 | 19742758 | chr22 | 19742789 | 19743052 | chr22 | 19748561 | 19748909 |
| chr22 | 19748961 | 19749040 | chr22 | 20792482 | 20792689 | chr22 | 21153919 | 21154084 |
| chr22 | 21304980 | 21305098 | chr22 | 21368513 | 21368692 | chr22 | 21977249 | 21977451 |
| chr22 | 21982708 | 21983062 | chr22 | 22006004 | 22006243 | chr22 | 22058102 | 22058341 |
| chr22 | 22090520 | 22090528 | chr22 | 22862704 | 22862863 | chr22 | 22863220 | 22863243 |
| chr22 | 22901011 | 22901550 | chr22 | 23791328 | 23791507 | chr22 | 23801388 | 23801567 |
| chr22 | 24180608 | 24180847 | chr22 | 24560283 | 24560522 | chr22 | 24820244 | 24820483 |
| chr22 | 25678654 | 25678869 | chr22 | 25679043 | 25679250 | chr22 | 25679268 | 25679433 |
| chr22 | 25817025 | 25817264 | chr22 | 25817356 | 25817715 | chr22 | 28198468 | 28198601 |
| chr22 | 28371575 | 28371754 | chr22 | 28838105 | 28838396 | chr22 | 28838411 | 28838524 |
| chr22 | 29091752 | 29091929 | chr22 | 29445659 | 29446018 | chr22 | 29876117 | 29876189 |
| chr22 | 29877142 | 29877381 | chr22 | 29977650 | 29977755 | chr22 | 30116824 | 30117147 |
| chr22 | 30158246 | 30158365 | chr22 | 30938434 | 30938507 | chr22 | 30938543 | 30938673 |
| chr22 | 31198416 | 31198715 | chr22 | 31218436 | 31218615 | chr22 | 31218693 | 31218932 |
| chr22 | 31481052 | 31481411 | chr22 | 32748862 | 32749041 | chr22 | 33197509 | 33197748 |
| chr22 | 33453802 | 33454075 | chr22 | 33454194 | 33454259 | chr22 | 33454346 | 33454452 |
| chr22 | 35848275 | 35848476 | chr22 | 36902217 | 36902456 | chr22 | 38199683 | 38199982 |
| chr22 | 38220568 | 38221287 | chr22 | 38476983 | 38477132 | chr22 | 38477297 | 38477882 |
| chr22 | 38592953 | 38593132 | chr22 | 38639155 | 38639308 | chr22 | 39784390 | 39784599 |
| chr22 | 39830257 | 39830492 | chr22 | 39853438 | 39853590 | chr22 | 39853592 | 39853657 |
| chr22 | 39932459 | 39932638 | chr22 | 39954323 | 39954400 | chr22 | 39954429 | 39954615 |
| chr22 | 40042536 | 40042835 | chr22 | 40075089 | 40075328 | chr22 | 40226368 | 40226487 |
| chr22 | 41048654 | 41048951 | chr22 | 41634334 | 41634618 | chr22 | 41636999 | 41637217 |
| chr22 | 41657217 | 41657442 | chr22 | 42095992 | 42096276 | chr22 | 42310005 | 42310304 |
| chr22 | 42311435 | 42311674 | chr22 | 42353530 | 42353992 | chr22 | 42667276 | 42667501 |
| chr22 | 42679917 | 42679935 | chr22 | 43012441 | 43012560 | chr22 | 43012883 | 43012980 |
| chr22 | 43083029 | 43083145 | chr22 | 43434340 | 43434579 | chr22 | 43739987 | 43740226 |
| chr22 | 43808205 | 43808502 | chr22 | 44208422 | 44208523 | chr22 | 44258287 | 44258586 |
| chr22 | 44287554 | 44287793 | chr22 | 44455605 | 44455844 | chr22 | 45088524 | 45088823 |
| chr22 | 45135840 | 45136079 | chr22 | 45277218 | 45277397 | chr22 | 45402991 | 45403230 |
| chr22 | 45404106 | 45404525 | chr22 | 45404909 | 45405011 | chr22 | 45405047 | 45405148 |
| chr22 | 45405219 | 45405432 | chr22 | 45405477 | 45405518 | chr22 | 45405545 | 45405627 |
| chr22 | 45405629 | 45405803 | chr22 | 45406181 | 45406420 | chr22 | 45593572 | 45593799 |
| chr22 | 45604107 | 45604444 | chr22 | 46262368 | 46263052 | chr22 | 46263512 | 46263624 |
| chr22 | 46263744 | 46263911 | chr22 | 46367955 | 46367987 | chr22 | 46368103 | 46368124 |
| chr22 | 46438002 | 46438112 | chr22 | 46658700 | 46658743 | chr22 | 46931177 | 46931336 |
| chr22 | 46933014 | 46933104 | chr22 | 47004990 | 47005253 | chr22 | 47023028 | 47023267 |
| chr22 | 47054612 | 47054700 | chr22 | 47193234 | 47193473 | chr22 | 47525747 | 47525986 |
| chr22 | 48027582 | 48027731 | chr22 | 48884960 | 48884960 | chr22 | 48885530 | 48885838 |
| chr22 | 48885908 | 48885989 | chr22 | 48886575 | 48886934 | chr22 | 48931805 | 48932104 |
| chr22 | 48971533 | 48971680 | chr22 | 48971759 | 48971829 | chr22 | 48972042 | 48972136 |
| chr22 | 48972220 | 48972466 | chr22 | 49852543 | 49852722 | chr22 | 49979553 | 49979835 |
| chr22 | 50001612 | 50001912 | chr22 | 50002684 | 50002911 | chr22 | 50003130 | 50003309 |
| chr22 | 50010037 | 50010336 | chr22 | 50010374 | 50010673 | chr22 | 50031617 | 50031796 |
| chr22 | 50149332 | 50149548 | chr22 | 50466931 | 50467045 | chr22 | 50496972 | 50497000 |
| chr22 | 50497068 | 50497183 | chr22 | 50497214 | 50497367 | chr22 | 50623613 | 50623715 |

TABLE 15-continued

| chr | start | end | chr | start | end | chr | start | end |
|---|---|---|---|---|---|---|---|---|
| chr22 | 50623742 | 50623894 | chr22 | 50899214 | 50899753 | chr22 | 50943082 | 50943358 |
| chr22 | 51042185 | 51042405 | chr22 | 51042458 | 51042566 | chr22 | 51112072 | 51112311 |
| chrX | 3746538 | 3746717 | chrX | 6145241 | 6145720 | chrX | 8698761 | 8699000 |
| chrX | 8699416 | 8699655 | chrX | 136656523 | 136656534 | AC211950.2_11234-25326 | 181 | 343 |
| AC211950.2_11234-25326 | 13241 | 13420 | AC211950.2_11234-25326 | 13667 | 13966 | AC241851.2_88-34049 | 15187 | 15426 |
| AEKP01168736.1_1-4752 | 1662 | 1781 | AEKP01168736.1_1-4752 | 1874 | 2381 | JH636052.4 | 5118687 | 5118986 |
| NW_001838016.1_818233-828058 | 6095 | 6142 | — | — | — | — | — | — |

17. The method of claim 15, wherein at least 50 of the at least 500 target genomic regions are selected from one or more of Tables 16-24 as follows:

TABLE 16

| chr | start | end | chr | start | end | chr | start | end |
|---|---|---|---|---|---|---|---|---|
| chr1 | 15251121 | 15251211 | chr1 | 15480854 | 15480892 | chr1 | 64240031 | 64240118 |
| chr1 | 64240618 | 64240673 | chr1 | 183774245 | 183774363 | chr1 | 202183372 | 202183401 |
| chr1 | 214724532 | 214724561 | chr1 | 232765226 | 232765301 | chr1 | 233750126 | 233750302 |
| chr2 | 14722762 | 14772823 | chr2 | 14774475 | 14774567 | chr2 | 46526303 | 46526331 |
| chr2 | 75427370 | 75427399 | chr2 | 101436638 | 101436708 | chr2 | 103236166 | 103236277 |
| chr2 | 151342979 | 151343218 | chr2 | 171571265 | 171571315 | chr2 | 171571890 | 171571997 |
| chr2 | 189157513 | 189157617 | chr2 | 235860803 | 235860808 | chr2 | 236402772 | 236402901 |
| chr2 | 236403271 | 236403419 | chr2 | 238395907 | 238395961 | chr3 | 37901952 | 37901953 |
| chr3 | 45187297 | 45187328 | chr3 | 126373521 | 126373619 | chr3 | 126373669 | 126373704 |
| che3 | 133748141 | 133748206 | chr3 | 133748552 | 133748576 | chr3 | 153838819 | 153838870 |
| che3 | 153839519 | 153839559 | chr3 | 153839641 | 153839775 | chr3 | 171527953 | 171527971 |
| chr4 | 24914639 | 24914668 | chr4 | 152246133 | 152246237 | chr4 | 170947288 | 170947325 |
| chr4 | 184019693 | 184019736 | chr4 | 184020107 | 184020179 | chr5 | 34656933 | 34657034 |
| chr5 | 22416247 | 72416262 | chr5 | 72733094 | 72733185 | chr5 | 107005984 | 107006186 |
| chr5 | 121413538 | 121413590 | chr6 | 1312001 | 1312095 | chr6 | 1312680 | 1312708 |
| chr6 | 1314089 | 1314101 | chr6 | 26987968 | 26988166 | chr6 | 42928322 | 42928454 |
| chr7 | 27275514 | 27275532 | chr7 | 28995658 | 28995978 | chr7 | 28996458 | 28996495 |
| chr7 | 32997125 | 32997454 | chr7 | 50860227 | 50860393 | chr7 | 50860960 | 50861103 |
| chr7 | 51384328 | 51384440 | chr7 | 51384916 | 51384951 | chr7 | 55086481 | 55086601 |
| chr7 | 55086984 | 55087533 | chr7 | 121945823 | 121945920 | chr7 | 155602752 | 155602805 |
| chr8 | 25041747 | 25041864 | chr8 | 95651539 | 95651599 | chr8 | 95651637 | 95651655 |
| chr8 | 102505798 | 102505934 | chr8 | 120220429 | 120220592 | chr9 | 14312995 | 14313096 |
| chr9 | 21559295 | 21559381 | chr9 | 21559678 | 21559702 | chr9 | 38620642 | 38620725 |
| chr9 | 110251389 | 110251418 | chr9 | 110252364 | 110252455 | chr9 | 134421818 | 134421835 |
| chr10 | 21462534 | 21462607 | chr10 | 30026077 | 30026090 | chr10 | 33624167 | 33624230 |
| chr10 | 33624493 | 33624550 | chr10 | 72973131 | 72973180 | chr10 | 116164249 | 116164341 |
| chr11 | 12132625 | 12132559 | chr11 | 12399041 | 12399145 | chr11 | 12399181 | 12399222 |
| chr11 | 12695482 | 12695496 | chr11 | 12695573 | 12695611 | chr11 | 12696512 | 12696746 |
| chr11 | 16628820 | 16628933 | chr11 | 33037468 | 33037556 | chr11 | 66790622 | 66790655 |
| chr11 | 120039834 | 120039865 | chr11 | 129245747 | 129245810 | chr11 | 130318961 | 130318997 |
| chr11 | 134201503 | 134201543 | chr11 | 134201842 | 134202084 | chr12 | 16500577 | 16500621 |
| chr12 | 56882365 | 56882380 | chr12 | 107486551 | 107486672 | chr12 | 107487195 | 107487855 |
| chr12 | 107712274 | 107712303 | chr13 | 100634315 | 100634382 | chr14 | 34420251 | 34420288 |
| chr14 | 61747389 | 61747528 | chr14 | 61747583 | 61747816 | chr14 | 61748002 | 61748033 |
| chr15 | 62456923 | 62456952 | chr15 | 71055770 | 71055815 | chr15 | 96874363 | 96874416 |
| chr15 | 98504115 | 98504144 | chr15 | 99193207 | 99193345 | chr15 | 99193350 | 99193465 |
| chr16 | 54964949 | 54965114 | chr16 | 68771167 | 68771298 | chr16 | 80966400 | 80966431 |
| chr16 | 84402245 | 84402319 | chr16 | 84853289 | 84853376 | chr17 | 42061337 | 42061381 |
| chr17 | 72427854 | 72427963 | chr17 | 72428345 | 72428381 | chr17 | 75207840 | 75207944 |
| chr17 | 80693343 | 80693554 | chr18 | 19750309 | 19750346 | chr18 | 21269350 | 21269390 |
| chr18 | 21269660 | 21269740 | chr18 | 78006004 | 78005051 | chr19 | 462182 | 462235 |
| chr19 | 33792412 | 33792524 | chr20 | 1206856 | 1207034 | chr20 | 6748926 | 6749036 |
| chr20 | 18039824 | 18039897 | chr20 | 22564236 | 22564265 | chr20 | 50384768 | 50384896 |
| chr21 | 38070706 | 38070765 | chr22 | 31198493 | 31198637 | — | — | — |

TABLE 17

| chr | start | end | chr | start | end | chr | start | end |
|---|---|---|---|---|---|---|---|---|
| chr1 | 2336398 | 2336427 | chr1 | 2521025 | 2521062 | chr1 | 6507964 | 6508126 |
| chr1 | 21573736 | 21574203 | chr1 | 23885071 | 23885088 | chr1 | 155043332 | 155043657 |
| chr1 | 167823371 | 167823461 | chr1 | 185073819 | 185073966 | chr2 | 44497709 | 44497842 |
| chr2 | 61135116 | 61135137 | chr2 | 127863602 | 127863725 | chr3 | 12977068 | 12977144 |
| chr3 | 183728814 | 183728926 | chr5 | 43007937 | 43007966 | chr5 | 176764101 | 176764169 |
| chr6 | 41773521 | 41773844 | chr6 | 43748464 | 43748616 | chr7 | 907657 | 907709 |
| chr7 | 6188552 | 6188831 | chr7 | 6188926 | 6189061 | chr7 | 55410020 | 55410126 |
| chr7 | 127371130 | 127371234 | chr7 | 129800244 | 129800434 | chr7 | 131041516 | 131041596 |
| chr7 | 134918504 | 134918637 | chr8 | 61777576 | 61777622 | chr8 | 142367673 | 142367790 |
| chr8 | 144668567 | 144668667 | chr8 | 144668910 | 144668972 | chr9 | 34224349 | 34224474 |
| chr9 | 34372806 | 34372983 | chr9 | 129401098 | 129401195 | chr9 | 139888946 | 139888980 |
| chr10 | 6003403 | 6003625 | chr10 | 22047362 | 22047601 | chr11 | 232864 | 233062 |
| chr11 | 63641073 | 63641104 | chr12 | 110353415 | 110353451 | chr13 | 28239910 | 28240164 |
| chr14 | 102564465 | 102564502 | chr16 | 3802982 | 3803074 | chr16 | 85699690 | 85699921 |
| chr17 | 26961771 | 26961833 | chr17 | 42092191 | 42092220 | chr17 | 70026544 | 70026667 |
| chr18 | 74755509 | 74755577 | chr19 | 14181306 | 14181682 | chr19 | 33468019 | 33468055 |
| chr19 | 38782560 | 38782589 | chr19 | 40829794 | 40830032 | chr19 | 45570402 | 45570450 |
| chr19 | 45574774 | 45574782 | chr19 | 45574837 | 45574888 | chr20 | 6022813 | 6023045 |
| chr20 | 32301800 | 32301953 | chr20 | 60620233 | 60620421 | chr20 | 60772886 | 60773878 |
| chr21 | 37775035 | 37775141 | chr21 | 46935740 | 46935936 | chr22 | 21977315 | 21977342 |
| chr22 | 23801460 | 23801567 | chr22 | 24560376 | 24560522 | chr22 | 39830356 | 39830457 |
| chr22 | 41657234 | 41657350 | — | — | — | — | — | — |

TABLE 18

| chr | start | end | chr | start | end | chr | star | end |
|---|---|---|---|---|---|---|---|---|
| chr1 | 3659551 | 3659643 | chr1 | 3659672 | 3659716 | chr1 | 3663533 | 3663562 |
| chr1 | 12123244 | 12123276 | chr1 | 38511662 | 38511757 | chr2 | 12858453 | 12858499 |
| chr2 | 29338159 | 29338748 | chr2 | 29338810 | 29338969 | chr2 | 31360307 | 31360590 |
| chr2 | 31360631 | 31360693 | chr2 | 31360695 | 31360756 | chr2 | 31360804 | 31360831 |
| chr2 | 31456893 | 31457039 | chr2 | 100937837 | 100938164 | chr2 | 100938481 | 100938545 |
| chr2 | 100938575 | 100938799 | chr2 | 100938801 | 100938810 | chr2 | 100938985 | 100939155 |
| chr2 | 144694753 | 144695135 | chr2 | 172367022 | 172367125 | chr2 | 241542045 | 241542344 |
| chr3 | 142791152 | 142791173 | chr3 | 142839563 | 142839578 | chr3 | 142839580 | 142839607 |
| chr3 | 179168977 | 179169016 | chr4 | 718082 | 718112 | chr4 | 79689652 | 79689732 |
| chr4 | 156297417 | 156297556 | chr4 | 156297980 | 156298073 | chr5 | 38845676 | 38845705 |
| chr5 | 82769015 | 52769061 | chr5 | 111987788 | 111987818 | chr5 | 146257500 | 146257602 |
| chr6 | 73331516 | 73331851 | chr6 | 73331876 | 73332169 | chr6 | 73332392 | 73332674 |
| chr6 | 73332987 | 73333099 | chr6 | 127440332 | 127440510 | chr6 | 127440512 | 127440524 |
| chr6 | 151815056 | 151815089 | chr6 | 152957954 | 152957995 | chr6 | 163834315 | 163834383 |
| chr6 | 163834406 | 163834533 | chr6 | 163836569 | 163836900 | chr7 | 2728069 | 2728108 |
| chr7 | 28449277 | 28449291 | chr7 | 44364839 | 44364903 | chr7 | 69064591 | 69064772 |
| chr7 | 69064834 | 69064858 | chr7 | 76033251 | 76033289 | chr7 | 90226290 | 90226363 |
| chr7 | 106797775 | 106797804 | chr7 | 107483695 | 107483918 | chr7 | 134143808 | 134143908 |
| chr7 | 140027009 | 140027043 | chr7 | 149411542 | 149411728 | chr7 | 149411835 | 149412304 |
| chr7 | 150069099 | 150069346 | chr7 | 150070022 | 150070058 | chr8 | 53853998 | 53854027 |
| chr8 | 80803674 | 80803831 | chr8 | 97507150 | 97507246 | chr8 | 143533745 | 143533774 |
| chr9 | 37026964 | 37026993 | chr9 | 93698030 | 93698051 | chr9 | 140024843 | 140024919 |
| chr9 | 140024957 | 140025023 | chr10 | 3641379 | 3641396 | chr10 | 7450525 | 7450567 |
| chr10 | 7452350 | 7452550 | chr10 | 7453492 | 7453521 | chr10 | 49731643 | 49731749 |
| chr10 | 64578319 | 64578355 | chr10 | 101089410 | 101089439 | chr10 | 125851518 | 125851645 |
| chr10 | 125852300 | 125852498 | chr10 | 125852754 | 125853191 | chr10 | 133795401 | 133795430 |
| chr11 | 2040108 | 2040148 | chr11 | 3169689 | 3169835 | chr11 | 94275795 | 94275813 |
| chr11 | 94473683 | 94473769 | chr11 | 94473803 | 94473984 | chr11 | 94502453 | 94502489 |
| chr12 | 104850506 | 104850537 | chr12 | 104850578 | 104850592 | chr12 | 104851078 | 104851186 |
| chr13 | 26625302 | 26625502 | chr13 | 28366066 | 28366122 | chr13 | 36920350 | 36920379 |
| che13 | 36920629 | 36920769 | chr13 | 73619661 | 73619698 | chr13 | 95364499 | 95364528 |
| che13 | 95364771 | 95364800 | chr13 | 95620022 | 95620057 | chr13 | 110959797 | 110959860 |
| chr15 | 45670503 | 45670839 | chr15 | 48937059 | 48937095 | chr15 | 48937428 | 48937646 |
| chr15 | 48937710 | 48937987 | chr15 | 79383948 | 79383977 | chr15 | 83776497 | 83776596 |
| chr16 | 10276758 | 10276799 | chr16 | 1027680) | 10276841 | chr16 | 71715780 | 71715809 |
| chr17 | 32908287 | 32908371 | chr17 | 46125007 | 46125061 | chr17 | 47574091 | 47574149 |
| chr17 | 80535383 | 80535469 | chr19 | 3578139 | 3578223 | chr19 | 10823679 | 10823708 |
| chr19 | 50316245 | 50316330 | chr19 | 57862640 | 57862783 | chr20 | 4803922 | 4804008 |
| chr20 | 33547579 | 33547585 | chr20 | 36531800 | 36531910 | chr20 | 37434553 | 37434722 |
| chr20 | 37434737 | 37434744 | chr20 | 39317088 | 39317196 | chr21 | 27012374 | 27012431 |
| chr21 | 45508618 | 45508647 | chr22 | 39853522 | 39853590 | chr22 | 39853592 | 39853592 |

TABLE 19

| chr | start | end | chr | start | end | chr | start | end |
|---|---|---|---|---|---|---|---|---|
| chr1 | 3663875 | 3663921 | chr1 | 9712075 | 9712104 | chr1 | 11538796 | 11538821 |
| chr1 | 11539176 | 11539205 | chr1 | 11539411 | 11539440 | chr1 | 29450492 | 29450543 |
| chr1 | 38512386 | 38512415 | chr1 | 53068387 | 53068425 | chr1 | 91869989 | 91870018 |
| chr1 | 170633608 | 170633637 | chr1 | 202679216 | 202679327 | chr1 | 209381133 | 209381165 |
| chr1 | 230561780 | 230561824 | chr1 | 244014222 | 244014376 | chr2 | 31456683 | 31456712 |
| chr2 | 56410918 | 56410996 | chr2 | 56411692 | 56411733 | chr2 | 228029471 | 228029500 |
| chr3 | 37493520 | 37493621 | chr3 | 46924935 | 46924964 | chr3 | 49907094 | 49907130 |
| chr3 | 55519220 | 55519228 | chr3 | 98620892 | 98620980 | chr4 | 331323 | 331352 |
| chr4 | 57687721 | 57687782 | chr4 | 75858574 | 75858611 | chr4 | 87515338 | 87515367 |
| chr4 | 155665446 | 155665475 | chr5 | 129240069 | 129240101 | chr6 | 53212553 | 53213932 |
| chr6 | 71665639 | 71665723 | chr6 | 168719984 | 168720019 | chr7 | 409827 | 409872 |
| chr7 | 409887 | 409892 | chr7 | 54609992 | 54610006 | chr7 | 87104817 | 87105101 |
| chr7 | 87257964 | 87258054 | chr7 | 106685283 | 106685345 | chr7 | 113726510 | 113726539 |
| chr8 | 107282164 | 107282195 | chr8 | 110704002 | 110704029 | chr8 | 110704098 | 110704144 |
| chr9 | 21974208 | 21974237 | chr9 | 36037069 | 36037098 | chr9 | 112403365 | 112403394 |
| chr9 | 132805319 | 132805445 | chr9 | 132805750 | 132805893 | chr10 | 116853876 | 116853908 |
| chr10 | 134755905 | 134755934 | chr11 | 20618293 | 20618322 | chr11 | 20618527 | 20618556 |
| chr11 | 64410724 | 64410759 | chr11 | 107461624 | 107461653 | chr11 | 114113023 | 114113062 |
| chr12 | 8850659 | 8850744 | chr12 | 95267525 | 95267554 | chr12 | 133463737 | 133463876 |
| chr12 | 133758049 | 133758107 | chr13 | 46961495 | 46961533 | chr13 | 49794118 | 49794179 |
| chr13 | 78492724 | 78492748 | chr13 | 92050761 | 92050814 | chr14 | 51561766 | 51562012 |
| chr15 | 53082444 | 53082.491 | chr15 | 65669860 | 65669899 | chr15 | 83378213 | 83378370 |
| chr15 | 91643361 | 91643586 | chr16 | 23313465 | 23313522 | chr16 | 23313780 | 23313893 |
| chr16 | 80838052 | 80838143 | chr17 | 14204213 | 14204242 | chr17 | 14204528 | 14204620 |
| chr17 | 40333045 | 40333226 | chr17 | 42907565 | 42907630 | chr17 | 48071021 | 48071050 |
| chr17 | 51901005 | 51901034 | chr17 | 56327272 | 56327301 | chr17 | 56833708 | 56833953 |
| chr19 | 10527166 | 10527243 | chr19 | 12163452 | 12163672 | chr19 | 12163894 | 12163923 |
| chr19 | 12175446 | 12175504 | chr19 | 12476501 | 12476556 | chr19 | 12606382 | 12606511 |
| che19 | 23433144 | 23433223 | chr19 | 24216976 | 24217023 | chr19 | 33685545 | 33685581 |
| chr19 | 35264086 | 35264092 | chr19 | 37263533 | 37263584 | chr19 | 37341762 | 37341962 |
| chr19 | 37569394 | 37569554 | chr19 | 38085255 | 38085759 | chr19 | 38085958 | 38086066 |
| chr19 | 38146063 | 38146247 | chr19 | 38146458 | 38146568 | chr19 | 52097690 | 52097732 |
| chr19 | 53031202 | 53031215 | chr19 | 53193859 | 53193893 | chr19 | 58740087 | 58740118 |
| chr20 | 4230571 | 4230600 | chr20 | 20348527 | 20348605 | chr20 | 20349575 | 20349604 |
| chr20 | 39317751 | 39318138 | chr20 | 62680682 | 62680739 | chr21 | 33244922 | 33245040 |
| chr21 | 33245716 | 33245718 | chr21 | 33246038 | 33246190 | chr22 | 21368588 | 21368617 |
| chr22 | 24820331 | 24820396 | chr22 | 44208422 | 44208448 | — | — | — |

TABLE 20

| chr | start | end | chr | start | end | chr | start | end |
|---|---|---|---|---|---|---|---|---|
| chr1 | 898655 | 898690 | chr1 | 1856437 | 1856466 | chr1 | 1910416 | 1910445 |
| chr1 | 2375149 | 2375355 | chr1 | 10166522 | 10166551 | chr1 | 32180398 | 32180427 |
| chr1 | 97185263 | 97185357 | chr1 | 177150774 | 177150803 | chr1 | 246488176 | 246488316 |
| chr3 | 154797384 | 154797416 | chr4 | 146853952 | 146853981 | chr4 | 185089697 | 185089797 |
| chr5 | 57878711 | 57878752 | chr5 | 87976104 | 87976308 | chr5 | 87976526 | 87976559 |
| chr5 | 174220972 | 174221001 | chr7 | 44097691 | 44097875 | chr8 | 67025054 | 67025365 |
| chr9 | 140709047 | 140709174 | chr9 | 140727472 | 140727511 | chr9 | 140727846 | 140727930 |
| chr10 | 524755 | 524770 | chr11 | 392577 | 392720 | chr11 | 1027541 | 1027574 |
| chr11 | 66454425 | 66454454 | chr11 | 94884131 | 94884160 | chr12 | 54399617 | 54399646 |
| chr13 | 114807745 | 114807815 | chr14 | 21100749 | 21100778 | chr14 | 21100802 | 21100831 |
| chr16 | 1397455 | 1397484 | chr16 | 2128578 | 2128682 | chr16 | 2129145 | 2129332 |
| chr16 | 88757467 | 88757496 | chr17 | 1536129 | 1536146 | chr17 | 7348886 | 7348997 |
| chr17 | 17062575 | 17062752 | chr17 | 17123964 | 17123993 | chr18 | 32557847 | 32557864 |
| chr18 | 74501145 | 74501183 | chr19 | 1308066 | 1308081 | chr19 | 1775077 | 1775239 |
| chr19 | 58144495 | 58144701 | chr21 | 39047777 | 39047838 | chr21 | 44283611 | 44283774 |
| chr22 | 36902292 | 36902381 | chr22 | 42096003 | 42096190 | chr22 | 47023045 | 47023191 |
| chr22 | 47054687 | 47054700 | chr22 | 50943094 | 50943262 | chrX | 3746613 | 3746642 |

TABLE 21

| chr | start | end | chr | start | end | chr | start | end |
|---|---|---|---|---|---|---|---|---|
| chr1 | 213123890 | 213123919 | chr2 | 1653023 | 1653230 | chr5 | 17512116 | 17512144 |
| chr6 | 26284812 | 26284898 | chr7 | 6543151 | 6543216 | chr7 | 64330412 | 64330470 |
| chr10 | 7213532 | 7213535 | chr10 | 7424627 | 7424687 | chr11 | 68409559 | 68409588 |
| chr12 | 105478324 | 105478359 | chr15 | 99456300 | 99456329 | chr16 | 47177526 | 47177606 |
| chr16 | 88942120 | 88942160 | chr17 | 29298081 | 29298184 | chr17 | 29298186 | 29298463 |

TABLE 21-continued

| chr | start | end | chr | start | end | chr | start | end |
|---|---|---|---|---|---|---|---|---|
| chr17 | 42402885 | 42402917 | chr17 | 62777336 | 62777450 | chr18 | 77309534 | 77309563 |
| chr22 | 40075158 | 40075302 | — | | | — | | |

TABLE 22

| chr | start | end | chr | start | end | chr | start | end |
|---|---|---|---|---|---|---|---|---|
| chr1 | 12251874 | 12251958 | chr1 | 23586244 | 29586563 | chr1 | 50891347 | 50891376 |
| chr1 | 78511638 | 78511718 | chr1 | 91180277 | 91180306 | chr1 | 156010529 | 156010548 |
| chr1 | 161471751 | 161471779 | chr1 | 180204063 | 180204092 | chr1 | 200012190 | 200012191 |
| chr1 | 223936996 | 223937014 | chr1 | 228645141 | 228645244 | chr1 | 228645306 | 228645536 |
| chr2 | 43451910 | 43452327 | chr2 | 55289095 | 55289274 | chr2 | 106060616 | 106060792 |
| chr2 | 111875279 | 111875518 | chr2 | 118981668 | 118981738 | chr2 | 162272990 | 162273057 |
| chr2 | 175192104 | 175192136 | chr2 | 175193269 | 175193324 | chr2 | 175200141 | 175200170 |
| chr2 | 177001532 | 177001561 | chr2 | 223158970 | 223158999 | chr2 | 223165435 | 223165503 |
| chr2 | 223169835 | 223169864 | chr2 | 223176152 | 223176181 | chr2 | 230795536 | 230795565 |
| chr2 | 236877263 | 236877367 | chr2 | 242523908 | 242523985 | chr3 | 50402318 | 50402944 |
| chr3 | 181442377 | 181442410 | chr3 | 184057527 | 184057557 | chr4 | 3446992 | 3447021 |
| chr4 | 41750224 | 41750262 | chr4 | 42398843 | 42398872 | chr4 | 83323507 | 83323675 |
| chr4 | 166414897 | 166414921 | chr5 | 6687381 | 6687431 | chr5 | 10333726 | 10333762 |
| chr5 | 43215539 | 43215562 | chr5 | 50264821 | 50264850 | chr6 | 10416119 | 10416148 |
| chr6 | 18035868 | 18036015 | chr6 | 26332179 | 26332218 | chr6 | 28303563 | 28303571 |
| chr6 | 2830384Z | 28304263 | chr6 | 50691066 | 50691095 | chr6 | 126068093 | 126068158 |
| chr6 | 152623016 | 152623493 | chr6 | 154970559 | 154970587 | chr7 | 2238119 | 2238235 |
| chr7 | 5262472 | 5262562 | chr7 | 27136761 | 27136790 | chr7 | 27195483 | 27195492 |
| chr7 | 113722940 | 113722969 | chr7 | 156801417 | 156801446 | chr8 | 108509544 | 108509650 |
| chr8 | 128931157 | 128931261 | chr8 | 142292553 | 142292774 | chr9 | 21965102 | 21965372 |
| chr9 | 21965686 | 21965757 | chr9 | 96721121 | 96721275 | chr9 | 96722477 | 96722548 |
| chr9 | 126349070 | 126349104 | chr10 | 3678618 | 3678637 | chr10 | 71327726 | 71327755 |
| chr10 | 102986586 | 102986758 | chr10 | 118890981 | 118891010 | chr10 | 124910364 | 124910439 |
| chr10 | 131937393 | 131937428 | chr11 | 67781387 | 67781564 | chr12 | 28127931 | 2812799Z |
| chr12 | 28128620 | 28129054 | chr12 | 64783186 | 64783308 | chr12 | 72332642 | 72332696 |
| chr12 | 117474066 | 117474125 | chr14 | 37124038 | 37124067 | chr14 | 55765286 | 55765686 |
| chr14 | 73318472 | 73318629 | chr14 | 91691167 | 91691306 | chr14 | 91766189 | 91766450 |
| chr14 | 102682120 | 102682149 | chr15 | 37402975 | 37403087 | chr15 | 37403116 | 37403127 |
| chr15 | 65862054 | 65862121 | chr15 | 68125459 | 68125496 | chr16 | 142650 | 142775 |
| chr16 | 667548 | 667561 | chr16 | 677973 | 677993 | chr16 | 1407819 | 1407846 |
| chr16 | 2281250 | 2281314 | chr16 | 30907011 | 30907049 | chr16 | 30907123 | 30907148 |
| chr16 | 79623805 | 79623854 | chr16 | 85517346 | 85517388 | chr17 | 27181284 | 27181371 |
| chr17 | 37757154 | 37757217 | chr17 | 46655149 | 46655178 | chr17 | 46675420 | 46675449 |
| chr17 | 46691988 | 46692022 | chr17 | 46801219 | 46801277 | chr17 | 59539492 | 59539601 |
| chr17 | 75733979 | 75734108 | chr18 | 31902794 | 31902944 | chr18 | 55850846 | 55850987 |
| chr18 | 77550281 | 77550367 | chr19 | 8576915 | 8577000 | chr19 | 10407091 | 10407120 |
| chr20 | 44452732 | 44453063 | chr22 | 18328128 | 18328268 | chr22 | 19706634 | 19706677 |
| chr22 | 22058204 | 22058238 | chr22 | 28838201 | 28838292 | chr22 | 29445753 | 29445923 |

TABLE 23

| chr | start | end | chr | start | end | chr | start | end |
|---|---|---|---|---|---|---|---|---|
| chr1 | 2331364 | 2331437 | chr1 | 90309344 | 90309490 | chr1 | 219347395 | 219347472 |
| chr1 | 234620965 | 234620979 | chr1 | 245494496 | 245494578 | chr2 | 47200592 | 47200621 |
| chr2 | 47249735 | 47249848 | chr2 | 178973004 | 178973042 | chr2 | 209225238 | 209225275 |
| chr2 | 220080582 | 220080941 | chr2 | 240319921 | 240320012 | chr3 | 193419703 | 193419732 |
| chr4 | 1008741 | 1008806 | chr4 | 1282516 | 1282545 | chr4 | 57777438 | 57777577 |
| chr6 | 43639549 | 43639710 | chr7 | 127615922 | 127615951 | chr7 | 138042222 | 138042288 |
| chr7 | 140180180 | 140180298 | chr8 | 59058942 | 59059233 | chr8 | 141596887 | 141597022 |
| chr8 | 143558473 | 143558604 | chr8 | 144203654 | 144203708 | chr8 | 144303563 | 144303592 |
| chr10 | 135018033 | 135018070 | chr11 | 66658258 | 56658290 | chr11 | 120998702 | 120998825 |
| chr14 | 105512064 | 105512395 | chr16 | 4431127 | 4431189 | chr17 | 7368948 | 7369139 |
| chr17 | 77084519 | 77084667 | chr19 | 56201644 | 56201812 | chr22 | 46931261 | 46931332 |

TABLE 24

| chr | start | end | chr | start | end | chr | start | end |
|---|---|---|---|---|---|---|---|---|
| chr1 | 2472175 | 2472301 | chr1 | 6186512 | 6186546 | chr1 | 16475032 | 16475207 |
| chr1 | 17445858 | 17445943 | chr1 | 53705675 | 53705701 | chr1 | 62793238 | 62793267 |
| chr1 | 91182806 | 91182835 | chr1 | 98515143 | 98515191 | chr1 | 98519024 | 98519056 |
| chr1 | 115631868 | 115631915 | chr1 | 115880364 | 115880395 | chr1 | 156815693 | 156815745 |
| chr1 | 182584084 | 182584340 | chr1 | 182584404 | 182584613 | chr1 | 217307385 | 217307437 |
| chr1 | 240256664 | 240256780 | chr2 | 5833900 | 5833932 | chr2 | 7164468 | 7164704 |
| chr2 | 7571718 | 7571747 | chr2 | 18059782 | 18059841 | chr2 | 47193958 | 47193960 |
| chr2 | 99439478 | 99439507 | chr2 | 131594990 | 131595019 | chr2 | 145282120 | 145282149 |
| chr2 | 171822429 | 171822480 | chr3 | 5137961 | 5138019 | chr3 | 13679285 | 13679319 |
| chr3 | 38030619 | 38030782 | chr3 | 140770070 | 140770099 | chr3 | 152877667 | 152877696 |
| chr3 | 184319829 | 184319843 | chr3 | 184319874 | 184319891 | chr3 | 195601240 | 195601312 |
| chr3 | 195602364 | 195602435 | chr4 | 1093537 | 1093558 | chr4 | 1331676 | 1331705 |
| chr4 | 5892136 | 5892194 | chr4 | 7758477 | 7758561 | chr4 | 42154663 | 42154697 |
| chr4 | 57803529 | 57803558 | chr4 | 113431916 | 113431930 | chr4 | 183064875 | 183064966 |
| chr4 | 184921856 | 184921885 | chr5 | 1930991 | 1931005 | chr5 | 2753049 | 2753078 |
| chr5 | 3595850 | 3595876 | chr5 | 17218196 | 17218225 | chr5 | 76940341 | 76940374 |
| chr5 | 138273818 | 138273845 | chr6 | 711143 | 711293 | chr6 | 26199138 | 26199167 |
| chr6 | 26199687 | 26199716 | chr6 | 52344376 | 52344405 | chr6 | 72596273 | 72596315 |
| chr7 | 1970843 | 1970872 | chr7 | 20826885 | 20826939 | che7 | 45614930 | 45615020 |
| chr7 | 100808467 | 100808502 | chr8 | 41166306 | 41166374 | chr9 | 77113806 | 77113825 |
| chr9 | 135456477 | 135456544 | chr9 | 140033002 | 140033050 | chr10 | 73157868 | 73158027 |
| chr10 | 85954426 | 85954457 | chr10 | 128994871 | 128994903 | chr10 | 130338728 | 130338761 |
| chr10 | 133849599 | 133849628 | chr11 | 27744451 | 27744480 | chr11 | 131564971 | 131565073 |
| chr12 | 4274272 | 4274409 | chr12 | 4379358 | 4379491 | chr12 | 4382007 | 4382162 |
| chr12 | 5541101 | 5541177 | chr12 | 79257223 | 79257351 | chr12 | 94544023 | 94544052 |
| chr12 | 101025381 | 101025410 | chr12 | 103889161 | 103889211 | chr12 | 127940087 | 127940189 |
| chr13 | 32605035 | 32605212 | chr13 | 32605443 | 32605596 | chr13 | 32605675 | 32605965 |
| chr14 | 32597621 | 325976SZ | chr14 | 69014045 | 69014110 | chr14 | 92979918 | 92979991 |
| chr14 | 105714416 | 105714442 | chr14 | 105715248 | 105715393 | chr15 | 68128595 | 68128597 |
| chr15 | 74818773 | 74818789 | chr15 | 89943411 | 89943440 | chr16 | 12996949 | 12997011 |
| chr16 | 89007521 | 89007558 | chr16 | 89008563 | 89008592 | chr18 | 3215043 | 3215256 |
| chr18 | 57364659 | 57364691 | chr18 | 75362932 | 75362985 | chr19 | 869338 | 869363 |
| chr19 | 1764294 | 1764339 | chr19 | 1776505 | 1776534 | chr19 | 4054436 | 4054463 |
| chr19 | 5292813 | 5292844 | chr19 | 12996170 | 12996280 | chr19 | 41018717 | 41018746 |
| chr19 | 42028503 | 42028549 | chr19 | 51228050 | 51228079 | chr19 | 52552105 | 52552120 |
| chr20 | 52311464 | 52311505 | chr20 | 59804233 | 59804235 | chr20 | 62321824 | 62321881 |
| chr22 | 22006004 | 22006243 | chr22 | 41634394 | 41634423 | — | — | —. |

18. The method of claim 1, wherein the non-overlapping sequences are at least 50 nucleotides in length.

19. The method of claim 1, wherein the overlapping and non-overlapping sequences together are at least 75 nucleotides in length.

20. The method of claim 1, wherein each of the at least 1,000 different oligonucleotide probes is less than 300 nucleotides in length.

21. The method of claim 1, wherein (i) the target genomic region is a region of a human genome; and (ii) none of the at least 1,000 different oligonucleotide probes comprises a contiguous 45 bases having at least 90% sequence complementarity to at least 20 off-target regions in a GRCh37/hg19 genome.

* * * * *